(12) United States Patent
Borhani et al.

(10) Patent No.: US 7,400,979 B2
(45) Date of Patent: Jul. 15, 2008

(54) METHOD OF IDENTIFYING INHIBITORS OF LCK

(75) Inventors: David W. Borhani, Worcester, MA (US); David Calderwood, Framingham, MA (US); Richard W. Dixon, Jefferson, MA (US); Gavin C. Hirst, Princeton, MA (US); Peter Hrnciar, Lexington, MA (US); Andreas Loew, Worcester, MA (US); Adelaine Leung, Mississauga (CA); Kurt Ritter, Frankfurt (DE)

(73) Assignee: Abbott Laboratories, Abbott Park, IL (US)

( * ) Notice: Subject to any disclaimer, the term of this patent is extended or adjusted under 35 U.S.C. 154(b) by 174 days.

(21) Appl. No.: 10/212,346

(22) Filed: Aug. 5, 2002

(65) Prior Publication Data

US 2003/0175935 A1 Sep. 18, 2003

Related U.S. Application Data

(60) Provisional application No. 60/310,051, filed on Aug. 3, 2001.

(51) Int. Cl.
*G06F 17/11* (2006.01)
*G06F 17/50* (2006.01)
*G06F 19/00* (2006.01)

(52) U.S. Cl. .......................... 702/19; 435/15
(58) Field of Classification Search .................. 702/19; 435/15
See application file for complete search history.

(56) References Cited

U.S. PATENT DOCUMENTS 6,589,758 B1 * 7/2003 Zhu ............................ 435/15

FOREIGN PATENT DOCUMENTS

| WO | 00/70030 | 11/2000 |
| WO | 01/25238 | 4/2001 |

OTHER PUBLICATIONS

Drenth, Jan. Principles of Protein X-ray Crystallography. 1994. Springer-Verlag. pp. 1-19.*
Sequence Alignment of amino acids 237-501 of instant Seq ID No. 1 with Seq ID No. 1 of U.S. Patent No. 6,589,758. 1 page.*
Brunger, A.T., (1992). "The free R value: a novel statistical quantity for assessing the accuracy of crystal structures", Nature 355, 472-474.
Brünger, A. T., Adams, P. D., Clore, G. M., Gros, P., Grosse-Kunstleve, R. W., Jiang, J.-S., Kuszewski, J., Nilges, N., Pannu, N. S., Read, R. J., et al. , (1998). "Crystallography & NMR system (CNS): A new software system for macromolecular structure determination", Acta Crystallogr D54, 905-921.
Brünger, A. T., et al. (1987). Solution of a Protein Crystal Structure With a Model Obtained From NMR Interproton Distance Restraints. Science 235, 1049-1053.
Collaborative Computational Project, N. (1994). The CCP4 suite: programs for protein crystallography. Acta Crystallogr D50 760-763.
Dajani, R., Fraser, E., Roe, S. M., Young, N., Good, V., Dale, T. C., and Pearl, L. H. (2001). Crystal structure of glycogen synthase kinase 3 beta: structural basis for phosphate-primed substrate specificity and autoinhibition. Cell 105, 721-732.
Davies, T. G., Tunnah, P., Meijer, L., Marko, D., Eisenbrand, G., Endicott, J. A., and Noble, M. E. (2001). Inhibitor binding to active and inactive CDK2: the crystal structure of CDK2-cyclin A/indirubin-5-sulphonate. Structure (Camb) 9, 389-397.
Evans, P. R. (1997). Scala. Joint CCP4 and ESF-EA CBM Newsletter 33, 22-24.
Gosser, Y. Q., Zheng, J., Overduin, M., Mayer, B. J., and Cowburn, D. (1995). The solution structure of Abl SH3, and its relationship to SH2 in the SH(32) construct. Structure 3, 1075-1086.
Hubbard, S. R., Wei, L., Ellis, L., and Hendrickson, W. A. (1994). Crystal structure of the tyrosine kinase domain of the human insulin receptor. Nature 372, 746-754.
Jones, T. A., Zou, J. Y., Cowan, S. W., and Kjelgaard, M. (1991). Improved methods for building protein models in electron density maps and the location of errors in these models. Acta Crystallogr A47, 110-119.
Kabsch, W. (1993). Automatic processing of rotation diffraction data from crystals of initially unknown symmetry and cell constants. J Appl Crystallogr 26, 795-800.
Knighton, D. R., Zheng, J. H., Ten Eyck, L. F., Xuong, N. H., Taylor, S. S., and Sowadski, J. M. (1991). Structure of a peptide inhibitor bound to the catalytic subunit of cyclic adenosine monophosphate-dependent protein kinase. Science 253, 414-420.
Laskowski, R. A., MacArthur, M. W., Moss, D. S., and Thornton, J. M. (1993). Procheck: a program to check the stereochemical quality of protein structures. J Appl Crystallogr 26, 283-291.
Lei, M., Lu, W., Meng, W., Parrini, M. C., Eck, M. J., Mayer, B. J., and Harrison, S. C. (2000). Structure of PAK1 in an autoinhibited conformation reveals a multistage activation switch. Cell 102, 387-397.

(Continued)

*Primary Examiner*—Michael Borin
(74) *Attorney, Agent, or Firm*—Ken Zwicker; Gayle O'Brien

(57) ABSTRACT

The present invention relates to polypeptides which comprise the ligand binding domain of Lck, crystalline forms of these polypeptides, and the use of these crystalline forms to determine the three dimensional structure of the catalytic domain of Lck. The invention also relates to the use of the three dimensional structure of the Lck catalytic domain both alone, or in complex with inhibitors, in methods of designing and/or identifying potential inhibitors of Lck activity, for example, compounds which inhibit the binding of a native substrate to the Lck catalytic domain. The invention also relates to the use of the three dimensional structure of the Lck catalytic domain both alone, or in complex with inhibitors, in methods of designing and/or identifying potential selective inhibitors of Lck activity, for example, compounds which inhibit the binding of a native substrate to the Lck catalytic domain selectively.

3 Claims, 896 Drawing Sheets

OTHER PUBLICATIONS

Eck et al. "Strucutre of the regulatory domains of the Src-family tyrosine kinase Lck" Nature, Apr. 21, 1994, vol. 368 (6473), pp. 764-769.

Matthews, B. W. (1968). Solvent content of protein crystals. J Mol Biol 33, 491-497.

McTigue, M. A., Wickersham, J. A., Pinko, C., Showalter, R. E., Parast, C. V., Tempczyk-Russell, A., Gehring, M. R., Mroczkowski, B., Kan, C. C., Villafranca, J. E., and Appelt, K. (1999). Crystal structure of the kinase domain of human vascular endothelial growth factor receptor 2: a key enzyme in angiogenesis. Structure Fold Des 7, 319-330.

Mohammadi, M., Schlessinger, J., and Hubbard, S. R. (1996). Structure of the FGF receptor tyrosine kinase domain reveals a novel autoinhibitory mechanism. Cell 86, 577-587.

Narula, S. S., Yuan, R. W., Adams, S. E., Green, O. M., Green, J., Philips, T. B., Zydowsky, L. D., Botfield, M. C., Hatada, M., Laird, E. R., and et al. (1995). Solution structure of the C-terminal SH2 domain of the human tyrosine kinase Syk complexed with a phosphotyrosine pentapeptide. Structure 3, 1061-1073.

Navaza, J. (1994). AMoRe: an automated package for molecular replacement. Acta Crystallogr A50, 157-163.

Noble, M. E., Musacchio, A., Saraste, M., Courtneidge, S. A., and Wierenga, R. K. (1993). Crystal structure of the SH3 domain in human Fyn; comparison of the three-dimensional structures of SH3 domains in tyrosine kinases and spectrin. Embo J 12, 2617-2624.

Otwinowski, Z., and Minor, W. (1997). Processing of x-ray diffraction data collected in oscillation mode. Meth Enzymol 276, 307-326.

Read, R. J. (1986). Improved Fourier coefficients for maps using phases from partial structures with errors. Acta Crystallogr A42, 140-149.

Russo, A. A., Jeffrey, P. D., Patten, A. K., Massague, J., and Pavletich, N. P. (1996). Crystal structure of the p27Kip1 cyclin-dependent-kinase inhibitor bound to the cyclin A-Cdk2 complex. Nature 382, 325-331.

Schindler, T., Bornmann, W., Pellicena, P., Miller, W. T., Clarkson, B., and Kuriyan, J. (2000). Structural mechanism for STI-571 inhibition of abelson tyrosine kinase. Science 289, 1938-1942.

Schindler, T., Sicheri, F., Pico, A., Gazit, A., Levitzki, A., and Kuriyan, J. (1999). Crystal structure of Hck in complex with a Src family-selective tyrosine kinase inhibitor. Mol Cell 3, 639-648.

Schulze-Gahmen, U., De Bondt, H. L., and Kim, S. H. (1996). High-resolution crystal structures of human cyclin-dependent kinase 2 with and without ATP: bound waters and natural ligand as guides for inhibitor design. J Med Chem 39, 4540-4546.

Shewchuk, L. M., Hassell, A. M., Ellis, B., Holmes, W. D., Davis, R., Horne, E. L., Kadwell, S. H., McKee, D. D., and Moore, J. T. (2000). Structure of the Tie2 RTK domain: self-inhibition by the nucleotide binding loop, activation loop, and C-terminal tail. Structure Fold Des 8, 1105-1113.

Sicheri, F., Moarefi, I., and Kuriyan, J. (1997). Crystal structure of the Src family tyrosine kinase Hck. Nature 385, 602-609.

Su, Y., Dostmann, W. R., Herberg, F. W., Durick, K. Xuong, N. H., Ten Eyck, L., Taylor, S. S., and Varughese, K. I. (1995). Regulatory subunit of protein kinase A: structure of deletion mutant with cAMP binding domains. Science 269, 807-813.

Superti-Furga, G. (1995). Regulation of the Src protein tyrosine kinase. FEBS Lett 369, 62-66.

Vriend, G. (1990). Whatif: a molecular modelling and drug design program. J Mol Graphics 8, 52-56.

Waksman, G., Kominos, D., Robertson, S. C., Pant, N., Baltimore, D., Birge, R. B., Cowburn, D., Hanafusa, H., Mayer, B. J., Overduin, M., and et al. (1992). Crystal structure of the phosphotyrosine recognition domain SH2 of v-src complexed with tyrosine-phosphorylated peptides. Nature 358, 646-653.

Williams, J. C., Weijland, A., Gonfloni, S., Thompson, A., Courtneidge, S. A., Superti-Furga, G., and Wierenga, R. K. (1997). The 2.35 A crystal structure of the inactivated form of chicken Src: a dynamic molecule with multiple regulatory interactions. J Mol Biol 274, 757-775.

Xu, W., Harrison, S. C., and Eck, M. J. (1997). Three-dimensional structure of the tyrosine kinase c-Src. Nature 385, 595-602.

Yamaguchi, H., and Hendrickson, W. A. (1996). Structural basis for activation of human lymphocyte kinase Lck upon tyrosine phosphorylation. Nature 384, 484-489.

Zhu, X., Kim, J. L., Newcomb, J. R., Rose, P. E., Stover, D. R., Toledo, L. M., Zhao, H., and Morgenstern, K. A. (1999). Structural analysis of the lymphocyte-specific kinase Lck in complex with non-selective and Src family selective kinase inhibitors. Structure Fold Des 7, 651-661.

French, S., and Wilson, K. (1978). On the Treatment of Negative Intensity Observations. Acta Crystallogr A34, 517-525.

Eck, M.J. et al., (1994). Structure of the regulatory domains of the Src-family tyrosine kinase Lck. Nature, 368, 764-769.

Hooft, R. W. W., et al., "Errors in Protein Structurs", Nature, 381:272, (1996).

Xu, W., et al., "Crystal Structurs of c-Src Reveal Features of Its Autoinhibitory Mechanism", Mol Cell., 3:629-638, (1999).

* cited by examiner

Figure 1.

SEQ ID NO. 1:

```
              10          20          30          40          50          60
              |           |           |           |           |           |
    MGCGCSSHPE  DDWMENIDVC  ENCHYPIVPL  DGKGTLLIRN  GSEVRDPLVT  YEGSNPPASP
              70          80          90         100         110         120
              |           |           |           |           |           |
    LQDNLVIALH  SYEPSHDGDL  GFEKGEQLRI  LEQSGEWWKA  QSLTTGQEGF  IPFNFVAKAN
             130         140         150         160         170         180
              |           |           |           |           |           |
    SLEPEPWFFK  NLSRKDAERQ  LLAPGNTHGS  FLIRESESTA  GSFSLSVRDF  DQNQGEVVKH
             190         200         210         220         230         240
              |           |           |           |           |           |
    YKIRNLDNGG  FYISPRITFP  GLHELVRHYT  NASDGLCTRL  SRPCQTQKPQ  KPWWEDEWEV
             250         260         270         280         290         300
              |           |           |           |           |           |
    PRETLKLVER  LGAGQFGEVW  MGYYNGHTKV  AVKSLKQGSM  SPDAFLAEAN  LMKQLQHQRL
             310         320         330         340         350         360
              |           |           |           |           |           |
    VRLYAVVTQE  PIYIITEYME  NGSLVDFLKT  PSGIKLTINK  LLDMAAQIAE  GMAFIEERNY
             370         380         390         400         410         420
              |           |           |           |           |           |
    IHRDLRAANI  LVSDTLSCKI  ADFGLARLIE  DNEYTAREGA  KFPIKWTAPE  AINYGTFTIK
             430         440         450         460         470         480
              |           |           |           |           |           |
    SDVWSFGILL  TEIVTHGRIP  YPGMTNPEVI  QNLERGYRMV  RPDNCPEELY  QLMRLCWKER
             490         500         509
              |           |           |
    PEDRPTFDYL  RSVLEDFFTA  TEGQYQPQP
```

Figure 2.

SEQ ID NO. 2:

```
     237
      |
     EWEV 250        260        270        280        290        300
             |          |          |          |          |          |
     PRETLKLVER LGAGQFGEVW MGYYNGHTKV AVKSLKQGSM SPDAFLAEAN LMKQLQHQRL 310        320        330        340        350        360
             |          |          |          |          |          |
     VRLYAVVTQE PIYIITEYME NGSLVDFLKT PSGIKLTINK LLDMAAQIAE GMAFIEERNY 370        380        390        400        410        420
             +          |          |          *          |          |
     IHRNLRAANI LVSDTLSCKI ADFGLARLIE DNEYTAREGA KFPIKWTAPE AINYGTFTIK 430        440        450        460        470        480
             |          |          |          |          |          |
     SDVWSFGILL TEIVTHGRIP YPGMTNPEVI QNLERGYRMV RPDNCPEELY QLMRLCWKER 490        500 501
             |          |   |
     PEDRPTFDYL RSVLEDFFTA T
```

Figure 3.

SEQ ID NO. 3

```
           231       240
            |         |
           KPWWEDEWEV 250       260        270        280        290        300
            |         |          |          |          |          |
           PRETLKLVER LGAGQFGEVW MGYYNGHTKV AVKSLKQGSM SPDAFLAEAN LMKQLQHQRL 310       320        330        340        350        360
            |         |          |          |          |          |
           VRLYAVVTQE PIYIITEYME NGSLVDFLKT PSGIKLTINK LLDMAAQIAE GMAFIEERNY 370       380        390        400        410        420
            +         |          |          *          |          |
           IHRNLRAANI LVSDTLSCKI ADFGLARLIE DNEYTAREGA KFPIKWTAPE AINYGTFTIK 430       440        450        460        470        480
            |         |          |          |          |          |
           SDVWSFGILL TEIVTHGRIP YPGMTNPEVI QNLERGYRMV RPDNCPEELY QLMRLCWKER 490       500 501
            |         |   |
           PEDRPTFDYL RSVLEDFFTA T
```

```
CRYST1   57.611   44.641  121.580  90.00   90.17   90.00 P21              1
SCALE1      0.017358  0.000000  0.000052        0.00000
SCALE2      0.000000  0.022401  0.000000        0.00000
SCALE3      0.000000  0.000000  0.008225        0.00000
ATOM       1   CB   TRP A 238      17.239   -5.551   28.068  1.00 61.01      A    C
ATOM       2   CG   TRP A 238      16.804   -6.100   26.701  1.00 63.28      A    C
ATOM       3   CD2  TRP A 238      17.408   -5.833   25.414  1.00 63.96      A    C
ATOM       4   CE2  TRP A 238      16.662   -6.550   24.443  1.00 64.42      A    C
ATOM       5   CE3  TRP A 238      18.505   -5.065   24.994  1.00 64.01      A    C
ATOM       6   CD1  TRP A 238      15.747   -6.941   26.451  1.00 63.91      A    C
ATOM       7   NE1  TRP A 238      15.658   -7.212   25.101  1.00 64.29      A    N
ATOM       8   CZ2  TRP A 238      16.982   -6.517   23.070  1.00 64.82      A    C
ATOM       9   CZ3  TRP A 238      18.823   -5.034   23.621  1.00 63.76      A    C
ATOM      10   CH2  TRP A 238      18.063   -5.757   22.684  1.00 63.98      A    C
ATOM      11   C    TRP A 238      18.901   -5.528   29.978  1.00 57.77      A    C
ATOM      12   O    TRP A 238      19.423   -4.417   29.907  1.00 56.89      A    O
ATOM      13   N    TRP A 238      18.169   -7.697   28.952  1.00 58.53      A    N
ATOM      14   CA   TRP A 238      18.459   -6.258   28.701  1.00 58.69      A    C
ATOM      15   N    GLU A 239      18.675   -6.143   31.140  1.00 57.43      A    N
ATOM      16   CA   GLU A 239      19.074   -5.550   32.425  1.00 56.55      A    C
ATOM      17   CB   GLU A 239      18.207   -6.073   33.571  1.00 59.08      A    C
ATOM      18   CG   GLU A 239      17.148   -5.105   34.054  1.00 62.51      A    C
ATOM      19   CD   GLU A 239      15.945   -5.035   33.131  1.00 64.73      A    C
ATOM      20   OE1  GLU A 239      16.077   -4.493   32.007  1.00 65.89      A    O
ATOM      21   OE2  GLU A 239      14.862   -5.519   33.538  1.00 66.11      A    O
ATOM      22   C    GLU A 239      20.520   -5.892   32.738  1.00 54.37      A    C
ATOM      23   O    GLU A 239      20.927   -7.054   32.620  1.00 54.88      A    O
ATOM      24   N    VAL A 240      21.295   -4.887   33.136  1.00 50.06      A    N
ATOM      25   CA   VAL A 240      22.698   -5.103   33.473  1.00 45.68      A    C
ATOM      26   CB   VAL A 240      23.657   -4.660   32.330  1.00 43.88      A    C
ATOM      27   CG1  VAL A 240      23.352   -5.417   31.061  1.00 42.89      A    C
ATOM      28   CG2  VAL A 240      23.592   -3.153   32.116  1.00 42.23      A    C
ATOM      29   C    VAL A 240      23.089   -4.363   34.748  1.00 44.71      A    C
ATOM      30   O    VAL A 240      22.388   -3.440   35.194  1.00 43.08      A    O
ATOM      31   N    PRO A 241      24.173   -4.824   35.400  1.00 43.46      A    N
ATOM      32   CD   PRO A 241      24.779   -6.155   35.232  1.00 43.24      A    C
ATOM      33   CA   PRO A 241      24.663   -4.199   36.624  1.00 42.30      A    C
ATOM      34   CB   PRO A 241      25.698   -5.209   37.121  1.00 41.87      A    C
ATOM      35   CG   PRO A 241      25.167   -6.497   36.648  1.00 42.12      A    C
ATOM      36   C    PRO A 241      25.306   -2.844   36.335  1.00 42.53      A    C
ATOM      37   O    PRO A 241      25.945   -2.644   35.300  1.00 40.91      A    O
ATOM      38   N    ARG A 242      25.100   -1.913   37.261  1.00 43.88      A    N
ATOM      39   CA   ARG A 242      25.647   -0.567   37.189  1.00 45.00      A    C
ATOM      40   CB   ARG A 242      25.267    0.161   38.479  1.00 45.81      A    C
ATOM      41   CG   ARG A 242      25.851    1.536   38.643  1.00 47.79      A    C
ATOM      42   CD   ARG A 242      25.288    2.493   37.620  1.00 48.72      A    C
ATOM      43   NE   ARG A 242      23.826    2.588   37.678  1.00 49.77      A    N
ATOM      44   CZ   ARG A 242      23.127    3.088   38.697  1.00 48.71      A    C
ATOM      45   NH1  ARG A 242      23.733    3.550   39.786  1.00 48.82      A    N
ATOM      46   NH2  ARG A 242      21.807    3.144   38.608  1.00 47.73      A    N
ATOM      47   C    ARG A 242      27.176   -0.640   37.050  1.00 45.68      A    C
```

Figure 4

| | | | | | | | | | | | |
|---|---|---|---|---|---|---|---|---|---|---|---|
| ATOM | 48 | O | ARG | A | 242 | 27.788 | 0.213 | 36.419 | 1.00 | 44.62 | A | O |
| ATOM | 49 | N | GLU | A | 243 | 27.751 | -1.701 | 37.618 | 1.00 | 47.32 | A | N |
| ATOM | 50 | CA | GLU | A | 243 | 29.192 | -1.979 | 37.642 | 1.00 | 48.31 | A | C |
| ATOM | 51 | CB | GLU | A | 243 | 29.467 | -3.312 | 38.371 | 1.00 | 50.83 | A | C |
| ATOM | 52 | CG | GLU | A | 243 | 29.106 | -3.355 | 39.870 | 1.00 | 54.77 | A | C |
| ATOM | 53 | CD | GLU | A | 243 | 27.690 | -2.859 | 40.173 | 1.00 | 56.07 | A | C |
| ATOM | 54 | OE1 | GLU | A | 243 | 26.717 | -3.626 | 39.993 | 1.00 | 56.41 | A | O |
| ATOM | 55 | OE2 | GLU | A | 243 | 27.554 | -1.680 | 40.569 | 1.00 | 56.97 | A | O |
| ATOM | 56 | C | GLU | A | 243 | 29.772 | -2.078 | 36.246 | 1.00 | 46.51 | A | C |
| ATOM | 57 | O | GLU | A | 243 | 30.883 | -1.606 | 36.001 | 1.00 | 46.69 | A | O |
| ATOM | 58 | N | THR | A | 244 | 29.015 | -2.695 | 35.338 | 1.00 | 43.64 | A | N |
| ATOM | 59 | CA | THR | A | 244 | 29.451 | -2.882 | 33.952 | 1.00 | 41.30 | A | C |
| ATOM | 60 | CB | THR | A | 244 | 28.532 | -3.867 | 33.219 | 1.00 | 40.65 | A | C |
| ATOM | 61 | OG1 | THR | A | 244 | 27.242 | -3.273 | 33.035 | 1.00 | 40.71 | A | O |
| ATOM | 62 | CG2 | THR | A | 244 | 28.400 | -5.147 | 34.011 | 1.00 | 40.86 | A | C |
| ATOM | 63 | C | THR | A | 244 | 29.499 | -1.584 | 33.134 | 1.00 | 40.30 | A | C |
| ATOM | 64 | O | THR | A | 244 | 29.861 | -1.588 | 31.945 | 1.00 | 38.78 | A | O |
| ATOM | 65 | N | LEU | A | 245 | 29.227 | -0.469 | 33.802 | 1.00 | 38.92 | A | N |
| ATOM | 66 | CA | LEU | A | 245 | 29.164 | 0.813 | 33.142 | 1.00 | 37.89 | A | C |
| ATOM | 67 | CB | LEU | A | 245 | 27.701 | 1.240 | 33.136 | 1.00 | 38.14 | A | C |
| ATOM | 68 | CG | LEU | A | 245 | 27.181 | 2.004 | 31.938 | 1.00 | 39.76 | A | C |
| ATOM | 69 | CD1 | LEU | A | 245 | 27.263 | 1.110 | 30.705 | 1.00 | 39.77 | A | C |
| ATOM | 70 | CD2 | LEU | A | 245 | 25.744 | 2.435 | 32.221 | 1.00 | 40.31 | A | C |
| ATOM | 71 | C | LEU | A | 245 | 30.007 | 1.922 | 33.770 | 1.00 | 37.42 | A | C |
| ATOM | 72 | O | LEU | A | 245 | 29.895 | 2.184 | 34.973 | 1.00 | 38.07 | A | O |
| ATOM | 73 | N | LYS | A | 246 | 30.853 | 2.561 | 32.955 | 1.00 | 35.40 | A | N |
| ATOM | 74 | CA | LYS | A | 246 | 31.654 | 3.685 | 33.423 | 1.00 | 33.42 | A | C |
| ATOM | 75 | CB | LYS | A | 246 | 33.170 | 3.453 | 33.250 | 1.00 | 34.41 | A | C |
| ATOM | 76 | CG | LYS | A | 246 | 34.014 | 4.684 | 33.697 | 1.00 | 36.27 | A | C |
| ATOM | 77 | CD | LYS | A | 246 | 35.508 | 4.418 | 33.895 | 1.00 | 37.77 | A | C |
| ATOM | 78 | CE | LYS | A | 246 | 36.191 | 3.912 | 32.631 | 1.00 | 39.33 | A | C |
| ATOM | 79 | NZ | LYS | A | 246 | 37.667 | 3.769 | 32.854 | 1.00 | 41.99 | A | N |
| ATOM | 80 | C | LYS | A | 246 | 31.228 | 4.937 | 32.660 | 1.00 | 32.39 | A | C |
| ATOM | 81 | O | LYS | A | 246 | 31.352 | 4.990 | 31.440 | 1.00 | 32.57 | A | O |
| ATOM | 82 | N | LEU | A | 247 | 30.664 | 5.916 | 33.370 | 1.00 | 30.73 | A | N |
| ATOM | 83 | CA | LEU | A | 247 | 30.245 | 7.168 | 32.748 | 1.00 | 28.45 | A | C |
| ATOM | 84 | CB | LEU | A | 247 | 29.062 | 7.806 | 33.492 | 1.00 | 25.56 | A | C |
| ATOM | 85 | CG | LEU | A | 247 | 27.675 | 7.310 | 33.052 | 1.00 | 24.31 | A | C |
| ATOM | 86 | CD1 | LEU | A | 247 | 27.524 | 5.797 | 33.257 | 1.00 | 22.68 | A | C |
| ATOM | 87 | CD2 | LEU | A | 247 | 26.588 | 8.076 | 33.793 | 1.00 | 22.97 | A | C |
| ATOM | 88 | C | LEU | A | 247 | 31.452 | 8.082 | 32.745 | 1.00 | 29.32 | A | C |
| ATOM | 89 | O | LEU | A | 247 | 32.069 | 8.310 | 33.787 | 1.00 | 29.73 | A | O |
| ATOM | 90 | N | VAL | A | 248 | 31.790 | 8.594 | 31.564 | 1.00 | 29.09 | A | N |
| ATOM | 91 | CA | VAL | A | 248 | 32.957 | 9.455 | 31.396 | 1.00 | 29.22 | A | C |
| ATOM | 92 | CB | VAL | A | 248 | 33.877 | 8.918 | 30.246 | 1.00 | 28.27 | A | C |
| ATOM | 93 | CG1 | VAL | A | 248 | 35.096 | 9.812 | 30.068 | 1.00 | 28.03 | A | C |
| ATOM | 94 | CG2 | VAL | A | 248 | 34.302 | 7.501 | 30.533 | 1.00 | 27.74 | A | C |
| ATOM | 95 | C | VAL | A | 248 | 32.724 | 10.957 | 31.178 | 1.00 | 29.50 | A | C |
| ATOM | 96 | O | VAL | A | 248 | 33.206 | 11.799 | 31.948 | 1.00 | 30.41 | A | O |
| ATOM | 97 | N | GLU | A | 249 | 31.974 | 11.292 | 30.142 | 1.00 | 30.37 | A | N |
| ATOM | 98 | CA | GLU | A | 249 | 31.747 | 12.684 | 29.796 | 1.00 | 30.64 | A | C |
| ATOM | 99 | CB | GLU | A | 249 | 32.516 | 12.948 | 28.510 | 1.00 | 30.88 | A | C |
| ATOM | 100 | CG | GLU | A | 249 | 32.510 | 14.356 | 28.021 | 1.00 | 33.25 | A | C |
| ATOM | 101 | CD | GLU | A | 249 | 33.165 | 14.478 | 26.663 | 1.00 | 34.39 | A | C |
| ATOM | 102 | OE1 | GLU | A | 249 | 33.972 | 13.591 | 26.307 | 1.00 | 34.57 | A | O |
| ATOM | 103 | OE2 | GLU | A | 249 | 32.857 | 15.448 | 25.942 | 1.00 | 36.36 | A | O |
| ATOM | 104 | C | GLU | A | 249 | 30.273 | 13.019 | 29.594 | 1.00 | 29.22 | A | C |
| ATOM | 105 | O | GLU | A | 249 | 29.573 | 12.302 | 28.901 | 1.00 | 29.35 | A | O |
| ATOM | 106 | N | ARG | A | 250 | 29.797 | 14.095 | 30.205 | 1.00 | 27.22 | A | N |
| ATOM | 107 | CA | ARG | A | 250 | 28.412 | 14.453 | 30.009 | 1.00 | 28.18 | A | C |

Figure 4

| ATOM | 108 | CB | ARG A 250 | 27.876 | 15.304 | 31.137 | 1.00 | 28.55 | A | C |
| ATOM | 109 | CG | ARG A 250 | 26.375 | 15.321 | 31.114 | 1.00 | 29.38 | A | C |
| ATOM | 110 | CD | ARG A 250 | 25.848 | 16.124 | 32.243 | 1.00 | 31.29 | A | C |
| ATOM | 111 | NE | ARG A 250 | 26.076 | 17.543 | 32.031 | 1.00 | 32.31 | A | N |
| ATOM | 112 | CZ | ARG A 250 | 25.938 | 18.464 | 32.973 | 1.00 | 33.76 | A | C |
| ATOM | 113 | NH1 | ARG A 250 | 25.573 | 18.108 | 34.193 | 1.00 | 35.03 | A | N |
| ATOM | 114 | NH2 | ARG A 250 | 26.146 | 19.740 | 32.697 | 1.00 | 35.49 | A | N |
| ATOM | 115 | C | ARG A 250 | 28.251 | 15.207 | 28.704 | 1.00 | 28.76 | A | C |
| ATOM | 116 | O | ARG A 250 | 28.855 | 16.270 | 28.495 | 1.00 | 28.55 | A | O |
| ATOM | 117 | N | LEU A 251 | 27.423 | 14.645 | 27.830 | 1.00 | 28.36 | A | N |
| ATOM | 118 | CA | LEU A 251 | 27.164 | 15.237 | 26.532 | 1.00 | 28.06 | A | C |
| ATOM | 119 | CB | LEU A 251 | 26.818 | 14.146 | 25.517 | 1.00 | 27.07 | A | C |
| ATOM | 120 | CG | LEU A 251 | 27.915 | 13.084 | 25.412 | 1.00 | 26.73 | A | C |
| ATOM | 121 | CD1 | LEU A 251 | 27.523 | 12.036 | 24.398 | 1.00 | 28.33 | A | C |
| ATOM | 122 | CD2 | LEU A 251 | 29.252 | 13.714 | 25.025 | 1.00 | 27.12 | A | C |
| ATOM | 123 | C | LEU A 251 | 26.084 | 16.310 | 26.614 | 1.00 | 28.24 | A | C |
| ATOM | 124 | O | LEU A 251 | 26.190 | 17.356 | 25.978 | 1.00 | 30.01 | A | O |
| ATOM | 125 | N | GLY A 252 | 25.083 | 16.093 | 27.456 | 1.00 | 28.63 | A | N |
| ATOM | 126 | CA | GLY A 252 | 24.023 | 17.078 | 27.586 | 1.00 | 26.25 | A | C |
| ATOM | 127 | C | GLY A 252 | 23.177 | 16.907 | 28.828 | 1.00 | 24.81 | A | C |
| ATOM | 128 | O | GLY A 252 | 23.129 | 15.828 | 29.413 | 1.00 | 23.39 | A | O |
| ATOM | 129 | N | ALA A 253 | 22.550 | 18.005 | 29.243 | 1.00 | 26.68 | A | N |
| ATOM | 130 | CA | ALA A 253 | 21.682 | 18.040 | 30.412 | 1.00 | 27.62 | A | C |
| ATOM | 131 | CB | ALA A 253 | 22.438 | 18.605 | 31.613 | 1.00 | 27.19 | A | C |
| ATOM | 132 | C | ALA A 253 | 20.415 | 18.874 | 30.124 | 1.00 | 29.84 | A | C |
| ATOM | 133 | O | ALA A 253 | 20.486 | 20.001 | 29.599 | 1.00 | 29.17 | A | O |
| ATOM | 134 | N | GLY A 254 | 19.258 | 18.296 | 30.452 | 1.00 | 31.37 | A | N |
| ATOM | 135 | CA | GLY A 254 | 17.992 | 18.967 | 30.231 | 1.00 | 31.45 | A | C |
| ATOM | 136 | C | GLY A 254 | 17.001 | 18.758 | 31.358 | 1.00 | 32.56 | A | C |
| ATOM | 137 | O | GLY A 254 | 17.310 | 18.138 | 32.376 | 1.00 | 32.49 | A | O |
| ATOM | 138 | N | GLN A 255 | 15.780 | 19.225 | 31.129 | 1.00 | 33.97 | A | N |
| ATOM | 139 | CA | GLN A 255 | 14.698 | 19.156 | 32.107 | 1.00 | 35.46 | A | C |
| ATOM | 140 | CB | GLN A 255 | 13.419 | 19.778 | 31.508 | 1.00 | 38.72 | A | C |
| ATOM | 141 | CG | GLN A 255 | 12.477 | 20.399 | 32.547 | 1.00 | 44.23 | A | C |
| ATOM | 142 | CD | GLN A 255 | 10.988 | 20.301 | 32.179 | 1.00 | 46.44 | A | C |
| ATOM | 143 | OE1 | GLN A 255 | 10.122 | 20.263 | 33.073 | 1.00 | 48.16 | A | O |
| ATOM | 144 | NE2 | GLN A 255 | 10.685 | 20.246 | 30.876 | 1.00 | 45.65 | A | N |
| ATOM | 145 | C | GLN A 255 | 14.394 | 17.763 | 32.683 | 1.00 | 32.65 | A | C |
| ATOM | 146 | O | GLN A 255 | 14.140 | 17.625 | 33.880 | 1.00 | 31.62 | A | O |
| ATOM | 147 | N | PHE A 256 | 14.464 | 16.741 | 31.836 | 1.00 | 30.28 | A | N |
| ATOM | 148 | CA | PHE A 256 | 14.157 | 15.366 | 32.227 | 1.00 | 29.13 | A | C |
| ATOM | 149 | CB | PHE A 256 | 13.362 | 14.654 | 31.115 | 1.00 | 30.08 | A | C |
| ATOM | 150 | CG | PHE A 256 | 11.923 | 15.094 | 30.971 | 1.00 | 28.88 | A | C |
| ATOM | 151 | CD1 | PHE A 256 | 11.402 | 16.158 | 31.710 | 1.00 | 29.63 | A | C |
| ATOM | 152 | CD2 | PHE A 256 | 11.087 | 14.420 | 30.078 | 1.00 | 29.21 | A | C |
| ATOM | 153 | CE1 | PHE A 256 | 10.066 | 16.545 | 31.565 | 1.00 | 29.86 | A | C |
| ATOM | 154 | CE2 | PHE A 256 | 9.756 | 14.795 | 29.926 | 1.00 | 29.09 | A | C |
| ATOM | 155 | CZ | PHE A 256 | 9.246 | 15.863 | 30.673 | 1.00 | 29.30 | A | C |
| ATOM | 156 | C | PHE A 256 | 15.342 | 14.473 | 32.585 | 1.00 | 28.24 | A | C |
| ATOM | 157 | O | PHE A 256 | 15.148 | 13.331 | 33.020 | 1.00 | 27.89 | A | O |
| ATOM | 158 | N | GLY A 257 | 16.559 | 14.949 | 32.345 | 1.00 | 27.87 | A | N |
| ATOM | 159 | CA | GLY A 257 | 17.722 | 14.138 | 32.657 | 1.00 | 27.46 | A | C |
| ATOM | 160 | C | GLY A 257 | 18.966 | 14.534 | 31.880 | 1.00 | 27.49 | A | C |
| ATOM | 161 | O | GLY A 257 | 19.106 | 15.670 | 31.420 | 1.00 | 25.74 | A | O |
| ATOM | 162 | N | GLU A 258 | 19.864 | 13.571 | 31.700 | 1.00 | 29.05 | A | N |
| ATOM | 163 | CA | GLU A 258 | 21.114 | 13.828 | 31.001 | 1.00 | 28.24 | A | C |
| ATOM | 164 | CB | GLU A 258 | 22.211 | 14.079 | 32.021 | 1.00 | 30.08 | A | C |
| ATOM | 165 | CG | GLU A 258 | 21.850 | 15.127 | 33.052 | 1.00 | 32.28 | A | C |
| ATOM | 166 | CD | GLU A 258 | 22.912 | 15.283 | 34.113 | 1.00 | 35.60 | A | C |
| ATOM | 167 | OE1 | GLU A 258 | 23.617 | 14.297 | 34.405 | 1.00 | 37.17 | A | O |

Figure 4

```
ATOM    168  OE2 GLU A 258      23.054  16.402  34.654  1.00 37.93      A   O
ATOM    169  C   GLU A 258      21.541  12.692  30.090  1.00 27.62      A   C
ATOM    170  O   GLU A 258      20.938  11.619  30.080  1.00 28.07      A   O
ATOM    171  N   VAL A 259      22.559  12.967  29.281  1.00 28.35      A   N
ATOM    172  CA  VAL A 259      23.109  11.974  28.368  1.00 27.78      A   C
ATOM    173  CB  VAL A 259      22.687  12.228  26.915  1.00 27.69      A   C
ATOM    174  CG1 VAL A 259      23.263  11.123  26.028  1.00 26.65      A   C
ATOM    175  CG2 VAL A 259      21.144  12.291  26.809  1.00 27.40      A   C
ATOM    176  C   VAL A 259      24.622  12.053  28.490  1.00 27.68      A   C
ATOM    177  O   VAL A 259      25.198  13.139  28.428  1.00 28.96      A   O
ATOM    178  N   TRP A 260      25.253  10.895  28.660  1.00 28.58      A   N
ATOM    179  CA  TRP A 260      26.702  10.809  28.845  1.00 27.90      A   C
ATOM    180  CB  TRP A 260      27.026  10.257  30.244  1.00 28.19      A   C
ATOM    181  CG  TRP A 260      26.787  11.179  31.367  1.00 28.29      A   C
ATOM    182  CD2 TRP A 260      27.768  11.688  32.270  1.00 28.70      A   C
ATOM    183  CE2 TRP A 260      27.114  12.599  33.130  1.00 30.72      A   C
ATOM    184  CE3 TRP A 260      29.141  11.468  32.437  1.00 28.64      A   C
ATOM    185  CD1 TRP A 260      25.606  11.770  31.712  1.00 29.15      A   C
ATOM    186  NE1 TRP A 260      25.793  12.632  32.761  1.00 30.27      A   N
ATOM    187  CZ2 TRP A 260      27.791  13.296  34.147  1.00 30.87      A   C
ATOM    188  CZ3 TRP A 260      29.811  12.158  33.436  1.00 28.51      A   C
ATOM    189  CH2 TRP A 260      29.136  13.062  34.279  1.00 30.30      A   C
ATOM    190  C   TRP A 260      27.388   9.867  27.896  1.00 26.79      A   C
ATOM    191  O   TRP A 260      26.790   8.914  27.432  1.00 25.38      A   O
ATOM    192  N   MET A 261      28.653  10.149  27.605  1.00 27.84      A   N
ATOM    193  CA  MET A 261      29.453   9.224  26.829  1.00 28.85      A   C
ATOM    194  CB  MET A 261      30.550   9.950  26.042  1.00 28.25      A   C
ATOM    195  CG  MET A 261      31.483   8.993  25.263  1.00 28.42      A   C
ATOM    196  SD  MET A 261      32.813   8.233  26.275  1.00 27.54      A   S
ATOM    197  CE  MET A 261      33.914   9.663  26.435  1.00 27.20      A   C
ATOM    198  C   MET A 261      30.076   8.340  27.935  1.00 29.04      A   C
ATOM    199  O   MET A 261      30.346   8.812  29.041  1.00 28.77      A   O
ATOM    200  N   GLY A 262      30.276   7.061  27.658  1.00 29.60      A   N
ATOM    201  CA  GLY A 262      30.859   6.200  28.664  1.00 28.47      A   C
ATOM    202  C   GLY A 262      31.340   4.922  28.035  1.00 28.71      A   C
ATOM    203  O   GLY A 262      31.338   4.793  26.813  1.00 28.14      A   O
ATOM    204  N   TYR A 263      31.760   3.979  28.872  1.00 29.11      A   N
ATOM    205  CA  TYR A 263      32.244   2.697  28.395  1.00 29.72      A   C
ATOM    206  CB  TYR A 263      33.768   2.589  28.580  1.00 27.16      A   C
ATOM    207  CG  TYR A 263      34.516   3.580  27.712  1.00 25.67      A   C
ATOM    208  CD1 TYR A 263      34.807   3.288  26.370  1.00 25.34      A   C
ATOM    209  CE1 TYR A 263      35.441   4.231  25.541  1.00 25.97      A   C
ATOM    210  CD2 TYR A 263      34.867   4.841  28.205  1.00 24.67      A   C
ATOM    211  CE2 TYR A 263      35.494   5.788  27.393  1.00 24.86      A   C
ATOM    212  CZ  TYR A 263      35.775   5.481  26.059  1.00 25.71      A   C
ATOM    213  OH  TYR A 263      36.385   6.426  25.255  1.00 26.45      A   O
ATOM    214  C   TYR A 263      31.497   1.540  29.036  1.00 31.08      A   C
ATOM    215  O   TYR A 263      31.255   1.518  30.242  1.00 31.52      A   O
ATOM    216  N   TYR A 264      31.067   0.623  28.179  1.00 35.18      A   N
ATOM    217  CA  TYR A 264      30.319  -0.566  28.568  1.00 38.85      A   C
ATOM    218  CB  TYR A 264      29.087  -0.695  27.657  1.00 38.95      A   C
ATOM    219  CG  TYR A 264      28.163  -1.851  27.946  1.00 40.06      A   C
ATOM    220  CD1 TYR A 264      27.762  -2.168  29.252  1.00 40.00      A   C
ATOM    221  CE1 TYR A 264      26.905  -3.250  29.496  1.00 40.82      A   C
ATOM    222  CD2 TYR A 264      27.692  -2.636  26.900  1.00 40.44      A   C
ATOM    223  CE2 TYR A 264      26.840  -3.707  27.125  1.00 40.99      A   C
ATOM    224  CZ  TYR A 264      26.448  -4.018  28.417  1.00 41.53      A   C
ATOM    225  OH  TYR A 264      25.580  -5.083  28.589  1.00 42.95      A   O
ATOM    226  C   TYR A 264      31.276  -1.762  28.443  1.00 40.38      A   C
ATOM    227  O   TYR A 264      31.740  -2.096  27.346  1.00 39.40      A   O
```

Figure 4

| | | | | | | | | | | | |
|---|---|---|---|---|---|---|---|---|---|---|---|
| ATOM | 228 | N | ASN | A | 265 | 31.574 | -2.376 | 29.592 | 1.00 | 43.04 | A N |
| ATOM | 229 | CA | ASN | A | 265 | 32.511 | -3.499 | 29.699 | 1.00 | 44.29 | A C |
| ATOM | 230 | CB | ASN | A | 265 | 32.118 | -4.655 | 28.781 | 1.00 | 43.67 | A C |
| ATOM | 231 | CG | ASN | A | 265 | 30.697 | -5.123 | 29.007 | 1.00 | 43.46 | A C |
| ATOM | 232 | OD1 | ASN | A | 265 | 30.280 | -5.373 | 30.143 | 1.00 | 42.18 | A O |
| ATOM | 233 | ND2 | ASN | A | 265 | 29.939 | -5.240 | 27.920 | 1.00 | 43.25 | A N |
| ATOM | 234 | C | ASN | A | 265 | 33.913 | -2.978 | 29.361 | 1.00 | 45.66 | A C |
| ATOM | 235 | O | ASN | A | 265 | 34.651 | -3.580 | 28.579 | 1.00 | 44.81 | A O |
| ATOM | 236 | N | GLY | A | 266 | 34.211 | -1.794 | 29.895 | 1.00 | 47.42 | A N |
| ATOM | 237 | CA | GLY | A | 266 | 35.499 | -1.156 | 29.703 | 1.00 | 49.84 | A C |
| ATOM | 238 | C | GLY | A | 266 | 35.889 | -0.687 | 28.312 | 1.00 | 51.40 | A C |
| ATOM | 239 | O | GLY | A | 266 | 36.580 | 0.331 | 28.193 | 1.00 | 51.66 | A O |
| ATOM | 240 | N | HIS | A | 267 | 35.424 | -1.364 | 27.258 | 1.00 | 52.71 | A N |
| ATOM | 241 | CA | HIS | A | 267 | 35.824 | -0.980 | 25.900 | 1.00 | 53.61 | A C |
| ATOM | 242 | CB | HIS | A | 267 | 36.765 | -2.040 | 25.315 | 1.00 | 57.88 | A C |
| ATOM | 243 | CG | HIS | A | 267 | 38.104 | -2.082 | 25.991 | 1.00 | 61.70 | A C |
| ATOM | 244 | CD2 | HIS | A | 267 | 39.049 | -1.120 | 26.147 | 1.00 | 62.53 | A C |
| ATOM | 245 | ND1 | HIS | A | 267 | 38.579 | -3.195 | 26.653 | 1.00 | 62.50 | A N |
| ATOM | 246 | CE1 | HIS | A | 267 | 39.754 | -2.918 | 27.190 | 1.00 | 63.56 | A C |
| ATOM | 247 | NE2 | HIS | A | 267 | 40.064 | -1.665 | 26.897 | 1.00 | 63.06 | A N |
| ATOM | 248 | C | HIS | A | 267 | 34.796 | -0.536 | 24.859 | 1.00 | 50.58 | A C |
| ATOM | 249 | O | HIS | A | 267 | 35.166 | 0.117 | 23.887 | 1.00 | 50.72 | A O |
| ATOM | 250 | N | THR | A | 268 | 33.527 | -0.901 | 25.022 | 1.00 | 47.12 | A N |
| ATOM | 251 | CA | THR | A | 268 | 32.503 | -0.469 | 24.061 | 1.00 | 42.49 | A C |
| ATOM | 252 | CB | THR | A | 268 | 31.277 | -1.425 | 24.053 | 1.00 | 42.94 | A C |
| ATOM | 253 | OG1 | THR | A | 268 | 31.701 | -2.746 | 23.691 | 1.00 | 44.03 | A O |
| ATOM | 254 | CG2 | THR | A | 268 | 30.218 | -0.958 | 23.055 | 1.00 | 42.13 | A C |
| ATOM | 255 | C | THR | A | 268 | 32.050 | 0.960 | 24.387 | 1.00 | 39.12 | A C |
| ATOM | 256 | O | THR | A | 268 | 31.560 | 1.229 | 25.481 | 1.00 | 37.28 | A O |
| ATOM | 257 | N | LYS | A | 269 | 32.244 | 1.885 | 23.458 | 1.00 | 35.79 | A N |
| ATOM | 258 | CA | LYS | A | 269 | 31.837 | 3.278 | 23.651 | 1.00 | 32.86 | A C |
| ATOM | 259 | CB | LYS | A | 269 | 32.527 | 4.176 | 22.626 | 1.00 | 30.17 | A C |
| ATOM | 260 | CG | LYS | A | 269 | 32.764 | 5.587 | 23.131 | 1.00 | 28.34 | A C |
| ATOM | 261 | CD | LYS | A | 269 | 33.696 | 6.337 | 22.220 | 1.00 | 28.43 | A C |
| ATOM | 262 | CE | LYS | A | 269 | 33.928 | 7.743 | 22.739 | 1.00 | 27.55 | A C |
| ATOM | 263 | NZ | LYS | A | 269 | 34.825 | 8.528 | 21.849 | 1.00 | 29.21 | A N |
| ATOM | 264 | C | LYS | A | 269 | 30.333 | 3.424 | 23.565 | 1.00 | 31.98 | A C |
| ATOM | 265 | O | LYS | A | 269 | 29.698 | 2.907 | 22.638 | 1.00 | 32.62 | A O |
| ATOM | 266 | N | VAL | A | 270 | 29.728 | 4.157 | 24.569 | 1.00 | 30.68 | A N |
| ATOM | 267 | CA | VAL | A | 270 | 28.271 | 4.316 | 24.681 | 1.00 | 28.25 | A C |
| ATOM | 268 | CB | VAL | A | 270 | 27.741 | 3.453 | 25.845 | 1.00 | 27.86 | A C |
| ATOM | 269 | CG1 | VAL | A | 270 | 28.042 | 1.984 | 25.588 | 1.00 | 27.77 | A C |
| ATOM | 270 | CG2 | VAL | A | 270 | 28.342 | 3.898 | 27.159 | 1.00 | 25.40 | A C |
| ATOM | 271 | C | VAL | A | 270 | 27.747 | 5.728 | 24.950 | 1.00 | 27.96 | A C |
| ATOM | 272 | O | VAL | A | 270 | 28.489 | 6.676 | 25.225 | 1.00 | 27.14 | A O |
| ATOM | 273 | N | ALA | A | 271 | 26.450 | 5.782 | 24.860 | 1.00 | 27.82 | A N |
| ATOM | 274 | CA | ALA | A | 271 | 25.712 | 6.942 | 25.219 | 1.00 | 26.72 | A C |
| ATOM | 275 | CB | ALA | A | 271 | 24.859 | 7.485 | 24.098 | 1.00 | 27.48 | A C |
| ATOM | 276 | C | ALA | A | 271 | 24.871 | 6.388 | 26.315 | 1.00 | 26.75 | A C |
| ATOM | 277 | O | ALA | A | 271 | 24.312 | 5.305 | 26.171 | 1.00 | 27.73 | A O |
| ATOM | 278 | N | VAL | A | 272 | 24.752 | 7.125 | 27.407 | 1.00 | 26.16 | A N |
| ATOM | 279 | CA | VAL | A | 272 | 23.953 | 6.668 | 28.520 | 1.00 | 25.48 | A C |
| ATOM | 280 | CB | VAL | A | 272 | 24.863 | 6.321 | 29.769 | 1.00 | 25.57 | A C |
| ATOM | 281 | CG1 | VAL | A | 272 | 24.009 | 5.834 | 30.946 | 1.00 | 26.52 | A C |
| ATOM | 282 | CG2 | VAL | A | 272 | 25.920 | 5.267 | 29.409 | 1.00 | 22.48 | A C |
| ATOM | 283 | C | VAL | A | 272 | 22.982 | 7.774 | 28.878 | 1.00 | 25.28 | A C |
| ATOM | 284 | O | VAL | A | 272 | 23.406 | 8.876 | 29.233 | 1.00 | 26.14 | A O |
| ATOM | 285 | N | LYS | A | 273 | 21.687 | 7.504 | 28.712 | 1.00 | 25.10 | A N |
| ATOM | 286 | CA | LYS | A | 273 | 20.654 | 8.476 | 29.067 | 1.00 | 24.80 | A C |
| ATOM | 287 | CB | LYS | A | 273 | 19.526 | 8.478 | 28.027 | 1.00 | 25.49 | A C |

Figure 4

```
ATOM    288  CG  LYS A 273      18.415   9.502  28.299  1.00 26.34      A    C
ATOM    289  CD  LYS A 273      17.400   9.591  27.148  1.00 26.86      A    C
ATOM    290  CE  LYS A 273      17.845  10.582  26.071  1.00 26.16      A    C
ATOM    291  NZ  LYS A 273      16.814  10.703  25.011  1.00 25.93      A    N
ATOM    292  C   LYS A 273      20.111   8.183  30.475  1.00 24.36      A    C
ATOM    293  O   LYS A 273      19.649   7.073  30.765  1.00 21.98      A    O
ATOM    294  N   SER A 274      20.205   9.172  31.355  1.00 25.48      A    N
ATOM    295  CA  SER A 274      19.739   8.998  32.717  1.00 29.32      A    C
ATOM    296  CB  SER A 274      20.853   9.308  33.714  1.00 30.91      A    C
ATOM    297  OG  SER A 274      21.202  10.679  33.671  1.00 33.97      A    O
ATOM    298  C   SER A 274      18.535   9.868  33.009  1.00 30.39      A    C
ATOM    299  O   SER A 274      18.419  10.989  32.500  1.00 30.83      A    O
ATOM    300  N   LEU A 275      17.649   9.338  33.846  1.00 32.31      A    N
ATOM    301  CA  LEU A 275      16.427  10.033  34.235  1.00 33.55      A    C
ATOM    302  CB  LEU A 275      15.277   9.027  34.382  1.00 31.43      A    C
ATOM    303  CG  LEU A 275      13.999   9.527  35.065  1.00 31.20      A    C
ATOM    304  CD1 LEU A 275      13.258  10.509  34.151  1.00 31.10      A    C
ATOM    305  CD2 LEU A 275      13.102   8.342  35.419  1.00 30.30      A    C
ATOM    306  C   LEU A 275      16.551  10.839  35.530  1.00 35.66      A    C
ATOM    307  O   LEU A 275      17.068  10.350  36.544  1.00 37.07      A    O
ATOM    308  N   LYS A 276      16.096  12.088  35.473  1.00 37.45      A    N
ATOM    309  CA  LYS A 276      16.086  12.968  36.634  1.00 39.84      A    C
ATOM    310  CB  LYS A 276      15.989  14.430  36.185  1.00 39.64      A    C
ATOM    311  CG  LYS A 276      15.809  15.447  37.300  1.00 41.28      A    C
ATOM    312  CD  LYS A 276      15.759  16.872  36.754  1.00 43.78      A    C
ATOM    313  CE  LYS A 276      16.996  17.183  35.910  1.00 46.91      A    C
ATOM    314  NZ  LYS A 276      17.043  18.565  35.333  1.00 49.10      A    N
ATOM    315  C   LYS A 276      14.831  12.558  37.413  1.00 42.02      A    C
ATOM    316  O   LYS A 276      13.706  12.747  36.931  1.00 40.61      A    O
ATOM    317  N   GLN A 277      15.030  11.926  38.576  1.00 44.64      A    N
ATOM    318  CA  GLN A 277      13.968  11.443  39.448  1.00 45.50      A    C
ATOM    319  CB  GLN A 277      14.527  11.090  40.828  1.00 48.97      A    C
ATOM    320  CG  GLN A 277      13.542  10.366  41.730  1.00 54.92      A    C
ATOM    321  CD  GLN A 277      14.124  10.049  43.093  1.00 58.03      A    C
ATOM    322  OE1 GLN A 277      15.278  10.373  43.376  1.00 57.42      A    O
ATOM    323  NE2 GLN A 277      13.506   9.424  44.089  1.00 59.93      A    N
ATOM    324  C   GLN A 277      12.850  12.471  39.575  1.00 43.63      A    C
ATOM    325  O   GLN A 277      13.091  13.626  39.929  1.00 41.80      A    O
ATOM    326  N   GLY A 278      11.630  12.059  39.199  1.00 43.48      A    N
ATOM    327  CA  GLY A 278      10.471  12.939  39.288  1.00 43.38      A    C
ATOM    328  C   GLY A 278       9.941  13.497  37.973  1.00 43.80      A    C
ATOM    329  O   GLY A 278       8.788  13.933  37.886  1.00 44.14      A    O
ATOM    330  N   SER A 279      10.788  13.505  36.949  1.00 42.95      A    N
ATOM    331  CA  SER A 279      10.403  14.002  35.628  1.00 41.92      A    C
ATOM    332  CB  SER A 279      11.619  13.968  34.707  1.00 41.54      A    C
ATOM    333  OG  SER A 279      12.689  14.688  35.301  1.00 41.27      A    O
ATOM    334  C   SER A 279       9.266  13.154  35.055  1.00 40.45      A    C
ATOM    335  O   SER A 279       8.392  13.645  34.352  1.00 39.19      A    O
ATOM    336  N   MET A 280       9.319  11.867  35.373  1.00 39.74      A    N
ATOM    337  CA  MET A 280       8.361  10.876  34.970  1.00 38.76      A    C
ATOM    338  CB  MET A 280       8.383  10.654  33.451  1.00 37.07      A    C
ATOM    339  CG  MET A 280       9.595   9.889  32.927  1.00 36.64      A    C
ATOM    340  SD  MET A 280       9.649   9.846  31.122  1.00 35.34      A    S
ATOM    341  CE  MET A 280       9.091   8.178  30.796  1.00 34.46      A    C
ATOM    342  C   MET A 280       8.722   9.645  35.760  1.00 39.01      A    C
ATOM    343  O   MET A 280       9.750   9.583  36.428  1.00 38.14      A    O
ATOM    344  N   SER A 281       7.869   8.685  35.720  1.00 40.39      A    N
ATOM    345  CA  SER A 281       7.969   7.464  36.496  1.00 41.46      A    C
ATOM    346  CB  SER A 281       6.590   6.808  36.646  1.00 40.43      A    C
ATOM    347  OG  SER A 281       6.367   5.863  35.615  1.00 39.50      A    O
```

Figure 4

```
ATOM    348  C    SER A 281       8.870   6.429  35.880  1.00 43.67           A  C
ATOM    349  O    SER A 281       8.873   6.221  34.674  1.00 42.98           A  O
ATOM    350  N    PRO A 282       9.649   5.782  36.740  1.00 45.05           A  N
ATOM    351  CD   PRO A 282      10.353   6.418  37.868  1.00 45.98           A  C
ATOM    352  CA   PRO A 282      10.529   4.763  36.221  1.00 46.83           A  C
ATOM    353  CB   PRO A 282      11.153   4.152  37.469  1.00 46.76           A  C
ATOM    354  CG   PRO A 282      11.370   5.384  38.277  1.00 46.26           A  C
ATOM    355  C    PRO A 282       9.972   3.848  35.198  1.00 48.31           A  C
ATOM    356  O    PRO A 282      10.460   3.806  34.055  1.00 49.86           A  O
ATOM    357  N    ASP A 283       9.024   3.095  35.528  1.00 50.08           A  N
ATOM    358  CA   ASP A 283       8.659   2.185  34.524  1.00 51.48           A  C
ATOM    359  CB   ASP A 283       7.605   1.236  35.081  1.00 54.16           A  C
ATOM    360  CG   ASP A 283       8.236   0.465  36.241  1.00 56.42           A  C
ATOM    361  OD1  ASP A 283       9.485   0.427  36.318  1.00 57.35           A  O
ATOM    362  OD2  ASP A 283       7.493  -0.081  37.081  1.00 56.66           A  O
ATOM    363  C    ASP A 283       8.273   2.888  33.215  1.00 50.81           A  C
ATOM    364  O    ASP A 283       8.186   2.250  32.163  1.00 50.36           A  O
ATOM    365  N    ALA A 284       8.053   4.204  33.258  1.00 50.09           A  N
ATOM    366  CA   ALA A 284       7.663   4.996  32.059  1.00 49.31           A  C
ATOM    367  CB   ALA A 284       6.989   6.298  32.487  1.00 49.62           A  C
ATOM    368  C    ALA A 284       8.869   5.301  31.159  1.00 48.92           A  C
ATOM    369  O    ALA A 284       8.815   5.186  29.932  1.00 49.53           A  O
ATOM    370  N    PHE A 285       9.958   5.684  31.794  1.00 47.74           A  N
ATOM    371  CA   PHE A 285      11.184   5.969  31.161  1.00 45.84           A  C
ATOM    372  CB   PHE A 285      12.151   6.546  32.176  1.00 45.15           A  C
ATOM    373  CG   PHE A 285      13.535   6.845  31.689  1.00 45.54           A  C
ATOM    374  CD1  PHE A 285      13.777   7.980  30.913  1.00 44.79           A  C
ATOM    375  CD2  PHE A 285      14.615   6.032  32.041  1.00 44.90           A  C
ATOM    376  CE1  PHE A 285      15.080   8.301  30.504  1.00 44.04           A  C
ATOM    377  CE2  PHE A 285      15.920   6.349  31.634  1.00 43.86           A  C
ATOM    378  CZ   PHE A 285      16.149   7.485  30.869  1.00 43.77           A  C
ATOM    379  C    PHE A 285      11.745   4.671  30.562  1.00 43.97           A  C
ATOM    380  O    PHE A 285      12.178   4.624  29.423  1.00 41.47           A  O
ATOM    381  N    LEU A 286      11.736   3.617  31.374  1.00 42.38           A  N
ATOM    382  CA   LEU A 286      12.215   2.309  30.961  1.00 43.22           A  C
ATOM    383  CB   LEU A 286      12.274   1.356  32.159  1.00 42.25           A  C
ATOM    384  CG   LEU A 286      13.423   1.627  33.137  1.00 41.48           A  C
ATOM    385  CD1  LEU A 286      13.126   0.991  34.492  1.00 40.04           A  C
ATOM    386  CD2  LEU A 286      14.754   1.137  32.540  1.00 40.33           A  C
ATOM    387  C    LEU A 286      11.278   1.767  29.911  1.00 43.76           A  C
ATOM    388  O    LEU A 286      11.694   1.017  29.031  1.00 44.07           A  O
ATOM    389  N    ALA A 287      10.011   2.170  30.010  1.00 45.45           A  N
ATOM    390  CA   ALA A 287       8.973   1.756  29.067  1.00 45.94           A  C
ATOM    391  CB   ALA A 287       7.588   2.230  29.548  1.00 44.90           A  C
ATOM    392  C    ALA A 287       9.282   2.310  27.666  1.00 45.74           A  C
ATOM    393  O    ALA A 287       8.977   1.667  26.657  1.00 46.86           A  O
ATOM    394  N    GLU A 288       9.912   3.484  27.618  1.00 45.22           A  N
ATOM    395  CA   GLU A 288      10.283   4.121  26.355  1.00 46.70           A  C
ATOM    396  CB   GLU A 288      10.716   5.577  26.592  1.00 46.24           A  C
ATOM    397  CG   GLU A 288       9.671   6.457  27.286  1.00 46.72           A  C
ATOM    398  CD   GLU A 288      10.003   7.950  27.244  1.00 47.21           A  C
ATOM    399  OE1  GLU A 288      11.163   8.339  27.528  1.00 48.28           A  O
ATOM    400  OE2  GLU A 288       9.089   8.738  26.920  1.00 46.68           A  O
ATOM    401  C    GLU A 288      11.412   3.355  25.646  1.00 48.19           A  C
ATOM    402  O    GLU A 288      11.535   3.389  24.418  1.00 48.26           A  O
ATOM    403  N    ALA A 289      12.220   2.643  26.427  1.00 49.42           A  N
ATOM    404  CA   ALA A 289      13.337   1.878  25.885  1.00 49.73           A  C
ATOM    405  CB   ALA A 289      14.344   1.569  26.985  1.00 51.08           A  C
ATOM    406  C    ALA A 289      12.905   0.589  25.216  1.00 50.06           A  C
ATOM    407  O    ALA A 289      13.604   0.087  24.337  1.00 49.06           A  O
```

Figure 4

```
ATOM    408  N    ASN A 290      11.759   0.056  25.641  1.00 52.14      A  N
ATOM    409  CA   ASN A 290      11.209  -1.201  25.107  1.00 53.78      A  C
ATOM    410  CB   ASN A 290       9.936  -1.599  25.857  1.00 54.99      A  C
ATOM    411  CG   ASN A 290      10.203  -1.980  27.300  1.00 56.14      A  C
ATOM    412  OD1  ASN A 290       9.416  -1.657  28.195  1.00 57.48      A  O
ATOM    413  ND2  ASN A 290      11.317  -2.665  27.537  1.00 55.92      A  N
ATOM    414  C    ASN A 290      10.929  -1.193  23.607  1.00 53.82      A  C
ATOM    415  O    ASN A 290      10.813  -2.251  22.987  1.00 53.56      A  O
ATOM    416  N    LEU A 291      10.788   0.004  23.052  1.00 54.41      A  N
ATOM    417  CA   LEU A 291      10.560   0.161  21.612  1.00 55.72      A  C
ATOM    418  CB   LEU A 291      10.062   1.576  21.296  1.00 56.27      A  C
ATOM    419  CG   LEU A 291       8.746   2.000  21.953  1.00 55.93      A  C
ATOM    420  CD1  LEU A 291       8.382   3.423  21.557  1.00 56.27      A  C
ATOM    421  CD2  LEU A 291       7.626   1.040  21.584  1.00 55.42      A  C
ATOM    422  C    LEU A 291      11.825  -0.134  20.803  1.00 55.83      A  C
ATOM    423  O    LEU A 291      11.794  -0.834  19.801  1.00 56.08      A  O
ATOM    424  N    MET A 292      12.927   0.418  21.299  1.00 55.33      A  N
ATOM    425  CA   MET A 292      14.232   0.223  20.689  1.00 55.90      A  C
ATOM    426  CB   MET A 292      15.266   0.962  21.531  1.00 56.34      A  C
ATOM    427  CG   MET A 292      16.421   1.532  20.780  1.00 55.98      A  C
ATOM    428  SD   MET A 292      17.198   2.734  21.839  1.00 56.23      A  S
ATOM    429  CE   MET A 292      16.582   4.291  21.079  1.00 56.93      A  C
ATOM    430  C    MET A 292      14.561  -1.280  20.631  1.00 56.46      A  C
ATOM    431  O    MET A 292      15.257  -1.745  19.726  1.00 56.64      A  O
ATOM    432  N    LYS A 293      14.060  -2.031  21.610  1.00 56.60      A  N
ATOM    433  CA   LYS A 293      14.275  -3.469  21.671  1.00 56.55      A  C
ATOM    434  CB   LYS A 293      13.666  -4.043  22.946  1.00 56.84      A  C
ATOM    435  CG   LYS A 293      14.250  -3.528  24.239  1.00 57.45      A  C
ATOM    436  CD   LYS A 293      13.644  -4.291  25.417  1.00 58.55      A  C
ATOM    437  CE   LYS A 293      14.211  -3.829  26.754  1.00 60.01      A  C
ATOM    438  NZ   LYS A 293      13.596  -4.586  27.878  1.00 61.52      A  N
ATOM    439  C    LYS A 293      13.571  -4.108  20.488  1.00 56.55      A  C
ATOM    440  O    LYS A 293      14.147  -4.926  19.764  1.00 57.43      A  O
ATOM    441  N    GLN A 294      12.318  -3.700  20.302  1.00 55.79      A  N
ATOM    442  CA   GLN A 294      11.449  -4.195  19.239  1.00 55.09      A  C
ATOM    443  CB   GLN A 294      10.049  -3.592  19.408  1.00 57.51      A  C
ATOM    444  CG   GLN A 294       9.447  -3.840  20.791  1.00 61.32      A  C
ATOM    445  CD   GLN A 294       9.543  -5.310  21.233  1.00 63.52      A  C
ATOM    446  OE1  GLN A 294      10.340  -5.661  22.115  1.00 63.83      A  O
ATOM    447  NE2  GLN A 294       8.733  -6.172  20.610  1.00 64.95      A  N
ATOM    448  C    GLN A 294      11.956  -3.965  17.810  1.00 53.22      A  C
ATOM    449  O    GLN A 294      12.045  -4.906  17.006  1.00 52.24      A  O
ATOM    450  N    LEU A 295      12.285  -2.717  17.495  1.00 50.60      A  N
ATOM    451  CA   LEU A 295      12.772  -2.365  16.168  1.00 48.32      A  C
ATOM    452  CB   LEU A 295      12.126  -1.037  15.694  1.00 48.35      A  C
ATOM    453  CG   LEU A 295      10.639  -1.065  15.375  1.00 47.96      A  C
ATOM    454  CD1  LEU A 295      10.186   0.254  14.762  1.00 49.23      A  C
ATOM    455  CD2  LEU A 295      10.324  -2.207  14.433  1.00 48.05      A  C
ATOM    456  C    LEU A 295      14.276  -2.207  16.139  1.00 46.54      A  C
ATOM    457  O    LEU A 295      14.837  -1.340  16.800  1.00 47.58      A  O
ATOM    458  N    GLN A 296      14.936  -3.064  15.386  1.00 43.69      A  N
ATOM    459  CA   GLN A 296      16.349  -2.936  15.169  1.00 42.26      A  C
ATOM    460  CB   GLN A 296      17.100  -4.208  15.595  1.00 44.10      A  C
ATOM    461  CG   GLN A 296      17.305  -4.353  17.092  1.00 46.45      A  C
ATOM    462  CD   GLN A 296      17.321  -5.786  17.544  1.00 48.87      A  C
ATOM    463  OE1  GLN A 296      17.356  -6.704  16.726  1.00 49.07      A  O
ATOM    464  NE2  GLN A 296      17.315  -6.210  18.793  1.00 50.23      A  N
ATOM    465  C    GLN A 296      16.537  -2.744  13.683  1.00 40.17      A  C
ATOM    466  O    GLN A 296      15.768  -3.282  12.868  1.00 39.66      A  O
ATOM    467  N    HIS A 297      17.558  -1.982  13.317  1.00 37.68      A  N
```

Figure 4

| | | | | | | | | | | | |
|---|---|---|---|---|---|---|---|---|---|---|---|
| ATOM | 468 | CA | HIS | A | 297 | 17.876 | -1.680 | 11.962 | 1.00 | 35.86 | A | C |
| ATOM | 469 | CB | HIS | A | 297 | 16.716 | -0.947 | 11.290 | 1.00 | 34.29 | A | C |
| ATOM | 470 | CG | HIS | A | 297 | 16.858 | -0.850 | 9.736 | 1.00 | 32.18 | A | C |
| ATOM | 471 | CD2 | HIS | A | 297 | 16.481 | -1.697 | 8.746 | 1.00 | 30.92 | A | C |
| ATOM | 472 | ND1 | HIS | A | 297 | 17.463 | 0.222 | 9.114 | 1.00 | 31.37 | A | N |
| ATOM | 473 | CE1 | HIS | A | 297 | 17.456 | 0.031 | 7.806 | 1.00 | 30.23 | A | C |
| ATOM | 474 | NE2 | HIS | A | 297 | 16.867 | -1.124 | 7.557 | 1.00 | 30.78 | A | N |
| ATOM | 475 | C | HIS | A | 297 | 19.129 | -0.802 | 11.952 | 1.00 | 35.62 | A | C |
| ATOM | 476 | O | HIS | A | 297 | 19.369 | -0.067 | 12.902 | 1.00 | 33.93 | A | O |
| ATOM | 477 | N | GLN | A | 298 | 19.919 | -0.848 | 10.879 | 1.00 | 37.42 | A | N |
| ATOM | 478 | CA | GLN | A | 298 | 21.126 | -0.028 | 10.772 | 1.00 | 38.84 | A | C |
| ATOM | 479 | CB | GLN | A | 298 | 21.943 | -0.369 | 9.522 | 1.00 | 41.28 | A | C |
| ATOM | 480 | CG | GLN | A | 298 | 22.873 | -1.587 | 9.683 | 1.00 | 45.96 | A | C |
| ATOM | 481 | CD | GLN | A | 298 | 23.805 | -1.521 | 10.923 | 1.00 | 47.62 | A | C |
| ATOM | 482 | OE1 | GLN | A | 298 | 23.916 | -2.494 | 11.677 | 1.00 | 47.97 | A | O |
| ATOM | 483 | NE2 | GLN | A | 298 | 24.473 | -0.382 | 11.124 | 1.00 | 48.06 | A | N |
| ATOM | 484 | C | GLN | A | 298 | 20.841 | 1.462 | 10.781 | 1.00 | 37.86 | A | C |
| ATOM | 485 | O | GLN | A | 298 | 21.703 | 2.252 | 11.160 | 1.00 | 37.78 | A | O |
| ATOM | 486 | N | ARG | A | 299 | 19.639 | 1.847 | 10.362 | 1.00 | 36.25 | A | N |
| ATOM | 487 | CA | ARG | A | 299 | 19.265 | 3.265 | 10.336 | 1.00 | 34.95 | A | C |
| ATOM | 488 | CB | ARG | A | 299 | 18.446 | 3.582 | 9.082 | 1.00 | 35.24 | A | C |
| ATOM | 489 | CG | ARG | A | 299 | 19.198 | 3.361 | 7.784 | 1.00 | 35.44 | A | C |
| ATOM | 490 | CD | ARG | A | 299 | 20.395 | 4.256 | 7.702 | 1.00 | 35.83 | A | C |
| ATOM | 491 | NE | ARG | A | 299 | 21.427 | 3.620 | 6.907 | 1.00 | 38.99 | A | N |
| ATOM | 492 | CZ | ARG | A | 299 | 22.731 | 3.758 | 7.120 | 1.00 | 39.91 | A | C |
| ATOM | 493 | NH1 | ARG | A | 299 | 23.183 | 4.514 | 8.116 | 1.00 | 39.59 | A | N |
| ATOM | 494 | NH2 | ARG | A | 299 | 23.587 | 3.150 | 6.310 | 1.00 | 41.61 | A | N |
| ATOM | 495 | C | ARG | A | 299 | 18.536 | 3.749 | 11.595 | 1.00 | 33.37 | A | C |
| ATOM | 496 | O | ARG | A | 299 | 18.055 | 4.875 | 11.650 | 1.00 | 32.51 | A | O |
| ATOM | 497 | N | LEU | A | 300 | 18.465 | 2.886 | 12.605 | 1.00 | 32.46 | A | N |
| ATOM | 498 | CA | LEU | A | 300 | 17.835 | 3.192 | 13.893 | 1.00 | 31.29 | A | C |
| ATOM | 499 | CB | LEU | A | 300 | 16.681 | 2.226 | 14.168 | 1.00 | 30.90 | A | C |
| ATOM | 500 | CG | LEU | A | 300 | 15.270 | 2.504 | 13.662 | 1.00 | 29.90 | A | C |
| ATOM | 501 | CD1 | LEU | A | 300 | 15.269 | 2.931 | 12.225 | 1.00 | 30.51 | A | C |
| ATOM | 502 | CD2 | LEU | A | 300 | 14.445 | 1.254 | 13.853 | 1.00 | 29.76 | A | C |
| ATOM | 503 | C | LEU | A | 300 | 18.871 | 3.015 | 15.002 | 1.00 | 31.98 | A | C |
| ATOM | 504 | O | LEU | A | 300 | 19.698 | 2.092 | 14.949 | 1.00 | 31.74 | A | O |
| ATOM | 505 | N | VAL | A | 301 | 18.817 | 3.878 | 16.017 | 1.00 | 33.07 | A | N |
| ATOM | 506 | CA | VAL | A | 301 | 19.760 | 3.784 | 17.130 | 1.00 | 33.20 | A | C |
| ATOM | 507 | CB | VAL | A | 301 | 19.632 | 4.955 | 18.095 | 1.00 | 31.42 | A | C |
| ATOM | 508 | CG1 | VAL | A | 301 | 20.509 | 4.714 | 19.286 | 1.00 | 31.56 | A | C |
| ATOM | 509 | CG2 | VAL | A | 301 | 20.034 | 6.243 | 17.406 | 1.00 | 31.37 | A | C |
| ATOM | 510 | C | VAL | A | 301 | 19.530 | 2.480 | 17.894 | 1.00 | 34.68 | A | C |
| ATOM | 511 | O | VAL | A | 301 | 18.397 | 2.157 | 18.273 | 1.00 | 32.85 | A | O |
| ATOM | 512 | N | ARG | A | 302 | 20.621 | 1.735 | 18.080 | 1.00 | 37.00 | A | N |
| ATOM | 513 | CA | ARG | A | 302 | 20.614 | 0.445 | 18.760 | 1.00 | 37.70 | A | C |
| ATOM | 514 | CB | ARG | A | 302 | 21.701 | -0.458 | 18.166 | 1.00 | 40.52 | A | C |
| ATOM | 515 | CG | ARG | A | 302 | 21.831 | -1.842 | 18.786 | 1.00 | 44.23 | A | C |
| ATOM | 516 | CD | ARG | A | 302 | 22.789 | -1.828 | 19.975 | 1.00 | 47.68 | A | C |
| ATOM | 517 | NE | ARG | A | 302 | 23.419 | -3.128 | 20.209 | 1.00 | 51.11 | A | N |
| ATOM | 518 | CZ | ARG | A | 302 | 24.297 | -3.706 | 19.382 | 1.00 | 52.57 | A | C |
| ATOM | 519 | NH1 | ARG | A | 302 | 24.667 | -3.111 | 18.248 | 1.00 | 51.36 | A | N |
| ATOM | 520 | NH2 | ARG | A | 302 | 24.814 | -4.892 | 19.696 | 1.00 | 54.00 | A | N |
| ATOM | 521 | C | ARG | A | 302 | 20.788 | 0.574 | 20.264 | 1.00 | 37.52 | A | C |
| ATOM | 522 | O | ARG | A | 302 | 21.586 | 1.376 | 20.763 | 1.00 | 36.32 | A | O |
| ATOM | 523 | N | LEU | A | 303 | 20.009 | -0.234 | 20.972 | 1.00 | 39.08 | A | N |
| ATOM | 524 | CA | LEU | A | 303 | 20.017 | -0.282 | 22.427 | 1.00 | 39.63 | A | C |
| ATOM | 525 | CB | LEU | A | 303 | 18.602 | -0.445 | 22.940 | 1.00 | 38.89 | A | C |
| ATOM | 526 | CG | LEU | A | 303 | 18.569 | -0.493 | 24.452 | 1.00 | 40.91 | A | C |
| ATOM | 527 | CD1 | LEU | A | 303 | 18.269 | 0.903 | 24.946 | 1.00 | 42.25 | A | C |

Figure 4

| | | | | | | | | | | | |
|---|---|---|---|---|---|---|---|---|---|---|---|
| ATOM | 528 | CD2 | LEU | A | 303 | 17.535 | -1.508 | 24.951 | 1.00 | 42.98 | A C |
| ATOM | 529 | C | LEU | A | 303 | 20.829 | -1.478 | 22.912 | 1.00 | 39.87 | A C |
| ATOM | 530 | O | LEU | A | 303 | 20.614 | -2.607 | 22.463 | 1.00 | 41.02 | A O |
| ATOM | 531 | N | TYR | A | 304 | 21.772 | -1.224 | 23.814 | 1.00 | 40.45 | A N |
| ATOM | 532 | CA | TYR | A | 304 | 22.588 | -2.297 | 24.379 | 1.00 | 40.01 | A C |
| ATOM | 533 | CB | TYR | A | 304 | 23.994 | -1.797 | 24.701 | 1.00 | 41.04 | A C |
| ATOM | 534 | CG | TYR | A | 304 | 24.833 | -1.525 | 23.480 | 1.00 | 43.99 | A C |
| ATOM | 535 | CD1 | TYR | A | 304 | 24.819 | -0.276 | 22.873 | 1.00 | 45.36 | A C |
| ATOM | 536 | CE1 | TYR | A | 304 | 25.571 | -0.022 | 21.731 | 1.00 | 45.61 | A C |
| ATOM | 537 | CD2 | TYR | A | 304 | 25.632 | -2.524 | 22.908 | 1.00 | 45.74 | A C |
| ATOM | 538 | CE2 | TYR | A | 304 | 26.394 | -2.271 | 21.755 | 1.00 | 45.70 | A C |
| ATOM | 539 | CZ | TYR | A | 304 | 26.349 | -1.013 | 21.183 | 1.00 | 45.30 | A C |
| ATOM | 540 | OH | TYR | A | 304 | 27.080 | -0.728 | 20.062 | 1.00 | 46.87 | A O |
| ATOM | 541 | C | TYR | A | 304 | 21.923 | -2.851 | 25.644 | 1.00 | 39.06 | A C |
| ATOM | 542 | O | TYR | A | 304 | 21.626 | -4.034 | 25.730 | 1.00 | 38.84 | A O |
| ATOM | 543 | N | ALA | A | 305 | 21.606 | -1.972 | 26.589 | 1.00 | 38.55 | A N |
| ATOM | 544 | CA | ALA | A | 305 | 21.004 | -2.410 | 27.834 | 1.00 | 37.12 | A C |
| ATOM | 545 | CB | ALA | A | 305 | 22.067 | -3.118 | 28.665 | 1.00 | 37.85 | A C |
| ATOM | 546 | C | ALA | A | 305 | 20.397 | -1.268 | 28.635 | 1.00 | 36.12 | A C |
| ATOM | 547 | O | ALA | A | 305 | 20.390 | -0.119 | 28.193 | 1.00 | 34.50 | A O |
| ATOM | 548 | N | VAL | A | 306 | 19.880 | -1.613 | 29.814 | 1.00 | 36.98 | A N |
| ATOM | 549 | CA | VAL | A | 306 | 19.290 | -0.660 | 30.753 | 1.00 | 38.37 | A C |
| ATOM | 550 | CB | VAL | A | 306 | 17.738 | -0.533 | 30.571 | 1.00 | 38.64 | A C |
| ATOM | 551 | CG1 | VAL | A | 306 | 17.410 | 0.439 | 29.446 | 1.00 | 37.95 | A C |
| ATOM | 552 | CG2 | VAL | A | 306 | 17.116 | -1.900 | 30.281 | 1.00 | 38.81 | A C |
| ATOM | 553 | C | VAL | A | 306 | 19.610 | -1.042 | 32.213 | 1.00 | 38.94 | A C |
| ATOM | 554 | O | VAL | A | 306 | 19.863 | -2.212 | 32.527 | 1.00 | 38.36 | A O |
| ATOM | 555 | N | VAL | A | 307 | 19.643 | -0.033 | 33.083 | 1.00 | 39.75 | A N |
| ATOM | 556 | CA | VAL | A | 307 | 19.893 | -0.214 | 34.512 | 1.00 | 40.22 | A C |
| ATOM | 557 | CB | VAL | A | 307 | 21.136 | 0.582 | 34.976 | 1.00 | 37.81 | A C |
| ATOM | 558 | CG1 | VAL | A | 307 | 21.414 | 0.304 | 36.448 | 1.00 | 37.88 | A C |
| ATOM | 559 | CG2 | VAL | A | 307 | 22.335 | 0.211 | 34.125 | 1.00 | 36.08 | A C |
| ATOM | 560 | C | VAL | A | 307 | 18.632 | 0.270 | 35.261 | 1.00 | 42.67 | A C |
| ATOM | 561 | O | VAL | A | 307 | 18.367 | 1.472 | 35.352 | 1.00 | 41.91 | A O |
| ATOM | 562 | N | THR | A | 308 | 17.860 | -0.682 | 35.789 | 1.00 | 45.24 | A N |
| ATOM | 563 | CA | THR | A | 308 | 16.609 | -0.384 | 36.485 | 1.00 | 46.10 | A C |
| ATOM | 564 | CB | THR | A | 308 | 15.734 | -1.644 | 36.616 | 1.00 | 44.58 | A C |
| ATOM | 565 | OG1 | THR | A | 308 | 16.462 | -2.673 | 37.288 | 1.00 | 45.04 | A O |
| ATOM | 566 | CG2 | THR | A | 308 | 15.337 | -2.147 | 35.262 | 1.00 | 44.01 | A C |
| ATOM | 567 | C | THR | A | 308 | 16.695 | 0.327 | 37.835 | 1.00 | 48.74 | A C |
| ATOM | 568 | O | THR | A | 308 | 15.863 | 1.169 | 38.133 | 1.00 | 49.42 | A O |
| ATOM | 569 | N | GLN | A | 309 | 17.674 | -0.019 | 38.664 | 1.00 | 52.83 | A N |
| ATOM | 570 | CA | GLN | A | 309 | 17.792 | 0.671 | 39.941 | 1.00 | 56.39 | A C |
| ATOM | 571 | CB | GLN | A | 309 | 18.795 | -0.045 | 40.846 | 1.00 | 59.39 | A C |
| ATOM | 572 | CG | GLN | A | 309 | 18.416 | -1.478 | 41.184 | 1.00 | 63.22 | A C |
| ATOM | 573 | CD | GLN | A | 309 | 17.089 | -1.572 | 41.911 | 1.00 | 64.66 | A C |
| ATOM | 574 | OE1 | GLN | A | 309 | 16.431 | -0.561 | 42.158 | 1.00 | 64.09 | A O |
| ATOM | 575 | NE2 | GLN | A | 309 | 16.507 | -2.684 | 42.346 | 1.00 | 64.86 | A N |
| ATOM | 576 | C | GLN | A | 309 | 18.197 | 2.128 | 39.745 | 1.00 | 56.93 | A C |
| ATOM | 577 | O | GLN | A | 309 | 19.008 | 2.428 | 38.872 | 1.00 | 56.59 | A O |
| ATOM | 578 | N | GLU | A | 310 | 17.601 | 3.012 | 40.522 | 1.00 | 58.66 | A N |
| ATOM | 579 | CA | GLU | A | 310 | 17.865 | 4.451 | 40.456 | 1.00 | 60.36 | A C |
| ATOM | 580 | CB | GLU | A | 310 | 16.869 | 5.198 | 41.373 | 1.00 | 63.71 | A C |
| ATOM | 581 | CG | GLU | A | 310 | 16.756 | 4.644 | 42.839 | 1.00 | 67.70 | A C |
| ATOM | 582 | CD | GLU | A | 310 | 15.460 | 3.833 | 43.129 | 1.00 | 68.91 | A C |
| ATOM | 583 | OE1 | GLU | A | 310 | 14.405 | 4.108 | 42.497 | 1.00 | 69.84 | A O |
| ATOM | 584 | OE2 | GLU | A | 310 | 15.502 | 2.933 | 44.007 | 1.00 | 67.89 | A O |
| ATOM | 585 | C | GLU | A | 310 | 19.321 | 4.852 | 40.813 | 1.00 | 59.58 | A C |
| ATOM | 586 | O | GLU | A | 310 | 19.900 | 4.316 | 41.776 | 1.00 | 59.94 | A O |
| ATOM | 587 | N | PRO | A | 311 | 19.944 | 5.757 | 40.016 | 1.00 | 58.01 | A N |

Figure 4

| ATOM | 588 | CD  | PRO | A | 311 | 21.287 | 6.257 | 40.380 | 1.00 | 57.69 | A | C |
| ATOM | 589 | CA  | PRO | A | 311 | 19.445 | 6.483 | 38.833 | 1.00 | 55.68 | A | C |
| ATOM | 590 | CB  | PRO | A | 311 | 20.572 | 7.488 | 38.532 | 1.00 | 55.95 | A | C |
| ATOM | 591 | CG  | PRO | A | 311 | 21.255 | 7.666 | 39.848 | 1.00 | 56.81 | A | C |
| ATOM | 592 | C   | PRO | A | 311 | 19.224 | 5.576 | 37.616 | 1.00 | 52.81 | A | C |
| ATOM | 593 | O   | PRO | A | 311 | 20.104 | 4.792 | 37.250 | 1.00 | 52.75 | A | O |
| ATOM | 594 | N   | ILE | A | 312 | 18.060 | 5.709 | 36.983 | 1.00 | 49.25 | A | N |
| ATOM | 595 | CA  | ILE | A | 312 | 17.723 | 4.909 | 35.795 | 1.00 | 44.76 | A | C |
| ATOM | 596 | CB  | ILE | A | 312 | 16.225 | 5.104 | 35.373 | 1.00 | 44.07 | A | C |
| ATOM | 597 | CG2 | ILE | A | 312 | 15.796 | 3.987 | 34.423 | 1.00 | 43.65 | A | C |
| ATOM | 598 | CG1 | ILE | A | 312 | 15.309 | 5.118 | 36.599 | 1.00 | 43.67 | A | C |
| ATOM | 599 | CD1 | ILE | A | 312 | 15.206 | 3.799 | 37.308 | 1.00 | 43.24 | A | C |
| ATOM | 600 | C   | ILE | A | 312 | 18.619 | 5.296 | 34.596 | 1.00 | 40.50 | A | C |
| ATOM | 601 | O   | ILE | A | 312 | 18.884 | 6.485 | 34.361 | 1.00 | 38.53 | A | O |
| ATOM | 602 | N   | TYR | A | 313 | 19.060 | 4.290 | 33.841 | 1.00 | 36.94 | A | N |
| ATOM | 603 | CA  | TYR | A | 313 | 19.905 | 4.501 | 32.662 | 1.00 | 35.48 | A | C |
| ATOM | 604 | CB  | TYR | A | 313 | 21.338 | 3.995 | 32.876 | 1.00 | 35.48 | A | C |
| ATOM | 605 | CG  | TYR | A | 313 | 22.227 | 4.692 | 33.877 | 1.00 | 36.81 | A | C |
| ATOM | 606 | CD1 | TYR | A | 313 | 21.977 | 5.992 | 34.310 | 1.00 | 38.30 | A | C |
| ATOM | 607 | CE1 | TYR | A | 313 | 22.858 | 6.641 | 35.185 | 1.00 | 38.28 | A | C |
| ATOM | 608 | CD2 | TYR | A | 313 | 23.381 | 4.053 | 34.343 | 1.00 | 37.78 | A | C |
| ATOM | 609 | CE2 | TYR | A | 313 | 24.264 | 4.684 | 35.204 | 1.00 | 37.33 | A | C |
| ATOM | 610 | CZ  | TYR | A | 313 | 24.003 | 5.972 | 35.619 | 1.00 | 38.39 | A | C |
| ATOM | 611 | OH  | TYR | A | 313 | 24.901 | 6.589 | 36.459 | 1.00 | 38.72 | A | O |
| ATOM | 612 | C   | TYR | A | 313 | 19.410 | 3.715 | 31.454 | 1.00 | 32.68 | A | C |
| ATOM | 613 | O   | TYR | A | 313 | 18.945 | 2.582 | 31.576 | 1.00 | 30.53 | A | O |
| ATOM | 614 | N   | ILE | A | 314 | 19.603 | 4.310 | 30.281 | 1.00 | 31.56 | A | N |
| ATOM | 615 | CA  | ILE | A | 314 | 19.299 | 3.661 | 29.014 | 1.00 | 30.03 | A | C |
| ATOM | 616 | CB  | ILE | A | 314 | 18.194 | 4.364 | 28.208 | 1.00 | 28.72 | A | C |
| ATOM | 617 | CG2 | ILE | A | 314 | 17.995 | 3.625 | 26.891 | 1.00 | 30.78 | A | C |
| ATOM | 618 | CG1 | ILE | A | 314 | 16.881 | 4.378 | 28.997 | 1.00 | 30.73 | A | C |
| ATOM | 619 | CD1 | ILE | A | 314 | 15.734 | 5.041 | 28.267 | 1.00 | 31.27 | A | C |
| ATOM | 620 | C   | ILE | A | 314 | 20.627 | 3.744 | 28.248 | 1.00 | 28.40 | A | C |
| ATOM | 621 | O   | ILE | A | 314 | 21.151 | 4.829 | 28.001 | 1.00 | 26.31 | A | O |
| ATOM | 622 | N   | ILE | A | 315 | 21.196 | 2.588 | 27.934 | 1.00 | 29.18 | A | N |
| ATOM | 623 | CA  | ILE | A | 315 | 22.474 | 2.525 | 27.234 | 1.00 | 30.01 | A | C |
| ATOM | 624 | CB  | ILE | A | 315 | 23.450 | 1.502 | 27.910 | 1.00 | 30.30 | A | C |
| ATOM | 625 | CG2 | ILE | A | 315 | 24.706 | 1.292 | 27.050 | 1.00 | 30.30 | A | C |
| ATOM | 626 | CG1 | ILE | A | 315 | 23.842 | 1.989 | 29.312 | 1.00 | 30.89 | A | C |
| ATOM | 627 | CD1 | ILE | A | 315 | 22.859 | 1.624 | 30.409 | 1.00 | 30.25 | A | C |
| ATOM | 628 | C   | ILE | A | 315 | 22.289 | 2.161 | 25.770 | 1.00 | 29.00 | A | C |
| ATOM | 629 | O   | ILE | A | 315 | 21.747 | 1.099 | 25.443 | 1.00 | 29.23 | A | O |
| ATOM | 630 | N   | THR | A | 316 | 22.723 | 3.065 | 24.895 | 1.00 | 27.67 | A | N |
| ATOM | 631 | CA  | THR | A | 316 | 22.617 | 2.856 | 23.461 | 1.00 | 28.38 | A | C |
| ATOM | 632 | CB  | THR | A | 316 | 21.682 | 3.869 | 22.771 | 1.00 | 25.55 | A | C |
| ATOM | 633 | OG1 | THR | A | 316 | 22.275 | 5.174 | 22.822 | 1.00 | 23.55 | A | O |
| ATOM | 634 | CG2 | THR | A | 316 | 20.308 | 3.892 | 23.425 | 1.00 | 25.78 | A | C |
| ATOM | 635 | C   | THR | A | 316 | 23.981 | 3.090 | 22.878 | 1.00 | 29.67 | A | C |
| ATOM | 636 | O   | THR | A | 316 | 24.903 | 3.512 | 23.578 | 1.00 | 30.36 | A | O |
| ATOM | 637 | N   | GLU | A | 317 | 24.092 | 2.841 | 21.578 | 1.00 | 30.10 | A | N |
| ATOM | 638 | CA  | GLU | A | 317 | 25.337 | 3.056 | 20.866 | 1.00 | 29.04 | A | C |
| ATOM | 639 | CB  | GLU | A | 317 | 25.215 | 2.566 | 19.421 | 1.00 | 30.63 | A | C |
| ATOM | 640 | CG  | GLU | A | 317 | 24.111 | 3.251 | 18.617 | 1.00 | 32.24 | A | C |
| ATOM | 641 | CD  | GLU | A | 317 | 24.174 | 2.899 | 17.156 | 1.00 | 33.58 | A | C |
| ATOM | 642 | OE1 | GLU | A | 317 | 23.151 | 2.431 | 16.613 | 1.00 | 33.63 | A | O |
| ATOM | 643 | OE2 | GLU | A | 317 | 25.260 | 3.079 | 16.555 | 1.00 | 35.31 | A | O |
| ATOM | 644 | C   | GLU | A | 317 | 25.655 | 4.545 | 20.893 | 1.00 | 26.38 | A | C |
| ATOM | 645 | O   | GLU | A | 317 | 24.766 | 5.385 | 21.055 | 1.00 | 26.77 | A | O |
| ATOM | 646 | N   | TYR | A | 318 | 26.937 | 4.852 | 20.777 | 1.00 | 24.56 | A | N |
| ATOM | 647 | CA  | TYR | A | 318 | 27.422 | 6.225 | 20.782 | 1.00 | 24.80 | A | C |

Figure 4

| ATOM | 648 | CB  | TYR A 318 | 28.848 | 6.250  | 21.380 | 1.00 | 23.76 | A | C |
|------|-----|-----|-----------|--------|--------|--------|------|-------|---|---|
| ATOM | 649 | CG  | TYR A 318 | 29.517 | 7.602  | 21.413 | 1.00 | 24.30 | A | C |
| ATOM | 650 | CD1 | TYR A 318 | 29.044 | 8.621  | 22.245 | 1.00 | 24.62 | A | C |
| ATOM | 651 | CE1 | TYR A 318 | 29.637 | 9.881  | 22.253 | 1.00 | 25.17 | A | C |
| ATOM | 652 | CD2 | TYR A 318 | 30.610 | 7.874  | 20.590 | 1.00 | 25.08 | A | C |
| ATOM | 653 | CE2 | TYR A 318 | 31.221 | 9.136  | 20.592 | 1.00 | 25.20 | A | C |
| ATOM | 654 | CZ  | TYR A 318 | 30.731 | 10.128 | 21.421 | 1.00 | 25.68 | A | C |
| ATOM | 655 | OH  | TYR A 318 | 31.334 | 11.366 | 21.420 | 1.00 | 26.64 | A | O |
| ATOM | 656 | C   | TYR A 318 | 27.409 | 6.804  | 19.361 | 1.00 | 25.16 | A | C |
| ATOM | 657 | O   | TYR A 318 | 27.710 | 6.105  | 18.392 | 1.00 | 26.38 | A | O |
| ATOM | 658 | N   | MET A 319 | 26.991 | 8.058  | 19.233 | 1.00 | 25.80 | A | N |
| ATOM | 659 | CA  | MET A 319 | 26.959 | 8.729  | 17.937 | 1.00 | 26.78 | A | C |
| ATOM | 660 | CB  | MET A 319 | 25.533 | 9.143  | 17.553 | 1.00 | 26.98 | A | C |
| ATOM | 661 | CG  | MET A 319 | 24.583 | 7.966  | 17.285 | 1.00 | 27.18 | A | C |
| ATOM | 662 | SD  | MET A 319 | 25.055 | 6.796  | 15.954 | 1.00 | 30.43 | A | S |
| ATOM | 663 | CE  | MET A 319 | 24.745 | 7.781  | 14.516 | 1.00 | 28.54 | A | C |
| ATOM | 664 | C   | MET A 319 | 27.868 | 9.933  | 18.071 | 1.00 | 27.22 | A | C |
| ATOM | 665 | O   | MET A 319 | 27.488 | 10.944 | 18.641 | 1.00 | 26.26 | A | O |
| ATOM | 666 | N   | GLU A 320 | 29.096 | 9.760  | 17.588 | 1.00 | 30.01 | A | N |
| ATOM | 667 | CA  | GLU A 320 | 30.174 | 10.746 | 17.635 | 1.00 | 30.57 | A | C |
| ATOM | 668 | CB  | GLU A 320 | 31.324 | 10.286 | 16.730 | 1.00 | 35.15 | A | C |
| ATOM | 669 | CG  | GLU A 320 | 32.382 | 11.339 | 16.409 | 1.00 | 40.28 | A | C |
| ATOM | 670 | CD  | GLU A 320 | 33.716 | 11.096 | 17.103 | 1.00 | 42.13 | A | C |
| ATOM | 671 | OE1 | GLU A 320 | 34.003 | 9.933  | 17.476 | 1.00 | 43.34 | A | O |
| ATOM | 672 | OE2 | GLU A 320 | 34.475 | 12.082 | 17.267 | 1.00 | 43.43 | A | O |
| ATOM | 673 | C   | GLU A 320 | 29.809 | 12.181 | 17.327 | 1.00 | 28.39 | A | C |
| ATOM | 674 | O   | GLU A 320 | 30.221 | 13.083 | 18.048 | 1.00 | 28.49 | A | O |
| ATOM | 675 | N   | ASN A 321 | 29.038 | 12.411 | 16.272 | 1.00 | 27.18 | A | N |
| ATOM | 676 | CA  | ASN A 321 | 28.664 | 13.779 | 15.929 | 1.00 | 25.92 | A | C |
| ATOM | 677 | CB  | ASN A 321 | 28.769 | 13.995 | 14.427 | 1.00 | 26.12 | A | C |
| ATOM | 678 | CG  | ASN A 321 | 30.199 | 14.059 | 13.976 | 1.00 | 26.44 | A | C |
| ATOM | 679 | OD1 | ASN A 321 | 30.941 | 14.962 | 14.375 | 1.00 | 27.19 | A | O |
| ATOM | 680 | ND2 | ASN A 321 | 30.617 | 13.080 | 13.185 | 1.00 | 26.29 | A | N |
| ATOM | 681 | C   | ASN A 321 | 27.330 | 14.262 | 16.494 | 1.00 | 25.76 | A | C |
| ATOM | 682 | O   | ASN A 321 | 26.846 | 15.361 | 16.152 | 1.00 | 25.00 | A | O |
| ATOM | 683 | N   | GLY A 322 | 26.780 | 13.440 | 17.392 | 1.00 | 25.72 | A | N |
| ATOM | 684 | CA  | GLY A 322 | 25.542 | 13.738 | 18.095 | 1.00 | 26.23 | A | C |
| ATOM | 685 | C   | GLY A 322 | 24.275 | 13.985 | 17.315 | 1.00 | 25.06 | A | C |
| ATOM | 686 | O   | GLY A 322 | 23.876 | 13.150 | 16.532 | 1.00 | 26.76 | A | O |
| ATOM | 687 | N   | SER A 323 | 23.633 | 15.117 | 17.580 | 1.00 | 24.48 | A | N |
| ATOM | 688 | CA  | SER A 323 | 22.395 | 15.503 | 16.928 | 1.00 | 26.78 | A | C |
| ATOM | 689 | CB  | SER A 323 | 21.618 | 16.439 | 17.844 | 1.00 | 26.49 | A | C |
| ATOM | 690 | OG  | SER A 323 | 20.376 | 16.788 | 17.271 | 1.00 | 29.99 | A | O |
| ATOM | 691 | C   | SER A 323 | 22.629 | 16.190 | 15.585 | 1.00 | 25.63 | A | C |
| ATOM | 692 | O   | SER A 323 | 23.437 | 17.115 | 15.484 | 1.00 | 25.20 | A | O |
| ATOM | 693 | N   | LEU A 324 | 21.886 | 15.753 | 14.571 | 1.00 | 26.32 | A | N |
| ATOM | 694 | CA  | LEU A 324 | 21.980 | 16.319 | 13.216 | 1.00 | 26.99 | A | C |
| ATOM | 695 | CB  | LEU A 324 | 21.079 | 15.544 | 12.240 | 1.00 | 27.17 | A | C |
| ATOM | 696 | CG  | LEU A 324 | 20.958 | 15.966 | 10.760 | 1.00 | 26.43 | A | C |
| ATOM | 697 | CD1 | LEU A 324 | 22.291 | 15.780 | 10.015 | 1.00 | 24.23 | A | C |
| ATOM | 698 | CD2 | LEU A 324 | 19.853 | 15.135 | 10.095 | 1.00 | 24.66 | A | C |
| ATOM | 699 | C   | LEU A 324 | 21.671 | 17.822 | 13.133 | 1.00 | 27.04 | A | C |
| ATOM | 700 | O   | LEU A 324 | 22.323 | 18.546 | 12.376 | 1.00 | 28.33 | A | O |
| ATOM | 701 | N   | VAL A 325 | 20.699 | 18.301 | 13.908 | 1.00 | 27.43 | A | N |
| ATOM | 702 | CA  | VAL A 325 | 20.369 | 19.722 | 13.875 | 1.00 | 27.54 | A | C |
| ATOM | 703 | CB  | VAL A 325 | 19.085 | 20.041 | 14.694 | 1.00 | 25.91 | A | C |
| ATOM | 704 | CG1 | VAL A 325 | 19.331 | 19.917 | 16.185 | 1.00 | 25.76 | A | C |
| ATOM | 705 | CG2 | VAL A 325 | 18.565 | 21.423 | 14.349 | 1.00 | 25.07 | A | C |
| ATOM | 706 | C   | VAL A 325 | 21.582 | 20.545 | 14.355 | 1.00 | 29.40 | A | C |
| ATOM | 707 | O   | VAL A 325 | 21.861 | 21.641 | 13.839 | 1.00 | 29.93 | A | O |

Figure 4

| | | | | | | | | | | |
|---|---|---|---|---|---|---|---|---|---|---|
| ATOM | 708 | N | ASP | A | 326 | 22.336 | 19.971 | 15.291 | 1.00 30.35 | A N |
| ATOM | 709 | CA | ASP | A | 326 | 23.532 | 20.618 | 15.831 | 1.00 31.76 | A C |
| ATOM | 710 | CB | ASP | A | 326 | 23.868 | 20.046 | 17.204 | 1.00 31.36 | A C |
| ATOM | 711 | CG | ASP | A | 326 | 22.919 | 20.506 | 18.271 | 1.00 30.81 | A C |
| ATOM | 712 | OD1 | ASP | A | 326 | 22.430 | 21.657 | 18.193 | 1.00 30.30 | A O |
| ATOM | 713 | OD2 | ASP | A | 326 | 22.680 | 19.714 | 19.203 | 1.00 31.66 | A O |
| ATOM | 714 | C | ASP | A | 326 | 24.743 | 20.443 | 14.916 | 1.00 32.64 | A C |
| ATOM | 715 | O | ASP | A | 326 | 25.545 | 21.364 | 14.736 | 1.00 34.53 | A O |
| ATOM | 716 | N | PHE | A | 327 | 24.879 | 19.249 | 14.355 | 1.00 32.87 | A N |
| ATOM | 717 | CA | PHE | A | 327 | 25.980 | 18.943 | 13.469 | 1.00 32.44 | A C |
| ATOM | 718 | CB | PHE | A | 327 | 25.967 | 17.463 | 13.108 | 1.00 32.87 | A C |
| ATOM | 719 | CG | PHE | A | 327 | 27.059 | 17.070 | 12.170 | 1.00 35.21 | A C |
| ATOM | 720 | CD1 | PHE | A | 327 | 28.399 | 17.247 | 12.537 | 1.00 35.00 | A C |
| ATOM | 721 | CD2 | PHE | A | 327 | 26.759 | 16.574 | 10.891 | 1.00 35.48 | A C |
| ATOM | 722 | CE1 | PHE | A | 327 | 29.421 | 16.944 | 11.644 | 1.00 36.13 | A C |
| ATOM | 723 | CE2 | PHE | A | 327 | 27.782 | 16.265 | 9.985 | 1.00 35.99 | A C |
| ATOM | 724 | CZ | PHE | A | 327 | 29.111 | 16.451 | 10.360 | 1.00 36.42 | A C |
| ATOM | 725 | C | PHE | A | 327 | 25.944 | 19.782 | 12.195 | 1.00 32.80 | A C |
| ATOM | 726 | O | PHE | A | 327 | 26.985 | 20.194 | 11.702 | 1.00 33.24 | A O |
| ATOM | 727 | N | LEU | A | 328 | 24.754 | 20.046 | 11.667 | 1.00 32.15 | A N |
| ATOM | 728 | CA | LEU | A | 328 | 24.636 | 20.830 | 10.441 | 1.00 33.04 | A C |
| ATOM | 729 | CB | LEU | A | 328 | 23.187 | 20.822 | 9.930 | 1.00 31.61 | A C |
| ATOM | 730 | CG | LEU | A | 328 | 22.666 | 19.555 | 9.246 | 1.00 30.78 | A C |
| ATOM | 731 | CD1 | LEU | A | 328 | 21.177 | 19.684 | 8.970 | 1.00 31.33 | A C |
| ATOM | 732 | CD2 | LEU | A | 328 | 23.424 | 19.301 | 7.967 | 1.00 30.45 | A C |
| ATOM | 733 | C | LEU | A | 328 | 25.156 | 22.270 | 10.556 | 1.00 34.51 | A C |
| ATOM | 734 | O | LEU | A | 328 | 25.417 | 22.915 | 9.541 | 1.00 35.45 | A O |
| ATOM | 735 | N | LYS | A | 329 | 25.305 | 22.771 | 11.782 | 1.00 36.11 | A N |
| ATOM | 736 | CA | LYS | A | 329 | 25.794 | 24.134 | 12.005 | 1.00 37.59 | A C |
| ATOM | 737 | CB | LYS | A | 329 | 25.049 | 24.790 | 13.165 | 1.00 38.56 | A C |
| ATOM | 738 | CG | LYS | A | 329 | 23.544 | 24.769 | 13.056 | 1.00 39.48 | A C |
| ATOM | 739 | CD | LYS | A | 329 | 22.937 | 25.511 | 14.223 | 1.00 40.74 | A C |
| ATOM | 740 | CE | LYS | A | 329 | 21.429 | 25.414 | 14.219 | 1.00 41.61 | A C |
| ATOM | 741 | NZ | LYS | A | 329 | 20.970 | 24.018 | 14.452 | 1.00 41.99 | A N |
| ATOM | 742 | C | LYS | A | 329 | 27.308 | 24.212 | 12.280 | 1.00 38.23 | A C |
| ATOM | 743 | O | LYS | A | 329 | 27.890 | 25.306 | 12.230 | 1.00 39.67 | A O |
| ATOM | 744 | N | THR | A | 330 | 27.932 | 23.064 | 12.564 | 1.00 36.72 | A N |
| ATOM | 745 | CA | THR | A | 330 | 29.366 | 22.996 | 12.844 | 1.00 35.44 | A C |
| ATOM | 746 | CB | THR | A | 330 | 29.769 | 21.597 | 13.344 | 1.00 34.35 | A O |
| ATOM | 747 | OG1 | THR | A | 330 | 29.546 | 20.626 | 12.322 | 1.00 33.66 | A O |
| ATOM | 748 | CG2 | THR | A | 330 | 28.977 | 21.226 | 14.583 | 1.00 33.43 | A C |
| ATOM | 749 | C | THR | A | 330 | 30.173 | 23.332 | 11.590 | 1.00 36.70 | A C |
| ATOM | 750 | O | THR | A | 330 | 29.657 | 23.197 | 10.483 | 1.00 39.18 | A O |
| ATOM | 751 | N | PRO | A | 331 | 31.443 | 23.789 | 11.743 | 1.00 36.61 | A N |
| ATOM | 752 | CD | PRO | A | 331 | 32.165 | 24.097 | 12.991 | 1.00 35.85 | A C |
| ATOM | 753 | CA | PRO | A | 331 | 32.276 | 24.132 | 10.583 | 1.00 35.76 | A C |
| ATOM | 754 | CB | PRO | A | 331 | 33.656 | 24.312 | 11.210 | 1.00 35.94 | A C |
| ATOM | 755 | CG | PRO | A | 331 | 33.322 | 24.958 | 12.503 | 1.00 34.87 | A C |
| ATOM | 756 | C | PRO | A | 331 | 32.279 | 23.063 | 9.507 | 1.00 34.54 | A C |
| ATOM | 757 | O | PRO | A | 331 | 32.182 | 23.385 | 8.340 | 1.00 34.91 | A O |
| ATOM | 758 | N | SER | A | 332 | 32.372 | 21.801 | 9.921 | 1.00 35.36 | A N |
| ATOM | 759 | CA | SER | A | 332 | 32.377 | 20.639 | 9.023 | 1.00 37.33 | A C |
| ATOM | 760 | CB | SER | A | 332 | 32.751 | 19.371 | 9.794 | 1.00 38.41 | A C |
| ATOM | 761 | OG | SER | A | 332 | 33.944 | 19.572 | 10.535 | 1.00 43.00 | A O |
| ATOM | 762 | C | SER | A | 332 | 31.014 | 20.414 | 8.366 | 1.00 38.42 | A C |
| ATOM | 763 | O | SER | A | 332 | 30.942 | 20.027 | 7.187 | 1.00 37.76 | A O |
| ATOM | 764 | N | GLY | A | 333 | 29.953 | 20.611 | 9.158 | 1.00 37.92 | A N |
| ATOM | 765 | CA | GLY | A | 333 | 28.578 | 20.450 | 8.695 | 1.00 36.25 | A C |
| ATOM | 766 | C | GLY | A | 333 | 28.145 | 21.507 | 7.690 | 1.00 35.12 | A C |
| ATOM | 767 | O | GLY | A | 333 | 27.367 | 21.226 | 6.780 | 1.00 35.73 | A O |

Figure 4

| ATOM | 768 | N | ILE | A | 334 | 28.631 | 22.730 | 7.871 | 1.00 | 34.72 | A | N |
|---|---|---|---|---|---|---|---|---|---|---|---|---|
| ATOM | 769 | CA | ILE | A | 334 | 28.333 | 23.824 | 6.956 | 1.00 | 35.38 | A | C |
| ATOM | 770 | CB | ILE | A | 334 | 28.944 | 25.157 | 7.468 | 1.00 | 36.41 | A | C |
| ATOM | 771 | CG2 | ILE | A | 334 | 28.943 | 26.207 | 6.358 | 1.00 | 37.26 | A | C |
| ATOM | 772 | CG1 | ILE | A | 334 | 28.192 | 25.676 | 8.703 | 1.00 | 36.44 | A | C |
| ATOM | 773 | CD1 | ILE | A | 334 | 26.885 | 26.439 | 8.396 | 1.00 | 36.74 | A | C |
| ATOM | 774 | C | ILE | A | 334 | 28.943 | 23.501 | 5.580 | 1.00 | 36.01 | A | C |
| ATOM | 775 | O | ILE | A | 334 | 28.330 | 23.751 | 4.540 | 1.00 | 36.01 | A | O |
| ATOM | 776 | N | LYS | A | 335 | 30.132 | 22.896 | 5.602 | 1.00 | 36.77 | A | N |
| ATOM | 777 | CA | LYS | A | 335 | 30.880 | 22.540 | 4.397 | 1.00 | 35.89 | A | C |
| ATOM | 778 | CB | LYS | A | 335 | 32.348 | 22.306 | 4.747 | 1.00 | 36.72 | A | C |
| ATOM | 779 | CG | LYS | A | 335 | 33.058 | 23.497 | 5.353 | 1.00 | 38.38 | A | C |
| ATOM | 780 | CD | LYS | A | 335 | 34.426 | 23.075 | 5.884 | 1.00 | 39.80 | A | C |
| ATOM | 781 | CE | LYS | A | 335 | 34.951 | 24.094 | 6.890 | 1.00 | 41.77 | A | C |
| ATOM | 782 | NZ | LYS | A | 335 | 35.797 | 23.468 | 7.964 | 1.00 | 42.16 | A | N |
| ATOM | 783 | C | LYS | A | 335 | 30.383 | 21.335 | 3.611 | 1.00 | 35.32 | A | C |
| ATOM | 784 | O | LYS | A | 335 | 30.854 | 21.102 | 2.502 | 1.00 | 35.07 | A | O |
| ATOM | 785 | N | LEU | A | 336 | 29.449 | 20.565 | 4.168 | 1.00 | 35.60 | A | N |
| ATOM | 786 | CA | LEU | A | 336 | 28.917 | 19.371 | 3.486 | 1.00 | 34.00 | A | C |
| ATOM | 787 | CB | LEU | A | 336 | 27.865 | 18.665 | 4.367 | 1.00 | 33.34 | A | C |
| ATOM | 788 | CG | LEU | A | 336 | 28.316 | 18.035 | 5.693 | 1.00 | 31.61 | A | C |
| ATOM | 789 | CD1 | LEU | A | 336 | 27.135 | 17.701 | 6.578 | 1.00 | 30.63 | A | C |
| ATOM | 790 | CD2 | LEU | A | 336 | 29.131 | 16.796 | 5.419 | 1.00 | 31.56 | A | C |
| ATOM | 791 | C | LEU | A | 336 | 28.322 | 19.678 | 2.099 | 1.00 | 32.70 | A | C |
| ATOM | 792 | O | LEU | A | 336 | 27.661 | 20.704 | 1.897 | 1.00 | 32.02 | A | O |
| ATOM | 793 | N | THR | A | 337 | 28.590 | 18.795 | 1.144 | 1.00 | 31.63 | A | N |
| ATOM | 794 | CA | THR | A | 337 | 28.082 | 18.964 | -0.204 | 1.00 | 33.27 | A | C |
| ATOM | 795 | CB | THR | A | 337 | 28.919 | 18.159 | -1.255 | 1.00 | 34.22 | A | C |
| ATOM | 796 | OG1 | THR | A | 337 | 28.841 | 16.753 | -0.991 | 1.00 | 35.18 | A | O |
| ATOM | 797 | CG2 | THR | A | 337 | 30.380 | 18.594 | -1.224 | 1.00 | 34.21 | A | C |
| ATOM | 798 | C | THR | A | 337 | 26.607 | 18.552 | -0.298 | 1.00 | 34.01 | A | C |
| ATOM | 799 | O | THR | A | 337 | 26.116 | 17.767 | 0.524 | 1.00 | 32.75 | A | O |
| ATOM | 800 | N | ILE | A | 338 | 25.917 | 19.076 | -1.313 | 1.00 | 33.67 | A | N |
| ATOM | 801 | CA | ILE | A | 338 | 24.512 | 18.758 | -1.535 | 1.00 | 33.70 | A | C |
| ATOM | 802 | CB | ILE | A | 338 | 23.927 | 19.494 | -2.785 | 1.00 | 33.52 | A | C |
| ATOM | 803 | CG2 | ILE | A | 338 | 24.588 | 18.990 | -4.084 | 1.00 | 33.09 | A | C |
| ATOM | 804 | CG1 | ILE | A | 338 | 22.406 | 19.292 | -2.847 | 1.00 | 32.85 | A | C |
| ATOM | 805 | CD1 | ILE | A | 338 | 21.631 | 19.892 | -1.678 | 1.00 | 31.35 | A | C |
| ATOM | 806 | C | ILE | A | 338 | 24.397 | 17.253 | -1.719 | 1.00 | 34.03 | A | C |
| ATOM | 807 | O | ILE | A | 338 | 23.393 | 16.648 | -1.359 | 1.00 | 33.91 | A | O |
| ATOM | 808 | N | ASN | A | 339 | 25.454 | 16.643 | -2.241 | 1.00 | 34.18 | A | N |
| ATOM | 809 | CA | ASN | A | 339 | 25.477 | 15.202 | -2.455 | 1.00 | 33.87 | A | C |
| ATOM | 810 | CB | ASN | A | 339 | 26.745 | 14.806 | -3.185 | 1.00 | 34.40 | A | C |
| ATOM | 811 | CG | ASN | A | 339 | 26.746 | 15.269 | -4.591 | 1.00 | 36.28 | A | C |
| ATOM | 812 | OD1 | ASN | A | 339 | 26.381 | 14.510 | -5.490 | 1.00 | 36.98 | A | O |
| ATOM | 813 | ND2 | ASN | A | 339 | 27.100 | 16.540 | -4.807 | 1.00 | 37.06 | A | N |
| ATOM | 814 | C | ASN | A | 339 | 25.428 | 14.457 | -1.148 | 1.00 | 33.52 | A | C |
| ATOM | 815 | O | ASN | A | 339 | 24.714 | 13.465 | -1.013 | 1.00 | 33.52 | A | O |
| ATOM | 816 | N | LYS | A | 340 | 26.251 | 14.915 | -0.214 | 1.00 | 32.69 | A | N |
| ATOM | 817 | CA | LYS | A | 340 | 26.346 | 14.314 | 1.097 | 1.00 | 33.71 | A | C |
| ATOM | 818 | CB | LYS | A | 340 | 27.537 | 14.939 | 1.847 | 1.00 | 34.32 | A | C |
| ATOM | 819 | CG | LYS | A | 340 | 27.730 | 14.440 | 3.282 | 1.00 | 34.83 | A | C |
| ATOM | 820 | CD | LYS | A | 340 | 28.030 | 12.950 | 3.316 | 1.00 | 35.83 | A | C |
| ATOM | 821 | CE | LYS | A | 340 | 27.859 | 12.389 | 4.716 | 1.00 | 35.34 | A | C |
| ATOM | 822 | NZ | LYS | A | 340 | 27.965 | 10.904 | 4.721 | 1.00 | 36.18 | A | N |
| ATOM | 823 | C | LYS | A | 340 | 25.023 | 14.487 | 1.873 | 1.00 | 32.25 | A | C |
| ATOM | 824 | O | LYS | A | 340 | 24.527 | 13.540 | 2.495 | 1.00 | 31.56 | A | O |
| ATOM | 825 | N | LEU | A | 341 | 24.441 | 15.682 | 1.791 | 1.00 | 32.73 | A | N |
| ATOM | 826 | CA | LEU | A | 341 | 23.179 | 16.001 | 2.464 | 1.00 | 32.81 | A | C |
| ATOM | 827 | CB | LEU | A | 341 | 22.803 | 17.466 | 2.211 | 1.00 | 32.37 | A | C |

Figure 4

| | | | | | | | | | | | |
|---|---|---|---|---|---|---|---|---|---|---|---|
| ATOM | 828 | CG | LEU | A | 341 | 23.828 | 18.528 | 2.616 | 1.00 | 32.35 | A C |
| ATOM | 829 | CD1 | LEU | A | 341 | 23.327 | 19.925 | 2.277 | 1.00 | 32.02 | A C |
| ATOM | 830 | CD2 | LEU | A | 341 | 24.102 | 18.408 | 4.101 | 1.00 | 32.73 | A C |
| ATOM | 831 | C | LEU | A | 341 | 22.039 | 15.090 | 2.013 | 1.00 | 32.21 | A C |
| ATOM | 832 | O | LEU | A | 341 | 21.265 | 14.601 | 2.832 | 1.00 | 31.98 | A O |
| ATOM | 833 | N | LEU | A | 342 | 21.954 | 14.836 | 0.711 | 1.00 | 33.05 | A N |
| ATOM | 834 | CA | LEU | A | 342 | 20.910 | 13.975 | 0.171 | 1.00 | 34.48 | A C |
| ATOM | 835 | CB | LEU | A | 342 | 20.849 | 14.081 | -1.350 | 1.00 | 36.58 | A C |
| ATOM | 836 | CG | LEU | A | 342 | 20.397 | 15.454 | -1.829 | 1.00 | 38.22 | A C |
| ATOM | 837 | CD1 | LEU | A | 342 | 20.166 | 15.344 | -3.283 | 1.00 | 41.39 | A C |
| ATOM | 838 | CD2 | LEU | A | 342 | 19.121 | 15.899 | -1.173 | 1.00 | 40.52 | A C |
| ATOM | 839 | C | LEU | A | 342 | 21.069 | 12.528 | 0.581 | 1.00 | 34.08 | A C |
| ATOM | 840 | O | LEU | A | 342 | 20.083 | 11.813 | 0.763 | 1.00 | 33.63 | A O |
| ATOM | 841 | N | ASP | A | 343 | 22.299 | 12.052 | 0.667 | 1.00 | 33.39 | A N |
| ATOM | 842 | CA | ASP | A | 343 | 22.463 | 10.685 | 1.076 | 1.00 | 34.14 | A C |
| ATOM | 843 | CB | ASP | A | 343 | 23.855 | 10.143 | 0.766 | 1.00 | 38.75 | A C |
| ATOM | 844 | CG | ASP | A | 343 | 23.876 | 8.620 | 0.796 | 1.00 | 43.42 | A C |
| ATOM | 845 | OD1 | ASP | A | 343 | 23.403 | 8.013 | -0.209 | 1.00 | 44.48 | A O |
| ATOM | 846 | OD2 | ASP | A | 343 | 24.285 | 8.039 | 1.847 | 1.00 | 43.35 | A O |
| ATOM | 847 | C | ASP | A | 343 | 22.155 | 10.591 | 2.561 | 1.00 | 31.84 | A C |
| ATOM | 848 | O | ASP | A | 343 | 21.753 | 9.541 | 3.045 | 1.00 | 30.72 | A O |
| ATOM | 849 | N | MET | A | 344 | 22.361 | 11.684 | 3.284 | 1.00 | 29.48 | A N |
| ATOM | 850 | CA | MET | A | 344 | 22.040 | 11.695 | 4.695 | 1.00 | 29.98 | A C |
| ATOM | 851 | CB | MET | A | 344 | 22.568 | 12.967 | 5.360 | 1.00 | 32.58 | A C |
| ATOM | 852 | CG | MET | A | 344 | 24.095 | 12.984 | 5.568 | 1.00 | 34.11 | A C |
| ATOM | 853 | SD | MET | A | 344 | 24.600 | 14.406 | 6.564 | 1.00 | 36.34 | A S |
| ATOM | 854 | CE | MET | A | 344 | 25.199 | 13.601 | 7.995 | 1.00 | 35.74 | A C |
| ATOM | 855 | C | MET | A | 344 | 20.519 | 11.610 | 4.817 | 1.00 | 28.48 | A C |
| ATOM | 856 | O | MET | A | 344 | 19.999 | 10.818 | 5.599 | 1.00 | 27.61 | A O |
| ATOM | 857 | N | ALA | A | 345 | 19.818 | 12.400 | 4.002 | 1.00 | 25.72 | A N |
| ATOM | 858 | CA | ALA | A | 345 | 18.358 | 12.408 | 3.974 | 1.00 | 23.55 | A C |
| ATOM | 859 | CB | ALA | A | 345 | 17.850 | 13.467 | 3.003 | 1.00 | 23.60 | A C |
| ATOM | 860 | C | ALA | A | 345 | 17.835 | 11.036 | 3.566 | 1.00 | 22.68 | A C |
| ATOM | 861 | O | ALA | A | 345 | 16.913 | 10.532 | 4.177 | 1.00 | 24.31 | A O |
| ATOM | 862 | N | ALA | A | 346 | 18.441 | 10.430 | 2.547 | 1.00 | 21.71 | A N |
| ATOM | 863 | CA | ALA | A | 346 | 18.042 | 9.111 | 2.069 | 1.00 | 20.97 | A C |
| ATOM | 864 | CB | ALA | A | 346 | 18.831 | 8.756 | 0.844 | 1.00 | 20.79 | A C |
| ATOM | 865 | C | ALA | A | 346 | 18.225 | 8.033 | 3.152 | 1.00 | 23.19 | A C |
| ATOM | 866 | O | ALA | A | 346 | 17.543 | 6.994 | 3.148 | 1.00 | 22.78 | A O |
| ATOM | 867 | N | GLN | A | 347 | 19.164 | 8.273 | 4.067 | 1.00 | 24.77 | A N |
| ATOM | 868 | CA | GLN | A | 347 | 19.432 | 7.348 | 5.166 | 1.00 | 24.88 | A C |
| ATOM | 869 | CB | GLN | A | 347 | 20.719 | 7.727 | 5.870 | 1.00 | 26.66 | A C |
| ATOM | 870 | CG | GLN | A | 347 | 21.961 | 7.442 | 5.087 | 1.00 | 28.88 | A C |
| ATOM | 871 | CD | GLN | A | 347 | 23.178 | 7.650 | 5.937 | 1.00 | 30.94 | A C |
| ATOM | 872 | OE1 | GLN | A | 347 | 23.812 | 6.691 | 6.362 | 1.00 | 35.14 | A O |
| ATOM | 873 | NE2 | GLN | A | 347 | 23.483 | 8.902 | 6.242 | 1.00 | 31.13 | A N |
| ATOM | 874 | C | GLN | A | 347 | 18.301 | 7.396 | 6.171 | 1.00 | 22.83 | A C |
| ATOM | 875 | O | GLN | A | 347 | 17.878 | 6.368 | 6.693 | 1.00 | 22.87 | A O |
| ATOM | 876 | N | ILE | A | 348 | 17.838 | 8.610 | 6.451 | 1.00 | 22.18 | A N |
| ATOM | 877 | CA | ILE | A | 348 | 16.749 | 8.855 | 7.384 | 1.00 | 21.06 | A C |
| ATOM | 878 | CB | ILE | A | 348 | 16.620 | 10.362 | 7.681 | 1.00 | 21.29 | A C |
| ATOM | 879 | CG2 | ILE | A | 348 | 15.450 | 10.611 | 8.645 | 1.00 | 22.42 | A C |
| ATOM | 880 | CG1 | ILE | A | 348 | 17.929 | 10.900 | 8.287 | 1.00 | 19.74 | A C |
| ATOM | 881 | CD1 | ILE | A | 348 | 18.020 | 12.396 | 8.312 | 1.00 | 16.26 | A C |
| ATOM | 882 | C | ILE | A | 348 | 15.462 | 8.317 | 6.754 | 1.00 | 20.46 | A C |
| ATOM | 883 | O | ILE | A | 348 | 14.648 | 7.676 | 7.412 | 1.00 | 19.98 | A O |
| ATOM | 884 | N | ALA | A | 349 | 15.326 | 8.529 | 5.449 | 1.00 | 20.79 | A N |
| ATOM | 885 | CA | ALA | A | 349 | 14.178 | 8.045 | 4.713 | 1.00 | 20.36 | A C |
| ATOM | 886 | CB | ALA | A | 349 | 14.210 | 8.580 | 3.297 | 1.00 | 18.11 | A C |
| ATOM | 887 | C | ALA | A | 349 | 14.181 | 6.501 | 4.735 | 1.00 | 21.50 | A C |

Figure 4

| ATOM | 888 | O | ALA | A | 349 | 13.115 | 5.876 | 4.799 | 1.00 | 22.69 | A | O |
|------|-----|-----|-----|---|-----|--------|-------|-------|------|-------|---|---|
| ATOM | 889 | N | GLU | A | 350 | 15.372 | 5.896 | 4.774 | 1.00 | 22.53 | A | N |
| ATOM | 890 | CA | GLU | A | 350 | 15.492 | 4.439 | 4.813 | 1.00 | 23.09 | A | C |
| ATOM | 891 | CB | GLU | A | 350 | 16.930 | 3.986 | 4.506 | 1.00 | 26.13 | A | C |
| ATOM | 892 | CG | GLU | A | 350 | 17.131 | 2.456 | 4.554 | 1.00 | 27.95 | A | C |
| ATOM | 893 | CD | GLU | A | 350 | 18.572 | 2.010 | 4.314 | 1.00 | 28.87 | A | C |
| ATOM | 894 | OE1 | GLU | A | 350 | 19.458 | 2.860 | 4.106 | 1.00 | 28.91 | A | O |
| ATOM | 895 | OE2 | GLU | A | 350 | 18.819 | 0.791 | 4.334 | 1.00 | 30.73 | A | O |
| ATOM | 896 | C | GLU | A | 350 | 15.025 | 3.850 | 6.139 | 1.00 | 23.14 | A | C |
| ATOM | 897 | O | GLU | A | 350 | 14.345 | 2.823 | 6.149 | 1.00 | 23.75 | A | O |
| ATOM | 898 | N | GLY | A | 351 | 15.420 | 4.472 | 7.252 | 1.00 | 23.67 | A | N |
| ATOM | 899 | CA | GLY | A | 351 | 14.999 | 3.996 | 8.565 | 1.00 | 22.04 | A | C |
| ATOM | 900 | C | GLY | A | 351 | 13.494 | 4.162 | 8.733 | 1.00 | 22.33 | A | C |
| ATOM | 901 | O | GLY | A | 351 | 12.837 | 3.327 | 9.353 | 1.00 | 21.40 | A | O |
| ATOM | 902 | N | MET | A | 352 | 12.956 | 5.247 | 8.170 | 1.00 | 22.05 | A | N |
| ATOM | 903 | CA | MET | A | 352 | 11.529 | 5.550 | 8.215 | 1.00 | 22.06 | A | C |
| ATOM | 904 | CB | MET | A | 352 | 11.261 | 6.985 | 7.776 | 1.00 | 21.30 | A | C |
| ATOM | 905 | CG | MET | A | 352 | 11.551 | 8.046 | 8.831 | 1.00 | 20.72 | A | C |
| ATOM | 906 | SD | MET | A | 352 | 10.906 | 7.689 | 10.492 | 1.00 | 22.06 | A | S |
| ATOM | 907 | CE | MET | A | 352 | 9.112 | 7.336 | 10.171 | 1.00 | 20.10 | A | C |
| ATOM | 908 | C | MET | A | 352 | 10.745 | 4.588 | 7.342 | 1.00 | 22.54 | A | C |
| ATOM | 909 | O | MET | A | 352 | 9.593 | 4.278 | 7.632 | 1.00 | 22.59 | A | O |
| ATOM | 910 | N | ALA | A | 353 | 11.380 | 4.105 | 6.277 | 1.00 | 24.54 | A | N |
| ATOM | 911 | CA | ALA | A | 353 | 10.745 | 3.141 | 5.386 | 1.00 | 26.25 | A | C |
| ATOM | 912 | CB | ALA | A | 353 | 11.568 | 2.968 | 4.117 | 1.00 | 26.99 | A | C |
| ATOM | 913 | C | ALA | A | 353 | 10.616 | 1.808 | 6.133 | 1.00 | 28.25 | A | C |
| ATOM | 914 | O | ALA | A | 353 | 9.638 | 1.072 | 5.954 | 1.00 | 29.51 | A | O |
| ATOM | 915 | N | PHE | A | 354 | 11.621 | 1.486 | 6.946 | 1.00 | 28.37 | A | N |
| ATOM | 916 | CA | PHE | A | 354 | 11.595 | 0.266 | 7.744 | 1.00 | 26.86 | A | C |
| ATOM | 917 | CB | PHE | A | 354 | 12.952 | 0.041 | 8.435 | 1.00 | 25.79 | A | C |
| ATOM | 918 | CG | PHE | A | 354 | 12.957 | -1.122 | 9.409 | 1.00 | 24.64 | A | C |
| ATOM | 919 | CD1 | PHE | A | 354 | 12.853 | -2.438 | 8.952 | 1.00 | 25.00 | A | C |
| ATOM | 920 | CD2 | PHE | A | 354 | 13.080 | -0.899 | 10.776 | 1.00 | 24.63 | A | C |
| ATOM | 921 | CE1 | PHE | A | 354 | 12.872 | -3.511 | 9.843 | 1.00 | 24.48 | A | C |
| ATOM | 922 | CE2 | PHE | A | 354 | 13.101 | -1.961 | 11.675 | 1.00 | 23.72 | A | C |
| ATOM | 923 | CZ | PHE | A | 354 | 12.999 | -3.267 | 11.207 | 1.00 | 23.80 | A | C |
| ATOM | 924 | C | PHE | A | 354 | 10.486 | 0.390 | 8.795 | 1.00 | 25.21 | A | C |
| ATOM | 925 | O | PHE | A | 354 | 9.737 | -0.551 | 9.015 | 1.00 | 27.94 | A | O |
| ATOM | 926 | N | ILE | A | 355 | 10.411 | 1.554 | 9.441 | 1.00 | 24.44 | A | N |
| ATOM | 927 | CA | ILE | A | 355 | 9.416 | 1.859 | 10.480 | 1.00 | 24.16 | A | C |
| ATOM | 928 | CB | ILE | A | 355 | 9.698 | 3.279 | 11.108 | 1.00 | 23.09 | A | C |
| ATOM | 929 | CG2 | ILE | A | 355 | 8.488 | 3.810 | 11.883 | 1.00 | 21.00 | A | C |
| ATOM | 930 | CG1 | ILE | A | 355 | 10.955 | 3.218 | 12.002 | 1.00 | 21.79 | A | C |
| ATOM | 931 | CD1 | ILE | A | 355 | 11.484 | 4.562 | 12.449 | 1.00 | 19.16 | A | C |
| ATOM | 932 | C | ILE | A | 355 | 8.000 | 1.757 | 9.894 | 1.00 | 25.88 | A | C |
| ATOM | 933 | O | ILE | A | 355 | 7.101 | 1.178 | 10.508 | 1.00 | 25.95 | A | O |
| ATOM | 934 | N | GLU | A | 356 | 7.855 | 2.237 | 8.661 | 1.00 | 26.65 | A | N |
| ATOM | 935 | CA | GLU | A | 356 | 6.604 | 2.219 | 7.907 | 1.00 | 27.57 | A | C |
| ATOM | 936 | CB | GLU | A | 356 | 6.789 | 3.069 | 6.649 | 1.00 | 27.74 | A | C |
| ATOM | 937 | CG | GLU | A | 356 | 5.658 | 3.100 | 5.643 | 1.00 | 25.27 | A | C |
| ATOM | 938 | CD | GLU | A | 356 | 6.062 | 3.861 | 4.397 | 1.00 | 24.42 | A | C |
| ATOM | 939 | OE1 | GLU | A | 356 | 6.795 | 3.301 | 3.572 | 1.00 | 24.46 | A | O |
| ATOM | 940 | OE2 | GLU | A | 356 | 5.680 | 5.029 | 4.237 | 1.00 | 25.11 | A | O |
| ATOM | 941 | C | GLU | A | 356 | 6.232 | 0.788 | 7.532 | 1.00 | 29.32 | A | C |
| ATOM | 942 | O | GLU | A | 356 | 5.073 | 0.378 | 7.651 | 1.00 | 32.39 | A | O |
| ATOM | 943 | N | GLU | A | 357 | 7.231 | 0.030 | 7.111 | 1.00 | 29.96 | A | N |
| ATOM | 944 | CA | GLU | A | 357 | 7.072 | -1.360 | 6.732 | 1.00 | 32.71 | A | C |
| ATOM | 945 | CB | GLU | A | 357 | 8.448 | -1.892 | 6.341 | 1.00 | 36.39 | A | C |
| ATOM | 946 | CG | GLU | A | 357 | 8.611 | -3.398 | 6.414 | 1.00 | 40.01 | A | C |
| ATOM | 947 | CD | GLU | A | 357 | 8.120 | -4.085 | 5.165 | 1.00 | 41.77 | A | C |

Figure 4

| | | | | | | | | | | |
|---|---|---|---|---|---|---|---|---|---|---|
|ATOM|948|OE1|GLU|A|357|8.740|-3.843|4.106|1.00 43.70|A O|
|ATOM|949|OE2|GLU|A|357|7.132|-4.857|5.238|1.00 43.04|A O|
|ATOM|950|C|GLU|A|357|6.518|-2.191|7.896|1.00 33.48|A C|
|ATOM|951|O|GLU|A|357|5.646|-3.053|7.715|1.00 33.22|A O|
|ATOM|952|N|ARG|A|358|7.031|-1.913|9.089|1.00 34.57|A N|
|ATOM|953|CA|ARG|A|358|6.648|-2.628|10.294|1.00 37.64|A C|
|ATOM|954|CB|ARG|A|358|7.814|-2.615|11.277|1.00 38.91|A C|
|ATOM|955|CG|ARG|A|358|9.079|-3.241|10.699|1.00 42.50|A C|
|ATOM|956|CD|ARG|A|358|8.977|-4.757|10.545|1.00 46.27|A C|
|ATOM|957|NE|ARG|A|358|8.821|-5.420|11.845|1.00 52.44|A N|
|ATOM|958|CZ|ARG|A|358|9.713|-5.381|12.845|1.00 55.14|A C|
|ATOM|959|NH1|ARG|A|358|10.850|-4.715|12.721|1.00 56.98|A N|
|ATOM|960|NH2|ARG|A|358|9.467|-5.990|13.997|1.00 56.70|A N|
|ATOM|961|C|ARG|A|358|5.377|-2.111|10.957|1.00 37.80|A C|
|ATOM|962|O|ARG|A|358|4.966|-2.620|11.998|1.00 38.77|A O|
|ATOM|963|N|ASN|A|359|4.764|-1.101|10.348|1.00 39.10|A N|
|ATOM|964|CA|ASN|A|359|3.517|-0.489|10.831|1.00 39.72|A C|
|ATOM|965|CB|ASN|A|359|2.386|-1.516|10.838|1.00 42.40|A C|
|ATOM|966|CG|ASN|A|359|2.257|-2.231|9.490|1.00 45.70|A C|
|ATOM|967|OD1|ASN|A|359|1.910|-1.608|8.464|1.00 46.28|A O|
|ATOM|968|ND2|ASN|A|359|2.599|-3.531|9.470|1.00 45.25|A N|
|ATOM|969|C|ASN|A|359|3.584|0.307|12.138|1.00 37.74|A C|
|ATOM|970|O|ASN|A|359|2.701|0.234|13.000|1.00 36.33|A O|
|ATOM|971|N|TYR|A|360|4.638|1.108|12.232|1.00 35.15|A N|
|ATOM|972|CA|TYR|A|360|4.875|2.000|13.352|1.00 32.41|A C|
|ATOM|973|CB|TYR|A|360|6.286|1.789|13.918|1.00 33.72|A C|
|ATOM|974|CG|TYR|A|360|6.434|0.633|14.869|1.00 34.86|A C|
|ATOM|975|CD1|TYR|A|360|6.421|-0.683|14.406|1.00 35.86|A C|
|ATOM|976|CE1|TYR|A|360|6.541|-1.752|15.272|1.00 35.96|A C|
|ATOM|977|CD2|TYR|A|360|6.575|0.854|16.233|1.00 35.62|A C|
|ATOM|978|CE2|TYR|A|360|6.699|-0.211|17.112|1.00 37.58|A C|
|ATOM|979|CZ|TYR|A|360|6.676|-1.513|16.621|1.00 38.02|A C|
|ATOM|980|OH|TYR|A|360|6.774|-2.576|17.489|1.00 40.40|A O|
|ATOM|981|C|TYR|A|360|4.837|3.407|12.765|1.00 30.99|A C|
|ATOM|982|O|TYR|A|360|4.678|3.602|11.555|1.00 31.29|A O|
|ATOM|983|N|ILE|A|361|4.971|4.387|13.643|1.00 28.78|A N|
|ATOM|984|CA|ILE|A|361|5.054|5.775|13.242|1.00 28.11|A C|
|ATOM|985|CB|ILE|A|361|3.742|6.557|13.501|1.00 26.64|A C|
|ATOM|986|CG2|ILE|A|361|2.583|5.895|12.734|1.00 24.36|A C|
|ATOM|987|CG1|ILE|A|361|3.458|6.639|15.006|1.00 26.36|A C|
|ATOM|988|CD1|ILE|A|361|2.621|7.827|15.415|1.00 25.81|A C|
|ATOM|989|C|ILE|A|361|6.186|6.291|14.141|1.00 29.17|A C|
|ATOM|990|O|ILE|A|361|6.663|5.578|15.036|1.00 30.59|A O|
|ATOM|991|N|HIS|A|362|6.646|7.504|13.899|1.00 28.44|A N|
|ATOM|992|CA|HIS|A|362|7.706|8.053|14.717|1.00 26.94|A C|
|ATOM|993|CB|HIS|A|362|8.709|8.811|13.850|1.00 25.14|A C|
|ATOM|994|CG|HIS|A|362|9.954|9.199|14.577|1.00 22.61|A C|
|ATOM|995|CD2|HIS|A|362|11.235|8.811|14.409|1.00 21.63|A C|
|ATOM|996|ND1|HIS|A|362|9.956|10.074|15.642|1.00 21.42|A N|
|ATOM|997|CE1|HIS|A|362|11.185|10.210|16.099|1.00 22.00|A C|
|ATOM|998|NE2|HIS|A|362|11.982|9.451|15.366|1.00 22.38|A N|
|ATOM|999|C|HIS|A|362|7.051|9.009|15.684|1.00 28.91|A C|
|ATOM|1000|O|HIS|A|362|7.140|8.824|16.888|1.00 29.76|A O|
|ATOM|1001|N|ARG|A|363|6.339|9.973|15.095|1.00 29.67|A N|
|ATOM|1002|CA|ARG|A|363|5.588|11.080|15.706|1.00 29.77|A C|
|ATOM|1003|CB|ARG|A|363|4.486|10.641|16.708|1.00 35.57|A C|
|ATOM|1004|CG|ARG|A|363|4.926|9.840|17.943|1.00 39.62|A C|
|ATOM|1005|CD|ARG|A|363|3.738|9.329|18.775|1.00 41.42|A C|
|ATOM|1006|NE|ARG|A|363|3.045|10.415|19.460|1.00 41.78|A N|
|ATOM|1007|CZ|ARG|A|363|1.751|10.673|19.315|1.00 43.02|A C|

Figure 4

| | | | | | | | | | | | |
|---|---|---|---|---|---|---|---|---|---|---|---|
| ATOM | 1008 | NH1 | ARG | A | 363 | 1.017 | 9.915 | 18.511 | 1.00 | 42.70 | A N |
| ATOM | 1009 | NH2 | ARG | A | 363 | 1.198 | 11.710 | 19.936 | 1.00 | 43.53 | A N |
| ATOM | 1010 | C | ARG | A | 363 | 6.428 | 12.228 | 16.225 | 1.00 | 27.78 | A C |
| ATOM | 1011 | O | ARG | A | 363 | 5.903 | 13.297 | 16.499 | 1.00 | 24.58 | A O |
| ATOM | 1012 | N | ASP | A | 364 | 7.748 | 12.046 | 16.234 | 1.00 | 26.23 | A N |
| ATOM | 1013 | CA | ASP | A | 364 | 8.662 | 13.074 | 16.706 | 1.00 | 25.47 | A C |
| ATOM | 1014 | CB | ASP | A | 364 | 9.200 | 12.694 | 18.077 | 1.00 | 25.98 | A C |
| ATOM | 1015 | CG | ASP | A | 364 | 8.220 | 12.967 | 19.178 | 1.00 | 24.87 | A C |
| ATOM | 1016 | OD1 | ASP | A | 364 | 7.969 | 14.165 | 19.460 | 1.00 | 24.80 | A O |
| ATOM | 1017 | OD2 | ASP | A | 364 | 7.727 | 11.981 | 19.764 | 1.00 | 25.11 | A O |
| ATOM | 1018 | C | ASP | A | 364 | 9.830 | 13.307 | 15.747 | 1.00 | 26.62 | A C |
| ATOM | 1019 | O | ASP | A | 364 | 10.896 | 13.781 | 16.143 | 1.00 | 24.70 | A O |
| ATOM | 1020 | N | LEU | A | 365 | 9.602 | 12.993 | 14.477 | 1.00 | 26.57 | A N |
| ATOM | 1021 | CA | LEU | A | 365 | 10.589 | 13.137 | 13.419 | 1.00 | 24.74 | A C |
| ATOM | 1022 | CB | LEU | A | 365 | 10.062 | 12.459 | 12.155 | 1.00 | 24.17 | A C |
| ATOM | 1023 | CG | LEU | A | 365 | 11.031 | 12.297 | 10.993 | 1.00 | 24.55 | A C |
| ATOM | 1024 | CD1 | LEU | A | 365 | 12.262 | 11.518 | 11.487 | 1.00 | 24.99 | A C |
| ATOM | 1025 | CD2 | LEU | A | 365 | 10.333 | 11.584 | 9.823 | 1.00 | 22.69 | A C |
| ATOM | 1026 | C | LEU | A | 365 | 10.970 | 14.584 | 13.117 | 1.00 | 25.37 | A C |
| ATOM | 1027 | O | LEU | A | 365 | 10.149 | 15.394 | 12.714 | 1.00 | 26.45 | A O |
| ATOM | 1028 | N | ARG | A | 366 | 12.229 | 14.901 | 13.364 | 1.00 | 25.95 | A N |
| ATOM | 1029 | CA | ARG | A | 366 | 12.799 | 16.219 | 13.109 | 1.00 | 26.34 | A C |
| ATOM | 1030 | CB | ARG | A | 366 | 12.308 | 17.267 | 14.114 | 1.00 | 28.35 | A C |
| ATOM | 1031 | CG | ARG | A | 366 | 12.633 | 17.014 | 15.565 | 1.00 | 31.81 | A C |
| ATOM | 1032 | CD | ARG | A | 366 | 12.344 | 18.259 | 16.392 | 1.00 | 34.12 | A C |
| ATOM | 1033 | NE | ARG | A | 366 | 12.003 | 17.927 | 17.770 | 1.00 | 37.36 | A N |
| ATOM | 1034 | CZ | ARG | A | 366 | 10.886 | 17.292 | 18.109 | 1.00 | 39.43 | A C |
| ATOM | 1035 | NH1 | ARG | A | 366 | 10.018 | 16.929 | 17.161 | 1.00 | 41.38 | A N |
| ATOM | 1036 | NH2 | ARG | A | 366 | 10.627 | 17.025 | 19.382 | 1.00 | 39.35 | A N |
| ATOM | 1037 | C | ARG | A | 366 | 14.313 | 16.013 | 13.171 | 1.00 | 25.91 | A C |
| ATOM | 1038 | O | ARG | A | 366 | 14.757 | 14.959 | 13.633 | 1.00 | 26.21 | A O |
| ATOM | 1039 | N | ALA | A | 367 | 15.102 | 16.956 | 12.664 | 1.00 | 24.69 | A N |
| ATOM | 1040 | CA | ALA | A | 367 | 16.565 | 16.785 | 12.669 | 1.00 | 25.84 | A C |
| ATOM | 1041 | CB | ALA | A | 367 | 17.249 | 17.916 | 11.925 | 1.00 | 24.55 | A C |
| ATOM | 1042 | C | ALA | A | 367 | 17.164 | 16.622 | 14.070 | 1.00 | 26.25 | A C |
| ATOM | 1043 | O | ALA | A | 367 | 18.167 | 15.924 | 14.238 | 1.00 | 26.37 | A O |
| ATOM | 1044 | N | ALA | A | 368 | 16.522 | 17.226 | 15.072 | 1.00 | 24.80 | A N |
| ATOM | 1045 | CA | ALA | A | 368 | 16.977 | 17.138 | 16.451 | 1.00 | 23.78 | A C |
| ATOM | 1046 | CB | ALA | A | 368 | 16.088 | 17.982 | 17.352 | 1.00 | 22.89 | A C |
| ATOM | 1047 | C | ALA | A | 368 | 16.986 | 15.695 | 16.927 | 1.00 | 23.25 | A C |
| ATOM | 1048 | O | ALA | A | 368 | 17.820 | 15.308 | 17.730 | 1.00 | 23.63 | A O |
| ATOM | 1049 | N | ASN | A | 369 | 16.104 | 14.882 | 16.369 | 1.00 | 23.46 | A N |
| ATOM | 1050 | CA | ASN | A | 369 | 15.999 | 13.486 | 16.758 | 1.00 | 24.34 | A C |
| ATOM | 1051 | CB | ASN | A | 369 | 14.532 | 13.138 | 17.028 | 1.00 | 24.00 | A C |
| ATOM | 1052 | CG | ASN | A | 369 | 13.940 | 14.017 | 18.111 | 1.00 | 24.16 | A C |
| ATOM | 1053 | OD1 | ASN | A | 369 | 14.573 | 14.235 | 19.153 | 1.00 | 25.29 | A O |
| ATOM | 1054 | ND2 | ASN | A | 369 | 12.791 | 14.612 | 17.839 | 1.00 | 23.50 | A N |
| ATOM | 1055 | C | ASN | A | 369 | 16.703 | 12.487 | 15.843 | 1.00 | 23.64 | A C |
| ATOM | 1056 | O | ASN | A | 369 | 16.393 | 11.288 | 15.838 | 1.00 | 23.58 | A O |
| ATOM | 1057 | N | ILE | A | 370 | 17.648 | 13.004 | 15.060 | 1.00 | 21.94 | A N |
| ATOM | 1058 | CA | ILE | A | 370 | 18.469 | 12.172 | 14.195 | 1.00 | 21.24 | A C |
| ATOM | 1059 | CB | ILE | A | 370 | 18.466 | 12.637 | 12.708 | 1.00 | 20.68 | A C |
| ATOM | 1060 | CG2 | ILE | A | 370 | 19.296 | 11.651 | 11.835 | 1.00 | 17.57 | A C |
| ATOM | 1061 | CG1 | ILE | A | 370 | 17.030 | 12.689 | 12.181 | 1.00 | 20.52 | A C |
| ATOM | 1062 | CD1 | ILE | A | 370 | 16.352 | 11.322 | 12.084 | 1.00 | 18.91 | A C |
| ATOM | 1063 | C | ILE | A | 370 | 19.897 | 12.296 | 14.755 | 1.00 | 21.70 | A C |
| ATOM | 1064 | O | ILE | A | 370 | 20.344 | 13.377 | 15.136 | 1.00 | 20.16 | A O |
| ATOM | 1065 | N | LEU | A | 371 | 20.590 | 11.173 | 14.844 | 1.00 | 23.30 | A N |
| ATOM | 1066 | CA | LEU | A | 371 | 21.943 | 11.179 | 15.345 | 1.00 | 23.71 | A C |
| ATOM | 1067 | CB | LEU | A | 371 | 22.086 | 10.169 | 16.480 | 1.00 | 22.42 | A C |

Figure 4

| | | | | | | | | | | | |
|---|---|---|---|---|---|---|---|---|---|---|---|
| ATOM | 1068 | CG | LEU | A | 371 | 21.201 | 10.432 | 17.695 | 1.00 | 20.92 | A C |
| ATOM | 1069 | CD1 | LEU | A | 371 | 21.419 | 9.345 | 18.728 | 1.00 | 20.55 | A C |
| ATOM | 1070 | CD2 | LEU | A | 371 | 21.476 | 11.812 | 18.281 | 1.00 | 20.48 | A C |
| ATOM | 1071 | C | LEU | A | 371 | 22.908 | 10.875 | 14.208 | 1.00 | 25.26 | A C |
| ATOM | 1072 | O | LEU | A | 371 | 22.571 | 10.149 | 13.264 | 1.00 | 24.75 | A O |
| ATOM | 1073 | N | VAL | A | 372 | 24.108 | 11.446 | 14.317 | 1.00 | 27.11 | A N |
| ATOM | 1074 | CA | VAL | A | 372 | 25.169 | 11.313 | 13.322 | 1.00 | 27.63 | A C |
| ATOM | 1075 | CB | VAL | A | 372 | 25.612 | 12.717 | 12.827 | 1.00 | 26.99 | A C |
| ATOM | 1076 | CG1 | VAL | A | 372 | 26.528 | 12.598 | 11.606 | 1.00 | 27.11 | A C |
| ATOM | 1077 | CG2 | VAL | A | 372 | 24.398 | 13.584 | 12.528 | 1.00 | 25.86 | A C |
| ATOM | 1078 | C | VAL | A | 372 | 26.403 | 10.606 | 13.908 | 1.00 | 29.29 | A C |
| ATOM | 1079 | O | VAL | A | 372 | 26.916 | 11.004 | 14.965 | 1.00 | 30.28 | A O |
| ATOM | 1080 | N | SER | A | 373 | 26.887 | 9.577 | 13.213 | 1.00 | 30.24 | A N |
| ATOM | 1081 | CA | SER | A | 373 | 28.067 | 8.841 | 13.660 | 1.00 | 31.02 | A C |
| ATOM | 1082 | CB | SER | A | 373 | 28.060 | 7.418 | 13.102 | 1.00 | 29.92 | A C |
| ATOM | 1083 | OG | SER | A | 373 | 28.355 | 7.417 | 11.717 | 1.00 | 29.30 | A O |
| ATOM | 1084 | C | SER | A | 373 | 29.374 | 9.537 | 13.249 | 1.00 | 32.84 | A C |
| ATOM | 1085 | O | SER | A | 373 | 29.365 | 10.625 | 12.659 | 1.00 | 31.23 | A O |
| ATOM | 1086 | N | ASP | A | 374 | 30.495 | 8.900 | 13.589 | 1.00 | 35.99 | A N |
| ATOM | 1087 | CA | ASP | A | 374 | 31.817 | 9.416 | 13.246 | 1.00 | 37.75 | A C |
| ATOM | 1088 | CB | ASP | A | 374 | 32.927 | 8.720 | 14.065 | 1.00 | 39.56 | A C |
| ATOM | 1089 | CG | ASP | A | 374 | 32.850 | 7.205 | 14.006 | 1.00 | 41.82 | A C |
| ATOM | 1090 | OD1 | ASP | A | 374 | 31.831 | 6.637 | 14.451 | 1.00 | 43.77 | A O |
| ATOM | 1091 | OD2 | ASP | A | 374 | 33.824 | 6.574 | 13.540 | 1.00 | 43.70 | A O |
| ATOM | 1092 | C | ASP | A | 374 | 32.057 | 9.315 | 11.736 | 1.00 | 37.12 | A C |
| ATOM | 1093 | O | ASP | A | 374 | 32.749 | 10.154 | 11.161 | 1.00 | 37.12 | A O |
| ATOM | 1094 | N | THR | A | 375 | 31.424 | 8.337 | 11.086 | 1.00 | 36.87 | A N |
| ATOM | 1095 | CA | THR | A | 375 | 31.542 | 8.177 | 9.641 | 1.00 | 36.55 | A C |
| ATOM | 1096 | CB | THR | A | 375 | 31.483 | 6.707 | 9.212 | 1.00 | 36.31 | A C |
| ATOM | 1097 | OG1 | THR | A | 375 | 30.170 | 6.184 | 9.433 | 1.00 | 38.46 | A O |
| ATOM | 1098 | CG2 | THR | A | 375 | 32.481 | 5.890 | 9.981 | 1.00 | 36.60 | A C |
| ATOM | 1099 | C | THR | A | 375 | 30.405 | 8.945 | 8.952 | 1.00 | 37.62 | A C |
| ATOM | 1100 | O | THR | A | 375 | 30.037 | 8.649 | 7.814 | 1.00 | 39.09 | A O |
| ATOM | 1101 | N | LEU | A | 376 | 29.829 | 9.900 | 9.682 | 1.00 | 38.27 | A N |
| ATOM | 1102 | CA | LEU | A | 376 | 28.750 | 10.770 | 9.219 | 1.00 | 38.74 | A C |
| ATOM | 1103 | CB | LEU | A | 376 | 29.265 | 11.777 | 8.196 | 1.00 | 40.57 | A C |
| ATOM | 1104 | CG | LEU | A | 376 | 30.528 | 12.550 | 8.585 | 1.00 | 42.12 | A C |
| ATOM | 1105 | CD1 | LEU | A | 376 | 30.798 | 13.598 | 7.528 | 1.00 | 43.28 | A C |
| ATOM | 1106 | CD2 | LEU | A | 376 | 30.381 | 13.194 | 9.958 | 1.00 | 42.55 | A C |
| ATOM | 1107 | C | LEU | A | 376 | 27.475 | 10.123 | 8.708 | 1.00 | 38.78 | A C |
| ATOM | 1108 | O | LEU | A | 376 | 26.721 | 10.751 | 7.962 | 1.00 | 37.17 | A O |
| ATOM | 1109 | N | SER | A | 377 | 27.228 | 8.878 | 9.117 | 1.00 | 38.78 | A N |
| ATOM | 1110 | CA | SER | A | 377 | 26.010 | 8.171 | 8.725 | 1.00 | 38.46 | A C |
| ATOM | 1111 | CB | SER | A | 377 | 26.240 | 6.656 | 8.681 | 1.00 | 39.26 | A C |
| ATOM | 1112 | OG | SER | A | 377 | 26.415 | 6.125 | 9.983 | 1.00 | 40.81 | A O |
| ATOM | 1113 | C | SER | A | 377 | 24.906 | 8.515 | 9.740 | 1.00 | 38.17 | A C |
| ATOM | 1114 | O | SER | A | 377 | 25.177 | 8.649 | 10.946 | 1.00 | 39.02 | A O |
| ATOM | 1115 | N | CYS | A | 378 | 23.666 | 8.643 | 9.260 | 1.00 | 35.37 | A N |
| ATOM | 1116 | CA | CYS | A | 378 | 22.543 | 9.004 | 10.126 | 1.00 | 32.22 | A C |
| ATOM | 1117 | CB | CYS | A | 378 | 21.640 | 10.026 | 9.429 | 1.00 | 31.24 | A C |
| ATOM | 1118 | SG | CYS | A | 378 | 22.470 | 11.568 | 8.981 | 1.00 | 29.62 | A S |
| ATOM | 1119 | C | CYS | A | 378 | 21.698 | 7.838 | 10.623 | 1.00 | 30.84 | A C |
| ATOM | 1120 | O | CYS | A | 378 | 21.467 | 6.858 | 9.901 | 1.00 | 31.12 | A O |
| ATOM | 1121 | N | LYS | A | 379 | 21.263 | 7.960 | 11.880 | 1.00 | 29.13 | A N |
| ATOM | 1122 | CA | LYS | A | 379 | 20.404 | 6.977 | 12.547 | 1.00 | 26.98 | A C |
| ATOM | 1123 | CB | LYS | A | 379 | 21.226 | 6.126 | 13.524 | 1.00 | 25.37 | A C |
| ATOM | 1124 | CG | LYS | A | 379 | 21.896 | 4.898 | 12.890 | 1.00 | 25.92 | A C |
| ATOM | 1125 | CD | LYS | A | 379 | 23.076 | 4.387 | 13.742 | 1.00 | 27.57 | A C |
| ATOM | 1126 | CE | LYS | A | 379 | 23.638 | 3.018 | 13.319 | 1.00 | 28.14 | A C |
| ATOM | 1127 | NZ | LYS | A | 379 | 22.834 | 1.834 | 13.857 | 1.00 | 30.73 | A N |

Figure 4

| | | | | | | | | | | |
|---|---|---|---|---|---|---|---|---|---|---|
| ATOM | 1128 | C | LYS | A | 379 | 19.205 | 7.677 | 13.256 | 1.00 25.82 | A C |
| ATOM | 1129 | O | LYS | A | 379 | 19.330 | 8.783 | 13.815 | 1.00 25.36 | A O |
| ATOM | 1130 | N | ILE | A | 380 | 18.041 | 7.037 | 13.203 | 1.00 25.22 | A N |
| ATOM | 1131 | CA | ILE | A | 380 | 16.814 | 7.571 | 13.802 | 1.00 25.30 | A C |
| ATOM | 1132 | CB | ILE | A | 380 | 15.556 | 7.059 | 13.039 | 1.00 26.39 | A C |
| ATOM | 1133 | CG2 | ILE | A | 380 | 14.301 | 7.573 | 13.679 | 1.00 25.00 | A C |
| ATOM | 1134 | CG1 | ILE | A | 380 | 15.594 | 7.514 | 11.577 | 1.00 27.32 | A C |
| ATOM | 1135 | CD1 | ILE | A | 380 | 14.470 | 6.960 | 10.752 | 1.00 27.44 | A C |
| ATOM | 1136 | C | ILE | A | 380 | 16.676 | 7.206 | 15.283 | 1.00 24.64 | A C |
| ATOM | 1137 | O | ILE | A | 380 | 16.729 | 6.028 | 15.664 | 1.00 24.90 | A O |
| ATOM | 1138 | N | ALA | A | 381 | 16.479 | 8.221 | 16.114 | 1.00 24.28 | A N |
| ATOM | 1139 | CA | ALA | A | 381 | 16.313 | 8.008 | 17.546 | 1.00 25.53 | A C |
| ATOM | 1140 | CB | ALA | A | 381 | 17.371 | 8.785 | 18.312 | 1.00 24.35 | A C |
| ATOM | 1141 | C | ALA | A | 381 | 14.921 | 8.434 | 18.022 | 1.00 25.28 | A C |
| ATOM | 1142 | O | ALA | A | 381 | 14.229 | 9.203 | 17.349 | 1.00 24.61 | A O |
| ATOM | 1143 | N | ASP | A | 382 | 14.536 | 7.924 | 19.192 | 1.00 25.70 | A N |
| ATOM | 1144 | CA | ASP | A | 382 | 13.272 | 8.259 | 19.848 | 1.00 25.56 | A C |
| ATOM | 1145 | CB | ASP | A | 382 | 13.361 | 9.668 | 20.468 | 1.00 25.65 | A C |
| ATOM | 1146 | CG | ASP | A | 382 | 14.264 | 9.717 | 21.683 | 1.00 24.70 | A C |
| ATOM | 1147 | OD1 | ASP | A | 382 | 14.337 | 8.715 | 22.418 | 1.00 27.60 | A O |
| ATOM | 1148 | OD2 | ASP | A | 382 | 14.897 | 10.760 | 21.906 | 1.00 24.90 | A O |
| ATOM | 1149 | C | ASP | A | 382 | 12.021 | 8.125 | 18.997 | 1.00 25.53 | A C |
| ATOM | 1150 | O | ASP | A | 382 | 11.175 | 9.012 | 18.959 | 1.00 24.60 | A O |
| ATOM | 1151 | N | PHE | A | 383 | 11.902 | 6.990 | 18.334 | 1.00 27.65 | A N |
| ATOM | 1152 | CA | PHE | A | 383 | 10.758 | 6.693 | 17.481 | 1.00 29.95 | A C |
| ATOM | 1153 | CB | PHE | A | 383 | 11.234 | 5.924 | 16.245 | 1.00 29.78 | A C |
| ATOM | 1154 | CG | PHE | A | 383 | 12.001 | 4.675 | 16.578 | 1.00 32.52 | A C |
| ATOM | 1155 | CD1 | PHE | A | 383 | 11.366 | 3.426 | 16.581 | 1.00 32.53 | A C |
| ATOM | 1156 | CD2 | PHE | A | 383 | 13.348 | 4.756 | 16.966 | 1.00 33.60 | A C |
| ATOM | 1157 | CE1 | PHE | A | 383 | 12.057 | 2.283 | 16.973 | 1.00 33.09 | A C |
| ATOM | 1158 | CE2 | PHE | A | 383 | 14.046 | 3.620 | 17.361 | 1.00 34.16 | A C |
| ATOM | 1159 | CZ | PHE | A | 383 | 13.402 | 2.381 | 17.368 | 1.00 33.35 | A C |
| ATOM | 1160 | C | PHE | A | 383 | 9.748 | 5.836 | 18.242 | 1.00 30.27 | A C |
| ATOM | 1161 | O | PHE | A | 383 | 10.104 | 5.128 | 19.193 | 1.00 32.82 | A O |
| ATOM | 1162 | N | GLY | A | 384 | 8.492 | 5.902 | 17.822 | 1.00 30.14 | A N |
| ATOM | 1163 | CA | GLY | A | 384 | 7.461 | 5.097 | 18.444 | 1.00 29.90 | A C |
| ATOM | 1164 | C | GLY | A | 384 | 7.063 | 5.439 | 19.863 | 1.00 30.84 | A C |
| ATOM | 1165 | O | GLY | A | 384 | 6.392 | 4.637 | 20.481 | 1.00 32.86 | A O |
| ATOM | 1166 | N | LEU | A | 385 | 7.470 | 6.590 | 20.395 | 1.00 31.15 | A N |
| ATOM | 1167 | CA | LEU | A | 385 | 7.098 | 6.985 | 21.762 | 1.00 33.33 | A C |
| ATOM | 1168 | CB | LEU | A | 385 | 7.951 | 8.186 | 22.232 | 1.00 31.89 | A C |
| ATOM | 1169 | CG | LEU | A | 385 | 9.485 | 8.068 | 22.146 | 1.00 30.91 | A C |
| ATOM | 1170 | CD1 | LEU | A | 385 | 10.111 | 9.350 | 22.627 | 1.00 30.32 | A C |
| ATOM | 1171 | CD2 | LEU | A | 385 | 10.015 | 6.902 | 22.960 | 1.00 29.77 | A C |
| ATOM | 1172 | C | LEU | A | 385 | 5.594 | 7.354 | 21.831 | 1.00 35.87 | A C |
| ATOM | 1173 | O | LEU | A | 385 | 5.012 | 7.834 | 20.853 | 1.00 35.25 | A O |
| ATOM | 1174 | N | ALA | A | 386 | 4.972 | 7.093 | 22.981 | 1.00 37.12 | A N |
| ATOM | 1175 | CA | ALA | A | 386 | 3.546 | 7.395 | 23.185 | 1.00 38.13 | A C |
| ATOM | 1176 | CB | ALA | A | 386 | 3.027 | 6.626 | 24.392 | 1.00 37.73 | A C |
| ATOM | 1177 | C | ALA | A | 386 | 3.290 | 8.869 | 23.384 | 1.00 38.32 | A C |
| ATOM | 1178 | O | ALA | A | 386 | 2.151 | 9.321 | 23.358 | 1.00 38.49 | A O |
| ATOM | 1179 | N | ARG | A | 387 | 4.363 | 9.626 | 23.566 | 1.00 38.61 | A N |
| ATOM | 1180 | CA | ARG | A | 387 | 4.260 | 11.060 | 23.802 | 1.00 37.40 | A C |
| ATOM | 1181 | CB | ARG | A | 387 | 4.730 | 11.358 | 25.234 | 1.00 37.59 | A C |
| ATOM | 1182 | CG | ARG | A | 387 | 6.180 | 10.944 | 25.505 | 1.00 37.93 | A C |
| ATOM | 1183 | CD | ARG | A | 387 | 6.642 | 11.411 | 26.877 | 1.00 37.96 | A C |
| ATOM | 1184 | NE | ARG | A | 387 | 8.084 | 11.274 | 27.031 | 1.00 38.15 | A N |
| ATOM | 1185 | CZ | ARG | A | 387 | 8.940 | 12.276 | 26.898 | 1.00 39.26 | A C |
| ATOM | 1186 | NH1 | ARG | A | 387 | 8.501 | 13.501 | 26.619 | 1.00 40.10 | A N |
| ATOM | 1187 | NH2 | ARG | A | 387 | 10.241 | 12.042 | 27.012 | 1.00 41.33 | A N |

Figure 4

| | | | | | | | | | | | |
|---|---|---|---|---|---|---|---|---|---|---|---|
| ATOM | 1188 | C | ARG | A | 387 | 5.064 | 11.913 | 22.822 | 1.00 | 36.40 | A C |
| ATOM | 1189 | O | ARG | A | 387 | 5.887 | 11.400 | 22.065 | 1.00 | 37.58 | A O |
| ATOM | 1190 | N | LEU | A | 388 | 4.807 | 13.221 | 22.847 | 1.00 | 34.55 | A N |
| ATOM | 1191 | CA | LEU | A | 388 | 5.512 | 14.177 | 22.015 | 1.00 | 31.57 | A C |
| ATOM | 1192 | CB | LEU | A | 388 | 4.550 | 15.267 | 21.561 | 1.00 | 30.67 | A C |
| ATOM | 1193 | CG | LEU | A | 388 | 3.317 | 14.760 | 20.815 | 1.00 | 31.65 | A C |
| ATOM | 1194 | CD1 | LEU | A | 388 | 2.306 | 15.882 | 20.655 | 1.00 | 30.39 | A C |
| ATOM | 1195 | CD2 | LEU | A | 388 | 3.724 | 14.176 | 19.460 | 1.00 | 30.55 | A C |
| ATOM | 1196 | C | LEU | A | 388 | 6.631 | 14.782 | 22.863 | 1.00 | 30.56 | A C |
| ATOM | 1197 | O | LEU | A | 388 | 6.376 | 15.446 | 23.866 | 1.00 | 31.83 | A O |
| ATOM | 1198 | N | ILE | A | 389 | 7.870 | 14.582 | 22.417 | 1.00 | 30.07 | A N |
| ATOM | 1199 | CA | ILE | A | 389 | 9.045 | 15.067 | 23.156 | 1.00 | 27.91 | A C |
| ATOM | 1200 | CB | ILE | A | 389 | 10.228 | 14.054 | 23.069 | 1.00 | 26.03 | A C |
| ATOM | 1201 | CG2 | ILE | A | 389 | 9.769 | 12.649 | 23.465 | 1.00 | 25.80 | A C |
| ATOM | 1202 | CG1 | ILE | A | 389 | 10.822 | 14.024 | 21.651 | 1.00 | 24.69 | A C |
| ATOM | 1203 | CD1 | ILE | A | 389 | 11.707 | 12.824 | 21.386 | 1.00 | 23.88 | A C |
| ATOM | 1204 | C | ILE | A | 389 | 9.520 | 16.464 | 22.725 | 1.00 | 29.43 | A C |
| ATOM | 1205 | O | ILE | A | 389 | 9.182 | 16.964 | 21.640 | 1.00 | 30.37 | A O |
| ATOM | 1206 | N | GLU | A | 390 | 10.291 | 17.082 | 23.586 | 1.00 | 31.19 | A N |
| ATOM | 1207 | CA | GLU | A | 390 | 10.874 | 18.376 | 23.325 | 1.00 | 33.30 | A C |
| ATOM | 1208 | CB | GLU | A | 390 | 10.363 | 19.419 | 24.313 | 1.00 | 33.22 | A C |
| ATOM | 1209 | CG | GLU | A | 390 | 8.838 | 19.604 | 24.220 | 1.00 | 36.48 | A C |
| ATOM | 1210 | CD | GLU | A | 390 | 8.322 | 20.735 | 25.069 | 1.00 | 37.50 | A C |
| ATOM | 1211 | OE1 | GLU | A | 390 | 7.089 | 20.834 | 25.240 | 1.00 | 39.01 | A O |
| ATOM | 1212 | OE2 | GLU | A | 390 | 9.144 | 21.523 | 25.576 | 1.00 | 39.43 | A O |
| ATOM | 1213 | C | GLU | A | 390 | 12.402 | 18.265 | 23.404 | 1.00 | 33.69 | A C |
| ATOM | 1214 | O | GLU | A | 390 | 12.957 | 17.352 | 24.033 | 1.00 | 34.08 | A O |
| ATOM | 1215 | N | ASP | A | 391 | 13.028 | 19.221 | 22.758 | 1.00 | 34.07 | A N |
| ATOM | 1216 | CA | ASP | A | 391 | 14.479 | 19.224 | 22.682 | 1.00 | 35.78 | A C |
| ATOM | 1217 | CB | ASP | A | 391 | 14.963 | 20.185 | 21.592 | 1.00 | 36.68 | A C |
| ATOM | 1218 | CG | ASP | A | 391 | 14.399 | 19.871 | 20.230 | 1.00 | 38.10 | A C |
| ATOM | 1219 | OD1 | ASP | A | 391 | 14.106 | 18.685 | 19.951 | 1.00 | 39.38 | A O |
| ATOM | 1220 | OD2 | ASP | A | 391 | 14.242 | 20.811 | 19.434 | 1.00 | 40.10 | A O |
| ATOM | 1221 | C | ASP | A | 391 | 15.165 | 19.569 | 24.008 | 1.00 | 36.48 | A C |
| ATOM | 1222 | O | ASP | A | 391 | 16.249 | 19.069 | 24.271 | 1.00 | 39.05 | A O |
| ATOM | 1223 | N | ASN | A | 392 | 14.534 | 20.405 | 24.833 | 1.00 | 36.21 | A N |
| ATOM | 1224 | CA | ASN | A | 392 | 15.100 | 20.798 | 26.128 | 1.00 | 35.11 | A C |
| ATOM | 1225 | CB | ASN | A | 392 | 14.401 | 22.075 | 26.636 | 1.00 | 36.58 | A C |
| ATOM | 1226 | CG | ASN | A | 392 | 12.947 | 21.824 | 27.116 | 1.00 | 37.59 | A C |
| ATOM | 1227 | OD1 | ASN | A | 392 | 12.400 | 20.726 | 26.977 | 1.00 | 38.00 | A O |
| ATOM | 1228 | ND2 | ASN | A | 392 | 12.332 | 22.855 | 27.692 | 1.00 | 38.52 | A N |
| ATOM | 1229 | C | ASN | A | 392 | 15.057 | 19.720 | 27.233 | 1.00 | 33.63 | A C |
| ATOM | 1230 | O | ASN | A | 392 | 15.419 | 20.002 | 28.380 | 1.00 | 33.86 | A O |
| ATOM | 1231 | N | GLU | A | 393 | 14.654 | 18.499 | 26.885 | 1.00 | 31.30 | A N |
| ATOM | 1232 | CA | GLU | A | 393 | 14.528 | 17.436 | 27.872 | 1.00 | 30.53 | A C |
| ATOM | 1233 | CB | GLU | A | 393 | 13.514 | 16.395 | 27.400 | 1.00 | 29.33 | A C |
| ATOM | 1234 | CG | GLU | A | 393 | 12.090 | 16.955 | 27.301 | 1.00 | 28.13 | A C |
| ATOM | 1235 | CD | GLU | A | 393 | 11.100 | 15.994 | 26.667 | 1.00 | 26.58 | A C |
| ATOM | 1236 | OE1 | GLU | A | 393 | 11.502 | 14.899 | 26.215 | 1.00 | 27.21 | A O |
| ATOM | 1237 | OE2 | GLU | A | 393 | 9.905 | 16.343 | 26.621 | 1.00 | 26.19 | A C |
| ATOM | 1238 | C | GLU | A | 393 | 15.816 | 16.769 | 28.335 | 1.00 | 31.05 | A C |
| ATOM | 1239 | O | GLU | A | 393 | 15.928 | 16.364 | 29.482 | 1.00 | 31.04 | A O |
| ATOM | 1240 | N | TYR | A | 394 | 16.777 | 16.634 | 27.441 | 1.00 | 31.52 | A N |
| ATOM | 1241 | CA | TYR | A | 394 | 18.032 | 16.012 | 27.817 | 1.00 | 31.58 | A C |
| ATOM | 1242 | CB | TYR | A | 394 | 18.082 | 14.584 | 27.281 | 1.00 | 30.75 | A C |
| ATOM | 1243 | CG | TYR | A | 394 | 16.990 | 13.707 | 27.844 | 1.00 | 29.73 | A C |
| ATOM | 1244 | CD1 | TYR | A | 394 | 15.768 | 13.602 | 27.203 | 1.00 | 29.15 | A C |
| ATOM | 1245 | CE1 | TYR | A | 394 | 14.740 | 12.819 | 27.726 | 1.00 | 31.45 | A C |
| ATOM | 1246 | CD2 | TYR | A | 394 | 17.176 | 13.000 | 29.031 | 1.00 | 30.28 | A C |
| ATOM | 1247 | CE2 | TYR | A | 394 | 16.153 | 12.203 | 29.575 | 1.00 | 31.72 | A C |

Figure 4

```
ATOM   1248  CZ   TYR A 394      14.925  12.117  28.917  1.00 32.19      A    C
ATOM   1249  OH   TYR A 394      13.870  11.372  29.452  1.00 31.53      A    O
ATOM   1250  C    TYR A 394      19.222  16.854  27.356  1.00 33.05      A    C
ATOM   1251  O    TYR A 394      20.373  16.465  27.530  1.00 33.76      A    O
ATOM   1252  N    THR A 395      18.918  18.005  26.755  1.00 35.22      A    N
ATOM   1253  CA   THR A 395      19.914  18.983  26.297  1.00 38.13      A    C
ATOM   1254  CB   THR A 395      20.245  18.889  24.765  1.00 37.41      A    C
ATOM   1255  OG1  THR A 395      19.099  18.467  24.017  1.00 35.96      A    O
ATOM   1256  CG2  THR A 395      21.405  17.934  24.526  1.00 38.35      A    C
ATOM   1257  C    THR A 395      19.392  20.384  26.642  1.00 40.70      A    C
ATOM   1258  O    THR A 395      18.299  20.520  27.199  1.00 42.34      A    O
ATOM   1259  N    ALA A 396      20.159  21.423  26.320  1.00 43.32      A    N
ATOM   1260  CA   ALA A 396      19.733  22.783  26.633  1.00 45.98      A    C
ATOM   1261  CB   ALA A 396      20.690  23.409  27.655  1.00 45.35      A    C
ATOM   1262  C    ALA A 396      19.540  23.711  25.425  1.00 47.64      A    C
ATOM   1263  O    ALA A 396      20.061  24.832  25.398  1.00 48.12      A    O
ATOM   1264  N    ARG A 397      18.752  23.265  24.453  1.00 49.91      A    N
ATOM   1265  CA   ARG A 397      18.508  24.075  23.272  1.00 52.14      A    C
ATOM   1266  CB   ARG A 397      18.081  23.192  22.111  1.00 52.87      A    C
ATOM   1267  CG   ARG A 397      19.113  22.180  21.712  1.00 54.48      A    C
ATOM   1268  CD   ARG A 397      19.093  22.028  20.201  1.00 57.32      A    C
ATOM   1269  NE   ARG A 397      19.837  20.858  19.748  1.00 59.23      A    N
ATOM   1270  CZ   ARG A 397      19.371  19.612  19.783  1.00 60.31      A    C
ATOM   1271  NH1  ARG A 397      18.150  19.356  20.248  1.00 60.82      A    N
ATOM   1272  NH2  ARG A 397      20.125  18.616  19.340  1.00 60.51      A    N
ATOM   1273  C    ARG A 397      17.451  25.150  23.535  1.00 53.39      A    C
ATOM   1274  O    ARG A 397      17.690  26.313  23.129  1.00 53.81      A    O
ATOM   1275  CB   PRO A 403       7.270  20.059  19.401  1.00 35.34      A    C
ATOM   1276  CG   PRO A 403       8.083  20.744  20.478  1.00 34.73      A    C
ATOM   1277  C    PRO A 403       6.063  21.164  17.281  1.00 36.12      A    C
ATOM   1278  O    PRO A 403       5.675  20.128  16.730  1.00 37.41      A    O
ATOM   1279  N    PRO A 403       7.008  22.332  19.223  1.00 35.67      A    N
ATOM   1280  CD   PRO A 403       7.872  22.225  20.402  1.00 34.26      A    C
ATOM   1281  CA   PRO A 403       7.133  21.156  18.362  1.00 35.74      A    C
ATOM   1282  N    ILE A 404       5.572  22.396  17.038  1.00 33.14      A    N
ATOM   1283  CA   ILE A 404       4.484  22.615  16.073  1.00 29.96      A    C
ATOM   1284  CB   ILE A 404       3.664  23.861  16.434  1.00 30.56      A    C
ATOM   1285  CG2  ILE A 404       3.251  24.614  15.177  1.00 29.48      A    C
ATOM   1286  CG1  ILE A 404       2.437  23.459  17.251  1.00 31.77      A    C
ATOM   1287  CD1  ILE A 404       1.723  22.233  16.713  1.00 32.32      A    C
ATOM   1288  C    ILE A 404       4.975  22.680  14.634  1.00 25.56      A    C
ATOM   1289  O    ILE A 404       4.286  22.184  13.748  1.00 23.92      A    O
ATOM   1290  N    LYS A 405       6.136  23.271  14.351  1.00 23.03      A    N
ATOM   1291  CA   LYS A 405       6.609  23.383  12.984  1.00 22.22      A    C
ATOM   1292  CB   LYS A 405       7.795  24.334  12.917  1.00 22.99      A    C
ATOM   1293  CG   LYS A 405       7.432  25.739  13.291  1.00 24.22      A    C
ATOM   1294  CD   LYS A 405       8.612  26.669  13.125  1.00 26.99      A    C
ATOM   1295  CE   LYS A 405       8.236  28.109  13.376  1.00 28.96      A    C
ATOM   1296  NZ   LYS A 405       9.281  29.045  12.859  1.00 32.60      A    N
ATOM   1297  C    LYS A 405       6.867  22.124  12.154  1.00 21.56      A    C
ATOM   1298  O    LYS A 405       7.118  22.237  10.956  1.00 19.13      A    O
ATOM   1299  N    TRP A 406       6.761  20.941  12.764  1.00 20.31      A    N
ATOM   1300  CA   TRP A 406       6.939  19.682  12.049  1.00 20.34      A    C
ATOM   1301  CB   TRP A 406       8.032  18.823  12.702  1.00 20.69      A    C
ATOM   1302  CG   TRP A 406       9.443  19.386  12.632  1.00 21.81      A    C
ATOM   1303  CD2  TRP A 406       9.993  20.431  13.445  1.00 21.90      A    C
ATOM   1304  CE2  TRP A 406      11.333  20.604  13.049  1.00 21.95      A    C
ATOM   1305  CE3  TRP A 406       9.477  21.237  14.472  1.00 22.21      A    C
ATOM   1306  CD1  TRP A 406      10.451  18.975  11.797  1.00 21.80      A    C
ATOM   1307  NE1  TRP A 406      11.586  19.707  12.043  1.00 22.71      A    N
```

Figure 4

| | | | | | | | | | | |
|---|---|---|---|---|---|---|---|---|---|---|
| ATOM | 1308 | CZ2 | TRP | A | 406 | 12.164 | 21.551 | 13.643 | 1.00 22.34 | A C |
| ATOM | 1309 | CZ3 | TRP | A | 406 | 10.300 | 22.178 | 15.062 | 1.00 23.74 | A C |
| ATOM | 1310 | CH2 | TRP | A | 406 | 11.633 | 22.328 | 14.646 | 1.00 23.32 | A C |
| ATOM | 1311 | C | TRP | A | 406 | 5.644 | 18.858 | 12.025 | 1.00 20.17 | A C |
| ATOM | 1312 | O | TRP | A | 406 | 5.598 | 17.787 | 11.427 | 1.00 20.39 | A O |
| ATOM | 1313 | N | THR | A | 407 | 4.591 | 19.356 | 12.660 | 1.00 21.00 | A N |
| ATOM | 1314 | CA | THR | A | 407 | 3.307 | 18.643 | 12.748 | 1.00 21.18 | A C |
| ATOM | 1315 | CB | THR | A | 407 | 2.562 | 19.037 | 14.086 | 1.00 20.73 | A C |
| ATOM | 1316 | OG1 | THR | A | 407 | 3.523 | 19.160 | 15.140 | 1.00 21.65 | A O |
| ATOM | 1317 | CG2 | THR | A | 407 | 1.539 | 17.977 | 14.508 | 1.00 17.72 | A C |
| ATOM | 1318 | C | THR | A | 407 | 2.383 | 18.877 | 11.532 | 1.00 20.36 | A C |
| ATOM | 1319 | O | THR | A | 407 | 2.191 | 20.020 | 11.107 | 1.00 20.94 | A O |
| ATOM | 1320 | N | ALA | A | 408 | 1.833 | 17.792 | 10.979 | 1.00 19.09 | A N |
| ATOM | 1321 | CA | ALA | A | 408 | 0.909 | 17.852 | 9.837 | 1.00 20.29 | A C |
| ATOM | 1322 | CB | ALA | A | 408 | 0.660 | 16.453 | 9.289 | 1.00 18.54 | A C |
| ATOM | 1323 | C | ALA | A | 408 | -0.413 | 18.501 | 10.263 | 1.00 21.16 | A C |
| ATOM | 1324 | O | ALA | A | 408 | -0.808 | 18.393 | 11.411 | 1.00 23.43 | A O |
| ATOM | 1325 | N | PRO | A | 409 | -1.122 | 19.179 | 9.339 | 1.00 22.92 | A N |
| ATOM | 1326 | CD | PRO | A | 409 | -0.825 | 19.394 | 7.912 | 1.00 22.65 | A C |
| ATOM | 1327 | CA | PRO | A | 409 | -2.393 | 19.832 | 9.692 | 1.00 23.80 | A C |
| ATOM | 1328 | CB | PRO | A | 409 | -2.914 | 20.320 | 8.339 | 1.00 23.47 | A C |
| ATOM | 1329 | CG | PRO | A | 409 | -1.652 | 20.621 | 7.595 | 1.00 22.91 | A C |
| ATOM | 1330 | C | PRO | A | 409 | -3.408 | 18.942 | 10.419 | 1.00 23.63 | A C |
| ATOM | 1331 | O | PRO | A | 409 | -4.034 | 19.373 | 11.391 | 1.00 23.53 | A O |
| ATOM | 1332 | N | GLU | A | 410 | -3.537 | 17.692 | 9.987 | 1.00 23.31 | A N |
| ATOM | 1333 | CA | GLU | A | 410 | -4.485 | 16.768 | 10.613 | 1.00 23.78 | A C |
| ATOM | 1334 | CB | GLU | A | 410 | -4.705 | 15.513 | 9.750 | 1.00 23.80 | A C |
| ATOM | 1335 | CG | GLU | A | 410 | -3.564 | 14.481 | 9.707 | 1.00 24.87 | A C |
| ATOM | 1336 | CD | GLU | A | 410 | -2.443 | 14.791 | 8.694 | 1.00 24.39 | A C |
| ATOM | 1337 | OE1 | GLU | A | 410 | -2.432 | 15.883 | 8.092 | 1.00 24.52 | A O |
| ATOM | 1338 | OE2 | GLU | A | 410 | -1.563 | 13.923 | 8.509 | 1.00 23.55 | A O |
| ATOM | 1339 | C | GLU | A | 410 | -4.086 | 16.366 | 12.034 | 1.00 24.43 | A C |
| ATOM | 1340 | O | GLU | A | 410 | -4.937 | 16.009 | 12.855 | 1.00 24.96 | A O |
| ATOM | 1341 | N | ALA | A | 411 | -2.787 | 16.429 | 12.318 | 1.00 24.22 | A N |
| ATOM | 1342 | CA | ALA | A | 411 | -2.261 | 16.080 | 13.634 | 1.00 23.44 | A C |
| ATOM | 1343 | CB | ALA | A | 411 | -0.800 | 15.702 | 13.528 | 1.00 20.40 | A C |
| ATOM | 1344 | C | ALA | A | 411 | -2.453 | 17.267 | 14.580 | 1.00 24.90 | A C |
| ATOM | 1345 | O | ALA | A | 411 | -2.638 | 17.093 | 15.787 | 1.00 25.63 | A O |
| ATOM | 1346 | N | ILE | A | 412 | -2.459 | 18.467 | 14.004 | 1.00 25.93 | A N |
| ATOM | 1347 | CA | ILE | A | 412 | -2.650 | 19.694 | 14.761 | 1.00 27.86 | A C |
| ATOM | 1348 | CB | ILE | A | 412 | -2.165 | 20.918 | 13.969 | 1.00 28.10 | A C |
| ATOM | 1349 | CG2 | ILE | A | 412 | -2.549 | 22.207 | 14.701 | 1.00 29.09 | A C |
| ATOM | 1350 | CG1 | ILE | A | 412 | -0.657 | 20.848 | 13.744 | 1.00 27.87 | A C |
| ATOM | 1351 | CD1 | ILE | A | 412 | -0.123 | 22.060 | 13.055 | 1.00 28.24 | A C |
| ATOM | 1352 | C | ILE | A | 412 | -4.116 | 19.946 | 15.127 | 1.00 29.58 | A C |
| ATOM | 1353 | O | ILE | A | 412 | -4.418 | 20.347 | 16.253 | 1.00 30.37 | A O |
| ATOM | 1354 | N | ASN | A | 413 | -5.008 | 19.729 | 14.162 | 1.00 29.94 | A N |
| ATOM | 1355 | CA | ASN | A | 413 | -6.441 | 19.968 | 14.341 | 1.00 30.72 | A C |
| ATOM | 1356 | CB | ASN | A | 413 | -7.120 | 20.241 | 13.000 | 1.00 30.05 | A C |
| ATOM | 1357 | CG | ASN | A | 413 | -6.591 | 21.470 | 12.317 | 1.00 30.98 | A C |
| ATOM | 1358 | OD1 | ASN | A | 413 | -6.365 | 22.502 | 12.958 | 1.00 32.44 | A O |
| ATOM | 1359 | ND2 | ASN | A | 413 | -6.402 | 21.379 | 11.002 | 1.00 30.07 | A N |
| ATOM | 1360 | C | ASN | A | 413 | -7.209 | 18.866 | 15.029 | 1.00 30.66 | A C |
| ATOM | 1361 | O | ASN | A | 413 | -8.130 | 19.147 | 15.797 | 1.00 32.98 | A O |
| ATOM | 1362 | N | TYR | A | 414 | -6.857 | 17.619 | 14.741 | 1.00 31.15 | A N |
| ATOM | 1363 | CA | TYR | A | 414 | -7.568 | 16.502 | 15.330 | 1.00 32.64 | A C |
| ATOM | 1364 | CB | TYR | A | 414 | -8.344 | 15.754 | 14.240 | 1.00 34.62 | A C |
| ATOM | 1365 | CG | TYR | A | 414 | -9.204 | 16.664 | 13.388 | 1.00 37.02 | A C |
| ATOM | 1366 | CD1 | TYR | A | 414 | -10.427 | 17.163 | 13.868 | 1.00 37.34 | A C |
| ATOM | 1367 | CE1 | TYR | A | 414 | -11.191 | 18.029 | 13.104 | 1.00 38.21 | A C |

Figure 4

```
ATOM   1368  CD2 TYR A 414      -8.778  17.059  12.117  1.00 37.68      A   C
ATOM   1369  CE2 TYR A 414      -9.536  17.925  11.345  1.00 39.35      A   C
ATOM   1370  CZ  TYR A 414     -10.738  18.410  11.840  1.00 40.00      A   C
ATOM   1371  OH  TYR A 414     -11.467  19.288  11.061  1.00 42.08      A   O
ATOM   1372  C   TYR A 414      -6.696  15.539  16.132  1.00 32.95      A   C
ATOM   1373  O   TYR A 414      -7.215  14.612  16.767  1.00 32.27      A   O
ATOM   1374  N   GLY A 415      -5.375  15.742  16.086  1.00 32.69      A   N
ATOM   1375  CA  GLY A 415      -4.459  14.893  16.832  1.00 29.07      A   C
ATOM   1376  C   GLY A 415      -4.330  13.497  16.277  1.00 28.10      A   C
ATOM   1377  O   GLY A 415      -4.066  12.544  17.010  1.00 28.82      A   O
ATOM   1378  N   THR A 416      -4.542  13.369  14.976  1.00 28.22      A   N
ATOM   1379  CA  THR A 416      -4.431  12.073  14.327  1.00 28.09      A   C
ATOM   1380  CB  THR A 416      -5.568  11.856  13.270  1.00 27.92      A   C
ATOM   1381  OG1 THR A 416      -5.017  11.381  12.036  1.00 28.57      A   O
ATOM   1382  CG2 THR A 416      -6.366  13.124  13.039  1.00 26.38      A   C
ATOM   1383  C   THR A 416      -3.023  11.940  13.736  1.00 26.85      A   C
ATOM   1384  O   THR A 416      -2.642  12.682  12.838  1.00 28.09      A   O
ATOM   1385  N   PHE A 417      -2.226  11.071  14.345  1.00 26.40      A   N
ATOM   1386  CA  PHE A 417      -0.859  10.838  13.913  1.00 24.42      A   C
ATOM   1387  CB  PHE A 417       0.094  10.858  15.109  1.00 25.37      A   C
ATOM   1388  CG  PHE A 417       0.281  12.221  15.742  1.00 26.87      A   C
ATOM   1389  CD1 PHE A 417      -0.558  12.657  16.781  1.00 26.83      A   C
ATOM   1390  CD2 PHE A 417       1.322  13.061  15.327  1.00 25.37      A   C
ATOM   1391  CE1 PHE A 417      -0.369  13.908  17.398  1.00 25.94      A   C
ATOM   1392  CE2 PHE A 417       1.516  14.317  15.938  1.00 26.20      A   C
ATOM   1393  CZ  PHE A 417       0.670  14.739  16.976  1.00 25.51      A   C
ATOM   1394  C   PHE A 417      -0.739   9.488  13.225  1.00 24.63      A   C
ATOM   1395  O   PHE A 417      -1.131   8.461  13.773  1.00 26.49      A   O
ATOM   1396  N   THR A 418      -0.236   9.504  11.999  1.00 23.76      A   N
ATOM   1397  CA  THR A 418      -0.014   8.298  11.218  1.00 22.39      A   C
ATOM   1398  CB  THR A 418      -1.061   8.113  10.113  1.00 23.14      A   C
ATOM   1399  OG1 THR A 418      -0.944   9.178   9.169  1.00 23.22      A   O
ATOM   1400  CG2 THR A 418      -2.474   8.081  10.704  1.00 23.34      A   C
ATOM   1401  C   THR A 418       1.352   8.437  10.546  1.00 22.54      A   C
ATOM   1402  O   THR A 418       2.053   9.437  10.720  1.00 23.06      A   O
ATOM   1403  N   ILE A 419       1.730   7.428   9.774  1.00 23.33      A   N
ATOM   1404  CA  ILE A 419       3.000   7.446   9.075  1.00 22.80      A   C
ATOM   1405  CB  ILE A 419       3.291   6.069   8.389  1.00 22.71      A   C
ATOM   1406  CG2 ILE A 419       2.385   5.842   7.220  1.00 20.57      A   C
ATOM   1407  CG1 ILE A 419       4.753   5.990   7.957  1.00 23.60      A   C
ATOM   1408  CD1 ILE A 419       5.735   5.955   9.131  1.00 22.55      A   C
ATOM   1409  C   ILE A 419       2.950   8.591   8.060  1.00 22.79      A   C
ATOM   1410  O   ILE A 419       3.987   9.119   7.668  1.00 22.27      A   O
ATOM   1411  N   LYS A 420       1.739   9.010   7.686  1.00 21.72      A   N
ATOM   1412  CA  LYS A 420       1.586  10.104   6.738  1.00 21.82      A   C
ATOM   1413  CB  LYS A 420       0.205  10.093   6.091  1.00 21.11      A   C
ATOM   1414  CG  LYS A 420       0.001   8.912   5.168  1.00 19.93      A   C
ATOM   1415  CD  LYS A 420       0.939   8.969   3.978  1.00 18.98      A   C
ATOM   1416  CE  LYS A 420       0.734   7.745   3.114  1.00 18.23      A   C
ATOM   1417  NZ  LYS A 420       1.658   7.748   1.979  1.00 19.03      A   N
ATOM   1418  C   LYS A 420       1.896  11.444   7.372  1.00 20.98      A   C
ATOM   1419  O   LYS A 420       2.296  12.378   6.669  1.00 22.25      A   O
ATOM   1420  N   SER A 421       1.690  11.563   8.685  1.00 20.31      A   N
ATOM   1421  CA  SER A 421       2.046  12.805   9.347  1.00 20.44      A   C
ATOM   1422  CB  SER A 421       1.233  13.062  10.631  1.00 19.00      A   C
ATOM   1423  OG  SER A 421       1.195  11.959  11.502  1.00 21.89      A   O
ATOM   1424  C   SER A 421       3.585  12.828   9.543  1.00 20.31      A   C
ATOM   1425  O   SER A 421       4.184  13.889   9.632  1.00 21.51      A   O
ATOM   1426  N   ASP A 422       4.224  11.659   9.523  1.00 19.45      A   N
ATOM   1427  CA  ASP A 422       5.693  11.587   9.634  1.00 19.76      A   C
```

Figure 4

| | | | | | | | | | | | |
|---|---|---|---|---|---|---|---|---|---|---|---|
| ATOM | 1428 | CB | ASP | A | 422 | 6.191 | 10.165 | 9.899 | 1.00 | 17.22 | A C |
| ATOM | 1429 | CG | ASP | A | 422 | 5.981 | 9.721 | 11.320 | 1.00 | 16.24 | A C |
| ATOM | 1430 | OD1 | ASP | A | 422 | 6.060 | 10.558 | 12.244 | 1.00 | 19.68 | A O |
| ATOM | 1431 | OD2 | ASP | A | 422 | 5.749 | 8.518 | 11.513 | 1.00 | 16.90 | A O |
| ATOM | 1432 | C | ASP | A | 422 | 6.289 | 12.039 | 8.325 | 1.00 | 20.36 | A C |
| ATOM | 1433 | O | ASP | A | 422 | 7.340 | 12.680 | 8.307 | 1.00 | 22.06 | A O |
| ATOM | 1434 | N | VAL | A | 423 | 5.649 | 11.626 | 7.226 | 1.00 | 21.16 | A N |
| ATOM | 1435 | CA | VAL | A | 423 | 6.086 | 12.005 | 5.880 | 1.00 | 20.86 | A C |
| ATOM | 1436 | CB | VAL | A | 423 | 5.158 | 11.419 | 4.764 | 1.00 | 21.55 | A C |
| ATOM | 1437 | CG1 | VAL | A | 423 | 5.581 | 11.935 | 3.377 | 1.00 | 19.15 | A C |
| ATOM | 1438 | CG2 | VAL | A | 423 | 5.196 | 9.882 | 4.787 | 1.00 | 21.24 | A C |
| ATOM | 1439 | C | VAL | A | 423 | 6.088 | 13.528 | 5.812 | 1.00 | 20.57 | A C |
| ATOM | 1440 | O | VAL | A | 423 | 7.013 | 14.118 | 5.251 | 1.00 | 21.24 | A O |
| ATOM | 1441 | N | TRP | A | 424 | 5.064 | 14.155 | 6.405 | 1.00 | 19.94 | A N |
| ATOM | 1442 | CA | TRP | A | 424 | 4.970 | 15.617 | 6.454 | 1.00 | 20.05 | A C |
| ATOM | 1443 | CB | TRP | A | 424 | 3.654 | 16.061 | 7.116 | 1.00 | 17.73 | A C |
| ATOM | 1444 | CG | TRP | A | 424 | 3.563 | 17.548 | 7.322 | 1.00 | 16.99 | A C |
| ATOM | 1445 | CD2 | TRP | A | 424 | 2.709 | 18.473 | 6.622 | 1.00 | 19.00 | A C |
| ATOM | 1446 | CE2 | TRP | A | 424 | 3.012 | 19.771 | 7.116 | 1.00 | 19.08 | A C |
| ATOM | 1447 | CE3 | TRP | A | 424 | 1.722 | 18.346 | 5.631 | 1.00 | 18.77 | A C |
| ATOM | 1448 | CD1 | TRP | A | 424 | 4.311 | 18.300 | 8.175 | 1.00 | 16.91 | A C |
| ATOM | 1449 | NE1 | TRP | A | 424 | 3.998 | 19.630 | 8.057 | 1.00 | 18.40 | A N |
| ATOM | 1450 | CZ2 | TRP | A | 424 | 2.370 | 20.933 | 6.643 | 1.00 | 18.54 | A C |
| ATOM | 1451 | CZ3 | TRP | A | 424 | 1.091 | 19.499 | 5.161 | 1.00 | 17.24 | A C |
| ATOM | 1452 | CH2 | TRP | A | 424 | 1.417 | 20.770 | 5.670 | 1.00 | 18.30 | A C |
| ATOM | 1453 | C | TRP | A | 424 | 6.195 | 16.176 | 7.221 | 1.00 | 21.25 | A C |
| ATOM | 1454 | O | TRP | A | 424 | 6.852 | 17.118 | 6.750 | 1.00 | 20.19 | A O |
| ATOM | 1455 | N | SER | A | 425 | 6.471 | 15.592 | 8.394 | 1.00 | 22.71 | A N |
| ATOM | 1456 | CA | SER | A | 425 | 7.610 | 15.961 | 9.246 | 1.00 | 24.22 | A C |
| ATOM | 1457 | CB | SER | A | 425 | 7.639 | 15.081 | 10.506 | 1.00 | 25.94 | A C |
| ATOM | 1458 | OG | SER | A | 425 | 6.758 | 15.553 | 11.502 | 1.00 | 27.28 | A O |
| ATOM | 1459 | C | SER | A | 425 | 8.952 | 15.807 | 8.517 | 1.00 | 22.98 | A C |
| ATOM | 1460 | O | SER | A | 425 | 9.868 | 16.601 | 8.726 | 1.00 | 23.19 | A O |
| ATOM | 1461 | N | PHE | A | 426 | 9.070 | 14.740 | 7.730 | 1.00 | 22.13 | A N |
| ATOM | 1462 | CA | PHE | A | 426 | 10.269 | 14.467 | 6.960 | 1.00 | 23.42 | A C |
| ATOM | 1463 | CB | PHE | A | 426 | 10.181 | 13.097 | 6.286 | 1.00 | 22.46 | A C |
| ATOM | 1464 | CG | PHE | A | 426 | 11.408 | 12.742 | 5.480 | 1.00 | 23.45 | A C |
| ATOM | 1465 | CD1 | PHE | A | 426 | 12.590 | 12.373 | 6.120 | 1.00 | 21.41 | A C |
| ATOM | 1466 | CD2 | PHE | A | 426 | 11.374 | 12.764 | 4.068 | 1.00 | 23.21 | A C |
| ATOM | 1467 | CE1 | PHE | A | 426 | 13.724 | 12.024 | 5.382 | 1.00 | 23.18 | A C |
| ATOM | 1468 | CE2 | PHE | A | 426 | 12.515 | 12.414 | 3.315 | 1.00 | 24.01 | A C |
| ATOM | 1469 | CZ | PHE | A | 426 | 13.688 | 12.043 | 3.980 | 1.00 | 23.24 | A C |
| ATOM | 1470 | C | PHE | A | 426 | 10.511 | 15.573 | 5.917 | 1.00 | 23.82 | A C |
| ATOM | 1471 | O | PHE | A | 426 | 11.673 | 15.962 | 5.668 | 1.00 | 24.85 | A O |
| ATOM | 1472 | N | GLY | A | 427 | 9.424 | 16.051 | 5.301 | 1.00 | 21.51 | A N |
| ATOM | 1473 | CA | GLY | A | 427 | 9.513 | 17.137 | 4.341 | 1.00 | 18.76 | A C |
| ATOM | 1474 | C | GLY | A | 427 | 10.054 | 18.365 | 5.053 | 1.00 | 19.35 | A C |
| ATOM | 1475 | O | GLY | A | 427 | 10.908 | 19.072 | 4.512 | 1.00 | 19.74 | A O |
| ATOM | 1476 | N | ILE | A | 428 | 9.565 | 18.621 | 6.272 | 1.00 | 19.93 | A N |
| ATOM | 1477 | CA | ILE | A | 428 | 10.046 | 19.758 | 7.077 | 1.00 | 20.26 | A C |
| ATOM | 1478 | CB | ILE | A | 428 | 9.201 | 19.959 | 8.374 | 1.00 | 17.34 | A C |
| ATOM | 1479 | CG2 | ILE | A | 428 | 9.699 | 21.172 | 9.140 | 1.00 | 15.21 | A C |
| ATOM | 1480 | CG1 | ILE | A | 428 | 7.716 | 20.153 | 8.032 | 1.00 | 17.25 | A C |
| ATOM | 1481 | CD1 | ILE | A | 428 | 7.399 | 21.414 | 7.193 | 1.00 | 14.63 | A C |
| ATOM | 1482 | C | ILE | A | 428 | 11.539 | 19.526 | 7.449 | 1.00 | 20.45 | A C |
| ATOM | 1483 | O | ILE | A | 428 | 12.342 | 20.466 | 7.461 | 1.00 | 20.19 | A O |
| ATOM | 1484 | N | LEU | A | 429 | 11.889 | 18.265 | 7.704 | 1.00 | 19.33 | A N |
| ATOM | 1485 | CA | LEU | A | 429 | 13.244 | 17.866 | 8.055 | 1.00 | 20.47 | A C |
| ATOM | 1486 | CB | LEU | A | 429 | 13.255 | 16.383 | 8.499 | 1.00 | 20.02 | A C |
| ATOM | 1487 | CG | LEU | A | 429 | 14.506 | 15.761 | 9.132 | 1.00 | 18.99 | A C |

Figure 4

| | | | | | | | | | | |
|---|---|---|---|---|---|---|---|---|---|---|
|ATOM|1488|CD1|LEU|A|429|14.168|14.454|9.819|1.00 19.64|A C|
|ATOM|1489|CD2|LEU|A|429|15.567|15.524|8.089|1.00 20.82|A C|
|ATOM|1490|C|LEU|A|429|14.190|18.097|6.865|1.00 21.45|A C|
|ATOM|1491|O|LEU|A|429|15.360|18.446|7.059|1.00 20.91|A O|
|ATOM|1492|N|LEU|A|430|13.682|17.897|5.642|1.00 20.66|A N|
|ATOM|1493|CA|LEU|A|430|14.482|18.091|4.437|1.00 19.40|A C|
|ATOM|1494|CB|LEU|A|430|13.721|17.678|3.177|1.00 18.72|A C|
|ATOM|1495|CG|LEU|A|430|13.481|16.199|2.888|1.00 18.57|A C|
|ATOM|1496|CD1|LEU|A|430|12.513|16.084|1.707|1.00 16.63|A C|
|ATOM|1497|CD2|LEU|A|430|14.823|15.473|2.616|1.00 17.42|A C|
|ATOM|1498|C|LEU|A|430|14.909|19.534|4.313|1.00 19.76|A C|
|ATOM|1499|O|LEU|A|430|15.974|19.796|3.786|1.00 21.96|A O|
|ATOM|1500|N|THR|A|431|14.067|20.471|4.751|1.00 20.74|A N|
|ATOM|1501|CA|THR|A|431|14.417|21.890|4.699|1.00 21.83|A C|
|ATOM|1502|CB|THR|A|431|13.186|22.826|4.908|1.00 21.37|A C|
|ATOM|1503|OG1|THR|A|431|12.757|22.807|6.278|1.00 23.51|A O|
|ATOM|1504|CG2|THR|A|431|12.044|22.391|4.028|1.00 19.63|A C|
|ATOM|1505|C|THR|A|431|15.519|22.197|5.728|1.00 22.98|A C|
|ATOM|1506|O|THR|A|431|16.353|23.067|5.498|1.00 24.81|A O|
|ATOM|1507|N|GLU|A|432|15.527|21.470|6.851|1.00 23.25|A N|
|ATOM|1508|CA|GLU|A|432|16.549|21.630|7.882|1.00 23.06|A C|
|ATOM|1509|CB|GLU|A|432|16.222|20.794|9.116|1.00 22.48|A C|
|ATOM|1510|CG|GLU|A|432|15.104|21.344|9.972|1.00 23.06|A C|
|ATOM|1511|CD|GLU|A|432|14.851|20.477|11.204|1.00 22.96|A C|
|ATOM|1512|OE1|GLU|A|432|14.329|19.349|11.046|1.00 21.98|A O|
|ATOM|1513|OE2|GLU|A|432|15.184|20.913|12.329|1.00 21.72|A O|
|ATOM|1514|C|GLU|A|432|17.876|21.141|7.322|1.00 23.93|A C|
|ATOM|1515|O|GLU|A|432|18.900|21.788|7.487|1.00 26.03|A O|
|ATOM|1516|N|ILE|A|433|17.844|19.951|6.675|1.00 24.96|A N|
|ATOM|1517|CA|ILE|A|433|19.027|19.313|6.110|1.00 24.47|A C|
|ATOM|1518|CB|ILE|A|433|18.680|17.990|5.417|1.00 23.16|A C|
|ATOM|1519|CG2|ILE|A|433|19.751|17.595|4.409|1.00 22.20|A C|
|ATOM|1520|CG1|ILE|A|433|18.500|16.932|6.482|1.00 23.94|A C|
|ATOM|1521|CD1|ILE|A|433|18.293|15.544|5.914|1.00 23.96|A C|
|ATOM|1522|C|ILE|A|433|19.651|20.147|5.038|1.00 27.89|A C|
|ATOM|1523|O|ILE|A|433|20.830|20.023|4.736|1.00 28.52|A O|
|ATOM|1524|N|VAL|A|434|18.842|21.056|4.497|1.00 27.27|A N|
|ATOM|1525|CA|VAL|A|434|19.332|21.800|3.343|1.00 28.24|A C|
|ATOM|1526|CB|VAL|A|434|18.325|21.760|2.178|1.00 27.33|A C|
|ATOM|1527|CG1|VAL|A|434|18.134|20.333|1.688|1.00 24.85|A C|
|ATOM|1528|CG2|VAL|A|434|16.997|22.369|2.600|1.00 29.24|A C|
|ATOM|1529|C|VAL|A|434|19.649|23.249|3.704|1.00 29.55|A C|
|ATOM|1530|O|VAL|A|434|20.199|23.980|2.847|1.00 31.77|A O|
|ATOM|1531|N|THR|A|435|19.320|23.670|4.866|1.00 31.22|A N|
|ATOM|1532|CA|THR|A|435|19.611|25.036|5.217|1.00 31.21|A C|
|ATOM|1533|CB|THR|A|435|18.316|25.768|5.589|1.00 30.57|A C|
|ATOM|1534|OG1|THR|A|435|17.602|25.007|6.568|1.00 29.24|A O|
|ATOM|1535|CG2|THR|A|435|17.444|25.950|4.366|1.00 30.32|A C|
|ATOM|1536|C|THR|A|435|20.555|25.032|6.423|1.00 32.35|A C|
|ATOM|1537|O|THR|A|435|20.656|26.002|7.177|1.00 30.72|A O|
|ATOM|1538|N|HIS|A|436|21.234|23.902|6.581|1.00 35.33|A N|
|ATOM|1539|CA|HIS|A|436|22.180|23.688|7.673|1.00 37.08|A C|
|ATOM|1540|CB|HIS|A|436|23.460|24.506|7.461|1.00 41.16|A C|
|ATOM|1541|CG|HIS|A|436|24.091|24.274|6.121|1.00 44.42|A C|
|ATOM|1542|CD2|HIS|A|436|24.685|25.127|5.249|1.00 45.91|A C|
|ATOM|1543|ND1|HIS|A|436|24.054|23.047|5.489|1.00 45.79|A N|
|ATOM|1544|CE1|HIS|A|436|24.590|23.153|4.284|1.00 46.88|A C|
|ATOM|1545|NE2|HIS|A|436|24.979|24.404|4.115|1.00 48.06|A N|
|ATOM|1546|C|HIS|A|436|21.589|23.900|9.053|1.00 35.93|A C|
|ATOM|1547|O|HIS|A|436|22.067|24.732|9.827|1.00 34.91|A O|

Figure 4

| ATOM | 1548 | N   | GLY | A | 437 | 20.546 | 23.117 | 9.330  | 1.00 | 34.97 | A | N |
| ATOM | 1549 | CA  | GLY | A | 437 | 19.866 | 23.139 | 10.609 | 1.00 | 35.57 | A | C |
| ATOM | 1550 | C   | GLY | A | 437 | 19.052 | 24.370 | 10.934 | 1.00 | 35.74 | A | C |
| ATOM | 1551 | O   | GLY | A | 437 | 18.740 | 24.609 | 12.097 | 1.00 | 34.86 | A | O |
| ATOM | 1552 | N   | ARG | A | 438 | 18.711 | 25.152 | 9.917  | 1.00 | 36.71 | A | N |
| ATOM | 1553 | CA  | ARG | A | 438 | 17.910 | 26.357 | 10.113 | 1.00 | 37.10 | A | C |
| ATOM | 1554 | CB  | ARG | A | 438 | 17.899 | 27.171 | 8.815  | 1.00 | 40.55 | A | C |
| ATOM | 1555 | CG  | ARG | A | 438 | 17.504 | 28.645 | 8.931  | 1.00 | 44.89 | A | C |
| ATOM | 1556 | CD  | ARG | A | 438 | 15.984 | 28.871 | 8.923  | 1.00 | 47.34 | A | C |
| ATOM | 1557 | NE  | ARG | A | 438 | 15.310 | 28.313 | 7.744  | 1.00 | 49.70 | A | N |
| ATOM | 1558 | CZ  | ARG | A | 438 | 15.450 | 28.771 | 6.499  | 1.00 | 50.60 | A | C |
| ATOM | 1559 | NH1 | ARG | A | 438 | 16.253 | 29.804 | 6.250  | 1.00 | 51.13 | A | N |
| ATOM | 1560 | NH2 | ARG | A | 438 | 14.775 | 28.203 | 5.503  | 1.00 | 50.43 | A | N |
| ATOM | 1561 | C   | ARG | A | 438 | 16.480 | 25.946 | 10.535 | 1.00 | 34.62 | A | C |
| ATOM | 1562 | O   | ARG | A | 438 | 15.977 | 24.888 | 10.135 | 1.00 | 32.85 | A | O |
| ATOM | 1563 | N   | ILE | A | 439 | 15.880 | 26.761 | 11.399 | 1.00 | 31.40 | A | N |
| ATOM | 1564 | CA  | ILE | A | 439 | 14.537 | 26.536 | 11.912 | 1.00 | 31.16 | A | C |
| ATOM | 1565 | CB  | ILE | A | 439 | 14.247 | 27.470 | 13.116 | 1.00 | 31.18 | A | C |
| ATOM | 1566 | CG2 | ILE | A | 439 | 12.774 | 27.419 | 13.499 | 1.00 | 31.45 | A | C |
| ATOM | 1567 | CG1 | ILE | A | 439 | 15.093 | 27.031 | 14.316 | 1.00 | 32.41 | A | C |
| ATOM | 1568 | CD1 | ILE | A | 439 | 15.058 | 28.002 | 15.500 | 1.00 | 33.27 | A | C |
| ATOM | 1569 | C   | ILE | A | 439 | 13.486 | 26.719 | 10.820 | 1.00 | 30.03 | A | C |
| ATOM | 1570 | O   | ILE | A | 439 | 13.576 | 27.647 | 10.013 | 1.00 | 31.12 | A | O |
| ATOM | 1571 | N   | PRO | A | 440 | 12.504 | 25.801 | 10.748 | 1.00 | 28.80 | A | N |
| ATOM | 1572 | CD  | PRO | A | 440 | 12.357 | 24.592 | 11.581 | 1.00 | 26.82 | A | C |
| ATOM | 1573 | CA  | PRO | A | 440 | 11.436 | 25.875 | 9.739  | 1.00 | 28.63 | A | C |
| ATOM | 1574 | CB  | PRO | A | 440 | 10.564 | 24.658 | 10.083 | 1.00 | 27.39 | A | C |
| ATOM | 1575 | CG  | PRO | A | 440 | 11.551 | 23.690 | 10.697 | 1.00 | 26.71 | A | C |
| ATOM | 1576 | C   | PRO | A | 440 | 10.636 | 27.184 | 9.863  | 1.00 | 28.23 | A | C |
| ATOM | 1577 | O   | PRO | A | 440 | 10.605 | 27.792 | 10.936 | 1.00 | 27.02 | A | O |
| ATOM | 1578 | N   | TYR | A | 441 | 10.023 | 27.619 | 8.759  | 1.00 | 27.57 | A | N |
| ATOM | 1579 | CA  | TYR | A | 441 | 9.225  | 28.847 | 8.738  | 1.00 | 27.67 | A | C |
| ATOM | 1580 | CB  | TYR | A | 441 | 7.865  | 28.619 | 9.404  | 1.00 | 27.62 | A | C |
| ATOM | 1581 | CG  | TYR | A | 441 | 7.110  | 27.412 | 8.924  | 1.00 | 25.71 | A | C |
| ATOM | 1582 | CD1 | TYR | A | 441 | 6.243  | 27.492 | 7.818  | 1.00 | 25.06 | A | C |
| ATOM | 1583 | CE1 | TYR | A | 441 | 5.552  | 26.364 | 7.365  | 1.00 | 25.83 | A | C |
| ATOM | 1584 | CD2 | TYR | A | 441 | 7.273  | 26.182 | 9.559  | 1.00 | 24.46 | A | C |
| ATOM | 1585 | CE2 | TYR | A | 441 | 6.593  | 25.049 | 9.120  | 1.00 | 25.44 | A | C |
| ATOM | 1586 | CZ  | TYR | A | 441 | 5.740  | 25.145 | 8.019  | 1.00 | 25.72 | A | C |
| ATOM | 1587 | OH  | TYR | A | 441 | 5.076  | 24.023 | 7.593  | 1.00 | 26.40 | A | O |
| ATOM | 1588 | C   | TYR | A | 441 | 9.911  | 30.002 | 9.453  | 1.00 | 29.03 | A | C |
| ATOM | 1589 | O   | TYR | A | 441 | 9.376  | 30.555 | 10.417 | 1.00 | 28.15 | A | O |
| ATOM | 1590 | N   | PRO | A | 442 | 11.102 | 30.397 | 8.983  | 1.00 | 32.09 | A | N |
| ATOM | 1591 | CD  | PRO | A | 442 | 11.783 | 29.985 | 7.742  | 1.00 | 32.71 | A | C |
| ATOM | 1592 | CA  | PRO | A | 442 | 11.806 | 31.505 | 9.642  | 1.00 | 34.68 | A | C |
| ATOM | 1593 | CB  | PRO | A | 442 | 13.074 | 31.641 | 8.809  | 1.00 | 34.52 | A | C |
| ATOM | 1594 | CG  | PRO | A | 442 | 12.612 | 31.204 | 7.414  | 1.00 | 34.07 | A | C |
| ATOM | 1595 | C   | PRO | A | 442 | 10.972 | 32.800 | 9.661  | 1.00 | 37.20 | A | C |
| ATOM | 1596 | O   | PRO | A | 442 | 10.265 | 33.116 | 8.703  | 1.00 | 37.93 | A | O |
| ATOM | 1597 | N   | GLY | A | 443 | 11.021 | 33.526 | 10.772 | 1.00 | 39.44 | A | N |
| ATOM | 1598 | CA  | GLY | A | 443 | 10.245 | 34.749 | 10.867 | 1.00 | 41.37 | A | C |
| ATOM | 1599 | C   | GLY | A | 443 | 8.810  | 34.480 | 11.297 | 1.00 | 42.68 | A | C |
| ATOM | 1600 | O   | GLY | A | 443 | 7.957  | 35.380 | 11.278 | 1.00 | 45.02 | A | O |
| ATOM | 1601 | N   | MET | A | 444 | 8.534  | 33.232 | 11.668 | 1.00 | 41.31 | A | N |
| ATOM | 1602 | CA  | MET | A | 444 | 7.208  | 32.849 | 12.117 | 1.00 | 40.28 | A | C |
| ATOM | 1603 | CB  | MET | A | 444 | 6.564  | 31.875 | 11.130 | 1.00 | 40.63 | A | C |
| ATOM | 1604 | CG  | MET | A | 444 | 5.788  | 32.539 | 10.029 | 1.00 | 41.31 | A | C |
| ATOM | 1605 | SD  | MET | A | 444 | 5.490  | 31.459 | 8.631  | 1.00 | 43.39 | A | S |
| ATOM | 1606 | CE  | MET | A | 444 | 4.034  | 30.703 | 9.111  | 1.00 | 43.28 | A | C |
| ATOM | 1607 | C   | MET | A | 444 | 7.276  | 32.212 | 13.492 | 1.00 | 40.09 | A | C |

Figure 4

| | | | | | | | | | | |
|---|---|---|---|---|---|---|---|---|---|---|
| ATOM | 1608 | O | MET | A | 444 | 8.236 | 31.510 | 13.813 | 1.00 41.16 | A | O |
| ATOM | 1609 | N | THR | A | 445 | 6.268 | 32.499 | 14.311 | 1.00 39.16 | A | N |
| ATOM | 1610 | CA | THR | A | 445 | 6.149 | 31.938 | 15.649 | 1.00 38.69 | A | C |
| ATOM | 1611 | CB | THR | A | 445 | 5.565 | 32.980 | 16.640 | 1.00 38.94 | A | C |
| ATOM | 1612 | OG1 | THR | A | 445 | 4.225 | 33.317 | 16.264 | 1.00 39.15 | A | O |
| ATOM | 1613 | CG2 | THR | A | 445 | 6.386 | 34.250 | 16.618 | 1.00 39.67 | A | C |
| ATOM | 1614 | C | THR | A | 445 | 5.165 | 30.776 | 15.499 | 1.00 38.79 | A | C |
| ATOM | 1615 | O | THR | A | 445 | 4.492 | 30.658 | 14.475 | 1.00 36.87 | A | O |
| ATOM | 1616 | N | ASN | A | 446 | 5.064 | 29.919 | 16.509 | 1.00 41.19 | A | N |
| ATOM | 1617 | CA | ASN | A | 446 | 4.127 | 28.790 | 16.443 | 1.00 42.44 | A | C |
| ATOM | 1618 | CB | ASN | A | 446 | 4.134 | 27.967 | 17.736 | 1.00 42.43 | A | C |
| ATOM | 1619 | CG | ASN | A | 446 | 5.259 | 26.949 | 17.772 | 1.00 43.67 | A | C |
| ATOM | 1620 | OD1 | ASN | A | 446 | 6.180 | 26.968 | 16.933 | 1.00 41.28 | A | O |
| ATOM | 1621 | ND2 | ASN | A | 446 | 5.190 | 26.044 | 18.746 | 1.00 45.00 | A | N |
| ATOM | 1622 | C | ASN | A | 446 | 2.699 | 29.183 | 16.084 | 1.00 42.26 | A | C |
| ATOM | 1623 | O | ASN | A | 446 | 2.095 | 28.560 | 15.200 | 1.00 41.97 | A | O |
| ATOM | 1624 | N | PRO | A | 447 | 2.126 | 30.204 | 16.771 | 1.00 42.50 | A | N |
| ATOM | 1625 | CD | PRO | A | 447 | 2.649 | 30.984 | 17.911 | 1.00 41.28 | A | C |
| ATOM | 1626 | CA | PRO | A | 447 | 0.751 | 30.623 | 16.457 | 1.00 41.27 | A | C |
| ATOM | 1627 | CB | PRO | A | 447 | 0.485 | 31.745 | 17.477 | 1.00 41.97 | A | C |
| ATOM | 1628 | CG | PRO | A | 447 | 1.855 | 32.261 | 17.813 | 1.00 41.62 | A | C |
| ATOM | 1629 | C | PRO | A | 447 | 0.609 | 31.100 | 15.014 | 1.00 38.73 | A | C |
| ATOM | 1630 | O | PRO | A | 447 | -0.419 | 30.880 | 14.388 | 1.00 38.04 | A | O |
| ATOM | 1631 | N | GLU | A | 448 | 1.665 | 31.706 | 14.482 | 1.00 36.43 | A | N |
| ATOM | 1632 | CA | GLU | A | 448 | 1.654 | 32.198 | 13.112 | 1.00 36.64 | A | C |
| ATOM | 1633 | CB | GLU | A | 448 | 2.812 | 33.176 | 12.881 | 1.00 38.56 | A | C |
| ATOM | 1634 | CG | GLU | A | 448 | 2.728 | 34.447 | 13.694 | 1.00 41.25 | A | C |
| ATOM | 1635 | CD | GLU | A | 448 | 3.983 | 35.297 | 13.593 | 1.00 42.39 | A | C |
| ATOM | 1636 | OE1 | GLU | A | 448 | 5.018 | 34.805 | 13.104 | 1.00 44.95 | A | O |
| ATOM | 1637 | OE2 | GLU | A | 448 | 3.943 | 36.469 | 14.009 | 1.00 43.75 | A | O |
| ATOM | 1638 | C | GLU | A | 448 | 1.711 | 31.066 | 12.081 | 1.00 34.80 | A | C |
| ATOM | 1639 | O | GLU | A | 448 | 1.114 | 31.167 | 11.009 | 1.00 33.88 | A | O |
| ATOM | 1640 | N | VAL | A | 449 | 2.461 | 30.008 | 12.388 | 1.00 33.75 | A | N |
| ATOM | 1641 | CA | VAL | A | 449 | 2.571 | 28.861 | 11.483 | 1.00 31.12 | A | C |
| ATOM | 1642 | CB | VAL | A | 449 | 3.612 | 27.798 | 11.981 | 1.00 30.06 | A | C |
| ATOM | 1643 | CG1 | VAL | A | 449 | 3.422 | 26.463 | 11.252 | 1.00 27.51 | A | C |
| ATOM | 1644 | CG2 | VAL | A | 449 | 5.032 | 28.306 | 11.751 | 1.00 28.28 | A | C |
| ATOM | 1645 | C | VAL | A | 449 | 1.195 | 28.234 | 11.381 | 1.00 30.25 | A | C |
| ATOM | 1646 | O | VAL | A | 449 | 0.795 | 27.778 | 10.308 | 1.00 28.49 | A | O |
| ATOM | 1647 | N | ILE | A | 450 | 0.484 | 28.230 | 12.511 | 1.00 31.26 | A | N |
| ATOM | 1648 | CA | ILE | A | 450 | -0.876 | 27.693 | 12.598 | 1.00 32.41 | A | C |
| ATOM | 1649 | CB | ILE | A | 450 | -1.390 | 27.690 | 14.059 | 1.00 34.00 | A | C |
| ATOM | 1650 | CG2 | ILE | A | 450 | -2.846 | 27.205 | 14.123 | 1.00 34.26 | A | C |
| ATOM | 1651 | CG1 | ILE | A | 450 | -0.484 | 26.821 | 14.928 | 1.00 35.40 | A | C |
| ATOM | 1652 | CD1 | ILE | A | 450 | -0.337 | 25.423 | 14.418 | 1.00 37.85 | A | C |
| ATOM | 1653 | C | ILE | A | 450 | -1.870 | 28.473 | 11.720 | 1.00 30.33 | A | C |
| ATOM | 1654 | O | ILE | A | 450 | -2.615 | 27.871 | 10.944 | 1.00 30.13 | A | O |
| ATOM | 1655 | N | GLN | A | 451 | -1.859 | 29.803 | 11.813 | 1.00 29.45 | A | N |
| ATOM | 1656 | CA | GLN | A | 451 | -2.774 | 30.597 | 11.000 | 1.00 30.23 | A | C |
| ATOM | 1657 | CB | GLN | A | 451 | -3.044 | 31.994 | 11.599 | 1.00 32.65 | A | C |
| ATOM | 1658 | CG | GLN | A | 451 | -1.842 | 32.908 | 11.781 | 1.00 37.73 | A | C |
| ATOM | 1659 | CD | GLN | A | 451 | -1.992 | 33.852 | 12.977 | 1.00 38.93 | A | C |
| ATOM | 1660 | OE1 | GLN | A | 451 | -1.556 | 35.008 | 12.935 | 1.00 40.50 | A | O |
| ATOM | 1661 | NE2 | GLN | A | 451 | -2.570 | 33.345 | 14.064 | 1.00 40.00 | A | N |
| ATOM | 1662 | C | GLN | A | 451 | -2.419 | 30.648 | 9.517 | 1.00 27.54 | A | C |
| ATOM | 1663 | O | GLN | A | 451 | -3.282 | 30.951 | 8.698 | 1.00 27.12 | A | O |
| ATOM | 1664 | N | ASN | A | 452 | -1.167 | 30.321 | 9.178 | 1.00 25.73 | A | N |
| ATOM | 1665 | CA | ASN | A | 452 | -0.701 | 30.273 | 7.786 | 1.00 23.63 | A | C |
| ATOM | 1666 | CB | ASN | A | 452 | 0.813 | 30.430 | 7.705 | 1.00 25.30 | A | C |
| ATOM | 1667 | CG | ASN | A | 452 | 1.235 | 31.856 | 7.506 | 1.00 27.09 | A | C |

Figure 4

| | | | | | | | | | | |
|---|---|---|---|---|---|---|---|---|---|---|
| ATOM | 1668 | OD1 | ASN | A | 452 | 1.515 | 32.282 | 6.388 | 1.00 28.97 | A O |
| ATOM | 1669 | ND2 | ASN | A | 452 | 1.290 | 32.614 | 8.597 | 1.00 27.68 | A N |
| ATOM | 1670 | C | ASN | A | 452 | -1.073 | 28.911 | 7.205 | 1.00 22.60 | A C |
| ATOM | 1671 | O | ASN | A | 452 | -1.462 | 28.821 | 6.053 | 1.00 22.31 | A O |
| ATOM | 1672 | N | LEU | A | 453 | -0.907 | 27.852 | 7.999 | 1.00 21.64 | A N |
| ATOM | 1673 | CA | LEU | A | 453 | -1.259 | 26.501 | 7.581 | 1.00 22.35 | A C |
| ATOM | 1674 | CB | LEU | A | 453 | -0.821 | 25.465 | 8.616 | 1.00 23.27 | A C |
| ATOM | 1675 | CG | LEU | A | 453 | 0.634 | 25.003 | 8.570 | 1.00 24.29 | A C |
| ATOM | 1676 | CD1 | LEU | A | 453 | 0.784 | 23.835 | 9.527 | 1.00 25.84 | A C |
| ATOM | 1677 | CD2 | LEU | A | 453 | 1.026 | 24.567 | 7.158 | 1.00 24.25 | A C |
| ATOM | 1678 | C | LEU | A | 453 | -2.761 | 26.412 | 7.396 | 1.00 23.16 | A C |
| ATOM | 1679 | O | LEU | A | 453 | -3.245 | 25.609 | 6.600 | 1.00 22.58 | A O |
| ATOM | 1680 | N | GLU | A | 454 | -3.497 | 27.187 | 8.187 | 1.00 23.24 | A N |
| ATOM | 1681 | CA | GLU | A | 454 | -4.946 | 27.235 | 8.066 | 1.00 26.50 | A C |
| ATOM | 1682 | CB | GLU | A | 454 | -5.552 | 28.202 | 9.083 | 1.00 30.40 | A C |
| ATOM | 1683 | CG | GLU | A | 454 | -5.722 | 27.663 | 10.508 | 1.00 35.60 | A C |
| ATOM | 1684 | CD | GLU | A | 454 | -6.003 | 28.778 | 11.532 | 1.00 38.23 | A C |
| ATOM | 1685 | OE1 | GLU | A | 454 | -5.836 | 28.521 | 12.752 | 1.00 38.98 | A O |
| ATOM | 1686 | OE2 | GLU | A | 454 | -6.367 | 29.912 | 11.106 | 1.00 39.46 | A O |
| ATOM | 1687 | C | GLU | A | 454 | -5.280 | 27.739 | 6.667 | 1.00 24.97 | A C |
| ATOM | 1688 | O | GLU | A | 454 | -6.244 | 27.291 | 6.060 | 1.00 24.35 | A O |
| ATOM | 1689 | N | ARG | A | 455 | -4.477 | 28.683 | 6.179 | 1.00 24.06 | A N |
| ATOM | 1690 | CA | ARG | A | 455 | -4.651 | 29.278 | 4.865 | 1.00 23.80 | A C |
| ATOM | 1691 | CB | ARG | A | 455 | -4.208 | 30.737 | 4.888 | 1.00 25.87 | A C |
| ATOM | 1692 | CG | ARG | A | 455 | -4.949 | 31.678 | 5.849 | 1.00 29.54 | A C |
| ATOM | 1693 | CD | ARG | A | 455 | -4.353 | 33.105 | 5.735 | 1.00 33.07 | A C |
| ATOM | 1694 | NE | ARG | A | 455 | -2.914 | 32.996 | 5.499 | 1.00 38.56 | A N |
| ATOM | 1695 | CZ | ARG | A | 455 | -2.294 | 33.317 | 4.359 | 1.00 39.36 | A C |
| ATOM | 1696 | NH1 | ARG | A | 455 | -2.979 | 33.823 | 3.343 | 1.00 38.59 | A N |
| ATOM | 1697 | NH2 | ARG | A | 455 | -1.029 | 32.936 | 4.159 | 1.00 39.05 | A N |
| ATOM | 1698 | C | ARG | A | 455 | -3.915 | 28.533 | 3.739 | 1.00 21.83 | A C |
| ATOM | 1699 | O | ARG | A | 455 | -3.778 | 29.039 | 2.625 | 1.00 19.50 | A O |
| ATOM | 1700 | N | GLY | A | 456 | -3.433 | 27.336 | 4.049 | 1.00 22.91 | A N |
| ATOM | 1701 | CA | GLY | A | 456 | -2.725 | 26.511 | 3.081 | 1.00 21.54 | A C |
| ATOM | 1702 | C | GLY | A | 456 | -1.290 | 26.879 | 2.756 | 1.00 21.27 | A C |
| ATOM | 1703 | O | GLY | A | 456 | -0.746 | 26.408 | 1.760 | 1.00 21.75 | A O |
| ATOM | 1704 | N | TYR | A | 457 | -0.659 | 27.696 | 3.591 | 1.00 22.36 | A N |
| ATOM | 1705 | CA | TYR | A | 457 | 0.717 | 28.120 | 3.351 | 1.00 21.28 | A C |
| ATOM | 1706 | CB | TYR | A | 457 | 1.130 | 29.141 | 4.402 | 1.00 20.55 | A C |
| ATOM | 1707 | CG | TYR | A | 457 | 2.519 | 29.698 | 4.249 | 1.00 21.22 | A C |
| ATOM | 1708 | CD1 | TYR | A | 457 | 2.743 | 30.937 | 3.630 | 1.00 20.56 | A C |
| ATOM | 1709 | CE1 | TYR | A | 457 | 4.034 | 31.460 | 3.535 | 1.00 20.93 | A C |
| ATOM | 1710 | CD2 | TYR | A | 457 | 3.621 | 29.000 | 4.762 | 1.00 22.40 | A C |
| ATOM | 1711 | CE2 | TYR | A | 457 | 4.922 | 29.512 | 4.671 | 1.00 21.20 | A C |
| ATOM | 1712 | CZ | TYR | A | 457 | 5.116 | 30.733 | 4.061 | 1.00 21.45 | A C |
| ATOM | 1713 | OH | TYR | A | 457 | 6.396 | 31.220 | 3.984 | 1.00 21.02 | A O |
| ATOM | 1714 | C | TYR | A | 457 | 1.756 | 27.011 | 3.269 | 1.00 21.59 | A C |
| ATOM | 1715 | O | TYR | A | 457 | 1.699 | 26.015 | 3.996 | 1.00 21.74 | A O |
| ATOM | 1716 | N | ARG | A | 458 | 2.692 | 27.189 | 2.337 | 1.00 22.46 | A N |
| ATOM | 1717 | CA | ARG | A | 458 | 3.802 | 26.270 | 2.132 | 1.00 22.12 | A C |
| ATOM | 1718 | CB | ARG | A | 458 | 3.640 | 25.427 | 0.859 | 1.00 20.92 | A C |
| ATOM | 1719 | CG | ARG | A | 458 | 2.501 | 24.428 | 0.884 | 1.00 19.39 | A C |
| ATOM | 1720 | CD | ARG | A | 458 | 2.600 | 23.481 | 2.067 | 1.00 19.40 | A C |
| ATOM | 1721 | NE | ARG | A | 458 | 1.514 | 22.503 | 2.082 | 1.00 18.66 | A N |
| ATOM | 1722 | CZ | ARG | A | 458 | 0.426 | 22.583 | 2.842 | 1.00 18.51 | A C |
| ATOM | 1723 | NH1 | ARG | A | 458 | 0.268 | 23.602 | 3.669 | 1.00 20.42 | A N |
| ATOM | 1724 | NH2 | ARG | A | 458 | -0.529 | 21.666 | 2.748 | 1.00 17.89 | A N |
| ATOM | 1725 | C | ARG | A | 458 | 5.064 | 27.111 | 2.028 | 1.00 23.26 | A C |
| ATOM | 1726 | O | ARG | A | 458 | 5.052 | 28.205 | 1.460 | 1.00 23.14 | A O |
| ATOM | 1727 | N | MET | A | 459 | 6.138 | 26.621 | 2.638 | 1.00 25.41 | A N |

Figure 4

```
ATOM   1728  CA  MET A 459       7.428  27.293   2.586  1.00 25.27      A  C
ATOM   1729  CB  MET A 459       8.469  26.530   3.399  1.00 25.60      A  C
ATOM   1730  CG  MET A 459       8.388  26.746   4.892  1.00 28.41      A  C
ATOM   1731  SD  MET A 459       9.765  25.951   5.707  1.00 30.98      A  S
ATOM   1732  CE  MET A 459       9.159  24.285   5.941  1.00 28.47      A  C
ATOM   1733  C   MET A 459       7.910  27.335   1.151  1.00 24.88      A  C
ATOM   1734  O   MET A 459       7.671  26.397   0.369  1.00 23.10      A  O
ATOM   1735  N   VAL A 460       8.598  28.422   0.808  1.00 27.28      A  N
ATOM   1736  CA  VAL A 460       9.146  28.583  -0.542  1.00 28.77      A  C
ATOM   1737  CB  VAL A 460       9.384  30.071  -0.870  1.00 28.41      A  C
ATOM   1738  CG1 VAL A 460       8.099  30.846  -0.638  1.00 28.73      A  C
ATOM   1739  CG2 VAL A 460      10.505  30.646  -0.008  1.00 27.40      A  C
ATOM   1740  C   VAL A 460      10.437  27.757  -0.669  1.00 29.21      A  C
ATOM   1741  O   VAL A 460      10.901  27.193   0.322  1.00 28.96      A  O
ATOM   1742  N   ARG A 461      10.994  27.640  -1.873  1.00 28.87      A  N
ATOM   1743  CA  ARG A 461      12.218  26.856  -2.054  1.00 28.19      A  C
ATOM   1744  CB  ARG A 461      12.534  26.694  -3.537  1.00 29.37      A  C
ATOM   1745  CG  ARG A 461      13.508  25.568  -3.855  1.00 31.40      A  C
ATOM   1746  CD  ARG A 461      13.907  25.582  -5.313  1.00 34.60      A  C
ATOM   1747  NE  ARG A 461      14.325  26.919  -5.726  1.00 39.27      A  N
ATOM   1748  CZ  ARG A 461      15.485  27.487  -5.392  1.00 42.75      A  C
ATOM   1749  NH1 ARG A 461      16.389  26.837  -4.647  1.00 44.03      A  N
ATOM   1750  NH2 ARG A 461      15.704  28.755  -5.717  1.00 44.44      A  N
ATOM   1751  C   ARG A 461      13.393  27.501  -1.314  1.00 27.96      A  C
ATOM   1752  O   ARG A 461      13.711  28.668  -1.531  1.00 25.00      A  O
ATOM   1753  N   PRO A 462      14.018  26.751  -0.388  1.00 29.44      A  N
ATOM   1754  CD  PRO A 462      13.677  25.362  -0.031  1.00 29.26      A  C
ATOM   1755  CA  PRO A 462      15.162  27.226   0.411  1.00 31.97      A  C
ATOM   1756  CB  PRO A 462      15.491  26.018   1.308  1.00 30.75      A  C
ATOM   1757  CG  PRO A 462      14.184  25.277   1.393  1.00 30.30      A  C
ATOM   1758  C   PRO A 462      16.367  27.582  -0.457  1.00 32.88      A  C
ATOM   1759  O   PRO A 462      16.628  26.921  -1.467  1.00 31.38      A  O
ATOM   1760  N   ASP A 463      17.075  28.645  -0.083  1.00 36.51      A  N
ATOM   1761  CA  ASP A 463      18.265  29.045  -0.825  1.00 40.68      A  C
ATOM   1762  CB  ASP A 463      18.995  30.210  -0.134  1.00 41.49      A  C
ATOM   1763  CG  ASP A 463      18.217  31.526  -0.183  1.00 41.94      A  C
ATOM   1764  OD1 ASP A 463      17.331  31.675  -1.048  1.00 42.58      A  O
ATOM   1765  OD2 ASP A 463      18.505  32.424   0.642  1.00 42.08      A  O
ATOM   1766  C   ASP A 463      19.158  27.802  -0.837  1.00 43.01      A  C
ATOM   1767  O   ASP A 463      19.365  27.160   0.205  1.00 43.80      A  O
ATOM   1768  N   ASN A 464      19.594  27.416  -2.034  1.00 44.63      A  N
ATOM   1769  CA  ASN A 464      20.441  26.242  -2.221  1.00 45.52      A  C
ATOM   1770  CB  ASN A 464      21.738  26.396  -1.437  1.00 48.78      A  C
ATOM   1771  CG  ASN A 464      22.600  27.507  -1.991  1.00 51.28      A  C
ATOM   1772  OD1 ASN A 464      22.955  27.493  -3.181  1.00 52.16      A  O
ATOM   1773  ND2 ASN A 464      22.902  28.505  -1.155  1.00 51.55      A  N
ATOM   1774  C   ASN A 464      19.767  24.898  -1.944  1.00 44.56      A  C
ATOM   1775  O   ASN A 464      20.197  24.109  -1.099  1.00 45.35      A  O
ATOM   1776  N   CYS A 465      18.708  24.651  -2.705  1.00 41.29      A  N
ATOM   1777  CA  CYS A 465      17.924  23.430  -2.630  1.00 36.36      A  C
ATOM   1778  CB  CYS A 465      16.671  23.658  -1.771  1.00 35.30      A  C
ATOM   1779  SG  CYS A 465      15.426  22.331  -1.814  1.00 31.71      A  S
ATOM   1780  C   CYS A 465      17.512  23.209  -4.078  1.00 35.28      A  C
ATOM   1781  O   CYS A 465      16.964  24.119  -4.692  1.00 37.06      A  O
ATOM   1782  N   PRO A 466      17.833  22.039  -4.660  1.00 32.51      A  N
ATOM   1783  CD  PRO A 466      18.574  20.920  -4.055  1.00 31.47      A  C
ATOM   1784  CA  PRO A 466      17.470  21.737  -6.047  1.00 32.10      A  C
ATOM   1785  CB  PRO A 466      17.920  20.287  -6.195  1.00 31.46      A  C
ATOM   1786  CG  PRO A 466      19.063  20.186  -5.266  1.00 32.05      A  C
ATOM   1787  C   PRO A 466      15.946  21.837  -6.215  1.00 33.51      A  C
```

Figure 4

| ATOM | 1788 | O   | PRO A 466 | 15.217 | 21.691 | -5.246  | 1.00 | 35.07 | A | O |
|------|------|-----|-----------|--------|--------|---------|------|-------|---|---|
| ATOM | 1789 | N   | GLU A 467 | 15.458 | 22.079 | -7.427  | 1.00 | 34.71 | A | N |
| ATOM | 1790 | CA  | GLU A 467 | 14.014 | 22.178 | -7.636  | 1.00 | 35.31 | A | C |
| ATOM | 1791 | CB  | GLU A 467 | 13.672 | 22.761 | -9.015  | 1.00 | 36.02 | A | C |
| ATOM | 1792 | CG  | GLU A 467 | 12.989 | 24.140 | -8.954  | 1.00 | 37.51 | A | C |
| ATOM | 1793 | CD  | GLU A 467 | 11.560 | 24.104 | -8.386  | 1.00 | 38.04 | A | C |
| ATOM | 1794 | OE1 | GLU A 467 | 11.249 | 24.915 | -7.481  | 1.00 | 37.18 | A | O |
| ATOM | 1795 | OE2 | GLU A 467 | 10.738 | 23.291 | -8.869  | 1.00 | 37.45 | A | O |
| ATOM | 1796 | C   | GLU A 467 | 13.333 | 20.840 | -7.461  | 1.00 | 34.61 | A | C |
| ATOM | 1797 | O   | GLU A 467 | 12.240 | 20.783 | -6.921  | 1.00 | 35.23 | A | O |
| ATOM | 1798 | N   | GLU A 468 | 13.968 | 19.767 | -7.921  | 1.00 | 35.09 | A | N |
| ATOM | 1799 | CA  | GLU A 468 | 13.384 | 18.437 | -7.781  | 1.00 | 36.69 | A | C |
| ATOM | 1800 | CB  | GLU A 468 | 14.247 | 17.360 | -8.458  | 1.00 | 40.85 | A | C |
| ATOM | 1801 | CG  | GLU A 468 | 14.455 | 17.521 | -9.964  | 1.00 | 44.67 | A | C |
| ATOM | 1802 | CD  | GLU A 468 | 15.418 | 18.659 | -10.322 | 1.00 | 48.81 | A | C |
| ATOM | 1803 | OE1 | GLU A 468 | 16.349 | 18.977 | -9.527  | 1.00 | 48.90 | A | O |
| ATOM | 1804 | OE2 | GLU A 468 | 15.240 | 19.235 | -11.421 | 1.00 | 51.49 | A | O |
| ATOM | 1805 | C   | GLU A 468 | 13.217 | 18.109 | -6.293  | 1.00 | 35.41 | A | C |
| ATOM | 1806 | O   | GLU A 468 | 12.202 | 17.517 | -5.893  | 1.00 | 34.91 | A | O |
| ATOM | 1807 | N   | LEU A 469 | 14.198 | 18.513 | -5.475  | 1.00 | 31.88 | A | N |
| ATOM | 1808 | CA  | LEU A 469 | 14.139 | 18.282 | -4.026  | 1.00 | 27.62 | A | C |
| ATOM | 1809 | CB  | LEU A 469 | 15.467 | 18.648 | -3.340  | 1.00 | 25.02 | A | C |
| ATOM | 1810 | CG  | LEU A 469 | 15.501 | 18.410 | -1.824  | 1.00 | 25.25 | A | C |
| ATOM | 1811 | CD1 | LEU A 469 | 15.311 | 16.936 | -1.507  | 1.00 | 24.23 | A | C |
| ATOM | 1812 | CD2 | LEU A 469 | 16.799 | 18.908 | -1.235  | 1.00 | 24.27 | A | C |
| ATOM | 1813 | C   | LEU A 469 | 12.964 | 19.055 | -3.396  | 1.00 | 25.08 | A | C |
| ATOM | 1814 | O   | LEU A 469 | 12.294 | 18.538 | -2.491  | 1.00 | 23.24 | A | O |
| ATOM | 1815 | N   | TYR A 470 | 12.717 | 20.277 | -3.885  | 1.00 | 24.16 | A | N |
| ATOM | 1816 | CA  | TYR A 470 | 11.611 | 21.109 | -3.397  | 1.00 | 24.77 | A | C |
| ATOM | 1817 | CB  | TYR A 470 | 11.705 | 22.554 | -3.898  | 1.00 | 22.54 | A | C |
| ATOM | 1818 | CG  | TYR A 470 | 10.553 | 23.433 | -3.447  | 1.00 | 23.25 | A | C |
| ATOM | 1819 | CD1 | TYR A 470 | 10.355 | 23.728 | -2.095  | 1.00 | 24.25 | A | C |
| ATOM | 1820 | CE1 | TYR A 470 | 9.286  | 24.537 | -1.675  | 1.00 | 23.89 | A | C |
| ATOM | 1821 | CD2 | TYR A 470 | 9.646  | 23.969 | -4.374  | 1.00 | 24.00 | A | C |
| ATOM | 1822 | CE2 | TYR A 470 | 8.570  | 24.781 | -3.964  | 1.00 | 23.70 | A | C |
| ATOM | 1823 | CZ  | TYR A 470 | 8.400  | 25.054 | -2.615  | 1.00 | 23.70 | A | C |
| ATOM | 1824 | OH  | TYR A 470 | 7.347  | 25.821 | -2.184  | 1.00 | 23.54 | A | O |
| ATOM | 1825 | C   | TYR A 470 | 10.257 | 20.514 | -3.787  | 1.00 | 25.73 | A | C |
| ATOM | 1826 | O   | TYR A 470 | 9.297  | 20.590 | -3.018  | 1.00 | 28.05 | A | O |
| ATOM | 1827 | N   | GLN A 471 | 10.166 | 19.928 | -4.976  | 1.00 | 24.45 | A | N |
| ATOM | 1828 | CA  | GLN A 471 | 8.905  | 19.331 | -5.383  | 1.00 | 24.28 | A | C |
| ATOM | 1829 | CB  | GLN A 471 | 8.898  | 19.023 | -6.883  | 1.00 | 24.68 | A | C |
| ATOM | 1830 | CG  | GLN A 471 | 8.793  | 20.276 | -7.762  | 1.00 | 23.63 | A | C |
| ATOM | 1831 | CD  | GLN A 471 | 7.692  | 21.213 | -7.315  | 1.00 | 24.36 | A | C |
| ATOM | 1832 | OE1 | GLN A 471 | 6.585  | 20.786 | -6.980  | 1.00 | 24.93 | A | O |
| ATOM | 1833 | NE2 | GLN A 471 | 7.999  | 22.497 | -7.275  | 1.00 | 24.94 | A | N |
| ATOM | 1834 | C   | GLN A 471 | 8.658  | 18.085 | -4.537  | 1.00 | 24.43 | A | C |
| ATOM | 1835 | O   | GLN A 471 | 7.511  | 17.720 | -4.252  | 1.00 | 21.74 | A | O |
| ATOM | 1836 | N   | LEU A 472 | 9.748  | 17.497 | -4.055  | 1.00 | 24.66 | A | N |
| ATOM | 1837 | CA  | LEU A 472 | 9.653  | 16.322 | -3.210  | 1.00 | 25.02 | A | C |
| ATOM | 1838 | CB  | LEU A 472 | 10.998 | 15.606 | -3.129  | 1.00 | 28.36 | A | C |
| ATOM | 1839 | CG  | LEU A 472 | 10.932 | 14.086 | -3.011  | 1.00 | 29.95 | A | C |
| ATOM | 1840 | CD1 | LEU A 472 | 10.201 | 13.483 | -4.209  | 1.00 | 28.61 | A | C |
| ATOM | 1841 | CD2 | LEU A 472 | 12.362 | 13.549 | -2.911  | 1.00 | 30.96 | A | C |
| ATOM | 1842 | C   | LEU A 472 | 9.169  | 16.748 | -1.825  | 1.00 | 23.98 | A | C |
| ATOM | 1843 | O   | LEU A 472 | 8.454  | 15.991 | -1.171  | 1.00 | 26.63 | A | O |
| ATOM | 1844 | N   | MET A 473 | 9.533  | 17.951 | -1.380  | 1.00 | 21.07 | A | N |
| ATOM | 1845 | CA  | MET A 473 | 9.064  | 18.448 | -0.084  | 1.00 | 19.93 | A | C |
| ATOM | 1846 | CB  | MET A 473 | 9.819  | 19.711 | 0.323   | 1.00 | 19.55 | A | C |
| ATOM | 1847 | CG  | MET A 473 | 11.344 | 19.575 | 0.407   | 1.00 | 18.75 | A | C |

Figure 4

| | | | | | | | | | | | |
|---|---|---|---|---|---|---|---|---|---|---|---|
| ATOM | 1848 | SD | MET | A | 473 | 12.065 | 21.157 | 0.761 | 1.00 | 22.31 | A S |
| ATOM | 1849 | CE | MET | A | 473 | 13.753 | 20.688 | 1.248 | 1.00 | 16.61 | A C |
| ATOM | 1850 | C | MET | A | 473 | 7.570 | 18.788 | -0.236 | 1.00 | 20.87 | A C |
| ATOM | 1851 | O | MET | A | 473 | 6.755 | 18.479 | 0.634 | 1.00 | 17.40 | A O |
| ATOM | 1852 | N | ARG | A | 474 | 7.215 | 19.387 | -1.376 | 1.00 | 21.93 | A N |
| ATOM | 1853 | CA | ARG | A | 474 | 5.821 | 19.767 | -1.677 | 1.00 | 22.30 | A C |
| ATOM | 1854 | CB | ARG | A | 474 | 5.737 | 20.544 | -2.998 | 1.00 | 19.95 | A C |
| ATOM | 1855 | CG | ARG | A | 474 | 6.365 | 21.912 | -2.910 | 1.00 | 20.27 | A C |
| ATOM | 1856 | CD | ARG | A | 474 | 5.720 | 22.752 | -1.810 | 1.00 | 23.49 | A C |
| ATOM | 1857 | NE | ARG | A | 474 | 4.319 | 23.053 | -2.117 | 1.00 | 25.88 | A N |
| ATOM | 1858 | CZ | ARG | A | 474 | 3.885 | 24.191 | -2.658 | 1.00 | 25.60 | A C |
| ATOM | 1859 | NH1 | ARG | A | 474 | 4.732 | 25.164 | -2.958 | 1.00 | 23.82 | A N |
| ATOM | 1860 | NH2 | ARG | A | 474 | 2.599 | 24.348 | -2.919 | 1.00 | 24.99 | A N |
| ATOM | 1861 | C | ARG | A | 474 | 4.861 | 18.567 | -1.678 | 1.00 | 20.89 | A C |
| ATOM | 1862 | O | ARG | A | 474 | 3.696 | 18.685 | -1.268 | 1.00 | 19.14 | A O |
| ATOM | 1863 | N | LEU | A | 475 | 5.365 | 17.419 | -2.133 | 1.00 | 20.76 | A N |
| ATOM | 1864 | CA | LEU | A | 475 | 4.587 | 16.194 | -2.154 | 1.00 | 20.87 | A C |
| ATOM | 1865 | CB | LEU | A | 475 | 5.240 | 15.138 | -3.050 | 1.00 | 22.06 | A C |
| ATOM | 1866 | CG | LEU | A | 475 | 5.059 | 15.332 | -4.566 | 1.00 | 23.94 | A C |
| ATOM | 1867 | CD1 | LEU | A | 475 | 5.624 | 14.127 | -5.301 | 1.00 | 23.31 | A C |
| ATOM | 1868 | CD2 | LEU | A | 475 | 3.585 | 15.516 | -4.919 | 1.00 | 22.72 | A C |
| ATOM | 1869 | C | LEU | A | 475 | 4.419 | 15.676 | -0.717 | 1.00 | 22.46 | A C |
| ATOM | 1870 | O | LEU | A | 475 | 3.393 | 15.076 | -0.387 | 1.00 | 22.14 | A O |
| ATOM | 1871 | N | CYS | A | 476 | 5.424 | 15.906 | 0.133 | 1.00 | 20.65 | A N |
| ATOM | 1872 | CA | CYS | A | 476 | 5.356 | 15.496 | 1.539 | 1.00 | 21.14 | A C |
| ATOM | 1873 | CB | CYS | A | 476 | 6.725 | 15.628 | 2.233 | 1.00 | 20.99 | A C |
| ATOM | 1874 | SG | CYS | A | 476 | 8.060 | 14.516 | 1.657 | 1.00 | 21.78 | A S |
| ATOM | 1875 | C | CYS | A | 476 | 4.358 | 16.387 | 2.289 | 1.00 | 19.10 | A C |
| ATOM | 1876 | O | CYS | A | 476 | 3.852 | 15.990 | 3.334 | 1.00 | 17.00 | A O |
| ATOM | 1877 | N | TRP | A | 477 | 4.159 | 17.613 | 1.783 | 1.00 | 18.44 | A N |
| ATOM | 1878 | CA | TRP | A | 477 | 3.247 | 18.585 | 2.375 | 1.00 | 18.94 | A C |
| ATOM | 1879 | CB | TRP | A | 477 | 3.858 | 19.999 | 2.388 | 1.00 | 18.39 | A C |
| ATOM | 1880 | CG | TRP | A | 477 | 5.202 | 20.114 | 3.066 | 1.00 | 19.63 | A C |
| ATOM | 1881 | CD2 | TRP | A | 477 | 6.253 | 21.033 | 2.729 | 1.00 | 19.52 | A C |
| ATOM | 1882 | CE2 | TRP | A | 477 | 7.345 | 20.757 | 3.583 | 1.00 | 20.00 | A C |
| ATOM | 1883 | CE3 | TRP | A | 477 | 6.373 | 22.071 | 1.784 | 1.00 | 19.31 | A C |
| ATOM | 1884 | CD1 | TRP | A | 477 | 5.693 | 19.338 | 4.089 | 1.00 | 18.96 | A C |
| ATOM | 1885 | NE1 | TRP | A | 477 | 6.974 | 19.715 | 4.399 | 1.00 | 19.47 | A N |
| ATOM | 1886 | CZ2 | TRP | A | 477 | 8.564 | 21.479 | 3.521 | 1.00 | 20.81 | A C |
| ATOM | 1887 | CZ3 | TRP | A | 477 | 7.584 | 22.791 | 1.718 | 1.00 | 19.44 | A C |
| ATOM | 1888 | CH2 | TRP | A | 477 | 8.658 | 22.490 | 2.588 | 1.00 | 20.34 | A C |
| ATOM | 1889 | C | TRP | A | 477 | 1.850 | 18.652 | 1.722 | 1.00 | 17.34 | A C |
| ATOM | 1890 | O | TRP | A | 477 | 1.194 | 19.692 | 1.796 | 1.00 | 19.84 | A O |
| ATOM | 1891 | N | LYS | A | 478 | 1.398 | 17.578 | 1.079 | 1.00 | 17.08 | A N |
| ATOM | 1892 | CA | LYS | A | 478 | 0.056 | 17.595 | 0.486 | 1.00 | 18.97 | A C |
| ATOM | 1893 | CB | LYS | A | 478 | -0.238 | 16.329 | -0.328 | 1.00 | 18.36 | A C |
| ATOM | 1894 | CG | LYS | A | 478 | 0.489 | 16.226 | -1.658 | 1.00 | 20.44 | A C |
| ATOM | 1895 | CD | LYS | A | 478 | 0.189 | 17.378 | -2.611 | 1.00 | 21.35 | A C |
| ATOM | 1896 | CE | LYS | A | 478 | -1.063 | 17.126 | -3.443 | 1.00 | 23.36 | A C |
| ATOM | 1897 | NZ | LYS | A | 478 | -1.536 | 18.404 | -4.032 | 1.00 | 26.46 | A N |
| ATOM | 1898 | C | LYS | A | 478 | -0.934 | 17.694 | 1.642 | 1.00 | 20.05 | A C |
| ATOM | 1899 | O | LYS | A | 478 | -0.697 | 17.104 | 2.706 | 1.00 | 21.55 | A O |
| ATOM | 1900 | N | GLU | A | 479 | -2.022 | 18.442 | 1.454 | 1.00 | 21.13 | A N |
| ATOM | 1901 | CA | GLU | A | 479 | -3.015 | 18.619 | 2.510 | 1.00 | 21.81 | A C |
| ATOM | 1902 | CB | GLU | A | 479 | -4.130 | 19.550 | 2.023 | 1.00 | 21.21 | A C |
| ATOM | 1903 | CG | GLU | A | 479 | -5.066 | 20.038 | 3.116 | 1.00 | 21.87 | A C |
| ATOM | 1904 | CD | GLU | A | 479 | -4.342 | 20.839 | 4.184 | 1.00 | 24.16 | A C |
| ATOM | 1905 | OE1 | GLU | A | 479 | -3.444 | 21.636 | 3.845 | 1.00 | 25.36 | A O |
| ATOM | 1906 | OE2 | GLU | A | 479 | -4.641 | 20.665 | 5.375 | 1.00 | 23.99 | A O |
| ATOM | 1907 | C | GLU | A | 479 | -3.580 | 17.273 | 2.994 | 1.00 | 21.81 | A C |

Figure 4

| | | | | | | | | | | |
|---|---|---|---|---|---|---|---|---|---|---|
| ATOM | 1908 | O | GLU | A | 479 | -3.689 | 17.023 | 4.205 | 1.00 19.36 | A O |
| ATOM | 1909 | N | ARG | A | 480 | -3.876 | 16.390 | 2.042 | 1.00 24.03 | A N |
| ATOM | 1910 | CA | ARG | A | 480 | -4.421 | 15.067 | 2.353 | 1.00 25.55 | A C |
| ATOM | 1911 | CB | ARG | A | 480 | -5.368 | 14.603 | 1.261 | 1.00 27.04 | A C |
| ATOM | 1912 | CG | ARG | A | 480 | -6.598 | 15.407 | 1.109 | 1.00 29.38 | A C |
| ATOM | 1913 | CD | ARG | A | 480 | -7.132 | 15.066 | -0.233 | 1.00 35.00 | A C |
| ATOM | 1914 | NE | ARG | A | 480 | -8.432 | 15.653 | -0.469 | 1.00 41.35 | A N |
| ATOM | 1915 | CZ | ARG | A | 480 | -8.969 | 15.807 | -1.673 | 1.00 44.79 | A C |
| ATOM | 1916 | NH1 | ARG | A | 480 | -8.309 | 15.415 | -2.765 | 1.00 46.65 | A N |
| ATOM | 1917 | NH2 | ARG | A | 480 | -10.176 | 16.355 | -1.781 | 1.00 47.20 | A N |
| ATOM | 1918 | C | ARG | A | 480 | -3.322 | 14.026 | 2.520 | 1.00 23.56 | A C |
| ATOM | 1919 | O | ARG | A | 480 | -2.520 | 13.820 | 1.615 | 1.00 23.44 | A O |
| ATOM | 1920 | N | PRO | A | 481 | -3.358 | 13.282 | 3.639 | 1.00 22.95 | A N |
| ATOM | 1921 | CD | PRO | A | 481 | -4.431 | 13.309 | 4.651 | 1.00 23.26 | A C |
| ATOM | 1922 | CA | PRO | A | 481 | -2.392 | 12.249 | 3.977 | 1.00 23.29 | A C |
| ATOM | 1923 | CB | PRO | A | 481 | -3.039 | 11.583 | 5.203 | 1.00 23.17 | A C |
| ATOM | 1924 | CG | PRO | A | 481 | -3.771 | 12.668 | 5.831 | 1.00 22.08 | A C |
| ATOM | 1925 | C | PRO | A | 481 | -2.146 | 11.247 | 2.850 | 1.00 23.88 | A C |
| ATOM | 1926 | O | PRO | A | 481 | -0.992 | 10.866 | 2.590 | 1.00 22.61 | A O |
| ATOM | 1927 | N | GLU | A | 482 | -3.223 | 10.838 | 2.177 | 1.00 22.42 | A N |
| ATOM | 1928 | CA | GLU | A | 482 | -3.145 | 9.857 | 1.095 | 1.00 20.83 | A C |
| ATOM | 1929 | CB | GLU | A | 482 | -4.558 | 9.367 | 0.710 | 1.00 22.56 | A C |
| ATOM | 1930 | CG | GLU | A | 482 | -5.427 | 10.374 | -0.057 | 1.00 22.87 | A C |
| ATOM | 1931 | CD | GLU | A | 482 | -6.338 | 11.210 | 0.819 | 1.00 24.98 | A C |
| ATOM | 1932 | OE1 | GLU | A | 482 | -6.125 | 11.292 | 2.059 | 1.00 24.82 | A O |
| ATOM | 1933 | OE2 | GLU | A | 482 | -7.291 | 11.786 | 0.249 | 1.00 26.49 | A O |
| ATOM | 1934 | C | GLU | A | 482 | -2.384 | 10.344 | -0.146 | 1.00 19.35 | A C |
| ATOM | 1935 | O | GLU | A | 482 | -1.929 | 9.539 | -0.960 | 1.00 20.45 | A O |
| ATOM | 1936 | N | ASP | A | 483 | -2.261 | 11.658 | -0.297 | 1.00 19.48 | A N |
| ATOM | 1937 | CA | ASP | A | 483 | -1.534 | 12.223 | -1.432 | 1.00 20.25 | A C |
| ATOM | 1938 | CB | ASP | A | 483 | -2.125 | 13.574 | -1.810 | 1.00 21.20 | A C |
| ATOM | 1939 | CG | ASP | A | 483 | -3.510 | 13.451 | -2.396 | 1.00 24.34 | A C |
| ATOM | 1940 | OD1 | ASP | A | 483 | -3.755 | 12.472 | -3.127 | 1.00 24.39 | A O |
| ATOM | 1941 | OD2 | ASP | A | 483 | -4.356 | 14.329 | -2.128 | 1.00 24.14 | A O |
| ATOM | 1942 | C | ASP | A | 483 | -0.024 | 12.362 | -1.185 | 1.00 19.21 | A C |
| ATOM | 1943 | O | ASP | A | 483 | 0.728 | 12.740 | -2.090 | 1.00 17.70 | A O |
| ATOM | 1944 | N | ARG | A | 484 | 0.404 | 12.083 | 0.050 | 1.00 19.85 | A N |
| ATOM | 1945 | CA | ARG | A | 484 | 1.813 | 12.142 | 0.453 | 1.00 19.35 | A C |
| ATOM | 1946 | CB | ARG | A | 484 | 1.917 | 12.431 | 1.952 | 1.00 18.39 | A C |
| ATOM | 1947 | CG | ARG | A | 484 | 1.249 | 13.736 | 2.338 | 1.00 17.40 | A C |
| ATOM | 1948 | CD | ARG | A | 484 | 1.320 | 13.940 | 3.824 | 1.00 18.59 | A C |
| ATOM | 1949 | NE | ARG | A | 484 | 0.466 | 15.044 | 4.233 | 1.00 20.70 | A N |
| ATOM | 1950 | CZ | ARG | A | 484 | -0.204 | 15.099 | 5.382 | 1.00 21.60 | A C |
| ATOM | 1951 | NH1 | ARG | A | 484 | -0.116 | 14.105 | 6.255 | 1.00 21.17 | A N |
| ATOM | 1952 | NH2 | ARG | A | 484 | -1.004 | 16.139 | 5.637 | 1.00 21.02 | A N |
| ATOM | 1953 | C | ARG | A | 484 | 2.489 | 10.816 | 0.101 | 1.00 18.91 | A C |
| ATOM | 1954 | O | ARG | A | 484 | 1.901 | 9.745 | 0.244 | 1.00 18.81 | A O |
| ATOM | 1955 | N | PRO | A | 485 | 3.749 | 10.865 | -0.342 | 1.00 18.48 | A N |
| ATOM | 1956 | CD | PRO | A | 485 | 4.614 | 12.046 | -0.424 | 1.00 19.71 | A C |
| ATOM | 1957 | CA | PRO | A | 485 | 4.492 | 9.662 | -0.716 | 1.00 19.62 | A C |
| ATOM | 1958 | CB | PRO | A | 485 | 5.827 | 10.219 | -1.235 | 1.00 20.76 | A C |
| ATOM | 1959 | CG | PRO | A | 485 | 5.560 | 11.651 | -1.508 | 1.00 21.41 | A C |
| ATOM | 1960 | C | PRO | A | 485 | 4.762 | 8.718 | 0.451 | 1.00 19.74 | A C |
| ATOM | 1961 | O | PRO | A | 485 | 4.664 | 9.104 | 1.613 | 1.00 21.04 | A O |
| ATOM | 1962 | N | THR | A | 486 | 5.073 | 7.473 | 0.132 | 1.00 18.78 | A N |
| ATOM | 1963 | CA | THR | A | 486 | 5.432 | 6.520 | 1.149 | 1.00 20.90 | A C |
| ATOM | 1964 | CB | THR | A | 486 | 5.322 | 5.054 | 0.647 | 1.00 19.71 | A C |
| ATOM | 1965 | OG1 | THR | A | 486 | 6.093 | 4.885 | -0.541 | 1.00 20.73 | A O |
| ATOM | 1966 | CG2 | THR | A | 486 | 3.891 | 4.680 | 0.379 | 1.00 17.95 | A C |
| ATOM | 1967 | C | THR | A | 486 | 6.912 | 6.825 | 1.405 | 1.00 22.01 | A C |

Figure 4

```
ATOM   1968  O    THR A 486       7.551   7.551   0.643  1.00 23.24          A  O
ATOM   1969  N    PHE A 487       7.439   6.338   2.513  1.00 24.01          A  N
ATOM   1970  CA   PHE A 487       8.848   6.540   2.824  1.00 23.18          A  C
ATOM   1971  CB   PHE A 487       9.123   6.268   4.297  1.00 21.05          A  C
ATOM   1972  CG   PHE A 487       8.827   7.434   5.187  1.00 20.99          A  C
ATOM   1973  CD1  PHE A 487       9.604   8.588   5.120  1.00 20.00          A  C
ATOM   1974  CD2  PHE A 487       7.812   7.363   6.138  1.00 21.24          A  C
ATOM   1975  CE1  PHE A 487       9.388   9.643   5.980  1.00 18.42          A  C
ATOM   1976  CE2  PHE A 487       7.590   8.421   7.006  1.00 19.18          A  C
ATOM   1977  CZ   PHE A 487       8.385   9.564   6.924  1.00 19.20          A  C
ATOM   1978  C    PHE A 487       9.633   5.580   1.943  1.00 25.30          A  C
ATOM   1979  O    PHE A 487      10.825   5.779   1.715  1.00 25.97          A  O
ATOM   1980  N    ASP A 488       8.948   4.538   1.455  1.00 26.54          A  N
ATOM   1981  CA   ASP A 488       9.540   3.556   0.552  1.00 28.59          A  C
ATOM   1982  CB   ASP A 488       8.567   2.392   0.328  1.00 32.01          A  C
ATOM   1983  CG   ASP A 488       9.090   1.353  -0.669  1.00 35.18          A  C
ATOM   1984  OD1  ASP A 488      10.308   1.081  -0.660  1.00 36.71          A  O
ATOM   1985  OD2  ASP A 488       8.280   0.795  -1.455  1.00 36.16          A  O
ATOM   1986  C    ASP A 488       9.868   4.268  -0.769  1.00 28.46          A  C
ATOM   1987  O    ASP A 488      10.904   4.016  -1.376  1.00 29.40          A  O
ATOM   1988  N    TYR A 489       8.999   5.187  -1.189  1.00 26.86          A  N
ATOM   1989  CA   TYR A 489       9.235   5.947  -2.402  1.00 24.98          A  C
ATOM   1990  CB   TYR A 489       7.952   6.610  -2.906  1.00 23.64          A  C
ATOM   1991  CG   TYR A 489       8.214   7.647  -3.988  1.00 24.49          A  C
ATOM   1992  CD1  TYR A 489       8.532   7.264  -5.289  1.00 23.40          A  C
ATOM   1993  CE1  TYR A 489       8.822   8.209  -6.270  1.00 23.83          A  C
ATOM   1994  CD2  TYR A 489       8.192   9.014  -3.696  1.00 25.36          A  C
ATOM   1995  CE2  TYR A 489       8.490   9.975  -4.671  1.00 24.93          A  C
ATOM   1996  CZ   TYR A 489       8.806   9.564  -5.957  1.00 24.96          A  C
ATOM   1997  OH   TYR A 489       9.126  10.503  -6.925  1.00 26.27          A  O
ATOM   1998  C    TYR A 489      10.305   7.007  -2.146  1.00 25.87          A  C
ATOM   1999  O    TYR A 489      11.195   7.201  -2.974  1.00 26.09          A  O
ATOM   2000  N    LEU A 490      10.203   7.697  -1.009  1.00 25.58          A  N
ATOM   2001  CA   LEU A 490      11.155   8.738  -0.629  1.00 26.18          A  C
ATOM   2002  CB   LEU A 490      10.726   9.390   0.698  1.00 26.47          A  C
ATOM   2003  CG   LEU A 490       9.461  10.270   0.688  1.00 24.58          A  C
ATOM   2004  CD1  LEU A 490       8.979  10.546   2.110  1.00 22.38          A  C
ATOM   2005  CD2  LEU A 490       9.755  11.565  -0.058  1.00 24.50          A  C
ATOM   2006  C    LEU A 490      12.613   8.253  -0.545  1.00 27.09          A  C
ATOM   2007  O    LEU A 490      13.524   8.984  -0.918  1.00 27.78          A  O
ATOM   2008  N    ARG A 491      12.829   7.033  -0.047  1.00 28.94          A  N
ATOM   2009  CA   ARG A 491      14.172   6.446   0.054  1.00 30.11          A  C
ATOM   2010  CB   ARG A 491      14.123   5.130   0.842  1.00 31.74          A  C
ATOM   2011  CG   ARG A 491      15.385   4.299   0.731  1.00 36.66          A  C
ATOM   2012  CD   ARG A 491      15.133   2.830   1.086  1.00 41.42          A  C
ATOM   2013  NE   ARG A 491      13.983   2.254   0.372  1.00 46.39          A  N
ATOM   2014  CZ   ARG A 491      13.964   1.923  -0.924  1.00 48.20          A  C
ATOM   2015  NH1  ARG A 491      15.032   2.104  -1.700  1.00 49.87          A  N
ATOM   2016  NH2  ARG A 491      12.872   1.384  -1.448  1.00 47.58          A  N
ATOM   2017  C    ARG A 491      14.728   6.205  -1.363  1.00 29.82          A  C
ATOM   2018  O    ARG A 491      15.843   6.628  -1.676  1.00 29.37          A  O
ATOM   2019  N    SER A 492      13.916   5.582  -2.223  1.00 30.08          A  N
ATOM   2020  CA   SER A 492      14.283   5.293  -3.611  1.00 31.09          A  C
ATOM   2021  CB   SER A 492      13.102   4.703  -4.379  1.00 30.76          A  C
ATOM   2022  OG   SER A 492      12.765   3.424  -3.885  1.00 35.64          A  O
ATOM   2023  C    SER A 492      14.740   6.536  -4.348  1.00 32.21          A  C
ATOM   2024  O    SER A 492      15.848   6.567  -4.875  1.00 32.90          A  O
ATOM   2025  N    VAL A 493      13.880   7.557  -4.364  1.00 32.85          A  N
ATOM   2026  CA   VAL A 493      14.147   8.821  -5.048  1.00 32.14          A  C
ATOM   2027  CB   VAL A 493      12.875   9.734  -5.086  1.00 32.69          A  C
```

Figure 4

| | | | | | | | | | | | |
|---|---|---|---|---|---|---|---|---|---|---|---|
| ATOM | 2028 | CG1 | VAL | A | 493 | 12.426 | 10.100 | -3.686 | 1.00 | 33.40 | A C |
| ATOM | 2029 | CG2 | VAL | A | 493 | 13.150 | 11.001 | -5.891 | 1.00 | 33.49 | A C |
| ATOM | 2030 | C | VAL | A | 493 | 15.349 | 9.589 | -4.501 | 1.00 | 32.90 | A C |
| ATOM | 2031 | O | VAL | A | 493 | 16.111 | 10.177 | -5.275 | 1.00 | 31.63 | A O |
| ATOM | 2032 | N | LEU | A | 494 | 15.536 | 9.557 | -3.179 | 1.00 | 33.64 | A N |
| ATOM | 2033 | CA | LEU | A | 494 | 16.651 | 10.255 | -2.541 | 1.00 | 34.32 | A C |
| ATOM | 2034 | CB | LEU | A | 494 | 16.372 | 10.481 | -1.047 | 1.00 | 32.86 | A C |
| ATOM | 2035 | CG | LEU | A | 494 | 15.326 | 11.557 | -0.690 | 1.00 | 32.29 | A C |
| ATOM | 2036 | CD1 | LEU | A | 494 | 15.015 | 11.532 | 0.810 | 1.00 | 30.10 | A C |
| ATOM | 2037 | CD2 | LEU | A | 494 | 15.816 | 12.946 | -1.112 | 1.00 | 31.30 | A C |
| ATOM | 2038 | C | LEU | A | 494 | 17.990 | 9.540 | -2.767 | 1.00 | 35.08 | A C |
| ATOM | 2039 | O | LEU | A | 494 | 19.034 | 10.189 | -2.866 | 1.00 | 35.01 | A O |
| ATOM | 2040 | N | GLU | A | 495 | 17.942 | 8.215 | -2.906 | 1.00 | 36.75 | A N |
| ATOM | 2041 | CA | GLU | A | 495 | 19.141 | 7.408 | -3.151 | 1.00 | 38.53 | A C |
| ATOM | 2042 | CB | GLU | A | 495 | 18.817 | 5.917 | -3.049 | 1.00 | 38.02 | A C |
| ATOM | 2043 | CG | GLU | A | 495 | 18.792 | 5.363 | -1.637 | 1.00 | 39.50 | A C |
| ATOM | 2044 | CD | GLU | A | 495 | 18.467 | 3.878 | -1.587 | 1.00 | 40.24 | A C |
| ATOM | 2045 | OE1 | GLU | A | 495 | 18.437 | 3.234 | -2.666 | 1.00 | 41.08 | A O |
| ATOM | 2046 | OE2 | GLU | A | 495 | 18.239 | 3.359 | -0.465 | 1.00 | 40.56 | A O |
| ATOM | 2047 | C | GLU | A | 495 | 19.691 | 7.678 | -4.546 | 1.00 | 40.55 | A C |
| ATOM | 2048 | O | GLU | A | 495 | 20.895 | 7.925 | -4.730 | 1.00 | 40.89 | A O |
| ATOM | 2049 | N | ASP | A | 496 | 18.787 | 7.616 | -5.523 | 1.00 | 41.54 | A N |
| ATOM | 2050 | CA | ASP | A | 496 | 19.108 | 7.819 | -6.928 | 1.00 | 42.71 | A C |
| ATOM | 2051 | CB | ASP | A | 496 | 18.111 | 7.061 | -7.815 | 1.00 | 43.21 | A C |
| ATOM | 2052 | CG | ASP | A | 496 | 18.190 | 5.547 | -7.656 | 1.00 | 45.04 | A C |
| ATOM | 2053 | OD1 | ASP | A | 496 | 19.225 | 5.003 | -7.202 | 1.00 | 46.37 | A O |
| ATOM | 2054 | OD2 | ASP | A | 496 | 17.203 | 4.886 | -8.030 | 1.00 | 46.88 | A O |
| ATOM | 2055 | C | ASP | A | 496 | 19.092 | 9.273 | -7.358 | 1.00 | 43.10 | A C |
| ATOM | 2056 | O | ASP | A | 496 | 19.218 | 9.547 | -8.548 | 1.00 | 44.35 | A O |
| ATOM | 2057 | N | PHE | A | 497 | 18.961 | 10.204 | -6.416 | 1.00 | 43.67 | A N |
| ATOM | 2058 | CA | PHE | A | 497 | 18.879 | 11.618 | -6.771 | 1.00 | 44.91 | A C |
| ATOM | 2059 | CB | PHE | A | 497 | 18.898 | 12.507 | -5.524 | 1.00 | 41.83 | A C |
| ATOM | 2060 | CG | PHE | A | 497 | 18.263 | 13.843 | -5.736 | 1.00 | 40.83 | A C |
| ATOM | 2061 | CD1 | PHE | A | 497 | 16.910 | 14.020 | -5.516 | 1.00 | 41.75 | A C |
| ATOM | 2062 | CD2 | PHE | A | 497 | 19.011 | 14.922 | -6.187 | 1.00 | 41.02 | A C |
| ATOM | 2063 | CE1 | PHE | A | 497 | 16.298 | 15.260 | -5.744 | 1.00 | 41.66 | A C |
| ATOM | 2064 | CE2 | PHE | A | 497 | 18.420 | 16.167 | -6.420 | 1.00 | 41.09 | A C |
| ATOM | 2065 | CZ | PHE | A | 497 | 17.055 | 16.339 | -6.198 | 1.00 | 41.01 | A C |
| ATOM | 2066 | C | PHE | A | 497 | 19.919 | 12.075 | -7.822 | 1.00 | 48.11 | A C |
| ATOM | 2067 | O | PHE | A | 497 | 19.563 | 12.731 | -8.807 | 1.00 | 49.95 | A O |
| ATOM | 2068 | N | PHE | A | 498 | 21.184 | 11.697 | -7.633 | 1.00 | 50.04 | A N |
| ATOM | 2069 | CA | PHE | A | 498 | 22.259 | 12.049 | -8.567 | 1.00 | 51.44 | A C |
| ATOM | 2070 | CB | PHE | A | 498 | 22.355 | 13.574 | -8.809 | 1.00 | 50.92 | A C |
| ATOM | 2071 | CG | PHE | A | 498 | 22.537 | 14.418 | -7.556 | 1.00 | 51.07 | A C |
| ATOM | 2072 | CD1 | PHE | A | 498 | 22.928 | 13.852 | -6.339 | 1.00 | 50.73 | A C |
| ATOM | 2073 | CD2 | PHE | A | 498 | 22.289 | 15.797 | -7.605 | 1.00 | 50.95 | A C |
| ATOM | 2074 | CE1 | PHE | A | 498 | 23.066 | 14.651 | -5.201 | 1.00 | 50.51 | A C |
| ATOM | 2075 | CE2 | PHE | A | 498 | 22.426 | 16.601 | -6.461 | 1.00 | 49.95 | A C |
| ATOM | 2076 | CZ | PHE | A | 498 | 22.812 | 16.023 | -5.265 | 1.00 | 49.62 | A C |
| ATOM | 2077 | C | PHE | A | 498 | 23.606 | 11.490 | -8.130 | 1.00 | 52.30 | A C |
| ATOM | 2078 | O | PHE | A | 498 | 23.820 | 10.292 | -8.396 | 1.00 | 54.54 | A O |
| ATOM | 2079 | N1 | LIG | A | 500 | 22.416 | 12.504 | 22.610 | 1.00 | 16.92 | A N |
| ATOM | 2080 | C2 | LIG | A | 500 | 25.464 | 10.794 | 21.236 | 1.00 | 15.69 | A C |
| ATOM | 2081 | N3 | LIG | A | 500 | 24.682 | 11.853 | 21.679 | 1.00 | 14.95 | A N |
| ATOM | 2082 | C4 | LIG | A | 500 | 23.383 | 11.635 | 22.125 | 1.00 | 19.51 | A C |
| ATOM | 2083 | C5 | LIG | A | 500 | 22.851 | 10.351 | 22.127 | 1.00 | 18.34 | A C |
| ATOM | 2084 | C6 | LIG | A | 500 | 23.644 | 9.288 | 21.672 | 1.00 | 18.09 | A C |
| ATOM | 2085 | N7 | LIG | A | 500 | 24.937 | 9.516 | 21.232 | 1.00 | 16.77 | A N |
| ATOM | 2086 | N8 | LIG | A | 500 | 21.297 | 11.754 | 22.919 | 1.00 | 19.06 | A N |
| ATOM | 2087 | C9 | LIG | A | 500 | 21.558 | 10.429 | 22.626 | 1.00 | 16.67 | A C |

Figure 4

| | | | | | | | | | | | |
|---|---|---|---|---|---|---|---|---|---|---|---|
| ATOM | 2088 | N10 | LIG | A | 500 | 23.164 | 8.028 | 21.646 | 1.00 | 15.37 | A N |
| ATOM | 2089 | C11 | LIG | A | 500 | 20.451 | 9.511 | 22.921 | 1.00 | 16.81 | A C |
| ATOM | 2090 | C12 | LIG | A | 500 | 20.699 | 8.399 | 23.749 | 1.00 | 17.35 | A C |
| ATOM | 2091 | C13 | LIG | A | 500 | 19.670 | 7.504 | 24.065 | 1.00 | 19.29 | A C |
| ATOM | 2092 | C14 | LIG | A | 500 | 18.380 | 7.707 | 23.559 | 1.00 | 18.96 | A C |
| ATOM | 2093 | C15 | LIG | A | 500 | 18.115 | 8.818 | 22.724 | 1.00 | 17.02 | A C |
| ATOM | 2094 | C16 | LIG | A | 500 | 19.156 | 9.725 | 22.402 | 1.00 | 15.16 | A C |
| ATOM | 2095 | C24 | LIG | A | 500 | 17.283 | 6.734 | 23.913 | 1.00 | 16.99 | A C |
| ATOM | 2096 | C28 | LIG | A | 500 | 22.537 | 13.987 | 22.653 | 1.00 | 22.83 | A C |
| ATOM | 2097 | C29 | LIG | A | 500 | 21.239 | 14.669 | 23.094 | 1.00 | 25.14 | A C |
| ATOM | 2098 | C33 | LIG | A | 500 | 22.876 | 14.604 | 21.296 | 1.00 | 24.71 | A C |
| ATOM | 2099 | C37 | LIG | A | 500 | 23.622 | 14.461 | 23.630 | 1.00 | 27.58 | A C |
| ATOM | 2100 | OH2 | H2O | A | 600 | 4.823 | 22.166 | 9.324 | 1.00 | 22.27 | A O |
| ATOM | 2101 | OH2 | H2O | A | 601 | 1.150 | 2.895 | -0.911 | 1.00 | 65.23 | A O |
| ATOM | 2102 | OH2 | H2O | A | 602 | -1.432 | 24.146 | 0.417 | 1.00 | 17.30 | A O |
| ATOM | 2103 | OH2 | H2O | A | 604 | 6.003 | 2.311 | -2.591 | 1.00 | 40.44 | A O |
| ATOM | 2104 | OH2 | H2O | A | 605 | -5.942 | 25.312 | 1.987 | 1.00 | 33.71 | A O |
| ATOM | 2105 | OH2 | H2O | A | 606 | 6.818 | 13.139 | 13.179 | 1.00 | 16.51 | A O |
| ATOM | 2106 | OH2 | H2O | A | 607 | -3.629 | 16.565 | -0.787 | 1.00 | 19.48 | A O |
| ATOM | 2107 | OH2 | H2O | A | 608 | 0.605 | 9.106 | -2.672 | 1.00 | 43.40 | A O |
| ATOM | 2108 | OH2 | H2O | A | 609 | -1.122 | 30.563 | 1.894 | 1.00 | 22.08 | A O |
| ATOM | 2109 | OH2 | H2O | A | 610 | 5.723 | 24.363 | 4.282 | 1.00 | 16.30 | A O |
| ATOM | 2110 | OH2 | H2O | A | 611 | 5.694 | 18.322 | -6.065 | 1.00 | 22.98 | A O |
| ATOM | 2111 | OH2 | H2O | A | 612 | 0.374 | 5.433 | 0.254 | 1.00 | 30.40 | A O |
| ATOM | 2112 | OH2 | H2O | A | 613 | -0.491 | 28.204 | -0.524 | 1.00 | 52.35 | A O |
| ATOM | 2113 | OH2 | H2O | A | 614 | 8.406 | 9.006 | 18.925 | 1.00 | 22.32 | A O |
| ATOM | 2114 | OH2 | H2O | A | 615 | -9.652 | 7.786 | -3.384 | 1.00 | 26.83 | A O |
| ATOM | 2115 | OH2 | H2O | A | 616 | -2.112 | 6.719 | -0.376 | 1.00 | 27.02 | A O |
| ATOM | 2116 | OH2 | H2O | A | 617 | 2.206 | 29.662 | -0.180 | 1.00 | 45.64 | A O |
| ATOM | 2117 | OH2 | H2O | A | 618 | 7.779 | 24.588 | 16.351 | 1.00 | 26.13 | A O |
| ATOM | 2118 | OH2 | H2O | A | 619 | -1.470 | 4.985 | 3.860 | 1.00 | 70.55 | A O |
| ATOM | 2119 | OH2 | H2O | A | 620 | 1.152 | 26.920 | -3.067 | 1.00 | 39.37 | A O |
| ATOM | 2120 | OH2 | H2O | A | 621 | 29.231 | 13.688 | 21.040 | 1.00 | 29.87 | A O |
| ATOM | 2121 | OH2 | H2O | A | 622 | 3.728 | 0.503 | -1.730 | 1.00 | 41.97 | A O |
| ATOM | 2122 | OH2 | H2O | A | 623 | -3.872 | 23.221 | 1.725 | 1.00 | 37.54 | A O |
| ATOM | 2123 | OH2 | H2O | A | 624 | 35.140 | 11.349 | 22.615 | 1.00 | 31.67 | A O |
| ATOM | 2124 | OH2 | H2O | A | 625 | 19.975 | 5.052 | 2.090 | 1.00 | 43.97 | A O |
| ATOM | 2125 | OH2 | H2O | A | 626 | 14.918 | 19.691 | 14.691 | 1.00 | 24.23 | A O |
| ATOM | 2126 | OH2 | H2O | A | 627 | 3.300 | 6.007 | 3.882 | 1.00 | 17.72 | A O |
| ATOM | 2127 | OH2 | H2O | A | 628 | 3.390 | 15.339 | 11.700 | 1.00 | 30.51 | A O |
| ATOM | 2128 | OH2 | H2O | A | 630 | 8.670 | 14.914 | -7.027 | 1.00 | 50.07 | A O |
| ATOM | 2129 | OH2 | H2O | A | 631 | 32.776 | -1.725 | 33.870 | 1.00 | 34.84 | A O |
| ATOM | 2130 | OH2 | H2O | A | 632 | 5.172 | 27.676 | -1.429 | 1.00 | 28.42 | A O |
| ATOM | 2131 | OH2 | H2O | A | 633 | 16.511 | 12.473 | 20.108 | 1.00 | 43.02 | A O |
| ATOM | 2132 | OH2 | H2O | A | 634 | 16.834 | -1.030 | 4.818 | 1.00 | 35.25 | A O |
| ATOM | 2133 | OH2 | H2O | A | 635 | -1.851 | 11.555 | 9.695 | 1.00 | 32.35 | A O |
| ATOM | 2134 | OH2 | H2O | A | 636 | -2.188 | 12.249 | -5.188 | 1.00 | 26.13 | A O |
| ATOM | 2135 | OH2 | H2O | A | 638 | -8.304 | 8.191 | -5.691 | 1.00 | 38.83 | A O |
| ATOM | 2136 | OH2 | H2O | A | 639 | 15.742 | 10.446 | -7.910 | 1.00 | 42.50 | A O |
| ATOM | 2137 | OH2 | H2O | A | 640 | -2.213 | 23.613 | 5.629 | 1.00 | 19.85 | A O |
| ATOM | 2138 | OH2 | H2O | A | 641 | -3.028 | 6.326 | 2.147 | 1.00 | 29.63 | A O |
| ATOM | 2139 | OH2 | H2O | A | 642 | 18.915 | -0.614 | 15.901 | 1.00 | 26.16 | A O |
| ATOM | 2140 | OH2 | H2O | A | 643 | 25.604 | 22.247 | 33.903 | 1.00 | 74.81 | A O |
| ATOM | 2141 | OH2 | H2O | A | 644 | 2.974 | 21.114 | -0.629 | 1.00 | 20.57 | A O |
| ATOM | 2142 | OH2 | H2O | A | 645 | -4.620 | 23.616 | 9.408 | 1.00 | 25.88 | A O |
| ATOM | 2143 | OH2 | H2O | A | 646 | 27.625 | 0.957 | 41.809 | 1.00 | 45.00 | A O |
| ATOM | 2144 | OH2 | H2O | A | 647 | 3.962 | 35.798 | 6.895 | 1.00 | 40.68 | A O |
| ATOM | 2145 | OH2 | H2O | A | 648 | 0.513 | 4.814 | 10.631 | 1.00 | 28.08 | A O |
| ATOM | 2146 | OH2 | H2O | A | 649 | -12.995 | 5.765 | -2.778 | 1.00 | 48.63 | A O |
| ATOM | 2147 | OH2 | H2O | A | 650 | 11.675 | 28.269 | 2.901 | 1.00 | 33.94 | A O |

Figure 4

```
ATOM   2148  OH2 H2O A 651       2.561  -2.612   1.022  1.00 30.15      A    O
ATOM   2149  OH2 H2O A 652      -1.814  20.622  -0.765  1.00 34.78      A    O
ATOM   2150  OH2 H2O A 653       3.024  22.489  11.461  1.00 20.35      A    O
ATOM   2151  OH2 H2O A 654       3.670  30.993  -4.362  1.00 23.92      A    O
ATOM   2152  OH2 H2O A 655      23.385  20.277  27.335  1.00 30.04      A    O
ATOM   2153  OH2 H2O A 656       4.078   3.527  16.445  1.00 27.31      A    O
ATOM   2154  OH2 H2O A 657       1.038   3.226   6.573  1.00 67.15      A    O
ATOM   2155  OH2 H2O A 658      -1.700  24.654  -5.736  1.00 43.25      A    O
ATOM   2156  OH2 H2O A 659       9.440  27.979  -4.326  1.00 25.17      A    O
ATOM   2157  OH2 H2O A 660      23.161  21.178  21.838  1.00 28.14      A    O
ATOM   2158  OH2 H2O A 661      14.253  14.809  24.056  1.00 29.50      A    O
ATOM   2159  OH2 H2O A 662      -6.275  10.709  -3.279  1.00 52.85      A    O
ATOM   2160  OH2 H2O A 663       6.284  34.320   3.837  1.00 31.16      A    O
ATOM   2161  OH2 H2O A 664      25.846  21.364  20.942  1.00 34.29      A    O
ATOM   2162  OH2 H2O A 665       2.071   2.522   3.245  1.00 46.32      A    O
ATOM   2163  OH2 H2O A 666      -2.241  24.453  -2.058  1.00 46.72      A    O
ATOM   2164  OH2 H2O A 667       8.359   0.821   3.561  1.00 23.91      A    O
ATOM   2165  OH2 H2O A 668      22.668  23.338   0.212  1.00 38.11      A    O
ATOM   2166  OH2 H2O A 669       4.518   0.972   2.149  1.00 41.07      A    O
ATOM   2167  OH2 H2O A 670      -5.485  24.358  -2.389  1.00 54.08      A    O
ATOM   2168  OH2 H2O A 671      -2.729   7.920   6.675  1.00 34.48      A    O
ATOM   2169  OH2 H2O A 672       5.521   2.469  19.328  1.00 29.98      A    O
ATOM   2170  OH2 H2O A 673      33.025  20.594  12.819  1.00 34.63      A    O
ATOM   2171  OH2 H2O A 674      14.056   0.374   4.777  1.00 32.66      A    O
ATOM   2172  OH2 H2O A 675      -3.459  24.722  11.428  1.00 29.24      A    O
ATOM   2173  OH2 H2O A 676      30.775   4.114  19.016  1.00 30.59      A    O
ATOM   2174  OH2 H2O A 677       4.766  15.101  14.239  1.00 27.27      A    O
ATOM   2175  OH2 H2O A 678      -5.974  18.901   6.646  1.00 41.24      A    O
ATOM   2176  OH2 H2O A 679      14.165  21.042  16.762  1.00 35.45      A    O
ATOM   2177  OH2 H2O A 680      31.187  15.587  32.199  1.00 41.52      A    O
ATOM   2178  OH2 H2O A 681      -7.035  18.870   9.572  1.00 39.04      A    O
ATOM   2179  OH2 H2O A 682      28.587   2.602  20.033  1.00 36.55      A    O
ATOM   2180  OH2 H2O A 683      18.695  16.517  20.263  1.00 33.15      A    O
ATOM   2181  OH2 H2O A 684      14.125  25.012   7.657  1.00 31.33      A    O
ATOM   2182  OH2 H2O A 685      -4.959  22.963   6.804  1.00 26.50      A    O
ATOM   2183  OH2 H2O A 686      17.256  24.064  -8.704  1.00 38.48      A    O
ATOM   2184  OH2 H2O A 687      -1.752  26.908  -3.985  1.00 39.18      A    O
ATOM   2185  OH2 H2O A 688      33.315  12.794  12.206  1.00 43.60      A    O
ATOM   2186  OH2 H2O A 689      -5.358  24.967  13.333  1.00 42.67      A    O
ATOM   2187  OH2 H2O A 690       3.531   4.805  33.133  1.00 42.39      A    O
ATOM   2188  OH2 H2O A 691      17.927  -1.786  19.817  1.00 32.60      A    O
ATOM   2189  OH2 H2O A 692      11.711  21.802  18.524  1.00 47.47      A    O
ATOM   2190  OH2 H2O A 693      15.754  23.429  12.806  1.00 41.13      A    O
ATOM   2191  OH2 H2O A 694      16.715   0.017  17.820  1.00 40.45      A    O
ATOM   2192  OH2 H2O A 695      -9.867  10.386  -6.690  1.00 41.79      A    O
ATOM   2193  OH2 H2O A 696      30.649  16.475   2.187  1.00 35.43      A    O
ATOM   2194  OH2 H2O A 697      10.950  16.182  -7.900  1.00 46.77      A    O
ATOM   2195  OH2 H2O A 698      23.884  11.654  35.003  1.00 42.68      A    O
ATOM   2196  OH2 H2O A 699      -4.936  21.851  -0.495  1.00 32.84      A    O
ATOM   2197  OH2 H2O A 700       6.429  11.465  -7.987  1.00 54.36      A    O
ATOM   2198  OH2 H2O A 701      32.814  11.806  24.130  1.00 32.47      A    O
ATOM   2199  CB  TRP B 238      46.107  27.897  32.761  1.00 61.01      B    C
ATOM   2200  CG  TRP B 238      45.666  28.450  34.124  1.00 63.28      B    C
ATOM   2201  CD2 TRP B 238      46.261  28.181  35.415  1.00 63.96      B    C
ATOM   2202  CE2 TRP B 238      45.512  28.903  36.381  1.00 64.42      B    C
ATOM   2203  CE3 TRP B 238      47.352  27.409  35.843  1.00 64.01      B    C
ATOM   2204  CD1 TRP B 238      44.611  29.295  34.367  1.00 63.91      B    C
ATOM   2205  NE1 TRP B 238      44.515  29.568  35.716  1.00 64.29      B    N
ATOM   2206  CZ2 TRP B 238      45.824  28.870  37.756  1.00 64.82      B    C
ATOM   2207  CZ3 TRP B 238      47.661  27.378  37.218  1.00 63.76      B    C
```

Figure 4

```
ATOM   2208  CH2  TRP B 238      46.899  28.106  38.150  1.00 63.98      B    C
ATOM   2209  C    TRP B 238      47.781  27.865  30.861  1.00 57.77      B    C
ATOM   2210  O    TRP B 238      48.298  26.752  30.937  1.00 56.89      B    O
ATOM   2211  N    TRP B 238      47.052  30.038  31.880  1.00 58.53      B    N
ATOM   2212  CA   TRP B 238      47.334  28.598  32.135  1.00 58.69      B    C
ATOM   2213  N    GLU B 239      47.565  28.480  29.697  1.00 57.43      B    N
ATOM   2214  CA   GLU B 239      47.969  27.883  28.415  1.00 56.55      B    C
ATOM   2215  CB   GLU B 239      47.112  28.409  27.263  1.00 59.08      B    C
ATOM   2216  CG   GLU B 239      46.052  27.445  26.775  1.00 62.51      B    C
ATOM   2217  CD   GLU B 239      44.843  27.381  27.690  1.00 64.73      B    C
ATOM   2218  OE1  GLU B 239      44.965  26.840  28.816  1.00 65.89      B    O
ATOM   2219  OE2  GLU B 239      43.764  27.869  27.276  1.00 66.11      B    O
ATOM   2220  C    GLU B 239      49.419  28.219  28.111  1.00 54.37      B    C
ATOM   2221  O    GLU B 239      49.830  29.379  28.230  1.00 54.88      B    O
ATOM   2222  N    VAL B 240      50.192  27.210  27.719  1.00 50.06      B    N
ATOM   2223  CA   VAL B 240      51.598  27.419  27.390  1.00 45.68      B    C
ATOM   2224  CB   VAL B 240      52.548  26.974  28.540  1.00 43.88      B    C
ATOM   2225  CG1  VAL B 240      52.238  27.733  29.806  1.00 42.89      B    C
ATOM   2226  CG2  VAL B 240      52.475  25.467  28.755  1.00 42.23      B    C
ATOM   2227  C    VAL B 240      51.994  26.676  26.119  1.00 44.71      B    C
ATOM   2228  O    VAL B 240      51.291  25.756  25.669  1.00 43.08      B    O
ATOM   2229  N    PRO B 241      53.084  27.132  25.473  1.00 43.46      B    N
ATOM   2230  CD   PRO B 241      53.694  28.460  25.643  1.00 43.24      B    C
ATOM   2231  CA   PRO B 241      53.578  26.503  24.253  1.00 42.30      B    C
ATOM   2232  CB   PRO B 241      54.621  27.508  23.761  1.00 41.87      B    C
ATOM   2233  CG   PRO B 241      54.093  28.799  24.229  1.00 42.12      B    C
ATOM   2234  C    PRO B 241      54.214  25.146  24.547  1.00 42.53      B    C
ATOM   2235  O    PRO B 241      54.845  24.944  25.586  1.00 40.91      B    O
ATOM   2236  N    ARG B 242      54.010  24.215  23.621  1.00 43.88      B    N
ATOM   2237  CA   ARG B 242      54.550  22.867  23.698  1.00 45.00      B    C
ATOM   2238  CB   ARG B 242      54.175  22.139  22.406  1.00 45.81      B    C
ATOM   2239  CG   ARG B 242      54.754  20.761  22.247  1.00 47.79      B    C
ATOM   2240  CD   ARG B 242      54.181  19.808  23.268  1.00 48.72      B    C
ATOM   2241  NE   ARG B 242      52.719  19.719  23.201  1.00 49.77      B    N
ATOM   2242  CZ   ARG B 242      52.024  19.221  22.178  1.00 48.71      B    C
ATOM   2243  NH1  ARG B 242      52.635  18.755  21.093  1.00 48.82      B    N
ATOM   2244  NH2  ARG B 242      50.703  19.171  22.259  1.00 47.73      B    N
ATOM   2245  C    ARG B 242      56.079  22.933  23.846  1.00 45.68      B    C
ATOM   2246  O    ARG B 242      56.683  22.078  24.482  1.00 44.62      B    O
ATOM   2247  N    GLU B 243      56.662  23.991  23.281  1.00 47.32      B    N
ATOM   2248  CA   GLU B 243      58.104  24.263  23.265  1.00 48.31      B    C
ATOM   2249  CB   GLU B 243      58.389  25.594  22.536  1.00 50.83      B    C
ATOM   2250  CG   GLU B 243      58.038  25.637  21.035  1.00 54.77      B    C
ATOM   2251  CD   GLU B 243      56.622  25.146  20.724  1.00 56.07      B    C
ATOM   2252  OE1  GLU B 243      55.651  25.918  20.897  1.00 56.41      B    O
ATOM   2253  OE2  GLU B 243      56.483  23.967  20.328  1.00 56.97      B    O
ATOM   2254  C    GLU B 243      58.676  24.361  24.665  1.00 46.51      B    C
ATOM   2255  O    GLU B 243      59.783  23.884  24.917  1.00 46.69      B    O
ATOM   2256  N    THR B 244      57.916  24.982  25.567  1.00 43.64      B    N
ATOM   2257  CA   THR B 244      58.344  25.169  26.956  1.00 41.30      B    C
ATOM   2258  CB   THR B 244      57.425  26.159  27.682  1.00 40.65      B    C
ATOM   2259  OG1  THR B 244      56.131  25.570  27.859  1.00 40.71      B    O
ATOM   2260  CG2  THR B 244      57.303  27.438  26.888  1.00 40.86      B    C
ATOM   2261  C    THR B 244      58.381  23.871  27.775  1.00 40.30      B    C
ATOM   2262  O    THR B 244      58.736  23.875  28.967  1.00 38.78      B    O
ATOM   2263  N    LEU B 245      58.109  22.757  27.107  1.00 38.92      B    N
ATOM   2264  CA   LEU B 245      58.036  21.476  27.768  1.00 37.89      B    C
ATOM   2265  CB   LEU B 245      56.571  21.055  27.765  1.00 38.14      B    C
ATOM   2266  CG   LEU B 245      56.040  20.295  28.961  1.00 39.76      B    C
ATOM   2267  CD1  LEU B 245      56.119  21.190  30.193  1.00 39.77      B    C
```

Figure 4

| ATOM | 2268 | CD2 | LEU | B | 245 | 54.603 | 19.870 | 28.669 | 1.00 | 40.31 | B | C |
| ATOM | 2269 | C | LEU | B | 245 | 58.878 | 20.363 | 27.146 | 1.00 | 37.42 | B | C |
| ATOM | 2270 | O | LEU | B | 245 | 58.772 | 20.100 | 25.943 | 1.00 | 38.07 | B | O |
| ATOM | 2271 | N | LYS | B | 246 | 59.716 | 19.721 | 27.967 | 1.00 | 35.40 | B | N |
| ATOM | 2272 | CA | LYS | B | 246 | 60.515 | 18.593 | 27.506 | 1.00 | 33.42 | B | C |
| ATOM | 2273 | CB | LYS | B | 246 | 62.031 | 18.818 | 27.688 | 1.00 | 34.41 | B | C |
| ATOM | 2274 | CG | LYS | B | 246 | 62.872 | 17.583 | 27.247 | 1.00 | 36.27 | B | C |
| ATOM | 2275 | CD | LYS | B | 246 | 64.369 | 17.843 | 27.058 | 1.00 | 37.77 | B | C |
| ATOM | 2276 | CE | LYS | B | 246 | 65.046 | 18.347 | 28.326 | 1.00 | 39.33 | B | C |
| ATOM | 2277 | NZ | LYS | B | 246 | 66.524 | 18.483 | 28.112 | 1.00 | 41.99 | B | N |
| ATOM | 2278 | C | LYS | B | 246 | 60.079 | 17.344 | 28.267 | 1.00 | 32.39 | B | C |
| ATOM | 2279 | O | LYS | B | 246 | 60.195 | 17.291 | 29.488 | 1.00 | 32.57 | B | O |
| ATOM | 2280 | N | LEU | B | 247 | 59.515 | 16.366 | 27.555 | 1.00 | 30.73 | B | N |
| ATOM | 2281 | CA | LEU | B | 247 | 59.087 | 15.117 | 28.176 | 1.00 | 28.45 | B | C |
| ATOM | 2282 | CB | LEU | B | 247 | 57.906 | 14.483 | 27.425 | 1.00 | 25.56 | B | C |
| ATOM | 2283 | CG | LEU | B | 247 | 56.518 | 14.986 | 27.856 | 1.00 | 24.31 | B | C |
| ATOM | 2284 | CD1 | LEU | B | 247 | 56.375 | 16.499 | 27.648 | 1.00 | 22.68 | B | C |
| ATOM | 2285 | CD2 | LEU | B | 247 | 55.433 | 14.223 | 27.109 | 1.00 | 22.97 | B | C |
| ATOM | 2286 | C | LEU | B | 247 | 60.290 | 14.198 | 28.187 | 1.00 | 29.32 | B | C |
| ATOM | 2287 | O | LEU | B | 247 | 60.912 | 13.966 | 27.149 | 1.00 | 29.73 | B | O |
| ATOM | 2288 | N | VAL | B | 248 | 60.618 | 13.685 | 29.371 | 1.00 | 29.09 | B | N |
| ATOM | 2289 | CA | VAL | B | 248 | 61.780 | 12.820 | 29.547 | 1.00 | 29.22 | B | C |
| ATOM | 2290 | CB | VAL | B | 248 | 62.696 | 13.354 | 30.702 | 1.00 | 28.27 | B | C |
| ATOM | 2291 | CG1 | VAL | B | 248 | 63.910 | 12.455 | 30.889 | 1.00 | 28.03 | B | C |
| ATOM | 2292 | CG2 | VAL | B | 248 | 63.129 | 14.769 | 30.416 | 1.00 | 27.74 | B | C |
| ATOM | 2293 | C | VAL | B | 248 | 61.540 | 11.319 | 29.765 | 1.00 | 29.50 | B | C |
| ATOM | 2294 | O | VAL | B | 248 | 62.023 | 10.474 | 28.999 | 1.00 | 30.41 | B | O |
| ATOM | 2295 | N | GLU | B | 249 | 60.782 | 10.988 | 30.797 | 1.00 | 30.37 | B | N |
| ATOM | 2296 | CA | GLU | B | 249 | 60.547 | 9.598 | 31.143 | 1.00 | 30.64 | B | C |
| ATOM | 2297 | CB | GLU | B | 249 | 61.306 | 9.332 | 32.434 | 1.00 | 30.88 | B | C |
| ATOM | 2298 | CG | GLU | B | 249 | 61.291 | 7.924 | 32.925 | 1.00 | 33.25 | B | C |
| ATOM | 2299 | CD | GLU | B | 249 | 61.937 | 7.801 | 34.287 | 1.00 | 34.39 | B | C |
| ATOM | 2300 | OE1 | GLU | B | 249 | 62.746 | 8.685 | 34.647 | 1.00 | 34.57 | B | O |
| ATOM | 2301 | OE2 | GLU | B | 249 | 61.621 | 6.833 | 35.007 | 1.00 | 36.36 | B | O |
| ATOM | 2302 | C | GLU | B | 249 | 59.070 | 9.269 | 31.336 | 1.00 | 29.22 | B | C |
| ATOM | 2303 | O | GLU | B | 249 | 58.369 | 9.990 | 32.024 | 1.00 | 29.35 | B | O |
| ATOM | 2304 | N | ARG | B | 250 | 58.593 | 8.195 | 30.723 | 1.00 | 27.22 | B | N |
| ATOM | 2305 | CA | ARG | B | 250 | 57.205 | 7.843 | 30.911 | 1.00 | 28.18 | B | C |
| ATOM | 2306 | CB | ARG | B | 250 | 56.673 | 6.993 | 29.781 | 1.00 | 28.55 | B | C |
| ATOM | 2307 | CG | ARG | B | 250 | 55.171 | 6.982 | 29.795 | 1.00 | 29.38 | B | C |
| ATOM | 2308 | CD | ARG | B | 250 | 54.648 | 6.180 | 28.663 | 1.00 | 31.29 | B | C |
| ATOM | 2309 | NE | ARG | B | 250 | 54.869 | 4.761 | 28.878 | 1.00 | 32.31 | B | N |
| ATOM | 2310 | CZ | ARG | B | 250 | 54.732 | 3.839 | 27.936 | 1.00 | 33.76 | B | C |
| ATOM | 2311 | NH1 | ARG | B | 250 | 54.377 | 4.195 | 26.714 | 1.00 | 35.03 | B | N |
| ATOM | 2312 | NH2 | ARG | B | 250 | 54.933 | 2.563 | 28.215 | 1.00 | 35.49 | B | N |
| ATOM | 2313 | C | ARG | B | 250 | 57.033 | 7.091 | 32.216 | 1.00 | 28.76 | B | C |
| ATOM | 2314 | O | ARG | B | 250 | 57.631 | 6.026 | 32.430 | 1.00 | 28.55 | B | O |
| ATOM | 2315 | N | LEU | B | 251 | 56.202 | 7.658 | 33.084 | 1.00 | 28.36 | B | N |
| ATOM | 2316 | CA | LEU | B | 251 | 55.932 | 7.068 | 34.381 | 1.00 | 28.06 | B | C |
| ATOM | 2317 | CB | LEU | B | 251 | 55.585 | 8.162 | 35.393 | 1.00 | 27.07 | B | C |
| ATOM | 2318 | CG | LEU | B | 251 | 56.686 | 9.219 | 35.504 | 1.00 | 26.73 | B | C |
| ATOM | 2319 | CD1 | LEU | B | 251 | 56.292 | 10.270 | 36.514 | 1.00 | 28.33 | B | C |
| ATOM | 2320 | CD2 | LEU | B | 251 | 58.018 | 8.584 | 35.900 | 1.00 | 27.12 | B | C |
| ATOM | 2321 | C | LEU | B | 251 | 54.848 | 6.000 | 34.294 | 1.00 | 28.24 | B | C |
| ATOM | 2322 | O | LEU | B | 251 | 54.946 | 4.954 | 34.932 | 1.00 | 30.01 | B | O |
| ATOM | 2323 | N | GLY | B | 252 | 53.853 | 6.220 | 33.445 | 1.00 | 28.63 | B | N |
| ATOM | 2324 | CA | GLY | B | 252 | 52.790 | 5.240 | 33.310 | 1.00 | 26.25 | B | C |
| ATOM | 2325 | C | GLY | B | 252 | 51.952 | 5.413 | 32.062 | 1.00 | 24.81 | B | C |
| ATOM | 2326 | O | GLY | B | 252 | 51.913 | 6.491 | 31.476 | 1.00 | 23.39 | B | O |
| ATOM | 2327 | N | ALA | B | 253 | 51.323 | 4.317 | 31.645 | 1.00 | 26.68 | B | N |

Figure 4

| ATOM | 2328 | CA | ALA | B | 253 | 50.462 | 4.285 | 30.470 | 1.00 | 27.62 | B | C |
| --- | --- | --- | --- | --- | --- | --- | --- | --- | --- | --- | --- | --- |
| ATOM | 2329 | CB | ALA | B | 253 | 51.223 | 3.715 | 29.275 | 1.00 | 27.19 | B | C |
| ATOM | 2330 | C | ALA | B | 253 | 49.190 | 3.456 | 30.751 | 1.00 | 29.84 | B | C |
| ATOM | 2331 | O | ALA | B | 253 | 49.253 | 2.330 | 31.278 | 1.00 | 29.17 | B | O |
| ATOM | 2332 | N | GLY | B | 254 | 48.038 | 4.039 | 30.416 | 1.00 | 31.37 | B | N |
| ATOM | 2333 | CA | GLY | B | 254 | 46.767 | 3.374 | 30.629 | 1.00 | 31.45 | B | C |
| ATOM | 2334 | C | GLY | B | 254 | 45.784 | 3.586 | 29.496 | 1.00 | 32.56 | B | C |
| ATOM | 2335 | O | GLY | B | 254 | 46.102 | 4.203 | 28.479 | 1.00 | 32.49 | B | O |
| ATOM | 2336 | N | GLN | B | 255 | 44.560 | 3.124 | 29.718 | 1.00 | 33.97 | B | N |
| ATOM | 2337 | CA | GLN | B | 255 | 43.484 | 3.197 | 28.733 | 1.00 | 35.46 | B | C |
| ATOM | 2338 | CB | GLN | B | 255 | 42.199 | 2.581 | 29.325 | 1.00 | 38.72 | B | C |
| ATOM | 2339 | CG | GLN | B | 255 | 41.261 | 1.963 | 28.281 | 1.00 | 44.23 | B | C |
| ATOM | 2340 | CD | GLN | B | 255 | 39.770 | 2.068 | 28.639 | 1.00 | 46.44 | B | C |
| ATOM | 2341 | OE1 | GLN | B | 255 | 38.910 | 2.109 | 27.740 | 1.00 | 48.16 | B | O |
| ATOM | 2342 | NE2 | GLN | B | 255 | 39.459 | 2.126 | 29.940 | 1.00 | 45.65 | B | N |
| ATOM | 2343 | C | GLN | B | 255 | 43.190 | 4.591 | 28.154 | 1.00 | 32.65 | B | C |
| ATOM | 2344 | O | GLN | B | 255 | 42.944 | 4.728 | 26.955 | 1.00 | 31.62 | B | O |
| ATOM | 2345 | N | PHE | B | 256 | 43.259 | 5.613 | 29.000 | 1.00 | 30.28 | B | N |
| ATOM | 2346 | CA | PHE | B | 256 | 42.961 | 6.989 | 28.606 | 1.00 | 29.13 | B | C |
| ATOM | 2347 | CB | PHE | B | 256 | 42.162 | 7.706 | 29.712 | 1.00 | 30.08 | B | C |
| ATOM | 2348 | CG | PHE | B | 256 | 40.720 | 7.272 | 29.847 | 1.00 | 28.88 | B | C |
| ATOM | 2349 | CD1 | PHE | B | 256 | 40.199 | 6.210 | 29.106 | 1.00 | 29.63 | B | C |
| ATOM | 2350 | CD2 | PHE | B | 256 | 39.881 | 7.951 | 30.734 | 1.00 | 29.21 | B | C |
| ATOM | 2351 | CE1 | PHE | B | 256 | 38.860 | 5.829 | 29.243 | 1.00 | 29.86 | B | C |
| ATOM | 2352 | CE2 | PHE | B | 256 | 38.548 | 7.582 | 30.879 | 1.00 | 29.09 | B | C |
| ATOM | 2353 | CZ | PHE | B | 256 | 38.038 | 6.515 | 30.130 | 1.00 | 29.30 | B | C |
| ATOM | 2354 | C | PHE | B | 256 | 44.152 | 7.877 | 28.254 | 1.00 | 28.24 | B | C |
| ATOM | 2355 | O | PHE | B | 256 | 43.965 | 9.019 | 27.817 | 1.00 | 27.89 | B | O |
| ATOM | 2356 | N | GLY | B | 257 | 45.365 | 7.396 | 28.502 | 1.00 | 27.87 | B | N |
| ATOM | 2357 | CA | GLY | B | 257 | 46.533 | 8.201 | 28.196 | 1.00 | 27.46 | B | C |
| ATOM | 2358 | C | GLY | B | 257 | 47.771 | 7.801 | 28.982 | 1.00 | 27.49 | B | C |
| ATOM | 2359 | O | GLY | B | 257 | 47.903 | 6.665 | 29.444 | 1.00 | 25.74 | B | O |
| ATOM | 2360 | N | GLU | B | 258 | 48.672 | 8.760 | 29.166 | 1.00 | 29.05 | B | N |
| ATOM | 2361 | CA | GLU | B | 258 | 49.916 | 8.498 | 29.873 | 1.00 | 28.24 | B | C |
| ATOM | 2362 | CB | GLU | B | 258 | 51.019 | 8.241 | 28.860 | 1.00 | 30.08 | B | C |
| ATOM | 2363 | CG | GLU | B | 258 | 50.659 | 7.194 | 27.828 | 1.00 | 32.28 | B | C |
| ATOM | 2364 | CD | GLU | B | 258 | 51.727 | 7.032 | 26.774 | 1.00 | 35.60 | B | C |
| ATOM | 2365 | OE1 | GLU | B | 258 | 52.438 | 8.015 | 26.485 | 1.00 | 37.17 | B | O |
| ATOM | 2366 | OE2 | GLU | B | 258 | 51.868 | 5.912 | 26.235 | 1.00 | 37.93 | B | O |
| ATOM | 2367 | C | GLU | B | 258 | 50.343 | 9.633 | 30.786 | 1.00 | 27.62 | B | C |
| ATOM | 2368 | O | GLU | B | 258 | 49.744 | 10.709 | 30.791 | 1.00 | 28.07 | B | O |
| ATOM | 2369 | N | VAL | B | 259 | 51.354 | 9.355 | 31.601 | 1.00 | 28.35 | B | N |
| ATOM | 2370 | CA | VAL | B | 259 | 51.903 | 10.347 | 32.517 | 1.00 | 27.78 | B | C |
| ATOM | 2371 | CB | VAL | B | 259 | 51.471 | 10.096 | 33.967 | 1.00 | 27.69 | B | C |
| ATOM | 2372 | CG1 | VAL | B | 259 | 52.046 | 11.200 | 34.856 | 1.00 | 26.65 | B | C |
| ATOM | 2373 | CG2 | VAL | B | 259 | 49.927 | 10.040 | 34.064 | 1.00 | 27.40 | B | C |
| ATOM | 2374 | C | VAL | B | 259 | 53.416 | 10.261 | 32.404 | 1.00 | 27.68 | B | C |
| ATOM | 2375 | O | VAL | B | 259 | 53.987 | 9.173 | 32.471 | 1.00 | 28.96 | B | O |
| ATOM | 2376 | N | TRP | B | 260 | 54.053 | 11.416 | 32.237 | 1.00 | 28.58 | B | N |
| ATOM | 2377 | CA | TRP | B | 260 | 55.504 | 11.496 | 32.061 | 1.00 | 27.90 | B | C |
| ATOM | 2378 | CB | TRP | B | 260 | 55.839 | 12.045 | 30.663 | 1.00 | 28.19 | B | C |
| ATOM | 2379 | CG | TRP | B | 260 | 55.603 | 11.122 | 29.540 | 1.00 | 28.29 | B | C |
| ATOM | 2380 | CD2 | TRP | B | 260 | 56.587 | 10.608 | 28.643 | 1.00 | 28.70 | B | C |
| ATOM | 2381 | CE2 | TRP | B | 260 | 55.935 | 9.699 | 27.780 | 1.00 | 30.72 | B | C |
| ATOM | 2382 | CE3 | TRP | B | 260 | 57.962 | 10.822 | 28.485 | 1.00 | 28.64 | B | C |
| ATOM | 2383 | CD1 | TRP | B | 260 | 54.422 | 10.536 | 29.188 | 1.00 | 29.15 | B | C |
| ATOM | 2384 | NE1 | TRP | B | 260 | 54.611 | 9.672 | 28.141 | 1.00 | 30.27 | B | N |
| ATOM | 2385 | CZ2 | TRP | B | 260 | 56.615 | 8.998 | 26.768 | 1.00 | 30.87 | B | C |
| ATOM | 2386 | CZ3 | TRP | B | 260 | 58.636 | 10.128 | 27.490 | 1.00 | 28.51 | B | C |
| ATOM | 2387 | CH2 | TRP | B | 260 | 57.962 | 9.226 | 26.644 | 1.00 | 30.30 | B | C |

Figure 4

```
ATOM   2388  C    TRP B 260      56.188  12.436  33.013  1.00 26.79      B  C
ATOM   2389  O    TRP B 260      55.591  13.392  33.472  1.00 25.38      B  O
ATOM   2390  N    MET B 261      57.450  12.148  33.312  1.00 27.84      B  N
ATOM   2391  CA   MET B 261      58.249  13.071  34.092  1.00 28.85      B  C
ATOM   2392  CB   MET B 261      59.338  12.341  34.887  1.00 28.25      B  C
ATOM   2393  CG   MET B 261      60.270  13.295  35.670  1.00 28.42      B  C
ATOM   2394  SD   MET B 261      61.610  14.048  34.666  1.00 27.54      B  S
ATOM   2395  CE   MET B 261      62.706  12.613  34.514  1.00 27.20      B  C
ATOM   2396  C    MET B 261      58.883  13.951  32.989  1.00 29.04      B  C
ATOM   2397  O    MET B 261      59.158  13.476  31.885  1.00 28.77      B  O
ATOM   2398  N    GLY B 262      59.087  15.229  33.266  1.00 29.60      B  N
ATOM   2399  CA   GLY B 262      59.680  16.087  32.262  1.00 28.47      B  C
ATOM   2400  C    GLY B 262      60.162  17.363  32.893  1.00 28.71      B  C
ATOM   2401  O    GLY B 262      60.153  17.494  34.115  1.00 28.14      B  O
ATOM   2402  N    TYR B 263      60.592  18.303  32.058  1.00 29.11      B  N
ATOM   2403  CA   TYR B 263      61.078  19.584  32.536  1.00 29.72      B  C
ATOM   2404  CB   TYR B 263      62.604  19.685  32.360  1.00 27.16      B  C
ATOM   2405  CG   TYR B 263      63.342  18.692  33.234  1.00 25.67      B  C
ATOM   2406  CD1  TYR B 263      63.626  18.984  34.578  1.00 25.34      B  C
ATOM   2407  CE1  TYR B 263      64.251  18.039  35.412  1.00 25.97      B  C
ATOM   2408  CD2  TYR B 263      63.691  17.429  32.745  1.00 24.67      B  C
ATOM   2409  CE2  TYR B 263      64.308  16.480  33.562  1.00 24.86      B  C
ATOM   2410  CZ   TYR B 263      64.583  16.787  34.897  1.00 25.71      B  C
ATOM   2411  OH   TYR B 263      65.183  15.841  35.706  1.00 26.45      B  O
ATOM   2412  C    TYR B 263      60.340  20.743  31.889  1.00 31.08      B  C
ATOM   2413  O    TYR B 263      60.106  20.765  30.682  1.00 31.52      B  O
ATOM   2414  N    TYR B 264      59.909  21.663  32.743  1.00 35.18      B  N
ATOM   2415  CA   TYR B 264      59.168  22.855  32.348  1.00 38.85      B  C
ATOM   2416  CB   TYR B 264      57.931  22.990  33.251  1.00 38.95      B  C
ATOM   2417  CG   TYR B 264      57.014  24.150  32.955  1.00 40.06      B  C
ATOM   2418  CD1  TYR B 264      56.623  24.467  31.646  1.00 40.00      B  C
ATOM   2419  CE1  TYR B 264      55.772  25.553  31.395  1.00 40.82      B  C
ATOM   2420  CD2  TYR B 264      56.540  24.938  33.997  1.00 40.44      B  C
ATOM   2421  CE2  TYR B 264      55.694  26.013  33.765  1.00 40.99      B  C
ATOM   2422  CZ   TYR B 264      55.312  26.324  32.471  1.00 41.53      B  C
ATOM   2423  OH   TYR B 264      54.449  27.392  32.292  1.00 42.95      B  O
ATOM   2424  C    TYR B 264      60.130  24.047  32.477  1.00 40.38      B  C
ATOM   2425  O    TYR B 264      60.589  24.380  33.577  1.00 39.40      B  O
ATOM   2426  N    ASN B 265      60.438  24.658  31.329  1.00 43.04      B  N
ATOM   2427  CA   ASN B 265      61.380  25.777  31.227  1.00 44.29      B  C
ATOM   2428  CB   ASN B 265      60.987  26.936  32.141  1.00 43.67      B  C
ATOM   2429  CG   ASN B 265      59.569  27.410  31.906  1.00 43.46      B  C
ATOM   2430  OD1  ASN B 265      59.160  27.660  30.767  1.00 42.18      B  O
ATOM   2431  ND2  ASN B 265      58.805  27.531  32.988  1.00 43.25      B  N
ATOM   2432  C    ASN B 265      62.778  25.251  31.574  1.00 45.66      B  C
ATOM   2433  O    ASN B 265      63.514  25.850  32.360  1.00 44.81      B  O
ATOM   2434  N    GLY B 266      63.074  24.065  31.043  1.00 47.42      B  N
ATOM   2435  CA   GLY B 266      64.358  23.421  31.244  1.00 49.84      B  C
ATOM   2436  C    GLY B 266      64.737  22.952  32.638  1.00 51.40      B  C
ATOM   2437  O    GLY B 266      65.423  21.931  32.762  1.00 51.66      B  O
ATOM   2438  N    HIS B 267      64.269  23.632  33.688  1.00 52.71      B  N
ATOM   2439  CA   HIS B 267      64.659  23.248  35.049  1.00 53.61      B  C
ATOM   2440  CB   HIS B 267      65.601  24.305  35.639  1.00 57.88      B  C
ATOM   2441  CG   HIS B 267      66.944  24.340  34.971  1.00 61.70      B  C
ATOM   2442  CD2  HIS B 267      67.886  23.374  34.822  1.00 62.53      B  C
ATOM   2443  ND1  HIS B 267      67.428  25.450  34.311  1.00 62.50      B  N
ATOM   2444  CE1  HIS B 267      68.605  25.168  33.782  1.00 63.56      B  C
ATOM   2445  NE2  HIS B 267      68.908  23.914  34.078  1.00 63.06      B  N
ATOM   2446  C    HIS B 267      63.622  22.810  36.084  1.00 50.58      B  C
ATOM   2447  O    HIS B 267      63.983  22.156  37.059  1.00 50.72      B  O
```

Figure 4

| | | | | | | | | | | | |
|---|---|---|---|---|---|---|---|---|---|---|---|
| ATOM | 2448 | N | THR | B | 268 | 62.356 | 23.180 | 35.913 | 1.00 | 47.12 | B | N |
| ATOM | 2449 | CA | THR | B | 268 | 61.324 | 22.754 | 36.868 | 1.00 | 42.49 | B | C |
| ATOM | 2450 | CB | THR | B | 268 | 60.102 | 23.715 | 36.868 | 1.00 | 42.94 | B | C |
| ATOM | 2451 | OG1 | THR | B | 268 | 60.530 | 25.035 | 37.231 | 1.00 | 44.03 | B | O |
| ATOM | 2452 | CG2 | THR | B | 268 | 59.035 | 23.254 | 37.859 | 1.00 | 42.13 | B | C |
| ATOM | 2453 | C | THR | B | 268 | 60.867 | 21.326 | 36.541 | 1.00 | 39.12 | B | C |
| ATOM | 2454 | O | THR | B | 268 | 60.382 | 21.058 | 35.444 | 1.00 | 37.28 | B | O |
| ATOM | 2455 | N | LYS | B | 269 | 61.051 | 20.401 | 37.472 | 1.00 | 35.79 | B | N |
| ATOM | 2456 | CA | LYS | B | 269 | 60.639 | 19.010 | 37.278 | 1.00 | 32.86 | B | C |
| ATOM | 2457 | CB | LYS | B | 269 | 61.319 | 18.110 | 38.308 | 1.00 | 30.17 | B | C |
| ATOM | 2458 | CG | LYS | B | 269 | 61.553 | 16.698 | 37.806 | 1.00 | 28.34 | B | C |
| ATOM | 2459 | CD | LYS | B | 269 | 62.476 | 15.945 | 38.724 | 1.00 | 28.43 | B | C |
| ATOM | 2460 | CE | LYS | B | 269 | 62.705 | 14.537 | 38.208 | 1.00 | 27.55 | B | C |
| ATOM | 2461 | NZ | LYS | B | 269 | 63.593 | 13.749 | 39.104 | 1.00 | 29.21 | B | N |
| ATOM | 2462 | C | LYS | B | 269 | 59.134 | 18.871 | 37.355 | 1.00 | 31.98 | B | C |
| ATOM | 2463 | O | LYS | B | 269 | 58.496 | 19.391 | 38.277 | 1.00 | 32.62 | B | O |
| ATOM | 2464 | N | VAL | B | 270 | 58.532 | 18.139 | 36.348 | 1.00 | 30.68 | B | N |
| ATOM | 2465 | CA | VAL | B | 270 | 57.075 | 17.986 | 36.227 | 1.00 | 28.25 | B | C |
| ATOM | 2466 | CB | VAL | B | 270 | 56.556 | 18.850 | 35.059 | 1.00 | 27.86 | B | C |
| ATOM | 2467 | CG1 | VAL | B | 270 | 56.862 | 20.318 | 35.316 | 1.00 | 27.77 | B | C |
| ATOM | 2468 | CG2 | VAL | B | 270 | 57.163 | 18.401 | 33.749 | 1.00 | 25.40 | B | C |
| ATOM | 2469 | C | VAL | B | 270 | 56.547 | 16.576 | 35.956 | 1.00 | 27.96 | B | C |
| ATOM | 2470 | O | VAL | B | 270 | 57.286 | 15.625 | 35.687 | 1.00 | 27.14 | B | O |
| ATOM | 2471 | N | ALA | B | 271 | 55.249 | 16.528 | 36.038 | 1.00 | 27.82 | B | N |
| ATOM | 2472 | CA | ALA | B | 271 | 54.508 | 15.371 | 35.676 | 1.00 | 26.72 | B | C |
| ATOM | 2473 | CB | ALA | B | 271 | 53.646 | 14.833 | 36.792 | 1.00 | 27.48 | B | C |
| ATOM | 2474 | C | ALA | B | 271 | 53.676 | 15.927 | 34.574 | 1.00 | 26.75 | B | C |
| ATOM | 2475 | O | ALA | B | 271 | 53.121 | 17.013 | 34.714 | 1.00 | 27.73 | B | O |
| ATOM | 2476 | N | VAL | B | 272 | 53.561 | 15.190 | 33.482 | 1.00 | 26.16 | B | N |
| ATOM | 2477 | CA | VAL | B | 272 | 52.771 | 15.649 | 32.364 | 1.00 | 25.48 | B | C |
| ATOM | 2478 | CB | VAL | B | 272 | 53.690 | 15.990 | 31.120 | 1.00 | 25.57 | B | C |
| ATOM | 2479 | CG1 | VAL | B | 272 | 52.846 | 16.480 | 29.937 | 1.00 | 26.52 | B | C |
| ATOM | 2480 | CG2 | VAL | B | 272 | 54.750 | 17.040 | 31.486 | 1.00 | 22.48 | B | C |
| ATOM | 2481 | C | VAL | B | 272 | 51.797 | 14.547 | 32.001 | 1.00 | 25.28 | B | C |
| ATOM | 2482 | O | VAL | B | 272 | 52.219 | 13.442 | 31.650 | 1.00 | 26.14 | B | O |
| ATOM | 2483 | N | LYS | B | 273 | 50.503 | 14.822 | 32.159 | 1.00 | 25.10 | B | N |
| ATOM | 2484 | CA | LYS | B | 273 | 49.468 | 13.854 | 31.798 | 1.00 | 24.80 | B | C |
| ATOM | 2485 | CB | LYS | B | 273 | 48.333 | 13.859 | 32.831 | 1.00 | 25.49 | B | C |
| ATOM | 2486 | CG | LYS | B | 273 | 47.219 | 12.839 | 32.554 | 1.00 | 26.34 | B | C |
| ATOM | 2487 | CD | LYS | B | 273 | 46.197 | 12.756 | 33.698 | 1.00 | 26.86 | B | C |
| ATOM | 2488 | CE | LYS | B | 273 | 46.631 | 11.764 | 34.779 | 1.00 | 26.16 | B | C |
| ATOM | 2489 | NZ | LYS | B | 273 | 45.593 | 11.649 | 35.833 | 1.00 | 25.93 | B | N |
| ATOM | 2490 | C | LYS | B | 273 | 48.935 | 14.148 | 30.387 | 1.00 | 24.36 | B | C |
| ATOM | 2491 | O | LYS | B | 273 | 48.479 | 15.260 | 30.093 | 1.00 | 21.98 | B | O |
| ATOM | 2492 | N | SER | B | 274 | 49.030 | 13.158 | 29.508 | 1.00 | 25.48 | B | N |
| ATOM | 2493 | CA | SER | B | 274 | 48.573 | 13.332 | 28.143 | 1.00 | 29.32 | B | C |
| ATOM | 2494 | CB | SER | B | 274 | 49.692 | 13.016 | 27.154 | 1.00 | 30.91 | B | C |
| ATOM | 2495 | OG | SER | B | 274 | 50.035 | 11.644 | 27.200 | 1.00 | 33.97 | B | O |
| ATOM | 2496 | C | SER | B | 274 | 47.367 | 12.467 | 27.845 | 1.00 | 30.39 | B | C |
| ATOM | 2497 | O | SER | B | 274 | 47.243 | 11.347 | 28.354 | 1.00 | 30.83 | B | O |
| ATOM | 2498 | N | LEU | B | 275 | 46.489 | 13.000 | 27.002 | 1.00 | 32.31 | B | N |
| ATOM | 2499 | CA | LEU | B | 275 | 45.266 | 12.310 | 26.606 | 1.00 | 33.55 | B | C |
| ATOM | 2500 | CB | LEU | B | 275 | 44.121 | 13.321 | 26.451 | 1.00 | 31.43 | B | C |
| ATOM | 2501 | CG | LEU | B | 275 | 42.846 | 12.826 | 25.760 | 1.00 | 31.20 | B | C |
| ATOM | 2502 | CD1 | LEU | B | 275 | 42.095 | 11.848 | 26.671 | 1.00 | 31.10 | B | C |
| ATOM | 2503 | CD2 | LEU | B | 275 | 41.956 | 14.014 | 25.399 | 1.00 | 30.30 | B | C |
| ATOM | 2504 | C | LEU | B | 275 | 45.395 | 11.502 | 25.313 | 1.00 | 35.66 | B | C |
| ATOM | 2505 | O | LEU | B | 275 | 45.920 | 11.988 | 24.301 | 1.00 | 37.07 | B | O |
| ATOM | 2506 | N | LYS | B | 276 | 44.934 | 10.255 | 25.368 | 1.00 | 37.45 | B | N |
| ATOM | 2507 | CA | LYS | B | 276 | 44.927 | 9.374 | 24.208 | 1.00 | 39.84 | B | C |

Figure 4

| | | | | | | | | | | | |
|---|---|---|---|---|---|---|---|---|---|---|---|
| ATOM | 2508 | CB | LYS | B | 276 | 44.821 | 7.913 | 24.658 | 1.00 | 39.64 | B C |
| ATOM | 2509 | CG | LYS | B | 276 | 44.644 | 6.895 | 23.543 | 1.00 | 41.28 | B C |
| ATOM | 2510 | CD | LYS | B | 276 | 44.584 | 5.471 | 24.090 | 1.00 | 43.78 | B C |
| ATOM | 2511 | CE | LYS | B | 276 | 45.814 | 5.156 | 24.942 | 1.00 | 46.91 | B C |
| ATOM | 2512 | NZ | LYS | B | 276 | 45.852 | 3.774 | 25.521 | 1.00 | 49.10 | B N |
| ATOM | 2513 | C | LYS | B | 276 | 43.679 | 9.788 | 23.421 | 1.00 | 42.02 | B C |
| ATOM | 2514 | O | LYS | B | 276 | 42.550 | 9.605 | 23.896 | 1.00 | 40.61 | B O |
| ATOM | 2515 | N | GLN | B | 277 | 43.888 | 10.418 | 22.258 | 1.00 | 44.64 | B N |
| ATOM | 2516 | CA | GLN | B | 277 | 42.833 | 10.905 | 21.379 | 1.00 | 45.50 | B C |
| ATOM | 2517 | CB | GLN | B | 277 | 43.403 | 11.254 | 20.002 | 1.00 | 48.97 | B C |
| ATOM | 2518 | CG | GLN | B | 277 | 42.426 | 11.981 | 19.094 | 1.00 | 54.92 | B C |
| ATOM | 2519 | CD | GLN | B | 277 | 43.018 | 12.294 | 17.734 | 1.00 | 58.03 | B C |
| ATOM | 2520 | OE1 | GLN | B | 277 | 44.172 | 11.965 | 17.458 | 1.00 | 57.42 | B O |
| ATOM | 2521 | NE2 | GLN | B | 277 | 42.409 | 12.921 | 16.733 | 1.00 | 59.93 | B N |
| ATOM | 2522 | C | GLN | B | 277 | 41.712 | 9.881 | 21.246 | 1.00 | 43.63 | B C |
| ATOM | 2523 | O | GLN | B | 277 | 41.950 | 8.725 | 20.895 | 1.00 | 41.80 | B O |
| ATOM | 2524 | N | GLY | B | 278 | 40.491 | 10.299 | 21.614 | 1.00 | 43.48 | B N |
| ATOM | 2525 | CA | GLY | B | 278 | 39.329 | 9.424 | 21.519 | 1.00 | 43.38 | B C |
| ATOM | 2526 | C | GLY | B | 278 | 38.788 | 8.870 | 22.831 | 1.00 | 43.80 | B C |
| ATOM | 2527 | O | GLY | B | 278 | 37.633 | 8.439 | 22.912 | 1.00 | 44.14 | B O |
| ATOM | 2528 | N | SER | B | 279 | 39.629 | 8.859 | 23.861 | 1.00 | 42.95 | B N |
| ATOM | 2529 | CA | SER | B | 279 | 39.234 | 8.366 | 25.180 | 1.00 | 41.92 | B C |
| ATOM | 2530 | CB | SER | B | 279 | 40.444 | 8.395 | 26.108 | 1.00 | 41.54 | B C |
| ATOM | 2531 | OG | SER | B | 279 | 41.515 | 7.670 | 25.522 | 1.00 | 41.27 | B O |
| ATOM | 2532 | C | SER | B | 279 | 38.097 | 9.219 | 25.745 | 1.00 | 40.45 | B C |
| ATOM | 2533 | O | SER | B | 279 | 37.216 | 8.733 | 26.443 | 1.00 | 39.19 | B O |
| ATOM | 2534 | N | MET | B | 280 | 38.157 | 10.506 | 25.426 | 1.00 | 39.74 | B N |
| ATOM | 2535 | CA | MET | B | 280 | 37.201 | 11.501 | 25.822 | 1.00 | 38.76 | B C |
| ATOM | 2536 | CB | MET | B | 280 | 37.215 | 11.725 | 27.341 | 1.00 | 37.07 | B C |
| ATOM | 2537 | CG | MET | B | 280 | 38.427 | 12.485 | 27.871 | 1.00 | 36.64 | B C |
| ATOM | 2538 | SD | MET | B | 280 | 38.470 | 12.530 | 29.677 | 1.00 | 35.34 | B S |
| ATOM | 2539 | CE | MET | B | 280 | 37.917 | 14.201 | 29.997 | 1.00 | 34.46 | B C |
| ATOM | 2540 | C | MET | B | 280 | 37.572 | 12.730 | 25.033 | 1.00 | 39.01 | B C |
| ATOM | 2541 | O | MET | B | 280 | 38.605 | 12.786 | 24.371 | 1.00 | 38.14 | B O |
| ATOM | 2542 | N | SER | B | 281 | 36.723 | 13.693 | 25.066 | 1.00 | 40.39 | B N |
| ATOM | 2543 | CA | SER | B | 281 | 36.834 | 14.913 | 24.290 | 1.00 | 41.46 | B C |
| ATOM | 2544 | CB | SER | B | 281 | 35.458 | 15.575 | 24.130 | 1.00 | 40.43 | B C |
| ATOM | 2545 | OG | SER | B | 281 | 35.233 | 16.522 | 25.159 | 1.00 | 39.50 | B O |
| ATOM | 2546 | C | SER | B | 281 | 37.735 | 15.945 | 24.910 | 1.00 | 43.67 | B C |
| ATOM | 2547 | O | SER | B | 281 | 37.732 | 16.154 | 26.116 | 1.00 | 42.98 | B O |
| ATOM | 2548 | N | PRO | B | 282 | 38.522 | 16.587 | 24.054 | 1.00 | 45.05 | B N |
| ATOM | 2549 | CD | PRO | B | 282 | 39.231 | 15.947 | 22.931 | 1.00 | 45.98 | B C |
| ATOM | 2550 | CA | PRO | B | 282 | 39.403 | 17.603 | 24.578 | 1.00 | 46.83 | B C |
| ATOM | 2551 | CB | PRO | B | 282 | 40.038 | 18.210 | 23.333 | 1.00 | 46.76 | B C |
| ATOM | 2552 | CG | PRO | B | 282 | 40.255 | 16.976 | 22.527 | 1.00 | 46.26 | B C |
| ATOM | 2553 | C | PRO | B | 282 | 38.844 | 18.522 | 25.596 | 1.00 | 48.31 | B C |
| ATOM | 2554 | O | PRO | B | 282 | 39.325 | 18.563 | 26.742 | 1.00 | 49.86 | B O |
| ATOM | 2555 | N | ASP | B | 283 | 37.901 | 19.279 | 25.259 | 1.00 | 50.08 | B N |
| ATOM | 2556 | CA | ASP | B | 283 | 37.534 | 20.191 | 26.260 | 1.00 | 51.48 | B C |
| ATOM | 2557 | CB | ASP | B | 283 | 36.488 | 21.144 | 25.695 | 1.00 | 54.16 | B C |
| ATOM | 2558 | CG | ASP | B | 283 | 37.129 | 21.911 | 24.539 | 1.00 | 56.42 | B C |
| ATOM | 2559 | OD1 | ASP | B | 283 | 38.379 | 21.944 | 24.469 | 1.00 | 57.35 | B O |
| ATOM | 2560 | OD2 | ASP | B | 283 | 36.394 | 22.459 | 23.693 | 1.00 | 56.66 | B O |
| ATOM | 2561 | C | ASP | B | 283 | 37.137 | 19.491 | 27.567 | 1.00 | 50.81 | B C |
| ATOM | 2562 | O | ASP | B | 283 | 37.046 | 20.131 | 28.618 | 1.00 | 50.36 | B O |
| ATOM | 2563 | N | ALA | B | 284 | 36.912 | 18.176 | 27.524 | 1.00 | 50.09 | B N |
| ATOM | 2564 | CA | ALA | B | 284 | 36.511 | 17.387 | 28.722 | 1.00 | 49.31 | B C |
| ATOM | 2565 | CB | ALA | B | 284 | 35.834 | 16.088 | 28.291 | 1.00 | 49.62 | B C |
| ATOM | 2566 | C | ALA | B | 284 | 37.710 | 17.078 | 29.630 | 1.00 | 48.92 | B C |
| ATOM | 2567 | O | ALA | B | 284 | 37.649 | 17.195 | 30.856 | 1.00 | 49.53 | B O |

Figure 4

| | | | | | | | | | | | |
|---|---|---|---|---|---|---|---|---|---|---|---|
| ATOM | 2568 | N | PHE | B | 285 | 38.801 | 16.690 | 29.002 | 1.00 | 47.74 | B | N |
| ATOM | 2569 | CA | PHE | B | 285 | 40.022 | 16.400 | 29.643 | 1.00 | 45.84 | B | C |
| ATOM | 2570 | CB | PHE | B | 285 | 40.993 | 15.818 | 28.634 | 1.00 | 45.15 | B | C |
| ATOM | 2571 | CG | PHE | B | 285 | 42.372 | 15.513 | 29.130 | 1.00 | 45.54 | B | C |
| ATOM | 2572 | CD1 | PHE | B | 285 | 42.604 | 14.378 | 29.909 | 1.00 | 44.79 | B | C |
| ATOM | 2573 | CD2 | PHE | B | 285 | 43.458 | 16.321 | 28.784 | 1.00 | 44.90 | B | C |
| ATOM | 2574 | CE1 | PHE | B | 285 | 43.903 | 14.052 | 30.327 | 1.00 | 44.04 | B | C |
| ATOM | 2575 | CE2 | PHE | B | 285 | 44.759 | 15.999 | 29.200 | 1.00 | 43.86 | B | C |
| ATOM | 2576 | CZ | PHE | B | 285 | 44.978 | 14.863 | 29.967 | 1.00 | 43.77 | B | C |
| ATOM | 2577 | C | PHE | B | 285 | 40.585 | 17.696 | 30.244 | 1.00 | 43.97 | B | C |
| ATOM | 2578 | O | PHE | B | 285 | 41.011 | 17.743 | 31.385 | 1.00 | 41.47 | B | O |
| ATOM | 2579 | N | LEU | B | 286 | 40.585 | 18.749 | 29.431 | 1.00 | 42.38 | B | N |
| ATOM | 2580 | CA | LEU | B | 286 | 41.067 | 20.056 | 29.845 | 1.00 | 43.22 | B | C |
| ATOM | 2581 | CB | LEU | B | 286 | 41.138 | 21.007 | 28.647 | 1.00 | 42.25 | B | C |
| ATOM | 2582 | CG | LEU | B | 286 | 42.292 | 20.730 | 27.676 | 1.00 | 41.48 | B | C |
| ATOM | 2583 | CD1 | LEU | B | 286 | 42.006 | 21.366 | 26.318 | 1.00 | 40.04 | B | C |
| ATOM | 2584 | CD2 | LEU | B | 286 | 43.621 | 21.215 | 28.281 | 1.00 | 40.33 | B | C |
| ATOM | 2585 | C | LEU | B | 286 | 40.126 | 20.603 | 30.889 | 1.00 | 43.76 | B | C |
| ATOM | 2586 | O | LEU | B | 286 | 40.540 | 21.352 | 31.770 | 1.00 | 44.07 | B | O |
| ATOM | 2587 | N | ALA | B | 287 | 38.858 | 20.205 | 30.782 | 1.00 | 45.45 | B | N |
| ATOM | 2588 | CA | ALA | B | 287 | 37.816 | 20.625 | 31.718 | 1.00 | 45.94 | B | C |
| ATOM | 2589 | CB | ALA | B | 287 | 36.432 | 20.156 | 31.229 | 1.00 | 44.90 | B | C |
| ATOM | 2590 | C | ALA | B | 287 | 38.114 | 20.071 | 33.122 | 1.00 | 45.74 | B | C |
| ATOM | 2591 | O | ALA | B | 287 | 37.806 | 20.717 | 34.128 | 1.00 | 46.86 | B | O |
| ATOM | 2592 | N | GLU | B | 288 | 38.739 | 18.895 | 33.175 | 1.00 | 45.22 | B | N |
| ATOM | 2593 | CA | GLU | B | 288 | 39.099 | 18.257 | 34.441 | 1.00 | 46.70 | B | C |
| ATOM | 2594 | CB | GLU | B | 288 | 39.527 | 16.799 | 34.208 | 1.00 | 46.24 | B | C |
| ATOM | 2595 | CG | GLU | B | 288 | 38.483 | 15.923 | 33.509 | 1.00 | 46.72 | B | C |
| ATOM | 2596 | CD | GLU | B | 288 | 38.808 | 14.429 | 33.555 | 1.00 | 47.21 | B | C |
| ATOM | 2597 | OE1 | GLU | B | 288 | 39.968 | 14.034 | 33.278 | 1.00 | 48.28 | B | O |
| ATOM | 2598 | OE2 | GLU | B | 288 | 37.888 | 13.645 | 33.874 | 1.00 | 46.68 | B | O |
| ATOM | 2599 | C | GLU | B | 288 | 40.227 | 19.019 | 35.156 | 1.00 | 48.19 | B | C |
| ATOM | 2600 | O | GLU | B | 288 | 40.342 | 18.986 | 36.385 | 1.00 | 48.26 | B | O |
| ATOM | 2601 | N | ALA | B | 289 | 41.043 | 19.727 | 34.380 | 1.00 | 49.42 | B | N |
| ATOM | 2602 | CA | ALA | B | 289 | 42.160 | 20.488 | 34.928 | 1.00 | 49.73 | B | C |
| ATOM | 2603 | CB | ALA | B | 289 | 43.175 | 20.791 | 33.834 | 1.00 | 51.08 | B | C |
| ATOM | 2604 | C | ALA | B | 289 | 41.729 | 21.779 | 35.592 | 1.00 | 50.06 | B | C |
| ATOM | 2605 | O | ALA | B | 289 | 42.425 | 22.279 | 36.475 | 1.00 | 49.06 | B | O |
| ATOM | 2606 | N | ASN | B | 290 | 40.588 | 22.317 | 35.160 | 1.00 | 52.14 | B | N |
| ATOM | 2607 | CA | ASN | B | 290 | 40.040 | 23.577 | 35.689 | 1.00 | 53.78 | B | C |
| ATOM | 2608 | CB | ASN | B | 290 | 38.774 | 23.979 | 34.931 | 1.00 | 54.99 | B | C |
| ATOM | 2609 | CG | ASN | B | 290 | 39.051 | 24.358 | 33.489 | 1.00 | 56.14 | B | C |
| ATOM | 2610 | OD1 | ASN | B | 290 | 38.269 | 24.037 | 32.589 | 1.00 | 57.48 | B | O |
| ATOM | 2611 | ND2 | ASN | B | 290 | 40.170 | 25.038 | 33.258 | 1.00 | 55.92 | B | N |
| ATOM | 2612 | C | ASN | B | 290 | 39.751 | 23.572 | 37.187 | 1.00 | 53.82 | B | C |
| ATOM | 2613 | O | ASN | B | 290 | 39.636 | 24.631 | 37.805 | 1.00 | 53.56 | B | O |
| ATOM | 2614 | N | LEU | B | 291 | 39.601 | 22.376 | 37.743 | 1.00 | 54.41 | B | N |
| ATOM | 2615 | CA | LEU | B | 291 | 39.364 | 22.221 | 39.181 | 1.00 | 55.72 | B | C |
| ATOM | 2616 | CB | LEU | B | 291 | 38.858 | 20.809 | 39.496 | 1.00 | 56.27 | B | C |
| ATOM | 2617 | CG | LEU | B | 291 | 37.544 | 20.390 | 38.831 | 1.00 | 55.93 | B | C |
| ATOM | 2618 | CD1 | LEU | B | 291 | 37.171 | 18.969 | 39.226 | 1.00 | 56.27 | B | C |
| ATOM | 2619 | CD2 | LEU | B | 291 | 36.426 | 21.355 | 39.192 | 1.00 | 55.42 | B | C |
| ATOM | 2620 | C | LEU | B | 291 | 40.625 | 22.512 | 39.998 | 1.00 | 55.83 | B | C |
| ATOM | 2621 | O | LEU | B | 291 | 40.591 | 23.213 | 40.999 | 1.00 | 56.08 | B | O |
| ATOM | 2622 | N | MET | B | 292 | 41.728 | 21.955 | 39.509 | 1.00 | 55.33 | B | N |
| ATOM | 2623 | CA | MET | B | 292 | 43.030 | 22.145 | 40.127 | 1.00 | 55.90 | B | C |
| ATOM | 2624 | CB | MET | B | 292 | 44.066 | 21.400 | 39.292 | 1.00 | 56.34 | B | C |
| ATOM | 2625 | CG | MET | B | 292 | 45.213 | 20.826 | 40.051 | 1.00 | 55.98 | B | C |
| ATOM | 2626 | SD | MET | B | 292 | 45.992 | 19.619 | 38.998 | 1.00 | 56.23 | B | S |
| ATOM | 2627 | CE | MET | B | 292 | 45.364 | 18.066 | 39.756 | 1.00 | 56.93 | B | C |

Figure 4

| ATOM | 2628 | C   | MET | B | 292 | 43.365 | 23.646 | 40.186 | 1.00 | 56.46 | B | C |
|------|------|-----|-----|---|-----|--------|--------|--------|------|-------|---|---|
| ATOM | 2629 | O   | MET | B | 292 | 44.057 | 24.109 | 41.094 | 1.00 | 56.64 | B | O |
| ATOM | 2630 | N   | LYS | B | 293 | 42.873 | 24.398 | 39.203 | 1.00 | 56.60 | B | N |
| ATOM | 2631 | CA  | LYS | B | 293 | 43.095 | 25.835 | 39.141 | 1.00 | 56.55 | B | C |
| ATOM | 2632 | CB  | LYS | B | 293 | 42.496 | 26.410 | 37.862 | 1.00 | 56.84 | B | C |
| ATOM | 2633 | CG  | LYS | B | 293 | 43.086 | 25.892 | 36.573 | 1.00 | 57.45 | B | C |
| ATOM | 2634 | CD  | LYS | B | 293 | 42.491 | 26.656 | 35.391 | 1.00 | 58.55 | B | C |
| ATOM | 2635 | CE  | LYS | B | 293 | 43.064 | 26.190 | 34.058 | 1.00 | 60.01 | B | C |
| ATOM | 2636 | NZ  | LYS | B | 293 | 42.459 | 26.948 | 32.929 | 1.00 | 61.52 | B | N |
| ATOM | 2637 | C   | LYS | B | 293 | 42.386 | 26.479 | 40.319 | 1.00 | 56.55 | B | C |
| ATOM | 2638 | O   | LYS | B | 293 | 42.961 | 27.295 | 41.046 | 1.00 | 57.43 | B | O |
| ATOM | 2639 | N   | GLN | B | 294 | 41.130 | 26.076 | 40.498 | 1.00 | 55.79 | B | N |
| ATOM | 2640 | CA  | GLN | B | 294 | 40.257 | 26.576 | 41.555 | 1.00 | 55.09 | B | C |
| ATOM | 2641 | CB  | GLN | B | 294 | 38.855 | 25.979 | 41.378 | 1.00 | 57.51 | B | C |
| ATOM | 2642 | CG  | GLN | B | 294 | 38.263 | 26.228 | 39.991 | 1.00 | 61.32 | B | C |
| ATOM | 2643 | CD  | GLN | B | 294 | 38.368 | 27.697 | 39.548 | 1.00 | 63.52 | B | C |
| ATOM | 2644 | OE1 | GLN | B | 294 | 39.172 | 28.044 | 38.671 | 1.00 | 63.83 | B | O |
| ATOM | 2645 | NE2 | GLN | B | 294 | 37.558 | 28.563 | 40.165 | 1.00 | 64.95 | B | N |
| ATOM | 2646 | C   | GLN | B | 294 | 40.754 | 26.346 | 42.987 | 1.00 | 53.22 | B | C |
| ATOM | 2647 | O   | GLN | B | 294 | 40.842 | 27.287 | 43.791 | 1.00 | 52.24 | B | O |
| ATOM | 2648 | N   | LEU | B | 295 | 41.076 | 25.097 | 43.306 | 1.00 | 50.60 | B | N |
| ATOM | 2649 | CA  | LEU | B | 295 | 41.553 | 24.744 | 44.636 | 1.00 | 48.32 | B | C |
| ATOM | 2650 | CB  | LEU | B | 295 | 40.898 | 23.419 | 45.108 | 1.00 | 48.35 | B | C |
| ATOM | 2651 | CG  | LEU | B | 295 | 39.409 | 23.454 | 45.417 | 1.00 | 47.96 | B | C |
| ATOM | 2652 | CD1 | LEU | B | 295 | 38.947 | 22.138 | 46.029 | 1.00 | 49.23 | B | C |
| ATOM | 2653 | CD2 | LEU | B | 295 | 39.093 | 24.599 | 46.356 | 1.00 | 48.05 | B | C |
| ATOM | 2654 | C   | LEU | B | 295 | 43.056 | 24.580 | 44.675 | 1.00 | 46.54 | B | C |
| ATOM | 2655 | O   | LEU | B | 295 | 43.617 | 23.709 | 44.018 | 1.00 | 47.58 | B | O |
| ATOM | 2656 | N   | GLN | B | 296 | 43.715 | 25.435 | 45.431 | 1.00 | 43.69 | B | N |
| ATOM | 2657 | CA  | GLN | B | 296 | 45.126 | 25.301 | 45.657 | 1.00 | 42.26 | B | C |
| ATOM | 2658 | CB  | GLN | B | 296 | 45.885 | 26.569 | 45.234 | 1.00 | 44.10 | B | C |
| ATOM | 2659 | CG  | GLN | B | 296 | 46.100 | 26.711 | 43.738 | 1.00 | 46.45 | B | C |
| ATOM | 2660 | CD  | GLN | B | 296 | 46.125 | 28.144 | 43.285 | 1.00 | 48.87 | B | C |
| ATOM | 2661 | OE1 | GLN | B | 296 | 46.159 | 29.062 | 44.102 | 1.00 | 49.07 | B | O |
| ATOM | 2662 | NE2 | GLN | B | 296 | 46.129 | 28.566 | 42.035 | 1.00 | 50.23 | B | N |
| ATOM | 2663 | C   | GLN | B | 296 | 45.304 | 25.109 | 47.144 | 1.00 | 40.17 | B | C |
| ATOM | 2664 | O   | GLN | B | 296 | 44.532 | 25.652 | 47.954 | 1.00 | 39.66 | B | O |
| ATOM | 2665 | N   | HIS | B | 297 | 46.319 | 24.343 | 47.517 | 1.00 | 37.68 | B | N |
| ATOM | 2666 | CA  | HIS | B | 297 | 46.627 | 24.042 | 48.875 | 1.00 | 35.86 | B | C |
| ATOM | 2667 | CB  | HIS | B | 297 | 45.460 | 23.314 | 49.540 | 1.00 | 34.29 | B | C |
| ATOM | 2668 | CG  | HIS | B | 297 | 45.592 | 23.219 | 51.095 | 1.00 | 32.18 | B | C |
| ATOM | 2669 | CD2 | HIS | B | 297 | 45.213 | 24.068 | 52.082 | 1.00 | 30.92 | B | C |
| ATOM | 2670 | ND1 | HIS | B | 297 | 46.189 | 22.145 | 51.722 | 1.00 | 31.37 | B | N |
| ATOM | 2671 | CE1 | HIS | B | 297 | 46.174 | 22.337 | 53.030 | 1.00 | 30.23 | B | C |
| ATOM | 2672 | NE2 | HIS | B | 297 | 45.589 | 23.495 | 53.274 | 1.00 | 30.78 | B | N |
| ATOM | 2673 | C   | HIS | B | 297 | 47.877 | 23.158 | 48.893 | 1.00 | 35.62 | B | C |
| ATOM | 2674 | O   | HIS | B | 297 | 48.119 | 22.421 | 47.946 | 1.00 | 33.93 | B | O |
| ATOM | 2675 | N   | GLN | B | 298 | 48.660 | 23.202 | 49.971 | 1.00 | 37.42 | B | N |
| ATOM | 2676 | CA  | GLN | B | 298 | 49.863 | 22.377 | 50.087 | 1.00 | 38.84 | B | C |
| ATOM | 2677 | CB  | GLN | B | 298 | 50.674 | 22.716 | 51.341 | 1.00 | 41.28 | B | C |
| ATOM | 2678 | CG  | GLN | B | 298 | 51.610 | 23.930 | 51.185 | 1.00 | 45.96 | B | C |
| ATOM | 2679 | CD  | GLN | B | 298 | 52.549 | 23.858 | 49.951 | 1.00 | 47.62 | B | C |
| ATOM | 2680 | OE1 | GLN | B | 298 | 52.669 | 24.830 | 49.196 | 1.00 | 47.97 | B | O |
| ATOM | 2681 | NE2 | GLN | B | 298 | 53.213 | 22.716 | 49.755 | 1.00 | 48.06 | B | N |
| ATOM | 2682 | C   | GLN | B | 298 | 49.571 | 20.888 | 50.078 | 1.00 | 37.86 | B | C |
| ATOM | 2683 | O   | GLN | B | 298 | 50.432 | 20.094 | 49.705 | 1.00 | 37.78 | B | O |
| ATOM | 2684 | N   | ARG | B | 299 | 48.365 | 20.509 | 50.489 | 1.00 | 36.25 | B | N |
| ATOM | 2685 | CA  | ARG | B | 299 | 47.985 | 19.092 | 50.515 | 1.00 | 34.95 | B | C |
| ATOM | 2686 | CB  | ARG | B | 299 | 47.157 | 18.780 | 51.764 | 1.00 | 35.24 | B | C |
| ATOM | 2687 | CG  | ARG | B | 299 | 47.902 | 19.000 | 53.066 | 1.00 | 35.44 | B | C |

Figure 4

| | | | | | | | | | | | |
|---|---|---|---|---|---|---|---|---|---|---|---|
| ATOM | 2688 | CD | ARG | B | 299 | 49.094 | 18.100 | 53.157 | 1.00 | 35.83 | B C |
| ATOM | 2689 | NE | ARG | B | 299 | 50.124 | 18.732 | 53.957 | 1.00 | 38.99 | B N |
| ATOM | 2690 | CZ | ARG | B | 299 | 51.429 | 18.588 | 53.753 | 1.00 | 39.91 | B C |
| ATOM | 2691 | NH1 | ARG | B | 299 | 51.884 | 17.829 | 52.760 | 1.00 | 39.59 | B N |
| ATOM | 2692 | NH2 | ARG | B | 299 | 52.282 | 19.193 | 54.567 | 1.00 | 41.61 | B N |
| ATOM | 2693 | C | ARG | B | 299 | 47.262 | 18.610 | 49.252 | 1.00 | 33.37 | B C |
| ATOM | 2694 | O | ARG | B | 299 | 46.776 | 17.486 | 49.195 | 1.00 | 32.51 | B O |
| ATOM | 2695 | N | LEU | B | 300 | 47.201 | 19.472 | 48.240 | 1.00 | 32.46 | B N |
| ATOM | 2696 | CA | LEU | B | 300 | 46.577 | 19.168 | 46.949 | 1.00 | 31.29 | B C |
| ATOM | 2697 | CB | LEU | B | 300 | 45.429 | 20.138 | 46.666 | 1.00 | 30.90 | B C |
| ATOM | 2698 | CG | LEU | B | 300 | 44.014 | 19.867 | 47.163 | 1.00 | 29.90 | B C |
| ATOM | 2699 | CD1 | LEU | B | 300 | 44.002 | 19.442 | 48.600 | 1.00 | 30.51 | B C |
| ATOM | 2700 | CD2 | LEU | B | 300 | 43.196 | 21.120 | 46.966 | 1.00 | 29.76 | B C |
| ATOM | 2701 | C | LEU | B | 300 | 47.621 | 19.339 | 45.846 | 1.00 | 31.98 | B C |
| ATOM | 2702 | O | LEU | B | 300 | 48.452 | 20.258 | 45.903 | 1.00 | 31.74 | B O |
| ATOM | 2703 | N | VAL | B | 301 | 47.570 | 18.475 | 44.832 | 1.00 | 33.07 | B N |
| ATOM | 2704 | CA | VAL | B | 301 | 48.520 | 18.564 | 43.724 | 1.00 | 33.20 | B C |
| ATOM | 2705 | CB | VAL | B | 301 | 48.393 | 17.392 | 42.760 | 1.00 | 31.42 | B C |
| ATOM | 2706 | CG1 | VAL | B | 301 | 49.278 | 17.628 | 41.574 | 1.00 | 31.56 | B C |
| ATOM | 2707 | CG2 | VAL | B | 301 | 48.785 | 16.103 | 43.453 | 1.00 | 31.37 | B C |
| ATOM | 2708 | C | VAL | B | 301 | 48.300 | 19.868 | 42.958 | 1.00 | 34.68 | B C |
| ATOM | 2709 | O | VAL | B | 301 | 47.171 | 20.195 | 42.571 | 1.00 | 32.85 | B O |
| ATOM | 2710 | N | ARG | B | 302 | 49.396 | 20.608 | 42.778 | 1.00 | 37.00 | B N |
| ATOM | 2711 | CA | ARG | B | 302 | 49.398 | 21.897 | 42.096 | 1.00 | 37.70 | B C |
| ATOM | 2712 | CB | ARG | B | 302 | 50.486 | 22.796 | 42.696 | 1.00 | 40.52 | B C |
| ATOM | 2713 | CG | ARG | B | 302 | 50.625 | 24.179 | 42.075 | 1.00 | 44.23 | B C |
| ATOM | 2714 | CD | ARG | B | 302 | 51.591 | 24.159 | 40.892 | 1.00 | 47.68 | B C |
| ATOM | 2715 | NE | ARG | B | 302 | 52.228 | 25.456 | 40.661 | 1.00 | 51.11 | B N |
| ATOM | 2716 | CZ | ARG | B | 302 | 53.103 | 26.031 | 41.492 | 1.00 | 52.57 | B C |
| ATOM | 2717 | NH1 | ARG | B | 302 | 53.464 | 25.436 | 42.629 | 1.00 | 51.36 | B N |
| ATOM | 2718 | NH2 | ARG | B | 302 | 53.627 | 27.215 | 41.180 | 1.00 | 54.00 | B N |
| ATOM | 2719 | C | ARG | B | 302 | 49.581 | 21.766 | 40.593 | 1.00 | 37.52 | B C |
| ATOM | 2720 | O | ARG | B | 302 | 50.379 | 20.960 | 40.100 | 1.00 | 36.32 | B O |
| ATOM | 2721 | N | LEU | B | 303 | 48.810 | 22.576 | 39.880 | 1.00 | 39.08 | B N |
| ATOM | 2722 | CA | LEU | B | 303 | 48.827 | 22.623 | 38.425 | 1.00 | 39.63 | B C |
| ATOM | 2723 | CB | LEU | B | 303 | 47.416 | 22.791 | 37.903 | 1.00 | 38.89 | B C |
| ATOM | 2724 | CG | LEU | B | 303 | 47.393 | 22.838 | 36.391 | 1.00 | 40.91 | B C |
| ATOM | 2725 | CD1 | LEU | B | 303 | 47.090 | 21.442 | 35.896 | 1.00 | 42.25 | B C |
| ATOM | 2726 | CD2 | LEU | B | 303 | 46.366 | 23.856 | 35.884 | 1.00 | 42.98 | B C |
| ATOM | 2727 | C | LEU | B | 303 | 49.648 | 23.815 | 37.943 | 1.00 | 39.87 | B C |
| ATOM | 2728 | O | LEU | B | 303 | 49.435 | 24.945 | 38.390 | 1.00 | 41.02 | B O |
| ATOM | 2729 | N | TYR | B | 304 | 50.595 | 23.555 | 37.048 | 1.00 | 40.45 | B N |
| ATOM | 2730 | CA | TYR | B | 304 | 51.419 | 24.624 | 36.487 | 1.00 | 40.01 | B C |
| ATOM | 2731 | CB | TYR | B | 304 | 52.825 | 24.118 | 36.174 | 1.00 | 41.04 | B C |
| ATOM | 2732 | CG | TYR | B | 304 | 53.655 | 23.844 | 37.400 | 1.00 | 43.99 | B C |
| ATOM | 2733 | CD1 | TYR | B | 304 | 53.632 | 22.595 | 38.009 | 1.00 | 45.36 | B C |
| ATOM | 2734 | CE1 | TYR | B | 304 | 54.376 | 22.339 | 39.156 | 1.00 | 45.61 | B C |
| ATOM | 2735 | CD2 | TYR | B | 304 | 54.455 | 24.840 | 37.976 | 1.00 | 45.74 | B C |
| ATOM | 2736 | CE2 | TYR | B | 304 | 55.209 | 24.585 | 39.134 | 1.00 | 45.70 | B C |
| ATOM | 2737 | CZ | TYR | B | 304 | 55.155 | 23.328 | 39.707 | 1.00 | 45.30 | B C |
| ATOM | 2738 | OH | TYR | B | 304 | 55.877 | 23.041 | 40.833 | 1.00 | 46.87 | B O |
| ATOM | 2739 | C | TYR | B | 304 | 50.764 | 25.180 | 35.217 | 1.00 | 39.06 | B C |
| ATOM | 2740 | O | TYR | B | 304 | 50.473 | 26.364 | 35.128 | 1.00 | 38.84 | B O |
| ATOM | 2741 | N | ALA | B | 305 | 50.450 | 24.301 | 34.271 | 1.00 | 38.55 | B N |
| ATOM | 2742 | CA | ALA | B | 305 | 49.857 | 24.740 | 33.022 | 1.00 | 37.12 | B C |
| ATOM | 2743 | CB | ALA | B | 305 | 50.928 | 25.443 | 32.196 | 1.00 | 37.85 | B C |
| ATOM | 2744 | C | ALA | B | 305 | 49.250 | 23.600 | 32.218 | 1.00 | 36.12 | B C |
| ATOM | 2745 | O | ALA | B | 305 | 49.236 | 22.451 | 32.661 | 1.00 | 34.50 | B O |
| ATOM | 2746 | N | VAL | B | 306 | 48.742 | 23.946 | 31.036 | 1.00 | 36.98 | B N |
| ATOM | 2747 | CA | VAL | B | 306 | 48.154 | 22.994 | 30.094 | 1.00 | 38.37 | B C |

Figure 4

```
ATOM   2748  CB   VAL B 306      46.600  22.874  30.266  1.00 38.64      B    C
ATOM   2749  CG1  VAL B 306      46.261  21.905  31.390  1.00 37.95      B    C
ATOM   2750  CG2  VAL B 306      45.982  24.244  30.551  1.00 38.81      B    C
ATOM   2751  C    VAL B 306      48.485  23.373  28.636  1.00 38.94      B    C
ATOM   2752  O    VAL B 306      48.745  24.542  28.322  1.00 38.36      B    O
ATOM   2753  N    VAL B 307      48.519  22.363  27.767  1.00 39.75      B    N
ATOM   2754  CA   VAL B 307      48.778  22.542  26.339  1.00 40.22      B    C
ATOM   2755  CB   VAL B 307      50.021  21.740  25.884  1.00 37.81      B    C
ATOM   2756  CG1  VAL B 307      50.309  22.015  24.413  1.00 37.88      B    C
ATOM   2757  CG2  VAL B 307      51.216  22.106  26.742  1.00 36.08      B    C
ATOM   2758  C    VAL B 307      47.520  22.062  25.583  1.00 42.67      B    C
ATOM   2759  O    VAL B 307      47.250  20.861  25.492  1.00 41.91      B    O
ATOM   2760  N    THR B 308      46.755  23.017  25.049  1.00 45.24      B    N
ATOM   2761  CA   THR B 308      45.507  22.724  24.346  1.00 46.10      B    C
ATOM   2762  CB   THR B 308      44.639  23.987  24.208  1.00 44.58      B    C
ATOM   2763  OG1  THR B 308      45.375  25.012  23.539  1.00 45.04      B    O
ATOM   2764  CG2  THR B 308      44.235  24.493  25.559  1.00 44.01      B    C
ATOM   2765  C    THR B 308      45.599  22.011  22.997  1.00 48.74      B    C
ATOM   2766  O    THR B 308      44.765  21.172  22.695  1.00 49.42      B    O
ATOM   2767  N    GLN B 309      46.584  22.351  22.174  1.00 52.83      B    N
ATOM   2768  CA   GLN B 309      46.707  21.660  20.898  1.00 56.39      B    C
ATOM   2769  CB   GLN B 309      47.719  22.370  19.999  1.00 59.39      B    C
ATOM   2770  CG   GLN B 309      47.348  23.804  19.657  1.00 63.22      B    C
ATOM   2771  CD   GLN B 309      46.026  23.903  18.921  1.00 64.66      B    C
ATOM   2772  OE1  GLN B 309      45.365  22.895  18.671  1.00 64.09      B    O
ATOM   2773  NE2  GLN B 309      45.452  25.017  18.482  1.00 64.86      B    N
ATOM   2774  C    GLN B 309      47.105  20.201  21.098  1.00 56.93      B    C
ATOM   2775  O    GLN B 309      47.909  19.898  21.977  1.00 56.59      B    O
ATOM   2776  N    GLU B 310      46.510  19.319  20.319  1.00 58.66      B    N
ATOM   2777  CA   GLU B 310      46.767  17.879  20.388  1.00 60.36      B    C
ATOM   2778  CB   GLU B 310      45.773  17.135  19.466  1.00 63.71      B    C
ATOM   2779  CG   GLU B 310      45.672  17.688  17.998  1.00 67.70      B    C
ATOM   2780  CD   GLU B 310      44.381  18.504  17.699  1.00 68.91      B    C
ATOM   2781  OE1  GLU B 310      43.321  18.234  18.325  1.00 69.84      B    O
ATOM   2782  OE2  GLU B 310      44.433  19.403  16.821  1.00 67.89      B    O
ATOM   2783  C    GLU B 310      48.223  17.471  20.040  1.00 59.58      B    C
ATOM   2784  O    GLU B 310      48.811  18.003  19.080  1.00 59.94      B    O
ATOM   2785  N    PRO B 311      48.837  16.564  20.842  1.00 58.01      B    N
ATOM   2786  CD   PRO B 311      50.181  16.058  20.487  1.00 57.69      B    C
ATOM   2787  CA   PRO B 311      48.328  15.842  22.023  1.00 55.68      B    C
ATOM   2788  CB   PRO B 311      49.449  14.832  22.332  1.00 55.95      B    C
ATOM   2789  CG   PRO B 311      50.139  14.650  21.020  1.00 56.81      B    C
ATOM   2790  C    PRO B 311      48.103  16.751  23.238  1.00 52.81      B    C
ATOM   2791  O    PRO B 311      48.984  17.532  23.608  1.00 52.75      B    O
ATOM   2792  N    ILE B 312      46.935  16.624  23.863  1.00 49.25      B    N
ATOM   2793  CA   ILE B 312      46.594  17.427  25.048  1.00 44.76      B    C
ATOM   2794  CB   ILE B 312      45.093  17.239  25.461  1.00 44.07      B    C
ATOM   2795  CG2  ILE B 312      44.663  18.358  26.407  1.00 43.65      B    C
ATOM   2796  CG1  ILE B 312      44.184  17.227  24.230  1.00 43.67      B    C
ATOM   2797  CD1  ILE B 312      44.091  18.546  23.519  1.00 43.24      B    C
ATOM   2798  C    ILE B 312      47.481  17.037  26.253  1.00 40.50      B    C
ATOM   2799  O    ILE B 312      47.739  15.847  26.491  1.00 38.53      B    O
ATOM   2800  N    TYR B 313      47.922  18.042  27.010  1.00 36.94      B    N
ATOM   2801  CA   TYR B 313      48.758  17.829  28.194  1.00 35.48      B    C
ATOM   2802  CB   TYR B 313      50.195  18.328  27.989  1.00 35.48      B    C
ATOM   2803  CG   TYR B 313      51.087  17.626  26.994  1.00 36.81      B    C
ATOM   2804  CD1  TYR B 313      50.834  16.327  26.561  1.00 38.30      B    C
ATOM   2805  CE1  TYR B 313      51.718  15.673  25.692  1.00 38.28      B    C
ATOM   2806  CD2  TYR B 313      52.247  18.260  26.535  1.00 37.78      B    C
ATOM   2807  CE2  TYR B 313      53.132  17.624  25.680  1.00 37.33      B    C
```

Figure 4

| | | | | | | | | | | | |
|---|---|---|---|---|---|---|---|---|---|---|---|
| ATOM | 2808 | CZ  | TYR | B | 313 | 52.868 | 16.337 | 25.265 | 1.00 | 38.39 | B | C |
| ATOM | 2809 | OH  | TYR | B | 313 | 53.769 | 15.715 | 24.431 | 1.00 | 38.72 | B | O |
| ATOM | 2810 | C   | TYR | B | 313 | 48.259 | 18.618 | 29.398 | 1.00 | 32.68 | B | C |
| ATOM | 2811 | O   | TYR | B | 313 | 47.800 | 19.753 | 29.272 | 1.00 | 30.53 | B | O |
| ATOM | 2812 | N   | ILE | B | 314 | 48.442 | 18.024 | 30.573 | 1.00 | 31.56 | B | N |
| ATOM | 2813 | CA  | ILE | B | 314 | 48.133 | 18.675 | 31.838 | 1.00 | 30.03 | B | C |
| ATOM | 2814 | CB  | ILE | B | 314 | 47.020 | 17.978 | 32.638 | 1.00 | 30.78 | B | C |
| ATOM | 2815 | CG2 | ILE | B | 314 | 46.816 | 18.719 | 33.953 | 1.00 | 28.72 | B | C |
| ATOM | 2816 | CG1 | ILE | B | 314 | 45.712 | 17.969 | 31.840 | 1.00 | 30.73 | B | C |
| ATOM | 2817 | CD1 | ILE | B | 314 | 44.558 | 17.312 | 32.564 | 1.00 | 31.27 | B | C |
| ATOM | 2818 | C   | ILE | B | 314 | 49.456 | 18.587 | 32.612 | 1.00 | 28.40 | B | C |
| ATOM | 2819 | O   | ILE | B | 314 | 49.974 | 17.500 | 32.863 | 1.00 | 26.31 | B | O |
| ATOM | 2820 | N   | ILE | B | 315 | 50.028 | 19.741 | 32.928 | 1.00 | 29.18 | B | N |
| ATOM | 2821 | CA  | ILE | B | 315 | 51.302 | 19.800 | 33.636 | 1.00 | 30.01 | B | C |
| ATOM | 2822 | CB  | ILE | B | 315 | 52.287 | 20.818 | 32.965 | 1.00 | 30.30 | B | C |
| ATOM | 2823 | CG2 | ILE | B | 315 | 53.538 | 21.023 | 33.833 | 1.00 | 30.30 | B | C |
| ATOM | 2824 | CG1 | ILE | B | 315 | 52.685 | 20.327 | 31.566 | 1.00 | 30.89 | B | C |
| ATOM | 2825 | CD1 | ILE | B | 315 | 51.711 | 20.695 | 30.463 | 1.00 | 30.25 | B | C |
| ATOM | 2826 | C   | ILE | B | 315 | 51.110 | 20.166 | 35.099 | 1.00 | 29.00 | B | C |
| ATOM | 2827 | O   | ILE | B | 315 | 50.570 | 21.231 | 35.421 | 1.00 | 29.23 | B | O |
| ATOM | 2828 | N   | THR | B | 316 | 51.534 | 19.261 | 35.977 | 1.00 | 27.67 | B | N |
| ATOM | 2829 | CA  | THR | B | 316 | 51.420 | 19.472 | 37.410 | 1.00 | 28.38 | B | C |
| ATOM | 2830 | CB  | THR | B | 316 | 50.476 | 18.464 | 38.096 | 1.00 | 25.55 | B | C |
| ATOM | 2831 | OG1 | THR | B | 316 | 51.064 | 17.156 | 38.050 | 1.00 | 23.55 | B | O |
| ATOM | 2832 | CG2 | THR | B | 316 | 49.106 | 18.446 | 37.433 | 1.00 | 25.78 | B | C |
| ATOM | 2833 | C   | THR | B | 316 | 52.779 | 19.233 | 38.002 | 1.00 | 29.67 | B | C |
| ATOM | 2834 | O   | THR | B | 316 | 53.704 | 18.806 | 37.308 | 1.00 | 30.36 | B | O |
| ATOM | 2835 | N   | GLU | B | 317 | 52.883 | 19.483 | 39.302 | 1.00 | 30.10 | B | N |
| ATOM | 2836 | CA  | GLU | B | 317 | 54.123 | 19.263 | 40.022 | 1.00 | 29.04 | B | C |
| ATOM | 2837 | CB  | GLU | B | 317 | 53.994 | 19.755 | 41.466 | 1.00 | 30.63 | B | C |
| ATOM | 2838 | CG  | GLU | B | 317 | 52.882 | 19.076 | 42.264 | 1.00 | 32.24 | B | C |
| ATOM | 2839 | CD  | GLU | B | 317 | 52.938 | 19.430 | 43.725 | 1.00 | 33.58 | B | C |
| ATOM | 2840 | OE1 | GLU | B | 317 | 51.913 | 19.903 | 44.261 | 1.00 | 33.63 | B | O |
| ATOM | 2841 | OE2 | GLU | B | 317 | 54.019 | 19.246 | 44.333 | 1.00 | 35.31 | B | O |
| ATOM | 2842 | C   | GLU | B | 317 | 54.435 | 17.773 | 39.999 | 1.00 | 26.38 | B | C |
| ATOM | 2843 | O   | GLU | B | 317 | 53.543 | 16.937 | 39.832 | 1.00 | 26.77 | B | O |
| ATOM | 2844 | N   | TYR | B | 318 | 55.715 | 17.461 | 40.123 | 1.00 | 24.56 | B | N |
| ATOM | 2845 | CA  | TYR | B | 318 | 56.194 | 16.085 | 40.123 | 1.00 | 24.80 | B | C |
| ATOM | 2846 | CB  | TYR | B | 318 | 57.623 | 16.054 | 39.534 | 1.00 | 23.76 | B | C |
| ATOM | 2847 | CG  | TYR | B | 318 | 58.287 | 14.699 | 39.506 | 1.00 | 24.30 | B | C |
| ATOM | 2848 | CD1 | TYR | B | 318 | 57.814 | 13.681 | 38.673 | 1.00 | 24.62 | B | C |
| ATOM | 2849 | CE1 | TYR | B | 318 | 58.402 | 12.418 | 38.670 | 1.00 | 25.17 | B | C |
| ATOM | 2850 | CD2 | TYR | B | 318 | 59.373 | 14.423 | 40.337 | 1.00 | 25.08 | B | C |
| ATOM | 2851 | CE2 | TYR | B | 318 | 59.979 | 13.158 | 40.340 | 1.00 | 25.20 | B | C |
| ATOM | 2852 | CZ  | TYR | B | 318 | 59.490 | 12.167 | 39.509 | 1.00 | 25.68 | B | C |
| ATOM | 2853 | OH  | TYR | B | 318 | 60.087 | 10.927 | 39.515 | 1.00 | 26.64 | B | O |
| ATOM | 2854 | C   | TYR | B | 318 | 56.169 | 15.508 | 41.544 | 1.00 | 25.16 | B | C |
| ATOM | 2855 | O   | TYR | B | 318 | 56.467 | 16.207 | 42.514 | 1.00 | 26.38 | B | O |
| ATOM | 2856 | N   | MET | B | 319 | 55.745 | 14.256 | 41.671 | 1.00 | 25.80 | B | N |
| ATOM | 2857 | CA  | MET | B | 319 | 55.702 | 13.587 | 42.968 | 1.00 | 26.78 | B | C |
| ATOM | 2858 | CB  | MET | B | 319 | 54.272 | 13.179 | 43.343 | 1.00 | 26.98 | B | C |
| ATOM | 2859 | CG  | MET | B | 319 | 53.326 | 14.361 | 43.604 | 1.00 | 27.18 | B | C |
| ATOM | 2860 | SD  | MET | B | 319 | 53.794 | 15.530 | 44.937 | 1.00 | 30.43 | B | S |
| ATOM | 2861 | CE  | MET | B | 319 | 53.471 | 14.548 | 46.374 | 1.00 | 28.54 | B | C |
| ATOM | 2862 | C   | MET | B | 319 | 56.607 | 12.379 | 42.841 | 1.00 | 27.22 | B | C |
| ATOM | 2863 | O   | MET | B | 319 | 56.226 | 11.369 | 42.269 | 1.00 | 26.26 | B | O |
| ATOM | 2864 | N   | GLU | B | 320 | 57.832 | 12.547 | 43.331 | 1.00 | 30.01 | B | N |
| ATOM | 2865 | CA  | GLU | B | 320 | 58.906 | 11.556 | 43.292 | 1.00 | 30.57 | B | C |
| ATOM | 2866 | CB  | GLU | B | 320 | 60.053 | 12.012 | 44.204 | 1.00 | 35.15 | B | C |
| ATOM | 2867 | CG  | GLU | B | 320 | 61.104 | 10.955 | 44.532 | 1.00 | 40.28 | B | C |

Figure 4

| | | | | | | | | | | | |
|---|---|---|---|---|---|---|---|---|---|---|---|
| ATOM | 2868 | CD | GLU | B | 320 | 62.444 | 11.191 | 43.846 | 1.00 | 42.13 | B | C |
| ATOM | 2869 | OE1 | GLU | B | 320 | 62.738 | 12.353 | 43.474 | 1.00 | 43.34 | B | O |
| ATOM | 2870 | OE2 | GLU | B | 320 | 63.199 | 10.202 | 43.688 | 1.00 | 43.43 | B | O |
| ATOM | 2871 | C | GLU | B | 320 | 58.533 | 10.123 | 43.599 | 1.00 | 28.39 | B | C |
| ATOM | 2872 | O | GLU | B | 320 | 58.946 | 9.218 | 42.882 | 1.00 | 28.49 | B | O |
| ATOM | 2873 | N | ASN | B | 321 | 57.755 | 9.898 | 44.650 | 1.00 | 27.18 | B | N |
| ATOM | 2874 | CA | ASN | B | 321 | 57.373 | 8.532 | 44.992 | 1.00 | 25.92 | B | C |
| ATOM | 2875 | CB | ASN | B | 321 | 57.467 | 8.317 | 46.495 | 1.00 | 26.12 | B | C |
| ATOM | 2876 | CG | ASN | B | 321 | 58.894 | 8.247 | 46.955 | 1.00 | 26.44 | B | C |
| ATOM | 2877 | OD1 | ASN | B | 321 | 59.635 | 7.340 | 46.561 | 1.00 | 27.19 | B | O |
| ATOM | 2878 | ND2 | ASN | B | 321 | 59.312 | 9.225 | 47.747 | 1.00 | 26.29 | B | N |
| ATOM | 2879 | C | ASN | B | 321 | 56.040 | 8.054 | 44.419 | 1.00 | 25.76 | B | C |
| ATOM | 2880 | O | ASN | B | 321 | 55.549 | 6.957 | 44.759 | 1.00 | 25.00 | B | O |
| ATOM | 2881 | N | GLY | B | 322 | 55.499 | 8.877 | 43.517 | 1.00 | 25.72 | B | N |
| ATOM | 2882 | CA | GLY | B | 322 | 54.264 | 8.584 | 42.806 | 1.00 | 26.23 | B | C |
| ATOM | 2883 | C | GLY | B | 322 | 52.992 | 8.343 | 43.579 | 1.00 | 25.06 | B | C |
| ATOM | 2884 | O | GLY | B | 322 | 52.591 | 9.181 | 44.358 | 1.00 | 26.76 | B | O |
| ATOM | 2885 | N | SER | B | 323 | 52.346 | 7.214 | 43.311 | 1.00 | 24.48 | B | N |
| ATOM | 2886 | CA | SER | B | 323 | 51.103 | 6.834 | 43.956 | 1.00 | 26.78 | B | C |
| ATOM | 2887 | CB | SER | B | 323 | 50.327 | 5.900 | 43.036 | 1.00 | 26.49 | B | C |
| ATOM | 2888 | OG | SER | B | 323 | 49.080 | 5.557 | 43.602 | 1.00 | 29.99 | B | O |
| ATOM | 2889 | C | SER | B | 323 | 51.325 | 6.147 | 45.301 | 1.00 | 25.63 | B | C |
| ATOM | 2890 | O | SER | B | 323 | 52.129 | 5.219 | 45.408 | 1.00 | 25.20 | B | O |
| ATOM | 2891 | N | LEU | B | 324 | 50.578 | 6.588 | 46.310 | 1.00 | 26.32 | B | N |
| ATOM | 2892 | CA | LEU | B | 324 | 50.661 | 6.024 | 47.666 | 1.00 | 26.99 | B | C |
| ATOM | 2893 | CB | LEU | B | 324 | 49.757 | 6.804 | 48.635 | 1.00 | 27.17 | B | C |
| ATOM | 2894 | CG | LEU | B | 324 | 49.625 | 6.384 | 50.115 | 1.00 | 26.43 | B | C |
| ATOM | 2895 | CD1 | LEU | B | 324 | 50.954 | 6.565 | 50.868 | 1.00 | 24.23 | B | C |
| ATOM | 2896 | CD2 | LEU | B | 324 | 48.520 | 7.220 | 50.772 | 1.00 | 24.66 | B | C |
| ATOM | 2897 | C | LEU | B | 324 | 50.345 | 4.522 | 47.749 | 1.00 | 27.04 | B | C |
| ATOM | 2898 | O | LEU | B | 324 | 50.989 | 3.796 | 48.511 | 1.00 | 28.33 | B | O |
| ATOM | 2899 | N | VAL | B | 325 | 49.376 | 4.046 | 46.968 | 1.00 | 27.43 | B | N |
| ATOM | 2900 | CA | VAL | B | 325 | 49.039 | 2.627 | 47.001 | 1.00 | 27.54 | B | C |
| ATOM | 2901 | CB | VAL | B | 325 | 47.759 | 2.313 | 46.174 | 1.00 | 25.91 | B | C |
| ATOM | 2902 | CG1 | VAL | B | 325 | 48.015 | 2.434 | 44.684 | 1.00 | 25.76 | B | C |
| ATOM | 2903 | CG2 | VAL | B | 325 | 47.231 | 0.933 | 46.517 | 1.00 | 25.07 | B | C |
| ATOM | 2904 | C | VAL | B | 325 | 50.252 | 1.798 | 46.529 | 1.00 | 29.40 | B | C |
| ATOM | 2905 | O | VAL | B | 325 | 50.523 | 0.701 | 47.048 | 1.00 | 29.93 | B | O |
| ATOM | 2906 | N | ASP | B | 326 | 51.014 | 2.368 | 45.597 | 1.00 | 30.35 | B | N |
| ATOM | 2907 | CA | ASP | B | 326 | 52.211 | 1.715 | 45.065 | 1.00 | 31.76 | B | C |
| ATOM | 2908 | CB | ASP | B | 326 | 52.558 | 2.284 | 43.694 | 1.00 | 31.36 | B | C |
| ATOM | 2909 | CG | ASP | B | 326 | 51.613 | 1.827 | 42.621 | 1.00 | 30.81 | B | C |
| ATOM | 2910 | OD1 | ASP | B | 326 | 51.119 | 0.678 | 42.698 | 1.00 | 30.30 | B | O |
| ATOM | 2911 | OD2 | ASP | B | 326 | 51.383 | 2.619 | 41.687 | 1.00 | 31.66 | B | O |
| ATOM | 2912 | C | ASP | B | 326 | 53.417 | 1.886 | 45.988 | 1.00 | 32.64 | B | C |
| ATOM | 2913 | O | ASP | B | 326 | 54.213 | 0.962 | 46.174 | 1.00 | 34.53 | B | O |
| ATOM | 2914 | N | PHE | B | 327 | 53.554 | 3.080 | 46.548 | 1.00 | 32.87 | B | N |
| ATOM | 2915 | CA | PHE | B | 327 | 54.651 | 3.382 | 47.441 | 1.00 | 32.44 | B | C |
| ATOM | 2916 | CB | PHE | B | 327 | 54.642 | 4.862 | 47.800 | 1.00 | 32.87 | B | C |
| ATOM | 2917 | CG | PHE | B | 327 | 55.730 | 5.252 | 48.744 | 1.00 | 35.21 | B | C |
| ATOM | 2918 | CD1 | PHE | B | 327 | 57.072 | 5.069 | 48.386 | 1.00 | 35.00 | B | C |
| ATOM | 2919 | CD2 | PHE | B | 327 | 55.424 | 5.751 | 50.021 | 1.00 | 35.48 | B | C |
| ATOM | 2920 | CE1 | PHE | B | 327 | 58.089 | 5.368 | 49.285 | 1.00 | 36.13 | B | C |
| ATOM | 2921 | CE2 | PHE | B | 327 | 56.443 | 6.056 | 50.933 | 1.00 | 35.99 | B | C |
| ATOM | 2922 | CZ | PHE | B | 327 | 57.774 | 5.864 | 50.566 | 1.00 | 36.42 | B | C |
| ATOM | 2923 | C | PHE | B | 327 | 54.604 | 2.545 | 48.715 | 1.00 | 32.80 | B | C |
| ATOM | 2924 | O | PHE | B | 327 | 55.640 | 2.129 | 49.215 | 1.00 | 33.24 | B | O |
| ATOM | 2925 | N | LEU | B | 328 | 53.409 | 2.286 | 49.236 | 1.00 | 32.15 | B | N |
| ATOM | 2926 | CA | LEU | B | 328 | 53.280 | 1.504 | 50.462 | 1.00 | 33.04 | B | C |
| ATOM | 2927 | CB | LEU | B | 328 | 51.828 | 1.519 | 50.964 | 1.00 | 31.61 | B | C |

Figure 4

| | | | | | | | | | | | |
|---|---|---|---|---|---|---|---|---|---|---|---|
| ATOM | 2928 | CG | LEU | B | 328 | 51.308 | 2.789 | 51.644 | 1.00 | 30.78 | B C |
| ATOM | 2929 | CD1 | LEU | B | 328 | 49.817 | 2.667 | 51.911 | 1.00 | 31.33 | B C |
| ATOM | 2930 | CD2 | LEU | B | 328 | 52.059 | 3.041 | 52.927 | 1.00 | 30.45 | B C |
| ATOM | 2931 | C | LEU | B | 328 | 53.795 | 0.062 | 50.352 | 1.00 | 34.51 | B C |
| ATOM | 2932 | O | LEU | B | 328 | 54.046 | -0.583 | 51.370 | 1.00 | 35.45 | B O |
| ATOM | 2933 | N | LYS | B | 329 | 53.949 | -0.441 | 49.128 | 1.00 | 36.11 | B N |
| ATOM | 2934 | CA | LYS | B | 329 | 54.433 | -1.806 | 48.909 | 1.00 | 37.59 | B C |
| ATOM | 2935 | CB | LYS | B | 329 | 53.693 | -2.461 | 47.745 | 1.00 | 38.56 | B C |
| ATOM | 2936 | CG | LYS | B | 329 | 52.187 | -2.433 | 47.845 | 1.00 | 39.48 | B C |
| ATOM | 2937 | CD | LYS | B | 329 | 51.584 | -3.174 | 46.675 | 1.00 | 40.74 | B C |
| ATOM | 2938 | CE | LYS | B | 329 | 50.077 | -3.070 | 46.670 | 1.00 | 41.61 | B C |
| ATOM | 2939 | NZ | LYS | B | 329 | 49.625 | -1.672 | 46.432 | 1.00 | 41.99 | B N |
| ATOM | 2940 | C | LYS | B | 329 | 55.949 | -1.891 | 48.644 | 1.00 | 38.23 | B C |
| ATOM | 2941 | O | LYS | B | 329 | 56.526 | -2.988 | 48.699 | 1.00 | 39.67 | B O |
| ATOM | 2942 | N | THR | B | 330 | 56.580 | -0.746 | 48.362 | 1.00 | 36.72 | B N |
| ATOM | 2943 | CA | THR | B | 330 | 58.016 | -0.685 | 48.091 | 1.00 | 35.44 | B C |
| ATOM | 2944 | CB | THR | B | 330 | 58.428 | 0.712 | 47.592 | 1.00 | 34.35 | B C |
| ATOM | 2945 | OG1 | THR | B | 330 | 58.203 | 1.685 | 48.612 | 1.00 | 33.66 | B O |
| ATOM | 2946 | CG2 | THR | B | 330 | 57.645 | 1.085 | 46.348 | 1.00 | 33.43 | B C |
| ATOM | 2947 | C | THR | B | 330 | 58.813 | -1.023 | 49.351 | 1.00 | 36.70 | B C |
| ATOM | 2948 | O | THR | B | 330 | 58.291 | -0.885 | 50.454 | 1.00 | 39.18 | B O |
| ATOM | 2949 | N | PRO | B | 331 | 60.082 | -1.486 | 49.206 | 1.00 | 36.61 | B N |
| ATOM | 2950 | CD | PRO | B | 331 | 60.811 | -1.798 | 47.963 | 1.00 | 35.85 | B C |
| ATOM | 2951 | CA | PRO | B | 331 | 60.906 | -1.831 | 50.372 | 1.00 | 35.76 | B C |
| ATOM | 2952 | CB | PRO | B | 331 | 62.290 | -2.018 | 49.753 | 1.00 | 35.94 | B C |
| ATOM | 2953 | CG | PRO | B | 331 | 61.961 | -2.664 | 48.459 | 1.00 | 34.87 | B C |
| ATOM | 2954 | C | PRO | B | 331 | 60.907 | -0.761 | 51.446 | 1.00 | 34.54 | B C |
| ATOM | 2955 | O | PRO | B | 331 | 60.802 | -1.081 | 52.613 | 1.00 | 34.91 | B O |
| ATOM | 2956 | N | SER | B | 332 | 61.008 | 0.500 | 51.032 | 1.00 | 35.36 | B N |
| ATOM | 2957 | CA | SER | B | 332 | 61.013 | 1.663 | 51.928 | 1.00 | 37.33 | B C |
| ATOM | 2958 | CB | SER | B | 332 | 61.397 | 2.929 | 51.158 | 1.00 | 38.41 | B C |
| ATOM | 2959 | OG | SER | B | 332 | 62.594 | 2.722 | 50.425 | 1.00 | 43.00 | B O |
| ATOM | 2960 | C | SER | B | 332 | 59.647 | 1.895 | 52.577 | 1.00 | 38.42 | B C |
| ATOM | 2961 | O | SER | B | 332 | 59.569 | 2.284 | 53.755 | 1.00 | 37.76 | B O |
| ATOM | 2962 | N | GLY | B | 333 | 58.590 | 1.702 | 51.778 | 1.00 | 37.92 | B N |
| ATOM | 2963 | CA | GLY | B | 333 | 57.213 | 1.869 | 52.232 | 1.00 | 36.25 | B C |
| ATOM | 2964 | C | GLY | B | 333 | 56.769 | 0.815 | 53.236 | 1.00 | 35.12 | B C |
| ATOM | 2965 | O | GLY | B | 333 | 55.987 | 1.101 | 54.141 | 1.00 | 35.73 | B O |
| ATOM | 2966 | N | ILE | B | 334 | 57.251 | -0.410 | 53.059 | 1.00 | 34.72 | B N |
| ATOM | 2967 | CA | ILE | B | 334 | 56.942 | -1.502 | 53.974 | 1.00 | 35.38 | B C |
| ATOM | 2968 | CB | ILE | B | 334 | 57.551 | -2.838 | 53.467 | 1.00 | 36.41 | B C |
| ATOM | 2969 | CG2 | ILE | B | 334 | 57.538 | -3.887 | 54.578 | 1.00 | 37.26 | B C |
| ATOM | 2970 | CG1 | ILE | B | 334 | 56.804 | -3.355 | 52.228 | 1.00 | 36.44 | B C |
| ATOM | 2971 | CD1 | ILE | B | 334 | 55.492 | -4.112 | 52.527 | 1.00 | 36.74 | B C |
| ATOM | 2972 | C | ILE | B | 334 | 57.545 | -1.180 | 55.353 | 1.00 | 36.01 | B C |
| ATOM | 2973 | O | ILE | B | 334 | 56.925 | -1.426 | 56.389 | 1.00 | 36.01 | B O |
| ATOM | 2974 | N | LYS | B | 335 | 58.737 | -0.580 | 55.338 | 1.00 | 36.77 | B N |
| ATOM | 2975 | CA | LYS | B | 335 | 59.479 | -0.226 | 56.547 | 1.00 | 35.89 | B C |
| ATOM | 2976 | CB | LYS | B | 335 | 60.950 | 0.001 | 56.206 | 1.00 | 36.72 | B C |
| ATOM | 2977 | CG | LYS | B | 335 | 61.659 | -1.193 | 55.606 | 1.00 | 38.38 | B C |
| ATOM | 2978 | CD | LYS | B | 335 | 63.032 | -0.778 | 55.083 | 1.00 | 39.80 | B C |
| ATOM | 2979 | CE | LYS | B | 335 | 63.559 | -1.800 | 54.081 | 1.00 | 41.77 | B C |
| ATOM | 2980 | NZ | LYS | B | 335 | 64.414 | -1.179 | 53.012 | 1.00 | 42.16 | B N |
| ATOM | 2981 | C | LYS | B | 335 | 58.982 | 0.982 | 57.329 | 1.00 | 35.32 | B C |
| ATOM | 2982 | O | LYS | B | 335 | 59.447 | 1.214 | 58.440 | 1.00 | 35.07 | B O |
| ATOM | 2983 | N | LEU | B | 336 | 58.055 | 1.755 | 56.765 | 1.00 | 35.60 | B N |
| ATOM | 2984 | CA | LEU | B | 336 | 57.524 | 2.953 | 57.442 | 1.00 | 34.00 | B C |
| ATOM | 2985 | CB | LEU | B | 336 | 56.481 | 3.662 | 56.554 | 1.00 | 33.34 | B C |
| ATOM | 2986 | CG | LEU | B | 336 | 56.943 | 4.289 | 55.230 | 1.00 | 31.61 | B C |
| ATOM | 2987 | CD1 | LEU | B | 336 | 55.769 | 4.627 | 54.337 | 1.00 | 30.63 | B C |

Figure 4

| | | | | | | | | | | | |
|---|---|---|---|---|---|---|---|---|---|---|---|
| ATOM | 2988 | CD2 | LEU | B | 336 | 57.761 | 5.524 | 55.508 | 1.00 | 31.56 | B | C |
| ATOM | 2989 | C | LEU | B | 336 | 56.919 | 2.650 | 58.826 | 1.00 | 32.70 | B | C |
| ATOM | 2990 | O | LEU | B | 336 | 56.253 | 1.627 | 59.025 | 1.00 | 32.02 | B | O |
| ATOM | 2991 | N | THR | B | 337 | 57.185 | 3.533 | 59.782 | 1.00 | 31.63 | B | N |
| ATOM | 2992 | CA | THR | B | 337 | 56.668 | 3.367 | 61.127 | 1.00 | 33.27 | B | C |
| ATOM | 2993 | CB | THR | B | 337 | 57.502 | 4.170 | 62.182 | 1.00 | 34.22 | B | C |
| ATOM | 2994 | OG1 | THR | B | 337 | 57.432 | 5.576 | 61.916 | 1.00 | 35.18 | B | O |
| ATOM | 2995 | CG2 | THR | B | 337 | 58.961 | 3.728 | 62.160 | 1.00 | 34.21 | B | C |
| ATOM | 2996 | C | THR | B | 337 | 55.194 | 3.786 | 61.211 | 1.00 | 34.01 | B | C |
| ATOM | 2997 | O | THR | B | 337 | 54.712 | 4.572 | 60.385 | 1.00 | 32.75 | B | O |
| ATOM | 2998 | N | ILE | B | 338 | 54.496 | 3.266 | 62.222 | 1.00 | 33.67 | B | N |
| ATOM | 2999 | CA | ILE | B | 338 | 53.091 | 3.590 | 62.435 | 1.00 | 33.70 | B | C |
| ATOM | 3000 | CB | ILE | B | 338 | 52.495 | 2.858 | 63.682 | 1.00 | 33.52 | B | C |
| ATOM | 3001 | CG2 | ILE | B | 338 | 53.150 | 3.361 | 64.985 | 1.00 | 33.09 | B | C |
| ATOM | 3002 | CG1 | ILE | B | 338 | 50.974 | 3.067 | 63.735 | 1.00 | 32.85 | B | C |
| ATOM | 3003 | CD1 | ILE | B | 338 | 50.204 | 2.469 | 62.561 | 1.00 | 31.35 | B | C |
| ATOM | 3004 | C | ILE | B | 338 | 52.981 | 5.096 | 62.617 | 1.00 | 34.03 | B | C |
| ATOM | 3005 | O | ILE | B | 338 | 51.982 | 5.705 | 62.250 | 1.00 | 33.91 | B | O |
| ATOM | 3006 | N | ASN | B | 339 | 54.037 | 5.702 | 63.145 | 1.00 | 34.18 | B | N |
| ATOM | 3007 | CA | ASN | B | 339 | 54.065 | 7.143 | 63.357 | 1.00 | 33.87 | B | C |
| ATOM | 3008 | CB | ASN | B | 339 | 55.331 | 7.534 | 64.095 | 1.00 | 34.40 | B | C |
| ATOM | 3009 | CG | ASN | B | 339 | 55.321 | 7.073 | 65.501 | 1.00 | 36.28 | B | C |
| ATOM | 3010 | OD1 | ASN | B | 339 | 54.954 | 7.835 | 66.397 | 1.00 | 36.98 | B | O |
| ATOM | 3011 | ND2 | ASN | B | 339 | 55.668 | 5.801 | 65.721 | 1.00 | 37.06 | B | N |
| ATOM | 3012 | C | ASN | B | 339 | 54.028 | 7.887 | 62.049 | 1.00 | 33.52 | B | C |
| ATOM | 3013 | O | ASN | B | 339 | 53.319 | 8.882 | 61.909 | 1.00 | 33.52 | B | O |
| ATOM | 3014 | N | LYS | B | 340 | 54.855 | 7.424 | 61.121 | 1.00 | 32.69 | B | N |
| ATOM | 3015 | CA | LYS | B | 340 | 54.960 | 8.023 | 59.810 | 1.00 | 33.71 | B | C |
| ATOM | 3016 | CB | LYS | B | 340 | 56.153 | 7.392 | 59.068 | 1.00 | 34.32 | B | C |
| ATOM | 3017 | CG | LYS | B | 340 | 56.357 | 7.889 | 57.633 | 1.00 | 34.83 | B | C |
| ATOM | 3018 | CD | LYS | B | 340 | 56.664 | 9.378 | 57.600 | 1.00 | 35.83 | B | C |
| ATOM | 3019 | CE | LYS | B | 340 | 56.504 | 9.938 | 56.198 | 1.00 | 35.34 | B | C |
| ATOM | 3020 | NZ | LYS | B | 340 | 56.617 | 11.422 | 56.192 | 1.00 | 36.18 | B | N |
| ATOM | 3021 | C | LYS | B | 340 | 53.641 | 7.855 | 59.026 | 1.00 | 32.25 | B | C |
| ATOM | 3022 | O | LYS | B | 340 | 53.153 | 8.804 | 58.400 | 1.00 | 31.56 | B | O |
| ATOM | 3023 | N | LEU | B | 341 | 53.054 | 6.663 | 59.105 | 1.00 | 32.73 | B | N |
| ATOM | 3024 | CA | LEU | B | 341 | 51.795 | 6.349 | 58.425 | 1.00 | 32.81 | B | C |
| ATOM | 3025 | CB | LEU | B | 341 | 51.411 | 4.885 | 58.677 | 1.00 | 32.37 | B | C |
| ATOM | 3026 | CG | LEU | B | 341 | 52.434 | 3.819 | 58.280 | 1.00 | 32.35 | B | C |
| ATOM | 3027 | CD1 | LEU | B | 341 | 51.924 | 2.424 | 58.617 | 1.00 | 32.02 | B | C |
| ATOM | 3028 | CD2 | LEU | B | 341 | 52.717 | 3.936 | 56.796 | 1.00 | 32.73 | B | C |
| ATOM | 3029 | C | LEU | B | 341 | 50.656 | 7.265 | 58.868 | 1.00 | 32.21 | B | C |
| ATOM | 3030 | O | LEU | B | 341 | 49.889 | 7.756 | 58.043 | 1.00 | 31.98 | B | O |
| ATOM | 3031 | N | LEU | B | 342 | 50.564 | 7.521 | 60.169 | 1.00 | 33.05 | B | N |
| ATOM | 3032 | CA | LEU | B | 342 | 49.520 | 8.387 | 60.701 | 1.00 | 34.48 | B | C |
| ATOM | 3033 | CB | LEU | B | 342 | 49.449 | 8.283 | 62.222 | 1.00 | 36.58 | B | C |
| ATOM | 3034 | CG | LEU | B | 342 | 48.988 | 6.912 | 62.700 | 1.00 | 38.22 | B | C |
| ATOM | 3035 | CD1 | LEU | B | 342 | 48.749 | 7.025 | 64.152 | 1.00 | 41.39 | B | C |
| ATOM | 3036 | CD2 | LEU | B | 342 | 47.715 | 6.472 | 62.036 | 1.00 | 40.52 | B | C |
| ATOM | 3037 | C | LEU | B | 342 | 49.688 | 9.833 | 60.291 | 1.00 | 34.08 | B | C |
| ATOM | 3038 | O | LEU | B | 342 | 48.706 | 10.552 | 60.102 | 1.00 | 33.63 | B | O |
| ATOM | 3039 | N | ASP | B | 343 | 50.921 | 10.303 | 60.212 | 1.00 | 33.39 | B | N |
| ATOM | 3040 | CA | ASP | B | 343 | 51.093 | 11.669 | 59.803 | 1.00 | 34.14 | B | C |
| ATOM | 3041 | CB | ASP | B | 343 | 52.485 | 12.205 | 60.121 | 1.00 | 38.75 | B | C |
| ATOM | 3042 | CG | ASP | B | 343 | 52.513 | 13.728 | 60.089 | 1.00 | 43.42 | B | C |
| ATOM | 3043 | OD1 | ASP | B | 343 | 52.037 | 14.338 | 61.090 | 1.00 | 44.48 | B | O |
| ATOM | 3044 | OD2 | ASP | B | 343 | 52.931 | 14.306 | 59.040 | 1.00 | 43.35 | B | O |
| ATOM | 3045 | C | ASP | B | 343 | 50.795 | 11.763 | 58.316 | 1.00 | 31.84 | B | C |
| ATOM | 3046 | O | ASP | B | 343 | 50.400 | 12.814 | 57.828 | 1.00 | 30.72 | B | O |
| ATOM | 3047 | N | MET | B | 344 | 51.000 | 10.668 | 57.595 | 1.00 | 29.48 | B | N |

Figure 4

| | | | | | | | | | | | |
|---|---|---|---|---|---|---|---|---|---|---|---|
| ATOM | 3048 | CA | MET | B | 344 | 50.688 | 10.657 | 56.182 | 1.00 | 29.98 | B | C |
| ATOM | 3049 | CB | MET | B | 344 | 51.215 | 9.382 | 55.522 | 1.00 | 32.58 | B | C |
| ATOM | 3050 | CG | MET | B | 344 | 52.743 | 9.358 | 55.323 | 1.00 | 34.11 | B | C |
| ATOM | 3051 | SD | MET | B | 344 | 53.248 | 7.933 | 54.332 | 1.00 | 36.34 | B | S |
| ATOM | 3052 | CE | MET | B | 344 | 53.859 | 8.734 | 52.904 | 1.00 | 35.74 | B | C |
| ATOM | 3053 | C | MET | B | 344 | 49.168 | 10.748 | 56.051 | 1.00 | 28.48 | B | C |
| ATOM | 3054 | O | MET | B | 344 | 48.657 | 11.542 | 55.264 | 1.00 | 27.61 | B | O |
| ATOM | 3055 | N | ALA | B | 345 | 48.459 | 9.962 | 56.862 | 1.00 | 25.72 | B | N |
| ATOM | 3056 | CA | ALA | B | 345 | 46.999 | 9.961 | 56.881 | 1.00 | 23.55 | B | C |
| ATOM | 3057 | CB | ALA | B | 345 | 46.480 | 8.905 | 57.850 | 1.00 | 23.60 | B | C |
| ATOM | 3058 | C | ALA | B | 345 | 46.479 | 11.335 | 57.284 | 1.00 | 22.68 | B | C |
| ATOM | 3059 | O | ALA | B | 345 | 45.563 | 11.843 | 56.667 | 1.00 | 24.31 | B | O |
| ATOM | 3060 | N | ALA | B | 346 | 47.081 | 11.940 | 58.306 | 1.00 | 21.71 | B | N |
| ATOM | 3061 | CA | ALA | B | 346 | 46.685 | 13.261 | 58.780 | 1.00 | 20.97 | B | C |
| ATOM | 3062 | CB | ALA | B | 346 | 47.468 | 13.614 | 60.010 | 1.00 | 20.79 | B | C |
| ATOM | 3063 | C | ALA | B | 346 | 46.880 | 14.337 | 57.697 | 1.00 | 23.19 | B | C |
| ATOM | 3064 | O | ALA | B | 346 | 46.202 | 15.379 | 57.696 | 1.00 | 22.78 | B | O |
| ATOM | 3065 | N | GLN | B | 347 | 47.823 | 14.092 | 56.788 | 1.00 | 24.77 | B | N |
| ATOM | 3066 | CA | GLN | B | 347 | 48.102 | 15.015 | 55.690 | 1.00 | 24.88 | B | C |
| ATOM | 3067 | CB | GLN | B | 347 | 49.392 | 14.629 | 54.995 | 1.00 | 26.66 | B | C |
| ATOM | 3068 | CG | GLN | B | 347 | 50.630 | 14.910 | 55.785 | 1.00 | 28.88 | B | C |
| ATOM | 3069 | CD | GLN | B | 347 | 51.851 | 14.696 | 54.943 | 1.00 | 30.94 | B | C |
| ATOM | 3070 | OE1 | GLN | B | 347 | 52.492 | 15.651 | 54.521 | 1.00 | 35.14 | B | O |
| ATOM | 3071 | NE2 | GLN | B | 347 | 52.153 | 13.442 | 54.641 | 1.00 | 31.13 | B | N |
| ATOM | 3072 | C | GLN | B | 347 | 46.977 | 14.970 | 54.678 | 1.00 | 22.83 | B | C |
| ATOM | 3073 | O | GLN | B | 347 | 46.562 | 16.000 | 54.152 | 1.00 | 22.87 | B | O |
| ATOM | 3074 | N | ILE | B | 348 | 46.511 | 13.758 | 54.397 | 1.00 | 22.18 | B | N |
| ATOM | 3075 | CA | ILE | B | 348 | 45.426 | 13.517 | 53.457 | 1.00 | 21.06 | B | C |
| ATOM | 3076 | CB | ILE | B | 348 | 45.293 | 12.010 | 53.161 | 1.00 | 21.29 | B | C |
| ATOM | 3077 | CG2 | ILE | B | 348 | 44.128 | 11.765 | 52.190 | 1.00 | 22.42 | B | C |
| ATOM | 3078 | CG1 | ILE | B | 348 | 46.603 | 11.466 | 52.564 | 1.00 | 19.74 | B | C |
| ATOM | 3079 | CD1 | ILE | B | 348 | 46.688 | 9.969 | 52.541 | 1.00 | 16.26 | B | C |
| ATOM | 3080 | C | ILE | B | 348 | 44.138 | 14.061 | 54.079 | 1.00 | 20.46 | B | C |
| ATOM | 3081 | O | ILE | B | 348 | 43.331 | 14.705 | 53.415 | 1.00 | 19.98 | B | O |
| ATOM | 3082 | N | ALA | B | 349 | 43.993 | 13.851 | 55.383 | 1.00 | 20.79 | B | N |
| ATOM | 3083 | CA | ALA | B | 349 | 42.842 | 14.341 | 56.111 | 1.00 | 20.36 | B | C |
| ATOM | 3084 | CB | ALA | B | 349 | 42.863 | 13.807 | 57.528 | 1.00 | 18.11 | B | C |
| ATOM | 3085 | C | ALA | B | 349 | 42.852 | 15.885 | 56.088 | 1.00 | 21.50 | B | C |
| ATOM | 3086 | O | ALA | B | 349 | 41.789 | 16.514 | 56.016 | 1.00 | 22.69 | B | O |
| ATOM | 3087 | N | GLU | B | 350 | 44.046 | 16.485 | 56.055 | 1.00 | 22.53 | B | N |
| ATOM | 3088 | CA | GLU | B | 350 | 44.173 | 17.941 | 56.015 | 1.00 | 23.09 | B | C |
| ATOM | 3089 | CB | GLU | B | 350 | 45.611 | 18.388 | 56.331 | 1.00 | 26.13 | B | C |
| ATOM | 3090 | CG | GLU | B | 350 | 45.819 | 19.917 | 56.282 | 1.00 | 27.95 | B | C |
| ATOM | 3091 | CD | GLU | B | 350 | 47.260 | 20.357 | 56.531 | 1.00 | 28.87 | B | C |
| ATOM | 3092 | OE1 | GLU | B | 350 | 48.141 | 19.504 | 56.745 | 1.00 | 28.91 | B | O |
| ATOM | 3093 | OE2 | GLU | B | 350 | 47.512 | 21.575 | 56.511 | 1.00 | 30.73 | B | O |
| ATOM | 3094 | C | GLU | B | 350 | 43.716 | 18.531 | 54.686 | 1.00 | 23.14 | B | C |
| ATOM | 3095 | O | GLU | B | 350 | 43.041 | 19.561 | 54.671 | 1.00 | 23.75 | B | O |
| ATOM | 3096 | N | GLY | B | 351 | 44.116 | 17.906 | 53.576 | 1.00 | 23.67 | B | N |
| ATOM | 3097 | CA | GLY | B | 351 | 43.705 | 18.382 | 52.260 | 1.00 | 22.04 | B | C |
| ATOM | 3098 | C | GLY | B | 351 | 42.200 | 18.222 | 52.083 | 1.00 | 22.33 | B | C |
| ATOM | 3099 | O | GLY | B | 351 | 41.551 | 19.059 | 51.458 | 1.00 | 21.40 | B | O |
| ATOM | 3100 | N | MET | B | 352 | 41.654 | 17.140 | 52.644 | 1.00 | 22.05 | B | N |
| ATOM | 3101 | CA | MET | B | 352 | 40.226 | 16.843 | 52.590 | 1.00 | 22.06 | B | C |
| ATOM | 3102 | CB | MET | B | 352 | 39.949 | 15.410 | 53.029 | 1.00 | 21.30 | B | C |
| ATOM | 3103 | CG | MET | B | 352 | 40.241 | 14.347 | 51.977 | 1.00 | 20.72 | B | C |
| ATOM | 3104 | SD | MET | B | 352 | 39.608 | 14.705 | 50.312 | 1.00 | 22.06 | B | S |
| ATOM | 3105 | CE | MET | B | 352 | 37.813 | 15.066 | 50.621 | 1.00 | 20.10 | B | C |
| ATOM | 3106 | C | MET | B | 352 | 39.441 | 17.810 | 53.457 | 1.00 | 22.54 | B | C |
| ATOM | 3107 | O | MET | B | 352 | 38.292 | 18.124 | 53.160 | 1.00 | 22.59 | B | O |

Figure 4

| | | | | | | | | | | |
|---|---|---|---|---|---|---|---|---|---|---|
| ATOM | 3108 | N   | ALA | B 353 | 40.071 | 18.291 | 54.525 | 1.00 24.54 | B | N |
| ATOM | 3109 | CA  | ALA | B 353 | 39.435 | 19.259 | 55.411 | 1.00 26.25 | B | C |
| ATOM | 3110 | CB  | ALA | B 353 | 40.251 | 19.430 | 56.685 | 1.00 26.99 | B | C |
| ATOM | 3111 | C   | ALA | B 353 | 39.316 | 20.592 | 54.662 | 1.00 28.25 | B | C |
| ATOM | 3112 | O   | ALA | B 353 | 38.340 | 21.332 | 54.834 | 1.00 29.51 | B | O |
| ATOM | 3113 | N   | PHE | B 354 | 40.328 | 20.908 | 53.855 | 1.00 28.37 | B | N |
| ATOM | 3114 | CA  | PHE | B 354 | 40.312 | 22.128 | 53.056 | 1.00 26.86 | B | C |
| ATOM | 3115 | CB  | PHE | B 354 | 41.674 | 22.346 | 52.373 | 1.00 25.79 | B | C |
| ATOM | 3116 | CG  | PHE | B 354 | 41.690 | 23.508 | 51.398 | 1.00 24.64 | B | C |
| ATOM | 3117 | CD1 | PHE | B 354 | 41.589 | 24.825 | 51.853 | 1.00 25.00 | B | C |
| ATOM | 3118 | CD2 | PHE | B 354 | 41.821 | 23.283 | 50.032 | 1.00 24.63 | B | C |
| ATOM | 3119 | CE1 | PHE | B 354 | 41.618 | 25.897 | 50.960 | 1.00 24.48 | B | C |
| ATOM | 3120 | CE2 | PHE | B 354 | 41.852 | 24.344 | 49.132 | 1.00 23.72 | B | C |
| ATOM | 3121 | CZ  | PHE | B 354 | 41.753 | 25.651 | 49.598 | 1.00 23.80 | B | C |
| ATOM | 3122 | C   | PHE | B 354 | 39.209 | 22.007 | 51.998 | 1.00 25.21 | B | C |
| ATOM | 3123 | O   | PHE | B 354 | 38.466 | 22.951 | 51.772 | 1.00 27.94 | B | O |
| ATOM | 3124 | N   | ILE | B 355 | 39.133 | 20.843 | 51.353 | 1.00 24.44 | B | N |
| ATOM | 3125 | CA  | ILE | B 355 | 38.143 | 20.541 | 50.308 | 1.00 24.16 | B | C |
| ATOM | 3126 | CB  | ILE | B 355 | 38.423 | 19.119 | 49.683 | 1.00 23.09 | B | C |
| ATOM | 3127 | CG2 | ILE | B 355 | 37.215 | 18.592 | 48.901 | 1.00 21.00 | B | C |
| ATOM | 3128 | CG1 | ILE | B 355 | 39.686 | 19.174 | 48.797 | 1.00 21.79 | B | C |
| ATOM | 3129 | CD1 | ILE | B 355 | 40.212 | 17.827 | 48.355 | 1.00 19.16 | B | C |
| ATOM | 3130 | C   | ILE | B 355 | 36.724 | 20.650 | 50.885 | 1.00 25.88 | B | C |
| ATOM | 3131 | O   | ILE | B 355 | 35.831 | 21.232 | 50.265 | 1.00 25.95 | B | O |
| ATOM | 3132 | N   | GLU | B 356 | 36.569 | 20.172 | 52.118 | 1.00 26.65 | B | N |
| ATOM | 3133 | CA  | GLU | B 356 | 35.314 | 20.196 | 52.864 | 1.00 27.57 | B | C |
| ATOM | 3134 | CB  | GLU | B 356 | 35.487 | 19.347 | 54.124 | 1.00 27.74 | B | C |
| ATOM | 3135 | CG  | GLU | B 356 | 34.350 | 19.322 | 55.123 | 1.00 25.27 | B | C |
| ATOM | 3136 | CD  | GLU | B 356 | 34.743 | 18.560 | 56.372 | 1.00 24.42 | B | C |
| ATOM | 3137 | OE1 | GLU | B 356 | 35.473 | 19.118 | 57.201 | 1.00 24.46 | B | O |
| ATOM | 3138 | OE2 | GLU | B 356 | 34.355 | 17.394 | 56.531 | 1.00 25.11 | B | O |
| ATOM | 3139 | C   | GLU | B 356 | 34.946 | 21.629 | 53.235 | 1.00 29.32 | B | C |
| ATOM | 3140 | O   | GLU | B 356 | 33.789 | 22.044 | 53.108 | 1.00 32.39 | B | O |
| ATOM | 3141 | N   | GLU | B 357 | 35.945 | 22.383 | 53.661 | 1.00 29.96 | B | N |
| ATOM | 3142 | CA  | GLU | B 357 | 35.790 | 23.774 | 54.038 | 1.00 32.71 | B | C |
| ATOM | 3143 | CB  | GLU | B 357 | 37.166 | 24.301 | 54.437 | 1.00 36.39 | B | C |
| ATOM | 3144 | CG  | GLU | B 357 | 37.336 | 25.806 | 54.363 | 1.00 40.01 | B | C |
| ATOM | 3145 | CD  | GLU | B 357 | 36.840 | 26.497 | 55.608 | 1.00 41.77 | B | C |
| ATOM | 3146 | OE1 | GLU | B 357 | 37.452 | 26.253 | 56.671 | 1.00 43.70 | B | O |
| ATOM | 3147 | OE2 | GLU | B 357 | 35.856 | 27.273 | 55.528 | 1.00 43.04 | B | O |
| ATOM | 3148 | C   | GLU | B 357 | 35.247 | 24.606 | 52.869 | 1.00 33.48 | B | C |
| ATOM | 3149 | O   | GLU | B 357 | 34.377 | 25.472 | 53.044 | 1.00 33.22 | B | O |
| ATOM | 3150 | N   | ARG | B 358 | 35.766 | 24.325 | 51.680 | 1.00 34.57 | B | N |
| ATOM | 3151 | CA  | ARG | B 358 | 35.394 | 25.040 | 50.472 | 1.00 37.64 | B | C |
| ATOM | 3152 | CB  | ARG | B 358 | 36.566 | 25.021 | 49.496 | 1.00 38.91 | B | C |
| ATOM | 3153 | CG  | ARG | B 358 | 37.830 | 25.642 | 50.081 | 1.00 42.50 | B | C |
| ATOM | 3154 | CD  | ARG | B 358 | 37.733 | 27.159 | 50.233 | 1.00 46.27 | B | C |
| ATOM | 3155 | NE  | ARG | B 358 | 37.588 | 27.821 | 48.931 | 1.00 52.44 | B | N |
| ATOM | 3156 | CZ  | ARG | B 358 | 38.486 | 27.777 | 47.937 | 1.00 55.14 | B | C |
| ATOM | 3157 | NH1 | ARG | B 358 | 39.620 | 27.106 | 48.069 | 1.00 56.98 | B | N |
| ATOM | 3158 | NH2 | ARG | B 358 | 38.250 | 28.386 | 46.783 | 1.00 56.70 | B | N |
| ATOM | 3159 | C   | ARG | B 358 | 34.124 | 24.528 | 49.801 | 1.00 37.80 | B | C |
| ATOM | 3160 | O   | ARG | B 358 | 33.722 | 25.038 | 48.757 | 1.00 38.77 | B | O |
| ATOM | 3161 | N   | ASN | B 359 | 33.503 | 23.521 | 50.408 | 1.00 39.10 | B | N |
| ATOM | 3162 | CA  | ASN | B 359 | 32.257 | 22.914 | 49.918 | 1.00 39.72 | B | C |
| ATOM | 3163 | CB  | ASN | B 359 | 31.130 | 23.946 | 49.902 | 1.00 42.40 | B | C |
| ATOM | 3164 | CG  | ASN | B 359 | 30.996 | 24.663 | 51.249 | 1.00 45.70 | B | C |
| ATOM | 3165 | OD1 | ASN | B 359 | 30.640 | 24.043 | 52.273 | 1.00 46.28 | B | O |
| ATOM | 3166 | ND2 | ASN | B 359 | 31.343 | 25.962 | 51.270 | 1.00 45.25 | B | N |
| ATOM | 3167 | C   | ASN | B 359 | 32.328 | 22.116 | 48.612 | 1.00 37.74 | B | C |

Figure 4

```
ATOM   3168  O    ASN B 359      31.451  22.192  47.744  1.00 36.33      B  O
ATOM   3169  N    TYR B 360      33.379  21.311  48.525  1.00 35.15      B  N
ATOM   3170  CA   TYR B 360      33.620  20.416  47.408  1.00 32.41      B  C
ATOM   3171  CB   TYR B 360      35.035  20.621  46.850  1.00 33.72      B  C
ATOM   3172  CG   TYR B 360      35.194  21.775  45.899  1.00 34.86      B  C
ATOM   3173  CD1  TYR B 360      35.184  23.092  46.361  1.00 35.86      B  C
ATOM   3174  CE1  TYR B 360      35.314  24.159  45.494  1.00 35.96      B  C
ATOM   3175  CD2  TYR B 360      35.342  21.552  44.536  1.00 35.62      B  C
ATOM   3176  CE2  TYR B 360      35.476  22.615  43.657  1.00 37.58      B  C
ATOM   3177  CZ   TYR B 360      35.456  23.918  44.146  1.00 38.02      B  C
ATOM   3178  OH   TYR B 360      35.564  24.980  43.278  1.00 40.40      B  O
ATOM   3179  C    TYR B 360      33.572  19.010  47.996  1.00 30.99      B  C
ATOM   3180  O    TYR B 360      33.404  18.817  49.205  1.00 31.29      B  O
ATOM   3181  N    ILE B 361      33.707  18.029  47.120  1.00 28.78      B  N
ATOM   3182  CA   ILE B 361      33.781  16.641  47.523  1.00 28.11      B  C
ATOM   3183  CB   ILE B 361      32.468  15.864  47.257  1.00 26.64      B  C
ATOM   3184  CG2  ILE B 361      31.307  16.532  48.016  1.00 24.36      B  C
ATOM   3185  CG1  ILE B 361      32.193  15.782  45.750  1.00 26.36      B  C
ATOM   3186  CD1  ILE B 361      31.353  14.597  45.337  1.00 25.81      B  C
ATOM   3187  C    ILE B 361      34.917  16.119  46.632  1.00 29.17      B  C
ATOM   3188  O    ILE B 361      35.402  16.829  45.739  1.00 30.59      B  O
ATOM   3189  N    HIS B 362      35.370  14.904  46.878  1.00 28.44      B  N
ATOM   3190  CA   HIS B 362      36.433  14.350  46.067  1.00 26.94      B  C
ATOM   3191  CB   HIS B 362      37.427  13.588  46.941  1.00 25.14      B  C
ATOM   3192  CG   HIS B 362      38.675  13.194  46.222  1.00 22.61      B  C
ATOM   3193  CD2  HIS B 362      39.956  13.577  46.398  1.00 21.63      B  C
ATOM   3194  ND1  HIS B 362      38.680  12.318  45.158  1.00 21.42      B  N
ATOM   3195  CE1  HIS B 362      39.911  12.176  44.709  1.00 22.00      B  C
ATOM   3196  NE2  HIS B 362      40.707  12.932  45.446  1.00 22.38      B  N
ATOM   3197  C    HIS B 362      35.780  13.395  45.097  1.00 28.91      B  C
ATOM   3198  O    HIS B 362      35.877  13.579  43.894  1.00 29.76      B  O
ATOM   3199  N    ARG B 363      35.060  12.435  45.683  1.00 29.67      B  N
ATOM   3200  CA   ARG B 363      34.308  11.331  45.068  1.00 29.77      B  C
ATOM   3201  CB   ARG B 363      33.214  11.773  44.059  1.00 35.57      B  C
ATOM   3202  CG   ARG B 363      33.665  12.571  42.826  1.00 39.62      B  C
ATOM   3203  CD   ARG B 363      32.484  13.086  41.986  1.00 41.42      B  C
ATOM   3204  NE   ARG B 363      31.791  12.003  41.298  1.00 41.78      B  N
ATOM   3205  CZ   ARG B 363      30.495  11.750  41.435  1.00 43.02      B  C
ATOM   3206  NH1  ARG B 363      29.759  12.512  42.234  1.00 42.70      B  N
ATOM   3207  NH2  ARG B 363      29.941  10.715  40.812  1.00 43.53      B  N
ATOM   3208  C    ARG B 363      35.146  10.179  44.556  1.00 27.78      B  C
ATOM   3209  O    ARG B 363      34.618   9.112  44.280  1.00 24.58      B  O
ATOM   3210  N    ASP B 364      36.467  10.355  44.555  1.00 26.23      B  N
ATOM   3211  CA   ASP B 364      37.379   9.322  44.090  1.00 25.47      B  C
ATOM   3212  CB   ASP B 364      37.927   9.698  42.722  1.00 25.98      B  C
ATOM   3213  CG   ASP B 364      36.953   9.429  41.615  1.00 24.87      B  C
ATOM   3214  OD1  ASP B 364      36.699   8.231  41.333  1.00 24.80      B  O
ATOM   3215  OD2  ASP B 364      36.468  10.416  41.025  1.00 25.11      B  O
ATOM   3216  C    ASP B 364      38.540   9.085  45.056  1.00 26.62      B  C
ATOM   3217  O    ASP B 364      39.607   8.606  44.667  1.00 24.70      B  O
ATOM   3218  N    LEU B 365      38.306   9.402  46.324  1.00 26.57      B  N
ATOM   3219  CA   LEU B 365      39.285   9.255  47.389  1.00 24.74      B  C
ATOM   3220  CB   LEU B 365      38.754   9.936  48.649  1.00 24.17      B  C
ATOM   3221  CG   LEU B 365      39.716  10.096  49.816  1.00 24.55      B  C
ATOM   3222  CD1  LEU B 365      40.953  10.869  49.329  1.00 24.99      B  C
ATOM   3223  CD2  LEU B 365      39.014  10.813  50.981  1.00 22.69      B  C
ATOM   3224  C    LEU B 365      39.658   7.806  47.695  1.00 25.37      B  C
ATOM   3225  O    LEU B 365      38.831   7.000  48.093  1.00 26.45      B  O
ATOM   3226  N    ARG B 366      40.917   7.484  47.456  1.00 25.95      B  N
ATOM   3227  CA   ARG B 366      41.480   6.164  47.716  1.00 26.34      B  C
```

Figure 4

```
ATOM   3228  CB  ARG B 366      40.991   5.117  46.709  1.00 28.35      B    C
ATOM   3229  CG  ARG B 366      41.326   5.366  45.260  1.00 31.81      B    C
ATOM   3230  CD  ARG B 366      41.037   4.122  44.432  1.00 34.12      B    C
ATOM   3231  NE  ARG B 366      40.706   4.454  43.052  1.00 37.36      B    N
ATOM   3232  CZ  ARG B 366      39.594   5.093  42.705  1.00 39.43      B    C
ATOM   3233  NH1 ARG B 366      38.721   5.461  43.647  1.00 41.38      B    N
ATOM   3234  NH2 ARG B 366      39.344   5.360  41.430  1.00 39.35      B    N
ATOM   3235  C   ARG B 366      42.995   6.363  47.663  1.00 25.91      B    C
ATOM   3236  O   ARG B 366      43.447   7.414  47.203  1.00 26.21      B    O
ATOM   3237  N   ALA B 367      43.777   5.417  48.176  1.00 24.69      B    N
ATOM   3238  CA  ALA B 367      45.241   5.582  48.180  1.00 25.84      B    C
ATOM   3239  CB  ALA B 367      45.915   4.449  48.929  1.00 24.55      B    C
ATOM   3240  C   ALA B 367      45.849   5.741  46.782  1.00 26.25      B    C
ATOM   3241  O   ALA B 367      46.856   6.434  46.620  1.00 26.37      B    O
ATOM   3242  N   ALA B 368      45.211   5.138  45.777  1.00 24.80      B    N
ATOM   3243  CA  ALA B 368      45.675   5.223  44.401  1.00 23.78      B    C
ATOM   3244  CB  ALA B 368      44.788   4.382  43.495  1.00 22.89      B    C
ATOM   3245  C   ALA B 368      45.693   6.665  43.923  1.00 23.25      B    C
ATOM   3246  O   ALA B 368      46.534   7.048  43.125  1.00 23.63      B    O
ATOM   3247  N   ASN B 369      44.811   7.483  44.475  1.00 23.46      B    N
ATOM   3248  CA  ASN B 369      44.715   8.879  44.084  1.00 24.34      B    C
ATOM   3249  CB  ASN B 369      43.251   9.233  43.804  1.00 24.00      B    C
ATOM   3250  CG  ASN B 369      42.662   8.355  42.719  1.00 24.16      B    C
ATOM   3251  OD1 ASN B 369      43.300   8.133  41.681  1.00 25.29      B    O
ATOM   3252  ND2 ASN B 369      41.508   7.765  42.984  1.00 23.50      B    N
ATOM   3253  C   ASN B 369      45.417   9.875  45.002  1.00 23.64      B    C
ATOM   3254  O   ASN B 369      45.112  11.076  45.004  1.00 23.58      B    O
ATOM   3255  N   ILE B 370      46.355   9.355  45.791  1.00 21.94      B    N
ATOM   3256  CA  ILE B 370      47.174  10.185  46.661  1.00 21.24      B    C
ATOM   3257  CB  ILE B 370      47.160   9.721  48.148  1.00 20.68      B    C
ATOM   3258  CG2 ILE B 370      47.989  10.705  49.025  1.00 17.57      B    C
ATOM   3259  CG1 ILE B 370      45.721   9.676  48.666  1.00 20.52      B    C
ATOM   3260  CD1 ILE B 370      45.048  11.046  48.757  1.00 18.91      B    C
ATOM   3261  C   ILE B 370      48.605  10.054  46.110  1.00 21.70      B    C
ATOM   3262  O   ILE B 370      49.050   8.971  45.733  1.00 20.16      B    O
ATOM   3263  N   LEU B 371      49.304  11.174  46.024  1.00 23.30      B    N
ATOM   3264  CA  LEU B 371      50.660  11.161  45.531  1.00 23.71      B    C
ATOM   3265  CB  LEU B 371      50.814  12.169  44.396  1.00 22.42      B    C
ATOM   3266  CG  LEU B 371      49.935  11.909  43.176  1.00 20.92      B    C
ATOM   3267  CD1 LEU B 371      50.165  12.994  42.143  1.00 20.55      B    C
ATOM   3268  CD2 LEU B 371      50.208  10.527  42.593  1.00 20.48      B    C
ATOM   3269  C   LEU B 371      51.619  11.462  46.674  1.00 25.26      B    C
ATOM   3270  O   LEU B 371      51.279  12.191  47.615  1.00 24.75      B    O
ATOM   3271  N   VAL B 372      52.817  10.886  46.573  1.00 27.11      B    N
ATOM   3272  CA  VAL B 372      53.872  11.016  47.574  1.00 27.63      B    C
ATOM   3273  CB  VAL B 372      54.306   9.610  48.074  1.00 26.99      B    C
ATOM   3274  CG1 VAL B 372      55.215   9.727  49.300  1.00 27.11      B    C
ATOM   3275  CG2 VAL B 372      53.087   8.749  48.366  1.00 25.86      B    C
ATOM   3276  C   VAL B 372      55.113  11.717  46.995  1.00 29.29      B    C
ATOM   3277  O   VAL B 372      55.631  11.315  45.942  1.00 30.28      B    O
ATOM   3278  N   SER B 373      55.597  12.744  47.692  1.00 30.24      B    N
ATOM   3279  CA  SER B 373      56.783  13.475  47.252  1.00 31.02      B    C
ATOM   3280  CB  SER B 373      56.779  14.898  47.808  1.00 29.92      B    C
ATOM   3281  OG  SER B 373      57.065  14.900  49.195  1.00 29.30      B    O
ATOM   3282  C   SER B 373      58.084  12.773  47.671  1.00 32.84      B    C
ATOM   3283  O   SER B 373      58.067  11.686  48.263  1.00 31.23      B    O
ATOM   3284  N   ASP B 374      59.210  13.405  47.338  1.00 35.99      B    N
ATOM   3285  CA  ASP B 374      60.528  12.884  47.690  1.00 37.75      B    C
ATOM   3286  CB  ASP B 374      61.646  13.574  46.877  1.00 39.56      B    C
ATOM   3287  CG  ASP B 374      61.575  15.090  46.934  1.00 41.82      B    C
```

Figure 4

| | | | | | | | | | | | |
|---|---|---|---|---|---|---|---|---|---|---|---|
|ATOM|3288|OD1|ASP|B|374|60.561|15.661|46.482|1.00 43.77|B|O|
|ATOM|3289|OD2|ASP|B|374|62.549|15.717|47.405|1.00 43.70|B|O|
|ATOM|3290|C|ASP|B|374|60.759|12.986|49.201|1.00 37.12|B|C|
|ATOM|3291|O|ASP|B|374|61.444|12.144|49.781|1.00 37.12|B|O|
|ATOM|3292|N|THR|B|375|60.126|13.967|49.846|1.00 36.87|B|N|
|ATOM|3293|CA|THR|B|375|60.236|14.128|51.291|1.00 36.55|B|C|
|ATOM|3294|CB|THR|B|375|60.181|15.599|51.718|1.00 36.31|B|C|
|ATOM|3295|OG1|THR|B|375|58.871|16.127|51.489|1.00 38.46|B|O|
|ATOM|3296|CG2|THR|B|375|61.187|16.411|50.955|1.00 36.60|B|C|
|ATOM|3297|C|THR|B|375|59.091|13.366|51.974|1.00 37.62|B|C|
|ATOM|3298|O|THR|B|375|58.718|13.665|53.110|1.00 39.09|B|O|
|ATOM|3299|N|LEU|B|376|58.516|12.413|51.242|1.00 38.27|B|N|
|ATOM|3300|CA|LEU|B|376|57.430|11.548|51.699|1.00 38.74|B|C|
|ATOM|3301|CB|LEU|B|376|57.934|10.540|52.726|1.00 40.57|B|C|
|ATOM|3302|CG|LEU|B|376|59.196|9.761|52.346|1.00 42.12|B|C|
|ATOM|3303|CD1|LEU|B|376|59.455|8.713|53.406|1.00 43.28|B|C|
|ATOM|3304|CD2|LEU|B|376|59.055|9.116|50.973|1.00 42.55|B|C|
|ATOM|3305|C|LEU|B|376|56.155|12.201|52.201|1.00 38.78|B|C|
|ATOM|3306|O|LEU|B|376|55.393|11.577|52.943|1.00 37.17|B|O|
|ATOM|3307|N|SER|B|377|55.916|13.446|51.789|1.00 38.78|B|N|
|ATOM|3308|CA|SER|B|377|54.698|14.159|52.173|1.00 38.46|B|C|
|ATOM|3309|CB|SER|B|377|54.935|15.673|52.217|1.00 39.26|B|C|
|ATOM|3310|OG|SER|B|377|55.120|16.202|50.915|1.00 40.81|B|O|
|ATOM|3311|C|SER|B|377|53.599|13.819|51.152|1.00 38.17|B|C|
|ATOM|3312|O|SER|B|377|53.877|13.682|49.947|1.00 39.02|B|O|
|ATOM|3313|N|CYS|B|378|52.356|13.697|51.624|1.00 35.37|B|N|
|ATOM|3314|CA|CYS|B|378|51.237|13.340|50.751|1.00 32.22|B|C|
|ATOM|3315|CB|CYS|B|378|50.325|12.322|51.444|1.00 31.24|B|C|
|ATOM|3316|SG|CYS|B|378|51.145|10.777|51.899|1.00 29.62|B|S|
|ATOM|3317|C|CYS|B|378|50.400|14.509|50.248|1.00 30.84|B|C|
|ATOM|3318|O|CYS|B|378|50.169|15.490|50.967|1.00 31.12|B|O|
|ATOM|3319|N|LYS|B|379|49.972|14.387|48.988|1.00 29.13|B|N|
|ATOM|3320|CA|LYS|B|379|49.121|15.373|48.315|1.00 26.98|B|C|
|ATOM|3321|CB|LYS|B|379|49.953|16.219|47.342|1.00 25.37|B|C|
|ATOM|3322|CG|LYS|B|379|50.625|17.445|47.979|1.00 25.92|B|C|
|ATOM|3323|CD|LYS|B|379|51.812|17.950|47.134|1.00 27.57|B|C|
|ATOM|3324|CE|LYS|B|379|52.377|19.317|47.559|1.00 28.14|B|C|
|ATOM|3325|NZ|LYS|B|379|51.582|20.504|47.014|1.00 30.73|B|N|
|ATOM|3326|C|LYS|B|379|47.924|14.678|47.599|1.00 25.82|B|C|
|ATOM|3327|O|LYS|B|379|48.048|13.570|47.042|1.00 25.36|B|O|
|ATOM|3328|N|ILE|B|380|46.762|15.323|47.644|1.00 25.22|B|N|
|ATOM|3329|CA|ILE|B|380|45.537|14.793|47.038|1.00 25.30|B|C|
|ATOM|3330|CB|ILE|B|380|44.276|15.312|47.793|1.00 26.39|B|C|
|ATOM|3331|CG2|ILE|B|380|43.023|14.802|47.146|1.00 25.00|B|C|
|ATOM|3332|CG1|ILE|B|380|44.303|14.858|49.256|1.00 27.32|B|C|
|ATOM|3333|CD1|ILE|B|380|43.177|15.418|50.073|1.00 27.44|B|C|
|ATOM|3334|C|ILE|B|380|45.410|15.157|45.556|1.00 24.64|B|C|
|ATOM|3335|O|ILE|B|380|45.470|16.335|45.174|1.00 24.90|B|O|
|ATOM|3336|N|ALA|B|381|45.213|14.142|44.725|1.00 24.28|B|N|
|ATOM|3337|CA|ALA|B|381|45.057|14.354|43.292|1.00 25.53|B|C|
|ATOM|3338|CB|ALA|B|381|46.117|13.572|42.533|1.00 24.35|B|C|
|ATOM|3339|C|ALA|B|381|43.666|13.934|42.807|1.00 25.28|B|C|
|ATOM|3340|O|ALA|B|381|42.967|13.168|43.477|1.00 24.61|B|O|
|ATOM|3341|N|ASP|B|382|43.291|14.444|41.635|1.00 25.70|B|N|
|ATOM|3342|CA|ASP|B|382|42.029|14.114|40.971|1.00 25.56|B|C|
|ATOM|3343|CB|ASP|B|382|42.116|12.704|40.353|1.00 25.65|B|C|
|ATOM|3344|CG|ASP|B|382|43.027|12.649|39.144|1.00 24.70|B|C|
|ATOM|3345|OD1|ASP|B|382|43.108|13.650|38.408|1.00 27.60|B|O|
|ATOM|3346|OD2|ASP|B|382|43.656|11.603|38.926|1.00 24.90|B|O|
|ATOM|3347|C|ASP|B|382|40.774|14.254|41.814|1.00 25.53|B|C|

Figure 4

```
ATOM   3348  O    ASP B 382      39.924  13.371  41.848  1.00 24.60      B   O
ATOM   3349  N    PHE B 383      40.656  15.390  42.475  1.00 27.65      B   N
ATOM   3350  CA   PHE B 383      39.508  15.693  43.321  1.00 29.95      B   C
ATOM   3351  CB   PHE B 383      39.979  16.462  44.559  1.00 29.78      B   C
ATOM   3352  CG   PHE B 383      40.754  17.707  44.229  1.00 32.52      B   C
ATOM   3353  CD1  PHE B 383      40.124  18.959  44.221  1.00 32.53      B   C
ATOM   3354  CD2  PHE B 383      42.103  17.620  43.850  1.00 33.60      B   C
ATOM   3355  CE1  PHE B 383      40.823  20.098  43.832  1.00 33.09      B   C
ATOM   3356  CE2  PHE B 383      42.808  18.752  43.458  1.00 34.16      B   C
ATOM   3357  CZ   PHE B 383      42.170  19.994  43.445  1.00 33.35      B   C
ATOM   3358  C    PHE B 383      38.506  16.554  42.552  1.00 30.27      B   C
ATOM   3359  O    PHE B 383      38.871  17.259  41.603  1.00 32.82      B   O
ATOM   3360  N    GLY B 384      37.247  16.494  42.965  1.00 30.14      B   N
ATOM   3361  CA   GLY B 384      36.224  17.303  42.335  1.00 29.90      B   C
ATOM   3362  C    GLY B 384      35.833  16.961  40.914  1.00 30.84      B   C
ATOM   3363  O    GLY B 384      35.169  17.765  40.291  1.00 32.86      B   O
ATOM   3364  N    LEU B 385      36.238  15.807  40.386  1.00 31.15      B   N
ATOM   3365  CA   LEU B 385      35.873  15.412  39.017  1.00 33.33      B   C
ATOM   3366  CB   LEU B 385      36.724  14.207  38.554  1.00 31.89      B   C
ATOM   3367  CG   LEU B 385      38.258  14.319  38.649  1.00 30.91      B   C
ATOM   3368  CD1  LEU B 385      38.881  13.033  38.174  1.00 30.32      B   C
ATOM   3369  CD2  LEU B 385      38.798  15.481  37.837  1.00 29.77      B   C
ATOM   3370  C    LEU B 385      34.368  15.050  38.939  1.00 35.87      B   C
ATOM   3371  O    LEU B 385      33.778  14.573  39.914  1.00 35.25      B   O
ATOM   3372  N    ALA B 386      33.754  15.312  37.785  1.00 37.12      B   N
ATOM   3373  CA   ALA B 386      32.328  15.016  37.573  1.00 38.13      B   C
ATOM   3374  CB   ALA B 386      31.820  15.786  36.362  1.00 37.73      B   C
ATOM   3375  C    ALA B 386      32.067  13.543  37.374  1.00 38.32      B   C
ATOM   3376  O    ALA B 386      30.926  13.096  37.393  1.00 38.49      B   O
ATOM   3377  N    ARG B 387      33.138  12.781  37.199  1.00 38.61      B   N
ATOM   3378  CA   ARG B 387      33.030  11.347  36.964  1.00 37.40      B   C
ATOM   3379  CB   ARG B 387      33.508  11.046  35.535  1.00 37.59      B   C
ATOM   3380  CG   ARG B 387      34.961  11.453  35.273  1.00 37.93      B   C
ATOM   3381  CD   ARG B 387      35.430  10.983  33.904  1.00 37.96      B   C
ATOM   3382  NE   ARG B 387      36.873  11.113  33.759  1.00 38.15      B   N
ATOM   3383  CZ   ARG B 387      37.724  10.108  33.899  1.00 39.26      B   C
ATOM   3384  NH1  ARG B 387      37.278   8.885  34.176  1.00 40.10      B   N
ATOM   3385  NH2  ARG B 387      39.027  10.336  33.793  1.00 41.33      B   N
ATOM   3386  C    ARG B 387      33.824  10.492  37.950  1.00 36.40      B   C
ATOM   3387  O    ARG B 387      34.645  11.002  38.712  1.00 37.58      B   O
ATOM   3388  N    LEU B 388      33.562   9.185  37.925  1.00 34.55      B   N
ATOM   3389  CA   LEU B 388      34.257   8.227  38.762  1.00 31.57      B   C
ATOM   3390  CB   LEU B 388      33.288   7.142  39.212  1.00 30.67      B   C
ATOM   3391  CG   LEU B 388      32.053   7.655  39.949  1.00 31.65      B   C
ATOM   3392  CD1  LEU B 388      31.036   6.538  40.104  1.00 30.39      B   C
ATOM   3393  CD2  LEU B 388      32.454   8.239  41.306  1.00 30.55      B   C
ATOM   3394  C    LEU B 388      35.379   7.616  37.922  1.00 30.56      B   C
ATOM   3395  O    LEU B 388      35.127   6.952  36.918  1.00 31.83      B   O
ATOM   3396  N    ILE B 389      36.616   7.811  38.375  1.00 30.07      B   N
ATOM   3397  CA   ILE B 389      37.794   7.320  37.644  1.00 27.91      B   C
ATOM   3398  CB   ILE B 389      38.980   8.328  37.738  1.00 26.03      B   C
ATOM   3399  CG2  ILE B 389      38.530   9.735  37.337  1.00 25.80      B   C
ATOM   3400  CG1  ILE B 389      39.566   8.357  39.159  1.00 24.69      B   C
ATOM   3401  CD1  ILE B 389      40.454   9.554  39.428  1.00 23.88      B   C
ATOM   3402  C    ILE B 389      38.260   5.922  38.080  1.00 29.43      B   C
ATOM   3403  O    ILE B 389      37.913   5.425  39.163  1.00 30.37      B   O
ATOM   3404  N    GLU B 390      39.034   5.300  37.224  1.00 31.19      B   N
ATOM   3405  CA   GLU B 390      39.609   4.003  37.490  1.00 33.30      B   C
ATOM   3406  CB   GLU B 390      39.100   2.962  36.500  1.00 33.22      B   C
ATOM   3407  CG   GLU B 390      37.574   2.783  36.584  1.00 36.48      B   C
```

Figure 4

| | | | | | | | | | | | |
|---|---|---|---|---|---|---|---|---|---|---|---|
| ATOM | 3408 | CD | GLU | B | 390 | 37.058 | 1.654 | 35.733 | 1.00 | 37.50 | B C |
| ATOM | 3409 | OE1 | GLU | B | 390 | 35.826 | 1.560 | 35.555 | 1.00 | 39.01 | B O |
| ATOM | 3410 | OE2 | GLU | B | 390 | 37.880 | 0.861 | 35.232 | 1.00 | 39.43 | B O |
| ATOM | 3411 | C | GLU | B | 390 | 41.138 | 4.108 | 37.421 | 1.00 | 33.69 | B C |
| ATOM | 3412 | O | GLU | B | 390 | 41.701 | 5.018 | 36.794 | 1.00 | 34.08 | B O |
| ATOM | 3413 | N | ASP | B | 391 | 41.756 | 3.150 | 38.072 | 1.00 | 34.07 | B N |
| ATOM | 3414 | CA | ASP | B | 391 | 43.206 | 3.140 | 38.157 | 1.00 | 35.78 | B C |
| ATOM | 3415 | CB | ASP | B | 391 | 43.680 | 2.179 | 39.251 | 1.00 | 36.68 | B C |
| ATOM | 3416 | CG | ASP | B | 391 | 43.108 | 2.497 | 40.609 | 1.00 | 38.10 | B C |
| ATOM | 3417 | OD1 | ASP | B | 391 | 42.819 | 3.684 | 40.885 | 1.00 | 39.38 | B O |
| ATOM | 3418 | OD2 | ASP | B | 391 | 42.942 | 1.558 | 41.405 | 1.00 | 40.10 | B O |
| ATOM | 3419 | C | ASP | B | 391 | 43.899 | 2.791 | 36.835 | 1.00 | 36.48 | B C |
| ATOM | 3420 | O | ASP | B | 391 | 44.987 | 3.286 | 36.579 | 1.00 | 39.05 | B O |
| ATOM | 3421 | N | ASN | B | 392 | 43.270 | 1.957 | 36.007 | 1.00 | 36.21 | B N |
| ATOM | 3422 | CA | ASN | B | 392 | 43.842 | 1.560 | 34.716 | 1.00 | 35.11 | B C |
| ATOM | 3423 | CB | ASN | B | 392 | 43.141 | 0.285 | 34.205 | 1.00 | 36.58 | B C |
| ATOM | 3424 | CG | ASN | B | 392 | 41.691 | 0.542 | 33.716 | 1.00 | 37.59 | B C |
| ATOM | 3425 | OD1 | ASN | B | 392 | 41.148 | 1.643 | 33.850 | 1.00 | 38.00 | B O |
| ATOM | 3426 | ND2 | ASN | B | 392 | 41.075 | -0.487 | 33.137 | 1.00 | 38.52 | B N |
| ATOM | 3427 | C | ASN | B | 392 | 43.811 | 2.637 | 33.610 | 1.00 | 33.63 | B C |
| ATOM | 3428 | O | ASN | B | 392 | 44.178 | 2.352 | 32.466 | 1.00 | 33.86 | B O |
| ATOM | 3429 | N | GLU | B | 393 | 43.411 | 3.860 | 33.954 | 1.00 | 31.30 | B N |
| ATOM | 3430 | CA | GLU | B | 393 | 43.295 | 4.922 | 32.965 | 1.00 | 30.53 | B C |
| ATOM | 3431 | CB | GLU | B | 393 | 42.283 | 5.968 | 33.430 | 1.00 | 29.33 | B C |
| ATOM | 3432 | CG | GLU | B | 393 | 40.856 | 5.415 | 33.520 | 1.00 | 28.13 | B C |
| ATOM | 3433 | CD | GLU | B | 393 | 39.866 | 6.381 | 34.147 | 1.00 | 26.58 | B C |
| ATOM | 3434 | OE1 | GLU | B | 393 | 40.270 | 7.474 | 34.600 | 1.00 | 27.21 | B O |
| ATOM | 3435 | OE2 | GLU | B | 393 | 38.670 | 6.037 | 34.186 | 1.00 | 26.19 | B O |
| ATOM | 3436 | C | GLU | B | 393 | 44.589 | 5.583 | 32.509 | 1.00 | 31.05 | B C |
| ATOM | 3437 | O | GLU | B | 393 | 44.710 | 5.987 | 31.363 | 1.00 | 31.04 | B O |
| ATOM | 3438 | N | TYR | B | 394 | 45.545 | 5.715 | 33.409 | 1.00 | 31.52 | B N |
| ATOM | 3439 | CA | TYR | B | 394 | 46.805 | 6.331 | 33.040 | 1.00 | 31.58 | B C |
| ATOM | 3440 | CB | TYR | B | 394 | 46.858 | 7.760 | 33.575 | 1.00 | 30.75 | B C |
| ATOM | 3441 | CG | TYR | B | 394 | 45.773 | 8.641 | 33.004 | 1.00 | 29.73 | B C |
| ATOM | 3442 | CD1 | TYR | B | 394 | 44.548 | 8.752 | 33.638 | 1.00 | 29.15 | B C |
| ATOM | 3443 | CE1 | TYR | B | 394 | 43.527 | 9.539 | 33.107 | 1.00 | 31.45 | B C |
| ATOM | 3444 | CD2 | TYR | B | 394 | 45.970 | 9.346 | 31.818 | 1.00 | 30.28 | B C |
| ATOM | 3445 | CE2 | TYR | B | 394 | 44.954 | 10.146 | 31.267 | 1.00 | 31.72 | B C |
| ATOM | 3446 | CZ | TYR | B | 394 | 43.722 | 10.238 | 31.917 | 1.00 | 32.19 | B C |
| ATOM | 3447 | OH | TYR | B | 394 | 42.674 | 10.987 | 31.374 | 1.00 | 31.53 | B O |
| ATOM | 3448 | C | TYR | B | 394 | 47.989 | 5.485 | 33.510 | 1.00 | 33.05 | B C |
| ATOM | 3449 | O | TYR | B | 394 | 49.142 | 5.868 | 33.342 | 1.00 | 33.76 | B O |
| ATOM | 3450 | N | THR | B | 395 | 47.676 | 4.336 | 34.110 | 1.00 | 35.22 | B N |
| ATOM | 3451 | CA | THR | B | 395 | 48.665 | 3.354 | 34.575 | 1.00 | 38.13 | B C |
| ATOM | 3452 | CB | THR | B | 395 | 48.987 | 3.448 | 36.109 | 1.00 | 37.41 | B C |
| ATOM | 3453 | OG1 | THR | B | 395 | 47.838 | 3.876 | 36.850 | 1.00 | 35.96 | B O |
| ATOM | 3454 | CG2 | THR | B | 395 | 50.149 | 4.398 | 36.354 | 1.00 | 38.35 | B C |
| ATOM | 3455 | C | THR | B | 395 | 48.139 | 1.955 | 34.229 | 1.00 | 40.70 | B C |
| ATOM | 3456 | O | THR | B | 395 | 47.049 | 1.823 | 33.665 | 1.00 | 42.34 | B O |
| ATOM | 3457 | N | ALA | B | 396 | 48.899 | 0.913 | 34.557 | 1.00 | 43.32 | B N |
| ATOM | 3458 | CA | ALA | B | 396 | 48.469 | -0.446 | 34.242 | 1.00 | 45.98 | B C |
| ATOM | 3459 | CB | ALA | B | 396 | 49.430 | -1.077 | 33.227 | 1.00 | 45.35 | B C |
| ATOM | 3460 | C | ALA | B | 396 | 48.265 | -1.371 | 35.450 | 1.00 | 47.64 | B C |
| ATOM | 3461 | O | ALA | B | 396 | 48.781 | -2.495 | 35.482 | 1.00 | 48.12 | B O |
| ATOM | 3462 | N | ARG | B | 397 | 47.473 | -0.921 | 36.417 | 1.00 | 49.91 | B N |
| ATOM | 3463 | CA | ARG | B | 397 | 47.218 | -1.729 | 37.597 | 1.00 | 52.14 | B C |
| ATOM | 3464 | CB | ARG | B | 397 | 46.788 | -0.842 | 38.754 | 1.00 | 52.87 | B C |
| ATOM | 3465 | CG | ARG | B | 397 | 47.821 | 0.166 | 39.159 | 1.00 | 54.48 | B C |
| ATOM | 3466 | CD | ARG | B | 397 | 47.793 | 0.319 | 40.669 | 1.00 | 57.32 | B C |
| ATOM | 3467 | NE | ARG | B | 397 | 48.539 | 1.487 | 41.126 | 1.00 | 59.23 | B N |

Figure 4

| ATOM | 3468 | CZ | ARG | B | 397 | 48.079 | 2.735 | 41.086 | 1.00 | 60.31 | B | C |
| ATOM | 3469 | NH1 | ARG | B | 397 | 46.862 | 2.995 | 40.614 | 1.00 | 60.82 | B | N |
| ATOM | 3470 | NH2 | ARG | B | 397 | 48.834 | 3.728 | 41.533 | 1.00 | 60.51 | B | N |
| ATOM | 3471 | C | ARG | B | 397 | 46.158 | -2.799 | 37.329 | 1.00 | 53.39 | B | C |
| ATOM | 3472 | O | ARG | B | 397 | 46.389 | -3.963 | 37.737 | 1.00 | 53.81 | B | O |
| ATOM | 3473 | CB | PRO | B | 403 | 35.974 | 2.340 | 41.394 | 1.00 | 35.34 | B | C |
| ATOM | 3474 | CG | PRO | B | 403 | 36.790 | 1.651 | 40.323 | 1.00 | 34.73 | B | C |
| ATOM | 3475 | C | PRO | B | 403 | 34.749 | 1.243 | 43.507 | 1.00 | 36.12 | B | C |
| ATOM | 3476 | O | PRO | B | 403 | 34.362 | 2.281 | 44.055 | 1.00 | 37.41 | B | O |
| ATOM | 3477 | N | PRO | B | 403 | 35.701 | 0.069 | 41.573 | 1.00 | 35.67 | B | N |
| ATOM | 3478 | CD | PRO | B | 403 | 36.572 | 0.171 | 40.399 | 1.00 | 34.26 | B | C |
| ATOM | 3479 | CA | PRO | B | 403 | 35.825 | 1.245 | 42.433 | 1.00 | 35.74 | B | C |
| ATOM | 3480 | N | ILE | B | 404 | 34.251 | 0.013 | 43.749 | 1.00 | 33.14 | B | N |
| ATOM | 3481 | CA | ILE | B | 404 | 33.156 | -0.200 | 44.707 | 1.00 | 29.96 | B | C |
| ATOM | 3482 | CB | ILE | B | 404 | 32.333 | -1.443 | 44.342 | 1.00 | 30.56 | B | C |
| ATOM | 3483 | CG2 | ILE | B | 404 | 31.909 | -2.192 | 45.598 | 1.00 | 29.48 | B | C |
| ATOM | 3484 | CG1 | ILE | B | 404 | 31.113 | -1.036 | 43.517 | 1.00 | 31.77 | B | C |
| ATOM | 3485 | CD1 | ILE | B | 404 | 30.401 | 0.194 | 44.050 | 1.00 | 32.32 | B | C |
| ATOM | 3486 | C | ILE | B | 404 | 33.638 | -0.265 | 46.149 | 1.00 | 25.56 | B | C |
| ATOM | 3487 | O | ILE | B | 404 | 32.945 | 0.235 | 47.030 | 1.00 | 23.92 | B | O |
| ATOM | 3488 | N | LYS | B | 405 | 34.794 | -0.861 | 46.440 | 1.00 | 23.03 | B | N |
| ATOM | 3489 | CA | LYS | B | 405 | 35.258 | -0.973 | 47.810 | 1.00 | 22.22 | B | C |
| ATOM | 3490 | CB | LYS | B | 405 | 36.440 | -1.929 | 47.886 | 1.00 | 22.99 | B | C |
| ATOM | 3491 | CG | LYS | B | 405 | 36.073 | -3.333 | 47.511 | 1.00 | 24.22 | B | C |
| ATOM | 3492 | CD | LYS | B | 405 | 37.248 | -4.268 | 47.685 | 1.00 | 26.99 | B | C |
| ATOM | 3493 | CE | LYS | B | 405 | 36.867 | -5.707 | 47.433 | 1.00 | 28.96 | B | C |
| ATOM | 3494 | NZ | LYS | B | 405 | 37.905 | -6.647 | 47.958 | 1.00 | 32.60 | B | N |
| ATOM | 3495 | C | LYS | B | 405 | 35.517 | 0.285 | 48.640 | 1.00 | 21.56 | B | C |
| ATOM | 3496 | O | LYS | B | 405 | 35.760 | 0.173 | 49.840 | 1.00 | 19.13 | B | O |
| ATOM | 3497 | N | TRP | B | 406 | 35.420 | 1.468 | 48.028 | 1.00 | 20.31 | B | N |
| ATOM | 3498 | CA | TRP | B | 406 | 35.599 | 2.727 | 48.743 | 1.00 | 20.34 | B | C |
| ATOM | 3499 | CB | TRP | B | 406 | 36.699 | 3.581 | 48.096 | 1.00 | 20.69 | B | C |
| ATOM | 3500 | CG | TRP | B | 406 | 38.107 | 3.012 | 48.175 | 1.00 | 21.81 | B | C |
| ATOM | 3501 | CD2 | TRP | B | 406 | 38.658 | 1.963 | 47.367 | 1.00 | 21.90 | B | C |
| ATOM | 3502 | CE2 | TRP | B | 406 | 39.995 | 1.785 | 47.771 | 1.00 | 21.95 | B | C |
| ATOM | 3503 | CE3 | TRP | B | 406 | 38.145 | 1.158 | 46.338 | 1.00 | 22.21 | B | C |
| ATOM | 3504 | CD1 | TRP | B | 406 | 39.112 | 3.419 | 49.016 | 1.00 | 21.80 | B | C |
| ATOM | 3505 | NE1 | TRP | B | 406 | 40.245 | 2.682 | 48.778 | 1.00 | 22.71 | B | N |
| ATOM | 3506 | CZ2 | TRP | B | 406 | 40.825 | 0.834 | 47.184 | 1.00 | 22.34 | B | C |
| ATOM | 3507 | CZ3 | TRP | B | 406 | 38.967 | 0.213 | 45.754 | 1.00 | 23.74 | B | C |
| ATOM | 3508 | CH2 | TRP | B | 406 | 40.297 | 0.058 | 46.178 | 1.00 | 23.32 | B | C |
| ATOM | 3509 | C | TRP | B | 406 | 34.307 | 3.557 | 48.758 | 1.00 | 20.17 | B | C |
| ATOM | 3510 | O | TRP | B | 406 | 34.262 | 4.629 | 49.355 | 1.00 | 20.39 | B | O |
| ATOM | 3511 | N | THR | B | 407 | 33.256 | 3.063 | 48.117 | 1.00 | 21.00 | B | N |
| ATOM | 3512 | CA | THR | B | 407 | 31.976 | 3.781 | 48.020 | 1.00 | 21.18 | B | C |
| ATOM | 3513 | CB | THR | B | 407 | 31.237 | 3.389 | 46.678 | 1.00 | 20.73 | B | C |
| ATOM | 3514 | OG1 | THR | B | 407 | 32.204 | 3.260 | 45.630 | 1.00 | 21.65 | B | O |
| ATOM | 3515 | CG2 | THR | B | 407 | 30.221 | 4.453 | 46.249 | 1.00 | 17.72 | B | C |
| ATOM | 3516 | C | THR | B | 407 | 31.043 | 3.552 | 49.231 | 1.00 | 20.36 | B | C |
| ATOM | 3517 | O | THR | B | 407 | 30.843 | 2.411 | 49.656 | 1.00 | 20.94 | B | O |
| ATOM | 3518 | N | ALA | B | 408 | 30.494 | 4.640 | 49.779 | 1.00 | 19.09 | B | N |
| ATOM | 3519 | CA | ALA | B | 408 | 29.563 | 4.586 | 50.916 | 1.00 | 20.29 | B | C |
| ATOM | 3520 | CB | ALA | B | 408 | 29.317 | 5.986 | 51.460 | 1.00 | 18.54 | B | C |
| ATOM | 3521 | C | ALA | B | 408 | 28.241 | 3.942 | 50.482 | 1.00 | 21.16 | B | C |
| ATOM | 3522 | O | ALA | B | 408 | 27.853 | 4.050 | 49.331 | 1.00 | 23.43 | B | O |
| ATOM | 3523 | N | PRO | B | 409 | 27.523 | 3.268 | 51.402 | 1.00 | 22.92 | B | N |
| ATOM | 3524 | CD | PRO | B | 409 | 27.810 | 3.053 | 52.831 | 1.00 | 22.65 | B | C |
| ATOM | 3525 | CA | PRO | B | 409 | 26.252 | 2.620 | 51.042 | 1.00 | 23.80 | B | C |
| ATOM | 3526 | CB | PRO | B | 409 | 25.720 | 2.136 | 52.392 | 1.00 | 23.47 | B | C |
| ATOM | 3527 | CG | PRO | B | 409 | 26.976 | 1.830 | 53.145 | 1.00 | 22.91 | B | C |

Figure 4

| ATOM | 3528 | C | PRO | B | 409 | 25.245 | 3.514 | 50.308 | 1.00 | 23.63 | B | C |
|------|------|------|-----|---|-----|--------|-------|--------|------|-------|---|---|
| ATOM | 3529 | O | PRO | B | 409 | 24.623 | 3.084 | 49.332 | 1.00 | 23.53 | B | O |
| ATOM | 3530 | N | GLU | B | 410 | 25.119 | 4.765 | 50.738 | 1.00 | 23.31 | B | N |
| ATOM | 3531 | CA | GLU | B | 410 | 24.179 | 5.692 | 50.105 | 1.00 | 23.78 | B | C |
| ATOM | 3532 | CB | GLU | B | 410 | 23.959 | 6.949 | 50.965 | 1.00 | 23.80 | B | C |
| ATOM | 3533 | CG | GLU | B | 410 | 25.104 | 7.976 | 51.014 | 1.00 | 24.87 | B | C |
| ATOM | 3534 | CD | GLU | B | 410 | 26.217 | 7.663 | 52.034 | 1.00 | 24.39 | B | C |
| ATOM | 3535 | OE1 | GLU | B | 410 | 26.220 | 6.571 | 52.638 | 1.00 | 24.52 | B | O |
| ATOM | 3536 | OE2 | GLU | B | 410 | 27.100 | 8.527 | 52.224 | 1.00 | 23.55 | B | O |
| ATOM | 3537 | C | GLU | B | 410 | 24.588 | 6.091 | 48.686 | 1.00 | 24.43 | B | C |
| ATOM | 3538 | O | GLU | B | 410 | 23.744 | 6.451 | 47.859 | 1.00 | 24.96 | B | O |
| ATOM | 3539 | N | ALA | B | 411 | 25.889 | 6.022 | 48.410 | 1.00 | 24.22 | B | N |
| ATOM | 3540 | CA | ALA | B | 411 | 26.424 | 6.367 | 47.097 | 1.00 | 23.44 | B | C |
| ATOM | 3541 | CB | ALA | B | 411 | 27.886 | 6.739 | 47.212 | 1.00 | 20.40 | B | C |
| ATOM | 3542 | C | ALA | B | 411 | 26.233 | 5.180 | 46.151 | 1.00 | 24.90 | B | C |
| ATOM | 3543 | O | ALA | B | 411 | 26.056 | 5.353 | 44.943 | 1.00 | 25.63 | B | O |
| ATOM | 3544 | N | ILE | B | 412 | 26.218 | 3.981 | 46.728 | 1.00 | 25.93 | B | N |
| ATOM | 3545 | CA | ILE | B | 412 | 26.027 | 2.754 | 45.972 | 1.00 | 27.86 | B | C |
| ATOM | 3546 | CB | ILE | B | 412 | 26.501 | 1.528 | 46.768 | 1.00 | 28.10 | B | C |
| ATOM | 3547 | CG2 | ILE | B | 412 | 26.116 | 0.240 | 46.035 | 1.00 | 29.09 | B | C |
| ATOM | 3548 | CG1 | ILE | B | 412 | 28.008 | 1.592 | 47.002 | 1.00 | 27.87 | B | C |
| ATOM | 3549 | CD1 | ILE | B | 412 | 28.533 | 0.379 | 47.696 | 1.00 | 28.24 | B | C |
| ATOM | 3550 | C | ILE | B | 412 | 24.562 | 2.508 | 45.597 | 1.00 | 29.58 | B | C |
| ATOM | 3551 | O | ILE | B | 412 | 24.265 | 2.107 | 44.469 | 1.00 | 30.37 | B | O |
| ATOM | 3552 | N | ASN | B | 413 | 23.665 | 2.730 | 46.556 | 1.00 | 29.94 | B | N |
| ATOM | 3553 | CA | ASN | B | 413 | 22.232 | 2.497 | 46.368 | 1.00 | 30.72 | B | C |
| ATOM | 3554 | CB | ASN | B | 413 | 21.544 | 2.228 | 47.705 | 1.00 | 30.05 | B | C |
| ATOM | 3555 | CG | ASN | B | 413 | 22.063 | 0.998 | 48.393 | 1.00 | 30.98 | B | C |
| ATOM | 3556 | OD1 | ASN | B | 413 | 22.288 | -0.036 | 47.754 | 1.00 | 32.44 | B | O |
| ATOM | 3557 | ND2 | ASN | B | 413 | 22.244 | 1.089 | 49.709 | 1.00 | 30.07 | B | N |
| ATOM | 3558 | C | ASN | B | 413 | 21.473 | 3.601 | 45.674 | 1.00 | 30.66 | B | C |
| ATOM | 3559 | O | ASN | B | 413 | 20.556 | 3.323 | 44.901 | 1.00 | 32.98 | B | O |
| ATOM | 3560 | N | TYR | B | 414 | 21.829 | 4.847 | 45.963 | 1.00 | 31.15 | B | N |
| ATOM | 3561 | CA | TYR | B | 414 | 21.126 | 5.966 | 45.368 | 1.00 | 32.64 | B | C |
| ATOM | 3562 | CB | TYR | B | 414 | 20.347 | 6.719 | 46.453 | 1.00 | 34.62 | B | C |
| ATOM | 3563 | CG | TYR | B | 414 | 19.478 | 5.814 | 47.300 | 1.00 | 37.02 | B | C |
| ATOM | 3564 | CD1 | TYR | B | 414 | 18.255 | 5.319 | 46.813 | 1.00 | 37.34 | B | C |
| ATOM | 3565 | CE1 | TYR | B | 414 | 17.483 | 4.458 | 47.574 | 1.00 | 38.21 | B | C |
| ATOM | 3566 | CD2 | TYR | B | 414 | 19.894 | 5.418 | 48.574 | 1.00 | 37.68 | B | C |
| ATOM | 3567 | CE2 | TYR | B | 414 | 19.127 | 4.556 | 49.343 | 1.00 | 39.35 | B | C |
| ATOM | 3568 | CZ | TYR | B | 414 | 17.926 | 4.076 | 48.841 | 1.00 | 40.00 | B | C |
| ATOM | 3569 | OH | TYR | B | 414 | 17.189 | 3.202 | 49.616 | 1.00 | 42.08 | B | O |
| ATOM | 3570 | C | TYR | B | 414 | 22.007 | 6.925 | 44.571 | 1.00 | 32.95 | B | C |
| ATOM | 3571 | O | TYR | B | 414 | 21.496 | 7.853 | 43.932 | 1.00 | 32.27 | B | O |
| ATOM | 3572 | N | GLY | B | 415 | 23.327 | 6.716 | 44.625 | 1.00 | 32.69 | B | N |
| ATOM | 3573 | CA | GLY | B | 415 | 24.251 | 7.560 | 43.884 | 1.00 | 29.07 | B | C |
| ATOM | 3574 | C | GLY | B | 415 | 24.383 | 8.956 | 44.438 | 1.00 | 28.10 | B | C |
| ATOM | 3575 | O | GLY | B | 415 | 24.656 | 9.907 | 43.706 | 1.00 | 28.82 | B | O |
| ATOM | 3576 | N | THR | B | 416 | 24.164 | 9.087 | 45.738 | 1.00 | 28.22 | B | N |
| ATOM | 3577 | CA | THR | B | 416 | 24.276 | 10.383 | 46.386 | 1.00 | 28.09 | B | C |
| ATOM | 3578 | CB | THR | B | 416 | 23.134 | 10.606 | 47.436 | 1.00 | 27.92 | B | C |
| ATOM | 3579 | OG1 | THR | B | 416 | 23.679 | 11.080 | 48.673 | 1.00 | 28.57 | B | O |
| ATOM | 3580 | CG2 | THR | B | 416 | 22.329 | 9.342 | 47.663 | 1.00 | 26.38 | B | C |
| ATOM | 3581 | C | THR | B | 416 | 25.681 | 10.510 | 46.986 | 1.00 | 26.85 | B | C |
| ATOM | 3582 | O | THR | B | 416 | 26.053 | 9.768 | 47.887 | 1.00 | 28.09 | B | O |
| ATOM | 3583 | N | PHE | B | 417 | 26.486 | 11.375 | 46.381 | 1.00 | 26.40 | B | N |
| ATOM | 3584 | CA | PHE | B | 417 | 27.851 | 11.603 | 46.821 | 1.00 | 24.42 | B | C |
| ATOM | 3585 | CB | PHE | B | 417 | 28.811 | 11.577 | 45.631 | 1.00 | 25.37 | B | C |
| ATOM | 3586 | CG | PHE | B | 417 | 28.996 | 10.213 | 45.001 | 1.00 | 26.87 | B | C |
| ATOM | 3587 | CD1 | PHE | B | 417 | 28.162 | 9.779 | 43.957 | 1.00 | 26.83 | B | C |

Figure 4

```
ATOM   3588  CD2 PHE B 417      30.031   9.369  45.423  1.00 25.37      B  C
ATOM   3589  CE1 PHE B 417      28.349   8.527  43.342  1.00 25.94      B  C
ATOM   3590  CE2 PHE B 417      30.223   8.111  44.815  1.00 26.20      B  C
ATOM   3591  CZ  PHE B 417      29.382   7.692  43.772  1.00 25.51      B  C
ATOM   3592  C   PHE B 417      27.972  12.953  47.508  1.00 24.63      B  C
ATOM   3593  O   PHE B 417      27.588  13.981  46.957  1.00 26.49      B  O
ATOM   3594  N   THR B 418      28.468  12.936  48.737  1.00 23.76      B  N
ATOM   3595  CA  THR B 418      28.690  14.142  49.518  1.00 22.39      B  C
ATOM   3596  CB  THR B 418      27.637  14.333  50.617  1.00 23.14      B  C
ATOM   3597  OG1 THR B 418      27.744  13.268  51.562  1.00 23.22      B  O
ATOM   3598  CG2 THR B 418      26.228  14.370  50.017  1.00 23.34      B  C
ATOM   3599  C   THR B 418      30.051  13.998  50.199  1.00 22.54      B  C
ATOM   3600  O   THR B 418      30.749  12.995  50.030  1.00 23.06      B  O
ATOM   3601  N   ILE B 419      30.429  15.006  50.972  1.00 23.33      B  N
ATOM   3602  CA  ILE B 419      31.694  14.983  51.679  1.00 22.80      B  C
ATOM   3603  CB  ILE B 419      31.987  16.360  52.365  1.00 22.71      B  C
ATOM   3604  CG2 ILE B 419      31.075  16.592  53.528  1.00 20.57      B  C
ATOM   3605  CG1 ILE B 419      33.447  16.433  52.806  1.00 23.60      B  C
ATOM   3606  CD1 ILE B 419      34.436  16.463  51.638  1.00 22.55      B  C
ATOM   3607  C   ILE B 419      31.633  13.840  52.695  1.00 22.79      B  C
ATOM   3608  O   ILE B 419      32.665  13.308  53.094  1.00 22.27      B  O
ATOM   3609  N   LYS B 420      30.418  13.426  53.062  1.00 21.72      B  N
ATOM   3610  CA  LYS B 420      30.254  12.334  54.010  1.00 21.82      B  C
ATOM   3611  CB  LYS B 420      28.869  12.352  54.649  1.00 21.11      B  C
ATOM   3612  CG  LYS B 420      28.665  13.535  55.569  1.00 19.93      B  C
ATOM   3613  CD  LYS B 420      29.595  13.475  56.765  1.00 18.98      B  C
ATOM   3614  CE  LYS B 420      29.390  14.701  57.626  1.00 18.23      B  C
ATOM   3615  NZ  LYS B 420      30.307  14.695  58.767  1.00 19.03      B  N
ATOM   3616  C   LYS B 420      30.562  10.992  53.380  1.00 20.98      B  C
ATOM   3617  O   LYS B 420      30.954  10.057  54.086  1.00 22.25      B  O
ATOM   3618  N   SER B 421      30.364  10.873  52.065  1.00 20.31      B  N
ATOM   3619  CA  SER B 421      30.719   9.628  51.407  1.00 20.44      B  C
ATOM   3620  CB  SER B 421      29.913   9.373  50.118  1.00 19.00      B  C
ATOM   3621  OG  SER B 421      29.885  10.476  49.246  1.00 21.89      B  O
ATOM   3622  C   SER B 421      32.259   9.598  51.221  1.00 20.31      B  C
ATOM   3623  O   SER B 421      32.854   8.535  51.137  1.00 21.51      B  O
ATOM   3624  N   ASP B 422      32.903  10.765  51.243  1.00 19.45      B  N
ATOM   3625  CA  ASP B 422      34.373  10.830  51.141  1.00 19.76      B  C
ATOM   3626  CB  ASP B 422      34.879  12.250  50.878  1.00 17.22      B  C
ATOM   3627  CG  ASP B 422      34.679  12.693  49.455  1.00 16.24      B  C
ATOM   3628  OD1 ASP B 422      34.760  11.855  48.533  1.00 19.68      B  O
ATOM   3629  OD2 ASP B 422      34.454  13.897  49.259  1.00 16.90      B  O
ATOM   3630  C   ASP B 422      34.959  10.377  52.455  1.00 20.36      B  C
ATOM   3631  O   ASP B 422      36.007   9.732  52.480  1.00 22.06      B  O
ATOM   3632  N   VAL B 423      34.314  10.794  53.549  1.00 21.16      B  N
ATOM   3633  CA  VAL B 423      34.741  10.415  54.898  1.00 20.86      B  C
ATOM   3634  CB  VAL B 423      33.808  11.006  56.008  1.00 21.55      B  C
ATOM   3635  CG1 VAL B 423      34.220  10.490  57.398  1.00 19.15      B  C
ATOM   3636  CG2 VAL B 423      33.853  12.543  55.983  1.00 21.24      B  C
ATOM   3637  C   VAL B 423      34.736   8.892  54.968  1.00 20.57      B  C
ATOM   3638  O   VAL B 423      35.655   8.298  55.535  1.00 21.24      B  O
ATOM   3639  N   TRP B 424      33.713   8.269  54.369  1.00 19.94      B  N
ATOM   3640  CA  TRP B 424      33.613   6.807  54.321  1.00 20.05      B  C
ATOM   3641  CB  TRP B 424      32.299   6.368  53.652  1.00 17.73      B  C
ATOM   3642  CG  TRP B 424      32.203   4.881  53.447  1.00 16.99      B  C
ATOM   3643  CD2 TRP B 424      31.340   3.961  54.142  1.00 19.00      B  C
ATOM   3644  CE2 TRP B 424      31.641   2.661  53.652  1.00 19.08      B  C
ATOM   3645  CE3 TRP B 424      30.348   4.093  55.127  1.00 18.77      B  C
ATOM   3646  CD1 TRP B 424      32.953   4.125  52.599  1.00 16.91      B  C
ATOM   3647  NE1 TRP B 424      32.633   2.796  52.717  1.00 18.40      B  N
```

Figure 4

| | | | | | | | | | | |
|---|---|---|---|---|---|---|---|---|---|---|
| ATOM | 3648 | CZ2 | TRP | B | 424 | 30.991 | 1.502 | 54.122 | 1.00 18.54 | B C |
| ATOM | 3649 | CZ3 | TRP | B | 424 | 29.709 | 2.943 | 55.594 | 1.00 17.24 | B C |
| ATOM | 3650 | CH2 | TRP | B | 424 | 30.032 | 1.670 | 55.089 | 1.00 18.30 | B C |
| ATOM | 3651 | C | TRP | B | 424 | 34.840 | 6.242 | 53.563 | 1.00 21.25 | B C |
| ATOM | 3652 | O | TRP | B | 424 | 35.490 | 5.297 | 54.039 | 1.00 20.19 | B O |
| ATOM | 3653 | N | SER | B | 425 | 35.126 | 6.823 | 52.391 | 1.00 22.71 | B N |
| ATOM | 3654 | CA | SER | B | 425 | 36.268 | 6.448 | 51.546 | 1.00 24.22 | B C |
| ATOM | 3655 | CB | SER | B | 425 | 36.309 | 7.327 | 50.285 | 1.00 25.94 | B C |
| ATOM | 3656 | OG | SER | B | 425 | 35.432 | 6.858 | 49.284 | 1.00 27.28 | B O |
| ATOM | 3657 | C | SER | B | 425 | 37.606 | 6.597 | 52.283 | 1.00 22.98 | B C |
| ATOM | 3658 | O | SER | B | 425 | 38.520 | 5.799 | 52.081 | 1.00 23.19 | B O |
| ATOM | 3659 | N | PHE | B | 426 | 37.724 | 7.665 | 53.070 | 1.00 22.13 | B N |
| ATOM | 3660 | CA | PHE | B | 426 | 38.920 | 7.933 | 53.847 | 1.00 23.42 | B C |
| ATOM | 3661 | CB | PHE | B | 426 | 38.833 | 9.305 | 54.519 | 1.00 22.46 | B C |
| ATOM | 3662 | CG | PHE | B | 426 | 40.057 | 9.655 | 55.332 | 1.00 23.45 | B C |
| ATOM | 3663 | CD1 | PHE | B | 426 | 41.244 | 10.018 | 54.699 | 1.00 21.41 | B C |
| ATOM | 3664 | CD2 | PHE | B | 426 | 40.014 | 9.635 | 56.744 | 1.00 23.21 | B C |
| ATOM | 3665 | CE1 | PHE | B | 426 | 42.375 | 10.363 | 55.444 | 1.00 23.18 | B C |
| ATOM | 3666 | CE2 | PHE | B | 426 | 41.152 | 9.981 | 57.504 | 1.00 24.01 | B C |
| ATOM | 3667 | CZ | PHE | B | 426 | 42.330 | 10.346 | 56.846 | 1.00 23.24 | B C |
| ATOM | 3668 | C | PHE | B | 426 | 39.150 | 6.828 | 54.893 | 1.00 23.82 | B C |
| ATOM | 3669 | O | PHE | B | 426 | 40.309 | 6.434 | 55.149 | 1.00 24.85 | B O |
| ATOM | 3670 | N | GLY | B | 427 | 38.057 | 6.355 | 55.502 | 1.00 21.51 | B N |
| ATOM | 3671 | CA | GLY | B | 427 | 38.136 | 5.270 | 56.464 | 1.00 18.76 | B C |
| ATOM | 3672 | C | GLY | B | 427 | 38.676 | 4.039 | 55.757 | 1.00 19.35 | B C |
| ATOM | 3673 | O | GLY | B | 427 | 39.523 | 3.328 | 56.304 | 1.00 19.74 | B O |
| ATOM | 3674 | N | ILE | B | 428 | 38.193 | 3.783 | 54.535 | 1.00 19.93 | B N |
| ATOM | 3675 | CA | ILE | B | 428 | 38.674 | 2.643 | 53.734 | 1.00 20.26 | B C |
| ATOM | 3676 | CB | ILE | B | 428 | 37.837 | 2.444 | 52.432 | 1.00 17.34 | B C |
| ATOM | 3677 | CG2 | ILE | B | 428 | 38.334 | 1.228 | 51.671 | 1.00 15.21 | B C |
| ATOM | 3678 | CG1 | ILE | B | 428 | 36.349 | 2.257 | 52.765 | 1.00 17.25 | B C |
| ATOM | 3679 | CD1 | ILE | B | 428 | 36.021 | 0.999 | 53.604 | 1.00 14.63 | B C |
| ATOM | 3680 | C | ILE | B | 428 | 40.171 | 2.868 | 53.371 | 1.00 20.45 | B C |
| ATOM | 3681 | O | ILE | B | 428 | 40.970 | 1.925 | 53.365 | 1.00 20.19 | B O |
| ATOM | 3682 | N | LEU | B | 429 | 40.528 | 4.128 | 53.117 | 1.00 19.33 | B N |
| ATOM | 3683 | CA | LEU | B | 429 | 41.887 | 4.520 | 52.774 | 1.00 20.47 | B C |
| ATOM | 3684 | CB | LEU | B | 429 | 41.907 | 6.003 | 52.329 | 1.00 20.02 | B C |
| ATOM | 3685 | CG | LEU | B | 429 | 43.164 | 6.619 | 51.703 | 1.00 18.99 | B C |
| ATOM | 3686 | CD1 | LEU | B | 429 | 42.836 | 7.926 | 51.012 | 1.00 19.64 | B C |
| ATOM | 3687 | CD2 | LEU | B | 429 | 44.220 | 6.852 | 52.752 | 1.00 20.82 | B C |
| ATOM | 3688 | C | LEU | B | 429 | 42.824 | 4.287 | 53.970 | 1.00 21.45 | B C |
| ATOM | 3689 | O | LEU | B | 429 | 43.994 | 3.932 | 53.784 | 1.00 20.91 | B O |
| ATOM | 3690 | N | LEU | B | 430 | 42.309 | 4.490 | 55.190 | 1.00 20.66 | B N |
| ATOM | 3691 | CA | LEU | B | 430 | 43.101 | 4.294 | 56.400 | 1.00 19.40 | B C |
| ATOM | 3692 | CB | LEU | B | 430 | 42.334 | 4.712 | 57.655 | 1.00 18.72 | B C |
| ATOM | 3693 | CG | LEU | B | 430 | 42.099 | 6.192 | 57.941 | 1.00 18.57 | B C |
| ATOM | 3694 | CD1 | LEU | B | 430 | 41.124 | 6.313 | 59.116 | 1.00 16.63 | B C |
| ATOM | 3695 | CD2 | LEU | B | 430 | 43.442 | 6.913 | 58.220 | 1.00 17.42 | B C |
| ATOM | 3696 | C | LEU | B | 430 | 43.521 | 2.849 | 56.528 | 1.00 19.76 | B C |
| ATOM | 3697 | O | LEU | B | 430 | 44.582 | 2.583 | 57.062 | 1.00 21.96 | B O |
| ATOM | 3698 | N | THR | B | 431 | 42.678 | 1.915 | 56.086 | 1.00 20.74 | B N |
| ATOM | 3699 | CA | THR | B | 431 | 43.021 | 0.495 | 56.142 | 1.00 21.83 | B C |
| ATOM | 3700 | CB | THR | B | 431 | 41.787 | -0.436 | 55.926 | 1.00 21.37 | B O |
| ATOM | 3701 | OG1 | THR | B | 431 | 41.367 | -0.417 | 54.554 | 1.00 23.51 | B C |
| ATOM | 3702 | CG2 | THR | B | 431 | 40.642 | 0.005 | 56.799 | 1.00 19.63 | B C |
| ATOM | 3703 | C | THR | B | 431 | 44.128 | 0.182 | 55.120 | 1.00 22.98 | B C |
| ATOM | 3704 | O | THR | B | 431 | 44.957 | -0.691 | 55.356 | 1.00 24.81 | B O |
| ATOM | 3705 | N | GLU | B | 432 | 44.146 | 0.908 | 53.996 | 1.00 23.25 | B N |
| ATOM | 3706 | CA | GLU | B | 432 | 45.174 | 0.742 | 52.972 | 1.00 23.06 | B C |
| ATOM | 3707 | CB | GLU | B | 432 | 44.858 | 1.578 | 51.735 | 1.00 22.48 | B C |

Figure 4

| | | | | | | | | | | | |
|---|---|---|---|---|---|---|---|---|---|---|---|
| ATOM | 3708 | CG | GLU | B | 432 | 43.743 | 1.032 | 50.873 | 1.00 23.06 | B | C |
| ATOM | 3709 | CD | GLU | B | 432 | 43.502 | 1.899 | 49.638 | 1.00 22.96 | B | C |
| ATOM | 3710 | OE1 | GLU | B | 432 | 42.984 | 3.029 | 49.792 | 1.00 21.98 | B | O |
| ATOM | 3711 | OE2 | GLU | B | 432 | 43.840 | 1.460 | 48.516 | 1.00 21.72 | B | O |
| ATOM | 3712 | C | GLU | B | 432 | 46.500 | 1.226 | 53.540 | 1.00 23.93 | B | C |
| ATOM | 3713 | O | GLU | B | 432 | 47.522 | 0.574 | 53.382 | 1.00 26.03 | B | O |
| ATOM | 3714 | N | ILE | B | 433 | 46.469 | 2.417 | 54.185 | 1.00 24.96 | B | N |
| ATOM | 3715 | CA | ILE | B | 433 | 47.651 | 3.050 | 54.757 | 1.00 24.47 | B | C |
| ATOM | 3716 | CB | ILE | B | 433 | 47.305 | 4.376 | 55.446 | 1.00 23.16 | B | C |
| ATOM | 3717 | CG2 | ILE | B | 433 | 48.372 | 4.767 | 56.460 | 1.00 22.20 | B | C |
| ATOM | 3718 | CG1 | ILE | B | 433 | 47.137 | 5.433 | 54.379 | 1.00 23.94 | B | C |
| ATOM | 3719 | CD1 | ILE | B | 433 | 46.932 | 6.823 | 54.944 | 1.00 23.96 | B | C |
| ATOM | 3720 | C | ILE | B | 433 | 48.265 | 2.215 | 55.834 | 1.00 27.89 | B | C |
| ATOM | 3721 | O | ILE | B | 433 | 49.442 | 2.334 | 56.143 | 1.00 28.52 | B | O |
| ATOM | 3722 | N | VAL | B | 434 | 47.448 | 1.310 | 56.370 | 1.00 27.27 | B | N |
| ATOM | 3723 | CA | VAL | B | 434 | 47.928 | 0.565 | 57.528 | 1.00 28.24 | B | C |
| ATOM | 3724 | CB | VAL | B | 434 | 46.914 | 0.611 | 58.687 | 1.00 27.33 | B | C |
| ATOM | 3725 | CG1 | VAL | B | 434 | 46.726 | 2.039 | 59.174 | 1.00 24.85 | B | C |
| ATOM | 3726 | CG2 | VAL | B | 434 | 45.586 | 0.007 | 58.257 | 1.00 29.24 | B | C |
| ATOM | 3727 | C | VAL | B | 434 | 48.241 | -0.886 | 57.171 | 1.00 29.55 | B | C |
| ATOM | 3728 | O | VAL | B | 434 | 48.782 | -1.618 | 58.032 | 1.00 31.77 | B | O |
| ATOM | 3729 | N | THR | B | 435 | 47.917 | -1.306 | 56.007 | 1.00 31.22 | B | N |
| ATOM | 3730 | CA | THR | B | 435 | 48.205 | -2.674 | 55.660 | 1.00 31.21 | B | C |
| ATOM | 3731 | CB | THR | B | 435 | 46.909 | -3.401 | 55.280 | 1.00 30.57 | B | C |
| ATOM | 3732 | OG1 | THR | B | 435 | 46.204 | -2.638 | 54.296 | 1.00 29.24 | B | O |
| ATOM | 3733 | CG2 | THR | B | 435 | 46.028 | -3.578 | 56.498 | 1.00 30.32 | B | C |
| ATOM | 3734 | C | THR | B | 435 | 49.156 | -2.675 | 54.460 | 1.00 32.35 | B | C |
| ATOM | 3735 | O | THR | B | 435 | 49.258 | -3.647 | 53.707 | 1.00 30.72 | B | O |
| ATOM | 3736 | N | HIS | B | 436 | 49.841 | -1.549 | 54.305 | 1.00 35.33 | B | N |
| ATOM | 3737 | CA | HIS | B | 436 | 50.795 | -1.340 | 53.218 | 1.00 37.08 | B | C |
| ATOM | 3738 | CB | HIS | B | 436 | 52.070 | -2.163 | 53.439 | 1.00 41.16 | B | C |
| ATOM | 3739 | CG | HIS | B | 436 | 52.693 | -1.932 | 54.783 | 1.00 44.42 | B | C |
| ATOM | 3740 | CD2 | HIS | B | 436 | 53.278 | -2.787 | 55.659 | 1.00 45.91 | B | C |
| ATOM | 3741 | ND1 | HIS | B | 436 | 52.658 | -0.705 | 55.413 | 1.00 45.79 | B | N |
| ATOM | 3742 | CE1 | HIS | B | 436 | 53.186 | -0.812 | 56.622 | 1.00 46.88 | B | C |
| ATOM | 3743 | NE2 | HIS | B | 436 | 53.568 | -2.064 | 56.794 | 1.00 48.06 | B | N |
| ATOM | 3744 | C | HIS | B | 436 | 50.211 | -1.551 | 51.835 | 1.00 35.93 | B | C |
| ATOM | 3745 | O | HIS | B | 436 | 50.690 | -2.386 | 51.065 | 1.00 34.91 | B | O |
| ATOM | 3746 | N | GLY | B | 437 | 49.173 | -0.764 | 51.550 | 1.00 34.97 | B | N |
| ATOM | 3747 | CA | GLY | B | 437 | 48.501 | -0.784 | 50.267 | 1.00 35.57 | B | C |
| ATOM | 3748 | C | GLY | B | 437 | 47.684 | -2.012 | 49.939 | 1.00 35.74 | B | C |
| ATOM | 3749 | O | GLY | B | 437 | 47.378 | -2.251 | 48.774 | 1.00 34.86 | B | O |
| ATOM | 3750 | N | ARG | B | 438 | 47.333 | -2.791 | 50.954 | 1.00 36.71 | B | N |
| ATOM | 3751 | CA | ARG | B | 438 | 46.528 | -3.993 | 50.755 | 1.00 37.10 | B | C |
| ATOM | 3752 | CB | ARG | B | 438 | 46.506 | -4.806 | 52.053 | 1.00 40.55 | B | C |
| ATOM | 3753 | CG | ARG | B | 438 | 46.105 | -6.278 | 51.937 | 1.00 44.89 | B | C |
| ATOM | 3754 | CD | ARG | B | 438 | 44.584 | -6.497 | 51.935 | 1.00 47.34 | B | C |
| ATOM | 3755 | NE | ARG | B | 438 | 43.905 | -5.935 | 53.110 | 1.00 49.70 | B | N |
| ATOM | 3756 | CZ | ARG | B | 438 | 44.035 | -6.392 | 54.356 | 1.00 50.60 | B | C |
| ATOM | 3757 | NH1 | ARG | B | 438 | 44.832 | -7.429 | 54.611 | 1.00 51.13 | B | N |
| ATOM | 3758 | NH2 | ARG | B | 438 | 43.357 | -5.820 | 55.347 | 1.00 50.43 | B | N |
| ATOM | 3759 | C | ARG | B | 438 | 45.103 | -3.576 | 50.323 | 1.00 34.62 | B | C |
| ATOM | 3760 | O | ARG | B | 438 | 44.602 | -2.516 | 50.719 | 1.00 32.85 | B | O |
| ATOM | 3761 | N | ILE | B | 439 | 44.505 | -4.390 | 49.456 | 1.00 31.40 | B | N |
| ATOM | 3762 | CA | ILE | B | 439 | 43.166 | -4.160 | 48.935 | 1.00 31.16 | B | C |
| ATOM | 3763 | CB | ILE | B | 439 | 42.879 | -5.094 | 47.730 | 1.00 31.18 | B | C |
| ATOM | 3764 | CG2 | ILE | B | 439 | 41.409 | -5.037 | 47.338 | 1.00 31.45 | B | C |
| ATOM | 3765 | CG1 | ILE | B | 439 | 43.735 | -4.660 | 46.535 | 1.00 32.41 | B | C |
| ATOM | 3766 | CD1 | ILE | B | 439 | 43.703 | -5.632 | 45.352 | 1.00 33.27 | B | C |
| ATOM | 3767 | C | ILE | B | 439 | 42.107 | -4.337 | 50.021 | 1.00 30.03 | B | C |

Figure 4

| | | | | | | | | | | | |
|---|---|---|---|---|---|---|---|---|---|---|---|
| ATOM | 3768 | O | ILE | B | 439 | 42.188 | -5.264 | 50.829 | 1.00 | 31.12 | B O |
| ATOM | 3769 | N | PRO | B | 440 | 41.129 | -3.414 | 50.085 | 1.00 | 28.80 | B N |
| ATOM | 3770 | CD | PRO | B | 440 | 40.992 | -2.206 | 49.250 | 1.00 | 26.82 | B C |
| ATOM | 3771 | CA | PRO | B | 440 | 40.054 | -3.483 | 51.088 | 1.00 | 28.63 | B C |
| ATOM | 3772 | CB | PRO | B | 440 | 39.190 | -2.262 | 50.737 | 1.00 | 27.39 | B C |
| ATOM | 3773 | CG | PRO | B | 440 | 40.185 | -1.299 | 50.128 | 1.00 | 26.71 | B C |
| ATOM | 3774 | C | PRO | B | 440 | 39.249 | -4.788 | 50.960 | 1.00 | 28.23 | B C |
| ATOM | 3775 | O | PRO | B | 440 | 39.222 | -5.397 | 49.888 | 1.00 | 27.02 | B O |
| ATOM | 3776 | N | TYR | B | 441 | 38.628 | -5.219 | 52.061 | 1.00 | 27.57 | B N |
| ATOM | 3777 | CA | TYR | B | 441 | 37.824 | -6.444 | 52.078 | 1.00 | 27.67 | B C |
| ATOM | 3778 | CB | TYR | B | 441 | 36.469 | -6.211 | 51.404 | 1.00 | 27.62 | B C |
| ATOM | 3779 | CG | TYR | B | 441 | 35.717 | -5.000 | 51.878 | 1.00 | 25.71 | B C |
| ATOM | 3780 | CD1 | TYR | B | 441 | 34.842 | -5.075 | 52.978 | 1.00 | 25.06 | B C |
| ATOM | 3781 | CE1 | TYR | B | 441 | 34.154 | -3.944 | 53.426 | 1.00 | 25.83 | B C |
| ATOM | 3782 | CD2 | TYR | B | 441 | 35.889 | -3.771 | 51.242 | 1.00 | 24.46 | B C |
| ATOM | 3783 | CE2 | TYR | B | 441 | 35.211 | -2.635 | 51.676 | 1.00 | 25.44 | B C |
| ATOM | 3784 | CZ | TYR | B | 441 | 34.351 | -2.726 | 52.772 | 1.00 | 25.72 | B C |
| ATOM | 3785 | OH | TYR | B | 441 | 33.689 | -1.601 | 53.192 | 1.00 | 26.40 | B O |
| ATOM | 3786 | C | TYR | B | 441 | 38.510 | -7.603 | 51.369 | 1.00 | 29.03 | B C |
| ATOM | 3787 | O | TYR | B | 441 | 37.978 | -8.154 | 50.402 | 1.00 | 28.15 | B O |
| ATOM | 3788 | N | PRO | B | 442 | 39.696 | -8.002 | 51.847 | 1.00 | 32.09 | B N |
| ATOM | 3789 | CD | PRO | B | 442 | 40.371 | -7.592 | 53.091 | 1.00 | 32.71 | B C |
| ATOM | 3790 | CA | PRO | B | 442 | 40.399 | -9.114 | 51.193 | 1.00 | 34.68 | B C |
| ATOM | 3791 | CB | PRO | B | 442 | 41.661 | -9.255 | 52.034 | 1.00 | 34.52 | B C |
| ATOM | 3792 | CG | PRO | B | 442 | 41.193 | -8.814 | 53.426 | 1.00 | 34.07 | B C |
| ATOM | 3793 | C | PRO | B | 442 | 39.560 | -10.406 | 51.171 | 1.00 | 37.20 | B C |
| ATOM | 3794 | O | PRO | B | 442 | 38.845 | -10.717 | 52.124 | 1.00 | 37.93 | B O |
| ATOM | 3795 | N | GLY | B | 443 | 39.612 | -11.133 | 50.061 | 1.00 | 39.44 | B N |
| ATOM | 3796 | CA | GLY | B | 443 | 38.832 | -12.353 | 49.962 | 1.00 | 41.37 | B C |
| ATOM | 3797 | C | GLY | B | 443 | 37.401 | -12.078 | 49.523 | 1.00 | 42.68 | B C |
| ATOM | 3798 | O | GLY | B | 443 | 36.544 | -12.974 | 49.538 | 1.00 | 45.02 | B O |
| ATOM | 3799 | N | MET | B | 444 | 37.132 | -10.829 | 49.149 | 1.00 | 41.31 | B N |
| ATOM | 3800 | CA | MET | B | 444 | 35.811 | -10.441 | 48.691 | 1.00 | 40.28 | B C |
| ATOM | 3801 | CB | MET | B | 444 | 35.165 | -9.463 | 49.673 | 1.00 | 40.63 | B C |
| ATOM | 3802 | CG | MET | B | 444 | 34.379 | -10.122 | 50.770 | 1.00 | 41.31 | B C |
| ATOM | 3803 | SD | MET | B | 444 | 34.077 | -9.040 | 52.165 | 1.00 | 43.39 | B S |
| ATOM | 3804 | CE | MET | B | 444 | 32.628 | -8.278 | 51.675 | 1.00 | 43.28 | B C |
| ATOM | 3805 | C | MET | B | 444 | 35.890 | -9.806 | 47.316 | 1.00 | 40.09 | B C |
| ATOM | 3806 | O | MET | B | 444 | 36.855 | -9.108 | 47.000 | 1.00 | 41.16 | B O |
| ATOM | 3807 | N | THR | B | 445 | 34.886 | -10.089 | 46.491 | 1.00 | 39.16 | B N |
| ATOM | 3808 | CA | THR | B | 445 | 34.778 | -9.529 | 45.152 | 1.00 | 38.69 | B C |
| ATOM | 3809 | CB | THR | B | 445 | 34.195 | -10.570 | 44.158 | 1.00 | 38.94 | B C |
| ATOM | 3810 | OG1 | THR | B | 445 | 32.852 | -10.901 | 44.526 | 1.00 | 39.15 | B O |
| ATOM | 3811 | CG2 | THR | B | 445 | 35.011 | -11.843 | 44.187 | 1.00 | 39.67 | B C |
| ATOM | 3812 | C | THR | B | 445 | 33.798 | -8.363 | 45.294 | 1.00 | 38.79 | B C |
| ATOM | 3813 | O | THR | B | 445 | 33.119 | -8.241 | 46.314 | 1.00 | 36.87 | B O |
| ATOM | 3814 | N | ASN | B | 446 | 33.707 | -7.507 | 44.283 | 1.00 | 41.19 | B N |
| ATOM | 3815 | CA | ASN | B | 446 | 32.774 | -6.374 | 44.342 | 1.00 | 42.44 | B C |
| ATOM | 3816 | CB | ASN | B | 446 | 32.793 | -5.552 | 43.048 | 1.00 | 42.43 | B C |
| ATOM | 3817 | CG | ASN | B | 446 | 33.923 | -4.539 | 43.018 | 1.00 | 43.67 | B C |
| ATOM | 3818 | OD1 | ASN | B | 446 | 34.838 | -4.561 | 43.862 | 1.00 | 41.28 | B O |
| ATOM | 3819 | ND2 | ASN | B | 446 | 33.864 | -3.635 | 42.042 | 1.00 | 45.00 | B N |
| ATOM | 3820 | C | ASN | B | 446 | 31.343 | -6.760 | 44.692 | 1.00 | 42.26 | B C |
| ATOM | 3821 | O | ASN | B | 446 | 30.736 | -6.133 | 45.572 | 1.00 | 41.97 | B O |
| ATOM | 3822 | N | PRO | B | 447 | 30.769 | -7.779 | 44.003 | 1.00 | 42.50 | B N |
| ATOM | 3823 | CD | PRO | B | 447 | 31.296 | -8.563 | 42.867 | 1.00 | 41.28 | B C |
| ATOM | 3824 | CA | PRO | B | 447 | 29.391 | -8.192 | 44.309 | 1.00 | 41.27 | B C |
| ATOM | 3825 | CB | PRO | B | 447 | 29.126 | -9.314 | 43.288 | 1.00 | 41.97 | B C |
| ATOM | 3826 | CG | PRO | B | 447 | 30.496 | -9.836 | 42.961 | 1.00 | 41.62 | B C |
| ATOM | 3827 | C | PRO | B | 447 | 29.238 | -8.667 | 45.751 | 1.00 | 38.73 | B C |

Figure 4

| ATOM | 3828 | O | PRO | B | 447 | 28.207 | -8.441 | 46.371 | 1.00 | 38.04 | B | O |
| --- | --- | --- | --- | --- | --- | --- | --- | --- | --- | --- | --- | --- |
| ATOM | 3829 | N | GLU | B | 448 | 30.288 | -9.277 | 46.291 | 1.00 | 36.43 | B | N |
| ATOM | 3830 | CA | GLU | B | 448 | 30.266 | -9.767 | 47.661 | 1.00 | 36.64 | B | C |
| ATOM | 3831 | CB | GLU | B | 448 | 31.418 | -10.750 | 47.900 | 1.00 | 38.56 | B | C |
| ATOM | 3832 | CG | GLU | B | 448 | 31.334 | -12.021 | 47.088 | 1.00 | 41.25 | B | C |
| ATOM | 3833 | CD | GLU | B | 448 | 32.585 | -12.877 | 47.198 | 1.00 | 42.39 | B | C |
| ATOM | 3834 | OE1 | GLU | B | 448 | 33.619 | -12.389 | 47.693 | 1.00 | 44.95 | B | O |
| ATOM | 3835 | OE2 | GLU | B | 448 | 32.542 | -14.049 | 46.783 | 1.00 | 43.75 | B | O |
| ATOM | 3836 | C | GLU | B | 448 | 30.322 | -8.634 | 48.691 | 1.00 | 34.80 | B | C |
| ATOM | 3837 | O | GLU | B | 448 | 29.717 | -8.731 | 49.759 | 1.00 | 33.88 | B | O |
| ATOM | 3838 | N | VAL | B | 449 | 31.078 | -7.580 | 48.388 | 1.00 | 33.75 | B | N |
| ATOM | 3839 | CA | VAL | B | 449 | 31.187 | -6.432 | 49.292 | 1.00 | 31.12 | B | C |
| ATOM | 3840 | CB | VAL | B | 449 | 32.236 | -5.374 | 48.799 | 1.00 | 30.06 | B | C |
| ATOM | 3841 | CG1 | VAL | B | 449 | 32.047 | -4.038 | 49.526 | 1.00 | 27.51 | B | C |
| ATOM | 3842 | CG2 | VAL | B | 449 | 33.652 | -5.888 | 49.039 | 1.00 | 28.28 | B | C |
| ATOM | 3843 | C | VAL | B | 449 | 29.814 | -5.799 | 49.385 | 1.00 | 30.25 | B | C |
| ATOM | 3844 | O | VAL | B | 449 | 29.409 | -5.340 | 50.455 | 1.00 | 28.49 | B | O |
| ATOM | 3845 | N | ILE | B | 450 | 29.110 | -5.793 | 48.250 | 1.00 | 31.26 | B | N |
| ATOM | 3846 | CA | ILE | B | 450 | 27.752 | -5.251 | 48.154 | 1.00 | 32.41 | B | C |
| ATOM | 3847 | CB | ILE | B | 450 | 27.248 | -5.247 | 46.690 | 1.00 | 34.00 | B | C |
| ATOM | 3848 | CG2 | ILE | B | 450 | 25.794 | -4.756 | 46.617 | 1.00 | 34.26 | B | C |
| ATOM | 3849 | CG1 | ILE | B | 450 | 28.163 | -4.383 | 45.826 | 1.00 | 35.40 | B | C |
| ATOM | 3850 | CD1 | ILE | B | 450 | 28.313 | -2.985 | 46.335 | 1.00 | 37.85 | B | C |
| ATOM | 3851 | C | ILE | B | 450 | 26.750 | -6.025 | 49.027 | 1.00 | 30.33 | B | C |
| ATOM | 3852 | O | ILE | B | 450 | 26.002 | -5.419 | 49.798 | 1.00 | 30.13 | B | O |
| ATOM | 3853 | N | GLN | B | 451 | 26.755 | -7.355 | 48.935 | 1.00 | 29.45 | B | N |
| ATOM | 3854 | CA | GLN | B | 451 | 25.832 | -8.144 | 49.744 | 1.00 | 30.23 | B | C |
| ATOM | 3855 | CB | GLN | B | 451 | 25.560 | -9.541 | 49.145 | 1.00 | 32.65 | B | C |
| ATOM | 3856 | CG | GLN | B | 451 | 26.759 | -10.460 | 48.971 | 1.00 | 37.73 | B | C |
| ATOM | 3857 | CD | GLN | B | 451 | 26.612 | -11.405 | 47.775 | 1.00 | 38.93 | B | C |
| ATOM | 3858 | OE1 | GLN | B | 451 | 27.043 | -12.563 | 47.821 | 1.00 | 40.50 | B | O |
| ATOM | 3859 | NE2 | GLN | B | 451 | 26.043 | -10.897 | 46.684 | 1.00 | 40.00 | B | N |
| ATOM | 3860 | C | GLN | B | 451 | 26.178 | -8.195 | 51.229 | 1.00 | 27.54 | B | C |
| ATOM | 3861 | O | GLN | B | 451 | 25.308 | -8.494 | 52.043 | 1.00 | 27.12 | B | O |
| ATOM | 3862 | N | ASN | B | 452 | 27.429 | -7.873 | 51.575 | 1.00 | 25.73 | B | N |
| ATOM | 3863 | CA | ASN | B | 452 | 27.886 | -7.826 | 52.970 | 1.00 | 23.63 | B | C |
| ATOM | 3864 | CB | ASN | B | 452 | 29.399 | -7.989 | 53.061 | 1.00 | 25.30 | B | C |
| ATOM | 3865 | CG | ASN | B | 452 | 29.814 | -9.417 | 53.264 | 1.00 | 27.09 | B | C |
| ATOM | 3866 | OD1 | ASN | B | 452 | 30.085 | -9.843 | 54.384 | 1.00 | 28.97 | B | O |
| ATOM | 3867 | ND2 | ASN | B | 452 | 29.872 | -10.176 | 52.174 | 1.00 | 27.68 | B | N |
| ATOM | 3868 | C | ASN | B | 452 | 27.517 | -6.462 | 53.547 | 1.00 | 22.60 | B | C |
| ATOM | 3869 | O | ASN | B | 452 | 27.121 | -6.369 | 54.697 | 1.00 | 22.31 | B | O |
| ATOM | 3870 | N | LEU | B | 453 | 27.692 | -5.404 | 52.753 | 1.00 | 21.64 | B | N |
| ATOM | 3871 | CA | LEU | B | 453 | 27.343 | -4.051 | 53.168 | 1.00 | 22.35 | B | C |
| ATOM | 3872 | CB | LEU | B | 453 | 27.792 | -3.018 | 52.134 | 1.00 | 23.27 | B | C |
| ATOM | 3873 | CG | LEU | B | 453 | 29.249 | -2.563 | 52.189 | 1.00 | 24.29 | B | C |
| ATOM | 3874 | CD1 | LEU | B | 453 | 29.410 | -1.396 | 51.231 | 1.00 | 25.84 | B | C |
| ATOM | 3875 | CD2 | LEU | B | 453 | 29.634 | -2.127 | 53.603 | 1.00 | 24.25 | B | C |
| ATOM | 3876 | C | LEU | B | 453 | 25.841 | -3.956 | 53.343 | 1.00 | 23.16 | B | C |
| ATOM | 3877 | O | LEU | B | 453 | 25.355 | -3.150 | 54.135 | 1.00 | 22.58 | B | O |
| ATOM | 3878 | N | GLU | B | 454 | 25.106 | -4.728 | 52.548 | 1.00 | 23.24 | B | N |
| ATOM | 3879 | CA | GLU | B | 454 | 23.656 | -4.770 | 52.660 | 1.00 | 26.50 | B | C |
| ATOM | 3880 | CB | GLU | B | 454 | 23.053 | -5.735 | 51.641 | 1.00 | 30.40 | B | C |
| ATOM | 3881 | CG | GLU | B | 454 | 22.894 | -5.197 | 50.214 | 1.00 | 35.60 | B | C |
| ATOM | 3882 | CD | GLU | B | 454 | 22.614 | -6.312 | 49.190 | 1.00 | 38.23 | B | C |
| ATOM | 3883 | OE1 | GLU | B | 454 | 22.790 | -6.057 | 47.970 | 1.00 | 38.98 | B | O |
| ATOM | 3884 | OE2 | GLU | B | 454 | 22.243 | -7.444 | 49.615 | 1.00 | 39.46 | B | O |
| ATOM | 3885 | C | GLU | B | 454 | 23.312 | -5.271 | 54.058 | 1.00 | 24.97 | B | C |
| ATOM | 3886 | O | GLU | B | 454 | 22.346 | -4.818 | 54.658 | 1.00 | 24.35 | B | O |
| ATOM | 3887 | N | ARG | B | 455 | 24.107 | -6.218 | 54.552 | 1.00 | 24.06 | B | N |

Figure 4

| | | | | | | | | | | | |
|---|---|---|---|---|---|---|---|---|---|---|---|
| ATOM | 3888 | CA   | ARG | B | 455 | 23.923 | -6.810  | 55.865 | 1.00 | 23.80 | B | C |
| ATOM | 3889 | CB   | ARG | B | 455 | 24.359 | -8.271  | 55.847 | 1.00 | 25.87 | B | C |
| ATOM | 3890 | CG   | ARG | B | 455 | 23.620 | -9.210  | 54.882 | 1.00 | 29.54 | B | C |
| ATOM | 3891 | CD   | ARG | B | 455 | 24.209 | -10.640 | 55.001 | 1.00 | 33.07 | B | C |
| ATOM | 3892 | NE   | ARG | B | 455 | 25.647 | -10.537 | 55.246 | 1.00 | 38.56 | B | N |
| ATOM | 3893 | CZ   | ARG | B | 455 | 26.259 | -10.859 | 56.390 | 1.00 | 39.36 | B | C |
| ATOM | 3894 | NH1  | ARG | B | 455 | 25.565 | -11.361 | 57.403 | 1.00 | 38.59 | B | N |
| ATOM | 3895 | NH2  | ARG | B | 455 | 27.524 | -10.483 | 56.598 | 1.00 | 39.05 | B | N |
| ATOM | 3896 | C    | ARG | B | 455 | 24.655 | -6.067  | 56.995 | 1.00 | 21.83 | B | C |
| ATOM | 3897 | O    | ARG | B | 455 | 24.783 | -6.573  | 58.111 | 1.00 | 19.50 | B | O |
| ATOM | 3898 | N    | GLY | B | 456 | 25.144 | -4.873  | 56.687 | 1.00 | 22.91 | B | N |
| ATOM | 3899 | CA   | GLY | B | 456 | 25.850 | -4.050  | 57.658 | 1.00 | 21.54 | B | C |
| ATOM | 3900 | C    | GLY | B | 456 | 27.281 | -4.424  | 57.993 | 1.00 | 21.27 | B | C |
| ATOM | 3901 | O    | GLY | B | 456 | 27.821 | -3.954  | 58.991 | 1.00 | 21.75 | B | O |
| ATOM | 3902 | N    | TYR | B | 457 | 27.913 | -5.244  | 57.162 | 1.00 | 22.36 | B | N |
| ATOM | 3903 | CA   | TYR | B | 457 | 29.286 | -5.674  | 57.411 | 1.00 | 21.28 | B | C |
| ATOM | 3904 | CB   | TYR | B | 457 | 29.701 | -6.698  | 56.364 | 1.00 | 20.55 | B | C |
| ATOM | 3905 | CG   | TYR | B | 457 | 31.087 | -7.261  | 56.526 | 1.00 | 21.22 | B | C |
| ATOM | 3906 | CD1  | TYR | B | 457 | 31.302 | -8.500  | 57.148 | 1.00 | 20.56 | B | C |
| ATOM | 3907 | CE1  | TYR | B | 457 | 32.590 | -9.029  | 57.252 | 1.00 | 20.93 | B | C |
| ATOM | 3908 | CD2  | TYR | B | 457 | 32.195 | -6.568  | 56.020 | 1.00 | 22.40 | B | C |
| ATOM | 3909 | CE2  | TYR | B | 457 | 33.493 | -7.086  | 56.119 | 1.00 | 21.20 | B | C |
| ATOM | 3910 | CZ   | TYR | B | 457 | 33.678 | -8.307  | 56.732 | 1.00 | 21.45 | B | C |
| ATOM | 3911 | OH   | TYR | B | 457 | 34.955 | -8.799  | 56.817 | 1.00 | 21.02 | B | O |
| ATOM | 3912 | C    | TYR | B | 457 | 30.329 | -4.569  | 57.499 | 1.00 | 21.59 | B | C |
| ATOM | 3913 | O    | TYR | B | 457 | 30.281 | -3.574  | 56.770 | 1.00 | 21.74 | B | O |
| ATOM | 3914 | N    | ARG | B | 458 | 31.259 | -4.750  | 58.437 | 1.00 | 22.46 | B | N |
| ATOM | 3915 | CA   | ARG | B | 458 | 32.371 | -3.836  | 58.648 | 1.00 | 22.12 | B | C |
| ATOM | 3916 | CB   | ARG | B | 458 | 32.205 | -2.991  | 59.919 | 1.00 | 20.92 | B | C |
| ATOM | 3917 | CG   | ARG | B | 458 | 31.071 | -1.987  | 59.885 | 1.00 | 19.39 | B | C |
| ATOM | 3918 | CD   | ARG | B | 458 | 31.181 | -1.042  | 58.702 | 1.00 | 19.40 | B | C |
| ATOM | 3919 | NE   | ARG | B | 458 | 30.100 | -0.059  | 58.679 | 1.00 | 18.66 | B | N |
| ATOM | 3920 | CZ   | ARG | B | 458 | 29.016 | -0.135  | 57.913 | 1.00 | 18.51 | B | C |
| ATOM | 3921 | NH1  | ARG | B | 458 | 28.859 | -1.154  | 57.086 | 1.00 | 20.42 | B | N |
| ATOM | 3922 | NH2  | ARG | B | 458 | 28.064 | 0.786   | 58.000 | 1.00 | 17.89 | B | N |
| ATOM | 3923 | C    | ARG | B | 458 | 33.629 | -4.682  | 58.760 | 1.00 | 23.26 | B | C |
| ATOM | 3924 | O    | ARG | B | 458 | 33.609 | -5.776  | 59.330 | 1.00 | 23.14 | B | O |
| ATOM | 3925 | N    | MET | B | 459 | 34.709 | -4.198  | 58.157 | 1.00 | 25.41 | B | N |
| ATOM | 3926 | CA   | MET | B | 459 | 35.996 | -4.875  | 58.217 | 1.00 | 25.27 | B | C |
| ATOM | 3927 | CB   | MET | B | 459 | 37.045 | -4.118  | 57.410 | 1.00 | 25.60 | B | C |
| ATOM | 3928 | CG   | MET | B | 459 | 36.972 | -4.335  | 55.917 | 1.00 | 28.41 | B | C |
| ATOM | 3929 | SD   | MET | B | 459 | 38.358 | -3.547  | 55.109 | 1.00 | 30.98 | B | S |
| ATOM | 3930 | CE   | MET | B | 459 | 37.761 | -1.879  | 54.870 | 1.00 | 28.47 | B | C |
| ATOM | 3931 | C    | MET | B | 459 | 36.469 | -4.918  | 59.655 | 1.00 | 24.88 | B | C |
| ATOM | 3932 | O    | MET | B | 459 | 36.229 | -3.978  | 60.435 | 1.00 | 23.10 | B | O |
| ATOM | 3933 | N    | VAL | B | 460 | 37.150 | -6.007  | 60.004 | 1.00 | 27.28 | B | N |
| ATOM | 3934 | CA   | VAL | B | 460 | 37.689 | -6.169  | 61.357 | 1.00 | 28.77 | B | C |
| ATOM | 3935 | CB   | VAL | B | 460 | 37.918 | -7.658  | 61.688 | 1.00 | 28.41 | B | C |
| ATOM | 3936 | CG1  | VAL | B | 460 | 36.631 | -8.427  | 61.449 | 1.00 | 28.73 | B | C |
| ATOM | 3937 | CG2  | VAL | B | 460 | 39.042 | -8.239  | 60.834 | 1.00 | 27.40 | B | C |
| ATOM | 3938 | C    | VAL | B | 460 | 38.982 | -5.349  | 61.491 | 1.00 | 29.21 | B | C |
| ATOM | 3939 | O    | VAL | B | 460 | 39.455 | -4.788  | 60.503 | 1.00 | 28.96 | B | O |
| ATOM | 3940 | N    | ARG | B | 461 | 39.532 | -5.233  | 62.699 | 1.00 | 28.87 | B | N |
| ATOM | 3941 | CA   | ARG | B | 461 | 40.759 | -4.454  | 62.887 | 1.00 | 28.19 | B | C |
| ATOM | 3942 | CB   | ARG | B | 461 | 41.066 | -4.291  | 64.371 | 1.00 | 29.37 | B | C |
| ATOM | 3943 | CG   | ARG | B | 461 | 42.043 | -3.169  | 64.694 | 1.00 | 31.40 | B | C |
| ATOM | 3944 | CD   | ARG | B | 461 | 42.433 | -3.183  | 66.155 | 1.00 | 34.60 | B | C |
| ATOM | 3945 | NE   | ARG | B | 461 | 42.843 | -4.522  | 66.572 | 1.00 | 39.27 | B | N |
| ATOM | 3946 | CZ   | ARG | B | 461 | 44.002 | -5.095  | 66.245 | 1.00 | 42.75 | B | C |
| ATOM | 3947 | NH1  | ARG | B | 461 | 44.914 | -4.450  | 65.505 | 1.00 | 44.03 | B | N |

Figure 4

| ATOM | 3948 | NH2 | ARG | B | 461 | 44.214 | -6.364 | 66.573 | 1.00 | 44.44 | B | N |
|------|------|-----|-----|---|-----|--------|--------|--------|------|-------|---|---|
| ATOM | 3949 | C | ARG | B | 461 | 41.935 | -5.105 | 62.155 | 1.00 | 27.96 | B | C |
| ATOM | 3950 | O | ARG | B | 461 | 42.247 | -6.273 | 62.375 | 1.00 | 25.00 | B | O |
| ATOM | 3951 | N | PRO | B | 462 | 42.569 | -4.358 | 61.232 | 1.00 | 29.44 | B | N |
| ATOM | 3952 | CD | PRO | B | 462 | 42.237 | -2.968 | 60.871 | 1.00 | 29.26 | B | C |
| ATOM | 3953 | CA | PRO | B | 462 | 43.716 | -4.839 | 60.440 | 1.00 | 31.97 | B | C |
| ATOM | 3954 | CB | PRO | B | 462 | 44.056 | -3.634 | 59.544 | 1.00 | 30.75 | B | C |
| ATOM | 3955 | CG | PRO | B | 462 | 42.753 | -2.887 | 59.450 | 1.00 | 30.30 | B | C |
| ATOM | 3956 | C | PRO | B | 462 | 44.914 | -5.200 | 61.316 | 1.00 | 32.88 | B | C |
| ATOM | 3957 | O | PRO | B | 462 | 45.172 | -4.539 | 62.327 | 1.00 | 31.38 | B | O |
| ATOM | 3958 | N | ASP | B | 463 | 45.620 | -6.266 | 60.948 | 1.00 | 36.51 | B | N |
| ATOM | 3959 | CA | ASP | B | 463 | 46.804 | -6.670 | 61.698 | 1.00 | 40.68 | B | C |
| ATOM | 3960 | CB | ASP | B | 463 | 47.533 | -7.839 | 61.012 | 1.00 | 41.49 | B | C |
| ATOM | 3961 | CG | ASP | B | 463 | 46.749 | -9.152 | 61.058 | 1.00 | 41.94 | B | C |
| ATOM | 3962 | OD1 | ASP | B | 463 | 45.857 | -9.296 | 61.918 | 1.00 | 42.58 | B | O |
| ATOM | 3963 | OD2 | ASP | B | 463 | 47.038 | -10.052 | 60.236 | 1.00 | 42.08 | B | O |
| ATOM | 3964 | C | ASP | B | 463 | 47.702 | -5.431 | 61.714 | 1.00 | 43.01 | B | C |
| ATOM | 3965 | O | ASP | B | 463 | 47.918 | -4.791 | 60.672 | 1.00 | 43.80 | B | O |
| ATOM | 3966 | N | ASN | B | 464 | 48.132 | -5.046 | 62.913 | 1.00 | 44.63 | B | N |
| ATOM | 3967 | CA | ASN | B | 464 | 48.983 | -3.875 | 63.104 | 1.00 | 45.52 | B | C |
| ATOM | 3968 | CB | ASN | B | 464 | 50.284 | -4.036 | 62.328 | 1.00 | 48.78 | B | C |
| ATOM | 3969 | CG | ASN | B | 464 | 51.138 | -5.150 | 62.889 | 1.00 | 51.28 | B | C |
| ATOM | 3970 | OD1 | ASN | B | 464 | 51.486 | -5.136 | 64.081 | 1.00 | 52.16 | B | O |
| ATOM | 3971 | ND2 | ASN | B | 464 | 51.441 | -6.150 | 62.056 | 1.00 | 51.55 | B | N |
| ATOM | 3972 | C | ASN | B | 464 | 48.317 | -2.529 | 62.821 | 1.00 | 44.56 | B | C |
| ATOM | 3973 | O | ASN | B | 464 | 48.755 | -1.742 | 61.978 | 1.00 | 45.35 | B | O |
| ATOM | 3974 | N | CYS | B | 465 | 47.254 | -2.276 | 63.575 | 1.00 | 41.29 | B | N |
| ATOM | 3975 | CA | CYS | B | 465 | 46.476 | -1.052 | 63.494 | 1.00 | 36.36 | B | C |
| ATOM | 3976 | CB | CYS | B | 465 | 45.227 | -1.275 | 62.628 | 1.00 | 35.30 | B | C |
| ATOM | 3977 | SG | CYS | B | 465 | 43.988 | 0.057 | 62.662 | 1.00 | 31.71 | B | S |
| ATOM | 3978 | C | CYS | B | 465 | 46.056 | -0.827 | 64.939 | 1.00 | 35.28 | B | C |
| ATOM | 3979 | O | CYS | B | 465 | 45.500 | -1.734 | 65.551 | 1.00 | 37.06 | B | O |
| ATOM | 3980 | N | PRO | B | 466 | 46.378 | 0.342 | 65.522 | 1.00 | 32.51 | B | N |
| ATOM | 3981 | CD | PRO | B | 466 | 47.128 | 1.457 | 64.920 | 1.00 | 31.47 | B | C |
| ATOM | 3982 | CA | PRO | B | 466 | 46.008 | 0.647 | 66.906 | 1.00 | 32.10 | B | C |
| ATOM | 3983 | CB | PRO | B | 466 | 46.463 | 2.095 | 67.056 | 1.00 | 31.46 | B | C |
| ATOM | 3984 | CG | PRO | B | 466 | 47.612 | 2.190 | 66.134 | 1.00 | 32.05 | B | C |
| ATOM | 3985 | C | PRO | B | 466 | 44.483 | 0.554 | 67.065 | 1.00 | 33.51 | B | C |
| ATOM | 3986 | O | PRO | B | 466 | 43.760 | 0.702 | 66.091 | 1.00 | 35.07 | B | O |
| ATOM | 3987 | N | GLU | B | 467 | 43.986 | 0.315 | 68.274 | 1.00 | 34.71 | B | N |
| ATOM | 3988 | CA | GLU | B | 467 | 42.540 | 0.223 | 68.474 | 1.00 | 35.31 | B | C |
| ATOM | 3989 | CB | GLU | B | 467 | 42.187 | -0.357 | 69.852 | 1.00 | 36.02 | B | C |
| ATOM | 3990 | CG | GLU | B | 467 | 41.499 | -1.733 | 69.788 | 1.00 | 37.51 | B | C |
| ATOM | 3991 | CD | GLU | B | 467 | 40.073 | -1.692 | 69.211 | 1.00 | 38.04 | B | C |
| ATOM | 3992 | OE1 | GLU | B | 467 | 39.764 | -2.502 | 68.305 | 1.00 | 37.18 | B | O |
| ATOM | 3993 | OE2 | GLU | B | 467 | 39.252 | -0.875 | 69.688 | 1.00 | 37.45 | B | O |
| ATOM | 3994 | C | GLU | B | 467 | 41.866 | 1.563 | 68.294 | 1.00 | 34.61 | B | C |
| ATOM | 3995 | O | GLU | B | 467 | 40.777 | 1.625 | 67.747 | 1.00 | 35.23 | B | O |
| ATOM | 3996 | N | GLU | B | 468 | 42.503 | 2.634 | 68.757 | 1.00 | 35.09 | B | N |
| ATOM | 3997 | CA | GLU | B | 468 | 41.926 | 3.967 | 68.611 | 1.00 | 36.69 | B | C |
| ATOM | 3998 | CB | GLU | B | 468 | 42.789 | 5.041 | 69.293 | 1.00 | 40.85 | B | C |
| ATOM | 3999 | CG | GLU | B | 468 | 42.987 | 4.880 | 70.800 | 1.00 | 44.67 | B | C |
| ATOM | 4000 | CD | GLU | B | 468 | 43.943 | 3.739 | 71.165 | 1.00 | 48.81 | B | C |
| ATOM | 4001 | OE1 | GLU | B | 468 | 44.877 | 3.416 | 70.376 | 1.00 | 48.90 | B | O |
| ATOM | 4002 | OE2 | GLU | B | 468 | 43.755 | 3.165 | 72.264 | 1.00 | 51.49 | B | O |
| ATOM | 4003 | C | GLU | B | 468 | 41.769 | 4.294 | 67.122 | 1.00 | 35.41 | B | C |
| ATOM | 4004 | O | GLU | B | 468 | 40.759 | 4.890 | 66.715 | 1.00 | 34.91 | B | O |
| ATOM | 4005 | N | LEU | B | 469 | 42.754 | 3.884 | 66.311 | 1.00 | 31.88 | B | N |
| ATOM | 4006 | CA | LEU | B | 469 | 42.705 | 4.114 | 64.861 | 1.00 | 27.62 | B | C |
| ATOM | 4007 | CB | LEU | B | 469 | 44.035 | 3.741 | 64.184 | 1.00 | 25.02 | B | C |

Figure 4

```
ATOM   4008  CG   LEU B 469      44.080    3.978   62.668  1.00 25.25      B    C
ATOM   4009  CD1  LEU B 469      43.898    5.452   62.348  1.00 24.23      B    C
ATOM   4010  CD2  LEU B 469      45.379    3.473   62.087  1.00 24.27      B    C
ATOM   4011  C    LEU B 469      41.530    3.345   64.225  1.00 25.08      B    C
ATOM   4012  O    LEU B 469      40.868    3.864   63.315  1.00 23.24      B    O
ATOM   4013  N    TYR B 470      41.275    2.125   64.713  1.00 24.16      B    N
ATOM   4014  CA   TYR B 470      40.168    1.297   64.219  1.00 24.77      B    C
ATOM   4015  CB   TYR B 470      40.253   -0.148   64.723  1.00 22.54      B    C
ATOM   4016  CG   TYR B 470      39.100   -1.022   64.265  1.00 23.25      B    C
ATOM   4017  CD1  TYR B 470      38.909   -1.318   62.912  1.00 24.25      B    C
ATOM   4018  CE1  TYR B 470      37.839   -2.123   62.487  1.00 23.89      B    C
ATOM   4019  CD2  TYR B 470      38.185   -1.553   65.187  1.00 24.00      B    C
ATOM   4020  CE2  TYR B 470      37.108   -2.361   64.772  1.00 23.70      B    C
ATOM   4021  CZ   TYR B 470      36.945   -2.635   63.422  1.00 23.70      B    C
ATOM   4022  OH   TYR B 470      35.892   -3.398   62.985  1.00 23.54      B    O
ATOM   4023  C    TYR B 470      38.815    1.899   64.600  1.00 25.73      B    C
ATOM   4024  O    TYR B 470      37.859    1.826   63.825  1.00 28.05      B    O
ATOM   4025  N    GLN B 471      38.719    2.486   65.788  1.00 24.45      B    N
ATOM   4026  CA   GLN B 471      37.458    3.089   66.187  1.00 24.28      B    C
ATOM   4027  CB   GLN B 471      37.443    3.399   67.686  1.00 24.68      B    C
ATOM   4028  CG   GLN B 471      37.327    2.147   68.566  1.00 23.63      B    C
ATOM   4029  CD   GLN B 471      36.225    1.215   68.113  1.00 24.36      B    C
ATOM   4030  OE1  GLN B 471      35.122    1.646   67.771  1.00 24.93      B    O
ATOM   4031  NE2  GLN B 471      36.526   -0.071   68.076  1.00 24.94      B    N
ATOM   4032  C    GLN B 471      37.221    4.335   65.338  1.00 24.43      B    C
ATOM   4033  O    GLN B 471      36.078    4.705   65.045  1.00 21.74      B    O
ATOM   4034  N    LEU B 472      38.317    4.918   64.862  1.00 24.66      B    N
ATOM   4035  CA   LEU B 472      38.232    6.093   64.015  1.00 25.02      B    C
ATOM   4036  CB   LEU B 472      39.581    6.803   63.942  1.00 28.36      B    C
ATOM   4037  CG   LEU B 472      39.522    8.323   63.821  1.00 29.95      B    C
ATOM   4038  CD1  LEU B 472      38.786    8.930   65.014  1.00 28.61      B    C
ATOM   4039  CD2  LEU B 472      40.955    8.853   63.730  1.00 30.96      B    C
ATOM   4040  C    LEU B 472      37.755    5.667   62.627  1.00 23.98      B    C
ATOM   4041  O    LEU B 472      37.047    6.426   61.968  1.00 26.63      B    O
ATOM   4042  N    MET B 473      38.117    4.462   62.186  1.00 21.07      B    N
ATOM   4043  CA   MET B 473      37.654    3.966   60.888  1.00 19.93      B    C
ATOM   4044  CB   MET B 473      38.406    2.699   60.487  1.00 19.55      B    C
ATOM   4045  CG   MET B 473      39.932    2.828   60.412  1.00 18.75      B    C
ATOM   4046  SD   MET B 473      40.648    1.243   60.064  1.00 22.31      B    S
ATOM   4047  CE   MET B 473      42.341    1.704   59.587  1.00 16.61      B    C
ATOM   4048  C    MET B 473      36.157    3.632   61.031  1.00 20.87      B    C
ATOM   4049  O    MET B 473      35.349    3.944   60.155  1.00 17.40      B    O
ATOM   4050  N    ARG B 474      35.792    3.036   62.169  1.00 21.93      B    N
ATOM   4051  CA   ARG B 474      34.395    2.662   62.462  1.00 22.30      B    C
ATOM   4052  CB   ARG B 474      34.299    1.887   63.783  1.00 19.95      B    C
ATOM   4053  CG   ARG B 474      34.922    0.516   63.701  1.00 20.27      B    C
ATOM   4054  CD   ARG B 474      34.280   -0.322   62.598  1.00 23.49      B    C
ATOM   4055  NE   ARG B 474      32.876   -0.617   62.896  1.00 25.88      B    N
ATOM   4056  CZ   ARG B 474      32.434   -1.752   63.436  1.00 25.60      B    C
ATOM   4057  NH1  ARG B 474      33.275   -2.728   63.742  1.00 23.82      B    N
ATOM   4058  NH2  ARG B 474      31.145   -1.903   63.689  1.00 24.99      B    N
ATOM   4059  C    ARG B 474      33.440    3.867   62.456  1.00 20.89      B    C
ATOM   4060  O    ARG B 474      32.277    3.753   62.039  1.00 19.14      B    O
ATOM   4061  N    LEU B 475      33.946    5.013   62.913  1.00 20.76      B    N
ATOM   4062  CA   LEU B 475      33.174    6.241   62.927  1.00 20.87      B    C
ATOM   4063  CB   LEU B 475      33.826    7.295   63.826  1.00 22.06      B    C
ATOM   4064  CG   LEU B 475      33.634    7.104   65.341  1.00 23.94      B    C
ATOM   4065  CD1  LEU B 475      34.200    8.307   66.078  1.00 23.31      B    C
ATOM   4066  CD2  LEU B 475      32.157    6.927   65.685  1.00 22.72      B    C
ATOM   4067  C    LEU B 475      33.017    6.758   61.489  1.00 22.46      B    C
```

Figure 4

| ATOM | 4068 | O | LEU | B | 475 | 31.995 | 7.362 | 61.152 | 1.00 | 22.14 | B | O |
|------|------|------|------|---|-----|--------|-------|--------|------|-------|---|---|
| ATOM | 4069 | N | CYS | B | 476 | 34.026 | 6.523 | 60.645 | 1.00 | 20.65 | B | N |
| ATOM | 4070 | CA | CYS | B | 476 | 33.969 | 6.932 | 59.238 | 1.00 | 21.14 | B | C |
| ATOM | 4071 | CB | CYS | B | 476 | 35.341 | 6.793 | 58.553 | 1.00 | 20.99 | B | C |
| ATOM | 4072 | SG | CYS | B | 476 | 36.677 | 7.900 | 59.136 | 1.00 | 21.78 | B | S |
| ATOM | 4073 | C | CYS | B | 476 | 32.971 | 6.044 | 58.483 | 1.00 | 19.10 | B | C |
| ATOM | 4074 | O | CYS | B | 476 | 32.474 | 6.442 | 57.435 | 1.00 | 17.00 | B | O |
| ATOM | 4075 | N | TRP | B | 477 | 32.764 | 4.820 | 58.989 | 1.00 | 18.44 | B | N |
| ATOM | 4076 | CA | TRP | B | 477 | 31.851 | 3.851 | 58.393 | 1.00 | 18.94 | B | C |
| ATOM | 4077 | CB | TRP | B | 477 | 32.456 | 2.434 | 58.385 | 1.00 | 18.39 | B | C |
| ATOM | 4078 | CG | TRP | B | 477 | 33.804 | 2.313 | 57.716 | 1.00 | 19.63 | B | C |
| ATOM | 4079 | CD2 | TRP | B | 477 | 34.849 | 1.390 | 58.060 | 1.00 | 19.52 | B | C |
| ATOM | 4080 | CE2 | TRP | B | 477 | 35.947 | 1.660 | 57.213 | 1.00 | 20.00 | B | C |
| ATOM | 4081 | CE3 | TRP | B | 477 | 34.958 | 0.352 | 59.007 | 1.00 | 19.31 | B | C |
| ATOM | 4082 | CD1 | TRP | B | 477 | 34.305 | 3.086 | 56.695 | 1.00 | 18.96 | B | C |
| ATOM | 4083 | NE1 | TRP | B | 477 | 35.586 | 2.703 | 56.393 | 1.00 | 19.47 | B | N |
| ATOM | 4084 | CZ2 | TRP | B | 477 | 37.163 | 0.933 | 57.283 | 1.00 | 20.81 | B | C |
| ATOM | 4085 | CZ3 | TRP | B | 477 | 36.166 | -0.373 | 59.081 | 1.00 | 19.44 | B | C |
| ATOM | 4086 | CH2 | TRP | B | 477 | 37.247 | -0.078 | 58.218 | 1.00 | 20.34 | B | C |
| ATOM | 4087 | C | TRP | B | 477 | 30.450 | 3.791 | 59.037 | 1.00 | 17.34 | B | C |
| ATOM | 4088 | O | TRP | B | 477 | 29.790 | 2.754 | 58.960 | 1.00 | 19.84 | B | O |
| ATOM | 4089 | N | LYS | B | 478 | 29.999 | 4.867 | 59.676 | 1.00 | 17.08 | B | N |
| ATOM | 4090 | CA | LYS | B | 478 | 28.653 | 4.857 | 60.261 | 1.00 | 18.97 | B | C |
| ATOM | 4091 | CB | LYS | B | 478 | 28.359 | 6.125 | 61.072 | 1.00 | 18.36 | B | C |
| ATOM | 4092 | CG | LYS | B | 478 | 29.079 | 6.226 | 62.406 | 1.00 | 20.44 | B | C |
| ATOM | 4093 | CD | LYS | B | 478 | 28.768 | 5.077 | 63.358 | 1.00 | 21.35 | B | C |
| ATOM | 4094 | CE | LYS | B | 478 | 27.512 | 5.335 | 64.182 | 1.00 | 23.36 | B | C |
| ATOM | 4095 | NZ | LYS | B | 478 | 27.029 | 4.060 | 64.770 | 1.00 | 26.46 | B | N |
| ATOM | 4096 | C | LYS | B | 478 | 27.670 | 4.761 | 59.099 | 1.00 | 20.05 | B | C |
| ATOM | 4097 | O | LYS | B | 478 | 27.916 | 5.349 | 58.036 | 1.00 | 21.55 | B | O |
| ATOM | 4098 | N | GLU | B | 479 | 26.577 | 4.018 | 59.281 | 1.00 | 21.13 | B | N |
| ATOM | 4099 | CA | GLU | B | 479 | 25.590 | 3.844 | 58.219 | 1.00 | 21.81 | B | C |
| ATOM | 4100 | CB | GLU | B | 479 | 24.468 | 2.918 | 58.700 | 1.00 | 21.21 | B | C |
| ATOM | 4101 | CG | GLU | B | 479 | 23.537 | 2.433 | 57.602 | 1.00 | 21.87 | B | C |
| ATOM | 4102 | CD | GLU | B | 479 | 24.264 | 1.628 | 56.539 | 1.00 | 24.16 | B | C |
| ATOM | 4103 | OE1 | GLU | B | 479 | 25.156 | 0.827 | 56.884 | 1.00 | 25.36 | B | O |
| ATOM | 4104 | OE2 | GLU | B | 479 | 23.973 | 1.802 | 55.346 | 1.00 | 23.99 | B | O |
| ATOM | 4105 | C | GLU | B | 479 | 25.034 | 5.192 | 57.730 | 1.00 | 21.81 | B | C |
| ATOM | 4106 | O | GLU | B | 479 | 24.934 | 5.441 | 56.518 | 1.00 | 19.36 | B | O |
| ATOM | 4107 | N | ARG | B | 480 | 24.736 | 6.077 | 58.679 | 1.00 | 24.03 | B | N |
| ATOM | 4108 | CA | ARG | B | 480 | 24.199 | 7.402 | 58.363 | 1.00 | 25.55 | B | C |
| ATOM | 4109 | CB | ARG | B | 480 | 23.247 | 7.872 | 59.449 | 1.00 | 27.04 | B | C |
| ATOM | 4110 | CG | ARG | B | 480 | 22.013 | 7.073 | 59.594 | 1.00 | 29.38 | B | C |
| ATOM | 4111 | CD | ARG | B | 480 | 21.472 | 7.418 | 60.932 | 1.00 | 35.00 | B | C |
| ATOM | 4112 | NE | ARG | B | 480 | 20.168 | 6.837 | 61.161 | 1.00 | 41.35 | B | N |
| ATOM | 4113 | CZ | ARG | B | 480 | 19.623 | 6.686 | 62.362 | 1.00 | 44.79 | B | C |
| ATOM | 4114 | NH1 | ARG | B | 480 | 20.278 | 7.077 | 63.457 | 1.00 | 46.65 | B | N |
| ATOM | 4115 | NH2 | ARG | B | 480 | 18.413 | 6.144 | 62.463 | 1.00 | 47.20 | B | N |
| ATOM | 4116 | C | ARG | B | 480 | 25.303 | 8.438 | 58.202 | 1.00 | 23.56 | B | C |
| ATOM | 4117 | O | ARG | B | 480 | 26.101 | 8.642 | 59.112 | 1.00 | 23.44 | B | O |
| ATOM | 4118 | N | PRO | B | 481 | 25.277 | 9.181 | 57.082 | 1.00 | 22.95 | B | N |
| ATOM | 4119 | CD | PRO | B | 481 | 24.211 | 9.158 | 56.063 | 1.00 | 23.26 | B | C |
| ATOM | 4120 | CA | PRO | B | 481 | 26.250 | 10.210 | 56.749 | 1.00 | 23.29 | B | C |
| ATOM | 4121 | CB | PRO | B | 481 | 25.614 | 10.877 | 55.518 | 1.00 | 23.17 | B | C |
| ATOM | 4122 | CG | PRO | B | 481 | 24.881 | 9.794 | 54.887 | 1.00 | 22.08 | B | C |
| ATOM | 4123 | C | PRO | B | 481 | 26.493 | 11.212 | 57.876 | 1.00 | 23.88 | B | C |
| ATOM | 4124 | O | PRO | B | 481 | 27.647 | 11.588 | 58.143 | 1.00 | 22.61 | B | O |
| ATOM | 4125 | N | GLU | B | 482 | 25.414 | 11.626 | 58.542 | 1.00 | 22.42 | B | N |
| ATOM | 4126 | CA | GLU | B | 482 | 25.489 | 12.608 | 59.623 | 1.00 | 20.83 | B | C |
| ATOM | 4127 | CB | GLU | B | 482 | 24.076 | 13.105 | 59.999 | 1.00 | 22.56 | B | C |

Figure 4

| ATOM | 4128 | CG  | GLU | B | 482 | 23.198 | 12.102 | 60.762 | 1.00 | 22.87 | B | C |
| ---- | ---- | --- | --- | - | --- | ------ | ------ | ------ | ---- | ----- | - | - |
| ATOM | 4129 | CD  | GLU | B | 482 | 22.289 | 11.269 | 59.881 | 1.00 | 24.98 | B | C |
| ATOM | 4130 | OE1 | GLU | B | 482 | 22.509 | 11.185 | 58.642 | 1.00 | 24.82 | B | O |
| ATOM | 4131 | OE2 | GLU | B | 482 | 21.330 | 10.698 | 60.446 | 1.00 | 26.49 | B | O |
| ATOM | 4132 | C   | GLU | B | 482 | 26.241 | 12.119 | 60.870 | 1.00 | 19.35 | B | C |
| ATOM | 4133 | O   | GLU | B | 482 | 26.694 | 12.923 | 61.686 | 1.00 | 20.45 | B | O |
| ATOM | 4134 | N   | ASP | B | 483 | 26.357 | 10.805 | 61.023 | 1.00 | 19.48 | B | N |
| ATOM | 4135 | CA  | ASP | B | 483 | 27.074 | 10.238 | 62.163 | 1.00 | 20.25 | B | C |
| ATOM | 4136 | CB  | ASP | B | 483 | 26.475 |  8.890 | 62.539 | 1.00 | 21.20 | B | C |
| ATOM | 4137 | CG  | ASP | B | 483 | 25.087 |  9.020 | 63.116 | 1.00 | 24.34 | B | C |
| ATOM | 4138 | OD1 | ASP | B | 483 | 24.842 | 10.001 | 63.844 | 1.00 | 24.39 | B | O |
| ATOM | 4139 | OD2 | ASP | B | 483 | 24.239 |  8.145 | 62.844 | 1.00 | 24.14 | B | O |
| ATOM | 4140 | C   | ASP | B | 483 | 28.585 | 10.092 | 61.925 | 1.00 | 19.21 | B | C |
| ATOM | 4141 | O   | ASP | B | 483 | 29.330 |  9.712 | 62.836 | 1.00 | 17.70 | B | O |
| ATOM | 4142 | N   | ARG | B | 484 | 29.022 | 10.368 | 60.693 | 1.00 | 19.85 | B | N |
| ATOM | 4143 | CA  | ARG | B | 484 | 30.433 | 10.302 | 60.299 | 1.00 | 19.35 | B | C |
| ATOM | 4144 | CB  | ARG | B | 484 | 30.545 | 10.011 | 58.801 | 1.00 | 18.39 | B | C |
| ATOM | 4145 | CG  | ARG | B | 484 | 29.874 |  8.709 | 58.412 | 1.00 | 17.40 | B | C |
| ATOM | 4146 | CD  | ARG | B | 484 | 29.954 |  8.503 | 56.927 | 1.00 | 18.59 | B | C |
| ATOM | 4147 | NE  | ARG | B | 484 | 29.097 |  7.402 | 56.514 | 1.00 | 20.70 | B | N |
| ATOM | 4148 | CZ  | ARG | B | 484 | 28.434 |  7.349 | 55.360 | 1.00 | 21.60 | B | C |
| ATOM | 4149 | NH1 | ARG | B | 484 | 28.532 |  8.341 | 54.487 | 1.00 | 21.17 | B | N |
| ATOM | 4150 | NH2 | ARG | B | 484 | 27.631 |  6.312 | 55.102 | 1.00 | 21.02 | B | N |
| ATOM | 4151 | C   | ARG | B | 484 | 31.113 | 11.626 | 60.653 | 1.00 | 18.91 | B | C |
| ATOM | 4152 | O   | ARG | B | 484 | 30.531 | 12.699 | 60.506 | 1.00 | 18.81 | B | O |
| ATOM | 4153 | N   | PRO | B | 485 | 32.370 | 11.572 | 61.104 | 1.00 | 18.48 | B | N |
| ATOM | 4154 | CD  | PRO | B | 485 | 33.229 | 10.387 | 61.193 | 1.00 | 19.71 | B | C |
| ATOM | 4155 | CA  | PRO | B | 485 | 33.116 | 12.772 | 61.482 | 1.00 | 19.62 | B | C |
| ATOM | 4156 | CB  | PRO | B | 485 | 34.445 | 12.210 | 62.010 | 1.00 | 20.76 | B | C |
| ATOM | 4157 | CG  | PRO | B | 485 | 34.170 | 10.779 | 62.282 | 1.00 | 21.41 | B | C |
| ATOM | 4158 | C   | PRO | B | 485 | 33.397 | 13.714 | 60.315 | 1.00 | 19.74 | B | C |
| ATOM | 4159 | O   | PRO | B | 485 | 33.305 | 13.327 | 59.153 | 1.00 | 21.04 | B | O |
| ATOM | 4160 | N   | THR | B | 486 | 33.712 | 14.958 | 60.635 | 1.00 | 18.78 | B | N |
| ATOM | 4161 | CA  | THR | B | 486 | 34.081 | 15.908 | 59.619 | 1.00 | 20.90 | B | C |
| ATOM | 4162 | CB  | THR | B | 486 | 33.974 | 17.375 | 60.119 | 1.00 | 19.71 | B | C |
| ATOM | 4163 | OG1 | THR | B | 486 | 34.739 | 17.542 | 61.311 | 1.00 | 20.73 | B | O |
| ATOM | 4164 | CG2 | THR | B | 486 | 32.543 | 17.755 | 60.377 | 1.00 | 17.95 | B | C |
| ATOM | 4165 | C   | THR | B | 486 | 35.561 | 15.596 | 59.373 | 1.00 | 22.01 | B | C |
| ATOM | 4166 | O   | THR | B | 486 | 36.192 | 14.868 | 60.139 | 1.00 | 23.24 | B | O |
| ATOM | 4167 | N   | PHE | B | 487 | 36.097 | 16.080 | 58.267 | 1.00 | 24.01 | B | N |
| ATOM | 4168 | CA  | PHE | B | 487 | 37.507 | 15.871 | 57.965 | 1.00 | 23.18 | B | C |
| ATOM | 4169 | CB  | PHE | B | 487 | 37.793 | 16.140 | 56.494 | 1.00 | 21.05 | B | C |
| ATOM | 4170 | CG  | PHE | B | 487 | 37.497 | 14.975 | 55.603 | 1.00 | 20.99 | B | C |
| ATOM | 4171 | CD1 | PHE | B | 487 | 38.269 | 13.817 | 55.676 | 1.00 | 20.00 | B | C |
| ATOM | 4172 | CD2 | PHE | B | 487 | 36.488 | 15.049 | 54.646 | 1.00 | 21.24 | B | C |
| ATOM | 4173 | CE1 | PHE | B | 487 | 38.053 | 12.762 | 54.816 | 1.00 | 18.42 | B | C |
| ATOM | 4174 | CE2 | PHE | B | 487 | 36.267 | 13.991 | 53.778 | 1.00 | 19.18 | B | C |
| ATOM | 4175 | CZ  | PHE | B | 487 | 37.057 | 12.845 | 53.866 | 1.00 | 19.20 | B | C |
| ATOM | 4176 | C   | PHE | B | 487 | 38.291 | 16.829 | 58.850 | 1.00 | 25.30 | B | C |
| ATOM | 4177 | O   | PHE | B | 487 | 39.481 | 16.625 | 59.086 | 1.00 | 25.97 | B | O |
| ATOM | 4178 | N   | ASP | B | 488 | 37.607 | 17.874 | 59.333 | 1.00 | 26.54 | B | N |
| ATOM | 4179 | CA  | ASP | B | 488 | 38.198 | 18.855 | 60.238 | 1.00 | 28.59 | B | C |
| ATOM | 4180 | CB  | ASP | B | 488 | 37.229 | 20.023 | 60.455 | 1.00 | 32.01 | B | C |
| ATOM | 4181 | CG  | ASP | B | 488 | 37.750 | 21.061 | 61.454 | 1.00 | 35.18 | B | C |
| ATOM | 4182 | OD1 | ASP | B | 488 | 38.969 | 21.328 | 61.452 | 1.00 | 36.71 | B | O |
| ATOM | 4183 | OD2 | ASP | B | 488 | 36.938 | 21.623 | 62.234 | 1.00 | 36.16 | B | O |
| ATOM | 4184 | C   | ASP | B | 488 | 38.515 | 18.143 | 61.562 | 1.00 | 28.46 | B | C |
| ATOM | 4185 | O   | ASP | B | 488 | 39.548 | 18.391 | 62.175 | 1.00 | 29.40 | B | O |
| ATOM | 4186 | N   | TYR | B | 489 | 37.639 | 17.228 | 61.978 | 1.00 | 26.86 | B | N |
| ATOM | 4187 | CA  | TYR | B | 489 | 37.864 | 16.468 | 63.193 | 1.00 | 24.98 | B | C |

Figure 4

| | | | | | | | | | | | |
|---|---|---|---|---|---|---|---|---|---|---|---|
| ATOM | 4188 | CB | TYR | B | 489 | 36.575 | 15.811 | 63.690 | 1.00 | 23.64 | B C |
| ATOM | 4189 | CG | TYR | B | 489 | 36.826 | 14.775 | 64.774 | 1.00 | 24.49 | B C |
| ATOM | 4190 | CD1 | TYR | B | 489 | 37.138 | 15.158 | 66.077 | 1.00 | 23.40 | B C |
| ATOM | 4191 | CE1 | TYR | B | 489 | 37.418 | 14.212 | 67.061 | 1.00 | 23.83 | B C |
| ATOM | 4192 | CD2 | TYR | B | 489 | 36.800 | 13.407 | 64.484 | 1.00 | 25.36 | B C |
| ATOM | 4193 | CE2 | TYR | B | 489 | 37.088 | 12.446 | 65.462 | 1.00 | 24.93 | B C |
| ATOM | 4194 | CZ | TYR | B | 489 | 37.398 | 12.857 | 66.749 | 1.00 | 24.96 | B C |
| ATOM | 4195 | OH | TYR | B | 489 | 37.707 | 11.918 | 67.720 | 1.00 | 26.27 | B O |
| ATOM | 4196 | C | TYR | B | 489 | 38.931 | 15.403 | 62.945 | 1.00 | 25.87 | B C |
| ATOM | 4197 | O | TYR | B | 489 | 39.815 | 15.206 | 63.779 | 1.00 | 26.09 | B O |
| ATOM | 4198 | N | LEU | B | 490 | 38.833 | 14.713 | 61.808 | 1.00 | 25.58 | B N |
| ATOM | 4199 | CA | LEU | B | 490 | 39.783 | 13.667 | 61.435 | 1.00 | 26.18 | B C |
| ATOM | 4200 | CB | LEU | B | 490 | 39.360 | 13.015 | 60.106 | 1.00 | 26.47 | B C |
| ATOM | 4201 | CG | LEU | B | 490 | 38.091 | 12.141 | 60.109 | 1.00 | 24.58 | B C |
| ATOM | 4202 | CD1 | LEU | B | 490 | 37.616 | 11.865 | 58.685 | 1.00 | 22.38 | B C |
| ATOM | 4203 | CD2 | LEU | B | 490 | 38.375 | 10.845 | 60.858 | 1.00 | 24.50 | B C |
| ATOM | 4204 | C | LEU | B | 490 | 41.244 | 14.146 | 61.360 | 1.00 | 27.09 | B C |
| ATOM | 4205 | O | LEU | B | 490 | 42.149 | 13.411 | 61.739 | 1.00 | 27.78 | B O |
| ATOM | 4206 | N | ARG | B | 491 | 41.468 | 15.364 | 60.862 | 1.00 | 28.94 | B N |
| ATOM | 4207 | CA | ARG | B | 491 | 42.814 | 15.945 | 60.768 | 1.00 | 30.11 | B C |
| ATOM | 4208 | CB | ARG | B | 491 | 42.776 | 17.260 | 59.979 | 1.00 | 31.74 | B C |
| ATOM | 4209 | CG | ARG | B | 491 | 44.041 | 18.086 | 60.096 | 1.00 | 36.66 | B C |
| ATOM | 4210 | CD | ARG | B | 491 | 43.797 | 19.556 | 59.738 | 1.00 | 41.42 | B C |
| ATOM | 4211 | NE | ARG | B | 491 | 42.646 | 20.138 | 60.445 | 1.00 | 46.39 | B N |
| ATOM | 4212 | CZ | ARG | B | 491 | 42.620 | 20.470 | 61.740 | 1.00 | 48.20 | B C |
| ATOM | 4213 | NH1 | ARG | B | 491 | 43.682 | 20.285 | 62.523 | 1.00 | 49.87 | B N |
| ATOM | 4214 | NH2 | ARG | B | 491 | 41.527 | 21.014 | 62.257 | 1.00 | 47.58 | B N |
| ATOM | 4215 | C | ARG | B | 491 | 43.363 | 16.185 | 62.188 | 1.00 | 29.82 | B C |
| ATOM | 4216 | O | ARG | B | 491 | 44.474 | 15.758 | 62.509 | 1.00 | 29.37 | B O |
| ATOM | 4217 | N | SER | B | 492 | 42.548 | 16.813 | 63.043 | 1.00 | 30.08 | B N |
| ATOM | 4218 | CA | SER | B | 492 | 42.908 | 17.102 | 64.433 | 1.00 | 31.09 | B C |
| ATOM | 4219 | CB | SER | B | 492 | 41.724 | 17.698 | 65.193 | 1.00 | 30.76 | B C |
| ATOM | 4220 | OG | SER | B | 492 | 41.396 | 18.978 | 64.695 | 1.00 | 35.64 | B O |
| ATOM | 4221 | C | SER | B | 492 | 43.355 | 15.858 | 65.174 | 1.00 | 32.21 | B C |
| ATOM | 4222 | O | SER | B | 492 | 44.459 | 15.822 | 65.708 | 1.00 | 32.90 | B O |
| ATOM | 4223 | N | VAL | B | 493 | 42.490 | 14.840 | 65.186 | 1.00 | 32.85 | B N |
| ATOM | 4224 | CA | VAL | B | 493 | 42.747 | 13.576 | 65.873 | 1.00 | 32.14 | B C |
| ATOM | 4225 | CB | VAL | B | 493 | 41.471 | 12.669 | 65.904 | 1.00 | 32.69 | B C |
| ATOM | 4226 | CG1 | VAL | B | 493 | 41.029 | 12.303 | 64.501 | 1.00 | 33.40 | B C |
| ATOM | 4227 | CG2 | VAL | B | 493 | 41.736 | 11.401 | 66.712 | 1.00 | 33.49 | B C |
| ATOM | 4228 | C | VAL | B | 493 | 43.949 | 12.802 | 65.334 | 1.00 | 32.90 | B C |
| ATOM | 4229 | O | VAL | B | 493 | 44.704 | 12.212 | 66.113 | 1.00 | 31.63 | B O |
| ATOM | 4230 | N | LEU | B | 494 | 44.145 | 12.832 | 64.013 | 1.00 | 33.64 | B N |
| ATOM | 4231 | CA | LEU | B | 494 | 45.261 | 12.128 | 63.383 | 1.00 | 34.32 | B C |
| ATOM | 4232 | CB | LEU | B | 494 | 44.990 | 11.902 | 61.887 | 1.00 | 32.86 | B C |
| ATOM | 4233 | CG | LEU | B | 494 | 43.941 | 10.830 | 61.525 | 1.00 | 32.29 | B C |
| ATOM | 4234 | CD1 | LEU | B | 494 | 43.640 | 10.855 | 60.023 | 1.00 | 30.10 | B C |
| ATOM | 4235 | CD2 | LEU | B | 494 | 44.423 | 9.439 | 61.952 | 1.00 | 31.30 | B C |
| ATOM | 4236 | C | LEU | B | 494 | 46.601 | 12.838 | 63.616 | 1.00 | 35.08 | B C |
| ATOM | 4237 | O | LEU | B | 494 | 47.642 | 12.184 | 63.723 | 1.00 | 35.01 | B O |
| ATOM | 4238 | N | GLU | B | 495 | 46.558 | 14.163 | 63.754 | 1.00 | 36.75 | B N |
| ATOM | 4239 | CA | GLU | B | 495 | 47.759 | 14.965 | 64.005 | 1.00 | 38.53 | B C |
| ATOM | 4240 | CB | GLU | B | 495 | 47.442 | 16.458 | 63.900 | 1.00 | 38.02 | B C |
| ATOM | 4241 | CG | GLU | B | 495 | 47.428 | 17.010 | 62.487 | 1.00 | 39.50 | B C |
| ATOM | 4242 | CD | GLU | B | 495 | 47.110 | 18.496 | 62.433 | 1.00 | 40.24 | B C |
| ATOM | 4243 | OE1 | GLU | B | 495 | 47.076 | 19.142 | 63.511 | 1.00 | 41.08 | B O |
| ATOM | 4244 | OE2 | GLU | B | 495 | 46.891 | 19.015 | 61.309 | 1.00 | 40.56 | B O |
| ATOM | 4245 | C | GLU | B | 495 | 48.299 | 14.694 | 65.404 | 1.00 | 40.55 | B C |
| ATOM | 4246 | O | GLU | B | 495 | 49.501 | 14.442 | 65.596 | 1.00 | 40.89 | B O |
| ATOM | 4247 | N | ASP | B | 496 | 47.389 | 14.761 | 66.375 | 1.00 | 41.54 | B N |

Figure 4

| ATOM | 4248 | CA | ASP | B | 496 | 47.701 | 14.559 | 67.782 | 1.00 | 42.71 | B | C |
|------|------|-----|-----|---|-----|--------|--------|--------|------|-------|---|---|
| ATOM | 4249 | CB | ASP | B | 496 | 46.702 | 15.322 | 68.662 | 1.00 | 43.21 | B | C |
| ATOM | 4250 | CG | ASP | B | 496 | 46.788 | 16.835 | 68.502 | 1.00 | 45.04 | B | C |
| ATOM | 4251 | OD1 | ASP | B | 496 | 47.828 | 17.374 | 68.054 | 1.00 | 46.37 | B | O |
| ATOM | 4252 | OD2 | ASP | B | 496 | 45.802 | 17.501 | 68.869 | 1.00 | 46.88 | B | O |
| ATOM | 4253 | C | ASP | B | 496 | 47.676 | 13.105 | 68.214 | 1.00 | 43.10 | B | C |
| ATOM | 4254 | O | ASP | B | 496 | 47.793 | 12.832 | 69.405 | 1.00 | 44.35 | B | O |
| ATOM | 4255 | N | PHE | B | 497 | 47.547 | 12.174 | 67.272 | 1.00 | 43.67 | B | N |
| ATOM | 4256 | CA | PHE | B | 497 | 47.456 | 10.761 | 67.628 | 1.00 | 44.91 | B | C |
| ATOM | 4257 | CB | PHE | B | 497 | 47.479 | 9.870 | 66.382 | 1.00 | 41.83 | B | C |
| ATOM | 4258 | CG | PHE | B | 497 | 46.837 | 8.537 | 66.592 | 1.00 | 40.83 | B | C |
| ATOM | 4259 | CD1 | PHE | B | 497 | 45.485 | 8.366 | 66.364 | 1.00 | 41.75 | B | C |
| ATOM | 4260 | CD2 | PHE | B | 497 | 47.578 | 7.455 | 67.049 | 1.00 | 41.02 | B | C |
| ATOM | 4261 | CE1 | PHE | B | 497 | 44.866 | 7.129 | 66.589 | 1.00 | 41.66 | B | C |
| ATOM | 4262 | CE2 | PHE | B | 497 | 46.980 | 6.213 | 67.279 | 1.00 | 41.09 | B | C |
| ATOM | 4263 | CZ | PHE | B | 497 | 45.615 | 6.047 | 67.049 | 1.00 | 41.01 | B | C |
| ATOM | 4264 | C | PHE | B | 497 | 48.488 | 10.300 | 68.686 | 1.00 | 48.11 | B | C |
| ATOM | 4265 | O | PHE | B | 497 | 48.123 | 9.647 | 69.670 | 1.00 | 49.95 | B | O |
| ATOM | 4266 | N | PHE | B | 498 | 49.756 | 10.672 | 68.505 | 1.00 | 50.04 | B | N |
| ATOM | 4267 | CA | PHE | B | 498 | 50.823 | 10.317 | 69.446 | 1.00 | 51.44 | B | C |
| ATOM | 4268 | CB | PHE | B | 498 | 50.911 | 8.792 | 69.690 | 1.00 | 50.92 | B | C |
| ATOM | 4269 | CG | PHE | B | 498 | 51.097 | 7.946 | 68.439 | 1.00 | 51.07 | B | C |
| ATOM | 4270 | CD1 | PHE | B | 498 | 51.498 | 8.508 | 67.224 | 1.00 | 50.73 | B | C |
| ATOM | 4271 | CD2 | PHE | B | 498 | 50.843 | 6.568 | 68.488 | 1.00 | 50.95 | B | C |
| ATOM | 4272 | CE1 | PHE | B | 498 | 51.640 | 7.708 | 66.088 | 1.00 | 50.51 | B | C |
| ATOM | 4273 | CE2 | PHE | B | 498 | 50.984 | 5.762 | 67.346 | 1.00 | 49.95 | B | C |
| ATOM | 4274 | CZ | PHE | B | 498 | 51.379 | 6.337 | 66.151 | 1.00 | 49.62 | B | C |
| ATOM | 4275 | C | PHE | B | 498 | 52.175 | 10.870 | 69.016 | 1.00 | 52.30 | B | C |
| ATOM | 4276 | O | PHE | B | 498 | 52.393 | 12.067 | 69.282 | 1.00 | 54.54 | B | O |
| ATOM | 4277 | N1 | LIG | B | 500 | 51.172 | 9.826 | 38.271 | 1.00 | 16.92 | B | N |
| ATOM | 4278 | C2 | LIG | B | 500 | 54.219 | 11.524 | 39.662 | 1.00 | 15.69 | B | C |
| ATOM | 4279 | N3 | LIG | B | 500 | 53.435 | 10.468 | 39.215 | 1.00 | 14.95 | B | N |
| ATOM | 4280 | C4 | LIG | B | 500 | 52.140 | 10.691 | 38.761 | 1.00 | 19.51 | B | C |
| ATOM | 4281 | C5 | LIG | B | 500 | 51.613 | 11.978 | 38.754 | 1.00 | 18.34 | B | C |
| ATOM | 4282 | C6 | LIG | B | 500 | 52.408 | 13.038 | 39.213 | 1.00 | 18.09 | B | C |
| ATOM | 4283 | N7 | LIG | B | 500 | 53.697 | 12.805 | 39.661 | 1.00 | 16.77 | B | N |
| ATOM | 4284 | N8 | LIG | B | 500 | 50.058 | 10.581 | 37.954 | 1.00 | 19.06 | B | N |
| ATOM | 4285 | C9 | LIG | B | 500 | 50.323 | 11.905 | 38.247 | 1.00 | 16.67 | B | C |
| ATOM | 4286 | N10 | LIG | B | 500 | 51.933 | 14.300 | 39.234 | 1.00 | 15.37 | B | N |
| ATOM | 4287 | C11 | LIG | B | 500 | 49.222 | 12.827 | 37.944 | 1.00 | 16.81 | B | C |
| ATOM | 4288 | C12 | LIG | B | 500 | 49.480 | 13.937 | 37.117 | 1.00 | 17.35 | B | C |
| ATOM | 4289 | C13 | LIG | B | 500 | 48.457 | 14.836 | 36.793 | 1.00 | 19.29 | B | C |
| ATOM | 4290 | C14 | LIG | B | 500 | 47.163 | 14.639 | 37.291 | 1.00 | 18.96 | B | C |
| ATOM | 4291 | C15 | LIG | B | 500 | 46.888 | 13.531 | 38.126 | 1.00 | 17.02 | B | C |
| ATOM | 4292 | C16 | LIG | B | 500 | 47.923 | 12.619 | 38.455 | 1.00 | 15.16 | B | C |
| ATOM | 4293 | C24 | LIG | B | 500 | 46.072 | 15.617 | 36.929 | 1.00 | 16.99 | B | C |
| ATOM | 4294 | C28 | LIG | B | 500 | 51.287 | 8.343 | 38.230 | 1.00 | 22.83 | B | C |
| ATOM | 4295 | C29 | LIG | B | 500 | 49.989 | 7.666 | 37.782 | 1.00 | 25.14 | B | C |
| ATOM | 4296 | C33 | LIG | B | 500 | 51.615 | 7.726 | 39.590 | 1.00 | 24.71 | B | C |
| ATOM | 4297 | C37 | LIG | B | 500 | 52.376 | 7.863 | 37.260 | 1.00 | 27.58 | B | C |
| ATOM | 4298 | OH2 | H2O | B | 600 | 33.455 | 0.255 | 51.458 | 1.00 | 22.27 | B | O |
| ATOM | 4299 | OH2 | H2O | B | 601 | 29.802 | 19.554 | 61.648 | 1.00 | 65.23 | B | O |
| ATOM | 4300 | OH2 | H2O | B | 602 | 27.136 | -1.687 | 60.328 | 1.00 | 17.30 | B | O |
| ATOM | 4301 | OH2 | H2O | B | 604 | 34.647 | 20.119 | 63.358 | 1.00 | 40.44 | B | O |
| ATOM | 4302 | OH2 | H2O | B | 605 | 22.631 | -2.836 | 58.731 | 1.00 | 33.71 | B | O |
| ATOM | 4303 | OH2 | H2O | B | 606 | 35.513 | 9.269 | 47.605 | 1.00 | 16.51 | B | O |
| ATOM | 4304 | OH2 | H2O | B | 607 | 24.965 | 5.904 | 61.510 | 1.00 | 19.48 | B | O |
| ATOM | 4305 | OH2 | H2O | B | 608 | 29.219 | 13.347 | 63.413 | 1.00 | 43.40 | B | O |
| ATOM | 4306 | OH2 | H2O | B | 609 | 27.428 | -8.107 | 58.860 | 1.00 | 22.08 | B | O |
| ATOM | 4307 | OH2 | H2O | B | 610 | 34.314 | -1.940 | 56.508 | 1.00 | 16.30 | B | O |

Figure 4

```
ATOM   4308  OH2 H2O B 611      34.247    4.113   66.847  1.00 22.98       B   O
ATOM   4309  OH2 H2O B 612      29.022   17.018   60.481  1.00 30.40       B   O
ATOM   4310  OH2 H2O B 613      28.054   -5.748   61.279  1.00 52.35       B   O
ATOM   4311  OH2 H2O B 614      37.155   13.389   41.865  1.00 22.32       B   O
ATOM   4312  OH2 H2O B 615      18.964   14.712   64.060  1.00 26.83       B   O
ATOM   4313  OH2 H2O B 616      26.527   15.743   61.097  1.00 27.02       B   O
ATOM   4314  OH2 H2O B 617      30.746   -7.218   60.953  1.00 45.64       B   O
ATOM   4315  OH2 H2O B 618      36.444   -2.187   44.452  1.00 26.13       B   O
ATOM   4316  OH2 H2O B 619      27.203   17.470   56.863  1.00 70.55       B   O
ATOM   4317  OH2 H2O B 620      29.686   -4.469   63.831  1.00 39.37       B   O
ATOM   4318  OH2 H2O B 621      57.972    8.614   39.884  1.00 29.87       B   O
ATOM   4319  OH2 H2O B 622      32.385   21.935   62.481  1.00 41.97       B   O
ATOM   4320  OH2 H2O B 623      24.708   -0.753   59.004  1.00 37.54       B   O
ATOM   4321  OH2 H2O B 624      63.901   10.926   38.344  1.00 31.67       B   O
ATOM   4322  OH2 H2O B 625      48.636   17.312   58.767  1.00 43.97       B   O
ATOM   4323  OH2 H2O B 626      43.594    2.681   46.151  1.00 24.23       B   O
ATOM   4324  OH2 H2O B 627      31.968   16.427   56.872  1.00 17.72       B   O
ATOM   4325  OH2 H2O B 628      32.066    7.086   49.065  1.00 30.51       B   O
ATOM   4326  OH2 H2O B 630      37.232    7.509   67.824  1.00 50.07       B   O
ATOM   4327  OH2 H2O B 631      61.663   23.997   27.060  1.00 34.84       B   O
ATOM   4328  OH2 H2O B 632      33.713   -5.244   62.219  1.00 28.42       B   O
ATOM   4329  OH2 H2O B 633      45.252    9.886   40.736  1.00 43.02       B   O
ATOM   4330  OH2 H2O B 634      45.538   23.404   56.013  1.00 35.25       B   O
ATOM   4331  OH2 H2O B 635      26.830   10.895   51.033  1.00 32.35       B   O
ATOM   4332  OH2 H2O B 636      26.397   10.219   65.915  1.00 26.13       B   O
ATOM   4333  OH2 H2O B 638      20.296   14.304   66.375  1.00 38.83       B   O
ATOM   4334  OH2 H2O B 639      44.317   11.947   68.746  1.00 42.50       B   O
ATOM   4335  OH2 H2O B 640      26.390   -1.157   55.110  1.00 19.85       B   O
ATOM   4336  OH2 H2O B 641      25.628   16.137   58.568  1.00 29.63       B   O
ATOM   4337  OH2 H2O B 642      47.686   22.967   44.943  1.00 26.16       B   O
ATOM   4338  OH2 H2O B 643      54.388    0.057   27.008  1.00 74.81       B   O
ATOM   4339  OH2 H2O B 644      31.549    1.327   61.398  1.00 20.57       B   O
ATOM   4340  OH2 H2O B 645      24.006   -1.154   51.316  1.00 25.88       B   O
ATOM   4341  OH2 H2O B 646      56.550   21.329   19.092  1.00 45.00       B   O
ATOM   4342  OH2 H2O B 647      32.520  -13.370   53.896  1.00 40.68       B   O
ATOM   4343  OH2 H2O B 648      29.229   17.624   50.105  1.00 28.08       B   O
ATOM   4344  OH2 H2O B 649      15.633   16.747   63.431  1.00 48.63       B   O
ATOM   4345  OH2 H2O B 650      40.240   -5.870   57.930  1.00 33.94       B   O
ATOM   4346  OH2 H2O B 651      31.249   25.052   59.718  1.00 30.15       B   O
ATOM   4347  OH2 H2O B 652      26.762    1.840   61.503  1.00 34.78       B   O
ATOM   4348  OH2 H2O B 653      31.668   -0.062   49.310  1.00 20.35       B   O
ATOM   4349  OH2 H2O B 654      32.179   -8.551   65.146  1.00 23.92       B   O
ATOM   4350  OH2 H2O B 655      52.137    2.044   33.560  1.00 30.04       B   O
ATOM   4351  OH2 H2O B 656      32.835   18.889   44.312  1.00 27.31       B   O
ATOM   4352  OH2 H2O B 657      29.735   19.215   54.164  1.00 67.15       B   O
ATOM   4353  OH2 H2O B 658      26.828   -2.187   66.479  1.00 43.25       B   O
ATOM   4354  OH2 H2O B 659      37.962   -5.562   65.142  1.00 25.17       B   O
ATOM   4355  OH2 H2O B 660      51.875    1.150   39.057  1.00 28.14       B   O
ATOM   4356  OH2 H2O B 661      43.008    7.555   36.776  1.00 29.50       B   O
ATOM   4357  OH2 H2O B 662      22.329   11.775   63.979  1.00 52.85       B   O
ATOM   4358  OH2 H2O B 663      34.829  -11.899   56.967  1.00 31.16       B   O
ATOM   4359  OH2 H2O B 664      54.553    0.953   39.970  1.00 34.29       B   O
ATOM   4360  OH2 H2O B 665      30.751   19.918   57.498  1.00 46.32       B   O
ATOM   4361  OH2 H2O B 666      26.311   -1.988   62.798  1.00 46.72       B   O
ATOM   4362  OH2 H2O B 667      37.048   21.591   57.219  1.00 23.91       B   O
ATOM   4363  OH2 H2O B 668      51.238   -0.984   60.682  1.00 38.11       B   O
ATOM   4364  OH2 H2O B 669      33.197   21.459   58.607  1.00 41.07       B   O
ATOM   4365  OH2 H2O B 670      23.065   -1.879   63.109  1.00 54.08       B   O
ATOM   4366  OH2 H2O B 671      25.949   14.537   54.044  1.00 34.48       B   O
ATOM   4367  OH2 H2O B 672      34.301   19.938   41.437  1.00 29.98       B   O
```

Figure 4

```
ATOM   4368  OH2  H2O B 673    61.685   1.701  48.136  1.00 34.63       B   O
ATOM   4369  OH2  H2O B 674    42.754  22.012  56.038  1.00 32.66       B   O
ATOM   4370  OH2  H2O B 675    25.175  -2.267  49.305  1.00 29.24       B   O
ATOM   4371  OH2  H2O B 676    59.545  18.184  41.907  1.00 30.59       B   O
ATOM   4372  OH2  H2O B 677    33.459   7.315  46.535  1.00 27.27       B   O
ATOM   4373  OH2  H2O B 678    22.656   3.570  54.065  1.00 41.24       B   O
ATOM   4374  OH2  H2O B 679    42.848   1.331  44.077  1.00 35.45       B   O
ATOM   4375  OH2  H2O B 680    59.989   6.694  28.740  1.00 41.52       B   O
ATOM   4376  OH2  H2O B 681    21.613   3.602  51.132  1.00 39.04       B   O
ATOM   4377  OH2  H2O B 682    57.370  19.704  40.875  1.00 36.55       B   O
ATOM   4378  OH2  H2O B 683    47.419   5.832  40.599  1.00 33.15       B   O
ATOM   4379  OH2  H2O B 684    42.734  -2.629  53.186  1.00 31.33       B   O
ATOM   4380  OH2  H2O B 685    23.654  -0.496  53.918  1.00 26.50       B   O
ATOM   4381  OH2  H2O B 686    45.767  -1.676  69.565  1.00 38.48       B   O
ATOM   4382  OH2  H2O B 687    26.777  -4.443  64.731  1.00 39.18       B   O
ATOM   4383  OH2  H2O B 688    62.005   9.501  48.743  1.00 43.60       B   O
ATOM   4384  OH2  H2O B 689    23.287  -2.506  47.388  1.00 42.67       B   O
ATOM   4385  OH2  H2O B 690    32.386  17.595  27.622  1.00 42.39       B   O
ATOM   4386  OH2  H2O B 691    46.728  24.139  41.020  1.00 32.60       B   O
ATOM   4387  OH2  H2O B 692    40.402   0.579  42.300  1.00 47.47       B   O
ATOM   4388  OH2  H2O B 693    44.402  -1.059  48.045  1.00 41.13       B   O
ATOM   4389  OH2  H2O B 694    45.496  22.343  43.011  1.00 40.45       B   O
ATOM   4390  OH2  H2O B 695    18.717  12.117  67.367  1.00 41.79       B   O
ATOM   4391  OH2  H2O B 696    59.261   5.842  58.749  1.00 35.43       B   O
ATOM   4392  OH2  H2O B 697    39.501   6.232  68.713  1.00 46.77       B   O
ATOM   4393  OH2  H2O B 698    52.721  10.656  25.886  1.00 42.68       B   O
ATOM   4394  OH2  H2O B 699    23.637   0.624  61.215  1.00 32.84       B   O
ATOM   4395  OH2  H2O B 700    35.000  10.969  68.766  1.00 54.36       B   O
ATOM   4396  OH2  H2O B 701    61.582  10.477  36.815  1.00 32.47       B   O
END
```

Figure 4

```
CRYST1   57.135   44.437  119.881  90.00  90.06  90.00 P21            1
SCALE1      0.017502  0.000000  0.000018        0.00000
SCALE2      0.000000  0.022504  0.000000        0.00000
SCALE3      0.000000  0.000000  0.008342        0.00000
ATOM      1  CB  TRP A 238      17.436  -5.451  27.536  1.00 49.56
ATOM      2  CG  TRP A 238      16.983  -5.803  26.146  1.00 51.18
ATOM      3  CD2 TRP A 238      17.654  -5.499  24.910  1.00 51.17
ATOM      4  CE2 TRP A 238      16.867  -6.034  23.867  1.00 51.84
ATOM      5  CE3 TRP A 238      18.844  -4.833  24.585  1.00 50.52
ATOM      6  CD1 TRP A 238      15.850  -6.483  25.807  1.00 52.07
ATOM      7  NE1 TRP A 238      15.775  -6.628  24.444  1.00 52.75
ATOM      8  CZ2 TRP A 238      17.230  -5.925  22.516  1.00 51.78
ATOM      9  CZ3 TRP A 238      19.207  -4.725  23.242  1.00 50.31
ATOM     10  CH2 TRP A 238      18.400  -5.269  22.225  1.00 50.90
ATOM     11  C   TRP A 238      19.189  -5.620  29.292  1.00 48.29
ATOM     12  O   TRP A 238      19.734  -4.525  29.145  1.00 48.38
ATOM     13  N   TRP A 238      18.095  -7.719  28.345  1.00 47.91
ATOM     14  CA  TRP A 238      18.569  -6.326  28.086  1.00 48.44
ATOM     15  N   GLU A 239      19.069  -6.212  30.481  1.00 48.16
ATOM     16  CA  GLU A 239      19.637  -5.614  31.695  1.00 47.27
ATOM     17  CB  GLU A 239      18.887  -6.040  32.961  1.00 50.05
ATOM     18  CG  GLU A 239      17.836  -5.077  33.454  1.00 53.34
ATOM     19  CD  GLU A 239      16.440  -5.516  33.064  1.00 56.79
ATOM     20  OE1 GLU A 239      15.955  -5.082  31.991  1.00 58.08
ATOM     21  OE2 GLU A 239      15.829  -6.301  33.830  1.00 57.65
ATOM     22  C   GLU A 239      21.081  -6.002  31.893  1.00 45.37
ATOM     23  O   GLU A 239      21.468  -7.142  31.650  1.00 44.63
ATOM     24  N   VAL A 240      21.863  -5.043  32.372  1.00 43.86
ATOM     25  CA  VAL A 240      23.270  -5.263  32.662  1.00 42.20
ATOM     26  CB  VAL A 240      24.192  -4.802  31.508  1.00 41.83
ATOM     27  CG1 VAL A 240      23.886  -5.590  30.242  1.00 40.95
ATOM     28  CG2 VAL A 240      24.062  -3.309  31.274  1.00 41.38
ATOM     29  C   VAL A 240      23.601  -4.490  33.931  1.00 41.37
ATOM     30  O   VAL A 240      22.967  -3.473  34.232  1.00 41.56
ATOM     31  N   PRO A 241      24.536  -5.009  34.736  1.00 39.93
ATOM     32  CD  PRO A 241      25.175  -6.331  34.646  1.00 39.11
ATOM     33  CA  PRO A 241      24.916  -4.331  35.975  1.00 39.46
ATOM     34  CB  PRO A 241      25.853  -5.346  36.628  1.00 38.90
ATOM     35  CG  PRO A 241      25.378  -6.658  36.081  1.00 38.54
ATOM     36  C   PRO A 241      25.635  -3.005  35.686  1.00 39.69
ATOM     37  O   PRO A 241      26.388  -2.900  34.712  1.00 40.04
ATOM     38  N   ARG A 242      25.403  -1.996  36.523  1.00 39.34
ATOM     39  CA  ARG A 242      26.040  -0.689  36.356  1.00 39.38
ATOM     40  CB  ARG A 242      25.568   0.266  37.459  1.00 38.78
ATOM     41  CG  ARG A 242      26.445   1.502  37.646  1.00 40.17
ATOM     42  CD  ARG A 242      25.786   2.570  38.516  1.00 39.38
ATOM     43  NE  ARG A 242      24.673   3.175  37.804  1.00 38.52
ATOM     44  CZ  ARG A 242      23.401   3.012  38.126  1.00 37.61
ATOM     45  NH1 ARG A 242      23.062   2.271  39.164  1.00 38.84
ATOM     46  NH2 ARG A 242      22.468   3.547  37.371  1.00 37.77
ATOM     47  C   ARG A 242      27.579  -0.774  36.321  1.00 39.88
```

Figure 5

| | | | | | | | | | |
|---|---|---|---|---|---|---|---|---|---|
| ATOM | 48 | O | ARG | A | 242 | 28.247 | 0.074 | 35.712 | 1.00 40.19 |
| ATOM | 49 | N | GLU | A | 243 | 28.124 | -1.813 | 36.955 | 1.00 40.01 |
| ATOM | 50 | CA | GLU | A | 243 | 29.567 | -2.077 | 37.033 | 1.00 40.52 |
| ATOM | 51 | CB | GLU | A | 243 | 29.814 | -3.401 | 37.794 | 1.00 43.75 |
| ATOM | 52 | CG | GLU | A | 243 | 29.642 | -3.361 | 39.327 | 1.00 48.92 |
| ATOM | 53 | CD | GLU | A | 243 | 28.209 | -3.064 | 39.806 | 1.00 51.46 |
| ATOM | 54 | OE1 | GLU | A | 243 | 27.414 | -4.027 | 39.945 | 1.00 53.23 |
| ATOM | 55 | OE2 | GLU | A | 243 | 27.893 | -1.875 | 40.079 | 1.00 52.09 |
| ATOM | 56 | C | GLU | A | 243 | 30.233 | -2.179 | 35.648 | 1.00 38.72 |
| ATOM | 57 | O | GLU | A | 243 | 31.415 | -1.852 | 35.476 | 1.00 38.22 |
| ATOM | 58 | N | THR | A | 244 | 29.464 | -2.657 | 34.672 | 1.00 36.80 |
| ATOM | 59 | CA | THR | A | 244 | 29.926 | -2.856 | 33.294 | 1.00 34.57 |
| ATOM | 60 | CB | THR | A | 244 | 29.034 | -3.895 | 32.602 | 1.00 34.40 |
| ATOM | 61 | OG1 | THR | A | 244 | 27.767 | -3.306 | 32.276 | 1.00 33.00 |
| ATOM | 62 | CG2 | THR | A | 244 | 28.796 | -5.068 | 33.544 | 1.00 34.59 |
| ATOM | 63 | C | THR | A | 244 | 29.919 | -1.587 | 32.442 | 1.00 32.93 |
| ATOM | 64 | O | THR | A | 244 | 30.158 | -1.628 | 31.234 | 1.00 31.79 |
| ATOM | 65 | N | LEU | A | 245 | 29.716 | -0.456 | 33.098 | 1.00 32.02 |
| ATOM | 66 | CA | LEU | A | 245 | 29.621 | 0.805 | 32.414 | 1.00 30.91 |
| ATOM | 67 | CB | LEU | A | 245 | 28.137 | 1.127 | 32.271 | 1.00 31.48 |
| ATOM | 68 | CG | LEU | A | 245 | 27.711 | 2.046 | 31.145 | 1.00 31.91 |
| ATOM | 69 | CD1 | LEU | A | 245 | 27.899 | 1.319 | 29.851 | 1.00 34.08 |
| ATOM | 70 | CD2 | LEU | A | 245 | 26.268 | 2.430 | 31.324 | 1.00 32.84 |
| ATOM | 71 | C | LEU | A | 245 | 30.347 | 1.956 | 33.131 | 1.00 30.53 |
| ATOM | 72 | O | LEU | A | 245 | 30.193 | 2.160 | 34.345 | 1.00 30.99 |
| ATOM | 73 | N | LYS | A | 246 | 31.146 | 2.693 | 32.361 | 1.00 28.64 |
| ATOM | 74 | CA | LYS | A | 246 | 31.874 | 3.841 | 32.865 | 1.00 27.09 |
| ATOM | 75 | CB | LYS | A | 246 | 33.389 | 3.588 | 32.836 | 1.00 29.29 |
| ATOM | 76 | CG | LYS | A | 246 | 34.236 | 4.766 | 33.360 | 1.00 30.62 |
| ATOM | 77 | CD | LYS | A | 246 | 35.714 | 4.439 | 33.460 | 1.00 31.16 |
| ATOM | 78 | CE | LYS | A | 246 | 36.278 | 3.946 | 32.149 | 1.00 31.69 |
| ATOM | 79 | NZ | LYS | A | 246. | 37.722 | 3.597 | 32.287 | 1.00 34.05 |
| ATOM | 80 | C | LYS | A | 246 | 31.517 | 5.058 | 31.999 | 1.00 25.34 |
| ATOM | 81 | O | LYS | A | 246 | 31.693 | 5.040 | 30.785 | 1.00 24.31 |
| ATOM | 82 | N | LEU | A | 247 | 30.905 | 6.056 | 32.637 | 1.00 23.80 |
| ATOM | 83 | CA | LEU | A | 247 | 30.507 | 7.298 | 31.999 | 1.00 21.41 |
| ATOM | 84 | CB | LEU | A | 247 | 29.353 | 7.954 | 32.764 | 1.00 19.06 |
| ATOM | 85 | CG | LEU | A | 247 | 27.940 | 7.450 | 32.441 | 1.00 18.69 |
| ATOM | 86 | CD1 | LEU | A | 247 | 27.820 | 5.947 | 32.713 | 1.00 17.59 |
| ATOM | 87 | CD2 | LEU | A | 247 | 26.890 | 8.249 | 33.218 | 1.00 17.07 |
| ATOM | 88 | C | LEU | A | 247 | 31.748 | 8.168 | 32.031 | 1.00 21.89 |
| ATOM | 89 | O | LEU | A | 247 | 32.445 | 8.229 | 33.051 | 1.00 22.94 |
| ATOM | 90 | N | VAL | A | 248 | 32.040 | 8.813 | 30.907 | 1.00 21.02 |
| ATOM | 91 | CA | VAL | A | 248 | 33.236 | 9.634 | 30.791 | 1.00 19.93 |
| ATOM | 92 | CB | VAL | A | 248 | 34.222 | 9.018 | 29.753 | 1.00 18.58 |
| ATOM | 93 | CG1 | VAL | A | 248 | 35.476 | 9.872 | 29.625 | 1.00 17.84 |
| ATOM | 94 | CG2 | VAL | A | 248 | 34.588 | 7.604 | 30.144 | 1.00 15.29 |
| ATOM | 95 | C | VAL | A | 248 | 32.998 | 11.106 | 30.457 | 1.00 20.58 |
| ATOM | 96 | O | VAL | A | 248 | 33.657 | 11.999 | 31.004 | 1.00 21.63 |
| ATOM | 97 | N | GLU | A | 249 | 32.040 | 11.378 | 29.589 | 1.00 20.25 |
| ATOM | 98 | CA | GLU | A | 249 | 31.801 | 12.753 | 29.217 | 1.00 19.81 |
| ATOM | 99 | CB | GLU | A | 249 | 32.495 | 13.014 | 27.896 | 1.00 19.66 |
| ATOM | 100 | CG | GLU | A | 249 | 32.454 | 14.441 | 27.480 | 1.00 22.02 |
| ATOM | 101 | CD | GLU | A | 249 | 33.179 | 14.681 | 26.190 | 1.00 24.05 |
| ATOM | 102 | OE1 | GLU | A | 249 | 33.916 | 13.772 | 25.732 | 1.00 23.22 |
| ATOM | 103 | OE2 | GLU | A | 249 | 33.005 | 15.792 | 25.639 | 1.00 27.44 |
| ATOM | 104 | C | GLU | A | 249 | 30.329 | 13.082 | 29.096 | 1.00 19.53 |
| ATOM | 105 | O | GLU | A | 249 | 29.568 | 12.304 | 28.536 | 1.00 17.98 |
| ATOM | 106 | N | ARG | A | 250 | 29.925 | 14.236 | 29.624 | 1.00 19.65 |
| ATOM | 107 | CA | ARG | A | 250 | 28.527 | 14.629 | 29.530 | 1.00 20.15 |

Figure 5

| | | | | | | | | | |
|---|---|---|---|---|---|---|---|---|---|
| ATOM | 108 | CB | ARG | A | 250 | 28.101 | 15.447 | 30.746 | 1.00 21.33 |
| ATOM | 109 | CG | ARG | A | 250 | 26.599 | 15.405 | 30.982 | 1.00 22.63 |
| ATOM | 110 | CD | ARG | A | 250 | 26.195 | 16.236 | 32.178 | 1.00 23.11 |
| ATOM | 111 | NE | ARG | A | 250 | 26.489 | 17.645 | 31.956 | 1.00 23.92 |
| ATOM | 112 | CZ | ARG | A | 250 | 26.151 | 18.621 | 32.792 | 1.00 24.62 |
| ATOM | 113 | NH1 | ARG | A | 250 | 25.504 | 18.344 | 33.917 | 1.00 24.65 |
| ATOM | 114 | NH2 | ARG | A | 250 | 26.456 | 19.881 | 32.501 | 1.00 25.12 |
| ATOM | 115 | C | ARG | A | 250 | 28.250 | 15.409 | 28.253 | 1.00 20.04 |
| ATOM | 116 | O | ARG | A | 250 | 28.664 | 16.558 | 28.124 | 1.00 21.15 |
| ATOM | 117 | N | LEU | A | 251 | 27.546 | 14.781 | 27.313 | 1.00 19.04 |
| ATOM | 118 | CA | LEU | A | 251 | 27.223 | 15.418 | 26.037 | 1.00 17.60 |
| ATOM | 119 | CB | LEU | A | 251 | 26.869 | 14.355 | 24.986 | 1.00 16.19 |
| ATOM | 120 | CG | LEU | A | 251 | 27.921 | 13.244 | 24.794 | 1.00 15.53 |
| ATOM | 121 | CD1 | LEU | A | 251 | 27.386 | 12.112 | 23.919 | 1.00 13.93 |
| ATOM | 122 | CD2 | LEU | A | 251 | 29.211 | 13.815 | 24.215 | 1.00 12.30 |
| ATOM | 123 | C | LEU | A | 251 | 26.107 | 16.462 | 26.165 | 1.00 17.87 |
| ATOM | 124 | O | LEU | A | 251 | 26.118 | 17.476 | 25.472 | 1.00 17.58 |
| ATOM | 125 | N | GLY | A | 252 | 25.165 | 16.222 | 27.078 | 1.00 18.87 |
| ATOM | 126 | CA | GLY | A | 252 | 24.067 | 17.156 | 27.288 | 1.00 17.34 |
| ATOM | 127 | C | GLY | A | 252 | 23.299 | 16.988 | 28.597 | 1.00 17.50 |
| ATOM | 128 | O | GLY | A | 252 | 23.238 | 15.904 | 29.187 | 1.00 15.20 |
| ATOM | 129 | N | ALA | A | 253 | 22.709 | 18.092 | 29.044 | 1.00 18.41 |
| ATOM | 130 | CA | ALA | A | 253 | 21.918 | 18.134 | 30.263 | 1.00 19.16 |
| ATOM | 131 | CB | ALA | A | 253 | 22.712 | 18.771 | 31.394 | 1.00 18.49 |
| ATOM | 132 | C | ALA | A | 253 | 20.638 | 18.933 | 29.996 | 1.00 20.79 |
| ATOM | 133 | O | ALA | A | 253 | 20.677 | 20.096 | 29.555 | 1.00 19.67 |
| ATOM | 134 | N | GLY | A | 254 | 19.507 | 18.286 | 30.263 | 1.00 22.03 |
| ATOM | 135 | CA | GLY | A | 254 | 18.218 | 18.912 | 30.058 | 1.00 23.23 |
| ATOM | 136 | C | GLY | A | 254 | 17.234 | 18.642 | 31.182 | 1.00 24.94 |
| ATOM | 137 | O | GLY | A | 254 | 17.571 | 18.027 | 32.201 | 1.00 26.15 |
| ATOM | 138 | N | GLN | A | 255 | 15.988 | 19.036 | 30.947 | 1.00 25.43 |
| ATOM | 139 | CA | GLN | A | 255 | 14.912 | 18.894 | 31.917 | 1.00 25.44 |
| ATOM | 140 | CB | GLN | A | 255 | 13.626 | 19.478 | 31.326 | 1.00 27.36 |
| ATOM | 141 | CG | GLN | A | 255 | 12.709 | 20.104 | 32.365 | 1.00 31.75 |
| ATOM | 142 | CD | GLN | A | 255 | 11.235 | 20.095 | 31.959 | 1.00 34.54 |
| ATOM | 143 | OE1 | GLN | A | 255 | 10.348 | 20.176 | 32.824 | 1.00 33.70 |
| ATOM | 144 | NE2 | GLN | A | 255 | 10.966 | 19.990 | 30.642 | 1.00 35.17 |
| ATOM | 145 | C | GLN | A | 255 | 14.648 | 17.480 | 32.453 | 1.00 23.66 |
| ATOM | 146 | O | GLN | A | 255 | 14.469 | 17.299 | 33.653 | 1.00 23.60 |
| ATOM | 147 | N | PHE | A | 256 | 14.644 | 16.489 | 31.568 | 1.00 22.05 |
| ATOM | 148 | CA | PHE | A | 256 | 14.362 | 15.104 | 31.943 | 1.00 20.38 |
| ATOM | 149 | CB | PHE | A | 256 | 13.559 | 14.417 | 30.845 | 1.00 19.94 |
| ATOM | 150 | CG | PHE | A | 256 | 12.212 | 15.023 | 30.611 | 1.00 19.98 |
| ATOM | 151 | CD1 | PHE | A | 256 | 11.758 | 16.075 | 31.398 | 1.00 20.28 |
| ATOM | 152 | CD2 | PHE | A | 256 | 11.377 | 14.520 | 29.623 | 1.00 20.40 |
| ATOM | 153 | CE1 | PHE | A | 256 | 10.489 | 16.614 | 31.210 | 1.00 21.05 |
| ATOM | 154 | CE2 | PHE | A | 256 | 10.108 | 15.051 | 29.427 | 1.00 20.18 |
| ATOM | 155 | CZ | PHE | A | 256 | 9.666 | 16.098 | 30.226 | 1.00 20.84 |
| ATOM | 156 | C | PHE | A | 256 | 15.540 | 14.220 | 32.282 | 1.00 20.32 |
| ATOM | 157 | O | PHE | A | 256 | 15.351 | 13.092 | 32.757 | 1.00 19.33 |
| ATOM | 158 | N | GLY | A | 257 | 16.748 | 14.706 | 32.003 | 1.00 21.08 |
| ATOM | 159 | CA | GLY | A | 257 | 17.949 | 13.923 | 32.274 | 1.00 21.18 |
| ATOM | 160 | C | GLY | A | 257 | 19.173 | 14.375 | 31.494 | 1.00 20.90 |
| ATOM | 161 | O | GLY | A | 257 | 19.254 | 15.529 | 31.053 | 1.00 19.82 |
| ATOM | 162 | N | GLU | A | 258 | 20.094 | 13.440 | 31.267 | 1.00 21.06 |
| ATOM | 163 | CA | GLU | A | 258 | 21.343 | 13.738 | 30.569 | 1.00 21.32 |
| ATOM | 164 | CB | GLU | A | 258 | 22.446 | 13.946 | 31.606 | 1.00 22.30 |
| ATOM | 165 | CG | GLU | A | 258 | 22.135 | 15.027 | 32.621 | 1.00 25.82 |
| ATOM | 166 | CD | GLU | A | 258 | 23.054 | 15.011 | 33.826 | 1.00 28.69 |
| ATOM | 167 | OE1 | GLU | A | 258 | 23.517 | 13.912 | 34.228 | 1.00 29.77 |

Figure 5

| | | | | | | | | |
|---|---|---|---|---|---|---|---|---|
| ATOM | 168 | OE2 | GLU | A | 258 | 23.300 | 16.109 | 34.384 | 1.00 31.37 |
| ATOM | 169 | C | GLU | A | 258 | 21.798 | 12.654 | 29.593 | 1.00 20.90 |
| ATOM | 170 | O | GLU | A | 258 | 21.278 | 11.539 | 29.602 | 1.00 20.98 |
| ATOM | 171 | N | VAL | A | 259 | 22.766 | 13.008 | 28.742 | 1.00 20.68 |
| ATOM | 172 | CA | VAL | A | 259 | 23.365 | 12.081 | 27.759 | 1.00 19.84 |
| ATOM | 173 | CB | VAL | A | 259 | 23.030 | 12.458 | 26.297 | 1.00 18.74 |
| ATOM | 174 | CG1 | VAL | A | 259 | 23.647 | 11.449 | 25.335 | 1.00 15.96 |
| ATOM | 175 | CG2 | VAL | A | 259 | 21.523 | 12.516 | 26.111 | 1.00 19.19 |
| ATOM | 176 | C | VAL | A | 259 | 24.885 | 12.108 | 27.952 | 1.00 19.12 |
| ATOM | 177 | O | VAL | A | 259 | 25.493 | 13.181 | 28.018 | 1.00 19.01 |
| ATOM | 178 | N | TRP | A | 260 | 25.479 | 10.927 | 28.086 | 1.00 17.90 |
| ATOM | 179 | CA | TRP | A | 260 | 26.910 | 10.807 | 28.309 | 1.00 18.23 |
| ATOM | 180 | CB | TRP | A | 260 | 27.195 | 10.272 | 29.727 | 1.00 19.27 |
| ATOM | 181 | CG | TRP | A | 260 | 26.998 | 11.236 | 30.854 | 1.00 21.71 |
| ATOM | 182 | CD2 | TRP | A | 260 | 28.000 | 11.708 | 31.758 | 1.00 22.99 |
| ATOM | 183 | CE2 | TRP | A | 260 | 27.363 | 12.569 | 32.676 | 1.00 23.87 |
| ATOM | 184 | CE3 | TRP | A | 260 | 29.381 | 11.487 | 31.881 | 1.00 24.19 |
| ATOM | 185 | CD1 | TRP | A | 260 | 25.825 | 11.818 | 31.247 | 1.00 22.65 |
| ATOM | 186 | NE1 | TRP | A | 260 | 26.036 | 12.619 | 32.338 | 1.00 23.39 |
| ATOM | 187 | CZ2 | TRP | A | 260 | 28.056 | 13.208 | 33.710 | 1.00 24.10 |
| ATOM | 188 | CZ3 | TRP | A | 260 | 30.071 | 12.124 | 32.906 | 1.00 23.90 |
| ATOM | 189 | CH2 | TRP | A | 260 | 29.406 | 12.974 | 33.806 | 1.00 24.80 |
| ATOM | 190 | C | TRP | A | 260 | 27.591 | 9.853 | 27.346 | 1.00 17.77 |
| ATOM | 191 | O | TRP | A | 260 | 27.002 | 8.878 | 26.882 | 1.00 17.73 |
| ATOM | 192 | N | MET | A | 261 | 28.858 | 10.139 | 27.081 | 1.00 17.32 |
| ATOM | 193 | CA | MET | A | 261 | 29.701 | 9.290 | 26.260 | 1.00 16.53 |
| ATOM | 194 | CB | MET | A | 261 | 30.703 | 10.142 | 25.481 | 1.00 15.42 |
| ATOM | 195 | CG | MET | A | 261 | 31.672 | 9.347 | 24.620 | 1.00 15.58 |
| ATOM | 196 | SD | MET | A | 261 | 33.041 | 8.547 | 25.524 | 1.00 15.96 |
| ATOM | 197 | CE | MET | A | 261 | 33.992 | 9.974 | 26.014 | 1.00 11.37 |
| ATOM | 198 | C | MET | A | 261 | 30.400 | 8.434 | 27.332 | 1.00 16.19 |
| ATOM | 199 | O | MET | A | 261 | 30.647 | 8.896 | 28.446 | 1.00 15.47 |
| ATOM | 200 | N | GLY | A | 262 | 30.666 | 7.176 | 27.024 | 1.00 16.29 |
| ATOM | 201 | CA | GLY | A | 262 | 31.292 | 6.309 | 28.005 | 1.00 16.20 |
| ATOM | 202 | C | GLY | A | 262 | 31.687 | 5.000 | 27.375 | 1.00 16.43 |
| ATOM | 203 | O | GLY | A | 262 | 31.571 | 4.837 | 26.168 | 1.00 17.31 |
| ATOM | 204 | N | TYR | A | 263 | 32.161 | 4.059 | 28.171 | 1.00 16.91 |
| ATOM | 205 | CA | TYR | A | 263 | 32.566 | 2.789 | 27.604 | 1.00 18.14 |
| ATOM | 206 | CB | TYR | A | 263 | 34.093 | 2.622 | 27.681 | 1.00 17.89 |
| ATOM | 207 | CG | TYR | A | 263 | 34.858 | 3.647 | 26.842 | 1.00 15.78 |
| ATOM | 208 | CD1 | TYR | A | 263 | 35.249 | 3.355 | 25.535 | 1.00 14.65 |
| ATOM | 209 | CE1 | TYR | A | 263 | 35.880 | 4.316 | 24.737 | 1.00 14.90 |
| ATOM | 210 | CD2 | TYR | A | 263 | 35.131 | 4.931 | 27.340 | 1.00 15.20 |
| ATOM | 211 | CE2 | TYR | A | 263 | 35.764 | 5.906 | 26.546 | 1.00 13.95 |
| ATOM | 212 | CZ | TYR | A | 263 | 36.134 | 5.590 | 25.246 | 1.00 15.45 |
| ATOM | 213 | OH | TYR | A | 263 | 36.736 | 6.547 | 24.443 | 1.00 15.72 |
| ATOM | 214 | C | TYR | A | 263 | 31.810 | 1.664 | 28.271 | 1.00 19.65 |
| ATOM | 215 | O | TYR | A | 263 | 31.492 | 1.731 | 29.456 | 1.00 20.52 |
| ATOM | 216 | N | TYR | A | 264 | 31.440 | 0.681 | 27.464 | 1.00 21.48 |
| ATOM | 217 | CA | TYR | A | 264 | 30.668 | -0.472 | 27.904 | 1.00 24.12 |
| ATOM | 218 | CB | TYR | A | 264 | 29.409 | -0.566 | 27.015 | 1.00 23.87 |
| ATOM | 219 | CG | TYR | A | 264 | 28.471 | -1.739 | 27.223 | 1.00 23.75 |
| ATOM | 220 | CD1 | TYR | A | 264 | 28.068 | -2.144 | 28.496 | 1.00 23.72 |
| ATOM | 221 | CE1 | TYR | A | 264 | 27.232 | -3.246 | 28.664 | 1.00 22.58 |
| ATOM | 222 | CD2 | TYR | A | 264 | 28.006 | -2.465 | 26.127 | 1.00 23.32 |
| ATOM | 223 | CE2 | TYR | A | 264 | 27.183 | -3.553 | 26.286 | 1.00 23.19 |
| ATOM | 224 | CZ | TYR | A | 264 | 26.798 | -3.943 | 27.548 | 1.00 22.50 |
| ATOM | 225 | OH | TYR | A | 264 | 25.967 | -5.034 | 27.666 | 1.00 23.80 |
| ATOM | 226 | C | TYR | A | 264 | 31.608 | -1.667 | 27.761 | 1.00 26.68 |
| ATOM | 227 | O | TYR | A | 264 | 32.263 | -1.835 | 26.732 | 1.00 27.05 |

Figure 5

| | | | | | | | | | |
|---|---|---|---|---|---|---|---|---|---|
| ATOM | 228 | N | ASN | A | 265 | 31.714 | -2.461 | 28.824 | 1.00 29.44 |
| ATOM | 229 | CA | ASN | A | 265 | 32.618 | -3.608 | 28.852 | 1.00 31.52 |
| ATOM | 230 | CB | ASN | A | 265 | 32.200 | -4.685 | 27.843 | 1.00 31.11 |
| ATOM | 231 | CG | ASN | A | 265 | 30.831 | -5.279 | 28.144 | 1.00 31.28 |
| ATOM | 232 | OD1 | ASN | A | 265 | 30.494 | -5.565 | 29.298 | 1.00 30.86 |
| ATOM | 233 | ND2 | ASN | A | 265 | 30.037 | -5.483 | 27.096 | 1.00 31.80 |
| ATOM | 234 | C | ASN | A | 265 | 34.034 | -3.104 | 28.566 | 1.00 33.37 |
| ATOM | 235 | O | ASN | A | 265 | 34.818 | -3.766 | 27.888 | 1.00 34.01 |
| ATOM | 236 | N | GLY | A | 266 | 34.313 | -1.884 | 29.025 | 1.00 35.02 |
| ATOM | 237 | CA | GLY | A | 266 | 35.623 | -1.278 | 28.855 | 1.00 37.23 |
| ATOM | 238 | C | GLY | A | 266 | 36.086 | -0.808 | 27.480 | 1.00 38.89 |
| ATOM | 239 | O | GLY | A | 266 | 36.913 | 0.101 | 27.409 | 1.00 39.61 |
| ATOM | 240 | N | HIS | A | 267 | 35.598 | -1.409 | 26.394 | 1.00 40.04 |
| ATOM | 241 | CA | HIS | A | 267 | 36.038 | -0.999 | 25.058 | 1.00 40.87 |
| ATOM | 242 | CB | HIS | A | 267 | 36.956 | -2.073 | 24.443 | 1.00 45.34 |
| ATOM | 243 | CG | HIS | A | 267 | 38.328 | -2.093 | 25.049 | 1.00 50.92 |
| ATOM | 244 | CD2 | HIS | A | 267 | 39.312 | -1.158 | 25.063 | 1.00 52.55 |
| ATOM | 245 | ND1 | HIS | A | 267 | 38.787 | -3.137 | 25.831 | 1.00 52.86 |
| ATOM | 246 | CE1 | HIS | A | 267 | 39.984 | -2.839 | 26.304 | 1.00 54.07 |
| ATOM | 247 | NE2 | HIS | A | 267 | 40.327 | -1.642 | 25.854 | 1.00 53.84 |
| ATOM | 248 | C | HIS | A | 267 | 35.005 | -0.507 | 24.037 | 1.00 38.95 |
| ATOM | 249 | O | HIS | A | 267 | 35.372 | 0.168 | 23.074 | 1.00 39.32 |
| ATOM | 250 | N | THR | A | 268 | 33.729 | -0.823 | 24.236 | 1.00 35.93 |
| ATOM | 251 | CA | THR | A | 268 | 32.694 | -0.370 | 23.307 | 1.00 33.15 |
| ATOM | 252 | CB | THR | A | 268 | 31.455 | -1.270 | 23.351 | 1.00 32.95 |
| ATOM | 253 | OG1 | THR | A | 268 | 31.858 | -2.633 | 23.209 | 1.00 34.93 |
| ATOM | 254 | CG2 | THR | A | 268 | 30.508 | -0.918 | 22.224 | 1.00 31.97 |
| ATOM | 255 | C | THR | A | 268 | 32.265 | 1.041 | 23.672 | 1.00 30.78 |
| ATOM | 256 | O | THR | A | 268 | 31.661 | 1.261 | 24.721 | 1.00 31.24 |
| ATOM | 257 | N | LYS | A | 269 | 32.573 | 1.999 | 22.812 | 1.00 27.55 |
| ATOM | 258 | CA | LYS | A | 269 | 32.196 | 3.377 | 23.083 | 1.00 24.79 |
| ATOM | 259 | CB | LYS | A | 269 | 32.885 | 4.304 | 22.094 | 1.00 24.24 |
| ATOM | 260 | CG | LYS | A | 269 | 32.932 | 5.746 | 22.516 | 1.00 24.10 |
| ATOM | 261 | CD | LYS | A | 269 | 33.736 | 6.520 | 21.504 | 1.00 24.78 |
| ATOM | 262 | CE | LYS | A | 269 | 34.272 | 7.800 | 22.093 | 1.00 25.75 |
| ATOM | 263 | NZ | LYS | A | 269 | 35.234 | 8.435 | 21.156 | 1.00 25.85 |
| ATOM | 264 | C | LYS | A | 269 | 30.675 | 3.477 | 22.958 | 1.00 23.63 |
| ATOM | 265 | O | LYS | A | 269 | 30.094 | 3.022 | 21.970 | 1.00 23.25 |
| ATOM | 266 | N | VAL | A | 270 | 30.026 | 4.057 | 23.966 | 1.00 21.85 |
| ATOM | 267 | CA | VAL | A | 270 | 28.571 | 4.171 | 23.967 | 1.00 19.75 |
| ATOM | 268 | CB | VAL | A | 270 | 27.917 | 3.036 | 24.836 | 1.00 18.90 |
| ATOM | 269 | CG1 | VAL | A | 270 | 28.260 | 1.672 | 24.288 | 1.00 17.27 |
| ATOM | 270 | CG2 | VAL | A | 270 | 28.350 | 3.144 | 26.294 | 1.00 18.10 |
| ATOM | 271 | C | VAL | A | 270 | 28.043 | 5.524 | 24.459 | 1.00 19.35 |
| ATOM | 272 | O | VAL | A | 270 | 28.794 | 6.329 | 25.017 | 1.00 19.03 |
| ATOM | 273 | N | ALA | A | 271 | 26.772 | 5.801 | 24.148 | 1.00 17.87 |
| ATOM | 274 | CA | ALA | A | 271 | 26.081 | 7.009 | 24.607 | 1.00 16.42 |
| ATOM | 275 | CB | ALA | A | 271 | 25.268 | 7.643 | 23.508 | 1.00 15.47 |
| ATOM | 276 | C | ALA | A | 271 | 25.155 | 6.429 | 25.647 | 1.00 16.44 |
| ATOM | 277 | O | ALA | A | 271 | 24.607 | 5.339 | 25.457 | 1.00 15.85 |
| ATOM | 278 | N | VAL | A | 272 | 24.981 | 7.137 | 26.751 | 1.00 16.90 |
| ATOM | 279 | CA | VAL | A | 272 | 24.144 | 6.628 | 27.817 | 1.00 16.60 |
| ATOM | 280 | CB | VAL | A | 272 | 24.990 | 6.215 | 29.055 | 1.00 15.78 |
| ATOM | 281 | CG1 | VAL | A | 272 | 24.153 | 5.427 | 30.024 | 1.00 13.68 |
| ATOM | 282 | CG2 | VAL | A | 272 | 26.245 | 5.433 | 28.634 | 1.00 15.28 |
| ATOM | 283 | C | VAL | A | 272 | 23.212 | 7.724 | 28.237 | 1.00 17.63 |
| ATOM | 284 | O | VAL | A | 272 | 23.669 | 8.781 | 28.675 | 1.00 20.16 |
| ATOM | 285 | N | LYS | A | 273 | 21.912 | 7.509 | 28.043 | 1.00 17.61 |
| ATOM | 286 | CA | LYS | A | 273 | 20.912 | 8.484 | 28.452 | 1.00 16.54 |
| ATOM | 287 | CB | LYS | A | 273 | 19.777 | 8.558 | 27.428 | 1.00 17.48 |

Figure 5

```
ATOM    288   CG   LYS A 273      18.636    9.467   27.849  1.00 19.62
ATOM    289   CD   LYS A 273      17.523    9.471   26.826  1.00 22.19
ATOM    290   CE   LYS A 273      17.959   10.179   25.551  1.00 23.99
ATOM    291   NZ   LYS A 273      16.810   10.511   24.662  1.00 23.28
ATOM    292   C    LYS A 273      20.397    8.082   29.842  1.00 16.42
ATOM    293   O    LYS A 273      19.999    6.936   30.071  1.00 14.07
ATOM    294   N    SER A 274      20.496    9.011   30.787  1.00 17.95
ATOM    295   CA   SER A 274      20.047    8.760   32.144  1.00 20.26
ATOM    296   CB   SER A 274      21.193    8.968   33.145  1.00 21.64
ATOM    297   OG   SER A 274      21.522   10.335   33.277  1.00 25.81
ATOM    298   C    SER A 274      18.852    9.640   32.499  1.00 20.69
ATOM    299   O    SER A 274      18.706   10.747   31.977  1.00 19.15
ATOM    300   N    LEU A 275      18.016    9.123   33.401  1.00 22.50
ATOM    301   CA   LEU A 275      16.801    9.787   33.864  1.00 23.33
ATOM    302   CB   LEU A 275      15.685    8.747   34.049  1.00 21.45
ATOM    303   CG   LEU A 275      14.355    9.188   34.696  1.00 22.22
ATOM    304   CD1  LEU A 275      13.645   10.211   33.809  1.00 19.66
ATOM    305   CD2  LEU A 275      13.442    7.973   34.981  1.00 21.08
ATOM    306   C    LEU A 275      16.955   10.584   35.158  1.00 25.32
ATOM    307   O    LEU A 275      17.415   10.068   36.176  1.00 25.79
ATOM    308   N    LYS A 276      16.558   11.850   35.102  1.00 27.79
ATOM    309   CA   LYS A 276      16.577   12.725   36.271  1.00 30.62
ATOM    310   CB   LYS A 276      16.461   14.192   35.820  1.00 29.71
ATOM    311   CG   LYS A 276      16.186   15.191   36.934  1.00 29.80
ATOM    312   CD   LYS A 276      16.110   16.625   36.402  1.00 31.40
ATOM    313   CE   LYS A 276      17.402   17.033   35.689  1.00 33.48
ATOM    314   NZ   LYS A 276      17.477   18.479   35.272  1.00 34.48
ATOM    315   C    LYS A 276      15.343   12.320   37.099  1.00 32.41
ATOM    316   O    LYS A 276      14.208   12.626   36.706  1.00 33.41
ATOM    317   N    GLN A 277      15.557   11.601   38.207  1.00 34.07
ATOM    318   CA   GLN A 277      14.457   11.147   39.077  1.00 35.26
ATOM    319   CB   GLN A 277      14.977   10.674   40.454  1.00 38.51
ATOM    320   CG   GLN A 277      15.469    9.197   40.507  1.00 45.76
ATOM    321   CD   GLN A 277      16.981    9.020   40.872  1.00 49.98
ATOM    322   OE1  GLN A 277      17.641    8.085   40.396  1.00 51.18
ATOM    323   NE2  GLN A 277      17.508    9.903   41.728  1.00 52.28
ATOM    324   C    GLN A 277      13.378   12.214   39.265  1.00 33.81
ATOM    325   O    GLN A 277      13.668   13.370   39.591  1.00 33.01
ATOM    326   N    GLY A 278      12.145   11.834   38.950  1.00 33.20
ATOM    327   CA   GLY A 278      11.020   12.741   39.095  1.00 32.56
ATOM    328   C    GLY A 278      10.392   13.226   37.801  1.00 31.48
ATOM    329   O    GLY A 278       9.192   13.471   37.745  1.00 31.34
ATOM    330   N    SER A 279      11.202   13.372   36.763  1.00 30.90
ATOM    331   CA   SER A 279      10.722   13.840   35.466  1.00 30.31
ATOM    332   CB   SER A 279      11.905   13.913   34.499  1.00 30.49
ATOM    333   OG   SER A 279      12.907   14.767   35.033  1.00 28.68
ATOM    334   C    SER A 279       9.592   12.970   34.908  1.00 29.02
ATOM    335   O    SER A 279       8.682   13.466   34.249  1.00 28.29
ATOM    336   N    MET A 280       9.667   11.678   35.221  1.00 28.12
ATOM    337   CA   MET A 280       8.699   10.654   34.830  1.00 26.58
ATOM    338   CB   MET A 280       8.685   10.450   33.307  1.00 26.48
ATOM    339   CG   MET A 280       9.924    9.773   32.721  1.00 26.05
ATOM    340   SD   MET A 280      10.269   10.195   30.993  1.00 23.19
ATOM    341   CE   MET A 280       9.406    8.984   30.197  1.00 25.77
ATOM    342   C    MET A 280       9.135    9.377   35.565  1.00 26.36
ATOM    343   O    MET A 280      10.203    9.346   36.188  1.00 26.49
ATOM    344   N    SER A 281       8.286    8.355   35.566  1.00 26.55
ATOM    345   CA   SER A 281       8.617    7.108   36.249  1.00 26.44
ATOM    346   CB   SER A 281       7.359    6.268   36.489  1.00 26.16
ATOM    347   OG   SER A 281       7.029    5.473   35.357  1.00 24.75
```

Figure 5

| ATOM | 348 | C   | SER | A | 281 | 9.615  | 6.282  | 35.441 | 1.00 | 27.48 |
|------|-----|-----|-----|---|-----|--------|--------|--------|------|-------|
| ATOM | 349 | O   | SER | A | 281 | 9.702  | 6.407  | 34.216 | 1.00 | 27.71 |
| ATOM | 350 | N   | PRO | A | 282 | 10.413 | 5.456  | 36.126 | 1.00 | 27.73 |
| ATOM | 351 | CD  | PRO | A | 282 | 10.637 | 5.467  | 37.585 | 1.00 | 27.29 |
| ATOM | 352 | CA  | PRO | A | 282 | 11.398 | 4.608  | 35.462 | 1.00 | 28.67 |
| ATOM | 353 | CB  | PRO | A | 282 | 11.890 | 3.729  | 36.608 | 1.00 | 27.75 |
| ATOM | 354 | CG  | PRO | A | 282 | 11.942 | 4.708  | 37.730 | 1.00 | 26.47 |
| ATOM | 355 | C   | PRO | A | 282 | 10.800 | 3.784  | 34.325 | 1.00 | 29.60 |
| ATOM | 356 | O   | PRO | A | 282 | 11.444 | 3.577  | 33.301 | 1.00 | 30.23 |
| ATOM | 357 | N   | ASP | A | 283 | 9.548  | 3.368  | 34.489 | 1.00 | 30.89 |
| ATOM | 358 | CA  | ASP | A | 283 | 8.841  | 2.561  | 33.486 | 1.00 | 30.92 |
| ATOM | 359 | CB  | ASP | A | 283 | 7.535  | 2.007  | 34.088 | 1.00 | 33.37 |
| ATOM | 360 | CG  | ASP | A | 283 | 7.746  | 0.721  | 34.905 | 1.00 | 36.12 |
| ATOM | 361 | OD1 | ASP | A | 283 | 7.584  | -0.371 | 34.322 | 1.00 | 37.15 |
| ATOM | 362 | OD2 | ASP | A | 283 | 8.045  | 0.794  | 36.123 | 1.00 | 37.38 |
| ATOM | 363 | C   | ASP | A | 283 | 8.569  | 3.273  | 32.138 | 1.00 | 29.98 |
| ATOM | 364 | O   | ASP | A | 283 | 8.674  | 2.656  | 31.076 | 1.00 | 28.71 |
| ATOM | 365 | N   | ALA | A | 284 | 8.233  | 4.563  | 32.190 | 1.00 | 28.87 |
| ATOM | 366 | CA  | ALA | A | 284 | 7.954  | 5.359  | 30.991 | 1.00 | 27.40 |
| ATOM | 367 | CB  | ALA | A | 284 | 7.183  | 6.607  | 31.363 | 1.00 | 26.23 |
| ATOM | 368 | C   | ALA | A | 284 | 9.245  | 5.745  | 30.276 | 1.00 | 27.14 |
| ATOM | 369 | O   | ALA | A | 284 | 9.248  | 5.978  | 29.057 | 1.00 | 26.68 |
| ATOM | 370 | N   | PHE | A | 285 | 10.329 | 5.863  | 31.048 | 1.00 | 26.33 |
| ATOM | 371 | CA  | PHE | A | 285 | 11.643 | 6.219  | 30.502 | 1.00 | 25.36 |
| ATOM | 372 | CB  | PHE | A | 285 | 12.607 | 6.612  | 31.630 | 1.00 | 24.23 |
| ATOM | 373 | CG  | PHE | A | 285 | 13.997 | 6.937  | 31.164 | 1.00 | 21.36 |
| ATOM | 374 | CD1 | PHE | A | 285 | 14.242 | 8.068  | 30.399 | 1.00 | 19.87 |
| ATOM | 375 | CD2 | PHE | A | 285 | 15.062 | 6.104  | 31.481 | 1.00 | 20.02 |
| ATOM | 376 | CE1 | PHE | A | 285 | 15.525 | 8.358  | 29.954 | 1.00 | 19.34 |
| ATOM | 377 | CE2 | PHE | A | 285 | 16.350 | 6.395  | 31.039 | 1.00 | 19.49 |
| ATOM | 378 | CZ  | PHE | A | 285 | 16.581 | 7.520  | 30.277 | 1.00 | 18.74 |
| ATOM | 379 | C   | PHE | A | 285 | 12.181 | 5.013  | 29.755 | 1.00 | 25.70 |
| ATOM | 380 | O   | PHE | A | 285 | 12.510 | 5.103  | 28.578 | 1.00 | 25.10 |
| ATOM | 381 | N   | LEU | A | 286 | 12.259 | 3.879  | 30.446 | 1.00 | 26.63 |
| ATOM | 382 | CA  | LEU | A | 286 | 12.730 | 2.639  | 29.841 | 1.00 | 28.06 |
| ATOM | 383 | CB  | LEU | A | 286 | 12.822 | 1.534  | 30.895 | 1.00 | 28.53 |
| ATOM | 384 | CG  | LEU | A | 286 | 13.908 | 1.783  | 31.953 | 1.00 | 29.45 |
| ATOM | 385 | CD1 | LEU | A | 286 | 13.715 | 0.916  | 33.195 | 1.00 | 30.23 |
| ATOM | 386 | CD2 | LEU | A | 286 | 15.271 | 1.547  | 31.328 | 1.00 | 28.96 |
| ATOM | 387 | C   | LEU | A | 286 | 11.803 | 2.227  | 28.708 | 1.00 | 29.59 |
| ATOM | 388 | O   | LEU | A | 286 | 12.236 | 1.610  | 27.737 | 1.00 | 29.62 |
| ATOM | 389 | N   | ALA | A | 287 | 10.525 | 2.592  | 28.833 | 1.00 | 32.20 |
| ATOM | 390 | CA  | ALA | A | 287 | 9.510  | 2.291  | 27.822 | 1.00 | 33.52 |
| ATOM | 391 | CB  | ALA | A | 287 | 8.117  | 2.624  | 28.334 | 1.00 | 33.33 |
| ATOM | 392 | C   | ALA | A | 287 | 9.783  | 3.063  | 26.550 | 1.00 | 35.15 |
| ATOM | 393 | O   | ALA | A | 287 | 9.190  | 2.779  | 25.522 | 1.00 | 36.59 |
| ATOM | 394 | N   | GLU | A | 288 | 10.619 | 4.093  | 26.631 | 1.00 | 36.99 |
| ATOM | 395 | CA  | GLU | A | 288 | 10.970 | 4.874  | 25.445 | 1.00 | 38.41 |
| ATOM | 396 | CB  | GLU | A | 288 | 11.515 | 6.247  | 25.828 | 1.00 | 39.19 |
| ATOM | 397 | CG  | GLU | A | 288 | 10.515 | 7.178  | 26.497 | 1.00 | 39.81 |
| ATOM | 398 | CD  | GLU | A | 288 | 11.078 | 8.581  | 26.724 | 1.00 | 41.03 |
| ATOM | 399 | OE1 | GLU | A | 288 | 12.320 | 8.787  | 26.572 | 1.00 | 38.68 |
| ATOM | 400 | OE2 | GLU | A | 288 | 10.260 | 9.474  | 27.057 | 1.00 | 40.80 |
| ATOM | 401 | C   | GLU | A | 288 | 12.038 | 4.125  | 24.654 | 1.00 | 39.49 |
| ATOM | 402 | O   | GLU | A | 288 | 12.321 | 4.449  | 23.501 | 1.00 | 39.03 |
| ATOM | 403 | N   | ALA | A | 289 | 12.652 | 3.142  | 25.301 | 1.00 | 41.02 |
| ATOM | 404 | CA  | ALA | A | 289 | 13.683 | 2.348  | 24.672 | 1.00 | 42.45 |
| ATOM | 405 | CB  | ALA | A | 289 | 14.730 | 1.938  | 25.687 | 1.00 | 43.03 |
| ATOM | 406 | C   | ALA | A | 289 | 13.156 | 1.127  | 23.957 | 1.00 | 43.76 |
| ATOM | 407 | O   | ALA | A | 289 | 13.592 | 0.858  | 22.861 | 1.00 | 43.61 |

Figure 5

| ATOM | 408 | N | ASN A 290 | 12.229 | 0.398 | 24.576 | 1.00 | 45.93 |
|------|-----|-----|-----------|--------|--------|--------|------|-------|
| ATOM | 409 | CA | ASN A 290 | 11.677 | -0.839 | 23.988 | 1.00 | 48.39 |
| ATOM | 410 | CB | ASN A 290 | 10.651 | -1.503 | 24.941 | 1.00 | 50.03 |
| ATOM | 411 | CG | ASN A 290 | 9.523 | -0.572 | 25.337 | 1.00 | 51.25 |
| ATOM | 412 | OD1 | ASN A 290 | 9.338 | 0.470 | 24.722 | 1.00 | 51.62 |
| ATOM | 413 | ND2 | ASN A 290 | 8.750 | -0.956 | 26.357 | 1.00 | 52.02 |
| ATOM | 414 | C | ASN A 290 | 11.149 | -0.793 | 22.524 | 1.00 | 47.76 |
| ATOM | 415 | O | ASN A 290 | 10.743 | -1.807 | 21.950 | 1.00 | 48.27 |
| ATOM | 416 | N | LEU A 291 | 11.211 | 0.386 | 21.920 | 1.00 | 46.68 |
| ATOM | 417 | CA | LEU A 291 | 10.798 | 0.601 | 20.530 | 1.00 | 45.44 |
| ATOM | 418 | CB | LEU A 291 | 10.455 | 2.082 | 20.364 | 1.00 | 46.36 |
| ATOM | 419 | CG | LEU A 291 | 9.876 | 2.800 | 21.597 | 1.00 | 45.76 |
| ATOM | 420 | CD1 | LEU A 291 | 10.134 | 4.262 | 21.491 | 1.00 | 45.07 |
| ATOM | 421 | CD2 | LEU A 291 | 8.397 | 2.519 | 21.792 | 1.00 | 46.55 |
| ATOM | 422 | C | LEU A 291 | 12.028 | 0.262 | 19.673 | 1.00 | 44.64 |
| ATOM | 423 | O | LEU A 291 | 11.941 | -0.158 | 18.516 | 1.00 | 44.14 |
| ATOM | 424 | N | MET A 292 | 13.188 | 0.456 | 20.296 | 1.00 | 43.98 |
| ATOM | 425 | CA | MET A 292 | 14.521 | 0.222 | 19.739 | 1.00 | 42.03 |
| ATOM | 426 | CB | MET A 292 | 15.518 | 1.088 | 20.524 | 1.00 | 38.70 |
| ATOM | 427 | CG | MET A 292 | 16.823 | 1.439 | 19.814 | 1.00 | 34.23 |
| ATOM | 428 | SD | MET A 292 | 17.678 | 2.740 | 20.731 | 1.00 | 27.52 |
| ATOM | 429 | CE | MET A 292 | 16.641 | 2.961 | 22.184 | 1.00 | 28.62 |
| ATOM | 430 | C | MET A 292 | 14.866 | -1.253 | 19.879 | 1.00 | 42.53 |
| ATOM | 431 | O | MET A 292 | 15.777 | -1.745 | 19.211 | 1.00 | 42.77 |
| ATOM | 432 | N | LYS A 293 | 14.164 | -1.933 | 20.793 | 1.00 | 43.53 |
| ATOM | 433 | CA | LYS A 293 | 14.362 | -3.358 | 21.042 | 1.00 | 43.74 |
| ATOM | 434 | CB | LYS A 293 | 13.719 | -3.779 | 22.342 | 1.00 | 45.02 |
| ATOM | 435 | CG | LYS A 293 | 14.273 | -3.141 | 23.602 | 1.00 | 46.94 |
| ATOM | 436 | CD | LYS A 293 | 13.637 | -3.867 | 24.803 | 1.00 | 50.22 |
| ATOM | 437 | CE | LYS A 293 | 14.267 | -3.505 | 26.155 | 1.00 | 52.20 |
| ATOM | 438 | NZ | LYS A 293 | 13.885 | -4.490 | 27.241 | 1.00 | 52.88 |
| ATOM | 439 | C | LYS A 293 | 13.723 | -4.136 | 19.910 | 1.00 | 44.11 |
| ATOM | 440 | O | LYS A 293 | 14.271 | -5.128 | 19.440 | 1.00 | 44.75 |
| ATOM | 441 | N | GLN A 294 | 12.564 | -3.682 | 19.448 | 1.00 | 44.76 |
| ATOM | 442 | CA | GLN A 294 | 11.854 | -4.351 | 18.354 | 1.00 | 44.99 |
| ATOM | 443 | CB | GLN A 294 | 10.383 | -3.910 | 18.296 | 1.00 | 46.50 |
| ATOM | 444 | CG | GLN A 294 | 9.592 | -4.120 | 19.600 | 1.00 | 50.09 |
| ATOM | 445 | CD | GLN A 294 | 9.517 | -5.592 | 20.049 | 1.00 | 52.70 |
| ATOM | 446 | OE1 | GLN A 294 | 10.200 | -6.011 | 21.001 | 1.00 | 52.78 |
| ATOM | 447 | NE2 | GLN A 294 | 8.664 | -6.372 | 19.384 | 1.00 | 52.35 |
| ATOM | 448 | C | GLN A 294 | 12.534 | -4.106 | 16.996 | 1.00 | 43.96 |
| ATOM | 449 | O | GLN A 294 | 12.917 | -5.053 | 16.311 | 1.00 | 44.05 |
| ATOM | 450 | N | LEU A 295 | 12.743 | -2.839 | 16.646 | 1.00 | 42.44 |
| ATOM | 451 | CA | LEU A 295 | 13.354 | -2.486 | 15.368 | 1.00 | 40.70 |
| ATOM | 452 | CB | LEU A 295 | 12.706 | -1.218 | 14.822 | 1.00 | 41.54 |
| ATOM | 453 | CG | LEU A 295 | 11.188 | -1.241 | 14.686 | 1.00 | 41.72 |
| ATOM | 454 | CD1 | LEU A 295 | 10.722 | 0.121 | 14.185 | 1.00 | 42.04 |
| ATOM | 455 | CD2 | LEU A 295 | 10.755 | -2.373 | 13.748 | 1.00 | 40.74 |
| ATOM | 456 | C | LEU A 295 | 14.872 | -2.326 | 15.343 | 1.00 | 38.91 |
| ATOM | 457 | O | LEU A 295 | 15.452 | -1.542 | 16.096 | 1.00 | 38.49 |
| ATOM | 458 | N | GLN A 296 | 15.505 | -3.043 | 14.425 | 1.00 | 37.61 |
| ATOM | 459 | CA | GLN A 296 | 16.953 | -2.983 | 14.265 | 1.00 | 36.74 |
| ATOM | 460 | CB | GLN A 296 | 17.593 | -4.264 | 14.806 | 1.00 | 38.70 |
| ATOM | 461 | CG | GLN A 296 | 17.336 | -4.445 | 16.301 | 1.00 | 41.04 |
| ATOM | 462 | CD | GLN A 296 | 17.522 | -5.862 | 16.764 | 1.00 | 42.86 |
| ATOM | 463 | OE1 | GLN A 296 | 17.637 | -6.783 | 15.953 | 1.00 | 44.31 |
| ATOM | 464 | NE2 | GLN A 296 | 17.545 | -6.055 | 18.080 | 1.00 | 44.03 |
| ATOM | 465 | C | GLN A 296 | 17.285 | -2.756 | 12.796 | 1.00 | 34.65 |
| ATOM | 466 | O | GLN A 296 | 16.805 | -3.463 | 11.903 | 1.00 | 34.35 |
| ATOM | 467 | N | HIS A 297 | 18.093 | -1.738 | 12.549 | 1.00 | 32.41 |

Figure 5

```
ATOM    468  CA   HIS A 297      18.443  -1.388  11.192  1.00 30.01
ATOM    469  CB   HIS A 297      17.314  -0.549  10.592  1.00 28.26
ATOM    470  CG   HIS A 297      17.316  -0.512   9.099  1.00 25.35
ATOM    471  CD2  HIS A 297      16.713  -1.313   8.190  1.00 23.95
ATOM    472  ND1  HIS A 297      18.037   0.413   8.379  1.00 24.44
ATOM    473  CE1  HIS A 297      17.885   0.176   7.088  1.00 24.04
ATOM    474  NE2  HIS A 297      17.086  -0.866   6.948  1.00 23.04
ATOM    475  C    HIS A 297      19.714  -0.577  11.178  1.00 30.14
ATOM    476  O    HIS A 297      20.062   0.073  12.167  1.00 29.22
ATOM    477  N    GLN A 298      20.379  -0.584  10.027  1.00 31.20
ATOM    478  CA   GLN A 298      21.621   0.159   9.848  1.00 32.04
ATOM    479  CB   GLN A 298      22.298  -0.265   8.540  1.00 35.65
ATOM    480  CG   GLN A 298      22.923  -1.679   8.615  1.00 42.31
ATOM    481  CD   GLN A 298      23.984  -1.823   9.745  1.00 45.11
ATOM    482  OE1  GLN A 298      24.100  -2.887  10.378  1.00 45.07
ATOM    483  NE2  GLN A 298      24.745  -0.747   9.998  1.00 44.65
ATOM    484  C    GLN A 298      21.426   1.679   9.910  1.00 30.06
ATOM    485  O    GLN A 298      22.369   2.424  10.177  1.00 29.31
ATOM    486  N    ARG A 299      20.182   2.115   9.716  1.00 28.46
ATOM    487  CA   ARG A 299      19.818   3.531   9.739  1.00 26.47
ATOM    488  CB   ARG A 299      18.919   3.855   8.549  1.00 26.40
ATOM    489  CG   ARG A 299      19.567   3.614   7.213  1.00 27.82
ATOM    490  CD   ARG A 299      20.664   4.606   6.974  1.00 28.44
ATOM    491  NE   ARG A 299      21.683   4.044   6.103  1.00 30.20
ATOM    492  CZ   ARG A 299      22.974   4.007   6.413  1.00 32.09
ATOM    493  NH1  ARG A 299      23.408   4.505   7.580  1.00 32.17
ATOM    494  NH2  ARG A 299      23.830   3.482   5.551  1.00 31.28
ATOM    495  C    ARG A 299      19.097   3.895  11.035  1.00 24.72
ATOM    496  O    ARG A 299      18.622   5.010  11.194  1.00 24.06
ATOM    497  N    LEU A 300      18.962   2.915  11.920  1.00 24.02
ATOM    498  CA   LEU A 300      18.314   3.090  13.216  1.00 22.90
ATOM    499  CB   LEU A 300      17.243   2.017  13.405  1.00 21.50
ATOM    500  CG   LEU A 300      15.792   2.467  13.342  1.00 20.70
ATOM    501  CD1  LEU A 300      15.564   3.286  12.086  1.00 19.26
ATOM    502  CD2  LEU A 300      14.870   1.261  13.415  1.00 19.11
ATOM    503  C    LEU A 300      19.332   2.952  14.336  1.00 22.73
ATOM    504  O    LEU A 300      20.170   2.051  14.298  1.00 23.12
ATOM    505  N    VAL A 301      19.269   3.844  15.323  1.00 22.98
ATOM    506  CA   VAL A 301      20.181   3.775  16.464  1.00 23.00
ATOM    507  CB   VAL A 301      20.017   4.967  17.403  1.00 21.85
ATOM    508  CG1  VAL A 301      20.699   4.688  18.720  1.00 22.08
ATOM    509  CG2  VAL A 301      20.621   6.204  16.778  1.00 20.55
ATOM    510  C    VAL A 301      19.963   2.464  17.223  1.00 24.56
ATOM    511  O    VAL A 301      18.839   2.101  17.581  1.00 25.82
ATOM    512  N    ARG A 302      21.056   1.732  17.391  1.00 26.35
ATOM    513  CA   ARG A 302      21.076   0.434  18.047  1.00 26.94
ATOM    514  CB   ARG A 302      22.201  -0.410  17.419  1.00 29.41
ATOM    515  CG   ARG A 302      22.317  -1.854  17.870  1.00 34.53
ATOM    516  CD   ARG A 302      23.410  -1.996  18.912  1.00 39.93
ATOM    517  NE   ARG A 302      23.747  -3.383  19.243  1.00 43.01
ATOM    518  CZ   ARG A 302      24.736  -4.072  18.674  1.00 44.52
ATOM    519  NH1  ARG A 302      25.482  -3.514  17.728  1.00 44.13
ATOM    520  NH2  ARG A 302      25.038  -5.287  19.117  1.00 45.46
ATOM    521  C    ARG A 302      21.218   0.521  19.565  1.00 25.73
ATOM    522  O    ARG A 302      21.972   1.339  20.111  1.00 25.14
ATOM    523  N    LEU A 303      20.413  -0.288  20.234  1.00 24.80
ATOM    524  CA   LEU A 303      20.425  -0.376  21.678  1.00 24.22
ATOM    525  CB   LEU A 303      19.023  -0.692  22.189  1.00 22.84
ATOM    526  CG   LEU A 303      18.833  -0.665  23.703  1.00 21.81
ATOM    527  CD1  LEU A 303      18.719   0.766  24.186  1.00 20.65
```

Figure 5

| | | | | | | | | | |
|---|---|---|---|---|---|---|---|---|---|
| ATOM | 528 | CD2 | LEU | A | 303 | 17.585 | -1.434 | 24.062 | 1.00 21.30 |
| ATOM | 529 | C | LEU | A | 303 | 21.366 | -1.513 | 22.076 | 1.00 24.74 |
| ATOM | 530 | O | LEU | A | 303 | 21.473 | -2.525 | 21.364 | 1.00 24.22 |
| ATOM | 531 | N | TYR | A | 304 | 22.079 | -1.315 | 23.185 | 1.00 25.26 |
| ATOM | 532 | CA | TYR | A | 304 | 22.989 | -2.318 | 23.713 | 1.00 25.95 |
| ATOM | 533 | CB | TYR | A | 304 | 24.387 | -1.748 | 23.967 | 1.00 27.38 |
| ATOM | 534 | CG | TYR | A | 304 | 25.252 | -1.607 | 22.733 | 1.00 29.55 |
| ATOM | 535 | CD1 | TYR | A | 304 | 25.532 | -0.349 | 22.200 | 1.00 31.28 |
| ATOM | 536 | CE1 | TYR | A | 304 | 26.362 | -0.194 | 21.098 | 1.00 32.02 |
| ATOM | 537 | CD2 | TYR | A | 304 | 25.829 | -2.719 | 22.123 | 1.00 31.65 |
| ATOM | 538 | CE2 | TYR | A | 304 | 26.672 | -2.574 | 21.009 | 1.00 33.14 |
| ATOM | 539 | CZ | TYR | A | 304 | 26.927 | -1.301 | 20.511 | 1.00 33.44 |
| ATOM | 540 | OH | TYR | A | 304 | 27.760 | -1.118 | 19.440 | 1.00 35.95 |
| ATOM | 541 | C | TYR | A | 304 | 22.411 | -2.838 | 25.013 | 1.00 25.83 |
| ATOM | 542 | O | TYR | A | 304 | 22.273 | -4.046 | 25.195 | 1.00 26.99 |
| ATOM | 543 | N | ALA | A | 305 | 22.018 | -1.926 | 25.895 | 1.00 24.70 |
| ATOM | 544 | CA | ALA | A | 305 | 21.475 | -2.334 | 27.178 | 1.00 24.51 |
| ATOM | 545 | CB | ALA | A | 305 | 22.569 | -3.020 | 27.992 | 1.00 24.90 |
| ATOM | 546 | C | ALA | A | 305 | 20.873 | -1.178 | 27.971 | 1.00 24.77 |
| ATOM | 547 | O | ALA | A | 305 | 20.845 | -0.047 | 27.504 | 1.00 23.88 |
| ATOM | 548 | N | VAL | A | 306 | 20.391 | -1.485 | 29.177 | 1.00 26.07 |
| ATOM | 549 | CA | VAL | A | 306 | 19.786 | -0.500 | 30.083 | 1.00 27.47 |
| ATOM | 550 | CB | VAL | A | 306 | 18.234 | -0.436 | 29.931 | 1.00 28.10 |
| ATOM | 551 | CG1 | VAL | A | 306 | 17.849 | 0.040 | 28.543 | 1.00 28.90 |
| ATOM | 552 | CG2 | VAL | A | 306 | 17.597 | -1.798 | 30.222 | 1.00 26.80 |
| ATOM | 553 | C | VAL | A | 306 | 20.074 | -0.889 | 31.531 | 1.00 28.34 |
| ATOM | 554 | O | VAL | A | 306 | 20.303 | -2.059 | 31.823 | 1.00 28.56 |
| ATOM | 555 | N | VAL | A | 307 | 20.098 | 0.094 | 32.427 | 1.00 29.44 |
| ATOM | 556 | CA | VAL | A | 307 | 20.319 | -0.164 | 33.851 | 1.00 31.34 |
| ATOM | 557 | CB | VAL | A | 307 | 21.555 | 0.573 | 34.413 | 1.00 30.66 |
| ATOM | 558 | CG1 | VAL | A | 307 | 21.658 | 0.345 | 35.925 | 1.00 31.17 |
| ATOM | 559 | CG2 | VAL | A | 307 | 22.815 | 0.080 | 33.726 | 1.00 29.02 |
| ATOM | 560 | C | VAL | A | 307 | 19.061 | 0.252 | 34.623 | 1.00 33.68 |
| ATOM | 561 | O | VAL | A | 307 | 18.680 | 1.434 | 34.661 | 1.00 33.96 |
| ATOM | 562 | N | THR | A | 308 | 18.441 | -0.731 | 35.267 | 1.00 35.65 |
| ATOM | 563 | CA | THR | A | 308 | 17.205 | -0.515 | 35.993 | 1.00 37.70 |
| ATOM | 564 | CB | THR | A | 308 | 16.352 | -1.777 | 35.946 | 1.00 38.11 |
| ATOM | 565 | OG1 | THR | A | 308 | 17.173 | -2.918 | 36.235 | 1.00 39.99 |
| ATOM | 566 | CG2 | THR | A | 308 | 15.764 | -1.931 | 34.549 | 1.00 36.91 |
| ATOM | 567 | C | THR | A | 308 | 17.244 | 0.090 | 37.394 | 1.00 39.36 |
| ATOM | 568 | O | THR | A | 308 | 16.239 | 0.624 | 37.847 | 1.00 39.70 |
| ATOM | 569 | N | GLN | A | 309 | 18.367 | 0.012 | 38.100 | 1.00 41.45 |
| ATOM | 570 | CA | GLN | A | 309 | 18.419 | 0.642 | 39.421 | 1.00 43.91 |
| ATOM | 571 | CB | GLN | A | 309 | 19.440 | -0.044 | 40.355 | 1.00 46.53 |
| ATOM | 572 | CG | GLN | A | 309 | 20.912 | 0.044 | 39.909 | 1.00 51.47 |
| ATOM | 573 | CD | GLN | A | 309 | 21.922 | -0.328 | 41.014 | 1.00 53.56 |
| ATOM | 574 | OE1 | GLN | A | 309 | 21.649 | -0.174 | 42.214 | 1.00 53.36 |
| ATOM | 575 | NE2 | GLN | A | 309 | 23.098 | -0.808 | 40.600 | 1.00 54.13 |
| ATOM | 576 | C | GLN | A | 309 | 18.760 | 2.122 | 39.197 | 1.00 43.72 |
| ATOM | 577 | O | GLN | A | 309 | 19.575 | 2.448 | 38.332 | 1.00 43.85 |
| ATOM | 578 | N | GLU | A | 310 | 18.118 | 3.015 | 39.942 | 1.00 43.46 |
| ATOM | 579 | CA | GLU | A | 310 | 18.351 | 4.452 | 39.789 | 1.00 44.09 |
| ATOM | 580 | CB | GLU | A | 310 | 17.368 | 5.249 | 40.658 | 1.00 47.80 |
| ATOM | 581 | CG | GLU | A | 310 | 17.359 | 4.899 | 42.164 | 1.00 52.71 |
| ATOM | 582 | CD | GLU | A | 310 | 16.469 | 3.689 | 42.532 | 1.00 55.35 |
| ATOM | 583 | OE1 | GLU | A | 310 | 15.228 | 3.755 | 42.304 | 1.00 55.37 |
| ATOM | 584 | OE2 | GLU | A | 310 | 17.019 | 2.687 | 43.067 | 1.00 56.11 |
| ATOM | 585 | C | GLU | A | 310 | 19.791 | 4.896 | 40.069 | 1.00 42.41 |
| ATOM | 586 | O | GLU | A | 310 | 20.422 | 4.403 | 41.005 | 1.00 42.48 |
| ATOM | 587 | N | PRO | A | 311 | 20.360 | 5.784 | 39.219 | 1.00 40.90 |

Figure 5

| | | | | | | | | | |
|---|---|---|---|---|---|---|---|---|---|
| ATOM | 588 | CD | PRO | A | 311 | 21.721 | 6.294 | 39.478 | 1.00 40.40 |
| ATOM | 589 | CA | PRO | A | 311 | 19.802 | 6.424 | 38.014 | 1.00 38.58 |
| ATOM | 590 | CB | PRO | A | 311 | 20.916 | 7.388 | 37.584 | 1.00 38.82 |
| ATOM | 591 | CG | PRO | A | 311 | 21.674 | 7.653 | 38.839 | 1.00 39.67 |
| ATOM | 592 | C | PRO | A | 311 | 19.528 | 5.416 | 36.894 | 1.00 36.22 |
| ATOM | 593 | O | PRO | A | 311 | 20.307 | 4.492 | 36.663 | 1.00 35.72 |
| ATOM | 594 | N | ILE | A | 312 | 18.415 | 5.600 | 36.197 | 1.00 33.57 |
| ATOM | 595 | CA | ILE | A | 312 | 18.052 | 4.706 | 35.103 | 1.00 29.75 |
| ATOM | 596 | CB | ILE | A | 312 | 16.543 | 4.846 | 34.758 | 1.00 30.11 |
| ATOM | 597 | CG2 | ILE | A | 312 | 16.060 | 3.635 | 33.973 | 1.00 29.28 |
| ATOM | 598 | CG1 | ILE | A | 312 | 15.716 | 5.063 | 36.042 | 1.00 31.29 |
| ATOM | 599 | CD1 | ILE | A | 312 | 15.868 | 3.984 | 37.116 | 1.00 31.62 |
| ATOM | 600 | C | ILE | A | 312 | 18.903 | 5.115 | 33.897 | 1.00 26.53 |
| ATOM | 601 | O | ILE | A | 312 | 19.075 | 6.313 | 33.641 | 1.00 25.51 |
| ATOM | 602 | N | TYR | A | 313 | 19.494 | 4.125 | 33.223 | 1.00 23.00 |
| ATOM | 603 | CA | TYR | A | 313 | 20.332 | 4.347 | 32.035 | 1.00 19.81 |
| ATOM | 604 | CB | TYR | A | 313 | 21.775 | 3.827 | 32.233 | 1.00 20.14 |
| ATOM | 605 | CG | TYR | A | 313 | 22.667 | 4.559 | 33.226 | 1.00 21.06 |
| ATOM | 606 | CD1 | TYR | A | 313 | 22.325 | 5.819 | 33.723 | 1.00 21.91 |
| ATOM | 607 | CE1 | TYR | A | 313 | 23.157 | 6.490 | 34.642 | 1.00 23.44 |
| ATOM | 608 | CD2 | TYR | A | 313 | 23.865 | 3.979 | 33.670 | 1.00 20.84 |
| ATOM | 609 | CE2 | TYR | A | 313 | 24.704 | 4.638 | 34.582 | 1.00 22.00 |
| ATOM | 610 | CZ | TYR | A | 313 | 24.345 | 5.896 | 35.072 | 1.00 23.28 |
| ATOM | 611 | OH | TYR | A | 313 | 25.147 | 6.560 | 35.994 | 1.00 23.09 |
| ATOM | 612 | C | TYR | A | 313 | 19.786 | 3.615 | 30.821 | 1.00 17.53 |
| ATOM | 613 | O | TYR | A | 313 | 19.216 | 2.532 | 30.933 | 1.00 15.68 |
| ATOM | 614 | N | ILE | A | 314 | 19.989 | 4.223 | 29.658 | 1.00 16.56 |
| ATOM | 615 | CA | ILE | A | 314 | 19.617 | 3.640 | 28.375 | 1.00 16.74 |
| ATOM | 616 | CB | ILE | A | 314 | 18.544 | 4.459 | 27.602 | 1.00 16.78 |
| ATOM | 617 | CG2 | ILE | A | 314 | 18.504 | 4.012 | 26.133 | 1.00 15.96 |
| ATOM | 618 | CG1 | ILE | A | 314 | 17.156 | 4.288 | 28.243 | 1.00 16.18 |
| ATOM | 619 | CD1 | ILE | A | 314 | 16.034 | 5.050 | 27.514 | 1.00 16.98 |
| ATOM | 620 | C | ILE | A | 314 | 20.922 | 3.738 | 27.616 | 1.00 16.92 |
| ATOM | 621 | O | ILE | A | 314 | 21.398 | 4.840 | 27.355 | 1.00 18.51 |
| ATOM | 622 | N | ILE | A | 315 | 21.527 | 2.601 | 27.306 | 1.00 16.65 |
| ATOM | 623 | CA | ILE | A | 315 | 22.805 | 2.587 | 26.602 | 1.00 17.15 |
| ATOM | 624 | CB | ILE | A | 315 | 23.791 | 1.555 | 27.252 | 1.00 18.45 |
| ATOM | 625 | CG2 | ILE | A | 315 | 25.110 | 1.520 | 26.505 | 1.00 19.25 |
| ATOM | 626 | CG1 | ILE | A | 315 | 24.070 | 1.919 | 28.713 | 1.00 19.04 |
| ATOM | 627 | CD1 | ILE | A | 315 | 23.130 | 1.294 | 29.718 | 1.00 19.53 |
| ATOM | 628 | C | ILE | A | 315 | 22.669 | 2.273 | 25.114 | 1.00 16.77 |
| ATOM | 629 | O | ILE | A | 315 | 22.192 | 1.209 | 24.732 | 1.00 15.73 |
| ATOM | 630 | N | THR | A | 316 | 23.099 | 3.206 | 24.276 | 1.00 16.75 |
| ATOM | 631 | CA | THR | A | 316 | 23.040 | 3.004 | 22.838 | 1.00 18.21 |
| ATOM | 632 | CB | THR | A | 316 | 22.074 | 4.002 | 22.162 | 1.00 17.87 |
| ATOM | 633 | OG1 | THR | A | 316 | 22.513 | 5.343 | 22.427 | 1.00 17.68 |
| ATOM | 634 | CG2 | THR | A | 316 | 20.656 | 3.810 | 22.691 | 1.00 16.51 |
| ATOM | 635 | C | THR | A | 316 | 24.427 | 3.190 | 22.235 | 1.00 19.52 |
| ATOM | 636 | O | THR | A | 316 | 25.355 | 3.658 | 22.899 | 1.00 19.12 |
| ATOM | 637 | N | GLU | A | 317 | 24.562 | 2.823 | 20.962 | 1.00 20.68 |
| ATOM | 638 | CA | GLU | A | 317 | 25.825 | 2.988 | 20.252 | 1.00 21.16 |
| ATOM | 639 | CB | GLU | A | 317 | 25.697 | 2.514 | 18.807 | 1.00 21.29 |
| ATOM | 640 | CG | GLU | A | 317 | 24.743 | 3.329 | 17.963 | 1.00 22.75 |
| ATOM | 641 | CD | GLU | A | 317 | 24.850 | 2.982 | 16.499 | 1.00 23.87 |
| ATOM | 642 | OE1 | GLU | A | 317 | 23.821 | 2.586 | 15.905 | 1.00 23.58 |
| ATOM | 643 | OE2 | GLU | A | 317 | 25.973 | 3.099 | 15.950 | 1.00 24.66 |
| ATOM | 644 | C | GLU | A | 317 | 26.165 | 4.469 | 20.282 | 1.00 20.85 |
| ATOM | 645 | O | GLU | A | 317 | 25.305 | 5.307 | 20.542 | 1.00 21.03 |
| ATOM | 646 | N | TYR | A | 318 | 27.415 | 4.800 | 20.029 | 1.00 21.25 |
| ATOM | 647 | CA | TYR | A | 318 | 27.806 | 6.198 | 20.076 | 1.00 22.04 |

Figure 5

| ATOM | 648 | CB | TYR | A | 318 | 29.138 | 6.318 | 20.802 | 1.00 | 21.57 |
| ATOM | 649 | CG | TYR | A | 318 | 29.712 | 7.700 | 20.834 | 1.00 | 22.03 |
| ATOM | 650 | CD1 | TYR | A | 318 | 29.158 | 8.685 | 21.650 | 1.00 | 21.71 |
| ATOM | 651 | CE1 | TYR | A | 318 | 29.712 | 9.967 | 21.703 | 1.00 | 22.45 |
| ATOM | 652 | CD2 | TYR | A | 318 | 30.838 | 8.024 | 20.061 | 1.00 | 22.24 |
| ATOM | 653 | CE2 | TYR | A | 318 | 31.404 | 9.304 | 20.102 | 1.00 | 21.93 |
| ATOM | 654 | CZ | TYR | A | 318 | 30.839 | 10.268 | 20.928 | 1.00 | 23.04 |
| ATOM | 655 | OH | TYR | A | 318 | 31.411 | 11.523 | 20.999 | 1.00 | 24.37 |
| ATOM | 656 | C | TYR | A | 318 | 27.878 | 6.825 | 18.692 | 1.00 | 22.66 |
| ATOM | 657 | O | TYR | A | 318 | 28.351 | 6.198 | 17.745 | 1.00 | 22.76 |
| ATOM | 658 | N | MET | A | 319 | 27.368 | 8.047 | 18.573 | 1.00 | 23.16 |
| ATOM | 659 | CA | MET | A | 319 | 27.393 | 8.777 | 17.308 | 1.00 | 24.62 |
| ATOM | 660 | CB | MET | A | 319 | 25.978 | 9.144 | 16.877 | 1.00 | 24.54 |
| ATOM | 661 | CG | MET | A | 319 | 25.082 | 7.937 | 16.611 | 1.00 | 24.60 |
| ATOM | 662 | SD | MET | A | 319 | 25.620 | 6.901 | 15.220 | 1.00 | 27.09 |
| ATOM | 663 | CE | MET | A | 319 | 25.001 | 7.827 | 13.808 | 1.00 | 25.43 |
| ATOM | 664 | C | MET | A | 319 | 28.284 | 10.027 | 17.424 | 1.00 | 25.92 |
| ATOM | 665 | O | MET | A | 319 | 27.880 | 11.056 | 17.985 | 1.00 | 25.36 |
| ATOM | 666 | N | GLU | A | 320 | 29.515 | 9.873 | 16.921 | 1.00 | 26.31 |
| ATOM | 667 | CA | GLU | A | 320 | 30.586 | 10.872 | 16.908 | 1.00 | 25.91 |
| ATOM | 668 | CB | GLU | A | 320 | 31.669 | 10.423 | 15.932 | 1.00 | 28.81 |
| ATOM | 669 | CG | GLU | A | 320 | 32.874 | 11.367 | 15.788 | 1.00 | 34.68 |
| ATOM | 670 | CD | GLU | A | 320 | 33.964 | 11.142 | 16.827 | 1.00 | 36.09 |
| ATOM | 671 | OE1 | GLU | A | 320 | 34.169 | 9.977 | 17.253 | 1.00 | 37.91 |
| ATOM | 672 | OE2 | GLU | A | 320 | 34.621 | 12.141 | 17.204 | 1.00 | 36.37 |
| ATOM | 673 | C | GLU | A | 320 | 30.211 | 12.311 | 16.606 | 1.00 | 25.01 |
| ATOM | 674 | O | GLU | A | 320 | 30.489 | 13.206 | 17.398 | 1.00 | 25.63 |
| ATOM | 675 | N | ASN | A | 321 | 29.590 | 12.549 | 15.461 | 1.00 | 24.29 |
| ATOM | 676 | CA | ASN | A | 321 | 29.218 | 13.911 | 15.111 | 1.00 | 23.15 |
| ATOM | 677 | CB | ASN | A | 321 | 29.388 | 14.129 | 13.617 | 1.00 | 22.72 |
| ATOM | 678 | CG | ASN | A | 321 | 30.831 | 13.984 | 13.191 | 1.00 | 21.60 |
| ATOM | 679 | OD1 | ASN | A | 321 | 31.727 | 14.625 | 13.748 | 1.00 | 20.74 |
| ATOM | 680 | ND2 | ASN | A | 321 | 31.072 | 13.115 | 12.233 | 1.00 | 21.52 |
| ATOM | 681 | C | ASN | A | 321 | 27.868 | 14.387 | 15.629 | 1.00 | 22.86 |
| ATOM | 682 | O | ASN | A | 321 | 27.358 | 15.434 | 15.217 | 1.00 | 23.51 |
| ATOM | 683 | N | GLY | A | 322 | 27.321 | 13.608 | 16.559 | 1.00 | 22.62 |
| ATOM | 684 | CA | GLY | A | 322 | 26.067 | 13.919 | 17.228 | 1.00 | 21.88 |
| ATOM | 685 | C | GLY | A | 322 | 24.818 | 14.218 | 16.432 | 1.00 | 21.08 |
| ATOM | 686 | O | GLY | A | 322 | 24.414 | 13.458 | 15.567 | 1.00 | 20.65 |
| ATOM | 687 | N | SER | A | 323 | 24.175 | 15.320 | 16.801 | 1.00 | 21.21 |
| ATOM | 688 | CA | SER | A | 323 | 22.944 | 15.785 | 16.176 | 1.00 | 20.52 |
| ATOM | 689 | CB | SER | A | 323 | 22.281 | 16.815 | 17.084 | 1.00 | 20.45 |
| ATOM | 690 | OG | SER | A | 323 | 20.969 | 17.102 | 16.651 | 1.00 | 21.60 |
| ATOM | 691 | C | SER | A | 323 | 23.204 | 16.405 | 14.817 | 1.00 | 20.72 |
| ATOM | 692 | O | SER | A | 323 | 24.086 | 17.254 | 14.659 | 1.00 | 21.94 |
| ATOM | 693 | N | LEU | A | 324 | 22.414 | 16.002 | 13.836 | 1.00 | 20.41 |
| ATOM | 694 | CA | LEU | A | 324 | 22.566 | 16.527 | 12.489 | 1.00 | 20.52 |
| ATOM | 695 | CB | LEU | A | 324 | 21.544 | 15.860 | 11.555 | 1.00 | 20.02 |
| ATOM | 696 | CG | LEU | A | 324 | 21.468 | 16.203 | 10.068 | 1.00 | 18.23 |
| ATOM | 697 | CD1 | LEU | A | 324 | 22.733 | 15.788 | 9.367 | 1.00 | 17.28 |
| ATOM | 698 | CD2 | LEU | A | 324 | 20.271 | 15.497 | 9.455 | 1.00 | 18.18 |
| ATOM | 699 | C | LEU | A | 324 | 22.376 | 18.050 | 12.502 | 1.00 | 20.92 |
| ATOM | 700 | O | LEU | A | 324 | 23.220 | 18.781 | 11.984 | 1.00 | 21.42 |
| ATOM | 701 | N | VAL | A | 325 | 21.308 | 18.506 | 13.158 | 1.00 | 20.81 |
| ATOM | 702 | CA | VAL | A | 325 | 20.973 | 19.921 | 13.241 | 1.00 | 22.10 |
| ATOM | 703 | CB | VAL | A | 325 | 19.722 | 20.165 | 14.139 | 1.00 | 21.15 |
| ATOM | 704 | CG1 | VAL | A | 325 | 20.081 | 20.352 | 15.596 | 1.00 | 21.91 |
| ATOM | 705 | CG2 | VAL | A | 325 | 18.902 | 21.333 | 13.615 | 1.00 | 20.91 |
| ATOM | 706 | C | VAL | A | 325 | 22.177 | 20.786 | 13.696 | 1.00 | 23.53 |
| ATOM | 707 | O | VAL | A | 325 | 22.372 | 21.899 | 13.206 | 1.00 | 23.33 |

Figure 5

| | | | | | | | | |
|---|---|---|---|---|---|---|---|---|
|ATOM|708|N|ASP|A|326|23.006|20.220|14.579|1.00|25.54|
|ATOM|709|CA|ASP|A|326|24.215|20.896|15.056|1.00|27.53|
|ATOM|710|CB|ASP|A|326|24.579|20.434|16.438|1.00|27.94|
|ATOM|711|CG|ASP|A|326|23.647|20.938|17.467|1.00|28.89|
|ATOM|712|OD1|ASP|A|326|23.420|22.183|17.495|1.00|30.26|
|ATOM|713|OD2|ASP|A|326|23.085|20.118|18.203|1.00|31.50|
|ATOM|714|C|ASP|A|326|25.423|20.704|14.156|1.00|28.25|
|ATOM|715|O|ASP|A|326|26.253|21.596|14.000|1.00|28.22|
|ATOM|716|N|PHE|A|327|25.525|19.507|13.568|1.00|29.05|
|ATOM|717|CA|PHE|A|327|26.638|19.200|12.694|1.00|29.79|
|ATOM|718|CB|PHE|A|327|26.655|17.691|12.391|1.00|30.53|
|ATOM|719|CG|PHE|A|327|27.659|17.283|11.328|1.00|31.28|
|ATOM|720|CD1|PHE|A|327|29.020|17.186|11.641|1.00|31.34|
|ATOM|721|CD2|PHE|A|327|27.259|17.014|10.021|1.00|31.44|
|ATOM|722|CE1|PHE|A|327|29.963|16.838|10.665|1.00|31.20|
|ATOM|723|CE2|PHE|A|327|28.180|16.666|9.032|1.00|31.48|
|ATOM|724|CZ|PHE|A|327|29.547|16.580|9.355|1.00|31.92|
|ATOM|725|C|PHE|A|327|26.620|19.986|11.377|1.00|30.80|
|ATOM|726|O|PHE|A|327|27.660|20.438|10.929|1.00|31.94|
|ATOM|727|N|LEU|A|328|25.437|20.139|10.773|1.00|31.14|
|ATOM|728|CA|LEU|A|328|25.342|20.877|9.510|1.00|30.71|
|ATOM|729|CB|LEU|A|328|23.899|20.914|9.007|1.00|29.37|
|ATOM|730|CG|LEU|A|328|23.232|19.598|8.613|1.00|27.77|
|ATOM|731|CD1|LEU|A|328|21.731|19.814|8.464|1.00|26.66|
|ATOM|732|CD2|LEU|A|328|23.849|19.037|7.338|1.00|26.01|
|ATOM|733|C|LEU|A|328|25.894|22.299|9.623|1.00|31.98|
|ATOM|734|O|LEU|A|328|26.381|22.857|8.632|1.00|32.10|
|ATOM|735|N|LYS|A|329|25.821|22.854|10.838|1.00|32.91|
|ATOM|736|CA|LYS|A|329|26.321|24.199|11.131|1.00|33.90|
|ATOM|737|CB|LYS|A|329|25.620|24.795|12.361|1.00|32.59|
|ATOM|738|CG|LYS|A|329|24.126|24.924|12.288|1.00|31.13|
|ATOM|739|CD|LYS|A|329|23.649|25.779|13.435|1.00|32.00|
|ATOM|740|CE|LYS|A|329|22.143|25.699|13.620|1.00|32.49|
|ATOM|741|NZ|LYS|A|329|21.713|24.378|14.156|1.00|33.57|
|ATOM|742|C|LYS|A|329|27.840|24.265|11.371|1.00|35.27|
|ATOM|743|O|LYS|A|329|28.425|25.347|11.268|1.00|36.28|
|ATOM|744|N|THR|A|330|28.456|23.137|11.742|1.00|35.68|
|ATOM|745|CA|THR|A|330|29.904|23.080|11.999|1.00|35.44|
|ATOM|746|CB|THR|A|330|30.349|21.689|12.509|1.00|34.59|
|ATOM|747|OG1|THR|A|330|30.219|20.734|11.455|1.00|35.49|
|ATOM|748|CG2|THR|A|330|29.506|21.241|13.690|1.00|34.51|
|ATOM|749|C|THR|A|330|30.676|23.374|10.713|1.00|35.87|
|ATOM|750|O|THR|A|330|30.163|23.139|9.630|1.00|35.96|
|ATOM|751|N|PRO|A|331|31.934|23.852|10.825|1.00|36.69|
|ATOM|752|CD|PRO|A|331|32.669|24.056|12.092|1.00|36.95|
|ATOM|753|CA|PRO|A|331|32.793|24.180|9.677|1.00|36.95|
|ATOM|754|CB|PRO|A|331|34.173|24.304|10.324|1.00|36.62|
|ATOM|755|CG|PRO|A|331|33.854|24.892|11.652|1.00|36.73|
|ATOM|756|C|PRO|A|331|32.796|23.112|8.579|1.00|37.49|
|ATOM|757|O|PRO|A|331|32.746|23.435|7.396|1.00|37.39|
|ATOM|758|N|SER|A|332|32.848|21.848|8.997|1.00|38.12|
|ATOM|759|CA|SER|A|332|32.861|20.693|8.100|1.00|39.00|
|ATOM|760|CB|SER|A|332|33.189|19.425|8.899|1.00|39.20|
|ATOM|761|OG|SER|A|332|34.130|19.687|9.928|1.00|39.60|
|ATOM|762|C|SER|A|332|31.496|20.499|7.440|1.00|39.88|
|ATOM|763|O|SER|A|332|31.405|20.149|6.254|1.00|39.82|
|ATOM|764|N|GLY|A|333|30.448|20.674|8.249|1.00|40.33|
|ATOM|765|CA|GLY|A|333|29.075|20.520|7.796|1.00|40.54|
|ATOM|766|C|GLY|A|333|28.657|21.587|6.815|1.00|40.49|
|ATOM|767|O|GLY|A|333|27.972|21.297|5.840|1.00|41.20|

Figure 5

| | | | | | | | | |
|---|---|---|---|---|---|---|---|---|
| ATOM | 768 | N | ILE | A | 334 | 29.017 | 22.829 | 7.108 | 1.00 40.28 |
| ATOM | 769 | CA | ILE | A | 334 | 28.719 | 23.953 | 6.229 | 1.00 40.58 |
| ATOM | 770 | CB | ILE | A | 334 | 29.342 | 25.262 | 6.785 | 1.00 41.37 |
| ATOM | 771 | CG2 | ILE | A | 334 | 29.424 | 26.330 | 5.703 | 1.00 43.23 |
| ATOM | 772 | CG1 | ILE | A | 334 | 28.548 | 25.766 | 7.999 | 1.00 42.79 |
| ATOM | 773 | CD1 | ILE | A | 334 | 27.100 | 26.207 | 7.706 | 1.00 43.27 |
| ATOM | 774 | C | ILE | A | 334 | 29.294 | 23.678 | 4.834 | 1.00 40.15 |
| ATOM | 775 | O | ILE | A | 334 | 28.633 | 23.920 | 3.830 | 1.00 40.80 |
| ATOM | 776 | N | LYS | A | 335 | 30.501 | 23.118 | 4.783 | 1.00 40.00 |
| ATOM | 777 | CA | LYS | A | 335 | 31.177 | 22.826 | 3.517 | 1.00 39.63 |
| ATOM | 778 | CB | LYS | A | 335 | 32.696 | 22.678 | 3.729 | 1.00 40.96 |
| ATOM | 779 | CG | LYS | A | 335 | 33.421 | 23.883 | 4.359 | 1.00 42.32 |
| ATOM | 780 | CD | LYS | A | 335 | 34.950 | 23.664 | 4.367 | 1.00 43.90 |
| ATOM | 781 | CE | LYS | A | 335 | 35.704 | 24.696 | 5.216 | 1.00 44.49 |
| ATOM | 782 | NZ | LYS | A | 335 | 36.157 | 24.131 | 6.536 | 1.00 45.84 |
| ATOM | 783 | C | LYS | A | 335 | 30.657 | 21.607 | 2.749 | 1.00 38.72 |
| ATOM | 784 | O | LYS | A | 335 | 31.115 | 21.349 | 1.630 | 1.00 38.26 |
| ATOM | 785 | N | LEU | A | 336 | 29.731 | 20.849 | 3.346 | 1.00 38.08 |
| ATOM | 786 | CA | LEU | A | 336 | 29.154 | 19.655 | 2.690 | 1.00 36.98 |
| ATOM | 787 | CB | LEU | A | 336 | 28.219 | 18.884 | 3.633 | 1.00 35.49 |
| ATOM | 788 | CG | LEU | A | 336 | 28.825 | 17.891 | 4.624 | 1.00 34.25 |
| ATOM | 789 | CD1 | LEU | A | 336 | 27.706 | 17.088 | 5.295 | 1.00 33.37 |
| ATOM | 790 | CD2 | LEU | A | 336 | 29.792 | 16.969 | 3.897 | 1.00 32.62 |
| ATOM | 791 | C | LEU | A | 336 | 28.423 | 19.923 | 1.364 | 1.00 36.30 |
| ATOM | 792 | O | LEU | A | 336 | 27.540 | 20.793 | 1.273 | 1.00 36.11 |
| ATOM | 793 | N | THR | A | 337 | 28.770 | 19.122 | 0.360 | 1.00 35.15 |
| ATOM | 794 | CA | THR | A | 337 | 28.197 | 19.239 | -0.976 | 1.00 34.58 |
| ATOM | 795 | CB | THR | A | 337 | 29.051 | 18.460 | -2.019 | 1.00 33.89 |
| ATOM | 796 | OG1 | THR | A | 337 | 28.861 | 17.050 | -1.865 | 1.00 33.02 |
| ATOM | 797 | CG2 | THR | A | 337 | 30.521 | 18.759 | -1.816 | 1.00 34.37 |
| ATOM | 798 | C | THR | A | 337 | 26.730 | 18.789 | -1.057 | 1.00 34.45 |
| ATOM | 799 | O | THR | A | 337 | 26.258 | 18.026 | -0.209 | 1.00 35.10 |
| ATOM | 800 | N | ILE | A | 338 | 26.016 | 19.282 | -2.072 | 1.00 33.23 |
| ATOM | 801 | CA | ILE | A | 338 | 24.614 | 18.934 | -2.277 | 1.00 31.71 |
| ATOM | 802 | CB | ILE | A | 338 | 24.000 | 19.665 | -3.522 | 1.00 31.58 |
| ATOM | 803 | CG2 | ILE | A | 338 | 24.674 | 19.196 | -4.825 | 1.00 31.03 |
| ATOM | 804 | CG1 | ILE | A | 338 | 22.482 | 19.435 | -3.597 | 1.00 29.66 |
| ATOM | 805 | CD1 | ILE | A | 338 | 21.697 | 19.982 | -2.431 | 1.00 28.44 |
| ATOM | 806 | C | ILE | A | 338 | 24.500 | 17.424 | -2.442 | 1.00 31.40 |
| ATOM | 807 | O | ILE | A | 338 | 23.562 | 16.811 | -1.945 | 1.00 31.90 |
| ATOM | 808 | N | ASN | A | 339 | 25.481 | 16.827 | -3.112 | 1.00 30.93 |
| ATOM | 809 | CA | ASN | A | 339 | 25.508 | 15.382 | -3.322 | 1.00 30.48 |
| ATOM | 810 | CB | ASN | A | 339 | 26.735 | 14.987 | -4.163 | 1.00 31.24 |
| ATOM | 811 | CG | ASN | A | 339 | 26.823 | 15.760 | -5.461 | 1.00 32.13 |
| ATOM | 812 | OD1 | ASN | A | 339 | 26.485 | 15.234 | -6.525 | 1.00 31.69 |
| ATOM | 813 | ND2 | ASN | A | 339 | 27.256 | 17.027 | -5.380 | 1.00 31.33 |
| ATOM | 814 | C | ASN | A | 339 | 25.544 | 14.626 | -1.991 | 1.00 29.47 |
| ATOM | 815 | O | ASN | A | 339 | 24.918 | 13.581 | -1.850 | 1.00 30.94 |
| ATOM | 816 | N | LYS | A | 340 | 26.285 | 15.152 | -1.023 | 1.00 28.23 |
| ATOM | 817 | CA | LYS | A | 340 | 26.408 | 14.523 | 0.285 | 1.00 27.69 |
| ATOM | 818 | CB | LYS | A | 340 | 27.682 | 15.008 | 0.986 | 1.00 27.59 |
| ATOM | 819 | CG | LYS | A | 340 | 27.902 | 14.464 | 2.382 | 1.00 28.08 |
| ATOM | 820 | CD | LYS | A | 340 | 27.966 | 12.942 | 2.454 | 1.00 27.68 |
| ATOM | 821 | CE | LYS | A | 340 | 28.035 | 12.501 | 3.930 | 1.00 28.55 |
| ATOM | 822 | NZ | LYS | A | 340 | 27.862 | 11.024 | 4.149 | 1.00 28.90 |
| ATOM | 823 | C | LYS | A | 340 | 25.161 | 14.776 | 1.129 | 1.00 27.41 |
| ATOM | 824 | O | LYS | A | 340 | 24.716 | 13.888 | 1.862 | 1.00 28.48 |
| ATOM | 825 | N | LEU | A | 341 | 24.566 | 15.961 | 0.989 | 1.00 26.41 |
| ATOM | 826 | CA | LEU | A | 341 | 23.338 | 16.301 | 1.720 | 1.00 24.40 |
| ATOM | 827 | CB | LEU | A | 341 | 22.970 | 17.762 | 1.500 | 1.00 22.84 |

Figure 5

| | | | | | | | | |
|---|---|---|---|---|---|---|---|---|
| ATOM | 828 | CG | LEU | A | 341 | 23.953 | 18.793 | 2.052 | 1.00 21.94 |
| ATOM | 829 | CD1 | LEU | A | 341 | 23.339 | 20.178 | 1.913 | 1.00 20.91 |
| ATOM | 830 | CD2 | LEU | A | 341 | 24.268 | 18.510 | 3.512 | 1.00 20.67 |
| ATOM | 831 | C | LEU | A | 341 | 22.169 | 15.409 | 1.304 | 1.00 23.99 |
| ATOM | 832 | O | LEU | A | 341 | 21.413 | 14.922 | 2.135 | 1.00 24.30 |
| ATOM | 833 | N | LEU | A | 342 | 22.036 | 15.176 | 0.010 | 1.00 24.58 |
| ATOM | 834 | CA | LEU | A | 342 | 20.958 | 14.333 | -0.488 | 1.00 25.19 |
| ATOM | 835 | CB | LEU | A | 342 | 20.823 | 14.438 | -2.000 | 1.00 25.66 |
| ATOM | 836 | CG | LEU | A | 342 | 20.354 | 15.793 | -2.485 | 1.00 26.09 |
| ATOM | 837 | CD1 | LEU | A | 342 | 20.230 | 15.733 | -3.958 | 1.00 28.29 |
| ATOM | 838 | CD2 | LEU | A | 342 | 19.028 | 16.145 | -1.872 | 1.00 28.91 |
| ATOM | 839 | C | LEU | A | 342 | 21.146 | 12.884 | -0.121 | 1.00 24.82 |
| ATOM | 840 | O | LEU | A | 342 | 20.167 | 12.152 | 0.010 | 1.00 25.34 |
| ATOM | 841 | N | ASP | A | 343 | 22.400 | 12.457 | 0.011 | 1.00 24.82 |
| ATOM | 842 | CA | ASP | A | 343 | 22.650 | 11.078 | 0.370 | 1.00 24.71 |
| ATOM | 843 | CB | ASP | A | 343 | 24.111 | 10.676 | 0.181 | 1.00 28.11 |
| ATOM | 844 | CG | ASP | A | 343 | 24.314 | 9.163 | 0.344 | 1.00 33.22 |
| ATOM | 845 | OD1 | ASP | A | 343 | 23.588 | 8.392 | -0.343 | 1.00 35.48 |
| ATOM | 846 | OD2 | ASP | A | 343 | 25.154 | 8.739 | 1.181 | 1.00 35.29 |
| ATOM | 847 | C | ASP | A | 343 | 22.241 | 10.890 | 1.810 | 1.00 23.20 |
| ATOM | 848 | O | ASP | A | 343 | 21.655 | 9.872 | 2.157 | 1.00 22.67 |
| ATOM | 849 | N | MET | A | 344 | 22.535 | 11.890 | 2.638 | 1.00 21.88 |
| ATOM | 850 | CA | MET | A | 344 | 22.176 | 11.850 | 4.053 | 1.00 20.71 |
| ATOM | 851 | CB | MET | A | 344 | 22.715 | 13.083 | 4.779 | 1.00 19.26 |
| ATOM | 852 | CG | MET | A | 344 | 24.231 | 13.137 | 4.832 | 1.00 18.30 |
| ATOM | 853 | SD | MET | A | 344 | 24.825 | 14.617 | 5.679 | 1.00 18.36 |
| ATOM | 854 | CE | MET | A | 344 | 25.565 | 13.889 | 7.105 | 1.00 18.25 |
| ATOM | 855 | C | MET | A | 344 | 20.654 | 11.746 | 4.210 | 1.00 20.18 |
| ATOM | 856 | O | MET | A | 344 | 20.159 | 10.941 | 5.009 | 1.00 19.56 |
| ATOM | 857 | N | ALA | A | 345 | 19.933 | 12.540 | 3.412 | 1.00 19.24 |
| ATOM | 858 | CA | ALA | A | 345 | 18.472 | 12.560 | 3.387 | 1.00 18.22 |
| ATOM | 859 | CB | ALA | A | 345 | 17.984 | 13.627 | 2.412 | 1.00 18.53 |
| ATOM | 860 | C | ALA | A | 345 | 17.944 | 11.199 | 2.960 | 1.00 17.93 |
| ATOM | 861 | O | ALA | A | 345 | 16.896 | 10.759 | 3.419 | 1.00 17.73 |
| ATOM | 862 | N | ALA | A | 346 | 18.674 | 10.548 | 2.062 | 1.00 18.05 |
| ATOM | 863 | CA | ALA | A | 346 | 18.303 | 9.230 | 1.572 | 1.00 18.61 |
| ATOM | 864 | CB | ALA | A | 346 | 19.189 | 8.845 | 0.419 | 1.00 17.37 |
| ATOM | 865 | C | ALA | A | 346 | 18.418 | 8.194 | 2.681 | 1.00 19.61 |
| ATOM | 866 | O | ALA | A | 346 | 17.568 | 7.312 | 2.811 | 1.00 20.84 |
| ATOM | 867 | N | GLN | A | 347 | 19.470 | 8.304 | 3.488 | 1.00 19.89 |
| ATOM | 868 | CA | GLN | A | 347 | 19.683 | 7.365 | 4.585 | 1.00 19.43 |
| ATOM | 869 | CB | GLN | A | 347 | 21.023 | 7.634 | 5.277 | 1.00 21.48 |
| ATOM | 870 | CG | GLN | A | 347 | 22.208 | 7.677 | 4.336 | 1.00 24.37 |
| ATOM | 871 | CD | GLN | A | 347 | 23.501 | 7.986 | 5.057 | 1.00 27.58 |
| ATOM | 872 | OE1 | GLN | A | 347 | 24.191 | 7.081 | 5.508 | 1.00 31.54 |
| ATOM | 873 | NE2 | GLN | A | 347 | 23.829 | 9.266 | 5.187 | 1.00 29.35 |
| ATOM | 874 | C | GLN | A | 347 | 18.533 | 7.473 | 5.587 | 1.00 18.38 |
| ATOM | 875 | O | GLN | A | 347 | 18.026 | 6.455 | 6.069 | 1.00 17.95 |
| ATOM | 876 | N | ILE | A | 348 | 18.111 | 8.709 | 5.867 | 1.00 16.83 |
| ATOM | 877 | CA | ILE | A | 348 | 17.012 | 8.990 | 6.799 | 1.00 15.83 |
| ATOM | 878 | CB | ILE | A | 348 | 16.869 | 10.518 | 7.041 | 1.00 15.23 |
| ATOM | 879 | CG2 | ILE | A | 348 | 15.734 | 10.800 | 8.011 | 1.00 14.42 |
| ATOM | 880 | CG1 | ILE | A | 348 | 18.179 | 11.074 | 7.594 | 1.00 13.78 |
| ATOM | 881 | CD1 | ILE | A | 348 | 18.216 | 12.553 | 7.698 | 1.00 14.13 |
| ATOM | 882 | C | ILE | A | 348 | 15.683 | 8.426 | 6.277 | 1.00 15.71 |
| ATOM | 883 | O | ILE | A | 348 | 14.920 | 7.817 | 7.024 | 1.00 15.82 |
| ATOM | 884 | N | ALA | A | 349 | 15.430 | 8.623 | 4.985 | 1.00 15.54 |
| ATOM | 885 | CA | ALA | A | 349 | 14.221 | 8.135 | 4.338 | 1.00 14.65 |
| ATOM | 886 | CB | ALA | A | 349 | 14.111 | 8.723 | 2.950 | 1.00 14.65 |
| ATOM | 887 | C | ALA | A | 349 | 14.239 | 6.602 | 4.284 | 1.00 15.21 |

Figure 5

| ATOM | 888 | O | ALA | A | 349 | 13.183 | 5.969 | 4.329 | 1.00 | 15.05 |
|------|-----|-----|-----|---|-----|--------|-------|-------|------|-------|
| ATOM | 889 | N | GLU | A | 350 | 15.438 | 6.013 | 4.198 | 1.00 | 16.12 |
| ATOM | 890 | CA | GLU | A | 350 | 15.612 | 4.555 | 4.181 | 1.00 | 17.04 |
| ATOM | 891 | CB | GLU | A | 350 | 17.046 | 4.183 | 3.824 | 1.00 | 17.46 |
| ATOM | 892 | CG | GLU | A | 350 | 17.319 | 2.667 | 3.790 | 1.00 | 18.76 |
| ATOM | 893 | CD | GLU | A | 350 | 18.808 | 2.326 | 3.699 | 1.00 | 19.32 |
| ATOM | 894 | OE1 | GLU | A | 350 | 19.610 | 3.203 | 3.303 | 1.00 | 17.47 |
| ATOM | 895 | OE2 | GLU | A | 350 | 19.175 | 1.173 | 4.021 | 1.00 | 20.33 |
| ATOM | 896 | C | GLU | A | 350 | 15.250 | 3.973 | 5.555 | 1.00 | 18.05 |
| ATOM | 897 | O | GLU | A | 350 | 14.542 | 2.971 | 5.650 | 1.00 | 19.50 |
| ATOM | 898 | N | GLY | A | 351 | 15.714 | 4.621 | 6.621 | 1.00 | 18.74 |
| ATOM | 899 | CA | GLY | A | 351 | 15.381 | 4.157 | 7.955 | 1.00 | 18.04 |
| ATOM | 900 | C | GLY | A | 351 | 13.885 | 4.292 | 8.169 | 1.00 | 17.75 |
| ATOM | 901 | O | GLY | A | 351 | 13.268 | 3.420 | 8.791 | 1.00 | 16.73 |
| ATOM | 902 | N | MET | A | 352 | 13.312 | 5.396 | 7.671 | 1.00 | 17.44 |
| ATOM | 903 | CA | MET | A | 352 | 11.872 | 5.657 | 7.785 | 1.00 | 16.84 |
| ATOM | 904 | CB | MET | A | 352 | 11.538 | 7.099 | 7.414 | 1.00 | 14.87 |
| ATOM | 905 | CG | MET | A | 352 | 11.838 | 8.131 | 8.503 | 1.00 | 14.36 |
| ATOM | 906 | SD | MET | A | 352 | 11.141 | 7.786 | 10.142 | 1.00 | 14.42 |
| ATOM | 907 | CE | MET | A | 352 | 9.479 | 7.232 | 9.727 | 1.00 | 11.48 |
| ATOM | 908 | C | MET | A | 352 | 11.090 | 4.703 | 6.892 | 1.00 | 17.38 |
| ATOM | 909 | O | MET | A | 352 | 9.941 | 4.382 | 7.168 | 1.00 | 16.71 |
| ATOM | 910 | N | ALA | A | 353 | 11.728 | 4.252 | 5.815 | 1.00 | 18.28 |
| ATOM | 911 | CA | ALA | A | 353 | 11.111 | 3.310 | 4.895 | 1.00 | 19.12 |
| ATOM | 912 | CB | ALA | A | 353 | 12.051 | 3.030 | 3.741 | 1.00 | 19.20 |
| ATOM | 913 | C | ALA | A | 353 | 10.851 | 2.027 | 5.665 | 1.00 | 20.41 |
| ATOM | 914 | O | ALA | A | 353 | 9.807 | 1.398 | 5.509 | 1.00 | 21.65 |
| ATOM | 915 | N | PHE | A | 354 | 11.830 | 1.648 | 6.486 | 1.00 | 21.12 |
| ATOM | 916 | CA | PHE | A | 354 | 11.780 | 0.449 | 7.320 | 1.00 | 20.29 |
| ATOM | 917 | CB | PHE | A | 354 | 13.159 | 0.204 | 7.949 | 1.00 | 22.11 |
| ATOM | 918 | CG | PHE | A | 354 | 13.228 | -1.038 | 8.797 | 1.00 | 23.58 |
| ATOM | 919 | CD1 | PHE | A | 354 | 13.112 | -2.301 | 8.212 | 1.00 | 24.05 |
| ATOM | 920 | CD2 | PHE | A | 354 | 13.389 | -0.948 | 10.182 | 1.00 | 23.71 |
| ATOM | 921 | CE1 | PHE | A | 354 | 13.150 | -3.458 | 8.991 | 1.00 | 23.62 |
| ATOM | 922 | CE2 | PHE | A | 354 | 13.429 | -2.105 | 10.970 | 1.00 | 23.94 |
| ATOM | 923 | CZ | PHE | A | 354 | 13.310 | -3.358 | 10.371 | 1.00 | 22.83 |
| ATOM | 924 | C | PHE | A | 354 | 10.728 | 0.558 | 8.410 | 1.00 | 18.66 |
| ATOM | 925 | O | PHE | A | 354 | 10.020 | -0.389 | 8.680 | 1.00 | 18.83 |
| ATOM | 926 | N | ILE | A | 355 | 10.683 | 1.700 | 9.079 | 1.00 | 18.89 |
| ATOM | 927 | CA | ILE | A | 355 | 9.707 | 1.948 | 10.137 | 1.00 | 19.14 |
| ATOM | 928 | CB | ILE | A | 355 | 9.926 | 3.353 | 10.779 | 1.00 | 16.77 |
| ATOM | 929 | CG2 | ILE | A | 355 | 8.744 | 3.752 | 11.654 | 1.00 | 15.07 |
| ATOM | 930 | CG1 | ILE | A | 355 | 11.249 | 3.367 | 11.555 | 1.00 | 14.27 |
| ATOM | 931 | CD1 | ILE | A | 355 | 11.603 | 4.695 | 12.151 | 1.00 | 11.70 |
| ATOM | 932 | C | ILE | A | 355 | 8.312 | 1.854 | 9.524 | 1.00 | 21.46 |
| ATOM | 933 | O | ILE | A | 355 | 7.438 | 1.164 | 10.061 | 1.00 | 21.99 |
| ATOM | 934 | N | GLU | A | 356 | 8.138 | 2.512 | 8.374 | 1.00 | 22.60 |
| ATOM | 935 | CA | GLU | A | 356 | 6.880 | 2.513 | 7.636 | 1.00 | 23.83 |
| ATOM | 936 | CB | GLU | A | 356 | 7.032 | 3.354 | 6.380 | 1.00 | 22.96 |
| ATOM | 937 | CG | GLU | A | 356 | 5.888 | 3.234 | 5.411 | 1.00 | 20.38 |
| ATOM | 938 | CD | GLU | A | 356 | 6.145 | 3.998 | 4.156 | 1.00 | 18.26 |
| ATOM | 939 | OE1 | GLU | A | 356 | 6.744 | 3.436 | 3.214 | 1.00 | 20.44 |
| ATOM | 940 | OE2 | GLU | A | 356 | 5.773 | 5.180 | 4.119 | 1.00 | 18.40 |
| ATOM | 941 | C | GLU | A | 356 | 6.507 | 1.097 | 7.234 | 1.00 | 26.27 |
| ATOM | 942 | O | GLU | A | 356 | 5.370 | 0.658 | 7.411 | 1.00 | 27.92 |
| ATOM | 943 | N | GLU | A | 357 | 7.490 | 0.397 | 6.690 | 1.00 | 27.74 |
| ATOM | 944 | CA | GLU | A | 357 | 7.355 | -0.976 | 6.248 | 1.00 | 30.27 |
| ATOM | 945 | CB | GLU | A | 357 | 8.706 | -1.406 | 5.658 | 1.00 | 33.14 |
| ATOM | 946 | CG | GLU | A | 357 | 9.191 | -2.798 | 5.984 | 1.00 | 37.59 |
| ATOM | 947 | CD | GLU | A | 357 | 8.655 | -3.807 | 5.026 | 1.00 | 40.74 |

Figure 5

| | | | | | | | | |
|---|---|---|---|---|---|---|---|---|
| ATOM | 948  | OE1 | GLU | A | 357 | 9.136  | -3.800 | 3.878  | 1.00 | 43.95 |
| ATOM | 949  | OE2 | GLU | A | 357 | 7.757  | -4.592 | 5.407  | 1.00 | 41.90 |
| ATOM | 950  | C   | GLU | A | 357 | 6.895  | -1.920 | 7.371  | 1.00 | 30.74 |
| ATOM | 951  | O   | GLU | A | 357 | 6.178  | -2.887 | 7.113  | 1.00 | 31.36 |
| ATOM | 952  | N   | ARG | A | 358 | 7.288  | -1.623 | 8.611  | 1.00 | 31.19 |
| ATOM | 953  | CA  | ARG | A | 358 | 6.930  | -2.450 | 9.773  | 1.00 | 30.90 |
| ATOM | 954  | CB  | ARG | A | 358 | 8.121  | -2.570 | 10.728 | 1.00 | 31.78 |
| ATOM | 955  | CG  | ARG | A | 358 | 9.338  | -3.254 | 10.117 | 1.00 | 33.74 |
| ATOM | 956  | CD  | ARG | A | 358 | 9.166  | -4.772 | 9.978  | 1.00 | 37.40 |
| ATOM | 957  | NE  | ARG | A | 358 | 9.082  | -5.441 | 11.277 | 1.00 | 41.97 |
| ATOM | 958  | CZ  | ARG | A | 358 | 10.088 | -5.539 | 12.153 | 1.00 | 44.52 |
| ATOM | 959  | NH1 | ARG | A | 358 | 11.282 | -5.022 | 11.886 | 1.00 | 45.61 |
| ATOM | 960  | NH2 | ARG | A | 358 | 9.895  | -6.122 | 13.330 | 1.00 | 45.39 |
| ATOM | 961  | C   | ARG | A | 358 | 5.697  | -1.945 | 10.516 | 1.00 | 30.75 |
| ATOM | 962  | O   | ARG | A | 358 | 5.364  | -2.414 | 11.613 | 1.00 | 29.50 |
| ATOM | 963  | N   | ASN | A | 359 | 5.022  | -0.987 | 9.891  | 1.00 | 31.58 |
| ATOM | 964  | CA  | ASN | A | 359 | 3.802  | -0.386 | 10.419 | 1.00 | 31.84 |
| ATOM | 965  | CB  | ASN | A | 359 | 2.671  | -1.414 | 10.395 | 1.00 | 33.83 |
| ATOM | 966  | CG  | ASN | A | 359 | 2.546  | -2.087 | 9.027  | 1.00 | 37.38 |
| ATOM | 967  | OD1 | ASN | A | 359 | 2.147  | -1.451 | 8.039  | 1.00 | 38.70 |
| ATOM | 968  | ND2 | ASN | A | 359 | 2.958  | -3.355 | 8.947  | 1.00 | 38.39 |
| ATOM | 969  | C   | ASN | A | 359 | 3.950  | 0.287  | 11.778 | 1.00 | 30.83 |
| ATOM | 970  | O   | ASN | A | 359 | 3.211  | 0.006  | 12.722 | 1.00 | 31.26 |
| ATOM | 971  | N   | TYR | A | 360 | 4.919  | 1.192  | 11.850 | 1.00 | 29.49 |
| ATOM | 972  | CA  | TYR | A | 360 | 5.197  | 1.973  | 13.047 | 1.00 | 29.03 |
| ATOM | 973  | CB  | TYR | A | 360 | 6.519  | 1.541  | 13.677 | 1.00 | 30.03 |
| ATOM | 974  | CG  | TYR | A | 360 | 6.430  | 0.311  | 14.543 | 1.00 | 31.97 |
| ATOM | 975  | CD1 | TYR | A | 360 | 7.194  | -0.828 | 14.257 | 1.00 | 32.04 |
| ATOM | 976  | CE1 | TYR | A | 360 | 7.134  | -1.952 | 15.059 | 1.00 | 32.46 |
| ATOM | 977  | CD2 | TYR | A | 360 | 5.599  | 0.287  | 15.657 | 1.00 | 32.07 |
| ATOM | 978  | CE2 | TYR | A | 360 | 5.529  | -0.834 | 16.169 | 1.00 | 33.34 |
| ATOM | 979  | CZ  | TYR | A | 360 | 6.297  | -1.951 | 16.169 | 1.00 | 34.05 |
| ATOM | 980  | OH  | TYR | A | 360 | 6.223  | -3.060 | 16.990 | 1.00 | 36.20 |
| ATOM | 981  | C   | TYR | A | 360 | 5.349  | 3.419  | 12.600 | 1.00 | 28.56 |
| ATOM | 982  | O   | TYR | A | 360 | 5.423  | 3.694  | 11.402 | 1.00 | 28.97 |
| ATOM | 983  | N   | ILE | A | 361 | 5.348  | 4.348  | 13.551 | 1.00 | 26.89 |
| ATOM | 984  | CA  | ILE | A | 361 | 5.563  | 5.746  | 13.214 | 1.00 | 25.41 |
| ATOM | 985  | CB  | ILE | A | 361 | 4.309  | 6.633  | 13.404 | 1.00 | 23.70 |
| ATOM | 986  | CG2 | ILE | A | 361 | 3.165  | 6.160  | 12.512 | 1.00 | 24.32 |
| ATOM | 987  | CG1 | ILE | A | 361 | 3.863  | 6.643  | 14.853 | 1.00 | 22.87 |
| ATOM | 988  | CD1 | ILE | A | 361 | 2.843  | 7.723  | 15.138 | 1.00 | 23.09 |
| ATOM | 989  | C   | ILE | A | 361 | 6.725  | 6.243  | 14.078 | 1.00 | 26.25 |
| ATOM | 990  | O   | ILE | A | 361 | 7.210  | 5.526  | 14.961 | 1.00 | 27.16 |
| ATOM | 991  | N   | HIS | A | 362 | 7.211  | 7.441  | 13.783 | 1.00 | 24.92 |
| ATOM | 992  | CA  | HIS | A | 362 | 8.308  | 8.034  | 14.523 | 1.00 | 23.10 |
| ATOM | 993  | CB  | HIS | A | 362 | 9.261  | 8.699  | 13.530 | 1.00 | 21.01 |
| ATOM | 994  | CG  | HIS | A | 362 | 10.521 | 9.211  | 14.148 | 1.00 | 17.62 |
| ATOM | 995  | CD2 | HIS | A | 362 | 11.819 | 8.970  | 13.853 | 1.00 | 16.84 |
| ATOM | 996  | ND1 | HIS | A | 362 | 10.529 | 10.086 | 15.208 | 1.00 | 15.96 |
| ATOM | 997  | CE1 | HIS | A | 362 | 11.776 | 10.362 | 15.543 | 1.00 | 15.93 |
| ATOM | 998  | NE2 | HIS | A | 362 | 12.578 | 9.697  | 14.736 | 1.00 | 15.35 |
| ATOM | 999  | C   | HIS | A | 362 | 7.731  | 9.071  | 15.486 | 1.00 | 22.93 |
| ATOM | 1000 | O   | HIS | A | 362 | 8.033  | 9.077  | 16.680 | 1.00 | 23.88 |
| ATOM | 1001 | N   | ARG | A | 363 | 6.864  | 9.903  | 14.920 | 1.00 | 22.29 |
| ATOM | 1002 | CA  | ARG | A | 363 | 6.147  | 11.009 | 15.549 | 1.00 | 21.92 |
| ATOM | 1003 | CB  | ARG | A | 363 | 5.085  | 10.548 | 16.561 | 1.00 | 23.68 |
| ATOM | 1004 | CG  | ARG | A | 363 | 5.568  | 10.017 | 17.871 | 1.00 | 26.31 |
| ATOM | 1005 | CD  | ARG | A | 363 | 4.381  | 9.512  | 18.687 | 1.00 | 28.67 |
| ATOM | 1006 | NE  | ARG | A | 363 | 3.478  | 10.568 | 19.142 | 1.00 | 28.72 |
| ATOM | 1007 | CZ  | ARG | A | 363 | 2.151  | 10.461 | 19.121 | 1.00 | 29.40 |

Figure 5

```
ATOM   1008  NH1 ARG A 363      1.590   9.343  18.659  1.00 26.78
ATOM   1009  NH2 ARG A 363      1.388  11.446  19.605  1.00 28.46
ATOM   1010  C   ARG A 363      6.937  12.198  16.055  1.00 20.39
ATOM   1011  O   ARG A 363      6.361  13.148  16.580  1.00 20.45
ATOM   1012  N   ASP A 364      8.247  12.171  15.849  1.00 18.60
ATOM   1013  CA  ASP A 364      9.116  13.274  16.261  1.00 16.90
ATOM   1014  CB  ASP A 364      9.662  13.057  17.675  1.00 15.58
ATOM   1015  CG  ASP A 364      8.628  13.287  18.740  1.00 15.14
ATOM   1016  OD1 ASP A 364      8.170  14.446  18.920  1.00 14.37
ATOM   1017  OD2 ASP A 364      8.271  12.288  19.399  1.00 16.64
ATOM   1018  C   ASP A 364     10.277  13.392  15.289  1.00 15.91
ATOM   1019  O   ASP A 364     11.421  13.499  15.698  1.00 15.17
ATOM   1020  N   LEU A 365      9.984  13.334  14.000  1.00 15.26
ATOM   1021  CA  LEU A 365     11.037  13.416  13.010  1.00 15.84
ATOM   1022  CB  LEU A 365     10.657  12.607  11.772  1.00 13.41
ATOM   1023  CG  LEU A 365     11.646  12.591  10.608  1.00 12.67
ATOM   1024  CD1 LEU A 365     12.875  11.743  10.910  1.00 11.35
ATOM   1025  CD2 LEU A 365     10.919  12.059   9.414  1.00 11.97
ATOM   1026  C   LEU A 365     11.439  14.844  12.629  1.00 17.43
ATOM   1027  O   LEU A 365     10.648  15.636  12.117  1.00 18.34
ATOM   1028  N   ARG A 366     12.689  15.160  12.919  1.00 18.64
ATOM   1029  CA  ARG A 366     13.279  16.445  12.600  1.00 19.45
ATOM   1030  CB  ARG A 366     12.814  17.543  13.566  1.00 22.64
ATOM   1031  CG  ARG A 366     12.816  17.192  15.029  1.00 25.45
ATOM   1032  CD  ARG A 366     12.478  18.407  15.879  1.00 29.02
ATOM   1033  NE  ARG A 366     12.055  18.017  17.222  1.00 32.27
ATOM   1034  CZ  ARG A 366     10.912  17.387  17.479  1.00 33.33
ATOM   1035  NH1 ARG A 366     10.081  17.087  16.483  1.00 34.00
ATOM   1036  NH2 ARG A 366     10.609  17.039  18.722  1.00 32.67
ATOM   1037  C   ARG A 366     14.770  16.224  12.663  1.00 18.67
ATOM   1038  O   ARG A 366     15.219  15.242  13.228  1.00 18.99
ATOM   1039  N   ALA A 367     15.533  17.110  12.043  1.00 19.44
ATOM   1040  CA  ALA A 367     16.985  16.992  12.011  1.00 20.02
ATOM   1041  CB  ALA A 367     17.598  18.191  11.330  1.00 19.63
ATOM   1042  C   ALA A 367     17.593  16.812  13.388  1.00 20.93
ATOM   1043  O   ALA A 367     18.494  15.995  13.554  1.00 21.86
ATOM   1044  N   ALA A 368     17.049  17.509  14.387  1.00 20.74
ATOM   1045  CA  ALA A 368     17.578  17.415  15.744  1.00 19.96
ATOM   1046  CB  ALA A 368     16.816  18.344  16.677  1.00 20.26
ATOM   1047  C   ALA A 368     17.573  15.987  16.288  1.00 19.80
ATOM   1048  O   ALA A 368     18.408  15.625  17.110  1.00 20.05
ATOM   1049  N   ASN A 369     16.667  15.156  15.795  1.00 19.48
ATOM   1050  CA  ASN A 369     16.614  13.788  16.274  1.00 19.49
ATOM   1051  CB  ASN A 369     15.160  13.378  16.525  1.00 20.48
ATOM   1052  CG  ASN A 369     14.482  14.256  17.580  1.00 21.95
ATOM   1053  OD1 ASN A 369     15.094  14.655  18.581  1.00 23.78
ATOM   1054  ND2 ASN A 369     13.225  14.581  17.346  1.00 21.75
ATOM   1055  C   ASN A 369     17.345  12.789  15.376  1.00 18.50
ATOM   1056  O   ASN A 369     17.128  11.581  15.485  1.00 19.10
ATOM   1057  N   ILE A 370     18.204  13.296  14.490  1.00 16.84
ATOM   1058  CA  ILE A 370     18.984  12.439  13.598  1.00 15.96
ATOM   1059  CB  ILE A 370     18.844  12.833  12.108  1.00 15.83
ATOM   1060  CG2 ILE A 370     19.832  12.009  11.246  1.00 13.63
ATOM   1061  CG1 ILE A 370     17.398  12.645  11.642  1.00 13.36
ATOM   1062  CD1 ILE A 370     16.923  11.248  11.765  1.00 11.99
ATOM   1063  C   ILE A 370     20.453  12.525  13.990  1.00 15.62
ATOM   1064  O   ILE A 370     21.002  13.610  14.143  1.00 15.51
ATOM   1065  N   LEU A 371     21.100  11.372  14.086  1.00 15.54
ATOM   1066  CA  LEU A 371     22.488  11.317  14.495  1.00 15.75
ATOM   1067  CB  LEU A 371     22.646  10.326  15.657  1.00 14.37
```

Figure 5

| | | | | | | | | |
|---|---|---|---|---|---|---|---|---|
| ATOM | 1068 | CG | LEU | A | 371 | 21.765 | 10.568 | 16.895 | 1.00 14.87 |
| ATOM | 1069 | CD1 | LEU | A | 371 | 22.027 | 9.510 | 17.919 | 1.00 15.75 |
| ATOM | 1070 | CD2 | LEU | A | 371 | 22.008 | 11.931 | 17.528 | 1.00 14.16 |
| ATOM | 1071 | C | LEU | A | 371 | 23.492 | 11.035 | 13.366 | 1.00 16.27 |
| ATOM | 1072 | O | LEU | A | 371 | 23.223 | 10.279 | 12.436 | 1.00 15.25 |
| ATOM | 1073 | N | VAL | A | 372 | 24.632 | 11.710 | 13.442 | 1.00 16.52 |
| ATOM | 1074 | CA | VAL | A | 372 | 25.685 | 11.566 | 12.458 | 1.00 18.56 |
| ATOM | 1075 | CB | VAL | A | 372 | 26.164 | 12.972 | 11.963 | 1.00 18.16 |
| ATOM | 1076 | CG1 | VAL | A | 372 | 27.171 | 12.835 | 10.806 | 1.00 17.55 |
| ATOM | 1077 | CG2 | VAL | A | 372 | 24.968 | 13.806 | 11.535 | 1.00 15.94 |
| ATOM | 1078 | C | VAL | A | 372 | 26.848 | 10.763 | 13.071 | 1.00 19.68 |
| ATOM | 1079 | O | VAL | A | 372 | 27.199 | 10.946 | 14.242 | 1.00 19.72 |
| ATOM | 1080 | N | SER | A | 373 | 27.400 | 9.836 | 12.294 | 1.00 20.97 |
| ATOM | 1081 | CA | SER | A | 373 | 28.509 | 9.014 | 12.766 | 1.00 23.64 |
| ATOM | 1082 | CB | SER | A | 373 | 28.431 | 7.620 | 12.154 | 1.00 23.29 |
| ATOM | 1083 | OG | SER | A | 373 | 28.640 | 7.700 | 10.754 | 1.00 25.41 |
| ATOM | 1084 | C | SER | A | 373 | 29.840 | 9.652 | 12.380 | 1.00 25.67 |
| ATOM | 1085 | O | SER | A | 373 | 29.867 | 10.714 | 11.749 | 1.00 26.36 |
| ATOM | 1086 | N | ASP | A | 374 | 30.937 | 8.988 | 12.752 | 1.00 27.49 |
| ATOM | 1087 | CA | ASP | A | 374 | 32.286 | 9.455 | 12.432 | 1.00 29.09 |
| ATOM | 1088 | CB | ASP | A | 374 | 33.332 | 8.604 | 13.168 | 1.00 29.79 |
| ATOM | 1089 | CG | ASP | A | 374 | 33.152 | 7.112 | 12.931 | 1.00 29.95 |
| ATOM | 1090 | OD1 | ASP | A | 374 | 32.874 | 6.376 | 13.895 | 1.00 31.17 |
| ATOM | 1091 | OD2 | ASP | A | 374 | 33.302 | 6.666 | 11.785 | 1.00 30.27 |
| ATOM | 1092 | C | ASP | A | 374 | 32.511 | 9.413 | 10.909 | 1.00 29.73 |
| ATOM | 1093 | O | ASP | A | 374 | 33.310 | 10.194 | 10.357 | 1.00 29.69 |
| ATOM | 1094 | N | THR | A | 375 | 31.771 | 8.508 | 10.256 | 1.00 29.57 |
| ATOM | 1095 | CA | THR | A | 375 | 31.812 | 8.311 | 8.812 | 1.00 29.21 |
| ATOM | 1096 | CB | THR | A | 375 | 31.585 | 6.812 | 8.414 | 1.00 30.07 |
| ATOM | 1097 | OG1 | THR | A | 375 | 30.280 | 6.379 | 8.823 | 1.00 30.17 |
| ATOM | 1098 | CG2 | THR | A | 375 | 32.649 | 5.910 | 9.039 | 1.00 29.34 |
| ATOM | 1099 | C | THR | A | 375 | 30.750 | 9.160 | 8.115 | 1.00 28.52 |
| ATOM | 1100 | O | THR | A | 375 | 30.477 | 8.962 | 6.935 | 1.00 28.76 |
| ATOM | 1101 | N | LEU | A | 376 | 30.139 | 10.077 | 8.865 | 1.00 28.20 |
| ATOM | 1102 | CA | LEU | A | 376 | 29.098 | 11.004 | 8.375 | 1.00 27.01 |
| ATOM | 1103 | CB | LEU | A | 376 | 29.659 | 11.953 | 7.315 | 1.00 26.84 |
| ATOM | 1104 | CG | LEU | A | 376 | 30.929 | 12.731 | 7.640 | 1.00 27.19 |
| ATOM | 1105 | CD1 | LEU | A | 376 | 31.219 | 13.704 | 6.510 | 1.00 27.65 |
| ATOM | 1106 | CD2 | LEU | A | 376 | 30.773 | 13.465 | 8.961 | 1.00 26.78 |
| ATOM | 1107 | C | LEU | A | 376 | 27.789 | 10.400 | 7.865 | 1.00 26.66 |
| ATOM | 1108 | O | LEU | A | 376 | 27.080 | 11.020 | 7.078 | 1.00 26.40 |
| ATOM | 1109 | N | SER | A | 377 | 27.496 | 9.170 | 8.262 | 1.00 27.04 |
| ATOM | 1110 | CA | SER | A | 377 | 26.257 | 8.526 | 7.853 | 1.00 26.53 |
| ATOM | 1111 | CB | SER | A | 377 | 26.438 | 7.011 | 7.738 | 1.00 26.51 |
| ATOM | 1112 | OG | SER | A | 377 | 26.719 | 6.432 | 8.999 | 1.00 28.21 |
| ATOM | 1113 | C | SER | A | 377 | 25.209 | 8.867 | 8.911 | 1.00 25.99 |
| ATOM | 1114 | O | SER | A | 377 | 25.552 | 9.124 | 10.071 | 1.00 26.13 |
| ATOM | 1115 | N | CYS | A | 378 | 23.939 | 8.874 | 8.506 | 1.00 25.13 |
| ATOM | 1116 | CA | CYS | A | 378 | 22.838 | 9.209 | 9.411 | 1.00 23.26 |
| ATOM | 1117 | CB | CYS | A | 378 | 21.851 | 10.150 | 8.710 | 1.00 22.79 |
| ATOM | 1118 | SG | CYS | A | 378 | 22.605 | 11.636 | 8.021 | 1.00 20.86 |
| ATOM | 1119 | C | CYS | A | 378 | 22.083 | 8.000 | 9.961 | 1.00 21.87 |
| ATOM | 1120 | O | CYS | A | 378 | 21.906 | 7.013 | 9.256 | 1.00 21.61 |
| ATOM | 1121 | N | LYS | A | 379 | 21.649 | 8.115 | 11.223 | 1.00 21.42 |
| ATOM | 1122 | CA | LYS | A | 379 | 20.879 | 7.103 | 11.960 | 1.00 20.62 |
| ATOM | 1123 | CB | LYS | A | 379 | 21.756 | 6.344 | 12.946 | 1.00 21.35 |
| ATOM | 1124 | CG | LYS | A | 379 | 22.344 | 5.069 | 12.370 | 1.00 23.63 |
| ATOM | 1125 | CD | LYS | A | 379 | 23.547 | 4.613 | 13.157 | 1.00 25.31 |
| ATOM | 1126 | CE | LYS | A | 379 | 24.150 | 3.350 | 12.585 | 1.00 25.51 |
| ATOM | 1127 | NZ | LYS | A | 379 | 25.555 | 3.194 | 13.059 | 1.00 26.65 |

Figure 5

| ATOM | 1128 | C | LYS | A | 379 | 19.750 | 7.795 | 12.705 | 1.00 | 20.53 |
|------|------|-----|-----|---|-----|--------|--------|--------|------|-------|
| ATOM | 1129 | O | LYS | A | 379 | 19.925 | 8.892 | 13.227 | 1.00 | 21.20 |
| ATOM | 1130 | N | ILE | A | 380 | 18.594 | 7.144 | 12.769 | 1.00 | 20.27 |
| ATOM | 1131 | CA | ILE | A | 380 | 17.418 | 7.721 | 13.406 | 1.00 | 20.00 |
| ATOM | 1132 | CB | ILE | A | 380 | 16.135 | 7.248 | 12.715 | 1.00 | 18.60 |
| ATOM | 1133 | CG2 | ILE | A | 380 | 14.916 | 7.740 | 13.462 | 1.00 | 16.04 |
| ATOM | 1134 | CG1 | ILE | A | 380 | 16.122 | 7.726 | 11.271 | 1.00 | 17.24 |
| ATOM | 1135 | CD1 | ILE | A | 380 | 15.085 | 7.033 | 10.452 | 1.00 | 17.57 |
| ATOM | 1136 | C | ILE | A | 380 | 17.312 | 7.398 | 14.883 | 1.00 | 21.18 |
| ATOM | 1137 | O | ILE | A | 380 | 17.243 | 6.221 | 15.279 | 1.00 | 21.67 |
| ATOM | 1138 | N | ALA | A | 381 | 17.248 | 8.455 | 15.690 | 1.00 | 21.44 |
| ATOM | 1139 | CA | ALA | A | 381 | 17.138 | 8.313 | 17.131 | 1.00 | 21.58 |
| ATOM | 1140 | CB | ALA | A | 381 | 18.194 | 9.134 | 17.801 | 1.00 | 21.22 |
| ATOM | 1141 | C | ALA | A | 381 | 15.765 | 8.778 | 17.570 | 1.00 | 21.84 |
| ATOM | 1142 | O | ALA | A | 381 | 15.056 | 9.441 | 16.816 | 1.00 | 21.57 |
| ATOM | 1143 | N | ASP | A | 382 | 15.398 | 8.413 | 18.792 | 1.00 | 22.91 |
| ATOM | 1144 | CA | ASP | A | 382 | 14.124 | 8.805 | 19.399 | 1.00 | 23.34 |
| ATOM | 1145 | CB | ASP | A | 382 | 14.161 | 10.293 | 19.777 | 1.00 | 22.62 |
| ATOM | 1146 | CG | ASP | A | 382 | 15.002 | 10.565 | 21.022 | 1.00 | 21.21 |
| ATOM | 1147 | OD1 | ASP | A | 382 | 14.851 | 9.824 | 22.013 | 1.00 | 22.61 |
| ATOM | 1148 | OD2 | ASP | A | 382 | 15.799 | 11.525 | 21.021 | 1.00 | 19.79 |
| ATOM | 1149 | C | ASP | A | 382 | 12.868 | 8.481 | 18.590 | 1.00 | 24.00 |
| ATOM | 1150 | O | ASP | A | 382 | 11.891 | 9.232 | 18.611 | 1.00 | 23.99 |
| ATOM | 1151 | N | PHE | A | 383 | 12.884 | 7.328 | 17.929 | 1.00 | 24.57 |
| ATOM | 1152 | CA | PHE | A | 383 | 11.755 | 6.893 | 17.120 | 1.00 | 25.35 |
| ATOM | 1153 | CB | PHE | A | 383 | 12.216 | 6.109 | 15.865 | 1.00 | 23.86 |
| ATOM | 1154 | CG | PHE | A | 383 | 13.174 | 4.975 | 16.153 | 1.00 | 23.54 |
| ATOM | 1155 | CD1 | PHE | A | 383 | 12.699 | 3.678 | 16.355 | 1.00 | 23.09 |
| ATOM | 1156 | CD2 | PHE | A | 383 | 14.552 | 5.208 | 16.230 | 1.00 | 22.78 |
| ATOM | 1157 | CE1 | PHE | A | 383 | 13.578 | 2.630 | 16.635 | 1.00 | 22.40 |
| ATOM | 1158 | CE2 | PHE | A | 383 | 15.435 | 4.170 | 16.505 | 1.00 | 22.54 |
| ATOM | 1159 | CZ | PHE | A | 383 | 14.943 | 2.874 | 16.710 | 1.00 | 22.40 |
| ATOM | 1160 | C | PHE | A | 383 | 10.774 | 6.060 | 17.919 | 1.00 | 26.08 |
| ATOM | 1161 | O | PHE | A | 383 | 11.142 | 5.410 | 18.893 | 1.00 | 26.81 |
| ATOM | 1162 | N | GLY | A | 384 | 9.512 | 6.140 | 17.528 | 1.00 | 26.95 |
| ATOM | 1163 | CA | GLY | A | 384 | 8.478 | 5.360 | 18.169 | 1.00 | 27.95 |
| ATOM | 1164 | C | GLY | A | 384 | 8.029 | 5.762 | 19.553 | 1.00 | 28.98 |
| ATOM | 1165 | O | GLY | A | 384 | 7.355 | 4.961 | 20.202 | 1.00 | 30.38 |
| ATOM | 1166 | N | LEU | A | 385 | 8.384 | 6.960 | 20.025 | 1.00 | 29.26 |
| ATOM | 1167 | CA | LEU | A | 385 | 7.948 | 7.379 | 21.357 | 1.00 | 28.85 |
| ATOM | 1168 | CB | LEU | A | 385 | 8.647 | 8.667 | 21.819 | 1.00 | 27.07 |
| ATOM | 1169 | CG | LEU | A | 385 | 10.186 | 8.733 | 21.959 | 1.00 | 26.00 |
| ATOM | 1170 | CD1 | LEU | A | 385 | 10.530 | 9.683 | 23.079 | 1.00 | 24.35 |
| ATOM | 1171 | CD2 | LEU | A | 385 | 10.818 | 7.396 | 22.247 | 1.00 | 24.19 |
| ATOM | 1172 | C | LEU | A | 385 | 6.423 | 7.533 | 21.369 | 1.00 | 29.87 |
| ATOM | 1173 | O | LEU | A | 385 | 5.803 | 7.709 | 20.325 | 1.00 | 30.13 |
| ATOM | 1174 | N | ALA | A | 386 | 5.820 | 7.374 | 22.542 | 1.00 | 30.91 |
| ATOM | 1175 | CA | ALA | A | 386 | 4.370 | 7.471 | 22.698 | 1.00 | 31.41 |
| ATOM | 1176 | CB | ALA | A | 386 | 3.934 | 6.669 | 23.945 | 1.00 | 32.02 |
| ATOM | 1177 | C | ALA | A | 386 | 3.905 | 8.919 | 22.826 | 1.00 | 31.42 |
| ATOM | 1178 | O | ALA | A | 386 | 2.705 | 9.214 | 22.744 | 1.00 | 32.41 |
| ATOM | 1179 | N | ARG | A | 387 | 4.866 | 9.817 | 23.018 | 1.00 | 30.65 |
| ATOM | 1180 | CA | ARG | A | 387 | 4.582 | 11.231 | 23.201 | 1.00 | 29.03 |
| ATOM | 1181 | CB | ARG | A | 387 | 4.895 | 11.609 | 24.647 | 1.00 | 28.04 |
| ATOM | 1182 | CG | ARG | A | 387 | 6.359 | 11.366 | 24.993 | 1.00 | 28.37 |
| ATOM | 1183 | CD | ARG | A | 387 | 6.656 | 11.614 | 26.452 | 1.00 | 27.81 |
| ATOM | 1184 | NE | ARG | A | 387 | 8.080 | 11.486 | 26.733 | 1.00 | 26.82 |
| ATOM | 1185 | CZ | ARG | A | 387 | 8.952 | 12.467 | 26.545 | 1.00 | 28.10 |
| ATOM | 1186 | NH1 | ARG | A | 387 | 8.533 | 13.645 | 26.093 | 1.00 | 28.17 |
| ATOM | 1187 | NH2 | ARG | A | 387 | 10.250 | 12.253 | 26.737 | 1.00 | 29.02 |

Figure 5

```
ATOM   1188  C    ARG A 387      5.421  12.102  22.276  1.00 28.43
ATOM   1189  O    ARG A 387      6.249  11.600  21.508  1.00 27.70
ATOM   1190  N    LEU A 388      5.163  13.409  22.347  1.00 27.29
ATOM   1191  CA   LEU A 388      5.887  14.393  21.572  1.00 26.40
ATOM   1192  CB   LEU A 388      4.964  15.514  21.124  1.00 25.97
ATOM   1193  CG   LEU A 388      3.722  15.141  20.313  1.00 26.65
ATOM   1194  CD1  LEU A 388      3.139  16.423  19.723  1.00 27.27
ATOM   1195  CD2  LEU A 388      4.054  14.167  19.200  1.00 26.29
ATOM   1196  C    LEU A 388      6.987  14.961  22.463  1.00 26.83
ATOM   1197  O    LEU A 388      6.727  15.418  23.585  1.00 27.01
ATOM   1198  N    ILE A 389      8.217  14.930  21.953  1.00 25.88
ATOM   1199  CA   ILE A 389      9.361  15.419  22.700  1.00 24.42
ATOM   1200  CB   ILE A 389     10.546  14.413  22.650  1.00 23.06
ATOM   1201  CG2  ILE A 389     10.067  13.012  23.047  1.00 20.74
ATOM   1202  CG1  ILE A 389     11.220  14.447  21.269  1.00 21.82
ATOM   1203  CD1  ILE A 389     12.193  13.324  21.004  1.00 19.26
ATOM   1204  C    ILE A 389      9.850  16.782  22.244  1.00 25.29
ATOM   1205  O    ILE A 389      9.551  17.243  21.149  1.00 25.90
ATOM   1206  N    GLU A 390     10.603  17.421  23.125  1.00 26.90
ATOM   1207  CA   GLU A 390     11.195  18.722  22.877  1.00 27.96
ATOM   1208  CB   GLU A 390     10.678  19.734  23.907  1.00 29.57
ATOM   1209  CG   GLU A 390      9.150  19.731  24.000  1.00 33.57
ATOM   1210  CD   GLU A 390      8.563  20.906  24.766  1.00 35.89
ATOM   1211  OE1  GLU A 390      9.254  21.500  25.625  1.00 36.90
ATOM   1212  OE2  GLU A 390      7.383  21.225  24.505  1.00 38.26
ATOM   1213  C    GLU A 390     12.721  18.584  22.924  1.00 27.23
ATOM   1214  O    GLU A 390     13.258  17.641  23.501  1.00 25.57
ATOM   1215  N    ASP A 391     13.411  19.540  22.316  1.00 28.24
ATOM   1216  CA   ASP A 391     14.868  19.525  22.243  1.00 29.13
ATOM   1217  CB   ASP A 391     15.328  20.455  21.121  1.00 31.43
ATOM   1218  CG   ASP A 391     14.847  19.993  19.755  1.00 34.64
ATOM   1219  OD1  ASP A 391     14.456  18.797  19.616  1.00 35.73
ATOM   1220  OD2  ASP A 391     14.856  20.833  18.825  1.00 36.19
ATOM   1221  C    ASP A 391     15.655  19.799  23.519  1.00 28.71
ATOM   1222  O    ASP A 391     16.828  19.434  23.604  1.00 28.74
ATOM   1223  N    ASN A 392     15.002  20.408  24.510  1.00 28.30
ATOM   1224  CA   ASN A 392     15.626  20.744  25.789  1.00 26.87
ATOM   1225  CB   ASN A 392     15.076  22.091  26.310  1.00 27.56
ATOM   1226  CG   ASN A 392     13.565  22.053  26.634  1.00 28.68
ATOM   1227  OD1  ASN A 392     12.897  21.018  26.516  1.00 27.71
ATOM   1228  ND2  ASN A 392     13.035  23.195  27.068  1.00 29.09
ATOM   1229  C    ASN A 392     15.431  19.650  26.848  1.00 26.43
ATOM   1230  O    ASN A 392     15.750  19.859  28.024  1.00 26.32
ATOM   1231  N    GLU A 393     14.947  18.477  26.435  1.00 24.81
ATOM   1232  CA   GLU A 393     14.695  17.405  27.381  1.00 23.67
ATOM   1233  CB   GLU A 393     13.739  16.359  26.803  1.00 21.93
ATOM   1234  CG   GLU A 393     12.320  16.892  26.659  1.00 19.39
ATOM   1235  CD   GLU A 393     11.304  15.863  26.210  1.00 19.01
ATOM   1236  OE1  GLU A 393     11.652  14.672  26.049  1.00 18.49
ATOM   1237  OE2  GLU A 393     10.128  16.253  26.036  1.00 18.87
ATOM   1238  C    GLU A 393     15.939  16.766  27.927  1.00 24.84
ATOM   1239  O    GLU A 393     16.017  16.511  29.119  1.00 24.66
ATOM   1240  N    TYR A 394     16.925  16.530  27.073  1.00 26.65
ATOM   1241  CA   TYR A 394     18.170  15.921  27.528  1.00 28.60
ATOM   1242  CB   TYR A 394     18.279  14.464  27.054  1.00 28.07
ATOM   1243  CG   TYR A 394     17.140  13.566  27.525  1.00 27.98
ATOM   1244  CD1  TYR A 394     15.934  13.517  26.820  1.00 28.11
ATOM   1245  CE1  TYR A 394     14.882  12.698  27.230  1.00 28.60
ATOM   1246  CD2  TYR A 394     17.266  12.768  28.667  1.00 26.98
ATOM   1247  CE2  TYR A 394     16.214  11.940  29.097  1.00 27.42
```

Figure 5

```
ATOM   1248  CZ   TYR A 394      15.015  11.909  28.368  1.00 28.70
ATOM   1249  OH   TYR A 394      13.950  11.097  28.746  1.00 27.07
ATOM   1250  C    TYR A 394      19.412  16.739  27.157  1.00 30.26
ATOM   1251  O    TYR A 394      20.536  16.236  27.222  1.00 29.77
ATOM   1252  N    THR A 395      19.189  17.987  26.741  1.00 32.64
ATOM   1253  CA   THR A 395      20.260  18.926  26.401  1.00 36.52
ATOM   1254  CB   THR A 395      20.827  18.756  24.967  1.00 36.87
ATOM   1255  OG1  THR A 395      19.772  18.482  24.030  1.00 38.40
ATOM   1256  CG2  THR A 395      21.860  17.660  24.944  1.00 36.46
ATOM   1257  C    THR A 395      19.788  20.354  26.593  1.00 39.20
ATOM   1258  O    THR A 395      18.769  20.588  27.242  1.00 40.87
ATOM   1259  N    ALA A 396      20.511  21.315  26.025  1.00 42.18
ATOM   1260  CA   ALA A 396      20.129  22.709  26.195  1.00 44.53
ATOM   1261  CB   ALA A 396      21.004  23.357  27.285  1.00 44.44
ATOM   1262  C    ALA A 396      20.110  23.571  24.922  1.00 46.12
ATOM   1263  O    ALA A 396      20.940  24.476  24.760  1.00 47.48
ATOM   1264  N    ARG A 397      19.164  23.296  24.024  1.00 46.61
ATOM   1265  CA   ARG A 397      19.043  24.093  22.807  1.00 47.06
ATOM   1266  CB   ARG A 397      18.395  23.291  21.686  1.00 46.68
ATOM   1267  CG   ARG A 397      19.326  22.281  21.067  1.00 46.96
ATOM   1268  CD   ARG A 397      19.089  22.160  19.568  1.00 47.14
ATOM   1269  NE   ARG A 397      19.850  21.053  18.995  1.00 46.16
ATOM   1270  CZ   ARG A 397      19.605  19.769  19.249  1.00 45.54
ATOM   1271  NH1  ARG A 397      18.610  19.419  20.060  1.00 44.69
ATOM   1272  NH2  ARG A 397      20.382  18.834  18.722  1.00 44.70
ATOM   1273  C    ARG A 397      18.248  25.376  23.060  1.00 47.72
ATOM   1274  O    ARG A 397      18.783  26.456  22.713  1.00 48.15
ATOM   1275  CB   PRO A 403       7.846  20.272  18.637  1.00 26.63
ATOM   1276  CG   PRO A 403       8.482  20.782  19.926  1.00 28.23
ATOM   1277  C    PRO A 403       6.707  21.553  16.751  1.00 26.91
ATOM   1278  O    PRO A 403       6.638  20.655  15.879  1.00 27.14
ATOM   1279  N    PRO A 403       7.611  22.666  18.845  1.00 27.02
ATOM   1280  CD   PRO A 403       7.827  22.144  20.206  1.00 27.12
ATOM   1281  CA   PRO A 403       7.801  21.565  17.848  1.00 26.91
ATOM   1282  N    ILE A 404       5.905  22.615  16.780  1.00 25.22
ATOM   1283  CA   ILE A 404       4.805  22.829  15.853  1.00 22.26
ATOM   1284  CB   ILE A 404       4.003  24.116  16.266  1.00 22.11
ATOM   1285  CG2  ILE A 404       3.059  24.568  15.169  1.00 23.57
ATOM   1286  CG1  ILE A 404       3.193  23.828  17.523  1.00 23.25
ATOM   1287  CD1  ILE A 404       2.238  22.638  17.364  1.00 24.98
ATOM   1288  C    ILE A 404       5.222  22.895  14.383  1.00 19.32
ATOM   1289  O    ILE A 404       4.466  22.479  13.519  1.00 19.89
ATOM   1290  N    LYS A 405       6.442  23.345  14.111  1.00 16.67
ATOM   1291  CA   LYS A 405       6.919  23.489  12.737  1.00 15.71
ATOM   1292  CB   LYS A 405       8.167  24.373  12.697  1.00 15.79
ATOM   1293  CG   LYS A 405       7.942  25.735  13.331  1.00 16.64
ATOM   1294  CD   LYS A 405       9.055  26.704  13.005  1.00 16.21
ATOM   1295  CE   LYS A 405       8.722  28.082  13.539  1.00 16.45
ATOM   1296  NZ   LYS A 405       9.609  29.122  12.960  1.00 18.33
ATOM   1297  C    LYS A 405       7.131  22.222  11.914  1.00 14.61
ATOM   1298  O    LYS A 405       7.344  22.287  10.711  1.00 13.13
ATOM   1299  N    TRP A 406       7.076  21.076  12.574  1.00 15.37
ATOM   1300  CA   TRP A 406       7.240  19.785  11.917  1.00 15.76
ATOM   1301  CB   TRP A 406       8.336  18.972  12.607  1.00 16.16
ATOM   1302  CG   TRP A 406       9.719  19.516  12.407  1.00 16.96
ATOM   1303  CD2  TRP A 406      10.356  20.549  13.171  1.00 17.70
ATOM   1304  CE2  TRP A 406      11.654  20.719  12.641  1.00 17.16
ATOM   1305  CE3  TRP A 406       9.956  21.347  14.254  1.00 18.00
ATOM   1306  CD1  TRP A 406      10.632  19.110  11.475  1.00 17.20
ATOM   1307  NE1  TRP A 406      11.795  19.829  11.609  1.00 17.95
```

Figure 5

| | | | | | | | | |
|---|---|---|---|---|---|---|---|---|
| ATOM | 1308 | CZ2 | TRP | A | 406 | 12.553 | 21.652 | 13.153 | 1.00 16.55 |
| ATOM | 1309 | CZ3 | TRP | A | 406 | 10.857 | 22.276 | 14.765 | 1.00 16.62 |
| ATOM | 1310 | CH2 | TRP | A | 406 | 12.138 | 22.419 | 14.209 | 1.00 17.31 |
| ATOM | 1311 | C | TRP | A | 406 | 5.941 | 18.984 | 11.956 | 1.00 15.66 |
| ATOM | 1312 | O | TRP | A | 406 | 5.892 | 17.866 | 11.457 | 1.00 16.38 |
| ATOM | 1313 | N | THR | A | 407 | 4.897 | 19.553 | 12.555 | 1.00 15.20 |
| ATOM | 1314 | CA | THR | A | 407 | 3.602 | 18.879 | 12.667 | 1.00 14.83 |
| ATOM | 1315 | CB | THR | A | 407 | 2.919 | 19.224 | 14.026 | 1.00 13.66 |
| ATOM | 1316 | OG1 | THR | A | 407 | 3.876 | 19.112 | 15.076 | 1.00 15.14 |
| ATOM | 1317 | CG2 | THR | A | 407 | 1.824 | 18.244 | 14.339 | 1.00 12.76 |
| ATOM | 1318 | C | THR | A | 407 | 2.595 | 19.106 | 11.516 | 1.00 14.39 |
| ATOM | 1319 | O | THR | A | 407 | 2.190 | 20.244 | 11.238 | 1.00 15.26 |
| ATOM | 1320 | N | ALA | A | 408 | 2.172 | 18.000 | 10.896 | 1.00 13.51 |
| ATOM | 1321 | CA | ALA | A | 408 | 1.195 | 18.003 | 9.804 | 1.00 12.75 |
| ATOM | 1322 | CB | ALA | A | 408 | 0.876 | 16.582 | 9.356 | 1.00 11.12 |
| ATOM | 1323 | C | ALA | A | 408 | -0.068 | 18.659 | 10.275 | 1.00 13.41 |
| ATOM | 1324 | O | ALA | A | 408 | -0.377 | 18.640 | 11.464 | 1.00 15.14 |
| ATOM | 1325 | N | PRO | A | 409 | -0.862 | 19.193 | 9.343 | 1.00 13.42 |
| ATOM | 1326 | CD | PRO | A | 409 | -0.583 | 19.358 | 7.913 | 1.00 12.29 |
| ATOM | 1327 | CA | PRO | A | 409 | -2.115 | 19.856 | 9.707 | 1.00 13.46 |
| ATOM | 1328 | CB | PRO | A | 409 | -2.653 | 20.318 | 8.359 | 1.00 13.22 |
| ATOM | 1329 | CG | PRO | A | 409 | -1.412 | 20.556 | 7.577 | 1.00 12.77 |
| ATOM | 1330 | C | PRO | A | 409 | -3.111 | 18.955 | 10.422 | 1.00 13.93 |
| ATOM | 1331 | O | PRO | A | 409 | -3.747 | 19.376 | 11.381 | 1.00 15.33 |
| ATOM | 1332 | N | GLU | A | 410 | -3.251 | 17.717 | 9.970 | 1.00 15.04 |
| ATOM | 1333 | CA | GLU | A | 410 | -4.207 | 16.812 | 10.598 | 1.00 16.75 |
| ATOM | 1334 | CB | GLU | A | 410 | -4.369 | 15.515 | 9.786 | 1.00 16.29 |
| ATOM | 1335 | CG | GLU | A | 410 | -3.216 | 14.519 | 9.907 | 1.00 16.29 |
| ATOM | 1336 | CD | GLU | A | 410 | -2.137 | 14.653 | 8.842 | 1.00 16.45 |
| ATOM | 1337 | OE1 | GLU | A | 410 | -2.147 | 15.629 | 8.050 | 1.00 11.96 |
| ATOM | 1338 | OE2 | GLU | A | 410 | -1.280 | 13.735 | 8.810 | 1.00 17.73 |
| ATOM | 1339 | C | GLU | A | 410 | -3.813 | 16.503 | 12.037 | 1.00 18.07 |
| ATOM | 1340 | O | GLU | A | 410 | -4.678 | 16.271 | 12.884 | 1.00 19.26 |
| ATOM | 1341 | N | ALA | A | 411 | -2.508 | 16.503 | 12.313 | 1.00 19.26 |
| ATOM | 1342 | CA | ALA | A | 411 | -2.010 | 16.239 | 13.660 | 1.00 19.78 |
| ATOM | 1343 | CB | ALA | A | 411 | -0.535 | 15.960 | 13.621 | 1.00 19.10 |
| ATOM | 1344 | C | ALA | A | 411 | -2.305 | 17.423 | 14.586 | 1.00 20.85 |
| ATOM | 1345 | O | ALA | A | 411 | -2.668 | 17.241 | 15.743 | 1.00 21.18 |
| ATOM | 1346 | N | ILE | A | 412 | -2.178 | 18.636 | 14.052 | 1.00 21.81 |
| ATOM | 1347 | CA | ILE | A | 412 | -2.437 | 19.858 | 14.810 | 1.00 22.35 |
| ATOM | 1348 | CB | ILE | A | 412 | -2.048 | 21.112 | 14.000 | 1.00 21.60 |
| ATOM | 1349 | CG2 | ILE | A | 412 | -2.618 | 22.385 | 14.679 | 1.00 19.60 |
| ATOM | 1350 | CG1 | ILE | A | 412 | -0.521 | 21.153 | 13.828 | 1.00 20.77 |
| ATOM | 1351 | CD1 | ILE | A | 412 | 0.002 | 22.284 | 12.992 | 1.00 18.38 |
| ATOM | 1352 | C | ILE | A | 412 | -3.894 | 20.013 | 15.208 | 1.00 23.78 |
| ATOM | 1353 | O | ILE | A | 412 | -4.201 | 20.319 | 16.373 | 1.00 23.51 |
| ATOM | 1354 | N | ASN | A | 413 | -4.771 | 19.820 | 14.217 | 1.00 24.72 |
| ATOM | 1355 | CA | ASN | A | 413 | -6.215 | 19.958 | 14.379 | 1.00 24.69 |
| ATOM | 1356 | CB | ASN | A | 413 | -6.884 | 20.151 | 13.025 | 1.00 25.11 |
| ATOM | 1357 | CG | ASN | A | 413 | -6.469 | 21.428 | 12.350 | 1.00 26.42 |
| ATOM | 1358 | OD1 | ASN | A | 413 | -6.263 | 22.456 | 13.008 | 1.00 27.21 |
| ATOM | 1359 | ND2 | ASN | A | 413 | -6.344 | 21.380 | 11.022 | 1.00 25.18 |
| ATOM | 1360 | C | ASN | A | 413 | -6.925 | 18.835 | 15.095 | 1.00 24.84 |
| ATOM | 1361 | O | ASN | A | 413 | -7.859 | 19.088 | 15.853 | 1.00 25.17 |
| ATOM | 1362 | N | TYR | A | 414 | -6.533 | 17.596 | 14.826 | 1.00 24.84 |
| ATOM | 1363 | CA | TYR | A | 414 | -7.210 | 16.468 | 15.462 | 1.00 25.33 |
| ATOM | 1364 | CB | TYR | A | 414 | -8.041 | 15.711 | 14.410 | 1.00 27.92 |
| ATOM | 1365 | CG | TYR | A | 414 | -8.903 | 16.611 | 13.528 | 1.00 31.30 |
| ATOM | 1366 | CD1 | TYR | A | 414 | -10.199 | 16.978 | 13.913 | 1.00 31.73 |
| ATOM | 1367 | CE1 | TYR | A | 414 | -10.974 | 17.839 | 13.122 | 1.00 33.21 |

Figure 5

| ATOM | 1368 | CD2 | TYR | A | 414 | -8.403 | 17.125 | 12.320 | 1.00 | 32.81 |
| --- | --- | --- | --- | --- | --- | --- | --- | --- | --- | --- |
| ATOM | 1369 | CE2 | TYR | A | 414 | -9.171 | 17.989 | 11.521 | 1.00 | 33.10 |
| ATOM | 1370 | CZ | TYR | A | 414 | -10.454 | 18.343 | 11.932 | 1.00 | 34.12 |
| ATOM | 1371 | OH | TYR | A | 414 | -11.206 | 19.219 | 11.168 | 1.00 | 35.83 |
| ATOM | 1372 | C | TYR | A | 414 | -6.322 | 15.502 | 16.275 | 1.00 | 24.05 |
| ATOM | 1373 | O | TYR | A | 414 | -6.827 | 14.576 | 16.907 | 1.00 | 23.98 |
| ATOM | 1374 | N | GLY | A | 415 | -5.009 | 15.734 | 16.278 | 1.00 | 23.15 |
| ATOM | 1375 | CA | GLY | A | 415 | -4.093 | 14.874 | 17.019 | 1.00 | 20.49 |
| ATOM | 1376 | C | GLY | A | 415 | -3.966 | 13.488 | 16.422 | 1.00 | 19.78 |
| ATOM | 1377 | O | GLY | A | 415 | -3.758 | 12.492 | 17.140 | 1.00 | 19.85 |
| ATOM | 1378 | N | THR | A | 416 | -4.160 | 13.409 | 15.108 | 1.00 | 18.68 |
| ATOM | 1379 | CA | THR | A | 416 | -4.047 | 12.140 | 14.419 | 1.00 | 17.48 |
| ATOM | 1380 | CB | THR | A | 416 | -5.221 | 11.858 | 13.393 | 1.00 | 17.87 |
| ATOM | 1381 | OG1 | THR | A | 416 | -4.690 | 11.320 | 12.173 | 1.00 | 17.28 |
| ATOM | 1382 | CG2 | THR | A | 416 | -6.056 | 13.087 | 13.114 | 1.00 | 14.79 |
| ATOM | 1383 | C | THR | A | 416 | -2.660 | 12.039 | 13.799 | 1.00 | 16.58 |
| ATOM | 1384 | O | THR | A | 416 | -2.309 | 12.762 | 12.879 | 1.00 | 16.78 |
| ATOM | 1385 | N | PHE | A | 417 | -1.856 | 11.183 | 14.412 | 1.00 | 15.68 |
| ATOM | 1386 | CA | PHE | A | 417 | -0.491 | 10.926 | 14.018 | 1.00 | 13.57 |
| ATOM | 1387 | CB | PHE | A | 417 | 0.393 | 10.947 | 15.269 | 1.00 | 14.42 |
| ATOM | 1388 | CG | PHE | A | 417 | 0.555 | 12.323 | 15.890 | 1.00 | 14.86 |
| ATOM | 1389 | CD1 | PHE | A | 417 | -0.384 | 12.826 | 16.805 | 1.00 | 13.28 |
| ATOM | 1390 | CD2 | PHE | A | 417 | 1.649 | 13.128 | 15.541 | 1.00 | 14.36 |
| ATOM | 1391 | CE1 | PHE | A | 417 | -0.231 | 14.114 | 17.350 | 1.00 | 12.42 |
| ATOM | 1392 | CE2 | PHE | A | 417 | 1.805 | 14.417 | 16.086 | 1.00 | 12.49 |
| ATOM | 1393 | CZ | PHE | A | 417 | 0.870 | 14.906 | 16.982 | 1.00 | 10.97 |
| ATOM | 1394 | C | PHE | A | 417 | -0.352 | 9.584 | 13.299 | 1.00 | 12.65 |
| ATOM | 1395 | O | PHE | A | 417 | -0.782 | 8.547 | 13.795 | 1.00 | 13.05 |
| ATOM | 1396 | N | THR | A | 418 | 0.243 | 9.624 | 12.115 | 1.00 | 12.46 |
| ATOM | 1397 | CA | THR | A | 418 | 0.475 | 8.440 | 11.285 | 1.00 | 11.85 |
| ATOM | 1398 | CB | THR | A | 418 | -0.632 | 8.260 | 10.197 | 1.00 | 12.14 |
| ATOM | 1399 | OG1 | THR | A | 418 | -0.540 | 9.303 | 9.217 | 1.00 | 13.16 |
| ATOM | 1400 | CG2 | THR | A | 418 | -2.012 | 8.300 | 10.826 | 1.00 | 11.62 |
| ATOM | 1401 | C | THR | A | 418 | 1.813 | 8.575 | 10.572 | 1.00 | 11.40 |
| ATOM | 1402 | O | THR | A | 418 | 2.565 | 9.530 | 10.804 | 1.00 | 11.59 |
| ATOM | 1403 | N | ILE | A | 419 | 2.102 | 7.616 | 9.699 | 1.00 | 11.82 |
| ATOM | 1404 | CA | ILE | A | 419 | 3.338 | 7.623 | 8.915 | 1.00 | 11.42 |
| ATOM | 1405 | CB | ILE | A | 419 | 3.544 | 6.290 | 8.135 | 1.00 | 10.97 |
| ATOM | 1406 | CG2 | ILE | A | 419 | 2.554 | 6.146 | 6.976 | 1.00 | 9.50 |
| ATOM | 1407 | CG1 | ILE | A | 419 | 4.962 | 6.216 | 7.591 | 1.00 | 11.72 |
| ATOM | 1408 | CD1 | ILE | A | 419 | 5.997 | 6.125 | 8.659 | 1.00 | 11.22 |
| ATOM | 1409 | C | ILE | A | 419 | 3.291 | 8.807 | 7.952 | 1.00 | 12.53 |
| ATOM | 1410 | O | ILE | A | 419 | 4.322 | 9.386 | 7.632 | 1.00 | 14.07 |
| ATOM | 1411 | N | LYS | A | 420 | 2.082 | 9.211 | 7.562 | 1.00 | 12.37 |
| ATOM | 1412 | CA | LYS | A | 420 | 1.881 | 10.333 | 6.656 | 1.00 | 11.66 |
| ATOM | 1413 | CB | LYS | A | 420 | 0.453 | 10.346 | 6.155 | 1.00 | 10.50 |
| ATOM | 1414 | CG | LYS | A | 420 | 0.127 | 9.156 | 5.286 | 1.00 | 10.64 |
| ATOM | 1415 | CD | LYS | A | 420 | 1.070 | 9.106 | 4.101 | 1.00 | 9.48 |
| ATOM | 1416 | CE | LYS | A | 420 | 0.734 | 7.961 | 3.188 | 1.00 | 6.27 |
| ATOM | 1417 | NZ | LYS | A | 420 | 1.643 | 8.031 | 2.037 | 1.00 | 3.85 |
| ATOM | 1418 | C | LYS | A | 420 | 2.243 | 11.663 | 7.298 | 1.00 | 12.17 |
| ATOM | 1419 | O | LYS | A | 420 | 2.724 | 12.571 | 6.623 | 1.00 | 11.80 |
| ATOM | 1420 | N | SER | A | 421 | 1.980 | 11.798 | 8.595 | 1.00 | 13.09 |
| ATOM | 1421 | CA | SER | A | 421 | 2.363 | 13.020 | 9.291 | 1.00 | 12.94 |
| ATOM | 1422 | CB | SER | A | 421 | 1.605 | 13.203 | 10.601 | 1.00 | 10.48 |
| ATOM | 1423 | OG | SER | A | 421 | 1.407 | 11.981 | 11.241 | 1.00 | 10.74 |
| ATOM | 1424 | C | SER | A | 421 | 3.878 | 13.005 | 9.496 | 1.00 | 14.26 |
| ATOM | 1425 | O | SER | A | 421 | 4.488 | 14.043 | 9.770 | 1.00 | 17.73 |
| ATOM | 1426 | N | ASP | A | 422 | 4.477 | 11.821 | 9.358 | 1.00 | 14.12 |
| ATOM | 1427 | CA | ASP | A | 422 | 5.926 | 11.651 | 9.452 | 1.00 | 13.33 |

Figure 5

```
ATOM   1428  CB   ASP A 422      6.314  10.181   9.614  1.00 13.98
ATOM   1429  CG   ASP A 422      6.343   9.723  11.052  1.00 13.48
ATOM   1430  OD1  ASP A 422      6.165  10.529  11.975  1.00 15.44
ATOM   1431  OD2  ASP A 422      6.561   8.527  11.266  1.00 13.97
ATOM   1432  C    ASP A 422      6.514  12.129   8.144  1.00 13.18
ATOM   1433  O    ASP A 422      7.573  12.747   8.128  1.00 14.14
ATOM   1434  N    VAL A 423      5.870  11.764   7.037  1.00 12.68
ATOM   1435  CA   VAL A 423      6.325  12.201   5.724  1.00 11.07
ATOM   1436  CB   VAL A 423      5.537  11.541   4.561  1.00 10.88
ATOM   1437  CG1  VAL A 423      5.893  12.196   3.234  1.00  7.93
ATOM   1438  CG2  VAL A 423      5.867  10.039   4.482  1.00  8.65
ATOM   1439  C    VAL A 423      6.225  13.721   5.687  1.00 11.57
ATOM   1440  O    VAL A 423      7.104  14.380   5.136  1.00 13.05
ATOM   1441  N    TRP A 424      5.214  14.290   6.342  1.00 11.03
ATOM   1442  CA   TRP A 424      5.103  15.747   6.385  1.00 11.25
ATOM   1443  CB   TRP A 424      3.858  16.209   7.146  1.00  9.77
ATOM   1444  CG   TRP A 424      3.790  17.719   7.274  1.00  8.20
ATOM   1445  CD2  TRP A 424      2.909  18.610   6.577  1.00  7.60
ATOM   1446  CE2  TRP A 424      3.249  19.925   6.968  1.00  7.46
ATOM   1447  CE3  TRP A 424      1.870  18.426   5.651  1.00  8.05
ATOM   1448  CD1  TRP A 424      4.596  18.513   8.049  1.00  8.09
ATOM   1449  NE1  TRP A 424      4.280  19.835   7.865  1.00  7.69
ATOM   1450  CZ2  TRP A 424      2.590  21.054   6.467  1.00  7.89
ATOM   1451  CZ3  TRP A 424      1.212  19.548   5.152  1.00  7.99
ATOM   1452  CH2  TRP A 424      1.581  20.847   5.564  1.00  8.91
ATOM   1453  C    TRP A 424      6.361  16.261   7.072  1.00 12.24
ATOM   1454  O    TRP A 424      7.056  17.110   6.520  1.00 13.56
ATOM   1455  N    SER A 425      6.665  15.703   8.248  1.00 13.32
ATOM   1456  CA   SER A 425      7.863  16.059   9.038  1.00 14.86
ATOM   1457  CB   SER A 425      8.000  15.162  10.265  1.00 14.95
ATOM   1458  OG   SER A 425      7.104  15.561  11.271  1.00 18.52
ATOM   1459  C    SER A 425      9.159  15.929   8.273  1.00 14.21
ATOM   1460  O    SER A 425     10.086  16.698   8.469  1.00 15.16
ATOM   1461  N    PHE A 426      9.245  14.881   7.471  1.00 14.89
ATOM   1462  CA   PHE A 426     10.430  14.626   6.680  1.00 14.89
ATOM   1463  CB   PHE A 426     10.313  13.291   5.951  1.00 14.99
ATOM   1464  CG   PHE A 426     11.510  12.966   5.123  1.00 15.28
ATOM   1465  CD1  PHE A 426     12.704  12.603   5.732  1.00 14.53
ATOM   1466  CD2  PHE A 426     11.471  13.087   3.749  1.00 15.51
ATOM   1467  CE1  PHE A 426     13.833  12.377   4.986  1.00 15.21
ATOM   1468  CE2  PHE A 426     12.609  12.860   2.992  1.00 15.88
ATOM   1469  CZ   PHE A 426     13.793  12.506   3.617  1.00 15.74
ATOM   1470  C    PHE A 426     10.664  15.746   5.675  1.00 15.03
ATOM   1471  O    PHE A 426     11.798  16.174   5.481  1.00 15.62
ATOM   1472  N    GLY A 427      9.594  16.195   5.020  1.00 14.66
ATOM   1473  CA   GLY A 427      9.718  17.267   4.053  1.00 14.04
ATOM   1474  C    GLY A 427     10.229  18.509   4.752  1.00 14.24
ATOM   1475  O    GLY A 427     11.021  19.263   4.192  1.00 14.55
ATOM   1476  N    ILE A 428      9.778  18.721   5.988  1.00 14.15
ATOM   1477  CA   ILE A 428     10.216  19.869   6.766  1.00 13.78
ATOM   1478  CB   ILE A 428      9.446  19.996   8.095  1.00 13.41
ATOM   1479  CG2  ILE A 428     10.056  21.098   8.926  1.00 13.48
ATOM   1480  CG1  ILE A 428      7.973  20.326   7.844  1.00 13.94
ATOM   1481  CD1  ILE A 428      7.749  21.680   7.125  1.00 12.77
ATOM   1482  C    ILE A 428     11.688  19.655   7.074  1.00 14.71
ATOM   1483  O    ILE A 428     12.496  20.570   6.953  1.00 15.26
ATOM   1484  N    LEU A 429     12.029  18.412   7.407  1.00 14.71
ATOM   1485  CA   LEU A 429     13.397  18.040   7.721  1.00 14.66
ATOM   1486  CB   LEU A 429     13.469  16.554   8.106  1.00 14.23
ATOM   1487  CG   LEU A 429     14.742  15.969   8.743  1.00 13.20
```

Figure 5

| | | | | | | | | | |
|---|---|---|---|---|---|---|---|---|---|
| ATOM | 1488 | CD1 | LEU | A | 429 | 14.434 | 14.643 | 9.391 | 1.00 13.30 |
| ATOM | 1489 | CD2 | LEU | A | 429 | 15.825 | 15.798 | 7.735 | 1.00 12.99 |
| ATOM | 1490 | C | LEU | A | 429 | 14.303 | 18.315 | 6.534 | 1.00 14.82 |
| ATOM | 1491 | O | LEU | A | 429 | 15.432 | 18.759 | 6.717 | 1.00 16.52 |
| ATOM | 1492 | N | LEU | A | 430 | 13.804 | 18.057 | 5.327 | 1.00 14.49 |
| ATOM | 1493 | CA | LEU | A | 430 | 14.574 | 18.266 | 4.109 | 1.00 14.55 |
| ATOM | 1494 | CB | LEU | A | 430 | 13.771 | 17.853 | 2.888 | 1.00 12.71 |
| ATOM | 1495 | CG | LEU | A | 430 | 13.696 | 16.390 | 2.487 | 1.00 11.72 |
| ATOM | 1496 | CD1 | LEU | A | 430 | 12.771 | 16.288 | 1.269 | 1.00 8.20 |
| ATOM | 1497 | CD2 | LEU | A | 430 | 15.079 | 15.862 | 2.159 | 1.00 9.95 |
| ATOM | 1498 | C | LEU | A | 430 | 15.043 | 19.712 | 3.947 | 1.00 16.10 |
| ATOM | 1499 | O | LEU | A | 430 | 16.087 | 19.958 | 3.339 | 1.00 17.27 |
| ATOM | 1500 | N | THR | A | 431 | 14.270 | 20.669 | 4.463 | 1.00 16.36 |
| ATOM | 1501 | CA | THR | A | 431 | 14.669 | 22.073 | 4.383 | 1.00 15.56 |
| ATOM | 1502 | CB | THR | A | 431 | 13.518 | 23.016 | 4.703 | 1.00 13.77 |
| ATOM | 1503 | OG1 | THR | A | 431 | 13.053 | 22.743 | 6.023 | 1.00 13.07 |
| ATOM | 1504 | CG2 | THR | A | 431 | 12.386 | 22.854 | 3.715 | 1.00 12.97 |
| ATOM | 1505 | C | THR | A | 431 | 15.802 | 22.324 | 5.392 | 1.00 17.31 |
| ATOM | 1506 | O | THR | A | 431 | 16.698 | 23.118 | 5.122 | 1.00 17.77 |
| ATOM | 1507 | N | GLU | A | 432 | 15.734 | 21.670 | 6.560 | 1.00 18.24 |
| ATOM | 1508 | CA | GLU | A | 432 | 16.768 | 21.782 | 7.594 | 1.00 18.18 |
| ATOM | 1509 | CB | GLU | A | 432 | 16.430 | 20.928 | 8.818 | 1.00 18.25 |
| ATOM | 1510 | CG | GLU | A | 432 | 15.403 | 21.511 | 9.771 | 1.00 20.34 |
| ATOM | 1511 | CD | GLU | A | 432 | 15.078 | 20.562 | 10.922 | 1.00 20.99 |
| ATOM | 1512 | OE1 | GLU | A | 432 | 14.507 | 19.483 | 10.668 | 1.00 18.50 |
| ATOM | 1513 | OE2 | GLU | A | 432 | 15.394 | 20.896 | 12.086 | 1.00 22.98 |
| ATOM | 1514 | C | GLU | A | 432 | 18.080 | 21.271 | 7.013 | 1.00 19.09 |
| ATOM | 1515 | O | GLU | A | 432 | 19.137 | 21.833 | 7.271 | 1.00 19.94 |
| ATOM | 1516 | N | ILE | A | 433 | 18.007 | 20.180 | 6.257 | 1.00 18.89 |
| ATOM | 1517 | CA | ILE | A | 433 | 19.186 | 19.596 | 5.626 | 1.00 19.28 |
| ATOM | 1518 | CB | ILE | A | 433 | 18.856 | 18.249 | 4.959 | 1.00 19.10 |
| ATOM | 1519 | CG2 | ILE | A | 433 | 20.040 | 17.745 | 4.143 | 1.00 19.45 |
| ATOM | 1520 | CG1 | ILE | A | 433 | 18.494 | 17.219 | 6.022 | 1.00 20.56 |
| ATOM | 1521 | CD1 | ILE | A | 433 | 18.361 | 15.814 | 5.480 | 1.00 21.17 |
| ATOM | 1522 | C | ILE | A | 433 | 19.808 | 20.479 | 4.552 | 1.00 20.05 |
| ATOM | 1523 | O | ILE | A | 433 | 21.028 | 20.614 | 4.482 | 1.00 20.49 |
| ATOM | 1524 | N | VAL | A | 434 | 18.970 | 21.076 | 3.712 | 1.00 21.11 |
| ATOM | 1525 | CA | VAL | A | 434 | 19.465 | 21.888 | 2.613 | 1.00 22.20 |
| ATOM | 1526 | CB | VAL | A | 434 | 18.485 | 21.826 | 1.433 | 1.00 22.20 |
| ATOM | 1527 | CG1 | VAL | A | 434 | 17.379 | 22.856 | 1.591 | 1.00 22.15 |
| ATOM | 1528 | CG2 | VAL | A | 434 | 19.218 | 21.987 | 0.136 | 1.00 23.46 |
| ATOM | 1529 | C | VAL | A | 434 | 19.847 | 23.338 | 2.958 | 1.00 23.75 |
| ATOM | 1530 | O | VAL | A | 434 | 20.507 | 24.019 | 2.166 | 1.00 25.10 |
| ATOM | 1531 | N | THR | A | 435 | 19.451 | 23.790 | 4.148 | 1.00 24.58 |
| ATOM | 1532 | CA | THR | A | 435 | 19.742 | 25.144 | 4.627 | 1.00 24.34 |
| ATOM | 1533 | CB | THR | A | 435 | 18.471 | 25.849 | 5.148 | 1.00 24.10 |
| ATOM | 1534 | OG1 | THR | A | 435 | 17.977 | 25.156 | 6.305 | 1.00 23.37 |
| ATOM | 1535 | CG2 | THR | A | 435 | 17.390 | 25.897 | 4.072 | 1.00 22.56 |
| ATOM | 1536 | C | THR | A | 435 | 20.721 | 25.041 | 5.783 | 1.00 25.54 |
| ATOM | 1537 | O | THR | A | 435 | 20.797 | 25.929 | 6.629 | 1.00 25.71 |
| ATOM | 1538 | N | HIS | A | 436 | 21.402 | 23.904 | 5.846 | 1.00 27.37 |
| ATOM | 1539 | CA | HIS | A | 436 | 22.372 | 23.604 | 6.886 | 1.00 28.77 |
| ATOM | 1540 | CB | HIS | A | 436 | 23.708 | 24.246 | 6.543 | 1.00 30.50 |
| ATOM | 1541 | CG | HIS | A | 436 | 24.305 | 23.719 | 5.277 | 1.00 33.96 |
| ATOM | 1542 | CD2 | HIS | A | 436 | 24.815 | 22.504 | 4.971 | 1.00 35.33 |
| ATOM | 1543 | ND1 | HIS | A | 436 | 24.389 | 24.472 | 4.126 | 1.00 36.03 |
| ATOM | 1544 | CE1 | HIS | A | 436 | 24.922 | 23.739 | 3.162 | 1.00 35.81 |
| ATOM | 1545 | NE2 | HIS | A | 436 | 25.190 | 22.542 | 3.649 | 1.00 35.76 |
| ATOM | 1546 | C | HIS | A | 436 | 21.957 | 23.917 | 8.327 | 1.00 29.31 |
| ATOM | 1547 | O | HIS | A | 436 | 22.682 | 24.596 | 9.055 | 1.00 29.96 |

Figure 5

| ATOM | 1548 | N | GLY | A | 437 | 20.779 | 23.447 | 8.725 | 1.00 | 28.83 |
| --- | --- | --- | --- | --- | --- | --- | --- | --- | --- | --- |
| ATOM | 1549 | CA | GLY | A | 437 | 20.330 | 23.649 | 10.089 | 1.00 | 29.20 |
| ATOM | 1550 | C | GLY | A | 437 | 19.413 | 24.812 | 10.373 | 1.00 | 29.68 |
| ATOM | 1551 | O | GLY | A | 437 | 19.081 | 25.064 | 11.529 | 1.00 | 29.75 |
| ATOM | 1552 | N | ARG | A | 438 | 18.973 | 25.503 | 9.332 | 1.00 | 30.70 |
| ATOM | 1553 | CA | ARG | A | 438 | 18.079 | 26.647 | 9.518 | 1.00 | 32.22 |
| ATOM | 1554 | CB | ARG | A | 438 | 17.918 | 27.396 | 8.186 | 1.00 | 35.65 |
| ATOM | 1555 | CG | ARG | A | 438 | 17.480 | 28.864 | 8.265 | 1.00 | 39.03 |
| ATOM | 1556 | CD | ARG | A | 438 | 15.968 | 29.035 | 8.448 | 1.00 | 43.00 |
| ATOM | 1557 | NE | ARG | A | 438 | 15.148 | 28.366 | 7.425 | 1.00 | 46.56 |
| ATOM | 1558 | CZ | ARG | A | 438 | 15.077 | 28.739 | 6.144 | 1.00 | 48.47 |
| ATOM | 1559 | NH1 | ARG | A | 438 | 15.787 | 29.784 | 5.713 | 1.00 | 50.04 |
| ATOM | 1560 | NH2 | ARG | A | 438 | 14.284 | 28.082 | 5.298 | 1.00 | 47.18 |
| ATOM | 1561 | C | ARG | A | 438 | 16.721 | 26.194 | 10.062 | 1.00 | 30.97 |
| ATOM | 1562 | O | ARG | A | 438 | 16.219 | 25.131 | 9.707 | 1.00 | 31.37 |
| ATOM | 1563 | N | ILE | A | 439 | 16.161 | 26.980 | 10.973 | 1.00 | 30.20 |
| ATOM | 1564 | CA | ILE | A | 439 | 14.865 | 26.661 | 11.568 | 1.00 | 29.07 |
| ATOM | 1565 | CB | ILE | A | 439 | 14.636 | 27.492 | 12.863 | 1.00 | 28.98 |
| ATOM | 1566 | CG2 | ILE | A | 439 | 13.229 | 27.262 | 13.424 | 1.00 | 26.96 |
| ATOM | 1567 | CG1 | ILE | A | 439 | 15.695 | 27.100 | 13.900 | 1.00 | 29.85 |
| ATOM | 1568 | CD1 | ILE | A | 439 | 15.621 | 27.866 | 15.208 | 1.00 | 30.50 |
| ATOM | 1569 | C | ILE | A | 439 | 13.744 | 26.904 | 10.550 | 1.00 | 28.08 |
| ATOM | 1570 | O | ILE | A | 439 | 13.686 | 27.961 | 9.923 | 1.00 | 27.85 |
| ATOM | 1571 | N | PRO | A | 440 | 12.829 | 25.932 | 10.388 | 1.00 | 27.15 |
| ATOM | 1572 | CD | PRO | A | 440 | 12.737 | 24.678 | 11.152 | 1.00 | 25.90 |
| ATOM | 1573 | CA | PRO | A | 440 | 11.710 | 26.043 | 9.441 | 1.00 | 27.19 |
| ATOM | 1574 | CB | PRO | A | 440 | 10.870 | 24.813 | 9.775 | 1.00 | 27.25 |
| ATOM | 1575 | CG | PRO | A | 440 | 11.898 | 23.831 | 10.259 | 1.00 | 25.93 |
| ATOM | 1576 | C | PRO | A | 440 | 10.916 | 27.329 | 9.639 | 1.00 | 26.99 |
| ATOM | 1577 | O | PRO | A | 440 | 10.929 | 27.892 | 10.735 | 1.00 | 26.93 |
| ATOM | 1578 | N | TYR | A | 441 | 10.276 | 27.814 | 8.572 | 1.00 | 27.22 |
| ATOM | 1579 | CA | TYR | A | 441 | 9.471 | 29.042 | 8.621 | 1.00 | 27.75 |
| ATOM | 1580 | CB | TYR | A | 441 | 8.148 | 28.770 | 9.332 | 1.00 | 26.67 |
| ATOM | 1581 | CG | TYR | A | 441 | 7.365 | 27.621 | 8.747 | 1.00 | 25.96 |
| ATOM | 1582 | CD1 | TYR | A | 441 | 6.526 | 27.810 | 7.648 | 1.00 | 24.09 |
| ATOM | 1583 | CE1 | TYR | A | 441 | 5.806 | 26.762 | 7.118 | 1.00 | 23.77 |
| ATOM | 1584 | CD2 | TYR | A | 441 | 7.456 | 26.344 | 9.297 | 1.00 | 24.44 |
| ATOM | 1585 | CE2 | TYR | A | 441 | 6.734 | 25.281 | 8.766 | 1.00 | 24.12 |
| ATOM | 1586 | CZ | TYR | A | 441 | 5.914 | 25.496 | 7.682 | 1.00 | 23.52 |
| ATOM | 1587 | OH | TYR | A | 441 | 5.202 | 24.443 | 7.163 | 1.00 | 23.72 |
| ATOM | 1588 | C | TYR | A | 441 | 10.210 | 30.171 | 9.349 | 1.00 | 29.59 |
| ATOM | 1589 | O | TYR | A | 441 | 9.789 | 30.611 | 10.425 | 1.00 | 29.80 |
| ATOM | 1590 | N | PRO | A | 442 | 11.319 | 30.659 | 8.771 | 1.00 | 31.00 |
| ATOM | 1591 | CD | PRO | A | 442 | 11.874 | 30.348 | 7.438 | 1.00 | 31.64 |
| ATOM | 1592 | CA | PRO | A | 442 | 12.074 | 31.730 | 9.421 | 1.00 | 31.70 |
| ATOM | 1593 | CB | PRO | A | 442 | 13.248 | 31.938 | 8.461 | 1.00 | 32.72 |
| ATOM | 1594 | CG | PRO | A | 442 | 12.660 | 31.591 | 7.113 | 1.00 | 31.71 |
| ATOM | 1595 | C | PRO | A | 442 | 11.245 | 32.999 | 9.622 | 1.00 | 32.55 |
| ATOM | 1596 | O | PRO | A | 442 | 10.509 | 33.422 | 8.723 | 1.00 | 32.46 |
| ATOM | 1597 | N | GLY | A | 443 | 11.351 | 33.581 | 10.817 | 1.00 | 32.96 |
| ATOM | 1598 | CA | GLY | A | 443 | 10.612 | 34.792 | 11.129 | 1.00 | 33.36 |
| ATOM | 1599 | C | GLY | A | 443 | 9.113 | 34.594 | 11.306 | 1.00 | 33.93 |
| ATOM | 1600 | O | GLY | A | 443 | 8.301 | 35.447 | 10.931 | 1.00 | 35.09 |
| ATOM | 1601 | N | MET | A | 444 | 8.746 | 33.472 | 11.909 | 1.00 | 32.95 |
| ATOM | 1602 | CA | MET | A | 444 | 7.353 | 33.131 | 12.156 | 1.00 | 32.05 |
| ATOM | 1603 | CB | MET | A | 444 | 6.824 | 32.171 | 11.078 | 1.00 | 31.95 |
| ATOM | 1604 | CG | MET | A | 444 | 6.239 | 32.802 | 9.826 | 1.00 | 30.81 |
| ATOM | 1605 | SD | MET | A | 444 | 5.422 | 31.578 | 8.742 | 1.00 | 29.14 |
| ATOM | 1606 | CE | MET | A | 444 | 5.186 | 32.523 | 7.234 | 1.00 | 29.01 |
| ATOM | 1607 | C | MET | A | 444 | 7.339 | 32.394 | 13.479 | 1.00 | 32.14 |

Figure 5

```
ATOM   1608  O    MET A 444       8.160  31.500  13.688  1.00 32.14
ATOM   1609  N    THR A 445       6.438  32.767  14.381  1.00 32.25
ATOM   1610  CA   THR A 445       6.356  32.066  15.662  1.00 32.74
ATOM   1611  CB   THR A 445       5.771  32.951  16.787  1.00 32.97
ATOM   1612  OG1  THR A 445       4.458  33.398  16.423  1.00 33.29
ATOM   1613  CG2  THR A 445       6.668  34.155  17.037  1.00 33.74
ATOM   1614  C    THR A 445       5.472  30.844  15.460  1.00 32.75
ATOM   1615  O    THR A 445       4.985  30.603  14.358  1.00 33.62
ATOM   1616  N    ASN A 446       5.268  30.066  16.512  1.00 32.90
ATOM   1617  CA   ASN A 446       4.423  28.884  16.404  1.00 32.90
ATOM   1618  CB   ASN A 446       4.472  28.039  17.690  1.00 34.38
ATOM   1619  CG   ASN A 446       5.699  27.136  17.744  1.00 36.41
ATOM   1620  OD1  ASN A 446       6.585  27.225  16.886  1.00 38.19
ATOM   1621  ND2  ASN A 446       5.744  26.240  18.729  1.00 37.18
ATOM   1622  C    ASN A 446       2.986  29.223  15.998  1.00 31.45
ATOM   1623  O    ASN A 446       2.509  28.727  14.974  1.00 30.17
ATOM   1624  N    PRO A 447       2.306  30.119  16.750  1.00 30.85
ATOM   1625  CD   PRO A 447       2.757  30.857  17.947  1.00 31.01
ATOM   1626  CA   PRO A 447       0.924  30.490  16.417  1.00 29.52
ATOM   1627  CB   PRO A 447       0.540  31.456  17.549  1.00 29.66
ATOM   1628  CG   PRO A 447       1.838  32.057  17.947  1.00 30.33
ATOM   1629  C    PRO A 447       0.771  31.115  15.023  1.00 28.09
ATOM   1630  O    PRO A 447      -0.318  31.072  14.440  1.00 27.41
ATOM   1631  N    GLU A 448       1.872  31.651  14.488  1.00 26.27
ATOM   1632  CA   GLU A 448       1.888  32.259  13.158  1.00 24.86
ATOM   1633  CB   GLU A 448       3.070  33.216  12.999  1.00 27.56
ATOM   1634  CG   GLU A 448       2.878  34.543  13.722  1.00 31.42
ATOM   1635  CD   GLU A 448       4.077  35.481  13.620  1.00 34.19
ATOM   1636  OE1  GLU A 448       5.018  35.212  12.842  1.00 35.85
ATOM   1637  OE2  GLU A 448       4.065  36.510  14.329  1.00 36.17
ATOM   1638  C    GLU A 448       1.942  31.188  12.088  1.00 22.92
ATOM   1639  O    GLU A 448       1.377  31.354  11.014  1.00 21.94
ATOM   1640  N    VAL A 449       2.662  30.105  12.377  1.00 22.28
ATOM   1641  CA   VAL A 449       2.767  28.964  11.471  1.00 20.31
ATOM   1642  CB   VAL A 449       3.824  27.940  11.971  1.00 19.41
ATOM   1643  CG1  VAL A 449       3.691  26.606  11.227  1.00 17.83
ATOM   1644  CG2  VAL A 449       5.233  28.515  11.800  1.00 16.96
ATOM   1645  C    VAL A 449       1.378  28.327  11.441  1.00 20.14
ATOM   1646  O    VAL A 449       0.857  28.019  10.375  1.00 21.19
ATOM   1647  N    ILE A 450       0.755  28.208  12.609  1.00 19.99
ATOM   1648  CA   ILE A 450      -0.589  27.646  12.726  1.00 20.16
ATOM   1649  CB   ILE A 450      -1.103  27.717  14.191  1.00 19.60
ATOM   1650  CG2  ILE A 450      -2.533  27.169  14.292  1.00 18.69
ATOM   1651  CG1  ILE A 450      -0.137  27.006  15.147  1.00 19.20
ATOM   1652  CD1  ILE A 450      -0.337  25.540  15.286  1.00 19.48
ATOM   1653  C    ILE A 450      -1.574  28.415  11.828  1.00 21.02
ATOM   1654  O    ILE A 450      -2.272  27.816  11.007  1.00 21.36
ATOM   1655  N    GLN A 451      -1.586  29.742  11.939  1.00 21.87
ATOM   1656  CA   GLN A 451      -2.511  30.545  11.147  1.00 22.67
ATOM   1657  CB   GLN A 451      -2.750  31.933  11.772  1.00 25.06
ATOM   1658  CG   GLN A 451      -1.580  32.894  11.784  1.00 29.23
ATOM   1659  CD   GLN A 451      -1.703  33.946  12.893  1.00 32.99
ATOM   1660  OE1  GLN A 451      -1.108  35.032  12.813  1.00 34.75
ATOM   1661  NE2  GLN A 451      -2.443  33.609  13.957  1.00 33.95
ATOM   1662  C    GLN A 451      -2.203  30.635   9.663  1.00 21.29
ATOM   1663  O    GLN A 451      -3.077  30.978   8.868  1.00 22.11
ATOM   1664  N    ASN A 452      -0.977  30.286   9.289  1.00 20.42
ATOM   1665  CA   ASN A 452      -0.579  30.298   7.893  1.00 17.91
ATOM   1666  CB   ASN A 452       0.915  30.493   7.760  1.00 17.01
ATOM   1667  CG   ASN A 452       1.272  31.919   7.501  1.00 18.28
```

Figure 5

| ATOM | 1668 | OD1 | ASN A 452 | 1.271 | 32.388 | 6.352 | 1.00 | 17.74 |
| ATOM | 1669 | ND2 | ASN A 452 | 1.523 | 32.650 | 8.571 | 1.00 | 19.49 |
| ATOM | 1670 | C | ASN A 452 | -0.976 | 28.979 | 7.288 | 1.00 | 17.75 |
| ATOM | 1671 | O | ASN A 452 | -1.406 | 28.914 | 6.143 | 1.00 | 17.52 |
| ATOM | 1672 | N | LEU A 453 | -0.816 | 27.922 | 8.071 | 1.00 | 17.63 |
| ATOM | 1673 | CA | LEU A 453 | -1.175 | 26.591 | 7.630 | 1.00 | 17.27 |
| ATOM | 1674 | CB | LEU A 453 | -0.784 | 25.555 | 8.671 | 1.00 | 17.52 |
| ATOM | 1675 | CG | LEU A 453 | 0.697 | 25.226 | 8.757 | 1.00 | 19.45 |
| ATOM | 1676 | CD1 | LEU A 453 | 0.858 | 24.051 | 9.712 | 1.00 | 18.85 |
| ATOM | 1677 | CD2 | LEU A 453 | 1.247 | 24.879 | 7.360 | 1.00 | 20.06 |
| ATOM | 1678 | C | LEU A 453 | -2.661 | 26.507 | 7.388 | 1.00 | 17.49 |
| ATOM | 1679 | O | LEU A 453 | -3.097 | 25.775 | 6.518 | 1.00 | 17.45 |
| ATOM | 1680 | N | GLU A 454 | -3.451 | 27.203 | 8.199 | 1.00 | 18.00 |
| ATOM | 1681 | CA | GLU A 454 | -4.888 | 27.184 | 8.009 | 1.00 | 18.98 |
| ATOM | 1682 | CB | GLU A 454 | -5.581 | 28.094 | 9.002 | 1.00 | 24.08 |
| ATOM | 1683 | CG | GLU A 454 | -5.408 | 27.758 | 10.457 | 1.00 | 30.78 |
| ATOM | 1684 | CD | GLU A 454 | -6.085 | 28.802 | 11.350 | 1.00 | 35.58 |
| ATOM | 1685 | OE1 | GLU A 454 | -5.602 | 29.004 | 12.497 | 1.00 | 36.68 |
| ATOM | 1686 | OE2 | GLU A 454 | -7.093 | 29.423 | 10.893 | 1.00 | 36.73 |
| ATOM | 1687 | C | GLU A 454 | -5.210 | 27.697 | 6.618 | 1.00 | 17.34 |
| ATOM | 1688 | O | GLU A 454 | -6.095 | 27.188 | 5.967 | 1.00 | 17.75 |
| ATOM | 1689 | N | ARG A 455 | -4.479 | 28.722 | 6.192 | 1.00 | 17.01 |
| ATOM | 1690 | CA | ARG A 455 | -4.633 | 29.358 | 4.888 | 1.00 | 15.73 |
| ATOM | 1691 | CB | ARG A 455 | -4.142 | 30.816 | 4.968 | 1.00 | 16.77 |
| ATOM | 1692 | CG | ARG A 455 | -4.926 | 31.723 | 5.927 | 1.00 | 20.67 |
| ATOM | 1693 | CD | ARG A 455 | -4.398 | 33.174 | 5.899 | 1.00 | 23.27 |
| ATOM | 1694 | NE | ARG A 455 | -3.781 | 33.558 | 7.174 | 1.00 | 28.74 |
| ATOM | 1695 | CZ | ARG A 455 | -2.613 | 34.190 | 7.310 | 1.00 | 29.90 |
| ATOM | 1696 | NH1 | ARG A 455 | -1.895 | 34.532 | 6.250 | 1.00 | 32.24 |
| ATOM | 1697 | NH2 | ARG A 455 | -2.149 | 34.471 | 8.523 | 1.00 | 33.10 |
| ATOM | 1698 | C | ARG A 455 | -3.884 | 28.602 | 3.760 | 1.00 | 14.38 |
| ATOM | 1699 | O | ARG A 455 | -3.772 | 29.087 | 2.634 | 1.00 | 13.92 |
| ATOM | 1700 | N | GLY A 456 | -3.310 | 27.453 | 4.091 | 1.00 | 12.99 |
| ATOM | 1701 | CA | GLY A 456 | -2.611 | 26.645 | 3.105 | 1.00 | 12.03 |
| ATOM | 1702 | C | GLY A 456 | -1.211 | 27.055 | 2.711 | 1.00 | 11.91 |
| ATOM | 1703 | O | GLY A 456 | -0.749 | 26.730 | 1.621 | 1.00 | 13.01 |
| ATOM | 1704 | N | TYR A 457 | -0.523 | 27.744 | 3.607 | 1.00 | 11.48 |
| ATOM | 1705 | CA | TYR A 457 | 0.833 | 28.203 | 3.367 | 1.00 | 10.63 |
| ATOM | 1706 | CB | TYR A 457 | 1.245 | 29.136 | 4.507 | 1.00 | 9.77 |
| ATOM | 1707 | CG | TYR A 457 | 2.617 | 29.726 | 4.362 | 1.00 | 9.75 |
| ATOM | 1708 | CD1 | TYR A 457 | 2.835 | 30.851 | 3.565 | 1.00 | 8.54 |
| ATOM | 1709 | CE1 | TYR A 457 | 4.115 | 31.384 | 3.399 | 1.00 | 8.87 |
| ATOM | 1710 | CD2 | TYR A 457 | 3.717 | 29.139 | 4.999 | 1.00 | 11.26 |
| ATOM | 1711 | CE2 | TYR A 457 | 5.016 | 29.664 | 4.834 | 1.00 | 11.25 |
| ATOM | 1712 | CZ | TYR A 457 | 5.198 | 30.783 | 4.037 | 1.00 | 10.82 |
| ATOM | 1713 | OH | TYR A 457 | 6.471 | 31.286 | 3.887 | 1.00 | 12.13 |
| ATOM | 1714 | C | TYR A 457 | 1.852 | 27.075 | 3.241 | 1.00 | 11.09 |
| ATOM | 1715 | O | TYR A 457 | 1.772 | 26.070 | 3.946 | 1.00 | 11.86 |
| ATOM | 1716 | N | ARG A 458 | 2.780 | 27.235 | 2.297 | 1.00 | 12.01 |
| ATOM | 1717 | CA | ARG A 458 | 3.869 | 26.292 | 2.086 | 1.00 | 12.67 |
| ATOM | 1718 | CB | ARG A 458 | 3.666 | 25.430 | 0.847 | 1.00 | 10.84 |
| ATOM | 1719 | CG | ARG A 458 | 2.510 | 24.478 | 0.914 | 1.00 | 9.63 |
| ATOM | 1720 | CD | ARG A 458 | 2.600 | 23.512 | 2.080 | 1.00 | 9.14 |
| ATOM | 1721 | NE | ARG A 458 | 1.489 | 22.553 | 2.076 | 1.00 | 7.40 |
| ATOM | 1722 | CZ | ARG A 458 | 0.377 | 22.671 | 2.795 | 1.00 | 6.60 |
| ATOM | 1723 | NH1 | ARG A 458 | 0.189 | 23.710 | 3.595 | 1.00 | 6.30 |
| ATOM | 1724 | NH2 | ARG A 458 | -0.539 | 21.721 | 2.741 | 1.00 | 8.04 |
| ATOM | 1725 | C | ARG A 458 | 5.125 | 27.127 | 1.906 | 1.00 | 14.93 |
| ATOM | 1726 | O | ARG A 458 | 5.092 | 28.150 | 1.218 | 1.00 | 15.31 |
| ATOM | 1727 | N | MET A 459 | 6.199 | 26.733 | 2.587 | 1.00 | 16.21 |

Figure 5

| | | | | | | | | |
|---|---|---|---|---|---|---|---|---|
| ATOM | 1728 | CA | MET | A | 459 | 7.473 | 27.422 | 2.476 | 1.00 18.98 |
| ATOM | 1729 | CB | MET | A | 459 | 8.541 | 26.671 | 3.247 | 1.00 19.26 |
| ATOM | 1730 | CG | MET | A | 459 | 8.367 | 26.737 | 4.732 | 1.00 22.64 |
| ATOM | 1731 | SD | MET | A | 459 | 9.866 | 26.164 | 5.546 | 1.00 24.27 |
| ATOM | 1732 | CE | MET | A | 459 | 9.304 | 24.518 | 6.132 | 1.00 23.33 |
| ATOM | 1733 | C | MET | A | 459 | 7.933 | 27.516 | 1.027 | 1.00 21.00 |
| ATOM | 1734 | O | MET | A | 459 | 7.669 | 26.618 | 0.224 | 1.00 21.35 |
| ATOM | 1735 | N | VAL | A | 460 | 8.636 | 28.596 | 0.692 | 1.00 22.92 |
| ATOM | 1736 | CA | VAL | A | 460 | 9.137 | 28.770 | -0.675 | 1.00 24.75 |
| ATOM | 1737 | CB | VAL | A | 460 | 9.395 | 30.269 | -0.999 | 1.00 24.19 |
| ATOM | 1738 | CG1 | VAL | A | 460 | 8.162 | 31.076 | -0.677 | 1.00 23.29 |
| ATOM | 1739 | CG2 | VAL | A | 460 | 10.599 | 30.804 | -0.217 | 1.00 22.57 |
| ATOM | 1740 | C | VAL | A | 460 | 10.417 | 27.941 | -0.879 | 1.00 25.99 |
| ATOM | 1741 | O | VAL | A | 460 | 10.935 | 27.358 | 0.078 | 1.00 25.69 |
| ATOM | 1742 | N | ARG | A | 461 | 10.918 | 27.879 | -2.114 | 1.00 27.24 |
| ATOM | 1743 | CA | ARG | A | 461 | 12.134 | 27.116 | -2.372 | 1.00 29.00 |
| ATOM | 1744 | CB | ARG | A | 461 | 12.442 | 26.985 | -3.866 | 1.00 30.79 |
| ATOM | 1745 | CG | ARG | A | 461 | 13.634 | 26.065 | -4.114 | 1.00 33.12 |
| ATOM | 1746 | CD | ARG | A | 461 | 14.035 | 25.993 | -5.561 | 1.00 36.53 |
| ATOM | 1747 | NE | ARG | A | 461 | 14.401 | 27.304 | -6.077 | 1.00 41.30 |
| ATOM | 1748 | CZ | ARG | A | 461 | 14.459 | 27.606 | -7.371 | 1.00 44.60 |
| ATOM | 1749 | NH1 | ARG | A | 461 | 14.184 | 26.683 | -8.290 | 1.00 45.37 |
| ATOM | 1750 | NH2 | ARG | A | 461 | 14.736 | 28.849 | -7.749 | 1.00 45.43 |
| ATOM | 1751 | C | ARG | A | 461 | 13.310 | 27.775 | -1.669 | 1.00 29.51 |
| ATOM | 1752 | O | ARG | A | 461 | 13.578 | 28.965 | -1.856 | 1.00 29.05 |
| ATOM | 1753 | N | PRO | A | 462 | 13.972 | 27.023 | -0.778 | 1.00 30.54 |
| ATOM | 1754 | CD | PRO | A | 462 | 13.508 | 25.716 | -0.280 | 1.00 30.15 |
| ATOM | 1755 | CA | PRO | A | 462 | 15.130 | 27.474 | -0.002 | 1.00 31.14 |
| ATOM | 1756 | CB | PRO | A | 462 | 15.425 | 26.264 | 0.880 | 1.00 29.80 |
| ATOM | 1757 | CG | PRO | A | 462 | 14.078 | 25.697 | 1.110 | 1.00 29.47 |
| ATOM | 1758 | C | PRO | A | 462 | 16.335 | 27.803 | -0.874 | 1.00 31.99 |
| ATOM | 1759 | O | PRO | A | 462 | 16.505 | 27.236 | -1.956 | 1.00 31.56 |
| ATOM | 1760 | N | ASP | A | 463 | 17.175 | 28.717 | -0.395 | 1.00 33.12 |
| ATOM | 1761 | CA | ASP | A | 463 | 18.374 | 29.081 | -1.134 | 1.00 34.25 |
| ATOM | 1762 | CB | ASP | A | 463 | 19.099 | 30.250 | -0.449 | 1.00 34.23 |
| ATOM | 1763 | CG | ASP | A | 463 | 18.278 | 31.548 | -0.463 | 1.00 34.49 |
| ATOM | 1764 | OD1 | ASP | A | 463 | 17.685 | 31.887 | -1.514 | 1.00 34.91 |
| ATOM | 1765 | OD2 | ASP | A | 463 | 18.222 | 32.235 | 0.580 | 1.00 33.86 |
| ATOM | 1766 | C | ASP | A | 463 | 19.272 | 27.837 | -1.259 | 1.00 34.63 |
| ATOM | 1767 | O | ASP | A | 463 | 19.446 | 27.081 | -0.295 | 1.00 33.69 |
| ATOM | 1768 | N | ASN | A | 464 | 19.750 | 27.588 | -2.481 | 1.00 35.42 |
| ATOM | 1769 | CA | ASN | A | 464 | 20.611 | 26.442 | -2.795 | 1.00 36.32 |
| ATOM | 1770 | CB | ASN | A | 464 | 21.904 | 26.461 | -1.953 | 1.00 39.79 |
| ATOM | 1771 | CG | ASN | A | 464 | 22.885 | 27.566 | -2.397 | 1.00 43.52 |
| ATOM | 1772 | OD1 | ASN | A | 464 | 23.546 | 27.450 | -3.446 | 1.00 43.83 |
| ATOM | 1773 | ND2 | ASN | A | 464 | 22.979 | 28.645 | -1.596 | 1.00 43.85 |
| ATOM | 1774 | C | ASN | A | 464 | 19.887 | 25.102 | -2.653 | 1.00 35.10 |
| ATOM | 1775 | O | ASN | A | 464 | 20.389 | 24.168 | -2.015 | 1.00 34.59 |
| ATOM | 1776 | N | CYS | A | 465 | 18.713 | 25.020 | -3.278 | 1.00 33.38 |
| ATOM | 1777 | CA | CYS | A | 465 | 17.880 | 23.816 | -3.250 | 1.00 31.10 |
| ATOM | 1778 | CB | CYS | A | 465 | 16.760 | 23.972 | -2.217 | 1.00 28.11 |
| ATOM | 1779 | SG | CYS | A | 465 | 15.581 | 22.619 | -2.196 | 1.00 23.45 |
| ATOM | 1780 | C | CYS | A | 465 | 17.275 | 23.548 | -4.633 | 1.00 30.73 |
| ATOM | 1781 | O | CYS | A | 465 | 16.518 | 24.367 | -5.158 | 1.00 32.08 |
| ATOM | 1782 | N | PRO | A | 466 | 17.600 | 22.395 | -5.238 | 1.00 28.85 |
| ATOM | 1783 | CD | PRO | A | 466 | 18.492 | 21.346 | -4.708 | 1.00 27.84 |
| ATOM | 1784 | CA | PRO | A | 466 | 17.082 | 22.036 | -6.561 | 1.00 28.04 |
| ATOM | 1785 | CB | PRO | A | 466 | 17.581 | 20.606 | -6.729 | 1.00 28.00 |
| ATOM | 1786 | CG | PRO | A | 466 | 18.865 | 20.589 | -5.938 | 1.00 27.91 |
| ATOM | 1787 | C | PRO | A | 466 | 15.553 | 22.104 | -6.642 | 1.00 28.24 |

Figure 5

```
ATOM   1788  O    PRO A 466      14.879  22.030  -5.624  1.00 28.27
ATOM   1789  N    GLU A 467      15.008  22.266  -7.847  1.00 28.89
ATOM   1790  CA   GLU A 467      13.553  22.317  -8.024  1.00 29.40
ATOM   1791  CB   GLU A 467      13.177  22.891  -9.383  1.00 30.71
ATOM   1792  CG   GLU A 467      12.590  24.294  -9.326  1.00 33.46
ATOM   1793  CD   GLU A 467      11.255  24.365  -8.619  1.00 34.89
ATOM   1794  OE1  GLU A 467      11.083  25.281  -7.780  1.00 35.57
ATOM   1795  OE2  GLU A 467      10.367  23.534  -8.931  1.00 36.00
ATOM   1796  C    GLU A 467      12.912  20.943  -7.885  1.00 28.86
ATOM   1797  O    GLU A 467      11.765  20.828  -7.458  1.00 29.42
ATOM   1798  N    GLU A 468      13.634  19.907  -8.288  1.00 27.54
ATOM   1799  CA   GLU A 468      13.114  18.557  -8.182  1.00 26.94
ATOM   1800  CB   GLU A 468      14.032  17.554  -8.881  1.00 29.54
ATOM   1801  CG   GLU A 468      14.271  17.836 -10.359  1.00 33.46
ATOM   1802  CD   GLU A 468      15.217  19.023 -10.606  1.00 34.95
ATOM   1803  OE1  GLU A 468      16.166  19.223  -9.803  1.00 33.69
ATOM   1804  OE2  GLU A 468      15.006  19.747 -11.612  1.00 35.47
ATOM   1805  C    GLU A 468      13.022  18.225  -6.704  1.00 25.15
ATOM   1806  O    GLU A 468      12.097  17.525  -6.281  1.00 25.08
ATOM   1807  N    LEU A 469      13.972  18.757  -5.924  1.00 22.62
ATOM   1808  CA   LEU A 469      13.996  18.532  -4.479  1.00 20.47
ATOM   1809  CB   LEU A 469      15.383  18.792  -3.879  1.00 18.36
ATOM   1810  CG   LEU A 469      15.511  18.546  -2.363  1.00 16.18
ATOM   1811  CD1  LEU A 469      15.167  17.109  -2.020  1.00 14.90
ATOM   1812  CD2  LEU A 469      16.904  18.872  -1.893  1.00 14.11
ATOM   1813  C    LEU A 469      12.933  19.368  -3.770  1.00 19.26
ATOM   1814  O    LEU A 469      12.351  18.928  -2.778  1.00 19.52
ATOM   1815  N    TYR A 470      12.705  20.580  -4.252  1.00 18.56
ATOM   1816  CA   TYR A 470      11.670  21.406  -3.668  1.00 18.63
ATOM   1817  CB   TYR A 470      11.717  22.844  -4.180  1.00 18.05
ATOM   1818  CG   TYR A 470      10.543  23.676  -3.703  1.00 17.77
ATOM   1819  CD1  TYR A 470      10.346  23.927  -2.349  1.00 18.02
ATOM   1820  CE1  TYR A 470       9.254  24.701  -1.902  1.00 19.12
ATOM   1821  CD2  TYR A 470       9.624  24.214  -4.606  1.00 18.89
ATOM   1822  CE2  TYR A 470       8.527  24.993  -4.167  1.00 18.67
ATOM   1823  CZ   TYR A 470       8.353  25.230  -2.813  1.00 19.11
ATOM   1824  OH   TYR A 470       7.286  25.992  -2.366  1.00 18.89
ATOM   1825  C    TYR A 470      10.318  20.801  -4.012  1.00 18.80
ATOM   1826  O    TYR A 470       9.370  20.942  -3.254  1.00 19.96
ATOM   1827  N    GLN A 471      10.214  20.128  -5.153  1.00 19.28
ATOM   1828  CA   GLN A 471       8.935  19.529  -5.527  1.00 18.24
ATOM   1829  CB   GLN A 471       8.835  19.315  -7.038  1.00 18.76
ATOM   1830  CG   GLN A 471       8.547  20.603  -7.822  1.00 18.35
ATOM   1831  CD   GLN A 471       7.279  21.359  -7.352  1.00 20.11
ATOM   1832  OE1  GLN A 471       6.296  20.759  -6.858  1.00 18.71
ATOM   1833  NE2  GLN A 471       7.298  22.681  -7.525  1.00 19.44
ATOM   1834  C    GLN A 471       8.636  18.262  -4.748  1.00 17.49
ATOM   1835  O    GLN A 471       7.484  17.883  -4.580  1.00 17.84
ATOM   1836  N    LEU A 472       9.686  17.630  -4.241  1.00 17.75
ATOM   1837  CA   LEU A 472       9.547  16.430  -3.434  1.00 16.87
ATOM   1838  CB   LEU A 472      10.904  15.782  -3.250  1.00 18.53
ATOM   1839  CG   LEU A 472      10.933  14.269  -3.428  1.00 20.72
ATOM   1840  CD1  LEU A 472      10.323  13.856  -4.784  1.00 20.13
ATOM   1841  CD2  LEU A 472      12.391  13.825  -3.316  1.00 22.06
ATOM   1842  C    LEU A 472       8.998  16.857  -2.078  1.00 15.90
ATOM   1843  O    LEU A 472       8.149  16.172  -1.500  1.00 16.20
ATOM   1844  N    MET A 473       9.513  17.978  -1.569  1.00 13.87
ATOM   1845  CA   MET A 473       9.057  18.555  -0.299  1.00 13.28
ATOM   1846  CB   MET A 473       9.775  19.862  -0.016  1.00 11.99
ATOM   1847  CG   MET A 473      11.236  19.763   0.204  1.00  9.50
```

Figure 5

| | | | | | | | | |
|---|---|---|---|---|---|---|---|---|
| ATOM | 1848 | SD  | MET | A | 473 | 11.857 | 21.432 |  0.235 | 1.00 | 11.27 |
| ATOM | 1849 | CE  | MET | A | 473 | 13.647 | 21.118 |  0.424 | 1.00 |  4.99 |
| ATOM | 1850 | C   | MET | A | 473 |  7.573 | 18.893 | -0.406 | 1.00 | 13.94 |
| ATOM | 1851 | O   | MET | A | 473 |  6.785 | 18.623 |  0.502 | 1.00 | 13.30 |
| ATOM | 1852 | N   | ARG | A | 474 |  7.214 | 19.526 | -1.519 | 1.00 | 14.65 |
| ATOM | 1853 | CA  | ARG | A | 474 |  5.842 | 19.905 | -1.783 | 1.00 | 15.50 |
| ATOM | 1854 | CB  | ARG | A | 474 |  5.750 | 20.623 | -3.119 | 1.00 | 14.79 |
| ATOM | 1855 | CG  | ARG | A | 474 |  6.398 | 21.980 | -3.087 | 1.00 | 15.77 |
| ATOM | 1856 | CD  | ARG | A | 474 |  5.754 | 22.863 | -2.024 | 1.00 | 17.21 |
| ATOM | 1857 | NE  | ARG | A | 474 |  4.337 | 23.122 | -2.298 | 1.00 | 18.81 |
| ATOM | 1858 | CZ  | ARG | A | 474 |  3.857 | 24.258 | -2.806 | 1.00 | 17.10 |
| ATOM | 1859 | NH1 | ARG | A | 474 |  4.675 | 25.258 | -3.112 | 1.00 | 15.43 |
| ATOM | 1860 | NH2 | ARG | A | 474 |  2.547 | 24.414 | -2.946 | 1.00 | 15.40 |
| ATOM | 1861 | C   | ARG | A | 474 |  4.920 | 18.698 | -1.763 | 1.00 | 16.68 |
| ATOM | 1862 | O   | ARG | A | 474 |  3.753 | 18.809 | -1.355 | 1.00 | 18.48 |
| ATOM | 1863 | N   | LEU | A | 475 |  5.441 | 17.541 | -2.178 | 1.00 | 16.47 |
| ATOM | 1864 | CA  | LEU | A | 475 |  4.637 | 16.324 | -2.180 | 1.00 | 15.35 |
| ATOM | 1865 | CB  | LEU | A | 475 |  5.208 | 15.257 | -3.137 | 1.00 | 15.37 |
| ATOM | 1866 | CG  | LEU | A | 475 |  4.919 | 15.541 | -4.635 | 1.00 | 15.03 |
| ATOM | 1867 | CD1 | LEU | A | 475 |  5.608 | 14.552 | -5.575 | 1.00 | 11.34 |
| ATOM | 1868 | CD2 | LEU | A | 475 |  3.413 | 15.526 | -4.855 | 1.00 | 14.58 |
| ATOM | 1869 | C   | LEU | A | 475 |  4.515 | 15.828 | -0.754 | 1.00 | 14.32 |
| ATOM | 1870 | O   | LEU | A | 475 |  3.499 | 15.270 | -0.384 | 1.00 | 14.84 |
| ATOM | 1871 | N   | CYS | A | 476 |  5.522 | 16.097 |  0.067 | 1.00 | 13.73 |
| ATOM | 1872 | CA  | CYS | A | 476 |  5.483 | 15.689 |  1.474 | 1.00 | 12.85 |
| ATOM | 1873 | CB  | CYS | A | 476 |  6.845 | 15.879 |  2.145 | 1.00 | 12.07 |
| ATOM | 1874 | SG  | CYS | A | 476 |  8.169 | 14.798 |  1.547 | 1.00 | 12.45 |
| ATOM | 1875 | C   | CYS | A | 476 |  4.472 | 16.544 |  2.202 | 1.00 | 12.78 |
| ATOM | 1876 | O   | CYS | A | 476 |  3.848 | 16.088 |  3.145 | 1.00 | 13.37 |
| ATOM | 1877 | N   | TRP | A | 477 |  4.286 | 17.774 |  1.727 | 1.00 | 12.99 |
| ATOM | 1878 | CA  | TRP | A | 477 |  3.368 | 18.725 |  2.346 | 1.00 | 13.56 |
| ATOM | 1879 | CB  | TRP | A | 477 |  3.970 | 20.139 |  2.320 | 1.00 | 12.56 |
| ATOM | 1880 | CG  | TRP | A | 477 |  5.298 | 20.250 |  2.969 | 1.00 | 10.27 |
| ATOM | 1881 | CD2 | TRP | A | 477 |  6.327 | 21.177 |  2.643 | 1.00 | 11.06 |
| ATOM | 1882 | CE2 | TRP | A | 477 |  7.436 | 20.871 |  3.467 | 1.00 | 10.92 |
| ATOM | 1883 | CE3 | TRP | A | 477 |  6.431 | 22.235 |  1.727 | 1.00 | 11.11 |
| ATOM | 1884 | CD1 | TRP | A | 477 |  5.798 | 19.452 |  3.956 | 1.00 | 10.18 |
| ATOM | 1885 | NE1 | TRP | A | 477 |  7.076 | 19.815 |  4.261 | 1.00 |  9.69 |
| ATOM | 1886 | CZ2 | TRP | A | 477 |  8.647 | 21.586 |  3.402 | 1.00 | 10.26 |
| ATOM | 1887 | CZ3 | TRP | A | 477 |  7.640 | 22.947 |  1.662 | 1.00 |  9.84 |
| ATOM | 1888 | CH2 | TRP | A | 477 |  8.729 | 22.615 |  2.497 | 1.00 |  9.76 |
| ATOM | 1889 | C   | TRP | A | 477 |  1.957 | 18.805 |  1.762 | 1.00 | 15.45 |
| ATOM | 1890 | O   | TRP | A | 477 |  1.306 | 19.850 |  1.880 | 1.00 | 16.40 |
| ATOM | 1891 | N   | LYS | A | 478 |  1.469 | 17.739 |  1.136 | 1.00 | 15.81 |
| ATOM | 1892 | CA  | LYS | A | 478 |  0.119 | 17.783 |  0.588 | 1.00 | 16.59 |
| ATOM | 1893 | CB  | LYS | A | 478 | -0.152 | 16.595 | -0.338 | 1.00 | 17.26 |
| ATOM | 1894 | CG  | LYS | A | 478 |  0.709 | 16.558 | -1.624 | 1.00 | 19.61 |
| ATOM | 1895 | CD  | LYS | A | 478 |  0.371 | 17.665 | -2.637 | 1.00 | 20.03 |
| ATOM | 1896 | CE  | LYS | A | 478 | -1.006 | 17.463 | -3.268 | 1.00 | 21.20 |
| ATOM | 1897 | NZ  | LYS | A | 478 | -1.410 | 18.635 | -4.092 | 1.00 | 23.30 |
| ATOM | 1898 | C   | LYS | A | 478 | -0.835 | 17.792 |  1.771 | 1.00 | 17.05 |
| ATOM | 1899 | O   | LYS | A | 478 | -0.574 | 17.162 |  2.779 | 1.00 | 17.76 |
| ATOM | 1900 | N   | GLU | A | 479 | -1.913 | 18.553 |  1.664 | 1.00 | 18.01 |
| ATOM | 1901 | CA  | GLU | A | 479 | -2.887 | 18.681 |  2.742 | 1.00 | 18.73 |
| ATOM | 1902 | CB  | GLU | A | 479 | -3.982 | 19.665 |  2.307 | 1.00 | 18.95 |
| ATOM | 1903 | CG  | GLU | A | 479 | -5.002 | 20.046 |  3.387 | 1.00 | 19.82 |
| ATOM | 1904 | CD  | GLU | A | 479 | -4.400 | 20.831 |  4.551 | 1.00 | 20.13 |
| ATOM | 1905 | OE1 | GLU | A | 479 | -3.472 | 21.641 |  4.310 | 1.00 | 20.31 |
| ATOM | 1906 | OE2 | GLU | A | 479 | -4.873 | 20.642 |  5.699 | 1.00 | 19.40 |
| ATOM | 1907 | C   | GLU | A | 479 | -3.488 | 17.349 |  3.220 | 1.00 | 18.91 |

Figure 5

| | | | | | | | | | |
|---|---|---|---|---|---|---|---|---|---|
| ATOM | 1908 | O | GLU | A | 479 | -3.660 | 17.116 | 4.427 | 1.00 19.61 |
| ATOM | 1909 | N | ARG | A | 480 | -3.828 | 16.490 | 2.269 | 1.00 19.32 |
| ATOM | 1910 | CA | ARG | A | 480 | -4.396 | 15.180 | 2.576 | 1.00 18.30 |
| ATOM | 1911 | CB | ARG | A | 480 | -5.281 | 14.722 | 1.426 | 1.00 20.49 |
| ATOM | 1912 | CG | ARG | A | 480 | -6.514 | 15.538 | 1.244 | 1.00 23.34 |
| ATOM | 1913 | CD | ARG | A | 480 | -7.002 | 15.306 | -0.137 | 1.00 29.25 |
| ATOM | 1914 | NE | ARG | A | 480 | -8.358 | 15.795 | -0.345 | 1.00 34.60 |
| ATOM | 1915 | CZ | ARG | A | 480 | -8.973 | 15.788 | -1.523 | 1.00 37.70 |
| ATOM | 1916 | NH1 | ARG | A | 480 | -8.357 | 15.315 | -2.607 | 1.00 39.53 |
| ATOM | 1917 | NH2 | ARG | A | 480 | -10.191 | 16.288 | -1.623 | 1.00 39.69 |
| ATOM | 1918 | C | ARG | A | 480 | -3.264 | 14.190 | 2.777 | 1.00 16.06 |
| ATOM | 1919 | O | ARG | A | 480 | -2.420 | 14.027 | 1.907 | 1.00 15.41 |
| ATOM | 1920 | N | PRO | A | 481 | -3.288 | 13.444 | 3.887 | 1.00 14.79 |
| ATOM | 1921 | CD | PRO | A | 481 | -4.363 | 13.269 | 4.884 | 1.00 13.81 |
| ATOM | 1922 | CA | PRO | A | 481 | -2.208 | 12.489 | 4.119 | 1.00 13.45 |
| ATOM | 1923 | CB | PRO | A | 481 | -2.640 | 11.788 | 5.414 | 1.00 13.21 |
| ATOM | 1924 | CG | PRO | A | 481 | -3.618 | 12.737 | 6.052 | 1.00 13.16 |
| ATOM | 1925 | C | PRO | A | 481 | -2.041 | 11.477 | 3.008 | 1.00 13.35 |
| ATOM | 1926 | O | PRO | A | 481 | -0.946 | 10.986 | 2.788 | 1.00 14.29 |
| ATOM | 1927 | N | GLU | A | 482 | -3.125 | 11.178 | 2.302 | 1.00 13.75 |
| ATOM | 1928 | CA | GLU | A | 482 | -3.118 | 10.172 | 1.244 | 1.00 14.27 |
| ATOM | 1929 | CB | GLU | A | 482 | -4.562 | 9.772 | 0.893 | 1.00 15.76 |
| ATOM | 1930 | CG | GLU | A | 482 | -5.374 | 10.863 | 0.157 | 1.00 17.97 |
| ATOM | 1931 | CD | GLU | A | 482 | -6.487 | 11.498 | 1.001 | 1.00 18.75 |
| ATOM | 1932 | OE1 | GLU | A | 482 | -6.340 | 11.597 | 2.238 | 1.00 17.56 |
| ATOM | 1933 | OE2 | GLU | A | 482 | -7.519 | 11.906 | 0.410 | 1.00 20.01 |
| ATOM | 1934 | C | GLU | A | 482 | -2.370 | 10.554 | -0.028 | 1.00 15.01 |
| ATOM | 1935 | O | GLU | A | 482 | -1.947 | 9.682 | -0.784 | 1.00 16.26 |
| ATOM | 1936 | N | ASP | A | 483 | -2.197 | 11.854 | -0.258 | 1.00 15.14 |
| ATOM | 1937 | CA | ASP | A | 483 | -1.530 | 12.356 | -1.457 | 1.00 14.20 |
| ATOM | 1938 | CB | ASP | A | 483 | -2.154 | 13.691 | -1.903 | 1.00 14.94 |
| ATOM | 1939 | CG | ASP | A | 483 | -3.631 | 13.569 | -2.316 | 1.00 14.77 |
| ATOM | 1940 | OD1 | ASP | A | 483 | -4.043 | 12.528 | -2.860 | 1.00 16.72 |
| ATOM | 1941 | OD2 | ASP | A | 483 | -4.382 | 14.547 | -2.119 | 1.00 17.30 |
| ATOM | 1942 | C | ASP | A | 483 | -0.026 | 12.523 | -1.287 | 1.00 13.56 |
| ATOM | 1943 | O | ASP | A | 483 | 0.666 | 12.907 | -2.241 | 1.00 14.01 |
| ATOM | 1944 | N | ARG | A | 484 | 0.458 | 12.258 | -0.071 | 1.00 12.65 |
| ATOM | 1945 | CA | ARG | A | 484 | 1.885 | 12.348 | 0.277 | 1.00 11.64 |
| ATOM | 1946 | CB | ARG | A | 484 | 2.048 | 12.634 | 1.779 | 1.00 10.26 |
| ATOM | 1947 | CG | ARG | A | 484 | 1.271 | 13.839 | 2.285 | 1.00 8.86 |
| ATOM | 1948 | CD | ARG | A | 484 | 1.481 | 14.093 | 3.787 | 1.00 7.20 |
| ATOM | 1949 | NE | ARG | A | 484 | 0.621 | 15.178 | 4.249 | 1.00 9.15 |
| ATOM | 1950 | CZ | ARG | A | 484 | -0.005 | 15.220 | 5.426 | 1.00 9.46 |
| ATOM | 1951 | NH1 | ARG | A | 484 | 0.129 | 14.232 | 6.300 | 1.00 10.79 |
| ATOM | 1952 | NH2 | ARG | A | 484 | -0.807 | 16.238 | 5.717 | 1.00 7.17 |
| ATOM | 1953 | C | ARG | A | 484 | 2.577 | 11.011 | -0.073 | 1.00 11.85 |
| ATOM | 1954 | O | ARG | A | 484 | 2.013 | 9.937 | 0.149 | 1.00 11.30 |
| ATOM | 1955 | N | PRO | A | 485 | 3.840 | 11.054 | -0.535 | 1.00 12.10 |
| ATOM | 1956 | CD | PRO | A | 485 | 4.743 | 12.208 | -0.666 | 1.00 10.97 |
| ATOM | 1957 | CA | PRO | A | 485 | 4.537 | 9.809 | -0.892 | 1.00 12.69 |
| ATOM | 1958 | CB | PRO | A | 485 | 5.887 | 10.311 | -1.436 | 1.00 12.94 |
| ATOM | 1959 | CG | PRO | A | 485 | 5.652 | 11.753 | -1.763 | 1.00 12.15 |
| ATOM | 1960 | C | PRO | A | 485 | 4.766 | 8.824 | 0.261 | 1.00 13.49 |
| ATOM | 1961 | O | PRO | A | 485 | 4.586 | 9.160 | 1.426 | 1.00 14.29 |
| ATOM | 1962 | N | THR | A | 486 | 5.079 | 7.580 | -0.083 | 1.00 13.28 |
| ATOM | 1963 | CA | THR | A | 486 | 5.411 | 6.575 | 0.910 | 1.00 12.67 |
| ATOM | 1964 | CB | THR | A | 486 | 5.201 | 5.134 | 0.365 | 1.00 11.90 |
| ATOM | 1965 | OG1 | THR | A | 486 | 5.902 | 4.961 | -0.876 | 1.00 11.75 |
| ATOM | 1966 | CG2 | THR | A | 486 | 3.731 | 4.853 | 0.161 | 1.00 11.89 |
| ATOM | 1967 | C | THR | A | 486 | 6.909 | 6.849 | 1.090 | 1.00 13.83 |

Figure 5

| | | | | | | | | | |
|---|---|---|---|---|---|---|---|---|---|
| ATOM | 1968 | O | THR | A | 486 | 7.513 | 7.484 | 0.218 | 1.00 14.88 |
| ATOM | 1969 | N | PHE | A | 487 | 7.498 | 6.462 | 2.225 | 1.00 13.95 |
| ATOM | 1970 | CA | PHE | A | 487 | 8.932 | 6.676 | 2.451 | 1.00 13.61 |
| ATOM | 1971 | CB | PHE | A | 487 | 9.315 | 6.390 | 3.897 | 1.00 12.04 |
| ATOM | 1972 | CG | PHE | A | 487 | 9.152 | 7.567 | 4.810 | 1.00 11.23 |
| ATOM | 1973 | CD1 | PHE | A | 487 | 10.005 | 8.654 | 4.719 | 1.00 8.64 |
| ATOM | 1974 | CD2 | PHE | A | 487 | 8.167 | 7.569 | 5.804 | 1.00 11.80 |
| ATOM | 1975 | CE1 | PHE | A | 487 | 9.891 | 9.720 | 5.603 | 1.00 8.02 |
| ATOM | 1976 | CE2 | PHE | A | 487 | 8.049 | 8.631 | 6.690 | 1.00 8.67 |
| ATOM | 1977 | CZ | PHE | A | 487 | 8.918 | 9.707 | 6.587 | 1.00 9.24 |
| ATOM | 1978 | C | PHE | A | 487 | 9.707 | 5.760 | 1.513 | 1.00 15.50 |
| ATOM | 1979 | O | PHE | A | 487 | 10.831 | 6.060 | 1.121 | 1.00 16.30 |
| ATOM | 1980 | N | ASP | A | 488 | 9.092 | 4.635 | 1.165 | 1.00 16.50 |
| ATOM | 1981 | CA | ASP | A | 488 | 9.674 | 3.696 | 0.234 | 1.00 18.64 |
| ATOM | 1982 | CB | ASP | A | 488 | 8.669 | 2.573 | -0.047 | 1.00 22.06 |
| ATOM | 1983 | CG | ASP | A | 488 | 9.187 | 1.538 | -1.049 | 1.00 24.60 |
| ATOM | 1984 | OD1 | ASP | A | 488 | 10.430 | 1.367 | -1.170 | 1.00 25.57 |
| ATOM | 1985 | OD2 | ASP | A | 488 | 8.333 | 0.889 | -1.712 | 1.00 25.07 |
| ATOM | 1986 | C | ASP | A | 488 | 9.999 | 4.460 | -1.050 | 1.00 19.57 |
| ATOM | 1987 | O | ASP | A | 488 | 11.064 | 4.280 | -1.634 | 1.00 21.40 |
| ATOM | 1988 | N | TYR | A | 489 | 9.108 | 5.362 | -1.453 | 1.00 19.91 |
| ATOM | 1989 | CA | TYR | A | 489 | 9.321 | 6.161 | -2.655 | 1.00 19.05 |
| ATOM | 1990 | CB | TYR | A | 489 | 8.000 | 6.777 | -3.128 | 1.00 18.20 |
| ATOM | 1991 | CG | TYR | A | 489 | 8.181 | 7.786 | -4.241 | 1.00 18.87 |
| ATOM | 1992 | CD1 | TYR | A | 489 | 8.471 | 7.383 | -5.545 | 1.00 19.25 |
| ATOM | 1993 | CE1 | TYR | A | 489 | 8.701 | 8.322 | -6.555 | 1.00 19.27 |
| ATOM | 1994 | CD2 | TYR | A | 489 | 8.120 | 9.152 | -3.978 | 1.00 19.18 |
| ATOM | 1995 | CE2 | TYR | A | 489 | 8.344 | 10.090 | -4.965 | 1.00 18.18 |
| ATOM | 1996 | CZ | TYR | A | 489 | 8.634 | 9.680 | -6.249 | 1.00 19.53 |
| ATOM | 1997 | OH | TYR | A | 489 | 8.857 | 10.636 | -7.221 | 1.00 20.54 |
| ATOM | 1998 | C | TYR | A | 489 | 10.375 | 7.254 | -2.456 | 1.00 19.17 |
| ATOM | 1999 | O | TYR | A | 489 | 11.234 | 7.470 | -3.318 | 1.00 19.33 |
| ATOM | 2000 | N | LEU | A | 490 | 10.287 | 7.956 | -1.330 | 1.00 19.23 |
| ATOM | 2001 | CA | LEU | A | 490 | 11.217 | 9.028 | -0.992 | 1.00 18.68 |
| ATOM | 2002 | CB | LEU | A | 490 | 10.881 | 9.601 | 0.390 | 1.00 16.22 |
| ATOM | 2003 | CG | LEU | A | 490 | 9.660 | 10.531 | 0.412 | 1.00 13.94 |
| ATOM | 2004 | CD1 | LEU | A | 490 | 9.203 | 10.825 | 1.816 | 1.00 10.31 |
| ATOM | 2005 | CD2 | LEU | A | 490 | 10.015 | 11.813 | -0.299 | 1.00 13.71 |
| ATOM | 2006 | C | LEU | A | 490 | 12.656 | 8.541 | -1.023 | 1.00 21.13 |
| ATOM | 2007 | O | LEU | A | 490 | 13.530 | 9.230 | -1.551 | 1.00 22.40 |
| ATOM | 2008 | N | ARG | A | 491 | 12.899 | 7.352 | -0.465 | 1.00 22.63 |
| ATOM | 2009 | CA | ARG | A | 491 | 14.231 | 6.755 | -0.437 | 1.00 24.30 |
| ATOM | 2010 | CB | ARG | A | 491 | 14.194 | 5.431 | 0.328 | 1.00 25.91 |
| ATOM | 2011 | CG | ARG | A | 491 | 15.477 | 4.597 | 0.169 | 1.00 29.85 |
| ATOM | 2012 | CD | ARG | A | 491 | 15.258 | 3.107 | 0.447 | 1.00 31.83 |
| ATOM | 2013 | NE | ARG | A | 491 | 14.132 | 2.577 | -0.323 | 1.00 34.22 |
| ATOM | 2014 | CZ | ARG | A | 491 | 14.196 | 2.196 | -1.598 | 1.00 34.71 |
| ATOM | 2015 | NH1 | ARG | A | 491 | 15.339 | 2.275 | -2.279 | 1.00 32.96 |
| ATOM | 2016 | NH2 | ARG | A | 491 | 13.104 | 1.719 | -2.189 | 1.00 35.20 |
| ATOM | 2017 | C | ARG | A | 491 | 14.739 | 6.496 | -1.865 | 1.00 25.51 |
| ATOM | 2018 | O | ARG | A | 491 | 15.908 | 6.733 | -2.175 | 1.00 25.87 |
| ATOM | 2019 | N | SER | A | 492 | 13.849 | 5.968 | -2.707 | 1.00 26.28 |
| ATOM | 2020 | CA | SER | A | 492 | 14.136 | 5.650 | -4.103 | 1.00 26.24 |
| ATOM | 2021 | CB | SER | A | 492 | 12.898 | 5.052 | -4.774 | 1.00 27.28 |
| ATOM | 2022 | OG | SER | A | 492 | 12.636 | 3.746 | -4.309 | 1.00 29.20 |
| ATOM | 2023 | C | SER | A | 492 | 14.577 | 6.854 | -4.913 | 1.00 26.29 |
| ATOM | 2024 | O | SER | A | 492 | 15.595 | 6.809 | -5.597 | 1.00 26.65 |
| ATOM | 2025 | N | VAL | A | 493 | 13.788 | 7.922 | -4.877 | 1.00 26.01 |
| ATOM | 2026 | CA | VAL | A | 493 | 14.141 | 9.106 | -5.642 | 1.00 25.65 |
| ATOM | 2027 | CB | VAL | A | 493 | 12.930 | 10.049 | -5.855 | 1.00 25.37 |

Figure 5

| | | | | | | | | | |
|---|---|---|---|---|---|---|---|---|---|
| ATOM | 2028 | CG1 | VAL | A | 493 | 12.291 | 10.406 | -4.545 | 1.00 25.90 |
| ATOM | 2029 | CG2 | VAL | A | 493 | 13.364 | 11.300 | -6.602 | 1.00 25.20 |
| ATOM | 2030 | C | VAL | A | 493 | 15.351 | 9.820 | -5.056 | 1.00 25.53 |
| ATOM | 2031 | O | VAL | A | 493 | 16.164 | 10.380 | -5.795 | 1.00 25.30 |
| ATOM | 2032 | N | LEU | A | 494 | 15.518 | 9.714 | -3.737 | 1.00 26.54 |
| ATOM | 2033 | CA | LEU | A | 494 | 16.650 | 10.338 | -3.054 | 1.00 26.12 |
| ATOM | 2034 | CB | LEU | A | 494 | 16.396 | 10.430 | -1.550 | 1.00 24.07 |
| ATOM | 2035 | CG | LEU | A | 494 | 15.405 | 11.535 | -1.171 | 1.00 23.83 |
| ATOM | 2036 | CD1 | LEU | A | 494 | 15.095 | 11.543 | 0.321 | 1.00 20.97 |
| ATOM | 2037 | CD2 | LEU | A | 494 | 15.957 | 12.879 | -1.633 | 1.00 22.35 |
| ATOM | 2038 | C | LEU | A | 494 | 17.977 | 9.646 | -3.348 | 1.00 26.73 |
| ATOM | 2039 | O | LEU | A | 494 | 18.987 | 10.318 | -3.526 | 1.00 26.31 |
| ATOM | 2040 | N | GLU | A | 495 | 17.967 | 8.319 | -3.446 | 1.00 28.36 |
| ATOM | 2041 | CA | GLU | A | 495 | 19.186 | 7.560 | -3.740 | 1.00 31.84 |
| ATOM | 2042 | CB | GLU | A | 495 | 18.934 | 6.061 | -3.591 | 1.00 31.85 |
| ATOM | 2043 | CG | GLU | A | 495 | 18.703 | 5.601 | -2.171 | 1.00 33.22 |
| ATOM | 2044 | CD | GLU | A | 495 | 18.507 | 4.102 | -2.045 | 1.00 34.86 |
| ATOM | 2045 | OE1 | GLU | A | 495 | 18.473 | 3.395 | -3.087 | 1.00 34.99 |
| ATOM | 2046 | OE2 | GLU | A | 495 | 18.383 | 3.638 | -0.882 | 1.00 34.67 |
| ATOM | 2047 | C | GLU | A | 495 | 19.681 | 7.826 | -5.156 | 1.00 34.45 |
| ATOM | 2048 | O | GLU | A | 495 | 20.870 | 8.063 | -5.380 | 1.00 34.68 |
| ATOM | 2049 | N | ASP | A | 496 | 18.747 | 7.767 | -6.106 | 1.00 37.81 |
| ATOM | 2050 | CA | ASP | A | 496 | 19.023 | 7.983 | -7.527 | 1.00 40.34 |
| ATOM | 2051 | CB | ASP | A | 496 | 18.019 | 7.198 | -8.402 | 1.00 41.67 |
| ATOM | 2052 | CG | ASP | A | 496 | 17.917 | 5.710 | -8.045 | 1.00 44.24 |
| ATOM | 2053 | OD1 | ASP | A | 496 | 18.962 | 5.013 | -7.978 | 1.00 45.15 |
| ATOM | 2054 | OD2 | ASP | A | 496 | 16.764 | 5.226 | -7.890 | 1.00 44.77 |
| ATOM | 2055 | C | ASP | A | 496 | 18.894 | 9.459 | -7.927 | 1.00 41.66 |
| ATOM | 2056 | O | ASP | A | 496 | 18.695 | 9.754 | -9.103 | 1.00 42.33 |
| ATOM | 2057 | N | PHE | A | 497 | 19.051 | 10.391 | -6.994 | 1.00 42.71 |
| ATOM | 2058 | CA | PHE | A | 497 | 18.862 | 11.791 | -7.352 | 1.00 43.71 |
| ATOM | 2059 | CB | PHE | A | 497 | 18.982 | 12.714 | -6.138 | 1.00 42.48 |
| ATOM | 2060 | CG | PHE | A | 497 | 18.258 | 14.022 | -6.315 | 1.00 41.03 |
| ATOM | 2061 | CD1 | PHE | A | 497 | 16.894 | 14.117 | -6.057 | 1.00 38.96 |
| ATOM | 2062 | CD2 | PHE | A | 497 | 18.934 | 15.149 | -6.790 | 1.00 40.05 |
| ATOM | 2063 | CE1 | PHE | A | 497 | 16.216 | 15.312 | -6.271 | 1.00 38.63 |
| ATOM | 2064 | CE2 | PHE | A | 497 | 18.265 | 16.347 | -7.006 | 1.00 39.63 |
| ATOM | 2065 | CZ | PHE | A | 497 | 16.903 | 16.430 | -6.748 | 1.00 38.50 |
| ATOM | 2066 | C | PHE | A | 497 | 19.666 | 12.316 | -8.547 | 1.00 45.10 |
| ATOM | 2067 | O | PHE | A | 497 | 19.125 | 13.066 | -9.360 | 1.00 45.52 |
| ATOM | 2068 | N | PHE | A | 498 | 20.941 | 11.946 | -8.654 | 1.00 46.76 |
| ATOM | 2069 | CA | PHE | A | 498 | 21.771 | 12.370 | -9.794 | 1.00 48.40 |
| ATOM | 2070 | CB | PHE | A | 498 | 22.069 | 13.891 | -9.801 | 1.00 49.21 |
| ATOM | 2071 | CG | PHE | A | 498 | 22.446 | 14.487 | -8.447 | 1.00 49.45 |
| ATOM | 2072 | CD1 | PHE | A | 498 | 23.178 | 13.765 | -7.504 | 1.00 49.14 |
| ATOM | 2073 | CD2 | PHE | A | 498 | 22.065 | 15.799 | -8.136 | 1.00 49.15 |
| ATOM | 2074 | CE1 | PHE | A | 498 | 23.516 | 14.340 | -6.281 | 1.00 49.40 |
| ATOM | 2075 | CE2 | PHE | A | 498 | 22.399 | 16.383 | -6.920 | 1.00 48.47 |
| ATOM | 2076 | CZ | PHE | A | 498 | 23.124 | 15.657 | -5.991 | 1.00 49.05 |
| ATOM | 2077 | C | PHE | A | 498 | 23.052 | 11.567 | -10.005 | 1.00 49.25 |
| ATOM | 2078 | O | PHE | A | 498 | 23.077 | 10.823 | -11.014 | 1.00 50.13 |
| ATOM | 2079 | OH2 | H2O | A | 600 | 9.435 | 27.991 | -4.272 | 1.00 19.56 |
| ATOM | 2080 | OH2 | H2O | A | 601 | 6.703 | 11.393 | 38.435 | 1.00 31.02 |
| ATOM | 2081 | OH2 | H2O | A | 602 | 35.515 | 12.070 | 22.097 | 1.00 33.92 |
| ATOM | 2082 | OH2 | H2O | A | 603 | 5.785 | 24.405 | 4.245 | 1.00 3.73 |
| ATOM | 2083 | OH2 | H2O | A | 604 | 0.163 | 5.712 | -0.421 | 1.00 35.83 |
| ATOM | 2084 | OH2 | H2O | A | 605 | -1.066 | 28.574 | -0.892 | 1.00 34.80 |
| ATOM | 2085 | OH2 | H2O | A | 606 | 7.228 | 12.998 | 12.762 | 1.00 11.06 |
| ATOM | 2086 | OH2 | H2O | A | 607 | 3.587 | 0.880 | -2.383 | 1.00 44.81 |
| ATOM | 2087 | OH2 | H2O | A | 608 | -3.787 | 23.194 | 1.589 | 1.00 28.86 |

Figure 5

| | | | | | | | | |
|---|---|---|---|---|---|---|---|---|
| ATOM | 2088 | OH2 | H2O | A | 609 | 25.515 | 17.395 | 17.835 | 1.00 23.54 |
| ATOM | 2089 | OH2 | H2O | A | 610 | 4.913 | 22.386 | 8.979 | 1.00 19.20 |
| ATOM | 2090 | OH2 | H2O | A | 611 | -5.816 | 25.048 | 2.226 | 1.00 18.35 |
| ATOM | 2091 | OH2 | H2O | A | 612 | 9.652 | 30.474 | 3.007 | 1.00 25.10 |
| ATOM | 2092 | OH2 | H2O | A | 613 | 19.792 | -4.052 | 18.990 | 1.00 48.04 |
| ATOM | 2093 | OH2 | H2O | A | 614 | 33.365 | -0.207 | 31.272 | 1.00 14.70 |
| ATOM | 2094 | OH2 | H2O | A | 615 | 5.128 | 14.595 | 13.709 | 1.00 19.05 |
| ATOM | 2095 | OH2 | H2O | A | 616 | 16.940 | 16.942 | 24.032 | 1.00 17.02 |
| ATOM | 2096 | OH2 | H2O | A | 617 | 7.018 | 0.024 | 23.959 | 1.00 29.21 |
| ATOM | 2097 | OH2 | H2O | A | 618 | -1.562 | 24.467 | 0.505 | 1.00 11.54 |
| ATOM | 2098 | OH2 | H2O | A | 619 | 1.644 | 29.623 | 0.704 | 1.00 46.06 |
| ATOM | 2099 | OH2 | H2O | A | 620 | -2.644 | 6.953 | 0.540 | 1.00 43.38 |
| ATOM | 2100 | OH2 | H2O | A | 621 | -2.277 | 24.506 | -2.460 | 1.00 19.52 |
| ATOM | 2101 | OH2 | H2O | A | 622 | 30.796 | 7.432 | 15.608 | 1.00 38.61 |
| ATOM | 2102 | OH2 | H2O | A | 623 | 17.112 | -0.806 | 4.380 | 1.00 34.23 |
| ATOM | 2103 | OH2 | H2O | A | 624 | 1.084 | 12.225 | 23.176 | 1.00 17.96 |
| ATOM | 2104 | OH2 | H2O | A | 625 | -3.264 | 10.988 | 9.557 | 1.00 37.91 |
| ATOM | 2105 | OH2 | H2O | A | 626 | 34.432 | -4.398 | 24.684 | 1.00 24.80 |
| ATOM | 2106 | OH2 | H2O | A | 627 | 23.065 | 27.466 | 9.256 | 1.00 25.31 |
| ATOM | 2107 | OH2 | H2O | A | 628 | 25.813 | 1.425 | 11.013 | 1.00 40.13 |
| ATOM | 2108 | OH2 | H2O | A | 629 | -6.101 | 9.227 | 4.150 | 1.00 21.07 |
| ATOM | 2109 | OH2 | H2O | A | 630 | 3.232 | 6.269 | 3.620 | 1.00 27.83 |
| ATOM | 2110 | OH2 | H2O | A | 631 | 24.541 | -5.757 | 24.525 | 1.00 21.14 |
| ATOM | 2111 | OH2 | H2O | A | 632 | 20.348 | 5.100 | 1.072 | 1.00 28.14 |
| ATOM | 2112 | OH2 | H2O | A | 633 | 20.031 | -3.539 | 35.427 | 1.00 26.06 |
| ATOM | 2113 | OH2 | H2O | A | 634 | 18.504 | 12.082 | 39.043 | 1.00 19.87 |
| ATOM | 2114 | OH2 | H2O | A | 635 | -3.454 | 8.675 | 4.218 | 1.00 17.50 |
| ATOM | 2115 | OH2 | H2O | A | 636 | 3.058 | 3.193 | 10.089 | 1.00 23.67 |
| ATOM | 2116 | OH2 | H2O | A | 637 | 23.802 | 20.694 | 27.983 | 1.00 32.46 |
| ATOM | 2117 | OH2 | H2O | A | 638 | 4.038 | 11.924 | 13.139 | 1.00 29.44 |
| ATOM | 2118 | OH2 | H2O | A | 639 | 28.306 | 9.632 | 38.410 | 1.00 44.84 |
| ATOM | 2119 | OH2 | H2O | A | 640 | 13.733 | -4.299 | 34.134 | 1.00 29.81 |
| ATOM | 2120 | OH2 | H2O | A | 641 | 20.475 | 12.327 | 35.092 | 1.00 22.45 |
| ATOM | 2121 | OH2 | H2O | A | 642 | 29.030 | 2.299 | 19.418 | 1.00 25.61 |
| ATOM | 2122 | OH2 | H2O | A | 643 | 26.833 | 26.062 | 2.893 | 1.00 44.82 |
| ATOM | 2123 | OH2 | H2O | A | 644 | -2.108 | 23.746 | 5.538 | 1.00 23.11 |
| ATOM | 2124 | OH2 | H2O | A | 645 | 20.016 | 17.321 | 34.083 | 1.00 37.74 |
| ATOM | 2125 | N1 | LIG | A | 500 | 23.752 | 18.327 | 21.908 | 1.00 33.35 |
| ATOM | 2126 | C1 | LIG | A | 500 | 23.228 | 16.897 | 21.839 | 1.00 30.98 |
| ATOM | 2127 | C2 | LIG | A | 500 | 23.701 | 16.127 | 20.571 | 1.00 29.21 |
| ATOM | 2128 | C3 | LIG | A | 500 | 23.245 | 14.635 | 20.545 | 1.00 27.58 |
| ATOM | 2129 | C4 | LIG | A | 500 | 23.762 | 13.875 | 21.837 | 1.00 26.42 |
| ATOM | 2130 | C5 | LIG | A | 500 | 23.182 | 14.585 | 23.062 | 1.00 26.87 |
| ATOM | 2131 | C6 | LIG | A | 500 | 23.668 | 16.051 | 23.095 | 1.00 28.97 |
| ATOM | 2132 | N2 | LIG | A | 500 | 23.368 | 12.451 | 21.702 | 1.00 25.13 |
| ATOM | 2133 | C7 | LIG | A | 500 | 22.205 | 11.921 | 22.025 | 1.00 24.77 |
| ATOM | 2134 | C8 | LIG | A | 500 | 22.226 | 10.585 | 21.757 | 1.00 23.72 |
| ATOM | 2135 | C9 | LIG | A | 500 | 23.600 | 10.279 | 21.206 | 1.00 23.97 |
| ATOM | 2136 | C10 | LIG | A | 500 | 24.292 | 9.124 | 20.742 | 1.00 24.64 |
| ATOM | 2137 | N3 | LIG | A | 500 | 25.576 | 9.340 | 20.324 | 1.00 24.26 |
| ATOM | 2138 | C11 | LIG | A | 500 | 26.164 | 10.553 | 20.353 | 1.00 22.83 |
| ATOM | 2139 | N4 | LIG | A | 500 | 25.504 | 11.628 | 20.804 | 1.00 22.62 |
| ATOM | 2140 | C12 | LIG | A | 500 | 24.226 | 11.513 | 21.226 | 1.00 24.17 |
| ATOM | 2141 | N5 | LIG | A | 500 | 23.780 | 7.916 | 20.678 | 1.00 25.14 |
| ATOM | 2142 | C13 | LIG | A | 500 | 21.020 | 9.706 | 22.039 | 1.00 23.85 |
| ATOM | 2143 | C14 | LIG | A | 500 | 19.731 | 10.070 | 21.584 | 1.00 23.19 |
| ATOM | 2144 | C15 | LIG | A | 500 | 18.633 | 9.238 | 21.873 | 1.00 23.89 |
| ATOM | 2145 | C16 | LIG | A | 500 | 18.815 | 8.045 | 22.614 | 1.00 25.56 |
| ATOM | 2146 | O1 | LIG | A | 500 | 17.719 | 7.227 | 22.885 | 1.00 26.74 |
| ATOM | 2147 | C17 | LIG | A | 500 | 16.715 | 6.697 | 22.073 | 1.00 28.78 |

Figure 5

| | | | | | | | | |
|---|---|---|---|---|---|---|---|---|
| ATOM | 2148 | C18 | LIG | A | 500 | 15.385 | 6.632 | 22.524 | 1.00 28.53 |
| ATOM | 2149 | C19 | LIG | A | 500 | 14.384 | 6.102 | 21.694 | 1.00 28.45 |
| ATOM | 2150 | C20 | LIG | A | 500 | 14.701 | 5.628 | 20.408 | 1.00 27.49 |
| ATOM | 2151 | C21 | LIG | A | 500 | 16.031 | 5.688 | 19.944 | 1.00 28.77 |
| ATOM | 2152 | C22 | LIG | A | 500 | 17.043 | 6.221 | 20.772 | 1.00 28.79 |
| ATOM | 2153 | C23 | LIG | A | 500 | 20.100 | 7.689 | 23.057 | 1.00 24.73 |
| ATOM | 2154 | C24 | LIG | A | 500 | 21.190 | 8.516 | 22.767 | 1.00 23.79 |
| ATOM | 2155 | C25 | LIG | A | 500 | 24.139 | 18.930 | 20.608 | 1.00 37.39 |
| ATOM | 2156 | C26 | LIG | A | 500 | 24.708 | 20.407 | 20.741 | 1.00 39.14 |
| ATOM | 2157 | N6 | LIG | A | 500 | 23.676 | 21.291 | 21.379 | 1.00 38.96 |
| ATOM | 2158 | C27 | LIG | A | 500 | 24.171 | 22.697 | 21.523 | 1.00 40.26 |
| ATOM | 2159 | C28 | LIG | A | 500 | 23.321 | 20.719 | 22.674 | 1.00 38.32 |
| ATOM | 2160 | C29 | LIG | A | 500 | 22.805 | 19.263 | 22.550 | 1.00 36.36 |
| ATOM | 2161 | CB | TRP | B | 238 | 46.019 | 27.821 | 32.380 | 1.00 49.56 |
| ATOM | 2162 | CG | TRP | B | 238 | 45.564 | 28.174 | 33.769 | 1.00 51.18 |
| ATOM | 2163 | CD2 | TRP | B | 238 | 46.232 | 27.869 | 35.007 | 1.00 51.17 |
| ATOM | 2164 | CE2 | TRP | B | 238 | 45.444 | 28.405 | 36.048 | 1.00 51.84 |
| ATOM | 2165 | CE3 | TRP | B | 238 | 47.421 | 27.202 | 35.334 | 1.00 50.52 |
| ATOM | 2166 | CD1 | TRP | B | 238 | 44.431 | 28.855 | 34.106 | 1.00 52.07 |
| ATOM | 2167 | NE1 | TRP | B | 238 | 44.353 | 29.000 | 35.469 | 1.00 52.75 |
| ATOM | 2168 | CZ2 | TRP | B | 238 | 45.804 | 28.296 | 37.400 | 1.00 51.78 |
| ATOM | 2169 | CZ3 | TRP | B | 238 | 47.781 | 27.094 | 36.678 | 1.00 50.31 |
| ATOM | 2170 | CH2 | TRP | B | 238 | 46.973 | 27.639 | 37.693 | 1.00 50.90 |
| ATOM | 2171 | C | TRP | B | 238 | 47.775 | 27.988 | 30.627 | 1.00 48.29 |
| ATOM | 2172 | O | TRP | B | 238 | 48.319 | 26.892 | 30.776 | 1.00 48.38 |
| ATOM | 2173 | N | TRP | B | 238 | 46.682 | 30.088 | 31.572 | 1.00 47.91 |
| ATOM | 2174 | CA | TRP | B | 238 | 47.154 | 28.695 | 31.832 | 1.00 48.44 |
| ATOM | 2175 | N | GLU | B | 239 | 47.658 | 28.580 | 29.438 | 1.00 48.16 |
| ATOM | 2176 | CA | GLU | B | 239 | 48.228 | 27.981 | 28.225 | 1.00 47.27 |
| ATOM | 2177 | CB | GLU | B | 239 | 47.480 | 28.408 | 26.958 | 1.00 50.05 |
| ATOM | 2178 | CG | GLU | B | 239 | 46.429 | 27.446 | 26.463 | 1.00 53.34 |
| ATOM | 2179 | CD | GLU | B | 239 | 45.033 | 27.886 | 26.850 | 1.00 56.79 |
| ATOM | 2180 | OE1 | GLU | B | 239 | 44.546 | 27.453 | 27.923 | 1.00 58.08 |
| ATOM | 2181 | OE2 | GLU | B | 239 | 44.424 | 28.672 | 26.083 | 1.00 57.65 |
| ATOM | 2182 | C | GLU | B | 239 | 49.672 | 28.367 | 28.030 | 1.00 45.37 |
| ATOM | 2183 | O | GLU | B | 239 | 50.060 | 29.507 | 28.273 | 1.00 44.63 |
| ATOM | 2184 | N | VAL | B | 240 | 50.454 | 27.408 | 27.552 | 1.00 43.86 |
| ATOM | 2185 | CA | VAL | B | 240 | 51.862 | 27.626 | 27.265 | 1.00 42.20 |
| ATOM | 2186 | CB | VAL | B | 240 | 52.781 | 27.164 | 28.421 | 1.00 41.83 |
| ATOM | 2187 | CG1 | VAL | B | 240 | 52.474 | 27.953 | 29.686 | 1.00 40.95 |
| ATOM | 2188 | CG2 | VAL | B | 240 | 52.649 | 25.671 | 28.655 | 1.00 41.38 |
| ATOM | 2189 | C | VAL | B | 240 | 52.194 | 26.853 | 25.997 | 1.00 41.37 |
| ATOM | 2190 | O | VAL | B | 240 | 51.560 | 25.836 | 25.695 | 1.00 41.56 |
| ATOM | 2191 | N | PRO | B | 241 | 53.131 | 27.370 | 25.193 | 1.00 39.93 |
| ATOM | 2192 | CD | PRO | B | 241 | 53.772 | 28.692 | 25.284 | 1.00 39.11 |
| ATOM | 2193 | CA | PRO | B | 241 | 53.513 | 26.692 | 23.955 | 1.00 39.46 |
| ATOM | 2194 | CB | PRO | B | 241 | 54.452 | 27.706 | 23.304 | 1.00 38.90 |
| ATOM | 2195 | CG | PRO | B | 241 | 53.978 | 29.018 | 23.850 | 1.00 38.54 |
| ATOM | 2196 | C | PRO | B | 241 | 54.230 | 25.365 | 24.246 | 1.00 39.69 |
| ATOM | 2197 | O | PRO | B | 241 | 54.981 | 25.259 | 25.221 | 1.00 40.04 |
| ATOM | 2198 | N | ARG | B | 242 | 53.999 | 24.356 | 23.408 | 1.00 39.34 |
| ATOM | 2199 | CA | ARG | B | 242 | 54.634 | 23.049 | 23.577 | 1.00 39.38 |
| ATOM | 2200 | CB | ARG | B | 242 | 54.163 | 22.094 | 22.473 | 1.00 38.78 |
| ATOM | 2201 | CG | ARG | B | 242 | 55.039 | 20.857 | 22.288 | 1.00 40.17 |
| ATOM | 2202 | CD | ARG | B | 242 | 54.380 | 19.790 | 21.417 | 1.00 39.38 |
| ATOM | 2203 | NE | ARG | B | 242 | 53.266 | 19.186 | 22.127 | 1.00 38.52 |
| ATOM | 2204 | CZ | ARG | B | 242 | 51.994 | 19.350 | 21.802 | 1.00 37.61 |
| ATOM | 2205 | NH1 | ARG | B | 242 | 51.658 | 20.091 | 20.764 | 1.00 38.84 |
| ATOM | 2206 | NH2 | ARG | B | 242 | 51.059 | 18.816 | 22.556 | 1.00 37.77 |
| ATOM | 2207 | C | ARG | B | 242 | 56.173 | 23.132 | 23.614 | 1.00 39.88 |

Figure 5

| | | | | | | | | |
|---|---|---|---|---|---|---|---|---|
| ATOM | 2208 | O | ARG | B | 242 | 56.839 | 22.283 | 24.225 | 1.00 | 40.19 |
| ATOM | 2209 | N | GLU | B | 243 | 56.720 | 24.170 | 22.981 | 1.00 | 40.01 |
| ATOM | 2210 | CA | GLU | B | 243 | 58.164 | 24.433 | 22.906 | 1.00 | 40.52 |
| ATOM | 2211 | CB | GLU | B | 243 | 58.413 | 25.756 | 22.145 | 1.00 | 43.75 |
| ATOM | 2212 | CG | GLU | B | 243 | 58.244 | 25.716 | 20.612 | 1.00 | 48.92 |
| ATOM | 2213 | CD | GLU | B | 243 | 56.812 | 25.421 | 20.130 | 1.00 | 51.46 |
| ATOM | 2214 | OE1 | GLU | B | 243 | 56.018 | 26.385 | 19.990 | 1.00 | 53.23 |
| ATOM | 2215 | OE2 | GLU | B | 243 | 56.495 | 24.232 | 19.857 | 1.00 | 52.09 |
| ATOM | 2216 | C | GLU | B | 243 | 58.827 | 24.534 | 24.292 | 1.00 | 38.72 |
| ATOM | 2217 | O | GLU | B | 243 | 60.008 | 24.206 | 24.466 | 1.00 | 38.22 |
| ATOM | 2218 | N | THR | B | 244 | 58.057 | 25.013 | 25.267 | 1.00 | 36.80 |
| ATOM | 2219 | CA | THR | B | 244 | 58.517 | 25.212 | 26.645 | 1.00 | 34.57 |
| ATOM | 2220 | CB | THR | B | 244 | 57.624 | 26.252 | 27.336 | 1.00 | 34.40 |
| ATOM | 2221 | OG1 | THR | B | 244 | 56.356 | 25.664 | 27.659 | 1.00 | 33.00 |
| ATOM | 2222 | CG2 | THR | B | 244 | 57.389 | 27.425 | 26.393 | 1.00 | 34.59 |
| ATOM | 2223 | C | THR | B | 244 | 58.507 | 23.943 | 27.498 | 1.00 | 32.93 |
| ATOM | 2224 | O | THR | B | 244 | 58.744 | 23.984 | 28.706 | 1.00 | 31.79 |
| ATOM | 2225 | N | LEU | B | 245 | 58.304 | 22.812 | 26.841 | 1.00 | 32.02 |
| ATOM | 2226 | CA | LEU | B | 245 | 58.206 | 21.551 | 27.525 | 1.00 | 30.91 |
| ATOM | 2227 | CB | LEU | B | 245 | 56.722 | 21.231 | 27.666 | 1.00 | 31.48 |
| ATOM | 2228 | CG | LEU | B | 245 | 56.292 | 20.313 | 28.791 | 1.00 | 31.91 |
| ATOM | 2229 | CD1 | LEU | B | 245 | 56.479 | 21.040 | 30.085 | 1.00 | 34.08 |
| ATOM | 2230 | CD2 | LEU | B | 245 | 54.849 | 19.930 | 28.610 | 1.00 | 32.84 |
| ATOM | 2231 | C | LEU | B | 245 | 58.932 | 20.400 | 26.810 | 1.00 | 30.53 |
| ATOM | 2232 | O | LEU | B | 245 | 58.780 | 20.196 | 25.596 | 1.00 | 30.99 |
| ATOM | 2233 | N | LYS | B | 246 | 59.729 | 19.662 | 27.581 | 1.00 | 28.64 |
| ATOM | 2234 | CA | LYS | B | 246 | 60.457 | 18.513 | 27.079 | 1.00 | 27.09 |
| ATOM | 2235 | CB | LYS | B | 246 | 61.972 | 18.764 | 27.111 | 1.00 | 29.29 |
| ATOM | 2236 | CG | LYS | B | 246 | 62.819 | 17.585 | 26.588 | 1.00 | 30.62 |
| ATOM | 2237 | CD | LYS | B | 246 | 64.297 | 17.911 | 26.491 | 1.00 | 31.16 |
| ATOM | 2238 | CE | LYS | B | 246 | 64.859 | 18.404 | 27.803 | 1.00 | 31.69 |
| ATOM | 2239 | NZ | LYS | B | 246 | 66.304 | 18.751 | 27.668 | 1.00 | 34.05 |
| ATOM | 2240 | C | LYS | B | 246 | 60.097 | 17.297 | 27.945 | 1.00 | 25.34 |
| ATOM | 2241 | O | LYS | B | 246 | 60.271 | 17.315 | 29.159 | 1.00 | 24.31 |
| ATOM | 2242 | N | LEU | B | 247 | 59.485 | 16.299 | 27.306 | 1.00 | 23.80 |
| ATOM | 2243 | CA | LEU | B | 247 | 59.085 | 15.058 | 27.943 | 1.00 | 21.41 |
| ATOM | 2244 | CB | LEU | B | 247 | 57.931 | 14.403 | 27.176 | 1.00 | 19.06 |
| ATOM | 2245 | CG | LEU | B | 247 | 56.518 | 14.908 | 27.496 | 1.00 | 18.69 |
| ATOM | 2246 | CD1 | LEU | B | 247 | 56.400 | 16.411 | 27.224 | 1.00 | 17.59 |
| ATOM | 2247 | CD2 | LEU | B | 247 | 55.469 | 14.110 | 26.718 | 1.00 | 17.07 |
| ATOM | 2248 | C | LEU | B | 247 | 60.325 | 14.186 | 27.913 | 1.00 | 21.89 |
| ATOM | 2249 | O | LEU | B | 247 | 61.024 | 14.124 | 26.895 | 1.00 | 22.94 |
| ATOM | 2250 | N | VAL | B | 248 | 60.614 | 13.541 | 29.038 | 1.00 | 21.02 |
| ATOM | 2251 | CA | VAL | B | 248 | 61.809 | 12.719 | 29.156 | 1.00 | 19.93 |
| ATOM | 2252 | CB | VAL | B | 248 | 62.794 | 13.334 | 30.196 | 1.00 | 18.58 |
| ATOM | 2253 | CG1 | VAL | B | 248 | 64.047 | 12.479 | 30.326 | 1.00 | 17.84 |
| ATOM | 2254 | CG2 | VAL | B | 248 | 63.162 | 14.748 | 29.805 | 1.00 | 15.29 |
| ATOM | 2255 | C | VAL | B | 248 | 61.569 | 11.247 | 29.490 | 1.00 | 20.58 |
| ATOM | 2256 | O | VAL | B | 248 | 62.228 | 10.353 | 28.944 | 1.00 | 21.63 |
| ATOM | 2257 | N | GLU | B | 249 | 60.609 | 10.976 | 30.356 | 1.00 | 20.25 |
| ATOM | 2258 | CA | GLU | B | 249 | 60.368 | 9.602 | 30.728 | 1.00 | 19.81 |
| ATOM | 2259 | CB | GLU | B | 249 | 61.059 | 9.340 | 32.050 | 1.00 | 19.66 |
| ATOM | 2260 | CG | GLU | B | 249 | 61.016 | 7.913 | 32.467 | 1.00 | 22.02 |
| ATOM | 2261 | CD | GLU | B | 249 | 61.738 | 7.673 | 33.758 | 1.00 | 24.05 |
| ATOM | 2262 | OE1 | GLU | B | 249 | 62.475 | 8.581 | 34.217 | 1.00 | 23.22 |
| ATOM | 2263 | OE2 | GLU | B | 249 | 61.562 | 6.562 | 34.309 | 1.00 | 27.44 |
| ATOM | 2264 | C | GLU | B | 249 | 58.895 | 9.274 | 30.846 | 1.00 | 19.53 |
| ATOM | 2265 | O | GLU | B | 249 | 58.134 | 10.053 | 31.405 | 1.00 | 17.98 |
| ATOM | 2266 | N | ARG | B | 250 | 58.491 | 8.121 | 30.318 | 1.00 | 19.65 |
| ATOM | 2267 | CA | ARG | B | 250 | 57.092 | 7.729 | 30.409 | 1.00 | 20.15 |

Figure 5

| | | | | | | | | |
|---|---|---|---|---|---|---|---|---|
| ATOM | 2268 | CB | ARG | B | 250 | 56.668 | 6.911 | 29.193 | 1.00 21.33 |
| ATOM | 2269 | CG | ARG | B | 250 | 55.166 | 6.955 | 28.954 | 1.00 22.63 |
| ATOM | 2270 | CD | ARG | B | 250 | 54.764 | 6.124 | 27.757 | 1.00 23.11 |
| ATOM | 2271 | NE | ARG | B | 250 | 55.056 | 4.715 | 27.980 | 1.00 23.92 |
| ATOM | 2272 | CZ | ARG | B | 250 | 54.718 | 3.739 | 27.144 | 1.00 24.62 |
| ATOM | 2273 | NH1 | ARG | B | 250 | 54.074 | 4.017 | 26.017 | 1.00 24.65 |
| ATOM | 2274 | NH2 | ARG | B | 250 | 55.021 | 2.479 | 27.435 | 1.00 25.12 |
| ATOM | 2275 | C | ARG | B | 250 | 56.812 | 6.949 | 31.686 | 1.00 20.04 |
| ATOM | 2276 | O | ARG | B | 250 | 57.225 | 5.800 | 31.816 | 1.00 21.15 |
| ATOM | 2277 | N | LEU | B | 251 | 56.107 | 7.578 | 32.625 | 1.00 19.04 |
| ATOM | 2278 | CA | LEU | B | 251 | 55.781 | 6.942 | 33.900 | 1.00 17.60 |
| ATOM | 2279 | CB | LEU | B | 251 | 55.426 | 8.005 | 34.950 | 1.00 16.19 |
| ATOM | 2280 | CG | LEU | B | 251 | 56.479 | 9.115 | 35.144 | 1.00 15.53 |
| ATOM | 2281 | CD1 | LEU | B | 251 | 55.944 | 10.248 | 36.018 | 1.00 13.93 |
| ATOM | 2282 | CD2 | LEU | B | 251 | 57.768 | 8.543 | 35.726 | 1.00 12.30 |
| ATOM | 2283 | C | LEU | B | 251 | 54.664 | 5.899 | 33.770 | 1.00 17.87 |
| ATOM | 2284 | O | LEU | B | 251 | 54.673 | 4.885 | 34.463 | 1.00 17.58 |
| ATOM | 2285 | N | GLY | B | 252 | 53.724 | 6.140 | 32.855 | 1.00 18.87 |
| ATOM | 2286 | CA | GLY | B | 252 | 52.626 | 5.207 | 32.644 | 1.00 17.34 |
| ATOM | 2287 | C | GLY | B | 252 | 51.860 | 5.376 | 31.333 | 1.00 17.50 |
| ATOM | 2288 | O | GLY | B | 252 | 51.801 | 6.460 | 30.743 | 1.00 15.20 |
| ATOM | 2289 | N | ALA | B | 253 | 51.270 | 4.272 | 30.885 | 1.00 18.41 |
| ATOM | 2290 | CA | ALA | B | 253 | 50.481 | 4.231 | 29.665 | 1.00 19.16 |
| ATOM | 2291 | CB | ALA | B | 253 | 51.276 | 3.593 | 28.535 | 1.00 18.49 |
| ATOM | 2292 | C | ALA | B | 253 | 49.200 | 3.433 | 29.930 | 1.00 20.79 |
| ATOM | 2293 | O | ALA | B | 253 | 49.237 | 2.270 | 30.371 | 1.00 19.67 |
| ATOM | 2294 | N | GLY | B | 254 | 48.070 | 4.081 | 29.660 | 1.00 22.03 |
| ATOM | 2295 | CA | GLY | B | 254 | 46.780 | 3.457 | 29.863 | 1.00 23.23 |
| ATOM | 2296 | C | GLY | B | 254 | 45.798 | 3.728 | 28.737 | 1.00 24.94 |
| ATOM | 2297 | O | GLY | B | 254 | 46.138 | 4.342 | 27.719 | 1.00 26.15 |
| ATOM | 2298 | N | GLN | B | 255 | 44.551 | 3.335 | 28.970 | 1.00 25.43 |
| ATOM | 2299 | CA | GLN | B | 255 | 43.477 | 3.478 | 27.998 | 1.00 25.44 |
| ATOM | 2300 | CB | GLN | B | 255 | 42.190 | 2.895 | 28.587 | 1.00 27.36 |
| ATOM | 2301 | CG | GLN | B | 255 | 41.274 | 2.270 | 27.546 | 1.00 31.75 |
| ATOM | 2302 | CD | GLN | B | 255 | 39.799 | 2.281 | 27.950 | 1.00 34.54 |
| ATOM | 2303 | OE1 | GLN | B | 255 | 38.914 | 2.201 | 27.083 | 1.00 33.70 |
| ATOM | 2304 | NE2 | GLN | B | 255 | 39.528 | 2.386 | 29.266 | 1.00 35.17 |
| ATOM | 2305 | C | GLN | B | 255 | 43.216 | 4.892 | 27.461 | 1.00 23.66 |
| ATOM | 2306 | O | GLN | B | 255 | 43.039 | 5.073 | 26.261 | 1.00 23.60 |
| ATOM | 2307 | N | PHE | B | 256 | 43.211 | 5.883 | 28.346 | 1.00 22.05 |
| ATOM | 2308 | CA | PHE | B | 256 | 42.931 | 7.268 | 27.971 | 1.00 20.38 |
| ATOM | 2309 | CB | PHE | B | 256 | 42.127 | 7.956 | 29.067 | 1.00 19.94 |
| ATOM | 2310 | CG | PHE | B | 256 | 40.779 | 7.352 | 29.299 | 1.00 19.98 |
| ATOM | 2311 | CD1 | PHE | B | 256 | 40.325 | 6.300 | 28.511 | 1.00 20.28 |
| ATOM | 2312 | CD2 | PHE | B | 256 | 39.943 | 7.856 | 30.285 | 1.00 20.40 |
| ATOM | 2313 | CE1 | PHE | B | 256 | 39.055 | 5.763 | 28.697 | 1.00 21.05 |
| ATOM | 2314 | CE2 | PHE | B | 256 | 38.673 | 7.326 | 30.479 | 1.00 20.18 |
| ATOM | 2315 | CZ | PHE | B | 256 | 38.231 | 6.280 | 29.679 | 1.00 20.84 |
| ATOM | 2316 | C | PHE | B | 256 | 44.111 | 8.151 | 27.634 | 1.00 20.32 |
| ATOM | 2317 | O | PHE | B | 256 | 43.924 | 9.279 | 27.158 | 1.00 19.33 |
| ATOM | 2318 | N | GLY | B | 257 | 45.318 | 7.664 | 27.915 | 1.00 21.08 |
| ATOM | 2319 | CA | GLY | B | 257 | 46.520 | 8.446 | 27.646 | 1.00 21.18 |
| ATOM | 2320 | C | GLY | B | 257 | 47.742 | 7.993 | 28.428 | 1.00 20.90 |
| ATOM | 2321 | O | GLY | B | 257 | 47.821 | 6.838 | 28.870 | 1.00 19.82 |
| ATOM | 2322 | N | GLU | B | 258 | 48.664 | 8.927 | 28.657 | 1.00 21.06 |
| ATOM | 2323 | CA | GLU | B | 258 | 49.911 | 8.627 | 29.357 | 1.00 21.32 |
| ATOM | 2324 | CB | GLU | B | 258 | 51.016 | 8.418 | 28.322 | 1.00 22.30 |
| ATOM | 2325 | CG | GLU | B | 258 | 50.706 | 7.337 | 27.307 | 1.00 25.82 |
| ATOM | 2326 | CD | GLU | B | 258 | 51.627 | 7.352 | 26.103 | 1.00 28.69 |
| ATOM | 2327 | OE1 | GLU | B | 258 | 52.092 | 8.451 | 25.702 | 1.00 29.77 |

Figure 5

| ATOM | 2328 | OE2 | GLU | B | 258 | 51.873 | 6.254 | 25.546 | 1.00 | 31.37 |
|------|------|-----|-----|---|-----|--------|-------|--------|------|-------|
| ATOM | 2329 | C | GLU | B | 258 | 50.366 | 9.711 | 30.334 | 1.00 | 20.90 |
| ATOM | 2330 | O | GLU | B | 258 | 49.847 | 10.827 | 30.324 | 1.00 | 20.98 |
| ATOM | 2331 | N | VAL | B | 259 | 51.332 | 9.356 | 31.187 | 1.00 | 20.68 |
| ATOM | 2332 | CA | VAL | B | 259 | 51.930 | 10.283 | 32.171 | 1.00 | 19.84 |
| ATOM | 2333 | CB | VAL | B | 259 | 51.592 | 9.906 | 33.632 | 1.00 | 18.74 |
| ATOM | 2334 | CG1 | VAL | B | 259 | 52.208 | 10.915 | 34.595 | 1.00 | 15.96 |
| ATOM | 2335 | CG2 | VAL | B | 259 | 50.084 | 9.850 | 33.815 | 1.00 | 19.19 |
| ATOM | 2336 | C | VAL | B | 259 | 53.450 | 10.254 | 31.980 | 1.00 | 19.12 |
| ATOM | 2337 | O | VAL | B | 259 | 54.057 | 9.180 | 31.916 | 1.00 | 19.01 |
| ATOM | 2338 | N | TRP | B | 260 | 54.046 | 11.434 | 31.847 | 1.00 | 17.90 |
| ATOM | 2339 | CA | TRP | B | 260 | 55.477 | 11.553 | 31.627 | 1.00 | 18.23 |
| ATOM | 2340 | CB | TRP | B | 260 | 55.765 | 12.087 | 30.209 | 1.00 | 19.27 |
| ATOM | 2341 | CG | TRP | B | 260 | 55.569 | 11.123 | 29.082 | 1.00 | 21.71 |
| ATOM | 2342 | CD2 | TRP | B | 260 | 56.573 | 10.650 | 28.180 | 1.00 | 22.99 |
| ATOM | 2343 | CE2 | TRP | B | 260 | 55.936 | 9.790 | 27.261 | 1.00 | 23.87 |
| ATOM | 2344 | CE3 | TRP | B | 260 | 57.954 | 10.870 | 28.060 | 1.00 | 24.19 |
| ATOM | 2345 | CD1 | TRP | B | 260 | 54.396 | 10.543 | 28.687 | 1.00 | 22.65 |
| ATOM | 2346 | NE1 | TRP | B | 260 | 54.609 | 9.741 | 27.597 | 1.00 | 23.39 |
| ATOM | 2347 | CZ2 | TRP | B | 260 | 56.631 | 9.150 | 26.228 | 1.00 | 24.10 |
| ATOM | 2348 | CZ3 | TRP | B | 260 | 58.645 | 10.232 | 27.036 | 1.00 | 23.90 |
| ATOM | 2349 | CH2 | TRP | B | 260 | 57.981 | 9.382 | 26.135 | 1.00 | 24.80 |
| ATOM | 2350 | C | TRP | B | 260 | 56.157 | 12.506 | 32.591 | 1.00 | 17.77 |
| ATOM | 2351 | O | TRP | B | 260 | 55.569 | 13.482 | 33.054 | 1.00 | 17.73 |
| ATOM | 2352 | N | MET | B | 261 | 57.424 | 12.219 | 32.858 | 1.00 | 17.32 |
| ATOM | 2353 | CA | MET | B | 261 | 58.266 | 13.067 | 33.681 | 1.00 | 16.53 |
| ATOM | 2354 | CB | MET | B | 261 | 59.266 | 12.214 | 34.462 | 1.00 | 15.42 |
| ATOM | 2355 | CG | MET | B | 261 | 60.234 | 13.008 | 35.324 | 1.00 | 15.58 |
| ATOM | 2356 | SD | MET | B | 261 | 61.605 | 13.807 | 34.423 | 1.00 | 15.96 |
| ATOM | 2357 | CE | MET | B | 261 | 62.556 | 12.379 | 33.935 | 1.00 | 11.37 |
| ATOM | 2358 | C | MET | B | 261 | 58.968 | 13.922 | 32.610 | 1.00 | 16.19 |
| ATOM | 2359 | O | MET | B | 261 | 59.216 | 13.460 | 31.496 | 1.00 | 15.47 |
| ATOM | 2360 | N | GLY | B | 262 | 59.235 | 15.180 | 32.918 | 1.00 | 16.29 |
| ATOM | 2361 | CA | GLY | B | 262 | 59.863 | 16.046 | 31.938 | 1.00 | 16.20 |
| ATOM | 2362 | C | GLY | B | 262 | 60.259 | 17.355 | 32.569 | 1.00 | 16.43 |
| ATOM | 2363 | O | GLY | B | 262 | 60.140 | 17.518 | 33.776 | 1.00 | 17.31 |
| ATOM | 2364 | N | TYR | B | 263 | 60.735 | 18.295 | 31.774 | 1.00 | 16.91 |
| ATOM | 2365 | CA | TYR | B | 263 | 61.140 | 19.565 | 32.341 | 1.00 | 18.14 |
| ATOM | 2366 | CB | TYR | B | 263 | 62.668 | 19.730 | 32.267 | 1.00 | 17.89 |
| ATOM | 2367 | CG | TYR | B | 263 | 63.430 | 18.705 | 33.107 | 1.00 | 15.78 |
| ATOM | 2368 | CD1 | TYR | B | 263 | 63.819 | 18.997 | 34.415 | 1.00 | 14.65 |
| ATOM | 2369 | CE1 | TYR | B | 263 | 64.447 | 18.035 | 35.214 | 1.00 | 14.90 |
| ATOM | 2370 | CD2 | TYR | B | 263 | 63.703 | 17.420 | 32.610 | 1.00 | 15.20 |
| ATOM | 2371 | CE2 | TYR | B | 263 | 64.333 | 16.445 | 33.405 | 1.00 | 13.95 |
| ATOM | 2372 | CZ | TYR | B | 263 | 64.701 | 16.761 | 34.706 | 1.00 | 15.45 |
| ATOM | 2373 | OH | TYR | B | 263 | 65.301 | 15.803 | 35.510 | 1.00 | 15.72 |
| ATOM | 2374 | C | TYR | B | 263 | 60.387 | 20.691 | 31.673 | 1.00 | 19.65 |
| ATOM | 2375 | O | TYR | B | 263 | 60.071 | 20.624 | 30.487 | 1.00 | 20.52 |
| ATOM | 2376 | N | TYR | B | 264 | 60.016 | 21.674 | 32.479 | 1.00 | 21.48 |
| ATOM | 2377 | CA | TYR | B | 264 | 59.246 | 22.828 | 32.037 | 1.00 | 24.12 |
| ATOM | 2378 | CB | TYR | B | 264 | 57.986 | 22.923 | 32.924 | 1.00 | 23.87 |
| ATOM | 2379 | CG | TYR | B | 264 | 57.049 | 24.097 | 32.714 | 1.00 | 23.75 |
| ATOM | 2380 | CD1 | TYR | B | 264 | 56.649 | 24.503 | 31.440 | 1.00 | 23.72 |
| ATOM | 2381 | CE1 | TYR | B | 264 | 55.815 | 25.605 | 31.270 | 1.00 | 22.58 |
| ATOM | 2382 | CD2 | TYR | B | 264 | 56.583 | 24.824 | 33.809 | 1.00 | 23.32 |
| ATOM | 2383 | CE2 | TYR | B | 264 | 55.761 | 25.913 | 33.648 | 1.00 | 23.19 |
| ATOM | 2384 | CZ | TYR | B | 264 | 55.379 | 26.303 | 32.386 | 1.00 | 22.50 |
| ATOM | 2385 | OH | TYR | B | 264 | 54.550 | 27.395 | 32.266 | 1.00 | 23.80 |
| ATOM | 2386 | C | TYR | B | 264 | 60.187 | 24.022 | 32.182 | 1.00 | 26.68 |
| ATOM | 2387 | O | TYR | B | 264 | 60.840 | 24.190 | 33.212 | 1.00 | 27.05 |

Figure 5

| ATOM | 2388 | N   | ASN | B | 265 | 60.296 | 24.816 | 31.119 | 1.00 | 29.44 |
| ATOM | 2389 | CA  | ASN | B | 265 | 61.201 | 25.962 | 31.092 | 1.00 | 31.52 |
| ATOM | 2390 | CB  | ASN | B | 265 | 60.782 | 27.039 | 32.100 | 1.00 | 31.11 |
| ATOM | 2391 | CG  | ASN | B | 265 | 59.415 | 27.635 | 31.797 | 1.00 | 31.28 |
| ATOM | 2392 | OD1 | ASN | B | 265 | 59.080 | 27.921 | 30.642 | 1.00 | 30.86 |
| ATOM | 2393 | ND2 | ASN | B | 265 | 58.619 | 27.840 | 32.843 | 1.00 | 31.80 |
| ATOM | 2394 | C   | ASN | B | 265 | 62.616 | 25.456 | 31.381 | 1.00 | 33.37 |
| ATOM | 2395 | O   | ASN | B | 265 | 63.400 | 26.118 | 32.060 | 1.00 | 34.01 |
| ATOM | 2396 | N   | GLY | B | 266 | 62.895 | 24.236 | 30.923 | 1.00 | 35.02 |
| ATOM | 2397 | CA  | GLY | B | 266 | 64.204 | 23.629 | 31.095 | 1.00 | 37.23 |
| ATOM | 2398 | C   | GLY | B | 266 | 64.664 | 23.158 | 32.471 | 1.00 | 38.89 |
| ATOM | 2399 | O   | GLY | B | 266 | 65.490 | 22.249 | 32.544 | 1.00 | 39.61 |
| ATOM | 2400 | N   | HIS | B | 267 | 64.174 | 23.760 | 33.556 | 1.00 | 40.04 |
| ATOM | 2401 | CA  | HIS | B | 267 | 64.612 | 23.350 | 34.893 | 1.00 | 40.87 |
| ATOM | 2402 | CB  | HIS | B | 267 | 65.530 | 24.423 | 35.509 | 1.00 | 45.34 |
| ATOM | 2403 | CG  | HIS | B | 267 | 66.903 | 24.441 | 34.906 | 1.00 | 50.92 |
| ATOM | 2404 | CD2 | HIS | B | 267 | 67.886 | 23.505 | 34.894 | 1.00 | 52.55 |
| ATOM | 2405 | ND1 | HIS | B | 267 | 67.364 | 25.485 | 34.125 | 1.00 | 52.86 |
| ATOM | 2406 | CE1 | HIS | B | 267 | 68.562 | 25.185 | 33.654 | 1.00 | 54.07 |
| ATOM | 2407 | NE2 | HIS | B | 267 | 68.903 | 23.988 | 34.105 | 1.00 | 53.84 |
| ATOM | 2408 | C   | HIS | B | 267 | 63.576 | 22.859 | 35.912 | 1.00 | 38.95 |
| ATOM | 2409 | O   | HIS | B | 267 | 63.941 | 22.184 | 36.876 | 1.00 | 39.32 |
| ATOM | 2410 | N   | THR | B | 268 | 62.301 | 23.176 | 35.711 | 1.00 | 35.93 |
| ATOM | 2411 | CA  | THR | B | 268 | 61.264 | 22.725 | 36.638 | 1.00 | 33.15 |
| ATOM | 2412 | CB  | THR | B | 268 | 60.026 | 23.626 | 36.591 | 1.00 | 32.95 |
| ATOM | 2413 | OG1 | THR | B | 268 | 60.430 | 24.988 | 36.734 | 1.00 | 34.93 |
| ATOM | 2414 | CG2 | THR | B | 268 | 59.076 | 23.275 | 37.717 | 1.00 | 31.97 |
| ATOM | 2415 | C   | THR | B | 268 | 60.834 | 21.314 | 36.272 | 1.00 | 30.78 |
| ATOM | 2416 | O   | THR | B | 268 | 60.232 | 21.094 | 35.222 | 1.00 | 31.24 |
| ATOM | 2417 | N   | LYS | B | 269 | 61.139 | 20.356 | 37.133 | 1.00 | 27.55 |
| ATOM | 2418 | CA  | LYS | B | 269 | 60.761 | 18.978 | 36.861 | 1.00 | 24.79 |
| ATOM | 2419 | CB  | LYS | B | 269 | 61.448 | 18.051 | 37.852 | 1.00 | 24.24 |
| ATOM | 2420 | CG  | LYS | B | 269 | 61.494 | 16.608 | 37.430 | 1.00 | 24.10 |
| ATOM | 2421 | CD  | LYS | B | 269 | 62.295 | 15.834 | 38.444 | 1.00 | 24.78 |
| ATOM | 2422 | CE  | LYS | B | 269 | 62.831 | 14.553 | 37.856 | 1.00 | 25.75 |
| ATOM | 2423 | NZ  | LYS | B | 269 | 63.791 | 13.917 | 38.795 | 1.00 | 25.85 |
| ATOM | 2424 | C   | LYS | B | 269 | 59.240 | 18.880 | 36.984 | 1.00 | 23.63 |
| ATOM | 2425 | O   | LYS | B | 269 | 58.658 | 19.335 | 37.971 | 1.00 | 23.25 |
| ATOM | 2426 | N   | VAL | B | 270 | 58.592 | 18.300 | 35.975 | 1.00 | 21.85 |
| ATOM | 2427 | CA  | VAL | B | 270 | 57.137 | 18.188 | 35.971 | 1.00 | 19.75 |
| ATOM | 2428 | CB  | VAL | B | 270 | 56.486 | 19.323 | 35.101 | 1.00 | 18.90 |
| ATOM | 2429 | CG1 | VAL | B | 270 | 56.829 | 20.687 | 35.649 | 1.00 | 17.27 |
| ATOM | 2430 | CG2 | VAL | B | 270 | 56.921 | 19.215 | 33.643 | 1.00 | 18.10 |
| ATOM | 2431 | C   | VAL | B | 270 | 56.609 | 16.835 | 35.478 | 1.00 | 19.35 |
| ATOM | 2432 | O   | VAL | B | 270 | 57.360 | 16.029 | 34.922 | 1.00 | 19.03 |
| ATOM | 2433 | N   | ALA | B | 271 | 55.337 | 16.560 | 35.787 | 1.00 | 17.87 |
| ATOM | 2434 | CA  | ALA | B | 271 | 54.645 | 15.352 | 35.327 | 1.00 | 16.42 |
| ATOM | 2435 | CB  | ALA | B | 271 | 53.830 | 14.719 | 36.424 | 1.00 | 15.47 |
| ATOM | 2436 | C   | ALA | B | 271 | 53.722 | 15.933 | 34.285 | 1.00 | 16.44 |
| ATOM | 2437 | O   | ALA | B | 271 | 53.175 | 17.024 | 34.474 | 1.00 | 15.85 |
| ATOM | 2438 | N   | VAL | B | 272 | 53.549 | 15.225 | 33.181 | 1.00 | 16.90 |
| ATOM | 2439 | CA  | VAL | B | 272 | 52.715 | 15.735 | 32.113 | 1.00 | 16.60 |
| ATOM | 2440 | CB  | VAL | B | 272 | 53.563 | 16.147 | 30.877 | 1.00 | 15.78 |
| ATOM | 2441 | CG1 | VAL | B | 272 | 52.729 | 16.936 | 29.906 | 1.00 | 13.68 |
| ATOM | 2442 | CG2 | VAL | B | 272 | 54.818 | 16.928 | 31.300 | 1.00 | 15.28 |
| ATOM | 2443 | C   | VAL | B | 272 | 51.782 | 14.640 | 31.692 | 1.00 | 17.63 |
| ATOM | 2444 | O   | VAL | B | 272 | 52.239 | 13.582 | 31.255 | 1.00 | 20.16 |
| ATOM | 2445 | N   | LYS | B | 273 | 50.482 | 14.856 | 31.883 | 1.00 | 17.61 |
| ATOM | 2446 | CA  | LYS | B | 273 | 49.482 | 13.882 | 31.473 | 1.00 | 16.54 |
| ATOM | 2447 | CB  | LYS | B | 273 | 48.345 | 13.809 | 32.495 | 1.00 | 17.48 |

Figure 5

| ATOM | 2448 | CG  | LYS | B | 273 | 47.204 | 12.902 | 32.072 | 1.00 | 19.62 |
|------|------|-----|-----|---|-----|--------|--------|--------|------|-------|
| ATOM | 2449 | CD  | LYS | B | 273 | 46.089 | 12.899 | 33.093 | 1.00 | 22.19 |
| ATOM | 2450 | CE  | LYS | B | 273 | 46.522 | 12.191 | 34.368 | 1.00 | 23.99 |
| ATOM | 2451 | NZ  | LYS | B | 273 | 45.371 | 11.860 | 35.255 | 1.00 | 23.28 |
| ATOM | 2452 | C   | LYS | B | 273 | 48.970 | 14.284 | 30.082 | 1.00 | 16.42 |
| ATOM | 2453 | O   | LYS | B | 273 | 48.573 | 15.431 | 29.852 | 1.00 | 14.07 |
| ATOM | 2454 | N   | SER | B | 274 | 49.070 | 13.355 | 29.137 | 1.00 | 17.95 |
| ATOM | 2455 | CA  | SER | B | 274 | 48.623 | 13.606 | 27.779 | 1.00 | 20.26 |
| ATOM | 2456 | CB  | SER | B | 274 | 49.771 | 13.397 | 26.780 | 1.00 | 21.64 |
| ATOM | 2457 | OG  | SER | B | 274 | 50.099 | 12.030 | 26.649 | 1.00 | 25.81 |
| ATOM | 2458 | C   | SER | B | 274 | 47.428 | 12.728 | 27.422 | 1.00 | 20.69 |
| ATOM | 2459 | O   | SER | B | 274 | 47.280 | 11.621 | 27.944 | 1.00 | 19.15 |
| ATOM | 2460 | N   | LEU | B | 275 | 46.594 | 13.245 | 26.518 | 1.00 | 22.50 |
| ATOM | 2461 | CA  | LEU | B | 275 | 45.379 | 12.583 | 26.053 | 1.00 | 23.33 |
| ATOM | 2462 | CB  | LEU | B | 275 | 44.265 | 13.624 | 25.866 | 1.00 | 21.45 |
| ATOM | 2463 | CG  | LEU | B | 275 | 42.936 | 13.184 | 25.217 | 1.00 | 22.22 |
| ATOM | 2464 | CD1 | LEU | B | 275 | 42.223 | 12.162 | 26.103 | 1.00 | 19.66 |
| ATOM | 2465 | CD2 | LEU | B | 275 | 42.024 | 14.400 | 24.930 | 1.00 | 21.08 |
| ATOM | 2466 | C   | LEU | B | 275 | 45.535 | 11.785 | 24.760 | 1.00 | 25.32 |
| ATOM | 2467 | O   | LEU | B | 275 | 45.997 | 12.301 | 23.742 | 1.00 | 25.79 |
| ATOM | 2468 | N   | LYS | B | 276 | 45.137 | 10.520 | 24.815 | 1.00 | 27.79 |
| ATOM | 2469 | CA  | LYS | B | 276 | 45.157 |  9.645 | 23.646 | 1.00 | 30.62 |
| ATOM | 2470 | CB  | LYS | B | 276 | 45.038 |  8.178 | 24.097 | 1.00 | 29.71 |
| ATOM | 2471 | CG  | LYS | B | 276 | 44.764 |  7.179 | 22.983 | 1.00 | 29.80 |
| ATOM | 2472 | CD  | LYS | B | 276 | 44.686 |  5.745 | 23.515 | 1.00 | 31.40 |
| ATOM | 2473 | CE  | LYS | B | 276 | 45.976 |  5.336 | 24.230 | 1.00 | 33.48 |
| ATOM | 2474 | NZ  | LYS | B | 276 | 46.049 |  3.890 | 24.648 | 1.00 | 34.48 |
| ATOM | 2475 | C   | LYS | B | 276 | 43.925 | 10.051 | 22.816 | 1.00 | 32.41 |
| ATOM | 2476 | O   | LYS | B | 276 | 42.789 |  9.746 | 23.207 | 1.00 | 33.41 |
| ATOM | 2477 | N   | GLN | B | 277 | 44.141 | 10.769 | 21.708 | 1.00 | 34.07 |
| ATOM | 2478 | CA  | GLN | B | 277 | 43.044 | 11.224 | 20.836 | 1.00 | 35.26 |
| ATOM | 2479 | CB  | GLN | B | 277 | 43.567 | 11.697 | 19.460 | 1.00 | 38.51 |
| ATOM | 2480 | CG  | GLN | B | 277 | 44.060 | 13.173 | 19.408 | 1.00 | 45.76 |
| ATOM | 2481 | CD  | GLN | B | 277 | 45.573 | 13.348 | 19.046 | 1.00 | 49.98 |
| ATOM | 2482 | OE1 | GLN | B | 277 | 46.233 | 14.283 | 19.523 | 1.00 | 51.18 |
| ATOM | 2483 | NE2 | GLN | B | 277 | 46.101 | 12.465 | 18.191 | 1.00 | 52.28 |
| ATOM | 2484 | C   | GLN | B | 277 | 41.964 | 10.158 | 20.646 | 1.00 | 33.81 |
| ATOM | 2485 | O   | GLN | B | 277 | 42.253 |  9.002 | 20.321 | 1.00 | 33.01 |
| ATOM | 2486 | N   | GLY | B | 278 | 40.731 | 10.540 | 20.959 | 1.00 | 33.20 |
| ATOM | 2487 | CA  | GLY | B | 278 | 39.605 |  9.634 | 20.812 | 1.00 | 32.56 |
| ATOM | 2488 | C   | GLY | B | 278 | 38.974 |  9.150 | 22.105 | 1.00 | 31.48 |
| ATOM | 2489 | O   | GLY | B | 278 | 37.774 |  8.906 | 22.159 | 1.00 | 31.34 |
| ATOM | 2490 | N   | SER | B | 279 | 39.782 |  9.003 | 23.145 | 1.00 | 30.90 |
| ATOM | 2491 | CA  | SER | B | 279 | 39.299 |  8.536 | 24.441 | 1.00 | 30.31 |
| ATOM | 2492 | CB  | SER | B | 279 | 40.480 |  8.462 | 25.410 | 1.00 | 30.49 |
| ATOM | 2493 | OG  | SER | B | 279 | 41.482 |  7.607 | 24.878 | 1.00 | 28.68 |
| ATOM | 2494 | C   | SER | B | 279 | 38.169 |  9.407 | 24.997 | 1.00 | 29.02 |
| ATOM | 2495 | O   | SER | B | 279 | 37.257 |  8.912 | 25.654 | 1.00 | 28.29 |
| ATOM | 2496 | N   | MET | B | 280 | 38.246 | 10.699 | 24.683 | 1.00 | 28.12 |
| ATOM | 2497 | CA  | MET | B | 280 | 37.278 | 11.724 | 25.073 | 1.00 | 26.58 |
| ATOM | 2498 | CB  | MET | B | 280 | 37.262 | 11.928 | 26.596 | 1.00 | 26.48 |
| ATOM | 2499 | CG  | MET | B | 280 | 38.500 | 12.604 | 27.184 | 1.00 | 26.05 |
| ATOM | 2500 | SD  | MET | B | 280 | 38.842 | 12.182 | 28.912 | 1.00 | 23.19 |
| ATOM | 2501 | CE  | MET | B | 280 | 37.979 | 13.394 | 29.707 | 1.00 | 25.77 |
| ATOM | 2502 | C   | MET | B | 280 | 37.717 | 13.000 | 24.338 | 1.00 | 26.36 |
| ATOM | 2503 | O   | MET | B | 280 | 38.786 | 13.030 | 23.717 | 1.00 | 26.49 |
| ATOM | 2504 | N   | SER | B | 281 | 36.869 | 14.023 | 24.335 | 1.00 | 26.55 |
| ATOM | 2505 | CA  | SER | B | 281 | 37.203 | 15.270 | 23.653 | 1.00 | 26.44 |
| ATOM | 2506 | CB  | SER | B | 281 | 35.946 | 16.111 | 23.411 | 1.00 | 26.16 |
| ATOM | 2507 | OG  | SER | B | 281 | 35.615 | 16.907 | 24.542 | 1.00 | 24.75 |

Figure 5

```
ATOM   2508  C    SER B 281      38.200  16.095  24.463  1.00 27.48
ATOM   2509  O    SER B 281      38.285  15.970  25.688  1.00 27.71
ATOM   2510  N    PRO B 282      39.000  16.920  23.779  1.00 27.73
ATOM   2511  CD   PRO B 282      39.227  16.909  22.320  1.00 27.29
ATOM   2512  CA   PRO B 282      39.985  17.767  24.445  1.00 28.67
ATOM   2513  CB   PRO B 282      40.480  18.645  23.299  1.00 27.75
ATOM   2514  CG   PRO B 282      40.533  17.666  22.178  1.00 26.47
ATOM   2515  C    PRO B 282      39.386  18.592  25.580  1.00 29.60
ATOM   2516  O    PRO B 282      40.028  18.798  26.606  1.00 30.23
ATOM   2517  N    ASP B 283      38.134  19.009  25.414  1.00 30.89
ATOM   2518  CA   ASP B 283      37.426  19.817  26.416  1.00 30.92
ATOM   2519  CB   ASP B 283      36.122  20.372  25.811  1.00 33.37
ATOM   2520  CG   ASP B 283      36.336  21.658  24.994  1.00 36.12
ATOM   2521  OD1  ASP B 283      36.174  22.750  25.577  1.00 37.15
ATOM   2522  OD2  ASP B 283      36.637  21.584  23.777  1.00 37.38
ATOM   2523  C    ASP B 283      37.151  19.105  27.763  1.00 29.98
ATOM   2524  O    ASP B 283      37.255  19.723  28.825  1.00 28.71
ATOM   2525  N    ALA B 284      36.814  17.816  27.711  1.00 28.87
ATOM   2526  CA   ALA B 284      36.532  17.020  28.909  1.00 27.40
ATOM   2527  CB   ALA B 284      35.760  15.773  28.536  1.00 26.23
ATOM   2528  C    ALA B 284      37.821  16.633  29.627  1.00 27.14
ATOM   2529  O    ALA B 284      37.822  16.400  30.846  1.00 26.68
ATOM   2530  N    PHE B 285      38.906  16.514  28.857  1.00 26.33
ATOM   2531  CA   PHE B 285      40.219  16.157  29.405  1.00 25.36
ATOM   2532  CB   PHE B 285      41.185  15.762  28.279  1.00 24.23
ATOM   2533  CG   PHE B 285      42.573  15.436  28.748  1.00 21.36
ATOM   2534  CD1  PHE B 285      42.816  14.305  29.513  1.00 19.87
ATOM   2535  CD2  PHE B 285      43.640  16.268  28.433  1.00 20.02
ATOM   2536  CE1  PHE B 285      44.098  14.014  29.961  1.00 19.34
ATOM   2537  CE2  PHE B 285      44.927  15.976  28.877  1.00 19.49
ATOM   2538  CZ   PHE B 285      45.155  14.850  29.640  1.00 18.74
ATOM   2539  C    PHE B 285      40.757  17.362  30.153  1.00 25.70
ATOM   2540  O    PHE B 285      41.084  17.272  31.331  1.00 25.10
ATOM   2541  N    LEU B 286      40.837  18.496  29.462  1.00 26.63
ATOM   2542  CA   LEU B 286      41.309  19.735  30.068  1.00 28.06
ATOM   2543  CB   LEU B 286      41.404  20.840  29.014  1.00 28.53
ATOM   2544  CG   LEU B 286      42.491  20.590  27.958  1.00 29.45
ATOM   2545  CD1  LEU B 286      42.301  21.457  26.715  1.00 30.23
ATOM   2546  CD2  LEU B 286      43.853  20.825  28.585  1.00 28.96
ATOM   2547  C    LEU B 286      40.380  20.149  31.199  1.00 29.59
ATOM   2548  O    LEU B 286      40.812  20.765  32.171  1.00 29.62
ATOM   2549  N    ALA B 287      39.102  19.785  31.072  1.00 32.20
ATOM   2550  CA   ALA B 287      38.085  20.087  32.081  1.00 33.52
ATOM   2551  CB   ALA B 287      36.693  19.756  31.566  1.00 33.33
ATOM   2552  C    ALA B 287      38.355  19.315  33.353  1.00 35.15
ATOM   2553  O    ALA B 287      37.760  19.600  34.380  1.00 36.59
ATOM   2554  N    GLU B 288      39.190  18.284  33.274  1.00 36.99
ATOM   2555  CA   GLU B 288      39.538  17.503  34.461  1.00 38.41
ATOM   2556  CB   GLU B 288      40.082  16.129  34.079  1.00 39.19
ATOM   2557  CG   GLU B 288      39.083  15.199  33.408  1.00 39.81
ATOM   2558  CD   GLU B 288      39.645  13.796  33.183  1.00 41.03
ATOM   2559  OE1  GLU B 288      40.886  13.588  33.337  1.00 38.68
ATOM   2560  OE2  GLU B 288      38.826  12.903  32.848  1.00 40.80
ATOM   2561  C    GLU B 288      40.605  18.251  35.254  1.00 39.49
ATOM   2562  O    GLU B 288      40.886  17.927  36.407  1.00 39.03
ATOM   2563  N    ALA B 289      41.222  19.233  34.608  1.00 41.02
ATOM   2564  CA   ALA B 289      42.252  20.026  35.238  1.00 42.45
ATOM   2565  CB   ALA B 289      43.302  20.435  34.225  1.00 43.03
ATOM   2566  C    ALA B 289      41.725  21.248  35.952  1.00 43.76
ATOM   2567  O    ALA B 289      42.160  21.517  37.049  1.00 43.61
```

Figure 5

| | | | | | | | | | |
|---|---|---|---|---|---|---|---|---|---|
| ATOM | 2568 | N | ASN | B | 290 | 40.800 | 21.978 | 35.332 | 1.00 45.93 |
| ATOM | 2569 | CA | ASN | B | 290 | 40.248 | 23.215 | 35.918 | 1.00 48.39 |
| ATOM | 2570 | CB | ASN | B | 290 | 39.225 | 23.880 | 34.963 | 1.00 50.03 |
| ATOM | 2571 | CG | ASN | B | 290 | 38.097 | 22.950 | 34.565 | 1.00 51.25 |
| ATOM | 2572 | OD1 | ASN | B | 290 | 37.909 | 21.909 | 35.180 | 1.00 51.62 |
| ATOM | 2573 | ND2 | ASN | B | 290 | 37.326 | 23.335 | 33.544 | 1.00 52.02 |
| ATOM | 2574 | C | ASN | B | 290 | 39.718 | 23.170 | 37.381 | 1.00 47.76 |
| ATOM | 2575 | O | ASN | B | 290 | 39.312 | 24.185 | 37.955 | 1.00 48.27 |
| ATOM | 2576 | N | LEU | B | 291 | 39.777 | 21.991 | 37.986 | 1.00 46.68 |
| ATOM | 2577 | CA | LEU | B | 291 | 39.362 | 21.777 | 39.375 | 1.00 45.44 |
| ATOM | 2578 | CB | LEU | B | 291 | 39.017 | 20.296 | 39.541 | 1.00 46.36 |
| ATOM | 2579 | CG | LEU | B | 291 | 38.439 | 19.579 | 38.307 | 1.00 45.76 |
| ATOM | 2580 | CD1 | LEU | B | 291 | 38.696 | 18.116 | 38.413 | 1.00 45.07 |
| ATOM | 2581 | CD2 | LEU | B | 291 | 36.961 | 19.861 | 38.109 | 1.00 46.55 |
| ATOM | 2582 | C | LEU | B | 291 | 40.590 | 22.115 | 40.234 | 1.00 44.64 |
| ATOM | 2583 | O | LEU | B | 291 | 40.502 | 22.535 | 41.391 | 1.00 44.14 |
| ATOM | 2584 | N | MET | B | 292 | 41.751 | 21.919 | 39.613 | 1.00 43.98 |
| ATOM | 2585 | CA | MET | B | 292 | 43.084 | 22.152 | 40.173 | 1.00 42.03 |
| ATOM | 2586 | CB | MET | B | 292 | 44.081 | 21.285 | 39.390 | 1.00 38.70 |
| ATOM | 2587 | CG | MET | B | 292 | 45.384 | 20.933 | 40.102 | 1.00 34.23 |
| ATOM | 2588 | SD | MET | B | 292 | 46.240 | 19.631 | 39.187 | 1.00 27.52 |
| ATOM | 2589 | CE | MET | B | 292 | 45.205 | 19.411 | 37.732 | 1.00 28.62 |
| ATOM | 2590 | C | MET | B | 292 | 43.430 | 23.627 | 40.033 | 1.00 42.53 |
| ATOM | 2591 | O | MET | B | 292 | 44.341 | 24.118 | 40.703 | 1.00 42.77 |
| ATOM | 2592 | N | LYS | B | 293 | 42.731 | 24.307 | 39.118 | 1.00 43.53 |
| ATOM | 2593 | CA | LYS | B | 293 | 42.931 | 25.732 | 38.869 | 1.00 43.74 |
| ATOM | 2594 | CB | LYS | B | 293 | 42.291 | 26.154 | 37.568 | 1.00 45.02 |
| ATOM | 2595 | CG | LYS | B | 293 | 42.846 | 25.515 | 36.309 | 1.00 46.94 |
| ATOM | 2596 | CD | LYS | B | 293 | 42.213 | 26.241 | 35.107 | 1.00 50.22 |
| ATOM | 2597 | CE | LYS | B | 293 | 42.845 | 25.878 | 33.756 | 1.00 52.20 |
| ATOM | 2598 | NZ | LYS | B | 293 | 42.466 | 26.864 | 32.669 | 1.00 52.88 |
| ATOM | 2599 | C | LYS | B | 293 | 42.290 | 26.511 | 40.000 | 1.00 44.11 |
| ATOM | 2600 | O | LYS | B | 293 | 42.839 | 27.502 | 40.470 | 1.00 44.75 |
| ATOM | 2601 | N | GLN | B | 294 | 41.130 | 26.058 | 40.460 | 1.00 44.76 |
| ATOM | 2602 | CA | GLN | B | 294 | 40.419 | 26.728 | 41.552 | 1.00 44.99 |
| ATOM | 2603 | CB | GLN | B | 294 | 38.947 | 26.289 | 41.608 | 1.00 46.50 |
| ATOM | 2604 | CG | GLN | B | 294 | 38.159 | 26.499 | 40.302 | 1.00 50.09 |
| ATOM | 2605 | CD | GLN | B | 294 | 38.086 | 27.971 | 39.853 | 1.00 52.70 |
| ATOM | 2606 | OE1 | GLN | B | 294 | 38.771 | 28.389 | 38.902 | 1.00 52.78 |
| ATOM | 2607 | NE2 | GLN | B | 294 | 37.233 | 28.752 | 40.516 | 1.00 52.35 |
| ATOM | 2608 | C | GLN | B | 294 | 41.096 | 26.483 | 42.911 | 1.00 43.96 |
| ATOM | 2609 | O | GLN | B | 294 | 41.479 | 27.429 | 43.597 | 1.00 44.05 |
| ATOM | 2610 | N | LEU | B | 295 | 41.303 | 25.215 | 43.262 | 1.00 42.44 |
| ATOM | 2611 | CA | LEU | B | 295 | 41.911 | 24.862 | 44.541 | 1.00 40.70 |
| ATOM | 2612 | CB | LEU | B | 295 | 41.261 | 23.595 | 45.086 | 1.00 41.54 |
| ATOM | 2613 | CG | LEU | B | 295 | 39.743 | 23.619 | 45.219 | 1.00 41.72 |
| ATOM | 2614 | CD1 | LEU | B | 295 | 39.275 | 22.258 | 45.720 | 1.00 42.04 |
| ATOM | 2615 | CD2 | LEU | B | 295 | 39.309 | 24.752 | 46.156 | 1.00 40.74 |
| ATOM | 2616 | C | LEU | B | 295 | 43.429 | 24.700 | 44.569 | 1.00 38.91 |
| ATOM | 2617 | O | LEU | B | 295 | 44.010 | 23.916 | 43.817 | 1.00 38.49 |
| ATOM | 2618 | N | GLN | B | 296 | 44.061 | 25.417 | 45.488 | 1.00 37.61 |
| ATOM | 2619 | CA | GLN | B | 296 | 45.509 | 25.355 | 45.651 | 1.00 36.74 |
| ATOM | 2620 | CB | GLN | B | 296 | 46.151 | 26.636 | 45.111 | 1.00 38.70 |
| ATOM | 2621 | CG | GLN | B | 296 | 45.897 | 26.817 | 43.615 | 1.00 41.04 |
| ATOM | 2622 | CD | GLN | B | 296 | 46.085 | 28.233 | 43.152 | 1.00 42.86 |
| ATOM | 2623 | OE1 | GLN | B | 296 | 46.200 | 29.154 | 43.963 | 1.00 44.31 |
| ATOM | 2624 | NE2 | GLN | B | 296 | 46.111 | 28.426 | 41.836 | 1.00 44.03 |
| ATOM | 2625 | C | GLN | B | 296 | 45.838 | 25.128 | 47.120 | 1.00 34.65 |
| ATOM | 2626 | O | GLN | B | 296 | 45.357 | 25.836 | 48.012 | 1.00 34.35 |
| ATOM | 2627 | N | HIS | B | 297 | 46.644 | 24.109 | 47.369 | 1.00 32.41 |

Figure 5

```
ATOM   2628  CA   HIS B 297      46.992  23.759  48.727  1.00 30.01
ATOM   2629  CB   HIS B 297      45.861  22.921  49.325  1.00 28.26
ATOM   2630  CG   HIS B 297      45.860  22.885  50.818  1.00 25.35
ATOM   2631  CD2  HIS B 297      45.256  23.686  51.725  1.00 23.95
ATOM   2632  ND1  HIS B 297      46.579  21.959  51.539  1.00 24.44
ATOM   2633  CE1  HIS B 297      46.424  22.196  52.830  1.00 24.04
ATOM   2634  NE2  HIS B 297      45.626  23.239  52.968  1.00 23.04
ATOM   2635  C    HIS B 297      48.262  22.947  48.743  1.00 30.14
ATOM   2636  O    HIS B 297      48.611  22.296  47.755  1.00 29.22
ATOM   2637  N    GLN B 298      48.925  22.953  49.895  1.00 31.20
ATOM   2638  CA   GLN B 298      50.166  22.209  50.077  1.00 32.04
ATOM   2639  CB   GLN B 298      50.841  22.633  51.386  1.00 35.65
ATOM   2640  CG   GLN B 298      51.467  24.046  51.312  1.00 42.31
ATOM   2641  CD   GLN B 298      52.530  24.189  50.184  1.00 45.11
ATOM   2642  OE1  GLN B 298      52.649  25.252  49.551  1.00 45.07
ATOM   2643  NE2  GLN B 298      53.291  23.112  49.932  1.00 44.65
ATOM   2644  C    GLN B 298      49.969  20.689  50.015  1.00 30.06
ATOM   2645  O    GLN B 298      50.912  19.943  49.749  1.00 29.31
ATOM   2646  N    ARG B 299      48.724  20.255  50.206  1.00 28.46
ATOM   2647  CA   ARG B 299      48.359  18.839  50.183  1.00 26.47
ATOM   2648  CB   ARG B 299      47.457  18.516  51.371  1.00 26.40
ATOM   2649  CG   ARG B 299      48.103  18.757  52.708  1.00 27.82
ATOM   2650  CD   ARG B 299      49.199  17.764  52.950  1.00 28.44
ATOM   2651  NE   ARG B 299      50.217  18.325  53.822  1.00 30.20
ATOM   2652  CZ   ARG B 299      51.508  18.360  53.515  1.00 32.09
ATOM   2653  NH1  ARG B 299      51.944  17.862  52.349  1.00 32.17
ATOM   2654  NH2  ARG B 299      52.363  18.884  54.378  1.00 31.28
ATOM   2655  C    ARG B 299      47.640  18.476  48.886  1.00 24.72
ATOM   2656  O    ARG B 299      47.164  17.361  48.726  1.00 24.06
ATOM   2657  N    LEU B 300      47.507  19.456  48.000  1.00 24.02
ATOM   2658  CA   LEU B 300      46.862  19.281  46.703  1.00 22.90
ATOM   2659  CB   LEU B 300      45.792  20.355  46.512  1.00 21.50
ATOM   2660  CG   LEU B 300      44.341  19.907  46.572  1.00 20.70
ATOM   2661  CD1  LEU B 300      44.109  19.088  47.828  1.00 19.26
ATOM   2662  CD2  LEU B 300      43.420  21.114  46.497  1.00 19.11
ATOM   2663  C    LEU B 300      47.882  19.418  45.585  1.00 22.73
ATOM   2664  O    LEU B 300      48.721  20.318  45.624  1.00 23.12
ATOM   2665  N    VAL B 301      47.820  18.526  44.598  1.00 22.98
ATOM   2666  CA   VAL B 301      48.734  18.594  43.459  1.00 23.00
ATOM   2667  CB   VAL B 301      48.570  17.402  42.519  1.00 21.85
ATOM   2668  CG1  VAL B 301      49.255  17.680  41.204  1.00 22.08
ATOM   2669  CG2  VAL B 301      49.172  16.164  43.146  1.00 20.55
ATOM   2670  C    VAL B 301      48.519  19.905  42.699  1.00 24.56
ATOM   2671  O    VAL B 301      47.396  20.269  42.339  1.00 25.82
ATOM   2672  N    ARG B 302      49.613  20.636  42.533  1.00 26.35
ATOM   2673  CA   ARG B 302      49.635  21.933  41.877  1.00 26.94
ATOM   2674  CB   ARG B 302      50.760  22.776  42.507  1.00 29.41
ATOM   2675  CG   ARG B 302      50.878  24.220  42.056  1.00 34.53
ATOM   2676  CD   ARG B 302      51.973  24.361  41.016  1.00 39.93
ATOM   2677  NE   ARG B 302      52.312  25.747  40.685  1.00 43.01
ATOM   2678  CZ   ARG B 302      53.301  26.436  41.256  1.00 44.52
ATOM   2679  NH1  ARG B 302      54.045  25.877  42.203  1.00 44.13
ATOM   2680  NH2  ARG B 302      53.605  27.650  40.813  1.00 45.46
ATOM   2681  C    ARG B 302      49.780  21.846  40.359  1.00 25.73
ATOM   2682  O    ARG B 302      50.534  21.027  39.814  1.00 25.14
ATOM   2683  N    LEU B 303      48.977  22.656  39.688  1.00 24.80
ATOM   2684  CA   LEU B 303      48.992  22.744  38.244  1.00 24.22
ATOM   2685  CB   LEU B 303      47.591  23.061  37.731  1.00 22.84
ATOM   2686  CG   LEU B 303      47.404  23.034  36.216  1.00 21.81
ATOM   2687  CD1  LEU B 303      47.289  21.603  35.733  1.00 20.65
```

Figure 5

```
ATOM  2688  CD2  LEU  B  303    46.157  23.804  35.855  1.00  21.30
ATOM  2689  C    LEU  B  303    49.935  23.880  37.848  1.00  24.74
ATOM  2690  O    LEU  B  303    50.041  24.892  38.560  1.00  24.22
ATOM  2691  N    TYR  B  304    50.649  23.681  36.740  1.00  25.26
ATOM  2692  CA   TYR  B  304    51.561  24.683  36.214  1.00  25.95
ATOM  2693  CB   TYR  B  304    52.959  24.111  35.962  1.00  27.38
ATOM  2694  CG   TYR  B  304    53.822  23.969  37.198  1.00  29.55
ATOM  2695  CD1  TYR  B  304    54.100  22.711  37.732  1.00  31.28
ATOM  2696  CE1  TYR  B  304    54.927  22.555  38.835  1.00  32.02
ATOM  2697  CD2  TYR  B  304    54.399  25.081  37.809  1.00  31.65
ATOM  2698  CE2  TYR  B  304    55.240  24.935  38.925  1.00  33.14
ATOM  2699  CZ   TYR  B  304    55.493  23.662  39.423  1.00  33.44
ATOM  2700  OH   TYR  B  304    56.323  23.478  40.496  1.00  35.95
ATOM  2701  C    TYR  B  304    50.986  25.203  34.913  1.00  25.83
ATOM  2702  O    TYR  B  304    50.850  26.411  34.730  1.00  26.99
ATOM  2703  N    ALA  B  305    50.594  24.291  34.030  1.00  24.70
ATOM  2704  CA   ALA  B  305    50.054  24.700  32.746  1.00  24.51
ATOM  2705  CB   ALA  B  305    51.150  25.384  31.934  1.00  24.90
ATOM  2706  C    ALA  B  305    49.452  23.544  31.952  1.00  24.77
ATOM  2707  O    ALA  B  305    49.422  22.413  32.419  1.00  23.88
ATOM  2708  N    VAL  B  306    48.973  23.852  30.745  1.00  26.07
ATOM  2709  CA   VAL  B  306    48.368  22.867  29.838  1.00  27.47
ATOM  2710  CB   VAL  B  306    46.816  22.805  29.987  1.00  28.10
ATOM  2711  CG1  VAL  B  306    46.428  22.329  31.375  1.00  28.90
ATOM  2712  CG2  VAL  B  306    46.181  24.167  29.695  1.00  26.80
ATOM  2713  C    VAL  B  306    48.659  23.256  28.391  1.00  28.34
ATOM  2714  O    VAL  B  306    48.890  24.425  28.099  1.00  28.56
ATOM  2715  N    VAL  B  307    48.684  22.272  27.495  1.00  29.44
ATOM  2716  CA   VAL  B  307    48.908  22.530  26.071  1.00  31.34
ATOM  2717  CB   VAL  B  307    50.144  21.792  25.512  1.00  30.66
ATOM  2718  CG1  VAL  B  307    50.250  22.019  24.000  1.00  31.17
ATOM  2719  CG2  VAL  B  307    51.403  22.283  26.201  1.00  29.02
ATOM  2720  C    VAL  B  307    47.651  22.115  25.297  1.00  33.68
ATOM  2721  O    VAL  B  307    47.269  20.934  25.259  1.00  33.96
ATOM  2722  N    THR  B  308    47.033  23.099  24.652  1.00  35.65
ATOM  2723  CA   THR  B  308    45.798  22.884  23.924  1.00  37.70
ATOM  2724  CB   THR  B  308    44.946  24.147  23.969  1.00  38.11
ATOM  2725  OG1  THR  B  308    45.769  25.287  23.681  1.00  39.99
ATOM  2726  CG2  THR  B  308    44.356  24.302  25.365  1.00  36.91
ATOM  2727  C    THR  B  308    45.839  22.279  22.523  1.00  39.36
ATOM  2728  O    THR  B  308    44.834  21.746  22.068  1.00  39.70
ATOM  2729  N    GLN  B  309    46.963  22.355  21.819  1.00  41.45
ATOM  2730  CA   GLN  B  309    47.017  21.725  20.498  1.00  43.91
ATOM  2731  CB   GLN  B  309    48.041  22.410  19.566  1.00  46.53
ATOM  2732  CG   GLN  B  309    49.512  22.320  20.014  1.00  51.47
ATOM  2733  CD   GLN  B  309    50.524  22.691  18.911  1.00  53.56
ATOM  2734  OE1  GLN  B  309    50.253  22.537  17.711  1.00  53.36
ATOM  2735  NE2  GLN  B  309    51.700  23.170  19.327  1.00  54.13
ATOM  2736  C    GLN  B  309    47.356  20.245  20.723  1.00  43.72
ATOM  2737  O    GLN  B  309    48.169  19.918  21.589  1.00  43.85
ATOM  2738  N    GLU  B  310    46.715  19.352  19.977  1.00  43.46
ATOM  2739  CA   GLU  B  310    46.946  17.915  20.130  1.00  44.09
ATOM  2740  CB   GLU  B  310    45.964  17.119  19.260  1.00  47.80
ATOM  2741  CG   GLU  B  310    45.958  17.469  17.754  1.00  52.71
ATOM  2742  CD   GLU  B  310    45.070  18.680  17.384  1.00  55.35
ATOM  2743  OE1  GLU  B  310    43.828  18.615  17.610  1.00  55.37
ATOM  2744  OE2  GLU  B  310    45.622  19.681  16.850  1.00  56.11
ATOM  2745  C    GLU  B  310    48.386  17.470  19.853  1.00  42.41
ATOM  2746  O    GLU  B  310    49.019  17.962  18.918  1.00  42.48
ATOM  2747  N    PRO  B  311    48.952  16.581  20.704  1.00  40.90
```

Figure 5

| | | | | | | | | |
|---|---|---|---|---|---|---|---|---|
| ATOM | 2748 | CD | PRO | B | 311 | 50.313 | 16.070 | 20.448 | 1.00 40.40 |
| ATOM | 2749 | CA | PRO | B | 311 | 48.392 | 15.942 | 21.908 | 1.00 38.58 |
| ATOM | 2750 | CB | PRO | B | 311 | 49.504 | 14.977 | 22.340 | 1.00 38.82 |
| ATOM | 2751 | CG | PRO | B | 311 | 50.264 | 14.711 | 21.087 | 1.00 39.67 |
| ATOM | 2752 | C | PRO | B | 311 | 48.117 | 16.950 | 23.028 | 1.00 36.22 |
| ATOM | 2753 | O | PRO | B | 311 | 48.896 | 17.874 | 23.260 | 1.00 35.72 |
| ATOM | 2754 | N | ILE | B | 312 | 47.002 | 16.768 | 23.723 | 1.00 33.57 |
| ATOM | 2755 | CA | ILE | B | 312 | 46.638 | 17.662 | 24.816 | 1.00 29.75 |
| ATOM | 2756 | CB | ILE | B | 312 | 45.128 | 17.524 | 25.158 | 1.00 30.11 |
| ATOM | 2757 | CG2 | ILE | B | 312 | 44.645 | 18.735 | 25.942 | 1.00 29.28 |
| ATOM | 2758 | CG1 | ILE | B | 312 | 44.303 | 17.307 | 23.873 | 1.00 31.29 |
| ATOM | 2759 | CD1 | ILE | B | 312 | 44.458 | 18.386 | 22.799 | 1.00 31.62 |
| ATOM | 2760 | C | ILE | B | 312 | 47.486 | 17.252 | 26.023 | 1.00 26.53 |
| ATOM | 2761 | O | ILE | B | 312 | 47.657 | 16.054 | 26.280 | 1.00 25.51 |
| ATOM | 2762 | N | TYR | B | 313 | 48.077 | 18.242 | 26.698 | 1.00 23.00 |
| ATOM | 2763 | CA | TYR | B | 313 | 48.913 | 18.019 | 27.888 | 1.00 19.81 |
| ATOM | 2764 | CB | TYR | B | 313 | 50.357 | 18.538 | 27.693 | 1.00 20.14 |
| ATOM | 2765 | CG | TYR | B | 313 | 51.250 | 17.805 | 26.701 | 1.00 21.06 |
| ATOM | 2766 | CD1 | TYR | B | 313 | 50.907 | 16.545 | 26.204 | 1.00 21.91 |
| ATOM | 2767 | CE1 | TYR | B | 313 | 51.740 | 15.873 | 25.286 | 1.00 23.44 |
| ATOM | 2768 | CD2 | TYR | B | 313 | 52.449 | 18.383 | 26.259 | 1.00 20.84 |
| ATOM | 2769 | CE2 | TYR | B | 313 | 53.289 | 17.723 | 25.349 | 1.00 22.00 |
| ATOM | 2770 | CZ | TYR | B | 313 | 52.930 | 16.466 | 24.859 | 1.00 23.28 |
| ATOM | 2771 | OH | TYR | B | 313 | 53.733 | 15.801 | 23.938 | 1.00 23.09 |
| ATOM | 2772 | C | TYR | B | 313 | 48.365 | 18.752 | 29.101 | 1.00 17.53 |
| ATOM | 2773 | O | TYR | B | 313 | 47.797 | 19.836 | 28.988 | 1.00 15.68 |
| ATOM | 2774 | N | ILE | B | 314 | 48.566 | 18.144 | 30.264 | 1.00 16.56 |
| ATOM | 2775 | CA | ILE | B | 314 | 48.192 | 18.727 | 31.547 | 1.00 16.74 |
| ATOM | 2776 | CB | ILE | B | 314 | 47.117 | 17.910 | 32.318 | 1.00 16.78 |
| ATOM | 2777 | CG2 | ILE | B | 314 | 47.074 | 18.357 | 33.787 | 1.00 15.96 |
| ATOM | 2778 | CG1 | ILE | B | 314 | 45.730 | 18.082 | 31.674 | 1.00 16.18 |
| ATOM | 2779 | CD1 | ILE | B | 314 | 44.606 | 17.321 | 32.401 | 1.00 16.98 |
| ATOM | 2780 | C | ILE | B | 314 | 49.495 | 18.628 | 32.308 | 1.00 16.92 |
| ATOM | 2781 | O | ILE | B | 314 | 49.970 | 17.526 | 32.570 | 1.00 18.51 |
| ATOM | 2782 | N | ILE | B | 315 | 50.101 | 19.765 | 32.619 | 1.00 16.65 |
| ATOM | 2783 | CA | ILE | B | 315 | 51.378 | 19.777 | 33.325 | 1.00 17.15 |
| ATOM | 2784 | CB | ILE | B | 315 | 52.366 | 20.808 | 32.677 | 1.00 18.45 |
| ATOM | 2785 | CG2 | ILE | B | 315 | 53.684 | 20.842 | 33.426 | 1.00 19.25 |
| ATOM | 2786 | CG1 | ILE | B | 315 | 52.647 | 20.444 | 31.216 | 1.00 19.04 |
| ATOM | 2787 | CD1 | ILE | B | 315 | 51.710 | 21.070 | 30.210 | 1.00 19.53 |
| ATOM | 2788 | C | ILE | B | 315 | 51.239 | 20.092 | 34.813 | 1.00 16.77 |
| ATOM | 2789 | O | ILE | B | 315 | 50.763 | 21.156 | 35.194 | 1.00 15.73 |
| ATOM | 2790 | N | THR | B | 316 | 51.667 | 19.158 | 35.652 | 1.00 16.75 |
| ATOM | 2791 | CA | THR | B | 316 | 51.605 | 19.361 | 37.090 | 1.00 18.21 |
| ATOM | 2792 | CB | THR | B | 316 | 50.637 | 18.364 | 37.764 | 1.00 17.87 |
| ATOM | 2793 | OG1 | THR | B | 316 | 51.075 | 17.022 | 37.500 | 1.00 17.68 |
| ATOM | 2794 | CG2 | THR | B | 316 | 49.220 | 18.557 | 37.232 | 1.00 16.51 |
| ATOM | 2795 | C | THR | B | 316 | 52.991 | 19.173 | 37.695 | 1.00 19.52 |
| ATOM | 2796 | O | THR | B | 316 | 53.920 | 18.704 | 37.033 | 1.00 19.12 |
| ATOM | 2797 | N | GLU | B | 317 | 53.124 | 19.540 | 38.968 | 1.00 20.68 |
| ATOM | 2798 | CA | GLU | B | 317 | 54.386 | 19.374 | 39.681 | 1.00 21.16 |
| ATOM | 2799 | CB | GLU | B | 317 | 54.255 | 19.849 | 41.125 | 1.00 21.29 |
| ATOM | 2800 | CG | GLU | B | 317 | 53.299 | 19.035 | 41.968 | 1.00 22.75 |
| ATOM | 2801 | CD | GLU | B | 317 | 53.404 | 19.382 | 43.432 | 1.00 23.87 |
| ATOM | 2802 | OE1 | GLU | B | 317 | 52.374 | 19.779 | 44.024 | 1.00 23.58 |
| ATOM | 2803 | OE2 | GLU | B | 317 | 54.526 | 19.264 | 43.983 | 1.00 24.66 |
| ATOM | 2804 | C | GLU | B | 317 | 54.724 | 17.893 | 39.652 | 1.00 20.85 |
| ATOM | 2805 | O | GLU | B | 317 | 53.864 | 17.056 | 39.390 | 1.00 21.03 |
| ATOM | 2806 | N | TYR | B | 318 | 55.973 | 17.561 | 39.907 | 1.00 21.25 |
| ATOM | 2807 | CA | TYR | B | 318 | 56.363 | 16.162 | 39.861 | 1.00 22.04 |

Figure 5

| | | | | | | | | | |
|---|---|---|---|---|---|---|---|---|---|
| ATOM | 2808 | CB | TYR | B | 318 | 57.696 | 16.041 | 39.137 | 1.00 21.57 |
| ATOM | 2809 | CG | TYR | B | 318 | 58.269 | 14.658 | 39.107 | 1.00 22.03 |
| ATOM | 2810 | CD1 | TYR | B | 318 | 57.715 | 13.673 | 38.290 | 1.00 21.71 |
| ATOM | 2811 | CE1 | TYR | B | 318 | 58.268 | 12.391 | 38.238 | 1.00 22.45 |
| ATOM | 2812 | CD2 | TYR | B | 318 | 59.393 | 14.333 | 39.882 | 1.00 22.24 |
| ATOM | 2813 | CE2 | TYR | B | 318 | 59.958 | 13.052 | 39.842 | 1.00 21.93 |
| ATOM | 2814 | CZ | TYR | B | 318 | 59.393 | 12.089 | 39.015 | 1.00 23.04 |
| ATOM | 2815 | OH | TYR | B | 318 | 59.964 | 10.833 | 38.945 | 1.00 24.37 |
| ATOM | 2816 | C | TYR | B | 318 | 56.432 | 15.535 | 41.245 | 1.00 22.66 |
| ATOM | 2817 | O | TYR | B | 318 | 56.904 | 16.162 | 42.193 | 1.00 22.76 |
| ATOM | 2818 | N | MET | B | 319 | 55.920 | 14.314 | 41.363 | 1.00 23.16 |
| ATOM | 2819 | CA | MET | B | 319 | 55.942 | 13.584 | 42.628 | 1.00 24.62 |
| ATOM | 2820 | CB | MET | B | 319 | 54.526 | 13.219 | 43.057 | 1.00 24.54 |
| ATOM | 2821 | CG | MET | B | 319 | 53.631 | 14.426 | 43.321 | 1.00 24.60 |
| ATOM | 2822 | SD | MET | B | 319 | 54.167 | 15.462 | 44.713 | 1.00 27.09 |
| ATOM | 2823 | CE | MET | B | 319 | 53.545 | 14.537 | 46.124 | 1.00 25.43 |
| ATOM | 2824 | C | MET | B | 319 | 56.832 | 12.333 | 42.514 | 1.00 25.92 |
| ATOM | 2825 | O | MET | B | 319 | 56.428 | 11.304 | 41.953 | 1.00 25.36 |
| ATOM | 2826 | N | GLU | B | 320 | 58.062 | 12.486 | 43.020 | 1.00 26.31 |
| ATOM | 2827 | CA | GLU | B | 320 | 59.132 | 11.486 | 43.035 | 1.00 25.91 |
| ATOM | 2828 | CB | GLU | B | 320 | 60.214 | 11.934 | 44.013 | 1.00 28.81 |
| ATOM | 2829 | CG | GLU | B | 320 | 61.418 | 10.988 | 44.159 | 1.00 34.68 |
| ATOM | 2830 | CD | GLU | B | 320 | 62.510 | 11.212 | 43.122 | 1.00 36.09 |
| ATOM | 2831 | OE1 | GLU | B | 320 | 62.717 | 12.377 | 42.696 | 1.00 37.91 |
| ATOM | 2832 | OE2 | GLU | B | 320 | 63.166 | 10.212 | 42.746 | 1.00 36.37 |
| ATOM | 2833 | C | GLU | B | 320 | 58.755 | 10.047 | 43.336 | 1.00 25.01 |
| ATOM | 2834 | O | GLU | B | 320 | 59.034 | 9.152 | 42.545 | 1.00 25.63 |
| ATOM | 2835 | N | ASN | B | 321 | 58.132 | 9.810 | 44.480 | 1.00 24.29 |
| ATOM | 2836 | CA | ASN | B | 321 | 57.758 | 8.448 | 44.830 | 1.00 23.15 |
| ATOM | 2837 | CB | ASN | B | 321 | 57.925 | 8.230 | 46.324 | 1.00 22.72 |
| ATOM | 2838 | CG | ASN | B | 321 | 59.367 | 8.374 | 46.753 | 1.00 21.60 |
| ATOM | 2839 | OD1 | ASN | B | 321 | 60.264 | 7.732 | 46.197 | 1.00 20.74 |
| ATOM | 2840 | ND2 | ASN | B | 321 | 59.607 | 9.243 | 47.711 | 1.00 21.52 |
| ATOM | 2841 | C | ASN | B | 321 | 56.408 | 7.974 | 44.309 | 1.00 22.86 |
| ATOM | 2842 | O | ASN | B | 321 | 55.896 | 6.927 | 44.720 | 1.00 23.51 |
| ATOM | 2843 | N | GLY | B | 322 | 55.864 | 8.753 | 43.378 | 1.00 22.62 |
| ATOM | 2844 | CA | GLY | B | 322 | 54.611 | 8.443 | 42.707 | 1.00 21.88 |
| ATOM | 2845 | C | GLY | B | 322 | 53.360 | 8.146 | 43.501 | 1.00 21.08 |
| ATOM | 2846 | O | GLY | B | 322 | 52.955 | 8.906 | 44.365 | 1.00 20.65 |
| ATOM | 2847 | N | SER | B | 323 | 52.716 | 7.044 | 43.131 | 1.00 21.21 |
| ATOM | 2848 | CA | SER | B | 323 | 51.484 | 6.581 | 43.753 | 1.00 20.52 |
| ATOM | 2849 | CB | SER | B | 323 | 50.821 | 5.551 | 42.844 | 1.00 20.45 |
| ATOM | 2850 | OG | SER | B | 323 | 49.508 | 5.266 | 43.275 | 1.00 21.60 |
| ATOM | 2851 | C | SER | B | 323 | 51.741 | 5.961 | 45.113 | 1.00 20.72 |
| ATOM | 2852 | O | SER | B | 323 | 52.621 | 5.111 | 45.273 | 1.00 21.94 |
| ATOM | 2853 | N | LEU | B | 324 | 50.949 | 6.365 | 46.092 | 1.00 20.41 |
| ATOM | 2854 | CA | LEU | B | 324 | 51.098 | 5.840 | 47.440 | 1.00 20.52 |
| ATOM | 2855 | CB | LEU | B | 324 | 50.075 | 6.508 | 48.372 | 1.00 20.02 |
| ATOM | 2856 | CG | LEU | B | 324 | 49.996 | 6.165 | 49.859 | 1.00 18.23 |
| ATOM | 2857 | CD1 | LEU | B | 324 | 51.260 | 6.579 | 50.562 | 1.00 17.28 |
| ATOM | 2858 | CD2 | LEU | B | 324 | 48.799 | 6.873 | 50.469 | 1.00 18.18 |
| ATOM | 2859 | C | LEU | B | 324 | 50.907 | 4.317 | 47.427 | 1.00 20.92 |
| ATOM | 2860 | O | LEU | B | 324 | 51.749 | 3.585 | 47.946 | 1.00 21.42 |
| ATOM | 2861 | N | VAL | B | 325 | 49.839 | 3.862 | 46.769 | 1.00 20.81 |
| ATOM | 2862 | CA | VAL | B | 325 | 49.503 | 2.447 | 46.685 | 1.00 22.10 |
| ATOM | 2863 | CB | VAL | B | 325 | 48.253 | 2.204 | 45.785 | 1.00 21.15 |
| ATOM | 2864 | CG1 | VAL | B | 325 | 48.615 | 2.017 | 44.329 | 1.00 21.91 |
| ATOM | 2865 | CG2 | VAL | B | 325 | 47.431 | 1.037 | 46.308 | 1.00 20.91 |
| ATOM | 2866 | C | VAL | B | 325 | 50.707 | 1.581 | 46.233 | 1.00 23.53 |
| ATOM | 2867 | O | VAL | B | 325 | 50.900 | 0.468 | 46.723 | 1.00 23.33 |

Figure 5

| | | | | | | | | |
|---|---|---|---|---|---|---|---|---|
| ATOM | 2868 | N | ASP | B | 326 | 51.538 | 2.146 | 45.351 | 1.00 25.54 |
| ATOM | 2869 | CA | ASP | B | 326 | 52.747 | 1.469 | 44.876 | 1.00 27.53 |
| ATOM | 2870 | CB | ASP | B | 326 | 53.114 | 1.930 | 43.495 | 1.00 27.94 |
| ATOM | 2871 | CG | ASP | B | 326 | 52.184 | 1.427 | 42.464 | 1.00 28.89 |
| ATOM | 2872 | OD1 | ASP | B | 326 | 51.955 | 0.182 | 42.436 | 1.00 30.26 |
| ATOM | 2873 | OD2 | ASP | B | 326 | 51.624 | 2.247 | 41.727 | 1.00 31.50 |
| ATOM | 2874 | C | ASP | B | 326 | 53.954 | 1.659 | 45.779 | 1.00 28.25 |
| ATOM | 2875 | O | ASP | B | 326 | 54.783 | 0.767 | 45.936 | 1.00 28.22 |
| ATOM | 2876 | N | PHE | B | 327 | 54.056 | 2.856 | 46.367 | 1.00 29.05 |
| ATOM | 2877 | CA | PHE | B | 327 | 55.168 | 3.162 | 47.243 | 1.00 29.79 |
| ATOM | 2878 | CB | PHE | B | 327 | 55.186 | 4.671 | 47.545 | 1.00 30.53 |
| ATOM | 2879 | CG | PHE | B | 327 | 56.188 | 5.079 | 48.610 | 1.00 31.28 |
| ATOM | 2880 | CD1 | PHE | B | 327 | 57.550 | 5.174 | 48.300 | 1.00 31.34 |
| ATOM | 2881 | CD2 | PHE | B | 327 | 55.786 | 5.348 | 49.916 | 1.00 31.44 |
| ATOM | 2882 | CE1 | PHE | B | 327 | 58.492 | 5.521 | 49.277 | 1.00 31.20 |
| ATOM | 2883 | CE2 | PHE | B | 327 | 56.706 | 5.695 | 50.907 | 1.00 31.48 |
| ATOM | 2884 | CZ | PHE | B | 327 | 58.073 | 5.780 | 50.587 | 1.00 31.92 |
| ATOM | 2885 | C | PHE | B | 327 | 55.147 | 2.377 | 48.560 | 1.00 30.80 |
| ATOM | 2886 | O | PHE | B | 327 | 56.185 | 1.924 | 49.010 | 1.00 31.94 |
| ATOM | 2887 | N | LEU | B | 328 | 53.962 | 2.225 | 49.162 | 1.00 31.14 |
| ATOM | 2888 | CA | LEU | B | 328 | 53.864 | 1.487 | 50.424 | 1.00 30.71 |
| ATOM | 2889 | CB | LEU | B | 328 | 52.420 | 1.452 | 50.925 | 1.00 29.37 |
| ATOM | 2890 | CG | LEU | B | 328 | 51.754 | 2.769 | 51.317 | 1.00 27.77 |
| ATOM | 2891 | CD1 | LEU | B | 328 | 50.252 | 2.554 | 51.464 | 1.00 26.66 |
| ATOM | 2892 | CD2 | LEU | B | 328 | 52.369 | 3.329 | 52.593 | 1.00 26.01 |
| ATOM | 2893 | C | LEU | B | 328 | 54.415 | 0.065 | 50.313 | 1.00 31.98 |
| ATOM | 2894 | O | LEU | B | 328 | 54.900 | -0.494 | 51.305 | 1.00 32.10 |
| ATOM | 2895 | N | LYS | B | 329 | 54.344 | -0.490 | 49.098 | 1.00 32.91 |
| ATOM | 2896 | CA | LYS | B | 329 | 54.843 | -1.836 | 48.806 | 1.00 33.90 |
| ATOM | 2897 | CB | LYS | B | 329 | 54.143 | -2.431 | 47.575 | 1.00 32.59 |
| ATOM | 2898 | CG | LYS | B | 329 | 52.649 | -2.559 | 47.645 | 1.00 31.13 |
| ATOM | 2899 | CD | LYS | B | 329 | 52.173 | -3.414 | 46.497 | 1.00 32.00 |
| ATOM | 2900 | CE | LYS | B | 329 | 50.668 | -3.332 | 46.309 | 1.00 32.49 |
| ATOM | 2901 | NZ | LYS | B | 329 | 50.240 | -2.011 | 45.772 | 1.00 33.57 |
| ATOM | 2902 | C | LYS | B | 329 | 56.362 | -1.904 | 48.569 | 1.00 35.27 |
| ATOM | 2903 | O | LYS | B | 329 | 56.946 | -2.986 | 48.673 | 1.00 36.28 |
| ATOM | 2904 | N | THR | B | 330 | 56.980 | -0.776 | 48.198 | 1.00 35.68 |
| ATOM | 2905 | CA | THR | B | 330 | 58.428 | -0.721 | 47.944 | 1.00 35.44 |
| ATOM | 2906 | CB | THR | B | 330 | 58.876 | 0.670 | 47.435 | 1.00 34.59 |
| ATOM | 2907 | OG1 | THR | B | 330 | 58.745 | 1.625 | 48.488 | 1.00 35.49 |
| ATOM | 2908 | CG2 | THR | B | 330 | 58.035 | 1.118 | 46.252 | 1.00 34.51 |
| ATOM | 2909 | C | THR | B | 330 | 59.198 | -1.015 | 49.232 | 1.00 35.87 |
| ATOM | 2910 | O | THR | B | 330 | 58.683 | -0.780 | 50.314 | 1.00 35.96 |
| ATOM | 2911 | N | PRO | B | 331 | 60.456 | -1.495 | 49.122 | 1.00 36.69 |
| ATOM | 2912 | CD | PRO | B | 331 | 61.193 | -1.700 | 47.856 | 1.00 36.95 |
| ATOM | 2913 | CA | PRO | B | 331 | 61.312 | -1.824 | 50.272 | 1.00 36.95 |
| ATOM | 2914 | CB | PRO | B | 331 | 62.693 | -1.949 | 49.627 | 1.00 36.62 |
| ATOM | 2915 | CG | PRO | B | 331 | 62.376 | -2.537 | 48.299 | 1.00 36.73 |
| ATOM | 2916 | C | PRO | B | 331 | 61.314 | -0.755 | 51.369 | 1.00 37.49 |
| ATOM | 2917 | O | PRO | B | 331 | 61.262 | -1.078 | 52.552 | 1.00 37.39 |
| ATOM | 2918 | N | SER | B | 332 | 61.368 | 0.508 | 50.951 | 1.00 38.12 |
| ATOM | 2919 | CA | SER | B | 332 | 61.381 | 1.664 | 51.848 | 1.00 39.00 |
| ATOM | 2920 | CB | SER | B | 332 | 61.712 | 2.931 | 51.050 | 1.00 39.20 |
| ATOM | 2921 | OG | SER | B | 332 | 62.654 | 2.668 | 50.022 | 1.00 39.60 |
| ATOM | 2922 | C | SER | B | 332 | 60.015 | 1.859 | 52.506 | 1.00 39.88 |
| ATOM | 2923 | O | SER | B | 332 | 59.922 | 2.209 | 53.691 | 1.00 39.82 |
| ATOM | 2924 | N | GLY | B | 333 | 58.968 | 1.685 | 51.695 | 1.00 40.33 |
| ATOM | 2925 | CA | GLY | B | 333 | 57.594 | 1.841 | 52.145 | 1.00 40.54 |
| ATOM | 2926 | C | GLY | B | 333 | 57.174 | 0.774 | 53.126 | 1.00 40.49 |
| ATOM | 2927 | O | GLY | B | 333 | 56.487 | 1.065 | 54.099 | 1.00 41.20 |

Figure 5

| | | | | | | | | | |
|---|---|---|---|---|---|---|---|---|---|
| ATOM | 2928 | N | ILE | B | 334 | 57.533 | -0.468 | 52.833 | 1.00 40.28 |
| ATOM | 2929 | CA | ILE | B | 334 | 57.232 | -1.592 | 53.712 | 1.00 40.58 |
| ATOM | 2930 | CB | ILE | B | 334 | 57.855 | -2.902 | 53.157 | 1.00 41.37 |
| ATOM | 2931 | CG2 | ILE | B | 334 | 57.934 | -3.969 | 54.240 | 1.00 43.23 |
| ATOM | 2932 | CG1 | ILE | B | 334 | 57.062 | -3.405 | 51.942 | 1.00 42.79 |
| ATOM | 2933 | CD1 | ILE | B | 334 | 55.613 | -3.844 | 52.232 | 1.00 43.27 |
| ATOM | 2934 | C | ILE | B | 334 | 57.805 | -1.317 | 55.108 | 1.00 40.15 |
| ATOM | 2935 | O | ILE | B | 334 | 57.142 | -1.558 | 56.111 | 1.00 40.80 |
| ATOM | 2936 | N | LYS | B | 335 | 59.012 | -0.758 | 55.161 | 1.00 40.00 |
| ATOM | 2937 | CA | LYS | B | 335 | 59.686 | -0.467 | 56.428 | 1.00 39.63 |
| ATOM | 2938 | CB | LYS | B | 335 | 61.206 | -0.321 | 56.219 | 1.00 40.96 |
| ATOM | 2939 | CG | LYS | B | 335 | 61.931 | -1.526 | 55.591 | 1.00 42.32 |
| ATOM | 2940 | CD | LYS | B | 335 | 63.460 | -1.309 | 55.585 | 1.00 43.90 |
| ATOM | 2941 | CE | LYS | B | 335 | 64.214 | -2.342 | 54.738 | 1.00 44.49 |
| ATOM | 2942 | NZ | LYS | B | 335 | 64.670 | -1.778 | 53.419 | 1.00 45.84 |
| ATOM | 2943 | C | LYS | B | 335 | 59.166 | 0.753 | 57.195 | 1.00 38.72 |
| ATOM | 2944 | O | LYS | B | 335 | 59.622 | 1.010 | 58.315 | 1.00 38.26 |
| ATOM | 2945 | N | LEU | B | 336 | 58.242 | 1.512 | 56.596 | 1.00 38.08 |
| ATOM | 2946 | CA | LEU | B | 336 | 57.665 | 2.706 | 57.251 | 1.00 36.98 |
| ATOM | 2947 | CB | LEU | B | 336 | 56.733 | 3.478 | 56.306 | 1.00 35.49 |
| ATOM | 2948 | CG | LEU | B | 336 | 57.341 | 4.470 | 55.316 | 1.00 34.25 |
| ATOM | 2949 | CD1 | LEU | B | 336 | 56.224 | 5.274 | 54.643 | 1.00 33.37 |
| ATOM | 2950 | CD2 | LEU | B | 336 | 58.308 | 5.391 | 56.045 | 1.00 32.62 |
| ATOM | 2951 | C | LEU | B | 336 | 56.931 | 2.439 | 58.576 | 1.00 36.30 |
| ATOM | 2952 | O | LEU | B | 336 | 56.047 | 1.570 | 58.665 | 1.00 36.11 |
| ATOM | 2953 | N | THR | B | 337 | 57.277 | 3.240 | 59.580 | 1.00 35.15 |
| ATOM | 2954 | CA | THR | B | 337 | 56.702 | 3.124 | 60.915 | 1.00 34.58 |
| ATOM | 2955 | CB | THR | B | 337 | 57.555 | 3.902 | 61.960 | 1.00 33.89 |
| ATOM | 2956 | OG1 | THR | B | 337 | 57.366 | 5.312 | 61.805 | 1.00 33.02 |
| ATOM | 2957 | CG2 | THR | B | 337 | 59.025 | 3.601 | 61.760 | 1.00 34.37 |
| ATOM | 2958 | C | THR | B | 337 | 55.235 | 3.575 | 60.994 | 1.00 34.45 |
| ATOM | 2959 | O | THR | B | 337 | 54.765 | 4.339 | 60.145 | 1.00 35.10 |
| ATOM | 2960 | N | ILE | B | 338 | 54.519 | 3.083 | 62.007 | 1.00 33.23 |
| ATOM | 2961 | CA | ILE | B | 338 | 53.117 | 3.433 | 62.210 | 1.00 31.71 |
| ATOM | 2962 | CB | ILE | B | 338 | 52.500 | 2.703 | 63.454 | 1.00 31.58 |
| ATOM | 2963 | CG2 | ILE | B | 338 | 53.172 | 3.171 | 64.758 | 1.00 31.03 |
| ATOM | 2964 | CG1 | ILE | B | 338 | 50.982 | 2.934 | 63.526 | 1.00 29.66 |
| ATOM | 2965 | CD1 | ILE | B | 338 | 50.198 | 2.388 | 62.359 | 1.00 28.44 |
| ATOM | 2966 | C | ILE | B | 338 | 53.004 | 4.943 | 62.374 | 1.00 31.40 |
| ATOM | 2967 | O | ILE | B | 338 | 52.068 | 5.557 | 61.876 | 1.00 31.90 |
| ATOM | 2968 | N | ASN | B | 339 | 53.984 | 5.539 | 63.046 | 1.00 30.93 |
| ATOM | 2969 | CA | ASN | B | 339 | 54.013 | 6.984 | 63.256 | 1.00 30.48 |
| ATOM | 2970 | CB | ASN | B | 339 | 55.238 | 7.378 | 64.099 | 1.00 31.24 |
| ATOM | 2971 | CG | ASN | B | 339 | 55.323 | 6.605 | 65.397 | 1.00 32.13 |
| ATOM | 2972 | OD1 | ASN | B | 339 | 54.984 | 7.131 | 66.461 | 1.00 31.69 |
| ATOM | 2973 | ND2 | ASN | B | 339 | 55.755 | 5.337 | 65.317 | 1.00 31.33 |
| ATOM | 2974 | C | ASN | B | 339 | 54.052 | 7.740 | 61.925 | 1.00 29.47 |
| ATOM | 2975 | O | ASN | B | 339 | 53.427 | 8.785 | 61.783 | 1.00 30.94 |
| ATOM | 2976 | N | LYS | B | 340 | 54.794 | 7.213 | 60.958 | 1.00 28.23 |
| ATOM | 2977 | CA | LYS | B | 340 | 54.920 | 7.841 | 59.650 | 1.00 27.69 |
| ATOM | 2978 | CB | LYS | B | 340 | 56.195 | 7.355 | 58.952 | 1.00 27.59 |
| ATOM | 2979 | CG | LYS | B | 340 | 56.418 | 7.899 | 57.556 | 1.00 28.08 |
| ATOM | 2980 | CD | LYS | B | 340 | 56.484 | 9.421 | 57.484 | 1.00 27.68 |
| ATOM | 2981 | CE | LYS | B | 340 | 56.556 | 9.861 | 56.008 | 1.00 28.55 |
| ATOM | 2982 | NZ | LYS | B | 340 | 56.385 | 11.338 | 55.789 | 1.00 28.90 |
| ATOM | 2983 | C | LYS | B | 340 | 53.674 | 7.590 | 58.804 | 1.00 27.41 |
| ATOM | 2984 | O | LYS | B | 340 | 53.232 | 8.478 | 58.070 | 1.00 28.48 |
| ATOM | 2985 | N | LEU | B | 341 | 53.078 | 6.405 | 58.943 | 1.00 26.41 |
| ATOM | 2986 | CA | LEU | B | 341 | 51.851 | 6.066 | 58.210 | 1.00 24.40 |
| ATOM | 2987 | CB | LEU | B | 341 | 51.481 | 4.606 | 58.430 | 1.00 22.84 |

Figure 5

```
ATOM   2988  CG   LEU B 341      52.464   3.574  57.880  1.00 21.94
ATOM   2989  CD1  LEU B 341      51.848   2.189  58.018  1.00 20.91
ATOM   2990  CD2  LEU B 341      52.782   3.856  56.420  1.00 20.67
ATOM   2991  C    LEU B 341      50.682   6.960  58.624  1.00 23.99
ATOM   2992  O    LEU B 341      49.928   7.447  57.791  1.00 24.30
ATOM   2993  N    LEU B 342      50.547   7.193  59.918  1.00 24.58
ATOM   2994  CA   LEU B 342      49.469   8.037  60.413  1.00 25.19
ATOM   2995  CB   LEU B 342      49.331   7.933  61.925  1.00 25.66
ATOM   2996  CG   LEU B 342      48.860   6.578  62.410  1.00 26.09
ATOM   2997  CD1  LEU B 342      48.733   6.639  63.882  1.00 28.29
ATOM   2998  CD2  LEU B 342      47.534   6.228  61.794  1.00 28.91
ATOM   2999  C    LEU B 342      49.659   9.486  60.047  1.00 24.82
ATOM   3000  O    LEU B 342      48.681  10.219  59.914  1.00 25.34
ATOM   3001  N    ASP B 343      50.914   9.912  59.917  1.00 24.82
ATOM   3002  CA   ASP B 343      51.166  11.290  59.558  1.00 24.71
ATOM   3003  CB   ASP B 343      52.627  11.691  59.750  1.00 28.11
ATOM   3004  CG   ASP B 343      52.832  13.204  59.587  1.00 33.22
ATOM   3005  OD1  ASP B 343      52.105  13.976  60.272  1.00 35.48
ATOM   3006  OD2  ASP B 343      53.674  13.627  58.751  1.00 35.29
ATOM   3007  C    ASP B 343      50.760  11.479  58.117  1.00 23.20
ATOM   3008  O    ASP B 343      50.175  12.497  57.769  1.00 22.67
ATOM   3009  N    MET B 344      51.054  10.478  57.290  1.00 21.88
ATOM   3010  CA   MET B 344      50.698  10.518  55.874  1.00 20.71
ATOM   3011  CB   MET B 344      51.237   9.285  55.150  1.00 19.26
ATOM   3012  CG   MET B 344      52.753   9.229  55.099  1.00 18.30
ATOM   3013  SD   MET B 344      53.347   7.748  54.254  1.00 18.36
ATOM   3014  CE   MET B 344      54.090   8.475  52.829  1.00 18.25
ATOM   3015  C    MET B 344      49.176  10.624  55.715  1.00 20.18
ATOM   3016  O    MET B 344      48.683  11.429  54.915  1.00 19.56
ATOM   3017  N    ALA B 345      48.453   9.831  56.511  1.00 19.24
ATOM   3018  CA   ALA B 345      46.992   9.812  56.534  1.00 18.22
ATOM   3019  CB   ALA B 345      46.501   8.746  57.508  1.00 18.53
ATOM   3020  C    ALA B 345      46.464  11.174  56.960  1.00 17.93
ATOM   3021  O    ALA B 345      45.418  11.615  56.499  1.00 17.73
ATOM   3022  N    ALA B 346      47.193  11.824  57.859  1.00 18.05
ATOM   3023  CA   ALA B 346      46.823  13.143  58.348  1.00 18.61
ATOM   3024  CB   ALA B 346      47.707  13.527  59.502  1.00 17.37
ATOM   3025  C    ALA B 346      46.941  14.178  57.239  1.00 19.61
ATOM   3026  O    ALA B 346      46.092  15.061  57.107  1.00 20.84
ATOM   3027  N    GLN B 347      47.994  14.067  56.434  1.00 19.89
ATOM   3028  CA   GLN B 347      48.210  15.006  55.337  1.00 19.43
ATOM   3029  CB   GLN B 347      49.551  14.735  54.648  1.00 21.48
ATOM   3030  CG   GLN B 347      50.735  14.691  55.591  1.00 24.37
ATOM   3031  CD   GLN B 347      52.029  14.381  54.872  1.00 27.58
ATOM   3032  OE1  GLN B 347      52.720  15.285  54.422  1.00 31.54
ATOM   3033  NE2  GLN B 347      52.355  13.100  54.743  1.00 29.35
ATOM   3034  C    GLN B 347      47.062  14.899  54.333  1.00 18.38
ATOM   3035  O    GLN B 347      46.557  15.917  53.850  1.00 17.95
ATOM   3036  N    ILE B 348      46.639  13.663  54.052  1.00 16.83
ATOM   3037  CA   ILE B 348      45.542  13.383  53.119  1.00 15.83
ATOM   3038  CB   ILE B 348      45.398  11.855  52.876  1.00 15.23
ATOM   3039  CG2  ILE B 348      44.264  11.575  51.904  1.00 14.42
ATOM   3040  CG1  ILE B 348      46.708  11.298  52.326  1.00 13.78
ATOM   3041  CD1  ILE B 348      46.744   9.819  52.222  1.00 14.13
ATOM   3042  C    ILE B 348      44.212  13.949  53.638  1.00 15.71
ATOM   3043  O    ILE B 348      43.451  14.559  52.890  1.00 15.82
ATOM   3044  N    ALA B 349      43.957  13.752  54.930  1.00 15.54
ATOM   3045  CA   ALA B 349      42.747  14.242  55.574  1.00 14.65
ATOM   3046  CB   ALA B 349      42.634  13.654  56.962  1.00 14.65
ATOM   3047  C    ALA B 349      42.767  15.775  55.628  1.00 15.21
```

Figure 5

| ATOM | 3048 | O   | ALA | B | 349 | 41.711 | 16.409 | 55.581 | 1.00 | 15.05 |
|------|------|-----|-----|---|-----|--------|--------|--------|------|-------|
| ATOM | 3049 | N   | GLU | B | 350 | 43.966 | 16.362 | 55.716 | 1.00 | 16.12 |
| ATOM | 3050 | CA  | GLU | B | 350 | 44.142 | 17.820 | 55.733 | 1.00 | 17.04 |
| ATOM | 3051 | CB  | GLU | B | 350 | 45.575 | 18.191 | 56.093 | 1.00 | 17.46 |
| ATOM | 3052 | CG  | GLU | B | 350 | 45.850 | 19.706 | 56.127 | 1.00 | 18.76 |
| ATOM | 3053 | CD  | GLU | B | 350 | 47.339 | 20.046 | 56.221 | 1.00 | 19.32 |
| ATOM | 3054 | OE1 | GLU | B | 350 | 48.139 | 19.168 | 56.618 | 1.00 | 17.47 |
| ATOM | 3055 | OE2 | GLU | B | 350 | 47.708 | 21.198 | 55.899 | 1.00 | 20.33 |
| ATOM | 3056 | C   | GLU | B | 350 | 43.783 | 18.402 | 54.359 | 1.00 | 18.05 |
| ATOM | 3057 | O   | GLU | B | 350 | 43.076 | 19.405 | 54.262 | 1.00 | 19.50 |
| ATOM | 3058 | N   | GLY | B | 351 | 44.248 | 17.754 | 53.294 | 1.00 | 18.74 |
| ATOM | 3059 | CA  | GLY | B | 351 | 43.918 | 18.218 | 51.959 | 1.00 | 18.04 |
| ATOM | 3060 | C   | GLY | B | 351 | 42.422 | 18.084 | 51.742 | 1.00 | 17.75 |
| ATOM | 3061 | O   | GLY | B | 351 | 41.807 | 18.957 | 51.119 | 1.00 | 16.73 |
| ATOM | 3062 | N   | MET | B | 352 | 41.847 | 16.981 | 52.239 | 1.00 | 17.44 |
| ATOM | 3063 | CA  | MET | B | 352 | 40.407 | 16.722 | 52.123 | 1.00 | 16.84 |
| ATOM | 3064 | CB  | MET | B | 352 | 40.071 | 15.280 | 52.493 | 1.00 | 14.87 |
| ATOM | 3065 | CG  | MET | B | 352 | 40.372 | 14.248 | 51.405 | 1.00 | 14.36 |
| ATOM | 3066 | SD  | MET | B | 352 | 39.678 | 14.593 | 49.765 | 1.00 | 14.42 |
| ATOM | 3067 | CE  | MET | B | 352 | 38.016 | 15.149 | 50.176 | 1.00 | 11.48 |
| ATOM | 3068 | C   | MET | B | 352 | 39.624 | 17.677 | 53.014 | 1.00 | 17.38 |
| ATOM | 3069 | O   | MET | B | 352 | 38.476 | 17.999 | 52.736 | 1.00 | 16.71 |
| ATOM | 3070 | N   | ALA | B | 353 | 40.261 | 18.127 | 54.092 | 1.00 | 18.28 |
| ATOM | 3071 | CA  | ALA | B | 353 | 39.643 | 19.070 | 55.011 | 1.00 | 19.12 |
| ATOM | 3072 | CB  | ALA | B | 353 | 40.581 | 19.349 | 56.167 | 1.00 | 19.20 |
| ATOM | 3073 | C   | ALA | B | 353 | 39.386 | 20.353 | 54.240 | 1.00 | 20.41 |
| ATOM | 3074 | O   | ALA | B | 353 | 38.342 | 20.983 | 54.394 | 1.00 | 21.65 |
| ATOM | 3075 | N   | PHE | B | 354 | 40.367 | 20.731 | 53.421 | 1.00 | 21.12 |
| ATOM | 3076 | CA  | PHE | B | 354 | 40.320 | 21.930 | 52.587 | 1.00 | 20.29 |
| ATOM | 3077 | CB  | PHE | B | 354 | 41.700 | 22.173 | 51.960 | 1.00 | 22.11 |
| ATOM | 3078 | CG  | PHE | B | 354 | 41.772 | 23.415 | 51.112 | 1.00 | 23.58 |
| ATOM | 3079 | CD1 | PHE | B | 354 | 41.656 | 24.678 | 51.697 | 1.00 | 24.05 |
| ATOM | 3080 | CD2 | PHE | B | 354 | 41.935 | 23.325 | 49.727 | 1.00 | 23.71 |
| ATOM | 3081 | CE1 | PHE | B | 354 | 41.697 | 25.835 | 50.918 | 1.00 | 23.62 |
| ATOM | 3082 | CE2 | PHE | B | 354 | 41.978 | 24.481 | 48.939 | 1.00 | 23.94 |
| ATOM | 3083 | CZ  | PHE | B | 354 | 41.859 | 25.735 | 49.538 | 1.00 | 22.83 |
| ATOM | 3084 | C   | PHE | B | 354 | 39.270 | 21.822 | 51.495 | 1.00 | 18.66 |
| ATOM | 3085 | O   | PHE | B | 354 | 38.563 | 22.769 | 51.223 | 1.00 | 18.83 |
| ATOM | 3086 | N   | ILE | B | 355 | 39.225 | 20.680 | 50.826 | 1.00 | 18.89 |
| ATOM | 3087 | CA  | ILE | B | 355 | 38.250 | 20.433 | 49.766 | 1.00 | 19.14 |
| ATOM | 3088 | CB  | ILE | B | 355 | 38.469 | 19.027 | 49.125 | 1.00 | 16.77 |
| ATOM | 3089 | CG2 | ILE | B | 355 | 37.288 | 18.629 | 48.248 | 1.00 | 15.07 |
| ATOM | 3090 | CG1 | ILE | B | 355 | 39.793 | 19.012 | 48.351 | 1.00 | 14.27 |
| ATOM | 3091 | CD1 | ILE | B | 355 | 40.147 | 17.683 | 47.756 | 1.00 | 11.70 |
| ATOM | 3092 | C   | ILE | B | 355 | 36.854 | 20.528 | 50.377 | 1.00 | 21.46 |
| ATOM | 3093 | O   | ILE | B | 355 | 35.982 | 21.219 | 49.838 | 1.00 | 21.99 |
| ATOM | 3094 | N   | GLU | B | 356 | 36.677 | 19.870 | 51.526 | 1.00 | 22.60 |
| ATOM | 3095 | CA  | GLU | B | 356 | 35.418 | 19.871 | 52.262 | 1.00 | 23.83 |
| ATOM | 3096 | CB  | GLU | B | 356 | 35.567 | 19.030 | 53.518 | 1.00 | 22.96 |
| ATOM | 3097 | CG  | GLU | B | 356 | 34.421 | 19.151 | 54.485 | 1.00 | 20.38 |
| ATOM | 3098 | CD  | GLU | B | 356 | 34.675 | 18.387 | 55.741 | 1.00 | 18.26 |
| ATOM | 3099 | OE1 | GLU | B | 356 | 35.273 | 18.949 | 56.684 | 1.00 | 20.44 |
| ATOM | 3100 | OE2 | GLU | B | 356 | 34.302 | 17.205 | 55.777 | 1.00 | 18.40 |
| ATOM | 3101 | C   | GLU | B | 356 | 35.046 | 21.287 | 52.663 | 1.00 | 26.27 |
| ATOM | 3102 | O   | GLU | B | 356 | 33.910 | 21.727 | 52.484 | 1.00 | 27.92 |
| ATOM | 3103 | N   | GLU | B | 357 | 36.029 | 21.986 | 53.209 | 1.00 | 27.74 |
| ATOM | 3104 | CA  | GLU | B | 357 | 35.894 | 23.360 | 53.650 | 1.00 | 30.27 |
| ATOM | 3105 | CB  | GLU | B | 357 | 37.245 | 23.788 | 54.243 | 1.00 | 33.14 |
| ATOM | 3106 | CG  | GLU | B | 357 | 37.732 | 25.180 | 53.918 | 1.00 | 37.59 |
| ATOM | 3107 | CD  | GLU | B | 357 | 37.195 | 26.189 | 54.874 | 1.00 | 40.74 |

Figure 5

```
ATOM   3108  OE1 GLU B 357      37.674  26.182  56.023  1.00 43.95
ATOM   3109  OE2 GLU B 357      36.298  26.975  54.492  1.00 41.90
ATOM   3110  C   GLU B 357      35.437  24.304  52.526  1.00 30.74
ATOM   3111  O   GLU B 357      34.721  25.272  52.783  1.00 31.36
ATOM   3112  N   ARG B 358      35.832  24.006  51.287  1.00 31.19
ATOM   3113  CA  ARG B 358      35.477  24.833  50.124  1.00 30.90
ATOM   3114  CB  ARG B 358      36.670  24.952  49.172  1.00 31.78
ATOM   3115  CG  ARG B 358      37.887  25.635  49.785  1.00 33.74
ATOM   3116  CD  ARG B 358      37.716  27.153  49.923  1.00 37.40
ATOM   3117  NE  ARG B 358      37.635  27.822  48.624  1.00 41.97
ATOM   3118  CZ  ARG B 358      38.643  27.919  47.750  1.00 44.52
ATOM   3119  NH1 ARG B 358      39.836  27.401  48.019  1.00 45.61
ATOM   3120  NH2 ARG B 358      38.453  28.502  46.572  1.00 45.39
ATOM   3121  C   ARG B 358      34.245  24.330  49.379  1.00 30.75
ATOM   3122  O   ARG B 358      33.914  24.799  48.282  1.00 29.50
ATOM   3123  N   ASN B 359      33.568  23.372  50.003  1.00 31.58
ATOM   3124  CA  ASN B 359      32.348  22.773  49.473  1.00 31.84
ATOM   3125  CB  ASN B 359      31.218  23.802  49.495  1.00 33.83
ATOM   3126  CG  ASN B 359      31.091  24.475  50.862  1.00 37.38
ATOM   3127  OD1 ASN B 359      30.690  23.840  51.850  1.00 38.70
ATOM   3128  ND2 ASN B 359      31.505  25.743  50.943  1.00 38.39
ATOM   3129  C   ASN B 359      32.498  22.099  48.114  1.00 30.83
ATOM   3130  O   ASN B 359      31.761  22.381  47.169  1.00 31.26
ATOM   3131  N   TYR B 360      33.466  21.193  48.044  1.00 29.49
ATOM   3132  CA  TYR B 360      33.746  20.412  46.848  1.00 29.03
ATOM   3133  CB  TYR B 360      35.069  20.842  46.220  1.00 30.03
ATOM   3134  CG  TYR B 360      34.983  22.072  45.354  1.00 31.97
ATOM   3135  CD1 TYR B 360      35.748  23.211  45.641  1.00 32.04
ATOM   3136  CE1 TYR B 360      35.690  24.334  44.839  1.00 32.46
ATOM   3137  CD2 TYR B 360      34.154  22.097  44.238  1.00 32.07
ATOM   3138  CE2 TYR B 360      34.087  23.218  43.425  1.00 33.34
ATOM   3139  CZ  TYR B 360      34.855  24.334  43.727  1.00 34.05
ATOM   3140  OH  TYR B 360      34.784  25.443  42.906  1.00 36.20
ATOM   3141  C   TYR B 360      33.895  18.966  47.295  1.00 28.56
ATOM   3142  O   TYR B 360      33.967  18.691  48.494  1.00 28.97
ATOM   3143  N   ILE B 361      33.895  18.037  46.345  1.00 26.89
ATOM   3144  CA  ILE B 361      34.108  16.638  46.682  1.00 25.41
ATOM   3145  CB  ILE B 361      32.853  15.753  46.490  1.00 23.70
ATOM   3146  CG2 ILE B 361      31.708  16.227  47.380  1.00 24.32
ATOM   3147  CG1 ILE B 361      32.410  15.743  45.040  1.00 22.87
ATOM   3148  CD1 ILE B 361      31.389  14.664  44.753  1.00 23.09
ATOM   3149  C   ILE B 361      35.271  16.140  45.820  1.00 26.25
ATOM   3150  O   ILE B 361      35.758  16.856  44.938  1.00 27.16
ATOM   3151  N   HIS B 362      35.755  14.942  46.116  1.00 24.92
ATOM   3152  CA  HIS B 362      36.853  14.347  45.378  1.00 23.10
ATOM   3153  CB  HIS B 362      37.803  13.681  46.373  1.00 21.01
ATOM   3154  CG  HIS B 362      39.064  13.168  45.758  1.00 17.62
ATOM   3155  CD2 HIS B 362      40.362  13.408  46.055  1.00 16.84
ATOM   3156  ND1 HIS B 362      39.073  12.293  44.698  1.00 15.96
ATOM   3157  CE1 HIS B 362      40.320  12.016  44.365  1.00 15.93
ATOM   3158  NE2 HIS B 362      41.122  12.680  45.174  1.00 15.35
ATOM   3159  C   HIS B 362      36.277  13.311  44.415  1.00 22.93
ATOM   3160  O   HIS B 362      36.581  13.304  43.221  1.00 23.88
ATOM   3161  N   ARG B 363      35.408  12.480  44.979  1.00 22.29
ATOM   3162  CA  ARG B 363      34.691  11.374  44.349  1.00 21.92
ATOM   3163  CB  ARG B 363      33.631  11.836  43.335  1.00 23.68
ATOM   3164  CG  ARG B 363      34.117  12.367  42.026  1.00 26.31
ATOM   3165  CD  ARG B 363      32.932  12.873  41.207  1.00 28.67
ATOM   3166  NE  ARG B 363      32.029  11.818  40.751  1.00 28.72
ATOM   3167  CZ  ARG B 363      30.702  11.926  40.770  1.00 29.40
```

Figure 5

```
ATOM   3168  NH1 ARG B 363      30.141   13.045   41.230  1.00 26.78
ATOM   3169  NH2 ARG B 363      29.939   10.942   40.284  1.00 28.46
ATOM   3170  C   ARG B 363      35.480   10.185   43.845  1.00 20.39
ATOM   3171  O   ARG B 363      34.904    9.235   43.319  1.00 20.45
ATOM   3172  N   ASP B 364      36.790   10.210   44.053  1.00 18.60
ATOM   3173  CA  ASP B 364      37.659    9.106   43.643  1.00 16.90
ATOM   3174  CB  ASP B 364      38.207    9.322   42.230  1.00 15.58
ATOM   3175  CG  ASP B 364      37.175    9.093   41.163  1.00 15.14
ATOM   3176  OD1 ASP B 364      36.716    7.935   40.982  1.00 14.37
ATOM   3177  OD2 ASP B 364      36.820   10.093   40.503  1.00 16.64
ATOM   3178  C   ASP B 364      38.818    8.987   44.617  1.00 15.91
ATOM   3179  O   ASP B 364      39.962    8.879   44.210  1.00 15.17
ATOM   3180  N   LEU B 365      38.522    9.046   45.905  1.00 15.26
ATOM   3181  CA  LEU B 365      39.573    8.963   46.897  1.00 15.84
ATOM   3182  CB  LEU B 365      39.192    9.772   48.134  1.00 13.41
ATOM   3183  CG  LEU B 365      40.179    9.787   49.300  1.00 12.67
ATOM   3184  CD1 LEU B 365      41.409   10.634   49.000  1.00 11.35
ATOM   3185  CD2 LEU B 365      39.450   10.320   50.493  1.00 11.97
ATOM   3186  C   LEU B 365      39.973    7.534   47.279  1.00 17.43
ATOM   3187  O   LEU B 365      39.181    6.743   47.790  1.00 18.34
ATOM   3188  N   ARG B 366      41.223    7.217   46.991  1.00 18.64
ATOM   3189  CA  ARG B 366      41.812    5.931   47.312  1.00 19.45
ATOM   3190  CB  ARG B 366      41.347    4.834   46.345  1.00 22.64
ATOM   3191  CG  ARG B 366      41.352    5.185   44.882  1.00 25.45
ATOM   3192  CD  ARG B 366      41.015    3.970   44.032  1.00 29.02
ATOM   3193  NE  ARG B 366      40.594    4.360   42.688  1.00 32.27
ATOM   3194  CZ  ARG B 366      39.452    4.991   42.429  1.00 33.33
ATOM   3195  NH1 ARG B 366      38.620    5.292   43.423  1.00 34.00
ATOM   3196  NH2 ARG B 366      39.152    5.339   41.185  1.00 32.67
ATOM   3197  C   ARG B 366      43.303    6.151   47.251  1.00 18.67
ATOM   3198  O   ARG B 366      43.754    7.132   46.687  1.00 18.99
ATOM   3199  N   ALA B 367      44.064    5.264   47.873  1.00 19.44
ATOM   3200  CA  ALA B 367      45.516    5.381   47.908  1.00 20.02
ATOM   3201  CB  ALA B 367      46.126    4.181   48.590  1.00 19.63
ATOM   3202  C   ALA B 367      46.127    5.560   46.532  1.00 20.93
ATOM   3203  O   ALA B 367      47.029    6.376   46.367  1.00 21.86
ATOM   3204  N   ALA B 368      45.584    4.863   45.532  1.00 20.74
ATOM   3205  CA  ALA B 368      46.115    4.956   44.176  1.00 19.96
ATOM   3206  CB  ALA B 368      45.354    4.028   43.242  1.00 20.26
ATOM   3207  C   ALA B 368      46.113    6.384   43.632  1.00 19.80
ATOM   3208  O   ALA B 368      46.950    6.745   42.811  1.00 20.05
ATOM   3209  N   ASN B 369      45.207    7.216   44.123  1.00 19.48
ATOM   3210  CA  ASN B 369      45.156    8.584   43.643  1.00 19.49
ATOM   3211  CB  ASN B 369      43.703    8.996   43.390  1.00 20.48
ATOM   3212  CG  ASN B 369      43.026    8.118   42.334  1.00 21.95
ATOM   3213  OD1 ASN B 369      43.639    7.719   41.334  1.00 23.78
ATOM   3214  ND2 ASN B 369      41.768    7.795   42.565  1.00 21.75
ATOM   3215  C   ASN B 369      45.886    9.583   44.543  1.00 18.50
ATOM   3216  O   ASN B 369      45.671   10.791   44.433  1.00 19.10
ATOM   3217  N   ILE B 370      46.743    9.075   45.430  1.00 16.84
ATOM   3218  CA  ILE B 370      47.523    9.931   46.324  1.00 15.96
ATOM   3219  CB  ILE B 370      47.379    9.538   47.813  1.00 15.83
ATOM   3220  CG2 ILE B 370      48.367   10.361   48.677  1.00 13.63
ATOM   3221  CG1 ILE B 370      45.933    9.727   48.277  1.00 13.36
ATOM   3222  CD1 ILE B 370      45.459   11.125   48.153  1.00 11.99
ATOM   3223  C   ILE B 370      48.992    9.844   45.934  1.00 15.62
ATOM   3224  O   ILE B 370      49.540    8.758   45.782  1.00 15.51
ATOM   3225  N   LEU B 371      49.641   10.996   45.839  1.00 15.54
ATOM   3226  CA  LEU B 371      51.029   11.050   45.433  1.00 15.75
ATOM   3227  CB  LEU B 371      51.191   12.040   44.271  1.00 14.37
```

Figure 5

| | | | | | | | | | |
|---|---|---|---|---|---|---|---|---|---|
| ATOM | 3228 | CG | LEU | B | 371 | 50.312 | 11.799 | 43.031 | 1.00 14.87 |
| ATOM | 3229 | CD1 | LEU | B | 371 | 50.577 | 12.856 | 42.008 | 1.00 15.75 |
| ATOM | 3230 | CD2 | LEU | B | 371 | 50.554 | 10.436 | 42.399 | 1.00 14.16 |
| ATOM | 3231 | C | LEU | B | 371 | 52.032 | 11.331 | 46.564 | 1.00 16.27 |
| ATOM | 3232 | O | LEU | B | 371 | 51.762 | 12.087 | 47.493 | 1.00 15.25 |
| ATOM | 3233 | N | VAL | B | 372 | 53.171 | 10.654 | 46.490 | 1.00 16.52 |
| ATOM | 3234 | CA | VAL | B | 372 | 54.222 | 10.797 | 47.476 | 1.00 18.56 |
| ATOM | 3235 | CB | VAL | B | 372 | 54.699 | 9.391 | 47.972 | 1.00 18.16 |
| ATOM | 3236 | CG1 | VAL | B | 372 | 55.704 | 9.527 | 49.131 | 1.00 17.55 |
| ATOM | 3237 | CG2 | VAL | B | 372 | 53.501 | 8.558 | 48.398 | 1.00 15.94 |
| ATOM | 3238 | C | VAL | B | 372 | 55.387 | 11.599 | 46.865 | 1.00 19.68 |
| ATOM | 3239 | O | VAL | B | 372 | 55.740 | 11.416 | 45.694 | 1.00 19.72 |
| ATOM | 3240 | N | SER | B | 373 | 55.939 | 12.526 | 47.643 | 1.00 20.97 |
| ATOM | 3241 | CA | SER | B | 373 | 57.050 | 13.346 | 47.173 | 1.00 23.64 |
| ATOM | 3242 | CB | SER | B | 373 | 56.972 | 14.741 | 47.784 | 1.00 23.29 |
| ATOM | 3243 | OG | SER | B | 373 | 57.178 | 14.661 | 49.185 | 1.00 25.41 |
| ATOM | 3244 | C | SER | B | 373 | 58.379 | 12.707 | 47.561 | 1.00 25.67 |
| ATOM | 3245 | O | SER | B | 373 | 58.404 | 11.645 | 48.192 | 1.00 26.36 |
| ATOM | 3246 | N | ASP | B | 374 | 59.478 | 13.370 | 47.191 | 1.00 27.49 |
| ATOM | 3247 | CA | ASP | B | 374 | 60.826 | 12.902 | 47.514 | 1.00 29.09 |
| ATOM | 3248 | CB | ASP | B | 374 | 61.874 | 13.751 | 46.779 | 1.00 29.79 |
| ATOM | 3249 | CG | ASP | B | 374 | 61.695 | 15.244 | 47.016 | 1.00 29.95 |
| ATOM | 3250 | OD1 | ASP | B | 374 | 61.419 | 15.980 | 46.051 | 1.00 31.17 |
| ATOM | 3251 | OD2 | ASP | B | 374 | 61.843 | 15.690 | 48.162 | 1.00 30.27 |
| ATOM | 3252 | C | ASP | B | 374 | 61.048 | 12.944 | 49.037 | 1.00 29.73 |
| ATOM | 3253 | O | ASP | B | 374 | 61.845 | 12.162 | 49.590 | 1.00 29.69 |
| ATOM | 3254 | N | THR | B | 375 | 60.308 | 13.849 | 49.688 | 1.00 29.57 |
| ATOM | 3255 | CA | THR | B | 375 | 60.346 | 14.047 | 51.132 | 1.00 29.21 |
| ATOM | 3256 | CB | THR | B | 375 | 60.120 | 15.546 | 51.530 | 1.00 30.07 |
| ATOM | 3257 | OG1 | THR | B | 375 | 58.816 | 15.980 | 51.118 | 1.00 30.17 |
| ATOM | 3258 | CG2 | THR | B | 375 | 61.186 | 16.447 | 50.907 | 1.00 29.34 |
| ATOM | 3259 | C | THR | B | 375 | 59.282 | 13.199 | 51.828 | 1.00 28.52 |
| ATOM | 3260 | O | THR | B | 375 | 59.007 | 13.397 | 53.007 | 1.00 28.76 |
| ATOM | 3261 | N | LEU | B | 376 | 58.671 | 12.282 | 51.077 | 1.00 28.20 |
| ATOM | 3262 | CA | LEU | B | 376 | 57.628 | 11.356 | 51.565 | 1.00 27.01 |
| ATOM | 3263 | CB | LEU | B | 376 | 58.187 | 10.407 | 52.626 | 1.00 26.84 |
| ATOM | 3264 | CG | LEU | B | 376 | 59.456 | 9.628 | 52.303 | 1.00 27.19 |
| ATOM | 3265 | CD1 | LEU | B | 376 | 59.743 | 8.655 | 53.434 | 1.00 27.65 |
| ATOM | 3266 | CD2 | LEU | B | 376 | 59.302 | 8.894 | 50.982 | 1.00 26.78 |
| ATOM | 3267 | C | LEU | B | 376 | 56.319 | 11.962 | 52.072 | 1.00 26.66 |
| ATOM | 3268 | O | LEU | B | 376 | 55.608 | 11.343 | 52.858 | 1.00 26.40 |
| ATOM | 3269 | N | SER | B | 377 | 56.028 | 13.192 | 51.675 | 1.00 27.04 |
| ATOM | 3270 | CA | SER | B | 377 | 54.789 | 13.838 | 52.081 | 1.00 26.53 |
| ATOM | 3271 | CB | SER | B | 377 | 54.972 | 15.352 | 52.196 | 1.00 26.51 |
| ATOM | 3272 | OG | SER | B | 377 | 55.255 | 15.931 | 50.936 | 1.00 28.21 |
| ATOM | 3273 | C | SER | B | 377 | 53.743 | 13.497 | 51.021 | 1.00 25.99 |
| ATOM | 3274 | O | SER | B | 377 | 54.088 | 13.240 | 49.862 | 1.00 26.13 |
| ATOM | 3275 | N | CYS | B | 378 | 52.472 | 13.492 | 51.424 | 1.00 25.13 |
| ATOM | 3276 | CA | CYS | B | 378 | 51.372 | 13.158 | 50.517 | 1.00 23.26 |
| ATOM | 3277 | CB | CYS | B | 378 | 50.383 | 12.218 | 51.217 | 1.00 22.79 |
| ATOM | 3278 | SG | CYS | B | 378 | 51.134 | 10.731 | 51.907 | 1.00 20.86 |
| ATOM | 3279 | C | CYS | B | 378 | 50.620 | 14.368 | 49.966 | 1.00 21.87 |
| ATOM | 3280 | O | CYS | B | 378 | 50.442 | 15.355 | 50.670 | 1.00 21.61 |
| ATOM | 3281 | N | LYS | B | 379 | 50.188 | 14.253 | 48.703 | 1.00 21.42 |
| ATOM | 3282 | CA | LYS | B | 379 | 49.420 | 15.266 | 47.964 | 1.00 20.62 |
| ATOM | 3283 | CB | LYS | B | 379 | 50.300 | 16.023 | 46.980 | 1.00 21.35 |
| ATOM | 3284 | CG | LYS | B | 379 | 50.888 | 17.298 | 47.557 | 1.00 23.63 |
| ATOM | 3285 | CD | LYS | B | 379 | 52.093 | 17.753 | 46.772 | 1.00 25.31 |
| ATOM | 3286 | CE | LYS | B | 379 | 52.696 | 19.015 | 47.345 | 1.00 25.51 |
| ATOM | 3287 | NZ | LYS | B | 379 | 54.102 | 19.170 | 46.873 | 1.00 26.65 |

Figure 5

| ATOM | 3288 | C   | LYS B 379 | 48.292 | 14.575 | 47.217 | 1.00 | 20.53 |
| ATOM | 3289 | O   | LYS B 379 | 48.467 | 13.477 | 46.696 | 1.00 | 21.20 |
| ATOM | 3290 | N   | ILE B 380 | 47.137 | 15.227 | 47.151 | 1.00 | 20.27 |
| ATOM | 3291 | CA  | ILE B 380 | 45.961 | 14.651 | 46.512 | 1.00 | 20.00 |
| ATOM | 3292 | CB  | ILE B 380 | 44.677 | 15.125 | 47.201 | 1.00 | 18.60 |
| ATOM | 3293 | CG2 | ILE B 380 | 43.459 | 14.635 | 46.451 | 1.00 | 16.04 |
| ATOM | 3294 | CG1 | ILE B 380 | 44.661 | 14.648 | 48.645 | 1.00 | 17.24 |
| ATOM | 3295 | CD1 | ILE B 380 | 43.623 | 15.342 | 49.462 | 1.00 | 17.57 |
| ATOM | 3296 | C   | ILE B 380 | 45.858 | 14.974 | 45.035 | 1.00 | 21.18 |
| ATOM | 3297 | O   | ILE B 380 | 45.791 | 16.151 | 44.639 | 1.00 | 21.67 |
| ATOM | 3298 | N   | ALA B 381 | 45.795 | 13.917 | 44.228 | 1.00 | 21.44 |
| ATOM | 3299 | CA  | ALA B 381 | 45.687 | 14.059 | 42.787 | 1.00 | 21.58 |
| ATOM | 3300 | CB  | ALA B 381 | 46.744 | 13.237 | 42.119 | 1.00 | 21.22 |
| ATOM | 3301 | C   | ALA B 381 | 44.315 | 13.595 | 42.345 | 1.00 | 21.84 |
| ATOM | 3302 | O   | ALA B 381 | 43.604 | 12.933 | 43.098 | 1.00 | 21.57 |
| ATOM | 3303 | N   | ASP B 382 | 43.950 | 13.960 | 41.122 | 1.00 | 22.91 |
| ATOM | 3304 | CA  | ASP B 382 | 42.677 | 13.570 | 40.513 | 1.00 | 23.34 |
| ATOM | 3305 | CB  | ASP B 382 | 42.713 | 12.081 | 40.135 | 1.00 | 22.62 |
| ATOM | 3306 | CG  | ASP B 382 | 43.556 | 11.808 | 38.892 | 1.00 | 21.21 |
| ATOM | 3307 | OD1 | ASP B 382 | 43.408 | 12.549 | 37.901 | 1.00 | 22.61 |
| ATOM | 3308 | OD2 | ASP B 382 | 44.352 | 10.848 | 38.895 | 1.00 | 19.79 |
| ATOM | 3309 | C   | ASP B 382 | 41.420 | 13.895 | 41.320 | 1.00 | 24.00 |
| ATOM | 3310 | O   | ASP B 382 | 40.442 | 13.145 | 41.297 | 1.00 | 23.99 |
| ATOM | 3311 | N   | PHE B 383 | 41.436 | 15.048 | 41.981 | 1.00 | 24.57 |
| ATOM | 3312 | CA  | PHE B 383 | 40.306 | 15.484 | 42.788 | 1.00 | 25.35 |
| ATOM | 3313 | CB  | PHE B 383 | 40.765 | 16.268 | 44.043 | 1.00 | 23.86 |
| ATOM | 3314 | CG  | PHE B 383 | 41.725 | 17.401 | 43.757 | 1.00 | 23.54 |
| ATOM | 3315 | CD1 | PHE B 383 | 41.252 | 18.698 | 43.554 | 1.00 | 23.09 |
| ATOM | 3316 | CD2 | PHE B 383 | 43.103 | 17.167 | 43.682 | 1.00 | 22.78 |
| ATOM | 3317 | CE1 | PHE B 383 | 42.132 | 19.746 | 43.275 | 1.00 | 22.40 |
| ATOM | 3318 | CE2 | PHE B 383 | 43.988 | 18.204 | 43.409 | 1.00 | 22.54 |
| ATOM | 3319 | CZ  | PHE B 383 | 43.497 | 19.500 | 43.203 | 1.00 | 22.40 |
| ATOM | 3320 | C   | PHE B 383 | 39.327 | 16.318 | 41.987 | 1.00 | 26.08 |
| ATOM | 3321 | O   | PHE B 383 | 39.698 | 16.968 | 41.013 | 1.00 | 26.81 |
| ATOM | 3322 | N   | GLY B 384 | 38.064 | 16.240 | 42.375 | 1.00 | 26.95 |
| ATOM | 3323 | CA  | GLY B 384 | 37.032 | 17.021 | 41.732 | 1.00 | 27.95 |
| ATOM | 3324 | C   | GLY B 384 | 36.585 | 16.619 | 40.348 | 1.00 | 28.98 |
| ATOM | 3325 | O   | GLY B 384 | 35.913 | 17.421 | 39.697 | 1.00 | 30.38 |
| ATOM | 3326 | N   | LEU B 385 | 36.940 | 15.420 | 39.876 | 1.00 | 29.26 |
| ATOM | 3327 | CA  | LEU B 385 | 36.506 | 15.002 | 38.544 | 1.00 | 28.85 |
| ATOM | 3328 | CB  | LEU B 385 | 37.205 | 13.713 | 38.083 | 1.00 | 27.07 |
| ATOM | 3329 | CG  | LEU B 385 | 38.744 | 13.645 | 37.946 | 1.00 | 26.00 |
| ATOM | 3330 | CD1 | LEU B 385 | 39.089 | 12.695 | 36.827 | 1.00 | 24.35 |
| ATOM | 3331 | CD2 | LEU B 385 | 39.378 | 14.982 | 37.659 | 1.00 | 24.19 |
| ATOM | 3332 | C   | LEU B 385 | 34.981 | 14.849 | 38.529 | 1.00 | 29.87 |
| ATOM | 3333 | O   | LEU B 385 | 34.359 | 14.674 | 39.572 | 1.00 | 30.13 |
| ATOM | 3334 | N   | ALA B 386 | 34.380 | 15.009 | 37.355 | 1.00 | 30.91 |
| ATOM | 3335 | CA  | ALA B 386 | 32.930 | 14.913 | 37.196 | 1.00 | 31.41 |
| ATOM | 3336 | CB  | ALA B 386 | 32.498 | 15.716 | 35.948 | 1.00 | 32.02 |
| ATOM | 3337 | C   | ALA B 386 | 32.464 | 13.466 | 37.068 | 1.00 | 31.42 |
| ATOM | 3338 | O   | ALA B 386 | 31.264 | 13.172 | 37.147 | 1.00 | 32.41 |
| ATOM | 3339 | N   | ARG B 387 | 33.425 | 12.567 | 36.877 | 1.00 | 30.65 |
| ATOM | 3340 | CA  | ARG B 387 | 33.139 | 11.153 | 36.694 | 1.00 | 29.03 |
| ATOM | 3341 | CB  | ARG B 387 | 33.455 | 10.774 | 35.249 | 1.00 | 28.04 |
| ATOM | 3342 | CG  | ARG B 387 | 34.920 | 11.016 | 34.905 | 1.00 | 28.37 |
| ATOM | 3343 | CD  | ARG B 387 | 35.219 | 10.767 | 33.447 | 1.00 | 27.81 |
| ATOM | 3344 | NE  | ARG B 387 | 36.644 | 10.894 | 33.169 | 1.00 | 26.82 |
| ATOM | 3345 | CZ  | ARG B 387 | 37.514 |  9.912 | 33.358 | 1.00 | 28.10 |
| ATOM | 3346 | NH1 | ARG B 387 | 37.093 |  8.734 | 33.810 | 1.00 | 28.17 |
| ATOM | 3347 | NH2 | ARG B 387 | 38.813 | 10.125 | 33.169 | 1.00 | 29.02 |

Figure 5

```
ATOM   3348  C   ARG B 387      33.976  10.281  37.621  1.00 28.43
ATOM   3349  O   ARG B 387      34.803  10.782  38.390  1.00 27.70
ATOM   3350  N   LEU B 388      33.717   8.974  37.549  1.00 27.29
ATOM   3351  CA  LEU B 388      34.438   7.990  38.326  1.00 26.40
ATOM   3352  CB  LEU B 388      33.513   6.870  38.772  1.00 25.97
ATOM   3353  CG  LEU B 388      32.270   7.244  39.581  1.00 26.65
ATOM   3354  CD1 LEU B 388      31.685   5.963  40.170  1.00 27.27
ATOM   3355  CD2 LEU B 388      32.601   8.218  40.695  1.00 26.29
ATOM   3356  C   LEU B 388      35.539   7.421  37.437  1.00 26.83
ATOM   3357  O   LEU B 388      35.281   6.964  36.315  1.00 27.01
ATOM   3358  N   ILE B 389      36.768   7.450  37.949  1.00 25.88
ATOM   3359  CA  ILE B 389      37.913   6.960  37.204  1.00 24.42
ATOM   3360  CB  ILE B 389      39.099   7.965  37.256  1.00 23.06
ATOM   3361  CG2 ILE B 389      38.622   9.366  36.858  1.00 20.74
ATOM   3362  CG1 ILE B 389      39.771   7.930  38.639  1.00 21.82
ATOM   3363  CD1 ILE B 389      40.744   9.052  38.905  1.00 19.26
ATOM   3364  C   ILE B 389      38.400   5.597  37.662  1.00 25.29
ATOM   3365  O   ILE B 389      38.098   5.136  38.756  1.00 25.90
ATOM   3366  N   GLU B 390      39.154   4.957  36.782  1.00 26.90
ATOM   3367  CA  GLU B 390      39.744   3.655  37.031  1.00 27.96
ATOM   3368  CB  GLU B 390      39.228   2.643  36.000  1.00 29.57
ATOM   3369  CG  GLU B 390      37.700   2.648  35.905  1.00 33.57
ATOM   3370  CD  GLU B 390      37.113   1.474  35.138  1.00 35.89
ATOM   3371  OE1 GLU B 390      37.805   0.879  34.280  1.00 36.90
ATOM   3372  OE2 GLU B 390      35.932   1.156  35.397  1.00 38.26
ATOM   3373  C   GLU B 390      41.270   3.792  36.987  1.00 27.23
ATOM   3374  O   GLU B 390      41.809   4.734  36.411  1.00 25.57
ATOM   3375  N   ASP B 391      41.958   2.835  37.596  1.00 28.24
ATOM   3376  CA  ASP B 391      43.415   2.848  37.672  1.00 29.13
ATOM   3377  CB  ASP B 391      43.872   1.918  38.795  1.00 31.43
ATOM   3378  CG  ASP B 391      43.389   2.381  40.160  1.00 34.64
ATOM   3379  OD1 ASP B 391      42.999   3.577  40.298  1.00 35.73
ATOM   3380  OD2 ASP B 391      43.395   1.541  41.090  1.00 36.19
ATOM   3381  C   ASP B 391      44.204   2.573  36.398  1.00 28.71
ATOM   3382  O   ASP B 391      45.378   2.937  36.315  1.00 28.74
ATOM   3383  N   ASN B 392      43.552   1.965  35.405  1.00 28.30
ATOM   3384  CA  ASN B 392      44.178   1.628  34.128  1.00 26.87
ATOM   3385  CB  ASN B 392      43.628   0.282  33.606  1.00 27.56
ATOM   3386  CG  ASN B 392      42.117   0.321  33.279  1.00 28.68
ATOM   3387  OD1 ASN B 392      41.450   1.357  33.396  1.00 27.71
ATOM   3388  ND2 ASN B 392      41.587  -0.820  32.844  1.00 29.09
ATOM   3389  C   ASN B 392      43.986   2.722  33.068  1.00 26.43
ATOM   3390  O   ASN B 392      44.307   2.513  31.893  1.00 26.32
ATOM   3391  N   GLU B 393      43.503   3.896  33.480  1.00 24.81
ATOM   3392  CA  GLU B 393      43.254   4.968  32.534  1.00 23.67
ATOM   3393  CB  GLU B 393      42.298   6.015  33.110  1.00 21.93
ATOM   3394  CG  GLU B 393      40.878   5.483  33.251  1.00 19.39
ATOM   3395  CD  GLU B 393      39.862   6.514  33.698  1.00 19.01
ATOM   3396  OE1 GLU B 393      40.211   7.704  33.860  1.00 18.49
ATOM   3397  OE2 GLU B 393      38.685   6.125  33.870  1.00 18.87
ATOM   3398  C   GLU B 393      44.499   5.605  31.990  1.00 24.84
ATOM   3399  O   GLU B 393      44.580   5.860  30.798  1.00 24.66
ATOM   3400  N   TYR B 394      45.484   5.841  32.845  1.00 26.65
ATOM   3401  CA  TYR B 394      46.730   6.448  32.393  1.00 28.60
ATOM   3402  CB  TYR B 394      46.840   7.905  32.867  1.00 28.07
ATOM   3403  CG  TYR B 394      45.703   8.804  32.393  1.00 27.98
ATOM   3404  CD1 TYR B 394      44.496   8.855  33.096  1.00 28.11
ATOM   3405  CE1 TYR B 394      43.445   9.675  32.684  1.00 28.60
ATOM   3406  CD2 TYR B 394      45.832   9.602  31.252  1.00 26.98
ATOM   3407  CE2 TYR B 394      44.781  10.431  30.820  1.00 27.42
```

Figure 5

| | | | | | | | | |
|---|---|---|---|---|---|---|---|---|
| ATOM | 3408 | CZ | TYR | B | 394 | 43.581 | 10.463 | 31.546 | 1.00 28.70 |
| ATOM | 3409 | OH | TYR | B | 394 | 42.518 | 11.276 | 31.166 | 1.00 27.07 |
| ATOM | 3410 | C | TYR | B | 394 | 47.971 | 5.629 | 32.766 | 1.00 30.26 |
| ATOM | 3411 | O | TYR | B | 394 | 49.095 | 6.131 | 32.703 | 1.00 29.77 |
| ATOM | 3412 | N | THR | B | 395 | 47.746 | 4.381 | 33.182 | 1.00 32.64 |
| ATOM | 3413 | CA | THR | B | 395 | 48.815 | 3.441 | 33.524 | 1.00 36.52 |
| ATOM | 3414 | CB | THR | B | 395 | 49.380 | 3.611 | 34.959 | 1.00 36.87 |
| ATOM | 3415 | OG1 | THR | B | 395 | 48.323 | 3.886 | 35.894 | 1.00 38.40 |
| ATOM | 3416 | CG2 | THR | B | 395 | 50.414 | 4.706 | 34.984 | 1.00 36.46 |
| ATOM | 3417 | C | THR | B | 395 | 48.342 | 2.014 | 33.331 | 1.00 39.20 |
| ATOM | 3418 | O | THR | B | 395 | 47.324 | 1.781 | 32.680 | 1.00 40.87 |
| ATOM | 3419 | N | ALA | B | 396 | 49.063 | 1.052 | 33.901 | 1.00 42.18 |
| ATOM | 3420 | CA | ALA | B | 396 | 48.680 | -0.342 | 33.730 | 1.00 44.53 |
| ATOM | 3421 | CB | ALA | B | 396 | 49.556 | -0.991 | 32.642 | 1.00 44.44 |
| ATOM | 3422 | C | ALA | B | 396 | 48.658 | -1.204 | 35.003 | 1.00 46.12 |
| ATOM | 3423 | O | ALA | B | 396 | 49.486 | -2.109 | 35.167 | 1.00 47.48 |
| ATOM | 3424 | N | ARG | B | 397 | 47.710 | -0.927 | 35.900 | 1.00 46.61 |
| ATOM | 3425 | CA | ARG | B | 397 | 47.586 | -1.724 | 37.116 | 1.00 47.06 |
| ATOM | 3426 | CB | ARG | B | 397 | 46.937 | -0.921 | 38.236 | 1.00 46.68 |
| ATOM | 3427 | CG | ARG | B | 397 | 47.868 | 0.088 | 38.857 | 1.00 46.96 |
| ATOM | 3428 | CD | ARG | B | 397 | 47.628 | 0.209 | 40.355 | 1.00 47.14 |
| ATOM | 3429 | NE | ARG | B | 397 | 48.389 | 1.316 | 40.929 | 1.00 46.16 |
| ATOM | 3430 | CZ | ARG | B | 397 | 48.146 | 2.600 | 40.675 | 1.00 45.54 |
| ATOM | 3431 | NH1 | ARG | B | 397 | 47.153 | 2.951 | 39.862 | 1.00 44.69 |
| ATOM | 3432 | NH2 | ARG | B | 397 | 48.923 | 3.534 | 41.203 | 1.00 44.70 |
| ATOM | 3433 | C | ARG | B | 397 | 46.790 | -3.006 | 36.862 | 1.00 47.72 |
| ATOM | 3434 | O | ARG | B | 397 | 47.324 | -4.087 | 37.210 | 1.00 48.15 |
| ATOM | 3435 | CB | PRO | B | 403 | 36.386 | 2.109 | 41.265 | 1.00 26.63 |
| ATOM | 3436 | CG | PRO | B | 403 | 37.023 | 1.598 | 39.978 | 1.00 28.23 |
| ATOM | 3437 | C | PRO | B | 403 | 35.242 | 0.830 | 43.149 | 1.00 26.91 |
| ATOM | 3438 | O | PRO | B | 403 | 35.172 | 1.728 | 44.021 | 1.00 27.14 |
| ATOM | 3439 | N | PRO | B | 403 | 36.148 | -0.285 | 41.057 | 1.00 27.02 |
| ATOM | 3440 | CD | PRO | B | 403 | 36.368 | 0.237 | 39.697 | 1.00 27.12 |
| ATOM | 3441 | CA | PRO | B | 403 | 36.338 | 0.816 | 42.054 | 1.00 26.91 |
| ATOM | 3442 | N | ILE | B | 404 | 34.439 | -0.231 | 43.119 | 1.00 25.22 |
| ATOM | 3443 | CA | ILE | B | 404 | 33.337 | -0.444 | 44.044 | 1.00 22.26 |
| ATOM | 3444 | CB | ILE | B | 404 | 32.534 | -1.730 | 43.630 | 1.00 22.11 |
| ATOM | 3445 | CG2 | ILE | B | 404 | 31.588 | -2.181 | 44.725 | 1.00 23.57 |
| ATOM | 3446 | CG1 | ILE | B | 404 | 31.727 | -1.442 | 42.371 | 1.00 23.25 |
| ATOM | 3447 | CD1 | ILE | B | 404 | 30.773 | -0.251 | 42.528 | 1.00 24.98 |
| ATOM | 3448 | C | ILE | B | 404 | 33.751 | -0.510 | 45.515 | 1.00 19.32 |
| ATOM | 3449 | O | ILE | B | 404 | 32.994 | -0.093 | 46.377 | 1.00 19.89 |
| ATOM | 3450 | N | LYS | B | 405 | 34.970 | -0.962 | 45.789 | 1.00 16.67 |
| ATOM | 3451 | CA | LYS | B | 405 | 35.444 | -1.106 | 47.164 | 1.00 15.71 |
| ATOM | 3452 | CB | LYS | B | 405 | 36.691 | -1.991 | 47.207 | 1.00 15.79 |
| ATOM | 3453 | CG | LYS | B | 405 | 36.466 | -3.353 | 46.572 | 1.00 16.64 |
| ATOM | 3454 | CD | LYS | B | 405 | 37.578 | -4.323 | 46.901 | 1.00 16.21 |
| ATOM | 3455 | CE | LYS | B | 405 | 37.244 | -5.701 | 46.366 | 1.00 16.45 |
| ATOM | 3456 | NZ | LYS | B | 405 | 38.129 | -6.742 | 46.947 | 1.00 18.33 |
| ATOM | 3457 | C | LYS | B | 405 | 35.656 | 0.161 | 47.987 | 1.00 14.61 |
| ATOM | 3458 | O | LYS | B | 405 | 35.867 | 0.096 | 49.191 | 1.00 13.13 |
| ATOM | 3459 | N | TRP | B | 406 | 35.604 | 1.307 | 47.327 | 1.00 15.37 |
| ATOM | 3460 | CA | TRP | B | 406 | 35.768 | 2.598 | 47.984 | 1.00 15.76 |
| ATOM | 3461 | CB | TRP | B | 406 | 36.866 | 3.410 | 47.296 | 1.00 16.16 |
| ATOM | 3462 | CG | TRP | B | 406 | 38.248 | 2.864 | 47.499 | 1.00 16.96 |
| ATOM | 3463 | CD2 | TRP | B | 406 | 38.885 | 1.830 | 46.736 | 1.00 17.70 |
| ATOM | 3464 | CE2 | TRP | B | 406 | 40.182 | 1.659 | 47.268 | 1.00 17.16 |
| ATOM | 3465 | CE3 | TRP | B | 406 | 38.486 | 1.033 | 45.652 | 1.00 18.00 |
| ATOM | 3466 | CD1 | TRP | B | 406 | 39.160 | 3.269 | 48.432 | 1.00 17.20 |
| ATOM | 3467 | NE1 | TRP | B | 406 | 40.322 | 2.549 | 48.301 | 1.00 17.95 |

Figure 5

| | | | | | | | | | |
|---|---|---|---|---|---|---|---|---|---|
| ATOM | 3468 | CZ2 | TRP | B | 406 | 41.081 | 0.725 | 46.758 | 1.00 16.55 |
| ATOM | 3469 | CZ3 | TRP | B | 406 | 39.387 | 0.103 | 45.143 | 1.00 16.62 |
| ATOM | 3470 | CH2 | TRP | B | 406 | 40.667 | -0.042 | 45.702 | 1.00 17.31 |
| ATOM | 3471 | C | TRP | B | 406 | 34.470 | 3.400 | 47.943 | 1.00 15.66 |
| ATOM | 3472 | O | TRP | B | 406 | 34.421 | 4.518 | 48.441 | 1.00 16.38 |
| ATOM | 3473 | N | THR | B | 407 | 33.426 | 2.832 | 47.342 | 1.00 15.20 |
| ATOM | 3474 | CA | THR | B | 407 | 32.132 | 3.508 | 47.227 | 1.00 14.83 |
| ATOM | 3475 | CB | THR | B | 407 | 31.451 | 3.163 | 45.867 | 1.00 13.66 |
| ATOM | 3476 | OG1 | THR | B | 407 | 32.410 | 3.274 | 44.819 | 1.00 15.14 |
| ATOM | 3477 | CG2 | THR | B | 407 | 30.358 | 4.144 | 45.552 | 1.00 12.76 |
| ATOM | 3478 | C | THR | B | 407 | 31.123 | 3.282 | 48.377 | 1.00 14.39 |
| ATOM | 3479 | O | THR | B | 407 | 30.716 | 2.144 | 48.654 | 1.00 15.26 |
| ATOM | 3480 | N | ALA | B | 408 | 30.700 | 4.388 | 48.996 | 1.00 13.51 |
| ATOM | 3481 | CA | ALA | B | 408 | 29.721 | 4.386 | 50.086 | 1.00 12.75 |
| ATOM | 3482 | CB | ALA | B | 408 | 29.403 | 5.808 | 50.533 | 1.00 11.12 |
| ATOM | 3483 | C | ALA | B | 408 | 28.458 | 3.732 | 49.613 | 1.00 13.41 |
| ATOM | 3484 | O | ALA | B | 408 | 28.151 | 3.751 | 48.423 | 1.00 15.14 |
| ATOM | 3485 | N | PRO | B | 409 | 27.662 | 3.199 | 50.543 | 1.00 13.42 |
| ATOM | 3486 | CD | PRO | B | 409 | 27.938 | 3.034 | 51.974 | 1.00 12.29 |
| ATOM | 3487 | CA | PRO | B | 409 | 26.409 | 2.537 | 50.177 | 1.00 13.46 |
| ATOM | 3488 | CB | PRO | B | 409 | 25.868 | 2.076 | 51.524 | 1.00 13.22 |
| ATOM | 3489 | CG | PRO | B | 409 | 27.107 | 1.837 | 52.308 | 1.00 12.77 |
| ATOM | 3490 | C | PRO | B | 409 | 25.415 | 3.439 | 49.460 | 1.00 13.93 |
| ATOM | 3491 | O | PRO | B | 409 | 24.780 | 3.018 | 48.500 | 1.00 15.33 |
| ATOM | 3492 | N | GLU | B | 410 | 25.275 | 4.677 | 49.912 | 1.00 15.04 |
| ATOM | 3493 | CA | GLU | B | 410 | 24.322 | 5.583 | 49.282 | 1.00 16.75 |
| ATOM | 3494 | CB | GLU | B | 410 | 24.159 | 6.880 | 50.093 | 1.00 16.29 |
| ATOM | 3495 | CG | GLU | B | 410 | 25.314 | 7.875 | 49.974 | 1.00 16.29 |
| ATOM | 3496 | CD | GLU | B | 410 | 26.391 | 7.740 | 51.041 | 1.00 16.45 |
| ATOM | 3497 | OE1 | GLU | B | 410 | 26.378 | 6.764 | 51.833 | 1.00 11.96 |
| ATOM | 3498 | OE2 | GLU | B | 410 | 27.248 | 8.657 | 51.075 | 1.00 17.73 |
| ATOM | 3499 | C | GLU | B | 410 | 24.719 | 5.891 | 47.844 | 1.00 18.07 |
| ATOM | 3500 | O | GLU | B | 410 | 23.855 | 6.124 | 46.995 | 1.00 19.26 |
| ATOM | 3501 | N | ALA | B | 411 | 26.024 | 5.890 | 47.570 | 1.00 19.26 |
| ATOM | 3502 | CA | ALA | B | 411 | 26.525 | 6.153 | 46.224 | 1.00 19.78 |
| ATOM | 3503 | CB | ALA | B | 411 | 28.000 | 6.431 | 46.265 | 1.00 19.10 |
| ATOM | 3504 | C | ALA | B | 411 | 26.230 | 4.969 | 45.297 | 1.00 20.85 |
| ATOM | 3505 | O | ALA | B | 411 | 25.870 | 5.152 | 44.140 | 1.00 21.18 |
| ATOM | 3506 | N | ILE | B | 412 | 26.355 | 3.756 | 45.832 | 1.00 21.81 |
| ATOM | 3507 | CA | ILE | B | 412 | 26.096 | 2.535 | 45.074 | 1.00 22.35 |
| ATOM | 3508 | CB | ILE | B | 412 | 26.482 | 1.280 | 45.884 | 1.00 21.60 |
| ATOM | 3509 | CG2 | ILE | B | 412 | 25.912 | 0.008 | 45.205 | 1.00 19.60 |
| ATOM | 3510 | CG1 | ILE | B | 412 | 28.009 | 1.238 | 46.059 | 1.00 20.77 |
| ATOM | 3511 | CD1 | ILE | B | 412 | 28.529 | 0.106 | 46.896 | 1.00 18.38 |
| ATOM | 3512 | C | ILE | B | 412 | 24.640 | 2.381 | 44.673 | 1.00 23.78 |
| ATOM | 3513 | O | ILE | B | 412 | 24.334 | 2.075 | 43.507 | 1.00 23.51 |
| ATOM | 3514 | N | ASN | B | 413 | 23.761 | 2.575 | 45.662 | 1.00 24.72 |
| ATOM | 3515 | CA | ASN | B | 413 | 22.317 | 2.439 | 45.498 | 1.00 24.69 |
| ATOM | 3516 | CB | ASN | B | 413 | 21.646 | 2.246 | 46.850 | 1.00 25.11 |
| ATOM | 3517 | CG | ASN | B | 413 | 22.058 | 0.969 | 47.526 | 1.00 26.42 |
| ATOM | 3518 | OD1 | ASN | B | 413 | 22.264 | -0.059 | 46.869 | 1.00 27.21 |
| ATOM | 3519 | ND2 | ASN | B | 413 | 22.181 | 1.017 | 48.855 | 1.00 25.18 |
| ATOM | 3520 | C | ASN | B | 413 | 21.610 | 3.562 | 44.780 | 1.00 24.84 |
| ATOM | 3521 | O | ASN | B | 413 | 20.677 | 3.310 | 44.020 | 1.00 25.17 |
| ATOM | 3522 | N | TYR | B | 414 | 22.002 | 4.801 | 45.050 | 1.00 24.84 |
| ATOM | 3523 | CA | TYR | B | 414 | 21.328 | 5.929 | 44.412 | 1.00 25.33 |
| ATOM | 3524 | CB | TYR | B | 414 | 20.496 | 6.687 | 45.463 | 1.00 27.92 |
| ATOM | 3525 | CG | TYR | B | 414 | 19.631 | 5.788 | 46.343 | 1.00 31.30 |
| ATOM | 3526 | CD1 | TYR | B | 414 | 18.335 | 5.423 | 45.956 | 1.00 31.73 |
| ATOM | 3527 | CE1 | TYR | B | 414 | 17.558 | 4.563 | 46.746 | 1.00 33.21 |

Figure 5

```
ATOM   3528  CD2  TYR B 414      20.128    5.274   47.552  1.00 32.81
ATOM   3529  CE2  TYR B 414      19.358    4.411   48.350  1.00 33.10
ATOM   3530  CZ   TYR B 414      18.075    4.058   47.937  1.00 34.12
ATOM   3531  OH   TYR B 414      17.321    3.183   48.699  1.00 35.83
ATOM   3532  C    TYR B 414      22.218    6.894   43.601  1.00 24.05
ATOM   3533  O    TYR B 414      21.715    7.821   42.968  1.00 23.98
ATOM   3534  N    GLY B 415      23.531    6.661   43.600  1.00 23.15
ATOM   3535  CA   GLY B 415      24.449    7.520   42.861  1.00 20.49
ATOM   3536  C    GLY B 415      24.577    8.906   43.458  1.00 19.78
ATOM   3537  O    GLY B 415      24.787    9.902   42.740  1.00 19.85
ATOM   3538  N    THR B 416      24.380    8.985   44.771  1.00 18.68
ATOM   3539  CA   THR B 416      24.493   10.254   45.460  1.00 17.48
ATOM   3540  CB   THR B 416      23.318   10.538   46.484  1.00 17.87
ATOM   3541  OG1  THR B 416      23.847   11.075   47.705  1.00 17.28
ATOM   3542  CG2  THR B 416      22.481    9.310   46.762  1.00 14.79
ATOM   3543  C    THR B 416      25.879   10.354   46.083  1.00 16.58
ATOM   3544  O    THR B 416      26.228    9.631   47.004  1.00 16.78
ATOM   3545  N    PHE B 417      26.685   11.209   45.471  1.00 15.68
ATOM   3546  CA   PHE B 417      28.050   11.465   45.868  1.00 13.57
ATOM   3547  CB   PHE B 417      28.936   11.443   44.618  1.00 14.42
ATOM   3548  CG   PHE B 417      29.098   10.066   43.998  1.00 14.86
ATOM   3549  CD1  PHE B 417      28.160    9.564   43.081  1.00 13.28
ATOM   3550  CD2  PHE B 417      30.190    9.260   44.349  1.00 14.36
ATOM   3551  CE1  PHE B 417      28.313    8.276   42.537  1.00 12.42
ATOM   3552  CE2  PHE B 417      30.346    7.971   43.804  1.00 12.49
ATOM   3553  CZ   PHE B 417      29.412    7.483   42.907  1.00 10.97
ATOM   3554  C    PHE B 417      28.189   12.807   46.587  1.00 12.65
ATOM   3555  O    PHE B 417      27.761   13.844   46.090  1.00 13.05
ATOM   3556  N    THR B 418      28.782   12.766   47.772  1.00 12.46
ATOM   3557  CA   THR B 418      29.014   13.950   48.602  1.00 11.85
ATOM   3558  CB   THR B 418      27.905   14.131   49.688  1.00 12.14
ATOM   3559  OG1  THR B 418      27.994   13.088   50.668  1.00 13.16
ATOM   3560  CG2  THR B 418      26.526   14.093   49.057  1.00 11.62
ATOM   3561  C    THR B 418      30.350   13.814   49.318  1.00 11.40
ATOM   3562  O    THR B 418      31.102   12.858   49.087  1.00 11.59
ATOM   3563  N    ILE B 419      30.639   14.773   50.191  1.00 11.82
ATOM   3564  CA   ILE B 419      31.873   14.764   50.977  1.00 11.42
ATOM   3565  CB   ILE B 419      32.079   16.097   51.757  1.00 10.97
ATOM   3566  CG2  ILE B 419      31.087   16.242   52.915  1.00  9.50
ATOM   3567  CG1  ILE B 419      33.496   16.170   52.304  1.00 11.72
ATOM   3568  CD1  ILE B 419      34.533   16.260   51.238  1.00 11.22
ATOM   3569  C    ILE B 419      31.823   13.581   51.940  1.00 12.53
ATOM   3570  O    ILE B 419      32.853   13.001   52.262  1.00 14.07
ATOM   3571  N    LYS B 420      30.613   13.178   52.328  1.00 12.37
ATOM   3572  CA   LYS B 420      30.409   12.056   53.234  1.00 11.66
ATOM   3573  CB   LYS B 420      28.980   12.045   53.732  1.00 10.50
ATOM   3574  CG   LYS B 420      28.654   13.235   54.601  1.00 10.64
ATOM   3575  CD   LYS B 420      29.595   13.284   55.787  1.00  9.48
ATOM   3576  CE   LYS B 420      29.258   14.430   56.700  1.00  6.27
ATOM   3577  NZ   LYS B 420      30.165   14.359   57.852  1.00  3.85
ATOM   3578  C    LYS B 420      30.771   10.726   52.593  1.00 12.17
ATOM   3579  O    LYS B 420      31.250    9.817   53.269  1.00 11.80
ATOM   3580  N    SER B 421      30.510   10.591   51.295  1.00 13.09
ATOM   3581  CA   SER B 421      30.893    9.368   50.600  1.00 12.94
ATOM   3582  CB   SER B 421      30.137    9.186   49.289  1.00 10.48
ATOM   3583  OG   SER B 421      29.942   10.408   48.648  1.00 10.74
ATOM   3584  C    SER B 421      32.408    9.382   50.398  1.00 14.26
ATOM   3585  O    SER B 421      33.018    8.343   50.125  1.00 17.73
ATOM   3586  N    ASP B 422      33.008   10.565   50.537  1.00 14.12
ATOM   3587  CA   ASP B 422      34.458   10.734   50.446  1.00 13.33
```

Figure 5

| | | | | | | | | | |
|---|---|---|---|---|---|---|---|---|---|
| ATOM | 3588 | CB | ASP | B | 422 | 34.848 | 12.203 | 50.284 | 1.00 13.98 |
| ATOM | 3589 | CG | ASP | B | 422 | 34.880 | 12.661 | 48.846 | 1.00 13.48 |
| ATOM | 3590 | OD1 | ASP | B | 422 | 34.703 | 11.855 | 47.923 | 1.00 15.44 |
| ATOM | 3591 | OD2 | ASP | B | 422 | 35.099 | 13.857 | 48.632 | 1.00 13.97 |
| ATOM | 3592 | C | ASP | B | 422 | 35.043 | 10.255 | 51.755 | 1.00 13.18 |
| ATOM | 3593 | O | ASP | B | 422 | 36.101 | 9.636 | 51.773 | 1.00 14.14 |
| ATOM | 3594 | N | VAL | B | 423 | 34.397 | 10.621 | 52.861 | 1.00 12.68 |
| ATOM | 3595 | CA | VAL | B | 423 | 34.849 | 10.184 | 54.174 | 1.00 11.07 |
| ATOM | 3596 | CB | VAL | B | 423 | 34.060 | 10.845 | 55.336 | 1.00 10.88 |
| ATOM | 3597 | CG1 | VAL | B | 423 | 34.413 | 10.189 | 56.664 | 1.00 7.93 |
| ATOM | 3598 | CG2 | VAL | B | 423 | 34.391 | 12.346 | 55.415 | 1.00 8.65 |
| ATOM | 3599 | C | VAL | B | 423 | 34.748 | 8.664 | 54.211 | 1.00 11.57 |
| ATOM | 3600 | O | VAL | B | 423 | 35.625 | 8.004 | 54.764 | 1.00 13.05 |
| ATOM | 3601 | N | TRP | B | 424 | 33.737 | 8.096 | 53.555 | 1.00 11.03 |
| ATOM | 3602 | CA | TRP | B | 424 | 33.625 | 6.639 | 53.512 | 1.00 11.25 |
| ATOM | 3603 | CB | TRP | B | 424 | 32.381 | 6.178 | 52.748 | 1.00 9.77 |
| ATOM | 3604 | CG | TRP | B | 424 | 32.312 | 4.668 | 52.621 | 1.00 8.20 |
| ATOM | 3605 | CD2 | TRP | B | 424 | 31.428 | 3.778 | 53.316 | 1.00 7.60 |
| ATOM | 3606 | CE2 | TRP | B | 424 | 31.768 | 2.463 | 52.926 | 1.00 7.46 |
| ATOM | 3607 | CE3 | TRP | B | 424 | 30.388 | 3.963 | 54.240 | 1.00 8.05 |
| ATOM | 3608 | CD1 | TRP | B | 424 | 33.118 | 3.873 | 51.847 | 1.00 8.09 |
| ATOM | 3609 | NE1 | TRP | B | 424 | 32.800 | 2.552 | 52.031 | 1.00 7.69 |
| ATOM | 3610 | CZ2 | TRP | B | 424 | 31.107 | 1.334 | 53.426 | 1.00 7.89 |
| ATOM | 3611 | CZ3 | TRP | B | 424 | 29.728 | 2.842 | 54.738 | 1.00 7.99 |
| ATOM | 3612 | CH2 | TRP | B | 424 | 30.096 | 1.543 | 54.327 | 1.00 8.91 |
| ATOM | 3613 | C | TRP | B | 424 | 34.884 | 6.123 | 52.827 | 1.00 12.24 |
| ATOM | 3614 | O | TRP | B | 424 | 35.577 | 5.274 | 53.380 | 1.00 13.56 |
| ATOM | 3615 | N | SER | B | 425 | 35.190 | 6.681 | 51.652 | 1.00 13.32 |
| ATOM | 3616 | CA | SER | B | 425 | 36.389 | 6.324 | 50.864 | 1.00 14.86 |
| ATOM | 3617 | CB | SER | B | 425 | 36.530 | 7.220 | 49.637 | 1.00 14.95 |
| ATOM | 3618 | OG | SER | B | 425 | 35.635 | 6.822 | 48.629 | 1.00 18.52 |
| ATOM | 3619 | C | SER | B | 425 | 37.684 | 6.452 | 51.631 | 1.00 14.21 |
| ATOM | 3620 | O | SER | B | 425 | 38.611 | 5.682 | 51.437 | 1.00 15.16 |
| ATOM | 3621 | N | PHE | B | 426 | 37.770 | 7.500 | 52.433 | 1.00 14.89 |
| ATOM | 3622 | CA | PHE | B | 426 | 38.954 | 7.754 | 53.226 | 1.00 14.89 |
| ATOM | 3623 | CB | PHE | B | 426 | 38.837 | 9.089 | 53.955 | 1.00 14.99 |
| ATOM | 3624 | CG | PHE | B | 426 | 40.033 | 9.413 | 54.785 | 1.00 15.28 |
| ATOM | 3625 | CD1 | PHE | B | 426 | 41.228 | 9.775 | 54.178 | 1.00 14.53 |
| ATOM | 3626 | CD2 | PHE | B | 426 | 39.991 | 9.293 | 56.159 | 1.00 15.51 |
| ATOM | 3627 | CE1 | PHE | B | 426 | 42.356 | 10.000 | 54.926 | 1.00 15.21 |
| ATOM | 3628 | CE2 | PHE | B | 426 | 41.128 | 9.519 | 56.918 | 1.00 15.88 |
| ATOM | 3629 | CZ | PHE | B | 426 | 42.313 | 9.871 | 56.295 | 1.00 15.74 |
| ATOM | 3630 | C | PHE | B | 426 | 39.185 | 6.634 | 54.232 | 1.00 15.03 |
| ATOM | 3631 | O | PHE | B | 426 | 40.318 | 6.205 | 54.428 | 1.00 15.62 |
| ATOM | 3632 | N | GLY | B | 427 | 38.113 | 6.186 | 54.885 | 1.00 14.66 |
| ATOM | 3633 | CA | GLY | B | 427 | 38.234 | 5.114 | 55.852 | 1.00 14.04 |
| ATOM | 3634 | C | GLY | B | 427 | 38.745 | 3.872 | 55.154 | 1.00 14.24 |
| ATOM | 3635 | O | GLY | B | 427 | 39.535 | 3.117 | 55.716 | 1.00 14.55 |
| ATOM | 3636 | N | ILE | B | 428 | 38.296 | 3.660 | 53.918 | 1.00 14.15 |
| ATOM | 3637 | CA | ILE | B | 428 | 38.734 | 2.511 | 53.141 | 1.00 13.78 |
| ATOM | 3638 | CB | ILE | B | 428 | 37.967 | 2.385 | 51.810 | 1.00 13.41 |
| ATOM | 3639 | CG2 | ILE | B | 428 | 38.577 | 1.282 | 50.981 | 1.00 13.48 |
| ATOM | 3640 | CG1 | ILE | B | 428 | 36.493 | 2.057 | 52.059 | 1.00 13.94 |
| ATOM | 3641 | CD1 | ILE | B | 428 | 36.266 | 0.703 | 52.777 | 1.00 12.77 |
| ATOM | 3642 | C | ILE | B | 428 | 40.207 | 2.724 | 52.835 | 1.00 14.71 |
| ATOM | 3643 | O | ILE | B | 428 | 41.014 | 1.808 | 52.958 | 1.00 15.26 |
| ATOM | 3644 | N | LEU | B | 429 | 40.550 | 3.966 | 52.503 | 1.00 14.71 |
| ATOM | 3645 | CA | LEU | B | 429 | 41.919 | 4.337 | 52.191 | 1.00 14.66 |
| ATOM | 3646 | CB | LEU | B | 429 | 41.993 | 5.823 | 51.806 | 1.00 14.23 |
| ATOM | 3647 | CG | LEU | B | 429 | 43.268 | 6.406 | 51.171 | 1.00 13.20 |

Figure 5

| | | | | | | | | | |
|---|---|---|---|---|---|---|---|---|---|
| ATOM | 3648 | CD1 | LEU | B | 429 | 42.963 | 7.733 | 50.523 | 1.00 13.30 |
| ATOM | 3649 | CD2 | LEU | B | 429 | 44.349 | 6.576 | 52.181 | 1.00 12.99 |
| ATOM | 3650 | C | LEU | B | 429 | 42.823 | 4.061 | 53.380 | 1.00 14.82 |
| ATOM | 3651 | O | LEU | B | 429 | 43.951 | 3.616 | 53.199 | 1.00 16.52 |
| ATOM | 3652 | N | LEU | B | 430 | 42.322 | 4.320 | 54.586 | 1.00 14.49 |
| ATOM | 3653 | CA | LEU | B | 430 | 43.089 | 4.110 | 55.805 | 1.00 14.55 |
| ATOM | 3654 | CB | LEU | B | 430 | 42.284 | 4.524 | 57.025 | 1.00 12.71 |
| ATOM | 3655 | CG | LEU | B | 430 | 42.210 | 5.987 | 57.425 | 1.00 11.72 |
| ATOM | 3656 | CD1 | LEU | B | 430 | 41.283 | 6.091 | 58.642 | 1.00 8.20 |
| ATOM | 3657 | CD2 | LEU | B | 430 | 43.593 | 6.514 | 57.756 | 1.00 9.95 |
| ATOM | 3658 | C | LEU | B | 430 | 43.556 | 2.664 | 55.968 | 1.00 16.10 |
| ATOM | 3659 | O | LEU | B | 430 | 44.599 | 2.417 | 56.578 | 1.00 17.27 |
| ATOM | 3660 | N | THR | B | 431 | 42.783 | 1.708 | 55.451 | 1.00 16.36 |
| ATOM | 3661 | CA | THR | B | 431 | 43.181 | 0.303 | 55.532 | 1.00 15.56 |
| ATOM | 3662 | CB | THR | B | 431 | 42.029 | -0.639 | 55.210 | 1.00 13.77 |
| ATOM | 3663 | OG1 | THR | B | 431 | 41.567 | -0.365 | 53.889 | 1.00 13.07 |
| ATOM | 3664 | CG2 | THR | B | 431 | 40.896 | -0.475 | 56.196 | 1.00 12.97 |
| ATOM | 3665 | C | THR | B | 431 | 44.315 | 0.051 | 54.525 | 1.00 17.31 |
| ATOM | 3666 | O | THR | B | 431 | 45.210 | -0.744 | 54.797 | 1.00 17.77 |
| ATOM | 3667 | N | GLU | B | 432 | 44.250 | 0.705 | 53.357 | 1.00 18.24 |
| ATOM | 3668 | CA | GLU | B | 432 | 45.286 | 0.592 | 52.325 | 1.00 18.18 |
| ATOM | 3669 | CB | GLU | B | 432 | 44.951 | 1.446 | 51.100 | 1.00 18.25 |
| ATOM | 3670 | CG | GLU | B | 432 | 43.925 | 0.864 | 50.145 | 1.00 20.34 |
| ATOM | 3671 | CD | GLU | B | 432 | 43.603 | 1.813 | 48.994 | 1.00 20.99 |
| ATOM | 3672 | OE1 | GLU | B | 432 | 43.033 | 2.892 | 49.246 | 1.00 18.50 |
| ATOM | 3673 | OE2 | GLU | B | 432 | 43.921 | 1.478 | 47.830 | 1.00 22.98 |
| ATOM | 3674 | C | GLU | B | 432 | 46.597 | 1.101 | 52.908 | 1.00 19.09 |
| ATOM | 3675 | O | GLU | B | 432 | 47.654 | 0.538 | 52.652 | 1.00 19.94 |
| ATOM | 3676 | N | ILE | B | 433 | 46.524 | 2.192 | 53.664 | 1.00 18.89 |
| ATOM | 3677 | CA | ILE | B | 433 | 47.702 | 2.775 | 54.297 | 1.00 19.28 |
| ATOM | 3678 | CB | ILE | B | 433 | 47.373 | 4.123 | 54.963 | 1.00 19.10 |
| ATOM | 3679 | CG2 | ILE | B | 433 | 48.556 | 4.626 | 55.781 | 1.00 19.45 |
| ATOM | 3680 | CG1 | ILE | B | 433 | 47.014 | 5.153 | 53.899 | 1.00 20.56 |
| ATOM | 3681 | CD1 | ILE | B | 433 | 46.881 | 6.558 | 54.441 | 1.00 21.17 |
| ATOM | 3682 | C | ILE | B | 433 | 48.322 | 1.892 | 55.372 | 1.00 20.05 |
| ATOM | 3683 | O | ILE | B | 433 | 49.541 | 1.755 | 55.445 | 1.00 20.49 |
| ATOM | 3684 | N | VAL | B | 434 | 47.481 | 1.296 | 56.211 | 1.00 21.11 |
| ATOM | 3685 | CA | VAL | B | 434 | 47.974 | 0.483 | 57.311 | 1.00 22.20 |
| ATOM | 3686 | CB | VAL | B | 434 | 46.991 | 0.547 | 58.489 | 1.00 22.20 |
| ATOM | 3687 | CG1 | VAL | B | 434 | 45.885 | -0.482 | 58.329 | 1.00 22.15 |
| ATOM | 3688 | CG2 | VAL | B | 434 | 47.722 | 0.385 | 59.787 | 1.00 23.46 |
| ATOM | 3689 | C | VAL | B | 434 | 48.355 | -0.967 | 56.967 | 1.00 23.75 |
| ATOM | 3690 | O | VAL | B | 434 | 49.013 | -1.649 | 57.760 | 1.00 25.10 |
| ATOM | 3691 | N | THR | B | 435 | 47.960 | -1.419 | 55.776 | 1.00 24.58 |
| ATOM | 3692 | CA | THR | B | 435 | 48.251 | -2.773 | 55.298 | 1.00 24.34 |
| ATOM | 3693 | CB | THR | B | 435 | 46.980 | -3.477 | 54.775 | 1.00 24.10 |
| ATOM | 3694 | OG1 | THR | B | 435 | 46.489 | -2.784 | 53.617 | 1.00 23.37 |
| ATOM | 3695 | CG2 | THR | B | 435 | 45.897 | -3.524 | 55.849 | 1.00 22.56 |
| ATOM | 3696 | C | THR | B | 435 | 49.232 | -2.671 | 54.144 | 1.00 25.54 |
| ATOM | 3697 | O | THR | B | 435 | 49.309 | -3.560 | 53.298 | 1.00 25.71 |
| ATOM | 3698 | N | HIS | B | 436 | 49.914 | -1.535 | 54.082 | 1.00 27.37 |
| ATOM | 3699 | CA | HIS | B | 436 | 50.887 | -1.236 | 53.043 | 1.00 28.77 |
| ATOM | 3700 | CB | HIS | B | 436 | 52.221 | -1.880 | 53.389 | 1.00 30.50 |
| ATOM | 3701 | CG | HIS | B | 436 | 52.817 | -1.353 | 54.656 | 1.00 33.96 |
| ATOM | 3702 | CD2 | HIS | B | 436 | 53.327 | -0.139 | 54.963 | 1.00 35.33 |
| ATOM | 3703 | ND1 | HIS | B | 436 | 52.898 | -2.106 | 55.807 | 1.00 36.03 |
| ATOM | 3704 | CE1 | HIS | B | 436 | 53.430 | -1.373 | 56.772 | 1.00 35.81 |
| ATOM | 3705 | NE2 | HIS | B | 436 | 53.700 | -0.177 | 56.285 | 1.00 35.76 |
| ATOM | 3706 | C | HIS | B | 436 | 50.474 | -1.549 | 51.602 | 1.00 29.31 |
| ATOM | 3707 | O | HIS | B | 436 | 51.200 | -2.229 | 50.875 | 1.00 29.96 |

Figure 5

| | | | | | | | | | |
|---|---|---|---|---|---|---|---|---|---|
| ATOM | 3708 | N | GLY | B | 437 | 49.297 | -1.078 | 51.201 | 1.00 28.83 |
| ATOM | 3709 | CA | GLY | B | 437 | 48.850 | -1.280 | 49.837 | 1.00 29.20 |
| ATOM | 3710 | C | GLY | B | 437 | 47.933 | -2.442 | 49.551 | 1.00 29.68 |
| ATOM | 3711 | O | GLY | B | 437 | 47.603 | -2.693 | 48.395 | 1.00 29.75 |
| ATOM | 3712 | N | ARG | B | 438 | 47.490 | -3.132 | 50.591 | 1.00 30.70 |
| ATOM | 3713 | CA | ARG | B | 438 | 46.595 | -4.275 | 50.404 | 1.00 32.22 |
| ATOM | 3714 | CB | ARG | B | 438 | 46.431 | -5.024 | 51.736 | 1.00 35.65 |
| ATOM | 3715 | CG | ARG | B | 438 | 45.992 | -6.491 | 51.656 | 1.00 39.03 |
| ATOM | 3716 | CD | ARG | B | 438 | 44.480 | -6.661 | 51.470 | 1.00 43.00 |
| ATOM | 3717 | NE | ARG | B | 438 | 43.659 | -5.991 | 52.492 | 1.00 46.56 |
| ATOM | 3718 | CZ | ARG | B | 438 | 43.585 | -6.364 | 53.773 | 1.00 48.47 |
| ATOM | 3719 | NH1 | ARG | B | 438 | 44.293 | -7.409 | 54.205 | 1.00 50.04 |
| ATOM | 3720 | NH2 | ARG | B | 438 | 42.791 | -5.706 | 54.617 | 1.00 47.18 |
| ATOM | 3721 | C | ARG | B | 438 | 45.239 | -3.821 | 49.857 | 1.00 30.97 |
| ATOM | 3722 | O | ARG | B | 438 | 44.737 | -2.757 | 50.211 | 1.00 31.37 |
| ATOM | 3723 | N | ILE | B | 439 | 44.680 | -4.606 | 48.946 | 1.00 30.20 |
| ATOM | 3724 | CA | ILE | B | 439 | 43.385 | -4.286 | 48.348 | 1.00 29.07 |
| ATOM | 3725 | CB | ILE | B | 439 | 43.157 | -5.117 | 47.053 | 1.00 28.98 |
| ATOM | 3726 | CG2 | ILE | B | 439 | 41.752 | -4.886 | 46.489 | 1.00 26.96 |
| ATOM | 3727 | CG1 | ILE | B | 439 | 44.219 | -4.726 | 46.018 | 1.00 29.85 |
| ATOM | 3728 | CD1 | ILE | B | 439 | 44.146 | -5.492 | 44.710 | 1.00 30.50 |
| ATOM | 3729 | C | ILE | B | 439 | 42.262 | -4.528 | 49.364 | 1.00 28.08 |
| ATOM | 3730 | O | ILE | B | 439 | 42.202 | -5.585 | 49.991 | 1.00 27.85 |
| ATOM | 3731 | N | PRO | B | 440 | 41.348 | -3.555 | 49.524 | 1.00 27.15 |
| ATOM | 3732 | CD | PRO | B | 440 | 41.258 | -2.301 | 48.760 | 1.00 25.90 |
| ATOM | 3733 | CA | PRO | B | 440 | 40.227 | -3.664 | 50.469 | 1.00 27.19 |
| ATOM | 3734 | CB | PRO | B | 440 | 39.389 | -2.434 | 50.134 | 1.00 27.25 |
| ATOM | 3735 | CG | PRO | B | 440 | 40.419 | -1.453 | 49.651 | 1.00 25.93 |
| ATOM | 3736 | C | PRO | B | 440 | 39.432 | -4.950 | 50.270 | 1.00 26.99 |
| ATOM | 3737 | O | PRO | B | 440 | 39.446 | -5.513 | 49.174 | 1.00 26.93 |
| ATOM | 3738 | N | TYR | B | 441 | 38.789 | -5.434 | 51.336 | 1.00 27.22 |
| ATOM | 3739 | CA | TYR | B | 441 | 37.983 | -6.661 | 51.286 | 1.00 27.75 |
| ATOM | 3740 | CB | TYR | B | 441 | 36.662 | -6.388 | 50.572 | 1.00 26.67 |
| ATOM | 3741 | CG | TYR | B | 441 | 35.879 | -5.238 | 51.156 | 1.00 25.96 |
| ATOM | 3742 | CD1 | TYR | B | 441 | 35.038 | -5.426 | 52.253 | 1.00 24.09 |
| ATOM | 3743 | CE1 | TYR | B | 441 | 34.318 | -4.377 | 52.782 | 1.00 23.77 |
| ATOM | 3744 | CD2 | TYR | B | 441 | 35.972 | -3.961 | 50.606 | 1.00 24.44 |
| ATOM | 3745 | CE2 | TYR | B | 441 | 35.250 | -2.897 | 51.135 | 1.00 24.12 |
| ATOM | 3746 | CZ | TYR | B | 441 | 34.428 | -3.111 | 52.218 | 1.00 23.52 |
| ATOM | 3747 | OH | TYR | B | 441 | 33.716 | -2.057 | 52.735 | 1.00 23.72 |
| ATOM | 3748 | C | TYR | B | 441 | 38.722 | -7.791 | 50.559 | 1.00 29.59 |
| ATOM | 3749 | O | TYR | B | 441 | 38.303 | -8.231 | 49.482 | 1.00 29.80 |
| ATOM | 3750 | N | PRO | B | 442 | 39.830 | -8.280 | 51.139 | 1.00 31.00 |
| ATOM | 3751 | CD | PRO | B | 442 | 40.383 | -7.969 | 52.473 | 1.00 31.64 |
| ATOM | 3752 | CA | PRO | B | 442 | 40.585 | -9.352 | 50.491 | 1.00 31.70 |
| ATOM | 3753 | CB | PRO | B | 442 | 41.757 | -9.561 | 51.453 | 1.00 32.72 |
| ATOM | 3754 | CG | PRO | B | 442 | 41.167 | -9.213 | 52.800 | 1.00 31.71 |
| ATOM | 3755 | C | PRO | B | 442 | 39.755 | -10.620 | 50.288 | 1.00 32.55 |
| ATOM | 3756 | O | PRO | B | 442 | 39.017 | -11.042 | 51.186 | 1.00 32.46 |
| ATOM | 3757 | N | GLY | B | 443 | 39.862 | -11.202 | 49.094 | 1.00 32.96 |
| ATOM | 3758 | CA | GLY | B | 443 | 39.123 | -12.413 | 48.781 | 1.00 33.36 |
| ATOM | 3759 | C | GLY | B | 443 | 37.624 | -12.213 | 48.601 | 1.00 33.93 |
| ATOM | 3760 | O | GLY | B | 443 | 36.811 | -13.065 | 48.974 | 1.00 35.09 |
| ATOM | 3761 | N | MET | B | 444 | 37.259 | -11.091 | 47.997 | 1.00 32.95 |
| ATOM | 3762 | CA | MET | B | 444 | 35.867 | -10.748 | 47.747 | 1.00 32.05 |
| ATOM | 3763 | CB | MET | B | 444 | 35.337 | -9.788 | 48.824 | 1.00 31.95 |
| ATOM | 3764 | CG | MET | B | 444 | 34.749 | -10.418 | 50.075 | 1.00 30.81 |
| ATOM | 3765 | SD | MET | B | 444 | 33.932 | -9.193 | 51.158 | 1.00 29.14 |
| ATOM | 3766 | CE | MET | B | 444 | 33.692 | -10.137 | 52.665 | 1.00 29.01 |
| ATOM | 3767 | C | MET | B | 444 | 35.856 | -10.011 | 46.424 | 1.00 32.14 |

Figure 5

| | | | | | | | | | |
|---|---|---|---|---|---|---|---|---|---|
| ATOM | 3768 | O | MET | B | 444 | 36.679 | -9.118 | 46.217 | 1.00 32.14 |
| ATOM | 3769 | N | THR | B | 445 | 34.957 | -10.384 | 45.521 | 1.00 32.25 |
| ATOM | 3770 | CA | THR | B | 445 | 34.878 | -9.683 | 44.239 | 1.00 32.74 |
| ATOM | 3771 | CB | THR | B | 445 | 34.294 | -10.567 | 43.113 | 1.00 32.97 |
| ATOM | 3772 | OG1 | THR | B | 445 | 32.980 | -11.013 | 43.475 | 1.00 33.29 |
| ATOM | 3773 | CG2 | THR | B | 445 | 35.190 | -11.772 | 42.865 | 1.00 33.74 |
| ATOM | 3774 | C | THR | B | 445 | 33.995 | -8.460 | 44.440 | 1.00 32.75 |
| ATOM | 3775 | O | THR | B | 445 | 33.506 | -8.218 | 45.541 | 1.00 33.62 |
| ATOM | 3776 | N | ASN | B | 446 | 33.793 | -7.682 | 43.387 | 1.00 32.90 |
| ATOM | 3777 | CA | ASN | B | 446 | 32.950 | -6.499 | 43.493 | 1.00 32.90 |
| ATOM | 3778 | CB | ASN | B | 446 | 33.002 | -5.654 | 42.207 | 1.00 34.38 |
| ATOM | 3779 | CG | ASN | B | 446 | 34.230 | -4.752 | 42.155 | 1.00 36.41 |
| ATOM | 3780 | OD1 | ASN | B | 446 | 35.114 | -4.842 | 43.015 | 1.00 38.19 |
| ATOM | 3781 | ND2 | ASN | B | 446 | 34.278 | -3.857 | 41.170 | 1.00 37.18 |
| ATOM | 3782 | C | ASN | B | 446 | 31.511 | -6.836 | 43.897 | 1.00 31.45 |
| ATOM | 3783 | O | ASN | B | 446 | 31.033 | -6.340 | 44.920 | 1.00 30.17 |
| ATOM | 3784 | N | PRO | B | 447 | 30.832 | -7.732 | 43.144 | 1.00 30.85 |
| ATOM | 3785 | CD | PRO | B | 447 | 31.284 | -8.470 | 41.948 | 1.00 31.01 |
| ATOM | 3786 | CA | PRO | B | 447 | 29.449 | -8.101 | 43.474 | 1.00 29.52 |
| ATOM | 3787 | CB | PRO | B | 447 | 29.066 | -9.067 | 42.342 | 1.00 29.66 |
| ATOM | 3788 | CG | PRO | B | 447 | 30.364 | -9.669 | 41.946 | 1.00 30.33 |
| ATOM | 3789 | C | PRO | B | 447 | 29.293 | -8.726 | 44.868 | 1.00 28.09 |
| ATOM | 3790 | O | PRO | B | 447 | 28.203 | -8.682 | 45.449 | 1.00 27.41 |
| ATOM | 3791 | N | GLU | B | 448 | 30.392 | -9.263 | 45.405 | 1.00 26.27 |
| ATOM | 3792 | CA | GLU | B | 448 | 30.405 | -9.871 | 46.735 | 1.00 24.86 |
| ATOM | 3793 | CB | GLU | B | 448 | 31.586 | -10.829 | 46.896 | 1.00 27.56 |
| ATOM | 3794 | CG | GLU | B | 448 | 31.394 | -12.156 | 46.173 | 1.00 31.42 |
| ATOM | 3795 | CD | GLU | B | 448 | 32.592 | -13.095 | 46.278 | 1.00 34.19 |
| ATOM | 3796 | OE1 | GLU | B | 448 | 33.531 | -12.827 | 47.057 | 1.00 35.85 |
| ATOM | 3797 | OE2 | GLU | B | 448 | 32.580 | -14.124 | 45.569 | 1.00 36.17 |
| ATOM | 3798 | C | GLU | B | 448 | 30.458 | -8.800 | 47.805 | 1.00 22.92 |
| ATOM | 3799 | O | GLU | B | 448 | 29.891 | -8.965 | 48.878 | 1.00 21.94 |
| ATOM | 3800 | N | VAL | B | 449 | 31.180 | -7.717 | 47.517 | 1.00 22.28 |
| ATOM | 3801 | CA | VAL | B | 449 | 31.284 | -6.576 | 48.423 | 1.00 20.31 |
| ATOM | 3802 | CB | VAL | B | 449 | 32.343 | -5.554 | 47.925 | 1.00 19.41 |
| ATOM | 3803 | CG1 | VAL | B | 449 | 32.210 | -4.219 | 48.669 | 1.00 17.83 |
| ATOM | 3804 | CG2 | VAL | B | 449 | 33.751 | -6.130 | 48.099 | 1.00 16.96 |
| ATOM | 3805 | C | VAL | B | 449 | 29.896 | -5.938 | 48.451 | 1.00 20.14 |
| ATOM | 3806 | O | VAL | B | 449 | 29.373 | -5.629 | 49.516 | 1.00 21.19 |
| ATOM | 3807 | N | ILE | B | 450 | 29.275 | -5.818 | 47.282 | 1.00 19.99 |
| ATOM | 3808 | CA | ILE | B | 450 | 27.932 | -5.255 | 47.162 | 1.00 20.16 |
| ATOM | 3809 | CB | ILE | B | 450 | 27.421 | -5.326 | 45.696 | 1.00 19.60 |
| ATOM | 3810 | CG2 | ILE | B | 450 | 25.991 | -4.776 | 45.592 | 1.00 18.69 |
| ATOM | 3811 | CG1 | ILE | B | 450 | 28.389 | -4.616 | 44.742 | 1.00 19.20 |
| ATOM | 3812 | CD1 | ILE | B | 450 | 28.191 | -3.150 | 44.602 | 1.00 19.48 |
| ATOM | 3813 | C | ILE | B | 450 | 26.945 | -6.023 | 48.058 | 1.00 21.02 |
| ATOM | 3814 | O | ILE | B | 450 | 26.246 | -5.423 | 48.878 | 1.00 21.36 |
| ATOM | 3815 | N | GLN | B | 451 | 26.931 | -7.350 | 47.947 | 1.00 21.87 |
| ATOM | 3816 | CA | GLN | B | 451 | 26.004 | -8.152 | 48.738 | 1.00 22.67 |
| ATOM | 3817 | CB | GLN | B | 451 | 25.765 | -9.540 | 48.113 | 1.00 25.06 |
| ATOM | 3818 | CG | GLN | B | 451 | 26.934 | -10.502 | 48.103 | 1.00 29.23 |
| ATOM | 3819 | CD | GLN | B | 451 | 26.812 | -11.554 | 46.994 | 1.00 32.99 |
| ATOM | 3820 | OE1 | GLN | B | 451 | 27.406 | -12.641 | 47.075 | 1.00 34.75 |
| ATOM | 3821 | NE2 | GLN | B | 451 | 26.074 | -11.216 | 45.928 | 1.00 33.95 |
| ATOM | 3822 | C | GLN | B | 451 | 26.309 | -8.242 | 50.222 | 1.00 21.29 |
| ATOM | 3823 | O | GLN | B | 451 | 25.434 | -8.584 | 51.016 | 1.00 22.11 |
| ATOM | 3824 | N | ASN | B | 452 | 27.535 | -7.894 | 50.599 | 1.00 20.42 |
| ATOM | 3825 | CA | ASN | B | 452 | 27.930 | -7.906 | 51.995 | 1.00 17.91 |
| ATOM | 3826 | CB | ASN | B | 452 | 29.424 | -8.103 | 52.131 | 1.00 17.01 |
| ATOM | 3827 | CG | ASN | B | 452 | 29.779 | -9.529 | 52.391 | 1.00 18.28 |

Figure 5

| ATOM | 3828 | OD1 | ASN | B | 452 | 29.775 | -9.998 | 53.540 | 1.00 | 17.74 |
|---|---|---|---|---|---|---|---|---|---|---|
| ATOM | 3829 | ND2 | ASN | B | 452 | 30.031 | -10.261 | 51.322 | 1.00 | 19.49 |
| ATOM | 3830 | C | ASN | B | 452 | 27.534 | -6.587 | 52.599 | 1.00 | 17.75 |
| ATOM | 3831 | O | ASN | B | 452 | 27.102 | -6.521 | 53.744 | 1.00 | 17.52 |
| ATOM | 3832 | N | LEU | B | 453 | 27.696 | -5.530 | 51.817 | 1.00 | 17.63 |
| ATOM | 3833 | CA | LEU | B | 453 | 27.338 | -4.199 | 52.257 | 1.00 | 17.27 |
| ATOM | 3834 | CB | LEU | B | 453 | 27.732 | -3.163 | 51.216 | 1.00 | 17.52 |
| ATOM | 3835 | CG | LEU | B | 453 | 29.213 | -2.836 | 51.133 | 1.00 | 19.45 |
| ATOM | 3836 | CD1 | LEU | B | 453 | 29.377 | -1.661 | 50.178 | 1.00 | 18.85 |
| ATOM | 3837 | CD2 | LEU | B | 453 | 29.761 | -2.489 | 52.531 | 1.00 | 20.06 |
| ATOM | 3838 | C | LEU | B | 453 | 25.852 | -4.113 | 52.496 | 1.00 | 17.49 |
| ATOM | 3839 | O | LEU | B | 453 | 25.415 | -3.381 | 53.365 | 1.00 | 17.45 |
| ATOM | 3840 | N | GLU | B | 454 | 25.062 | -4.808 | 51.684 | 1.00 | 18.00 |
| ATOM | 3841 | CA | GLU | B | 454 | 23.625 | -4.788 | 51.871 | 1.00 | 18.98 |
| ATOM | 3842 | CB | GLU | B | 454 | 22.933 | -5.697 | 50.877 | 1.00 | 24.08 |
| ATOM | 3843 | CG | GLU | B | 454 | 23.109 | -5.362 | 49.422 | 1.00 | 30.78 |
| ATOM | 3844 | CD | GLU | B | 454 | 22.432 | -6.405 | 48.528 | 1.00 | 35.58 |
| ATOM | 3845 | OE1 | GLU | B | 454 | 22.917 | -6.608 | 47.382 | 1.00 | 36.68 |
| ATOM | 3846 | OE2 | GLU | B | 454 | 21.423 | -7.025 | 48.983 | 1.00 | 36.73 |
| ATOM | 3847 | C | GLU | B | 454 | 23.300 | -5.300 | 53.262 | 1.00 | 17.34 |
| ATOM | 3848 | O | GLU | B | 454 | 22.414 | -4.790 | 53.911 | 1.00 | 17.75 |
| ATOM | 3849 | N | ARG | B | 455 | 24.029 | -6.326 | 53.689 | 1.00 | 17.01 |
| ATOM | 3850 | CA | ARG | B | 455 | 23.872 | -6.962 | 54.993 | 1.00 | 15.73 |
| ATOM | 3851 | CB | ARG | B | 455 | 24.362 | -8.420 | 54.914 | 1.00 | 16.77 |
| ATOM | 3852 | CG | ARG | B | 455 | 23.578 | -9.327 | 53.954 | 1.00 | 20.67 |
| ATOM | 3853 | CD | ARG | B | 455 | 24.105 | -10.778 | 53.983 | 1.00 | 23.27 |
| ATOM | 3854 | NE | ARG | B | 455 | 24.724 | -11.163 | 52.709 | 1.00 | 28.74 |
| ATOM | 3855 | CZ | ARG | B | 455 | 25.891 | -11.796 | 52.575 | 1.00 | 29.90 |
| ATOM | 3856 | NH1 | ARG | B | 455 | 26.607 | -12.139 | 53.637 | 1.00 | 32.24 |
| ATOM | 3857 | NH2 | ARG | B | 455 | 26.357 | -12.078 | 51.363 | 1.00 | 33.10 |
| ATOM | 3858 | C | ARG | B | 455 | 24.620 | -6.206 | 56.122 | 1.00 | 14.38 |
| ATOM | 3859 | O | ARG | B | 455 | 24.729 | -6.691 | 57.248 | 1.00 | 13.92 |
| ATOM | 3860 | N | GLY | B | 456 | 25.196 | -5.058 | 55.792 | 1.00 | 12.99 |
| ATOM | 3861 | CA | GLY | B | 456 | 25.894 | -4.251 | 56.779 | 1.00 | 12.03 |
| ATOM | 3862 | C | GLY | B | 456 | 27.292 | -4.662 | 57.176 | 1.00 | 11.91 |
| ATOM | 3863 | O | GLY | B | 456 | 27.753 | -4.337 | 58.267 | 1.00 | 13.01 |
| ATOM | 3864 | N | TYR | B | 457 | 27.981 | -5.352 | 56.281 | 1.00 | 11.48 |
| ATOM | 3865 | CA | TYR | B | 457 | 29.336 | -5.812 | 56.524 | 1.00 | 10.63 |
| ATOM | 3866 | CB | TYR | B | 457 | 29.750 | -6.746 | 55.385 | 1.00 | 9.77 |
| ATOM | 3867 | CG | TYR | B | 457 | 31.121 | -7.337 | 55.532 | 1.00 | 9.75 |
| ATOM | 3868 | CD1 | TYR | B | 457 | 31.336 | -8.462 | 56.330 | 1.00 | 8.54 |
| ATOM | 3869 | CE1 | TYR | B | 457 | 32.615 | -8.997 | 56.498 | 1.00 | 8.87 |
| ATOM | 3870 | CD2 | TYR | B | 457 | 32.222 | -6.751 | 54.897 | 1.00 | 11.26 |
| ATOM | 3871 | CE2 | TYR | B | 457 | 33.521 | -7.278 | 55.065 | 1.00 | 11.25 |
| ATOM | 3872 | CZ | TYR | B | 457 | 33.700 | -8.397 | 55.862 | 1.00 | 10.82 |
| ATOM | 3873 | OH | TYR | B | 457 | 34.972 | -8.901 | 56.014 | 1.00 | 12.13 |
| ATOM | 3874 | C | TYR | B | 457 | 30.356 | -4.685 | 56.651 | 1.00 | 11.09 |
| ATOM | 3875 | O | TYR | B | 457 | 30.279 | -3.680 | 55.946 | 1.00 | 11.86 |
| ATOM | 3876 | N | ARG | B | 458 | 31.282 | -4.846 | 57.597 | 1.00 | 12.01 |
| ATOM | 3877 | CA | ARG | B | 458 | 32.372 | -3.904 | 57.810 | 1.00 | 12.67 |
| ATOM | 3878 | CB | ARG | B | 458 | 32.168 | -3.042 | 59.048 | 1.00 | 10.84 |
| ATOM | 3879 | CG | ARG | B | 458 | 31.013 | -2.089 | 58.979 | 1.00 | 9.63 |
| ATOM | 3880 | CD | ARG | B | 458 | 31.106 | -1.123 | 57.813 | 1.00 | 9.14 |
| ATOM | 3881 | NE | ARG | B | 458 | 29.996 | -0.163 | 57.815 | 1.00 | 7.40 |
| ATOM | 3882 | CZ | ARG | B | 458 | 28.885 | -0.280 | 57.094 | 1.00 | 6.60 |
| ATOM | 3883 | NH1 | ARG | B | 458 | 28.698 | -1.319 | 56.294 | 1.00 | 6.30 |
| ATOM | 3884 | NH2 | ARG | B | 458 | 27.970 | 0.671 | 57.146 | 1.00 | 8.04 |
| ATOM | 3885 | C | ARG | B | 458 | 33.627 | -4.740 | 57.992 | 1.00 | 14.93 |
| ATOM | 3886 | O | ARG | B | 458 | 33.592 | -5.763 | 58.680 | 1.00 | 15.31 |
| ATOM | 3887 | N | MET | B | 459 | 34.702 | -4.348 | 57.313 | 1.00 | 16.21 |

Figure 5

| ATOM | 3888 | CA  | MET | B | 459 | 35.976 | -5.038 | 57.427 | 1.00 | 18.98 |
| ATOM | 3889 | CB  | MET | B | 459 | 37.046 | -4.288 | 56.658 | 1.00 | 19.26 |
| ATOM | 3890 | CG  | MET | B | 459 | 36.874 | -4.354 | 55.172 | 1.00 | 22.64 |
| ATOM | 3891 | SD  | MET | B | 459 | 38.375 | -3.783 | 54.361 | 1.00 | 24.27 |
| ATOM | 3892 | CE  | MET | B | 459 | 37.816 | -2.136 | 53.774 | 1.00 | 23.33 |
| ATOM | 3893 | C   | MET | B | 459 | 36.433 | -5.132 | 58.877 | 1.00 | 21.00 |
| ATOM | 3894 | O   | MET | B | 459 | 36.168 | -4.234 | 59.679 | 1.00 | 21.35 |
| ATOM | 3895 | N   | VAL | B | 460 | 37.134 | -6.213 | 59.213 | 1.00 | 22.92 |
| ATOM | 3896 | CA  | VAL | B | 460 | 37.632 | -6.387 | 60.581 | 1.00 | 24.75 |
| ATOM | 3897 | CB  | VAL | B | 460 | 37.888 | -7.887 | 60.906 | 1.00 | 24.19 |
| ATOM | 3898 | CG1 | VAL | B | 460 | 36.655 | -8.692 | 60.581 | 1.00 | 23.29 |
| ATOM | 3899 | CG2 | VAL | B | 460 | 39.093 | -8.423 | 60.126 | 1.00 | 22.57 |
| ATOM | 3900 | C   | VAL | B | 460 | 38.913 | -5.560 | 60.787 | 1.00 | 25.99 |
| ATOM | 3901 | O   | VAL | B | 460 | 39.433 | -4.977 | 59.831 | 1.00 | 25.69 |
| ATOM | 3902 | N   | ARG | B | 461 | 39.412 | -5.498 | 62.023 | 1.00 | 27.24 |
| ATOM | 3903 | CA  | ARG | B | 461 | 40.628 | -4.736 | 62.283 | 1.00 | 29.00 |
| ATOM | 3904 | CB  | ARG | B | 461 | 40.933 | -4.605 | 63.778 | 1.00 | 30.79 |
| ATOM | 3905 | CG  | ARG | B | 461 | 42.126 | -3.687 | 64.028 | 1.00 | 33.12 |
| ATOM | 3906 | CD  | ARG | B | 461 | 42.524 | -3.615 | 65.475 | 1.00 | 36.53 |
| ATOM | 3907 | NE  | ARG | B | 461 | 42.888 | -4.926 | 65.992 | 1.00 | 41.30 |
| ATOM | 3908 | CZ  | ARG | B | 461 | 42.943 | -5.228 | 67.286 | 1.00 | 44.60 |
| ATOM | 3909 | NH1 | ARG | B | 461 | 42.668 | -4.304 | 68.205 | 1.00 | 45.37 |
| ATOM | 3910 | NH2 | ARG | B | 461 | 43.218 | -6.471 | 67.665 | 1.00 | 45.43 |
| ATOM | 3911 | C   | ARG | B | 461 | 41.805 | -5.397 | 61.582 | 1.00 | 29.51 |
| ATOM | 3912 | O   | ARG | B | 461 | 42.071 | -6.587 | 61.770 | 1.00 | 29.05 |
| ATOM | 3913 | N   | PRO | B | 462 | 42.469 | -4.645 | 60.693 | 1.00 | 30.54 |
| ATOM | 3914 | CD  | PRO | B | 462 | 42.007 | -3.338 | 60.193 | 1.00 | 30.15 |
| ATOM | 3915 | CA  | PRO | B | 462 | 43.628 | -5.098 | 59.919 | 1.00 | 31.14 |
| ATOM | 3916 | CB  | PRO | B | 462 | 43.926 | -3.888 | 59.037 | 1.00 | 29.80 |
| ATOM | 3917 | CG  | PRO | B | 462 | 42.580 | -3.320 | 58.805 | 1.00 | 29.47 |
| ATOM | 3918 | C   | PRO | B | 462 | 44.831 | -5.428 | 60.793 | 1.00 | 31.99 |
| ATOM | 3919 | O   | PRO | B | 462 | 45.000 | -4.861 | 61.875 | 1.00 | 31.56 |
| ATOM | 3920 | N   | ASP | B | 463 | 45.671 | -6.343 | 60.316 | 1.00 | 33.12 |
| ATOM | 3921 | CA  | ASP | B | 463 | 46.868 | -6.708 | 61.057 | 1.00 | 34.25 |
| ATOM | 3922 | CB  | ASP | B | 463 | 47.593 | -7.878 | 60.373 | 1.00 | 34.23 |
| ATOM | 3923 | CG  | ASP | B | 463 | 46.771 | -9.175 | 60.386 | 1.00 | 34.49 |
| ATOM | 3924 | OD1 | ASP | B | 463 | 46.176 | -9.513 | 61.436 | 1.00 | 34.91 |
| ATOM | 3925 | OD2 | ASP | B | 463 | 46.716 | -9.862 | 59.343 | 1.00 | 33.86 |
| ATOM | 3926 | C   | ASP | B | 463 | 47.767 | -5.465 | 61.183 | 1.00 | 34.63 |
| ATOM | 3927 | O   | ASP | B | 463 | 47.944 | -4.709 | 60.220 | 1.00 | 33.69 |
| ATOM | 3928 | N   | ASN | B | 464 | 48.243 | -5.216 | 62.406 | 1.00 | 35.42 |
| ATOM | 3929 | CA  | ASN | B | 464 | 49.105 | -4.071 | 62.722 | 1.00 | 36.32 |
| ATOM | 3930 | CB  | ASN | B | 464 | 50.399 | -4.091 | 61.882 | 1.00 | 39.79 |
| ATOM | 3931 | CG  | ASN | B | 464 | 51.378 | -5.197 | 62.328 | 1.00 | 43.52 |
| ATOM | 3932 | OD1 | ASN | B | 464 | 52.038 | -5.082 | 63.378 | 1.00 | 43.83 |
| ATOM | 3933 | ND2 | ASN | B | 464 | 51.473 | -6.277 | 61.527 | 1.00 | 43.85 |
| ATOM | 3934 | C   | ASN | B | 464 | 48.383 | -2.730 | 62.578 | 1.00 | 35.10 |
| ATOM | 3935 | O   | ASN | B | 464 | 48.887 | -1.797 | 61.941 | 1.00 | 34.59 |
| ATOM | 3936 | N   | CYS | B | 465 | 47.208 | -2.647 | 63.201 | 1.00 | 33.38 |
| ATOM | 3937 | CA  | CYS | B | 465 | 46.376 | -1.442 | 63.171 | 1.00 | 31.10 |
| ATOM | 3938 | CB  | CYS | B | 465 | 45.258 | -1.597 | 62.136 | 1.00 | 28.11 |
| ATOM | 3939 | SG  | CYS | B | 465 | 44.080 | -0.243 | 62.113 | 1.00 | 23.45 |
| ATOM | 3940 | C   | CYS | B | 465 | 45.769 | -1.173 | 64.553 | 1.00 | 30.73 |
| ATOM | 3941 | O   | CYS | B | 465 | 45.010 | -1.991 | 65.077 | 1.00 | 32.08 |
| ATOM | 3942 | N   | PRO | B | 466 | 46.094 | -0.021 | 65.158 | 1.00 | 28.85 |
| ATOM | 3943 | CD  | PRO | B | 466 | 46.988 | 1.027  | 64.630 | 1.00 | 27.84 |
| ATOM | 3944 | CA  | PRO | B | 466 | 45.574 | 0.339  | 66.480 | 1.00 | 28.04 |
| ATOM | 3945 | CB  | PRO | B | 466 | 46.074 | 1.769  | 66.649 | 1.00 | 28.00 |
| ATOM | 3946 | CG  | PRO | B | 466 | 47.359 | 1.784  | 65.861 | 1.00 | 27.91 |
| ATOM | 3947 | C   | PRO | B | 466 | 44.044 | 0.273  | 66.559 | 1.00 | 28.24 |

Figure 5

| | | | | | | | | | |
|---|---|---|---|---|---|---|---|---|---|
|ATOM|3948|O|PRO|B|466|43.372|0.347|65.539|1.00 28.27|
|ATOM|3949|N|GLU|B|467|43.497|0.112|67.763|1.00 28.89|
|ATOM|3950|CA|GLU|B|467|42.042|0.062|67.937|1.00 29.40|
|ATOM|3951|CB|GLU|B|467|41.663|-0.511|69.295|1.00 30.71|
|ATOM|3952|CG|GLU|B|467|41.074|-1.914|69.238|1.00 33.46|
|ATOM|3953|CD|GLU|B|467|39.740|-1.983|68.528|1.00 34.89|
|ATOM|3954|OE1|GLU|B|467|39.569|-2.899|67.689|1.00 35.57|
|ATOM|3955|OE2|GLU|B|467|38.853|-1.151|68.838|1.00 36.00|
|ATOM|3956|C|GLU|B|467|41.402|1.437|67.797|1.00 28.86|
|ATOM|3957|O|GLU|B|467|40.256|1.553|67.368|1.00 29.42|
|ATOM|3958|N|GLU|B|468|42.125|2.472|68.201|1.00 27.54|
|ATOM|3959|CA|GLU|B|468|41.606|3.823|68.094|1.00 26.94|
|ATOM|3960|CB|GLU|B|468|42.524|4.825|68.794|1.00 29.54|
|ATOM|3961|CG|GLU|B|468|42.760|4.543|70.273|1.00 33.46|
|ATOM|3962|CD|GLU|B|468|43.704|3.355|70.522|1.00 34.95|
|ATOM|3963|OE1|GLU|B|468|44.655|3.154|69.720|1.00 33.69|
|ATOM|3964|OE2|GLU|B|468|43.491|2.631|71.527|1.00 35.47|
|ATOM|3965|C|GLU|B|468|41.517|4.154|66.616|1.00 25.15|
|ATOM|3966|O|GLU|B|468|40.594|4.855|66.191|1.00 25.08|
|ATOM|3967|N|LEU|B|469|42.468|3.621|65.837|1.00 22.62|
|ATOM|3968|CA|LEU|B|469|42.495|3.846|64.392|1.00 20.47|
|ATOM|3969|CB|LEU|B|469|43.883|3.585|63.795|1.00 18.36|
|ATOM|3970|CG|LEU|B|469|44.014|3.830|62.279|1.00 16.18|
|ATOM|3971|CD1|LEU|B|469|43.672|5.268|61.935|1.00 14.90|
|ATOM|3972|CD2|LEU|B|469|45.408|3.503|61.812|1.00 14.11|
|ATOM|3973|C|LEU|B|469|41.433|3.011|63.682|1.00 19.26|
|ATOM|3974|O|LEU|B|469|40.853|3.452|62.688|1.00 19.52|
|ATOM|3975|N|TYR|B|470|41.202|1.799|64.163|1.00 18.56|
|ATOM|3976|CA|TYR|B|470|40.168|0.974|63.577|1.00 18.63|
|ATOM|3977|CB|TYR|B|470|40.212|-0.464|64.090|1.00 18.05|
|ATOM|3978|CG|TYR|B|470|39.038|-1.294|63.611|1.00 17.77|
|ATOM|3979|CD1|TYR|B|470|38.843|-1.545|62.256|1.00 18.02|
|ATOM|3980|CE1|TYR|B|470|37.751|-2.318|61.808|1.00 19.12|
|ATOM|3981|CD2|TYR|B|470|38.117|-1.831|64.512|1.00 18.89|
|ATOM|3982|CE2|TYR|B|470|37.020|-2.609|64.071|1.00 18.67|
|ATOM|3983|CZ|TYR|B|470|36.848|-2.846|62.717|1.00 19.11|
|ATOM|3984|OH|TYR|B|470|35.781|-3.607|62.268|1.00 18.89|
|ATOM|3985|C|TYR|B|470|38.816|1.581|63.919|1.00 18.80|
|ATOM|3986|O|TYR|B|470|37.869|1.441|63.159|1.00 19.96|
|ATOM|3987|N|GLN|B|471|38.710|2.254|65.060|1.00 19.28|
|ATOM|3988|CA|GLN|B|471|37.431|2.855|65.431|1.00 18.24|
|ATOM|3989|CB|GLN|B|471|37.329|3.069|66.942|1.00 18.76|
|ATOM|3990|CG|GLN|B|471|37.038|1.781|67.726|1.00 18.35|
|ATOM|3991|CD|GLN|B|471|35.770|1.027|67.253|1.00 20.11|
|ATOM|3992|OE1|GLN|B|471|34.788|1.628|66.758|1.00 18.71|
|ATOM|3993|NE2|GLN|B|471|35.787|-0.295|67.427|1.00 19.44|
|ATOM|3994|C|GLN|B|471|37.135|4.122|64.651|1.00 17.49|
|ATOM|3995|O|GLN|B|471|35.984|4.502|64.481|1.00 17.84|
|ATOM|3996|N|LEU|B|472|38.187|4.753|64.146|1.00 17.75|
|ATOM|3997|CA|LEU|B|472|38.050|5.953|63.339|1.00 16.87|
|ATOM|3998|CB|LEU|B|472|39.408|6.599|63.157|1.00 18.53|
|ATOM|3999|CG|LEU|B|472|39.439|8.112|63.335|1.00 20.72|
|ATOM|4000|CD1|LEU|B|472|38.826|8.526|64.690|1.00 20.13|
|ATOM|4001|CD2|LEU|B|472|40.897|8.555|63.226|1.00 22.06|
|ATOM|4002|C|LEU|B|472|37.503|5.526|61.982|1.00 15.90|
|ATOM|4003|O|LEU|B|472|36.656|6.212|61.402|1.00 16.20|
|ATOM|4004|N|MET|B|473|38.018|4.404|61.474|1.00 13.87|
|ATOM|4005|CA|MET|B|473|37.564|3.828|60.203|1.00 13.28|
|ATOM|4006|CB|MET|B|473|38.281|2.520|59.922|1.00 11.99|
|ATOM|4007|CG|MET|B|473|39.742|2.617|59.704|1.00 9.50|

Figure 5

| | | | | | | | | | |
|---|---|---|---|---|---|---|---|---|---|
| ATOM | 4008 | SD | MET | B | 473 | 40.362 | 0.948 | 59.675 | 1.00 11.27 |
| ATOM | 4009 | CE | MET | B | 473 | 42.152 | 1.260 | 59.489 | 1.00  4.99 |
| ATOM | 4010 | C | MET | B | 473 | 36.079 | 3.491 | 60.308 | 1.00 13.94 |
| ATOM | 4011 | O | MET | B | 473 | 35.293 | 3.762 | 59.398 | 1.00 13.30 |
| ATOM | 4012 | N | ARG | B | 474 | 35.718 | 2.859 | 61.420 | 1.00 14.65 |
| ATOM | 4013 | CA | ARG | B | 474 | 34.345 | 2.481 | 61.682 | 1.00 15.50 |
| ATOM | 4014 | CB | ARG | B | 474 | 34.249 | 1.764 | 63.018 | 1.00 14.79 |
| ATOM | 4015 | CG | ARG | B | 474 | 34.896 | 0.406 | 62.987 | 1.00 15.77 |
| ATOM | 4016 | CD | ARG | B | 474 | 34.253 | -0.477 | 61.923 | 1.00 17.21 |
| ATOM | 4017 | NE | ARG | B | 474 | 32.835 | -0.734 | 62.194 | 1.00 18.81 |
| ATOM | 4018 | CZ | ARG | B | 474 | 32.353 | -1.869 | 62.702 | 1.00 17.10 |
| ATOM | 4019 | NH1 | ARG | B | 474 | 33.170 | -2.870 | 63.009 | 1.00 15.43 |
| ATOM | 4020 | NH2 | ARG | B | 474 | 31.043 | -2.024 | 62.839 | 1.00 15.40 |
| ATOM | 4021 | C | ARG | B | 474 | 33.424 | 3.689 | 61.660 | 1.00 16.68 |
| ATOM | 4022 | O | ARG | B | 474 | 32.258 | 3.579 | 61.250 | 1.00 18.48 |
| ATOM | 4023 | N | LEU | B | 475 | 33.945 | 4.846 | 62.076 | 1.00 16.47 |
| ATOM | 4024 | CA | LEU | B | 475 | 33.143 | 6.064 | 62.076 | 1.00 15.35 |
| ATOM | 4025 | CB | LEU | B | 475 | 33.713 | 7.130 | 63.034 | 1.00 15.37 |
| ATOM | 4026 | CG | LEU | B | 475 | 33.421 | 6.847 | 64.531 | 1.00 15.03 |
| ATOM | 4027 | CD1 | LEU | B | 475 | 34.109 | 7.835 | 65.472 | 1.00 11.34 |
| ATOM | 4028 | CD2 | LEU | B | 475 | 31.915 | 6.863 | 64.749 | 1.00 14.58 |
| ATOM | 4029 | C | LEU | B | 475 | 33.024 | 6.560 | 60.650 | 1.00 14.32 |
| ATOM | 4030 | O | LEU | B | 475 | 32.009 | 7.119 | 60.278 | 1.00 14.84 |
| ATOM | 4031 | N | CYS | B | 476 | 34.032 | 6.289 | 59.830 | 1.00 13.73 |
| ATOM | 4032 | CA | CYS | B | 476 | 33.996 | 6.697 | 58.423 | 1.00 12.85 |
| ATOM | 4033 | CB | CYS | B | 476 | 35.359 | 6.506 | 57.755 | 1.00 12.07 |
| ATOM | 4034 | SG | CYS | B | 476 | 36.683 | 7.585 | 58.355 | 1.00 12.45 |
| ATOM | 4035 | C | CYS | B | 476 | 32.985 | 5.843 | 57.694 | 1.00 12.78 |
| ATOM | 4036 | O | CYS | B | 476 | 32.364 | 6.300 | 56.749 | 1.00 13.37 |
| ATOM | 4037 | N | TRP | B | 477 | 32.797 | 4.613 | 58.168 | 1.00 12.99 |
| ATOM | 4038 | CA | TRP | B | 477 | 31.879 | 3.663 | 57.548 | 1.00 13.56 |
| ATOM | 4039 | CB | TRP | B | 477 | 32.480 | 2.249 | 57.575 | 1.00 12.56 |
| ATOM | 4040 | CG | TRP | B | 477 | 33.809 | 2.136 | 56.929 | 1.00 10.27 |
| ATOM | 4041 | CD2 | TRP | B | 477 | 34.836 | 1.208 | 57.257 | 1.00 11.06 |
| ATOM | 4042 | CE2 | TRP | B | 477 | 35.947 | 1.513 | 56.435 | 1.00 10.92 |
| ATOM | 4043 | CE3 | TRP | B | 477 | 34.938 | 0.150 | 58.173 | 1.00 11.11 |
| ATOM | 4044 | CD1 | TRP | B | 477 | 34.312 | 2.933 | 55.942 | 1.00 10.18 |
| ATOM | 4045 | NE1 | TRP | B | 477 | 35.590 | 2.569 | 55.640 | 1.00  9.69 |
| ATOM | 4046 | CZ2 | TRP | B | 477 | 37.157 | 0.797 | 56.502 | 1.00 10.26 |
| ATOM | 4047 | CZ3 | TRP | B | 477 | 36.146 | -0.563 | 58.240 | 1.00  9.84 |
| ATOM | 4048 | CH2 | TRP | B | 477 | 37.237 | -0.232 | 57.407 | 1.00  9.76 |
| ATOM | 4049 | C | TRP | B | 477 | 30.467 | 3.585 | 58.129 | 1.00 15.45 |
| ATOM | 4050 | O | TRP | B | 477 | 29.815 | 2.540 | 58.010 | 1.00 16.40 |
| ATOM | 4051 | N | LYS | B | 478 | 29.979 | 4.651 | 58.754 | 1.00 15.81 |
| ATOM | 4052 | CA | LYS | B | 478 | 28.628 | 4.609 | 59.300 | 1.00 16.59 |
| ATOM | 4053 | CB | LYS | B | 478 | 28.357 | 5.797 | 60.225 | 1.00 17.26 |
| ATOM | 4054 | CG | LYS | B | 478 | 29.215 | 5.834 | 61.513 | 1.00 19.61 |
| ATOM | 4055 | CD | LYS | B | 478 | 28.874 | 4.727 | 62.525 | 1.00 20.03 |
| ATOM | 4056 | CE | LYS | B | 478 | 27.497 | 4.931 | 63.154 | 1.00 21.20 |
| ATOM | 4057 | NZ | LYS | B | 478 | 27.090 | 3.759 | 63.977 | 1.00 23.30 |
| ATOM | 4058 | C | LYS | B | 478 | 27.676 | 4.601 | 58.115 | 1.00 17.05 |
| ATOM | 4059 | O | LYS | B | 478 | 27.940 | 5.230 | 57.108 | 1.00 17.76 |
| ATOM | 4060 | N | GLU | B | 479 | 26.597 | 3.841 | 58.220 | 1.00 18.01 |
| ATOM | 4061 | CA | GLU | B | 479 | 25.625 | 3.714 | 57.140 | 1.00 18.73 |
| ATOM | 4062 | CB | GLU | B | 479 | 24.528 | 2.731 | 57.574 | 1.00 18.95 |
| ATOM | 4063 | CG | GLU | B | 479 | 23.510 | 2.351 | 56.492 | 1.00 19.82 |
| ATOM | 4064 | CD | GLU | B | 479 | 24.113 | 1.565 | 55.329 | 1.00 20.13 |
| ATOM | 4065 | OE1 | GLU | B | 479 | 25.040 | 0.754 | 55.572 | 1.00 20.31 |
| ATOM | 4066 | OE2 | GLU | B | 479 | 23.643 | 1.754 | 54.180 | 1.00 19.40 |
| ATOM | 4067 | C | GLU | B | 479 | 25.026 | 5.046 | 56.661 | 1.00 18.91 |

Figure 5

| | | | | | | | | |
|---|---|---|---|---|---|---|---|---|
| ATOM | 4068 | O | GLU | B | 479 | 24.857 | 5.279 | 55.454 | 1.00 | 19.61 |
| ATOM | 4069 | N | ARG | B | 480 | 24.686 | 5.906 | 57.611 | 1.00 | 19.32 |
| ATOM | 4070 | CA | ARG | B | 480 | 24.120 | 7.216 | 57.303 | 1.00 | 18.30 |
| ATOM | 4071 | CB | ARG | B | 480 | 23.233 | 7.675 | 58.452 | 1.00 | 20.49 |
| ATOM | 4072 | CG | ARG | B | 480 | 21.999 | 6.861 | 58.631 | 1.00 | 23.34 |
| ATOM | 4073 | CD | ARG | B | 480 | 21.508 | 7.093 | 60.011 | 1.00 | 29.25 |
| ATOM | 4074 | NE | ARG | B | 480 | 20.152 | 6.606 | 60.217 | 1.00 | 34.60 |
| ATOM | 4075 | CZ | ARG | B | 480 | 19.534 | 6.614 | 61.394 | 1.00 | 37.70 |
| ATOM | 4076 | NH1 | ARG | B | 480 | 20.149 | 7.086 | 62.479 | 1.00 | 39.53 |
| ATOM | 4077 | NH2 | ARG | B | 480 | 18.316 | 6.115 | 61.492 | 1.00 | 39.69 |
| ATOM | 4078 | C | ARG | B | 480 | 25.253 | 8.205 | 57.104 | 1.00 | 16.06 |
| ATOM | 4079 | O | ARG | B | 480 | 26.096 | 8.367 | 57.976 | 1.00 | 15.41 |
| ATOM | 4080 | N | PRO | B | 481 | 25.232 | 8.951 | 55.994 | 1.00 | 14.79 |
| ATOM | 4081 | CD | PRO | B | 481 | 24.159 | 9.127 | 54.995 | 1.00 | 13.81 |
| ATOM | 4082 | CA | PRO | B | 481 | 26.313 | 9.905 | 55.764 | 1.00 | 13.45 |
| ATOM | 4083 | CB | PRO | B | 481 | 25.884 | 10.606 | 54.468 | 1.00 | 13.21 |
| ATOM | 4084 | CG | PRO | B | 481 | 24.906 | 9.658 | 53.828 | 1.00 | 13.16 |
| ATOM | 4085 | C | PRO | B | 481 | 26.479 | 10.917 | 56.875 | 1.00 | 13.35 |
| ATOM | 4086 | O | PRO | B | 481 | 27.574 | 11.407 | 57.097 | 1.00 | 14.29 |
| ATOM | 4087 | N | GLU | B | 482 | 25.394 | 11.217 | 57.579 | 1.00 | 13.75 |
| ATOM | 4088 | CA | GLU | B | 482 | 25.400 | 12.223 | 58.637 | 1.00 | 14.27 |
| ATOM | 4089 | CB | GLU | B | 482 | 23.956 | 12.625 | 58.985 | 1.00 | 15.76 |
| ATOM | 4090 | CG | GLU | B | 482 | 23.142 | 11.535 | 59.720 | 1.00 | 17.97 |
| ATOM | 4091 | CD | GLU | B | 482 | 22.030 | 10.901 | 58.874 | 1.00 | 18.75 |
| ATOM | 4092 | OE1 | GLU | B | 482 | 22.179 | 10.801 | 57.637 | 1.00 | 17.56 |
| ATOM | 4093 | OE2 | GLU | B | 482 | 20.996 | 10.494 | 59.463 | 1.00 | 20.01 |
| ATOM | 4094 | C | GLU | B | 482 | 26.146 | 11.841 | 59.910 | 1.00 | 15.01 |
| ATOM | 4095 | O | GLU | B | 482 | 26.568 | 12.712 | 60.667 | 1.00 | 16.26 |
| ATOM | 4096 | N | ASP | B | 483 | 26.317 | 10.540 | 60.141 | 1.00 | 15.14 |
| ATOM | 4097 | CA | ASP | B | 483 | 26.981 | 10.038 | 61.341 | 1.00 | 14.20 |
| ATOM | 4098 | CB | ASP | B | 483 | 26.355 | 8.704 | 61.786 | 1.00 | 14.94 |
| ATOM | 4099 | CG | ASP | B | 483 | 24.877 | 8.827 | 62.196 | 1.00 | 14.77 |
| ATOM | 4100 | OD1 | ASP | B | 483 | 24.465 | 9.869 | 62.739 | 1.00 | 16.72 |
| ATOM | 4101 | OD2 | ASP | B | 483 | 24.126 | 7.850 | 61.998 | 1.00 | 17.30 |
| ATOM | 4102 | C | ASP | B | 483 | 28.485 | 9.869 | 61.174 | 1.00 | 13.56 |
| ATOM | 4103 | O | ASP | B | 483 | 29.175 | 9.485 | 62.129 | 1.00 | 14.01 |
| ATOM | 4104 | N | ARG | B | 484 | 28.972 | 10.134 | 59.959 | 1.00 | 12.65 |
| ATOM | 4105 | CA | ARG | B | 484 | 30.399 | 10.042 | 59.613 | 1.00 | 11.64 |
| ATOM | 4106 | CB | ARG | B | 484 | 30.565 | 9.756 | 58.112 | 1.00 | 10.26 |
| ATOM | 4107 | CG | ARG | B | 484 | 29.787 | 8.551 | 57.604 | 1.00 | 8.86 |
| ATOM | 4108 | CD | ARG | B | 484 | 30.000 | 8.297 | 56.103 | 1.00 | 7.20 |
| ATOM | 4109 | NE | ARG | B | 484 | 29.140 | 7.213 | 55.639 | 1.00 | 9.15 |
| ATOM | 4110 | CZ | ARG | B | 484 | 28.516 | 7.171 | 54.461 | 1.00 | 9.46 |
| ATOM | 4111 | NH1 | ARG | B | 484 | 28.652 | 8.159 | 53.587 | 1.00 | 10.79 |
| ATOM | 4112 | NH2 | ARG | B | 484 | 27.713 | 6.154 | 54.169 | 1.00 | 7.17 |
| ATOM | 4113 | C | ARG | B | 484 | 31.092 | 11.378 | 59.964 | 1.00 | 11.85 |
| ATOM | 4114 | O | ARG | B | 484 | 30.530 | 12.453 | 59.741 | 1.00 | 11.30 |
| ATOM | 4115 | N | PRO | B | 485 | 32.354 | 11.334 | 60.429 | 1.00 | 12.10 |
| ATOM | 4116 | CD | PRO | B | 485 | 33.256 | 10.179 | 60.562 | 1.00 | 10.97 |
| ATOM | 4117 | CA | PRO | B | 485 | 33.052 | 12.579 | 60.787 | 1.00 | 12.69 |
| ATOM | 4118 | CB | PRO | B | 485 | 34.400 | 12.075 | 61.333 | 1.00 | 12.94 |
| ATOM | 4119 | CG | PRO | B | 485 | 34.163 | 10.633 | 61.660 | 1.00 | 12.15 |
| ATOM | 4120 | C | PRO | B | 485 | 33.284 | 13.563 | 59.634 | 1.00 | 13.49 |
| ATOM | 4121 | O | PRO | B | 485 | 33.106 | 13.227 | 58.469 | 1.00 | 14.29 |
| ATOM | 4122 | N | THR | B | 486 | 33.598 | 14.807 | 59.978 | 1.00 | 13.28 |
| ATOM | 4123 | CA | THR | B | 486 | 33.933 | 15.811 | 58.986 | 1.00 | 12.67 |
| ATOM | 4124 | CB | THR | B | 486 | 33.723 | 17.253 | 59.530 | 1.00 | 11.90 |
| ATOM | 4125 | OG1 | THR | B | 486 | 34.422 | 17.425 | 60.773 | 1.00 | 11.75 |
| ATOM | 4126 | CG2 | THR | B | 486 | 32.253 | 17.535 | 59.732 | 1.00 | 11.89 |
| ATOM | 4127 | C | THR | B | 486 | 35.431 | 15.536 | 58.809 | 1.00 | 13.83 |

Figure 5

| | | | | | | | | | |
|---|---|---|---|---|---|---|---|---|---|
| ATOM | 4128 | O | THR | B | 486 | 36.032 | 14.900 | 59.682 | 1.00 14.88 |
| ATOM | 4129 | N | PHE | B | 487 | 36.022 | 15.922 | 57.675 | 1.00 13.95 |
| ATOM | 4130 | CA | PHE | B | 487 | 37.456 | 15.706 | 57.451 | 1.00 13.61 |
| ATOM | 4131 | CB | PHE | B | 487 | 37.842 | 15.992 | 56.006 | 1.00 12.04 |
| ATOM | 4132 | CG | PHE | B | 487 | 37.680 | 14.815 | 55.093 | 1.00 11.23 |
| ATOM | 4133 | CD1 | PHE | B | 487 | 38.531 | 13.727 | 55.186 | 1.00  8.64 |
| ATOM | 4134 | CD2 | PHE | B | 487 | 36.696 | 14.814 | 54.097 | 1.00 11.80 |
| ATOM | 4135 | CE1 | PHE | B | 487 | 38.418 | 12.661 | 54.302 | 1.00  8.02 |
| ATOM | 4136 | CE2 | PHE | B | 487 | 36.579 | 13.752 | 53.211 | 1.00  8.67 |
| ATOM | 4137 | CZ | PHE | B | 487 | 37.447 | 12.675 | 53.316 | 1.00  9.24 |
| ATOM | 4138 | C | PHE | B | 487 | 38.230 | 16.622 | 58.391 | 1.00 15.50 |
| ATOM | 4139 | O | PHE | B | 487 | 39.353 | 16.321 | 58.785 | 1.00 16.30 |
| ATOM | 4140 | N | ASP | B | 488 | 37.616 | 17.747 | 58.737 | 1.00 16.50 |
| ATOM | 4141 | CA | ASP | B | 488 | 38.197 | 18.686 | 59.669 | 1.00 18.64 |
| ATOM | 4142 | CB | ASP | B | 488 | 37.193 | 19.810 | 59.948 | 1.00 22.06 |
| ATOM | 4143 | CG | ASP | B | 488 | 37.710 | 20.845 | 60.951 | 1.00 24.60 |
| ATOM | 4144 | OD1 | ASP | B | 488 | 38.953 | 21.014 | 61.074 | 1.00 25.57 |
| ATOM | 4145 | OD2 | ASP | B | 488 | 36.856 | 21.495 | 61.612 | 1.00 25.07 |
| ATOM | 4146 | C | ASP | B | 488 | 38.519 | 17.922 | 60.954 | 1.00 19.57 |
| ATOM | 4147 | O | ASP | B | 488 | 39.583 | 18.101 | 61.540 | 1.00 21.40 |
| ATOM | 4148 | N | TYR | B | 489 | 37.626 | 17.021 | 61.356 | 1.00 19.91 |
| ATOM | 4149 | CA | TYR | B | 489 | 37.836 | 16.222 | 62.558 | 1.00 19.05 |
| ATOM | 4150 | CB | TYR | B | 489 | 36.514 | 15.607 | 63.029 | 1.00 18.20 |
| ATOM | 4151 | CG | TYR | B | 489 | 36.692 | 14.598 | 64.142 | 1.00 18.87 |
| ATOM | 4152 | CD1 | TYR | B | 489 | 36.980 | 15.001 | 65.447 | 1.00 19.25 |
| ATOM | 4153 | CE1 | TYR | B | 489 | 37.207 | 14.062 | 66.457 | 1.00 19.27 |
| ATOM | 4154 | CD2 | TYR | B | 489 | 36.630 | 13.232 | 63.879 | 1.00 19.18 |
| ATOM | 4155 | CE2 | TYR | B | 489 | 36.851 | 12.294 | 64.867 | 1.00 18.18 |
| ATOM | 4156 | CZ | TYR | B | 489 | 37.139 | 12.704 | 66.151 | 1.00 19.53 |
| ATOM | 4157 | OH | TYR | B | 489 | 37.359 | 11.748 | 67.124 | 1.00 20.54 |
| ATOM | 4158 | C | TYR | B | 489 | 38.890 | 15.128 | 62.361 | 1.00 19.17 |
| ATOM | 4159 | O | TYR | B | 489 | 39.747 | 14.911 | 63.225 | 1.00 19.33 |
| ATOM | 4160 | N | LEU | B | 490 | 38.803 | 14.426 | 61.235 | 1.00 19.23 |
| ATOM | 4161 | CA | LEU | B | 490 | 39.732 | 13.353 | 60.899 | 1.00 18.68 |
| ATOM | 4162 | CB | LEU | B | 490 | 39.398 | 12.780 | 59.516 | 1.00 16.22 |
| ATOM | 4163 | CG | LEU | B | 490 | 38.176 | 11.851 | 59.492 | 1.00 13.94 |
| ATOM | 4164 | CD1 | LEU | B | 490 | 37.722 | 11.557 | 58.087 | 1.00 10.31 |
| ATOM | 4165 | CD2 | LEU | B | 490 | 38.529 | 10.569 | 60.204 | 1.00 13.71 |
| ATOM | 4166 | C | LEU | B | 490 | 41.172 | 13.838 | 60.932 | 1.00 21.13 |
| ATOM | 4167 | O | LEU | B | 490 | 42.044 | 13.148 | 61.462 | 1.00 22.40 |
| ATOM | 4168 | N | ARG | B | 491 | 41.417 | 15.027 | 60.375 | 1.00 22.63 |
| ATOM | 4169 | CA | ARG | B | 491 | 42.750 | 15.622 | 60.349 | 1.00 24.30 |
| ATOM | 4170 | CB | ARG | B | 491 | 42.716 | 16.946 | 59.584 | 1.00 25.91 |
| ATOM | 4171 | CG | ARG | B | 491 | 43.999 | 17.779 | 59.745 | 1.00 29.85 |
| ATOM | 4172 | CD | ARG | B | 491 | 43.782 | 19.269 | 59.466 | 1.00 31.83 |
| ATOM | 4173 | NE | ARG | B | 491 | 42.655 | 19.800 | 60.234 | 1.00 34.22 |
| ATOM | 4174 | CZ | ARG | B | 491 | 42.717 | 20.182 | 61.509 | 1.00 34.71 |
| ATOM | 4175 | NH1 | ARG | B | 491 | 43.859 | 20.101 | 62.192 | 1.00 32.96 |
| ATOM | 4176 | NH2 | ARG | B | 491 | 41.625 | 20.660 | 62.098 | 1.00 35.20 |
| ATOM | 4177 | C | ARG | B | 491 | 43.256 | 15.881 | 61.778 | 1.00 25.51 |
| ATOM | 4178 | O | ARG | B | 491 | 44.424 | 15.643 | 62.090 | 1.00 25.87 |
| ATOM | 4179 | N | SER | B | 492 | 42.365 | 16.410 | 62.618 | 1.00 26.28 |
| ATOM | 4180 | CA | SER | B | 492 | 42.649 | 16.728 | 64.015 | 1.00 26.24 |
| ATOM | 4181 | CB | SER | B | 492 | 41.411 | 17.327 | 64.683 | 1.00 27.28 |
| ATOM | 4182 | OG | SER | B | 492 | 41.151 | 18.634 | 64.218 | 1.00 29.20 |
| ATOM | 4183 | C | SER | B | 492 | 43.088 | 15.524 | 64.826 | 1.00 26.29 |
| ATOM | 4184 | O | SER | B | 492 | 44.104 | 15.568 | 65.512 | 1.00 26.65 |
| ATOM | 4185 | N | VAL | B | 493 | 42.298 | 14.456 | 64.788 | 1.00 26.01 |
| ATOM | 4186 | CA | VAL | B | 493 | 42.648 | 13.272 | 65.554 | 1.00 25.65 |
| ATOM | 4187 | CB | VAL | B | 493 | 41.435 | 12.330 | 65.765 | 1.00 25.37 |

Figure 5

| | | | | | | | | |
|---|---|---|---|---|---|---|---|---|
| ATOM | 4188 | CG1 | VAL | B | 493 | 40.799 | 11.974 | 64.454 | 1.00 25.90 |
| ATOM | 4189 | CG2 | VAL | B | 493 | 41.867 | 11.079 | 66.513 | 1.00 25.20 |
| ATOM | 4190 | C | VAL | B | 493 | 43.858 | 12.557 | 64.971 | 1.00 25.53 |
| ATOM | 4191 | O | VAL | B | 493 | 44.669 | 11.996 | 65.711 | 1.00 25.30 |
| ATOM | 4192 | N | LEU | B | 494 | 44.028 | 12.662 | 63.652 | 1.00 26.54 |
| ATOM | 4193 | CA | LEU | B | 494 | 45.160 | 12.037 | 62.971 | 1.00 26.12 |
| ATOM | 4194 | CB | LEU | B | 494 | 44.909 | 11.945 | 61.467 | 1.00 24.07 |
| ATOM | 4195 | CG | LEU | B | 494 | 43.917 | 10.841 | 61.086 | 1.00 23.83 |
| ATOM | 4196 | CD1 | LEU | B | 494 | 43.610 | 10.833 | 59.593 | 1.00 20.97 |
| ATOM | 4197 | CD2 | LEU | B | 494 | 44.467 | 9.497 | 61.549 | 1.00 22.35 |
| ATOM | 4198 | C | LEU | B | 494 | 46.487 | 12.728 | 63.267 | 1.00 26.73 |
| ATOM | 4199 | O | LEU | B | 494 | 47.496 | 12.055 | 63.447 | 1.00 26.31 |
| ATOM | 4200 | N | GLU | B | 495 | 46.479 | 14.055 | 63.365 | 1.00 28.36 |
| ATOM | 4201 | CA | GLU | B | 495 | 47.698 | 14.813 | 63.661 | 1.00 31.84 |
| ATOM | 4202 | CB | GLU | B | 495 | 47.448 | 16.312 | 63.512 | 1.00 31.85 |
| ATOM | 4203 | CG | GLU | B | 495 | 47.220 | 16.772 | 62.091 | 1.00 33.22 |
| ATOM | 4204 | CD | GLU | B | 495 | 47.026 | 18.271 | 61.965 | 1.00 34.86 |
| ATOM | 4205 | OE1 | GLU | B | 495 | 46.991 | 18.978 | 63.006 | 1.00 34.99 |
| ATOM | 4206 | OE2 | GLU | B | 495 | 46.904 | 18.735 | 60.801 | 1.00 34.67 |
| ATOM | 4207 | C | GLU | B | 495 | 48.190 | 14.546 | 65.078 | 1.00 34.45 |
| ATOM | 4208 | O | GLU | B | 495 | 49.378 | 14.308 | 65.304 | 1.00 34.68 |
| ATOM | 4209 | N | ASP | B | 496 | 47.254 | 14.606 | 66.026 | 1.00 37.81 |
| ATOM | 4210 | CA | ASP | B | 496 | 47.528 | 14.390 | 67.448 | 1.00 40.34 |
| ATOM | 4211 | CB | ASP | B | 496 | 46.523 | 15.177 | 68.321 | 1.00 41.67 |
| ATOM | 4212 | CG | ASP | B | 496 | 46.423 | 16.665 | 67.964 | 1.00 44.24 |
| ATOM | 4213 | OD1 | ASP | B | 496 | 47.469 | 17.360 | 67.898 | 1.00 45.15 |
| ATOM | 4214 | OD2 | ASP | B | 496 | 45.271 | 17.150 | 67.806 | 1.00 44.77 |
| ATOM | 4215 | C | ASP | B | 496 | 47.396 | 12.915 | 67.848 | 1.00 41.66 |
| ATOM | 4216 | O | ASP | B | 496 | 47.195 | 12.620 | 69.024 | 1.00 42.33 |
| ATOM | 4217 | N | PHE | B | 497 | 47.554 | 11.982 | 66.915 | 1.00 42.71 |
| ATOM | 4218 | CA | PHE | B | 497 | 47.363 | 10.582 | 67.273 | 1.00 43.71 |
| ATOM | 4219 | CB | PHE | B | 497 | 47.484 | 9.659 | 66.060 | 1.00 42.48 |
| ATOM | 4220 | CG | PHE | B | 497 | 46.758 | 8.352 | 66.235 | 1.00 41.03 |
| ATOM | 4221 | CD1 | PHE | B | 497 | 45.395 | 8.258 | 65.975 | 1.00 38.96 |
| ATOM | 4222 | CD2 | PHE | B | 497 | 47.432 | 7.224 | 66.712 | 1.00 40.05 |
| ATOM | 4223 | CE1 | PHE | B | 497 | 44.715 | 7.064 | 66.188 | 1.00 38.63 |
| ATOM | 4224 | CE2 | PHE | B | 497 | 46.762 | 6.027 | 66.927 | 1.00 39.63 |
| ATOM | 4225 | CZ | PHE | B | 497 | 45.400 | 5.945 | 66.666 | 1.00 38.50 |
| ATOM | 4226 | C | PHE | B | 497 | 48.164 | 10.057 | 68.470 | 1.00 45.10 |
| ATOM | 4227 | O | PHE | B | 497 | 47.621 | 9.307 | 69.282 | 1.00 45.52 |
| ATOM | 4228 | N | PHE | B | 498 | 49.439 | 10.425 | 68.579 | 1.00 46.76 |
| ATOM | 4229 | CA | PHE | B | 498 | 50.267 | 10.001 | 69.721 | 1.00 48.40 |
| ATOM | 4230 | CB | PHE | B | 498 | 50.563 | 8.479 | 69.728 | 1.00 49.21 |
| ATOM | 4231 | CG | PHE | B | 498 | 50.942 | 7.883 | 68.375 | 1.00 49.45 |
| ATOM | 4232 | CD1 | PHE | B | 498 | 51.677 | 8.604 | 67.433 | 1.00 49.14 |
| ATOM | 4233 | CD2 | PHE | B | 498 | 50.560 | 6.571 | 68.064 | 1.00 49.15 |
| ATOM | 4234 | CE1 | PHE | B | 498 | 52.016 | 8.028 | 66.211 | 1.00 49.40 |
| ATOM | 4235 | CE2 | PHE | B | 498 | 50.896 | 5.987 | 66.848 | 1.00 48.47 |
| ATOM | 4236 | CZ | PHE | B | 498 | 51.623 | 6.712 | 65.921 | 1.00 49.05 |
| ATOM | 4237 | C | PHE | B | 498 | 51.548 | 10.802 | 69.934 | 1.00 49.25 |
| ATOM | 4238 | O | PHE | B | 498 | 51.572 | 11.547 | 70.943 | 1.00 50.13 |
| ATOM | 4239 | OH2 | H2O | B | 600 | 37.925 | -5.608 | 64.178 | 1.00 19.56 |
| ATOM | 4240 | OH2 | H2O | B | 601 | 35.288 | 10.987 | 21.464 | 1.00 31.02 |
| ATOM | 4241 | OH2 | H2O | B | 602 | 64.069 | 10.282 | 37.855 | 1.00 33.92 |
| ATOM | 4242 | OH2 | H2O | B | 603 | 34.294 | -2.020 | 55.654 | 1.00 3.73 |
| ATOM | 4243 | OH2 | H2O | B | 604 | 28.683 | 16.680 | 60.307 | 1.00 35.83 |
| ATOM | 4244 | OH2 | H2O | B | 605 | 27.429 | -6.181 | 60.779 | 1.00 34.80 |
| ATOM | 4245 | OH2 | H2O | B | 606 | 35.764 | 9.385 | 47.138 | 1.00 11.06 |
| ATOM | 4246 | OH2 | H2O | B | 607 | 32.108 | 21.509 | 62.275 | 1.00 44.81 |
| ATOM | 4247 | OH2 | H2O | B | 608 | 24.718 | -0.798 | 58.292 | 1.00 28.86 |

Figure 5

| | | | | | | | | | |
|---|---|---|---|---|---|---|---|---|---|
| ATOM | 4248 | OH2 | H2O | B | 609 | 54.056 | 4.968 | 42.099 | 1.00 23.54 |
| ATOM | 4249 | OH2 | H2O | B | 610 | 33.433 | 0.000 | 50.918 | 1.00 19.20 |
| ATOM | 4250 | OH2 | H2O | B | 611 | 22.689 | -2.650 | 57.652 | 1.00 18.35 |
| ATOM | 4251 | OH2 | H2O | B | 612 | 38.152 | -8.092 | 56.900 | 1.00 25.10 |
| ATOM | 4252 | OH2 | H2O | B | 613 | 48.358 | 26.421 | 40.931 | 1.00 48.04 |
| ATOM | 4253 | OH2 | H2O | B | 614 | 61.949 | 22.560 | 28.674 | 1.00 14.70 |
| ATOM | 4254 | OH2 | H2O | B | 615 | 33.665 | 7.790 | 46.188 | 1.00 19.05 |
| ATOM | 4255 | OH2 | H2O | B | 616 | 45.493 | 5.429 | 35.887 | 1.00 17.02 |
| ATOM | 4256 | OH2 | H2O | B | 617 | 35.589 | 22.357 | 35.939 | 1.00 29.21 |
| ATOM | 4257 | OH2 | H2O | B | 618 | 26.940 | -2.073 | 59.381 | 1.00 11.54 |
| ATOM | 4258 | OH2 | H2O | B | 619 | 30.141 | -7.233 | 59.188 | 1.00 46.06 |
| ATOM | 4259 | OH2 | H2O | B | 620 | 25.876 | 15.442 | 59.341 | 1.00 43.38 |
| ATOM | 4260 | OH2 | H2O | B | 621 | 26.220 | -2.111 | 62.344 | 1.00 19.52 |
| ATOM | 4261 | OH2 | H2O | B | 622 | 59.343 | 14.926 | 44.335 | 1.00 38.61 |
| ATOM | 4262 | OH2 | H2O | B | 623 | 45.648 | 23.180 | 55.536 | 1.00 34.23 |
| ATOM | 4263 | OH2 | H2O | B | 624 | 29.640 | 10.163 | 36.713 | 1.00 17.96 |
| ATOM | 4264 | OH2 | H2O | B | 625 | 25.269 | 11.406 | 50.324 | 1.00 37.91 |
| ATOM | 4265 | OH2 | H2O | B | 626 | 63.008 | 26.751 | 35.263 | 1.00 24.80 |
| ATOM | 4266 | OH2 | H2O | B | 627 | 51.580 | -5.099 | 50.675 | 1.00 25.31 |
| ATOM | 4267 | OH2 | H2O | B | 628 | 54.358 | 20.939 | 48.920 | 1.00 40.13 |
| ATOM | 4268 | OH2 | H2O | B | 629 | 22.424 | 13.171 | 55.725 | 1.00 21.07 |
| ATOM | 4269 | OH2 | H2O | B | 630 | 31.759 | 16.119 | 56.272 | 1.00 27.83 |
| ATOM | 4270 | OH2 | H2O | B | 631 | 53.119 | 28.120 | 35.404 | 1.00 21.14 |
| ATOM | 4271 | OH2 | H2O | B | 632 | 48.871 | 17.271 | 58.851 | 1.00 28.14 |
| ATOM | 4272 | OH2 | H2O | B | 633 | 48.626 | 25.905 | 24.494 | 1.00 26.06 |
| ATOM | 4273 | OH2 | H2O | B | 634 | 47.089 | 10.285 | 20.878 | 1.00 19.87 |
| ATOM | 4274 | OH2 | H2O | B | 635 | 25.071 | 13.720 | 55.662 | 1.00 17.50 |
| ATOM | 4275 | OH2 | H2O | B | 636 | 31.600 | 19.194 | 49.802 | 1.00 23.67 |
| ATOM | 4276 | OH2 | H2O | B | 637 | 52.358 | 1.669 | 31.949 | 1.00 32.46 |
| ATOM | 4277 | OH2 | H2O | B | 638 | 32.576 | 10.462 | 46.755 | 1.00 29.44 |
| ATOM | 4278 | OH2 | H2O | B | 639 | 56.893 | 12.725 | 21.528 | 1.00 44.84 |
| ATOM | 4279 | OH2 | H2O | B | 640 | 42.327 | 26.672 | 25.776 | 1.00 29.81 |
| ATOM | 4280 | OH2 | H2O | B | 641 | 49.053 | 10.039 | 24.832 | 1.00 22.45 |
| ATOM | 4281 | OH2 | H2O | B | 642 | 57.590 | 20.060 | 40.521 | 1.00 25.61 |
| ATOM | 4282 | OH2 | H2O | D | 643 | 55.338 | -3.698 | 57.045 | 1.00 44.82 |
| ATOM | 4283 | OH2 | H2O | B | 644 | 26.404 | -1.352 | 54.347 | 1.00 23.11 |
| ATOM | 4284 | OH2 | H2O | B | 645 | 48.587 | 5.045 | 25.841 | 1.00 37.74 |
| ATOM | 4285 | N1 | LIG | B | 500 | 52.300 | 4.037 | 38.023 | 1.00 33.35 |
| ATOM | 4286 | C1 | LIG | B | 500 | 51.777 | 5.468 | 38.091 | 1.00 30.98 |
| ATOM | 4287 | C2 | LIG | B | 500 | 52.248 | 6.237 | 39.360 | 1.00 29.21 |
| ATOM | 4288 | C3 | LIG | B | 500 | 51.794 | 7.730 | 39.385 | 1.00 27.58 |
| ATOM | 4289 | C4 | LIG | B | 500 | 52.314 | 8.489 | 38.094 | 1.00 26.42 |
| ATOM | 4290 | C5 | LIG | B | 500 | 51.736 | 7.780 | 36.868 | 1.00 26.87 |
| ATOM | 4291 | C6 | LIG | B | 500 | 52.220 | 6.313 | 36.836 | 1.00 28.97 |
| ATOM | 4292 | N2 | LIG | B | 500 | 51.921 | 9.914 | 38.228 | 1.00 25.13 |
| ATOM | 4293 | C7 | LIG | B | 500 | 50.760 | 10.445 | 37.902 | 1.00 24.77 |
| ATOM | 4294 | C8 | LIG | B | 500 | 50.781 | 11.781 | 38.170 | 1.00 23.72 |
| ATOM | 4295 | C9 | LIG | B | 500 | 52.155 | 12.085 | 38.724 | 1.00 23.97 |
| ATOM | 4296 | C10 | LIG | B | 500 | 52.847 | 13.240 | 39.189 | 1.00 24.64 |
| ATOM | 4297 | N3 | LIG | B | 500 | 54.130 | 13.022 | 39.609 | 1.00 24.26 |
| ATOM | 4298 | C11 | LIG | B | 500 | 54.717 | 11.809 | 39.581 | 1.00 22.83 |
| ATOM | 4299 | N4 | LIG | B | 500 | 54.057 | 10.734 | 39.129 | 1.00 22.62 |
| ATOM | 4300 | C12 | LIG | B | 500 | 52.779 | 10.851 | 38.705 | 1.00 24.17 |
| ATOM | 4301 | N5 | LIG | B | 500 | 52.336 | 14.448 | 39.252 | 1.00 25.14 |
| ATOM | 4302 | C13 | LIG | B | 500 | 49.577 | 12.661 | 37.886 | 1.00 23.85 |
| ATOM | 4303 | C14 | LIG | B | 500 | 48.287 | 12.298 | 38.339 | 1.00 23.19 |
| ATOM | 4304 | C15 | LIG | B | 500 | 47.190 | 13.131 | 38.048 | 1.00 23.89 |
| ATOM | 4305 | C16 | LIG | B | 500 | 47.375 | 14.324 | 37.307 | 1.00 25.56 |
| ATOM | 4306 | O1 | LIG | B | 500 | 46.280 | 15.143 | 37.034 | 1.00 26.74 |
| ATOM | 4307 | C17 | LIG | B | 500 | 45.275 | 15.674 | 37.844 | 1.00 28.78 |

Figure 5

| ATOM | 4308 | C18 | LIG | B | 500 | 43.946 | 15.741 | 37.390 | 1.00 | 28.53 |
| ATOM | 4309 | C19 | LIG | B | 500 | 42.944 | 16.272 | 38.218 | 1.00 | 28.45 |
| ATOM | 4310 | C20 | LIG | B | 500 | 43.259 | 16.746 | 39.505 | 1.00 | 27.49 |
| ATOM | 4311 | C21 | LIG | B | 500 | 44.588 | 16.684 | 39.971 | 1.00 | 28.77 |
| ATOM | 4312 | C22 | LIG | B | 500 | 45.601 | 16.150 | 39.145 | 1.00 | 28.79 |
| ATOM | 4313 | C23 | LIG | B | 500 | 48.661 | 14.679 | 36.866 | 1.00 | 24.73 |
| ATOM | 4314 | C24 | LIG | B | 500 | 49.749 | 13.851 | 37.158 | 1.00 | 23.79 |
| ATOM | 4315 | C25 | LIG | B | 500 | 52.684 | 3.434 | 39.324 | 1.00 | 37.39 |
| ATOM | 4316 | C26 | LIG | B | 500 | 53.251 | 1.956 | 39.192 | 1.00 | 39.14 |
| ATOM | 4317 | N6 | LIG | B | 500 | 52.220 | 1.073 | 38.552 | 1.00 | 38.96 |
| ATOM | 4318 | C27 | LIG | B | 500 | 52.713 | -0.333 | 38.410 | 1.00 | 40.26 |
| ATOM | 4319 | C28 | LIG | B | 500 | 51.867 | 1.645 | 37.257 | 1.00 | 38.32 |
| ATOM | 4320 | C29 | LIG | B | 500 | 51.353 | 3.102 | 37.380 | 1.00 | 36.36 |
| END | | | | | | | | | | |

Figure 5

```
CRYST1   57.251   44.335  120.777  90.00  90.01  90.00 P21          1
SCALE1      0.017467  0.000000  0.000003        0.00000
SCALE2      0.000000  0.022556  0.000000        0.00000
SCALE3      0.000000  0.000000  0.008280        0.00000
ATOM      1  CB  TRP A 238      17.601  -5.703  27.746  1.00 54.61
ATOM      2  CG  TRP A 238      17.185  -6.123  26.359  1.00 55.31
ATOM      3  CD2 TRP A 238      17.787  -5.720  25.116  1.00 55.04
ATOM      4  CE2 TRP A 238      17.038  -6.317  24.079  1.00 55.13
ATOM      5  CE3 TRP A 238      18.885  -4.919  24.778  1.00 55.22
ATOM      6  CD1 TRP A 238      16.129  -6.924  26.029  1.00 55.03
ATOM      7  NE1 TRP A 238      16.033  -7.045  24.666  1.00 55.23
ATOM      8  CZ2 TRP A 238      17.351  -6.136  22.722  1.00 55.67
ATOM      9  CZ3 TRP A 238      19.199  -4.741  23.426  1.00 54.90
ATOM     10  CH2 TRP A 238      18.433  -5.349  22.419  1.00 54.62
ATOM     11  C   TRP A 238      19.267  -5.716  29.591  1.00 53.69
ATOM     12  O   TRP A 238      19.677  -4.557  29.493  1.00 54.40
ATOM     13  N   TRP A 238      18.447  -7.898  28.556  1.00 52.49
ATOM     14  CA  TRP A 238      18.794  -6.463  28.335  1.00 53.51
ATOM     15  N   GLU A 239      19.145  -6.347  30.757  1.00 53.76
ATOM     16  CA  GLU A 239      19.572  -5.736  32.034  1.00 52.06
ATOM     17  CB  GLU A 239      18.667  -6.187  33.195  1.00 52.69
ATOM     18  CG  GLU A 239      17.200  -5.783  33.067  0.00 53.14
ATOM     19  CD  GLU A 239      16.352  -6.257  34.242  0.00 53.36
ATOM     20  OE1 GLU A 239      16.897  -6.895  35.173  0.00 53.54
ATOM     21  OE2 GLU A 239      15.133  -5.992  34.236  0.00 53.51
ATOM     22  C   GLU A 239      21.025  -6.125  32.343  1.00 50.22
ATOM     23  O   GLU A 239      21.432  -7.274  32.139  1.00 50.22
ATOM     24  N   VAL A 240      21.810  -5.155  32.822  1.00 47.27
ATOM     25  CA  VAL A 240      23.214  -5.387  33.159  1.00 44.98
ATOM     26  CB  VAL A 240      24.159  -4.891  32.026  1.00 43.89
ATOM     27  CG1 VAL A 240      23.879  -5.638  30.730  1.00 43.03
ATOM     28  CG2 VAL A 240      24.023  -3.386  31.834  1.00 42.05
ATOM     29  C   VAL A 240      23.607  -4.669  34.455  1.00 44.40
ATOM     30  O   VAL A 240      22.906  -3.769  34.915  1.00 45.06
ATOM     31  N   PRO A 241      24.687  -5.122  35.107  1.00 43.64
ATOM     32  CD  PRO A 241      25.317  -6.444  34.945  1.00 43.02
ATOM     33  CA  PRO A 241      25.135  -4.484  36.351  1.00 43.35
ATOM     34  CB  PRO A 241      26.193  -5.462  36.860  1.00 42.99
ATOM     35  CG  PRO A 241      25.697  -6.787  36.364  1.00 42.48
ATOM     36  C   PRO A 241      25.749  -3.105  36.065  1.00 43.73
ATOM     37  O   PRO A 241      26.400  -2.923  35.044  1.00 44.39
ATOM     38  N   ARG A 242      25.551  -2.147  36.964  1.00 44.49
ATOM     39  CA  ARG A 242      26.092  -0.792  36.809  1.00 45.99
ATOM     40  CB  ARG A 242      25.673   0.042  38.023  1.00 46.88
ATOM     41  CG  ARG A 242      26.403   1.369  38.233  1.00 48.13
ATOM     42  CD  ARG A 242      25.859   2.463  37.353  1.00 49.75
ATOM     43  NE  ARG A 242      24.395   2.528  37.399  1.00 51.26
ATOM     44  CZ  ARG A 242      23.674   2.929  38.440  1.00 50.32
ATOM     45  NH1 ARG A 242      24.262   3.316  39.560  1.00 51.78
ATOM     46  NH2 ARG A 242      22.354   2.933  38.362  1.00 49.86
```

Figure 6

| ATOM | 47 | C | ARG | A | 242 | 27.622 | -0.747 | 36.651 | 1.00 | 46.60 |
|------|-----|-----|-----|---|-----|--------|--------|--------|------|-------|
| ATOM | 48 | O | ARG | A | 242 | 28.164 | 0.210 | 36.095 | 1.00 | 46.63 |
| ATOM | 49 | N | GLU | A | 243 | 28.298 | -1.780 | 37.157 | 1.00 | 48.02 |
| ATOM | 50 | CA | GLU | A | 243 | 29.768 | -1.898 | 37.125 | 1.00 | 48.73 |
| ATOM | 51 | CB | GLU | A | 243 | 30.253 | -3.030 | 38.059 | 1.00 | 51.20 |
| ATOM | 52 | CG | GLU | A | 243 | 30.102 | -2.784 | 39.576 | 1.00 | 54.40 |
| ATOM | 53 | CD | GLU | A | 243 | 28.639 | -2.717 | 40.062 | 1.00 | 55.70 |
| ATOM | 54 | OE1 | GLU | A | 243 | 27.875 | -3.691 | 39.828 | 1.00 | 54.94 |
| ATOM | 55 | OE2 | GLU | A | 243 | 28.265 | -1.687 | 40.687 | 1.00 | 56.50 |
| ATOM | 56 | C | GLU | A | 243 | 30.335 | -2.136 | 35.727 | 1.00 | 47.24 |
| ATOM | 57 | O | GLU | A | 243 | 31.466 | -1.754 | 35.431 | 1.00 | 47.59 |
| ATOM | 58 | N | THR | A | 244 | 29.545 | -2.773 | 34.875 | 1.00 | 44.51 |
| ATOM | 59 | CA | THR | A | 244 | 29.963 | -3.072 | 33.512 | 1.00 | 42.01 |
| ATOM | 60 | CB | THR | A | 244 | 29.031 | -4.121 | 32.898 | 1.00 | 42.33 |
| ATOM | 61 | OG1 | THR | A | 244 | 27.780 | -3.513 | 32.549 | 1.00 | 42.76 |
| ATOM | 62 | CG2 | THR | A | 244 | 28.772 | -5.234 | 33.896 | 1.00 | 42.84 |
| ATOM | 63 | C | THR | A | 244 | 29.960 | -1.821 | 32.621 | 1.00 | 40.59 |
| ATOM | 64 | O | THR | A | 244 | 30.315 | -1.885 | 31.444 | 1.00 | 39.05 |
| ATOM | 65 | N | LEU | A | 245 | 29.621 | -0.682 | 33.215 | 1.00 | 39.00 |
| ATOM | 66 | CA | LEU | A | 245 | 29.529 | 0.574 | 32.498 | 1.00 | 38.10 |
| ATOM | 67 | CB | LEU | A | 245 | 28.047 | 0.939 | 32.344 | 1.00 | 38.93 |
| ATOM | 68 | CG | LEU | A | 245 | 27.691 | 2.227 | 31.605 | 1.00 | 40.52 |
| ATOM | 69 | CD1 | LEU | A | 245 | 28.038 | 2.095 | 30.126 | 1.00 | 39.69 |
| ATOM | 70 | CD2 | LEU | A | 245 | 26.204 | 2.525 | 31.797 | 1.00 | 41.59 |
| ATOM | 71 | C | LEU | A | 245 | 30.265 | 1.702 | 33.214 | 1.00 | 37.75 |
| ATOM | 72 | O | LEU | A | 245 | 30.150 | 1.847 | 34.443 | 1.00 | 37.93 |
| ATOM | 73 | N | LYS | A | 246 | 31.018 | 2.489 | 32.436 | 1.00 | 35.78 |
| ATOM | 74 | CA | LYS | A | 246 | 31.771 | 3.633 | 32.951 | 1.00 | 33.73 |
| ATOM | 75 | CB | LYS | A | 246 | 33.289 | 3.402 | 32.855 | 1.00 | 35.16 |
| ATOM | 76 | CG | LYS | A | 246 | 34.128 | 4.660 | 33.177 | 1.00 | 36.91 |
| ATOM | 77 | CD | LYS | A | 246 | 35.618 | 4.380 | 33.417 | 1.00 | 39.03 |
| ATOM | 78 | CE | LYS | A | 246 | 36.326 | 3.883 | 32.159 | 1.00 | 40.56 |
| ATOM | 79 | NZ | LYS | A | 246 | 37.804 | 3.741 | 32.347 | 1.00 | 41.84 |
| ATOM | 80 | C | LYS | A | 246 | 31.413 | 4.917 | 32.210 | 1.00 | 32.28 |
| ATOM | 81 | O | LYS | A | 246 | 31.590 | 5.015 | 31.002 | 1.00 | 32.03 |
| ATOM | 82 | N | LEU | A | 247 | 30.902 | 5.896 | 32.949 | 1.00 | 30.73 |
| ATOM | 83 | CA | LEU | A | 247 | 30.538 | 7.188 | 32.384 | 1.00 | 28.35 |
| ATOM | 84 | CB | LEU | A | 247 | 29.438 | 7.845 | 33.203 | 1.00 | 26.51 |
| ATOM | 85 | CG | LEU | A | 247 | 28.039 | 7.383 | 32.807 | 1.00 | 26.31 |
| ATOM | 86 | CD1 | LEU | A | 247 | 27.883 | 5.873 | 32.920 | 1.00 | 25.54 |
| ATOM | 87 | CD2 | LEU | A | 247 | 27.035 | 8.122 | 33.671 | 1.00 | 27.78 |
| ATOM | 88 | C | LEU | A | 247 | 31.765 | 8.071 | 32.333 | 1.00 | 28.99 |
| ATOM | 89 | O | LEU | A | 247 | 32.473 | 8.240 | 33.334 | 1.00 | 30.07 |
| ATOM | 90 | N | VAL | A | 248 | 31.992 | 8.677 | 31.175 | 1.00 | 26.79 |
| ATOM | 91 | CA | VAL | A | 248 | 33.169 | 9.498 | 30.989 | 1.00 | 25.93 |
| ATOM | 92 | CB | VAL | A | 248 | 34.042 | 8.933 | 29.835 | 1.00 | 24.91 |
| ATOM | 93 | CG1 | VAL | A | 248 | 35.351 | 9.694 | 29.744 | 1.00 | 25.08 |
| ATOM | 94 | CG2 | VAL | A | 248 | 34.300 | 7.451 | 30.030 | 1.00 | 20.94 |
| ATOM | 95 | C | VAL | A | 248 | 32.963 | 10.988 | 30.751 | 1.00 | 26.69 |
| ATOM | 96 | O | VAL | A | 248 | 33.675 | 11.824 | 31.314 | 1.00 | 29.23 |
| ATOM | 97 | N | GLU | A | 249 | 31.964 | 11.344 | 29.968 | 1.00 | 27.66 |
| ATOM | 98 | CA | GLU | A | 249 | 31.781 | 12.748 | 29.646 | 1.00 | 27.59 |
| ATOM | 99 | CB | GLU | A | 249 | 32.658 | 13.043 | 28.430 | 1.00 | 27.78 |
| ATOM | 100 | CG | GLU | A | 249 | 32.544 | 14.425 | 27.829 | 1.00 | 28.76 |
| ATOM | 101 | CD | GLU | A | 249 | 33.361 | 14.552 | 26.569 | 1.00 | 29.09 |
| ATOM | 102 | OE1 | GLU | A | 249 | 34.075 | 13.586 | 26.203 | 1.00 | 28.13 |
| ATOM | 103 | OE2 | GLU | A | 249 | 33.288 | 15.624 | 25.943 | 1.00 | 30.98 |
| ATOM | 104 | C | GLU | A | 249 | 30.326 | 13.107 | 29.365 | 1.00 | 27.12 |
| ATOM | 105 | O | GLU | A | 249 | 29.617 | 12.389 | 28.666 | 1.00 | 25.49 |

Figure 6

```
ATOM    106  N    ARG A 250      29.899  14.248  29.885  1.00 26.37
ATOM    107  CA   ARG A 250      28.534  14.685  29.697  1.00 27.55
ATOM    108  CB   ARG A 250      28.108  15.603  30.837  1.00 27.02
ATOM    109  CG   ARG A 250      26.670  15.400  31.248  1.00 27.56
ATOM    110  CD   ARG A 250      26.291  16.289  32.402  1.00 26.77
ATOM    111  NE   ARG A 250      26.499  17.689  32.063  1.00 26.91
ATOM    112  CZ   ARG A 250      26.184  18.704  32.856  1.00 28.14
ATOM    113  NH1  ARG A 250      25.644  18.470  34.041  1.00 27.53
ATOM    114  NH2  ARG A 250      26.381  19.956  32.452  1.00 28.59
ATOM    115  C    ARG A 250      28.363  15.387  28.368  1.00 27.49
ATOM    116  O    ARG A 250      28.955  16.440  28.140  1.00 28.04
ATOM    117  N    LEU A 251      27.585  14.767  27.479  1.00 27.14
ATOM    118  CA   LEU A 251      27.299  15.321  26.157  1.00 25.67
ATOM    119  CB   LEU A 251      26.894  14.218  25.182  1.00 22.61
ATOM    120  CG   LEU A 251      27.966  13.142  24.996  1.00 22.62
ATOM    121  CD1  LEU A 251      27.531  12.121  23.946  1.00 21.58
ATOM    122  CD2  LEU A 251      29.291  13.785  24.611  1.00 21.67
ATOM    123  C    LEU A 251      26.199  16.384  26.251  1.00 25.91
ATOM    124  O    LEU A 251      26.197  17.374  25.508  1.00 26.98
ATOM    125  N    GLY A 252      25.290  16.195  27.200  1.00 26.29
ATOM    126  CA   GLY A 252      24.213  17.151  27.378  1.00 24.17
ATOM    127  C    GLY A 252      23.459  16.973  28.674  1.00 23.07
ATOM    128  O    GLY A 252      23.433  15.884  29.257  1.00 20.94
ATOM    129  N    ALA A 253      22.829  18.056  29.107  1.00 23.87
ATOM    130  CA   ALA A 253      22.043  18.073  30.337  1.00 23.68
ATOM    131  CB   ALA A 253      22.829  18.717  31.457  1.00 22.55
ATOM    132  C    ALA A 253      20.775  18.863  30.079  1.00 25.41
ATOM    133  O    ALA A 253      20.829  19.971  29.545  1.00 24.27
ATOM    134  N    GLY A 254      19.634  18.294  30.460  1.00 27.61
ATOM    135  CA   GLY A 254      18.376  18.974  30.255  1.00 29.74
ATOM    136  C    GLY A 254      17.370  18.775  31.368  1.00 32.05
ATOM    137  O    GLY A 254      17.706  18.287  32.439  1.00 33.66
ATOM    138  N    GLN A 255      16.117  19.113  31.066  1.00 34.35
ATOM    139  CA   GLN A 255      14.991  19.035  31.995  1.00 35.31
ATOM    140  CB   GLN A 255      13.735  19.600  31.302  1.00 38.22
ATOM    141  CG   GLN A 255      12.900  20.568  32.161  1.00 44.28
ATOM    142  CD   GLN A 255      11.360  20.334  32.065  1.00 47.35
ATOM    143  OE1  GLN A 255      10.643  20.350  33.100  1.00 46.52
ATOM    144  NE2  GLN A 255      10.857  20.116  30.827  1.00 46.91
ATOM    145  C    GLN A 255      14.690  17.644  32.584  1.00 33.38
ATOM    146  O    GLN A 255      14.431  17.524  33.783  1.00 32.90
ATOM    147  N    PHE A 256      14.708  16.610  31.735  1.00 31.04
ATOM    148  CA   PHE A 256      14.409  15.226  32.148  1.00 28.74
ATOM    149  CB   PHE A 256      13.584  14.490  31.062  1.00 29.13
ATOM    150  CG   PHE A 256      12.198  15.058  30.809  1.00 29.23
ATOM    151  CD1  PHE A 256      11.792  16.278  31.341  1.00 29.93
ATOM    152  CD2  PHE A 256      11.297  14.347  30.015  1.00 30.20
ATOM    153  CE1  PHE A 256      10.504  16.784  31.088  1.00 30.43
ATOM    154  CE2  PHE A 256      10.019  14.839  29.757  1.00 30.27
ATOM    155  CZ   PHE A 256       9.622  16.061  30.297  1.00 30.60
ATOM    156  C    PHE A 256      15.619  14.340  32.478  1.00 27.36
ATOM    157  O    PHE A 256      15.459  13.192  32.910  1.00 26.84
ATOM    158  N    GLY A 257      16.822  14.832  32.228  1.00 26.88
ATOM    159  CA   GLY A 257      17.989  14.018  32.501  1.00 25.41
ATOM    160  C    GLY A 257      19.216  14.510  31.768  1.00 26.92
ATOM    161  O    GLY A 257      19.325  15.697  31.438  1.00 25.56
ATOM    162  N    GLU A 258      20.133  13.583  31.500  1.00 28.26
ATOM    163  CA   GLU A 258      21.401  13.884  30.832  1.00 29.52
ATOM    164  CB   GLU A 258      22.496  14.078  31.879  1.00 30.16
```

Figure 6

| | | | | | | | | |
|---|---|---|---|---|---|---|---|---|
| ATOM | 165 | CG | GLU | A | 258 | 22.139 | 15.043 | 32.979 | 1.00 | 31.32 |
| ATOM | 166 | CD | GLU | A | 258 | 23.282 | 15.295 | 33.927 | 1.00 | 32.44 |
| ATOM | 167 | OE1 | GLU | A | 258 | 23.989 | 14.329 | 34.293 | 1.00 | 32.53 |
| ATOM | 168 | OE2 | GLU | A | 258 | 23.466 | 16.475 | 34.300 | 1.00 | 33.80 |
| ATOM | 169 | C | GLU | A | 258 | 21.863 | 12.756 | 29.913 | 1.00 | 29.95 |
| ATOM | 170 | O | GLU | A | 258 | 21.458 | 11.602 | 30.086 | 1.00 | 30.75 |
| ATOM | 171 | N | VAL | A | 259 | 22.742 | 13.094 | 28.961 | 1.00 | 29.56 |
| ATOM | 172 | CA | VAL | A | 259 | 23.317 | 12.110 | 28.036 | 1.00 | 29.37 |
| ATOM | 173 | CB | VAL | A | 259 | 23.009 | 12.428 | 26.547 | 1.00 | 29.04 |
| ATOM | 174 | CG1 | VAL | A | 259 | 23.466 | 11.268 | 25.658 | 1.00 | 27.76 |
| ATOM | 175 | CG2 | VAL | A | 259 | 21.515 | 12.670 | 26.352 | 1.00 | 29.93 |
| ATOM | 176 | C | VAL | A | 259 | 24.832 | 12.140 | 28.263 | 1.00 | 29.18 |
| ATOM | 177 | O | VAL | A | 259 | 25.435 | 13.212 | 28.327 | 1.00 | 29.62 |
| ATOM | 178 | N | TRP | A | 260 | 25.431 | 10.962 | 28.416 | 1.00 | 28.26 |
| ATOM | 179 | CA | TRP | A | 260 | 26.866 | 10.828 | 28.671 | 1.00 | 28.17 |
| ATOM | 180 | CB | TRP | A | 260 | 27.111 | 10.215 | 30.085 | 1.00 | 28.37 |
| ATOM | 181 | CG | TRP | A | 260 | 26.960 | 11.156 | 31.261 | 1.00 | 30.44 |
| ATOM | 182 | CD2 | TRP | A | 260 | 28.006 | 11.633 | 32.130 | 1.00 | 32.08 |
| ATOM | 183 | CE2 | TRP | A | 260 | 27.426 | 12.584 | 32.999 | 1.00 | 33.61 |
| ATOM | 184 | CE3 | TRP | A | 260 | 29.377 | 11.359 | 32.246 | 1.00 | 32.96 |
| ATOM | 185 | CD1 | TRP | A | 260 | 25.822 | 11.804 | 31.654 | 1.00 | 31.77 |
| ATOM | 186 | NE1 | TRP | A | 260 | 26.095 | 12.673 | 32.686 | 1.00 | 33.14 |
| ATOM | 187 | CZ2 | TRP | A | 260 | 28.174 | 13.264 | 33.976 | 1.00 | 33.70 |
| ATOM | 188 | CZ3 | TRP | A | 260 | 30.120 | 12.039 | 33.218 | 1.00 | 32.45 |
| ATOM | 189 | CH2 | TRP | A | 260 | 29.515 | 12.979 | 34.064 | 1.00 | 33.26 |
| ATOM | 190 | C | TRP | A | 260 | 27.567 | 9.915 | 27.661 | 1.00 | 27.32 |
| ATOM | 191 | O | TRP | A | 260 | 26.970 | 8.980 | 27.136 | 1.00 | 25.45 |
| ATOM | 192 | N | MET | A | 261 | 28.815 | 10.237 | 27.338 | 1.00 | 27.36 |
| ATOM | 193 | CA | MET | A | 261 | 29.616 | 9.351 | 26.504 | 1.00 | 28.40 |
| ATOM | 194 | CB | MET | A | 261 | 30.682 | 10.132 | 25.719 | 1.00 | 28.20 |
| ATOM | 195 | CG | MET | A | 261 | 31.606 | 9.236 | 24.866 | 1.00 | 27.59 |
| ATOM | 196 | SD | MET | A | 261 | 33.065 | 8.499 | 25.719 | 1.00 | 28.13 |
| ATOM | 197 | CE | MET | A | 261 | 34.034 | 9.980 | 26.038 | 1.00 | 25.59 |
| ATOM | 198 | C | MET | A | 261 | 30.287 | 8.441 | 27.563 | 1.00 | 27.31 |
| ATOM | 199 | O | MET | A | 261 | 30.618 | 8.897 | 28.644 | 1.00 | 27.94 |
| ATOM | 200 | N | GLY | A | 262 | 30.450 | 7.163 | 27.274 | 1.00 | 26.05 |
| ATOM | 201 | CA | GLY | A | 262 | 31.060 | 6.272 | 28.239 | 1.00 | 24.84 |
| ATOM | 202 | C | GLY | A | 262 | 31.500 | 4.973 | 27.604 | 1.00 | 26.16 |
| ATOM | 203 | O | GLY | A | 262 | 31.386 | 4.803 | 26.400 | 1.00 | 26.70 |
| ATOM | 204 | N | TYR | A | 263 | 32.005 | 4.051 | 28.411 | 1.00 | 26.39 |
| ATOM | 205 | CA | TYR | A | 263 | 32.463 | 2.781 | 27.890 | 1.00 | 27.63 |
| ATOM | 206 | CB | TYR | A | 263 | 33.970 | 2.670 | 28.069 | 1.00 | 26.26 |
| ATOM | 207 | CG | TYR | A | 263 | 34.690 | 3.693 | 27.221 | 1.00 | 24.67 |
| ATOM | 208 | CD1 | TYR | A | 263 | 35.006 | 3.414 | 25.894 | 1.00 | 23.72 |
| ATOM | 209 | CE1 | TYR | A | 263 | 35.584 | 4.360 | 25.080 | 1.00 | 23.51 |
| ATOM | 210 | CD2 | TYR | A | 263 | 34.982 | 4.968 | 27.718 | 1.00 | 23.22 |
| ATOM | 211 | CE2 | TYR | A | 263 | 35.564 | 5.935 | 26.906 | 1.00 | 23.17 |
| ATOM | 212 | CZ | TYR | A | 263 | 35.859 | 5.617 | 25.582 | 1.00 | 24.18 |
| ATOM | 213 | OH | TYR | A | 263 | 36.417 | 6.550 | 24.736 | 1.00 | 24.06 |
| ATOM | 214 | C | TYR | A | 263 | 31.721 | 1.611 | 28.493 | 1.00 | 30.94 |
| ATOM | 215 | O | TYR | A | 263 | 31.457 | 1.573 | 29.695 | 1.00 | 33.21 |
| ATOM | 216 | N | TYR | A | 264 | 31.311 | 0.702 | 27.621 | 1.00 | 34.50 |
| ATOM | 217 | CA | TYR | A | 264 | 30.550 | -0.486 | 27.987 | 1.00 | 37.03 |
| ATOM | 218 | CB | TYR | A | 264 | 29.321 | -0.590 | 27.067 | 1.00 | 36.85 |
| ATOM | 219 | CG | TYR | A | 264 | 28.406 | -1.761 | 27.317 | 1.00 | 37.67 |
| ATOM | 220 | CD1 | TYR | A | 264 | 28.068 | -2.153 | 28.621 | 1.00 | 37.49 |
| ATOM | 221 | CE1 | TYR | A | 264 | 27.224 | -3.241 | 28.852 | 1.00 | 36.80 |
| ATOM | 222 | CD2 | TYR | A | 264 | 27.881 | -2.485 | 26.249 | 1.00 | 37.41 |
| ATOM | 223 | CE2 | TYR | A | 264 | 27.040 | -3.572 | 26.465 | 1.00 | 37.40 |

Figure 6

| ATOM | 224 | CZ | TYR | A | 264 | 26.715 | -3.943 | 27.766 | 1.00 | 37.32 |
| ATOM | 225 | OH | TYR | A | 264 | 25.870 | -5.006 | 27.965 | 1.00 | 36.89 |
| ATOM | 226 | C | TYR | A | 264 | 31.499 | -1.674 | 27.840 | 1.00 | 39.34 |
| ATOM | 227 | O | TYR | A | 264 | 32.096 | -1.879 | 26.780 | 1.00 | 40.17 |
| ATOM | 228 | N | ASN | A | 265 | 31.671 | -2.414 | 28.935 | 1.00 | 42.02 |
| ATOM | 229 | CA | ASN | A | 265 | 32.571 | -3.565 | 28.998 | 1.00 | 43.12 |
| ATOM | 230 | CB | ASN | A | 265 | 32.120 | -4.686 | 28.058 | 1.00 | 43.64 |
| ATOM | 231 | CG | ASN | A | 265 | 30.750 | -5.230 | 28.420 | 1.00 | 44.35 |
| ATOM | 232 | OD1 | ASN | A | 265 | 30.478 | -5.567 | 29.582 | 1.00 | 44.25 |
| ATOM | 233 | ND2 | ASN | A | 265 | 29.870 | -5.302 | 27.432 | 1.00 | 44.40 |
| ATOM | 234 | C | ASN | A | 265 | 33.991 | -3.118 | 28.684 | 1.00 | 43.44 |
| ATOM | 235 | O | ASN | A | 265 | 34.691 | -3.731 | 27.887 | 1.00 | 44.54 |
| ATOM | 236 | N | GLY | A | 266 | 34.371 | -1.990 | 29.272 | 1.00 | 44.04 |
| ATOM | 237 | CA | GLY | A | 266 | 35.701 | -1.451 | 29.091 | 1.00 | 45.45 |
| ATOM | 238 | C | GLY | A | 266 | 36.047 | -0.841 | 27.746 | 1.00 | 46.56 |
| ATOM | 239 | O | GLY | A | 266 | 36.653 | 0.237 | 27.700 | 1.00 | 47.77 |
| ATOM | 240 | N | HIS | A | 267 | 35.620 | -1.469 | 26.655 | 1.00 | 46.25 |
| ATOM | 241 | CA | HIS | A | 267 | 35.990 | -0.962 | 25.339 | 1.00 | 46.01 |
| ATOM | 242 | CB | HIS | A | 267 | 36.967 | -1.947 | 24.672 | 1.00 | 46.92 |
| ATOM | 243 | CG | HIS | A | 267 | 38.281 | -2.054 | 25.380 | 0.00 | 47.65 |
| ATOM | 244 | CD2 | HIS | A | 267 | 39.271 | -1.146 | 25.563 | 0.00 | 47.95 |
| ATOM | 245 | ND1 | HIS | A | 267 | 38.681 | -3.191 | 26.046 | 0.00 | 47.93 |
| ATOM | 246 | CE1 | HIS | A | 267 | 39.857 | -2.979 | 26.610 | 0.00 | 48.16 |
| ATOM | 247 | NE2 | HIS | A | 267 | 40.235 | -1.745 | 26.333 | 0.00 | 48.15 |
| ATOM | 248 | C | HIS | A | 267 | 34.918 | -0.451 | 24.352 | 1.00 | 44.24 |
| ATOM | 249 | O | HIS | A | 267 | 35.220 | 0.427 | 23.538 | 1.00 | 44.65 |
| ATOM | 250 | N | THR | A | 268 | 33.679 | -0.943 | 24.431 | 1.00 | 41.00 |
| ATOM | 251 | CA | THR | A | 268 | 32.636 | -0.476 | 23.507 | 1.00 | 38.04 |
| ATOM | 252 | CB | THR | A | 268 | 31.346 | -1.353 | 23.560 | 1.00 | 39.13 |
| ATOM | 253 | OG1 | THR | A | 268 | 31.654 | -2.701 | 23.188 | 1.00 | 40.58 |
| ATOM | 254 | CG2 | THR | A | 268 | 30.286 | -0.829 | 22.583 | 1.00 | 38.64 |
| ATOM | 255 | C | THR | A | 268 | 32.239 | 0.943 | 23.863 | 1.00 | 34.08 |
| ATOM | 256 | O | THR | A | 268 | 31.747 | 1.174 | 24.952 | 1.00 | 33.42 |
| ATOM | 257 | N | LYS | A | 269 | 32.462 | 1.893 | 22.958 | 1.00 | 31.28 |
| ATOM | 258 | CA | LYS | A | 269 | 32.085 | 3.279 | 23.219 | 1.00 | 28.31 |
| ATOM | 259 | CB | LYS | A | 269 | 32.755 | 4.224 | 22.224 | 1.00 | 26.05 |
| ATOM | 260 | CG | LYS | A | 269 | 32.776 | 5.687 | 22.638 | 1.00 | 23.71 |
| ATOM | 261 | CD | LYS | A | 269 | 33.764 | 6.468 | 21.767 | 1.00 | 22.41 |
| ATOM | 262 | CE | LYS | A | 269 | 34.024 | 7.867 | 22.312 | 1.00 | 22.34 |
| ATOM | 263 | NZ | LYS | A | 269 | 35.070 | 8.629 | 21.551 | 1.00 | 21.55 |
| ATOM | 264 | C | LYS | A | 269 | 30.563 | 3.349 | 23.101 | 1.00 | 29.34 |
| ATOM | 265 | O | LYS | A | 269 | 29.966 | 2.752 | 22.196 | 1.00 | 28.86 |
| ATOM | 266 | N | VAL | A | 270 | 29.940 | 4.018 | 24.069 | 1.00 | 28.30 |
| ATOM | 267 | CA | VAL | A | 270 | 28.493 | 4.140 | 24.112 | 1.00 | 25.54 |
| ATOM | 268 | CB | VAL | A | 270 | 27.857 | 3.037 | 25.010 | 1.00 | 25.74 |
| ATOM | 269 | CG1 | VAL | A | 270 | 28.181 | 1.659 | 24.490 | 1.00 | 24.66 |
| ATOM | 270 | CG2 | VAL | A | 270 | 28.308 | 3.190 | 26.468 | 1.00 | 24.42 |
| ATOM | 271 | C | VAL | A | 270 | 28.058 | 5.482 | 24.683 | 1.00 | 25.66 |
| ATOM | 272 | O | VAL | A | 270 | 28.858 | 6.234 | 25.236 | 1.00 | 25.13 |
| ATOM | 273 | N | ALA | A | 271 | 26.779 | 5.782 | 24.475 | 1.00 | 25.16 |
| ATOM | 274 | CA | ALA | A | 271 | 26.135 | 6.975 | 24.991 | 1.00 | 23.37 |
| ATOM | 275 | CB | ALA | A | 271 | 25.390 | 7.700 | 23.900 | 1.00 | 24.89 |
| ATOM | 276 | C | ALA | A | 271 | 25.161 | 6.371 | 25.989 | 1.00 | 22.69 |
| ATOM | 277 | O | ALA | A | 271 | 24.591 | 5.299 | 25.751 | 1.00 | 22.20 |
| ATOM | 278 | N | VAL | A | 272 | 24.988 | 7.056 | 27.110 | 1.00 | 21.94 |
| ATOM | 279 | CA | VAL | A | 272 | 24.131 | 6.582 | 28.186 | 1.00 | 21.14 |
| ATOM | 280 | CB | VAL | A | 272 | 25.000 | 6.250 | 29.446 | 1.00 | 20.42 |
| ATOM | 281 | CG1 | VAL | A | 272 | 24.139 | 5.782 | 30.594 | 1.00 | 20.76 |
| ATOM | 282 | CG2 | VAL | A | 272 | 26.077 | 5.227 | 29.127 | 1.00 | 18.34 |

Figure 6

| | | | | | | | | | |
|---|---|---|---|---|---|---|---|---|---|
| ATOM | 283 | C | VAL | A | 272 | 23.146 | 7.684 | 28.559 | 1.00 22.04 |
| ATOM | 284 | O | VAL | A | 272 | 23.557 | 8.805 | 28.836 | 1.00 23.79 |
| ATOM | 285 | N | LYS | A | 273 | 21.852 | 7.383 | 28.535 | 1.00 22.11 |
| ATOM | 286 | CA | LYS | A | 273 | 20.841 | 8.370 | 28.928 | 1.00 24.75 |
| ATOM | 287 | CB | LYS | A | 273 | 19.634 | 8.346 | 27.973 | 1.00 24.99 |
| ATOM | 288 | CG | LYS | A | 273 | 19.317 | 9.687 | 27.297 | 1.00 24.88 |
| ATOM | 289 | CD | LYS | A | 273 | 18.224 | 9.530 | 26.235 | 1.00 23.97 |
| ATOM | 290 | CE | LYS | A | 273 | 18.097 | 10.774 | 25.361 | 1.00 23.74 |
| ATOM | 291 | NZ | LYS | A | 273 | 16.888 | 10.704 | 24.494 | 1.00 24.29 |
| ATOM | 292 | C | LYS | A | 273 | 20.379 | 8.040 | 30.363 | 1.00 26.01 |
| ATOM | 293 | O | LYS | A | 273 | 20.046 | 6.887 | 30.670 | 1.00 24.92 |
| ATOM | 294 | N | SER | A | 274 | 20.427 | 9.030 | 31.248 | 1.00 26.64 |
| ATOM | 295 | CA | SER | A | 274 | 20.015 | 8.833 | 32.636 | 1.00 28.87 |
| ATOM | 296 | CB | SER | A | 274 | 21.132 | 9.250 | 33.561 | 1.00 29.02 |
| ATOM | 297 | OG | SER | A | 274 | 21.351 | 10.630 | 33.396 | 1.00 31.90 |
| ATOM | 298 | C | SER | A | 274 | 18.787 | 9.676 | 32.943 | 1.00 29.41 |
| ATOM | 299 | O | SER | A | 274 | 18.654 | 10.775 | 32.418 | 1.00 31.35 |
| ATOM | 300 | N | LEU | A | 275 | 17.929 | 9.192 | 33.835 | 1.00 29.31 |
| ATOM | 301 | CA | LEU | A | 275 | 16.702 | 9.916 | 34.195 | 1.00 29.80 |
| ATOM | 302 | CB | LEU | A | 275 | 15.553 | 8.910 | 34.446 | 1.00 27.56 |
| ATOM | 303 | CG | LEU | A | 275 | 14.202 | 9.361 | 35.034 | 1.00 25.31 |
| ATOM | 304 | CD1 | LEU | A | 275 | 13.486 | 10.329 | 34.092 | 1.00 25.02 |
| ATOM | 305 | CD2 | LEU | A | 275 | 13.329 | 8.155 | 35.317 | 1.00 24.06 |
| ATOM | 306 | C | LEU | A | 275 | 16.846 | 10.822 | 35.425 | 1.00 31.95 |
| ATOM | 307 | O | LEU | A | 275 | 17.270 | 10.372 | 36.481 | 1.00 32.65 |
| ATOM | 308 | N | LYS | A | 276 | 16.497 | 12.099 | 35.286 | 1.00 33.83 |
| ATOM | 309 | CA | LYS | A | 276 | 16.530 | 13.025 | 36.419 | 1.00 34.80 |
| ATOM | 310 | CB | LYS | A | 276 | 16.441 | 14.473 | 35.934 | 1.00 35.67 |
| ATOM | 311 | CG | LYS | A | 276 | 16.243 | 15.500 | 37.042 | 1.00 35.72 |
| ATOM | 312 | CD | LYS | A | 276 | 16.228 | 16.927 | 36.485 | 1.00 37.73 |
| ATOM | 313 | CE | LYS | A | 276 | 17.505 | 17.234 | 35.688 | 1.00 39.22 |
| ATOM | 314 | NZ | LYS | A | 276 | 17.579 | 18.645 | 35.192 | 1.00 39.47 |
| ATOM | 315 | C | LYS | A | 276 | 15.291 | 12.691 | 37.246 | 1.00 35.96 |
| ATOM | 316 | O | LYS | A | 276 | 14.175 | 13.046 | 36.860 | 1.00 35.95 |
| ATOM | 317 | N | GLN | A | 277 | 15.495 | 11.986 | 38.360 | 1.00 38.22 |
| ATOM | 318 | CA | GLN | A | 277 | 14.413 | 11.551 | 39.258 | 1.00 38.63 |
| ATOM | 319 | CB | GLN | A | 277 | 14.982 | 11.193 | 40.634 | 1.00 41.75 |
| ATOM | 320 | CG | GLN | A | 277 | 14.025 | 10.421 | 41.540 | 1.00 46.04 |
| ATOM | 321 | CD | GLN | A | 277 | 14.687 | 9.962 | 42.837 | 1.00 47.69 |
| ATOM | 322 | OE1 | GLN | A | 277 | 15.832 | 10.329 | 43.131 | 1.00 49.61 |
| ATOM | 323 | NE2 | GLN | A | 277 | 13.976 | 9.148 | 43.611 | 1.00 47.67 |
| ATOM | 324 | C | GLN | A | 277 | 13.274 | 12.549 | 39.409 | 1.00 35.95 |
| ATOM | 325 | O | GLN | A | 277 | 13.491 | 13.705 | 39.767 | 1.00 33.68 |
| ATOM | 326 | N | GLY | A | 278 | 12.071 | 12.098 | 39.063 | 1.00 36.00 |
| ATOM | 327 | CA | GLY | A | 278 | 10.894 | 12.941 | 39.158 | 1.00 36.50 |
| ATOM | 328 | C | GLY | A | 278 | 10.322 | 13.474 | 37.852 | 1.00 36.89 |
| ATOM | 329 | O | GLY | A | 278 | 9.184 | 13.927 | 37.831 | 1.00 37.41 |
| ATOM | 330 | N | SER | A | 279 | 11.102 | 13.452 | 36.773 | 1.00 37.33 |
| ATOM | 331 | CA | SER | A | 279 | 10.633 | 13.948 | 35.480 | 1.00 36.11 |
| ATOM | 332 | CB | SER | A | 279 | 11.796 | 14.056 | 34.521 | 1.00 34.76 |
| ATOM | 333 | OG | SER | A | 279 | 12.707 | 15.004 | 35.030 | 1.00 35.41 |
| ATOM | 334 | C | SER | A | 279 | 9.547 | 13.056 | 34.904 | 1.00 35.83 |
| ATOM | 335 | O | SER | A | 279 | 8.661 | 13.518 | 34.183 | 1.00 36.11 |
| ATOM | 336 | N | MET | A | 280 | 9.610 | 11.785 | 35.275 | 1.00 34.60 |
| ATOM | 337 | CA | MET | A | 280 | 8.653 | 10.765 | 34.859 | 1.00 33.96 |
| ATOM | 338 | CB | MET | A | 280 | 8.691 | 10.518 | 33.336 | 1.00 32.70 |
| ATOM | 339 | CG | MET | A | 280 | 10.051 | 10.079 | 32.760 | 1.00 31.64 |
| ATOM | 340 | SD | MET | A | 280 | 10.192 | 10.069 | 30.922 | 1.00 28.96 |
| ATOM | 341 | CE | MET | A | 280 | 9.435 | 8.578 | 30.601 | 1.00 27.97 |

Figure 6

| ATOM | 342 | C | MET | A | 280 | 9.066 | 9.516 | 35.623 | 1.00 | 33.00 |
|------|-----|-----|-----|---|-----|--------|--------|--------|------|-------|
| ATOM | 343 | O | MET | A | 280 | 10.156 | 9.472 | 36.188 | 1.00 | 33.78 |
| ATOM | 344 | N | SER | A | 281 | 8.210 | 8.509 | 35.650 | 1.00 | 32.29 |
| ATOM | 345 | CA | SER | A | 281 | 8.529 | 7.291 | 36.374 | 1.00 | 33.29 |
| ATOM | 346 | CB | SER | A | 281 | 7.271 | 6.459 | 36.601 | 1.00 | 32.47 |
| ATOM | 347 | OG | SER | A | 281 | 6.939 | 5.719 | 35.441 | 1.00 | 33.18 |
| ATOM | 348 | C | SER | A | 281 | 9.564 | 6.419 | 35.672 | 1.00 | 35.43 |
| ATOM | 349 | O | SER | A | 281 | 9.702 | 6.448 | 34.445 | 1.00 | 35.12 |
| ATOM | 350 | N | PRO | A | 282 | 10.337 | 5.657 | 36.455 | 1.00 | 36.87 |
| ATOM | 351 | CD | PRO | A | 282 | 10.508 | 5.835 | 37.910 | 1.00 | 36.87 |
| ATOM | 352 | CA | PRO | A | 282 | 11.361 | 4.761 | 35.925 | 1.00 | 38.02 |
| ATOM | 353 | CB | PRO | A | 282 | 11.856 | 4.061 | 37.179 | 1.00 | 37.56 |
| ATOM | 354 | CG | PRO | A | 282 | 11.851 | 5.190 | 38.161 | 1.00 | 37.30 |
| ATOM | 355 | C | PRO | A | 282 | 10.763 | 3.782 | 34.924 | 1.00 | 38.94 |
| ATOM | 356 | O | PRO | A | 282 | 11.386 | 3.464 | 33.922 | 1.00 | 40.29 |
| ATOM | 357 | N | ASP | A | 283 | 9.543 | 3.325 | 35.183 | 1.00 | 40.57 |
| ATOM | 358 | CA | ASP | A | 283 | 8.876 | 2.393 | 34.279 | 1.00 | 41.40 |
| ATOM | 359 | CB | ASP | A | 283 | 7.648 | 1.754 | 34.942 | 1.00 | 43.73 |
| ATOM | 360 | CG | ASP | A | 283 | 8.008 | 0.546 | 35.824 | 1.00 | 44.93 |
| ATOM | 361 | OD1 | ASP | A | 283 | 9.212 | 0.265 | 36.044 | 1.00 | 45.23 |
| ATOM | 362 | OD2 | ASP | A | 283 | 7.071 | -0.137 | 36.293 | 1.00 | 46.39 |
| ATOM | 363 | C | ASP | A | 283 | 8.509 | 3.036 | 32.948 | 1.00 | 39.58 |
| ATOM | 364 | O | ASP | A | 283 | 8.521 | 2.376 | 31.919 | 1.00 | 40.67 |
| ATOM | 365 | N | ALA | A | 284 | 8.196 | 4.324 | 32.966 | 1.00 | 38.76 |
| ATOM | 366 | CA | ALA | A | 284 | 7.871 | 5.031 | 31.732 | 1.00 | 38.27 |
| ATOM | 367 | CB | ALA | A | 284 | 7.177 | 6.352 | 32.033 | 1.00 | 37.46 |
| ATOM | 368 | C | ALA | A | 284 | 9.148 | 5.281 | 30.925 | 1.00 | 38.40 |
| ATOM | 369 | O | ALA | A | 284 | 9.157 | 5.103 | 29.716 | 1.00 | 40.22 |
| ATOM | 370 | N | PHE | A | 285 | 10.217 | 5.696 | 31.611 | 1.00 | 37.47 |
| ATOM | 371 | CA | PHE | A | 285 | 11.524 | 5.985 | 31.003 | 1.00 | 34.51 |
| ATOM | 372 | CB | PHE | A | 285 | 12.496 | 6.465 | 32.092 | 1.00 | 31.02 |
| ATOM | 373 | CG | PHE | A | 285 | 13.888 | 6.741 | 31.602 | 1.00 | 28.30 |
| ATOM | 374 | CD1 | PHE | A | 285 | 14.166 | 7.883 | 30.862 | 1.00 | 27.45 |
| ATOM | 375 | CD2 | PHE | A | 285 | 14.927 | 5.862 | 31.888 | 1.00 | 26.33 |
| ATOM | 376 | CE1 | PHE | A | 285 | 15.447 | 8.144 | 30.417 | 1.00 | 25.69 |
| ATOM | 377 | CE2 | PHE | A | 285 | 16.206 | 6.120 | 31.445 | 1.00 | 24.61 |
| ATOM | 378 | CZ | PHE | A | 285 | 16.464 | 7.262 | 30.710 | 1.00 | 25.17 |
| ATOM | 379 | C | PHE | A | 285 | 12.077 | 4.743 | 30.317 | 1.00 | 35.37 |
| ATOM | 380 | O | PHE | A | 285 | 12.445 | 4.775 | 29.141 | 1.00 | 33.44 |
| ATOM | 381 | N | LEU | A | 286 | 12.082 | 3.644 | 31.066 | 1.00 | 36.42 |
| ATOM | 382 | CA | LEU | A | 286 | 12.575 | 2.352 | 30.598 | 1.00 | 38.12 |
| ATOM | 383 | CB | LEU | A | 286 | 12.618 | 1.358 | 31.759 | 1.00 | 36.82 |
| ATOM | 384 | CG | LEU | A | 286 | 13.721 | 1.606 | 32.777 | 1.00 | 36.31 |
| ATOM | 385 | CD1 | LEU | A | 286 | 13.462 | 0.769 | 34.015 | 1.00 | 36.61 |
| ATOM | 386 | CD2 | LEU | A | 286 | 15.076 | 1.292 | 32.153 | 1.00 | 35.48 |
| ATOM | 387 | C | LEU | A | 286 | 11.742 | 1.753 | 29.481 | 1.00 | 38.92 |
| ATOM | 388 | O | LEU | A | 286 | 12.274 | 1.065 | 28.611 | 1.00 | 39.23 |
| ATOM | 389 | N | ALA | A | 287 | 10.429 | 1.970 | 29.545 | 1.00 | 40.94 |
| ATOM | 390 | CA | ALA | A | 287 | 9.510 | 1.440 | 28.536 | 1.00 | 41.92 |
| ATOM | 391 | CB | ALA | A | 287 | 8.061 | 1.643 | 28.974 | 1.00 | 41.52 |
| ATOM | 392 | C | ALA | A | 287 | 9.757 | 2.092 | 27.176 | 1.00 | 41.48 |
| ATOM | 393 | O | ALA | A | 287 | 9.557 | 1.458 | 26.139 | 1.00 | 42.75 |
| ATOM | 394 | N | GLU | A | 288 | 10.212 | 3.346 | 27.197 | 1.00 | 40.02 |
| ATOM | 395 | CA | GLU | A | 288 | 10.502 | 4.081 | 25.973 | 1.00 | 40.65 |
| ATOM | 396 | CB | GLU | A | 288 | 10.890 | 5.547 | 26.277 | 1.00 | 39.30 |
| ATOM | 397 | CG | GLU | A | 288 | 9.793 | 6.381 | 26.942 | 1.00 | 38.95 |
| ATOM | 398 | CD | GLU | A | 288 | 10.077 | 7.886 | 26.965 | 1.00 | 39.58 |
| ATOM | 399 | OE1 | GLU | A | 288 | 11.235 | 8.301 | 27.203 | 1.00 | 40.41 |
| ATOM | 400 | OE2 | GLU | A | 288 | 9.136 | 8.676 | 26.764 | 1.00 | 39.51 |

Figure 6

| | | | | | | | | | |
|---|---|---|---|---|---|---|---|---|---|
| ATOM | 401 | C | GLU | A | 288 | 11.622 | 3.374 | 25.204 | 1.00 42.06 |
| ATOM | 402 | O | GLU | A | 288 | 11.712 | 3.496 | 23.984 | 1.00 44.37 |
| ATOM | 403 | N | ALA | A | 289 | 12.463 | 2.625 | 25.923 | 1.00 42.18 |
| ATOM | 404 | CA | ALA | A | 289 | 13.578 | 1.895 | 25.315 | 1.00 40.64 |
| ATOM | 405 | CB | ALA | A | 289 | 14.690 | 1.674 | 26.327 | 1.00 42.10 |
| ATOM | 406 | C | ALA | A | 289 | 13.174 | 0.577 | 24.696 | 1.00 40.03 |
| ATOM | 407 | O | ALA | A | 289 | 13.970 | -0.019 | 23.973 | 1.00 40.96 |
| ATOM | 408 | N | ASN | A | 290 | 11.967 | 0.097 | 25.001 | 1.00 39.66 |
| ATOM | 409 | CA | ASN | A | 290 | 11.478 | -1.163 | 24.418 | 1.00 39.36 |
| ATOM | 410 | CB | ASN | A | 290 | 10.141 | -1.584 | 25.029 | 1.00 40.92 |
| ATOM | 411 | CG | ASN | A | 290 | 10.233 | -1.841 | 26.502 | 1.00 41.92 |
| ATOM | 412 | OD1 | ASN | A | 290 | 9.290 | -1.568 | 27.234 | 1.00 42.16 |
| ATOM | 413 | ND2 | ASN | A | 290 | 11.367 | -2.379 | 26.950 | 1.00 41.75 |
| ATOM | 414 | C | ASN | A | 290 | 11.290 | -0.986 | 22.913 | 1.00 37.87 |
| ATOM | 415 | O | ASN | A | 290 | 11.256 | -1.951 | 22.156 | 1.00 37.86 |
| ATOM | 416 | N | LEU | A | 291 | 11.142 | 0.263 | 22.497 | 1.00 36.35 |
| ATOM | 417 | CA | LEU | A | 291 | 10.987 | 0.591 | 21.101 | 1.00 35.78 |
| ATOM | 418 | CB | LEU | A | 291 | 10.664 | 2.078 | 20.959 | 1.00 35.42 |
| ATOM | 419 | CG | LEU | A | 291 | 9.311 | 2.339 | 21.624 | 1.00 34.92 |
| ATOM | 420 | CD1 | LEU | A | 291 | 9.127 | 3.788 | 21.947 | 1.00 34.99 |
| ATOM | 421 | CD2 | LEU | A | 291 | 8.206 | 1.838 | 20.739 | 1.00 34.77 |
| ATOM | 422 | C | LEU | A | 291 | 12.262 | 0.194 | 20.350 | 1.00 35.90 |
| ATOM | 423 | O | LEU | A | 291 | 12.183 | -0.292 | 19.227 | 1.00 36.01 |
| ATOM | 424 | N | MET | A | 292 | 13.428 | 0.336 | 20.987 | 1.00 35.10 |
| ATOM | 425 | CA | MET | A | 292 | 14.679 | -0.072 | 20.344 | 1.00 33.51 |
| ATOM | 426 | CB | MET | A | 292 | 15.874 | 0.622 | 20.973 | 1.00 31.36 |
| ATOM | 427 | CG | MET | A | 292 | 16.006 | 2.043 | 20.541 | 1.00 29.89 |
| ATOM | 428 | SD | MET | A | 292 | 17.344 | 2.897 | 21.364 | 1.00 26.90 |
| ATOM | 429 | CE | MET | A | 292 | 16.605 | 3.157 | 22.979 | 1.00 27.22 |
| ATOM | 430 | C | MET | A | 292 | 14.879 | -1.579 | 20.385 | 1.00 35.26 |
| ATOM | 431 | O | MET | A | 292 | 15.801 | -2.101 | 19.769 | 1.00 35.91 |
| ATOM | 432 | N | LYS | A | 293 | 14.039 | -2.274 | 21.145 | 1.00 37.77 |
| ATOM | 433 | CA | LYS | A | 293 | 14.118 | -3.725 | 21.226 | 1.00 40.45 |
| ATOM | 434 | CB | LYS | A | 293 | 13.592 | -4.239 | 22.574 | 1.00 40.92 |
| ATOM | 435 | CG | LYS | A | 293 | 14.407 | -3.812 | 23.782 | 1.00 42.03 |
| ATOM | 436 | CD | LYS | A | 293 | 13.845 | -4.399 | 25.073 | 1.00 42.36 |
| ATOM | 437 | CE | LYS | A | 293 | 14.523 | -3.780 | 26.294 | 1.00 43.08 |
| ATOM | 438 | NZ | LYS | A | 293 | 14.026 | -4.343 | 27.579 | 1.00 43.48 |
| ATOM | 439 | C | LYS | A | 293 | 13.272 | -4.307 | 20.103 | 1.00 41.75 |
| ATOM | 440 | O | LYS | A | 293 | 13.599 | -5.357 | 19.537 | 1.00 42.69 |
| ATOM | 441 | N | GLN | A | 294 | 12.190 | -3.603 | 19.777 | 1.00 43.15 |
| ATOM | 442 | CA | GLN | A | 294 | 11.257 | -4.030 | 18.729 | 1.00 44.35 |
| ATOM | 443 | CB | GLN | A | 294 | 9.841 | -3.497 | 19.020 | 1.00 45.59 |
| ATOM | 444 | CG | GLN | A | 294 | 9.312 | -3.793 | 20.434 | 1.00 48.81 |
| ATOM | 445 | CD | GLN | A | 294 | 9.420 | -5.271 | 20.846 | 1.00 51.50 |
| ATOM | 446 | OE1 | GLN | A | 294 | 10.058 | -5.606 | 21.861 | 1.00 52.12 |
| ATOM | 447 | NE2 | GLN | A | 294 | 8.781 | -6.158 | 20.075 | 1.00 51.83 |
| ATOM | 448 | C | GLN | A | 294 | 11.680 | -3.710 | 17.271 | 1.00 43.69 |
| ATOM | 449 | O | GLN | A | 294 | 11.352 | -4.465 | 16.346 | 1.00 44.24 |
| ATOM | 450 | N | LEU | A | 295 | 12.406 | -2.610 | 17.069 | 1.00 42.01 |
| ATOM | 451 | CA | LEU | A | 295 | 12.857 | -2.238 | 15.724 | 1.00 40.85 |
| ATOM | 452 | CB | LEU | A | 295 | 12.209 | -0.921 | 15.292 | 1.00 41.39 |
| ATOM | 453 | CG | LEU | A | 295 | 10.687 | -0.831 | 15.247 | 1.00 40.84 |
| ATOM | 454 | CD1 | LEU | A | 295 | 10.296 | 0.585 | 14.922 | 1.00 40.71 |
| ATOM | 455 | CD2 | LEU | A | 295 | 10.139 | -1.799 | 14.210 | 1.00 41.44 |
| ATOM | 456 | C | LEU | A | 295 | 14.376 | -2.101 | 15.634 | 1.00 40.36 |
| ATOM | 457 | O | LEU | A | 295 | 14.951 | -1.152 | 16.167 | 1.00 40.24 |
| ATOM | 458 | N | GLN | A | 296 | 15.020 | -3.032 | 14.937 | 1.00 39.80 |
| ATOM | 459 | CA | GLN | A | 296 | 16.474 | -3.000 | 14.782 | 1.00 39.38 |

Figure 6

| ATOM | 460 | CB | GLN A 296 | 17.079 | -4.284 | 15.336 | 1.00 | 40.76 |
| --- | --- | --- | --- | --- | --- | --- | --- | --- |
| ATOM | 461 | CG | GLN A 296 | 16.600 | -4.609 | 16.746 | 1.00 | 42.46 |
| ATOM | 462 | CD | GLN A 296 | 17.255 | -5.849 | 17.318 | 1.00 | 44.01 |
| ATOM | 463 | OE1 | GLN A 296 | 17.786 | -6.676 | 16.585 | 1.00 | 45.49 |
| ATOM | 464 | NE2 | GLN A 296 | 17.251 | -5.965 | 18.642 | 1.00 | 45.40 |
| ATOM | 465 | C | GLN A 296 | 16.829 | -2.820 | 13.315 | 1.00 | 38.22 |
| ATOM | 466 | O | GLN A 296 | 16.345 | -3.564 | 12.458 | 1.00 | 39.28 |
| ATOM | 467 | N | HIS A 297 | 17.676 | -1.841 | 13.021 | 1.00 | 35.78 |
| ATOM | 468 | CA | HIS A 297 | 18.047 | -1.569 | 11.641 | 1.00 | 34.65 |
| ATOM | 469 | CB | HIS A 297 | 16.881 | -0.845 | 10.958 | 1.00 | 32.80 |
| ATOM | 470 | CG | HIS A 297 | 17.020 | -0.733 | 9.473 | 1.00 | 32.18 |
| ATOM | 471 | CD2 | HIS A 297 | 16.626 | -1.551 | 8.477 | 1.00 | 31.50 |
| ATOM | 472 | ND1 | HIS A 297 | 17.634 | 0.342 | 8.861 | 1.00 | 31.70 |
| ATOM | 473 | CE1 | HIS A 297 | 17.613 | 0.176 | 7.557 | 1.00 | 30.77 |
| ATOM | 474 | NE2 | HIS A 297 | 17.005 | -0.967 | 7.289 | 1.00 | 31.08 |
| ATOM | 475 | C | HIS A 297 | 19.297 | -0.695 | 11.590 | 1.00 | 35.17 |
| ATOM | 476 | O | HIS A 297 | 19.547 | 0.082 | 12.515 | 1.00 | 34.38 |
| ATOM | 477 | N | GLN A 298 | 20.052 | -0.787 | 10.492 | 1.00 | 36.04 |
| ATOM | 478 | CA | GLN A 298 | 21.268 | 0.006 | 10.344 | 1.00 | 38.29 |
| ATOM | 479 | CB | GLN A 298 | 22.045 | -0.391 | 9.080 | 1.00 | 43.19 |
| ATOM | 480 | CG | GLN A 298 | 23.002 | -1.584 | 9.272 | 1.00 | 49.73 |
| ATOM | 481 | CD | GLN A 298 | 23.937 | -1.421 | 10.494 | 1.00 | 52.93 |
| ATOM | 482 | OE1 | GLN A 298 | 24.138 | -2.366 | 11.281 | 1.00 | 53.63 |
| ATOM | 483 | NE2 | GLN A 298 | 24.496 | -0.215 | 10.660 | 1.00 | 53.74 |
| ATOM | 484 | C | GLN A 298 | 21.049 | 1.511 | 10.367 | 1.00 | 36.70 |
| ATOM | 485 | O | GLN A 298 | 21.971 | 2.274 | 10.619 | 1.00 | 36.57 |
| ATOM | 486 | N | ARG A 299 | 19.818 | 1.934 | 10.132 | 1.00 | 35.43 |
| ATOM | 487 | CA | ARG A 299 | 19.480 | 3.355 | 10.129 | 1.00 | 34.50 |
| ATOM | 488 | CB | ARG A 299 | 18.612 | 3.673 | 8.919 | 1.00 | 34.85 |
| ATOM | 489 | CG | ARG A 299 | 19.307 | 3.415 | 7.608 | 1.00 | 35.85 |
| ATOM | 490 | CD | ARG A 299 | 20.409 | 4.411 | 7.377 | 1.00 | 35.25 |
| ATOM | 491 | NE | ARG A 299 | 21.480 | 3.797 | 6.618 | 1.00 | 37.33 |
| ATOM | 492 | CZ | ARG A 299 | 22.752 | 3.803 | 6.999 | 1.00 | 38.90 |
| ATOM | 493 | NH1 | ARG A 299 | 23.109 | 4.399 | 8.135 | 1.00 | 38.63 |
| ATOM | 494 | NH2 | ARG A 299 | 23.670 | 3.236 | 6.230 | 1.00 | 39.41 |
| ATOM | 495 | C | ARG A 299 | 18.782 | 3.844 | 11.410 | 1.00 | 33.66 |
| ATOM | 496 | O | ARG A 299 | 18.441 | 5.023 | 11.525 | 1.00 | 32.09 |
| ATOM | 497 | N | LEU A 300 | 18.541 | 2.926 | 12.345 | 1.00 | 33.61 |
| ATOM | 498 | CA | LEU A 300 | 17.911 | 3.249 | 13.628 | 1.00 | 31.54 |
| ATOM | 499 | CB | LEU A 300 | 16.741 | 2.298 | 13.891 | 1.00 | 29.58 |
| ATOM | 500 | CG | LEU A 300 | 15.339 | 2.655 | 13.388 | 1.00 | 28.29 |
| ATOM | 501 | CD1 | LEU A 300 | 15.356 | 3.255 | 12.008 | 1.00 | 26.61 |
| ATOM | 502 | CD2 | LEU A 300 | 14.490 | 1.397 | 13.418 | 1.00 | 27.82 |
| ATOM | 503 | C | LEU A 300 | 18.961 | 3.107 | 14.738 | 1.00 | 32.02 |
| ATOM | 504 | O | LEU A 300 | 19.849 | 2.244 | 14.654 | 1.00 | 31.97 |
| ATOM | 505 | N | VAL A 301 | 18.882 | 3.992 | 15.737 | 1.00 | 32.73 |
| ATOM | 506 | CA | VAL A 301 | 19.791 | 3.985 | 16.892 | 1.00 | 31.61 |
| ATOM | 507 | CB | VAL A 301 | 19.438 | 5.110 | 17.871 | 1.00 | 30.59 |
| ATOM | 508 | CG1 | VAL A 301 | 20.099 | 4.870 | 19.211 | 1.00 | 31.54 |
| ATOM | 509 | CG2 | VAL A 301 | 19.876 | 6.451 | 17.303 | 1.00 | 30.61 |
| ATOM | 510 | C | VAL A 301 | 19.654 | 2.642 | 17.598 | 1.00 | 32.77 |
| ATOM | 511 | O | VAL A 301 | 18.547 | 2.223 | 17.934 | 1.00 | 32.51 |
| ATOM | 512 | N | ARG A 302 | 20.784 | 1.982 | 17.827 | 1.00 | 34.64 |
| ATOM | 513 | CA | ARG A 302 | 20.816 | 0.657 | 18.445 | 1.00 | 35.29 |
| ATOM | 514 | CB | ARG A 302 | 21.966 | -0.140 | 17.809 | 1.00 | 37.56 |
| ATOM | 515 | CG | ARG A 302 | 22.164 | -1.552 | 18.304 | 1.00 | 40.90 |
| ATOM | 516 | CD | ARG A 302 | 23.204 | -1.593 | 19.422 | 1.00 | 44.59 |
| ATOM | 517 | NE | ARG A 302 | 23.711 | -2.943 | 19.683 | 1.00 | 47.45 |
| ATOM | 518 | CZ | ARG A 302 | 24.473 | -3.636 | 18.834 | 1.00 | 48.51 |

Figure 6

| | | | | | | | | | |
|---|---|---|---|---|---|---|---|---|---|
| ATOM | 519 | NH1 | ARG | A | 302 | 24.823 | -3.120 | 17.659 | 1.00 48.43 |
| ATOM | 520 | NH2 | ARG | A | 302 | 24.906 | -4.841 | 19.172 | 1.00 49.50 |
| ATOM | 521 | C | ARG | A | 302 | 20.910 | 0.666 | 19.979 | 1.00 34.05 |
| ATOM | 522 | O | ARG | A | 302 | 21.560 | 1.535 | 20.573 | 1.00 33.33 |
| ATOM | 523 | N | LEU | A | 303 | 20.217 | -0.284 | 20.609 | 1.00 32.63 |
| ATOM | 524 | CA | LEU | A | 303 | 20.222 | -0.424 | 22.072 | 1.00 31.40 |
| ATOM | 525 | CB | LEU | A | 303 | 18.818 | -0.751 | 22.602 | 1.00 28.46 |
| ATOM | 526 | CG | LEU | A | 303 | 18.677 | -0.996 | 24.115 | 1.00 27.11 |
| ATOM | 527 | CD1 | LEU | A | 303 | 18.767 | 0.316 | 24.860 | 1.00 26.69 |
| ATOM | 528 | CD2 | LEU | A | 303 | 17.359 | -1.686 | 24.463 | 1.00 24.47 |
| ATOM | 529 | C | LEU | A | 303 | 21.172 | -1.555 | 22.483 | 1.00 31.54 |
| ATOM | 530 | O | LEU | A | 303 | 21.214 | -2.603 | 21.826 | 1.00 30.76 |
| ATOM | 531 | N | TYR | A | 304 | 21.959 | -1.314 | 23.536 | 1.00 31.70 |
| ATOM | 532 | CA | TYR | A | 304 | 22.886 | -2.307 | 24.080 | 1.00 31.77 |
| ATOM | 533 | CB | TYR | A | 304 | 24.239 | -1.668 | 24.395 | 1.00 33.80 |
| ATOM | 534 | CG | TYR | A | 304 | 25.126 | -1.409 | 23.198 | 1.00 35.87 |
| ATOM | 535 | CD1 | TYR | A | 304 | 25.259 | -0.124 | 22.676 | 1.00 37.55 |
| ATOM | 536 | CE1 | TYR | A | 304 | 26.106 | 0.133 | 21.602 | 1.00 38.50 |
| ATOM | 537 | CD2 | TYR | A | 304 | 25.869 | -2.441 | 22.610 | 1.00 37.53 |
| ATOM | 538 | CE2 | TYR | A | 304 | 26.726 | -2.192 | 21.527 | 1.00 38.34 |
| ATOM | 539 | CZ | TYR | A | 304 | 26.834 | -0.899 | 21.036 | 1.00 38.49 |
| ATOM | 540 | OH | TYR | A | 304 | 27.671 | -0.619 | 19.990 | 1.00 38.12 |
| ATOM | 541 | C | TYR | A | 304 | 22.294 | -2.878 | 25.378 | 1.00 31.79 |
| ATOM | 542 | O | TYR | A | 304 | 22.133 | -4.083 | 25.528 | 1.00 32.82 |
| ATOM | 543 | N | ALA | A | 305 | 21.941 | -2.008 | 26.311 | 1.00 30.93 |
| ATOM | 544 | CA | ALA | A | 305 | 21.379 | -2.475 | 27.561 | 1.00 30.00 |
| ATOM | 545 | CB | ALA | A | 305 | 22.447 | -3.198 | 28.360 | 1.00 30.30 |
| ATOM | 546 | C | ALA | A | 305 | 20.795 | -1.346 | 28.385 | 1.00 30.43 |
| ATOM | 547 | O | ALA | A | 305 | 20.870 | -0.172 | 28.009 | 1.00 26.21 |
| ATOM | 548 | N | VAL | A | 306 | 20.208 | -1.726 | 29.518 | 1.00 32.96 |
| ATOM | 549 | CA | VAL | A | 306 | 19.606 | -0.778 | 30.458 | 1.00 35.15 |
| ATOM | 550 | CB | VAL | A | 306 | 18.050 | -0.751 | 30.343 | 1.00 35.61 |
| ATOM | 551 | CG1 | VAL | A | 306 | 17.609 | -0.161 | 28.994 | 1.00 35.09 |
| ATOM | 552 | CG2 | VAL | A | 306 | 17.480 | -2.155 | 30.538 | 1.00 35.46 |
| ATOM | 553 | C | VAL | A | 306 | 19.971 | -1.106 | 31.916 | 1.00 35.65 |
| ATOM | 554 | O | VAL | A | 306 | 20.217 | -2.263 | 32.258 | 1.00 35.11 |
| ATOM | 555 | N | VAL | A | 307 | 20.064 | -0.067 | 32.746 | 1.00 36.54 |
| ATOM | 556 | CA | VAL | A | 307 | 20.350 | -0.218 | 34.171 | 1.00 36.89 |
| ATOM | 557 | CB | VAL | A | 307 | 21.605 | 0.552 | 34.610 | 1.00 35.19 |
| ATOM | 558 | CG1 | VAL | A | 307 | 21.791 | 0.438 | 36.114 | 1.00 34.73 |
| ATOM | 559 | CG2 | VAL | A | 307 | 22.810 | -0.012 | 33.904 | 1.00 33.44 |
| ATOM | 560 | C | VAL | A | 307 | 19.109 | 0.270 | 34.918 | 1.00 38.90 |
| ATOM | 561 | O | VAL | A | 307 | 18.774 | 1.463 | 34.938 | 1.00 36.56 |
| ATOM | 562 | N | THR | A | 308 | 18.417 | -0.694 | 35.502 | 1.00 42.23 |
| ATOM | 563 | CA | THR | A | 308 | 17.178 | -0.443 | 36.213 | 1.00 46.54 |
| ATOM | 564 | CB | THR | A | 308 | 16.306 | -1.703 | 36.164 | 1.00 47.52 |
| ATOM | 565 | OG1 | THR | A | 308 | 17.080 | -2.829 | 36.603 | 1.00 48.64 |
| ATOM | 566 | CG2 | THR | A | 308 | 15.839 | -1.960 | 34.709 | 1.00 47.94 |
| ATOM | 567 | C | THR | A | 308 | 17.216 | 0.158 | 37.634 | 1.00 48.59 |
| ATOM | 568 | O | THR | A | 308 | 16.215 | 0.721 | 38.077 | 1.00 48.67 |
| ATOM | 569 | N | GLN | A | 309 | 18.351 | 0.075 | 38.335 | 1.00 50.37 |
| ATOM | 570 | CA | GLN | A | 309 | 18.461 | 0.651 | 39.681 | 1.00 51.23 |
| ATOM | 571 | CB | GLN | A | 309 | 19.438 | -0.160 | 40.551 | 1.00 51.25 |
| ATOM | 572 | CG | GLN | A | 309 | 18.961 | -1.559 | 40.890 | 0.00 51.61 |
| ATOM | 573 | CD | GLN | A | 309 | 17.683 | -1.568 | 41.708 | 0.00 51.69 |
| ATOM | 574 | OE1 | GLN | A | 309 | 17.114 | -0.520 | 42.026 | 0.00 51.74 |
| ATOM | 575 | NE2 | GLN | A | 309 | 17.227 | -2.759 | 42.058 | 0.00 51.78 |
| ATOM | 576 | C | GLN | A | 309 | 18.894 | 2.120 | 39.614 | 1.00 51.49 |
| ATOM | 577 | O | GLN | A | 309 | 19.818 | 2.462 | 38.872 | 1.00 50.74 |

Figure 6

| ATOM | 578 | N   | GLU | A | 310 | 18.223 | 2.979 | 40.390 | 1.00 | 52.14 |
| ATOM | 579 | CA  | GLU | A | 310 | 18.523 | 4.418 | 40.423 | 1.00 | 53.39 |
| ATOM | 580 | CB  | GLU | A | 310 | 17.627 | 5.156 | 41.439 | 1.00 | 53.96 |
| ATOM | 581 | CG  | GLU | A | 310 | 17.569 | 4.564 | 42.839 | 0.00 | 54.16 |
| ATOM | 582 | CD  | GLU | A | 310 | 16.371 | 3.661 | 43.044 | 0.00 | 54.38 |
| ATOM | 583 | OE1 | GLU | A | 310 | 15.261 | 4.011 | 42.586 | 0.00 | 54.40 |
| ATOM | 584 | OE2 | GLU | A | 310 | 16.539 | 2.603 | 43.680 | 0.00 | 54.55 |
| ATOM | 585 | C   | GLU | A | 310 | 19.998 | 4.752 | 40.698 | 1.00 | 53.26 |
| ATOM | 586 | O   | GLU | A | 310 | 20.582 | 4.242 | 41.664 | 1.00 | 54.04 |
| ATOM | 587 | N   | PRO | A | 311 | 20.630 | 5.601 | 39.837 | 1.00 | 52.53 |
| ATOM | 588 | CD  | PRO | A | 311 | 21.997 | 6.100 | 40.065 | 1.00 | 52.14 |
| ATOM | 589 | CA  | PRO | A | 311 | 20.052 | 6.249 | 38.642 | 1.00 | 50.84 |
| ATOM | 590 | CB  | PRO | A | 311 | 21.117 | 7.303 | 38.270 | 1.00 | 51.03 |
| ATOM | 591 | CG  | PRO | A | 311 | 21.905 | 7.504 | 39.533 | 1.00 | 51.57 |
| ATOM | 592 | C   | PRO | A | 311 | 19.810 | 5.275 | 37.472 | 1.00 | 48.55 |
| ATOM | 593 | O   | PRO | A | 311 | 20.664 | 4.439 | 37.150 | 1.00 | 48.30 |
| ATOM | 594 | N   | ILE | A | 312 | 18.644 | 5.399 | 36.834 | 1.00 | 45.41 |
| ATOM | 595 | CA  | ILE | A | 312 | 18.286 | 4.536 | 35.709 | 1.00 | 41.74 |
| ATOM | 596 | CB  | ILE | A | 312 | 16.767 | 4.640 | 35.359 | 1.00 | 43.02 |
| ATOM | 597 | CG2 | ILE | A | 312 | 16.307 | 3.364 | 34.666 | 1.00 | 43.60 |
| ATOM | 598 | CG1 | ILE | A | 312 | 15.915 | 4.913 | 36.615 | 1.00 | 42.22 |
| ATOM | 599 | CD1 | ILE | A | 312 | 15.913 | 3.806 | 37.634 | 1.00 | 41.60 |
| ATOM | 600 | C   | ILE | A | 312 | 19.090 | 4.975 | 34.487 | 1.00 | 37.94 |
| ATOM | 601 | O   | ILE | A | 312 | 19.254 | 6.183 | 34.263 | 1.00 | 35.28 |
| ATOM | 602 | N   | TYR | A | 313 | 19.555 | 3.996 | 33.703 | 1.00 | 35.20 |
| ATOM | 603 | CA  | TYR | A | 313 | 20.356 | 4.236 | 32.485 | 1.00 | 32.53 |
| ATOM | 604 | CB  | TYR | A | 313 | 21.812 | 3.796 | 32.670 | 1.00 | 32.89 |
| ATOM | 605 | CG  | TYR | A | 313 | 22.699 | 4.577 | 33.611 | 1.00 | 33.11 |
| ATOM | 606 | CD1 | TYR | A | 313 | 22.428 | 5.893 | 33.952 | 1.00 | 33.33 |
| ATOM | 607 | CE1 | TYR | A | 313 | 23.291 | 6.603 | 34.778 | 1.00 | 34.09 |
| ATOM | 608 | CD2 | TYR | A | 313 | 23.856 | 3.992 | 34.123 | 1.00 | 33.24 |
| ATOM | 609 | CE2 | TYR | A | 313 | 24.718 | 4.692 | 34.943 | 1.00 | 33.46 |
| ATOM | 610 | CZ  | TYR | A | 313 | 24.433 | 5.993 | 35.265 | 1.00 | 34.18 |
| ATOM | 611 | OH  | TYR | A | 313 | 25.292 | 6.696 | 36.079 | 1.00 | 36.66 |
| ATOM | 612 | C   | TYR | A | 313 | 19.907 | 3.449 | 31.248 | 1.00 | 31.53 |
| ATOM | 613 | O   | TYR | A | 313 | 19.614 | 2.259 | 31.322 | 1.00 | 31.00 |
| ATOM | 614 | N   | ILE | A | 314 | 19.956 | 4.104 | 30.093 | 1.00 | 29.61 |
| ATOM | 615 | CA  | ILE | A | 314 | 19.660 | 3.454 | 28.821 | 1.00 | 27.72 |
| ATOM | 616 | CB  | ILE | A | 314 | 18.519 | 4.154 | 28.042 | 1.00 | 27.83 |
| ATOM | 617 | CG2 | ILE | A | 314 | 18.484 | 3.653 | 26.598 | 1.00 | 26.69 |
| ATOM | 618 | CG1 | ILE | A | 314 | 17.175 | 3.877 | 28.736 | 1.00 | 27.69 |
| ATOM | 619 | CD1 | ILE | A | 314 | 16.003 | 4.660 | 28.178 | 1.00 | 28.12 |
| ATOM | 620 | C   | ILE | A | 314 | 20.981 | 3.566 | 28.071 | 1.00 | 25.98 |
| ATOM | 621 | O   | ILE | A | 314 | 21.519 | 4.656 | 27.940 | 1.00 | 23.32 |
| ATOM | 622 | N   | ILE | A | 315 | 21.546 | 2.424 | 27.696 | 1.00 | 25.82 |
| ATOM | 623 | CA  | ILE | A | 315 | 22.825 | 2.378 | 27.000 | 1.00 | 28.42 |
| ATOM | 624 | CB  | ILE | A | 315 | 23.775 | 1.273 | 27.573 | 1.00 | 29.78 |
| ATOM | 625 | CG2 | ILE | A | 315 | 25.042 | 1.176 | 26.743 | 1.00 | 28.81 |
| ATOM | 626 | CG1 | ILE | A | 315 | 24.155 | 1.567 | 29.024 | 1.00 | 30.47 |
| ATOM | 627 | CD1 | ILE | A | 315 | 23.276 | 0.898 | 30.032 | 1.00 | 31.22 |
| ATOM | 628 | C   | ILE | A | 315 | 22.646 | 2.121 | 25.506 | 1.00 | 29.09 |
| ATOM | 629 | O   | ILE | A | 315 | 22.256 | 1.028 | 25.093 | 1.00 | 29.06 |
| ATOM | 630 | N   | THR | A | 316 | 22.985 | 3.115 | 24.695 | 1.00 | 27.79 |
| ATOM | 631 | CA  | THR | A | 316 | 22.847 | 2.980 | 23.255 | 1.00 | 28.28 |
| ATOM | 632 | CB  | THR | A | 316 | 21.839 | 3.997 | 22.670 | 1.00 | 26.98 |
| ATOM | 633 | OG1 | THR | A | 316 | 22.292 | 5.333 | 22.941 | 1.00 | 26.88 |
| ATOM | 634 | CG2 | THR | A | 316 | 20.459 | 3.784 | 23.256 | 1.00 | 24.66 |
| ATOM | 635 | C   | THR | A | 316 | 24.184 | 3.241 | 22.601 | 1.00 | 29.89 |
| ATOM | 636 | O   | THR | A | 316 | 25.099 | 3.760 | 23.234 | 1.00 | 31.00 |

Figure 6

| | | | | | | | | |
|---|---|---|---|---|---|---|---|---|
| ATOM | 637 | N | GLU | A | 317 | 24.287 | 2.891 | 21.320 | 1.00 | 30.39 |
| ATOM | 638 | CA | GLU | A | 317 | 25.513 | 3.117 | 20.563 | 1.00 | 28.41 |
| ATOM | 639 | CB | GLU | A | 317 | 25.334 | 2.682 | 19.113 | 1.00 | 28.56 |
| ATOM | 640 | CG | GLU | A | 317 | 24.331 | 3.520 | 18.353 | 1.00 | 28.33 |
| ATOM | 641 | CD | GLU | A | 317 | 24.260 | 3.134 | 16.913 | 1.00 | 27.50 |
| ATOM | 642 | OE1 | GLU | A | 317 | 23.144 | 2.835 | 16.441 | 1.00 | 27.21 |
| ATOM | 643 | OE2 | GLU | A | 317 | 25.328 | 3.120 | 16.262 | 1.00 | 28.89 |
| ATOM | 644 | C | GLU | A | 317 | 25.845 | 4.593 | 20.600 | 1.00 | 25.75 |
| ATOM | 645 | O | GLU | A | 317 | 24.966 | 5.430 | 20.818 | 1.00 | 24.15 |
| ATOM | 646 | N | TYR | A | 318 | 27.123 | 4.901 | 20.424 | 1.00 | 25.19 |
| ATOM | 647 | CA | TYR | A | 318 | 27.585 | 6.285 | 20.437 | 1.00 | 24.32 |
| ATOM | 648 | CB | TYR | A | 318 | 28.984 | 6.355 | 21.069 | 1.00 | 21.98 |
| ATOM | 649 | CG | TYR | A | 318 | 29.600 | 7.721 | 21.072 | 1.00 | 20.86 |
| ATOM | 650 | CD1 | TYR | A | 318 | 29.115 | 8.716 | 21.904 | 1.00 | 20.96 |
| ATOM | 651 | CE1 | TYR | A | 318 | 29.676 | 9.979 | 21.917 | 1.00 | 21.41 |
| ATOM | 652 | CD2 | TYR | A | 318 | 30.666 | 8.020 | 20.245 | 1.00 | 20.22 |
| ATOM | 653 | CE2 | TYR | A | 318 | 31.238 | 9.277 | 20.249 | 1.00 | 20.63 |
| ATOM | 654 | CZ | TYR | A | 318 | 30.740 | 10.257 | 21.088 | 1.00 | 21.95 |
| ATOM | 655 | OH | TYR | A | 318 | 31.306 | 11.521 | 21.108 | 1.00 | 23.52 |
| ATOM | 656 | C | TYR | A | 318 | 27.599 | 6.816 | 19.003 | 1.00 | 24.38 |
| ATOM | 657 | O | TYR | A | 318 | 27.934 | 6.087 | 18.076 | 1.00 | 25.13 |
| ATOM | 658 | N | MET | A | 319 | 27.180 | 8.062 | 18.827 | 1.00 | 24.00 |
| ATOM | 659 | CA | MET | A | 319 | 27.158 | 8.702 | 17.522 | 1.00 | 25.59 |
| ATOM | 660 | CB | MET | A | 319 | 25.725 | 9.041 | 17.109 | 1.00 | 25.37 |
| ATOM | 661 | CG | MET | A | 319 | 24.840 | 7.818 | 16.782 | 1.00 | 26.62 |
| ATOM | 662 | SD | MET | A | 319 | 25.223 | 6.907 | 15.218 | 1.00 | 28.75 |
| ATOM | 663 | CE | MET | A | 319 | 24.634 | 8.074 | 13.999 | 1.00 | 27.43 |
| ATOM | 664 | C | MET | A | 319 | 28.026 | 9.958 | 17.626 | 1.00 | 27.86 |
| ATOM | 665 | O | MET | A | 319 | 27.592 | 11.017 | 18.088 | 1.00 | 27.24 |
| ATOM | 666 | N | GLU | A | 320 | 29.279 | 9.797 | 17.222 | 1.00 | 31.24 |
| ATOM | 667 | CA | GLU | A | 320 | 30.308 | 10.839 | 17.267 | 1.00 | 33.53 |
| ATOM | 668 | CB | GLU | A | 320 | 31.454 | 10.447 | 16.332 | 1.00 | 37.68 |
| ATOM | 669 | CG | GLU | A | 320 | 32.433 | 11.577 | 15.982 | 1.00 | 42.21 |
| ATOM | 670 | CD | GLU | A | 320 | 33.714 | 11.544 | 16.791 | 1.00 | 44.17 |
| ATOM | 671 | OE1 | GLU | A | 320 | 34.007 | 10.520 | 17.444 | 1.00 | 46.41 |
| ATOM | 672 | OE2 | GLU | A | 320 | 34.441 | 12.552 | 16.754 | 1.00 | 45.46 |
| ATOM | 673 | C | GLU | A | 320 | 29.922 | 12.301 | 17.019 | 1.00 | 32.53 |
| ATOM | 674 | O | GLU | A | 320 | 30.271 | 13.189 | 17.821 | 1.00 | 33.28 |
| ATOM | 675 | N | ASN | A | 321 | 29.234 | 12.569 | 15.915 | 1.00 | 29.61 |
| ATOM | 676 | CA | ASN | A | 321 | 28.870 | 13.940 | 15.608 | 1.00 | 27.37 |
| ATOM | 677 | CB | ASN | A | 321 | 29.005 | 14.189 | 14.122 | 1.00 | 28.33 |
| ATOM | 678 | CG | ASN | A | 321 | 30.448 | 14.179 | 13.686 | 1.00 | 26.84 |
| ATOM | 679 | OD1 | ASN | A | 321 | 31.231 | 15.021 | 14.114 | 1.00 | 26.71 |
| ATOM | 680 | ND2 | ASN | A | 321 | 30.814 | 13.217 | 12.861 | 1.00 | 24.91 |
| ATOM | 681 | C | ASN | A | 321 | 27.557 | 14.450 | 16.182 | 1.00 | 27.04 |
| ATOM | 682 | O | ASN | A | 321 | 27.088 | 15.550 | 15.848 | 1.00 | 27.08 |
| ATOM | 683 | N | GLY | A | 322 | 27.016 | 13.664 | 17.106 | 1.00 | 26.70 |
| ATOM | 684 | CA | GLY | A | 322 | 25.804 | 14.032 | 17.811 | 1.00 | 25.35 |
| ATOM | 685 | C | GLY | A | 322 | 24.536 | 14.192 | 17.014 | 1.00 | 24.50 |
| ATOM | 686 | O | GLY | A | 322 | 24.164 | 13.322 | 16.235 | 1.00 | 25.04 |
| ATOM | 687 | N | SER | A | 323 | 23.872 | 15.318 | 17.222 | 1.00 | 22.46 |
| ATOM | 688 | CA | SER | A | 323 | 22.613 | 15.597 | 16.569 | 1.00 | 22.62 |
| ATOM | 689 | CB | SER | A | 323 | 21.718 | 16.397 | 17.526 | 1.00 | 21.96 |
| ATOM | 690 | OG | SER | A | 323 | 20.487 | 16.768 | 16.934 | 1.00 | 23.89 |
| ATOM | 691 | C | SER | A | 323 | 22.801 | 16.330 | 15.245 | 1.00 | 22.79 |
| ATOM | 692 | O | SER | A | 323 | 23.511 | 17.332 | 15.175 | 1.00 | 21.66 |
| ATOM | 693 | N | LEU | A | 324 | 22.105 | 15.858 | 14.211 | 1.00 | 22.81 |
| ATOM | 694 | CA | LEU | A | 324 | 22.184 | 16.443 | 12.876 | 1.00 | 21.75 |
| ATOM | 695 | CB | LEU | A | 324 | 21.261 | 15.704 | 11.913 | 1.00 | 21.29 |

Figure 6

| ATOM | 696 | CG | LEU | A | 324 | 21.057 | 16.251 | 10.497 | 1.00 | 20.10 |
| --- | --- | --- | --- | --- | --- | --- | --- | --- | --- | --- |
| ATOM | 697 | CD1 | LEU | A | 324 | 22.348 | 16.106 | 9.720 | 1.00 | 19.25 |
| ATOM | 698 | CD2 | LEU | A | 324 | 19.936 | 15.493 | 9.812 | 1.00 | 18.54 |
| ATOM | 699 | C | LEU | A | 324 | 21.888 | 17.929 | 12.817 | 1.00 | 22.09 |
| ATOM | 700 | O | LEU | A | 324 | 22.547 | 18.642 | 12.076 | 1.00 | 23.60 |
| ATOM | 701 | N | VAL | A | 325 | 20.902 | 18.407 | 13.572 | 1.00 | 23.77 |
| ATOM | 702 | CA | VAL | A | 325 | 20.589 | 19.835 | 13.544 | 1.00 | 24.53 |
| ATOM | 703 | CB | VAL | A | 325 | 19.311 | 20.177 | 14.365 | 1.00 | 22.97 |
| ATOM | 704 | CG1 | VAL | A | 325 | 19.565 | 20.004 | 15.853 | 1.00 | 22.49 |
| ATOM | 705 | CG2 | VAL | A | 325 | 18.833 | 21.592 | 14.047 | 1.00 | 20.81 |
| ATOM | 706 | C | VAL | A | 325 | 21.799 | 20.610 | 14.068 | 1.00 | 26.41 |
| ATOM | 707 | O | VAL | A | 325 | 22.000 | 21.772 | 13.722 | 1.00 | 26.94 |
| ATOM | 708 | N | ASP | A | 326 | 22.610 | 19.938 | 14.887 | 1.00 | 28.96 |
| ATOM | 709 | CA | ASP | A | 326 | 23.822 | 20.531 | 15.451 | 1.00 | 30.40 |
| ATOM | 710 | CB | ASP | A | 326 | 24.182 | 19.869 | 16.787 | 1.00 | 28.74 |
| ATOM | 711 | CG | ASP | A | 326 | 23.275 | 20.303 | 17.903 | 1.00 | 28.73 |
| ATOM | 712 | OD1 | ASP | A | 326 | 22.657 | 21.387 | 17.773 | 1.00 | 26.73 |
| ATOM | 713 | OD2 | ASP | A | 326 | 23.192 | 19.570 | 18.912 | 1.00 | 28.73 |
| ATOM | 714 | C | ASP | A | 326 | 25.001 | 20.424 | 14.486 | 1.00 | 31.18 |
| ATOM | 715 | O | ASP | A | 326 | 25.713 | 21.400 | 14.254 | 1.00 | 32.41 |
| ATOM | 716 | N | PHE | A | 327 | 25.165 | 19.245 | 13.900 | 1.00 | 30.53 |
| ATOM | 717 | CA | PHE | A | 327 | 26.251 | 18.979 | 12.979 | 1.00 | 30.97 |
| ATOM | 718 | CB | PHE | A | 327 | 26.255 | 17.506 | 12.577 | 1.00 | 31.38 |
| ATOM | 719 | CG | PHE | A | 327 | 27.373 | 17.136 | 11.649 | 1.00 | 32.82 |
| ATOM | 720 | CD1 | PHE | A | 327 | 28.697 | 17.181 | 12.081 | 1.00 | 33.23 |
| ATOM | 721 | CD2 | PHE | A | 327 | 27.108 | 16.767 | 10.331 | 1.00 | 32.62 |
| ATOM | 722 | CE1 | PHE | A | 327 | 29.748 | 16.866 | 11.207 | 1.00 | 34.66 |
| ATOM | 723 | CE2 | PHE | A | 327 | 28.144 | 16.451 | 9.449 | 1.00 | 33.04 |
| ATOM | 724 | CZ | PHE | A | 327 | 29.467 | 16.499 | 9.883 | 1.00 | 33.56 |
| ATOM | 725 | C | PHE | A | 327 | 26.259 | 19.868 | 11.740 | 1.00 | 31.73 |
| ATOM | 726 | O | PHE | A | 327 | 27.316 | 20.367 | 11.356 | 1.00 | 31.65 |
| ATOM | 727 | N | LEU | A | 328 | 25.084 | 20.087 | 11.145 | 1.00 | 31.00 |
| ATOM | 728 | CA | LEU | A | 328 | 24.940 | 20.910 | 9.932 | 1.00 | 29.05 |
| ATOM | 729 | CB | LEU | A | 328 | 23.475 | 20.948 | 9.475 | 1.00 | 27.97 |
| ATOM | 730 | CG | LEU | A | 328 | 22.727 | 19.673 | 9.101 | 1.00 | 26.17 |
| ATOM | 731 | CD1 | LEU | A | 328 | 21.252 | 19.982 | 9.003 | 1.00 | 25.16 |
| ATOM | 732 | CD2 | LEU | A | 328 | 23.269 | 19.093 | 7.800 | 1.00 | 26.57 |
| ATOM | 733 | C | LEU | A | 328 | 25.445 | 22.346 | 10.118 | 1.00 | 30.46 |
| ATOM | 734 | O | LEU | A | 328 | 25.761 | 23.036 | 9.138 | 1.00 | 31.04 |
| ATOM | 735 | N | LYS | A | 329 | 25.483 | 22.800 | 11.373 | 1.00 | 31.42 |
| ATOM | 736 | CA | LYS | A | 329 | 25.949 | 24.146 | 11.712 | 1.00 | 30.49 |
| ATOM | 737 | CB | LYS | A | 329 | 25.227 | 24.682 | 12.948 | 1.00 | 29.88 |
| ATOM | 738 | CG | LYS | A | 329 | 23.737 | 24.804 | 12.827 | 1.00 | 29.99 |
| ATOM | 739 | CD | LYS | A | 329 | 23.226 | 25.818 | 13.819 | 1.00 | 31.38 |
| ATOM | 740 | CE | LYS | A | 329 | 21.720 | 25.782 | 13.920 | 1.00 | 32.98 |
| ATOM | 741 | NZ | LYS | A | 329 | 21.284 | 24.424 | 14.319 | 1.00 | 34.08 |
| ATOM | 742 | C | LYS | A | 329 | 27.460 | 24.237 | 11.955 | 1.00 | 30.26 |
| ATOM | 743 | O | LYS | A | 329 | 28.029 | 25.327 | 11.860 | 1.00 | 30.17 |
| ATOM | 744 | N | THR | A | 330 | 28.094 | 23.111 | 12.302 | 1.00 | 30.56 |
| ATOM | 745 | CA | THR | A | 330 | 29.540 | 23.079 | 12.564 | 1.00 | 33.02 |
| ATOM | 746 | CB | THR | A | 330 | 30.020 | 21.700 | 13.106 | 1.00 | 31.61 |
| ATOM | 747 | OG1 | THR | A | 330 | 29.784 | 20.679 | 12.136 | 1.00 | 30.28 |
| ATOM | 748 | CG2 | THR | A | 330 | 29.299 | 21.338 | 14.383 | 1.00 | 30.69 |
| ATOM | 749 | C | THR | A | 330 | 30.334 | 23.429 | 11.297 | 1.00 | 35.87 |
| ATOM | 750 | O | THR | A | 330 | 29.855 | 23.201 | 10.182 | 1.00 | 37.27 |
| ATOM | 751 | N | PRO | A | 331 | 31.562 | 23.969 | 11.451 | 1.00 | 37.54 |
| ATOM | 752 | CD | PRO | A | 331 | 32.279 | 24.281 | 12.701 | 1.00 | 37.22 |
| ATOM | 753 | CA | PRO | A | 331 | 32.380 | 24.336 | 10.291 | 1.00 | 37.70 |
| ATOM | 754 | CB | PRO | A | 331 | 33.757 | 24.570 | 10.917 | 1.00 | 37.57 |

Figure 6

| ATOM | 755 | CG  | PRO | A | 331 | 33.388 | 25.203 | 12.215 | 1.00 | 36.82 |
| ATOM | 756 | C   | PRO | A | 331 | 32.403 | 23.273 | 9.196  | 1.00 | 38.17 |
| ATOM | 757 | O   | PRO | A | 331 | 32.463 | 23.617 | 8.017  | 1.00 | 38.93 |
| ATOM | 758 | N   | SER | A | 332 | 32.343 | 22.000 | 9.601  | 1.00 | 38.08 |
| ATOM | 759 | CA  | SER | A | 332 | 32.334 | 20.852 | 8.683  | 1.00 | 38.63 |
| ATOM | 760 | CB  | SER | A | 332 | 32.704 | 19.570 | 9.423  | 1.00 | 38.51 |
| ATOM | 761 | OG  | SER | A | 332 | 33.811 | 19.781 | 10.270 | 1.00 | 41.65 |
| ATOM | 762 | C   | SER | A | 332 | 30.960 | 20.646 | 8.054  | 1.00 | 39.00 |
| ATOM | 763 | O   | SER | A | 332 | 30.857 | 20.327 | 6.868  | 1.00 | 39.50 |
| ATOM | 764 | N   | GLY | A | 333 | 29.916 | 20.789 | 8.873  | 1.00 | 38.32 |
| ATOM | 765 | CA  | GLY | A | 333 | 28.550 | 20.623 | 8.408  | 1.00 | 38.23 |
| ATOM | 766 | C   | GLY | A | 333 | 28.163 | 21.711 | 7.431  | 1.00 | 39.03 |
| ATOM | 767 | O   | GLY | A | 333 | 27.317 | 21.508 | 6.552  | 1.00 | 40.45 |
| ATOM | 768 | N   | ILE | A | 334 | 28.781 | 22.875 | 7.595  | 1.00 | 38.57 |
| ATOM | 769 | CA  | ILE | A | 334 | 28.546 | 24.008 | 6.720  | 1.00 | 39.29 |
| ATOM | 770 | CB  | ILE | A | 334 | 29.207 | 25.288 | 7.282  | 1.00 | 39.00 |
| ATOM | 771 | CG2 | ILE | A | 334 | 29.416 | 26.325 | 6.177  | 1.00 | 38.70 |
| ATOM | 772 | CG1 | ILE | A | 334 | 28.400 | 25.837 | 8.468  | 1.00 | 38.64 |
| ATOM | 773 | CD1 | ILE | A | 334 | 26.948 | 26.157 | 8.162  | 1.00 | 37.03 |
| ATOM | 774 | C   | ILE | A | 334 | 29.133 | 23.723 | 5.341  | 1.00 | 40.98 |
| ATOM | 775 | O   | ILE | A | 334 | 28.545 | 24.100 | 4.334  | 1.00 | 42.24 |
| ATOM | 776 | N   | LYS | A | 335 | 30.273 | 23.029 | 5.309  | 1.00 | 42.20 |
| ATOM | 777 | CA  | LYS | A | 335 | 30.979 | 22.706 | 4.066  | 1.00 | 41.87 |
| ATOM | 778 | CB  | LYS | A | 335 | 32.453 | 22.414 | 4.363  | 1.00 | 43.95 |
| ATOM | 779 | CG  | LYS | A | 335 | 33.250 | 23.592 | 4.904  | 1.00 | 45.84 |
| ATOM | 780 | CD  | LYS | A | 335 | 34.509 | 23.098 | 5.609  | 1.00 | 48.37 |
| ATOM | 781 | CE  | LYS | A | 335 | 35.254 | 24.255 | 6.258  | 1.00 | 51.13 |
| ATOM | 782 | NZ  | LYS | A | 335 | 36.131 | 23.831 | 7.398  | 1.00 | 52.42 |
| ATOM | 783 | C   | LYS | A | 335 | 30.415 | 21.555 | 3.239  | 1.00 | 40.83 |
| ATOM | 784 | O   | LYS | A | 335 | 30.801 | 21.393 | 2.089  | 1.00 | 41.08 |
| ATOM | 785 | N   | LEU | A | 336 | 29.533 | 20.747 | 3.825  | 1.00 | 40.16 |
| ATOM | 786 | CA  | LEU | A | 336 | 28.933 | 19.588 | 3.135  | 1.00 | 38.20 |
| ATOM | 787 | CB  | LEU | A | 336 | 27.913 | 18.885 | 4.046  | 1.00 | 38.82 |
| ATOM | 788 | CG  | LEU | A | 336 | 28.433 | 18.119 | 5.264  | 1.00 | 38.16 |
| ATOM | 789 | CD1 | LEU | A | 336 | 27.318 | 17.857 | 6.252  | 1.00 | 37.61 |
| ATOM | 790 | CD2 | LEU | A | 336 | 29.050 | 16.823 | 4.805  | 1.00 | 38.42 |
| ATOM | 791 | C   | LEU | A | 336 | 28.279 | 19.933 | 1.800  | 1.00 | 36.36 |
| ATOM | 792 | O   | LEU | A | 336 | 27.569 | 20.936 | 1.685  | 1.00 | 35.90 |
| ATOM | 793 | N   | THR | A | 337 | 28.539 | 19.095 | 0.798  | 1.00 | 35.16 |
| ATOM | 794 | CA  | THR | A | 337 | 28.000 | 19.287 | -0.546 | 1.00 | 34.34 |
| ATOM | 795 | CB  | THR | A | 337 | 28.914 | 18.637 | -1.648 | 1.00 | 33.06 |
| ATOM | 796 | OG1 | THR | A | 337 | 28.839 | 17.204 | -1.593 | 1.00 | 31.81 |
| ATOM | 797 | CG2 | THR | A | 337 | 30.364 | 19.064 | -1.463 | 1.00 | 31.07 |
| ATOM | 798 | C   | THR | A | 337 | 26.576 | 18.735 | -0.658 | 1.00 | 36.02 |
| ATOM | 799 | O   | THR | A | 337 | 26.173 | 17.850 | 0.119  | 1.00 | 36.23 |
| ATOM | 800 | N   | ILE | A | 338 | 25.819 | 19.270 | -1.621 | 1.00 | 35.35 |
| ATOM | 801 | CA  | ILE | A | 338 | 24.439 | 18.854 | -1.856 | 1.00 | 33.75 |
| ATOM | 802 | CB  | ILE | A | 338 | 23.820 | 19.583 | -3.073 | 1.00 | 34.57 |
| ATOM | 803 | CG2 | ILE | A | 338 | 24.501 | 19.122 | -4.377 | 1.00 | 33.85 |
| ATOM | 804 | CG1 | ILE | A | 338 | 22.310 | 19.310 | -3.145 | 1.00 | 33.45 |
| ATOM | 805 | CD1 | ILE | A | 338 | 21.499 | 19.922 | -2.023 | 1.00 | 32.93 |
| ATOM | 806 | C   | ILE | A | 338 | 24.340 | 17.353 | -2.084 | 1.00 | 33.48 |
| ATOM | 807 | O   | ILE | A | 338 | 23.331 | 16.743 | -1.764 | 1.00 | 32.91 |
| ATOM | 808 | N   | ASN | A | 339 | 25.386 | 16.769 | -2.657 | 1.00 | 34.03 |
| ATOM | 809 | CA  | ASN | A | 339 | 25.417 | 15.337 | -2.921 | 1.00 | 35.32 |
| ATOM | 810 | CB  | ASN | A | 339 | 26.684 | 14.966 | -3.687 | 1.00 | 36.15 |
| ATOM | 811 | CG  | ASN | A | 339 | 26.700 | 15.526 | -5.087 | 1.00 | 36.58 |
| ATOM | 812 | OD1 | ASN | A | 339 | 26.505 | 14.789 | -6.051 | 1.00 | 35.73 |
| ATOM | 813 | ND2 | ASN | A | 339 | 26.936 | 16.838 | -5.212 | 1.00 | 37.41 |

Figure 6

| | | | | | | | | | |
|---|---|---|---|---|---|---|---|---|---|
| ATOM | 814 | C | ASN | A | 339 | 25.394 | 14.560 | -1.625 | 1.00 35.94 |
| ATOM | 815 | O | ASN | A | 339 | 24.638 | 13.599 | -1.481 | 1.00 38.27 |
| ATOM | 816 | N | LYS | A | 340 | 26.238 | 14.988 | -0.687 | 1.00 36.37 |
| ATOM | 817 | CA | LYS | A | 340 | 26.376 | 14.352 | 0.623 | 1.00 35.89 |
| ATOM | 818 | CB | LYS | A | 340 | 27.617 | 14.921 | 1.337 | 1.00 37.19 |
| ATOM | 819 | CG | LYS | A | 340 | 27.914 | 14.344 | 2.717 | 1.00 39.27 |
| ATOM | 820 | CD | LYS | A | 340 | 28.051 | 12.827 | 2.716 | 1.00 40.05 |
| ATOM | 821 | CE | LYS | A | 340 | 28.132 | 12.314 | 4.153 | 1.00 40.47 |
| ATOM | 822 | NZ | LYS | A | 340 | 27.892 | 10.833 | 4.299 | 1.00 41.35 |
| ATOM | 823 | C | LYS | A | 340 | 25.107 | 14.533 | 1.462 | 1.00 34.61 |
| ATOM | 824 | O | LYS | A | 340 | 24.612 | 13.576 | 2.070 | 1.00 33.10 |
| ATOM | 825 | N | LEU | A | 341 | 24.578 | 15.757 | 1.455 | 1.00 32.74 |
| ATOM | 826 | CA | LEU | A | 341 | 23.363 | 16.090 | 2.186 | 1.00 31.37 |
| ATOM | 827 | CB | LEU | A | 341 | 22.968 | 17.550 | 1.934 | 1.00 29.12 |
| ATOM | 828 | CG | LEU | A | 341 | 23.905 | 18.656 | 2.424 | 1.00 27.00 |
| ATOM | 829 | CD1 | LEU | A | 341 | 23.337 | 20.013 | 2.105 | 1.00 25.55 |
| ATOM | 830 | CD2 | LEU | A | 341 | 24.084 | 18.529 | 3.903 | 1.00 27.32 |
| ATOM | 831 | C | LEU | A | 341 | 22.213 | 15.159 | 1.790 | 1.00 32.18 |
| ATOM | 832 | O | LEU | A | 341 | 21.578 | 14.545 | 2.644 | 1.00 31.62 |
| ATOM | 833 | N | LEU | A | 342 | 21.987 | 15.014 | 0.491 | 1.00 33.34 |
| ATOM | 834 | CA | LEU | A | 342 | 20.913 | 14.159 | -0.007 | 1.00 34.56 |
| ATOM | 835 | CB | LEU | A | 342 | 20.738 | 14.329 | -1.519 | 1.00 36.88 |
| ATOM | 836 | CG | LEU | A | 342 | 20.428 | 15.772 | -1.929 | 1.00 38.53 |
| ATOM | 837 | CD1 | LEU | A | 342 | 19.863 | 15.765 | -3.295 | 1.00 39.01 |
| ATOM | 838 | CD2 | LEU | A | 342 | 19.432 | 16.416 | -0.971 | 1.00 39.74 |
| ATOM | 839 | C | LEU | A | 342 | 21.112 | 12.705 | 0.324 | 1.00 33.39 |
| ATOM | 840 | O | LEU | A | 342 | 20.154 | 11.962 | 0.483 | 1.00 32.08 |
| ATOM | 841 | N | ASP | A | 343 | 22.366 | 12.292 | 0.397 | 1.00 33.80 |
| ATOM | 842 | CA | ASP | A | 343 | 22.658 | 10.918 | 0.728 | 1.00 34.74 |
| ATOM | 843 | CB | ASP | A | 343 | 24.134 | 10.603 | 0.546 | 1.00 38.14 |
| ATOM | 844 | CG | ASP | A | 343 | 24.414 | 9.130 | 0.728 | 1.00 41.80 |
| ATOM | 845 | OD1 | ASP | A | 343 | 23.610 | 8.310 | 0.199 | 1.00 43.42 |
| ATOM | 846 | OD2 | ASP | A | 343 | 25.397 | 8.792 | 1.429 | 1.00 42.41 |
| ATOM | 847 | C | ASP | A | 343 | 22.277 | 10.724 | 2.174 | 1.00 32.44 |
| ATOM | 848 | O | ASP | A | 343 | 21.842 | 9.658 | 2.577 | 1.00 32.93 |
| ATOM | 849 | N | MET | A | 344 | 22.465 | 11.766 | 2.966 | 1.00 30.24 |
| ATOM | 850 | CA | MET | A | 344 | 22.095 | 11.705 | 4.366 | 1.00 28.65 |
| ATOM | 851 | CB | MET | A | 344 | 22.624 | 12.928 | 5.102 | 1.00 29.56 |
| ATOM | 852 | CG | MET | A | 344 | 24.139 | 12.966 | 5.173 | 1.00 29.43 |
| ATOM | 853 | SD | MET | A | 344 | 24.703 | 14.473 | 5.890 | 1.00 30.93 |
| ATOM | 854 | CE | MET | A | 344 | 25.285 | 13.857 | 7.462 | 1.00 31.49 |
| ATOM | 855 | C | MET | A | 344 | 20.577 | 11.639 | 4.415 | 1.00 26.69 |
| ATOM | 856 | O | MET | A | 344 | 20.034 | 10.720 | 5.013 | 1.00 27.80 |
| ATOM | 857 | N | ALA | A | 345 | 19.915 | 12.561 | 3.705 | 1.00 24.10 |
| ATOM | 858 | CA | ALA | A | 345 | 18.452 | 12.632 | 3.594 | 1.00 21.03 |
| ATOM | 859 | CB | ALA | A | 345 | 18.051 | 13.695 | 2.582 | 1.00 20.08 |
| ATOM | 860 | C | ALA | A | 345 | 17.881 | 11.285 | 3.175 | 1.00 20.04 |
| ATOM | 861 | O | ALA | A | 345 | 16.824 | 10.884 | 3.651 | 1.00 21.75 |
| ATOM | 862 | N | ALA | A | 346 | 18.614 | 10.583 | 2.312 | 1.00 18.78 |
| ATOM | 863 | CA | ALA | A | 346 | 18.240 | 9.259 | 1.814 | 1.00 19.86 |
| ATOM | 864 | CB | ALA | A | 346 | 19.171 | 8.843 | 0.675 | 1.00 17.57 |
| ATOM | 865 | C | ALA | A | 346 | 18.300 | 8.218 | 2.923 | 1.00 20.91 |
| ATOM | 866 | O | ALA | A | 346 | 17.455 | 7.331 | 3.009 | 1.00 22.43 |
| ATOM | 867 | N | GLN | A | 347 | 19.347 | 8.304 | 3.730 | 1.00 22.71 |
| ATOM | 868 | CA | GLN | A | 347 | 19.558 | 7.405 | 4.865 | 1.00 23.01 |
| ATOM | 869 | CB | GLN | A | 347 | 20.892 | 7.711 | 5.512 | 1.00 25.10 |
| ATOM | 870 | CG | GLN | A | 347 | 22.069 | 7.158 | 4.772 | 1.00 27.76 |
| ATOM | 871 | CD | GLN | A | 347 | 23.341 | 7.391 | 5.543 | 1.00 29.91 |
| ATOM | 872 | OE1 | GLN | A | 347 | 24.062 | 6.445 | 5.862 | 1.00 31.61 |

Figure 6

| | | | | | | | | | |
|---|---|---|---|---|---|---|---|---|---|
| ATOM | 873 | NE2 | GLN | A | 347 | 23.618 | 8.654 | 5.877 | 1.00 30.65 |
| ATOM | 874 | C | GLN | A | 347 | 18.465 | 7.505 | 5.926 | 1.00 21.21 |
| ATOM | 875 | O | GLN | A | 347 | 18.072 | 6.511 | 6.526 | 1.00 20.20 |
| ATOM | 876 | N | ILE | A | 348 | 18.010 | 8.726 | 6.171 | 1.00 19.76 |
| ATOM | 877 | CA | ILE | A | 348 | 16.952 | 8.990 | 7.122 | 1.00 18.92 |
| ATOM | 878 | CB | ILE | A | 348 | 16.815 | 10.510 | 7.317 | 1.00 18.30 |
| ATOM | 879 | CG2 | ILE | A | 348 | 15.576 | 10.828 | 8.133 | 1.00 18.66 |
| ATOM | 880 | CG1 | ILE | A | 348 | 18.090 | 11.077 | 7.952 | 1.00 15.43 |
| ATOM | 881 | CD1 | ILE | A | 348 | 18.221 | 12.573 | 7.857 | 1.00 13.57 |
| ATOM | 882 | C | ILE | A | 348 | 15.643 | 8.409 | 6.561 | 1.00 21.07 |
| ATOM | 883 | O | ILE | A | 348 | 14.878 | 7.740 | 7.277 | 1.00 21.22 |
| ATOM | 884 | N | ALA | A | 349 | 15.408 | 8.646 | 5.260 | 1.00 21.20 |
| ATOM | 885 | CA | ALA | A | 349 | 14.210 | 8.154 | 4.580 | 1.00 19.78 |
| ATOM | 886 | CB | ALA | A | 349 | 14.080 | 8.783 | 3.210 | 1.00 20.60 |
| ATOM | 887 | C | ALA | A | 349 | 14.241 | 6.638 | 4.485 | 1.00 20.77 |
| ATOM | 888 | O | ALA | A | 349 | 13.194 | 5.993 | 4.464 | 1.00 22.87 |
| ATOM | 889 | N | GLU | A | 350 | 15.438 | 6.065 | 4.452 | 1.00 20.02 |
| ATOM | 890 | CA | GLU | A | 350 | 15.568 | 4.618 | 4.413 | 1.00 21.72 |
| ATOM | 891 | CB | GLU | A | 350 | 16.997 | 4.210 | 4.085 | 1.00 23.43 |
| ATOM | 892 | CG | GLU | A | 350 | 17.197 | 2.702 | 4.139 | 1.00 24.35 |
| ATOM | 893 | CD | GLU | A | 350 | 18.656 | 2.267 | 4.004 | 1.00 25.13 |
| ATOM | 894 | OE1 | GLU | A | 350 | 19.569 | 3.118 | 3.847 | 1.00 22.13 |
| ATOM | 895 | OE2 | GLU | A | 350 | 18.877 | 1.037 | 4.060 | 1.00 27.13 |
| ATOM | 896 | C | GLU | A | 350 | 15.184 | 4.012 | 5.763 | 1.00 23.80 |
| ATOM | 897 | O | GLU | A | 350 | 14.604 | 2.924 | 5.833 | 1.00 25.54 |
| ATOM | 898 | N | GLY | A | 351 | 15.524 | 4.709 | 6.843 | 1.00 24.35 |
| ATOM | 899 | CA | GLY | A | 351 | 15.197 | 4.205 | 8.158 | 1.00 23.68 |
| ATOM | 900 | C | GLY | A | 351 | 13.713 | 4.329 | 8.378 | 1.00 23.71 |
| ATOM | 901 | O | GLY | A | 351 | 13.084 | 3.415 | 8.916 | 1.00 23.49 |
| ATOM | 902 | N | MET | A | 352 | 13.166 | 5.471 | 7.962 | 1.00 23.50 |
| ATOM | 903 | CA | MET | A | 352 | 11.739 | 5.753 | 8.090 | 1.00 22.48 |
| ATOM | 904 | CB | MET | A | 352 | 11.430 | 7.190 | 7.665 | 1.00 22.21 |
| ATOM | 905 | CG | MET | A | 352 | 11.650 | 8.249 | 8.738 | 1.00 21.58 |
| ATOM | 906 | SD | MET | A | 352 | 10.952 | 7.797 | 10.330 | 1.00 18.90 |
| ATOM | 907 | CE | MET | A | 352 | 9.215 | 7.383 | 9.958 | 1.00 18.03 |
| ATOM | 908 | C | MET | A | 352 | 10.901 | 4.786 | 7.263 | 1.00 23.42 |
| ATOM | 909 | O | MET | A | 352 | 9.761 | 4.482 | 7.629 | 1.00 25.33 |
| ATOM | 910 | N | ALA | A | 353 | 11.455 | 4.324 | 6.140 | 1.00 22.69 |
| ATOM | 911 | CA | ALA | A | 353 | 10.762 | 3.367 | 5.280 | 1.00 22.57 |
| ATOM | 912 | CB | ALA | A | 353 | 11.532 | 3.164 | 3.987 | 1.00 23.51 |
| ATOM | 913 | C | ALA | A | 353 | 10.621 | 2.041 | 6.024 | 1.00 22.96 |
| ATOM | 914 | O | ALA | A | 353 | 9.654 | 1.322 | 5.837 | 1.00 23.70 |
| ATOM | 915 | N | PHE | A | 354 | 11.618 | 1.715 | 6.847 | 1.00 24.61 |
| ATOM | 916 | CA | PHE | A | 354 | 11.607 | 0.505 | 7.671 | 1.00 23.66 |
| ATOM | 917 | CB | PHE | A | 354 | 12.975 | 0.310 | 8.334 | 1.00 24.13 |
| ATOM | 918 | CG | PHE | A | 354 | 13.017 | -0.839 | 9.295 | 1.00 24.79 |
| ATOM | 919 | CD1 | PHE | A | 354 | 12.891 | -2.147 | 8.833 | 1.00 25.21 |
| ATOM | 920 | CD2 | PHE | A | 354 | 13.163 | -0.617 | 10.666 | 1.00 25.50 |
| ATOM | 921 | CE1 | PHE | A | 354 | 12.907 | -3.224 | 9.714 | 1.00 25.00 |
| ATOM | 922 | CE2 | PHE | A | 354 | 13.182 | -1.687 | 11.568 | 1.00 25.73 |
| ATOM | 923 | CZ | PHE | A | 354 | 13.053 | -2.995 | 11.089 | 1.00 25.78 |
| ATOM | 924 | C | PHE | A | 354 | 10.536 | 0.638 | 8.754 | 1.00 22.38 |
| ATOM | 925 | O | PHE | A | 354 | 9.810 | -0.307 | 9.039 | 1.00 22.06 |
| ATOM | 926 | N | ILE | A | 355 | 10.472 | 1.819 | 9.364 | 1.00 22.61 |
| ATOM | 927 | CA | ILE | A | 355 | 9.494 | 2.129 | 10.408 | 1.00 23.73 |
| ATOM | 928 | CB | ILE | A | 355 | 9.816 | 3.521 | 11.067 | 1.00 23.01 |
| ATOM | 929 | CG2 | ILE | A | 355 | 8.611 | 4.097 | 11.798 | 1.00 21.27 |
| ATOM | 930 | CG1 | ILE | A | 355 | 11.022 | 3.385 | 12.011 | 1.00 21.33 |
| ATOM | 931 | CD1 | ILE | A | 355 | 11.503 | 4.688 | 12.614 | 1.00 21.43 |

Figure 6

| ATOM | 932 | C   | ILE A 355 | 8.095  | 2.090  | 9.784  | 1.00 | 25.81 |
| ATOM | 933 | O   | ILE A 355 | 7.141  | 1.616  | 10.398 | 1.00 | 26.49 |
| ATOM | 934 | N   | GLU A 356 | 8.003  | 2.533  | 8.528  | 1.00 | 26.38 |
| ATOM | 935 | CA  | GLU A 356 | 6.754  | 2.530  | 7.787  | 1.00 | 26.91 |
| ATOM | 936 | CB  | GLU A 356 | 6.952  | 3.294  | 6.483  | 1.00 | 26.37 |
| ATOM | 937 | CG  | GLU A 356 | 5.744  | 3.361  | 5.576  | 1.00 | 24.82 |
| ATOM | 938 | CD  | GLU A 356 | 6.022  | 4.167  | 4.325  | 1.00 | 25.74 |
| ATOM | 939 | OE1 | GLU A 356 | 6.773  | 3.679  | 3.455  | 1.00 | 24.98 |
| ATOM | 940 | OE2 | GLU A 356 | 5.518  | 5.308  | 4.212  | 1.00 | 26.17 |
| ATOM | 941 | C   | GLU A 356 | 6.388  | 1.067  | 7.507  | 1.00 | 29.21 |
| ATOM | 942 | O   | GLU A 356 | 5.283  | 0.603  | 7.807  | 1.00 | 30.15 |
| ATOM | 943 | N   | GLU A 357 | 7.365  | 0.329  | 7.006  | 1.00 | 31.08 |
| ATOM | 944 | CA  | GLU A 357 | 7.216  | -1.074 | 6.681  | 1.00 | 32.29 |
| ATOM | 945 | CB  | GLU A 357 | 8.594  | -1.628 | 6.356  | 1.00 | 33.63 |
| ATOM | 946 | CG  | GLU A 357 | 8.744  | -3.124 | 6.516  | 1.00 | 37.04 |
| ATOM | 947 | CD  | GLU A 357 | 8.359  | -3.879 | 5.276  | 1.00 | 38.43 |
| ATOM | 948 | OE1 | GLU A 357 | 9.087  | -3.744 | 4.269  | 1.00 | 39.94 |
| ATOM | 949 | OE2 | GLU A 357 | 7.344  | -4.610 | 5.306  | 1.00 | 40.07 |
| ATOM | 950 | C   | GLU A 357 | 6.622  | -1.869 | 7.819  | 1.00 | 33.68 |
| ATOM | 951 | O   | GLU A 357 | 5.694  | -2.648 | 7.633  | 1.00 | 35.93 |
| ATOM | 952 | N   | ARG A 358 | 7.147  | -1.644 | 9.014  | 1.00 | 35.80 |
| ATOM | 953 | CA  | ARG A 358 | 6.724  | -2.375 | 10.197 | 1.00 | 35.65 |
| ATOM | 954 | CB  | ARG A 358 | 7.888  | -2.411 | 11.184 | 1.00 | 36.32 |
| ATOM | 955 | CG  | ARG A 358 | 9.127  | -3.029 | 10.592 | 1.00 | 37.04 |
| ATOM | 956 | CD  | ARG A 358 | 8.955  | -4.515 | 10.450 | 1.00 | 40.69 |
| ATOM | 957 | NE  | ARG A 358 | 8.714  | -5.123 | 11.754 | 1.00 | 46.01 |
| ATOM | 958 | CZ  | ARG A 358 | 9.595  | -5.123 | 12.757 | 1.00 | 48.53 |
| ATOM | 959 | NH1 | ARG A 358 | 10.779 | -4.556 | 12.600 | 1.00 | 50.03 |
| ATOM | 960 | NH2 | ARG A 358 | 9.287  | -5.666 | 13.926 | 1.00 | 49.77 |
| ATOM | 961 | C   | ARG A 358 | 5.452  | -1.875 | 10.872 | 1.00 | 35.31 |
| ATOM | 962 | O   | ARG A 358 | 4.996  | -2.461 | 11.856 | 1.00 | 36.57 |
| ATOM | 963 | N   | ASN A 359 | 4.865  | -0.822 | 10.319 | 1.00 | 35.24 |
| ATOM | 964 | CA  | ASN A 359 | 3.634  | -0.219 | 10.840 | 1.00 | 36.51 |
| ATOM | 965 | CB  | ASN A 359 | 2.466  | -1.216 | 10.861 | 1.00 | 39.49 |
| ATOM | 966 | CG  | ASN A 359 | 2.219  | -1.840 | 9.500  | 1.00 | 43.16 |
| ATOM | 967 | OD1 | ASN A 359 | 1.781  | -1.167 | 8.556  | 1.00 | 43.72 |
| ATOM | 968 | ND2 | ASN A 359 | 2.543  | -3.134 | 9.377  | 1.00 | 44.78 |
| ATOM | 969 | C   | ASN A 359 | 3.765  | 0.502  | 12.179 | 1.00 | 34.20 |
| ATOM | 970 | O   | ASN A 359 | 2.978  | 0.307  | 13.106 | 1.00 | 32.57 |
| ATOM | 971 | N   | TYR A 360 | 4.781  | 1.349  | 12.245 | 1.00 | 31.16 |
| ATOM | 972 | CA  | TYR A 360 | 5.049  | 2.191  | 13.395 | 1.00 | 27.78 |
| ATOM | 973 | CB  | TYR A 360 | 6.442  | 1.883  | 13.969 | 1.00 | 26.83 |
| ATOM | 974 | CG  | TYR A 360 | 6.499  | 0.681  | 14.891 | 1.00 | 25.58 |
| ATOM | 975 | CD1 | TYR A 360 | 6.792  | -0.594 | 14.405 | 1.00 | 24.36 |
| ATOM | 976 | CE1 | TYR A 360 | 6.833  | -1.702 | 15.248 | 1.00 | 22.77 |
| ATOM | 977 | CD2 | TYR A 360 | 6.253  | 0.818  | 16.249 | 1.00 | 25.55 |
| ATOM | 978 | CE2 | TYR A 360 | 6.290  | -0.286 | 17.100 | 1.00 | 25.14 |
| ATOM | 979 | CZ  | TYR A 360 | 6.581  | -1.539 | 16.591 | 1.00 | 23.77 |
| ATOM | 980 | OH  | TYR A 360 | 6.598  | -2.617 | 17.440 | 1.00 | 25.34 |
| ATOM | 981 | C   | TYR A 360 | 5.043  | 3.609  | 12.821 | 1.00 | 27.74 |
| ATOM | 982 | O   | TYR A 360 | 4.883  | 3.799  | 11.607 | 1.00 | 30.08 |
| ATOM | 983 | N   | ILE A 361 | 5.127  | 4.599  | 13.696 | 1.00 | 24.93 |
| ATOM | 984 | CA  | ILE A 361 | 5.216  | 5.984  | 13.284 | 1.00 | 23.25 |
| ATOM | 985 | CB  | ILE A 361 | 3.911  | 6.785  | 13.496 | 1.00 | 22.45 |
| ATOM | 986 | CG2 | ILE A 361 | 2.765  | 6.133  | 12.752 | 1.00 | 22.81 |
| ATOM | 987 | CG1 | ILE A 361 | 3.588  | 6.946  | 14.975 | 1.00 | 21.19 |
| ATOM | 988 | CD1 | ILE A 361 | 2.488  | 7.921  | 15.217 | 1.00 | 19.44 |
| ATOM | 989 | C   | ILE A 361 | 6.315  | 6.529  | 14.176 | 1.00 | 25.47 |
| ATOM | 990 | O   | ILE A 361 | 6.739  | 5.863  | 15.113 | 1.00 | 27.70 |

Figure 6

| | | | | | | | | | |
|---|---|---|---|---|---|---|---|---|---|
| ATOM | 991 | N | HIS | A | 362 | 6.806 | 7.719 | 13.889 | 1.00 24.68 |
| ATOM | 992 | CA | HIS | A | 362 | 7.852 | 8.278 | 14.703 | 1.00 23.28 |
| ATOM | 993 | CB | HIS | A | 362 | 8.886 | 8.945 | 13.809 | 1.00 20.07 |
| ATOM | 994 | CG | HIS | A | 362 | 10.112 | 9.391 | 14.531 | 1.00 17.06 |
| ATOM | 995 | CD2 | HIS | A | 362 | 11.368 | 8.899 | 14.530 | 1.00 16.22 |
| ATOM | 996 | ND1 | HIS | A | 362 | 10.128 | 10.475 | 15.381 | 1.00 16.95 |
| ATOM | 997 | CE1 | HIS | A | 362 | 11.341 | 10.631 | 15.874 | 1.00 17.06 |
| ATOM | 998 | NE2 | HIS | A | 362 | 12.113 | 9.686 | 15.373 | 1.00 17.30 |
| ATOM | 999 | C | HIS | A | 362 | 7.207 | 9.287 | 15.619 | 1.00 25.88 |
| ATOM | 1000 | O | HIS | A | 362 | 7.295 | 9.167 | 16.816 | 1.00 28.28 |
| ATOM | 1001 | N | ARG | A | 363 | 6.520 | 10.240 | 14.999 | 1.00 27.16 |
| ATOM | 1002 | CA | ARG | A | 363 | 5.793 | 11.371 | 15.582 | 1.00 27.36 |
| ATOM | 1003 | CB | ARG | A | 363 | 4.658 | 10.967 | 16.540 | 1.00 31.72 |
| ATOM | 1004 | CG | ARG | A | 363 | 5.031 | 10.251 | 17.796 | 1.00 36.20 |
| ATOM | 1005 | CD | ARG | A | 363 | 3.827 | 9.739 | 18.575 | 1.00 38.76 |
| ATOM | 1006 | NE | ARG | A | 363 | 3.093 | 10.830 | 19.196 | 1.00 40.14 |
| ATOM | 1007 | CZ | ARG | A | 363 | 1.767 | 10.919 | 19.208 | 1.00 41.26 |
| ATOM | 1008 | NH1 | ARG | A | 363 | 1.032 | 9.973 | 18.641 | 1.00 40.18 |
| ATOM | 1009 | NH2 | ARG | A | 363 | 1.180 | 11.978 | 19.750 | 1.00 41.98 |
| ATOM | 1010 | C | ARG | A | 363 | 6.622 | 12.487 | 16.134 | 1.00 25.59 |
| ATOM | 1011 | O | ARG | A | 363 | 6.087 | 13.499 | 16.556 | 1.00 25.14 |
| ATOM | 1012 | N | ASP | A | 364 | 7.935 | 12.346 | 16.037 | 1.00 24.88 |
| ATOM | 1013 | CA | ASP | A | 364 | 8.883 | 13.357 | 16.527 | 1.00 23.45 |
| ATOM | 1014 | CB | ASP | A | 364 | 9.466 | 12.924 | 17.893 | 1.00 21.37 |
| ATOM | 1015 | CG | ASP | A | 364 | 8.455 | 13.038 | 19.039 | 1.00 19.99 |
| ATOM | 1016 | OD1 | ASP | A | 364 | 8.095 | 14.222 | 19.347 | 1.00 17.84 |
| ATOM | 1017 | OD2 | ASP | A | 364 | 8.049 | 11.948 | 19.562 | 1.00 19.20 |
| ATOM | 1018 | C | ASP | A | 364 | 10.008 | 13.540 | 15.506 | 1.00 23.68 |
| ATOM | 1019 | O | ASP | A | 364 | 11.136 | 13.876 | 15.865 | 1.00 22.79 |
| ATOM | 1020 | N | LEU | A | 365 | 9.700 | 13.303 | 14.236 | 1.00 23.74 |
| ATOM | 1021 | CA | LEU | A | 365 | 10.692 | 13.400 | 13.190 | 1.00 22.37 |
| ATOM | 1022 | CB | LEU | A | 365 | 10.200 | 12.646 | 11.954 | 1.00 21.12 |
| ATOM | 1023 | CG | LEU | A | 365 | 11.144 | 12.622 | 10.771 | 1.00 20.76 |
| ATOM | 1024 | CD1 | LEU | A | 365 | 12.406 | 11.852 | 11.132 | 1.00 20.08 |
| ATOM | 1025 | CD2 | LEU | A | 365 | 10.453 | 12.010 | 9.548 | 1.00 18.68 |
| ATOM | 1026 | C | LEU | A | 365 | 11.158 | 14.812 | 12.835 | 1.00 23.62 |
| ATOM | 1027 | O | LEU | A | 365 | 10.381 | 15.657 | 12.382 | 1.00 24.43 |
| ATOM | 1028 | N | ARG | A | 366 | 12.447 | 15.050 | 13.071 | 1.00 24.12 |
| ATOM | 1029 | CA | ARG | A | 366 | 13.129 | 16.308 | 12.792 | 1.00 23.67 |
| ATOM | 1030 | CB | ARG | A | 366 | 12.698 | 17.431 | 13.733 | 1.00 25.84 |
| ATOM | 1031 | CG | ARG | A | 366 | 12.796 | 17.163 | 15.235 | 1.00 28.88 |
| ATOM | 1032 | CD | ARG | A | 366 | 12.377 | 18.418 | 16.018 | 1.00 30.98 |
| ATOM | 1033 | NE | ARG | A | 366 | 12.135 | 18.156 | 17.433 | 1.00 33.32 |
| ATOM | 1034 | CZ | ARG | A | 366 | 11.117 | 17.434 | 17.899 | 1.00 34.04 |
| ATOM | 1035 | NH1 | ARG | A | 366 | 10.226 | 16.894 | 17.071 | 1.00 34.36 |
| ATOM | 1036 | NH2 | ARG | A | 366 | 11.012 | 17.215 | 19.200 | 1.00 33.83 |
| ATOM | 1037 | C | ARG | A | 366 | 14.637 | 16.096 | 12.843 | 1.00 23.14 |
| ATOM | 1038 | O | ARG | A | 366 | 15.100 | 15.058 | 13.305 | 1.00 23.84 |
| ATOM | 1039 | N | ALA | A | 367 | 15.408 | 17.057 | 12.343 | 1.00 22.57 |
| ATOM | 1040 | CA | ALA | A | 367 | 16.869 | 16.944 | 12.326 | 1.00 22.59 |
| ATOM | 1041 | CB | ALA | A | 367 | 17.473 | 18.191 | 11.752 | 1.00 22.02 |
| ATOM | 1042 | C | ALA | A | 367 | 17.437 | 16.662 | 13.713 | 1.00 24.50 |
| ATOM | 1043 | O | ALA | A | 367 | 18.273 | 15.763 | 13.882 | 1.00 24.06 |
| ATOM | 1044 | N | ALA | A | 368 | 16.904 | 17.379 | 14.707 | 1.00 24.16 |
| ATOM | 1045 | CA | ALA | A | 368 | 17.319 | 17.249 | 16.094 | 1.00 22.68 |
| ATOM | 1046 | CB | ALA | A | 368 | 16.442 | 18.097 | 16.983 | 1.00 22.63 |
| ATOM | 1047 | C | ALA | A | 368 | 17.301 | 15.802 | 16.558 | 1.00 22.68 |
| ATOM | 1048 | O | ALA | A | 368 | 18.195 | 15.373 | 17.296 | 1.00 24.74 |
| ATOM | 1049 | N | ASN | A | 369 | 16.319 | 15.040 | 16.074 | 1.00 22.06 |

Figure 6

| | | | | | | | | |
|---|---|---|---|---|---|---|---|---|
| ATOM | 1050 | CA | ASN | A 369 | 16.181 | 13.628 | 16.430 | 1.00 21.45 |
| ATOM | 1051 | CB | ASN | A 369 | 14.716 | 13.284 | 16.676 | 1.00 21.59 |
| ATOM | 1052 | CG | ASN | A 369 | 14.149 | 14.046 | 17.859 | 1.00 21.57 |
| ATOM | 1053 | OD1 | ASN | A 369 | 14.847 | 14.288 | 18.844 | 1.00 22.65 |
| ATOM | 1054 | ND2 | ASN | A 369 | 12.921 | 14.497 | 17.739 | 1.00 20.49 |
| ATOM | 1055 | C | ASN | A 369 | 16.864 | 12.625 | 15.490 | 1.00 21.54 |
| ATOM | 1056 | O | ASN | A 369 | 16.523 | 11.431 | 15.461 | 1.00 21.53 |
| ATOM | 1057 | N | ILE | A 370 | 17.868 | 13.115 | 14.766 | 1.00 20.25 |
| ATOM | 1058 | CA | ILE | A 370 | 18.650 | 12.287 | 13.866 | 1.00 18.84 |
| ATOM | 1059 | CB | ILE | A 370 | 18.587 | 12.793 | 12.389 | 1.00 18.29 |
| ATOM | 1060 | CG2 | ILE | A 370 | 19.432 | 11.885 | 11.486 | 1.00 17.53 |
| ATOM | 1061 | CG1 | ILE | A 370 | 17.135 | 12.878 | 11.886 | 1.00 15.89 |
| ATOM | 1062 | CD1 | ILE | A 370 | 16.439 | 11.549 | 11.783 | 1.00 14.76 |
| ATOM | 1063 | C | ILE | A 370 | 20.085 | 12.427 | 14.367 | 1.00 17.48 |
| ATOM | 1064 | O | ILE | A 370 | 20.534 | 13.525 | 14.685 | 1.00 16.02 |
| ATOM | 1065 | N | LEU | A 371 | 20.792 | 11.312 | 14.464 | 1.00 17.00 |
| ATOM | 1066 | CA | LEU | A 371 | 22.173 | 11.335 | 14.916 | 1.00 17.35 |
| ATOM | 1067 | CB | LEU | A 371 | 22.338 | 10.369 | 16.094 | 1.00 15.95 |
| ATOM | 1068 | CG | LEU | A 371 | 21.412 | 10.621 | 17.300 | 1.00 14.77 |
| ATOM | 1069 | CD1 | LEU | A 371 | 21.565 | 9.499 | 18.299 | 1.00 12.92 |
| ATOM | 1070 | CD2 | LEU | A 371 | 21.693 | 11.973 | 17.952 | 1.00 12.07 |
| ATOM | 1071 | C | LEU | A 371 | 23.155 | 11.015 | 13.776 | 1.00 18.10 |
| ATOM | 1072 | O | LEU | A 371 | 22.840 | 10.252 | 12.877 | 1.00 18.82 |
| ATOM | 1073 | N | VAL | A 372 | 24.337 | 11.626 | 13.823 | 1.00 20.14 |
| ATOM | 1074 | CA | VAL | A 372 | 25.389 | 11.455 | 12.821 | 1.00 21.52 |
| ATOM | 1075 | CB | VAL | A 372 | 25.824 | 12.848 | 12.302 | 1.00 21.31 |
| ATOM | 1076 | CG1 | VAL | A 372 | 26.625 | 12.730 | 11.004 | 1.00 21.11 |
| ATOM | 1077 | CG2 | VAL | A 372 | 24.615 | 13.736 | 12.116 | 1.00 20.32 |
| ATOM | 1078 | C | VAL | A 372 | 26.636 | 10.735 | 13.397 | 1.00 23.94 |
| ATOM | 1079 | O | VAL | A 372 | 27.232 | 11.175 | 14.388 | 1.00 25.89 |
| ATOM | 1080 | N | SER | A 373 | 27.072 | 9.662 | 12.753 | 1.00 25.78 |
| ATOM | 1081 | CA | SER | A 373 | 28.244 | 8.937 | 13.231 | 1.00 28.04 |
| ATOM | 1082 | CB | SER | A 373 | 28.246 | 7.516 | 12.686 | 1.00 28.41 |
| ATOM | 1083 | OG | SER | A 373 | 28.374 | 7.540 | 11.285 | 1.00 30.86 |
| ATOM | 1084 | C | SER | A 373 | 29.530 | 9.657 | 12.834 | 1.00 30.26 |
| ATOM | 1085 | O | SER | A 373 | 29.484 | 10.808 | 12.403 | 1.00 30.17 |
| ATOM | 1086 | N | ASP | A 374 | 30.680 | 9.009 | 13.045 | 1.00 34.16 |
| ATOM | 1087 | CA | ASP | A 374 | 31.982 | 9.599 | 12.685 | 1.00 36.33 |
| ATOM | 1088 | CB | ASP | A 374 | 33.138 | 8.931 | 13.449 | 1.00 39.01 |
| ATOM | 1089 | CG | ASP | A 374 | 33.084 | 7.422 | 13.392 | 1.00 41.21 |
| ATOM | 1090 | OD1 | ASP | A 374 | 32.730 | 6.816 | 14.421 | 1.00 43.07 |
| ATOM | 1091 | OD2 | ASP | A 374 | 33.392 | 6.836 | 12.334 | 1.00 42.41 |
| ATOM | 1092 | C | ASP | A 374 | 32.225 | 9.531 | 11.183 | 1.00 35.56 |
| ATOM | 1093 | O | ASP | A 374 | 32.979 | 10.331 | 10.635 | 1.00 34.94 |
| ATOM | 1094 | N | THR | A 375 | 31.581 | 8.559 | 10.536 | 1.00 34.84 |
| ATOM | 1095 | CA | THR | A 375 | 31.668 | 8.375 | 9.093 | 1.00 33.52 |
| ATOM | 1096 | CB | THR | A 375 | 31.580 | 6.892 | 8.695 | 1.00 33.98 |
| ATOM | 1097 | OG1 | THR | A 375 | 30.344 | 6.332 | 9.151 | 1.00 33.85 |
| ATOM | 1098 | CG2 | THR | A 375 | 32.752 | 6.107 | 9.282 | 1.00 34.60 |
| ATOM | 1099 | C | THR | A 375 | 30.514 | 9.105 | 8.434 | 1.00 33.63 |
| ATOM | 1100 | O | THR | A 375 | 30.043 | 8.690 | 7.373 | 1.00 34.06 |
| ATOM | 1101 | N | LEU | A 376 | 30.034 | 10.149 | 9.112 | 1.00 32.65 |
| ATOM | 1102 | CA | LEU | A 376 | 28.933 | 11.010 | 8.674 | 1.00 30.96 |
| ATOM | 1103 | CB | LEU | A 376 | 29.415 | 12.002 | 7.619 | 1.00 31.43 |
| ATOM | 1104 | CG | LEU | A 376 | 30.660 | 12.830 | 7.941 | 1.00 31.66 |
| ATOM | 1105 | CD1 | LEU | A 376 | 30.715 | 13.970 | 6.958 | 1.00 32.00 |
| ATOM | 1106 | CD2 | LEU | A 376 | 30.623 | 13.379 | 9.348 | 1.00 32.07 |
| ATOM | 1107 | C | LEU | A 376 | 27.633 | 10.347 | 8.222 | 1.00 30.77 |
| ATOM | 1108 | O | LEU | A 376 | 26.840 | 10.962 | 7.517 | 1.00 29.77 |

Figure 6

| | | | | | | | | | |
|---|---|---|---|---|---|---|---|---|---|
| ATOM | 1109 | N | SER | A | 377 | 27.402 | 9.107 | 8.642 | 1.00 31.37 |
| ATOM | 1110 | CA | SER | A | 377 | 26.170 | 8.394 | 8.289 | 1.00 32.40 |
| ATOM | 1111 | CB | SER | A | 377 | 26.398 | 6.876 | 8.288 | 1.00 33.12 |
| ATOM | 1112 | OG | SER | A | 377 | 26.530 | 6.378 | 9.608 | 1.00 36.48 |
| ATOM | 1113 | C | SER | A | 377 | 25.065 | 8.762 | 9.293 | 1.00 31.04 |
| ATOM | 1114 | O | SER | A | 377 | 25.354 | 9.043 | 10.459 | 1.00 31.80 |
| ATOM | 1115 | N | CYS | A | 378 | 23.807 | 8.719 | 8.853 | 1.00 28.42 |
| ATOM | 1116 | CA | CYS | A | 378 | 22.686 | 9.077 | 9.711 | 1.00 24.24 |
| ATOM | 1117 | CB | CYS | A | 378 | 21.775 | 10.049 | 8.987 | 1.00 22.76 |
| ATOM | 1118 | SG | CYS | A | 378 | 22.584 | 11.598 | 8.664 | 1.00 19.43 |
| ATOM | 1119 | C | CYS | A | 378 | 21.865 | 7.933 | 10.278 | 1.00 23.78 |
| ATOM | 1120 | O | CYS | A | 378 | 21.687 | 6.907 | 9.634 | 1.00 24.14 |
| ATOM | 1121 | N | LYS | A | 379 | 21.374 | 8.147 | 11.501 | 1.00 24.05 |
| ATOM | 1122 | CA | LYS | A | 379 | 20.539 | 7.196 | 12.250 | 1.00 24.79 |
| ATOM | 1123 | CB | LYS | A | 379 | 21.380 | 6.423 | 13.284 | 1.00 24.08 |
| ATOM | 1124 | CG | LYS | A | 379 | 22.052 | 5.148 | 12.737 | 1.00 24.57 |
| ATOM | 1125 | CD | LYS | A | 379 | 23.266 | 4.741 | 13.568 | 1.00 25.42 |
| ATOM | 1126 | CE | LYS | A | 379 | 23.924 | 3.433 | 13.107 | 1.00 25.08 |
| ATOM | 1127 | NZ | LYS | A | 379 | 23.227 | 2.184 | 13.588 | 1.00 26.96 |
| ATOM | 1128 | C | LYS | A | 379 | 19.341 | 7.923 | 12.924 | 1.00 25.00 |
| ATOM | 1129 | O | LYS | A | 379 | 19.457 | 9.076 | 13.366 | 1.00 23.10 |
| ATOM | 1130 | N | ILE | A | 380 | 18.174 | 7.273 | 12.911 | 1.00 24.91 |
| ATOM | 1131 | CA | ILE | A | 380 | 16.956 | 7.840 | 13.495 | 1.00 26.43 |
| ATOM | 1132 | CB | ILE | A | 380 | 15.685 | 7.274 | 12.843 | 1.00 26.24 |
| ATOM | 1133 | CG2 | ILE | A | 380 | 14.451 | 7.922 | 13.453 | 1.00 25.27 |
| ATOM | 1134 | CG1 | ILE | A | 380 | 15.709 | 7.527 | 11.339 | 1.00 26.47 |
| ATOM | 1135 | CD1 | ILE | A | 380 | 14.576 | 6.915 | 10.647 | 1.00 26.44 |
| ATOM | 1136 | C | ILE | A | 380 | 16.877 | 7.538 | 14.973 | 1.00 26.34 |
| ATOM | 1137 | O | ILE | A | 380 | 16.953 | 6.385 | 15.374 | 1.00 26.60 |
| ATOM | 1138 | N | ALA | A | 381 | 16.684 | 8.573 | 15.770 | 1.00 26.74 |
| ATOM | 1139 | CA | ALA | A | 381 | 16.608 | 8.391 | 17.207 | 1.00 28.23 |
| ATOM | 1140 | CB | ALA | A | 381 | 17.699 | 9.199 | 17.899 | 1.00 26.50 |
| ATOM | 1141 | C | ALA | A | 381 | 15.248 | 8.812 | 17.709 | 1.00 28.61 |
| ATOM | 1142 | O | ALA | A | 381 | 14.506 | 9.477 | 16.990 | 1.00 29.05 |
| ATOM | 1143 | N | ASP | A | 382 | 14.933 | 8.396 | 18.939 | 1.00 29.09 |
| ATOM | 1144 | CA | ASP | A | 382 | 13.687 | 8.733 | 19.628 | 1.00 27.65 |
| ATOM | 1145 | CB | ASP | A | 382 | 13.776 | 10.153 | 20.201 | 1.00 28.01 |
| ATOM | 1146 | CG | ASP | A | 382 | 14.703 | 10.226 | 21.418 | 1.00 28.35 |
| ATOM | 1147 | OD1 | ASP | A | 382 | 14.641 | 9.298 | 22.270 | 1.00 30.59 |
| ATOM | 1148 | OD2 | ASP | A | 382 | 15.477 | 11.201 | 21.540 | 1.00 26.23 |
| ATOM | 1149 | C | ASP | A | 382 | 12.431 | 8.530 | 18.804 | 1.00 26.91 |
| ATOM | 1150 | O | ASP | A | 382 | 11.609 | 9.442 | 18.647 | 1.00 26.24 |
| ATOM | 1151 | N | PHE | A | 383 | 12.282 | 7.306 | 18.321 | 1.00 26.07 |
| ATOM | 1152 | CA | PHE | A | 383 | 11.162 | 6.932 | 17.480 | 1.00 27.61 |
| ATOM | 1153 | CB | PHE | A | 383 | 11.686 | 6.169 | 16.251 | 1.00 25.30 |
| ATOM | 1154 | CG | PHE | A | 383 | 12.556 | 4.993 | 16.593 | 1.00 24.66 |
| ATOM | 1155 | CD1 | PHE | A | 383 | 12.000 | 3.731 | 16.768 | 1.00 24.30 |
| ATOM | 1156 | CD2 | PHE | A | 383 | 13.929 | 5.154 | 16.774 | 1.00 24.45 |
| ATOM | 1157 | CE1 | PHE | A | 383 | 12.787 | 2.649 | 17.121 | 1.00 23.38 |
| ATOM | 1158 | CE2 | PHE | A | 383 | 14.728 | 4.080 | 17.127 | 1.00 23.61 |
| ATOM | 1159 | CZ | PHE | A | 383 | 14.157 | 2.822 | 17.304 | 1.00 23.56 |
| ATOM | 1160 | C | PHE | A | 383 | 10.125 | 6.085 | 18.197 | 1.00 28.15 |
| ATOM | 1161 | O | PHE | A | 383 | 10.441 | 5.374 | 19.150 | 1.00 31.08 |
| ATOM | 1162 | N | GLY | A | 384 | 8.880 | 6.186 | 17.757 | 1.00 28.27 |
| ATOM | 1163 | CA | GLY | A | 384 | 7.832 | 5.381 | 18.348 | 1.00 29.12 |
| ATOM | 1164 | C | GLY | A | 384 | 7.365 | 5.733 | 19.745 | 1.00 30.76 |
| ATOM | 1165 | O | GLY | A | 384 | 6.677 | 4.921 | 20.369 | 1.00 32.23 |
| ATOM | 1166 | N | LEU | A | 385 | 7.767 | 6.899 | 20.256 | 1.00 31.42 |
| ATOM | 1167 | CA | LEU | A | 385 | 7.356 | 7.348 | 21.584 | 1.00 31.16 |

Figure 6

| ATOM | 1168 | CB  | LEU A 385 |  8.142 |  8.591 | 22.027 | 1.00 | 28.60 |
|------|------|-----|-----------|--------|--------|--------|------|-------|
| ATOM | 1169 | CG  | LEU A 385 |  9.654 |  8.401 | 22.185 | 1.00 | 28.19 |
| ATOM | 1170 | CD1 | LEU A 385 | 10.219 |  9.593 | 22.889 | 1.00 | 27.68 |
| ATOM | 1171 | CD2 | LEU A 385 |  9.976 |  7.137 | 22.939 | 1.00 | 26.78 |
| ATOM | 1172 | C   | LEU A 385 |  5.867 |  7.666 | 21.571 | 1.00 | 33.80 |
| ATOM | 1173 | O   | LEU A 385 |  5.309 |  8.085 | 20.550 | 1.00 | 34.85 |
| ATOM | 1174 | N   | ALA A 386 |  5.211 |  7.423 | 22.699 | 1.00 | 35.39 |
| ATOM | 1175 | CA  | ALA A 386 |  3.792 |  7.694 | 22.807 | 1.00 | 35.08 |
| ATOM | 1176 | CB  | ALA A 386 |  3.222 |  6.957 | 24.018 | 1.00 | 35.69 |
| ATOM | 1177 | C   | ALA A 386 |  3.558 |  9.195 | 22.942 | 1.00 | 34.06 |
| ATOM | 1178 | O   | ALA A 386 |  2.469 |  9.681 | 22.656 | 1.00 | 35.06 |
| ATOM | 1179 | N   | ARG A 387 |  4.610 |  9.932 | 23.288 | 1.00 | 31.72 |
| ATOM | 1180 | CA  | ARG A 387 |  4.501 | 11.370 | 23.510 | 1.00 | 30.70 |
| ATOM | 1181 | CB  | ARG A 387 |  4.930 | 11.649 | 24.947 | 1.00 | 31.86 |
| ATOM | 1182 | CG  | ARG A 387 |  6.349 | 11.140 | 25.242 | 1.00 | 32.38 |
| ATOM | 1183 | CD  | ARG A 387 |  6.789 | 11.524 | 26.616 | 1.00 | 32.56 |
| ATOM | 1184 | NE  | ARG A 387 |  8.224 | 11.385 | 26.788 | 1.00 | 31.09 |
| ATOM | 1185 | CZ  | ARG A 387 |  9.066 | 12.412 | 26.786 | 1.00 | 32.34 |
| ATOM | 1186 | NH1 | ARG A 387 |  8.606 | 13.647 | 26.612 | 1.00 | 31.07 |
| ATOM | 1187 | NH2 | ARG A 387 | 10.366 | 12.201 | 26.957 | 1.00 | 32.85 |
| ATOM | 1188 | C   | ARG A 387 |  5.299 | 12.280 | 22.580 | 1.00 | 29.62 |
| ATOM | 1189 | O   | ARG A 387 |  6.214 | 11.847 | 21.900 | 1.00 | 32.65 |
| ATOM | 1190 | N   | LEU A 388 |  4.967 | 13.559 | 22.581 | 1.00 | 26.81 |
| ATOM | 1191 | CA  | LEU A 388 |  5.685 | 14.525 | 21.776 | 1.00 | 25.28 |
| ATOM | 1192 | CB  | LEU A 388 |  4.757 | 15.649 | 21.351 | 1.00 | 24.89 |
| ATOM | 1193 | CG  | LEU A 388 |  3.440 | 15.137 | 20.801 | 1.00 | 25.53 |
| ATOM | 1194 | CD1 | LEU A 388 |  2.563 | 16.324 | 20.503 | 1.00 | 24.85 |
| ATOM | 1195 | CD2 | LEU A 388 |  3.701 | 14.272 | 19.563 | 1.00 | 27.79 |
| ATOM | 1196 | C   | LEU A 388 |  6.786 | 15.105 | 22.655 | 1.00 | 25.56 |
| ATOM | 1197 | O   | LEU A 388 |  6.503 | 15.752 | 23.665 | 1.00 | 26.87 |
| ATOM | 1198 | N   | ILE A 389 |  8.039 | 14.882 | 22.273 | 1.00 | 24.71 |
| ATOM | 1199 | CA  | ILE A 389 |  9.185 | 15.375 | 23.030 | 1.00 | 21.69 |
| ATOM | 1200 | CB  | ILE A 389 | 10.376 | 14.392 | 22.949 | 1.00 | 19.44 |
| ATOM | 1201 | CG2 | ILE A 389 |  9.933 | 12.970 | 23.331 | 1.00 | 18.14 |
| ATOM | 1202 | CG1 | ILE A 389 | 10.994 | 14.423 | 21.545 | 1.00 | 17.45 |
| ATOM | 1203 | CD1 | ILE A 389 | 12.006 | 13.340 | 21.279 | 1.00 | 13.44 |
| ATOM | 1204 | C   | ILE A 389 |  9.675 | 16.750 | 22.601 | 1.00 | 23.93 |
| ATOM | 1205 | O   | ILE A 389 |  9.322 | 17.261 | 21.550 | 1.00 | 24.62 |
| ATOM | 1206 | N   | GLU A 390 | 10.465 | 17.362 | 23.466 | 1.00 | 26.76 |
| ATOM | 1207 | CA  | GLU A 390 | 11.062 | 18.653 | 23.197 | 1.00 | 30.53 |
| ATOM | 1208 | CB  | GLU A 390 | 10.581 | 19.682 | 24.212 | 1.00 | 31.35 |
| ATOM | 1209 | CG  | GLU A 390 |  9.140 | 20.090 | 24.025 | 1.00 | 33.53 |
| ATOM | 1210 | CD  | GLU A 390 |  8.646 | 21.018 | 25.119 | 1.00 | 35.59 |
| ATOM | 1211 | OE1 | GLU A 390 |  7.419 | 21.106 | 25.304 | 1.00 | 37.46 |
| ATOM | 1212 | OE2 | GLU A 390 |  9.474 | 21.657 | 25.802 | 1.00 | 36.58 |
| ATOM | 1213 | C   | GLU A 390 | 12.578 | 18.478 | 23.278 | 1.00 | 31.99 |
| ATOM | 1214 | O   | GLU A 390 | 13.077 | 17.606 | 23.977 | 1.00 | 31.91 |
| ATOM | 1215 | N   | ASP A 391 | 13.305 | 19.314 | 22.557 | 1.00 | 33.75 |
| ATOM | 1216 | CA  | ASP A 391 | 14.757 | 19.239 | 22.527 | 1.00 | 35.89 |
| ATOM | 1217 | CB  | ASP A 391 | 15.287 | 20.169 | 21.457 | 1.00 | 38.24 |
| ATOM | 1218 | CG  | ASP A 391 | 14.826 | 19.792 | 20.085 | 1.00 | 40.28 |
| ATOM | 1219 | OD1 | ASP A 391 | 14.247 | 18.693 | 19.872 | 1.00 | 39.85 |
| ATOM | 1220 | OD2 | ASP A 391 | 15.068 | 20.634 | 19.211 | 1.00 | 43.01 |
| ATOM | 1221 | C   | ASP A 391 | 15.460 | 19.568 | 23.824 | 1.00 | 35.41 |
| ATOM | 1222 | O   | ASP A 391 | 16.548 | 19.062 | 24.078 | 1.00 | 35.74 |
| ATOM | 1223 | N   | ASN A 392 | 14.860 | 20.451 | 24.616 | 1.00 | 34.39 |
| ATOM | 1224 | CA  | ASN A 392 | 15.436 | 20.861 | 25.891 | 1.00 | 33.99 |
| ATOM | 1225 | CB  | ASN A 392 | 14.799 | 22.188 | 26.348 | 1.00 | 33.27 |
| ATOM | 1226 | CG  | ASN A 392 | 13.358 | 22.024 | 26.821 | 1.00 | 33.82 |

Figure 6

| | | | | | | | | |
|---|---|---|---|---|---|---|---|---|
| ATOM | 1227 | OD1 | ASN | A | 392 | 12.779 | 20.939 | 26.747 | 1.00 33.78 |
| ATOM | 1228 | ND2 | ASN | A | 392 | 12.775 | 23.105 | 27.318 | 1.00 33.65 |
| ATOM | 1229 | C | ASN | A | 392 | 15.344 | 19.787 | 27.015 | 1.00 33.53 |
| ATOM | 1230 | O | ASN | A | 392 | 15.641 | 20.072 | 28.177 | 1.00 34.75 |
| ATOM | 1231 | N | GLU | A | 393 | 14.998 | 18.552 | 26.662 | 1.00 31.91 |
| ATOM | 1232 | CA | GLU | A | 393 | 14.863 | 17.491 | 27.651 | 1.00 31.40 |
| ATOM | 1233 | CB | GLU | A | 393 | 13.906 | 16.419 | 27.140 | 1.00 31.63 |
| ATOM | 1234 | CG | GLU | A | 393 | 12.556 | 17.011 | 26.780 | 1.00 32.17 |
| ATOM | 1235 | CD | GLU | A | 393 | 11.478 | 15.988 | 26.525 | 1.00 33.26 |
| ATOM | 1236 | OE1 | GLU | A | 393 | 11.776 | 14.767 | 26.493 | 1.00 32.96 |
| ATOM | 1237 | OE2 | GLU | A | 393 | 10.311 | 16.427 | 26.370 | 1.00 33.74 |
| ATOM | 1238 | C | GLU | A | 393 | 16.159 | 16.882 | 28.166 | 1.00 31.71 |
| ATOM | 1239 | O | GLU | A | 393 | 16.278 | 16.602 | 29.346 | 1.00 31.85 |
| ATOM | 1240 | N | TYR | A | 394 | 17.124 | 16.659 | 27.281 | 1.00 33.00 |
| ATOM | 1241 | CA | TYR | A | 394 | 18.410 | 16.104 | 27.682 | 1.00 32.83 |
| ATOM | 1242 | CB | TYR | A | 394 | 18.526 | 14.648 | 27.252 | 1.00 32.62 |
| ATOM | 1243 | CG | TYR | A | 394 | 17.486 | 13.730 | 27.843 | 1.00 32.99 |
| ATOM | 1244 | CD1 | TYR | A | 394 | 16.194 | 13.706 | 27.341 | 1.00 33.00 |
| ATOM | 1245 | CE1 | TYR | A | 394 | 15.247 | 12.823 | 27.835 | 1.00 33.22 |
| ATOM | 1246 | CD2 | TYR | A | 394 | 17.811 | 12.841 | 28.872 | 1.00 33.79 |
| ATOM | 1247 | CE2 | TYR | A | 394 | 16.868 | 11.947 | 29.379 | 1.00 33.40 |
| ATOM | 1248 | CZ | TYR | A | 394 | 15.584 | 11.945 | 28.855 | 1.00 34.35 |
| ATOM | 1249 | OH | TYR | A | 394 | 14.625 | 11.075 | 29.347 | 1.00 35.56 |
| ATOM | 1250 | C | TYR | A | 394 | 19.589 | 16.922 | 27.141 | 1.00 33.66 |
| ATOM | 1251 | O | TYR | A | 394 | 20.728 | 16.458 | 27.129 | 1.00 35.65 |
| ATOM | 1252 | N | THR | A | 395 | 19.285 | 18.105 | 26.619 | 1.00 34.08 |
| ATOM | 1253 | CA | THR | A | 395 | 20.282 | 19.050 | 26.106 | 1.00 36.56 |
| ATOM | 1254 | CB | THR | A | 395 | 20.476 | 19.008 | 24.557 | 1.00 36.73 |
| ATOM | 1255 | OG1 | THR | A | 395 | 19.240 | 18.699 | 23.895 | 1.00 37.12 |
| ATOM | 1256 | CG2 | THR | A | 395 | 21.560 | 18.014 | 24.167 | 1.00 36.64 |
| ATOM | 1257 | C | THR | A | 395 | 19.762 | 20.424 | 26.495 | 1.00 38.93 |
| ATOM | 1258 | O | THR | A | 395 | 18.647 | 20.544 | 27.003 | 1.00 39.88 |
| ATOM | 1259 | N | ALA | A | 396 | 20.546 | 21.466 | 26.250 | 1.00 42.34 |
| ATOM | 1260 | CA | ALA | A | 396 | 20.111 | 22.806 | 26.621 | 1.00 45.91 |
| ATOM | 1261 | CB | ALA | A | 396 | 21.156 | 23.466 | 27.540 | 1.00 45.22 |
| ATOM | 1262 | C | ALA | A | 396 | 19.737 | 23.724 | 25.441 | 1.00 48.16 |
| ATOM | 1263 | O | ALA | A | 396 | 20.179 | 24.881 | 25.371 | 1.00 49.52 |
| ATOM | 1264 | N | ARG | A | 397 | 18.918 | 23.209 | 24.520 | 1.00 49.87 |
| ATOM | 1265 | CA | ARG | A | 397 | 18.470 | 23.997 | 23.378 | 1.00 50.87 |
| ATOM | 1266 | CB | ARG | A | 397 | 18.154 | 23.106 | 22.176 | 1.00 50.78 |
| ATOM | 1267 | CG | ARG | A | 397 | 19.327 | 22.276 | 21.671 | 1.00 51.83 |
| ATOM | 1268 | CD | ARG | A | 397 | 19.223 | 22.079 | 20.163 | 1.00 52.62 |
| ATOM | 1269 | NE | ARG | A | 397 | 20.044 | 20.979 | 19.655 | 1.00 52.36 |
| ATOM | 1270 | CZ | ARG | A | 397 | 19.667 | 19.702 | 19.664 | 1.00 52.13 |
| ATOM | 1271 | NH1 | ARG | A | 397 | 18.490 | 19.353 | 20.168 | 1.00 51.01 |
| ATOM | 1272 | NH2 | ARG | A | 397 | 20.433 | 18.781 | 19.101 | 1.00 51.86 |
| ATOM | 1273 | C | ARG | A | 397 | 17.225 | 24.788 | 23.777 | 1.00 51.76 |
| ATOM | 1274 | O | ARG | A | 397 | 17.345 | 26.030 | 23.891 | 1.00 52.31 |
| ATOM | 1275 | CB | PRO | A | 403 | 7.737 | 20.469 | 19.059 | 1.00 34.86 |
| ATOM | 1276 | CG | PRO | A | 403 | 8.256 | 21.039 | 20.415 | 1.00 34.24 |
| ATOM | 1277 | C | PRO | A | 403 | 6.658 | 21.684 | 17.107 | 1.00 35.70 |
| ATOM | 1278 | O | PRO | A | 403 | 6.675 | 20.766 | 16.256 | 1.00 36.62 |
| ATOM | 1279 | N | PRO | A | 403 | 7.386 | 22.851 | 19.235 | 1.00 34.64 |
| ATOM | 1280 | CD | PRO | A | 403 | 7.601 | 22.395 | 20.628 | 1.00 34.08 |
| ATOM | 1281 | CA | PRO | A | 403 | 7.693 | 21.763 | 18.263 | 1.00 34.48 |
| ATOM | 1282 | N | ILE | A | 404 | 5.845 | 22.725 | 17.029 | 1.00 33.66 |
| ATOM | 1283 | CA | ILE | A | 404 | 4.778 | 22.846 | 16.030 | 1.00 30.22 |
| ATOM | 1284 | CB | ILE | A | 404 | 3.902 | 24.069 | 16.381 | 1.00 29.05 |
| ATOM | 1285 | CG2 | ILE | A | 404 | 3.233 | 24.652 | 15.168 | 1.00 28.97 |

Figure 6

| | | | | | | | | | |
|---|---|---|---|---|---|---|---|---|---|
| ATOM | 1286 | CG1 | ILE | A | 404 | 2.901 | 23.684 | 17.454 | 1.00 28.60 |
| ATOM | 1287 | CD1 | ILE | A | 404 | 2.129 | 22.415 | 17.125 | 1.00 28.58 |
| ATOM | 1288 | C | ILE | A | 404 | 5.185 | 22.884 | 14.561 | 1.00 28.40 |
| ATOM | 1289 | O | ILE | A | 404 | 4.454 | 22.386 | 13.706 | 1.00 29.52 |
| ATOM | 1290 | N | LYS | A | 405 | 6.363 | 23.429 | 14.260 | 1.00 24.47 |
| ATOM | 1291 | CA | LYS | A | 405 | 6.823 | 23.563 | 12.877 | 1.00 21.61 |
| ATOM | 1292 | CB | LYS | A | 405 | 8.026 | 24.496 | 12.787 | 1.00 20.33 |
| ATOM | 1293 | CG | LYS | A | 405 | 7.711 | 25.890 | 13.254 | 1.00 19.80 |
| ATOM | 1294 | CD | LYS | A | 405 | 8.833 | 26.830 | 12.976 | 1.00 20.95 |
| ATOM | 1295 | CE | LYS | A | 405 | 8.581 | 28.195 | 13.569 | 1.00 22.86 |
| ATOM | 1296 | NZ | LYS | A | 405 | 9.597 | 29.166 | 13.078 | 1.00 25.30 |
| ATOM | 1297 | C | LYS | A | 405 | 7.045 | 22.304 | 12.016 | 1.00 21.33 |
| ATOM | 1298 | O | LYS | A | 405 | 7.266 | 22.412 | 10.811 | 1.00 21.94 |
| ATOM | 1299 | N | TRP | A | 406 | 6.973 | 21.129 | 12.642 | 1.00 19.38 |
| ATOM | 1300 | CA | TRP | A | 406 | 7.135 | 19.838 | 11.982 | 1.00 18.76 |
| ATOM | 1301 | CB | TRP | A | 406 | 8.230 | 19.009 | 12.678 | 1.00 19.52 |
| ATOM | 1302 | CG | TRP | A | 406 | 9.631 | 19.541 | 12.534 | 1.00 20.41 |
| ATOM | 1303 | CD2 | TRP | A | 406 | 10.230 | 20.608 | 13.286 | 1.00 20.69 |
| ATOM | 1304 | CE2 | TRP | A | 406 | 11.550 | 20.761 | 12.803 | 1.00 20.51 |
| ATOM | 1305 | CE3 | TRP | A | 406 | 9.784 | 21.442 | 14.322 | 1.00 22.36 |
| ATOM | 1306 | CD1 | TRP | A | 406 | 10.590 | 19.103 | 11.655 | 1.00 19.82 |
| ATOM | 1307 | NE1 | TRP | A | 406 | 11.737 | 19.837 | 11.812 | 1.00 19.77 |
| ATOM | 1308 | CZ2 | TRP | A | 406 | 12.429 | 21.725 | 13.324 | 1.00 22.51 |
| ATOM | 1309 | CZ3 | TRP | A | 406 | 10.662 | 22.406 | 14.843 | 1.00 22.45 |
| ATOM | 1310 | CH2 | TRP | A | 406 | 11.969 | 22.534 | 14.340 | 1.00 22.51 |
| ATOM | 1311 | C | TRP | A | 406 | 5.837 | 19.002 | 11.986 | 1.00 17.48 |
| ATOM | 1312 | O | TRP | A | 406 | 5.783 | 17.913 | 11.414 | 1.00 17.41 |
| ATOM | 1313 | N | THR | A | 407 | 4.796 | 19.517 | 12.627 | 1.00 17.45 |
| ATOM | 1314 | CA | THR | A | 407 | 3.516 | 18.803 | 12.756 | 1.00 17.95 |
| ATOM | 1315 | CB | THR | A | 407 | 2.763 | 19.211 | 14.085 | 1.00 17.02 |
| ATOM | 1316 | OG1 | THR | A | 407 | 3.715 | 19.415 | 15.134 | 1.00 19.35 |
| ATOM | 1317 | CG2 | THR | A | 407 | 1.785 | 18.130 | 14.513 | 1.00 14.71 |
| ATOM | 1318 | C | THR | A | 407 | 2.559 | 19.024 | 11.564 | 1.00 17.00 |
| ATOM | 1319 | O | THR | A | 407 | 2.215 | 20.172 | 11.234 | 1.00 13.94 |
| ATOM | 1320 | N | ALA | A | 408 | 2.077 | 17.918 | 10.982 | 1.00 16.85 |
| ATOM | 1321 | CA | ALA | A | 408 | 1.138 | 17.955 | 9.845 | 1.00 19.43 |
| ATOM | 1322 | CB | ALA | A | 408 | 0.802 | 16.554 | 9.374 | 1.00 17.33 |
| ATOM | 1323 | C | ALA | A | 408 | -0.124 | 18.657 | 10.300 | 1.00 20.84 |
| ATOM | 1324 | O | ALA | A | 408 | -0.470 | 18.590 | 11.473 | 1.00 22.53 |
| ATOM | 1325 | N | PRO | A | 409 | -0.848 | 19.319 | 9.377 | 1.00 23.20 |
| ATOM | 1326 | CD | PRO | A | 409 | -0.616 | 19.395 | 7.928 | 1.00 22.87 |
| ATOM | 1327 | CA | PRO | A | 409 | -2.081 | 20.034 | 9.733 | 1.00 23.46 |
| ATOM | 1328 | CB | PRO | A | 409 | -2.592 | 20.513 | 8.380 | 1.00 23.84 |
| ATOM | 1329 | CG | PRO | A | 409 | -1.336 | 20.661 | 7.581 | 1.00 24.05 |
| ATOM | 1330 | C | PRO | A | 409 | -3.131 | 19.188 | 10.458 | 1.00 23.64 |
| ATOM | 1331 | O | PRO | A | 409 | -3.751 | 19.656 | 11.415 | 1.00 23.96 |
| ATOM | 1332 | N | GLU | A | 410 | -3.324 | 17.946 | 10.022 | 1.00 23.26 |
| ATOM | 1333 | CA | GLU | A | 410 | -4.317 | 17.098 | 10.663 | 1.00 24.77 |
| ATOM | 1334 | CB | GLU | A | 410 | -4.617 | 15.835 | 9.841 | 1.00 23.34 |
| ATOM | 1335 | CG | GLU | A | 410 | -3.555 | 14.753 | 9.813 | 1.00 24.46 |
| ATOM | 1336 | CD | GLU | A | 410 | -2.399 | 15.057 | 8.865 | 1.00 23.81 |
| ATOM | 1337 | OE1 | GLU | A | 410 | -2.370 | 16.136 | 8.258 | 1.00 24.35 |
| ATOM | 1338 | OE2 | GLU | A | 410 | -1.503 | 14.200 | 8.722 | 1.00 22.93 |
| ATOM | 1339 | C | GLU | A | 410 | -3.918 | 16.756 | 12.089 | 1.00 25.94 |
| ATOM | 1340 | O | GLU | A | 410 | -4.773 | 16.636 | 12.967 | 1.00 28.86 |
| ATOM | 1341 | N | ALA | A | 411 | -2.620 | 16.615 | 12.321 | 1.00 25.51 |
| ATOM | 1342 | CA | ALA | A | 411 | -2.111 | 16.301 | 13.648 | 1.00 25.96 |
| ATOM | 1343 | CB | ALA | A | 411 | -0.642 | 15.917 | 13.584 | 1.00 24.83 |
| ATOM | 1344 | C | ALA | A | 411 | -2.314 | 17.520 | 14.555 | 1.00 26.68 |

Figure 6

```
ATOM   1345  O    ALA A 411      -2.637  17.367  15.726  1.00 28.50
ATOM   1346  N    ILE A 412      -2.176  18.725  14.003  1.00 26.71
ATOM   1347  CA   ILE A 412      -2.370  19.950  14.782  1.00 27.17
ATOM   1348  CB   ILE A 412      -1.872  21.207  14.031  1.00 26.78
ATOM   1349  CG2  ILE A 412      -2.280  22.488  14.794  1.00 26.08
ATOM   1350  CG1  ILE A 412      -0.359  21.168  13.867  1.00 25.10
ATOM   1351  CD1  ILE A 412       0.174  22.417  13.270  1.00 23.54
ATOM   1352  C    ILE A 412      -3.836  20.210  15.152  1.00 29.59
ATOM   1353  O    ILE A 412      -4.129  20.653  16.270  1.00 29.28
ATOM   1354  N    ASN A 413      -4.742  19.932  14.209  1.00 29.95
ATOM   1355  CA   ASN A 413      -6.162  20.177  14.399  1.00 29.06
ATOM   1356  CB   ASN A 413      -6.808  20.514  13.065  1.00 29.77
ATOM   1357  CG   ASN A 413      -6.167  21.714  12.398  1.00 31.50
ATOM   1358  OD1  ASN A 413      -5.827  22.716  13.049  1.00 30.98
ATOM   1359  ND2  ASN A 413      -5.997  21.623  11.087  1.00 31.79
ATOM   1360  C    ASN A 413      -6.977  19.108  15.099  1.00 29.58
ATOM   1361  O    ASN A 413      -7.875  19.432  15.890  1.00 29.50
ATOM   1362  N    TYR A 414      -6.660  17.847  14.828  1.00 29.43
ATOM   1363  CA   TYR A 414      -7.397  16.733  15.421  1.00 30.13
ATOM   1364  CB   TYR A 414      -8.181  15.999  14.333  1.00 32.55
ATOM   1365  CG   TYR A 414      -8.955  16.942  13.445  1.00 35.81
ATOM   1366  CD1  TYR A 414     -10.262  17.313  13.760  1.00 36.16
ATOM   1367  CE1  TYR A 414     -10.958  18.232  12.978  1.00 37.87
ATOM   1368  CD2  TYR A 414      -8.361  17.514  12.319  1.00 37.50
ATOM   1369  CE2  TYR A 414      -9.049  18.433  11.532  1.00 38.33
ATOM   1370  CZ   TYR A 414     -10.345  18.789  11.865  1.00 38.81
ATOM   1371  OH   TYR A 414     -11.025  19.691  11.071  1.00 40.92
ATOM   1372  C    TYR A 414      -6.504  15.745  16.170  1.00 29.83
ATOM   1373  O    TYR A 414      -6.997  14.791  16.791  1.00 28.58
ATOM   1374  N    GLY A 415      -5.192  15.965  16.099  1.00 28.47
ATOM   1375  CA   GLY A 415      -4.258  15.092  16.777  1.00 27.14
ATOM   1376  C    GLY A 415      -4.098  13.725  16.145  1.00 26.88
ATOM   1377  O    GLY A 415      -3.620  12.784  16.780  1.00 28.91
ATOM   1378  N    THR A 416      -4.493  13.586  14.895  1.00 26.46
ATOM   1379  CA   THR A 416      -4.335  12.293  14.260  1.00 25.87
ATOM   1380  CB   THR A 416      -5.459  12.037  13.189  1.00 25.32
ATOM   1381  OG1  THR A 416      -4.921  11.359  12.046  1.00 26.12
ATOM   1382  CG2  THR A 416      -6.125  13.330  12.759  1.00 23.44
ATOM   1383  C    THR A 416      -2.895  12.194  13.711  1.00 23.50
ATOM   1384  O    THR A 416      -2.489  12.990  12.873  1.00 23.91
ATOM   1385  N    PHE A 417      -2.097  11.318  14.323  1.00 22.58
ATOM   1386  CA   PHE A 417      -0.702  11.078  13.931  1.00 19.59
ATOM   1387  CB   PHE A 417       0.242  11.055  15.149  1.00 18.78
ATOM   1388  CG   PHE A 417       0.537  12.412  15.735  1.00 19.23
ATOM   1389  CD1  PHE A 417      -0.176  12.881  16.857  1.00 19.90
ATOM   1390  CD2  PHE A 417       1.529  13.224  15.179  1.00 16.99
ATOM   1391  CE1  PHE A 417       0.102  14.148  17.411  1.00 19.63
ATOM   1392  CE2  PHE A 417       1.820  14.491  15.715  1.00 16.68
ATOM   1393  CZ   PHE A 417       1.109  14.961  16.833  1.00 17.80
ATOM   1394  C    PHE A 417      -0.586   9.733  13.234  1.00 19.78
ATOM   1395  O    PHE A 417      -1.059   8.719  13.736  1.00 21.16
ATOM   1396  N    THR A 418       0.045   9.730  12.066  1.00 20.35
ATOM   1397  CA   THR A 418       0.259   8.513  11.293  1.00 18.90
ATOM   1398  CB   THR A 418      -0.868   8.279  10.233  1.00 18.09
ATOM   1399  OG1  THR A 418      -0.843   9.335   9.268  1.00 17.54
ATOM   1400  CG2  THR A 418      -2.255   8.235  10.895  1.00 18.13
ATOM   1401  C    THR A 418       1.609   8.644  10.579  1.00 19.18
ATOM   1402  O    THR A 418       2.310   9.657  10.703  1.00 18.48
ATOM   1403  N    ILE A 419       1.975   7.606   9.843  1.00 20.17
```

Figure 6

| | | | | | | | | | |
|---|---|---|---|---|---|---|---|---|---|
| ATOM | 1404 | CA | ILE | A | 419 | 3.210 | 7.616 | 9.087 | 1.00 21.11 |
| ATOM | 1405 | CB | ILE | A | 419 | 3.392 | 6.290 | 8.324 | 1.00 21.40 |
| ATOM | 1406 | CG2 | ILE | A | 419 | 2.416 | 6.191 | 7.142 | 1.00 18.94 |
| ATOM | 1407 | CG1 | ILE | A | 419 | 4.849 | 6.150 | 7.902 | 1.00 20.80 |
| ATOM | 1408 | CD1 | ILE | A | 419 | 5.787 | 6.075 | 9.088 | 1.00 19.14 |
| ATOM | 1409 | C | ILE | A | 419 | 3.199 | 8.780 | 8.085 | 1.00 22.27 |
| ATOM | 1410 | O | ILE | A | 419 | 4.252 | 9.322 | 7.756 | 1.00 24.82 |
| ATOM | 1411 | N | LYS | A | 420 | 2.001 | 9.198 | 7.664 | 1.00 20.37 |
| ATOM | 1412 | CA | LYS | A | 420 | 1.823 | 10.284 | 6.700 | 1.00 18.82 |
| ATOM | 1413 | CB | LYS | A | 420 | 0.411 | 10.267 | 6.116 | 1.00 18.53 |
| ATOM | 1414 | CG | LYS | A | 420 | 0.136 | 9.068 | 5.230 | 1.00 16.51 |
| ATOM | 1415 | CD | LYS | A | 420 | 1.066 | 9.091 | 4.041 | 1.00 17.86 |
| ATOM | 1416 | CE | LYS | A | 420 | 0.714 | 8.009 | 3.071 | 1.00 19.22 |
| ATOM | 1417 | NZ | LYS | A | 420 | 1.761 | 7.906 | 2.058 | 1.00 18.74 |
| ATOM | 1418 | C | LYS | A | 420 | 2.119 | 11.642 | 7.275 | 1.00 18.27 |
| ATOM | 1419 | O | LYS | A | 420 | 2.430 | 12.570 | 6.536 | 1.00 18.68 |
| ATOM | 1420 | N | SER | A | 421 | 1.933 | 11.795 | 8.582 | 1.00 19.19 |
| ATOM | 1421 | CA | SER | A | 421 | 2.261 | 13.062 | 9.204 | 1.00 19.14 |
| ATOM | 1422 | CB | SER | A | 421 | 1.457 | 13.289 | 10.498 | 1.00 18.74 |
| ATOM | 1423 | OG | SER | A | 421 | 1.230 | 12.090 | 11.208 | 1.00 18.58 |
| ATOM | 1424 | C | SER | A | 421 | 3.794 | 13.062 | 9.409 | 1.00 20.04 |
| ATOM | 1425 | O | SER | A | 421 | 4.419 | 14.119 | 9.469 | 1.00 19.85 |
| ATOM | 1426 | N | ASP | A | 422 | 4.400 | 11.870 | 9.449 | 1.00 18.69 |
| ATOM | 1427 | CA | ASP | A | 422 | 5.848 | 11.766 | 9.555 | 1.00 18.51 |
| ATOM | 1428 | CB | ASP | A | 422 | 6.295 | 10.338 | 9.796 | 1.00 17.93 |
| ATOM | 1429 | CG | ASP | A | 422 | 6.026 | 9.858 | 11.198 | 1.00 19.06 |
| ATOM | 1430 | OD1 | ASP | A | 422 | 5.745 | 10.664 | 12.122 | 1.00 20.44 |
| ATOM | 1431 | OD2 | ASP | A | 422 | 6.118 | 8.634 | 11.377 | 1.00 19.59 |
| ATOM | 1432 | C | ASP | A | 422 | 6.385 | 12.199 | 8.203 | 1.00 20.51 |
| ATOM | 1433 | O | ASP | A | 422 | 7.448 | 12.814 | 8.127 | 1.00 22.07 |
| ATOM | 1434 | N | VAL | A | 423 | 5.684 | 11.816 | 7.132 | 1.00 20.75 |
| ATOM | 1435 | CA | VAL | A | 423 | 6.076 | 12.208 | 5.769 | 1.00 19.33 |
| ATOM | 1436 | CB | VAL | A | 423 | 5.147 | 11.604 | 4.678 | 1.00 18.66 |
| ATOM | 1437 | CG1 | VAL | A | 423 | 5.508 | 12.165 | 3.304 | 1.00 17.96 |
| ATOM | 1438 | CG2 | VAL | A | 423 | 5.272 | 10.089 | 4.664 | 1.00 17.80 |
| ATOM | 1439 | C | VAL | A | 423 | 6.054 | 13.735 | 5.678 | 1.00 19.49 |
| ATOM | 1440 | O | VAL | A | 423 | 6.875 | 14.324 | 4.977 | 1.00 21.06 |
| ATOM | 1441 | N | TRP | A | 424 | 5.132 | 14.374 | 6.394 | 1.00 18.70 |
| ATOM | 1442 | CA | TRP | A | 424 | 5.061 | 15.835 | 6.404 | 1.00 18.20 |
| ATOM | 1443 | CB | TRP | A | 424 | 3.786 | 16.301 | 7.114 | 1.00 15.94 |
| ATOM | 1444 | CG | TRP | A | 424 | 3.711 | 17.778 | 7.314 | 1.00 14.20 |
| ATOM | 1445 | CD2 | TRP | A | 424 | 2.872 | 18.701 | 6.616 | 1.00 13.72 |
| ATOM | 1446 | CE2 | TRP | A | 424 | 3.192 | 19.998 | 7.077 | 1.00 14.72 |
| ATOM | 1447 | CE3 | TRP | A | 424 | 1.878 | 18.563 | 5.635 | 1.00 13.75 |
| ATOM | 1448 | CD1 | TRP | A | 424 | 4.475 | 18.529 | 8.160 | 1.00 14.89 |
| ATOM | 1449 | NE1 | TRP | A | 424 | 4.180 | 19.864 | 8.021 | 1.00 14.50 |
| ATOM | 1450 | CZ2 | TRP | A | 424 | 2.561 | 21.146 | 6.593 | 1.00 14.48 |
| ATOM | 1451 | CZ3 | TRP | A | 424 | 1.256 | 19.691 | 5.158 | 1.00 11.23 |
| ATOM | 1452 | CH2 | TRP | A | 424 | 1.595 | 20.967 | 5.632 | 1.00 13.61 |
| ATOM | 1453 | C | TRP | A | 424 | 6.301 | 16.362 | 7.128 | 1.00 19.76 |
| ATOM | 1454 | O | TRP | A | 424 | 6.934 | 17.308 | 6.676 | 1.00 20.07 |
| ATOM | 1455 | N | SER | A | 425 | 6.653 | 15.720 | 8.242 | 1.00 23.33 |
| ATOM | 1456 | CA | SER | A | 425 | 7.814 | 16.114 | 9.051 | 1.00 23.23 |
| ATOM | 1457 | CB | SER | A | 425 | 7.897 | 15.280 | 10.333 | 1.00 23.30 |
| ATOM | 1458 | OG | SER | A | 425 | 6.835 | 15.585 | 11.212 | 1.00 24.21 |
| ATOM | 1459 | C | SER | A | 425 | 9.108 | 15.962 | 8.271 | 1.00 22.68 |
| ATOM | 1460 | O | SER | A | 425 | 9.976 | 16.834 | 8.321 | 1.00 23.33 |
| ATOM | 1461 | N | PHE | A | 426 | 9.220 | 14.853 | 7.549 | 1.00 21.10 |
| ATOM | 1462 | CA | PHE | A | 426 | 10.394 | 14.576 | 6.744 | 1.00 22.17 |

Figure 6

| | | | | | | | | |
|---|---|---|---|---|---|---|---|---|
| ATOM | 1463 | CB | PHE | A | 426 | 10.250 | 13.244 | 6.012 | 1.00 | 22.94 |
| ATOM | 1464 | CG | PHE | A | 426 | 11.439 | 12.898 | 5.160 | 1.00 | 24.30 |
| ATOM | 1465 | CD1 | PHE | A | 426 | 12.616 | 12.448 | 5.748 | 1.00 | 24.56 |
| ATOM | 1466 | CD2 | PHE | A | 426 | 11.386 | 13.029 | 3.776 | 1.00 | 23.58 |
| ATOM | 1467 | CE1 | PHE | A | 426 | 13.730 | 12.128 | 4.972 | 1.00 | 26.25 |
| ATOM | 1468 | CE2 | PHE | A | 426 | 12.490 | 12.712 | 2.993 | 1.00 | 25.28 |
| ATOM | 1469 | CZ | PHE | A | 426 | 13.668 | 12.259 | 3.594 | 1.00 | 25.56 |
| ATOM | 1470 | C | PHE | A | 426 | 10.645 | 15.691 | 5.732 | 1.00 | 22.44 |
| ATOM | 1471 | O | PHE | A | 426 | 11.795 | 16.007 | 5.431 | 1.00 | 23.33 |
| ATOM | 1472 | N | GLY | A | 427 | 9.572 | 16.269 | 5.202 | 1.00 | 21.27 |
| ATOM | 1473 | CA | GLY | A | 427 | 9.718 | 17.344 | 4.242 | 1.00 | 20.51 |
| ATOM | 1474 | C | GLY | A | 427 | 10.205 | 18.605 | 4.914 | 1.00 | 20.27 |
| ATOM | 1475 | O | GLY | A | 427 | 10.859 | 19.446 | 4.301 | 1.00 | 20.90 |
| ATOM | 1476 | N | ILE | A | 428 | 9.816 | 18.773 | 6.168 | 1.00 | 21.52 |
| ATOM | 1477 | CA | ILE | A | 428 | 10.242 | 19.935 | 6.948 | 1.00 | 21.70 |
| ATOM | 1478 | CB | ILE | A | 428 | 9.403 | 20.085 | 8.239 | 1.00 | 19.71 |
| ATOM | 1479 | CG2 | ILE | A | 428 | 9.858 | 21.306 | 9.008 | 1.00 | 18.13 |
| ATOM | 1480 | CG1 | ILE | A | 428 | 7.914 | 20.188 | 7.889 | 1.00 | 18.97 |
| ATOM | 1481 | CD1 | ILE | A | 428 | 7.553 | 21.393 | 7.042 | 1.00 | 19.23 |
| ATOM | 1482 | C | ILE | A | 428 | 11.708 | 19.709 | 7.332 | 1.00 | 22.20 |
| ATOM | 1483 | O | ILE | A | 428 | 12.483 | 20.659 | 7.432 | 1.00 | 22.73 |
| ATOM | 1484 | N | LEU | A | 429 | 12.074 | 18.431 | 7.491 | 1.00 | 20.95 |
| ATOM | 1485 | CA | LEU | A | 429 | 13.416 | 18.009 | 7.866 | 1.00 | 18.86 |
| ATOM | 1486 | CB | LEU | A | 429 | 13.399 | 16.527 | 8.250 | 1.00 | 16.64 |
| ATOM | 1487 | CG | LEU | A | 429 | 14.550 | 15.887 | 9.029 | 1.00 | 15.68 |
| ATOM | 1488 | CD1 | LEU | A | 429 | 14.149 | 14.502 | 9.434 | 1.00 | 15.83 |
| ATOM | 1489 | CD2 | LEU | A | 429 | 15.829 | 15.834 | 8.239 | 1.00 | 15.73 |
| ATOM | 1490 | C | LEU | A | 429 | 14.362 | 18.240 | 6.704 | 1.00 | 20.36 |
| ATOM | 1491 | O | LEU | A | 429 | 15.520 | 18.608 | 6.928 | 1.00 | 20.64 |
| ATOM | 1492 | N | LEU | A | 430 | 13.875 | 18.017 | 5.471 | 1.00 | 20.76 |
| ATOM | 1493 | CA | LEU | A | 430 | 14.678 | 18.202 | 4.263 | 1.00 | 19.64 |
| ATOM | 1494 | CB | LEU | A | 430 | 13.934 | 17.766 | 2.999 | 1.00 | 18.40 |
| ATOM | 1495 | CG | LEU | A | 430 | 13.660 | 16.290 | 2.709 | 1.00 | 18.21 |
| ATOM | 1496 | CD1 | LEU | A | 430 | 12.735 | 16.162 | 1.514 | 1.00 | 16.14 |
| ATOM | 1497 | CD2 | LEU | A | 430 | 14.944 | 15.533 | 2.459 | 1.00 | 18.64 |
| ATOM | 1498 | C | LEU | A | 430 | 15.082 | 19.648 | 4.103 | 1.00 | 21.92 |
| ATOM | 1499 | O | LEU | A | 430 | 16.096 | 19.923 | 3.474 | 1.00 | 24.71 |
| ATOM | 1500 | N | THR | A | 431 | 14.277 | 20.577 | 4.610 | 1.00 | 22.79 |
| ATOM | 1501 | CA | THR | A | 431 | 14.629 | 21.997 | 4.511 | 1.00 | 23.56 |
| ATOM | 1502 | CB | THR | A | 431 | 13.442 | 22.960 | 4.790 | 1.00 | 24.27 |
| ATOM | 1503 | OG1 | THR | A | 431 | 13.129 | 22.949 | 6.191 | 1.00 | 25.78 |
| ATOM | 1504 | CG2 | THR | A | 431 | 12.211 | 22.573 | 3.968 | 1.00 | 22.47 |
| ATOM | 1505 | C | THR | A | 431 | 15.733 | 22.270 | 5.521 | 1.00 | 24.80 |
| ATOM | 1506 | O | THR | A | 431 | 16.557 | 23.148 | 5.317 | 1.00 | 26.79 |
| ATOM | 1507 | N | GLU | A | 432 | 15.696 | 21.551 | 6.646 | 1.00 | 25.64 |
| ATOM | 1508 | CA | GLU | A | 432 | 16.722 | 21.663 | 7.676 | 1.00 | 24.33 |
| ATOM | 1509 | CB | GLU | A | 432 | 16.377 | 20.780 | 8.872 | 1.00 | 23.63 |
| ATOM | 1510 | CG | GLU | A | 432 | 15.242 | 21.323 | 9.707 | 1.00 | 24.68 |
| ATOM | 1511 | CD | GLU | A | 432 | 15.011 | 20.521 | 10.973 | 1.00 | 24.85 |
| ATOM | 1512 | OE1 | GLU | A | 432 | 14.492 | 19.392 | 10.892 | 1.00 | 23.86 |
| ATOM | 1513 | OE2 | GLU | A | 432 | 15.349 | 21.030 | 12.058 | 1.00 | 25.56 |
| ATOM | 1514 | C | GLU | A | 432 | 18.070 | 21.232 | 7.100 | 1.00 | 24.16 |
| ATOM | 1515 | O | GLU | A | 432 | 19.077 | 21.868 | 7.346 | 1.00 | 26.89 |
| ATOM | 1516 | N | ILE | A | 433 | 18.069 | 20.171 | 6.307 | 1.00 | 23.06 |
| ATOM | 1517 | CA | ILE | A | 433 | 19.277 | 19.641 | 5.688 | 1.00 | 23.10 |
| ATOM | 1518 | CB | ILE | A | 433 | 18.956 | 18.281 | 5.039 | 1.00 | 22.50 |
| ATOM | 1519 | CG2 | ILE | A | 433 | 20.146 | 17.727 | 4.316 | 1.00 | 21.70 |
| ATOM | 1520 | CG1 | ILE | A | 433 | 18.486 | 17.295 | 6.102 | 1.00 | 22.32 |
| ATOM | 1521 | CD1 | ILE | A | 433 | 18.211 | 15.894 | 5.557 | 1.00 | 23.81 |

Figure 6

| ATOM | 1522 | C | ILE A 433 | 19.939 | 20.568 | 4.652 | 1.00 | 25.56 |
|------|------|------|-----------|--------|--------|-------|------|-------|
| ATOM | 1523 | O | ILE A 433 | 21.159 | 20.792 | 4.680 | 1.00 | 28.24 |
| ATOM | 1524 | N | VAL A 434 | 19.133 | 21.145 | 3.768 | 1.00 | 27.93 |
| ATOM | 1525 | CA | VAL A 434 | 19.654 | 22.003 | 2.707 | 1.00 | 27.41 |
| ATOM | 1526 | CB | VAL A 434 | 18.767 | 21.951 | 1.436 | 1.00 | 26.59 |
| ATOM | 1527 | CG1 | VAL A 434 | 18.756 | 20.530 | 0.881 | 1.00 | 25.57 |
| ATOM | 1528 | CG2 | VAL A 434 | 17.347 | 22.453 | 1.734 | 1.00 | 24.18 |
| ATOM | 1529 | C | VAL A 434 | 19.927 | 23.443 | 3.092 | 1.00 | 29.03 |
| ATOM | 1530 | O | VAL A 434 | 20.454 | 24.212 | 2.281 | 1.00 | 30.58 |
| ATOM | 1531 | N | THR A 435 | 19.541 | 23.824 | 4.304 | 1.00 | 29.67 |
| ATOM | 1532 | CA | THR A 435 | 19.789 | 25.180 | 4.780 | 1.00 | 31.95 |
| ATOM | 1533 | CB | THR A 435 | 18.491 | 25.880 | 5.208 | 1.00 | 31.75 |
| ATOM | 1534 | OG1 | THR A 435 | 17.900 | 25.180 | 6.310 | 1.00 | 31.27 |
| ATOM | 1535 | CG2 | THR A 435 | 17.514 | 25.942 | 4.044 | 1.00 | 31.52 |
| ATOM | 1536 | C | THR A 435 | 20.736 | 25.117 | 5.972 | 1.00 | 34.10 |
| ATOM | 1537 | O | THR A 435 | 20.827 | 26.062 | 6.751 | 1.00 | 34.10 |
| ATOM | 1538 | N | HIS A 436 | 21.407 | 23.974 | 6.113 | 1.00 | 36.75 |
| ATOM | 1539 | CA | HIS A 436 | 22.351 | 23.722 | 7.192 | 1.00 | 39.18 |
| ATOM | 1540 | CB | HIS A 436 | 23.664 | 24.474 | 6.938 | 1.00 | 43.38 |
| ATOM | 1541 | CG | HIS A 436 | 24.330 | 24.096 | 5.649 | 1.00 | 47.82 |
| ATOM | 1542 | CD2 | HIS A 436 | 24.763 | 24.852 | 4.611 | 1.00 | 48.73 |
| ATOM | 1543 | ND1 | HIS A 436 | 24.577 | 22.783 | 5.292 | 1.00 | 48.77 |
| ATOM | 1544 | CE1 | HIS A 436 | 25.132 | 22.750 | 4.092 | 1.00 | 48.46 |
| ATOM | 1545 | NE2 | HIS A 436 | 25.253 | 23.991 | 3.657 | 1.00 | 49.33 |
| ATOM | 1546 | C | HIS A 436 | 21.812 | 24.001 | 8.595 | 1.00 | 38.42 |
| ATOM | 1547 | O | HIS A 436 | 22.404 | 24.765 | 9.357 | 1.00 | 38.35 |
| ATOM | 1548 | N | GLY A 437 | 20.686 | 23.371 | 8.926 | 1.00 | 36.15 |
| ATOM | 1549 | CA | GLY A 437 | 20.092 | 23.519 | 10.243 | 1.00 | 36.82 |
| ATOM | 1550 | C | GLY A 437 | 19.260 | 24.744 | 10.572 | 1.00 | 37.12 |
| ATOM | 1551 | O | GLY A 437 | 18.992 | 25.006 | 11.743 | 1.00 | 38.42 |
| ATOM | 1552 | N | ARG A 438 | 18.829 | 25.477 | 9.554 | 1.00 | 37.13 |
| ATOM | 1553 | CA | ARG A 438 | 18.003 | 26.670 | 9.744 | 1.00 | 36.69 |
| ATOM | 1554 | CB | ARG A 438 | 17.853 | 27.373 | 8.387 | 1.00 | 38.70 |
| ATOM | 1555 | CG | ARG A 438 | 17.444 | 28.844 | 8.402 | 1.00 | 41.09 |
| ATOM | 1556 | CD | ARG A 438 | 15.931 | 29.057 | 8.468 | 1.00 | 44.82 |
| ATOM | 1557 | NE | ARG A 438 | 15.187 | 28.410 | 7.385 | 1.00 | 46.62 |
| ATOM | 1558 | CZ | ARG A 438 | 15.248 | 28.770 | 6.102 | 1.00 | 48.62 |
| ATOM | 1559 | NH1 | ARG A 438 | 16.025 | 29.783 | 5.717 | 1.00 | 48.18 |
| ATOM | 1560 | NH2 | ARG A 438 | 14.533 | 28.108 | 5.193 | 1.00 | 48.71 |
| ATOM | 1561 | C | ARG A 438 | 16.628 | 26.251 | 10.299 | 1.00 | 36.17 |
| ATOM | 1562 | O | ARG A 438 | 16.122 | 25.181 | 9.967 | 1.00 | 35.76 |
| ATOM | 1563 | N | ILE A 439 | 16.044 | 27.070 | 11.171 | 1.00 | 34.95 |
| ATOM | 1564 | CA | ILE A 439 | 14.729 | 26.772 | 11.747 | 1.00 | 34.53 |
| ATOM | 1565 | CB | ILE A 439 | 14.459 | 27.671 | 12.982 | 1.00 | 34.51 |
| ATOM | 1566 | CG2 | ILE A 439 | 12.973 | 27.860 | 13.223 | 1.00 | 33.62 |
| ATOM | 1567 | CG1 | ILE A 439 | 15.120 | 27.045 | 14.216 | 1.00 | 35.47 |
| ATOM | 1568 | CD1 | ILE A 439 | 15.382 | 28.026 | 15.360 | 1.00 | 35.08 |
| ATOM | 1569 | C | ILE A 439 | 13.620 | 26.940 | 10.695 | 1.00 | 35.74 |
| ATOM | 1570 | O | ILE A 439 | 13.601 | 27.948 | 9.968 | 1.00 | 37.02 |
| ATOM | 1571 | N | PRO A 440 | 12.695 | 25.949 | 10.591 | 1.00 | 33.93 |
| ATOM | 1572 | CD | PRO A 440 | 12.673 | 24.684 | 11.349 | 1.00 | 32.97 |
| ATOM | 1573 | CA | PRO A 440 | 11.587 | 25.985 | 9.627 | 1.00 | 32.95 |
| ATOM | 1574 | CB | PRO A 440 | 10.750 | 24.784 | 10.033 | 1.00 | 33.41 |
| ATOM | 1575 | CG | PRO A 440 | 11.806 | 23.811 | 10.483 | 1.00 | 32.94 |
| ATOM | 1576 | C | PRO A 440 | 10.813 | 27.274 | 9.751 | 1.00 | 32.82 |
| ATOM | 1577 | O | PRO A 440 | 10.787 | 27.875 | 10.824 | 1.00 | 34.39 |
| ATOM | 1578 | N | TYR A 441 | 10.233 | 27.724 | 8.641 | 1.00 | 32.05 |
| ATOM | 1579 | CA | TYR A 441 | 9.476 | 28.976 | 8.588 | 1.00 | 31.34 |
| ATOM | 1580 | CB | TYR A 441 | 8.084 | 28.816 | 9.191 | 1.00 | 29.27 |

Figure 6

| | | | | | | | | | |
|---|---|---|---|---|---|---|---|---|---|
| ATOM | 1581 | CG  | TYR | A | 441 |  7.342 | 27.601 |  8.738 | 1.00 26.74 |
| ATOM | 1582 | CD1 | TYR | A | 441 |  6.446 | 27.665 |  7.679 | 1.00 25.41 |
| ATOM | 1583 | CE1 | TYR | A | 441 |  5.758 | 26.540 |  7.268 | 1.00 24.86 |
| ATOM | 1584 | CD2 | TYR | A | 441 |  7.527 | 26.389 |  9.377 | 1.00 25.40 |
| ATOM | 1585 | CE2 | TYR | A | 441 |  6.845 | 25.263 |  8.980 | 1.00 25.86 |
| ATOM | 1586 | CZ  | TYR | A | 441 |  5.961 | 25.342 |  7.926 | 1.00 25.46 |
| ATOM | 1587 | OH  | TYR | A | 441 |  5.265 | 24.216 |  7.563 | 1.00 26.23 |
| ATOM | 1588 | C   | TYR | A | 441 | 10.198 | 30.106 |  9.316 | 1.00 32.97 |
| ATOM | 1589 | O   | TYR | A | 441 |  9.850 | 30.468 | 10.446 | 1.00 33.02 |
| ATOM | 1590 | N   | PRO | A | 442 | 11.260 | 30.637 |  8.710 | 1.00 35.08 |
| ATOM | 1591 | CD  | PRO | A | 442 | 11.903 | 30.284 |  7.429 | 1.00 35.28 |
| ATOM | 1592 | CA  | PRO | A | 442 | 11.964 | 31.729 |  9.389 | 1.00 36.53 |
| ATOM | 1593 | CB  | PRO | A | 442 | 13.177 | 31.959 |  8.483 | 1.00 36.38 |
| ATOM | 1594 | CG  | PRO | A | 442 | 12.685 | 31.534 |  7.109 | 1.00 35.77 |
| ATOM | 1595 | C   | PRO | A | 442 | 11.069 | 32.974 |  9.482 | 1.00 38.28 |
| ATOM | 1596 | O   | PRO | A | 442 | 10.185 | 33.169 |  8.653 | 1.00 38.39 |
| ATOM | 1597 | N   | GLY | A | 443 | 11.242 | 33.769 | 10.534 | 1.00 40.15 |
| ATOM | 1598 | CA  | GLY | A | 443 | 10.448 | 34.981 | 10.672 | 1.00 41.89 |
| ATOM | 1599 | C   | GLY | A | 443 |  9.019 | 34.744 | 11.118 | 1.00 43.33 |
| ATOM | 1600 | O   | GLY | A | 443 |  8.186 | 35.657 | 11.109 | 1.00 45.58 |
| ATOM | 1601 | N   | MET | A | 444 |  8.727 | 33.506 | 11.491 | 1.00 43.17 |
| ATOM | 1602 | CA  | MET | A | 444 |  7.399 | 33.154 | 11.965 | 1.00 43.48 |
| ATOM | 1603 | CB  | MET | A | 444 |  6.712 | 32.208 | 10.978 | 1.00 43.58 |
| ATOM | 1604 | CG  | MET | A | 444 |  6.217 | 32.867 |  9.710 | 1.00 44.02 |
| ATOM | 1605 | SD  | MET | A | 444 |  5.595 | 31.633 |  8.546 | 1.00 43.60 |
| ATOM | 1606 | CE  | MET | A | 444 |  4.327 | 31.006 |  9.463 | 1.00 43.04 |
| ATOM | 1607 | C   | MET | A | 444 |  7.504 | 32.478 | 13.332 | 1.00 43.14 |
| ATOM | 1608 | O   | MET | A | 444 |  8.470 | 31.759 | 13.602 | 1.00 43.67 |
| ATOM | 1609 | N   | THR | A | 445 |  6.531 | 32.749 | 14.199 | 1.00 41.60 |
| ATOM | 1610 | CA  | THR | A | 445 |  6.479 | 32.144 | 15.518 | 1.00 40.57 |
| ATOM | 1611 | CB  | THR | A | 445 |  5.978 | 33.156 | 16.564 | 1.00 41.96 |
| ATOM | 1612 | OG1 | THR | A | 445 |  4.586 | 33.425 | 16.355 | 1.00 43.32 |
| ATOM | 1613 | CG2 | THR | A | 445 |  6.755 | 34.470 | 16.450 | 1.00 40.64 |
| ATOM | 1614 | C   | THR | A | 445 |  5.488 | 30.996 | 15.382 | 1.00 40.44 |
| ATOM | 1615 | O   | THR | A | 445 |  4.838 | 30.876 | 14.354 | 1.00 41.53 |
| ATOM | 1616 | N   | ASN | A | 446 |  5.364 | 30.141 | 16.388 | 1.00 40.64 |
| ATOM | 1617 | CA  | ASN | A | 446 |  4.420 | 29.033 | 16.300 | 1.00 41.36 |
| ATOM | 1618 | CB  | ASN | A | 446 |  4.410 | 28.207 | 17.578 | 1.00 42.11 |
| ATOM | 1619 | CG  | ASN | A | 446 |  5.479 | 27.162 | 17.584 | 1.00 43.34 |
| ATOM | 1620 | OD1 | ASN | A | 446 |  6.417 | 27.207 | 16.780 | 1.00 42.99 |
| ATOM | 1621 | ND2 | ASN | A | 446 |  5.348 | 26.195 | 18.480 | 1.00 44.70 |
| ATOM | 1622 | C   | ASN | A | 446 |  2.999 | 29.445 | 15.952 | 1.00 41.90 |
| ATOM | 1623 | O   | ASN | A | 446 |  2.436 | 28.952 | 14.975 | 1.00 40.46 |
| ATOM | 1624 | N   | PRO | A | 447 |  2.401 | 30.360 | 16.743 | 1.00 42.73 |
| ATOM | 1625 | CD  | PRO | A | 447 |  2.947 | 31.110 | 17.890 | 1.00 41.75 |
| ATOM | 1626 | CA  | PRO | A | 447 |  1.027 | 30.790 | 16.447 | 1.00 42.21 |
| ATOM | 1627 | CB  | PRO | A | 447 |  0.777 | 31.891 | 17.486 | 1.00 42.12 |
| ATOM | 1628 | CG  | PRO | A | 447 |  2.168 | 32.391 | 17.820 | 1.00 42.07 |
| ATOM | 1629 | C   | PRO | A | 447 |  0.831 | 31.277 | 15.008 | 1.00 41.11 |
| ATOM | 1630 | O   | PRO | A | 447 | -0.233 | 31.062 | 14.425 | 1.00 41.72 |
| ATOM | 1631 | N   | GLU | A | 448 |  1.863 | 31.899 | 14.439 | 1.00 38.77 |
| ATOM | 1632 | CA  | GLU | A | 448 |  1.812 | 32.393 | 13.066 | 1.00 39.05 |
| ATOM | 1633 | CB  | GLU | A | 448 |  2.952 | 33.363 | 12.786 | 1.00 40.15 |
| ATOM | 1634 | CG  | GLU | A | 448 |  2.812 | 34.666 | 13.525 | 1.00 43.47 |
| ATOM | 1635 | CD  | GLU | A | 448 |  3.920 | 35.639 | 13.213 | 1.00 44.66 |
| ATOM | 1636 | OE1 | GLU | A | 448 |  4.964 | 35.218 | 12.672 | 1.00 46.97 |
| ATOM | 1637 | OE2 | GLU | A | 448 |  3.745 | 36.837 | 13.510 | 1.00 46.27 |
| ATOM | 1638 | C   | GLU | A | 448 |  1.855 | 31.259 | 12.057 | 1.00 38.02 |
| ATOM | 1639 | O   | GLU | A | 448 |  1.172 | 31.318 | 11.031 | 1.00 38.92 |

Figure 6

| | | | | | | | | | |
|---|---|---|---|---|---|---|---|---|---|
| ATOM | 1640 | N | VAL | A | 449 | 2.672 | 30.244 | 12.341 | 1.00 35.10 |
| ATOM | 1641 | CA | VAL | A | 449 | 2.781 | 29.071 | 11.474 | 1.00 32.14 |
| ATOM | 1642 | CB | VAL | A | 449 | 3.855 | 28.063 | 11.996 | 1.00 31.14 |
| ATOM | 1643 | CG1 | VAL | A | 449 | 3.686 | 26.678 | 11.368 | 1.00 29.25 |
| ATOM | 1644 | CG2 | VAL | A | 449 | 5.249 | 28.592 | 11.687 | 1.00 30.08 |
| ATOM | 1645 | C | VAL | A | 449 | 1.416 | 28.418 | 11.425 | 1.00 31.55 |
| ATOM | 1646 | O | VAL | A | 449 | 0.994 | 27.935 | 10.383 | 1.00 30.77 |
| ATOM | 1647 | N | ILE | A | 450 | 0.724 | 28.443 | 12.561 | 1.00 32.84 |
| ATOM | 1648 | CA | ILE | A | 450 | -0.608 | 27.871 | 12.681 | 1.00 32.55 |
| ATOM | 1649 | CB | ILE | A | 450 | -1.089 | 27.870 | 14.150 | 1.00 32.54 |
| ATOM | 1650 | CG2 | ILE | A | 450 | -2.469 | 27.245 | 14.254 | 1.00 32.66 |
| ATOM | 1651 | CG1 | ILE | A | 450 | -0.110 | 27.095 | 15.036 | 1.00 33.01 |
| ATOM | 1652 | CD1 | ILE | A | 450 | 0.029 | 25.638 | 14.683 | 1.00 32.53 |
| ATOM | 1653 | C | ILE | A | 450 | -1.627 | 28.626 | 11.818 | 1.00 31.41 |
| ATOM | 1654 | O | ILE | A | 450 | -2.378 | 28.005 | 11.069 | 1.00 29.01 |
| ATOM | 1655 | N | GLN | A | 451 | -1.632 | 29.955 | 11.899 | 1.00 31.93 |
| ATOM | 1656 | CA | GLN | A | 451 | -2.595 | 30.725 | 11.129 | 1.00 33.33 |
| ATOM | 1657 | CB | GLN | A | 451 | -2.838 | 32.136 | 11.684 | 1.00 34.51 |
| ATOM | 1658 | CG | GLN | A | 451 | -1.651 | 33.066 | 11.807 | 1.00 38.35 |
| ATOM | 1659 | CD | GLN | A | 451 | -1.818 | 34.056 | 12.988 | 1.00 40.70 |
| ATOM | 1660 | OE1 | GLN | A | 451 | -1.347 | 35.200 | 12.943 | 1.00 41.83 |
| ATOM | 1661 | NE2 | GLN | A | 451 | -2.472 | 33.599 | 14.053 | 1.00 40.54 |
| ATOM | 1662 | C | GLN | A | 451 | -2.289 | 30.745 | 9.666 | 1.00 31.92 |
| ATOM | 1663 | O | GLN | A | 451 | -3.190 | 30.916 | 8.856 | 1.00 32.38 |
| ATOM | 1664 | N | ASN | A | 452 | -1.028 | 30.506 | 9.336 | 1.00 31.64 |
| ATOM | 1665 | CA | ASN | A | 452 | -0.589 | 30.465 | 7.944 | 1.00 30.16 |
| ATOM | 1666 | CB | ASN | A | 452 | 0.914 | 30.715 | 7.824 | 1.00 31.10 |
| ATOM | 1667 | CG | ASN | A | 452 | 1.233 | 32.137 | 7.446 | 1.00 31.39 |
| ATOM | 1668 | OD1 | ASN | A | 452 | 1.332 | 32.467 | 6.268 | 1.00 32.79 |
| ATOM | 1669 | ND2 | ASN | A | 452 | 1.390 | 32.994 | 8.442 | 1.00 32.99 |
| ATOM | 1670 | C | ASN | A | 452 | -0.924 | 29.116 | 7.349 | 1.00 29.37 |
| ATOM | 1671 | O | ASN | A | 452 | -1.259 | 29.032 | 6.179 | 1.00 29.73 |
| ATOM | 1672 | N | LEU | A | 453 | -0.802 | 28.058 | 8.147 | 1.00 28.78 |
| ATOM | 1673 | CA | LEU | A | 453 | -1.125 | 26.712 | 7.692 | 1.00 27.98 |
| ATOM | 1674 | CB | LEU | A | 453 | -0.653 | 25.667 | 8.688 | 1.00 28.87 |
| ATOM | 1675 | CG | LEU | A | 453 | 0.824 | 25.295 | 8.663 | 1.00 30.06 |
| ATOM | 1676 | CD1 | LEU | A | 453 | 1.011 | 24.160 | 9.659 | 1.00 30.96 |
| ATOM | 1677 | CD2 | LEU | A | 453 | 1.265 | 24.858 | 7.268 | 1.00 29.70 |
| ATOM | 1678 | C | LEU | A | 453 | -2.620 | 26.562 | 7.474 | 1.00 27.52 |
| ATOM | 1679 | O | LEU | A | 453 | -3.035 | 25.803 | 6.605 | 1.00 27.55 |
| ATOM | 1680 | N | GLU | A | 454 | -3.425 | 27.239 | 8.296 | 1.00 27.54 |
| ATOM | 1681 | CA | GLU | A | 454 | -4.881 | 27.223 | 8.150 | 1.00 28.72 |
| ATOM | 1682 | CB | GLU | A | 454 | -5.525 | 28.211 | 9.123 | 1.00 31.71 |
| ATOM | 1683 | CG | GLU | A | 454 | -5.740 | 27.752 | 10.551 | 1.00 35.16 |
| ATOM | 1684 | CD | GLU | A | 454 | -6.050 | 28.931 | 11.480 | 1.00 36.71 |
| ATOM | 1685 | OE1 | GLU | A | 454 | -5.788 | 28.802 | 12.697 | 1.00 38.89 |
| ATOM | 1686 | OE2 | GLU | A | 454 | -6.527 | 29.992 | 10.994 | 1.00 37.15 |
| ATOM | 1687 | C | GLU | A | 454 | -5.217 | 27.701 | 6.729 | 1.00 27.50 |
| ATOM | 1688 | O | GLU | A | 454 | -6.189 | 27.260 | 6.120 | 1.00 25.59 |
| ATOM | 1689 | N | ARG | A | 455 | -4.417 | 28.651 | 6.251 | 1.00 25.93 |
| ATOM | 1690 | CA | ARG | A | 455 | -4.547 | 29.257 | 4.935 | 1.00 24.89 |
| ATOM | 1691 | CB | ARG | A | 455 | -4.060 | 30.722 | 4.988 | 1.00 26.68 |
| ATOM | 1692 | CG | ARG | A | 455 | -4.992 | 31.653 | 5.756 | 1.00 31.07 |
| ATOM | 1693 | CD | ARG | A | 455 | -4.455 | 33.086 | 5.871 | 1.00 33.92 |
| ATOM | 1694 | NE | ARG | A | 455 | -3.525 | 33.212 | 6.988 | 1.00 39.15 |
| ATOM | 1695 | CZ | ARG | A | 455 | -2.755 | 34.270 | 7.215 | 1.00 40.88 |
| ATOM | 1696 | NH1 | ARG | A | 455 | -2.807 | 35.321 | 6.412 | 1.00 42.93 |
| ATOM | 1697 | NH2 | ARG | A | 455 | -1.877 | 34.245 | 8.209 | 1.00 43.19 |
| ATOM | 1698 | C | ARG | A | 455 | -3.822 | 28.493 | 3.813 | 1.00 23.15 |

Figure 6

| ATOM | 1699 | O   | ARG | A | 455 | -3.763 | 28.962 | 2.676  | 1.00 | 24.28 |
| ATOM | 1700 | N   | GLY | A | 456 | -3.244 | 27.344 | 4.146  | 1.00 | 20.54 |
| ATOM | 1701 | CA  | GLY | A | 456 | -2.550 | 26.536 | 3.162  | 1.00 | 19.36 |
| ATOM | 1702 | C   | GLY | A | 456 | -1.158 | 26.975 | 2.758  | 1.00 | 19.44 |
| ATOM | 1703 | O   | GLY | A | 456 | -0.649 | 26.550 | 1.724  | 1.00 | 19.96 |
| ATOM | 1704 | N   | TYR | A | 457 | -0.542 | 27.821 | 3.569  | 1.00 | 19.57 |
| ATOM | 1705 | CA  | TYR | A | 457 | 0.814  | 28.302 | 3.313  | 1.00 | 18.86 |
| ATOM | 1706 | CB  | TYR | A | 457 | 1.246  | 29.236 | 4.432  | 1.00 | 16.96 |
| ATOM | 1707 | CG  | TYR | A | 457 | 2.615  | 29.846 | 4.253  | 1.00 | 16.08 |
| ATOM | 1708 | CD1 | TYR | A | 457 | 2.759  | 31.121 | 3.685  | 1.00 | 15.38 |
| ATOM | 1709 | CE1 | TYR | A | 457 | 4.018  | 31.692 | 3.504  | 1.00 | 16.37 |
| ATOM | 1710 | CD2 | TYR | A | 457 | 3.774  | 29.153 | 4.634  | 1.00 | 15.96 |
| ATOM | 1711 | CE2 | TYR | A | 457 | 5.043  | 29.711 | 4.452  | 1.00 | 15.41 |
| ATOM | 1712 | CZ  | TYR | A | 457 | 5.157  | 30.981 | 3.884  | 1.00 | 16.49 |
| ATOM | 1713 | OH  | TYR | A | 457 | 6.407  | 31.541 | 3.695  | 1.00 | 16.08 |
| ATOM | 1714 | C   | TYR | A | 457 | 1.828  | 27.174 | 3.238  | 1.00 | 20.60 |
| ATOM | 1715 | O   | TYR | A | 457 | 1.758  | 26.195 | 3.998  | 1.00 | 20.26 |
| ATOM | 1716 | N   | ARG | A | 458 | 2.768  | 27.321 | 2.304  | 1.00 | 21.24 |
| ATOM | 1717 | CA  | ARG | A | 458 | 3.852  | 26.362 | 2.105  | 1.00 | 20.68 |
| ATOM | 1718 | CB  | ARG | A | 458 | 3.630  | 25.541 | 0.834  | 1.00 | 18.02 |
| ATOM | 1719 | CG  | ARG | A | 458 | 2.437  | 24.625 | 0.881  | 1.00 | 16.48 |
| ATOM | 1720 | CD  | ARG | A | 458 | 2.644  | 23.577 | 1.928  | 1.00 | 17.88 |
| ATOM | 1721 | NE  | ARG | A | 458 | 1.534  | 22.641 | 2.055  | 1.00 | 16.66 |
| ATOM | 1722 | CZ  | ARG | A | 458 | 0.431  | 22.890 | 2.753  | 1.00 | 17.51 |
| ATOM | 1723 | NH1 | ARG | A | 458 | 0.291  | 24.051 | 3.378  | 1.00 | 18.86 |
| ATOM | 1724 | NH2 | ARG | A | 458 | -0.524 | 21.974 | 2.855  | 1.00 | 17.04 |
| ATOM | 1725 | C   | ARG | A | 458 | 5.145  | 27.180 | 2.003  | 1.00 | 22.56 |
| ATOM | 1726 | O   | ARG | A | 458 | 5.122  | 28.320 | 1.525  | 1.00 | 21.61 |
| ATOM | 1727 | N   | MET | A | 459 | 6.245  | 26.651 | 2.536  | 1.00 | 22.77 |
| ATOM | 1728 | CA  | MET | A | 459 | 7.508  | 27.369 | 2.460  | 1.00 | 24.84 |
| ATOM | 1729 | CB  | MET | A | 459 | 8.581  | 26.665 | 3.279  | 1.00 | 25.20 |
| ATOM | 1730 | CG  | MET | A | 459 | 8.539  | 26.957 | 4.759  | 1.00 | 25.79 |
| ATOM | 1731 | SD  | MET | A | 459 | 9.922  | 26.191 | 5.600  | 1.00 | 26.85 |
| ATOM | 1732 | CE  | MET | A | 459 | 9.314  | 24.495 | 5.866  | 1.00 | 22.55 |
| ATOM | 1733 | C   | MET | A | 459 | 7.960  | 27.449 | 1.016  | 1.00 | 25.15 |
| ATOM | 1734 | O   | MET | A | 459 | 7.727  | 26.514 | 0.253  | 1.00 | 25.00 |
| ATOM | 1735 | N   | VAL | A | 460 | 8.594  | 28.560 | 0.643  | 1.00 | 26.07 |
| ATOM | 1736 | CA  | VAL | A | 460 | 9.101  | 28.730 | -0.719 | 1.00 | 27.35 |
| ATOM | 1737 | CB  | VAL | A | 460 | 9.387  | 30.221 | -1.051 | 1.00 | 26.52 |
| ATOM | 1738 | CG1 | VAL | A | 460 | 8.127  | 31.045 | -0.862 | 1.00 | 24.25 |
| ATOM | 1739 | CG2 | VAL | A | 460 | 10.542 | 30.761 | -0.199 | 1.00 | 25.34 |
| ATOM | 1740 | C   | VAL | A | 460 | 10.374 | 27.893 | -0.868 | 1.00 | 28.93 |
| ATOM | 1741 | O   | VAL | A | 460 | 10.799 | 27.247 | 0.084  | 1.00 | 29.70 |
| ATOM | 1742 | N   | ARG | A | 461 | 10.971 | 27.867 | -2.054 | 1.00 | 30.18 |
| ATOM | 1743 | CA  | ARG | A | 461 | 12.179 | 27.077 | -2.247 | 1.00 | 30.76 |
| ATOM | 1744 | CB  | ARG | A | 461 | 12.487 | 26.910 | -3.737 | 1.00 | 34.02 |
| ATOM | 1745 | CG  | ARG | A | 461 | 13.501 | 25.807 | -4.038 | 1.00 | 35.72 |
| ATOM | 1746 | CD  | ARG | A | 461 | 13.859 | 25.782 | -5.506 | 1.00 | 39.57 |
| ATOM | 1747 | NE  | ARG | A | 461 | 14.321 | 27.096 | -5.944 | 1.00 | 44.40 |
| ATOM | 1748 | CZ  | ARG | A | 461 | 15.506 | 27.620 | -5.633 | 1.00 | 47.43 |
| ATOM | 1749 | NH1 | ARG | A | 461 | 16.374 | 26.934 | -4.894 | 1.00 | 48.79 |
| ATOM | 1750 | NH2 | ARG | A | 461 | 15.799 | 28.867 | -5.992 | 1.00 | 48.60 |
| ATOM | 1751 | C   | ARG | A | 461 | 13.380 | 27.667 | -1.510 | 1.00 | 30.23 |
| ATOM | 1752 | O   | ARG | A | 461 | 13.714 | 28.840 | -1.667 | 1.00 | 28.07 |
| ATOM | 1753 | N   | PRO | A | 462 | 13.997 | 26.870 | -0.628 | 1.00 | 31.47 |
| ATOM | 1754 | CD  | PRO | A | 462 | 13.543 | 25.539 | -0.191 | 1.00 | 30.90 |
| ATOM | 1755 | CA  | PRO | A | 462 | 15.163 | 27.283 | 0.154  | 1.00 | 33.07 |
| ATOM | 1756 | CB  | PRO | A | 462 | 15.487 | 26.021 | 0.954  | 1.00 | 31.79 |
| ATOM | 1757 | CG  | PRO | A | 462 | 14.156 | 25.432 | 1.178  | 1.00 | 30.32 |

Figure 6

| ATOM | 1758 | C | PRO | A | 462 | 16.339 | 27.663 | -0.735 | 1.00 | 34.15 |
| --- | --- | --- | --- | --- | --- | --- | --- | --- | --- | --- |
| ATOM | 1759 | O | PRO | A | 462 | 16.553 | 27.033 | -1.768 | 1.00 | 32.98 |
| ATOM | 1760 | N | ASP | A | 463 | 17.079 | 28.699 | -0.332 | 1.00 | 37.18 |
| ATOM | 1761 | CA | ASP | A | 463 | 18.266 | 29.154 | -1.062 | 1.00 | 40.49 |
| ATOM | 1762 | CB | ASP | A | 463 | 19.020 | 30.229 | -0.253 | 1.00 | 42.06 |
| ATOM | 1763 | CG | ASP | A | 463 | 18.384 | 31.616 | -0.350 | 1.00 | 43.33 |
| ATOM | 1764 | OD1 | ASP | A | 463 | 17.393 | 31.777 | -1.098 | 1.00 | 43.47 |
| ATOM | 1765 | OD2 | ASP | A | 463 | 18.893 | 32.552 | 0.322 | 1.00 | 43.08 |
| ATOM | 1766 | C | ASP | A | 463 | 19.178 | 27.939 | -1.233 | 1.00 | 41.66 |
| ATOM | 1767 | O | ASP | A | 463 | 19.373 | 27.170 | -0.282 | 1.00 | 43.03 |
| ATOM | 1768 | N | ASN | A | 464 | 19.674 | 27.728 | -2.449 | 1.00 | 41.66 |
| ATOM | 1769 | CA | ASN | A | 464 | 20.562 | 26.600 | -2.730 | 1.00 | 42.43 |
| ATOM | 1770 | CB | ASN | A | 464 | 21.839 | 26.685 | -1.877 | 1.00 | 45.69 |
| ATOM | 1771 | CG | ASN | A | 464 | 22.755 | 27.831 | -2.296 | 1.00 | 47.43 |
| ATOM | 1772 | OD1 | ASN | A | 464 | 23.365 | 27.782 | -3.370 | 1.00 | 49.24 |
| ATOM | 1773 | ND2 | ASN | A | 464 | 22.877 | 28.852 | -1.438 | 1.00 | 46.73 |
| ATOM | 1774 | C | ASN | A | 464 | 19.904 | 25.235 | -2.536 | 1.00 | 41.62 |
| ATOM | 1775 | O | ASN | A | 464 | 20.435 | 24.362 | -1.847 | 1.00 | 40.90 |
| ATOM | 1776 | N | CYS | A | 465 | 18.731 | 25.068 | -3.136 | 1.00 | 40.50 |
| ATOM | 1777 | CA | CYS | A | 465 | 17.993 | 23.809 | -3.066 | 1.00 | 36.84 |
| ATOM | 1778 | CB | CYS | A | 465 | 16.791 | 23.940 | -2.123 | 1.00 | 35.63 |
| ATOM | 1779 | SG | CYS | A | 465 | 15.685 | 22.490 | -2.084 | 1.00 | 32.30 |
| ATOM | 1780 | C | CYS | A | 465 | 17.508 | 23.511 | -4.477 | 1.00 | 34.54 |
| ATOM | 1781 | O | CYS | A | 465 | 16.976 | 24.398 | -5.139 | 1.00 | 34.73 |
| ATOM | 1782 | N | PRO | A | 466 | 17.752 | 22.289 | -4.978 | 1.00 | 30.99 |
| ATOM | 1783 | CD | PRO | A | 466 | 18.588 | 21.253 | -4.345 | 1.00 | 30.50 |
| ATOM | 1784 | CA | PRO | A | 466 | 17.340 | 21.863 | -6.315 | 1.00 | 30.14 |
| ATOM | 1785 | CB | PRO | A | 466 | 17.839 | 20.424 | -6.375 | 1.00 | 29.92 |
| ATOM | 1786 | CG | PRO | A | 466 | 19.047 | 20.446 | -5.533 | 1.00 | 29.97 |
| ATOM | 1787 | C | PRO | A | 466 | 15.830 | 21.895 | -6.458 | 1.00 | 31.45 |
| ATOM | 1788 | O | PRO | A | 466 | 15.122 | 21.497 | -5.548 | 1.00 | 33.16 |
| ATOM | 1789 | N | GLU | A | 467 | 15.333 | 22.354 | -7.602 | 1.00 | 32.62 |
| ATOM | 1790 | CA | GLU | A | 467 | 13.889 | 22.397 | -7.821 | 1.00 | 33.42 |
| ATOM | 1791 | CB | GLU | A | 467 | 13.563 | 22.983 | -9.199 | 1.00 | 34.95 |
| ATOM | 1792 | CG | GLU | A | 467 | 12.855 | 24.338 | -9.189 | 1.00 | 36.69 |
| ATOM | 1793 | CD | GLU | A | 467 | 11.468 | 24.290 | -8.565 | 1.00 | 37.64 |
| ATOM | 1794 | OE1 | GLU | A | 467 | 11.139 | 25.201 | -7.779 | 1.00 | 38.23 |
| ATOM | 1795 | OE2 | GLU | A | 467 | 10.697 | 23.363 | -8.870 | 1.00 | 37.01 |
| ATOM | 1796 | C | GLU | A | 467 | 13.242 | 21.011 | -7.705 | 1.00 | 33.80 |
| ATOM | 1797 | O | GLU | A | 467 | 12.076 | 20.900 | -7.310 | 1.00 | 33.65 |
| ATOM | 1798 | N | GLU | A | 468 | 13.980 | 19.963 | -8.077 | 1.00 | 33.45 |
| ATOM | 1799 | CA | GLU | A | 468 | 13.442 | 18.608 | -7.986 | 1.00 | 34.98 |
| ATOM | 1800 | CB | GLU | A | 468 | 14.358 | 17.589 | -8.660 | 1.00 | 37.32 |
| ATOM | 1801 | CG | GLU | A | 468 | 14.596 | 17.822 | -10.139 | 1.00 | 41.22 |
| ATOM | 1802 | CD | GLU | A | 468 | 15.527 | 19.020 | -10.434 | 1.00 | 44.02 |
| ATOM | 1803 | OE1 | GLU | A | 468 | 16.544 | 19.206 | -9.708 | 1.00 | 41.76 |
| ATOM | 1804 | OE2 | GLU | A | 468 | 15.235 | 19.766 | -11.412 | 1.00 | 45.49 |
| ATOM | 1805 | C | GLU | A | 468 | 13.252 | 18.232 | -6.517 | 1.00 | 35.00 |
| ATOM | 1806 | O | GLU | A | 468 | 12.258 | 17.596 | -6.151 | 1.00 | 36.16 |
| ATOM | 1807 | N | LEU | A | 469 | 14.188 | 18.652 | -5.669 | 1.00 | 32.38 |
| ATOM | 1808 | CA | LEU | A | 469 | 14.079 | 18.365 | -4.258 | 1.00 | 30.39 |
| ATOM | 1809 | CB | LEU | A | 469 | 15.374 | 18.695 | -3.525 | 1.00 | 30.96 |
| ATOM | 1810 | CG | LEU | A | 469 | 15.480 | 18.228 | -2.070 | 1.00 | 29.76 |
| ATOM | 1811 | CD1 | LEU | A | 469 | 15.489 | 16.712 | -2.017 | 1.00 | 29.75 |
| ATOM | 1812 | CD2 | LEU | A | 469 | 16.750 | 18.775 | -1.465 | 1.00 | 28.46 |
| ATOM | 1813 | C | LEU | A | 469 | 12.920 | 19.164 | -3.678 | 1.00 | 29.65 |
| ATOM | 1814 | O | LEU | A | 469 | 12.169 | 18.630 | -2.870 | 1.00 | 31.49 |
| ATOM | 1815 | N | TYR | A | 470 | 12.745 | 20.419 | -4.108 | 1.00 | 27.55 |
| ATOM | 1816 | CA | TYR | A | 470 | 11.635 | 21.240 | -3.610 | 1.00 | 28.21 |

Figure 6

| | | | | | | | | |
|---|---|---|---|---|---|---|---|---|
| ATOM | 1817 | CB | TYR | A | 470 | 11.699 | 22.691 | -4.101 | 1.00 27.35 |
| ATOM | 1818 | CG | TYR | A | 470 | 10.539 | 23.573 | -3.620 | 1.00 26.97 |
| ATOM | 1819 | CD1 | TYR | A | 470 | 10.358 | 23.870 | -2.268 | 1.00 26.68 |
| ATOM | 1820 | CE1 | TYR | A | 470 | 9.321 | 24.730 | -1.847 | 1.00 26.21 |
| ATOM | 1821 | CD2 | TYR | A | 470 | 9.652 | 24.147 | -4.532 | 1.00 27.20 |
| ATOM | 1822 | CE2 | TYR | A | 470 | 8.614 | 25.001 | -4.120 | 1.00 25.16 |
| ATOM | 1823 | CZ | TYR | A | 470 | 8.454 | 25.290 | -2.784 | 1.00 25.52 |
| ATOM | 1824 | OH | TYR | A | 470 | 7.442 | 26.142 | -2.389 | 1.00 23.88 |
| ATOM | 1825 | C | TYR | A | 470 | 10.266 | 20.669 | -3.976 | 1.00 29.59 |
| ATOM | 1826 | O | TYR | A | 470 | 9.291 | 20.911 | -3.259 | 1.00 32.59 |
| ATOM | 1827 | N | GLN | A | 471 | 10.168 | 19.955 | -5.097 | 1.00 28.05 |
| ATOM | 1828 | CA | GLN | A | 471 | 8.883 | 19.385 | -5.486 | 1.00 26.66 |
| ATOM | 1829 | CB | GLN | A | 471 | 8.809 | 19.172 | -7.003 | 1.00 26.83 |
| ATOM | 1830 | CG | GLN | A | 471 | 8.741 | 20.478 | -7.808 | 1.00 24.18 |
| ATOM | 1831 | CD | GLN | A | 471 | 7.567 | 21.389 | -7.405 | 1.00 25.38 |
| ATOM | 1832 | OE1 | GLN | A | 471 | 6.524 | 20.918 | -6.931 | 1.00 23.88 |
| ATOM | 1833 | NE2 | GLN | A | 471 | 7.738 | 22.704 | -7.593 | 1.00 24.82 |
| ATOM | 1834 | C | GLN | A | 471 | 8.623 | 18.103 | -4.712 | 1.00 26.41 |
| ATOM | 1835 | O | GLN | A | 471 | 7.484 | 17.660 | -4.577 | 1.00 25.93 |
| ATOM | 1836 | N | LEU | A | 472 | 9.692 | 17.522 | -4.180 | 1.00 26.80 |
| ATOM | 1837 | CA | LEU | A | 472 | 9.576 | 16.320 | -3.360 | 1.00 26.77 |
| ATOM | 1838 | CB | LEU | A | 472 | 10.933 | 15.643 | -3.236 | 1.00 29.70 |
| ATOM | 1839 | CG | LEU | A | 472 | 10.988 | 14.120 | -3.236 | 1.00 31.57 |
| ATOM | 1840 | CD1 | LEU | A | 472 | 10.310 | 13.556 | -4.469 | 1.00 30.74 |
| ATOM | 1841 | CD2 | LEU | A | 472 | 12.452 | 13.705 | -3.205 | 1.00 32.90 |
| ATOM | 1842 | C | LEU | A | 472 | 9.078 | 16.774 | -1.980 | 1.00 23.92 |
| ATOM | 1843 | O | LEU | A | 472 | 8.349 | 16.045 | -1.316 | 1.00 25.58 |
| ATOM | 1844 | N | MET | A | 473 | 9.452 | 17.990 | -1.579 | 1.00 19.35 |
| ATOM | 1845 | CA | MET | A | 473 | 9.018 | 18.582 | -0.314 | 1.00 18.95 |
| ATOM | 1846 | CB | MET | A | 473 | 9.749 | 19.903 | -0.064 | 1.00 17.33 |
| ATOM | 1847 | CG | MET | A | 473 | 11.225 | 19.808 | 0.221 | 1.00 14.92 |
| ATOM | 1848 | SD | MET | A | 473 | 11.962 | 21.453 | 0.362 | 1.00 16.08 |
| ATOM | 1849 | CE | MET | A | 473 | 13.665 | 21.020 | 0.700 | 1.00 13.07 |
| ATOM | 1850 | C | MET | A | 473 | 7.511 | 18.865 | -0.358 | 1.00 20.03 |
| ATOM | 1851 | O | MET | A | 473 | 6.753 | 18.480 | 0.540 | 1.00 18.42 |
| ATOM | 1852 | N | ARG | A | 474 | 7.092 | 19.550 | -1.419 | 1.00 21.26 |
| ATOM | 1853 | CA | ARG | A | 474 | 5.693 | 19.912 | -1.650 | 1.00 22.27 |
| ATOM | 1854 | CB | ARG | A | 474 | 5.580 | 20.741 | -2.919 | 1.00 21.33 |
| ATOM | 1855 | CG | ARG | A | 474 | 6.331 | 22.047 | -2.849 | 1.00 22.38 |
| ATOM | 1856 | CD | ARG | A | 474 | 5.645 | 23.030 | -1.926 | 1.00 25.59 |
| ATOM | 1857 | NE | ARG | A | 474 | 4.284 | 23.339 | -2.371 | 1.00 27.16 |
| ATOM | 1858 | CZ | ARG | A | 474 | 3.867 | 24.533 | -2.776 | 1.00 26.15 |
| ATOM | 1859 | NH1 | ARG | A | 474 | 4.697 | 25.561 | -2.813 | 1.00 25.39 |
| ATOM | 1860 | NH2 | ARG | A | 474 | 2.599 | 24.702 | -3.106 | 1.00 26.09 |
| ATOM | 1861 | C | ARG | A | 474 | 4.745 | 18.716 | -1.711 | 1.00 22.95 |
| ATOM | 1862 | O | ARG | A | 474 | 3.566 | 18.840 | -1.393 | 1.00 23.63 |
| ATOM | 1863 | N | LEU | A | 475 | 5.244 | 17.573 | -2.165 | 1.00 24.14 |
| ATOM | 1864 | CA | LEU | A | 475 | 4.432 | 16.364 | -2.199 | 1.00 24.96 |
| ATOM | 1865 | CB | LEU | A | 475 | 5.029 | 15.309 | -3.134 | 1.00 26.25 |
| ATOM | 1866 | CG | LEU | A | 475 | 4.726 | 15.516 | -4.630 | 1.00 27.04 |
| ATOM | 1867 | CD1 | LEU | A | 475 | 5.472 | 14.494 | -5.464 | 1.00 26.41 |
| ATOM | 1868 | CD2 | LEU | A | 475 | 3.231 | 15.422 | -4.876 | 1.00 25.30 |
| ATOM | 1869 | C | LEU | A | 475 | 4.341 | 15.843 | -0.764 | 1.00 25.68 |
| ATOM | 1870 | O | LEU | A | 475 | 3.329 | 15.252 | -0.374 | 1.00 27.72 |
| ATOM | 1871 | N | CYS | A | 476 | 5.389 | 16.091 | 0.026 | 1.00 23.41 |
| ATOM | 1872 | CA | CYS | A | 476 | 5.399 | 15.695 | 1.431 | 1.00 22.23 |
| ATOM | 1873 | CB | CYS | A | 476 | 6.783 | 15.918 | 2.055 | 1.00 22.37 |
| ATOM | 1874 | SG | CYS | A | 476 | 7.991 | 14.640 | 1.745 | 1.00 23.91 |
| ATOM | 1875 | C | CYS | A | 476 | 4.384 | 16.574 | 2.174 | 1.00 20.11 |

Figure 6

| ATOM | 1876 | O   | CYS | A | 476 | 3.771   | 16.130 | 3.128  | 1.00 | 18.04 |
|------|------|-----|-----|---|-----|---------|--------|--------|------|-------|
| ATOM | 1877 | N   | TRP | A | 477 | 4.239   | 17.820 | 1.721  | 1.00 | 18.13 |
| ATOM | 1878 | CA  | TRP | A | 477 | 3.330   | 18.804 | 2.312  | 1.00 | 17.01 |
| ATOM | 1879 | CB  | TRP | A | 477 | 3.949   | 20.203 | 2.264  | 1.00 | 16.76 |
| ATOM | 1880 | CG  | TRP | A | 477 | 5.295   | 20.307 | 2.907  | 1.00 | 16.69 |
| ATOM | 1881 | CD2 | TRP | A | 477 | 6.304   | 21.295 | 2.630  | 1.00 | 16.28 |
| ATOM | 1882 | CE2 | TRP | A | 477 | 7.423   | 20.972 | 3.420  | 1.00 | 16.28 |
| ATOM | 1883 | CE3 | TRP | A | 477 | 6.367   | 22.408 | 1.784  | 1.00 | 16.80 |
| ATOM | 1884 | CD1 | TRP | A | 477 | 5.828   | 19.465 | 3.831  | 1.00 | 15.81 |
| ATOM | 1885 | NE1 | TRP | A | 477 | 7.107   | 19.856 | 4.141  | 1.00 | 16.39 |
| ATOM | 1886 | CZ2 | TRP | A | 477 | 8.598   | 21.730 | 3.388  | 1.00 | 15.76 |
| ATOM | 1887 | CZ3 | TRP | A | 477 | 7.533   | 23.158 | 1.750  | 1.00 | 17.17 |
| ATOM | 1888 | CH2 | TRP | A | 477 | 8.633   | 22.814 | 2.548  | 1.00 | 16.30 |
| ATOM | 1889 | C   | TRP | A | 477 | 1.926   | 18.896 | 1.717  | 1.00 | 16.86 |
| ATOM | 1890 | O   | TRP | A | 477 | 1.279   | 19.930 | 1.824  | 1.00 | 16.49 |
| ATOM | 1891 | N   | LYS | A | 478 | 1.440   | 17.826 | 1.110  | 1.00 | 18.49 |
| ATOM | 1892 | CA  | LYS | A | 478 | 0.090   | 17.861 | 0.548  | 1.00 | 20.54 |
| ATOM | 1893 | CB  | LYS | A | 478 | -0.198  | 16.634 | -0.337 | 1.00 | 20.72 |
| ATOM | 1894 | CG  | LYS | A | 478 | 0.645   | 16.540 | -1.609 | 1.00 | 21.58 |
| ATOM | 1895 | CD  | LYS | A | 478 | 0.301   | 17.622 | -2.609 | 1.00 | 22.46 |
| ATOM | 1896 | CE  | LYS | A | 478 | -0.996  | 17.304 | -3.317 | 1.00 | 24.14 |
| ATOM | 1897 | NZ  | LYS | A | 478 | -1.552  | 18.525 | -3.994 | 1.00 | 26.44 |
| ATOM | 1898 | C   | LYS | A | 478 | -0.895  | 17.917 | 1.708  | 1.00 | 21.73 |
| ATOM | 1899 | O   | LYS | A | 478 | -0.718  | 17.230 | 2.720  | 1.00 | 22.29 |
| ATOM | 1900 | N   | GLU | A | 479 | -1.916  | 18.756 | 1.575  | 1.00 | 22.52 |
| ATOM | 1901 | CA  | GLU | A | 479 | -2.926  | 18.899 | 2.607  | 1.00 | 23.91 |
| ATOM | 1902 | CB  | GLU | A | 479 | -4.012  | 19.860 | 2.149  | 1.00 | 23.95 |
| ATOM | 1903 | CG  | GLU | A | 479 | -4.948  | 20.298 | 3.255  | 1.00 | 24.94 |
| ATOM | 1904 | CD  | GLU | A | 479 | -4.238  | 21.030 | 4.399  | 1.00 | 25.69 |
| ATOM | 1905 | OE1 | GLU | A | 479 | -3.322  | 21.847 | 4.134  | 1.00 | 24.19 |
| ATOM | 1906 | OE2 | GLU | A | 479 | -4.617  | 20.796 | 5.569  | 1.00 | 24.93 |
| ATOM | 1907 | C   | GLU | A | 479 | -3.532  | 17.563 | 3.041  | 1.00 | 25.28 |
| ATOM | 1908 | O   | GLU | A | 479 | -3.766  | 17.361 | 4.229  | 1.00 | 26.24 |
| ATOM | 1909 | N   | ARG | A | 480 | -3.758  | 16.644 | 2.100  | 1.00 | 24.79 |
| ATOM | 1910 | CA  | ARG | A | 480 | -4.316  | 15.328 | 2.436  | 1.00 | 26.12 |
| ATOM | 1911 | CB  | ARG | A | 480 | -5.253  | 14.842 | 1.345  | 1.00 | 28.92 |
| ATOM | 1912 | CG  | ARG | A | 480 | -6.488  | 15.648 | 1.167  | 1.00 | 32.19 |
| ATOM | 1913 | CD  | ARG | A | 480 | -7.054  | 15.289 | -0.165 | 1.00 | 35.78 |
| ATOM | 1914 | NE  | ARG | A | 480 | -8.354  | 15.892 | -0.378 | 1.00 | 41.10 |
| ATOM | 1915 | CZ  | ARG | A | 480 | -8.931  | 16.030 | -1.568 | 1.00 | 43.81 |
| ATOM | 1916 | NH1 | ARG | A | 480 | -8.314  | 15.610 | -2.670 | 1.00 | 45.29 |
| ATOM | 1917 | NH2 | ARG | A | 480 | -10.150 | 16.549 | -1.646 | 1.00 | 45.05 |
| ATOM | 1918 | C   | ARG | A | 480 | -3.231  | 14.268 | 2.642  | 1.00 | 24.65 |
| ATOM | 1919 | O   | ARG | A | 480 | -2.358  | 14.088 | 1.806  | 1.00 | 25.97 |
| ATOM | 1920 | N   | PRO | A | 481 | -3.344  | 13.470 | 3.702  | 1.00 | 23.55 |
| ATOM | 1921 | CD  | PRO | A | 481 | -4.382  | 13.428 | 4.746  | 1.00 | 22.38 |
| ATOM | 1922 | CA  | PRO | A | 481 | -2.329  | 12.451 | 3.945  | 1.00 | 23.17 |
| ATOM | 1923 | CB  | PRO | A | 481 | -2.817  | 11.780 | 5.237  | 1.00 | 22.40 |
| ATOM | 1924 | CG  | PRO | A | 481 | -3.647  | 12.809 | 5.878  | 1.00 | 21.02 |
| ATOM | 1925 | C   | PRO | A | 481 | -2.145  | 11.418 | 2.844  | 1.00 | 22.62 |
| ATOM | 1926 | O   | PRO | A | 481 | -1.036  | 10.903 | 2.653  | 1.00 | 23.94 |
| ATOM | 1927 | N   | GLU | A | 482 | -3.225  | 11.080 | 2.148  | 1.00 | 21.88 |
| ATOM | 1928 | CA  | GLU | A | 482 | -3.159  | 10.056 | 1.114  | 1.00 | 21.73 |
| ATOM | 1929 | CB  | GLU | A | 482 | -4.574  | 9.581  | 0.749  | 1.00 | 23.27 |
| ATOM | 1930 | CG  | GLU | A | 482 | -5.415  | 10.563 | -0.093 | 1.00 | 26.43 |
| ATOM | 1931 | CD  | GLU | A | 482 | -6.294  | 11.523 | 0.717  | 1.00 | 28.13 |
| ATOM | 1932 | OE1 | GLU | A | 482 | -6.106  | 11.653 | 1.941  | 1.00 | 28.01 |
| ATOM | 1933 | OE2 | GLU | A | 482 | -7.196  | 12.148 | 0.113  | 1.00 | 29.42 |
| ATOM | 1934 | C   | GLU | A | 482 | -2.390  | 10.508 | -0.122 | 1.00 | 20.37 |

Figure 6

| ATOM | 1935 | O | GLU | A | 482 | -1.909 | 9.688 | -0.894 | 1.00 | 19.33 |
| ATOM | 1936 | N | ASP | A | 483 | -2.241 | 11.818 | -0.269 | 1.00 | 18.43 |
| ATOM | 1937 | CA | ASP | A | 483 | -1.561 | 12.417 | -1.404 | 1.00 | 18.01 |
| ATOM | 1938 | CB | ASP | A | 483 | -2.171 | 13.783 | -1.707 | 1.00 | 19.95 |
| ATOM | 1939 | CG | ASP | A | 483 | -3.541 | 13.681 | -2.367 | 1.00 | 22.10 |
| ATOM | 1940 | OD1 | ASP | A | 483 | -3.766 | 12.682 | -3.077 | 1.00 | 22.44 |
| ATOM | 1941 | OD2 | ASP | A | 483 | -4.388 | 14.586 | -2.184 | 1.00 | 22.97 |
| ATOM | 1942 | C | ASP | A | 483 | -0.068 | 12.571 | -1.228 | 1.00 | 19.74 |
| ATOM | 1943 | O | ASP | A | 483 | 0.632 | 12.971 | -2.162 | 1.00 | 22.90 |
| ATOM | 1944 | N | ARG | A | 484 | 0.417 | 12.265 | -0.028 | 1.00 | 18.91 |
| ATOM | 1945 | CA | ARG | A | 484 | 1.836 | 12.363 | 0.302 | 1.00 | 18.00 |
| ATOM | 1946 | CB | ARG | A | 484 | 2.008 | 12.682 | 1.793 | 1.00 | 17.59 |
| ATOM | 1947 | CG | ARG | A | 484 | 1.367 | 13.966 | 2.249 | 1.00 | 17.42 |
| ATOM | 1948 | CD | ARG | A | 484 | 1.454 | 14.106 | 3.762 | 1.00 | 17.73 |
| ATOM | 1949 | NE | ARG | A | 484 | 0.631 | 15.213 | 4.236 | 1.00 | 19.12 |
| ATOM | 1950 | CZ | ARG | A | 484 | -0.002 | 15.246 | 5.411 | 1.00 | 19.06 |
| ATOM | 1951 | NH1 | ARG | A | 484 | 0.094 | 14.240 | 6.258 | 1.00 | 19.07 |
| ATOM | 1952 | NH2 | ARG | A | 484 | -0.800 | 16.266 | 5.704 | 1.00 | 20.21 |
| ATOM | 1953 | C | ARG | A | 484 | 2.524 | 11.039 | -0.028 | 1.00 | 18.32 |
| ATOM | 1954 | O | ARG | A | 484 | 1.986 | 9.980 | 0.253 | 1.00 | 17.10 |
| ATOM | 1955 | N | PRO | A | 485 | 3.767 | 11.087 | -0.540 | 1.00 | 18.66 |
| ATOM | 1956 | CD | PRO | A | 485 | 4.620 | 12.281 | -0.666 | 1.00 | 18.51 |
| ATOM | 1957 | CA | PRO | A | 485 | 4.512 | 9.872 | -0.899 | 1.00 | 19.10 |
| ATOM | 1958 | CB | PRO | A | 485 | 5.857 | 10.424 | -1.400 | 1.00 | 19.65 |
| ATOM | 1959 | CG | PRO | A | 485 | 5.580 | 11.858 | -1.743 | 1.00 | 19.87 |
| ATOM | 1960 | C | PRO | A | 485 | 4.767 | 8.921 | 0.282 | 1.00 | 20.52 |
| ATOM | 1961 | O | PRO | A | 485 | 4.673 | 9.320 | 1.441 | 1.00 | 20.36 |
| ATOM | 1962 | N | THR | A | 486 | 5.039 | 7.652 | -0.032 | 1.00 | 19.37 |
| ATOM | 1963 | CA | THR | A | 486 | 5.386 | 6.661 | 0.970 | 1.00 | 19.38 |
| ATOM | 1964 | CB | THR | A | 486 | 5.146 | 5.206 | 0.462 | 1.00 | 17.30 |
| ATOM | 1965 | OG1 | THR | A | 486 | 5.830 | 5.000 | -0.772 | 1.00 | 18.44 |
| ATOM | 1966 | CG2 | THR | A | 486 | 3.676 | 4.955 | 0.258 | 1.00 | 15.92 |
| ATOM | 1967 | C | THR | A | 486 | 6.884 | 6.883 | 1.225 | 1.00 | 21.73 |
| ATOM | 1968 | O | THR | A | 486 | 7.553 | 7.531 | 0.416 | 1.00 | 23.10 |
| ATOM | 1969 | N | PHE | A | 487 | 7.403 | 6.427 | 2.365 | 1.00 | 22.47 |
| ATOM | 1970 | CA | PHE | A | 487 | 8.836 | 6.604 | 2.644 | 1.00 | 22.44 |
| ATOM | 1971 | CB | PHE | A | 487 | 9.176 | 6.351 | 4.135 | 1.00 | 19.41 |
| ATOM | 1972 | CG | PHE | A | 487 | 8.954 | 7.560 | 5.035 | 1.00 | 17.41 |
| ATOM | 1973 | CD1 | PHE | A | 487 | 9.739 | 8.703 | 4.904 | 1.00 | 15.33 |
| ATOM | 1974 | CD2 | PHE | A | 487 | 7.954 | 7.556 | 6.009 | 1.00 | 17.05 |
| ATOM | 1975 | CE1 | PHE | A | 487 | 9.529 | 9.824 | 5.723 | 1.00 | 13.40 |
| ATOM | 1976 | CE2 | PHE | A | 487 | 7.745 | 8.680 | 6.829 | 1.00 | 15.22 |
| ATOM | 1977 | CZ | PHE | A | 487 | 8.540 | 9.816 | 6.677 | 1.00 | 13.38 |
| ATOM | 1978 | C | PHE | A | 487 | 9.632 | 5.672 | 1.718 | 1.00 | 23.73 |
| ATOM | 1979 | O | PHE | A | 487 | 10.784 | 5.939 | 1.375 | 1.00 | 24.84 |
| ATOM | 1980 | N | ASP | A | 488 | 8.987 | 4.598 | 1.283 | 1.00 | 25.05 |
| ATOM | 1981 | CA | ASP | A | 488 | 9.600 | 3.648 | 0.370 | 1.00 | 26.06 |
| ATOM | 1982 | CB | ASP | A | 488 | 8.603 | 2.534 | 0.092 | 1.00 | 28.54 |
| ATOM | 1983 | CG | ASP | A | 488 | 9.101 | 1.552 | -0.919 | 1.00 | 30.59 |
| ATOM | 1984 | OD1 | ASP | A | 488 | 10.332 | 1.374 | -1.035 | 1.00 | 31.70 |
| ATOM | 1985 | OD2 | ASP | A | 488 | 8.249 | 0.946 | -1.590 | 1.00 | 32.32 |
| ATOM | 1986 | C | ASP | A | 488 | 9.942 | 4.400 | -0.920 | 1.00 | 26.22 |
| ATOM | 1987 | O | ASP | A | 488 | 10.989 | 4.173 | -1.531 | 1.00 | 28.55 |
| ATOM | 1988 | N | TYR | A | 489 | 9.061 | 5.324 | -1.298 | 1.00 | 25.09 |
| ATOM | 1989 | CA | TYR | A | 489 | 9.242 | 6.135 | -2.477 | 1.00 | 23.58 |
| ATOM | 1990 | CB | TYR | A | 489 | 7.947 | 6.849 | -2.850 | 1.00 | 23.60 |
| ATOM | 1991 | CG | TYR | A | 489 | 8.132 | 7.856 | -3.968 | 1.00 | 25.22 |
| ATOM | 1992 | CD1 | TYR | A | 489 | 8.359 | 7.438 | -5.281 | 1.00 | 25.78 |
| ATOM | 1993 | CE1 | TYR | A | 489 | 8.595 | 8.366 | -6.311 | 1.00 | 27.01 |

Figure 6

| ATOM | 1994 | CD2 | TYR | A | 489 | 8.145 | 9.229 | -3.703 | 1.00 | 26.45 |
| --- | --- | --- | --- | --- | --- | --- | --- | --- | --- | --- |
| ATOM | 1995 | CE2 | TYR | A | 489 | 8.379 | 10.170 | -4.711 | 1.00 | 26.37 |
| ATOM | 1996 | CZ | TYR | A | 489 | 8.610 | 9.736 | -6.021 | 1.00 | 28.24 |
| ATOM | 1997 | OH | TYR | A | 489 | 8.871 | 10.660 | -7.031 | 1.00 | 27.74 |
| ATOM | 1998 | C | TYR | A | 489 | 10.326 | 7.169 | -2.269 | 1.00 | 24.39 |
| ATOM | 1999 | O | TYR | A | 489 | 11.222 | 7.305 | -3.099 | 1.00 | 26.86 |
| ATOM | 2000 | N | LEU | A | 490 | 10.207 | 7.945 | -1.198 | 1.00 | 23.68 |
| ATOM | 2001 | CA | LEU | A | 490 | 11.182 | 8.992 | -0.897 | 1.00 | 23.42 |
| ATOM | 2002 | CB | LEU | A | 490 | 10.813 | 9.742 | 0.385 | 1.00 | 23.13 |
| ATOM | 2003 | CG | LEU | A | 490 | 9.605 | 10.673 | 0.325 | 1.00 | 21.07 |
| ATOM | 2004 | CD1 | LEU | A | 490 | 9.000 | 10.825 | 1.692 | 1.00 | 20.29 |
| ATOM | 2005 | CD2 | LEU | A | 490 | 10.017 | 12.008 | -0.232 | 1.00 | 20.17 |
| ATOM | 2006 | C | LEU | A | 490 | 12.598 | 8.457 | -0.786 | 1.00 | 25.24 |
| ATOM | 2007 | O | LEU | A | 490 | 13.557 | 9.188 | -1.062 | 1.00 | 25.35 |
| ATOM | 2008 | N | ARG | A | 491 | 12.734 | 7.200 | -0.362 | 1.00 | 26.16 |
| ATOM | 2009 | CA | ARG | A | 491 | 14.041 | 6.572 | -0.254 | 1.00 | 28.99 |
| ATOM | 2010 | CB | ARG | A | 491 | 13.949 | 5.233 | 0.463 | 1.00 | 31.12 |
| ATOM | 2011 | CG | ARG | A | 491 | 15.262 | 4.468 | 0.432 | 1.00 | 35.83 |
| ATOM | 2012 | CD | ARG | A | 491 | 15.081 | 2.979 | 0.664 | 1.00 | 40.67 |
| ATOM | 2013 | NE | ARG | A | 491 | 13.982 | 2.416 | -0.130 | 1.00 | 45.96 |
| ATOM | 2014 | CZ | ARG | A | 491 | 14.071 | 1.977 | -1.396 | 1.00 | 47.72 |
| ATOM | 2015 | NH1 | ARG | A | 491 | 15.221 | 2.024 | -2.078 | 1.00 | 47.28 |
| ATOM | 2016 | NH2 | ARG | A | 491 | 12.998 | 1.436 | -1.973 | 1.00 | 48.17 |
| ATOM | 2017 | C | ARG | A | 491 | 14.591 | 6.344 | -1.664 | 1.00 | 30.45 |
| ATOM | 2018 | O | ARG | A | 491 | 15.736 | 6.705 | -1.960 | 1.00 | 30.22 |
| ATOM | 2019 | N | SER | A | 492 | 13.770 | 5.745 | -2.526 | 1.00 | 31.23 |
| ATOM | 2020 | CA | SER | A | 492 | 14.143 | 5.467 | -3.914 | 1.00 | 30.94 |
| ATOM | 2021 | CB | SER | A | 492 | 12.965 | 4.853 | -4.657 | 1.00 | 30.96 |
| ATOM | 2022 | OG | SER | A | 492 | 12.636 | 3.602 | -4.099 | 1.00 | 32.25 |
| ATOM | 2023 | C | SER | A | 492 | 14.582 | 6.713 | -4.665 | 1.00 | 31.09 |
| ATOM | 2024 | O | SER | A | 492 | 15.622 | 6.714 | -5.321 | 1.00 | 31.18 |
| ATOM | 2025 | N | VAL | A | 493 | 13.771 | 7.764 | -4.583 | 1.00 | 31.86 |
| ATOM | 2026 | CA | VAL | A | 493 | 14.070 | 9.016 | -5.266 | 1.00 | 33.13 |
| ATOM | 2027 | CB | VAL | A | 493 | 12.843 | 9.981 | -5.308 | 1.00 | 34.15 |
| ATOM | 2028 | CG1 | VAL | A | 493 | 12.239 | 10.160 | -3.926 | 1.00 | 36.38 |
| ATOM | 2029 | CG2 | VAL | A | 493 | 13.246 | 11.333 | -5.869 | 1.00 | 34.62 |
| ATOM | 2030 | C | VAL | A | 493 | 15.293 | 9.718 | -4.704 | 1.00 | 33.71 |
| ATOM | 2031 | O | VAL | A | 493 | 16.052 | 10.317 | -5.461 | 1.00 | 35.55 |
| ATOM | 2032 | N | LEU | A | 494 | 15.498 | 9.628 | -3.390 | 1.00 | 34.35 |
| ATOM | 2033 | CA | LEU | A | 494 | 16.659 | 10.257 | -2.750 | 1.00 | 32.81 |
| ATOM | 2034 | CB | LEU | A | 494 | 16.422 | 10.433 | -1.244 | 1.00 | 31.44 |
| ATOM | 2035 | CG | LEU | A | 494 | 15.427 | 11.558 | -0.956 | 1.00 | 31.44 |
| ATOM | 2036 | CD1 | LEU | A | 494 | 15.064 | 11.562 | 0.496 | 1.00 | 32.11 |
| ATOM | 2037 | CD2 | LEU | A | 494 | 15.992 | 12.913 | -1.385 | 1.00 | 31.77 |
| ATOM | 2038 | C | LEU | A | 494 | 17.983 | 9.536 | -3.048 | 1.00 | 31.76 |
| ATOM | 2039 | O | LEU | A | 494 | 19.010 | 10.181 | -3.241 | 1.00 | 29.75 |
| ATOM | 2040 | N | GLU | A | 495 | 17.950 | 8.211 | -3.107 | 1.00 | 32.82 |
| ATOM | 2041 | CA | GLU | A | 495 | 19.141 | 7.431 | -3.423 | 1.00 | 37.76 |
| ATOM | 2042 | CB | GLU | A | 495 | 18.819 | 5.930 | -3.380 | 1.00 | 39.48 |
| ATOM | 2043 | CG | GLU | A | 495 | 18.694 | 5.306 | -1.999 | 1.00 | 43.46 |
| ATOM | 2044 | CD | GLU | A | 495 | 18.216 | 3.848 | -2.030 | 1.00 | 45.59 |
| ATOM | 2045 | OE1 | GLU | A | 495 | 18.050 | 3.286 | -3.146 | 1.00 | 45.97 |
| ATOM | 2046 | OE2 | GLU | A | 495 | 18.001 | 3.269 | -0.926 | 1.00 | 46.33 |
| ATOM | 2047 | C | GLU | A | 495 | 19.623 | 7.770 | -4.843 | 1.00 | 40.59 |
| ATOM | 2048 | O | GLU | A | 495 | 20.796 | 8.085 | -5.076 | 1.00 | 42.01 |
| ATOM | 2049 | N | ASP | A | 496 | 18.689 | 7.710 | -5.787 | 1.00 | 42.61 |
| ATOM | 2050 | CA | ASP | A | 496 | 18.972 | 7.961 | -7.193 | 1.00 | 43.27 |
| ATOM | 2051 | CB | ASP | A | 496 | 18.021 | 7.134 | -8.080 | 1.00 | 43.95 |
| ATOM | 2052 | CG | ASP | A | 496 | 18.082 | 5.630 | -7.786 | 1.00 | 45.08 |

Figure 6

```
ATOM  2053  OD1  ASP A 496    19.192   5.093  -7.541  1.00 44.55
ATOM  2054  OD2  ASP A 496    17.007   4.981  -7.825  1.00 45.99
ATOM  2055  C    ASP A 496    18.886   9.424  -7.610  1.00 43.90
ATOM  2056  O    ASP A 496    18.830   9.699  -8.810  1.00 45.03
ATOM  2057  N    PHE A 497    18.879  10.360  -6.658  1.00 43.30
ATOM  2058  CA   PHE A 497    18.764  11.784  -7.004  1.00 42.84
ATOM  2059  CB   PHE A 497    18.834  12.670  -5.752  1.00 39.47
ATOM  2060  CG   PHE A 497    18.240  14.039  -5.946  1.00 37.10
ATOM  2061  CD1  PHE A 497    16.865  14.224  -5.896  1.00 36.78
ATOM  2062  CD2  PHE A 497    19.049  15.137  -6.203  1.00 36.89
ATOM  2063  CE1  PHE A 497    16.297  15.482  -6.099  1.00 36.19
ATOM  2064  CE2  PHE A 497    18.497  16.407  -6.408  1.00 36.90
ATOM  2065  CZ   PHE A 497    17.117  16.577  -6.355  1.00 36.71
ATOM  2066  C    PHE A 497    19.797  12.228  -8.052  1.00 44.97
ATOM  2067  O    PHE A 497    19.462  12.950  -8.998  1.00 45.35
ATOM  2068  N    PHE A 498    21.040  11.780  -7.882  1.00 47.97
ATOM  2069  CA   PHE A 498    22.126  12.093  -8.815  1.00 50.82
ATOM  2070  CB   PHE A 498    22.289  13.611  -9.040  1.00 50.46
ATOM  2071  CG   PHE A 498    22.492  14.424  -7.778  1.00 49.37
ATOM  2072  CD1  PHE A 498    22.989  13.850  -6.606  1.00 49.20
ATOM  2073  CD2  PHE A 498    22.171  15.783  -7.775  1.00 48.95
ATOM  2074  CE1  PHE A 498    23.154  14.618  -5.462  1.00 49.20
ATOM  2075  CE2  PHE A 498    22.334  16.560  -6.635  1.00 48.25
ATOM  2076  CZ   PHE A 498    22.825  15.978  -5.477  1.00 48.59
ATOM  2077  C    PHE A 498    23.452  11.475  -8.396  1.00 52.46
ATOM  2078  O    PHE A 498    23.589  10.261  -8.642  1.00 55.24
ATOM  2079  N1   LIG A 500    23.525   8.062  21.004  1.00 22.17
ATOM  2080  C1   LIG A 500    24.109   9.319  21.049  1.00 22.30
ATOM  2081  N2   LIG A 500    25.370   9.457  20.674  1.00 22.08
ATOM  2082  C2   LIG A 500    25.973  10.624  20.685  1.00 21.72
ATOM  2083  N3   LIG A 500    25.389  11.721  21.082  1.00 22.42
ATOM  2084  C3   LIG A 500    24.110  11.719  21.488  1.00 23.15
ATOM  2085  N4   LIG A 500    23.248  12.710  21.947  1.00 22.48
ATOM  2086  C4   LIG A 500    23.622  14.142  22.070  1.00 21.86
ATOM  2087  C5   LIG A 500    22.659  15.016  21.275  1.00 21.73
ATOM  2088  C6   LIG A 500    23.598  14.585  23.526  1.00 20.47
ATOM  2089  C7   LIG A 500    22.015  12.161  22.239  1.00 22.74
ATOM  2090  C8   LIG A 500    22.035  10.802  21.979  1.00 23.86
ATOM  2091  C9   LIG A 500    20.898   9.861  22.171  1.00 24.73
ATOM  2092  C10  LIG A 500    21.053   8.618  22.817  1.00 24.26
ATOM  2093  C11  LIG A 500    19.952   7.773  22.948  1.00 25.84
ATOM  2094  C12  LIG A 500    18.695   8.163  22.441  1.00 26.75
ATOM  2095  N5   LIG A 500    17.567   7.316  22.567  1.00 30.72
ATOM  2096  C13  LIG A 500    16.857   6.820  21.485  1.00 33.55
ATOM  2097  O1   LIG A 500    17.326   6.859  20.348  1.00 33.33
ATOM  2098  C14  LIG A 500    15.499   6.223  21.693  1.00 34.65
ATOM  2099  C15  LIG A 500    14.927   6.172  22.987  1.00 35.74
ATOM  2100  C16  LIG A 500    13.672   5.614  23.161  1.00 34.38
ATOM  2101  C17  LIG A 500    12.981   5.107  22.073  1.00 33.37
ATOM  2102  C18  LIG A 500    13.530   5.148  20.806  1.00 34.11
ATOM  2103  C19  LIG A 500    14.782   5.705  20.604  1.00 34.59
ATOM  2104  C20  LIG A 500    18.558   9.387  21.797  1.00 26.11
ATOM  2105  C21  LIG A 500    19.639  10.232  21.660  1.00 24.96
ATOM  2106  C22  LIG A 500    23.406  10.483  21.485  1.00 22.87
ATOM  2107  OH2  H2O A 600     5.166  22.233   9.245  1.00 19.28
ATOM  2108  OH2  H2O A 602    -1.376  24.290   0.572  1.00  9.37
ATOM  2109  OH2  H2O A 605    -5.673  25.098   2.363  1.00 21.57
ATOM  2110  OH2  H2O A 606     7.087  12.947  13.001  1.00 10.13
ATOM  2111  OH2  H2O A 607    -3.650  16.830  -1.014  1.00 21.25
```

Figure 6

| | | | | | | | | |
|---|---|---|---|---|---|---|---|---|
| ATOM | 2112 | OH2 | H2O | A | 609 | -0.668 | 30.940 | 2.578 | 1.00 24.41 |
| ATOM | 2113 | OH2 | H2O | A | 610 | 5.843 | 24.510 | 4.283 | 1.00 12.50 |
| ATOM | 2114 | OH2 | H2O | A | 611 | 5.543 | 18.742 | -6.255 | 1.00 22.60 |
| ATOM | 2115 | OH2 | H2O | A | 612 | 0.486 | 5.999 | 0.301 | 1.00 18.74 |
| ATOM | 2116 | OH2 | H2O | A | 614 | 8.879 | 9.609 | 18.797 | 1.00 17.70 |
| ATOM | 2117 | OH2 | H2O | A | 615 | -9.707 | 8.237 | -2.855 | 1.00 41.05 |
| ATOM | 2118 | OH2 | H2O | A | 616 | -1.960 | 7.314 | -0.215 | 1.00 22.11 |
| ATOM | 2119 | OH2 | H2O | A | 618 | 7.899 | 24.831 | 16.217 | 1.00 30.84 |
| ATOM | 2120 | OH2 | H2O | A | 620 | 1.275 | 26.991 | -3.022 | 1.00 32.05 |
| ATOM | 2121 | OH2 | H2O | A | 621 | 29.628 | 13.914 | 20.558 | 1.00 22.64 |
| ATOM | 2122 | OH2 | H2O | A | 623 | -3.769 | 23.272 | 1.792 | 1.00 14.66 |
| ATOM | 2123 | OH2 | H2O | A | 624 | 35.040 | 11.279 | 22.000 | 1.00 28.05 |
| ATOM | 2124 | OH2 | H2O | A | 626 | 15.016 | 19.576 | 14.534 | 1.00 32.83 |
| ATOM | 2125 | OH2 | H2O | A | 627 | 3.040 | 6.047 | 3.789 | 1.00 12.23 |
| ATOM | 2126 | OH2 | H2O | A | 628 | 3.494 | 15.567 | 11.524 | 1.00 18.53 |
| ATOM | 2127 | OH2 | H2O | A | 630 | 8.957 | 15.007 | -7.428 | 1.00 55.46 |
| ATOM | 2128 | OH2 | H2O | A | 631 | 33.465 | -0.771 | 33.715 | 1.00 47.78 |
| ATOM | 2129 | OH2 | H2O | A | 632 | 5.323 | 27.756 | -1.484 | 1.00 12.36 |
| ATOM | 2130 | OH2 | H2O | A | 633 | 16.837 | 12.402 | 19.557 | 1.00 48.88 |
| ATOM | 2131 | OH2 | H2O | A | 634 | 16.678 | -0.491 | 4.609 | 1.00 26.65 |
| ATOM | 2132 | OH2 | H2O | A | 635 | -1.747 | 11.629 | 9.684 | 1.00 25.33 |
| ATOM | 2133 | OH2 | H2O | A | 636 | -2.047 | 12.450 | -5.259 | 1.00 27.43 |
| ATOM | 2134 | OH2 | H2O | A | 638 | -8.306 | 8.271 | -5.475 | 1.00 28.31 |
| ATOM | 2135 | OH2 | H2O | A | 640 | -1.982 | 23.590 | 5.620 | 1.00 16.32 |
| ATOM | 2136 | OH2 | H2O | A | 641 | -3.079 | 6.501 | 2.223 | 1.00 23.25 |
| ATOM | 2137 | OH2 | H2O | A | 642 | 18.818 | -0.458 | 15.511 | 1.00 24.61 |
| ATOM | 2138 | OH2 | H2O | A | 644 | 2.772 | 21.406 | -0.841 | 1.00 24.74 |
| ATOM | 2139 | OH2 | H2O | A | 645 | -4.382 | 23.904 | 9.559 | 1.00 20.84 |
| ATOM | 2140 | OH2 | H2O | A | 647 | 3.815 | 35.332 | 6.901 | 1.00 38.83 |
| ATOM | 2141 | OH2 | H2O | A | 648 | 0.688 | 4.980 | 10.381 | 1.00 29.01 |
| ATOM | 2142 | OH2 | H2O | A | 650 | 12.190 | 27.916 | 2.634 | 1.00 33.09 |
| ATOM | 2143 | OH2 | H2O | A | 652 | -2.004 | 20.290 | -0.881 | 1.00 27.47 |
| ATOM | 2144 | OH2 | H2O | A | 653 | 3.302 | 22.394 | 11.187 | 1.00 16.30 |
| ATOM | 2145 | OH2 | H2O | A | 654 | 3.425 | 30.961 | -4.275 | 1.00 18.66 |
| ATOM | 2146 | OH2 | H2O | A | 655 | 23.462 | 20.278 | 27.079 | 1.00 32.00 |
| ATOM | 2147 | OH2 | H2O | A | 656 | 4.438 | 3.629 | 16.598 | 1.00 21.11 |
| ATOM | 2148 | OH2 | H2O | A | 659 | 9.422 | 28.363 | -4.515 | 1.00 20.96 |
| ATOM | 2149 | OH2 | H2O | A | 660 | 22.517 | 20.810 | 21.887 | 1.00 45.85 |
| ATOM | 2150 | OH2 | H2O | A | 661 | 14.602 | 15.061 | 24.345 | 1.00 38.43 |
| ATOM | 2151 | OH2 | H2O | A | 663 | 6.147 | 34.357 | 3.296 | 1.00 52.41 |
| ATOM | 2152 | OH2 | H2O | A | 664 | 25.767 | 21.379 | 20.895 | 1.00 25.92 |
| ATOM | 2153 | OH2 | H2O | A | 666 | -2.694 | 24.576 | -2.677 | 1.00 39.42 |
| ATOM | 2154 | OH2 | H2O | A | 667 | 7.955 | 1.328 | 3.457 | 1.00 36.59 |
| ATOM | 2155 | OH2 | H2O | A | 668 | 22.491 | 23.772 | 0.196 | 1.00 35.56 |
| ATOM | 2156 | OH2 | H2O | A | 669 | 5.102 | 1.344 | 2.095 | 1.00 38.40 |
| ATOM | 2157 | OH2 | H2O | A | 671 | -2.599 | 7.531 | 7.112 | 1.00 45.47 |
| ATOM | 2158 | OH2 | H2O | A | 672 | 5.904 | 2.815 | 19.040 | 1.00 28.22 |
| ATOM | 2159 | OH2 | H2O | A | 674 | 14.013 | 0.375 | 4.575 | 1.00 22.02 |
| ATOM | 2160 | OH2 | H2O | A | 677 | 5.081 | 14.864 | 13.904 | 1.00 35.01 |
| ATOM | 2161 | OH2 | H2O | A | 679 | 14.517 | 21.388 | 16.518 | 1.00 47.78 |
| ATOM | 2162 | OH2 | H2O | A | 680 | 31.203 | 15.681 | 32.227 | 1.00 50.11 |
| ATOM | 2163 | OH2 | H2O | A | 681 | -7.058 | 19.496 | 9.544 | 1.00 29.59 |
| ATOM | 2164 | OH2 | H2O | A | 682 | 28.638 | 2.736 | 19.526 | 1.00 22.22 |
| ATOM | 2165 | OH2 | H2O | A | 683 | 19.016 | 16.667 | 20.486 | 1.00 41.97 |
| ATOM | 2166 | OH2 | H2O | A | 684 | 14.039 | 25.566 | 7.123 | 1.00 34.71 |
| ATOM | 2167 | OH2 | H2O | A | 685 | -4.781 | 23.134 | 6.994 | 1.00 27.21 |
| ATOM | 2168 | OH2 | H2O | A | 688 | 33.554 | 12.865 | 11.865 | 1.00 29.27 |
| ATOM | 2169 | OH2 | H2O | A | 689 | -5.010 | 25.378 | 13.009 | 1.00 41.83 |
| ATOM | 2170 | OH2 | H2O | A | 691 | 18.388 | -2.071 | 19.402 | 1.00 19.95 |

Figure 6

| ATOM | 2171 | OH2 | H2O | A | 692 | 12.018 | 21.785 | 18.011 | 1.00 | 39.35 |
|------|------|-----|-----|---|-----|--------|--------|--------|------|-------|
| ATOM | 2172 | OH2 | H2O | A | 693 | 15.768 | 23.631 | 12.484 | 1.00 | 37.42 |
| ATOM | 2173 | OH2 | H2O | A | 694 | 16.802 | -0.093 | 17.486 | 1.00 | 51.04 |
| ATOM | 2174 | OH2 | H2O | A | 695 | -9.488 | 10.374 | -6.636 | 1.00 | 33.50 |
| ATOM | 2175 | OH2 | H2O | A | 698 | 24.158 | 11.917 | 35.373 | 1.00 | 45.10 |
| ATOM | 2176 | OH2 | H2O | A | 699 | -5.244 | 21.823 | -0.370 | 1.00 | 34.04 |
| ATOM | 2177 | OH2 | H2O | A | 701 | 32.786 | 11.975 | 23.555 | 1.00 | 36.95 |
| ATOM | 2178 | OH2 | H2O | A | 702 | 0.769 | 0.146 | 0.517 | 1.00 | 37.37 |
| ATOM | 2179 | OH2 | H2O | A | 703 | 0.293 | 22.322 | -1.032 | 1.00 | 46.34 |
| ATOM | 2180 | OH2 | H2O | A | 704 | -5.559 | 4.932 | 6.069 | 1.00 | 50.33 |
| ATOM | 2181 | OH2 | H2O | A | 705 | 4.926 | 27.153 | -5.595 | 1.00 | 43.09 |
| ATOM | 2182 | OH2 | H2O | A | 706 | 9.805 | 27.269 | -7.122 | 1.00 | 26.23 |
| ATOM | 2183 | OH2 | H2O | A | 707 | 19.399 | -4.066 | 35.075 | 1.00 | 29.86 |
| ATOM | 2184 | OH2 | H2O | A | 708 | -5.606 | 9.103 | 4.009 | 1.00 | 48.25 |
| ATOM | 2185 | OH2 | H2O | A | 709 | 6.447 | 32.106 | -3.931 | 1.00 | 52.93 |
| ATOM | 2186 | OH2 | H2O | A | 710 | 12.344 | -1.872 | 5.641 | 1.00 | 37.59 |
| ATOM | 2187 | OH2 | H2O | A | 711 | 0.183 | 14.271 | -4.621 | 1.00 | 52.75 |
| ATOM | 2188 | OH2 | H2O | A | 712 | -0.230 | 36.102 | 4.573 | 1.00 | 50.33 |
| ATOM | 2189 | OH2 | H2O | A | 713 | 33.522 | -0.016 | 31.192 | 1.00 | 24.09 |
| ATOM | 2190 | OH2 | H2O | A | 714 | 0.889 | 12.237 | 22.678 | 1.00 | 46.63 |
| ATOM | 2191 | OH2 | H2O | A | 715 | 7.907 | 16.739 | 19.315 | 1.00 | 35.69 |
| ATOM | 2192 | OH2 | H2O | A | 716 | 5.853 | -5.531 | 20.814 | 1.00 | 45.97 |
| ATOM | 2193 | OH2 | H2O | A | 717 | 15.249 | -3.485 | 5.698 | 1.00 | 43.03 |
| ATOM | 2194 | OH2 | H2O | A | 718 | 30.639 | 10.202 | 37.313 | 1.00 | 52.67 |
| ATOM | 2195 | OH2 | H2O | A | 719 | 28.881 | 14.234 | 38.126 | 1.00 | 40.62 |
| ATOM | 2196 | OH2 | H2O | A | 720 | 27.812 | 7.861 | 5.675 | 1.00 | 32.00 |
| ATOM | 2197 | OH2 | H2O | A | 721 | 13.761 | 7.010 | 27.381 | 1.00 | 45.97 |
| ATOM | 2198 | OH2 | H2O | A | 722 | 9.053 | 21.978 | -10.858 | 1.00 | 36.85 |
| ATOM | 2199 | OH2 | H2O | A | 723 | 23.866 | -2.598 | 39.231 | 1.00 | 32.07 |
| ATOM | 2200 | OH2 | H2O | A | 724 | 9.668 | 8.977 | -9.347 | 1.00 | 58.48 |
| ATOM | 2201 | OH2 | H2O | A | 725 | -9.758 | 31.601 | 9.583 | 1.00 | 60.40 |
| ATOM | 2202 | OH2 | H2O | A | 726 | 13.558 | 11.124 | 24.733 | 1.00 | 26.77 |
| ATOM | 2203 | CB | TRP | B | 238 | 46.260 | 28.095 | 32.654 | 1.00 | 54.61 |
| ATOM | 2204 | CG | TRP | B | 238 | 45.842 | 28.514 | 34.041 | 1.00 | 55.31 |
| ATOM | 2205 | CD2 | TRP | B | 238 | 46.442 | 28.109 | 35.285 | 1.00 | 55.04 |
| ATOM | 2206 | CE2 | TRP | B | 238 | 45.692 | 28.705 | 36.321 | 1.00 | 55.13 |
| ATOM | 2207 | CE3 | TRP | B | 238 | 47.539 | 27.307 | 35.623 | 1.00 | 55.22 |
| ATOM | 2208 | CD1 | TRP | B | 238 | 44.786 | 29.315 | 34.371 | 1.00 | 55.03 |
| ATOM | 2209 | NE1 | TRP | B | 238 | 44.688 | 29.434 | 35.734 | 1.00 | 55.23 |
| ATOM | 2210 | CZ2 | TRP | B | 238 | 46.003 | 28.522 | 37.678 | 1.00 | 55.67 |
| ATOM | 2211 | CZ3 | TRP | B | 238 | 47.851 | 27.127 | 36.975 | 1.00 | 54.90 |
| ATOM | 2212 | CH2 | TRP | B | 238 | 47.084 | 27.734 | 37.982 | 1.00 | 54.62 |
| ATOM | 2213 | C | TRP | B | 238 | 47.928 | 28.110 | 30.812 | 1.00 | 53.69 |
| ATOM | 2214 | O | TRP | B | 238 | 48.337 | 26.950 | 30.909 | 1.00 | 54.40 |
| ATOM | 2215 | N | TRP | B | 238 | 47.108 | 30.291 | 31.848 | 1.00 | 52.49 |
| ATOM | 2216 | CA | TRP | B | 238 | 47.454 | 28.855 | 32.068 | 1.00 | 53.51 |
| ATOM | 2217 | N | GLU | B | 239 | 47.808 | 28.742 | 29.646 | 1.00 | 53.76 |
| ATOM | 2218 | CA | GLU | B | 239 | 48.237 | 28.132 | 28.369 | 1.00 | 52.06 |
| ATOM | 2219 | CB | GLU | B | 239 | 47.334 | 28.585 | 27.207 | 1.00 | 52.69 |
| ATOM | 2220 | CG | GLU | B | 239 | 45.866 | 28.182 | 27.333 | 0.00 | 53.14 |
| ATOM | 2221 | CD | GLU | B | 239 | 45.020 | 28.658 | 26.157 | 0.00 | 53.36 |
| ATOM | 2222 | OE1 | GLU | B | 239 | 45.567 | 29.297 | 25.228 | 0.00 | 53.54 |
| ATOM | 2223 | OE2 | GLU | B | 239 | 43.801 | 28.394 | 26.161 | 0.00 | 53.51 |
| ATOM | 2224 | C | GLU | B | 239 | 49.690 | 28.521 | 28.063 | 1.00 | 50.22 |
| ATOM | 2225 | O | GLU | B | 239 | 50.098 | 29.669 | 28.269 | 1.00 | 50.22 |
| ATOM | 2226 | N | VAL | B | 240 | 50.476 | 27.551 | 27.584 | 1.00 | 47.27 |
| ATOM | 2227 | CA | VAL | B | 240 | 51.880 | 27.783 | 27.249 | 1.00 | 44.98 |
| ATOM | 2228 | CB | VAL | B | 240 | 52.823 | 27.285 | 28.383 | 1.00 | 43.89 |
| ATOM | 2229 | CG1 | VAL | B | 240 | 52.542 | 28.030 | 29.679 | 1.00 | 43.03 |

Figure 6

| | | | | | | | | | |
|---|---|---|---|---|---|---|---|---|---|
| ATOM | 2230 | CG2 | VAL | B | 240 | 52.686 | 25.780 | 28.573 | 1.00 42.05 |
| ATOM | 2231 | C | VAL | B | 240 | 52.275 | 27.066 | 25.953 | 1.00 44.40 |
| ATOM | 2232 | O | VAL | B | 240 | 51.574 | 26.167 | 25.491 | 1.00 45.06 |
| ATOM | 2233 | N | PRO | B | 241 | 53.356 | 27.519 | 25.303 | 1.00 43.64 |
| ATOM | 2234 | CD | PRO | B | 241 | 53.986 | 28.841 | 25.467 | 1.00 43.02 |
| ATOM | 2235 | CA | PRO | B | 241 | 53.805 | 26.882 | 24.059 | 1.00 43.35 |
| ATOM | 2236 | CB | PRO | B | 241 | 54.865 | 27.860 | 23.552 | 1.00 42.99 |
| ATOM | 2237 | CG | PRO | B | 241 | 54.369 | 29.185 | 24.049 | 1.00 42.48 |
| ATOM | 2238 | C | PRO | B | 241 | 54.418 | 25.503 | 24.344 | 1.00 43.73 |
| ATOM | 2239 | O | PRO | B | 241 | 55.068 | 25.319 | 25.366 | 1.00 44.39 |
| ATOM | 2240 | N | ARG | B | 242 | 54.221 | 24.546 | 23.443 | 1.00 44.49 |
| ATOM | 2241 | CA | ARG | B | 242 | 54.761 | 23.190 | 23.598 | 1.00 45.99 |
| ATOM | 2242 | CB | ARG | B | 242 | 54.343 | 22.358 | 22.382 | 1.00 46.88 |
| ATOM | 2243 | CG | ARG | B | 242 | 55.073 | 21.031 | 22.171 | 1.00 48.13 |
| ATOM | 2244 | CD | ARG | B | 242 | 54.527 | 19.936 | 23.049 | 1.00 49.75 |
| ATOM | 2245 | NE | ARG | B | 242 | 53.063 | 19.872 | 23.001 | 1.00 51.26 |
| ATOM | 2246 | CZ | ARG | B | 242 | 52.343 | 19.473 | 21.959 | 1.00 50.32 |
| ATOM | 2247 | NH1 | ARG | B | 242 | 52.933 | 19.087 | 20.839 | 1.00 51.78 |
| ATOM | 2248 | NH2 | ARG | B | 242 | 51.023 | 19.469 | 22.035 | 1.00 49.86 |
| ATOM | 2249 | C | ARG | B | 242 | 56.291 | 23.144 | 23.758 | 1.00 46.60 |
| ATOM | 2250 | O | ARG | B | 242 | 56.831 | 22.186 | 24.313 | 1.00 46.63 |
| ATOM | 2251 | N | GLU | B | 243 | 56.968 | 24.178 | 23.254 | 1.00 48.02 |
| ATOM | 2252 | CA | GLU | B | 243 | 58.438 | 24.295 | 23.288 | 1.00 48.73 |
| ATOM | 2253 | CB | GLU | B | 243 | 58.925 | 25.428 | 22.356 | 1.00 51.20 |
| ATOM | 2254 | CG | GLU | B | 243 | 58.776 | 25.184 | 20.839 | 1.00 54.40 |
| ATOM | 2255 | CD | GLU | B | 243 | 57.314 | 25.118 | 20.351 | 1.00 55.70 |
| ATOM | 2256 | OE1 | GLU | B | 243 | 56.550 | 26.092 | 20.585 | 1.00 54.94 |
| ATOM | 2257 | OE2 | GLU | B | 243 | 56.940 | 24.089 | 19.724 | 1.00 56.50 |
| ATOM | 2258 | C | GLU | B | 243 | 59.003 | 24.531 | 24.687 | 1.00 47.24 |
| ATOM | 2259 | O | GLU | B | 243 | 60.133 | 24.148 | 24.985 | 1.00 47.59 |
| ATOM | 2260 | N | THR | B | 244 | 58.212 | 25.167 | 25.539 | 1.00 44.51 |
| ATOM | 2261 | CA | THR | B | 244 | 58.628 | 25.464 | 26.903 | 1.00 42.01 |
| ATOM | 2262 | CB | THR | B | 244 | 57.696 | 26.513 | 27.517 | 1.00 42.33 |
| ATOM | 2263 | OG1 | THR | B | 244 | 56.444 | 25.905 | 27.863 | 1.00 42.76 |
| ATOM | 2264 | CG2 | THR | B | 244 | 57.439 | 27.627 | 26.520 | 1.00 42.84 |
| ATOM | 2265 | C | THR | B | 244 | 58.623 | 24.212 | 27.792 | 1.00 40.59 |
| ATOM | 2266 | O | THR | B | 244 | 58.977 | 24.275 | 28.970 | 1.00 39.05 |
| ATOM | 2267 | N | LEU | B | 245 | 58.285 | 23.074 | 27.197 | 1.00 39.00 |
| ATOM | 2268 | CA | LEU | B | 245 | 58.191 | 21.817 | 27.912 | 1.00 38.10 |
| ATOM | 2269 | CB | LEU | B | 245 | 56.708 | 21.453 | 28.063 | 1.00 38.93 |
| ATOM | 2270 | CG | LEU | B | 245 | 56.351 | 20.164 | 28.800 | 1.00 40.52 |
| ATOM | 2271 | CD1 | LEU | B | 245 | 56.696 | 20.294 | 30.280 | 1.00 39.69 |
| ATOM | 2272 | CD2 | LEU | B | 245 | 54.864 | 19.867 | 28.606 | 1.00 41.59 |
| ATOM | 2273 | C | LEU | B | 245 | 58.927 | 20.690 | 27.196 | 1.00 37.75 |
| ATOM | 2274 | O | LEU | B | 245 | 58.814 | 20.546 | 25.966 | 1.00 37.93 |
| ATOM | 2275 | N | LYS | B | 246 | 59.679 | 19.901 | 27.974 | 1.00 35.78 |
| ATOM | 2276 | CA | LYS | B | 246 | 60.432 | 18.758 | 27.458 | 1.00 33.73 |
| ATOM | 2277 | CB | LYS | B | 246 | 61.950 | 18.988 | 27.557 | 1.00 35.16 |
| ATOM | 2278 | CG | LYS | B | 246 | 62.789 | 17.730 | 27.235 | 1.00 36.91 |
| ATOM | 2279 | CD | LYS | B | 246 | 64.279 | 18.009 | 26.997 | 1.00 39.03 |
| ATOM | 2280 | CE | LYS | B | 246 | 64.986 | 18.504 | 28.257 | 1.00 40.56 |
| ATOM | 2281 | NZ | LYS | B | 246 | 66.464 | 18.645 | 28.071 | 1.00 41.84 |
| ATOM | 2282 | C | LYS | B | 246 | 60.072 | 17.473 | 28.197 | 1.00 32.28 |
| ATOM | 2283 | O | LYS | B | 246 | 60.247 | 17.373 | 29.405 | 1.00 32.03 |
| ATOM | 2284 | N | LEU | B | 247 | 59.562 | 16.495 | 27.456 | 1.00 30.73 |
| ATOM | 2285 | CA | LEU | B | 247 | 59.196 | 15.203 | 28.019 | 1.00 28.35 |
| ATOM | 2286 | CB | LEU | B | 247 | 58.097 | 14.547 | 27.198 | 1.00 26.51 |
| ATOM | 2287 | CG | LEU | B | 247 | 56.698 | 15.010 | 27.592 | 1.00 26.31 |
| ATOM | 2288 | CD1 | LEU | B | 247 | 56.543 | 16.520 | 27.481 | 1.00 25.54 |

Figure 6

```
ATOM   2289  CD2 LEU B 247      55.694  14.272  26.726  1.00 27.78
ATOM   2290  C   LEU B 247      60.422  14.319  28.071  1.00 28.99
ATOM   2291  O   LEU B 247      61.132  14.151  27.071  1.00 30.07
ATOM   2292  N   VAL B 248      60.647  13.711  29.229  1.00 26.79
ATOM   2293  CA  VAL B 248      61.824  12.889  29.415  1.00 25.93
ATOM   2294  CB  VAL B 248      62.695  13.453  30.571  1.00 24.91
ATOM   2295  CG1 VAL B 248      64.004  12.691  30.663  1.00 25.08
ATOM   2296  CG2 VAL B 248      62.954  14.935  30.378  1.00 20.94
ATOM   2297  C   VAL B 248      61.616  11.399  29.651  1.00 26.69
ATOM   2298  O   VAL B 248      62.329  10.564  29.088  1.00 29.23
ATOM   2299  N   GLU B 249      60.616  11.043  30.432  1.00 27.66
ATOM   2300  CA  GLU B 249      60.432   9.639  30.752  1.00 27.59
ATOM   2301  CB  GLU B 249      61.307   9.342  31.969  1.00 27.78
ATOM   2302  CG  GLU B 249      61.191   7.959  32.568  1.00 28.76
ATOM   2303  CD  GLU B 249      62.006   7.830  33.829  1.00 29.09
ATOM   2304  OE1 GLU B 249      62.720   8.795  34.198  1.00 28.13
ATOM   2305  OE2 GLU B 249      61.932   6.757  34.454  1.00 30.98
ATOM   2306  C   GLU B 249      58.976   9.280  31.031  1.00 27.12
ATOM   2307  O   GLU B 249      58.267   9.998  31.730  1.00 25.49
ATOM   2308  N   ARG B 250      58.549   8.140  30.509  1.00 26.37
ATOM   2309  CA  ARG B 250      57.184   7.703  30.694  1.00 27.55
ATOM   2310  CB  ARG B 250      56.759   6.787  29.552  1.00 27.02
ATOM   2311  CG  ARG B 250      55.322   6.991  29.140  1.00 27.56
ATOM   2312  CD  ARG B 250      54.944   6.104  27.984  1.00 26.77
ATOM   2313  NE  ARG B 250      55.151   4.703  28.322  1.00 26.91
ATOM   2314  CZ  ARG B 250      54.836   3.690  27.527  1.00 28.14
ATOM   2315  NH1 ARG B 250      54.298   3.925  26.341  1.00 27.53
ATOM   2316  NH2 ARG B 250      55.032   2.437  27.930  1.00 28.59
ATOM   2317  C   ARG B 250      57.011   7.000  32.022  1.00 27.49
ATOM   2318  O   ARG B 250      57.602   5.946  32.250  1.00 28.04
ATOM   2319  N   LEU B 251      56.232   7.619  32.911  1.00 27.14
ATOM   2320  CA  LEU B 251      55.943   7.064  34.232  1.00 25.67
ATOM   2321  CB  LEU B 251      55.538   8.166  35.207  1.00 22.61
ATOM   2322  CG  LEU B 251      56.610   9.241  35.396  1.00 22.62
ATOM   2323  CD1 LEU B 251      56.174  10.261  36.447  1.00 21.58
ATOM   2324  CD2 LEU B 251      57.934   8.597  35.782  1.00 21.67
ATOM   2325  C   LEU B 251      54.843   6.002  34.135  1.00 25.91
ATOM   2326  O   LEU B 251      54.839   5.011  34.877  1.00 26.98
ATOM   2327  N   GLY B 252      53.935   6.192  33.185  1.00 26.29
ATOM   2328  CA  GLY B 252      52.858   5.237  33.004  1.00 24.17
ATOM   2329  C   GLY B 252      52.106   5.417  31.707  1.00 23.07
ATOM   2330  O   GLY B 252      52.082   6.507  31.125  1.00 20.94
ATOM   2331  N   ALA B 253      51.476   4.335  31.272  1.00 23.87
ATOM   2332  CA  ALA B 253      50.692   4.320  30.041  1.00 23.68
ATOM   2333  CB  ALA B 253      51.479   3.677  28.921  1.00 22.55
ATOM   2334  C   ALA B 253      49.423   3.530  30.296  1.00 25.41
ATOM   2335  O   ALA B 253      49.476   2.422  30.829  1.00 24.27
ATOM   2336  N   GLY B 254      48.283   4.100  29.914  1.00 27.61
ATOM   2337  CA  GLY B 254      47.024   3.421  30.116  1.00 29.74
ATOM   2338  C   GLY B 254      46.020   3.622  29.002  1.00 32.05
ATOM   2339  O   GLY B 254      46.358   4.111  27.932  1.00 33.66
ATOM   2340  N   GLN B 255      44.766   3.284  29.302  1.00 34.35
ATOM   2341  CA  GLN B 255      43.642   3.364  28.371  1.00 35.31
ATOM   2342  CB  GLN B 255      42.384   2.799  29.062  1.00 38.22
ATOM   2343  CG  GLN B 255      41.550   1.832  28.200  1.00 44.28
ATOM   2344  CD  GLN B 255      40.010   2.067  28.294  1.00 47.35
ATOM   2345  OE1 GLN B 255      39.295   2.053  27.258  1.00 46.52
ATOM   2346  NE2 GLN B 255      39.505   2.284  29.532  1.00 46.91
ATOM   2347  C   GLN B 255      43.342   4.756  27.784  1.00 33.38
```

Figure 6

| | | | | | | | | | |
|---|---|---|---|---|---|---|---|---|---|
| ATOM | 2348 | O | GLN | B | 255 | 43.085 | 4.877 | 26.584 | 1.00 32.90 |
| ATOM | 2349 | N | PHE | B | 256 | 43.360 | 5.789 | 28.634 | 1.00 31.04 |
| ATOM | 2350 | CA | PHE | B | 256 | 43.062 | 7.173 | 28.222 | 1.00 28.74 |
| ATOM | 2351 | CB | PHE | B | 256 | 42.236 | 7.909 | 29.308 | 1.00 29.13 |
| ATOM | 2352 | CG | PHE | B | 256 | 40.849 | 7.341 | 29.558 | 1.00 29.23 |
| ATOM | 2353 | CD1 | PHE | B | 256 | 40.443 | 6.122 | 29.024 | 1.00 29.93 |
| ATOM | 2354 | CD2 | PHE | B | 256 | 39.948 | 8.052 | 30.352 | 1.00 30.20 |
| ATOM | 2355 | CE1 | PHE | B | 256 | 39.155 | 5.616 | 29.275 | 1.00 30.43 |
| ATOM | 2356 | CE2 | PHE | B | 256 | 38.669 | 7.560 | 30.607 | 1.00 30.27 |
| ATOM | 2357 | CZ | PHE | B | 256 | 38.272 | 6.339 | 30.065 | 1.00 30.60 |
| ATOM | 2358 | C | PHE | B | 256 | 44.273 | 8.059 | 27.895 | 1.00 27.36 |
| ATOM | 2359 | O | PHE | B | 256 | 44.114 | 9.208 | 27.464 | 1.00 26.84 |
| ATOM | 2360 | N | GLY | B | 257 | 45.475 | 7.566 | 28.146 | 1.00 26.88 |
| ATOM | 2361 | CA | GLY | B | 257 | 46.643 | 8.380 | 27.876 | 1.00 25.41 |
| ATOM | 2362 | C | GLY | B | 257 | 47.869 | 7.886 | 28.610 | 1.00 26.92 |
| ATOM | 2363 | O | GLY | B | 257 | 47.977 | 6.699 | 28.939 | 1.00 25.56 |
| ATOM | 2364 | N | GLU | B | 258 | 48.786 | 8.812 | 28.880 | 1.00 28.26 |
| ATOM | 2365 | CA | GLU | B | 258 | 50.053 | 8.510 | 29.550 | 1.00 29.52 |
| ATOM | 2366 | CB | GLU | B | 258 | 51.149 | 8.317 | 28.504 | 1.00 30.16 |
| ATOM | 2367 | CG | GLU | B | 258 | 50.793 | 7.353 | 27.403 | 1.00 31.32 |
| ATOM | 2368 | CD | GLU | B | 258 | 51.938 | 7.102 | 26.456 | 1.00 32.44 |
| ATOM | 2369 | OE1 | GLU | B | 258 | 52.646 | 8.068 | 26.092 | 1.00 32.53 |
| ATOM | 2370 | OE2 | GLU | B | 258 | 52.122 | 5.922 | 26.082 | 1.00 33.80 |
| ATOM | 2371 | C | GLU | B | 258 | 50.514 | 9.636 | 30.471 | 1.00 29.95 |
| ATOM | 2372 | O | GLU | B | 258 | 50.110 | 10.791 | 30.299 | 1.00 30.75 |
| ATOM | 2373 | N | VAL | B | 259 | 51.392 | 9.297 | 31.424 | 1.00 29.56 |
| ATOM | 2374 | CA | VAL | B | 259 | 51.966 | 10.279 | 32.351 | 1.00 29.37 |
| ATOM | 2375 | CB | VAL | B | 259 | 51.656 | 9.960 | 33.839 | 1.00 29.04 |
| ATOM | 2376 | CG1 | VAL | B | 259 | 52.112 | 11.118 | 34.730 | 1.00 27.76 |
| ATOM | 2377 | CG2 | VAL | B | 259 | 50.161 | 9.718 | 34.032 | 1.00 29.93 |
| ATOM | 2378 | C | VAL | B | 259 | 53.481 | 10.249 | 32.126 | 1.00 29.18 |
| ATOM | 2379 | O | VAL | B | 259 | 54.084 | 9.177 | 32.062 | 1.00 29.62 |
| ATOM | 2380 | N | TRP | B | 260 | 54.081 | 11.427 | 31.975 | 1.00 28.26 |
| ATOM | 2381 | CA | TRP | B | 260 | 55.517 | 11.560 | 31.723 | 1.00 28.17 |
| ATOM | 2382 | CB | TRP | B | 260 | 55.764 | 12.175 | 30.310 | 1.00 28.37 |
| ATOM | 2383 | CG | TRP | B | 260 | 55.614 | 11.235 | 29.132 | 1.00 30.44 |
| ATOM | 2384 | CD2 | TRP | B | 260 | 56.661 | 10.759 | 28.264 | 1.00 32.08 |
| ATOM | 2385 | CE2 | TRP | B | 260 | 56.082 | 9.809 | 27.393 | 1.00 33.61 |
| ATOM | 2386 | CE3 | TRP | B | 260 | 58.032 | 11.032 | 28.150 | 1.00 32.96 |
| ATOM | 2387 | CD1 | TRP | B | 260 | 54.476 | 10.588 | 28.737 | 1.00 31.77 |
| ATOM | 2388 | NE1 | TRP | B | 260 | 54.750 | 9.720 | 27.704 | 1.00 33.14 |
| ATOM | 2389 | CZ2 | TRP | B | 260 | 56.831 | 9.130 | 26.416 | 1.00 33.70 |
| ATOM | 2390 | CZ3 | TRP | B | 260 | 58.776 | 10.353 | 27.179 | 1.00 32.45 |
| ATOM | 2391 | CH2 | TRP | B | 260 | 58.172 | 9.414 | 26.331 | 1.00 33.26 |
| ATOM | 2392 | C | TRP | B | 260 | 56.217 | 12.472 | 32.735 | 1.00 27.32 |
| ATOM | 2393 | O | TRP | B | 260 | 55.619 | 13.406 | 33.260 | 1.00 25.45 |
| ATOM | 2394 | N | MET | B | 261 | 57.464 | 12.148 | 33.059 | 1.00 27.36 |
| ATOM | 2395 | CA | MET | B | 261 | 58.264 | 13.033 | 33.895 | 1.00 28.40 |
| ATOM | 2396 | CB | MET | B | 261 | 59.329 | 12.250 | 34.681 | 1.00 28.20 |
| ATOM | 2397 | CG | MET | B | 261 | 60.252 | 13.145 | 35.536 | 1.00 27.59 |
| ATOM | 2398 | SD | MET | B | 261 | 61.713 | 13.882 | 34.686 | 1.00 28.13 |
| ATOM | 2399 | CE | MET | B | 261 | 62.681 | 12.401 | 34.367 | 1.00 25.59 |
| ATOM | 2400 | C | MET | B | 261 | 58.937 | 13.944 | 32.838 | 1.00 27.31 |
| ATOM | 2401 | O | MET | B | 261 | 59.270 | 13.489 | 31.757 | 1.00 27.94 |
| ATOM | 2402 | N | GLY | B | 262 | 59.101 | 15.221 | 33.129 | 1.00 26.05 |
| ATOM | 2403 | CA | GLY | B | 262 | 59.713 | 16.113 | 32.166 | 1.00 24.84 |
| ATOM | 2404 | C | GLY | B | 262 | 60.152 | 17.411 | 32.803 | 1.00 26.16 |
| ATOM | 2405 | O | GLY | B | 262 | 60.037 | 17.580 | 34.007 | 1.00 26.70 |
| ATOM | 2406 | N | TYR | B | 263 | 60.659 | 18.334 | 31.998 | 1.00 26.39 |

Figure 6

| | | | | | | | | | |
|---|---|---|---|---|---|---|---|---|---|
| ATOM | 2407 | CA | TYR | B | 263 | 61.117 | 19.603 | 32.521 | 1.00 27.63 |
| ATOM | 2408 | CB | TYR | B | 263 | 62.624 | 19.713 | 32.345 | 1.00 26.26 |
| ATOM | 2409 | CG | TYR | B | 263 | 63.342 | 18.689 | 33.193 | 1.00 24.67 |
| ATOM | 2410 | CD1 | TYR | B | 263 | 63.657 | 18.966 | 34.520 | 1.00 23.72 |
| ATOM | 2411 | CE1 | TYR | B | 263 | 64.233 | 18.019 | 35.334 | 1.00 23.51 |
| ATOM | 2412 | CD2 | TYR | B | 263 | 63.634 | 17.414 | 32.694 | 1.00 23.22 |
| ATOM | 2413 | CE2 | TYR | B | 263 | 64.215 | 16.446 | 33.506 | 1.00 23.17 |
| ATOM | 2414 | CZ | TYR | B | 263 | 64.508 | 16.762 | 34.831 | 1.00 24.18 |
| ATOM | 2415 | OH | TYR | B | 263 | 65.064 | 15.828 | 35.677 | 1.00 24.06 |
| ATOM | 2416 | C | TYR | B | 263 | 60.377 | 20.774 | 31.919 | 1.00 30.94 |
| ATOM | 2417 | O | TYR | B | 263 | 60.114 | 20.814 | 30.716 | 1.00 33.21 |
| ATOM | 2418 | N | TYR | B | 264 | 59.966 | 21.682 | 32.791 | 1.00 34.50 |
| ATOM | 2419 | CA | TYR | B | 264 | 59.206 | 22.871 | 32.426 | 1.00 37.03 |
| ATOM | 2420 | CB | TYR | B | 264 | 57.976 | 22.975 | 33.344 | 1.00 36.85 |
| ATOM | 2421 | CG | TYR | B | 264 | 57.062 | 24.147 | 33.094 | 1.00 37.67 |
| ATOM | 2422 | CD1 | TYR | B | 264 | 56.726 | 24.540 | 31.790 | 1.00 37.49 |
| ATOM | 2423 | CE1 | TYR | B | 264 | 55.883 | 25.629 | 31.559 | 1.00 36.80 |
| ATOM | 2424 | CD2 | TYR | B | 264 | 56.536 | 24.870 | 34.162 | 1.00 37.41 |
| ATOM | 2425 | CE2 | TYR | B | 264 | 55.695 | 25.957 | 33.946 | 1.00 37.40 |
| ATOM | 2426 | CZ | TYR | B | 264 | 55.373 | 26.330 | 32.645 | 1.00 37.32 |
| ATOM | 2427 | OH | TYR | B | 264 | 54.528 | 27.394 | 32.446 | 1.00 36.89 |
| ATOM | 2428 | C | TYR | B | 264 | 60.155 | 24.059 | 32.575 | 1.00 39.34 |
| ATOM | 2429 | O | TYR | B | 264 | 60.751 | 24.262 | 33.637 | 1.00 40.17 |
| ATOM | 2430 | N | ASN | B | 265 | 60.329 | 24.800 | 31.482 | 1.00 42.02 |
| ATOM | 2431 | CA | ASN | B | 265 | 61.230 | 25.950 | 31.421 | 1.00 43.12 |
| ATOM | 2432 | CB | ASN | B | 265 | 60.778 | 27.070 | 32.362 | 1.00 43.64 |
| ATOM | 2433 | CG | ASN | B | 265 | 59.409 | 27.616 | 31.999 | 1.00 44.35 |
| ATOM | 2434 | OD1 | ASN | B | 265 | 59.139 | 27.954 | 30.837 | 1.00 44.25 |
| ATOM | 2435 | ND2 | ASN | B | 265 | 58.528 | 27.687 | 32.986 | 1.00 44.40 |
| ATOM | 2436 | C | ASN | B | 265 | 62.649 | 25.502 | 31.737 | 1.00 43.44 |
| ATOM | 2437 | O | ASN | B | 265 | 63.349 | 26.114 | 32.536 | 1.00 44.54 |
| ATOM | 2438 | N | GLY | B | 266 | 63.030 | 24.375 | 31.148 | 1.00 44.04 |
| ATOM | 2439 | CA | GLY | B | 266 | 64.359 | 23.835 | 31.330 | 1.00 45.45 |
| ATOM | 2440 | C | GLY | B | 266 | 64.703 | 23.223 | 32.675 | 1.00 46.56 |
| ATOM | 2441 | O | GLY | B | 266 | 65.308 | 22.144 | 32.721 | 1.00 47.77 |
| ATOM | 2442 | N | HIS | B | 267 | 64.275 | 23.850 | 33.766 | 1.00 46.25 |
| ATOM | 2443 | CA | HIS | B | 267 | 64.642 | 23.341 | 35.082 | 1.00 46.01 |
| ATOM | 2444 | CB | HIS | B | 267 | 65.619 | 24.325 | 35.752 | 1.00 46.92 |
| ATOM | 2445 | CG | HIS | B | 267 | 66.934 | 24.432 | 35.046 | 0.00 47.65 |
| ATOM | 2446 | CD2 | HIS | B | 267 | 67.924 | 23.523 | 34.863 | 0.00 47.95 |
| ATOM | 2447 | ND1 | HIS | B | 267 | 67.336 | 25.569 | 34.382 | 0.00 47.93 |
| ATOM | 2448 | CE1 | HIS | B | 267 | 68.512 | 25.357 | 33.819 | 0.00 48.16 |
| ATOM | 2449 | NE2 | HIS | B | 267 | 68.889 | 24.123 | 34.095 | 0.00 48.15 |
| ATOM | 2450 | C | HIS | B | 267 | 63.569 | 22.829 | 36.067 | 1.00 44.24 |
| ATOM | 2451 | O | HIS | B | 267 | 63.869 | 21.950 | 36.880 | 1.00 44.65 |
| ATOM | 2452 | N | THR | B | 268 | 62.330 | 23.322 | 35.987 | 1.00 41.00 |
| ATOM | 2453 | CA | THR | B | 268 | 61.285 | 22.855 | 36.909 | 1.00 38.04 |
| ATOM | 2454 | CB | THR | B | 268 | 59.996 | 23.732 | 36.855 | 1.00 39.13 |
| ATOM | 2455 | OG1 | THR | B | 268 | 60.304 | 25.080 | 37.229 | 1.00 40.58 |
| ATOM | 2456 | CG2 | THR | B | 268 | 58.934 | 23.208 | 37.830 | 1.00 38.64 |
| ATOM | 2457 | C | THR | B | 268 | 60.888 | 21.436 | 36.550 | 1.00 34.08 |
| ATOM | 2458 | O | THR | B | 268 | 60.398 | 21.207 | 35.460 | 1.00 33.42 |
| ATOM | 2459 | N | LYS | B | 269 | 61.109 | 20.485 | 37.454 | 1.00 31.28 |
| ATOM | 2460 | CA | LYS | B | 269 | 60.732 | 19.100 | 37.191 | 1.00 28.31 |
| ATOM | 2461 | CB | LYS | B | 269 | 61.400 | 18.153 | 38.186 | 1.00 26.05 |
| ATOM | 2462 | CG | LYS | B | 269 | 61.421 | 16.690 | 37.770 | 1.00 23.71 |
| ATOM | 2463 | CD | LYS | B | 269 | 62.407 | 15.908 | 38.642 | 1.00 22.41 |
| ATOM | 2464 | CE | LYS | B | 269 | 62.667 | 14.509 | 38.095 | 1.00 22.34 |
| ATOM | 2465 | NZ | LYS | B | 269 | 63.712 | 13.746 | 38.857 | 1.00 21.55 |

Figure 6

| | | | | | | | | | |
|---|---|---|---|---|---|---|---|---|---|
| ATOM | 2466 | C | LYS | B | 269 | 59.210 | 19.030 | 37.307 | 1.00 29.34 |
| ATOM | 2467 | O | LYS | B | 269 | 58.612 | 19.627 | 38.212 | 1.00 28.86 |
| ATOM | 2468 | N | VAL | B | 270 | 58.588 | 18.363 | 36.337 | 1.00 28.30 |
| ATOM | 2469 | CA | VAL | B | 270 | 57.141 | 18.242 | 36.292 | 1.00 25.54 |
| ATOM | 2470 | CB | VAL | B | 270 | 56.507 | 19.346 | 35.394 | 1.00 25.74 |
| ATOM | 2471 | CG1 | VAL | B | 270 | 56.831 | 20.723 | 35.917 | 1.00 24.66 |
| ATOM | 2472 | CG2 | VAL | B | 270 | 56.960 | 19.195 | 33.937 | 1.00 24.42 |
| ATOM | 2473 | C | VAL | B | 270 | 56.706 | 16.901 | 35.719 | 1.00 25.66 |
| ATOM | 2474 | O | VAL | B | 270 | 57.506 | 16.149 | 35.166 | 1.00 25.13 |
| ATOM | 2475 | N | ALA | B | 271 | 55.426 | 16.601 | 35.925 | 1.00 25.16 |
| ATOM | 2476 | CA | ALA | B | 271 | 54.782 | 15.409 | 35.406 | 1.00 23.37 |
| ATOM | 2477 | CB | ALA | B | 271 | 54.035 | 14.683 | 36.495 | 1.00 24.89 |
| ATOM | 2478 | C | ALA | B | 271 | 53.810 | 16.015 | 34.407 | 1.00 22.69 |
| ATOM | 2479 | O | ALA | B | 271 | 53.240 | 17.087 | 34.646 | 1.00 22.20 |
| ATOM | 2480 | N | VAL | B | 272 | 53.638 | 15.331 | 33.285 | 1.00 21.94 |
| ATOM | 2481 | CA | VAL | B | 272 | 52.783 | 15.807 | 32.209 | 1.00 21.14 |
| ATOM | 2482 | CB | VAL | B | 272 | 53.654 | 16.140 | 30.950 | 1.00 20.42 |
| ATOM | 2483 | CG1 | VAL | B | 272 | 52.795 | 16.610 | 29.802 | 1.00 20.76 |
| ATOM | 2484 | CG2 | VAL | B | 272 | 54.731 | 17.162 | 31.272 | 1.00 18.34 |
| ATOM | 2485 | C | VAL | B | 272 | 51.798 | 14.706 | 31.833 | 1.00 22.04 |
| ATOM | 2486 | O | VAL | B | 272 | 52.209 | 13.585 | 31.555 | 1.00 23.79 |
| ATOM | 2487 | N | LYS | B | 273 | 50.504 | 15.008 | 31.855 | 1.00 22.11 |
| ATOM | 2488 | CA | LYS | B | 273 | 49.493 | 14.022 | 31.460 | 1.00 24.75 |
| ATOM | 2489 | CB | LYS | B | 273 | 48.285 | 14.045 | 32.413 | 1.00 24.99 |
| ATOM | 2490 | CG | LYS | B | 273 | 47.966 | 12.704 | 33.087 | 1.00 24.88 |
| ATOM | 2491 | CD | LYS | B | 273 | 46.872 | 12.860 | 34.148 | 1.00 23.97 |
| ATOM | 2492 | CE | LYS | B | 273 | 46.743 | 11.615 | 35.020 | 1.00 23.74 |
| ATOM | 2493 | NZ | LYS | B | 273 | 45.533 | 11.685 | 35.885 | 1.00 24.29 |
| ATOM | 2494 | C | LYS | B | 273 | 49.034 | 14.354 | 30.025 | 1.00 26.01 |
| ATOM | 2495 | O | LYS | B | 273 | 48.702 | 15.507 | 29.718 | 1.00 24.92 |
| ATOM | 2496 | N | SER | B | 274 | 49.082 | 13.365 | 29.138 | 1.00 26.64 |
| ATOM | 2497 | CA | SER | B | 274 | 48.672 | 13.564 | 27.750 | 1.00 28.87 |
| ATOM | 2498 | CB | SER | B | 274 | 49.791 | 13.147 | 26.826 | 1.00 29.02 |
| ATOM | 2499 | OG | SER | B | 274 | 50.009 | 11.767 | 26.990 | 1.00 31.90 |
| ATOM | 2500 | C | SER | B | 274 | 47.444 | 12.722 | 27.440 | 1.00 29.41 |
| ATOM | 2501 | O | SER | B | 274 | 47.310 | 11.622 | 27.964 | 1.00 31.35 |
| ATOM | 2502 | N | LEU | B | 275 | 46.588 | 13.207 | 26.548 | 1.00 29.31 |
| ATOM | 2503 | CA | LEU | B | 275 | 45.361 | 12.485 | 26.185 | 1.00 29.80 |
| ATOM | 2504 | CB | LEU | B | 275 | 44.213 | 13.492 | 25.933 | 1.00 27.56 |
| ATOM | 2505 | CG | LEU | B | 275 | 42.863 | 13.042 | 25.343 | 1.00 25.31 |
| ATOM | 2506 | CD1 | LEU | B | 275 | 42.145 | 12.073 | 26.283 | 1.00 25.02 |
| ATOM | 2507 | CD2 | LEU | B | 275 | 41.991 | 14.249 | 25.060 | 1.00 24.06 |
| ATOM | 2508 | C | LEU | B | 275 | 45.506 | 11.580 | 24.954 | 1.00 31.95 |
| ATOM | 2509 | O | LEU | B | 275 | 45.932 | 12.031 | 23.899 | 1.00 32.65 |
| ATOM | 2510 | N | LYS | B | 276 | 45.156 | 10.303 | 25.091 | 1.00 33.83 |
| ATOM | 2511 | CA | LYS | B | 276 | 45.191 | 9.378 | 23.957 | 1.00 34.80 |
| ATOM | 2512 | CB | LYS | B | 276 | 45.100 | 7.930 | 24.440 | 1.00 35.67 |
| ATOM | 2513 | CG | LYS | B | 276 | 44.903 | 6.904 | 23.330 | 1.00 35.72 |
| ATOM | 2514 | CD | LYS | B | 276 | 44.886 | 5.477 | 23.886 | 1.00 37.73 |
| ATOM | 2515 | CE | LYS | B | 276 | 46.162 | 5.168 | 24.684 | 1.00 39.22 |
| ATOM | 2516 | NZ | LYS | B | 276 | 46.235 | 3.756 | 25.179 | 1.00 39.47 |
| ATOM | 2517 | C | LYS | B | 276 | 43.953 | 9.714 | 23.129 | 1.00 35.96 |
| ATOM | 2518 | O | LYS | B | 276 | 42.836 | 9.359 | 23.512 | 1.00 35.95 |
| ATOM | 2519 | N | GLN | B | 277 | 44.159 | 10.420 | 22.016 | 1.00 38.22 |
| ATOM | 2520 | CA | GLN | B | 277 | 43.079 | 10.857 | 21.117 | 1.00 38.63 |
| ATOM | 2521 | CB | GLN | B | 277 | 43.650 | 11.216 | 19.742 | 1.00 41.75 |
| ATOM | 2522 | CG | GLN | B | 277 | 42.694 | 11.990 | 18.835 | 1.00 46.04 |
| ATOM | 2523 | CD | GLN | B | 277 | 43.359 | 12.450 | 17.540 | 1.00 47.69 |
| ATOM | 2524 | OE1 | GLN | B | 277 | 44.504 | 12.083 | 17.247 | 1.00 49.61 |

Figure 6

```
ATOM   2525  NE2 GLN B 277      42.649  13.266  16.766  1.00 47.67
ATOM   2526  C   GLN B 277      41.939   9.860  20.963  1.00 35.95
ATOM   2527  O   GLN B 277      42.156   8.704  20.604  1.00 33.68
ATOM   2528  N   GLY B 278      40.736  10.311  21.308  1.00 36.00
ATOM   2529  CA  GLY B 278      39.559   9.469  21.210  1.00 36.50
ATOM   2530  C   GLY B 278      38.984   8.935  22.514  1.00 36.89
ATOM   2531  O   GLY B 278      37.846   8.482  22.533  1.00 37.41
ATOM   2532  N   SER B 279      39.763   8.955  23.595  1.00 37.33
ATOM   2533  CA  SER B 279      39.292   8.458  24.886  1.00 36.11
ATOM   2534  CB  SER B 279      40.453   8.348  25.847  1.00 34.76
ATOM   2535  OG  SER B 279      41.364   7.400  25.338  1.00 35.41
ATOM   2536  C   SER B 279      38.205   9.350  25.462  1.00 35.83
ATOM   2537  O   SER B 279      37.318   8.887  26.181  1.00 36.11
ATOM   2538  N   MET B 280      38.270  10.621  25.092  1.00 34.60
ATOM   2539  CA  MET B 280      37.313  11.641  25.508  1.00 33.96
ATOM   2540  CB  MET B 280      37.349  11.886  27.032  1.00 32.70
ATOM   2541  CG  MET B 280      38.708  12.324  27.610  1.00 31.64
ATOM   2542  SD  MET B 280      38.846  12.331  29.448  1.00 28.96
ATOM   2543  CE  MET B 280      38.090  13.822  29.770  1.00 27.97
ATOM   2544  C   MET B 280      37.727  12.891  24.746  1.00 33.00
ATOM   2545  O   MET B 280      38.818  12.935  24.183  1.00 33.78
ATOM   2546  N   SER B 281      36.872  13.898  24.719  1.00 32.29
ATOM   2547  CA  SER B 281      37.193  15.117  23.997  1.00 33.29
ATOM   2548  CB  SER B 281      35.936  15.950  23.769  1.00 32.47
ATOM   2549  OG  SER B 281      35.602  16.689  24.930  1.00 33.18
ATOM   2550  C   SER B 281      38.227  15.987  24.702  1.00 35.43
ATOM   2551  O   SER B 281      38.363  15.957  25.929  1.00 35.12
ATOM   2552  N   PRO B 282      39.002  16.750  23.921  1.00 36.87
ATOM   2553  CD  PRO B 282      39.175  16.574  22.466  1.00 36.87
ATOM   2554  CA  PRO B 282      40.026  17.645  24.453  1.00 38.02
ATOM   2555  CB  PRO B 282      40.523  18.346  23.201  1.00 37.56
ATOM   2556  CG  PRO B 282      40.519  17.218  22.218  1.00 37.30
ATOM   2557  C   PRO B 282      39.427  18.623  25.455  1.00 38.94
ATOM   2558  O   PRO B 282      40.048  18.939  26.458  1.00 40.29
ATOM   2559  N   ASP B 283      38.207  19.081  25.195  1.00 40.57
ATOM   2560  CA  ASP B 283      37.539  20.012  26.099  1.00 41.40
ATOM   2561  CB  ASP B 283      36.313  20.653  25.435  1.00 43.73
ATOM   2562  CG  ASP B 283      36.675  21.862  24.555  1.00 44.93
ATOM   2563  OD1 ASP B 283      37.879  22.142  24.337  1.00 45.23
ATOM   2564  OD2 ASP B 283      35.739  22.546  24.085  1.00 46.39
ATOM   2565  C   ASP B 283      37.170  19.368  27.428  1.00 39.58
ATOM   2566  O   ASP B 283      37.181  20.026  28.458  1.00 40.67
ATOM   2567  N   ALA B 284      36.856  18.080  27.408  1.00 38.76
ATOM   2568  CA  ALA B 284      36.529  17.372  28.641  1.00 38.27
ATOM   2569  CB  ALA B 284      35.835  16.051  28.337  1.00 37.46
ATOM   2570  C   ALA B 284      37.805  17.120  29.450  1.00 38.40
ATOM   2571  O   ALA B 284      37.812  17.296  30.659  1.00 40.22
ATOM   2572  N   PHE B 285      38.875  16.705  28.765  1.00 37.47
ATOM   2573  CA  PHE B 285      40.181  16.415  29.374  1.00 34.51
ATOM   2574  CB  PHE B 285      41.154  15.935  28.286  1.00 31.02
ATOM   2575  CG  PHE B 285      42.545  15.658  28.778  1.00 28.30
ATOM   2576  CD1 PHE B 285      42.821  14.515  29.517  1.00 27.45
ATOM   2577  CD2 PHE B 285      43.585  16.537  28.494  1.00 26.33
ATOM   2578  CE1 PHE B 285      44.102  14.253  29.963  1.00 25.69
ATOM   2579  CE2 PHE B 285      44.863  16.278  28.939  1.00 24.61
ATOM   2580  CZ  PHE B 285      45.120  15.135  29.673  1.00 25.17
ATOM   2581  C   PHE B 285      40.733  17.656  30.063  1.00 35.37
ATOM   2582  O   PHE B 285      41.100  17.622  31.239  1.00 33.44
ATOM   2583  N   LEU B 286      40.740  18.755  29.315  1.00 36.42
```

Figure 6

| | | | | | | | | | |
|---|---|---|---|---|---|---|---|---|---|
| ATOM | 2584 | CA | LEU | B | 286 | 41.233 | 20.047 | 29.785 | 1.00 38.12 |
| ATOM | 2585 | CB | LEU | B | 286 | 41.278 | 21.042 | 28.625 | 1.00 36.82 |
| ATOM | 2586 | CG | LEU | B | 286 | 42.383 | 20.795 | 27.609 | 1.00 36.31 |
| ATOM | 2587 | CD1 | LEU | B | 286 | 42.126 | 21.633 | 26.371 | 1.00 36.61 |
| ATOM | 2588 | CD2 | LEU | B | 286 | 43.737 | 21.107 | 28.235 | 1.00 35.48 |
| ATOM | 2589 | C | LEU | B | 286 | 40.399 | 20.645 | 30.902 | 1.00 38.92 |
| ATOM | 2590 | O | LEU | B | 286 | 40.930 | 21.331 | 31.773 | 1.00 39.23 |
| ATOM | 2591 | N | ALA | B | 287 | 39.086 | 20.428 | 30.836 | 1.00 40.94 |
| ATOM | 2592 | CA | ALA | B | 287 | 38.166 | 20.958 | 31.844 | 1.00 41.92 |
| ATOM | 2593 | CB | ALA | B | 287 | 36.717 | 20.756 | 31.403 | 1.00 41.52 |
| ATOM | 2594 | C | ALA | B | 287 | 38.410 | 20.304 | 33.203 | 1.00 41.48 |
| ATOM | 2595 | O | ALA | B | 287 | 38.209 | 20.937 | 34.241 | 1.00 42.75 |
| ATOM | 2596 | N | GLU | B | 288 | 38.865 | 19.050 | 33.182 | 1.00 40.02 |
| ATOM | 2597 | CA | GLU | B | 288 | 39.152 | 18.313 | 34.405 | 1.00 40.65 |
| ATOM | 2598 | CB | GLU | B | 288 | 39.540 | 16.847 | 34.100 | 1.00 39.30 |
| ATOM | 2599 | CG | GLU | B | 288 | 38.444 | 16.015 | 33.432 | 1.00 38.95 |
| ATOM | 2600 | CD | GLU | B | 288 | 38.727 | 14.510 | 33.408 | 1.00 39.58 |
| ATOM | 2601 | OE1 | GLU | B | 288 | 39.885 | 14.094 | 33.171 | 1.00 40.41 |
| ATOM | 2602 | OE2 | GLU | B | 288 | 37.785 | 13.720 | 33.606 | 1.00 39.51 |
| ATOM | 2603 | C | GLU | B | 288 | 40.272 | 19.019 | 35.177 | 1.00 42.06 |
| ATOM | 2604 | O | GLU | B | 288 | 40.360 | 18.895 | 36.396 | 1.00 44.37 |
| ATOM | 2605 | N | ALA | B | 289 | 41.114 | 19.768 | 34.460 | 1.00 42.18 |
| ATOM | 2606 | CA | ALA | B | 289 | 42.229 | 20.497 | 35.070 | 1.00 40.64 |
| ATOM | 2607 | CB | ALA | B | 289 | 43.342 | 20.718 | 34.060 | 1.00 42.10 |
| ATOM | 2608 | C | ALA | B | 289 | 41.825 | 21.814 | 35.690 | 1.00 40.03 |
| ATOM | 2609 | O | ALA | B | 289 | 42.620 | 22.409 | 36.415 | 1.00 40.96 |
| ATOM | 2610 | N | ASN | B | 290 | 40.618 | 22.295 | 35.384 | 1.00 39.66 |
| ATOM | 2611 | CA | ASN | B | 290 | 40.129 | 23.555 | 35.968 | 1.00 39.36 |
| ATOM | 2612 | CB | ASN | B | 290 | 38.793 | 23.977 | 35.355 | 1.00 40.92 |
| ATOM | 2613 | CG | ASN | B | 290 | 38.888 | 24.236 | 33.883 | 1.00 41.92 |
| ATOM | 2614 | OD1 | ASN | B | 290 | 37.945 | 23.964 | 33.149 | 1.00 42.16 |
| ATOM | 2615 | ND2 | ASN | B | 290 | 40.023 | 24.774 | 33.437 | 1.00 41.75 |
| ATOM | 2616 | C | ASN | B | 290 | 39.939 | 23.376 | 37.472 | 1.00 37.87 |
| ATOM | 2617 | O | ASN | B | 290 | 39.904 | 24.340 | 38.230 | 1.00 37.86 |
| ATOM | 2618 | N | LEU | B | 291 | 39.790 | 22.127 | 37.887 | 1.00 36.35 |
| ATOM | 2619 | CA | LEU | B | 291 | 39.632 | 21.797 | 39.282 | 1.00 35.78 |
| ATOM | 2620 | CB | LEU | B | 291 | 39.308 | 20.310 | 39.422 | 1.00 35.42 |
| ATOM | 2621 | CG | LEU | B | 291 | 37.956 | 20.050 | 38.754 | 1.00 34.92 |
| ATOM | 2622 | CD1 | LEU | B | 291 | 37.772 | 18.602 | 38.429 | 1.00 34.99 |
| ATOM | 2623 | CD2 | LEU | B | 291 | 36.850 | 20.551 | 39.638 | 1.00 34.77 |
| ATOM | 2624 | C | LEU | B | 291 | 40.907 | 22.192 | 40.035 | 1.00 35.90 |
| ATOM | 2625 | O | LEU | B | 291 | 40.826 | 22.677 | 41.159 | 1.00 36.01 |
| ATOM | 2626 | N | MET | B | 292 | 42.073 | 22.050 | 39.400 | 1.00 35.10 |
| ATOM | 2627 | CA | MET | B | 292 | 43.324 | 22.457 | 40.045 | 1.00 33.51 |
| ATOM | 2628 | CB | MET | B | 292 | 44.519 | 21.763 | 39.417 | 1.00 31.36 |
| ATOM | 2629 | CG | MET | B | 292 | 44.650 | 20.341 | 39.847 | 1.00 29.89 |
| ATOM | 2630 | SD | MET | B | 292 | 45.988 | 19.488 | 39.025 | 1.00 26.90 |
| ATOM | 2631 | CE | MET | B | 292 | 45.252 | 19.230 | 37.409 | 1.00 27.22 |
| ATOM | 2632 | C | MET | B | 292 | 43.525 | 23.964 | 40.006 | 1.00 35.26 |
| ATOM | 2633 | O | MET | B | 292 | 44.446 | 24.485 | 40.624 | 1.00 35.91 |
| ATOM | 2634 | N | LYS | B | 293 | 42.686 | 24.660 | 39.246 | 1.00 37.77 |
| ATOM | 2635 | CA | LYS | B | 293 | 42.766 | 26.111 | 39.167 | 1.00 40.45 |
| ATOM | 2636 | CB | LYS | B | 293 | 42.242 | 26.627 | 37.819 | 1.00 40.92 |
| ATOM | 2637 | CG | LYS | B | 293 | 43.059 | 26.201 | 36.611 | 1.00 42.03 |
| ATOM | 2638 | CD | LYS | B | 293 | 42.499 | 26.790 | 35.320 | 1.00 42.36 |
| ATOM | 2639 | CE | LYS | B | 293 | 43.178 | 26.172 | 34.099 | 1.00 43.08 |
| ATOM | 2640 | NZ | LYS | B | 293 | 42.684 | 26.737 | 32.814 | 1.00 43.48 |
| ATOM | 2641 | C | LYS | B | 293 | 41.919 | 26.692 | 40.289 | 1.00 41.75 |
| ATOM | 2642 | O | LYS | B | 293 | 42.245 | 27.742 | 40.857 | 1.00 42.69 |

Figure 6

| | | | | | | | | | |
|---|---|---|---|---|---|---|---|---|---|
| ATOM | 2643 | N | GLN | B | 294 | 40.836 | 25.989 | 40.613 | 1.00 43.15 |
| ATOM | 2644 | CA | GLN | B | 294 | 39.902 | 26.415 | 41.660 | 1.00 44.35 |
| ATOM | 2645 | CB | GLN | B | 294 | 38.486 | 25.883 | 41.366 | 1.00 45.59 |
| ATOM | 2646 | CG | GLN | B | 294 | 37.959 | 26.181 | 39.952 | 1.00 48.81 |
| ATOM | 2647 | CD | GLN | B | 294 | 38.068 | 27.659 | 39.542 | 1.00 51.50 |
| ATOM | 2648 | OE1 | GLN | B | 294 | 38.708 | 27.995 | 38.528 | 1.00 52.12 |
| ATOM | 2649 | NE2 | GLN | B | 294 | 37.429 | 28.546 | 40.313 | 1.00 51.83 |
| ATOM | 2650 | C | GLN | B | 294 | 40.322 | 26.093 | 43.118 | 1.00 43.69 |
| ATOM | 2651 | O | GLN | B | 294 | 39.993 | 26.847 | 44.044 | 1.00 44.24 |
| ATOM | 2652 | N | LEU | B | 295 | 41.047 | 24.992 | 43.320 | 1.00 42.01 |
| ATOM | 2653 | CA | LEU | B | 295 | 41.496 | 24.618 | 44.665 | 1.00 40.85 |
| ATOM | 2654 | CB | LEU | B | 295 | 40.847 | 23.301 | 45.095 | 1.00 41.39 |
| ATOM | 2655 | CG | LEU | B | 295 | 39.325 | 23.212 | 45.137 | 1.00 40.84 |
| ATOM | 2656 | CD1 | LEU | B | 295 | 38.932 | 21.796 | 45.460 | 1.00 40.71 |
| ATOM | 2657 | CD2 | LEU | B | 295 | 38.776 | 24.179 | 46.175 | 1.00 41.44 |
| ATOM | 2658 | C | LEU | B | 295 | 43.015 | 24.480 | 44.757 | 1.00 40.36 |
| ATOM | 2659 | O | LEU | B | 295 | 43.590 | 23.532 | 44.224 | 1.00 40.24 |
| ATOM | 2660 | N | GLN | B | 296 | 43.659 | 25.410 | 45.456 | 1.00 39.80 |
| ATOM | 2661 | CA | GLN | B | 296 | 45.112 | 25.377 | 45.613 | 1.00 39.38 |
| ATOM | 2662 | CB | GLN | B | 296 | 45.719 | 26.661 | 45.062 | 1.00 40.76 |
| ATOM | 2663 | CG | GLN | B | 296 | 45.242 | 26.988 | 43.651 | 1.00 42.46 |
| ATOM | 2664 | CD | GLN | B | 296 | 45.899 | 28.229 | 43.082 | 1.00 44.01 |
| ATOM | 2665 | OE1 | GLN | B | 296 | 46.429 | 29.055 | 43.817 | 1.00 45.49 |
| ATOM | 2666 | NE2 | GLN | B | 296 | 45.897 | 28.346 | 41.758 | 1.00 45.40 |
| ATOM | 2667 | C | GLN | B | 296 | 45.465 | 25.195 | 47.081 | 1.00 38.22 |
| ATOM | 2668 | O | GLN | B | 296 | 44.980 | 25.938 | 47.938 | 1.00 39.28 |
| ATOM | 2669 | N | HIS | B | 297 | 46.311 | 24.215 | 47.375 | 1.00 35.78 |
| ATOM | 2670 | CA | HIS | B | 297 | 46.680 | 23.941 | 48.755 | 1.00 34.65 |
| ATOM | 2671 | CB | HIS | B | 297 | 45.513 | 23.217 | 49.435 | 1.00 32.80 |
| ATOM | 2672 | CG | HIS | B | 297 | 45.649 | 23.103 | 50.920 | 1.00 32.18 |
| ATOM | 2673 | CD2 | HIS | B | 297 | 45.254 | 23.920 | 51.917 | 1.00 31.50 |
| ATOM | 2674 | ND1 | HIS | B | 297 | 46.262 | 22.027 | 51.532 | 1.00 31.70 |
| ATOM | 2675 | CE1 | HIS | B | 297 | 46.239 | 22.192 | 52.836 | 1.00 30.77 |
| ATOM | 2676 | NE2 | HIS | B | 297 | 45.631 | 23.335 | 53.105 | 1.00 31.08 |
| ATOM | 2677 | C | HIS | B | 297 | 47.929 | 23.067 | 48.807 | 1.00 35.17 |
| ATOM | 2678 | O | HIS | B | 297 | 48.180 | 22.291 | 47.881 | 1.00 34.38 |
| ATOM | 2679 | N | GLN | B | 298 | 48.683 | 23.157 | 49.906 | 1.00 36.04 |
| ATOM | 2680 | CA | GLN | B | 298 | 49.898 | 22.363 | 50.055 | 1.00 38.29 |
| ATOM | 2681 | CB | GLN | B | 298 | 50.674 | 22.758 | 51.320 | 1.00 43.19 |
| ATOM | 2682 | CG | GLN | B | 298 | 51.631 | 23.951 | 51.131 | 1.00 49.73 |
| ATOM | 2683 | CD | GLN | B | 298 | 52.568 | 23.789 | 49.910 | 1.00 52.93 |
| ATOM | 2684 | OE1 | GLN | B | 298 | 52.771 | 24.735 | 49.125 | 1.00 53.63 |
| ATOM | 2685 | NE2 | GLN | B | 298 | 53.127 | 22.583 | 49.743 | 1.00 53.74 |
| ATOM | 2686 | C | GLN | B | 298 | 49.678 | 20.858 | 50.029 | 1.00 36.70 |
| ATOM | 2687 | O | GLN | B | 298 | 50.600 | 20.095 | 49.778 | 1.00 36.57 |
| ATOM | 2688 | N | ARG | B | 299 | 48.447 | 20.436 | 50.262 | 1.00 35.43 |
| ATOM | 2689 | CA | ARG | B | 299 | 48.108 | 19.015 | 50.263 | 1.00 34.50 |
| ATOM | 2690 | CB | ARG | B | 299 | 47.238 | 18.696 | 51.471 | 1.00 34.85 |
| ATOM | 2691 | CG | ARG | B | 299 | 47.931 | 18.952 | 52.784 | 1.00 35.85 |
| ATOM | 2692 | CD | ARG | B | 299 | 49.032 | 17.955 | 53.015 | 1.00 35.25 |
| ATOM | 2693 | NE | ARG | B | 299 | 50.103 | 18.567 | 53.776 | 1.00 37.33 |
| ATOM | 2694 | CZ | ARG | B | 299 | 51.375 | 18.561 | 53.397 | 1.00 38.90 |
| ATOM | 2695 | NH1 | ARG | B | 299 | 51.733 | 17.966 | 52.261 | 1.00 38.63 |
| ATOM | 2696 | NH2 | ARG | B | 299 | 52.292 | 19.127 | 54.168 | 1.00 39.41 |
| ATOM | 2697 | C | ARG | B | 299 | 47.412 | 18.528 | 48.980 | 1.00 33.66 |
| ATOM | 2698 | O | ARG | B | 299 | 47.070 | 17.349 | 48.863 | 1.00 32.09 |
| ATOM | 2699 | N | LEU | B | 300 | 47.172 | 19.447 | 48.046 | 1.00 33.61 |
| ATOM | 2700 | CA | LEU | B | 300 | 46.544 | 19.126 | 46.762 | 1.00 31.54 |
| ATOM | 2701 | CB | LEU | B | 300 | 45.375 | 20.078 | 46.498 | 1.00 29.58 |

Figure 6

| ATOM | 2702 | CG | LEU | B | 300 | 43.972 | 19.721 | 46.999 | 1.00 | 28.29 |
|---|---|---|---|---|---|---|---|---|---|---|
| ATOM | 2703 | CD1 | LEU | B | 300 | 43.987 | 19.119 | 48.378 | 1.00 | 26.61 |
| ATOM | 2704 | CD2 | LEU | B | 300 | 43.124 | 20.980 | 46.969 | 1.00 | 27.82 |
| ATOM | 2705 | C | LEU | B | 300 | 47.596 | 19.269 | 45.653 | 1.00 | 32.02 |
| ATOM | 2706 | O | LEU | B | 300 | 48.484 | 20.131 | 45.740 | 1.00 | 31.97 |
| ATOM | 2707 | N | VAL | B | 301 | 47.518 | 18.385 | 44.653 | 1.00 | 32.73 |
| ATOM | 2708 | CA | VAL | B | 301 | 48.428 | 18.393 | 43.500 | 1.00 | 31.61 |
| ATOM | 2709 | CB | VAL | B | 301 | 48.076 | 17.269 | 42.519 | 1.00 | 30.59 |
| ATOM | 2710 | CG1 | VAL | B | 301 | 48.739 | 17.510 | 41.180 | 1.00 | 31.54 |
| ATOM | 2711 | CG2 | VAL | B | 301 | 48.513 | 15.927 | 43.086 | 1.00 | 30.61 |
| ATOM | 2712 | C | VAL | B | 301 | 48.293 | 19.737 | 42.795 | 1.00 | 32.77 |
| ATOM | 2713 | O | VAL | B | 301 | 47.187 | 20.157 | 42.458 | 1.00 | 32.51 |
| ATOM | 2714 | N | ARG | B | 302 | 49.424 | 20.396 | 42.568 | 1.00 | 34.64 |
| ATOM | 2715 | CA | ARG | B | 302 | 49.458 | 21.722 | 41.952 | 1.00 | 35.29 |
| ATOM | 2716 | CB | ARG | B | 302 | 50.607 | 22.518 | 42.591 | 1.00 | 37.56 |
| ATOM | 2717 | CG | ARG | B | 302 | 50.807 | 23.930 | 42.098 | 1.00 | 40.90 |
| ATOM | 2718 | CD | ARG | B | 302 | 51.848 | 23.972 | 40.981 | 1.00 | 44.59 |
| ATOM | 2719 | NE | ARG | B | 302 | 52.356 | 25.322 | 40.723 | 1.00 | 47.45 |
| ATOM | 2720 | CZ | ARG | B | 302 | 53.117 | 26.014 | 41.574 | 1.00 | 48.51 |
| ATOM | 2721 | NH1 | ARG | B | 302 | 53.465 | 25.496 | 42.749 | 1.00 | 48.43 |
| ATOM | 2722 | NH2 | ARG | B | 302 | 53.552 | 27.219 | 41.238 | 1.00 | 49.50 |
| ATOM | 2723 | C | ARG | B | 302 | 49.554 | 21.715 | 40.418 | 1.00 | 34.05 |
| ATOM | 2724 | O | ARG | B | 302 | 50.204 | 20.846 | 39.824 | 1.00 | 33.33 |
| ATOM | 2725 | N | LEU | B | 303 | 48.862 | 22.666 | 39.788 | 1.00 | 32.63 |
| ATOM | 2726 | CA | LEU | B | 303 | 48.869 | 22.808 | 38.326 | 1.00 | 31.40 |
| ATOM | 2727 | CB | LEU | B | 303 | 47.466 | 23.136 | 37.794 | 1.00 | 28.46 |
| ATOM | 2728 | CG | LEU | B | 303 | 47.328 | 23.383 | 36.281 | 1.00 | 27.11 |
| ATOM | 2729 | CD1 | LEU | B | 303 | 47.418 | 22.072 | 35.535 | 1.00 | 26.69 |
| ATOM | 2730 | CD2 | LEU | B | 303 | 46.011 | 24.074 | 35.932 | 1.00 | 24.47 |
| ATOM | 2731 | C | LEU | B | 303 | 49.821 | 23.939 | 37.917 | 1.00 | 31.54 |
| ATOM | 2732 | O | LEU | B | 303 | 49.862 | 24.986 | 38.576 | 1.00 | 30.76 |
| ATOM | 2733 | N | TYR | B | 304 | 50.609 | 23.699 | 36.865 | 1.00 | 31.70 |
| ATOM | 2734 | CA | TYR | B | 304 | 51.537 | 24.692 | 36.324 | 1.00 | 31.77 |
| ATOM | 2735 | CB | TYR | B | 304 | 52.890 | 24.052 | 36.010 | 1.00 | 33.80 |
| ATOM | 2736 | CG | TYR | B | 304 | 53.776 | 23.791 | 37.208 | 1.00 | 35.87 |
| ATOM | 2737 | CD1 | TYR | B | 304 | 53.907 | 22.506 | 37.729 | 1.00 | 37.55 |
| ATOM | 2738 | CE1 | TYR | B | 304 | 54.752 | 22.247 | 38.803 | 1.00 | 38.50 |
| ATOM | 2739 | CD2 | TYR | B | 304 | 54.518 | 24.822 | 37.798 | 1.00 | 37.53 |
| ATOM | 2740 | CE2 | TYR | B | 304 | 55.374 | 24.572 | 38.882 | 1.00 | 38.34 |
| ATOM | 2741 | CZ | TYR | B | 304 | 55.480 | 23.278 | 39.372 | 1.00 | 38.49 |
| ATOM | 2742 | OH | TYR | B | 304 | 56.315 | 22.996 | 40.419 | 1.00 | 38.12 |
| ATOM | 2743 | C | TYR | B | 304 | 50.948 | 25.265 | 35.026 | 1.00 | 31.79 |
| ATOM | 2744 | O | TYR | B | 304 | 50.787 | 26.470 | 34.877 | 1.00 | 32.82 |
| ATOM | 2745 | N | ALA | B | 305 | 50.595 | 24.396 | 34.091 | 1.00 | 30.93 |
| ATOM | 2746 | CA | ALA | B | 305 | 50.035 | 24.865 | 32.841 | 1.00 | 30.00 |
| ATOM | 2747 | CB | ALA | B | 305 | 51.105 | 25.588 | 32.044 | 1.00 | 30.30 |
| ATOM | 2748 | C | ALA | B | 305 | 49.452 | 23.737 | 32.015 | 1.00 | 30.43 |
| ATOM | 2749 | O | ALA | B | 305 | 49.526 | 22.563 | 32.389 | 1.00 | 26.21 |
| ATOM | 2750 | N | VAL | B | 306 | 48.867 | 24.119 | 30.881 | 1.00 | 32.96 |
| ATOM | 2751 | CA | VAL | B | 306 | 48.266 | 23.172 | 29.939 | 1.00 | 35.15 |
| ATOM | 2752 | CB | VAL | B | 306 | 46.710 | 23.146 | 30.052 | 1.00 | 35.61 |
| ATOM | 2753 | CG1 | VAL | B | 306 | 46.266 | 22.555 | 31.399 | 1.00 | 35.09 |
| ATOM | 2754 | CG2 | VAL | B | 306 | 46.141 | 24.551 | 29.858 | 1.00 | 35.46 |
| ATOM | 2755 | C | VAL | B | 306 | 48.633 | 23.502 | 28.482 | 1.00 | 35.65 |
| ATOM | 2756 | O | VAL | B | 306 | 48.880 | 24.659 | 28.142 | 1.00 | 35.11 |
| ATOM | 2757 | N | VAL | B | 307 | 48.727 | 22.464 | 27.651 | 1.00 | 36.54 |
| ATOM | 2758 | CA | VAL | B | 307 | 49.015 | 22.617 | 26.227 | 1.00 | 36.89 |
| ATOM | 2759 | CB | VAL | B | 307 | 50.270 | 21.846 | 25.788 | 1.00 | 35.19 |
| ATOM | 2760 | CG1 | VAL | B | 307 | 50.458 | 21.962 | 24.285 | 1.00 | 34.73 |

Figure 6

```
ATOM   2761  CG2  VAL B 307      51.474  22.409  26.497  1.00 33.44
ATOM   2762  C    VAL B 307      47.775  22.130  25.477  1.00 38.90
ATOM   2763  O    VAL B 307      47.439  20.937  25.455  1.00 36.56
ATOM   2764  N    THR B 308      47.084  23.095  24.893  1.00 42.23
ATOM   2765  CA   THR B 308      45.846  22.846  24.180  1.00 46.54
ATOM   2766  CB   THR B 308      44.974  24.106  24.230  1.00 47.52
ATOM   2767  OG1  THR B 308      45.750  25.232  23.793  1.00 48.64
ATOM   2768  CG2  THR B 308      44.506  24.362  25.684  1.00 47.94
ATOM   2769  C    THR B 308      45.886  22.247  22.759  1.00 48.59
ATOM   2770  O    THR B 308      44.885  21.685  22.313  1.00 48.67
ATOM   2771  N    GLN B 309      47.022  22.330  22.059  1.00 50.37
ATOM   2772  CA   GLN B 309      47.133  21.755  20.713  1.00 51.23
ATOM   2773  CB   GLN B 309      48.112  22.567  19.845  1.00 51.25
ATOM   2774  CG   GLN B 309      47.636  23.966  19.507  0.00 51.61
ATOM   2775  CD   GLN B 309      46.359  23.977  18.687  0.00 51.69
ATOM   2776  OE1  GLN B 309      45.790  22.930  18.367  0.00 51.74
ATOM   2777  NE2  GLN B 309      45.905  25.169  18.338  0.00 51.78
ATOM   2778  C    GLN B 309      47.565  20.286  20.779  1.00 51.49
ATOM   2779  O    GLN B 309      48.488  19.943  21.522  1.00 50.74
ATOM   2780  N    GLU B 310      46.895  19.428  20.001  1.00 52.14
ATOM   2781  CA   GLU B 310      47.194  17.989  19.966  1.00 53.39
ATOM   2782  CB   GLU B 310      46.299  17.253  18.948  1.00 53.96
ATOM   2783  CG   GLU B 310      46.244  17.847  17.549  0.00 54.16
ATOM   2784  CD   GLU B 310      45.046  18.751  17.343  0.00 54.38
ATOM   2785  OE1  GLU B 310      43.936  18.401  17.799  0.00 54.40
ATOM   2786  OE2  GLU B 310      45.216  19.809  16.709  0.00 54.55
ATOM   2787  C    GLU B 310      48.669  17.655  19.693  1.00 53.26
ATOM   2788  O    GLU B 310      49.255  18.166  18.728  1.00 54.04
ATOM   2789  N    PRO B 311      49.300  16.804  20.554  1.00 52.53
ATOM   2790  CD   PRO B 311      50.667  16.305  20.327  1.00 52.14
ATOM   2791  CA   PRO B 311      48.720  16.155  21.747  1.00 50.84
ATOM   2792  CB   PRO B 311      49.783  15.100  22.119  1.00 51.03
ATOM   2793  CG   PRO B 311      50.573  14.900  20.857  1.00 51.57
ATOM   2794  C    PRO B 311      48.476  17.128  22.918  1.00 48.55
ATOM   2795  O    PRO B 311      49.330  17.963  23.242  1.00 48.30
ATOM   2796  N    ILE B 312      47.309  17.004  23.554  1.00 45.41
ATOM   2797  CA   ILE B 312      46.950  17.866  24.680  1.00 41.74
ATOM   2798  CB   ILE B 312      45.431  17.762  25.027  1.00 43.02
ATOM   2799  CG2  ILE B 312      44.970  19.037  25.721  1.00 43.60
ATOM   2800  CG1  ILE B 312      44.580  17.491  23.770  1.00 42.22
ATOM   2801  CD1  ILE B 312      44.581  18.599  22.752  1.00 41.60
ATOM   2802  C    ILE B 312      47.752  17.425  25.902  1.00 37.94
ATOM   2803  O    ILE B 312      47.915  16.216  26.125  1.00 35.28
ATOM   2804  N    TYR B 313      48.217  18.402  26.688  1.00 35.20
ATOM   2805  CA   TYR B 313      49.016  18.160  27.907  1.00 32.53
ATOM   2806  CB   TYR B 313      50.472  18.600  27.725  1.00 32.89
ATOM   2807  CG   TYR B 313      51.360  17.820  26.784  1.00 33.11
ATOM   2808  CD1  TYR B 313      51.089  16.504  26.441  1.00 33.33
ATOM   2809  CE1  TYR B 313      51.953  15.795  25.615  1.00 34.09
ATOM   2810  CD2  TYR B 313      52.518  18.404  26.274  1.00 33.24
ATOM   2811  CE2  TYR B 313      53.381  17.705  25.455  1.00 33.46
ATOM   2812  CZ   TYR B 313      53.096  16.405  25.131  1.00 34.18
ATOM   2813  OH   TYR B 313      53.956  15.702  24.317  1.00 36.66
ATOM   2814  C    TYR B 313      48.565  18.946  29.144  1.00 31.53
ATOM   2815  O    TYR B 313      48.273  20.136  29.071  1.00 31.00
ATOM   2816  N    ILE B 314      48.612  18.290  30.299  1.00 29.61
ATOM   2817  CA   ILE B 314      48.315  18.938  31.571  1.00 27.72
ATOM   2818  CB   ILE B 314      47.172  18.238  32.348  1.00 27.83
ATOM   2819  CG2  ILE B 314      47.136  18.737  33.792  1.00 26.69
```

Figure 6

```
ATOM   2820  CG1 ILE B 314      45.830  18.517  31.652  1.00 27.69
ATOM   2821  CD1 ILE B 314      44.656  17.734  32.207  1.00 28.12
ATOM   2822  C   ILE B 314      49.635  18.825  32.323  1.00 25.98
ATOM   2823  O   ILE B 314      50.172  17.734  32.453  1.00 23.32
ATOM   2824  N   ILE B 315      50.200  19.966  32.700  1.00 25.82
ATOM   2825  CA  ILE B 315      51.478  20.010  33.398  1.00 28.42
ATOM   2826  CB  ILE B 315      52.429  21.116  32.828  1.00 29.78
ATOM   2827  CG2 ILE B 315      53.695  21.211  33.660  1.00 28.81
ATOM   2828  CG1 ILE B 315      52.811  20.823  31.377  1.00 30.47
ATOM   2829  CD1 ILE B 315      51.934  21.494  30.368  1.00 31.22
ATOM   2830  C   ILE B 315      51.297  20.266  34.892  1.00 29.09
ATOM   2831  O   ILE B 315      50.907  21.358  35.306  1.00 29.06
ATOM   2832  N   THR B 316      51.634  19.270  35.702  1.00 27.79
ATOM   2833  CA  THR B 316      51.494  19.404  37.142  1.00 28.28
ATOM   2834  CB  THR B 316      50.485  18.387  37.725  1.00 26.98
ATOM   2835  OG1 THR B 316      50.937  17.051  37.453  1.00 26.88
ATOM   2836  CG2 THR B 316      49.106  18.601  37.137  1.00 24.66
ATOM   2837  C   THR B 316      52.830  19.141  37.798  1.00 29.89
ATOM   2838  O   THR B 316      53.746  18.623  37.166  1.00 31.00
ATOM   2839  N   GLU B 317      52.931  19.490  39.079  1.00 30.39
ATOM   2840  CA  GLU B 317      54.156  19.262  39.838  1.00 28.41
ATOM   2841  CB  GLU B 317      53.975  19.695  41.288  1.00 28.56
ATOM   2842  CG  GLU B 317      52.971  18.857  42.046  1.00 28.33
ATOM   2843  CD  GLU B 317      52.898  19.241  43.486  1.00 27.50
ATOM   2844  OE1 GLU B 317      51.781  19.540  43.957  1.00 27.21
ATOM   2845  OE2 GLU B 317      53.965  19.254  44.139  1.00 28.89
ATOM   2846  C   GLU B 317      54.487  17.786  39.800  1.00 25.75
ATOM   2847  O   GLU B 317      53.608  16.950  39.579  1.00 24.15
ATOM   2848  N   TYR B 318      55.765  17.477  39.977  1.00 25.19
ATOM   2849  CA  TYR B 318      56.226  16.093  39.963  1.00 24.32
ATOM   2850  CB  TYR B 318      57.626  16.023  39.333  1.00 21.98
ATOM   2851  CG  TYR B 318      58.241  14.656  39.329  1.00 20.86
ATOM   2852  CD1 TYR B 318      57.757  13.663  38.495  1.00 20.96
ATOM   2853  CE1 TYR B 318      58.317  12.399  38.482  1.00 21.41
ATOM   2854  CD2 TYR B 318      59.306  14.356  40.157  1.00 20.22
ATOM   2855  CE2 TYR B 318      59.877  13.098  40.153  1.00 20.63
ATOM   2856  CZ  TYR B 318      59.380  12.120  39.312  1.00 21.95
ATOM   2857  OH  TYR B 318      59.945  10.855  39.291  1.00 23.52
ATOM   2858  C   TYR B 318      56.238  15.560  41.396  1.00 24.38
ATOM   2859  O   TYR B 318      56.572  16.288  42.325  1.00 25.13
ATOM   2860  N   MET B 319      55.818  14.314  41.570  1.00 24.00
ATOM   2861  CA  MET B 319      55.794  13.672  42.874  1.00 25.59
ATOM   2862  CB  MET B 319      54.360  13.334  43.285  1.00 25.37
ATOM   2863  CG  MET B 319      53.475  14.557  43.612  1.00 26.62
ATOM   2864  SD  MET B 319      53.856  15.466  45.178  1.00 28.75
ATOM   2865  CE  MET B 319      53.265  14.298  46.395  1.00 27.43
ATOM   2866  C   MET B 319      56.661  12.416  42.770  1.00 27.86
ATOM   2867  O   MET B 319      56.227  11.358  42.306  1.00 27.24
ATOM   2868  N   GLU B 320      57.914  12.576  43.176  1.00 31.24
ATOM   2869  CA  GLU B 320      58.942  11.533  43.131  1.00 33.53
ATOM   2870  CB  GLU B 320      60.087  11.924  44.069  1.00 37.68
ATOM   2871  CG  GLU B 320      61.065  10.793  44.419  1.00 42.21
ATOM   2872  CD  GLU B 320      62.347  10.826  43.612  1.00 44.17
ATOM   2873  OE1 GLU B 320      62.641  11.850  42.960  1.00 46.41
ATOM   2874  OE2 GLU B 320      63.073   9.817  43.648  1.00 45.46
ATOM   2875  C   GLU B 320      58.555  10.071  43.377  1.00 32.53
ATOM   2876  O   GLU B 320      58.905   9.184  42.575  1.00 33.28
ATOM   2877  N   ASN B 321      57.865   9.802  44.480  1.00 29.61
ATOM   2878  CA  ASN B 321      57.500   8.431  44.785  1.00 27.37
```

Figure 6

| | | | | | | | | | |
|---|---|---|---|---|---|---|---|---|---|
| ATOM | 2879 | CB  | ASN | B | 321 | 57.633 | 8.180  | 46.270 | 1.00 28.33 |
| ATOM | 2880 | CG  | ASN | B | 321 | 59.075 | 8.189  | 46.709 | 1.00 26.84 |
| ATOM | 2881 | OD1 | ASN | B | 321 | 59.858 | 7.347  | 46.281 | 1.00 26.71 |
| ATOM | 2882 | ND2 | ASN | B | 321 | 59.440 | 9.150  | 47.535 | 1.00 24.91 |
| ATOM | 2883 | C   | ASN | B | 321 | 56.187 | 7.923  | 44.208 | 1.00 27.04 |
| ATOM | 2884 | O   | ASN | B | 321 | 55.717 | 6.822  | 44.540 | 1.00 27.08 |
| ATOM | 2885 | N   | GLY | B | 322 | 55.648 | 8.710  | 43.284 | 1.00 26.70 |
| ATOM | 2886 | CA  | GLY | B | 322 | 54.437 | 8.344  | 42.577 | 1.00 25.35 |
| ATOM | 2887 | C   | GLY | B | 322 | 53.168 | 8.183  | 43.372 | 1.00 24.50 |
| ATOM | 2888 | O   | GLY | B | 322 | 52.795 | 9.053  | 44.152 | 1.00 25.04 |
| ATOM | 2889 | N   | SER | B | 323 | 52.503 | 7.058  | 43.162 | 1.00 22.46 |
| ATOM | 2890 | CA  | SER | B | 323 | 51.243 | 6.779  | 43.813 | 1.00 22.62 |
| ATOM | 2891 | CB  | SER | B | 323 | 50.349 | 5.980  | 42.853 | 1.00 21.96 |
| ATOM | 2892 | OG  | SER | B | 323 | 49.117 | 5.609  | 43.443 | 1.00 23.89 |
| ATOM | 2893 | C   | SER | B | 323 | 51.429 | 6.044  | 45.136 | 1.00 22.79 |
| ATOM | 2894 | O   | SER | B | 323 | 52.138 | 5.042  | 45.206 | 1.00 21.66 |
| ATOM | 2895 | N   | LEU | B | 324 | 50.732 | 6.515  | 46.169 | 1.00 22.81 |
| ATOM | 2896 | CA  | LEU | B | 324 | 50.809 | 5.929  | 47.504 | 1.00 21.75 |
| ATOM | 2897 | CB  | LEU | B | 324 | 49.885 | 6.667  | 48.466 | 1.00 21.29 |
| ATOM | 2898 | CG  | LEU | B | 324 | 49.678 | 6.118  | 49.881 | 1.00 20.10 |
| ATOM | 2899 | CD1 | LEU | B | 324 | 50.968 | 6.262  | 50.660 | 1.00 19.25 |
| ATOM | 2900 | CD2 | LEU | B | 324 | 48.557 | 6.876  | 50.566 | 1.00 18.54 |
| ATOM | 2901 | C   | LEU | B | 324 | 50.512 | 4.443  | 47.561 | 1.00 22.09 |
| ATOM | 2902 | O   | LEU | B | 324 | 51.169 | 3.728  | 48.302 | 1.00 23.60 |
| ATOM | 2903 | N   | VAL | B | 325 | 49.526 | 3.966  | 46.804 | 1.00 23.77 |
| ATOM | 2904 | CA  | VAL | B | 325 | 49.213 | 2.538  | 46.829 | 1.00 24.53 |
| ATOM | 2905 | CB  | VAL | B | 325 | 47.936 | 2.198  | 46.006 | 1.00 22.97 |
| ATOM | 2906 | CG1 | VAL | B | 325 | 48.192 | 2.373  | 44.519 | 1.00 22.49 |
| ATOM | 2907 | CG2 | VAL | B | 325 | 47.456 | 0.783  | 46.322 | 1.00 20.81 |
| ATOM | 2908 | C   | VAL | B | 325 | 50.423 | 1.763  | 46.306 | 1.00 26.41 |
| ATOM | 2909 | O   | VAL | B | 325 | 50.623 | 0.601  | 46.651 | 1.00 26.94 |
| ATOM | 2910 | N   | ASP | B | 326 | 51.236 | 2.436  | 45.489 | 1.00 28.96 |
| ATOM | 2911 | CA  | ASP | B | 326 | 52.448 | 1.843  | 44.926 | 1.00 30.40 |
| ATOM | 2912 | CB  | ASP | B | 326 | 52.810 | 2.506  | 43.592 | 1.00 28.74 |
| ATOM | 2913 | CG  | ASP | B | 326 | 51.905 | 2.074  | 42.474 | 1.00 28.73 |
| ATOM | 2914 | OD1 | ASP | B | 326 | 51.286 | 0.990  | 42.602 | 1.00 26.73 |
| ATOM | 2915 | OD2 | ASP | B | 326 | 51.824 | 2.808  | 41.466 | 1.00 28.73 |
| ATOM | 2916 | C   | ASP | B | 326 | 53.626 | 1.948  | 45.893 | 1.00 31.18 |
| ATOM | 2917 | O   | ASP | B | 326 | 54.337 | 0.971  | 46.125 | 1.00 32.41 |
| ATOM | 2918 | N   | PHE | B | 327 | 53.789 | 3.126  | 46.481 | 1.00 30.53 |
| ATOM | 2919 | CA  | PHE | B | 327 | 54.874 | 3.390  | 47.404 | 1.00 30.97 |
| ATOM | 2920 | CB  | PHE | B | 327 | 54.879 | 4.863  | 47.807 | 1.00 31.38 |
| ATOM | 2921 | CG  | PHE | B | 327 | 55.995 | 5.231  | 48.738 | 1.00 32.82 |
| ATOM | 2922 | CD1 | PHE | B | 327 | 57.320 | 5.186  | 48.307 | 1.00 33.23 |
| ATOM | 2923 | CD2 | PHE | B | 327 | 55.729 | 5.599  | 50.056 | 1.00 32.62 |
| ATOM | 2924 | CE1 | PHE | B | 327 | 58.370 | 5.499  | 49.183 | 1.00 34.66 |
| ATOM | 2925 | CE2 | PHE | B | 327 | 56.764 | 5.913  | 50.939 | 1.00 33.04 |
| ATOM | 2926 | CZ  | PHE | B | 327 | 58.087 | 5.865  | 50.507 | 1.00 33.56 |
| ATOM | 2927 | C   | PHE | B | 327 | 54.880 | 2.500  | 48.642 | 1.00 31.73 |
| ATOM | 2928 | O   | PHE | B | 327 | 55.936 | 2.000  | 49.026 | 1.00 31.65 |
| ATOM | 2929 | N   | LEU | B | 328 | 53.704 | 2.281  | 49.235 | 1.00 31.00 |
| ATOM | 2930 | CA  | LEU | B | 328 | 53.558 | 1.456  | 50.446 | 1.00 29.05 |
| ATOM | 2931 | CB  | LEU | B | 328 | 52.092 | 1.419  | 50.901 | 1.00 27.97 |
| ATOM | 2932 | CG  | LEU | B | 328 | 51.344 | 2.694  | 51.276 | 1.00 26.17 |
| ATOM | 2933 | CD1 | LEU | B | 328 | 49.869 | 2.385  | 51.371 | 1.00 25.16 |
| ATOM | 2934 | CD2 | LEU | B | 328 | 51.885 | 3.272  | 52.578 | 1.00 26.57 |
| ATOM | 2935 | C   | LEU | B | 328 | 54.062 | 0.020  | 50.259 | 1.00 30.46 |
| ATOM | 2936 | O   | LEU | B | 328 | 54.376 | -0.671 | 51.239 | 1.00 31.04 |
| ATOM | 2937 | N   | LYS | B | 329 | 54.102 | -0.432 | 49.004 | 1.00 31.42 |

Figure 6

| | | | | | | | | | |
|---|---|---|---|---|---|---|---|---|---|
| ATOM | 2938 | CA  | LYS | B | 329 | 54.568 | -1.778 | 48.664 | 1.00 30.49 |
| ATOM | 2939 | CB  | LYS | B | 329 | 53.847 | -2.312 | 47.426 | 1.00 29.88 |
| ATOM | 2940 | CG  | LYS | B | 329 | 52.357 | -2.433 | 47.545 | 1.00 29.99 |
| ATOM | 2941 | CD  | LYS | B | 329 | 51.847 | -3.446 | 46.551 | 1.00 31.38 |
| ATOM | 2942 | CE  | LYS | B | 329 | 50.341 | -3.409 | 46.448 | 1.00 32.98 |
| ATOM | 2943 | NZ  | LYS | B | 329 | 49.906 | -2.050 | 46.050 | 1.00 34.08 |
| ATOM | 2944 | C   | LYS | B | 329 | 56.079 | -1.870 | 48.423 | 1.00 30.26 |
| ATOM | 2945 | O   | LYS | B | 329 | 56.647 | -2.960 | 48.517 | 1.00 30.17 |
| ATOM | 2946 | N   | THR | B | 330 | 56.714 | -0.743 | 48.078 | 1.00 30.56 |
| ATOM | 2947 | CA  | THR | B | 330 | 58.160 | -0.712 | 47.818 | 1.00 33.02 |
| ATOM | 2948 | CB  | THR | B | 330 | 58.642 |  0.667 | 47.279 | 1.00 31.61 |
| ATOM | 2949 | OG1 | THR | B | 330 | 58.405 |  1.687 | 48.250 | 1.00 30.28 |
| ATOM | 2950 | CG2 | THR | B | 330 | 57.923 |  1.031 | 46.001 | 1.00 30.69 |
| ATOM | 2951 | C   | THR | B | 330 | 58.952 | -1.064 | 49.086 | 1.00 35.87 |
| ATOM | 2952 | O   | THR | B | 330 | 58.472 | -0.837 | 50.201 | 1.00 37.27 |
| ATOM | 2953 | N   | PRO | B | 331 | 60.180 | -1.604 | 48.933 | 1.00 37.54 |
| ATOM | 2954 | CD  | PRO | B | 331 | 60.899 | -1.915 | 47.684 | 1.00 37.22 |
| ATOM | 2955 | CA  | PRO | B | 331 | 60.996 | -1.973 | 50.094 | 1.00 37.70 |
| ATOM | 2956 | CB  | PRO | B | 331 | 62.374 | -2.207 | 49.470 | 1.00 37.57 |
| ATOM | 2957 | CG  | PRO | B | 331 | 62.007 | -2.839 | 48.170 | 1.00 36.82 |
| ATOM | 2958 | C   | PRO | B | 331 | 61.018 | -0.912 | 51.190 | 1.00 38.17 |
| ATOM | 2959 | O   | PRO | B | 331 | 61.076 | -1.257 | 52.369 | 1.00 38.93 |
| ATOM | 2960 | N   | SER | B | 332 | 60.960 |  0.362 | 50.787 | 1.00 38.08 |
| ATOM | 2961 | CA  | SER | B | 332 | 60.950 |  1.509 | 51.706 | 1.00 38.63 |
| ATOM | 2962 | CB  | SER | B | 332 | 61.322 |  2.791 | 50.968 | 1.00 38.51 |
| ATOM | 2963 | OG  | SER | B | 332 | 62.430 |  2.581 | 50.123 | 1.00 41.65 |
| ATOM | 2964 | C   | SER | B | 332 | 59.575 |  1.715 | 52.333 | 1.00 39.00 |
| ATOM | 2965 | O   | SER | B | 332 | 59.471 |  2.032 | 53.520 | 1.00 39.50 |
| ATOM | 2966 | N   | GLY | B | 333 | 58.532 |  1.573 | 51.513 | 1.00 38.32 |
| ATOM | 2967 | CA  | GLY | B | 333 | 57.166 |  1.740 | 51.976 | 1.00 38.23 |
| ATOM | 2968 | C   | GLY | B | 333 | 56.777 |  0.651 | 52.951 | 1.00 39.03 |
| ATOM | 2969 | O   | GLY | B | 333 | 55.930 |  0.853 | 53.829 | 1.00 40.45 |
| ATOM | 2970 | N   | ILE | B | 334 | 57.394 | -0.514 | 52.787 | 1.00 38.57 |
| ATOM | 2971 | CA  | ILE | B | 334 | 57.157 | -1.648 | 53.660 | 1.00 39.29 |
| ATOM | 2972 | CB  | ILE | B | 334 | 57.818 | -2.927 | 53.097 | 1.00 39.00 |
| ATOM | 2973 | CG2 | ILE | B | 334 | 58.025 | -3.966 | 54.201 | 1.00 38.70 |
| ATOM | 2974 | CG1 | ILE | B | 334 | 57.013 | -3.474 | 51.909 | 1.00 38.64 |
| ATOM | 2975 | CD1 | ILE | B | 334 | 55.560 | -3.794 | 52.213 | 1.00 37.03 |
| ATOM | 2976 | C   | ILE | B | 334 | 57.743 | -1.365 | 55.040 | 1.00 40.98 |
| ATOM | 2977 | O   | ILE | B | 334 | 57.153 | -1.742 | 56.046 | 1.00 42.24 |
| ATOM | 2978 | N   | LYS | B | 335 | 58.883 | -0.671 | 55.075 | 1.00 42.20 |
| ATOM | 2979 | CA  | LYS | B | 335 | 59.587 | -0.350 | 56.319 | 1.00 41.87 |
| ATOM | 2980 | CB  | LYS | B | 335 | 61.062 | -0.059 | 56.024 | 1.00 43.95 |
| ATOM | 2981 | CG  | LYS | B | 335 | 61.859 | -1.236 | 55.483 | 1.00 45.84 |
| ATOM | 2982 | CD  | LYS | B | 335 | 63.119 | -0.742 | 54.781 | 1.00 48.37 |
| ATOM | 2983 | CE  | LYS | B | 335 | 63.865 | -1.899 | 54.131 | 1.00 51.13 |
| ATOM | 2984 | NZ  | LYS | B | 335 | 64.743 | -1.474 | 52.993 | 1.00 52.42 |
| ATOM | 2985 | C   | LYS | B | 335 | 59.023 |  0.800 | 57.147 | 1.00 40.83 |
| ATOM | 2986 | O   | LYS | B | 335 | 59.407 |  0.961 | 58.297 | 1.00 41.08 |
| ATOM | 2987 | N   | LEU | B | 336 | 58.142 |  1.609 | 56.560 | 1.00 40.16 |
| ATOM | 2988 | CA  | LEU | B | 336 | 57.542 |  2.768 | 57.251 | 1.00 38.20 |
| ATOM | 2989 | CB  | LEU | B | 336 | 56.523 |  3.473 | 56.339 | 1.00 38.82 |
| ATOM | 2990 | CG  | LEU | B | 336 | 57.046 |  4.240 | 55.123 | 1.00 38.16 |
| ATOM | 2991 | CD1 | LEU | B | 336 | 55.932 |  4.504 | 54.134 | 1.00 37.61 |
| ATOM | 2992 | CD2 | LEU | B | 336 | 57.663 |  5.535 | 55.584 | 1.00 38.42 |
| ATOM | 2993 | C   | LEU | B | 336 | 56.886 |  2.422 | 58.584 | 1.00 36.36 |
| ATOM | 2994 | O   | LEU | B | 336 | 56.175 |  1.419 | 58.697 | 1.00 35.90 |
| ATOM | 2995 | N   | THR | B | 337 | 57.145 |  3.258 | 59.588 | 1.00 35.16 |
| ATOM | 2996 | CA  | THR | B | 337 | 56.604 |  3.065 | 60.931 | 1.00 34.34 |

Figure 6

| | | | | | | | | | |
|---|---|---|---|---|---|---|---|---|---|
| ATOM | 2997 | CB | THR | B | 337 | 57.516 | 3.713 | 62.035 | 1.00 33.06 |
| ATOM | 2998 | OG1 | THR | B | 337 | 57.442 | 5.146 | 61.982 | 1.00 31.81 |
| ATOM | 2999 | CG2 | THR | B | 337 | 58.966 | 3.285 | 61.851 | 1.00 31.07 |
| ATOM | 3000 | C | THR | B | 337 | 55.180 | 3.618 | 61.041 | 1.00 36.02 |
| ATOM | 3001 | O | THR | B | 337 | 54.778 | 4.504 | 60.265 | 1.00 36.23 |
| ATOM | 3002 | N | ILE | B | 338 | 54.421 | 3.082 | 62.003 | 1.00 35.35 |
| ATOM | 3003 | CA | ILE | B | 338 | 53.041 | 3.498 | 62.236 | 1.00 33.75 |
| ATOM | 3004 | CB | ILE | B | 338 | 52.420 | 2.768 | 63.451 | 1.00 34.57 |
| ATOM | 3005 | CG2 | ILE | B | 338 | 53.099 | 3.227 | 64.757 | 1.00 33.85 |
| ATOM | 3006 | CG1 | ILE | B | 338 | 50.910 | 3.042 | 63.522 | 1.00 33.45 |
| ATOM | 3007 | CD1 | ILE | B | 338 | 50.100 | 2.432 | 62.398 | 1.00 32.93 |
| ATOM | 3008 | C | ILE | B | 338 | 52.942 | 4.999 | 62.466 | 1.00 33.48 |
| ATOM | 3009 | O | ILE | B | 338 | 51.934 | 5.610 | 62.145 | 1.00 32.91 |
| ATOM | 3010 | N | ASN | B | 339 | 53.988 | 5.582 | 63.041 | 1.00 34.03 |
| ATOM | 3011 | CA | ASN | B | 339 | 54.019 | 7.014 | 63.307 | 1.00 35.32 |
| ATOM | 3012 | CB | ASN | B | 339 | 55.285 | 7.383 | 64.075 | 1.00 36.15 |
| ATOM | 3013 | CG | ASN | B | 339 | 55.299 | 6.821 | 65.474 | 1.00 36.58 |
| ATOM | 3014 | OD1 | ASN | B | 339 | 55.103 | 7.557 | 66.439 | 1.00 35.73 |
| ATOM | 3015 | ND2 | ASN | B | 339 | 55.534 | 5.509 | 65.598 | 1.00 37.41 |
| ATOM | 3016 | C | ASN | B | 339 | 53.999 | 7.792 | 62.012 | 1.00 35.94 |
| ATOM | 3017 | O | ASN | B | 339 | 53.243 | 8.754 | 61.868 | 1.00 38.27 |
| ATOM | 3018 | N | LYS | B | 340 | 54.844 | 7.365 | 61.074 | 1.00 36.37 |
| ATOM | 3019 | CA | LYS | B | 340 | 54.984 | 8.002 | 59.765 | 1.00 35.89 |
| ATOM | 3020 | CB | LYS | B | 340 | 56.226 | 7.433 | 59.053 | 1.00 37.19 |
| ATOM | 3021 | CG | LYS | B | 340 | 56.525 | 8.012 | 57.674 | 1.00 39.27 |
| ATOM | 3022 | CD | LYS | B | 340 | 56.663 | 9.529 | 57.677 | 1.00 40.05 |
| ATOM | 3023 | CE | LYS | B | 340 | 56.746 | 10.044 | 56.240 | 1.00 40.47 |
| ATOM | 3024 | NZ | LYS | B | 340 | 56.507 | 11.525 | 56.096 | 1.00 41.35 |
| ATOM | 3025 | C | LYS | B | 340 | 53.716 | 7.823 | 58.924 | 1.00 34.61 |
| ATOM | 3026 | O | LYS | B | 340 | 53.223 | 8.781 | 58.317 | 1.00 33.10 |
| ATOM | 3027 | N | LEU | B | 341 | 53.186 | 6.599 | 58.929 | 1.00 32.74 |
| ATOM | 3028 | CA | LEU | B | 341 | 51.972 | 6.268 | 58.196 | 1.00 31.37 |
| ATOM | 3029 | CB | LEU | B | 341 | 51.576 | 4.808 | 58.446 | 1.00 29.12 |
| ATOM | 3030 | CG | LEU | B | 341 | 52.513 | 3.702 | 57.956 | 1.00 27.00 |
| ATOM | 3031 | CD1 | LEU | B | 341 | 51.944 | 2.345 | 58.272 | 1.00 25.55 |
| ATOM | 3032 | CD2 | LEU | B | 341 | 52.694 | 3.831 | 56.477 | 1.00 27.32 |
| ATOM | 3033 | C | LEU | B | 341 | 50.822 | 7.199 | 58.591 | 1.00 32.18 |
| ATOM | 3034 | O | LEU | B | 341 | 50.189 | 7.814 | 57.737 | 1.00 31.62 |
| ATOM | 3035 | N | LEU | B | 342 | 50.594 | 7.343 | 59.890 | 1.00 33.34 |
| ATOM | 3036 | CA | LEU | B | 342 | 49.520 | 8.198 | 60.388 | 1.00 34.56 |
| ATOM | 3037 | CB | LEU | B | 342 | 49.343 | 8.026 | 61.899 | 1.00 36.88 |
| ATOM | 3038 | CG | LEU | B | 342 | 49.032 | 6.583 | 62.307 | 1.00 38.53 |
| ATOM | 3039 | CD1 | LEU | B | 342 | 48.465 | 6.588 | 63.672 | 1.00 39.01 |
| ATOM | 3040 | CD2 | LEU | B | 342 | 48.037 | 5.940 | 61.347 | 1.00 39.74 |
| ATOM | 3041 | C | LEU | B | 342 | 49.720 | 9.652 | 60.059 | 1.00 33.39 |
| ATOM | 3042 | O | LEU | B | 342 | 48.763 | 10.396 | 59.899 | 1.00 32.08 |
| ATOM | 3043 | N | ASP | B | 343 | 50.975 | 10.064 | 59.988 | 1.00 33.80 |
| ATOM | 3044 | CA | ASP | B | 343 | 51.268 | 11.439 | 59.659 | 1.00 34.74 |
| ATOM | 3045 | CB | ASP | B | 343 | 52.744 | 11.752 | 59.844 | 1.00 38.14 |
| ATOM | 3046 | CG | ASP | B | 343 | 53.025 | 13.226 | 59.664 | 1.00 41.80 |
| ATOM | 3047 | OD1 | ASP | B | 343 | 52.221 | 14.045 | 60.193 | 1.00 43.42 |
| ATOM | 3048 | OD2 | ASP | B | 343 | 54.009 | 13.564 | 58.965 | 1.00 42.41 |
| ATOM | 3049 | C | ASP | B | 343 | 50.889 | 11.634 | 58.213 | 1.00 32.44 |
| ATOM | 3050 | O | ASP | B | 343 | 50.455 | 12.701 | 57.811 | 1.00 32.93 |
| ATOM | 3051 | N | MET | B | 344 | 51.078 | 10.593 | 57.420 | 1.00 30.24 |
| ATOM | 3052 | CA | MET | B | 344 | 50.710 | 10.656 | 56.019 | 1.00 28.65 |
| ATOM | 3053 | CB | MET | B | 344 | 51.239 | 9.434 | 55.283 | 1.00 29.56 |
| ATOM | 3054 | CG | MET | B | 344 | 52.754 | 9.395 | 55.214 | 1.00 29.43 |
| ATOM | 3055 | SD | MET | B | 344 | 53.319 | 7.889 | 54.496 | 1.00 30.93 |

Figure 6

| ATOM | 3056 | CE | MET | B | 344 | 53.903 | 8.506 | 52.925 | 1.00 | 31.49 |
| ATOM | 3057 | C | MET | B | 344 | 49.192 | 10.723 | 55.968 | 1.00 | 26.69 |
| ATOM | 3058 | O | MET | B | 344 | 48.650 | 11.643 | 55.371 | 1.00 | 27.80 |
| ATOM | 3059 | N | ALA | B | 345 | 48.528 | 9.801 | 56.676 | 1.00 | 24.10 |
| ATOM | 3060 | CA | ALA | B | 345 | 47.065 | 9.730 | 56.785 | 1.00 | 21.03 |
| ATOM | 3061 | CB | ALA | B | 345 | 46.662 | 8.666 | 57.795 | 1.00 | 20.08 |
| ATOM | 3062 | C | ALA | B | 345 | 46.494 | 11.077 | 57.205 | 1.00 | 20.04 |
| ATOM | 3063 | O | ALA | B | 345 | 45.438 | 11.479 | 56.728 | 1.00 | 21.75 |
| ATOM | 3064 | N | ALA | B | 346 | 47.227 | 11.778 | 58.070 | 1.00 | 18.78 |
| ATOM | 3065 | CA | ALA | B | 346 | 46.853 | 13.101 | 58.569 | 1.00 | 19.86 |
| ATOM | 3066 | CB | ALA | B | 346 | 47.782 | 13.515 | 59.710 | 1.00 | 17.57 |
| ATOM | 3067 | C | ALA | B | 346 | 46.915 | 14.144 | 57.461 | 1.00 | 20.91 |
| ATOM | 3068 | O | ALA | B | 346 | 46.070 | 15.031 | 57.375 | 1.00 | 22.43 |
| ATOM | 3069 | N | GLN | B | 347 | 47.963 | 14.058 | 56.656 | 1.00 | 22.71 |
| ATOM | 3070 | CA | GLN | B | 347 | 48.176 | 14.958 | 55.522 | 1.00 | 23.01 |
| ATOM | 3071 | CB | GLN | B | 347 | 49.511 | 14.652 | 54.877 | 1.00 | 25.10 |
| ATOM | 3072 | CG | GLN | B | 347 | 50.687 | 15.204 | 55.619 | 1.00 | 27.76 |
| ATOM | 3073 | CD | GLN | B | 347 | 51.960 | 14.971 | 54.850 | 1.00 | 29.91 |
| ATOM | 3074 | OE1 | GLN | B | 347 | 52.682 | 15.917 | 54.533 | 1.00 | 31.61 |
| ATOM | 3075 | NE2 | GLN | B | 347 | 52.237 | 13.708 | 54.514 | 1.00 | 30.65 |
| ATOM | 3076 | C | GLN | B | 347 | 47.085 | 14.860 | 54.459 | 1.00 | 21.21 |
| ATOM | 3077 | O | GLN | B | 347 | 46.693 | 15.855 | 53.860 | 1.00 | 20.20 |
| ATOM | 3078 | N | ILE | B | 348 | 46.629 | 13.640 | 54.212 | 1.00 | 19.76 |
| ATOM | 3079 | CA | ILE | B | 348 | 45.572 | 13.378 | 53.259 | 1.00 | 18.92 |
| ATOM | 3080 | CB | ILE | B | 348 | 45.435 | 11.858 | 53.062 | 1.00 | 18.30 |
| ATOM | 3081 | CG2 | ILE | B | 348 | 44.197 | 11.542 | 52.244 | 1.00 | 18.66 |
| ATOM | 3082 | CG1 | ILE | B | 348 | 46.710 | 11.291 | 52.428 | 1.00 | 15.43 |
| ATOM | 3083 | CD1 | ILE | B | 348 | 46.840 | 9.795 | 52.522 | 1.00 | 13.57 |
| ATOM | 3084 | C | ILE | B | 348 | 44.263 | 13.959 | 53.819 | 1.00 | 21.07 |
| ATOM | 3085 | O | ILE | B | 348 | 43.499 | 14.629 | 53.103 | 1.00 | 21.22 |
| ATOM | 3086 | N | ALA | B | 349 | 44.026 | 13.720 | 55.120 | 1.00 | 21.20 |
| ATOM | 3087 | CA | ALA | B | 349 | 42.827 | 14.212 | 55.798 | 1.00 | 19.78 |
| ATOM | 3088 | CB | ALA | B | 349 | 42.695 | 13.581 | 57.167 | 1.00 | 20.60 |
| ATOM | 3089 | C | ALA | B | 349 | 42.859 | 15.728 | 55.895 | 1.00 | 20.77 |
| ATOM | 3090 | O | ALA | B | 349 | 41.812 | 16.373 | 55.916 | 1.00 | 22.87 |
| ATOM | 3091 | N | GLU | B | 350 | 44.056 | 16.300 | 55.931 | 1.00 | 20.02 |
| ATOM | 3092 | CA | GLU | B | 350 | 44.187 | 17.747 | 55.972 | 1.00 | 21.72 |
| ATOM | 3093 | CB | GLU | B | 350 | 45.616 | 18.154 | 56.302 | 1.00 | 23.43 |
| ATOM | 3094 | CG | GLU | B | 350 | 45.817 | 19.662 | 56.250 | 1.00 | 24.35 |
| ATOM | 3095 | CD | GLU | B | 350 | 47.276 | 20.096 | 56.388 | 1.00 | 25.13 |
| ATOM | 3096 | OE1 | GLU | B | 350 | 48.188 | 19.244 | 56.545 | 1.00 | 22.13 |
| ATOM | 3097 | OE2 | GLU | B | 350 | 47.497 | 21.326 | 56.334 | 1.00 | 27.13 |
| ATOM | 3098 | C | GLU | B | 350 | 43.805 | 18.355 | 54.622 | 1.00 | 23.80 |
| ATOM | 3099 | O | GLU | B | 350 | 43.226 | 19.443 | 54.552 | 1.00 | 25.54 |
| ATOM | 3100 | N | GLY | B | 351 | 44.146 | 17.659 | 53.542 | 1.00 | 24.35 |
| ATOM | 3101 | CA | GLY | B | 351 | 43.822 | 18.165 | 52.227 | 1.00 | 23.68 |
| ATOM | 3102 | C | GLY | B | 351 | 42.338 | 18.042 | 52.004 | 1.00 | 23.71 |
| ATOM | 3103 | O | GLY | B | 351 | 41.710 | 18.957 | 51.467 | 1.00 | 23.49 |
| ATOM | 3104 | N | MET | B | 352 | 41.790 | 16.900 | 52.418 | 1.00 | 23.50 |
| ATOM | 3105 | CA | MET | B | 352 | 40.363 | 16.619 | 52.288 | 1.00 | 22.48 |
| ATOM | 3106 | CB | MET | B | 352 | 40.052 | 15.181 | 52.711 | 1.00 | 22.21 |
| ATOM | 3107 | CG | MET | B | 352 | 40.273 | 14.123 | 51.637 | 1.00 | 21.58 |
| ATOM | 3108 | SD | MET | B | 352 | 39.578 | 14.578 | 50.044 | 1.00 | 18.90 |
| ATOM | 3109 | CE | MET | B | 352 | 37.840 | 14.992 | 50.414 | 1.00 | 18.03 |
| ATOM | 3110 | C | MET | B | 352 | 39.524 | 17.585 | 53.115 | 1.00 | 23.42 |
| ATOM | 3111 | O | MET | B | 352 | 38.385 | 17.890 | 52.747 | 1.00 | 25.33 |
| ATOM | 3112 | N | ALA | B | 353 | 40.077 | 18.045 | 54.239 | 1.00 | 22.69 |
| ATOM | 3113 | CA | ALA | B | 353 | 39.383 | 19.002 | 55.099 | 1.00 | 22.57 |
| ATOM | 3114 | CB | ALA | B | 353 | 40.151 | 19.203 | 56.394 | 1.00 | 23.51 |

Figure 6

| | | | | | | | | | |
|---|---|---|---|---|---|---|---|---|---|
| ATOM | 3115 | C | ALA | B | 353 | 39.244 | 20.329 | 54.357 | 1.00 22.96 |
| ATOM | 3116 | O | ALA | B | 353 | 38.277 | 21.048 | 54.543 | 1.00 23.70 |
| ATOM | 3117 | N | PHE | B | 354 | 40.242 | 20.655 | 53.536 | 1.00 24.61 |
| ATOM | 3118 | CA | PHE | B | 354 | 40.233 | 21.866 | 52.713 | 1.00 23.66 |
| ATOM | 3119 | CB | PHE | B | 354 | 41.602 | 22.061 | 52.052 | 1.00 24.13 |
| ATOM | 3120 | CG | PHE | B | 354 | 41.646 | 23.211 | 51.093 | 1.00 24.79 |
| ATOM | 3121 | CD1 | PHE | B | 354 | 41.520 | 24.519 | 51.556 | 1.00 25.21 |
| ATOM | 3122 | CD2 | PHE | B | 354 | 41.794 | 22.991 | 49.722 | 1.00 25.50 |
| ATOM | 3123 | CE1 | PHE | B | 354 | 41.538 | 25.597 | 50.676 | 1.00 25.00 |
| ATOM | 3124 | CE2 | PHE | B | 354 | 41.815 | 24.062 | 48.821 | 1.00 25.73 |
| ATOM | 3125 | CZ | PHE | B | 354 | 41.686 | 25.370 | 49.301 | 1.00 25.78 |
| ATOM | 3126 | C | PHE | B | 354 | 39.164 | 21.735 | 51.628 | 1.00 22.38 |
| ATOM | 3127 | O | PHE | B | 354 | 38.438 | 22.681 | 51.343 | 1.00 22.06 |
| ATOM | 3128 | N | ILE | B | 355 | 39.100 | 20.555 | 51.017 | 1.00 22.61 |
| ATOM | 3129 | CA | ILE | B | 355 | 38.123 | 20.247 | 49.971 | 1.00 23.73 |
| ATOM | 3130 | CB | ILE | B | 355 | 38.445 | 18.855 | 49.311 | 1.00 23.01 |
| ATOM | 3131 | CG2 | ILE | B | 355 | 37.241 | 18.281 | 48.577 | 1.00 21.27 |
| ATOM | 3132 | CG1 | ILE | B | 355 | 39.653 | 18.992 | 48.369 | 1.00 21.33 |
| ATOM | 3133 | CD1 | ILE | B | 355 | 40.134 | 17.689 | 47.765 | 1.00 21.43 |
| ATOM | 3134 | C | ILE | B | 355 | 36.723 | 20.286 | 50.593 | 1.00 25.81 |
| ATOM | 3135 | O | ILE | B | 355 | 35.770 | 20.761 | 49.978 | 1.00 26.49 |
| ATOM | 3136 | N | GLU | B | 356 | 36.629 | 19.841 | 51.848 | 1.00 26.38 |
| ATOM | 3137 | CA | GLU | B | 356 | 35.379 | 19.844 | 52.587 | 1.00 26.91 |
| ATOM | 3138 | CB | GLU | B | 356 | 35.575 | 19.078 | 53.891 | 1.00 26.37 |
| ATOM | 3139 | CG | GLU | B | 356 | 34.365 | 19.011 | 54.796 | 1.00 24.82 |
| ATOM | 3140 | CD | GLU | B | 356 | 34.641 | 18.203 | 56.046 | 1.00 25.74 |
| ATOM | 3141 | OE1 | GLU | B | 356 | 35.391 | 18.690 | 56.918 | 1.00 24.98 |
| ATOM | 3142 | OE2 | GLU | B | 356 | 34.136 | 17.062 | 56.157 | 1.00 26.17 |
| ATOM | 3143 | C | GLU | B | 356 | 35.013 | 21.307 | 52.869 | 1.00 29.21 |
| ATOM | 3144 | O | GLU | B | 356 | 33.909 | 21.772 | 52.568 | 1.00 30.15 |
| ATOM | 3145 | N | GLU | B | 357 | 35.990 | 22.044 | 53.372 | 1.00 31.08 |
| ATOM | 3146 | CA | GLU | B | 357 | 35.841 | 23.446 | 53.699 | 1.00 32.29 |
| ATOM | 3147 | CB | GLU | B | 357 | 37.219 | 23.999 | 54.026 | 1.00 33.63 |
| ATOM | 3148 | CG | GLU | B | 357 | 37.370 | 25.495 | 53.868 | 1.00 37.04 |
| ATOM | 3149 | CD | GLU | B | 357 | 36.984 | 26.249 | 55.109 | 1.00 38.43 |
| ATOM | 3150 | OE1 | GLU | B | 357 | 37.710 | 26.112 | 56.116 | 1.00 39.94 |
| ATOM | 3151 | OE2 | GLU | B | 357 | 35.969 | 26.981 | 55.078 | 1.00 40.07 |
| ATOM | 3152 | C | GLU | B | 357 | 35.250 | 24.243 | 52.561 | 1.00 33.68 |
| ATOM | 3153 | O | GLU | B | 357 | 34.322 | 25.022 | 52.746 | 1.00 35.93 |
| ATOM | 3154 | N | ARG | B | 358 | 35.776 | 24.019 | 51.366 | 1.00 35.80 |
| ATOM | 3155 | CA | ARG | B | 358 | 35.355 | 24.752 | 50.183 | 1.00 35.65 |
| ATOM | 3156 | CB | ARG | B | 358 | 36.521 | 24.789 | 49.198 | 1.00 36.32 |
| ATOM | 3157 | CG | ARG | B | 358 | 37.759 | 25.405 | 49.793 | 1.00 37.04 |
| ATOM | 3158 | CD | ARG | B | 358 | 37.588 | 26.891 | 49.936 | 1.00 40.69 |
| ATOM | 3159 | NE | ARG | B | 358 | 37.349 | 27.501 | 48.633 | 1.00 46.01 |
| ATOM | 3160 | CZ | ARG | B | 358 | 38.232 | 27.502 | 47.631 | 1.00 48.53 |
| ATOM | 3161 | NH1 | ARG | B | 358 | 39.415 | 26.934 | 47.789 | 1.00 50.03 |
| ATOM | 3162 | NH2 | ARG | B | 358 | 37.926 | 28.046 | 46.462 | 1.00 49.77 |
| ATOM | 3163 | C | ARG | B | 358 | 34.084 | 24.254 | 49.506 | 1.00 35.31 |
| ATOM | 3164 | O | ARG | B | 358 | 33.630 | 24.841 | 48.522 | 1.00 36.57 |
| ATOM | 3165 | N | ASN | B | 359 | 33.496 | 23.200 | 50.057 | 1.00 35.24 |
| ATOM | 3166 | CA | ASN | B | 359 | 32.265 | 22.599 | 49.533 | 1.00 36.51 |
| ATOM | 3167 | CB | ASN | B | 359 | 31.098 | 23.596 | 49.512 | 1.00 39.49 |
| ATOM | 3168 | CG | ASN | B | 359 | 30.849 | 24.219 | 50.873 | 1.00 43.16 |
| ATOM | 3169 | OD1 | ASN | B | 359 | 30.409 | 23.545 | 51.816 | 1.00 43.72 |
| ATOM | 3170 | ND2 | ASN | B | 359 | 31.174 | 25.512 | 50.998 | 1.00 44.78 |
| ATOM | 3171 | C | ASN | B | 359 | 32.398 | 21.879 | 48.194 | 1.00 34.20 |
| ATOM | 3172 | O | ASN | B | 359 | 31.612 | 22.076 | 47.266 | 1.00 32.57 |
| ATOM | 3173 | N | TYR | B | 360 | 33.413 | 21.032 | 48.128 | 1.00 31.16 |

Figure 6

```
ATOM   3174  CA   TYR B 360      33.682  20.191  46.977  1.00 27.78
ATOM   3175  CB   TYR B 360      35.076  20.499  46.406  1.00 26.83
ATOM   3176  CG   TYR B 360      35.135  21.702  45.485  1.00 25.58
ATOM   3177  CD1  TYR B 360      35.428  22.976  45.973  1.00 24.36
ATOM   3178  CE1  TYR B 360      35.471  24.085  45.132  1.00 22.77
ATOM   3179  CD2  TYR B 360      34.891  21.567  44.127  1.00 25.55
ATOM   3180  CE2  TYR B 360      34.930  22.672  43.277  1.00 25.14
ATOM   3181  CZ   TYR B 360      35.221  23.924  43.788  1.00 23.77
ATOM   3182  OH   TYR B 360      35.240  25.003  42.941  1.00 25.34
ATOM   3183  C    TYR B 360      33.675  18.772  47.550  1.00 27.74
ATOM   3184  O    TYR B 360      33.513  18.581  48.763  1.00 30.08
ATOM   3185  N    ILE B 361      33.759  17.783  46.674  1.00 24.93
ATOM   3186  CA   ILE B 361      33.847  16.398  47.084  1.00 23.25
ATOM   3187  CB   ILE B 361      32.542  15.598  46.869  1.00 22.45
ATOM   3188  CG2  ILE B 361      31.395  16.249  47.612  1.00 22.81
ATOM   3189  CG1  ILE B 361      32.221  15.439  45.390  1.00 21.19
ATOM   3190  CD1  ILE B 361      31.121  14.465  45.145  1.00 19.44
ATOM   3191  C    ILE B 361      34.947  15.853  46.193  1.00 25.47
ATOM   3192  O    ILE B 361      35.373  16.520  45.257  1.00 27.70
ATOM   3193  N    HIS B 362      35.437  14.662  46.479  1.00 24.68
ATOM   3194  CA   HIS B 362      36.484  14.104  45.666  1.00 23.28
ATOM   3195  CB   HIS B 362      37.516  13.435  46.561  1.00 20.07
ATOM   3196  CG   HIS B 362      38.743  12.989  45.840  1.00 17.06
ATOM   3197  CD2  HIS B 362      39.999  13.481  45.843  1.00 16.22
ATOM   3198  ND1  HIS B 362      38.760  11.906  44.989  1.00 16.95
ATOM   3199  CE1  HIS B 362      39.973  11.750  44.497  1.00 17.06
ATOM   3200  NE2  HIS B 362      40.745  12.694  45.001  1.00 17.30
ATOM   3201  C    HIS B 362      35.840  13.096  44.748  1.00 25.88
ATOM   3202  O    HIS B 362      35.929  13.218  43.551  1.00 28.28
ATOM   3203  N    ARG B 363      35.151  12.143  45.366  1.00 27.16
ATOM   3204  CA   ARG B 363      34.424  11.013  44.780  1.00 27.36
ATOM   3205  CB   ARG B 363      33.291  11.419  43.821  1.00 31.72
ATOM   3206  CG   ARG B 363      33.666  12.136  42.567  1.00 36.20
ATOM   3207  CD   ARG B 363      32.464  12.650  41.786  1.00 38.76
ATOM   3208  NE   ARG B 363      31.730  11.560  41.163  1.00 40.14
ATOM   3209  CZ   ARG B 363      30.404  11.472  41.149  1.00 41.26
ATOM   3210  NH1  ARG B 363      29.669  12.418  41.716  1.00 40.18
ATOM   3211  NH2  ARG B 363      29.817  10.414  40.605  1.00 41.98
ATOM   3212  C    ARG B 363      35.254   9.897  44.228  1.00 25.59
ATOM   3213  O    ARG B 363      34.719   8.886  43.804  1.00 25.14
ATOM   3214  N    ASP B 364      36.566  10.037  44.327  1.00 24.88
ATOM   3215  CA   ASP B 364      37.515   9.027  43.837  1.00 23.45
ATOM   3216  CB   ASP B 364      38.100   9.461  42.473  1.00 21.37
ATOM   3217  CG   ASP B 364      37.090   9.349  41.325  1.00 19.99
ATOM   3218  OD1  ASP B 364      36.730   8.165  41.015  1.00 17.84
ATOM   3219  OD2  ASP B 364      36.686  10.440  40.803  1.00 19.20
ATOM   3220  C    ASP B 364      38.638   8.842  44.860  1.00 23.68
ATOM   3221  O    ASP B 364      39.766   8.505  44.502  1.00 22.79
ATOM   3222  N    LEU B 365      38.328   9.077  46.130  1.00 23.74
ATOM   3223  CA   LEU B 365      39.319   8.978  47.177  1.00 22.37
ATOM   3224  CB   LEU B 365      38.825   9.731  48.413  1.00 21.12
ATOM   3225  CG   LEU B 365      39.768   9.753  49.598  1.00 20.76
ATOM   3226  CD1  LEU B 365      41.031  10.523  49.239  1.00 20.08
ATOM   3227  CD2  LEU B 365      39.075  10.364  50.820  1.00 18.68
ATOM   3228  C    LEU B 365      39.783   7.566  47.531  1.00 23.62
ATOM   3229  O    LEU B 365      39.005   6.721  47.982  1.00 24.43
ATOM   3230  N    ARG B 366      41.073   7.327  47.296  1.00 24.12
ATOM   3231  CA   ARG B 366      41.754   6.069  47.575  1.00 23.67
ATOM   3232  CB   ARG B 366      41.323   4.947  46.632  1.00 25.84
```

Figure 6

| | | | | | | | | | |
|---|---|---|---|---|---|---|---|---|---|
| ATOM | 3233 | CG | ARG | B | 366 | 41.424 | 5.217 | 45.130 | 1.00 28.88 |
| ATOM | 3234 | CD | ARG | B | 366 | 41.005 | 3.963 | 44.345 | 1.00 30.98 |
| ATOM | 3235 | NE | ARG | B | 366 | 40.765 | 4.227 | 42.930 | 1.00 33.32 |
| ATOM | 3236 | CZ | ARG | B | 366 | 39.748 | 4.950 | 42.464 | 1.00 34.04 |
| ATOM | 3237 | NH1 | ARG | B | 366 | 38.856 | 5.489 | 43.291 | 1.00 34.36 |
| ATOM | 3238 | NH2 | ARG | B | 366 | 39.645 | 5.171 | 41.163 | 1.00 33.83 |
| ATOM | 3239 | C | ARG | B | 366 | 43.262 | 6.280 | 47.526 | 1.00 23.14 |
| ATOM | 3240 | O | ARG | B | 366 | 43.726 | 7.318 | 47.066 | 1.00 23.84 |
| ATOM | 3241 | N | ALA | B | 367 | 44.031 | 5.318 | 48.026 | 1.00 22.57 |
| ATOM | 3242 | CA | ALA | B | 367 | 45.492 | 5.430 | 48.046 | 1.00 22.59 |
| ATOM | 3243 | CB | ALA | B | 367 | 46.095 | 4.182 | 48.619 | 1.00 22.02 |
| ATOM | 3244 | C | ALA | B | 367 | 46.063 | 5.713 | 46.660 | 1.00 24.50 |
| ATOM | 3245 | O | ALA | B | 367 | 46.899 | 6.612 | 46.493 | 1.00 24.06 |
| ATOM | 3246 | N | ALA | B | 368 | 45.531 | 4.998 | 45.664 | 1.00 24.16 |
| ATOM | 3247 | CA | ALA | B | 368 | 45.948 | 5.129 | 44.278 | 1.00 22.68 |
| ATOM | 3248 | CB | ALA | B | 368 | 45.072 | 4.283 | 43.387 | 1.00 22.63 |
| ATOM | 3249 | C | ALA | B | 368 | 45.931 | 6.577 | 43.816 | 1.00 22.68 |
| ATOM | 3250 | O | ALA | B | 368 | 46.827 | 7.006 | 43.079 | 1.00 24.74 |
| ATOM | 3251 | N | ASN | B | 369 | 44.949 | 7.339 | 44.299 | 1.00 22.06 |
| ATOM | 3252 | CA | ASN | B | 369 | 44.812 | 8.751 | 43.945 | 1.00 21.45 |
| ATOM | 3253 | CB | ASN | B | 369 | 43.348 | 9.096 | 43.697 | 1.00 21.59 |
| ATOM | 3254 | CG | ASN | B | 369 | 42.782 | 8.336 | 42.512 | 1.00 21.57 |
| ATOM | 3255 | OD1 | ASN | B | 369 | 43.481 | 8.095 | 41.528 | 1.00 22.65 |
| ATOM | 3256 | ND2 | ASN | B | 369 | 41.554 | 7.886 | 42.630 | 1.00 20.49 |
| ATOM | 3257 | C | ASN | B | 369 | 45.494 | 9.753 | 44.887 | 1.00 21.54 |
| ATOM | 3258 | O | ASN | B | 369 | 45.154 | 10.947 | 44.917 | 1.00 21.53 |
| ATOM | 3259 | N | ILE | B | 370 | 46.497 | 9.261 | 45.612 | 1.00 20.25 |
| ATOM | 3260 | CA | ILE | B | 370 | 47.278 | 10.088 | 46.514 | 1.00 18.84 |
| ATOM | 3261 | CB | ILE | B | 370 | 47.213 | 9.580 | 47.990 | 1.00 18.29 |
| ATOM | 3262 | CG2 | ILE | B | 370 | 48.057 | 10.486 | 48.895 | 1.00 17.53 |
| ATOM | 3263 | CG1 | ILE | B | 370 | 45.760 | 9.495 | 48.491 | 1.00 15.89 |
| ATOM | 3264 | CD1 | ILE | B | 370 | 45.065 | 10.824 | 48.595 | 1.00 14.76 |
| ATOM | 3265 | C | ILE | B | 370 | 48.714 | 9.948 | 46.015 | 1.00 17.48 |
| ATOM | 3266 | O | ILE | B | 370 | 49.163 | 8.850 | 45.696 | 1.00 16.02 |
| ATOM | 3267 | N | LEU | B | 371 | 49.422 | 11.062 | 45.920 | 1.00 17.00 |
| ATOM | 3268 | CA | LEU | B | 371 | 50.803 | 11.039 | 45.470 | 1.00 17.35 |
| ATOM | 3269 | CB | LEU | B | 371 | 50.971 | 12.006 | 44.293 | 1.00 15.95 |
| ATOM | 3270 | CG | LEU | B | 371 | 50.046 | 11.756 | 43.086 | 1.00 14.77 |
| ATOM | 3271 | CD1 | LEU | B | 371 | 50.201 | 12.880 | 42.088 | 1.00 12.92 |
| ATOM | 3272 | CD2 | LEU | B | 371 | 50.327 | 10.405 | 42.433 | 1.00 12.07 |
| ATOM | 3273 | C | LEU | B | 371 | 51.784 | 11.357 | 46.612 | 1.00 18.10 |
| ATOM | 3274 | O | LEU | B | 371 | 51.468 | 12.119 | 47.511 | 1.00 18.82 |
| ATOM | 3275 | N | VAL | B | 372 | 52.966 | 10.745 | 46.566 | 1.00 20.14 |
| ATOM | 3276 | CA | VAL | B | 372 | 54.016 | 10.915 | 47.570 | 1.00 21.52 |
| ATOM | 3277 | CB | VAL | B | 372 | 54.450 | 9.521 | 48.088 | 1.00 21.31 |
| ATOM | 3278 | CG1 | VAL | B | 372 | 55.249 | 9.637 | 49.387 | 1.00 21.11 |
| ATOM | 3279 | CG2 | VAL | B | 372 | 53.240 | 8.633 | 48.271 | 1.00 20.32 |
| ATOM | 3280 | C | VAL | B | 372 | 55.265 | 11.635 | 46.996 | 1.00 23.94 |
| ATOM | 3281 | O | VAL | B | 372 | 55.862 | 11.196 | 46.006 | 1.00 25.89 |
| ATOM | 3282 | N | SER | B | 373 | 55.700 | 12.707 | 47.642 | 1.00 25.78 |
| ATOM | 3283 | CA | SER | B | 373 | 56.873 | 13.432 | 47.167 | 1.00 28.04 |
| ATOM | 3284 | CB | SER | B | 373 | 56.875 | 14.852 | 47.714 | 1.00 28.41 |
| ATOM | 3285 | OG | SER | B | 373 | 57.001 | 14.826 | 49.115 | 1.00 30.86 |
| ATOM | 3286 | C | SER | B | 373 | 58.158 | 12.710 | 47.565 | 1.00 30.26 |
| ATOM | 3287 | O | SER | B | 373 | 58.111 | 11.559 | 47.994 | 1.00 30.17 |
| ATOM | 3288 | N | ASP | B | 374 | 59.309 | 13.358 | 47.356 | 1.00 34.16 |
| ATOM | 3289 | CA | ASP | B | 374 | 60.610 | 12.767 | 47.717 | 1.00 36.33 |
| ATOM | 3290 | CB | ASP | B | 374 | 61.768 | 13.435 | 46.956 | 1.00 39.01 |
| ATOM | 3291 | CG | ASP | B | 374 | 61.714 | 14.944 | 47.015 | 1.00 41.21 |

Figure 6

| | | | | | | | | | |
|---|---|---|---|---|---|---|---|---|---|
| ATOM | 3292 | OD1 | ASP | B | 374 | 61.362 | 15.551 | 45.986 | 1.00 43.07 |
| ATOM | 3293 | OD2 | ASP | B | 374 | 62.021 | 15.529 | 48.074 | 1.00 42.41 |
| ATOM | 3294 | C | ASP | B | 374 | 60.851 | 12.833 | 49.220 | 1.00 35.56 |
| ATOM | 3295 | O | ASP | B | 374 | 61.604 | 12.032 | 49.768 | 1.00 34.94 |
| ATOM | 3296 | N | THR | B | 375 | 60.207 | 13.804 | 49.867 | 1.00 34.84 |
| ATOM | 3297 | CA | THR | B | 375 | 60.292 | 13.987 | 51.310 | 1.00 33.52 |
| ATOM | 3298 | CB | THR | B | 375 | 60.204 | 15.469 | 51.710 | 1.00 33.98 |
| ATOM | 3299 | OG1 | THR | B | 375 | 58.969 | 16.030 | 51.253 | 1.00 33.85 |
| ATOM | 3300 | CG2 | THR | B | 375 | 61.377 | 16.254 | 51.126 | 1.00 34.60 |
| ATOM | 3301 | C | THR | B | 375 | 59.136 | 13.256 | 51.967 | 1.00 33.63 |
| ATOM | 3302 | O | THR | B | 375 | 58.664 | 13.670 | 53.028 | 1.00 34.06 |
| ATOM | 3303 | N | LEU | B | 376 | 58.657 | 12.214 | 51.287 | 1.00 32.65 |
| ATOM | 3304 | CA | LEU | B | 376 | 57.555 | 11.353 | 51.722 | 1.00 30.96 |
| ATOM | 3305 | CB | LEU | B | 376 | 58.034 | 10.359 | 52.777 | 1.00 31.43 |
| ATOM | 3306 | CG | LEU | B | 376 | 59.279 | 9.531 | 52.456 | 1.00 31.66 |
| ATOM | 3307 | CD1 | LEU | B | 376 | 59.332 | 8.390 | 53.437 | 1.00 32.00 |
| ATOM | 3308 | CD2 | LEU | B | 376 | 59.244 | 8.984 | 51.048 | 1.00 32.07 |
| ATOM | 3309 | C | LEU | B | 376 | 56.254 | 12.016 | 52.173 | 1.00 30.77 |
| ATOM | 3310 | O | LEU | B | 376 | 55.460 | 11.400 | 52.876 | 1.00 29.77 |
| ATOM | 3311 | N | SER | B | 377 | 56.025 | 13.256 | 51.754 | 1.00 31.37 |
| ATOM | 3312 | CA | SER | B | 377 | 54.792 | 13.970 | 52.106 | 1.00 32.40 |
| ATOM | 3313 | CB | SER | B | 377 | 55.021 | 15.488 | 52.110 | 1.00 33.12 |
| ATOM | 3314 | OG | SER | B | 377 | 55.155 | 15.987 | 50.790 | 1.00 36.48 |
| ATOM | 3315 | C | SER | B | 377 | 53.689 | 13.604 | 51.100 | 1.00 31.04 |
| ATOM | 3316 | O | SER | B | 377 | 53.979 | 13.324 | 49.934 | 1.00 31.80 |
| ATOM | 3317 | N | CYS | B | 378 | 52.430 | 13.647 | 51.539 | 1.00 28.42 |
| ATOM | 3318 | CA | CYS | B | 378 | 51.310 | 13.290 | 50.679 | 1.00 24.24 |
| ATOM | 3319 | CB | CYS | B | 378 | 50.398 | 12.318 | 51.400 | 1.00 22.76 |
| ATOM | 3320 | SG | CYS | B | 378 | 51.205 | 10.768 | 51.722 | 1.00 19.43 |
| ATOM | 3321 | C | CYS | B | 378 | 50.491 | 14.436 | 50.112 | 1.00 23.78 |
| ATOM | 3322 | O | CYS | B | 378 | 50.312 | 15.461 | 50.757 | 1.00 24.14 |
| ATOM | 3323 | N | LYS | B | 379 | 50.001 | 14.223 | 48.888 | 1.00 24.05 |
| ATOM | 3324 | CA | LYS | B | 379 | 49.168 | 15.176 | 48.139 | 1.00 24.79 |
| ATOM | 3325 | CB | LYS | B | 379 | 50.011 | 15.950 | 47.107 | 1.00 24.08 |
| ATOM | 3326 | CG | LYS | B | 379 | 50.683 | 17.223 | 47.656 | 1.00 24.57 |
| ATOM | 3327 | CD | LYS | B | 379 | 51.898 | 17.631 | 46.828 | 1.00 25.42 |
| ATOM | 3328 | CE | LYS | B | 379 | 52.556 | 18.938 | 47.291 | 1.00 25.08 |
| ATOM | 3329 | NZ | LYS | B | 379 | 51.861 | 20.188 | 46.811 | 1.00 26.96 |
| ATOM | 3330 | C | LYS | B | 379 | 47.970 | 14.450 | 47.462 | 1.00 25.00 |
| ATOM | 3331 | O | LYS | B | 379 | 48.086 | 13.298 | 47.019 | 1.00 23.10 |
| ATOM | 3332 | N | ILE | B | 380 | 46.804 | 15.101 | 47.474 | 1.00 24.91 |
| ATOM | 3333 | CA | ILE | B | 380 | 45.586 | 14.535 | 46.888 | 1.00 26.43 |
| ATOM | 3334 | CB | ILE | B | 380 | 44.315 | 15.101 | 47.539 | 1.00 26.24 |
| ATOM | 3335 | CG2 | ILE | B | 380 | 43.081 | 14.455 | 46.926 | 1.00 25.27 |
| ATOM | 3336 | CG1 | ILE | B | 380 | 44.336 | 14.846 | 49.042 | 1.00 26.47 |
| ATOM | 3337 | CD1 | ILE | B | 380 | 43.203 | 15.458 | 49.733 | 1.00 26.44 |
| ATOM | 3338 | C | ILE | B | 380 | 45.510 | 14.839 | 45.410 | 1.00 26.34 |
| ATOM | 3339 | O | ILE | B | 380 | 45.587 | 15.993 | 45.011 | 1.00 26.60 |
| ATOM | 3340 | N | ALA | B | 381 | 45.317 | 13.805 | 44.611 | 1.00 26.74 |
| ATOM | 3341 | CA | ALA | B | 381 | 45.243 | 13.989 | 43.175 | 1.00 28.23 |
| ATOM | 3342 | CB | ALA | B | 381 | 46.335 | 13.181 | 42.483 | 1.00 26.50 |
| ATOM | 3343 | C | ALA | B | 381 | 43.884 | 13.569 | 42.670 | 1.00 28.61 |
| ATOM | 3344 | O | ALA | B | 381 | 43.140 | 12.904 | 43.387 | 1.00 29.05 |
| ATOM | 3345 | N | ASP | B | 382 | 43.571 | 13.987 | 41.440 | 1.00 29.09 |
| ATOM | 3346 | CA | ASP | B | 382 | 42.326 | 13.652 | 40.749 | 1.00 27.65 |
| ATOM | 3347 | CB | ASP | B | 382 | 42.415 | 12.232 | 40.174 | 1.00 28.01 |
| ATOM | 3348 | CG | ASP | B | 382 | 43.343 | 12.160 | 38.959 | 1.00 28.35 |
| ATOM | 3349 | OD1 | ASP | B | 382 | 43.283 | 13.089 | 38.108 | 1.00 30.59 |
| ATOM | 3350 | OD2 | ASP | B | 382 | 44.117 | 11.185 | 38.837 | 1.00 26.23 |

Figure 6

| ATOM | 3351 | C | ASP | B | 382 | 41.069 | 13.854 | 41.571 | 1.00 | 26.91 |
| --- | --- | --- | --- | --- | --- | --- | --- | --- | --- | --- |
| ATOM | 3352 | O | ASP | B | 382 | 40.246 | 12.943 | 41.726 | 1.00 | 26.24 |
| ATOM | 3353 | N | PHE | B | 383 | 40.920 | 15.078 | 42.056 | 1.00 | 26.07 |
| ATOM | 3354 | CA | PHE | B | 383 | 39.799 | 15.451 | 42.896 | 1.00 | 27.61 |
| ATOM | 3355 | CB | PHE | B | 383 | 40.321 | 16.213 | 44.126 | 1.00 | 25.30 |
| ATOM | 3356 | CG | PHE | B | 383 | 41.192 | 17.389 | 43.787 | 1.00 | 24.66 |
| ATOM | 3357 | CD1 | PHE | B | 383 | 40.637 | 18.651 | 43.613 | 1.00 | 24.30 |
| ATOM | 3358 | CD2 | PHE | B | 383 | 42.566 | 17.227 | 43.608 | 1.00 | 24.45 |
| ATOM | 3359 | CE1 | PHE | B | 383 | 41.425 | 19.733 | 43.262 | 1.00 | 23.38 |
| ATOM | 3360 | CE2 | PHE | B | 383 | 43.366 | 18.301 | 43.257 | 1.00 | 23.61 |
| ATOM | 3361 | CZ | PHE | B | 383 | 42.796 | 19.559 | 43.081 | 1.00 | 23.56 |
| ATOM | 3362 | C | PHE | B | 383 | 38.763 | 16.300 | 42.178 | 1.00 | 28.15 |
| ATOM | 3363 | O | PHE | B | 383 | 39.081 | 17.012 | 41.226 | 1.00 | 31.08 |
| ATOM | 3364 | N | GLY | B | 384 | 37.517 | 16.199 | 42.616 | 1.00 | 28.27 |
| ATOM | 3365 | CA | GLY | B | 384 | 36.471 | 17.005 | 42.025 | 1.00 | 29.12 |
| ATOM | 3366 | C | GLY | B | 384 | 36.006 | 16.655 | 40.626 | 1.00 | 30.76 |
| ATOM | 3367 | O | GLY | B | 384 | 35.319 | 17.468 | 40.002 | 1.00 | 32.23 |
| ATOM | 3368 | N | LEU | B | 385 | 36.408 | 15.490 | 40.115 | 1.00 | 31.42 |
| ATOM | 3369 | CA | LEU | B | 385 | 35.998 | 15.043 | 38.785 | 1.00 | 31.16 |
| ATOM | 3370 | CB | LEU | B | 385 | 36.784 | 13.800 | 38.342 | 1.00 | 28.60 |
| ATOM | 3371 | CG | LEU | B | 385 | 38.297 | 13.989 | 38.187 | 1.00 | 28.19 |
| ATOM | 3372 | CD1 | LEU | B | 385 | 38.862 | 12.798 | 37.482 | 1.00 | 27.68 |
| ATOM | 3373 | CD2 | LEU | B | 385 | 38.620 | 15.254 | 37.435 | 1.00 | 26.78 |
| ATOM | 3374 | C | LEU | B | 385 | 34.509 | 14.725 | 38.796 | 1.00 | 33.80 |
| ATOM | 3375 | O | LEU | B | 385 | 33.949 | 14.305 | 39.816 | 1.00 | 34.85 |
| ATOM | 3376 | N | ALA | B | 386 | 33.855 | 14.970 | 37.667 | 1.00 | 35.39 |
| ATOM | 3377 | CA | ALA | B | 386 | 32.436 | 14.700 | 37.557 | 1.00 | 35.08 |
| ATOM | 3378 | CB | ALA | B | 386 | 31.868 | 15.439 | 36.346 | 1.00 | 35.69 |
| ATOM | 3379 | C | ALA | B | 386 | 32.201 | 13.199 | 37.420 | 1.00 | 34.06 |
| ATOM | 3380 | O | ALA | B | 386 | 31.112 | 12.714 | 37.704 | 1.00 | 35.06 |
| ATOM | 3381 | N | ARG | B | 387 | 33.253 | 12.462 | 37.074 | 1.00 | 31.72 |
| ATOM | 3382 | CA | ARG | B | 387 | 33.144 | 11.025 | 36.850 | 1.00 | 30.70 |
| ATOM | 3383 | CB | ARG | B | 387 | 33.575 | 10.747 | 35.414 | 1.00 | 31.86 |
| ATOM | 3384 | CG | ARG | B | 387 | 34.994 | 11.256 | 35.121 | 1.00 | 32.38 |
| ATOM | 3385 | CD | ARG | B | 387 | 35.436 | 10.873 | 33.748 | 1.00 | 32.56 |
| ATOM | 3386 | NE | ARG | B | 387 | 36.872 | 11.011 | 33.578 | 1.00 | 31.09 |
| ATOM | 3387 | CZ | ARG | B | 387 | 37.713 | 9.984 | 33.580 | 1.00 | 32.34 |
| ATOM | 3388 | NH1 | ARG | B | 387 | 37.252 | 8.749 | 33.752 | 1.00 | 31.07 |
| ATOM | 3389 | NH2 | ARG | B | 387 | 39.013 | 10.194 | 33.411 | 1.00 | 32.85 |
| ATOM | 3390 | C | ARG | B | 387 | 33.940 | 10.113 | 37.781 | 1.00 | 29.62 |
| ATOM | 3391 | O | ARG | B | 387 | 34.854 | 10.545 | 38.462 | 1.00 | 32.65 |
| ATOM | 3392 | N | LEU | B | 388 | 33.607 | 8.834 | 37.777 | 1.00 | 26.81 |
| ATOM | 3393 | CA | LEU | B | 388 | 34.324 | 7.867 | 38.582 | 1.00 | 25.28 |
| ATOM | 3394 | CB | LEU | B | 388 | 33.394 | 6.743 | 39.005 | 1.00 | 24.89 |
| ATOM | 3395 | CG | LEU | B | 388 | 32.077 | 7.255 | 39.553 | 1.00 | 25.53 |
| ATOM | 3396 | CD1 | LEU | B | 388 | 31.199 | 6.068 | 39.849 | 1.00 | 24.85 |
| ATOM | 3397 | CD2 | LEU | B | 388 | 32.336 | 8.118 | 40.793 | 1.00 | 27.79 |
| ATOM | 3398 | C | LEU | B | 388 | 35.425 | 7.287 | 37.704 | 1.00 | 25.56 |
| ATOM | 3399 | O | LEU | B | 388 | 35.144 | 6.642 | 36.693 | 1.00 | 26.87 |
| ATOM | 3400 | N | ILE | B | 389 | 36.678 | 7.509 | 38.088 | 1.00 | 24.71 |
| ATOM | 3401 | CA | ILE | B | 389 | 37.825 | 7.016 | 37.332 | 1.00 | 21.69 |
| ATOM | 3402 | CB | ILE | B | 389 | 39.016 | 7.999 | 37.416 | 1.00 | 19.44 |
| ATOM | 3403 | CG2 | ILE | B | 389 | 38.575 | 9.421 | 37.035 | 1.00 | 18.14 |
| ATOM | 3404 | CG1 | ILE | B | 389 | 39.632 | 7.965 | 38.821 | 1.00 | 17.45 |
| ATOM | 3405 | CD1 | ILE | B | 389 | 40.644 | 9.048 | 39.090 | 1.00 | 13.44 |
| ATOM | 3406 | C | ILE | B | 389 | 38.313 | 5.640 | 37.760 | 1.00 | 23.93 |
| ATOM | 3407 | O | ILE | B | 389 | 37.959 | 5.128 | 38.810 | 1.00 | 24.62 |
| ATOM | 3408 | N | GLU | B | 390 | 39.104 | 5.029 | 36.896 | 1.00 | 26.76 |
| ATOM | 3409 | CA | GLU | B | 390 | 39.700 | 3.737 | 37.164 | 1.00 | 30.53 |

Figure 6

```
ATOM  3410  CB   GLU B 390      39.220   2.710  36.147  1.00 31.35
ATOM  3411  CG   GLU B 390      37.779   2.303  36.332  1.00 33.53
ATOM  3412  CD   GLU B 390      37.286   1.376  35.236  1.00 35.59
ATOM  3413  OE1  GLU B 390      36.059   1.289  35.049  1.00 37.46
ATOM  3414  OE2  GLU B 390      38.114   0.737  34.553  1.00 36.58
ATOM  3415  C    GLU B 390      41.216   3.912  37.085  1.00 31.99
ATOM  3416  O    GLU B 390      41.717   4.784  36.388  1.00 31.91
ATOM  3417  N    ASP B 391      41.942   3.074  37.807  1.00 33.75
ATOM  3418  CA   ASP B 391      43.394   3.149  37.839  1.00 35.89
ATOM  3419  CB   ASP B 391      43.922   2.217  38.908  1.00 38.24
ATOM  3420  CG   ASP B 391      43.459   2.593  40.280  1.00 40.28
ATOM  3421  OD1  ASP B 391      42.880   3.692  40.494  1.00 39.85
ATOM  3422  OD2  ASP B 391      43.699   1.749  41.153  1.00 43.01
ATOM  3423  C    ASP B 391      44.099   2.821  36.542  1.00 35.41
ATOM  3424  O    ASP B 391      45.187   3.326  36.291  1.00 35.74
ATOM  3425  N    ASN B 392      43.499   1.939  35.748  1.00 34.39
ATOM  3426  CA   ASN B 392      44.077   1.530  34.474  1.00 33.99
ATOM  3427  CB   ASN B 392      43.440   0.204  34.014  1.00 33.27
ATOM  3428  CG   ASN B 392      42.000   0.370  33.539  1.00 33.82
ATOM  3429  OD1  ASN B 392      41.421   1.455  33.614  1.00 33.78
ATOM  3430  ND2  ASN B 392      41.417  -0.711  33.040  1.00 33.65
ATOM  3431  C    ASN B 392      43.987   2.606  33.351  1.00 33.53
ATOM  3432  O    ASN B 392      44.286   2.322  32.189  1.00 34.75
ATOM  3433  N    GLU B 393      43.641   3.840  33.705  1.00 31.91
ATOM  3434  CA   GLU B 393      43.508   4.903  32.717  1.00 31.40
ATOM  3435  CB   GLU B 393      42.551   5.975  33.228  1.00 31.63
ATOM  3436  CG   GLU B 393      41.200   5.383  33.585  1.00 32.17
ATOM  3437  CD   GLU B 393      40.123   6.406  33.840  1.00 33.26
ATOM  3438  OE1  GLU B 393      40.421   7.627  33.874  1.00 32.96
ATOM  3439  OE2  GLU B 393      38.955   5.968  33.993  1.00 33.74
ATOM  3440  C    GLU B 393      44.805   5.512  32.205  1.00 31.71
ATOM  3441  O    GLU B 393      44.926   5.793  31.025  1.00 31.85
ATOM  3442  N    TYR B 394      45.769   5.733  33.091  1.00 33.00
ATOM  3443  CA   TYR B 394      47.056   6.288  32.693  1.00 32.83
ATOM  3444  CB   TYR B 394      47.172   7.743  33.125  1.00 32.62
ATOM  3445  CG   TYR B 394      46.134   8.662  32.533  1.00 32.99
ATOM  3446  CD1  TYR B 394      44.841   8.687  33.034  1.00 33.00
ATOM  3447  CE1  TYR B 394      43.895   9.571  32.539  1.00 33.22
ATOM  3448  CD2  TYR B 394      46.461   9.553  31.506  1.00 33.79
ATOM  3449  CE2  TYR B 394      45.519  10.448  30.999  1.00 33.40
ATOM  3450  CZ   TYR B 394      44.234  10.450  31.521  1.00 34.35
ATOM  3451  OH   TYR B 394      43.276  11.321  31.028  1.00 35.56
ATOM  3452  C    TYR B 394      48.234   5.468  33.235  1.00 33.66
ATOM  3453  O    TYR B 394      49.373   5.932  33.249  1.00 35.65
ATOM  3454  N    THR B 395      47.929   4.285  33.755  1.00 34.08
ATOM  3455  CA   THR B 395      48.924   3.339  34.268  1.00 36.56
ATOM  3456  CB   THR B 395      49.116   3.379  35.817  1.00 36.73
ATOM  3457  OG1  THR B 395      47.879   3.688  36.478  1.00 37.12
ATOM  3458  CG2  THR B 395      50.200   4.372  36.210  1.00 36.64
ATOM  3459  C    THR B 395      48.404   1.966  33.877  1.00 38.93
ATOM  3460  O    THR B 395      47.290   1.847  33.367  1.00 39.88
ATOM  3461  N    ALA B 396      49.187   0.923  34.121  1.00 42.34
ATOM  3462  CA   ALA B 396      48.752  -0.417  33.748  1.00 45.91
ATOM  3463  CB   ALA B 396      49.798  -1.076  32.830  1.00 45.22
ATOM  3464  C    ALA B 396      48.376  -1.336  34.926  1.00 48.16
ATOM  3465  O    ALA B 396      48.817  -2.493  34.996  1.00 49.52
ATOM  3466  N    ARG B 397      47.556  -0.821  35.847  1.00 49.87
ATOM  3467  CA   ARG B 397      47.106  -1.611  36.987  1.00 50.87
ATOM  3468  CB   ARG B 397      46.788  -0.721  38.190  1.00 50.78
```

Figure 6

| | | | | | | | | | |
|---|---|---|---|---|---|---|---|---|---|
| ATOM | 3469 | CG | ARG | B | 397 | 47.961 | 0.108 | 38.698 | 1.00 51.83 |
| ATOM | 3470 | CD | ARG | B | 397 | 47.855 | 0.303 | 40.206 | 1.00 52.62 |
| ATOM | 3471 | NE | ARG | B | 397 | 48.676 | 1.402 | 40.716 | 1.00 52.36 |
| ATOM | 3472 | CZ | ARG | B | 397 | 48.300 | 2.679 | 40.708 | 1.00 52.13 |
| ATOM | 3473 | NH1 | ARG | B | 397 | 47.123 | 3.030 | 40.203 | 1.00 51.01 |
| ATOM | 3474 | NH2 | ARG | B | 397 | 49.065 | 3.599 | 41.273 | 1.00 51.86 |
| ATOM | 3475 | C | ARG | B | 397 | 45.861 | -2.400 | 36.586 | 1.00 51.76 |
| ATOM | 3476 | O | ARG | B | 397 | 45.980 | -3.642 | 36.470 | 1.00 52.31 |
| ATOM | 3477 | CB | PRO | B | 403 | 36.368 | 1.918 | 41.295 | 1.00 34.86 |
| ATOM | 3478 | CG | PRO | B | 403 | 36.889 | 1.350 | 39.939 | 1.00 34.24 |
| ATOM | 3479 | C | PRO | B | 403 | 35.286 | 0.701 | 43.244 | 1.00 35.70 |
| ATOM | 3480 | O | PRO | B | 403 | 35.302 | 1.618 | 44.096 | 1.00 36.62 |
| ATOM | 3481 | N | PRO | B | 403 | 36.016 | -0.463 | 41.116 | 1.00 34.64 |
| ATOM | 3482 | CD | PRO | B | 403 | 36.233 | -0.006 | 39.724 | 1.00 34.08 |
| ATOM | 3483 | CA | PRO | B | 403 | 36.322 | 0.623 | 42.089 | 1.00 34.48 |
| ATOM | 3484 | N | ILE | B | 404 | 34.472 | -0.339 | 43.320 | 1.00 33.66 |
| ATOM | 3485 | CA | ILE | B | 404 | 33.404 | -0.461 | 44.317 | 1.00 30.22 |
| ATOM | 3486 | CB | ILE | B | 404 | 32.527 | -1.683 | 43.963 | 1.00 29.05 |
| ATOM | 3487 | CG2 | ILE | B | 404 | 31.856 | -2.267 | 45.174 | 1.00 28.97 |
| ATOM | 3488 | CG1 | ILE | B | 404 | 31.528 | -1.296 | 42.889 | 1.00 28.60 |
| ATOM | 3489 | CD1 | ILE | B | 404 | 30.756 | -0.027 | 43.219 | 1.00 28.58 |
| ATOM | 3490 | C | ILE | B | 404 | 33.808 | -0.501 | 45.786 | 1.00 28.40 |
| ATOM | 3491 | O | ILE | B | 404 | 33.076 | -0.003 | 46.641 | 1.00 29.52 |
| ATOM | 3492 | N | LYS | B | 405 | 34.986 | -1.047 | 46.088 | 1.00 24.47 |
| ATOM | 3493 | CA | LYS | B | 405 | 35.444 | -1.183 | 47.472 | 1.00 21.61 |
| ATOM | 3494 | CB | LYS | B | 405 | 36.646 | -2.117 | 47.563 | 1.00 20.33 |
| ATOM | 3495 | CG | LYS | B | 405 | 36.331 | -3.510 | 47.093 | 1.00 19.80 |
| ATOM | 3496 | CD | LYS | B | 405 | 37.452 | -4.451 | 47.372 | 1.00 20.95 |
| ATOM | 3497 | CE | LYS | B | 405 | 37.200 | -5.815 | 46.777 | 1.00 22.86 |
| ATOM | 3498 | NZ | LYS | B | 405 | 38.215 | -6.787 | 47.268 | 1.00 25.30 |
| ATOM | 3499 | C | LYS | B | 405 | 35.665 | 0.075 | 48.335 | 1.00 21.33 |
| ATOM | 3500 | O | LYS | B | 405 | 35.884 | -0.035 | 49.540 | 1.00 21.94 |
| ATOM | 3501 | N | TRP | B | 406 | 35.595 | 1.251 | 47.710 | 1.00 19.38 |
| ATOM | 3502 | CA | TRP | B | 406 | 35.756 | 2.541 | 48.372 | 1.00 18.76 |
| ATOM | 3503 | CB | TRP | B | 406 | 36.853 | 3.370 | 47.679 | 1.00 19.52 |
| ATOM | 3504 | CG | TRP | B | 406 | 38.253 | 2.837 | 47.824 | 1.00 20.41 |
| ATOM | 3505 | CD2 | TRP | B | 406 | 38.853 | 1.771 | 47.071 | 1.00 20.69 |
| ATOM | 3506 | CE2 | TRP | B | 406 | 40.172 | 1.616 | 47.556 | 1.00 20.51 |
| ATOM | 3507 | CE3 | TRP | B | 406 | 38.408 | 0.938 | 46.034 | 1.00 22.36 |
| ATOM | 3508 | CD1 | TRP | B | 406 | 39.211 | 3.274 | 48.705 | 1.00 19.82 |
| ATOM | 3509 | NE1 | TRP | B | 406 | 40.358 | 2.539 | 48.549 | 1.00 19.77 |
| ATOM | 3510 | CZ2 | TRP | B | 406 | 41.051 | 0.653 | 47.035 | 1.00 22.51 |
| ATOM | 3511 | CZ3 | TRP | B | 406 | 39.286 | -0.026 | 45.513 | 1.00 22.45 |
| ATOM | 3512 | CH2 | TRP | B | 406 | 40.592 | -0.155 | 46.018 | 1.00 22.51 |
| ATOM | 3513 | C | TRP | B | 406 | 34.459 | 3.378 | 48.367 | 1.00 17.48 |
| ATOM | 3514 | O | TRP | B | 406 | 34.405 | 4.466 | 48.940 | 1.00 17.41 |
| ATOM | 3515 | N | THR | B | 407 | 33.418 | 2.864 | 47.724 | 1.00 17.45 |
| ATOM | 3516 | CA | THR | B | 407 | 32.139 | 3.579 | 47.594 | 1.00 17.95 |
| ATOM | 3517 | CB | THR | B | 407 | 31.388 | 3.173 | 46.263 | 1.00 17.02 |
| ATOM | 3518 | OG1 | THR | B | 407 | 32.341 | 2.970 | 45.216 | 1.00 19.35 |
| ATOM | 3519 | CG2 | THR | B | 407 | 30.411 | 4.255 | 45.835 | 1.00 14.71 |
| ATOM | 3520 | C | THR | B | 407 | 31.180 | 3.357 | 48.784 | 1.00 17.00 |
| ATOM | 3521 | O | THR | B | 407 | 30.835 | 2.209 | 49.112 | 1.00 13.94 |
| ATOM | 3522 | N | ALA | B | 408 | 30.698 | 4.463 | 49.367 | 1.00 16.85 |
| ATOM | 3523 | CA | ALA | B | 408 | 29.757 | 4.425 | 50.503 | 1.00 19.43 |
| ATOM | 3524 | CB | ALA | B | 408 | 29.421 | 5.825 | 50.975 | 1.00 17.33 |
| ATOM | 3525 | C | ALA | B | 408 | 28.496 | 3.724 | 50.045 | 1.00 20.84 |
| ATOM | 3526 | O | ALA | B | 408 | 28.151 | 3.793 | 48.871 | 1.00 22.53 |
| ATOM | 3527 | N | PRO | B | 409 | 27.770 | 3.061 | 50.966 | 1.00 23.20 |

Figure 6

| | | | | | | | | | |
|---|---|---|---|---|---|---|---|---|---|
| ATOM | 3528 | CD | PRO | B | 409 | 28.000 | 2.983 | 52.415 | 1.00 22.87 |
| ATOM | 3529 | CA | PRO | B | 409 | 26.537 | 2.347 | 50.607 | 1.00 23.46 |
| ATOM | 3530 | CB | PRO | B | 409 | 26.024 | 1.867 | 51.959 | 1.00 23.84 |
| ATOM | 3531 | CG | PRO | B | 409 | 27.279 | 1.717 | 52.760 | 1.00 24.05 |
| ATOM | 3532 | C | PRO | B | 409 | 25.489 | 3.195 | 49.882 | 1.00 23.64 |
| ATOM | 3533 | O | PRO | B | 409 | 24.870 | 2.728 | 48.923 | 1.00 23.96 |
| ATOM | 3534 | N | GLU | B | 410 | 25.296 | 4.437 | 50.319 | 1.00 23.26 |
| ATOM | 3535 | CA | GLU | B | 410 | 24.304 | 5.286 | 49.678 | 1.00 24.77 |
| ATOM | 3536 | CB | GLU | B | 410 | 24.004 | 6.548 | 50.501 | 1.00 23.34 |
| ATOM | 3537 | CG | GLU | B | 410 | 25.066 | 7.629 | 50.532 | 1.00 24.46 |
| ATOM | 3538 | CD | GLU | B | 410 | 26.221 | 7.324 | 51.481 | 1.00 23.81 |
| ATOM | 3539 | OE1 | GLU | B | 410 | 26.248 | 6.244 | 52.087 | 1.00 24.35 |
| ATOM | 3540 | OE2 | GLU | B | 410 | 27.117 | 8.180 | 51.626 | 1.00 22.93 |
| ATOM | 3541 | C | GLU | B | 410 | 24.705 | 5.629 | 48.253 | 1.00 25.94 |
| ATOM | 3542 | O | GLU | B | 410 | 23.852 | 5.751 | 47.374 | 1.00 28.86 |
| ATOM | 3543 | N | ALA | B | 411 | 26.004 | 5.770 | 48.023 | 1.00 25.51 |
| ATOM | 3544 | CA | ALA | B | 411 | 26.515 | 6.085 | 46.697 | 1.00 25.96 |
| ATOM | 3545 | CB | ALA | B | 411 | 27.984 | 6.468 | 46.763 | 1.00 24.83 |
| ATOM | 3546 | C | ALA | B | 411 | 26.312 | 4.867 | 45.788 | 1.00 26.68 |
| ATOM | 3547 | O | ALA | B | 411 | 25.991 | 5.022 | 44.617 | 1.00 28.50 |
| ATOM | 3548 | N | ILE | B | 412 | 26.449 | 3.662 | 46.339 | 1.00 26.71 |
| ATOM | 3549 | CA | ILE | B | 412 | 26.255 | 2.438 | 45.558 | 1.00 27.17 |
| ATOM | 3550 | CB | ILE | B | 412 | 26.752 | 1.180 | 46.308 | 1.00 26.78 |
| ATOM | 3551 | CG2 | ILE | B | 412 | 26.344 | -0.100 | 45.543 | 1.00 26.08 |
| ATOM | 3552 | CG1 | ILE | B | 412 | 28.264 | 1.218 | 46.474 | 1.00 25.10 |
| ATOM | 3553 | CD1 | ILE | B | 412 | 28.796 | -0.033 | 47.071 | 1.00 23.54 |
| ATOM | 3554 | C | ILE | B | 412 | 24.790 | 2.179 | 45.186 | 1.00 29.59 |
| ATOM | 3555 | O | ILE | B | 412 | 24.498 | 1.738 | 44.067 | 1.00 29.28 |
| ATOM | 3556 | N | ASN | B | 413 | 23.883 | 2.456 | 46.128 | 1.00 29.95 |
| ATOM | 3557 | CA | ASN | B | 413 | 22.463 | 2.212 | 45.935 | 1.00 29.06 |
| ATOM | 3558 | CB | ASN | B | 413 | 21.815 | 1.874 | 47.268 | 1.00 29.77 |
| ATOM | 3559 | CG | ASN | B | 413 | 22.454 | 0.673 | 47.934 | 1.00 31.50 |
| ATOM | 3560 | OD1 | ASN | B | 413 | 22.794 | -0.328 | 47.283 | 1.00 30.98 |
| ATOM | 3561 | ND2 | ASN | B | 413 | 22.622 | 0.762 | 49.246 | 1.00 31.79 |
| ATOM | 3562 | C | ASN | B | 413 | 21.649 | 3.283 | 45.235 | 1.00 29.58 |
| ATOM | 3563 | O | ASN | B | 413 | 20.752 | 2.960 | 44.443 | 1.00 29.50 |
| ATOM | 3564 | N | TYR | B | 414 | 21.967 | 4.543 | 45.508 | 1.00 29.43 |
| ATOM | 3565 | CA | TYR | B | 414 | 21.231 | 5.658 | 44.916 | 1.00 30.13 |
| ATOM | 3566 | CB | TYR | B | 414 | 20.446 | 6.391 | 46.003 | 1.00 32.55 |
| ATOM | 3567 | CG | TYR | B | 414 | 19.670 | 5.448 | 46.889 | 1.00 35.81 |
| ATOM | 3568 | CD1 | TYR | B | 414 | 18.363 | 5.078 | 46.572 | 1.00 36.16 |
| ATOM | 3569 | CE1 | TYR | B | 414 | 17.666 | 4.158 | 47.352 | 1.00 37.87 |
| ATOM | 3570 | CD2 | TYR | B | 414 | 20.262 | 4.874 | 48.015 | 1.00 37.50 |
| ATOM | 3571 | CE2 | TYR | B | 414 | 19.573 | 3.955 | 48.800 | 1.00 38.33 |
| ATOM | 3572 | CZ | TYR | B | 414 | 18.277 | 3.600 | 48.465 | 1.00 38.81 |
| ATOM | 3573 | OH | TYR | B | 414 | 17.595 | 2.697 | 49.257 | 1.00 40.92 |
| ATOM | 3574 | C | TYR | B | 414 | 22.126 | 6.647 | 44.169 | 1.00 29.83 |
| ATOM | 3575 | O | TYR | B | 414 | 21.634 | 7.602 | 43.549 | 1.00 28.58 |
| ATOM | 3576 | N | GLY | B | 415 | 23.438 | 6.426 | 44.242 | 1.00 28.47 |
| ATOM | 3577 | CA | GLY | B | 415 | 24.373 | 7.299 | 43.566 | 1.00 27.14 |
| ATOM | 3578 | C | GLY | B | 415 | 24.533 | 8.665 | 44.200 | 1.00 26.88 |
| ATOM | 3579 | O | GLY | B | 415 | 25.012 | 9.607 | 43.567 | 1.00 28.91 |
| ATOM | 3580 | N | THR | B | 416 | 24.136 | 8.803 | 45.450 | 1.00 26.46 |
| ATOM | 3581 | CA | THR | B | 416 | 24.294 | 10.095 | 46.087 | 1.00 25.87 |
| ATOM | 3582 | CB | THR | B | 416 | 23.169 | 10.351 | 47.156 | 1.00 25.32 |
| ATOM | 3583 | OG1 | THR | B | 416 | 23.705 | 11.027 | 48.301 | 1.00 26.12 |
| ATOM | 3584 | CG2 | THR | B | 416 | 22.501 | 9.057 | 47.584 | 1.00 23.44 |
| ATOM | 3585 | C | THR | B | 416 | 25.733 | 10.193 | 46.638 | 1.00 23.50 |
| ATOM | 3586 | O | THR | B | 416 | 26.138 | 9.395 | 47.475 | 1.00 23.91 |

Figure 6

| | | | | | | | | | |
|---|---|---|---|---|---|---|---|---|---|
| ATOM | 3587 | N | PHE | B | 417 | 26.533 | 11.069 | 46.028 | 1.00 22.58 |
| ATOM | 3588 | CA | PHE | B | 417 | 27.927 | 11.308 | 46.422 | 1.00 19.59 |
| ATOM | 3589 | CB | PHE | B | 417 | 28.873 | 11.332 | 45.206 | 1.00 18.78 |
| ATOM | 3590 | CG | PHE | B | 417 | 29.168 | 9.975 | 44.618 | 1.00 19.23 |
| ATOM | 3591 | CD1 | PHE | B | 417 | 28.456 | 9.508 | 43.495 | 1.00 19.90 |
| ATOM | 3592 | CD2 | PHE | B | 417 | 30.159 | 9.162 | 45.175 | 1.00 16.99 |
| ATOM | 3593 | CE1 | PHE | B | 417 | 28.734 | 8.242 | 42.940 | 1.00 19.63 |
| ATOM | 3594 | CE2 | PHE | B | 417 | 30.450 | 7.896 | 44.638 | 1.00 16.68 |
| ATOM | 3595 | CZ | PHE | B | 417 | 29.740 | 7.427 | 43.518 | 1.00 17.80 |
| ATOM | 3596 | C | PHE | B | 417 | 28.043 | 12.652 | 47.121 | 1.00 19.78 |
| ATOM | 3597 | O | PHE | B | 417 | 27.571 | 13.667 | 46.620 | 1.00 21.16 |
| ATOM | 3598 | N | THR | B | 418 | 28.672 | 12.653 | 48.290 | 1.00 20.35 |
| ATOM | 3599 | CA | THR | B | 418 | 28.886 | 13.869 | 49.065 | 1.00 18.90 |
| ATOM | 3600 | CB | THR | B | 418 | 27.757 | 14.102 | 50.123 | 1.00 18.09 |
| ATOM | 3601 | OG1 | THR | B | 418 | 27.780 | 13.045 | 51.087 | 1.00 17.54 |
| ATOM | 3602 | CG2 | THR | B | 418 | 26.371 | 14.148 | 49.459 | 1.00 18.13 |
| ATOM | 3603 | C | THR | B | 418 | 30.235 | 13.736 | 49.781 | 1.00 19.18 |
| ATOM | 3604 | O | THR | B | 418 | 30.935 | 12.723 | 49.656 | 1.00 18.48 |
| ATOM | 3605 | N | ILE | B | 419 | 30.600 | 14.773 | 50.518 | 1.00 20.17 |
| ATOM | 3606 | CA | ILE | B | 419 | 31.834 | 14.762 | 51.276 | 1.00 21.11 |
| ATOM | 3607 | CB | ILE | B | 419 | 32.016 | 16.087 | 52.041 | 1.00 21.40 |
| ATOM | 3608 | CG2 | ILE | B | 419 | 31.038 | 16.185 | 53.222 | 1.00 18.94 |
| ATOM | 3609 | CG1 | ILE | B | 419 | 33.472 | 16.225 | 52.465 | 1.00 20.80 |
| ATOM | 3610 | CD1 | ILE | B | 419 | 34.412 | 16.301 | 51.281 | 1.00 19.14 |
| ATOM | 3611 | C | ILE | B | 419 | 31.821 | 13.596 | 52.277 | 1.00 22.27 |
| ATOM | 3612 | O | ILE | B | 419 | 32.873 | 13.053 | 52.607 | 1.00 24.82 |
| ATOM | 3613 | N | LYS | B | 420 | 30.622 | 13.179 | 52.695 | 1.00 20.37 |
| ATOM | 3614 | CA | LYS | B | 420 | 30.442 | 12.092 | 53.658 | 1.00 18.82 |
| ATOM | 3615 | CB | LYS | B | 420 | 29.029 | 12.109 | 54.240 | 1.00 18.53 |
| ATOM | 3616 | CG | LYS | B | 420 | 28.754 | 13.307 | 55.127 | 1.00 16.51 |
| ATOM | 3617 | CD | LYS | B | 420 | 29.682 | 13.282 | 56.317 | 1.00 17.86 |
| ATOM | 3618 | CE | LYS | B | 420 | 29.329 | 14.363 | 57.288 | 1.00 19.22 |
| ATOM | 3619 | NZ | LYS | B | 420 | 30.375 | 14.464 | 58.303 | 1.00 18.74 |
| ATOM | 3620 | C | LYS | B | 420 | 30.738 | 10.734 | 53.082 | 1.00 18.27 |
| ATOM | 3621 | O | LYS | B | 420 | 31.048 | 9.805 | 53.820 | 1.00 18.68 |
| ATOM | 3622 | N | SER | B | 421 | 30.554 | 10.583 | 51.774 | 1.00 19.19 |
| ATOM | 3623 | CA | SER | B | 421 | 30.882 | 9.316 | 51.151 | 1.00 19.14 |
| ATOM | 3624 | CB | SER | B | 421 | 30.080 | 9.091 | 49.856 | 1.00 18.74 |
| ATOM | 3625 | OG | SER | B | 421 | 29.855 | 10.291 | 49.147 | 1.00 18.58 |
| ATOM | 3626 | C | SER | B | 421 | 32.415 | 9.316 | 50.948 | 1.00 20.04 |
| ATOM | 3627 | O | SER | B | 421 | 33.040 | 8.258 | 50.888 | 1.00 19.85 |
| ATOM | 3628 | N | ASP | B | 422 | 33.022 | 10.507 | 50.911 | 1.00 18.69 |
| ATOM | 3629 | CA | ASP | B | 422 | 34.470 | 10.611 | 50.807 | 1.00 18.51 |
| ATOM | 3630 | CB | ASP | B | 422 | 34.919 | 12.039 | 50.568 | 1.00 17.93 |
| ATOM | 3631 | CG | ASP | B | 422 | 34.652 | 12.521 | 49.167 | 1.00 19.06 |
| ATOM | 3632 | OD1 | ASP | B | 422 | 34.372 | 11.716 | 48.241 | 1.00 20.44 |
| ATOM | 3633 | OD2 | ASP | B | 422 | 34.745 | 13.745 | 48.989 | 1.00 19.59 |
| ATOM | 3634 | C | ASP | B | 422 | 35.005 | 10.176 | 52.159 | 1.00 20.51 |
| ATOM | 3635 | O | ASP | B | 422 | 36.068 | 9.560 | 52.236 | 1.00 22.07 |
| ATOM | 3636 | N | VAL | B | 423 | 34.303 | 10.558 | 53.230 | 1.00 20.75 |
| ATOM | 3637 | CA | VAL | B | 423 | 34.693 | 10.164 | 54.593 | 1.00 19.33 |
| ATOM | 3638 | CB | VAL | B | 423 | 33.762 | 10.767 | 55.683 | 1.00 18.66 |
| ATOM | 3639 | CG1 | VAL | B | 423 | 34.121 | 10.204 | 57.057 | 1.00 17.96 |
| ATOM | 3640 | CG2 | VAL | B | 423 | 33.888 | 12.282 | 55.699 | 1.00 17.80 |
| ATOM | 3641 | C | VAL | B | 423 | 34.670 | 8.637 | 54.682 | 1.00 19.49 |
| ATOM | 3642 | O | VAL | B | 423 | 35.489 | 8.047 | 55.383 | 1.00 21.06 |
| ATOM | 3643 | N | TRP | B | 424 | 33.748 | 7.999 | 53.964 | 1.00 18.70 |
| ATOM | 3644 | CA | TRP | B | 424 | 33.677 | 6.538 | 53.952 | 1.00 18.20 |
| ATOM | 3645 | CB | TRP | B | 424 | 32.402 | 6.074 | 53.239 | 1.00 15.94 |

Figure 6

```
ATOM   3646  CG   TRP B 424      32.327    4.597   53.037  1.00 14.20
ATOM   3647  CD2  TRP B 424      31.486    3.674   53.733  1.00 13.72
ATOM   3648  CE2  TRP B 424      31.806    2.377   53.271  1.00 14.72
ATOM   3649  CE3  TRP B 424      30.491    3.811   54.713  1.00 13.75
ATOM   3650  CD1  TRP B 424      33.092    3.847   52.192  1.00 14.89
ATOM   3651  NE1  TRP B 424      32.796    2.512   52.329  1.00 14.50
ATOM   3652  CZ2  TRP B 424      31.174    1.229   53.753  1.00 14.48
ATOM   3653  CZ3  TRP B 424      29.868    2.683   55.188  1.00 11.23
ATOM   3654  CH2  TRP B 424      30.207    1.407   54.713  1.00 13.61
ATOM   3655  C    TRP B 424      34.917    6.012   53.229  1.00 19.76
ATOM   3656  O    TRP B 424      35.549    5.065   53.681  1.00 20.07
ATOM   3657  N    SER B 425      35.271    6.655   52.116  1.00 23.33
ATOM   3658  CA   SER B 425      36.433    6.261   51.308  1.00 23.23
ATOM   3659  CB   SER B 425      36.519    7.097   50.028  1.00 23.30
ATOM   3660  OG   SER B 425      35.458    6.793   49.147  1.00 24.21
ATOM   3661  C    SER B 425      37.726    6.411   52.091  1.00 22.68
ATOM   3662  O    SER B 425      38.594    5.539   52.041  1.00 23.33
ATOM   3663  N    PHE B 426      37.838    7.519   52.814  1.00 21.10
ATOM   3664  CA   PHE B 426      39.011    7.795   53.621  1.00 22.17
ATOM   3665  CB   PHE B 426      38.866    9.126   54.354  1.00 22.94
ATOM   3666  CG   PHE B 426      40.054    9.470   55.209  1.00 24.30
ATOM   3667  CD1  PHE B 426      41.233    9.920   54.623  1.00 24.56
ATOM   3668  CD2  PHE B 426      39.999    9.338   56.592  1.00 23.58
ATOM   3669  CE1  PHE B 426      42.346   10.239   55.401  1.00 26.25
ATOM   3670  CE2  PHE B 426      41.102    9.653   57.377  1.00 25.28
ATOM   3671  CZ   PHE B 426      42.281   10.106   56.779  1.00 25.56
ATOM   3672  C    PHE B 426      39.260    6.678   54.632  1.00 22.44
ATOM   3673  O    PHE B 426      40.409    6.361   54.934  1.00 23.33
ATOM   3674  N    GLY B 427      38.186    6.100   55.160  1.00 21.27
ATOM   3675  CA   GLY B 427      38.330    5.024   56.119  1.00 20.51
ATOM   3676  C    GLY B 427      38.817    3.764   55.446  1.00 20.27
ATOM   3677  O    GLY B 427      39.469    2.922   56.059  1.00 20.90
ATOM   3678  N    ILE B 428      38.430    3.597   54.191  1.00 21.52
ATOM   3679  CA   ILE B 428      38.856    2.436   53.410  1.00 21.70
ATOM   3680  CB   ILE B 428      38.019    2.288   52.118  1.00 19.71
ATOM   3681  CG2  ILE B 428      38.474    1.068   51.348  1.00 18.13
ATOM   3682  CG1  ILE B 428      36.529    2.186   52.466  1.00 18.97
ATOM   3683  CD1  ILE B 428      36.166    0.980   53.311  1.00 19.23
ATOM   3684  C    ILE B 428      40.323    2.662   53.029  1.00 22.20
ATOM   3685  O    ILE B 428      41.097    1.711   52.929  1.00 22.73
ATOM   3686  N    LEU B 429      40.690    3.940   52.872  1.00 20.95
ATOM   3687  CA   LEU B 429      42.032    4.361   52.499  1.00 18.86
ATOM   3688  CB   LEU B 429      42.017    5.844   52.117  1.00 16.64
ATOM   3689  CG   LEU B 429      43.169    6.484   51.340  1.00 15.68
ATOM   3690  CD1  LEU B 429      42.770    7.870   50.937  1.00 15.83
ATOM   3691  CD2  LEU B 429      44.447    6.536   52.132  1.00 15.73
ATOM   3692  C    LEU B 429      42.977    4.128   53.662  1.00 20.36
ATOM   3693  O    LEU B 429      44.135    3.760   53.440  1.00 20.64
ATOM   3694  N    LEU B 430      42.488    4.350   54.895  1.00 20.76
ATOM   3695  CA   LEU B 430      43.289    4.163   56.104  1.00 19.64
ATOM   3696  CB   LEU B 430      42.544    4.598   57.367  1.00 18.40
ATOM   3697  CG   LEU B 430      42.270    6.074   57.659  1.00 18.21
ATOM   3698  CD1  LEU B 430      41.343    6.201   58.853  1.00 16.14
ATOM   3699  CD2  LEU B 430      43.554    6.830   57.911  1.00 18.64
ATOM   3700  C    LEU B 430      43.692    2.717   56.263  1.00 21.92
ATOM   3701  O    LEU B 430      44.705    2.441   56.893  1.00 24.71
ATOM   3702  N    THR B 431      42.887    1.789   55.753  1.00 22.79
ATOM   3703  CA   THR B 431      43.238    0.369   55.851  1.00 23.56
ATOM   3704  CB   THR B 431      42.051   -0.593   55.569  1.00 24.27
```

Figure 6

| | | | | | | | | | |
|---|---|---|---|---|---|---|---|---|---|
| ATOM | 3705 | OG1 | THR | B | 431 | 41.740 | -0.580 | 54.168 | 1.00 25.78 |
| ATOM | 3706 | CG2 | THR | B | 431 | 40.819 | -0.207 | 56.390 | 1.00 22.47 |
| ATOM | 3707 | C | THR | B | 431 | 44.344 | 0.096 | 54.842 | 1.00 24.80 |
| ATOM | 3708 | O | THR | B | 431 | 45.167 | -0.782 | 55.047 | 1.00 26.79 |
| ATOM | 3709 | N | GLU | B | 432 | 44.309 | 0.817 | 53.718 | 1.00 25.64 |
| ATOM | 3710 | CA | GLU | B | 432 | 45.336 | 0.705 | 52.690 | 1.00 24.33 |
| ATOM | 3711 | CB | GLU | B | 432 | 44.993 | 1.590 | 51.494 | 1.00 23.63 |
| ATOM | 3712 | CG | GLU | B | 432 | 43.859 | 1.049 | 50.657 | 1.00 24.68 |
| ATOM | 3713 | CD | GLU | B | 432 | 43.631 | 1.852 | 49.392 | 1.00 24.85 |
| ATOM | 3714 | OE1 | GLU | B | 432 | 43.112 | 2.981 | 49.473 | 1.00 23.86 |
| ATOM | 3715 | OE2 | GLU | B | 432 | 43.970 | 1.344 | 48.306 | 1.00 25.56 |
| ATOM | 3716 | C | GLU | B | 432 | 46.684 | 1.135 | 53.268 | 1.00 24.16 |
| ATOM | 3717 | O | GLU | B | 432 | 47.691 | 0.499 | 53.023 | 1.00 26.89 |
| ATOM | 3718 | N | ILE | B | 433 | 46.682 | 2.195 | 54.062 | 1.00 23.06 |
| ATOM | 3719 | CA | ILE | B | 433 | 47.889 | 2.723 | 54.684 | 1.00 23.10 |
| ATOM | 3720 | CB | ILE | B | 433 | 47.568 | 4.083 | 55.334 | 1.00 22.50 |
| ATOM | 3721 | CG2 | ILE | B | 433 | 48.757 | 4.635 | 56.059 | 1.00 21.70 |
| ATOM | 3722 | CG1 | ILE | B | 433 | 47.100 | 5.070 | 54.271 | 1.00 22.32 |
| ATOM | 3723 | CD1 | ILE | B | 433 | 46.825 | 6.471 | 54.818 | 1.00 23.81 |
| ATOM | 3724 | C | ILE | B | 433 | 48.549 | 1.795 | 55.720 | 1.00 25.56 |
| ATOM | 3725 | O | ILE | B | 433 | 49.769 | 1.570 | 55.693 | 1.00 28.24 |
| ATOM | 3726 | N | VAL | B | 434 | 47.742 | 1.217 | 56.602 | 1.00 27.93 |
| ATOM | 3727 | CA | VAL | B | 434 | 48.261 | 0.358 | 57.662 | 1.00 27.41 |
| ATOM | 3728 | CB | VAL | B | 434 | 47.372 | 0.409 | 58.932 | 1.00 26.59 |
| ATOM | 3729 | CG1 | VAL | B | 434 | 47.361 | 1.829 | 59.489 | 1.00 25.57 |
| ATOM | 3730 | CG2 | VAL | B | 434 | 45.952 | -0.092 | 58.632 | 1.00 24.18 |
| ATOM | 3731 | C | VAL | B | 434 | 48.533 | -1.082 | 57.276 | 1.00 29.03 |
| ATOM | 3732 | O | VAL | B | 434 | 49.059 | -1.852 | 58.087 | 1.00 30.58 |
| ATOM | 3733 | N | THR | B | 435 | 48.149 | -1.461 | 56.063 | 1.00 29.67 |
| ATOM | 3734 | CA | THR | B | 435 | 48.397 | -2.817 | 55.586 | 1.00 31.95 |
| ATOM | 3735 | CB | THR | B | 435 | 47.099 | -3.516 | 55.155 | 1.00 31.75 |
| ATOM | 3736 | OG1 | THR | B | 435 | 46.510 | -2.814 | 54.053 | 1.00 31.27 |
| ATOM | 3737 | CG2 | THR | B | 435 | 46.120 | -3.579 | 56.318 | 1.00 31.52 |
| ATOM | 3738 | C | THR | B | 435 | 49.346 | -2.753 | 54.395 | 1.00 34.10 |
| ATOM | 3739 | O | THR | B | 435 | 49.437 | -3.697 | 53.615 | 1.00 34.10 |
| ATOM | 3740 | N | HIS | B | 436 | 50.018 | -1.610 | 54.257 | 1.00 36.75 |
| ATOM | 3741 | CA | HIS | B | 436 | 50.963 | -1.357 | 53.179 | 1.00 39.18 |
| ATOM | 3742 | CB | HIS | B | 436 | 52.275 | -2.110 | 53.434 | 1.00 43.38 |
| ATOM | 3743 | CG | HIS | B | 436 | 52.940 | -1.734 | 54.725 | 1.00 47.82 |
| ATOM | 3744 | CD2 | HIS | B | 436 | 53.371 | -2.492 | 55.762 | 1.00 48.73 |
| ATOM | 3745 | ND1 | HIS | B | 436 | 53.187 | -0.422 | 55.084 | 1.00 48.77 |
| ATOM | 3746 | CE1 | HIS | B | 436 | 53.740 | -0.391 | 56.284 | 1.00 48.46 |
| ATOM | 3747 | NE2 | HIS | B | 436 | 53.860 | -1.632 | 56.718 | 1.00 49.33 |
| ATOM | 3748 | C | HIS | B | 436 | 50.426 | -1.634 | 51.775 | 1.00 38.42 |
| ATOM | 3749 | O | HIS | B | 436 | 51.019 | -2.398 | 51.013 | 1.00 38.35 |
| ATOM | 3750 | N | GLY | B | 437 | 49.301 | -1.003 | 51.443 | 1.00 36.15 |
| ATOM | 3751 | CA | GLY | B | 437 | 48.709 | -1.149 | 50.125 | 1.00 36.82 |
| ATOM | 3752 | C | GLY | B | 437 | 47.877 | -2.374 | 49.794 | 1.00 37.12 |
| ATOM | 3753 | O | GLY | B | 437 | 47.610 | -2.634 | 48.622 | 1.00 38.42 |
| ATOM | 3754 | N | ARG | B | 438 | 47.444 | -3.108 | 50.810 | 1.00 37.13 |
| ATOM | 3755 | CA | ARG | B | 438 | 46.617 | -4.300 | 50.617 | 1.00 36.69 |
| ATOM | 3756 | CB | ARG | B | 438 | 46.465 | -5.004 | 51.973 | 1.00 38.70 |
| ATOM | 3757 | CG | ARG | B | 438 | 46.055 | -6.475 | 51.956 | 1.00 41.09 |
| ATOM | 3758 | CD | ARG | B | 438 | 44.542 | -6.687 | 51.887 | 1.00 44.82 |
| ATOM | 3759 | NE | ARG | B | 438 | 43.797 | -6.041 | 52.970 | 1.00 46.62 |
| ATOM | 3760 | CZ | ARG | B | 438 | 43.856 | -6.403 | 54.253 | 1.00 48.62 |
| ATOM | 3761 | NH1 | ARG | B | 438 | 44.632 | -7.417 | 54.638 | 1.00 48.18 |
| ATOM | 3762 | NH2 | ARG | B | 438 | 43.140 | -5.741 | 55.162 | 1.00 48.71 |
| ATOM | 3763 | C | ARG | B | 438 | 45.243 | -3.879 | 50.061 | 1.00 36.17 |

Figure 6

| ATOM | 3764 | O   | ARG | B | 438 | 44.737 | -2.810  | 50.393 | 1.00 | 35.76 |
|------|------|-----|-----|---|-----|--------|---------|--------|------|-------|
| ATOM | 3765 | N   | ILE | B | 439 | 44.660 | -4.697  | 49.187 | 1.00 | 34.95 |
| ATOM | 3766 | CA  | ILE | B | 439 | 43.346 | -4.398  | 48.609 | 1.00 | 34.53 |
| ATOM | 3767 | CB  | ILE | B | 439 | 43.077 | -5.295  | 47.373 | 1.00 | 34.51 |
| ATOM | 3768 | CG2 | ILE | B | 439 | 41.592 | -5.483  | 47.130 | 1.00 | 33.62 |
| ATOM | 3769 | CG1 | ILE | B | 439 | 43.741 | -4.668  | 46.141 | 1.00 | 35.47 |
| ATOM | 3770 | CD1 | ILE | B | 439 | 44.004 | -5.648  | 44.996 | 1.00 | 35.08 |
| ATOM | 3771 | C   | ILE | B | 439 | 42.236 | -4.566  | 49.660 | 1.00 | 35.74 |
| ATOM | 3772 | O   | ILE | B | 439 | 42.215 | -5.575  | 50.385 | 1.00 | 37.02 |
| ATOM | 3773 | N   | PRO | B | 440 | 41.311 | -3.575  | 49.764 | 1.00 | 33.93 |
| ATOM | 3774 | CD  | PRO | B | 440 | 41.291 | -2.309  | 49.007 | 1.00 | 32.97 |
| ATOM | 3775 | CA  | PRO | B | 440 | 40.201 | -3.611  | 50.726 | 1.00 | 32.95 |
| ATOM | 3776 | CB  | PRO | B | 440 | 39.366 | -2.409  | 50.320 | 1.00 | 33.41 |
| ATOM | 3777 | CG  | PRO | B | 440 | 40.423 | -1.436  | 49.873 | 1.00 | 32.94 |
| ATOM | 3778 | C   | PRO | B | 440 | 39.427 | -4.900  | 50.599 | 1.00 | 32.82 |
| ATOM | 3779 | O   | PRO | B | 440 | 39.402 | -5.499  | 49.525 | 1.00 | 34.39 |
| ATOM | 3780 | N   | TYR | B | 441 | 38.845 | -5.351  | 51.708 | 1.00 | 32.05 |
| ATOM | 3781 | CA  | TYR | B | 441 | 38.087 | -6.602  | 51.758 | 1.00 | 31.34 |
| ATOM | 3782 | CB  | TYR | B | 441 | 36.696 | -6.441  | 51.153 | 1.00 | 29.27 |
| ATOM | 3783 | CG  | TYR | B | 441 | 35.954 | -5.226  | 51.607 | 1.00 | 26.74 |
| ATOM | 3784 | CD1 | TYR | B | 441 | 35.057 | -5.291  | 52.664 | 1.00 | 25.41 |
| ATOM | 3785 | CE1 | TYR | B | 441 | 34.369 | -4.166  | 53.076 | 1.00 | 24.86 |
| ATOM | 3786 | CD2 | TYR | B | 441 | 36.141 | -4.013  | 50.970 | 1.00 | 25.40 |
| ATOM | 3787 | CE2 | TYR | B | 441 | 35.459 | -2.888  | 51.367 | 1.00 | 25.86 |
| ATOM | 3788 | CZ  | TYR | B | 441 | 34.573 | -2.967  | 52.420 | 1.00 | 25.46 |
| ATOM | 3789 | OH  | TYR | B | 441 | 33.878 | -1.841  | 52.783 | 1.00 | 26.23 |
| ATOM | 3790 | C   | TYR | B | 441 | 38.810 | -7.732  | 51.030 | 1.00 | 32.97 |
| ATOM | 3791 | O   | TYR | B | 441 | 38.463 | -8.092  | 49.899 | 1.00 | 33.02 |
| ATOM | 3792 | N   | PRO | B | 442 | 39.871 | -8.264  | 51.637 | 1.00 | 35.08 |
| ATOM | 3793 | CD  | PRO | B | 442 | 40.512 | -7.913  | 52.919 | 1.00 | 35.28 |
| ATOM | 3794 | CA  | PRO | B | 442 | 40.575 | -9.356  | 50.957 | 1.00 | 36.53 |
| ATOM | 3795 | CB  | PRO | B | 442 | 41.786 | -9.588  | 51.865 | 1.00 | 36.38 |
| ATOM | 3796 | CG  | PRO | B | 442 | 41.293 | -9.164  | 53.239 | 1.00 | 35.77 |
| ATOM | 3797 | C   | PRO | B | 442 | 39.679 | -10.600 | 50.862 | 1.00 | 38.28 |
| ATOM | 3798 | O   | PRO | B | 442 | 38.794 | -10.796 | 51.689 | 1.00 | 38.39 |
| ATOM | 3799 | N   | GLY | B | 443 | 39.853 | -11.394 | 49.809 | 1.00 | 40.15 |
| ATOM | 3800 | CA  | GLY | B | 443 | 39.059 | -12.605 | 49.668 | 1.00 | 41.89 |
| ATOM | 3801 | C   | GLY | B | 443 | 37.631 | -12.367 | 49.221 | 1.00 | 43.33 |
| ATOM | 3802 | O   | GLY | B | 443 | 36.797 | -13.280 | 49.227 | 1.00 | 45.58 |
| ATOM | 3803 | N   | MET | B | 444 | 37.340 | -11.129 | 48.849 | 1.00 | 43.17 |
| ATOM | 3804 | CA  | MET | B | 444 | 36.013 | -10.775 | 48.373 | 1.00 | 43.48 |
| ATOM | 3805 | CB  | MET | B | 444 | 35.325 | -9.830  | 49.360 | 1.00 | 43.58 |
| ATOM | 3806 | CG  | MET | B | 444 | 34.828 | -10.490 | 50.627 | 1.00 | 44.02 |
| ATOM | 3807 | SD  | MET | B | 444 | 34.205 | -9.257  | 51.791 | 1.00 | 43.60 |
| ATOM | 3808 | CE  | MET | B | 444 | 32.938 | -8.628  | 50.873 | 1.00 | 43.04 |
| ATOM | 3809 | C   | MET | B | 444 | 36.120 | -10.098 | 47.007 | 1.00 | 43.14 |
| ATOM | 3810 | O   | MET | B | 444 | 37.087 | -9.379  | 46.739 | 1.00 | 43.67 |
| ATOM | 3811 | N   | THR | B | 445 | 35.148 | -10.367 | 46.138 | 1.00 | 41.60 |
| ATOM | 3812 | CA  | THR | B | 445 | 35.099 | -9.760  | 44.820 | 1.00 | 40.57 |
| ATOM | 3813 | CB  | THR | B | 445 | 34.599 | -10.771 | 43.772 | 1.00 | 41.96 |
| ATOM | 3814 | OG1 | THR | B | 445 | 33.206 | -11.039 | 43.979 | 1.00 | 43.32 |
| ATOM | 3815 | CG2 | THR | B | 445 | 35.375 | -12.085 | 43.886 | 1.00 | 40.64 |
| ATOM | 3816 | C   | THR | B | 445 | 34.108 | -8.612  | 44.956 | 1.00 | 40.44 |
| ATOM | 3817 | O   | THR | B | 445 | 33.457 | -8.493  | 45.983 | 1.00 | 41.53 |
| ATOM | 3818 | N   | ASN | B | 446 | 33.986 | -7.756  | 43.951 | 1.00 | 40.64 |
| ATOM | 3819 | CA  | ASN | B | 446 | 33.042 | -6.647  | 44.039 | 1.00 | 41.36 |
| ATOM | 3820 | CB  | ASN | B | 446 | 33.035 | -5.820  | 42.762 | 1.00 | 42.11 |
| ATOM | 3821 | CG  | ASN | B | 446 | 34.104 | -4.775  | 42.759 | 1.00 | 43.34 |
| ATOM | 3822 | OD1 | ASN | B | 446 | 35.041 | -4.822  | 43.564 | 1.00 | 42.99 |

Figure 6

| ATOM | 3823 | ND2 | ASN | B | 446 | 33.975 | -3.807 | 41.864 | 1.00 | 44.70 |
|------|------|-----|-----|---|-----|--------|--------|--------|------|-------|
| ATOM | 3824 | C | ASN | B | 446 | 31.621 | -7.059 | 44.384 | 1.00 | 41.90 |
| ATOM | 3825 | O | ASN | B | 446 | 31.057 | -6.567 | 45.361 | 1.00 | 40.46 |
| ATOM | 3826 | N | PRO | B | 447 | 31.023 | -7.973 | 43.591 | 1.00 | 42.73 |
| ATOM | 3827 | CD | PRO | B | 447 | 31.571 | -8.721 | 42.444 | 1.00 | 41.75 |
| ATOM | 3828 | CA | PRO | B | 447 | 29.649 | -8.402 | 43.885 | 1.00 | 42.21 |
| ATOM | 3829 | CB | PRO | B | 447 | 29.400 | -9.502 | 42.844 | 1.00 | 42.12 |
| ATOM | 3830 | CG | PRO | B | 447 | 30.791 | -10.002 | 42.511 | 1.00 | 42.07 |
| ATOM | 3831 | C | PRO | B | 447 | 29.450 | -8.891 | 45.323 | 1.00 | 41.11 |
| ATOM | 3832 | O | PRO | B | 447 | 28.386 | -8.676 | 45.905 | 1.00 | 41.72 |
| ATOM | 3833 | N | GLU | B | 448 | 30.481 | -9.514 | 45.893 | 1.00 | 38.77 |
| ATOM | 3834 | CA | GLU | B | 448 | 30.428 | -10.010 | 47.265 | 1.00 | 39.05 |
| ATOM | 3835 | CB | GLU | B | 448 | 31.567 | -10.981 | 47.545 | 1.00 | 40.15 |
| ATOM | 3836 | CG | GLU | B | 448 | 31.427 | -12.283 | 46.805 | 1.00 | 43.47 |
| ATOM | 3837 | CD | GLU | B | 448 | 32.534 | -13.257 | 47.117 | 1.00 | 44.66 |
| ATOM | 3838 | OE1 | GLU | B | 448 | 33.578 | -12.837 | 47.660 | 1.00 | 46.97 |
| ATOM | 3839 | OE2 | GLU | B | 448 | 32.359 | -14.454 | 46.818 | 1.00 | 46.27 |
| ATOM | 3840 | C | GLU | B | 448 | 30.470 | -8.877 | 48.275 | 1.00 | 38.02 |
| ATOM | 3841 | O | GLU | B | 448 | 29.786 | -8.937 | 49.300 | 1.00 | 38.92 |
| ATOM | 3842 | N | VAL | B | 449 | 31.288 | -7.862 | 47.994 | 1.00 | 35.10 |
| ATOM | 3843 | CA | VAL | B | 449 | 31.396 | -6.690 | 48.862 | 1.00 | 32.14 |
| ATOM | 3844 | CB | VAL | B | 449 | 32.472 | -5.682 | 48.343 | 1.00 | 31.14 |
| ATOM | 3845 | CG1 | VAL | B | 449 | 32.303 | -4.298 | 48.973 | 1.00 | 29.25 |
| ATOM | 3846 | CG2 | VAL | B | 449 | 33.865 | -6.212 | 48.654 | 1.00 | 30.08 |
| ATOM | 3847 | C | VAL | B | 449 | 30.032 | -6.036 | 48.910 | 1.00 | 31.55 |
| ATOM | 3848 | O | VAL | B | 449 | 29.609 | -5.554 | 49.952 | 1.00 | 30.77 |
| ATOM | 3849 | N | ILE | B | 450 | 29.341 | -6.060 | 47.773 | 1.00 | 32.84 |
| ATOM | 3850 | CA | ILE | B | 450 | 28.010 | -5.487 | 47.652 | 1.00 | 32.55 |
| ATOM | 3851 | CB | ILE | B | 450 | 27.531 | -5.484 | 46.182 | 1.00 | 32.54 |
| ATOM | 3852 | CG2 | ILE | B | 450 | 26.152 | -4.858 | 46.077 | 1.00 | 32.66 |
| ATOM | 3853 | CG1 | ILE | B | 450 | 28.512 | -4.708 | 45.299 | 1.00 | 33.01 |
| ATOM | 3854 | CD1 | ILE | B | 450 | 28.651 | -3.252 | 45.654 | 1.00 | 32.53 |
| ATOM | 3855 | C | ILE | B | 450 | 26.989 | -6.242 | 48.513 | 1.00 | 31.41 |
| ATOM | 3856 | O | ILE | B | 450 | 26.237 | -5.622 | 49.261 | 1.00 | 29.01 |
| ATOM | 3857 | N | GLN | B | 451 | 26.984 | -7.571 | 48.430 | 1.00 | 31.93 |
| ATOM | 3858 | CA | GLN | B | 451 | 26.019 | -8.342 | 49.198 | 1.00 | 33.33 |
| ATOM | 3859 | CB | GLN | B | 451 | 25.776 | -9.752 | 48.641 | 1.00 | 34.51 |
| ATOM | 3860 | CG | GLN | B | 451 | 26.963 | -10.682 | 48.518 | 1.00 | 38.35 |
| ATOM | 3861 | CD | GLN | B | 451 | 26.797 | -11.671 | 47.336 | 1.00 | 40.70 |
| ATOM | 3862 | OE1 | GLN | B | 451 | 27.267 | -12.815 | 47.380 | 1.00 | 41.83 |
| ATOM | 3863 | NE2 | GLN | B | 451 | 26.145 | -11.212 | 46.270 | 1.00 | 40.54 |
| ATOM | 3864 | C | GLN | B | 451 | 26.323 | -8.364 | 50.661 | 1.00 | 31.92 |
| ATOM | 3865 | O | GLN | B | 451 | 25.421 | -8.535 | 51.469 | 1.00 | 32.38 |
| ATOM | 3866 | N | ASN | B | 452 | 27.584 | -8.126 | 50.993 | 1.00 | 31.64 |
| ATOM | 3867 | CA | ASN | B | 452 | 28.021 | -8.087 | 52.386 | 1.00 | 30.16 |
| ATOM | 3868 | CB | ASN | B | 452 | 29.523 | -8.338 | 52.508 | 1.00 | 31.10 |
| ATOM | 3869 | CG | ASN | B | 452 | 29.841 | -9.760 | 52.884 | 1.00 | 31.39 |
| ATOM | 3870 | OD1 | ASN | B | 452 | 29.938 | -10.092 | 54.062 | 1.00 | 32.79 |
| ATOM | 3871 | ND2 | ASN | B | 452 | 29.999 | -10.616 | 51.888 | 1.00 | 32.99 |
| ATOM | 3872 | C | ASN | B | 452 | 27.685 | -6.738 | 52.982 | 1.00 | 29.37 |
| ATOM | 3873 | O | ASN | B | 452 | 27.349 | -6.655 | 54.152 | 1.00 | 29.73 |
| ATOM | 3874 | N | LEU | B | 453 | 27.809 | -5.679 | 52.185 | 1.00 | 28.78 |
| ATOM | 3875 | CA | LEU | B | 453 | 27.486 | -4.334 | 52.642 | 1.00 | 27.98 |
| ATOM | 3876 | CB | LEU | B | 453 | 27.960 | -3.288 | 51.648 | 1.00 | 28.87 |
| ATOM | 3877 | CG | LEU | B | 453 | 29.438 | -2.916 | 51.675 | 1.00 | 30.06 |
| ATOM | 3878 | CD1 | LEU | B | 453 | 29.627 | -1.780 | 50.681 | 1.00 | 30.96 |
| ATOM | 3879 | CD2 | LEU | B | 453 | 29.877 | -2.481 | 53.071 | 1.00 | 29.70 |
| ATOM | 3880 | C | LEU | B | 453 | 25.991 | -4.183 | 52.858 | 1.00 | 27.52 |
| ATOM | 3881 | O | LEU | B | 453 | 25.575 | -3.425 | 53.727 | 1.00 | 27.55 |

Figure 6

| | | | | | | | | | |
|---|---|---|---|---|---|---|---|---|---|
| ATOM | 3882 | N | GLU | B | 454 | 25.187 | -4.859 | 52.034 | 1.00 27.54 |
| ATOM | 3883 | CA | GLU | B | 454 | 23.731 | -4.842 | 52.178 | 1.00 28.72 |
| ATOM | 3884 | CB | GLU | B | 454 | 23.088 | -5.828 | 51.202 | 1.00 31.71 |
| ATOM | 3885 | CG | GLU | B | 454 | 22.875 | -5.367 | 49.775 | 1.00 35.16 |
| ATOM | 3886 | CD | GLU | B | 454 | 22.566 | -6.545 | 48.844 | 1.00 36.71 |
| ATOM | 3887 | OE1 | GLU | B | 454 | 22.829 | -6.415 | 47.627 | 1.00 38.89 |
| ATOM | 3888 | OE2 | GLU | B | 454 | 22.087 | -7.606 | 49.328 | 1.00 37.15 |
| ATOM | 3889 | C | GLU | B | 454 | 23.392 | -5.321 | 53.597 | 1.00 27.50 |
| ATOM | 3890 | O | GLU | B | 454 | 22.420 | -4.881 | 54.206 | 1.00 25.59 |
| ATOM | 3891 | N | ARG | B | 455 | 24.191 | -6.272 | 54.075 | 1.00 25.93 |
| ATOM | 3892 | CA | ARG | B | 455 | 24.059 | -6.880 | 55.391 | 1.00 24.89 |
| ATOM | 3893 | CB | ARG | B | 455 | 24.545 | -8.345 | 55.336 | 1.00 26.68 |
| ATOM | 3894 | CG | ARG | B | 455 | 23.614 | -9.275 | 54.566 | 1.00 31.07 |
| ATOM | 3895 | CD | ARG | B | 455 | 24.150 | -10.708 | 54.450 | 1.00 33.92 |
| ATOM | 3896 | NE | ARG | B | 455 | 25.082 | -10.833 | 53.334 | 1.00 39.15 |
| ATOM | 3897 | CZ | ARG | B | 455 | 25.851 | -11.891 | 53.107 | 1.00 40.88 |
| ATOM | 3898 | NH1 | ARG | B | 455 | 25.798 | -12.943 | 53.909 | 1.00 42.93 |
| ATOM | 3899 | NH2 | ARG | B | 455 | 26.731 | -11.866 | 52.114 | 1.00 43.19 |
| ATOM | 3900 | C | ARG | B | 455 | 24.783 | -6.118 | 56.515 | 1.00 23.15 |
| ATOM | 3901 | O | ARG | B | 455 | 24.840 | -6.588 | 57.651 | 1.00 24.28 |
| ATOM | 3902 | N | GLY | B | 456 | 25.362 | -4.969 | 56.184 | 1.00 20.54 |
| ATOM | 3903 | CA | GLY | B | 456 | 26.055 | -4.162 | 57.170 | 1.00 19.36 |
| ATOM | 3904 | C | GLY | B | 456 | 27.446 | -4.603 | 57.575 | 1.00 19.44 |
| ATOM | 3905 | O | GLY | B | 456 | 27.954 | -4.179 | 58.610 | 1.00 19.96 |
| ATOM | 3906 | N | TYR | B | 457 | 28.063 | -5.448 | 56.764 | 1.00 19.57 |
| ATOM | 3907 | CA | TYR | B | 457 | 29.418 | -5.930 | 57.021 | 1.00 18.86 |
| ATOM | 3908 | CB | TYR | B | 457 | 29.851 | -6.863 | 55.902 | 1.00 16.96 |
| ATOM | 3909 | CG | TYR | B | 457 | 31.220 | -7.474 | 56.082 | 1.00 16.08 |
| ATOM | 3910 | CD1 | TYR | B | 457 | 31.362 | -8.750 | 56.649 | 1.00 15.38 |
| ATOM | 3911 | CE1 | TYR | B | 457 | 32.620 | -9.322 | 56.831 | 1.00 16.37 |
| ATOM | 3912 | CD2 | TYR | B | 457 | 32.379 | -6.781 | 55.704 | 1.00 15.96 |
| ATOM | 3913 | CE2 | TYR | B | 457 | 33.648 | -7.340 | 55.887 | 1.00 15.41 |
| ATOM | 3914 | CZ | TYR | B | 457 | 33.760 | -8.611 | 56.453 | 1.00 16.49 |
| ATOM | 3915 | OH | TYR | B | 457 | 35.010 | -9.172 | 56.644 | 1.00 16.08 |
| ATOM | 3916 | C | TYR | B | 457 | 30.433 | -4.803 | 57.099 | 1.00 20.60 |
| ATOM | 3917 | O | TYR | B | 457 | 30.364 | -3.823 | 56.340 | 1.00 20.26 |
| ATOM | 3918 | N | ARG | B | 458 | 31.371 | -4.951 | 58.034 | 1.00 21.24 |
| ATOM | 3919 | CA | ARG | B | 458 | 32.455 | -3.993 | 58.236 | 1.00 20.68 |
| ATOM | 3920 | CB | ARG | B | 458 | 32.232 | -3.174 | 59.508 | 1.00 18.02 |
| ATOM | 3921 | CG | ARG | B | 458 | 31.040 | -2.257 | 59.460 | 1.00 16.48 |
| ATOM | 3922 | CD | ARG | B | 458 | 31.249 | -1.208 | 58.415 | 1.00 17.88 |
| ATOM | 3923 | NE | ARG | B | 458 | 30.139 | -0.271 | 58.287 | 1.00 16.66 |
| ATOM | 3924 | CZ | ARG | B | 458 | 29.037 | -0.518 | 57.588 | 1.00 17.51 |
| ATOM | 3925 | NH1 | ARG | B | 458 | 28.898 | -1.679 | 56.961 | 1.00 18.86 |
| ATOM | 3926 | NH2 | ARG | B | 458 | 28.083 | 0.398 | 57.485 | 1.00 17.04 |
| ATOM | 3927 | C | ARG | B | 458 | 33.748 | -4.812 | 58.339 | 1.00 22.56 |
| ATOM | 3928 | O | ARG | B | 458 | 33.723 | -5.953 | 58.816 | 1.00 21.61 |
| ATOM | 3929 | N | MET | B | 459 | 34.849 | -4.283 | 57.808 | 1.00 22.77 |
| ATOM | 3930 | CA | MET | B | 459 | 36.111 | -5.002 | 57.885 | 1.00 24.84 |
| ATOM | 3931 | CB | MET | B | 459 | 37.186 | -4.297 | 57.069 | 1.00 25.20 |
| ATOM | 3932 | CG | MET | B | 459 | 37.146 | -4.588 | 55.588 | 1.00 25.79 |
| ATOM | 3933 | SD | MET | B | 459 | 38.531 | -3.821 | 54.750 | 1.00 26.85 |
| ATOM | 3934 | CE | MET | B | 459 | 37.924 | -2.125 | 54.485 | 1.00 22.55 |
| ATOM | 3935 | C | MET | B | 459 | 36.561 | -5.084 | 59.330 | 1.00 25.15 |
| ATOM | 3936 | O | MET | B | 459 | 36.328 | -4.150 | 60.094 | 1.00 25.00 |
| ATOM | 3937 | N | VAL | B | 460 | 37.194 | -6.196 | 59.702 | 1.00 26.07 |
| ATOM | 3938 | CA | VAL | B | 460 | 37.699 | -6.368 | 61.065 | 1.00 27.35 |
| ATOM | 3939 | CB | VAL | B | 460 | 37.984 | -7.859 | 61.396 | 1.00 26.52 |
| ATOM | 3940 | CG1 | VAL | B | 460 | 36.723 | -8.682 | 61.204 | 1.00 24.25 |

Figure 6

| | | | | | | | | | |
|---|---|---|---|---|---|---|---|---|---|
| ATOM | 3941 | CG2 | VAL | B | 460 | 39.140 | -8.399 | 60.545 | 1.00 25.34 |
| ATOM | 3942 | C | VAL | B | 460 | 38.972 | -5.531 | 61.217 | 1.00 28.93 |
| ATOM | 3943 | O | VAL | B | 460 | 39.399 | -4.885 | 60.266 | 1.00 29.70 |
| ATOM | 3944 | N | ARG | B | 461 | 39.568 | -5.507 | 62.404 | 1.00 30.18 |
| ATOM | 3945 | CA | ARG | B | 461 | 40.776 | -4.718 | 62.599 | 1.00 30.76 |
| ATOM | 3946 | CB | ARG | B | 461 | 41.082 | -4.553 | 64.090 | 1.00 34.02 |
| ATOM | 3947 | CG | ARG | B | 461 | 42.096 | -3.451 | 64.394 | 1.00 35.72 |
| ATOM | 3948 | CD | ARG | B | 461 | 42.452 | -3.428 | 65.862 | 1.00 39.57 |
| ATOM | 3949 | NE | ARG | B | 461 | 42.912 | -4.743 | 66.299 | 1.00 44.40 |
| ATOM | 3950 | CZ | ARG | B | 461 | 44.097 | -5.267 | 65.990 | 1.00 47.43 |
| ATOM | 3951 | NH1 | ARG | B | 461 | 44.967 | -4.581 | 65.253 | 1.00 48.79 |
| ATOM | 3952 | NH2 | ARG | B | 461 | 44.389 | -6.515 | 66.347 | 1.00 48.60 |
| ATOM | 3953 | C | ARG | B | 461 | 41.977 | -5.308 | 61.863 | 1.00 30.23 |
| ATOM | 3954 | O | ARG | B | 461 | 42.311 | -6.481 | 62.019 | 1.00 28.07 |
| ATOM | 3955 | N | PRO | B | 462 | 42.596 | -4.510 | 60.983 | 1.00 31.47 |
| ATOM | 3956 | CD | PRO | B | 462 | 42.144 | -3.178 | 60.547 | 1.00 30.90 |
| ATOM | 3957 | CA | PRO | B | 462 | 43.763 | -4.923 | 60.202 | 1.00 33.07 |
| ATOM | 3958 | CB | PRO | B | 462 | 44.089 | -3.660 | 59.404 | 1.00 31.79 |
| ATOM | 3959 | CG | PRO | B | 462 | 42.759 | -3.070 | 59.179 | 1.00 30.32 |
| ATOM | 3960 | C | PRO | B | 462 | 44.938 | -5.305 | 61.093 | 1.00 34.15 |
| ATOM | 3961 | O | PRO | B | 462 | 45.150 | -4.676 | 62.127 | 1.00 32.98 |
| ATOM | 3962 | N | ASP | B | 463 | 45.678 | -6.341 | 60.690 | 1.00 37.18 |
| ATOM | 3963 | CA | ASP | B | 463 | 46.863 | -6.797 | 61.421 | 1.00 40.49 |
| ATOM | 3964 | CB | ASP | B | 463 | 47.618 | -7.872 | 60.611 | 1.00 42.06 |
| ATOM | 3965 | CG | ASP | B | 463 | 46.981 | -9.258 | 60.706 | 1.00 43.33 |
| ATOM | 3966 | OD1 | ASP | B | 463 | 45.989 | -9.420 | 61.452 | 1.00 43.47 |
| ATOM | 3967 | OD2 | ASP | B | 463 | 47.490 | -10.194 | 60.033 | 1.00 43.08 |
| ATOM | 3968 | C | ASP | B | 463 | 47.776 | -5.583 | 61.594 | 1.00 41.66 |
| ATOM | 3969 | O | ASP | B | 463 | 47.972 | -4.813 | 60.645 | 1.00 43.03 |
| ATOM | 3970 | N | ASN | B | 464 | 48.270 | -5.374 | 62.811 | 1.00 41.66 |
| ATOM | 3971 | CA | ASN | B | 464 | 49.158 | -4.247 | 63.095 | 1.00 42.43 |
| ATOM | 3972 | CB | ASN | B | 464 | 50.436 | -4.331 | 62.244 | 1.00 45.69 |
| ATOM | 3973 | CG | ASN | B | 464 | 51.351 | -5.478 | 62.663 | 1.00 47.43 |
| ATOM | 3974 | OD1 | ASN | B | 464 | 51.960 | -5.431 | 63.738 | 1.00 49.24 |
| ATOM | 3975 | ND2 | ASN | B | 464 | 51.474 | -6.498 | 61.804 | 1.00 46.73 |
| ATOM | 3976 | C | ASN | B | 464 | 48.501 | -2.881 | 62.902 | 1.00 41.62 |
| ATOM | 3977 | O | ASN | B | 464 | 49.034 | -2.007 | 62.215 | 1.00 40.90 |
| ATOM | 3978 | N | CYS | B | 465 | 47.328 | -2.714 | 63.500 | 1.00 40.50 |
| ATOM | 3979 | CA | CYS | B | 465 | 46.590 | -1.454 | 63.431 | 1.00 36.84 |
| ATOM | 3980 | CB | CYS | B | 465 | 45.390 | -1.584 | 62.486 | 1.00 35.63 |
| ATOM | 3981 | SG | CYS | B | 465 | 44.285 | -0.133 | 62.447 | 1.00 32.30 |
| ATOM | 3982 | C | CYS | B | 465 | 46.103 | -1.158 | 64.841 | 1.00 34.54 |
| ATOM | 3983 | O | CYS | B | 465 | 45.570 | -2.045 | 65.502 | 1.00 34.73 |
| ATOM | 3984 | N | PRO | B | 466 | 46.347 | 0.063 | 65.344 | 1.00 30.99 |
| ATOM | 3985 | CD | PRO | B | 466 | 47.185 | 1.100 | 64.714 | 1.00 30.50 |
| ATOM | 3986 | CA | PRO | B | 466 | 45.934 | 0.488 | 66.681 | 1.00 30.14 |
| ATOM | 3987 | CB | PRO | B | 466 | 46.433 | 1.927 | 66.744 | 1.00 29.92 |
| ATOM | 3988 | CG | PRO | B | 466 | 47.643 | 1.905 | 65.903 | 1.00 29.97 |
| ATOM | 3989 | C | PRO | B | 466 | 44.424 | 0.457 | 66.822 | 1.00 31.45 |
| ATOM | 3990 | O | PRO | B | 466 | 43.717 | 0.856 | 65.911 | 1.00 33.16 |
| ATOM | 3991 | N | GLU | B | 467 | 43.925 | -0.003 | 67.965 | 1.00 32.62 |
| ATOM | 3992 | CA | GLU | B | 467 | 42.480 | -0.046 | 68.182 | 1.00 33.42 |
| ATOM | 3993 | CB | GLU | B | 467 | 42.152 | -0.633 | 69.558 | 1.00 34.95 |
| ATOM | 3994 | CG | GLU | B | 467 | 41.443 | -1.988 | 69.546 | 1.00 36.69 |
| ATOM | 3995 | CD | GLU | B | 467 | 40.057 | -1.938 | 68.920 | 1.00 37.64 |
| ATOM | 3996 | OE1 | GLU | B | 467 | 39.729 | -2.848 | 68.132 | 1.00 38.23 |
| ATOM | 3997 | OE2 | GLU | B | 467 | 39.286 | -1.011 | 69.225 | 1.00 37.01 |
| ATOM | 3998 | C | GLU | B | 467 | 41.834 | 1.341 | 68.066 | 1.00 33.80 |
| ATOM | 3999 | O | GLU | B | 467 | 40.669 | 1.453 | 67.670 | 1.00 33.65 |

Figure 6

| | | | | | | | | | |
|---|---|---|---|---|---|---|---|---|---|
| ATOM | 4000 | N | GLU | B | 468 | 42.572 | 2.388 | 68.441 | 1.00 33.45 |
| ATOM | 4001 | CA | GLU | B | 468 | 42.035 | 3.743 | 68.351 | 1.00 34.98 |
| ATOM | 4002 | CB | GLU | B | 468 | 42.951 | 4.761 | 69.027 | 1.00 37.32 |
| ATOM | 4003 | CG | GLU | B | 468 | 43.186 | 4.526 | 70.506 | 1.00 41.22 |
| ATOM | 4004 | CD | GLU | B | 468 | 44.116 | 3.327 | 70.801 | 1.00 44.02 |
| ATOM | 4005 | OE1 | GLU | B | 468 | 45.134 | 3.141 | 70.076 | 1.00 41.76 |
| ATOM | 4006 | OE2 | GLU | B | 468 | 43.823 | 2.580 | 71.778 | 1.00 45.49 |
| ATOM | 4007 | C | GLU | B | 468 | 41.847 | 4.121 | 66.882 | 1.00 35.00 |
| ATOM | 4008 | O | GLU | B | 468 | 40.854 | 4.758 | 66.515 | 1.00 36.16 |
| ATOM | 4009 | N | LEU | B | 469 | 42.784 | 3.702 | 66.035 | 1.00 32.38 |
| ATOM | 4010 | CA | LEU | B | 469 | 42.678 | 3.990 | 64.624 | 1.00 30.39 |
| ATOM | 4011 | CB | LEU | B | 469 | 43.974 | 3.660 | 63.892 | 1.00 30.96 |
| ATOM | 4012 | CG | LEU | B | 469 | 44.082 | 4.129 | 62.438 | 1.00 29.76 |
| ATOM | 4013 | CD1 | LEU | B | 469 | 44.092 | 5.645 | 62.387 | 1.00 29.75 |
| ATOM | 4014 | CD2 | LEU | B | 469 | 45.352 | 3.582 | 61.834 | 1.00 28.46 |
| ATOM | 4015 | C | LEU | B | 469 | 41.519 | 3.193 | 64.041 | 1.00 29.65 |
| ATOM | 4016 | O | LEU | B | 469 | 40.770 | 3.728 | 63.233 | 1.00 31.49 |
| ATOM | 4017 | N | TYR | B | 470 | 41.343 | 1.937 | 64.469 | 1.00 27.55 |
| ATOM | 4018 | CA | TYR | B | 470 | 40.233 | 1.117 | 63.969 | 1.00 28.21 |
| ATOM | 4019 | CB | TYR | B | 470 | 40.295 | -0.334 | 64.458 | 1.00 27.35 |
| ATOM | 4020 | CG | TYR | B | 470 | 39.136 | -1.215 | 63.974 | 1.00 26.97 |
| ATOM | 4021 | CD1 | TYR | B | 470 | 38.956 | -1.510 | 62.622 | 1.00 26.68 |
| ATOM | 4022 | CE1 | TYR | B | 470 | 37.920 | -2.369 | 62.198 | 1.00 26.21 |
| ATOM | 4023 | CD2 | TYR | B | 470 | 38.247 | -1.790 | 64.884 | 1.00 27.20 |
| ATOM | 4024 | CE2 | TYR | B | 470 | 37.209 | -2.642 | 64.470 | 1.00 25.16 |
| ATOM | 4025 | CZ | TYR | B | 470 | 37.051 | -2.930 | 63.133 | 1.00 25.52 |
| ATOM | 4026 | OH | TYR | B | 470 | 36.039 | -3.781 | 62.736 | 1.00 23.88 |
| ATOM | 4027 | C | TYR | B | 470 | 38.864 | 1.689 | 64.333 | 1.00 29.59 |
| ATOM | 4028 | O | TYR | B | 470 | 37.890 | 1.448 | 63.615 | 1.00 32.59 |
| ATOM | 4029 | N | GLN | B | 471 | 38.765 | 2.401 | 65.455 | 1.00 28.05 |
| ATOM | 4030 | CA | GLN | B | 471 | 37.479 | 2.972 | 65.843 | 1.00 26.66 |
| ATOM | 4031 | CB | GLN | B | 471 | 37.403 | 3.183 | 67.360 | 1.00 26.83 |
| ATOM | 4032 | CG | GLN | B | 471 | 37.333 | 1.876 | 68.163 | 1.00 24.18 |
| ATOM | 4033 | CD | GLN | B | 471 | 36.159 | 0.966 | 67.758 | 1.00 25.38 |
| ATOM | 4034 | OE1 | GLN | B | 471 | 35.117 | 1.438 | 67.283 | 1.00 23.88 |
| ATOM | 4035 | NE2 | GLN | B | 471 | 36.329 | -0.349 | 67.944 | 1.00 24.82 |
| ATOM | 4036 | C | GLN | B | 471 | 37.221 | 4.255 | 65.070 | 1.00 26.41 |
| ATOM | 4037 | O | GLN | B | 471 | 36.083 | 4.699 | 64.934 | 1.00 25.93 |
| ATOM | 4038 | N | LEU | B | 472 | 38.291 | 4.836 | 64.540 | 1.00 26.80 |
| ATOM | 4039 | CA | LEU | B | 472 | 38.177 | 6.039 | 63.722 | 1.00 26.77 |
| ATOM | 4040 | CB | LEU | B | 472 | 39.535 | 6.715 | 63.601 | 1.00 29.70 |
| ATOM | 4041 | CG | LEU | B | 472 | 39.591 | 8.238 | 63.602 | 1.00 31.57 |
| ATOM | 4042 | CD1 | LEU | B | 472 | 38.911 | 8.801 | 64.835 | 1.00 30.74 |
| ATOM | 4043 | CD2 | LEU | B | 472 | 41.055 | 8.652 | 63.574 | 1.00 32.90 |
| ATOM | 4044 | C | LEU | B | 472 | 37.681 | 5.587 | 62.340 | 1.00 23.92 |
| ATOM | 4045 | O | LEU | B | 472 | 36.953 | 6.317 | 61.676 | 1.00 25.58 |
| ATOM | 4046 | N | MET | B | 473 | 38.055 | 4.371 | 61.939 | 1.00 19.35 |
| ATOM | 4047 | CA | MET | B | 473 | 37.622 | 3.781 | 60.672 | 1.00 18.95 |
| ATOM | 4048 | CB | MET | B | 473 | 38.353 | 2.460 | 60.422 | 1.00 17.33 |
| ATOM | 4049 | CG | MET | B | 473 | 39.829 | 2.554 | 60.139 | 1.00 14.92 |
| ATOM | 4050 | SD | MET | B | 473 | 40.566 | 0.909 | 59.997 | 1.00 16.08 |
| ATOM | 4051 | CE | MET | B | 473 | 42.269 | 1.342 | 59.662 | 1.00 13.07 |
| ATOM | 4052 | C | MET | B | 473 | 36.115 | 3.499 | 60.714 | 1.00 20.03 |
| ATOM | 4053 | O | MET | B | 473 | 35.359 | 3.885 | 59.815 | 1.00 18.42 |
| ATOM | 4054 | N | ARG | B | 474 | 35.694 | 2.813 | 61.773 | 1.00 21.26 |
| ATOM | 4055 | CA | ARG | B | 474 | 34.295 | 2.451 | 62.002 | 1.00 22.27 |
| ATOM | 4056 | CB | ARG | B | 474 | 34.179 | 1.621 | 63.270 | 1.00 21.33 |
| ATOM | 4057 | CG | ARG | B | 474 | 34.930 | 0.314 | 63.199 | 1.00 22.38 |
| ATOM | 4058 | CD | ARG | B | 474 | 34.244 | -0.667 | 62.274 | 1.00 25.59 |

Figure 6

```
ATOM   4059  NE   ARG B 474      32.883   -0.976   62.717  1.00 27.16
ATOM   4060  CZ   ARG B 474      32.464   -2.170   63.119  1.00 26.15
ATOM   4061  NH1  ARG B 474      33.294   -3.199   63.156  1.00 25.39
ATOM   4062  NH2  ARG B 474      31.196   -2.339   63.447  1.00 26.09
ATOM   4063  C    ARG B 474      33.347    3.648   62.063  1.00 22.95
ATOM   4064  O    ARG B 474      32.169    3.525   61.743  1.00 23.63
ATOM   4065  N    LEU B 475      33.846    4.790   62.519  1.00 24.14
ATOM   4066  CA   LEU B 475      33.035    5.999   62.553  1.00 24.96
ATOM   4067  CB   LEU B 475      33.631    7.053   63.490  1.00 26.25
ATOM   4068  CG   LEU B 475      33.326    6.844   64.986  1.00 27.04
ATOM   4069  CD1  LEU B 475      34.071    7.865   65.822  1.00 26.41
ATOM   4070  CD2  LEU B 475      31.830    6.939   65.230  1.00 25.30
ATOM   4071  C    LEU B 475      32.946    6.522   61.119  1.00 25.68
ATOM   4072  O    LEU B 475      31.935    7.114   60.728  1.00 27.72
ATOM   4073  N    CYS B 476      33.995    6.274   60.330  1.00 23.41
ATOM   4074  CA   CYS B 476      34.007    6.672   58.925  1.00 22.23
ATOM   4075  CB   CYS B 476      35.392    6.449   58.303  1.00 22.37
ATOM   4076  SG   CYS B 476      36.600    7.726   58.616  1.00 23.91
ATOM   4077  C    CYS B 476      32.993    5.795   58.180  1.00 20.11
ATOM   4078  O    CYS B 476      32.382    6.240   57.226  1.00 18.04
ATOM   4079  N    TRP B 477      32.847    4.548   58.631  1.00 18.13
ATOM   4080  CA   TRP B 477      31.938    3.565   58.038  1.00 17.01
ATOM   4081  CB   TRP B 477      32.556    2.166   58.085  1.00 16.76
ATOM   4082  CG   TRP B 477      33.903    2.062   57.444  1.00 16.69
ATOM   4083  CD2  TRP B 477      34.911    1.073   57.721  1.00 16.28
ATOM   4084  CE2  TRP B 477      36.031    1.396   56.933  1.00 16.28
ATOM   4085  CE3  TRP B 477      34.972   -0.041   58.566  1.00 16.80
ATOM   4086  CD1  TRP B 477      34.438    2.905   56.521  1.00 15.81
ATOM   4087  NE1  TRP B 477      35.717    2.513   56.213  1.00 16.39
ATOM   4088  CZ2  TRP B 477      37.206    0.638   56.966  1.00 15.76
ATOM   4089  CZ3  TRP B 477      36.138   -0.792   58.600  1.00 17.17
ATOM   4090  CH2  TRP B 477      37.239   -0.447   57.804  1.00 16.30
ATOM   4091  C    TRP B 477      30.533    3.473   58.631  1.00 16.86
ATOM   4092  O    TRP B 477      29.886    2.440   58.521  1.00 16.49
ATOM   4093  N    LYS B 478      30.047    4.543   59.238  1.00 18.49
ATOM   4094  CA   LYS B 478      28.696    4.508   59.798  1.00 20.54
ATOM   4095  CB   LYS B 478      28.407    5.734   60.684  1.00 20.72
ATOM   4096  CG   LYS B 478      29.249    5.826   61.958  1.00 21.58
ATOM   4097  CD   LYS B 478      28.903    4.743   62.956  1.00 22.46
ATOM   4098  CE   LYS B 478      27.605    5.061   63.662  1.00 24.14
ATOM   4099  NZ   LYS B 478      27.047    3.839   64.337  1.00 26.44
ATOM   4100  C    LYS B 478      27.713    4.454   58.637  1.00 21.73
ATOM   4101  O    LYS B 478      27.891    5.142   57.626  1.00 22.29
ATOM   4102  N    GLU B 479      26.691    3.615   58.767  1.00 22.52
ATOM   4103  CA   GLU B 479      25.682    3.474   57.734  1.00 23.91
ATOM   4104  CB   GLU B 479      24.595    2.513   58.189  1.00 23.95
ATOM   4105  CG   GLU B 479      23.660    2.077   57.081  1.00 24.94
ATOM   4106  CD   GLU B 479      24.372    1.346   55.937  1.00 25.69
ATOM   4107  OE1  GLU B 479      25.287    0.528   56.202  1.00 24.19
ATOM   4108  OE2  GLU B 479      23.995    1.582   54.767  1.00 24.93
ATOM   4109  C    GLU B 479      25.078    4.811   57.300  1.00 25.28
ATOM   4110  O    GLU B 479      24.846    5.015   56.112  1.00 26.24
ATOM   4111  N    ARG B 480      24.851    5.729   58.242  1.00 24.79
ATOM   4112  CA   ARG B 480      24.294    7.046   57.907  1.00 26.12
ATOM   4113  CB   ARG B 480      23.356    7.531   58.997  1.00 28.92
ATOM   4114  CG   ARG B 480      22.120    6.726   59.172  1.00 32.19
ATOM   4115  CD   ARG B 480      21.552    7.083   60.504  1.00 35.78
ATOM   4116  NE   ARG B 480      20.252    6.481   60.714  1.00 41.10
ATOM   4117  CZ   ARG B 480      19.673    6.342   61.903  1.00 43.81
```

Figure 6

```
ATOM   4118  NH1 ARG B 480      20.289    6.760   63.007  1.00 45.29
ATOM   4119  NH2 ARG B 480      18.454    5.823   61.979  1.00 45.05
ATOM   4120  C   ARG B 480      25.380    8.105   57.704  1.00 24.65
ATOM   4121  O   ARG B 480      26.252    8.284   58.541  1.00 25.97
ATOM   4122  N   PRO B 481      25.269    8.905   56.645  1.00 23.55
ATOM   4123  CD  PRO B 481      24.233    8.949   55.599  1.00 22.38
ATOM   4124  CA  PRO B 481      26.285    9.924   56.404  1.00 23.17
ATOM   4125  CB  PRO B 481      25.799   10.596   55.112  1.00 22.40
ATOM   4126  CG  PRO B 481      24.970    9.569   54.469  1.00 21.02
ATOM   4127  C   PRO B 481      26.468   10.955   57.507  1.00 22.62
ATOM   4128  O   PRO B 481      27.577   11.469   57.700  1.00 23.94
ATOM   4129  N   GLU B 482      25.387   11.293   58.202  1.00 21.88
ATOM   4130  CA  GLU B 482      25.452   12.316   59.237  1.00 21.73
ATOM   4131  CB  GLU B 482      24.037   12.791   59.600  1.00 23.27
ATOM   4132  CG  GLU B 482      23.194   11.808   60.440  1.00 26.43
ATOM   4133  CD  GLU B 482      22.316   10.850   59.628  1.00 28.13
ATOM   4134  OE1 GLU B 482      22.505   10.721   58.404  1.00 28.01
ATOM   4135  OE2 GLU B 482      21.413   10.225   60.230  1.00 29.42
ATOM   4136  C   GLU B 482      26.219   11.862   60.474  1.00 20.37
ATOM   4137  O   GLU B 482      26.699   12.680   61.247  1.00 19.33
ATOM   4138  N   ASP B 483      26.367   10.551   60.619  1.00 18.43
ATOM   4139  CA  ASP B 483      27.045    9.951   61.754  1.00 18.01
ATOM   4140  CB  ASP B 483      26.434    8.585   62.055  1.00 19.95
ATOM   4141  CG  ASP B 483      25.063    8.687   62.713  1.00 22.10
ATOM   4142  OD1 ASP B 483      24.838    9.685   63.424  1.00 22.44
ATOM   4143  OD2 ASP B 483      24.216    7.782   62.528  1.00 22.97
ATOM   4144  C   ASP B 483      28.538    9.796   61.580  1.00 19.74
ATOM   4145  O   ASP B 483      29.237    9.394   62.515  1.00 22.90
ATOM   4146  N   ARG B 484      29.025   10.103   60.381  1.00 18.91
ATOM   4147  CA  ARG B 484      30.445   10.005   60.053  1.00 18.00
ATOM   4148  CB  ARG B 484      30.619    9.687   58.562  1.00 17.59
ATOM   4149  CG  ARG B 484      29.978    8.404   58.104  1.00 17.42
ATOM   4150  CD  ARG B 484      30.067    8.266   56.591  1.00 17.73
ATOM   4151  NE  ARG B 484      29.244    7.160   56.114  1.00 19.12
ATOM   4152  CZ  ARG B 484      28.612    7.129   54.938  1.00 19.06
ATOM   4153  NH1 ARG B 484      28.710    8.136   54.093  1.00 19.07
ATOM   4154  NH2 ARG B 484      27.814    6.110   54.643  1.00 20.21
ATOM   4155  C   ARG B 484      31.133   11.328   60.386  1.00 18.32
ATOM   4156  O   ARG B 484      30.596   12.388   60.105  1.00 17.10
ATOM   4157  N   PRO B 485      32.375   11.279   60.900  1.00 18.66
ATOM   4158  CD  PRO B 485      33.227   10.084   61.025  1.00 18.51
ATOM   4159  CA  PRO B 485      33.120   12.493   61.261  1.00 19.10
ATOM   4160  CB  PRO B 485      34.464   11.939   61.764  1.00 19.65
ATOM   4161  CG  PRO B 485      34.186   10.505   62.104  1.00 19.87
ATOM   4162  C   PRO B 485      33.378   13.445   60.082  1.00 20.52
ATOM   4163  O   PRO B 485      33.285   13.048   58.922  1.00 20.36
ATOM   4164  N   THR B 486      33.650   14.714   60.398  1.00 19.37
ATOM   4165  CA  THR B 486      33.999   15.706   59.397  1.00 19.38
ATOM   4166  CB  THR B 486      33.759   17.160   59.907  1.00 17.30
ATOM   4167  OG1 THR B 486      34.441   17.364   61.142  1.00 18.44
ATOM   4168  CG2 THR B 486      32.289   17.412   60.109  1.00 15.92
ATOM   4169  C   THR B 486      35.497   15.483   59.144  1.00 21.73
ATOM   4170  O   THR B 486      36.165   14.834   59.954  1.00 23.10
ATOM   4171  N   PHE B 487      36.018   15.940   58.006  1.00 22.47
ATOM   4172  CA  PHE B 487      37.451   15.763   57.729  1.00 22.44
ATOM   4173  CB  PHE B 487      37.794   16.017   56.238  1.00 19.41
ATOM   4174  CG  PHE B 487      37.572   14.809   55.337  1.00 17.41
ATOM   4175  CD1 PHE B 487      38.356   13.666   55.467  1.00 15.33
ATOM   4176  CD2 PHE B 487      36.574   14.815   54.361  1.00 17.05
```

Figure 6

| | | | | | | | | | |
|---|---|---|---|---|---|---|---|---|---|
| ATOM | 4177 | CE1 | PHE | B | 487 | 38.147 | 12.546 | 54.647 | 1.00 13.40 |
| ATOM | 4178 | CE2 | PHE | B | 487 | 36.365 | 13.692 | 53.539 | 1.00 15.22 |
| ATOM | 4179 | CZ | PHE | B | 487 | 37.159 | 12.556 | 53.691 | 1.00 13.38 |
| ATOM | 4180 | C | PHE | B | 487 | 38.246 | 16.693 | 58.657 | 1.00 23.73 |
| ATOM | 4181 | O | PHE | B | 487 | 39.398 | 16.425 | 59.001 | 1.00 24.84 |
| ATOM | 4182 | N | ASP | B | 488 | 37.601 | 17.767 | 59.092 | 1.00 25.05 |
| ATOM | 4183 | CA | ASP | B | 488 | 38.214 | 18.715 | 60.007 | 1.00 26.06 |
| ATOM | 4184 | CB | ASP | B | 488 | 37.217 | 19.830 | 60.285 | 1.00 28.54 |
| ATOM | 4185 | CG | ASP | B | 488 | 37.714 | 20.810 | 61.298 | 1.00 30.59 |
| ATOM | 4186 | OD1 | ASP | B | 488 | 38.945 | 20.987 | 61.416 | 1.00 31.70 |
| ATOM | 4187 | OD2 | ASP | B | 488 | 36.861 | 21.416 | 61.969 | 1.00 32.32 |
| ATOM | 4188 | C | ASP | B | 488 | 38.553 | 17.962 | 61.297 | 1.00 26.22 |
| ATOM | 4189 | O | ASP | B | 488 | 39.600 | 18.187 | 61.910 | 1.00 28.55 |
| ATOM | 4190 | N | TYR | B | 489 | 37.671 | 17.038 | 61.672 | 1.00 25.09 |
| ATOM | 4191 | CA | TYR | B | 489 | 37.850 | 16.225 | 62.851 | 1.00 23.58 |
| ATOM | 4192 | CB | TYR | B | 489 | 36.554 | 15.511 | 63.221 | 1.00 23.60 |
| ATOM | 4193 | CG | TYR | B | 489 | 36.737 | 14.503 | 64.338 | 1.00 25.22 |
| ATOM | 4194 | CD1 | TYR | B | 489 | 36.962 | 14.919 | 65.652 | 1.00 25.78 |
| ATOM | 4195 | CE1 | TYR | B | 489 | 37.196 | 13.990 | 66.681 | 1.00 27.01 |
| ATOM | 4196 | CD2 | TYR | B | 489 | 36.750 | 13.130 | 64.071 | 1.00 26.45 |
| ATOM | 4197 | CE2 | TYR | B | 489 | 36.982 | 12.188 | 65.078 | 1.00 26.37 |
| ATOM | 4198 | CZ | TYR | B | 489 | 37.211 | 12.620 | 66.389 | 1.00 28.24 |
| ATOM | 4199 | OH | TYR | B | 489 | 37.470 | 11.695 | 67.399 | 1.00 27.74 |
| ATOM | 4200 | C | TYR | B | 489 | 38.934 | 15.191 | 62.643 | 1.00 24.39 |
| ATOM | 4201 | O | TYR | B | 489 | 39.829 | 15.053 | 63.474 | 1.00 26.86 |
| ATOM | 4202 | N | LEU | B | 490 | 38.816 | 14.416 | 61.571 | 1.00 23.68 |
| ATOM | 4203 | CA | LEU | B | 490 | 39.791 | 13.369 | 61.270 | 1.00 23.42 |
| ATOM | 4204 | CB | LEU | B | 490 | 39.423 | 12.621 | 59.987 | 1.00 23.13 |
| ATOM | 4205 | CG | LEU | B | 490 | 38.215 | 11.690 | 60.044 | 1.00 21.07 |
| ATOM | 4206 | CD1 | LEU | B | 490 | 37.612 | 11.540 | 58.676 | 1.00 20.29 |
| ATOM | 4207 | CD2 | LEU | B | 490 | 38.625 | 10.354 | 60.600 | 1.00 20.17 |
| ATOM | 4208 | C | LEU | B | 490 | 41.207 | 13.903 | 61.162 | 1.00 25.24 |
| ATOM | 4209 | O | LEU | B | 490 | 42.165 | 13.171 | 61.438 | 1.00 25.35 |
| ATOM | 4210 | N | ARG | B | 491 | 41.345 | 15.161 | 60.739 | 1.00 26.16 |
| ATOM | 4211 | CA | ARG | B | 491 | 42.652 | 15.788 | 60.634 | 1.00 28.99 |
| ATOM | 4212 | CB | ARG | B | 491 | 42.562 | 17.128 | 59.919 | 1.00 31.12 |
| ATOM | 4213 | CG | ARG | B | 491 | 43.875 | 17.892 | 59.952 | 1.00 35.83 |
| ATOM | 4214 | CD | ARG | B | 491 | 43.695 | 19.382 | 59.722 | 1.00 40.67 |
| ATOM | 4215 | NE | ARG | B | 491 | 42.596 | 19.944 | 60.515 | 1.00 45.96 |
| ATOM | 4216 | CZ | ARG | B | 491 | 42.683 | 20.382 | 61.782 | 1.00 47.72 |
| ATOM | 4217 | NH1 | ARG | B | 491 | 43.832 | 20.333 | 62.465 | 1.00 47.28 |
| ATOM | 4218 | NH2 | ARG | B | 491 | 41.610 | 20.923 | 62.358 | 1.00 48.17 |
| ATOM | 4219 | C | ARG | B | 491 | 43.200 | 16.014 | 62.045 | 1.00 30.45 |
| ATOM | 4220 | O | ARG | B | 491 | 44.345 | 15.652 | 62.342 | 1.00 30.22 |
| ATOM | 4221 | N | SER | B | 492 | 42.378 | 16.613 | 62.907 | 1.00 31.23 |
| ATOM | 4222 | CA | SER | B | 492 | 42.749 | 16.889 | 64.296 | 1.00 30.94 |
| ATOM | 4223 | CB | SER | B | 492 | 41.571 | 17.502 | 65.038 | 1.00 30.96 |
| ATOM | 4224 | OG | SER | B | 492 | 41.243 | 18.754 | 64.481 | 1.00 32.25 |
| ATOM | 4225 | C | SER | B | 492 | 43.187 | 15.641 | 65.046 | 1.00 31.09 |
| ATOM | 4226 | O | SER | B | 492 | 44.226 | 15.639 | 65.703 | 1.00 31.18 |
| ATOM | 4227 | N | VAL | B | 493 | 42.375 | 14.591 | 64.961 | 1.00 31.86 |
| ATOM | 4228 | CA | VAL | B | 493 | 42.672 | 13.338 | 65.643 | 1.00 33.13 |
| ATOM | 4229 | CB | VAL | B | 493 | 41.445 | 12.374 | 65.682 | 1.00 34.15 |
| ATOM | 4230 | CG1 | VAL | B | 493 | 40.843 | 12.197 | 64.299 | 1.00 36.38 |
| ATOM | 4231 | CG2 | VAL | B | 493 | 41.846 | 11.021 | 66.242 | 1.00 34.62 |
| ATOM | 4232 | C | VAL | B | 493 | 43.896 | 12.636 | 65.082 | 1.00 33.71 |
| ATOM | 4233 | O | VAL | B | 493 | 44.653 | 12.036 | 65.839 | 1.00 35.55 |
| ATOM | 4234 | N | LEU | B | 494 | 44.103 | 12.728 | 63.768 | 1.00 34.35 |
| ATOM | 4235 | CA | LEU | B | 494 | 45.264 | 12.099 | 63.129 | 1.00 32.81 |

Figure 6

| | | | | | | | | | |
|---|---|---|---|---|---|---|---|---|---|
| ATOM | 4236 | CB | LEU | B | 494 | 45.030 | 11.925 | 61.623 | 1.00 31.44 |
| ATOM | 4237 | CG | LEU | B | 494 | 44.034 | 10.801 | 61.332 | 1.00 31.44 |
| ATOM | 4238 | CD1 | LEU | B | 494 | 43.673 | 10.799 | 59.879 | 1.00 32.11 |
| ATOM | 4239 | CD2 | LEU | B | 494 | 44.598 | 9.445 | 61.760 | 1.00 31.77 |
| ATOM | 4240 | C | LEU | B | 494 | 46.588 | 12.819 | 63.430 | 1.00 31.76 |
| ATOM | 4241 | O | LEU | B | 494 | 47.615 | 12.173 | 63.624 | 1.00 29.75 |
| ATOM | 4242 | N | GLU | B | 495 | 46.556 | 14.143 | 63.491 | 1.00 32.82 |
| ATOM | 4243 | CA | GLU | B | 495 | 47.747 | 14.922 | 63.809 | 1.00 37.76 |
| ATOM | 4244 | CB | GLU | B | 495 | 47.426 | 16.424 | 63.768 | 1.00 39.48 |
| ATOM | 4245 | CG | GLU | B | 495 | 47.303 | 17.049 | 62.387 | 1.00 43.46 |
| ATOM | 4246 | CD | GLU | B | 495 | 46.826 | 18.508 | 62.419 | 1.00 45.59 |
| ATOM | 4247 | OE1 | GLU | B | 495 | 46.659 | 19.068 | 63.536 | 1.00 45.97 |
| ATOM | 4248 | OE2 | GLU | B | 495 | 46.613 | 19.088 | 61.316 | 1.00 46.33 |
| ATOM | 4249 | C | GLU | B | 495 | 48.227 | 14.581 | 65.230 | 1.00 40.59 |
| ATOM | 4250 | O | GLU | B | 495 | 49.399 | 14.265 | 65.464 | 1.00 42.01 |
| ATOM | 4251 | N | ASP | B | 496 | 47.291 | 14.641 | 66.172 | 1.00 42.61 |
| ATOM | 4252 | CA | ASP | B | 496 | 47.572 | 14.388 | 67.579 | 1.00 43.27 |
| ATOM | 4253 | CB | ASP | B | 496 | 46.620 | 15.214 | 68.465 | 1.00 43.95 |
| ATOM | 4254 | CG | ASP | B | 496 | 46.683 | 16.719 | 68.173 | 1.00 45.08 |
| ATOM | 4255 | OD1 | ASP | B | 496 | 47.793 | 17.255 | 67.930 | 1.00 44.55 |
| ATOM | 4256 | OD2 | ASP | B | 496 | 45.608 | 17.368 | 68.211 | 1.00 45.99 |
| ATOM | 4257 | C | ASP | B | 496 | 47.485 | 12.924 | 67.994 | 1.00 43.90 |
| ATOM | 4258 | O | ASP | B | 496 | 47.427 | 12.648 | 69.193 | 1.00 45.03 |
| ATOM | 4259 | N | PHE | B | 497 | 47.479 | 11.990 | 67.040 | 1.00 43.30 |
| ATOM | 4260 | CA | PHE | B | 497 | 47.362 | 10.565 | 67.385 | 1.00 42.84 |
| ATOM | 4261 | CB | PHE | B | 497 | 47.434 | 9.681 | 66.132 | 1.00 39.47 |
| ATOM | 4262 | CG | PHE | B | 497 | 46.839 | 8.312 | 66.323 | 1.00 37.10 |
| ATOM | 4263 | CD1 | PHE | B | 497 | 45.464 | 8.128 | 66.271 | 1.00 36.78 |
| ATOM | 4264 | CD2 | PHE | B | 497 | 47.647 | 7.213 | 66.580 | 1.00 36.89 |
| ATOM | 4265 | CE1 | PHE | B | 497 | 44.895 | 6.870 | 66.471 | 1.00 36.19 |
| ATOM | 4266 | CE2 | PHE | B | 497 | 47.094 | 5.943 | 66.783 | 1.00 36.90 |
| ATOM | 4267 | CZ | PHE | B | 497 | 45.714 | 5.774 | 66.727 | 1.00 36.71 |
| ATOM | 4268 | C | PHE | B | 497 | 48.394 | 10.119 | 68.434 | 1.00 44.97 |
| ATOM | 4269 | O | PHE | B | 497 | 48.057 | 9.396 | 69.378 | 1.00 45.35 |
| ATOM | 4270 | N | PHE | B | 498 | 49.637 | 10.567 | 68.266 | 1.00 47.97 |
| ATOM | 4271 | CA | PHE | B | 498 | 50.722 | 10.252 | 69.200 | 1.00 50.82 |
| ATOM | 4272 | CB | PHE | B | 498 | 50.883 | 8.734 | 69.423 | 1.00 50.46 |
| ATOM | 4273 | CG | PHE | B | 498 | 51.088 | 7.922 | 68.161 | 1.00 49.37 |
| ATOM | 4274 | CD1 | PHE | B | 498 | 51.587 | 8.497 | 66.990 | 1.00 49.20 |
| ATOM | 4275 | CD2 | PHE | B | 498 | 50.766 | 6.563 | 68.156 | 1.00 48.95 |
| ATOM | 4276 | CE1 | PHE | B | 498 | 51.753 | 7.731 | 65.845 | 1.00 49.20 |
| ATOM | 4277 | CE2 | PHE | B | 498 | 50.930 | 5.788 | 67.015 | 1.00 48.25 |
| ATOM | 4278 | CZ | PHE | B | 498 | 51.423 | 6.371 | 65.858 | 1.00 48.59 |
| ATOM | 4279 | C | PHE | B | 498 | 52.049 | 10.870 | 68.784 | 1.00 52.46 |
| ATOM | 4280 | O | PHE | B | 498 | 52.186 | 12.084 | 69.031 | 1.00 55.24 |
| ATOM | 4281 | N1 | LIG | B | 500 | 52.166 | 14.319 | 39.388 | 1.00 22.17 |
| ATOM | 4282 | C1 | LIG | B | 500 | 52.749 | 13.061 | 39.342 | 1.00 22.30 |
| ATOM | 4283 | N2 | LIG | B | 500 | 54.010 | 12.922 | 39.719 | 1.00 22.08 |
| ATOM | 4284 | C2 | LIG | B | 500 | 54.612 | 11.755 | 39.707 | 1.00 21.72 |
| ATOM | 4285 | N3 | LIG | B | 500 | 54.028 | 10.659 | 39.308 | 1.00 22.42 |
| ATOM | 4286 | C3 | LIG | B | 500 | 52.750 | 10.662 | 38.900 | 1.00 23.15 |
| ATOM | 4287 | N4 | LIG | B | 500 | 51.888 | 9.672 | 38.439 | 1.00 22.48 |
| ATOM | 4288 | C4 | LIG | B | 500 | 52.261 | 8.240 | 38.315 | 1.00 21.86 |
| ATOM | 4289 | C5 | LIG | B | 500 | 51.297 | 7.366 | 39.107 | 1.00 21.73 |
| ATOM | 4290 | C6 | LIG | B | 500 | 52.239 | 7.799 | 36.858 | 1.00 20.47 |
| ATOM | 4291 | C7 | LIG | B | 500 | 50.656 | 10.222 | 38.146 | 1.00 22.74 |
| ATOM | 4292 | C8 | LIG | B | 500 | 50.676 | 11.581 | 38.408 | 1.00 23.86 |
| ATOM | 4293 | C9 | LIG | B | 500 | 49.540 | 12.523 | 38.215 | 1.00 24.73 |
| ATOM | 4294 | C10 | LIG | B | 500 | 49.696 | 13.766 | 37.571 | 1.00 24.26 |

Figure 6

```
ATOM   4295  C11 LIG B 500      48.596  14.612  37.439  1.00 25.84
ATOM   4296  C12 LIG B 500      47.338  14.222  37.944  1.00 26.75
ATOM   4297  N5  LIG B 500      46.211  15.070  37.817  1.00 30.72
ATOM   4298  C13 LIG B 500      45.499  15.565  38.899  1.00 33.55
ATOM   4299  O1  LIG B 500      45.967  15.524  40.037  1.00 33.33
ATOM   4300  C14 LIG B 500      44.142  16.163  38.690  1.00 34.65
ATOM   4301  C15 LIG B 500      43.572  16.216  37.395  1.00 35.74
ATOM   4302  C16 LIG B 500      42.318  16.775  37.220  1.00 34.38
ATOM   4303  C17 LIG B 500      41.625  17.281  38.307  1.00 33.37
ATOM   4304  C18 LIG B 500      42.172  17.238  39.575  1.00 34.11
ATOM   4305  C19 LIG B 500      43.424  16.680  39.778  1.00 34.59
ATOM   4306  C20 LIG B 500      47.199  12.997  38.586  1.00 26.11
ATOM   4307  C21 LIG B 500      48.280  12.152  38.724  1.00 24.96
ATOM   4308  C22 LIG B 500      52.046  11.898  38.904  1.00 22.87
ATOM   4309  OH2 H2O B 600      33.782   0.144  51.103  1.00 19.28
ATOM   4310  OH2 H2O B 602      27.226  -1.920  59.764  1.00  9.37
ATOM   4311  OH2 H2O B 605      22.932  -2.723  57.966  1.00 21.57
ATOM   4312  OH2 H2O B 606      35.714   9.433  47.361  1.00 10.13
ATOM   4313  OH2 H2O B 607      24.954   5.539  61.356  1.00 21.25
ATOM   4314  OH2 H2O B 609      27.934  -8.568  57.751  1.00 24.41
ATOM   4315  OH2 H2O B 610      34.451  -2.140  56.063  1.00 12.50
ATOM   4316  OH2 H2O B 611      34.139   3.616  66.608  1.00 22.60
ATOM   4317  OH2 H2O B 612      29.098  16.370  60.060  1.00 18.74
ATOM   4318  OH2 H2O B 614      37.516  12.777  41.572  1.00 17.70
ATOM   4319  OH2 H2O B 615      18.899  14.133  63.199  1.00 41.05
ATOM   4320  OH2 H2O B 616      26.651  15.055  60.571  1.00 22.11
ATOM   4321  OH2 H2O B 618      36.524  -2.447  44.132  1.00 30.84
ATOM   4322  OH2 H2O B 620      29.871  -4.627  63.359  1.00 32.05
ATOM   4323  OH2 H2O B 621      58.265   8.463  39.836  1.00 22.64
ATOM   4324  OH2 H2O B 623      24.836  -0.899  58.542  1.00 14.66
ATOM   4325  OH2 H2O B 624      63.681  11.096  38.405  1.00 28.05
ATOM   4326  OH2 H2O B 626      43.641   2.802  45.832  1.00 32.83
ATOM   4327  OH2 H2O B 627      31.657  16.324  56.576  1.00 12.23
ATOM   4328  OH2 H2O B 628      32.117   6.813  48.830  1.00 18.53
ATOM   4329  OH2 H2O B 630      37.553   7.347  67.790  1.00 55.46
ATOM   4330  OH2 H2O B 631      62.129  23.162  26.702  1.00 47.78
ATOM   4331  OH2 H2O B 632      33.920  -5.392  61.826  1.00 12.36
ATOM   4332  OH2 H2O B 633      45.474   9.981  40.820  1.00 48.88
ATOM   4333  OH2 H2O B 634      45.300  22.856  55.784  1.00 26.65
ATOM   4334  OH2 H2O B 635      26.876  10.752  50.667  1.00 25.33
ATOM   4335  OH2 H2O B 636      26.554   9.913  65.609  1.00 27.43
ATOM   4336  OH2 H2O B 638      20.297  14.095  65.821  1.00 28.31
ATOM   4337  OH2 H2O B 640      26.628  -1.214  54.716  1.00 16.32
ATOM   4338  OH2 H2O B 641      25.536  15.872  58.132  1.00 23.25
ATOM   4339  OH2 H2O B 642      47.456  22.835  44.885  1.00 24.61
ATOM   4340  OH2 H2O B 644      31.374   0.960  61.187  1.00 24.74
ATOM   4341  OH2 H2O B 645      24.234  -1.521  50.773  1.00 20.84
ATOM   4342  OH2 H2O B 647      32.420 -12.957  53.429  1.00 38.83
ATOM   4343  OH2 H2O B 648      29.315  17.401  49.982  1.00 29.01
ATOM   4344  OH2 H2O B 650      40.793  -5.551  57.717  1.00 33.09
ATOM   4345  OH2 H2O B 652      26.599   2.078  61.221  1.00 27.47
ATOM   4346  OH2 H2O B 653      31.921  -0.014  49.158  1.00 16.30
ATOM   4347  OH2 H2O B 654      32.017  -8.600  64.610  1.00 18.66
ATOM   4348  OH2 H2O B 655      52.105   2.110  33.298  1.00 32.00
ATOM   4349  OH2 H2O B 656      33.075  18.757  43.772  1.00 21.11
ATOM   4350  OH2 H2O B 659      38.015  -6.005  64.862  1.00 20.96
ATOM   4351  OH2 H2O B 660      51.152   1.572  38.488  1.00 45.85
ATOM   4352  OH2 H2O B 661      43.244   7.329  36.026  1.00 38.43
ATOM   4353  OH2 H2O B 663      34.748 -11.988  57.039  1.00 52.41
```

Figure 6

```
ATOM   4354  OH2 H2O B 664      54.400    1.000  39.484  1.00 25.92
ATOM   4355  OH2 H2O B 666      25.903   -2.209  63.011  1.00 39.42
ATOM   4356  OH2 H2O B 667      36.574   21.040  56.921  1.00 36.59
ATOM   4357  OH2 H2O B 668      51.093   -1.416  60.175  1.00 35.56
ATOM   4358  OH2 H2O B 669      33.719   21.024  58.279  1.00 38.40
ATOM   4359  OH2 H2O B 671      26.022   14.848  53.243  1.00 45.47
ATOM   4360  OH2 H2O B 672      34.545   19.573  41.333  1.00 28.22
ATOM   4361  OH2 H2O B 674      42.635   21.991  55.813  1.00 22.02
ATOM   4362  OH2 H2O B 677      33.708    7.518  46.453  1.00 35.01
ATOM   4363  OH2 H2O B 679      43.144    0.992  43.845  1.00 47.78
ATOM   4364  OH2 H2O B 680      59.856    6.709  28.167  1.00 50.11
ATOM   4365  OH2 H2O B 681      21.560    2.888  50.790  1.00 29.59
ATOM   4366  OH2 H2O B 682      57.280   19.640  40.880  1.00 22.22
ATOM   4367  OH2 H2O B 683      47.651    5.716  39.889  1.00 41.97
ATOM   4368  OH2 H2O B 684      42.650   -3.197  53.234  1.00 34.71
ATOM   4369  OH2 H2O B 685      23.831   -0.754  53.339  1.00 27.21
ATOM   4370  OH2 H2O B 688      62.179    9.499  48.536  1.00 29.27
ATOM   4371  OH2 H2O B 689      23.610   -2.991  47.321  1.00 41.83
ATOM   4372  OH2 H2O B 691      47.032   24.453  40.995  1.00 19.95
ATOM   4373  OH2 H2O B 692      40.647    0.599  42.348  1.00 39.35
ATOM   4374  OH2 H2O B 693      44.388   -1.256  47.878  1.00 37.42
ATOM   4375  OH2 H2O B 694      45.443   22.473  42.906  1.00 51.04
ATOM   4376  OH2 H2O B 695      19.112   11.992  66.977  1.00 33.50
ATOM   4377  OH2 H2O B 698      52.818   10.481  25.015  1.00 45.10
ATOM   4378  OH2 H2O B 699      23.358    0.548  60.704  1.00 34.04
ATOM   4379  OH2 H2O B 701      61.429   10.404  36.846  1.00 36.95
ATOM   4380  OH2 H2O B 702      29.385   22.223  59.852  1.00 37.37
ATOM   4381  OH2 H2O B 703      28.894    0.045  61.373  1.00 46.34
ATOM   4382  OH2 H2O B 704      23.062   17.447  54.285  1.00 50.33
ATOM   4383  OH2 H2O B 705      33.518   -4.794  65.937  1.00 43.09
ATOM   4384  OH2 H2O B 706      38.395   -4.915  67.471  1.00 26.23
ATOM   4385  OH2 H2O B 707      48.067   26.466  25.326  1.00 29.86
ATOM   4386  OH2 H2O B 708      23.010   13.273  56.340  1.00 48.25
ATOM   4387  OH2 H2O B 709      35.038   -9.746  64.269  1.00 52.93
ATOM   4388  OH2 H2O B 710      40.968   24.240  54.747  1.00 37.59
ATOM   4389  OH2 H2O B 711      28.783    8.092  64.972  1.00 52.75
ATOM   4390  OH2 H2O B 712      28.371  -13.728  55.750  1.00 50.33
ATOM   4391  OH2 H2O B 713      62.182   22.403  29.224  1.00 24.09
ATOM   4392  OH2 H2O B 714      29.530   10.159  37.676  1.00 46.63
ATOM   4393  OH2 H2O B 715      36.541    5.648  41.044  1.00 35.69
ATOM   4394  OH2 H2O B 716      34.501   27.921  39.569  1.00 45.97
ATOM   4395  OH2 H2O B 717      43.874   25.852  54.696  1.00 43.03
ATOM   4396  OH2 H2O B 718      59.302   12.195  23.087  1.00 52.67
ATOM   4397  OH2 H2O B 719      57.543    8.165  22.266  1.00 40.62
ATOM   4398  OH2 H2O B 720      56.431   14.499  54.723  1.00 32.00
ATOM   4399  OH2 H2O B 721      42.412   15.384  32.998  1.00 45.97
ATOM   4400  OH2 H2O B 722      37.640    0.372  71.212  1.00 36.85
ATOM   4401  OH2 H2O B 723      52.539   25.001  21.175  1.00 32.07
ATOM   4402  OH2 H2O B 724      38.265   13.375  69.718  1.00 58.48
ATOM   4403  OH2 H2O B 725      18.853   -9.215  50.732  1.00 60.40
ATOM   4404  OH2 H2O B 726      42.203   11.267  35.641  1.00 26.77
END
```

Figure 6

```
CRYST1    57.755   44.361  126.167  90.00  90.01  90.00 P21              1
SCALE1      0.017315  0.000000  0.000003        0.00000
SCALE2      0.000000  0.022542  0.000000        0.00000
SCALE3      0.000000  0.000000  0.007926        0.00000
ATOM      1  CB   TRP A 238      15.687  -5.436  28.460  1.00 49.35
ATOM      2  CG   TRP A 238      15.260  -5.784  27.051  1.00 49.28
ATOM      3  CD2  TRP A 238      15.933  -5.429  25.831  1.00 48.18
ATOM      4  CE2  TRP A 238      15.186  -5.986  24.766  1.00 47.87
ATOM      5  CE3  TRP A 238      17.098  -4.703  25.534  1.00 47.36
ATOM      6  CD1  TRP A 238      14.160  -6.516  26.681  1.00 48.44
ATOM      7  NE1  TRP A 238      14.114  -6.640  25.314  1.00 47.53
ATOM      8  CZ2  TRP A 238      15.568  -5.835  23.425  1.00 47.00
ATOM      9  CZ3  TRP A 238      17.477  -4.556  24.195  1.00 45.88
ATOM     10  CH2  TRP A 238      16.714  -5.120  23.163  1.00 46.45
ATOM     11  C    TRP A 238      17.365  -5.677  30.296  1.00 50.43
ATOM     12  O    TRP A 238      18.057  -4.671  30.169  1.00 49.69
ATOM     13  N    TRP A 238      16.232  -7.735  29.297  1.00 50.01
ATOM     14  CA   TRP A 238      16.768  -6.353  29.056  1.00 50.06
ATOM     15  N    GLU A 239      17.070  -6.205  31.489  1.00 51.64
ATOM     16  CA   GLU A 239      17.602  -5.637  32.739  1.00 52.49
ATOM     17  CB   GLU A 239      16.788  -6.071  33.973  1.00 55.11
ATOM     18  CG   GLU A 239      15.621  -5.161  34.362  1.00 59.39
ATOM     19  CD   GLU A 239      14.310  -5.524  33.648  1.00 62.69
ATOM     20  OE1  GLU A 239      14.193  -5.286  32.418  1.00 63.53
ATOM     21  OE2  GLU A 239      13.391  -6.049  34.323  1.00 63.97
ATOM     22  C    GLU A 239      19.039  -6.057  32.984  1.00 51.60
ATOM     23  O    GLU A 239      19.421  -7.203  32.723  1.00 51.41
ATOM     24  N    VAL A 240      19.830  -5.116  33.490  1.00 50.83
ATOM     25  CA   VAL A 240      21.228  -5.369  33.828  1.00 49.19
ATOM     26  CB   VAL A 240      22.227  -4.835  32.765  1.00 48.17
ATOM     27  CG1  VAL A 240      21.971  -5.483  31.411  1.00 47.30
ATOM     28  CG2  VAL A 240      22.177  -3.310  32.693  1.00 47.62
ATOM     29  C    VAL A 240      21.541  -4.705  35.165  1.00 48.93
ATOM     30  O    VAL A 240      20.857  -3.766  35.591  1.00 47.08
ATOM     31  N    PRO A 241      22.550  -5.231  35.872  1.00 49.91
ATOM     32  CD   PRO A 241      23.301  -6.461  35.555  1.00 49.85
ATOM     33  CA   PRO A 241      22.957  -4.683  37.169  1.00 50.54
ATOM     34  CB   PRO A 241      24.058  -5.653  37.613  1.00 50.35
ATOM     35  CG   PRO A 241      23.695  -6.938  36.916  1.00 50.63
ATOM     36  C    PRO A 241      23.528  -3.270  37.001  1.00 50.82
ATOM     37  O    PRO A 241      24.250  -3.003  36.036  1.00 50.61
ATOM     38  N    ARG A 242      23.184  -2.375  37.927  1.00 51.51
ATOM     39  CA   ARG A 242      23.682  -1.001  37.924  1.00 52.31
ATOM     40  CB   ARG A 242      23.177  -0.305  39.182  1.00 53.79
ATOM     41  CG   ARG A 242      23.802   1.044  39.455  1.00 57.42
ATOM     42  CD   ARG A 242      23.274   2.076  38.495  1.00 59.94
ATOM     43  NE   ARG A 242      21.817   2.139  38.582  1.00 62.88
ATOM     44  CZ   ARG A 242      21.144   2.810  39.514  1.00 63.04
ATOM     45  NH1  ARG A 242      21.795   3.498  40.447  1.00 63.76
ATOM     46  NH2  ARG A 242      19.818   2.764  39.533  1.00 62.45
```

Figure 7

| | | | | | | | | | |
|---|---|---|---|---|---|---|---|---|---|
| ATOM | 47 | C | ARG | A | 242 | 25.227 | -0.995 | 37.914 | 1.00 52.87 |
| ATOM | 48 | O | ARG | A | 242 | 25.865 | -0.082 | 37.382 | 1.00 53.27 |
| ATOM | 49 | N | GLU | A | 243 | 25.802 | -2.041 | 38.509 | 1.00 52.53 |
| ATOM | 50 | CA | GLU | A | 243 | 27.243 | -2.255 | 38.625 | 1.00 50.72 |
| ATOM | 51 | CB | GLU | A | 243 | 27.518 | -3.646 | 39.213 | 1.00 52.29 |
| ATOM | 52 | CG | GLU | A | 243 | 27.161 | -3.804 | 40.679 | 1.00 56.23 |
| ATOM | 53 | CD | GLU | A | 243 | 25.704 | -3.487 | 40.975 | 1.00 58.82 |
| ATOM | 54 | OE1 | GLU | A | 243 | 24.831 | -4.342 | 40.693 | 1.00 59.49 |
| ATOM | 55 | OE2 | GLU | A | 243 | 25.434 | -2.371 | 41.473 | 1.00 60.91 |
| ATOM | 56 | C | GLU | A | 243 | 27.961 | -2.163 | 37.294 | 1.00 48.90 |
| ATOM | 57 | O | GLU | A | 243 | 29.031 | -1.553 | 37.215 | 1.00 49.27 |
| ATOM | 58 | N | THR | A | 244 | 27.374 | -2.792 | 36.269 | 1.00 46.23 |
| ATOM | 59 | CA | THR | A | 244 | 27.934 | -2.836 | 34.907 | 1.00 43.24 |
| ATOM | 60 | CB | THR | A | 244 | 27.090 | -3.751 | 33.951 | 1.00 42.95 |
| ATOM | 61 | OG1 | THR | A | 244 | 25.775 | -3.211 | 33.786 | 1.00 39.98 |
| ATOM | 62 | CG2 | THR | A | 244 | 26.979 | -5.167 | 34.495 | 1.00 42.96 |
| ATOM | 63 | C | THR | A | 244 | 28.070 | -1.472 | 34.239 | 1.00 41.22 |
| ATOM | 64 | O | THR | A | 244 | 28.775 | -1.325 | 33.239 | 1.00 40.14 |
| ATOM | 65 | N | LEU | A | 245 | 27.447 | -0.466 | 34.835 | 1.00 39.56 |
| ATOM | 66 | CA | LEU | A | 245 | 27.465 | 0.871 | 34.277 | 1.00 39.32 |
| ATOM | 67 | CB | LEU | A | 245 | 26.025 | 1.352 | 34.136 | 1.00 39.62 |
| ATOM | 68 | CG | LEU | A | 245 | 25.537 | 1.828 | 32.775 | 1.00 40.29 |
| ATOM | 69 | CD1 | LEU | A | 245 | 25.699 | 0.757 | 31.707 | 1.00 39.40 |
| ATOM | 70 | CD2 | LEU | A | 245 | 24.081 | 2.191 | 32.952 | 1.00 42.24 |
| ATOM | 71 | C | LEU | A | 245 | 28.274 | 1.936 | 35.028 | 1.00 38.65 |
| ATOM | 72 | O | LEU | A | 245 | 28.137 | 2.114 | 36.250 | 1.00 38.90 |
| ATOM | 73 | N | LYS | A | 246 | 29.097 | 2.664 | 34.279 | 1.00 36.71 |
| ATOM | 74 | CA | LYS | A | 246 | 29.877 | 3.747 | 34.858 | 1.00 35.72 |
| ATOM | 75 | CB | LYS | A | 246 | 31.400 | 3.464 | 34.828 | 1.00 38.04 |
| ATOM | 76 | CG | LYS | A | 246 | 32.244 | 4.616 | 35.436 | 1.00 39.82 |
| ATOM | 77 | CD | LYS | A | 246 | 33.732 | 4.297 | 35.628 | 1.00 39.92 |
| ATOM | 78 | CE | LYS | A | 246 | 34.508 | 4.203 | 34.339 | 1.00 38.68 |
| ATOM | 79 | NZ | LYS | A | 246 | 35.917 | 3.814 | 34.614 | 1.00 38.73 |
| ATOM | 80 | C | LYS | A | 246 | 29.551 | 5.016 | 34.087 | 1.00 32.89 |
| ATOM | 81 | O | LYS | A | 246 | 29.917 | 5.162 | 32.924 | 1.00 32.72 |
| ATOM | 82 | N | LEU | A | 247 | 28.826 | 5.909 | 34.744 | 1.00 31.01 |
| ATOM | 83 | CA | LEU | A | 247 | 28.436 | 7.179 | 34.154 | 1.00 30.55 |
| ATOM | 84 | CB | LEU | A | 247 | 27.180 | 7.719 | 34.845 | 1.00 29.55 |
| ATOM | 85 | CG | LEU | A | 247 | 25.852 | 7.264 | 34.236 | 1.00 28.11 |
| ATOM | 86 | CD1 | LEU | A | 247 | 25.733 | 5.752 | 34.189 | 1.00 26.60 |
| ATOM | 87 | CD2 | LEU | A | 247 | 24.730 | 7.884 | 35.043 | 1.00 29.89 |
| ATOM | 88 | C | LEU | A | 247 | 29.594 | 8.145 | 34.276 | 1.00 30.65 |
| ATOM | 89 | O | LEU | A | 247 | 30.052 | 8.438 | 35.380 | 1.00 30.86 |
| ATOM | 90 | N | VAL | A | 248 | 30.042 | 8.660 | 33.134 | 1.00 30.94 |
| ATOM | 91 | CA | VAL | A | 248 | 31.205 | 9.540 | 33.077 | 1.00 29.95 |
| ATOM | 92 | CB | VAL | A | 248 | 32.176 | 9.026 | 31.984 | 1.00 30.08 |
| ATOM | 93 | CG1 | VAL | A | 248 | 33.434 | 9.872 | 31.923 | 1.00 31.30 |
| ATOM | 94 | CG2 | VAL | A | 248 | 32.523 | 7.568 | 32.252 | 1.00 30.10 |
| ATOM | 95 | C | VAL | A | 248 | 30.962 | 11.028 | 32.877 | 1.00 30.27 |
| ATOM | 96 | O | VAL | A | 248 | 31.609 | 11.872 | 33.521 | 1.00 29.80 |
| ATOM | 97 | N | GLU | A | 249 | 30.020 | 11.357 | 32.003 | 1.00 30.37 |
| ATOM | 98 | CA | GLU | A | 249 | 29.761 | 12.756 | 31.715 | 1.00 30.53 |
| ATOM | 99 | CB | GLU | A | 249 | 30.736 | 13.191 | 30.614 | 1.00 31.15 |
| ATOM | 100 | CG | GLU | A | 249 | 30.431 | 14.490 | 29.888 | 1.00 30.53 |
| ATOM | 101 | CD | GLU | A | 249 | 31.198 | 14.605 | 28.585 | 1.00 31.31 |
| ATOM | 102 | OE1 | GLU | A | 249 | 31.879 | 13.635 | 28.169 | 1.00 29.83 |
| ATOM | 103 | OE2 | GLU | A | 249 | 31.112 | 15.680 | 27.966 | 1.00 33.75 |
| ATOM | 104 | C | GLU | A | 249 | 28.313 | 13.021 | 31.310 | 1.00 30.45 |
| ATOM | 105 | O | GLU | A | 249 | 27.709 | 12.237 | 30.576 | 1.00 30.24 |

Figure 7

| | | | | | | | | | |
|---|---|---|---|---|---|---|---|---|---|
| ATOM | 106 | N | ARG | A | 250 | 27.770 | 14.141 | 31.778 | 1.00 30.16 |
| ATOM | 107 | CA | ARG | A | 250 | 26.401 | 14.502 | 31.457 | 1.00 30.87 |
| ATOM | 108 | CB | ARG | A | 250 | 25.777 | 15.306 | 32.574 | 1.00 32.62 |
| ATOM | 109 | CG | ARG | A | 250 | 24.266 | 15.227 | 32.550 | 1.00 36.76 |
| ATOM | 110 | CD | ARG | A | 250 | 23.688 | 15.980 | 33.712 | 1.00 38.07 |
| ATOM | 111 | NE | ARG | A | 250 | 23.894 | 17.406 | 33.537 | 1.00 39.70 |
| ATOM | 112 | CZ | ARG | A | 250 | 23.688 | 18.308 | 34.482 | 1.00 40.81 |
| ATOM | 113 | NH1 | ARG | A | 250 | 23.275 | 17.932 | 35.680 | 1.00 40.85 |
| ATOM | 114 | NH2 | ARG | A | 250 | 23.900 | 19.591 | 34.223 | 1.00 41.71 |
| ATOM | 115 | C | ARG | A | 250 | 26.323 | 15.294 | 30.177 | 1.00 29.49 |
| ATOM | 116 | O | ARG | A | 250 | 26.911 | 16.359 | 30.074 | 1.00 29.12 |
| ATOM | 117 | N | LEU | A | 251 | 25.594 | 14.750 | 29.206 | 1.00 29.00 |
| ATOM | 118 | CA | LEU | A | 251 | 25.419 | 15.378 | 27.900 | 1.00 29.26 |
| ATOM | 119 | CB | LEU | A | 251 | 25.120 | 14.320 | 26.828 | 1.00 26.77 |
| ATOM | 120 | CG | LEU | A | 251 | 26.071 | 13.122 | 26.764 | 1.00 25.89 |
| ATOM | 121 | CD1 | LEU | A | 251 | 25.640 | 12.173 | 25.675 | 1.00 25.03 |
| ATOM | 122 | CD2 | LEU | A | 251 | 27.498 | 13.590 | 26.538 | 1.00 25.22 |
| ATOM | 123 | C | LEU | A | 251 | 24.300 | 16.408 | 27.930 | 1.00 30.61 |
| ATOM | 124 | O | LEU | A | 251 | 24.346 | 17.409 | 27.214 | 1.00 30.95 |
| ATOM | 125 | N | GLY | A | 252 | 23.295 | 16.165 | 28.769 | 1.00 32.32 |
| ATOM | 126 | CA | GLY | A | 252 | 22.186 | 17.093 | 28.865 | 1.00 31.84 |
| ATOM | 127 | C | GLY | A | 252 | 21.297 | 16.830 | 30.053 | 1.00 32.31 |
| ATOM | 128 | O | GLY | A | 252 | 21.214 | 15.704 | 30.544 | 1.00 31.93 |
| ATOM | 129 | N | ALA | A | 253 | 20.652 | 17.891 | 30.520 | 1.00 33.24 |
| ATOM | 130 | CA | ALA | A | 253 | 19.736 | 17.831 | 31.657 | 1.00 34.91 |
| ATOM | 131 | CB | ALA | A | 253 | 20.403 | 18.376 | 32.902 | 1.00 34.33 |
| ATOM | 132 | C | ALA | A | 253 | 18.492 | 18.657 | 31.325 | 1.00 35.58 |
| ATOM | 133 | O | ALA | A | 253 | 18.590 | 19.837 | 30.983 | 1.00 36.94 |
| ATOM | 134 | N | GLY | A | 254 | 17.326 | 18.025 | 31.403 | 1.00 35.51 |
| ATOM | 135 | CA | GLY | A | 254 | 16.086 | 18.712 | 31.103 | 1.00 35.57 |
| ATOM | 136 | C | GLY | A | 254 | 14.955 | 18.407 | 32.063 | 1.00 36.26 |
| ATOM | 137 | O | GLY | A | 254 | 15.134 | 17.757 | 33.093 | 1.00 36.24 |
| ATOM | 138 | N | GLN | A | 255 | 13.763 | 18.832 | 31.681 | 1.00 36.84 |
| ATOM | 139 | CA | GLN | A | 255 | 12.573 | 18.649 | 32.503 | 1.00 38.01 |
| ATOM | 140 | CB | GLN | A | 255 | 11.339 | 19.029 | 31.696 | 1.00 41.62 |
| ATOM | 141 | CG | GLN | A | 255 | 10.338 | 19.825 | 32.492 | 1.00 45.91 |
| ATOM | 142 | CD | GLN | A | 255 | 8.947 | 19.712 | 31.930 | 1.00 48.92 |
| ATOM | 143 | OE1 | GLN | A | 255 | 7.963 | 19.795 | 32.675 | 1.00 50.97 |
| ATOM | 144 | NE2 | GLN | A | 255 | 8.846 | 19.510 | 30.611 | 1.00 48.26 |
| ATOM | 145 | C | GLN | A | 255 | 12.337 | 17.286 | 33.161 | 1.00 36.17 |
| ATOM | 146 | O | GLN | A | 255 | 12.178 | 17.204 | 34.379 | 1.00 35.87 |
| ATOM | 147 | N | PHE | A | 256 | 12.326 | 16.224 | 32.362 | 1.00 35.19 |
| ATOM | 148 | CA | PHE | A | 256 | 12.058 | 14.867 | 32.862 | 1.00 34.33 |
| ATOM | 149 | CB | PHE | A | 256 | 11.171 | 14.095 | 31.865 | 1.00 33.34 |
| ATOM | 150 | CG | PHE | A | 256 | 9.828 | 14.724 | 31.626 | 1.00 31.44 |
| ATOM | 151 | CD1 | PHE | A | 256 | 9.321 | 15.675 | 32.512 | 1.00 31.36 |
| ATOM | 152 | CD2 | PHE | A | 256 | 9.080 | 14.384 | 30.504 | 1.00 29.70 |
| ATOM | 153 | CE1 | PHE | A | 256 | 8.090 | 16.279 | 32.283 | 1.00 32.64 |
| ATOM | 154 | CE2 | PHE | A | 256 | 7.847 | 14.980 | 30.260 | 1.00 29.31 |
| ATOM | 155 | CZ | PHE | A | 256 | 7.347 | 15.931 | 31.148 | 1.00 31.56 |
| ATOM | 156 | C | PHE | A | 256 | 13.265 | 14.003 | 33.211 | 1.00 34.23 |
| ATOM | 157 | O | PHE | A | 256 | 13.112 | 12.867 | 33.670 | 1.00 33.31 |
| ATOM | 158 | N | GLY | A | 257 | 14.462 | 14.513 | 32.957 | 1.00 34.60 |
| ATOM | 159 | CA | GLY | A | 257 | 15.641 | 13.731 | 33.251 | 1.00 34.38 |
| ATOM | 160 | C | GLY | A | 257 | 16.895 | 14.260 | 32.593 | 1.00 33.91 |
| ATOM | 161 | O | GLY | A | 257 | 16.960 | 15.417 | 32.178 | 1.00 32.11 |
| ATOM | 162 | N | GLU | A | 258 | 17.884 | 13.377 | 32.478 | 1.00 35.10 |
| ATOM | 163 | CA | GLU | A | 258 | 19.183 | 13.718 | 31.904 | 1.00 35.10 |
| ATOM | 164 | CB | GLU | A | 258 | 20.191 | 13.959 | 33.041 | 1.00 35.83 |

Figure 7

| | | | | | | | | | |
|---|---|---|---|---|---|---|---|---|---|
| ATOM | 165 | CG | GLU | A | 258 | 19.740 | 14.964 | 34.102 | 1.00 38.33 |
| ATOM | 166 | CD | GLU | A | 258 | 20.719 | 15.113 | 35.261 | 1.00 39.52 |
| ATOM | 167 | OE1 | GLU | A | 258 | 21.386 | 14.117 | 35.621 | 1.00 39.36 |
| ATOM | 168 | OE2 | GLU | A | 258 | 20.807 | 16.235 | 35.818 | 1.00 40.40 |
| ATOM | 169 | C | GLU | A | 258 | 19.696 | 12.579 | 31.027 | 1.00 34.63 |
| ATOM | 170 | O | GLU | A | 258 | 19.189 | 11.447 | 31.108 | 1.00 34.73 |
| ATOM | 171 | N | VAL | A | 259 | 20.657 | 12.902 | 30.154 | 1.00 33.75 |
| ATOM | 172 | CA | VAL | A | 259 | 21.302 | 11.902 | 29.289 | 1.00 32.25 |
| ATOM | 173 | CB | VAL | A | 259 | 21.074 | 12.154 | 27.765 | 1.00 31.88 |
| ATOM | 174 | CG1 | VAL | A | 259 | 21.628 | 10.986 | 26.944 | 1.00 29.84 |
| ATOM | 175 | CG2 | VAL | A | 259 | 19.605 | 12.340 | 27.469 | 1.00 31.00 |
| ATOM | 176 | C | VAL | A | 259 | 22.787 | 12.023 | 29.614 | 1.00 31.46 |
| ATOM | 177 | O | VAL | A | 259 | 23.304 | 13.135 | 29.769 | 1.00 30.64 |
| ATOM | 178 | N | TRP | A | 260 | 23.440 | 10.880 | 29.799 | 1.00 31.45 |
| ATOM | 179 | CA | TRP | A | 260 | 24.861 | 10.824 | 30.136 | 1.00 31.41 |
| ATOM | 180 | CB | TRP | A | 260 | 25.080 | 10.241 | 31.552 | 1.00 32.25 |
| ATOM | 181 | CG | TRP | A | 260 | 24.670 | 11.113 | 32.727 | 1.00 35.13 |
| ATOM | 182 | CD2 | TRP | A | 260 | 25.538 | 11.653 | 33.738 | 1.00 35.28 |
| ATOM | 183 | CE2 | TRP | A | 260 | 24.730 | 12.391 | 34.638 | 1.00 35.49 |
| ATOM | 184 | CE3 | TRP | A | 260 | 26.918 | 11.585 | 33.971 | 1.00 35.02 |
| ATOM | 185 | CD1 | TRP | A | 260 | 23.403 | 11.533 | 33.052 | 1.00 34.98 |
| ATOM | 186 | NE1 | TRP | A | 260 | 23.436 | 12.301 | 34.194 | 1.00 35.52 |
| ATOM | 187 | CZ2 | TRP | A | 260 | 25.259 | 13.057 | 35.750 | 1.00 34.24 |
| ATOM | 188 | CZ3 | TRP | A | 260 | 27.443 | 12.251 | 35.079 | 1.00 34.67 |
| ATOM | 189 | CH2 | TRP | A | 260 | 26.613 | 12.975 | 35.949 | 1.00 33.94 |
| ATOM | 190 | C | TRP | A | 260 | 25.596 | 9.908 | 29.181 | 1.00 30.25 |
| ATOM | 191 | O | TRP | A | 260 | 25.008 | 9.060 | 28.517 | 1.00 28.98 |
| ATOM | 192 | N | MET | A | 261 | 26.908 | 10.098 | 29.131 | 1.00 30.66 |
| ATOM | 193 | CA | MET | A | 261 | 27.808 | 9.266 | 28.343 | 1.00 29.49 |
| ATOM | 194 | CB | MET | A | 261 | 28.861 | 10.123 | 27.620 | 1.00 28.23 |
| ATOM | 195 | CG | MET | A | 261 | 29.918 | 9.334 | 26.841 | 1.00 27.90 |
| ATOM | 196 | SD | MET | A | 261 | 31.238 | 8.600 | 27.871 | 1.00 26.43 |
| ATOM | 197 | CE | MET | A | 261 | 31.902 | 10.098 | 28.566 | 1.00 26.74 |
| ATOM | 198 | C | MET | A | 261 | 28.468 | 8.403 | 29.423 | 1.00 29.47 |
| ATOM | 199 | O | MET | A | 261 | 28.735 | 8.875 | 30.533 | 1.00 30.71 |
| ATOM | 200 | N | GLY | A | 262 | 28.682 | 7.133 | 29.125 | 1.00 29.18 |
| ATOM | 201 | CA | GLY | A | 262 | 29.287 | 6.271 | 30.109 | 1.00 29.01 |
| ATOM | 202 | C | GLY | A | 262 | 29.803 | 5.017 | 29.472 | 1.00 29.69 |
| ATOM | 203 | O | GLY | A | 262 | 29.845 | 4.916 | 28.253 | 1.00 28.34 |
| ATOM | 204 | N | TYR | A | 263 | 30.168 | 4.051 | 30.305 | 1.00 32.47 |
| ATOM | 205 | CA | TYR | A | 263 | 30.705 | 2.789 | 29.834 | 1.00 35.28 |
| ATOM | 206 | CB | TYR | A | 263 | 32.223 | 2.746 | 30.064 | 1.00 32.75 |
| ATOM | 207 | CG | TYR | A | 263 | 32.961 | 3.771 | 29.214 | 1.00 30.35 |
| ATOM | 208 | CD1 | TYR | A | 263 | 33.366 | 3.460 | 27.907 | 1.00 26.74 |
| ATOM | 209 | CE1 | TYR | A | 263 | 33.954 | 4.429 | 27.084 | 1.00 25.05 |
| ATOM | 210 | CD2 | TYR | A | 263 | 33.174 | 5.078 | 29.682 | 1.00 27.75 |
| ATOM | 211 | CE2 | TYR | A | 263 | 33.760 | 6.054 | 28.862 | 1.00 25.89 |
| ATOM | 212 | CZ | TYR | A | 263 | 34.142 | 5.718 | 27.567 | 1.00 24.48 |
| ATOM | 213 | OH | TYR | A | 263 | 34.708 | 6.671 | 26.758 | 1.00 23.66 |
| ATOM | 214 | C | TYR | A | 263 | 29.986 | 1.582 | 30.436 | 1.00 38.59 |
| ATOM | 215 | O | TYR | A | 263 | 29.687 | 1.516 | 31.638 | 1.00 38.00 |
| ATOM | 216 | N | TYR | A | 264 | 29.711 | 0.634 | 29.550 | 1.00 42.63 |
| ATOM | 217 | CA | TYR | A | 264 | 28.992 | -0.596 | 29.845 | 1.00 48.24 |
| ATOM | 218 | CB | TYR | A | 264 | 27.970 | -0.814 | 28.716 | 1.00 52.16 |
| ATOM | 219 | CG | TYR | A | 264 | 26.963 | -1.942 | 28.858 | 1.00 56.53 |
| ATOM | 220 | CD1 | TYR | A | 264 | 26.567 | -2.426 | 30.106 | 1.00 57.81 |
| ATOM | 221 | CE1 | TYR | A | 264 | 25.583 | -3.435 | 30.209 | 1.00 59.91 |
| ATOM | 222 | CD2 | TYR | A | 264 | 26.357 | -2.490 | 27.710 | 1.00 58.59 |
| ATOM | 223 | CE2 | TYR | A | 264 | 25.375 | -3.488 | 27.797 | 1.00 58.87 |

Figure 7

| ATOM | 224 | CZ | TYR A 264 | 24.989 | -3.958 | 29.046 | 1.00 | 59.86 |
| ATOM | 225 | OH | TYR A 264 | 24.009 | -4.932 | 29.124 | 1.00 | 59.28 |
| ATOM | 226 | C | TYR A 264 | 29.988 | -1.740 | 29.908 | 1.00 | 49.78 |
| ATOM | 227 | O | TYR A 264 | 30.795 | -1.920 | 28.995 | 1.00 | 49.95 |
| ATOM | 228 | N | ASN A 265 | 29.941 | -2.493 | 31.007 | 1.00 | 51.34 |
| ATOM | 229 | CA | ASN A 265 | 30.831 | -3.633 | 31.232 | 1.00 | 52.26 |
| ATOM | 230 | CB | ASN A 265 | 30.470 | -4.806 | 30.292 | 1.00 | 54.27 |
| ATOM | 231 | CG | ASN A 265 | 28.949 | -5.084 | 30.230 | 1.00 | 56.02 |
| ATOM | 232 | OD1 | ASN A 265 | 28.290 | -5.321 | 31.251 | 1.00 | 57.42 |
| ATOM | 233 | ND2 | ASN A 265 | 28.404 | -5.072 | 29.019 | 1.00 | 54.31 |
| ATOM | 234 | C | ASN A 265 | 32.295 | -3.203 | 31.042 | 1.00 | 51.61 |
| ATOM | 235 | O | ASN A 265 | 33.144 | -4.001 | 30.649 | 1.00 | 51.31 |
| ATOM | 236 | N | GLY A 266 | 32.565 | -1.923 | 31.288 | 1.00 | 51.49 |
| ATOM | 237 | CA | GLY A 266 | 33.909 | -1.400 | 31.166 | 1.00 | 51.38 |
| ATOM | 238 | C | GLY A 266 | 34.415 | -0.930 | 29.816 | 1.00 | 51.65 |
| ATOM | 239 | O | GLY A 266 | 35.152 | 0.057 | 29.770 | 1.00 | 52.02 |
| ATOM | 240 | N | HIS A 267 | 34.042 | -1.600 | 28.723 | 1.00 | 51.98 |
| ATOM | 241 | CA | HIS A 267 | 34.545 | -1.202 | 27.397 | 1.00 | 51.74 |
| ATOM | 242 | CB | HIS A 267 | 35.470 | -2.293 | 26.841 | 1.00 | 57.38 |
| ATOM | 243 | CG | HIS A 267 | 36.760 | -2.418 | 27.602 | 1.00 | 63.68 |
| ATOM | 244 | CD2 | HIS A 267 | 37.850 | -1.614 | 27.642 | 1.00 | 65.69 |
| ATOM | 245 | ND1 | HIS A 267 | 36.993 | -3.424 | 28.520 | 1.00 | 65.52 |
| ATOM | 246 | CE1 | HIS A 267 | 38.166 | -3.228 | 29.097 | 1.00 | 67.05 |
| ATOM | 247 | NE2 | HIS A 267 | 38.707 | -2.138 | 28.583 | 1.00 | 67.87 |
| ATOM | 248 | C | HIS A 267 | 33.607 | -0.678 | 26.300 | 1.00 | 47.69 |
| ATOM | 249 | O | HIS A 267 | 34.070 | -0.075 | 25.331 | 1.00 | 47.58 |
| ATOM | 250 | N | THR A 268 | 32.305 | -0.892 | 26.451 | 1.00 | 42.94 |
| ATOM | 251 | CA | THR A 268 | 31.333 | -0.416 | 25.470 | 1.00 | 37.60 |
| ATOM | 252 | CB | THR A 268 | 30.126 | -1.390 | 25.356 | 1.00 | 37.66 |
| ATOM | 253 | OG1 | THR A 268 | 30.583 | -2.697 | 24.969 | 1.00 | 35.87 |
| ATOM | 254 | CG2 | THR A 268 | 29.127 | -0.893 | 24.321 | 1.00 | 37.34 |
| ATOM | 255 | C | THR A 268 | 30.852 | 0.987 | 25.870 | 1.00 | 34.00 |
| ATOM | 256 | O | THR A 268 | 30.385 | 1.195 | 26.984 | 1.00 | 33.62 |
| ATOM | 257 | N | LYS A 269 | 31.002 | 1.952 | 24.970 | 1.00 | 30.04 |
| ATOM | 258 | CA | LYS A 269 | 30.588 | 3.325 | 25.230 | 1.00 | 27.53 |
| ATOM | 259 | CB | LYS A 269 | 31.353 | 4.287 | 24.340 | 1.00 | 24.11 |
| ATOM | 260 | CG | LYS A 269 | 31.334 | 5.706 | 24.817 | 1.00 | 22.00 |
| ATOM | 261 | CD | LYS A 269 | 32.248 | 6.513 | 23.948 | 1.00 | 22.43 |
| ATOM | 262 | CE | LYS A 269 | 32.303 | 7.962 | 24.363 | 1.00 | 21.59 |
| ATOM | 263 | NZ | LYS A 269 | 33.219 | 8.698 | 23.445 | 1.00 | 23.21 |
| ATOM | 264 | C | LYS A 269 | 29.091 | 3.449 | 24.978 | 1.00 | 27.62 |
| ATOM | 265 | O | LYS A 269 | 28.587 | 2.976 | 23.967 | 1.00 | 28.04 |
| ATOM | 266 | N | VAL A 270 | 28.380 | 4.098 | 25.894 | 1.00 | 27.10 |
| ATOM | 267 | CA | VAL A 270 | 26.934 | 4.203 | 25.771 | 1.00 | 26.23 |
| ATOM | 268 | CB | VAL A 270 | 26.215 | 3.121 | 26.660 | 1.00 | 26.31 |
| ATOM | 269 | CG1 | VAL A 270 | 26.548 | 1.712 | 26.183 | 1.00 | 25.18 |
| ATOM | 270 | CG2 | VAL A 270 | 26.587 | 3.283 | 28.158 | 1.00 | 23.57 |
| ATOM | 271 | C | VAL A 270 | 26.347 | 5.548 | 26.134 | 1.00 | 26.14 |
| ATOM | 272 | O | VAL A 270 | 27.036 | 6.438 | 26.624 | 1.00 | 25.80 |
| ATOM | 273 | N | ALA A 271 | 25.063 | 5.689 | 25.817 | 1.00 | 27.41 |
| ATOM | 274 | CA | ALA A 271 | 24.286 | 6.869 | 26.163 | 1.00 | 28.01 |
| ATOM | 275 | CB | ALA A 271 | 23.585 | 7.427 | 24.959 | 1.00 | 28.97 |
| ATOM | 276 | C | ALA A 271 | 23.268 | 6.323 | 27.169 | 1.00 | 28.22 |
| ATOM | 277 | O | ALA A 271 | 22.665 | 5.264 | 26.947 | 1.00 | 27.92 |
| ATOM | 278 | N | VAL A 272 | 23.118 | 7.012 | 28.291 | 1.00 | 27.87 |
| ATOM | 279 | CA | VAL A 272 | 22.208 | 6.573 | 29.324 | 1.00 | 27.37 |
| ATOM | 280 | CB | VAL A 272 | 22.975 | 6.254 | 30.637 | 1.00 | 28.19 |
| ATOM | 281 | CG1 | VAL A 272 | 22.032 | 5.709 | 31.688 | 1.00 | 27.78 |
| ATOM | 282 | CG2 | VAL A 272 | 24.102 | 5.259 | 30.380 | 1.00 | 28.57 |

Figure 7

| | | | | | | | | | |
|---|---|---|---|---|---|---|---|---|---|
| ATOM | 283 | C | VAL | A | 272 | 21.200 | 7.665 | 29.602 | 1.00 27.75 |
| ATOM | 284 | O | VAL | A | 272 | 21.561 | 8.815 | 29.869 | 1.00 26.10 |
| ATOM | 285 | N | LYS | A | 273 | 19.926 | 7.322 | 29.459 | 1.00 29.03 |
| ATOM | 286 | CA | LYS | A | 273 | 18.869 | 8.272 | 29.747 | 1.00 29.80 |
| ATOM | 287 | CB | LYS | A | 273 | 17.802 | 8.264 | 28.644 | 1.00 29.13 |
| ATOM | 288 | CG | LYS | A | 273 | 16.813 | 9.425 | 28.763 | 1.00 30.04 |
| ATOM | 289 | CD | LYS | A | 273 | 15.861 | 9.504 | 27.582 | 1.00 31.36 |
| ATOM | 290 | CE | LYS | A | 273 | 16.455 | 10.277 | 26.429 | 1.00 30.36 |
| ATOM | 291 | NZ | LYS | A | 273 | 15.457 | 10.418 | 25.346 | 1.00 31.70 |
| ATOM | 292 | C | LYS | A | 273 | 18.294 | 7.881 | 31.116 | 1.00 29.91 |
| ATOM | 293 | O | LYS | A | 273 | 17.925 | 6.727 | 31.337 | 1.00 29.07 |
| ATOM | 294 | N | SER | A | 274 | 18.303 | 8.828 | 32.051 | 1.00 31.27 |
| ATOM | 295 | CA | SER | A | 274 | 17.800 | 8.587 | 33.401 | 1.00 32.84 |
| ATOM | 296 | CB | SER | A | 274 | 18.874 | 8.904 | 34.437 | 1.00 34.39 |
| ATOM | 297 | OG | SER | A | 274 | 19.097 | 10.305 | 34.485 | 1.00 37.44 |
| ATOM | 298 | C | SER | A | 274 | 16.588 | 9.453 | 33.684 | 1.00 33.10 |
| ATOM | 299 | O | SER | A | 274 | 16.506 | 10.595 | 33.216 | 1.00 33.07 |
| ATOM | 300 | N | LEU | A | 275 | 15.676 | 8.907 | 34.490 | 1.00 33.40 |
| ATOM | 301 | CA | LEU | A | 275 | 14.431 | 9.574 | 34.875 | 1.00 32.26 |
| ATOM | 302 | CB | LEU | A | 275 | 13.341 | 8.507 | 35.088 | 1.00 31.03 |
| ATOM | 303 | CG | LEU | A | 275 | 11.967 | 8.898 | 35.677 | 1.00 30.27 |
| ATOM | 304 | CD1 | LEU | A | 275 | 11.213 | 9.821 | 34.709 | 1.00 28.21 |
| ATOM | 305 | CD2 | LEU | A | 275 | 11.152 | 7.643 | 36.016 | 1.00 26.40 |
| ATOM | 306 | C | LEU | A | 275 | 14.535 | 10.441 | 36.140 | 1.00 32.82 |
| ATOM | 307 | O | LEU | A | 275 | 15.002 | 9.975 | 37.184 | 1.00 33.23 |
| ATOM | 308 | N | LYS | A | 276 | 14.102 | 11.698 | 36.046 | 1.00 33.88 |
| ATOM | 309 | CA | LYS | A | 276 | 14.085 | 12.593 | 37.208 | 1.00 36.58 |
| ATOM | 310 | CB | LYS | A | 276 | 13.907 | 14.058 | 36.769 | 1.00 38.01 |
| ATOM | 311 | CG | LYS | A | 276 | 13.879 | 15.099 | 37.910 | 1.00 41.35 |
| ATOM | 312 | CD | LYS | A | 276 | 13.927 | 16.545 | 37.370 | 1.00 45.79 |
| ATOM | 313 | CE | LYS | A | 276 | 15.216 | 16.784 | 36.539 | 1.00 51.26 |
| ATOM | 314 | NZ | LYS | A | 276 | 15.416 | 18.158 | 35.959 | 1.00 51.78 |
| ATOM | 315 | C | LYS | A | 276 | 12.867 | 12.137 | 38.018 | 1.00 38.25 |
| ATOM | 316 | O | LYS | A | 276 | 11.727 | 12.310 | 37.578 | 1.00 37.74 |
| ATOM | 317 | N | GLN | A | 277 | 13.112 | 11.468 | 39.145 | 1.00 39.57 |
| ATOM | 318 | CA | GLN | A | 277 | 12.038 | 10.980 | 40.010 | 1.00 41.11 |
| ATOM | 319 | CB | GLN | A | 277 | 12.593 | 10.594 | 41.389 | 1.00 45.87 |
| ATOM | 320 | CG | GLN | A | 277 | 11.537 | 10.015 | 42.358 | 1.00 53.60 |
| ATOM | 321 | CD | GLN | A | 277 | 12.105 | 9.568 | 43.721 | 1.00 58.47 |
| ATOM | 322 | OE1 | GLN | A | 277 | 13.255 | 9.863 | 44.077 | 1.00 61.52 |
| ATOM | 323 | NE2 | GLN | A | 277 | 11.285 | 8.859 | 44.489 | 1.00 59.81 |
| ATOM | 324 | C | GLN | A | 277 | 10.923 | 12.021 | 40.182 | 1.00 40.26 |
| ATOM | 325 | O | GLN | A | 277 | 11.188 | 13.183 | 40.515 | 1.00 40.36 |
| ATOM | 326 | N | GLY | A | 278 | 9.686 | 11.607 | 39.903 | 1.00 38.88 |
| ATOM | 327 | CA | GLY | A | 278 | 8.547 | 12.501 | 40.040 | 1.00 37.17 |
| ATOM | 328 | C | GLY | A | 278 | 8.072 | 13.161 | 38.755 | 1.00 36.92 |
| ATOM | 329 | O | GLY | A | 278 | 7.100 | 13.933 | 38.764 | 1.00 37.53 |
| ATOM | 330 | N | SER | A | 279 | 8.767 | 12.892 | 37.655 | 1.00 34.69 |
| ATOM | 331 | CA | SER | A | 279 | 8.388 | 13.464 | 36.377 | 1.00 32.97 |
| ATOM | 332 | CB | SER | A | 279 | 9.591 | 13.468 | 35.439 | 1.00 32.74 |
| ATOM | 333 | OG | SER | A | 279 | 10.515 | 14.448 | 35.869 | 1.00 30.12 |
| ATOM | 334 | C | SER | A | 279 | 7.226 | 12.664 | 35.798 | 1.00 32.00 |
| ATOM | 335 | O | SER | A | 279 | 6.263 | 13.220 | 35.285 | 1.00 31.27 |
| ATOM | 336 | N | MET | A | 280 | 7.345 | 11.349 | 35.896 | 1.00 31.85 |
| ATOM | 337 | CA | MET | A | 280 | 6.331 | 10.401 | 35.449 | 1.00 32.70 |
| ATOM | 338 | CB | MET | A | 280 | 6.388 | 10.190 | 33.930 | 1.00 32.25 |
| ATOM | 339 | CG | MET | A | 280 | 7.586 | 9.412 | 33.416 | 1.00 31.51 |
| ATOM | 340 | SD | MET | A | 280 | 7.867 | 9.857 | 31.705 | 1.00 32.58 |
| ATOM | 341 | CE | MET | A | 280 | 7.044 | 8.673 | 30.930 | 1.00 31.92 |

Figure 7

| | | | | | | | | | |
|---|---|---|---|---|---|---|---|---|---|
| ATOM | 342 | C | MET | A | 280 | 6.685 | 9.125 | 36.183 | 1.00 33.48 |
| ATOM | 343 | O | MET | A | 280 | 7.723 | 9.066 | 36.845 | 1.00 34.77 |
| ATOM | 344 | N | SER | A | 281 | 5.844 | 8.104 | 36.095 | 1.00 33.57 |
| ATOM | 345 | CA | SER | A | 281 | 6.158 | 6.873 | 36.793 | 1.00 34.24 |
| ATOM | 346 | CB | SER | A | 281 | 4.913 | 5.999 | 36.969 | 1.00 33.79 |
| ATOM | 347 | OG | SER | A | 281 | 4.636 | 5.241 | 35.801 | 1.00 31.69 |
| ATOM | 348 | C | SER | A | 281 | 7.221 | 6.081 | 36.042 | 1.00 35.76 |
| ATOM | 349 | O | SER | A | 281 | 7.442 | 6.292 | 34.839 | 1.00 35.89 |
| ATOM | 350 | N | PRO | A | 282 | 7.930 | 5.197 | 36.760 | 1.00 36.52 |
| ATOM | 351 | CD | PRO | A | 282 | 7.955 | 5.154 | 38.235 | 1.00 36.86 |
| ATOM | 352 | CA | PRO | A | 282 | 8.983 | 4.341 | 36.199 | 1.00 36.53 |
| ATOM | 353 | CB | PRO | A | 282 | 9.363 | 3.465 | 37.393 | 1.00 36.49 |
| ATOM | 354 | CG | PRO | A | 282 | 9.273 | 4.444 | 38.529 | 1.00 37.32 |
| ATOM | 355 | C | PRO | A | 282 | 8.430 | 3.503 | 35.045 | 1.00 36.36 |
| ATOM | 356 | O | PRO | A | 282 | 9.084 | 3.337 | 34.016 | 1.00 35.71 |
| ATOM | 357 | N | ASP | A | 283 | 7.203 | 3.019 | 35.216 | 1.00 36.89 |
| ATOM | 358 | CA | ASP | A | 283 | 6.532 | 2.201 | 34.207 | 1.00 35.98 |
| ATOM | 359 | CB | ASP | A | 283 | 5.247 | 1.589 | 34.786 | 1.00 39.66 |
| ATOM | 360 | CG | ASP | A | 283 | 5.525 | 0.443 | 35.774 | 1.00 45.17 |
| ATOM | 361 | OD1 | ASP | A | 283 | 6.606 | -0.194 | 35.692 | 1.00 47.89 |
| ATOM | 362 | OD2 | ASP | A | 283 | 4.647 | 0.161 | 36.623 | 1.00 47.88 |
| ATOM | 363 | C | ASP | A | 283 | 6.242 | 2.983 | 32.930 | 1.00 33.48 |
| ATOM | 364 | O | ASP | A | 283 | 6.396 | 2.460 | 31.831 | 1.00 32.39 |
| ATOM | 365 | N | ALA | A | 284 | 5.891 | 4.253 | 33.081 | 1.00 31.28 |
| ATOM | 366 | CA | ALA | A | 284 | 5.590 | 5.109 | 31.940 | 1.00 30.39 |
| ATOM | 367 | CB | ALA | A | 284 | 4.886 | 6.353 | 32.404 | 1.00 28.64 |
| ATOM | 368 | C | ALA | A | 284 | 6.847 | 5.482 | 31.148 | 1.00 30.43 |
| ATOM | 369 | O | ALA | A | 284 | 6.808 | 5.604 | 29.916 | 1.00 30.10 |
| ATOM | 370 | N | PHE | A | 285 | 7.954 | 5.668 | 31.871 | 1.00 30.71 |
| ATOM | 371 | CA | PHE | A | 285 | 9.244 | 6.030 | 31.292 | 1.00 29.07 |
| ATOM | 372 | CB | PHE | A | 285 | 10.188 | 6.481 | 32.407 | 1.00 28.92 |
| ATOM | 373 | CG | PHE | A | 285 | 11.581 | 6.811 | 31.942 | 1.00 29.20 |
| ATOM | 374 | CD1 | PHE | A | 285 | 11.844 | 7.999 | 31.271 | 1.00 28.47 |
| ATOM | 375 | CD2 | PHE | A | 285 | 12.640 | 5.942 | 32.210 | 1.00 27.76 |
| ATOM | 376 | CE1 | PHE | A | 285 | 13.142 | 8.311 | 30.881 | 1.00 28.04 |
| ATOM | 377 | CE2 | PHE | A | 285 | 13.933 | 6.251 | 31.822 | 1.00 26.81 |
| ATOM | 378 | CZ | PHE | A | 285 | 14.184 | 7.433 | 31.161 | 1.00 27.55 |
| ATOM | 379 | C | PHE | A | 285 | 9.830 | 4.859 | 30.516 | 1.00 28.27 |
| ATOM | 380 | O | PHE | A | 285 | 10.257 | 5.018 | 29.379 | 1.00 27.62 |
| ATOM | 381 | N | LEU | A | 286 | 9.820 | 3.686 | 31.134 | 1.00 29.14 |
| ATOM | 382 | CA | LEU | A | 286 | 10.325 | 2.462 | 30.526 | 1.00 31.38 |
| ATOM | 383 | CB | LEU | A | 286 | 10.323 | 1.331 | 31.557 | 1.00 32.67 |
| ATOM | 384 | CG | LEU | A | 286 | 11.266 | 1.487 | 32.761 | 1.00 35.43 |
| ATOM | 385 | CD1 | LEU | A | 286 | 10.865 | 0.540 | 33.885 | 1.00 35.04 |
| ATOM | 386 | CD2 | LEU | A | 286 | 12.719 | 1.252 | 32.334 | 1.00 36.05 |
| ATOM | 387 | C | LEU | A | 286 | 9.495 | 2.036 | 29.321 | 1.00 32.89 |
| ATOM | 388 | O | LEU | A | 286 | 10.011 | 1.434 | 28.376 | 1.00 31.81 |
| ATOM | 389 | N | ALA | A | 287 | 8.204 | 2.353 | 29.372 | 1.00 35.21 |
| ATOM | 390 | CA | ALA | A | 287 | 7.256 | 2.013 | 28.314 | 1.00 37.52 |
| ATOM | 391 | CB | ALA | A | 287 | 5.853 | 2.517 | 28.683 | 1.00 36.61 |
| ATOM | 392 | C | ALA | A | 287 | 7.682 | 2.584 | 26.980 | 1.00 39.44 |
| ATOM | 393 | O | ALA | A | 287 | 7.524 | 1.940 | 25.939 | 1.00 41.04 |
| ATOM | 394 | N | GLU | A | 288 | 8.207 | 3.801 | 27.014 | 1.00 41.49 |
| ATOM | 395 | CA | GLU | A | 288 | 8.671 | 4.485 | 25.813 | 1.00 45.58 |
| ATOM | 396 | CB | GLU | A | 288 | 9.005 | 5.926 | 26.161 | 1.00 46.37 |
| ATOM | 397 | CG | GLU | A | 288 | 7.811 | 6.649 | 26.758 | 1.00 49.85 |
| ATOM | 398 | CD | GLU | A | 288 | 8.115 | 8.073 | 27.158 | 1.00 53.01 |
| ATOM | 399 | OE1 | GLU | A | 288 | 9.297 | 8.362 | 27.445 | 1.00 54.72 |
| ATOM | 400 | OE2 | GLU | A | 288 | 7.174 | 8.905 | 27.191 | 1.00 54.54 |

Figure 7

| | | | | | | | | | |
|---|---|---|---|---|---|---|---|---|---|
| ATOM | 401 | C | GLU | A | 288 | 9.857 | 3.778 | 25.147 | 1.00 47.61 |
| ATOM | 402 | O | GLU | A | 288 | 10.088 | 3.921 | 23.949 | 1.00 47.44 |
| ATOM | 403 | N | ALA | A | 289 | 10.589 | 3.001 | 25.941 | 1.00 50.11 |
| ATOM | 404 | CA | ALA | A | 289 | 11.722 | 2.225 | 25.465 | 1.00 52.37 |
| ATOM | 405 | CB | ALA | A | 289 | 12.646 | 1.896 | 26.625 | 1.00 52.85 |
| ATOM | 406 | C | ALA | A | 289 | 11.216 | 0.933 | 24.827 | 1.00 54.58 |
| ATOM | 407 | O | ALA | A | 289 | 11.792 | 0.457 | 23.860 | 1.00 54.25 |
| ATOM | 408 | N | ASN | A | 290 | 10.152 | 0.362 | 25.399 | 1.00 57.42 |
| ATOM | 409 | CA | ASN | A | 290 | 9.529 | -0.894 | 24.928 | 1.00 58.55 |
| ATOM | 410 | CB | ASN | A | 290 | 8.276 | -1.212 | 25.771 | 1.00 59.89 |
| ATOM | 411 | CG | ASN | A | 290 | 8.604 | -1.572 | 27.226 | 1.00 61.62 |
| ATOM | 412 | OD1 | ASN | A | 290 | 7.751 | -1.435 | 28.110 | 1.00 62.66 |
| ATOM | 413 | ND2 | ASN | A | 290 | 9.828 | -2.055 | 27.472 | 1.00 61.45 |
| ATOM | 414 | C | ASN | A | 290 | 9.173 | -0.971 | 23.428 | 1.00 57.27 |
| ATOM | 415 | O | ASN | A | 290 | 8.682 | -1.987 | 22.939 | 1.00 58.32 |
| ATOM | 416 | N | LEU | A | 291 | 9.479 | 0.094 | 22.706 | 1.00 55.72 |
| ATOM | 417 | CA | LEU | A | 291 | 9.203 | 0.220 | 21.275 | 1.00 54.04 |
| ATOM | 418 | CB | LEU | A | 291 | 8.559 | 1.593 | 21.063 | 1.00 57.04 |
| ATOM | 419 | CG | LEU | A | 291 | 7.734 | 2.007 | 22.308 | 1.00 58.68 |
| ATOM | 420 | CD1 | LEU | A | 291 | 7.532 | 3.506 | 22.390 | 1.00 56.97 |
| ATOM | 421 | CD2 | LEU | A | 291 | 6.401 | 1.244 | 22.363 | 1.00 61.46 |
| ATOM | 422 | C | LEU | A | 291 | 10.498 | 0.079 | 20.448 | 1.00 51.92 |
| ATOM | 423 | O | LEU | A | 291 | 10.477 | -0.277 | 19.267 | 1.00 51.58 |
| ATOM | 424 | N | MET | A | 292 | 11.616 | 0.402 | 21.095 | 1.00 49.47 |
| ATOM | 425 | CA | MET | A | 292 | 12.972 | 0.310 | 20.542 | 1.00 45.59 |
| ATOM | 426 | CB | MET | A | 292 | 13.877 | 1.262 | 21.329 | 1.00 42.45 |
| ATOM | 427 | CG | MET | A | 292 | 15.308 | 1.412 | 20.853 | 1.00 40.53 |
| ATOM | 428 | SD | MET | A | 292 | 16.205 | 2.631 | 21.883 | 1.00 34.75 |
| ATOM | 429 | CE | MET | A | 292 | 16.143 | 4.081 | 20.798 | 1.00 35.14 |
| ATOM | 430 | C | MET | A | 292 | 13.390 | -1.154 | 20.773 | 1.00 44.67 |
| ATOM | 431 | O | MET | A | 292 | 14.282 | -1.684 | 20.106 | 1.00 43.41 |
| ATOM | 432 | N | LYS | A | 293 | 12.706 | -1.794 | 21.724 | 1.00 44.49 |
| ATOM | 433 | CA | LYS | A | 293 | 12.914 | -3.193 | 22.076 | 1.00 44.40 |
| ATOM | 434 | CB | LYS | A | 293 | 12.108 | -3.557 | 23.325 | 1.00 44.27 |
| ATOM | 435 | CG | LYS | A | 293 | 12.580 | -2.970 | 24.625 | 1.00 45.56 |
| ATOM | 436 | CD | LYS | A | 293 | 11.926 | -3.714 | 25.767 | 1.00 48.23 |
| ATOM | 437 | CE | LYS | A | 293 | 12.539 | -3.364 | 27.115 | 1.00 51.69 |
| ATOM | 438 | NZ | LYS | A | 293 | 12.117 | -4.315 | 28.206 | 1.00 55.08 |
| ATOM | 439 | C | LYS | A | 293 | 12.421 | -4.089 | 20.955 | 1.00 44.42 |
| ATOM | 440 | O | LYS | A | 293 | 12.930 | -5.189 | 20.770 | 1.00 45.57 |
| ATOM | 441 | N | GLN | A | 294 | 11.377 | -3.635 | 20.262 | 1.00 44.82 |
| ATOM | 442 | CA | GLN | A | 294 | 10.758 | -4.390 | 19.172 | 1.00 45.38 |
| ATOM | 443 | CB | GLN | A | 294 | 9.262 | -4.040 | 19.046 | 1.00 48.18 |
| ATOM | 444 | CG | GLN | A | 294 | 8.458 | -4.085 | 20.355 | 1.00 53.82 |
| ATOM | 445 | CD | GLN | A | 294 | 8.464 | -5.461 | 21.023 | 1.00 57.34 |
| ATOM | 446 | OE1 | GLN | A | 294 | 9.048 | -5.649 | 22.103 | 1.00 58.94 |
| ATOM | 447 | NE2 | GLN | A | 294 | 7.784 | -6.421 | 20.397 | 1.00 58.98 |
| ATOM | 448 | C | GLN | A | 294 | 11.414 | -4.206 | 17.811 | 1.00 44.12 |
| ATOM | 449 | O | GLN | A | 294 | 11.598 | -5.171 | 17.076 | 1.00 44.89 |
| ATOM | 450 | N | LEU | A | 295 | 11.779 | -2.972 | 17.480 | 1.00 42.32 |
| ATOM | 451 | CA | LEU | A | 295 | 12.367 | -2.696 | 16.173 | 1.00 40.69 |
| ATOM | 452 | CB | LEU | A | 295 | 11.659 | -1.516 | 15.501 | 1.00 40.36 |
| ATOM | 453 | CG | LEU | A | 295 | 10.164 | -1.619 | 15.193 | 1.00 40.60 |
| ATOM | 454 | CD1 | LEU | A | 295 | 9.724 | -0.339 | 14.513 | 1.00 40.56 |
| ATOM | 455 | CD2 | LEU | A | 295 | 9.874 | -2.821 | 14.305 | 1.00 38.48 |
| ATOM | 456 | C | LEU | A | 295 | 13.860 | -2.453 | 16.149 | 1.00 39.49 |
| ATOM | 457 | O | LEU | A | 295 | 14.357 | -1.531 | 16.784 | 1.00 38.98 |
| ATOM | 458 | N | GLN | A | 296 | 14.559 | -3.253 | 15.352 | 1.00 37.64 |
| ATOM | 459 | CA | GLN | A | 296 | 16.002 | -3.123 | 15.214 | 1.00 37.46 |

Figure 7

| ATOM | 460 | CB | GLN | A | 296 | 16.712 | -4.304 | 15.899 | 1.00 | 39.63 |
| ATOM | 461 | CG | GLN | A | 296 | 16.469 | -4.323 | 17.422 | 1.00 | 44.10 |
| ATOM | 462 | CD | GLN | A | 296 | 16.149 | -5.696 | 17.958 | 1.00 | 47.07 |
| ATOM | 463 | OE1 | GLN | A | 296 | 15.777 | -6.596 | 17.203 | 1.00 | 49.52 |
| ATOM | 464 | NE2 | GLN | A | 296 | 16.277 | -5.868 | 19.272 | 1.00 | 48.80 |
| ATOM | 465 | C | GLN | A | 296 | 16.373 | -2.984 | 13.736 | 1.00 | 35.77 |
| ATOM | 466 | O | GLN | A | 296 | 15.870 | -3.716 | 12.882 | 1.00 | 35.79 |
| ATOM | 467 | N | HIS | A | 297 | 17.198 | -1.982 | 13.442 | 1.00 | 33.84 |
| ATOM | 468 | CA | HIS | A | 297 | 17.625 | -1.691 | 12.073 | 1.00 | 32.96 |
| ATOM | 469 | CB | HIS | A | 297 | 16.513 | -0.901 | 11.361 | 1.00 | 31.72 |
| ATOM | 470 | CG | HIS | A | 297 | 16.720 | -0.756 | 9.888 | 1.00 | 29.18 |
| ATOM | 471 | CD2 | HIS | A | 297 | 16.394 | -1.572 | 8.856 | 1.00 | 28.54 |
| ATOM | 472 | ND1 | HIS | A | 297 | 17.403 | 0.300 | 9.332 | 1.00 | 28.57 |
| ATOM | 473 | CE1 | HIS | A | 297 | 17.504 | 0.130 | 8.026 | 1.00 | 27.39 |
| ATOM | 474 | NE2 | HIS | A | 297 | 16.899 | -1.001 | 7.716 | 1.00 | 28.85 |
| ATOM | 475 | C | HIS | A | 297 | 18.919 | -0.861 | 12.102 | 1.00 | 32.96 |
| ATOM | 476 | O | HIS | A | 297 | 19.224 | -0.233 | 13.115 | 1.00 | 32.64 |
| ATOM | 477 | N | GLN | A | 298 | 19.676 | -0.856 | 11.001 | 1.00 | 33.21 |
| ATOM | 478 | CA | GLN | A | 298 | 20.922 | -0.075 | 10.942 | 1.00 | 34.54 |
| ATOM | 479 | CB | GLN | A | 298 | 21.778 | -0.405 | 9.704 | 1.00 | 36.37 |
| ATOM | 480 | CG | GLN | A | 298 | 22.694 | -1.640 | 9.869 | 1.00 | 44.33 |
| ATOM | 481 | CD | GLN | A | 298 | 23.289 | -1.824 | 11.290 | 1.00 | 46.62 |
| ATOM | 482 | OE1 | GLN | A | 298 | 22.997 | -2.817 | 11.967 | 1.00 | 47.54 |
| ATOM | 483 | NE2 | GLN | A | 298 | 24.134 | -0.882 | 11.727 | 1.00 | 48.19 |
| ATOM | 484 | C | GLN | A | 298 | 20.719 | 1.426 | 11.005 | 1.00 | 33.50 |
| ATOM | 485 | O | GLN | A | 298 | 21.664 | 2.169 | 11.282 | 1.00 | 34.40 |
| ATOM | 486 | N | ARG | A | 299 | 19.479 | 1.862 | 10.794 | 1.00 | 32.24 |
| ATOM | 487 | CA | ARG | A | 299 | 19.136 | 3.282 | 10.788 | 1.00 | 30.45 |
| ATOM | 488 | CB | ARG | A | 299 | 18.333 | 3.629 | 9.527 | 1.00 | 29.33 |
| ATOM | 489 | CG | ARG | A | 299 | 19.054 | 3.302 | 8.245 | 1.00 | 29.90 |
| ATOM | 490 | CD | ARG | A | 299 | 20.261 | 4.175 | 8.137 | 1.00 | 31.69 |
| ATOM | 491 | NE | ARG | A | 299 | 21.272 | 3.686 | 7.208 | 1.00 | 32.36 |
| ATOM | 492 | CZ | ARG | A | 299 | 22.578 | 3.725 | 7.477 | 1.00 | 34.32 |
| ATOM | 493 | NH1 | ARG | A | 299 | 23.000 | 4.201 | 8.649 | 1.00 | 35.45 |
| ATOM | 494 | NH2 | ARG | A | 299 | 23.458 | 3.398 | 6.548 | 1.00 | 32.91 |
| ATOM | 495 | C | ARG | A | 299 | 18.351 | 3.665 | 12.029 | 1.00 | 29.45 |
| ATOM | 496 | O | ARG | A | 299 | 17.804 | 4.762 | 12.111 | 1.00 | 29.16 |
| ATOM | 497 | N | LEU | A | 300 | 18.232 | 2.727 | 12.956 | 1.00 | 29.63 |
| ATOM | 498 | CA | LEU | A | 300 | 17.534 | 2.972 | 14.211 | 1.00 | 30.82 |
| ATOM | 499 | CB | LEU | A | 300 | 16.372 | 1.989 | 14.387 | 1.00 | 30.34 |
| ATOM | 500 | CG | LEU | A | 300 | 14.956 | 2.356 | 13.939 | 1.00 | 29.72 |
| ATOM | 501 | CD1 | LEU | A | 300 | 14.936 | 3.020 | 12.573 | 1.00 | 29.47 |
| ATOM | 502 | CD2 | LEU | A | 300 | 14.113 | 1.091 | 13.944 | 1.00 | 28.53 |
| ATOM | 503 | C | LEU | A | 300 | 18.544 | 2.788 | 15.342 | 1.00 | 31.27 |
| ATOM | 504 | O | LEU | A | 300 | 19.365 | 1.865 | 15.306 | 1.00 | 31.07 |
| ATOM | 505 | N | VAL | A | 301 | 18.494 | 3.683 | 16.326 | 1.00 | 32.54 |
| ATOM | 506 | CA | VAL | A | 301 | 19.388 | 3.616 | 17.473 | 1.00 | 32.47 |
| ATOM | 507 | CB | VAL | A | 301 | 19.276 | 4.886 | 18.345 | 1.00 | 31.52 |
| ATOM | 508 | CG1 | VAL | A | 301 | 19.995 | 4.690 | 19.666 | 1.00 | 29.51 |
| ATOM | 509 | CG2 | VAL | A | 301 | 19.894 | 6.079 | 17.600 | 1.00 | 28.56 |
| ATOM | 510 | C | VAL | A | 301 | 19.077 | 2.335 | 18.253 | 1.00 | 33.35 |
| ATOM | 511 | O | VAL | A | 301 | 17.920 | 2.011 | 18.513 | 1.00 | 32.24 |
| ATOM | 512 | N | ARG | A | 302 | 20.134 | 1.588 | 18.561 | 1.00 | 34.82 |
| ATOM | 513 | CA | ARG | A | 302 | 20.047 | 0.312 | 19.251 | 1.00 | 37.12 |
| ATOM | 514 | CB | ARG | A | 302 | 21.204 | -0.581 | 18.757 | 1.00 | 40.38 |
| ATOM | 515 | CG | ARG | A | 302 | 21.237 | -2.027 | 19.255 | 1.00 | 47.36 |
| ATOM | 516 | CD | ARG | A | 302 | 22.157 | -2.177 | 20.481 | 1.00 | 54.67 |
| ATOM | 517 | NE | ARG | A | 302 | 22.599 | -3.560 | 20.746 | 1.00 | 60.06 |
| ATOM | 518 | CZ | ARG | A | 302 | 23.579 | -4.190 | 20.087 | 1.00 | 62.11 |

Figure 7

| | | | | | | | | | |
|---|---|---|---|---|---|---|---|---|---|
| ATOM | 519 | NH1 | ARG | A | 302 | 24.236 | -3.572 | 19.110 | 1.00 63.76 |
| ATOM | 520 | NH2 | ARG | A | 302 | 23.945 | -5.418 | 20.438 | 1.00 61.82 |
| ATOM | 521 | C | ARG | A | 302 | 20.029 | 0.439 | 20.777 | 1.00 37.35 |
| ATOM | 522 | O | ARG | A | 302 | 20.802 | 1.204 | 21.368 | 1.00 38.29 |
| ATOM | 523 | N | LEU | A | 303 | 19.112 | -0.295 | 21.405 | 1.00 36.71 |
| ATOM | 524 | CA | LEU | A | 303 | 18.969 | -0.318 | 22.862 | 1.00 35.81 |
| ATOM | 525 | CB | LEU | A | 303 | 17.501 | -0.557 | 23.229 | 1.00 35.19 |
| ATOM | 526 | CG | LEU | A | 303 | 17.130 | -0.590 | 24.710 | 1.00 35.17 |
| ATOM | 527 | CD1 | LEU | A | 303 | 17.211 | 0.807 | 25.289 | 1.00 35.38 |
| ATOM | 528 | CD2 | LEU | A | 303 | 15.730 | -1.147 | 24.879 | 1.00 35.68 |
| ATOM | 529 | C | LEU | A | 303 | 19.819 | -1.462 | 23.414 | 1.00 35.50 |
| ATOM | 530 | O | LEU | A | 303 | 19.784 | -2.580 | 22.891 | 1.00 35.39 |
| ATOM | 531 | N | TYR | A | 304 | 20.610 | -1.182 | 24.442 | 1.00 35.36 |
| ATOM | 532 | CA | TYR | A | 304 | 21.455 | -2.217 | 25.048 | 1.00 36.40 |
| ATOM | 533 | CB | TYR | A | 304 | 22.820 | -1.650 | 25.464 | 1.00 37.54 |
| ATOM | 534 | CG | TYR | A | 304 | 23.779 | -1.413 | 24.322 | 1.00 40.66 |
| ATOM | 535 | CD1 | TYR | A | 304 | 24.453 | -0.206 | 24.198 | 1.00 41.98 |
| ATOM | 536 | CE1 | TYR | A | 304 | 25.364 | 0.012 | 23.172 | 1.00 43.08 |
| ATOM | 537 | CD2 | TYR | A | 304 | 24.035 | -2.403 | 23.383 | 1.00 42.41 |
| ATOM | 538 | CE2 | TYR | A | 304 | 24.949 | -2.188 | 22.347 | 1.00 44.15 |
| ATOM | 539 | CZ | TYR | A | 304 | 25.607 | -0.981 | 22.251 | 1.00 43.48 |
| ATOM | 540 | OH | TYR | A | 304 | 26.525 | -0.770 | 21.249 | 1.00 44.87 |
| ATOM | 541 | C | TYR | A | 304 | 20.803 | -2.857 | 26.263 | 1.00 35.49 |
| ATOM | 542 | O | TYR | A | 304 | 20.657 | -4.073 | 26.337 | 1.00 34.41 |
| ATOM | 543 | N | ALA | A | 305 | 20.392 | -2.014 | 27.199 | 1.00 35.37 |
| ATOM | 544 | CA | ALA | A | 305 | 19.785 | -2.487 | 28.418 | 1.00 35.95 |
| ATOM | 545 | CB | ALA | A | 305 | 20.871 | -3.008 | 29.338 | 1.00 35.00 |
| ATOM | 546 | C | ALA | A | 305 | 19.009 | -1.387 | 29.115 | 1.00 36.82 |
| ATOM | 547 | O | ALA | A | 305 | 18.880 | -0.270 | 28.606 | 1.00 36.50 |
| ATOM | 548 | N | VAL | A | 306 | 18.496 | -1.725 | 30.295 | 1.00 38.51 |
| ATOM | 549 | CA | VAL | A | 306 | 17.744 | -0.808 | 31.146 | 1.00 39.58 |
| ATOM | 550 | CB | VAL | A | 306 | 16.192 | -0.859 | 30.877 | 1.00 40.69 |
| ATOM | 551 | CG1 | VAL | A | 306 | 15.877 | -0.556 | 29.404 | 1.00 41.59 |
| ATOM | 552 | CG2 | VAL | A | 306 | 15.607 | -2.216 | 31.282 | 1.00 39.76 |
| ATOM | 553 | C | VAL | A | 306 | 17.984 | -1.227 | 32.594 | 1.00 40.16 |
| ATOM | 554 | O | VAL | A | 306 | 18.284 | -2.395 | 32.875 | 1.00 39.55 |
| ATOM | 555 | N | VAL | A | 307 | 17.922 | -0.254 | 33.496 | 1.00 41.40 |
| ATOM | 556 | CA | VAL | A | 307 | 18.068 | -0.498 | 34.926 | 1.00 42.40 |
| ATOM | 557 | CB | VAL | A | 307 | 19.253 | 0.310 | 35.537 | 1.00 41.78 |
| ATOM | 558 | CG1 | VAL | A | 307 | 19.300 | 0.146 | 37.044 | 1.00 40.03 |
| ATOM | 559 | CG2 | VAL | A | 307 | 20.567 | -0.168 | 34.937 | 1.00 41.68 |
| ATOM | 560 | C | VAL | A | 307 | 16.722 | -0.068 | 35.509 | 1.00 43.34 |
| ATOM | 561 | O | VAL | A | 307 | 16.352 | 1.108 | 35.455 | 1.00 41.81 |
| ATOM | 562 | N | THR | A | 308 | 15.979 | -1.051 | 36.014 | 1.00 46.06 |
| ATOM | 563 | CA | THR | A | 308 | 14.650 | -0.828 | 36.575 | 1.00 48.71 |
| ATOM | 564 | CB | THR | A | 308 | 13.780 | -2.094 | 36.451 | 1.00 49.35 |
| ATOM | 565 | OG1 | THR | A | 308 | 14.379 | -3.173 | 37.182 | 1.00 52.63 |
| ATOM | 566 | CG2 | THR | A | 308 | 13.653 | -2.492 | 34.995 | 1.00 47.45 |
| ATOM | 567 | C | THR | A | 308 | 14.570 | -0.250 | 37.996 | 1.00 50.32 |
| ATOM | 568 | O | THR | A | 308 | 13.500 | 0.194 | 38.414 | 1.00 51.17 |
| ATOM | 569 | N | GLN | A | 309 | 15.679 | -0.260 | 38.739 | 1.00 51.63 |
| ATOM | 570 | CA | GLN | A | 309 | 15.704 | 0.321 | 40.084 | 1.00 53.18 |
| ATOM | 571 | CB | GLN | A | 309 | 16.764 | -0.362 | 40.953 | 1.00 57.15 |
| ATOM | 572 | CG | GLN | A | 309 | 16.411 | -1.787 | 41.351 | 1.00 62.61 |
| ATOM | 573 | CD | GLN | A | 309 | 15.112 | -1.863 | 42.151 | 1.00 67.18 |
| ATOM | 574 | OE1 | GLN | A | 309 | 14.608 | -0.849 | 42.660 | 1.00 68.61 |
| ATOM | 575 | NE2 | GLN | A | 309 | 14.564 | -3.070 | 42.266 | 1.00 69.00 |
| ATOM | 576 | C | GLN | A | 309 | 16.017 | 1.808 | 39.949 | 1.00 52.01 |
| ATOM | 577 | O | GLN | A | 309 | 16.958 | 2.175 | 39.238 | 1.00 51.07 |

Figure 7

| | | | | | | | | | |
|---|---|---|---|---|---|---|---|---|---|
| ATOM | 578 | N | GLU | A | 310 | 15.266 | 2.656 | 40.650 | 1.00 51.14 |
| ATOM | 579 | CA | GLU | A | 310 | 15.471 | 4.097 | 40.540 | 1.00 52.25 |
| ATOM | 580 | CB | GLU | A | 310 | 14.308 | 4.879 | 41.168 | 1.00 55.54 |
| ATOM | 581 | CG | GLU | A | 310 | 14.362 | 5.006 | 42.683 | 1.00 63.91 |
| ATOM | 582 | CD | GLU | A | 310 | 13.176 | 4.349 | 43.381 | 1.00 68.42 |
| ATOM | 583 | OE1 | GLU | A | 310 | 12.020 | 4.687 | 43.011 | 1.00 71.41 |
| ATOM | 584 | OE2 | GLU | A | 310 | 13.405 | 3.506 | 44.296 | 1.00 68.45 |
| ATOM | 585 | C | GLU | A | 310 | 16.820 | 4.563 | 41.099 | 1.00 51.09 |
| ATOM | 586 | O | GLU | A | 310 | 17.300 | 4.013 | 42.090 | 1.00 51.54 |
| ATOM | 587 | N | PRO | A | 311 | 17.487 | 5.526 | 40.421 | 1.00 49.47 |
| ATOM | 588 | CD | PRO | A | 311 | 18.743 | 6.101 | 40.935 | 1.00 49.19 |
| ATOM | 589 | CA | PRO | A | 311 | 17.087 | 6.212 | 39.178 | 1.00 47.38 |
| ATOM | 590 | CB | PRO | A | 311 | 18.241 | 7.188 | 38.943 | 1.00 48.66 |
| ATOM | 591 | CG | PRO | A | 311 | 18.732 | 7.480 | 40.329 | 1.00 48.71 |
| ATOM | 592 | C | PRO | A | 311 | 16.932 | 5.253 | 37.996 | 1.00 44.97 |
| ATOM | 593 | O | PRO | A | 311 | 17.777 | 4.384 | 37.776 | 1.00 44.47 |
| ATOM | 594 | N | ILE | A | 312 | 15.828 | 5.395 | 37.261 | 1.00 42.82 |
| ATOM | 595 | CA | ILE | A | 312 | 15.553 | 4.525 | 36.108 | 1.00 39.29 |
| ATOM | 596 | CB | ILE | A | 312 | 14.067 | 4.623 | 35.647 | 1.00 37.92 |
| ATOM | 597 | CG2 | ILE | A | 312 | 13.700 | 3.407 | 34.823 | 1.00 36.27 |
| ATOM | 598 | CG1 | ILE | A | 312 | 13.131 | 4.683 | 36.857 | 1.00 38.30 |
| ATOM | 599 | CD1 | ILE | A | 312 | 13.083 | 3.414 | 37.667 | 1.00 38.71 |
| ATOM | 600 | C | ILE | A | 312 | 16.482 | 4.883 | 34.939 | 1.00 36.67 |
| ATOM | 601 | O | ILE | A | 312 | 16.640 | 6.063 | 34.598 | 1.00 35.72 |
| ATOM | 602 | N | TYR | A | 313 | 17.118 | 3.855 | 34.365 | 1.00 34.66 |
| ATOM | 603 | CA | TYR | A | 313 | 18.051 | 4.005 | 33.243 | 1.00 32.13 |
| ATOM | 604 | CB | TYR | A | 313 | 19.442 | 3.479 | 33.614 | 1.00 31.75 |
| ATOM | 605 | CG | TYR | A | 313 | 20.247 | 4.283 | 34.617 | 1.00 33.03 |
| ATOM | 606 | CD1 | TYR | A | 313 | 19.869 | 5.568 | 34.997 | 1.00 34.17 |
| ATOM | 607 | CE1 | TYR | A | 313 | 20.642 | 6.307 | 35.906 | 1.00 35.14 |
| ATOM | 608 | CD2 | TYR | A | 313 | 21.418 | 3.754 | 35.168 | 1.00 33.54 |
| ATOM | 609 | CE2 | TYR | A | 313 | 22.194 | 4.484 | 36.073 | 1.00 32.83 |
| ATOM | 610 | CZ | TYR | A | 313 | 21.799 | 5.753 | 36.435 | 1.00 34.26 |
| ATOM | 611 | OH | TYR | A | 313 | 22.545 | 6.465 | 37.343 | 1.00 34.91 |
| ATOM | 612 | C | TYR | A | 313 | 17.648 | 3.261 | 31.972 | 1.00 30.89 |
| ATOM | 613 | O | TYR | A | 313 | 17.190 | 2.121 | 32.020 | 1.00 30.73 |
| ATOM | 614 | N | ILE | A | 314 | 17.852 | 3.918 | 30.835 | 1.00 30.05 |
| ATOM | 615 | CA | ILE | A | 314 | 17.618 | 3.333 | 29.514 | 1.00 28.73 |
| ATOM | 616 | CB | ILE | A | 314 | 16.511 | 4.071 | 28.722 | 1.00 28.07 |
| ATOM | 617 | CG2 | ILE | A | 314 | 16.568 | 3.694 | 27.251 | 1.00 26.27 |
| ATOM | 618 | CG1 | ILE | A | 314 | 15.150 | 3.674 | 29.280 | 1.00 27.38 |
| ATOM | 619 | CD1 | ILE | A | 314 | 14.038 | 4.530 | 28.811 | 1.00 27.49 |
| ATOM | 620 | C | ILE | A | 314 | 18.988 | 3.515 | 28.852 | 1.00 28.09 |
| ATOM | 621 | O | ILE | A | 314 | 19.498 | 4.631 | 28.774 | 1.00 28.66 |
| ATOM | 622 | N | ILE | A | 315 | 19.613 | 2.410 | 28.458 | 1.00 27.24 |
| ATOM | 623 | CA | ILE | A | 315 | 20.943 | 2.462 | 27.861 | 1.00 26.37 |
| ATOM | 624 | CB | ILE | A | 315 | 21.947 | 1.505 | 28.591 | 1.00 26.21 |
| ATOM | 625 | CG2 | ILE | A | 315 | 23.315 | 1.577 | 27.962 | 1.00 25.10 |
| ATOM | 626 | CG1 | ILE | A | 315 | 22.039 | 1.833 | 30.077 | 1.00 25.54 |
| ATOM | 627 | CD1 | ILE | A | 315 | 21.083 | 1.023 | 30.915 | 1.00 27.66 |
| ATOM | 628 | C | ILE | A | 315 | 20.943 | 2.096 | 26.389 | 1.00 25.84 |
| ATOM | 629 | O | ILE | A | 315 | 20.564 | 0.988 | 26.016 | 1.00 25.06 |
| ATOM | 630 | N | THR | A | 316 | 21.427 | 3.019 | 25.567 | 1.00 25.45 |
| ATOM | 631 | CA | THR | A | 316 | 21.508 | 2.798 | 24.135 | 1.00 25.87 |
| ATOM | 632 | CB | THR | A | 316 | 20.607 | 3.807 | 23.355 | 1.00 24.45 |
| ATOM | 633 | OG1 | THR | A | 316 | 21.097 | 5.134 | 23.540 | 1.00 23.35 |
| ATOM | 634 | CG2 | THR | A | 316 | 19.167 | 3.765 | 23.849 | 1.00 24.48 |
| ATOM | 635 | C | THR | A | 316 | 22.969 | 2.974 | 23.680 | 1.00 27.24 |
| ATOM | 636 | O | THR | A | 316 | 23.858 | 3.323 | 24.479 | 1.00 26.97 |

Figure 7

| | | | | | | | | | |
|---|---|---|---|---|---|---|---|---|---|
| ATOM | 637 | N | GLU | A | 317 | 23.213 | 2.717 | 22.395 | 1.00 27.63 |
| ATOM | 638 | CA | GLU | A | 317 | 24.542 | 2.883 | 21.833 | 1.00 26.96 |
| ATOM | 639 | CB | GLU | A | 317 | 24.574 | 2.400 | 20.375 | 1.00 26.82 |
| ATOM | 640 | CG | GLU | A | 317 | 23.857 | 3.311 | 19.380 | 1.00 27.07 |
| ATOM | 641 | CD | GLU | A | 317 | 23.804 | 2.734 | 17.990 | 1.00 27.96 |
| ATOM | 642 | OE1 | GLU | A | 317 | 22.696 | 2.375 | 17.538 | 1.00 28.70 |
| ATOM | 643 | OE2 | GLU | A | 317 | 24.863 | 2.645 | 17.339 | 1.00 30.59 |
| ATOM | 644 | C | GLU | A | 317 | 24.862 | 4.371 | 21.901 | 1.00 27.09 |
| ATOM | 645 | O | GLU | A | 317 | 23.956 | 5.203 | 22.020 | 1.00 28.33 |
| ATOM | 646 | N | TYR | A | 318 | 26.144 | 4.708 | 21.899 | 1.00 26.51 |
| ATOM | 647 | CA | TYR | A | 318 | 26.517 | 6.108 | 21.935 | 1.00 25.56 |
| ATOM | 648 | CB | TYR | A | 318 | 27.765 | 6.305 | 22.789 | 1.00 24.65 |
| ATOM | 649 | CG | TYR | A | 318 | 28.217 | 7.735 | 22.898 | 1.00 23.50 |
| ATOM | 650 | CD1 | TYR | A | 318 | 27.538 | 8.649 | 23.704 | 1.00 23.38 |
| ATOM | 651 | CE1 | TYR | A | 318 | 27.973 | 9.979 | 23.807 | 1.00 24.86 |
| ATOM | 652 | CD2 | TYR | A | 318 | 29.339 | 8.175 | 22.197 | 1.00 24.31 |
| ATOM | 653 | CE2 | TYR | A | 318 | 29.784 | 9.489 | 22.292 | 1.00 24.42 |
| ATOM | 654 | CZ | TYR | A | 318 | 29.100 | 10.386 | 23.095 | 1.00 26.32 |
| ATOM | 655 | OH | TYR | A | 318 | 29.552 | 11.683 | 23.174 | 1.00 27.92 |
| ATOM | 656 | C | TYR | A | 318 | 26.731 | 6.612 | 20.507 | 1.00 24.93 |
| ATOM | 657 | O | TYR | A | 318 | 27.329 | 5.932 | 19.680 | 1.00 23.33 |
| ATOM | 658 | N | MET | A | 319 | 26.147 | 7.771 | 20.215 | 1.00 26.46 |
| ATOM | 659 | CA | MET | A | 319 | 26.254 | 8.403 | 18.900 | 1.00 26.76 |
| ATOM | 660 | CB | MET | A | 319 | 24.884 | 8.875 | 18.412 | 1.00 26.35 |
| ATOM | 661 | CG | MET | A | 319 | 23.931 | 7.721 | 18.171 | 1.00 26.77 |
| ATOM | 662 | SD | MET | A | 319 | 24.594 | 6.499 | 17.032 | 1.00 29.68 |
| ATOM | 663 | CE | MET | A | 319 | 24.359 | 7.353 | 15.466 | 1.00 31.01 |
| ATOM | 664 | C | MET | A | 319 | 27.229 | 9.558 | 19.007 | 1.00 26.72 |
| ATOM | 665 | O | MET | A | 319 | 26.891 | 10.647 | 19.454 | 1.00 25.95 |
| ATOM | 666 | N | GLU | A | 320 | 28.460 | 9.262 | 18.613 | 1.00 26.98 |
| ATOM | 667 | CA | GLU | A | 320 | 29.578 | 10.181 | 18.649 | 1.00 28.23 |
| ATOM | 668 | CB | GLU | A | 320 | 30.703 | 9.608 | 17.772 | 1.00 32.29 |
| ATOM | 669 | CG | GLU | A | 320 | 32.054 | 10.291 | 17.915 | 1.00 37.44 |
| ATOM | 670 | CD | GLU | A | 320 | 32.523 | 10.417 | 19.372 | 1.00 40.91 |
| ATOM | 671 | OE1 | GLU | A | 320 | 32.549 | 9.393 | 20.118 | 1.00 37.26 |
| ATOM | 672 | OE2 | GLU | A | 320 | 32.875 | 11.563 | 19.753 | 1.00 42.45 |
| ATOM | 673 | C | GLU | A | 320 | 29.312 | 11.656 | 18.339 | 1.00 27.17 |
| ATOM | 674 | O | GLU | A | 320 | 29.742 | 12.518 | 19.094 | 1.00 27.19 |
| ATOM | 675 | N | ASN | A | 321 | 28.592 | 11.952 | 17.260 | 1.00 26.51 |
| ATOM | 676 | CA | ASN | A | 321 | 28.309 | 13.342 | 16.887 | 1.00 25.15 |
| ATOM | 677 | CB | ASN | A | 321 | 28.458 | 13.516 | 15.389 | 1.00 25.47 |
| ATOM | 678 | CG | ASN | A | 321 | 29.890 | 13.555 | 14.968 | 1.00 27.05 |
| ATOM | 679 | OD1 | ASN | A | 321 | 30.668 | 14.366 | 15.475 | 1.00 28.74 |
| ATOM | 680 | ND2 | ASN | A | 321 | 30.267 | 12.670 | 14.062 | 1.00 27.80 |
| ATOM | 681 | C | ASN | A | 321 | 27.001 | 13.967 | 17.365 | 1.00 25.09 |
| ATOM | 682 | O | ASN | A | 321 | 26.621 | 15.061 | 16.930 | 1.00 24.76 |
| ATOM | 683 | N | GLY | A | 322 | 26.322 | 13.270 | 18.270 | 1.00 25.16 |
| ATOM | 684 | CA | GLY | A | 322 | 25.086 | 13.766 | 18.839 | 1.00 24.80 |
| ATOM | 685 | C | GLY | A | 322 | 23.872 | 13.929 | 17.953 | 1.00 25.47 |
| ATOM | 686 | O | GLY | A | 322 | 23.585 | 13.117 | 17.075 | 1.00 26.04 |
| ATOM | 687 | N | SER | A | 323 | 23.139 | 14.993 | 18.239 | 1.00 25.73 |
| ATOM | 688 | CA | SER | A | 323 | 21.925 | 15.344 | 17.536 | 1.00 26.47 |
| ATOM | 689 | CB | SER | A | 323 | 21.111 | 16.293 | 18.416 | 1.00 27.95 |
| ATOM | 690 | OG | SER | A | 323 | 19.895 | 16.674 | 17.806 | 1.00 32.00 |
| ATOM | 691 | C | SER | A | 323 | 22.238 | 15.997 | 16.199 | 1.00 26.26 |
| ATOM | 692 | O | SER | A | 323 | 23.118 | 16.842 | 16.109 | 1.00 26.10 |
| ATOM | 693 | N | LEU | A | 324 | 21.503 | 15.599 | 15.164 | 1.00 26.77 |
| ATOM | 694 | CA | LEU | A | 324 | 21.680 | 16.139 | 13.827 | 1.00 25.66 |
| ATOM | 695 | CB | LEU | A | 324 | 20.790 | 15.391 | 12.827 | 1.00 25.84 |

Figure 7

| | | | | | | | | |
|---|---|---|---|---|---|---|---|---|
| ATOM | 696 | CG | LEU | A | 324 | 20.779 | 15.884 | 11.366 | 1.00 | 24.56 |
| ATOM | 697 | CD1 | LEU | A | 324 | 22.140 | 15.631 | 10.710 | 1.00 | 20.66 |
| ATOM | 698 | CD2 | LEU | A | 324 | 19.654 | 15.201 | 10.581 | 1.00 | 22.84 |
| ATOM | 699 | C | LEU | A | 324 | 21.394 | 17.639 | 13.758 | 1.00 | 25.67 |
| ATOM | 700 | O | LEU | A | 324 | 22.105 | 18.378 | 13.084 | 1.00 | 26.23 |
| ATOM | 701 | N | VAL | A | 325 | 20.360 | 18.101 | 14.448 | 1.00 | 25.81 |
| ATOM | 702 | CA | VAL | A | 325 | 20.039 | 19.524 | 14.410 | 1.00 | 27.25 |
| ATOM | 703 | CB | VAL | A | 325 | 18.764 | 19.843 | 15.234 | 1.00 | 26.49 |
| ATOM | 704 | CG1 | VAL | A | 325 | 19.068 | 19.877 | 16.724 | 1.00 | 26.24 |
| ATOM | 705 | CG2 | VAL | A | 325 | 18.142 | 21.140 | 14.765 | 1.00 | 25.72 |
| ATOM | 706 | C | VAL | A | 325 | 21.234 | 20.370 | 14.886 | 1.00 | 28.43 |
| ATOM | 707 | O | VAL | A | 325 | 21.506 | 21.437 | 14.340 | 1.00 | 28.15 |
| ATOM | 708 | N | ASP | A | 326 | 21.963 | 19.857 | 15.877 | 1.00 | 29.02 |
| ATOM | 709 | CA | ASP | A | 326 | 23.134 | 20.538 | 16.418 | 1.00 | 29.63 |
| ATOM | 710 | CB | ASP | A | 326 | 23.455 | 19.999 | 17.810 | 1.00 | 29.72 |
| ATOM | 711 | CG | ASP | A | 326 | 22.461 | 20.444 | 18.840 | 1.00 | 29.64 |
| ATOM | 712 | OD1 | ASP | A | 326 | 21.791 | 21.472 | 18.629 | 1.00 | 31.48 |
| ATOM | 713 | OD2 | ASP | A | 326 | 22.351 | 19.773 | 19.876 | 1.00 | 34.01 |
| ATOM | 714 | C | ASP | A | 326 | 24.348 | 20.347 | 15.531 | 1.00 | 30.07 |
| ATOM | 715 | O | ASP | A | 326 | 25.098 | 21.293 | 15.274 | 1.00 | 30.76 |
| ATOM | 716 | N | PHE | A | 327 | 24.541 | 19.102 | 15.102 | 1.00 | 29.96 |
| ATOM | 717 | CA | PHE | A | 327 | 25.655 | 18.722 | 14.261 | 1.00 | 30.33 |
| ATOM | 718 | CB | PHE | A | 327 | 25.586 | 17.240 | 13.912 | 1.00 | 29.99 |
| ATOM | 719 | CG | PHE | A | 327 | 26.706 | 16.792 | 13.029 | 1.00 | 31.28 |
| ATOM | 720 | CD1 | PHE | A | 327 | 28.022 | 16.815 | 13.493 | 1.00 | 31.91 |
| ATOM | 721 | CD2 | PHE | A | 327 | 26.464 | 16.404 | 11.723 | 1.00 | 31.34 |
| ATOM | 722 | CE1 | PHE | A | 327 | 29.074 | 16.465 | 12.669 | 1.00 | 30.90 |
| ATOM | 723 | CE2 | PHE | A | 327 | 27.513 | 16.050 | 10.881 | 1.00 | 32.34 |
| ATOM | 724 | CZ | PHE | A | 327 | 28.823 | 16.082 | 11.356 | 1.00 | 32.88 |
| ATOM | 725 | C | PHE | A | 327 | 25.748 | 19.528 | 12.983 | 1.00 | 31.07 |
| ATOM | 726 | O | PHE | A | 327 | 26.840 | 19.855 | 12.533 | 1.00 | 31.17 |
| ATOM | 727 | N | LEU | A | 328 | 24.596 | 19.828 | 12.397 | 1.00 | 32.26 |
| ATOM | 728 | CA | LEU | A | 328 | 24.532 | 20.585 | 11.148 | 1.00 | 34.42 |
| ATOM | 729 | CB | LEU | A | 328 | 23.105 | 20.572 | 10.588 | 1.00 | 33.77 |
| ATOM | 730 | CG | LEU | A | 328 | 22.602 | 19.331 | 9.850 | 1.00 | 32.79 |
| ATOM | 731 | CD1 | LEU | A | 328 | 21.103 | 19.476 | 9.573 | 1.00 | 33.37 |
| ATOM | 732 | CD2 | LEU | A | 328 | 23.384 | 19.133 | 8.569 | 1.00 | 30.61 |
| ATOM | 733 | C | LEU | A | 328 | 25.001 | 22.030 | 11.294 | 1.00 | 35.98 |
| ATOM | 734 | O | LEU | A | 328 | 25.324 | 22.681 | 10.296 | 1.00 | 36.10 |
| ATOM | 735 | N | LYS | A | 329 | 24.996 | 22.541 | 12.524 | 1.00 | 37.05 |
| ATOM | 736 | CA | LYS | A | 329 | 25.422 | 23.908 | 12.766 | 1.00 | 37.93 |
| ATOM | 737 | CB | LYS | A | 329 | 24.604 | 24.544 | 13.892 | 1.00 | 38.09 |
| ATOM | 738 | CG | LYS | A | 329 | 23.114 | 24.604 | 13.630 | 1.00 | 37.14 |
| ATOM | 739 | CD | LYS | A | 329 | 22.415 | 25.414 | 14.702 | 1.00 | 38.24 |
| ATOM | 740 | CE | LYS | A | 329 | 20.897 | 25.331 | 14.584 | 1.00 | 39.62 |
| ATOM | 741 | NZ | LYS | A | 329 | 20.388 | 23.997 | 15.012 | 1.00 | 41.20 |
| ATOM | 742 | C | LYS | A | 329 | 26.907 | 23.988 | 13.084 | 1.00 | 39.06 |
| ATOM | 743 | O | LYS | A | 329 | 27.475 | 25.092 | 13.064 | 1.00 | 39.86 |
| ATOM | 744 | N | THR | A | 330 | 27.530 | 22.831 | 13.353 | 1.00 | 40.08 |
| ATOM | 745 | CA | THR | A | 330 | 28.966 | 22.768 | 13.679 | 1.00 | 41.20 |
| ATOM | 746 | CB | THR | A | 330 | 29.382 | 21.413 | 14.335 | 1.00 | 40.17 |
| ATOM | 747 | OG1 | THR | A | 330 | 29.207 | 20.339 | 13.405 | 1.00 | 39.58 |
| ATOM | 748 | CG2 | THR | A | 330 | 28.586 | 21.144 | 15.601 | 1.00 | 39.23 |
| ATOM | 749 | C | THR | A | 330 | 29.840 | 22.994 | 12.440 | 1.00 | 42.92 |
| ATOM | 750 | O | THR | A | 330 | 29.403 | 22.751 | 11.313 | 1.00 | 43.20 |
| ATOM | 751 | N | PRO | A | 331 | 31.093 | 23.453 | 12.637 | 1.00 | 44.17 |
| ATOM | 752 | CD | PRO | A | 331 | 31.715 | 23.781 | 13.936 | 1.00 | 44.06 |
| ATOM | 753 | CA | PRO | A | 331 | 32.032 | 23.716 | 11.540 | 1.00 | 44.79 |
| ATOM | 754 | CB | PRO | A | 331 | 33.361 | 23.854 | 12.277 | 1.00 | 45.11 |

Figure 7

| | | | | | | | | | |
|---|---|---|---|---|---|---|---|---|---|
| ATOM | 755 | CG | PRO | A | 331 | 32.935 | 24.584 | 13.526 | 1.00 43.90 |
| ATOM | 756 | C | PRO | A | 331 | 32.070 | 22.646 | 10.442 | 1.00 44.76 |
| ATOM | 757 | O | PRO | A | 331 | 31.997 | 22.979 | 9.253 | 1.00 44.78 |
| ATOM | 758 | N | SER | A | 332 | 32.146 | 21.375 | 10.836 | 1.00 44.48 |
| ATOM | 759 | CA | SER | A | 332 | 32.172 | 20.279 | 9.866 | 1.00 44.97 |
| ATOM | 760 | CB | SER | A | 332 | 32.530 | 18.950 | 10.545 | 1.00 46.14 |
| ATOM | 761 | OG | SER | A | 332 | 33.874 | 18.941 | 10.993 | 1.00 49.22 |
| ATOM | 762 | C | SER | A | 332 | 30.820 | 20.139 | 9.159 | 1.00 44.29 |
| ATOM | 763 | O | SER | A | 332 | 30.759 | 19.806 | 7.969 | 1.00 44.30 |
| ATOM | 764 | N | GLY | A | 333 | 29.747 | 20.402 | 9.904 | 1.00 43.13 |
| ATOM | 765 | CA | GLY | A | 333 | 28.400 | 20.304 | 9.361 | 1.00 42.43 |
| ATOM | 766 | C | GLY | A | 333 | 28.042 | 21.392 | 8.367 | 1.00 41.59 |
| ATOM | 767 | O | GLY | A | 333 | 27.324 | 21.148 | 7.400 | 1.00 40.98 |
| ATOM | 768 | N | ILE | A | 334 | 28.544 | 22.597 | 8.611 | 1.00 41.62 |
| ATOM | 769 | CA | ILE | A | 334 | 28.297 | 23.735 | 7.736 | 1.00 41.42 |
| ATOM | 770 | CB | ILE | A | 334 | 28.935 | 25.020 | 8.334 | 1.00 41.88 |
| ATOM | 771 | CG2 | ILE | A | 334 | 29.077 | 26.101 | 7.271 | 1.00 42.74 |
| ATOM | 772 | CG1 | ILE | A | 334 | 28.110 | 25.525 | 9.524 | 1.00 40.76 |
| ATOM | 773 | CD1 | ILE | A | 334 | 26.703 | 25.974 | 9.158 | 1.00 40.47 |
| ATOM | 774 | C | ILE | A | 334 | 28.889 | 23.461 | 6.352 | 1.00 41.45 |
| ATOM | 775 | O | ILE | A | 334 | 28.302 | 23.829 | 5.328 | 1.00 41.41 |
| ATOM | 776 | N | LYS | A | 335 | 30.026 | 22.766 | 6.344 | 1.00 41.33 |
| ATOM | 777 | CA | LYS | A | 335 | 30.755 | 22.430 | 5.124 | 1.00 40.77 |
| ATOM | 778 | CB | LYS | A | 335 | 32.250 | 22.245 | 5.436 | 1.00 42.29 |
| ATOM | 779 | CG | LYS | A | 335 | 32.926 | 23.414 | 6.155 | 1.00 46.33 |
| ATOM | 780 | CD | LYS | A | 335 | 34.312 | 22.997 | 6.694 | 1.00 50.33 |
| ATOM | 781 | CE | LYS | A | 335 | 34.876 | 23.990 | 7.737 | 1.00 52.40 |
| ATOM | 782 | NZ | LYS | A | 335 | 35.636 | 23.304 | 8.849 | 1.00 52.32 |
| ATOM | 783 | C | LYS | A | 335 | 30.261 | 21.192 | 4.383 | 1.00 39.37 |
| ATOM | 784 | O | LYS | A | 335 | 30.794 | 20.881 | 3.325 | 1.00 39.47 |
| ATOM | 785 | N | LEU | A | 336 | 29.277 | 20.468 | 4.921 | 1.00 38.46 |
| ATOM | 786 | CA | LEU | A | 336 | 28.772 | 19.254 | 4.249 | 1.00 36.39 |
| ATOM | 787 | CB | LEU | A | 336 | 27.713 | 18.534 | 5.098 | 1.00 35.74 |
| ATOM | 788 | CG | LEU | A | 336 | 28.161 | 17.824 | 6.381 | 1.00 34.77 |
| ATOM | 789 | CD1 | LEU | A | 336 | 26.971 | 17.335 | 7.178 | 1.00 33.52 |
| ATOM | 790 | CD2 | LEU | A | 336 | 29.076 | 16.661 | 6.032 | 1.00 34.32 |
| ATOM | 791 | C | LEU | A | 336 | 28.194 | 19.567 | 2.876 | 1.00 35.51 |
| ATOM | 792 | O | LEU | A | 336 | 27.438 | 20.538 | 2.718 | 1.00 35.47 |
| ATOM | 793 | N | THR | A | 337 | 28.581 | 18.757 | 1.887 | 1.00 33.83 |
| ATOM | 794 | CA | THR | A | 337 | 28.123 | 18.907 | 0.509 | 1.00 32.09 |
| ATOM | 795 | CB | THR | A | 337 | 29.000 | 18.107 | -0.498 | 1.00 31.29 |
| ATOM | 796 | OG1 | THR | A | 337 | 28.835 | 16.697 | -0.291 | 1.00 28.12 |
| ATOM | 797 | CG2 | THR | A | 337 | 30.474 | 18.478 | -0.355 | 1.00 31.66 |
| ATOM | 798 | C | THR | A | 337 | 26.684 | 18.428 | 0.339 | 1.00 32.57 |
| ATOM | 799 | O | THR | A | 337 | 26.203 | 17.575 | 1.087 | 1.00 33.01 |
| ATOM | 800 | N | ILE | A | 338 | 26.017 | 18.951 | -0.683 | 1.00 32.04 |
| ATOM | 801 | CA | ILE | A | 338 | 24.637 | 18.578 | -0.969 | 1.00 31.14 |
| ATOM | 802 | CB | ILE | A | 338 | 24.121 | 19.323 | -2.234 | 1.00 30.72 |
| ATOM | 803 | CG2 | ILE | A | 338 | 24.910 | 18.892 | -3.468 | 1.00 30.49 |
| ATOM | 804 | CG1 | ILE | A | 338 | 22.616 | 19.109 | -2.412 | 1.00 30.73 |
| ATOM | 805 | CD1 | ILE | A | 338 | 21.770 | 19.649 | -1.269 | 1.00 31.67 |
| ATOM | 806 | C | ILE | A | 338 | 24.494 | 17.056 | -1.130 | 1.00 29.90 |
| ATOM | 807 | O | ILE | A | 338 | 23.494 | 16.473 | -0.728 | 1.00 29.37 |
| ATOM | 808 | N | ASN | A | 339 | 25.546 | 16.418 | -1.632 | 1.00 30.15 |
| ATOM | 809 | CA | ASN | A | 339 | 25.560 | 14.975 | -1.851 | 1.00 30.36 |
| ATOM | 810 | CB | ASN | A | 339 | 26.827 | 14.564 | -2.584 | 1.00 29.83 |
| ATOM | 811 | CG | ASN | A | 339 | 27.042 | 15.346 | -3.839 | 1.00 31.46 |
| ATOM | 812 | OD1 | ASN | A | 339 | 26.850 | 14.822 | -4.928 | 1.00 33.15 |
| ATOM | 813 | ND2 | ASN | A | 339 | 27.460 | 16.611 | -3.705 | 1.00 31.27 |

Figure 7

| | | | | | | | | |
|---|---|---|---|---|---|---|---|---|
| ATOM | 814 | C | ASN | A | 339 | 25.514 | 14.214 | -0.549 | 1.00 | 30.48 |
| ATOM | 815 | O | ASN | A | 339 | 24.889 | 13.152 | -0.462 | 1.00 | 31.48 |
| ATOM | 816 | N | LYS | A | 340 | 26.245 | 14.734 | 0.434 | 1.00 | 30.52 |
| ATOM | 817 | CA | LYS | A | 340 | 26.316 | 14.122 | 1.752 | 1.00 | 30.59 |
| ATOM | 818 | CB | LYS | A | 340 | 27.489 | 14.702 | 2.549 | 1.00 | 31.34 |
| ATOM | 819 | CG | LYS | A | 340 | 27.565 | 14.190 | 3.970 | 1.00 | 33.30 |
| ATOM | 820 | CD | LYS | A | 340 | 27.595 | 12.653 | 4.048 | 1.00 | 36.15 |
| ATOM | 821 | CE | LYS | A | 340 | 27.535 | 12.166 | 5.510 | 1.00 | 36.58 |
| ATOM | 822 | NZ | LYS | A | 340 | 27.425 | 10.676 | 5.659 | 1.00 | 37.55 |
| ATOM | 823 | C | LYS | A | 340 | 25.005 | 14.333 | 2.484 | 1.00 | 29.48 |
| ATOM | 824 | O | LYS | A | 340 | 24.455 | 13.397 | 3.052 | 1.00 | 30.28 |
| ATOM | 825 | N | LEU | A | 341 | 24.512 | 15.568 | 2.452 | 1.00 | 28.58 |
| ATOM | 826 | CA | LEU | A | 341 | 23.251 | 15.927 | 3.090 | 1.00 | 28.16 |
| ATOM | 827 | CB | LEU | A | 341 | 22.924 | 17.402 | 2.813 | 1.00 | 27.02 |
| ATOM | 828 | CG | LEU | A | 341 | 23.857 | 18.465 | 3.384 | 1.00 | 24.82 |
| ATOM | 829 | CD1 | LEU | A | 341 | 23.330 | 19.843 | 3.033 | 1.00 | 24.24 |
| ATOM | 830 | CD2 | LEU | A | 341 | 23.933 | 18.298 | 4.883 | 1.00 | 25.60 |
| ATOM | 831 | C | LEU | A | 341 | 22.107 | 15.044 | 2.573 | 1.00 | 28.09 |
| ATOM | 832 | O | LEU | A | 341 | 21.227 | 14.639 | 3.329 | 1.00 | 28.27 |
| ATOM | 833 | N | LEU | A | 342 | 22.139 | 14.729 | 1.286 | 1.00 | 29.14 |
| ATOM | 834 | CA | LEU | A | 342 | 21.112 | 13.917 | 0.683 | 1.00 | 30.35 |
| ATOM | 835 | CB | LEU | A | 342 | 21.124 | 14.065 | -0.831 | 1.00 | 33.74 |
| ATOM | 836 | CG | LEU | A | 342 | 20.496 | 15.373 | -1.304 | 1.00 | 36.07 |
| ATOM | 837 | CD1 | LEU | A | 342 | 19.989 | 15.149 | -2.676 | 1.00 | 36.54 |
| ATOM | 838 | CD2 | LEU | A | 342 | 19.325 | 15.773 | -0.410 | 1.00 | 37.94 |
| ATOM | 839 | C | LEU | A | 342 | 21.230 | 12.446 | 1.050 | 1.00 | 30.24 |
| ATOM | 840 | O | LEU | A | 342 | 20.216 | 11.707 | 1.046 | 1.00 | 29.35 |
| ATOM | 841 | N | ASP | A | 343 | 22.462 | 12.017 | 1.321 | 1.00 | 29.66 |
| ATOM | 842 | CA | ASP | A | 343 | 22.700 | 10.638 | 1.712 | 1.00 | 29.33 |
| ATOM | 843 | CB | ASP | A | 343 | 24.195 | 10.324 | 1.644 | 1.00 | 31.90 |
| ATOM | 844 | CG | ASP | A | 343 | 24.505 | 8.868 | 1.928 | 1.00 | 36.82 |
| ATOM | 845 | OD1 | ASP | A | 343 | 23.865 | 7.987 | 1.303 | 1.00 | 39.94 |
| ATOM | 846 | OD2 | ASP | A | 343 | 25.358 | 8.604 | 2.806 | 1.00 | 40.21 |
| ATOM | 847 | C | ASP | A | 343 | 22.166 | 10.479 | 3.137 | 1.00 | 27.30 |
| ATOM | 848 | O | ASP | A | 343 | 21.558 | 9.473 | 3.470 | 1.00 | 27.27 |
| ATOM | 849 | N | MET | A | 344 | 22.329 | 11.518 | 3.943 | 1.00 | 26.93 |
| ATOM | 850 | CA | MET | A | 344 | 21.837 | 11.481 | 5.308 | 1.00 | 26.63 |
| ATOM | 851 | CB | MET | A | 344 | 22.342 | 12.692 | 6.080 | 1.00 | 28.71 |
| ATOM | 852 | CG | MET | A | 344 | 23.863 | 12.783 | 6.177 | 1.00 | 30.38 |
| ATOM | 853 | SD | MET | A | 344 | 24.373 | 14.261 | 7.073 | 1.00 | 33.61 |
| ATOM | 854 | CE | MET | A | 344 | 24.550 | 13.614 | 8.716 | 1.00 | 33.33 |
| ATOM | 855 | C | MET | A | 344 | 20.313 | 11.452 | 5.294 | 1.00 | 26.20 |
| ATOM | 856 | O | MET | A | 344 | 19.710 | 10.706 | 6.076 | 1.00 | 27.13 |
| ATOM | 857 | N | ALA | A | 345 | 19.693 | 12.240 | 4.406 | 1.00 | 24.39 |
| ATOM | 858 | CA | ALA | A | 345 | 18.236 | 12.286 | 4.270 | 1.00 | 23.04 |
| ATOM | 859 | CB | ALA | A | 345 | 17.831 | 13.341 | 3.250 | 1.00 | 20.95 |
| ATOM | 860 | C | ALA | A | 345 | 17.755 | 10.906 | 3.837 | 1.00 | 22.68 |
| ATOM | 861 | O | ALA | A | 345 | 16.775 | 10.390 | 4.361 | 1.00 | 22.97 |
| ATOM | 862 | N | ALA | A | 346 | 18.500 | 10.296 | 2.920 | 1.00 | 23.09 |
| ATOM | 863 | CA | ALA | A | 346 | 18.205 | 8.967 | 2.403 | 1.00 | 22.87 |
| ATOM | 864 | CB | ALA | A | 346 | 19.206 | 8.596 | 1.305 | 1.00 | 23.18 |
| ATOM | 865 | C | ALA | A | 346 | 18.254 | 7.925 | 3.510 | 1.00 | 22.98 |
| ATOM | 866 | O | ALA | A | 346 | 17.465 | 6.972 | 3.504 | 1.00 | 22.86 |
| ATOM | 867 | N | GLN | A | 347 | 19.211 | 8.087 | 4.429 | 1.00 | 23.91 |
| ATOM | 868 | CA | GLN | A | 347 | 19.382 | 7.166 | 5.562 | 1.00 | 23.53 |
| ATOM | 869 | CB | GLN | A | 347 | 20.684 | 7.461 | 6.313 | 1.00 | 24.80 |
| ATOM | 870 | CG | GLN | A | 347 | 21.955 | 7.188 | 5.517 | 1.00 | 27.63 |
| ATOM | 871 | CD | GLN | A | 347 | 23.218 | 7.470 | 6.312 | 1.00 | 28.82 |
| ATOM | 872 | OE1 | GLN | A | 347 | 24.163 | 6.685 | 6.280 | 1.00 | 32.64 |

Figure 7

| ATOM | 873 | NE2 | GLN | A | 347 | 23.241 | 8.591 | 7.027 | 1.00 | 27.39 |
| --- | --- | --- | --- | --- | --- | --- | --- | --- | --- | --- |
| ATOM | 874 | C | GLN | A | 347 | 18.203 | 7.230 | 6.536 | 1.00 | 22.80 |
| ATOM | 875 | O | GLN | A | 347 | 17.736 | 6.196 | 7.034 | 1.00 | 21.93 |
| ATOM | 876 | N | ILE | A | 348 | 17.748 | 8.451 | 6.820 | 1.00 | 23.17 |
| ATOM | 877 | CA | ILE | A | 348 | 16.612 | 8.678 | 7.720 | 1.00 | 22.40 |
| ATOM | 878 | CB | ILE | A | 348 | 16.416 | 10.198 | 8.003 | 1.00 | 21.00 |
| ATOM | 879 | CG2 | ILE | A | 348 | 15.234 | 10.418 | 8.950 | 1.00 | 20.04 |
| ATOM | 880 | CG1 | ILE | A | 348 | 17.706 | 10.788 | 8.589 | 1.00 | 17.89 |
| ATOM | 881 | CD1 | ILE | A | 348 | 17.745 | 12.287 | 8.594 | 1.00 | 17.24 |
| ATOM | 882 | C | ILE | A | 348 | 15.355 | 8.093 | 7.080 | 1.00 | 23.40 |
| ATOM | 883 | O | ILE | A | 348 | 14.568 | 7.423 | 7.749 | 1.00 | 24.52 |
| ATOM | 884 | N | ALA | A | 349 | 15.207 | 8.295 | 5.767 | 1.00 | 23.99 |
| ATOM | 885 | CA | ALA | A | 349 | 14.056 | 7.776 | 5.011 | 1.00 | 24.90 |
| ATOM | 886 | CB | ALA | A | 349 | 14.024 | 8.371 | 3.589 | 1.00 | 24.95 |
| ATOM | 887 | C | ALA | A | 349 | 14.061 | 6.242 | 4.938 | 1.00 | 25.10 |
| ATOM | 888 | O | ALA | A | 349 | 13.005 | 5.619 | 4.794 | 1.00 | 25.96 |
| ATOM | 889 | N | GLU | A | 350 | 15.248 | 5.643 | 4.991 | 1.00 | 24.40 |
| ATOM | 890 | CA | GLU | A | 350 | 15.367 | 4.194 | 4.956 | 1.00 | 24.74 |
| ATOM | 891 | CB | GLU | A | 350 | 16.814 | 3.804 | 4.678 | 1.00 | 26.97 |
| ATOM | 892 | CG | GLU | A | 350 | 17.060 | 2.308 | 4.727 | 1.00 | 30.45 |
| ATOM | 893 | CD | GLU | A | 350 | 18.523 | 1.959 | 4.618 | 1.00 | 33.17 |
| ATOM | 894 | OE1 | GLU | A | 350 | 19.342 | 2.876 | 4.371 | 1.00 | 33.26 |
| ATOM | 895 | OE2 | GLU | A | 350 | 18.849 | 0.763 | 4.778 | 1.00 | 35.21 |
| ATOM | 896 | C | GLU | A | 350 | 14.888 | 3.572 | 6.273 | 1.00 | 23.54 |
| ATOM | 897 | O | GLU | A | 350 | 14.254 | 2.521 | 6.276 | 1.00 | 23.97 |
| ATOM | 898 | N | GLY | A | 351 | 15.194 | 4.237 | 7.384 | 1.00 | 23.49 |
| ATOM | 899 | CA | GLY | A | 351 | 14.778 | 3.760 | 8.689 | 1.00 | 22.34 |
| ATOM | 900 | C | GLY | A | 351 | 13.299 | 4.018 | 8.901 | 1.00 | 22.70 |
| ATOM | 901 | O | GLY | A | 351 | 12.634 | 3.274 | 9.625 | 1.00 | 23.70 |
| ATOM | 902 | N | MET | A | 352 | 12.796 | 5.109 | 8.320 | 1.00 | 21.01 |
| ATOM | 903 | CA | MET | A | 352 | 11.377 | 5.437 | 8.406 | 1.00 | 19.45 |
| ATOM | 904 | CB | MET | A | 352 | 11.121 | 6.868 | 7.949 | 1.00 | 17.11 |
| ATOM | 905 | CG | MET | A | 352 | 11.379 | 7.924 | 9.010 | 1.00 | 14.65 |
| ATOM | 906 | SD | MET | A | 352 | 10.636 | 7.571 | 10.638 | 1.00 | 19.62 |
| ATOM | 907 | CE | MET | A | 352 | 8.879 | 7.287 | 10.261 | 1.00 | 12.07 |
| ATOM | 908 | C | MET | A | 352 | 10.603 | 4.461 | 7.539 | 1.00 | 19.21 |
| ATOM | 909 | O | MET | A | 352 | 9.480 | 4.102 | 7.851 | 1.00 | 19.74 |
| ATOM | 910 | N | ALA | A | 353 | 11.229 | 4.014 | 6.456 | 1.00 | 21.15 |
| ATOM | 911 | CA | ALA | A | 353 | 10.630 | 3.039 | 5.557 | 1.00 | 22.54 |
| ATOM | 912 | CB | ALA | A | 353 | 11.462 | 2.906 | 4.291 | 1.00 | 20.42 |
| ATOM | 913 | C | ALA | A | 353 | 10.496 | 1.676 | 6.266 | 1.00 | 23.90 |
| ATOM | 914 | O | ALA | A | 353 | 9.578 | 0.921 | 5.979 | 1.00 | 24.92 |
| ATOM | 915 | N | PHE | A | 354 | 11.405 | 1.383 | 7.203 | 1.00 | 25.36 |
| ATOM | 916 | CA | PHE | A | 354 | 11.380 | 0.130 | 7.970 | 1.00 | 25.68 |
| ATOM | 917 | CB | PHE | A | 354 | 12.715 | -0.085 | 8.697 | 1.00 | 28.26 |
| ATOM | 918 | CG | PHE | A | 354 | 12.748 | -1.322 | 9.555 | 1.00 | 29.78 |
| ATOM | 919 | CD1 | PHE | A | 354 | 12.597 | -2.587 | 8.988 | 1.00 | 29.08 |
| ATOM | 920 | CD2 | PHE | A | 354 | 12.907 | -1.226 | 10.937 | 1.00 | 30.84 |
| ATOM | 921 | CE1 | PHE | A | 354 | 12.607 | -3.733 | 9.783 | 1.00 | 29.34 |
| ATOM | 922 | CE2 | PHE | A | 354 | 12.915 | -2.378 | 11.740 | 1.00 | 30.13 |
| ATOM | 923 | CZ | PHE | A | 354 | 12.763 | -3.626 | 11.160 | 1.00 | 28.56 |
| ATOM | 924 | C | PHE | A | 354 | 10.240 | 0.207 | 8.975 | 1.00 | 24.98 |
| ATOM | 925 | O | PHE | A | 354 | 9.473 | -0.732 | 9.144 | 1.00 | 25.26 |
| ATOM | 926 | N | ILE | A | 355 | 10.160 | 1.341 | 9.652 | 1.00 | 25.42 |
| ATOM | 927 | CA | ILE | A | 355 | 9.114 | 1.624 | 10.618 | 1.00 | 24.76 |
| ATOM | 928 | CB | ILE | A | 355 | 9.359 | 3.019 | 11.231 | 1.00 | 23.49 |
| ATOM | 929 | CG2 | ILE | A | 355 | 8.069 | 3.587 | 11.832 | 1.00 | 23.64 |
| ATOM | 930 | CG1 | ILE | A | 355 | 10.515 | 2.931 | 12.244 | 1.00 | 21.59 |
| ATOM | 931 | CD1 | ILE | A | 355 | 11.003 | 4.271 | 12.734 | 1.00 | 19.63 |

Figure 7

| | | | | | | | | | |
|---|---|---|---|---|---|---|---|---|---|
| ATOM | 932 | C | ILE | A | 355 | 7.751 | 1.542 | 9.919 | 1.00 25.65 |
| ATOM | 933 | O | ILE | A | 355 | 6.802 | 0.957 | 10.452 | 1.00 24.38 |
| ATOM | 934 | N | GLU | A | 356 | 7.702 | 2.093 | 8.698 | 1.00 26.70 |
| ATOM | 935 | CA | GLU | A | 356 | 6.521 | 2.105 | 7.827 | 1.00 27.36 |
| ATOM | 936 | CB | GLU | A | 356 | 6.825 | 2.909 | 6.565 | 1.00 25.87 |
| ATOM | 937 | CG | GLU | A | 356 | 5.740 | 2.877 | 5.513 | 1.00 25.33 |
| ATOM | 938 | CD | GLU | A | 356 | 6.072 | 3.750 | 4.325 | 1.00 24.99 |
| ATOM | 939 | OE1 | GLU | A | 356 | 6.708 | 3.257 | 3.365 | 1.00 24.63 |
| ATOM | 940 | OE2 | GLU | A | 356 | 5.707 | 4.940 | 4.357 | 1.00 25.73 |
| ATOM | 941 | C | GLU | A | 356 | 6.143 | 0.665 | 7.462 | 1.00 28.52 |
| ATOM | 942 | O | GLU | A | 356 | 5.000 | 0.256 | 7.630 | 1.00 28.60 |
| ATOM | 943 | N | GLU | A | 357 | 7.135 | -0.092 | 7.001 | 1.00 30.06 |
| ATOM | 944 | CA | GLU | A | 357 | 7.018 | -1.505 | 6.637 | 1.00 32.11 |
| ATOM | 945 | CB | GLU | A | 357 | 8.441 | -2.043 | 6.384 | 1.00 37.76 |
| ATOM | 946 | CG | GLU | A | 357 | 8.625 | -3.570 | 6.328 | 1.00 43.01 |
| ATOM | 947 | CD | GLU | A | 357 | 8.139 | -4.175 | 5.027 | 1.00 47.59 |
| ATOM | 948 | OE1 | GLU | A | 357 | 8.270 | -3.507 | 3.977 | 1.00 50.98 |
| ATOM | 949 | OE2 | GLU | A | 357 | 7.624 | -5.319 | 5.047 | 1.00 50.37 |
| ATOM | 950 | C | GLU | A | 357 | 6.384 | -2.320 | 7.761 | 1.00 31.57 |
| ATOM | 951 | O | GLU | A | 357 | 5.524 | -3.163 | 7.535 | 1.00 30.62 |
| ATOM | 952 | N | ARG | A | 358 | 6.833 | -2.059 | 8.981 | 1.00 32.07 |
| ATOM | 953 | CA | ARG | A | 358 | 6.364 | -2.777 | 10.156 | 1.00 33.00 |
| ATOM | 954 | CB | ARG | A | 358 | 7.483 | -2.828 | 11.209 | 1.00 33.78 |
| ATOM | 955 | CG | ARG | A | 358 | 8.821 | -3.402 | 10.695 | 1.00 35.92 |
| ATOM | 956 | CD | ARG | A | 358 | 8.739 | -4.891 | 10.315 | 1.00 39.63 |
| ATOM | 957 | NE | ARG | A | 358 | 8.357 | -5.691 | 11.472 | 1.00 45.18 |
| ATOM | 958 | CZ | ARG | A | 358 | 9.170 | -5.990 | 12.486 | 1.00 48.16 |
| ATOM | 959 | NH1 | ARG | A | 358 | 10.437 | -5.590 | 12.476 | 1.00 49.31 |
| ATOM | 960 | NH2 | ARG | A | 358 | 8.670 | -6.528 | 13.597 | 1.00 49.00 |
| ATOM | 961 | C | ARG | A | 358 | 5.085 | -2.205 | 10.749 | 1.00 33.51 |
| ATOM | 962 | O | ARG | A | 358 | 4.688 | -2.574 | 11.848 | 1.00 34.43 |
| ATOM | 963 | N | ASN | A | 359 | 4.464 | -1.273 | 10.031 | 1.00 34.35 |
| ATOM | 964 | CA | ASN | A | 359 | 3.206 | -0.647 | 10.445 | 1.00 34.09 |
| ATOM | 965 | CB | ASN | A | 359 | 2.062 | -1.657 | 10.355 | 1.00 36.01 |
| ATOM | 966 | CG | ASN | A | 359 | 1.936 | -2.261 | 8.967 | 1.00 37.24 |
| ATOM | 967 | OD1 | ASN | A | 359 | 1.790 | -1.537 | 7.968 | 1.00 38.43 |
| ATOM | 968 | ND2 | ASN | A | 359 | 2.028 | -3.594 | 8.891 | 1.00 36.54 |
| ATOM | 969 | C | ASN | A | 359 | 3.171 | 0.100 | 11.778 | 1.00 33.23 |
| ATOM | 970 | O | ASN | A | 359 | 2.219 | 0.000 | 12.552 | 1.00 31.79 |
| ATOM | 971 | N | TYR | A | 360 | 4.221 | 0.880 | 12.018 | 1.00 33.62 |
| ATOM | 972 | CA | TYR | A | 360 | 4.333 | 1.713 | 13.212 | 1.00 33.29 |
| ATOM | 973 | CB | TYR | A | 360 | 5.558 | 1.336 | 14.043 | 1.00 34.02 |
| ATOM | 974 | CG | TYR | A | 360 | 5.382 | 0.066 | 14.804 | 1.00 35.88 |
| ATOM | 975 | CD1 | TYR | A | 360 | 5.965 | -1.116 | 14.363 | 1.00 37.17 |
| ATOM | 976 | CE1 | TYR | A | 360 | 5.785 | -2.311 | 15.056 | 1.00 38.79 |
| ATOM | 977 | CD2 | TYR | A | 360 | 4.615 | 0.036 | 15.960 | 1.00 37.74 |
| ATOM | 978 | CE2 | TYR | A | 360 | 4.428 | -1.155 | 16.670 | 1.00 39.72 |
| ATOM | 979 | CZ | TYR | A | 360 | 5.019 | -2.322 | 16.211 | 1.00 39.50 |
| ATOM | 980 | OH | TYR | A | 360 | 4.850 | -3.491 | 16.911 | 1.00 41.10 |
| ATOM | 981 | C | TYR | A | 360 | 4.513 | 3.135 | 12.721 | 1.00 31.85 |
| ATOM | 982 | O | TYR | A | 360 | 4.557 | 3.382 | 11.514 | 1.00 31.99 |
| ATOM | 983 | N | ILE | A | 361 | 4.585 | 4.071 | 13.653 | 1.00 30.59 |
| ATOM | 984 | CA | ILE | A | 361 | 4.806 | 5.457 | 13.292 | 1.00 29.32 |
| ATOM | 985 | CB | ILE | A | 361 | 3.532 | 6.313 | 13.466 | 1.00 28.14 |
| ATOM | 986 | CG2 | ILE | A | 361 | 2.355 | 5.651 | 12.767 | 1.00 28.12 |
| ATOM | 987 | CG1 | ILE | A | 361 | 3.194 | 6.513 | 14.934 | 1.00 27.88 |
| ATOM | 988 | CD1 | ILE | A | 361 | 2.212 | 7.661 | 15.162 | 1.00 27.12 |
| ATOM | 989 | C | ILE | A | 361 | 5.924 | 5.933 | 14.202 | 1.00 28.99 |
| ATOM | 990 | O | ILE | A | 361 | 6.342 | 5.206 | 15.088 | 1.00 29.75 |

Figure 7

| | | | | | | | | |
|---|---|---|---|---|---|---|---|---|
| ATOM | 991 | N | HIS | A | 362 | 6.455 | 7.119 | 13.943 | 1.00 27.95 |
| ATOM | 992 | CA | HIS | A | 362 | 7.510 | 7.695 | 14.758 | 1.00 25.71 |
| ATOM | 993 | CB | HIS | A | 362 | 8.531 | 8.414 | 13.857 | 1.00 24.65 |
| ATOM | 994 | CG | HIS | A | 362 | 9.739 | 8.930 | 14.585 | 1.00 22.71 |
| ATOM | 995 | CD2 | HIS | A | 362 | 11.059 | 8.738 | 14.356 | 1.00 21.49 |
| ATOM | 996 | ND1 | HIS | A | 362 | 9.660 | 9.731 | 15.704 | 1.00 22.12 |
| ATOM | 997 | CE1 | HIS | A | 362 | 10.878 | 10.009 | 16.134 | 1.00 22.53 |
| ATOM | 998 | NE2 | HIS | A | 362 | 11.745 | 9.419 | 15.333 | 1.00 21.78 |
| ATOM | 999 | C | HIS | A | 362 | 6.875 | 8.702 | 15.718 | 1.00 25.82 |
| ATOM | 1000 | O | HIS | A | 362 | 7.051 | 8.611 | 16.933 | 1.00 26.36 |
| ATOM | 1001 | N | ARG | A | 363 | 6.104 | 9.614 | 15.123 | 1.00 25.63 |
| ATOM | 1002 | CA | ARG | A | 363 | 5.393 | 10.742 | 15.727 | 1.00 26.53 |
| ATOM | 1003 | CB | ARG | A | 363 | 4.205 | 10.348 | 16.624 | 1.00 31.97 |
| ATOM | 1004 | CG | ARG | A | 363 | 4.492 | 9.672 | 17.930 | 1.00 36.30 |
| ATOM | 1005 | CD | ARG | A | 363 | 3.183 | 9.229 | 18.542 | 1.00 38.11 |
| ATOM | 1006 | NE | ARG | A | 363 | 2.433 | 10.351 | 19.091 | 1.00 41.24 |
| ATOM | 1007 | CZ | ARG | A | 363 | 1.101 | 10.411 | 19.099 | 1.00 44.85 |
| ATOM | 1008 | NH1 | ARG | A | 363 | 0.399 | 9.405 | 18.573 | 1.00 44.64 |
| ATOM | 1009 | NH2 | ARG | A | 363 | 0.468 | 11.430 | 19.694 | 1.00 43.90 |
| ATOM | 1010 | C | ARG | A | 363 | 6.174 | 11.909 | 16.296 | 1.00 25.07 |
| ATOM | 1011 | O | ARG | A | 363 | 5.584 | 12.924 | 16.652 | 1.00 24.36 |
| ATOM | 1012 | N | ASP | A | 364 | 7.500 | 11.800 | 16.309 | 1.00 24.51 |
| ATOM | 1013 | CA | ASP | A | 364 | 8.352 | 12.887 | 16.792 | 1.00 24.20 |
| ATOM | 1014 | CB | ASP | A | 364 | 8.852 | 12.636 | 18.225 | 1.00 23.99 |
| ATOM | 1015 | CG | ASP | A | 364 | 7.798 | 12.962 | 19.273 | 1.00 23.93 |
| ATOM | 1016 | OD1 | ASP | A | 364 | 7.527 | 14.167 | 19.488 | 1.00 23.36 |
| ATOM | 1017 | OD2 | ASP | A | 364 | 7.219 | 12.014 | 19.855 | 1.00 24.50 |
| ATOM | 1018 | C | ASP | A | 364 | 9.519 | 13.073 | 15.844 | 1.00 23.77 |
| ATOM | 1019 | O | ASP | A | 364 | 10.617 | 13.415 | 16.267 | 1.00 24.09 |
| ATOM | 1020 | N | LEU | A | 365 | 9.261 | 12.860 | 14.555 | 1.00 22.07 |
| ATOM | 1021 | CA | LEU | A | 365 | 10.282 | 12.991 | 13.537 | 1.00 20.94 |
| ATOM | 1022 | CB | LEU | A | 365 | 9.840 | 12.264 | 12.280 | 1.00 18.49 |
| ATOM | 1023 | CG | LEU | A | 365 | 10.824 | 12.191 | 11.128 | 1.00 17.40 |
| ATOM | 1024 | CD1 | LEU | A | 365 | 12.076 | 11.436 | 11.567 | 1.00 18.42 |
| ATOM | 1025 | CD2 | LEU | A | 365 | 10.160 | 11.504 | 9.954 | 1.00 16.73 |
| ATOM | 1026 | C | LEU | A | 365 | 10.718 | 14.430 | 13.208 | 1.00 22.81 |
| ATOM | 1027 | O | LEU | A | 365 | 9.972 | 15.229 | 12.643 | 1.00 23.33 |
| ATOM | 1028 | N | ARG | A | 366 | 11.949 | 14.742 | 13.599 | 1.00 24.28 |
| ATOM | 1029 | CA | ARG | A | 366 | 12.576 | 16.037 | 13.362 | 1.00 23.29 |
| ATOM | 1030 | CB | ARG | A | 366 | 12.023 | 17.126 | 14.291 | 1.00 23.28 |
| ATOM | 1031 | CG | ARG | A | 366 | 11.896 | 16.764 | 15.724 | 1.00 23.71 |
| ATOM | 1032 | CD | ARG | A | 366 | 11.153 | 17.863 | 16.471 | 1.00 23.71 |
| ATOM | 1033 | NE | ARG | A | 366 | 11.122 | 17.588 | 17.906 | 1.00 25.54 |
| ATOM | 1034 | CZ | ARG | A | 366 | 10.221 | 16.819 | 18.517 | 1.00 25.68 |
| ATOM | 1035 | NH1 | ARG | A | 366 | 9.239 | 16.240 | 17.828 | 1.00 26.45 |
| ATOM | 1036 | NH2 | ARG | A | 366 | 10.332 | 16.593 | 19.815 | 1.00 26.42 |
| ATOM | 1037 | C | ARG | A | 366 | 14.073 | 15.838 | 13.532 | 1.00 21.99 |
| ATOM | 1038 | O | ARG | A | 366 | 14.485 | 14.803 | 14.040 | 1.00 20.80 |
| ATOM | 1039 | N | ALA | A | 367 | 14.875 | 16.789 | 13.042 | 1.00 21.52 |
| ATOM | 1040 | CA | ALA | A | 367 | 16.341 | 16.712 | 13.103 | 1.00 21.10 |
| ATOM | 1041 | CB | ALA | A | 367 | 16.962 | 17.928 | 12.451 | 1.00 17.94 |
| ATOM | 1042 | C | ALA | A | 367 | 16.885 | 16.535 | 14.522 | 1.00 21.95 |
| ATOM | 1043 | O | ALA | A | 367 | 17.930 | 15.907 | 14.708 | 1.00 22.26 |
| ATOM | 1044 | N | ALA | A | 368 | 16.179 | 17.080 | 15.514 | 1.00 22.20 |
| ATOM | 1045 | CA | ALA | A | 368 | 16.590 | 16.947 | 16.909 | 1.00 22.28 |
| ATOM | 1046 | CB | ALA | A | 368 | 15.679 | 17.761 | 17.820 | 1.00 19.92 |
| ATOM | 1047 | C | ALA | A | 368 | 16.599 | 15.484 | 17.345 | 1.00 24.31 |
| ATOM | 1048 | O | ALA | A | 368 | 17.380 | 15.098 | 18.218 | 1.00 25.08 |
| ATOM | 1049 | N | ASN | A | 369 | 15.746 | 14.666 | 16.723 | 1.00 24.21 |

Figure 7

```
ATOM   1050  CA   ASN A 369      15.654  13.246  17.070  1.00 23.36
ATOM   1051  CB   ASN A 369      14.191  12.835  17.299  1.00 26.18
ATOM   1052  CG   ASN A 369      13.537  13.629  18.427  1.00 28.36
ATOM   1053  OD1  ASN A 369      14.079  13.715  19.539  1.00 29.65
ATOM   1054  ND2  ASN A 369      12.395  14.247  18.137  1.00 28.73
ATOM   1055  C    ASN A 369      16.368  12.290  16.129  1.00 21.74
ATOM   1056  O    ASN A 369      16.035  11.102  16.047  1.00 19.15
ATOM   1057  N    ILE A 370      17.303  12.843  15.361  1.00 21.65
ATOM   1058  CA   ILE A 370      18.136  12.045  14.475  1.00 21.51
ATOM   1059  CB   ILE A 370      18.139  12.548  13.021  1.00 20.80
ATOM   1060  CG2  ILE A 370      19.044  11.638  12.170  1.00 21.02
ATOM   1061  CG1  ILE A 370      16.712  12.609  12.463  1.00 17.96
ATOM   1062  CD1  ILE A 370      16.020  11.275  12.354  1.00 15.59
ATOM   1063  C    ILE A 370      19.536  12.207  15.058  1.00 22.27
ATOM   1064  O    ILE A 370      19.921  13.302  15.464  1.00 21.15
ATOM   1065  N    LEU A 371      20.260  11.101  15.194  1.00 24.95
ATOM   1066  CA   LEU A 371      21.610  11.124  15.760  1.00 26.20
ATOM   1067  CB   LEU A 371      21.722  10.140  16.930  1.00 24.75
ATOM   1068  CG   LEU A 371      20.725  10.365  18.056  1.00 23.72
ATOM   1069  CD1  LEU A 371      20.865   9.287  19.101  1.00 22.69
ATOM   1070  CD2  LEU A 371      20.943  11.734  18.659  1.00 24.75
ATOM   1071  C    LEU A 371      22.665  10.810  14.717  1.00 27.56
ATOM   1072  O    LEU A 371      22.426  10.048  13.775  1.00 27.94
ATOM   1073  N    VAL A 372      23.838  11.409  14.899  1.00 28.16
ATOM   1074  CA   VAL A 372      24.951  11.218  13.979  1.00 28.88
ATOM   1075  CB   VAL A 372      25.493  12.593  13.492  1.00 28.42
ATOM   1076  CG1  VAL A 372      26.366  12.415  12.270  1.00 26.78
ATOM   1077  CG2  VAL A 372      24.341  13.555  13.205  1.00 27.63
ATOM   1078  C    VAL A 372      26.086  10.412  14.638  1.00 29.88
ATOM   1079  O    VAL A 372      26.439  10.643  15.794  1.00 29.75
ATOM   1080  N    SER A 373      26.614   9.426  13.919  1.00 31.80
ATOM   1081  CA   SER A 373      27.714   8.608  14.428  1.00 32.49
ATOM   1082  CB   SER A 373      27.633   7.186  13.877  1.00 30.79
ATOM   1083  OG   SER A 373      27.980   7.155  12.511  1.00 30.31
ATOM   1084  C    SER A 373      29.048   9.232  14.020  1.00 33.98
ATOM   1085  O    SER A 373      29.082  10.278  13.371  1.00 33.73
ATOM   1086  N    ASP A 374      30.141   8.582  14.415  1.00 36.20
ATOM   1087  CA   ASP A 374      31.500   9.040  14.095  1.00 37.68
ATOM   1088  CB   ASP A 374      32.548   8.245  14.901  1.00 40.07
ATOM   1089  CG   ASP A 374      32.363   6.724  14.802  1.00 42.83
ATOM   1090  OD1  ASP A 374      31.233   6.223  14.989  1.00 45.63
ATOM   1091  OD2  ASP A 374      33.363   6.014  14.565  1.00 44.21
ATOM   1092  C    ASP A 374      31.793   8.979  12.593  1.00 37.44
ATOM   1093  O    ASP A 374      32.571   9.780  12.063  1.00 37.69
ATOM   1094  N    THR A 375      31.120   8.059  11.906  1.00 37.28
ATOM   1095  CA   THR A 375      31.281   7.891  10.466  1.00 36.99
ATOM   1096  CB   THR A 375      31.092   6.411  10.051  1.00 37.45
ATOM   1097  OG1  THR A 375      29.758   5.991  10.360  1.00 39.62
ATOM   1098  CG2  THR A 375      32.083   5.512  10.797  1.00 36.42
ATOM   1099  C    THR A 375      30.306   8.790   9.690  1.00 36.14
ATOM   1100  O    THR A 375      30.203   8.701   8.463  1.00 35.72
ATOM   1101  N    LEU A 376      29.614   9.662  10.424  1.00 36.01
ATOM   1102  CA   LEU A 376      28.642  10.613   9.877  1.00 36.03
ATOM   1103  CB   LEU A 376      29.296  11.571   8.871  1.00 36.62
ATOM   1104  CG   LEU A 376      30.492  12.424   9.311  1.00 36.31
ATOM   1105  CD1  LEU A 376      30.711  13.510   8.278  1.00 36.84
ATOM   1106  CD2  LEU A 376      30.251  13.042  10.683  1.00 34.61
ATOM   1107  C    LEU A 376      27.372  10.013   9.280  1.00 35.83
ATOM   1108  O    LEU A 376      26.722  10.647   8.446  1.00 34.72
```

Figure 7

| | | | | | | | | | |
|---|---|---|---|---|---|---|---|---|---|
| ATOM | 1109 | N | SER | A | 377 | 27.045 | 8.780 | 9.672 | 1.00 36.51 |
| ATOM | 1110 | CA | SER | A | 377 | 25.817 | 8.121 | 9.205 | 1.00 36.48 |
| ATOM | 1111 | CB | SER | A | 377 | 26.020 | 6.607 | 9.042 | 1.00 36.99 |
| ATOM | 1112 | OG | SER | A | 377 | 26.097 | 5.958 | 10.301 | 1.00 40.41 |
| ATOM | 1113 | C | SER | A | 377 | 24.702 | 8.432 | 10.227 | 1.00 35.41 |
| ATOM | 1114 | O | SER | A | 377 | 24.976 | 8.635 | 11.420 | 1.00 35.53 |
| ATOM | 1115 | N | CYS | A | 378 | 23.453 | 8.463 | 9.768 | 1.00 33.71 |
| ATOM | 1116 | CA | CYS | A | 378 | 22.333 | 8.801 | 10.644 | 1.00 31.18 |
| ATOM | 1117 | CB | CYS | A | 378 | 21.366 | 9.763 | 9.929 | 1.00 31.64 |
| ATOM | 1118 | SG | CYS | A | 378 | 22.057 | 11.404 | 9.506 | 1.00 30.20 |
| ATOM | 1119 | C | CYS | A | 378 | 21.558 | 7.618 | 11.203 | 1.00 28.86 |
| ATOM | 1120 | O | CYS | A | 378 | 21.465 | 6.557 | 10.584 | 1.00 27.30 |
| ATOM | 1121 | N | LYS | A | 379 | 21.050 | 7.819 | 12.414 | 1.00 27.71 |
| ATOM | 1122 | CA | LYS | A | 379 | 20.249 | 6.832 | 13.111 | 1.00 26.13 |
| ATOM | 1123 | CB | LYS | A | 379 | 21.109 | 6.044 | 14.111 | 1.00 26.73 |
| ATOM | 1124 | CG | LYS | A | 379 | 21.915 | 4.881 | 13.503 | 1.00 26.85 |
| ATOM | 1125 | CD | LYS | A | 379 | 22.987 | 4.357 | 14.461 | 1.00 28.24 |
| ATOM | 1126 | CE | LYS | A | 379 | 23.527 | 2.970 | 14.096 | 1.00 28.92 |
| ATOM | 1127 | NZ | LYS | A | 379 | 22.633 | 1.842 | 14.558 | 1.00 33.13 |
| ATOM | 1128 | C | LYS | A | 379 | 19.093 | 7.565 | 13.802 | 1.00 25.15 |
| ATOM | 1129 | O | LYS | A | 379 | 19.271 | 8.627 | 14.400 | 1.00 23.50 |
| ATOM | 1130 | N | ILE | A | 380 | 17.890 | 7.034 | 13.626 | 1.00 25.58 |
| ATOM | 1131 | CA | ILE | A | 380 | 16.660 | 7.582 | 14.194 | 1.00 24.26 |
| ATOM | 1132 | CB | ILE | A | 380 | 15.429 | 6.988 | 13.453 | 1.00 23.48 |
| ATOM | 1133 | CG2 | ILE | A | 380 | 14.151 | 7.541 | 14.001 | 1.00 22.67 |
| ATOM | 1134 | CG1 | ILE | A | 380 | 15.522 | 7.257 | 11.955 | 1.00 24.20 |
| ATOM | 1135 | CD1 | ILE | A | 380 | 14.386 | 6.653 | 11.185 | 1.00 23.85 |
| ATOM | 1136 | C | ILE | A | 380 | 16.529 | 7.241 | 15.689 | 1.00 24.14 |
| ATOM | 1137 | O | ILE | A | 380 | 16.683 | 6.090 | 16.091 | 1.00 23.25 |
| ATOM | 1138 | N | ALA | A | 381 | 16.196 | 8.240 | 16.497 | 1.00 24.51 |
| ATOM | 1139 | CA | ALA | A | 381 | 16.009 | 8.058 | 17.931 | 1.00 25.70 |
| ATOM | 1140 | CB | ALA | A | 381 | 17.050 | 8.866 | 18.691 | 1.00 25.61 |
| ATOM | 1141 | C | ALA | A | 381 | 14.593 | 8.502 | 18.337 | 1.00 26.91 |
| ATOM | 1142 | O | ALA | A | 381 | 13.827 | 9.018 | 17.503 | 1.00 26.52 |
| ATOM | 1143 | N | ASP | A | 382 | 14.260 | 8.295 | 19.612 | 1.00 27.78 |
| ATOM | 1144 | CA | ASP | A | 382 | 12.962 | 8.668 | 20.187 | 1.00 29.15 |
| ATOM | 1145 | CB | ASP | A | 382 | 12.946 | 10.167 | 20.535 | 1.00 30.72 |
| ATOM | 1146 | CG | ASP | A | 382 | 13.832 | 10.516 | 21.724 | 1.00 32.90 |
| ATOM | 1147 | OD1 | ASP | A | 382 | 13.844 | 9.774 | 22.727 | 1.00 35.39 |
| ATOM | 1148 | OD2 | ASP | A | 382 | 14.502 | 11.562 | 21.674 | 1.00 36.36 |
| ATOM | 1149 | C | ASP | A | 382 | 11.743 | 8.346 | 19.321 | 1.00 30.21 |
| ATOM | 1150 | O | ASP | A | 382 | 10.851 | 9.183 | 19.184 | 1.00 29.63 |
| ATOM | 1151 | N | PHE | A | 383 | 11.697 | 7.140 | 18.753 | 1.00 31.12 |
| ATOM | 1152 | CA | PHE | A | 383 | 10.581 | 6.735 | 17.890 | 1.00 32.37 |
| ATOM | 1153 | CB | PHE | A | 383 | 11.077 | 6.052 | 16.594 | 1.00 31.76 |
| ATOM | 1154 | CG | PHE | A | 383 | 12.033 | 4.907 | 16.826 | 1.00 32.46 |
| ATOM | 1155 | CD1 | PHE | A | 383 | 11.559 | 3.601 | 16.992 | 1.00 33.08 |
| ATOM | 1156 | CD2 | PHE | A | 383 | 13.408 | 5.141 | 16.922 | 1.00 30.33 |
| ATOM | 1157 | CE1 | PHE | A | 383 | 12.444 | 2.549 | 17.253 | 1.00 31.58 |
| ATOM | 1158 | CE2 | PHE | A | 383 | 14.296 | 4.107 | 17.179 | 1.00 30.00 |
| ATOM | 1159 | CZ | PHE | A | 383 | 13.813 | 2.803 | 17.349 | 1.00 32.40 |
| ATOM | 1160 | C | PHE | A | 383 | 9.534 | 5.854 | 18.549 | 1.00 33.32 |
| ATOM | 1161 | O | PHE | A | 383 | 9.829 | 5.035 | 19.425 | 1.00 32.66 |
| ATOM | 1162 | N | GLY | A | 384 | 8.297 | 6.052 | 18.123 | 1.00 34.21 |
| ATOM | 1163 | CA | GLY | A | 384 | 7.210 | 5.254 | 18.638 | 1.00 35.07 |
| ATOM | 1164 | C | GLY | A | 384 | 6.648 | 5.673 | 19.968 | 1.00 35.26 |
| ATOM | 1165 | O | GLY | A | 384 | 5.871 | 4.914 | 20.537 | 1.00 36.35 |
| ATOM | 1166 | N | LEU | A | 385 | 7.023 | 6.846 | 20.478 | 1.00 35.95 |
| ATOM | 1167 | CA | LEU | A | 385 | 6.488 | 7.304 | 21.763 | 1.00 36.11 |

Figure 7

| | | | | | | | | | |
|---|---|---|---|---|---|---|---|---|---|
| ATOM | 1168 | CB | LEU | A | 385 | 7.159 | 8.587 | 22.262 | 1.00 36.32 |
| ATOM | 1169 | CG | LEU | A | 385 | 8.659 | 8.596 | 22.553 | 1.00 37.61 |
| ATOM | 1170 | CD1 | LEU | A | 385 | 8.889 | 9.440 | 23.780 | 1.00 36.80 |
| ATOM | 1171 | CD2 | LEU | A | 385 | 9.199 | 7.194 | 22.774 | 1.00 38.83 |
| ATOM | 1172 | C | LEU | A | 385 | 5.002 | 7.541 | 21.583 | 1.00 36.26 |
| ATOM | 1173 | O | LEU | A | 385 | 4.542 | 7.754 | 20.459 | 1.00 36.07 |
| ATOM | 1174 | N | ALA | A | 386 | 4.250 | 7.502 | 22.679 | 1.00 36.01 |
| ATOM | 1175 | CA | ALA | A | 386 | 2.809 | 7.662 | 22.630 | 1.00 36.23 |
| ATOM | 1176 | CB | ALA | A | 386 | 2.175 | 7.016 | 23.858 | 1.00 37.64 |
| ATOM | 1177 | C | ALA | A | 386 | 2.342 | 9.110 | 22.492 | 1.00 36.19 |
| ATOM | 1178 | O | ALA | A | 386 | 1.278 | 9.366 | 21.949 | 1.00 36.70 |
| ATOM | 1179 | N | ARG | A | 387 | 3.111 | 10.046 | 23.031 | 1.00 35.92 |
| ATOM | 1180 | CA | ARG | A | 387 | 2.753 | 11.458 | 22.952 | 1.00 34.54 |
| ATOM | 1181 | CB | ARG | A | 387 | 2.696 | 12.071 | 24.360 | 1.00 33.66 |
| ATOM | 1182 | CG | ARG | A | 387 | 3.998 | 11.949 | 25.104 | 1.00 33.25 |
| ATOM | 1183 | CD | ARG | A | 387 | 3.933 | 12.432 | 26.519 | 1.00 34.17 |
| ATOM | 1184 | NE | ARG | A | 387 | 5.228 | 12.236 | 27.151 | 1.00 37.78 |
| ATOM | 1185 | CZ | ARG | A | 387 | 6.131 | 13.197 | 27.301 | 1.00 38.54 |
| ATOM | 1186 | NH1 | ARG | A | 387 | 5.879 | 14.431 | 26.871 | 1.00 38.23 |
| ATOM | 1187 | NH2 | ARG | A | 387 | 7.293 | 12.906 | 27.871 | 1.00 38.68 |
| ATOM | 1188 | C | ARG | A | 387 | 3.778 | 12.213 | 22.118 | 1.00 34.35 |
| ATOM | 1189 | O | ARG | A | 387 | 4.707 | 11.639 | 21.540 | 1.00 33.06 |
| ATOM | 1190 | N | LEU | A | 388 | 3.579 | 13.517 | 22.047 | 1.00 35.01 |
| ATOM | 1191 | CA | LEU | A | 388 | 4.498 | 14.370 | 21.324 | 1.00 35.82 |
| ATOM | 1192 | CB | LEU | A | 388 | 3.757 | 15.500 | 20.636 | 1.00 38.53 |
| ATOM | 1193 | CG | LEU | A | 388 | 2.700 | 15.040 | 19.638 | 1.00 40.49 |
| ATOM | 1194 | CD1 | LEU | A | 388 | 1.259 | 15.032 | 20.294 | 1.00 41.30 |
| ATOM | 1195 | CD2 | LEU | A | 388 | 2.797 | 15.989 | 18.448 | 1.00 38.82 |
| ATOM | 1196 | C | LEU | A | 388 | 5.386 | 14.917 | 22.428 | 1.00 34.90 |
| ATOM | 1197 | O | LEU | A | 388 | 4.890 | 15.379 | 23.463 | 1.00 35.61 |
| ATOM | 1198 | N | ILE | A | 389 | 6.690 | 14.754 | 22.253 | 1.00 33.35 |
| ATOM | 1199 | CA | ILE | A | 389 | 7.652 | 15.201 | 23.247 | 1.00 30.40 |
| ATOM | 1200 | CB | ILE | A | 389 | 8.715 | 14.107 | 23.510 | 1.00 26.91 |
| ATOM | 1201 | CG2 | ILE | A | 389 | 8.028 | 12.782 | 23.798 | 1.00 23.23 |
| ATOM | 1202 | CG1 | ILE | A | 389 | 9.642 | 13.955 | 22.303 | 1.00 25.51 |
| ATOM | 1203 | CD1 | ILE | A | 389 | 10.505 | 12.719 | 22.353 | 1.00 23.38 |
| ATOM | 1204 | C | ILE | A | 389 | 8.334 | 16.493 | 22.830 | 1.00 32.06 |
| ATOM | 1205 | O | ILE | A | 389 | 8.390 | 16.837 | 21.651 | 1.00 31.41 |
| ATOM | 1206 | N | GLU | A | 390 | 8.801 | 17.236 | 23.822 | 1.00 34.18 |
| ATOM | 1207 | CA | GLU | A | 390 | 9.507 | 18.486 | 23.598 | 1.00 35.55 |
| ATOM | 1208 | CB | GLU | A | 390 | 9.037 | 19.537 | 24.585 | 1.00 36.67 |
| ATOM | 1209 | CG | GLU | A | 390 | 7.583 | 19.888 | 24.418 | 1.00 39.69 |
| ATOM | 1210 | CD | GLU | A | 390 | 7.088 | 20.808 | 25.494 | 1.00 42.17 |
| ATOM | 1211 | OE1 | GLU | A | 390 | 5.981 | 20.577 | 26.004 | 1.00 46.38 |
| ATOM | 1212 | OE2 | GLU | A | 390 | 7.797 | 21.767 | 25.837 | 1.00 45.07 |
| ATOM | 1213 | C | GLU | A | 390 | 10.989 | 18.216 | 23.769 | 1.00 36.01 |
| ATOM | 1214 | O | GLU | A | 390 | 11.381 | 17.311 | 24.503 | 1.00 35.02 |
| ATOM | 1215 | N | ASP | A | 391 | 11.809 | 19.000 | 23.081 | 1.00 38.18 |
| ATOM | 1216 | CA | ASP | A | 391 | 13.261 | 18.827 | 23.119 | 1.00 39.77 |
| ATOM | 1217 | CB | ASP | A | 391 | 13.899 | 19.648 | 21.997 | 1.00 40.60 |
| ATOM | 1218 | CG | ASP | A | 391 | 13.294 | 19.325 | 20.635 | 1.00 41.85 |
| ATOM | 1219 | OD1 | ASP | A | 391 | 12.946 | 18.143 | 20.392 | 1.00 42.36 |
| ATOM | 1220 | OD2 | ASP | A | 391 | 13.145 | 20.252 | 19.817 | 1.00 41.93 |
| ATOM | 1221 | C | ASP | A | 391 | 13.916 | 19.127 | 24.462 | 1.00 39.72 |
| ATOM | 1222 | O | ASP | A | 391 | 14.970 | 18.569 | 24.782 | 1.00 39.95 |
| ATOM | 1223 | N | ASN | A | 392 | 13.239 | 19.935 | 25.275 | 1.00 39.59 |
| ATOM | 1224 | CA | ASN | A | 392 | 13.757 | 20.325 | 26.580 | 1.00 40.22 |
| ATOM | 1225 | CB | ASN | A | 392 | 13.220 | 21.724 | 26.976 | 1.00 43.35 |
| ATOM | 1226 | CG | ASN | A | 392 | 11.798 | 21.690 | 27.603 | 1.00 48.29 |

Figure 7

| | | | | | | | | | |
|---|---|---|---|---|---|---|---|---|---|
| ATOM | 1227 | OD1 | ASN | A | 392 | 10.953 | 20.840 | 27.271 | 1.00 50.32 |
| ATOM | 1228 | ND2 | ASN | A | 392 | 11.540 | 22.630 | 28.514 | 1.00 48.97 |
| ATOM | 1229 | C | ASN | A | 392 | 13.497 | 19.300 | 27.691 | 1.00 38.48 |
| ATOM | 1230 | O | ASN | A | 392 | 13.788 | 19.560 | 28.852 | 1.00 39.75 |
| ATOM | 1231 | N | GLU | A | 393 | 12.970 | 18.132 | 27.339 | 1.00 36.12 |
| ATOM | 1232 | CA | GLU | A | 393 | 12.666 | 17.117 | 28.338 | 1.00 33.60 |
| ATOM | 1233 | CB | GLU | A | 393 | 11.633 | 16.119 | 27.794 | 1.00 31.39 |
| ATOM | 1234 | CG | GLU | A | 393 | 10.258 | 16.745 | 27.557 | 1.00 27.40 |
| ATOM | 1235 | CD | GLU | A | 393 | 9.206 | 15.765 | 27.082 | 1.00 24.92 |
| ATOM | 1236 | OE1 | GLU | A | 393 | 9.421 | 14.553 | 27.168 | 1.00 25.71 |
| ATOM | 1237 | OE2 | GLU | A | 393 | 8.140 | 16.204 | 26.633 | 1.00 25.86 |
| ATOM | 1238 | C | GLU | A | 393 | 13.882 | 16.412 | 28.930 | 1.00 34.40 |
| ATOM | 1239 | O | GLU | A | 393 | 13.844 | 15.993 | 30.090 | 1.00 34.25 |
| ATOM | 1240 | N | TYR | A | 394 | 14.962 | 16.286 | 28.152 | 1.00 35.25 |
| ATOM | 1241 | CA | TYR | A | 394 | 16.190 | 15.643 | 28.647 | 1.00 35.72 |
| ATOM | 1242 | CB | TYR | A | 394 | 16.341 | 14.223 | 28.099 | 1.00 34.10 |
| ATOM | 1243 | CG | TYR | A | 394 | 15.230 | 13.307 | 28.545 | 1.00 34.73 |
| ATOM | 1244 | CD1 | TYR | A | 394 | 14.068 | 13.173 | 27.789 | 1.00 34.34 |
| ATOM | 1245 | CE1 | TYR | A | 394 | 12.999 | 12.415 | 28.241 | 1.00 34.48 |
| ATOM | 1246 | CD2 | TYR | A | 394 | 15.299 | 12.641 | 29.763 | 1.00 35.81 |
| ATOM | 1247 | CE2 | TYR | A | 394 | 14.226 | 11.871 | 30.229 | 1.00 35.37 |
| ATOM | 1248 | CZ | TYR | A | 394 | 13.080 | 11.769 | 29.462 | 1.00 35.19 |
| ATOM | 1249 | OH | TYR | A | 394 | 11.999 | 11.053 | 29.924 | 1.00 35.28 |
| ATOM | 1250 | C | TYR | A | 394 | 17.429 | 16.467 | 28.342 | 1.00 37.25 |
| ATOM | 1251 | O | TYR | A | 394 | 18.558 | 16.017 | 28.583 | 1.00 35.95 |
| ATOM | 1252 | N | THR | A | 395 | 17.215 | 17.660 | 27.785 | 1.00 39.83 |
| ATOM | 1253 | CA | THR | A | 395 | 18.292 | 18.592 | 27.474 | 1.00 43.70 |
| ATOM | 1254 | CB | THR | A | 395 | 18.778 | 18.538 | 25.989 | 1.00 43.92 |
| ATOM | 1255 | OG1 | THR | A | 395 | 18.118 | 17.495 | 25.257 | 1.00 41.67 |
| ATOM | 1256 | CG2 | THR | A | 395 | 20.284 | 18.316 | 25.975 | 1.00 43.00 |
| ATOM | 1257 | C | THR | A | 395 | 17.840 | 20.010 | 27.761 | 1.00 46.59 |
| ATOM | 1258 | O | THR | A | 395 | 16.769 | 20.218 | 28.340 | 1.00 46.44 |
| ATOM | 1259 | N | ALA | A | 396 | 18.632 | 20.993 | 27.332 | 1.00 50.59 |
| ATOM | 1260 | CA | ALA | A | 396 | 18.313 | 22.393 | 27.567 | 1.00 54.34 |
| ATOM | 1261 | CB | ALA | A | 396 | 19.194 | 22.940 | 28.687 | 1.00 54.72 |
| ATOM | 1262 | C | ALA | A | 396 | 18.420 | 23.293 | 26.326 | 1.00 56.94 |
| ATOM | 1263 | O | ALA | A | 396 | 19.288 | 24.179 | 26.282 | 1.00 59.09 |
| ATOM | 1264 | N | ARG | A | 397 | 17.559 | 23.063 | 25.331 | 1.00 57.84 |
| ATOM | 1265 | CA | ARG | A | 397 | 17.563 | 23.887 | 24.119 | 1.00 58.22 |
| ATOM | 1266 | CB | ARG | A | 397 | 17.141 | 23.075 | 22.895 | 1.00 58.92 |
| ATOM | 1267 | CG | ARG | A | 397 | 18.190 | 22.103 | 22.375 | 1.00 58.34 |
| ATOM | 1268 | CD | ARG | A | 397 | 18.102 | 22.006 | 20.852 | 1.00 58.36 |
| ATOM | 1269 | NE | ARG | A | 397 | 18.933 | 20.940 | 20.300 | 1.00 57.60 |
| ATOM | 1270 | CZ | ARG | A | 397 | 18.628 | 19.645 | 20.363 | 1.00 57.73 |
| ATOM | 1271 | NH1 | ARG | A | 397 | 17.510 | 19.249 | 20.965 | 1.00 57.75 |
| ATOM | 1272 | NH2 | ARG | A | 397 | 19.437 | 18.745 | 19.816 | 1.00 57.51 |
| ATOM | 1273 | C | ARG | A | 397 | 16.670 | 25.130 | 24.256 | 1.00 58.56 |
| ATOM | 1274 | O | ARG | A | 397 | 17.183 | 26.253 | 24.022 | 1.00 58.57 |
| ATOM | 1275 | CB | PRO | A | 403 | 6.991 | 19.631 | 18.764 | 1.00 26.43 |
| ATOM | 1276 | CG | PRO | A | 403 | 7.262 | 19.995 | 20.205 | 1.00 27.52 |
| ATOM | 1277 | C | PRO | A | 403 | 5.990 | 21.090 | 16.965 | 1.00 26.93 |
| ATOM | 1278 | O | PRO | A | 403 | 5.919 | 20.223 | 16.065 | 1.00 25.42 |
| ATOM | 1279 | N | PRO | A | 403 | 6.629 | 21.988 | 19.218 | 1.00 26.10 |
| ATOM | 1280 | CD | PRO | A | 403 | 6.553 | 21.310 | 20.511 | 1.00 27.95 |
| ATOM | 1281 | CA | PRO | A | 403 | 7.002 | 21.005 | 18.128 | 1.00 27.54 |
| ATOM | 1282 | N | ILE | A | 404 | 5.191 | 22.154 | 17.018 | 1.00 26.66 |
| ATOM | 1283 | CA | ILE | A | 404 | 4.154 | 22.448 | 16.048 | 1.00 25.51 |
| ATOM | 1284 | CB | ILE | A | 404 | 3.442 | 23.754 | 16.456 | 1.00 26.20 |
| ATOM | 1285 | CG2 | ILE | A | 404 | 2.877 | 24.508 | 15.243 | 1.00 26.04 |

Figure 7

```
ATOM   1286  CG1 ILE A 404       2.392  23.444  17.523  1.00 26.73
ATOM   1287  CD1 ILE A 404       1.413  22.388  17.069  1.00 28.74
ATOM   1288  C   ILE A 404       4.633  22.511  14.603  1.00 24.73
ATOM   1289  O   ILE A 404       3.975  21.989  13.703  1.00 24.97
ATOM   1290  N   LYS A 405       5.819  23.073  14.397  1.00 23.66
ATOM   1291  CA  LYS A 405       6.378  23.236  13.056  1.00 22.22
ATOM   1292  CB  LYS A 405       7.581  24.168  13.096  1.00 21.92
ATOM   1293  CG  LYS A 405       7.232  25.554  13.585  1.00 22.89
ATOM   1294  CD  LYS A 405       8.458  26.443  13.619  1.00 22.85
ATOM   1295  CE  LYS A 405       8.071  27.858  13.955  1.00 21.86
ATOM   1296  NZ  LYS A 405       9.110  28.765  13.440  1.00 24.56
ATOM   1297  C   LYS A 405       6.703  21.981  12.241  1.00 21.44
ATOM   1298  O   LYS A 405       7.035  22.093  11.056  1.00 22.01
ATOM   1299  N   TRP A 406       6.594  20.804  12.865  1.00 21.15
ATOM   1300  CA  TRP A 406       6.837  19.520  12.186  1.00 20.04
ATOM   1301  CB  TRP A 406       7.889  18.683  12.929  1.00 20.63
ATOM   1302  CG  TRP A 406       9.275  19.212  12.852  1.00 20.26
ATOM   1303  CD2 TRP A 406       9.827  20.252  13.662  1.00 21.13
ATOM   1304  CE2 TRP A 406      11.148  20.459  13.228  1.00 20.84
ATOM   1305  CE3 TRP A 406       9.325  21.040  14.715  1.00 20.18
ATOM   1306  CD1 TRP A 406      10.259  18.834  11.980  1.00 19.53
ATOM   1307  NE1 TRP A 406      11.384  19.582  12.196  1.00 19.66
ATOM   1308  CZ2 TRP A 406      11.982  21.424  13.811  1.00 20.68
ATOM   1309  CZ3 TRP A 406      10.154  22.001  15.287  1.00 19.70
ATOM   1310  CH2 TRP A 406      11.466  22.182  14.833  1.00 18.94
ATOM   1311  C   TRP A 406       5.569  18.675  12.125  1.00 20.04
ATOM   1312  O   TRP A 406       5.563  17.621  11.487  1.00 17.79
ATOM   1313  N   THR A 407       4.513  19.146  12.799  1.00 20.32
ATOM   1314  CA  THR A 407       3.239  18.447  12.918  1.00 21.81
ATOM   1315  CB  THR A 407       2.631  18.786  14.283  1.00 21.95
ATOM   1316  OG1 THR A 407       3.641  18.575  15.270  1.00 23.28
ATOM   1317  CG2 THR A 407       1.450  17.895  14.628  1.00 23.20
ATOM   1318  C   THR A 407       2.236  18.693  11.785  1.00 22.35
ATOM   1319  O   THR A 407       1.889  19.839  11.494  1.00 23.83
ATOM   1320  N   ALA A 408       1.807  17.604  11.130  1.00 22.33
ATOM   1321  CA  ALA A 408       0.850  17.669  10.016  1.00 22.25
ATOM   1322  CB  ALA A 408       0.669  16.286   9.396  1.00 20.16
ATOM   1323  C   ALA A 408      -0.497  18.243  10.465  1.00 21.65
ATOM   1324  O   ALA A 408      -0.883  18.082  11.605  1.00 21.04
ATOM   1325  N   PRO A 409      -1.230  18.908   9.557  1.00 22.63
ATOM   1326  CD  PRO A 409      -0.832  19.151   8.160  1.00 22.65
ATOM   1327  CA  PRO A 409      -2.538  19.524   9.827  1.00 23.54
ATOM   1328  CB  PRO A 409      -2.964  20.024   8.451  1.00 22.78
ATOM   1329  CG  PRO A 409      -1.657  20.354   7.806  1.00 22.31
ATOM   1330  C   PRO A 409      -3.618  18.659  10.483  1.00 23.62
ATOM   1331  O   PRO A 409      -4.261  19.088  11.436  1.00 22.95
ATOM   1332  N   GLU A 410      -3.837  17.460   9.958  1.00 23.60
ATOM   1333  CA  GLU A 410      -4.817  16.556  10.546  1.00 24.31
ATOM   1334  CB  GLU A 410      -4.973  15.288   9.695  1.00 23.84
ATOM   1335  CG  GLU A 410      -3.778  14.338   9.699  1.00 24.04
ATOM   1336  CD  GLU A 410      -2.689  14.688   8.692  1.00 22.69
ATOM   1337  OE1 GLU A 410      -2.624  15.826   8.179  1.00 23.35
ATOM   1338  OE2 GLU A 410      -1.882  13.795   8.397  1.00 23.18
ATOM   1339  C   GLU A 410      -4.399  16.198  11.982  1.00 25.97
ATOM   1340  O   GLU A 410      -5.244  15.901  12.826  1.00 26.43
ATOM   1341  N   ALA A 411      -3.097  16.253  12.259  1.00 27.47
ATOM   1342  CA  ALA A 411      -2.574  15.947  13.587  1.00 28.62
ATOM   1343  CB  ALA A 411      -1.082  15.617  13.519  1.00 27.05
ATOM   1344  C   ALA A 411      -2.820  17.131  14.519  1.00 29.82
```

Figure 7

```
ATOM   1345  O    ALA A 411      -3.200  16.951  15.676  1.00 31.71
ATOM   1346  N    ILE A 412      -2.636  18.340  14.006  1.00 30.54
ATOM   1347  CA   ILE A 412      -2.849  19.541  14.804  1.00 31.65
ATOM   1348  CB   ILE A 412      -2.406  20.809  14.031  1.00 31.57
ATOM   1349  CG2  ILE A 412      -2.935  22.082  14.699  1.00 30.37
ATOM   1350  CG1  ILE A 412      -0.884  20.845  13.892  1.00 30.74
ATOM   1351  CD1  ILE A 412      -0.394  21.939  12.981  1.00 31.20
ATOM   1352  C    ILE A 412      -4.332  19.667  15.150  1.00 33.62
ATOM   1353  O    ILE A 412      -4.694  19.797  16.318  1.00 34.83
ATOM   1354  N    ASN A 413      -5.179  19.592  14.125  1.00 34.19
ATOM   1355  CA   ASN A 413      -6.624  19.726  14.273  1.00 34.38
ATOM   1356  CB   ASN A 413      -7.269  19.931  12.908  1.00 35.06
ATOM   1357  CG   ASN A 413      -6.750  21.153  12.202  1.00 36.18
ATOM   1358  OD1  ASN A 413      -6.235  22.076  12.835  1.00 37.89
ATOM   1359  ND2  ASN A 413      -6.866  21.168  10.879  1.00 35.70
ATOM   1360  C    ASN A 413      -7.360  18.604  14.980  1.00 34.58
ATOM   1361  O    ASN A 413      -8.059  18.844  15.955  1.00 35.17
ATOM   1362  N    TYR A 414      -7.222  17.381  14.481  1.00 34.63
ATOM   1363  CA   TYR A 414      -7.938  16.252  15.062  1.00 34.51
ATOM   1364  CB   TYR A 414      -8.767  15.554  13.963  1.00 37.57
ATOM   1365  CG   TYR A 414      -9.584  16.522  13.095  1.00 40.66
ATOM   1366  CD1  TYR A 414     -10.681  17.223  13.619  1.00 41.84
ATOM   1367  CE1  TYR A 414     -11.378  18.173  12.842  1.00 43.56
ATOM   1368  CD2  TYR A 414      -9.213  16.783  11.770  1.00 42.26
ATOM   1369  CE2  TYR A 414      -9.899  17.723  10.991  1.00 43.68
ATOM   1370  CZ   TYR A 414     -10.979  18.420  11.532  1.00 44.92
ATOM   1371  OH   TYR A 414     -11.632  19.379  10.774  1.00 44.79
ATOM   1372  C    TYR A 414      -7.066  15.261  15.848  1.00 33.07
ATOM   1373  O    TYR A 414      -7.549  14.239  16.329  1.00 32.66
ATOM   1374  N    GLY A 415      -5.786  15.585  16.005  1.00 31.79
ATOM   1375  CA   GLY A 415      -4.887  14.721  16.745  1.00 29.59
ATOM   1376  C    GLY A 415      -4.673  13.356  16.132  1.00 29.72
ATOM   1377  O    GLY A 415      -4.287  12.414  16.822  1.00 30.18
ATOM   1378  N    THR A 416      -4.926  13.230  14.834  1.00 29.14
ATOM   1379  CA   THR A 416      -4.723  11.952  14.169  1.00 27.76
ATOM   1380  CB   THR A 416      -5.813  11.688  13.081  1.00 28.40
ATOM   1381  OG1  THR A 416      -5.218  11.548  11.785  1.00 31.63
ATOM   1382  CG2  THR A 416      -6.834  12.804  13.059  1.00 27.20
ATOM   1383  C    THR A 416      -3.273  11.817  13.646  1.00 26.61
ATOM   1384  O    THR A 416      -2.819  12.591  12.802  1.00 26.50
ATOM   1385  N    PHE A 417      -2.535  10.881  14.240  1.00 24.47
ATOM   1386  CA   PHE A 417      -1.150  10.609  13.880  1.00 23.60
ATOM   1387  CB   PHE A 417      -0.270  10.552  15.141  1.00 22.05
ATOM   1388  CG   PHE A 417      -0.057  11.881  15.791  1.00 21.98
ATOM   1389  CD1  PHE A 417      -0.972  12.370  16.725  1.00 23.26
ATOM   1390  CD2  PHE A 417       1.024  12.682  15.430  1.00 20.61
ATOM   1391  CE1  PHE A 417      -0.814  13.653  17.284  1.00 22.48
ATOM   1392  CE2  PHE A 417       1.188  13.956  15.977  1.00 21.04
ATOM   1393  CZ   PHE A 417       0.269  14.445  16.903  1.00 21.72
ATOM   1394  C    PHE A 417      -1.036   9.287  13.138  1.00 23.39
ATOM   1395  O    PHE A 417      -1.493   8.264  13.636  1.00 24.02
ATOM   1396  N    THR A 418      -0.440   9.310  11.948  1.00 22.27
ATOM   1397  CA   THR A 418      -0.248   8.102  11.143  1.00 23.29
ATOM   1398  CB   THR A 418      -1.289   7.978  10.002  1.00 24.53
ATOM   1399  OG1  THR A 418      -1.118   9.061   9.077  1.00 26.51
ATOM   1400  CG2  THR A 418      -2.724   8.001  10.554  1.00 23.13
ATOM   1401  C    THR A 418       1.138   8.161  10.501  1.00 22.16
ATOM   1402  O    THR A 418       1.872   9.128  10.700  1.00 22.30
ATOM   1403  N    ILE A 419       1.503   7.136   9.738  1.00 20.90
```

Figure 7

| ATOM | 1404 | CA  | ILE | A | 419 | 2.803  | 7.138  | 9.080  | 1.00 | 20.09 |
| ATOM | 1405 | CB  | ILE | A | 419 | 3.088  | 5.798  | 8.329  | 1.00 | 19.49 |
| ATOM | 1406 | CG2 | ILE | A | 419 | 2.213  | 5.666  | 7.076  | 1.00 | 16.42 |
| ATOM | 1407 | CG1 | ILE | A | 419 | 4.572  | 5.697  | 7.947  | 1.00 | 19.91 |
| ATOM | 1408 | CD1 | ILE | A | 419 | 5.545  | 5.737  | 9.119  | 1.00 | 15.99 |
| ATOM | 1409 | C   | ILE | A | 419 | 2.853  | 8.333  | 8.118  | 1.00 | 19.58 |
| ATOM | 1410 | O   | ILE | A | 419 | 3.921  | 8.884  | 7.866  | 1.00 | 20.16 |
| ATOM | 1411 | N   | LYS | A | 420 | 1.678  | 8.761  | 7.642  | 1.00 | 18.73 |
| ATOM | 1412 | CA  | LYS | A | 420 | 1.556  | 9.907  | 6.719  | 1.00 | 16.80 |
| ATOM | 1413 | CB  | LYS | A | 420 | 0.197  | 9.907  | 6.006  | 1.00 | 15.69 |
| ATOM | 1414 | CG  | LYS | A | 420 | -0.011 | 8.742  | 5.064  | 1.00 | 12.82 |
| ATOM | 1415 | CD  | LYS | A | 420 | 1.036  | 8.730  | 4.003  | 1.00 | 13.01 |
| ATOM | 1416 | CE  | LYS | A | 420 | 0.645  | 7.804  | 2.894  | 1.00 | 13.88 |
| ATOM | 1417 | NZ  | LYS | A | 420 | 1.813  | 7.594  | 2.017  | 1.00 | 17.10 |
| ATOM | 1418 | C   | LYS | A | 420 | 1.809  | 11.264 | 7.386  | 1.00 | 16.12 |
| ATOM | 1419 | O   | LYS | A | 420 | 2.204  | 12.224 | 6.719  | 1.00 | 15.54 |
| ATOM | 1420 | N   | SER | A | 421 | 1.522  | 11.372 | 8.681  | 1.00 | 16.70 |
| ATOM | 1421 | CA  | SER | A | 421 | 1.821  | 12.614 | 9.374  | 1.00 | 18.15 |
| ATOM | 1422 | CB  | SER | A | 421 | 0.953  | 12.823 | 10.632 | 1.00 | 17.99 |
| ATOM | 1423 | OG  | SER | A | 421 | 1.014  | 11.755 | 11.546 | 1.00 | 22.15 |
| ATOM | 1424 | C   | SER | A | 421 | 3.346  | 12.673 | 9.631  | 1.00 | 18.39 |
| ATOM | 1425 | O   | SER | A | 421 | 3.915  | 13.755 | 9.747  | 1.00 | 18.96 |
| ATOM | 1426 | N   | ASP | A | 422 | 4.001  | 11.508 | 9.647  | 1.00 | 18.79 |
| ATOM | 1427 | CA  | ASP | A | 422 | 5.460  | 11.439 | 9.790  | 1.00 | 18.62 |
| ATOM | 1428 | CB  | ASP | A | 422 | 5.966  | 10.012 | 10.050 | 1.00 | 18.97 |
| ATOM | 1429 | CG  | ASP | A | 422 | 5.595  | 9.485  | 11.424 | 1.00 | 20.61 |
| ATOM | 1430 | OD1 | ASP | A | 422 | 5.364  | 10.291 | 12.350 | 1.00 | 22.75 |
| ATOM | 1431 | OD2 | ASP | A | 422 | 5.540  | 8.249  | 11.572 | 1.00 | 20.85 |
| ATOM | 1432 | C   | ASP | A | 422 | 6.056  | 11.888 | 8.467  | 1.00 | 19.26 |
| ATOM | 1433 | O   | ASP | A | 422 | 7.091  | 12.548 | 8.452  | 1.00 | 21.08 |
| ATOM | 1434 | N   | VAL | A | 423 | 5.425  | 11.490 | 7.357  | 1.00 | 18.90 |
| ATOM | 1435 | CA  | VAL | A | 423 | 5.893  | 11.873 | 6.017  | 1.00 | 18.85 |
| ATOM | 1436 | CB  | VAL | A | 423 | 4.997  | 11.273 | 4.872  | 1.00 | 18.70 |
| ATOM | 1437 | CG1 | VAL | A | 423 | 5.374  | 11.889 | 3.521  | 1.00 | 18.05 |
| ATOM | 1438 | CG2 | VAL | A | 423 | 5.165  | 9.756  | 4.796  | 1.00 | 16.30 |
| ATOM | 1439 | C   | VAL | A | 423 | 5.932  | 13.405 | 5.925  | 1.00 | 19.05 |
| ATOM | 1440 | O   | VAL | A | 423 | 6.867  | 13.986 | 5.346  | 1.00 | 19.86 |
| ATOM | 1441 | N   | TRP | A | 424 | 4.943  | 14.043 | 6.544  | 1.00 | 18.31 |
| ATOM | 1442 | CA  | TRP | A | 424 | 4.861  | 15.498 | 6.575  | 1.00 | 18.28 |
| ATOM | 1443 | CB  | TRP | A | 424 | 3.525  | 15.929 | 7.196  | 1.00 | 17.39 |
| ATOM | 1444 | CG  | TRP | A | 424 | 3.408  | 17.424 | 7.385  | 1.00 | 19.03 |
| ATOM | 1445 | CD2 | TRP | A | 424 | 2.564  | 18.333 | 6.660  | 1.00 | 18.06 |
| ATOM | 1446 | CE2 | TRP | A | 424 | 2.823  | 19.629 | 7.161  | 1.00 | 19.04 |
| ATOM | 1447 | CE3 | TRP | A | 424 | 1.618  | 18.178 | 5.644  | 1.00 | 15.97 |
| ATOM | 1448 | CD1 | TRP | A | 424 | 4.115  | 18.192 | 8.271  | 1.00 | 19.41 |
| ATOM | 1449 | NE1 | TRP | A | 424 | 3.772  | 19.509 | 8.140  | 1.00 | 18.89 |
| ATOM | 1450 | CZ2 | TRP | A | 424 | 2.168  | 20.769 | 6.677  | 1.00 | 19.66 |
| ATOM | 1451 | CZ3 | TRP | A | 424 | 0.966  | 19.305 | 5.166  | 1.00 | 17.20 |
| ATOM | 1452 | CH2 | TRP | A | 424 | 1.243  | 20.586 | 5.682  | 1.00 | 20.15 |
| ATOM | 1453 | C   | TRP | A | 424 | 6.043  | 16.037 | 7.402  | 1.00 | 17.83 |
| ATOM | 1454 | O   | TRP | A | 424 | 6.698  | 16.995 | 7.005  | 1.00 | 17.75 |
| ATOM | 1455 | N   | SER | A | 425 | 6.309  | 15.414 | 8.550  | 1.00 | 18.06 |
| ATOM | 1456 | CA  | SER | A | 425 | 7.427  | 15.821 | 9.413  | 1.00 | 19.43 |
| ATOM | 1457 | CB  | SER | A | 425 | 7.470  | 14.977 | 10.686 | 1.00 | 19.26 |
| ATOM | 1458 | OG  | SER | A | 425 | 6.321  | 15.181 | 11.476 | 1.00 | 21.61 |
| ATOM | 1459 | C   | SER | A | 425 | 8.753  | 15.663 | 8.703  | 1.00 | 19.00 |
| ATOM | 1460 | O   | SER | A | 425 | 9.662  | 16.446 | 8.911  | 1.00 | 21.22 |
| ATOM | 1461 | N   | PHE | A | 426 | 8.868  | 14.596 | 7.923  | 1.00 | 18.15 |
| ATOM | 1462 | CA  | PHE | A | 426 | 10.080 | 14.311 | 7.178  | 1.00 | 18.91 |

Figure 7

```
ATOM   1463  CB   PHE A 426       9.934  12.991   6.415  1.00 18.40
ATOM   1464  CG   PHE A 426      11.163  12.591   5.671  1.00 18.57
ATOM   1465  CD1  PHE A 426      12.292  12.144   6.363  1.00 17.51
ATOM   1466  CD2  PHE A 426      11.214  12.688   4.280  1.00 18.40
ATOM   1467  CE1  PHE A 426      13.447  11.805   5.686  1.00 17.55
ATOM   1468  CE2  PHE A 426      12.372  12.347   3.585  1.00 19.48
ATOM   1469  CZ   PHE A 426      13.494  11.904   4.295  1.00 19.32
ATOM   1470  C    PHE A 426      10.426  15.439   6.211  1.00 18.64
ATOM   1471  O    PHE A 426      11.591  15.826   6.113  1.00 19.11
ATOM   1472  N    GLY A 427       9.424  15.930   5.475  1.00 18.05
ATOM   1473  CA   GLY A 427       9.633  17.032   4.542  1.00 16.71
ATOM   1474  C    GLY A 427      10.085  18.301   5.238  1.00 16.58
ATOM   1475  O    GLY A 427      10.782  19.119   4.656  1.00 16.36
ATOM   1476  N    ILE A 428       9.653  18.484   6.484  1.00 18.13
ATOM   1477  CA   ILE A 428      10.053  19.638   7.285  1.00 18.14
ATOM   1478  CB   ILE A 428       9.180  19.786   8.559  1.00 17.57
ATOM   1479  CG2  ILE A 428       9.680  20.931   9.408  1.00 16.37
ATOM   1480  CG1  ILE A 428       7.708  19.995   8.183  1.00 17.69
ATOM   1481  CD1  ILE A 428       7.388  21.319   7.456  1.00 17.37
ATOM   1482  C    ILE A 428      11.500  19.389   7.694  1.00 18.75
ATOM   1483  O    ILE A 428      12.318  20.298   7.697  1.00 18.90
ATOM   1484  N    LEU A 429      11.807  18.133   8.001  1.00 19.34
ATOM   1485  CA   LEU A 429      13.153  17.715   8.389  1.00 19.43
ATOM   1486  CB   LEU A 429      13.166  16.221   8.759  1.00 20.32
ATOM   1487  CG   LEU A 429      14.297  15.644   9.624  1.00 20.57
ATOM   1488  CD1  LEU A 429      13.989  14.209   9.932  1.00 21.56
ATOM   1489  CD2  LEU A 429      15.659  15.743   8.974  1.00 21.83
ATOM   1490  C    LEU A 429      14.091  17.966   7.225  1.00 18.98
ATOM   1491  O    LEU A 429      15.218  18.372   7.428  1.00 20.75
ATOM   1492  N    LEU A 430      13.632  17.725   6.002  1.00 19.49
ATOM   1493  CA   LEU A 430      14.468  17.962   4.830  1.00 20.28
ATOM   1494  CB   LEU A 430      13.747  17.598   3.528  1.00 19.77
ATOM   1495  CG   LEU A 430      13.520  16.129   3.168  1.00 19.75
ATOM   1496  CD1  LEU A 430      12.661  16.038   1.920  1.00 18.89
ATOM   1497  CD2  LEU A 430      14.848  15.411   2.960  1.00 19.13
ATOM   1498  C    LEU A 430      14.903  19.415   4.765  1.00 21.00
ATOM   1499  O    LEU A 430      16.023  19.695   4.337  1.00 21.46
ATOM   1500  N    THR A 431      14.030  20.337   5.193  1.00 21.27
ATOM   1501  CA   THR A 431      14.373  21.760   5.163  1.00 20.84
ATOM   1502  CB   THR A 431      13.162  22.723   5.431  1.00 19.74
ATOM   1503  OG1  THR A 431      12.702  22.607   6.776  1.00 19.43
ATOM   1504  CG2  THR A 431      12.021  22.423   4.493  1.00 19.47
ATOM   1505  C    THR A 431      15.499  22.017   6.141  1.00 20.57
ATOM   1506  O    THR A 431      16.425  22.742   5.825  1.00 20.87
ATOM   1507  N    GLU A 432      15.448  21.347   7.291  1.00 22.66
ATOM   1508  CA   GLU A 432      16.482  21.473   8.314  1.00 22.58
ATOM   1509  CB   GLU A 432      16.134  20.660   9.556  1.00 21.11
ATOM   1510  CG   GLU A 432      14.870  21.095  10.266  1.00 21.14
ATOM   1511  CD   GLU A 432      14.597  20.269  11.509  1.00 21.58
ATOM   1512  OE1  GLU A 432      14.052  19.147  11.395  1.00 19.32
ATOM   1513  OE2  GLU A 432      14.948  20.738  12.611  1.00 23.61
ATOM   1514  C    GLU A 432      17.791  20.961   7.743  1.00 23.19
ATOM   1515  O    GLU A 432      18.827  21.601   7.884  1.00 25.50
ATOM   1516  N    ILE A 433      17.740  19.825   7.064  1.00 22.96
ATOM   1517  CA   ILE A 433      18.938  19.247   6.472  1.00 24.06
ATOM   1518  CB   ILE A 433      18.615  17.885   5.833  1.00 22.74
ATOM   1519  CG2  ILE A 433      19.644  17.510   4.775  1.00 23.15
ATOM   1520  CG1  ILE A 433      18.522  16.826   6.932  1.00 22.86
ATOM   1521  CD1  ILE A 433      18.021  15.469   6.453  1.00 20.64
```

Figure 7

| | | | | | | | | | |
|---|---|---|---|---|---|---|---|---|---|
| ATOM | 1522 | C | ILE | A | 433 | 19.675 | 20.185 | 5.499 | 1.00 25.84 |
| ATOM | 1523 | O | ILE | A | 433 | 20.871 | 20.438 | 5.680 | 1.00 25.08 |
| ATOM | 1524 | N | VAL | A | 434 | 18.945 | 20.744 | 4.525 | 1.00 27.55 |
| ATOM | 1525 | CA | VAL | A | 434 | 19.512 | 21.648 | 3.520 | 1.00 28.03 |
| ATOM | 1526 | CB | VAL | A | 434 | 18.625 | 21.768 | 2.258 | 1.00 27.39 |
| ATOM | 1527 | CG1 | VAL | A | 434 | 18.533 | 20.438 | 1.588 | 1.00 28.69 |
| ATOM | 1528 | CG2 | VAL | A | 434 | 17.244 | 22.300 | 2.592 | 1.00 27.31 |
| ATOM | 1529 | C | VAL | A | 434 | 19.873 | 23.046 | 3.993 | 1.00 28.80 |
| ATOM | 1530 | O | VAL | A | 434 | 20.636 | 23.742 | 3.335 | 1.00 30.53 |
| ATOM | 1531 | N | THR | A | 435 | 19.336 | 23.461 | 5.129 | 1.00 29.98 |
| ATOM | 1532 | CA | THR | A | 435 | 19.657 | 24.783 | 5.654 | 1.00 30.92 |
| ATOM | 1533 | CB | THR | A | 435 | 18.396 | 25.532 | 6.103 | 1.00 29.65 |
| ATOM | 1534 | OG1 | THR | A | 435 | 17.802 | 24.838 | 7.211 | 1.00 29.95 |
| ATOM | 1535 | CG2 | THR | A | 435 | 17.400 | 25.666 | 4.933 | 1.00 26.99 |
| ATOM | 1536 | C | THR | A | 435 | 20.636 | 24.697 | 6.828 | 1.00 32.61 |
| ATOM | 1537 | O | THR | A | 435 | 20.843 | 25.676 | 7.544 | 1.00 33.21 |
| ATOM | 1538 | N | HIS | A | 436 | 21.228 | 23.518 | 7.019 | 1.00 34.55 |
| ATOM | 1539 | CA | HIS | A | 436 | 22.185 | 23.271 | 8.094 | 1.00 36.31 |
| ATOM | 1540 | CB | HIS | A | 436 | 23.471 | 24.064 | 7.857 | 1.00 39.42 |
| ATOM | 1541 | CG | HIS | A | 436 | 24.120 | 23.776 | 6.539 | 1.00 42.33 |
| ATOM | 1542 | CD2 | HIS | A | 436 | 24.515 | 24.605 | 5.539 | 1.00 45.07 |
| ATOM | 1543 | ND1 | HIS | A | 436 | 24.424 | 22.500 | 6.116 | 1.00 43.90 |
| ATOM | 1544 | CE1 | HIS | A | 436 | 24.983 | 22.551 | 4.917 | 1.00 44.19 |
| ATOM | 1545 | NE2 | HIS | A | 436 | 25.047 | 23.818 | 4.546 | 1.00 46.14 |
| ATOM | 1546 | C | HIS | A | 436 | 21.623 | 23.553 | 9.485 | 1.00 36.23 |
| ATOM | 1547 | O | HIS | A | 436 | 22.213 | 24.293 | 10.276 | 1.00 36.90 |
| ATOM | 1548 | N | GLY | A | 437 | 20.468 | 22.944 | 9.761 | 1.00 36.33 |
| ATOM | 1549 | CA | GLY | A | 437 | 19.802 | 23.075 | 11.043 | 1.00 35.79 |
| ATOM | 1550 | C | GLY | A | 437 | 19.012 | 24.336 | 11.315 | 1.00 35.94 |
| ATOM | 1551 | O | GLY | A | 437 | 18.754 | 24.650 | 12.472 | 1.00 37.33 |
| ATOM | 1552 | N | ARG | A | 438 | 18.607 | 25.043 | 10.268 | 1.00 35.84 |
| ATOM | 1553 | CA | ARG | A | 438 | 17.829 | 26.273 | 10.421 | 1.00 36.13 |
| ATOM | 1554 | CB | ARG | A | 438 | 17.872 | 27.051 | 9.098 | 1.00 38.09 |
| ATOM | 1555 | CG | ARG | A | 438 | 17.569 | 28.544 | 9.152 | 1.00 42.51 |
| ATOM | 1556 | CD | ARG | A | 438 | 16.059 | 28.846 | 9.216 | 1.00 46.42 |
| ATOM | 1557 | NE | ARG | A | 438 | 15.269 | 28.138 | 8.202 | 1.00 48.96 |
| ATOM | 1558 | CZ | ARG | A | 438 | 15.166 | 28.508 | 6.929 | 1.00 50.77 |
| ATOM | 1559 | NH1 | ARG | A | 438 | 15.811 | 29.593 | 6.510 | 1.00 53.02 |
| ATOM | 1560 | NH2 | ARG | A | 438 | 14.420 | 27.801 | 6.078 | 1.00 50.51 |
| ATOM | 1561 | C | ARG | A | 438 | 16.384 | 25.902 | 10.799 | 1.00 34.61 |
| ATOM | 1562 | O | ARG | A | 438 | 15.826 | 24.946 | 10.272 | 1.00 34.48 |
| ATOM | 1563 | N | ILE | A | 439 | 15.808 | 26.639 | 11.744 | 1.00 33.51 |
| ATOM | 1564 | CA | ILE | A | 439 | 14.438 | 26.414 | 12.218 | 1.00 32.27 |
| ATOM | 1565 | CB | ILE | A | 439 | 14.102 | 27.353 | 13.409 | 1.00 31.69 |
| ATOM | 1566 | CG2 | ILE | A | 439 | 12.607 | 27.412 | 13.663 | 1.00 32.66 |
| ATOM | 1567 | CG1 | ILE | A | 439 | 14.789 | 26.842 | 14.676 | 1.00 34.66 |
| ATOM | 1568 | CD1 | ILE | A | 439 | 14.705 | 27.797 | 15.882 | 1.00 35.77 |
| ATOM | 1569 | C | ILE | A | 439 | 13.394 | 26.600 | 11.127 | 1.00 31.24 |
| ATOM | 1570 | O | ILE | A | 439 | 13.433 | 27.572 | 10.375 | 1.00 32.20 |
| ATOM | 1571 | N | PRO | A | 440 | 12.443 | 25.660 | 11.021 | 1.00 30.07 |
| ATOM | 1572 | CD | PRO | A | 440 | 12.346 | 24.403 | 11.784 | 1.00 28.25 |
| ATOM | 1573 | CA | PRO | A | 440 | 11.382 | 25.750 | 10.003 | 1.00 29.93 |
| ATOM | 1574 | CB | PRO | A | 440 | 10.542 | 24.500 | 10.278 | 1.00 29.71 |
| ATOM | 1575 | CG | PRO | A | 440 | 11.548 | 23.531 | 10.856 | 1.00 29.39 |
| ATOM | 1576 | C | PRO | A | 440 | 10.538 | 27.031 | 10.163 | 1.00 28.94 |
| ATOM | 1577 | O | PRO | A | 440 | 10.439 | 27.578 | 11.259 | 1.00 28.24 |
| ATOM | 1578 | N | TYR | A | 441 | 9.936 | 27.494 | 9.066 | 1.00 29.37 |
| ATOM | 1579 | CA | TYR | A | 441 | 9.094 | 28.698 | 9.060 | 1.00 29.43 |
| ATOM | 1580 | CB | TYR | A | 441 | 7.710 | 28.421 | 9.665 | 1.00 28.15 |

Figure 7

| | | | | | | | | |
|---|---|---|---|---|---|---|---|---|
| ATOM | 1581 | CG | TYR | A | 441 | 6.967 | 27.237 | 9.088 | 1.00 | 25.63 |
| ATOM | 1582 | CD1 | TYR | A | 441 | 6.090 | 27.392 | 8.013 | 1.00 | 24.38 |
| ATOM | 1583 | CE1 | TYR | A | 441 | 5.376 | 26.303 | 7.511 | 1.00 | 24.97 |
| ATOM | 1584 | CD2 | TYR | A | 441 | 7.118 | 25.963 | 9.644 | 1.00 | 23.65 |
| ATOM | 1585 | CE2 | TYR | A | 441 | 6.416 | 24.865 | 9.154 | 1.00 | 22.76 |
| ATOM | 1586 | CZ | TYR | A | 441 | 5.545 | 25.040 | 8.093 | 1.00 | 24.43 |
| ATOM | 1587 | OH | TYR | A | 441 | 4.834 | 23.962 | 7.623 | 1.00 | 25.16 |
| ATOM | 1588 | C | TYR | A | 441 | 9.759 | 29.829 | 9.846 | 1.00 | 30.78 |
| ATOM | 1589 | O | TYR | A | 441 | 9.202 | 30.318 | 10.833 | 1.00 | 29.68 |
| ATOM | 1590 | N | PRO | A | 442 | 10.959 | 30.261 | 9.405 | 1.00 | 32.11 |
| ATOM | 1591 | CD | PRO | A | 442 | 11.567 | 29.850 | 8.125 | 1.00 | 30.87 |
| ATOM | 1592 | CA | PRO | A | 442 | 11.748 | 31.333 | 10.038 | 1.00 | 33.48 |
| ATOM | 1593 | CB | PRO | A | 442 | 12.947 | 31.462 | 9.094 | 1.00 | 33.85 |
| ATOM | 1594 | CG | PRO | A | 442 | 12.360 | 31.067 | 7.746 | 1.00 | 32.40 |
| ATOM | 1595 | C | PRO | A | 442 | 10.983 | 32.660 | 10.167 | 1.00 | 34.36 |
| ATOM | 1596 | O | PRO | A | 442 | 10.439 | 33.175 | 9.183 | 1.00 | 34.53 |
| ATOM | 1597 | N | GLY | A | 443 | 10.938 | 33.214 | 11.374 | 1.00 | 34.64 |
| ATOM | 1598 | CA | GLY | A | 443 | 10.226 | 34.468 | 11.574 | 1.00 | 35.80 |
| ATOM | 1599 | C | GLY | A | 443 | 8.722 | 34.319 | 11.774 | 1.00 | 36.34 |
| ATOM | 1600 | O | GLY | A | 443 | 7.957 | 35.265 | 11.565 | 1.00 | 37.07 |
| ATOM | 1601 | N | MET | A | 444 | 8.299 | 33.105 | 12.122 | 1.00 | 35.99 |
| ATOM | 1602 | CA | MET | A | 444 | 6.901 | 32.788 | 12.391 | 1.00 | 34.84 |
| ATOM | 1603 | CB | MET | A | 444 | 6.329 | 31.838 | 11.333 | 1.00 | 34.19 |
| ATOM | 1604 | CG | MET | A | 444 | 5.860 | 32.499 | 10.053 | 1.00 | 33.78 |
| ATOM | 1605 | SD | MET | A | 444 | 5.104 | 31.324 | 8.893 | 1.00 | 33.61 |
| ATOM | 1606 | CE | MET | A | 444 | 3.532 | 31.320 | 9.416 | 1.00 | 33.83 |
| ATOM | 1607 | C | MET | A | 444 | 6.860 | 32.098 | 13.739 | 1.00 | 34.75 |
| ATOM | 1608 | O | MET | A | 444 | 7.731 | 31.291 | 14.052 | 1.00 | 35.56 |
| ATOM | 1609 | N | THR | A | 445 | 5.862 | 32.424 | 14.550 | 1.00 | 34.78 |
| ATOM | 1610 | CA | THR | A | 445 | 5.720 | 31.800 | 15.856 | 1.00 | 34.53 |
| ATOM | 1611 | CB | THR | A | 445 | 5.010 | 32.739 | 16.859 | 1.00 | 34.48 |
| ATOM | 1612 | OG1 | THR | A | 445 | 3.710 | 33.076 | 16.361 | 1.00 | 35.52 |
| ATOM | 1613 | CG2 | THR | A | 445 | 5.802 | 34.013 | 17.049 | 1.00 | 34.60 |
| ATOM | 1614 | C | THR | A | 445 | 4.863 | 30.546 | 15.682 | 1.00 | 34.57 |
| ATOM | 1615 | O | THR | A | 445 | 4.315 | 30.309 | 14.603 | 1.00 | 33.24 |
| ATOM | 1616 | N | ASN | A | 446 | 4.730 | 29.764 | 16.755 | 1.00 | 34.60 |
| ATOM | 1617 | CA | ASN | A | 446 | 3.905 | 28.557 | 16.720 | 1.00 | 34.15 |
| ATOM | 1618 | CB | ASN | A | 446 | 3.922 | 27.828 | 18.072 | 1.00 | 30.88 |
| ATOM | 1619 | CG | ASN | A | 446 | 5.025 | 26.793 | 18.167 | 1.00 | 30.10 |
| ATOM | 1620 | OD1 | ASN | A | 446 | 5.953 | 26.773 | 17.347 | 1.00 | 29.09 |
| ATOM | 1621 | ND2 | ASN | A | 446 | 4.929 | 25.914 | 19.159 | 1.00 | 28.30 |
| ATOM | 1622 | C | ASN | A | 446 | 2.468 | 28.898 | 16.297 | 1.00 | 35.29 |
| ATOM | 1623 | O | ASN | A | 446 | 1.893 | 28.209 | 15.450 | 1.00 | 35.58 |
| ATOM | 1624 | N | PRO | A | 447 | 1.855 | 29.937 | 16.913 | 1.00 | 35.69 |
| ATOM | 1625 | CD | PRO | A | 447 | 2.219 | 30.600 | 18.180 | 1.00 | 34.55 |
| ATOM | 1626 | CA | PRO | A | 447 | 0.485 | 30.295 | 16.521 | 1.00 | 34.63 |
| ATOM | 1627 | CB | PRO | A | 447 | 0.051 | 31.280 | 17.614 | 1.00 | 34.86 |
| ATOM | 1628 | CG | PRO | A | 447 | 1.338 | 31.798 | 18.174 | 1.00 | 34.83 |
| ATOM | 1629 | C | PRO | A | 447 | 0.360 | 30.867 | 15.101 | 1.00 | 34.05 |
| ATOM | 1630 | O | PRO | A | 447 | -0.685 | 30.698 | 14.462 | 1.00 | 34.05 |
| ATOM | 1631 | N | GLU | A | 448 | 1.417 | 31.517 | 14.605 | 1.00 | 33.50 |
| ATOM | 1632 | CA | GLU | A | 448 | 1.417 | 32.071 | 13.238 | 1.00 | 33.48 |
| ATOM | 1633 | CB | GLU | A | 448 | 2.597 | 33.016 | 13.016 | 1.00 | 36.16 |
| ATOM | 1634 | CG | GLU | A | 448 | 2.464 | 34.370 | 13.694 | 1.00 | 42.15 |
| ATOM | 1635 | CD | GLU | A | 448 | 3.755 | 35.189 | 13.638 | 1.00 | 45.16 |
| ATOM | 1636 | OE1 | GLU | A | 448 | 4.513 | 35.058 | 12.648 | 1.00 | 47.68 |
| ATOM | 1637 | OE2 | GLU | A | 448 | 4.012 | 35.962 | 14.593 | 1.00 | 46.43 |
| ATOM | 1638 | C | GLU | A | 448 | 1.482 | 30.939 | 12.214 | 1.00 | 31.37 |
| ATOM | 1639 | O | GLU | A | 448 | 0.877 | 31.020 | 11.147 | 1.00 | 31.35 |

Figure 7

| ATOM | 1640 | N   | VAL | A | 449 | 2.231  | 29.887 | 12.541 | 1.00 | 29.69 |
| ATOM | 1641 | CA  | VAL | A | 449 | 2.338  | 28.724 | 11.666 | 1.00 | 27.17 |
| ATOM | 1642 | CB  | VAL | A | 449 | 3.436  | 27.742 | 12.161 | 1.00 | 24.85 |
| ATOM | 1643 | CG1 | VAL | A | 449 | 3.317  | 26.387 | 11.483 | 1.00 | 21.93 |
| ATOM | 1644 | CG2 | VAL | A | 449 | 4.796  | 28.324 | 11.868 | 1.00 | 23.76 |
| ATOM | 1645 | C   | VAL | A | 449 | 0.961  | 28.057 | 11.591 | 1.00 | 26.99 |
| ATOM | 1646 | O   | VAL | A | 449 | 0.517  | 27.661 | 10.516 | 1.00 | 28.07 |
| ATOM | 1647 | N   | ILE | A | 450 | 0.257  | 28.017 | 12.720 | 1.00 | 26.91 |
| ATOM | 1648 | CA  | ILE | A | 450 | -1.077 | 27.420 | 12.781 | 1.00 | 26.90 |
| ATOM | 1649 | CB  | ILE | A | 450 | -1.687 | 27.473 | 14.228 | 1.00 | 26.57 |
| ATOM | 1650 | CG2 | ILE | A | 450 | -2.990 | 26.708 | 14.272 | 1.00 | 26.21 |
| ATOM | 1651 | CG1 | ILE | A | 450 | -0.724 | 26.905 | 15.270 | 1.00 | 26.19 |
| ATOM | 1652 | CD1 | ILE | A | 450 | -0.603 | 25.426 | 15.270 | 1.00 | 26.58 |
| ATOM | 1653 | C   | ILE | A | 450 | -2.042 | 28.171 | 11.844 | 1.00 | 26.36 |
| ATOM | 1654 | O   | ILE | A | 450 | -2.759 | 27.557 | 11.060 | 1.00 | 26.27 |
| ATOM | 1655 | N   | GLN | A | 451 | -2.054 | 29.497 | 11.923 | 1.00 | 26.00 |
| ATOM | 1656 | CA  | GLN | A | 451 | -2.955 | 30.264 | 11.086 | 1.00 | 26.88 |
| ATOM | 1657 | CB  | GLN | A | 451 | -3.187 | 31.673 | 11.644 | 1.00 | 30.97 |
| ATOM | 1658 | CG  | GLN | A | 451 | -1.942 | 32.442 | 11.958 | 1.00 | 38.67 |
| ATOM | 1659 | CD  | GLN | A | 451 | -2.174 | 33.569 | 12.959 | 1.00 | 42.54 |
| ATOM | 1660 | OE1 | GLN | A | 451 | -1.523 | 34.615 | 12.890 | 1.00 | 45.27 |
| ATOM | 1661 | NE2 | GLN | A | 451 | -3.071 | 33.343 | 13.919 | 1.00 | 42.14 |
| ATOM | 1662 | C   | GLN | A | 451 | -2.580 | 30.297 | 9.620  | 1.00 | 25.50 |
| ATOM | 1663 | O   | GLN | A | 451 | -3.440 | 30.475 | 8.773  | 1.00 | 25.40 |
| ATOM | 1664 | N   | ASN | A | 452 | -1.302 | 30.126 | 9.310  | 1.00 | 24.55 |
| ATOM | 1665 | CA  | ASN | A | 452 | -0.898 | 30.107 | 7.921  | 1.00 | 23.92 |
| ATOM | 1666 | CB  | ASN | A | 452 | 0.590  | 30.372 | 7.791  | 1.00 | 26.09 |
| ATOM | 1667 | CG  | ASN | A | 452 | 0.880  | 31.817 | 7.474  | 1.00 | 27.72 |
| ATOM | 1668 | OD1 | ASN | A | 452 | 0.909  | 32.212 | 6.306  | 1.00 | 26.46 |
| ATOM | 1669 | ND2 | ASN | A | 452 | 1.069  | 32.625 | 8.514  | 1.00 | 27.38 |
| ATOM | 1670 | C   | ASN | A | 452 | -1.265 | 28.771 | 7.306  | 1.00 | 22.53 |
| ATOM | 1671 | O   | ASN | A | 452 | -1.618 | 28.703 | 6.142  | 1.00 | 21.28 |
| ATOM | 1672 | N   | LEU | A | 453 | -1.185 | 27.714 | 8.106  | 1.00 | 23.33 |
| ATOM | 1673 | CA  | LEU | A | 453 | -1.535 | 26.373 | 7.664  | 1.00 | 23.75 |
| ATOM | 1674 | CB  | LEU | A | 453 | -1.116 | 25.329 | 8.684  | 1.00 | 25.73 |
| ATOM | 1675 | CG  | LEU | A | 453 | 0.367  | 24.976 | 8.721  | 1.00 | 27.47 |
| ATOM | 1676 | CD1 | LEU | A | 453 | 0.502  | 23.702 | 9.537  | 1.00 | 29.93 |
| ATOM | 1677 | CD2 | LEU | A | 453 | 0.914  | 24.758 | 7.316  | 1.00 | 26.92 |
| ATOM | 1678 | C   | LEU | A | 453 | -3.021 | 26.249 | 7.385  | 1.00 | 24.14 |
| ATOM | 1679 | O   | LEU | A | 453 | -3.422 | 25.497 | 6.495  | 1.00 | 24.19 |
| ATOM | 1680 | N   | GLU | A | 454 | -3.842 | 26.955 | 8.164  | 1.00 | 24.78 |
| ATOM | 1681 | CA  | GLU | A | 454 | -5.295 | 26.970 | 7.932  | 1.00 | 25.31 |
| ATOM | 1682 | CB  | GLU | A | 454 | -5.999 | 27.941 | 8.858  | 1.00 | 27.19 |
| ATOM | 1683 | CG  | GLU | A | 454 | -6.253 | 27.449 | 10.234 | 1.00 | 34.82 |
| ATOM | 1684 | CD  | GLU | A | 454 | -6.585 | 28.595 | 11.176 | 1.00 | 39.79 |
| ATOM | 1685 | OE1 | GLU | A | 454 | -6.773 | 28.337 | 12.387 | 1.00 | 41.52 |
| ATOM | 1686 | OE2 | GLU | A | 454 | -6.636 | 29.760 | 10.707 | 1.00 | 43.60 |
| ATOM | 1687 | C   | GLU | A | 454 | -5.521 | 27.489 | 6.517  | 1.00 | 23.43 |
| ATOM | 1688 | O   | GLU | A | 454 | -6.365 | 26.992 | 5.786  | 1.00 | 23.28 |
| ATOM | 1689 | N   | ARG | A | 455 | -4.744 | 28.502 | 6.152  | 1.00 | 22.10 |
| ATOM | 1690 | CA  | ARG | A | 455 | -4.813 | 29.102 | 4.832  | 1.00 | 20.47 |
| ATOM | 1691 | CB  | ARG | A | 455 | -4.363 | 30.559 | 4.924  | 1.00 | 21.16 |
| ATOM | 1692 | CG  | ARG | A | 455 | -5.254 | 31.404 | 5.814  | 1.00 | 21.71 |
| ATOM | 1693 | CD  | ARG | A | 455 | -4.919 | 32.868 | 5.689  | 1.00 | 24.13 |
| ATOM | 1694 | NE  | ARG | A | 455 | -3.522 | 33.100 | 6.021  | 1.00 | 29.30 |
| ATOM | 1695 | CZ  | ARG | A | 455 | -3.098 | 33.940 | 6.960  | 1.00 | 30.32 |
| ATOM | 1696 | NH1 | ARG | A | 455 | -3.964 | 34.639 | 7.679  | 1.00 | 32.30 |
| ATOM | 1697 | NH2 | ARG | A | 455 | -1.800 | 34.086 | 7.169  | 1.00 | 30.29 |
| ATOM | 1698 | C   | ARG | A | 455 | -4.037 | 28.332 | 3.764  | 1.00 | 18.90 |

Figure 7

```
ATOM   1699  O    ARG A 455      -3.925  28.788   2.637  1.00 18.49
ATOM   1700  N    GLY A 456      -3.531  27.152   4.129  1.00 19.76
ATOM   1701  CA   GLY A 456      -2.777  26.282   3.231  1.00 17.61
ATOM   1702  C    GLY A 456      -1.361  26.693   2.863  1.00 18.03
ATOM   1703  O    GLY A 456      -0.840  26.292   1.828  1.00 16.65
ATOM   1704  N    TYR A 457      -0.728  27.490   3.713  1.00 19.32
ATOM   1705  CA   TYR A 457       0.628  27.972   3.479  1.00 19.80
ATOM   1706  CB   TYR A 457       1.026  28.969   4.581  1.00 19.83
ATOM   1707  CG   TYR A 457       2.440  29.526   4.467  1.00 20.00
ATOM   1708  CD1  TYR A 457       2.691  30.722   3.774  1.00 18.86
ATOM   1709  CE1  TYR A 457       3.962  31.258   3.709  1.00 19.39
ATOM   1710  CD2  TYR A 457       3.526  28.887   5.088  1.00 18.88
ATOM   1711  CE2  TYR A 457       4.815  29.424   5.019  1.00 18.89
ATOM   1712  CZ   TYR A 457       5.017  30.610   4.325  1.00 19.66
ATOM   1713  OH   TYR A 457       6.271  31.153   4.215  1.00 20.18
ATOM   1714  C    TYR A 457       1.667  26.864   3.429  1.00 19.81
ATOM   1715  O    TYR A 457       1.611  25.911   4.211  1.00 20.73
ATOM   1716  N    ARG A 458       2.631  27.030   2.524  1.00 20.05
ATOM   1717  CA   ARG A 458       3.746  26.108   2.372  1.00 20.32
ATOM   1718  CB   ARG A 458       3.589  25.218   1.130  1.00 17.80
ATOM   1719  CG   ARG A 458       2.379  24.312   1.123  1.00 16.80
ATOM   1720  CD   ARG A 458       2.357  23.409   2.326  1.00 16.76
ATOM   1721  NE   ARG A 458       1.300  22.413   2.233  1.00 15.01
ATOM   1722  CZ   ARG A 458       0.198  22.418   2.968  1.00 13.99
ATOM   1723  NH1  ARG A 458      -0.002  23.373   3.856  1.00 17.15
ATOM   1724  NH2  ARG A 458      -0.683  21.445   2.843  1.00 13.35
ATOM   1725  C    ARG A 458       5.031  26.947   2.232  1.00 21.34
ATOM   1726  O    ARG A 458       5.036  27.968   1.539  1.00 22.17
ATOM   1727  N    MET A 459       6.085  26.551   2.949  1.00 22.35
ATOM   1728  CA   MET A 459       7.386  27.221   2.884  1.00 21.36
ATOM   1729  CB   MET A 459       8.447  26.468   3.713  1.00 21.07
ATOM   1730  CG   MET A 459       8.397  26.652   5.219  1.00 23.83
ATOM   1731  SD   MET A 459       9.793  25.850   6.099  1.00 24.52
ATOM   1732  CE   MET A 459       9.179  24.219   6.311  1.00 23.82
ATOM   1733  C    MET A 459       7.872  27.208   1.442  1.00 21.55
ATOM   1734  O    MET A 459       7.588  26.267   0.684  1.00 19.62
ATOM   1735  N    VAL A 460       8.643  28.238   1.089  1.00 22.33
ATOM   1736  CA   VAL A 460       9.234  28.358  -0.241  1.00 22.60
ATOM   1737  CB   VAL A 460       9.480  29.848  -0.621  1.00 22.54
ATOM   1738  CG1  VAL A 460       8.182  30.589  -0.549  1.00 22.19
ATOM   1739  CG2  VAL A 460      10.518  30.489   0.303  1.00 21.05
ATOM   1740  C    VAL A 460      10.543  27.553  -0.273  1.00 22.85
ATOM   1741  O    VAL A 460      11.028  27.110   0.770  1.00 22.17
ATOM   1742  N    ARG A 461      11.087  27.333  -1.468  1.00 23.74
ATOM   1743  CA   ARG A 461      12.330  26.570  -1.634  1.00 25.84
ATOM   1744  CB   ARG A 461      12.716  26.495  -3.125  1.00 27.15
ATOM   1745  CG   ARG A 461      13.874  25.541  -3.460  1.00 30.66
ATOM   1746  CD   ARG A 461      14.277  25.582  -4.953  1.00 35.10
ATOM   1747  NE   ARG A 461      14.737  26.914  -5.320  1.00 42.71
ATOM   1748  CZ   ARG A 461      15.864  27.472  -4.866  1.00 48.26
ATOM   1749  NH1  ARG A 461      16.681  26.804  -4.048  1.00 49.64
ATOM   1750  NH2  ARG A 461      16.105  28.758  -5.101  1.00 50.48
ATOM   1751  C    ARG A 461      13.451  27.233  -0.834  1.00 26.79
ATOM   1752  O    ARG A 461      13.719  28.430  -0.983  1.00 27.17
ATOM   1753  N    PRO A 462      14.092  26.478   0.064  1.00 27.70
ATOM   1754  CD   PRO A 462      13.825  25.091   0.474  1.00 27.55
ATOM   1755  CA   PRO A 462      15.177  27.062   0.857  1.00 29.16
ATOM   1756  CB   PRO A 462      15.553  25.921   1.812  1.00 27.82
ATOM   1757  CG   PRO A 462      14.279  25.102   1.907  1.00 27.46
```

Figure 7

| | | | | | | | | | |
|---|---|---|---|---|---|---|---|---|---|
| ATOM | 1758 | C | PRO | A | 462 | 16.363 | 27.438 | -0.033 | 1.00 31.54 |
| ATOM | 1759 | O | PRO | A | 462 | 16.566 | 26.840 | -1.091 | 1.00 31.21 |
| ATOM | 1760 | N | ASP | A | 463 | 17.129 | 28.446 | 0.379 | 1.00 35.19 |
| ATOM | 1761 | CA | ASP | A | 463 | 18.312 | 28.846 | -0.384 | 1.00 37.55 |
| ATOM | 1762 | CB | ASP | A | 463 | 19.082 | 29.972 | 0.323 | 1.00 38.42 |
| ATOM | 1763 | CG | ASP | A | 463 | 18.384 | 31.318 | 0.237 | 1.00 41.02 |
| ATOM | 1764 | OD1 | ASP | A | 463 | 17.488 | 31.490 | -0.627 | 1.00 42.59 |
| ATOM | 1765 | OD2 | ASP | A | 463 | 18.745 | 32.216 | 1.034 | 1.00 41.48 |
| ATOM | 1766 | C | ASP | A | 463 | 19.217 | 27.624 | -0.458 | 1.00 38.32 |
| ATOM | 1767 | O | ASP | A | 463 | 19.389 | 26.907 | 0.537 | 1.00 38.59 |
| ATOM | 1768 | N | ASN | A | 464 | 19.748 | 27.367 | -1.652 | 1.00 39.95 |
| ATOM | 1769 | CA | ASN | A | 464 | 20.663 | 26.246 | -1.884 | 1.00 40.16 |
| ATOM | 1770 | CB | ASN | A | 464 | 21.923 | 26.421 | -1.018 | 1.00 41.59 |
| ATOM | 1771 | CG | ASN | A | 464 | 22.656 | 27.745 | -1.310 | 1.00 43.31 |
| ATOM | 1772 | OD1 | ASN | A | 464 | 23.150 | 27.955 | -2.420 | 1.00 44.40 |
| ATOM | 1773 | ND2 | ASN | A | 464 | 22.697 | 28.647 | -0.325 | 1.00 42.62 |
| ATOM | 1774 | C | ASN | A | 464 | 19.995 | 24.878 | -1.670 | 1.00 39.13 |
| ATOM | 1775 | O | ASN | A | 464 | 20.490 | 24.013 | -0.933 | 1.00 40.37 |
| ATOM | 1776 | N | CYS | A | 465 | 18.856 | 24.712 | -2.333 | 1.00 36.02 |
| ATOM | 1777 | CA | CYS | A | 465 | 18.065 | 23.486 | -2.285 | 1.00 33.53 |
| ATOM | 1778 | CB | CYS | A | 465 | 16.798 | 23.699 | -1.425 | 1.00 31.66 |
| ATOM | 1779 | SG | CYS | A | 465 | 15.532 | 22.370 | -1.431 | 1.00 27.31 |
| ATOM | 1780 | C | CYS | A | 465 | 17.667 | 23.158 | -3.730 | 1.00 32.12 |
| ATOM | 1781 | O | CYS | A | 465 | 17.150 | 24.012 | -4.445 | 1.00 32.77 |
| ATOM | 1782 | N | PRO | A | 466 | 17.989 | 21.943 | -4.201 | 1.00 30.61 |
| ATOM | 1783 | CD | PRO | A | 466 | 18.707 | 20.856 | -3.501 | 1.00 29.34 |
| ATOM | 1784 | CA | PRO | A | 466 | 17.626 | 21.558 | -5.570 | 1.00 28.94 |
| ATOM | 1785 | CB | PRO | A | 466 | 17.970 | 20.070 | -5.602 | 1.00 27.67 |
| ATOM | 1786 | CG | PRO | A | 466 | 19.108 | 19.956 | -4.642 | 1.00 29.64 |
| ATOM | 1787 | C | PRO | A | 466 | 16.118 | 21.751 | -5.769 | 1.00 28.75 |
| ATOM | 1788 | O | PRO | A | 466 | 15.352 | 21.636 | -4.809 | 1.00 28.67 |
| ATOM | 1789 | N | GLU | A | 467 | 15.696 | 22.074 | -6.992 | 1.00 29.10 |
| ATOM | 1790 | CA | GLU | A | 467 | 14.281 | 22.258 | -7.280 | 1.00 28.33 |
| ATOM | 1791 | CB | GLU | A | 467 | 14.070 | 22.776 | -8.698 | 1.00 29.19 |
| ATOM | 1792 | CG | GLU | A | 467 | 13.302 | 24.097 | -8.767 | 1.00 34.76 |
| ATOM | 1793 | CD | GLU | A | 467 | 11.949 | 24.080 | -8.042 | 1.00 35.38 |
| ATOM | 1794 | OE1 | GLU | A | 467 | 11.779 | 24.866 | -7.089 | 1.00 38.09 |
| ATOM | 1795 | OE2 | GLU | A | 467 | 11.042 | 23.328 | -8.445 | 1.00 36.11 |
| ATOM | 1796 | C | GLU | A | 467 | 13.575 | 20.927 | -7.150 | 1.00 28.54 |
| ATOM | 1797 | O | GLU | A | 467 | 12.416 | 20.864 | -6.757 | 1.00 29.69 |
| ATOM | 1798 | N | GLU | A | 468 | 14.292 | 19.855 | -7.467 | 1.00 28.29 |
| ATOM | 1799 | CA | GLU | A | 468 | 13.738 | 18.505 | -7.401 | 1.00 28.64 |
| ATOM | 1800 | CB | GLU | A | 468 | 14.660 | 17.509 | -8.112 | 1.00 32.06 |
| ATOM | 1801 | CG | GLU | A | 468 | 15.001 | 17.867 | -9.565 | 1.00 37.29 |
| ATOM | 1802 | CD | GLU | A | 468 | 15.931 | 19.084 | -9.681 | 1.00 41.42 |
| ATOM | 1803 | OE1 | GLU | A | 468 | 16.913 | 19.187 | -8.894 | 1.00 40.45 |
| ATOM | 1804 | OE2 | GLU | A | 468 | 15.660 | 19.947 | -10.553 | 1.00 43.36 |
| ATOM | 1805 | C | GLU | A | 468 | 13.477 | 18.053 | -5.964 | 1.00 27.04 |
| ATOM | 1806 | O | GLU | A | 468 | 12.503 | 17.333 | -5.718 | 1.00 27.45 |
| ATOM | 1807 | N | LEU | A | 469 | 14.358 | 18.442 | -5.032 | 1.00 23.96 |
| ATOM | 1808 | CA | LEU | A | 469 | 14.192 | 18.111 | -3.617 | 1.00 22.03 |
| ATOM | 1809 | CB | LEU | A | 469 | 15.479 | 18.402 | -2.835 | 1.00 20.18 |
| ATOM | 1810 | CG | LEU | A | 469 | 15.506 | 18.064 | -1.335 | 1.00 20.14 |
| ATOM | 1811 | CD1 | LEU | A | 469 | 15.376 | 16.579 | -1.116 | 1.00 19.00 |
| ATOM | 1812 | CD2 | LEU | A | 469 | 16.788 | 18.538 | -0.727 | 1.00 19.37 |
| ATOM | 1813 | C | LEU | A | 469 | 13.022 | 18.938 | -3.052 | 1.00 21.76 |
| ATOM | 1814 | O | LEU | A | 469 | 12.247 | 18.471 | -2.217 | 1.00 21.22 |
| ATOM | 1815 | N | TYR | A | 470 | 12.906 | 20.178 | -3.513 | 1.00 21.37 |
| ATOM | 1816 | CA | TYR | A | 470 | 11.814 | 21.018 | -3.071 | 1.00 21.56 |

Figure 7

| | | | | | | | | | |
|---|---|---|---|---|---|---|---|---|---|
| ATOM | 1817 | CB | TYR | A | 470 | 11.934 | 22.438 | -3.608 | 1.00 20.22 |
| ATOM | 1818 | CG | TYR | A | 470 | 10.784 | 23.296 | -3.150 | 1.00 19.98 |
| ATOM | 1819 | CD1 | TYR | A | 470 | 10.512 | 23.468 | -1.790 | 1.00 18.82 |
| ATOM | 1820 | CE1 | TYR | A | 470 | 9.449 | 24.249 | -1.365 | 1.00 18.64 |
| ATOM | 1821 | CD2 | TYR | A | 470 | 9.958 | 23.923 | -4.066 | 1.00 19.74 |
| ATOM | 1822 | CE2 | TYR | A | 470 | 8.885 | 24.712 | -3.648 | 1.00 19.69 |
| ATOM | 1823 | CZ | TYR | A | 470 | 8.640 | 24.872 | -2.302 | 1.00 18.16 |
| ATOM | 1824 | OH | TYR | A | 470 | 7.604 | 25.679 | -1.894 | 1.00 18.23 |
| ATOM | 1825 | C | TYR | A | 470 | 10.459 | 20.420 | -3.458 | 1.00 21.34 |
| ATOM | 1826 | O | TYR | A | 470 | 9.533 | 20.423 | -2.656 | 1.00 23.07 |
| ATOM | 1827 | N | GLN | A | 471 | 10.341 | 19.921 | -4.682 | 1.00 21.47 |
| ATOM | 1828 | CA | GLN | A | 471 | 9.094 | 19.297 | -5.118 | 1.00 22.41 |
| ATOM | 1829 | CB | GLN | A | 471 | 9.142 | 18.950 | -6.611 | 1.00 23.79 |
| ATOM | 1830 | CG | GLN | A | 471 | 9.115 | 20.179 | -7.521 | 1.00 25.72 |
| ATOM | 1831 | CD | GLN | A | 471 | 7.991 | 21.141 | -7.163 | 1.00 26.89 |
| ATOM | 1832 | OE1 | GLN | A | 471 | 6.901 | 20.717 | -6.777 | 1.00 28.62 |
| ATOM | 1833 | NE2 | GLN | A | 471 | 8.258 | 22.443 | -7.267 | 1.00 24.65 |
| ATOM | 1834 | C | GLN | A | 471 | 8.804 | 18.046 | -4.285 | 1.00 22.35 |
| ATOM | 1835 | O | GLN | A | 471 | 7.643 | 17.666 | -4.096 | 1.00 21.60 |
| ATOM | 1836 | N | LEU | A | 472 | 9.862 | 17.442 | -3.748 | 1.00 21.90 |
| ATOM | 1837 | CA | LEU | A | 472 | 9.714 | 16.260 | -2.917 | 1.00 21.92 |
| ATOM | 1838 | CB | LEU | A | 472 | 11.066 | 15.608 | -2.668 | 1.00 22.34 |
| ATOM | 1839 | CG | LEU | A | 472 | 11.082 | 14.082 | -2.609 | 1.00 24.46 |
| ATOM | 1840 | CD1 | LEU | A | 472 | 10.537 | 13.492 | -3.920 | 1.00 24.06 |
| ATOM | 1841 | CD2 | LEU | A | 472 | 12.509 | 13.610 | -2.371 | 1.00 24.39 |
| ATOM | 1842 | C | LEU | A | 472 | 9.076 | 16.690 | -1.603 | 1.00 21.61 |
| ATOM | 1843 | O | LEU | A | 472 | 8.203 | 15.999 | -1.077 | 1.00 21.67 |
| ATOM | 1844 | N | MET | A | 473 | 9.485 | 17.860 | -1.111 | 1.00 21.02 |
| ATOM | 1845 | CA | MET | A | 473 | 8.944 | 18.422 | 0.127 | 1.00 20.21 |
| ATOM | 1846 | CB | MET | A | 473 | 9.669 | 19.717 | 0.484 | 1.00 20.05 |
| ATOM | 1847 | CG | MET | A | 473 | 11.169 | 19.546 | 0.715 | 1.00 20.41 |
| ATOM | 1848 | SD | MET | A | 473 | 11.968 | 21.141 | 0.834 | 1.00 20.97 |
| ATOM | 1849 | CE | MET | A | 473 | 13.589 | 20.641 | 1.396 | 1.00 17.90 |
| ATOM | 1850 | C | MET | A | 473 | 7.472 | 18.720 | -0.084 | 1.00 19.88 |
| ATOM | 1851 | O | MET | A | 473 | 6.629 | 18.370 | 0.730 | 1.00 19.27 |
| ATOM | 1852 | N | ARG | A | 474 | 7.166 | 19.343 | -1.209 | 1.00 20.70 |
| ATOM | 1853 | CA | ARG | A | 474 | 5.789 | 19.687 | -1.549 | 1.00 21.39 |
| ATOM | 1854 | CB | ARG | A | 474 | 5.739 | 20.439 | -2.886 | 1.00 20.92 |
| ATOM | 1855 | CG | ARG | A | 474 | 6.442 | 21.798 | -2.820 | 1.00 21.53 |
| ATOM | 1856 | CD | ARG | A | 474 | 5.893 | 22.643 | -1.671 | 1.00 24.24 |
| ATOM | 1857 | NE | ARG | A | 474 | 4.459 | 22.915 | -1.839 | 1.00 25.95 |
| ATOM | 1858 | CZ | ARG | A | 474 | 3.945 | 24.006 | -2.414 | 1.00 25.78 |
| ATOM | 1859 | NH1 | ARG | A | 474 | 4.731 | 24.966 | -2.883 | 1.00 23.57 |
| ATOM | 1860 | NH2 | ARG | A | 474 | 2.635 | 24.103 | -2.582 | 1.00 26.33 |
| ATOM | 1861 | C | ARG | A | 474 | 4.866 | 18.470 | -1.545 | 1.00 20.44 |
| ATOM | 1862 | O | ARG | A | 474 | 3.700 | 18.578 | -1.174 | 1.00 20.96 |
| ATOM | 1863 | N | LEU | A | 475 | 5.396 | 17.316 | -1.954 | 1.00 21.07 |
| ATOM | 1864 | CA | LEU | A | 475 | 4.637 | 16.063 | -1.957 | 1.00 19.17 |
| ATOM | 1865 | CB | LEU | A | 475 | 5.367 | 14.981 | -2.751 | 1.00 19.34 |
| ATOM | 1866 | CG | LEU | A | 475 | 5.345 | 15.105 | -4.266 | 1.00 19.39 |
| ATOM | 1867 | CD1 | LEU | A | 475 | 6.086 | 13.930 | -4.866 | 1.00 18.39 |
| ATOM | 1868 | CD2 | LEU | A | 475 | 3.910 | 15.152 | -4.762 | 1.00 19.29 |
| ATOM | 1869 | C | LEU | A | 475 | 4.421 | 15.589 | -0.524 | 1.00 18.60 |
| ATOM | 1870 | O | LEU | A | 475 | 3.379 | 15.048 | -0.199 | 1.00 18.12 |
| ATOM | 1871 | N | CYS | A | 476 | 5.418 | 15.805 | 0.329 | 1.00 18.39 |
| ATOM | 1872 | CA | CYS | A | 476 | 5.332 | 15.435 | 1.738 | 1.00 18.26 |
| ATOM | 1873 | CB | CYS | A | 476 | 6.692 | 15.579 | 2.436 | 1.00 18.52 |
| ATOM | 1874 | SG | CYS | A | 476 | 7.908 | 14.375 | 1.924 | 1.00 19.89 |
| ATOM | 1875 | C | CYS | A | 476 | 4.336 | 16.326 | 2.449 | 1.00 18.12 |

Figure 7

```
ATOM   1876  O    CYS A 476       3.780  15.938   3.487  1.00 18.06
ATOM   1877  N    TRP A 477       4.117  17.522   1.895  1.00 17.84
ATOM   1878  CA   TRP A 477       3.195  18.482   2.496  1.00 17.38
ATOM   1879  CB   TRP A 477       3.780  19.889   2.496  1.00 16.58
ATOM   1880  CG   TRP A 477       5.084  20.025   3.197  1.00 16.44
ATOM   1881  CD2  TRP A 477       6.105  20.972   2.895  1.00 17.51
ATOM   1882  CE2  TRP A 477       7.191  20.696   3.753  1.00 17.68
ATOM   1883  CE3  TRP A 477       6.213  22.033   1.973  1.00 18.85
ATOM   1884  CD1  TRP A 477       5.572  19.242   4.213  1.00 15.59
ATOM   1885  NE1  TRP A 477       6.832  19.631   4.540  1.00 14.02
ATOM   1886  CZ2  TRP A 477       8.384  21.445   3.721  1.00 18.96
ATOM   1887  CZ3  TRP A 477       7.389  22.775   1.937  1.00 20.06
ATOM   1888  CH2  TRP A 477       8.464  22.474   2.810  1.00 20.77
ATOM   1889  C    TRP A 477       1.822  18.536   1.865  1.00 17.90
ATOM   1890  O    TRP A 477       1.097  19.506   2.050  1.00 19.42
ATOM   1891  N    LYS A 478       1.454  17.520   1.102  1.00 19.18
ATOM   1892  CA   LYS A 478       0.123  17.502   0.512  1.00 19.92
ATOM   1893  CB   LYS A 478      -0.066  16.254  -0.343  1.00 20.72
ATOM   1894  CG   LYS A 478       0.756  16.295  -1.611  1.00 24.02
ATOM   1895  CD   LYS A 478       0.353  17.459  -2.484  1.00 26.14
ATOM   1896  CE   LYS A 478      -1.004  17.210  -3.109  1.00 28.41
ATOM   1897  NZ   LYS A 478      -1.409  18.347  -3.993  1.00 33.77
ATOM   1898  C    LYS A 478      -0.883  17.555   1.647  1.00 20.45
ATOM   1899  O    LYS A 478      -0.693  16.927   2.687  1.00 20.77
ATOM   1900  N    GLU A 479      -1.920  18.367   1.473  1.00 21.45
ATOM   1901  CA   GLU A 479      -2.963  18.539   2.492  1.00 22.63
ATOM   1902  CB   GLU A 479      -4.059  19.460   1.937  1.00 23.30
ATOM   1903  CG   GLU A 479      -5.010  19.999   2.992  1.00 23.07
ATOM   1904  CD   GLU A 479      -4.313  20.827   4.042  1.00 22.19
ATOM   1905  OE1  GLU A 479      -3.413  21.616   3.700  1.00 25.66
ATOM   1906  OE2  GLU A 479      -4.663  20.691   5.216  1.00 20.22
ATOM   1907  C    GLU A 479      -3.562  17.208   2.952  1.00 21.37
ATOM   1908  O    GLU A 479      -3.684  16.932   4.151  1.00 21.32
ATOM   1909  N    ARG A 480      -3.964  16.409   1.972  1.00 20.93
ATOM   1910  CA   ARG A 480      -4.535  15.091   2.214  1.00 21.60
ATOM   1911  CB   ARG A 480      -5.373  14.657   1.027  1.00 24.15
ATOM   1912  CG   ARG A 480      -6.614  15.438   0.806  1.00 27.36
ATOM   1913  CD   ARG A 480      -7.207  14.860  -0.422  1.00 32.80
ATOM   1914  NE   ARG A 480      -8.419  15.536  -0.827  1.00 38.93
ATOM   1915  CZ   ARG A 480      -8.698  15.836  -2.088  1.00 42.91
ATOM   1916  NH1  ARG A 480      -7.834  15.526  -3.063  1.00 43.74
ATOM   1917  NH2  ARG A 480      -9.864  16.405  -2.377  1.00 44.87
ATOM   1918  C    ARG A 480      -3.451  14.040   2.420  1.00 20.11
ATOM   1919  O    ARG A 480      -2.605  13.843   1.539  1.00 19.83
ATOM   1920  N    PRO A 481      -3.506  13.304   3.554  1.00 19.01
ATOM   1921  CD   PRO A 481      -4.573  13.396   4.565  1.00 16.99
ATOM   1922  CA   PRO A 481      -2.550  12.255   3.919  1.00 18.17
ATOM   1923  CB   PRO A 481      -3.236  11.577   5.105  1.00 18.32
ATOM   1924  CG   PRO A 481      -3.990  12.669   5.720  1.00 17.28
ATOM   1925  C    PRO A 481      -2.280  11.256   2.801  1.00 19.05
ATOM   1926  O    PRO A 481      -1.141  10.885   2.567  1.00 19.08
ATOM   1927  N    GLU A 482      -3.332  10.862   2.079  1.00 19.81
ATOM   1928  CA   GLU A 482      -3.221   9.890   0.982  1.00 19.03
ATOM   1929  CB   GLU A 482      -4.622   9.465   0.486  1.00 19.36
ATOM   1930  CG   GLU A 482      -5.405  10.559  -0.260  1.00 19.58
ATOM   1931  CD   GLU A 482      -6.459  11.268   0.583  1.00 20.79
ATOM   1932  OE1  GLU A 482      -6.312  11.348   1.821  1.00 21.48
ATOM   1933  OE2  GLU A 482      -7.449  11.756  -0.002  1.00 23.57
ATOM   1934  C    GLU A 482      -2.377  10.364  -0.196  1.00 18.52
```

Figure 7

| | | | | | | | | | |
|---|---|---|---|---|---|---|---|---|---|
| ATOM | 1935 | O | GLU | A | 482 | -1.824 | 9.550 | -0.932 | 1.00 19.30 |
| ATOM | 1936 | N | ASP | A | 483 | -2.263 | 11.678 | -0.374 | 1.00 19.42 |
| ATOM | 1937 | CA | ASP | A | 483 | -1.496 | 12.239 | -1.490 | 1.00 19.45 |
| ATOM | 1938 | CB | ASP | A | 483 | -2.087 | 13.590 | -1.919 | 1.00 20.82 |
| ATOM | 1939 | CG | ASP | A | 483 | -3.532 | 13.482 | -2.421 | 1.00 21.00 |
| ATOM | 1940 | OD1 | ASP | A | 483 | -3.901 | 12.460 | -3.040 | 1.00 21.68 |
| ATOM | 1941 | OD2 | ASP | A | 483 | -4.299 | 14.441 | -2.208 | 1.00 20.29 |
| ATOM | 1942 | C | ASP | A | 483 | 0.006 | 12.364 | -1.234 | 1.00 19.18 |
| ATOM | 1943 | O | ASP | A | 483 | 0.769 | 12.675 | -2.146 | 1.00 19.37 |
| ATOM | 1944 | N | ARG | A | 484 | 0.417 | 12.135 | 0.016 | 1.00 19.83 |
| ATOM | 1945 | CA | ARG | A | 484 | 1.828 | 12.176 | 0.437 | 1.00 19.43 |
| ATOM | 1946 | CB | ARG | A | 484 | 1.906 | 12.401 | 1.944 | 1.00 18.64 |
| ATOM | 1947 | CG | ARG | A | 484 | 1.142 | 13.610 | 2.367 | 1.00 16.31 |
| ATOM | 1948 | CD | ARG | A | 484 | 1.145 | 13.761 | 3.865 | 1.00 17.90 |
| ATOM | 1949 | NE | ARG | A | 484 | 0.255 | 14.855 | 4.224 | 1.00 16.34 |
| ATOM | 1950 | CZ | ARG | A | 484 | -0.304 | 15.018 | 5.412 | 1.00 14.56 |
| ATOM | 1951 | NH1 | ARG | A | 484 | -0.052 | 14.160 | 6.384 | 1.00 13.08 |
| ATOM | 1952 | NH2 | ARG | A | 484 | -1.168 | 16.008 | 5.593 | 1.00 15.27 |
| ATOM | 1953 | C | ARG | A | 484 | 2.497 | 10.839 | 0.076 | 1.00 18.60 |
| ATOM | 1954 | O | ARG | A | 484 | 1.877 | 9.779 | 0.232 | 1.00 19.10 |
| ATOM | 1955 | N | PRO | A | 485 | 3.776 | 10.866 | -0.361 | 1.00 18.02 |
| ATOM | 1956 | CD | PRO | A | 485 | 4.676 | 12.024 | -0.357 | 1.00 17.21 |
| ATOM | 1957 | CA | PRO | A | 485 | 4.506 | 9.649 | -0.745 | 1.00 18.23 |
| ATOM | 1958 | CB | PRO | A | 485 | 5.847 | 10.193 | -1.261 | 1.00 18.92 |
| ATOM | 1959 | CG | PRO | A | 485 | 5.633 | 11.667 | -1.435 | 1.00 20.11 |
| ATOM | 1960 | C | PRO | A | 485 | 4.780 | 8.674 | 0.397 | 1.00 18.67 |
| ATOM | 1961 | O | PRO | A | 485 | 4.711 | 9.046 | 1.566 | 1.00 19.70 |
| ATOM | 1962 | N | THR | A | 486 | 5.077 | 7.421 | 0.061 | 1.00 18.49 |
| ATOM | 1963 | CA | THR | A | 486 | 5.443 | 6.457 | 1.093 | 1.00 19.61 |
| ATOM | 1964 | CB | THR | A | 486 | 5.319 | 4.998 | 0.618 | 1.00 15.75 |
| ATOM | 1965 | OG1 | THR | A | 486 | 6.117 | 4.805 | -0.553 | 1.00 17.13 |
| ATOM | 1966 | CG2 | THR | A | 486 | 3.889 | 4.657 | 0.327 | 1.00 17.81 |
| ATOM | 1967 | C | THR | A | 486 | 6.916 | 6.722 | 1.395 | 1.00 20.70 |
| ATOM | 1968 | O | THR | A | 486 | 7.593 | 7.415 | 0.628 | 1.00 21.74 |
| ATOM | 1969 | N | PHE | A | 487 | 7.402 | 6.230 | 2.532 | 1.00 21.86 |
| ATOM | 1970 | CA | PHE | A | 487 | 8.820 | 6.387 | 2.885 | 1.00 21.98 |
| ATOM | 1971 | CB | PHE | A | 487 | 9.049 | 6.102 | 4.371 | 1.00 19.91 |
| ATOM | 1972 | CG | PHE | A | 487 | 8.752 | 7.268 | 5.269 | 1.00 17.00 |
| ATOM | 1973 | CD1 | PHE | A | 487 | 9.585 | 8.380 | 5.283 | 1.00 15.77 |
| ATOM | 1974 | CD2 | PHE | A | 487 | 7.669 | 7.233 | 6.143 | 1.00 17.81 |
| ATOM | 1975 | CE1 | PHE | A | 487 | 9.351 | 9.431 | 6.153 | 1.00 12.97 |
| ATOM | 1976 | CE2 | PHE | A | 487 | 7.427 | 8.293 | 7.028 | 1.00 15.82 |
| ATOM | 1977 | CZ | PHE | A | 487 | 8.268 | 9.385 | 7.030 | 1.00 14.71 |
| ATOM | 1978 | C | PHE | A | 487 | 9.671 | 5.450 | 2.012 | 1.00 21.84 |
| ATOM | 1979 | O | PHE | A | 487 | 10.866 | 5.670 | 1.839 | 1.00 22.90 |
| ATOM | 1980 | N | ASP | A | 488 | 9.027 | 4.429 | 1.445 | 1.00 22.56 |
| ATOM | 1981 | CA | ASP | A | 488 | 9.678 | 3.477 | 0.550 | 1.00 23.66 |
| ATOM | 1982 | CB | ASP | A | 488 | 8.745 | 2.292 | 0.271 | 1.00 26.52 |
| ATOM | 1983 | CG | ASP | A | 488 | 9.342 | 1.284 | -0.708 | 1.00 31.61 |
| ATOM | 1984 | OD1 | ASP | A | 488 | 10.455 | 0.774 | -0.450 | 1.00 34.49 |
| ATOM | 1985 | OD2 | ASP | A | 488 | 8.695 | 1.000 | -1.740 | 1.00 32.74 |
| ATOM | 1986 | C | ASP | A | 488 | 10.020 | 4.227 | -0.741 | 1.00 23.30 |
| ATOM | 1987 | O | ASP | A | 488 | 11.093 | 4.042 | -1.319 | 1.00 24.31 |
| ATOM | 1988 | N | TYR | A | 489 | 9.109 | 5.084 | -1.186 | 1.00 21.72 |
| ATOM | 1989 | CA | TYR | A | 489 | 9.351 | 5.897 | -2.370 | 1.00 20.81 |
| ATOM | 1990 | CB | TYR | A | 489 | 8.071 | 6.583 | -2.845 | 1.00 21.35 |
| ATOM | 1991 | CG | TYR | A | 489 | 8.330 | 7.649 | -3.882 | 1.00 22.54 |
| ATOM | 1992 | CD1 | TYR | A | 489 | 8.616 | 7.309 | -5.213 | 1.00 23.03 |
| ATOM | 1993 | CE1 | TYR | A | 489 | 8.860 | 8.283 | -6.166 | 1.00 22.71 |

Figure 7

| | | | | | | | | | |
|---|---|---|---|---|---|---|---|---|---|
| ATOM | 1994 | CD2 | TYR | A | 489 | 8.302 | 8.998 | -3.533 | 1.00 22.63 |
| ATOM | 1995 | CE2 | TYR | A | 489 | 8.549 | 9.983 | -4.473 | 1.00 22.59 |
| ATOM | 1996 | CZ | TYR | A | 489 | 8.824 | 9.622 | -5.789 | 1.00 24.94 |
| ATOM | 1997 | OH | TYR | A | 489 | 9.032 | 10.611 | -6.731 | 1.00 26.84 |
| ATOM | 1998 | C | TYR | A | 489 | 10.387 | 6.959 | -2.057 | 1.00 20.19 |
| ATOM | 1999 | O | TYR | A | 489 | 11.285 | 7.195 | -2.850 | 1.00 20.63 |
| ATOM | 2000 | N | LEU | A | 490 | 10.217 | 7.633 | -0.920 | 1.00 20.58 |
| ATOM | 2001 | CA | LEU | A | 490 | 11.134 | 8.682 | -0.481 | 1.00 21.78 |
| ATOM | 2002 | CB | LEU | A | 490 | 10.681 | 9.273 | 0.858 | 1.00 20.74 |
| ATOM | 2003 | CG | LEU | A | 490 | 9.502 | 10.246 | 0.795 | 1.00 19.87 |
| ATOM | 2004 | CD1 | LEU | A | 490 | 8.990 | 10.557 | 2.193 | 1.00 18.37 |
| ATOM | 2005 | CD2 | LEU | A | 490 | 9.942 | 11.507 | 0.085 | 1.00 19.82 |
| ATOM | 2006 | C | LEU | A | 490 | 12.572 | 8.181 | -0.375 | 1.00 23.71 |
| ATOM | 2007 | O | LEU | A | 490 | 13.494 | 8.873 | -0.791 | 1.00 23.87 |
| ATOM | 2008 | N | ARG | A | 491 | 12.757 | 6.983 | 0.179 | 1.00 26.59 |
| ATOM | 2009 | CA | ARG | A | 491 | 14.083 | 6.370 | 0.307 | 1.00 28.92 |
| ATOM | 2010 | CB | ARG | A | 491 | 13.998 | 5.029 | 1.058 | 1.00 32.42 |
| ATOM | 2011 | CG | ARG | A | 491 | 15.296 | 4.191 | 1.001 | 1.00 36.79 |
| ATOM | 2012 | CD | ARG | A | 491 | 15.074 | 2.703 | 1.336 | 1.00 42.05 |
| ATOM | 2013 | NE | ARG | A | 491 | 13.976 | 2.124 | 0.548 | 1.00 46.12 |
| ATOM | 2014 | CZ | ARG | A | 491 | 14.064 | 1.733 | -0.727 | 1.00 45.98 |
| ATOM | 2015 | NH1 | ARG | A | 491 | 15.211 | 1.830 | -1.397 | 1.00 45.77 |
| ATOM | 2016 | NH2 | ARG | A | 491 | 12.980 | 1.303 | -1.359 | 1.00 44.96 |
| ATOM | 2017 | C | ARG | A | 491 | 14.688 | 6.128 | -1.083 | 1.00 28.73 |
| ATOM | 2018 | O | ARG | A | 491 | 15.863 | 6.402 | -1.314 | 1.00 28.47 |
| ATOM | 2019 | N | SER | A | 492 | 13.870 | 5.639 | -2.009 | 1.00 28.31 |
| ATOM | 2020 | CA | SER | A | 492 | 14.329 | 5.356 | -3.363 | 1.00 30.26 |
| ATOM | 2021 | CB | SER | A | 492 | 13.212 | 4.703 | -4.168 | 1.00 32.42 |
| ATOM | 2022 | OG | SER | A | 492 | 12.825 | 3.475 | -3.573 | 1.00 39.06 |
| ATOM | 2023 | C | SER | A | 492 | 14.826 | 6.581 | -4.111 | 1.00 30.81 |
| ATOM | 2024 | O | SER | A | 492 | 15.898 | 6.559 | -4.723 | 1.00 30.69 |
| ATOM | 2025 | N | VAL | A | 493 | 14.043 | 7.652 | -4.048 | 1.00 31.75 |
| ATOM | 2026 | CA | VAL | A | 493 | 14.365 | 8.887 | -4.740 | 1.00 31.72 |
| ATOM | 2027 | CB | VAL | A | 493 | 13.100 | 9.788 | -4.857 | 1.00 32.61 |
| ATOM | 2028 | CG1 | VAL | A | 493 | 12.639 | 10.242 | -3.502 | 1.00 33.39 |
| ATOM | 2029 | CG2 | VAL | A | 493 | 13.359 | 10.973 | -5.760 | 1.00 34.98 |
| ATOM | 2030 | C | VAL | A | 493 | 15.573 | 9.619 | -4.139 | 1.00 30.92 |
| ATOM | 2031 | O | VAL | A | 493 | 16.402 | 10.148 | -4.880 | 1.00 30.26 |
| ATOM | 2032 | N | LEU | A | 494 | 15.706 | 9.599 | -2.810 | 1.00 30.79 |
| ATOM | 2033 | CA | LEU | A | 494 | 16.843 | 10.251 | -2.135 | 1.00 30.45 |
| ATOM | 2034 | CB | LEU | A | 494 | 16.589 | 10.405 | -0.628 | 1.00 26.88 |
| ATOM | 2035 | CG | LEU | A | 494 | 15.514 | 11.434 | -0.256 | 1.00 25.84 |
| ATOM | 2036 | CD1 | LEU | A | 494 | 15.177 | 11.403 | 1.224 | 1.00 24.19 |
| ATOM | 2037 | CD2 | LEU | A | 494 | 15.980 | 12.802 | -0.673 | 1.00 24.38 |
| ATOM | 2038 | C | LEU | A | 494 | 18.122 | 9.461 | -2.379 | 1.00 32.11 |
| ATOM | 2039 | O | LEU | A | 494 | 19.196 | 10.040 | -2.459 | 1.00 32.04 |
| ATOM | 2040 | N | GLU | A | 495 | 17.989 | 8.140 | -2.509 | 1.00 34.55 |
| ATOM | 2041 | CA | GLU | A | 495 | 19.115 | 7.246 | -2.775 | 1.00 37.52 |
| ATOM | 2042 | CB | GLU | A | 495 | 18.688 | 5.783 | -2.689 | 1.00 39.45 |
| ATOM | 2043 | CG | GLU | A | 495 | 18.850 | 5.131 | -1.337 | 1.00 42.52 |
| ATOM | 2044 | CD | GLU | A | 495 | 18.426 | 3.673 | -1.356 | 1.00 45.01 |
| ATOM | 2045 | OE1 | GLU | A | 495 | 18.461 | 3.054 | -2.449 | 1.00 45.46 |
| ATOM | 2046 | OE2 | GLU | A | 495 | 18.061 | 3.153 | -0.273 | 1.00 46.81 |
| ATOM | 2047 | C | GLU | A | 495 | 19.689 | 7.450 | -4.166 | 1.00 39.51 |
| ATOM | 2048 | O | GLU | A | 495 | 20.907 | 7.394 | -4.345 | 1.00 40.08 |
| ATOM | 2049 | N | ASP | A | 496 | 18.813 | 7.628 | -5.158 | 1.00 41.00 |
| ATOM | 2050 | CA | ASP | A | 496 | 19.255 | 7.816 | -6.543 | 1.00 43.22 |
| ATOM | 2051 | CB | ASP | A | 496 | 18.370 | 6.998 | -7.507 | 1.00 45.69 |
| ATOM | 2052 | CG | ASP | A | 496 | 18.464 | 5.483 | -7.270 | 1.00 50.69 |

Figure 7

```
ATOM   2053  OD1 ASP A 496      19.566    4.979   -6.932  1.00 52.83
ATOM   2054  OD2 ASP A 496      17.433    4.786   -7.430  1.00 52.71
ATOM   2055  C   ASP A 496      19.323    9.275   -7.013  1.00 43.38
ATOM   2056  O   ASP A 496      19.427    9.533   -8.216  1.00 43.37
ATOM   2057  N   PHE A 497      19.318   10.222   -6.077  1.00 43.17
ATOM   2058  CA  PHE A 497      19.343   11.644   -6.428  1.00 44.24
ATOM   2059  CB  PHE A 497      19.346   12.509   -5.168  1.00 41.78
ATOM   2060  CG  PHE A 497      18.583   13.796   -5.320  1.00 39.28
ATOM   2061  CD1 PHE A 497      17.209   13.833   -5.106  1.00 37.15
ATOM   2062  CD2 PHE A 497      19.244   14.978   -5.670  1.00 38.05
ATOM   2063  CE1 PHE A 497      16.503   15.026   -5.240  1.00 36.63
ATOM   2064  CE2 PHE A 497      18.546   16.179   -5.804  1.00 36.38
ATOM   2065  CZ  PHE A 497      17.174   16.201   -5.588  1.00 36.72
ATOM   2066  C   PHE A 497      20.479   12.047   -7.385  1.00 46.13
ATOM   2067  O   PHE A 497      20.227   12.708   -8.398  1.00 46.14
ATOM   2068  N   PHE A 498      21.715   11.671   -7.048  1.00 48.27
ATOM   2069  CA  PHE A 498      22.900   11.929   -7.889  1.00 49.55
ATOM   2070  CB  PHE A 498      23.222   13.431   -8.081  1.00 49.92
ATOM   2071  CG  PHE A 498      23.134   14.282   -6.820  1.00 49.70
ATOM   2072  CD1 PHE A 498      23.266   13.728   -5.544  1.00 49.72
ATOM   2073  CD2 PHE A 498      22.893   15.657   -6.932  1.00 47.75
ATOM   2074  CE1 PHE A 498      23.160   14.538   -4.406  1.00 50.10
ATOM   2075  CE2 PHE A 498      22.783   16.474   -5.812  1.00 47.74
ATOM   2076  CZ  PHE A 498      22.913   15.920   -4.545  1.00 49.18
ATOM   2077  C   PHE A 498      24.142   11.181   -7.420  1.00 50.38
ATOM   2078  O   PHE A 498      24.163    9.949   -7.641  1.00 51.20
ATOM   2079  N1  LIG A 500      22.250    7.826   22.153  1.00 23.47
ATOM   2080  C1  LIG A 500      22.846    9.091   22.209  1.00 24.19
ATOM   2081  N2  LIG A 500      24.133    9.231   21.902  1.00 23.26
ATOM   2082  C2  LIG A 500      24.732   10.415   21.935  1.00 23.46
ATOM   2083  N3  LIG A 500      24.101   11.524   22.267  1.00 24.29
ATOM   2084  C3  LIG A 500      22.804   11.497   22.598  1.00 25.85
ATOM   2085  N4  LIG A 500      21.929   12.470   22.972  1.00 26.42
ATOM   2086  C4  LIG A 500      22.315   13.858   23.093  1.00 28.21
ATOM   2087  C5  LIG A 500      21.751   14.470   24.408  1.00 28.67
ATOM   2088  C6  LIG A 500      22.239   15.925   24.482  1.00 30.78
ATOM   2089  C7  LIG A 500      21.724   16.701   23.246  1.00 32.37
ATOM   2090  N5  LIG A 500      22.203   18.102   23.224  1.00 35.08
ATOM   2091  C8  LIG A 500      21.158   19.150   23.113  1.00 36.04
ATOM   2092  C9  LIG A 500      21.789   20.543   22.898  1.00 37.42
ATOM   2093  N6  LIG A 500      22.636   20.866   24.071  1.00 38.94
ATOM   2094  C10 LIG A 500      23.246   22.198   23.851  1.00 38.65
ATOM   2095  C11 LIG A 500      23.705   19.849   24.159  1.00 38.31
ATOM   2096  C12 LIG A 500      23.061   18.479   24.386  1.00 36.52
ATOM   2097  C13 LIG A 500      22.238   16.110   21.946  1.00 29.71
ATOM   2098  C14 LIG A 500      21.806   14.638   21.854  1.00 28.38
ATOM   2099  C15 LIG A 500      20.691   11.946   23.207  1.00 26.30
ATOM   2100  C16 LIG A 500      20.721   10.594   22.989  1.00 26.28
ATOM   2101  C17 LIG A 500      19.544    9.630   23.164  1.00 26.83
ATOM   2102  C18 LIG A 500      18.320    9.769   22.483  1.00 27.15
ATOM   2103  C19 LIG A 500      17.302    8.866   22.738  1.00 27.74
ATOM   2104  C20 LIG A 500      17.476    7.829   23.656  1.00 28.10
ATOM   2105  N7  LIG A 500      16.417    6.934   23.905  1.00 29.94
ATOM   2106  C21 LIG A 500      15.358    6.470   23.211  1.00 32.65
ATOM   2107  O1  LIG A 500      15.165    6.835   22.066  1.00 32.28
ATOM   2108  C22 LIG A 500      14.414    5.486   23.861  1.00 33.89
ATOM   2109  C23 LIG A 500      12.993    6.080   23.856  1.00 35.25
ATOM   2110  C24 LIG A 500      12.788    6.973   25.067  1.00 35.37
ATOM   2111  C25 LIG A 500      12.466    8.316   24.900  1.00 35.97
```

Figure 7

```
ATOM   2112  C26 LIG A 500      12.278    9.133   26.003  1.00 36.52
ATOM   2113  C27 LIG A 500      12.418    8.611   27.281  1.00 37.17
ATOM   2114  C28 LIG A 500      12.738    7.268   27.451  1.00 37.32
ATOM   2115  C29 LIG A 500      12.927    6.454   26.344  1.00 36.25
ATOM   2116  C30 LIG A 500      18.687    7.686   24.329  1.00 27.66
ATOM   2117  O2  LIG A 500      18.852    6.667   25.223  1.00 27.66
ATOM   2118  C31 LIG A 500      19.894    6.579   26.192  1.00 26.92
ATOM   2119  C32 LIG A 500      19.715    8.582   24.087  1.00 27.46
ATOM   2120  C33 LIG A 500      22.054   10.166   22.580  1.00 25.12
ATOM   2121  OH2 H2O A 600       4.665   21.923    9.467  1.00 26.49
ATOM   2122  OH2 H2O A 601      -1.601   24.092    0.482  1.00 19.17
ATOM   2123  OH2 H2O A 602       6.111    2.522   -3.795  1.00 35.09
ATOM   2124  OH2 H2O A 603      -5.986   25.056    2.216  1.00 24.23
ATOM   2125  OH2 H2O A 604       6.557   12.757   13.210  1.00 15.73
ATOM   2126  OH2 H2O A 605      -3.738   16.777   -0.736  1.00 16.83
ATOM   2127  OH2 H2O A 606       2.622   11.176   -3.522  1.00 31.90
ATOM   2128  OH2 H2O A 607      -0.988   30.435    2.035  1.00 22.66
ATOM   2129  OH2 H2O A 608       5.615   23.956    4.612  1.00 18.93
ATOM   2130  OH2 H2O A 609       5.764   18.545   -5.821  1.00 19.51
ATOM   2131  OH2 H2O A 610       0.581    5.750    0.113  1.00 24.10
ATOM   2132  OH2 H2O A 611       8.166    9.455   19.022  1.00 23.71
ATOM   2133  OH2 H2O A 612      -9.897    7.535   -4.016  1.00 23.99
ATOM   2134  OH2 H2O A 613      -1.821    7.009   -0.439  1.00 22.74
ATOM   2135  OH2 H2O A 614       7.432   24.474   16.542  1.00 18.58
ATOM   2136  OH2 H2O A 615       1.179   26.815   -3.060  1.00 26.26
ATOM   2137  OH2 H2O A 616       3.768    0.784   -1.530  1.00 20.37
ATOM   2138  OH2 H2O A 617      34.000   12.168   23.377  1.00 31.73
ATOM   2139  OH2 H2O A 618      20.131    4.639    2.421  1.00 41.99
ATOM   2140  OH2 H2O A 619      14.275   19.461   15.037  1.00 18.75
ATOM   2141  OH2 H2O A 620       3.309    6.274    3.941  1.00 27.82
ATOM   2142  OH2 H2O A 621       3.165   15.060   12.022  1.00 23.07
ATOM   2143  OH2 H2O A 622      31.689   -2.086   34.745  1.00 42.66
ATOM   2144  OH2 H2O A 623       5.274   27.916   -1.214  1.00 22.65
ATOM   2145  OH2 H2O A 624      16.626   -1.462    4.841  1.00 52.30
ATOM   2146  OH2 H2O A 625      -2.047   11.552    9.991  1.00 38.10
ATOM   2147  OH2 H2O A 626      -2.088   12.122   -5.217  1.00 19.55
ATOM   2148  OH2 H2O A 627      -8.262    8.000   -6.178  1.00 26.48
ATOM   2149  OH2 H2O A 628      -2.262   23.428    5.323  1.00 18.42
ATOM   2150  OH2 H2O A 629      -2.933    6.267    1.969  1.00 27.89
ATOM   2151  OH2 H2O A 630      18.505   -0.792   15.806  1.00 34.59
ATOM   2152  OH2 H2O A 631       2.604   21.186   -0.570  1.00 15.86
ATOM   2153  OH2 H2O A 632      -4.951   23.190    9.451  1.00 29.19
ATOM   2154  OH2 H2O A 633      25.986    0.911   41.482  1.00 51.70
ATOM   2155  OH2 H2O A 634       3.820   36.084    7.319  1.00 51.30
ATOM   2156  OH2 H2O A 635       0.113    4.676   10.321  1.00 24.75
ATOM   2157  OH2 H2O A 636      12.247   27.970    3.211  1.00 25.41
ATOM   2158  OH2 H2O A 637       2.286   -2.178    0.838  1.00 20.14
ATOM   2159  OH2 H2O A 638      -0.570   21.246   -1.121  1.00 29.57
ATOM   2160  OH2 H2O A 639       2.898   22.377   11.284  1.00 17.93
ATOM   2161  OH2 H2O A 640       3.473   30.510   -4.261  1.00 19.76
ATOM   2162  OH2 H2O A 641      24.362   18.941   31.066  1.00 42.65
ATOM   2163  OH2 H2O A 642       4.045    3.402   16.657  1.00 31.02
ATOM   2164  OH2 H2O A 643       9.502   28.124   -3.706  1.00 25.16
ATOM   2165  OH2 H2O A 644       9.740   10.920   28.156  1.00 37.15
ATOM   2166  OH2 H2O A 645      13.611   15.398   24.694  1.00 51.12
ATOM   2167  OH2 H2O A 646      -7.702   12.506   -6.135  1.00 46.10
ATOM   2168  OH2 H2O A 647       6.138   34.087    3.879  1.00 16.98
ATOM   2169  OH2 H2O A 648      25.352   20.794   21.671  1.00 42.13
ATOM   2170  OH2 H2O A 649      -2.834   24.423   -1.945  1.00 29.69
```

Figure 7

| | | | | | | | | | |
|---|---|---|---|---|---|---|---|---|---|
| ATOM | 2171 | OH2 | H2O | A | 650 | 8.129 | 0.844 | 3.642 | 1.00 25.96 |
| ATOM | 2172 | OH2 | H2O | A | 651 | 22.530 | 23.347 | 0.897 | 1.00 45.71 |
| ATOM | 2173 | OH2 | H2O | A | 652 | 5.211 | 1.014 | 1.747 | 1.00 53.85 |
| ATOM | 2174 | OH2 | H2O | A | 653 | -2.877 | 7.806 | 6.833 | 1.00 25.26 |
| ATOM | 2175 | OH2 | H2O | A | 654 | 11.374 | 3.699 | 21.239 | 1.00 26.09 |
| ATOM | 2176 | OH2 | H2O | A | 655 | 32.672 | 20.362 | 13.601 | 1.00 38.17 |
| ATOM | 2177 | OH2 | H2O | A | 656 | 13.852 | 0.056 | 5.173 | 1.00 30.17 |
| ATOM | 2178 | OH2 | H2O | A | 657 | -3.638 | 24.622 | 11.087 | 1.00 37.87 |
| ATOM | 2179 | OH2 | H2O | A | 658 | 30.465 | 4.524 | 20.719 | 1.00 42.01 |
| ATOM | 2180 | OH2 | H2O | A | 659 | 4.476 | 14.842 | 14.612 | 1.00 29.74 |
| ATOM | 2181 | OH2 | H2O | A | 660 | -5.739 | 18.591 | 6.632 | 1.00 41.77 |
| ATOM | 2182 | OH2 | H2O | A | 661 | 13.800 | 21.088 | 17.127 | 1.00 56.18 |
| ATOM | 2183 | OH2 | H2O | A | 662 | 29.210 | 15.653 | 33.669 | 1.00 26.28 |
| ATOM | 2184 | OH2 | H2O | A | 663 | -7.203 | 18.950 | 9.238 | 1.00 29.41 |
| ATOM | 2185 | OH2 | H2O | A | 664 | 27.638 | 2.049 | 21.713 | 1.00 37.05 |
| ATOM | 2186 | OH2 | H2O | A | 665 | 18.165 | 16.582 | 20.799 | 1.00 40.20 |
| ATOM | 2187 | OH2 | H2O | A | 666 | 14.078 | 24.716 | 8.108 | 1.00 22.05 |
| ATOM | 2188 | OH2 | H2O | A | 667 | -5.297 | 23.094 | 6.589 | 1.00 34.93 |
| ATOM | 2189 | OH2 | H2O | A | 668 | 17.512 | 23.971 | -8.419 | 1.00 31.63 |
| ATOM | 2190 | OH2 | H2O | A | 669 | -1.577 | 26.133 | -3.452 | 1.00 35.64 |
| ATOM | 2191 | OH2 | H2O | A | 670 | 33.341 | 12.183 | 13.381 | 1.00 35.88 |
| ATOM | 2192 | OH2 | H2O | A | 671 | -5.516 | 24.903 | 13.069 | 1.00 46.04 |
| ATOM | 2193 | OH2 | H2O | A | 672 | 1.636 | 4.575 | 33.610 | 1.00 46.12 |
| ATOM | 2194 | OH2 | H2O | A | 673 | 16.933 | -1.851 | 19.939 | 1.00 28.39 |
| ATOM | 2195 | OH2 | H2O | A | 674 | 15.822 | 23.235 | 13.138 | 1.00 27.32 |
| ATOM | 2196 | OH2 | H2O | A | 675 | 16.560 | -0.122 | 17.575 | 1.00 31.07 |
| ATOM | 2197 | OH2 | H2O | A | 676 | -9.237 | 10.376 | -7.473 | 1.00 30.10 |
| ATOM | 2198 | OH2 | H2O | A | 677 | 21.732 | 8.965 | 38.059 | 1.00 40.82 |
| ATOM | 2199 | OH2 | H2O | A | 678 | 6.065 | 9.617 | -9.526 | 1.00 35.16 |
| ATOM | 2200 | OH2 | H2O | A | 679 | 30.908 | 12.227 | 25.921 | 1.00 28.55 |
| ATOM | 2201 | OH2 | H2O | A | 680 | 8.561 | 1.809 | 17.141 | 1.00 30.27 |
| ATOM | 2202 | OH2 | H2O | A | 681 | 22.110 | 10.491 | -2.341 | 1.00 41.23 |
| ATOM | 2203 | CB | TRP | B | 238 | 44.489 | 27.831 | 34.562 | 1.00 49.35 |
| ATOM | 2204 | CG | TRP | B | 238 | 44.062 | 28.179 | 35.971 | 1.00 49.28 |
| ATOM | 2205 | CD2 | TRP | B | 238 | 44.737 | 27.828 | 37.191 | 1.00 48.18 |
| ATOM | 2206 | CE2 | TRP | B | 238 | 43.988 | 28.384 | 38.255 | 1.00 47.87 |
| ATOM | 2207 | CE3 | TRP | B | 238 | 45.904 | 27.106 | 37.488 | 1.00 47.36 |
| ATOM | 2208 | CD1 | TRP | B | 238 | 42.960 | 28.908 | 36.340 | 1.00 48.44 |
| ATOM | 2209 | NE1 | TRP | B | 238 | 42.914 | 29.034 | 37.707 | 1.00 47.53 |
| ATOM | 2210 | CZ2 | TRP | B | 238 | 44.372 | 28.236 | 39.596 | 1.00 47.00 |
| ATOM | 2211 | CZ3 | TRP | B | 238 | 46.284 | 26.962 | 38.827 | 1.00 45.88 |
| ATOM | 2212 | CH2 | TRP | B | 238 | 45.520 | 27.525 | 39.859 | 1.00 46.45 |
| ATOM | 2213 | C | TRP | B | 238 | 46.165 | 28.074 | 32.724 | 1.00 50.43 |
| ATOM | 2214 | O | TRP | B | 238 | 46.861 | 27.071 | 32.852 | 1.00 49.69 |
| ATOM | 2215 | N | TRP | B | 238 | 45.026 | 30.130 | 33.721 | 1.00 50.01 |
| ATOM | 2216 | CA | TRP | B | 238 | 45.567 | 28.750 | 33.964 | 1.00 50.06 |
| ATOM | 2217 | N | GLU | B | 239 | 45.868 | 28.600 | 31.531 | 1.00 51.64 |
| ATOM | 2218 | CA | GLU | B | 239 | 46.401 | 28.032 | 30.281 | 1.00 52.49 |
| ATOM | 2219 | CB | GLU | B | 239 | 45.585 | 28.461 | 29.047 | 1.00 55.11 |
| ATOM | 2220 | CG | GLU | B | 239 | 44.421 | 27.547 | 28.660 | 1.00 59.39 |
| ATOM | 2221 | CD | GLU | B | 239 | 43.109 | 27.907 | 29.374 | 1.00 62.69 |
| ATOM | 2222 | OE1 | GLU | B | 239 | 42.993 | 27.670 | 30.605 | 1.00 63.53 |
| ATOM | 2223 | OE2 | GLU | B | 239 | 42.188 | 28.428 | 28.699 | 1.00 63.97 |
| ATOM | 2224 | C | GLU | B | 239 | 47.837 | 28.456 | 30.035 | 1.00 51.60 |
| ATOM | 2225 | O | GLU | B | 239 | 48.215 | 29.603 | 30.294 | 1.00 51.41 |
| ATOM | 2226 | N | VAL | B | 240 | 48.630 | 27.517 | 29.530 | 1.00 50.83 |
| ATOM | 2227 | CA | VAL | B | 240 | 50.027 | 27.774 | 29.191 | 1.00 49.19 |
| ATOM | 2228 | CB | VAL | B | 240 | 51.029 | 27.244 | 30.254 | 1.00 48.17 |
| ATOM | 2229 | CG1 | VAL | B | 240 | 50.771 | 27.893 | 31.607 | 1.00 47.30 |

Figure 7

| | | | | | | | | | |
|---|---|---|---|---|---|---|---|---|---|
| ATOM | 2230 | CG2 | VAL | B | 240 | 50.983 | 25.719 | 30.328 | 1.00 47.62 |
| ATOM | 2231 | C | VAL | B | 240 | 50.342 | 27.109 | 27.854 | 1.00 48.93 |
| ATOM | 2232 | O | VAL | B | 240 | 49.660 | 26.167 | 27.430 | 1.00 47.08 |
| ATOM | 2233 | N | PRO | B | 241 | 51.349 | 27.637 | 27.146 | 1.00 49.91 |
| ATOM | 2234 | CD | PRO | B | 241 | 52.096 | 28.870 | 27.461 | 1.00 49.85 |
| ATOM | 2235 | CA | PRO | B | 241 | 51.757 | 27.088 | 25.850 | 1.00 50.54 |
| ATOM | 2236 | CB | PRO | B | 241 | 52.854 | 28.061 | 25.404 | 1.00 50.35 |
| ATOM | 2237 | CG | PRO | B | 241 | 52.488 | 29.346 | 26.099 | 1.00 50.63 |
| ATOM | 2238 | C | PRO | B | 241 | 52.332 | 25.677 | 26.019 | 1.00 50.82 |
| ATOM | 2239 | O | PRO | B | 241 | 53.055 | 25.414 | 26.984 | 1.00 50.61 |
| ATOM | 2240 | N | ARG | B | 242 | 51.990 | 24.780 | 25.095 | 1.00 51.51 |
| ATOM | 2241 | CA | ARG | B | 242 | 52.493 | 23.408 | 25.099 | 1.00 52.31 |
| ATOM | 2242 | CB | ARG | B | 242 | 51.989 | 22.708 | 23.843 | 1.00 53.79 |
| ATOM | 2243 | CG | ARG | B | 242 | 52.618 | 21.361 | 23.571 | 1.00 57.42 |
| ATOM | 2244 | CD | ARG | B | 242 | 52.094 | 20.328 | 24.533 | 1.00 59.94 |
| ATOM | 2245 | NE | ARG | B | 242 | 50.637 | 20.261 | 24.447 | 1.00 62.88 |
| ATOM | 2246 | CZ | ARG | B | 242 | 49.966 | 19.586 | 23.516 | 1.00 63.04 |
| ATOM | 2247 | NH1 | ARG | B | 242 | 50.618 | 18.899 | 22.584 | 1.00 63.76 |
| ATOM | 2248 | NH2 | ARG | B | 242 | 48.640 | 19.628 | 23.498 | 1.00 62.45 |
| ATOM | 2249 | C | ARG | B | 242 | 54.038 | 23.406 | 25.109 | 1.00 52.87 |
| ATOM | 2250 | O | ARG | B | 242 | 54.679 | 22.496 | 25.641 | 1.00 53.27 |
| ATOM | 2251 | N | GLU | B | 243 | 54.609 | 24.453 | 24.512 | 1.00 52.53 |
| ATOM | 2252 | CA | GLU | B | 243 | 56.049 | 24.672 | 24.395 | 1.00 50.72 |
| ATOM | 2253 | CB | GLU | B | 243 | 56.320 | 26.063 | 23.805 | 1.00 52.29 |
| ATOM | 2254 | CG | GLU | B | 243 | 55.961 | 26.218 | 22.339 | 1.00 56.23 |
| ATOM | 2255 | CD | GLU | B | 243 | 54.505 | 25.896 | 22.044 | 1.00 58.82 |
| ATOM | 2256 | OE1 | GLU | B | 243 | 53.630 | 26.748 | 22.325 | 1.00 59.49 |
| ATOM | 2257 | OE2 | GLU | B | 243 | 54.238 | 24.778 | 21.548 | 1.00 60.91 |
| ATOM | 2258 | C | GLU | B | 243 | 56.768 | 24.584 | 25.725 | 1.00 48.90 |
| ATOM | 2259 | O | GLU | B | 243 | 57.840 | 23.977 | 25.805 | 1.00 49.27 |
| ATOM | 2260 | N | THR | B | 244 | 56.180 | 25.212 | 26.750 | 1.00 46.23 |
| ATOM | 2261 | CA | THR | B | 244 | 56.741 | 25.260 | 28.111 | 1.00 43.24 |
| ATOM | 2262 | CB | THR | B | 244 | 55.894 | 26.174 | 29.067 | 1.00 42.95 |
| ATOM | 2263 | OG1 | THR | B | 244 | 54.581 | 25.630 | 29.233 | 1.00 39.98 |
| ATOM | 2264 | CG2 | THR | B | 244 | 55.778 | 27.589 | 28.521 | 1.00 42.96 |
| ATOM | 2265 | C | THR | B | 244 | 56.881 | 23.897 | 28.781 | 1.00 41.22 |
| ATOM | 2266 | O | THR | B | 244 | 57.587 | 23.754 | 29.781 | 1.00 40.14 |
| ATOM | 2267 | N | LEU | B | 245 | 56.261 | 22.889 | 28.187 | 1.00 39.56 |
| ATOM | 2268 | CA | LEU | B | 245 | 56.284 | 21.553 | 28.747 | 1.00 39.32 |
| ATOM | 2269 | CB | LEU | B | 245 | 54.845 | 21.067 | 28.889 | 1.00 39.62 |
| ATOM | 2270 | CG | LEU | B | 245 | 54.359 | 20.592 | 30.251 | 1.00 40.29 |
| ATOM | 2271 | CD1 | LEU | B | 245 | 54.519 | 21.665 | 31.318 | 1.00 39.40 |
| ATOM | 2272 | CD2 | LEU | B | 245 | 52.905 | 20.224 | 30.076 | 1.00 42.24 |
| ATOM | 2273 | C | LEU | B | 245 | 57.096 | 20.489 | 27.997 | 1.00 38.65 |
| ATOM | 2274 | O | LEU | B | 245 | 56.958 | 20.309 | 26.775 | 1.00 38.90 |
| ATOM | 2275 | N | LYS | B | 246 | 57.921 | 19.765 | 28.746 | 1.00 36.71 |
| ATOM | 2276 | CA | LYS | B | 246 | 58.704 | 18.683 | 28.169 | 1.00 35.72 |
| ATOM | 2277 | CB | LYS | B | 246 | 60.226 | 18.971 | 28.197 | 1.00 38.04 |
| ATOM | 2278 | CG | LYS | B | 246 | 61.074 | 17.821 | 27.590 | 1.00 39.82 |
| ATOM | 2279 | CD | LYS | B | 246 | 62.561 | 18.144 | 27.397 | 1.00 39.92 |
| ATOM | 2280 | CE | LYS | B | 246 | 63.337 | 18.243 | 28.686 | 1.00 38.68 |
| ATOM | 2281 | NZ | LYS | B | 246 | 64.745 | 18.636 | 28.409 | 1.00 38.73 |
| ATOM | 2282 | C | LYS | B | 246 | 58.383 | 17.414 | 28.942 | 1.00 32.89 |
| ATOM | 2283 | O | LYS | B | 246 | 58.750 | 17.271 | 30.104 | 1.00 32.72 |
| ATOM | 2284 | N | LEU | B | 247 | 57.660 | 16.518 | 28.286 | 1.00 31.01 |
| ATOM | 2285 | CA | LEU | B | 247 | 57.275 | 15.248 | 28.878 | 1.00 30.55 |
| ATOM | 2286 | CB | LEU | B | 247 | 56.020 | 14.703 | 28.189 | 1.00 29.55 |
| ATOM | 2287 | CG | LEU | B | 247 | 54.691 | 15.155 | 28.798 | 1.00 28.11 |
| ATOM | 2288 | CD1 | LEU | B | 247 | 54.567 | 16.666 | 28.843 | 1.00 26.60 |

Figure 7

```
ATOM   2289  CD2 LEU B 247      53.570  14.530  27.992  1.00 29.89
ATOM   2290  C   LEU B 247      58.435  14.285  28.757  1.00 30.65
ATOM   2291  O   LEU B 247      58.894  13.992  27.653  1.00 30.86
ATOM   2292  N   VAL B 248      58.886  13.773  29.899  1.00 30.94
ATOM   2293  CA  VAL B 248      60.052  12.897  29.957  1.00 29.95
ATOM   2294  CB  VAL B 248      61.022  13.416  31.049  1.00 30.08
ATOM   2295  CG1 VAL B 248      62.282  12.574  31.110  1.00 31.30
ATOM   2296  CG2 VAL B 248      61.364  14.874  30.778  1.00 30.10
ATOM   2297  C   VAL B 248      59.813  11.409  30.159  1.00 30.27
ATOM   2298  O   VAL B 248      60.463  10.566  29.516  1.00 29.80
ATOM   2299  N   GLU B 249      58.873  11.078  31.034  1.00 30.37
ATOM   2300  CA  GLU B 249      58.618   9.678  31.324  1.00 30.53
ATOM   2301  CB  GLU B 249      59.595   9.248  32.425  1.00 31.15
ATOM   2302  CG  GLU B 249      59.295   7.949  33.153  1.00 30.53
ATOM   2303  CD  GLU B 249      60.063   7.838  34.456  1.00 31.31
ATOM   2304  OE1 GLU B 249      60.741   8.811  34.870  1.00 29.83
ATOM   2305  OE2 GLU B 249      59.981   6.764  35.077  1.00 33.75
ATOM   2306  C   GLU B 249      57.172   9.409  31.730  1.00 30.45
ATOM   2307  O   GLU B 249      56.565  10.193  32.464  1.00 30.24
ATOM   2308  N   ARG B 250      56.632   8.287  31.264  1.00 30.16
ATOM   2309  CA  ARG B 250      55.264   7.922  31.587  1.00 30.87
ATOM   2310  CB  ARG B 250      54.642   7.115  30.471  1.00 32.62
ATOM   2311  CG  ARG B 250      53.131   7.189  30.496  1.00 36.76
ATOM   2312  CD  ARG B 250      52.555   6.433  29.335  1.00 38.07
ATOM   2313  NE  ARG B 250      52.765   5.007  29.512  1.00 39.70
ATOM   2314  CZ  ARG B 250      52.561   4.103  28.568  1.00 40.81
ATOM   2315  NH1 ARG B 250      52.147   4.476  27.370  1.00 40.85
ATOM   2316  NH2 ARG B 250      52.778   2.822  28.829  1.00 41.71
ATOM   2317  C   ARG B 250      55.189   7.132  32.868  1.00 29.49
ATOM   2318  O   ARG B 250      55.781   6.069  32.972  1.00 29.12
ATOM   2319  N   LEU B 251      54.459   7.675  33.838  1.00 29.00
ATOM   2320  CA  LEU B 251      54.287   7.048  35.145  1.00 29.26
ATOM   2321  CB  LEU B 251      53.985   8.107  36.216  1.00 26.77
ATOM   2322  CG  LEU B 251      54.932   9.308  36.278  1.00 25.89
ATOM   2323  CD1 LEU B 251      54.499  10.257  37.366  1.00 25.03
ATOM   2324  CD2 LEU B 251      56.361   8.845  36.504  1.00 25.22
ATOM   2325  C   LEU B 251      53.171   6.015  35.117  1.00 30.61
ATOM   2326  O   LEU B 251      53.221   5.015  35.835  1.00 30.95
ATOM   2327  N   GLY B 252      52.165   6.253  34.279  1.00 32.32
ATOM   2328  CA  GLY B 252      51.059   5.322  34.185  1.00 31.84
ATOM   2329  C   GLY B 252      50.168   5.580  32.997  1.00 32.31
ATOM   2330  O   GLY B 252      50.081   6.705  32.504  1.00 31.93
ATOM   2331  N   ALA B 253      49.526   4.516  32.532  1.00 33.24
ATOM   2332  CA  ALA B 253      48.610   4.572  31.395  1.00 34.91
ATOM   2333  CB  ALA B 253      49.278   4.027  30.150  1.00 34.33
ATOM   2334  C   ALA B 253      47.368   3.743  31.729  1.00 35.58
ATOM   2335  O   ALA B 253      47.470   2.563  32.072  1.00 36.94
ATOM   2336  N   GLY B 254      46.200   4.371  31.651  1.00 35.51
ATOM   2337  CA  GLY B 254      44.963   3.680  31.952  1.00 35.57
ATOM   2338  C   GLY B 254      43.830   3.980  30.992  1.00 36.26
ATOM   2339  O   GLY B 254      44.006   4.629  29.961  1.00 36.24
ATOM   2340  N   GLN B 255      42.640   3.552  31.376  1.00 36.84
ATOM   2341  CA  GLN B 255      41.449   3.730  30.554  1.00 38.01
ATOM   2342  CB  GLN B 255      40.216   3.348  31.362  1.00 41.62
ATOM   2343  CG  GLN B 255      39.217   2.547  30.568  1.00 45.91
ATOM   2344  CD  GLN B 255      37.826   2.657  31.131  1.00 48.92
ATOM   2345  OE1 GLN B 255      36.842   2.570  30.386  1.00 50.97
ATOM   2346  NE2 GLN B 255      37.725   2.860  32.449  1.00 48.26
ATOM   2347  C   GLN B 255      41.208   5.092  29.894  1.00 36.17
```

Figure 7

| | | | | | | | | | |
|---|---|---|---|---|---|---|---|---|---|
| ATOM | 2348 | O | GLN | B | 255 | 41.048 | 5.171 | 28.676 | 1.00 35.87 |
| ATOM | 2349 | N | PHE | B | 256 | 41.194 | 6.155 | 30.692 | 1.00 35.19 |
| ATOM | 2350 | CA | PHE | B | 256 | 40.922 | 7.510 | 30.190 | 1.00 34.33 |
| ATOM | 2351 | CB | PHE | B | 256 | 40.033 | 8.281 | 31.187 | 1.00 33.34 |
| ATOM | 2352 | CG | PHE | B | 256 | 38.692 | 7.648 | 31.427 | 1.00 31.44 |
| ATOM | 2353 | CD1 | PHE | B | 256 | 38.187 | 6.694 | 30.543 | 1.00 31.36 |
| ATOM | 2354 | CD2 | PHE | B | 256 | 37.943 | 7.987 | 32.549 | 1.00 29.70 |
| ATOM | 2355 | CE1 | PHE | B | 256 | 36.958 | 6.086 | 30.773 | 1.00 32.64 |
| ATOM | 2356 | CE2 | PHE | B | 256 | 36.712 | 7.388 | 32.795 | 1.00 29.31 |
| ATOM | 2357 | CZ | PHE | B | 256 | 36.215 | 6.434 | 31.908 | 1.00 31.56 |
| ATOM | 2358 | C | PHE | B | 256 | 42.126 | 8.377 | 29.839 | 1.00 34.23 |
| ATOM | 2359 | O | PHE | B | 256 | 41.969 | 9.512 | 29.379 | 1.00 33.31 |
| ATOM | 2360 | N | GLY | B | 257 | 43.324 | 7.872 | 30.093 | 1.00 34.60 |
| ATOM | 2361 | CA | GLY | B | 257 | 44.501 | 8.657 | 29.798 | 1.00 34.38 |
| ATOM | 2362 | C | GLY | B | 257 | 45.757 | 8.133 | 30.456 | 1.00 33.91 |
| ATOM | 2363 | O | GLY | B | 257 | 45.826 | 6.977 | 30.872 | 1.00 32.11 |
| ATOM | 2364 | N | GLU | B | 258 | 46.743 | 9.019 | 30.569 | 1.00 35.10 |
| ATOM | 2365 | CA | GLU | B | 258 | 48.043 | 8.683 | 31.143 | 1.00 35.10 |
| ATOM | 2366 | CB | GLU | B | 258 | 49.052 | 8.443 | 30.005 | 1.00 35.83 |
| ATOM | 2367 | CG | GLU | B | 258 | 48.603 | 7.436 | 28.946 | 1.00 38.33 |
| ATOM | 2368 | CD | GLU | B | 258 | 49.582 | 7.288 | 27.787 | 1.00 39.52 |
| ATOM | 2369 | OE1 | GLU | B | 258 | 50.246 | 8.286 | 27.425 | 1.00 39.36 |
| ATOM | 2370 | OE2 | GLU | B | 258 | 49.673 | 6.166 | 27.231 | 1.00 40.40 |
| ATOM | 2371 | C | GLU | B | 258 | 48.553 | 9.825 | 32.018 | 1.00 34.63 |
| ATOM | 2372 | O | GLU | B | 258 | 48.043 | 10.955 | 31.935 | 1.00 34.73 |
| ATOM | 2373 | N | VAL | B | 259 | 49.516 | 9.506 | 32.891 | 1.00 33.75 |
| ATOM | 2374 | CA | VAL | B | 259 | 50.158 | 10.509 | 33.754 | 1.00 32.25 |
| ATOM | 2375 | CB | VAL | B | 259 | 49.932 | 10.259 | 35.278 | 1.00 31.88 |
| ATOM | 2376 | CG1 | VAL | B | 259 | 50.483 | 11.429 | 36.097 | 1.00 29.84 |
| ATOM | 2377 | CG2 | VAL | B | 259 | 48.464 | 10.068 | 35.575 | 1.00 31.00 |
| ATOM | 2378 | C | VAL | B | 259 | 51.643 | 10.392 | 33.428 | 1.00 31.46 |
| ATOM | 2379 | O | VAL | B | 259 | 52.164 | 9.282 | 33.274 | 1.00 30.64 |
| ATOM | 2380 | N | TRP | B | 260 | 52.293 | 11.537 | 33.241 | 1.00 31.45 |
| ATOM | 2381 | CA | TRP | B | 260 | 53.713 | 11.597 | 32.903 | 1.00 31.41 |
| ATOM | 2382 | CB | TRP | B | 260 | 53.930 | 12.179 | 31.486 | 1.00 32.25 |
| ATOM | 2383 | CG | TRP | B | 260 | 53.522 | 11.304 | 30.313 | 1.00 35.13 |
| ATOM | 2384 | CD2 | TRP | B | 260 | 54.391 | 10.765 | 29.302 | 1.00 35.28 |
| ATOM | 2385 | CE2 | TRP | B | 260 | 53.585 | 10.024 | 28.404 | 1.00 35.49 |
| ATOM | 2386 | CE3 | TRP | B | 260 | 55.771 | 10.837 | 29.068 | 1.00 35.02 |
| ATOM | 2387 | CD1 | TRP | B | 260 | 52.256 | 10.880 | 29.989 | 1.00 34.98 |
| ATOM | 2388 | NE1 | TRP | B | 260 | 52.291 | 10.110 | 28.848 | 1.00 35.52 |
| ATOM | 2389 | CZ2 | TRP | B | 260 | 54.115 | 9.358 | 27.292 | 1.00 34.24 |
| ATOM | 2390 | CZ3 | TRP | B | 260 | 56.297 | 10.171 | 27.961 | 1.00 34.67 |
| ATOM | 2391 | CH2 | TRP | B | 260 | 55.469 | 9.444 | 27.092 | 1.00 33.94 |
| ATOM | 2392 | C | TRP | B | 260 | 54.446 | 12.517 | 33.857 | 1.00 30.25 |
| ATOM | 2393 | O | TRP | B | 260 | 53.856 | 13.364 | 34.520 | 1.00 28.98 |
| ATOM | 2394 | N | MET | B | 261 | 55.759 | 12.331 | 33.906 | 1.00 30.66 |
| ATOM | 2395 | CA | MET | B | 261 | 56.656 | 13.167 | 34.692 | 1.00 29.49 |
| ATOM | 2396 | CB | MET | B | 261 | 57.712 | 12.314 | 35.416 | 1.00 28.23 |
| ATOM | 2397 | CG | MET | B | 261 | 58.767 | 13.108 | 36.193 | 1.00 27.90 |
| ATOM | 2398 | SD | MET | B | 261 | 60.085 | 13.844 | 35.162 | 1.00 26.43 |
| ATOM | 2399 | CE | MET | B | 261 | 60.753 | 12.348 | 34.468 | 1.00 26.74 |
| ATOM | 2400 | C | MET | B | 261 | 57.313 | 14.031 | 33.611 | 1.00 29.47 |
| ATOM | 2401 | O | MET | B | 261 | 57.581 | 13.558 | 32.501 | 1.00 30.71 |
| ATOM | 2402 | N | GLY | B | 262 | 57.523 | 15.302 | 33.907 | 1.00 29.18 |
| ATOM | 2403 | CA | GLY | B | 262 | 58.125 | 16.164 | 32.921 | 1.00 29.01 |
| ATOM | 2404 | C | GLY | B | 262 | 58.637 | 17.421 | 33.556 | 1.00 29.69 |
| ATOM | 2405 | O | GLY | B | 262 | 58.680 | 17.523 | 34.775 | 1.00 28.34 |
| ATOM | 2406 | N | TYR | B | 263 | 58.999 | 18.387 | 32.722 | 1.00 32.47 |

Figure 7

| ATOM | 2407 | CA  | TYR | B | 263 | 59.532 | 19.651 | 33.191 | 1.00 | 35.28 |
|------|------|-----|-----|---|-----|--------|--------|--------|------|-------|
| ATOM | 2408 | CB  | TYR | B | 263 | 61.050 | 19.698 | 32.960 | 1.00 | 32.75 |
| ATOM | 2409 | CG  | TYR | B | 263 | 61.792 | 18.677 | 33.811 | 1.00 | 30.35 |
| ATOM | 2410 | CD1 | TYR | B | 263 | 62.196 | 18.991 | 35.117 | 1.00 | 26.74 |
| ATOM | 2411 | CE1 | TYR | B | 263 | 62.788 | 18.025 | 35.941 | 1.00 | 25.05 |
| ATOM | 2412 | CD2 | TYR | B | 263 | 62.008 | 17.370 | 33.345 | 1.00 | 27.75 |
| ATOM | 2413 | CE2 | TYR | B | 263 | 62.598 | 16.397 | 34.166 | 1.00 | 25.89 |
| ATOM | 2414 | CZ  | TYR | B | 263 | 62.980 | 16.736 | 35.460 | 1.00 | 24.48 |
| ATOM | 2415 | OH  | TYR | B | 263 | 63.549 | 15.786 | 36.270 | 1.00 | 23.66 |
| ATOM | 2416 | C   | TYR | B | 263 | 58.809 | 20.855 | 32.587 | 1.00 | 38.59 |
| ATOM | 2417 | O   | TYR | B | 263 | 58.509 | 20.918 | 31.386 | 1.00 | 38.00 |
| ATOM | 2418 | N   | TYR | B | 264 | 58.532 | 21.803 | 33.472 | 1.00 | 42.63 |
| ATOM | 2419 | CA  | TYR | B | 264 | 57.808 | 23.031 | 33.176 | 1.00 | 48.24 |
| ATOM | 2420 | CB  | TYR | B | 264 | 56.786 | 23.247 | 34.305 | 1.00 | 52.16 |
| ATOM | 2421 | CG  | TYR | B | 264 | 55.776 | 24.372 | 34.162 | 1.00 | 56.53 |
| ATOM | 2422 | CD1 | TYR | B | 264 | 55.378 | 24.853 | 32.914 | 1.00 | 57.81 |
| ATOM | 2423 | CE1 | TYR | B | 264 | 54.390 | 25.858 | 32.810 | 1.00 | 59.91 |
| ATOM | 2424 | CD2 | TYR | B | 264 | 55.169 | 24.919 | 35.310 | 1.00 | 58.59 |
| ATOM | 2425 | CE2 | TYR | B | 264 | 54.184 | 25.914 | 35.222 | 1.00 | 58.87 |
| ATOM | 2426 | CZ  | TYR | B | 264 | 53.795 | 26.381 | 33.973 | 1.00 | 59.86 |
| ATOM | 2427 | OH  | TYR | B | 264 | 52.812 | 27.352 | 33.894 | 1.00 | 59.28 |
| ATOM | 2428 | C   | TYR | B | 264 | 58.801 | 24.178 | 33.111 | 1.00 | 49.78 |
| ATOM | 2429 | O   | TYR | B | 264 | 59.608 | 24.361 | 34.023 | 1.00 | 49.95 |
| ATOM | 2430 | N   | ASN | B | 265 | 58.751 | 24.929 | 32.011 | 1.00 | 51.34 |
| ATOM | 2431 | CA  | ASN | B | 265 | 59.637 | 26.071 | 31.784 | 1.00 | 52.26 |
| ATOM | 2432 | CB  | ASN | B | 265 | 59.273 | 27.245 | 32.722 | 1.00 | 54.27 |
| ATOM | 2433 | CG  | ASN | B | 265 | 57.751 | 27.518 | 32.785 | 1.00 | 56.02 |
| ATOM | 2434 | OD1 | ASN | B | 265 | 57.091 | 27.751 | 31.764 | 1.00 | 57.42 |
| ATOM | 2435 | ND2 | ASN | B | 265 | 57.207 | 27.506 | 33.996 | 1.00 | 54.31 |
| ATOM | 2436 | C   | ASN | B | 265 | 61.103 | 25.646 | 31.973 | 1.00 | 51.61 |
| ATOM | 2437 | O   | ASN | B | 265 | 61.949 | 26.447 | 32.365 | 1.00 | 51.31 |
| ATOM | 2438 | N   | GLY | B | 266 | 61.376 | 24.367 | 31.729 | 1.00 | 51.49 |
| ATOM | 2439 | CA  | GLY | B | 266 | 62.722 | 23.848 | 31.851 | 1.00 | 51.38 |
| ATOM | 2440 | C   | GLY | B | 266 | 63.230 | 23.382 | 33.201 | 1.00 | 51.65 |
| ATOM | 2441 | O   | GLY | B | 266 | 63.971 | 22.397 | 33.248 | 1.00 | 52.02 |
| ATOM | 2442 | N   | HIS | B | 267 | 62.856 | 24.052 | 34.294 | 1.00 | 51.98 |
| ATOM | 2443 | CA  | HIS | B | 267 | 63.361 | 23.657 | 35.620 | 1.00 | 51.74 |
| ATOM | 2444 | CB  | HIS | B | 267 | 64.283 | 24.752 | 36.174 | 1.00 | 57.38 |
| ATOM | 2445 | CG  | HIS | B | 267 | 65.572 | 24.880 | 35.412 | 1.00 | 63.68 |
| ATOM | 2446 | CD2 | HIS | B | 267 | 66.664 | 24.079 | 35.373 | 1.00 | 65.69 |
| ATOM | 2447 | ND1 | HIS | B | 267 | 65.801 | 25.886 | 34.492 | 1.00 | 65.52 |
| ATOM | 2448 | CE1 | HIS | B | 267 | 66.975 | 25.692 | 33.915 | 1.00 | 67.05 |
| ATOM | 2449 | NE2 | HIS | B | 267 | 67.519 | 24.605 | 34.430 | 1.00 | 67.87 |
| ATOM | 2450 | C   | HIS | B | 267 | 62.425 | 23.132 | 36.718 | 1.00 | 47.69 |
| ATOM | 2451 | O   | HIS | B | 267 | 62.891 | 22.532 | 37.688 | 1.00 | 47.58 |
| ATOM | 2452 | N   | THR | B | 268 | 61.122 | 23.342 | 36.568 | 1.00 | 42.94 |
| ATOM | 2453 | CA  | THR | B | 268 | 60.153 | 22.864 | 37.550 | 1.00 | 37.60 |
| ATOM | 2454 | CB  | THR | B | 268 | 58.943 | 23.834 | 37.663 | 1.00 | 37.66 |
| ATOM | 2455 | OG1 | THR | B | 268 | 59.396 | 25.143 | 38.048 | 1.00 | 35.87 |
| ATOM | 2456 | CG2 | THR | B | 268 | 57.946 | 23.336 | 38.699 | 1.00 | 37.34 |
| ATOM | 2457 | C   | THR | B | 268 | 59.676 | 21.459 | 37.152 | 1.00 | 34.00 |
| ATOM | 2458 | O   | THR | B | 268 | 59.209 | 21.248 | 36.039 | 1.00 | 33.62 |
| ATOM | 2459 | N   | LYS | B | 269 | 59.829 | 20.496 | 38.053 | 1.00 | 30.04 |
| ATOM | 2460 | CA  | LYS | B | 269 | 59.419 | 19.121 | 37.796 | 1.00 | 27.53 |
| ATOM | 2461 | CB  | LYS | B | 269 | 60.188 | 18.163 | 38.686 | 1.00 | 24.11 |
| ATOM | 2462 | CG  | LYS | B | 269 | 60.173 | 16.743 | 38.211 | 1.00 | 22.00 |
| ATOM | 2463 | CD  | LYS | B | 269 | 61.090 | 15.940 | 39.081 | 1.00 | 22.43 |
| ATOM | 2464 | CE  | LYS | B | 269 | 61.149 | 14.491 | 38.668 | 1.00 | 21.59 |
| ATOM | 2465 | NZ  | LYS | B | 269 | 62.068 | 13.759 | 39.587 | 1.00 | 23.21 |

Figure 7

| | | | | | | | | | |
|---|---|---|---|---|---|---|---|---|---|
| ATOM | 2466 | C | LYS | B | 269 | 57.923 | 18.993 | 38.049 | 1.00 27.62 |
| ATOM | 2467 | O | LYS | B | 269 | 57.418 | 19.466 | 39.059 | 1.00 28.04 |
| ATOM | 2468 | N | VAL | B | 270 | 57.213 | 18.340 | 37.134 | 1.00 27.10 |
| ATOM | 2469 | CA | VAL | B | 270 | 55.768 | 18.231 | 37.258 | 1.00 26.23 |
| ATOM | 2470 | CB | VAL | B | 270 | 55.045 | 19.309 | 36.368 | 1.00 26.31 |
| ATOM | 2471 | CG1 | VAL | B | 270 | 55.374 | 20.720 | 36.843 | 1.00 25.18 |
| ATOM | 2472 | CG2 | VAL | B | 270 | 55.417 | 19.146 | 34.870 | 1.00 23.57 |
| ATOM | 2473 | C | VAL | B | 270 | 55.185 | 16.883 | 36.897 | 1.00 26.14 |
| ATOM | 2474 | O | VAL | B | 270 | 55.876 | 15.995 | 36.408 | 1.00 25.80 |
| ATOM | 2475 | N | ALA | B | 271 | 53.902 | 16.739 | 37.215 | 1.00 27.41 |
| ATOM | 2476 | CA | ALA | B | 271 | 53.128 | 15.556 | 36.871 | 1.00 28.01 |
| ATOM | 2477 | CB | ALA | B | 271 | 52.430 | 14.997 | 38.076 | 1.00 28.97 |
| ATOM | 2478 | C | ALA | B | 271 | 52.108 | 16.097 | 35.865 | 1.00 28.22 |
| ATOM | 2479 | O | ALA | B | 271 | 51.502 | 17.155 | 36.086 | 1.00 27.92 |
| ATOM | 2480 | N | VAL | B | 272 | 51.959 | 15.406 | 34.744 | 1.00 27.87 |
| ATOM | 2481 | CA | VAL | B | 272 | 51.047 | 15.841 | 33.711 | 1.00 27.37 |
| ATOM | 2482 | CB | VAL | B | 272 | 51.813 | 16.161 | 32.397 | 1.00 28.19 |
| ATOM | 2483 | CG1 | VAL | B | 272 | 50.867 | 16.701 | 31.346 | 1.00 27.78 |
| ATOM | 2484 | CG2 | VAL | B | 272 | 52.937 | 17.159 | 32.652 | 1.00 28.57 |
| ATOM | 2485 | C | VAL | B | 272 | 50.043 | 14.745 | 33.435 | 1.00 27.75 |
| ATOM | 2486 | O | VAL | B | 272 | 50.407 | 13.596 | 33.169 | 1.00 26.10 |
| ATOM | 2487 | N | LYS | B | 273 | 48.768 | 15.085 | 33.578 | 1.00 29.03 |
| ATOM | 2488 | CA | LYS | B | 273 | 47.714 | 14.131 | 33.292 | 1.00 29.80 |
| ATOM | 2489 | CB | LYS | B | 273 | 46.647 | 14.137 | 34.396 | 1.00 29.13 |
| ATOM | 2490 | CG | LYS | B | 273 | 45.662 | 12.973 | 34.279 | 1.00 30.04 |
| ATOM | 2491 | CD | LYS | B | 273 | 44.711 | 12.892 | 35.461 | 1.00 31.36 |
| ATOM | 2492 | CE | LYS | B | 273 | 45.308 | 12.123 | 36.614 | 1.00 30.36 |
| ATOM | 2493 | NZ | LYS | B | 273 | 44.311 | 11.980 | 37.698 | 1.00 31.70 |
| ATOM | 2494 | C | LYS | B | 273 | 47.137 | 14.518 | 31.923 | 1.00 29.91 |
| ATOM | 2495 | O | LYS | B | 273 | 46.764 | 15.671 | 31.700 | 1.00 29.07 |
| ATOM | 2496 | N | SER | B | 274 | 47.148 | 13.570 | 30.989 | 1.00 31.27 |
| ATOM | 2497 | CA | SER | B | 274 | 46.643 | 13.807 | 29.639 | 1.00 32.84 |
| ATOM | 2498 | CB | SER | B | 274 | 47.718 | 13.492 | 28.603 | 1.00 34.39 |
| ATOM | 2499 | OG | SER | B | 274 | 47.945 | 12.092 | 28.557 | 1.00 37.44 |
| ATOM | 2500 | C | SER | B | 274 | 45.434 | 12.937 | 29.358 | 1.00 33.10 |
| ATOM | 2501 | O | SER | B | 274 | 45.356 | 11.796 | 29.828 | 1.00 33.07 |
| ATOM | 2502 | N | LEU | B | 275 | 44.520 | 13.479 | 28.552 | 1.00 33.40 |
| ATOM | 2503 | CA | LEU | B | 275 | 43.277 | 12.808 | 28.168 | 1.00 32.26 |
| ATOM | 2504 | CB | LEU | B | 275 | 42.183 | 13.871 | 27.955 | 1.00 31.03 |
| ATOM | 2505 | CG | LEU | B | 275 | 40.810 | 13.475 | 27.367 | 1.00 30.27 |
| ATOM | 2506 | CD1 | LEU | B | 275 | 40.060 | 12.551 | 28.337 | 1.00 28.21 |
| ATOM | 2507 | CD2 | LEU | B | 275 | 39.991 | 14.727 | 27.027 | 1.00 26.40 |
| ATOM | 2508 | C | LEU | B | 275 | 43.383 | 11.939 | 26.905 | 1.00 32.82 |
| ATOM | 2509 | O | LEU | B | 275 | 43.848 | 12.405 | 25.860 | 1.00 33.23 |
| ATOM | 2510 | N | LYS | B | 276 | 42.954 | 10.681 | 27.001 | 1.00 33.88 |
| ATOM | 2511 | CA | LYS | B | 276 | 42.939 | 9.784 | 25.840 | 1.00 36.58 |
| ATOM | 2512 | CB | LYS | B | 276 | 42.766 | 8.319 | 26.281 | 1.00 38.01 |
| ATOM | 2513 | CG | LYS | B | 276 | 42.740 | 7.277 | 25.141 | 1.00 41.35 |
| ATOM | 2514 | CD | LYS | B | 276 | 42.793 | 5.832 | 25.683 | 1.00 45.79 |
| ATOM | 2515 | CE | LYS | B | 276 | 44.083 | 5.598 | 26.514 | 1.00 51.26 |
| ATOM | 2516 | NZ | LYS | B | 276 | 44.288 | 4.225 | 27.096 | 1.00 51.78 |
| ATOM | 2517 | C | LYS | B | 276 | 41.719 | 10.235 | 25.030 | 1.00 38.25 |
| ATOM | 2518 | O | LYS | B | 276 | 40.580 | 10.059 | 25.471 | 1.00 37.74 |
| ATOM | 2519 | N | GLN | B | 277 | 41.961 | 10.904 | 23.902 | 1.00 39.57 |
| ATOM | 2520 | CA | GLN | B | 277 | 40.885 | 11.387 | 23.037 | 1.00 41.11 |
| ATOM | 2521 | CB | GLN | B | 277 | 41.438 | 11.773 | 21.657 | 1.00 45.87 |
| ATOM | 2522 | CG | GLN | B | 277 | 40.380 | 12.347 | 20.688 | 1.00 53.60 |
| ATOM | 2523 | CD | GLN | B | 277 | 40.946 | 12.794 | 19.324 | 1.00 58.47 |
| ATOM | 2524 | OE1 | GLN | B | 277 | 42.096 | 12.502 | 18.968 | 1.00 61.52 |

Figure 7

| | | | | | | | | | |
|---|---|---|---|---|---|---|---|---|---|
| ATOM | 2525 | NE2 | GLN | B | 277 | 40.123 | 13.499 | 18.555 | 1.00 59.81 |
| ATOM | 2526 | C | GLN | B | 277 | 39.773 | 10.342 | 22.867 | 1.00 40.26 |
| ATOM | 2527 | O | GLN | B | 277 | 40.042 | 9.181 | 22.535 | 1.00 40.36 |
| ATOM | 2528 | N | GLY | B | 278 | 38.535 | 10.753 | 23.146 | 1.00 38.88 |
| ATOM | 2529 | CA | GLY | B | 278 | 37.399 | 9.855 | 23.011 | 1.00 37.17 |
| ATOM | 2530 | C | GLY | B | 278 | 36.927 | 9.195 | 24.297 | 1.00 36.92 |
| ATOM | 2531 | O | GLY | B | 278 | 35.957 | 8.420 | 24.290 | 1.00 37.53 |
| ATOM | 2532 | N | SER | B | 279 | 37.622 | 9.468 | 25.396 | 1.00 34.69 |
| ATOM | 2533 | CA | SER | B | 279 | 37.245 | 8.897 | 26.675 | 1.00 32.97 |
| ATOM | 2534 | CB | SER | B | 279 | 38.449 | 8.898 | 27.613 | 1.00 32.74 |
| ATOM | 2535 | OG | SER | B | 279 | 39.376 | 7.920 | 27.183 | 1.00 30.12 |
| ATOM | 2536 | C | SER | B | 279 | 36.081 | 9.694 | 27.254 | 1.00 32.00 |
| ATOM | 2537 | O | SER | B | 279 | 35.120 | 9.135 | 27.768 | 1.00 31.27 |
| ATOM | 2538 | N | MET | B | 280 | 36.196 | 11.009 | 27.154 | 1.00 31.85 |
| ATOM | 2539 | CA | MET | B | 280 | 35.179 | 11.954 | 27.600 | 1.00 32.70 |
| ATOM | 2540 | CB | MET | B | 280 | 35.236 | 12.168 | 29.119 | 1.00 32.25 |
| ATOM | 2541 | CG | MET | B | 280 | 36.432 | 12.950 | 29.631 | 1.00 31.51 |
| ATOM | 2542 | SD | MET | B | 280 | 36.715 | 12.509 | 31.343 | 1.00 32.58 |
| ATOM | 2543 | CE | MET | B | 280 | 35.889 | 13.691 | 32.116 | 1.00 31.92 |
| ATOM | 2544 | C | MET | B | 280 | 35.529 | 13.231 | 26.864 | 1.00 33.48 |
| ATOM | 2545 | O | MET | B | 280 | 36.566 | 13.292 | 26.202 | 1.00 34.77 |
| ATOM | 2546 | N | SER | B | 281 | 34.684 | 14.249 | 26.951 | 1.00 33.57 |
| ATOM | 2547 | CA | SER | B | 281 | 34.994 | 15.480 | 26.251 | 1.00 34.24 |
| ATOM | 2548 | CB | SER | B | 281 | 33.746 | 16.350 | 26.075 | 1.00 33.79 |
| ATOM | 2549 | OG | SER | B | 281 | 33.468 | 17.109 | 27.242 | 1.00 31.69 |
| ATOM | 2550 | C | SER | B | 281 | 36.055 | 16.276 | 27.001 | 1.00 35.76 |
| ATOM | 2551 | O | SER | B | 281 | 36.277 | 16.068 | 28.204 | 1.00 35.89 |
| ATOM | 2552 | N | PRO | B | 282 | 36.761 | 17.162 | 26.281 | 1.00 36.52 |
| ATOM | 2553 | CD | PRO | B | 282 | 36.785 | 17.203 | 24.806 | 1.00 36.86 |
| ATOM | 2554 | CA | PRO | B | 282 | 37.812 | 18.022 | 26.840 | 1.00 36.53 |
| ATOM | 2555 | CB | PRO | B | 282 | 38.188 | 18.897 | 25.645 | 1.00 36.49 |
| ATOM | 2556 | CG | PRO | B | 282 | 38.101 | 17.916 | 24.510 | 1.00 37.32 |
| ATOM | 2557 | C | PRO | B | 282 | 37.257 | 18.860 | 27.993 | 1.00 36.36 |
| ATOM | 2558 | O | PRO | B | 282 | 37.911 | 19.029 | 29.022 | 1.00 35.71 |
| ATOM | 2559 | N | ASP | B | 283 | 36.028 | 19.339 | 27.822 | 1.00 36.89 |
| ATOM | 2560 | CA | ASP | B | 283 | 35.355 | 20.157 | 28.831 | 1.00 35.98 |
| ATOM | 2561 | CB | ASP | B | 283 | 34.068 | 20.764 | 28.252 | 1.00 39.66 |
| ATOM | 2562 | CG | ASP | B | 283 | 34.342 | 21.909 | 27.262 | 1.00 45.17 |
| ATOM | 2563 | OD1 | ASP | B | 283 | 35.421 | 22.550 | 27.342 | 1.00 47.89 |
| ATOM | 2564 | OD2 | ASP | B | 283 | 33.462 | 22.187 | 26.413 | 1.00 47.88 |
| ATOM | 2565 | C | ASP | B | 283 | 35.068 | 19.376 | 30.109 | 1.00 33.48 |
| ATOM | 2566 | O | ASP | B | 283 | 35.221 | 19.901 | 31.207 | 1.00 32.39 |
| ATOM | 2567 | N | ALA | B | 284 | 34.721 | 18.104 | 29.960 | 1.00 31.28 |
| ATOM | 2568 | CA | ALA | B | 284 | 34.423 | 17.249 | 31.102 | 1.00 30.39 |
| ATOM | 2569 | CB | ALA | B | 284 | 33.723 | 16.002 | 30.640 | 1.00 28.64 |
| ATOM | 2570 | C | ALA | B | 284 | 35.682 | 16.881 | 31.894 | 1.00 30.43 |
| ATOM | 2571 | O | ALA | B | 284 | 35.644 | 16.761 | 33.126 | 1.00 30.10 |
| ATOM | 2572 | N | PHE | B | 285 | 36.789 | 16.698 | 31.171 | 1.00 30.71 |
| ATOM | 2573 | CA | PHE | B | 285 | 38.081 | 16.340 | 31.749 | 1.00 29.07 |
| ATOM | 2574 | CB | PHE | B | 285 | 39.025 | 15.891 | 30.635 | 1.00 28.92 |
| ATOM | 2575 | CG | PHE | B | 285 | 40.420 | 15.566 | 31.099 | 1.00 29.20 |
| ATOM | 2576 | CD1 | PHE | B | 285 | 40.687 | 14.380 | 31.772 | 1.00 28.47 |
| ATOM | 2577 | CD2 | PHE | B | 285 | 41.476 | 16.438 | 30.829 | 1.00 27.76 |
| ATOM | 2578 | CE1 | PHE | B | 285 | 41.986 | 14.072 | 32.161 | 1.00 28.04 |
| ATOM | 2579 | CE2 | PHE | B | 285 | 42.770 | 16.133 | 31.217 | 1.00 26.81 |
| ATOM | 2580 | CZ | PHE | B | 285 | 43.025 | 14.953 | 31.880 | 1.00 27.55 |
| ATOM | 2581 | C | PHE | B | 285 | 38.663 | 17.514 | 32.523 | 1.00 28.27 |
| ATOM | 2582 | O | PHE | B | 285 | 39.092 | 17.358 | 33.660 | 1.00 27.62 |
| ATOM | 2583 | N | LEU | B | 286 | 38.649 | 18.686 | 31.904 | 1.00 29.14 |

Figure 7

```
ATOM   2584  CA   LEU B 286      39.151  19.913  32.510  1.00 31.38
ATOM   2585  CB   LEU B 286      39.145  21.042  31.477  1.00 32.67
ATOM   2586  CG   LEU B 286      40.087  20.888  30.273  1.00 35.43
ATOM   2587  CD1  LEU B 286      39.683  21.832  29.148  1.00 35.04
ATOM   2588  CD2  LEU B 286      41.540  21.128  30.699  1.00 36.05
ATOM   2589  C    LEU B 286      38.320  20.338  33.715  1.00 32.89
ATOM   2590  O    LEU B 286      38.835  20.943  34.659  1.00 31.81
ATOM   2591  N    ALA B 287      37.030  20.017  33.665  1.00 35.21
ATOM   2592  CA   ALA B 287      36.082  20.355  34.723  1.00 37.52
ATOM   2593  CB   ALA B 287      34.680  19.846  34.355  1.00 36.61
ATOM   2594  C    ALA B 287      36.510  19.788  36.058  1.00 39.44
ATOM   2595  O    ALA B 287      36.351  20.432  37.098  1.00 41.04
ATOM   2596  N    GLU B 288      37.039  18.572  36.025  1.00 41.49
ATOM   2597  CA   GLU B 288      37.506  17.891  37.227  1.00 45.58
ATOM   2598  CB   GLU B 288      37.844  16.451  36.880  1.00 46.37
ATOM   2599  CG   GLU B 288      36.652  15.723  36.285  1.00 49.85
ATOM   2600  CD   GLU B 288      36.960  14.300  35.887  1.00 53.01
ATOM   2601  OE1  GLU B 288      38.143  14.014  35.600  1.00 54.72
ATOM   2602  OE2  GLU B 288      36.022  13.465  35.856  1.00 54.54
ATOM   2603  C    GLU B 288      38.690  18.603  37.891  1.00 47.61
ATOM   2604  O    GLU B 288      38.922  18.462  39.089  1.00 47.44
ATOM   2605  N    ALA B 289      39.419  19.381  37.095  1.00 50.11
ATOM   2606  CA   ALA B 289      40.550  20.161  37.570  1.00 52.37
ATOM   2607  CB   ALA B 289      41.472  20.492  36.409  1.00 52.85
ATOM   2608  C    ALA B 289      40.040  21.453  38.206  1.00 54.58
ATOM   2609  O    ALA B 289      40.615  21.932  39.172  1.00 54.25
ATOM   2610  N    ASN B 290      38.974  22.019  37.634  1.00 57.42
ATOM   2611  CA   ASN B 290      38.347  23.274  38.104  1.00 58.55
ATOM   2612  CB   ASN B 290      37.093  23.587  37.261  1.00 59.89
ATOM   2613  CG   ASN B 290      37.419  23.946  35.805  1.00 61.62
ATOM   2614  OD1  ASN B 290      36.566  23.805  34.922  1.00 62.66
ATOM   2615  ND2  ASN B 290      38.641  24.433  35.558  1.00 61.45
ATOM   2616  C    ASN B 290      37.992  23.352  39.604  1.00 57.27
ATOM   2617  O    ASN B 290      37.498  24.367  40.092  1.00 58.32
ATOM   2618  N    LEU B 291      38.302  22.289  40.327  1.00 55.72
ATOM   2619  CA   LEU B 291      38.027  22.164  41.758  1.00 54.04
ATOM   2620  CB   LEU B 291      37.387  20.790  41.973  1.00 57.04
ATOM   2621  CG   LEU B 291      36.563  20.371  40.729  1.00 58.68
ATOM   2622  CD1  LEU B 291      36.366  18.871  40.649  1.00 56.97
ATOM   2623  CD2  LEU B 291      35.228  21.130  40.673  1.00 61.46
ATOM   2624  C    LEU B 291      39.322  22.310  42.584  1.00 51.92
ATOM   2625  O    LEU B 291      39.301  22.668  43.765  1.00 51.58
ATOM   2626  N    MET B 292      40.441  21.990  41.937  1.00 49.47
ATOM   2627  CA   MET B 292      41.797  22.087  42.489  1.00 45.59
ATOM   2628  CB   MET B 292      42.704  21.137  41.703  1.00 42.45
ATOM   2629  CG   MET B 292      44.136  20.992  42.179  1.00 40.53
ATOM   2630  SD   MET B 292      45.036  19.774  41.150  1.00 34.75
ATOM   2631  CE   MET B 292      44.979  18.326  42.237  1.00 35.14
ATOM   2632  C    MET B 292      42.210  23.552  42.256  1.00 44.67
ATOM   2633  O    MET B 292      43.101  24.086  42.922  1.00 43.41
ATOM   2634  N    LYS B 293      41.523  24.189  41.305  1.00 44.49
ATOM   2635  CA   LYS B 293      41.727  25.588  40.950  1.00 44.40
ATOM   2636  CB   LYS B 293      40.919  25.948  39.701  1.00 44.27
ATOM   2637  CG   LYS B 293      41.392  25.360  38.402  1.00 45.56
ATOM   2638  CD   LYS B 293      40.735  26.101  37.259  1.00 48.23
ATOM   2639  CE   LYS B 293      41.348  25.751  35.911  1.00 51.69
ATOM   2640  NZ   LYS B 293      40.923  26.699  34.819  1.00 55.08
ATOM   2641  C    LYS B 293      41.232  26.484  42.070  1.00 44.42
ATOM   2642  O    LYS B 293      41.737  27.586  42.254  1.00 45.57
```

Figure 7

| ATOM | 2643 | N   | GLN | B | 294 | 40.189 | 26.027 | 42.765 | 1.00 | 44.82 |
|------|------|-----|-----|---|-----|--------|--------|--------|------|-------|
| ATOM | 2644 | CA  | GLN | B | 294 | 39.569 | 26.782 | 43.854 | 1.00 | 45.38 |
| ATOM | 2645 | CB  | GLN | B | 294 | 38.074 | 26.428 | 43.981 | 1.00 | 48.18 |
| ATOM | 2646 | CG  | GLN | B | 294 | 37.269 | 26.468 | 42.673 | 1.00 | 53.82 |
| ATOM | 2647 | CD  | GLN | B | 294 | 37.270 | 27.843 | 42.003 | 1.00 | 57.34 |
| ATOM | 2648 | OE1 | GLN | B | 294 | 37.853 | 28.032 | 40.922 | 1.00 | 58.94 |
| ATOM | 2649 | NE2 | GLN | B | 294 | 36.588 | 28.802 | 42.628 | 1.00 | 58.98 |
| ATOM | 2650 | C   | GLN | B | 294 | 40.226 | 26.602 | 45.215 | 1.00 | 44.12 |
| ATOM | 2651 | O   | GLN | B | 294 | 40.407 | 27.569 | 45.948 | 1.00 | 44.89 |
| ATOM | 2652 | N   | LEU | B | 295 | 40.595 | 25.370 | 45.547 | 1.00 | 42.32 |
| ATOM | 2653 | CA  | LEU | B | 295 | 41.185 | 25.097 | 46.854 | 1.00 | 40.69 |
| ATOM | 2654 | CB  | LEU | B | 295 | 40.481 | 23.916 | 47.529 | 1.00 | 40.36 |
| ATOM | 2655 | CG  | LEU | B | 295 | 38.986 | 24.015 | 47.837 | 1.00 | 40.60 |
| ATOM | 2656 | CD1 | LEU | B | 295 | 38.550 | 22.734 | 48.519 | 1.00 | 40.56 |
| ATOM | 2657 | CD2 | LEU | B | 295 | 38.692 | 25.217 | 48.724 | 1.00 | 38.48 |
| ATOM | 2658 | C   | LEU | B | 295 | 42.678 | 24.859 | 46.878 | 1.00 | 39.49 |
| ATOM | 2659 | O   | LEU | B | 295 | 43.178 | 23.938 | 46.244 | 1.00 | 38.98 |
| ATOM | 2660 | N   | GLN | B | 296 | 43.375 | 25.662 | 47.673 | 1.00 | 37.64 |
| ATOM | 2661 | CA  | GLN | B | 296 | 44.819 | 25.537 | 47.811 | 1.00 | 37.46 |
| ATOM | 2662 | CB  | GLN | B | 296 | 45.525 | 26.719 | 47.124 | 1.00 | 39.63 |
| ATOM | 2663 | CG  | GLN | B | 296 | 45.281 | 26.735 | 45.601 | 1.00 | 44.10 |
| ATOM | 2664 | CD  | GLN | B | 296 | 44.956 | 28.107 | 45.063 | 1.00 | 47.07 |
| ATOM | 2665 | OE1 | GLN | B | 296 | 44.582 | 29.007 | 45.817 | 1.00 | 49.52 |
| ATOM | 2666 | NE2 | GLN | B | 296 | 45.083 | 28.277 | 43.749 | 1.00 | 48.80 |
| ATOM | 2667 | C   | GLN | B | 296 | 45.191 | 25.401 | 49.289 | 1.00 | 35.77 |
| ATOM | 2668 | O   | GLN | B | 296 | 44.686 | 26.133 | 50.142 | 1.00 | 35.79 |
| ATOM | 2669 | N   | HIS | B | 297 | 46.019 | 24.402 | 49.584 | 1.00 | 33.84 |
| ATOM | 2670 | CA  | HIS | B | 297 | 46.448 | 24.115 | 50.953 | 1.00 | 32.96 |
| ATOM | 2671 | CB  | HIS | B | 297 | 45.339 | 23.322 | 51.667 | 1.00 | 31.72 |
| ATOM | 2672 | CG  | HIS | B | 297 | 45.547 | 23.180 | 53.140 | 1.00 | 29.18 |
| ATOM | 2673 | CD2 | HIS | B | 297 | 45.219 | 23.996 | 54.171 | 1.00 | 28.54 |
| ATOM | 2674 | ND1 | HIS | B | 297 | 46.234 | 22.127 | 53.697 | 1.00 | 28.57 |
| ATOM | 2675 | CE1 | HIS | B | 297 | 46.335 | 22.299 | 55.002 | 1.00 | 27.39 |
| ATOM | 2676 | NE2 | HIS | B | 297 | 45.727 | 23.428 | 55.311 | 1.00 | 28.85 |
| ATOM | 2677 | C   | HIS | B | 297 | 47.745 | 23.289 | 50.924 | 1.00 | 32.96 |
| ATOM | 2678 | O   | HIS | B | 297 | 48.051 | 22.660 | 49.912 | 1.00 | 32.64 |
| ATOM | 2679 | N   | GLN | B | 298 | 48.502 | 23.288 | 52.025 | 1.00 | 33.21 |
| ATOM | 2680 | CA  | GLN | B | 298 | 49.751 | 22.511 | 52.084 | 1.00 | 34.54 |
| ATOM | 2681 | CB  | GLN | B | 298 | 50.606 | 22.845 | 53.321 | 1.00 | 36.37 |
| ATOM | 2682 | CG  | GLN | B | 298 | 51.518 | 24.083 | 53.154 | 1.00 | 44.33 |
| ATOM | 2683 | CD  | GLN | B | 298 | 52.112 | 24.267 | 51.732 | 1.00 | 46.62 |
| ATOM | 2684 | OE1 | GLN | B | 298 | 51.817 | 25.258 | 51.054 | 1.00 | 47.54 |
| ATOM | 2685 | NE2 | GLN | B | 298 | 52.960 | 23.327 | 51.296 | 1.00 | 48.19 |
| ATOM | 2686 | C   | GLN | B | 298 | 49.553 | 21.009 | 52.023 | 1.00 | 33.50 |
| ATOM | 2687 | O   | GLN | B | 298 | 50.500 | 20.268 | 51.747 | 1.00 | 34.40 |
| ATOM | 2688 | N   | ARG | B | 299 | 48.314 | 20.569 | 52.236 | 1.00 | 32.24 |
| ATOM | 2689 | CA  | ARG | B | 299 | 47.975 | 19.148 | 52.244 | 1.00 | 30.45 |
| ATOM | 2690 | CB  | ARG | B | 299 | 47.174 | 18.800 | 53.506 | 1.00 | 29.33 |
| ATOM | 2691 | CG  | ARG | B | 299 | 47.895 | 19.132 | 54.787 | 1.00 | 29.90 |
| ATOM | 2692 | CD  | ARG | B | 299 | 49.105 | 18.262 | 54.896 | 1.00 | 31.69 |
| ATOM | 2693 | NE  | ARG | B | 299 | 50.115 | 18.756 | 55.823 | 1.00 | 32.36 |
| ATOM | 2694 | CZ  | ARG | B | 299 | 51.421 | 18.721 | 55.554 | 1.00 | 34.32 |
| ATOM | 2695 | NH1 | ARG | B | 299 | 51.844 | 18.244 | 54.382 | 1.00 | 35.45 |
| ATOM | 2696 | NH2 | ARG | B | 299 | 52.300 | 19.052 | 56.482 | 1.00 | 32.91 |
| ATOM | 2697 | C   | ARG | B | 299 | 47.191 | 18.761 | 51.004 | 1.00 | 29.45 |
| ATOM | 2698 | O   | ARG | B | 299 | 46.647 | 17.662 | 50.924 | 1.00 | 29.16 |
| ATOM | 2699 | N   | LEU | B | 300 | 47.069 | 19.697 | 50.076 | 1.00 | 29.63 |
| ATOM | 2700 | CA  | LEU | B | 300 | 46.371 | 19.448 | 48.821 | 1.00 | 30.82 |
| ATOM | 2701 | CB  | LEU | B | 300 | 45.205 | 20.427 | 48.645 | 1.00 | 30.34 |

Figure 7

| | | | | | | | | | |
|---|---|---|---|---|---|---|---|---|---|
| ATOM | 2702 | CG | LEU | B | 300 | 43.791 | 20.057 | 49.094 | 1.00 29.72 |
| ATOM | 2703 | CD1 | LEU | B | 300 | 43.774 | 19.394 | 50.461 | 1.00 29.47 |
| ATOM | 2704 | CD2 | LEU | B | 300 | 42.944 | 21.319 | 49.088 | 1.00 28.53 |
| ATOM | 2705 | C | LEU | B | 300 | 47.379 | 19.634 | 47.690 | 1.00 31.27 |
| ATOM | 2706 | O | LEU | B | 300 | 48.197 | 20.560 | 47.724 | 1.00 31.07 |
| ATOM | 2707 | N | VAL | B | 301 | 47.332 | 18.737 | 46.707 | 1.00 32.54 |
| ATOM | 2708 | CA | VAL | B | 301 | 48.225 | 18.806 | 45.559 | 1.00 32.47 |
| ATOM | 2709 | CB | VAL | B | 301 | 48.116 | 17.534 | 44.689 | 1.00 31.52 |
| ATOM | 2710 | CG1 | VAL | B | 301 | 48.834 | 17.730 | 43.367 | 1.00 29.51 |
| ATOM | 2711 | CG2 | VAL | B | 301 | 48.738 | 16.344 | 45.435 | 1.00 28.56 |
| ATOM | 2712 | C | VAL | B | 301 | 47.909 | 20.085 | 44.778 | 1.00 33.35 |
| ATOM | 2713 | O | VAL | B | 301 | 46.751 | 20.405 | 44.518 | 1.00 32.24 |
| ATOM | 2714 | N | ARG | B | 302 | 48.964 | 20.834 | 44.468 | 1.00 34.82 |
| ATOM | 2715 | CA | ARG | B | 302 | 48.872 | 22.109 | 43.776 | 1.00 37.12 |
| ATOM | 2716 | CB | ARG | B | 302 | 50.027 | 23.007 | 44.268 | 1.00 40.38 |
| ATOM | 2717 | CG | ARG | B | 302 | 50.055 | 24.452 | 43.768 | 1.00 47.36 |
| ATOM | 2718 | CD | ARG | B | 302 | 50.974 | 24.603 | 42.542 | 1.00 54.67 |
| ATOM | 2719 | NE | ARG | B | 302 | 51.411 | 25.987 | 42.274 | 1.00 60.06 |
| ATOM | 2720 | CZ | ARG | B | 302 | 52.390 | 26.621 | 42.932 | 1.00 62.11 |
| ATOM | 2721 | NH1 | ARG | B | 302 | 53.049 | 26.007 | 43.910 | 1.00 63.76 |
| ATOM | 2722 | NH2 | ARG | B | 302 | 52.752 | 27.850 | 42.579 | 1.00 61.82 |
| ATOM | 2723 | C | ARG | B | 302 | 48.854 | 21.980 | 42.250 | 1.00 37.35 |
| ATOM | 2724 | O | ARG | B | 302 | 49.629 | 21.217 | 41.660 | 1.00 38.29 |
| ATOM | 2725 | N | LEU | B | 303 | 47.934 | 22.710 | 41.622 | 1.00 36.71 |
| ATOM | 2726 | CA | LEU | B | 303 | 47.790 | 22.731 | 40.165 | 1.00 35.81 |
| ATOM | 2727 | CB | LEU | B | 303 | 46.321 | 22.965 | 39.799 | 1.00 35.19 |
| ATOM | 2728 | CG | LEU | B | 303 | 45.949 | 22.994 | 38.318 | 1.00 35.17 |
| ATOM | 2729 | CD1 | LEU | B | 303 | 46.035 | 21.597 | 37.741 | 1.00 35.38 |
| ATOM | 2730 | CD2 | LEU | B | 303 | 44.548 | 23.547 | 38.149 | 1.00 35.68 |
| ATOM | 2731 | C | LEU | B | 303 | 48.636 | 23.877 | 39.611 | 1.00 35.50 |
| ATOM | 2732 | O | LEU | B | 303 | 48.598 | 24.995 | 40.132 | 1.00 35.39 |
| ATOM | 2733 | N | TYR | B | 304 | 49.428 | 23.598 | 38.583 | 1.00 35.36 |
| ATOM | 2734 | CA | TYR | B | 304 | 50.269 | 24.635 | 37.975 | 1.00 36.40 |
| ATOM | 2735 | CB | TYR | B | 304 | 51.636 | 24.071 | 37.559 | 1.00 37.54 |
| ATOM | 2736 | CG | TYR | B | 304 | 52.596 | 23.839 | 38.701 | 1.00 40.66 |
| ATOM | 2737 | CD1 | TYR | B | 304 | 53.274 | 22.634 | 38.826 | 1.00 41.98 |
| ATOM | 2738 | CE1 | TYR | B | 304 | 54.186 | 22.420 | 39.852 | 1.00 43.08 |
| ATOM | 2739 | CD2 | TYR | B | 304 | 52.849 | 24.831 | 39.638 | 1.00 42.41 |
| ATOM | 2740 | CE2 | TYR | B | 304 | 53.765 | 24.620 | 40.674 | 1.00 44.15 |
| ATOM | 2741 | CZ | TYR | B | 304 | 54.427 | 23.416 | 40.771 | 1.00 43.48 |
| ATOM | 2742 | OH | TYR | B | 304 | 55.346 | 23.209 | 41.773 | 1.00 44.87 |
| ATOM | 2743 | C | TYR | B | 304 | 49.614 | 25.271 | 36.759 | 1.00 35.49 |
| ATOM | 2744 | O | TYR | B | 304 | 49.465 | 26.486 | 36.684 | 1.00 34.41 |
| ATOM | 2745 | N | ALA | B | 305 | 49.206 | 24.425 | 35.825 | 1.00 35.37 |
| ATOM | 2746 | CA | ALA | B | 305 | 48.596 | 24.895 | 34.606 | 1.00 35.95 |
| ATOM | 2747 | CB | ALA | B | 305 | 49.680 | 25.418 | 33.684 | 1.00 35.00 |
| ATOM | 2748 | C | ALA | B | 305 | 47.823 | 23.791 | 33.911 | 1.00 36.82 |
| ATOM | 2749 | O | ALA | B | 305 | 47.698 | 22.674 | 34.421 | 1.00 36.50 |
| ATOM | 2750 | N | VAL | B | 306 | 47.309 | 24.126 | 32.730 | 1.00 38.51 |
| ATOM | 2751 | CA | VAL | B | 306 | 46.559 | 23.205 | 31.881 | 1.00 39.58 |
| ATOM | 2752 | CB | VAL | B | 306 | 45.007 | 23.252 | 32.151 | 1.00 40.69 |
| ATOM | 2753 | CG1 | VAL | B | 306 | 44.694 | 22.950 | 33.624 | 1.00 41.59 |
| ATOM | 2754 | CG2 | VAL | B | 306 | 44.418 | 24.606 | 31.744 | 1.00 39.76 |
| ATOM | 2755 | C | VAL | B | 306 | 46.797 | 23.623 | 30.432 | 1.00 40.16 |
| ATOM | 2756 | O | VAL | B | 306 | 47.093 | 24.792 | 30.150 | 1.00 39.55 |
| ATOM | 2757 | N | VAL | B | 307 | 46.738 | 22.649 | 29.532 | 1.00 41.40 |
| ATOM | 2758 | CA | VAL | B | 307 | 46.882 | 22.891 | 28.101 | 1.00 42.40 |
| ATOM | 2759 | CB | VAL | B | 307 | 48.069 | 22.086 | 27.491 | 1.00 41.78 |
| ATOM | 2760 | CG1 | VAL | B | 307 | 48.115 | 22.248 | 25.984 | 1.00 40.03 |

Figure 7

| | | | | | | | | | |
|---|---|---|---|---|---|---|---|---|---|
| ATOM | 2761 | CG2 | VAL | B | 307 | 49.382 | 22.569 | 28.089 | 1.00 41.68 |
| ATOM | 2762 | C | VAL | B | 307 | 45.537 | 22.456 | 27.520 | 1.00 43.34 |
| ATOM | 2763 | O | VAL | B | 307 | 45.171 | 21.279 | 27.576 | 1.00 41.81 |
| ATOM | 2764 | N | THR | B | 308 | 44.791 | 23.436 | 27.014 | 1.00 46.06 |
| ATOM | 2765 | CA | THR | B | 308 | 43.462 | 23.208 | 26.454 | 1.00 48.71 |
| ATOM | 2766 | CB | THR | B | 308 | 42.588 | 24.471 | 26.577 | 1.00 49.35 |
| ATOM | 2767 | OG1 | THR | B | 308 | 43.183 | 25.551 | 25.844 | 1.00 52.63 |
| ATOM | 2768 | CG2 | THR | B | 308 | 42.461 | 24.871 | 28.032 | 1.00 47.45 |
| ATOM | 2769 | C | THR | B | 308 | 43.383 | 22.628 | 25.034 | 1.00 50.32 |
| ATOM | 2770 | O | THR | B | 308 | 42.314 | 22.180 | 24.617 | 1.00 51.17 |
| ATOM | 2771 | N | GLN | B | 309 | 44.492 | 22.640 | 24.290 | 1.00 51.63 |
| ATOM | 2772 | CA | GLN | B | 309 | 44.518 | 22.057 | 22.946 | 1.00 53.18 |
| ATOM | 2773 | CB | GLN | B | 309 | 45.575 | 22.743 | 22.075 | 1.00 57.15 |
| ATOM | 2774 | CG | GLN | B | 309 | 45.217 | 24.166 | 21.675 | 1.00 62.61 |
| ATOM | 2775 | CD | GLN | B | 309 | 43.918 | 24.237 | 20.876 | 1.00 67.18 |
| ATOM | 2776 | OE1 | GLN | B | 309 | 43.417 | 23.220 | 20.369 | 1.00 68.61 |
| ATOM | 2777 | NE2 | GLN | B | 309 | 43.366 | 25.442 | 20.760 | 1.00 69.00 |
| ATOM | 2778 | C | GLN | B | 309 | 44.835 | 20.572 | 23.083 | 1.00 52.01 |
| ATOM | 2779 | O | GLN | B | 309 | 45.778 | 20.209 | 23.794 | 1.00 51.07 |
| ATOM | 2780 | N | GLU | B | 310 | 44.087 | 19.720 | 22.383 | 1.00 51.14 |
| ATOM | 2781 | CA | GLU | B | 310 | 44.296 | 18.280 | 22.495 | 1.00 52.25 |
| ATOM | 2782 | CB | GLU | B | 310 | 43.135 | 17.494 | 21.869 | 1.00 55.54 |
| ATOM | 2783 | CG | GLU | B | 310 | 43.189 | 17.365 | 20.354 | 1.00 63.91 |
| ATOM | 2784 | CD | GLU | B | 310 | 42.001 | 18.017 | 19.656 | 1.00 68.42 |
| ATOM | 2785 | OE1 | GLU | B | 310 | 40.846 | 17.676 | 20.027 | 1.00 71.41 |
| ATOM | 2786 | OE2 | GLU | B | 310 | 42.226 | 18.859 | 18.740 | 1.00 68.45 |
| ATOM | 2787 | C | GLU | B | 310 | 45.646 | 17.818 | 21.936 | 1.00 51.09 |
| ATOM | 2788 | O | GLU | B | 310 | 46.124 | 18.368 | 20.944 | 1.00 51.54 |
| ATOM | 2789 | N | PRO | B | 311 | 46.317 | 16.858 | 22.615 | 1.00 49.47 |
| ATOM | 2790 | CD | PRO | B | 311 | 47.574 | 16.286 | 22.101 | 1.00 49.19 |
| ATOM | 2791 | CA | PRO | B | 311 | 45.920 | 16.172 | 23.859 | 1.00 47.38 |
| ATOM | 2792 | CB | PRO | B | 311 | 47.077 | 15.200 | 24.095 | 1.00 48.66 |
| ATOM | 2793 | CG | PRO | B | 311 | 47.568 | 14.908 | 22.709 | 1.00 48.71 |
| ATOM | 2794 | C | PRO | B | 311 | 45.762 | 17.132 | 25.040 | 1.00 44.97 |
| ATOM | 2795 | O | PRO | B | 311 | 46.605 | 18.004 | 25.258 | 1.00 44.47 |
| ATOM | 2796 | N | ILE | B | 312 | 44.659 | 16.988 | 25.776 | 1.00 42.82 |
| ATOM | 2797 | CA | ILE | B | 312 | 44.382 | 17.859 | 26.928 | 1.00 39.29 |
| ATOM | 2798 | CB | ILE | B | 312 | 42.897 | 17.756 | 27.390 | 1.00 37.92 |
| ATOM | 2799 | CG2 | ILE | B | 312 | 42.526 | 18.972 | 28.212 | 1.00 36.27 |
| ATOM | 2800 | CG1 | ILE | B | 312 | 41.960 | 17.692 | 26.180 | 1.00 38.30 |
| ATOM | 2801 | CD1 | ILE | B | 312 | 41.908 | 18.960 | 25.369 | 1.00 38.71 |
| ATOM | 2802 | C | ILE | B | 312 | 45.313 | 17.505 | 28.097 | 1.00 36.67 |
| ATOM | 2803 | O | ILE | B | 312 | 45.475 | 16.326 | 28.439 | 1.00 35.72 |
| ATOM | 2804 | N | TYR | B | 313 | 45.946 | 18.536 | 28.669 | 1.00 34.66 |
| ATOM | 2805 | CA | TYR | B | 313 | 46.880 | 18.390 | 29.791 | 1.00 32.13 |
| ATOM | 2806 | CB | TYR | B | 313 | 48.269 | 18.920 | 29.418 | 1.00 31.75 |
| ATOM | 2807 | CG | TYR | B | 313 | 49.076 | 18.117 | 28.416 | 1.00 33.03 |
| ATOM | 2808 | CD1 | TYR | B | 313 | 48.702 | 16.831 | 28.038 | 1.00 34.17 |
| ATOM | 2809 | CE1 | TYR | B | 313 | 49.477 | 16.093 | 27.129 | 1.00 35.14 |
| ATOM | 2810 | CD2 | TYR | B | 313 | 50.245 | 18.649 | 27.863 | 1.00 33.54 |
| ATOM | 2811 | CE2 | TYR | B | 313 | 51.023 | 17.920 | 26.959 | 1.00 32.83 |
| ATOM | 2812 | CZ | TYR | B | 313 | 50.632 | 16.650 | 26.599 | 1.00 34.26 |
| ATOM | 2813 | OH | TYR | B | 313 | 51.380 | 15.939 | 25.692 | 1.00 34.91 |
| ATOM | 2814 | C | TYR | B | 313 | 46.475 | 19.135 | 31.061 | 1.00 30.89 |
| ATOM | 2815 | O | TYR | B | 313 | 46.014 | 20.273 | 31.011 | 1.00 30.73 |
| ATOM | 2816 | N | ILE | B | 314 | 46.682 | 18.480 | 32.199 | 1.00 30.05 |
| ATOM | 2817 | CA | ILE | B | 314 | 46.447 | 19.066 | 33.519 | 1.00 28.73 |
| ATOM | 2818 | CB | ILE | B | 314 | 45.343 | 18.326 | 34.313 | 1.00 28.07 |
| ATOM | 2819 | CG2 | ILE | B | 314 | 45.400 | 18.705 | 35.783 | 1.00 26.27 |

Figure 7

| | | | | | | | | | |
|---|---|---|---|---|---|---|---|---|---|
| ATOM | 2820 | CG1 | ILE | B | 314 | 43.980 | 18.718 | 33.755 | 1.00 27.38 |
| ATOM | 2821 | CD1 | ILE | B | 314 | 42.871 | 17.859 | 34.226 | 1.00 27.49 |
| ATOM | 2822 | C | ILE | B | 314 | 47.818 | 18.889 | 34.180 | 1.00 28.09 |
| ATOM | 2823 | O | ILE | B | 314 | 48.332 | 17.775 | 34.260 | 1.00 28.66 |
| ATOM | 2824 | N | ILE | B | 315 | 48.440 | 19.997 | 34.572 | 1.00 27.24 |
| ATOM | 2825 | CA | ILE | B | 315 | 49.770 | 19.950 | 35.169 | 1.00 26.37 |
| ATOM | 2826 | CB | ILE | B | 315 | 50.771 | 20.909 | 34.437 | 1.00 26.21 |
| ATOM | 2827 | CG2 | ILE | B | 315 | 52.139 | 20.842 | 35.065 | 1.00 25.10 |
| ATOM | 2828 | CG1 | ILE | B | 315 | 50.863 | 20.579 | 32.951 | 1.00 25.54 |
| ATOM | 2829 | CD1 | ILE | B | 315 | 49.904 | 21.385 | 32.113 | 1.00 27.66 |
| ATOM | 2830 | C | ILE | B | 315 | 49.770 | 20.318 | 36.640 | 1.00 25.84 |
| ATOM | 2831 | O | ILE | B | 315 | 49.388 | 21.425 | 37.012 | 1.00 25.06 |
| ATOM | 2832 | N | THR | B | 316 | 50.257 | 19.398 | 37.463 | 1.00 25.45 |
| ATOM | 2833 | CA | THR | B | 316 | 50.338 | 19.621 | 38.895 | 1.00 25.87 |
| ATOM | 2834 | CB | THR | B | 316 | 49.441 | 18.610 | 39.677 | 1.00 24.45 |
| ATOM | 2835 | OG1 | THR | B | 316 | 49.935 | 17.285 | 39.493 | 1.00 23.35 |
| ATOM | 2836 | CG2 | THR | B | 316 | 48.001 | 18.647 | 39.184 | 1.00 24.48 |
| ATOM | 2837 | C | THR | B | 316 | 51.800 | 19.450 | 39.349 | 1.00 27.24 |
| ATOM | 2838 | O | THR | B | 316 | 52.690 | 19.103 | 38.550 | 1.00 26.97 |
| ATOM | 2839 | N | GLU | B | 317 | 52.044 | 19.710 | 40.634 | 1.00 27.63 |
| ATOM | 2840 | CA | GLU | B | 317 | 53.374 | 19.549 | 41.195 | 1.00 26.96 |
| ATOM | 2841 | CB | GLU | B | 317 | 53.405 | 20.034 | 42.653 | 1.00 26.82 |
| ATOM | 2842 | CG | GLU | B | 317 | 52.692 | 19.122 | 43.649 | 1.00 27.07 |
| ATOM | 2843 | CD | GLU | B | 317 | 52.638 | 19.701 | 45.039 | 1.00 27.96 |
| ATOM | 2844 | OE1 | GLU | B | 317 | 51.529 | 20.057 | 45.491 | 1.00 28.70 |
| ATOM | 2845 | OE2 | GLU | B | 317 | 53.697 | 19.794 | 45.689 | 1.00 30.59 |
| ATOM | 2846 | C | GLU | B | 317 | 53.699 | 18.062 | 41.129 | 1.00 27.09 |
| ATOM | 2847 | O | GLU | B | 317 | 52.795 | 17.227 | 41.012 | 1.00 28.33 |
| ATOM | 2848 | N | TYR | B | 318 | 54.982 | 17.729 | 41.131 | 1.00 26.51 |
| ATOM | 2849 | CA | TYR | B | 318 | 55.359 | 16.330 | 41.097 | 1.00 25.56 |
| ATOM | 2850 | CB | TYR | B | 318 | 56.607 | 16.136 | 40.242 | 1.00 24.65 |
| ATOM | 2851 | CG | TYR | B | 318 | 57.064 | 14.707 | 40.135 | 1.00 23.50 |
| ATOM | 2852 | CD1 | TYR | B | 318 | 56.387 | 13.790 | 39.331 | 1.00 23.38 |
| ATOM | 2853 | CE1 | TYR | B | 318 | 56.826 | 12.461 | 39.229 | 1.00 24.86 |
| ATOM | 2854 | CD2 | TYR | B | 318 | 58.187 | 14.271 | 40.836 | 1.00 24.31 |
| ATOM | 2855 | CE2 | TYR | B | 318 | 58.636 | 12.959 | 40.743 | 1.00 24.42 |
| ATOM | 2856 | CZ | TYR | B | 318 | 57.955 | 12.058 | 39.941 | 1.00 26.32 |
| ATOM | 2857 | OH | TYR | B | 318 | 58.411 | 10.763 | 39.864 | 1.00 27.92 |
| ATOM | 2858 | C | TYR | B | 318 | 55.575 | 15.829 | 42.525 | 1.00 24.93 |
| ATOM | 2859 | O | TYR | B | 318 | 56.172 | 16.512 | 43.351 | 1.00 23.33 |
| ATOM | 2860 | N | MET | B | 319 | 54.995 | 14.668 | 42.819 | 1.00 26.46 |
| ATOM | 2861 | CA | MET | B | 319 | 55.105 | 14.038 | 44.135 | 1.00 26.76 |
| ATOM | 2862 | CB | MET | B | 319 | 53.737 | 13.563 | 44.625 | 1.00 26.35 |
| ATOM | 2863 | CG | MET | B | 319 | 52.780 | 14.714 | 44.864 | 1.00 26.77 |
| ATOM | 2864 | SD | MET | B | 319 | 53.440 | 15.940 | 46.001 | 1.00 29.68 |
| ATOM | 2865 | CE | MET | B | 319 | 53.209 | 15.087 | 47.569 | 1.00 31.01 |
| ATOM | 2866 | C | MET | B | 319 | 56.084 | 12.886 | 44.029 | 1.00 26.72 |
| ATOM | 2867 | O | MET | B | 319 | 55.749 | 11.796 | 43.584 | 1.00 25.95 |
| ATOM | 2868 | N | GLU | B | 320 | 57.314 | 13.187 | 44.422 | 1.00 26.98 |
| ATOM | 2869 | CA | GLU | B | 320 | 58.435 | 12.271 | 44.387 | 1.00 28.23 |
| ATOM | 2870 | CB | GLU | B | 320 | 59.558 | 12.849 | 45.262 | 1.00 32.29 |
| ATOM | 2871 | CG | GLU | B | 320 | 60.911 | 12.170 | 45.119 | 1.00 37.44 |
| ATOM | 2872 | CD | GLU | B | 320 | 61.380 | 12.043 | 43.662 | 1.00 40.91 |
| ATOM | 2873 | OE1 | GLU | B | 320 | 61.402 | 13.066 | 42.915 | 1.00 37.26 |
| ATOM | 2874 | OE2 | GLU | B | 320 | 61.735 | 10.898 | 43.283 | 1.00 42.45 |
| ATOM | 2875 | C | GLU | B | 320 | 58.174 | 10.796 | 44.699 | 1.00 27.17 |
| ATOM | 2876 | O | GLU | B | 320 | 58.606 | 9.934 | 43.945 | 1.00 27.19 |
| ATOM | 2877 | N | ASN | B | 321 | 57.455 | 10.499 | 45.779 | 1.00 26.51 |
| ATOM | 2878 | CA | ASN | B | 321 | 57.177 | 9.109 | 46.154 | 1.00 25.15 |

Figure 7

```
ATOM   2879  CB   ASN B 321      57.327   8.937  47.652  1.00 25.47
ATOM   2880  CG   ASN B 321      58.759   8.903  48.072  1.00 27.05
ATOM   2881  OD1  ASN B 321      59.540   8.094  47.566  1.00 28.74
ATOM   2882  ND2  ASN B 321      59.134   9.791  48.977  1.00 27.80
ATOM   2883  C    ASN B 321      55.870   8.479  45.677  1.00 25.09
ATOM   2884  O    ASN B 321      55.494   7.384  46.114  1.00 24.76
ATOM   2885  N    GLY B 322      55.189   9.172  44.772  1.00 25.16
ATOM   2886  CA   GLY B 322      53.954   8.672  44.204  1.00 24.80
ATOM   2887  C    GLY B 322      52.741   8.506  45.091  1.00 25.47
ATOM   2888  O    GLY B 322      52.452   9.318  45.968  1.00 26.04
ATOM   2889  N    SER B 323      52.011   7.439  44.807  1.00 25.73
ATOM   2890  CA   SER B 323      50.799   7.086  45.511  1.00 26.47
ATOM   2891  CB   SER B 323      49.987   6.133  44.633  1.00 27.95
ATOM   2892  OG   SER B 323      48.773   5.749  45.244  1.00 32.00
ATOM   2893  C    SER B 323      51.114   6.435  46.849  1.00 26.26
ATOM   2894  O    SER B 323      51.997   5.593  46.940  1.00 26.10
ATOM   2895  N    LEU B 324      50.379   6.833  47.884  1.00 26.77
ATOM   2896  CA   LEU B 324      50.558   6.295  49.221  1.00 25.66
ATOM   2897  CB   LEU B 324      49.666   7.042  50.221  1.00 25.84
ATOM   2898  CG   LEU B 324      49.658   6.551  51.683  1.00 24.56
ATOM   2899  CD1  LEU B 324      51.018   6.809  52.338  1.00 20.66
ATOM   2900  CD2  LEU B 324      48.531   7.231  52.467  1.00 22.84
ATOM   2901  C    LEU B 324      50.277   4.794  49.293  1.00 25.67
ATOM   2902  O    LEU B 324      50.991   4.058  49.967  1.00 26.23
ATOM   2903  N    VAL B 325      49.244   4.328  48.604  1.00 25.81
ATOM   2904  CA   VAL B 325      48.928   2.904  48.644  1.00 27.25
ATOM   2905  CB   VAL B 325      47.653   2.580  47.821  1.00 26.49
ATOM   2906  CG1  VAL B 325      47.956   2.545  46.331  1.00 26.24
ATOM   2907  CG2  VAL B 325      47.035   1.282  48.292  1.00 25.72
ATOM   2908  C    VAL B 325      50.125   2.061  48.169  1.00 28.43
ATOM   2909  O    VAL B 325      50.401   0.996  48.716  1.00 28.15
ATOM   2910  N    ASP B 326      50.852   2.575  47.177  1.00 29.02
ATOM   2911  CA   ASP B 326      52.025   1.897  46.636  1.00 29.63
ATOM   2912  CB   ASP B 326      52.343   2.435  45.243  1.00 29.72
ATOM   2913  CG   ASP B 326      51.350   1.986  44.214  1.00 29.64
ATOM   2914  OD1  ASP B 326      50.683   0.956  44.427  1.00 31.48
ATOM   2915  OD2  ASP B 326      51.237   2.655  43.177  1.00 34.01
ATOM   2916  C    ASP B 326      53.238   2.093  47.522  1.00 30.07
ATOM   2917  O    ASP B 326      53.992   1.150  47.780  1.00 30.76
ATOM   2918  N    PHE B 327      53.428   3.339  47.949  1.00 29.96
ATOM   2919  CA   PHE B 327      54.541   3.724  48.789  1.00 30.33
ATOM   2920  CB   PHE B 327      54.468   5.206  49.136  1.00 29.99
ATOM   2921  CG   PHE B 327      55.587   5.659  50.018  1.00 31.28
ATOM   2922  CD1  PHE B 327      56.903   5.639  49.553  1.00 31.91
ATOM   2923  CD2  PHE B 327      55.344   6.048  51.323  1.00 31.34
ATOM   2924  CE1  PHE B 327      57.954   5.994  50.376  1.00 30.90
ATOM   2925  CE2  PHE B 327      56.393   6.407  52.164  1.00 32.34
ATOM   2926  CZ   PHE B 327      57.702   6.378  51.688  1.00 32.88
ATOM   2927  C    PHE B 327      54.637   2.920  50.068  1.00 31.07
ATOM   2928  O    PHE B 327      55.731   2.597  50.518  1.00 31.17
ATOM   2929  N    LEU B 328      53.487   2.617  50.655  1.00 32.26
ATOM   2930  CA   LEU B 328      53.426   1.862  51.905  1.00 34.42
ATOM   2931  CB   LEU B 328      51.999   1.871  52.466  1.00 33.77
ATOM   2932  CG   LEU B 328      51.492   3.112  53.202  1.00 32.79
ATOM   2933  CD1  LEU B 328      49.994   2.962  53.480  1.00 33.37
ATOM   2934  CD2  LEU B 328      52.275   3.314  54.483  1.00 30.61
ATOM   2935  C    LEU B 328      53.899   0.418  51.761  1.00 35.98
ATOM   2936  O    LEU B 328      54.225  -0.231  52.760  1.00 36.10
ATOM   2937  N    LYS B 329      53.895  -0.095  50.532  1.00 37.05
```

Figure 7

| ATOM | 2938 | CA  | LYS | B | 329 | 54.325 | -1.461 | 50.291 | 1.00 | 37.93 |
| ATOM | 2939 | CB  | LYS | B | 329 | 53.509 | -2.101 | 49.167 | 1.00 | 38.09 |
| ATOM | 2940 | CG  | LYS | B | 329 | 52.019 | -2.165 | 49.429 | 1.00 | 37.14 |
| ATOM | 2941 | CD  | LYS | B | 329 | 51.322 | -2.979 | 48.359 | 1.00 | 38.24 |
| ATOM | 2942 | CE  | LYS | B | 329 | 49.804 | -2.900 | 48.478 | 1.00 | 39.62 |
| ATOM | 2943 | NZ  | LYS | B | 329 | 49.290 | -1.569 | 48.048 | 1.00 | 41.20 |
| ATOM | 2944 | C   | LYS | B | 329 | 55.810 | -1.536 | 49.972 | 1.00 | 39.06 |
| ATOM | 2945 | O   | LYS | B | 329 | 56.382 | -2.639 | 49.994 | 1.00 | 39.86 |
| ATOM | 2946 | N   | THR | B | 330 | 56.430 | -0.378 | 49.702 | 1.00 | 40.08 |
| ATOM | 2947 | CA  | THR | B | 330 | 57.865 | -0.311 | 49.375 | 1.00 | 41.20 |
| ATOM | 2948 | CB  | THR | B | 330 | 58.276 | 1.045  | 48.716 | 1.00 | 40.17 |
| ATOM | 2949 | OG1 | THR | B | 330 | 58.099 | 2.119  | 49.645 | 1.00 | 39.58 |
| ATOM | 2950 | CG2 | THR | B | 330 | 57.479 | 1.309  | 47.451 | 1.00 | 39.23 |
| ATOM | 2951 | C   | THR | B | 330 | 58.741 | -0.532 | 50.613 | 1.00 | 42.92 |
| ATOM | 2952 | O   | THR | B | 330 | 58.303 | -0.289 | 51.740 | 1.00 | 43.20 |
| ATOM | 2953 | N   | PRO | B | 331 | 59.995 | -0.988 | 50.416 | 1.00 | 44.17 |
| ATOM | 2954 | CD  | PRO | B | 331 | 60.617 | -1.315 | 49.117 | 1.00 | 44.06 |
| ATOM | 2955 | CA  | PRO | B | 331 | 60.935 | -1.246 | 51.513 | 1.00 | 44.79 |
| ATOM | 2956 | CB  | PRO | B | 331 | 62.264 | -1.381 | 50.776 | 1.00 | 45.11 |
| ATOM | 2957 | CG  | PRO | B | 331 | 61.840 | -2.114 | 49.528 | 1.00 | 43.90 |
| ATOM | 2958 | C   | PRO | B | 331 | 60.971 | -0.174 | 52.610 | 1.00 | 44.76 |
| ATOM | 2959 | O   | PRO | B | 331 | 60.899 | -0.506 | 53.799 | 1.00 | 44.78 |
| ATOM | 2960 | N   | SER | B | 332 | 61.042 | 1.096  | 52.214 | 1.00 | 44.48 |
| ATOM | 2961 | CA  | SER | B | 332 | 61.065 | 2.194  | 53.182 | 1.00 | 44.97 |
| ATOM | 2962 | CB  | SER | B | 332 | 61.419 | 3.523  | 52.501 | 1.00 | 46.14 |
| ATOM | 2963 | OG  | SER | B | 332 | 62.763 | 3.535  | 52.052 | 1.00 | 49.22 |
| ATOM | 2964 | C   | SER | B | 332 | 59.713 | 2.330  | 53.890 | 1.00 | 44.29 |
| ATOM | 2965 | O   | SER | B | 332 | 59.652 | 2.665  | 55.079 | 1.00 | 44.30 |
| ATOM | 2966 | N   | GLY | B | 333 | 58.641 | 2.063  | 53.146 | 1.00 | 43.13 |
| ATOM | 2967 | CA  | GLY | B | 333 | 57.294 | 2.157  | 53.689 | 1.00 | 42.43 |
| ATOM | 2968 | C   | GLY | B | 333 | 56.940 | 1.070  | 54.685 | 1.00 | 41.59 |
| ATOM | 2969 | O   | GLY | B | 333 | 56.222 | 1.313  | 55.652 | 1.00 | 40.98 |
| ATOM | 2970 | N   | ILE | B | 334 | 57.445 | -0.134 | 54.443 | 1.00 | 41.62 |
| ATOM | 2971 | CA  | ILE | B | 334 | 57.203 | -1.272 | 55.319 | 1.00 | 41.42 |
| ATOM | 2972 | CB  | ILE | B | 334 | 57.844 | -2.555 | 54.723 | 1.00 | 41.88 |
| ATOM | 2973 | CG2 | ILE | B | 334 | 57.990 | -3.634 | 55.787 | 1.00 | 42.74 |
| ATOM | 2974 | CG1 | ILE | B | 334 | 57.020 | -3.065 | 53.534 | 1.00 | 40.76 |
| ATOM | 2975 | CD1 | ILE | B | 334 | 55.615 | -3.518 | 53.901 | 1.00 | 40.47 |
| ATOM | 2976 | C   | ILE | B | 334 | 57.794 | -0.994 | 56.703 | 1.00 | 41.45 |
| ATOM | 2977 | O   | ILE | B | 334 | 57.209 | -1.362 | 57.727 | 1.00 | 41.41 |
| ATOM | 2978 | N   | LYS | B | 335 | 58.929 | -0.295 | 56.709 | 1.00 | 41.33 |
| ATOM | 2979 | CA  | LYS | B | 335 | 59.658 | 0.045  | 57.928 | 1.00 | 40.77 |
| ATOM | 2980 | CB  | LYS | B | 335 | 61.152 | 0.234  | 57.615 | 1.00 | 42.29 |
| ATOM | 2981 | CG  | LYS | B | 335 | 61.831 | -0.934 | 56.897 | 1.00 | 46.33 |
| ATOM | 2982 | CD  | LYS | B | 335 | 63.216 | -0.513 | 56.357 | 1.00 | 50.33 |
| ATOM | 2983 | CE  | LYS | B | 335 | 63.782 | -1.506 | 55.315 | 1.00 | 52.40 |
| ATOM | 2984 | NZ  | LYS | B | 335 | 64.539 | -0.819 | 54.202 | 1.00 | 52.32 |
| ATOM | 2985 | C   | LYS | B | 335 | 59.160 | 1.282  | 58.668 | 1.00 | 39.37 |
| ATOM | 2986 | O   | LYS | B | 335 | 59.693 | 1.596  | 59.725 | 1.00 | 39.47 |
| ATOM | 2987 | N   | LEU | B | 336 | 58.174 | 2.002  | 58.129 | 1.00 | 38.46 |
| ATOM | 2988 | CA  | LEU | B | 336 | 57.665 | 3.216  | 58.800 | 1.00 | 36.39 |
| ATOM | 2989 | CB  | LEU | B | 336 | 56.604 | 3.931  | 57.950 | 1.00 | 35.74 |
| ATOM | 2990 | CG  | LEU | B | 336 | 57.049 | 4.641  | 56.666 | 1.00 | 34.77 |
| ATOM | 2991 | CD1 | LEU | B | 336 | 55.857 | 5.125  | 55.869 | 1.00 | 33.52 |
| ATOM | 2992 | CD2 | LEU | B | 336 | 57.960 | 5.807  | 57.013 | 1.00 | 34.32 |
| ATOM | 2993 | C   | LEU | B | 336 | 57.089 | 2.903  | 60.174 | 1.00 | 35.51 |
| ATOM | 2994 | O   | LEU | B | 336 | 56.336 | 1.930  | 60.333 | 1.00 | 35.47 |
| ATOM | 2995 | N   | THR | B | 337 | 57.474 | 3.715  | 61.161 | 1.00 | 33.83 |
| ATOM | 2996 | CA  | THR | B | 337 | 57.017 | 3.566  | 62.540 | 1.00 | 32.09 |

Figure 7

| | | | | | | | | | |
|---|---|---|---|---|---|---|---|---|---|
| ATOM | 2997 | CB | THR | B | 337 | 57.892 | 4.370 | 63.545 | 1.00 31.29 |
| ATOM | 2998 | OG1 | THR | B | 337 | 57.723 | 5.779 | 63.336 | 1.00 28.12 |
| ATOM | 2999 | CG2 | THR | B | 337 | 59.368 | 4.004 | 63.402 | 1.00 31.66 |
| ATOM | 3000 | C | THR | B | 337 | 55.577 | 4.041 | 62.710 | 1.00 32.57 |
| ATOM | 3001 | O | THR | B | 337 | 55.093 | 4.891 | 61.961 | 1.00 33.01 |
| ATOM | 3002 | N | ILE | B | 338 | 54.912 | 3.517 | 63.733 | 1.00 32.04 |
| ATOM | 3003 | CA | ILE | B | 338 | 53.531 | 3.886 | 64.019 | 1.00 31.14 |
| ATOM | 3004 | CB | ILE | B | 338 | 53.018 | 3.141 | 65.286 | 1.00 30.72 |
| ATOM | 3005 | CG2 | ILE | B | 338 | 53.807 | 3.576 | 66.518 | 1.00 30.49 |
| ATOM | 3006 | CG1 | ILE | B | 338 | 51.513 | 3.351 | 65.464 | 1.00 30.73 |
| ATOM | 3007 | CD1 | ILE | B | 338 | 50.668 | 2.806 | 64.322 | 1.00 31.67 |
| ATOM | 3008 | C | ILE | B | 338 | 53.384 | 5.408 | 64.178 | 1.00 29.90 |
| ATOM | 3009 | O | ILE | B | 338 | 52.381 | 5.987 | 63.776 | 1.00 29.37 |
| ATOM | 3010 | N | ASN | B | 339 | 54.434 | 6.050 | 64.679 | 1.00 30.15 |
| ATOM | 3011 | CA | ASN | B | 339 | 54.443 | 7.493 | 64.896 | 1.00 30.36 |
| ATOM | 3012 | CB | ASN | B | 339 | 55.709 | 7.909 | 65.627 | 1.00 29.83 |
| ATOM | 3013 | CG | ASN | B | 339 | 55.928 | 7.130 | 66.883 | 1.00 31.46 |
| ATOM | 3014 | OD1 | ASN | B | 339 | 55.735 | 7.655 | 67.972 | 1.00 33.15 |
| ATOM | 3015 | ND2 | ASN | B | 339 | 56.350 | 5.866 | 66.751 | 1.00 31.27 |
| ATOM | 3016 | C | ASN | B | 339 | 54.394 | 8.252 | 63.593 | 1.00 30.48 |
| ATOM | 3017 | O | ASN | B | 339 | 53.766 | 9.312 | 63.504 | 1.00 31.48 |
| ATOM | 3018 | N | LYS | B | 340 | 55.126 | 7.733 | 62.610 | 1.00 30.52 |
| ATOM | 3019 | CA | LYS | B | 340 | 55.195 | 8.343 | 61.291 | 1.00 30.59 |
| ATOM | 3020 | CB | LYS | B | 340 | 56.369 | 7.766 | 60.494 | 1.00 31.34 |
| ATOM | 3021 | CG | LYS | B | 340 | 56.443 | 8.276 | 59.072 | 1.00 33.30 |
| ATOM | 3022 | CD | LYS | B | 340 | 56.468 | 9.813 | 58.992 | 1.00 36.15 |
| ATOM | 3023 | CE | LYS | B | 340 | 56.405 | 10.298 | 57.530 | 1.00 36.58 |
| ATOM | 3024 | NZ | LYS | B | 340 | 56.291 | 11.788 | 57.379 | 1.00 37.55 |
| ATOM | 3025 | C | LYS | B | 340 | 53.884 | 8.127 | 60.560 | 1.00 29.48 |
| ATOM | 3026 | O | LYS | B | 340 | 53.331 | 9.061 | 59.991 | 1.00 30.28 |
| ATOM | 3027 | N | LEU | B | 341 | 53.395 | 6.891 | 60.594 | 1.00 28.58 |
| ATOM | 3028 | CA | LEU | B | 341 | 52.135 | 6.527 | 59.957 | 1.00 28.16 |
| ATOM | 3029 | CB | LEU | B | 341 | 51.812 | 5.051 | 60.237 | 1.00 27.02 |
| ATOM | 3030 | CG | LEU | B | 341 | 52.748 | 3.991 | 59.666 | 1.00 24.82 |
| ATOM | 3031 | CD1 | LEU | B | 341 | 52.226 | 2.611 | 60.020 | 1.00 24.24 |
| ATOM | 3032 | CD2 | LEU | B | 341 | 52.823 | 4.156 | 58.167 | 1.00 25.60 |
| ATOM | 3033 | C | LEU | B | 341 | 50.988 | 7.407 | 60.474 | 1.00 28.09 |
| ATOM | 3034 | O | LEU | B | 341 | 50.106 | 7.808 | 59.718 | 1.00 28.27 |
| ATOM | 3035 | N | LEU | B | 342 | 51.020 | 7.724 | 61.760 | 1.00 29.14 |
| ATOM | 3036 | CA | LEU | B | 342 | 49.991 | 8.534 | 62.363 | 1.00 30.35 |
| ATOM | 3037 | CB | LEU | B | 342 | 50.004 | 8.388 | 63.877 | 1.00 33.74 |
| ATOM | 3038 | CG | LEU | B | 342 | 49.380 | 7.078 | 64.352 | 1.00 36.07 |
| ATOM | 3039 | CD1 | LEU | B | 342 | 48.873 | 7.303 | 65.724 | 1.00 36.54 |
| ATOM | 3040 | CD2 | LEU | B | 342 | 48.210 | 6.674 | 63.459 | 1.00 37.94 |
| ATOM | 3041 | C | LEU | B | 342 | 50.104 | 10.004 | 61.994 | 1.00 30.24 |
| ATOM | 3042 | O | LEU | B | 342 | 49.087 | 10.740 | 61.997 | 1.00 29.35 |
| ATOM | 3043 | N | ASP | B | 343 | 51.334 | 10.437 | 61.721 | 1.00 29.66 |
| ATOM | 3044 | CA | ASP | B | 343 | 51.568 | 11.816 | 61.328 | 1.00 29.33 |
| ATOM | 3045 | CB | ASP | B | 343 | 53.062 | 12.135 | 61.395 | 1.00 31.90 |
| ATOM | 3046 | CG | ASP | B | 343 | 53.367 | 13.592 | 61.109 | 1.00 36.82 |
| ATOM | 3047 | OD1 | ASP | B | 343 | 52.725 | 14.471 | 61.733 | 1.00 39.94 |
| ATOM | 3048 | OD2 | ASP | B | 343 | 54.219 | 13.857 | 60.230 | 1.00 40.21 |
| ATOM | 3049 | C | ASP | B | 343 | 51.032 | 11.971 | 59.903 | 1.00 27.30 |
| ATOM | 3050 | O | ASP | B | 343 | 50.421 | 12.975 | 59.569 | 1.00 27.27 |
| ATOM | 3051 | N | MET | B | 344 | 51.198 | 10.932 | 59.099 | 1.00 26.93 |
| ATOM | 3052 | CA | MET | B | 344 | 50.705 | 10.965 | 57.734 | 1.00 26.63 |
| ATOM | 3053 | CB | MET | B | 344 | 51.214 | 9.755 | 56.963 | 1.00 28.71 |
| ATOM | 3054 | CG | MET | B | 344 | 52.735 | 9.669 | 56.866 | 1.00 30.38 |
| ATOM | 3055 | SD | MET | B | 344 | 53.249 | 8.191 | 55.971 | 1.00 33.61 |

Figure 7

| ATOM | 3056 | CE | MET | B | 344 | 53.423 | 8.836 | 54.327 | 1.00 | 33.33 |
| ATOM | 3057 | C | MET | B | 344 | 49.181 | 10.990 | 57.749 | 1.00 | 26.20 |
| ATOM | 3058 | O | MET | B | 344 | 48.575 | 11.733 | 56.966 | 1.00 | 27.13 |
| ATOM | 3059 | N | ALA | B | 345 | 48.564 | 10.201 | 58.638 | 1.00 | 24.39 |
| ATOM | 3060 | CA | ALA | B | 345 | 47.107 | 10.151 | 58.775 | 1.00 | 23.04 |
| ATOM | 3061 | CB | ALA | B | 345 | 46.706 | 9.096 | 59.797 | 1.00 | 20.95 |
| ATOM | 3062 | C | ALA | B | 345 | 46.622 | 11.530 | 59.206 | 1.00 | 22.68 |
| ATOM | 3063 | O | ALA | B | 345 | 45.640 | 12.042 | 58.682 | 1.00 | 22.97 |
| ATOM | 3064 | N | ALA | B | 346 | 47.366 | 12.143 | 60.122 | 1.00 | 23.09 |
| ATOM | 3065 | CA | ALA | B | 346 | 47.067 | 13.472 | 60.637 | 1.00 | 22.87 |
| ATOM | 3066 | CB | ALA | B | 346 | 48.068 | 13.848 | 61.734 | 1.00 | 23.18 |
| ATOM | 3067 | C | ALA | B | 346 | 47.112 | 14.513 | 59.529 | 1.00 | 22.98 |
| ATOM | 3068 | O | ALA | B | 346 | 46.320 | 15.463 | 59.534 | 1.00 | 22.86 |
| ATOM | 3069 | N | GLN | B | 347 | 48.069 | 14.352 | 58.610 | 1.00 | 23.91 |
| ATOM | 3070 | CA | GLN | B | 347 | 48.237 | 15.272 | 57.475 | 1.00 | 23.53 |
| ATOM | 3071 | CB | GLN | B | 347 | 49.539 | 14.980 | 56.724 | 1.00 | 24.80 |
| ATOM | 3072 | CG | GLN | B | 347 | 50.810 | 15.258 | 57.519 | 1.00 | 27.63 |
| ATOM | 3073 | CD | GLN | B | 347 | 52.073 | 14.979 | 56.723 | 1.00 | 28.82 |
| ATOM | 3074 | OE1 | GLN | B | 347 | 53.016 | 15.767 | 56.754 | 1.00 | 32.64 |
| ATOM | 3075 | NE2 | GLN | B | 347 | 52.099 | 13.857 | 56.010 | 1.00 | 27.39 |
| ATOM | 3076 | C | GLN | B | 347 | 47.057 | 15.203 | 56.502 | 1.00 | 22.80 |
| ATOM | 3077 | O | GLN | B | 347 | 46.587 | 16.235 | 56.003 | 1.00 | 21.93 |
| ATOM | 3078 | N | ILE | B | 348 | 46.606 | 13.980 | 56.220 | 1.00 | 23.17 |
| ATOM | 3079 | CA | ILE | B | 348 | 45.470 | 13.749 | 55.321 | 1.00 | 22.40 |
| ATOM | 3080 | CB | ILE | B | 348 | 45.279 | 12.228 | 55.040 | 1.00 | 21.00 |
| ATOM | 3081 | CG2 | ILE | B | 348 | 44.097 | 12.003 | 54.094 | 1.00 | 20.04 |
| ATOM | 3082 | CG1 | ILE | B | 348 | 46.570 | 11.641 | 54.454 | 1.00 | 17.89 |
| ATOM | 3083 | CD1 | ILE | B | 348 | 46.614 | 10.142 | 54.451 | 1.00 | 17.24 |
| ATOM | 3084 | C | ILE | B | 348 | 44.212 | 14.331 | 55.961 | 1.00 | 23.40 |
| ATOM | 3085 | O | ILE | B | 348 | 43.422 | 14.997 | 55.291 | 1.00 | 24.52 |
| ATOM | 3086 | N | ALA | B | 349 | 44.065 | 14.130 | 57.274 | 1.00 | 23.99 |
| ATOM | 3087 | CA | ALA | B | 349 | 42.913 | 14.646 | 58.030 | 1.00 | 24.90 |
| ATOM | 3088 | CB | ALA | B | 349 | 42.884 | 14.053 | 59.453 | 1.00 | 24.95 |
| ATOM | 3089 | C | ALA | B | 349 | 42.913 | 16.180 | 58.101 | 1.00 | 25.10 |
| ATOM | 3090 | O | ALA | B | 349 | 41.855 | 16.800 | 58.245 | 1.00 | 25.96 |
| ATOM | 3091 | N | GLU | B | 350 | 44.098 | 16.783 | 58.046 | 1.00 | 24.40 |
| ATOM | 3092 | CA | GLU | B | 350 | 44.213 | 18.233 | 58.079 | 1.00 | 24.74 |
| ATOM | 3093 | CB | GLU | B | 350 | 45.659 | 18.627 | 58.356 | 1.00 | 26.97 |
| ATOM | 3094 | CG | GLU | B | 350 | 45.900 | 20.124 | 58.305 | 1.00 | 30.45 |
| ATOM | 3095 | CD | GLU | B | 350 | 47.362 | 20.478 | 58.412 | 1.00 | 33.17 |
| ATOM | 3096 | OE1 | GLU | B | 350 | 48.184 | 19.564 | 58.660 | 1.00 | 33.26 |
| ATOM | 3097 | OE2 | GLU | B | 350 | 47.684 | 21.675 | 58.251 | 1.00 | 35.21 |
| ATOM | 3098 | C | GLU | B | 350 | 43.731 | 18.851 | 56.762 | 1.00 | 23.54 |
| ATOM | 3099 | O | GLU | B | 350 | 43.094 | 19.900 | 56.758 | 1.00 | 23.97 |
| ATOM | 3100 | N | GLY | B | 351 | 44.038 | 18.186 | 55.652 | 1.00 | 23.49 |
| ATOM | 3101 | CA | GLY | B | 351 | 43.620 | 18.659 | 54.346 | 1.00 | 22.34 |
| ATOM | 3102 | C | GLY | B | 351 | 42.142 | 18.396 | 54.135 | 1.00 | 22.70 |
| ATOM | 3103 | O | GLY | B | 351 | 41.474 | 19.137 | 53.411 | 1.00 | 23.70 |
| ATOM | 3104 | N | MET | B | 352 | 41.643 | 17.305 | 54.718 | 1.00 | 21.01 |
| ATOM | 3105 | CA | MET | B | 352 | 40.225 | 16.972 | 54.633 | 1.00 | 19.45 |
| ATOM | 3106 | CB | MET | B | 352 | 39.973 | 15.541 | 55.093 | 1.00 | 17.11 |
| ATOM | 3107 | CG | MET | B | 352 | 40.234 | 14.484 | 54.033 | 1.00 | 14.65 |
| ATOM | 3108 | SD | MET | B | 352 | 39.489 | 14.833 | 52.405 | 1.00 | 19.62 |
| ATOM | 3109 | CE | MET | B | 352 | 37.731 | 15.112 | 52.782 | 1.00 | 12.07 |
| ATOM | 3110 | C | MET | B | 352 | 39.448 | 17.947 | 55.499 | 1.00 | 19.21 |
| ATOM | 3111 | O | MET | B | 352 | 38.324 | 18.302 | 55.188 | 1.00 | 19.74 |
| ATOM | 3112 | N | ALA | B | 353 | 40.073 | 18.397 | 56.581 | 1.00 | 21.15 |
| ATOM | 3113 | CA | ALA | B | 353 | 39.472 | 19.372 | 57.479 | 1.00 | 22.54 |
| ATOM | 3114 | CB | ALA | B | 353 | 40.304 | 19.509 | 58.745 | 1.00 | 20.42 |

Figure 7

| ATOM | 3115 | C   | ALA | B | 353 | 39.333 | 20.733 | 56.769 | 1.00 | 23.90 |
| ATOM | 3116 | O   | ALA | B | 353 | 38.413 | 21.486 | 57.055 | 1.00 | 24.92 |
| ATOM | 3117 | N   | PHE | B | 354 | 40.241 | 21.028 | 55.831 | 1.00 | 25.36 |
| ATOM | 3118 | CA  | PHE | B | 354 | 40.211 | 22.280 | 55.062 | 1.00 | 25.68 |
| ATOM | 3119 | CB  | PHE | B | 354 | 41.545 | 22.498 | 54.334 | 1.00 | 28.26 |
| ATOM | 3120 | CG  | PHE | B | 354 | 41.574 | 23.734 | 53.474 | 1.00 | 29.78 |
| ATOM | 3121 | CD1 | PHE | B | 354 | 41.419 | 24.999 | 54.039 | 1.00 | 29.08 |
| ATOM | 3122 | CD2 | PHE | B | 354 | 41.732 | 23.636 | 52.092 | 1.00 | 30.84 |
| ATOM | 3123 | CE1 | PHE | B | 354 | 41.425 | 26.144 | 53.243 | 1.00 | 29.34 |
| ATOM | 3124 | CE2 | PHE | B | 354 | 41.736 | 24.787 | 51.288 | 1.00 | 30.13 |
| ATOM | 3125 | CZ  | PHE | B | 354 | 41.581 | 26.036 | 51.866 | 1.00 | 28.56 |
| ATOM | 3126 | C   | PHE | B | 354 | 39.071 | 22.198 | 54.058 | 1.00 | 24.98 |
| ATOM | 3127 | O   | PHE | B | 354 | 38.301 | 23.134 | 53.888 | 1.00 | 25.26 |
| ATOM | 3128 | N   | ILE | B | 355 | 38.994 | 21.063 | 53.382 | 1.00 | 25.42 |
| ATOM | 3129 | CA  | ILE | B | 355 | 37.948 | 20.775 | 52.417 | 1.00 | 24.76 |
| ATOM | 3130 | CB  | ILE | B | 355 | 38.197 | 19.380 | 51.806 | 1.00 | 23.49 |
| ATOM | 3131 | CG2 | ILE | B | 355 | 36.909 | 18.807 | 51.207 | 1.00 | 23.64 |
| ATOM | 3132 | CG1 | ILE | B | 355 | 39.353 | 19.470 | 50.792 | 1.00 | 21.59 |
| ATOM | 3133 | CD1 | ILE | B | 355 | 39.845 | 18.131 | 50.304 | 1.00 | 19.63 |
| ATOM | 3134 | C   | ILE | B | 355 | 36.586 | 20.854 | 53.117 | 1.00 | 25.65 |
| ATOM | 3135 | O   | ILE | B | 355 | 35.634 | 21.435 | 52.584 | 1.00 | 24.38 |
| ATOM | 3136 | N   | GLU | B | 356 | 36.539 | 20.304 | 54.339 | 1.00 | 26.70 |
| ATOM | 3137 | CA  | GLU | B | 356 | 35.359 | 20.290 | 55.210 | 1.00 | 27.36 |
| ATOM | 3138 | CB  | GLU | B | 356 | 35.666 | 19.488 | 56.473 | 1.00 | 25.87 |
| ATOM | 3139 | CG  | GLU | B | 356 | 34.581 | 19.518 | 57.526 | 1.00 | 25.33 |
| ATOM | 3140 | CD  | GLU | B | 356 | 34.917 | 18.648 | 58.715 | 1.00 | 24.99 |
| ATOM | 3141 | OE1 | GLU | B | 356 | 35.552 | 19.144 | 59.674 | 1.00 | 24.63 |
| ATOM | 3142 | OE2 | GLU | B | 356 | 34.555 | 17.457 | 58.685 | 1.00 | 25.73 |
| ATOM | 3143 | C   | GLU | B | 356 | 34.976 | 21.729 | 55.574 | 1.00 | 28.52 |
| ATOM | 3144 | O   | GLU | B | 356 | 33.832 | 22.134 | 55.406 | 1.00 | 28.60 |
| ATOM | 3145 | N   | GLU | B | 357 | 35.966 | 22.490 | 56.033 | 1.00 | 30.06 |
| ATOM | 3146 | CA  | GLU | B | 357 | 35.845 | 23.903 | 56.395 | 1.00 | 32.11 |
| ATOM | 3147 | CB  | GLU | B | 357 | 37.266 | 24.446 | 56.647 | 1.00 | 37.76 |
| ATOM | 3148 | CG  | GLU | B | 357 | 37.445 | 25.973 | 56.700 | 1.00 | 43.01 |
| ATOM | 3149 | CD  | GLU | B | 357 | 36.958 | 26.579 | 58.001 | 1.00 | 47.59 |
| ATOM | 3150 | OE1 | GLU | B | 357 | 37.092 | 25.912 | 59.052 | 1.00 | 50.98 |
| ATOM | 3151 | OE2 | GLU | B | 357 | 36.440 | 27.721 | 57.979 | 1.00 | 50.37 |
| ATOM | 3152 | C   | GLU | B | 357 | 35.208 | 24.714 | 55.270 | 1.00 | 31.57 |
| ATOM | 3153 | O   | GLU | B | 357 | 34.345 | 25.555 | 55.496 | 1.00 | 30.62 |
| ATOM | 3154 | N   | ARG | B | 358 | 35.657 | 24.453 | 54.050 | 1.00 | 32.07 |
| ATOM | 3155 | CA  | ARG | B | 358 | 35.185 | 25.168 | 52.875 | 1.00 | 33.00 |
| ATOM | 3156 | CB  | ARG | B | 358 | 36.303 | 25.221 | 51.821 | 1.00 | 33.78 |
| ATOM | 3157 | CG  | ARG | B | 358 | 37.640 | 25.800 | 52.333 | 1.00 | 35.92 |
| ATOM | 3158 | CD  | ARG | B | 358 | 37.553 | 27.289 | 52.711 | 1.00 | 39.63 |
| ATOM | 3159 | NE  | ARG | B | 358 | 37.168 | 28.086 | 51.554 | 1.00 | 45.18 |
| ATOM | 3160 | CZ  | ARG | B | 358 | 37.979 | 28.386 | 50.539 | 1.00 | 48.16 |
| ATOM | 3161 | NH1 | ARG | B | 358 | 39.248 | 27.990 | 50.549 | 1.00 | 49.31 |
| ATOM | 3162 | NH2 | ARG | B | 358 | 37.477 | 28.921 | 49.427 | 1.00 | 49.00 |
| ATOM | 3163 | C   | ARG | B | 358 | 33.907 | 24.591 | 52.283 | 1.00 | 33.51 |
| ATOM | 3164 | O   | ARG | B | 358 | 33.509 | 24.957 | 51.184 | 1.00 | 34.43 |
| ATOM | 3165 | N   | ASN | B | 359 | 33.290 | 23.658 | 53.003 | 1.00 | 34.35 |
| ATOM | 3166 | CA  | ASN | B | 359 | 32.033 | 23.028 | 52.591 | 1.00 | 34.09 |
| ATOM | 3167 | CB  | ASN | B | 359 | 30.886 | 24.034 | 52.680 | 1.00 | 36.01 |
| ATOM | 3168 | CG  | ASN | B | 359 | 30.759 | 24.640 | 54.067 | 1.00 | 37.24 |
| ATOM | 3169 | OD1 | ASN | B | 359 | 30.616 | 23.917 | 55.067 | 1.00 | 38.43 |
| ATOM | 3170 | ND2 | ASN | B | 359 | 30.847 | 25.973 | 54.141 | 1.00 | 36.54 |
| ATOM | 3171 | C   | ASN | B | 359 | 32.000 | 22.279 | 51.259 | 1.00 | 33.23 |
| ATOM | 3172 | O   | ASN | B | 359 | 31.047 | 22.374 | 50.485 | 1.00 | 31.79 |
| ATOM | 3173 | N   | TYR | B | 360 | 33.052 | 21.502 | 51.019 | 1.00 | 33.62 |

Figure 7

```
ATOM   3174  CA   TYR B 360      33.166  20.667  49.826  1.00 33.29
ATOM   3175  CB   TYR B 360      34.390  21.047  48.994  1.00 34.02
ATOM   3176  CG   TYR B 360      34.209  22.315  48.231  1.00 35.88
ATOM   3177  CD1  TYR B 360      34.789  23.500  48.670  1.00 37.17
ATOM   3178  CE1  TYR B 360      34.605  24.693  47.976  1.00 38.79
ATOM   3179  CD2  TYR B 360      33.441  22.341  47.076  1.00 37.74
ATOM   3180  CE2  TYR B 360      33.250  23.531  46.364  1.00 39.72
ATOM   3181  CZ   TYR B 360      33.838  24.700  46.821  1.00 39.50
ATOM   3182  OH   TYR B 360      33.665  25.868  46.120  1.00 41.10
ATOM   3183  C    TYR B 360      33.351  19.246  50.319  1.00 31.85
ATOM   3184  O    TYR B 360      33.396  19.001  51.526  1.00 31.99
ATOM   3185  N    ILE B 361      33.425  18.309  49.388  1.00 30.59
ATOM   3186  CA   ILE B 361      33.651  16.925  49.751  1.00 29.32
ATOM   3187  CB   ILE B 361      32.380  16.064  49.579  1.00 28.14
ATOM   3188  CG2  ILE B 361      31.201  16.724  50.278  1.00 28.12
ATOM   3189  CG1  ILE B 361      32.041  15.861  48.112  1.00 27.88
ATOM   3190  CD1  ILE B 361      31.063  14.710  47.886  1.00 27.12
ATOM   3191  C    ILE B 361      34.770  16.451  48.841  1.00 28.99
ATOM   3192  O    ILE B 361      35.185  17.178  47.954  1.00 29.75
ATOM   3193  N    HIS B 362      35.305  15.267  49.102  1.00 27.95
ATOM   3194  CA   HIS B 362      36.361  14.693  48.287  1.00 25.71
ATOM   3195  CB   HIS B 362      37.385  13.979  49.188  1.00 24.65
ATOM   3196  CG   HIS B 362      38.594  13.465  48.460  1.00 22.71
ATOM   3197  CD2  HIS B 362      39.914  13.662  48.688  1.00 21.49
ATOM   3198  ND1  HIS B 362      38.517  12.663  47.342  1.00 22.12
ATOM   3199  CE1  HIS B 362      39.736  12.388  46.912  1.00 22.53
ATOM   3200  NE2  HIS B 362      40.601  12.982  47.712  1.00 21.78
ATOM   3201  C    HIS B 362      35.729  13.683  47.328  1.00 25.82
ATOM   3202  O    HIS B 362      35.904  13.773  46.113  1.00 26.36
ATOM   3203  N    ARG B 363      34.961  12.769  47.925  1.00 25.63
ATOM   3204  CA   ARG B 363      34.253  11.638  47.323  1.00 26.53
ATOM   3205  CB   ARG B 363      33.064  12.027  46.426  1.00 31.97
ATOM   3206  CG   ARG B 363      33.348  12.702  45.119  1.00 36.30
ATOM   3207  CD   ARG B 363      32.037  13.140  44.507  1.00 38.11
ATOM   3208  NE   ARG B 363      31.290  12.015  43.960  1.00 41.24
ATOM   3209  CZ   ARG B 363      29.958  11.951  43.953  1.00 44.85
ATOM   3210  NH1  ARG B 363      29.253  12.955  44.478  1.00 44.64
ATOM   3211  NH2  ARG B 363      29.328  10.929  43.360  1.00 43.90
ATOM   3212  C    ARG B 363      35.038  10.473  46.755  1.00 25.07
ATOM   3213  O    ARG B 363      34.451   9.455  46.401  1.00 24.36
ATOM   3214  N    ASP B 364      36.363  10.586  46.741  1.00 24.51
ATOM   3215  CA   ASP B 364      37.218   9.501  46.260  1.00 24.20
ATOM   3216  CB   ASP B 364      37.717   9.751  44.826  1.00 23.99
ATOM   3217  CG   ASP B 364      36.663   9.421  43.779  1.00 23.93
ATOM   3218  OD1  ASP B 364      36.396   8.215  43.566  1.00 23.36
ATOM   3219  OD2  ASP B 364      36.081  10.366  43.196  1.00 24.50
ATOM   3220  C    ASP B 364      38.386   9.320  47.207  1.00 23.77
ATOM   3221  O    ASP B 364      39.485   8.981  46.784  1.00 24.09
ATOM   3222  N    LEU B 365      38.129   9.534  48.496  1.00 22.07
ATOM   3223  CA   LEU B 365      39.151   9.408  49.514  1.00 20.94
ATOM   3224  CB   LEU B 365      38.707  10.135  50.770  1.00 18.49
ATOM   3225  CG   LEU B 365      39.691  10.213  51.921  1.00 17.40
ATOM   3226  CD1  LEU B 365      40.941  10.971  51.480  1.00 18.42
ATOM   3227  CD2  LEU B 365      39.026  10.899  53.095  1.00 16.73
ATOM   3228  C    LEU B 365      39.591   7.970  49.844  1.00 22.81
ATOM   3229  O    LEU B 365      38.848   7.170  50.411  1.00 23.33
ATOM   3230  N    ARG B 366      40.823   7.662  49.453  1.00 24.28
ATOM   3231  CA   ARG B 366      41.454   6.369  49.692  1.00 23.29
ATOM   3232  CB   ARG B 366      40.904   5.277  48.764  1.00 23.28
```

Figure 7

| | | | | | | | | | |
|---|---|---|---|---|---|---|---|---|---|
| ATOM | 3233 | CG | ARG | B | 366 | 40.775 | 5.637 | 47.331 | 1.00 23.71 |
| ATOM | 3234 | CD | ARG | B | 366 | 40.035 | 4.534 | 46.586 | 1.00 23.71 |
| ATOM | 3235 | NE | ARG | B | 366 | 40.003 | 4.807 | 45.151 | 1.00 25.54 |
| ATOM | 3236 | CZ | ARG | B | 366 | 39.099 | 5.572 | 44.539 | 1.00 25.68 |
| ATOM | 3237 | NH1 | ARG | B | 366 | 38.115 | 6.149 | 45.228 | 1.00 26.45 |
| ATOM | 3238 | NH2 | ARG | B | 366 | 39.208 | 5.797 | 43.241 | 1.00 26.42 |
| ATOM | 3239 | C | ARG | B | 366 | 42.950 | 6.573 | 49.520 | 1.00 21.99 |
| ATOM | 3240 | O | ARG | B | 366 | 43.359 | 7.608 | 49.011 | 1.00 20.80 |
| ATOM | 3241 | N | ALA | B | 367 | 43.756 | 5.625 | 50.011 | 1.00 21.52 |
| ATOM | 3242 | CA | ALA | B | 367 | 45.221 | 5.706 | 49.949 | 1.00 21.10 |
| ATOM | 3243 | CB | ALA | B | 367 | 45.847 | 4.493 | 50.603 | 1.00 17.94 |
| ATOM | 3244 | C | ALA | B | 367 | 45.764 | 5.883 | 48.530 | 1.00 21.95 |
| ATOM | 3245 | O | ALA | B | 367 | 46.807 | 6.514 | 48.342 | 1.00 22.26 |
| ATOM | 3246 | N | ALA | B | 368 | 45.059 | 5.334 | 47.539 | 1.00 22.20 |
| ATOM | 3247 | CA | ALA | B | 368 | 45.469 | 5.467 | 46.144 | 1.00 22.28 |
| ATOM | 3248 | CB | ALA | B | 368 | 44.560 | 4.649 | 45.234 | 1.00 19.92 |
| ATOM | 3249 | C | ALA | B | 368 | 45.473 | 6.929 | 45.705 | 1.00 24.31 |
| ATOM | 3250 | O | ALA | B | 368 | 46.252 | 7.316 | 44.831 | 1.00 25.08 |
| ATOM | 3251 | N | ASN | B | 369 | 44.618 | 7.745 | 46.327 | 1.00 24.21 |
| ATOM | 3252 | CA | ASN | B | 369 | 44.521 | 9.165 | 45.978 | 1.00 23.36 |
| ATOM | 3253 | CB | ASN | B | 369 | 43.057 | 9.571 | 45.749 | 1.00 26.18 |
| ATOM | 3254 | CG | ASN | B | 369 | 42.405 | 8.773 | 44.623 | 1.00 28.36 |
| ATOM | 3255 | OD1 | ASN | B | 369 | 42.946 | 8.687 | 43.510 | 1.00 29.65 |
| ATOM | 3256 | ND2 | ASN | B | 369 | 41.265 | 8.152 | 44.914 | 1.00 28.73 |
| ATOM | 3257 | C | ASN | B | 369 | 45.233 | 10.124 | 46.917 | 1.00 21.74 |
| ATOM | 3258 | O | ASN | B | 369 | 44.896 | 11.311 | 46.998 | 1.00 19.15 |
| ATOM | 3259 | N | ILE | B | 370 | 46.170 | 9.575 | 47.685 | 1.00 21.65 |
| ATOM | 3260 | CA | ILE | B | 370 | 47.001 | 10.377 | 48.570 | 1.00 21.51 |
| ATOM | 3261 | CB | ILE | B | 370 | 47.006 | 9.876 | 50.024 | 1.00 20.80 |
| ATOM | 3262 | CG2 | ILE | B | 370 | 47.909 | 10.790 | 50.874 | 1.00 21.02 |
| ATOM | 3263 | CG1 | ILE | B | 370 | 45.580 | 9.811 | 50.583 | 1.00 17.96 |
| ATOM | 3264 | CD1 | ILE | B | 370 | 44.884 | 11.143 | 50.691 | 1.00 15.59 |
| ATOM | 3265 | C | ILE | B | 370 | 48.401 | 10.219 | 47.986 | 1.00 22.27 |
| ATOM | 3266 | O | ILE | B | 370 | 48.789 | 9.124 | 47.582 | 1.00 21.15 |
| ATOM | 3267 | N | LEU | B | 371 | 49.122 | 11.327 | 47.848 | 1.00 24.95 |
| ATOM | 3268 | CA | LEU | B | 371 | 50.471 | 11.307 | 47.282 | 1.00 26.20 |
| ATOM | 3269 | CB | LEU | B | 371 | 50.580 | 12.290 | 46.110 | 1.00 24.75 |
| ATOM | 3270 | CG | LEU | B | 371 | 49.583 | 12.060 | 44.985 | 1.00 23.72 |
| ATOM | 3271 | CD1 | LEU | B | 371 | 49.719 | 13.137 | 43.938 | 1.00 22.69 |
| ATOM | 3272 | CD2 | LEU | B | 371 | 49.805 | 10.691 | 44.384 | 1.00 24.75 |
| ATOM | 3273 | C | LEU | B | 371 | 51.526 | 11.626 | 48.323 | 1.00 27.56 |
| ATOM | 3274 | O | LEU | B | 371 | 51.285 | 12.388 | 49.265 | 1.00 27.94 |
| ATOM | 3275 | N | VAL | B | 372 | 52.701 | 11.030 | 48.142 | 1.00 28.16 |
| ATOM | 3276 | CA | VAL | B | 372 | 53.814 | 11.226 | 49.061 | 1.00 28.88 |
| ATOM | 3277 | CB | VAL | B | 372 | 54.360 | 9.853 | 49.549 | 1.00 28.42 |
| ATOM | 3278 | CG1 | VAL | B | 372 | 55.233 | 10.036 | 50.771 | 1.00 26.78 |
| ATOM | 3279 | CG2 | VAL | B | 372 | 53.211 | 8.888 | 49.838 | 1.00 27.63 |
| ATOM | 3280 | C | VAL | B | 372 | 54.946 | 12.035 | 48.400 | 1.00 29.88 |
| ATOM | 3281 | O | VAL | B | 372 | 55.299 | 11.803 | 47.244 | 1.00 29.75 |
| ATOM | 3282 | N | SER | B | 373 | 55.471 | 13.023 | 49.117 | 1.00 31.80 |
| ATOM | 3283 | CA | SER | B | 373 | 56.568 | 13.844 | 48.607 | 1.00 32.49 |
| ATOM | 3284 | CB | SER | B | 373 | 56.483 | 15.267 | 49.156 | 1.00 30.79 |
| ATOM | 3285 | OG | SER | B | 373 | 56.831 | 15.301 | 50.521 | 1.00 30.31 |
| ATOM | 3286 | C | SER | B | 373 | 57.904 | 13.225 | 49.015 | 1.00 33.98 |
| ATOM | 3287 | O | SER | B | 373 | 57.942 | 12.180 | 49.665 | 1.00 33.73 |
| ATOM | 3288 | N | ASP | B | 374 | 58.995 | 13.878 | 48.618 | 1.00 36.20 |
| ATOM | 3289 | CA | ASP | B | 374 | 60.356 | 13.425 | 48.938 | 1.00 37.68 |
| ATOM | 3290 | CB | ASP | B | 374 | 61.401 | 14.222 | 48.130 | 1.00 40.07 |
| ATOM | 3291 | CG | ASP | B | 374 | 61.211 | 15.742 | 48.227 | 1.00 42.83 |

Figure 7

```
ATOM   3292  OD1 ASP B 374      60.079  16.239  48.040  1.00 45.63
ATOM   3293  OD2 ASP B 374      62.209  16.456  48.463  1.00 44.21
ATOM   3294  C   ASP B 374      60.649  13.489  50.440  1.00 37.44
ATOM   3295  O   ASP B 374      61.430  12.691  50.970  1.00 37.69
ATOM   3296  N   THR B 375      59.974  14.407  51.126  1.00 37.28
ATOM   3297  CA  THR B 375      60.135  14.578  52.566  1.00 36.99
ATOM   3298  CB  THR B 375      59.942  16.058  52.979  1.00 37.45
ATOM   3299  OG1 THR B 375      58.606  16.473  52.670  1.00 39.62
ATOM   3300  CG2 THR B 375      60.929  16.959  52.231  1.00 36.42
ATOM   3301  C   THR B 375      59.163  13.677  53.343  1.00 36.14
ATOM   3302  O   THR B 375      59.061  13.767  54.570  1.00 35.72
ATOM   3303  N   LEU B 376      58.474  12.802  52.611  1.00 36.01
ATOM   3304  CA  LEU B 376      57.505  11.848  53.160  1.00 36.03
ATOM   3305  CB  LEU B 376      58.163  10.894  54.167  1.00 36.62
ATOM   3306  CG  LEU B 376      59.361  10.044  53.727  1.00 36.31
ATOM   3307  CD1 LEU B 376      59.584   8.960  54.762  1.00 36.84
ATOM   3308  CD2 LEU B 376      59.121   9.423  52.356  1.00 34.61
ATOM   3309  C   LEU B 376      56.233  12.445  53.757  1.00 35.83
ATOM   3310  O   LEU B 376      55.586  11.810  54.592  1.00 34.72
ATOM   3311  N   SER B 377      55.902  13.677  53.363  1.00 36.51
ATOM   3312  CA  SER B 377      54.673  14.332  53.830  1.00 36.48
ATOM   3313  CB  SER B 377      54.871  15.847  53.991  1.00 36.99
ATOM   3314  OG  SER B 377      54.945  16.495  52.731  1.00 40.41
ATOM   3315  C   SER B 377      53.558  14.017  52.809  1.00 35.41
ATOM   3316  O   SER B 377      53.832  13.813  51.616  1.00 35.53
ATOM   3317  N   CYS B 378      52.309  13.982  53.269  1.00 33.71
ATOM   3318  CA  CYS B 378      51.190  13.639  52.394  1.00 31.18
ATOM   3319  CB  CYS B 378      50.226  12.675  53.111  1.00 31.64
ATOM   3320  SG  CYS B 378      50.923  11.037  53.536  1.00 30.20
ATOM   3321  C   CYS B 378      50.411  14.819  51.834  1.00 28.86
ATOM   3322  O   CYS B 378      50.315  15.881  52.451  1.00 27.30
ATOM   3323  N   LYS B 379      49.903  14.615  50.623  1.00 27.71
ATOM   3324  CA  LYS B 379      49.098  15.598  49.925  1.00 26.13
ATOM   3325  CB  LYS B 379      49.955  16.388  48.924  1.00 26.73
ATOM   3326  CG  LYS B 379      50.758  17.554  49.530  1.00 26.85
ATOM   3327  CD  LYS B 379      51.828  18.080  48.570  1.00 28.24
ATOM   3328  CE  LYS B 379      52.364  19.469  48.933  1.00 28.92
ATOM   3329  NZ  LYS B 379      51.466  20.594  48.470  1.00 33.13
ATOM   3330  C   LYS B 379      47.944  14.861  49.236  1.00 25.15
ATOM   3331  O   LYS B 379      48.125  13.799  48.639  1.00 23.50
ATOM   3332  N   ILE B 380      46.740  15.388  49.412  1.00 25.58
ATOM   3333  CA  ILE B 380      45.511  14.836  48.845  1.00 24.26
ATOM   3334  CB  ILE B 380      44.279  15.427  49.586  1.00 23.48
ATOM   3335  CG2 ILE B 380      43.002  14.869  49.040  1.00 22.67
ATOM   3336  CG1 ILE B 380      44.373  15.160  51.085  1.00 24.20
ATOM   3337  CD1 ILE B 380      43.236  15.762  51.854  1.00 23.85
ATOM   3338  C   ILE B 380      45.378  15.174  47.350  1.00 24.14
ATOM   3339  O   ILE B 380      45.528  16.325  46.946  1.00 23.25
ATOM   3340  N   ALA B 381      45.048  14.173  46.544  1.00 24.51
ATOM   3341  CA  ALA B 381      44.860  14.352  45.109  1.00 25.70
ATOM   3342  CB  ALA B 381      45.903  13.547  44.350  1.00 25.61
ATOM   3343  C   ALA B 381      43.445  13.903  44.705  1.00 26.91
ATOM   3344  O   ALA B 381      42.681  13.386  45.540  1.00 26.52
ATOM   3345  N   ASP B 382      43.110  14.108  43.430  1.00 27.78
ATOM   3346  CA  ASP B 382      41.813  13.730  42.856  1.00 29.15
ATOM   3347  CB  ASP B 382      41.802  12.230  42.510  1.00 30.72
ATOM   3348  CG  ASP B 382      42.688  11.882  41.321  1.00 32.90
ATOM   3349  OD1 ASP B 382      42.697  12.623  40.317  1.00 35.39
ATOM   3350  OD2 ASP B 382      43.361  10.838  41.372  1.00 36.36
```

Figure 7

| | | | | | | | | | |
|---|---|---|---|---|---|---|---|---|---|
| ATOM | 3351 | C | ASP | B | 382 | 40.594 | 14.049 | 43.722 | 1.00 30.21 |
| ATOM | 3352 | O | ASP | B | 382 | 39.704 | 13.209 | 43.861 | 1.00 29.63 |
| ATOM | 3353 | N | PHE | B | 383 | 40.544 | 15.256 | 44.289 | 1.00 31.12 |
| ATOM | 3354 | CA | PHE | B | 383 | 39.427 | 15.658 | 45.152 | 1.00 32.37 |
| ATOM | 3355 | CB | PHE | B | 383 | 39.922 | 16.345 | 46.446 | 1.00 31.76 |
| ATOM | 3356 | CG | PHE | B | 383 | 40.874 | 17.492 | 46.212 | 1.00 32.46 |
| ATOM | 3357 | CD1 | PHE | B | 383 | 40.396 | 18.797 | 46.045 | 1.00 33.08 |
| ATOM | 3358 | CD2 | PHE | B | 383 | 42.250 | 17.263 | 46.116 | 1.00 30.33 |
| ATOM | 3359 | CE1 | PHE | B | 383 | 41.278 | 19.851 | 45.782 | 1.00 31.58 |
| ATOM | 3360 | CE2 | PHE | B | 383 | 43.134 | 18.299 | 45.857 | 1.00 30.00 |
| ATOM | 3361 | CZ | PHE | B | 383 | 42.647 | 19.601 | 45.685 | 1.00 32.40 |
| ATOM | 3362 | C | PHE | B | 383 | 38.377 | 16.535 | 44.492 | 1.00 33.32 |
| ATOM | 3363 | O | PHE | B | 383 | 38.669 | 17.354 | 43.615 | 1.00 32.66 |
| ATOM | 3364 | N | GLY | B | 384 | 37.141 | 16.334 | 44.919 | 1.00 34.21 |
| ATOM | 3365 | CA | GLY | B | 384 | 36.051 | 17.128 | 44.403 | 1.00 35.07 |
| ATOM | 3366 | C | GLY | B | 384 | 35.490 | 16.705 | 43.074 | 1.00 35.26 |
| ATOM | 3367 | O | GLY | B | 384 | 34.710 | 17.461 | 42.505 | 1.00 36.35 |
| ATOM | 3368 | N | LEU | B | 385 | 35.868 | 15.533 | 42.566 | 1.00 35.95 |
| ATOM | 3369 | CA | LEU | B | 385 | 35.334 | 15.071 | 41.282 | 1.00 36.11 |
| ATOM | 3370 | CB | LEU | B | 385 | 36.009 | 13.789 | 40.784 | 1.00 36.32 |
| ATOM | 3371 | CG | LEU | B | 385 | 37.509 | 13.785 | 40.492 | 1.00 37.61 |
| ATOM | 3372 | CD1 | LEU | B | 385 | 37.741 | 12.940 | 39.266 | 1.00 36.80 |
| ATOM | 3373 | CD2 | LEU | B | 385 | 38.044 | 15.188 | 40.269 | 1.00 38.83 |
| ATOM | 3374 | C | LEU | B | 385 | 33.849 | 14.830 | 41.463 | 1.00 36.26 |
| ATOM | 3375 | O | LEU | B | 385 | 33.390 | 14.617 | 42.588 | 1.00 36.07 |
| ATOM | 3376 | N | ALA | B | 386 | 33.096 | 14.865 | 40.367 | 1.00 36.01 |
| ATOM | 3377 | CA | ALA | B | 386 | 31.656 | 14.700 | 40.417 | 1.00 36.23 |
| ATOM | 3378 | CB | ALA | B | 386 | 31.019 | 15.343 | 39.189 | 1.00 37.64 |
| ATOM | 3379 | C | ALA | B | 386 | 31.193 | 13.251 | 40.558 | 1.00 36.19 |
| ATOM | 3380 | O | ALA | B | 386 | 30.130 | 12.992 | 41.102 | 1.00 36.70 |
| ATOM | 3381 | N | ARG | B | 387 | 31.965 | 12.317 | 40.020 | 1.00 35.92 |
| ATOM | 3382 | CA | ARG | B | 387 | 31.611 | 10.904 | 40.101 | 1.00 34.54 |
| ATOM | 3383 | CB | ARG | B | 387 | 31.556 | 10.289 | 38.694 | 1.00 33.66 |
| ATOM | 3384 | CG | ARG | B | 387 | 32.857 | 10.414 | 37.949 | 1.00 33.25 |
| ATOM | 3385 | CD | ARG | B | 387 | 32.792 | 9.928 | 36.534 | 1.00 34.17 |
| ATOM | 3386 | NE | ARG | B | 387 | 34.087 | 10.128 | 35.901 | 1.00 37.78 |
| ATOM | 3387 | CZ | ARG | B | 387 | 34.992 | 9.169 | 35.752 | 1.00 38.54 |
| ATOM | 3388 | NH1 | ARG | B | 387 | 34.745 | 7.935 | 36.184 | 1.00 38.23 |
| ATOM | 3389 | NH2 | ARG | B | 387 | 36.153 | 9.463 | 35.181 | 1.00 38.68 |
| ATOM | 3390 | C | ARG | B | 387 | 32.639 | 10.153 | 40.935 | 1.00 34.35 |
| ATOM | 3391 | O | ARG | B | 387 | 33.567 | 10.731 | 41.512 | 1.00 33.06 |
| ATOM | 3392 | N | LEU | B | 388 | 32.444 | 8.849 | 41.008 | 1.00 35.01 |
| ATOM | 3393 | CA | LEU | B | 388 | 33.367 | 7.999 | 41.732 | 1.00 35.82 |
| ATOM | 3394 | CB | LEU | B | 388 | 32.629 | 6.868 | 42.422 | 1.00 38.53 |
| ATOM | 3395 | CG | LEU | B | 388 | 31.572 | 7.326 | 43.420 | 1.00 40.49 |
| ATOM | 3396 | CD1 | LEU | B | 388 | 30.130 | 7.329 | 42.765 | 1.00 41.30 |
| ATOM | 3397 | CD2 | LEU | B | 388 | 31.672 | 6.379 | 44.611 | 1.00 38.82 |
| ATOM | 3398 | C | LEU | B | 388 | 34.256 | 7.454 | 40.628 | 1.00 34.90 |
| ATOM | 3399 | O | LEU | B | 388 | 33.760 | 6.989 | 39.594 | 1.00 35.61 |
| ATOM | 3400 | N | ILE | B | 389 | 35.559 | 7.621 | 40.802 | 1.00 33.35 |
| ATOM | 3401 | CA | ILE | B | 389 | 36.522 | 7.176 | 39.808 | 1.00 30.40 |
| ATOM | 3402 | CB | ILE | B | 389 | 37.581 | 8.273 | 39.543 | 1.00 26.91 |
| ATOM | 3403 | CG2 | ILE | B | 389 | 36.890 | 9.595 | 39.254 | 1.00 23.23 |
| ATOM | 3404 | CG1 | ILE | B | 389 | 38.509 | 8.429 | 40.749 | 1.00 25.51 |
| ATOM | 3405 | CD1 | ILE | B | 389 | 39.368 | 9.668 | 40.697 | 1.00 23.38 |
| ATOM | 3406 | C | ILE | B | 389 | 37.208 | 5.886 | 40.227 | 1.00 32.06 |
| ATOM | 3407 | O | ILE | B | 389 | 37.266 | 5.544 | 41.406 | 1.00 31.41 |
| ATOM | 3408 | N | GLU | B | 390 | 37.677 | 5.144 | 39.235 | 1.00 34.18 |
| ATOM | 3409 | CA | GLU | B | 390 | 38.387 | 3.896 | 39.461 | 1.00 35.55 |

Figure 7

```
ATOM   3410  CB   GLU B 390      37.920    2.842   38.475  1.00 36.67
ATOM   3411  CG   GLU B 390      36.467    2.487   38.644  1.00 39.69
ATOM   3412  CD   GLU B 390      35.974    1.564   37.569  1.00 42.17
ATOM   3413  OE1  GLU B 390      34.866    1.791   37.060  1.00 46.38
ATOM   3414  OE2  GLU B 390      36.686    0.607   37.227  1.00 45.07
ATOM   3415  C    GLU B 390      39.868    4.170   39.288  1.00 36.01
ATOM   3416  O    GLU B 390      40.257    5.076   38.553  1.00 35.02
ATOM   3417  N    ASP B 391      40.691    3.390   39.977  1.00 38.18
ATOM   3418  CA   ASP B 391      42.142    3.568   39.938  1.00 39.77
ATOM   3419  CB   ASP B 391      42.784    2.750   41.061  1.00 40.60
ATOM   3420  CG   ASP B 391      42.178    3.073   42.423  1.00 41.85
ATOM   3421  OD1  ASP B 391      41.827    4.254   42.664  1.00 42.36
ATOM   3422  OD2  ASP B 391      42.033    2.147   43.242  1.00 41.93
ATOM   3423  C    ASP B 391      42.798    3.268   38.595  1.00 39.72
ATOM   3424  O    ASP B 391      43.850    3.829   38.274  1.00 39.95
ATOM   3425  N    ASN B 392      42.123    2.456   37.784  1.00 39.59
ATOM   3426  CA   ASN B 392      42.641    2.066   36.479  1.00 40.22
ATOM   3427  CB   ASN B 392      42.108    0.665   36.085  1.00 43.35
ATOM   3428  CG   ASN B 392      40.686    0.694   35.459  1.00 48.29
ATOM   3429  OD1  ASN B 392      39.838    1.542   35.790  1.00 50.32
ATOM   3430  ND2  ASN B 392      40.430   -0.248   34.549  1.00 48.97
ATOM   3431  C    ASN B 392      42.377    3.089   35.367  1.00 38.48
ATOM   3432  O    ASN B 392      42.669    2.828   34.206  1.00 39.75
ATOM   3433  N    GLU B 393      41.847    4.256   35.717  1.00 36.12
ATOM   3434  CA   GLU B 393      41.539    5.268   34.717  1.00 33.60
ATOM   3435  CB   GLU B 393      40.503    6.264   35.260  1.00 31.39
ATOM   3436  CG   GLU B 393      39.130    5.634   35.499  1.00 27.40
ATOM   3437  CD   GLU B 393      38.076    6.611   35.973  1.00 24.92
ATOM   3438  OE1  GLU B 393      38.287    7.824   35.885  1.00 25.71
ATOM   3439  OE2  GLU B 393      37.011    6.170   36.423  1.00 25.86
ATOM   3440  C    GLU B 393      42.753    5.976   34.123  1.00 34.40
ATOM   3441  O    GLU B 393      42.713    6.394   32.963  1.00 34.25
ATOM   3442  N    TYR B 394      43.833    6.107   34.901  1.00 35.25
ATOM   3443  CA   TYR B 394      45.058    6.753   34.404  1.00 35.72
ATOM   3444  CB   TYR B 394      45.205    8.174   34.950  1.00 34.10
ATOM   3445  CG   TYR B 394      44.091    9.086   34.503  1.00 34.73
ATOM   3446  CD1  TYR B 394      42.929    9.218   35.260  1.00 34.34
ATOM   3447  CE1  TYR B 394      41.857    9.972   34.807  1.00 34.48
ATOM   3448  CD2  TYR B 394      44.157    9.751   33.284  1.00 35.81
ATOM   3449  CE2  TYR B 394      43.082   10.517   32.818  1.00 35.37
ATOM   3450  CZ   TYR B 394      41.936   10.616   33.585  1.00 35.19
ATOM   3451  OH   TYR B 394      40.852   11.328   33.123  1.00 35.28
ATOM   3452  C    TYR B 394      46.300    5.933   34.709  1.00 37.25
ATOM   3453  O    TYR B 394      47.428    6.387   34.467  1.00 35.95
ATOM   3454  N    THR B 395      46.090    4.740   35.268  1.00 39.83
ATOM   3455  CA   THR B 395      47.170    3.812   35.580  1.00 43.70
ATOM   3456  CB   THR B 395      47.657    3.870   37.064  1.00 43.92
ATOM   3457  OG1  THR B 395      46.994    4.912   37.795  1.00 41.67
ATOM   3458  CG2  THR B 395      49.162    4.097   37.077  1.00 43.00
ATOM   3459  C    THR B 395      46.723    2.392   35.295  1.00 46.59
ATOM   3460  O    THR B 395      45.652    2.180   34.717  1.00 46.44
ATOM   3461  N    ALA B 396      47.518    1.413   35.725  1.00 50.59
ATOM   3462  CA   ALA B 396      47.203    0.011   35.492  1.00 54.34
ATOM   3463  CB   ALA B 396      48.085   -0.535   34.372  1.00 54.72
ATOM   3464  C    ALA B 396      47.314   -0.887   36.734  1.00 56.94
ATOM   3465  O    ALA B 396      48.185   -1.770   36.779  1.00 59.09
ATOM   3466  N    ARG B 397      46.453   -0.658   37.730  1.00 57.84
ATOM   3467  CA   ARG B 397      46.460   -1.480   38.943  1.00 58.22
ATOM   3468  CB   ARG B 397      46.036   -0.668   40.166  1.00 58.92
```

Figure 7

```
ATOM   3469  CG   ARG B 397      47.082   0.308  40.684  1.00 58.34
ATOM   3470  CD   ARG B 397      46.995   0.407  42.207  1.00 58.36
ATOM   3471  NE   ARG B 397      47.823   1.476  42.757  1.00 57.60
ATOM   3472  CZ   ARG B 397      47.514   2.770  42.692  1.00 57.73
ATOM   3473  NH1  ARG B 397      46.394   3.162  42.090  1.00 57.75
ATOM   3474  NH2  ARG B 397      48.320   3.674  43.237  1.00 57.51
ATOM   3475  C    ARG B 397      45.571  -2.726  38.808  1.00 58.56
ATOM   3476  O    ARG B 397      46.087  -3.847  39.043  1.00 58.57
ATOM   3477  CB   PRO B 403      35.878   2.750  44.298  1.00 26.43
ATOM   3478  CG   PRO B 403      36.149   2.385  42.857  1.00 27.52
ATOM   3479  C    PRO B 403      34.882   1.290  46.099  1.00 26.93
ATOM   3480  O    PRO B 403      34.809   2.158  46.998  1.00 25.42
ATOM   3481  N    PRO B 403      35.523   0.391  43.847  1.00 26.10
ATOM   3482  CD   PRO B 403      35.444   1.067  42.553  1.00 27.95
ATOM   3483  CA   PRO B 403      35.893   1.377  44.936  1.00 27.54
ATOM   3484  N    ILE B 404      34.086   0.224  46.048  1.00 26.66
ATOM   3485  CA   ILE B 404      33.051  -0.072  47.019  1.00 25.51
ATOM   3486  CB   ILE B 404      32.343  -1.381  46.613  1.00 26.20
ATOM   3487  CG2  ILE B 404      31.781  -2.135  47.828  1.00 26.04
ATOM   3488  CG1  ILE B 404      31.291  -1.076  45.547  1.00 26.73
ATOM   3489  CD1  ILE B 404      30.309  -0.022  46.000  1.00 28.74
ATOM   3490  C    ILE B 404      33.531  -0.132  48.464  1.00 24.73
ATOM   3491  O    ILE B 404      32.872   0.390  49.364  1.00 24.97
ATOM   3492  N    LYS B 405      34.719  -0.690  48.670  1.00 23.66
ATOM   3493  CA   LYS B 405      35.279  -0.849  50.011  1.00 22.22
ATOM   3494  CB   LYS B 405      36.485  -1.777  49.972  1.00 21.92
ATOM   3495  CG   LYS B 405      36.140  -3.165  49.485  1.00 22.89
ATOM   3496  CD   LYS B 405      37.369  -4.050  49.451  1.00 22.85
ATOM   3497  CE   LYS B 405      36.986  -5.467  49.118  1.00 21.86
ATOM   3498  NZ   LYS B 405      38.028  -6.370  49.633  1.00 24.56
ATOM   3499  C    LYS B 405      35.601   0.408  50.824  1.00 21.44
ATOM   3500  O    LYS B 405      35.934   0.299  52.009  1.00 22.01
ATOM   3501  N    TRP B 406      35.488   1.584  50.199  1.00 21.15
ATOM   3502  CA   TRP B 406      35.727   2.870  50.876  1.00 20.04
ATOM   3503  CB   TRP B 406      36.776   3.709  50.131  1.00 20.63
ATOM   3504  CG   TRP B 406      38.164   3.184  50.208  1.00 20.26
ATOM   3505  CD2  TRP B 406      38.718   2.145  49.399  1.00 21.13
ATOM   3506  CE2  TRP B 406      40.040   1.943  49.832  1.00 20.84
ATOM   3507  CE3  TRP B 406      38.218   1.354  48.347  1.00 20.18
ATOM   3508  CD1  TRP B 406      39.147   3.567  51.079  1.00 19.53
ATOM   3509  NE1  TRP B 406      40.274   2.822  50.863  1.00 19.66
ATOM   3510  CZ2  TRP B 406      40.877   0.980  49.250  1.00 20.68
ATOM   3511  CZ3  TRP B 406      39.050   0.395  47.776  1.00 19.70
ATOM   3512  CH2  TRP B 406      40.363   0.219  48.230  1.00 18.94
ATOM   3513  C    TRP B 406      34.456   3.711  50.936  1.00 20.04
ATOM   3514  O    TRP B 406      34.447   4.766  51.573  1.00 17.79
ATOM   3515  N    THR B 407      33.401   3.235  50.263  1.00 20.32
ATOM   3516  CA   THR B 407      32.125   3.930  50.144  1.00 21.81
ATOM   3517  CB   THR B 407      31.517   3.587  48.780  1.00 21.95
ATOM   3518  OG1  THR B 407      32.526   3.800  47.792  1.00 23.28
ATOM   3519  CG2  THR B 407      30.333   4.474  48.434  1.00 23.20
ATOM   3520  C    THR B 407      31.124   3.683  51.278  1.00 22.35
ATOM   3521  O    THR B 407      30.780   2.536  51.571  1.00 23.83
ATOM   3522  N    ALA B 408      30.691   4.771  51.932  1.00 22.33
ATOM   3523  CA   ALA B 408      29.735   4.705  53.046  1.00 22.25
ATOM   3524  CB   ALA B 408      29.550   6.088  53.665  1.00 20.16
ATOM   3525  C    ALA B 408      28.390   4.126  52.599  1.00 21.65
ATOM   3526  O    ALA B 408      28.003   4.284  51.459  1.00 21.04
ATOM   3527  N    PRO B 409      27.659   3.460  53.508  1.00 22.63
```

Figure 7

| | | | | | | | | | |
|---|---|---|---|---|---|---|---|---|---|
| ATOM | 3528 | CD | PRO | B | 409 | 28.059 | 3.220 | 54.905 | 1.00 22.65 |
| ATOM | 3529 | CA | PRO | B | 409 | 26.353 | 2.839 | 53.240 | 1.00 23.54 |
| ATOM | 3530 | CB | PRO | B | 409 | 25.930 | 2.340 | 54.617 | 1.00 22.78 |
| ATOM | 3531 | CG | PRO | B | 409 | 27.238 | 2.015 | 55.262 | 1.00 22.31 |
| ATOM | 3532 | C | PRO | B | 409 | 25.270 | 3.700 | 52.583 | 1.00 23.62 |
| ATOM | 3533 | O | PRO | B | 409 | 24.628 | 3.268 | 51.631 | 1.00 22.95 |
| ATOM | 3534 | N | GLU | B | 410 | 25.048 | 4.899 | 53.107 | 1.00 23.60 |
| ATOM | 3535 | CA | GLU | B | 410 | 24.065 | 5.799 | 52.518 | 1.00 24.31 |
| ATOM | 3536 | CB | GLU | B | 410 | 23.905 | 7.068 | 53.367 | 1.00 23.84 |
| ATOM | 3537 | CG | GLU | B | 410 | 25.097 | 8.022 | 53.361 | 1.00 24.04 |
| ATOM | 3538 | CD | GLU | B | 410 | 26.188 | 7.677 | 54.368 | 1.00 22.69 |
| ATOM | 3539 | OE1 | GLU | B | 410 | 26.257 | 6.539 | 54.883 | 1.00 23.35 |
| ATOM | 3540 | OE2 | GLU | B | 410 | 26.992 | 8.572 | 54.662 | 1.00 23.18 |
| ATOM | 3541 | C | GLU | B | 410 | 24.481 | 6.157 | 51.081 | 1.00 25.97 |
| ATOM | 3542 | O | GLU | B | 410 | 23.634 | 6.450 | 50.237 | 1.00 26.43 |
| ATOM | 3543 | N | ALA | B | 411 | 25.783 | 6.105 | 50.804 | 1.00 27.47 |
| ATOM | 3544 | CA | ALA | B | 411 | 26.304 | 6.411 | 49.475 | 1.00 28.62 |
| ATOM | 3545 | CB | ALA | B | 411 | 27.795 | 6.746 | 49.542 | 1.00 27.05 |
| ATOM | 3546 | C | ALA | B | 411 | 26.061 | 5.225 | 48.545 | 1.00 29.82 |
| ATOM | 3547 | O | ALA | B | 411 | 25.680 | 5.402 | 47.388 | 1.00 31.71 |
| ATOM | 3548 | N | ILE | B | 412 | 26.249 | 4.017 | 49.059 | 1.00 30.54 |
| ATOM | 3549 | CA | ILE | B | 412 | 26.039 | 2.815 | 48.263 | 1.00 31.65 |
| ATOM | 3550 | CB | ILE | B | 412 | 26.487 | 1.549 | 49.038 | 1.00 31.57 |
| ATOM | 3551 | CG2 | ILE | B | 412 | 25.962 | 0.273 | 48.372 | 1.00 30.37 |
| ATOM | 3552 | CG1 | ILE | B | 412 | 28.009 | 1.518 | 49.176 | 1.00 30.74 |
| ATOM | 3553 | CD1 | ILE | B | 412 | 28.503 | 0.427 | 50.088 | 1.00 31.20 |
| ATOM | 3554 | C | ILE | B | 412 | 24.557 | 2.683 | 47.918 | 1.00 33.62 |
| ATOM | 3555 | O | ILE | B | 412 | 24.194 | 2.551 | 46.751 | 1.00 34.83 |
| ATOM | 3556 | N | ASN | B | 413 | 23.710 | 2.757 | 48.944 | 1.00 34.19 |
| ATOM | 3557 | CA | ASN | B | 413 | 22.265 | 2.618 | 48.797 | 1.00 34.38 |
| ATOM | 3558 | CB | ASN | B | 413 | 21.622 | 2.413 | 50.162 | 1.00 35.06 |
| ATOM | 3559 | CG | ASN | B | 413 | 22.145 | 1.194 | 50.870 | 1.00 36.18 |
| ATOM | 3560 | OD1 | ASN | B | 413 | 22.663 | 0.272 | 50.238 | 1.00 37.89 |
| ATOM | 3561 | ND2 | ASN | B | 413 | 22.030 | 1.180 | 52.193 | 1.00 35.70 |
| ATOM | 3562 | C | ASN | B | 413 | 21.525 | 3.737 | 48.088 | 1.00 34.58 |
| ATOM | 3563 | O | ASN | B | 413 | 20.827 | 3.493 | 47.114 | 1.00 35.17 |
| ATOM | 3564 | N | TYR | B | 414 | 21.660 | 4.961 | 48.586 | 1.00 34.63 |
| ATOM | 3565 | CA | TYR | B | 414 | 20.940 | 6.087 | 48.003 | 1.00 34.51 |
| ATOM | 3566 | CB | TYR | B | 414 | 20.109 | 6.784 | 49.102 | 1.00 37.57 |
| ATOM | 3567 | CG | TYR | B | 414 | 19.296 | 5.815 | 49.972 | 1.00 40.66 |
| ATOM | 3568 | CD1 | TYR | B | 414 | 18.201 | 5.110 | 49.449 | 1.00 41.84 |
| ATOM | 3569 | CE1 | TYR | B | 414 | 17.507 | 4.158 | 50.228 | 1.00 43.56 |
| ATOM | 3570 | CD2 | TYR | B | 414 | 19.669 | 5.557 | 51.297 | 1.00 42.26 |
| ATOM | 3571 | CE2 | TYR | B | 414 | 18.986 | 4.616 | 52.078 | 1.00 43.68 |
| ATOM | 3572 | CZ | TYR | B | 414 | 17.908 | 3.914 | 51.538 | 1.00 44.92 |
| ATOM | 3573 | OH | TYR | B | 414 | 17.258 | 2.955 | 52.298 | 1.00 44.79 |
| ATOM | 3574 | C | TYR | B | 414 | 21.808 | 7.080 | 47.216 | 1.00 33.07 |
| ATOM | 3575 | O | TYR | B | 414 | 21.322 | 8.100 | 46.733 | 1.00 32.66 |
| ATOM | 3576 | N | GLY | B | 415 | 23.089 | 6.760 | 47.058 | 1.00 31.79 |
| ATOM | 3577 | CA | GLY | B | 415 | 23.985 | 7.625 | 46.317 | 1.00 29.59 |
| ATOM | 3578 | C | GLY | B | 415 | 24.195 | 8.992 | 46.928 | 1.00 29.72 |
| ATOM | 3579 | O | GLY | B | 415 | 24.578 | 9.934 | 46.236 | 1.00 30.18 |
| ATOM | 3580 | N | THR | B | 416 | 23.943 | 9.119 | 48.226 | 1.00 29.14 |
| ATOM | 3581 | CA | THR | B | 416 | 24.142 | 10.398 | 48.889 | 1.00 27.76 |
| ATOM | 3582 | CB | THR | B | 416 | 23.052 | 10.661 | 49.977 | 1.00 28.40 |
| ATOM | 3583 | OG1 | THR | B | 416 | 23.647 | 10.804 | 51.272 | 1.00 31.63 |
| ATOM | 3584 | CG2 | THR | B | 416 | 22.034 | 9.541 | 50.001 | 1.00 27.20 |
| ATOM | 3585 | C | THR | B | 416 | 25.592 | 10.539 | 49.411 | 1.00 26.61 |
| ATOM | 3586 | O | THR | B | 416 | 26.049 | 9.767 | 50.255 | 1.00 26.50 |

Figure 7

| | | | | | | | | | |
|---|---|---|---|---|---|---|---|---|---|
| ATOM | 3587 | N | PHE | B | 417 | 26.327 | 11.476 | 48.815 | 1.00 24.47 |
| ATOM | 3588 | CA | PHE | B | 417 | 27.711 | 11.753 | 49.174 | 1.00 23.60 |
| ATOM | 3589 | CB | PHE | B | 417 | 28.590 | 11.811 | 47.912 | 1.00 22.05 |
| ATOM | 3590 | CG | PHE | B | 417 | 28.807 | 10.482 | 47.264 | 1.00 21.98 |
| ATOM | 3591 | CD1 | PHE | B | 417 | 27.893 | 9.989 | 46.331 | 1.00 23.26 |
| ATOM | 3592 | CD2 | PHE | B | 417 | 29.891 | 9.685 | 47.625 | 1.00 20.61 |
| ATOM | 3593 | CE1 | PHE | B | 417 | 28.055 | 8.705 | 45.774 | 1.00 22.48 |
| ATOM | 3594 | CE2 | PHE | B | 417 | 30.058 | 8.411 | 47.080 | 1.00 21.04 |
| ATOM | 3595 | CZ | PHE | B | 417 | 29.140 | 7.917 | 46.155 | 1.00 21.72 |
| ATOM | 3596 | C | PHE | B | 417 | 27.821 | 13.076 | 49.914 | 1.00 23.39 |
| ATOM | 3597 | O | PHE | B | 417 | 27.361 | 14.097 | 49.415 | 1.00 24.02 |
| ATOM | 3598 | N | THR | B | 418 | 28.418 | 13.057 | 51.103 | 1.00 22.27 |
| ATOM | 3599 | CA | THR | B | 418 | 28.607 | 14.267 | 51.907 | 1.00 23.29 |
| ATOM | 3600 | CB | THR | B | 418 | 27.566 | 14.389 | 53.048 | 1.00 24.53 |
| ATOM | 3601 | OG1 | THR | B | 418 | 27.741 | 13.308 | 53.975 | 1.00 26.51 |
| ATOM | 3602 | CG2 | THR | B | 418 | 26.131 | 14.361 | 52.497 | 1.00 23.13 |
| ATOM | 3603 | C | THR | B | 418 | 29.993 | 14.213 | 52.548 | 1.00 22.16 |
| ATOM | 3604 | O | THR | B | 418 | 30.730 | 13.248 | 52.350 | 1.00 22.30 |
| ATOM | 3605 | N | ILE | B | 419 | 30.355 | 15.240 | 53.309 | 1.00 20.90 |
| ATOM | 3606 | CA | ILE | B | 419 | 31.656 | 15.243 | 53.967 | 1.00 20.09 |
| ATOM | 3607 | CB | ILE | B | 419 | 31.937 | 16.585 | 54.716 | 1.00 19.49 |
| ATOM | 3608 | CG2 | ILE | B | 419 | 31.062 | 16.716 | 55.969 | 1.00 16.42 |
| ATOM | 3609 | CG1 | ILE | B | 419 | 33.421 | 16.691 | 55.097 | 1.00 19.91 |
| ATOM | 3610 | CD1 | ILE | B | 419 | 34.393 | 16.653 | 53.924 | 1.00 15.99 |
| ATOM | 3611 | C | ILE | B | 419 | 31.710 | 14.050 | 54.930 | 1.00 19.58 |
| ATOM | 3612 | O | ILE | B | 419 | 32.780 | 13.502 | 55.182 | 1.00 20.16 |
| ATOM | 3613 | N | LYS | B | 420 | 30.537 | 13.619 | 55.408 | 1.00 18.73 |
| ATOM | 3614 | CA | LYS | B | 420 | 30.419 | 12.474 | 56.332 | 1.00 16.80 |
| ATOM | 3615 | CB | LYS | B | 420 | 29.060 | 12.470 | 57.046 | 1.00 15.69 |
| ATOM | 3616 | CG | LYS | B | 420 | 28.849 | 13.636 | 57.986 | 1.00 12.82 |
| ATOM | 3617 | CD | LYS | B | 420 | 29.897 | 13.653 | 59.047 | 1.00 13.01 |
| ATOM | 3618 | CE | LYS | B | 420 | 29.503 | 14.579 | 60.155 | 1.00 13.88 |
| ATOM | 3619 | NZ | LYS | B | 420 | 30.671 | 14.794 | 61.031 | 1.00 17.10 |
| ATOM | 3620 | C | LYS | B | 420 | 30.676 | 11.116 | 55.667 | 1.00 16.12 |
| ATOM | 3621 | O | LYS | B | 420 | 31.074 | 10.159 | 56.335 | 1.00 15.54 |
| ATOM | 3622 | N | SER | B | 421 | 30.388 | 11.006 | 54.372 | 1.00 16.70 |
| ATOM | 3623 | CA | SER | B | 421 | 30.691 | 9.764 | 53.681 | 1.00 18.15 |
| ATOM | 3624 | CB | SER | B | 421 | 29.823 | 9.550 | 52.424 | 1.00 17.99 |
| ATOM | 3625 | OG | SER | B | 421 | 29.880 | 10.617 | 51.508 | 1.00 22.15 |
| ATOM | 3626 | C | SER | B | 421 | 32.216 | 9.709 | 53.423 | 1.00 18.39 |
| ATOM | 3627 | O | SER | B | 421 | 32.788 | 8.629 | 53.308 | 1.00 18.96 |
| ATOM | 3628 | N | ASP | B | 422 | 32.867 | 10.876 | 53.405 | 1.00 18.79 |
| ATOM | 3629 | CA | ASP | B | 422 | 34.326 | 10.950 | 53.261 | 1.00 18.62 |
| ATOM | 3630 | CB | ASP | B | 422 | 34.827 | 12.378 | 52.999 | 1.00 18.97 |
| ATOM | 3631 | CG | ASP | B | 422 | 34.454 | 12.902 | 51.624 | 1.00 20.61 |
| ATOM | 3632 | OD1 | ASP | B | 422 | 34.225 | 12.094 | 50.700 | 1.00 22.75 |
| ATOM | 3633 | OD2 | ASP | B | 422 | 34.395 | 14.137 | 51.475 | 1.00 20.85 |
| ATOM | 3634 | C | ASP | B | 422 | 34.924 | 10.504 | 54.584 | 1.00 19.26 |
| ATOM | 3635 | O | ASP | B | 422 | 35.961 | 9.848 | 54.600 | 1.00 21.08 |
| ATOM | 3636 | N | VAL | B | 423 | 34.292 | 10.902 | 55.694 | 1.00 18.90 |
| ATOM | 3637 | CA | VAL | B | 423 | 34.762 | 10.522 | 57.034 | 1.00 18.85 |
| ATOM | 3638 | CB | VAL | B | 423 | 33.865 | 11.121 | 58.179 | 1.00 18.70 |
| ATOM | 3639 | CG1 | VAL | B | 423 | 34.245 | 10.508 | 59.531 | 1.00 18.05 |
| ATOM | 3640 | CG2 | VAL | B | 423 | 34.028 | 12.639 | 58.253 | 1.00 16.30 |
| ATOM | 3641 | C | VAL | B | 423 | 34.806 | 8.991 | 57.129 | 1.00 19.05 |
| ATOM | 3642 | O | VAL | B | 423 | 35.743 | 8.413 | 57.708 | 1.00 19.86 |
| ATOM | 3643 | N | TRP | B | 424 | 33.819 | 8.349 | 56.511 | 1.00 18.31 |
| ATOM | 3644 | CA | TRP | B | 424 | 33.741 | 6.893 | 56.482 | 1.00 18.28 |
| ATOM | 3645 | CB | TRP | B | 424 | 32.406 | 6.457 | 55.862 | 1.00 17.39 |

Figure 7

| | | | | | | | | | |
|---|---|---|---|---|---|---|---|---|---|
| ATOM | 3646 | CG | TRP | B | 424 | 32.294 | 4.962 | 55.676 | 1.00 19.03 |
| ATOM | 3647 | CD2 | TRP | B | 424 | 31.453 | 4.051 | 56.402 | 1.00 18.06 |
| ATOM | 3648 | CE2 | TRP | B | 424 | 31.716 | 2.755 | 55.903 | 1.00 19.04 |
| ATOM | 3649 | CE3 | TRP | B | 424 | 30.507 | 4.204 | 57.419 | 1.00 15.97 |
| ATOM | 3650 | CD1 | TRP | B | 424 | 33.003 | 4.195 | 54.790 | 1.00 19.41 |
| ATOM | 3651 | NE1 | TRP | B | 424 | 32.664 | 2.877 | 54.923 | 1.00 18.89 |
| ATOM | 3652 | CZ2 | TRP | B | 424 | 31.065 | 1.614 | 56.389 | 1.00 19.66 |
| ATOM | 3653 | CZ3 | TRP | B | 424 | 29.859 | 3.076 | 57.899 | 1.00 17.20 |
| ATOM | 3654 | CH2 | TRP | B | 424 | 30.140 | 1.795 | 57.384 | 1.00 20.15 |
| ATOM | 3655 | C | TRP | B | 424 | 34.925 | 6.357 | 55.655 | 1.00 17.83 |
| ATOM | 3656 | O | TRP | B | 424 | 35.583 | 5.401 | 56.053 | 1.00 17.75 |
| ATOM | 3657 | N | SER | B | 425 | 35.188 | 6.979 | 54.506 | 1.00 18.06 |
| ATOM | 3658 | CA | SER | B | 425 | 36.307 | 6.574 | 53.643 | 1.00 19.43 |
| ATOM | 3659 | CB | SER | B | 425 | 36.346 | 7.417 | 52.369 | 1.00 19.26 |
| ATOM | 3660 | OG | SER | B | 425 | 35.198 | 7.208 | 51.580 | 1.00 21.61 |
| ATOM | 3661 | C | SER | B | 425 | 37.633 | 6.738 | 54.352 | 1.00 19.00 |
| ATOM | 3662 | O | SER | B | 425 | 38.544 | 5.957 | 54.145 | 1.00 21.22 |
| ATOM | 3663 | N | PHE | B | 426 | 37.745 | 7.806 | 55.131 | 1.00 18.15 |
| ATOM | 3664 | CA | PHE | B | 426 | 38.956 | 8.096 | 55.875 | 1.00 18.91 |
| ATOM | 3665 | CB | PHE | B | 426 | 38.807 | 9.416 | 56.636 | 1.00 18.40 |
| ATOM | 3666 | CG | PHE | B | 426 | 40.035 | 9.821 | 57.378 | 1.00 18.57 |
| ATOM | 3667 | CD1 | PHE | B | 426 | 41.162 | 10.271 | 56.685 | 1.00 17.51 |
| ATOM | 3668 | CD2 | PHE | B | 426 | 40.087 | 9.726 | 58.770 | 1.00 18.40 |
| ATOM | 3669 | CE1 | PHE | B | 426 | 42.316 | 10.614 | 57.361 | 1.00 17.55 |
| ATOM | 3670 | CE2 | PHE | B | 426 | 41.244 | 10.072 | 59.463 | 1.00 19.48 |
| ATOM | 3671 | CZ | PHE | B | 426 | 42.364 | 10.518 | 58.752 | 1.00 19.32 |
| ATOM | 3672 | C | PHE | B | 426 | 39.306 | 6.970 | 56.843 | 1.00 18.64 |
| ATOM | 3673 | O | PHE | B | 426 | 40.473 | 6.587 | 56.941 | 1.00 19.11 |
| ATOM | 3674 | N | GLY | B | 427 | 38.306 | 6.477 | 57.580 | 1.00 18.05 |
| ATOM | 3675 | CA | GLY | B | 427 | 38.519 | 5.377 | 58.515 | 1.00 16.71 |
| ATOM | 3676 | C | GLY | B | 427 | 38.975 | 4.109 | 57.820 | 1.00 16.58 |
| ATOM | 3677 | O | GLY | B | 427 | 39.675 | 3.294 | 58.403 | 1.00 16.36 |
| ATOM | 3678 | N | ILE | B | 428 | 38.543 | 3.922 | 56.575 | 1.00 18.13 |
| ATOM | 3679 | CA | ILE | B | 428 | 38.946 | 2.769 | 55.775 | 1.00 18.14 |
| ATOM | 3680 | CB | ILE | B | 428 | 38.073 | 2.616 | 54.502 | 1.00 17.57 |
| ATOM | 3681 | CG2 | ILE | B | 428 | 38.576 | 1.471 | 53.654 | 1.00 16.37 |
| ATOM | 3682 | CG1 | ILE | B | 428 | 36.602 | 2.403 | 54.879 | 1.00 17.69 |
| ATOM | 3683 | CD1 | ILE | B | 428 | 36.286 | 1.079 | 55.608 | 1.00 17.37 |
| ATOM | 3684 | C | ILE | B | 428 | 40.392 | 3.022 | 55.365 | 1.00 18.75 |
| ATOM | 3685 | O | ILE | B | 428 | 41.213 | 2.115 | 55.363 | 1.00 18.90 |
| ATOM | 3686 | N | LEU | B | 429 | 40.695 | 4.278 | 55.056 | 1.00 19.34 |
| ATOM | 3687 | CA | LEU | B | 429 | 42.039 | 4.700 | 54.667 | 1.00 19.43 |
| ATOM | 3688 | CB | LEU | B | 429 | 42.047 | 6.193 | 54.294 | 1.00 20.32 |
| ATOM | 3689 | CG | LEU | B | 429 | 43.176 | 6.773 | 53.428 | 1.00 20.57 |
| ATOM | 3690 | CD1 | LEU | B | 429 | 42.863 | 8.206 | 53.118 | 1.00 21.56 |
| ATOM | 3691 | CD2 | LEU | B | 429 | 44.539 | 6.679 | 54.077 | 1.00 21.83 |
| ATOM | 3692 | C | LEU | B | 429 | 42.979 | 4.453 | 55.830 | 1.00 18.98 |
| ATOM | 3693 | O | LEU | B | 429 | 44.107 | 4.051 | 55.627 | 1.00 20.75 |
| ATOM | 3694 | N | LEU | B | 430 | 42.520 | 4.695 | 57.053 | 1.00 19.49 |
| ATOM | 3695 | CA | LEU | B | 430 | 43.357 | 4.462 | 58.225 | 1.00 20.28 |
| ATOM | 3696 | CB | LEU | B | 430 | 42.636 | 4.825 | 59.527 | 1.00 19.77 |
| ATOM | 3697 | CG | LEU | B | 430 | 42.404 | 6.294 | 59.885 | 1.00 19.75 |
| ATOM | 3698 | CD1 | LEU | B | 430 | 41.546 | 6.384 | 61.133 | 1.00 18.89 |
| ATOM | 3699 | CD2 | LEU | B | 430 | 43.730 | 7.017 | 60.091 | 1.00 19.13 |
| ATOM | 3700 | C | LEU | B | 430 | 43.797 | 3.010 | 58.292 | 1.00 21.00 |
| ATOM | 3701 | O | LEU | B | 430 | 44.918 | 2.735 | 58.720 | 1.00 21.46 |
| ATOM | 3702 | N | THR | B | 431 | 42.926 | 2.085 | 57.866 | 1.00 21.27 |
| ATOM | 3703 | CA | THR | B | 431 | 43.274 | 0.663 | 57.897 | 1.00 20.84 |
| ATOM | 3704 | CB | THR | B | 431 | 42.066 | -0.304 | 57.632 | 1.00 19.74 |

Figure 7

| | | | | | | | | | |
|---|---|---|---|---|---|---|---|---|---|
| ATOM | 3705 | OG1 | THR | B | 431 | 41.605 | -0.191 | 56.287 | 1.00 19.43 |
| ATOM | 3706 | CG2 | THR | B | 431 | 40.924 | -0.006 | 58.570 | 1.00 19.47 |
| ATOM | 3707 | C | THR | B | 431 | 44.400 | 0.408 | 56.919 | 1.00 20.57 |
| ATOM | 3708 | O | THR | B | 431 | 45.329 | -0.313 | 57.236 | 1.00 20.87 |
| ATOM | 3709 | N | GLU | B | 432 | 44.346 | 1.077 | 55.768 | 1.00 22.66 |
| ATOM | 3710 | CA | GLU | B | 432 | 45.380 | 0.952 | 54.745 | 1.00 22.58 |
| ATOM | 3711 | CB | GLU | B | 432 | 45.029 | 1.763 | 53.502 | 1.00 21.11 |
| ATOM | 3712 | CG | GLU | B | 432 | 43.766 | 1.323 | 52.793 | 1.00 21.14 |
| ATOM | 3713 | CD | GLU | B | 432 | 43.490 | 2.146 | 51.549 | 1.00 21.58 |
| ATOM | 3714 | OE1 | GLU | B | 432 | 42.941 | 3.266 | 51.662 | 1.00 19.32 |
| ATOM | 3715 | OE2 | GLU | B | 432 | 43.841 | 1.677 | 50.448 | 1.00 23.61 |
| ATOM | 3716 | C | GLU | B | 432 | 46.688 | 1.469 | 55.314 | 1.00 23.19 |
| ATOM | 3717 | O | GLU | B | 432 | 47.726 | 0.832 | 55.174 | 1.00 25.50 |
| ATOM | 3718 | N | ILE | B | 433 | 46.634 | 2.606 | 55.992 | 1.00 22.96 |
| ATOM | 3719 | CA | ILE | B | 433 | 47.830 | 3.189 | 56.582 | 1.00 24.06 |
| ATOM | 3720 | CB | ILE | B | 433 | 47.503 | 4.551 | 57.220 | 1.00 22.74 |
| ATOM | 3721 | CG2 | ILE | B | 433 | 48.532 | 4.930 | 58.277 | 1.00 23.15 |
| ATOM | 3722 | CG1 | ILE | B | 433 | 47.406 | 5.608 | 56.119 | 1.00 22.86 |
| ATOM | 3723 | CD1 | ILE | B | 433 | 46.901 | 6.964 | 56.597 | 1.00 20.64 |
| ATOM | 3724 | C | ILE | B | 433 | 48.571 | 2.254 | 57.556 | 1.00 25.84 |
| ATOM | 3725 | O | ILE | B | 433 | 49.767 | 2.005 | 57.375 | 1.00 25.08 |
| ATOM | 3726 | N | VAL | B | 434 | 47.843 | 1.694 | 58.531 | 1.00 27.55 |
| ATOM | 3727 | CA | VAL | B | 434 | 48.413 | 0.794 | 59.537 | 1.00 28.03 |
| ATOM | 3728 | CB | VAL | B | 434 | 47.527 | 0.673 | 60.800 | 1.00 27.39 |
| ATOM | 3729 | CG1 | VAL | B | 434 | 47.432 | 2.003 | 61.468 | 1.00 28.69 |
| ATOM | 3730 | CG2 | VAL | B | 434 | 46.148 | 0.136 | 60.468 | 1.00 27.31 |
| ATOM | 3731 | C | VAL | B | 434 | 48.778 | -0.604 | 59.066 | 1.00 28.80 |
| ATOM | 3732 | O | VAL | B | 434 | 49.544 | -1.297 | 59.725 | 1.00 30.53 |
| ATOM | 3733 | N | THR | B | 435 | 48.242 | -1.022 | 57.931 | 1.00 29.98 |
| ATOM | 3734 | CA | THR | B | 435 | 48.567 | -2.344 | 57.408 | 1.00 30.92 |
| ATOM | 3735 | CB | THR | B | 435 | 47.308 | -3.097 | 56.960 | 1.00 29.65 |
| ATOM | 3736 | OG1 | THR | B | 435 | 46.711 | -2.407 | 55.852 | 1.00 29.95 |
| ATOM | 3737 | CG2 | THR | B | 435 | 46.313 | -3.233 | 58.131 | 1.00 26.99 |
| ATOM | 3738 | C | THR | B | 435 | 49.545 | -2.256 | 56.233 | 1.00 32.61 |
| ATOM | 3739 | O | THR | B | 435 | 49.755 | -3.236 | 55.518 | 1.00 33.21 |
| ATOM | 3740 | N | HIS | B | 436 | 50.133 | -1.076 | 56.040 | 1.00 34.55 |
| ATOM | 3741 | CA | HIS | B | 436 | 51.089 | -0.827 | 54.964 | 1.00 36.31 |
| ATOM | 3742 | CB | HIS | B | 436 | 52.378 | -1.616 | 55.202 | 1.00 39.42 |
| ATOM | 3743 | CG | HIS | B | 436 | 53.026 | -1.324 | 56.519 | 1.00 42.33 |
| ATOM | 3744 | CD2 | HIS | B | 436 | 53.425 | -2.150 | 57.520 | 1.00 45.07 |
| ATOM | 3745 | ND1 | HIS | B | 436 | 53.327 | -0.047 | 56.940 | 1.00 43.90 |
| ATOM | 3746 | CE1 | HIS | B | 436 | 53.886 | -0.094 | 58.139 | 1.00 44.19 |
| ATOM | 3747 | NE2 | HIS | B | 436 | 53.955 | -1.360 | 58.511 | 1.00 46.14 |
| ATOM | 3748 | C | HIS | B | 436 | 50.527 | -1.113 | 53.574 | 1.00 36.23 |
| ATOM | 3749 | O | HIS | B | 436 | 51.119 | -1.852 | 52.784 | 1.00 36.90 |
| ATOM | 3750 | N | GLY | B | 437 | 49.370 | -0.508 | 53.298 | 1.00 36.33 |
| ATOM | 3751 | CA | GLY | B | 437 | 48.704 | -0.643 | 52.016 | 1.00 35.79 |
| ATOM | 3752 | C | GLY | B | 437 | 47.917 | -1.907 | 51.746 | 1.00 35.94 |
| ATOM | 3753 | O | GLY | B | 437 | 47.660 | -2.223 | 50.590 | 1.00 37.33 |
| ATOM | 3754 | N | ARG | B | 438 | 47.515 | -2.614 | 52.795 | 1.00 35.84 |
| ATOM | 3755 | CA | ARG | B | 438 | 46.741 | -3.846 | 52.644 | 1.00 36.13 |
| ATOM | 3756 | CB | ARG | B | 438 | 46.787 | -4.622 | 53.968 | 1.00 38.09 |
| ATOM | 3757 | CG | ARG | B | 438 | 46.489 | -6.116 | 53.916 | 1.00 42.51 |
| ATOM | 3758 | CD | ARG | B | 438 | 44.980 | -6.423 | 53.853 | 1.00 46.42 |
| ATOM | 3759 | NE | ARG | B | 438 | 44.188 | -5.716 | 54.867 | 1.00 48.96 |
| ATOM | 3760 | CZ | ARG | B | 438 | 44.087 | -6.085 | 56.140 | 1.00 50.77 |
| ATOM | 3761 | NH1 | ARG | B | 438 | 44.736 | -7.167 | 56.561 | 1.00 53.02 |
| ATOM | 3762 | NH2 | ARG | B | 438 | 43.339 | -5.379 | 56.991 | 1.00 50.51 |
| ATOM | 3763 | C | ARG | B | 438 | 45.295 | -3.480 | 52.266 | 1.00 34.61 |

Figure 7

| | | | | | | | | | |
|---|---|---|---|---|---|---|---|---|---|
| ATOM | 3764 | O | ARG | B | 438 | 44.734 | -2.525 | 52.792 | 1.00 34.48 |
| ATOM | 3765 | N | ILE | B | 439 | 44.720 | -4.220 | 51.322 | 1.00 33.51 |
| ATOM | 3766 | CA | ILE | B | 439 | 43.349 | -4.000 | 50.849 | 1.00 32.27 |
| ATOM | 3767 | CB | ILE | B | 439 | 43.016 | -4.942 | 49.659 | 1.00 31.69 |
| ATOM | 3768 | CG2 | ILE | B | 439 | 41.521 | -5.006 | 49.406 | 1.00 32.66 |
| ATOM | 3769 | CG1 | ILE | B | 439 | 43.700 | -4.431 | 48.391 | 1.00 34.66 |
| ATOM | 3770 | CD1 | ILE | B | 439 | 43.619 | -5.388 | 47.187 | 1.00 35.77 |
| ATOM | 3771 | C | ILE | B | 439 | 42.307 | -4.188 | 51.941 | 1.00 31.24 |
| ATOM | 3772 | O | ILE | B | 439 | 42.349 | -5.159 | 52.694 | 1.00 32.20 |
| ATOM | 3773 | N | PRO | B | 440 | 41.353 | -3.251 | 52.046 | 1.00 30.07 |
| ATOM | 3774 | CD | PRO | B | 440 | 41.251 | -1.995 | 51.281 | 1.00 28.25 |
| ATOM | 3775 | CA | PRO | B | 440 | 40.293 | -3.343 | 53.065 | 1.00 29.93 |
| ATOM | 3776 | CB | PRO | B | 440 | 39.449 | -2.096 | 52.788 | 1.00 29.71 |
| ATOM | 3777 | CG | PRO | B | 440 | 40.451 | -1.125 | 52.209 | 1.00 29.39 |
| ATOM | 3778 | C | PRO | B | 440 | 39.453 | -4.627 | 52.907 | 1.00 28.94 |
| ATOM | 3779 | O | PRO | B | 440 | 39.355 | -5.176 | 51.812 | 1.00 28.24 |
| ATOM | 3780 | N | TYR | B | 441 | 38.853 | -5.090 | 54.005 | 1.00 29.37 |
| ATOM | 3781 | CA | TYR | B | 441 | 38.014 | -6.297 | 54.013 | 1.00 29.43 |
| ATOM | 3782 | CB | TYR | B | 441 | 36.629 | -6.025 | 53.409 | 1.00 28.15 |
| ATOM | 3783 | CG | TYR | B | 441 | 35.883 | -4.843 | 53.984 | 1.00 25.63 |
| ATOM | 3784 | CD1 | TYR | B | 441 | 35.007 | -4.999 | 55.060 | 1.00 24.38 |
| ATOM | 3785 | CE1 | TYR | B | 441 | 34.290 | -3.911 | 55.561 | 1.00 24.97 |
| ATOM | 3786 | CD2 | TYR | B | 441 | 36.030 | -3.569 | 53.426 | 1.00 23.65 |
| ATOM | 3787 | CE2 | TYR | B | 441 | 35.324 | -2.472 | 53.915 | 1.00 22.76 |
| ATOM | 3788 | CZ | TYR | B | 441 | 34.455 | -2.649 | 54.977 | 1.00 24.43 |
| ATOM | 3789 | OH | TYR | B | 441 | 33.740 | -1.572 | 55.446 | 1.00 25.16 |
| ATOM | 3790 | C | TYR | B | 441 | 38.683 | -7.427 | 53.228 | 1.00 30.78 |
| ATOM | 3791 | O | TYR | B | 441 | 38.127 | -7.919 | 52.242 | 1.00 29.68 |
| ATOM | 3792 | N | PRO | B | 442 | 39.884 | -7.854 | 53.669 | 1.00 32.11 |
| ATOM | 3793 | CD | PRO | B | 442 | 40.492 | -7.440 | 54.948 | 1.00 30.87 |
| ATOM | 3794 | CA | PRO | B | 442 | 40.676 | -8.925 | 53.037 | 1.00 33.48 |
| ATOM | 3795 | CB | PRO | B | 442 | 41.876 | -9.049 | 53.981 | 1.00 33.85 |
| ATOM | 3796 | CG | PRO | B | 442 | 41.289 | -8.654 | 55.329 | 1.00 32.40 |
| ATOM | 3797 | C | PRO | B | 442 | 39.915 | -10.254 | 52.911 | 1.00 34.36 |
| ATOM | 3798 | O | PRO | B | 442 | 39.374 | -10.770 | 53.896 | 1.00 34.53 |
| ATOM | 3799 | N | GLY | B | 443 | 39.871 | -10.810 | 51.704 | 1.00 34.64 |
| ATOM | 3800 | CA | GLY | B | 443 | 39.163 | -12.067 | 51.507 | 1.00 35.80 |
| ATOM | 3801 | C | GLY | B | 443 | 37.659 | -11.923 | 51.307 | 1.00 36.34 |
| ATOM | 3802 | O | GLY | B | 443 | 36.897 | -12.871 | 51.518 | 1.00 37.07 |
| ATOM | 3803 | N | MET | B | 444 | 37.232 | -10.711 | 50.958 | 1.00 35.99 |
| ATOM | 3804 | CA | MET | B | 444 | 35.833 | -10.398 | 50.689 | 1.00 34.84 |
| ATOM | 3805 | CB | MET | B | 444 | 35.258 | -9.449 | 51.746 | 1.00 34.19 |
| ATOM | 3806 | CG | MET | B | 444 | 34.792 | -10.109 | 53.027 | 1.00 33.78 |
| ATOM | 3807 | SD | MET | B | 444 | 34.033 | -8.935 | 54.186 | 1.00 33.61 |
| ATOM | 3808 | CE | MET | B | 444 | 32.461 | -8.937 | 53.664 | 1.00 33.83 |
| ATOM | 3809 | C | MET | B | 444 | 35.789 | -9.710 | 49.340 | 1.00 34.75 |
| ATOM | 3810 | O | MET | B | 444 | 36.657 | -8.901 | 49.026 | 1.00 35.56 |
| ATOM | 3811 | N | THR | B | 445 | 34.791 | -10.041 | 48.530 | 1.00 34.78 |
| ATOM | 3812 | CA | THR | B | 445 | 34.646 | -9.419 | 47.223 | 1.00 34.53 |
| ATOM | 3813 | CB | THR | B | 445 | 33.939 | -10.362 | 46.222 | 1.00 34.48 |
| ATOM | 3814 | OG1 | THR | B | 445 | 32.640 | -10.702 | 46.721 | 1.00 35.52 |
| ATOM | 3815 | CG2 | THR | B | 445 | 34.735 | -11.633 | 46.033 | 1.00 34.60 |
| ATOM | 3816 | C | THR | B | 445 | 33.786 | -8.167 | 47.396 | 1.00 34.57 |
| ATOM | 3817 | O | THR | B | 445 | 33.237 | -7.931 | 48.475 | 1.00 33.24 |
| ATOM | 3818 | N | ASN | B | 446 | 33.650 | -7.387 | 46.322 | 1.00 34.60 |
| ATOM | 3819 | CA | ASN | B | 446 | 32.821 | -6.183 | 46.356 | 1.00 34.15 |
| ATOM | 3820 | CB | ASN | B | 446 | 32.835 | -5.456 | 45.003 | 1.00 30.88 |
| ATOM | 3821 | CG | ASN | B | 446 | 33.934 | -4.417 | 44.906 | 1.00 30.10 |
| ATOM | 3822 | OD1 | ASN | B | 446 | 34.863 | -4.393 | 45.725 | 1.00 29.09 |

Figure 7

| ATOM | 3823 | ND2 | ASN | B | 446 | 33.835 | -3.540 | 43.913 | 1.00 | 28.30 |
| --- | --- | --- | --- | --- | --- | --- | --- | --- | --- | --- |
| ATOM | 3824 | C | ASN | B | 446 | 31.385 | -6.528 | 46.780 | 1.00 | 35.29 |
| ATOM | 3825 | O | ASN | B | 446 | 30.808 | -5.839 | 47.627 | 1.00 | 35.58 |
| ATOM | 3826 | N | PRO | B | 447 | 30.775 | -7.570 | 46.166 | 1.00 | 35.69 |
| ATOM | 3827 | CD | PRO | B | 447 | 31.140 | -8.233 | 44.900 | 1.00 | 34.55 |
| ATOM | 3828 | CA | PRO | B | 447 | 29.406 | -7.931 | 46.559 | 1.00 | 34.63 |
| ATOM | 3829 | CB | PRO | B | 447 | 28.975 | -8.919 | 45.468 | 1.00 | 34.86 |
| ATOM | 3830 | CG | PRO | B | 447 | 30.263 | -9.434 | 44.908 | 1.00 | 34.83 |
| ATOM | 3831 | C | PRO | B | 447 | 29.284 | -8.502 | 47.980 | 1.00 | 34.05 |
| ATOM | 3832 | O | PRO | B | 447 | 28.239 | -8.335 | 48.620 | 1.00 | 34.05 |
| ATOM | 3833 | N | GLU | B | 448 | 30.343 | -9.148 | 48.476 | 1.00 | 33.50 |
| ATOM | 3834 | CA | GLU | B | 448 | 30.346 | -9.700 | 49.844 | 1.00 | 33.48 |
| ATOM | 3835 | CB | GLU | B | 448 | 31.529 | -10.641 | 50.067 | 1.00 | 36.16 |
| ATOM | 3836 | CG | GLU | B | 448 | 31.400 | -11.996 | 49.391 | 1.00 | 42.15 |
| ATOM | 3837 | CD | GLU | B | 448 | 32.693 | -12.811 | 49.447 | 1.00 | 45.16 |
| ATOM | 3838 | OE1 | GLU | B | 448 | 33.452 | -12.676 | 50.437 | 1.00 | 47.68 |
| ATOM | 3839 | OE2 | GLU | B | 448 | 32.952 | -13.585 | 48.493 | 1.00 | 46.43 |
| ATOM | 3840 | C | GLU | B | 448 | 30.408 | -8.566 | 50.867 | 1.00 | 31.37 |
| ATOM | 3841 | O | GLU | B | 448 | 29.804 | -8.648 | 51.934 | 1.00 | 31.35 |
| ATOM | 3842 | N | VAL | B | 449 | 31.153 | -7.512 | 50.538 | 1.00 | 29.69 |
| ATOM | 3843 | CA | VAL | B | 449 | 31.257 | -6.348 | 51.411 | 1.00 | 27.17 |
| ATOM | 3844 | CB | VAL | B | 449 | 32.352 | -5.363 | 50.914 | 1.00 | 24.85 |
| ATOM | 3845 | CG1 | VAL | B | 449 | 32.229 | -4.007 | 51.590 | 1.00 | 21.93 |
| ATOM | 3846 | CG2 | VAL | B | 449 | 33.714 | -5.940 | 51.207 | 1.00 | 23.76 |
| ATOM | 3847 | C | VAL | B | 449 | 29.878 | -5.685 | 51.486 | 1.00 | 26.99 |
| ATOM | 3848 | O | VAL | B | 449 | 29.433 | -5.289 | 52.561 | 1.00 | 28.07 |
| ATOM | 3849 | N | ILE | B | 450 | 29.173 | -5.649 | 50.357 | 1.00 | 26.91 |
| ATOM | 3850 | CA | ILE | B | 450 | 27.837 | -5.056 | 50.296 | 1.00 | 26.90 |
| ATOM | 3851 | CB | ILE | B | 450 | 27.227 | -5.113 | 48.850 | 1.00 | 26.57 |
| ATOM | 3852 | CG2 | ILE | B | 450 | 25.921 | -4.352 | 48.805 | 1.00 | 26.21 |
| ATOM | 3853 | CG1 | ILE | B | 450 | 28.187 | -4.543 | 47.806 | 1.00 | 26.19 |
| ATOM | 3854 | CD1 | ILE | B | 450 | 28.304 | -3.064 | 47.804 | 1.00 | 26.58 |
| ATOM | 3855 | C | ILE | B | 450 | 26.875 | -5.809 | 51.235 | 1.00 | 26.36 |
| ATOM | 3856 | O | ILE | B | 450 | 26.157 | -5.196 | 52.018 | 1.00 | 26.27 |
| ATOM | 3857 | N | GLN | B | 451 | 26.867 | -7.135 | 51.158 | 1.00 | 26.00 |
| ATOM | 3858 | CA | GLN | B | 451 | 25.969 | -7.904 | 51.996 | 1.00 | 26.88 |
| ATOM | 3859 | CB | GLN | B | 451 | 25.741 | -9.314 | 51.440 | 1.00 | 30.97 |
| ATOM | 3860 | CG | GLN | B | 451 | 26.989 | -10.080 | 51.127 | 1.00 | 38.67 |
| ATOM | 3861 | CD | GLN | B | 451 | 26.760 | -11.209 | 50.127 | 1.00 | 42.54 |
| ATOM | 3862 | OE1 | GLN | B | 451 | 27.414 | -12.253 | 50.197 | 1.00 | 45.27 |
| ATOM | 3863 | NE2 | GLN | B | 451 | 25.861 | -10.987 | 49.168 | 1.00 | 42.14 |
| ATOM | 3864 | C | GLN | B | 451 | 26.345 | -7.933 | 53.462 | 1.00 | 25.50 |
| ATOM | 3865 | O | GLN | B | 451 | 25.486 | -8.113 | 54.310 | 1.00 | 25.40 |
| ATOM | 3866 | N | ASN | B | 452 | 27.623 | -7.758 | 53.771 | 1.00 | 24.55 |
| ATOM | 3867 | CA | ASN | B | 452 | 28.028 | -7.736 | 55.160 | 1.00 | 23.92 |
| ATOM | 3868 | CB | ASN | B | 452 | 29.517 | -7.996 | 55.289 | 1.00 | 26.09 |
| ATOM | 3869 | CG | ASN | B | 452 | 29.811 | -9.439 | 55.608 | 1.00 | 27.72 |
| ATOM | 3870 | OD1 | ASN | B | 452 | 29.842 | -9.833 | 56.777 | 1.00 | 26.46 |
| ATOM | 3871 | ND2 | ASN | B | 452 | 30.002 | -10.248 | 54.569 | 1.00 | 27.38 |
| ATOM | 3872 | C | ASN | B | 452 | 27.657 | -6.400 | 55.773 | 1.00 | 22.53 |
| ATOM | 3873 | O | ASN | B | 452 | 27.304 | -6.331 | 56.937 | 1.00 | 21.28 |
| ATOM | 3874 | N | LEU | B | 453 | 27.733 | -5.344 | 54.972 | 1.00 | 23.33 |
| ATOM | 3875 | CA | LEU | B | 453 | 27.379 | -4.003 | 55.412 | 1.00 | 23.75 |
| ATOM | 3876 | CB | LEU | B | 453 | 27.794 | -2.959 | 54.390 | 1.00 | 25.73 |
| ATOM | 3877 | CG | LEU | B | 453 | 29.276 | -2.602 | 54.352 | 1.00 | 27.47 |
| ATOM | 3878 | CD1 | LEU | B | 453 | 29.407 | -1.329 | 53.534 | 1.00 | 29.93 |
| ATOM | 3879 | CD2 | LEU | B | 453 | 29.823 | -2.380 | 55.756 | 1.00 | 26.92 |
| ATOM | 3880 | C | LEU | B | 453 | 25.893 | -3.884 | 55.692 | 1.00 | 24.14 |
| ATOM | 3881 | O | LEU | B | 453 | 25.490 | -3.132 | 56.581 | 1.00 | 24.19 |

Figure 7

| | | | | | | | | | |
|---|---|---|---|---|---|---|---|---|---|
| ATOM | 3882 | N | GLU | B | 454 | 25.074 | -4.593 | 54.914 | 1.00 24.78 |
| ATOM | 3883 | CA | GLU | B | 454 | 23.621 | -4.613 | 55.147 | 1.00 25.31 |
| ATOM | 3884 | CB | GLU | B | 454 | 22.919 | -5.587 | 54.223 | 1.00 27.19 |
| ATOM | 3885 | CG | GLU | B | 454 | 22.663 | -5.098 | 52.846 | 1.00 34.82 |
| ATOM | 3886 | CD | GLU | B | 454 | 22.334 | -6.246 | 51.906 | 1.00 39.79 |
| ATOM | 3887 | OE1 | GLU | B | 454 | 22.145 | -5.990 | 50.695 | 1.00 41.52 |
| ATOM | 3888 | OE2 | GLU | B | 454 | 22.287 | -7.411 | 52.377 | 1.00 43.60 |
| ATOM | 3889 | C | GLU | B | 454 | 23.397 | -5.130 | 56.563 | 1.00 23.43 |
| ATOM | 3890 | O | GLU | B | 454 | 22.552 | -4.635 | 57.294 | 1.00 23.28 |
| ATOM | 3891 | N | ARG | B | 455 | 24.178 | -6.140 | 56.929 | 1.00 22.10 |
| ATOM | 3892 | CA | ARG | B | 455 | 24.111 | -6.739 | 58.250 | 1.00 20.47 |
| ATOM | 3893 | CB | ARG | B | 455 | 24.566 | -8.194 | 58.159 | 1.00 21.16 |
| ATOM | 3894 | CG | ARG | B | 455 | 23.677 | -9.043 | 57.271 | 1.00 21.71 |
| ATOM | 3895 | CD | ARG | B | 455 | 24.017 | -10.506 | 57.398 | 1.00 24.13 |
| ATOM | 3896 | NE | ARG | B | 455 | 25.414 | -10.734 | 57.065 | 1.00 29.30 |
| ATOM | 3897 | CZ | ARG | B | 455 | 25.840 | -11.574 | 56.127 | 1.00 30.32 |
| ATOM | 3898 | NH1 | ARG | B | 455 | 24.976 | -12.277 | 55.410 | 1.00 32.30 |
| ATOM | 3899 | NH2 | ARG | B | 455 | 27.139 | -11.716 | 55.918 | 1.00 30.29 |
| ATOM | 3900 | C | ARG | B | 455 | 24.885 | -5.965 | 59.316 | 1.00 18.90 |
| ATOM | 3901 | O | ARG | B | 455 | 24.999 | -6.419 | 60.444 | 1.00 18.49 |
| ATOM | 3902 | N | GLY | B | 456 | 25.387 | -4.784 | 58.949 | 1.00 19.76 |
| ATOM | 3903 | CA | GLY | B | 456 | 26.139 | -3.910 | 59.846 | 1.00 17.61 |
| ATOM | 3904 | C | GLY | B | 456 | 27.557 | -4.316 | 60.213 | 1.00 18.03 |
| ATOM | 3905 | O | GLY | B | 456 | 28.077 | -3.912 | 61.247 | 1.00 16.65 |
| ATOM | 3906 | N | TYR | B | 457 | 28.192 | -5.112 | 59.364 | 1.00 19.32 |
| ATOM | 3907 | CA | TYR | B | 457 | 29.549 | -5.590 | 59.598 | 1.00 19.80 |
| ATOM | 3908 | CB | TYR | B | 457 | 29.950 | -6.587 | 58.497 | 1.00 19.83 |
| ATOM | 3909 | CG | TYR | B | 457 | 31.366 | -7.139 | 58.611 | 1.00 20.00 |
| ATOM | 3910 | CD1 | TYR | B | 457 | 31.621 | -8.334 | 59.306 | 1.00 18.86 |
| ATOM | 3911 | CE1 | TYR | B | 457 | 32.894 | -8.865 | 59.371 | 1.00 19.39 |
| ATOM | 3912 | CD2 | TYR | B | 457 | 32.449 | -6.498 | 57.989 | 1.00 18.88 |
| ATOM | 3913 | CE2 | TYR | B | 457 | 33.740 | -7.031 | 58.058 | 1.00 18.89 |
| ATOM | 3914 | CZ | TYR | B | 457 | 33.946 | -8.215 | 58.753 | 1.00 19.66 |
| ATOM | 3915 | OH | TYR | B | 457 | 35.202 | -8.754 | 58.863 | 1.00 20.18 |
| ATOM | 3916 | C | TYR | B | 457 | 30.585 | -4.478 | 59.646 | 1.00 19.81 |
| ATOM | 3917 | O | TYR | B | 457 | 30.525 | -3.527 | 58.863 | 1.00 20.73 |
| ATOM | 3918 | N | ARG | B | 458 | 31.550 | -4.640 | 60.550 | 1.00 20.05 |
| ATOM | 3919 | CA | ARG | B | 458 | 32.662 | -3.714 | 60.701 | 1.00 20.32 |
| ATOM | 3920 | CB | ARG | B | 458 | 32.503 | -2.823 | 61.941 | 1.00 17.80 |
| ATOM | 3921 | CG | ARG | B | 458 | 31.290 | -1.921 | 61.948 | 1.00 16.80 |
| ATOM | 3922 | CD | ARG | B | 458 | 31.265 | -1.020 | 60.744 | 1.00 16.76 |
| ATOM | 3923 | NE | ARG | B | 458 | 30.205 | -0.027 | 60.836 | 1.00 15.01 |
| ATOM | 3924 | CZ | ARG | B | 458 | 29.102 | -0.036 | 60.101 | 1.00 13.99 |
| ATOM | 3925 | NH1 | ARG | B | 458 | 28.905 | -0.993 | 59.215 | 1.00 17.15 |
| ATOM | 3926 | NH2 | ARG | B | 458 | 28.218 | 0.934 | 60.226 | 1.00 13.35 |
| ATOM | 3927 | C | ARG | B | 458 | 33.950 | -4.549 | 60.841 | 1.00 21.34 |
| ATOM | 3928 | O | ARG | B | 458 | 33.958 | -5.569 | 61.535 | 1.00 22.17 |
| ATOM | 3929 | N | MET | B | 459 | 35.002 | -4.151 | 60.123 | 1.00 22.35 |
| ATOM | 3930 | CA | MET | B | 459 | 36.305 | -4.817 | 60.188 | 1.00 21.36 |
| ATOM | 3931 | CB | MET | B | 459 | 37.363 | -4.061 | 59.357 | 1.00 21.07 |
| ATOM | 3932 | CG | MET | B | 459 | 37.313 | -4.248 | 57.852 | 1.00 23.83 |
| ATOM | 3933 | SD | MET | B | 459 | 38.706 | -3.443 | 56.970 | 1.00 24.52 |
| ATOM | 3934 | CE | MET | B | 459 | 38.087 | -1.814 | 56.756 | 1.00 23.82 |
| ATOM | 3935 | C | MET | B | 459 | 36.792 | -4.800 | 61.630 | 1.00 21.55 |
| ATOM | 3936 | O | MET | B | 459 | 36.506 | -3.859 | 62.387 | 1.00 19.62 |
| ATOM | 3937 | N | VAL | B | 460 | 37.567 | -5.827 | 61.984 | 1.00 22.33 |
| ATOM | 3938 | CA | VAL | B | 460 | 38.159 | -5.943 | 63.314 | 1.00 22.60 |
| ATOM | 3939 | CB | VAL | B | 460 | 38.410 | -7.432 | 63.696 | 1.00 22.54 |
| ATOM | 3940 | CG1 | VAL | B | 460 | 37.114 | -8.177 | 63.625 | 1.00 22.19 |

Figure 7

| | | | | | | | | | |
|---|---|---|---|---|---|---|---|---|---|
| ATOM | 3941 | CG2 | VAL | B | 460 | 39.449 | -8.071 | 62.772 | 1.00 21.05 |
| ATOM | 3942 | C | VAL | B | 460 | 39.465 | -5.134 | 63.344 | 1.00 22.85 |
| ATOM | 3943 | O | VAL | B | 460 | 39.948 | -4.691 | 62.300 | 1.00 22.17 |
| ATOM | 3944 | N | ARG | B | 461 | 40.009 | -4.911 | 64.538 | 1.00 23.74 |
| ATOM | 3945 | CA | ARG | B | 461 | 41.250 | -4.144 | 64.702 | 1.00 25.84 |
| ATOM | 3946 | CB | ARG | B | 461 | 41.636 | -4.065 | 66.193 | 1.00 27.15 |
| ATOM | 3947 | CG | ARG | B | 461 | 42.792 | -3.107 | 66.526 | 1.00 30.66 |
| ATOM | 3948 | CD | ARG | B | 461 | 43.196 | -3.145 | 68.019 | 1.00 35.10 |
| ATOM | 3949 | NE | ARG | B | 461 | 43.660 | -4.475 | 68.387 | 1.00 42.71 |
| ATOM | 3950 | CZ | ARG | B | 461 | 44.788 | -5.030 | 67.934 | 1.00 48.26 |
| ATOM | 3951 | NH1 | ARG | B | 461 | 45.603 | -4.361 | 67.114 | 1.00 49.64 |
| ATOM | 3952 | NH2 | ARG | B | 461 | 45.034 | -6.315 | 68.170 | 1.00 50.48 |
| ATOM | 3953 | C | ARG | B | 461 | 42.372 | -4.804 | 63.903 | 1.00 26.79 |
| ATOM | 3954 | O | ARG | B | 461 | 42.644 | -6.000 | 64.053 | 1.00 27.17 |
| ATOM | 3955 | N | PRO | B | 462 | 43.011 | -4.049 | 63.003 | 1.00 27.70 |
| ATOM | 3956 | CD | PRO | B | 462 | 42.739 | -2.663 | 62.591 | 1.00 27.55 |
| ATOM | 3957 | CA | PRO | B | 462 | 44.097 | -4.630 | 62.210 | 1.00 29.16 |
| ATOM | 3958 | CB | PRO | B | 462 | 44.469 | -3.489 | 61.254 | 1.00 27.82 |
| ATOM | 3959 | CG | PRO | B | 462 | 43.192 | -2.675 | 61.158 | 1.00 27.46 |
| ATOM | 3960 | C | PRO | B | 462 | 45.285 | -5.001 | 63.100 | 1.00 31.54 |
| ATOM | 3961 | O | PRO | B | 462 | 45.486 | -4.401 | 64.157 | 1.00 31.21 |
| ATOM | 3962 | N | ASP | B | 463 | 46.054 | -6.007 | 62.689 | 1.00 35.19 |
| ATOM | 3963 | CA | ASP | B | 463 | 47.238 | -6.403 | 63.452 | 1.00 37.55 |
| ATOM | 3964 | CB | ASP | B | 463 | 48.011 | -7.527 | 62.746 | 1.00 38.42 |
| ATOM | 3965 | CG | ASP | B | 463 | 47.318 | -8.875 | 62.835 | 1.00 41.02 |
| ATOM | 3966 | OD1 | ASP | B | 463 | 46.423 | -9.049 | 63.699 | 1.00 42.59 |
| ATOM | 3967 | OD2 | ASP | B | 463 | 47.681 | -9.773 | 62.039 | 1.00 41.48 |
| ATOM | 3968 | C | ASP | B | 463 | 48.139 | -5.178 | 63.524 | 1.00 38.32 |
| ATOM | 3969 | O | ASP | B | 463 | 48.309 | -4.462 | 62.528 | 1.00 38.59 |
| ATOM | 3970 | N | ASN | B | 464 | 48.670 | -4.917 | 64.717 | 1.00 39.95 |
| ATOM | 3971 | CA | ASN | B | 464 | 49.582 | -3.793 | 64.947 | 1.00 40.16 |
| ATOM | 3972 | CB | ASN | B | 464 | 50.842 | -3.965 | 64.081 | 1.00 41.59 |
| ATOM | 3973 | CG | ASN | B | 464 | 51.579 | -5.287 | 64.374 | 1.00 43.31 |
| ATOM | 3974 | OD1 | ASN | B | 464 | 52.075 | -5.494 | 65.484 | 1.00 44.40 |
| ATOM | 3975 | ND2 | ASN | B | 464 | 51.623 | -6.190 | 63.390 | 1.00 42.62 |
| ATOM | 3976 | C | ASN | B | 464 | 48.909 | -2.428 | 64.732 | 1.00 39.13 |
| ATOM | 3977 | O | ASN | B | 464 | 49.401 | -1.562 | 63.993 | 1.00 40.37 |
| ATOM | 3978 | N | CYS | B | 465 | 47.770 | -2.264 | 65.395 | 1.00 36.02 |
| ATOM | 3979 | CA | CYS | B | 465 | 46.975 | -1.041 | 65.346 | 1.00 33.53 |
| ATOM | 3980 | CB | CYS | B | 465 | 45.709 | -1.259 | 64.487 | 1.00 31.66 |
| ATOM | 3981 | SG | CYS | B | 465 | 44.438 | 0.066 | 64.492 | 1.00 27.31 |
| ATOM | 3982 | C | CYS | B | 465 | 46.577 | -0.712 | 66.791 | 1.00 32.12 |
| ATOM | 3983 | O | CYS | B | 465 | 46.063 | -1.567 | 67.507 | 1.00 32.77 |
| ATOM | 3984 | N | PRO | B | 466 | 46.896 | 0.505 | 67.260 | 1.00 30.61 |
| ATOM | 3985 | CD | PRO | B | 466 | 47.610 | 1.593 | 66.558 | 1.00 29.34 |
| ATOM | 3986 | CA | PRO | B | 466 | 46.532 | 0.890 | 68.628 | 1.00 28.94 |
| ATOM | 3987 | CB | PRO | B | 466 | 46.872 | 2.380 | 68.658 | 1.00 27.67 |
| ATOM | 3988 | CG | PRO | B | 466 | 48.009 | 2.496 | 67.697 | 1.00 29.64 |
| ATOM | 3989 | C | PRO | B | 466 | 45.025 | 0.693 | 68.828 | 1.00 28.75 |
| ATOM | 3990 | O | PRO | B | 466 | 44.258 | 0.804 | 67.869 | 1.00 28.67 |
| ATOM | 3991 | N | GLU | B | 467 | 44.605 | 0.370 | 70.052 | 1.00 29.10 |
| ATOM | 3992 | CA | GLU | B | 467 | 43.190 | 0.182 | 70.341 | 1.00 28.33 |
| ATOM | 3993 | CB | GLU | B | 467 | 42.982 | -0.334 | 71.760 | 1.00 29.19 |
| ATOM | 3994 | CG | GLU | B | 467 | 42.218 | -1.658 | 71.831 | 1.00 34.76 |
| ATOM | 3995 | CD | GLU | B | 467 | 40.865 | -1.646 | 71.107 | 1.00 35.38 |
| ATOM | 3996 | OE1 | GLU | B | 467 | 40.697 | -2.434 | 70.155 | 1.00 38.09 |
| ATOM | 3997 | OE2 | GLU | B | 467 | 39.955 | -0.896 | 71.510 | 1.00 36.11 |
| ATOM | 3998 | C | GLU | B | 467 | 42.480 | 1.511 | 70.210 | 1.00 28.54 |
| ATOM | 3999 | O | GLU | B | 467 | 41.321 | 1.570 | 69.817 | 1.00 29.69 |

Figure 7

```
ATOM   4000  N    GLU B 468      43.194    2.586   70.525  1.00  28.29
ATOM   4001  CA   GLU B 468      42.636    3.934   70.457  1.00  28.64
ATOM   4002  CB   GLU B 468      43.555    4.934   71.166  1.00  32.06
ATOM   4003  CG   GLU B 468      43.898    4.579   72.620  1.00  37.29
ATOM   4004  CD   GLU B 468      44.832    3.365   72.737  1.00  41.42
ATOM   4005  OE1  GLU B 468      45.814    3.264   71.949  1.00  40.45
ATOM   4006  OE2  GLU B 468      44.564    2.502   73.610  1.00  43.36
ATOM   4007  C    GLU B 468      42.372    4.383   69.020  1.00  27.04
ATOM   4008  O    GLU B 468      41.396    5.100   68.773  1.00  27.45
ATOM   4009  N    LEU B 469      43.254    3.995   68.088  1.00  23.96
ATOM   4010  CA   LEU B 469      43.086    4.324   66.672  1.00  22.03
ATOM   4011  CB   LEU B 469      44.374    4.036   65.890  1.00  20.18
ATOM   4012  CG   LEU B 469      44.399    4.372   64.390  1.00  20.14
ATOM   4013  CD1  LEU B 469      44.264    5.856   64.169  1.00  19.00
ATOM   4014  CD2  LEU B 469      45.682    3.901   63.782  1.00  19.37
ATOM   4015  C    LEU B 469      41.919    3.492   66.109  1.00  21.76
ATOM   4016  O    LEU B 469      41.142    3.956   65.274  1.00  21.22
ATOM   4017  N    TYR B 470      41.807    2.253   66.572  1.00  21.37
ATOM   4018  CA   TYR B 470      40.717    1.409   66.132  1.00  21.56
ATOM   4019  CB   TYR B 470      40.842   -0.010   66.671  1.00  20.22
ATOM   4020  CG   TYR B 470      39.694   -0.872   66.215  1.00  19.98
ATOM   4021  CD1  TYR B 470      39.422   -1.047   64.855  1.00  18.82
ATOM   4022  CE1  TYR B 470      38.361   -1.832   64.432  1.00  18.64
ATOM   4023  CD2  TYR B 470      38.871   -1.501   67.132  1.00  19.74
ATOM   4024  CE2  TYR B 470      37.800   -2.294   66.716  1.00  19.69
ATOM   4025  CZ   TYR B 470      37.555   -2.456   65.370  1.00  18.16
ATOM   4026  OH   TYR B 470      36.521   -3.267   64.964  1.00  18.23
ATOM   4027  C    TYR B 470      39.360    2.003   66.519  1.00  21.34
ATOM   4028  O    TYR B 470      38.434    1.996   65.717  1.00  23.07
ATOM   4029  N    GLN B 471      39.242    2.503   67.742  1.00  21.47
ATOM   4030  CA   GLN B 471      37.993    3.124   68.178  1.00  22.41
ATOM   4031  CB   GLN B 471      38.041    3.473   69.670  1.00  23.79
ATOM   4032  CG   GLN B 471      38.018    2.245   70.582  1.00  25.72
ATOM   4033  CD   GLN B 471      36.897    1.279   70.226  1.00  26.89
ATOM   4034  OE1  GLN B 471      35.805    1.699   69.840  1.00  28.62
ATOM   4035  NE2  GLN B 471      37.168   -0.022   70.332  1.00  24.65
ATOM   4036  C    GLN B 471      37.698    4.373   67.343  1.00  22.35
ATOM   4037  O    GLN B 471      36.536    4.749   67.155  1.00  21.60
ATOM   4038  N    LEU B 472      38.754    4.979   66.805  1.00  21.90
ATOM   4039  CA   LEU B 472      38.602    6.160   65.972  1.00  21.92
ATOM   4040  CB   LEU B 472      39.952    6.816   65.722  1.00  22.34
ATOM   4041  CG   LEU B 472      39.963    8.342   65.661  1.00  24.46
ATOM   4042  CD1  LEU B 472      39.417    8.932   66.971  1.00  24.06
ATOM   4043  CD2  LEU B 472      41.388    8.818   65.421  1.00  24.39
ATOM   4044  C    LEU B 472      37.965    5.726   64.659  1.00  21.61
ATOM   4045  O    LEU B 472      37.089    6.413   64.133  1.00  21.67
ATOM   4046  N    MET B 473      38.377    4.557   64.169  1.00  21.02
ATOM   4047  CA   MET B 473      37.837    3.991   62.932  1.00  20.21
ATOM   4048  CB   MET B 473      38.566    2.698   62.576  1.00  20.05
ATOM   4049  CG   MET B 473      40.065    2.873   62.344  1.00  20.41
ATOM   4050  SD   MET B 473      40.869    1.281   62.227  1.00  20.97
ATOM   4051  CE   MET B 473      42.488    1.785   61.663  1.00  17.90
ATOM   4052  C    MET B 473      36.366    3.689   63.144  1.00  19.88
ATOM   4053  O    MET B 473      35.522    4.035   62.330  1.00  19.27
ATOM   4054  N    ARG B 474      36.063    3.066   64.270  1.00  20.70
ATOM   4055  CA   ARG B 474      34.687    2.719   64.611  1.00  21.39
ATOM   4056  CB   ARG B 474      34.640    1.968   65.950  1.00  20.92
ATOM   4057  CG   ARG B 474      35.347    0.611   65.885  1.00  21.53
ATOM   4058  CD   ARG B 474      34.800   -0.237   64.738  1.00  24.24
```

Figure 7

| | | | | | | | | |
|---|---|---|---|---|---|---|---|---|
| ATOM | 4059 | NE | ARG | B | 474 | 33.367 | -0.513 | 64.907 | 1.00 25.95 |
| ATOM | 4060 | CZ | ARG | B | 474 | 32.857 | -1.605 | 65.484 | 1.00 25.78 |
| ATOM | 4061 | NH1 | ARG | B | 474 | 33.646 | -2.562 | 65.953 | 1.00 23.57 |
| ATOM | 4062 | NH2 | ARG | B | 474 | 31.548 | -1.706 | 65.652 | 1.00 26.33 |
| ATOM | 4063 | C | ARG | B | 474 | 33.760 | 3.933 | 64.606 | 1.00 20.44 |
| ATOM | 4064 | O | ARG | B | 474 | 32.594 | 3.820 | 64.236 | 1.00 20.96 |
| ATOM | 4065 | N | LEU | B | 475 | 34.287 | 5.089 | 65.013 | 1.00 21.07 |
| ATOM | 4066 | CA | LEU | B | 475 | 33.524 | 6.339 | 65.015 | 1.00 19.17 |
| ATOM | 4067 | CB | LEU | B | 475 | 34.251 | 7.425 | 65.807 | 1.00 19.34 |
| ATOM | 4068 | CG | LEU | B | 475 | 34.230 | 7.303 | 67.322 | 1.00 19.39 |
| ATOM | 4069 | CD1 | LEU | B | 475 | 34.968 | 8.481 | 67.920 | 1.00 18.39 |
| ATOM | 4070 | CD2 | LEU | B | 475 | 32.796 | 7.252 | 67.819 | 1.00 19.29 |
| ATOM | 4071 | C | LEU | B | 475 | 33.306 | 6.811 | 63.581 | 1.00 18.60 |
| ATOM | 4072 | O | LEU | B | 475 | 32.262 | 7.348 | 63.256 | 1.00 18.12 |
| ATOM | 4073 | N | CYS | B | 476 | 34.303 | 6.597 | 62.728 | 1.00 18.39 |
| ATOM | 4074 | CA | CYS | B | 476 | 34.215 | 6.964 | 61.319 | 1.00 18.26 |
| ATOM | 4075 | CB | CYS | B | 476 | 35.575 | 6.824 | 60.620 | 1.00 18.52 |
| ATOM | 4076 | SG | CYS | B | 476 | 36.787 | 8.032 | 61.130 | 1.00 19.89 |
| ATOM | 4077 | C | CYS | B | 476 | 33.221 | 6.069 | 60.610 | 1.00 18.12 |
| ATOM | 4078 | O | CYS | B | 476 | 32.663 | 6.454 | 59.571 | 1.00 18.06 |
| ATOM | 4079 | N | TRP | B | 477 | 33.006 | 4.873 | 61.165 | 1.00 17.84 |
| ATOM | 4080 | CA | TRP | B | 477 | 32.087 | 3.910 | 60.566 | 1.00 17.38 |
| ATOM | 4081 | CB | TRP | B | 477 | 32.676 | 2.505 | 60.568 | 1.00 16.58 |
| ATOM | 4082 | CG | TRP | B | 477 | 33.981 | 2.372 | 59.866 | 1.00 16.44 |
| ATOM | 4083 | CD2 | TRP | B | 477 | 35.005 | 1.428 | 60.169 | 1.00 17.51 |
| ATOM | 4084 | CE2 | TRP | B | 477 | 36.089 | 1.707 | 59.310 | 1.00 17.68 |
| ATOM | 4085 | CE3 | TRP | B | 477 | 35.117 | 0.369 | 61.092 | 1.00 18.85 |
| ATOM | 4086 | CD1 | TRP | B | 477 | 34.465 | 3.155 | 58.849 | 1.00 15.59 |
| ATOM | 4087 | NE1 | TRP | B | 477 | 35.727 | 2.769 | 58.522 | 1.00 14.02 |
| ATOM | 4088 | CZ2 | TRP | B | 477 | 37.285 | 0.961 | 59.342 | 1.00 18.96 |
| ATOM | 4089 | CZ3 | TRP | B | 477 | 36.295 | -0.369 | 61.129 | 1.00 20.06 |
| ATOM | 4090 | CH2 | TRP | B | 477 | 37.368 | -0.066 | 60.255 | 1.00 20.77 |
| ATOM | 4091 | C | TRP | B | 477 | 30.715 | 3.852 | 61.198 | 1.00 17.90 |
| ATOM | 4092 | O | TRP | B | 477 | 29.993 | 2.880 | 61.015 | 1.00 19.42 |
| ATOM | 4093 | N | LYS | B | 478 | 30.344 | 4.868 | 61.960 | 1.00 19.18 |
| ATOM | 4094 | CA | LYS | B | 478 | 29.013 | 4.883 | 62.551 | 1.00 19.92 |
| ATOM | 4095 | CB | LYS | B | 478 | 28.821 | 6.131 | 63.404 | 1.00 20.72 |
| ATOM | 4096 | CG | LYS | B | 478 | 29.644 | 6.095 | 64.672 | 1.00 24.02 |
| ATOM | 4097 | CD | LYS | B | 478 | 29.245 | 4.931 | 65.546 | 1.00 26.14 |
| ATOM | 4098 | CE | LYS | B | 478 | 27.887 | 5.176 | 66.172 | 1.00 28.41 |
| ATOM | 4099 | NZ | LYS | B | 478 | 27.486 | 4.039 | 67.058 | 1.00 33.77 |
| ATOM | 4100 | C | LYS | B | 478 | 28.007 | 4.825 | 61.416 | 1.00 20.45 |
| ATOM | 4101 | O | LYS | B | 478 | 28.194 | 5.452 | 60.375 | 1.00 20.77 |
| ATOM | 4102 | N | GLU | B | 479 | 26.972 | 4.010 | 61.592 | 1.00 21.45 |
| ATOM | 4103 | CA | GLU | B | 479 | 25.929 | 3.833 | 60.574 | 1.00 22.63 |
| ATOM | 4104 | CB | GLU | B | 479 | 24.836 | 2.910 | 61.131 | 1.00 23.30 |
| ATOM | 4105 | CG | GLU | B | 479 | 23.887 | 2.366 | 60.077 | 1.00 23.07 |
| ATOM | 4106 | CD | GLU | B | 479 | 24.586 | 1.539 | 59.028 | 1.00 22.19 |
| ATOM | 4107 | OE1 | GLU | B | 479 | 25.488 | 0.753 | 59.370 | 1.00 25.66 |
| ATOM | 4108 | OE2 | GLU | B | 479 | 24.235 | 1.672 | 57.854 | 1.00 20.22 |
| ATOM | 4109 | C | GLU | B | 479 | 25.326 | 5.162 | 60.112 | 1.00 21.37 |
| ATOM | 4110 | O | GLU | B | 479 | 25.202 | 5.436 | 58.913 | 1.00 21.32 |
| ATOM | 4111 | N | ARG | B | 480 | 24.922 | 5.961 | 61.091 | 1.00 20.93 |
| ATOM | 4112 | CA | ARG | B | 480 | 24.347 | 7.277 | 60.848 | 1.00 21.60 |
| ATOM | 4113 | CB | ARG | B | 480 | 23.508 | 7.710 | 62.035 | 1.00 24.15 |
| ATOM | 4114 | CG | ARG | B | 480 | 22.269 | 6.925 | 62.258 | 1.00 27.36 |
| ATOM | 4115 | CD | ARG | B | 480 | 21.675 | 7.503 | 63.485 | 1.00 32.80 |
| ATOM | 4116 | NE | ARG | B | 480 | 20.466 | 6.824 | 63.892 | 1.00 38.93 |
| ATOM | 4117 | CZ | ARG | B | 480 | 20.188 | 6.525 | 65.153 | 1.00 42.91 |

Figure 7

| ATOM | 4118 | NH1 | ARG | B | 480 | 21.052 | 6.839 | 66.127 | 1.00 | 43.74 |
|------|------|-----|-----|---|-----|--------|-------|--------|------|-------|
| ATOM | 4119 | NH2 | ARG | B | 480 | 19.024 | 5.952 | 65.444 | 1.00 | 44.87 |
| ATOM | 4120 | C   | ARG | B | 480 | 25.427 | 8.331 | 60.640 | 1.00 | 20.11 |
| ATOM | 4121 | O   | ARG | B | 480 | 26.273 | 8.532 | 61.520 | 1.00 | 19.83 |
| ATOM | 4122 | N   | PRO | B | 481 | 25.369 | 9.065 | 59.505 | 1.00 | 19.01 |
| ATOM | 4123 | CD  | PRO | B | 481 | 24.302 | 8.968 | 58.495 | 1.00 | 16.99 |
| ATOM | 4124 | CA  | PRO | B | 481 | 26.322 | 10.117 | 59.138 | 1.00 | 18.17 |
| ATOM | 4125 | CB  | PRO | B | 481 | 25.633 | 10.791 | 57.951 | 1.00 | 18.32 |
| ATOM | 4126 | CG  | PRO | B | 481 | 24.882 | 9.696 | 57.338 | 1.00 | 17.28 |
| ATOM | 4127 | C   | PRO | B | 481 | 26.589 | 11.118 | 60.254 | 1.00 | 19.05 |
| ATOM | 4128 | O   | PRO | B | 481 | 27.727 | 11.493 | 60.487 | 1.00 | 19.08 |
| ATOM | 4129 | N   | GLU | B | 482 | 25.536 | 11.510 | 60.976 | 1.00 | 19.81 |
| ATOM | 4130 | CA  | GLU | B | 482 | 25.645 | 12.484 | 62.072 | 1.00 | 19.03 |
| ATOM | 4131 | CB  | GLU | B | 482 | 24.243 | 12.905 | 62.568 | 1.00 | 19.36 |
| ATOM | 4132 | CG  | GLU | B | 482 | 23.464 | 11.809 | 63.316 | 1.00 | 19.58 |
| ATOM | 4133 | CD  | GLU | B | 482 | 22.411 | 11.096 | 62.475 | 1.00 | 20.79 |
| ATOM | 4134 | OE1 | GLU | B | 482 | 22.558 | 11.015 | 61.237 | 1.00 | 21.48 |
| ATOM | 4135 | OE2 | GLU | B | 482 | 21.423 | 10.606 | 63.061 | 1.00 | 23.57 |
| ATOM | 4136 | C   | GLU | B | 482 | 26.491 | 12.014 | 63.250 | 1.00 | 18.52 |
| ATOM | 4137 | O   | GLU | B | 482 | 27.042 | 12.831 | 63.985 | 1.00 | 19.30 |
| ATOM | 4138 | N   | ASP | B | 483 | 26.609 | 10.701 | 63.430 | 1.00 | 19.42 |
| ATOM | 4139 | CA  | ASP | B | 483 | 27.379 | 10.144 | 64.546 | 1.00 | 19.45 |
| ATOM | 4140 | CB  | ASP | B | 483 | 26.792 | 8.791 | 64.977 | 1.00 | 20.82 |
| ATOM | 4141 | CG  | ASP | B | 483 | 25.347 | 8.895 | 65.480 | 1.00 | 21.00 |
| ATOM | 4142 | OD1 | ASP | B | 483 | 24.975 | 9.917 | 66.098 | 1.00 | 21.68 |
| ATOM | 4143 | OD2 | ASP | B | 483 | 24.583 | 7.934 | 65.269 | 1.00 | 20.29 |
| ATOM | 4144 | C   | ASP | B | 483 | 28.881 | 10.023 | 64.289 | 1.00 | 19.18 |
| ATOM | 4145 | O   | ASP | B | 483 | 29.645 | 9.716 | 65.201 | 1.00 | 19.37 |
| ATOM | 4146 | N   | ARG | B | 484 | 29.290 | 10.251 | 63.039 | 1.00 | 19.83 |
| ATOM | 4147 | CA  | ARG | B | 484 | 30.701 | 10.214 | 62.617 | 1.00 | 19.43 |
| ATOM | 4148 | CB  | ARG | B | 484 | 30.779 | 9.987 | 61.110 | 1.00 | 18.64 |
| ATOM | 4149 | CG  | ARG | B | 484 | 30.019 | 8.775 | 60.690 | 1.00 | 16.31 |
| ATOM | 4150 | CD  | ARG | B | 484 | 30.021 | 8.622 | 59.192 | 1.00 | 17.90 |
| ATOM | 4151 | NE  | ARG | B | 484 | 29.135 | 7.525 | 58.835 | 1.00 | 16.34 |
| ATOM | 4152 | CZ  | ARG | B | 484 | 28.576 | 7.359 | 57.647 | 1.00 | 14.56 |
| ATOM | 4153 | NH1 | ARG | B | 484 | 28.824 | 8.216 | 56.674 | 1.00 | 13.08 |
| ATOM | 4154 | NH2 | ARG | B | 484 | 27.715 | 6.366 | 57.468 | 1.00 | 15.27 |
| ATOM | 4155 | C   | ARG | B | 484 | 31.366 | 11.554 | 62.976 | 1.00 | 18.60 |
| ATOM | 4156 | O   | ARG | B | 484 | 30.743 | 12.612 | 62.819 | 1.00 | 19.10 |
| ATOM | 4157 | N   | PRO | B | 485 | 32.646 | 11.532 | 63.412 | 1.00 | 18.02 |
| ATOM | 4158 | CD  | PRO | B | 485 | 33.549 | 10.376 | 63.409 | 1.00 | 17.21 |
| ATOM | 4159 | CA  | PRO | B | 485 | 33.372 | 12.751 | 63.794 | 1.00 | 18.23 |
| ATOM | 4160 | CB  | PRO | B | 485 | 34.715 | 12.212 | 64.310 | 1.00 | 18.92 |
| ATOM | 4161 | CG  | PRO | B | 485 | 34.506 | 10.738 | 64.486 | 1.00 | 20.11 |
| ATOM | 4162 | C   | PRO | B | 485 | 33.642 | 13.726 | 62.651 | 1.00 | 18.67 |
| ATOM | 4163 | O   | PRO | B | 485 | 33.574 | 13.352 | 61.482 | 1.00 | 19.70 |
| ATOM | 4164 | N   | THR | B | 486 | 33.936 | 14.980 | 62.985 | 1.00 | 18.49 |
| ATOM | 4165 | CA  | THR | B | 486 | 34.298 | 15.944 | 61.951 | 1.00 | 19.61 |
| ATOM | 4166 | CB  | THR | B | 486 | 34.170 | 17.403 | 62.424 | 1.00 | 15.75 |
| ATOM | 4167 | OG1 | THR | B | 486 | 34.968 | 17.600 | 63.594 | 1.00 | 17.13 |
| ATOM | 4168 | CG2 | THR | B | 486 | 32.739 | 17.740 | 62.716 | 1.00 | 17.81 |
| ATOM | 4169 | C   | THR | B | 486 | 35.772 | 15.683 | 61.649 | 1.00 | 20.70 |
| ATOM | 4170 | O   | THR | B | 486 | 36.451 | 14.993 | 62.416 | 1.00 | 21.74 |
| ATOM | 4171 | N   | PHE | B | 487 | 36.255 | 16.175 | 60.511 | 1.00 | 21.86 |
| ATOM | 4172 | CA  | PHE | B | 487 | 37.674 | 16.022 | 60.157 | 1.00 | 21.98 |
| ATOM | 4173 | CB  | PHE | B | 487 | 37.901 | 16.305 | 58.671 | 1.00 | 19.91 |
| ATOM | 4174 | CG  | PHE | B | 487 | 37.607 | 15.137 | 57.774 | 1.00 | 17.00 |
| ATOM | 4175 | CD1 | PHE | B | 487 | 38.444 | 14.028 | 57.761 | 1.00 | 15.77 |
| ATOM | 4176 | CD2 | PHE | B | 487 | 36.524 | 15.168 | 56.901 | 1.00 | 17.81 |

Figure 7

| | | | | | | | | | |
|---|---|---|---|---|---|---|---|---|---|
| ATOM | 4177 | CE1 | PHE | B | 487 | 38.212 | 12.975 | 56.893 | 1.00 12.97 |
| ATOM | 4178 | CE2 | PHE | B | 487 | 36.284 | 14.106 | 56.018 | 1.00 15.82 |
| ATOM | 4179 | CZ | PHE | B | 487 | 37.129 | 13.016 | 56.017 | 1.00 14.71 |
| ATOM | 4180 | C | PHE | B | 487 | 38.522 | 16.963 | 61.028 | 1.00 21.84 |
| ATOM | 4181 | O | PHE | B | 487 | 39.718 | 16.747 | 61.201 | 1.00 22.90 |
| ATOM | 4182 | N | ASP | B | 488 | 37.875 | 17.982 | 61.594 | 1.00 22.56 |
| ATOM | 4183 | CA | ASP | B | 488 | 38.524 | 18.938 | 62.488 | 1.00 23.66 |
| ATOM | 4184 | CB | ASP | B | 488 | 37.587 | 20.120 | 62.765 | 1.00 26.52 |
| ATOM | 4185 | CG | ASP | B | 488 | 38.182 | 21.131 | 63.743 | 1.00 31.61 |
| ATOM | 4186 | OD1 | ASP | B | 488 | 39.293 | 21.645 | 63.483 | 1.00 34.49 |
| ATOM | 4187 | OD2 | ASP | B | 488 | 37.534 | 21.415 | 64.775 | 1.00 32.74 |
| ATOM | 4188 | C | ASP | B | 488 | 38.869 | 18.191 | 63.779 | 1.00 23.30 |
| ATOM | 4189 | O | ASP | B | 488 | 39.942 | 18.380 | 64.357 | 1.00 24.31 |
| ATOM | 4190 | N | TYR | B | 489 | 37.961 | 17.331 | 64.226 | 1.00 21.72 |
| ATOM | 4191 | CA | TYR | B | 489 | 38.206 | 16.521 | 65.411 | 1.00 20.81 |
| ATOM | 4192 | CB | TYR | B | 489 | 36.929 | 15.831 | 65.888 | 1.00 21.35 |
| ATOM | 4193 | CG | TYR | B | 489 | 37.192 | 14.768 | 66.926 | 1.00 22.54 |
| ATOM | 4194 | CD1 | TYR | B | 489 | 37.477 | 15.111 | 68.257 | 1.00 23.03 |
| ATOM | 4195 | CE1 | TYR | B | 489 | 37.725 | 14.139 | 69.211 | 1.00 22.71 |
| ATOM | 4196 | CD2 | TYR | B | 489 | 37.168 | 13.418 | 66.579 | 1.00 22.63 |
| ATOM | 4197 | CE2 | TYR | B | 489 | 37.418 | 12.435 | 67.520 | 1.00 22.59 |
| ATOM | 4198 | CZ | TYR | B | 489 | 37.693 | 12.799 | 68.836 | 1.00 24.94 |
| ATOM | 4199 | OH | TYR | B | 489 | 37.904 | 11.812 | 69.779 | 1.00 26.84 |
| ATOM | 4200 | C | TYR | B | 489 | 39.245 | 15.462 | 65.099 | 1.00 20.19 |
| ATOM | 4201 | O | TYR | B | 489 | 40.145 | 15.230 | 65.892 | 1.00 20.63 |
| ATOM | 4202 | N | LEU | B | 490 | 39.077 | 14.786 | 63.963 | 1.00 20.58 |
| ATOM | 4203 | CA | LEU | B | 490 | 39.997 | 13.739 | 63.525 | 1.00 21.78 |
| ATOM | 4204 | CB | LEU | B | 490 | 39.545 | 13.145 | 62.187 | 1.00 20.74 |
| ATOM | 4205 | CG | LEU | B | 490 | 38.369 | 12.168 | 62.252 | 1.00 19.87 |
| ATOM | 4206 | CD1 | LEU | B | 490 | 37.857 | 11.853 | 60.855 | 1.00 18.37 |
| ATOM | 4207 | CD2 | LEU | B | 490 | 38.813 | 10.909 | 62.964 | 1.00 19.82 |
| ATOM | 4208 | C | LEU | B | 490 | 41.433 | 14.244 | 63.418 | 1.00 23.71 |
| ATOM | 4209 | O | LEU | B | 490 | 42.358 | 13.556 | 63.834 | 1.00 23.87 |
| ATOM | 4210 | N | ARG | B | 491 | 41.614 | 15.442 | 62.862 | 1.00 26.59 |
| ATOM | 4211 | CA | ARG | B | 491 | 42.938 | 16.059 | 62.732 | 1.00 28.92 |
| ATOM | 4212 | CB | ARG | B | 491 | 42.848 | 17.399 | 61.979 | 1.00 32.42 |
| ATOM | 4213 | CG | ARG | B | 491 | 44.144 | 18.241 | 62.034 | 1.00 36.79 |
| ATOM | 4214 | CD | ARG | B | 491 | 43.917 | 19.728 | 61.697 | 1.00 42.05 |
| ATOM | 4215 | NE | ARG | B | 491 | 42.818 | 20.304 | 62.485 | 1.00 46.12 |
| ATOM | 4216 | CZ | ARG | B | 491 | 42.905 | 20.697 | 63.760 | 1.00 45.98 |
| ATOM | 4217 | NH1 | ARG | B | 491 | 44.053 | 20.605 | 64.429 | 1.00 45.77 |
| ATOM | 4218 | NH2 | ARG | B | 491 | 41.820 | 21.125 | 64.392 | 1.00 44.96 |
| ATOM | 4219 | C | ARG | B | 491 | 43.543 | 16.305 | 64.121 | 1.00 28.73 |
| ATOM | 4220 | O | ARG | B | 491 | 44.719 | 16.035 | 64.352 | 1.00 28.47 |
| ATOM | 4221 | N | SER | B | 492 | 42.724 | 16.793 | 65.047 | 1.00 28.31 |
| ATOM | 4222 | CA | SER | B | 492 | 43.183 | 17.079 | 66.401 | 1.00 30.26 |
| ATOM | 4223 | CB | SER | B | 492 | 42.064 | 17.729 | 67.205 | 1.00 32.42 |
| ATOM | 4224 | OG | SER | B | 492 | 41.673 | 18.955 | 66.609 | 1.00 39.06 |
| ATOM | 4225 | C | SER | B | 492 | 43.684 | 15.856 | 67.150 | 1.00 30.81 |
| ATOM | 4226 | O | SER | B | 492 | 44.757 | 15.883 | 67.761 | 1.00 30.69 |
| ATOM | 4227 | N | VAL | B | 493 | 42.905 | 14.783 | 67.089 | 1.00 31.75 |
| ATOM | 4228 | CA | VAL | B | 493 | 43.231 | 13.550 | 67.782 | 1.00 31.72 |
| ATOM | 4229 | CB | VAL | B | 493 | 41.969 | 12.645 | 67.901 | 1.00 32.61 |
| ATOM | 4230 | CG1 | VAL | B | 493 | 41.508 | 12.188 | 66.547 | 1.00 33.39 |
| ATOM | 4231 | CG2 | VAL | B | 493 | 42.232 | 11.462 | 68.806 | 1.00 34.98 |
| ATOM | 4232 | C | VAL | B | 493 | 44.441 | 12.821 | 67.182 | 1.00 30.92 |
| ATOM | 4233 | O | VAL | B | 493 | 45.272 | 12.296 | 67.923 | 1.00 30.26 |
| ATOM | 4234 | N | LEU | B | 494 | 44.573 | 12.839 | 65.853 | 1.00 30.79 |
| ATOM | 4235 | CA | LEU | B | 494 | 45.712 | 12.190 | 65.178 | 1.00 30.45 |

Figure 7

| | | | | | | | | | |
|---|---|---|---|---|---|---|---|---|---|
| ATOM | 4236 | CB | LEU | B | 494 | 45.457 | 12.033 | 63.671 | 1.00 26.88 |
| ATOM | 4237 | CG | LEU | B | 494 | 44.385 | 11.000 | 63.301 | 1.00 25.84 |
| ATOM | 4238 | CD1 | LEU | B | 494 | 44.047 | 11.028 | 61.822 | 1.00 24.19 |
| ATOM | 4239 | CD2 | LEU | B | 494 | 44.856 | 9.634 | 63.720 | 1.00 24.38 |
| ATOM | 4240 | C | LEU | B | 494 | 46.988 | 12.984 | 65.420 | 1.00 32.11 |
| ATOM | 4241 | O | LEU | B | 494 | 48.064 | 12.409 | 65.500 | 1.00 32.04 |
| ATOM | 4242 | N | GLU | B | 495 | 46.851 | 14.305 | 65.548 | 1.00 34.55 |
| ATOM | 4243 | CA | GLU | B | 495 | 47.975 | 15.203 | 65.812 | 1.00 37.52 |
| ATOM | 4244 | CB | GLU | B | 495 | 47.543 | 16.665 | 65.725 | 1.00 39.45 |
| ATOM | 4245 | CG | GLU | B | 495 | 47.702 | 17.315 | 64.372 | 1.00 42.52 |
| ATOM | 4246 | CD | GLU | B | 495 | 47.274 | 18.772 | 64.389 | 1.00 45.01 |
| ATOM | 4247 | OE1 | GLU | B | 495 | 47.307 | 19.393 | 65.481 | 1.00 45.46 |
| ATOM | 4248 | OE2 | GLU | B | 495 | 46.906 | 19.289 | 63.305 | 1.00 46.81 |
| ATOM | 4249 | C | GLU | B | 495 | 48.550 | 15.003 | 67.203 | 1.00 39.51 |
| ATOM | 4250 | O | GLU | B | 495 | 49.768 | 15.063 | 67.382 | 1.00 40.08 |
| ATOM | 4251 | N | ASP | B | 496 | 47.675 | 14.824 | 68.196 | 1.00 41.00 |
| ATOM | 4252 | CA | ASP | B | 496 | 48.118 | 14.639 | 69.581 | 1.00 43.22 |
| ATOM | 4253 | CB | ASP | B | 496 | 47.231 | 15.455 | 70.545 | 1.00 45.69 |
| ATOM | 4254 | CG | ASP | B | 496 | 47.321 | 16.970 | 70.305 | 1.00 50.69 |
| ATOM | 4255 | OD1 | ASP | B | 496 | 48.421 | 17.477 | 69.966 | 1.00 52.83 |
| ATOM | 4256 | OD2 | ASP | B | 496 | 46.287 | 17.664 | 70.465 | 1.00 52.71 |
| ATOM | 4257 | C | ASP | B | 496 | 48.191 | 13.181 | 70.053 | 1.00 43.38 |
| ATOM | 4258 | O | ASP | B | 496 | 48.297 | 12.925 | 71.257 | 1.00 43.37 |
| ATOM | 4259 | N | PHE | B | 497 | 48.189 | 12.232 | 69.119 | 1.00 43.17 |
| ATOM | 4260 | CA | PHE | B | 497 | 48.218 | 10.811 | 69.472 | 1.00 44.24 |
| ATOM | 4261 | CB | PHE | B | 497 | 48.223 | 9.944 | 68.213 | 1.00 41.78 |
| ATOM | 4262 | CG | PHE | B | 497 | 47.465 | 8.655 | 68.367 | 1.00 39.28 |
| ATOM | 4263 | CD1 | PHE | B | 497 | 46.091 | 8.613 | 68.154 | 1.00 37.15 |
| ATOM | 4264 | CD2 | PHE | B | 497 | 48.130 | 7.476 | 68.718 | 1.00 38.05 |
| ATOM | 4265 | CE1 | PHE | B | 497 | 45.388 | 7.418 | 68.290 | 1.00 36.63 |
| ATOM | 4266 | CE2 | PHE | B | 497 | 47.435 | 6.273 | 68.854 | 1.00 36.38 |
| ATOM | 4267 | CZ | PHE | B | 497 | 46.063 | 6.246 | 68.639 | 1.00 36.72 |
| ATOM | 4268 | C | PHE | B | 497 | 49.356 | 10.413 | 70.428 | 1.00 46.13 |
| ATOM | 4269 | O | PHE | B | 497 | 49.107 | 9.753 | 71.442 | 1.00 46.14 |
| ATOM | 4270 | N | PHE | B | 498 | 50.591 | 10.792 | 70.090 | 1.00 48.27 |
| ATOM | 4271 | CA | PHE | B | 498 | 51.777 | 10.539 | 70.931 | 1.00 49.55 |
| ATOM | 4272 | CB | PHE | B | 498 | 52.104 | 9.039 | 71.125 | 1.00 49.92 |
| ATOM | 4273 | CG | PHE | B | 498 | 52.018 | 8.185 | 69.865 | 1.00 49.70 |
| ATOM | 4274 | CD1 | PHE | B | 498 | 52.148 | 8.738 | 68.588 | 1.00 49.72 |
| ATOM | 4275 | CD2 | PHE | B | 498 | 51.781 | 6.810 | 69.979 | 1.00 47.75 |
| ATOM | 4276 | CE1 | PHE | B | 498 | 52.043 | 7.926 | 67.451 | 1.00 50.10 |
| ATOM | 4277 | CE2 | PHE | B | 498 | 51.673 | 5.991 | 68.860 | 1.00 47.74 |
| ATOM | 4278 | CZ | PHE | B | 498 | 51.801 | 6.544 | 67.592 | 1.00 49.18 |
| ATOM | 4279 | C | PHE | B | 498 | 53.017 | 11.290 | 70.460 | 1.00 50.38 |
| ATOM | 4280 | O | PHE | B | 498 | 53.034 | 12.523 | 70.679 | 1.00 51.20 |
| ATOM | 4281 | N1 | LIG | B | 500 | 51.097 | 14.598 | 40.884 | 1.00 23.47 |
| ATOM | 4282 | C1 | LIG | B | 500 | 51.697 | 13.335 | 40.829 | 1.00 24.19 |
| ATOM | 4283 | N2 | LIG | B | 500 | 52.985 | 13.199 | 41.135 | 1.00 23.26 |
| ATOM | 4284 | C2 | LIG | B | 500 | 53.588 | 12.017 | 41.104 | 1.00 23.46 |
| ATOM | 4285 | N3 | LIG | B | 500 | 52.960 | 10.906 | 40.774 | 1.00 24.29 |
| ATOM | 4286 | C3 | LIG | B | 500 | 51.663 | 10.928 | 40.443 | 1.00 25.85 |
| ATOM | 4287 | N4 | LIG | B | 500 | 50.791 | 9.952 | 40.071 | 1.00 26.42 |
| ATOM | 4288 | C4 | LIG | B | 500 | 51.181 | 8.565 | 39.952 | 1.00 28.21 |
| ATOM | 4289 | C5 | LIG | B | 500 | 50.618 | 7.949 | 38.638 | 1.00 28.67 |
| ATOM | 4290 | C6 | LIG | B | 500 | 51.111 | 6.496 | 38.566 | 1.00 30.78 |
| ATOM | 4291 | C7 | LIG | B | 500 | 50.599 | 5.720 | 39.803 | 1.00 32.37 |
| ATOM | 4292 | N5 | LIG | B | 500 | 51.082 | 4.321 | 39.827 | 1.00 35.08 |
| ATOM | 4293 | C8 | LIG | B | 500 | 50.040 | 3.269 | 39.940 | 1.00 36.04 |
| ATOM | 4294 | C9 | LIG | B | 500 | 50.676 | 1.879 | 40.157 | 1.00 37.42 |

Figure 7

| | | | | | | | | | |
|---|---|---|---|---|---|---|---|---|---|
| ATOM | 4295 | N6  | LIG | B | 500 | 51.523 | 1.557   | 38.984 | 1.00 38.94 |
| ATOM | 4296 | C10 | LIG | B | 500 | 52.138 | 0.227   | 39.205 | 1.00 38.65 |
| ATOM | 4297 | C11 | LIG | B | 500 | 52.589 | 2.577   | 38.894 | 1.00 38.31 |
| ATOM | 4298 | C12 | LIG | B | 500 | 51.941 | 3.945   | 38.665 | 1.00 36.52 |
| ATOM | 4299 | C13 | LIG | B | 500 | 51.112 | 6.314   | 41.102 | 1.00 29.71 |
| ATOM | 4300 | C14 | LIG | B | 500 | 50.675 | 7.785   | 41.192 | 1.00 28.38 |
| ATOM | 4301 | C15 | LIG | B | 500 | 49.551 | 10.472  | 39.836 | 1.00 26.30 |
| ATOM | 4302 | C16 | LIG | B | 500 | 49.577 | 11.824  | 40.052 | 1.00 26.28 |
| ATOM | 4303 | C17 | LIG | B | 500 | 48.396 | 12.784  | 39.877 | 1.00 26.83 |
| ATOM | 4304 | C18 | LIG | B | 500 | 47.173 | 12.642  | 40.559 | 1.00 27.15 |
| ATOM | 4305 | C19 | LIG | B | 500 | 46.152 | 13.542  | 40.303 | 1.00 27.74 |
| ATOM | 4306 | C20 | LIG | B | 500 | 46.323 | 14.578  | 39.383 | 1.00 28.10 |
| ATOM | 4307 | N7  | LIG | B | 500 | 45.261 | 15.469  | 39.134 | 1.00 29.94 |
| ATOM | 4308 | C21 | LIG | B | 500 | 44.201 | 15.931  | 39.828 | 1.00 32.65 |
| ATOM | 4309 | O1  | LIG | B | 500 | 44.009 | 15.567  | 40.973 | 1.00 32.28 |
| ATOM | 4310 | C22 | LIG | B | 500 | 43.253 | 16.911  | 39.177 | 1.00 33.89 |
| ATOM | 4311 | C23 | LIG | B | 500 | 41.834 | 16.313  | 39.183 | 1.00 35.25 |
| ATOM | 4312 | C24 | LIG | B | 500 | 41.631 | 15.417  | 37.974 | 1.00 35.37 |
| ATOM | 4313 | C25 | LIG | B | 500 | 41.313 | 14.074  | 38.143 | 1.00 35.97 |
| ATOM | 4314 | C26 | LIG | B | 500 | 41.127 | 13.254  | 37.041 | 1.00 36.52 |
| ATOM | 4315 | C27 | LIG | B | 500 | 41.265 | 13.775  | 35.762 | 1.00 37.17 |
| ATOM | 4316 | C28 | LIG | B | 500 | 41.581 | 15.119  | 35.590 | 1.00 37.32 |
| ATOM | 4317 | C29 | LIG | B | 500 | 41.768 | 15.935  | 36.696 | 1.00 36.25 |
| ATOM | 4318 | C30 | LIG | B | 500 | 47.533 | 14.724  | 38.709 | 1.00 27.66 |
| ATOM | 4319 | O2  | LIG | B | 500 | 47.694 | 15.742  | 37.814 | 1.00 27.66 |
| ATOM | 4320 | C31 | LIG | B | 500 | 48.735 | 15.832  | 36.844 | 1.00 26.92 |
| ATOM | 4321 | C32 | LIG | B | 500 | 48.564 | 13.831  | 38.952 | 1.00 27.46 |
| ATOM | 4322 | C33 | LIG | B | 500 | 50.908 | 12.257  | 40.460 | 1.00 25.12 |
| ATOM | 4323 | OH2 | H2O | B | 600 | 33.564 | 0.464   | 53.599 | 1.00 26.49 |
| ATOM | 4324 | OH2 | H2O | B | 601 | 27.310 | -1.713  | 62.591 | 1.00 19.17 |
| ATOM | 4325 | OH2 | H2O | B | 602 | 34.956 | 19.888  | 66.833 | 1.00 35.09 |
| ATOM | 4326 | OH2 | H2O | B | 603 | 22.927 | -2.693  | 60.861 | 1.00 24.23 |
| ATOM | 4327 | OH2 | H2O | B | 604 | 35.425 | 9.630   | 49.842 | 1.00 15.73 |
| ATOM | 4328 | OH2 | H2O | B | 605 | 25.151 | 5.597   | 63.800 | 1.00 16.83 |
| ATOM | 4329 | OH2 | H2O | B | 606 | 31.494 | 11.222  | 66.574 | 1.00 31.90 |
| ATOM | 4330 | OH2 | H2O | B | 607 | 27.942 | -8.056  | 61.046 | 1.00 22.66 |
| ATOM | 4331 | OH2 | H2O | B | 608 | 34.523 | -1.560  | 58.457 | 1.00 18.93 |
| ATOM | 4332 | OH2 | H2O | B | 609 | 34.661 | 3.866   | 68.882 | 1.00 19.51 |
| ATOM | 4333 | OH2 | H2O | B | 610 | 29.434 | 16.637  | 62.933 | 1.00 24.10 |
| ATOM | 4334 | OH2 | H2O | B | 611 | 37.020 | 12.929  | 44.025 | 1.00 23.71 |
| ATOM | 4335 | OH2 | H2O | B | 612 | 18.964 | 14.825  | 67.070 | 1.00 23.99 |
| ATOM | 4336 | OH2 | H2O | B | 613 | 27.037 | 15.371  | 63.488 | 1.00 22.74 |
| ATOM | 4337 | OH2 | H2O | B | 614 | 36.335 | -2.089  | 46.526 | 1.00 18.58 |
| ATOM | 4338 | OH2 | H2O | B | 615 | 30.100 | -4.422  | 66.135 | 1.00 26.26 |
| ATOM | 4339 | OH2 | H2O | B | 616 | 32.607 | 21.615  | 64.567 | 1.00 20.37 |
| ATOM | 4340 | OH2 | H2O | B | 617 | 62.860 | 10.291  | 39.659 | 1.00 31.73 |
| ATOM | 4341 | OH2 | H2O | B | 618 | 48.979 | 17.806  | 60.612 | 1.00 41.99 |
| ATOM | 4342 | OH2 | H2O | B | 619 | 43.163 | 2.948   | 48.020 | 1.00 18.75 |
| ATOM | 4343 | OH2 | H2O | B | 620 | 32.162 | 16.116  | 59.104 | 1.00 27.82 |
| ATOM | 4344 | OH2 | H2O | B | 621 | 32.041 | 7.318   | 51.035 | 1.00 23.07 |
| ATOM | 4345 | OH2 | H2O | B | 622 | 60.498 | 24.522  | 28.272 | 1.00 42.66 |
| ATOM | 4346 | OH2 | H2O | B | 623 | 34.198 | -5.512  | 64.288 | 1.00 22.65 |
| ATOM | 4347 | OH2 | H2O | B | 624 | 45.454 | 23.893  | 58.186 | 1.00 52.30 |
| ATOM | 4348 | OH2 | H2O | B | 625 | 26.819 | 10.813  | 53.065 | 1.00 38.10 |
| ATOM | 4349 | OH2 | H2O | B | 626 | 26.788 | 10.264  | 68.273 | 1.00 19.55 |
| ATOM | 4350 | OH2 | H2O | B | 627 | 20.602 | 14.368  | 69.232 | 1.00 26.48 |
| ATOM | 4351 | OH2 | H2O | B | 628 | 26.644 | -1.057  | 57.749 | 1.00 18.42 |
| ATOM | 4352 | OH2 | H2O | B | 629 | 25.921 | 16.106  | 61.080 | 1.00 27.89 |
| ATOM | 4353 | OH2 | H2O | B | 630 | 47.329 | 23.213  | 47.221 | 1.00 34.59 |

Figure 7

```
ATOM  4354  OH2 H2O B 631    31.506   1.208  63.636  1.00 15.86
ATOM  4355  OH2 H2O B 632    23.952  -0.834  53.622  1.00 29.19
ATOM  4356  OH2 H2O B 633    54.801  21.498  21.543  1.00 51.70
ATOM  4357  OH2 H2O B 634    32.765 -13.697  55.767  1.00 51.30
ATOM  4358  OH2 H2O B 635    28.957  17.695  52.724  1.00 24.75
ATOM  4359  OH2 H2O B 636    41.168  -5.551  59.859  1.00 25.41
ATOM  4360  OH2 H2O B 637    31.114  24.569  62.196  1.00 20.14
ATOM  4361  OH2 H2O B 638    28.333   1.139  64.189  1.00 29.57
ATOM  4362  OH2 H2O B 639    31.797   0.002  51.784  1.00 17.93
ATOM  4363  OH2 H2O B 640    32.407  -8.108  67.340  1.00 19.76
ATOM  4364  OH2 H2O B 641    53.239   3.477  31.985  1.00 42.65
ATOM  4365  OH2 H2O B 642    32.882  18.973  46.384  1.00 31.02
ATOM  4366  OH2 H2O B 643    38.428  -5.704  66.778  1.00 25.16
ATOM  4367  OH2 H2O B 644    38.594  11.456  34.892  1.00 37.15
ATOM  4368  OH2 H2O B 645    42.481   6.995  38.358  1.00 51.12
ATOM  4369  OH2 H2O B 646    21.176   9.863  69.195  1.00 46.10
ATOM  4370  OH2 H2O B 647    35.078 -11.688  59.203  1.00 16.98
ATOM  4371  OH2 H2O B 648    54.240   1.641  41.382  1.00 42.13
ATOM  4372  OH2 H2O B 649    26.079  -2.044  65.019  1.00 29.69
ATOM  4373  OH2 H2O B 650    36.965  21.562  59.393  1.00 25.96
ATOM  4374  OH2 H2O B 651    51.438  -0.892  62.161  1.00 45.71
ATOM  4375  OH2 H2O B 652    34.048  21.385  61.290  1.00 53.85
ATOM  4376  OH2 H2O B 653    25.979  14.560  56.218  1.00 25.26
ATOM  4377  OH2 H2O B 654    40.209  18.692  41.798  1.00 26.09
ATOM  4378  OH2 H2O B 655    61.564   2.107  49.447  1.00 38.17
ATOM  4379  OH2 H2O B 656    42.685  22.365  57.857  1.00 30.17
ATOM  4380  OH2 H2O B 657    25.269  -2.264  51.988  1.00 37.87
ATOM  4381  OH2 H2O B 658    59.303  17.928  42.308  1.00 42.01
ATOM  4382  OH2 H2O B 659    33.350   7.537  48.444  1.00 29.74
ATOM  4383  OH2 H2O B 660    23.151   3.767  56.435  1.00 41.77
ATOM  4384  OH2 H2O B 661    42.692   1.317  45.933  1.00 56.18
ATOM  4385  OH2 H2O B 662    58.075   6.777  29.375  1.00 26.28
ATOM  4386  OH2 H2O B 663    21.687   3.400  53.831  1.00 29.41
ATOM  4387  OH2 H2O B 664    56.467  20.393  41.312  1.00 37.05
ATOM  4388  OH2 H2O B 665    47.041   5.831  42.252  1.00 40.20
ATOM  4389  OH2 H2O B 666    42.986  -2.298  54.957  1.00 22.05
ATOM  4390  OH2 H2O B 667    23.607  -0.735  56.484  1.00 34.93
ATOM  4391  OH2 H2O B 668    46.427  -1.519  71.481  1.00 31.63
ATOM  4392  OH2 H2O B 669    27.343  -3.748  66.528  1.00 35.64
ATOM  4393  OH2 H2O B 670    62.207  10.288  49.655  1.00 35.88
ATOM  4394  OH2 H2O B 671    23.390  -2.553  50.007  1.00 46.04
ATOM  4395  OH2 H2O B 672    30.467  17.768  29.434  1.00 46.12
ATOM  4396  OH2 H2O B 673    45.751  24.261  43.087  1.00 28.39
ATOM  4397  OH2 H2O B 674    44.723  -0.818  49.924  1.00 27.32
ATOM  4398  OH2 H2O B 675    45.385  22.535  45.454  1.00 31.07
ATOM  4399  OH2 H2O B 676    19.635  11.991  70.531  1.00 30.10
ATOM  4400  OH2 H2O B 677    50.574  13.435  24.979  1.00 40.82
ATOM  4401  OH2 H2O B 678    34.936  12.801  72.574  1.00 35.16
ATOM  4402  OH2 H2O B 679    59.767  10.219  37.117  1.00 28.55
ATOM  4403  OH2 H2O B 680    37.392  20.579  45.895  1.00 30.27
ATOM  4404  OH2 H2O B 681    50.980  11.967  65.381  1.00 41.23
END
```

Figure 7

```
CRYST1    57.643    44.609   120.029   90.00    90.07    90.00 P21              1
SCALE1      0.017348  0.000000  0.000021        0.00000
SCALE2      0.000000  0.022417  0.000000        0.00000
SCALE3      0.000000  0.000000  0.008331        0.00000
ATOM       1   CB    TRP  A 238      18.228   -5.776   28.037  1.00 54.26
ATOM       2   CG    TRP  A 238      17.900   -6.382   26.705  1.00 53.53
ATOM       3   CD2   TRP  A 238      18.456   -6.031   25.410  1.00 52.99
ATOM       4   CE2   TRP  A 238      17.748   -6.788   24.440  1.00 51.98
ATOM       5   CE3   TRP  A 238      19.471   -5.158   24.977  1.00 52.93
ATOM       6   CD1   TRP  A 238      16.935   -7.314   26.451  1.00 53.72
ATOM       7   NE1   TRP  A 238      16.829   -7.560   25.106  1.00 52.73
ATOM       8   CZ2   TRP  A 238      18.015   -6.685   23.062  1.00 52.21
ATOM       9   CZ3   TRP  A 238      19.735   -5.055   23.588  1.00 52.08
ATOM      10   CH2   TRP  A 238      19.015   -5.809   22.669  1.00 52.29
ATOM      11   C     TRP  A 238      19.897   -5.979   29.881  1.00 54.15
ATOM      12   O     TRP  A 238      20.771   -5.201   29.473  1.00 53.85
ATOM      13   N     TRP  A 238      17.991   -7.495   29.802  1.00 55.73
ATOM      14   CA    TRP  A 238      18.955   -6.745   28.939  1.00 54.83
ATOM      15   N     GLU  A 239      19.654   -6.186   31.161  1.00 53.01
ATOM      16   CA    GLU  A 239      20.349   -5.605   32.244  1.00 51.77
ATOM      17   CB    GLU  A 239      19.590   -6.039   33.497  1.00 52.33
ATOM      18   CG    GLU  A 239      20.083   -5.445   34.817  1.00 52.83
ATOM      19   CD    GLU  A 239      19.628   -4.007   34.995  1.00 53.22
ATOM      20   OE1   GLU  A 239      18.688   -3.593   34.287  1.00 54.48
ATOM      21   OE2   GLU  A 239      20.179   -3.289   35.857  1.00 53.06
ATOM      22   C     GLU  A 239      21.816   -6.027   32.359  1.00 50.40
ATOM      23   O     GLU  A 239      22.210   -7.157   32.053  1.00 50.89
ATOM      24   N     VAL  A 240      22.629   -5.033   32.694  1.00 48.41
ATOM      25   CA    VAL  A 240      24.046   -5.271   32.933  1.00 46.27
ATOM      26   CB    VAL  A 240      24.959   -4.785   31.790  1.00 45.31
ATOM      27   CG1   VAL  A 240      24.652   -5.549   30.513  1.00 44.57
ATOM      28   CG2   VAL  A 240      24.861   -3.297   31.599  1.00 44.48
ATOM      29   C     VAL  A 240      24.389   -4.550   34.241  1.00 45.44
ATOM      30   O     VAL  A 240      23.697   -3.606   34.642  1.00 45.59
ATOM      31   N     PRO  A 241      25.386   -5.061   34.994  1.00 44.38
ATOM      32   CD    PRO  A 241      26.034   -6.380   34.931  1.00 43.56
ATOM      33   CA    PRO  A 241      25.732   -4.378   36.250  1.00 43.77
ATOM      34   CB    PRO  A 241      26.717   -5.354   36.897  1.00 43.71
ATOM      35   CG    PRO  A 241      26.248   -6.682   36.395  1.00 43.84
ATOM      36   C     PRO  A 241      26.382   -3.023   35.965  1.00 43.47
ATOM      37   O     PRO  A 241      27.162   -2.881   35.028  1.00 43.42
ATOM      38   N     ARG  A 242      26.010   -2.013   36.737  1.00 43.27
ATOM      39   CA    ARG  A 242      26.555   -0.674   36.558  1.00 43.80
ATOM      40   CB    ARG  A 242      26.054    0.198   37.698  1.00 44.24
ATOM      41   CG    ARG  A 242      26.651    1.573   37.757  1.00 45.06
ATOM      42   CD    ARG  A 242      25.957    2.492   36.813  1.00 45.53
ATOM      43   NE    ARG  A 242      24.505    2.489   37.004  1.00 46.68
ATOM      44   CZ    ARG  A 242      23.877    2.857   38.117  1.00 45.19
ATOM      45   NH1   ARG  A 242      24.561    3.254   39.182  1.00 46.46
ATOM      46   NH2   ARG  A 242      22.553    2.873   38.141  1.00 44.16
ATOM      47   C     ARG  A 242      28.093   -0.648   36.507  1.00 44.54
```

Figure 8

| ATOM | 48 | O | ARG | A | 242 | 28.689 | 0.279 | 35.953 | 1.00 | 43.90 |
| ATOM | 49 | N | GLU | A | 243 | 28.716 | -1.664 | 37.108 | 1.00 | 45.64 |
| ATOM | 50 | CA | GLU | A | 243 | 30.175 | -1.814 | 37.166 | 1.00 | 45.92 |
| ATOM | 51 | CB | GLU | A | 243 | 30.566 | -3.025 | 38.030 | 1.00 | 48.88 |
| ATOM | 52 | CG | GLU | A | 243 | 30.355 | -2.870 | 39.534 | 1.00 | 53.59 |
| ATOM | 53 | CD | GLU | A | 243 | 28.889 | -2.981 | 39.971 | 1.00 | 55.79 |
| ATOM | 54 | OE1 | GLU | A | 243 | 28.444 | -4.116 | 40.301 | 1.00 | 56.14 |
| ATOM | 55 | OE2 | GLU | A | 243 | 28.204 | -1.930 | 40.015 | 1.00 | 55.03 |
| ATOM | 56 | C | GLU | A | 243 | 30.786 | -2.007 | 35.791 | 1.00 | 44.43 |
| ATOM | 57 | O | GLU | A | 243 | 31.949 | -1.702 | 35.577 | 1.00 | 44.60 |
| ATOM | 58 | N | THR | A | 244 | 30.008 | -2.559 | 34.873 | 1.00 | 43.27 |
| ATOM | 59 | CA | THR | A | 244 | 30.469 | -2.813 | 33.509 | 1.00 | 41.64 |
| ATOM | 60 | CB | THR | A | 244 | 29.526 | -3.825 | 32.820 | 1.00 | 41.26 |
| ATOM | 61 | OG1 | THR | A | 244 | 28.247 | -3.214 | 32.581 | 1.00 | 40.06 |
| ATOM | 62 | CG2 | THR | A | 244 | 29.332 | -5.046 | 33.717 | 1.00 | 39.93 |
| ATOM | 63 | C | THR | A | 244 | 30.515 | -1.547 | 32.653 | 1.00 | 41.10 |
| ATOM | 64 | O | THR | A | 244 | 30.956 | -1.582 | 31.505 | 1.00 | 40.99 |
| ATOM | 65 | N | LEU | A | 245 | 30.161 | -0.416 | 33.254 | 1.00 | 40.86 |
| ATOM | 66 | CA | LEU | A | 245 | 30.075 | 0.841 | 32.525 | 1.00 | 40.52 |
| ATOM | 67 | CB | LEU | A | 245 | 28.597 | 1.177 | 32.371 | 1.00 | 41.67 |
| ATOM | 68 | CG | LEU | A | 245 | 27.935 | 1.612 | 31.078 | 1.00 | 42.61 |
| ATOM | 69 | CD1 | LEU | A | 245 | 28.071 | 0.553 | 30.019 | 1.00 | 43.81 |
| ATOM | 70 | CD2 | LEU | A | 245 | 26.471 | 1.804 | 31.408 | 1.00 | 45.28 |
| ATOM | 71 | C | LEU | A | 245 | 30.766 | 2.022 | 33.191 | 1.00 | 39.79 |
| ATOM | 72 | O | LEU | A | 245 | 30.572 | 2.287 | 34.382 | 1.00 | 39.46 |
| ATOM | 73 | N | LYS | A | 246 | 31.526 | 2.767 | 32.396 | 1.00 | 39.09 |
| ATOM | 74 | CA | LYS | A | 246 | 32.229 | 3.941 | 32.901 | 1.00 | 38.29 |
| ATOM | 75 | CB | LYS | A | 246 | 33.756 | 3.716 | 32.885 | 1.00 | 39.86 |
| ATOM | 76 | CG | LYS | A | 246 | 34.575 | 4.878 | 33.487 | 1.00 | 42.14 |
| ATOM | 77 | CD | LYS | A | 246 | 36.072 | 4.604 | 33.524 | 1.00 | 43.69 |
| ATOM | 78 | CE | LYS | A | 246 | 36.627 | 4.291 | 32.143 | 1.00 | 43.85 |
| ATOM | 79 | NZ | LYS | A | 246 | 38.061 | 3.903 | 32.217 | 1.00 | 46.50 |
| ATOM | 80 | C | LYS | A | 246 | 31.858 | 5.199 | 32.107 | 1.00 | 36.17 |
| ATOM | 81 | O | LYS | A | 246 | 32.136 | 5.299 | 30.910 | 1.00 | 34.99 |
| ATOM | 82 | N | LEU | A | 247 | 31.173 | 6.125 | 32.776 | 1.00 | 34.36 |
| ATOM | 83 | CA | LEU | A | 247 | 30.775 | 7.388 | 32.171 | 1.00 | 32.53 |
| ATOM | 84 | CB | LEU | A | 247 | 29.590 | 8.008 | 32.919 | 1.00 | 30.52 |
| ATOM | 85 | CG | LEU | A | 247 | 28.194 | 7.539 | 32.465 | 1.00 | 29.82 |
| ATOM | 86 | CD1 | LEU | A | 247 | 28.038 | 6.016 | 32.533 | 1.00 | 27.92 |
| ATOM | 87 | CD2 | LEU | A | 247 | 27.145 | 8.224 | 33.318 | 1.00 | 29.57 |
| ATOM | 88 | C | LEU | A | 247 | 31.994 | 8.290 | 32.206 | 1.00 | 32.44 |
| ATOM | 89 | O | LEU | A | 247 | 32.643 | 8.436 | 33.246 | 1.00 | 33.76 |
| ATOM | 90 | N | VAL | A | 248 | 32.332 | 8.845 | 31.047 | 1.00 | 31.68 |
| ATOM | 91 | CA | VAL | A | 248 | 33.511 | 9.691 | 30.898 | 1.00 | 30.48 |
| ATOM | 92 | CB | VAL | A | 248 | 34.389 | 9.179 | 29.713 | 1.00 | 30.05 |
| ATOM | 93 | CG1 | VAL | A | 248 | 35.626 | 10.057 | 29.524 | 1.00 | 30.41 |
| ATOM | 94 | CG2 | VAL | A | 248 | 34.783 | 7.741 | 29.942 | 1.00 | 29.41 |
| ATOM | 95 | C | VAL | A | 248 | 33.282 | 11.189 | 30.710 | 1.00 | 29.68 |
| ATOM | 96 | O | VAL | A | 248 | 33.883 | 12.005 | 31.391 | 1.00 | 29.02 |
| ATOM | 97 | N | GLU | A | 249 | 32.406 | 11.541 | 29.785 | 1.00 | 30.24 |
| ATOM | 98 | CA | GLU | A | 249 | 32.154 | 12.935 | 29.454 | 1.00 | 30.07 |
| ATOM | 99 | CB | GLU | A | 249 | 32.949 | 13.233 | 28.198 | 1.00 | 30.60 |
| ATOM | 100 | CG | GLU | A | 249 | 32.731 | 14.554 | 27.579 | 1.00 | 34.00 |
| ATOM | 101 | CD | GLU | A | 249 | 33.456 | 14.661 | 26.256 | 1.00 | 36.44 |
| ATOM | 102 | OE1 | GLU | A | 249 | 34.590 | 14.162 | 26.154 | 1.00 | 38.02 |
| ATOM | 103 | OE2 | GLU | A | 249 | 32.892 | 15.231 | 25.302 | 1.00 | 40.54 |
| ATOM | 104 | C | GLU | A | 249 | 30.676 | 13.190 | 29.191 | 1.00 | 29.71 |
| ATOM | 105 | O | GLU | A | 249 | 30.009 | 12.403 | 28.519 | 1.00 | 28.64 |
| ATOM | 106 | N | ARG | A | 250 | 30.172 | 14.309 | 29.693 | 1.00 | 28.94 |
| ATOM | 107 | CA | ARG | A | 250 | 28.773 | 14.633 | 29.500 | 1.00 | 28.44 |

Figure 8

| | | | | | | | | |
|---|---|---|---|---|---|---|---|---|
| ATOM | 108 | CB | ARG | A | 250 | 28.225 | 15.411 | 30.680 | 1.00 | 27.60 |
| ATOM | 109 | CG | ARG | A | 250 | 26.727 | 15.284 | 30.779 | 1.00 | 28.51 |
| ATOM | 110 | CD | ARG | A | 250 | 26.202 | 16.052 | 31.940 | 1.00 | 27.73 |
| ATOM | 111 | NE | ARG | A | 250 | 26.460 | 17.466 | 31.744 | 1.00 | 28.57 |
| ATOM | 112 | CZ | ARG | A | 250 | 26.170 | 18.404 | 32.635 | 1.00 | 29.87 |
| ATOM | 113 | NH1 | ARG | A | 250 | 25.607 | 18.081 | 33.794 | 1.00 | 29.38 |
| ATOM | 114 | NH2 | ARG | A | 250 | 26.455 | 19.667 | 32.364 | 1.00 | 30.27 |
| ATOM | 115 | C | ARG | A | 250 | 28.550 | 15.401 | 28.215 | 1.00 | 28.53 |
| ATOM | 116 | O | ARG | A | 250 | 29.129 | 16.468 | 28.015 | 1.00 | 29.24 |
| ATOM | 117 | N | LEU | A | 251 | 27.730 | 14.826 | 27.338 | 1.00 | 27.63 |
| ATOM | 118 | CA | LEU | A | 251 | 27.407 | 15.419 | 26.050 | 1.00 | 27.28 |
| ATOM | 119 | CB | LEU | A | 251 | 27.140 | 14.322 | 25.002 | 1.00 | 25.23 |
| ATOM | 120 | CG | LEU | A | 251 | 28.307 | 13.369 | 24.731 | 1.00 | 22.11 |
| ATOM | 121 | CD1 | LEU | A | 251 | 27.840 | 12.160 | 23.955 | 1.00 | 22.05 |
| ATOM | 122 | CD2 | LEU | A | 251 | 29.389 | 14.087 | 23.991 | 1.00 | 19.40 |
| ATOM | 123 | C | LEU | A | 251 | 26.219 | 16.368 | 26.151 | 1.00 | 27.82 |
| ATOM | 124 | O | LEU | A | 251 | 26.106 | 17.313 | 25.366 | 1.00 | 29.09 |
| ATOM | 125 | N | GLY | A | 252 | 25.354 | 16.136 | 27.136 | 1.00 | 28.09 |
| ATOM | 126 | CA | GLY | A | 252 | 24.194 | 16.997 | 27.318 | 1.00 | 26.87 |
| ATOM | 127 | C | GLY | A | 252 | 23.440 | 16.793 | 28.623 | 1.00 | 26.83 |
| ATOM | 128 | O | GLY | A | 252 | 23.441 | 15.705 | 29.192 | 1.00 | 25.73 |
| ATOM | 129 | N | ALA | A | 253 | 22.790 | 17.854 | 29.089 | 1.00 | 27.54 |
| ATOM | 130 | CA | ALA | A | 253 | 22.002 | 17.817 | 30.317 | 1.00 | 28.55 |
| ATOM | 131 | CB | ALA | A | 253 | 22.818 | 18.359 | 31.481 | 1.00 | 28.20 |
| ATOM | 132 | C | ALA | A | 253 | 20.720 | 18.643 | 30.136 | 1.00 | 29.94 |
| ATOM | 133 | O | ALA | A | 253 | 20.774 | 19.837 | 29.790 | 1.00 | 28.91 |
| ATOM | 134 | N | GLY | A | 254 | 19.574 | 17.995 | 30.361 | 1.00 | 31.80 |
| ATOM | 135 | CA | GLY | A | 254 | 18.283 | 18.658 | 30.216 | 1.00 | 32.77 |
| ATOM | 136 | C | GLY | A | 254 | 17.293 | 18.482 | 31.352 | 1.00 | 33.45 |
| ATOM | 137 | O | GLY | A | 254 | 17.628 | 18.022 | 32.438 | 1.00 | 34.23 |
| ATOM | 138 | N | GLN | A | 255 | 16.045 | 18.821 | 31.077 | 1.00 | 34.51 |
| ATOM | 139 | CA | GLN | A | 255 | 14.985 | 18.744 | 32.071 | 1.00 | 35.32 |
| ATOM | 140 | CB | GLN | A | 255 | 13.691 | 19.304 | 31.476 | 1.00 | 38.18 |
| ATOM | 141 | CG | GLN | A | 255 | 12.785 | 20.016 | 32.484 | 1.00 | 41.65 |
| ATOM | 142 | CD | GLN | A | 255 | 11.323 | 20.053 | 32.048 | 1.00 | 43.29 |
| ATOM | 143 | OE1 | GLN | A | 255 | 10.422 | 20.159 | 32.895 | 1.00 | 42.94 |
| ATOM | 144 | NE2 | GLN | A | 255 | 11.077 | 19.941 | 30.728 | 1.00 | 43.02 |
| ATOM | 145 | C | GLN | A | 255 | 14.732 | 17.341 | 32.639 | 1.00 | 34.49 |
| ATOM | 146 | O | GLN | A | 255 | 14.527 | 17.186 | 33.853 | 1.00 | 34.51 |
| ATOM | 147 | N | PHE | A | 256 | 14.757 | 16.331 | 31.764 | 1.00 | 32.91 |
| ATOM | 148 | CA | PHE | A | 256 | 14.497 | 14.938 | 32.154 | 1.00 | 31.20 |
| ATOM | 149 | CB | PHE | A | 256 | 13.677 | 14.226 | 31.071 | 1.00 | 30.47 |
| ATOM | 150 | CG | PHE | A | 256 | 12.278 | 14.765 | 30.896 | 1.00 | 31.34 |
| ATOM | 151 | CD1 | PHE | A | 256 | 11.775 | 15.757 | 31.736 | 1.00 | 31.31 |
| ATOM | 152 | CD2 | PHE | A | 256 | 11.452 | 14.260 | 29.895 | 1.00 | 31.27 |
| ATOM | 153 | CE1 | PHE | A | 256 | 10.476 | 16.232 | 31.580 | 1.00 | 31.82 |
| ATOM | 154 | CE2 | PHE | A | 256 | 10.146 | 14.732 | 29.734 | 1.00 | 31.69 |
| ATOM | 155 | CZ | PHE | A | 256 | 9.660 | 15.718 | 30.579 | 1.00 | 31.24 |
| ATOM | 156 | C | PHE | A | 256 | 15.706 | 14.068 | 32.501 | 1.00 | 30.44 |
| ATOM | 157 | O | PHE | A | 256 | 15.541 | 12.959 | 33.018 | 1.00 | 30.46 |
| ATOM | 158 | N | GLY | A | 257 | 16.910 | 14.553 | 32.201 | 1.00 | 29.70 |
| ATOM | 159 | CA | GLY | A | 257 | 18.106 | 13.779 | 32.479 | 1.00 | 28.64 |
| ATOM | 160 | C | GLY | A | 257 | 19.343 | 14.247 | 31.737 | 1.00 | 28.48 |
| ATOM | 161 | O | GLY | A | 257 | 19.495 | 15.436 | 31.467 | 1.00 | 26.32 |
| ATOM | 162 | N | GLU | A | 258 | 20.204 | 13.298 | 31.364 | 1.00 | 29.35 |
| ATOM | 163 | CA | GLU | A | 258 | 21.462 | 13.611 | 30.679 | 1.00 | 30.95 |
| ATOM | 164 | CB | GLU | A | 258 | 22.573 | 13.789 | 31.722 | 1.00 | 32.61 |
| ATOM | 165 | CG | GLU | A | 258 | 22.218 | 14.737 | 32.861 | 1.00 | 36.09 |
| ATOM | 166 | CD | GLU | A | 258 | 23.348 | 14.927 | 33.859 | 1.00 | 39.23 |
| ATOM | 167 | OE1 | GLU | A | 258 | 24.023 | 13.929 | 34.218 | 1.00 | 40.41 |

Figure 8

```
ATOM    168  OE2 GLU A 258      23.556  16.084  34.294  1.00 40.81
ATOM    169  C   GLU A 258      21.930  12.541  29.690  1.00 30.74
ATOM    170  O   GLU A 258      21.474  11.392  29.736  1.00 31.89
ATOM    171  N   VAL A 259      22.861  12.927  28.816  1.00 29.88
ATOM    172  CA  VAL A 259      23.461  12.016  27.830  1.00 28.79
ATOM    173  CB  VAL A 259      23.077  12.361  26.385  1.00 27.64
ATOM    174  CG1 VAL A 259      23.646  11.298  25.451  1.00 25.48
ATOM    175  CG2 VAL A 259      21.551  12.481  26.244  1.00 25.60
ATOM    176  C   VAL A 259      24.988  12.120  27.979  1.00 29.15
ATOM    177  O   VAL A 259      25.549  13.230  27.970  1.00 29.25
ATOM    178  N   TRP A 260      25.634  10.962  28.146  1.00 28.58
ATOM    179  CA  TRP A 260      27.084  10.845  28.361  1.00 27.70
ATOM    180  CB  TRP A 260      27.371  10.259  29.760  1.00 25.66
ATOM    181  CG  TRP A 260      27.182  11.184  30.926  1.00 26.31
ATOM    182  CD2 TRP A 260      28.210  11.716  31.776  1.00 27.57
ATOM    183  CE2 TRP A 260      27.577  12.522  32.747  1.00 28.15
ATOM    184  CE3 TRP A 260      29.609  11.589  31.813  1.00 28.26
ATOM    185  CD1 TRP A 260      25.997  11.677  31.409  1.00 26.56
ATOM    186  NE1 TRP A 260      26.229  12.485  32.496  1.00 27.00
ATOM    187  CZ2 TRP A 260      28.300  13.200  33.745  1.00 27.85
ATOM    188  CZ3 TRP A 260      30.323  12.263  32.800  1.00 26.57
ATOM    189  CH2 TRP A 260      29.669  13.058  33.749  1.00 26.73
ATOM    190  C   TRP A 260      27.808   9.936  27.373  1.00 27.66
ATOM    191  O   TRP A 260      27.214   9.036  26.783  1.00 27.37
ATOM    192  N   MET A 261      29.104  10.194  27.192  1.00 28.33
ATOM    193  CA  MET A 261      29.950   9.342  26.356  1.00 28.13
ATOM    194  CB  MET A 261      31.013  10.149  25.606  1.00 27.51
ATOM    195  CG  MET A 261      31.984   9.274  24.771  1.00 27.27
ATOM    196  SD  MET A 261      33.389   8.467  25.665  1.00 27.54
ATOM    197  CE  MET A 261      34.320   9.974  26.221  1.00 24.52
ATOM    198  C   MET A 261      30.624   8.466  27.406  1.00 28.16
ATOM    199  O   MET A 261      30.994   8.960  28.475  1.00 27.01
ATOM    200  N   GLY A 262      30.756   7.175  27.124  1.00 28.34
ATOM    201  CA  GLY A 262      31.374   6.285  28.083  1.00 28.58
ATOM    202  C   GLY A 262      31.958   5.066  27.418  1.00 29.40
ATOM    203  O   GLY A 262      32.039   4.992  26.194  1.00 28.97
ATOM    204  N   TYR A 263      32.374   4.106  28.234  1.00 30.58
ATOM    205  CA  TYR A 263      32.956   2.881  27.725  1.00 32.19
ATOM    206  CB  TYR A 263      34.477   2.892  27.902  1.00 30.28
ATOM    207  CG  TYR A 263      35.165   3.900  26.999  1.00 26.77
ATOM    208  CD1 TYR A 263      35.534   3.557  25.705  1.00 24.78
ATOM    209  CE1 TYR A 263      36.114   4.482  24.865  1.00 25.32
ATOM    210  CD2 TYR A 263      35.402   5.209  27.432  1.00 26.23
ATOM    211  CE2 TYR A 263      35.986   6.150  26.593  1.00 25.52
ATOM    212  CZ  TYR A 263      36.341   5.777  25.313  1.00 26.22
ATOM    213  OH  TYR A 263      36.953   6.691  24.477  1.00 29.23
ATOM    214  C   TYR A 263      32.315   1.691  28.391  1.00 34.73
ATOM    215  O   TYR A 263      32.140   1.655  29.606  1.00 35.31
ATOM    216  N   TYR A 264      31.914   0.743  27.553  1.00 39.00
ATOM    217  CA  TYR A 264      31.234  -0.487  27.953  1.00 43.40
ATOM    218  CB  TYR A 264      30.105  -0.753  26.933  1.00 45.17
ATOM    219  CG  TYR A 264      29.134  -1.894  27.195  1.00 47.94
ATOM    220  CD1 TYR A 264      28.907  -2.397  28.486  1.00 48.62
ATOM    221  CE1 TYR A 264      27.974  -3.441  28.708  1.00 50.27
ATOM    222  CD2 TYR A 264      28.413  -2.459  26.127  1.00 49.61
ATOM    223  CE2 TYR A 264      27.485  -3.492  26.331  1.00 50.23
ATOM    224  CZ  TYR A 264      27.269  -3.983  27.620  1.00 50.32
ATOM    225  OH  TYR A 264      26.356  -5.006  27.802  1.00 49.92
ATOM    226  C   TYR A 264      32.264  -1.615  27.962  1.00 44.83
ATOM    227  O   TYR A 264      32.994  -1.809  26.988  1.00 45.59
```

Figure 8

```
ATOM    228  N   ASN A 265      32.349  -2.322  29.084  1.00 46.31
ATOM    229  CA  ASN A 265      33.292  -3.422  29.229  1.00 48.16
ATOM    230  CB  ASN A 265      32.916  -4.573  28.284  1.00 48.45
ATOM    231  CG  ASN A 265      31.464  -5.028  28.455  1.00 49.30
ATOM    232  OD1 ASN A 265      31.005  -5.268  29.574  1.00 48.84
ATOM    233  ND2 ASN A 265      30.738  -5.150  27.339  1.00 48.75
ATOM    234  C   ASN A 265      34.702  -2.903  28.942  1.00 49.30
ATOM    235  O   ASN A 265      35.517  -3.577  28.312  1.00 50.10
ATOM    236  N   GLY A 266      34.947  -1.661  29.348  1.00 50.16
ATOM    237  CA  GLY A 266      36.250  -1.054  29.159  1.00 51.61
ATOM    238  C   GLY A 266      36.637  -0.556  27.779  1.00 52.99
ATOM    239  O   GLY A 266      37.277   0.494  27.690  1.00 53.58
ATOM    240  N   HIS A 267      36.240  -1.252  26.707  1.00 53.74
ATOM    241  CA  HIS A 267      36.625  -0.829  25.353  1.00 53.81
ATOM    242  CB  HIS A 267      37.529  -1.881  24.712  1.00 59.24
ATOM    243  CG  HIS A 267      38.905  -1.929  25.306  1.00 64.80
ATOM    244  CD2 HIS A 267      39.817  -0.951  25.537  1.00 66.11
ATOM    245  ND1 HIS A 267      39.474  -3.098  25.768  1.00 67.09
ATOM    246  CE1 HIS A 267      40.674  -2.839  26.257  1.00 67.91
ATOM    247  NE2 HIS A 267      40.907  -1.544  26.131  1.00 67.36
ATOM    248  C   HIS A 267      35.601  -0.356  24.319  1.00 51.17
ATOM    249  O   HIS A 267      35.976   0.302  23.344  1.00 50.84
ATOM    250  N   THR A 268      34.337  -0.735  24.484  1.00 48.03
ATOM    251  CA  THR A 268      33.288  -0.323  23.549  1.00 44.23
ATOM    252  CB  THR A 268      32.040  -1.234  23.667  1.00 44.78
ATOM    253  OG1 THR A 268      32.434  -2.608  23.567  1.00 45.65
ATOM    254  CG2 THR A 268      31.011  -0.908  22.576  1.00 43.87
ATOM    255  C   THR A 268      32.866   1.100  23.891  1.00 41.32
ATOM    256  O   THR A 268      32.475   1.377  25.014  1.00 41.02
ATOM    257  N   LYS A 269      33.000   2.020  22.948  1.00 37.95
ATOM    258  CA  LYS A 269      32.586   3.393  23.199  1.00 34.62
ATOM    259  CB  LYS A 269      33.267   4.340  22.223  1.00 32.01
ATOM    260  CG  LYS A 269      33.161   5.778  22.599  1.00 28.83
ATOM    261  CD  LYS A 269      33.991   6.580  21.653  1.00 28.47
ATOM    262  CE  LYS A 269      34.295   7.941  22.204  1.00 28.61
ATOM    263  NZ  LYS A 269      35.385   8.538  21.422  1.00 29.50
ATOM    264  C   LYS A 269      31.064   3.443  23.021  1.00 34.47
ATOM    265  O   LYS A 269      30.536   3.044  21.968  1.00 34.37
ATOM    266  N   VAL A 270      30.365   3.908  24.061  1.00 32.91
ATOM    267  CA  VAL A 270      28.905   3.999  24.057  1.00 29.67
ATOM    268  CB  VAL A 270      28.295   2.936  25.020  1.00 29.21
ATOM    269  CG1 VAL A 270      28.585   1.521  24.540  1.00 26.86
ATOM    270  CG2 VAL A 270      28.809   3.152  26.436  1.00 25.72
ATOM    271  C   VAL A 270      28.355   5.374  24.488  1.00 29.27
ATOM    272  O   VAL A 270      29.096   6.243  24.937  1.00 29.14
ATOM    273  N   ALA A 271      27.054   5.576  24.275  1.00 28.24
ATOM    274  CA  ALA A 271      26.361   6.789  24.706  1.00 26.75
ATOM    275  CB  ALA A 271      25.589   7.423  23.573  1.00 25.50
ATOM    276  C   ALA A 271      25.409   6.252  25.773  1.00 26.39
ATOM    277  O   ALA A 271      24.832   5.173  25.607  1.00 26.72
ATOM    278  N   VAL A 272      25.341   6.936  26.910  1.00 25.81
ATOM    279  CA  VAL A 272      24.483   6.521  28.013  1.00 25.57
ATOM    280  CB  VAL A 272      25.309   6.219  29.304  1.00 25.31
ATOM    281  CG1 VAL A 272      24.378   5.801  30.448  1.00 23.58
ATOM    282  CG2 VAL A 272      26.377   5.162  29.036  1.00 22.95
ATOM    283  C   VAL A 272      23.512   7.631  28.360  1.00 26.26
ATOM    284  O   VAL A 272      23.932   8.758  28.640  1.00 26.51
ATOM    285  N   LYS A 273      22.216   7.333  28.296  1.00 26.65
ATOM    286  CA  LYS A 273      21.191   8.322  28.659  1.00 26.72
ATOM    287  CB  LYS A 273      20.026   8.318  27.657  1.00 27.63
```

Figure 8

| | | | | | | | | | |
|---|---|---|---|---|---|---|---|---|---|
| ATOM | 288 | CG | LYS | A | 273 | 18.881 | 9.251 | 28.036 | 1.00 28.97 |
| ATOM | 289 | CD | LYS | A | 273 | 17.751 | 9.170 | 27.043 | 1.00 29.76 |
| ATOM | 290 | CE | LYS | A | 273 | 18.098 | 9.893 | 25.772 | 1.00 31.47 |
| ATOM | 291 | NZ | LYS | A | 273 | 16.918 | 10.067 | 24.859 | 1.00 31.42 |
| ATOM | 292 | C | LYS | A | 273 | 20.716 | 7.954 | 30.069 | 1.00 26.63 |
| ATOM | 293 | O | LYS | A | 273 | 20.410 | 6.791 | 30.346 | 1.00 25.34 |
| ATOM | 294 | N | SER | A | 274 | 20.746 | 8.919 | 30.980 | 1.00 27.26 |
| ATOM | 295 | CA | SER | A | 274 | 20.334 | 8.660 | 32.352 | 1.00 28.24 |
| ATOM | 296 | CB | SER | A | 274 | 21.465 | 9.014 | 33.317 | 1.00 27.33 |
| ATOM | 297 | OG | SER | A | 274 | 21.714 | 10.405 | 33.284 | 1.00 28.38 |
| ATOM | 298 | C | SER | A | 274 | 19.092 | 9.468 | 32.695 | 1.00 29.08 |
| ATOM | 299 | O | SER | A | 274 | 18.906 | 10.574 | 32.183 | 1.00 29.00 |
| ATOM | 300 | N | LEU | A | 275 | 18.274 | 8.933 | 33.596 | 1.00 29.86 |
| ATOM | 301 | CA | LEU | A | 275 | 17.043 | 9.597 | 34.006 | 1.00 31.19 |
| ATOM | 302 | CB | LEU | A | 275 | 15.908 | 8.569 | 34.125 | 1.00 28.77 |
| ATOM | 303 | CG | LEU | A | 275 | 14.569 | 8.999 | 34.748 | 1.00 28.14 |
| ATOM | 304 | CD1 | LEU | A | 275 | 13.883 | 10.059 | 33.889 | 1.00 26.50 |
| ATOM | 305 | CD2 | LEU | A | 275 | 13.649 | 7.777 | 34.950 | 1.00 26.71 |
| ATOM | 306 | C | LEU | A | 275 | 17.144 | 10.378 | 35.320 | 1.00 33.78 |
| ATOM | 307 | O | LEU | A | 275 | 17.540 | 9.828 | 36.352 | 1.00 34.41 |
| ATOM | 308 | N | LYS | A | 276 | 16.811 | 11.667 | 35.263 | 1.00 35.36 |
| ATOM | 309 | CA | LYS | A | 276 | 16.769 | 12.515 | 36.445 | 1.00 37.00 |
| ATOM | 310 | CB | LYS | A | 276 | 16.641 | 13.984 | 36.021 | 1.00 37.30 |
| ATOM | 311 | CG | LYS | A | 276 | 16.420 | 14.992 | 37.142 | 1.00 37.99 |
| ATOM | 312 | CD | LYS | A | 276 | 16.283 | 16.425 | 36.591 | 1.00 40.28 |
| ATOM | 313 | CE | LYS | A | 276 | 17.520 | 16.850 | 35.782 | 1.00 42.42 |
| ATOM | 314 | NZ | LYS | A | 276 | 17.512 | 18.261 | 35.263 | 1.00 42.75 |
| ATOM | 315 | C | LYS | A | 276 | 15.477 | 12.055 | 37.124 | 1.00 38.78 |
| ATOM | 316 | O | LYS | A | 276 | 14.381 | 12.286 | 36.601 | 1.00 39.99 |
| ATOM | 317 | N | GLN | A | 277 | 15.612 | 11.341 | 38.238 | 1.00 39.73 |
| ATOM | 318 | CA | GLN | A | 277 | 14.468 | 10.823 | 38.998 | 1.00 40.26 |
| ATOM | 319 | CB | GLN | A | 277 | 14.956 | 10.249 | 40.323 | 1.00 43.98 |
| ATOM | 320 | CG | GLN | A | 277 | 13.854 | 9.918 | 41.296 | 1.00 49.21 |
| ATOM | 321 | CD | GLN | A | 277 | 14.350 | 9.941 | 42.715 | 1.00 52.99 |
| ATOM | 322 | OE1 | GLN | A | 277 | 15.114 | 10.834 | 43.110 | 1.00 55.15 |
| ATOM | 323 | NE2 | GLN | A | 277 | 13.913 | 8.971 | 43.505 | 1.00 55.81 |
| ATOM | 324 | C | GLN | A | 277 | 13.352 | 11.835 | 39.259 | 1.00 38.80 |
| ATOM | 325 | O | GLN | A | 277 | 13.599 | 12.985 | 39.642 | 1.00 36.62 |
| ATOM | 326 | N | GLY | A | 278 | 12.120 | 11.385 | 39.025 | 1.00 38.77 |
| ATOM | 327 | CA | GLY | A | 278 | 10.949 | 12.228 | 39.211 | 1.00 38.88 |
| ATOM | 328 | C | GLY | A | 278 | 10.439 | 12.864 | 37.920 | 1.00 39.33 |
| ATOM | 329 | O | GLY | A | 278 | 9.317 | 13.390 | 37.862 | 1.00 39.32 |
| ATOM | 330 | N | SER | A | 279 | 11.271 | 12.834 | 36.882 | 1.00 39.14 |
| ATOM | 331 | CA | SER | A | 279 | 10.918 | 13.412 | 35.588 | 1.00 39.11 |
| ATOM | 332 | CB | SER | A | 279 | 12.167 | 13.451 | 34.693 | 1.00 39.17 |
| ATOM | 333 | OG | SER | A | 279 | 13.182 | 14.254 | 35.283 | 1.00 37.91 |
| ATOM | 334 | C | SER | A | 279 | 9.783 | 12.620 | 34.934 | 1.00 38.51 |
| ATOM | 335 | O | SER | A | 279 | 8.942 | 13.161 | 34.202 | 1.00 37.96 |
| ATOM | 336 | N | MET | A | 280 | 9.783 | 11.329 | 35.234 | 1.00 37.91 |
| ATOM | 337 | CA | MET | A | 280 | 8.798 | 10.369 | 34.760 | 1.00 37.14 |
| ATOM | 338 | CB | MET | A | 280 | 8.835 | 10.242 | 33.229 | 1.00 37.42 |
| ATOM | 339 | CG | MET | A | 280 | 10.139 | 9.663 | 32.661 | 1.00 37.15 |
| ATOM | 340 | SD | MET | A | 280 | 10.344 | 9.951 | 30.898 | 1.00 36.61 |
| ATOM | 341 | CE | MET | A | 280 | 9.413 | 8.660 | 30.253 | 1.00 37.27 |
| ATOM | 342 | C | MET | A | 280 | 9.181 | 9.046 | 35.433 | 1.00 36.57 |
| ATOM | 343 | O | MET | A | 280 | 10.285 | 8.912 | 35.979 | 1.00 35.47 |
| ATOM | 344 | N | SER | A | 281 | 8.259 | 8.088 | 35.418 | 1.00 36.32 |
| ATOM | 345 | CA | SER | A | 281 | 8.514 | 6.801 | 36.034 | 1.00 36.20 |
| ATOM | 346 | CB | SER | A | 281 | 7.220 | 5.960 | 36.142 | 1.00 34.51 |
| ATOM | 347 | OG | SER | A | 281 | 6.841 | 5.365 | 34.905 | 1.00 32.79 |

Figure 8

| | | | | | | | | |
|---|---|---|---|---|---|---|---|---|
| ATOM | 348 | C | SER | A | 281 | 9.524 | 5.997 | 35.249 | 1.00 | 37.49 |
| ATOM | 349 | O | SER | A | 281 | 9.590 | 6.092 | 34.014 | 1.00 | 38.13 |
| ATOM | 350 | N | PRO | A | 282 | 10.292 | 5.154 | 35.933 | 1.00 | 37.99 |
| ATOM | 351 | CD | PRO | A | 282 | 10.384 | 5.113 | 37.421 | 1.00 | 38.31 |
| ATOM | 352 | CA | PRO | A | 282 | 11.318 | 4.295 | 35.361 | 1.00 | 38.45 |
| ATOM | 353 | CB | PRO | A | 282 | 11.730 | 3.420 | 36.516 | 1.00 | 37.93 |
| ATOM | 354 | CG | PRO | A | 282 | 11.688 | 4.408 | 37.628 | 1.00 | 38.06 |
| ATOM | 355 | C | PRO | A | 282 | 10.827 | 3.436 | 34.208 | 1.00 | 39.44 |
| ATOM | 356 | O | PRO | A | 282 | 11.554 | 3.299 | 33.236 | 1.00 | 40.64 |
| ATOM | 357 | N | ASP | A | 283 | 9.623 | 2.869 | 34.328 | 1.00 | 40.55 |
| ATOM | 358 | CA | ASP | A | 283 | 9.052 | 2.012 | 33.270 | 1.00 | 40.74 |
| ATOM | 359 | CB | ASP | A | 283 | 7.756 | 1.319 | 33.750 | 1.00 | 43.77 |
| ATOM | 360 | CG | ASP | A | 283 | 7.910 | 0.656 | 35.119 | 1.00 | 47.90 |
| ATOM | 361 | OD1 | ASP | A | 283 | 8.895 | -0.093 | 35.329 | 1.00 | 49.54 |
| ATOM | 362 | OD2 | ASP | A | 283 | 7.048 | 0.893 | 35.991 | 1.00 | 50.67 |
| ATOM | 363 | C | ASP | A | 283 | 8.763 | 2.842 | 32.012 | 1.00 | 39.36 |
| ATOM | 364 | O | ASP | A | 283 | 8.876 | 2.350 | 30.888 | 1.00 | 38.24 |
| ATOM | 365 | N | ALA | A | 284 | 8.417 | 4.111 | 32.229 | 1.00 | 38.43 |
| ATOM | 366 | CA | ALA | A | 284 | 8.119 | 5.042 | 31.137 | 1.00 | 37.76 |
| ATOM | 367 | CB | ALA | A | 284 | 7.489 | 6.314 | 31.688 | 1.00 | 37.18 |
| ATOM | 368 | C | ALA | A | 284 | 9.382 | 5.382 | 30.354 | 1.00 | 37.85 |
| ATOM | 369 | O | ALA | A | 284 | 9.353 | 5.505 | 29.124 | 1.00 | 38.73 |
| ATOM | 370 | N | PHE | A | 285 | 10.487 | 5.534 | 31.087 | 1.00 | 37.47 |
| ATOM | 371 | CA | PHE | A | 285 | 11.813 | 5.853 | 30.536 | 1.00 | 34.74 |
| ATOM | 372 | CB | PHE | A | 285 | 12.734 | 6.404 | 31.657 | 1.00 | 32.83 |
| ATOM | 373 | CG | PHE | A | 285 | 14.183 | 6.614 | 31.239 | 1.00 | 30.33 |
| ATOM | 374 | CD1 | PHE | A | 285 | 14.572 | 7.758 | 30.554 | 1.00 | 29.41 |
| ATOM | 375 | CD2 | PHE | A | 285 | 15.163 | 5.677 | 31.559 | 1.00 | 28.34 |
| ATOM | 376 | CE1 | PHE | A | 285 | 15.903 | 7.965 | 30.190 | 1.00 | 27.72 |
| ATOM | 377 | CE2 | PHE | A | 285 | 16.495 | 5.879 | 31.197 | 1.00 | 26.64 |
| ATOM | 378 | CZ | PHE | A | 285 | 16.861 | 7.025 | 30.515 | 1.00 | 26.48 |
| ATOM | 379 | C | PHE | A | 285 | 12.411 | 4.590 | 29.918 | 1.00 | 34.79 |
| ATOM | 380 | O | PHE | A | 285 | 12.909 | 4.649 | 28.791 | 1.00 | 34.46 |
| ATOM | 381 | N | LEU | A | 286 | 12.306 | 3.448 | 30.606 | 1.00 | 35.10 |
| ATOM | 382 | CA | LEU | A | 286 | 12.855 | 2.186 | 30.096 | 1.00 | 37.40 |
| ATOM | 383 | CB | LEU | A | 286 | 12.928 | 1.122 | 31.217 | 1.00 | 36.31 |
| ATOM | 384 | CG | LEU | A | 286 | 14.130 | 1.335 | 32.145 | 1.00 | 37.16 |
| ATOM | 385 | CD1 | LEU | A | 286 | 14.018 | 0.453 | 33.369 | 1.00 | 37.55 |
| ATOM | 386 | CD2 | LEU | A | 286 | 15.447 | 1.092 | 31.400 | 1.00 | 36.40 |
| ATOM | 387 | C | LEU | A | 286 | 12.104 | 1.653 | 28.866 | 1.00 | 39.30 |
| ATOM | 388 | O | LEU | A | 286 | 12.455 | 0.608 | 28.287 | 1.00 | 39.33 |
| ATOM | 389 | N | ALA | A | 287 | 11.175 | 2.485 | 28.389 | 1.00 | 41.74 |
| ATOM | 390 | CA | ALA | A | 287 | 10.334 | 2.154 | 27.249 | 1.00 | 43.21 |
| ATOM | 391 | CB | ALA | A | 287 | 9.050 | 2.936 | 27.308 | 1.00 | 42.49 |
| ATOM | 392 | C | ALA | A | 287 | 11.052 | 2.399 | 25.926 | 1.00 | 44.66 |
| ATOM | 393 | O | ALA | A | 287 | 10.746 | 1.761 | 24.926 | 1.00 | 44.65 |
| ATOM | 394 | N | GLU | A | 288 | 12.061 | 3.267 | 25.961 | 1.00 | 46.28 |
| ATOM | 395 | CA | GLU | A | 288 | 12.825 | 3.586 | 24.761 | 1.00 | 47.59 |
| ATOM | 396 | CB | GLU | A | 288 | 13.833 | 4.714 | 25.019 | 1.00 | 50.68 |
| ATOM | 397 | CG | GLU | A | 288 | 13.307 | 5.895 | 25.825 | 1.00 | 55.33 |
| ATOM | 398 | CD | GLU | A | 288 | 14.212 | 7.110 | 25.710 | 1.00 | 57.69 |
| ATOM | 399 | OE1 | GLU | A | 288 | 14.242 | 7.691 | 24.600 | 1.00 | 57.24 |
| ATOM | 400 | OE2 | GLU | A | 288 | 14.881 | 7.471 | 26.713 | 1.00 | 58.67 |
| ATOM | 401 | C | GLU | A | 288 | 13.589 | 2.321 | 24.362 | 1.00 | 47.10 |
| ATOM | 402 | O | GLU | A | 288 | 13.684 | 2.006 | 23.184 | 1.00 | 47.96 |
| ATOM | 403 | N | ALA | A | 289 | 14.112 | 1.609 | 25.364 | 1.00 | 46.36 |
| ATOM | 404 | CA | ALA | A | 289 | 14.849 | 0.387 | 25.121 | 1.00 | 45.35 |
| ATOM | 405 | CB | ALA | A | 289 | 15.450 | -0.175 | 26.402 | 1.00 | 45.23 |
| ATOM | 406 | C | ALA | A | 289 | 13.937 | -0.641 | 24.503 | 1.00 | 44.55 |
| ATOM | 407 | O | ALA | A | 289 | 14.362 | -1.353 | 23.617 | 1.00 | 44.88 |

Figure 8

| ATOM | 408 | N   | ASN | A | 290 | 12.696 | -0.723 | 24.984 | 1.00 | 43.45 |
| ---- | --- | --- | --- | - | --- | ------ | ------ | ------ | ---- | ----- |
| ATOM | 409 | CA  | ASN | A | 290 | 11.720 | -1.699 | 24.469 | 1.00 | 42.29 |
| ATOM | 410 | CB  | ASN | A | 290 | 10.400 | -1.577 | 25.251 | 1.00 | 43.52 |
| ATOM | 411 | CG  | ASN | A | 290 | 10.515 | -2.116 | 26.671 | 1.00 | 44.44 |
| ATOM | 412 | OD1 | ASN | A | 290 | 9.633  | -1.903 | 27.511 | 1.00 | 44.89 |
| ATOM | 413 | ND2 | ASN | A | 290 | 11.609 | -2.822 | 26.944 | 1.00 | 43.89 |
| ATOM | 414 | C   | ASN | A | 290 | 11.514 | -1.487 | 22.963 | 1.00 | 40.70 |
| ATOM | 415 | O   | ASN | A | 290 | 11.520 | -2.429 | 22.185 | 1.00 | 40.88 |
| ATOM | 416 | N   | LEU | A | 291 | 11.435 | -0.218 | 22.580 | 1.00 | 38.85 |
| ATOM | 417 | CA  | LEU | A | 291 | 11.270 | 0.156  | 21.207 | 1.00 | 37.09 |
| ATOM | 418 | CB  | LEU | A | 291 | 11.027 | 1.653  | 21.088 | 1.00 | 35.93 |
| ATOM | 419 | CG  | LEU | A | 291 | 9.570  | 1.974  | 21.409 | 1.00 | 34.22 |
| ATOM | 420 | CD1 | LEU | A | 291 | 9.352  | 3.442  | 21.738 | 1.00 | 34.08 |
| ATOM | 421 | CD2 | LEU | A | 291 | 8.686  | 1.513  | 20.267 | 1.00 | 34.58 |
| ATOM | 422 | C   | LEU | A | 291 | 12.476 | -0.239 | 20.354 | 1.00 | 36.63 |
| ATOM | 423 | O   | LEU | A | 291 | 12.318 | -0.626 | 19.208 | 1.00 | 36.89 |
| ATOM | 424 | N   | MET | A | 292 | 13.664 | -0.108 | 20.961 | 1.00 | 36.60 |
| ATOM | 425 | CA  | MET | A | 292 | 14.959 | -0.424 | 20.303 | 1.00 | 36.39 |
| ATOM | 426 | CB  | MET | A | 292 | 16.117 | 0.238  | 21.010 | 1.00 | 35.25 |
| ATOM | 427 | CG  | MET | A | 292 | 16.658 | 1.467  | 20.265 | 1.00 | 33.53 |
| ATOM | 428 | SD  | MET | A | 292 | 17.943 | 2.281  | 21.220 | 1.00 | 30.49 |
| ATOM | 429 | CE  | MET | A | 292 | 17.044 | 2.745  | 22.771 | 1.00 | 32.40 |
| ATOM | 430 | C   | MET | A | 292 | 15.192 | -1.936 | 20.107 | 1.00 | 37.76 |
| ATOM | 431 | O   | MET | A | 292 | 15.701 | -2.364 | 19.069 | 1.00 | 38.40 |
| ATOM | 432 | N   | LYS | A | 293 | 14.719 | -2.678 | 21.107 | 1.00 | 39.06 |
| ATOM | 433 | CA  | LYS | A | 293 | 14.747 | -4.142 | 21.070 | 1.00 | 40.23 |
| ATOM | 434 | CB  | LYS | A | 293 | 14.161 | -4.694 | 22.382 | 1.00 | 41.12 |
| ATOM | 435 | CG  | LYS | A | 293 | 14.927 | -4.308 | 23.630 | 1.00 | 42.43 |
| ATOM | 436 | CD  | LYS | A | 293 | 14.168 | -4.720 | 24.897 | 1.00 | 42.68 |
| ATOM | 437 | CE  | LYS | A | 293 | 14.895 | -4.315 | 26.163 | 1.00 | 42.72 |
| ATOM | 438 | NZ  | LYS | A | 293 | 14.325 | -4.933 | 27.391 | 1.00 | 43.14 |
| ATOM | 439 | C   | LYS | A | 293 | 13.820 | -4.619 | 19.916 | 1.00 | 40.75 |
| ATOM | 440 | O   | LYS | A | 293 | 14.208 | -5.428 | 19.082 | 1.00 | 41.55 |
| ATOM | 441 | N   | GLN | A | 294 | 12.607 | -4.069 | 19.888 | 1.00 | 40.89 |
| ATOM | 442 | CA  | GLN | A | 294 | 11.617 | -4.417 | 18.861 | 1.00 | 41.64 |
| ATOM | 443 | CB  | GLN | A | 294 | 10.269 | -3.737 | 19.162 | 1.00 | 43.92 |
| ATOM | 444 | CG  | GLN | A | 294 | 9.701  | -4.072 | 20.533 | 1.00 | 47.75 |
| ATOM | 445 | CD  | GLN | A | 294 | 9.814  | -5.561 | 20.876 | 1.00 | 51.49 |
| ATOM | 446 | OE1 | GLN | A | 294 | 10.436 | -5.944 | 21.885 | 1.00 | 52.37 |
| ATOM | 447 | NE2 | GLN | A | 294 | 9.209  | -6.410 | 20.036 | 1.00 | 52.61 |
| ATOM | 448 | C   | GLN | A | 294 | 12.035 | -4.081 | 17.419 | 1.00 | 40.68 |
| ATOM | 449 | O   | GLN | A | 294 | 11.783 | -4.850 | 16.472 | 1.00 | 41.34 |
| ATOM | 450 | N   | LEU | A | 295 | 12.696 | -2.944 | 17.243 | 1.00 | 39.60 |
| ATOM | 451 | CA  | LEU | A | 295 | 13.131 | -2.504 | 15.927 | 1.00 | 38.25 |
| ATOM | 452 | CB  | LEU | A | 295 | 12.474 | -1.157 | 15.613 | 1.00 | 38.06 |
| ATOM | 453 | CG  | LEU | A | 295 | 10.949 | -1.114 | 15.550 | 1.00 | 36.84 |
| ATOM | 454 | CD1 | LEU | A | 295 | 10.476 | 0.326  | 15.561 | 1.00 | 37.29 |
| ATOM | 455 | CD2 | LEU | A | 295 | 10.471 | -1.842 | 14.304 | 1.00 | 36.25 |
| ATOM | 456 | C   | LEU | A | 295 | 14.645 | -2.404 | 15.747 | 1.00 | 36.86 |
| ATOM | 457 | O   | LEU | A | 295 | 15.277 | -1.499 | 16.292 | 1.00 | 36.59 |
| ATOM | 458 | N   | GLN | A | 296 | 15.212 | -3.317 | 14.959 | 1.00 | 35.67 |
| ATOM | 459 | CA  | GLN | A | 296 | 16.655 | -3.312 | 14.679 | 1.00 | 35.75 |
| ATOM | 460 | CB  | GLN | A | 296 | 17.335 | -4.536 | 15.278 | 1.00 | 35.74 |
| ATOM | 461 | CG  | GLN | A | 296 | 17.304 | -4.556 | 16.787 | 1.00 | 37.95 |
| ATOM | 462 | CD  | GLN | A | 296 | 17.482 | -5.946 | 17.340 | 1.00 | 39.71 |
| ATOM | 463 | OE1 | GLN | A | 296 | 17.419 | -6.927 | 16.606 | 1.00 | 41.80 |
| ATOM | 464 | NE2 | GLN | A | 296 | 17.696 | -6.043 | 18.640 | 1.00 | 41.13 |
| ATOM | 465 | C   | GLN | A | 296 | 16.946 | -3.206 | 13.177 | 1.00 | 34.94 |
| ATOM | 466 | O   | GLN | A | 296 | 16.411 | -3.961 | 12.361 | 1.00 | 34.98 |
| ATOM | 467 | N   | HIS | A | 297.| 17.812 | -2.266 | 12.818 | 1.00 | 33.68 |

Figure 8

| | | | | | | | | |
|---|---|---|---|---|---|---|---|---|
| ATOM | 468 | CA | HIS | A 297 | 18.124 | -2.037 | 11.423 | 1.00 33.03 |
| ATOM | 469 | CB | HIS | A 297 | 16.931 | -1.300 | 10.792 | 1.00 31.82 |
| ATOM | 470 | CG | HIS | A 297 | 17.016 | -1.158 | 9.305 | 1.00 29.79 |
| ATOM | 471 | CD2 | HIS | A 297 | 16.561 | -1.951 | 8.308 | 1.00 28.97 |
| ATOM | 472 | ND1 | HIS | A 297 | 17.655 | -0.102 | 8.691 | 1.00 29.31 |
| ATOM | 473 | CE1 | HIS | A 297 | 17.597 | -0.253 | 7.381 | 1.00 28.13 |
| ATOM | 474 | NE2 | HIS | A 297 | 16.935 | -1.367 | 7.123 | 1.00 28.43 |
| ATOM | 475 | C | HIS | A 297 | 19.390 | -1.189 | 11.326 | 1.00 33.67 |
| ATOM | 476 | O | HIS | A 297 | 19.709 | -0.472 | 12.268 | 1.00 34.08 |
| ATOM | 477 | N | GLN | A 298 | 20.087 | -1.262 | 10.185 | 1.00 34.53 |
| ATOM | 478 | CA | GLN | A 298 | 21.315 | -0.487 | 9.952 | 1.00 36.27 |
| ATOM | 479 | CB | GLN | A 298 | 21.960 | -0.833 | 8.589 | 1.00 40.56 |
| ATOM | 480 | CG | GLN | A 298 | 23.036 | -1.956 | 8.635 | 1.00 48.58 |
| ATOM | 481 | CD | GLN | A 298 | 23.932 | -1.915 | 9.903 | 1.00 52.74 |
| ATOM | 482 | OE1 | GLN | A 298 | 23.931 | -2.863 | 10.712 | 1.00 54.37 |
| ATOM | 483 | NE2 | GLN | A 298 | 24.673 | -0.809 | 10.088 | 1.00 54.29 |
| ATOM | 484 | C | GLN | A 298 | 21.129 | 1.029 | 10.042 | 1.00 34.88 |
| ATOM | 485 | O | GLN | A 298 | 22.065 | 1.762 | 10.382 | 1.00 33.87 |
| ATOM | 486 | N | ARG | A 299 | 19.927 | 1.493 | 9.726 | 1.00 33.43 |
| ATOM | 487 | CA | ARG | A 299 | 19.620 | 2.913 | 9.767 | 1.00 33.31 |
| ATOM | 488 | CB | ARG | A 299 | 18.751 | 3.276 | 8.566 | 1.00 34.83 |
| ATOM | 489 | CG | ARG | A 299 | 19.448 | 3.030 | 7.244 | 1.00 37.10 |
| ATOM | 490 | CD | ARG | A 299 | 20.615 | 3.979 | 7.091 | 1.00 38.76 |
| ATOM | 491 | NE | ARG | A 299 | 21.679 | 3.449 | 6.246 | 1.00 40.88 |
| ATOM | 492 | CZ | ARG | A 299 | 22.972 | 3.529 | 6.556 | 1.00 42.40 |
| ATOM | 493 | NH1 | ARG | A 299 | 23.366 | 4.111 | 7.693 | 1.00 43.00 |
| ATOM | 494 | NH2 | ARG | A 299 | 23.876 | 3.067 | 5.711 | 1.00 42.30 |
| ATOM | 495 | C | ARG | A 299 | 18.962 | 3.357 | 11.081 | 1.00 32.96 |
| ATOM | 496 | O | ARG | A 299 | 18.501 | 4.496 | 11.207 | 1.00 32.72 |
| ATOM | 497 | N | LEU | A 300 | 18.934 | 2.456 | 12.062 | 1.00 32.22 |
| ATOM | 498 | CA | LEU | A 300 | 18.355 | 2.742 | 13.379 | 1.00 31.76 |
| ATOM | 499 | CB | LEU | A 300 | 17.187 | 1.779 | 13.656 | 1.00 31.66 |
| ATOM | 500 | CG | LEU | A 300 | 15.751 | 2.237 | 13.352 | 1.00 31.16 |
| ATOM | 501 | CD1 | LEU | A 300 | 15.630 | 2.857 | 11.972 | 1.00 30.24 |
| ATOM | 502 | CD2 | LEU | A 300 | 14.791 | 1.064 | 13.497 | 1.00 31.99 |
| ATOM | 503 | C | LEU | A 300 | 19.404 | 2.614 | 14.495 | 1.00 31.21 |
| ATOM | 504 | O | LEU | A 300 | 20.257 | 1.726 | 14.451 | 1.00 31.20 |
| ATOM | 505 | N | VAL | A 301 | 19.334 | 3.498 | 15.488 | 1.00 30.95 |
| ATOM | 506 | CA | VAL | A 301 | 20.261 | 3.467 | 16.623 | 1.00 31.58 |
| ATOM | 507 | CB | VAL | A 301 | 20.066 | 4.689 | 17.547 | 1.00 30.56 |
| ATOM | 508 | CG1 | VAL | A 301 | 20.790 | 4.481 | 18.864 | 1.00 30.65 |
| ATOM | 509 | CG2 | VAL | A 301 | 20.597 | 5.940 | 16.861 | 1.00 29.24 |
| ATOM | 510 | C | VAL | A 301 | 20.101 | 2.156 | 17.408 | 1.00 33.20 |
| ATOM | 511 | O | VAL | A 301 | 19.000 | 1.788 | 17.819 | 1.00 32.81 |
| ATOM | 512 | N | ARG | A 302 | 21.220 | 1.467 | 17.613 | 1.00 35.20 |
| ATOM | 513 | CA | ARG | A 302 | 21.254 | 0.173 | 18.288 | 1.00 37.15 |
| ATOM | 514 | CB | ARG | A 302 | 22.330 | -0.707 | 17.609 | 1.00 40.85 |
| ATOM | 515 | CG | ARG | A 302 | 22.476 | -2.133 | 18.109 | 1.00 46.78 |
| ATOM | 516 | CD | ARG | A 302 | 23.337 | -2.164 | 19.371 | 1.00 53.57 |
| ATOM | 517 | NE | ARG | A 302 | 23.908 | -3.481 | 19.660 | 1.00 57.92 |
| ATOM | 518 | CZ | ARG | A 302 | 24.797 | -4.104 | 18.888 | 1.00 59.74 |
| ATOM | 519 | NH1 | ARG | A 302 | 25.226 | -3.539 | 17.761 | 1.00 60.36 |
| ATOM | 520 | NH2 | ARG | A 302 | 25.290 | -5.277 | 19.268 | 1.00 61.00 |
| ATOM | 521 | C | ARG | A 302 | 21.437 | 0.286 | 19.808 | 1.00 36.46 |
| ATOM | 522 | O | ARG | A 302 | 22.165 | 1.146 | 20.311 | 1.00 36.82 |
| ATOM | 523 | N | LEU | A 303 | 20.704 | -0.552 | 20.529 | 1.00 35.68 |
| ATOM | 524 | CA | LEU | A 303 | 20.733 | -0.585 | 21.990 | 1.00 35.02 |
| ATOM | 525 | CB | LEU | A 303 | 19.318 | -0.837 | 22.524 | 1.00 33.88 |
| ATOM | 526 | CG | LEU | A 303 | 19.125 | -1.063 | 24.028 | 1.00 34.20 |
| ATOM | 527 | CD1 | LEU | A 303 | 18.993 | 0.265 | 24.740 | 1.00 32.87 |

Figure 8

| | | | | | | | | | |
|---|---|---|---|---|---|---|---|---|---|
| ATOM | 528 | CD2 | LEU | A | 303 | 17.883 | -1.934 | 24.300 | 1.00 32.48 |
| ATOM | 529 | C | LEU | A | 303 | 21.658 | -1.704 | 22.447 | 1.00 35.53 |
| ATOM | 530 | O | LEU | A | 303 | 21.602 | -2.812 | 21.910 | 1.00 35.47 |
| ATOM | 531 | N | TYR | A | 304 | 22.532 | -1.406 | 23.406 | 1.00 35.77 |
| ATOM | 532 | CA | TYR | A | 304 | 23.461 | -2.401 | 23.938 | 1.00 36.25 |
| ATOM | 533 | CB | TYR | A | 304 | 24.853 | -1.804 | 24.133 | 1.00 38.54 |
| ATOM | 534 | CG | TYR | A | 304 | 25.644 | -1.594 | 22.877 | 1.00 41.24 |
| ATOM | 535 | CD1 | TYR | A | 304 | 26.084 | -0.330 | 22.528 | 1.00 42.69 |
| ATOM | 536 | CE1 | TYR | A | 304 | 26.852 | -0.120 | 21.388 | 1.00 44.67 |
| ATOM | 537 | CD2 | TYR | A | 304 | 25.987 | -2.662 | 22.054 | 1.00 44.24 |
| ATOM | 538 | CE2 | TYR | A | 304 | 26.760 | -2.464 | 20.898 | 1.00 45.76 |
| ATOM | 539 | CZ | TYR | A | 304 | 27.185 | -1.182 | 20.576 | 1.00 45.14 |
| ATOM | 540 | OH | TYR | A | 304 | 27.916 | -0.944 | 19.438 | 1.00 45.03 |
| ATOM | 541 | C | TYR | A | 304 | 22.993 | -2.954 | 25.276 | 1.00 35.67 |
| ATOM | 542 | O | TYR | A | 304 | 23.150 | -4.134 | 25.544 | 1.00 36.61 |
| ATOM | 543 | N | ALA | A | 305 | 22.447 | -2.094 | 26.126 | 1.00 34.58 |
| ATOM | 544 | CA | ALA | A | 305 | 22.000 | -2.520 | 27.438 | 1.00 34.46 |
| ATOM | 545 | CB | ALA | A | 305 | 23.193 | -2.966 | 28.255 | 1.00 33.89 |
| ATOM | 546 | C | ALA | A | 305 | 21.266 | -1.418 | 28.179 | 1.00 35.21 |
| ATOM | 547 | O | ALA | A | 305 | 21.114 | -0.306 | 27.670 | 1.00 35.39 |
| ATOM | 548 | N | VAL | A | 306 | 20.837 | -1.741 | 29.400 | 1.00 35.90 |
| ATOM | 549 | CA | VAL | A | 306 | 20.120 | -0.819 | 30.290 | 1.00 36.94 |
| ATOM | 550 | CB | VAL | A | 306 | 18.554 | -0.909 | 30.090 | 1.00 37.61 |
| ATOM | 551 | CG1 | VAL | A | 306 | 18.148 | -0.656 | 28.639 | 1.00 35.75 |
| ATOM | 552 | CG2 | VAL | A | 306 | 18.034 | -2.270 | 30.532 | 1.00 37.72 |
| ATOM | 553 | C | VAL | A | 306 | 20.423 | -1.162 | 31.766 | 1.00 37.77 |
| ATOM | 554 | O | VAL | A | 306 | 20.686 | -2.320 | 32.097 | 1.00 38.35 |
| ATOM | 555 | N | VAL | A | 307 | 20.449 | -0.153 | 32.634 | 1.00 38.30 |
| ATOM | 556 | CA | VAL | A | 307 | 20.666 | -0.375 | 34.064 | 1.00 39.27 |
| ATOM | 557 | CB | VAL | A | 307 | 21.890 | 0.386 | 34.604 | 1.00 37.83 |
| ATOM | 558 | CG1 | VAL | A | 307 | 21.998 | 0.197 | 36.114 | 1.00 36.12 |
| ATOM | 559 | CG2 | VAL | A | 307 | 23.158 | -0.107 | 33.910 | 1.00 37.71 |
| ATOM | 560 | C | VAL | A | 307 | 19.399 | 0.090 | 34.785 | 1.00 40.93 |
| ATOM | 561 | O | VAL | A | 307 | 19.124 | 1.287 | 34.857 | 1.00 40.82 |
| ATOM | 562 | N | THR | A | 308 | 18.643 | -0.861 | 35.332 | 1.00 43.66 |
| ATOM | 563 | CA | THR | A | 308 | 17.384 | -0.559 | 36.007 | 1.00 46.09 |
| ATOM | 564 | CB | THR | A | 308 | 16.415 | -1.744 | 35.963 | 1.00 45.73 |
| ATOM | 565 | OG1 | THR | A | 308 | 17.065 | -2.900 | 36.494 | 1.00 48.56 |
| ATOM | 566 | CG2 | THR | A | 308 | 15.978 | -2.024 | 34.537 | 1.00 44.29 |
| ATOM | 567 | C | THR | A | 308 | 17.425 | 0.010 | 37.423 | 1.00 47.87 |
| ATOM | 568 | O | THR | A | 308 | 16.377 | 0.340 | 37.965 | 1.00 48.34 |
| ATOM | 569 | N | GLN | A | 309 | 18.598 | 0.103 | 38.044 | 1.00 49.51 |
| ATOM | 570 | CA | GLN | A | 309 | 18.670 | 0.706 | 39.379 | 1.00 51.64 |
| ATOM | 571 | CB | GLN | A | 309 | 19.698 | -0.002 | 40.270 | 1.00 54.89 |
| ATOM | 572 | CG | GLN | A | 309 | 19.277 | -1.406 | 40.712 | 1.00 59.48 |
| ATOM | 573 | CD | GLN | A | 309 | 17.947 | -1.444 | 41.482 | 1.00 61.80 |
| ATOM | 574 | OE1 | GLN | A | 309 | 17.339 | -0.406 | 41.793 | 1.00 62.57 |
| ATOM | 575 | NE2 | GLN | A | 309 | 17.497 | -2.655 | 41.798 | 1.00 63.37 |
| ATOM | 576 | C | GLN | A | 309 | 19.014 | 2.183 | 39.249 | 1.00 51.46 |
| ATOM | 577 | O | GLN | A | 309 | 19.862 | 2.547 | 38.446 | 1.00 51.29 |
| ATOM | 578 | N | GLU | A | 310 | 18.384 | 3.021 | 40.065 | 1.00 51.65 |
| ATOM | 579 | CA | GLU | A | 310 | 18.602 | 4.472 | 40.023 | 1.00 52.62 |
| ATOM | 580 | CB | GLU | A | 310 | 17.611 | 5.190 | 40.954 | 1.00 56.28 |
| ATOM | 581 | CG | GLU | A | 310 | 17.576 | 4.670 | 42.410 | 1.00 61.94 |
| ATOM | 582 | CD | GLU | A | 310 | 16.729 | 3.390 | 42.611 | 1.00 63.96 |
| ATOM | 583 | OE1 | GLU | A | 310 | 15.509 | 3.421 | 42.318 | 1.00 64.50 |
| ATOM | 584 | OE2 | GLU | A | 310 | 17.282 | 2.364 | 43.080 | 1.00 64.35 |
| ATOM | 585 | C | GLU | A | 310 | 20.038 | 4.952 | 40.293 | 1.00 51.16 |
| ATOM | 586 | O | GLU | A | 310 | 20.675 | 4.514 | 41.251 | 1.00 51.58 |
| ATOM | 587 | N | PRO | A | 311 | 20.581 | 5.835 | 39.418 | 1.00 49.34 |

Figure 8

```
ATOM    588  CD   PRO A 311      21.882   6.479  39.659  1.00 49.07
ATOM    589  CA   PRO A 311      19.953   6.402  38.209  1.00 46.90
ATOM    590  CB   PRO A 311      20.933   7.517  37.798  1.00 47.07
ATOM    591  CG   PRO A 311      21.669   7.847  39.061  1.00 48.41
ATOM    592  C    PRO A 311      19.801   5.370  37.078  1.00 44.51
ATOM    593  O    PRO A 311      20.726   4.598  36.795  1.00 44.67
ATOM    594  N    ILE A 312      18.622   5.352  36.455  1.00 41.73
ATOM    595  CA   ILE A 312      18.323   4.432  35.349  1.00 37.49
ATOM    596  CB   ILE A 312      16.817   4.513  34.947  1.00 38.25
ATOM    597  CG2  ILE A 312      16.423   3.295  34.121  1.00 38.04
ATOM    598  CG1  ILE A 312      15.923   4.587  36.185  1.00 38.53
ATOM    599  CD1  ILE A 312      15.837   3.296  36.966  1.00 38.67
ATOM    600  C    ILE A 312      19.177   4.820  34.128  1.00 34.20
ATOM    601  O    ILE A 312      19.360   6.017  33.842  1.00 32.80
ATOM    602  N    TYR A 313      19.701   3.814  33.428  1.00 30.90
ATOM    603  CA   TYR A 313      20.535   4.036  32.241  1.00 28.97
ATOM    604  CB   TYR A 313      21.965   3.532  32.469  1.00 29.75
ATOM    605  CG   TYR A 313      22.855   4.350  33.348  1.00 29.40
ATOM    606  CD1  TYR A 313      22.409   5.537  33.923  1.00 30.35
ATOM    607  CE1  TYR A 313      23.235   6.281  34.775  1.00 32.19
ATOM    608  CD2  TYR A 313      24.151   3.919  33.629  1.00 29.79
ATOM    609  CE2  TYR A 313      24.991   4.652  34.480  1.00 31.62
ATOM    610  CZ   TYR A 313      24.523   5.830  35.054  1.00 32.05
ATOM    611  OH   TYR A 313      25.308   6.531  35.941  1.00 32.13
ATOM    612  C    TYR A 313      20.065   3.311  30.992  1.00 27.25
ATOM    613  O    TYR A 313      19.608   2.178  31.071  1.00 26.76
ATOM    614  N    ILE A 314      20.238   3.948  29.837  1.00 25.59
ATOM    615  CA   ILE A 314      19.923   3.322  28.554  1.00 25.42
ATOM    616  CB   ILE A 314      18.752   4.041  27.789  1.00 25.73
ATOM    617  CG2  ILE A 314      18.745   3.625  26.332  1.00 24.01
ATOM    618  CG1  ILE A 314      17.401   3.678  28.419  1.00 25.22
ATOM    619  CD1  ILE A 314      16.236   4.460  27.881  1.00 26.45
ATOM    620  C    ILE A 314      21.248   3.447  27.813  1.00 25.42
ATOM    621  O    ILE A 314      21.828   4.528  27.763  1.00 27.06
ATOM    622  N    ILE A 315      21.769   2.341  27.303  1.00 24.67
ATOM    623  CA   ILE A 315      23.058   2.393  26.631  1.00 25.00
ATOM    624  CB   ILE A 315      24.099   1.474  27.342  1.00 25.21
ATOM    625  CG2  ILE A 315      25.415   1.439  26.589  1.00 24.22
ATOM    626  CG1  ILE A 315      24.333   1.972  28.760  1.00 24.70
ATOM    627  CD1  ILE A 315      23.458   1.304  29.786  1.00 26.62
ATOM    628  C    ILE A 315      22.976   2.048  25.166  1.00 24.74
ATOM    629  O    ILE A 315      22.574   0.956  24.804  1.00 25.21
ATOM    630  N    THR A 316      23.341   3.002  24.325  1.00 24.34
ATOM    631  CA   THR A 316      23.308   2.772  22.902  1.00 25.41
ATOM    632  CB   THR A 316      22.365   3.758  22.210  1.00 25.29
ATOM    633  OG1  THR A 316      22.936   5.069  22.269  1.00 23.93
ATOM    634  CG2  THR A 316      21.002   3.767  22.894  1.00 24.08
ATOM    635  C    THR A 316      24.691   2.932  22.273  1.00 26.73
ATOM    636  O    THR A 316      25.651   3.382  22.907  1.00 27.72
ATOM    637  N    GLU A 317      24.788   2.536  21.014  1.00 26.42
ATOM    638  CA   GLU A 317      26.014   2.697  20.277  1.00 26.48
ATOM    639  CB   GLU A 317      25.847   2.205  18.833  1.00 26.54
ATOM    640  CG   GLU A 317      24.821   2.980  17.989  1.00 26.56
ATOM    641  CD   GLU A 317      24.696   2.438  16.578  1.00 28.10
ATOM    642  OE1  GLU A 317      23.581   2.030  16.173  1.00 28.33
ATOM    643  OE2  GLU A 317      25.721   2.419  15.861  1.00 29.35
ATOM    644  C    GLU A 317      26.276   4.197  20.289  1.00 27.07
ATOM    645  O    GLU A 317      25.360   5.012  20.512  1.00 27.37
ATOM    646  N    TYR A 318      27.538   4.553  20.096  1.00 26.98
ATOM    647  CA   TYR A 318      27.939   5.939  20.080  1.00 26.33
```

Figure 8

| ATOM | 648 | CB  | TYR A 318 | 29.273 |  6.084 | 20.830 | 1.00 | 26.03 |
| ATOM | 649 | CG  | TYR A 318 | 29.851 |  7.478 | 20.835 | 1.00 | 27.78 |
| ATOM | 650 | CD1 | TYR A 318 | 29.440 |  8.443 | 21.771 | 1.00 | 28.41 |
| ATOM | 651 | CE1 | TYR A 318 | 29.990 |  9.737 | 21.766 | 1.00 | 27.92 |
| ATOM | 652 | CD2 | TYR A 318 | 30.817 |  7.838 | 19.899 | 1.00 | 28.37 |
| ATOM | 653 | CE2 | TYR A 318 | 31.364 |  9.102 | 19.886 | 1.00 | 29.02 |
| ATOM | 654 | CZ  | TYR A 318 | 30.958 | 10.048 | 20.817 | 1.00 | 29.42 |
| ATOM | 655 | OH  | TYR A 318 | 31.586 | 11.279 | 20.795 | 1.00 | 31.14 |
| ATOM | 656 | C   | TYR A 318 | 28.017 |  6.407 | 18.624 | 1.00 | 26.27 |
| ATOM | 657 | O   | TYR A 318 | 28.401 |  5.647 | 17.731 | 1.00 | 26.29 |
| ATOM | 658 | N   | MET A 319 | 27.543 |  7.629 | 18.389 | 1.00 | 26.64 |
| ATOM | 659 | CA  | MET A 319 | 27.546 |  8.252 | 17.070 | 1.00 | 27.16 |
| ATOM | 660 | CB  | MET A 319 | 26.132 |  8.672 | 16.687 | 1.00 | 27.71 |
| ATOM | 661 | CG  | MET A 319 | 25.175 |  7.512 | 16.517 | 1.00 | 26.84 |
| ATOM | 662 | SD  | MET A 319 | 25.683 |  6.412 | 15.199 | 1.00 | 28.43 |
| ATOM | 663 | CE  | MET A 319 | 25.115 |  7.284 | 13.757 | 1.00 | 27.30 |
| ATOM | 664 | C   | MET A 319 | 28.449 |  9.470 | 17.167 | 1.00 | 28.23 |
| ATOM | 665 | O   | MET A 319 | 28.065 | 10.505 | 17.712 | 1.00 | 28.00 |
| ATOM | 666 | N   | GLU A 320 | 29.687 |  9.274 | 16.724 | 1.00 | 30.06 |
| ATOM | 667 | CA  | GLU A 320 | 30.760 | 10.267 | 16.727 | 1.00 | 30.25 |
| ATOM | 668 | CB  | GLU A 320 | 31.831 |  9.816 | 15.740 | 1.00 | 32.62 |
| ATOM | 669 | CG  | GLU A 320 | 33.098 | 10.638 | 15.732 | 1.00 | 38.02 |
| ATOM | 670 | CD  | GLU A 320 | 33.877 | 10.527 | 17.025 | 1.00 | 39.55 |
| ATOM | 671 | OE1 | GLU A 320 | 34.113 |  9.382 | 17.484 | 1.00 | 40.27 |
| ATOM | 672 | OE2 | GLU A 320 | 34.244 | 11.594 | 17.574 | 1.00 | 40.56 |
| ATOM | 673 | C   | GLU A 320 | 30.380 | 11.725 | 16.462 | 1.00 | 29.83 |
| ATOM | 674 | O   | GLU A 320 | 30.756 | 12.609 | 17.233 | 1.00 | 29.75 |
| ATOM | 675 | N   | ASN A 321 | 29.619 | 11.981 | 15.404 | 1.00 | 28.75 |
| ATOM | 676 | CA  | ASN A 321 | 29.236 | 13.354 | 15.088 | 1.00 | 28.53 |
| ATOM | 677 | CB  | ASN A 321 | 29.315 | 13.569 | 13.584 | 1.00 | 28.06 |
| ATOM | 678 | CG  | ASN A 321 | 30.739 | 13.555 | 13.096 | 1.00 | 28.20 |
| ATOM | 679 | OD1 | ASN A 321 | 31.566 | 14.330 | 13.570 | 1.00 | 27.45 |
| ATOM | 680 | ND2 | ASN A 321 | 31.046 | 12.651 | 12.183 | 1.00 | 28.46 |
| ATOM | 681 | C   | ASN A 321 | 27.926 | 13.906 | 15.665 | 1.00 | 28.06 |
| ATOM | 682 | O   | ASN A 321 | 27.429 | 14.946 | 15.217 | 1.00 | 27.65 |
| ATOM | 683 | N   | GLY A 322 | 27.387 | 13.209 | 16.662 | 1.00 | 28.18 |
| ATOM | 684 | CA  | GLY A 322 | 26.162 | 13.626 | 17.326 | 1.00 | 28.85 |
| ATOM | 685 | C   | GLY A 322 | 24.895 | 13.826 | 16.508 | 1.00 | 29.97 |
| ATOM | 686 | O   | GLY A 322 | 24.579 | 13.070 | 15.592 | 1.00 | 30.11 |
| ATOM | 687 | N   | SER A 323 | 24.174 | 14.884 | 16.864 | 1.00 | 30.68 |
| ATOM | 688 | CA  | SER A 323 | 22.912 | 15.258 | 16.245 | 1.00 | 31.02 |
| ATOM | 689 | CB  | SER A 323 | 22.187 | 16.239 | 17.162 | 1.00 | 31.84 |
| ATOM | 690 | OG  | SER A 323 | 20.976 | 16.672 | 16.590 | 1.00 | 35.44 |
| ATOM | 691 | C   | SER A 323 | 23.126 | 15.902 | 14.892 | 1.00 | 30.91 |
| ATOM | 692 | O   | SER A 323 | 23.854 | 16.886 | 14.791 | 1.00 | 31.76 |
| ATOM | 693 | N   | LEU A 324 | 22.422 | 15.395 | 13.876 | 1.00 | 30.30 |
| ATOM | 694 | CA  | LEU A 324 | 22.531 | 15.900 | 12.508 | 1.00 | 30.27 |
| ATOM | 695 | CB  | LEU A 324 | 21.583 | 15.142 | 11.562 | 1.00 | 28.12 |
| ATOM | 696 | CG  | LEU A 324 | 21.409 | 15.674 | 10.123 | 1.00 | 26.96 |
| ATOM | 697 | CD1 | LEU A 324 | 22.690 | 15.537 |  9.315 | 1.00 | 24.74 |
| ATOM | 698 | CD2 | LEU A 324 | 20.283 | 14.935 |  9.431 | 1.00 | 25.87 |
| ATOM | 699 | C   | LEU A 324 | 22.308 | 17.413 | 12.395 | 1.00 | 31.39 |
| ATOM | 700 | O   | LEU A 324 | 23.067 | 18.096 | 11.711 | 1.00 | 32.48 |
| ATOM | 701 | N   | VAL A 325 | 21.310 | 17.941 | 13.100 | 1.00 | 31.72 |
| ATOM | 702 | CA  | VAL A 325 | 21.019 | 19.369 | 13.052 | 1.00 | 32.18 |
| ATOM | 703 | CB  | VAL A 325 | 19.760 | 19.718 | 13.893 | 1.00 | 31.79 |
| ATOM | 704 | CG1 | VAL A 325 | 20.082 | 19.713 | 15.356 | 1.00 | 32.17 |
| ATOM | 705 | CG2 | VAL A 325 | 19.178 | 21.043 | 13.462 | 1.00 | 30.73 |
| ATOM | 706 | C   | VAL A 325 | 22.226 | 20.211 | 13.486 | 1.00 | 32.85 |
| ATOM | 707 | O   | VAL A 325 | 22.435 | 21.313 | 12.971 | 1.00 | 33.17 |

Figure 8

| ATOM | 708 | N   | ASP | A | 326 | 23.040 | 19.661 | 14.391 | 1.00 | 33.60 |
|------|-----|-----|-----|---|-----|--------|--------|--------|------|-------|
| ATOM | 709 | CA  | ASP | A | 326 | 24.251 | 20.337 | 14.878 | 1.00 | 34.35 |
| ATOM | 710 | CB  | ASP | A | 326 | 24.682 | 19.796 | 16.246 | 1.00 | 33.93 |
| ATOM | 711 | CG  | ASP | A | 326 | 23.834 | 20.309 | 17.374 | 1.00 | 32.72 |
| ATOM | 712 | OD1 | ASP | A | 326 | 23.333 | 21.449 | 17.293 | 1.00 | 32.35 |
| ATOM | 713 | OD2 | ASP | A | 326 | 23.694 | 19.567 | 18.361 | 1.00 | 34.07 |
| ATOM | 714 | C   | ASP | A | 326 | 25.431 | 20.169 | 13.908 | 1.00 | 34.92 |
| ATOM | 715 | O   | ASP | A | 326 | 26.182 | 21.117 | 13.673 | 1.00 | 34.99 |
| ATOM | 716 | N   | PHE | A | 327 | 25.591 | 18.959 | 13.370 | 1.00 | 34.66 |
| ATOM | 717 | CA  | PHE | A | 327 | 26.668 | 18.640 | 12.443 | 1.00 | 34.92 |
| ATOM | 718 | CB  | PHE | A | 327 | 26.590 | 17.166 | 12.042 | 1.00 | 35.38 |
| ATOM | 719 | CG  | PHE | A | 327 | 27.675 | 16.738 | 11.082 | 1.00 | 35.86 |
| ATOM | 720 | CD1 | PHE | A | 327 | 29.009 | 16.701 | 11.485 | 1.00 | 36.40 |
| ATOM | 721 | CD2 | PHE | A | 327 | 27.367 | 16.377 | 9.781  | 1.00 | 35.61 |
| ATOM | 722 | CE1 | PHE | A | 327 | 30.017 | 16.312 | 10.602 | 1.00 | 36.02 |
| ATOM | 723 | CE2 | PHE | A | 327 | 28.370 | 15.985 | 8.895  | 1.00 | 35.78 |
| ATOM | 724 | CZ  | PHE | A | 327 | 29.696 | 15.954 | 9.310  | 1.00 | 36.04 |
| ATOM | 725 | C   | PHE | A | 327 | 26.678 | 19.495 | 11.178 | 1.00 | 35.82 |
| ATOM | 726 | O   | PHE | A | 327 | 27.744 | 19.892 | 10.697 | 1.00 | 35.35 |
| ATOM | 727 | N   | LEU | A | 328 | 25.486 | 19.758 | 10.637 | 1.00 | 36.84 |
| ATOM | 728 | CA  | LEU | A | 328 | 25.323 | 20.545 | 9.408  | 1.00 | 36.84 |
| ATOM | 729 | CB  | LEU | A | 328 | 23.864 | 20.548 | 8.938  | 1.00 | 35.59 |
| ATOM | 730 | CG  | LEU | A | 328 | 23.189 | 19.233 | 8.550  | 1.00 | 33.84 |
| ATOM | 731 | CD1 | LEU | A | 328 | 21.689 | 19.462 | 8.465  | 1.00 | 33.77 |
| ATOM | 732 | CD2 | LEU | A | 328 | 23.749 | 18.684 | 7.249  | 1.00 | 31.90 |
| ATOM | 733 | C   | LEU | A | 328 | 25.796 | 21.975 | 9.578  | 1.00 | 37.55 |
| ATOM | 734 | O   | LEU | A | 328 | 26.158 | 22.615 | 8.600  | 1.00 | 38.17 |
| ATOM | 735 | N   | LYS | A | 329 | 25.771 | 22.477 | 10.813 | 1.00 | 38.70 |
| ATOM | 736 | CA  | LYS | A | 329 | 26.219 | 23.837 | 11.090 | 1.00 | 40.04 |
| ATOM | 737 | CB  | LYS | A | 329 | 25.530 | 24.413 | 12.332 | 1.00 | 39.75 |
| ATOM | 738 | CG  | LYS | A | 329 | 24.017 | 24.532 | 12.262 | 1.00 | 40.19 |
| ATOM | 739 | CD  | LYS | A | 329 | 23.524 | 25.373 | 13.426 | 1.00 | 40.62 |
| ATOM | 740 | CE  | LYS | A | 329 | 22.054 | 25.195 | 13.662 | 1.00 | 40.86 |
| ATOM | 741 | NZ  | LYS | A | 329 | 21.775 | 23.802 | 14.092 | 1.00 | 42.74 |
| ATOM | 742 | C   | LYS | A | 329 | 27.734 | 23.947 | 11.267 | 1.00 | 40.99 |
| ATOM | 743 | O   | LYS | A | 329 | 28.273 | 25.051 | 11.133 | 1.00 | 41.48 |
| ATOM | 744 | N   | THR | A | 330 | 28.411 | 22.820 | 11.548 | 1.00 | 41.85 |
| ATOM | 745 | CA  | THR | A | 330 | 29.874 | 22.788 | 11.757 | 1.00 | 42.77 |
| ATOM | 746 | CB  | THR | A | 330 | 30.390 | 21.419 | 12.351 | 1.00 | 42.06 |
| ATOM | 747 | OG1 | THR | A | 330 | 30.254 | 20.374 | 11.380 | 1.00 | 41.70 |
| ATOM | 748 | CG2 | THR | A | 330 | 29.662 | 21.037 | 13.631 | 1.00 | 41.25 |
| ATOM | 749 | C   | THR | A | 330 | 30.639 | 23.032 | 10.458 | 1.00 | 44.32 |
| ATOM | 750 | O   | THR | A | 330 | 30.087 | 22.827 | 9.378  | 1.00 | 45.30 |
| ATOM | 751 | N   | PRO | A | 331 | 31.921 | 23.467 | 10.551 | 1.00 | 45.21 |
| ATOM | 752 | CD  | PRO | A | 331 | 32.619 | 23.791 | 11.811 | 1.00 | 45.59 |
| ATOM | 753 | CA  | PRO | A | 331 | 32.796 | 23.745 | 9.406  | 1.00 | 45.58 |
| ATOM | 754 | CB  | PRO | A | 331 | 34.179 | 23.780 | 10.053 | 1.00 | 45.91 |
| ATOM | 755 | CG  | PRO | A | 331 | 33.902 | 24.459 | 11.329 | 1.00 | 45.93 |
| ATOM | 756 | C   | PRO | A | 331 | 32.717 | 22.657 | 8.341  | 1.00 | 45.92 |
| ATOM | 757 | O   | PRO | A | 331 | 32.580 | 22.958 | 7.154  | 1.00 | 46.26 |
| ATOM | 758 | N   | SER | A | 332 | 32.762 | 21.401 | 8.786  | 1.00 | 46.09 |
| ATOM | 759 | CA  | SER | A | 332 | 32.694 | 20.232 | 7.901  | 1.00 | 47.06 |
| ATOM | 760 | CB  | SER | A | 332 | 33.024 | 18.957 | 8.671  | 1.00 | 47.81 |
| ATOM | 761 | OG  | SER | A | 332 | 34.215 | 19.108 | 9.412  | 1.00 | 50.87 |
| ATOM | 762 | C   | SER | A | 332 | 31.311 | 20.052 | 7.298  | 1.00 | 46.82 |
| ATOM | 763 | O   | SER | A | 332 | 31.181 | 19.649 | 6.141  | 1.00 | 46.15 |
| ATOM | 764 | N   | GLY | A | 333 | 30.289 | 20.284 | 8.123  | 1.00 | 46.91 |
| ATOM | 765 | CA  | GLY | A | 333 | 28.911 | 20.145 | 7.691  | 1.00 | 46.37 |
| ATOM | 766 | C   | GLY | A | 333 | 28.523 | 21.190 | 6.671  | 1.00 | 46.54 |
| ATOM | 767 | O   | GLY | A | 333 | 27.790 | 20.889 | 5.723  | 1.00 | 46.87 |

Figure 8

| ATOM | 768 | N   | ILE | A | 334 | 29.025 | 22.412 | 6.854  | 1.00 | 45.81 |
|------|-----|-----|-----|---|-----|--------|--------|--------|------|-------|
| ATOM | 769 | CA  | ILE | A | 334 | 28.729 | 23.501 | 5.933  | 1.00 | 45.90 |
| ATOM | 770 | CB  | ILE | A | 334 | 29.213 | 24.871 | 6.494  | 1.00 | 45.80 |
| ATOM | 771 | CG2 | ILE | A | 334 | 28.932 | 25.974 | 5.491  | 1.00 | 46.85 |
| ATOM | 772 | CG1 | ILE | A | 334 | 28.467 | 25.234 | 7.788  | 1.00 | 45.91 |
| ATOM | 773 | CD1 | ILE | A | 334 | 27.036 | 25.803 | 7.585  | 1.00 | 46.68 |
| ATOM | 774 | C   | ILE | A | 334 | 29.371 | 23.220 | 4.566  | 1.00 | 46.26 |
| ATOM | 775 | O   | ILE | A | 334 | 28.843 | 23.627 | 3.531  | 1.00 | 46.15 |
| ATOM | 776 | N   | LYS | A | 335 | 30.458 | 22.447 | 4.569  | 1.00 | 46.71 |
| ATOM | 777 | CA  | LYS | A | 335 | 31.186 | 22.096 | 3.346  | 1.00 | 46.99 |
| ATOM | 778 | CB  | LYS | A | 335 | 32.673 | 21.842 | 3.656  | 1.00 | 48.78 |
| ATOM | 779 | CG  | LYS | A | 335 | 33.501 | 23.044 | 4.125  | 1.00 | 50.52 |
| ATOM | 780 | CD  | LYS | A | 335 | 34.793 | 22.547 | 4.792  | 1.00 | 53.47 |
| ATOM | 781 | CE  | LYS | A | 335 | 35.607 | 23.684 | 5.442  | 1.00 | 55.24 |
| ATOM | 782 | NZ  | LYS | A | 335 | 36.521 | 23.183 | 6.534  | 1.00 | 54.86 |
| ATOM | 783 | C   | LYS | A | 335 | 30.634 | 20.878 | 2.585  | 1.00 | 46.52 |
| ATOM | 784 | O   | LYS | A | 335 | 31.083 | 20.596 | 1.471  | 1.00 | 47.06 |
| ATOM | 785 | N   | LEU | A | 336 | 29.706 | 20.129 | 3.182  | 1.00 | 45.51 |
| ATOM | 786 | CA  | LEU | A | 336 | 29.137 | 18.948 | 2.509  | 1.00 | 43.92 |
| ATOM | 787 | CB  | LEU | A | 336 | 28.094 | 18.241 | 3.399  | 1.00 | 43.44 |
| ATOM | 788 | CG  | LEU | A | 336 | 28.539 | 17.514 | 4.674  | 1.00 | 41.90 |
| ATOM | 789 | CD1 | LEU | A | 336 | 27.342 | 17.114 | 5.496  | 1.00 | 40.93 |
| ATOM | 790 | CD2 | LEU | A | 336 | 29.366 | 16.301 | 4.319  | 1.00 | 41.68 |
| ATOM | 791 | C   | LEU | A | 336 | 28.505 | 19.260 | 1.147  | 1.00 | 43.01 |
| ATOM | 792 | O   | LEU | A | 336 | 27.777 | 20.256 | 0.987  | 1.00 | 42.78 |
| ATOM | 793 | N   | THR | A | 337 | 28.771 | 18.383 | 0.180  | 1.00 | 41.71 |
| ATOM | 794 | CA  | THR | A | 337 | 28.231 | 18.542 | -1.166 | 1.00 | 40.92 |
| ATOM | 795 | CB  | THR | A | 337 | 29.078 | 17.771 | -2.252 | 1.00 | 40.77 |
| ATOM | 796 | OG1 | THR | A | 337 | 28.788 | 16.372 | -2.212 | 1.00 | 40.39 |
| ATOM | 797 | CG2 | THR | A | 337 | 30.585 | 17.959 | -2.022 | 1.00 | 40.94 |
| ATOM | 798 | C   | THR | A | 337 | 26.765 | 18.081 | -1.212 | 1.00 | 40.36 |
| ATOM | 799 | O   | THR | A | 337 | 26.316 | 17.315 | -0.345 | 1.00 | 40.24 |
| ATOM | 800 | N   | ILE | A | 338 | 26.032 | 18.571 | -2.215 | 1.00 | 38.79 |
| ATOM | 801 | CA  | ILE | A | 338 | 24.623 | 18.243 | -2.420 | 1.00 | 37.05 |
| ATOM | 802 | CB  | ILE | A | 338 | 24.048 | 18.982 | -3.659 | 1.00 | 35.59 |
| ATOM | 803 | CG2 | ILE | A | 338 | 24.795 | 18.570 | -4.913 | 1.00 | 34.04 |
| ATOM | 804 | CG1 | ILE | A | 338 | 22.557 | 18.669 | -3.832 | 1.00 | 34.80 |
| ATOM | 805 | CD1 | ILE | A | 338 | 21.660 | 19.216 | -2.752 | 1.00 | 32.52 |
| ATOM | 806 | C   | ILE | A | 338 | 24.441 | 16.744 | -2.599 | 1.00 | 37.21 |
| ATOM | 807 | O   | ILE | A | 338 | 23.442 | 16.173 | -2.181 | 1.00 | 37.07 |
| ATOM | 808 | N   | ASN | A | 339 | 25.438 | 16.105 | -3.192 | 1.00 | 37.59 |
| ATOM | 809 | CA  | ASN | A | 339 | 25.406 | 14.672 | -3.424 | 1.00 | 38.00 |
| ATOM | 810 | CB  | ASN | A | 339 | 26.596 | 14.268 | -4.290 | 1.00 | 40.33 |
| ATOM | 811 | CG  | ASN | A | 339 | 26.683 | 15.076 | -5.570 | 1.00 | 41.79 |
| ATOM | 812 | OD1 | ASN | A | 339 | 26.284 | 14.599 | -6.640 | 1.00 | 41.40 |
| ATOM | 813 | ND2 | ASN | A | 339 | 27.205 | 16.310 | -5.470 | 1.00 | 42.28 |
| ATOM | 814 | C   | ASN | A | 339 | 25.464 | 13.914 | -2.108 | 1.00 | 37.76 |
| ATOM | 815 | O   | ASN | A | 339 | 24.780 | 12.903 | -1.937 | 1.00 | 38.90 |
| ATOM | 816 | N   | LYS | A | 340 | 26.316 | 14.379 | -1.198 | 1.00 | 36.84 |
| ATOM | 817 | CA  | LYS | A | 340 | 26.468 | 13.748 | 0.106  | 1.00 | 36.34 |
| ATOM | 818 | CB  | LYS | A | 340 | 27.707 | 14.310 | 0.816  | 1.00 | 37.23 |
| ATOM | 819 | CG  | LYS | A | 340 | 27.952 | 13.747 | 2.218  | 1.00 | 39.62 |
| ATOM | 820 | CD  | LYS | A | 340 | 27.945 | 12.211 | 2.258  | 1.00 | 39.88 |
| ATOM | 821 | CE  | LYS | A | 340 | 27.742 | 11.718 | 3.688  | 1.00 | 40.84 |
| ATOM | 822 | NZ  | LYS | A | 340 | 27.611 | 10.236 | 3.793  | 1.00 | 41.37 |
| ATOM | 823 | C   | LYS | A | 340 | 25.187 | 13.935 | 0.940  | 1.00 | 35.24 |
| ATOM | 824 | O   | LYS | A | 340 | 24.667 | 12.973 | 1.503  | 1.00 | 35.18 |
| ATOM | 825 | N   | LEU | A | 341 | 24.659 | 15.162 | 0.949  | 1.00 | 34.13 |
| ATOM | 826 | CA  | LEU | A | 341 | 23.427 | 15.521 | 1.665  | 1.00 | 32.76 |
| ATOM | 827 | CB  | LEU | A | 341 | 23.058 | 16.992 | 1.393  | 1.00 | 30.36 |

Figure 8

| | | | | | | | | | |
|---|---|---|---|---|---|---|---|---|---|
|ATOM|828|CG|LEU|A|341|23.961|18.106|1.933|1.00 28.41|
|ATOM|829|CD1|LEU|A|341|23.444|19.432|1.479|1.00 27.04|
|ATOM|830|CD2|LEU|A|341|24.017|18.064|3.431|1.00 27.06|
|ATOM|831|C|LEU|A|341|22.252|14.627|1.254|1.00 32.79|
|ATOM|832|O|LEU|A|341|21.535|14.094|2.100|1.00 32.13|
|ATOM|833|N|LEU|A|342|22.055|14.476|-0.052|1.00 33.21|
|ATOM|834|CA|LEU|A|342|20.982|13.635|-0.559|1.00 34.02|
|ATOM|835|CB|LEU|A|342|20.846|13.789|-2.070|1.00 34.28|
|ATOM|836|CG|LEU|A|342|20.121|15.068|-2.484|1.00 34.84|
|ATOM|837|CD1|LEU|A|342|20.255|15.251|-3.945|1.00 35.62|
|ATOM|838|CD2|LEU|A|342|18.652|14.988|-2.120|1.00 36.93|
|ATOM|839|C|LEU|A|342|21.195|12.173|-0.180|1.00 34.17|
|ATOM|840|O|LEU|A|342|20.229|11.434|0.035|1.00 34.30|
|ATOM|841|N|ASP|A|343|22.454|11.756|-0.095|1.00 34.18|
|ATOM|842|CA|ASP|A|343|22.735|10.393|0.299|1.00 34.82|
|ATOM|843|CB|ASP|A|343|24.205|10.039|0.080|1.00 38.10|
|ATOM|844|CG|ASP|A|343|24.508|8.584|0.436|1.00 42.83|
|ATOM|845|OD1|ASP|A|343|23.775|7.669|-0.044|1.00 44.36|
|ATOM|846|OD2|ASP|A|343|25.462|8.365|1.222|1.00 44.80|
|ATOM|847|C|ASP|A|343|22.339|10.223|1.772|1.00 33.78|
|ATOM|848|O|ASP|A|343|21.808|9.176|2.159|1.00 33.99|
|ATOM|849|N|MET|A|344|22.563|11.262|2.580|1.00 32.07|
|ATOM|850|CA|MET|A|344|22.195|11.225|3.996|1.00 31.20|
|ATOM|851|CB|MET|A|344|22.737|12.449|4.740|1.00 32.06|
|ATOM|852|CG|MET|A|344|24.258|12.481|4.889|1.00 33.23|
|ATOM|853|SD|MET|A|344|24.892|13.976|5.752|1.00 34.04|
|ATOM|854|CE|MET|A|344|25.091|13.419|7.409|1.00 32.13|
|ATOM|855|C|MET|A|344|20.664|11.159|4.133|1.00 29.93|
|ATOM|856|O|MET|A|344|20.138|10.388|4.933|1.00 28.97|
|ATOM|857|N|ALA|A|345|19.967|11.953|3.322|1.00 29.22|
|ATOM|858|CA|ALA|A|345|18.506|11.986|3.307|1.00 28.36|
|ATOM|859|CB|ALA|A|345|18.015|13.061|2.333|1.00 27.44|
|ATOM|860|C|ALA|A|345|17.978|10.609|2.896|1.00 27.78|
|ATOM|861|O|ALA|A|345|16.986|10.143|3.435|1.00 27.80|
|ATOM|862|N|ALA|A|346|18.663|9.960|1.954|1.00 27.57|
|ATOM|863|CA|ALA|A|346|18.283|8.630|1.483|1.00 27.33|
|ATOM|864|CB|ALA|A|346|19.159|8.221|0.335|1.00 25.41|
|ATOM|865|C|ALA|A|346|18.378|7.595|2.610|1.00 28.73|
|ATOM|866|O|ALA|A|346|17.589|6.639|2.659|1.00 30.28|
|ATOM|867|N|GLN|A|347|19.342|7.785|3.512|1.00 28.48|
|ATOM|868|CA|GLN|A|347|19.537|6.882|4.651|1.00 27.49|
|ATOM|869|CB|GLN|A|347|20.882|7.142|5.324|1.00 29.36|
|ATOM|870|CG|GLN|A|347|22.072|6.876|4.434|1.00 31.75|
|ATOM|871|CD|GLN|A|347|23.372|7.145|5.133|1.00 32.64|
|ATOM|872|OE1|GLN|A|347|24.243|6.290|5.177|1.00 36.23|
|ATOM|873|NE2|GLN|A|347|23.512|8.329|5.691|1.00 33.41|
|ATOM|874|C|GLN|A|347|18.431|7.010|5.689|1.00 25.67|
|ATOM|875|O|GLN|A|347|18.003|6.021|6.277|1.00 25.27|
|ATOM|876|N|ILE|A|348|18.011|8.240|5.947|1.00 24.25|
|ATOM|877|CA|ILE|A|348|16.946|8.504|6.904|1.00 23.48|
|ATOM|878|CB|ILE|A|348|16.805|10.017|7.167|1.00 22.13|
|ATOM|879|CG2|ILE|A|348|15.625|10.279|8.094|1.00 22.04|
|ATOM|880|CG1|ILE|A|348|18.118|10.567|7.740|1.00 20.24|
|ATOM|881|CD1|ILE|A|348|18.218|12.078|7.761|1.00 16.28|
|ATOM|882|C|ILE|A|348|15.624|7.947|6.358|1.00 23.70|
|ATOM|883|O|ILE|A|348|14.816|7.402|7.116|1.00 23.19|
|ATOM|884|N|ALA|A|349|15.436|8.074|5.040|1.00 23.69|
|ATOM|885|CA|ALA|A|349|14.244|7.586|4.348|1.00 24.29|
|ATOM|886|CB|ALA|A|349|14.218|8.095|2.910|1.00 24.10|
|ATOM|887|C|ALA|A|349|14.212|6.060|4.359|1.00 25.56|

Figure 8

| | | | | | | | | | |
|---|---|---|---|---|---|---|---|---|---|
| ATOM | 888 | O | ALA | A | 349 | 13.139 | 5.452 | 4.413 | 1.00 26.62 |
| ATOM | 889 | N | GLU | A | 350 | 15.398 | 5.450 | 4.300 | 1.00 25.65 |
| ATOM | 890 | CA | GLU | A | 350 | 15.550 | 4.000 | 4.329 | 1.00 25.11 |
| ATOM | 891 | CB | GLU | A | 350 | 16.989 | 3.626 | 4.028 | 1.00 25.93 |
| ATOM | 892 | CG | GLU | A | 350 | 17.240 | 2.149 | 3.925 | 1.00 28.89 |
| ATOM | 893 | CD | GLU | A | 350 | 18.727 | 1.797 | 3.810 | 1.00 31.27 |
| ATOM | 894 | OE1 | GLU | A | 350 | 19.521 | 2.588 | 3.249 | 1.00 30.48 |
| ATOM | 895 | OE2 | GLU | A | 350 | 19.109 | 0.707 | 4.288 | 1.00 33.25 |
| ATOM | 896 | C | GLU | A | 350 | 15.154 | 3.470 | 5.696 | 1.00 25.21 |
| ATOM | 897 | O | GLU | A | 350 | 14.485 | 2.446 | 5.802 | 1.00 26.22 |
| ATOM | 898 | N | GLY | A | 351 | 15.552 | 4.182 | 6.747 | 1.00 24.99 |
| ATOM | 899 | CA | GLY | A | 351 | 15.199 | 3.765 | 8.089 | 1.00 23.89 |
| ATOM | 900 | C | GLY | A | 351 | 13.708 | 3.917 | 8.298 | 1.00 23.28 |
| ATOM | 901 | O | GLY | A | 351 | 13.075 | 3.072 | 8.928 | 1.00 24.29 |
| ATOM | 902 | N | MET | A | 352 | 13.153 | 5.014 | 7.793 | 1.00 23.08 |
| ATOM | 903 | CA | MET | A | 352 | 11.723 | 5.270 | 7.900 | 1.00 22.49 |
| ATOM | 904 | CB | MET | A | 352 | 11.382 | 6.672 | 7.436 | 1.00 19.92 |
| ATOM | 905 | CG | MET | A | 352 | 11.767 | 7.737 | 8.417 | 1.00 18.99 |
| ATOM | 906 | SD | MET | A | 352 | 11.259 | 7.347 | 10.116 | 1.00 21.65 |
| ATOM | 907 | CE | MET | A | 352 | 9.432 | 7.284 | 9.912 | 1.00 19.15 |
| ATOM | 908 | C | MET | A | 352 | 10.944 | 4.262 | 7.080 | 1.00 24.29 |
| ATOM | 909 | O | MET | A | 352 | 9.822 | 3.901 | 7.446 | 1.00 26.14 |
| ATOM | 910 | N | ALA | A | 353 | 11.528 | 3.815 | 5.965 | 1.00 24.72 |
| ATOM | 911 | CA | ALA | A | 353 | 10.894 | 2.811 | 5.110 | 1.00 25.35 |
| ATOM | 912 | CB | ALA | A | 353 | 11.741 | 2.566 | 3.880 | 1.00 24.62 |
| ATOM | 913 | C | ALA | A | 353 | 10.742 | 1.505 | 5.918 | 1.00 26.25 |
| ATOM | 914 | O | ALA | A | 353 | 9.771 | 0.766 | 5.750 | 1.00 26.44 |
| ATOM | 915 | N | PHE | A | 354 | 11.720 | 1.230 | 6.784 | 1.00 26.34 |
| ATOM | 916 | CA | PHE | A | 354 | 11.702 | 0.046 | 7.648 | 1.00 26.35 |
| ATOM | 917 | CB | PHE | A | 354 | 13.075 | -0.148 | 8.319 | 1.00 26.16 |
| ATOM | 918 | CG | PHE | A | 354 | 13.113 | -1.281 | 9.318 | 1.00 25.57 |
| ATOM | 919 | CD1 | PHE | A | 354 | 13.011 | -2.604 | 8.895 | 1.00 24.71 |
| ATOM | 920 | CD2 | PHE | A | 354 | 13.251 | -1.021 | 10.685 | 1.00 25.81 |
| ATOM | 921 | CE1 | PHE | A | 354 | 13.041 | -3.652 | 9.813 | 1.00 25.05 |
| ATOM | 922 | CE2 | PHE | A | 354 | 13.284 | -2.068 | 11.622 | 1.00 26.42 |
| ATOM | 923 | CZ | PHE | A | 354 | 13.179 | -3.386 | 11.181 | 1.00 25.28 |
| ATOM | 924 | C | PHE | A | 354 | 10.635 | 0.226 | 8.719 | 1.00 25.99 |
| ATOM | 925 | O | PHE | A | 354 | 9.896 | -0.695 | 9.037 | 1.00 25.71 |
| ATOM | 926 | N | ILE | A | 355 | 10.584 | 1.416 | 9.296 | 1.00 26.49 |
| ATOM | 927 | CA | ILE | A | 355 | 9.606 | 1.714 | 10.333 | 1.00 27.29 |
| ATOM | 928 | CB | ILE | A | 355 | 9.863 | 3.132 | 10.943 | 1.00 26.76 |
| ATOM | 929 | CG2 | ILE | A | 355 | 8.690 | 3.589 | 11.816 | 1.00 25.82 |
| ATOM | 930 | CG1 | ILE | A | 355 | 11.174 | 3.104 | 11.748 | 1.00 25.77 |
| ATOM | 931 | CD1 | ILE | A | 355 | 11.529 | 4.405 | 12.445 | 1.00 24.43 |
| ATOM | 932 | C | ILE | A | 355 | 8.207 | 1.590 | 9.724 | 1.00 27.95 |
| ATOM | 933 | O | ILE | A | 355 | 7.316 | 0.984 | 10.314 | 1.00 27.90 |
| ATOM | 934 | N | GLU | A | 356 | 8.060 | 2.054 | 8.491 | 1.00 28.64 |
| ATOM | 935 | CA | GLU | A | 356 | 6.782 | 1.994 | 7.793 | 1.00 29.93 |
| ATOM | 936 | CB | GLU | A | 356 | 6.913 | 2.741 | 6.490 | 1.00 27.75 |
| ATOM | 937 | CG | GLU | A | 356 | 5.691 | 2.829 | 5.649 | 1.00 25.70 |
| ATOM | 938 | CD | GLU | A | 356 | 5.998 | 3.610 | 4.410 | 1.00 25.14 |
| ATOM | 939 | OE1 | GLU | A | 356 | 6.676 | 3.058 | 3.517 | 1.00 26.30 |
| ATOM | 940 | OE2 | GLU | A | 356 | 5.627 | 4.792 | 4.354 | 1.00 24.46 |
| ATOM | 941 | C | GLU | A | 356 | 6.417 | 0.546 | 7.516 | 1.00 31.97 |
| ATOM | 942 | O | GLU | A | 356 | 5.304 | 0.104 | 7.777 | 1.00 33.57 |
| ATOM | 943 | N | GLU | A | 357 | 7.389 | -0.173 | 6.982 | 1.00 33.83 |
| ATOM | 944 | CA | GLU | A | 357 | 7.295 | -1.585 | 6.639 | 1.00 35.38 |
| ATOM | 945 | CB | GLU | A | 357 | 8.699 | -2.026 | 6.201 | 1.00 38.21 |
| ATOM | 946 | CG | GLU | A | 357 | 9.022 | -3.479 | 6.317 | 1.00 42.25 |
| ATOM | 947 | CD | GLU | A | 357 | 8.286 | -4.280 | 5.301 | 1.00 45.49 |

Figure 8

| ATOM | 948 | OE1 | GLU | A | 357 | 8.744 | -4.322 | 4.138 | 1.00 | 48.20 |
| --- | --- | --- | --- | --- | --- | --- | --- | --- | --- | --- |
| ATOM | 949 | OE2 | GLU | A | 357 | 7.244 | -4.857 | 5.660 | 1.00 | 47.61 |
| ATOM | 950 | C | GLU | A | 357 | 6.785 | -2.431 | 7.810 | 1.00 | 35.23 |
| ATOM | 951 | O | GLU | A | 357 | 5.910 | -3.274 | 7.643 | 1.00 | 35.34 |
| ATOM | 952 | N | ARG | A | 358 | 7.288 | -2.145 | 9.005 | 1.00 | 35.80 |
| ATOM | 953 | CA | ARG | A | 358 | 6.915 | -2.874 | 10.217 | 1.00 | 36.32 |
| ATOM | 954 | CB | ARG | A | 358 | 8.104 | -2.913 | 11.173 | 1.00 | 37.58 |
| ATOM | 955 | CG | ARG | A | 358 | 9.349 | -3.543 | 10.568 | 1.00 | 42.31 |
| ATOM | 956 | CD | ARG | A | 358 | 9.241 | -5.069 | 10.477 | 1.00 | 46.96 |
| ATOM | 957 | NE | ARG | A | 358 | 9.071 | -5.635 | 11.811 | 1.00 | 52.22 |
| ATOM | 958 | CZ | ARG | A | 358 | 10.006 | -5.604 | 12.763 | 1.00 | 55.41 |
| ATOM | 959 | NH1 | ARG | A | 358 | 11.192 | -5.062 | 12.521 | 1.00 | 57.01 |
| ATOM | 960 | NH2 | ARG | A | 358 | 9.718 | -5.987 | 14.005 | 1.00 | 56.65 |
| ATOM | 961 | C | ARG | A | 358 | 5.705 | -2.272 | 10.923 | 1.00 | 36.08 |
| ATOM | 962 | O | ARG | A | 358 | 5.407 | -2.613 | 12.061 | 1.00 | 35.12 |
| ATOM | 963 | N | ASN | A | 359 | 5.024 | -1.365 | 10.230 | 1.00 | 36.34 |
| ATOM | 964 | CA | ASN | A | 359 | 3.839 | -0.678 | 10.726 | 1.00 | 36.56 |
| ATOM | 965 | CB | ASN | A | 359 | 2.605 | -1.561 | 10.572 | 1.00 | 39.43 |
| ATOM | 966 | CG | ASN | A | 359 | 2.488 | -2.139 | 9.152 | 1.00 | 44.66 |
| ATOM | 967 | OD1 | ASN | A | 359 | 1.995 | -1.475 | 8.218 | 1.00 | 46.05 |
| ATOM | 968 | ND2 | ASN | A | 359 | 2.987 | -3.372 | 8.974 | 1.00 | 46.83 |
| ATOM | 969 | C | ASN | A | 359 | 3.942 | -0.020 | 12.107 | 1.00 | 36.07 |
| ATOM | 970 | O | ASN | A | 359 | 3.174 | -0.300 | 13.036 | 1.00 | 35.93 |
| ATOM | 971 | N | TYR | A | 360 | 4.931 | 0.865 | 12.208 | 1.00 | 34.52 |
| ATOM | 972 | CA | TYR | A | 360 | 5.192 | 1.676 | 13.392 | 1.00 | 33.23 |
| ATOM | 973 | CB | TYR | A | 360 | 6.577 | 1.397 | 13.981 | 1.00 | 32.62 |
| ATOM | 974 | CG | TYR | A | 360 | 6.650 | 0.225 | 14.919 | 1.00 | 33.34 |
| ATOM | 975 | CD1 | TYR | A | 360 | 6.900 | -1.060 | 14.434 | 1.00 | 34.33 |
| ATOM | 976 | CE1 | TYR | A | 360 | 7.008 | -2.155 | 15.293 | 1.00 | 34.24 |
| ATOM | 977 | CD2 | TYR | A | 360 | 6.506 | 0.397 | 16.296 | 1.00 | 33.67 |
| ATOM | 978 | CE2 | TYR | A | 360 | 6.615 | -0.691 | 17.171 | 1.00 | 35.65 |
| ATOM | 979 | CZ | TYR | A | 360 | 6.866 | -1.965 | 16.657 | 1.00 | 35.60 |
| ATOM | 980 | OH | TYR | A | 360 | 6.980 | -3.044 | 17.505 | 1.00 | 37.44 |
| ATOM | 981 | C | TYR | A | 360 | 5.234 | 3.081 | 12.827 | 1.00 | 32.74 |
| ATOM | 982 | O | TYR | A | 360 | 5.164 | 3.271 | 11.606 | 1.00 | 32.36 |
| ATOM | 983 | N | ILE | A | 361 | 5.371 | 4.061 | 13.711 | 1.00 | 31.78 |
| ATOM | 984 | CA | ILE | A | 361 | 5.492 | 5.451 | 13.298 | 1.00 | 30.98 |
| ATOM | 985 | CB | ILE | A | 361 | 4.164 | 6.246 | 13.444 | 1.00 | 30.24 |
| ATOM | 986 | CG2 | ILE | A | 361 | 3.060 | 5.580 | 12.646 | 1.00 | 29.71 |
| ATOM | 987 | CG1 | ILE | A | 361 | 3.765 | 6.387 | 14.906 | 1.00 | 30.01 |
| ATOM | 988 | CD1 | ILE | A | 361 | 2.747 | 7.488 | 15.146 | 1.00 | 30.33 |
| ATOM | 989 | C | ILE | A | 361 | 6.561 | 6.040 | 14.204 | 1.00 | 30.70 |
| ATOM | 990 | O | ILE | A | 361 | 6.820 | 5.497 | 15.273 | 1.00 | 31.81 |
| ATOM | 991 | N | HIS | A | 362 | 7.237 | 7.089 | 13.749 | 1.00 | 29.92 |
| ATOM | 992 | CA | HIS | A | 362 | 8.262 | 7.747 | 14.554 | 1.00 | 28.86 |
| ATOM | 993 | CB | HIS | A | 362 | 9.259 | 8.472 | 13.644 | 1.00 | 26.96 |
| ATOM | 994 | CG | HIS | A | 362 | 10.491 | 8.964 | 14.339 | 1.00 | 25.24 |
| ATOM | 995 | CD2 | HIS | A | 362 | 11.803 | 8.703 | 14.112 | 1.00 | 25.13 |
| ATOM | 996 | ND1 | HIS | A | 362 | 10.464 | 9.883 | 15.363 | 1.00 | 26.50 |
| ATOM | 997 | CE1 | HIS | A | 362 | 11.700 | 10.170 | 15.738 | 1.00 | 25.00 |
| ATOM | 998 | NE2 | HIS | A | 362 | 12.530 | 9.464 | 14.990 | 1.00 | 23.27 |
| ATOM | 999 | C | HIS | A | 362 | 7.564 | 8.759 | 15.457 | 1.00 | 29.12 |
| ATOM | 1000 | O | HIS | A | 362 | 7.674 | 8.695 | 16.688 | 1.00 | 29.78 |
| ATOM | 1001 | N | ARG | A | 363 | 6.846 | 9.674 | 14.810 | 1.00 | 27.97 |
| ATOM | 1002 | CA | ARG | A | 363 | 6.105 | 10.778 | 15.420 | 1.00 | 28.70 |
| ATOM | 1003 | CB | ARG | A | 363 | 5.019 | 10.317 | 16.410 | 1.00 | 31.24 |
| ATOM | 1004 | CG | ARG | A | 363 | 5.469 | 9.843 | 17.766 | 1.00 | 34.59 |
| ATOM | 1005 | CD | ARG | A | 363 | 4.284 | 9.391 | 18.610 | 1.00 | 36.61 |
| ATOM | 1006 | NE | ARG | A | 363 | 3.519 | 10.510 | 19.136 | 1.00 | 37.07 |
| ATOM | 1007 | CZ | ARG | A | 363 | 2.195 | 10.542 | 19.135 | 1.00 | 38.40 |

Figure 8

| ATOM | 1008 | NH1 | ARG A 363 | 1.527 | 9.507 | 18.635 | 1.00 | 38.21 |
|------|------|-----|-----------|-------|-------|--------|------|-------|
| ATOM | 1009 | NH2 | ARG A 363 | 1.546 | 11.599 | 19.617 | 1.00 | 37.83 |
| ATOM | 1010 | C | ARG A 363 | 6.923 | 11.935 | 15.978 | 1.00 | 27.53 |
| ATOM | 1011 | O | ARG A 363 | 6.355 | 12.911 | 16.443 | 1.00 | 26.60 |
| ATOM | 1012 | N | ASP A 364 | 8.251 | 11.837 | 15.891 | 1.00 | 27.29 |
| ATOM | 1013 | CA | ASP A 364 | 9.162 | 12.886 | 16.355 | 1.00 | 26.97 |
| ATOM | 1014 | CB | ASP A 364 | 9.762 | 12.529 | 17.724 | 1.00 | 26.39 |
| ATOM | 1015 | CG | ASP A 364 | 8.780 | 12.707 | 18.870 | 1.00 | 26.46 |
| ATOM | 1016 | OD1 | ASP A 364 | 8.460 | 13.871 | 19.204 | 1.00 | 26.89 |
| ATOM | 1017 | OD2 | ASP A 364 | 8.355 | 11.683 | 19.454 | 1.00 | 26.37 |
| ATOM | 1018 | C | ASP A 364 | 10.288 | 13.079 | 15.317 | 1.00 | 27.42 |
| ATOM | 1019 | O | ASP A 364 | 11.359 | 13.585 | 15.629 | 1.00 | 28.39 |
| ATOM | 1020 | N | LEU A 365 | 10.021 | 12.711 | 14.072 | 1.00 | 26.17 |
| ATOM | 1021 | CA | LEU A 365 | 11.009 | 12.819 | 13.016 | 1.00 | 25.30 |
| ATOM | 1022 | CB | LEU A 365 | 10.536 | 12.041 | 11.786 | 1.00 | 23.24 |
| ATOM | 1023 | CG | LEU A 365 | 11.545 | 11.818 | 10.654 | 1.00 | 23.91 |
| ATOM | 1024 | CD1 | LEU A 365 | 12.718 | 10.912 | 11.080 | 1.00 | 21.13 |
| ATOM | 1025 | CD2 | LEU A 365 | 10.792 | 11.235 | 9.463 | 1.00 | 22.46 |
| ATOM | 1026 | C | LEU A 365 | 11.398 | 14.253 | 12.649 | 1.00 | 25.99 |
| ATOM | 1027 | O | LEU A 365 | 10.570 | 15.061 | 12.225 | 1.00 | 27.30 |
| ATOM | 1028 | N | ARG A 366 | 12.670 | 14.562 | 12.876 | 1.00 | 26.23 |
| ATOM | 1029 | CA | ARG A 366 | 13.265 | 15.860 | 12.575 | 1.00 | 26.01 |
| ATOM | 1030 | CB | ARG A 366 | 12.785 | 16.948 | 13.530 | 1.00 | 26.35 |
| ATOM | 1031 | CG | ARG A 366 | 12.946 | 16.687 | 14.995 | 1.00 | 27.50 |
| ATOM | 1032 | CD | ARG A 366 | 12.615 | 17.959 | 15.750 | 1.00 | 29.86 |
| ATOM | 1033 | NE | ARG A 366 | 12.373 | 17.703 | 17.164 | 1.00 | 34.05 |
| ATOM | 1034 | CZ | ARG A 366 | 11.240 | 17.196 | 17.653 | 1.00 | 34.97 |
| ATOM | 1035 | NH1 | ARG A 366 | 10.226 | 16.898 | 16.842 | 1.00 | 36.96 |
| ATOM | 1036 | NH2 | ARG A 366 | 11.144 | 16.923 | 18.946 | 1.00 | 34.00 |
| ATOM | 1037 | C | ARG A 366 | 14.779 | 15.700 | 12.646 | 1.00 | 25.96 |
| ATOM | 1038 | O | ARG A 366 | 15.270 | 14.760 | 13.264 | 1.00 | 25.16 |
| ATOM | 1039 | N | ALA A 367 | 15.518 | 16.599 | 12.002 | 1.00 | 26.45 |
| ATOM | 1040 | CA | ALA A 367 | 16.984 | 16.520 | 11.978 | 1.00 | 26.07 |
| ATOM | 1041 | CB | ALA A 367 | 17.562 | 17.707 | 11.248 | 1.00 | 25.88 |
| ATOM | 1042 | C | ALA A 367 | 17.640 | 16.359 | 13.352 | 1.00 | 26.40 |
| ATOM | 1043 | O | ALA A 367 | 18.622 | 15.635 | 13.477 | 1.00 | 27.15 |
| ATOM | 1044 | N | ALA A 368 | 17.053 | 16.958 | 14.391 | 1.00 | 26.47 |
| ATOM | 1045 | CA | ALA A 368 | 17.596 | 16.865 | 15.755 | 1.00 | 25.82 |
| ATOM | 1046 | CB | ALA A 368 | 16.809 | 17.741 | 16.703 | 1.00 | 25.15 |
| ATOM | 1047 | C | ALA A 368 | 17.613 | 15.438 | 16.279 | 1.00 | 25.89 |
| ATOM | 1048 | O | ALA A 368 | 18.434 | 15.097 | 17.125 | 1.00 | 25.41 |
| ATOM | 1049 | N | ASN A 369 | 16.718 | 14.606 | 15.752 | 1.00 | 26.34 |
| ATOM | 1050 | CA | ASN A 369 | 16.612 | 13.207 | 16.168 | 1.00 | 26.83 |
| ATOM | 1051 | CB | ASN A 369 | 15.145 | 12.822 | 16.412 | 1.00 | 27.17 |
| ATOM | 1052 | CG | ASN A 369 | 14.505 | 13.681 | 17.496 | 1.00 | 28.07 |
| ATOM | 1053 | OD1 | ASN A 369 | 15.104 | 13.909 | 18.549 | 1.00 | 28.53 |
| ATOM | 1054 | ND2 | ASN A 369 | 13.336 | 14.224 | 17.216 | 1.00 | 25.55 |
| ATOM | 1055 | C | ASN A 369 | 17.307 | 12.209 | 15.252 | 1.00 | 26.36 |
| ATOM | 1056 | O | ASN A 369 | 17.014 | 11.022 | 15.288 | 1.00 | 27.21 |
| ATOM | 1057 | N | ILE A 370 | 18.203 | 12.706 | 14.405 | 1.00 | 25.68 |
| ATOM | 1058 | CA | ILE A 370 | 18.992 | 11.846 | 13.528 | 1.00 | 24.88 |
| ATOM | 1059 | CB | ILE A 370 | 18.923 | 12.294 | 12.057 | 1.00 | 24.39 |
| ATOM | 1060 | CG2 | ILE A 370 | 19.806 | 11.393 | 11.203 | 1.00 | 22.63 |
| ATOM | 1061 | CG1 | ILE A 370 | 17.467 | 12.297 | 11.563 | 1.00 | 22.80 |
| ATOM | 1062 | CD1 | ILE A 370 | 16.817 | 10.942 | 11.545 | 1.00 | 20.70 |
| ATOM | 1063 | C | ILE A 370 | 20.441 | 11.975 | 14.032 | 1.00 | 25.26 |
| ATOM | 1064 | O | ILE A 370 | 20.887 | 13.079 | 14.371 | 1.00 | 24.23 |
| ATOM | 1065 | N | LEU A 371 | 21.153 | 10.852 | 14.133 | 1.00 | 25.28 |
| ATOM | 1066 | CA | LEU A 371 | 22.534 | 10.880 | 14.625 | 1.00 | 25.00 |
| ATOM | 1067 | CB | LEU A 371 | 22.717 | 9.916 | 15.804 | 1.00 | 23.13 |

Figure 8

| | | | | | | | | | |
|---|---|---|---|---|---|---|---|---|---|
| ATOM | 1068 | CG | LEU | A | 371 | 21.829 | 10.151 | 17.029 | 1.00 21.42 |
| ATOM | 1069 | CD1 | LEU | A | 371 | 22.057 | 9.050 | 18.029 | 1.00 20.36 |
| ATOM | 1070 | CD2 | LEU | A | 371 | 22.096 | 11.511 | 17.640 | 1.00 19.56 |
| ATOM | 1071 | C | LEU | A | 371 | 23.493 | 10.553 | 13.496 | 1.00 25.89 |
| ATOM | 1072 | O | LEU | A | 371 | 23.156 | 9.763 | 12.614 | 1.00 26.21 |
| ATOM | 1073 | N | VAL | A | 372 | 24.659 | 11.200 | 13.501 | 1.00 26.46 |
| ATOM | 1074 | CA | VAL | A | 372 | 25.687 | 11.016 | 12.470 | 1.00 28.18 |
| ATOM | 1075 | CB | VAL | A | 372 | 26.137 | 12.396 | 11.908 | 1.00 27.75 |
| ATOM | 1076 | CG1 | VAL | A | 372 | 27.028 | 12.232 | 10.697 | 1.00 26.76 |
| ATOM | 1077 | CG2 | VAL | A | 372 | 24.935 | 13.242 | 11.577 | 1.00 26.88 |
| ATOM | 1078 | C | VAL | A | 372 | 26.921 | 10.265 | 13.020 | 1.00 29.94 |
| ATOM | 1079 | O | VAL | A | 372 | 27.468 | 10.624 | 14.063 | 1.00 30.51 |
| ATOM | 1080 | N | SER | A | 373 | 27.350 | 9.214 | 12.331 | 1.00 31.15 |
| ATOM | 1081 | CA | SER | A | 373 | 28.507 | 8.451 | 12.775 | 1.00 32.68 |
| ATOM | 1082 | CB | SER | A | 373 | 28.467 | 7.048 | 12.178 | 1.00 32.47 |
| ATOM | 1083 | OG | SER | A | 373 | 28.755 | 7.078 | 10.789 | 1.00 32.87 |
| ATOM | 1084 | C | SER | A | 373 | 29.777 | 9.145 | 12.316 | 1.00 34.38 |
| ATOM | 1085 | O | SER | A | 373 | 29.718 | 10.143 | 11.606 | 1.00 33.96 |
| ATOM | 1086 | N | ASP | A | 374 | 30.923 | 8.606 | 12.716 | 1.00 36.40 |
| ATOM | 1087 | CA | ASP | A | 374 | 32.209 | 9.163 | 12.307 | 1.00 38.47 |
| ATOM | 1088 | CB | ASP | A | 374 | 33.358 | 8.492 | 13.062 | 1.00 39.95 |
| ATOM | 1089 | CG | ASP | A | 374 | 33.189 | 6.992 | 13.166 | 1.00 41.84 |
| ATOM | 1090 | OD1 | ASP | A | 374 | 32.582 | 6.529 | 14.166 | 1.00 44.83 |
| ATOM | 1091 | OD2 | ASP | A | 374 | 33.648 | 6.282 | 12.248 | 1.00 41.86 |
| ATOM | 1092 | C | ASP | A | 374 | 32.414 | 9.028 | 10.798 | 1.00 38.86 |
| ATOM | 1093 | O | ASP | A | 374 | 33.116 | 9.837 | 10.199 | 1.00 39.44 |
| ATOM | 1094 | N | THR | A | 375 | 31.781 | 8.020 | 10.190 | 1.00 39.13 |
| ATOM | 1095 | CA | THR | A | 375 | 31.874 | 7.792 | 8.743 | 1.00 38.96 |
| ATOM | 1096 | CB | THR | A | 375 | 31.688 | 6.307 | 8.374 | 1.00 39.23 |
| ATOM | 1097 | OG1 | THR | A | 375 | 30.421 | 5.844 | 8.860 | 1.00 39.55 |
| ATOM | 1098 | CG2 | THR | A | 375 | 32.814 | 5.460 | 8.972 | 1.00 40.18 |
| ATOM | 1099 | C | THR | A | 375 | 30.816 | 8.600 | 7.996 | 1.00 38.85 |
| ATOM | 1100 | O | THR | A | 375 | 30.601 | 8.404 | 6.802 | 1.00 39.19 |
| ATOM | 1101 | N | LEU | A | 376 | 30.149 | 9.489 | 8.726 | 1.00 38.41 |
| ATOM | 1102 | CA | LEU | A | 376 | 29.100 | 10.366 | 8.207 | 1.00 37.68 |
| ATOM | 1103 | CB | LEU | A | 376 | 29.650 | 11.302 | 7.132 | 1.00 37.38 |
| ATOM | 1104 | CG | LEU | A | 376 | 30.929 | 12.085 | 7.447 | 1.00 38.43 |
| ATOM | 1105 | CD1 | LEU | A | 376 | 30.913 | 13.350 | 6.615 | 1.00 38.13 |
| ATOM | 1106 | CD2 | LEU | A | 376 | 31.035 | 12.446 | 8.912 | 1.00 38.72 |
| ATOM | 1107 | C | LEU | A | 376 | 27.796 | 9.704 | 7.732 | 1.00 37.41 |
| ATOM | 1108 | O | LEU | A | 376 | 27.080 | 10.266 | 6.900 | 1.00 37.45 |
| ATOM | 1109 | N | SER | A | 377 | 27.486 | 8.517 | 8.256 | 1.00 36.24 |
| ATOM | 1110 | CA | SER | A | 377 | 26.238 | 7.843 | 7.905 | 1.00 35.28 |
| ATOM | 1111 | CB | SER | A | 377 | 26.438 | 6.331 | 7.796 | 1.00 36.10 |
| ATOM | 1112 | OG | SER | A | 377 | 26.670 | 5.758 | 9.074 | 1.00 38.53 |
| ATOM | 1113 | C | SER | A | 377 | 25.181 | 8.168 | 8.984 | 1.00 34.33 |
| ATOM | 1114 | O | SER | A | 377 | 25.517 | 8.354 | 10.169 | 1.00 32.91 |
| ATOM | 1115 | N | CYS | A | 378 | 23.909 | 8.218 | 8.578 | 1.00 33.03 |
| ATOM | 1116 | CA | CYS | A | 378 | 22.826 | 8.545 | 9.501 | 1.00 30.69 |
| ATOM | 1117 | CB | CYS | A | 378 | 21.871 | 9.541 | 8.846 | 1.00 29.83 |
| ATOM | 1118 | SG | CYS | A | 378 | 22.664 | 11.033 | 8.222 | 1.00 27.59 |
| ATOM | 1119 | C | CYS | A | 378 | 22.034 | 7.355 | 10.060 | 1.00 30.32 |
| ATOM | 1120 | O | CYS | A | 378 | 21.815 | 6.345 | 9.374 | 1.00 30.88 |
| ATOM | 1121 | N | LYS | A | 379 | 21.637 | 7.497 | 11.328 | 1.00 28.67 |
| ATOM | 1122 | CA | LYS | A | 379 | 20.851 | 6.512 | 12.072 | 1.00 26.94 |
| ATOM | 1123 | CB | LYS | A | 379 | 21.724 | 5.766 | 13.094 | 1.00 25.70 |
| ATOM | 1124 | CG | LYS | A | 379 | 22.408 | 4.511 | 12.545 | 1.00 27.54 |
| ATOM | 1125 | CD | LYS | A | 379 | 23.668 | 4.136 | 13.328 | 1.00 29.36 |
| ATOM | 1126 | CE | LYS | A | 379 | 24.372 | 2.882 | 12.771 | 1.00 29.80 |
| ATOM | 1127 | NZ | LYS | A | 379 | 23.691 | 1.598 | 13.198 | 1.00 33.69 |

Figure 8

```
ATOM   1128  C    LYS A 379      19.725   7.295  12.768  1.00 26.70
ATOM   1129  O    LYS A 379      19.930   8.430  13.233  1.00 26.67
ATOM   1130  N    ILE A 380      18.530   6.709  12.791  1.00 26.01
ATOM   1131  CA   ILE A 380      17.347   7.344  13.391  1.00 25.37
ATOM   1132  CB   ILE A 380      16.030   6.844  12.696  1.00 25.11
ATOM   1133  CG2  ILE A 380      14.805   7.477  13.326  1.00 23.88
ATOM   1134  CG1  ILE A 380      16.055   7.169  11.206  1.00 24.52
ATOM   1135  CD1  ILE A 380      14.900   6.618  10.490  1.00 23.76
ATOM   1136  C    ILE A 380      17.269   7.030  14.885  1.00 24.61
ATOM   1137  O    ILE A 380      17.407   5.871  15.286  1.00 24.46
ATOM   1138  N    ALA A 381      17.051   8.057  15.702  1.00 23.77
ATOM   1139  CA   ALA A 381      16.947   7.864  17.143  1.00 22.98
ATOM   1140  CB   ALA A 381      18.029   8.635  17.861  1.00 21.65
ATOM   1141  C    ALA A 381      15.589   8.328  17.620  1.00 23.84
ATOM   1142  O    ALA A 381      14.855   8.982  16.882  1.00 22.57
ATOM   1143  N    ASP A 382      15.274   7.992  18.870  1.00 25.69
ATOM   1144  CA   ASP A 382      14.018   8.373  19.524  1.00 26.94
ATOM   1145  CB   ASP A 382      14.120   9.801  20.048  1.00 27.03
ATOM   1146  CG   ASP A 382      14.995   9.888  21.260  1.00 27.83
ATOM   1147  OD1  ASP A 382      14.653   9.238  22.266  1.00 31.05
ATOM   1148  OD2  ASP A 382      16.036  10.564  21.215  1.00 28.84
ATOM   1149  C    ASP A 382      12.725   8.163  18.742  1.00 27.76
ATOM   1150  O    ASP A 382      11.794   8.965  18.819  1.00 27.29
ATOM   1151  N    PHE A 383      12.640   6.994  18.113  1.00 28.80
ATOM   1152  CA   PHE A 383      11.501   6.605  17.298  1.00 29.73
ATOM   1153  CB   PHE A 383      11.999   5.826  16.075  1.00 28.35
ATOM   1154  CG   PHE A 383      12.886   4.656  16.418  1.00 28.60
ATOM   1155  CD1  PHE A 383      12.347   3.431  16.805  1.00 29.39
ATOM   1156  CD2  PHE A 383      14.268   4.784  16.372  1.00 28.34
ATOM   1157  CE1  PHE A 383      13.185   2.357  17.143  1.00 29.04
ATOM   1158  CE2  PHE A 383      15.114   3.716  16.706  1.00 27.59
ATOM   1159  CZ   PHE A 383      14.571   2.506  17.090  1.00 28.08
ATOM   1160  C    PHE A 383      10.468   5.757  18.044  1.00 30.92
ATOM   1161  O    PHE A 383      10.790   5.058  19.011  1.00 31.35
ATOM   1162  N    GLY A 384       9.225   5.823  17.582  1.00 31.40
ATOM   1163  CA   GLY A 384       8.178   5.025  18.181  1.00 32.32
ATOM   1164  C    GLY A 384       7.694   5.408  19.559  1.00 33.21
ATOM   1165  O    GLY A 384       7.010   4.612  20.174  1.00 33.93
ATOM   1166  N    LEU A 385       8.061   6.578  20.074  1.00 34.83
ATOM   1167  CA   LEU A 385       7.583   6.997  21.397  1.00 35.97
ATOM   1168  CB   LEU A 385       8.334   8.237  21.890  1.00 35.28
ATOM   1169  CG   LEU A 385       9.844   8.077  22.074  1.00 35.84
ATOM   1170  CD1  LEU A 385      10.401   9.316  22.724  1.00 36.00
ATOM   1171  CD2  LEU A 385      10.159   6.862  22.912  1.00 36.19
ATOM   1172  C    LEU A 385       6.082   7.292  21.363  1.00 37.46
ATOM   1173  O    LEU A 385       5.533   7.661  20.330  1.00 36.71
ATOM   1174  N    ALA A 386       5.416   7.099  22.498  1.00 39.30
ATOM   1175  CA   ALA A 386       3.977   7.346  22.601  1.00 39.96
ATOM   1176  CB   ALA A 386       3.412   6.654  23.847  1.00 40.37
ATOM   1177  C    ALA A 386       3.717   8.847  22.676  1.00 40.10
ATOM   1178  O    ALA A 386       2.686   9.342  22.216  1.00 41.29
ATOM   1179  N    ARG A 387       4.684   9.566  23.241  1.00 39.04
ATOM   1180  CA   ARG A 387       4.590  11.007  23.413  1.00 36.60
ATOM   1181  CB   ARG A 387       5.032  11.357  24.828  1.00 35.66
ATOM   1182  CG   ARG A 387       6.483  10.984  25.101  1.00 34.58
ATOM   1183  CD   ARG A 387       6.860  11.320  26.505  1.00 34.00
ATOM   1184  NE   ARG A 387       8.290  11.216  26.728  1.00 33.69
ATOM   1185  CZ   ARG A 387       9.114  12.256  26.698  1.00 34.83
ATOM   1186  NH1  ARG A 387       8.642  13.477  26.458  1.00 34.58
ATOM   1187  NH2  ARG A 387      10.415  12.073  26.880  1.00 35.04
```

Figure 8

| ATOM | 1188 | C | ARG | A | 387 | 5.425 | 11.826 | 22.421 | 1.00 | 35.20 |
| ATOM | 1189 | O | ARG | A | 387 | 6.266 | 11.303 | 21.692 | 1.00 | 34.43 |
| ATOM | 1190 | N | LEU | A | 388 | 5.198 | 13.134 | 22.465 | 1.00 | 33.69 |
| ATOM | 1191 | CA | LEU | A | 388 | 5.904 | 14.100 | 21.654 | 1.00 | 31.96 |
| ATOM | 1192 | CB | LEU | A | 388 | 4.940 | 15.194 | 21.219 | 1.00 | 31.42 |
| ATOM | 1193 | CG | LEU | A | 388 | 3.715 | 14.584 | 20.519 | 1.00 | 33.80 |
| ATOM | 1194 | CD1 | LEU | A | 388 | 2.717 | 15.660 | 20.112 | 1.00 | 34.04 |
| ATOM | 1195 | CD2 | LEU | A | 388 | 4.137 | 13.779 | 19.295 | 1.00 | 34.37 |
| ATOM | 1196 | C | LEU | A | 388 | 7.021 | 14.644 | 22.553 | 1.00 | 30.91 |
| ATOM | 1197 | O | LEU | A | 388 | 6.775 | 15.026 | 23.702 | 1.00 | 30.61 |
| ATOM | 1198 | N | ILE | A | 389 | 8.259 | 14.587 | 22.062 | 1.00 | 29.95 |
| ATOM | 1199 | CA | ILE | A | 389 | 9.413 | 15.039 | 22.839 | 1.00 | 29.27 |
| ATOM | 1200 | CB | ILE | A | 389 | 10.553 | 13.983 | 22.828 | 1.00 | 26.88 |
| ATOM | 1201 | CG2 | ILE | A | 389 | 10.009 | 12.616 | 23.190 | 1.00 | 25.49 |
| ATOM | 1202 | CG1 | ILE | A | 389 | 11.236 | 13.937 | 21.453 | 1.00 | 26.31 |
| ATOM | 1203 | CD1 | ILE | A | 389 | 12.241 | 12.817 | 21.277 | 1.00 | 23.98 |
| ATOM | 1204 | C | ILE | A | 389 | 9.985 | 16.398 | 22.442 | 1.00 | 30.91 |
| ATOM | 1205 | O | ILE | A | 389 | 9.799 | 16.877 | 21.328 | 1.00 | 31.52 |
| ATOM | 1206 | N | GLU | A | 390 | 10.697 | 17.014 | 23.372 | 1.00 | 33.14 |
| ATOM | 1207 | CA | GLU | A | 390 | 11.322 | 18.301 | 23.127 | 1.00 | 35.16 |
| ATOM | 1208 | CB | GLU | A | 390 | 10.834 | 19.334 | 24.139 | 1.00 | 36.75 |
| ATOM | 1209 | CG | GLU | A | 390 | 9.398 | 19.729 | 23.932 | 1.00 | 39.23 |
| ATOM | 1210 | CD | GLU | A | 390 | 8.887 | 20.659 | 24.998 | 1.00 | 42.07 |
| ATOM | 1211 | OE1 | GLU | A | 390 | 7.657 | 20.809 | 25.100 | 1.00 | 44.84 |
| ATOM | 1212 | OE2 | GLU | A | 390 | 9.697 | 21.237 | 25.744 | 1.00 | 43.78 |
| ATOM | 1213 | C | GLU | A | 390 | 12.832 | 18.168 | 23.196 | 1.00 | 35.86 |
| ATOM | 1214 | O | GLU | A | 390 | 13.358 | 17.281 | 23.862 | 1.00 | 34.38 |
| ATOM | 1215 | N | ASP | A | 391 | 13.520 | 19.066 | 22.498 | 1.00 | 38.40 |
| ATOM | 1216 | CA | ASP | A | 391 | 14.984 | 19.076 | 22.439 | 1.00 | 40.09 |
| ATOM | 1217 | CB | ASP | A | 391 | 15.443 | 19.974 | 21.279 | 1.00 | 41.93 |
| ATOM | 1218 | CG | ASP | A | 391 | 14.991 | 19.452 | 19.923 | 1.00 | 44.26 |
| ATOM | 1219 | OD1 | ASP | A | 391 | 14.664 | 18.241 | 19.807 | 1.00 | 46.06 |
| ATOM | 1220 | OD2 | ASP | A | 391 | 14.968 | 20.257 | 18.968 | 1.00 | 46.05 |
| ATOM | 1221 | C | ASP | A | 391 | 15.719 | 19.462 | 23.733 | 1.00 | 39.70 |
| ATOM | 1222 | O | ASP | A | 391 | 16.908 | 19.168 | 23.891 | 1.00 | 40.11 |
| ATOM | 1223 | N | ASN | A | 392 | 15.000 | 20.092 | 24.656 | 1.00 | 38.98 |
| ATOM | 1224 | CA | ASN | A | 392 | 15.562 | 20.539 | 25.929 | 1.00 | 38.24 |
| ATOM | 1225 | CB | ASN | A | 392 | 14.927 | 21.887 | 26.339 | 1.00 | 39.14 |
| ATOM | 1226 | CG | ASN | A | 392 | 13.443 | 21.762 | 26.785 | 1.00 | 40.35 |
| ATOM | 1227 | OD1 | ASN | A | 392 | 12.815 | 20.697 | 26.674 | 1.00 | 40.19 |
| ATOM | 1228 | ND2 | ASN | A | 392 | 12.895 | 22.860 | 27.304 | 1.00 | 39.69 |
| ATOM | 1229 | C | ASN | A | 392 | 15.407 | 19.515 | 27.061 | 1.00 | 37.34 |
| ATOM | 1230 | O | ASN | A | 392 | 15.537 | 19.856 | 28.241 | 1.00 | 37.61 |
| ATOM | 1231 | N | GLU | A | 393 | 15.137 | 18.264 | 26.705 | 1.00 | 35.98 |
| ATOM | 1232 | CA | GLU | A | 393 | 14.943 | 17.232 | 27.709 | 1.00 | 34.86 |
| ATOM | 1233 | CB | GLU | A | 393 | 13.972 | 16.179 | 27.187 | 1.00 | 33.73 |
| ATOM | 1234 | CG | GLU | A | 393 | 12.572 | 16.733 | 26.918 | 1.00 | 31.82 |
| ATOM | 1235 | CD | GLU | A | 393 | 11.608 | 15.673 | 26.432 | 1.00 | 30.67 |
| ATOM | 1236 | OE1 | GLU | A | 393 | 12.053 | 14.533 | 26.169 | 1.00 | 30.33 |
| ATOM | 1237 | OE2 | GLU | A | 393 | 10.400 | 15.975 | 26.322 | 1.00 | 31.63 |
| ATOM | 1238 | C | GLU | A | 393 | 16.227 | 16.591 | 28.215 | 1.00 | 34.95 |
| ATOM | 1239 | O | GLU | A | 393 | 16.362 | 16.306 | 29.402 | 1.00 | 34.24 |
| ATOM | 1240 | N | TYR | A | 394 | 17.181 | 16.385 | 27.319 | 1.00 | 35.38 |
| ATOM | 1241 | CA | TYR | A | 394 | 18.444 | 15.786 | 27.706 | 1.00 | 35.93 |
| ATOM | 1242 | CB | TYR | A | 394 | 18.540 | 14.352 | 27.186 | 1.00 | 34.01 |
| ATOM | 1243 | CG | TYR | A | 394 | 17.455 | 13.456 | 27.725 | 1.00 | 31.60 |
| ATOM | 1244 | CD1 | TYR | A | 394 | 16.236 | 13.349 | 27.081 | 1.00 | 31.15 |
| ATOM | 1245 | CE1 | TYR | A | 394 | 15.221 | 12.552 | 27.595 | 1.00 | 31.37 |
| ATOM | 1246 | CD2 | TYR | A | 394 | 17.637 | 12.740 | 28.898 | 1.00 | 31.68 |
| ATOM | 1247 | CE2 | TYR | A | 394 | 16.631 | 11.936 | 29.425 | 1.00 | 31.23 |

Figure 8

| | | | | | | | | | |
|---|---|---|---|---|---|---|---|---|---|
| ATOM | 1248 | CZ | TYR | A | 394 | 15.422 | 11.845 | 28.768 | 1.00 31.41 |
| ATOM | 1249 | OH | TYR | A | 394 | 14.418 | 11.046 | 29.275 | 1.00 29.87 |
| ATOM | 1250 | C | TYR | A | 394 | 19.645 | 16.618 | 27.266 | 1.00 38.03 |
| ATOM | 1251 | O | TYR | A | 394 | 20.764 | 16.132 | 27.324 | 1.00 38.81 |
| ATOM | 1252 | N | THR | A | 395 | 19.398 | 17.832 | 26.760 | 1.00 40.43 |
| ATOM | 1253 | CA | THR | A | 395 | 20.457 | 18.772 | 26.355 | 1.00 44.23 |
| ATOM | 1254 | CB | THR | A | 395 | 20.909 | 18.684 | 24.850 | 1.00 44.10 |
| ATOM | 1255 | OG1 | THR | A | 395 | 19.811 | 18.319 | 24.000 | 1.00 46.39 |
| ATOM | 1256 | CG2 | THR | A | 395 | 22.076 | 17.740 | 24.685 | 1.00 43.39 |
| ATOM | 1257 | C | THR | A | 395 | 20.014 | 20.198 | 26.636 | 1.00 47.00 |
| ATOM | 1258 | O | THR | A | 395 | 19.070 | 20.424 | 27.398 | 1.00 47.62 |
| ATOM | 1259 | N | ALA | A | 396 | 20.665 | 21.163 | 25.997 | 1.00 50.97 |
| ATOM | 1260 | CA | ALA | A | 396 | 20.315 | 22.556 | 26.229 | 1.00 55.16 |
| ATOM | 1261 | CB | ALA | A | 396 | 21.406 | 23.233 | 27.073 | 1.00 55.24 |
| ATOM | 1262 | C | ALA | A | 396 | 19.947 | 23.428 | 25.014 | 1.00 57.93 |
| ATOM | 1263 | O | ALA | A | 396 | 20.209 | 24.639 | 25.027 | 1.00 59.53 |
| ATOM | 1264 | N | ARG | A | 397 | 19.320 | 22.842 | 23.989 | 1.00 59.62 |
| ATOM | 1265 | CA | ARG | A | 397 | 18.895 | 23.626 | 22.821 | 1.00 60.73 |
| ATOM | 1266 | CB | ARG | A | 397 | 18.489 | 22.728 | 21.646 | 1.00 61.14 |
| ATOM | 1267 | CG | ARG | A | 397 | 19.631 | 21.953 | 20.998 | 1.00 62.46 |
| ATOM | 1268 | CD | ARG | A | 397 | 19.597 | 22.046 | 19.457 | 1.00 62.18 |
| ATOM | 1269 | NE | ARG | A | 397 | 20.283 | 20.925 | 18.806 | 1.00 61.68 |
| ATOM | 1270 | CZ | ARG | A | 397 | 19.856 | 19.663 | 18.860 | 1.00 61.30 |
| ATOM | 1271 | NH1 | ARG | A | 397 | 18.746 | 19.367 | 19.530 | 1.00 61.16 |
| ATOM | 1272 | NH2 | ARG | A | 397 | 20.539 | 18.693 | 18.260 | 1.00 59.70 |
| ATOM | 1273 | C | ARG | A | 397 | 17.698 | 24.501 | 23.217 | 1.00 61.52 |
| ATOM | 1274 | O | ARG | A | 397 | 17.885 | 25.736 | 23.351 | 1.00 62.34 |
| ATOM | 1275 | CB | PRO | A | 403 | 8.297 | 20.197 | 18.831 | 1.00 31.33 |
| ATOM | 1276 | CG | PRO | A | 403 | 8.734 | 20.723 | 20.200 | 1.00 32.39 |
| ATOM | 1277 | C | PRO | A | 403 | 7.098 | 21.371 | 16.951 | 1.00 33.69 |
| ATOM | 1278 | O | PRO | A | 403 | 7.008 | 20.380 | 16.183 | 1.00 35.10 |
| ATOM | 1279 | N | PRO | A | 403 | 7.913 | 22.597 | 19.015 | 1.00 32.25 |
| ATOM | 1280 | CD | PRO | A | 403 | 8.116 | 22.135 | 20.393 | 1.00 31.85 |
| ATOM | 1281 | CA | PRO | A | 403 | 8.193 | 21.484 | 18.031 | 1.00 32.80 |
| ATOM | 1282 | N | ILE | A | 404 | 6.293 | 22.426 | 16.874 | 1.00 32.80 |
| ATOM | 1283 | CA | ILE | A | 404 | 5.178 | 22.513 | 15.936 | 1.00 31.62 |
| ATOM | 1284 | CB | ILE | A | 404 | 4.288 | 23.739 | 16.289 | 1.00 31.37 |
| ATOM | 1285 | CG2 | ILE | A | 404 | 3.447 | 24.173 | 15.099 | 1.00 31.36 |
| ATOM | 1286 | CG1 | ILE | A | 404 | 3.368 | 23.372 | 17.442 | 1.00 32.90 |
| ATOM | 1287 | CD1 | ILE | A | 404 | 2.400 | 22.231 | 17.076 | 1.00 33.47 |
| ATOM | 1288 | C | ILE | A | 404 | 5.516 | 22.515 | 14.443 | 1.00 30.24 |
| ATOM | 1289 | O | ILE | A | 404 | 4.718 | 22.043 | 13.636 | 1.00 29.77 |
| ATOM | 1290 | N | LYS | A | 405 | 6.702 | 23.006 | 14.093 | 1.00 28.61 |
| ATOM | 1291 | CA | LYS | A | 405 | 7.126 | 23.119 | 12.695 | 1.00 27.41 |
| ATOM | 1292 | CB | LYS | A | 405 | 8.365 | 24.014 | 12.591 | 1.00 28.12 |
| ATOM | 1293 | CG | LYS | A | 405 | 8.079 | 25.440 | 13.018 | 1.00 28.68 |
| ATOM | 1294 | CD | LYS | A | 405 | 9.282 | 26.337 | 12.871 | 1.00 29.71 |
| ATOM | 1295 | CE | LYS | A | 405 | 8.939 | 27.777 | 13.234 | 1.00 30.63 |
| ATOM | 1296 | NZ | LYS | A | 405 | 9.952 | 28.740 | 12.699 | 1.00 32.42 |
| ATOM | 1297 | C | LYS | A | 405 | 7.295 | 21.843 | 11.868 | 1.00 25.83 |
| ATOM | 1298 | O | LYS | A | 405 | 7.463 | 21.911 | 10.646 | 1.00 25.21 |
| ATOM | 1299 | N | TRP | A | 406 | 7.191 | 20.692 | 12.528 | 1.00 24.27 |
| ATOM | 1300 | CA | TRP | A | 406 | 7.305 | 19.402 | 11.865 | 1.00 23.17 |
| ATOM | 1301 | CB | TRP | A | 406 | 8.407 | 18.563 | 12.517 | 1.00 23.13 |
| ATOM | 1302 | CG | TRP | A | 406 | 9.817 | 19.102 | 12.327 | 1.00 21.87 |
| ATOM | 1303 | CD2 | TRP | A | 406 | 10.454 | 20.122 | 13.103 | 1.00 20.55 |
| ATOM | 1304 | CE2 | TRP | A | 406 | 11.759 | 20.289 | 12.584 | 1.00 20.09 |
| ATOM | 1305 | CE3 | TRP | A | 406 | 10.047 | 20.915 | 14.187 | 1.00 19.72 |
| ATOM | 1306 | CD1 | TRP | A | 406 | 10.739 | 18.698 | 11.387 | 1.00 20.07 |
| ATOM | 1307 | NE1 | TRP | A | 406 | 11.901 | 19.410 | 11.538 | 1.00 19.88 |

Figure 8

```
ATOM   1308  CZ2  TRP A 406      12.664  21.217  13.120  1.00 19.06
ATOM   1309  CZ3  TRP A 406      10.946  21.833  14.713  1.00 19.49
ATOM   1310  CH2  TRP A 406      12.241  21.975  14.175  1.00 18.68
ATOM   1311  C    TRP A 406       6.005  18.610  11.913  1.00 23.58
ATOM   1312  O    TRP A 406       5.936  17.500  11.400  1.00 23.90
ATOM   1313  N    THR A 407       4.979  19.171  12.542  1.00 24.34
ATOM   1314  CA   THR A 407       3.694  18.487  12.676  1.00 24.20
ATOM   1315  CB   THR A 407       2.968  18.935  13.973  1.00 24.84
ATOM   1316  OG1  THR A 407       3.885  18.921  15.069  1.00 25.59
ATOM   1317  CG2  THR A 407       1.834  17.988  14.306  1.00 24.88
ATOM   1318  C    THR A 407       2.767  18.715  11.470  1.00 24.03
ATOM   1319  O    THR A 407       2.546  19.863  11.071  1.00 23.41
ATOM   1320  N    ALA A 408       2.233  17.622  10.905  1.00 23.23
ATOM   1321  CA   ALA A 408       1.312  17.676   9.762  1.00 22.45
ATOM   1322  CB   ALA A 408       1.023  16.278   9.253  1.00 22.81
ATOM   1323  C    ALA A 408       0.024  18.355  10.209  1.00 22.54
ATOM   1324  O    ALA A 408      -0.278  18.387  11.392  1.00 23.54
ATOM   1325  N    PRO A 409      -0.765  18.894   9.268  1.00 23.03
ATOM   1326  CD   PRO A 409      -0.543  19.032   7.821  1.00 21.74
ATOM   1327  CA   PRO A 409      -2.012  19.567   9.669  1.00 23.27
ATOM   1328  CB   PRO A 409      -2.577  20.055   8.334  1.00 22.91
ATOM   1329  CG   PRO A 409      -1.329  20.277   7.512  1.00 21.98
ATOM   1330  C    PRO A 409      -3.025  18.733  10.459  1.00 23.47
ATOM   1331  O    PRO A 409      -3.626  19.230  11.407  1.00 22.86
ATOM   1332  N    GLU A 410      -3.188  17.468  10.085  1.00 24.02
ATOM   1333  CA   GLU A 410      -4.138  16.584  10.756  1.00 25.28
ATOM   1334  CB   GLU A 410      -4.368  15.305   9.933  1.00 24.35
ATOM   1335  CG   GLU A 410      -3.191  14.313   9.897  1.00 25.31
ATOM   1336  CD   GLU A 410      -2.132  14.634   8.847  1.00 25.85
ATOM   1337  OE1  GLU A 410      -2.224  15.675   8.161  1.00 26.70
ATOM   1338  OE2  GLU A 410      -1.208  13.819   8.692  1.00 25.05
ATOM   1339  C    GLU A 410      -3.729  16.237  12.198  1.00 26.55
ATOM   1340  O    GLU A 410      -4.586  15.969  13.057  1.00 27.18
ATOM   1341  N    ALA A 411      -2.420  16.229  12.453  1.00 27.33
ATOM   1342  CA   ALA A 411      -1.879  15.929  13.779  1.00 27.30
ATOM   1343  CB   ALA A 411      -0.413  15.593  13.670  1.00 26.18
ATOM   1344  C    ALA A 411      -2.086  17.131  14.701  1.00 28.52
ATOM   1345  O    ALA A 411      -2.255  16.983  15.913  1.00 28.90
ATOM   1346  N    ILE A 412      -2.068  18.325  14.114  1.00 30.07
ATOM   1347  CA   ILE A 412      -2.272  19.560  14.858  1.00 31.09
ATOM   1348  CB   ILE A 412      -1.792  20.793  14.071  1.00 30.17
ATOM   1349  CG2  ILE A 412      -2.072  22.068  14.870  1.00 30.16
ATOM   1350  CG1  ILE A 412      -0.306  20.682  13.757  1.00 30.12
ATOM   1351  CD1  ILE A 412       0.240  21.863  12.989  1.00 28.23
ATOM   1352  C    ILE A 412      -3.744  19.789  15.183  1.00 32.37
ATOM   1353  O    ILE A 412      -4.068  20.152  16.312  1.00 33.40
ATOM   1354  N    ASN A 413      -4.621  19.587  14.198  1.00 33.41
ATOM   1355  CA   ASN A 413      -6.061  19.822  14.371  1.00 35.15
ATOM   1356  CB   ASN A 413      -6.729  20.096  13.017  1.00 36.57
ATOM   1357  CG   ASN A 413      -6.094  21.265  12.268  1.00 38.83
ATOM   1358  OD1  ASN A 413      -5.639  22.241  12.877  1.00 39.17
ATOM   1359  ND2  ASN A 413      -6.048  21.162  10.938  1.00 38.78
ATOM   1360  C    ASN A 413      -6.847  18.728  15.070  1.00 35.35
ATOM   1361  O    ASN A 413      -7.823  19.015  15.769  1.00 34.35
ATOM   1362  N    TYR A 414      -6.453  17.476  14.856  1.00 36.40
ATOM   1363  CA   TYR A 414      -7.169  16.359  15.473  1.00 37.48
ATOM   1364  CB   TYR A 414      -7.980  15.619  14.402  1.00 39.04
ATOM   1365  CG   TYR A 414      -8.862  16.545  13.594  1.00 43.07
ATOM   1366  CD1  TYR A 414      -9.970  17.172  14.178  1.00 43.90
ATOM   1367  CE1  TYR A 414     -10.766  18.063  13.447  1.00 45.17
```

Figure 8

```
ATOM   1368  CD2 TYR A 414      -8.570  16.827  12.251  1.00 44.87
ATOM   1369  CE2 TYR A 414      -9.357  17.714  11.508  1.00 45.32
ATOM   1370  CZ  TYR A 414     -10.454  18.330  12.111  1.00 46.11
ATOM   1371  OH  TYR A 414     -11.233  19.208  11.378  1.00 46.96
ATOM   1372  C   TYR A 414      -6.292  15.383  16.278  1.00 36.37
ATOM   1373  O   TYR A 414      -6.784  14.422  16.877  1.00 36.47
ATOM   1374  N   GLY A 415      -4.997  15.649  16.331  1.00 35.10
ATOM   1375  CA  GLY A 415      -4.113  14.762  17.069  1.00 33.50
ATOM   1376  C   GLY A 415      -3.971  13.386  16.440  1.00 31.60
ATOM   1377  O   GLY A 415      -3.653  12.408  17.120  1.00 30.99
ATOM   1378  N   THR A 416      -4.219  13.297  15.140  1.00 31.06
ATOM   1379  CA  THR A 416      -4.087  12.016  14.469  1.00 30.69
ATOM   1380  CB  THR A 416      -5.240  11.732  13.446  1.00 30.57
ATOM   1381  OG1 THR A 416      -4.688  11.273  12.207  1.00 31.13
ATOM   1382  CG2 THR A 416      -6.089  12.948  13.205  1.00 29.63
ATOM   1383  C   THR A 416      -2.707  11.874  13.826  1.00 29.30
ATOM   1384  O   THR A 416      -2.392  12.526  12.837  1.00 29.70
ATOM   1385  N   PHE A 417      -1.881  11.044  14.448  1.00 27.88
ATOM   1386  CA  PHE A 417      -0.537  10.773  13.975  1.00 27.07
ATOM   1387  CB  PHE A 417       0.451  10.790  15.160  1.00 27.21
ATOM   1388  CG  PHE A 417       0.704  12.166  15.749  1.00 27.38
ATOM   1389  CD1 PHE A 417      -0.096  12.662  16.794  1.00 27.66
ATOM   1390  CD2 PHE A 417       1.753  12.961  15.269  1.00 25.62
ATOM   1391  CE1 PHE A 417       0.147  13.940  17.349  1.00 27.01
ATOM   1392  CE2 PHE A 417       2.002  14.229  15.813  1.00 25.09
ATOM   1393  CZ  PHE A 417       1.202  14.719  16.852  1.00 26.05
ATOM   1394  C   PHE A 417      -0.431   9.420  13.256  1.00 25.57
ATOM   1395  O   PHE A 417      -0.818   8.396  13.799  1.00 26.17
ATOM   1396  N   THR A 418       0.053   9.423  12.019  1.00 24.08
ATOM   1397  CA  THR A 418       0.259   8.179  11.275  1.00 23.01
ATOM   1398  CB  THR A 418      -0.832   7.902  10.219  1.00 22.80
ATOM   1399  OG1 THR A 418      -0.766   8.887   9.186  1.00 22.72
ATOM   1400  CG2 THR A 418      -2.207   7.905  10.849  1.00 22.18
ATOM   1401  C   THR A 418       1.624   8.231  10.581  1.00 22.08
ATOM   1402  O   THR A 418       2.418   9.140  10.813  1.00 21.75
ATOM   1403  N   ILE A 419       1.910   7.242   9.748  1.00 21.81
ATOM   1404  CA  ILE A 419       3.183   7.208   9.043  1.00 20.88
ATOM   1405  CB  ILE A 419       3.421   5.840   8.373  1.00 20.43
ATOM   1406  CG2 ILE A 419       2.509   5.691   7.158  1.00 19.45
ATOM   1407  CG1 ILE A 419       4.893   5.695   7.990  1.00 20.38
ATOM   1408  CD1 ILE A 419       5.840   5.742   9.167  1.00 18.57
ATOM   1409  C   ILE A 419       3.164   8.309   7.990  1.00 20.56
ATOM   1410  O   ILE A 419       4.215   8.722   7.492  1.00 21.18
ATOM   1411  N   LYS A 420       1.964   8.760   7.627  1.00 19.35
ATOM   1412  CA  LYS A 420       1.844   9.832   6.648  1.00 18.25
ATOM   1413  CB  LYS A 420       0.453   9.889   6.042  1.00 16.79
ATOM   1414  CG  LYS A 420       0.163   8.750   5.111  1.00 14.19
ATOM   1415  CD  LYS A 420       1.078   8.784   3.932  1.00 12.97
ATOM   1416  CE  LYS A 420       0.803   7.606   3.055  1.00 13.60
ATOM   1417  NZ  LYS A 420       1.873   7.467   2.063  1.00 16.09
ATOM   1418  C   LYS A 420       2.213  11.179   7.236  1.00 17.93
ATOM   1419  O   LYS A 420       2.618  12.078   6.511  1.00 18.13
ATOM   1420  N   SER A 421       2.041  11.343   8.540  1.00 18.42
ATOM   1421  CA  SER A 421       2.438  12.601   9.148  1.00 20.44
ATOM   1422  CB  SER A 421       1.634  12.939  10.416  1.00 19.78
ATOM   1423  OG  SER A 421       1.297  11.801  11.166  1.00 22.84
ATOM   1424  C   SER A 421       3.957  12.605   9.373  1.00 20.33
ATOM   1425  O   SER A 421       4.558  13.666   9.531  1.00 20.08
ATOM   1426  N   ASP A 422       4.570  11.416   9.360  1.00 20.96
ATOM   1427  CA  ASP A 422       6.028  11.285   9.485  1.00 21.70
```

Figure 8

| | | | | | | | | | |
|---|---|---|---|---|---|---|---|---|---|
| ATOM | 1428 | CB | ASP | A | 422 | 6.462 | 9.840 | 9.767 | 1.00 22.21 |
| ATOM | 1429 | CG | ASP | A | 422 | 6.212 | 9.401 | 11.202 | 1.00 23.81 |
| ATOM | 1430 | OD1 | ASP | A | 422 | 6.097 | 10.244 | 12.125 | 1.00 25.31 |
| ATOM | 1431 | OD2 | ASP | A | 422 | 6.148 | 8.177 | 11.404 | 1.00 24.12 |
| ATOM | 1432 | C | ASP | A | 422 | 6.602 | 11.695 | 8.127 | 1.00 21.82 |
| ATOM | 1433 | O | ASP | A | 422 | 7.676 | 12.275 | 8.059 | 1.00 22.24 |
| ATOM | 1434 | N | VAL | A | 423 | 5.900 | 11.329 | 7.051 | 1.00 21.88 |
| ATOM | 1435 | CA | VAL | A | 423 | 6.293 | 11.693 | 5.688 | 1.00 21.06 |
| ATOM | 1436 | CB | VAL | A | 423 | 5.345 | 11.073 | 4.593 | 1.00 21.83 |
| ATOM | 1437 | CG1 | VAL | A | 423 | 5.689 | 11.626 | 3.182 | 1.00 20.22 |
| ATOM | 1438 | CG2 | VAL | A | 423 | 5.475 | 9.526 | 4.574 | 1.00 18.66 |
| ATOM | 1439 | C | VAL | A | 423 | 6.273 | 13.215 | 5.623 | 1.00 21.59 |
| ATOM | 1440 | O | VAL | A | 423 | 7.179 | 13.815 | 5.037 | 1.00 22.74 |
| ATOM | 1441 | N | TRP | A | 424 | 5.298 | 13.845 | 6.291 | 1.00 21.24 |
| ATOM | 1442 | CA | TRP | A | 424 | 5.215 | 15.306 | 6.321 | 1.00 20.32 |
| ATOM | 1443 | CB | TRP | A | 424 | 3.920 | 15.810 | 6.980 | 1.00 19.69 |
| ATOM | 1444 | CG | TRP | A | 424 | 3.880 | 17.319 | 7.185 | 1.00 18.95 |
| ATOM | 1445 | CD2 | TRP | A | 424 | 3.029 | 18.271 | 6.522 | 1.00 20.04 |
| ATOM | 1446 | CE2 | TRP | A | 424 | 3.353 | 19.556 | 7.041 | 1.00 19.33 |
| ATOM | 1447 | CE3 | TRP | A | 424 | 2.018 | 18.168 | 5.546 | 1.00 21.73 |
| ATOM | 1448 | CD1 | TRP | A | 424 | 4.658 | 18.047 | 8.047 | 1.00 19.24 |
| ATOM | 1449 | NE1 | TRP | A | 424 | 4.351 | 19.384 | 7.962 | 1.00 18.69 |
| ATOM | 1450 | CZ2 | TRP | A | 424 | 2.702 | 20.731 | 6.622 | 1.00 18.62 |
| ATOM | 1451 | CZ3 | TRP | A | 424 | 1.365 | 19.346 | 5.125 | 1.00 20.80 |
| ATOM | 1452 | CH2 | TRP | A | 424 | 1.718 | 20.610 | 5.672 | 1.00 20.09 |
| ATOM | 1453 | C | TRP | A | 424 | 6.449 | 15.840 | 7.049 | 1.00 20.63 |
| ATOM | 1454 | O | TRP | A | 424 | 7.074 | 16.771 | 6.570 | 1.00 21.11 |
| ATOM | 1455 | N | SER | A | 425 | 6.810 | 15.240 | 8.186 | 1.00 21.89 |
| ATOM | 1456 | CA | SER | A | 425 | 8.012 | 15.640 | 8.946 | 1.00 22.19 |
| ATOM | 1457 | CB | SER | A | 425 | 8.144 | 14.819 | 10.229 | 1.00 23.11 |
| ATOM | 1458 | OG | SER | A | 425 | 7.114 | 15.125 | 11.150 | 1.00 26.31 |
| ATOM | 1459 | C | SER | A | 425 | 9.300 | 15.475 | 8.134 | 1.00 21.85 |
| ATOM | 1460 | O | SER | A | 425 | 10.188 | 16.306 | 8.220 | 1.00 22.54 |
| ATOM | 1461 | N | PHE | A | 426 | 9.411 | 14.382 | 7.379 | 1.00 21.88 |
| ATOM | 1462 | CA | PHE | A | 426 | 10.586 | 14.133 | 6.541 | 1.00 22.81 |
| ATOM | 1463 | CB | PHE | A | 426 | 10.470 | 12.800 | 5.769 | 1.00 22.42 |
| ATOM | 1464 | CG | PHE | A | 426 | 11.749 | 12.391 | 5.040 | 1.00 24.24 |
| ATOM | 1465 | CD1 | PHE | A | 426 | 12.856 | 11.903 | 5.743 | 1.00 24.45 |
| ATOM | 1466 | CD2 | PHE | A | 426 | 11.849 | 12.484 | 3.654 | 1.00 24.63 |
| ATOM | 1467 | CE1 | PHE | A | 426 | 14.038 | 11.521 | 5.072 | 1.00 23.85 |
| ATOM | 1468 | CE2 | PHE | A | 426 | 13.036 | 12.101 | 2.983 | 1.00 23.81 |
| ATOM | 1469 | CZ | PHE | A | 426 | 14.119 | 11.623 | 3.700 | 1.00 22.44 |
| ATOM | 1470 | C | PHE | A | 426 | 10.762 | 15.264 | 5.539 | 1.00 22.66 |
| ATOM | 1471 | O | PHE | A | 426 | 11.884 | 15.566 | 5.141 | 1.00 23.41 |
| ATOM | 1472 | N | GLY | A | 427 | 9.648 | 15.845 | 5.094 | 1.00 22.15 |
| ATOM | 1473 | CA | GLY | A | 427 | 9.703 | 16.946 | 4.148 | 1.00 20.85 |
| ATOM | 1474 | C | GLY | A | 427 | 10.291 | 18.190 | 4.794 | 1.00 20.48 |
| ATOM | 1475 | O | GLY | A | 427 | 10.992 | 18.948 | 4.143 | 1.00 20.72 |
| ATOM | 1476 | N | ILE | A | 428 | 9.967 | 18.418 | 6.065 | 1.00 20.85 |
| ATOM | 1477 | CA | ILE | A | 428 | 10.477 | 19.556 | 6.823 | 1.00 20.62 |
| ATOM | 1478 | CB | ILE | A | 428 | 9.732 | 19.705 | 8.186 | 1.00 20.42 |
| ATOM | 1479 | CG2 | ILE | A | 428 | 10.148 | 20.983 | 8.900 | 1.00 20.17 |
| ATOM | 1480 | CG1 | ILE | A | 428 | 8.222 | 19.763 | 7.965 | 1.00 20.18 |
| ATOM | 1481 | CD1 | ILE | A | 428 | 7.761 | 20.959 | 7.127 | 1.00 20.96 |
| ATOM | 1482 | C | ILE | A | 428 | 11.967 | 19.290 | 7.071 | 1.00 21.84 |
| ATOM | 1483 | O | ILE | A | 428 | 12.798 | 20.179 | 6.933 | 1.00 23.65 |
| ATOM | 1484 | N | LEU | A | 429 | 12.293 | 18.040 | 7.389 | 1.00 22.68 |
| ATOM | 1485 | CA | LEU | A | 429 | 13.663 | 17.602 | 7.650 | 1.00 23.20 |
| ATOM | 1486 | CB | LEU | A | 429 | 13.632 | 16.134 | 8.089 | 1.00 22.13 |
| ATOM | 1487 | CG | LEU | A | 429 | 14.818 | 15.477 | 8.782 | 1.00 22.71 |

Figure 8

```
ATOM   1488  CD1 LEU A 429      14.345  14.225   9.482  1.00 22.25
ATOM   1489  CD2 LEU A 429      15.890  15.132   7.791  1.00 23.56
ATOM   1490  C   LEU A 429      14.551  17.774   6.404  1.00 23.60
ATOM   1491  O   LEU A 429      15.757  18.010   6.529  1.00 24.58
ATOM   1492  N   LEU A 430      13.958  17.628   5.215  1.00 22.56
ATOM   1493  CA  LEU A 430      14.696  17.778   3.972  1.00 21.51
ATOM   1494  CB  LEU A 430      13.875  17.323   2.771  1.00 20.28
ATOM   1495  CG  LEU A 430      13.683  15.827   2.502  1.00 19.22
ATOM   1496  CD1 LEU A 430      12.729  15.672   1.331  1.00 17.10
ATOM   1497  CD2 LEU A 430      15.016  15.115   2.212  1.00 17.95
ATOM   1498  C   LEU A 430      15.129  19.225   3.783  1.00 22.75
ATOM   1499  O   LEU A 430      16.153  19.471   3.149  1.00 24.23
ATOM   1500  N   THR A 431      14.343  20.180   4.296  1.00 23.05
ATOM   1501  CA  THR A 431      14.699  21.603   4.192  1.00 23.41
ATOM   1502  CB  THR A 431      13.508  22.596   4.509  1.00 22.82
ATOM   1503  OG1 THR A 431      13.188  22.575   5.909  1.00 21.86
ATOM   1504  CG2 THR A 431      12.266  22.260   3.671  1.00 20.43
ATOM   1505  C   THR A 431      15.850  21.852   5.153  1.00 24.38
ATOM   1506  O   THR A 431      16.782  22.579   4.825  1.00 25.41
ATOM   1507  N   GLU A 432      15.791  21.220   6.324  1.00 25.14
ATOM   1508  CA  GLU A 432      16.852  21.333   7.322  1.00 26.14
ATOM   1509  CB  GLU A 432      16.554  20.465   8.533  1.00 25.99
ATOM   1510  CG  GLU A 432      15.396  20.924   9.367  1.00 26.10
ATOM   1511  CD  GLU A 432      15.290  20.132  10.645  1.00 25.58
ATOM   1512  OE1 GLU A 432      14.729  19.013  10.636  1.00 25.35
ATOM   1513  OE2 GLU A 432      15.784  20.636  11.662  1.00 25.55
ATOM   1514  C   GLU A 432      18.160  20.833   6.743  1.00 27.16
ATOM   1515  O   GLU A 432      19.211  21.347   7.067  1.00 28.61
ATOM   1516  N   ILE A 433      18.089  19.767   5.954  1.00 27.61
ATOM   1517  CA  ILE A 433      19.258  19.184   5.333  1.00 28.07
ATOM   1518  CB  ILE A 433      18.921  17.809   4.735  1.00 28.31
ATOM   1519  CG2 ILE A 433      20.032  17.328   3.816  1.00 28.50
ATOM   1520  CG1 ILE A 433      18.663  16.805   5.859  1.00 28.86
ATOM   1521  CD1 ILE A 433      18.576  15.355   5.380  1.00 29.48
ATOM   1522  C   ILE A 433      19.906  20.082   4.271  1.00 29.40
ATOM   1523  O   ILE A 433      21.114  20.316   4.317  1.00 31.11
ATOM   1524  N   VAL A 434      19.117  20.613   3.339  1.00 29.47
ATOM   1525  CA  VAL A 434      19.673  21.462   2.280  1.00 28.97
ATOM   1526  CB  VAL A 434      18.749  21.502   1.033  1.00 28.48
ATOM   1527  CG1 VAL A 434      18.692  20.131   0.411  1.00 28.59
ATOM   1528  CG2 VAL A 434      17.330  21.966   1.408  1.00 28.24
ATOM   1529  C   VAL A 434      20.055  22.888   2.700  1.00 29.37
ATOM   1530  O   VAL A 434      20.784  23.565   1.982  1.00 29.66
ATOM   1531  N   THR A 435      19.590  23.333   3.864  1.00 30.07
ATOM   1532  CA  THR A 435      19.892  24.683   4.344  1.00 31.17
ATOM   1533  CB  THR A 435      18.598  25.463   4.756  1.00 31.11
ATOM   1534  OG1 THR A 435      17.965  24.820   5.868  1.00 31.26
ATOM   1535  CG2 THR A 435      17.608  25.550   3.600  1.00 29.39
ATOM   1536  C   THR A 435      20.853  24.649   5.532  1.00 32.66
ATOM   1537  O   THR A 435      20.967  25.621   6.278  1.00 32.63
ATOM   1538  N   HIS A 436      21.488  23.495   5.728  1.00 34.78
ATOM   1539  CA  HIS A 436      22.461  23.259   6.801  1.00 36.10
ATOM   1540  CB  HIS A 436      23.744  24.055   6.545  1.00 38.30
ATOM   1541  CG  HIS A 436      24.310  23.840   5.175  1.00 41.53
ATOM   1542  CD2 HIS A 436      24.485  24.695   4.139  1.00 42.27
ATOM   1543  ND1 HIS A 436      24.724  22.601   4.726  1.00 42.19
ATOM   1544  CE1 HIS A 436      25.128  22.701   3.472  1.00 42.27
ATOM   1545  NE2 HIS A 436      24.992  23.961   3.093  1.00 44.25
ATOM   1546  C   HIS A 436      21.972  23.466   8.223  1.00 36.02
ATOM   1547  O   HIS A 436      22.631  24.135   9.025  1.00 36.62
```

Figure 8

| | | | | | | | | |
|---|---|---|---|---|---|---|---|---|
| ATOM | 1548 | N | GLY | A | 437 | 20.844 | 22.841 | 8.543 | 1.00 | 35.26 |
| ATOM | 1549 | CA | GLY | A | 437 | 20.297 | 22.937 | 9.880 | 1.00 | 35.62 |
| ATOM | 1550 | C | GLY | A | 437 | 19.526 | 24.201 | 10.195 | 1.00 | 36.26 |
| ATOM | 1551 | O | GLY | A | 437 | 19.328 | 24.524 | 11.363 | 1.00 | 36.62 |
| ATOM | 1552 | N | ARG | A | 438 | 19.077 | 24.912 | 9.169 | 1.00 | 37.08 |
| ATOM | 1553 | CA | ARG | A | 438 | 18.295 | 26.134 | 9.368 | 1.00 | 38.45 |
| ATOM | 1554 | CB | ARG | A | 438 | 18.188 | 26.880 | 8.027 | 1.00 | 41.03 |
| ATOM | 1555 | CG | ARG | A | 438 | 17.762 | 28.351 | 8.074 | 1.00 | 44.20 |
| ATOM | 1556 | CD | ARG | A | 438 | 16.256 | 28.547 | 8.264 | 1.00 | 47.61 |
| ATOM | 1557 | NE | ARG | A | 438 | 15.418 | 27.852 | 7.274 | 1.00 | 49.83 |
| ATOM | 1558 | CZ | ARG | A | 438 | 15.334 | 28.180 | 5.984 | 1.00 | 50.90 |
| ATOM | 1559 | NH1 | ARG | A | 438 | 16.043 | 29.202 | 5.505 | 1.00 | 51.90 |
| ATOM | 1560 | NH2 | ARG | A | 438 | 14.529 | 27.493 | 5.177 | 1.00 | 49.88 |
| ATOM | 1561 | C | ARG | A | 438 | 16.894 | 25.772 | 9.923 | 1.00 | 37.17 |
| ATOM | 1562 | O | ARG | A | 438 | 16.343 | 24.711 | 9.609 | 1.00 | 36.70 |
| ATOM | 1563 | N | ILE | A | 439 | 16.351 | 26.636 | 10.777 | 1.00 | 36.01 |
| ATOM | 1564 | CA | ILE | A | 439 | 15.029 | 26.422 | 11.371 | 1.00 | 35.15 |
| ATOM | 1565 | CB | ILE | A | 439 | 14.804 | 27.368 | 12.606 | 1.00 | 35.63 |
| ATOM | 1566 | CG2 | ILE | A | 439 | 13.347 | 27.747 | 12.777 | 1.00 | 34.99 |
| ATOM | 1567 | CG1 | ILE | A | 439 | 15.292 | 26.659 | 13.875 | 1.00 | 37.92 |
| ATOM | 1568 | CD1 | ILE | A | 439 | 15.208 | 27.485 | 15.156 | 1.00 | 39.33 |
| ATOM | 1569 | C | ILE | A | 439 | 13.936 | 26.607 | 10.327 | 1.00 | 34.06 |
| ATOM | 1570 | O | ILE | A | 439 | 13.918 | 27.614 | 9.618 | 1.00 | 34.29 |
| ATOM | 1571 | N | PRO | A | 440 | 13.011 | 25.633 | 10.214 | 1.00 | 32.36 |
| ATOM | 1572 | CD | PRO | A | 440 | 12.926 | 24.391 | 10.999 | 1.00 | 31.57 |
| ATOM | 1573 | CA | PRO | A | 440 | 11.914 | 25.702 | 9.243 | 1.00 | 31.27 |
| ATOM | 1574 | CB | PRO | A | 440 | 11.103 | 24.444 | 9.566 | 1.00 | 31.25 |
| ATOM | 1575 | CG | PRO | A | 440 | 12.143 | 23.493 | 10.085 | 1.00 | 30.98 |
| ATOM | 1576 | C | PRO | A | 440 | 11.090 | 26.972 | 9.446 | 1.00 | 30.37 |
| ATOM | 1577 | O | PRO | A | 440 | 11.105 | 27.550 | 10.542 | 1.00 | 29.90 |
| ATOM | 1578 | N | TYR | A | 441 | 10.381 | 27.401 | 8.398 | 1.00 | 29.52 |
| ATOM | 1579 | CA | TYR | A | 441 | 9.556 | 28.613 | 8.449 | 1.00 | 29.51 |
| ATOM | 1580 | CB | TYR | A | 441 | 8.233 | 28.356 | 9.186 | 1.00 | 27.99 |
| ATOM | 1581 | CG | TYR | A | 441 | 7.450 | 27.170 | 8.671 | 1.00 | 27.09 |
| ATOM | 1582 | CD1 | TYR | A | 441 | 6.514 | 27.319 | 7.656 | 1.00 | 26.20 |
| ATOM | 1583 | CE1 | TYR | A | 441 | 5.828 | 26.228 | 7.162 | 1.00 | 27.00 |
| ATOM | 1584 | CD2 | TYR | A | 441 | 7.674 | 25.888 | 9.182 | 1.00 | 26.31 |
| ATOM | 1585 | CE2 | TYR | A | 441 | 6.995 | 24.789 | 8.696 | 1.00 | 26.42 |
| ATOM | 1586 | CZ | TYR | A | 441 | 6.077 | 24.958 | 7.681 | 1.00 | 27.50 |
| ATOM | 1587 | OH | TYR | A | 441 | 5.448 | 23.853 | 7.150 | 1.00 | 28.38 |
| ATOM | 1588 | C | TYR | A | 441 | 10.334 | 29.716 | 9.170 | 1.00 | 30.72 |
| ATOM | 1589 | O | TYR | A | 441 | 9.923 | 30.198 | 10.233 | 1.00 | 30.67 |
| ATOM | 1590 | N | PRO | A | 442 | 11.494 | 30.103 | 8.616 | 1.00 | 31.98 |
| ATOM | 1591 | CD | PRO | A | 442 | 12.015 | 29.728 | 7.283 | 1.00 | 31.50 |
| ATOM | 1592 | CA | PRO | A | 442 | 12.312 | 31.148 | 9.241 | 1.00 | 33.02 |
| ATOM | 1593 | CB | PRO | A | 442 | 13.492 | 31.272 | 8.274 | 1.00 | 33.00 |
| ATOM | 1594 | CG | PRO | A | 442 | 12.882 | 30.903 | 6.932 | 1.00 | 32.32 |
| ATOM | 1595 | C | PRO | A | 442 | 11.518 | 32.450 | 9.367 | 1.00 | 34.73 |
| ATOM | 1596 | O | PRO | A | 442 | 10.830 | 32.864 | 8.431 | 1.00 | 35.96 |
| ATOM | 1597 | N | GLY | A | 443 | 11.537 | 33.058 | 10.544 | 1.00 | 35.50 |
| ATOM | 1598 | CA | GLY | A | 443 | 10.796 | 34.299 | 10.702 | 1.00 | 36.63 |
| ATOM | 1599 | C | GLY | A | 443 | 9.299 | 34.134 | 10.870 | 1.00 | 36.96 |
| ATOM | 1600 | O | GLY | A | 443 | 8.516 | 34.972 | 10.417 | 1.00 | 38.07 |
| ATOM | 1601 | N | MET | A | 444 | 8.924 | 33.048 | 11.540 | 1.00 | 37.29 |
| ATOM | 1602 | CA | MET | A | 444 | 7.542 | 32.692 | 11.875 | 1.00 | 37.13 |
| ATOM | 1603 | CB | MET | A | 444 | 6.923 | 31.737 | 10.847 | 1.00 | 36.35 |
| ATOM | 1604 | CG | MET | A | 444 | 6.330 | 32.411 | 9.639 | 1.00 | 36.77 |
| ATOM | 1605 | SD | MET | A | 444 | 5.708 | 31.259 | 8.395 | 1.00 | 36.85 |
| ATOM | 1606 | CE | MET | A | 444 | 4.291 | 30.725 | 9.193 | 1.00 | 36.79 |
| ATOM | 1607 | C | MET | A | 444 | 7.615 | 31.973 | 13.222 | 1.00 | 37.67 |

Figure 8

| | | | | | | | | | |
|---|---|---|---|---|---|---|---|---|---|
| ATOM | 1608 | O | MET | A | 444 | 8.545 | 31.187 | 13.463 | 1.00 37.81 |
| ATOM | 1609 | N | THR | A | 445 | 6.691 | 32.299 | 14.123 | 1.00 37.21 |
| ATOM | 1610 | CA | THR | A | 445 | 6.637 | 31.649 | 15.430 | 1.00 36.94 |
| ATOM | 1611 | CB | THR | A | 445 | 6.148 | 32.609 | 16.506 | 1.00 36.82 |
| ATOM | 1612 | OG1 | THR | A | 445 | 4.797 | 32.987 | 16.233 | 1.00 38.19 |
| ATOM | 1613 | CG2 | THR | A | 445 | 7.000 | 33.855 | 16.500 | 1.00 38.01 |
| ATOM | 1614 | C | THR | A | 445 | 5.647 | 30.502 | 15.299 | 1.00 37.50 |
| ATOM | 1615 | O | THR | A | 445 | 4.971 | 30.390 | 14.275 | 1.00 38.30 |
| ATOM | 1616 | N | ASN | A | 446 | 5.539 | 29.655 | 16.319 | 1.00 37.77 |
| ATOM | 1617 | CA | ASN | A | 446 | 4.598 | 28.537 | 16.249 | 1.00 37.76 |
| ATOM | 1618 | CB | ASN | A | 446 | 4.659 | 27.672 | 17.509 | 1.00 37.82 |
| ATOM | 1619 | CG | ASN | A | 446 | 5.958 | 26.888 | 17.608 | 1.00 38.73 |
| ATOM | 1620 | OD1 | ASN | A | 446 | 6.870 | 27.060 | 16.787 | 1.00 38.85 |
| ATOM | 1621 | ND2 | ASN | A | 446 | 6.049 | 26.017 | 18.610 | 1.00 38.41 |
| ATOM | 1622 | C | ASN | A | 446 | 3.155 | 28.936 | 15.918 | 1.00 37.62 |
| ATOM | 1623 | O | ASN | A | 446 | 2.562 | 28.355 | 15.007 | 1.00 37.28 |
| ATOM | 1624 | N | PRO | A | 447 | 2.568 | 29.919 | 16.646 | 1.00 37.41 |
| ATOM | 1625 | CD | PRO | A | 447 | 2.978 | 30.508 | 17.938 | 1.00 36.86 |
| ATOM | 1626 | CA | PRO | A | 447 | 1.187 | 30.310 | 16.330 | 1.00 36.35 |
| ATOM | 1627 | CB | PRO | A | 447 | 0.841 | 31.328 | 17.430 | 1.00 36.40 |
| ATOM | 1628 | CG | PRO | A | 447 | 2.172 | 31.766 | 17.969 | 1.00 36.18 |
| ATOM | 1629 | C | PRO | A | 447 | 0.995 | 30.857 | 14.911 | 1.00 35.41 |
| ATOM | 1630 | O | PRO | A | 447 | -0.109 | 30.784 | 14.351 | 1.00 34.94 |
| ATOM | 1631 | N | GLU | A | 448 | 2.065 | 31.385 | 14.327 | 1.00 33.98 |
| ATOM | 1632 | CA | GLU | A | 448 | 1.990 | 31.892 | 12.970 | 1.00 33.98 |
| ATOM | 1633 | CB | GLU | A | 448 | 3.095 | 32.893 | 12.713 | 1.00 35.05 |
| ATOM | 1634 | CG | GLU | A | 448 | 2.814 | 34.223 | 13.342 | 1.00 38.00 |
| ATOM | 1635 | CD | GLU | A | 448 | 4.044 | 35.094 | 13.428 | 1.00 41.00 |
| ATOM | 1636 | OE1 | GLU | A | 448 | 4.998 | 34.889 | 12.638 | 1.00 42.81 |
| ATOM | 1637 | OE2 | GLU | A | 448 | 4.057 | 35.991 | 14.300 | 1.00 43.35 |
| ATOM | 1638 | C | GLU | A | 448 | 2.053 | 30.744 | 11.972 | 1.00 33.73 |
| ATOM | 1639 | O | GLU | A | 448 | 1.396 | 30.788 | 10.934 | 1.00 33.70 |
| ATOM | 1640 | N | VAL | A | 449 | 2.825 | 29.709 | 12.294 | 1.00 32.54 |
| ATOM | 1641 | CA | VAL | A | 449 | 2.931 | 28.534 | 11.428 | 1.00 31.36 |
| ATOM | 1642 | CB | VAL | A | 449 | 4.022 | 27.552 | 11.940 | 1.00 30.49 |
| ATOM | 1643 | CG1 | VAL | A | 449 | 3.937 | 26.211 | 11.236 | 1.00 28.67 |
| ATOM | 1644 | CG2 | VAL | A | 449 | 5.399 | 28.161 | 11.716 | 1.00 28.41 |
| ATOM | 1645 | C | VAL | A | 449 | 1.557 | 27.871 | 11.387 | 1.00 31.38 |
| ATOM | 1646 | O | VAL | A | 449 | 1.074 | 27.478 | 10.325 | 1.00 32.08 |
| ATOM | 1647 | N | ILE | A | 450 | 0.894 | 27.856 | 12.538 | 1.00 31.37 |
| ATOM | 1648 | CA | ILE | A | 450 | -0.438 | 27.278 | 12.674 | 1.00 31.53 |
| ATOM | 1649 | CB | ILE | A | 450 | -0.938 | 27.307 | 14.151 | 1.00 32.54 |
| ATOM | 1650 | CG2 | ILE | A | 450 | -2.260 | 26.554 | 14.269 | 1.00 31.66 |
| ATOM | 1651 | CG1 | ILE | A | 450 | 0.119 | 26.735 | 15.117 | 1.00 33.13 |
| ATOM | 1652 | CD1 | ILE | A | 450 | 0.239 | 25.232 | 15.148 | 1.00 33.77 |
| ATOM | 1653 | C | ILE | A | 450 | -1.468 | 28.018 | 11.812 | 1.00 31.09 |
| ATOM | 1654 | O | ILE | A | 450 | -2.237 | 27.380 | 11.100 | 1.00 30.83 |
| ATOM | 1655 | N | GLN | A | 451 | -1.480 | 29.351 | 11.866 | 1.00 31.43 |
| ATOM | 1656 | CA | GLN | A | 451 | -2.442 | 30.116 | 11.075 | 1.00 32.10 |
| ATOM | 1657 | CB | GLN | A | 451 | -2.671 | 31.512 | 11.643 | 1.00 35.06 |
| ATOM | 1658 | CG | GLN | A | 451 | -1.447 | 32.385 | 11.751 | 1.00 40.62 |
| ATOM | 1659 | CD | GLN | A | 451 | -1.606 | 33.467 | 12.822 | 1.00 42.86 |
| ATOM | 1660 | OE1 | GLN | A | 451 | -1.121 | 34.595 | 12.667 | 1.00 44.42 |
| ATOM | 1661 | NE2 | GLN | A | 451 | -2.261 | 33.113 | 13.928 | 1.00 43.65 |
| ATOM | 1662 | C | GLN | A | 451 | -2.127 | 30.164 | 9.598 | 1.00 30.69 |
| ATOM | 1663 | O | GLN | A | 451 | -2.991 | 30.442 | 8.785 | 1.00 32.21 |
| ATOM | 1664 | N | ASN | A | 452 | -0.885 | 29.886 | 9.246 | 1.00 29.53 |
| ATOM | 1665 | CA | ASN | A | 452 | -0.506 | 29.849 | 7.850 | 1.00 28.17 |
| ATOM | 1666 | CB | ASN | A | 452 | 0.987 | 30.087 | 7.687 | 1.00 27.91 |
| ATOM | 1667 | CG | ASN | A | 452 | 1.302 | 31.531 | 7.502 | 1.00 28.38 |

Figure 8

| ATOM | 1668 | OD1 | ASN A 452 | 1.165 | 32.063 | 6.398 | 1.00 | 30.04 |
| --- | --- | --- | --- | --- | --- | --- | --- | --- |
| ATOM | 1669 | ND2 | ASN A 452 | 1.660 | 32.206 | 8.588 | 1.00 | 27.80 |
| ATOM | 1670 | C | ASN A 452 | -0.903 | 28.497 | 7.274 | 1.00 | 27.65 |
| ATOM | 1671 | O | ASN A 452 | -1.408 | 28.428 | 6.166 | 1.00 | 26.71 |
| ATOM | 1672 | N | LEU A 453 | -0.691 | 27.427 | 8.041 | 1.00 | 26.83 |
| ATOM | 1673 | CA | LEU A 453 | -1.073 | 26.095 | 7.594 | 1.00 | 26.32 |
| ATOM | 1674 | CB | LEU A 453 | -0.532 | 25.004 | 8.513 | 1.00 | 26.50 |
| ATOM | 1675 | CG | LEU A 453 | 0.965 | 24.702 | 8.411 | 1.00 | 26.99 |
| ATOM | 1676 | CD1 | LEU A 453 | 1.236 | 23.519 | 9.318 | 1.00 | 27.22 |
| ATOM | 1677 | CD2 | LEU A 453 | 1.399 | 24.394 | 6.986 | 1.00 | 24.24 |
| ATOM | 1678 | C | LEU A 453 | -2.587 | 25.996 | 7.474 | 1.00 | 26.20 |
| ATOM | 1679 | O | LEU A 453 | -3.082 | 25.180 | 6.714 | 1.00 | 25.67 |
| ATOM | 1680 | N | GLU A 454 | -3.323 | 26.803 | 8.236 | 1.00 | 26.74 |
| ATOM | 1681 | CA | GLU A 454 | -4.778 | 26.825 | 8.119 | 1.00 | 28.02 |
| ATOM | 1682 | CB | GLU A 454 | -5.390 | 27.810 | 9.093 | 1.00 | 31.17 |
| ATOM | 1683 | CG | GLU A 454 | -5.197 | 27.514 | 10.545 | 1.00 | 38.22 |
| ATOM | 1684 | CD | GLU A 454 | -5.818 | 28.596 | 11.436 | 1.00 | 41.92 |
| ATOM | 1685 | OE1 | GLU A 454 | -5.657 | 28.511 | 12.683 | 1.00 | 43.68 |
| ATOM | 1686 | OE2 | GLU A 454 | -6.453 | 29.537 | 10.884 | 1.00 | 42.70 |
| ATOM | 1687 | C | GLU A 454 | -5.127 | 27.348 | 6.720 | 1.00 | 26.75 |
| ATOM | 1688 | O | GLU A 454 | -6.060 | 26.866 | 6.076 | 1.00 | 25.98 |
| ATOM | 1689 | N | ARG A 455 | -4.387 | 28.366 | 6.280 | 1.00 | 25.45 |
| ATOM | 1690 | CA | ARG A 455 | -4.601 | 28.978 | 4.970 | 1.00 | 24.94 |
| ATOM | 1691 | CB | ARG A 455 | -4.147 | 30.443 | 4.984 | 1.00 | 25.88 |
| ATOM | 1692 | CG | ARG A 455 | -4.822 | 31.357 | 6.025 | 1.00 | 29.50 |
| ATOM | 1693 | CD | ARG A 455 | -4.288 | 32.810 | 5.964 | 1.00 | 32.34 |
| ATOM | 1694 | NE | ARG A 455 | -2.856 | 32.811 | 5.684 | 1.00 | 39.12 |
| ATOM | 1695 | CZ | ARG A 455 | -2.312 | 33.145 | 4.506 | 1.00 | 41.76 |
| ATOM | 1696 | NH1 | ARG A 455 | -3.080 | 33.555 | 3.494 | 1.00 | 41.71 |
| ATOM | 1697 | NH2 | ARG A 455 | -1.021 | 32.888 | 4.272 | 1.00 | 42.21 |
| ATOM | 1698 | C | ARG A 455 | -3.868 | 28.206 | 3.858 | 1.00 | 23.87 |
| ATOM | 1699 | O | ARG A 455 | -3.779 | 28.670 | 2.721 | 1.00 | 23.42 |
| ATOM | 1700 | N | GLY A 456 | -3.302 | 27.053 | 4.217 | 1.00 | 22.90 |
| ATOM | 1701 | CA | GLY A 456 | -2.590 | 26.206 | 3.269 | 1.00 | 21.38 |
| ATOM | 1702 | C | GLY A 456 | -1.219 | 26.654 | 2.815 | 1.00 | 20.38 |
| ATOM | 1703 | O | GLY A 456 | -0.785 | 26.362 | 1.702 | 1.00 | 19.80 |
| ATOM | 1704 | N | TYR A 457 | -0.512 | 27.335 | 3.698 | 1.00 | 21.14 |
| ATOM | 1705 | CA | TYR A 457 | 0.811 | 27.831 | 3.381 | 1.00 | 20.99 |
| ATOM | 1706 | CB | TYR A 457 | 1.232 | 28.847 | 4.448 | 1.00 | 20.64 |
| ATOM | 1707 | CG | TYR A 457 | 2.641 | 29.375 | 4.284 | 1.00 | 22.42 |
| ATOM | 1708 | CD1 | TYR A 457 | 2.905 | 30.522 | 3.509 | 1.00 | 21.39 |
| ATOM | 1709 | CE1 | TYR A 457 | 4.206 | 30.985 | 3.338 | 1.00 | 21.11 |
| ATOM | 1710 | CD2 | TYR A 457 | 3.723 | 28.714 | 4.884 | 1.00 | 22.30 |
| ATOM | 1711 | CE2 | TYR A 457 | 5.022 | 29.170 | 4.712 | 1.00 | 22.43 |
| ATOM | 1712 | CZ | TYR A 457 | 5.253 | 30.300 | 3.941 | 1.00 | 22.21 |
| ATOM | 1713 | OH | TYR A 457 | 6.556 | 30.714 | 3.766 | 1.00 | 25.08 |
| ATOM | 1714 | C | TYR A 457 | 1.859 | 26.723 | 3.241 | 1.00 | 20.80 |
| ATOM | 1715 | O | TYR A 457 | 1.837 | 25.741 | 3.973 | 1.00 | 20.65 |
| ATOM | 1716 | N | ARG A 458 | 2.770 | 26.895 | 2.283 | 1.00 | 20.81 |
| ATOM | 1717 | CA | ARG A 458 | 3.863 | 25.957 | 2.058 | 1.00 | 21.25 |
| ATOM | 1718 | CB | ARG A 458 | 3.614 | 25.128 | 0.797 | 1.00 | 18.60 |
| ATOM | 1719 | CG | ARG A 458 | 2.438 | 24.187 | 0.889 | 1.00 | 15.12 |
| ATOM | 1720 | CD | ARG A 458 | 2.622 | 23.207 | 2.026 | 1.00 | 14.39 |
| ATOM | 1721 | NE | ARG A 458 | 1.603 | 22.173 | 2.013 | 1.00 | 14.00 |
| ATOM | 1722 | CZ | ARG A 458 | 0.483 | 22.218 | 2.733 | 1.00 | 16.22 |
| ATOM | 1723 | NH1 | ARG A 458 | 0.238 | 23.243 | 3.534 | 1.00 | 15.51 |
| ATOM | 1724 | NH2 | ARG A 458 | -0.420 | 21.250 | 2.637 | 1.00 | 15.82 |
| ATOM | 1725 | C | ARG A 458 | 5.168 | 26.743 | 1.903 | 1.00 | 22.68 |
| ATOM | 1726 | O | ARG A 458 | 5.176 | 27.816 | 1.303 | 1.00 | 23.02 |
| ATOM | 1727 | N | MET A 459 | 6.261 | 26.240 | 2.472 | 1.00 | 24.14 |

Figure 8

| | | | | | | | | | |
|---|---|---|---|---|---|---|---|---|---|
| ATOM | 1728 | CA | MET | A | 459 | 7.555 | 26.920 | 2.332 | 1.00 25.51 |
| ATOM | 1729 | CB | MET | A | 459 | 8.646 | 26.208 | 3.125 | 1.00 26.01 |
| ATOM | 1730 | CG | MET | A | 459 | 8.633 | 26.441 | 4.619 | 1.00 27.51 |
| ATOM | 1731 | SD | MET | A | 459 | 10.068 | 25.604 | 5.366 | 1.00 28.19 |
| ATOM | 1732 | CE | MET | A | 459 | 9.369 | 23.974 | 5.718 | 1.00 26.82 |
| ATOM | 1733 | C | MET | A | 459 | 8.005 | 26.971 | 0.870 | 1.00 26.62 |
| ATOM | 1734 | O | MET | A | 459 | 7.726 | 26.054 | 0.083 | 1.00 25.92 |
| ATOM | 1735 | N | VAL | A | 460 | 8.714 | 28.040 | 0.513 | 1.00 28.34 |
| ATOM | 1736 | CA | VAL | A | 460 | 9.221 | 28.198 | -0.849 | 1.00 29.54 |
| ATOM | 1737 | CB | VAL | A | 460 | 9.537 | 29.695 | -1.168 | 1.00 29.20 |
| ATOM | 1738 | CG1 | VAL | A | 460 | 8.316 | 30.550 | -0.882 | 1.00 28.53 |
| ATOM | 1739 | CG2 | VAL | A | 460 | 10.728 | 30.196 | -0.346 | 1.00 28.57 |
| ATOM | 1740 | C | VAL | A | 460 | 10.482 | 27.340 | -1.004 | 1.00 30.67 |
| ATOM | 1741 | O | VAL | A | 460 | 10.956 | 26.750 | -0.034 | 1.00 29.74 |
| ATOM | 1742 | N | ARG | A | 461 | 10.989 | 27.226 | -2.227 | 1.00 32.00 |
| ATOM | 1743 | CA | ARG | A | 461 | 12.202 | 26.458 | -2.484 | 1.00 33.86 |
| ATOM | 1744 | CB | ARG | A | 461 | 12.474 | 26.405 | -3.995 | 1.00 35.06 |
| ATOM | 1745 | CG | ARG | A | 461 | 13.553 | 25.405 | -4.421 | 1.00 37.08 |
| ATOM | 1746 | CD | ARG | A | 461 | 13.770 | 25.383 | -5.946 | 1.00 40.19 |
| ATOM | 1747 | NE | ARG | A | 461 | 14.244 | 26.671 | -6.445 | 1.00 44.05 |
| ATOM | 1748 | CZ | ARG | A | 461 | 15.398 | 27.239 | -6.087 | 1.00 47.49 |
| ATOM | 1749 | NH1 | ARG | A | 461 | 16.228 | 26.635 | -5.236 | 1.00 49.76 |
| ATOM | 1750 | NH2 | ARG | A | 461 | 15.683 | 28.469 | -6.489 | 1.00 48.64 |
| ATOM | 1751 | C | ARG | A | 461 | 13.390 | 27.107 | -1.743 | 1.00 34.96 |
| ATOM | 1752 | O | ARG | A | 461 | 13.751 | 28.259 | -2.021 | 1.00 34.62 |
| ATOM | 1753 | N | PRO | A | 462 | 14.000 | 26.383 | -0.776 | 1.00 36.17 |
| ATOM | 1754 | CD | PRO | A | 462 | 13.683 | 25.008 | -0.341 | 1.00 35.22 |
| ATOM | 1755 | CA | PRO | A | 462 | 15.140 | 26.916 | -0.014 | 1.00 37.35 |
| ATOM | 1756 | CB | PRO | A | 462 | 15.506 | 25.754 | 0.916 | 1.00 36.10 |
| ATOM | 1757 | CG | PRO | A | 462 | 14.228 | 24.985 | 1.053 | 1.00 34.69 |
| ATOM | 1758 | C | PRO | A | 462 | 16.314 | 27.239 | -0.937 | 1.00 39.34 |
| ATOM | 1759 | O | PRO | A | 462 | 16.426 | 26.680 | -2.025 | 1.00 39.30 |
| ATOM | 1760 | N | ASP | A | 463 | 17.186 | 28.138 | -0.503 | 1.00 42.76 |
| ATOM | 1761 | CA | ASP | A | 463 | 18.349 | 28.493 | -1.307 | 1.00 45.86 |
| ATOM | 1762 | CB | ASP | A | 463 | 19.145 | 29.630 | -0.651 | 1.00 48.76 |
| ATOM | 1763 | CG | ASP | A | 463 | 18.406 | 30.961 | -0.674 | 1.00 51.32 |
| ATOM | 1764 | OD1 | ASP | A | 463 | 17.622 | 31.203 | -1.622 | 1.00 52.75 |
| ATOM | 1765 | OD2 | ASP | A | 463 | 18.623 | 31.767 | 0.264 | 1.00 53.75 |
| ATOM | 1766 | C | ASP | A | 463 | 19.255 | 27.275 | -1.472 | 1.00 46.67 |
| ATOM | 1767 | O | ASP | A | 463 | 19.488 | 26.518 | -0.509 | 1.00 46.75 |
| ATOM | 1768 | N | ASN | A | 464 | 19.756 | 27.103 | -2.699 | 1.00 46.93 |
| ATOM | 1769 | CA | ASN | A | 464 | 20.657 | 26.003 | -3.055 | 1.00 46.95 |
| ATOM | 1770 | CB | ASN | A | 464 | 21.966 | 26.100 | -2.245 | 1.00 50.51 |
| ATOM | 1771 | CG | ASN | A | 464 | 22.785 | 27.365 | -2.582 | 1.00 53.25 |
| ATOM | 1772 | OD1 | ASN | A | 464 | 23.560 | 27.383 | -3.548 | 1.00 54.33 |
| ATOM | 1773 | ND2 | ASN | A | 464 | 22.625 | 28.416 | -1.769 | 1.00 53.90 |
| ATOM | 1774 | C | ASN | A | 464 | 20.013 | 24.620 | -2.884 | 1.00 45.49 |
| ATOM | 1775 | O | ASN | A | 464 | 20.599 | 23.718 | -2.273 | 1.00 45.51 |
| ATOM | 1776 | N | CYS | A | 465 | 18.806 | 24.473 | -3.439 | 1.00 42.92 |
| ATOM | 1777 | CA | CYS | A | 465 | 18.027 | 23.230 | -3.381 | 1.00 38.66 |
| ATOM | 1778 | CB | CYS | A | 465 | 16.840 | 23.405 | -2.406 | 1.00 37.19 |
| ATOM | 1779 | SG | CYS | A | 465 | 15.522 | 22.109 | -2.407 | 1.00 33.11 |
| ATOM | 1780 | C | CYS | A | 465 | 17.508 | 22.915 | -4.787 | 1.00 36.98 |
| ATOM | 1781 | O | CYS | A | 465 | 16.941 | 23.780 | -5.442 | 1.00 37.10 |
| ATOM | 1782 | N | PRO | A | 466 | 17.752 | 21.696 | -5.297 | 1.00 35.06 |
| ATOM | 1783 | CD | PRO | A | 466 | 18.625 | 20.644 | -4.751 | 1.00 33.45 |
| ATOM | 1784 | CA | PRO | A | 466 | 17.269 | 21.340 | -6.641 | 1.00 33.99 |
| ATOM | 1785 | CB | PRO | A | 466 | 17.774 | 19.908 | -6.810 | 1.00 33.19 |
| ATOM | 1786 | CG | PRO | A | 466 | 19.012 | 19.893 | -5.990 | 1.00 33.67 |
| ATOM | 1787 | C | PRO | A | 466 | 15.730 | 21.402 | -6.749 | 1.00 33.58 |

Figure 8

| | | | | | | | | |
|---|---|---|---|---|---|---|---|---|
| ATOM | 1788 | O | PRO | A | 466 | 15.030 | 21.129 | -5.782 | 1.00 33.99 |
| ATOM | 1789 | N | GLU | A | 467 | 15.203 | 21.736 | -7.925 | 1.00 33.60 |
| ATOM | 1790 | CA | GLU | A | 467 | 13.753 | 21.814 | -8.095 | 1.00 33.37 |
| ATOM | 1791 | CB | GLU | A | 467 | 13.358 | 22.474 | -9.422 | 1.00 33.92 |
| ATOM | 1792 | CG | GLU | A | 467 | 12.678 | 23.858 | -9.260 | 1.00 36.22 |
| ATOM | 1793 | CD | GLU | A | 467 | 11.231 | 23.812 | -8.716 | 1.00 36.57 |
| ATOM | 1794 | OE1 | GLU | A | 467 | 10.937 | 24.527 | -7.727 | 1.00 37.24 |
| ATOM | 1795 | OE2 | GLU | A | 467 | 10.373 | 23.113 | -9.305 | 1.00 36.28 |
| ATOM | 1796 | C | GLU | A | 467 | 13.109 | 20.449 | -7.984 | 1.00 32.66 |
| ATOM | 1797 | O | GLU | A | 467 | 11.956 | 20.347 | -7.594 | 1.00 32.70 |
| ATOM | 1798 | N | GLU | A | 468 | 13.847 | 19.395 | -8.308 | 1.00 32.02 |
| ATOM | 1799 | CA | GLU | A | 468 | 13.275 | 18.065 | -8.193 | 1.00 32.26 |
| ATOM | 1800 | CB | GLU | A | 468 | 14.103 | 17.008 | -8.922 | 1.00 35.27 |
| ATOM | 1801 | CG | GLU | A | 468 | 14.252 | 17.226 | -10.405 | 1.00 39.65 |
| ATOM | 1802 | CD | GLU | A | 468 | 15.197 | 18.374 | -10.727 | 1.00 43.11 |
| ATOM | 1803 | OE1 | GLU | A | 468 | 16.159 | 18.631 | -9.942 | 1.00 43.89 |
| ATOM | 1804 | OE2 | GLU | A | 468 | 14.968 | 19.019 | -11.777 | 1.00 45.31 |
| ATOM | 1805 | C | GLU | A | 468 | 13.166 | 17.689 | -6.723 | 1.00 31.33 |
| ATOM | 1806 | O | GLU | A | 468 | 12.302 | 16.911 | -6.355 | 1.00 32.11 |
| ATOM | 1807 | N | LEU | A | 469 | 14.069 | 18.204 | -5.888 | 1.00 29.63 |
| ATOM | 1808 | CA | LEU | A | 469 | 14.020 | 17.904 | -4.461 | 1.00 27.95 |
| ATOM | 1809 | CB | LEU | A | 469 | 15.332 | 18.271 | -3.757 | 1.00 26.75 |
| ATOM | 1810 | CG | LEU | A | 469 | 15.441 | 18.031 | -2.250 | 1.00 25.35 |
| ATOM | 1811 | CD1 | LEU | A | 469 | 15.249 | 16.572 | -1.904 | 1.00 25.51 |
| ATOM | 1812 | CD2 | LEU | A | 469 | 16.795 | 18.473 | -1.803 | 1.00 26.01 |
| ATOM | 1813 | C | LEU | A | 469 | 12.857 | 18.675 | -3.851 | 1.00 27.39 |
| ATOM | 1814 | O | LEU | A | 469 | 12.152 | 18.153 | -2.977 | 1.00 27.29 |
| ATOM | 1815 | N | TYR | A | 470 | 12.632 | 19.892 | -4.353 | 1.00 26.13 |
| ATOM | 1816 | CA | TYR | A | 470 | 11.541 | 20.732 | -3.858 | 1.00 25.37 |
| ATOM | 1817 | CB | TYR | A | 470 | 11.583 | 22.140 | -4.439 | 1.00 23.71 |
| ATOM | 1818 | CG | TYR | A | 470 | 10.466 | 23.016 | -3.891 | 1.00 23.88 |
| ATOM | 1819 | CD1 | TYR | A | 470 | 10.377 | 23.288 | -2.522 | 1.00 22.15 |
| ATOM | 1820 | CE1 | TYR | A | 470 | 9.383 | 24.112 | -2.015 | 1.00 22.32 |
| ATOM | 1821 | CD2 | TYR | A | 470 | 9.514 | 23.593 | -4.736 | 1.00 23.17 |
| ATOM | 1822 | CE2 | TYR | A | 470 | 8.509 | 24.425 | -4.228 | 1.00 22.21 |
| ATOM | 1823 | CZ | TYR | A | 470 | 8.449 | 24.682 | -2.873 | 1.00 23.09 |
| ATOM | 1824 | OH | TYR | A | 470 | 7.467 | 25.521 | -2.375 | 1.00 22.32 |
| ATOM | 1825 | C | TYR | A | 470 | 10.191 | 20.130 | -4.179 | 1.00 25.78 |
| ATOM | 1826 | O | TYR | A | 470 | 9.260 | 20.189 | -3.370 | 1.00 26.48 |
| ATOM | 1827 | N | GLN | A | 471 | 10.073 | 19.580 | -5.381 | 1.00 25.92 |
| ATOM | 1828 | CA | GLN | A | 471 | 8.827 | 18.968 | -5.774 | 1.00 25.50 |
| ATOM | 1829 | CB | GLN | A | 471 | 8.800 | 18.727 | -7.284 | 1.00 25.49 |
| ATOM | 1830 | CG | GLN | A | 471 | 8.659 | 20.040 | -8.094 | 1.00 26.26 |
| ATOM | 1831 | CD | GLN | A | 471 | 8.659 | 20.981 | -7.613 | 1.00 28.42 |
| ATOM | 1832 | OE1 | GLN | A | 471 | 7.501 | 20.981 | -7.222 | 1.00 27.13 |
| ATOM | 1833 | NE2 | GLN | A | 471 | 6.399 | 20.532 | -7.666 | 1.00 27.24 |
| ATOM | 1834 | C | GLN | A | 471 | 7.758 | 22.289 | -4.939 | 1.00 25.00 |
| ATOM | 1835 | O | GLN | A | 471 | 8.562 | 17.710 | -4.732 | 1.00 25.30 |
| ATOM | 1836 | N | LEU | A | 472 | 7.416 | 17.333 | -4.378 | 1.00 24.68 |
| ATOM | 1837 | CA | LEU | A | 472 | 9.620 | 17.131 | -3.523 | 1.00 24.20 |
| ATOM | 1838 | CB | LEU | A | 472 | 9.489 | 15.955 | -3.361 | 1.00 25.14 |
| ATOM | 1839 | CG | LEU | A | 472 | 10.827 | 15.247 | -3.235 | 1.00 25.87 |
| ATOM | 1840 | CD1 | LEU | A | 472 | 10.777 | 13.725 | -4.558 | 1.00 24.60 |
| ATOM | 1841 | CD2 | LEU | A | 472 | 10.383 | 13.092 | -2.809 | 1.00 27.28 |
| ATOM | 1842 | C | LEU | A | 472 | 12.146 | 13.230 | -2.166 | 1.00 23.89 |
| ATOM | 1843 | O | LEU | A | 472 | 8.998 | 16.441 | -1.539 | 1.00 25.19 |
| ATOM | 1844 | N | MET | A | 473 | 8.152 | 15.795 | -1.710 | 1.00 21.67 |
| ATOM | 1845 | CA | MET | A | 473 | 9.526 | 17.576 | -0.448 | 1.00 20.95 |
| ATOM | 1846 | CB | MET | A | 473 | 9.084 | 18.157 | -0.171 | 1.00 20.04 |
| ATOM | 1847 | CG | MET | A | 473 | 9.845 | 19.445 | 0.168 | 1.00 20.15 |

Figure 8

```
ATOM   1848  SD  MET A 473      12.065  20.898   0.239  1.00 21.31
ATOM   1849  CE  MET A 473      13.809  20.447   0.532  1.00 19.42
ATOM   1850  C   MET A 473       7.582  18.482  -0.526  1.00 20.51
ATOM   1851  O   MET A 473       6.832  18.259   0.417  1.00 20.74
ATOM   1852  N   ARG A 474       7.153  19.006  -1.667  1.00 20.82
ATOM   1853  CA  ARG A 474       5.765  19.374  -1.868  1.00 21.55
ATOM   1854  CB  ARG A 474       5.631  20.204  -3.151  1.00 22.33
ATOM   1855  CG  ARG A 474       6.312  21.593  -3.068  1.00 22.59
ATOM   1856  CD  ARG A 474       5.781  22.434  -1.881  1.00 23.27
ATOM   1857  NE  ARG A 474       4.354  22.742  -2.027  1.00 22.75
ATOM   1858  CZ  ARG A 474       3.870  23.750  -2.746  1.00 22.86
ATOM   1859  NH1 ARG A 474       4.682  24.576  -3.389  1.00 23.07
ATOM   1860  NH2 ARG A 474       2.561  23.911  -2.863  1.00 22.72
ATOM   1861  C   ARG A 474       4.806  18.176  -1.857  1.00 22.17
ATOM   1862  O   ARG A 474       3.630  18.323  -1.532  1.00 22.08
ATOM   1863  N   LEU A 475       5.315  16.994  -2.205  1.00 22.36
ATOM   1864  CA  LEU A 475       4.515  15.766  -2.194  1.00 22.55
ATOM   1865  CB  LEU A 475       5.163  14.666  -3.038  1.00 21.32
ATOM   1866  CG  LEU A 475       5.136  14.889  -4.556  1.00 22.13
ATOM   1867  CD1 LEU A 475       5.889  13.775  -5.267  1.00 20.68
ATOM   1868  CD2 LEU A 475       3.707  14.952  -5.063  1.00 21.02
ATOM   1869  C   LEU A 475       4.380  15.311  -0.745  1.00 23.54
ATOM   1870  O   LEU A 475       3.357  14.764  -0.343  1.00 25.08
ATOM   1871  N   CYS A 476       5.413  15.572   0.049  1.00 23.50
ATOM   1872  CA  CYS A 476       5.393  15.225   1.463  1.00 22.10
ATOM   1873  CB  CYS A 476       6.795  15.356   2.071  1.00 21.15
ATOM   1874  SG  CYS A 476       8.092  14.271   1.382  1.00 23.19
ATOM   1875  C   CYS A 476       4.433  16.174   2.185  1.00 21.76
ATOM   1876  O   CYS A 476       3.908  15.833   3.245  1.00 21.44
ATOM   1877  N   TRP A 477       4.187  17.348   1.596  1.00 21.62
ATOM   1878  CA  TRP A 477       3.298  18.342   2.206  1.00 21.77
ATOM   1879  CB  TRP A 477       3.930  19.743   2.186  1.00 20.77
ATOM   1880  CG  TRP A 477       5.295  19.799   2.788  1.00 21.23
ATOM   1881  CD2 TRP A 477       6.347  20.728   2.476  1.00 22.39
ATOM   1882  CE2 TRP A 477       7.463  20.378   3.277  1.00 23.26
ATOM   1883  CE3 TRP A 477       6.459  21.826   1.600  1.00 23.04
ATOM   1884  CD1 TRP A 477       5.799  18.960   3.735  1.00 22.15
ATOM   1885  NE1 TRP A 477       7.094  19.295   4.038  1.00 21.35
ATOM   1886  CZ2 TRP A 477       8.692  21.087   3.227  1.00 22.86
ATOM   1887  CZ3 TRP A 477       7.677  22.528   1.549  1.00 22.69
ATOM   1888  CH2 TRP A 477       8.776  22.150   2.360  1.00 22.27
ATOM   1889  C   TRP A 477       1.887  18.412   1.608  1.00 22.48
ATOM   1890  O   TRP A 477       1.212  19.432   1.759  1.00 24.19
ATOM   1891  N   LYS A 478       1.437  17.359   0.926  1.00 21.82
ATOM   1892  CA  LYS A 478       0.090  17.364   0.371  1.00 21.65
ATOM   1893  CB  LYS A 478      -0.210  16.075  -0.395  1.00 21.78
ATOM   1894  CG  LYS A 478       0.567  15.914  -1.686  1.00 23.10
ATOM   1895  CD  LYS A 478       0.296  17.038  -2.646  1.00 22.56
ATOM   1896  CE  LYS A 478      -1.095  16.935  -3.186  1.00 24.11
ATOM   1897  NZ  LYS A 478      -1.395  18.089  -4.073  1.00 28.05
ATOM   1898  C   LYS A 478      -0.847  17.474   1.550  1.00 22.22
ATOM   1899  O   LYS A 478      -0.574  16.925   2.609  1.00 23.17
ATOM   1900  N   GLU A 479      -1.948  18.192   1.378  1.00 23.55
ATOM   1901  CA  GLU A 479      -2.896  18.369   2.472  1.00 23.63
ATOM   1902  CB  GLU A 479      -4.061  19.260   2.058  1.00 22.67
ATOM   1903  CG  GLU A 479      -4.941  19.664   3.227  1.00 22.78
ATOM   1904  CD  GLU A 479      -4.189  20.471   4.290  1.00 24.52
ATOM   1905  OE1 GLU A 479      -3.302  21.290   3.939  1.00 23.01
ATOM   1906  OE2 GLU A 479      -4.497  20.285   5.489  1.00 25.50
ATOM   1907  C   GLU A 479      -3.420  17.045   2.986  1.00 23.83
```

Figure 8

```
ATOM   1908  O    GLU A 479      -3.400  16.800   4.182  1.00 25.36
ATOM   1909  N    ARG A 480      -3.865  16.184   2.083  1.00 23.50
ATOM   1910  CA   ARG A 480      -4.398  14.887   2.480  1.00 22.59
ATOM   1911  CB   ARG A 480      -5.370  14.391   1.441  1.00 25.16
ATOM   1912  CG   ARG A 480      -6.566  15.232   1.234  1.00 27.75
ATOM   1913  CD   ARG A 480      -7.232  14.631   0.050  1.00 34.02
ATOM   1914  NE   ARG A 480      -8.398  15.367  -0.394  1.00 40.66
ATOM   1915  CZ   ARG A 480      -8.715  15.538  -1.675  1.00 43.72
ATOM   1916  NH1  ARG A 480      -7.941  15.031  -2.639  1.00 43.83
ATOM   1917  NH2  ARG A 480      -9.831  16.183  -1.992  1.00 45.57
ATOM   1918  C    ARG A 480      -3.280  13.873   2.599  1.00 20.98
ATOM   1919  O    ARG A 480      -2.535  13.689   1.664  1.00 19.88
ATOM   1920  N    PRO A 481      -3.229  13.127   3.716  1.00 21.09
ATOM   1921  CD   PRO A 481      -4.283  13.140   4.753  1.00 20.16
ATOM   1922  CA   PRO A 481      -2.234  12.099   4.030  1.00 20.81
ATOM   1923  CB   PRO A 481      -2.817  11.447   5.290  1.00 20.51
ATOM   1924  CG   PRO A 481      -3.591  12.530   5.923  1.00 18.98
ATOM   1925  C    PRO A 481      -2.045  11.055   2.933  1.00 21.63
ATOM   1926  O    PRO A 481      -0.923  10.618   2.680  1.00 21.44
ATOM   1927  N    GLU A 482      -3.145  10.663   2.288  1.00 22.15
ATOM   1928  CA   GLU A 482      -3.122   9.646   1.234  1.00 22.20
ATOM   1929  CB   GLU A 482      -4.552   9.257   0.844  1.00 22.91
ATOM   1930  CG   GLU A 482      -5.300  10.375   0.131  1.00 24.00
ATOM   1931  CD   GLU A 482      -6.396  11.007   0.966  1.00 24.48
ATOM   1932  OE1  GLU A 482      -6.252  11.098   2.209  1.00 23.15
ATOM   1933  OE2  GLU A 482      -7.416  11.408   0.355  1.00 26.08
ATOM   1934  C    GLU A 482      -2.355  10.091  -0.006  1.00 21.31
ATOM   1935  O    GLU A 482      -1.860   9.269  -0.774  1.00 21.85
ATOM   1936  N    ASP A 483      -2.281  11.399  -0.207  1.00 21.17
ATOM   1937  CA   ASP A 483      -1.579  11.976  -1.346  1.00 20.30
ATOM   1938  CB   ASP A 483      -2.142  13.367  -1.663  1.00 20.87
ATOM   1939  CG   ASP A 483      -3.568  13.315  -2.210  1.00 21.74
ATOM   1940  OD1  ASP A 483      -3.940  12.309  -2.833  1.00 21.25
ATOM   1941  OD2  ASP A 483      -4.327  14.278  -2.015  1.00 23.25
ATOM   1942  C    ASP A 483      -0.078  12.067  -1.127  1.00 19.47
ATOM   1943  O    ASP A 483       0.649  12.433  -2.035  1.00 20.30
ATOM   1944  N    ARG A 484       0.382  11.761   0.080  1.00 19.15
ATOM   1945  CA   ARG A 484       1.813  11.801   0.403  1.00 19.66
ATOM   1946  CB   ARG A 484       2.008  12.124   1.900  1.00 18.19
ATOM   1947  CG   ARG A 484       1.359  13.421   2.321  1.00 15.37
ATOM   1948  CD   ARG A 484       1.466  13.647   3.811  1.00 16.29
ATOM   1949  NE   ARG A 484       0.567  14.727   4.241  1.00 18.07
ATOM   1950  CZ   ARG A 484      -0.018  14.823   5.440  1.00 17.07
ATOM   1951  NH1  ARG A 484       0.196  13.916   6.369  1.00 15.88
ATOM   1952  NH2  ARG A 484      -0.874  15.805   5.688  1.00 16.33
ATOM   1953  C    ARG A 484       2.486  10.462   0.024  1.00 19.94
ATOM   1954  O    ARG A 484       1.877   9.396   0.151  1.00 19.58
ATOM   1955  N    PRO A 485       3.745  10.504  -0.458  1.00 20.13
ATOM   1956  CD   PRO A 485       4.608  11.685  -0.602  1.00 20.12
ATOM   1957  CA   PRO A 485       4.466   9.290  -0.854  1.00 20.41
ATOM   1958  CB   PRO A 485       5.789   9.838  -1.399  1.00 21.61
ATOM   1959  CG   PRO A 485       5.505  11.260  -1.709  1.00 22.23
ATOM   1960  C    PRO A 485       4.762   8.345   0.306  1.00 21.14
ATOM   1961  O    PRO A 485       4.710   8.738   1.475  1.00 21.53
ATOM   1962  N    THR A 486       5.068   7.095  -0.021  1.00 19.94
ATOM   1963  CA   THR A 486       5.451   6.141   1.005  1.00 20.18
ATOM   1964  CB   THR A 486       5.283   4.700   0.536  1.00 18.76
ATOM   1965  OG1  THR A 486       5.912   4.546  -0.734  1.00 19.31
ATOM   1966  CG2  THR A 486       3.836   4.343   0.428  1.00 15.80
ATOM   1967  C    THR A 486       6.948   6.400   1.206  1.00 20.82
```

Figure 8

| | | | | | | | | |
|---|---|---|---|---|---|---|---|---|
| ATOM | 1968 | O | THR | A | 486 | 7.582 | 7.007 | 0.340 | 1.00 21.88 |
| ATOM | 1969 | N | PHE | A | 487 | 7.508 | 6.003 | 2.344 | 1.00 20.71 |
| ATOM | 1970 | CA | PHE | A | 487 | 8.938 | 6.196 | 2.551 | 1.00 20.45 |
| ATOM | 1971 | CB | PHE | A | 487 | 9.324 | 5.906 | 3.984 | 1.00 18.79 |
| ATOM | 1972 | CG | PHE | A | 487 | 9.052 | 7.035 | 4.910 | 1.00 18.42 |
| ATOM | 1973 | CD1 | PHE | A | 487 | 9.837 | 8.191 | 4.859 | 1.00 16.94 |
| ATOM | 1974 | CD2 | PHE | A | 487 | 8.044 | 6.945 | 5.864 | 1.00 17.83 |
| ATOM | 1975 | CE1 | PHE | A | 487 | 9.630 | 9.229 | 5.740 | 1.00 13.86 |
| ATOM | 1976 | CE2 | PHE | A | 487 | 7.828 | 7.987 | 6.757 | 1.00 17.19 |
| ATOM | 1977 | CZ | PHE | A | 487 | 8.627 | 9.133 | 6.693 | 1.00 16.38 |
| ATOM | 1978 | C | PHE | A | 487 | 9.659 | 5.242 | 1.633 | 1.00 21.55 |
| ATOM | 1979 | O | PHE | A | 487 | 10.796 | 5.459 | 1.252 | 1.00 21.63 |
| ATOM | 1980 | N | ASP | A | 488 | 8.966 | 4.176 | 1.267 | 1.00 23.84 |
| ATOM | 1981 | CA | ASP | A | 488 | 9.516 | 3.182 | 0.361 | 1.00 26.01 |
| ATOM | 1982 | CB | ASP | A | 488 | 8.489 | 2.068 | 0.165 | 1.00 28.39 |
| ATOM | 1983 | CG | ASP | A | 488 | 8.899 | 1.071 | -0.880 | 1.00 31.52 |
| ATOM | 1984 | OD1 | ASP | A | 488 | 10.098 | 0.715 | -0.934 | 1.00 35.19 |
| ATOM | 1985 | OD2 | ASP | A | 488 | 8.010 | 0.637 | -1.645 | 1.00 32.80 |
| ATOM | 1986 | C | ASP | A | 488 | 9.833 | 3.894 | -0.951 | 1.00 26.63 |
| ATOM | 1987 | O | ASP | A | 488 | 10.887 | 3.685 | -1.541 | 1.00 28.05 |
| ATOM | 1988 | N | TYR | A | 489 | 8.954 | 4.809 | -1.353 | 1.00 26.44 |
| ATOM | 1989 | CA | TYR | A | 489 | 9.151 | 5.562 | -2.575 | 1.00 25.51 |
| ATOM | 1990 | CB | TYR | A | 489 | 7.852 | 6.235 | -3.008 | 1.00 23.88 |
| ATOM | 1991 | CG | TYR | A | 489 | 8.052 | 7.236 | -4.112 | 1.00 20.99 |
| ATOM | 1992 | CD1 | TYR | A | 489 | 8.404 | 6.825 | -5.394 | 1.00 20.71 |
| ATOM | 1993 | CE1 | TYR | A | 489 | 8.679 | 7.756 | -6.405 | 1.00 19.41 |
| ATOM | 1994 | CD2 | TYR | A | 489 | 7.969 | 8.604 | -3.857 | 1.00 20.60 |
| ATOM | 1995 | CE2 | TYR | A | 489 | 8.244 | 9.543 | -4.845 | 1.00 18.63 |
| ATOM | 1996 | CZ | TYR | A | 489 | 8.602 | 9.116 | -6.114 | 1.00 20.13 |
| ATOM | 1997 | OH | TYR | A | 489 | 8.931 | 10.049 | -7.078 | 1.00 21.42 |
| ATOM | 1998 | C | TYR | A | 489 | 10.232 | 6.611 | -2.378 | 1.00 26.64 |
| ATOM | 1999 | O | TYR | A | 489 | 11.098 | 6.770 | -3.241 | 1.00 28.04 |
| ATOM | 2000 | N | LEU | A | 490 | 10.160 | 7.351 | -1.273 | 1.00 26.20 |
| ATOM | 2001 | CA | LEU | A | 490 | 11.149 | 8.377 | -0.968 | 1.00 26.57 |
| ATOM | 2002 | CB | LEU | A | 490 | 10.825 | 9.078 | 0.354 | 1.00 25.78 |
| ATOM | 2003 | CG | LEU | A | 490 | 9.549 | 9.926 | 0.373 | 1.00 24.78 |
| ATOM | 2004 | CD1 | LEU | A | 490 | 9.335 | 10.508 | 1.755 | 1.00 23.16 |
| ATOM | 2005 | CD2 | LEU | A | 490 | 9.625 | 11.020 | -0.681 | 1.00 23.73 |
| ATOM | 2006 | C | LEU | A | 490 | 12.585 | 7.846 | -0.949 | 1.00 27.94 |
| ATOM | 2007 | O | LEU | A | 490 | 13.498 | 8.527 | -1.416 | 1.00 28.42 |
| ATOM | 2008 | N | ARG | A | 491 | 12.796 | 6.632 | -0.439 | 1.00 29.41 |
| ATOM | 2009 | CA | ARG | A | 491 | 14.149 | 6.063 | -0.418 | 1.00 30.79 |
| ATOM | 2010 | CB | ARG | A | 491 | 14.193 | 4.766 | 0.378 | 1.00 31.61 |
| ATOM | 2011 | CG | ARG | A | 491 | 15.527 | 4.039 | 0.262 | 1.00 34.35 |
| ATOM | 2012 | CD | ARG | A | 491 | 15.398 | 2.572 | 0.644 | 1.00 38.43 |
| ATOM | 2013 | NE | ARG | A | 491 | 14.217 | 1.970 | 0.023 | 1.00 41.83 |
| ATOM | 2014 | CZ | ARG | A | 491 | 14.104 | 1.698 | -1.276 | 1.00 43.21 |
| ATOM | 2015 | NH1 | ARG | A | 491 | 15.113 | 1.952 | -2.116 | 1.00 41.81 |
| ATOM | 2016 | NH2 | ARG | A | 491 | 12.945 | 1.243 | -1.743 | 1.00 43.36 |
| ATOM | 2017 | C | ARG | A | 491 | 14.623 | 5.806 | -1.852 | 1.00 31.54 |
| ATOM | 2018 | O | ARG | A | 491 | 15.730 | 6.202 | -2.227 | 1.00 31.18 |
| ATOM | 2019 | N | SER | A | 492 | 13.748 | 5.189 | -2.652 | 1.00 31.96 |
| ATOM | 2020 | CA | SER | A | 492 | 14.015 | 4.877 | -4.055 | 1.00 31.95 |
| ATOM | 2021 | CB | SER | A | 492 | 12.743 | 4.390 | -4.750 | 1.00 31.72 |
| ATOM | 2022 | OG | SER | A | 492 | 12.484 | 3.034 | -4.452 | 1.00 33.49 |
| ATOM | 2023 | C | SER | A | 492 | 14.502 | 6.087 | -4.809 | 1.00 32.20 |
| ATOM | 2024 | O | SER | A | 492 | 15.560 | 6.060 | -5.424 | 1.00 32.25 |
| ATOM | 2025 | N | VAL | A | 493 | 13.701 | 7.147 | -4.767 | 1.00 33.30 |
| ATOM | 2026 | CA | VAL | A | 493 | 14.006 | 8.383 | -5.480 | 1.00 33.69 |
| ATOM | 2027 | CB | VAL | A | 493 | 12.732 | 9.262 | -5.647 | 1.00 33.01 |

Figure 8

```
ATOM   2028  CG1  VAL A 493      12.156    9.601   -4.310  1.00 33.01
ATOM   2029  CG2  VAL A 493      13.045   10.532   -6.444  1.00 34.01
ATOM   2030  C    VAL A 493      15.204    9.191   -4.961  1.00 34.31
ATOM   2031  O    VAL A 493      15.874    9.871   -5.748  1.00 34.65
ATOM   2032  N    LEU A 494      15.508    9.090   -3.664  1.00 35.08
ATOM   2033  CA   LEU A 494      16.654    9.806   -3.094  1.00 35.54
ATOM   2034  CB   LEU A 494      16.476   10.003   -1.585  1.00 33.35
ATOM   2035  CG   LEU A 494      15.463   11.086   -1.217  1.00 32.13
ATOM   2036  CD1  LEU A 494      15.185   11.062    0.262  1.00 29.61
ATOM   2037  CD2  LEU A 494      15.980   12.445   -1.675  1.00 31.30
ATOM   2038  C    LEU A 494      17.979    9.096   -3.394  1.00 36.75
ATOM   2039  O    LEU A 494      19.009    9.743   -3.584  1.00 35.78
ATOM   2040  N    GLU A 495      17.932    7.768   -3.475  1.00 38.96
ATOM   2041  CA   GLU A 495      19.117    6.969   -3.760  1.00 41.61
ATOM   2042  CB   GLU A 495      18.822    5.481   -3.569  1.00 42.04
ATOM   2043  CG   GLU A 495      18.544    5.069   -2.135  1.00 43.96
ATOM   2044  CD   GLU A 495      18.479    3.560   -1.943  1.00 44.48
ATOM   2045  OE1  GLU A 495      18.220    2.836   -2.937  1.00 44.76
ATOM   2046  OE2  GLU A 495      18.674    3.113   -0.785  1.00 43.53
ATOM   2047  C    GLU A 495      19.582    7.172   -5.188  1.00 43.55
ATOM   2048  O    GLU A 495      20.783    7.245   -5.461  1.00 44.37
ATOM   2049  N    ASP A 496      18.613    7.269   -6.093  1.00 45.07
ATOM   2050  CA   ASP A 496      18.885    7.417   -7.515  1.00 46.78
ATOM   2051  CB   ASP A 496      17.898    6.553   -8.308  1.00 47.27
ATOM   2052  CG   ASP A 496      17.846    5.096   -7.817  1.00 49.36
ATOM   2053  OD1  ASP A 496      18.899    4.521   -7.432  1.00 48.61
ATOM   2054  OD2  ASP A 496      16.729    4.521   -7.823  1.00 50.95
ATOM   2055  C    ASP A 496      18.807    8.851   -8.020  1.00 48.23
ATOM   2056  O    ASP A 496      18.781    9.076   -9.228  1.00 48.94
ATOM   2057  N    PHE A 497      18.837    9.818   -7.110  1.00 49.45
ATOM   2058  CA   PHE A 497      18.719   11.219   -7.484  1.00 50.97
ATOM   2059  CB   PHE A 497      18.829   12.109   -6.256  1.00 49.58
ATOM   2060  CG   PHE A 497      17.984   13.333   -6.335  1.00 47.98
ATOM   2061  CD1  PHE A 497      16.611   13.258   -6.122  1.00 47.22
ATOM   2062  CD2  PHE A 497      18.557   14.562   -6.627  1.00 48.49
ATOM   2063  CE1  PHE A 497      15.818   14.389   -6.194  1.00 47.61
ATOM   2064  CE2  PHE A 497      17.782   15.711   -6.704  1.00 48.96
ATOM   2065  CZ   PHE A 497      16.405   15.626   -6.487  1.00 49.12
ATOM   2066  C    PHE A 497      19.659   11.692   -8.589  1.00 52.99
ATOM   2067  O    PHE A 497      19.245   12.442   -9.471  1.00 53.90
ATOM   2068  N    PHE A 498      20.926   11.297   -8.522  1.00 55.02
ATOM   2069  CA   PHE A 498      21.895   11.662   -9.566  1.00 57.20
ATOM   2070  CB   PHE A 498      22.125   13.196   -9.692  1.00 57.52
ATOM   2071  CG   PHE A 498      22.364   13.920   -8.375  1.00 57.40
ATOM   2072  CD1  PHE A 498      23.000   13.293   -7.306  1.00 57.05
ATOM   2073  CD2  PHE A 498      21.927   15.239   -8.214  1.00 56.94
ATOM   2074  CE1  PHE A 498      23.193   13.963   -6.108  1.00 57.41
ATOM   2075  CE2  PHE A 498      22.115   15.920   -7.023  1.00 56.39
ATOM   2076  CZ   PHE A 498      22.746   15.282   -5.967  1.00 57.42
ATOM   2077  C    PHE A 498      23.217   10.910   -9.448  1.00 57.83
ATOM   2078  O    PHE A 498      23.211    9.761   -9.940  1.00 58.28
ATOM   2079  N1   LIG A 500      23.926    7.514   20.709  1.00 29.87
ATOM   2080  C1   LIG A 500      24.534    8.769   20.672  1.00 29.27
ATOM   2081  N2   LIG A 500      25.789    8.892   20.202  1.00 29.60
ATOM   2082  C2   LIG A 500      26.397   10.069   20.145  1.00 28.65
ATOM   2083  N3   LIG A 500      25.819   11.166   20.529  1.00 28.98
ATOM   2084  C3   LIG A 500      24.563   11.154   21.003  1.00 29.31
ATOM   2085  N4   LIG A 500      23.729   12.134   21.474  1.00 28.41
ATOM   2086  C4   LIG A 500      23.992   13.581   21.609  1.00 28.00
ATOM   2087  C5   LIG A 500      23.667   14.122   23.007  1.00 27.29
```

Figure 8

```
ATOM   2088  C6   LIG A 500      23.913  15.633  23.078  1.00 27.38
ATOM   2089  C7   LIG A 500      23.058  16.349  21.990  1.00 28.21
ATOM   2090  N5   LIG A 500      23.272  17.810  22.087  1.00 28.76
ATOM   2091  C8   LIG A 500      24.581  18.273  21.577  1.00 28.97
ATOM   2092  C9   LIG A 500      24.707  19.782  21.816  1.00 28.86
ATOM   2093  N6   LIG A 500      23.660  20.481  21.057  1.00 29.26
ATOM   2094  C10  LIG A 500      23.788  21.932  21.326  1.00 29.32
ATOM   2095  C11  LIG A 500      22.375  20.042  21.536  1.00 28.92
ATOM   2096  C12  LIG A 500      22.223  18.532  21.337  1.00 28.89
ATOM   2097  C13  LIG A 500      23.425  15.836  20.599  1.00 27.51
ATOM   2098  C14  LIG A 500      23.166  14.313  20.522  1.00 27.75
ATOM   2099  C15  LIG A 500      22.528  11.588  21.858  1.00 28.49
ATOM   2100  C16  LIG A 500      22.545  10.249  21.659  1.00 28.91
ATOM   2101  C17  LIG A 500      21.376   9.455  22.032  1.00 28.87
ATOM   2102  C18  LIG A 500      21.637   8.415  22.922  1.00 29.09
ATOM   2103  C19  LIG A 500      20.614   7.612  23.381  1.00 29.68
ATOM   2104  O1   LIG A 500      20.854   6.574  24.239  1.00 30.48
ATOM   2105  C20  LIG A 500      22.047   6.867  24.973  1.00 29.76
ATOM   2106  C21  LIG A 500      19.301   7.853  22.961  1.00 29.84
ATOM   2107  N7   LIG A 500      18.263   7.013  23.438  1.00 29.79
ATOM   2108  C22  LIG A 500      16.847   6.982  23.200  1.00 29.91
ATOM   2109  C23  LIG A 500      16.378   6.246  21.959  1.00 30.60
ATOM   2110  O2   LIG A 500      15.106   5.793  21.739  1.00 31.41
ATOM   2111  C24  LIG A 500      15.015   5.160  20.546  1.00 30.67
ATOM   2112  C25  LIG A 500      13.749   4.526  19.981  1.00 29.64
ATOM   2113  C26  LIG A 500      16.254   5.202  19.967  1.00 30.71
ATOM   2114  C27  LIG A 500      17.130   5.902  20.885  1.00 30.90
ATOM   2115  C28  LIG A 500      19.029   8.905  22.061  1.00 29.39
ATOM   2116  C29  LIG A 500      20.060   9.712  21.599  1.00 28.56
ATOM   2117  C30  LIG A 500      23.871   9.916  21.090  1.00 28.75
ATOM   2118  OH2  H2O A 600       5.191  21.957   9.036  1.00 26.52
ATOM   2119  OH2  H2O A 601       1.207   2.818  -1.688  1.00 72.57
ATOM   2120  OH2  H2O A 602      -1.498  23.815   0.322  1.00 17.51
ATOM   2121  OH2  H2O A 604       5.987   2.207  -2.944  1.00 42.59
ATOM   2122  OH2  H2O A 605      -5.911  25.208   1.816  1.00 55.99
ATOM   2123  OH2  H2O A 606       7.289  12.622  12.664  1.00 16.56
ATOM   2124  OH2  H2O A 607      -4.004  16.644  -0.797  1.00 19.20
ATOM   2125  OH2  H2O A 608       0.384   8.496  -3.168  1.00 60.27
ATOM   2126  OH2  H2O A 609      -1.072  29.909   1.745  1.00 42.11
ATOM   2127  OH2  H2O A 610       5.876  23.928   4.154  1.00 11.94
ATOM   2128  OH2  H2O A 611       5.284  18.216  -6.137  1.00 17.61
ATOM   2129  OH2  H2O A 612       0.584   5.390   0.194  1.00 33.65
ATOM   2130  OH2  H2O A 613      -0.456  28.240  -0.646  1.00 60.82
ATOM   2131  OH2  H2O A 614       9.085   9.072  18.690  1.00 19.30
ATOM   2132  OH2  H2O A 615      -9.695   7.612  -2.993  1.00 39.79
ATOM   2133  OH2  H2O A 616      -2.044   6.495  -0.396  1.00 31.85
ATOM   2134  OH2  H2O A 617       2.464  29.578  -0.199  1.00 78.12
ATOM   2135  OH2  H2O A 618       8.349  24.391  15.886  1.00 40.13
ATOM   2136  OH2  H2O A 619      -1.433   4.702   4.179  1.00 95.76
ATOM   2137  OH2  H2O A 620       1.221  26.736  -3.069  1.00 23.00
ATOM   2138  OH2  H2O A 621      29.630  12.923  20.402  1.00 52.30
ATOM   2139  OH2  H2O A 622       3.490   0.242  -2.046  1.00 46.71
ATOM   2140  OH2  H2O A 623      -3.976  23.163   1.635  1.00 28.76
ATOM   2141  OH2  H2O A 624      35.803  11.763  22.401  1.00 44.55
ATOM   2142  OH2  H2O A 625      19.908   4.637   1.358  1.00 47.41
ATOM   2143  OH2  H2O A 626      15.229  19.247  14.126  1.00 31.01
ATOM   2144  OH2  H2O A 627       3.407   5.894   3.720  1.00 17.86
ATOM   2145  OH2  H2O A 628       3.770  15.261  11.440  1.00 24.97
ATOM   2146  OH2  H2O A 630       8.282  14.393  -7.203  1.00 65.28
ATOM   2147  OH2  H2O A 631      33.652  -1.121  33.347  1.00 65.64
```

Figure 8

```
ATOM   2148  OH2 H2O A 632       5.238   27.541   -1.549  1.00 16.07
ATOM   2149  OH2 H2O A 633      16.800   12.120   19.100  1.00 48.96
ATOM   2150  OH2 H2O A 634      17.070   -1.137    4.469  1.00 34.07
ATOM   2151  OH2 H2O A 635      -1.610   11.418    9.489  1.00 27.18
ATOM   2152  OH2 H2O A 636      -2.403   11.889   -5.088  1.00 28.35
ATOM   2153  OH2 H2O A 638      -8.393    7.805   -5.531  1.00 40.40
ATOM   2154  OH2 H2O A 639      15.566   10.185   -8.490  1.00 40.47
ATOM   2155  OH2 H2O A 640      -1.944   23.207    5.345  1.00 23.63
ATOM   2156  OH2 H2O A 641      -3.058    6.037    2.302  1.00 21.22
ATOM   2157  OH2 H2O A 642      19.205   -0.921   15.238  1.00 23.66
ATOM   2158  OH2 H2O A 643      26.299   22.287   33.449  1.00100.00
ATOM   2159  OH2 H2O A 644       2.632   20.745   -0.702  1.00 26.32
ATOM   2160  OH2 H2O A 645      -4.642   23.621    9.568  1.00 37.53
ATOM   2161  OH2 H2O A 646      28.354    0.722   41.120  1.00 71.48
ATOM   2162  OH2 H2O A 647       4.236   35.710    6.745  1.00 55.48
ATOM   2163  OH2 H2O A 648       0.803    4.660   10.377  1.00 26.37
ATOM   2164  OH2 H2O A 649     -13.278    5.306   -2.391  1.00 67.99
ATOM   2165  OH2 H2O A 650      11.959   27.763    2.101  1.00 34.74
ATOM   2166  OH2 H2O A 651       2.738   -2.711    0.934  1.00 39.38
ATOM   2167  OH2 H2O A 652      -1.419   20.472   -1.023  1.00 40.67
ATOM   2168  OH2 H2O A 653       3.622   22.224   11.134  1.00 21.41
ATOM   2169  OH2 H2O A 654       3.260   30.588   -4.222  1.00 29.48
ATOM   2170  OH2 H2O A 655      23.846   20.060   26.474  1.00 77.25
ATOM   2171  OH2 H2O A 656       4.369    3.306   16.320  1.00 64.90
ATOM   2172  OH2 H2O A 657       1.123    2.714    6.231  1.00 97.08
ATOM   2173  OH2 H2O A 658      -2.219   24.458   -6.483  1.00 58.23
ATOM   2174  OH2 H2O A 659       9.522   27.788   -4.447  1.00 23.01
ATOM   2175  OH2 H2O A 660      25.585   17.235   17.834  1.00 34.53
ATOM   2176  OH2 H2O A 661      14.735   14.336   23.762  1.00 82.72
ATOM   2177  OH2 H2O A 662      -6.211   10.445   -3.097  1.00 58.97
ATOM   2178  OH2 H2O A 663       6.495   34.315    3.182  1.00 49.17
ATOM   2179  OH2 H2O A 664      27.088   20.709   19.914  1.00 65.69
ATOM   2180  OH2 H2O A 665       2.275    2.524    3.096  1.00 73.54
ATOM   2181  OH2 H2O A 666      -2.508   24.288   -2.231  1.00 42.90
ATOM   2182  OH2 H2O A 667       8.156    0.396    3.555  1.00 36.34
ATOM   2183  OH2 H2O A 668      22.350   22.731   -0.049  1.00 39.48
ATOM   2184  OH2 H2O A 669       5.197    0.863    1.698  1.00 40.24
ATOM   2185  OH2 H2O A 670      -6.254   24.313   -1.921  1.00 97.21
ATOM   2186  OH2 H2O A 671      -0.587    4.730   12.852  1.00 35.71
ATOM   2187  OH2 H2O A 672       6.095    2.347   18.791  1.00 47.97
ATOM   2188  OH2 H2O A 673      33.763   20.539   11.825  1.00 61.76
ATOM   2189  OH2 H2O A 674      14.101    0.040    4.630  1.00 40.74
ATOM   2190  OH2 H2O A 675      -2.805   24.756   11.128  1.00 38.17
ATOM   2191  OH2 H2O A 676      31.600    4.029   18.435  1.00 51.23
ATOM   2192  OH2 H2O A 677       5.375   14.764   13.854  1.00 35.39
ATOM   2193  OH2 H2O A 678      -5.000   17.719    6.650  1.00 41.58
ATOM   2194  OH2 H2O A 679      15.267   20.922   16.344  1.00 41.81
ATOM   2195  OH2 H2O A 680      31.567   15.362   31.954  1.00 57.08
ATOM   2196  OH2 H2O A 681      -6.967   18.717    9.644  1.00 46.43
ATOM   2197  OH2 H2O A 682      29.252    2.272   19.659  1.00 32.25
ATOM   2198  OH2 H2O A 683      18.757   16.975   20.584  1.00 42.99
ATOM   2199  OH2 H2O A 684      14.394   24.794    7.022  1.00 35.03
ATOM   2200  OH2 H2O A 685      -4.720   22.656    7.019  1.00 20.07
ATOM   2201  OH2 H2O A 686      16.833   23.362   -9.530  1.00 54.34
ATOM   2202  OH2 H2O A 687      -1.734   26.643   -4.426  1.00 45.50
ATOM   2203  OH2 H2O A 688      33.707   12.341   10.799  1.00 44.38
ATOM   2204  OH2 H2O A 689      -4.618   24.643   13.195  1.00 36.79
ATOM   2205  OH2 H2O A 690       3.963    4.911   33.137  1.00 44.12
ATOM   2206  OH2 H2O A 691      18.548   -2.255   19.171  1.00 28.71
ATOM   2207  OH2 H2O A 692      12.323   21.373   17.933  1.00 51.25
```

Figure 8

```
ATOM  2208  OH2  H2O  A  693    16.400   23.183   11.968  1.00  25.35
ATOM  2209  OH2  H2O  A  694    17.436   -0.423   17.227  1.00  37.56
ATOM  2210  OH2  H2O  A  695    -9.918   10.556   -6.610  1.00  37.76
ATOM  2211  OH2  H2O  A  696    30.667   16.015    1.251  1.00  47.11
ATOM  2212  OH2  H2O  A  697    10.589   15.948   -8.344  1.00  86.14
ATOM  2213  OH2  H2O  A  698    24.326   11.058   35.133  1.00  50.20
ATOM  2214  OH2  H2O  A  699    -5.999   21.663   -0.034  1.00  29.65
ATOM  2215  OH2  H2O  A  700     5.789   10.461   -8.356  1.00  89.72
ATOM  2216  OH2  H2O  A  701    33.373   12.196   24.000  1.00  66.36
ATOM  2217  CB   TRP  B  238    47.082   28.125   31.990  1.00  54.26
ATOM  2218  CG   TRP  B  238    46.752   28.732   33.321  1.00  53.53
ATOM  2219  CD2  TRP  B  238    47.304   28.381   34.617  1.00  52.99
ATOM  2220  CE2  TRP  B  238    46.594   29.140   35.585  1.00  51.98
ATOM  2221  CE3  TRP  B  238    48.316   27.507   35.054  1.00  52.93
ATOM  2222  CD1  TRP  B  238    45.787   29.666   33.571  1.00  53.72
ATOM  2223  NE1  TRP  B  238    45.678   29.913   34.916  1.00  52.73
ATOM  2224  CZ2  TRP  B  238    46.858   29.038   36.964  1.00  52.21
ATOM  2225  CZ3  TRP  B  238    48.577   27.405   36.443  1.00  52.08
ATOM  2226  CH2  TRP  B  238    47.855   28.160   37.360  1.00  52.29
ATOM  2227  C    TRP  B  238    48.757   28.324   30.150  1.00  54.15
ATOM  2228  O    TRP  B  238    49.628   27.545   30.561  1.00  53.85
ATOM  2229  N    TRP  B  238    46.853   29.843   30.223  1.00  55.73
ATOM  2230  CA   TRP  B  238    47.813   29.092   31.089  1.00  54.83
ATOM  2231  N    GLU  B  239    48.517   28.531   28.869  1.00  53.01
ATOM  2232  CA   GLU  B  239    49.214   27.948   27.789  1.00  51.77
ATOM  2233  CB   GLU  B  239    48.459   28.382   26.533  1.00  52.33
ATOM  2234  CG   GLU  B  239    48.955   27.786   25.215  1.00  52.83
ATOM  2235  CD   GLU  B  239    48.498   26.349   25.037  1.00  53.22
ATOM  2236  OE1  GLU  B  239    47.556   25.937   25.743  1.00  54.48
ATOM  2237  OE2  GLU  B  239    49.051   25.629   24.177  1.00  53.06
ATOM  2238  C    GLU  B  239    50.682   28.368   27.677  1.00  50.40
ATOM  2239  O    GLU  B  239    51.077   29.497   27.983  1.00  50.89
ATOM  2240  N    VAL  B  240    51.495   27.372   27.345  1.00  48.41
ATOM  2241  CA   VAL  B  240    52.913   27.608   27.110  1.00  46.27
ATOM  2242  CB   VAL  B  240    53.822   27.122   28.255  1.00  45.31
ATOM  2243  CG1  VAL  B  240    53.513   27.887   29.531  1.00  44.57
ATOM  2244  CG2  VAL  B  240    53.721   25.634   28.447  1.00  44.48
ATOM  2245  C    VAL  B  240    53.258   26.886   25.803  1.00  45.44
ATOM  2246  O    VAL  B  240    52.566   25.942   25.401  1.00  45.59
ATOM  2247  N    PRO  B  241    54.258   27.395   25.052  1.00  44.38
ATOM  2248  CD   PRO  B  241    54.908   28.713   25.116  1.00  43.56
ATOM  2249  CA   PRO  B  241    54.606   26.710   23.798  1.00  43.77
ATOM  2250  CB   PRO  B  241    55.594   27.685   23.153  1.00  43.71
ATOM  2251  CG   PRO  B  241    55.126   29.014   23.653  1.00  43.84
ATOM  2252  C    PRO  B  241    55.254   25.355   24.085  1.00  43.47
ATOM  2253  O    PRO  B  241    56.031   25.212   25.025  1.00  43.42
ATOM  2254  N    ARG  B  242    54.882   24.345   23.313  1.00  43.27
ATOM  2255  CA   ARG  B  242    55.425   23.005   23.495  1.00  43.80
ATOM  2256  CB   ARG  B  242    54.926   22.133   22.354  1.00  44.24
ATOM  2257  CG   ARG  B  242    55.521   20.757   22.297  1.00  45.06
ATOM  2258  CD   ARG  B  242    54.823   19.840   23.240  1.00  45.53
ATOM  2259  NE   ARG  B  242    53.371   19.845   23.045  1.00  46.68
ATOM  2260  CZ   ARG  B  242    52.746   19.477   21.931  1.00  45.19
ATOM  2261  NH1  ARG  B  242    53.432   19.078   20.868  1.00  46.46
ATOM  2262  NH2  ARG  B  242    51.422   19.463   21.903  1.00  44.16
ATOM  2263  C    ARG  B  242    56.963   22.977   23.550  1.00  44.54
ATOM  2264  O    ARG  B  242    57.556   22.049   24.106  1.00  43.90
ATOM  2265  N    GLU  B  243    57.589   23.992   22.950  1.00  45.64
ATOM  2266  CA   GLU  B  243    59.048   24.139   22.895  1.00  45.92
ATOM  2267  CB   GLU  B  243    59.443   25.349   22.032  1.00  48.88
```

Figure 8

```
ATOM   2268  CG   GLU B 243      59.236  25.194  20.527  1.00 53.59
ATOM   2269  CD   GLU B 243      57.771  25.306  20.086  1.00 55.79
ATOM   2270  OE1  GLU B 243      57.329  26.442  19.754  1.00 56.14
ATOM   2271  OE2  GLU B 243      57.085  24.256  20.041  1.00 55.03
ATOM   2272  C    GLU B 243      59.656  24.333  24.272  1.00 44.43
ATOM   2273  O    GLU B 243      60.818  24.026  24.489  1.00 44.60
ATOM   2274  N    THR B 244      58.876  24.886  25.187  1.00 43.27
ATOM   2275  CA   THR B 244      59.334  25.141  26.552  1.00 41.64
ATOM   2276  CB   THR B 244      58.390  26.154  27.238  1.00 41.26
ATOM   2277  OG1  THR B 244      57.110  25.545  27.474  1.00 40.06
ATOM   2278  CG2  THR B 244      58.200  27.375  26.340  1.00 39.93
ATOM   2279  C    THR B 244      59.376  23.875  27.409  1.00 41.10
ATOM   2280  O    THR B 244      59.814  23.910  28.559  1.00 40.99
ATOM   2281  N    LEU B 245      59.022  22.744  26.808  1.00 40.86
ATOM   2282  CA   LEU B 245      58.932  21.488  27.538  1.00 40.52
ATOM   2283  CB   LEU B 245      57.453  21.154  27.688  1.00 41.67
ATOM   2284  CG   LEU B 245      56.787  20.721  28.980  1.00 42.61
ATOM   2285  CD1  LEU B 245      56.922  21.780  30.038  1.00 43.81
ATOM   2286  CD2  LEU B 245      55.324  20.531  28.646  1.00 45.28
ATOM   2287  C    LEU B 245      59.623  20.305  26.875  1.00 39.79
ATOM   2288  O    LEU B 245      59.432  20.040  25.683  1.00 39.46
ATOM   2289  N    LYS B 246      60.380  19.560  27.672  1.00 39.09
ATOM   2290  CA   LYS B 246      61.083  18.385  27.170  1.00 38.29
ATOM   2291  CB   LYS B 246      62.610  18.607  27.190  1.00 39.86
ATOM   2292  CG   LYS B 246      63.429  17.444  26.591  1.00 42.14
ATOM   2293  CD   LYS B 246      64.926  17.716  26.558  1.00 43.69
ATOM   2294  CE   LYS B 246      65.478  18.029  27.940  1.00 43.85
ATOM   2295  NZ   LYS B 246      66.913  18.415  27.869  1.00 46.50
ATOM   2296  C    LYS B 246      60.708  17.128  27.964  1.00 36.17
ATOM   2297  O    LYS B 246      60.982  17.028  29.162  1.00 34.99
ATOM   2298  N    LEU B 247      60.023  16.202  27.294  1.00 34.36
ATOM   2299  CA   LEU B 247      59.622  14.940  27.898  1.00 32.53
ATOM   2300  CB   LEU B 247      58.438  14.321  27.148  1.00 30.52
ATOM   2301  CG   LEU B 247      57.041  14.793  27.598  1.00 29.82
ATOM   2302  CD1  LEU B 247      56.888  16.316  27.528  1.00 27.92
ATOM   2303  CD2  LEU B 247      55.994  14.108  26.742  1.00 29.57
ATOM   2304  C    LEU B 247      60.840  14.036  27.867  1.00 32.44
ATOM   2305  O    LEU B 247      61.491  13.889  26.829  1.00 33.76
ATOM   2306  N    VAL B 248      61.174  13.482  29.028  1.00 31.68
ATOM   2307  CA   VAL B 248      62.351  12.634  29.180  1.00 30.48
ATOM   2308  CB   VAL B 248      63.227  13.146  30.367  1.00 30.05
ATOM   2309  CG1  VAL B 248      64.462  12.266  30.560  1.00 30.41
ATOM   2310  CG2  VAL B 248      63.623  14.583  30.138  1.00 29.41
ATOM   2311  C    VAL B 248      62.119  11.137  29.369  1.00 29.68
ATOM   2312  O    VAL B 248      62.721  10.319  28.690  1.00 29.02
ATOM   2313  N    GLU B 249      61.241  10.787  30.292  1.00 30.24
ATOM   2314  CA   GLU B 249      60.986   9.393  30.623  1.00 30.07
ATOM   2315  CB   GLU B 249      61.777   9.095  31.881  1.00 30.60
ATOM   2316  CG   GLU B 249      61.555   7.775  32.501  1.00 34.00
ATOM   2317  CD   GLU B 249      62.277   7.668  33.826  1.00 36.44
ATOM   2318  OE1  GLU B 249      63.411   8.165  33.930  1.00 38.02
ATOM   2319  OE2  GLU B 249      61.709   7.099  34.779  1.00 40.54
ATOM   2320  C    GLU B 249      59.507   9.140  30.882  1.00 29.71
ATOM   2321  O    GLU B 249      58.839   9.929  31.552  1.00 28.64
ATOM   2322  N    ARG B 250      59.002   8.022  30.380  1.00 28.94
ATOM   2323  CA   ARG B 250      57.602   7.700  30.569  1.00 28.44
ATOM   2324  CB   ARG B 250      57.056   6.922  29.388  1.00 27.60
ATOM   2325  CG   ARG B 250      55.559   7.051  29.285  1.00 28.51
ATOM   2326  CD   ARG B 250      55.036   6.283  28.123  1.00 27.73
ATOM   2327  NE   ARG B 250      55.291   4.869  28.321  1.00 28.57
```

Figure 8

```
ATOM   2328  CZ   ARG B 250      55.002   3.930  27.430  1.00 29.87
ATOM   2329  NH1  ARG B 250      54.443   4.253  26.269  1.00 29.38
ATOM   2330  NH2  ARG B 250      55.285   2.667  27.703  1.00 30.27
ATOM   2331  C    ARG B 250      57.375   6.933  31.854  1.00 28.53
ATOM   2332  O    ARG B 250      57.952   5.865  32.056  1.00 29.24
ATOM   2333  N    LEU B 251      56.553   7.510  32.729  1.00 27.63
ATOM   2334  CA   LEU B 251      56.226   6.918  34.016  1.00 27.28
ATOM   2335  CB   LEU B 251      55.958   8.016  35.063  1.00 25.23
ATOM   2336  CG   LEU B 251      57.126   8.968  35.336  1.00 22.11
ATOM   2337  CD1  LEU B 251      56.658  10.178  36.110  1.00 22.05
ATOM   2338  CD2  LEU B 251      58.205   8.249  36.079  1.00 19.40
ATOM   2339  C    LEU B 251      55.037   5.971  33.913  1.00 27.82
ATOM   2340  O    LEU B 251      54.921   5.027  34.698  1.00 29.09
ATOM   2341  N    GLY B 252      54.175   6.203  32.925  1.00 28.09
ATOM   2342  CA   GLY B 252      53.014   5.344  32.741  1.00 26.87
ATOM   2343  C    GLY B 252      52.264   5.548  31.434  1.00 26.83
ATOM   2344  O    GLY B 252      52.268   6.636  30.864  1.00 25.73
ATOM   2345  N    ALA B 253      51.614   4.488  30.967  1.00 27.54
ATOM   2346  CA   ALA B 253      50.829   4.525  29.737  1.00 28.55
ATOM   2347  CB   ALA B 253      51.647   3.981  28.575  1.00 28.20
ATOM   2348  C    ALA B 253      49.545   3.701  29.915  1.00 29.94
ATOM   2349  O    ALA B 253      49.597   2.507  30.262  1.00 28.91
ATOM   2350  N    GLY B 254      48.401   4.350  29.686  1.00 31.80
ATOM   2351  CA   GLY B 254      47.109   3.689  29.828  1.00 32.77
ATOM   2352  C    GLY B 254      46.122   3.866  28.690  1.00 33.45
ATOM   2353  O    GLY B 254      46.460   4.325  27.604  1.00 34.23
ATOM   2354  N    GLN B 255      44.873   3.529  28.961  1.00 34.51
ATOM   2355  CA   GLN B 255      43.815   3.607  27.965  1.00 35.32
ATOM   2356  CB   GLN B 255      42.519   3.049  28.557  1.00 38.18
ATOM   2357  CG   GLN B 255      41.615   2.337  27.547  1.00 41.65
ATOM   2358  CD   GLN B 255      40.152   2.303  27.979  1.00 43.29
ATOM   2359  OE1  GLN B 255      39.253   2.197  27.130  1.00 42.94
ATOM   2360  NE2  GLN B 255      39.902   2.416  29.298  1.00 43.02
ATOM   2361  C    GLN B 255      43.566   5.009  27.395  1.00 34.49
ATOM   2362  O    GLN B 255      43.364   5.164  26.180  1.00 34.51
ATOM   2363  N    PHE B 256      43.590   6.020  28.269  1.00 32.91
ATOM   2364  CA   PHE B 256      43.333   7.413  27.878  1.00 31.20
ATOM   2365  CB   PHE B 256      42.511   8.127  28.958  1.00 30.47
ATOM   2366  CG   PHE B 256      41.111   7.590  29.130  1.00 31.34
ATOM   2367  CD1  PHE B 256      40.609   6.598  28.289  1.00 31.31
ATOM   2368  CD2  PHE B 256      40.283   8.097  30.128  1.00 31.27
ATOM   2369  CE1  PHE B 256      39.309   6.125  28.442  1.00 31.82
ATOM   2370  CE2  PHE B 256      38.976   7.627  30.286  1.00 31.69
ATOM   2371  CZ   PHE B 256      38.491   6.641  29.440  1.00 31.24
ATOM   2372  C    PHE B 256      44.544   8.281  27.533  1.00 30.44
ATOM   2373  O    PHE B 256      44.382   9.390  27.015  1.00 30.46
ATOM   2374  N    GLY B 257      45.747   7.795  27.837  1.00 29.70
ATOM   2375  CA   GLY B 257      46.945   8.567  27.561  1.00 28.64
ATOM   2376  C    GLY B 257      48.179   8.098  28.307  1.00 28.48
ATOM   2377  O    GLY B 257      48.329   6.909  28.578  1.00 26.32
ATOM   2378  N    GLU B 258      49.040   9.046  28.682  1.00 29.35
ATOM   2379  CA   GLU B 258      50.296   8.731  29.370  1.00 30.95
ATOM   2380  CB   GLU B 258      51.410   8.551  28.330  1.00 32.61
ATOM   2381  CG   GLU B 258      51.056   7.603  27.191  1.00 36.09
ATOM   2382  CD   GLU B 258      52.189   7.410  26.196  1.00 39.23
ATOM   2383  OE1  GLU B 258      52.866   8.407  25.838  1.00 40.41
ATOM   2384  OE2  GLU B 258      52.396   6.253  25.762  1.00 40.81
ATOM   2385  C    GLU B 258      50.763   9.801  30.360  1.00 30.74
ATOM   2386  O    GLU B 258      50.309  10.951  30.312  1.00 31.89
ATOM   2387  N    VAL B 259      51.691   9.415  31.236  1.00 29.88
```

Figure 8

| | | | | | | | | | |
|---|---|---|---|---|---|---|---|---|---|
| ATOM | 2388 | CA  | VAL | B | 259 | 52.290 | 10.326 | 32.223 | 1.00 28.79 |
| ATOM | 2389 | CB  | VAL | B | 259 | 51.901 |  9.982 | 33.668 | 1.00 27.64 |
| ATOM | 2390 | CG1 | VAL | B | 259 | 52.469 | 11.045 | 34.602 | 1.00 25.48 |
| ATOM | 2391 | CG2 | VAL | B | 259 | 50.375 |  9.864 | 33.805 | 1.00 25.60 |
| ATOM | 2392 | C   | VAL | B | 259 | 53.817 | 10.219 | 32.078 | 1.00 29.15 |
| ATOM | 2393 | O   | VAL | B | 259 | 54.376 |  9.109 | 32.090 | 1.00 29.25 |
| ATOM | 2394 | N   | TRP | B | 260 | 54.465 | 11.376 | 31.912 | 1.00 28.58 |
| ATOM | 2395 | CA  | TRP | B | 260 | 55.916 | 11.491 | 31.701 | 1.00 27.70 |
| ATOM | 2396 | CB  | TRP | B | 260 | 56.207 | 12.076 | 30.302 | 1.00 25.66 |
| ATOM | 2397 | CG  | TRP | B | 260 | 56.020 | 11.150 | 29.137 | 1.00 26.31 |
| ATOM | 2398 | CD2 | TRP | B | 260 | 57.050 | 10.616 | 28.290 | 1.00 27.57 |
| ATOM | 2399 | CE2 | TRP | B | 260 | 56.418 |  9.810 | 27.318 | 1.00 28.15 |
| ATOM | 2400 | CE3 | TRP | B | 260 | 58.449 | 10.741 | 28.256 | 1.00 28.26 |
| ATOM | 2401 | CD1 | TRP | B | 260 | 54.836 | 10.658 | 28.651 | 1.00 26.56 |
| ATOM | 2402 | NE1 | TRP | B | 260 | 55.069 |  9.849 | 27.565 | 1.00 27.00 |
| ATOM | 2403 | CZ2 | TRP | B | 260 | 57.143 |  9.131 | 26.322 | 1.00 27.85 |
| ATOM | 2404 | CZ3 | TRP | B | 260 | 59.165 | 10.065 | 27.272 | 1.00 26.57 |
| ATOM | 2405 | CH2 | TRP | B | 260 | 58.512 |  9.271 | 26.321 | 1.00 26.73 |
| ATOM | 2406 | C   | TRP | B | 260 | 56.638 | 12.400 | 32.690 | 1.00 27.66 |
| ATOM | 2407 | O   | TRP | B | 260 | 56.044 | 13.301 | 33.278 | 1.00 27.37 |
| ATOM | 2408 | N   | MET | B | 261 | 57.934 | 12.140 | 32.875 | 1.00 28.33 |
| ATOM | 2409 | CA  | MET | B | 261 | 58.779 | 12.991 | 33.713 | 1.00 28.13 |
| ATOM | 2410 | CB  | MET | B | 261 | 59.838 | 12.183 | 34.466 | 1.00 27.51 |
| ATOM | 2411 | CG  | MET | B | 261 | 60.808 | 13.058 | 35.303 | 1.00 27.27 |
| ATOM | 2412 | SD  | MET | B | 261 | 62.217 | 13.862 | 34.412 | 1.00 27.54 |
| ATOM | 2413 | CE  | MET | B | 261 | 63.147 | 12.353 | 33.860 | 1.00 24.52 |
| ATOM | 2414 | C   | MET | B | 261 | 59.457 | 13.866 | 32.664 | 1.00 28.16 |
| ATOM | 2415 | O   | MET | B | 261 | 59.829 | 13.370 | 31.596 | 1.00 27.01 |
| ATOM | 2416 | N   | GLY | B | 262 | 59.590 | 15.157 | 32.945 | 1.00 28.34 |
| ATOM | 2417 | CA  | GLY | B | 262 | 60.211 | 16.045 | 31.987 | 1.00 28.58 |
| ATOM | 2418 | C   | GLY | B | 262 | 60.795 | 17.264 | 32.653 | 1.00 29.40 |
| ATOM | 2419 | O   | GLY | B | 262 | 60.873 | 17.339 | 33.877 | 1.00 28.97 |
| ATOM | 2420 | N   | TYR | B | 263 | 61.215 | 18.223 | 31.837 | 1.00 30.58 |
| ATOM | 2421 | CA  | TYR | B | 263 | 61.797 | 19.447 | 32.347 | 1.00 32.19 |
| ATOM | 2422 | CB  | TYR | B | 263 | 63.319 | 19.434 | 32.174 | 1.00 30.28 |
| ATOM | 2423 | CG  | TYR | B | 263 | 64.003 | 18.426 | 33.080 | 1.00 26.77 |
| ATOM | 2424 | CD1 | TYR | B | 263 | 64.369 | 18.769 | 34.374 | 1.00 24.78 |
| ATOM | 2425 | CE1 | TYR | B | 263 | 64.945 | 17.844 | 35.216 | 1.00 25.32 |
| ATOM | 2426 | CD2 | TYR | B | 263 | 64.239 | 17.116 | 32.648 | 1.00 26.23 |
| ATOM | 2427 | CE2 | TYR | B | 263 | 64.820 | 16.175 | 33.489 | 1.00 25.52 |
| ATOM | 2428 | CZ  | TYR | B | 263 | 65.172 | 16.548 | 34.770 | 1.00 26.22 |
| ATOM | 2429 | OH  | TYR | B | 263 | 65.780 | 15.634 | 35.608 | 1.00 29.23 |
| ATOM | 2430 | C   | TYR | B | 263 | 61.160 | 20.638 | 31.678 | 1.00 34.73 |
| ATOM | 2431 | O   | TYR | B | 263 | 60.988 | 20.673 | 30.463 | 1.00 35.31 |
| ATOM | 2432 | N   | TYR | B | 264 | 60.758 | 21.587 | 32.515 | 1.00 39.00 |
| ATOM | 2433 | CA  | TYR | B | 264 | 60.081 | 22.817 | 32.112 | 1.00 43.40 |
| ATOM | 2434 | CB  | TYR | B | 264 | 58.949 | 23.086 | 33.129 | 1.00 45.17 |
| ATOM | 2435 | CG  | TYR | B | 264 | 57.981 | 24.228 | 32.864 | 1.00 47.94 |
| ATOM | 2436 | CD1 | TYR | B | 264 | 57.758 | 24.730 | 31.572 | 1.00 48.62 |
| ATOM | 2437 | CE1 | TYR | B | 264 | 56.827 | 25.776 | 31.346 | 1.00 50.27 |
| ATOM | 2438 | CD2 | TYR | B | 264 | 57.258 | 24.795 | 33.929 | 1.00 49.61 |
| ATOM | 2439 | CE2 | TYR | B | 264 | 56.332 | 25.829 | 33.722 | 1.00 50.23 |
| ATOM | 2440 | CZ  | TYR | B | 264 | 56.120 | 26.319 | 32.432 | 1.00 50.32 |
| ATOM | 2441 | OH  | TYR | B | 264 | 55.209 | 27.343 | 32.247 | 1.00 49.92 |
| ATOM | 2442 | C   | TYR | B | 264 | 61.112 | 23.944 | 32.105 | 1.00 44.83 |
| ATOM | 2443 | O   | TYR | B | 264 | 61.840 | 24.138 | 33.081 | 1.00 45.59 |
| ATOM | 2444 | N   | ASN | B | 265 | 61.201 | 24.650 | 30.983 | 1.00 46.31 |
| ATOM | 2445 | CA  | ASN | B | 265 | 62.146 | 25.749 | 30.839 | 1.00 48.16 |
| ATOM | 2446 | CB  | ASN | B | 265 | 61.769 | 26.901 | 31.783 | 1.00 48.45 |
| ATOM | 2447 | CG  | ASN | B | 265 | 60.318 | 27.358 | 31.607 | 1.00 49.30 |

Figure 8

| ATOM | 2448 | OD1 | ASN | B | 265 | 59.863 | 27.598 | 30.487 | 1.00 | 48.84 |
|------|------|-----|-----|---|-----|--------|--------|--------|------|-------|
| ATOM | 2449 | ND2 | ASN | B | 265 | 59.590 | 27.482 | 32.721 | 1.00 | 48.75 |
| ATOM | 2450 | C   | ASN | B | 265 | 63.555 | 25.228 | 31.131 | 1.00 | 49.30 |
| ATOM | 2451 | O   | ASN | B | 265 | 64.369 | 25.901 | 31.762 | 1.00 | 50.10 |
| ATOM | 2452 | N   | GLY | B | 266 | 63.799 | 23.985 | 30.726 | 1.00 | 50.16 |
| ATOM | 2453 | CA  | GLY | B | 266 | 65.101 | 23.377 | 30.919 | 1.00 | 51.61 |
| ATOM | 2454 | C   | GLY | B | 266 | 65.483 | 22.879 | 32.300 | 1.00 | 52.99 |
| ATOM | 2455 | O   | GLY | B | 266 | 66.122 | 21.828 | 32.392 | 1.00 | 53.58 |
| ATOM | 2456 | N   | HIS | B | 267 | 65.084 | 23.576 | 33.371 | 1.00 | 53.74 |
| ATOM | 2457 | CA  | HIS | B | 267 | 65.465 | 23.154 | 34.726 | 1.00 | 53.81 |
| ATOM | 2458 | CB  | HIS | B | 267 | 66.369 | 24.205 | 35.369 | 1.00 | 59.24 |
| ATOM | 2459 | CG  | HIS | B | 267 | 67.747 | 24.251 | 34.778 | 1.00 | 64.80 |
| ATOM | 2460 | CD2 | HIS | B | 267 | 68.658 | 23.271 | 34.550 | 1.00 | 66.11 |
| ATOM | 2461 | ND1 | HIS | B | 267 | 68.319 | 25.418 | 34.317 | 1.00 | 67.09 |
| ATOM | 2462 | CE1 | HIS | B | 267 | 69.520 | 25.157 | 33.831 | 1.00 | 67.91 |
| ATOM | 2463 | NE2 | HIS | B | 267 | 69.750 | 23.862 | 33.959 | 1.00 | 67.36 |
| ATOM | 2464 | C   | HIS | B | 267 | 64.438 | 22.683 | 35.758 | 1.00 | 51.17 |
| ATOM | 2465 | O   | HIS | B | 267 | 64.809 | 22.025 | 36.734 | 1.00 | 50.84 |
| ATOM | 2466 | N   | THR | B | 268 | 63.175 | 23.064 | 35.589 | 1.00 | 48.03 |
| ATOM | 2467 | CA  | THR | B | 268 | 62.123 | 22.654 | 36.522 | 1.00 | 44.23 |
| ATOM | 2468 | CB  | THR | B | 268 | 60.876 | 23.566 | 36.400 | 1.00 | 44.78 |
| ATOM | 2469 | OG1 | THR | B | 268 | 61.272 | 24.940 | 36.500 | 1.00 | 45.65 |
| ATOM | 2470 | CG2 | THR | B | 268 | 59.844 | 23.243 | 37.488 | 1.00 | 43.87 |
| ATOM | 2471 | C   | THR | B | 268 | 61.700 | 21.231 | 36.180 | 1.00 | 41.32 |
| ATOM | 2472 | O   | THR | B | 268 | 61.311 | 20.954 | 35.056 | 1.00 | 41.02 |
| ATOM | 2473 | N   | LYS | B | 269 | 61.830 | 20.312 | 37.124 | 1.00 | 37.95 |
| ATOM | 2474 | CA  | LYS | B | 269 | 61.415 | 18.939 | 36.872 | 1.00 | 34.62 |
| ATOM | 2475 | CB  | LYS | B | 269 | 62.092 | 17.992 | 37.851 | 1.00 | 32.01 |
| ATOM | 2476 | CG  | LYS | B | 269 | 61.985 | 16.554 | 37.476 | 1.00 | 28.83 |
| ATOM | 2477 | CD  | LYS | B | 269 | 62.811 | 15.751 | 38.424 | 1.00 | 28.47 |
| ATOM | 2478 | CE  | LYS | B | 269 | 63.115 | 14.389 | 37.875 | 1.00 | 28.61 |
| ATOM | 2479 | NZ  | LYS | B | 269 | 64.202 | 13.791 | 38.660 | 1.00 | 29.50 |
| ATOM | 2480 | C   | LYS | B | 269 | 59.892 | 18.891 | 37.046 | 1.00 | 34.47 |
| ATOM | 2481 | O   | LYS | B | 269 | 59.362 | 19.292 | 38.098 | 1.00 | 34.37 |
| ATOM | 2482 | N   | VAL | B | 270 | 59.195 | 18.426 | 36.005 | 1.00 | 32.91 |
| ATOM | 2483 | CA  | VAL | B | 270 | 57.735 | 18.338 | 36.005 | 1.00 | 29.67 |
| ATOM | 2484 | CB  | VAL | B | 270 | 57.129 | 19.401 | 35.040 | 1.00 | 29.21 |
| ATOM | 2485 | CG1 | VAL | B | 270 | 57.420 | 20.816 | 35.519 | 1.00 | 26.86 |
| ATOM | 2486 | CG2 | VAL | B | 270 | 57.647 | 19.183 | 33.625 | 1.00 | 25.72 |
| ATOM | 2487 | C   | VAL | B | 270 | 57.184 | 16.963 | 35.574 | 1.00 | 29.27 |
| ATOM | 2488 | O   | VAL | B | 270 | 57.925 | 16.093 | 35.127 | 1.00 | 29.14 |
| ATOM | 2489 | N   | ALA | B | 271 | 55.882 | 16.763 | 35.783 | 1.00 | 28.24 |
| ATOM | 2490 | CA  | ALA | B | 271 | 55.189 | 15.551 | 35.351 | 1.00 | 26.75 |
| ATOM | 2491 | CB  | ALA | B | 271 | 54.413 | 14.919 | 36.483 | 1.00 | 25.50 |
| ATOM | 2492 | C   | ALA | B | 271 | 54.240 | 16.088 | 34.281 | 1.00 | 26.39 |
| ATOM | 2493 | O   | ALA | B | 271 | 53.665 | 17.168 | 34.445 | 1.00 | 26.72 |
| ATOM | 2494 | N   | VAL | B | 272 | 54.174 | 15.404 | 33.145 | 1.00 | 25.81 |
| ATOM | 2495 | CA  | VAL | B | 272 | 53.320 | 15.819 | 32.039 | 1.00 | 25.57 |
| ATOM | 2496 | CB  | VAL | B | 272 | 54.150 | 16.119 | 30.750 | 1.00 | 25.31 |
| ATOM | 2497 | CG1 | VAL | B | 272 | 53.222 | 16.537 | 29.603 | 1.00 | 23.58 |
| ATOM | 2498 | CG2 | VAL | B | 272 | 55.219 | 17.175 | 31.020 | 1.00 | 22.95 |
| ATOM | 2499 | C   | VAL | B | 272 | 52.348 | 14.710 | 31.690 | 1.00 | 26.26 |
| ATOM | 2500 | O   | VAL | B | 272 | 52.767 | 13.582 | 31.412 | 1.00 | 26.51 |
| ATOM | 2501 | N   | LYS | B | 273 | 51.053 | 15.010 | 31.751 | 1.00 | 26.65 |
| ATOM | 2502 | CA  | LYS | B | 273 | 50.027 | 14.022 | 31.386 | 1.00 | 26.72 |
| ATOM | 2503 | CB  | LYS | B | 273 | 48.860 | 14.029 | 32.385 | 1.00 | 27.63 |
| ATOM | 2504 | CG  | LYS | B | 273 | 47.714 | 13.097 | 32.003 | 1.00 | 28.97 |
| ATOM | 2505 | CD  | LYS | B | 273 | 46.582 | 13.180 | 32.993 | 1.00 | 29.76 |
| ATOM | 2506 | CE  | LYS | B | 273 | 46.924 | 12.458 | 34.266 | 1.00 | 31.47 |
| ATOM | 2507 | NZ  | LYS | B | 273 | 45.742 | 12.286 | 35.176 | 1.00 | 31.42 |

Figure 8

| | | | | | | | | | |
|---|---|---|---|---|---|---|---|---|---|
| ATOM | 2508 | C | LYS | B | 273 | 49.556 | 14.390 | 29.974 | 1.00 26.63 |
| ATOM | 2509 | O | LYS | B | 273 | 49.253 | 15.553 | 29.696 | 1.00 25.34 |
| ATOM | 2510 | N | SER | B | 274 | 49.587 | 13.424 | 29.064 | 1.00 27.26 |
| ATOM | 2511 | CA | SER | B | 274 | 49.179 | 13.683 | 27.691 | 1.00 28.24 |
| ATOM | 2512 | CB | SER | B | 274 | 50.313 | 13.326 | 26.729 | 1.00 27.33 |
| ATOM | 2513 | OG | SER | B | 274 | 50.559 | 11.935 | 26.764 | 1.00 28.38 |
| ATOM | 2514 | C | SER | B | 274 | 47.937 | 12.876 | 27.345 | 1.00 29.08 |
| ATOM | 2515 | O | SER | B | 274 | 47.748 | 11.771 | 27.857 | 1.00 29.00 |
| ATOM | 2516 | N | LEU | B | 275 | 47.122 | 13.412 | 26.441 | 1.00 29.86 |
| ATOM | 2517 | CA | LEU | B | 275 | 45.892 | 12.749 | 26.029 | 1.00 31.19 |
| ATOM | 2518 | CB | LEU | B | 275 | 44.758 | 13.779 | 25.906 | 1.00 28.77 |
| ATOM | 2519 | CG | LEU | B | 275 | 43.420 | 13.350 | 25.280 | 1.00 28.14 |
| ATOM | 2520 | CD1 | LEU | B | 275 | 42.731 | 12.292 | 26.138 | 1.00 26.50 |
| ATOM | 2521 | CD2 | LEU | B | 275 | 42.503 | 14.573 | 25.074 | 1.00 26.71 |
| ATOM | 2522 | C | LEU | B | 275 | 45.995 | 11.967 | 24.715 | 1.00 33.78 |
| ATOM | 2523 | O | LEU | B | 275 | 46.394 | 12.516 | 23.684 | 1.00 34.41 |
| ATOM | 2524 | N | LYS | B | 276 | 45.660 | 10.679 | 24.772 | 1.00 35.36 |
| ATOM | 2525 | CA | LYS | B | 276 | 45.620 | 9.830 | 23.591 | 1.00 37.00 |
| ATOM | 2526 | CB | LYS | B | 276 | 45.489 | 8.361 | 24.016 | 1.00 37.30 |
| ATOM | 2527 | CG | LYS | B | 276 | 45.269 | 7.353 | 22.895 | 1.00 37.99 |
| ATOM | 2528 | CD | LYS | B | 276 | 45.129 | 5.921 | 23.446 | 1.00 40.28 |
| ATOM | 2529 | CE | LYS | B | 276 | 46.363 | 5.494 | 24.259 | 1.00 42.42 |
| ATOM | 2530 | NZ | LYS | B | 276 | 46.352 | 4.084 | 24.779 | 1.00 42.75 |
| ATOM | 2531 | C | LYS | B | 276 | 44.330 | 10.291 | 22.908 | 1.00 38.78 |
| ATOM | 2532 | O | LYS | B | 276 | 43.233 | 10.062 | 23.428 | 1.00 39.99 |
| ATOM | 2533 | N | GLN | B | 277 | 44.469 | 11.004 | 21.794 | 1.00 39.73 |
| ATOM | 2534 | CA | GLN | B | 277 | 43.328 | 11.523 | 21.031 | 1.00 40.26 |
| ATOM | 2535 | CB | GLN | B | 277 | 43.820 | 12.096 | 19.707 | 1.00 43.98 |
| ATOM | 2536 | CG | GLN | B | 277 | 42.721 | 12.428 | 18.730 | 1.00 49.21 |
| ATOM | 2537 | CD | GLN | B | 277 | 43.221 | 12.403 | 17.313 | 1.00 52.99 |
| ATOM | 2538 | OE1 | GLN | B | 277 | 43.985 | 11.509 | 16.920 | 1.00 55.15 |
| ATOM | 2539 | NE2 | GLN | B | 277 | 42.788 | 13.373 | 16.521 | 1.00 55.81 |
| ATOM | 2540 | C | GLN | B | 277 | 42.211 | 10.513 | 20.767 | 1.00 38.80 |
| ATOM | 2541 | O | GLN | B | 277 | 42.458 | 9.362 | 20.386 | 1.00 36.62 |
| ATOM | 2542 | N | GLY | B | 278 | 40.979 | 10.965 | 20.998 | 1.00 38.77 |
| ATOM | 2543 | CA | GLY | B | 278 | 39.808 | 10.123 | 20.809 | 1.00 38.88 |
| ATOM | 2544 | C | GLY | B | 278 | 39.293 | 9.489 | 22.099 | 1.00 39.33 |
| ATOM | 2545 | O | GLY | B | 278 | 38.170 | 8.964 | 22.155 | 1.00 39.32 |
| ATOM | 2546 | N | SER | B | 279 | 40.123 | 9.518 | 23.140 | 1.00 39.14 |
| ATOM | 2547 | CA | SER | B | 279 | 39.765 | 8.942 | 24.433 | 1.00 39.11 |
| ATOM | 2548 | CB | SER | B | 279 | 41.012 | 8.902 | 25.331 | 1.00 39.17 |
| ATOM | 2549 | OG | SER | B | 279 | 42.027 | 8.097 | 24.745 | 1.00 37.91 |
| ATOM | 2550 | C | SER | B | 279 | 38.630 | 9.736 | 25.084 | 1.00 38.51 |
| ATOM | 2551 | O | SER | B | 279 | 37.786 | 9.197 | 25.814 | 1.00 37.96 |
| ATOM | 2552 | N | MET | B | 280 | 38.632 | 11.027 | 24.783 | 1.00 37.91 |
| ATOM | 2553 | CA | MET | B | 280 | 37.647 | 11.988 | 25.253 | 1.00 37.14 |
| ATOM | 2554 | CB | MET | B | 280 | 37.681 | 12.116 | 26.784 | 1.00 37.42 |
| ATOM | 2555 | CG | MET | B | 280 | 38.984 | 12.694 | 27.355 | 1.00 37.15 |
| ATOM | 2556 | SD | MET | B | 280 | 39.184 | 12.407 | 29.119 | 1.00 36.61 |
| ATOM | 2557 | CE | MET | B | 280 | 38.253 | 13.700 | 29.761 | 1.00 37.27 |
| ATOM | 2558 | C | MET | B | 280 | 38.034 | 13.310 | 24.580 | 1.00 36.57 |
| ATOM | 2559 | O | MET | B | 280 | 39.140 | 13.442 | 24.037 | 1.00 35.47 |
| ATOM | 2560 | N | SER | B | 281 | 37.113 | 14.270 | 24.592 | 1.00 36.32 |
| ATOM | 2561 | CA | SER | B | 281 | 37.372 | 15.556 | 23.976 | 1.00 36.20 |
| ATOM | 2562 | CB | SER | B | 281 | 36.079 | 16.399 | 23.864 | 1.00 34.51 |
| ATOM | 2563 | OG | SER | B | 281 | 35.698 | 16.995 | 25.100 | 1.00 32.79 |
| ATOM | 2564 | C | SER | B | 281 | 38.381 | 16.359 | 24.763 | 1.00 37.49 |
| ATOM | 2565 | O | SER | B | 281 | 38.444 | 16.265 | 25.998 | 1.00 38.13 |
| ATOM | 2566 | N | PRO | B | 282 | 39.152 | 17.200 | 24.081 | 1.00 37.99 |
| ATOM | 2567 | CD | PRO | B | 282 | 39.248 | 17.240 | 22.593 | 1.00 38.31 |

Figure 8

```
ATOM   2568  CA   PRO B 282      40.178  18.058  24.655  1.00 38.45
ATOM   2569  CB   PRO B 282      40.594  18.932  23.500  1.00 37.93
ATOM   2570  CG   PRO B 282      40.553  17.943  22.389  1.00 38.06
ATOM   2571  C    PRO B 282      39.685  18.919  25.806  1.00 39.44
ATOM   2572  O    PRO B 282      40.409  19.056  26.780  1.00 40.64
ATOM   2573  N    ASP B 283      38.482  19.487  25.682  1.00 40.55
ATOM   2574  CA   ASP B 283      37.909  20.346  26.738  1.00 40.74
ATOM   2575  CB   ASP B 283      36.616  21.041  26.254  1.00 43.77
ATOM   2576  CG   ASP B 283      36.774  21.702  24.885  1.00 47.90
ATOM   2577  OD1  ASP B 283      37.761  22.450  24.677  1.00 49.54
ATOM   2578  OD2  ASP B 283      35.914  21.466  24.011  1.00 50.67
ATOM   2579  C    ASP B 283      37.616  19.517  27.996  1.00 39.36
ATOM   2580  O    ASP B 283      37.727  20.010  29.120  1.00 38.24
ATOM   2581  N    ALA B 284      37.269  18.249  27.779  1.00 38.43
ATOM   2582  CA   ALA B 284      36.966  17.319  28.871  1.00 37.76
ATOM   2583  CB   ALA B 284      36.336  16.047  28.319  1.00 37.18
ATOM   2584  C    ALA B 284      38.227  16.978  29.657  1.00 37.85
ATOM   2585  O    ALA B 284      38.194  16.856  30.887  1.00 38.73
ATOM   2586  N    PHE B 285      39.334  16.824  28.927  1.00 37.47
ATOM   2587  CA   PHE B 285      40.658  16.503  29.482  1.00 34.74
ATOM   2588  CB   PHE B 285      41.581  15.950  28.364  1.00 32.83
ATOM   2589  CG   PHE B 285      43.028  15.738  28.786  1.00 30.33
ATOM   2590  CD1  PHE B 285      43.414  14.594  29.473  1.00 29.41
ATOM   2591  CD2  PHE B 285      44.011  16.674  28.468  1.00 28.34
ATOM   2592  CE1  PHE B 285      44.744  14.386  29.840  1.00 27.72
ATOM   2593  CE2  PHE B 285      45.341  16.470  28.834  1.00 26.64
ATOM   2594  CZ   PHE B 285      45.704  15.324  29.517  1.00 26.48
ATOM   2595  C    PHE B 285      41.256  17.766  30.101  1.00 34.79
ATOM   2596  O    PHE B 285      41.751  17.707  31.229  1.00 34.46
ATOM   2597  N    LEU B 286      41.154  18.907  29.412  1.00 35.10
ATOM   2598  CA   LEU B 286      41.704  20.169  29.922  1.00 37.40
ATOM   2599  CB   LEU B 286      41.781  21.232  28.801  1.00 36.31
ATOM   2600  CG   LEU B 286      42.985  21.017  27.876  1.00 37.16
ATOM   2601  CD1  LEU B 286      42.878  21.898  26.651  1.00 37.55
ATOM   2602  CD2  LEU B 286      44.301  21.258  28.624  1.00 36.40
ATOM   2603  C    LEU B 286      40.950  20.704  31.150  1.00 39.30
ATOM   2604  O    LEU B 286      41.301  21.749  31.729  1.00 39.33
ATOM   2605  N    ALA B 287      40.019  19.874  31.625  1.00 41.74
ATOM   2606  CA   ALA B 287      39.175  20.207  32.763  1.00 43.21
ATOM   2607  CB   ALA B 287      37.890  19.426  32.701  1.00 42.49
ATOM   2608  C    ALA B 287      39.889  19.961  34.088  1.00 44.66
ATOM   2609  O    ALA B 287      39.582  20.601  35.086  1.00 44.65
ATOM   2610  N    GLU B 288      40.897  19.092  34.056  1.00 46.28
ATOM   2611  CA   GLU B 288      41.658  18.773  35.258  1.00 47.59
ATOM   2612  CB   GLU B 288      42.665  17.643  35.004  1.00 50.68
ATOM   2613  CG   GLU B 288      42.139  16.462  34.197  1.00 55.33
ATOM   2614  CD   GLU B 288      43.042  15.246  34.315  1.00 57.69
ATOM   2615  OE1  GLU B 288      43.068  14.666  35.426  1.00 57.24
ATOM   2616  OE2  GLU B 288      43.713  14.883  33.314  1.00 58.67
ATOM   2617  C    GLU B 288      42.422  20.037  35.658  1.00 47.10
ATOM   2618  O    GLU B 288      42.515  20.353  36.836  1.00 47.96
ATOM   2619  N    ALA B 289      42.949  20.748  34.657  1.00 46.36
ATOM   2620  CA   ALA B 289      43.687  21.969  34.901  1.00 45.35
ATOM   2621  CB   ALA B 289      44.292  22.529  33.621  1.00 45.23
ATOM   2622  C    ALA B 289      42.775  22.998  35.516  1.00 44.55
ATOM   2623  O    ALA B 289      43.199  23.710  36.403  1.00 44.88
ATOM   2624  N    ASN B 290      41.535  23.082  35.032  1.00 43.45
ATOM   2625  CA   ASN B 290      40.559  24.060  35.544  1.00 42.29
ATOM   2626  CB   ASN B 290      39.241  23.939  34.758  1.00 43.52
ATOM   2627  CG   ASN B 290      39.361  24.477  33.338  1.00 44.44
```

Figure 8

| | | | | | | | | | |
|---|---|---|---|---|---|---|---|---|---|
| ATOM | 2628 | OD1 | ASN | B | 290 | 38.481 | 24.264 | 32.496 | 1.00 44.89 |
| ATOM | 2629 | ND2 | ASN | B | 290 | 40.456 | 25.181 | 33.067 | 1.00 43.89 |
| ATOM | 2630 | C | ASN | B | 290 | 40.349 | 23.849 | 37.049 | 1.00 40.70 |
| ATOM | 2631 | O | ASN | B | 290 | 40.354 | 24.791 | 37.826 | 1.00 40.88 |
| ATOM | 2632 | N | LEU | B | 291 | 40.267 | 22.580 | 37.433 | 1.00 38.85 |
| ATOM | 2633 | CA | LEU | B | 291 | 40.098 | 22.207 | 38.806 | 1.00 37.09 |
| ATOM | 2634 | CB | LEU | B | 291 | 39.853 | 20.711 | 38.925 | 1.00 35.93 |
| ATOM | 2635 | CG | LEU | B | 291 | 38.396 | 20.392 | 38.600 | 1.00 34.22 |
| ATOM | 2636 | CD1 | LEU | B | 291 | 38.177 | 18.924 | 38.272 | 1.00 34.08 |
| ATOM | 2637 | CD2 | LEU | B | 291 | 37.510 | 20.855 | 39.740 | 1.00 34.58 |
| ATOM | 2638 | C | LEU | B | 291 | 41.302 | 22.601 | 39.662 | 1.00 36.63 |
| ATOM | 2639 | O | LEU | B | 291 | 41.142 | 22.989 | 40.807 | 1.00 36.89 |
| ATOM | 2640 | N | MET | B | 292 | 42.492 | 22.468 | 39.058 | 1.00 36.60 |
| ATOM | 2641 | CA | MET | B | 292 | 43.785 | 22.783 | 39.719 | 1.00 36.39 |
| ATOM | 2642 | CB | MET | B | 292 | 44.944 | 22.119 | 39.016 | 1.00 35.25 |
| ATOM | 2643 | CG | MET | B | 292 | 45.482 | 20.890 | 39.763 | 1.00 33.53 |
| ATOM | 2644 | SD | MET | B | 292 | 46.768 | 20.073 | 38.812 | 1.00 30.49 |
| ATOM | 2645 | CE | MET | B | 292 | 45.872 | 19.609 | 37.259 | 1.00 32.40 |
| ATOM | 2646 | C | MET | B | 292 | 44.020 | 24.295 | 39.915 | 1.00 37.76 |
| ATOM | 2647 | O | MET | B | 292 | 44.527 | 24.723 | 40.954 | 1.00 38.40 |
| ATOM | 2648 | N | LYS | B | 293 | 43.551 | 25.037 | 38.913 | 1.00 39.06 |
| ATOM | 2649 | CA | LYS | B | 293 | 43.581 | 26.501 | 38.949 | 1.00 40.23 |
| ATOM | 2650 | CB | LYS | B | 293 | 42.999 | 27.053 | 37.635 | 1.00 41.12 |
| ATOM | 2651 | CG | LYS | B | 293 | 43.768 | 26.665 | 36.389 | 1.00 42.43 |
| ATOM | 2652 | CD | LYS | B | 293 | 43.013 | 27.077 | 35.120 | 1.00 42.68 |
| ATOM | 2653 | CE | LYS | B | 293 | 43.742 | 26.670 | 33.856 | 1.00 42.72 |
| ATOM | 2654 | NZ | LYS | B | 293 | 43.177 | 27.288 | 32.626 | 1.00 43.14 |
| ATOM | 2655 | C | LYS | B | 293 | 42.651 | 26.980 | 40.100 | 1.00 40.75 |
| ATOM | 2656 | O | LYS | B | 293 | 43.038 | 27.789 | 40.934 | 1.00 41.55 |
| ATOM | 2657 | N | GLN | B | 294 | 41.438 | 26.432 | 40.125 | 1.00 40.89 |
| ATOM | 2658 | CA | GLN | B | 294 | 40.445 | 26.782 | 41.149 | 1.00 41.64 |
| ATOM | 2659 | CB | GLN | B | 294 | 39.097 | 26.103 | 40.845 | 1.00 43.92 |
| ATOM | 2660 | CG | GLN | B | 294 | 38.533 | 26.438 | 39.472 | 1.00 47.75 |
| ATOM | 2661 | CD | GLN | B | 294 | 38.649 | 27.927 | 39.129 | 1.00 51.49 |
| ATOM | 2662 | OE1 | GLN | B | 294 | 39.274 | 28.308 | 38.121 | 1.00 52.37 |
| ATOM | 2663 | NE2 | GLN | B | 294 | 38.043 | 28.777 | 39.967 | 1.00 52.61 |
| ATOM | 2664 | C | GLN | B | 294 | 40.859 | 26.446 | 42.593 | 1.00 40.68 |
| ATOM | 2665 | O | GLN | B | 294 | 40.606 | 27.216 | 43.538 | 1.00 41.34 |
| ATOM | 2666 | N | LEU | B | 295 | 41.518 | 25.308 | 42.771 | 1.00 39.60 |
| ATOM | 2667 | CA | LEU | B | 295 | 41.949 | 24.869 | 44.089 | 1.00 38.25 |
| ATOM | 2668 | CB | LEU | B | 295 | 41.289 | 23.523 | 44.402 | 1.00 38.06 |
| ATOM | 2669 | CG | LEU | B | 295 | 39.764 | 23.482 | 44.461 | 1.00 36.84 |
| ATOM | 2670 | CD1 | LEU | B | 295 | 39.289 | 22.043 | 44.450 | 1.00 37.29 |
| ATOM | 2671 | CD2 | LEU | B | 295 | 39.284 | 24.211 | 45.705 | 1.00 36.25 |
| ATOM | 2672 | C | LEU | B | 295 | 43.462 | 24.767 | 44.273 | 1.00 36.86 |
| ATOM | 2673 | O | LEU | B | 295 | 44.094 | 23.860 | 43.730 | 1.00 36.59 |
| ATOM | 2674 | N | GLN | B | 296 | 44.028 | 25.679 | 45.062 | 1.00 35.67 |
| ATOM | 2675 | CA | GLN | B | 296 | 45.471 | 25.672 | 45.345 | 1.00 35.75 |
| ATOM | 2676 | CB | GLN | B | 296 | 46.154 | 26.895 | 44.747 | 1.00 35.74 |
| ATOM | 2677 | CG | GLN | B | 296 | 46.127 | 26.914 | 43.238 | 1.00 37.95 |
| ATOM | 2678 | CD | GLN | B | 296 | 46.308 | 28.303 | 42.685 | 1.00 39.71 |
| ATOM | 2679 | OE1 | GLN | B | 296 | 46.245 | 29.285 | 43.418 | 1.00 41.80 |
| ATOM | 2680 | NE2 | GLN | B | 296 | 46.526 | 28.399 | 41.385 | 1.00 41.13 |
| ATOM | 2681 | C | GLN | B | 296 | 45.757 | 25.567 | 46.848 | 1.00 34.94 |
| ATOM | 2682 | O | GLN | B | 296 | 45.221 | 26.323 | 47.662 | 1.00 34.98 |
| ATOM | 2683 | N | HIS | B | 297 | 46.621 | 24.626 | 47.210 | 1.00 33.68 |
| ATOM | 2684 | CA | HIS | B | 297 | 46.929 | 24.398 | 48.606 | 1.00 33.03 |
| ATOM | 2685 | CB | HIS | B | 297 | 45.733 | 23.663 | 49.235 | 1.00 31.82 |
| ATOM | 2686 | CG | HIS | B | 297 | 45.814 | 23.522 | 50.722 | 1.00 29.79 |
| ATOM | 2687 | CD2 | HIS | B | 297 | 45.358 | 24.316 | 51.717 | 1.00 28.97 |

Figure 8

| ATOM | 2688 | ND1 | HIS | B | 297 | 46.450 | 22.465 | 51.338 | 1.00 | 29.31 |
| ATOM | 2689 | CE1 | HIS | B | 297 | 46.389 | 22.617 | 52.648 | 1.00 | 28.13 |
| ATOM | 2690 | NE2 | HIS | B | 297 | 45.728 | 23.732 | 52.904 | 1.00 | 28.43 |
| ATOM | 2691 | C | HIS | B | 297 | 48.194 | 23.548 | 48.707 | 1.00 | 33.67 |
| ATOM | 2692 | O | HIS | B | 297 | 48.514 | 22.830 | 47.767 | 1.00 | 34.08 |
| ATOM | 2693 | N | GLN | B | 298 | 48.888 | 23.621 | 49.850 | 1.00 | 34.53 |
| ATOM | 2694 | CA | GLN | B | 298 | 50.114 | 22.844 | 50.087 | 1.00 | 36.27 |
| ATOM | 2695 | CB | GLN | B | 298 | 50.756 | 23.190 | 51.451 | 1.00 | 40.56 |
| ATOM | 2696 | CG | GLN | B | 298 | 51.834 | 24.312 | 51.407 | 1.00 | 48.58 |
| ATOM | 2697 | CD | GLN | B | 298 | 52.733 | 24.269 | 50.142 | 1.00 | 52.74 |
| ATOM | 2698 | OE1 | GLN | B | 298 | 52.735 | 25.216 | 49.332 | 1.00 | 54.37 |
| ATOM | 2699 | NE2 | GLN | B | 298 | 53.473 | 23.161 | 49.959 | 1.00 | 54.29 |
| ATOM | 2700 | C | GLN | B | 298 | 49.926 | 21.328 | 49.997 | 1.00 | 34.88 |
| ATOM | 2701 | O | GLN | B | 298 | 50.862 | 20.594 | 49.660 | 1.00 | 33.87 |
| ATOM | 2702 | N | ARG | B | 299 | 48.723 | 20.866 | 50.310 | 1.00 | 33.43 |
| ATOM | 2703 | CA | ARG | B | 299 | 48.414 | 19.447 | 50.270 | 1.00 | 33.31 |
| ATOM | 2704 | CB | ARG | B | 299 | 47.541 | 19.086 | 51.469 | 1.00 | 34.83 |
| ATOM | 2705 | CG | ARG | B | 299 | 48.235 | 19.332 | 52.792 | 1.00 | 37.10 |
| ATOM | 2706 | CD | ARG | B | 299 | 49.400 | 18.381 | 52.949 | 1.00 | 38.76 |
| ATOM | 2707 | NE | ARG | B | 299 | 50.463 | 18.910 | 53.796 | 1.00 | 40.88 |
| ATOM | 2708 | CZ | ARG | B | 299 | 51.756 | 18.828 | 53.490 | 1.00 | 42.40 |
| ATOM | 2709 | NH1 | ARG | B | 299 | 52.153 | 18.245 | 52.354 | 1.00 | 43.00 |
| ATOM | 2710 | NH2 | ARG | B | 299 | 52.659 | 19.290 | 54.337 | 1.00 | 42.30 |
| ATOM | 2711 | C | ARG | B | 299 | 47.759 | 19.003 | 48.954 | 1.00 | 32.96 |
| ATOM | 2712 | O | ARG | B | 299 | 47.296 | 17.864 | 48.828 | 1.00 | 32.72 |
| ATOM | 2713 | N | LEU | B | 300 | 47.735 | 19.903 | 47.973 | 1.00 | 32.22 |
| ATOM | 2714 | CA | LEU | B | 300 | 47.159 | 19.617 | 46.654 | 1.00 | 31.76 |
| ATOM | 2715 | CB | LEU | B | 300 | 45.993 | 20.581 | 46.373 | 1.00 | 31.66 |
| ATOM | 2716 | CG | LEU | B | 300 | 44.555 | 20.126 | 46.674 | 1.00 | 31.16 |
| ATOM | 2717 | CD1 | LEU | B | 300 | 44.430 | 19.507 | 48.054 | 1.00 | 30.24 |
| ATOM | 2718 | CD2 | LEU | B | 300 | 43.597 | 21.300 | 46.526 | 1.00 | 31.99 |
| ATOM | 2719 | C | LEU | B | 300 | 48.211 | 19.743 | 45.541 | 1.00 | 31.21 |
| ATOM | 2720 | O | LEU | B | 300 | 49.065 | 20.630 | 45.587 | 1.00 | 31.20 |
| ATOM | 2721 | N | VAL | B | 301 | 48.142 | 18.858 | 44.548 | 1.00 | 30.95 |
| ATOM | 2722 | CA | VAL | B | 301 | 49.072 | 18.887 | 43.416 | 1.00 | 31.58 |
| ATOM | 2723 | CB | VAL | B | 301 | 48.878 | 17.665 | 42.492 | 1.00 | 30.56 |
| ATOM | 2724 | CG1 | VAL | B | 301 | 49.606 | 17.871 | 41.177 | 1.00 | 30.65 |
| ATOM | 2725 | CG2 | VAL | B | 301 | 49.405 | 16.413 | 43.180 | 1.00 | 29.24 |
| ATOM | 2726 | C | VAL | B | 301 | 48.916 | 20.198 | 42.629 | 1.00 | 33.20 |
| ATOM | 2727 | O | VAL | B | 301 | 47.817 | 20.567 | 42.215 | 1.00 | 32.81 |
| ATOM | 2728 | N | ARG | B | 302 | 50.037 | 20.885 | 42.427 | 1.00 | 35.20 |
| ATOM | 2729 | CA | ARG | B | 302 | 50.074 | 22.178 | 41.751 | 1.00 | 37.15 |
| ATOM | 2730 | CB | ARG | B | 302 | 51.150 | 23.057 | 42.432 | 1.00 | 40.85 |
| ATOM | 2731 | CG | ARG | B | 302 | 51.299 | 24.483 | 41.932 | 1.00 | 46.78 |
| ATOM | 2732 | CD | ARG | B | 302 | 52.163 | 24.512 | 40.672 | 1.00 | 53.57 |
| ATOM | 2733 | NE | ARG | B | 302 | 52.737 | 25.828 | 40.384 | 1.00 | 57.92 |
| ATOM | 2734 | CZ | ARG | B | 302 | 53.625 | 26.450 | 41.157 | 1.00 | 59.74 |
| ATOM | 2735 | NH1 | ARG | B | 302 | 54.050 | 25.885 | 42.286 | 1.00 | 60.36 |
| ATOM | 2736 | NH2 | ARG | B | 302 | 54.121 | 27.622 | 40.778 | 1.00 | 61.00 |
| ATOM | 2737 | C | ARG | B | 302 | 50.261 | 22.064 | 40.232 | 1.00 | 36.46 |
| ATOM | 2738 | O | ARG | B | 302 | 50.989 | 21.203 | 39.731 | 1.00 | 36.82 |
| ATOM | 2739 | N | LEU | B | 303 | 49.531 | 22.903 | 39.508 | 1.00 | 35.68 |
| ATOM | 2740 | CA | LEU | B | 303 | 49.564 | 22.935 | 38.047 | 1.00 | 35.02 |
| ATOM | 2741 | CB | LEU | B | 303 | 48.151 | 23.188 | 37.509 | 1.00 | 33.88 |
| ATOM | 2742 | CG | LEU | B | 303 | 47.962 | 23.413 | 36.005 | 1.00 | 34.20 |
| ATOM | 2743 | CD1 | LEU | B | 303 | 47.830 | 22.085 | 35.293 | 1.00 | 32.87 |
| ATOM | 2744 | CD2 | LEU | B | 303 | 46.722 | 24.286 | 35.729 | 1.00 | 32.48 |
| ATOM | 2745 | C | LEU | B | 303 | 50.492 | 24.052 | 37.592 | 1.00 | 35.53 |
| ATOM | 2746 | O | LEU | B | 303 | 50.436 | 25.160 | 38.128 | 1.00 | 35.47 |
| ATOM | 2747 | N | TYR | B | 304 | 51.368 | 23.752 | 36.635 | 1.00 | 35.77 |

Figure 8

| | | | | | | | | | |
|---|---|---|---|---|---|---|---|---|---|
| ATOM | 2748 | CA | TYR | B | 304 | 52.300 | 24.745 | 36.105 | 1.00 36.25 |
| ATOM | 2749 | CB | TYR | B | 304 | 53.691 | 24.146 | 35.914 | 1.00 38.54 |
| ATOM | 2750 | CG | TYR | B | 304 | 54.479 | 23.936 | 37.172 | 1.00 41.24 |
| ATOM | 2751 | CD1 | TYR | B | 304 | 54.916 | 22.672 | 37.524 | 1.00 42.69 |
| ATOM | 2752 | CE1 | TYR | B | 304 | 55.681 | 22.461 | 38.666 | 1.00 44.67 |
| ATOM | 2753 | CD2 | TYR | B | 304 | 54.821 | 25.004 | 37.996 | 1.00 44.24 |
| ATOM | 2754 | CE2 | TYR | B | 304 | 55.591 | 24.806 | 39.154 | 1.00 45.76 |
| ATOM | 2755 | CZ | TYR | B | 304 | 56.013 | 23.523 | 39.478 | 1.00 45.14 |
| ATOM | 2756 | OH | TYR | B | 304 | 56.741 | 23.285 | 40.618 | 1.00 45.03 |
| ATOM | 2757 | C | TYR | B | 304 | 51.836 | 25.298 | 34.766 | 1.00 35.67 |
| ATOM | 2758 | O | TYR | B | 304 | 51.996 | 26.478 | 34.497 | 1.00 36.61 |
| ATOM | 2759 | N | ALA | B | 305 | 51.291 | 24.438 | 33.915 | 1.00 34.58 |
| ATOM | 2760 | CA | ALA | B | 305 | 50.848 | 24.864 | 32.601 | 1.00 34.46 |
| ATOM | 2761 | CB | ALA | B | 305 | 52.044 | 25.308 | 31.787 | 1.00 33.89 |
| ATOM | 2762 | C | ALA | B | 305 | 50.115 | 23.762 | 31.859 | 1.00 35.21 |
| ATOM | 2763 | O | ALA | B | 305 | 49.960 | 22.651 | 32.368 | 1.00 35.39 |
| ATOM | 2764 | N | VAL | B | 306 | 49.689 | 24.085 | 30.637 | 1.00 35.90 |
| ATOM | 2765 | CA | VAL | B | 306 | 48.973 | 23.164 | 29.745 | 1.00 36.94 |
| ATOM | 2766 | CB | VAL | B | 306 | 47.407 | 23.256 | 29.941 | 1.00 37.61 |
| ATOM | 2767 | CG1 | VAL | B | 306 | 46.997 | 23.004 | 31.391 | 1.00 35.75 |
| ATOM | 2768 | CG2 | VAL | B | 306 | 46.890 | 24.617 | 29.497 | 1.00 37.72 |
| ATOM | 2769 | C | VAL | B | 306 | 49.281 | 23.505 | 28.270 | 1.00 37.77 |
| ATOM | 2770 | O | VAL | B | 306 | 49.546 | 24.662 | 27.939 | 1.00 38.35 |
| ATOM | 2771 | N | VAL | B | 307 | 49.308 | 22.495 | 27.403 | 1.00 38.30 |
| ATOM | 2772 | CA | VAL | B | 307 | 49.529 | 22.716 | 25.973 | 1.00 39.27 |
| ATOM | 2773 | CB | VAL | B | 307 | 50.753 | 21.953 | 25.437 | 1.00 37.83 |
| ATOM | 2774 | CG1 | VAL | B | 307 | 50.865 | 22.141 | 23.927 | 1.00 36.12 |
| ATOM | 2775 | CG2 | VAL | B | 307 | 52.020 | 22.445 | 26.134 | 1.00 37.71 |
| ATOM | 2776 | C | VAL | B | 307 | 48.263 | 22.252 | 25.249 | 1.00 40.93 |
| ATOM | 2777 | O | VAL | B | 307 | 47.987 | 21.056 | 25.177 | 1.00 40.82 |
| ATOM | 2778 | N | THR | B | 308 | 47.510 | 23.204 | 24.699 | 1.00 43.66 |
| ATOM | 2779 | CA | THR | B | 308 | 46.252 | 22.903 | 24.021 | 1.00 46.09 |
| ATOM | 2780 | CB | THR | B | 308 | 45.285 | 24.090 | 24.062 | 1.00 45.73 |
| ATOM | 2781 | OG1 | THR | B | 308 | 45.938 | 25.244 | 23.532 | 1.00 48.56 |
| ATOM | 2782 | CG2 | THR | B | 308 | 44.844 | 24.371 | 25.487 | 1.00 44.29 |
| ATOM | 2783 | C | THR | B | 308 | 46.296 | 22.333 | 22.606 | 1.00 47.87 |
| ATOM | 2784 | O | THR | B | 308 | 45.249 | 22.004 | 22.061 | 1.00 48.34 |
| ATOM | 2785 | N | GLN | B | 309 | 47.471 | 22.238 | 21.988 | 1.00 49.51 |
| ATOM | 2786 | CA | GLN | B | 309 | 47.545 | 21.634 | 20.654 | 1.00 51.64 |
| ATOM | 2787 | CB | GLN | B | 309 | 48.577 | 22.340 | 19.765 | 1.00 54.89 |
| ATOM | 2788 | CG | GLN | B | 309 | 48.159 | 23.744 | 19.321 | 1.00 59.48 |
| ATOM | 2789 | CD | GLN | B | 309 | 46.831 | 23.784 | 18.547 | 1.00 61.80 |
| ATOM | 2790 | OE1 | GLN | B | 309 | 46.222 | 22.746 | 18.235 | 1.00 62.57 |
| ATOM | 2791 | NE2 | GLN | B | 309 | 46.383 | 24.995 | 18.229 | 1.00 63.37 |
| ATOM | 2792 | C | GLN | B | 309 | 47.887 | 20.157 | 20.786 | 1.00 51.46 |
| ATOM | 2793 | O | GLN | B | 309 | 48.732 | 19.792 | 21.591 | 1.00 51.29 |
| ATOM | 2794 | N | GLU | B | 310 | 47.258 | 19.319 | 19.969 | 1.00 51.65 |
| ATOM | 2795 | CA | GLU | B | 310 | 47.474 | 17.868 | 20.012 | 1.00 52.62 |
| ATOM | 2796 | CB | GLU | B | 310 | 46.484 | 17.151 | 19.079 | 1.00 56.28 |
| ATOM | 2797 | CG | GLU | B | 310 | 46.454 | 17.670 | 17.623 | 1.00 61.94 |
| ATOM | 2798 | CD | GLU | B | 310 | 45.609 | 18.951 | 17.418 | 1.00 63.96 |
| ATOM | 2799 | OE1 | GLU | B | 310 | 44.388 | 18.922 | 17.708 | 1.00 64.50 |
| ATOM | 2800 | OE2 | GLU | B | 310 | 46.165 | 19.975 | 16.950 | 1.00 64.35 |
| ATOM | 2801 | C | GLU | B | 310 | 48.910 | 17.386 | 19.746 | 1.00 51.16 |
| ATOM | 2802 | O | GLU | B | 310 | 49.550 | 17.822 | 18.790 | 1.00 51.58 |
| ATOM | 2803 | N | PRO | B | 311 | 49.449 | 16.502 | 20.623 | 1.00 49.34 |
| ATOM | 2804 | CD | PRO | B | 311 | 50.750 | 15.856 | 20.386 | 1.00 49.07 |
| ATOM | 2805 | CA | PRO | B | 311 | 48.817 | 15.937 | 21.831 | 1.00 46.90 |
| ATOM | 2806 | CB | PRO | B | 311 | 49.794 | 14.821 | 22.245 | 1.00 47.07 |
| ATOM | 2807 | CG | PRO | B | 311 | 50.533 | 14.489 | 20.985 | 1.00 48.41 |

Figure 8

| | | | | | | | | | |
|---|---|---|---|---|---|---|---|---|---|
| ATOM | 2808 | C | PRO | B | 311 | 48.664 | 16.970 | 22.961 | 1.00 44.51 |
| ATOM | 2809 | O | PRO | B | 311 | 49.589 | 17.741 | 23.246 | 1.00 44.67 |
| ATOM | 2810 | N | ILE | B | 312 | 47.483 | 16.990 | 23.581 | 1.00 41.73 |
| ATOM | 2811 | CA | ILE | B | 312 | 47.182 | 17.911 | 24.685 | 1.00 37.49 |
| ATOM | 2812 | CB | ILE | B | 312 | 45.675 | 17.833 | 25.083 | 1.00 38.25 |
| ATOM | 2813 | CG2 | ILE | B | 312 | 45.281 | 19.052 | 25.908 | 1.00 38.04 |
| ATOM | 2814 | CG1 | ILE | B | 312 | 44.784 | 17.759 | 23.843 | 1.00 38.53 |
| ATOM | 2815 | CD1 | ILE | B | 312 | 44.702 | 19.050 | 23.061 | 1.00 38.67 |
| ATOM | 2816 | C | ILE | B | 312 | 48.033 | 17.523 | 25.909 | 1.00 34.20 |
| ATOM | 2817 | O | ILE | B | 312 | 48.213 | 16.326 | 26.196 | 1.00 32.80 |
| ATOM | 2818 | N | TYR | B | 313 | 48.556 | 18.529 | 26.610 | 1.00 30.90 |
| ATOM | 2819 | CA | TYR | B | 313 | 49.387 | 18.307 | 27.799 | 1.00 28.97 |
| ATOM | 2820 | CB | TYR | B | 313 | 50.818 | 18.808 | 27.574 | 1.00 29.75 |
| ATOM | 2821 | CG | TYR | B | 313 | 51.709 | 17.989 | 26.698 | 1.00 29.40 |
| ATOM | 2822 | CD1 | TYR | B | 313 | 51.263 | 16.802 | 26.123 | 1.00 30.35 |
| ATOM | 2823 | CE1 | TYR | B | 313 | 52.090 | 16.056 | 25.274 | 1.00 32.19 |
| ATOM | 2824 | CD2 | TYR | B | 313 | 53.007 | 18.417 | 26.420 | 1.00 29.79 |
| ATOM | 2825 | CE2 | TYR | B | 313 | 53.848 | 17.683 | 25.572 | 1.00 31.62 |
| ATOM | 2826 | CZ | TYR | B | 313 | 53.380 | 16.505 | 24.998 | 1.00 32.05 |
| ATOM | 2827 | OH | TYR | B | 313 | 54.166 | 15.802 | 24.113 | 1.00 32.13 |
| ATOM | 2828 | C | TYR | B | 313 | 48.914 | 19.033 | 29.046 | 1.00 27.25 |
| ATOM | 2829 | O | TYR | B | 313 | 48.459 | 20.167 | 28.965 | 1.00 26.76 |
| ATOM | 2830 | N | ILE | B | 314 | 49.083 | 18.397 | 30.202 | 1.00 25.59 |
| ATOM | 2831 | CA | ILE | B | 314 | 48.766 | 19.024 | 31.484 | 1.00 25.42 |
| ATOM | 2832 | CB | ILE | B | 314 | 47.592 | 18.307 | 32.246 | 1.00 25.73 |
| ATOM | 2833 | CG2 | ILE | B | 314 | 47.582 | 18.724 | 33.703 | 1.00 24.01 |
| ATOM | 2834 | CG1 | ILE | B | 314 | 46.243 | 18.672 | 31.612 | 1.00 25.22 |
| ATOM | 2835 | CD1 | ILE | B | 314 | 45.076 | 17.892 | 32.148 | 1.00 26.45 |
| ATOM | 2836 | C | ILE | B | 314 | 50.089 | 18.898 | 32.228 | 1.00 25.42 |
| ATOM | 2837 | O | ILE | B | 314 | 50.667 | 17.816 | 32.281 | 1.00 27.06 |
| ATOM | 2838 | N | ILE | B | 315 | 50.610 | 20.003 | 32.739 | 1.00 24.67 |
| ATOM | 2839 | CA | ILE | B | 315 | 51.897 | 19.950 | 33.414 | 1.00 25.00 |
| ATOM | 2840 | CB | ILE | B | 315 | 52.941 | 20.867 | 32.706 | 1.00 25.21 |
| ATOM | 2841 | CG2 | ILE | B | 315 | 54.255 | 20.901 | 33.462 | 1.00 24.22 |
| ATOM | 2842 | CG1 | ILE | B | 315 | 53.178 | 20.368 | 31.289 | 1.00 24.70 |
| ATOM | 2843 | CD1 | ILE | B | 315 | 52.307 | 21.036 | 30.260 | 1.00 26.62 |
| ATOM | 2844 | C | ILE | B | 315 | 51.812 | 20.296 | 34.879 | 1.00 24.74 |
| ATOM | 2845 | O | ILE | B | 315 | 51.410 | 21.389 | 35.239 | 1.00 25.21 |
| ATOM | 2846 | N | THR | B | 316 | 52.173 | 19.342 | 35.722 | 1.00 24.34 |
| ATOM | 2847 | CA | THR | B | 316 | 52.137 | 19.573 | 37.144 | 1.00 25.41 |
| ATOM | 2848 | CB | THR | B | 316 | 51.191 | 18.589 | 37.835 | 1.00 25.29 |
| ATOM | 2849 | OG1 | THR | B | 316 | 51.760 | 17.277 | 37.778 | 1.00 23.93 |
| ATOM | 2850 | CG2 | THR | B | 316 | 49.829 | 18.582 | 37.147 | 1.00 24.08 |
| ATOM | 2851 | C | THR | B | 316 | 53.518 | 19.412 | 37.777 | 1.00 26.73 |
| ATOM | 2852 | O | THR | B | 316 | 54.479 | 18.960 | 37.146 | 1.00 27.72 |
| ATOM | 2853 | N | GLU | B | 317 | 53.612 | 19.809 | 39.036 | 1.00 26.42 |
| ATOM | 2854 | CA | GLU | B | 317 | 54.836 | 19.646 | 39.776 | 1.00 26.48 |
| ATOM | 2855 | CB | GLU | B | 317 | 54.666 | 20.140 | 41.220 | 1.00 26.54 |
| ATOM | 2856 | CG | GLU | B | 317 | 53.636 | 19.367 | 42.062 | 1.00 26.56 |
| ATOM | 2857 | CD | GLU | B | 317 | 53.508 | 19.910 | 43.472 | 1.00 28.10 |
| ATOM | 2858 | OE1 | GLU | B | 317 | 52.393 | 20.320 | 43.874 | 1.00 28.33 |
| ATOM | 2859 | OE2 | GLU | B | 317 | 54.532 | 19.928 | 44.191 | 1.00 29.35 |
| ATOM | 2860 | C | GLU | B | 317 | 55.096 | 18.146 | 39.766 | 1.00 27.07 |
| ATOM | 2861 | O | GLU | B | 317 | 54.179 | 17.332 | 39.541 | 1.00 27.37 |
| ATOM | 2862 | N | TYR | B | 318 | 56.357 | 17.788 | 39.963 | 1.00 26.98 |
| ATOM | 2863 | CA | TYR | B | 318 | 56.756 | 16.402 | 39.981 | 1.00 26.33 |
| ATOM | 2864 | CB | TYR | B | 318 | 58.092 | 16.254 | 39.234 | 1.00 26.03 |
| ATOM | 2865 | CG | TYR | B | 318 | 58.668 | 14.859 | 39.232 | 1.00 27.78 |
| ATOM | 2866 | CD1 | TYR | B | 318 | 58.258 | 13.894 | 38.296 | 1.00 28.41 |
| ATOM | 2867 | CE1 | TYR | B | 318 | 58.806 | 12.600 | 38.303 | 1.00 27.92 |

Figure 8

```
ATOM   2868  CD2 TYR B 318      59.631  14.499  40.171  1.00 28.37
ATOM   2869  CE2 TYR B 318      60.176  13.234  40.186  1.00 29.02
ATOM   2870  CZ  TYR B 318      59.771  12.288  39.255  1.00 29.42
ATOM   2871  OH  TYR B 318      60.397  11.056  39.279  1.00 31.14
ATOM   2872  C   TYR B 318      56.829  15.935  41.437  1.00 26.27
ATOM   2873  O   TYR B 318      57.212  16.695  42.331  1.00 26.29
ATOM   2874  N   MET B 319      56.353  14.713  41.672  1.00 26.64
ATOM   2875  CA  MET B 319      56.352  14.091  42.991  1.00 27.16
ATOM   2876  CB  MET B 319      54.936  13.674  43.371  1.00 27.71
ATOM   2877  CG  MET B 319      53.980  14.835  43.538  1.00 26.84
ATOM   2878  SD  MET B 319      54.486  15.935  44.856  1.00 28.43
ATOM   2879  CE  MET B 319      53.913  15.065  46.297  1.00 27.30
ATOM   2880  C   MET B 319      57.253  12.872  42.898  1.00 28.23
ATOM   2881  O   MET B 319      56.869  11.837  42.352  1.00 28.00
ATOM   2882  N   GLU B 320      58.490  13.067  43.344  1.00 30.06
ATOM   2883  CA  GLU B 320      59.562  12.072  43.344  1.00 30.25
ATOM   2884  CB  GLU B 320      60.631  12.522  44.334  1.00 32.62
ATOM   2885  CG  GLU B 320      61.897  11.699  44.346  1.00 38.02
ATOM   2886  CD  GLU B 320      62.679  11.808  43.055  1.00 39.55
ATOM   2887  OE1 GLU B 320      62.918  12.952  42.596  1.00 40.27
ATOM   2888  OE2 GLU B 320      63.046  10.740  42.508  1.00 40.56
ATOM   2889  C   GLU B 320      59.179  10.615  43.609  1.00 29.83
ATOM   2890  O   GLU B 320      59.556   9.730  42.840  1.00 29.75
ATOM   2891  N   ASN B 321      58.415  10.361  44.666  1.00 28.75
ATOM   2892  CA  ASN B 321      58.029   8.988  44.981  1.00 28.53
ATOM   2893  CB  ASN B 321      58.104   8.774  46.486  1.00 28.06
ATOM   2894  CG  ASN B 321      59.527   8.787  46.978  1.00 28.20
ATOM   2895  OD1 ASN B 321      60.354   8.010  46.506  1.00 27.45
ATOM   2896  ND2 ASN B 321      59.832   9.691  47.891  1.00 28.46
ATOM   2897  C   ASN B 321      56.720   8.438  44.401  1.00 28.06
ATOM   2898  O   ASN B 321      56.220   7.399  44.849  1.00 27.65
ATOM   2899  N   GLY B 322      56.184   9.135  43.403  1.00 28.18
ATOM   2900  CA  GLY B 322      54.961   8.719  42.736  1.00 28.85
ATOM   2901  C   GLY B 322      53.691   8.522  43.550  1.00 29.97
ATOM   2902  O   GLY B 322      53.374   9.279  44.465  1.00 30.11
ATOM   2903  N   SER B 323      52.970   7.464  43.193  1.00 30.68
ATOM   2904  CA  SER B 323      51.705   7.093  43.809  1.00 31.02
ATOM   2905  CB  SER B 323      50.982   6.112  42.891  1.00 31.84
ATOM   2906  OG  SER B 323      49.768   5.681  43.460  1.00 35.44
ATOM   2907  C   SER B 323      51.915   6.449  45.163  1.00 30.91
ATOM   2908  O   SER B 323      52.641   5.464  45.267  1.00 31.76
ATOM   2909  N   LEU B 324      51.209   6.958  46.177  1.00 30.30
ATOM   2910  CA  LEU B 324      51.314   6.454  47.546  1.00 30.27
ATOM   2911  CB  LEU B 324      50.364   7.214  48.488  1.00 28.12
ATOM   2912  CG  LEU B 324      50.186   6.683  49.927  1.00 26.96
ATOM   2913  CD1 LEU B 324      51.465   6.819  50.739  1.00 24.74
ATOM   2914  CD2 LEU B 324      49.059   7.424  50.616  1.00 25.87
ATOM   2915  C   LEU B 324      51.088   4.941  47.659  1.00 31.39
ATOM   2916  O   LEU B 324      51.844   4.258  48.345  1.00 32.48
ATOM   2917  N   VAL B 325      50.091   4.414  46.952  1.00 31.72
ATOM   2918  CA  VAL B 325      49.798   2.986  47.000  1.00 32.18
ATOM   2919  CB  VAL B 325      48.541   2.639  46.156  1.00 31.79
ATOM   2920  CG1 VAL B 325      48.867   2.642  44.694  1.00 32.17
ATOM   2921  CG2 VAL B 325      47.956   1.315  46.586  1.00 30.73
ATOM   2922  C   VAL B 325      51.005   2.142  46.570  1.00 32.85
ATOM   2923  O   VAL B 325      51.211   1.041  47.086  1.00 33.17
ATOM   2924  N   ASP B 326      51.822   2.691  45.667  1.00 33.60
ATOM   2925  CA  ASP B 326      53.034   2.013  45.183  1.00 34.35
ATOM   2926  CB  ASP B 326      53.469   2.552  43.816  1.00 33.93
ATOM   2927  CG  ASP B 326      52.623   2.039  42.686  1.00 32.72
```

Figure 8

| ATOM | 2928 | OD1 | ASP | B | 326 | 52.121 | 0.900 | 42.767 | 1.00 | 32.35 |
|------|------|-----|-----|---|-----|--------|-------|--------|------|-------|
| ATOM | 2929 | OD2 | ASP | B | 326 | 52.487 | 2.781 | 41.698 | 1.00 | 34.07 |
| ATOM | 2930 | C   | ASP | B | 326 | 54.211 | 2.180 | 46.156 | 1.00 | 34.92 |
| ATOM | 2931 | O   | ASP | B | 326 | 54.960 | 1.231 | 46.394 | 1.00 | 34.99 |
| ATOM | 2932 | N   | PHE | B | 327 | 54.372 | 3.390 | 46.694 | 1.00 | 34.66 |
| ATOM | 2933 | CA  | PHE | B | 327 | 55.447 | 3.708 | 47.623 | 1.00 | 34.92 |
| ATOM | 2934 | CB  | PHE | B | 327 | 55.370 | 5.182 | 48.023 | 1.00 | 35.38 |
| ATOM | 2935 | CG  | PHE | B | 327 | 56.453 | 5.609 | 48.986 | 1.00 | 35.86 |
| ATOM | 2936 | CD1 | PHE | B | 327 | 57.788 | 5.644 | 48.586 | 1.00 | 36.40 |
| ATOM | 2937 | CD2 | PHE | B | 327 | 56.142 | 5.972 | 50.286 | 1.00 | 35.61 |
| ATOM | 2938 | CE1 | PHE | B | 327 | 58.794 | 6.033 | 49.472 | 1.00 | 36.02 |
| ATOM | 2939 | CE2 | PHE | B | 327 | 57.143 | 6.363 | 51.174 | 1.00 | 35.78 |
| ATOM | 2940 | CZ  | PHE | B | 327 | 58.470 | 6.392 | 50.763 | 1.00 | 36.04 |
| ATOM | 2941 | C   | PHE | B | 327 | 55.452 | 2.854 | 48.889 | 1.00 | 35.82 |
| ATOM | 2942 | O   | PHE | B | 327 | 56.516 | 2.456 | 49.373 | 1.00 | 35.35 |
| ATOM | 2943 | N   | LEU | B | 328 | 54.258 | 2.593 | 49.427 | 1.00 | 36.84 |
| ATOM | 2944 | CA  | LEU | B | 328 | 54.091 | 1.807 | 50.656 | 1.00 | 36.84 |
| ATOM | 2945 | CB  | LEU | B | 328 | 52.631 | 1.806 | 51.122 | 1.00 | 35.59 |
| ATOM | 2946 | CG  | LEU | B | 328 | 51.956 | 3.123 | 51.508 | 1.00 | 33.84 |
| ATOM | 2947 | CD1 | LEU | B | 328 | 50.456 | 2.896 | 51.589 | 1.00 | 33.77 |
| ATOM | 2948 | CD2 | LEU | B | 328 | 52.514 | 3.672 | 52.810 | 1.00 | 31.90 |
| ATOM | 2949 | C   | LEU | B | 328 | 54.562 | 0.376 | 50.488 | 1.00 | 37.55 |
| ATOM | 2950 | O   | LEU | B | 328 | 54.921 | -0.264 | 51.468 | 1.00 | 38.17 |
| ATOM | 2951 | N   | LYS | B | 329 | 54.540 | -0.127 | 49.254 | 1.00 | 38.70 |
| ATOM | 2952 | CA  | LYS | B | 329 | 54.987 | -1.487 | 48.979 | 1.00 | 40.04 |
| ATOM | 2953 | CB  | LYS | B | 329 | 54.300 | -2.063 | 47.735 | 1.00 | 39.75 |
| ATOM | 2954 | CG  | LYS | B | 329 | 52.787 | -2.180 | 47.802 | 1.00 | 40.19 |
| ATOM | 2955 | CD  | LYS | B | 329 | 52.296 | -3.021 | 46.637 | 1.00 | 40.62 |
| ATOM | 2956 | CE  | LYS | B | 329 | 50.827 | -2.841 | 46.397 | 1.00 | 40.86 |
| ATOM | 2957 | NZ  | LYS | B | 329 | 50.551 | -1.448 | 45.965 | 1.00 | 42.74 |
| ATOM | 2958 | C   | LYS | B | 329 | 56.502 | -1.600 | 48.806 | 1.00 | 40.99 |
| ATOM | 2959 | O   | LYS | B | 329 | 57.039 | -2.704 | 48.942 | 1.00 | 41.48 |
| ATOM | 2960 | N   | THR | B | 330 | 57.181 | -0.474 | 48.526 | 1.00 | 41.85 |
| ATOM | 2961 | CA  | THR | B | 330 | 58.645 | -0.444 | 48.321 | 1.00 | 42.77 |
| ATOM | 2962 | CB  | THR | B | 330 | 59.164 | 0.924 | 47.727 | 1.00 | 42.06 |
| ATOM | 2963 | OG1 | THR | B | 330 | 59.027 | 1.970 | 48.697 | 1.00 | 41.70 |
| ATOM | 2964 | CG2 | THR | B | 330 | 58.440 | 1.306 | 46.445 | 1.00 | 41.25 |
| ATOM | 2965 | C   | THR | B | 330 | 59.406 | -0.688 | 49.622 | 1.00 | 44.32 |
| ATOM | 2966 | O   | THR | B | 330 | 58.852 | -0.482 | 50.700 | 1.00 | 45.30 |
| ATOM | 2967 | N   | PRO | B | 331 | 60.688 | -1.125 | 49.533 | 1.00 | 45.21 |
| ATOM | 2968 | CD  | PRO | B | 331 | 61.389 | -1.451 | 48.275 | 1.00 | 45.59 |
| ATOM | 2969 | CA  | PRO | B | 331 | 61.559 | -1.404 | 50.680 | 1.00 | 45.58 |
| ATOM | 2970 | CB  | PRO | B | 331 | 62.944 | -1.441 | 50.037 | 1.00 | 45.91 |
| ATOM | 2971 | CG  | PRO | B | 331 | 62.669 | -2.120 | 48.761 | 1.00 | 45.93 |
| ATOM | 2972 | C   | PRO | B | 331 | 61.479 | -0.315 | 51.744 | 1.00 | 45.92 |
| ATOM | 2973 | O   | PRO | B | 331 | 61.338 | -0.615 | 52.931 | 1.00 | 46.26 |
| ATOM | 2974 | N   | SER | B | 332 | 61.527 | 0.941 | 51.298 | 1.00 | 46.09 |
| ATOM | 2975 | CA  | SER | B | 332 | 61.458 | 2.111 | 52.182 | 1.00 | 47.06 |
| ATOM | 2976 | CB  | SER | B | 332 | 61.792 | 3.385 | 51.412 | 1.00 | 47.81 |
| ATOM | 2977 | OG  | SER | B | 332 | 62.985 | 3.231 | 50.675 | 1.00 | 50.87 |
| ATOM | 2978 | C   | SER | B | 332 | 60.074 | 2.293 | 52.782 | 1.00 | 46.82 |
| ATOM | 2979 | O   | SER | B | 332 | 59.941 | 2.697 | 53.938 | 1.00 | 46.15 |
| ATOM | 2980 | N   | GLY | B | 333 | 59.054 | 2.062 | 51.954 | 1.00 | 46.91 |
| ATOM | 2981 | CA  | GLY | B | 333 | 57.675 | 2.203 | 52.382 | 1.00 | 46.37 |
| ATOM | 2982 | C   | GLY | B | 333 | 57.283 | 1.159 | 53.402 | 1.00 | 46.54 |
| ATOM | 2983 | O   | GLY | B | 333 | 56.548 | 1.462 | 54.348 | 1.00 | 46.87 |
| ATOM | 2984 | N   | ILE | B | 334 | 57.783 | -0.063 | 53.221 | 1.00 | 45.81 |
| ATOM | 2985 | CA  | ILE | B | 334 | 57.484 | -1.151 | 54.142 | 1.00 | 45.90 |
| ATOM | 2986 | CB  | ILE | B | 334 | 57.967 | -2.522 | 53.584 | 1.00 | 45.80 |
| ATOM | 2987 | CG2 | ILE | B | 334 | 57.682 | -3.624 | 54.587 | 1.00 | 46.85 |

Figure 8

| | | | | | | | | | |
|---|---|---|---|---|---|---|---|---|---|
| ATOM | 2988 | CG1 | ILE | B | 334 | 57.224 | -2.885 | 52.288 | 1.00 45.91 |
| ATOM | 2989 | CD1 | ILE | B | 334 | 55.792 | -3.452 | 52.487 | 1.00 46.68 |
| ATOM | 2990 | C | ILE | B | 334 | 58.122 | -0.870 | 55.511 | 1.00 46.26 |
| ATOM | 2991 | O | ILE | B | 334 | 57.591 | -1.276 | 56.545 | 1.00 46.15 |
| ATOM | 2992 | N | LYS | B | 335 | 59.210 | -0.099 | 55.510 | 1.00 46.71 |
| ATOM | 2993 | CA | LYS | B | 335 | 59.936 | 0.252 | 56.735 | 1.00 46.99 |
| ATOM | 2994 | CB | LYS | B | 335 | 61.424 | 0.504 | 56.429 | 1.00 48.78 |
| ATOM | 2995 | CG | LYS | B | 335 | 62.251 | -0.700 | 55.963 | 1.00 50.52 |
| ATOM | 2996 | CD | LYS | B | 335 | 63.546 | -0.205 | 55.299 | 1.00 53.47 |
| ATOM | 2997 | CE | LYS | B | 335 | 64.360 | -1.344 | 54.652 | 1.00 55.24 |
| ATOM | 2998 | NZ | LYS | B | 335 | 65.278 | -0.845 | 53.562 | 1.00 54.86 |
| ATOM | 2999 | C | LYS | B | 335 | 59.383 | 1.471 | 57.493 | 1.00 46.52 |
| ATOM | 3000 | O | LYS | B | 335 | 59.830 | 1.753 | 58.608 | 1.00 47.06 |
| ATOM | 3001 | N | LEU | B | 336 | 58.458 | 2.221 | 56.893 | 1.00 45.51 |
| ATOM | 3002 | CA | LEU | B | 336 | 57.889 | 3.404 | 57.564 | 1.00 43.92 |
| ATOM | 3003 | CB | LEU | B | 336 | 56.849 | 4.111 | 56.671 | 1.00 43.44 |
| ATOM | 3004 | CG | LEU | B | 336 | 57.299 | 4.837 | 55.397 | 1.00 41.90 |
| ATOM | 3005 | CD1 | LEU | B | 336 | 56.104 | 5.238 | 54.571 | 1.00 40.93 |
| ATOM | 3006 | CD2 | LEU | B | 336 | 58.126 | 6.049 | 55.753 | 1.00 41.68 |
| ATOM | 3007 | C | LEU | B | 336 | 57.253 | 3.093 | 58.925 | 1.00 43.01 |
| ATOM | 3008 | O | LEU | B | 336 | 56.523 | 2.099 | 59.083 | 1.00 42.78 |
| ATOM | 3009 | N | THR | B | 337 | 57.518 | 3.971 | 59.892 | 1.00 41.71 |
| ATOM | 3010 | CA | THR | B | 337 | 56.974 | 3.813 | 61.236 | 1.00 40.92 |
| ATOM | 3011 | CB | THR | B | 337 | 57.819 | 4.584 | 62.324 | 1.00 40.77 |
| ATOM | 3012 | OG1 | THR | B | 337 | 57.531 | 5.983 | 62.282 | 1.00 40.39 |
| ATOM | 3013 | CG2 | THR | B | 337 | 59.326 | 4.394 | 62.098 | 1.00 40.94 |
| ATOM | 3014 | C | THR | B | 337 | 55.508 | 4.276 | 61.278 | 1.00 40.36 |
| ATOM | 3015 | O | THR | B | 337 | 55.063 | 5.043 | 60.409 | 1.00 40.24 |
| ATOM | 3016 | N | ILE | B | 338 | 54.772 | 3.788 | 62.280 | 1.00 38.79 |
| ATOM | 3017 | CA | ILE | B | 338 | 53.363 | 4.118 | 62.481 | 1.00 37.05 |
| ATOM | 3018 | CB | ILE | B | 338 | 52.784 | 3.381 | 63.719 | 1.00 35.59 |
| ATOM | 3019 | CG2 | ILE | B | 338 | 53.528 | 3.793 | 64.974 | 1.00 34.04 |
| ATOM | 3020 | CG1 | ILE | B | 338 | 51.293 | 3.696 | 63.887 | 1.00 34.80 |
| ATOM | 3021 | CD1 | ILE | B | 338 | 50.398 | 3.150 | 62.805 | 1.00 32.52 |
| ATOM | 3022 | C | ILE | B | 338 | 53.182 | 5.618 | 62.658 | 1.00 37.21 |
| ATOM | 3023 | O | ILE | B | 338 | 52.185 | 6.190 | 62.237 | 1.00 37.07 |
| ATOM | 3024 | N | ASN | B | 339 | 54.179 | 6.256 | 63.253 | 1.00 37.59 |
| ATOM | 3025 | CA | ASN | B | 339 | 54.148 | 7.689 | 63.484 | 1.00 38.00 |
| ATOM | 3026 | CB | ASN | B | 339 | 55.337 | 8.092 | 64.353 | 1.00 40.33 |
| ATOM | 3027 | CG | ASN | B | 339 | 55.419 | 7.285 | 65.634 | 1.00 41.79 |
| ATOM | 3028 | OD1 | ASN | B | 339 | 55.018 | 7.763 | 66.702 | 1.00 41.40 |
| ATOM | 3029 | ND2 | ASN | B | 339 | 55.939 | 6.050 | 65.536 | 1.00 42.28 |
| ATOM | 3030 | C | ASN | B | 339 | 54.211 | 8.446 | 62.168 | 1.00 37.76 |
| ATOM | 3031 | O | ASN | B | 339 | 53.529 | 9.458 | 61.994 | 1.00 38.90 |
| ATOM | 3032 | N | LYS | B | 340 | 55.065 | 7.979 | 61.260 | 1.00 36.84 |
| ATOM | 3033 | CA | LYS | B | 340 | 55.221 | 8.609 | 59.956 | 1.00 36.34 |
| ATOM | 3034 | CB | LYS | B | 340 | 56.461 | 8.045 | 59.250 | 1.00 37.23 |
| ATOM | 3035 | CG | LYS | B | 340 | 56.710 | 8.606 | 57.848 | 1.00 39.62 |
| ATOM | 3036 | CD | LYS | B | 340 | 56.706 | 10.142 | 57.807 | 1.00 39.88 |
| ATOM | 3037 | CE | LYS | B | 340 | 56.507 | 10.635 | 56.376 | 1.00 40.84 |
| ATOM | 3038 | NZ | LYS | B | 340 | 56.379 | 12.117 | 56.270 | 1.00 41.37 |
| ATOM | 3039 | C | LYS | B | 340 | 53.942 | 8.423 | 59.119 | 1.00 35.24 |
| ATOM | 3040 | O | LYS | B | 340 | 53.425 | 9.386 | 58.554 | 1.00 35.18 |
| ATOM | 3041 | N | LEU | B | 341 | 53.412 | 7.197 | 59.110 | 1.00 34.13 |
| ATOM | 3042 | CA | LEU | B | 341 | 52.182 | 6.839 | 58.391 | 1.00 32.76 |
| ATOM | 3043 | CB | LEU | B | 341 | 51.810 | 5.369 | 58.663 | 1.00 30.36 |
| ATOM | 3044 | CG | LEU | B | 341 | 52.713 | 4.253 | 58.126 | 1.00 28.41 |
| ATOM | 3045 | CD1 | LEU | B | 341 | 52.192 | 2.928 | 58.579 | 1.00 27.04 |
| ATOM | 3046 | CD2 | LEU | B | 341 | 52.773 | 4.294 | 56.628 | 1.00 27.06 |
| ATOM | 3047 | C | LEU | B | 341 | 51.007 | 7.735 | 58.798 | 1.00 32.79 |

Figure 8

```
ATOM   3048  O   LEU B 341      50.293   8.269  57.950  1.00 32.13
ATOM   3049  N   LEU B 342      50.806   7.887  60.103  1.00 33.21
ATOM   3050  CA  LEU B 342      49.733   8.730  60.607  1.00 34.02
ATOM   3051  CB  LEU B 342      49.593   8.577  62.118  1.00 34.28
ATOM   3052  CG  LEU B 342      48.865   7.300  62.530  1.00 34.84
ATOM   3053  CD1 LEU B 342      48.995   7.118  63.992  1.00 35.62
ATOM   3054  CD2 LEU B 342      47.397   7.382  62.163  1.00 36.93
ATOM   3055  C   LEU B 342      49.949  10.192  60.227  1.00 34.17
ATOM   3056  O   LEU B 342      48.985  10.932  60.009  1.00 34.30
ATOM   3057  N   ASP B 343      51.209  10.607  60.145  1.00 34.18
ATOM   3058  CA  ASP B 343      51.493  11.969  59.751  1.00 34.82
ATOM   3059  CB  ASP B 343      52.963  12.321  59.974  1.00 38.10
ATOM   3060  CG  ASP B 343      53.269  13.775  59.618  1.00 42.83
ATOM   3061  OD1 ASP B 343      52.536  14.692  60.095  1.00 44.36
ATOM   3062  OD2 ASP B 343      54.225  13.993  58.834  1.00 44.80
ATOM   3063  C   ASP B 343      51.101  12.139  58.277  1.00 33.78
ATOM   3064  O   ASP B 343      50.573  13.186  57.888  1.00 33.99
ATOM   3065  N   MET B 344      51.326  11.099  57.470  1.00 32.07
ATOM   3066  CA  MET B 344      50.962  11.135  56.053  1.00 31.20
ATOM   3067  CB  MET B 344      51.504   9.910  55.312  1.00 32.06
ATOM   3068  CG  MET B 344      53.025   9.876  55.167  1.00 33.23
ATOM   3069  SD  MET B 344      53.660   8.379  54.306  1.00 34.04
ATOM   3070  CE  MET B 344      53.864   8.935  52.650  1.00 32.13
ATOM   3071  C   MET B 344      49.431  11.203  55.912  1.00 29.93
ATOM   3072  O   MET B 344      48.908  11.974  55.110  1.00 28.97
ATOM   3073  N   ALA B 345      48.731  10.411  56.722  1.00 29.22
ATOM   3074  CA  ALA B 345      47.270  10.380  56.733  1.00 28.36
ATOM   3075  CB  ALA B 345      46.775   9.306  57.707  1.00 27.44
ATOM   3076  C   ALA B 345      46.743  11.758  57.142  1.00 27.78
ATOM   3077  O   ALA B 345      45.753  12.225  56.600  1.00 27.80
ATOM   3078  N   ALA B 346      47.426  12.407  58.085  1.00 27.57
ATOM   3079  CA  ALA B 346      47.047  13.738  58.554  1.00 27.33
ATOM   3080  CB  ALA B 346      47.920  14.146  59.704  1.00 25.41
ATOM   3081  C   ALA B 346      47.146  14.772  57.427  1.00 28.73
ATOM   3082  O   ALA B 346      46.359  15.729  57.375  1.00 30.28
ATOM   3083  N   GLN B 347      48.112  14.580  56.527  1.00 28.48
ATOM   3084  CA  GLN B 347      48.312  15.482  55.388  1.00 27.49
ATOM   3085  CB  GLN B 347      49.658  15.219  54.719  1.00 29.36
ATOM   3086  CG  GLN B 347      50.846  15.484  55.612  1.00 31.75
ATOM   3087  CD  GLN B 347      52.148  15.213  54.917  1.00 32.64
ATOM   3088  OE1 GLN B 347      53.020  16.067  54.874  1.00 36.23
ATOM   3089  NE2 GLN B 347      52.287  14.028  54.360  1.00 33.41
ATOM   3090  C   GLN B 347      47.208  15.354  54.347  1.00 25.67
ATOM   3091  O   GLN B 347      46.783  16.344  53.758  1.00 25.27
ATOM   3092  N   ILE B 348      46.787  14.125  54.089  1.00 24.25
ATOM   3093  CA  ILE B 348      45.724  13.862  53.129  1.00 23.48
ATOM   3094  CB  ILE B 348      45.582  12.349  52.867  1.00 22.13
ATOM   3095  CG2 ILE B 348      44.404  12.088  51.937  1.00 22.04
ATOM   3096  CG1 ILE B 348      46.896  11.796  52.298  1.00 20.24
ATOM   3097  CD1 ILE B 348      46.994  10.285  52.278  1.00 16.28
ATOM   3098  C   ILE B 348      44.402  14.421  53.672  1.00 23.70
ATOM   3099  O   ILE B 348      43.596  14.966  52.911  1.00 23.19
ATOM   3100  N   ALA B 349      44.210  14.295  54.989  1.00 23.69
ATOM   3101  CA  ALA B 349      43.017  14.785  55.678  1.00 24.29
ATOM   3102  CB  ALA B 349      42.986  14.277  57.116  1.00 24.10
ATOM   3103  C   ALA B 349      42.987  16.311  55.666  1.00 25.56
ATOM   3104  O   ALA B 349      41.915  16.921  55.608  1.00 26.62
ATOM   3105  N   GLU B 350      44.174  16.920  55.727  1.00 25.65
ATOM   3106  CA  GLU B 350      44.328  18.369  55.698  1.00 25.11
ATOM   3107  CB  GLU B 350      45.767  18.742  56.002  1.00 25.93
```

Figure 8

| ATOM | 3108 | CG | GLU | B | 350 | 46.019 | 20.218 | 56.105 | 1.00 | 28.89 |
| ATOM | 3109 | CD | GLU | B | 350 | 47.507 | 20.568 | 56.223 | 1.00 | 31.27 |
| ATOM | 3110 | OE1 | GLU | B | 350 | 48.298 | 19.777 | 56.787 | 1.00 | 30.48 |
| ATOM | 3111 | OE2 | GLU | B | 350 | 47.891 | 21.657 | 55.746 | 1.00 | 33.25 |
| ATOM | 3112 | C | GLU | B | 350 | 43.936 | 18.899 | 54.329 | 1.00 | 25.21 |
| ATOM | 3113 | O | GLU | B | 350 | 43.269 | 19.924 | 54.221 | 1.00 | 26.22 |
| ATOM | 3114 | N | GLY | B | 351 | 44.336 | 18.186 | 53.280 | 1.00 | 24.99 |
| ATOM | 3115 | CA | GLY | B | 351 | 43.987 | 18.602 | 51.937 | 1.00 | 23.89 |
| ATOM | 3116 | C | GLY | B | 351 | 42.497 | 18.452 | 51.724 | 1.00 | 23.28 |
| ATOM | 3117 | O | GLY | B | 351 | 41.866 | 19.298 | 51.091 | 1.00 | 24.29 |
| ATOM | 3118 | N | MET | B | 352 | 41.939 | 17.356 | 52.228 | 1.00 | 23.08 |
| ATOM | 3119 | CA | MET | B | 352 | 40.509 | 17.102 | 52.117 | 1.00 | 22.49 |
| ATOM | 3120 | CB | MET | B | 352 | 40.164 | 15.701 | 52.581 | 1.00 | 19.92 |
| ATOM | 3121 | CG | MET | B | 352 | 40.550 | 14.635 | 51.602 | 1.00 | 18.99 |
| ATOM | 3122 | SD | MET | B | 352 | 40.048 | 15.024 | 49.902 | 1.00 | 21.65 |
| ATOM | 3123 | CE | MET | B | 352 | 38.220 | 15.090 | 50.101 | 1.00 | 19.15 |
| ATOM | 3124 | C | MET | B | 352 | 39.729 | 18.112 | 52.935 | 1.00 | 24.29 |
| ATOM | 3125 | O | MET | B | 352 | 38.608 | 18.474 | 52.565 | 1.00 | 26.14 |
| ATOM | 3126 | N | ALA | B | 353 | 40.311 | 18.559 | 54.051 | 1.00 | 24.72 |
| ATOM | 3127 | CA | ALA | B | 353 | 39.676 | 19.564 | 54.903 | 1.00 | 25.35 |
| ATOM | 3128 | CB | ALA | B | 353 | 40.520 | 19.809 | 56.136 | 1.00 | 24.62 |
| ATOM | 3129 | C | ALA | B | 353 | 39.528 | 20.870 | 54.094 | 1.00 | 26.25 |
| ATOM | 3130 | O | ALA | B | 353 | 38.557 | 21.611 | 54.259 | 1.00 | 26.44 |
| ATOM | 3131 | N | PHE | B | 354 | 40.508 | 21.143 | 53.231 | 1.00 | 26.34 |
| ATOM | 3132 | CA | PHE | B | 354 | 40.494 | 22.326 | 52.366 | 1.00 | 26.35 |
| ATOM | 3133 | CB | PHE | B | 354 | 41.869 | 22.518 | 51.698 | 1.00 | 26.16 |
| ATOM | 3134 | CG | PHE | B | 354 | 41.912 | 23.650 | 50.698 | 1.00 | 25.57 |
| ATOM | 3135 | CD1 | PHE | B | 354 | 41.810 | 24.974 | 51.120 | 1.00 | 24.71 |
| ATOM | 3136 | CD2 | PHE | B | 354 | 42.053 | 23.389 | 49.332 | 1.00 | 25.81 |
| ATOM | 3137 | CE1 | PHE | B | 354 | 41.844 | 26.021 | 50.202 | 1.00 | 25.05 |
| ATOM | 3138 | CE2 | PHE | B | 354 | 42.090 | 24.435 | 48.394 | 1.00 | 26.42 |
| ATOM | 3139 | CZ | PHE | B | 354 | 41.985 | 25.754 | 48.834 | 1.00 | 25.28 |
| ATOM | 3140 | C | PHE | B | 354 | 39.430 | 22.147 | 51.292 | 1.00 | 25.99 |
| ATOM | 3141 | O | PHE | B | 354 | 38.693 | 23.069 | 50.971 | 1.00 | 25.71 |
| ATOM | 3142 | N | ILE | B | 355 | 39.379 | 20.957 | 50.716 | 1.00 | 26.49 |
| ATOM | 3143 | CA | ILE | B | 355 | 38.403 | 20.660 | 49.676 | 1.00 | 27.29 |
| ATOM | 3144 | CB | ILE | B | 355 | 38.660 | 19.241 | 49.068 | 1.00 | 26.76 |
| ATOM | 3145 | CG2 | ILE | B | 355 | 37.488 | 18.785 | 48.192 | 1.00 | 25.82 |
| ATOM | 3146 | CG1 | ILE | B | 355 | 39.973 | 19.266 | 48.266 | 1.00 | 25.77 |
| ATOM | 3147 | CD1 | ILE | B | 355 | 40.328 | 17.964 | 47.571 | 1.00 | 24.43 |
| ATOM | 3148 | C | ILE | B | 355 | 37.003 | 20.786 | 50.281 | 1.00 | 27.95 |
| ATOM | 3149 | O | ILE | B | 355 | 36.114 | 21.393 | 49.689 | 1.00 | 27.90 |
| ATOM | 3150 | N | GLU | B | 356 | 36.852 | 20.323 | 51.514 | 1.00 | 28.64 |
| ATOM | 3151 | CA | GLU | B | 356 | 35.572 | 20.385 | 52.209 | 1.00 | 29.93 |
| ATOM | 3152 | CB | GLU | B | 356 | 35.698 | 19.639 | 53.513 | 1.00 | 27.75 |
| ATOM | 3153 | CG | GLU | B | 356 | 34.474 | 19.553 | 54.351 | 1.00 | 25.70 |
| ATOM | 3154 | CD | GLU | B | 356 | 34.777 | 18.773 | 55.591 | 1.00 | 25.14 |
| ATOM | 3155 | OE1 | GLU | B | 356 | 35.453 | 19.324 | 56.485 | 1.00 | 26.30 |
| ATOM | 3156 | OE2 | GLU | B | 356 | 34.404 | 17.591 | 55.647 | 1.00 | 24.46 |
| ATOM | 3157 | C | GLU | B | 356 | 35.208 | 21.834 | 52.484 | 1.00 | 31.97 |
| ATOM | 3158 | O | GLU | B | 356 | 34.097 | 22.277 | 52.220 | 1.00 | 33.57 |
| ATOM | 3159 | N | GLU | B | 357 | 36.180 | 22.552 | 53.020 | 1.00 | 33.83 |
| ATOM | 3160 | CA | GLU | B | 357 | 36.087 | 23.964 | 53.362 | 1.00 | 35.38 |
| ATOM | 3161 | CB | GLU | B | 357 | 37.490 | 24.404 | 53.803 | 1.00 | 38.21 |
| ATOM | 3162 | CG | GLU | B | 357 | 37.816 | 25.856 | 53.687 | 1.00 | 42.25 |
| ATOM | 3163 | CD | GLU | B | 357 | 37.078 | 26.659 | 54.701 | 1.00 | 45.49 |
| ATOM | 3164 | OE1 | GLU | B | 357 | 37.533 | 26.701 | 55.865 | 1.00 | 48.20 |
| ATOM | 3165 | OE2 | GLU | B | 357 | 36.038 | 27.237 | 54.338 | 1.00 | 47.61 |
| ATOM | 3166 | C | GLU | B | 357 | 35.581 | 24.810 | 52.189 | 1.00 | 35.23 |
| ATOM | 3167 | O | GLU | B | 357 | 34.707 | 25.655 | 52.353 | 1.00 | 35.34 |

Figure 8

| ATOM | 3168 | N   | ARG | B | 358 | 36.087 | 24.523 | 50.995 | 1.00 | 35.80 |
|------|------|-----|-----|---|-----|--------|--------|--------|------|-------|
| ATOM | 3169 | CA  | ARG | B | 358 | 35.718 | 25.251 | 49.782 | 1.00 | 36.32 |
| ATOM | 3170 | CB  | ARG | B | 358 | 36.910 | 25.288 | 48.829 | 1.00 | 37.58 |
| ATOM | 3171 | CG  | ARG | B | 358 | 38.154 | 25.917 | 49.437 | 1.00 | 42.31 |
| ATOM | 3172 | CD  | ARG | B | 358 | 38.048 | 27.443 | 49.527 | 1.00 | 46.96 |
| ATOM | 3173 | NE  | ARG | B | 358 | 37.882 | 28.008 | 48.192 | 1.00 | 52.22 |
| ATOM | 3174 | CZ  | ARG | B | 358 | 38.820 | 27.975 | 47.242 | 1.00 | 55.41 |
| ATOM | 3175 | NH1 | ARG | B | 358 | 40.004 | 27.432 | 47.488 | 1.00 | 57.01 |
| ATOM | 3176 | NH2 | ARG | B | 358 | 38.536 | 28.358 | 45.999 | 1.00 | 56.65 |
| ATOM | 3177 | C   | ARG | B | 358 | 34.509 | 24.651 | 49.073 | 1.00 | 36.08 |
| ATOM | 3178 | O   | ARG | B | 358 | 34.215 | 24.991 | 47.934 | 1.00 | 35.12 |
| ATOM | 3179 | N   | ASN | B | 359 | 33.825 | 23.745 | 49.765 | 1.00 | 36.34 |
| ATOM | 3180 | CA  | ASN | B | 359 | 32.640 | 23.059 | 49.266 | 1.00 | 36.56 |
| ATOM | 3181 | CB  | ASN | B | 359 | 31.407 | 23.944 | 49.416 | 1.00 | 39.43 |
| ATOM | 3182 | CG  | ASN | B | 359 | 31.287 | 24.523 | 50.836 | 1.00 | 44.66 |
| ATOM | 3183 | OD1 | ASN | B | 359 | 30.791 | 23.861 | 51.769 | 1.00 | 46.05 |
| ATOM | 3184 | ND2 | ASN | B | 359 | 31.788 | 25.756 | 51.014 | 1.00 | 46.83 |
| ATOM | 3185 | C   | ASN | B | 359 | 32.746 | 22.400 | 47.886 | 1.00 | 36.07 |
| ATOM | 3186 | O   | ASN | B | 359 | 31.981 | 22.681 | 46.955 | 1.00 | 35.93 |
| ATOM | 3187 | N   | TYR | B | 360 | 33.734 | 21.514 | 47.788 | 1.00 | 34.52 |
| ATOM | 3188 | CA  | TYR | B | 360 | 33.997 | 20.702 | 46.606 | 1.00 | 33.23 |
| ATOM | 3189 | CB  | TYR | B | 360 | 35.384 | 20.978 | 46.020 | 1.00 | 32.62 |
| ATOM | 3190 | CG  | TYR | B | 360 | 35.461 | 22.149 | 45.081 | 1.00 | 33.34 |
| ATOM | 3191 | CD1 | TYR | B | 360 | 35.712 | 23.434 | 45.566 | 1.00 | 34.33 |
| ATOM | 3192 | CE1 | TYR | B | 360 | 35.824 | 24.529 | 44.707 | 1.00 | 34.24 |
| ATOM | 3193 | CD2 | TYR | B | 360 | 35.321 | 21.977 | 43.704 | 1.00 | 33.67 |
| ATOM | 3194 | CE2 | TYR | B | 360 | 35.434 | 23.064 | 42.829 | 1.00 | 35.65 |
| ATOM | 3195 | CZ  | TYR | B | 360 | 35.685 | 24.338 | 43.342 | 1.00 | 35.60 |
| ATOM | 3196 | OH  | TYR | B | 360 | 35.803 | 25.416 | 42.494 | 1.00 | 37.44 |
| ATOM | 3197 | C   | TYR | B | 360 | 34.036 | 19.297 | 47.172 | 1.00 | 32.74 |
| ATOM | 3198 | O   | TYR | B | 360 | 33.962 | 19.108 | 48.393 | 1.00 | 32.36 |
| ATOM | 3199 | N   | ILE | B | 361 | 34.174 | 18.316 | 46.289 | 1.00 | 31.78 |
| ATOM | 3200 | CA  | ILE | B | 361 | 34.292 | 16.926 | 46.703 | 1.00 | 30.98 |
| ATOM | 3201 | CB  | ILE | B | 361 | 32.963 | 16.133 | 46.554 | 1.00 | 30.24 |
| ATOM | 3202 | CG2 | ILE | B | 361 | 31.858 | 16.801 | 47.349 | 1.00 | 29.71 |
| ATOM | 3203 | CG1 | ILE | B | 361 | 32.568 | 15.992 | 45.091 | 1.00 | 30.01 |
| ATOM | 3204 | CD1 | ILE | B | 361 | 31.549 | 14.892 | 44.849 | 1.00 | 30.33 |
| ATOM | 3205 | C   | ILE | B | 361 | 35.362 | 16.335 | 45.800 | 1.00 | 30.70 |
| ATOM | 3206 | O   | ILE | B | 361 | 35.625 | 16.877 | 44.732 | 1.00 | 31.81 |
| ATOM | 3207 | N   | HIS | B | 362 | 36.035 | 15.285 | 46.258 | 1.00 | 29.92 |
| ATOM | 3208 | CA  | HIS | B | 362 | 37.062 | 14.625 | 45.456 | 1.00 | 28.86 |
| ATOM | 3209 | CB  | HIS | B | 362 | 38.055 | 13.900 | 46.369 | 1.00 | 26.96 |
| ATOM | 3210 | CG  | HIS | B | 362 | 39.288 | 13.405 | 45.678 | 1.00 | 25.24 |
| ATOM | 3211 | CD2 | HIS | B | 362 | 40.600 | 13.665 | 45.908 | 1.00 | 25.13 |
| ATOM | 3212 | ND1 | HIS | B | 362 | 39.263 | 12.486 | 44.654 | 1.00 | 26.50 |
| ATOM | 3213 | CE1 | HIS | B | 362 | 40.499 | 12.197 | 44.283 | 1.00 | 25.00 |
| ATOM | 3214 | NE2 | HIS | B | 362 | 41.328 | 12.902 | 45.033 | 1.00 | 23.27 |
| ATOM | 3215 | C   | HIS | B | 362 | 36.365 | 13.614 | 44.552 | 1.00 | 29.12 |
| ATOM | 3216 | O   | HIS | B | 362 | 36.478 | 13.677 | 43.321 | 1.00 | 29.78 |
| ATOM | 3217 | N   | ARG | B | 363 | 35.644 | 12.700 | 45.198 | 1.00 | 27.97 |
| ATOM | 3218 | CA  | ARG | B | 363 | 34.903 | 11.597 | 44.586 | 1.00 | 28.70 |
| ATOM | 3219 | CB  | ARG | B | 363 | 33.820 | 12.059 | 43.593 | 1.00 | 31.24 |
| ATOM | 3220 | CG  | ARG | B | 363 | 34.274 | 12.531 | 42.238 | 1.00 | 34.59 |
| ATOM | 3221 | CD  | ARG | B | 363 | 33.092 | 12.984 | 41.391 | 1.00 | 36.61 |
| ATOM | 3222 | NE  | ARG | B | 363 | 32.327 | 11.866 | 40.863 | 1.00 | 37.07 |
| ATOM | 3223 | CZ  | ARG | B | 363 | 31.003 | 11.836 | 40.861 | 1.00 | 38.40 |
| ATOM | 3224 | NH1 | ARG | B | 363 | 30.335 | 12.872 | 41.358 | 1.00 | 38.21 |
| ATOM | 3225 | NH2 | ARG | B | 363 | 30.354 | 10.779 | 40.378 | 1.00 | 37.83 |
| ATOM | 3226 | C   | ARG | B | 363 | 35.721 | 10.438 | 44.031 | 1.00 | 27.53 |
| ATOM | 3227 | O   | ARG | B | 363 | 35.152 |  9.463 | 43.566 | 1.00 | 26.60 |

Figure 8

```
ATOM   3228  N    ASP B 364      37.048  10.535  44.122  1.00 27.29
ATOM   3229  CA   ASP B 364      37.959   9.484  43.661  1.00 26.97
ATOM   3230  CB   ASP B 364      38.563   9.839  42.293  1.00 26.39
ATOM   3231  CG   ASP B 364      37.584   9.662  41.145  1.00 26.46
ATOM   3232  OD1  ASP B 364      37.263   8.498  40.811  1.00 26.89
ATOM   3233  OD2  ASP B 364      37.162  10.686  40.559  1.00 26.37
ATOM   3234  C    ASP B 364      39.082   9.290  44.702  1.00 27.42
ATOM   3235  O    ASP B 364      40.153   8.782  44.393  1.00 28.39
ATOM   3236  N    LEU B 365      38.812   9.659  45.946  1.00 26.17
ATOM   3237  CA   LEU B 365      39.797   9.551  47.005  1.00 25.30
ATOM   3238  CB   LEU B 365      39.322  10.330  48.233  1.00 23.24
ATOM   3239  CG   LEU B 365      40.329  10.553  49.368  1.00 23.91
ATOM   3240  CD1  LEU B 365      41.504  11.457  48.944  1.00 21.13
ATOM   3241  CD2  LEU B 365      39.573  11.137  50.556  1.00 22.46
ATOM   3242  C    LEU B 365      40.183   8.116  47.374  1.00 25.99
ATOM   3243  O    LEU B 365      39.353   7.310  47.796  1.00 27.30
ATOM   3244  N    ARG B 366      41.456   7.805  47.150  1.00 26.23
ATOM   3245  CA   ARG B 366      42.048   6.507  47.454  1.00 26.01
ATOM   3246  CB   ARG B 366      41.569   5.419  46.498  1.00 26.35
ATOM   3247  CG   ARG B 366      41.734   5.679  45.034  1.00 27.50
ATOM   3248  CD   ARG B 366      41.403   4.406  44.279  1.00 29.86
ATOM   3249  NE   ARG B 366      41.166   4.662  42.864  1.00 34.05
ATOM   3250  CZ   ARG B 366      40.035   5.170  42.372  1.00 34.97
ATOM   3251  NH1  ARG B 366      39.019   5.470  43.180  1.00 36.96
ATOM   3252  NH2  ARG B 366      39.942   5.442  41.078  1.00 34.00
ATOM   3253  C    ARG B 366      43.562   6.665  47.387  1.00 25.96
ATOM   3254  O    ARG B 366      44.056   7.603  46.769  1.00 25.16
ATOM   3255  N    ALA B 367      44.298   5.765  48.033  1.00 26.45
ATOM   3256  CA   ALA B 367      45.764   5.842  48.061  1.00 26.07
ATOM   3257  CB   ALA B 367      46.339   4.655  48.794  1.00 25.88
ATOM   3258  C    ALA B 367      46.424   6.001  46.689  1.00 26.40
ATOM   3259  O    ALA B 367      47.408   6.724  46.566  1.00 27.15
ATOM   3260  N    ALA B 368      45.839   5.402  45.649  1.00 26.47
ATOM   3261  CA   ALA B 368      46.386   5.493  44.286  1.00 25.82
ATOM   3262  CB   ALA B 368      45.600   4.618  43.337  1.00 25.15
ATOM   3263  C    ALA B 368      46.406   6.920  43.761  1.00 25.89
ATOM   3264  O    ALA B 368      47.230   7.259  42.917  1.00 25.41
ATOM   3265  N    ASN B 369      45.511   7.754  44.285  1.00 26.34
ATOM   3266  CA   ASN B 369      45.408   9.153  43.868  1.00 26.83
ATOM   3267  CB   ASN B 369      43.942   9.539  43.620  1.00 27.17
ATOM   3268  CG   ASN B 369      43.304   8.681  42.535  1.00 28.07
ATOM   3269  OD1  ASN B 369      43.906   8.451  41.483  1.00 28.53
ATOM   3270  ND2  ASN B 369      42.134   8.139  42.812  1.00 25.55
ATOM   3271  C    ASN B 369      46.102  10.150  44.785  1.00 26.36
ATOM   3272  O    ASN B 369      45.811  11.338  44.747  1.00 27.21
ATOM   3273  N    ILE B 370      46.995   9.653  45.635  1.00 25.68
ATOM   3274  CA   ILE B 370      47.783  10.512  46.513  1.00 24.88
ATOM   3275  CB   ILE B 370      47.710  10.065  47.984  1.00 24.39
ATOM   3276  CG2  ILE B 370      48.592  10.966  48.840  1.00 22.63
ATOM   3277  CG1  ILE B 370      46.252  10.065  48.475  1.00 22.80
ATOM   3278  CD1  ILE B 370      45.604  11.420  48.490  1.00 20.70
ATOM   3279  C    ILE B 370      49.233  10.381  46.013  1.00 25.26
ATOM   3280  O    ILE B 370      49.679   9.276  45.676  1.00 24.23
ATOM   3281  N    LEU B 371      49.947  11.503  45.913  1.00 25.28
ATOM   3282  CA   LEU B 371      51.329  11.472  45.425  1.00 25.00
ATOM   3283  CB   LEU B 371      51.517  12.435  44.246  1.00 23.13
ATOM   3284  CG   LEU B 371      50.632  12.201  43.019  1.00 21.42
ATOM   3285  CD1  LEU B 371      50.864  13.300  42.018  1.00 20.36
ATOM   3286  CD2  LEU B 371      50.898  10.840  42.409  1.00 19.56
ATOM   3287  C    LEU B 371      52.286  11.799  46.556  1.00 25.89
```

Figure 8

| | | | | | | | | | |
|---|---|---|---|---|---|---|---|---|---|
| ATOM | 3288 | O   | LEU | B | 371 | 51.948 | 12.590 | 47.437 | 1.00 26.21 |
| ATOM | 3289 | N   | VAL | B | 372 | 53.451 | 11.150 | 46.555 | 1.00 26.46 |
| ATOM | 3290 | CA  | VAL | B | 372 | 54.476 | 11.333 | 47.588 | 1.00 28.18 |
| ATOM | 3291 | CB  | VAL | B | 372 | 54.923 | 9.953  | 48.153 | 1.00 27.75 |
| ATOM | 3292 | CG1 | VAL | B | 372 | 55.811 | 10.117 | 49.366 | 1.00 26.76 |
| ATOM | 3293 | CG2 | VAL | B | 372 | 53.719 | 9.109  | 48.481 | 1.00 26.88 |
| ATOM | 3294 | C   | VAL | B | 372 | 55.713 | 12.082 | 47.041 | 1.00 29.94 |
| ATOM | 3295 | O   | VAL | B | 372 | 56.262 | 11.722 | 46.000 | 1.00 30.51 |
| ATOM | 3296 | N   | SER | B | 373 | 56.142 | 13.133 | 47.731 | 1.00 31.15 |
| ATOM | 3297 | CA  | SER | B | 373 | 57.301 | 13.894 | 47.289 | 1.00 32.68 |
| ATOM | 3298 | CB  | SER | B | 373 | 57.261 | 15.298 | 47.885 | 1.00 32.47 |
| ATOM | 3299 | OG  | SER | B | 373 | 57.546 | 15.268 | 49.275 | 1.00 32.87 |
| ATOM | 3300 | C   | SER | B | 373 | 58.569 | 13.199 | 47.752 | 1.00 34.38 |
| ATOM | 3301 | O   | SER | B | 373 | 58.506 | 12.201 | 48.462 | 1.00 33.96 |
| ATOM | 3302 | N   | ASP | B | 374 | 59.717 | 13.736 | 47.355 | 1.00 36.40 |
| ATOM | 3303 | CA  | ASP | B | 374 | 61.001 | 13.177 | 47.767 | 1.00 38.47 |
| ATOM | 3304 | CB  | ASP | B | 374 | 62.153 | 13.846 | 47.015 | 1.00 39.95 |
| ATOM | 3305 | CG  | ASP | B | 374 | 61.986 | 15.346 | 46.909 | 1.00 41.84 |
| ATOM | 3306 | OD1 | ASP | B | 374 | 61.382 | 15.809 | 45.908 | 1.00 44.83 |
| ATOM | 3307 | OD2 | ASP | B | 374 | 62.444 | 16.056 | 47.828 | 1.00 41.86 |
| ATOM | 3308 | C   | ASP | B | 374 | 61.202 | 13.313 | 49.277 | 1.00 38.86 |
| ATOM | 3309 | O   | ASP | B | 374 | 61.901 | 12.503 | 49.878 | 1.00 39.44 |
| ATOM | 3310 | N   | THR | B | 375 | 60.569 | 14.322 | 49.882 | 1.00 39.13 |
| ATOM | 3311 | CA  | THR | B | 375 | 60.658 | 14.551 | 51.330 | 1.00 38.96 |
| ATOM | 3312 | CB  | THR | B | 375 | 60.473 | 16.037 | 51.697 | 1.00 39.23 |
| ATOM | 3313 | OG1 | THR | B | 375 | 59.208 | 16.501 | 51.207 | 1.00 39.55 |
| ATOM | 3314 | CG2 | THR | B | 375 | 61.602 | 16.882 | 51.101 | 1.00 40.18 |
| ATOM | 3315 | C   | THR | B | 375 | 59.597 | 13.745 | 52.074 | 1.00 38.85 |
| ATOM | 3316 | O   | THR | B | 375 | 59.379 | 13.942 | 53.268 | 1.00 39.19 |
| ATOM | 3317 | N   | LEU | B | 376 | 58.931 | 12.857 | 51.343 | 1.00 38.41 |
| ATOM | 3318 | CA  | LEU | B | 376 | 57.879 | 11.982 | 51.860 | 1.00 37.68 |
| ATOM | 3319 | CB  | LEU | B | 376 | 58.425 | 11.045 | 52.937 | 1.00 37.38 |
| ATOM | 3320 | CG  | LEU | B | 376 | 59.704 | 10.260 | 52.626 | 1.00 38.43 |
| ATOM | 3321 | CD1 | LEU | B | 376 | 59.684 | 8.996  | 53.459 | 1.00 38.13 |
| ATOM | 3322 | CD2 | LEU | B | 376 | 59.813 | 9.898  | 51.162 | 1.00 38.72 |
| ATOM | 3323 | C   | LEU | B | 376 | 56.575 | 12.646 | 52.331 | 1.00 37.41 |
| ATOM | 3324 | O   | LEU | B | 376 | 55.856 | 12.085 | 53.162 | 1.00 37.45 |
| ATOM | 3325 | N   | SER | B | 377 | 56.268 | 13.833 | 51.805 | 1.00 36.24 |
| ATOM | 3326 | CA  | SER | B | 377 | 55.020 | 14.509 | 52.153 | 1.00 35.28 |
| ATOM | 3327 | CB  | SER | B | 377 | 55.222 | 16.021 | 52.261 | 1.00 36.10 |
| ATOM | 3328 | OG  | SER | B | 377 | 55.458 | 16.592 | 50.983 | 1.00 38.53 |
| ATOM | 3329 | C   | SER | B | 377 | 53.965 | 14.184 | 51.071 | 1.00 34.33 |
| ATOM | 3330 | O   | SER | B | 377 | 54.304 | 13.997 | 49.887 | 1.00 32.91 |
| ATOM | 3331 | N   | CYS | B | 378 | 52.692 | 14.137 | 51.474 | 1.00 33.03 |
| ATOM | 3332 | CA  | CYS | B | 378 | 51.611 | 13.810 | 50.548 | 1.00 30.69 |
| ATOM | 3333 | CB  | CYS | B | 378 | 50.653 | 12.816 | 51.201 | 1.00 29.83 |
| ATOM | 3334 | SG  | CYS | B | 378 | 51.442 | 11.324 | 51.828 | 1.00 27.59 |
| ATOM | 3335 | C   | CYS | B | 378 | 50.822 | 15.001 | 49.986 | 1.00 30.32 |
| ATOM | 3336 | O   | CYS | B | 378 | 50.603 | 16.012 | 50.671 | 1.00 30.88 |
| ATOM | 3337 | N   | LYS | B | 379 | 50.428 | 14.859 | 48.717 | 1.00 28.67 |
| ATOM | 3338 | CA  | LYS | B | 379 | 49.646 | 15.844 | 47.970 | 1.00 26.94 |
| ATOM | 3339 | CB  | LYS | B | 379 | 50.523 | 16.588 | 46.950 | 1.00 25.70 |
| ATOM | 3340 | CG  | LYS | B | 379 | 51.207 | 17.843 | 47.500 | 1.00 27.54 |
| ATOM | 3341 | CD  | LYS | B | 379 | 52.469 | 18.216 | 46.720 | 1.00 29.36 |
| ATOM | 3342 | CE  | LYS | B | 379 | 53.174 | 19.469 | 47.278 | 1.00 29.80 |
| ATOM | 3343 | NZ  | LYS | B | 379 | 52.496 | 20.754 | 46.849 | 1.00 33.69 |
| ATOM | 3344 | C   | LYS | B | 379 | 48.521 | 15.063 | 47.272 | 1.00 26.70 |
| ATOM | 3345 | O   | LYS | B | 379 | 48.725 | 13.927 | 46.808 | 1.00 26.67 |
| ATOM | 3346 | N   | ILE | B | 380 | 47.326 | 15.650 | 47.245 | 1.00 26.01 |
| ATOM | 3347 | CA  | ILE | B | 380 | 46.144 | 15.016 | 46.643 | 1.00 25.37 |

Figure 8

| | | | | | | | | | |
|---|---|---|---|---|---|---|---|---|---|
| ATOM | 3348 | CB | ILE | B | 380 | 44.826 | 15.519 | 47.334 | 1.00 25.11 |
| ATOM | 3349 | CG2 | ILE | B | 380 | 43.602 | 14.887 | 46.701 | 1.00 23.88 |
| ATOM | 3350 | CG1 | ILE | B | 380 | 44.847 | 15.195 | 48.824 | 1.00 24.52 |
| ATOM | 3351 | CD1 | ILE | B | 380 | 43.691 | 15.748 | 49.537 | 1.00 23.76 |
| ATOM | 3352 | C | ILE | B | 380 | 46.071 | 15.329 | 45.148 | 1.00 24.61 |
| ATOM | 3353 | O | ILE | B | 380 | 46.211 | 16.488 | 44.747 | 1.00 24.46 |
| ATOM | 3354 | N | ALA | B | 381 | 45.853 | 14.302 | 44.331 | 1.00 23.77 |
| ATOM | 3355 | CA | ALA | B | 381 | 45.753 | 14.494 | 42.890 | 1.00 22.98 |
| ATOM | 3356 | CB | ALA | B | 381 | 46.836 | 13.721 | 42.175 | 1.00 21.65 |
| ATOM | 3357 | C | ALA | B | 381 | 44.396 | 14.032 | 42.410 | 1.00 23.84 |
| ATOM | 3358 | O | ALA | B | 381 | 43.659 | 13.379 | 43.146 | 1.00 22.57 |
| ATOM | 3359 | N | ASP | B | 382 | 44.085 | 14.367 | 41.159 | 1.00 25.69 |
| ATOM | 3360 | CA | ASP | B | 382 | 42.830 | 13.988 | 40.502 | 1.00 26.94 |
| ATOM | 3361 | CB | ASP | B | 382 | 42.931 | 12.559 | 39.979 | 1.00 27.03 |
| ATOM | 3362 | CG | ASP | B | 382 | 43.809 | 12.470 | 38.769 | 1.00 27.83 |
| ATOM | 3363 | OD1 | ASP | B | 382 | 43.471 | 13.120 | 37.762 | 1.00 31.05 |
| ATOM | 3364 | OD2 | ASP | B | 382 | 44.849 | 11.793 | 38.818 | 1.00 28.84 |
| ATOM | 3365 | C | ASP | B | 382 | 41.535 | 14.200 | 41.280 | 1.00 27.76 |
| ATOM | 3366 | O | ASP | B | 382 | 40.603 | 13.399 | 41.201 | 1.00 27.29 |
| ATOM | 3367 | N | PHE | B | 383 | 41.450 | 15.370 | 41.908 | 1.00 28.80 |
| ATOM | 3368 | CA | PHE | B | 383 | 40.310 | 15.761 | 42.720 | 1.00 29.73 |
| ATOM | 3369 | CB | PHE | B | 383 | 40.805 | 16.540 | 43.944 | 1.00 28.35 |
| ATOM | 3370 | CG | PHE | B | 383 | 41.695 | 17.709 | 43.602 | 1.00 28.60 |
| ATOM | 3371 | CD1 | PHE | B | 383 | 41.159 | 18.934 | 43.213 | 1.00 29.39 |
| ATOM | 3372 | CD2 | PHE | B | 383 | 43.077 | 17.579 | 43.652 | 1.00 28.34 |
| ATOM | 3373 | CE1 | PHE | B | 383 | 41.999 | 20.007 | 42.876 | 1.00 29.04 |
| ATOM | 3374 | CE2 | PHE | B | 383 | 43.925 | 18.645 | 43.319 | 1.00 27.59 |
| ATOM | 3375 | CZ | PHE | B | 383 | 43.385 | 19.856 | 42.933 | 1.00 28.08 |
| ATOM | 3376 | C | PHE | B | 383 | 39.280 | 16.610 | 41.970 | 1.00 30.92 |
| ATOM | 3377 | O | PHE | B | 383 | 39.605 | 17.308 | 41.004 | 1.00 31.35 |
| ATOM | 3378 | N | GLY | B | 384 | 38.035 | 16.546 | 42.429 | 1.00 31.40 |
| ATOM | 3379 | CA | GLY | B | 384 | 36.991 | 17.345 | 41.827 | 1.00 32.32 |
| ATOM | 3380 | C | GLY | B | 384 | 36.510 | 16.962 | 40.448 | 1.00 33.21 |
| ATOM | 3381 | O | GLY | B | 384 | 35.829 | 17.758 | 39.830 | 1.00 33.93 |
| ATOM | 3382 | N | LEU | B | 385 | 36.877 | 15.791 | 39.935 | 1.00 34.83 |
| ATOM | 3383 | CA | LEU | B | 385 | 36.402 | 15.372 | 38.611 | 1.00 35.97 |
| ATOM | 3384 | CB | LEU | B | 385 | 37.152 | 14.130 | 38.121 | 1.00 35.28 |
| ATOM | 3385 | CG | LEU | B | 385 | 38.663 | 14.288 | 37.940 | 1.00 35.84 |
| ATOM | 3386 | CD1 | LEU | B | 385 | 39.220 | 13.048 | 37.293 | 1.00 36.00 |
| ATOM | 3387 | CD2 | LEU | B | 385 | 38.982 | 15.502 | 37.102 | 1.00 36.19 |
| ATOM | 3388 | C | LEU | B | 385 | 34.900 | 15.079 | 38.641 | 1.00 37.46 |
| ATOM | 3389 | O | LEU | B | 385 | 34.348 | 14.711 | 39.673 | 1.00 36.71 |
| ATOM | 3390 | N | ALA | B | 386 | 34.238 | 15.272 | 37.504 | 1.00 39.30 |
| ATOM | 3391 | CA | ALA | B | 386 | 32.799 | 15.027 | 37.397 | 1.00 39.96 |
| ATOM | 3392 | CB | ALA | B | 386 | 32.238 | 15.719 | 36.149 | 1.00 40.37 |
| ATOM | 3393 | C | ALA | B | 386 | 32.537 | 13.526 | 37.323 | 1.00 40.10 |
| ATOM | 3394 | O | ALA | B | 386 | 31.504 | 13.033 | 37.780 | 1.00 41.29 |
| ATOM | 3395 | N | ARG | B | 387 | 33.504 | 12.805 | 36.761 | 1.00 39.04 |
| ATOM | 3396 | CA | ARG | B | 387 | 33.409 | 11.364 | 36.590 | 1.00 36.60 |
| ATOM | 3397 | CB | ARG | B | 387 | 33.854 | 11.013 | 35.176 | 1.00 35.66 |
| ATOM | 3398 | CG | ARG | B | 387 | 35.306 | 11.383 | 34.907 | 1.00 34.58 |
| ATOM | 3399 | CD | ARG | B | 387 | 35.686 | 11.046 | 33.504 | 1.00 34.00 |
| ATOM | 3400 | NE | ARG | B | 387 | 37.117 | 11.148 | 33.285 | 1.00 33.69 |
| ATOM | 3401 | CZ | ARG | B | 387 | 37.939 | 10.107 | 33.317 | 1.00 34.83 |
| ATOM | 3402 | NH1 | ARG | B | 387 | 37.465 | 8.886 | 33.557 | 1.00 34.58 |
| ATOM | 3403 | NH2 | ARG | B | 387 | 39.241 | 10.288 | 33.139 | 1.00 35.04 |
| ATOM | 3404 | C | ARG | B | 387 | 34.240 | 10.545 | 37.584 | 1.00 35.20 |
| ATOM | 3405 | O | ARG | B | 387 | 35.080 | 11.067 | 38.315 | 1.00 34.43 |
| ATOM | 3406 | N | LEU | B | 388 | 34.011 | 9.237 | 37.541 | 1.00 33.69 |
| ATOM | 3407 | CA | LEU | B | 388 | 34.714 | 8.271 | 38.354 | 1.00 31.96 |

Figure 8

| | | | | | | | | |
|---|---|---|---|---|---|---|---|---|
| ATOM | 3408 | CB | LEU | B | 388 | 33.747 | 7.178 | 38.787 | 1.00 31.42 |
| ATOM | 3409 | CG | LEU | B | 388 | 32.521 | 7.791 | 39.484 | 1.00 33.80 |
| ATOM | 3410 | CD1 | LEU | B | 388 | 31.520 | 6.716 | 39.889 | 1.00 34.04 |
| ATOM | 3411 | CD2 | LEU | B | 388 | 32.941 | 8.596 | 40.708 | 1.00 34.37 |
| ATOM | 3412 | C | LEU | B | 388 | 35.832 | 7.725 | 37.459 | 1.00 30.91 |
| ATOM | 3413 | O | LEU | B | 388 | 35.589 | 7.342 | 36.309 | 1.00 30.61 |
| ATOM | 3414 | N | ILE | B | 389 | 37.069 | 7.780 | 37.953 | 1.00 29.95 |
| ATOM | 3415 | CA | ILE | B | 389 | 38.224 | 7.326 | 37.179 | 1.00 29.27 |
| ATOM | 3416 | CB | ILE | B | 389 | 39.366 | 8.380 | 37.192 | 1.00 26.88 |
| ATOM | 3417 | CG2 | ILE | B | 389 | 38.825 | 9.748 | 36.828 | 1.00 25.49 |
| ATOM | 3418 | CG1 | ILE | B | 389 | 40.045 | 8.426 | 38.569 | 1.00 26.31 |
| ATOM | 3419 | CD1 | ILE | B | 389 | 41.051 | 9.545 | 38.747 | 1.00 23.98 |
| ATOM | 3420 | C | ILE | B | 389 | 38.793 | 5.966 | 37.579 | 1.00 30.91 |
| ATOM | 3421 | O | ILE | B | 389 | 38.604 | 5.488 | 38.693 | 1.00 31.52 |
| ATOM | 3422 | N | GLU | B | 390 | 39.507 | 5.349 | 36.651 | 1.00 33.14 |
| ATOM | 3423 | CA | GLU | B | 390 | 40.129 | 4.061 | 36.899 | 1.00 35.16 |
| ATOM | 3424 | CB | GLU | B | 390 | 39.643 | 3.028 | 35.886 | 1.00 36.75 |
| ATOM | 3425 | CG | GLU | B | 390 | 38.206 | 2.635 | 36.089 | 1.00 39.23 |
| ATOM | 3426 | CD | GLU | B | 390 | 37.696 | 1.705 | 35.023 | 1.00 42.07 |
| ATOM | 3427 | OE1 | GLU | B | 390 | 36.466 | 1.557 | 34.918 | 1.00 44.84 |
| ATOM | 3428 | OE2 | GLU | B | 390 | 38.507 | 1.125 | 34.279 | 1.00 43.78 |
| ATOM | 3429 | C | GLU | B | 390 | 41.640 | 4.192 | 36.833 | 1.00 35.86 |
| ATOM | 3430 | O | GLU | B | 390 | 42.169 | 5.078 | 36.168 | 1.00 34.38 |
| ATOM | 3431 | N | ASP | B | 391 | 42.325 | 3.293 | 37.534 | 1.00 38.40 |
| ATOM | 3432 | CA | ASP | B | 391 | 43.789 | 3.281 | 37.597 | 1.00 40.09 |
| ATOM | 3433 | CB | ASP | B | 391 | 44.243 | 2.384 | 38.759 | 1.00 41.93 |
| ATOM | 3434 | CG | ASP | B | 391 | 43.788 | 2.907 | 40.113 | 1.00 44.26 |
| ATOM | 3435 | OD1 | ASP | B | 391 | 43.463 | 4.119 | 40.227 | 1.00 46.06 |
| ATOM | 3436 | OD2 | ASP | B | 391 | 43.762 | 2.103 | 41.069 | 1.00 46.05 |
| ATOM | 3437 | C | ASP | B | 391 | 44.526 | 2.893 | 36.305 | 1.00 39.70 |
| ATOM | 3438 | O | ASP | B | 391 | 45.716 | 3.186 | 36.150 | 1.00 40.11 |
| ATOM | 3439 | N | ASN | B | 392 | 43.809 | 2.264 | 35.381 | 1.00 38.98 |
| ATOM | 3440 | CA | ASN | B | 392 | 44.374 | 1.815 | 34.109 | 1.00 38.24 |
| ATOM | 3441 | CB | ASN | B | 392 | 43.738 | 0.468 | 33.699 | 1.00 39.14 |
| ATOM | 3442 | CG | ASN | B | 392 | 42.255 | 0.594 | 33.249 | 1.00 40.35 |
| ATOM | 3443 | OD1 | ASN | B | 392 | 41.628 | 1.660 | 33.357 | 1.00 40.19 |
| ATOM | 3444 | ND2 | ASN | B | 392 | 41.707 | -0.503 | 32.729 | 1.00 39.69 |
| ATOM | 3445 | C | ASN | B | 392 | 44.223 | 2.838 | 32.976 | 1.00 37.34 |
| ATOM | 3446 | O | ASN | B | 392 | 44.356 | 2.496 | 31.797 | 1.00 37.61 |
| ATOM | 3447 | N | GLU | B | 393 | 43.954 | 4.090 | 33.331 | 1.00 35.98 |
| ATOM | 3448 | CA | GLU | B | 393 | 43.764 | 5.122 | 32.325 | 1.00 34.86 |
| ATOM | 3449 | CB | GLU | B | 393 | 42.793 | 6.176 | 32.844 | 1.00 33.73 |
| ATOM | 3450 | CG | GLU | B | 393 | 41.392 | 5.625 | 33.110 | 1.00 31.82 |
| ATOM | 3451 | CD | GLU | B | 393 | 40.428 | 6.686 | 33.592 | 1.00 30.67 |
| ATOM | 3452 | OE1 | GLU | B | 393 | 40.874 | 7.826 | 33.856 | 1.00 30.33 |
| ATOM | 3453 | OE2 | GLU | B | 393 | 39.219 | 6.386 | 33.700 | 1.00 31.63 |
| ATOM | 3454 | C | GLU | B | 393 | 45.050 | 5.761 | 31.822 | 1.00 34.95 |
| ATOM | 3455 | O | GLU | B | 393 | 45.189 | 6.044 | 30.636 | 1.00 34.24 |
| ATOM | 3456 | N | TYR | B | 394 | 46.002 | 5.966 | 32.721 | 1.00 35.38 |
| ATOM | 3457 | CA | TYR | B | 394 | 47.267 | 6.563 | 32.337 | 1.00 35.93 |
| ATOM | 3458 | CB | TYR | B | 394 | 47.364 | 7.997 | 32.856 | 1.00 34.01 |
| ATOM | 3459 | CG | TYR | B | 394 | 46.281 | 8.894 | 32.313 | 1.00 31.60 |
| ATOM | 3460 | CD1 | TYR | B | 394 | 45.061 | 9.003 | 32.954 | 1.00 31.15 |
| ATOM | 3461 | CE1 | TYR | B | 394 | 44.048 | 9.801 | 32.437 | 1.00 31.37 |
| ATOM | 3462 | CD2 | TYR | B | 394 | 46.468 | 9.609 | 31.140 | 1.00 31.68 |
| ATOM | 3463 | CE2 | TYR | B | 394 | 45.464 | 10.414 | 30.610 | 1.00 31.23 |
| ATOM | 3464 | CZ | TYR | B | 394 | 44.253 | 10.507 | 31.264 | 1.00 31.41 |
| ATOM | 3465 | OH | TYR | B | 394 | 43.252 | 11.307 | 30.754 | 1.00 29.87 |
| ATOM | 3466 | C | TYR | B | 394 | 48.466 | 5.729 | 32.780 | 1.00 38.03 |
| ATOM | 3467 | O | TYR | B | 394 | 49.586 | 6.214 | 32.725 | 1.00 38.81 |

Figure 8

| | | | | | | | | | |
|---|---|---|---|---|---|---|---|---|---|
| ATOM | 3468 | N | THR | B | 395 | 48.216 | 4.516 | 33.287 | 1.00 40.43 |
| ATOM | 3469 | CA | THR | B | 395 | 49.272 | 3.575 | 33.695 | 1.00 44.23 |
| ATOM | 3470 | CB | THR | B | 395 | 49.720 | 3.663 | 35.201 | 1.00 44.10 |
| ATOM | 3471 | OG1 | THR | B | 395 | 48.621 | 4.030 | 36.048 | 1.00 46.39 |
| ATOM | 3472 | CG2 | THR | B | 395 | 50.888 | 4.606 | 35.369 | 1.00 43.39 |
| ATOM | 3473 | C | THR | B | 395 | 48.828 | 2.149 | 33.414 | 1.00 47.00 |
| ATOM | 3474 | O | THR | B | 395 | 47.886 | 1.924 | 32.650 | 1.00 47.62 |
| ATOM | 3475 | N | ALA | B | 396 | 49.476 | 1.184 | 34.055 | 1.00 50.97 |
| ATOM | 3476 | CA | ALA | B | 396 | 49.125 | -0.209 | 33.823 | 1.00 55.16 |
| ATOM | 3477 | CB | ALA | B | 396 | 50.217 | -0.888 | 32.983 | 1.00 55.24 |
| ATOM | 3478 | C | ALA | B | 396 | 48.752 | -1.079 | 35.038 | 1.00 57.93 |
| ATOM | 3479 | O | ALA | B | 396 | 49.012 | -2.291 | 35.027 | 1.00 59.53 |
| ATOM | 3480 | N | ARG | B | 397 | 48.123 | -0.492 | 36.061 | 1.00 59.62 |
| ATOM | 3481 | CA | ARG | B | 397 | 47.694 | -1.274 | 37.228 | 1.00 60.73 |
| ATOM | 3482 | CB | ARG | B | 397 | 47.286 | -0.375 | 38.402 | 1.00 61.14 |
| ATOM | 3483 | CG | ARG | B | 397 | 48.428 | 0.399 | 39.052 | 1.00 62.46 |
| ATOM | 3484 | CD | ARG | B | 397 | 48.389 | 0.307 | 40.593 | 1.00 62.18 |
| ATOM | 3485 | NE | ARG | B | 397 | 49.075 | 1.427 | 41.245 | 1.00 61.68 |
| ATOM | 3486 | CZ | ARG | B | 397 | 48.650 | 2.690 | 41.189 | 1.00 61.30 |
| ATOM | 3487 | NH1 | ARG | B | 397 | 47.542 | 2.987 | 40.516 | 1.00 61.16 |
| ATOM | 3488 | NH2 | ARG | B | 397 | 49.333 | 3.659 | 41.790 | 1.00 59.70 |
| ATOM | 3489 | C | ARG | B | 397 | 46.497 | -2.148 | 36.830 | 1.00 61.52 |
| ATOM | 3490 | O | ARG | B | 397 | 46.683 | -3.383 | 36.697 | 1.00 62.34 |
| ATOM | 3491 | CB | PRO | B | 403 | 37.090 | 2.172 | 41.188 | 1.00 31.33 |
| ATOM | 3492 | CG | PRO | B | 403 | 37.530 | 1.645 | 39.820 | 1.00 32.39 |
| ATOM | 3493 | C | PRO | B | 403 | 35.885 | 1.001 | 43.066 | 1.00 33.69 |
| ATOM | 3494 | O | PRO | B | 403 | 35.794 | 1.993 | 43.833 | 1.00 35.10 |
| ATOM | 3495 | N | PRO | B | 403 | 36.704 | -0.227 | 41.005 | 1.00 32.25 |
| ATOM | 3496 | CD | PRO | B | 403 | 36.911 | 0.234 | 39.627 | 1.00 31.85 |
| ATOM | 3497 | CA | PRO | B | 403 | 36.982 | 0.886 | 41.989 | 1.00 32.80 |
| ATOM | 3498 | N | ILE | B | 404 | 35.078 | -0.052 | 43.141 | 1.00 32.80 |
| ATOM | 3499 | CA | ILE | B | 404 | 33.960 | -0.137 | 44.076 | 1.00 31.62 |
| ATOM | 3500 | CB | ILE | B | 404 | 33.070 | -1.362 | 43.722 | 1.00 31.37 |
| ATOM | 3501 | CG2 | ILE | B | 404 | 32.225 | -1.794 | 44.910 | 1.00 31.36 |
| ATOM | 3502 | CG1 | ILE | B | 404 | 32.153 | -0.995 | 42.566 | 1.00 32.90 |
| ATOM | 3503 | CD1 | ILE | B | 404 | 31.186 | 0.148 | 42.929 | 1.00 33.47 |
| ATOM | 3504 | C | ILE | B | 404 | 34.295 | -0.139 | 45.570 | 1.00 30.24 |
| ATOM | 3505 | O | ILE | B | 404 | 33.495 | 0.335 | 46.375 | 1.00 29.77 |
| ATOM | 3506 | N | LYS | B | 405 | 35.479 | -0.631 | 45.924 | 1.00 28.61 |
| ATOM | 3507 | CA | LYS | B | 405 | 35.899 | -0.744 | 47.323 | 1.00 27.41 |
| ATOM | 3508 | CB | LYS | B | 405 | 37.137 | -1.640 | 47.431 | 1.00 28.12 |
| ATOM | 3509 | CG | LYS | B | 405 | 36.850 | -3.066 | 47.004 | 1.00 28.68 |
| ATOM | 3510 | CD | LYS | B | 405 | 38.051 | -3.965 | 47.155 | 1.00 29.71 |
| ATOM | 3511 | CE | LYS | B | 405 | 37.707 | -5.405 | 46.792 | 1.00 30.63 |
| ATOM | 3512 | NZ | LYS | B | 405 | 38.717 | -6.369 | 47.330 | 1.00 32.42 |
| ATOM | 3513 | C | LYS | B | 405 | 36.068 | 0.533 | 48.149 | 1.00 25.83 |
| ATOM | 3514 | O | LYS | B | 405 | 36.232 | 0.465 | 49.372 | 1.00 25.21 |
| ATOM | 3515 | N | TRP | B | 406 | 35.967 | 1.683 | 47.488 | 1.00 24.27 |
| ATOM | 3516 | CA | TRP | B | 406 | 36.081 | 2.974 | 48.151 | 1.00 23.17 |
| ATOM | 3517 | CB | TRP | B | 406 | 37.186 | 3.811 | 47.501 | 1.00 23.13 |
| ATOM | 3518 | CG | TRP | B | 406 | 38.595 | 3.270 | 47.695 | 1.00 21.87 |
| ATOM | 3519 | CD2 | TRP | B | 406 | 39.232 | 2.248 | 46.922 | 1.00 20.55 |
| ATOM | 3520 | CE2 | TRP | B | 406 | 40.536 | 2.080 | 47.444 | 1.00 20.09 |
| ATOM | 3521 | CE3 | TRP | B | 406 | 38.827 | 1.455 | 45.837 | 1.00 19.72 |
| ATOM | 3522 | CD1 | TRP | B | 406 | 39.515 | 3.673 | 48.637 | 1.00 20.07 |
| ATOM | 3523 | NE1 | TRP | B | 406 | 40.676 | 2.959 | 48.490 | 1.00 19.88 |
| ATOM | 3524 | CZ2 | TRP | B | 406 | 41.441 | 1.150 | 46.911 | 1.00 19.06 |
| ATOM | 3525 | CZ3 | TRP | B | 406 | 39.726 | 0.536 | 45.314 | 1.00 19.49 |
| ATOM | 3526 | CH2 | TRP | B | 406 | 41.020 | 0.392 | 45.856 | 1.00 18.68 |
| ATOM | 3527 | C | TRP | B | 406 | 34.782 | 3.768 | 48.099 | 1.00 23.58 |

Figure 8

```
ATOM   3528  O    TRP B 406      34.714   4.878  48.611  1.00 23.90
ATOM   3529  N    THR B 407      33.757   3.208  47.467  1.00 24.34
ATOM   3530  CA   THR B 407      32.474   3.893  47.329  1.00 24.20
ATOM   3531  CB   THR B 407      31.750   3.445  46.031  1.00 24.84
ATOM   3532  OG1  THR B 407      32.670   3.457  44.937  1.00 25.59
ATOM   3533  CG2  THR B 407      30.619   4.394  45.694  1.00 24.88
ATOM   3534  C    THR B 407      31.543   3.667  48.533  1.00 24.03
ATOM   3535  O    THR B 407      31.319   2.520  48.932  1.00 23.41
ATOM   3536  N    ALA B 408      31.009   4.762  49.096  1.00 23.23
ATOM   3537  CA   ALA B 408      30.085   4.710  50.237  1.00 22.45
ATOM   3538  CB   ALA B 408      29.797   6.108  50.744  1.00 22.81
ATOM   3539  C    ALA B 408      28.797   4.032  49.787  1.00 22.54
ATOM   3540  O    ALA B 408      28.498   4.000  48.603  1.00 23.54
ATOM   3541  N    PRO B 409      28.005   3.495  50.726  1.00 23.03
ATOM   3542  CD   PRO B 409      28.223   3.358  52.174  1.00 21.74
ATOM   3543  CA   PRO B 409      26.758   2.823  50.322  1.00 23.27
ATOM   3544  CB   PRO B 409      26.189   2.337  51.656  1.00 22.91
ATOM   3545  CG   PRO B 409      27.434   2.114  52.481  1.00 21.98
ATOM   3546  C    PRO B 409      25.748   3.658  49.529  1.00 23.47
ATOM   3547  O    PRO B 409      25.149   3.161  48.580  1.00 22.86
ATOM   3548  N    GLU B 410      25.586   4.924  49.902  1.00 24.02
ATOM   3549  CA   GLU B 410      24.639   5.809  49.227  1.00 25.28
ATOM   3550  CB   GLU B 410      24.409   7.089  50.049  1.00 24.35
ATOM   3551  CG   GLU B 410      25.587   8.079  50.087  1.00 25.31
ATOM   3552  CD   GLU B 410      26.643   7.757  51.140  1.00 25.85
ATOM   3553  OE1  GLU B 410      26.548   6.717  51.827  1.00 26.70
ATOM   3554  OE2  GLU B 410      27.568   8.571  51.297  1.00 25.05
ATOM   3555  C    GLU B 410      25.053   6.154  47.786  1.00 26.55
ATOM   3556  O    GLU B 410      24.198   6.423  46.925  1.00 27.18
ATOM   3557  N    ALA B 411      26.362   6.160  47.535  1.00 27.33
ATOM   3558  CA   ALA B 411      26.907   6.458  46.210  1.00 27.30
ATOM   3559  CB   ALA B 411      28.373   6.792  46.323  1.00 26.18
ATOM   3560  C    ALA B 411      26.701   5.256  45.288  1.00 28.52
ATOM   3561  O    ALA B 411      26.535   5.403  44.076  1.00 28.90
ATOM   3562  N    ILE B 412      26.716   4.062  45.876  1.00 30.07
ATOM   3563  CA   ILE B 412      26.512   2.827  45.132  1.00 31.09
ATOM   3564  CB   ILE B 412      26.988   1.594  45.922  1.00 30.17
ATOM   3565  CG2  ILE B 412      26.708   0.319  45.123  1.00 30.16
ATOM   3566  CG1  ILE B 412      28.473   1.703  46.239  1.00 30.12
ATOM   3567  CD1  ILE B 412      29.016   0.522  47.010  1.00 28.23
ATOM   3568  C    ILE B 412      25.040   2.600  44.804  1.00 32.37
ATOM   3569  O    ILE B 412      24.719   2.237  43.674  1.00 33.40
ATOM   3570  N    ASN B 413      24.161   2.804  45.786  1.00 33.41
ATOM   3571  CA   ASN B 413      22.721   2.571  45.610  1.00 35.15
ATOM   3572  CB   ASN B 413      22.049   2.299  46.962  1.00 36.57
ATOM   3573  CG   ASN B 413      22.681   1.129  47.713  1.00 38.83
ATOM   3574  OD1  ASN B 413      23.136   0.152  47.106  1.00 39.17
ATOM   3575  ND2  ASN B 413      22.723   1.233  49.044  1.00 38.78
ATOM   3576  C    ASN B 413      21.939   3.665  44.908  1.00 35.35
ATOM   3577  O    ASN B 413      20.964   3.379  44.206  1.00 34.35
ATOM   3578  N    TYR B 414      22.334   4.917  45.122  1.00 36.40
ATOM   3579  CA   TYR B 414      21.621   6.035  44.502  1.00 37.48
ATOM   3580  CB   TYR B 414      20.808   6.776  45.571  1.00 39.04
ATOM   3581  CG   TYR B 414      19.923   5.852  46.377  1.00 43.07
ATOM   3582  CD1  TYR B 414      18.815   5.226  45.790  1.00 43.90
ATOM   3583  CE1  TYR B 414      18.016   4.337  46.520  1.00 45.17
ATOM   3584  CD2  TYR B 414      20.211   5.571  47.721  1.00 44.87
ATOM   3585  CE2  TYR B 414      19.421   4.685  48.462  1.00 45.32
ATOM   3586  CZ   TYR B 414      18.324   4.071  47.857  1.00 46.11
ATOM   3587  OH   TYR B 414      17.542   3.194  48.588  1.00 46.96
```

Figure 8

| | | | | | | | | | |
|---|---|---|---|---|---|---|---|---|---|
| ATOM | 3588 | C | TYR | B | 414 | 22.502 | 7.009 | 43.699 | 1.00 36.37 |
| ATOM | 3589 | O | TYR | B | 414 | 22.012 | 7.970 | 43.098 | 1.00 36.47 |
| ATOM | 3590 | N | GLY | B | 415 | 23.796 | 6.741 | 43.649 | 1.00 35.10 |
| ATOM | 3591 | CA | GLY | B | 415 | 24.683 | 7.626 | 42.913 | 1.00 33.50 |
| ATOM | 3592 | C | GLY | B | 415 | 24.826 | 9.002 | 43.542 | 1.00 31.60 |
| ATOM | 3593 | O | GLY | B | 415 | 25.147 | 9.979 | 42.862 | 1.00 30.99 |
| ATOM | 3594 | N | THR | B | 416 | 24.574 | 9.093 | 44.841 | 1.00 31.06 |
| ATOM | 3595 | CA | THR | B | 416 | 24.706 | 10.374 | 45.511 | 1.00 30.69 |
| ATOM | 3596 | CB | THR | B | 416 | 23.551 | 10.660 | 46.531 | 1.00 30.57 |
| ATOM | 3597 | OG1 | THR | B | 416 | 24.101 | 11.119 | 47.771 | 1.00 31.13 |
| ATOM | 3598 | CG2 | THR | B | 416 | 22.700 | 9.446 | 46.771 | 1.00 29.63 |
| ATOM | 3599 | C | THR | B | 416 | 26.085 | 10.514 | 46.158 | 1.00 29.30 |
| ATOM | 3600 | O | THR | B | 416 | 26.396 | 9.863 | 47.148 | 1.00 29.70 |
| ATOM | 3601 | N | PHE | B | 417 | 26.914 | 11.343 | 45.537 | 1.00 27.88 |
| ATOM | 3602 | CA | PHE | B | 417 | 28.257 | 11.612 | 46.014 | 1.00 27.07 |
| ATOM | 3603 | CB | PHE | B | 417 | 29.248 | 11.593 | 44.831 | 1.00 27.21 |
| ATOM | 3604 | CG | PHE | B | 417 | 29.501 | 10.216 | 44.244 | 1.00 27.38 |
| ATOM | 3605 | CD1 | PHE | B | 417 | 28.703 | 9.721 | 43.197 | 1.00 27.66 |
| ATOM | 3606 | CD2 | PHE | B | 417 | 30.547 | 9.420 | 44.727 | 1.00 25.62 |
| ATOM | 3607 | CE1 | PHE | B | 417 | 28.945 | 8.442 | 42.644 | 1.00 27.01 |
| ATOM | 3608 | CE2 | PHE | B | 417 | 30.796 | 8.151 | 44.185 | 1.00 25.09 |
| ATOM | 3609 | CZ | PHE | B | 417 | 29.998 | 7.662 | 43.144 | 1.00 26.05 |
| ATOM | 3610 | C | PHE | B | 417 | 28.363 | 12.966 | 46.732 | 1.00 25.57 |
| ATOM | 3611 | O | PHE | B | 417 | 27.979 | 13.990 | 46.187 | 1.00 26.17 |
| ATOM | 3612 | N | THR | B | 418 | 28.844 | 12.963 | 47.970 | 1.00 24.08 |
| ATOM | 3613 | CA | THR | B | 418 | 29.049 | 14.207 | 48.714 | 1.00 23.01 |
| ATOM | 3614 | CB | THR | B | 418 | 27.956 | 14.486 | 49.767 | 1.00 22.80 |
| ATOM | 3615 | OG1 | THR | B | 418 | 28.018 | 13.502 | 50.801 | 1.00 22.72 |
| ATOM | 3616 | CG2 | THR | B | 418 | 26.583 | 14.485 | 49.133 | 1.00 22.18 |
| ATOM | 3617 | C | THR | B | 418 | 30.413 | 14.154 | 49.412 | 1.00 22.08 |
| ATOM | 3618 | O | THR | B | 418 | 31.206 | 13.243 | 49.182 | 1.00 21.75 |
| ATOM | 3619 | N | ILE | B | 419 | 30.698 | 15.143 | 50.245 | 1.00 21.81 |
| ATOM | 3620 | CA | ILE | B | 419 | 31.969 | 15.176 | 50.953 | 1.00 20.88 |
| ATOM | 3621 | CB | ILE | B | 419 | 32.207 | 16.544 | 51.623 | 1.00 20.43 |
| ATOM | 3622 | CG2 | ILE | B | 419 | 31.292 | 16.695 | 52.835 | 1.00 19.45 |
| ATOM | 3623 | CG1 | ILE | B | 419 | 33.678 | 16.687 | 52.010 | 1.00 20.38 |
| ATOM | 3624 | CD1 | ILE | B | 419 | 34.628 | 16.638 | 50.835 | 1.00 18.57 |
| ATOM | 3625 | C | ILE | B | 419 | 31.946 | 14.075 | 52.007 | 1.00 20.56 |
| ATOM | 3626 | O | ILE | B | 419 | 32.995 | 13.661 | 52.508 | 1.00 21.18 |
| ATOM | 3627 | N | LYS | B | 420 | 30.744 | 13.626 | 52.367 | 1.00 19.35 |
| ATOM | 3628 | CA | LYS | B | 420 | 30.620 | 12.555 | 53.346 | 1.00 18.25 |
| ATOM | 3629 | CB | LYS | B | 420 | 29.227 | 12.500 | 53.949 | 1.00 16.79 |
| ATOM | 3630 | CG | LYS | B | 420 | 28.936 | 13.641 | 54.878 | 1.00 14.19 |
| ATOM | 3631 | CD | LYS | B | 420 | 29.848 | 13.606 | 56.060 | 1.00 12.97 |
| ATOM | 3632 | CE | LYS | B | 420 | 29.572 | 14.785 | 56.935 | 1.00 13.60 |
| ATOM | 3633 | NZ | LYS | B | 420 | 30.640 | 14.923 | 57.930 | 1.00 16.09 |
| ATOM | 3634 | C | LYS | B | 420 | 30.988 | 11.207 | 52.760 | 1.00 17.93 |
| ATOM | 3635 | O | LYS | B | 420 | 31.390 | 10.308 | 53.487 | 1.00 18.13 |
| ATOM | 3636 | N | SER | B | 421 | 30.820 | 11.042 | 51.456 | 1.00 18.42 |
| ATOM | 3637 | CA | SER | B | 421 | 31.217 | 9.783 | 50.850 | 1.00 20.44 |
| ATOM | 3638 | CB | SER | B | 421 | 30.415 | 9.446 | 49.580 | 1.00 19.78 |
| ATOM | 3639 | OG | SER | B | 421 | 30.082 | 10.584 | 48.828 | 1.00 22.84 |
| ATOM | 3640 | C | SER | B | 421 | 32.736 | 9.777 | 50.629 | 1.00 20.33 |
| ATOM | 3641 | O | SER | B | 421 | 33.336 | 8.715 | 50.473 | 1.00 20.08 |
| ATOM | 3642 | N | ASP | B | 422 | 33.351 | 10.965 | 50.643 | 1.00 20.96 |
| ATOM | 3643 | CA | ASP | B | 422 | 34.809 | 11.094 | 50.522 | 1.00 21.70 |
| ATOM | 3644 | CB | ASP | B | 422 | 35.246 | 12.538 | 50.240 | 1.00 22.21 |
| ATOM | 3645 | CG | ASP | B | 422 | 35.000 | 12.977 | 48.804 | 1.00 23.81 |
| ATOM | 3646 | OD1 | ASP | B | 422 | 34.887 | 12.133 | 47.881 | 1.00 25.31 |
| ATOM | 3647 | OD2 | ASP | B | 422 | 34.939 | 14.201 | 48.601 | 1.00 24.12 |

Figure 8

| | | | | | | | | | |
|---|---|---|---|---|---|---|---|---|---|
| ATOM | 3648 | C | ASP | B | 422 | 35.379 | 10.684 | 51.881 | 1.00 21.82 |
| ATOM | 3649 | O | ASP | B | 422 | 36.452 | 10.103 | 51.953 | 1.00 22.24 |
| ATOM | 3650 | N | VAL | B | 423 | 34.675 | 11.052 | 52.955 | 1.00 21.88 |
| ATOM | 3651 | CA | VAL | B | 423 | 35.064 | 10.689 | 54.320 | 1.00 21.06 |
| ATOM | 3652 | CB | VAL | B | 423 | 34.114 | 11.311 | 55.412 | 1.00 21.83 |
| ATOM | 3653 | CG1 | VAL | B | 423 | 34.453 | 10.758 | 56.824 | 1.00 20.22 |
| ATOM | 3654 | CG2 | VAL | B | 423 | 34.246 | 12.857 | 55.430 | 1.00 18.66 |
| ATOM | 3655 | C | VAL | B | 423 | 35.041 | 9.167 | 54.386 | 1.00 21.59 |
| ATOM | 3656 | O | VAL | B | 423 | 35.945 | 8.566 | 54.974 | 1.00 22.74 |
| ATOM | 3657 | N | TRP | B | 424 | 34.067 | 8.537 | 53.715 | 1.00 21.24 |
| ATOM | 3658 | CA | TRP | B | 424 | 33.982 | 7.077 | 53.686 | 1.00 20.32 |
| ATOM | 3659 | CB | TRP | B | 424 | 32.688 | 6.574 | 53.024 | 1.00 19.69 |
| ATOM | 3660 | CG | TRP | B | 424 | 32.647 | 5.065 | 52.820 | 1.00 18.95 |
| ATOM | 3661 | CD2 | TRP | B | 424 | 31.793 | 4.115 | 53.482 | 1.00 20.04 |
| ATOM | 3662 | CE2 | TRP | B | 424 | 32.116 | 2.829 | 52.964 | 1.00 19.33 |
| ATOM | 3663 | CE3 | TRP | B | 424 | 30.779 | 4.220 | 54.455 | 1.00 21.73 |
| ATOM | 3664 | CD1 | TRP | B | 424 | 33.426 | 4.335 | 51.961 | 1.00 19.24 |
| ATOM | 3665 | NE1 | TRP | B | 424 | 33.117 | 2.999 | 52.046 | 1.00 18.69 |
| ATOM | 3666 | CZ2 | TRP | B | 424 | 31.462 | 1.655 | 53.382 | 1.00 18.62 |
| ATOM | 3667 | CZ3 | TRP | B | 424 | 30.123 | 3.043 | 54.875 | 1.00 20.80 |
| ATOM | 3668 | CH2 | TRP | B | 424 | 30.476 | 1.778 | 54.330 | 1.00 20.09 |
| ATOM | 3669 | C | TRP | B | 424 | 35.217 | 6.540 | 52.962 | 1.00 20.63 |
| ATOM | 3670 | O | TRP | B | 424 | 35.840 | 5.609 | 53.443 | 1.00 21.11 |
| ATOM | 3671 | N | SER | B | 425 | 35.582 | 7.139 | 51.825 | 1.00 21.89 |
| ATOM | 3672 | CA | SER | B | 425 | 36.786 | 6.737 | 51.069 | 1.00 22.19 |
| ATOM | 3673 | CB | SER | B | 425 | 36.922 | 7.557 | 49.786 | 1.00 23.11 |
| ATOM | 3674 | OG | SER | B | 425 | 35.894 | 7.251 | 48.862 | 1.00 26.31 |
| ATOM | 3675 | C | SER | B | 425 | 38.072 | 6.901 | 51.884 | 1.00 21.85 |
| ATOM | 3676 | O | SER | B | 425 | 38.959 | 6.068 | 51.801 | 1.00 22.54 |
| ATOM | 3677 | N | PHE | B | 426 | 38.182 | 7.994 | 52.639 | 1.00 21.88 |
| ATOM | 3678 | CA | PHE | B | 426 | 39.355 | 8.242 | 53.480 | 1.00 22.81 |
| ATOM | 3679 | CB | PHE | B | 426 | 39.239 | 9.576 | 54.250 | 1.00 22.42 |
| ATOM | 3680 | CG | PHE | B | 426 | 40.517 | 9.983 | 54.982 | 1.00 24.24 |
| ATOM | 3681 | CD1 | PHE | B | 426 | 41.626 | 10.469 | 54.282 | 1.00 24.45 |
| ATOM | 3682 | CD2 | PHE | B | 426 | 40.613 | 9.891 | 56.369 | 1.00 24.63 |
| ATOM | 3683 | CE1 | PHE | B | 426 | 42.807 | 10.850 | 54.956 | 1.00 23.85 |
| ATOM | 3684 | CE2 | PHE | B | 426 | 41.799 | 10.273 | 57.043 | 1.00 23.81 |
| ATOM | 3685 | CZ | PHE | B | 426 | 42.884 | 10.749 | 56.328 | 1.00 22.44 |
| ATOM | 3686 | C | PHE | B | 426 | 39.527 | 7.111 | 54.483 | 1.00 22.66 |
| ATOM | 3687 | O | PHE | B | 426 | 40.648 | 6.808 | 54.884 | 1.00 23.41 |
| ATOM | 3688 | N | GLY | B | 427 | 38.411 | 6.532 | 54.925 | 1.00 22.15 |
| ATOM | 3689 | CA | GLY | B | 427 | 38.462 | 5.432 | 55.872 | 1.00 20.85 |
| ATOM | 3690 | C | GLY | B | 427 | 39.050 | 4.186 | 55.229 | 1.00 20.48 |
| ATOM | 3691 | O | GLY | B | 427 | 39.748 | 3.428 | 55.882 | 1.00 20.72 |
| ATOM | 3692 | N | ILE | B | 428 | 38.729 | 3.958 | 53.957 | 1.00 20.85 |
| ATOM | 3693 | CA | ILE | B | 428 | 39.240 | 2.819 | 53.201 | 1.00 20.62 |
| ATOM | 3694 | CB | ILE | B | 428 | 38.498 | 2.670 | 51.836 | 1.00 20.42 |
| ATOM | 3695 | CG2 | ILE | B | 428 | 38.914 | 1.391 | 51.124 | 1.00 20.17 |
| ATOM | 3696 | CG1 | ILE | B | 428 | 36.987 | 2.614 | 52.053 | 1.00 20.18 |
| ATOM | 3697 | CD1 | ILE | B | 428 | 36.522 | 1.419 | 52.891 | 1.00 20.96 |
| ATOM | 3698 | C | ILE | B | 428 | 40.731 | 3.083 | 52.957 | 1.00 21.84 |
| ATOM | 3699 | O | ILE | B | 428 | 41.560 | 2.192 | 53.098 | 1.00 23.65 |
| ATOM | 3700 | N | LEU | B | 429 | 41.059 | 4.332 | 52.639 | 1.00 22.68 |
| ATOM | 3701 | CA | LEU | B | 429 | 42.430 | 4.768 | 52.381 | 1.00 23.20 |
| ATOM | 3702 | CB | LEU | B | 429 | 42.403 | 6.235 | 51.941 | 1.00 22.13 |
| ATOM | 3703 | CG | LEU | B | 429 | 43.591 | 6.890 | 51.251 | 1.00 22.71 |
| ATOM | 3704 | CD1 | LEU | B | 429 | 43.122 | 8.142 | 50.549 | 1.00 22.25 |
| ATOM | 3705 | CD2 | LEU | B | 429 | 44.661 | 7.234 | 52.244 | 1.00 23.56 |
| ATOM | 3706 | C | LEU | B | 429 | 43.315 | 4.595 | 53.630 | 1.00 23.60 |
| ATOM | 3707 | O | LEU | B | 429 | 44.521 | 4.358 | 53.508 | 1.00 24.58 |

Figure 8

| ATOM | 3708 | N | LEU | B | 430 | 42.719 | 4.743 | 54.817 | 1.00 | 22.56 |
| ATOM | 3709 | CA | LEU | B | 430 | 43.453 | 4.593 | 56.062 | 1.00 | 21.51 |
| ATOM | 3710 | CB | LEU | B | 430 | 42.630 | 5.050 | 57.261 | 1.00 | 20.28 |
| ATOM | 3711 | CG | LEU | B | 430 | 42.439 | 6.546 | 57.528 | 1.00 | 19.22 |
| ATOM | 3712 | CD1 | LEU | B | 430 | 41.482 | 6.704 | 58.696 | 1.00 | 17.10 |
| ATOM | 3713 | CD2 | LEU | B | 430 | 43.773 | 7.257 | 57.821 | 1.00 | 17.95 |
| ATOM | 3714 | C | LEU | B | 430 | 43.884 | 3.145 | 56.253 | 1.00 | 22.75 |
| ATOM | 3715 | O | LEU | B | 430 | 44.906 | 2.898 | 56.890 | 1.00 | 24.23 |
| ATOM | 3716 | N | THR | B | 431 | 43.098 | 2.191 | 55.739 | 1.00 | 23.05 |
| ATOM | 3717 | CA | THR | B | 431 | 43.452 | 0.768 | 55.845 | 1.00 | 23.41 |
| ATOM | 3718 | CB | THR | B | 431 | 42.260 | -0.224 | 55.525 | 1.00 | 22.82 |
| ATOM | 3719 | OG1 | THR | B | 431 | 41.944 | -0.203 | 54.124 | 1.00 | 21.86 |
| ATOM | 3720 | CG2 | THR | B | 431 | 41.016 | 0.115 | 56.360 | 1.00 | 20.43 |
| ATOM | 3721 | C | THR | B | 431 | 44.605 | 0.516 | 54.887 | 1.00 | 24.38 |
| ATOM | 3722 | O | THR | B | 431 | 45.535 | -0.212 | 55.218 | 1.00 | 25.41 |
| ATOM | 3723 | N | GLU | B | 432 | 44.550 | 1.148 | 53.715 | 1.00 | 25.14 |
| ATOM | 3724 | CA | GLU | B | 432 | 45.613 | 1.032 | 52.720 | 1.00 | 26.14 |
| ATOM | 3725 | CB | GLU | B | 432 | 45.320 | 1.900 | 51.508 | 1.00 | 25.99 |
| ATOM | 3726 | CG | GLU | B | 432 | 44.163 | 1.442 | 50.671 | 1.00 | 26.10 |
| ATOM | 3727 | CD | GLU | B | 432 | 44.062 | 2.233 | 49.392 | 1.00 | 25.58 |
| ATOM | 3728 | OE1 | GLU | B | 432 | 43.502 | 3.353 | 49.399 | 1.00 | 25.35 |
| ATOM | 3729 | OE2 | GLU | B | 432 | 44.558 | 1.728 | 48.377 | 1.00 | 25.55 |
| ATOM | 3730 | C | GLU | B | 432 | 46.920 | 1.531 | 53.302 | 1.00 | 27.16 |
| ATOM | 3731 | O | GLU | B | 432 | 47.972 | 1.015 | 52.982 | 1.00 | 28.61 |
| ATOM | 3732 | N | ILE | B | 433 | 46.849 | 2.598 | 54.090 | 1.00 | 27.61 |
| ATOM | 3733 | CA | ILE | B | 433 | 48.017 | 3.179 | 54.714 | 1.00 | 28.07 |
| ATOM | 3734 | CB | ILE | B | 433 | 47.680 | 4.555 | 55.310 | 1.00 | 28.31 |
| ATOM | 3735 | CG2 | ILE | B | 433 | 48.790 | 5.035 | 56.232 | 1.00 | 28.50 |
| ATOM | 3736 | CG1 | ILE | B | 433 | 47.427 | 5.559 | 54.185 | 1.00 | 28.86 |
| ATOM | 3737 | CD1 | ILE | B | 433 | 47.341 | 7.009 | 54.663 | 1.00 | 29.48 |
| ATOM | 3738 | C | ILE | B | 433 | 48.661 | 2.281 | 55.778 | 1.00 | 29.40 |
| ATOM | 3739 | O | ILE | B | 433 | 49.869 | 2.046 | 55.736 | 1.00 | 31.11 |
| ATOM | 3740 | N | VAL | B | 434 | 47.869 | 1.752 | 56.709 | 1.00 | 29.47 |
| ATOM | 3741 | CA | VAL | B | 434 | 48.421 | 0.903 | 57.770 | 1.00 | 28.97 |
| ATOM | 3742 | CB | VAL | B | 434 | 47.493 | 0.865 | 59.014 | 1.00 | 28.48 |
| ATOM | 3743 | CG1 | VAL | B | 434 | 47.437 | 2.237 | 59.635 | 1.00 | 28.59 |
| ATOM | 3744 | CG2 | VAL | B | 434 | 46.075 | 0.403 | 58.636 | 1.00 | 28.24 |
| ATOM | 3745 | C | VAL | B | 434 | 48.802 | -0.524 | 57.352 | 1.00 | 29.37 |
| ATOM | 3746 | O | VAL | B | 434 | 49.528 | -1.201 | 58.072 | 1.00 | 29.66 |
| ATOM | 3747 | N | THR | B | 435 | 48.339 | -0.969 | 56.187 | 1.00 | 30.07 |
| ATOM | 3748 | CA | THR | B | 435 | 48.641 | -2.320 | 55.709 | 1.00 | 31.17 |
| ATOM | 3749 | CB | THR | B | 435 | 47.347 | -3.098 | 55.294 | 1.00 | 31.11 |
| ATOM | 3750 | OG1 | THR | B | 435 | 46.718 | -2.455 | 54.180 | 1.00 | 31.26 |
| ATOM | 3751 | CG2 | THR | B | 435 | 46.353 | -3.183 | 56.447 | 1.00 | 29.39 |
| ATOM | 3752 | C | THR | B | 435 | 49.605 | -2.288 | 54.523 | 1.00 | 32.66 |
| ATOM | 3753 | O | THR | B | 435 | 49.719 | -3.261 | 53.778 | 1.00 | 32.63 |
| ATOM | 3754 | N | HIS | B | 436 | 50.242 | -1.135 | 54.328 | 1.00 | 34.78 |
| ATOM | 3755 | CA | HIS | B | 436 | 51.218 | -0.901 | 53.257 | 1.00 | 36.10 |
| ATOM | 3756 | CB | HIS | B | 436 | 52.499 | -1.699 | 53.517 | 1.00 | 38.30 |
| ATOM | 3757 | CG | HIS | B | 436 | 53.062 | -1.484 | 54.889 | 1.00 | 41.53 |
| ATOM | 3758 | CD2 | HIS | B | 436 | 53.233 | -2.338 | 55.926 | 1.00 | 42.27 |
| ATOM | 3759 | ND1 | HIS | B | 436 | 53.477 | -0.245 | 55.338 | 1.00 | 42.19 |
| ATOM | 3760 | CE1 | HIS | B | 436 | 53.877 | -0.345 | 56.593 | 1.00 | 42.27 |
| ATOM | 3761 | NE2 | HIS | B | 436 | 53.738 | -1.604 | 56.973 | 1.00 | 44.25 |
| ATOM | 3762 | C | HIS | B | 436 | 50.733 | -1.108 | 51.834 | 1.00 | 36.02 |
| ATOM | 3763 | O | HIS | B | 436 | 51.393 | -1.779 | 51.035 | 1.00 | 36.62 |
| ATOM | 3764 | N | GLY | B | 437 | 49.606 | -0.482 | 51.511 | 1.00 | 35.26 |
| ATOM | 3765 | CA | GLY | B | 437 | 49.063 | -0.578 | 50.173 | 1.00 | 35.62 |
| ATOM | 3766 | C | GLY | B | 437 | 48.291 | -1.841 | 49.856 | 1.00 | 36.26 |
| ATOM | 3767 | O | GLY | B | 437 | 48.095 | -2.165 | 48.688 | 1.00 | 36.62 |

Figure 8

| ATOM | 3768 | N   | ARG | B | 438 | 47.838 | -2.551  | 50.882 | 1.00 | 37.08 |
|------|------|-----|-----|---|-----|--------|---------|--------|------|-------|
| ATOM | 3769 | CA  | ARG | B | 438 | 47.055 | -3.772  | 50.682 | 1.00 | 38.45 |
| ATOM | 3770 | CB  | ARG | B | 438 | 46.943 | -4.517  | 52.023 | 1.00 | 41.03 |
| ATOM | 3771 | CG  | ARG | B | 438 | 46.515 | -5.987  | 51.976 | 1.00 | 44.20 |
| ATOM | 3772 | CD  | ARG | B | 438 | 45.010 | -6.181  | 51.782 | 1.00 | 47.61 |
| ATOM | 3773 | NE  | ARG | B | 438 | 44.170 | -5.484  | 52.769 | 1.00 | 49.83 |
| ATOM | 3774 | CZ  | ARG | B | 438 | 44.082 | -5.811  | 54.059 | 1.00 | 50.90 |
| ATOM | 3775 | NH1 | ARG | B | 438 | 44.788 | -6.834  | 54.541 | 1.00 | 51.90 |
| ATOM | 3776 | NH2 | ARG | B | 438 | 43.276 | -5.123  | 54.863 | 1.00 | 49.88 |
| ATOM | 3777 | C   | ARG | B | 438 | 45.656 | -3.408  | 50.123 | 1.00 | 37.17 |
| ATOM | 3778 | O   | ARG | B | 438 | 45.106 | -2.346  | 50.434 | 1.00 | 36.70 |
| ATOM | 3779 | N   | ILE | B | 439 | 45.114 | -4.272  | 49.268 | 1.00 | 36.01 |
| ATOM | 3780 | CA  | ILE | B | 439 | 43.794 | -4.057  | 48.670 | 1.00 | 35.15 |
| ATOM | 3781 | CB  | ILE | B | 439 | 43.571 | -5.003  | 47.435 | 1.00 | 35.63 |
| ATOM | 3782 | CG2 | ILE | B | 439 | 42.114 | -5.380  | 47.261 | 1.00 | 34.99 |
| ATOM | 3783 | CG1 | ILE | B | 439 | 44.063 | -4.296  | 46.167 | 1.00 | 37.92 |
| ATOM | 3784 | CD1 | ILE | B | 439 | 43.981 | -5.123  | 44.886 | 1.00 | 39.33 |
| ATOM | 3785 | C   | ILE | B | 439 | 42.698 | -4.240  | 49.711 | 1.00 | 34.06 |
| ATOM | 3786 | O   | ILE | B | 439 | 42.677 | -5.246  | 50.421 | 1.00 | 34.29 |
| ATOM | 3787 | N   | PRO | B | 440 | 41.774 | -3.264  | 49.821 | 1.00 | 32.36 |
| ATOM | 3788 | CD  | PRO | B | 440 | 41.693 | -2.023  | 49.035 | 1.00 | 31.57 |
| ATOM | 3789 | CA  | PRO | B | 440 | 40.674 | -3.331  | 50.789 | 1.00 | 31.27 |
| ATOM | 3790 | CB  | PRO | B | 440 | 39.866 | -2.072  | 50.463 | 1.00 | 31.25 |
| ATOM | 3791 | CG  | PRO | B | 440 | 40.909 | -1.123  | 49.946 | 1.00 | 30.98 |
| ATOM | 3792 | C   | PRO | B | 440 | 39.849 | -4.600  | 50.585 | 1.00 | 30.37 |
| ATOM | 3793 | O   | PRO | B | 440 | 39.866 | -5.179  | 49.489 | 1.00 | 29.90 |
| ATOM | 3794 | N   | TYR | B | 441 | 39.137 | -5.027  | 51.631 | 1.00 | 29.52 |
| ATOM | 3795 | CA  | TYR | B | 441 | 38.310 | -6.238  | 51.579 | 1.00 | 29.51 |
| ATOM | 3796 | CB  | TYR | B | 441 | 36.989 | -5.980  | 50.838 | 1.00 | 27.99 |
| ATOM | 3797 | CG  | TYR | B | 441 | 36.207 | -4.792  | 51.351 | 1.00 | 27.09 |
| ATOM | 3798 | CD1 | TYR | B | 441 | 35.268 | -4.939  | 52.363 | 1.00 | 26.20 |
| ATOM | 3799 | CE1 | TYR | B | 441 | 34.582 | -3.847  | 52.855 | 1.00 | 27.00 |
| ATOM | 3800 | CD2 | TYR | B | 441 | 36.434 | -3.511  | 50.839 | 1.00 | 26.31 |
| ATOM | 3801 | CE2 | TYR | B | 441 | 35.755 | -2.411  | 51.323 | 1.00 | 26.42 |
| ATOM | 3802 | CZ  | TYR | B | 441 | 34.834 | -2.578  | 52.335 | 1.00 | 27.50 |
| ATOM | 3803 | OH  | TYR | B | 441 | 34.205 | -1.471  | 52.864 | 1.00 | 28.38 |
| ATOM | 3804 | C   | TYR | B | 441 | 39.088 | -7.343  | 50.861 | 1.00 | 30.72 |
| ATOM | 3805 | O   | TYR | B | 441 | 38.680 | -7.825  | 49.797 | 1.00 | 30.67 |
| ATOM | 3806 | N   | PRO | B | 442 | 40.246 | -7.731  | 51.418 | 1.00 | 31.98 |
| ATOM | 3807 | CD  | PRO | B | 442 | 40.764 | -7.356  | 52.752 | 1.00 | 31.50 |
| ATOM | 3808 | CA  | PRO | B | 442 | 41.065 | -8.777  | 50.796 | 1.00 | 33.02 |
| ATOM | 3809 | CB  | PRO | B | 442 | 42.242 | -8.902  | 51.766 | 1.00 | 33.00 |
| ATOM | 3810 | CG  | PRO | B | 442 | 41.629 | -8.532  | 53.107 | 1.00 | 32.32 |
| ATOM | 3811 | C   | PRO | B | 442 | 40.269 | -10.078 | 50.669 | 1.00 | 34.73 |
| ATOM | 3812 | O   | PRO | B | 442 | 39.578 | -10.491 | 51.603 | 1.00 | 35.96 |
| ATOM | 3813 | N   | GLY | B | 443 | 40.290 | -10.687 | 49.492 | 1.00 | 35.50 |
| ATOM | 3814 | CA  | GLY | B | 443 | 39.548 | -11.927 | 49.333 | 1.00 | 36.63 |
| ATOM | 3815 | C   | GLY | B | 443 | 38.052 | -11.760 | 49.161 | 1.00 | 36.96 |
| ATOM | 3816 | O   | GLY | B | 443 | 37.266 | -12.597 | 49.613 | 1.00 | 38.07 |
| ATOM | 3817 | N   | MET | B | 444 | 37.680 | -10.674 | 48.490 | 1.00 | 37.29 |
| ATOM | 3818 | CA  | MET | B | 444 | 36.299 | -10.317 | 48.151 | 1.00 | 37.13 |
| ATOM | 3819 | CB  | MET | B | 444 | 35.679 | -9.360  | 49.176 | 1.00 | 36.35 |
| ATOM | 3820 | CG  | MET | B | 444 | 35.082 | -10.032 | 50.383 | 1.00 | 36.77 |
| ATOM | 3821 | SD  | MET | B | 444 | 34.458 | -8.879  | 51.625 | 1.00 | 36.85 |
| ATOM | 3822 | CE  | MET | B | 444 | 33.044 | -8.343  | 50.823 | 1.00 | 36.79 |
| ATOM | 3823 | C   | MET | B | 444 | 36.377 | -9.599  | 46.803 | 1.00 | 37.67 |
| ATOM | 3824 | O   | MET | B | 444 | 37.309 | -8.814  | 46.564 | 1.00 | 37.81 |
| ATOM | 3825 | N   | THR | B | 445 | 35.455 | -9.924  | 45.900 | 1.00 | 37.21 |
| ATOM | 3826 | CA  | THR | B | 445 | 35.405 | -9.275  | 44.593 | 1.00 | 36.94 |
| ATOM | 3827 | CB  | THR | B | 445 | 34.918 | -10.235 | 43.516 | 1.00 | 36.82 |

Figure 8

```
ATOM   3828  OG1  THR B 445      33.565 -10.611  43.786  1.00 38.19
ATOM   3829  CG2  THR B 445      35.768 -11.482  43.525  1.00 38.01
ATOM   3830  C    THR B 445      34.417  -8.126  44.720  1.00 37.50
ATOM   3831  O    THR B 445      33.738  -8.013  45.742  1.00 38.30
ATOM   3832  N    ASN B 446      34.312  -7.280  43.699  1.00 37.77
ATOM   3833  CA   ASN B 446      33.373  -6.161  43.766  1.00 37.76
ATOM   3834  CB   ASN B 446      33.438  -5.297  42.506  1.00 37.82
ATOM   3835  CG   ASN B 446      34.739  -4.514  42.409  1.00 38.73
ATOM   3836  OD1  ASN B 446      35.648  -4.687  43.233  1.00 38.85
ATOM   3837  ND2  ASN B 446      34.834  -3.644  41.407  1.00 38.41
ATOM   3838  C    ASN B 446      31.928  -6.557  44.093  1.00 37.62
ATOM   3839  O    ASN B 446      31.334  -5.975  45.002  1.00 37.28
ATOM   3840  N    PRO B 447      31.342  -7.540  43.365  1.00 37.41
ATOM   3841  CD   PRO B 447      31.754  -8.130  42.074  1.00 36.86
ATOM   3842  CA   PRO B 447      29.960  -7.929  43.677  1.00 36.35
ATOM   3843  CB   PRO B 447      29.615  -8.947  42.577  1.00 36.40
ATOM   3844  CG   PRO B 447      30.947  -9.387  42.042  1.00 36.18
ATOM   3845  C    PRO B 447      29.763  -8.475  45.096  1.00 35.41
ATOM   3846  O    PRO B 447      28.658  -8.400  45.653  1.00 34.94
ATOM   3847  N    GLU B 448      30.831  -9.004  45.683  1.00 33.98
ATOM   3848  CA   GLU B 448      30.751  -9.510  47.040  1.00 33.98
ATOM   3849  CB   GLU B 448      31.854 -10.512  47.301  1.00 35.05
ATOM   3850  CG   GLU B 448      31.573 -11.842  46.672  1.00 38.00
ATOM   3851  CD   GLU B 448      32.802 -12.715  46.590  1.00 41.00
ATOM   3852  OE1  GLU B 448      33.754 -12.511  47.382  1.00 42.81
ATOM   3853  OE2  GLU B 448      32.816 -13.612  45.719  1.00 43.35
ATOM   3854  C    GLU B 448      30.813  -8.361  48.038  1.00 33.73
ATOM   3855  O    GLU B 448      30.154  -8.403  49.074  1.00 33.70
ATOM   3856  N    VAL B 449      31.588  -7.327  47.717  1.00 32.54
ATOM   3857  CA   VAL B 449      31.693  -6.152  48.583  1.00 31.36
ATOM   3858  CB   VAL B 449      32.787  -5.172  48.073  1.00 30.49
ATOM   3859  CG1  VAL B 449      32.702  -3.830  48.776  1.00 28.67
ATOM   3860  CG2  VAL B 449      34.162  -5.782  48.301  1.00 28.41
ATOM   3861  C    VAL B 449      30.320  -5.487  48.619  1.00 31.38
ATOM   3862  O    VAL B 449      29.835  -5.092  49.680  1.00 32.08
ATOM   3863  N    ILE B 450      29.660  -5.472  47.467  1.00 31.37
ATOM   3864  CA   ILE B 450      28.329  -4.892  47.327  1.00 31.53
ATOM   3865  CB   ILE B 450      27.833  -4.921  45.848  1.00 32.54
ATOM   3866  CG2  ILE B 450      26.512  -4.166  45.726  1.00 31.66
ATOM   3867  CG1  ILE B 450      28.893  -4.351  44.885  1.00 33.13
ATOM   3868  CD1  ILE B 450      29.016  -2.849  44.853  1.00 33.77
ATOM   3869  C    ILE B 450      27.296  -5.630  48.187  1.00 31.09
ATOM   3870  O    ILE B 450      26.526  -4.990  48.896  1.00 30.83
ATOM   3871  N    GLN B 451      27.282  -6.963  48.133  1.00 31.43
ATOM   3872  CA   GLN B 451      26.317  -7.726  48.922  1.00 32.10
ATOM   3873  CB   GLN B 451      26.087  -9.122  48.355  1.00 35.06
ATOM   3874  CG   GLN B 451      27.310  -9.997  48.251  1.00 40.62
ATOM   3875  CD   GLN B 451      27.153 -11.079  47.180  1.00 42.86
ATOM   3876  OE1  GLN B 451      27.636 -12.208  47.337  1.00 44.42
ATOM   3877  NE2  GLN B 451      26.501 -10.725  46.072  1.00 43.65
ATOM   3878  C    GLN B 451      26.628  -7.773  50.400  1.00 30.69
ATOM   3879  O    GLN B 451      25.761  -8.050  51.211  1.00 32.21
ATOM   3880  N    ASN B 452      27.869  -7.497  50.755  1.00 29.53
ATOM   3881  CA   ASN B 452      28.245  -7.459  52.152  1.00 28.17
ATOM   3882  CB   ASN B 452      29.737  -7.699  52.319  1.00 27.91
ATOM   3883  CG   ASN B 452      30.049  -9.144  52.506  1.00 28.38
ATOM   3884  OD1  ASN B 452      29.909  -9.675  53.610  1.00 30.04
ATOM   3885  ND2  ASN B 452      30.409  -9.820  51.422  1.00 27.80
ATOM   3886  C    ASN B 452      27.848  -6.106  52.726  1.00 27.65
ATOM   3887  O    ASN B 452      27.340  -6.036  53.833  1.00 26.71
```

Figure 8

| ATOM | 3888 | N | LEU | B | 453 | 28.064 | -5.037 | 51.959 | 1.00 | 26.83 |
|------|------|-----|-----|---|-----|--------|--------|--------|------|-------|
| ATOM | 3889 | CA | LEU | B | 453 | 27.682 | -3.704 | 52.404 | 1.00 | 26.32 |
| ATOM | 3890 | CB | LEU | B | 453 | 28.227 | -2.615 | 51.486 | 1.00 | 26.50 |
| ATOM | 3891 | CG | LEU | B | 453 | 29.724 | -2.315 | 51.592 | 1.00 | 26.99 |
| ATOM | 3892 | CD1 | LEU | B | 453 | 30.000 | -1.133 | 50.684 | 1.00 | 27.22 |
| ATOM | 3893 | CD2 | LEU | B | 453 | 30.155 | -2.006 | 53.018 | 1.00 | 24.24 |
| ATOM | 3894 | C | LEU | B | 453 | 26.168 | -3.603 | 52.520 | 1.00 | 26.20 |
| ATOM | 3895 | O | LEU | B | 453 | 25.672 | -2.786 | 53.278 | 1.00 | 25.67 |
| ATOM | 3896 | N | GLU | B | 454 | 25.433 | -4.410 | 51.757 | 1.00 | 26.74 |
| ATOM | 3897 | CA | GLU | B | 454 | 23.978 | -4.430 | 51.870 | 1.00 | 28.02 |
| ATOM | 3898 | CB | GLU | B | 454 | 23.367 | -5.414 | 50.895 | 1.00 | 31.17 |
| ATOM | 3899 | CG | GLU | B | 454 | 23.564 | -5.120 | 49.443 | 1.00 | 38.22 |
| ATOM | 3900 | CD | GLU | B | 454 | 22.944 | -6.201 | 48.551 | 1.00 | 41.92 |
| ATOM | 3901 | OE1 | GLU | B | 454 | 23.108 | -6.118 | 47.305 | 1.00 | 43.68 |
| ATOM | 3902 | OE2 | GLU | B | 454 | 22.306 | -7.141 | 49.102 | 1.00 | 42.70 |
| ATOM | 3903 | C | GLU | B | 454 | 23.624 | -4.951 | 53.268 | 1.00 | 26.75 |
| ATOM | 3904 | O | GLU | B | 454 | 22.690 | -4.467 | 53.910 | 1.00 | 25.98 |
| ATOM | 3905 | N | ARG | B | 455 | 24.362 | -5.970 | 53.711 | 1.00 | 25.45 |
| ATOM | 3906 | CA | ARG | B | 455 | 24.143 | -6.581 | 55.021 | 1.00 | 24.94 |
| ATOM | 3907 | CB | ARG | B | 455 | 24.595 | -8.046 | 55.009 | 1.00 | 25.88 |
| ATOM | 3908 | CG | ARG | B | 455 | 23.922 | -8.960 | 53.967 | 1.00 | 29.50 |
| ATOM | 3909 | CD | ARG | B | 455 | 24.454 | -10.414 | 54.030 | 1.00 | 32.34 |
| ATOM | 3910 | NE | ARG | B | 455 | 25.885 | -10.417 | 54.314 | 1.00 | 39.12 |
| ATOM | 3911 | CZ | ARG | B | 455 | 26.425 | -10.750 | 55.494 | 1.00 | 41.76 |
| ATOM | 3912 | NH1 | ARG | B | 455 | 25.654 | -11.159 | 56.504 | 1.00 | 41.71 |
| ATOM | 3913 | NH2 | ARG | B | 455 | 27.716 | -10.495 | 55.731 | 1.00 | 42.21 |
| ATOM | 3914 | C | ARG | B | 455 | 24.875 | -5.809 | 56.134 | 1.00 | 23.87 |
| ATOM | 3915 | O | ARG | B | 455 | 24.960 | -6.272 | 57.272 | 1.00 | 23.42 |
| ATOM | 3916 | N | GLY | B | 456 | 25.443 | -4.657 | 55.776 | 1.00 | 22.90 |
| ATOM | 3917 | CA | GLY | B | 456 | 26.154 | -3.810 | 56.725 | 1.00 | 21.38 |
| ATOM | 3918 | C | GLY | B | 456 | 27.523 | -4.260 | 57.183 | 1.00 | 20.38 |
| ATOM | 3919 | O | GLY | B | 456 | 27.954 | -3.968 | 58.297 | 1.00 | 19.80 |
| ATOM | 3920 | N | TYR | B | 457 | 28.231 | -4.942 | 56.303 | 1.00 | 21.14 |
| ATOM | 3921 | CA | TYR | B | 457 | 29.553 | -5.440 | 56.623 | 1.00 | 20.99 |
| ATOM | 3922 | CB | TYR | B | 457 | 29.975 | -6.457 | 55.558 | 1.00 | 20.64 |
| ATOM | 3923 | CG | TYR | B | 457 | 31.383 | -6.987 | 55.726 | 1.00 | 22.42 |
| ATOM | 3924 | CD1 | TYR | B | 457 | 31.643 | -8.134 | 56.503 | 1.00 | 21.39 |
| ATOM | 3925 | CE1 | TYR | B | 457 | 32.943 | -8.599 | 56.678 | 1.00 | 21.11 |
| ATOM | 3926 | CD2 | TYR | B | 457 | 32.467 | -6.328 | 55.129 | 1.00 | 22.30 |
| ATOM | 3927 | CE2 | TYR | B | 457 | 33.765 | -6.786 | 55.304 | 1.00 | 22.43 |
| ATOM | 3928 | CZ | TYR | B | 457 | 33.993 | -7.916 | 56.077 | 1.00 | 22.21 |
| ATOM | 3929 | OH | TYR | B | 457 | 35.295 | -8.331 | 56.256 | 1.00 | 25.08 |
| ATOM | 3930 | C | TYR | B | 457 | 30.602 | -4.333 | 56.765 | 1.00 | 20.80 |
| ATOM | 3931 | O | TYR | B | 457 | 30.583 | -3.352 | 56.033 | 1.00 | 20.65 |
| ATOM | 3932 | N | ARG | B | 458 | 31.510 | -4.506 | 57.726 | 1.00 | 20.81 |
| ATOM | 3933 | CA | ARG | B | 458 | 32.604 | -3.569 | 57.953 | 1.00 | 21.25 |
| ATOM | 3934 | CB | ARG | B | 458 | 32.353 | -2.739 | 59.213 | 1.00 | 18.60 |
| ATOM | 3935 | CG | ARG | B | 458 | 31.178 | -1.797 | 59.117 | 1.00 | 15.12 |
| ATOM | 3936 | CD | ARG | B | 458 | 31.367 | -0.818 | 57.980 | 1.00 | 14.39 |
| ATOM | 3937 | NE | ARG | B | 458 | 30.349 | 0.218 | 57.989 | 1.00 | 14.00 |
| ATOM | 3938 | CZ | ARG | B | 458 | 29.231 | 0.174 | 57.267 | 1.00 | 16.22 |
| ATOM | 3939 | NH1 | ARG | B | 458 | 28.987 | -0.851 | 56.466 | 1.00 | 15.51 |
| ATOM | 3940 | NH2 | ARG | B | 458 | 28.329 | 1.143 | 57.359 | 1.00 | 15.82 |
| ATOM | 3941 | C | ARG | B | 458 | 33.907 | -4.357 | 58.112 | 1.00 | 22.68 |
| ATOM | 3942 | O | ARG | B | 458 | 33.912 | -5.430 | 58.713 | 1.00 | 23.02 |
| ATOM | 3943 | N | MET | B | 459 | 35.003 | -3.856 | 57.546 | 1.00 | 24.14 |
| ATOM | 3944 | CA | MET | B | 459 | 36.295 | -4.538 | 57.690 | 1.00 | 25.51 |
| ATOM | 3945 | CB | MET | B | 459 | 37.389 | -3.828 | 56.899 | 1.00 | 26.01 |
| ATOM | 3946 | CG | MET | B | 459 | 37.380 | -4.062 | 55.405 | 1.00 | 27.51 |
| ATOM | 3947 | SD | MET | B | 459 | 38.818 | -3.228 | 54.661 | 1.00 | 28.19 |

Figure 8

| | | | | | | | | | |
|---|---|---|---|---|---|---|---|---|---|
| ATOM | 3948 | CE | MET | B | 459 | 38.122 | -1.597 | 54.306 | 1.00 26.82 |
| ATOM | 3949 | C | MET | B | 459 | 36.741 | -4.588 | 59.153 | 1.00 26.62 |
| ATOM | 3950 | O | MET | B | 459 | 36.462 | -3.671 | 59.938 | 1.00 25.92 |
| ATOM | 3951 | N | VAL | B | 460 | 37.448 | -5.658 | 59.512 | 1.00 28.34 |
| ATOM | 3952 | CA | VAL | B | 460 | 37.951 | -5.816 | 60.876 | 1.00 29.54 |
| ATOM | 3953 | CB | VAL | B | 460 | 38.264 | -7.313 | 61.197 | 1.00 29.20 |
| ATOM | 3954 | CG1 | VAL | B | 460 | 37.043 | -8.167 | 60.908 | 1.00 28.53 |
| ATOM | 3955 | CG2 | VAL | B | 460 | 39.456 | -7.816 | 60.378 | 1.00 28.57 |
| ATOM | 3956 | C | VAL | B | 460 | 39.213 | -4.960 | 61.034 | 1.00 30.67 |
| ATOM | 3957 | O | VAL | B | 460 | 39.690 | -4.371 | 60.064 | 1.00 29.74 |
| ATOM | 3958 | N | ARG | B | 461 | 39.717 | -4.846 | 62.258 | 1.00 32.00 |
| ATOM | 3959 | CA | ARG | B | 461 | 40.930 | -4.079 | 62.518 | 1.00 33.86 |
| ATOM | 3960 | CB | ARG | B | 461 | 41.198 | -4.025 | 64.029 | 1.00 35.06 |
| ATOM | 3961 | CG | ARG | B | 461 | 42.277 | -3.027 | 64.457 | 1.00 37.08 |
| ATOM | 3962 | CD | ARG | B | 461 | 42.490 | -3.004 | 65.983 | 1.00 40.19 |
| ATOM | 3963 | NE | ARG | B | 461 | 42.961 | -4.292 | 66.484 | 1.00 44.05 |
| ATOM | 3964 | CZ | ARG | B | 461 | 44.115 | -4.862 | 66.130 | 1.00 47.49 |
| ATOM | 3965 | NH1 | ARG | B | 461 | 44.949 | -4.260 | 65.280 | 1.00 49.76 |
| ATOM | 3966 | NH2 | ARG | B | 461 | 44.398 | -6.092 | 66.533 | 1.00 48.64 |
| ATOM | 3967 | C | ARG | B | 461 | 42.119 | -4.730 | 61.780 | 1.00 34.96 |
| ATOM | 3968 | O | ARG | B | 461 | 42.478 | -5.883 | 62.060 | 1.00 34.62 |
| ATOM | 3969 | N | PRO | B | 462 | 42.733 | -4.008 | 60.814 | 1.00 36.17 |
| ATOM | 3970 | CD | PRO | B | 462 | 42.419 | -2.633 | 60.377 | 1.00 35.22 |
| ATOM | 3971 | CA | PRO | B | 462 | 43.874 | -4.543 | 60.056 | 1.00 37.35 |
| ATOM | 3972 | CB | PRO | B | 462 | 44.244 | -3.382 | 59.126 | 1.00 36.10 |
| ATOM | 3973 | CG | PRO | B | 462 | 42.968 | -2.611 | 58.985 | 1.00 34.69 |
| ATOM | 3974 | C | PRO | B | 462 | 45.045 | -4.867 | 60.982 | 1.00 39.34 |
| ATOM | 3975 | O | PRO | B | 462 | 45.155 | -4.307 | 62.070 | 1.00 39.30 |
| ATOM | 3976 | N | ASP | B | 463 | 45.917 | -5.767 | 60.551 | 1.00 42.76 |
| ATOM | 3977 | CA | ASP | B | 463 | 47.077 | -6.124 | 61.358 | 1.00 45.86 |
| ATOM | 3978 | CB | ASP | B | 463 | 47.873 | -7.262 | 60.705 | 1.00 48.76 |
| ATOM | 3979 | CG | ASP | B | 463 | 47.133 | -8.592 | 60.727 | 1.00 51.32 |
| ATOM | 3980 | OD1 | ASP | B | 463 | 46.346 | -8.832 | 61.673 | 1.00 52.75 |
| ATOM | 3981 | OD2 | ASP | B | 463 | 47.351 | -9.399 | 59.790 | 1.00 53.75 |
| ATOM | 3982 | C | ASP | B | 463 | 47.985 | -4.907 | 61.525 | 1.00 46.67 |
| ATOM | 3983 | O | ASP | B | 463 | 48.221 | -4.151 | 60.562 | 1.00 46.75 |
| ATOM | 3984 | N | ASN | B | 464 | 48.483 | -4.735 | 62.753 | 1.00 46.93 |
| ATOM | 3985 | CA | ASN | B | 464 | 49.384 | -3.636 | 63.111 | 1.00 46.95 |
| ATOM | 3986 | CB | ASN | B | 464 | 50.695 | -3.735 | 62.304 | 1.00 50.51 |
| ATOM | 3987 | CG | ASN | B | 464 | 51.512 | -5.001 | 62.644 | 1.00 53.25 |
| ATOM | 3988 | OD1 | ASN | B | 464 | 52.284 | -5.019 | 63.612 | 1.00 54.33 |
| ATOM | 3989 | ND2 | ASN | B | 464 | 51.352 | -6.052 | 61.832 | 1.00 53.90 |
| ATOM | 3990 | C | ASN | B | 464 | 48.743 | -2.252 | 62.937 | 1.00 45.49 |
| ATOM | 3991 | O | ASN | B | 464 | 49.332 | -1.351 | 62.327 | 1.00 45.51 |
| ATOM | 3992 | N | CYS | B | 465 | 47.534 | -2.103 | 63.489 | 1.00 42.92 |
| ATOM | 3993 | CA | CYS | B | 465 | 46.757 | -0.859 | 63.428 | 1.00 38.66 |
| ATOM | 3994 | CB | CYS | B | 465 | 45.573 | -1.033 | 62.450 | 1.00 37.19 |
| ATOM | 3995 | SG | CYS | B | 465 | 44.256 | 0.265 | 62.446 | 1.00 33.11 |
| ATOM | 3996 | C | CYS | B | 465 | 46.235 | -0.542 | 64.832 | 1.00 36.98 |
| ATOM | 3997 | O | CYS | B | 465 | 45.665 | -1.406 | 65.486 | 1.00 37.10 |
| ATOM | 3998 | N | PRO | B | 466 | 46.479 | 0.677 | 65.342 | 1.00 35.06 |
| ATOM | 3999 | CD | PRO | B | 466 | 47.355 | 1.727 | 64.797 | 1.00 33.45 |
| ATOM | 4000 | CA | PRO | B | 466 | 45.993 | 1.035 | 66.684 | 1.00 33.99 |
| ATOM | 4001 | CB | PRO | B | 466 | 46.500 | 2.466 | 66.854 | 1.00 33.19 |
| ATOM | 4002 | CG | PRO | B | 466 | 47.740 | 2.479 | 66.037 | 1.00 33.67 |
| ATOM | 4003 | C | PRO | B | 466 | 44.454 | 0.975 | 66.788 | 1.00 33.58 |
| ATOM | 4004 | O | PRO | B | 466 | 43.757 | 1.248 | 65.819 | 1.00 33.99 |
| ATOM | 4005 | N | GLU | B | 467 | 43.923 | 0.643 | 67.963 | 1.00 33.60 |
| ATOM | 4006 | CA | GLU | B | 467 | 42.473 | 0.567 | 68.129 | 1.00 33.37 |
| ATOM | 4007 | CB | GLU | B | 467 | 42.073 | -0.092 | 69.456 | 1.00 33.92 |

Figure 8

| ATOM | 4008 | CG  | GLU | B | 467 | 41.392 | -1.475 | 69.293 | 1.00 | 36.22 |
|------|------|-----|-----|---|-----|--------|--------|--------|------|-------|
| ATOM | 4009 | CD  | GLU | B | 467 | 39.946 | -1.427 | 68.745 | 1.00 | 36.57 |
| ATOM | 4010 | OE1 | GLU | B | 467 | 39.654 | -2.143 | 67.756 | 1.00 | 37.24 |
| ATOM | 4011 | OE2 | GLU | B | 467 | 39.088 | -0.727 | 69.331 | 1.00 | 36.28 |
| ATOM | 4012 | C   | GLU | B | 467 | 41.831 |  1.933 | 68.016 | 1.00 | 32.66 |
| ATOM | 4013 | O   | GLU | B | 467 | 40.679 |  2.036 | 67.623 | 1.00 | 32.70 |
| ATOM | 4014 | N   | GLU | B | 468 | 42.570 |  2.986 | 68.341 | 1.00 | 32.02 |
| ATOM | 4015 | CA  | GLU | B | 468 | 42.000 |  4.316 | 68.223 | 1.00 | 32.26 |
| ATOM | 4016 | CB  | GLU | B | 468 | 42.827 |  5.373 | 68.954 | 1.00 | 35.27 |
| ATOM | 4017 | CG  | GLU | B | 468 | 42.972 |  5.156 | 70.437 | 1.00 | 39.65 |
| ATOM | 4018 | CD  | GLU | B | 468 | 43.915 |  4.007 | 70.763 | 1.00 | 43.11 |
| ATOM | 4019 | OE1 | GLU | B | 468 | 44.878 |  3.748 | 69.980 | 1.00 | 43.89 |
| ATOM | 4020 | OE2 | GLU | B | 468 | 43.682 |  3.363 | 71.813 | 1.00 | 45.31 |
| ATOM | 4021 | C   | GLU | B | 468 | 41.895 |  4.692 | 66.753 | 1.00 | 31.33 |
| ATOM | 4022 | O   | GLU | B | 468 | 41.033 |  5.471 | 66.382 | 1.00 | 32.11 |
| ATOM | 4023 | N   | LEU | B | 469 | 42.800 |  4.175 | 65.921 | 1.00 | 29.63 |
| ATOM | 4024 | CA  | LEU | B | 469 | 42.755 |  4.474 | 64.493 | 1.00 | 27.95 |
| ATOM | 4025 | CB  | LEU | B | 469 | 44.068 |  4.104 | 63.793 | 1.00 | 26.75 |
| ATOM | 4026 | CG  | LEU | B | 469 | 44.182 |  4.343 | 62.286 | 1.00 | 25.35 |
| ATOM | 4027 | CD1 | LEU | B | 469 | 43.993 |  5.802 | 61.939 | 1.00 | 25.51 |
| ATOM | 4028 | CD2 | LEU | B | 469 | 45.536 |  3.899 | 61.843 | 1.00 | 26.01 |
| ATOM | 4029 | C   | LEU | B | 469 | 41.592 |  3.704 | 63.881 | 1.00 | 27.39 |
| ATOM | 4030 | O   | LEU | B | 469 | 40.891 |  4.226 | 63.005 | 1.00 | 27.29 |
| ATOM | 4031 | N   | TYR | B | 470 | 41.364 |  2.488 | 64.383 | 1.00 | 26.13 |
| ATOM | 4032 | CA  | TYR | B | 470 | 40.274 |  1.649 | 63.886 | 1.00 | 25.37 |
| ATOM | 4033 | CB  | TYR | B | 470 | 40.312 |  0.241 | 64.468 | 1.00 | 23.71 |
| ATOM | 4034 | CG  | TYR | B | 470 | 39.195 | -0.634 | 63.918 | 1.00 | 23.88 |
| ATOM | 4035 | CD1 | TYR | B | 470 | 39.110 | -0.906 | 62.548 | 1.00 | 22.15 |
| ATOM | 4036 | CE1 | TYR | B | 470 | 38.116 | -1.729 | 62.039 | 1.00 | 22.32 |
| ATOM | 4037 | CD2 | TYR | B | 470 | 38.240 | -1.209 | 64.760 | 1.00 | 23.17 |
| ATOM | 4038 | CE2 | TYR | B | 470 | 37.235 | -2.040 | 64.250 | 1.00 | 22.21 |
| ATOM | 4039 | CZ  | TYR | B | 470 | 37.179 | -2.297 | 62.895 | 1.00 | 23.09 |
| ATOM | 4040 | OH  | TYR | B | 470 | 36.197 | -3.135 | 62.395 | 1.00 | 22.32 |
| ATOM | 4041 | C   | TYR | B | 470 | 38.924 |  2.253 | 64.203 | 1.00 | 25.78 |
| ATOM | 4042 | O   | TYR | B | 470 | 37.995 |  2.195 | 63.391 | 1.00 | 26.48 |
| ATOM | 4043 | N   | GLN | B | 471 | 38.803 |  2.804 | 65.404 | 1.00 | 25.92 |
| ATOM | 4044 | CA  | GLN | B | 471 | 37.557 |  3.418 | 65.793 | 1.00 | 25.50 |
| ATOM | 4045 | CB  | GLN | B | 471 | 37.526 |  3.660 | 67.303 | 1.00 | 25.49 |
| ATOM | 4046 | CG  | GLN | B | 471 | 37.381 |  2.348 | 68.114 | 1.00 | 26.26 |
| ATOM | 4047 | CD  | GLN | B | 471 | 36.223 |  1.408 | 67.630 | 1.00 | 28.42 |
| ATOM | 4048 | OE1 | GLN | B | 471 | 35.123 |  1.859 | 67.236 | 1.00 | 27.13 |
| ATOM | 4049 | NE2 | GLN | B | 471 | 36.478 |  0.100 | 67.685 | 1.00 | 27.24 |
| ATOM | 4050 | C   | GLN | B | 471 | 37.296 |  4.676 | 64.957 | 1.00 | 25.00 |
| ATOM | 4051 | O   | GLN | B | 471 | 36.151 |  5.054 | 64.746 | 1.00 | 25.30 |
| ATOM | 4052 | N   | LEU | B | 472 | 38.356 |  5.253 | 64.398 | 1.00 | 24.68 |
| ATOM | 4053 | CA  | LEU | B | 472 | 38.229 |  6.429 | 63.542 | 1.00 | 24.20 |
| ATOM | 4054 | CB  | LEU | B | 472 | 39.569 |  7.135 | 63.383 | 1.00 | 25.14 |
| ATOM | 4055 | CG  | LEU | B | 472 | 39.521 |  8.656 | 63.256 | 1.00 | 25.87 |
| ATOM | 4056 | CD1 | LEU | B | 472 | 39.125 |  9.291 | 64.577 | 1.00 | 24.60 |
| ATOM | 4057 | CD2 | LEU | B | 472 | 40.892 |  9.149 | 62.833 | 1.00 | 27.28 |
| ATOM | 4058 | C   | LEU | B | 472 | 37.741 |  5.942 | 62.184 | 1.00 | 23.89 |
| ATOM | 4059 | O   | LEU | B | 472 | 36.898 |  6.589 | 61.554 | 1.00 | 25.19 |
| ATOM | 4060 | N   | MET | B | 473 | 38.269 |  4.806 | 61.730 | 1.00 | 21.67 |
| ATOM | 4061 | CA  | MET | B | 473 | 37.829 |  4.225 | 60.467 | 1.00 | 20.95 |
| ATOM | 4062 | CB  | MET | B | 473 | 38.589 |  2.936 | 60.193 | 1.00 | 20.04 |
| ATOM | 4063 | CG  | MET | B | 473 | 40.044 |  3.103 | 59.858 | 1.00 | 20.15 |
| ATOM | 4064 | SD  | MET | B | 473 | 40.808 |  1.479 | 59.790 | 1.00 | 21.31 |
| ATOM | 4065 | CE  | MET | B | 473 | 42.554 |  1.928 | 59.502 | 1.00 | 19.42 |
| ATOM | 4066 | C   | MET | B | 473 | 36.327 |  3.902 | 60.542 | 1.00 | 20.51 |
| ATOM | 4067 | O   | MET | B | 473 | 35.579 |  4.125 | 59.597 | 1.00 | 20.74 |

Figure 8

| ATOM | 4068 | N   | ARG | B | 474 | 35.894 | 3.380  | 61.682 | 1.00 | 20.82 |
|------|------|-----|-----|---|-----|--------|--------|--------|------|-------|
| ATOM | 4069 | CA  | ARG | B | 474 | 34.505 | 3.014  | 61.880 | 1.00 | 21.55 |
| ATOM | 4070 | CB  | ARG | B | 474 | 34.366 | 2.185  | 63.163 | 1.00 | 22.33 |
| ATOM | 4071 | CG  | ARG | B | 474 | 35.045 | 0.795  | 63.083 | 1.00 | 22.59 |
| ATOM | 4072 | CD  | ARG | B | 474 | 34.516 | -0.046 | 61.895 | 1.00 | 23.27 |
| ATOM | 4073 | NE  | ARG | B | 474 | 33.089 | -0.352 | 62.037 | 1.00 | 22.75 |
| ATOM | 4074 | CZ  | ARG | B | 474 | 32.601 | -1.359 | 62.756 | 1.00 | 22.86 |
| ATOM | 4075 | NH1 | ARG | B | 474 | 33.410 | -2.186 | 63.401 | 1.00 | 23.07 |
| ATOM | 4076 | NH2 | ARG | B | 474 | 31.292 | -1.518 | 62.869 | 1.00 | 22.72 |
| ATOM | 4077 | C   | ARG | B | 474 | 33.548 | 4.213  | 61.865 | 1.00 | 22.17 |
| ATOM | 4078 | O   | ARG | B | 474 | 32.372 | 4.067  | 61.537 | 1.00 | 22.08 |
| ATOM | 4079 | N   | LEU | B | 475 | 34.057 | 5.394  | 62.214 | 1.00 | 22.36 |
| ATOM | 4080 | CA  | LEU | B | 475 | 33.259 | 6.624  | 62.200 | 1.00 | 22.55 |
| ATOM | 4081 | CB  | LEU | B | 475 | 33.906 | 7.723  | 63.045 | 1.00 | 21.32 |
| ATOM | 4082 | CG  | LEU | B | 475 | 33.875 | 7.501  | 64.563 | 1.00 | 22.13 |
| ATOM | 4083 | CD1 | LEU | B | 475 | 34.628 | 8.615  | 65.275 | 1.00 | 20.68 |
| ATOM | 4084 | CD2 | LEU | B | 475 | 32.445 | 7.441  | 65.066 | 1.00 | 21.02 |
| ATOM | 4085 | C   | LEU | B | 475 | 33.129 | 7.078  | 60.750 | 1.00 | 23.54 |
| ATOM | 4086 | O   | LEU | B | 475 | 32.107 | 7.626  | 60.345 | 1.00 | 25.08 |
| ATOM | 4087 | N   | CYS | B | 476 | 34.163 | 6.815  | 59.959 | 1.00 | 23.50 |
| ATOM | 4088 | CA  | CYS | B | 476 | 34.147 | 7.161  | 58.545 | 1.00 | 22.10 |
| ATOM | 4089 | CB  | CYS | B | 476 | 35.551 | 7.027  | 57.940 | 1.00 | 21.15 |
| ATOM | 4090 | SG  | CYS | B | 476 | 36.848 | 8.111  | 58.632 | 1.00 | 23.19 |
| ATOM | 4091 | C   | CYS | B | 476 | 33.188 | 6.213  | 57.821 | 1.00 | 21.76 |
| ATOM | 4092 | O   | CYS | B | 476 | 32.666 | 6.554  | 56.759 | 1.00 | 21.44 |
| ATOM | 4093 | N   | TRP | B | 477 | 32.939 | 5.039  | 58.410 | 1.00 | 21.62 |
| ATOM | 4094 | CA  | TRP | B | 477 | 32.050 | 4.046  | 57.798 | 1.00 | 21.77 |
| ATOM | 4095 | CB  | TRP | B | 477 | 32.680 | 2.644  | 57.821 | 1.00 | 20.77 |
| ATOM | 4096 | CG  | TRP | B | 477 | 34.047 | 2.586  | 57.223 | 1.00 | 21.23 |
| ATOM | 4097 | CD2 | TRP | B | 477 | 35.096 | 1.656  | 57.538 | 1.00 | 22.39 |
| ATOM | 4098 | CE2 | TRP | B | 477 | 36.215 | 2.004  | 56.740 | 1.00 | 23.26 |
| ATOM | 4099 | CE3 | TRP | B | 477 | 35.205 | 0.558  | 58.415 | 1.00 | 23.04 |
| ATOM | 4100 | CD1 | TRP | B | 477 | 34.554 | 3.424  | 56.276 | 1.00 | 22.15 |
| ATOM | 4101 | NE1 | TRP | B | 477 | 35.850 | 3.087  | 55.977 | 1.00 | 21.35 |
| ATOM | 4102 | CZ2 | TRP | B | 477 | 37.443 | 1.293  | 56.793 | 1.00 | 22.86 |
| ATOM | 4103 | CZ3 | TRP | B | 477 | 36.421 | -0.146 | 58.470 | 1.00 | 22.69 |
| ATOM | 4104 | CH2 | TRP | B | 477 | 37.523 | 0.230  | 57.661 | 1.00 | 22.27 |
| ATOM | 4105 | C   | TRP | B | 477 | 30.637 | 3.979  | 58.393 | 1.00 | 22.48 |
| ATOM | 4106 | O   | TRP | B | 477 | 29.961 | 2.959  | 58.241 | 1.00 | 24.19 |
| ATOM | 4107 | N   | LYS | B | 478 | 30.187 | 5.033  | 59.073 | 1.00 | 21.82 |
| ATOM | 4108 | CA  | LYS | B | 478 | 28.839 | 5.030  | 59.624 | 1.00 | 21.65 |
| ATOM | 4109 | CB  | LYS | B | 478 | 28.538 | 6.320  | 60.388 | 1.00 | 21.78 |
| ATOM | 4110 | CG  | LYS | B | 478 | 29.312 | 6.481  | 61.681 | 1.00 | 23.10 |
| ATOM | 4111 | CD  | LYS | B | 478 | 29.037 | 5.358  | 62.641 | 1.00 | 22.56 |
| ATOM | 4112 | CE  | LYS | B | 478 | 27.645 | 5.463  | 63.178 | 1.00 | 24.11 |
| ATOM | 4113 | NZ  | LYS | B | 478 | 27.341 | 4.310  | 64.065 | 1.00 | 28.05 |
| ATOM | 4114 | C   | LYS | B | 478 | 27.905 | 4.921  | 58.443 | 1.00 | 22.22 |
| ATOM | 4115 | O   | LYS | B | 478 | 28.181 | 5.468  | 57.384 | 1.00 | 23.17 |
| ATOM | 4116 | N   | GLU | B | 479 | 26.802 | 4.204  | 58.612 | 1.00 | 23.55 |
| ATOM | 4117 | CA  | GLU | B | 479 | 25.857 | 4.028  | 57.516 | 1.00 | 23.63 |
| ATOM | 4118 | CB  | GLU | B | 479 | 24.689 | 3.139  | 57.927 | 1.00 | 22.67 |
| ATOM | 4119 | CG  | GLU | B | 479 | 23.812 | 2.735  | 56.756 | 1.00 | 22.78 |
| ATOM | 4120 | CD  | GLU | B | 479 | 24.566 | 1.926  | 55.696 | 1.00 | 24.52 |
| ATOM | 4121 | OE1 | GLU | B | 479 | 25.450 | 1.106  | 56.050 | 1.00 | 23.01 |
| ATOM | 4122 | OE2 | GLU | B | 479 | 24.261 | 2.112  | 54.496 | 1.00 | 25.50 |
| ATOM | 4123 | C   | GLU | B | 479 | 25.336 | 5.352  | 57.000 | 1.00 | 23.83 |
| ATOM | 4124 | O   | GLU | B | 479 | 25.359 | 5.596  | 55.803 | 1.00 | 25.36 |
| ATOM | 4125 | N   | ARG | B | 480 | 24.890 | 6.214  | 57.901 | 1.00 | 23.50 |
| ATOM | 4126 | CA  | ARG | B | 480 | 24.360 | 7.512  | 57.501 | 1.00 | 22.59 |
| ATOM | 4127 | CB  | ARG | B | 480 | 23.386 | 8.010  | 58.538 | 1.00 | 25.16 |

Figure 8

| | | | | | | | | | |
|---|---|---|---|---|---|---|---|---|---|
| ATOM | 4128 | CG | ARG | B | 480 | 22.188 | 7.171 | 58.742 | 1.00 27.75 |
| ATOM | 4129 | CD | ARG | B | 480 | 21.520 | 7.774 | 59.924 | 1.00 34.02 |
| ATOM | 4130 | NE | ARG | B | 480 | 20.351 | 7.040 | 60.365 | 1.00 40.66 |
| ATOM | 4131 | CZ | ARG | B | 480 | 20.031 | 6.870 | 61.645 | 1.00 43.72 |
| ATOM | 4132 | NH1 | ARG | B | 480 | 20.803 | 7.377 | 62.611 | 1.00 43.83 |
| ATOM | 4133 | NH2 | ARG | B | 480 | 18.913 | 6.227 | 61.960 | 1.00 45.57 |
| ATOM | 4134 | C | ARG | B | 480 | 25.479 | 8.524 | 57.385 | 1.00 20.98 |
| ATOM | 4135 | O | ARG | B | 480 | 26.222 | 8.708 | 58.322 | 1.00 19.88 |
| ATOM | 4136 | N | PRO | B | 481 | 25.534 | 9.269 | 56.267 | 1.00 21.09 |
| ATOM | 4137 | CD | PRO | B | 481 | 24.483 | 9.257 | 55.228 | 1.00 20.16 |
| ATOM | 4138 | CA | PRO | B | 481 | 26.532 | 10.296 | 55.955 | 1.00 20.81 |
| ATOM | 4139 | CB | PRO | B | 481 | 25.953 | 10.948 | 54.693 | 1.00 20.51 |
| ATOM | 4140 | CG | PRO | B | 481 | 25.179 | 9.865 | 54.059 | 1.00 18.98 |
| ATOM | 4141 | C | PRO | B | 481 | 26.719 | 11.340 | 57.052 | 1.00 21.63 |
| ATOM | 4142 | O | PRO | B | 481 | 27.841 | 11.776 | 57.308 | 1.00 21.44 |
| ATOM | 4143 | N | GLU | B | 482 | 25.618 | 11.734 | 57.694 | 1.00 22.15 |
| ATOM | 4144 | CA | GLU | B | 482 | 25.640 | 12.752 | 58.747 | 1.00 22.20 |
| ATOM | 4145 | CB | GLU | B | 482 | 24.209 | 13.143 | 59.133 | 1.00 22.91 |
| ATOM | 4146 | CG | GLU | B | 482 | 23.458 | 12.027 | 59.845 | 1.00 24.00 |
| ATOM | 4147 | CD | GLU | B | 482 | 22.363 | 11.396 | 59.007 | 1.00 24.48 |
| ATOM | 4148 | OE1 | GLU | B | 482 | 22.510 | 11.304 | 57.765 | 1.00 23.15 |
| ATOM | 4149 | OE2 | GLU | B | 482 | 21.341 | 10.997 | 59.616 | 1.00 26.08 |
| ATOM | 4150 | C | GLU | B | 482 | 26.403 | 12.307 | 59.989 | 1.00 21.31 |
| ATOM | 4151 | O | GLU | B | 482 | 26.897 | 13.129 | 60.758 | 1.00 21.85 |
| ATOM | 4152 | N | ASP | B | 483 | 26.475 | 10.999 | 60.192 | 1.00 21.17 |
| ATOM | 4153 | CA | ASP | B | 483 | 27.173 | 10.422 | 61.333 | 1.00 20.30 |
| ATOM | 4154 | CB | ASP | B | 483 | 26.607 | 9.032 | 61.649 | 1.00 20.87 |
| ATOM | 4155 | CG | ASP | B | 483 | 25.179 | 9.086 | 62.193 | 1.00 21.74 |
| ATOM | 4156 | OD1 | ASP | B | 483 | 24.807 | 10.093 | 62.814 | 1.00 21.25 |
| ATOM | 4157 | OD2 | ASP | B | 483 | 24.420 | 8.124 | 61.996 | 1.00 23.25 |
| ATOM | 4158 | C | ASP | B | 483 | 28.674 | 10.328 | 61.118 | 1.00 19.47 |
| ATOM | 4159 | O | ASP | B | 483 | 29.398 | 9.962 | 62.028 | 1.00 20.30 |
| ATOM | 4160 | N | ARG | B | 484 | 29.138 | 10.633 | 59.912 | 1.00 19.15 |
| ATOM | 4161 | CA | ARG | B | 484 | 30.570 | 10.591 | 59.593 | 1.00 19.66 |
| ATOM | 4162 | CB | ARG | B | 484 | 30.768 | 10.266 | 58.096 | 1.00 18.19 |
| ATOM | 4163 | CG | ARG | B | 484 | 30.118 | 8.970 | 57.675 | 1.00 15.37 |
| ATOM | 4164 | CD | ARG | B | 484 | 30.229 | 8.743 | 56.185 | 1.00 16.29 |
| ATOM | 4165 | NE | ARG | B | 484 | 29.330 | 7.664 | 55.753 | 1.00 18.07 |
| ATOM | 4166 | CZ | ARG | B | 484 | 28.748 | 7.568 | 54.553 | 1.00 17.07 |
| ATOM | 4167 | NH1 | ARG | B | 484 | 28.965 | 8.474 | 53.624 | 1.00 15.88 |
| ATOM | 4168 | NH2 | ARG | B | 484 | 27.891 | 6.587 | 54.303 | 1.00 16.33 |
| ATOM | 4169 | C | ARG | B | 484 | 31.243 | 11.929 | 59.973 | 1.00 19.94 |
| ATOM | 4170 | O | ARG | B | 484 | 30.636 | 12.996 | 59.843 | 1.00 19.58 |
| ATOM | 4171 | N | PRO | B | 485 | 32.501 | 11.885 | 60.458 | 1.00 20.13 |
| ATOM | 4172 | CD | PRO | B | 485 | 33.362 | 10.703 | 60.605 | 1.00 20.12 |
| ATOM | 4173 | CA | PRO | B | 485 | 33.223 | 13.099 | 60.855 | 1.00 20.41 |
| ATOM | 4174 | CB | PRO | B | 485 | 34.544 | 12.549 | 61.404 | 1.00 21.61 |
| ATOM | 4175 | CG | PRO | B | 485 | 34.257 | 11.128 | 61.714 | 1.00 22.23 |
| ATOM | 4176 | C | PRO | B | 485 | 33.523 | 14.042 | 59.695 | 1.00 21.14 |
| ATOM | 4177 | O | PRO | B | 485 | 33.474 | 13.649 | 58.526 | 1.00 21.53 |
| ATOM | 4178 | N | THR | B | 486 | 33.830 | 15.292 | 60.022 | 1.00 19.94 |
| ATOM | 4179 | CA | THR | B | 486 | 34.217 | 16.245 | 58.996 | 1.00 20.18 |
| ATOM | 4180 | CB | THR | B | 486 | 34.050 | 17.687 | 59.464 | 1.00 18.76 |
| ATOM | 4181 | OG1 | THR | B | 486 | 34.676 | 17.841 | 60.735 | 1.00 19.31 |
| ATOM | 4182 | CG2 | THR | B | 486 | 32.603 | 18.046 | 59.568 | 1.00 15.80 |
| ATOM | 4183 | C | THR | B | 486 | 35.714 | 15.984 | 58.800 | 1.00 20.82 |
| ATOM | 4184 | O | THR | B | 486 | 36.345 | 15.376 | 59.668 | 1.00 21.88 |
| ATOM | 4185 | N | PHE | B | 487 | 36.278 | 16.379 | 57.663 | 1.00 20.71 |
| ATOM | 4186 | CA | PHE | B | 487 | 37.708 | 16.184 | 57.460 | 1.00 20.45 |
| ATOM | 4187 | CB | PHE | B | 487 | 38.098 | 16.472 | 56.027 | 1.00 18.79 |

Figure 8

```
ATOM   4188  CG   PHE B 487      37.827  15.343  55.102  1.00 18.42
ATOM   4189  CD1  PHE B 487      38.610  14.186  55.155  1.00 16.94
ATOM   4190  CD2  PHE B 487      36.822  15.434  54.145  1.00 17.83
ATOM   4191  CE1  PHE B 487      38.404  13.148  54.275  1.00 13.86
ATOM   4192  CE2  PHE B 487      36.607  14.392  53.252  1.00 17.19
ATOM   4193  CZ   PHE B 487      37.404  13.244  53.319  1.00 16.38
ATOM   4194  C    PHE B 487      38.428  17.138  58.379  1.00 21.55
ATOM   4195  O    PHE B 487      39.564  16.919  58.763  1.00 21.63
ATOM   4196  N    ASP B 488      37.736  18.205  58.742  1.00 23.84
ATOM   4197  CA   ASP B 488      38.285  19.199  59.649  1.00 26.01
ATOM   4198  CB   ASP B 488      37.259  20.314  59.842  1.00 28.39
ATOM   4199  CG   ASP B 488      37.667  21.311  60.887  1.00 31.52
ATOM   4200  OD1  ASP B 488      38.867  21.666  60.944  1.00 35.19
ATOM   4201  OD2  ASP B 488      36.777  21.747  61.649  1.00 32.80
ATOM   4202  C    ASP B 488      38.597  18.487  60.962  1.00 26.63
ATOM   4203  O    ASP B 488      39.650  18.695  61.555  1.00 28.05
ATOM   4204  N    TYR B 489      37.716  17.574  61.363  1.00 26.44
ATOM   4205  CA   TYR B 489      37.908  16.821  62.586  1.00 25.51
ATOM   4206  CB   TYR B 489      36.607  16.150  63.016  1.00 23.88
ATOM   4207  CG   TYR B 489      36.803  15.150  64.121  1.00 20.99
ATOM   4208  CD1  TYR B 489      37.152  15.561  65.404  1.00 20.71
ATOM   4209  CE1  TYR B 489      37.423  14.631  66.416  1.00 19.41
ATOM   4210  CD2  TYR B 489      36.719  13.782  63.867  1.00 20.60
ATOM   4211  CE2  TYR B 489      36.990  12.843  64.856  1.00 18.63
ATOM   4212  CZ   TYR B 489      37.345  13.271  66.126  1.00 20.13
ATOM   4213  OH   TYR B 489      37.670  12.338  67.091  1.00 21.42
ATOM   4214  C    TYR B 489      38.988  15.771  62.392  1.00 26.64
ATOM   4215  O    TYR B 489      39.852  15.611  63.258  1.00 28.04
ATOM   4216  N    LEU B 490      38.918  15.030  61.288  1.00 26.20
ATOM   4217  CA   LEU B 490      39.907  14.002  60.986  1.00 26.57
ATOM   4218  CB   LEU B 490      39.585  13.301  59.664  1.00 25.78
ATOM   4219  CG   LEU B 490      38.308  12.455  59.642  1.00 24.78
ATOM   4220  CD1  LEU B 490      38.097  11.872  58.260  1.00 23.16
ATOM   4221  CD2  LEU B 490      38.380  11.361  60.697  1.00 23.73
ATOM   4222  C    LEU B 490      41.343  14.531  60.970  1.00 27.94
ATOM   4223  O    LEU B 490      42.254  13.849  61.440  1.00 28.42
ATOM   4224  N    ARG B 491      41.558  15.745  60.460  1.00 29.41
ATOM   4225  CA   ARG B 491      42.911  16.312  60.442  1.00 30.79
ATOM   4226  CB   ARG B 491      42.959  17.608  59.646  1.00 31.61
ATOM   4227  CG   ARG B 491      44.294  18.333  59.765  1.00 34.35
ATOM   4228  CD   ARG B 491      44.168  19.800  59.381  1.00 38.43
ATOM   4229  NE   ARG B 491      42.986  20.404  59.999  1.00 41.83
ATOM   4230  CZ   ARG B 491      42.870  20.677  61.297  1.00 43.21
ATOM   4231  NH1  ARG B 491      43.877  20.423  62.140  1.00 41.81
ATOM   4232  NH2  ARG B 491      41.711  21.134  61.761  1.00 43.36
ATOM   4233  C    ARG B 491      43.382  16.569  61.877  1.00 31.54
ATOM   4234  O    ARG B 491      44.487  16.172  62.256  1.00 31.18
ATOM   4235  N    SER B 492      42.506  17.188  62.675  1.00 31.96
ATOM   4236  CA   SER B 492      42.769  17.500  64.078  1.00 31.95
ATOM   4237  CB   SER B 492      41.496  17.990  64.769  1.00 31.72
ATOM   4238  OG   SER B 492      41.240  19.346  64.470  1.00 33.49
ATOM   4239  C    SER B 492      43.253  16.290  64.834  1.00 32.20
ATOM   4240  O    SER B 492      44.309  16.316  65.452  1.00 32.25
ATOM   4241  N    VAL B 493      42.450  15.231  64.791  1.00 33.30
ATOM   4242  CA   VAL B 493      42.752  13.996  65.506  1.00 33.69
ATOM   4243  CB   VAL B 493      41.476  13.118  65.670  1.00 33.01
ATOM   4244  CG1  VAL B 493      40.903  12.779  64.332  1.00 33.01
ATOM   4245  CG2  VAL B 493      41.785  11.849  66.469  1.00 34.01
ATOM   4246  C    VAL B 493      43.950  13.185  64.990  1.00 34.31
ATOM   4247  O    VAL B 493      44.617  12.505  65.780  1.00 34.65
```

Figure 8

```
ATOM   4248  N    LEU B 494      44.258  13.285  63.694  1.00 35.08
ATOM   4249  CA   LEU B 494      45.404  12.567  63.128  1.00 35.54
ATOM   4250  CB   LEU B 494      45.230  12.369  61.618  1.00 33.35
ATOM   4251  CG   LEU B 494      44.216  11.287  61.248  1.00 32.13
ATOM   4252  CD1  LEU B 494      43.942  11.311  59.769  1.00 29.61
ATOM   4253  CD2  LEU B 494      44.730   9.928  61.709  1.00 31.30
ATOM   4254  C    LEU B 494      46.729  13.275  63.431  1.00 36.75
ATOM   4255  O    LEU B 494      47.758  12.627  63.624  1.00 35.78
ATOM   4256  N    GLU B 495      46.684  14.604  63.511  1.00 38.96
ATOM   4257  CA   GLU B 495      47.869  15.401  63.798  1.00 41.61
ATOM   4258  CB   GLU B 495      47.577  16.889  63.605  1.00 42.04
ATOM   4259  CG   GLU B 495      47.303  17.301  62.170  1.00 43.96
ATOM   4260  CD   GLU B 495      47.241  18.810  61.977  1.00 44.48
ATOM   4261  OE1  GLU B 495      46.980  19.535  62.970  1.00 44.76
ATOM   4262  OE2  GLU B 495      47.440  19.256  60.819  1.00 43.53
ATOM   4263  C    GLU B 495      48.330  15.198  65.227  1.00 43.55
ATOM   4264  O    GLU B 495      49.530  15.124  65.504  1.00 44.37
ATOM   4265  N    ASP B 496      47.359  15.103  66.130  1.00 45.07
ATOM   4266  CA   ASP B 496      47.627  14.956  67.553  1.00 46.78
ATOM   4267  CB   ASP B 496      46.639  15.822  68.343  1.00 47.27
ATOM   4268  CG   ASP B 496      46.590  17.279  67.850  1.00 49.36
ATOM   4269  OD1  ASP B 496      47.645  17.852  67.468  1.00 48.61
ATOM   4270  OD2  ASP B 496      45.474  17.855  67.853  1.00 50.95
ATOM   4271  C    ASP B 496      47.545  13.523  68.059  1.00 48.23
ATOM   4272  O    ASP B 496      47.516  13.298  69.267  1.00 48.94
ATOM   4273  N    PHE B 497      47.576  12.555  67.149  1.00 49.45
ATOM   4274  CA   PHE B 497      47.455  11.154  67.524  1.00 50.97
ATOM   4275  CB   PHE B 497      47.567  10.263  66.297  1.00 49.58
ATOM   4276  CG   PHE B 497      46.720   9.041  66.375  1.00 47.98
ATOM   4277  CD1  PHE B 497      45.348   9.117  66.158  1.00 47.22
ATOM   4278  CD2  PHE B 497      47.291   7.811  66.669  1.00 48.49
ATOM   4279  CE1  PHE B 497      44.553   7.987  66.229  1.00 47.61
ATOM   4280  CE2  PHE B 497      46.514   6.663  66.745  1.00 48.96
ATOM   4281  CZ   PHE B 497      45.138   6.750  66.524  1.00 49.12
ATOM   4282  C    PHE B 497      48.392  10.681  68.632  1.00 52.99
ATOM   4283  O    PHE B 497      47.974   9.932  69.513  1.00 53.90
ATOM   4284  N    PHE B 498      49.660  11.074  68.568  1.00 55.02
ATOM   4285  CA   PHE B 498      50.625  10.708  69.615  1.00 57.20
ATOM   4286  CB   PHE B 498      50.853   9.174  69.742  1.00 57.52
ATOM   4287  CG   PHE B 498      51.094   8.449  68.427  1.00 57.40
ATOM   4288  CD1  PHE B 498      51.734   9.074  67.359  1.00 57.05
ATOM   4289  CD2  PHE B 498      50.656   7.130  68.265  1.00 56.94
ATOM   4290  CE1  PHE B 498      51.929   8.403  66.162  1.00 57.41
ATOM   4291  CE2  PHE B 498      50.846   6.448  67.075  1.00 56.39
ATOM   4292  CZ   PHE B 498      51.481   7.085  66.021  1.00 57.42
ATOM   4293  C    PHE B 498      51.949  11.458  69.500  1.00 57.83
ATOM   4294  O    PHE B 498      51.943  12.608  69.991  1.00 58.28
ATOM   4295  N1   LIG B 500      52.742  14.832  39.342  1.00 29.87
ATOM   4296  C1   LIG B 500      53.348  13.576  39.382  1.00 29.27
ATOM   4297  N2   LIG B 500      54.602  13.452  39.855  1.00 29.60
ATOM   4298  C2   LIG B 500      55.208  12.274  39.915  1.00 28.65
ATOM   4299  N3   LIG B 500      54.630  11.177  39.530  1.00 28.98
ATOM   4300  C3   LIG B 500      53.375  11.191  39.053  1.00 29.31
ATOM   4301  N4   LIG B 500      52.541  10.212  38.580  1.00 28.41
ATOM   4302  C4   LIG B 500      52.802   8.764  38.447  1.00 28.00
ATOM   4303  C5   LIG B 500      52.480   8.223  37.048  1.00 27.29
ATOM   4304  C6   LIG B 500      52.724   6.711  36.979  1.00 27.38
ATOM   4305  C7   LIG B 500      51.865   5.997  38.065  1.00 28.21
ATOM   4306  N5   LIG B 500      52.077   4.536  37.970  1.00 28.76
ATOM   4307  C8   LIG B 500      53.384   4.071  38.484  1.00 28.97
```

Figure 8

| | | | | | | | | | |
|---|---|---|---|---|---|---|---|---|---|
| ATOM | 4308 | C9  | LIG | B | 500 | 53.509 |  2.562 | 38.246 | 1.00 28.86 |
| ATOM | 4309 | N6  | LIG | B | 500 | 52.459 |  1.865 | 39.003 | 1.00 29.26 |
| ATOM | 4310 | C10 | LIG | B | 500 | 52.585 |  0.414 | 38.735 | 1.00 29.32 |
| ATOM | 4311 | C11 | LIG | B | 500 | 51.176 |  2.306 | 38.520 | 1.00 28.92 |
| ATOM | 4312 | C12 | LIG | B | 500 | 51.025 |  3.816 | 38.718 | 1.00 28.89 |
| ATOM | 4313 | C13 | LIG | B | 500 | 52.229 |  6.511 | 39.457 | 1.00 27.51 |
| ATOM | 4314 | C14 | LIG | B | 500 | 51.972 |  8.034 | 39.532 | 1.00 27.75 |
| ATOM | 4315 | C15 | LIG | B | 500 | 51.342 | 10.759 | 38.193 | 1.00 28.49 |
| ATOM | 4316 | C16 | LIG | B | 500 | 51.360 | 12.098 | 38.391 | 1.00 28.91 |
| ATOM | 4317 | C17 | LIG | B | 500 | 50.193 | 12.894 | 38.014 | 1.00 28.87 |
| ATOM | 4318 | C18 | LIG | B | 500 | 50.458 | 13.933 | 37.124 | 1.00 29.09 |
| ATOM | 4319 | C19 | LIG | B | 500 | 49.437 | 14.737 | 36.662 | 1.00 29.68 |
| ATOM | 4320 | O1  | LIG | B | 500 | 49.681 | 15.774 | 35.804 | 1.00 30.48 |
| ATOM | 4321 | C20 | LIG | B | 500 | 50.875 | 15.479 | 35.073 | 1.00 29.76 |
| ATOM | 4322 | C21 | LIG | B | 500 | 48.123 | 14.498 | 37.078 | 1.00 29.84 |
| ATOM | 4323 | N7  | LIG | B | 500 | 47.087 | 15.339 | 36.598 | 1.00 29.79 |
| ATOM | 4324 | C22 | LIG | B | 500 | 45.671 | 15.372 | 36.832 | 1.00 29.91 |
| ATOM | 4325 | C23 | LIG | B | 500 | 45.199 | 16.110 | 38.071 | 1.00 30.60 |
| ATOM | 4326 | O2  | LIG | B | 500 | 43.927 | 16.565 | 38.288 | 1.00 31.41 |
| ATOM | 4327 | C24 | LIG | B | 500 | 43.834 | 17.199 | 39.480 | 1.00 30.67 |
| ATOM | 4328 | C25 | LIG | B | 500 | 42.568 | 17.835 | 40.041 | 1.00 29.64 |
| ATOM | 4329 | C26 | LIG | B | 500 | 45.072 | 17.155 | 40.062 | 1.00 30.71 |
| ATOM | 4330 | C27 | LIG | B | 500 | 45.949 | 16.453 | 39.147 | 1.00 30.90 |
| ATOM | 4331 | C28 | LIG | B | 500 | 47.847 | 13.447 | 37.978 | 1.00 29.39 |
| ATOM | 4332 | C29 | LIG | B | 500 | 48.876 | 12.639 | 38.444 | 1.00 28.56 |
| ATOM | 4333 | C30 | LIG | B | 500 | 52.685 | 12.430 | 38.963 | 1.00 28.75 |
| ATOM | 4334 | OH2 | H2O | B | 600 | 33.956 |  0.424 | 50.976 | 1.00 26.52 |
| ATOM | 4335 | OH2 | H2O | B | 601 | 29.971 | 19.576 | 61.676 | 1.00 72.57 |
| ATOM | 4336 | OH2 | H2O | B | 602 | 27.241 | -1.419 | 59.673 | 1.00 17.51 |
| ATOM | 4337 | OH2 | H2O | B | 604 | 34.748 | 20.181 | 62.944 | 1.00 42.59 |
| ATOM | 4338 | OH2 | H2O | B | 605 | 22.830 | -2.807 | 58.169 | 1.00 55.99 |
| ATOM | 4339 | OH2 | H2O | B | 606 | 36.077 |  9.753 | 47.347 | 1.00 16.56 |
| ATOM | 4340 | OH2 | H2O | B | 607 | 24.743 |  5.757 | 60.781 | 1.00 19.20 |
| ATOM | 4341 | OH2 | H2O | B | 608 | 29.136 | 13.900 | 63.158 | 1.00 60.27 |
| ATOM | 4342 | OH2 | H2O | B | 609 | 27.662 | -7.514 | 58.256 | 1.00 42.11 |
| ATOM | 4343 | OH2 | H2O | B | 610 | 34.625 | -1.545 | 55.861 | 1.00 11.94 |
| ATOM | 4344 | OH2 | H2O | B | 611 | 34.014 |  4.175 | 66.146 | 1.00 17.61 |
| ATOM | 4345 | OH2 | H2O | B | 612 | 29.349 | 17.003 | 59.794 | 1.00 33.65 |
| ATOM | 4346 | OH2 | H2O | B | 613 | 28.275 | -5.844 | 60.647 | 1.00 60.82 |
| ATOM | 4347 | OH2 | H2O | B | 614 | 37.894 | 13.296 | 41.323 | 1.00 19.30 |
| ATOM | 4348 | OH2 | H2O | B | 615 | 19.059 | 14.798 | 62.955 | 1.00 39.79 |
| ATOM | 4349 | OH2 | H2O | B | 616 | 26.718 | 15.903 | 60.378 | 1.00 31.85 |
| ATOM | 4350 | OH2 | H2O | B | 617 | 31.194 | -7.187 | 60.209 | 1.00 78.12 |
| ATOM | 4351 | OH2 | H2O | B | 618 | 37.129 | -2.020 | 44.136 | 1.00 40.13 |
| ATOM | 4352 | OH2 | H2O | B | 619 | 27.344 | 17.691 | 55.803 | 1.00 95.76 |
| ATOM | 4353 | OH2 | H2O | B | 620 | 29.947 | -4.341 | 63.074 | 1.00 23.00 |
| ATOM | 4354 | OH2 | H2O | B | 621 | 58.438 |  9.415 | 39.668 | 1.00 52.30 |
| ATOM | 4355 | OH2 | H2O | B | 622 | 32.256 | 22.149 | 62.038 | 1.00 46.71 |
| ATOM | 4356 | OH2 | H2O | B | 623 | 24.768 | -0.764 | 58.353 | 1.00 28.76 |
| ATOM | 4357 | OH2 | H2O | B | 624 | 64.618 | 10.565 | 37.685 | 1.00 44.55 |
| ATOM | 4358 | OH2 | H2O | B | 625 | 48.677 | 17.728 | 58.681 | 1.00 47.41 |
| ATOM | 4359 | OH2 | H2O | B | 626 | 44.011 |  3.116 | 45.911 | 1.00 31.01 |
| ATOM | 4360 | OH2 | H2O | B | 627 | 32.181 | 16.493 | 56.276 | 1.00 17.86 |
| ATOM | 4361 | OH2 | H2O | B | 628 | 32.551 |  7.120 | 48.563 | 1.00 24.97 |
| ATOM | 4362 | OH2 | H2O | B | 630 | 37.015 |  7.995 | 67.218 | 1.00 65.28 |
| ATOM | 4363 | OH2 | H2O | B | 631 | 62.514 | 23.444 | 26.724 | 1.00 65.64 |
| ATOM | 4364 | OH2 | H2O | B | 632 | 33.967 | -5.153 | 61.565 | 1.00 16.07 |
| ATOM | 4365 | OH2 | H2O | B | 633 | 45.606 | 10.237 | 40.936 | 1.00 48.96 |
| ATOM | 4366 | OH2 | H2O | B | 634 | 45.856 | 23.504 | 55.558 | 1.00 34.07 |
| ATOM | 4367 | OH2 | H2O | B | 635 | 27.171 | 10.972 | 50.497 | 1.00 27.18 |

Figure 8

```
ATOM   4368  OH2 H2O B 636      26.339   10.512  65.073  1.00  28.35
ATOM   4369  OH2 H2O B 638      20.354   14.605  65.497  1.00  40.40
ATOM   4370  OH2 H2O B 639      44.301   12.193  68.521  1.00  40.47
ATOM   4371  OH2 H2O B 640      26.810   -0.814  54.649  1.00  23.63
ATOM   4372  OH2 H2O B 641      25.712   16.360  57.677  1.00  21.22
ATOM   4373  OH2 H2O B 642      48.019   23.277  44.795  1.00  23.66
ATOM   4374  OH2 H2O B 643      55.128    0.047  26.619  1.00 100.00
ATOM   4375  OH2 H2O B 644      31.373    1.646  60.706  1.00  26.32
ATOM   4376  OH2 H2O B 645      24.122   -1.227  50.419  1.00  37.53
ATOM   4377  OH2 H2O B 646      57.234   21.603  18.938  1.00  71.48
ATOM   4378  OH2 H2O B 647      32.976  -13.326  53.274  1.00  55.48
ATOM   4379  OH2 H2O B 648      29.596   17.726  49.611  1.00  26.37
ATOM   4380  OH2 H2O B 649      15.480   17.109  62.342  1.00  67.99
ATOM   4381  OH2 H2O B 650      40.697   -5.387  57.933  1.00  34.74
ATOM   4382  OH2 H2O B 651      31.516   25.101  59.054  1.00  39.38
ATOM   4383  OH2 H2O B 652      27.322    1.925  61.016  1.00  40.67
ATOM   4384  OH2 H2O B 653      32.392    0.157  48.874  1.00  21.41
ATOM   4385  OH2 H2O B 654      31.978   -8.195  64.235  1.00  29.48
ATOM   4386  OH2 H2O B 655      52.660    2.282  33.586  1.00  77.25
ATOM   4387  OH2 H2O B 656      33.180   19.071  43.677  1.00  64.90
ATOM   4388  OH2 H2O B 657      29.908   19.674  53.757  1.00  97.08
ATOM   4389  OH2 H2O B 658      26.501   -2.056  66.477  1.00  58.23
ATOM   4390  OH2 H2O B 659      38.243   -5.404  64.474  1.00  23.01
ATOM   4391  OH2 H2O B 660      54.380    5.111  42.229  1.00  34.53
ATOM   4392  OH2 H2O B 661      43.550    8.021  36.270  1.00  82.72
ATOM   4393  OH2 H2O B 662      22.538   11.960  63.070  1.00  58.97
ATOM   4394  OH2 H2O B 663      35.227  -11.932  56.842  1.00  49.17
ATOM   4395  OH2 H2O B 664      55.883    1.633  40.155  1.00  65.69
ATOM   4396  OH2 H2O B 665      31.052   19.865  56.894  1.00  73.54
ATOM   4397  OH2 H2O B 666      26.224   -1.888  62.224  1.00  42.90
ATOM   4398  OH2 H2O B 667      36.937   21.984  56.449  1.00  36.34
ATOM   4399  OH2 H2O B 668      51.090   -0.368  60.107  1.00  39.48
ATOM   4400  OH2 H2O B 669      33.972   21.523  58.299  1.00  40.24
ATOM   4401  OH2 H2O B 670      22.479   -1.908  61.904  1.00  97.21
ATOM   4402  OH2 H2O B 671      28.212   17.656  47.132  1.00  35.71
ATOM   4403  OH2 H2O B 672      34.914   20.025  41.209  1.00  47.97
ATOM   4404  OH2 H2O B 673      62.537    1.799  48.262  1.00  61.76
ATOM   4405  OH2 H2O B 674      42.885   22.331  55.390  1.00  40.74
ATOM   4406  OH2 H2O B 675      25.962   -2.365  48.865  1.00  38.17
ATOM   4407  OH2 H2O B 676      60.415   18.308  41.634  1.00  51.23
ATOM   4408  OH2 H2O B 677      34.163    7.613  46.153  1.00  35.39
ATOM   4409  OH2 H2O B 678      23.765    4.678  53.332  1.00  41.58
ATOM   4410  OH2 H2O B 679      44.053    1.439  43.694  1.00  41.81
ATOM   4411  OH2 H2O B 680      60.402    6.965  28.123  1.00  57.08
ATOM   4412  OH2 H2O B 681      21.804    3.680  50.333  1.00  46.43
ATOM   4413  OH2 H2O B 682      58.073   20.067  40.403  1.00  32.25
ATOM   4414  OH2 H2O B 683      47.560    5.378  39.460  1.00  42.99
ATOM   4415  OH2 H2O B 684      43.150   -2.425  53.016  1.00  35.03
ATOM   4416  OH2 H2O B 685      24.039   -0.260  52.967  1.00  20.07
ATOM   4417  OH2 H2O B 686      45.547   -0.985  69.574  1.00  54.34
ATOM   4418  OH2 H2O B 687      26.989   -4.243  64.423  1.00  45.50
ATOM   4419  OH2 H2O B 688      62.490    9.998  49.282  1.00  44.38
ATOM   4420  OH2 H2O B 689      24.154   -2.251  46.793  1.00  36.79
ATOM   4421  OH2 H2O B 690      32.816   17.454  26.860  1.00  44.12
ATOM   4422  OH2 H2O B 691      47.374   24.610  40.859  1.00  28.71
ATOM   4423  OH2 H2O B 692      41.112    0.991  42.097  1.00  51.25
ATOM   4424  OH2 H2O B 693      45.171   -0.820  48.074  1.00  25.35
ATOM   4425  OH2 H2O B 694      46.254   22.781  42.802  1.00  37.56
ATOM   4426  OH2 H2O B 695      18.822   11.857  66.574  1.00  37.76
ATOM   4427  OH2 H2O B 696      59.420    6.335  58.824  1.00  47.11
```

Figure 8

```
ATOM   4428  OH2 H2O B 697      39.316    6.437  68.366  1.00 86.14
ATOM   4429  OH2 H2O B 698      53.175   11.277  24.922  1.00 50.20
ATOM   4430  OH2 H2O B 699      22.742    0.740  60.016  1.00 29.65
ATOM   4431  OH2 H2O B 700      34.524   11.931  68.361  1.00 89.72
ATOM   4432  OH2 H2O B 701      62.191   10.134  36.080  1.00 66.36
END
```

Figure 8

```
CRYST1   56.823    44.486   120.154  90.00   90.00   90.00 P21           1
SCALE1      0.017599  0.000000  0.000000        0.00000
SCALE2      0.000000  0.022479  0.000000        0.00000
SCALE3      0.000000  0.000000  0.008323        0.00000
ATOM      1  CB  TRP A 238      18.047  -5.634  27.316  1.00 56.27      A    C
ATOM      2  CG  TRP A 238      17.563  -6.157  25.985  1.00 56.49      A    C
ATOM      3  CD2 TRP A 238      18.036  -5.780  24.677  1.00 56.78      A    C
ATOM      4  CE2 TRP A 238      17.281  -6.511  23.734  1.00 56.69      A    C
ATOM      5  CE3 TRP A 238      19.024  -4.895  24.213  1.00 56.14      A    C
ATOM      6  CD1 TRP A 238      16.570  -7.074  25.780  1.00 56.48      A    C
ATOM      7  NE1 TRP A 238      16.396  -7.290  24.434  1.00 56.52      A    N
ATOM      8  CZ2 TRP A 238      17.482  -6.385  22.352  1.00 56.54      A    C
ATOM      9  CZ3 TRP A 238      19.223  -4.771  22.837  1.00 55.20      A    C
ATOM     10  CH2 TRP A 238      18.455  -5.513  21.925  1.00 55.64      A    C
ATOM     11  C   TRP A 238      19.743  -5.696  29.156  1.00 55.72      A    C
ATOM     12  O   TRP A 238      20.295  -4.601  29.050  1.00 55.61      A    O
ATOM     13  N   TRP A 238      18.840  -7.829  28.170  1.00 55.92      A    N
ATOM     14  CA  TRP A 238      19.224  -6.414  27.910  1.00 55.98      A    C
ATOM     15  N   GLU A 239      19.525  -6.285  30.333  1.00 55.48      A    N
ATOM     16  CA  GLU A 239      20.004  -5.694  31.585  1.00 54.91      A    C
ATOM     17  CB  GLU A 239      19.171  -6.146  32.786  1.00 57.76      A    C
ATOM     18  CG  GLU A 239      18.201  -5.099  33.300  1.00 62.28      A    C
ATOM     19  CD  GLU A 239      16.822  -5.223  32.664  1.00 66.29      A    C
ATOM     20  OE1 GLU A 239      16.596  -4.663  31.558  1.00 67.75      A    O
ATOM     21  OE2 GLU A 239      15.962  -5.900  33.274  1.00 67.97      A    O
ATOM     22  C   GLU A 239      21.449  -6.097  31.815  1.00 53.25      A    C
ATOM     23  O   GLU A 239      21.844  -7.218  31.493  1.00 53.33      A    O
ATOM     24  N   VAL A 240      22.235  -5.173  32.358  1.00 50.98      A    N
ATOM     25  CA  VAL A 240      23.645  -5.415  32.638  1.00 48.18      A    C
ATOM     26  CB  VAL A 240      24.552  -5.001  31.441  1.00 46.76      A    C
ATOM     27  CG1 VAL A 240      24.175  -5.768  30.188  1.00 44.77      A    C
ATOM     28  CG2 VAL A 240      24.465  -3.510  31.195  1.00 45.79      A    C
ATOM     29  C   VAL A 240      24.066  -4.630  33.879  1.00 47.42      A    C
ATOM     30  O   VAL A 240      23.442  -3.625  34.231  1.00 47.14      A    O
ATOM     31  N   PRO A 241      25.099  -5.115  34.590  1.00 46.77      A    N
ATOM     32  CD  PRO A 241      25.676  -6.459  34.410  1.00 46.22      A    C
ATOM     33  CA  PRO A 241      25.633  -4.487  35.802  1.00 46.34      A    C
ATOM     34  CB  PRO A 241      26.633  -5.529  36.304  1.00 46.25      A    C
ATOM     35  CG  PRO A 241      26.053  -6.816  35.816  1.00 46.20      A    C
ATOM     36  C   PRO A 241      26.332  -3.150  35.537  1.00 46.52      A    C
ATOM     37  O   PRO A 241      27.035  -2.992  34.540  1.00 46.44      A    O
ATOM     38  N   ARG A 242      26.142  -2.203  36.454  1.00 46.80      A    N
ATOM     39  CA  ARG A 242      26.748  -0.874  36.376  1.00 47.35      A    C
ATOM     40  CB  ARG A 242      26.444  -0.114  37.674  1.00 48.07      A    C
ATOM     41  CG  ARG A 242      27.102   1.259  37.835  1.00 50.12      A    C
ATOM     42  CD  ARG A 242      26.483   2.319  36.948  1.00 51.76      A    C
ATOM     43  NE  ARG A 242      25.020   2.376  37.048  1.00 54.49      A    N
ATOM     44  CZ  ARG A 242      24.338   2.905  38.061  1.00 54.44      A    C
ATOM     45  NH1 ARG A 242      24.967   3.442  39.097  1.00 55.89      A    N
ATOM     46  NH2 ARG A 242      23.014   2.906  38.030  1.00 54.88      A    N
```

Figure 9

| | | | | | | | | | | | |
|---|---|---|---|---|---|---|---|---|---|---|---|
| ATOM | 47 | C | ARG | A | 242 | 28.267 | -0.957 | 36.146 | 1.00 | 47.46 | A C |
| ATOM | 48 | O | ARG | A | 242 | 28.837 | -0.102 | 35.461 | 1.00 | 47.19 | A O |
| ATOM | 49 | N | GLU | A | 243 | 28.895 | -2.011 | 36.680 | 1.00 | 47.89 | A N |
| ATOM | 50 | CA | GLU | A | 243 | 30.348 | -2.241 | 36.561 | 1.00 | 48.48 | A C |
| ATOM | 51 | CB | GLU | A | 243 | 30.830 | -3.388 | 37.473 | 1.00 | 50.64 | A C |
| ATOM | 52 | CG | GLU | A | 243 | 30.729 | -3.126 | 38.970 | 1.00 | 54.55 | A C |
| ATOM | 53 | CD | GLU | A | 243 | 29.283 | -3.128 | 39.467 | 1.00 | 57.53 | A C |
| ATOM | 54 | OE1 | GLU | A | 243 | 28.502 | -4.012 | 39.031 | 1.00 | 58.15 | A O |
| ATOM | 55 | OE2 | GLU | A | 243 | 28.926 | -2.246 | 40.286 | 1.00 | 58.29 | A O |
| ATOM | 56 | C | GLU | A | 243 | 30.840 | -2.525 | 35.143 | 1.00 | 47.12 | A C |
| ATOM | 57 | O | GLU | A | 243 | 32.036 | -2.441 | 34.878 | 1.00 | 46.69 | A O |
| ATOM | 58 | N | THR | A | 244 | 29.939 | -2.904 | 34.244 | 1.00 | 45.42 | A N |
| ATOM | 59 | CA | THR | A | 244 | 30.335 | -3.178 | 32.866 | 1.00 | 43.79 | A C |
| ATOM | 60 | CB | THR | A | 244 | 29.348 | -4.136 | 32.186 | 1.00 | 44.78 | A C |
| ATOM | 61 | OG1 | THR | A | 244 | 28.033 | -3.562 | 32.201 | 1.00 | 45.26 | A O |
| ATOM | 62 | CG2 | THR | A | 244 | 29.334 | -5.483 | 32.898 | 1.00 | 46.23 | A C |
| ATOM | 63 | C | THR | A | 244 | 30.411 | -1.900 | 32.023 | 1.00 | 42.13 | A C |
| ATOM | 64 | O | THR | A | 244 | 30.680 | -1.956 | 30.821 | 1.00 | 41.45 | A O |
| ATOM | 65 | N | LEU | A | 245 | 30.197 | -0.752 | 32.655 | 1.00 | 40.20 | A N |
| ATOM | 66 | CA | LEU | A | 245 | 30.211 | 0.506 | 31.935 | 1.00 | 39.06 | A C |
| ATOM | 67 | CB | LEU | A | 245 | 28.767 | 0.999 | 31.729 | 1.00 | 38.85 | A C |
| ATOM | 68 | CG | LEU | A | 245 | 28.552 | 2.359 | 31.043 | 1.00 | 38.64 | A C |
| ATOM | 69 | CD1 | LEU | A | 245 | 28.581 | 2.197 | 29.527 | 1.00 | 39.01 | A C |
| ATOM | 70 | CD2 | LEU | A | 245 | 27.227 | 2.964 | 31.472 | 1.00 | 38.52 | A C |
| ATOM | 71 | C | LEU | A | 245 | 31.016 | 1.586 | 32.639 | 1.00 | 38.75 | A C |
| ATOM | 72 | O | LEU | A | 245 | 30.915 | 1.759 | 33.862 | 1.00 | 38.51 | A O |
| ATOM | 73 | N | LYS | A | 246 | 31.800 | 2.326 | 31.853 | 1.00 | 38.19 | A N |
| ATOM | 74 | CA | LYS | A | 246 | 32.590 | 3.424 | 32.390 | 1.00 | 37.96 | A C |
| ATOM | 75 | CB | LYS | A | 246 | 34.097 | 3.150 | 32.301 | 1.00 | 39.88 | A C |
| ATOM | 76 | CG | LYS | A | 246 | 34.937 | 4.256 | 32.987 | 1.00 | 43.53 | A C |
| ATOM | 77 | CD | LYS | A | 246 | 36.434 | 3.957 | 33.088 | 1.00 | 44.95 | A C |
| ATOM | 78 | CE | LYS | A | 246 | 37.049 | 3.549 | 31.764 | 1.00 | 45.09 | A C |
| ATOM | 79 | NZ | LYS | A | 246 | 38.528 | 3.456 | 31.930 | 1.00 | 47.78 | A N |
| ATOM | 80 | C | LYS | A | 246 | 32.260 | 4.751 | 31.708 | 1.00 | 36.47 | A C |
| ATOM | 81 | O | LYS | A | 246 | 32.529 | 4.940 | 30.526 | 1.00 | 36.23 | A O |
| ATOM | 82 | N | LEU | A | 247 | 31.672 | 5.663 | 32.477 | 1.00 | 35.54 | A N |
| ATOM | 83 | CA | LEU | A | 247 | 31.315 | 6.983 | 31.990 | 1.00 | 34.45 | A C |
| ATOM | 84 | CB | LEU | A | 247 | 30.250 | 7.635 | 32.886 | 1.00 | 35.08 | A C |
| ATOM | 85 | CG | LEU | A | 247 | 28.786 | 7.345 | 32.533 | 1.00 | 36.46 | A C |
| ATOM | 86 | CD1 | LEU | A | 247 | 28.494 | 5.856 | 32.507 | 1.00 | 36.39 | A C |
| ATOM | 87 | CD2 | LEU | A | 247 | 27.881 | 8.048 | 33.523 | 1.00 | 38.09 | A C |
| ATOM | 88 | C | LEU | A | 247 | 32.582 | 7.816 | 31.967 | 1.00 | 33.33 | A C |
| ATOM | 89 | O | LEU | A | 247 | 33.337 | 7.862 | 32.947 | 1.00 | 34.17 | A O |
| ATOM | 90 | N | VAL | A | 248 | 32.797 | 8.487 | 30.846 | 1.00 | 31.13 | A N |
| ATOM | 91 | CA | VAL | A | 248 | 33.984 | 9.293 | 30.666 | 1.00 | 28.82 | A C |
| ATOM | 92 | CB | VAL | A | 248 | 34.772 | 8.811 | 29.420 | 1.00 | 27.97 | A C |
| ATOM | 93 | CG1 | VAL | A | 248 | 36.106 | 9.526 | 29.328 | 1.00 | 26.98 | A C |
| ATOM | 94 | CG2 | VAL | A | 248 | 34.956 | 7.301 | 29.455 | 1.00 | 26.54 | A C |
| ATOM | 95 | C | VAL | A | 248 | 33.728 | 10.788 | 30.523 | 1.00 | 27.87 | A C |
| ATOM | 96 | O | VAL | A | 248 | 34.385 | 11.602 | 31.166 | 1.00 | 28.61 | A O |
| ATOM | 97 | N | GLU | A | 249 | 32.715 | 11.151 | 29.752 | 1.00 | 26.51 | A N |
| ATOM | 98 | CA | GLU | A | 249 | 32.474 | 12.559 | 29.490 | 1.00 | 25.42 | A C |
| ATOM | 99 | CB | GLU | A | 249 | 33.259 | 12.880 | 28.224 | 1.00 | 25.56 | A C |
| ATOM | 100 | CG | GLU | A | 249 | 33.108 | 14.258 | 27.646 | 1.00 | 27.24 | A C |
| ATOM | 101 | CD | GLU | A | 249 | 33.832 | 14.396 | 26.311 | 1.00 | 27.44 | A C |
| ATOM | 102 | OE1 | GLU | A | 249 | 34.606 | 13.478 | 25.927 | 1.00 | 26.77 | A O |
| ATOM | 103 | OE2 | GLU | A | 249 | 33.614 | 15.425 | 25.642 | 1.00 | 30.33 | A O |
| ATOM | 104 | C | GLU | A | 249 | 30.996 | 12.899 | 29.297 | 1.00 | 24.32 | A C |
| ATOM | 105 | O | GLU | A | 249 | 30.267 | 12.175 | 28.638 | 1.00 | 23.79 | A O |

Figure 9

| | | | | | | | | | | | |
|---|---|---|---|---|---|---|---|---|---|---|---|
| ATOM | 106 | N | ARG | A | 250 | 30.561 | 14.019 | 29.845 | 1.00 | 23.97 | A N |
| ATOM | 107 | CA | ARG | A | 250 | 29.170 | 14.406 | 29.692 | 1.00 | 25.30 | A C |
| ATOM | 108 | CB | ARG | A | 250 | 28.673 | 15.148 | 30.921 | 1.00 | 26.48 | A C |
| ATOM | 109 | CG | ARG | A | 250 | 27.183 | 15.095 | 31.090 | 1.00 | 26.56 | A C |
| ATOM | 110 | CD | ARG | A | 250 | 26.773 | 15.988 | 32.216 | 1.00 | 28.42 | A C |
| ATOM | 111 | NE | ARG | A | 250 | 26.995 | 17.377 | 31.852 | 1.00 | 29.17 | A N |
| ATOM | 112 | CZ | ARG | A | 250 | 26.796 | 18.405 | 32.664 | 1.00 | 30.10 | A C |
| ATOM | 113 | NH1 | ARG | A | 250 | 26.359 | 18.208 | 33.899 | 1.00 | 28.99 | A N |
| ATOM | 114 | NH2 | ARG | A | 250 | 27.067 | 19.633 | 32.241 | 1.00 | 31.91 | A N |
| ATOM | 115 | C | ARG | A | 250 | 29.012 | 15.297 | 28.481 | 1.00 | 25.64 | A C |
| ATOM | 116 | O | ARG | A | 250 | 29.476 | 16.440 | 28.471 | 1.00 | 25.58 | A O |
| ATOM | 117 | N | LEU | A | 251 | 28.335 | 14.762 | 27.470 | 1.00 | 25.84 | A N |
| ATOM | 118 | CA | LEU | A | 251 | 28.083 | 15.471 | 26.220 | 1.00 | 24.96 | A C |
| ATOM | 119 | CB | LEU | A | 251 | 27.750 | 14.463 | 25.117 | 1.00 | 23.28 | A C |
| ATOM | 120 | CG | LEU | A | 251 | 28.769 | 13.332 | 24.945 | 1.00 | 21.83 | A C |
| ATOM | 121 | CD1 | LEU | A | 251 | 28.202 | 12.219 | 24.102 | 1.00 | 20.23 | A C |
| ATOM | 122 | CD2 | LEU | A | 251 | 30.061 | 13.875 | 24.352 | 1.00 | 22.16 | A C |
| ATOM | 123 | C | LEU | A | 251 | 26.955 | 16.500 | 26.379 | 1.00 | 26.08 | A C |
| ATOM | 124 | O | LEU | A | 251 | 27.029 | 17.604 | 25.824 | 1.00 | 26.34 | A O |
| ATOM | 125 | N | GLY | A | 252 | 25.933 | 16.161 | 27.164 | 1.00 | 26.37 | A N |
| ATOM | 126 | CA | GLY | A | 252 | 24.832 | 17.086 | 27.357 | 1.00 | 26.01 | A C |
| ATOM | 127 | C | GLY | A | 252 | 24.047 | 16.928 | 28.653 | 1.00 | 26.70 | A C |
| ATOM | 128 | O | GLY | A | 252 | 23.998 | 15.849 | 29.249 | 1.00 | 26.01 | A O |
| ATOM | 129 | N | ALA | A | 253 | 23.424 | 18.024 | 29.081 | 1.00 | 26.80 | A N |
| ATOM | 130 | CA | ALA | A | 253 | 22.596 | 18.053 | 30.285 | 1.00 | 27.30 | A C |
| ATOM | 131 | CB | ALA | A | 253 | 23.343 | 18.739 | 31.422 | 1.00 | 27.93 | A C |
| ATOM | 132 | C | ALA | A | 253 | 21.283 | 18.798 | 29.975 | 1.00 | 27.67 | A C |
| ATOM | 133 | O | ALA | A | 253 | 21.292 | 19.942 | 29.505 | 1.00 | 26.69 | A O |
| ATOM | 134 | N | GLY | A | 254 | 20.156 | 18.139 | 30.218 | 1.00 | 28.79 | A N |
| ATOM | 135 | CA | GLY | A | 254 | 18.872 | 18.763 | 29.943 | 1.00 | 30.56 | A C |
| ATOM | 136 | C | GLY | A | 254 | 17.849 | 18.675 | 31.060 | 1.00 | 31.12 | A C |
| ATOM | 137 | O | GLY | A | 254 | 18.149 | 18.198 | 32.152 | 1.00 | 31.31 | A O |
| ATOM | 138 | N | GLN | A | 255 | 16.627 | 19.114 | 30.760 | 1.00 | 31.90 | A N |
| ATOM | 139 | CA | GLN | A | 255 | 15.518 | 19.124 | 31.716 | 1.00 | 31.90 | A C |
| ATOM | 140 | CB | GLN | A | 255 | 14.251 | 19.702 | 31.040 | 1.00 | 35.55 | A C |
| ATOM | 141 | CG | GLN | A | 255 | 13.279 | 20.437 | 32.006 | 1.00 | 42.08 | A C |
| ATOM | 142 | CD | GLN | A | 255 | 11.775 | 20.330 | 31.629 | 1.00 | 44.80 | A C |
| ATOM | 143 | OE1 | GLN | A | 255 | 10.898 | 20.294 | 32.517 | 1.00 | 44.86 | A O |
| ATOM | 144 | NE2 | GLN | A | 255 | 11.480 | 20.293 | 30.325 | 1.00 | 44.42 | A N |
| ATOM | 145 | C | GLN | A | 255 | 15.204 | 17.748 | 32.332 | 1.00 | 30.07 | A C |
| ATOM | 146 | O | GLN | A | 255 | 14.906 | 17.656 | 33.521 | 1.00 | 30.10 | A O |
| ATOM | 147 | N | PHE | A | 256 | 15.330 | 16.685 | 31.540 | 1.00 | 28.33 | A N |
| ATOM | 148 | CA | PHE | A | 256 | 15.002 | 15.325 | 31.981 | 1.00 | 27.74 | A C |
| ATOM | 149 | CB | PHE | A | 256 | 14.121 | 14.634 | 30.929 | 1.00 | 29.91 | A C |
| ATOM | 150 | CG | PHE | A | 256 | 12.715 | 15.181 | 30.835 | 1.00 | 31.57 | A C |
| ATOM | 151 | CD1 | PHE | A | 256 | 12.319 | 16.288 | 31.580 | 1.00 | 32.29 | A C |
| ATOM | 152 | CD2 | PHE | A | 256 | 11.787 | 14.578 | 30.000 | 1.00 | 32.87 | A C |
| ATOM | 153 | CE1 | PHE | A | 256 | 11.023 | 16.786 | 31.500 | 1.00 | 32.73 | A C |
| ATOM | 154 | CE2 | PHE | A | 256 | 10.490 | 15.066 | 29.911 | 1.00 | 33.18 | A C |
| ATOM | 155 | CZ | PHE | A | 256 | 10.110 | 16.174 | 30.664 | 1.00 | 33.34 | A C |
| ATOM | 156 | C | PHE | A | 256 | 16.144 | 14.374 | 32.312 | 1.00 | 27.10 | A C |
| ATOM | 157 | O | PHE | A | 256 | 15.906 | 13.265 | 32.800 | 1.00 | 26.08 | A O |
| ATOM | 158 | N | GLY | A | 257 | 17.373 | 14.777 | 32.004 | 1.00 | 26.83 | A N |
| ATOM | 159 | CA | GLY | A | 257 | 18.517 | 13.919 | 32.265 | 1.00 | 26.07 | A C |
| ATOM | 160 | C | GLY | A | 257 | 19.766 | 14.361 | 31.531 | 1.00 | 25.41 | A C |
| ATOM | 161 | O | GLY | A | 257 | 19.909 | 15.535 | 31.200 | 1.00 | 24.22 | A O |
| ATOM | 162 | N | GLU | A | 258 | 20.662 | 13.413 | 31.258 | 1.00 | 27.07 | A N |
| ATOM | 163 | CA | GLU | A | 258 | 21.924 | 13.719 | 30.580 | 1.00 | 27.74 | A C |
| ATOM | 164 | CB | GLU | A | 258 | 23.041 | 13.924 | 31.622 | 1.00 | 29.40 | A C |

Figure 9

| | | | | | | | | | | |
|---|---|---|---|---|---|---|---|---|---|---|
| ATOM | 165 | CG | GLU | A | 258 | 22.561 | 14.531 | 32.941 | 1.00 33.72 | A | C |
| ATOM | 166 | CD | GLU | A | 258 | 23.665 | 15.179 | 33.738 | 1.00 37.55 | A | C |
| ATOM | 167 | OE1 | GLU | A | 258 | 24.470 | 14.447 | 34.367 | 1.00 39.03 | A | O |
| ATOM | 168 | OE2 | GLU | A | 258 | 23.722 | 16.430 | 33.740 | 1.00 39.60 | A | O |
| ATOM | 169 | C | GLU | A | 258 | 22.369 | 12.642 | 29.599 | 1.00 26.75 | A | C |
| ATOM | 170 | O | GLU | A | 258 | 21.836 | 11.533 | 29.595 | 1.00 26.18 | A | O |
| ATOM | 171 | N | VAL | A | 259 | 23.323 | 13.002 | 28.739 | 1.00 26.10 | A | N |
| ATOM | 172 | CA | VAL | A | 259 | 23.914 | 12.065 | 27.773 | 1.00 25.03 | A | C |
| ATOM | 173 | CB | VAL | A | 259 | 23.597 | 12.429 | 26.315 | 1.00 23.74 | A | C |
| ATOM | 174 | CG1 | VAL | A | 259 | 24.037 | 11.302 | 25.403 | 1.00 22.13 | A | C |
| ATOM | 175 | CG2 | VAL | A | 259 | 22.110 | 12.711 | 26.153 | 1.00 25.46 | A | C |
| ATOM | 176 | C | VAL | A | 259 | 25.440 | 12.094 | 27.985 | 1.00 23.98 | A | C |
| ATOM | 177 | O | VAL | A | 259 | 26.041 | 13.165 | 28.092 | 1.00 22.76 | A | O |
| ATOM | 178 | N | TRP | A | 260 | 26.039 | 10.913 | 28.078 | 1.00 24.16 | A | N |
| ATOM | 179 | CA | TRP | A | 260 | 27.472 | 10.767 | 28.313 | 1.00 25.16 | A | C |
| ATOM | 180 | CB | TRP | A | 260 | 27.728 | 10.102 | 29.687 | 1.00 25.70 | A | C |
| ATOM | 181 | CG | TRP | A | 260 | 27.511 | 10.986 | 30.883 | 1.00 27.68 | A | C |
| ATOM | 182 | CD2 | TRP | A | 260 | 28.510 | 11.440 | 31.810 | 1.00 28.53 | A | C |
| ATOM | 183 | CE2 | TRP | A | 260 | 27.867 | 12.316 | 32.721 | 1.00 29.81 | A | C |
| ATOM | 184 | CE3 | TRP | A | 260 | 29.884 | 11.198 | 31.960 | 1.00 27.55 | A | C |
| ATOM | 185 | CD1 | TRP | A | 260 | 26.338 | 11.573 | 31.271 | 1.00 28.81 | A | C |
| ATOM | 186 | NE1 | TRP | A | 260 | 26.545 | 12.379 | 32.365 | 1.00 29.40 | A | N |
| ATOM | 187 | CZ2 | TRP | A | 260 | 28.558 | 12.954 | 33.768 | 1.00 28.65 | A | C |
| ATOM | 188 | CZ3 | TRP | A | 260 | 30.565 | 11.832 | 32.998 | 1.00 26.74 | A | C |
| ATOM | 189 | CH2 | TRP | A | 260 | 29.901 | 12.700 | 33.886 | 1.00 27.68 | A | C |
| ATOM | 190 | C | TRP | A | 260 | 28.143 | 9.880 | 27.280 | 1.00 24.62 | A | C |
| ATOM | 191 | O | TRP | A | 260 | 27.502 | 9.034 | 26.668 | 1.00 24.11 | A | O |
| ATOM | 192 | N | MET | A | 261 | 29.427 | 10.136 | 27.042 | 1.00 24.60 | A | N |
| ATOM | 193 | CA | MET | A | 261 | 30.225 | 9.283 | 26.182 | 1.00 23.03 | A | C |
| ATOM | 194 | CB | MET | A | 261 | 31.318 | 10.074 | 25.462 | 1.00 22.13 | A | C |
| ATOM | 195 | CG | MET | A | 261 | 32.211 | 9.224 | 24.556 | 1.00 21.14 | A | C |
| ATOM | 196 | SD | MET | A | 261 | 33.461 | 8.201 | 25.414 | 1.00 23.17 | A | S |
| ATOM | 197 | CE | MET | A | 261 | 34.612 | 9.461 | 25.842 | 1.00 22.43 | A | C |
| ATOM | 198 | C | MET | A | 261 | 30.853 | 8.342 | 27.224 | 1.00 23.53 | A | C |
| ATOM | 199 | O | MET | A | 261 | 31.187 | 8.770 | 28.336 | 1.00 22.96 | A | O |
| ATOM | 200 | N | GLY | A | 262 | 30.966 | 7.064 | 26.885 | 1.00 24.00 | A | N |
| ATOM | 201 | CA | GLY | A | 262 | 31.541 | 6.101 | 27.798 | 1.00 25.22 | A | C |
| ATOM | 202 | C | GLY | A | 262 | 32.048 | 4.888 | 27.050 | 1.00 26.90 | A | C |
| ATOM | 203 | O | GLY | A | 262 | 32.084 | 4.876 | 25.819 | 1.00 27.14 | A | O |
| ATOM | 204 | N | TYR | A | 263 | 32.482 | 3.879 | 27.795 | 1.00 28.25 | A | N |
| ATOM | 205 | CA | TYR | A | 263 | 32.979 | 2.650 | 27.199 | 1.00 29.24 | A | C |
| ATOM | 206 | CB | TYR | A | 263 | 34.494 | 2.518 | 27.405 | 1.00 27.57 | A | C |
| ATOM | 207 | CG | TYR | A | 263 | 35.279 | 3.526 | 26.590 | 1.00 25.16 | A | C |
| ATOM | 208 | CD1 | TYR | A | 263 | 35.622 | 3.260 | 25.261 | 1.00 23.59 | A | C |
| ATOM | 209 | CE1 | TYR | A | 263 | 36.264 | 4.212 | 24.480 | 1.00 23.22 | A | C |
| ATOM | 210 | CD2 | TYR | A | 263 | 35.610 | 4.780 | 27.121 | 1.00 24.93 | A | C |
| ATOM | 211 | CE2 | TYR | A | 263 | 36.257 | 5.748 | 26.343 | 1.00 23.43 | A | C |
| ATOM | 212 | CZ | TYR | A | 263 | 36.573 | 5.452 | 25.026 | 1.00 22.91 | A | C |
| ATOM | 213 | OH | TYR | A | 263 | 37.165 | 6.410 | 24.246 | 1.00 24.64 | A | O |
| ATOM | 214 | C | TYR | A | 263 | 32.222 | 1.474 | 27.791 | 1.00 30.73 | A | C |
| ATOM | 215 | O | TYR | A | 263 | 32.051 | 1.380 | 29.003 | 1.00 31.22 | A | O |
| ATOM | 216 | N | TYR | A | 264 | 31.719 | 0.620 | 26.909 | 1.00 32.93 | A | N |
| ATOM | 217 | CA | TYR | A | 264 | 30.945 | -0.557 | 27.279 | 1.00 36.10 | A | C |
| ATOM | 218 | CB | TYR | A | 264 | 29.730 | -0.674 | 26.345 | 1.00 35.76 | A | C |
| ATOM | 219 | CG | TYR | A | 264 | 28.762 | -1.784 | 26.678 | 1.00 35.57 | A | C |
| ATOM | 220 | CD1 | TYR | A | 264 | 28.307 | -1.979 | 27.988 | 1.00 35.13 | A | C |
| ATOM | 221 | CE1 | TYR | A | 264 | 27.434 | -3.014 | 28.298 | 1.00 34.83 | A | C |
| ATOM | 222 | CD2 | TYR | A | 264 | 28.313 | -2.652 | 25.684 | 1.00 35.70 | A | C |
| ATOM | 223 | CE2 | TYR | A | 264 | 27.438 | -3.689 | 25.985 | 1.00 36.52 | A | C |

Figure 9

```
ATOM    224  CZ   TYR A 264      27.005  -3.865  27.293  1.00 35.76      A    C
ATOM    225  OH   TYR A 264      26.159  -4.908  27.576  1.00 35.63      A    O
ATOM    226  C    TYR A 264      31.857  -1.776  27.167  1.00 38.16      A    C
ATOM    227  O    TYR A 264      32.334  -2.107  26.080  1.00 38.58      A    O
ATOM    228  N    ASN A 265      32.094  -2.433  28.302  1.00 40.61      A    N
ATOM    229  CA   ASN A 265      32.985  -3.588  28.372  1.00 42.82      A    C
ATOM    230  CB   ASN A 265      32.541  -4.700  27.418  1.00 42.76      A    C
ATOM    231  CG   ASN A 265      31.211  -5.315  27.817  1.00 42.69      A    C
ATOM    232  OD1  ASN A 265      30.855  -5.363  28.997  1.00 41.57      A    O
ATOM    233  ND2  ASN A 265      30.472  -5.791  26.829  1.00 42.52      A    N
ATOM    234  C    ASN A 265      34.415  -3.149  28.054  1.00 44.49      A    C
ATOM    235  O    ASN A 265      35.103  -3.777  27.247  1.00 44.67      A    O
ATOM    236  N    GLY A 266      34.816  -2.019  28.641  1.00 46.21      A    N
ATOM    237  CA   GLY A 266      36.156  -1.489  28.453  1.00 47.23      A    C
ATOM    238  C    GLY A 266      36.557  -0.903  27.105  1.00 47.91      A    C
ATOM    239  O    GLY A 266      37.264   0.117  27.071  1.00 48.44      A    O
ATOM    240  N    HIS A 267      36.092  -1.492  26.002  1.00 48.14      A    N
ATOM    241  CA   HIS A 267      36.493  -0.999  24.683  1.00 48.77      A    C
ATOM    242  CB   HIS A 267      37.441  -2.013  24.017  1.00 53.36      A    C
ATOM    243  CG   HIS A 267      38.779  -2.109  24.695  1.00 58.69      A    C
ATOM    244  CD2  HIS A 267      39.745  -1.175  24.893  1.00 60.48      A    C
ATOM    245  ND1  HIS A 267      39.227  -3.257  25.318  1.00 59.77      A    N
ATOM    246  CE1  HIS A 267      40.407  -3.026  25.872  1.00 61.08      A    C
ATOM    247  NE2  HIS A 267      40.743  -1.770  25.629  1.00 61.46      A    N
ATOM    248  C    HIS A 267      35.470  -0.449  23.675  1.00 46.06      A    C
ATOM    249  O    HIS A 267      35.856   0.262  22.745  1.00 46.21      A    O
ATOM    250  N    THR A 268      34.184  -0.741  23.853  1.00 42.64      A    N
ATOM    251  CA   THR A 268      33.158  -0.234  22.933  1.00 38.53      A    C
ATOM    252  CB   THR A 268      31.904  -1.131  22.939  1.00 39.68      A    C
ATOM    253  OG1  THR A 268      32.289  -2.482  22.655  1.00 41.54      A    O
ATOM    254  CG2  THR A 268      30.894  -0.658  21.896  1.00 38.28      A    C
ATOM    255  C    THR A 268      32.741   1.179  23.321  1.00 34.98      A    C
ATOM    256  O    THR A 268      32.258   1.402  24.420  1.00 34.28      A    O
ATOM    257  N    LYS A 269      32.945   2.137  22.424  1.00 32.23      A    N
ATOM    258  CA   LYS A 269      32.574   3.527  22.693  1.00 29.66      A    C
ATOM    259  CB   LYS A 269      33.277   4.456  21.709  1.00 28.41      A    C
ATOM    260  CG   LYS A 269      33.339   5.889  22.148  1.00 26.00      A    C
ATOM    261  CD   LYS A 269      34.235   6.667  21.221  1.00 26.10      A    C
ATOM    262  CE   LYS A 269      34.782   7.880  21.923  1.00 26.45      A    C
ATOM    263  NZ   LYS A 269      35.695   8.658  21.061  1.00 28.31      A    N
ATOM    264  C    LYS A 269      31.042   3.639  22.569  1.00 28.98      A    C
ATOM    265  O    LYS A 269      30.452   3.227  21.557  1.00 28.63      A    O
ATOM    266  N    VAL A 270      30.410   4.177  23.608  1.00 27.45      A    N
ATOM    267  CA   VAL A 270      28.955   4.288  23.657  1.00 24.96      A    C
ATOM    268  CB   VAL A 270      28.347   3.179  24.591  1.00 23.72      A    C
ATOM    269  CG1  VAL A 270      28.646   1.782  24.067  1.00 21.44      A    C
ATOM    270  CG2  VAL A 270      28.852   3.334  26.012  1.00 22.14      A    C
ATOM    271  C    VAL A 270      28.433   5.636  24.157  1.00 24.95      A    C
ATOM    272  O    VAL A 270      29.184   6.459  24.678  1.00 23.75      A    O
ATOM    273  N    ALA A 271      27.144   5.882  23.907  1.00 24.96      A    N
ATOM    274  CA   ALA A 271      26.467   7.071  24.403  1.00 24.79      A    C
ATOM    275  CB   ALA A 271      25.607   7.709  23.326  1.00 23.54      A    C
ATOM    276  C    ALA A 271      25.597   6.511  25.534  1.00 25.02      A    C
ATOM    277  O    ALA A 271      25.095   5.382  25.449  1.00 25.92      A    O
ATOM    278  N    VAL A 272      25.489   7.248  26.627  1.00 24.93      A    N
ATOM    279  CA   VAL A 272      24.699   6.776  27.750  1.00 25.06      A    C
ATOM    280  CB   VAL A 272      25.581   6.430  29.003  1.00 25.12      A    C
ATOM    281  CG1  VAL A 272      24.729   5.726  30.070  1.00 23.91      A    C
ATOM    282  CG2  VAL A 272      26.764   5.547  28.619  1.00 23.80      A    C
```

Figure 9

| ATOM | 283 | C | VAL | A | 272 | 23.711 | 7.855 | 28.127 | 1.00 | 25.12 | A | C |
|------|-----|-----|-----|---|-----|--------|--------|--------|------|-------|---|---|
| ATOM | 284 | O | VAL | A | 272 | 24.087 | 9.001 | 28.379 | 1.00 | 25.06 | A | O |
| ATOM | 285 | N | LYS | A | 273 | 22.434 | 7.496 | 28.124 | 1.00 | 25.92 | A | N |
| ATOM | 286 | CA | LYS | A | 273 | 21.389 | 8.431 | 28.500 | 1.00 | 26.61 | A | C |
| ATOM | 287 | CB | LYS | A | 273 | 20.194 | 8.243 | 27.573 | 1.00 | 27.50 | A | C |
| ATOM | 288 | CG | LYS | A | 273 | 19.496 | 9.526 | 27.232 | 1.00 | 29.99 | A | C |
| ATOM | 289 | CD | LYS | A | 273 | 18.458 | 9.300 | 26.162 | 1.00 | 30.78 | A | C |
| ATOM | 290 | CE | LYS | A | 273 | 18.375 | 10.519 | 25.297 | 1.00 | 31.99 | A | C |
| ATOM | 291 | NZ | LYS | A | 273 | 17.196 | 10.476 | 24.400 | 1.00 | 32.68 | A | N |
| ATOM | 292 | C | LYS | A | 273 | 21.009 | 8.113 | 29.953 | 1.00 | 26.76 | A | C |
| ATOM | 293 | O | LYS | A | 273 | 20.740 | 6.965 | 30.278 | 1.00 | 25.91 | A | O |
| ATOM | 294 | N | SER | A | 274 | 21.056 | 9.105 | 30.836 | 1.00 | 28.31 | A | N |
| ATOM | 295 | CA | SER | A | 274 | 20.705 | 8.880 | 32.242 | 1.00 | 30.74 | A | C |
| ATOM | 296 | CB | SER | A | 274 | 21.895 | 9.158 | 33.175 | 1.00 | 30.23 | A | C |
| ATOM | 297 | OG | SER | A | 274 | 22.222 | 10.534 | 33.186 | 1.00 | 32.44 | A | O |
| ATOM | 298 | C | SER | A | 274 | 19.508 | 9.734 | 32.659 | 1.00 | 31.74 | A | C |
| ATOM | 299 | O | SER | A | 274 | 19.377 | 10.896 | 32.248 | 1.00 | 32.77 | A | O |
| ATOM | 300 | N | LEU | A | 275 | 18.666 | 9.166 | 33.516 | 1.00 | 31.56 | A | N |
| ATOM | 301 | CA | LEU | A | 275 | 17.468 | 9.851 | 33.977 | 1.00 | 30.84 | A | C |
| ATOM | 302 | CB | LEU | A | 275 | 16.375 | 8.817 | 34.250 | 1.00 | 29.51 | A | C |
| ATOM | 303 | CG | LEU | A | 275 | 15.029 | 9.325 | 34.787 | 1.00 | 28.99 | A | C |
| ATOM | 304 | CD1 | LEU | A | 275 | 14.354 | 10.232 | 33.768 | 1.00 | 26.71 | A | C |
| ATOM | 305 | CD2 | LEU | A | 275 | 14.140 | 8.132 | 35.135 | 1.00 | 28.73 | A | C |
| ATOM | 306 | C | LEU | A | 275 | 17.627 | 10.737 | 35.213 | 1.00 | 31.54 | A | C |
| ATOM | 307 | O | LEU | A | 275 | 18.083 | 10.275 | 36.256 | 1.00 | 31.38 | A | O |
| ATOM | 308 | N | LYS | A | 276 | 17.264 | 12.012 | 35.090 | 1.00 | 32.44 | A | N |
| ATOM | 309 | CA | LYS | A | 276 | 17.292 | 12.906 | 36.239 | 1.00 | 34.28 | A | C |
| ATOM | 310 | CB | LYS | A | 276 | 17.096 | 14.360 | 35.813 | 1.00 | 33.13 | A | C |
| ATOM | 311 | CG | LYS | A | 276 | 16.904 | 15.331 | 36.982 | 1.00 | 34.49 | A | C |
| ATOM | 312 | CD | LYS | A | 276 | 16.646 | 16.771 | 36.505 | 1.00 | 37.14 | A | C |
| ATOM | 313 | CE | LYS | A | 276 | 17.779 | 17.268 | 35.595 | 1.00 | 39.39 | A | C |
| ATOM | 314 | NZ | LYS | A | 276 | 17.634 | 18.673 | 35.093 | 1.00 | 40.05 | A | N |
| ATOM | 315 | C | LYS | A | 276 | 16.067 | 12.430 | 37.020 | 1.00 | 36.66 | A | C |
| ATOM | 316 | O | LYS | A | 276 | 14.949 | 12.483 | 36.505 | 1.00 | 37.28 | A | O |
| ATOM | 317 | N | GLN | A | 277 | 16.278 | 11.888 | 38.216 | 1.00 | 38.47 | A | N |
| ATOM | 318 | CA | GLN | A | 277 | 15.174 | 11.382 | 39.029 | 1.00 | 40.06 | A | C |
| ATOM | 319 | CB | GLN | A | 277 | 15.690 | 10.928 | 40.387 | 1.00 | 43.65 | A | C |
| ATOM | 320 | CG | GLN | A | 277 | 14.607 | 10.418 | 41.321 | 1.00 | 49.13 | A | C |
| ATOM | 321 | CD | GLN | A | 277 | 15.131 | 10.177 | 42.718 | 1.00 | 53.12 | A | C |
| ATOM | 322 | OE1 | GLN | A | 277 | 16.177 | 10.719 | 43.107 | 1.00 | 54.85 | A | O |
| ATOM | 323 | NE2 | GLN | A | 277 | 14.412 | 9.370 | 43.490 | 1.00 | 55.37 | A | N |
| ATOM | 324 | C | GLN | A | 277 | 14.038 | 12.386 | 39.216 | 1.00 | 39.10 | A | C |
| ATOM | 325 | O | GLN | A | 277 | 14.269 | 13.560 | 39.513 | 1.00 | 38.17 | A | O |
| ATOM | 326 | N | GLY | A | 278 | 12.814 | 11.922 | 38.993 | 1.00 | 38.74 | A | N |
| ATOM | 327 | CA | GLY | A | 278 | 11.669 | 12.792 | 39.147 | 1.00 | 38.67 | A | C |
| ATOM | 328 | C | GLY | A | 278 | 11.117 | 13.338 | 37.843 | 1.00 | 38.95 | A | C |
| ATOM | 329 | O | GLY | A | 278 | 9.946 | 13.719 | 37.782 | 1.00 | 40.16 | A | O |
| ATOM | 330 | N | SER | A | 279 | 11.949 | 13.403 | 36.809 | 1.00 | 37.86 | A | N |
| ATOM | 331 | CA | SER | A | 279 | 11.517 | 13.906 | 35.504 | 1.00 | 37.52 | A | C |
| ATOM | 332 | CB | SER | A | 279 | 12.679 | 13.856 | 34.508 | 1.00 | 37.65 | A | C |
| ATOM | 333 | OG | SER | A | 279 | 13.699 | 14.745 | 34.907 | 1.00 | 38.16 | A | O |
| ATOM | 334 | C | SER | A | 279 | 10.354 | 13.079 | 34.972 | 1.00 | 36.27 | A | C |
| ATOM | 335 | O | SER | A | 279 | 9.384 | 13.612 | 34.416 | 1.00 | 36.28 | A | O |
| ATOM | 336 | N | MET | A | 280 | 10.496 | 11.767 | 35.132 | 1.00 | 34.66 | A | N |
| ATOM | 337 | CA | MET | A | 280 | 9.496 | 10.791 | 34.722 | 1.00 | 33.28 | A | C |
| ATOM | 338 | CB | MET | A | 280 | 9.526 | 10.558 | 33.196 | 1.00 | 33.28 | A | C |
| ATOM | 339 | CG | MET | A | 280 | 10.705 | 9.734 | 32.658 | 1.00 | 31.82 | A | C |
| ATOM | 340 | SD | MET | A | 280 | 10.944 | 9.908 | 30.866 | 1.00 | 30.03 | A | S |
| ATOM | 341 | CE | MET | A | 280 | 9.799 | 8.844 | 30.293 | 1.00 | 32.18 | A | C |

Figure 9

| ATOM | 342 | C | MET | A | 280 | 9.824 | 9.512 | 35.492 | 1.00 | 32.56 | A | C |
|------|-----|-----|-----|---|-----|-------|-------|--------|------|-------|---|---|
| ATOM | 343 | O | MET | A | 280 | 10.917 | 9.392 | 36.064 | 1.00 | 32.68 | A | O |
| ATOM | 344 | N | SER | A | 281 | 8.873 | 8.583 | 35.543 | 1.00 | 31.42 | A | N |
| ATOM | 345 | CA | SER | A | 281 | 9.075 | 7.336 | 36.263 | 1.00 | 29.77 | A | C |
| ATOM | 346 | CB | SER | A | 281 | 7.752 | 6.571 | 36.417 | 1.00 | 28.29 | A | C |
| ATOM | 347 | OG | SER | A | 281 | 7.478 | 5.747 | 35.298 | 1.00 | 25.29 | A | O |
| ATOM | 348 | C | SER | A | 281 | 10.088 | 6.445 | 35.556 | 1.00 | 30.71 | A | C |
| ATOM | 349 | O | SER | A | 281 | 10.254 | 6.505 | 34.334 | 1.00 | 30.09 | A | O |
| ATOM | 350 | N | PRO | A | 282 | 10.821 | 5.634 | 36.342 | 1.00 | 31.11 | A | N |
| ATOM | 351 | CD | PRO | A | 282 | 10.916 | 5.669 | 37.809 | 1.00 | 30.59 | A | C |
| ATOM | 352 | CA | PRO | A | 282 | 11.824 | 4.723 | 35.776 | 1.00 | 31.00 | A | C |
| ATOM | 353 | CB | PRO | A | 282 | 12.288 | 3.946 | 37.002 | 1.00 | 30.45 | A | C |
| ATOM | 354 | CG | PRO | A | 282 | 12.257 | 4.993 | 38.062 | 1.00 | 30.09 | A | C |
| ATOM | 355 | C | PRO | A | 282 | 11.223 | 3.802 | 34.720 | 1.00 | 31.21 | A | C |
| ATOM | 356 | O | PRO | A | 282 | 11.826 | 3.590 | 33.677 | 1.00 | 31.55 | A | O |
| ATOM | 357 | N | ASP | A | 283 | 10.028 | 3.266 | 34.982 | 1.00 | 31.64 | A | N |
| ATOM | 358 | CA | ASP | A | 283 | 9.362 | 2.368 | 34.039 | 1.00 | 31.86 | A | C |
| ATOM | 359 | CB | ASP | A | 283 | 8.066 | 1.792 | 34.641 | 1.00 | 34.05 | A | C |
| ATOM | 360 | CG | ASP | A | 283 | 8.325 | 0.638 | 35.632 | 1.00 | 36.94 | A | C |
| ATOM | 361 | OD1 | ASP | A | 283 | 9.501 | 0.259 | 35.822 | 1.00 | 39.48 | A | O |
| ATOM | 362 | OD2 | ASP | A | 283 | 7.363 | 0.098 | 36.219 | 1.00 | 38.07 | A | O |
| ATOM | 363 | C | ASP | A | 283 | 9.088 | 3.014 | 32.682 | 1.00 | 30.96 | A | C |
| ATOM | 364 | O | ASP | A | 283 | 9.214 | 2.361 | 31.652 | 1.00 | 30.80 | A | O |
| ATOM | 365 | N | ALA | A | 284 | 8.718 | 4.291 | 32.682 | 1.00 | 30.51 | A | N |
| ATOM | 366 | CA | ALA | A | 284 | 8.452 | 5.019 | 31.442 | 1.00 | 29.89 | A | C |
| ATOM | 367 | CB | ALA | A | 284 | 7.793 | 6.355 | 31.756 | 1.00 | 27.44 | A | C |
| ATOM | 368 | C | ALA | A | 284 | 9.753 | 5.245 | 30.642 | 1.00 | 30.02 | A | C |
| ATOM | 369 | O | ALA | A | 284 | 9.769 | 5.094 | 29.411 | 1.00 | 29.96 | A | O |
| ATOM | 370 | N | PHE | A | 285 | 10.822 | 5.631 | 31.352 | 1.00 | 29.71 | A | N |
| ATOM | 371 | CA | PHE | A | 285 | 12.146 | 5.886 | 30.758 | 1.00 | 29.30 | A | C |
| ATOM | 372 | CB | PHE | A | 285 | 13.123 | 6.380 | 31.839 | 1.00 | 30.08 | A | C |
| ATOM | 373 | CG | PHE | A | 285 | 14.499 | 6.763 | 31.320 | 1.00 | 30.46 | A | C |
| ATOM | 374 | CD1 | PHE | A | 285 | 14.692 | 7.946 | 30.598 | 1.00 | 30.87 | A | C |
| ATOM | 375 | CD2 | PHE | A | 285 | 15.606 | 5.966 | 31.599 | 1.00 | 30.12 | A | C |
| ATOM | 376 | CE1 | PHE | A | 285 | 15.966 | 8.329 | 30.166 | 1.00 | 30.58 | A | C |
| ATOM | 377 | CE2 | PHE | A | 285 | 16.884 | 6.343 | 31.171 | 1.00 | 30.23 | A | C |
| ATOM | 378 | CZ | PHE | A | 285 | 17.061 | 7.525 | 30.454 | 1.00 | 30.21 | A | C |
| ATOM | 379 | C | PHE | A | 285 | 12.693 | 4.624 | 30.102 | 1.00 | 28.50 | A | C |
| ATOM | 380 | O | PHE | A | 285 | 13.157 | 4.662 | 28.967 | 1.00 | 28.31 | A | O |
| ATOM | 381 | N | LEU | A | 286 | 12.618 | 3.508 | 30.819 | 1.00 | 28.56 | A | N |
| ATOM | 382 | CA | LEU | A | 286 | 13.086 | 2.230 | 30.309 | 1.00 | 29.44 | A | C |
| ATOM | 383 | CB | LEU | A | 286 | 13.154 | 1.194 | 31.435 | 1.00 | 30.24 | A | C |
| ATOM | 384 | CG | LEU | A | 286 | 14.310 | 1.342 | 32.443 | 1.00 | 31.05 | A | C |
| ATOM | 385 | CD1 | LEU | A | 286 | 14.103 | 0.434 | 33.657 | 1.00 | 29.86 | A | C |
| ATOM | 386 | CD2 | LEU | A | 286 | 15.633 | 1.026 | 31.752 | 1.00 | 29.36 | A | C |
| ATOM | 387 | C | LEU | A | 286 | 12.184 | 1.726 | 29.198 | 1.00 | 30.53 | A | C |
| ATOM | 388 | O | LEU | A | 286 | 12.623 | 0.967 | 28.334 | 1.00 | 30.10 | A | O |
| ATOM | 389 | N | ALA | A | 287 | 10.917 | 2.149 | 29.237 | 1.00 | 32.28 | A | N |
| ATOM | 390 | CA | ALA | A | 287 | 9.917 | 1.763 | 28.238 | 1.00 | 33.22 | A | C |
| ATOM | 391 | CB | ALA | A | 287 | 8.517 | 2.143 | 28.704 | 1.00 | 32.63 | A | C |
| ATOM | 392 | C | ALA | A | 287 | 10.227 | 2.407 | 26.889 | 1.00 | 34.08 | A | C |
| ATOM | 393 | O | ALA | A | 287 | 10.000 | 1.792 | 25.840 | 1.00 | 34.56 | A | O |
| ATOM | 394 | N | GLU | A | 288 | 10.745 | 3.639 | 26.923 | 1.00 | 34.20 | A | N |
| ATOM | 395 | CA | GLU | A | 288 | 11.132 | 4.356 | 25.705 | 1.00 | 35.20 | A | C |
| ATOM | 396 | CB | GLU | A | 288 | 11.599 | 5.780 | 26.010 | 1.00 | 35.99 | A | C |
| ATOM | 397 | CG | GLU | A | 288 | 10.514 | 6.724 | 26.503 | 1.00 | 37.93 | A | C |
| ATOM | 398 | CD | GLU | A | 288 | 10.989 | 8.172 | 26.620 | 1.00 | 40.15 | A | C |
| ATOM | 399 | OE1 | GLU | A | 288 | 12.220 | 8.421 | 26.610 | 1.00 | 41.10 | A | O |
| ATOM | 400 | OE2 | GLU | A | 288 | 10.120 | 9.072 | 26.715 | 1.00 | 41.28 | A | O |

Figure 9

| ATOM | 401 | C | GLU | A | 288 | 12.272 | 3.607 | 25.019 | 1.00 | 35.32 | A | C |
|------|-----|-----|-----|---|-----|--------|--------|--------|------|-------|---|---|
| ATOM | 402 | O | GLU | A | 288 | 12.375 | 3.625 | 23.802 | 1.00 | 35.91 | A | O |
| ATOM | 403 | N | ALA | A | 289 | 13.116 | 2.943 | 25.807 | 1.00 | 35.48 | A | N |
| ATOM | 404 | CA | ALA | A | 289 | 14.237 | 2.177 | 25.278 | 1.00 | 35.15 | A | C |
| ATOM | 405 | CB | ALA | A | 289 | 15.278 | 1.937 | 26.355 | 1.00 | 35.85 | A | C |
| ATOM | 406 | C | ALA | A | 289 | 13.800 | 0.853 | 24.682 | 1.00 | 35.16 | A | C |
| ATOM | 407 | O | ALA | A | 289 | 14.574 | 0.232 | 23.959 | 1.00 | 35.24 | A | O |
| ATOM | 408 | N | ASN | A | 290 | 12.592 | 0.393 | 25.018 | 1.00 | 35.07 | A | N |
| ATOM | 409 | CA | ASN | A | 290 | 12.059 | -0.857 | 24.457 | 1.00 | 35.54 | A | C |
| ATOM | 410 | CB | ASN | A | 290 | 10.724 | -1.237 | 25.117 | 1.00 | 38.38 | A | C |
| ATOM | 411 | CG | ASN | A | 290 | 10.882 | -1.762 | 26.526 | 1.00 | 40.64 | A | C |
| ATOM | 412 | OD1 | ASN | A | 290 | 9.944 | -1.684 | 27.329 | 1.00 | 42.05 | A | O |
| ATOM | 413 | ND2 | ASN | A | 290 | 12.047 | -2.332 | 26.833 | 1.00 | 40.76 | A | N |
| ATOM | 414 | C | ASN | A | 290 | 11.832 | -0.687 | 22.950 | 1.00 | 34.33 | A | C |
| ATOM | 415 | O | ASN | A | 290 | 11.806 | -1.658 | 22.201 | 1.00 | 33.24 | A | O |
| ATOM | 416 | N | LEU | A | 291 | 11.616 | 0.562 | 22.543 | 1.00 | 33.60 | A | N |
| ATOM | 417 | CA | LEU | A | 291 | 11.400 | 0.904 | 21.141 | 1.00 | 33.21 | A | C |
| ATOM | 418 | CB | LEU | A | 291 | 11.059 | 2.393 | 21.014 | 1.00 | 32.87 | A | C |
| ATOM | 419 | CG | LEU | A | 291 | 9.722 | 2.693 | 21.692 | 1.00 | 33.66 | A | C |
| ATOM | 420 | CD1 | LEU | A | 291 | 9.477 | 4.175 | 21.801 | 1.00 | 32.55 | A | C |
| ATOM | 421 | CD2 | LEU | A | 291 | 8.595 | 2.004 | 20.943 | 1.00 | 33.78 | A | C |
| ATOM | 422 | C | LEU | A | 291 | 12.615 | 0.512 | 20.282 | 1.00 | 32.98 | A | C |
| ATOM | 423 | O | LEU | A | 291 | 12.415 | 0.034 | 19.155 | 1.00 | 32.67 | A | O |
| ATOM | 424 | N | MET | A | 292 | 13.826 | 0.658 | 20.827 | 1.00 | 32.86 | A | N |
| ATOM | 425 | CA | MET | A | 292 | 15.041 | 0.266 | 20.095 | 1.00 | 32.55 | A | C |
| ATOM | 426 | CB | MET | A | 292 | 16.300 | 0.845 | 20.733 | 1.00 | 30.76 | A | C |
| ATOM | 427 | CG | MET | A | 292 | 16.478 | 2.303 | 20.472 | 1.00 | 29.27 | A | C |
| ATOM | 428 | SD | MET | A | 292 | 18.057 | 2.844 | 21.112 | 1.00 | 26.76 | A | S |
| ATOM | 429 | CE | MET | A | 292 | 17.711 | 2.687 | 22.831 | 1.00 | 29.26 | A | C |
| ATOM | 430 | C | MET | A | 292 | 15.166 | -1.261 | 19.994 | 1.00 | 33.84 | A | C |
| ATOM | 431 | O | MET | A | 292 | 15.755 | -1.756 | 19.044 | 1.00 | 33.71 | A | O |
| ATOM | 432 | N | LYS | A | 293 | 14.616 | -1.978 | 20.959 | 1.00 | 35.94 | A | N |
| ATOM | 433 | CA | LYS | A | 293 | 14.652 | -3.446 | 20.964 | 1.00 | 38.06 | A | C |
| ATOM | 434 | CB | LYS | A | 293 | 14.140 | -4.017 | 22.290 | 1.00 | 38.18 | A | C |
| ATOM | 435 | CG | LYS | A | 293 | 14.851 | -3.545 | 23.528 | 1.00 | 40.34 | A | C |
| ATOM | 436 | CD | LYS | A | 293 | 14.256 | -4.227 | 24.772 | 1.00 | 41.84 | A | C |
| ATOM | 437 | CE | LYS | A | 293 | 14.916 | -3.752 | 26.064 | 1.00 | 42.42 | A | C |
| ATOM | 438 | NZ | LYS | A | 293 | 14.348 | -4.478 | 27.235 | 1.00 | 44.04 | A | N |
| ATOM | 439 | C | LYS | A | 293 | 13.726 | -3.944 | 19.832 | 1.00 | 39.74 | A | C |
| ATOM | 440 | O | LYS | A | 293 | 14.078 | -4.831 | 19.050 | 1.00 | 40.47 | A | O |
| ATOM | 441 | N | GLN | A | 294 | 12.540 | -3.342 | 19.745 | 1.00 | 41.05 | A | N |
| ATOM | 442 | CA | GLN | A | 294 | 11.534 | -3.725 | 18.753 | 1.00 | 42.57 | A | C |
| ATOM | 443 | CB | GLN | A | 294 | 10.155 | -3.174 | 19.163 | 1.00 | 45.80 | A | C |
| ATOM | 444 | CG | GLN | A | 294 | 9.668 | -3.557 | 20.588 | 1.00 | 51.68 | A | C |
| ATOM | 445 | CD | GLN | A | 294 | 9.767 | -5.066 | 20.920 | 1.00 | 56.04 | A | C |
| ATOM | 446 | OE1 | GLN | A | 294 | 10.375 | -5.453 | 21.935 | 1.00 | 57.21 | A | O |
| ATOM | 447 | NE2 | GLN | A | 294 | 9.139 | -5.913 | 20.092 | 1.00 | 56.60 | A | N |
| ATOM | 448 | C | GLN | A | 294 | 11.859 | -3.339 | 17.292 | 1.00 | 41.42 | A | C |
| ATOM | 449 | O | GLN | A | 294 | 11.392 | -3.997 | 16.364 | 1.00 | 41.87 | A | O |
| ATOM | 450 | N | LEU | A | 295 | 12.646 | -2.279 | 17.095 | 1.00 | 39.51 | A | N |
| ATOM | 451 | CA | LEU | A | 295 | 13.013 | -1.833 | 15.732 | 1.00 | 36.77 | A | C |
| ATOM | 452 | CB | LEU | A | 295 | 12.401 | -0.452 | 15.445 | 1.00 | 36.26 | A | C |
| ATOM | 453 | CG | LEU | A | 295 | 10.887 | -0.293 | 15.413 | 1.00 | 34.83 | A | C |
| ATOM | 454 | CD1 | LEU | A | 295 | 10.521 | 1.173 | 15.241 | 1.00 | 33.74 | A | C |
| ATOM | 455 | CD2 | LEU | A | 295 | 10.315 | -1.118 | 14.276 | 1.00 | 35.11 | A | C |
| ATOM | 456 | C | LEU | A | 295 | 14.527 | -1.747 | 15.552 | 1.00 | 35.18 | A | C |
| ATOM | 457 | O | LEU | A | 295 | 15.147 | -0.771 | 15.980 | 1.00 | 34.49 | A | O |
| ATOM | 458 | N | GLN | A | 296 | 15.114 | -2.749 | 14.901 | 1.00 | 34.01 | A | N |
| ATOM | 459 | CA | GLN | A | 296 | 16.563 | -2.773 | 14.669 | 1.00 | 32.63 | A | C |

Figure 9

| ATOM | 460 | CB | GLN | A | 296 | 17.169 | -4.061 | 15.211 | 1.00 | 33.48 | A | C |
|------|-----|-----|-----|---|-----|--------|--------|--------|------|-------|---|---|
| ATOM | 461 | CG | GLN | A | 296 | 16.823 | -4.348 | 16.647 | 1.00 | 35.63 | A | C |
| ATOM | 462 | CD | GLN | A | 296 | 17.445 | -5.638 | 17.126 | 1.00 | 37.32 | A | C |
| ATOM | 463 | OE1 | GLN | A | 296 | 18.087 | -6.360 | 16.352 | 1.00 | 39.13 | A | O |
| ATOM | 464 | NE2 | GLN | A | 296 | 17.289 | -5.930 | 18.410 | 1.00 | 37.65 | A | N |
| ATOM | 465 | C | GLN | A | 296 | 16.892 | -2.653 | 13.190 | 1.00 | 31.37 | A | C |
| ATOM | 466 | O | GLN | A | 296 | 16.445 | -3.462 | 12.377 | 1.00 | 30.69 | A | O |
| ATOM | 467 | N | HIS | A | 297 | 17.756 | -1.695 | 12.877 | 1.00 | 30.10 | A | N |
| ATOM | 468 | CA | HIS | A | 297 | 18.156 | -1.429 | 11.508 | 1.00 | 29.31 | A | C |
| ATOM | 469 | CB | HIS | A | 297 | 17.032 | -0.659 | 10.822 | 1.00 | 27.21 | A | C |
| ATOM | 470 | CG | HIS | A | 297 | 17.124 | -0.666 | 9.325 | 1.00 | 24.99 | A | C |
| ATOM | 471 | CD2 | HIS | A | 297 | 16.606 | -1.512 | 8.409 | 1.00 | 22.26 | A | C |
| ATOM | 472 | ND1 | HIS | A | 297 | 17.806 | 0.298 | 8.619 | 1.00 | 24.04 | A | N |
| ATOM | 473 | CE1 | HIS | A | 297 | 17.704 | 0.045 | 7.330 | 1.00 | 23.02 | A | C |
| ATOM | 474 | NE2 | HIS | A | 297 | 16.980 | -1.050 | 7.177 | 1.00 | 22.62 | A | N |
| ATOM | 475 | C | HIS | A | 297 | 19.444 | -0.595 | 11.474 | 1.00 | 29.90 | A | C |
| ATOM | 476 | O | HIS | A | 297 | 19.738 | 0.146 | 12.424 | 1.00 | 29.26 | A | O |
| ATOM | 477 | N | GLN | A | 298 | 20.202 | -0.703 | 10.378 | 1.00 | 30.77 | A | N |
| ATOM | 478 | CA | GLN | A | 298 | 21.448 | 0.055 | 10.235 | 1.00 | 31.84 | A | C |
| ATOM | 479 | CB | GLN | A | 298 | 22.160 | -0.283 | 8.917 | 1.00 | 36.02 | A | C |
| ATOM | 480 | CG | GLN | A | 298 | 23.020 | -1.553 | 8.943 | 1.00 | 43.20 | A | C |
| ATOM | 481 | CD | GLN | A | 298 | 24.104 | -1.544 | 10.035 | 1.00 | 46.94 | A | C |
| ATOM | 482 | OE1 | GLN | A | 298 | 24.292 | -2.543 | 10.748 | 1.00 | 48.72 | A | O |
| ATOM | 483 | NE2 | GLN | A | 298 | 24.818 | -0.417 | 10.169 | 1.00 | 48.22 | A | N |
| ATOM | 484 | C | GLN | A | 298 | 21.226 | 1.556 | 10.286 | 1.00 | 30.04 | A | C |
| ATOM | 485 | O | GLN | A | 298 | 22.119 | 2.304 | 10.658 | 1.00 | 29.55 | A | O |
| ATOM | 486 | N | ARG | A | 299 | 20.032 | 1.986 | 9.892 | 1.00 | 28.30 | A | N |
| ATOM | 487 | CA | ARG | A | 299 | 19.679 | 3.403 | 9.856 | 1.00 | 26.67 | A | C |
| ATOM | 488 | CB | ARG | A | 299 | 18.746 | 3.672 | 8.680 | 1.00 | 27.57 | A | C |
| ATOM | 489 | CG | ARG | A | 299 | 19.413 | 3.451 | 7.364 | 1.00 | 29.79 | A | C |
| ATOM | 490 | CD | ARG | A | 299 | 20.543 | 4.425 | 7.240 | 1.00 | 31.67 | A | C |
| ATOM | 491 | NE | ARG | A | 299 | 21.595 | 3.906 | 6.385 | 1.00 | 35.80 | A | N |
| ATOM | 492 | CZ | ARG | A | 299 | 22.885 | 3.944 | 6.699 | 1.00 | 35.89 | A | C |
| ATOM | 493 | NH1 | ARG | A | 299 | 23.285 | 4.468 | 7.863 | 1.00 | 34.25 | A | N |
| ATOM | 494 | NH2 | ARG | A | 299 | 23.773 | 3.522 | 5.811 | 1.00 | 35.97 | A | N |
| ATOM | 495 | C | ARG | A | 299 | 19.062 | 3.956 | 11.126 | 1.00 | 24.95 | A | C |
| ATOM | 496 | O | ARG | A | 299 | 18.724 | 5.133 | 11.193 | 1.00 | 24.36 | A | O |
| ATOM | 497 | N | LEU | A | 300 | 18.904 | 3.093 | 12.119 | 1.00 | 23.78 | A | N |
| ATOM | 498 | CA | LEU | A | 300 | 18.330 | 3.463 | 13.400 | 1.00 | 22.98 | A | C |
| ATOM | 499 | CB | LEU | A | 300 | 17.068 | 2.627 | 13.684 | 1.00 | 21.22 | A | C |
| ATOM | 500 | CG | LEU | A | 300 | 15.678 | 2.987 | 13.134 | 1.00 | 18.38 | A | C |
| ATOM | 501 | CD1 | LEU | A | 300 | 15.691 | 3.334 | 11.676 | 1.00 | 16.12 | A | C |
| ATOM | 502 | CD2 | LEU | A | 300 | 14.766 | 1.810 | 13.395 | 1.00 | 18.38 | A | C |
| ATOM | 503 | C | LEU | A | 300 | 19.351 | 3.198 | 14.489 | 1.00 | 23.06 | A | C |
| ATOM | 504 | O | LEU | A | 300 | 20.030 | 2.174 | 14.456 | 1.00 | 23.36 | A | O |
| ATOM | 505 | N | VAL | A | 301 | 19.417 | 4.108 | 15.462 | 1.00 | 24.10 | A | N |
| ATOM | 506 | CA | VAL | A | 301 | 20.319 | 4.007 | 16.615 | 1.00 | 24.83 | A | C |
| ATOM | 507 | CB | VAL | A | 301 | 20.163 | 5.231 | 17.543 | 1.00 | 24.72 | A | C |
| ATOM | 508 | CG1 | VAL | A | 301 | 20.867 | 5.009 | 18.879 | 1.00 | 25.27 | A | C |
| ATOM | 509 | CG2 | VAL | A | 301 | 20.734 | 6.460 | 16.856 | 1.00 | 23.54 | A | C |
| ATOM | 510 | C | VAL | A | 301 | 20.062 | 2.706 | 17.382 | 1.00 | 25.80 | A | C |
| ATOM | 511 | O | VAL | A | 301 | 18.942 | 2.406 | 17.792 | 1.00 | 25.65 | A | O |
| ATOM | 512 | N | ARG | A | 302 | 21.127 | 1.927 | 17.518 | 1.00 | 27.20 | A | N |
| ATOM | 513 | CA | ARG | A | 302 | 21.118 | 0.622 | 18.168 | 1.00 | 28.35 | A | C |
| ATOM | 514 | CB | ARG | A | 302 | 22.219 | -0.234 | 17.517 | 1.00 | 30.00 | A | C |
| ATOM | 515 | CG | ARG | A | 302 | 22.393 | -1.645 | 18.024 | 1.00 | 33.86 | A | C |
| ATOM | 516 | CD | ARG | A | 302 | 23.461 | -1.704 | 19.101 | 1.00 | 37.21 | A | C |
| ATOM | 517 | NE | ARG | A | 302 | 23.971 | -3.057 | 19.335 | 1.00 | 40.15 | A | N |
| ATOM | 518 | CZ | ARG | A | 302 | 24.923 | -3.631 | 18.606 | 1.00 | 40.97 | A | C |

Figure 9

| ATOM | 519 | NH1 | ARG | A | 302 | 25.474 | -2.979 | 17.586 | 1.00 | 42.47 | A | N |
|------|-----|-----|-----|---|-----|--------|--------|--------|------|-------|---|---|
| ATOM | 520 | NH2 | ARG | A | 302 | 25.359 | -4.841 | 18.921 | 1.00 | 41.25 | A | N |
| ATOM | 521 | C | ARG | A | 302 | 21.275 | 0.689 | 19.690 | 1.00 | 28.07 | A | C |
| ATOM | 522 | O | ARG | A | 302 | 22.028 | 1.507 | 20.231 | 1.00 | 27.12 | A | O |
| ATOM | 523 | N | LEU | A | 303 | 20.524 | -0.167 | 20.369 | 1.00 | 28.35 | A | N |
| ATOM | 524 | CA | LEU | A | 303 | 20.570 | -0.249 | 21.824 | 1.00 | 29.42 | A | C |
| ATOM | 525 | CB | LEU | A | 303 | 19.171 | -0.508 | 22.401 | 1.00 | 28.11 | A | C |
| ATOM | 526 | CG | LEU | A | 303 | 19.093 | -0.790 | 23.907 | 1.00 | 28.29 | A | C |
| ATOM | 527 | CD1 | LEU | A | 303 | 19.466 | 0.443 | 24.717 | 1.00 | 27.44 | A | C |
| ATOM | 528 | CD2 | LEU | A | 303 | 17.694 | -1.248 | 24.269 | 1.00 | 29.37 | A | C |
| ATOM | 529 | C | LEU | A | 303 | 21.494 | -1.397 | 22.224 | 1.00 | 29.85 | A | C |
| ATOM | 530 | O | LEU | A | 303 | 21.385 | -2.502 | 21.682 | 1.00 | 30.05 | A | O |
| ATOM | 531 | N | TYR | A | 304 | 22.446 | -1.115 | 23.111 | 1.00 | 30.13 | A | N |
| ATOM | 532 | CA | TYR | A | 304 | 23.347 | -2.156 | 23.591 | 1.00 | 31.00 | A | C |
| ATOM | 533 | CB | TYR | A | 304 | 24.750 | -1.605 | 23.876 | 1.00 | 31.38 | A | C |
| ATOM | 534 | CG | TYR | A | 304 | 25.609 | -1.382 | 22.653 | 1.00 | 31.64 | A | C |
| ATOM | 535 | CD1 | TYR | A | 304 | 25.876 | -0.093 | 22.194 | 1.00 | 31.30 | A | C |
| ATOM | 536 | CE1 | TYR | A | 304 | 26.687 | 0.131 | 21.085 | 1.00 | 30.79 | A | C |
| ATOM | 537 | CD2 | TYR | A | 304 | 26.178 | -2.457 | 21.967 | 1.00 | 32.82 | A | C |
| ATOM | 538 | CE2 | TYR | A | 304 | 27.003 | -2.240 | 20.845 | 1.00 | 32.72 | A | C |
| ATOM | 539 | CZ | TYR | A | 304 | 27.245 | -0.939 | 20.420 | 1.00 | 31.97 | A | C |
| ATOM | 540 | OH | TYR | A | 304 | 28.043 | -0.698 | 19.332 | 1.00 | 33.18 | A | O |
| ATOM | 541 | C | TYR | A | 304 | 22.759 | -2.760 | 24.863 | 1.00 | 30.94 | A | C |
| ATOM | 542 | O | TYR | A | 304 | 22.646 | -3.978 | 24.976 | 1.00 | 31.17 | A | O |
| ATOM | 543 | N | ALA | A | 305 | 22.356 | -1.895 | 25.797 | 1.00 | 31.65 | A | N |
| ATOM | 544 | CA | ALA | A | 305 | 21.789 | -2.338 | 27.063 | 1.00 | 32.14 | A | C |
| ATOM | 545 | CB | ALA | A | 305 | 22.825 | -3.159 | 27.826 | 1.00 | 33.51 | A | C |
| ATOM | 546 | C | ALA | A | 305 | 21.269 | -1.193 | 27.940 | 1.00 | 32.79 | A | C |
| ATOM | 547 | O | ALA | A | 305 | 21.356 | -0.027 | 27.577 | 1.00 | 31.87 | A | O |
| ATOM | 548 | N | VAL | A | 306 | 20.724 | -1.556 | 29.099 | 1.00 | 34.27 | A | N |
| ATOM | 549 | CA | VAL | A | 306 | 20.180 | -0.610 | 30.074 | 1.00 | 35.61 | A | C |
| ATOM | 550 | CB | VAL | A | 306 | 18.612 | -0.573 | 30.036 | 1.00 | 36.17 | A | C |
| ATOM | 551 | CG1 | VAL | A | 306 | 18.112 | 0.098 | 28.771 | 1.00 | 36.44 | A | C |
| ATOM | 552 | CG2 | VAL | A | 306 | 18.035 | -1.975 | 30.129 | 1.00 | 35.79 | A | C |
| ATOM | 553 | C | VAL | A | 306 | 20.595 | -1.012 | 31.497 | 1.00 | 36.86 | A | C |
| ATOM | 554 | O | VAL | A | 306 | 20.820 | -2.184 | 31.768 | 1.00 | 36.92 | A | O |
| ATOM | 555 | N | VAL | A | 307 | 20.732 | -0.035 | 32.389 | 1.00 | 38.52 | A | N |
| ATOM | 556 | CA | VAL | A | 307 | 21.073 | -0.306 | 33.782 | 1.00 | 40.20 | A | C |
| ATOM | 557 | CB | VAL | A | 307 | 22.315 | 0.463 | 34.251 | 1.00 | 39.88 | A | C |
| ATOM | 558 | CG1 | VAL | A | 307 | 22.486 | 0.291 | 35.757 | 1.00 | 39.69 | A | C |
| ATOM | 559 | CG2 | VAL | A | 307 | 23.561 | -0.035 | 33.504 | 1.00 | 38.94 | A | C |
| ATOM | 560 | C | VAL | A | 307 | 19.864 | 0.168 | 34.565 | 1.00 | 42.04 | A | C |
| ATOM | 561 | O | VAL | A | 307 | 19.572 | 1.368 | 34.600 | 1.00 | 41.47 | A | O |
| ATOM | 562 | N | THR | A | 308 | 19.183 | -0.786 | 35.202 | 1.00 | 44.55 | A | N |
| ATOM | 563 | CA | THR | A | 308 | 17.959 | -0.518 | 35.954 | 1.00 | 46.71 | A | C |
| ATOM | 564 | CB | THR | A | 308 | 17.055 | -1.761 | 36.001 | 1.00 | 46.12 | A | C |
| ATOM | 565 | OG1 | THR | A | 308 | 17.714 | -2.816 | 36.705 | 1.00 | 47.40 | A | O |
| ATOM | 566 | CG2 | THR | A | 308 | 16.742 | -2.228 | 34.596 | 1.00 | 45.60 | A | C |
| ATOM | 567 | C | THR | A | 308 | 17.991 | 0.129 | 37.337 | 1.00 | 48.46 | A | C |
| ATOM | 568 | O | THR | A | 308 | 16.966 | 0.644 | 37.778 | 1.00 | 49.38 | A | O |
| ATOM | 569 | N | GLN | A | 309 | 19.113 | 0.101 | 38.045 | 1.00 | 50.58 | A | N |
| ATOM | 570 | CA | GLN | A | 309 | 19.132 | 0.750 | 39.357 | 1.00 | 53.18 | A | C |
| ATOM | 571 | CB | GLN | A | 309 | 20.020 | -0.005 | 40.351 | 1.00 | 56.95 | A | C |
| ATOM | 572 | CG | GLN | A | 309 | 19.539 | -1.447 | 40.654 | 1.00 | 62.35 | A | C |
| ATOM | 573 | CD | GLN | A | 309 | 18.091 | -1.537 | 41.189 | 1.00 | 64.47 | A | C |
| ATOM | 574 | OE1 | GLN | A | 309 | 17.402 | -0.520 | 41.371 | 1.00 | 65.42 | A | O |
| ATOM | 575 | NE2 | GLN | A | 309 | 17.638 | -2.763 | 41.453 | 1.00 | 65.19 | A | N |
| ATOM | 576 | C | GLN | A | 309 | 19.567 | 2.198 | 39.223 | 1.00 | 53.31 | A | C |
| ATOM | 577 | O | GLN | A | 309 | 20.466 | 2.497 | 38.441 | 1.00 | 53.76 | A | O |

Figure 9

| ATOM | 578 | N   | GLU | A | 310 | 18.913 | 3.095 | 39.962 | 1.00 | 53.25 | A | N |
| ATOM | 579 | CA  | GLU | A | 310 | 19.220 | 4.532 | 39.908 | 1.00 | 53.97 | A | C |
| ATOM | 580 | CB  | GLU | A | 310 | 18.222 | 5.364 | 40.751 | 1.00 | 56.42 | A | C |
| ATOM | 581 | CG  | GLU | A | 310 | 18.038 | 4.946 | 42.229 | 1.00 | 60.14 | A | C |
| ATOM | 582 | CD  | GLU | A | 310 | 16.973 | 3.852 | 42.440 | 1.00 | 62.58 | A | C |
| ATOM | 583 | OE1 | GLU | A | 310 | 15.772 | 4.131 | 42.203 | 1.00 | 63.40 | A | O |
| ATOM | 584 | OE2 | GLU | A | 310 | 17.336 | 2.722 | 42.858 | 1.00 | 63.02 | A | O |
| ATOM | 585 | C   | GLU | A | 310 | 20.668 | 4.919 | 40.252 | 1.00 | 53.05 | A | C |
| ATOM | 586 | O   | GLU | A | 310 | 21.238 | 4.420 | 41.229 | 1.00 | 53.67 | A | O |
| ATOM | 587 | N   | PRO | A | 311 | 21.296 | 5.796 | 39.427 | 1.00 | 51.51 | A | N |
| ATOM | 588 | CD  | PRO | A | 311 | 22.646 | 6.313 | 39.710 | 1.00 | 51.42 | A | C |
| ATOM | 589 | CA  | PRO | A | 311 | 20.750 | 6.438 | 38.215 | 1.00 | 49.03 | A | C |
| ATOM | 590 | CB  | PRO | A | 311 | 21.869 | 7.404 | 37.804 | 1.00 | 49.78 | A | C |
| ATOM | 591 | CG  | PRO | A | 311 | 22.590 | 7.681 | 39.084 | 1.00 | 50.65 | A | C |
| ATOM | 592 | C   | PRO | A | 311 | 20.477 | 5.419 | 37.105 | 1.00 | 46.32 | A | C |
| ATOM | 593 | O   | PRO | A | 311 | 21.246 | 4.471 | 36.926 | 1.00 | 46.11 | A | O |
| ATOM | 594 | N   | ILE | A | 312 | 19.380 | 5.607 | 36.369 | 1.00 | 42.90 | A | N |
| ATOM | 595 | CA  | ILE | A | 312 | 19.034 | 4.675 | 35.299 | 1.00 | 38.55 | A | C |
| ATOM | 596 | CB  | ILE | A | 312 | 17.515 | 4.719 | 34.936 | 1.00 | 39.23 | A | C |
| ATOM | 597 | CG2 | ILE | A | 312 | 17.087 | 3.370 | 34.348 | 1.00 | 38.20 | A | C |
| ATOM | 598 | CG1 | ILE | A | 312 | 16.651 | 5.032 | 36.169 | 1.00 | 39.98 | A | C |
| ATOM | 599 | CD1 | ILE | A | 312 | 16.503 | 3.886 | 37.149 | 1.00 | 40.11 | A | C |
| ATOM | 600 | C   | ILE | A | 312 | 19.836 | 5.057 | 34.068 | 1.00 | 34.65 | A | C |
| ATOM | 601 | O   | ILE | A | 312 | 20.000 | 6.246 | 33.787 | 1.00 | 33.09 | A | O |
| ATOM | 602 | N   | TYR | A | 313 | 20.319 | 4.043 | 33.347 | 1.00 | 31.93 | A | N |
| ATOM | 603 | CA  | TYR | A | 313 | 21.116 | 4.228 | 32.121 | 1.00 | 30.67 | A | C |
| ATOM | 604 | CB  | TYR | A | 313 | 22.566 | 3.731 | 32.327 | 1.00 | 30.06 | A | C |
| ATOM | 605 | CG  | TYR | A | 313 | 23.442 | 4.548 | 33.252 | 1.00 | 29.91 | A | C |
| ATOM | 606 | CD1 | TYR | A | 313 | 23.185 | 5.893 | 33.489 | 1.00 | 30.43 | A | C |
| ATOM | 607 | CE1 | TYR | A | 313 | 23.982 | 6.636 | 34.351 | 1.00 | 31.20 | A | C |
| ATOM | 608 | CD2 | TYR | A | 313 | 24.530 | 3.963 | 33.900 | 1.00 | 30.36 | A | C |
| ATOM | 609 | CE2 | TYR | A | 313 | 25.334 | 4.695 | 34.764 | 1.00 | 29.85 | A | C |
| ATOM | 610 | CZ  | TYR | A | 313 | 25.055 | 6.028 | 34.989 | 1.00 | 31.08 | A | C |
| ATOM | 611 | OH  | TYR | A | 313 | 25.827 | 6.762 | 35.864 | 1.00 | 32.07 | A | O |
| ATOM | 612 | C   | TYR | A | 313 | 20.590 | 3.505 | 30.865 | 1.00 | 28.77 | A | C |
| ATOM | 613 | O   | TYR | A | 313 | 20.195 | 2.347 | 30.933 | 1.00 | 28.38 | A | O |
| ATOM | 614 | N   | ILE | A | 314 | 20.603 | 4.190 | 29.725 | 1.00 | 27.22 | A | N |
| ATOM | 615 | CA  | ILE | A | 314 | 20.232 | 3.575 | 28.453 | 1.00 | 26.26 | A | C |
| ATOM | 616 | CB  | ILE | A | 314 | 19.099 | 4.326 | 27.685 | 1.00 | 27.70 | A | C |
| ATOM | 617 | CG2 | ILE | A | 314 | 18.910 | 3.706 | 26.303 | 1.00 | 25.55 | A | C |
| ATOM | 618 | CG1 | ILE | A | 314 | 17.767 | 4.245 | 28.443 | 1.00 | 28.30 | A | C |
| ATOM | 619 | CD1 | ILE | A | 314 | 16.675 | 5.091 | 27.814 | 1.00 | 29.44 | A | C |
| ATOM | 620 | C   | ILE | A | 314 | 21.524 | 3.688 | 27.649 | 1.00 | 25.16 | A | C |
| ATOM | 621 | O   | ILE | A | 314 | 22.013 | 4.786 | 27.392 | 1.00 | 25.82 | A | O |
| ATOM | 622 | N   | ILE | A | 315 | 22.074 | 2.558 | 27.247 | 1.00 | 24.71 | A | N |
| ATOM | 623 | CA  | ILE | A | 315 | 23.327 | 2.554 | 26.503 | 1.00 | 24.74 | A | C |
| ATOM | 624 | CB  | ILE | A | 315 | 24.311 | 1.512 | 27.099 | 1.00 | 25.17 | A | C |
| ATOM | 625 | CG2 | ILE | A | 315 | 25.590 | 1.399 | 26.251 | 1.00 | 23.48 | A | C |
| ATOM | 626 | CG1 | ILE | A | 315 | 24.644 | 1.900 | 28.533 | 1.00 | 25.32 | A | C |
| ATOM | 627 | CD1 | ILE | A | 315 | 24.528 | 0.739 | 29.490 | 1.00 | 27.57 | A | C |
| ATOM | 628 | C   | ILE | A | 315 | 23.128 | 2.295 | 25.021 | 1.00 | 24.01 | A | C |
| ATOM | 629 | O   | ILE | A | 315 | 22.748 | 1.199 | 24.619 | 1.00 | 24.17 | A | O |
| ATOM | 630 | N   | THR | A | 316 | 23.403 | 3.318 | 24.220 | 1.00 | 24.24 | A | N |
| ATOM | 631 | CA  | THR | A | 316 | 23.265 | 3.231 | 22.771 | 1.00 | 23.65 | A | C |
| ATOM | 632 | CB  | THR | A | 316 | 22.305 | 4.311 | 22.237 | 1.00 | 22.81 | A | C |
| ATOM | 633 | OG1 | THR | A | 316 | 22.844 | 5.609 | 22.507 | 1.00 | 21.70 | A | O |
| ATOM | 634 | CG2 | THR | A | 316 | 20.950 | 4.193 | 22.893 | 1.00 | 22.19 | A | C |
| ATOM | 635 | C   | THR | A | 316 | 24.613 | 3.405 | 22.055 | 1.00 | 23.62 | A | C |
| ATOM | 636 | O   | THR | A | 316 | 25.617 | 3.776 | 22.669 | 1.00 | 21.20 | A | O |

Figure 9

| ATOM | 637 | N | GLU | A | 317 | 24.616 | 3.159 | 20.748 | 1.00 | 24.27 | A | N |
|------|-----|-----|-----|---|-----|--------|-------|--------|------|-------|---|---|
| ATOM | 638 | CA | GLU | A | 317 | 25.829 | 3.304 | 19.965 | 1.00 | 24.80 | A | C |
| ATOM | 639 | CB | GLU | A | 317 | 25.647 | 2.769 | 18.543 | 1.00 | 26.47 | A | C |
| ATOM | 640 | CG | GLU | A | 317 | 24.786 | 3.608 | 17.628 | 1.00 | 26.49 | A | C |
| ATOM | 641 | CD | GLU | A | 317 | 24.602 | 2.947 | 16.283 | 1.00 | 28.75 | A | C |
| ATOM | 642 | OE1 | GLU | A | 317 | 23.457 | 2.543 | 15.973 | 1.00 | 28.59 | A | O |
| ATOM | 643 | OE2 | GLU | A | 317 | 25.601 | 2.812 | 15.534 | 1.00 | 29.74 | A | O |
| ATOM | 644 | C | GLU | A | 317 | 26.208 | 4.762 | 19.957 | 1.00 | 24.09 | A | C |
| ATOM | 645 | O | GLU | A | 317 | 25.351 | 5.642 | 20.063 | 1.00 | 25.17 | A | O |
| ATOM | 646 | N | TYR | A | 318 | 27.506 | 5.011 | 19.900 | 1.00 | 23.15 | A | N |
| ATOM | 647 | CA | TYR | A | 318 | 28.027 | 6.359 | 19.911 | 1.00 | 21.87 | A | C |
| ATOM | 648 | CB | TYR | A | 318 | 29.476 | 6.320 | 20.412 | 1.00 | 22.07 | A | C |
| ATOM | 649 | CG | TYR | A | 318 | 30.156 | 7.656 | 20.465 | 1.00 | 23.12 | A | C |
| ATOM | 650 | CD1 | TYR | A | 318 | 29.825 | 8.580 | 21.440 | 1.00 | 24.06 | A | C |
| ATOM | 651 | CE1 | TYR | A | 318 | 30.438 | 9.821 | 21.491 | 1.00 | 24.31 | A | C |
| ATOM | 652 | CD2 | TYR | A | 318 | 31.127 | 8.004 | 19.530 | 1.00 | 23.42 | A | C |
| ATOM | 653 | CE2 | TYR | A | 318 | 31.749 | 9.244 | 19.571 | 1.00 | 23.60 | A | C |
| ATOM | 654 | CZ | TYR | A | 318 | 31.397 | 10.148 | 20.557 | 1.00 | 24.11 | A | C |
| ATOM | 655 | OH | TYR | A | 318 | 31.983 | 11.395 | 20.614 | 1.00 | 25.72 | A | O |
| ATOM | 656 | C | TYR | A | 318 | 27.956 | 6.962 | 18.515 | 1.00 | 21.63 | A | C |
| ATOM | 657 | O | TYR | A | 318 | 28.235 | 6.287 | 17.526 | 1.00 | 21.38 | A | O |
| ATOM | 658 | N | MET | A | 319 | 27.531 | 8.215 | 18.434 | 1.00 | 21.96 | A | N |
| ATOM | 659 | CA | MET | A | 319 | 27.458 | 8.904 | 17.152 | 1.00 | 24.21 | A | C |
| ATOM | 660 | CB | MET | A | 319 | 26.019 | 9.256 | 16.777 | 1.00 | 24.17 | A | C |
| ATOM | 661 | CG | MET | A | 319 | 25.127 | 8.041 | 16.512 | 1.00 | 24.38 | A | C |
| ATOM | 662 | SD | MET | A | 319 | 25.650 | 7.008 | 15.123 | 1.00 | 25.82 | A | S |
| ATOM | 663 | CE | MET | A | 319 | 24.957 | 7.909 | 13.731 | 1.00 | 23.79 | A | C |
| ATOM | 664 | C | MET | A | 319 | 28.325 | 10.148 | 17.250 | 1.00 | 25.48 | A | C |
| ATOM | 665 | O | MET | A | 319 | 27.929 | 11.172 | 17.821 | 1.00 | 25.65 | A | O |
| ATOM | 666 | N | GLU | A | 320 | 29.550 | 9.986 | 16.754 | 1.00 | 27.68 | A | N |
| ATOM | 667 | CA | GLU | A | 320 | 30.615 | 10.996 | 16.729 | 1.00 | 28.80 | A | C |
| ATOM | 668 | CB | GLU | A | 320 | 31.634 | 10.586 | 15.662 | 1.00 | 32.86 | A | C |
| ATOM | 669 | CG | GLU | A | 320 | 32.763 | 11.576 | 15.418 | 1.00 | 36.83 | A | C |
| ATOM | 670 | CD | GLU | A | 320 | 33.843 | 11.443 | 16.444 | 1.00 | 38.61 | A | C |
| ATOM | 671 | OE1 | GLU | A | 320 | 34.499 | 10.380 | 16.455 | 1.00 | 40.28 | A | O |
| ATOM | 672 | OE2 | GLU | A | 320 | 34.018 | 12.384 | 17.245 | 1.00 | 39.53 | A | O |
| ATOM | 673 | C | GLU | A | 320 | 30.230 | 12.458 | 16.498 | 1.00 | 27.56 | A | C |
| ATOM | 674 | O | GLU | A | 320 | 30.515 | 13.333 | 17.333 | 1.00 | 26.81 | A | O |
| ATOM | 675 | N | ASN | A | 321 | 29.616 | 12.729 | 15.353 | 1.00 | 25.64 | A | N |
| ATOM | 676 | CA | ASN | A | 321 | 29.237 | 14.094 | 15.024 | 1.00 | 25.37 | A | C |
| ATOM | 677 | CB | ASN | A | 321 | 29.325 | 14.306 | 13.521 | 1.00 | 25.44 | A | C |
| ATOM | 678 | CG | ASN | A | 321 | 30.754 | 14.260 | 13.046 | 1.00 | 24.46 | A | C |
| ATOM | 679 | OD1 | ASN | A | 321 | 31.558 | 15.091 | 13.449 | 1.00 | 25.62 | A | O |
| ATOM | 680 | ND2 | ASN | A | 321 | 31.097 | 13.258 | 12.254 | 1.00 | 25.00 | A | N |
| ATOM | 681 | C | ASN | A | 321 | 27.941 | 14.622 | 15.618 | 1.00 | 24.58 | A | C |
| ATOM | 682 | O | ASN | A | 321 | 27.443 | 15.686 | 15.231 | 1.00 | 24.16 | A | O |
| ATOM | 683 | N | GLY | A | 322 | 27.437 | 13.886 | 16.601 | 1.00 | 24.06 | A | N |
| ATOM | 684 | CA | GLY | A | 322 | 26.239 | 14.286 | 17.302 | 1.00 | 24.40 | A | C |
| ATOM | 685 | C | GLY | A | 322 | 24.998 | 14.401 | 16.453 | 1.00 | 23.64 | A | C |
| ATOM | 686 | O | GLY | A | 322 | 24.765 | 13.600 | 15.559 | 1.00 | 23.10 | A | O |
| ATOM | 687 | N | SER | A | 323 | 24.230 | 15.441 | 16.738 | 1.00 | 23.76 | A | N |
| ATOM | 688 | CA | SER | A | 323 | 22.970 | 15.725 | 16.068 | 1.00 | 24.24 | A | C |
| ATOM | 689 | CB | SER | A | 323 | 22.112 | 16.554 | 17.010 | 1.00 | 24.14 | A | C |
| ATOM | 690 | OG | SER | A | 323 | 21.004 | 17.096 | 16.353 | 1.00 | 26.00 | A | O |
| ATOM | 691 | C | SER | A | 323 | 23.125 | 16.459 | 14.747 | 1.00 | 23.87 | A | C |
| ATOM | 692 | O | SER | A | 323 | 23.806 | 17.475 | 14.675 | 1.00 | 24.72 | A | O |
| ATOM | 693 | N | LEU | A | 324 | 22.448 | 15.962 | 13.716 | 1.00 | 23.93 | A | N |
| ATOM | 694 | CA | LEU | A | 324 | 22.488 | 16.569 | 12.379 | 1.00 | 23.07 | A | C |
| ATOM | 695 | CB | LEU | A | 324 | 21.491 | 15.861 | 11.432 | 1.00 | 22.18 | A | C |

Figure 9

| ATOM | 696 | CG | LEU | A | 324 | 21.412 | 16.306 | 9.958 | 1.00 | 20.86 | A | C |
|------|-----|-----|-----|---|-----|--------|--------|-------|------|-------|---|---|
| ATOM | 697 | CD1 | LEU | A | 324 | 22.743 | 15.960 | 9.242 | 1.00 | 19.78 | A | C |
| ATOM | 698 | CD2 | LEU | A | 324 | 20.233 | 15.642 | 9.259 | 1.00 | 17.32 | A | C |
| ATOM | 699 | C | LEU | A | 324 | 22.212 | 18.078 | 12.364 | 1.00 | 22.90 | A | C |
| ATOM | 700 | O | LEU | A | 324 | 22.842 | 18.814 | 11.609 | 1.00 | 22.52 | A | O |
| ATOM | 701 | N | VAL | A | 325 | 21.259 | 18.539 | 13.171 | 1.00 | 23.17 | A | N |
| ATOM | 702 | CA | VAL | A | 325 | 20.938 | 19.956 | 13.190 | 1.00 | 23.19 | A | C |
| ATOM | 703 | CB | VAL | A | 325 | 19.647 | 20.239 | 13.995 | 1.00 | 22.26 | A | C |
| ATOM | 704 | CG1 | VAL | A | 325 | 19.925 | 20.268 | 15.479 | 1.00 | 21.98 | A | C |
| ATOM | 705 | CG2 | VAL | A | 325 | 18.998 | 21.522 | 13.508 | 1.00 | 21.31 | A | C |
| ATOM | 706 | C | VAL | A | 325 | 22.123 | 20.807 | 13.663 | 1.00 | 24.75 | A | C |
| ATOM | 707 | O | VAL | A | 325 | 22.246 | 21.969 | 13.289 | 1.00 | 24.50 | A | O |
| ATOM | 708 | N | ASP | A | 326 | 23.010 | 20.216 | 14.459 | 1.00 | 26.49 | A | N |
| ATOM | 709 | CA | ASP | A | 326 | 24.198 | 20.928 | 14.947 | 1.00 | 28.05 | A | C |
| ATOM | 710 | CB | ASP | A | 326 | 24.609 | 20.429 | 16.335 | 1.00 | 28.62 | A | C |
| ATOM | 711 | CG | ASP | A | 326 | 23.530 | 20.642 | 17.380 | 1.00 | 29.35 | A | C |
| ATOM | 712 | OD1 | ASP | A | 326 | 22.947 | 21.749 | 17.440 | 1.00 | 28.94 | A | O |
| ATOM | 713 | OD2 | ASP | A | 326 | 23.284 | 19.695 | 18.157 | 1.00 | 30.99 | A | O |
| ATOM | 714 | C | ASP | A | 326 | 25.365 | 20.748 | 13.974 | 1.00 | 28.53 | A | C |
| ATOM | 715 | O | ASP | A | 326 | 26.046 | 21.718 | 13.622 | 1.00 | 29.01 | A | O |
| ATOM | 716 | N | PHE | A | 327 | 25.557 | 19.510 | 13.516 | 1.00 | 27.78 | A | N |
| ATOM | 717 | CA | PHE | A | 327 | 26.623 | 19.175 | 12.583 | 1.00 | 27.96 | A | C |
| ATOM | 718 | CB | PHE | A | 327 | 26.594 | 17.685 | 12.226 | 1.00 | 28.42 | A | C |
| ATOM | 719 | CG | PHE | A | 327 | 27.633 | 17.295 | 11.214 | 1.00 | 29.28 | A | C |
| ATOM | 720 | CD1 | PHE | A | 327 | 28.991 | 17.378 | 11.526 | 1.00 | 30.08 | A | C |
| ATOM | 721 | CD2 | PHE | A | 327 | 27.264 | 16.919 | 9.927 | 1.00 | 29.95 | A | C |
| ATOM | 722 | CE1 | PHE | A | 327 | 29.963 | 17.103 | 10.573 | 1.00 | 29.65 | A | C |
| ATOM | 723 | CE2 | PHE | A | 327 | 28.226 | 16.641 | 8.968 | 1.00 | 30.44 | A | C |
| ATOM | 724 | CZ | PHE | A | 327 | 29.582 | 16.734 | 9.290 | 1.00 | 30.07 | A | C |
| ATOM | 725 | C | PHE | A | 327 | 26.600 | 19.991 | 11.298 | 1.00 | 28.55 | A | C |
| ATOM | 726 | O | PHE | A | 327 | 27.651 | 20.350 | 10.778 | 1.00 | 28.99 | A | O |
| ATOM | 727 | N | LEU | A | 328 | 25.409 | 20.253 | 10.769 | 1.00 | 28.98 | A | N |
| ATOM | 728 | CA | LEU | A | 328 | 25.262 | 21.020 | 9.533 | 1.00 | 29.38 | A | C |
| ATOM | 729 | CB | LEU | A | 328 | 23.796 | 21.046 | 9.088 | 1.00 | 28.14 | A | C |
| ATOM | 730 | CG | LEU | A | 328 | 23.177 | 19.726 | 8.631 | 1.00 | 27.88 | A | C |
| ATOM | 731 | CD1 | LEU | A | 328 | 21.660 | 19.900 | 8.476 | 1.00 | 27.73 | A | C |
| ATOM | 732 | CD2 | LEU | A | 328 | 23.832 | 19.234 | 7.331 | 1.00 | 25.81 | A | C |
| ATOM | 733 | C | LEU | A | 328 | 25.794 | 22.445 | 9.647 | 1.00 | 30.15 | A | C |
| ATOM | 734 | O | LEU | A | 328 | 26.171 | 23.040 | 8.642 | 1.00 | 29.89 | A | O |
| ATOM | 735 | N | LYS | A | 329 | 25.822 | 22.984 | 10.868 | 1.00 | 32.06 | A | N |
| ATOM | 736 | CA | LYS | A | 329 | 26.313 | 24.344 | 11.113 | 1.00 | 33.94 | A | C |
| ATOM | 737 | CB | LYS | A | 329 | 25.542 | 25.012 | 12.254 | 1.00 | 34.07 | A | C |
| ATOM | 738 | CG | LYS | A | 329 | 24.038 | 25.047 | 12.082 | 1.00 | 35.82 | A | C |
| ATOM | 739 | CD | LYS | A | 329 | 23.409 | 25.920 | 13.156 | 1.00 | 37.56 | A | C |
| ATOM | 740 | CE | LYS | A | 329 | 21.908 | 25.740 | 13.237 | 1.00 | 38.23 | A | C |
| ATOM | 741 | NZ | LYS | A | 329 | 21.564 | 24.402 | 13.775 | 1.00 | 39.31 | A | N |
| ATOM | 742 | C | LYS | A | 329 | 27.821 | 24.452 | 11.396 | 1.00 | 34.93 | A | C |
| ATOM | 743 | O | LYS | A | 329 | 28.342 | 25.567 | 11.497 | 1.00 | 35.69 | A | O |
| ATOM | 744 | N | THR | A | 330 | 28.501 | 23.310 | 11.567 | 1.00 | 35.80 | A | N |
| ATOM | 745 | CA | THR | A | 330 | 29.956 | 23.267 | 11.819 | 1.00 | 35.98 | A | C |
| ATOM | 746 | CB | THR | A | 330 | 30.436 | 21.861 | 12.310 | 1.00 | 34.79 | A | C |
| ATOM | 747 | OG1 | THR | A | 330 | 30.263 | 20.895 | 11.268 | 1.00 | 33.55 | A | O |
| ATOM | 748 | CG2 | THR | A | 330 | 29.684 | 21.407 | 13.549 | 1.00 | 34.41 | A | C |
| ATOM | 749 | C | THR | A | 330 | 30.702 | 23.554 | 10.510 | 1.00 | 37.14 | A | C |
| ATOM | 750 | O | THR | A | 330 | 30.142 | 23.366 | 9.438 | 1.00 | 36.95 | A | O |
| ATOM | 751 | N | PRO | A | 331 | 31.968 | 24.019 | 10.583 | 1.00 | 38.38 | A | N |
| ATOM | 752 | CD | PRO | A | 331 | 32.714 | 24.455 | 11.783 | 1.00 | 39.28 | A | C |
| ATOM | 753 | CA | PRO | A | 331 | 32.749 | 24.311 | 9.379 | 1.00 | 39.17 | A | C |
| ATOM | 754 | CB | PRO | A | 331 | 34.154 | 24.506 | 9.942 | 1.00 | 38.66 | A | C |

Figure 9

| | | | | | | | | | | | |
|---|---|---|---|---|---|---|---|---|---|---|---|
| ATOM | 755 | CG | PRO | A | 331 | 33.863 | 25.267 | 11.190 | 1.00 | 37.84 | A C |
| ATOM | 756 | C | PRO | A | 331 | 32.692 | 23.202 | 8.324 | 1.00 | 39.94 | A C |
| ATOM | 757 | O | PRO | A | 331 | 32.517 | 23.496 | 7.146 | 1.00 | 40.11 | A O |
| ATOM | 758 | N | SER | A | 332 | 32.785 | 21.942 | 8.759 | 1.00 | 40.87 | A N |
| ATOM | 759 | CA | SER | A | 332 | 32.729 | 20.773 | 7.863 | 1.00 | 41.94 | A C |
| ATOM | 760 | CB | SER | A | 332 | 33.102 | 19.492 | 8.614 | 1.00 | 42.67 | A C |
| ATOM | 761 | OG | SER | A | 332 | 34.190 | 19.693 | 9.491 | 1.00 | 45.94 | A O |
| ATOM | 762 | C | SER | A | 332 | 31.318 | 20.566 | 7.289 | 1.00 | 42.09 | A C |
| ATOM | 763 | O | SER | A | 332 | 31.161 | 20.072 | 6.164 | 1.00 | 42.21 | A O |
| ATOM | 764 | N | GLY | A | 333 | 30.305 | 20.866 | 8.104 | 1.00 | 41.55 | A N |
| ATOM | 765 | CA | GLY | A | 333 | 28.923 | 20.718 | 7.677 | 1.00 | 41.03 | A C |
| ATOM | 766 | C | GLY | A | 333 | 28.579 | 21.713 | 6.590 | 1.00 | 40.72 | A C |
| ATOM | 767 | O | GLY | A | 333 | 28.021 | 21.343 | 5.556 | 1.00 | 40.36 | A O |
| ATOM | 768 | N | ILE | A | 334 | 28.932 | 22.975 | 6.831 | 1.00 | 40.80 | A N |
| ATOM | 769 | CA | ILE | A | 334 | 28.696 | 24.068 | 5.887 | 1.00 | 41.16 | A C |
| ATOM | 770 | CB | ILE | A | 334 | 29.309 | 25.409 | 6.409 | 1.00 | 41.71 | A C |
| ATOM | 771 | CG2 | ILE | A | 334 | 29.339 | 26.464 | 5.310 | 1.00 | 41.96 | A C |
| ATOM | 772 | CG1 | ILE | A | 334 | 28.550 | 25.911 | 7.649 | 1.00 | 42.52 | A C |
| ATOM | 773 | CD1 | ILE | A | 334 | 27.093 | 26.319 | 7.402 | 1.00 | 43.68 | A C |
| ATOM | 774 | C | ILE | A | 334 | 29.308 | 23.734 | 4.530 | 1.00 | 41.00 | A C |
| ATOM | 775 | O | ILE | A | 334 | 28.721 | 24.037 | 3.495 | 1.00 | 41.98 | A O |
| ATOM | 776 | N | LYS | A | 335 | 30.448 | 23.048 | 4.548 | 1.00 | 40.64 | A N |
| ATOM | 777 | CA | LYS | A | 335 | 31.173 | 22.668 | 3.336 | 1.00 | 40.41 | A C |
| ATOM | 778 | CB | LYS | A | 335 | 32.649 | 22.389 | 3.666 | 1.00 | 42.34 | A C |
| ATOM | 779 | CG | LYS | A | 335 | 33.476 | 23.614 | 4.109 | 1.00 | 45.46 | A C |
| ATOM | 780 | CD | LYS | A | 335 | 34.897 | 23.197 | 4.557 | 1.00 | 48.04 | A C |
| ATOM | 781 | CE | LYS | A | 335 | 35.579 | 24.280 | 5.420 | 1.00 | 50.01 | A C |
| ATOM | 782 | NZ | LYS | A | 335 | 36.324 | 23.705 | 6.597 | 1.00 | 50.56 | A N |
| ATOM | 783 | C | LYS | A | 335 | 30.620 | 21.493 | 2.522 | 1.00 | 39.31 | A C |
| ATOM | 784 | O | LYS | A | 335 | 31.048 | 21.285 | 1.385 | 1.00 | 38.87 | A O |
| ATOM | 785 | N | LEU | A | 336 | 29.682 | 20.727 | 3.084 | 1.00 | 38.49 | A N |
| ATOM | 786 | CA | LEU | A | 336 | 29.118 | 19.557 | 2.381 | 1.00 | 36.93 | A C |
| ATOM | 787 | CB | LEU | A | 336 | 28.106 | 18.802 | 3.262 | 1.00 | 36.49 | A C |
| ATOM | 788 | CG | LEU | A | 336 | 28.569 | 18.067 | 4.527 | 1.00 | 35.40 | A C |
| ATOM | 789 | CD1 | LEU | A | 336 | 27.359 | 17.492 | 5.239 | 1.00 | 34.28 | A C |
| ATOM | 790 | CD2 | LEU | A | 336 | 29.552 | 16.957 | 4.184 | 1.00 | 33.98 | A C |
| ATOM | 791 | C | LEU | A | 336 | 28.464 | 19.872 | 1.035 | 1.00 | 35.85 | A C |
| ATOM | 792 | O | LEU | A | 336 | 27.760 | 20.874 | 0.886 | 1.00 | 35.02 | A O |
| ATOM | 793 | N | THR | A | 337 | 28.690 | 18.989 | 0.068 | 1.00 | 35.38 | A N |
| ATOM | 794 | CA | THR | A | 337 | 28.132 | 19.140 | -1.273 | 1.00 | 34.97 | A C |
| ATOM | 795 | CB | THR | A | 337 | 28.927 | 18.330 | -2.328 | 1.00 | 35.07 | A C |
| ATOM | 796 | OG1 | THR | A | 337 | 28.754 | 16.926 | -2.101 | 1.00 | 34.97 | A O |
| ATOM | 797 | CG2 | THR | A | 337 | 30.417 | 18.669 | -2.265 | 1.00 | 35.37 | A C |
| ATOM | 798 | C | THR | A | 337 | 26.678 | 18.669 | -1.302 | 1.00 | 35.13 | A C |
| ATOM | 799 | O | THR | A | 337 | 26.249 | 17.897 | -0.436 | 1.00 | 35.24 | A O |
| ATOM | 800 | N | ILE | A | 338 | 25.935 | 19.119 | -2.313 | 1.00 | 34.05 | A N |
| ATOM | 801 | CA | ILE | A | 338 | 24.534 | 18.745 | -2.461 | 1.00 | 32.22 | A C |
| ATOM | 802 | CB | ILE | A | 338 | 23.861 | 19.499 | -3.652 | 1.00 | 32.23 | A C |
| ATOM | 803 | CG2 | ILE | A | 338 | 24.559 | 19.170 | -4.970 | 1.00 | 32.03 | A C |
| ATOM | 804 | CG1 | ILE | A | 338 | 22.370 | 19.146 | -3.738 | 1.00 | 32.74 | A C |
| ATOM | 805 | CD1 | ILE | A | 338 | 21.506 | 19.727 | -2.622 | 1.00 | 31.06 | A C |
| ATOM | 806 | C | ILE | A | 338 | 24.413 | 17.232 | -2.627 | 1.00 | 30.88 | A C |
| ATOM | 807 | O | ILE | A | 338 | 23.471 | 16.626 | -2.136 | 1.00 | 30.60 | A O |
| ATOM | 808 | N | ASN | A | 339 | 25.425 | 16.622 | -3.230 | 1.00 | 30.21 | A N |
| ATOM | 809 | CA | ASN | A | 339 | 25.449 | 15.177 | -3.453 | 1.00 | 30.02 | A C |
| ATOM | 810 | CB | ASN | A | 339 | 26.675 | 14.801 | -4.287 | 1.00 | 30.62 | A C |
| ATOM | 811 | CG | ASN | A | 339 | 26.739 | 15.563 | -5.592 | 1.00 | 31.42 | A C |
| ATOM | 812 | OD1 | ASN | A | 339 | 26.472 | 15.002 | -6.650 | 1.00 | 32.82 | A O |
| ATOM | 813 | ND2 | ASN | A | 339 | 27.079 | 16.849 | -5.527 | 1.00 | 31.05 | A N |

Figure 9

| ATOM | 814 | C   | ASN A 339 | 25.491 | 14.416 | -2.138 | 1.00 | 29.99 | A | C |
|------|-----|-----|-----------|--------|--------|--------|------|-------|---|---|
| ATOM | 815 | O   | ASN A 339 | 24.901 | 13.333 | -2.009 | 1.00 | 30.52 | A | O |
| ATOM | 816 | N   | LYS A 340 | 26.246 | 14.959 | -1.186 | 1.00 | 28.94 | A | N |
| ATOM | 817 | CA  | LYS A 340 | 26.374 | 14.355 | 0.132  | 1.00 | 28.52 | A | C |
| ATOM | 818 | CB  | LYS A 340 | 27.613 | 14.885 | 0.859  | 1.00 | 28.87 | A | C |
| ATOM | 819 | CG  | LYS A 340 | 27.743 | 14.398 | 2.284  | 1.00 | 28.98 | A | C |
| ATOM | 820 | CD  | LYS A 340 | 27.785 | 12.877 | 2.387  | 1.00 | 29.57 | A | C |
| ATOM | 821 | CE  | LYS A 340 | 27.808 | 12.467 | 3.861  | 1.00 | 31.49 | A | C |
| ATOM | 822 | NZ  | LYS A 340 | 27.883 | 10.994 | 4.088  | 1.00 | 33.98 | A | N |
| ATOM | 823 | C   | LYS A 340 | 25.116 | 14.632 | 0.953  | 1.00 | 27.10 | A | C |
| ATOM | 824 | O   | LYS A 340 | 24.615 | 13.740 | 1.630  | 1.00 | 27.37 | A | O |
| ATOM | 825 | N   | LEU A 341 | 24.610 | 15.861 | 0.876  | 1.00 | 26.17 | A | N |
| ATOM | 826 | CA  | LEU A 341 | 23.397 | 16.246 | 1.586  | 1.00 | 26.36 | A | C |
| ATOM | 827 | CB  | LEU A 341 | 23.060 | 17.714 | 1.319  | 1.00 | 25.26 | A | C |
| ATOM | 828 | CG  | LEU A 341 | 23.977 | 18.742 | 1.986  | 1.00 | 24.68 | A | C |
| ATOM | 829 | CD1 | LEU A 341 | 23.516 | 20.137 | 1.646  | 1.00 | 23.72 | A | C |
| ATOM | 830 | CD2 | LEU A 341 | 23.990 | 18.539 | 3.493  | 1.00 | 23.91 | A | C |
| ATOM | 831 | C   | LEU A 341 | 22.220 | 15.350 | 1.192  | 1.00 | 26.44 | A | C |
| ATOM | 832 | O   | LEU A 341 | 21.410 | 14.974 | 2.043  | 1.00 | 27.13 | A | O |
| ATOM | 833 | N   | LEU A 342 | 22.137 | 14.995 | -0.087 | 1.00 | 26.29 | A | N |
| ATOM | 834 | CA  | LEU A 342 | 21.073 | 14.124 | -0.568 | 1.00 | 26.25 | A | C |
| ATOM | 835 | CB  | LEU A 342 | 20.886 | 14.262 | -2.072 | 1.00 | 28.25 | A | C |
| ATOM | 836 | CG  | LEU A 342 | 20.441 | 15.664 | -2.487 | 1.00 | 30.90 | A | C |
| ATOM | 837 | CD1 | LEU A 342 | 20.034 | 15.630 | -3.909 | 1.00 | 32.59 | A | C |
| ATOM | 838 | CD2 | LEU A 342 | 19.277 | 16.168 | -1.648 | 1.00 | 32.43 | A | C |
| ATOM | 839 | C   | LEU A 342 | 21.276 | 12.667 | -0.183 | 1.00 | 25.62 | A | C |
| ATOM | 840 | O   | LEU A 342 | 20.296 | 11.930 | -0.023 | 1.00 | 25.08 | A | O |
| ATOM | 841 | N   | ASP A 343 | 22.532 | 12.241 | -0.043 | 1.00 | 24.95 | A | N |
| ATOM | 842 | CA  | ASP A 343 | 22.798 | 10.871 | 0.376  | 1.00 | 25.27 | A | C |
| ATOM | 843 | CB  | ASP A 343 | 24.267 | 10.511 | 0.221  | 1.00 | 29.26 | A | C |
| ATOM | 844 | CG  | ASP A 343 | 24.534 | 9.046  | 0.543  | 1.00 | 33.43 | A | C |
| ATOM | 845 | OD1 | ASP A 343 | 23.760 | 8.172  | 0.070  | 1.00 | 36.05 | A | O |
| ATOM | 846 | OD2 | ASP A 343 | 25.501 | 8.764  | 1.288  | 1.00 | 36.37 | A | O |
| ATOM | 847 | C   | ASP A 343 | 22.380 | 10.712 | 1.840  | 1.00 | 23.52 | A | C |
| ATOM | 848 | O   | ASP A 343 | 21.869 | 9.673  | 2.249  | 1.00 | 22.10 | A | O |
| ATOM | 849 | N   | MET A 344 | 22.614 | 11.753 | 2.627  | 1.00 | 22.83 | A | N |
| ATOM | 850 | CA  | MET A 344 | 22.220 | 11.749 | 4.028  | 1.00 | 23.12 | A | C |
| ATOM | 851 | CB  | MET A 344 | 22.749 | 13.003 | 4.711  | 1.00 | 23.05 | A | C |
| ATOM | 852 | CG  | MET A 344 | 24.250 | 13.064 | 4.750  | 1.00 | 24.94 | A | C |
| ATOM | 853 | SD  | MET A 344 | 24.784 | 14.601 | 5.444  | 1.00 | 27.67 | A | S |
| ATOM | 854 | CE  | MET A 344 | 25.391 | 14.103 | 7.021  | 1.00 | 27.49 | A | C |
| ATOM | 855 | C   | MET A 344 | 20.680 | 11.693 | 4.128  | 1.00 | 22.62 | A | C |
| ATOM | 856 | O   | MET A 344 | 20.130 | 10.954 | 4.944  | 1.00 | 22.28 | A | O |
| ATOM | 857 | N   | ALA A 345 | 20.012 | 12.495 | 3.292  | 1.00 | 22.00 | A | N |
| ATOM | 858 | CA  | ALA A 345 | 18.549 | 12.555 | 3.217  | 1.00 | 21.05 | A | C |
| ATOM | 859 | CB  | ALA A 345 | 18.124 | 13.587 | 2.159  | 1.00 | 20.28 | A | C |
| ATOM | 860 | C   | ALA A 345 | 18.006 | 11.171 | 2.853  | 1.00 | 20.45 | A | C |
| ATOM | 861 | O   | ALA A 345 | 17.038 | 10.710 | 3.443  | 1.00 | 18.96 | A | O |
| ATOM | 862 | N   | ALA A 346 | 18.682 | 10.505 | 1.912  | 1.00 | 20.36 | A | N |
| ATOM | 863 | CA  | ALA A 346 | 18.316 | 9.171  | 1.455  | 1.00 | 20.00 | A | C |
| ATOM | 864 | CB  | ALA A 346 | 19.156 | 8.792  | 0.259  | 1.00 | 19.73 | A | C |
| ATOM | 865 | C   | ALA A 346 | 18.480 | 8.121  | 2.548  | 1.00 | 21.16 | A | C |
| ATOM | 866 | O   | ALA A 346 | 17.754 | 7.125  | 2.574  | 1.00 | 21.48 | A | O |
| ATOM | 867 | N   | GLN A 347 | 19.476 | 8.307  | 3.411  | 1.00 | 21.30 | A | N |
| ATOM | 868 | CA  | GLN A 347 | 19.708 | 7.374  | 4.515  | 1.00 | 20.85 | A | C |
| ATOM | 869 | CB  | GLN A 347 | 21.034 | 7.663  | 5.227  | 1.00 | 20.78 | A | C |
| ATOM | 870 | CG  | GLN A 347 | 22.226 | 7.420  | 4.342  | 1.00 | 22.55 | A | C |
| ATOM | 871 | CD  | GLN A 347 | 23.534 | 7.669  | 5.037  | 1.00 | 24.40 | A | C |
| ATOM | 872 | OE1 | GLN A 347 | 24.391 | 6.795  | 5.049  | 1.00 | 27.31 | A | O |

Figure 9

| | | | | | | | | | | | |
|---|---|---|---|---|---|---|---|---|---|---|---|
| ATOM | 873 | NE2 | GLN | A | 347 | 23.714 | 8.865 | 5.597 | 1.00 | 23.42 | A | N |
| ATOM | 874 | C | GLN | A | 347 | 18.579 | 7.490 | 5.514 | 1.00 | 19.33 | A | C |
| ATOM | 875 | O | GLN | A | 347 | 18.136 | 6.485 | 6.069 | 1.00 | 18.81 | A | O |
| ATOM | 876 | N | ILE | A | 348 | 18.137 | 8.727 | 5.739 | 1.00 | 19.32 | A | N |
| ATOM | 877 | CA | ILE | A | 348 | 17.052 | 9.026 | 6.675 | 1.00 | 20.12 | A | C |
| ATOM | 878 | CB | ILE | A | 348 | 16.939 | 10.555 | 6.942 | 1.00 | 19.47 | A | C |
| ATOM | 879 | CG2 | ILE | A | 348 | 15.826 | 10.848 | 7.952 | 1.00 | 19.85 | A | C |
| ATOM | 880 | CG1 | ILE | A | 348 | 18.267 | 11.078 | 7.496 | 1.00 | 19.71 | A | C |
| ATOM | 881 | CD1 | ILE | A | 348 | 18.346 | 12.576 | 7.635 | 1.00 | 18.76 | A | C |
| ATOM | 882 | C | ILE | A | 348 | 15.729 | 8.455 | 6.141 | 1.00 | 20.36 | A | C |
| ATOM | 883 | O | ILE | A | 348 | 14.958 | 7.844 | 6.898 | 1.00 | 20.42 | A | O |
| ATOM | 884 | N | ALA | A | 349 | 15.499 | 8.626 | 4.837 | 1.00 | 19.77 | A | N |
| ATOM | 885 | CA | ALA | A | 349 | 14.303 | 8.106 | 4.180 | 1.00 | 19.46 | A | C |
| ATOM | 886 | CB | ALA | A | 349 | 14.264 | 8.549 | 2.715 | 1.00 | 17.97 | A | C |
| ATOM | 887 | C | ALA | A | 349 | 14.303 | 6.577 | 4.272 | 1.00 | 19.92 | A | C |
| ATOM | 888 | O | ALA | A | 349 | 13.261 | 5.963 | 4.498 | 1.00 | 20.73 | A | O |
| ATOM | 889 | N | GLU | A | 350 | 15.484 | 5.971 | 4.134 | 1.00 | 20.82 | A | N |
| ATOM | 890 | CA | GLU | A | 350 | 15.648 | 4.514 | 4.204 | 1.00 | 20.61 | A | C |
| ATOM | 891 | CB | GLU | A | 350 | 17.092 | 4.133 | 3.861 | 1.00 | 22.25 | A | C |
| ATOM | 892 | CG | GLU | A | 350 | 17.362 | 2.639 | 3.815 | 1.00 | 24.56 | A | C |
| ATOM | 893 | CD | GLU | A | 350 | 18.861 | 2.292 | 3.842 | 1.00 | 26.48 | A | C |
| ATOM | 894 | OE1 | GLU | A | 350 | 19.722 | 3.192 | 3.668 | 1.00 | 25.97 | A | O |
| ATOM | 895 | OE2 | GLU | A | 350 | 19.173 | 1.098 | 4.040 | 1.00 | 27.65 | A | O |
| ATOM | 896 | C | GLU | A | 350 | 15.272 | 3.983 | 5.591 | 1.00 | 20.05 | A | C |
| ATOM | 897 | O | GLU | A | 350 | 14.651 | 2.922 | 5.717 | 1.00 | 20.48 | A | O |
| ATOM | 898 | N | GLY | A | 351 | 15.654 | 4.724 | 6.628 | 1.00 | 19.00 | A | N |
| ATOM | 899 | CA | GLY | A | 351 | 15.320 | 4.332 | 7.986 | 1.00 | 17.16 | A | C |
| ATOM | 900 | C | GLY | A | 351 | 13.823 | 4.500 | 8.215 | 1.00 | 16.64 | A | C |
| ATOM | 901 | O | GLY | A | 351 | 13.200 | 3.668 | 8.855 | 1.00 | 16.32 | A | O |
| ATOM | 902 | N | MET | A | 352 | 13.246 | 5.566 | 7.668 | 1.00 | 16.33 | A | N |
| ATOM | 903 | CA | MET | A | 352 | 11.819 | 5.815 | 7.805 | 1.00 | 16.89 | A | C |
| ATOM | 904 | CB | MET | A | 352 | 11.473 | 7.237 | 7.396 | 1.00 | 16.19 | A | C |
| ATOM | 905 | CG | MET | A | 352 | 11.878 | 8.298 | 8.419 | 1.00 | 17.59 | A | C |
| ATOM | 906 | SD | MET | A | 352 | 11.301 | 7.974 | 10.123 | 1.00 | 18.20 | A | S |
| ATOM | 907 | CE | MET | A | 352 | 9.476 | 7.780 | 9.883 | 1.00 | 16.22 | A | C |
| ATOM | 908 | C | MET | A | 352 | 11.017 | 4.825 | 6.982 | 1.00 | 17.74 | A | C |
| ATOM | 909 | O | MET | A | 352 | 9.867 | 4.522 | 7.314 | 1.00 | 18.81 | A | O |
| ATOM | 910 | N | ALA | A | 353 | 11.627 | 4.305 | 5.917 | 1.00 | 18.00 | A | N |
| ATOM | 911 | CA | ALA | A | 353 | 10.963 | 3.330 | 5.070 | 1.00 | 18.74 | A | C |
| ATOM | 912 | CB | ALA | A | 353 | 11.722 | 3.136 | 3.789 | 1.00 | 17.04 | A | C |
| ATOM | 913 | C | ALA | A | 353 | 10.859 | 2.019 | 5.847 | 1.00 | 19.97 | A | C |
| ATOM | 914 | O | ALA | A | 353 | 9.941 | 1.221 | 5.625 | 1.00 | 21.46 | A | O |
| ATOM | 915 | N | PHE | A | 354 | 11.805 | 1.792 | 6.757 | 1.00 | 20.20 | A | N |
| ATOM | 916 | CA | PHE | A | 354 | 11.789 | 0.591 | 7.577 | 1.00 | 19.20 | A | C |
| ATOM | 917 | CB | PHE | A | 354 | 13.144 | 0.372 | 8.234 | 1.00 | 18.23 | A | C |
| ATOM | 918 | CG | PHE | A | 354 | 13.144 | -0.726 | 9.260 | 1.00 | 19.46 | A | C |
| ATOM | 919 | CD1 | PHE | A | 354 | 13.097 | -2.064 | 8.866 | 1.00 | 20.22 | A | C |
| ATOM | 920 | CD2 | PHE | A | 354 | 13.191 | -0.423 | 10.622 | 1.00 | 20.27 | A | C |
| ATOM | 921 | CE1 | PHE | A | 354 | 13.099 | -3.090 | 9.810 | 1.00 | 21.12 | A | C |
| ATOM | 922 | CE2 | PHE | A | 354 | 13.194 | -1.440 | 11.581 | 1.00 | 21.18 | A | C |
| ATOM | 923 | CZ | PHE | A | 354 | 13.148 | -2.777 | 11.174 | 1.00 | 21.60 | A | C |
| ATOM | 924 | C | PHE | A | 354 | 10.715 | 0.740 | 8.645 | 1.00 | 19.06 | A | C |
| ATOM | 925 | O | PHE | A | 354 | 9.981 | -0.200 | 8.931 | 1.00 | 18.96 | A | O |
| ATOM | 926 | N | ILE | A | 355 | 10.656 | 1.922 | 9.257 | 1.00 | 20.48 | A | N |
| ATOM | 927 | CA | ILE | A | 355 | 9.672 | 2.226 | 10.293 | 1.00 | 20.33 | A | C |
| ATOM | 928 | CB | ILE | A | 355 | 9.924 | 3.638 | 10.889 | 1.00 | 19.06 | A | C |
| ATOM | 929 | CG2 | ILE | A | 355 | 8.734 | 4.117 | 11.715 | 1.00 | 18.22 | A | C |
| ATOM | 930 | CG1 | ILE | A | 355 | 11.197 | 3.601 | 11.753 | 1.00 | 18.16 | A | C |
| ATOM | 931 | CD1 | ILE | A | 355 | 11.608 | 4.931 | 12.350 | 1.00 | 16.47 | A | C |

Figure 9

| ATOM | 932 | C | ILE A 355 | 8.276 | 2.084 | 9.678 | 1.00 | 21.92 | A | C |
|---|---|---|---|---|---|---|---|---|---|---|
| ATOM | 933 | O | ILE A 355 | 7.387 | 1.466 | 10.270 | 1.00 | 22.61 | A | O |
| ATOM | 934 | N | GLU A 356 | 8.140 | 2.566 | 8.447 | 1.00 | 22.70 | A | N |
| ATOM | 935 | CA | GLU A 356 | 6.901 | 2.491 | 7.676 | 1.00 | 24.16 | A | C |
| ATOM | 936 | CB | GLU A 356 | 7.127 | 3.211 | 6.355 | 1.00 | 22.56 | A | C |
| ATOM | 937 | CG | GLU A 356 | 5.954 | 3.239 | 5.394 | 1.00 | 20.20 | A | C |
| ATOM | 938 | CD | GLU A 356 | 6.261 | 4.110 | 4.201 | 1.00 | 18.46 | A | C |
| ATOM | 939 | OE1 | GLU A 356 | 6.900 | 3.627 | 3.243 | 1.00 | 20.94 | A | O |
| ATOM | 940 | OE2 | GLU A 356 | 5.901 | 5.298 | 4.236 | 1.00 | 19.17 | A | O |
| ATOM | 941 | C | GLU A 356 | 6.492 | 1.023 | 7.429 | 1.00 | 26.20 | A | C |
| ATOM | 942 | O | GLU A 356 | 5.375 | 0.615 | 7.731 | 1.00 | 27.28 | A | O |
| ATOM | 943 | N | GLU A 357 | 7.420 | 0.248 | 6.884 | 1.00 | 28.20 | A | N |
| ATOM | 944 | CA | GLU A 357 | 7.257 | -1.175 | 6.588 | 1.00 | 30.08 | A | C |
| ATOM | 945 | CB | GLU A 357 | 8.625 | -1.703 | 6.095 | 1.00 | 32.89 | A | C |
| ATOM | 946 | CG | GLU A 357 | 8.823 | -3.205 | 6.026 | 1.00 | 37.69 | A | C |
| ATOM | 947 | CD | GLU A 357 | 8.061 | -3.848 | 4.881 | 1.00 | 42.70 | A | C |
| ATOM | 948 | OE1 | GLU A 357 | 8.092 | -3.313 | 3.746 | 1.00 | 45.24 | A | O |
| ATOM | 949 | OE2 | GLU A 357 | 7.434 | -4.904 | 5.115 | 1.00 | 45.67 | A | O |
| ATOM | 950 | C | GLU A 357 | 6.795 | -1.960 | 7.826 | 1.00 | 30.27 | A | C |
| ATOM | 951 | O | GLU A 357 | 5.997 | -2.891 | 7.726 | 1.00 | 30.24 | A | O |
| ATOM | 952 | N | ARG A 358 | 7.287 | -1.562 | 8.995 | 1.00 | 30.44 | A | N |
| ATOM | 953 | CA | ARG A 358 | 6.953 | -2.239 | 10.239 | 1.00 | 31.47 | A | C |
| ATOM | 954 | CB | ARG A 358 | 8.166 | -2.218 | 11.175 | 1.00 | 34.23 | A | C |
| ATOM | 955 | CG | ARG A 358 | 9.437 | -2.841 | 10.575 | 1.00 | 38.73 | A | C |
| ATOM | 956 | CD | ARG A 358 | 9.314 | -4.363 | 10.341 | 1.00 | 42.43 | A | C |
| ATOM | 957 | NE | ARG A 358 | 9.061 | -5.076 | 11.592 | 1.00 | 47.26 | A | N |
| ATOM | 958 | CZ | ARG A 358 | 9.925 | -5.142 | 12.605 | 1.00 | 50.35 | A | C |
| ATOM | 959 | NH1 | ARG A 358 | 11.115 | -4.561 | 12.520 | 1.00 | 51.95 | A | N |
| ATOM | 960 | NH2 | ARG A 358 | 9.575 | -5.725 | 13.739 | 1.00 | 52.44 | A | N |
| ATOM | 961 | C | ARG A 358 | 5.727 | -1.677 | 10.954 | 1.00 | 30.76 | A | C |
| ATOM | 962 | O | ARG A 358 | 5.437 | -2.064 | 12.090 | 1.00 | 30.65 | A | O |
| ATOM | 963 | N | ASN A 359 | 4.999 | -0.800 | 10.262 | 1.00 | 29.83 | A | N |
| ATOM | 964 | CA | ASN A 359 | 3.795 | -0.139 | 10.768 | 1.00 | 29.51 | A | C |
| ATOM | 965 | CB | ASN A 359 | 2.590 | -1.075 | 10.777 | 1.00 | 32.41 | A | C |
| ATOM | 966 | CG | ASN A 359 | 2.283 | -1.626 | 9.393 | 1.00 | 36.67 | A | C |
| ATOM | 967 | OD1 | ASN A 359 | 1.907 | -0.883 | 8.472 | 1.00 | 38.64 | A | O |
| ATOM | 968 | ND2 | ASN A 359 | 2.493 | -2.933 | 9.223 | 1.00 | 38.54 | A | N |
| ATOM | 969 | C | ASN A 359 | 3.939 | 0.590 | 12.090 | 1.00 | 28.21 | A | C |
| ATOM | 970 | O | ASN A 359 | 3.114 | 0.473 | 12.995 | 1.00 | 27.59 | A | O |
| ATOM | 971 | N | TYR A 360 | 5.008 | 1.365 | 12.168 | 1.00 | 27.28 | A | N |
| ATOM | 972 | CA | TYR A 360 | 5.302 | 2.197 | 13.316 | 1.00 | 25.95 | A | C |
| ATOM | 973 | CB | TYR A 360 | 6.695 | 1.860 | 13.869 | 1.00 | 27.03 | A | C |
| ATOM | 974 | CG | TYR A 360 | 6.742 | 0.781 | 14.927 | 1.00 | 27.19 | A | C |
| ATOM | 975 | CD1 | TYR A 360 | 6.757 | -0.566 | 14.579 | 1.00 | 28.63 | A | C |
| ATOM | 976 | CE1 | TYR A 360 | 6.843 | -1.558 | 15.545 | 1.00 | 29.58 | A | C |
| ATOM | 977 | CD2 | TYR A 360 | 6.813 | 1.113 | 16.279 | 1.00 | 28.49 | A | C |
| ATOM | 978 | CE2 | TYR A 360 | 6.900 | 0.126 | 17.266 | 1.00 | 29.68 | A | C |
| ATOM | 979 | CZ | TYR A 360 | 6.916 | -1.205 | 16.889 | 1.00 | 30.60 | A | C |
| ATOM | 980 | OH | TYR A 360 | 7.026 | -2.187 | 17.850 | 1.00 | 33.18 | A | O |
| ATOM | 981 | C | TYR A 360 | 5.326 | 3.622 | 12.751 | 1.00 | 25.29 | A | C |
| ATOM | 982 | O | TYR A 360 | 5.087 | 3.842 | 11.562 | 1.00 | 25.26 | A | O |
| ATOM | 983 | N | ILE A 361 | 5.558 | 4.591 | 13.621 | 1.00 | 24.54 | A | N |
| ATOM | 984 | CA | ILE A 361 | 5.682 | 5.979 | 13.216 | 1.00 | 24.06 | A | C |
| ATOM | 985 | CB | ILE A 361 | 4.369 | 6.815 | 13.416 | 1.00 | 23.90 | A | C |
| ATOM | 986 | CG2 | ILE A 361 | 3.197 | 6.170 | 12.673 | 1.00 | 24.83 | A | C |
| ATOM | 987 | CG1 | ILE A 361 | 4.042 | 6.992 | 14.896 | 1.00 | 23.65 | A | C |
| ATOM | 988 | CD1 | ILE A 361 | 3.095 | 8.131 | 15.173 | 1.00 | 21.90 | A | C |
| ATOM | 989 | C | ILE A 361 | 6.821 | 6.539 | 14.080 | 1.00 | 23.71 | A | C |
| ATOM | 990 | O | ILE A 361 | 7.265 | 5.898 | 15.033 | 1.00 | 23.99 | A | O |

Figure 9

| | | | | | | | | | | | |
|---|---|---|---|---|---|---|---|---|---|---|---|
| ATOM | 991 | N | HIS | A | 362 | 7.312 | 7.715 | 13.734 | 1.00 | 22.45 | A N |
| ATOM | 992 | CA | HIS | A | 362 | 8.375 | 8.326 | 14.493 | 1.00 | 22.31 | A C |
| ATOM | 993 | CB | HIS | A | 362 | 9.341 | 9.029 | 13.538 | 1.00 | 20.50 | A C |
| ATOM | 994 | CG | HIS | A | 362 | 10.607 | 9.488 | 14.185 | 1.00 | 18.32 | A C |
| ATOM | 995 | CD2 | HIS | A | 362 | 11.898 | 9.166 | 13.939 | 1.00 | 18.10 | A C |
| ATOM | 996 | ND1 | HIS | A | 362 | 10.629 | 10.399 | 15.216 | 1.00 | 18.25 | A N |
| ATOM | 997 | CE1 | HIS | A | 362 | 11.881 | 10.619 | 15.580 | 1.00 | 17.29 | A C |
| ATOM | 998 | NE2 | HIS | A | 362 | 12.670 | 9.880 | 14.821 | 1.00 | 17.14 | A N |
| ATOM | 999 | C | HIS | A | 362 | 7.771 | 9.339 | 15.457 | 1.00 | 22.91 | A C |
| ATOM | 1000 | O | HIS | A | 362 | 7.993 | 9.259 | 16.663 | 1.00 | 23.62 | A O |
| ATOM | 1001 | N | ARG | A | 363 | 6.973 | 10.240 | 14.880 | 1.00 | 23.00 | A N |
| ATOM | 1002 | CA | ARG | A | 363 | 6.270 | 11.378 | 15.495 | 1.00 | 22.69 | A C |
| ATOM | 1003 | CB | ARG | A | 363 | 5.196 | 10.990 | 16.523 | 1.00 | 27.15 | A C |
| ATOM | 1004 | CG | ARG | A | 363 | 5.617 | 10.178 | 17.705 | 1.00 | 31.67 | A C |
| ATOM | 1005 | CD | ARG | A | 363 | 4.382 | 9.648 | 18.428 | 1.00 | 33.96 | A C |
| ATOM | 1006 | NE | ARG | A | 363 | 3.627 | 10.728 | 19.038 | 1.00 | 35.08 | A N |
| ATOM | 1007 | CZ | ARG | A | 363 | 2.300 | 10.771 | 19.065 | 1.00 | 37.48 | A C |
| ATOM | 1008 | NH1 | ARG | A | 363 | 1.591 | 9.779 | 18.526 | 1.00 | 33.87 | A N |
| ATOM | 1009 | NH2 | ARG | A | 363 | 1.686 | 11.828 | 19.597 | 1.00 | 39.50 | A N |
| ATOM | 1010 | C | ARG | A | 363 | 7.078 | 12.571 | 15.961 | 1.00 | 21.26 | A C |
| ATOM | 1011 | O | ARG | A | 363 | 6.515 | 13.613 | 16.298 | 1.00 | 19.90 | A O |
| ATOM | 1012 | N | ASP | A | 364 | 8.398 | 12.447 | 15.915 | 1.00 | 20.28 | A N |
| ATOM | 1013 | CA | ASP | A | 364 | 9.279 | 13.540 | 16.318 | 1.00 | 19.86 | A C |
| ATOM | 1014 | CB | ASP | A | 364 | 9.856 | 13.272 | 17.720 | 1.00 | 19.46 | A C |
| ATOM | 1015 | CG | ASP | A | 364 | 8.826 | 13.479 | 18.829 | 1.00 | 18.99 | A C |
| ATOM | 1016 | OD1 | ASP | A | 364 | 8.405 | 14.643 | 19.047 | 1.00 | 18.35 | A O |
| ATOM | 1017 | OD2 | ASP | A | 364 | 8.460 | 12.478 | 19.487 | 1.00 | 19.88 | A O |
| ATOM | 1018 | C | ASP | A | 364 | 10.397 | 13.713 | 15.299 | 1.00 | 19.31 | A C |
| ATOM | 1019 | O | ASP | A | 364 | 11.475 | 14.196 | 15.628 | 1.00 | 18.40 | A O |
| ATOM | 1020 | N | LEU | A | 365 | 10.115 | 13.335 | 14.052 | 1.00 | 18.66 | A N |
| ATOM | 1021 | CA | LEU | A | 365 | 11.095 | 13.419 | 12.985 | 1.00 | 18.26 | A C |
| ATOM | 1022 | CB | LEU | A | 365 | 10.603 | 12.653 | 11.741 | 1.00 | 17.89 | A C |
| ATOM | 1023 | CG | LEU | A | 365 | 11.545 | 12.601 | 10.522 | 1.00 | 19.11 | A C |
| ATOM | 1024 | CD1 | LEU | A | 365 | 12.869 | 11.907 | 10.877 | 1.00 | 18.18 | A C |
| ATOM | 1025 | CD2 | LEU | A | 365 | 10.877 | 11.892 | 9.344 | 1.00 | 18.30 | A C |
| ATOM | 1026 | C | LEU | A | 365 | 11.537 | 14.847 | 12.626 | 1.00 | 18.91 | A C |
| ATOM | 1027 | O | LEU | A | 365 | 10.729 | 15.698 | 12.240 | 1.00 | 19.70 | A O |
| ATOM | 1028 | N | ARG | A | 366 | 12.825 | 15.113 | 12.817 | 1.00 | 17.78 | A N |
| ATOM | 1029 | CA | ARG | A | 366 | 13.413 | 16.405 | 12.496 | 1.00 | 18.08 | A C |
| ATOM | 1030 | CB | ARG | A | 366 | 12.912 | 17.512 | 13.427 | 1.00 | 20.03 | A C |
| ATOM | 1031 | CG | ARG | A | 366 | 13.132 | 17.309 | 14.900 | 1.00 | 22.64 | A C |
| ATOM | 1032 | CD | ARG | A | 366 | 12.441 | 18.430 | 15.653 | 1.00 | 25.82 | A C |
| ATOM | 1033 | NE | ARG | A | 366 | 12.245 | 18.104 | 17.062 | 1.00 | 31.25 | A N |
| ATOM | 1034 | CZ | ARG | A | 366 | 11.172 | 17.480 | 17.556 | 1.00 | 30.66 | A C |
| ATOM | 1035 | NH1 | ARG | A | 366 | 10.166 | 17.108 | 16.765 | 1.00 | 30.75 | A N |
| ATOM | 1036 | NH2 | ARG | A | 366 | 11.129 | 17.192 | 18.848 | 1.00 | 31.39 | A N |
| ATOM | 1037 | C | ARG | A | 366 | 14.915 | 16.242 | 12.565 | 1.00 | 17.49 | A C |
| ATOM | 1038 | O | ARG | A | 366 | 15.394 | 15.227 | 13.074 | 1.00 | 16.59 | A O |
| ATOM | 1039 | N | ALA | A | 367 | 15.647 | 17.200 | 11.998 | 1.00 | 16.80 | A N |
| ATOM | 1040 | CA | ALA | A | 367 | 17.113 | 17.137 | 11.959 | 1.00 | 17.55 | A C |
| ATOM | 1041 | CB | ALA | A | 367 | 17.684 | 18.368 | 11.255 | 1.00 | 16.47 | A C |
| ATOM | 1042 | C | ALA | A | 367 | 17.757 | 16.960 | 13.336 | 1.00 | 18.06 | A C |
| ATOM | 1043 | O | ALA | A | 367 | 18.736 | 16.242 | 13.466 | 1.00 | 18.25 | A O |
| ATOM | 1044 | N | ALA | A | 368 | 17.179 | 17.597 | 14.356 | 1.00 | 18.36 | A N |
| ATOM | 1045 | CA | ALA | A | 368 | 17.676 | 17.519 | 15.723 | 1.00 | 18.23 | A C |
| ATOM | 1046 | CB | ALA | A | 368 | 16.859 | 18.440 | 16.637 | 1.00 | 17.93 | A C |
| ATOM | 1047 | C | ALA | A | 368 | 17.675 | 16.088 | 16.255 | 1.00 | 18.77 | A C |
| ATOM | 1048 | O | ALA | A | 368 | 18.479 | 15.743 | 17.117 | 1.00 | 19.54 | A O |
| ATOM | 1049 | N | ASN | A | 369 | 16.807 | 15.244 | 15.707 | 1.00 | 18.64 | A N |

Figure 9

| ATOM | 1050 | CA | ASN | A | 369 | 16.720 | 13.857 | 16.135 | 1.00 | 18.62 | A | C |
| --- | --- | --- | --- | --- | --- | --- | --- | --- | --- | --- | --- | --- |
| ATOM | 1051 | CB | ASN | A | 369 | 15.267 | 13.490 | 16.459 | 1.00 | 20.85 | A | C |
| ATOM | 1052 | CG | ASN | A | 369 | 14.736 | 14.251 | 17.662 | 1.00 | 22.16 | A | C |
| ATOM | 1053 | OD1 | ASN | A | 369 | 15.429 | 14.405 | 18.675 | 1.00 | 24.04 | A | O |
| ATOM | 1054 | ND2 | ASN | A | 369 | 13.514 | 14.741 | 17.556 | 1.00 | 20.54 | A | N |
| ATOM | 1055 | C | ASN | A | 369 | 17.361 | 12.851 | 15.184 | 1.00 | 17.98 | A | C |
| ATOM | 1056 | O | ASN | A | 369 | 17.042 | 11.665 | 15.195 | 1.00 | 19.28 | A | O |
| ATOM | 1057 | N | ILE | A | 370 | 18.222 | 13.349 | 14.306 | 1.00 | 17.24 | A | N |
| ATOM | 1058 | CA | ILE | A | 370 | 18.968 | 12.495 | 13.390 | 1.00 | 15.93 | A | C |
| ATOM | 1059 | CB | ILE | A | 370 | 18.923 | 13.006 | 11.921 | 1.00 | 15.05 | A | C |
| ATOM | 1060 | CG2 | ILE | A | 370 | 19.861 | 12.168 | 11.054 | 1.00 | 14.28 | A | C |
| ATOM | 1061 | CG1 | ILE | A | 370 | 17.493 | 12.940 | 11.376 | 1.00 | 13.28 | A | C |
| ATOM | 1062 | CD1 | ILE | A | 370 | 16.896 | 11.525 | 11.404 | 1.00 | 10.80 | A | C |
| ATOM | 1063 | C | ILE | A | 370 | 20.403 | 12.600 | 13.916 | 1.00 | 14.72 | A | C |
| ATOM | 1064 | O | ILE | A | 370 | 20.842 | 13.677 | 14.283 | 1.00 | 13.16 | A | O |
| ATOM | 1065 | N | LEU | A | 371 | 21.081 | 11.472 | 14.044 | 1.00 | 15.89 | A | N |
| ATOM | 1066 | CA | LEU | A | 371 | 22.454 | 11.481 | 14.535 | 1.00 | 17.53 | A | C |
| ATOM | 1067 | CB | LEU | A | 371 | 22.619 | 10.502 | 15.707 | 1.00 | 17.12 | A | C |
| ATOM | 1068 | CG | LEU | A | 371 | 21.704 | 10.781 | 16.917 | 1.00 | 17.03 | A | C |
| ATOM | 1069 | CD1 | LEU | A | 371 | 21.894 | 9.687 | 17.949 | 1.00 | 17.73 | A | C |
| ATOM | 1070 | CD2 | LEU | A | 371 | 21.960 | 12.159 | 17.532 | 1.00 | 15.47 | A | C |
| ATOM | 1071 | C | LEU | A | 371 | 23.442 | 11.202 | 13.405 | 1.00 | 17.84 | A | C |
| ATOM | 1072 | O | LEU | A | 371 | 23.106 | 10.516 | 12.439 | 1.00 | 17.45 | A | O |
| ATOM | 1073 | N | VAL | A | 372 | 24.636 | 11.787 | 13.511 | 1.00 | 18.62 | A | N |
| ATOM | 1074 | CA | VAL | A | 372 | 25.682 | 11.656 | 12.491 | 1.00 | 18.89 | A | C |
| ATOM | 1075 | CB | VAL | A | 372 | 26.096 | 13.062 | 11.945 | 1.00 | 19.12 | A | C |
| ATOM | 1076 | CG1 | VAL | A | 372 | 26.961 | 12.912 | 10.718 | 1.00 | 20.07 | A | C |
| ATOM | 1077 | CG2 | VAL | A | 372 | 24.878 | 13.911 | 11.604 | 1.00 | 17.28 | A | C |
| ATOM | 1078 | C | VAL | A | 372 | 26.938 | 10.941 | 13.025 | 1.00 | 19.66 | A | C |
| ATOM | 1079 | O | VAL | A | 372 | 27.522 | 11.358 | 14.024 | 1.00 | 18.63 | A | O |
| ATOM | 1080 | N | SER | A | 373 | 27.368 | 9.885 | 12.343 | 1.00 | 20.99 | A | N |
| ATOM | 1081 | CA | SER | A | 373 | 28.551 | 9.144 | 12.772 | 1.00 | 23.85 | A | C |
| ATOM | 1082 | CB | SER | A | 373 | 28.519 | 7.723 | 12.226 | 1.00 | 23.46 | A | C |
| ATOM | 1083 | OG | SER | A | 373 | 28.795 | 7.723 | 10.842 | 1.00 | 24.28 | A | O |
| ATOM | 1084 | C | SER | A | 373 | 29.871 | 9.803 | 12.354 | 1.00 | 25.72 | A | C |
| ATOM | 1085 | O | SER | A | 373 | 29.881 | 10.853 | 11.716 | 1.00 | 24.83 | A | O |
| ATOM | 1086 | N | ASP | A | 374 | 30.981 | 9.186 | 12.760 | 1.00 | 29.11 | A | N |
| ATOM | 1087 | CA | ASP | A | 374 | 32.326 | 9.665 | 12.429 | 1.00 | 31.52 | A | C |
| ATOM | 1088 | CB | ASP | A | 374 | 33.389 | 8.843 | 13.180 | 1.00 | 33.89 | A | C |
| ATOM | 1089 | CG | ASP | A | 374 | 33.210 | 7.344 | 13.003 | 1.00 | 36.53 | A | C |
| ATOM | 1090 | OD1 | ASP | A | 374 | 32.167 | 6.795 | 13.415 | 1.00 | 38.65 | A | O |
| ATOM | 1091 | OD2 | ASP | A | 374 | 34.126 | 6.705 | 12.450 | 1.00 | 39.99 | A | O |
| ATOM | 1092 | C | ASP | A | 374 | 32.544 | 9.574 | 10.927 | 1.00 | 32.12 | A | C |
| ATOM | 1093 | O | ASP | A | 374 | 33.240 | 10.396 | 10.337 | 1.00 | 32.39 | A | O |
| ATOM | 1094 | N | THR | A | 375 | 31.899 | 8.584 | 10.315 | 1.00 | 33.45 | A | N |
| ATOM | 1095 | CA | THR | A | 375 | 31.977 | 8.366 | 8.874 | 1.00 | 34.21 | A | C |
| ATOM | 1096 | CB | THR | A | 375 | 31.769 | 6.875 | 8.507 | 1.00 | 34.97 | A | C |
| ATOM | 1097 | OG1 | THR | A | 375 | 30.431 | 6.478 | 8.834 | 1.00 | 36.79 | A | O |
| ATOM | 1098 | CG2 | THR | A | 375 | 32.745 | 5.989 | 9.270 | 1.00 | 34.81 | A | C |
| ATOM | 1099 | C | THR | A | 375 | 30.923 | 9.203 | 8.143 | 1.00 | 33.85 | A | C |
| ATOM | 1100 | O | THR | A | 375 | 30.714 | 9.036 | 6.946 | 1.00 | 34.83 | A | O |
| ATOM | 1101 | N | LEU | A | 376 | 30.243 | 10.074 | 8.885 | 1.00 | 33.54 | A | N |
| ATOM | 1102 | CA | LEU | A | 376 | 29.202 | 10.963 | 8.357 | 1.00 | 33.18 | A | C |
| ATOM | 1103 | CB | LEU | A | 376 | 29.778 | 11.898 | 7.289 | 1.00 | 33.75 | A | C |
| ATOM | 1104 | CG | LEU | A | 376 | 31.041 | 12.653 | 7.719 | 1.00 | 34.84 | A | C |
| ATOM | 1105 | CD1 | LEU | A | 376 | 31.477 | 13.602 | 6.621 | 1.00 | 35.50 | A | C |
| ATOM | 1106 | CD2 | LEU | A | 376 | 30.792 | 13.402 | 9.014 | 1.00 | 34.15 | A | C |
| ATOM | 1107 | C | LEU | A | 376 | 27.909 | 10.295 | 7.855 | 1.00 | 32.73 | A | C |
| ATOM | 1108 | O | LEU | A | 376 | 27.242 | 10.814 | 6.951 | 1.00 | 32.90 | A | O |

Figure 9

| | | | | | | | | | | | |
|---|---|---|---|---|---|---|---|---|---|---|---|
| ATOM | 1109 | N | SER | A | 377 | 27.576 | 9.132 | 8.419 | 1.00 31.93 | A | N |
| ATOM | 1110 | CA | SER | A | 377 | 26.345 | 8.429 | 8.046 | 1.00 31.02 | A | C |
| ATOM | 1111 | CB | SER | A | 377 | 26.551 | 6.904 | 7.954 | 1.00 31.29 | A | C |
| ATOM | 1112 | OG | SER | A | 377 | 26.806 | 6.319 | 9.218 | 1.00 34.88 | A | O |
| ATOM | 1113 | C | SER | A | 377 | 25.244 | 8.791 | 9.048 | 1.00 29.11 | A | C |
| ATOM | 1114 | O | SER | A | 377 | 25.508 | 8.973 | 10.245 | 1.00 28.53 | A | O |
| ATOM | 1115 | N | CYS | A | 378 | 24.022 | 8.931 | 8.542 | 1.00 27.20 | A | N |
| ATOM | 1116 | CA | CYS | A | 378 | 22.886 | 9.301 | 9.373 | 1.00 25.33 | A | C |
| ATOM | 1117 | CB | CYS | A | 378 | 21.987 | 10.295 | 8.627 | 1.00 24.62 | A | C |
| ATOM | 1118 | SG | CYS | A | 378 | 22.785 | 11.875 | 8.291 | 1.00 23.79 | A | S |
| ATOM | 1119 | C | CYS | A | 378 | 22.071 | 8.122 | 9.896 | 1.00 23.62 | A | C |
| ATOM | 1120 | O | CYS | A | 378 | 21.870 | 7.132 | 9.194 | 1.00 22.93 | A | O |
| ATOM | 1121 | N | LYS | A | 379 | 21.705 | 8.209 | 11.176 | 1.00 22.80 | A | N |
| ATOM | 1122 | CA | LYS | A | 379 | 20.889 | 7.202 | 11.849 | 1.00 22.21 | A | C |
| ATOM | 1123 | CB | LYS | A | 379 | 21.728 | 6.378 | 12.833 | 1.00 22.70 | A | C |
| ATOM | 1124 | CG | LYS | A | 379 | 22.530 | 5.243 | 12.163 | 1.00 23.90 | A | C |
| ATOM | 1125 | CD | LYS | A | 379 | 23.616 | 4.693 | 13.070 | 1.00 24.84 | A | C |
| ATOM | 1126 | CE | LYS | A | 379 | 24.305 | 3.462 | 12.495 | 1.00 26.98 | A | C |
| ATOM | 1127 | NZ | LYS | A | 379 | 23.647 | 2.198 | 12.996 | 1.00 32.26 | A | N |
| ATOM | 1128 | C | LYS | A | 379 | 19.750 | 7.940 | 12.555 | 1.00 21.65 | A | C |
| ATOM | 1129 | O | LYS | A | 379 | 19.902 | 9.086 | 12.990 | 1.00 21.22 | A | O |
| ATOM | 1130 | N | ILE | A | 380 | 18.588 | 7.306 | 12.609 | 1.00 21.77 | A | N |
| ATOM | 1131 | CA | ILE | A | 380 | 17.413 | 7.905 | 13.229 | 1.00 21.91 | A | C |
| ATOM | 1132 | CB | ILE | A | 380 | 16.094 | 7.335 | 12.604 | 1.00 23.11 | A | C |
| ATOM | 1133 | CG2 | ILE | A | 380 | 14.871 | 8.008 | 13.210 | 1.00 22.13 | A | C |
| ATOM | 1134 | CG1 | ILE | A | 380 | 16.096 | 7.535 | 11.091 | 1.00 24.27 | A | C |
| ATOM | 1135 | CD1 | ILE | A | 380 | 14.866 | 7.010 | 10.443 | 1.00 23.78 | A | C |
| ATOM | 1136 | C | ILE | A | 380 | 17.389 | 7.641 | 14.731 | 1.00 21.20 | A | C |
| ATOM | 1137 | O | ILE | A | 380 | 17.513 | 6.494 | 15.171 | 1.00 20.60 | A | O |
| ATOM | 1138 | N | ALA | A | 381 | 17.197 | 8.706 | 15.505 | 1.00 21.04 | A | N |
| ATOM | 1139 | CA | ALA | A | 381 | 17.130 | 8.590 | 16.959 | 1.00 20.87 | A | C |
| ATOM | 1140 | CB | ALA | A | 381 | 18.173 | 9.479 | 17.601 | 1.00 19.64 | A | C |
| ATOM | 1141 | C | ALA | A | 381 | 15.748 | 8.991 | 17.453 | 1.00 20.33 | A | C |
| ATOM | 1142 | O | ALA | A | 381 | 14.985 | 9.630 | 16.726 | 1.00 19.52 | A | O |
| ATOM | 1143 | N | ASP | A | 382 | 15.450 | 8.594 | 18.690 | 1.00 20.28 | A | N |
| ATOM | 1144 | CA | ASP | A | 382 | 14.195 | 8.912 | 19.390 | 1.00 20.30 | A | C |
| ATOM | 1145 | CB | ASP | A | 382 | 14.242 | 10.339 | 19.919 | 1.00 20.57 | A | C |
| ATOM | 1146 | CG | ASP | A | 382 | 15.246 | 10.513 | 21.047 | 1.00 21.10 | A | C |
| ATOM | 1147 | OD1 | ASP | A | 382 | 15.398 | 9.585 | 21.861 | 1.00 20.70 | A | O |
| ATOM | 1148 | OD2 | ASP | A | 382 | 15.868 | 11.588 | 21.120 | 1.00 21.71 | A | O |
| ATOM | 1149 | C | ASP | A | 382 | 12.914 | 8.707 | 18.615 | 1.00 19.48 | A | C |
| ATOM | 1150 | O | ASP | A | 382 | 12.028 | 9.558 | 18.631 | 1.00 19.20 | A | O |
| ATOM | 1151 | N | PHE | A | 383 | 12.827 | 7.561 | 17.961 | 1.00 20.37 | A | N |
| ATOM | 1152 | CA | PHE | A | 383 | 11.681 | 7.184 | 17.158 | 1.00 22.59 | A | C |
| ATOM | 1153 | CB | PHE | A | 383 | 12.161 | 6.372 | 15.942 | 1.00 21.67 | A | C |
| ATOM | 1154 | CG | PHE | A | 383 | 13.096 | 5.235 | 16.294 | 1.00 21.87 | A | C |
| ATOM | 1155 | CD1 | PHE | A | 383 | 12.605 | 4.027 | 16.792 | 1.00 21.53 | A | C |
| ATOM | 1156 | CD2 | PHE | A | 383 | 14.479 | 5.390 | 16.156 | 1.00 22.38 | A | C |
| ATOM | 1157 | CE1 | PHE | A | 383 | 13.476 | 2.982 | 17.155 | 1.00 21.05 | A | C |
| ATOM | 1158 | CE2 | PHE | A | 383 | 15.360 | 4.358 | 16.514 | 1.00 21.77 | A | C |
| ATOM | 1159 | CZ | PHE | A | 383 | 14.857 | 3.152 | 17.015 | 1.00 22.42 | A | C |
| ATOM | 1160 | C | PHE | A | 383 | 10.654 | 6.355 | 17.936 | 1.00 24.01 | A | C |
| ATOM | 1161 | O | PHE | A | 383 | 11.010 | 5.575 | 18.826 | 1.00 24.21 | A | O |
| ATOM | 1162 | N | GLY | A | 384 | 9.388 | 6.520 | 17.569 | 1.00 25.26 | A | N |
| ATOM | 1163 | CA | GLY | A | 384 | 8.321 | 5.746 | 18.174 | 1.00 27.08 | A | C |
| ATOM | 1164 | C | GLY | A | 384 | 7.876 | 6.107 | 19.570 | 1.00 27.93 | A | C |
| ATOM | 1165 | O | GLY | A | 384 | 7.200 | 5.310 | 20.206 | 1.00 29.12 | A | O |
| ATOM | 1166 | N | LEU | A | 385 | 8.272 | 7.274 | 20.060 | 1.00 28.53 | A | N |
| ATOM | 1167 | CA | LEU | A | 385 | 7.869 | 7.704 | 21.389 | 1.00 29.45 | A | C |

Figure 9

| | | | | | | | | | | |
|---|---|---|---|---|---|---|---|---|---|---|
| ATOM | 1168 | CB | LEU | A | 385 | 8.669 | 8.932 | 21.825 | 1.00 27.62 | A C |
| ATOM | 1169 | CG | LEU | A | 385 | 10.191 | 8.752 | 21.901 | 1.00 28.14 | A C |
| ATOM | 1170 | CD1 | LEU | A | 385 | 10.830 | 10.016 | 22.426 | 1.00 27.39 | A C |
| ATOM | 1171 | CD2 | LEU | A | 385 | 10.556 | 7.580 | 22.785 | 1.00 26.90 | A C |
| ATOM | 1172 | C | LEU | A | 385 | 6.383 | 8.035 | 21.329 | 1.00 31.13 | A C |
| ATOM | 1173 | O | LEU | A | 385 | 5.900 | 8.504 | 20.314 | 1.00 31.06 | A O |
| ATOM | 1174 | N | ALA | A | 386 | 5.649 | 7.707 | 22.387 | 1.00 32.66 | A N |
| ATOM | 1175 | CA | ALA | A | 386 | 4.212 | 7.973 | 22.454 | 1.00 33.96 | A C |
| ATOM | 1176 | CB | ALA | A | 386 | 3.611 | 7.256 | 23.671 | 1.00 35.36 | A C |
| ATOM | 1177 | C | ALA | A | 386 | 3.940 | 9.464 | 22.565 | 1.00 34.42 | A C |
| ATOM | 1178 | O | ALA | A | 386 | 2.838 | 9.935 | 22.286 | 1.00 34.00 | A O |
| ATOM | 1179 | N | ARG | A | 387 | 4.960 | 10.204 | 22.969 | 1.00 35.23 | A N |
| ATOM | 1180 | CA | ARG | A | 387 | 4.827 | 11.637 | 23.162 | 1.00 35.46 | A C |
| ATOM | 1181 | CB | ARG | A | 387 | 5.253 | 11.975 | 24.593 | 1.00 36.36 | A C |
| ATOM | 1182 | CG | ARG | A | 387 | 6.669 | 11.496 | 24.938 | 1.00 37.12 | A C |
| ATOM | 1183 | CD | ARG | A | 387 | 7.099 | 11.951 | 26.311 | 1.00 37.31 | A C |
| ATOM | 1184 | NE | ARG | A | 387 | 8.512 | 11.684 | 26.567 | 1.00 38.55 | A N |
| ATOM | 1185 | CZ | ARG | A | 387 | 9.452 | 12.624 | 26.598 | 1.00 39.68 | A C |
| ATOM | 1186 | NH1 | ARG | A | 387 | 9.126 | 13.898 | 26.387 | 1.00 40.14 | A N |
| ATOM | 1187 | NH2 | ARG | A | 387 | 10.724 | 12.296 | 26.833 | 1.00 41.78 | A N |
| ATOM | 1188 | C | ARG | A | 387 | 5.601 | 12.524 | 22.190 | 1.00 34.80 | A C |
| ATOM | 1189 | O | ARG | A | 387 | 6.456 | 12.076 | 21.437 | 1.00 34.59 | A O |
| ATOM | 1190 | N | LEU | A | 388 | 5.277 | 13.803 | 22.233 | 1.00 34.07 | A N |
| ATOM | 1191 | CA | LEU | A | 388 | 5.949 | 14.787 | 21.425 | 1.00 33.84 | A C |
| ATOM | 1192 | CB | LEU | A | 388 | 4.988 | 15.907 | 21.069 | 1.00 35.19 | A C |
| ATOM | 1193 | CG | LEU | A | 388 | 3.770 | 15.463 | 20.266 | 1.00 37.34 | A C |
| ATOM | 1194 | CD1 | LEU | A | 388 | 3.148 | 16.693 | 19.634 | 1.00 37.78 | A C |
| ATOM | 1195 | CD2 | LEU | A | 388 | 4.185 | 14.487 | 19.179 | 1.00 38.11 | A C |
| ATOM | 1196 | C | LEU | A | 388 | 7.069 | 15.328 | 22.304 | 1.00 33.47 | A C |
| ATOM | 1197 | O | LEU | A | 388 | 6.804 | 15.844 | 23.398 | 1.00 33.35 | A O |
| ATOM | 1198 | N | ILE | A | 389 | 8.315 | 15.173 | 21.850 | 1.00 32.09 | A N |
| ATOM | 1199 | CA | ILE | A | 389 | 9.473 | 15.628 | 22.613 | 1.00 30.58 | A C |
| ATOM | 1200 | CB | ILE | A | 389 | 10.625 | 14.568 | 22.632 | 1.00 27.88 | A C |
| ATOM | 1201 | CG2 | ILE | A | 389 | 10.073 | 13.190 | 22.971 | 1.00 26.93 | A C |
| ATOM | 1202 | CG1 | ILE | A | 389 | 11.384 | 14.547 | 21.306 | 1.00 24.73 | A C |
| ATOM | 1203 | CD1 | ILE | A | 389 | 12.351 | 13.408 | 21.196 | 1.00 21.80 | A C |
| ATOM | 1204 | C | ILE | A | 389 | 10.022 | 16.974 | 22.180 | 1.00 31.62 | A C |
| ATOM | 1205 | O | ILE | A | 389 | 9.691 | 17.482 | 21.120 | 1.00 31.08 | A O |
| ATOM | 1206 | N | GLU | A | 390 | 10.814 | 17.562 | 23.066 | 1.00 33.79 | A N |
| ATOM | 1207 | CA | GLU | A | 390 | 11.467 | 18.844 | 22.857 | 1.00 36.46 | A C |
| ATOM | 1208 | CB | GLU | A | 390 | 11.050 | 19.836 | 23.936 | 1.00 36.83 | A C |
| ATOM | 1209 | CG | GLU | A | 390 | 9.624 | 20.312 | 23.786 | 1.00 38.91 | A C |
| ATOM | 1210 | CD | GLU | A | 390 | 9.136 | 21.114 | 24.971 | 1.00 40.01 | A C |
| ATOM | 1211 | OE1 | GLU | A | 390 | 7.915 | 21.060 | 25.241 | 1.00 42.61 | A O |
| ATOM | 1212 | OE2 | GLU | A | 390 | 9.956 | 21.793 | 25.631 | 1.00 39.98 | A O |
| ATOM | 1213 | C | GLU | A | 390 | 12.972 | 18.600 | 22.901 | 1.00 38.29 | A C |
| ATOM | 1214 | O | GLU | A | 390 | 13.469 | 17.727 | 23.630 | 1.00 38.90 | A O |
| ATOM | 1215 | N | ASP | A | 391 | 13.703 | 19.424 | 22.167 | 1.00 39.80 | A N |
| ATOM | 1216 | CA | ASP | A | 391 | 15.149 | 19.269 | 22.054 | 1.00 41.52 | A C |
| ATOM | 1217 | CB | ASP | A | 391 | 15.620 | 19.999 | 20.789 | 1.00 43.20 | A C |
| ATOM | 1218 | CG | ASP | A | 391 | 14.854 | 19.550 | 19.534 | 1.00 45.14 | A C |
| ATOM | 1219 | OD1 | ASP | A | 391 | 14.561 | 18.328 | 19.381 | 1.00 43.76 | A O |
| ATOM | 1220 | OD2 | ASP | A | 391 | 14.529 | 20.434 | 18.709 | 1.00 46.30 | A O |
| ATOM | 1221 | C | ASP | A | 391 | 16.006 | 19.650 | 23.263 | 1.00 41.30 | A C |
| ATOM | 1222 | O | ASP | A | 391 | 17.218 | 19.389 | 23.269 | 1.00 40.95 | A O |
| ATOM | 1223 | N | ASN | A | 392 | 15.363 | 20.213 | 24.289 | 1.00 40.78 | A N |
| ATOM | 1224 | CA | ASN | A | 392 | 16.037 | 20.659 | 25.507 | 1.00 39.99 | A C |
| ATOM | 1225 | CB | ASN | A | 392 | 15.444 | 22.005 | 25.961 | 1.00 41.20 | A C |
| ATOM | 1226 | CG | ASN | A | 392 | 13.998 | 21.879 | 26.471 | 1.00 42.13 | A C |

Figure 9

| ATOM | 1227 | OD1 | ASN | A | 392 | 13.358 | 20.831 | 26.325 | 1.00 | 41.81 | A | O |
| ATOM | 1228 | ND2 | ASN | A | 392 | 13.486 | 22.948 | 27.081 | 1.00 | 42.88 | A | N |
| ATOM | 1229 | C | ASN | A | 392 | 15.957 | 19.654 | 26.666 | 1.00 | 39.48 | A | C |
| ATOM | 1230 | O | ASN | A | 392 | 16.265 | 20.000 | 27.813 | 1.00 | 39.63 | A | O |
| ATOM | 1231 | N | GLU | A | 393 | 15.576 | 18.415 | 26.372 | 1.00 | 37.97 | A | N |
| ATOM | 1232 | CA | GLU | A | 393 | 15.433 | 17.411 | 27.422 | 1.00 | 37.63 | A | C |
| ATOM | 1233 | CB | GLU | A | 393 | 14.359 | 16.416 | 27.034 | 1.00 | 37.39 | A | C |
| ATOM | 1234 | CG | GLU | A | 393 | 13.003 | 17.070 | 26.972 | 1.00 | 37.59 | A | C |
| ATOM | 1235 | CD | GLU | A | 393 | 12.022 | 16.304 | 26.141 | 1.00 | 37.73 | A | C |
| ATOM | 1236 | OE1 | GLU | A | 393 | 12.288 | 15.130 | 25.825 | 1.00 | 38.65 | A | O |
| ATOM | 1237 | OE2 | GLU | A | 393 | 10.968 | 16.878 | 25.815 | 1.00 | 40.22 | A | O |
| ATOM | 1238 | C | GLU | A | 393 | 16.675 | 16.692 | 27.946 | 1.00 | 37.58 | A | C |
| ATOM | 1239 | O | GLU | A | 393 | 16.684 | 16.222 | 29.085 | 1.00 | 36.88 | A | O |
| ATOM | 1240 | N | TYR | A | 394 | 17.707 | 16.577 | 27.117 | 1.00 | 37.61 | A | N |
| ATOM | 1241 | CA | TYR | A | 394 | 18.946 | 15.938 | 27.544 | 1.00 | 37.62 | A | C |
| ATOM | 1242 | CB | TYR | A | 394 | 19.060 | 14.521 | 26.993 | 1.00 | 36.62 | A | C |
| ATOM | 1243 | CG | TYR | A | 394 | 17.973 | 13.596 | 27.484 | 1.00 | 36.36 | A | C |
| ATOM | 1244 | CD1 | TYR | A | 394 | 16.760 | 13.494 | 26.802 | 1.00 | 36.62 | A | C |
| ATOM | 1245 | CE1 | TYR | A | 394 | 15.744 | 12.655 | 27.255 | 1.00 | 35.66 | A | C |
| ATOM | 1246 | CD2 | TYR | A | 394 | 18.143 | 12.830 | 28.636 | 1.00 | 36.67 | A | C |
| ATOM | 1247 | CE2 | TYR | A | 394 | 17.130 | 11.981 | 29.099 | 1.00 | 35.42 | A | C |
| ATOM | 1248 | CZ | TYR | A | 394 | 15.934 | 11.903 | 28.403 | 1.00 | 36.10 | A | C |
| ATOM | 1249 | OH | TYR | A | 394 | 14.918 | 11.086 | 28.850 | 1.00 | 36.25 | A | O |
| ATOM | 1250 | C | TYR | A | 394 | 20.158 | 16.794 | 27.171 | 1.00 | 38.47 | A | C |
| ATOM | 1251 | O | TYR | A | 394 | 21.294 | 16.386 | 27.387 | 1.00 | 37.38 | A | O |
| ATOM | 1252 | N | THR | A | 395 | 19.885 | 17.976 | 26.606 | 1.00 | 40.43 | A | N |
| ATOM | 1253 | CA | THR | A | 395 | 20.892 | 18.973 | 26.216 | 1.00 | 43.18 | A | C |
| ATOM | 1254 | CB | THR | A | 395 | 21.344 | 18.872 | 24.741 | 1.00 | 44.01 | A | C |
| ATOM | 1255 | OG1 | THR | A | 395 | 20.212 | 18.812 | 23.859 | 1.00 | 45.23 | A | O |
| ATOM | 1256 | CG2 | THR | A | 395 | 22.187 | 17.665 | 24.568 | 1.00 | 44.52 | A | C |
| ATOM | 1257 | C | THR | A | 395 | 20.334 | 20.360 | 26.472 | 1.00 | 44.64 | A | C |
| ATOM | 1258 | O | THR | A | 395 | 19.235 | 20.489 | 26.998 | 1.00 | 44.86 | A | O |
| ATOM | 1259 | N | ALA | A | 396 | 21.053 | 21.395 | 26.049 | 1.00 | 47.06 | A | N |
| ATOM | 1260 | CA | ALA | A | 396 | 20.609 | 22.760 | 26.314 | 1.00 | 49.78 | A | C |
| ATOM | 1261 | CB | ALA | A | 396 | 21.626 | 23.460 | 27.232 | 1.00 | 49.00 | A | C |
| ATOM | 1262 | C | ALA | A | 396 | 20.247 | 23.662 | 25.122 | 1.00 | 51.62 | A | C |
| ATOM | 1263 | O | ALA | A | 396 | 20.670 | 24.820 | 25.065 | 1.00 | 53.45 | A | O |
| ATOM | 1264 | N | ARG | A | 397 | 19.437 | 23.162 | 24.194 | 1.00 | 52.68 | A | N |
| ATOM | 1265 | CA | ARG | A | 397 | 19.026 | 23.974 | 23.054 | 1.00 | 53.54 | A | C |
| ATOM | 1266 | CB | ARG | A | 397 | 18.425 | 23.088 | 21.962 | 1.00 | 54.42 | A | C |
| ATOM | 1267 | CG | ARG | A | 397 | 19.366 | 22.005 | 21.441 | 1.00 | 54.78 | A | C |
| ATOM | 1268 | CD | ARG | A | 397 | 19.551 | 22.130 | 19.935 | 1.00 | 55.24 | A | C |
| ATOM | 1269 | NE | ARG | A | 397 | 20.287 | 21.009 | 19.354 | 1.00 | 54.73 | A | N |
| ATOM | 1270 | CZ | ARG | A | 397 | 19.903 | 19.739 | 19.438 | 1.00 | 53.85 | A | C |
| ATOM | 1271 | NH1 | ARG | A | 397 | 18.795 | 19.414 | 20.088 | 1.00 | 53.22 | A | N |
| ATOM | 1272 | NH2 | ARG | A | 397 | 20.606 | 18.795 | 18.835 | 1.00 | 54.22 | A | N |
| ATOM | 1273 | C | ARG | A | 397 | 18.002 | 25.029 | 23.494 | 1.00 | 54.23 | A | C |
| ATOM | 1274 | O | ARG | A | 397 | 18.363 | 26.229 | 23.511 | 1.00 | 54.68 | A | O |
| ATOM | 1275 | CB | PRO | A | 403 | 7.935 | 20.417 | 18.879 | 1.00 | 35.60 | A | C |
| ATOM | 1276 | CG | PRO | A | 403 | 8.596 | 20.993 | 20.168 | 1.00 | 35.93 | A | C |
| ATOM | 1277 | C | PRO | A | 403 | 6.861 | 21.597 | 16.909 | 1.00 | 33.43 | A | C |
| ATOM | 1278 | O | PRO | A | 403 | 6.826 | 20.656 | 16.080 | 1.00 | 33.48 | A | O |
| ATOM | 1279 | N | PRO | A | 403 | 7.593 | 22.795 | 18.995 | 1.00 | 34.69 | A | N |
| ATOM | 1280 | CD | PRO | A | 403 | 7.930 | 22.397 | 20.369 | 1.00 | 35.76 | A | C |
| ATOM | 1281 | CA | PRO | A | 403 | 7.895 | 21.674 | 18.042 | 1.00 | 34.39 | A | C |
| ATOM | 1282 | N | ILE | A | 404 | 6.105 | 22.682 | 16.828 | 1.00 | 30.88 | A | N |
| ATOM | 1283 | CA | ILE | A | 404 | 5.040 | 22.886 | 15.862 | 1.00 | 28.31 | A | C |
| ATOM | 1284 | CB | ILE | A | 404 | 4.249 | 24.175 | 16.282 | 1.00 | 28.25 | A | C |
| ATOM | 1285 | CG2 | ILE | A | 404 | 3.644 | 24.896 | 15.098 | 1.00 | 28.01 | A | C |

Figure 9

| ATOM | 1286 | CG1 | ILE A 404 | 3.222 | 23.813 | 17.346 | 1.00 | 28.13 | A | C |
| ATOM | 1287 | CD1 | ILE A 404 | 2.216 | 22.776 | 16.859 | 1.00 | 29.17 | A | C |
| ATOM | 1288 | C | ILE A 404 | 5.494 | 22.951 | 14.385 | 1.00 | 26.26 | A | C |
| ATOM | 1289 | O | ILE A 404 | 4.775 | 22.488 | 13.509 | 1.00 | 25.93 | A | O |
| ATOM | 1290 | N | LYS A 405 | 6.698 | 23.454 | 14.115 | 1.00 | 23.95 | A | N |
| ATOM | 1291 | CA | LYS A 405 | 7.171 | 23.593 | 12.738 | 1.00 | 22.46 | A | C |
| ATOM | 1292 | CB | LYS A 405 | 8.392 | 24.518 | 12.676 | 1.00 | 22.34 | A | C |
| ATOM | 1293 | CG | LYS A 405 | 8.060 | 25.967 | 13.046 | 1.00 | 22.94 | A | C |
| ATOM | 1294 | CD | LYS A 405 | 9.278 | 26.878 | 12.898 | 1.00 | 24.78 | A | C |
| ATOM | 1295 | CE | LYS A 405 | 8.960 | 28.328 | 13.246 | 1.00 | 25.04 | A | C |
| ATOM | 1296 | NZ | LYS A 405 | 10.018 | 29.277 | 12.753 | 1.00 | 26.05 | A | N |
| ATOM | 1297 | C | LYS A 405 | 7.386 | 22.330 | 11.900 | 1.00 | 20.83 | A | C |
| ATOM | 1298 | O | LYS A 405 | 7.608 | 22.428 | 10.691 | 1.00 | 21.14 | A | O |
| ATOM | 1299 | N | TRP A 406 | 7.314 | 21.157 | 12.529 | 1.00 | 19.62 | A | N |
| ATOM | 1300 | CA | TRP A 406 | 7.462 | 19.888 | 11.820 | 1.00 | 19.96 | A | C |
| ATOM | 1301 | CB | TRP A 406 | 8.545 | 19.015 | 12.467 | 1.00 | 20.28 | A | C |
| ATOM | 1302 | CG | TRP A 406 | 9.941 | 19.565 | 12.315 | 1.00 | 21.33 | A | C |
| ATOM | 1303 | CD2 | TRP A 406 | 10.540 | 20.586 | 13.118 | 1.00 | 20.51 | A | C |
| ATOM | 1304 | CE2 | TRP A 406 | 11.811 | 20.863 | 12.561 | 1.00 | 20.53 | A | C |
| ATOM | 1305 | CE3 | TRP A 406 | 10.121 | 21.299 | 14.253 | 1.00 | 19.32 | A | C |
| ATOM | 1306 | CD1 | TRP A 406 | 10.856 | 19.253 | 11.337 | 1.00 | 20.95 | A | C |
| ATOM | 1307 | NE1 | TRP A 406 | 11.975 | 20.038 | 11.476 | 1.00 | 20.63 | A | N |
| ATOM | 1308 | CZ2 | TRP A 406 | 12.665 | 21.826 | 13.101 | 1.00 | 19.78 | A | C |
| ATOM | 1309 | CZ3 | TRP A 406 | 10.962 | 22.251 | 14.787 | 1.00 | 19.72 | A | C |
| ATOM | 1310 | CH2 | TRP A 406 | 12.225 | 22.510 | 14.211 | 1.00 | 20.81 | A | C |
| ATOM | 1311 | C | TRP A 406 | 6.160 | 19.087 | 11.804 | 1.00 | 20.59 | A | C |
| ATOM | 1312 | O | TRP A 406 | 6.082 | 18.031 | 11.170 | 1.00 | 21.22 | A | O |
| ATOM | 1313 | N | THR A 407 | 5.136 | 19.606 | 12.475 | 1.00 | 20.39 | A | N |
| ATOM | 1314 | CA | THR A 407 | 3.861 | 18.908 | 12.623 | 1.00 | 20.15 | A | C |
| ATOM | 1315 | CB | THR A 407 | 3.248 | 19.258 | 13.996 | 1.00 | 20.87 | A | C |
| ATOM | 1316 | OG1 | THR A 407 | 4.271 | 19.177 | 14.994 | 1.00 | 22.37 | A | O |
| ATOM | 1317 | CG2 | THR A 407 | 2.154 | 18.277 | 14.357 | 1.00 | 20.38 | A | C |
| ATOM | 1318 | C | THR A 407 | 2.846 | 19.131 | 11.504 | 1.00 | 18.70 | A | C |
| ATOM | 1319 | O | THR A 407 | 2.528 | 20.272 | 11.169 | 1.00 | 18.70 | A | O |
| ATOM | 1320 | N | ALA A 408 | 2.351 | 18.028 | 10.938 | 1.00 | 18.11 | A | N |
| ATOM | 1321 | CA | ALA A 408 | 1.369 | 18.061 | 9.846 | 1.00 | 18.84 | A | C |
| ATOM | 1322 | CB | ALA A 408 | 1.084 | 16.662 | 9.361 | 1.00 | 16.41 | A | C |
| ATOM | 1323 | C | ALA A 408 | 0.080 | 18.718 | 10.305 | 1.00 | 19.41 | A | C |
| ATOM | 1324 | O | ALA A 408 | -0.311 | 18.541 | 11.454 | 1.00 | 20.29 | A | O |
| ATOM | 1325 | N | PRO A 409 | -0.653 | 19.397 | 9.387 | 1.00 | 20.15 | A | N |
| ATOM | 1326 | CD | PRO A 409 | -0.432 | 19.512 | 7.937 | 1.00 | 18.77 | A | C |
| ATOM | 1327 | CA | PRO A 409 | -1.909 | 20.070 | 9.749 | 1.00 | 20.33 | A | C |
| ATOM | 1328 | CB | PRO A 409 | -2.434 | 20.571 | 8.401 | 1.00 | 20.84 | A | C |
| ATOM | 1329 | CG | PRO A 409 | -1.190 | 20.758 | 7.605 | 1.00 | 18.93 | A | C |
| ATOM | 1330 | C | PRO A 409 | -2.923 | 19.198 | 10.488 | 1.00 | 20.07 | A | C |
| ATOM | 1331 | O | PRO A 409 | -3.523 | 19.662 | 11.453 | 1.00 | 19.70 | A | O |
| ATOM | 1332 | N | GLU A 410 | -3.084 | 17.941 | 10.076 | 1.00 | 19.36 | A | N |
| ATOM | 1333 | CA | GLU A 410 | -4.027 | 17.055 | 10.752 | 1.00 | 20.87 | A | C |
| ATOM | 1334 | CB | GLU A 410 | -4.344 | 15.808 | 9.907 | 1.00 | 20.06 | A | C |
| ATOM | 1335 | CG | GLU A 410 | -3.237 | 14.747 | 9.798 | 1.00 | 20.00 | A | C |
| ATOM | 1336 | CD | GLU A 410 | -2.136 | 15.044 | 8.769 | 1.00 | 18.27 | A | C |
| ATOM | 1337 | OE1 | GLU A 410 | -2.167 | 16.086 | 8.076 | 1.00 | 18.54 | A | O |
| ATOM | 1338 | OE2 | GLU A 410 | -1.236 | 14.195 | 8.651 | 1.00 | 17.59 | A | O |
| ATOM | 1339 | C | GLU A 410 | -3.558 | 16.666 | 12.170 | 1.00 | 22.65 | A | C |
| ATOM | 1340 | O | GLU A 410 | -4.378 | 16.376 | 13.056 | 1.00 | 23.21 | A | O |
| ATOM | 1341 | N | ALA A 411 | -2.243 | 16.676 | 12.392 | 1.00 | 23.21 | A | N |
| ATOM | 1342 | CA | ALA A 411 | -1.700 | 16.345 | 13.700 | 1.00 | 22.95 | A | C |
| ATOM | 1343 | CB | ALA A 411 | -0.273 | 15.909 | 13.572 | 1.00 | 23.12 | A | C |
| ATOM | 1344 | C | ALA A 411 | -1.825 | 17.550 | 14.629 | 1.00 | 23.81 | A | C |

Figure 9

```
ATOM   1345  O    ALA A 411      -1.934  17.403  15.842  1.00 24.48           A  O
ATOM   1346  N    ILE A 412      -1.829  18.745  14.057  1.00 24.72           A  N
ATOM   1347  CA   ILE A 412      -1.965  19.961  14.844  1.00 26.06           A  C
ATOM   1348  CB   ILE A 412      -1.517  21.206  14.058  1.00 25.55           A  C
ATOM   1349  CG2  ILE A 412      -1.911  22.466  14.819  1.00 26.24           A  C
ATOM   1350  CG1  ILE A 412      -0.005  21.179  13.832  1.00 25.51           A  C
ATOM   1351  CD1  ILE A 412       0.508  22.314  12.990  1.00 23.45           A  C
ATOM   1352  C    ILE A 412      -3.418  20.182  15.280  1.00 28.11           A  C
ATOM   1353  O    ILE A 412      -3.679  20.446  16.455  1.00 28.43           A  O
ATOM   1354  N    ASN A 413      -4.344  20.062  14.323  1.00 28.85           A  N
ATOM   1355  CA   ASN A 413      -5.780  20.271  14.542  1.00 29.69           A  C
ATOM   1356  CB   ASN A 413      -6.486  20.517  13.206  1.00 29.63           A  C
ATOM   1357  CG   ASN A 413      -5.910  21.687  12.450  1.00 31.41           A  C
ATOM   1358  OD1  ASN A 413      -5.420  22.639  13.048  1.00 32.92           A  O
ATOM   1359  ND2  ASN A 413      -5.950  21.618  11.123  1.00 31.93           A  N
ATOM   1360  C    ASN A 413      -6.541  19.172  15.272  1.00 29.67           A  C
ATOM   1361  O    ASN A 413      -7.441  19.465  16.045  1.00 30.79           A  O
ATOM   1362  N    TYR A 414      -6.210  17.913  14.997  1.00 30.30           A  N
ATOM   1363  CA   TYR A 414      -6.921  16.787  15.606  1.00 29.92           A  C
ATOM   1364  CB   TYR A 414      -7.762  16.088  14.529  1.00 30.91           A  C
ATOM   1365  CG   TYR A 414      -8.598  17.055  13.734  1.00 33.99           A  C
ATOM   1366  CD1  TYR A 414      -9.689  17.699  14.318  1.00 35.69           A  C
ATOM   1367  CE1  TYR A 414     -10.415  18.667  13.620  1.00 36.71           A  C
ATOM   1368  CD2  TYR A 414      -8.256  17.392  12.418  1.00 35.55           A  C
ATOM   1369  CE2  TYR A 414      -8.976  18.360  11.706  1.00 35.70           A  C
ATOM   1370  CZ   TYR A 414     -10.050  18.994  12.320  1.00 37.57           A  C
ATOM   1371  OH   TYR A 414     -10.741  19.985  11.659  1.00 40.06           A  O
ATOM   1372  C    TYR A 414      -6.043  15.758  16.330  1.00 28.59           A  C
ATOM   1373  O    TYR A 414      -6.552  14.775  16.873  1.00 28.33           A  O
ATOM   1374  N    GLY A 415      -4.732  15.977  16.329  1.00 27.16           A  N
ATOM   1375  CA   GLY A 415      -3.838  15.043  16.984  1.00 25.41           A  C
ATOM   1376  C    GLY A 415      -3.731  13.708  16.274  1.00 24.76           A  C
ATOM   1377  O    GLY A 415      -3.367  12.694  16.879  1.00 25.17           A  O
ATOM   1378  N    THR A 416      -4.043  13.683  14.984  1.00 24.51           A  N
ATOM   1379  CA   THR A 416      -3.948  12.433  14.250  1.00 23.94           A  C
ATOM   1380  CB   THR A 416      -5.154  12.230  13.261  1.00 23.95           A  C
ATOM   1381  OG1  THR A 416      -4.705  11.651  12.033  1.00 27.71           A  O
ATOM   1382  CG2  THR A 416      -5.897  13.513  13.004  1.00 21.71           A  C
ATOM   1383  C    THR A 416      -2.546  12.261  13.635  1.00 23.05           A  C
ATOM   1384  O    THR A 416      -2.199  12.862  12.627  1.00 23.30           A  O
ATOM   1385  N    PHE A 417      -1.729  11.488  14.346  1.00 22.52           A  N
ATOM   1386  CA   PHE A 417      -0.350  11.192  13.986  1.00 20.91           A  C
ATOM   1387  CB   PHE A 417       0.548  11.197  15.239  1.00 20.23           A  C
ATOM   1388  CG   PHE A 417       0.796  12.565  15.827  1.00 20.96           A  C
ATOM   1389  CD1  PHE A 417      -0.084  13.114  16.763  1.00 21.29           A  C
ATOM   1390  CD2  PHE A 417       1.908  13.315  15.436  1.00 20.64           A  C
ATOM   1391  CE1  PHE A 417       0.143  14.392  17.293  1.00 20.61           A  C
ATOM   1392  CE2  PHE A 417       2.140  14.586  15.959  1.00 18.76           A  C
ATOM   1393  CZ   PHE A 417       1.265  15.127  16.881  1.00 19.70           A  C
ATOM   1394  C    PHE A 417      -0.249   9.835  13.319  1.00 19.85           A  C
ATOM   1395  O    PHE A 417      -0.655   8.828  13.887  1.00 20.66           A  O
ATOM   1396  N    THR A 418       0.303   9.813  12.109  1.00 19.64           A  N
ATOM   1397  CA   THR A 418       0.489   8.572  11.345  1.00 18.28           A  C
ATOM   1398  CB   THR A 418      -0.660   8.355  10.307  1.00 17.70           A  C
ATOM   1399  OG1  THR A 418      -0.572   9.340   9.264  1.00 18.02           A  O
ATOM   1400  CG2  THR A 418      -2.042   8.473  10.994  1.00 17.98           A  C
ATOM   1401  C    THR A 418       1.822   8.666  10.592  1.00 16.87           A  C
ATOM   1402  O    THR A 418       2.551   9.636  10.749  1.00 17.36           A  O
ATOM   1403  N    ILE A 419       2.127   7.669   9.772  1.00 17.29           A  N
```

Figure 9

| | | | | | | | | | | | |
|---|---|---|---|---|---|---|---|---|---|---|---|
| ATOM | 1404 | CA | ILE | A | 419 | 3.360 | 7.662 | 8.983 | 1.00 | 17.84 | A | C |
| ATOM | 1405 | CB | ILE | A | 419 | 3.576 | 6.294 | 8.248 | 1.00 | 18.88 | A | C |
| ATOM | 1406 | CG2 | ILE | A | 419 | 2.606 | 6.133 | 7.069 | 1.00 | 17.41 | A | C |
| ATOM | 1407 | CG1 | ILE | A | 419 | 5.023 | 6.176 | 7.743 | 1.00 | 18.45 | A | C |
| ATOM | 1408 | CD1 | ILE | A | 419 | 6.064 | 6.099 | 8.857 | 1.00 | 17.15 | A | C |
| ATOM | 1409 | C | ILE | A | 419 | 3.296 | 8.813 | 7.973 | 1.00 | 18.23 | A | C |
| ATOM | 1410 | O | ILE | A | 419 | 4.329 | 9.348 | 7.555 | 1.00 | 18.37 | A | O |
| ATOM | 1411 | N | LYS | A | 420 | 2.076 | 9.222 | 7.620 | 1.00 | 17.09 | A | N |
| ATOM | 1412 | CA | LYS | A | 420 | 1.891 | 10.328 | 6.688 | 1.00 | 16.49 | A | C |
| ATOM | 1413 | CB | LYS | A | 420 | 0.477 | 10.342 | 6.092 | 1.00 | 16.30 | A | C |
| ATOM | 1414 | CG | LYS | A | 420 | 0.196 | 9.174 | 5.165 | 1.00 | 14.54 | A | C |
| ATOM | 1415 | CD | LYS | A | 420 | 1.163 | 9.169 | 4.010 | 1.00 | 13.93 | A | C |
| ATOM | 1416 | CE | LYS | A | 420 | 0.849 | 8.039 | 3.084 | 1.00 | 13.19 | A | C |
| ATOM | 1417 | NZ | LYS | A | 420 | 1.892 | 7.921 | 2.067 | 1.00 | 14.18 | A | N |
| ATOM | 1418 | C | LYS | A | 420 | 2.236 | 11.667 | 7.327 | 1.00 | 15.57 | A | C |
| ATOM | 1419 | O | LYS | A | 420 | 2.680 | 12.576 | 6.626 | 1.00 | 16.46 | A | O |
| ATOM | 1420 | N | SER | A | 421 | 2.036 | 11.801 | 8.642 | 1.00 | 15.25 | A | N |
| ATOM | 1421 | CA | SER | A | 421 | 2.408 | 13.040 | 9.315 | 1.00 | 14.94 | A | C |
| ATOM | 1422 | CB | SER | A | 421 | 1.621 | 13.300 | 10.614 | 1.00 | 14.48 | A | C |
| ATOM | 1423 | OG | SER | A | 421 | 1.507 | 12.174 | 11.450 | 1.00 | 16.41 | A | O |
| ATOM | 1424 | C | SER | A | 421 | 3.931 | 13.072 | 9.480 | 1.00 | 14.70 | A | C |
| ATOM | 1425 | O | SER | A | 421 | 4.522 | 14.140 | 9.580 | 1.00 | 15.78 | A | O |
| ATOM | 1426 | N | ASP | A | 422 | 4.566 | 11.901 | 9.449 | 1.00 | 15.02 | A | N |
| ATOM | 1427 | CA | ASP | A | 422 | 6.032 | 11.831 | 9.492 | 1.00 | 15.59 | A | C |
| ATOM | 1428 | CB | ASP | A | 422 | 6.558 | 10.424 | 9.769 | 1.00 | 14.50 | A | C |
| ATOM | 1429 | CG | ASP | A | 422 | 6.339 | 9.968 | 11.180 | 1.00 | 14.41 | A | C |
| ATOM | 1430 | OD1 | ASP | A | 422 | 6.284 | 10.796 | 12.109 | 1.00 | 16.52 | A | O |
| ATOM | 1431 | OD2 | ASP | A | 422 | 6.259 | 8.744 | 11.348 | 1.00 | 15.07 | A | O |
| ATOM | 1432 | C | ASP | A | 422 | 6.538 | 12.208 | 8.096 | 1.00 | 15.53 | A | C |
| ATOM | 1433 | O | ASP | A | 422 | 7.634 | 12.740 | 7.974 | 1.00 | 16.83 | A | O |
| ATOM | 1434 | N | VAL | A | 423 | 5.789 | 11.849 | 7.045 | 1.00 | 15.56 | A | N |
| ATOM | 1435 | CA | VAL | A | 423 | 6.188 | 12.182 | 5.675 | 1.00 | 15.53 | A | C |
| ATOM | 1436 | CB | VAL | A | 423 | 5.264 | 11.551 | 4.569 | 1.00 | 15.51 | A | C |
| ATOM | 1437 | CG1 | VAL | A | 423 | 5.634 | 12.119 | 3.165 | 1.00 | 14.88 | A | C |
| ATOM | 1438 | CG2 | VAL | A | 423 | 5.429 | 10.044 | 4.534 | 1.00 | 14.19 | A | C |
| ATOM | 1439 | C | VAL | A | 423 | 6.218 | 13.694 | 5.548 | 1.00 | 15.68 | A | C |
| ATOM | 1440 | O | VAL | A | 423 | 7.110 | 14.246 | 4.901 | 1.00 | 16.43 | A | O |
| ATOM | 1441 | N | TRP | A | 424 | 5.273 | 14.357 | 6.218 | 1.00 | 15.20 | A | N |
| ATOM | 1442 | CA | TRP | A | 424 | 5.189 | 15.815 | 6.235 | 1.00 | 13.73 | A | C |
| ATOM | 1443 | CB | TRP | A | 424 | 3.930 | 16.264 | 6.999 | 1.00 | 12.03 | A | C |
| ATOM | 1444 | CG | TRP | A | 424 | 3.842 | 17.756 | 7.200 | 1.00 | 11.60 | A | C |
| ATOM | 1445 | CD2 | TRP | A | 424 | 2.984 | 18.673 | 6.501 | 1.00 | 12.28 | A | C |
| ATOM | 1446 | CE2 | TRP | A | 424 | 3.299 | 19.978 | 6.963 | 1.00 | 13.62 | A | C |
| ATOM | 1447 | CE3 | TRP | A | 424 | 1.984 | 18.525 | 5.526 | 1.00 | 12.06 | A | C |
| ATOM | 1448 | CD1 | TRP | A | 424 | 4.610 | 18.524 | 8.043 | 1.00 | 10.91 | A | C |
| ATOM | 1449 | NE1 | TRP | A | 424 | 4.297 | 19.855 | 7.896 | 1.00 | 11.15 | A | N |
| ATOM | 1450 | CZ2 | TRP | A | 424 | 2.645 | 21.125 | 6.479 | 1.00 | 14.76 | A | C |
| ATOM | 1451 | CZ3 | TRP | A | 424 | 1.339 | 19.657 | 5.048 | 1.00 | 11.78 | A | C |
| ATOM | 1452 | CH2 | TRP | A | 424 | 1.672 | 20.942 | 5.522 | 1.00 | 13.59 | A | C |
| ATOM | 1453 | C | TRP | A | 424 | 6.454 | 16.357 | 6.918 | 1.00 | 13.97 | A | C |
| ATOM | 1454 | O | TRP | A | 424 | 7.087 | 17.277 | 6.414 | 1.00 | 13.19 | A | O |
| ATOM | 1455 | N | SER | A | 425 | 6.810 | 15.768 | 8.063 | 1.00 | 15.55 | A | N |
| ATOM | 1456 | CA | SER | A | 425 | 8.003 | 16.161 | 8.840 | 1.00 | 17.99 | A | C |
| ATOM | 1457 | CB | SER | A | 425 | 8.104 | 15.345 | 10.129 | 1.00 | 17.88 | A | C |
| ATOM | 1458 | OG | SER | A | 425 | 7.079 | 15.691 | 11.033 | 1.00 | 20.80 | A | O |
| ATOM | 1459 | C | SER | A | 425 | 9.302 | 15.978 | 8.056 | 1.00 | 17.52 | A | C |
| ATOM | 1460 | O | SER | A | 425 | 10.206 | 16.801 | 8.135 | 1.00 | 19.83 | A | O |
| ATOM | 1461 | N | PHE | A | 426 | 9.394 | 14.877 | 7.328 | 1.00 | 16.92 | A | N |
| ATOM | 1462 | CA | PHE | A | 426 | 10.559 | 14.579 | 6.514 | 1.00 | 17.13 | A | C |

Figure 9

| | | | | | | | | | | |
|---|---|---|---|---|---|---|---|---|---|---|
| ATOM | 1463 | CB | PHE | A | 426 | 10.384 | 13.229 | 5.812 | 1.00 16.49 | A C |
| ATOM | 1464 | CG | PHE | A | 426 | 11.540 | 12.859 | 4.948 | 1.00 16.60 | A C |
| ATOM | 1465 | CD1 | PHE | A | 426 | 12.698 | 12.339 | 5.511 | 1.00 15.95 | A C |
| ATOM | 1466 | CD2 | PHE | A | 426 | 11.493 | 13.090 | 3.580 | 1.00 16.40 | A C |
| ATOM | 1467 | CE1 | PHE | A | 426 | 13.801 | 12.057 | 4.736 | 1.00 17.25 | A C |
| ATOM | 1468 | CE2 | PHE | A | 426 | 12.592 | 12.814 | 2.780 | 1.00 18.63 | A C |
| ATOM | 1469 | CZ | PHE | A | 426 | 13.757 | 12.295 | 3.363 | 1.00 18.95 | A C |
| ATOM | 1470 | C | PHE | A | 426 | 10.778 | 15.678 | 5.483 | 1.00 17.37 | A C |
| ATOM | 1471 | O | PHE | A | 426 | 11.922 | 16.000 | 5.143 | 1.00 19.14 | A O |
| ATOM | 1472 | N | GLY | A | 427 | 9.677 | 16.196 | 4.936 | 1.00 16.39 | A N |
| ATOM | 1473 | CA | GLY | A | 427 | 9.751 | 17.277 | 3.970 | 1.00 14.68 | A C |
| ATOM | 1474 | C | GLY | A | 427 | 10.293 | 18.544 | 4.615 | 1.00 14.40 | A C |
| ATOM | 1475 | O | GLY | A | 427 | 10.977 | 19.328 | 3.958 | 1.00 14.17 | A O |
| ATOM | 1476 | N | ILE | A | 428 | 9.931 | 18.778 | 5.878 | 1.00 14.67 | A N |
| ATOM | 1477 | CA | ILE | A | 428 | 10.424 | 19.947 | 6.627 | 1.00 15.74 | A C |
| ATOM | 1478 | CB | ILE | A | 428 | 9.667 | 20.150 | 7.978 | 1.00 15.25 | A C |
| ATOM | 1479 | CG2 | ILE | A | 428 | 10.202 | 21.376 | 8.709 | 1.00 14.38 | A C |
| ATOM | 1480 | CG1 | ILE | A | 428 | 8.168 | 20.312 | 7.739 | 1.00 14.19 | A C |
| ATOM | 1481 | CD1 | ILE | A | 428 | 7.779 | 21.600 | 7.009 | 1.00 12.56 | A C |
| ATOM | 1482 | C | ILE | A | 428 | 11.917 | 19.713 | 6.935 | 1.00 16.50 | A C |
| ATOM | 1483 | O | ILE | A | 428 | 12.732 | 20.636 | 6.866 | 1.00 16.80 | A O |
| ATOM | 1484 | N | LEU | A | 429 | 12.255 | 18.462 | 7.245 | 1.00 16.81 | A N |
| ATOM | 1485 | CA | LEU | A | 429 | 13.623 | 18.064 | 7.539 | 1.00 17.61 | A C |
| ATOM | 1486 | CB | LEU | A | 429 | 13.658 | 16.577 | 7.944 | 1.00 17.70 | A C |
| ATOM | 1487 | CG | LEU | A | 429 | 14.874 | 15.956 | 8.654 | 1.00 17.48 | A C |
| ATOM | 1488 | CD1 | LEU | A | 429 | 14.539 | 14.591 | 9.197 | 1.00 17.06 | A C |
| ATOM | 1489 | CD2 | LEU | A | 429 | 16.028 | 15.834 | 7.733 | 1.00 17.93 | A C |
| ATOM | 1490 | C | LEU | A | 429 | 14.511 | 18.313 | 6.304 | 1.00 18.22 | A C |
| ATOM | 1491 | O | LEU | A | 429 | 15.662 | 18.714 | 6.451 | 1.00 18.13 | A O |
| ATOM | 1492 | N | LEU | A | 430 | 13.973 | 18.087 | 5.099 | 1.00 18.41 | A N |
| ATOM | 1493 | CA | LEU | A | 430 | 14.725 | 18.302 | 3.853 | 1.00 18.31 | A C |
| ATOM | 1494 | CB | LEU | A | 430 | 13.925 | 17.857 | 2.618 | 1.00 16.26 | A C |
| ATOM | 1495 | CG | LEU | A | 430 | 13.752 | 16.376 | 2.280 | 1.00 13.87 | A C |
| ATOM | 1496 | CD1 | LEU | A | 430 | 12.834 | 16.240 | 1.084 | 1.00 13.72 | A C |
| ATOM | 1497 | CD2 | LEU | A | 430 | 15.090 | 15.722 | 1.989 | 1.00 13.07 | A C |
| ATOM | 1498 | C | LEU | A | 430 | 15.169 | 19.765 | 3.689 | 1.00 19.22 | A C |
| ATOM | 1499 | O | LEU | A | 430 | 16.229 | 20.026 | 3.117 | 1.00 19.75 | A O |
| ATOM | 1500 | N | THR | A | 431 | 14.345 | 20.713 | 4.153 | 1.00 20.01 | A N |
| ATOM | 1501 | CA | THR | A | 431 | 14.694 | 22.139 | 4.092 | 1.00 20.57 | A C |
| ATOM | 1502 | CB | THR | A | 431 | 13.479 | 23.086 | 4.425 | 1.00 19.56 | A C |
| ATOM | 1503 | OG1 | THR | A | 431 | 13.101 | 22.966 | 5.808 | 1.00 20.73 | A O |
| ATOM | 1504 | CG2 | THR | A | 431 | 12.284 | 22.756 | 3.554 | 1.00 20.54 | A C |
| ATOM | 1505 | C | THR | A | 431 | 15.867 | 22.406 | 5.065 | 1.00 21.34 | A C |
| ATOM | 1506 | O | THR | A | 431 | 16.768 | 23.190 | 4.765 | 1.00 21.38 | A O |
| ATOM | 1507 | N | GLU | A | 432 | 15.849 | 21.730 | 6.219 | 1.00 21.16 | A N |
| ATOM | 1508 | CA | GLU | A | 432 | 16.907 | 21.844 | 7.221 | 1.00 21.03 | A C |
| ATOM | 1509 | CB | GLU | A | 432 | 16.595 | 20.973 | 8.438 | 1.00 19.95 | A C |
| ATOM | 1510 | CG | GLU | A | 432 | 15.501 | 21.498 | 9.321 | 1.00 19.58 | A C |
| ATOM | 1511 | CD | GLU | A | 432 | 15.322 | 20.660 | 10.569 | 1.00 19.58 | A C |
| ATOM | 1512 | OE1 | GLU | A | 432 | 14.747 | 19.558 | 10.479 | 1.00 18.89 | A O |
| ATOM | 1513 | OE2 | GLU | A | 432 | 15.747 | 21.113 | 11.649 | 1.00 19.49 | A O |
| ATOM | 1514 | C | GLU | A | 432 | 18.229 | 21.368 | 6.633 | 1.00 21.56 | A C |
| ATOM | 1515 | O | GLU | A | 432 | 19.274 | 21.943 | 6.907 | 1.00 22.26 | A O |
| ATOM | 1516 | N | ILE | A | 433 | 18.174 | 20.286 | 5.860 | 1.00 22.19 | A N |
| ATOM | 1517 | CA | ILE | A | 433 | 19.357 | 19.712 | 5.233 | 1.00 21.74 | A C |
| ATOM | 1518 | CB | ILE | A | 433 | 19.058 | 18.316 | 4.661 | 1.00 20.42 | A C |
| ATOM | 1519 | CG2 | ILE | A | 433 | 20.203 | 17.832 | 3.786 | 1.00 21.42 | A C |
| ATOM | 1520 | CG1 | ILE | A | 433 | 18.846 | 17.323 | 5.798 | 1.00 20.57 | A C |
| ATOM | 1521 | CD1 | ILE | A | 433 | 18.598 | 15.886 | 5.335 | 1.00 19.15 | A C |

Figure 9

| | | | | | | | | | | |
|---|---|---|---|---|---|---|---|---|---|---|
| ATOM | 1522 | C | ILE | A | 433 | 19.967 | 20.594 | 4.141 | 1.00 23.03 | A C |
| ATOM | 1523 | O | ILE | A | 433 | 21.187 | 20.723 | 4.067 | 1.00 23.95 | A O |
| ATOM | 1524 | N | VAL | A | 434 | 19.139 | 21.228 | 3.316 | 1.00 23.38 | A N |
| ATOM | 1525 | CA | VAL | A | 434 | 19.674 | 22.056 | 2.239 | 1.00 25.23 | A C |
| ATOM | 1526 | CB | VAL | A | 434 | 18.788 | 22.006 | 0.963 | 1.00 24.82 | A C |
| ATOM | 1527 | CG1 | VAL | A | 434 | 18.731 | 20.576 | 0.450 | 1.00 23.79 | A C |
| ATOM | 1528 | CG2 | VAL | A | 434 | 17.372 | 22.561 | 1.237 | 1.00 24.50 | A C |
| ATOM | 1529 | C | VAL | A | 434 | 20.023 | 23.489 | 2.626 | 1.00 26.45 | A C |
| ATOM | 1530 | O | VAL | A | 434 | 20.632 | 24.218 | 1.846 | 1.00 28.89 | A O |
| ATOM | 1531 | N | THR | A | 435 | 19.651 | 23.888 | 3.837 | 1.00 27.18 | A N |
| ATOM | 1532 | CA | THR | A | 435 | 19.957 | 25.226 | 4.320 | 1.00 28.41 | A C |
| ATOM | 1533 | CB | THR | A | 435 | 18.697 | 25.930 | 4.826 | 1.00 27.96 | A C |
| ATOM | 1534 | OG1 | THR | A | 435 | 18.131 | 25.167 | 5.891 | 1.00 27.56 | A O |
| ATOM | 1535 | CG2 | THR | A | 435 | 17.671 | 26.086 | 3.698 | 1.00 26.58 | A C |
| ATOM | 1536 | C | THR | A | 435 | 20.959 | 25.149 | 5.475 | 1.00 29.63 | A C |
| ATOM | 1537 | O | THR | A | 435 | 21.168 | 26.127 | 6.186 | 1.00 30.12 | A O |
| ATOM | 1538 | N | HIS | A | 436 | 21.540 | 23.966 | 5.670 | 1.00 31.55 | A N |
| ATOM | 1539 | CA | HIS | A | 436 | 22.512 | 23.694 | 6.727 | 1.00 33.05 | A C |
| ATOM | 1540 | CB | HIS | A | 436 | 23.831 | 24.421 | 6.440 | 1.00 36.74 | A C |
| ATOM | 1541 | CG | HIS | A | 436 | 24.383 | 24.154 | 5.069 | 1.00 40.72 | A C |
| ATOM | 1542 | CD2 | HIS | A | 436 | 24.757 | 25.001 | 4.079 | 1.00 41.98 | A C |
| ATOM | 1543 | ND1 | HIS | A | 436 | 24.601 | 22.880 | 4.581 | 1.00 42.13 | A N |
| ATOM | 1544 | CE1 | HIS | A | 436 | 25.086 | 22.951 | 3.354 | 1.00 40.88 | A C |
| ATOM | 1545 | NE2 | HIS | A | 436 | 25.189 | 24.227 | 3.025 | 1.00 42.79 | A N |
| ATOM | 1546 | C | HIS | A | 436 | 22.023 | 23.986 | 8.157 | 1.00 32.62 | A C |
| ATOM | 1547 | O | HIS | A | 436 | 22.682 | 24.707 | 8.914 | 1.00 32.88 | A O |
| ATOM | 1548 | N | GLY | A | 437 | 20.875 | 23.412 | 8.517 | 1.00 31.42 | A N |
| ATOM | 1549 | CA | GLY | A | 437 | 20.322 | 23.575 | 9.855 | 1.00 31.57 | A C |
| ATOM | 1550 | C | GLY | A | 437 | 19.477 | 24.796 | 10.184 | 1.00 31.34 | A C |
| ATOM | 1551 | O | GLY | A | 437 | 19.164 | 25.040 | 11.355 | 1.00 30.17 | A O |
| ATOM | 1552 | N | ARG | A | 438 | 19.090 | 25.552 | 9.165 | 1.00 31.87 | A N |
| ATOM | 1553 | CA | ARG | A | 438 | 18.270 | 26.748 | 9.364 | 1.00 33.16 | A C |
| ATOM | 1554 | CB | ARG | A | 438 | 18.176 | 27.520 | 8.050 | 1.00 36.36 | A C |
| ATOM | 1555 | CG | ARG | A | 438 | 17.785 | 28.990 | 8.168 | 1.00 41.08 | A C |
| ATOM | 1556 | CD | ARG | A | 438 | 16.280 | 29.198 | 8.348 | 1.00 45.15 | A C |
| ATOM | 1557 | NE | ARG | A | 438 | 15.467 | 28.558 | 7.306 | 1.00 48.58 | A N |
| ATOM | 1558 | CZ | ARG | A | 438 | 15.474 | 28.909 | 6.020 | 1.00 50.61 | A C |
| ATOM | 1559 | NH1 | ARG | A | 438 | 16.257 | 29.905 | 5.606 | 1.00 51.48 | A N |
| ATOM | 1560 | NH2 | ARG | A | 438 | 14.718 | 28.249 | 5.143 | 1.00 50.52 | A N |
| ATOM | 1561 | C | ARG | A | 438 | 16.876 | 26.350 | 9.848 | 1.00 31.82 | A C |
| ATOM | 1562 | O | ARG | A | 438 | 16.311 | 25.364 | 9.376 | 1.00 31.39 | A O |
| ATOM | 1563 | N | ILE | A | 439 | 16.346 | 27.105 | 10.804 | 1.00 30.86 | A N |
| ATOM | 1564 | CA | ILE | A | 439 | 15.019 | 26.849 | 11.374 | 1.00 30.76 | A C |
| ATOM | 1565 | CB | ILE | A | 439 | 14.770 | 27.765 | 12.609 | 1.00 31.20 | A C |
| ATOM | 1566 | CG2 | ILE | A | 439 | 13.298 | 27.794 | 13.009 | 1.00 30.49 | A C |
| ATOM | 1567 | CG1 | ILE | A | 439 | 15.609 | 27.271 | 13.791 | 1.00 32.91 | A C |
| ATOM | 1568 | CD1 | ILE | A | 439 | 15.573 | 28.197 | 15.000 | 1.00 34.12 | A C |
| ATOM | 1569 | C | ILE | A | 439 | 13.914 | 27.042 | 10.326 | 1.00 30.22 | A C |
| ATOM | 1570 | O | ILE | A | 439 | 13.937 | 28.003 | 9.554 | 1.00 30.34 | A O |
| ATOM | 1571 | N | PRO | A | 440 | 12.947 | 26.109 | 10.270 | 1.00 29.33 | A N |
| ATOM | 1572 | CD | PRO | A | 440 | 12.876 | 24.858 | 11.043 | 1.00 28.40 | A C |
| ATOM | 1573 | CA | PRO | A | 440 | 11.840 | 26.188 | 9.307 | 1.00 29.05 | A C |
| ATOM | 1574 | CB | PRO | A | 440 | 11.025 | 24.940 | 9.633 | 1.00 28.95 | A C |
| ATOM | 1575 | CG | PRO | A | 440 | 12.082 | 23.981 | 10.136 | 1.00 28.71 | A C |
| ATOM | 1576 | C | PRO | A | 440 | 11.028 | 27.452 | 9.510 | 1.00 28.67 | A C |
| ATOM | 1577 | O | PRO | A | 440 | 11.021 | 28.005 | 10.598 | 1.00 28.48 | A O |
| ATOM | 1578 | N | TYR | A | 441 | 10.391 | 27.930 | 8.443 | 1.00 29.12 | A N |
| ATOM | 1579 | CA | TYR | A | 441 | 9.565 | 29.140 | 8.486 | 1.00 29.51 | A C |
| ATOM | 1580 | CB | TYR | A | 441 | 8.228 | 28.866 | 9.195 | 1.00 27.24 | A C |

Figure 9

| ATOM | 1581 | CG | TYR A 441 | 7.464 | 27.665 | 8.674 | 1.00 | 25.75 | A | C |
|------|------|-----|-----------|--------|--------|--------|------|-------|---|---|
| ATOM | 1582 | CD1 | TYR A 441 | 6.512 | 27.798 | 7.658 | 1.00 | 25.67 | A | C |
| ATOM | 1583 | CE1 | TYR A 441 | 5.796 | 26.702 | 7.193 | 1.00 | 25.21 | A | C |
| ATOM | 1584 | CD2 | TYR A 441 | 7.680 | 26.401 | 9.208 | 1.00 | 23.86 | A | C |
| ATOM | 1585 | CE2 | TYR A 441 | 6.976 | 25.305 | 8.757 | 1.00 | 24.49 | A | C |
| ATOM | 1586 | CZ | TYR A 441 | 6.034 | 25.454 | 7.748 | 1.00 | 24.95 | A | C |
| ATOM | 1587 | OH | TYR A 441 | 5.338 | 24.350 | 7.298 | 1.00 | 25.37 | A | O |
| ATOM | 1588 | C | TYR A 441 | 10.309 | 30.285 | 9.180 | 1.00 | 31.54 | A | C |
| ATOM | 1589 | O | TYR A 441 | 9.862 | 30.806 | 10.210 | 1.00 | 30.84 | A | O |
| ATOM | 1590 | N | PRO A 442 | 11.470 | 30.681 | 8.629 | 1.00 | 33.77 | A | N |
| ATOM | 1591 | CD | PRO A 442 | 12.062 | 30.246 | 7.349 | 1.00 | 33.27 | A | C |
| ATOM | 1592 | CA | PRO A 442 | 12.251 | 31.767 | 9.228 | 1.00 | 36.11 | A | C |
| ATOM | 1593 | CB | PRO A 442 | 13.411 | 31.924 | 8.242 | 1.00 | 35.88 | A | C |
| ATOM | 1594 | CG | PRO A 442 | 12.819 | 31.459 | 6.921 | 1.00 | 34.64 | A | C |
| ATOM | 1595 | C | PRO A 442 | 11.404 | 33.037 | 9.340 | 1.00 | 38.39 | A | C |
| ATOM | 1596 | O | PRO A 442 | 10.724 | 33.415 | 8.386 | 1.00 | 39.87 | A | O |
| ATOM | 1597 | N | GLY A 443 | 11.404 | 33.666 | 10.514 | 1.00 | 39.88 | A | N |
| ATOM | 1598 | CA | GLY A 443 | 10.614 | 34.875 | 10.703 | 1.00 | 40.75 | A | C |
| ATOM | 1599 | C | GLY A 443 | 9.183 | 34.628 | 11.158 | 1.00 | 41.27 | A | C |
| ATOM | 1600 | O | GLY A 443 | 8.381 | 35.560 | 11.252 | 1.00 | 43.01 | A | O |
| ATOM | 1601 | N | MET A 444 | 8.851 | 33.374 | 11.438 | 1.00 | 40.40 | A | N |
| ATOM | 1602 | CA | MET A 444 | 7.514 | 33.034 | 11.898 | 1.00 | 39.01 | A | C |
| ATOM | 1603 | CB | MET A 444 | 6.799 | 32.110 | 10.900 | 1.00 | 38.42 | A | C |
| ATOM | 1604 | CG | MET A 444 | 6.408 | 32.784 | 9.588 | 1.00 | 37.10 | A | C |
| ATOM | 1605 | SD | MET A 444 | 5.536 | 31.733 | 8.398 | 1.00 | 34.64 | A | S |
| ATOM | 1606 | CE | MET A 444 | 4.534 | 30.890 | 9.414 | 1.00 | 34.84 | A | C |
| ATOM | 1607 | C | MET A 444 | 7.608 | 32.359 | 13.256 | 1.00 | 39.20 | A | C |
| ATOM | 1608 | O | MET A 444 | 8.523 | 31.572 | 13.516 | 1.00 | 39.66 | A | O |
| ATOM | 1609 | N | THR A 445 | 6.687 | 32.722 | 14.137 | 1.00 | 38.75 | A | N |
| ATOM | 1610 | CA | THR A 445 | 6.623 | 32.152 | 15.474 | 1.00 | 38.66 | A | C |
| ATOM | 1611 | CB | THR A 445 | 6.111 | 33.204 | 16.478 | 1.00 | 39.54 | A | C |
| ATOM | 1612 | OG1 | THR A 445 | 4.716 | 33.458 | 16.243 | 1.00 | 39.63 | A | O |
| ATOM | 1613 | CG2 | THR A 445 | 6.892 | 34.517 | 16.298 | 1.00 | 38.88 | A | C |
| ATOM | 1614 | C | THR A 445 | 5.638 | 30.990 | 15.401 | 1.00 | 38.22 | A | C |
| ATOM | 1615 | O | THR A 445 | 4.889 | 30.883 | 14.430 | 1.00 | 38.38 | A | O |
| ATOM | 1616 | N | ASN A 446 | 5.628 | 30.119 | 16.407 | 1.00 | 38.00 | A | N |
| ATOM | 1617 | CA | ASN A 446 | 4.695 | 28.992 | 16.395 | 1.00 | 37.86 | A | C |
| ATOM | 1618 | CB | ASN A 446 | 4.770 | 28.183 | 17.692 | 1.00 | 37.86 | A | C |
| ATOM | 1619 | CG | ASN A 446 | 6.013 | 27.311 | 17.753 | 1.00 | 38.32 | A | C |
| ATOM | 1620 | OD1 | ASN A 446 | 6.918 | 27.439 | 16.919 | 1.00 | 37.65 | A | O |
| ATOM | 1621 | ND2 | ASN A 446 | 6.059 | 26.409 | 18.731 | 1.00 | 39.14 | A | N |
| ATOM | 1622 | C | ASN A 446 | 3.254 | 29.384 | 16.056 | 1.00 | 37.47 | A | C |
| ATOM | 1623 | O | ASN A 446 | 2.694 | 28.853 | 15.094 | 1.00 | 36.13 | A | O |
| ATOM | 1624 | N | PRO A 447 | 2.652 | 30.349 | 16.805 | 1.00 | 37.92 | A | N |
| ATOM | 1625 | CD | PRO A 447 | 3.144 | 31.074 | 17.995 | 1.00 | 37.20 | A | C |
| ATOM | 1626 | CA | PRO A 447 | 1.269 | 30.761 | 16.504 | 1.00 | 36.47 | A | C |
| ATOM | 1627 | CB | PRO A 447 | 1.009 | 31.892 | 17.516 | 1.00 | 36.28 | A | C |
| ATOM | 1628 | CG | PRO A 447 | 2.400 | 32.377 | 17.892 | 1.00 | 36.69 | A | C |
| ATOM | 1629 | C | PRO A 447 | 1.067 | 31.224 | 15.056 | 1.00 | 34.52 | A | C |
| ATOM | 1630 | O | PRO A 447 | 0.023 | 30.953 | 14.464 | 1.00 | 33.97 | A | O |
| ATOM | 1631 | N | GLU A 448 | 2.081 | 31.876 | 14.486 | 1.00 | 32.62 | A | N |
| ATOM | 1632 | CA | GLU A 448 | 2.012 | 32.365 | 13.117 | 1.00 | 31.49 | A | C |
| ATOM | 1633 | CB | GLU A 448 | 3.150 | 33.324 | 12.831 | 1.00 | 32.13 | A | C |
| ATOM | 1634 | CG | GLU A 448 | 2.934 | 34.680 | 13.429 | 1.00 | 35.46 | A | C |
| ATOM | 1635 | CD | GLU A 448 | 4.132 | 35.582 | 13.267 | 1.00 | 37.08 | A | C |
| ATOM | 1636 | OE1 | GLU A 448 | 5.098 | 35.201 | 12.568 | 1.00 | 37.76 | A | O |
| ATOM | 1637 | OE2 | GLU A 448 | 4.102 | 36.684 | 13.848 | 1.00 | 38.91 | A | O |
| ATOM | 1638 | C | GLU A 448 | 2.030 | 31.262 | 12.082 | 1.00 | 30.46 | A | C |
| ATOM | 1639 | O | GLU A 448 | 1.403 | 31.388 | 11.035 | 1.00 | 30.59 | A | O |

Figure 9

| | | | | | | | | | | |
|---|---|---|---|---|---|---|---|---|---|---|
| ATOM | 1640 | N | VAL | A | 449 | 2.793 | 30.209 | 12.361 | 1.00 29.22 | A N |
| ATOM | 1641 | CA | VAL | A | 449 | 2.903 | 29.063 | 11.463 | 1.00 26.79 | A C |
| ATOM | 1642 | CB | VAL | A | 449 | 4.005 | 28.071 | 11.937 | 1.00 25.99 | A C |
| ATOM | 1643 | CG1 | VAL | A | 449 | 3.898 | 26.743 | 11.198 | 1.00 23.57 | A C |
| ATOM | 1644 | CG2 | VAL | A | 449 | 5.393 | 28.696 | 11.725 | 1.00 22.87 | A C |
| ATOM | 1645 | C | VAL | A | 449 | 1.553 | 28.395 | 11.412 | 1.00 26.10 | A C |
| ATOM | 1646 | O | VAL | A | 449 | 1.069 | 28.038 | 10.348 | 1.00 25.38 | A O |
| ATOM | 1647 | N | ILE | A | 450 | 0.915 | 28.318 | 12.571 | 1.00 26.46 | A N |
| ATOM | 1648 | CA | ILE | A | 450 | -0.402 | 27.719 | 12.698 | 1.00 27.23 | A C |
| ATOM | 1649 | CB | ILE | A | 450 | -0.930 | 27.811 | 14.142 | 1.00 27.34 | A C |
| ATOM | 1650 | CG2 | ILE | A | 450 | -2.363 | 27.275 | 14.207 | 1.00 26.69 | A C |
| ATOM | 1651 | CG1 | ILE | A | 450 | 0.022 | 27.106 | 15.122 | 1.00 27.82 | A C |
| ATOM | 1652 | CD1 | ILE | A | 450 | 0.146 | 25.625 | 14.935 | 1.00 25.99 | A C |
| ATOM | 1653 | C | ILE | A | 450 | -1.402 | 28.448 | 11.812 | 1.00 27.25 | A C |
| ATOM | 1654 | O | ILE | A | 450 | -2.102 | 27.816 | 11.026 | 1.00 28.20 | A O |
| ATOM | 1655 | N | GLN | A | 451 | -1.468 | 29.770 | 11.945 | 1.00 27.18 | A N |
| ATOM | 1656 | CA | GLN | A | 451 | -2.410 | 30.558 | 11.157 | 1.00 27.14 | A C |
| ATOM | 1657 | CB | GLN | A | 451 | -2.581 | 31.969 | 11.732 | 1.00 29.72 | A C |
| ATOM | 1658 | CG | GLN | A | 451 | -1.348 | 32.844 | 11.706 | 1.00 35.19 | A C |
| ATOM | 1659 | CD | GLN | A | 451 | -1.393 | 33.919 | 12.780 | 1.00 37.91 | A C |
| ATOM | 1660 | OE1 | GLN | A | 451 | -0.890 | 35.032 | 12.594 | 1.00 39.97 | A O |
| ATOM | 1661 | NE2 | GLN | A | 451 | -1.986 | 33.581 | 13.920 | 1.00 38.98 | A N |
| ATOM | 1662 | C | GLN | A | 451 | -2.080 | 30.588 | 9.676 | 1.00 24.87 | A C |
| ATOM | 1663 | O | GLN | A | 451 | -2.957 | 30.794 | 8.856 | 1.00 23.56 | A O |
| ATOM | 1664 | N | ASN | A | 452 | -0.818 | 30.374 | 9.332 | 1.00 24.11 | A N |
| ATOM | 1665 | CA | ASN | A | 452 | -0.446 | 30.343 | 7.928 | 1.00 23.33 | A C |
| ATOM | 1666 | CB | ASN | A | 452 | 1.041 | 30.628 | 7.729 | 1.00 24.18 | A C |
| ATOM | 1667 | CG | ASN | A | 452 | 1.313 | 32.098 | 7.459 | 1.00 26.01 | A C |
| ATOM | 1668 | OD1 | ASN | A | 452 | 1.346 | 32.527 | 6.308 | 1.00 27.33 | A O |
| ATOM | 1669 | ND2 | ASN | A | 452 | 1.487 | 32.885 | 8.526 | 1.00 27.40 | A N |
| ATOM | 1670 | C | ASN | A | 452 | -0.823 | 28.999 | 7.338 | 1.00 22.60 | A C |
| ATOM | 1671 | O | ASN | A | 452 | -1.234 | 28.928 | 6.184 | 1.00 21.73 | A O |
| ATOM | 1672 | N | LEU | A | 453 | -0.736 | 27.943 | 8.147 | 1.00 22.06 | A N |
| ATOM | 1673 | CA | LEU | A | 453 | -1.098 | 26.616 | 7.676 | 1.00 21.95 | A C |
| ATOM | 1674 | CB | LEU | A | 453 | -0.590 | 25.522 | 8.601 | 1.00 22.96 | A C |
| ATOM | 1675 | CG | LEU | A | 453 | 0.907 | 25.251 | 8.683 | 1.00 23.63 | A C |
| ATOM | 1676 | CD1 | LEU | A | 453 | 1.081 | 24.093 | 9.669 | 1.00 23.05 | A C |
| ATOM | 1677 | CD2 | LEU | A | 453 | 1.496 | 24.916 | 7.313 | 1.00 22.87 | A C |
| ATOM | 1678 | C | LEU | A | 453 | -2.603 | 26.497 | 7.533 | 1.00 21.68 | A C |
| ATOM | 1679 | O | LEU | A | 453 | -3.065 | 25.703 | 6.728 | 1.00 21.51 | A O |
| ATOM | 1680 | N | GLU | A | 454 | -3.367 | 27.235 | 8.340 | 1.00 21.35 | A N |
| ATOM | 1681 | CA | GLU | A | 454 | -4.828 | 27.211 | 8.202 | 1.00 22.99 | A C |
| ATOM | 1682 | CB | GLU | A | 454 | -5.508 | 28.117 | 9.217 | 1.00 26.70 | A C |
| ATOM | 1683 | CG | GLU | A | 454 | -5.251 | 27.791 | 10.668 | 1.00 33.86 | A C |
| ATOM | 1684 | CD | GLU | A | 454 | -5.668 | 28.932 | 11.603 | 1.00 38.74 | A C |
| ATOM | 1685 | OE1 | GLU | A | 454 | -5.455 | 28.790 | 12.830 | 1.00 41.00 | A O |
| ATOM | 1686 | OE2 | GLU | A | 454 | -6.193 | 29.974 | 11.117 | 1.00 41.16 | A O |
| ATOM | 1687 | C | GLU | A | 454 | -5.174 | 27.758 | 6.811 | 1.00 21.57 | A C |
| ATOM | 1688 | O | GLU | A | 454 | -6.096 | 27.268 | 6.169 | 1.00 21.06 | A O |
| ATOM | 1689 | N | ARG | A | 455 | -4.424 | 28.777 | 6.370 | 1.00 20.50 | A N |
| ATOM | 1690 | CA | ARG | A | 455 | -4.623 | 29.407 | 5.062 | 1.00 20.31 | A C |
| ATOM | 1691 | CB | ARG | A | 455 | -4.138 | 30.861 | 5.081 | 1.00 20.98 | A C |
| ATOM | 1692 | CG | ARG | A | 455 | -4.787 | 31.763 | 6.133 | 1.00 26.90 | A C |
| ATOM | 1693 | CD | ARG | A | 455 | -4.160 | 33.186 | 6.179 | 1.00 31.73 | A C |
| ATOM | 1694 | NE | ARG | A | 455 | -2.726 | 33.122 | 5.913 | 1.00 40.08 | A N |
| ATOM | 1695 | CZ | ARG | A | 455 | -2.166 | 33.344 | 4.715 | 1.00 43.39 | A C |
| ATOM | 1696 | NH1 | ARG | A | 455 | -2.913 | 33.698 | 3.670 | 1.00 42.97 | A N |
| ATOM | 1697 | NH2 | ARG | A | 455 | -0.895 | 33.007 | 4.497 | 1.00 43.77 | A N |
| ATOM | 1698 | C | ARG | A | 455 | -3.924 | 28.634 | 3.918 | 1.00 19.22 | A C |

Figure 9

| ATOM | 1699 | O | ARG | A | 455 | -3.903 | 29.084 | 2.778 | 1.00 | 19.01 | A | O |
|------|------|-----|-----|---|-----|--------|--------|-------|------|-------|---|---|
| ATOM | 1700 | N | GLY | A | 456 | -3.331 | 27.485 | 4.238 | 1.00 | 18.89 | A | N |
| ATOM | 1701 | CA | GLY | A | 456 | -2.661 | 26.668 | 3.237 | 1.00 | 17.09 | A | C |
| ATOM | 1702 | C | GLY | A | 456 | -1.270 | 27.087 | 2.808 | 1.00 | 16.49 | A | C |
| ATOM | 1703 | O | GLY | A | 456 | -0.820 | 26.725 | 1.728 | 1.00 | 16.89 | A | O |
| ATOM | 1704 | N | TYR | A | 457 | -0.569 | 27.822 | 3.655 | 1.00 | 17.05 | A | N |
| ATOM | 1705 | CA | TYR | A | 457 | 0.782 | 28.279 | 3.349 | 1.00 | 15.88 | A | C |
| ATOM | 1706 | CB | TYR | A | 457 | 1.234 | 29.255 | 4.434 | 1.00 | 14.94 | A | C |
| ATOM | 1707 | CG | TYR | A | 457 | 2.631 | 29.788 | 4.257 | 1.00 | 15.15 | A | C |
| ATOM | 1708 | CD1 | TYR | A | 457 | 2.858 | 30.963 | 3.556 | 1.00 | 15.20 | A | C |
| ATOM | 1709 | CE1 | TYR | A | 457 | 4.140 | 31.460 | 3.386 | 1.00 | 16.78 | A | C |
| ATOM | 1710 | CD2 | TYR | A | 457 | 3.732 | 29.114 | 4.793 | 1.00 | 16.05 | A | C |
| ATOM | 1711 | CE2 | TYR | A | 457 | 5.024 | 29.605 | 4.633 | 1.00 | 15.85 | A | C |
| ATOM | 1712 | CZ | TYR | A | 457 | 5.220 | 30.775 | 3.928 | 1.00 | 17.62 | A | C |
| ATOM | 1713 | OH | TYR | A | 457 | 6.500 | 31.256 | 3.741 | 1.00 | 20.82 | A | O |
| ATOM | 1714 | C | TYR | A | 457 | 1.816 | 27.152 | 3.200 | 1.00 | 16.84 | A | C |
| ATOM | 1715 | O | TYR | A | 457 | 1.754 | 26.120 | 3.889 | 1.00 | 17.93 | A | O |
| ATOM | 1716 | N | ARG | A | 458 | 2.742 | 27.344 | 2.262 | 1.00 | 17.12 | A | N |
| ATOM | 1717 | CA | ARG | A | 458 | 3.836 | 26.402 | 2.041 | 1.00 | 17.73 | A | C |
| ATOM | 1718 | CB | ARG | A | 458 | 3.600 | 25.511 | 0.815 | 1.00 | 16.55 | A | C |
| ATOM | 1719 | CG | ARG | A | 458 | 2.419 | 24.548 | 0.915 | 1.00 | 13.92 | A | C |
| ATOM | 1720 | CD | ARG | A | 458 | 2.529 | 23.619 | 2.117 | 1.00 | 14.90 | A | C |
| ATOM | 1721 | NE | ARG | A | 458 | 1.466 | 22.621 | 2.126 | 1.00 | 13.42 | A | N |
| ATOM | 1722 | CZ | ARG | A | 458 | 0.336 | 22.718 | 2.825 | 1.00 | 13.61 | A | C |
| ATOM | 1723 | NH1 | ARG | A | 458 | 0.097 | 23.772 | 3.602 | 1.00 | 12.92 | A | N |
| ATOM | 1724 | NH2 | ARG | A | 458 | -0.573 | 21.759 | 2.721 | 1.00 | 13.56 | A | N |
| ATOM | 1725 | C | ARG | A | 458 | 5.109 | 27.221 | 1.848 | 1.00 | 18.64 | A | C |
| ATOM | 1726 | O | ARG | A | 458 | 5.079 | 28.277 | 1.202 | 1.00 | 18.55 | A | O |
| ATOM | 1727 | N | MET | A | 459 | 6.202 | 26.778 | 2.472 | 1.00 | 19.17 | A | N |
| ATOM | 1728 | CA | MET | A | 459 | 7.485 | 27.464 | 2.341 | 1.00 | 20.58 | A | C |
| ATOM | 1729 | CB | MET | A | 459 | 8.580 | 26.711 | 3.091 | 1.00 | 21.53 | A | C |
| ATOM | 1730 | CG | MET | A | 459 | 8.606 | 26.908 | 4.587 | 1.00 | 24.62 | A | C |
| ATOM | 1731 | SD | MET | A | 459 | 10.094 | 26.126 | 5.281 | 1.00 | 26.28 | A | S |
| ATOM | 1732 | CE | MET | A | 459 | 9.417 | 24.596 | 5.860 | 1.00 | 24.47 | A | C |
| ATOM | 1733 | C | MET | A | 459 | 7.905 | 27.509 | 0.878 | 1.00 | 21.27 | A | C |
| ATOM | 1734 | O | MET | A | 459 | 7.654 | 26.558 | 0.122 | 1.00 | 20.91 | A | O |
| ATOM | 1735 | N | VAL | A | 460 | 8.563 | 28.595 | 0.480 | 1.00 | 22.66 | A | N |
| ATOM | 1736 | CA | VAL | A | 460 | 9.054 | 28.716 | -0.896 | 1.00 | 23.87 | A | C |
| ATOM | 1737 | CB | VAL | A | 460 | 9.341 | 30.191 | -1.293 | 1.00 | 24.02 | A | C |
| ATOM | 1738 | CG1 | VAL | A | 460 | 8.107 | 31.041 | -1.066 | 1.00 | 24.02 | A | C |
| ATOM | 1739 | CG2 | VAL | A | 460 | 10.525 | 30.740 | -0.510 | 1.00 | 23.84 | A | C |
| ATOM | 1740 | C | VAL | A | 460 | 10.332 | 27.862 | -1.038 | 1.00 | 24.93 | A | C |
| ATOM | 1741 | O | VAL | A | 460 | 10.776 | 27.235 | -0.065 | 1.00 | 24.10 | A | O |
| ATOM | 1742 | N | ARG | A | 461 | 10.909 | 27.821 | -2.240 | 1.00 | 25.60 | A | N |
| ATOM | 1743 | CA | ARG | A | 461 | 12.117 | 27.033 | -2.472 | 1.00 | 27.14 | A | C |
| ATOM | 1744 | CB | ARG | A | 461 | 12.412 | 26.927 | -3.966 | 1.00 | 28.24 | A | C |
| ATOM | 1745 | CG | ARG | A | 461 | 13.475 | 25.890 | -4.317 | 1.00 | 30.84 | A | C |
| ATOM | 1746 | CD | ARG | A | 461 | 13.761 | 25.863 | -5.806 | 1.00 | 34.64 | A | C |
| ATOM | 1747 | NE | ARG | A | 461 | 14.134 | 27.189 | -6.286 | 1.00 | 40.71 | A | N |
| ATOM | 1748 | CZ | ARG | A | 461 | 15.290 | 27.794 | -6.016 | 1.00 | 43.85 | A | C |
| ATOM | 1749 | NH1 | ARG | A | 461 | 16.222 | 27.189 | -5.281 | 1.00 | 45.66 | A | N |
| ATOM | 1750 | NH2 | ARG | A | 461 | 15.473 | 29.054 | -6.389 | 1.00 | 45.41 | A | N |
| ATOM | 1751 | C | ARG | A | 461 | 13.280 | 27.695 | -1.742 | 1.00 | 27.77 | A | C |
| ATOM | 1752 | O | ARG | A | 461 | 13.546 | 28.880 | -1.939 | 1.00 | 27.14 | A | O |
| ATOM | 1753 | N | PRO | A | 462 | 13.933 | 26.957 | -0.824 | 1.00 | 29.27 | A | N |
| ATOM | 1754 | CD | PRO | A | 462 | 13.626 | 25.582 | -0.387 | 1.00 | 28.49 | A | C |
| ATOM | 1755 | CA | PRO | A | 462 | 15.068 | 27.496 | -0.064 | 1.00 | 30.90 | A | C |
| ATOM | 1756 | CB | PRO | A | 462 | 15.440 | 26.334 | 0.861 | 1.00 | 29.97 | A | C |
| ATOM | 1757 | CG | PRO | A | 462 | 14.152 | 25.581 | 1.023 | 1.00 | 29.12 | A | C |

Figure 9

```
ATOM   1758  C    PRO A 462      16.220  27.809  -1.009  1.00 32.35           A  C
ATOM   1759  O    PRO A 462      16.325  27.206  -2.077  1.00 31.09           A  O
ATOM   1760  N    ASP A 463      17.067  28.763  -0.633  1.00 35.53           A  N
ATOM   1761  CA   ASP A 463      18.213  29.106  -1.479  1.00 38.31           A  C
ATOM   1762  CB   ASP A 463      19.014  30.295  -0.916  1.00 40.26           A  C
ATOM   1763  CG   ASP A 463      18.204  31.603  -0.865  1.00 42.82           A  C
ATOM   1764  OD1  ASP A 463      17.296  31.814  -1.707  1.00 42.80           A  O
ATOM   1765  OD2  ASP A 463      18.489  32.429   0.033  1.00 44.33           A  O
ATOM   1766  C    ASP A 463      19.113  27.876  -1.598  1.00 38.90           A  C
ATOM   1767  O    ASP A 463      19.314  27.132  -0.622  1.00 38.76           A  O
ATOM   1768  N    ASN A 464      19.581  27.639  -2.822  1.00 40.16           A  N
ATOM   1769  CA   ASN A 464      20.461  26.517  -3.153  1.00 40.92           A  C
ATOM   1770  CB   ASN A 464      21.780  26.616  -2.380  1.00 44.27           A  C
ATOM   1771  CG   ASN A 464      22.590  27.837  -2.779  1.00 47.01           A  C
ATOM   1772  OD1  ASN A 464      22.941  28.008  -3.952  1.00 48.68           A  O
ATOM   1773  ND2  ASN A 464      22.860  28.715  -1.810  1.00 49.12           A  N
ATOM   1774  C    ASN A 464      19.804  25.159  -2.958  1.00 39.73           A  C
ATOM   1775  O    ASN A 464      20.380  24.230  -2.380  1.00 40.05           A  O
ATOM   1776  N    CYS A 465      18.587  25.060  -3.474  1.00 37.76           A  N
ATOM   1777  CA   CYS A 465      17.811  23.836  -3.403  1.00 35.26           A  C
ATOM   1778  CB   CYS A 465      16.637  24.018  -2.437  1.00 33.59           A  C
ATOM   1779  SG   CYS A 465      15.506  22.635  -2.403  1.00 29.27           A  S
ATOM   1780  C    CYS A 465      17.290  23.514  -4.799  1.00 33.74           A  C
ATOM   1781  O    CYS A 465      16.620  24.341  -5.411  1.00 33.81           A  O
ATOM   1782  N    PRO A 466      17.639  22.333  -5.340  1.00 32.33           A  N
ATOM   1783  CD   PRO A 466      18.534  21.333  -4.723  1.00 31.62           A  C
ATOM   1784  CA   PRO A 466      17.198  21.898  -6.674  1.00 31.81           A  C
ATOM   1785  CB   PRO A 466      17.687  20.448  -6.734  1.00 31.22           A  C
ATOM   1786  CG   PRO A 466      18.931  20.472  -5.901  1.00 31.60           A  C
ATOM   1787  C    PRO A 466      15.666  21.965  -6.797  1.00 31.67           A  C
ATOM   1788  O    PRO A 466      14.961  21.742  -5.808  1.00 31.84           A  O
ATOM   1789  N    GLU A 467      15.151  22.287  -7.988  1.00 31.18           A  N
ATOM   1790  CA   GLU A 467      13.701  22.374  -8.196  1.00 30.44           A  C
ATOM   1791  CB   GLU A 467      13.352  22.958  -9.561  1.00 31.41           A  C
ATOM   1792  CG   GLU A 467      12.709  24.349  -9.499  1.00 34.16           A  C
ATOM   1793  CD   GLU A 467      11.331  24.386  -8.823  1.00 34.80           A  C
ATOM   1794  OE1  GLU A 467      11.144  25.236  -7.923  1.00 35.45           A  O
ATOM   1795  OE2  GLU A 467      10.426  23.612  -9.221  1.00 35.55           A  O
ATOM   1796  C    GLU A 467      13.013  21.036  -8.046  1.00 29.43           A  C
ATOM   1797  O    GLU A 467      11.882  20.969  -7.578  1.00 29.31           A  O
ATOM   1798  N    GLU A 468      13.686  19.972  -8.462  1.00 28.51           A  N
ATOM   1799  CA   GLU A 468      13.129  18.635  -8.340  1.00 28.23           A  C
ATOM   1800  CB   GLU A 468      13.941  17.624  -9.164  1.00 31.65           A  C
ATOM   1801  CG   GLU A 468      14.132  17.988 -10.650  1.00 37.89           A  C
ATOM   1802  CD   GLU A 468      15.264  19.024 -10.903  1.00 42.15           A  C
ATOM   1803  OE1  GLU A 468      16.263  19.061 -10.137  1.00 42.26           A  O
ATOM   1804  OE2  GLU A 468      15.156  19.803 -11.884  1.00 44.97           A  O
ATOM   1805  C    GLU A 468      13.063  18.213  -6.861  1.00 26.64           A  C
ATOM   1806  O    GLU A 468      12.228  17.397  -6.490  1.00 26.78           A  O
ATOM   1807  N    LEU A 469      13.946  18.756  -6.021  1.00 24.42           A  N
ATOM   1808  CA   LEU A 469      13.932  18.439  -4.592  1.00 22.93           A  C
ATOM   1809  CB   LEU A 469      15.288  18.736  -3.918  1.00 21.28           A  C
ATOM   1810  CG   LEU A 469      15.358  18.493  -2.398  1.00 19.94           A  C
ATOM   1811  CD1  LEU A 469      15.199  17.027  -2.090  1.00 19.58           A  C
ATOM   1812  CD2  LEU A 469      16.657  18.993  -1.831  1.00 18.00           A  C
ATOM   1813  C    LEU A 469      12.827  19.265  -3.924  1.00 22.59           A  C
ATOM   1814  O    LEU A 469      12.172  18.801  -2.987  1.00 21.96           A  O
ATOM   1815  N    TYR A 470      12.631  20.492  -4.399  1.00 21.33           A  N
ATOM   1816  CA   TYR A 470      11.584  21.331  -3.843  1.00 21.48           A  C
```

Figure 9

| ATOM | 1817 | CB  | TYR A 470 | 11.647 | 22.761 | -4.394 | 1.00 | 21.24 | A | C |
|------|------|-----|-----------|--------|--------|--------|------|-------|---|---|
| ATOM | 1818 | CG  | TYR A 470 | 10.537 | 23.653 | -3.860 | 1.00 | 21.65 | A | C |
| ATOM | 1819 | CD1 | TYR A 470 | 10.359 | 23.836 | -2.481 | 1.00 | 20.43 | A | C |
| ATOM | 1820 | CE1 | TYR A 470 |  9.311 | 24.624 | -1.987 | 1.00 | 19.68 | A | C |
| ATOM | 1821 | CD2 | TYR A 470 |  9.639 | 24.285 | -4.731 | 1.00 | 21.32 | A | C |
| ATOM | 1822 | CE2 | TYR A 470 |  8.593 | 25.074 | -4.243 | 1.00 | 20.19 | A | C |
| ATOM | 1823 | CZ  | TYR A 470 |  8.438 | 25.237 | -2.879 | 1.00 | 19.82 | A | C |
| ATOM | 1824 | OH  | TYR A 470 |  7.406 | 26.011 | -2.415 | 1.00 | 19.03 | A | O |
| ATOM | 1825 | C   | TYR A 470 | 10.216 | 20.716 | -4.162 | 1.00 | 21.44 | A | C |
| ATOM | 1826 | O   | TYR A 470 |  9.284 | 20.809 | -3.361 | 1.00 | 21.57 | A | O |
| ATOM | 1827 | N   | GLN A 471 | 10.098 | 20.100 | -5.336 | 1.00 | 20.86 | A | N |
| ATOM | 1828 | CA  | GLN A 471 |  8.846 | 19.479 | -5.727 | 1.00 | 20.84 | A | C |
| ATOM | 1829 | CB  | GLN A 471 |  8.819 | 19.198 | -7.233 | 1.00 | 21.20 | A | C |
| ATOM | 1830 | CG  | GLN A 471 |  8.647 | 20.461 | -8.070 | 1.00 | 23.19 | A | C |
| ATOM | 1831 | CD  | GLN A 471 |  7.471 | 21.350 | -7.593 | 1.00 | 26.21 | A | C |
| ATOM | 1832 | OE1 | GLN A 471 |  6.399 | 20.847 | -7.220 | 1.00 | 27.08 | A | O |
| ATOM | 1833 | NE2 | GLN A 471 |  7.679 | 22.676 | -7.600 | 1.00 | 23.64 | A | N |
| ATOM | 1834 | C   | GLN A 471 |  8.584 | 18.233 | -4.886 | 1.00 | 20.32 | A | C |
| ATOM | 1835 | O   | GLN A 471 |  7.442 | 17.894 | -4.594 | 1.00 | 20.75 | A | O |
| ATOM | 1836 | N   | LEU A 472 |  9.652 | 17.588 | -4.444 | 1.00 | 20.41 | A | N |
| ATOM | 1837 | CA  | LEU A 472 |  9.534 | 16.419 | -3.589 | 1.00 | 20.53 | A | C |
| ATOM | 1838 | CB  | LEU A 472 | 10.905 | 15.763 | -3.440 | 1.00 | 22.54 | A | C |
| ATOM | 1839 | CG  | LEU A 472 | 10.910 | 14.278 | -3.101 | 1.00 | 24.73 | A | C |
| ATOM | 1840 | CD1 | LEU A 472 | 10.087 | 13.496 | -4.133 | 1.00 | 24.02 | A | C |
| ATOM | 1841 | CD2 | LEU A 472 | 12.364 | 13.795 | -3.047 | 1.00 | 26.05 | A | C |
| ATOM | 1842 | C   | LEU A 472 |  9.000 | 16.890 | -2.219 | 1.00 | 19.34 | A | C |
| ATOM | 1843 | O   | LEU A 472 |  8.157 | 16.226 | -1.623 | 1.00 | 20.16 | A | O |
| ATOM | 1844 | N   | MET A 473 |  9.481 | 18.043 | -1.750 | 1.00 | 17.26 | A | N |
| ATOM | 1845 | CA  | MET A 473 |  9.037 | 18.636 | -0.490 | 1.00 | 16.96 | A | C |
| ATOM | 1846 | CB  | MET A 473 |  9.784 | 19.936 | -0.210 | 1.00 | 16.26 | A | C |
| ATOM | 1847 | CG  | MET A 473 | 11.264 | 19.803 |  0.022 | 1.00 | 16.45 | A | C |
| ATOM | 1848 | SD  | MET A 473 | 12.007 | 21.440 |  0.147 | 1.00 | 17.70 | A | S |
| ATOM | 1849 | CE  | MET A 473 | 13.695 | 20.998 |  0.545 | 1.00 | 16.31 | A | C |
| ATOM | 1850 | C   | MET A 473 |  7.547 | 18.970 | -0.582 | 1.00 | 17.56 | A | C |
| ATOM | 1851 | O   | MET A 473 |  6.782 | 18.719 |  0.350 | 1.00 | 15.95 | A | O |
| ATOM | 1852 | N   | ARG A 474 |  7.148 | 19.538 | -1.718 | 1.00 | 18.23 | A | N |
| ATOM | 1853 | CA  | ARG A 474 |  5.755 | 19.920 | -1.943 | 1.00 | 19.01 | A | C |
| ATOM | 1854 | CB  | ARG A 474 |  5.610 | 20.717 | -3.246 | 1.00 | 18.61 | A | C |
| ATOM | 1855 | CG  | ARG A 474 |  6.359 | 22.038 | -3.244 | 1.00 | 19.29 | A | C |
| ATOM | 1856 | CD  | ARG A 474 |  5.867 | 22.968 | -2.140 | 1.00 | 23.46 | A | C |
| ATOM | 1857 | NE  | ARG A 474 |  4.435 | 23.277 | -2.264 | 1.00 | 24.61 | A | N |
| ATOM | 1858 | CZ  | ARG A 474 |  3.924 | 24.406 | -2.763 | 1.00 | 23.26 | A | C |
| ATOM | 1859 | NH1 | ARG A 474 |  4.701 | 25.395 | -3.199 | 1.00 | 20.27 | A | N |
| ATOM | 1860 | NH2 | ARG A 474 |  2.609 | 24.516 | -2.880 | 1.00 | 22.94 | A | N |
| ATOM | 1861 | C   | ARG A 474 |  4.831 | 18.706 | -1.929 | 1.00 | 18.63 | A | C |
| ATOM | 1862 | O   | ARG A 474 |  3.664 | 18.810 | -1.556 | 1.00 | 18.74 | A | O |
| ATOM | 1863 | N   | LEU A 475 |  5.363 | 17.557 | -2.327 | 1.00 | 19.09 | A | N |
| ATOM | 1864 | CA  | LEU A 475 |  4.594 | 16.326 | -2.311 | 1.00 | 19.09 | A | C |
| ATOM | 1865 | CB  | LEU A 475 |  5.280 | 15.243 | -3.126 | 1.00 | 20.12 | A | C |
| ATOM | 1866 | CG  | LEU A 475 |  5.092 | 15.370 | -4.635 | 1.00 | 21.43 | A | C |
| ATOM | 1867 | CD1 | LEU A 475 |  5.839 | 14.243 | -5.331 | 1.00 | 20.67 | A | C |
| ATOM | 1868 | CD2 | LEU A 475 |  3.592 | 15.345 | -4.972 | 1.00 | 20.98 | A | C |
| ATOM | 1869 | C   | LEU A 475 |  4.434 | 15.872 | -0.871 | 1.00 | 19.22 | A | C |
| ATOM | 1870 | O   | LEU A 475 |  3.382 | 15.359 | -0.488 | 1.00 | 19.47 | A | O |
| ATOM | 1871 | N   | CYS A 476 |  5.490 | 16.056 | -0.076 | 1.00 | 18.28 | A | N |
| ATOM | 1872 | CA  | CYS A 476 |  5.458 | 15.704 |  1.345 | 1.00 | 16.97 | A | C |
| ATOM | 1873 | CB  | CYS A 476 |  6.854 | 15.853 |  1.977 | 1.00 | 16.93 | A | C |
| ATOM | 1874 | SG  | CYS A 476 |  8.109 | 14.703 |  1.367 | 1.00 | 16.71 | A | S |
| ATOM | 1875 | C   | CYS A 476 |  4.478 | 16.619 |  2.097 | 1.00 | 15.98 | A | C |

Figure 9

```
ATOM   1876  O    CYS A 476       3.943  16.234   3.135  1.00 14.59      A    O
ATOM   1877  N    TRP A 477       4.264  17.828   1.574  1.00 15.43      A    N
ATOM   1878  CA   TRP A 477       3.371  18.787   2.209  1.00 16.11      A    C
ATOM   1879  CB   TRP A 477       3.958  20.199   2.166  1.00 14.59      A    C
ATOM   1880  CG   TRP A 477       5.292  20.311   2.786  1.00 15.49      A    C
ATOM   1881  CD2  TRP A 477       6.323  21.241   2.434  1.00 15.39      A    C
ATOM   1882  CE2  TRP A 477       7.445  20.941   3.236  1.00 15.99      A    C
ATOM   1883  CE3  TRP A 477       6.406  22.295   1.511  1.00 16.03      A    C
ATOM   1884  CD1  TRP A 477       5.812  19.516   3.771  1.00 14.61      A    C
ATOM   1885  NE1  TRP A 477       7.100  19.886   4.041  1.00 16.03      A    N
ATOM   1886  CZ2  TRP A 477       8.653  21.656   3.144  1.00 15.63      A    C
ATOM   1887  CZ3  TRP A 477       7.595  23.004   1.417  1.00 16.55      A    C
ATOM   1888  CH2  TRP A 477       8.710  22.678   2.235  1.00 16.05      A    C
ATOM   1889  C    TRP A 477       1.942  18.833   1.672  1.00 16.16      A    C
ATOM   1890  O    TRP A 477       1.241  19.808   1.911  1.00 17.18      A    O
ATOM   1891  N    LYS A 478       1.509  17.803   0.950  1.00 17.35      A    N
ATOM   1892  CA   LYS A 478       0.138  17.785   0.424  1.00 18.44      A    C
ATOM   1893  CB   LYS A 478      -0.150  16.512  -0.398  1.00 19.14      A    C
ATOM   1894  CG   LYS A 478       0.555  16.439  -1.784  1.00 22.21      A    C
ATOM   1895  CD   LYS A 478       0.191  17.596  -2.712  1.00 23.38      A    C
ATOM   1896  CE   LYS A 478      -1.140  17.391  -3.395  1.00 25.84      A    C
ATOM   1897  NZ   LYS A 478      -1.589  18.635  -4.091  1.00 29.85      A    N
ATOM   1898  C    LYS A 478      -0.804  17.857   1.607  1.00 17.86      A    C
ATOM   1899  O    LYS A 478      -0.544  17.240   2.631  1.00 17.40      A    O
ATOM   1900  N    GLU A 479      -1.879  18.631   1.472  1.00 18.59      A    N
ATOM   1901  CA   GLU A 479      -2.857  18.801   2.543  1.00 18.59      A    C
ATOM   1902  CB   GLU A 479      -3.976  19.731   2.079  1.00 19.04      A    C
ATOM   1903  CG   GLU A 479      -4.926  20.196   3.199  1.00 19.72      A    C
ATOM   1904  CD   GLU A 479      -4.242  21.035   4.274  1.00 20.82      A    C
ATOM   1905  OE1  GLU A 479      -3.313  21.800   3.952  1.00 21.21      A    O
ATOM   1906  OE2  GLU A 479      -4.637  20.933   5.453  1.00 21.32      A    O
ATOM   1907  C    GLU A 479      -3.439  17.483   3.066  1.00 18.32      A    C
ATOM   1908  O    GLU A 479      -3.534  17.267   4.272  1.00 17.51      A    O
ATOM   1909  N    ARG A 480      -3.848  16.619   2.148  1.00 18.95      A    N
ATOM   1910  CA   ARG A 480      -4.403  15.326   2.516  1.00 19.39      A    C
ATOM   1911  CB   ARG A 480      -5.346  14.839   1.426  1.00 22.37      A    C
ATOM   1912  CG   ARG A 480      -6.572  15.673   1.242  1.00 26.34      A    C
ATOM   1913  CD   ARG A 480      -7.294  15.123   0.068  1.00 32.03      A    C
ATOM   1914  NE   ARG A 480      -8.543  15.811  -0.202  1.00 38.75      A    N
ATOM   1915  CZ   ARG A 480      -8.959  16.148  -1.424  1.00 42.24      A    C
ATOM   1916  NH1  ARG A 480      -8.221  15.866  -2.500  1.00 42.97      A    N
ATOM   1917  NH2  ARG A 480     -10.133  16.753  -1.570  1.00 43.49      A    N
ATOM   1918  C    ARG A 480      -3.272  14.320   2.678  1.00 17.76      A    C
ATOM   1919  O    ARG A 480      -2.445  14.163   1.785  1.00 16.81      A    O
ATOM   1920  N    PRO A 481      -3.278  13.560   3.781  1.00 17.35      A    N
ATOM   1921  CD   PRO A 481      -4.243  13.582   4.895  1.00 17.29      A    C
ATOM   1922  CA   PRO A 481      -2.235  12.568   4.035  1.00 16.23      A    C
ATOM   1923  CB   PRO A 481      -2.704  11.909   5.350  1.00 16.83      A    C
ATOM   1924  CG   PRO A 481      -3.435  12.980   6.026  1.00 16.73      A    C
ATOM   1925  C    PRO A 481      -2.057  11.532   2.932  1.00 15.98      A    C
ATOM   1926  O    PRO A 481      -0.942  11.088   2.666  1.00 14.94      A    O
ATOM   1927  N    GLU A 482      -3.152  11.135   2.300  1.00 15.54      A    N
ATOM   1928  CA   GLU A 482      -3.082  10.123   1.261  1.00 15.76      A    C
ATOM   1929  CB   GLU A 482      -4.484   9.592   0.922  1.00 18.21      A    C
ATOM   1930  CG   GLU A 482      -5.402  10.571   0.176  1.00 20.45      A    C
ATOM   1931  CD   GLU A 482      -6.250  11.462   1.071  1.00 21.20      A    C
ATOM   1932  OE1  GLU A 482      -6.111  11.457   2.315  1.00 20.62      A    O
ATOM   1933  OE2  GLU A 482      -7.086  12.176   0.501  1.00 23.85      A    O
ATOM   1934  C    GLU A 482      -2.356  10.573   0.004  1.00 15.38      A    C
```

Figure 9

| | | | | | | | | | | | |
|---|---|---|---|---|---|---|---|---|---|---|---|
| ATOM | 1935 | O | GLU | A | 482 | -1.841 | 9.749 | -0.756 | 1.00 | 15.99 | A O |
| ATOM | 1936 | N | ASP | A | 483 | -2.270 | 11.882 | -0.195 | 1.00 | 15.45 | A N |
| ATOM | 1937 | CA | ASP | A | 483 | -1.602 | 12.430 | -1.365 | 1.00 | 15.40 | A C |
| ATOM | 1938 | CB | ASP | A | 483 | -2.205 | 13.784 | -1.738 | 1.00 | 17.09 | A C |
| ATOM | 1939 | CG | ASP | A | 483 | -3.630 | 13.667 | -2.249 | 1.00 | 18.21 | A C |
| ATOM | 1940 | OD1 | ASP | A | 483 | -3.961 | 12.621 | -2.827 | 1.00 | 18.84 | A O |
| ATOM | 1941 | OD2 | ASP | A | 483 | -4.416 | 14.615 | -2.067 | 1.00 | 19.12 | A O |
| ATOM | 1942 | C | ASP | A | 483 | -0.099 | 12.576 | -1.194 | 1.00 | 16.05 | A C |
| ATOM | 1943 | O | ASP | A | 483 | 0.590 | 12.969 | -2.139 | 1.00 | 16.50 | A O |
| ATOM | 1944 | N | ARG | A | 484 | 0.394 | 12.308 | 0.016 | 1.00 | 14.92 | A N |
| ATOM | 1945 | CA | ARG | A | 484 | 1.822 | 12.386 | 0.318 | 1.00 | 14.65 | A C |
| ATOM | 1946 | CB | ARG | A | 484 | 2.027 | 12.678 | 1.803 | 1.00 | 13.50 | A C |
| ATOM | 1947 | CG | ARG | A | 484 | 1.466 | 14.003 | 2.241 | 1.00 | 11.84 | A C |
| ATOM | 1948 | CD | ARG | A | 484 | 1.434 | 14.097 | 3.748 | 1.00 | 12.21 | A C |
| ATOM | 1949 | NE | ARG | A | 484 | 0.564 | 15.185 | 4.170 | 1.00 | 13.36 | A N |
| ATOM | 1950 | CZ | ARG | A | 484 | 0.046 | 15.314 | 5.385 | 1.00 | 13.15 | A C |
| ATOM | 1951 | NH1 | ARG | A | 484 | 0.324 | 14.422 | 6.333 | 1.00 | 11.61 | A N |
| ATOM | 1952 | NH2 | ARG | A | 484 | -0.820 | 16.294 | 5.621 | 1.00 | 13.09 | A N |
| ATOM | 1953 | C | ARG | A | 484 | 2.486 | 11.060 | -0.062 | 1.00 | 15.08 | A C |
| ATOM | 1954 | O | ARG | A | 484 | 1.897 | 9.989 | 0.145 | 1.00 | 15.06 | A O |
| ATOM | 1955 | N | PRO | A | 485 | 3.739 | 11.107 | -0.588 | 1.00 | 15.75 | A N |
| ATOM | 1956 | CD | PRO | A | 485 | 4.570 | 12.308 | -0.766 | 1.00 | 15.32 | A C |
| ATOM | 1957 | CA | PRO | A | 485 | 4.476 | 9.899 | -0.998 | 1.00 | 15.60 | A C |
| ATOM | 1958 | CB | PRO | A | 485 | 5.789 | 10.462 | -1.562 | 1.00 | 16.31 | A C |
| ATOM | 1959 | CG | PRO | A | 485 | 5.485 | 11.880 | -1.874 | 1.00 | 17.65 | A C |
| ATOM | 1960 | C | PRO | A | 485 | 4.792 | 8.961 | 0.163 | 1.00 | 15.23 | A C |
| ATOM | 1961 | O | PRO | A | 485 | 4.673 | 9.341 | 1.336 | 1.00 | 15.73 | A O |
| ATOM | 1962 | N | THR | A | 486 | 5.169 | 7.728 | -0.162 | 1.00 | 15.50 | A N |
| ATOM | 1963 | CA | THR | A | 486 | 5.571 | 6.778 | 0.867 | 1.00 | 16.07 | A C |
| ATOM | 1964 | CB | THR | A | 486 | 5.373 | 5.297 | 0.452 | 1.00 | 15.46 | A C |
| ATOM | 1965 | OG1 | THR | A | 486 | 6.090 | 5.032 | -0.756 | 1.00 | 18.22 | A O |
| ATOM | 1966 | CG2 | THR | A | 486 | 3.916 | 4.970 | 0.267 | 1.00 | 15.24 | A C |
| ATOM | 1967 | C | THR | A | 486 | 7.080 | 6.990 | 1.057 | 1.00 | 16.49 | A C |
| ATOM | 1968 | O | THR | A | 486 | 7.754 | 7.553 | 0.179 | 1.00 | 15.91 | A O |
| ATOM | 1969 | N | PHE | A | 487 | 7.586 | 6.584 | 2.215 | 1.00 | 16.91 | A N |
| ATOM | 1970 | CA | PHE | A | 487 | 9.012 | 6.676 | 2.508 | 1.00 | 18.27 | A C |
| ATOM | 1971 | CB | PHE | A | 487 | 9.278 | 6.355 | 3.974 | 1.00 | 16.51 | A C |
| ATOM | 1972 | CG | PHE | A | 487 | 9.088 | 7.535 | 4.878 | 1.00 | 16.65 | A C |
| ATOM | 1973 | CD1 | PHE | A | 487 | 9.930 | 8.643 | 4.769 | 1.00 | 15.10 | A C |
| ATOM | 1974 | CD2 | PHE | A | 487 | 8.063 | 7.559 | 5.820 | 1.00 | 16.74 | A C |
| ATOM | 1975 | CE1 | PHE | A | 487 | 9.754 | 9.749 | 5.580 | 1.00 | 14.94 | A C |
| ATOM | 1976 | CE2 | PHE | A | 487 | 7.881 | 8.666 | 6.636 | 1.00 | 15.28 | A C |
| ATOM | 1977 | CZ | PHE | A | 487 | 8.729 | 9.764 | 6.517 | 1.00 | 14.74 | A C |
| ATOM | 1978 | C | PHE | A | 487 | 9.751 | 5.716 | 1.591 | 1.00 | 19.93 | A C |
| ATOM | 1979 | O | PHE | A | 487 | 10.895 | 5.962 | 1.210 | 1.00 | 20.02 | A O |
| ATOM | 1980 | N | ASP | A | 488 | 9.057 | 4.651 | 1.193 | 1.00 | 21.18 | A N |
| ATOM | 1981 | CA | ASP | A | 488 | 9.604 | 3.670 | 0.266 | 1.00 | 22.31 | A C |
| ATOM | 1982 | CB | ASP | A | 488 | 8.568 | 2.559 | 0.050 | 1.00 | 25.55 | A C |
| ATOM | 1983 | CG | ASP | A | 488 | 8.956 | 1.572 | -1.051 | 1.00 | 29.61 | A C |
| ATOM | 1984 | OD1 | ASP | A | 488 | 10.156 | 1.457 | -1.395 | 1.00 | 31.02 | A O |
| ATOM | 1985 | OD2 | ASP | A | 488 | 8.031 | 0.905 | -1.580 | 1.00 | 31.64 | A O |
| ATOM | 1986 | C | ASP | A | 488 | 9.925 | 4.422 | -1.039 | 1.00 | 22.27 | A C |
| ATOM | 1987 | O | ASP | A | 488 | 11.022 | 4.300 | -1.591 | 1.00 | 22.49 | A O |
| ATOM | 1988 | N | TYR | A | 489 | 8.990 | 5.256 | -1.484 | 1.00 | 20.93 | A N |
| ATOM | 1989 | CA | TYR | A | 489 | 9.186 | 6.039 | -2.691 | 1.00 | 20.19 | A C |
| ATOM | 1990 | CB | TYR | A | 489 | 7.873 | 6.690 | -3.111 | 1.00 | 18.15 | A C |
| ATOM | 1991 | CG | TYR | A | 489 | 8.085 | 7.709 | -4.188 | 1.00 | 17.78 | A C |
| ATOM | 1992 | CD1 | TYR | A | 489 | 8.372 | 7.310 | -5.487 | 1.00 | 17.66 | A C |
| ATOM | 1993 | CE1 | TYR | A | 489 | 8.644 | 8.237 | -6.477 | 1.00 | 19.70 | A C |

Figure 9

| ATOM | 1994 | CD2 | TYR | A | 489 | 8.066 | 9.074 | -3.896 | 1.00 | 16.89 | A | C |
|------|------|-----|-----|---|-----|-------|-------|--------|------|-------|---|---|
| ATOM | 1995 | CE2 | TYR | A | 489 | 8.330 | 10.018 | -4.866 | 1.00 | 17.82 | A | C |
| ATOM | 1996 | CZ | TYR | A | 489 | 8.625 | 9.596 | -6.169 | 1.00 | 21.60 | A | C |
| ATOM | 1997 | OH | TYR | A | 489 | 8.919 | 10.512 | -7.167 | 1.00 | 21.74 | A | O |
| ATOM | 1998 | C | TYR | A | 489 | 10.271 | 7.120 | -2.513 | 1.00 | 21.20 | A | C |
| ATOM | 1999 | O | TYR | A | 489 | 11.111 | 7.312 | -3.395 | 1.00 | 21.38 | A | O |
| ATOM | 2000 | N | LEU | A | 490 | 10.217 | 7.853 | -1.399 | 1.00 | 21.45 | A | N |
| ATOM | 2001 | CA | LEU | A | 490 | 11.191 | 8.911 | -1.108 | 1.00 | 22.07 | A | C |
| ATOM | 2002 | CB | LEU | A | 490 | 10.864 | 9.604 | 0.224 | 1.00 | 21.29 | A | C |
| ATOM | 2003 | CG | LEU | A | 490 | 9.595 | 10.471 | 0.316 | 1.00 | 20.08 | A | C |
| ATOM | 2004 | CD1 | LEU | A | 490 | 9.205 | 10.717 | 1.755 | 1.00 | 17.47 | A | C |
| ATOM | 2005 | CD2 | LEU | A | 490 | 9.792 | 11.781 | -0.424 | 1.00 | 17.59 | A | C |
| ATOM | 2006 | C | LEU | A | 490 | 12.637 | 8.389 | -1.096 | 1.00 | 23.40 | A | C |
| ATOM | 2007 | O | LEU | A | 490 | 13.534 | 9.074 | -1.573 | 1.00 | 22.04 | A | O |
| ATOM | 2008 | N | ARG | A | 491 | 12.856 | 7.186 | -0.554 | 1.00 | 25.91 | A | N |
| ATOM | 2009 | CA | ARG | A | 491 | 14.195 | 6.580 | -0.518 | 1.00 | 28.51 | A | C |
| ATOM | 2010 | CB | ARG | A | 491 | 14.216 | 5.280 | 0.303 | 1.00 | 29.46 | A | C |
| ATOM | 2011 | CG | ARG | A | 491 | 15.563 | 4.540 | 0.223 | 1.00 | 33.10 | A | C |
| ATOM | 2012 | CD | ARG | A | 491 | 15.438 | 3.049 | 0.541 | 1.00 | 37.84 | A | C |
| ATOM | 2013 | NE | ARG | A | 491 | 14.267 | 2.437 | -0.099 | 1.00 | 43.28 | A | N |
| ATOM | 2014 | CZ | ARG | A | 491 | 14.182 | 2.101 | -1.389 | 1.00 | 45.45 | A | C |
| ATOM | 2015 | NH1 | ARG | A | 491 | 15.211 | 2.292 | -2.218 | 1.00 | 45.66 | A | N |
| ATOM | 2016 | NH2 | ARG | A | 491 | 13.033 | 1.630 | -1.869 | 1.00 | 45.52 | A | N |
| ATOM | 2017 | C | ARG | A | 491 | 14.697 | 6.297 | -1.944 | 1.00 | 29.69 | A | C |
| ATOM | 2018 | O | ARG | A | 491 | 15.843 | 6.609 | -2.267 | 1.00 | 30.38 | A | O |
| ATOM | 2019 | N | SER | A | 492 | 13.846 | 5.699 | -2.784 | 1.00 | 29.88 | A | N |
| ATOM | 2020 | CA | SER | A | 492 | 14.211 | 5.404 | -4.175 | 1.00 | 30.09 | A | C |
| ATOM | 2021 | CB | SER | A | 492 | 13.039 | 4.767 | -4.929 | 1.00 | 29.92 | A | C |
| ATOM | 2022 | OG | SER | A | 492 | 12.660 | 3.563 | -4.314 | 1.00 | 32.35 | A | O |
| ATOM | 2023 | C | SER | A | 492 | 14.629 | 6.668 | -4.923 | 1.00 | 29.84 | A | C |
| ATOM | 2024 | O | SER | A | 492 | 15.707 | 6.714 | -5.514 | 1.00 | 29.39 | A | O |
| ATOM | 2025 | N | VAL | A | 493 | 13.777 | 7.694 | -4.873 | 1.00 | 29.39 | A | N |
| ATOM | 2026 | CA | VAL | A | 493 | 14.038 | 8.950 | -5.563 | 1.00 | 29.29 | A | C |
| ATOM | 2027 | CB | VAL | A | 493 | 12.764 | 9.847 | -5.611 | 1.00 | 30.21 | A | C |
| ATOM | 2028 | CG1 | VAL | A | 493 | 12.243 | 10.123 | -4.222 | 1.00 | 32.50 | A | C |
| ATOM | 2029 | CG2 | VAL | A | 493 | 13.052 | 11.153 | -6.321 | 1.00 | 31.64 | A | C |
| ATOM | 2030 | C | VAL | A | 493 | 15.266 | 9.713 | -5.044 | 1.00 | 29.06 | A | C |
| ATOM | 2031 | O | VAL | A | 493 | 15.982 | 10.343 | -5.828 | 1.00 | 27.82 | A | O |
| ATOM | 2032 | N | LEU | A | 494 | 15.540 | 9.611 | -3.745 | 1.00 | 28.66 | A | N |
| ATOM | 2033 | CA | LEU | A | 494 | 16.691 | 10.288 | -3.155 | 1.00 | 29.07 | A | C |
| ATOM | 2034 | CB | LEU | A | 494 | 16.503 | 10.448 | -1.648 | 1.00 | 26.90 | A | C |
| ATOM | 2035 | CG | LEU | A | 494 | 15.463 | 11.508 | -1.271 | 1.00 | 27.92 | A | C |
| ATOM | 2036 | CD1 | LEU | A | 494 | 15.132 | 11.474 | 0.217 | 1.00 | 25.90 | A | C |
| ATOM | 2037 | CD2 | LEU | A | 494 | 15.955 | 12.896 | -1.701 | 1.00 | 26.79 | A | C |
| ATOM | 2038 | C | LEU | A | 494 | 17.987 | 9.550 | -3.486 | 1.00 | 30.21 | A | C |
| ATOM | 2039 | O | LEU | A | 494 | 19.015 | 10.170 | -3.704 | 1.00 | 30.77 | A | O |
| ATOM | 2040 | N | GLU | A | 495 | 17.918 | 8.226 | -3.560 | 1.00 | 32.47 | A | N |
| ATOM | 2041 | CA | GLU | A | 495 | 19.068 | 7.395 | -3.903 | 1.00 | 35.43 | A | C |
| ATOM | 2042 | CB | GLU | A | 495 | 18.696 | 5.915 | -3.803 | 1.00 | 35.93 | A | C |
| ATOM | 2043 | CG | GLU | A | 495 | 19.057 | 5.263 | -2.490 | 1.00 | 38.99 | A | C |
| ATOM | 2044 | CD | GLU | A | 495 | 18.657 | 3.796 | -2.421 | 1.00 | 40.48 | A | C |
| ATOM | 2045 | OE1 | GLU | A | 495 | 18.513 | 3.151 | -3.487 | 1.00 | 40.76 | A | O |
| ATOM | 2046 | OE2 | GLU | A | 495 | 18.489 | 3.293 | -1.283 | 1.00 | 42.06 | A | O |
| ATOM | 2047 | C | GLU | A | 495 | 19.537 | 7.657 | -5.330 | 1.00 | 37.32 | A | C |
| ATOM | 2048 | O | GLU | A | 495 | 20.734 | 7.674 | -5.616 | 1.00 | 37.86 | A | O |
| ATOM | 2049 | N | ASP | A | 496 | 18.580 | 7.848 | -6.229 | 1.00 | 39.67 | A | N |
| ATOM | 2050 | CA | ASP | A | 496 | 18.876 | 8.071 | -7.638 | 1.00 | 42.17 | A | C |
| ATOM | 2051 | CB | ASP | A | 496 | 17.899 | 7.253 | -8.502 | 1.00 | 43.55 | A | C |
| ATOM | 2052 | CG | ASP | A | 496 | 17.751 | 5.798 | -8.027 | 1.00 | 45.81 | A | C |

Figure 9

| | | | | | | | | | | |
|---|---|---|---|---|---|---|---|---|---|---|
| ATOM | 2053 | OD1 | ASP A 496 | 18.736 | 5.208 | -7.523 | 1.00 | 47.00 | A | O |
| ATOM | 2054 | OD2 | ASP A 496 | 16.634 | 5.239 | -8.162 | 1.00 | 47.27 | A | O |
| ATOM | 2055 | C | ASP A 496 | 18.837 | 9.536 | -8.088 | 1.00 | 43.61 | A | C |
| ATOM | 2056 | O | ASP A 496 | 18.802 | 9.796 | -9.290 | 1.00 | 44.48 | A | O |
| ATOM | 2057 | N | PHE A 497 | 18.917 | 10.482 | -7.151 | 1.00 | 44.60 | A | N |
| ATOM | 2058 | CA | PHE A 497 | 18.837 | 11.904 | -7.497 | 1.00 | 45.97 | A | C |
| ATOM | 2059 | CB | PHE A 497 | 18.941 | 12.783 | -6.257 | 1.00 | 45.15 | A | C |
| ATOM | 2060 | CG | PHE A 497 | 18.199 | 14.084 | -6.383 | 1.00 | 44.45 | A | C |
| ATOM | 2061 | CD1 | PHE A 497 | 16.838 | 14.152 | -6.084 | 1.00 | 44.53 | A | C |
| ATOM | 2062 | CD2 | PHE A 497 | 18.853 | 15.241 | -6.803 | 1.00 | 44.12 | A | C |
| ATOM | 2063 | CE1 | PHE A 497 | 16.139 | 15.353 | -6.200 | 1.00 | 44.19 | A | C |
| ATOM | 2064 | CE2 | PHE A 497 | 18.169 | 16.451 | -6.922 | 1.00 | 44.20 | A | C |
| ATOM | 2065 | CZ | PHE A 497 | 16.809 | 16.507 | -6.620 | 1.00 | 44.34 | A | C |
| ATOM | 2066 | C | PHE A 497 | 19.797 | 12.394 | -8.582 | 1.00 | 47.65 | A | C |
| ATOM | 2067 | O | PHE A 497 | 19.429 | 13.253 | -9.389 | 1.00 | 48.11 | A | O |
| ATOM | 2068 | N | PHE A 498 | 21.030 | 11.890 | -8.566 | 1.00 | 49.38 | A | N |
| ATOM | 2069 | CA | PHE A 498 | 22.049 | 12.227 | -9.581 | 1.00 | 51.16 | A | C |
| ATOM | 2070 | CB | PHE A 498 | 22.339 | 13.747 | -9.687 | 1.00 | 50.95 | A | C |
| ATOM | 2071 | CG | PHE A 498 | 22.492 | 14.470 | -8.356 | 1.00 | 50.16 | A | C |
| ATOM | 2072 | CD1 | PHE A 498 | 22.891 | 13.803 | -7.199 | 1.00 | 49.29 | A | C |
| ATOM | 2073 | CD2 | PHE A 498 | 22.221 | 15.834 | -8.279 | 1.00 | 49.21 | A | C |
| ATOM | 2074 | CE1 | PHE A 498 | 23.010 | 14.487 | -5.995 | 1.00 | 49.87 | A | C |
| ATOM | 2075 | CE2 | PHE A 498 | 22.337 | 16.525 | -7.084 | 1.00 | 48.82 | A | C |
| ATOM | 2076 | CZ | PHE A 498 | 22.731 | 15.855 | -5.941 | 1.00 | 49.19 | A | C |
| ATOM | 2077 | C | PHE A 498 | 23.351 | 11.443 | -9.422 | 1.00 | 52.07 | A | O |
| ATOM | 2078 | O | PHE A 498 | 23.240 | 10.198 | -9.343 | 1.00 | 53.11 | A | O |
| ATOM | 2079 | N1 | LIG A 500 | 24.069 | 8.248 | 20.566 | 1.00 | 22.83 | A | N |
| ATOM | 2080 | C1 | LIG A 500 | 24.736 | 9.453 | 20.688 | 1.00 | 24.37 | A | C |
| ATOM | 2081 | N2 | LIG A 500 | 26.051 | 9.526 | 20.383 | 1.00 | 25.37 | A | N |
| ATOM | 2082 | C2 | LIG A 500 | 26.733 | 10.668 | 20.471 | 1.00 | 25.10 | A | C |
| ATOM | 2083 | N3 | LIG A 500 | 26.149 | 11.792 | 20.865 | 1.00 | 24.75 | A | N |
| ATOM | 2084 | C3 | LIG A 500 | 24.835 | 11.831 | 21.196 | 1.00 | 24.66 | A | C |
| ATOM | 2085 | N4 | LIG A 500 | 23.994 | 12.850 | 21.626 | 1.00 | 25.33 | A | N |
| ATOM | 2086 | C4 | LIG A 500 | 24.266 | 14.316 | 21.867 | 1.00 | 25.51 | A | C |
| ATOM | 2087 | C5 | LIG A 500 | 23.980 | 14.657 | 23.328 | 1.00 | 25.51 | A | C |
| ATOM | 2088 | C6 | LIG A 500 | 24.186 | 16.158 | 23.576 | 1.00 | 26.08 | A | C |
| ATOM | 2089 | C7 | LIG A 500 | 24.613 | 16.859 | 22.273 | 1.00 | 26.88 | A | C |
| ATOM | 2090 | N5 | LIG A 500 | 24.790 | 18.077 | 22.504 | 0.00 | 20.00 | A | N |
| ATOM | 2091 | C8 | LIG A 500 | 25.839 | 18.237 | 23.517 | 0.00 | 20.00 | A | C |
| ATOM | 2092 | C9 | LIG A 500 | 26.228 | 19.714 | 23.624 | 0.00 | 20.00 | A | C |
| ATOM | 2093 | N6 | LIG A 500 | 26.792 | 20.168 | 22.348 | 0.00 | 20.00 | A | N |
| ATOM | 2094 | C10 | LIG A 500 | 27.030 | 21.612 | 22.482 | 0.00 | 20.00 | A | C |
| ATOM | 2095 | C11 | LIG A 500 | 25.741 | 20.007 | 21.334 | 0.00 | 20.00 | A | C |
| ATOM | 2096 | C12 | LIG A 500 | 25.353 | 18.530 | 21.227 | 0.00 | 20.00 | A | C |
| ATOM | 2097 | C13 | LIG A 500 | 23.516 | 16.669 | 21.209 | 1.00 | 26.67 | A | C |
| ATOM | 2098 | C14 | LIG A 500 | 23.348 | 15.171 | 20.950 | 1.00 | 26.03 | A | C |
| ATOM | 2099 | N8 | LIG A 500 | 22.742 | 12.360 | 21.824 | 1.00 | 24.56 | A | N |
| ATOM | 2100 | C16 | LIG A 500 | 22.727 | 11.021 | 21.537 | 1.00 | 23.95 | A | C |
| ATOM | 2101 | C17 | LIG A 500 | 21.470 | 10.233 | 21.670 | 1.00 | 24.06 | A | C |
| ATOM | 2102 | C18 | LIG A 500 | 20.245 | 10.845 | 21.361 | 1.00 | 24.03 | A | C |
| ATOM | 2103 | C19 | LIG A 500 | 19.089 | 10.122 | 21.459 | 1.00 | 24.31 | A | C |
| ATOM | 2104 | C21 | LIG A 500 | 19.116 | 8.800 | 21.888 | 1.00 | 24.98 | A | C |
| ATOM | 2105 | N7 | LIG A 500 | 17.908 | 8.136 | 21.937 | 1.00 | 25.94 | A | N |
| ATOM | 2106 | C22 | LIG A 500 | 17.765 | 6.744 | 22.315 | 1.00 | 26.26 | A | C |
| ATOM | 2107 | C23 | LIG A 500 | 16.299 | 6.387 | 22.157 | 1.00 | 26.19 | A | C |
| ATOM | 2108 | C24 | LIG A 500 | 15.862 | 5.942 | 20.911 | 1.00 | 25.78 | A | C |
| ATOM | 2109 | CL1 | LIG A 500 | 17.045 | 5.830 | 19.541 | 1.00 | 22.71 | A | CL |
| ATOM | 2110 | C26 | LIG A 500 | 14.522 | 5.599 | 20.725 | 1.00 | 25.83 | A | C |
| ATOM | 2111 | C27 | LIG A 500 | 13.623 | 5.685 | 21.781 | 1.00 | 26.26 | A | C |

Figure 9

```
ATOM   2112  C28  LIG A 500     14.046   6.128  23.041  1.00 26.61      A    C
ATOM   2113  C29  LIG A 500     15.379   6.473  23.244  1.00 26.31      A    C
ATOM   2114  F1   LIG A 500     15.777   6.893  24.475  1.00 27.47      A    F
ATOM   2115  C30  LIG A 500     20.337   8.169  22.187  1.00 24.82      A    C
ATOM   2116  C31  LIG A 500     21.514   8.900  22.086  1.00 23.67      A    C
ATOM   2117  C32  LIG A 500     24.091  10.646  21.117  1.00 24.56      A    C
ATOM   2118  OH2  H2O A 600      5.349  22.274   9.038  1.00 15.82      A    O
ATOM   2119  OH2  H2O A 601      1.097   3.268  -1.206  1.00 67.78      A    O
ATOM   2120  OH2  H2O A 602     -1.440  24.282   0.427  1.00 14.55      A    O
ATOM   2121  OH2  H2O A 604      5.842   2.650  -2.979  1.00 37.63      A    O
ATOM   2122  OH2  H2O A 605     -5.885  25.680   1.952  1.00 43.08      A    O
ATOM   2123  OH2  H2O A 606      7.371  13.132  12.791  1.00 12.42      A    O
ATOM   2124  OH2  H2O A 607     -3.822  17.009  -0.716  1.00 16.10      A    O
ATOM   2125  OH2  H2O A 608      0.480   9.375  -3.462  1.00 30.32      A    O
ATOM   2126  OH2  H2O A 609     -1.062  30.746   2.140  1.00 21.05      A    O
ATOM   2127  OH2  H2O A 610      5.970  24.564   4.251  1.00 14.80      A    O
ATOM   2128  OH2  H2O A 611      5.438  18.715  -6.236  1.00 17.36      A    O
ATOM   2129  OH2  H2O A 612      0.333   5.773   0.274  1.00 25.67      A    O
ATOM   2130  OH2  H2O A 613     -0.507  28.686  -0.466  1.00 69.35      A    O
ATOM   2131  OH2  H2O A 614      9.275   9.853  18.853  1.00 19.11      A    O
ATOM   2132  OH2  H2O A 615     -9.578   8.230  -2.757  1.00 39.60      A    O
ATOM   2133  OH2  H2O A 616     -2.059   6.829  -0.636  1.00 32.98      A    O
ATOM   2134  OH2  H2O A 617      2.187  30.042  -0.279  1.00 54.23      A    O
ATOM   2135  OH2  H2O A 618      8.232  24.791  16.130  1.00 21.86      A    O
ATOM   2136  OH2  H2O A 619     -1.106   5.307   4.154  1.00 74.08      A    O
ATOM   2137  OH2  H2O A 620      1.007  26.968  -2.797  1.00 24.54      A    O
ATOM   2138  OH2  H2O A 621     29.752  13.549  20.272  1.00 41.57      A    O
ATOM   2139  OH2  H2O A 622      3.718   0.562  -1.974  1.00 50.67      A    O
ATOM   2140  OH2  H2O A 623     -3.827  23.548   1.696  1.00 41.14      A    O
ATOM   2141  OH2  H2O A 624     35.937  11.283  21.646  1.00 38.73      A    O
ATOM   2142  OH2  H2O A 625     19.938   5.116   1.245  1.00 40.50      A    O
ATOM   2143  OH2  H2O A 626     15.332  19.886  14.139  1.00 22.97      A    O
ATOM   2144  OH2  H2O A 627      3.488   6.171   3.569  1.00 16.95      A    O
ATOM   2145  OH2  H2O A 628      3.885  15.505  11.683  1.00 22.71      A    O
ATOM   2146  OH2  H2O A 630      8.571  15.214  -7.493  1.00 72.13      A    O
ATOM   2147  OH2  H2O A 631     33.963  -0.913  32.866  1.00 50.17      A    O
ATOM   2148  OH2  H2O A 632      5.099  28.038  -1.610  1.00 18.83      A    O
ATOM   2149  OH2  H2O A 633     17.387  13.034  23.107  1.00 49.68      A    O
ATOM   2150  OH2  H2O A 634     16.902  -0.718   4.503  1.00 26.46      A    O
ATOM   2151  OH2  H2O A 635     -1.642  11.842   9.750  1.00 27.44      A    O
ATOM   2152  OH2  H2O A 636     -2.269  12.251  -4.976  1.00 22.82      A    O
ATOM   2153  OH2  H2O A 638     -8.338   8.398  -5.496  1.00 33.85      A    O
ATOM   2154  OH2  H2O A 639     15.479  10.435  -8.516  1.00 41.80      A    O
ATOM   2155  OH2  H2O A 640     -1.987  23.626   5.433  1.00 23.41      A    O
ATOM   2156  OH2  H2O A 641     -2.835   6.517   2.319  1.00 20.76      A    O
ATOM   2157  OH2  H2O A 642     19.262  -0.526  15.210  1.00 27.66      A    O
ATOM   2158  OH2  H2O A 643     26.701  22.282  32.865  1.00 78.33      A    O
ATOM   2159  OH2  H2O A 644      2.692  21.330  -0.856  1.00 15.84      A    O
ATOM   2160  OH2  H2O A 645     -4.403  23.982   9.677  1.00 26.48      A    O
ATOM   2161  OH2  H2O A 646     28.452   0.441  41.394  1.00 68.91      A    O
ATOM   2162  OH2  H2O A 647      4.107  35.723   6.944  1.00 48.08      A    O
ATOM   2163  OH2  H2O A 648      0.794   5.117  10.354  1.00 24.34      A    O
ATOM   2164  OH2  H2O A 649    -13.689   5.969  -2.513  1.00 72.20      A    O
ATOM   2165  OH2  H2O A 650     11.854  28.534   2.467  1.00 31.75      A    O
ATOM   2166  OH2  H2O A 651      2.391  -2.354   0.985  1.00 22.45      A    O
ATOM   2167  OH2  H2O A 652     -1.612  20.680  -1.100  1.00 34.66      A    O
ATOM   2168  OH2  H2O A 653      3.713  22.685  10.953  1.00 18.57      A    O
ATOM   2169  OH2  H2O A 654      3.348  30.809  -4.177  1.00 23.62      A    O
ATOM   2170  OH2  H2O A 655     23.980  20.259  26.894  1.00 48.74      A    O
```

Figure 9

| | | | | | | | | | | | |
|---|---|---|---|---|---|---|---|---|---|---|---|
| ATOM | 2171 | OH2 | H2O | A | 656 | 4.705 | 3.944 | 16.333 | 1.00 | 24.89 | A | O |
| ATOM | 2172 | OH2 | H2O | A | 657 | 1.144 | 3.298 | 6.368 | 1.00 | 85.14 | A | O |
| ATOM | 2173 | OH2 | H2O | A | 658 | -2.099 | 24.750 | -5.690 | 1.00 | 43.47 | A | O |
| ATOM | 2174 | OH2 | H2O | A | 659 | 9.416 | 28.442 | -4.563 | 1.00 | 17.83 | A | O |
| ATOM | 2175 | OH2 | H2O | A | 660 | 23.725 | 20.907 | 21.459 | 0.00 | 25.86 | A | O |
| ATOM | 2176 | OH2 | H2O | A | 661 | 14.722 | 14.906 | 23.842 | 1.00 | 39.95 | A | O |
| ATOM | 2177 | OH2 | H2O | A | 662 | -6.483 | 11.012 | -3.027 | 1.00 | 63.27 | A | O |
| ATOM | 2178 | OH2 | H2O | A | 663 | 6.434 | 34.662 | 3.317 | 1.00 | 29.30 | A | O |
| ATOM | 2179 | OH2 | H2O | A | 664 | 30.456 | 7.627 | 15.373 | 1.00 | 76.87 | A | O |
| ATOM | 2180 | OH2 | H2O | A | 665 | 2.409 | 2.727 | 3.263 | 1.00 | 66.81 | A | O |
| ATOM | 2181 | OH2 | H2O | A | 666 | -2.660 | 24.478 | -2.061 | 1.00 | 32.49 | A | O |
| ATOM | 2182 | OH2 | H2O | A | 667 | 8.458 | 0.884 | 3.396 | 1.00 | 26.59 | A | O |
| ATOM | 2183 | OH2 | H2O | A | 668 | 22.415 | 23.445 | -0.453 | 1.00 | 36.36 | A | O |
| ATOM | 2184 | OH2 | H2O | A | 669 | 4.989 | 1.090 | 2.242 | 1.00 | 28.13 | A | O |
| ATOM | 2185 | OH2 | H2O | A | 670 | -5.665 | 24.485 | -1.975 | 1.00 | 77.32 | A | O |
| ATOM | 2186 | OH2 | H2O | A | 671 | -2.324 | 8.294 | 6.950 | 1.00 | 30.39 | A | O |
| ATOM | 2187 | OH2 | H2O | A | 672 | 6.250 | 2.966 | 18.912 | 1.00 | 37.24 | A | O |
| ATOM | 2188 | OH2 | H2O | A | 673 | 33.693 | 21.295 | 11.695 | 1.00 | 41.74 | A | O |
| ATOM | 2189 | OH2 | H2O | A | 674 | 14.179 | 0.638 | 4.331 | 1.00 | 31.06 | A | O |
| ATOM | 2190 | OH2 | H2O | A | 675 | -2.695 | 25.118 | 11.363 | 1.00 | 27.39 | A | O |
| ATOM | 2191 | OH2 | H2O | A | 676 | 31.540 | 4.123 | 18.082 | 1.00 | 48.11 | A | O |
| ATOM | 2192 | OH2 | H2O | A | 677 | 5.588 | 15.392 | 14.117 | 1.00 | 35.18 | A | O |
| ATOM | 2193 | OH2 | H2O | A | 678 | -5.473 | 18.878 | 7.007 | 1.00 | 37.60 | A | O |
| ATOM | 2194 | OH2 | H2O | A | 679 | 14.950 | 21.275 | 16.348 | 1.00 | 43.89 | A | O |
| ATOM | 2195 | OH2 | H2O | A | 680 | 32.025 | 15.494 | 31.958 | 1.00 | 28.24 | A | O |
| ATOM | 2196 | OH2 | H2O | A | 681 | -6.413 | 19.268 | 9.612 | 1.00 | 40.86 | A | O |
| ATOM | 2197 | OH2 | H2O | A | 682 | 28.913 | 2.713 | 19.340 | 1.00 | 28.56 | A | O |
| ATOM | 2198 | OH2 | H2O | A | 683 | 17.413 | 16.213 | 24.200 | 1.00 | 52.78 | A | O |
| ATOM | 2199 | OH2 | H2O | A | 684 | 14.404 | 25.319 | 7.150 | 1.00 | 31.87 | A | O |
| ATOM | 2200 | OH2 | H2O | A | 685 | -4.745 | 23.325 | 6.846 | 1.00 | 30.17 | A | O |
| ATOM | 2201 | OH2 | H2O | A | 686 | 16.769 | 24.287 | -9.547 | 1.00 | 49.40 | A | O |
| ATOM | 2202 | OH2 | H2O | A | 687 | -1.862 | 27.093 | -4.000 | 1.00 | 29.75 | A | O |
| ATOM | 2203 | OH2 | H2O | A | 688 | 33.728 | 12.719 | 11.137 | 1.00 | 40.77 | A | O |
| ATOM | 2204 | OH2 | H2O | A | 689 | -4.790 | 25.308 | 13.315 | 1.00 | 37.31 | A | O |
| ATOM | 2205 | OH2 | H2O | A | 690 | 4.070 | 4.933 | 32.776 | 1.00 | 38.88 | A | O |
| ATOM | 2206 | OH2 | H2O | A | 691 | 18.568 | -2.096 | 19.160 | 1.00 | 26.80 | A | O |
| ATOM | 2207 | OH2 | H2O | A | 692 | 12.211 | 22.175 | 18.124 | 1.00 | 35.73 | A | O |
| ATOM | 2208 | OH2 | H2O | A | 693 | 16.202 | 23.720 | 12.092 | 1.00 | 32.02 | A | O |
| ATOM | 2209 | OH2 | H2O | A | 694 | 17.603 | 0.225 | 17.098 | 1.00 | 31.19 | A | O |
| ATOM | 2210 | OH2 | H2O | A | 695 | -9.584 | 10.643 | -6.537 | 1.00 | 26.71 | A | O |
| ATOM | 2211 | OH2 | H2O | A | 696 | 30.419 | 16.800 | 0.941 | 1.00 | 35.28 | A | O |
| ATOM | 2212 | OH2 | H2O | A | 697 | 10.939 | 16.418 | -8.557 | 1.00 | 68.09 | A | O |
| ATOM | 2213 | OH2 | H2O | A | 698 | 25.036 | 11.498 | 34.746 | 1.00 | 62.56 | A | O |
| ATOM | 2214 | OH2 | H2O | A | 699 | -5.302 | 22.028 | -0.204 | 1.00 | 25.89 | A | O |
| ATOM | 2215 | OH2 | H2O | A | 700 | 5.850 | 11.661 | -7.383 | 1.00 | 71.81 | A | O |
| ATOM | 2216 | OH2 | H2O | A | 701 | 33.866 | 12.190 | 23.262 | 1.00 | 34.22 | A | O |
| ATOM | 2217 | OH2 | H2O | A | 702 | 15.288 | 8.646 | 26.789 | 1.00 | 30.00 | A | O |
| ATOM | 2218 | CB | TRP | B | 238 | 46.460 | 28.014 | 32.756 | 1.00 | 56.27 | B | C |
| ATOM | 2219 | CG | TRP | B | 238 | 45.975 | 28.537 | 34.086 | 1.00 | 56.49 | B | C |
| ATOM | 2220 | CD2 | TRP | B | 238 | 46.447 | 28.161 | 35.395 | 1.00 | 56.78 | B | C |
| ATOM | 2221 | CE2 | TRP | B | 238 | 45.691 | 28.892 | 36.337 | 1.00 | 56.69 | B | C |
| ATOM | 2222 | CE3 | TRP | B | 238 | 47.436 | 27.277 | 35.860 | 1.00 | 56.14 | B | C |
| ATOM | 2223 | CD1 | TRP | B | 238 | 44.981 | 29.453 | 34.290 | 1.00 | 56.48 | B | C |
| ATOM | 2224 | NE1 | TRP | B | 238 | 44.806 | 29.670 | 35.636 | 1.00 | 56.52 | B | N |
| ATOM | 2225 | CZ2 | TRP | B | 238 | 45.891 | 28.766 | 37.719 | 1.00 | 56.54 | B | C |
| ATOM | 2226 | CZ3 | TRP | B | 238 | 47.634 | 27.153 | 37.236 | 1.00 | 55.20 | B | C |
| ATOM | 2227 | CH2 | TRP | B | 238 | 46.865 | 27.895 | 38.147 | 1.00 | 55.64 | B | C |
| ATOM | 2228 | C | TRP | B | 238 | 48.157 | 28.077 | 30.917 | 1.00 | 55.72 | B | C |
| ATOM | 2229 | O | TRP | B | 238 | 48.710 | 26.982 | 31.024 | 1.00 | 55.61 | B | O |

Figure 9

| ATOM | 2230 | N | TRP | B | 238 | 47.252 | 30.209 | 31.902 | 1.00 | 55.92 | B | N |
|------|------|-----|-----|---|-----|--------|--------|--------|------|-------|---|---|
| ATOM | 2231 | CA | TRP | B | 238 | 47.637 | 28.795 | 32.162 | 1.00 | 55.98 | B | C |
| ATOM | 2232 | N | GLU | B | 239 | 47.940 | 28.665 | 29.740 | 1.00 | 55.48 | B | N |
| ATOM | 2233 | CA | GLU | B | 239 | 48.420 | 28.074 | 28.488 | 1.00 | 54.91 | B | C |
| ATOM | 2234 | CB | GLU | B | 239 | 47.588 | 28.525 | 27.286 | 1.00 | 57.76 | B | C |
| ATOM | 2235 | CG | GLU | B | 239 | 46.619 | 27.477 | 26.772 | 1.00 | 62.28 | B | C |
| ATOM | 2236 | CD | GLU | B | 239 | 45.239 | 27.601 | 27.407 | 1.00 | 66.29 | B | C |
| ATOM | 2237 | OE1 | GLU | B | 239 | 45.013 | 27.041 | 28.513 | 1.00 | 67.75 | B | O |
| ATOM | 2238 | OE2 | GLU | B | 239 | 44.379 | 28.277 | 26.796 | 1.00 | 67.97 | B | O |
| ATOM | 2239 | C | GLU | B | 239 | 49.865 | 28.478 | 28.259 | 1.00 | 53.25 | B | C |
| ATOM | 2240 | O | GLU | B | 239 | 50.259 | 29.599 | 28.581 | 1.00 | 53.33 | B | O |
| ATOM | 2241 | N | VAL | B | 240 | 50.652 | 27.554 | 27.717 | 1.00 | 50.98 | B | N |
| ATOM | 2242 | CA | VAL | B | 240 | 52.062 | 27.797 | 27.438 | 1.00 | 48.18 | B | C |
| ATOM | 2243 | CB | VAL | B | 240 | 52.969 | 27.384 | 28.636 | 1.00 | 46.76 | B | C |
| ATOM | 2244 | CG1 | VAL | B | 240 | 52.590 | 28.152 | 29.888 | 1.00 | 44.77 | B | C |
| ATOM | 2245 | CG2 | VAL | B | 240 | 52.882 | 25.893 | 28.882 | 1.00 | 45.79 | B | C |
| ATOM | 2246 | C | VAL | B | 240 | 52.485 | 27.012 | 26.197 | 1.00 | 47.42 | B | C |
| ATOM | 2247 | O | VAL | B | 240 | 51.862 | 26.007 | 25.845 | 1.00 | 47.14 | B | O |
| ATOM | 2248 | N | PRO | B | 241 | 53.518 | 27.498 | 25.487 | 1.00 | 46.77 | B | N |
| ATOM | 2249 | CD | PRO | B | 241 | 54.094 | 28.842 | 25.667 | 1.00 | 46.22 | B | C |
| ATOM | 2250 | CA | PRO | B | 241 | 54.053 | 26.870 | 24.275 | 1.00 | 46.34 | B | C |
| ATOM | 2251 | CB | PRO | B | 241 | 55.053 | 27.912 | 23.774 | 1.00 | 46.25 | B | C |
| ATOM | 2252 | CG | PRO | B | 241 | 54.471 | 29.199 | 24.261 | 1.00 | 46.20 | B | C |
| ATOM | 2253 | C | PRO | B | 241 | 54.753 | 25.533 | 24.541 | 1.00 | 46.52 | B | C |
| ATOM | 2254 | O | PRO | B | 241 | 55.455 | 25.376 | 25.539 | 1.00 | 46.44 | B | O |
| ATOM | 2255 | N | ARG | B | 242 | 54.564 | 24.586 | 23.625 | 1.00 | 46.80 | B | N |
| ATOM | 2256 | CA | ARG | B | 242 | 55.171 | 23.257 | 23.703 | 1.00 | 47.35 | B | C |
| ATOM | 2257 | CB | ARG | B | 242 | 54.868 | 22.497 | 22.405 | 1.00 | 48.07 | B | C |
| ATOM | 2258 | CG | ARG | B | 242 | 55.528 | 21.124 | 22.245 | 1.00 | 50.12 | B | C |
| ATOM | 2259 | CD | ARG | B | 242 | 54.909 | 20.064 | 23.132 | 1.00 | 51.76 | B | C |
| ATOM | 2260 | NE | ARG | B | 242 | 53.446 | 20.006 | 23.031 | 1.00 | 54.49 | B | N |
| ATOM | 2261 | CZ | ARG | B | 242 | 52.765 | 19.476 | 22.018 | 1.00 | 54.44 | B | C |
| ATOM | 2262 | NH1 | ARG | B | 242 | 53.395 | 18.939 | 20.982 | 1.00 | 55.89 | B | N |
| ATOM | 2263 | NH2 | ARG | B | 242 | 51.441 | 19.474 | 22.048 | 1.00 | 54.88 | B | N |
| ATOM | 2264 | C | ARG | B | 242 | 56.690 | 23.342 | 23.934 | 1.00 | 47.46 | B | C |
| ATOM | 2265 | O | ARG | B | 242 | 57.260 | 22.487 | 24.620 | 1.00 | 47.19 | B | O |
| ATOM | 2266 | N | GLU | B | 243 | 57.317 | 24.396 | 23.401 | 1.00 | 47.89 | B | N |
| ATOM | 2267 | CA | GLU | B | 243 | 58.770 | 24.627 | 23.520 | 1.00 | 48.48 | B | C |
| ATOM | 2268 | CB | GLU | B | 243 | 59.252 | 25.774 | 22.608 | 1.00 | 50.64 | B | C |
| ATOM | 2269 | CG | GLU | B | 243 | 59.152 | 25.511 | 21.111 | 1.00 | 54.55 | B | C |
| ATOM | 2270 | CD | GLU | B | 243 | 57.707 | 25.512 | 20.613 | 1.00 | 57.53 | B | C |
| ATOM | 2271 | OE1 | GLU | B | 243 | 56.925 | 26.396 | 21.049 | 1.00 | 58.15 | B | O |
| ATOM | 2272 | OE2 | GLU | B | 243 | 57.351 | 24.630 | 19.794 | 1.00 | 58.29 | B | O |
| ATOM | 2273 | C | GLU | B | 243 | 59.261 | 24.912 | 24.939 | 1.00 | 47.12 | B | C |
| ATOM | 2274 | O | GLU | B | 243 | 60.457 | 24.829 | 25.205 | 1.00 | 46.69 | B | O |
| ATOM | 2275 | N | THR | B | 244 | 58.359 | 25.290 | 25.837 | 1.00 | 45.42 | B | N |
| ATOM | 2276 | CA | THR | B | 244 | 58.754 | 25.565 | 27.215 | 1.00 | 43.79 | B | C |
| ATOM | 2277 | CB | THR | B | 244 | 57.766 | 26.523 | 27.894 | 1.00 | 44.78 | B | C |
| ATOM | 2278 | OG1 | THR | B | 244 | 56.451 | 25.948 | 27.878 | 1.00 | 45.26 | B | O |
| ATOM | 2279 | CG2 | THR | B | 244 | 57.751 | 27.869 | 27.182 | 1.00 | 46.23 | B | C |
| ATOM | 2280 | C | THR | B | 244 | 58.830 | 24.287 | 28.059 | 1.00 | 42.13 | B | C |
| ATOM | 2281 | O | THR | B | 244 | 59.098 | 24.344 | 29.261 | 1.00 | 41.45 | B | O |
| ATOM | 2282 | N | LEU | B | 245 | 58.617 | 23.139 | 27.427 | 1.00 | 40.20 | B | N |
| ATOM | 2283 | CA | LEU | B | 245 | 58.632 | 21.881 | 28.147 | 1.00 | 39.06 | B | C |
| ATOM | 2284 | CB | LEU | B | 245 | 57.188 | 21.387 | 28.352 | 1.00 | 38.85 | B | C |
| ATOM | 2285 | CG | LEU | B | 245 | 56.974 | 20.027 | 29.039 | 1.00 | 38.64 | B | C |
| ATOM | 2286 | CD1 | LEU | B | 245 | 57.001 | 20.190 | 30.555 | 1.00 | 39.01 | B | C |
| ATOM | 2287 | CD2 | LEU | B | 245 | 55.649 | 19.421 | 28.609 | 1.00 | 38.52 | B | C |
| ATOM | 2288 | C | LEU | B | 245 | 59.438 | 20.802 | 27.444 | 1.00 | 38.75 | B | C |

Figure 9

| | | | | | | | | | | | |
|---|---|---|---|---|---|---|---|---|---|---|---|
| ATOM | 2289 | O | LEU | B | 245 | 59.338 | 20.628 | 26.221 | 1.00 | 38.51 | B | O |
| ATOM | 2290 | N | LYS | B | 246 | 60.222 | 20.062 | 28.231 | 1.00 | 38.19 | B | N |
| ATOM | 2291 | CA | LYS | B | 246 | 61.013 | 18.965 | 27.695 | 1.00 | 37.96 | B | C |
| ATOM | 2292 | CB | LYS | B | 246 | 62.520 | 19.240 | 27.785 | 1.00 | 39.88 | B | C |
| ATOM | 2293 | CG | LYS | B | 246 | 63.361 | 18.134 | 27.100 | 1.00 | 43.53 | B | C |
| ATOM | 2294 | CD | LYS | B | 246 | 64.858 | 18.434 | 27.000 | 1.00 | 44.95 | B | C |
| ATOM | 2295 | CE | LYS | B | 246 | 65.472 | 18.843 | 28.324 | 1.00 | 45.09 | B | C |
| ATOM | 2296 | NZ | LYS | B | 246 | 66.951 | 18.937 | 28.159 | 1.00 | 47.78 | B | N |
| ATOM | 2297 | C | LYS | B | 246 | 60.684 | 17.638 | 28.377 | 1.00 | 36.47 | B | C |
| ATOM | 2298 | O | LYS | B | 246 | 60.952 | 17.449 | 29.559 | 1.00 | 36.23 | B | O |
| ATOM | 2299 | N | LEU | B | 247 | 60.097 | 16.725 | 27.608 | 1.00 | 35.54 | B | N |
| ATOM | 2300 | CA | LEU | B | 247 | 59.741 | 15.405 | 28.095 | 1.00 | 34.45 | B | C |
| ATOM | 2301 | CB | LEU | B | 247 | 58.677 | 14.752 | 27.199 | 1.00 | 35.08 | B | C |
| ATOM | 2302 | CG | LEU | B | 247 | 57.212 | 15.041 | 27.550 | 1.00 | 36.46 | B | C |
| ATOM | 2303 | CD1 | LEU | B | 247 | 56.919 | 16.530 | 27.576 | 1.00 | 36.39 | B | C |
| ATOM | 2304 | CD2 | LEU | B | 247 | 56.308 | 14.337 | 26.560 | 1.00 | 38.09 | B | C |
| ATOM | 2305 | C | LEU | B | 247 | 61.008 | 14.573 | 28.119 | 1.00 | 33.33 | B | C |
| ATOM | 2306 | O | LEU | B | 247 | 61.764 | 14.527 | 27.140 | 1.00 | 34.17 | B | O |
| ATOM | 2307 | N | VAL | B | 248 | 61.223 | 13.902 | 29.241 | 1.00 | 31.13 | B | N |
| ATOM | 2308 | CA | VAL | B | 248 | 62.410 | 13.097 | 29.422 | 1.00 | 28.82 | B | C |
| ATOM | 2309 | CB | VAL | B | 248 | 63.197 | 13.580 | 30.668 | 1.00 | 27.97 | B | C |
| ATOM | 2310 | CG1 | VAL | B | 248 | 64.531 | 12.866 | 30.761 | 1.00 | 26.98 | B | C |
| ATOM | 2311 | CG2 | VAL | B | 248 | 63.380 | 15.090 | 30.633 | 1.00 | 26.54 | B | C |
| ATOM | 2312 | C | VAL | B | 248 | 62.155 | 11.602 | 29.565 | 1.00 | 27.87 | B | C |
| ATOM | 2313 | O | VAL | B | 248 | 62.813 | 10.789 | 28.923 | 1.00 | 28.61 | B | O |
| ATOM | 2314 | N | GLU | B | 249 | 61.142 | 11.239 | 30.335 | 1.00 | 26.51 | B | N |
| ATOM | 2315 | CA | GLU | B | 249 | 60.902 | 9.831 | 30.598 | 1.00 | 25.42 | B | C |
| ATOM | 2316 | CB | GLU | B | 249 | 61.686 | 9.511 | 31.864 | 1.00 | 25.56 | B | C |
| ATOM | 2317 | CG | GLU | B | 249 | 61.536 | 8.133 | 32.443 | 1.00 | 27.24 | B | C |
| ATOM | 2318 | CD | GLU | B | 249 | 62.259 | 7.996 | 33.778 | 1.00 | 27.44 | B | C |
| ATOM | 2319 | OE1 | GLU | B | 249 | 63.032 | 8.914 | 34.162 | 1.00 | 26.77 | B | O |
| ATOM | 2320 | OE2 | GLU | B | 249 | 62.041 | 6.967 | 34.447 | 1.00 | 30.33 | B | O |
| ATOM | 2321 | C | GLU | B | 249 | 59.424 | 9.490 | 30.790 | 1.00 | 24.32 | B | C |
| ATOM | 2322 | O | GLU | B | 249 | 58.694 | 10.213 | 31.448 | 1.00 | 23.79 | B | O |
| ATOM | 2323 | N | ARG | B | 250 | 58.990 | 8.369 | 30.242 | 1.00 | 23.97 | B | N |
| ATOM | 2324 | CA | ARG | B | 250 | 57.599 | 7.981 | 30.394 | 1.00 | 25.30 | B | C |
| ATOM | 2325 | CB | ARG | B | 250 | 57.104 | 7.239 | 29.165 | 1.00 | 26.48 | B | C |
| ATOM | 2326 | CG | ARG | B | 250 | 55.614 | 7.290 | 28.995 | 1.00 | 26.56 | B | C |
| ATOM | 2327 | CD | ARG | B | 250 | 55.205 | 6.397 | 27.869 | 1.00 | 28.42 | B | C |
| ATOM | 2328 | NE | ARG | B | 250 | 55.428 | 5.008 | 28.233 | 1.00 | 29.17 | B | N |
| ATOM | 2329 | CZ | ARG | B | 250 | 55.230 | 3.980 | 27.421 | 1.00 | 30.10 | B | C |
| ATOM | 2330 | NH1 | ARG | B | 250 | 54.794 | 4.176 | 26.186 | 1.00 | 28.99 | B | N |
| ATOM | 2331 | NH2 | ARG | B | 250 | 55.502 | 2.752 | 27.845 | 1.00 | 31.91 | B | N |
| ATOM | 2332 | C | ARG | B | 250 | 57.441 | 7.091 | 31.605 | 1.00 | 25.64 | B | C |
| ATOM | 2333 | O | ARG | B | 250 | 57.906 | 5.948 | 31.616 | 1.00 | 25.58 | B | O |
| ATOM | 2334 | N | LEU | B | 251 | 56.763 | 7.625 | 32.615 | 1.00 | 25.84 | B | N |
| ATOM | 2335 | CA | LEU | B | 251 | 56.511 | 6.917 | 33.865 | 1.00 | 24.96 | B | C |
| ATOM | 2336 | CB | LEU | B | 251 | 56.176 | 7.925 | 34.968 | 1.00 | 23.28 | B | C |
| ATOM | 2337 | CG | LEU | B | 251 | 57.194 | 9.056 | 35.140 | 1.00 | 21.83 | B | C |
| ATOM | 2338 | CD1 | LEU | B | 251 | 56.626 | 10.169 | 35.983 | 1.00 | 20.23 | B | C |
| ATOM | 2339 | CD2 | LEU | B | 251 | 58.486 | 8.515 | 35.734 | 1.00 | 22.16 | B | C |
| ATOM | 2340 | C | LEU | B | 251 | 55.383 | 5.887 | 33.706 | 1.00 | 26.08 | B | C |
| ATOM | 2341 | O | LEU | B | 251 | 55.458 | 4.783 | 34.261 | 1.00 | 26.34 | B | O |
| ATOM | 2342 | N | GLY | B | 252 | 54.362 | 6.225 | 32.920 | 1.00 | 26.37 | B | N |
| ATOM | 2343 | CA | GLY | B | 252 | 53.261 | 5.299 | 32.727 | 1.00 | 26.01 | B | C |
| ATOM | 2344 | C | GLY | B | 252 | 52.477 | 5.456 | 31.430 | 1.00 | 26.70 | B | C |
| ATOM | 2345 | O | GLY | B | 252 | 52.428 | 6.535 | 30.834 | 1.00 | 26.01 | B | O |
| ATOM | 2346 | N | ALA | B | 253 | 51.855 | 4.359 | 31.002 | 1.00 | 26.80 | B | N |
| ATOM | 2347 | CA | ALA | B | 253 | 51.028 | 4.329 | 29.797 | 1.00 | 27.30 | B | C |

Figure 9

| | | | | | | | | | | |
|---|---|---|---|---|---|---|---|---|---|---|
| ATOM | 2348 | CB | ALA | B | 253 | 51.777 | 3.644 | 28.661 | 1.00 27.93 | B | C |
| ATOM | 2349 | C | ALA | B | 253 | 49.716 | 3.584 | 30.107 | 1.00 27.67 | B | C |
| ATOM | 2350 | O | ALA | B | 253 | 49.725 | 2.440 | 30.577 | 1.00 26.69 | B | O |
| ATOM | 2351 | N | GLY | B | 254 | 48.588 | 4.242 | 29.863 | 1.00 28.79 | B | N |
| ATOM | 2352 | CA | GLY | B | 254 | 47.305 | 3.617 | 30.137 | 1.00 30.56 | B | C |
| ATOM | 2353 | C | GLY | B | 254 | 46.282 | 3.704 | 29.019 | 1.00 31.12 | B | C |
| ATOM | 2354 | O | GLY | B | 254 | 46.583 | 4.181 | 27.927 | 1.00 31.31 | B | O |
| ATOM | 2355 | N | GLN | B | 255 | 45.060 | 3.264 | 29.319 | 1.00 31.90 | B | N |
| ATOM | 2356 | CA | GLN | B | 255 | 43.952 | 3.253 | 28.362 | 1.00 31.90 | B | C |
| ATOM | 2357 | CB | GLN | B | 255 | 42.685 | 2.674 | 29.037 | 1.00 35.55 | B | C |
| ATOM | 2358 | CG | GLN | B | 255 | 41.714 | 1.938 | 28.071 | 1.00 42.08 | B | C |
| ATOM | 2359 | CD | GLN | B | 255 | 40.210 | 2.044 | 28.447 | 1.00 44.80 | B | C |
| ATOM | 2360 | OE1 | GLN | B | 255 | 39.333 | 2.079 | 27.558 | 1.00 44.86 | B | O |
| ATOM | 2361 | NE2 | GLN | B | 255 | 39.914 | 2.081 | 29.750 | 1.00 44.42 | B | N |
| ATOM | 2362 | C | GLN | B | 255 | 43.637 | 4.628 | 27.745 | 1.00 30.07 | B | C |
| ATOM | 2363 | O | GLN | B | 255 | 43.340 | 4.720 | 26.556 | 1.00 30.10 | B | O |
| ATOM | 2364 | N | PHE | B | 256 | 43.762 | 5.692 | 28.537 | 1.00 28.33 | B | N |
| ATOM | 2365 | CA | PHE | B | 256 | 43.433 | 7.051 | 28.095 | 1.00 27.74 | B | C |
| ATOM | 2366 | CB | PHE | B | 256 | 42.551 | 7.742 | 29.146 | 1.00 29.91 | B | C |
| ATOM | 2367 | CG | PHE | B | 256 | 41.146 | 7.194 | 29.240 | 1.00 31.57 | B | C |
| ATOM | 2368 | CD1 | PHE | B | 256 | 40.751 | 6.087 | 28.495 | 1.00 32.29 | B | C |
| ATOM | 2369 | CD2 | PHE | B | 256 | 40.217 | 7.797 | 30.074 | 1.00 32.87 | B | C |
| ATOM | 2370 | CE1 | PHE | B | 256 | 39.455 | 5.588 | 28.574 | 1.00 32.73 | B | C |
| ATOM | 2371 | CE2 | PHE | B | 256 | 38.920 | 7.308 | 30.162 | 1.00 33.18 | B | C |
| ATOM | 2372 | CZ | PHE | B | 256 | 38.541 | 6.199 | 29.409 | 1.00 33.34 | B | C |
| ATOM | 2373 | C | PHE | B | 256 | 44.575 | 8.003 | 27.765 | 1.00 27.10 | B | C |
| ATOM | 2374 | O | PHE | B | 256 | 44.337 | 9.112 | 27.276 | 1.00 26.08 | B | O |
| ATOM | 2375 | N | GLY | B | 257 | 45.804 | 7.601 | 28.074 | 1.00 26.83 | B | N |
| ATOM | 2376 | CA | GLY | B | 257 | 46.948 | 8.460 | 27.813 | 1.00 26.07 | B | C |
| ATOM | 2377 | C | GLY | B | 257 | 48.196 | 8.019 | 28.548 | 1.00 25.41 | B | C |
| ATOM | 2378 | O | GLY | B | 257 | 48.340 | 6.845 | 28.880 | 1.00 24.22 | B | O |
| ATOM | 2379 | N | GLU | B | 258 | 49.092 | 8.968 | 28.822 | 1.00 27.07 | B | N |
| ATOM | 2380 | CA | GLU | B | 258 | 50.353 | 8.663 | 29.501 | 1.00 27.74 | B | C |
| ATOM | 2381 | CB | GLU | B | 258 | 51.471 | 8.458 | 28.459 | 1.00 29.40 | B | C |
| ATOM | 2382 | CG | GLU | B | 258 | 50.993 | 7.851 | 27.140 | 1.00 33.72 | B | C |
| ATOM | 2383 | CD | GLU | B | 258 | 52.098 | 7.203 | 26.344 | 1.00 37.55 | B | C |
| ATOM | 2384 | OE1 | GLU | B | 258 | 52.903 | 7.935 | 25.716 | 1.00 39.03 | B | O |
| ATOM | 2385 | OE2 | GLU | B | 258 | 52.156 | 5.952 | 26.343 | 1.00 39.60 | B | O |
| ATOM | 2386 | C | GLU | B | 258 | 50.797 | 9.740 | 30.482 | 1.00 26.75 | B | C |
| ATOM | 2387 | O | GLU | B | 258 | 50.263 | 10.849 | 30.485 | 1.00 26.18 | B | O |
| ATOM | 2388 | N | VAL | B | 259 | 51.751 | 9.381 | 31.342 | 1.00 26.10 | B | N |
| ATOM | 2389 | CA | VAL | B | 259 | 52.340 | 10.319 | 32.308 | 1.00 25.03 | B | C |
| ATOM | 2390 | CB | VAL | B | 259 | 52.022 | 9.955 | 33.766 | 1.00 23.74 | B | C |
| ATOM | 2391 | CG1 | VAL | B | 259 | 52.461 | 11.083 | 34.678 | 1.00 22.13 | B | C |
| ATOM | 2392 | CG2 | VAL | B | 259 | 50.536 | 9.672 | 33.927 | 1.00 25.46 | B | C |
| ATOM | 2393 | C | VAL | B | 259 | 53.866 | 10.291 | 32.098 | 1.00 23.98 | B | C |
| ATOM | 2394 | O | VAL | B | 259 | 54.468 | 9.221 | 31.991 | 1.00 22.76 | B | O |
| ATOM | 2395 | N | TRP | B | 260 | 54.465 | 11.473 | 32.005 | 1.00 24.16 | B | N |
| ATOM | 2396 | CA | TRP | B | 260 | 55.898 | 11.619 | 31.771 | 1.00 25.16 | B | C |
| ATOM | 2397 | CB | TRP | B | 260 | 56.154 | 12.284 | 30.397 | 1.00 25.70 | B | C |
| ATOM | 2398 | CG | TRP | B | 260 | 55.939 | 11.400 | 29.201 | 1.00 27.68 | B | C |
| ATOM | 2399 | CD2 | TRP | B | 260 | 56.939 | 10.946 | 28.274 | 1.00 28.53 | B | C |
| ATOM | 2400 | CE2 | TRP | B | 260 | 56.297 | 10.069 | 27.363 | 1.00 29.81 | B | C |
| ATOM | 2401 | CE3 | TRP | B | 260 | 58.313 | 11.189 | 28.125 | 1.00 27.55 | B | C |
| ATOM | 2402 | CD1 | TRP | B | 260 | 54.766 | 10.812 | 28.812 | 1.00 28.81 | B | C |
| ATOM | 2403 | NE1 | TRP | B | 260 | 54.975 | 10.006 | 27.718 | 1.00 29.40 | B | N |
| ATOM | 2404 | CZ2 | TRP | B | 260 | 56.989 | 9.432 | 26.317 | 1.00 28.65 | B | C |
| ATOM | 2405 | CZ3 | TRP | B | 260 | 58.995 | 10.555 | 27.088 | 1.00 26.74 | B | C |
| ATOM | 2406 | CH2 | TRP | B | 260 | 58.332 | 9.686 | 26.200 | 1.00 27.68 | B | C |

Figure 9

| ATOM | 2407 | C | TRP | B | 260 | 56.567 | 12.507 | 32.804 | 1.00 | 24.62 | B | C |
| ATOM | 2408 | O | TRP | B | 260 | 55.925 | 13.353 | 33.415 | 1.00 | 24.11 | B | O |
| ATOM | 2409 | N | MET | B | 261 | 57.851 | 12.252 | 33.043 | 1.00 | 24.60 | B | N |
| ATOM | 2410 | CA | MET | B | 261 | 58.648 | 13.106 | 33.903 | 1.00 | 23.03 | B | C |
| ATOM | 2411 | CB | MET | B | 261 | 59.741 | 12.316 | 34.624 | 1.00 | 22.13 | B | C |
| ATOM | 2412 | CG | MET | B | 261 | 60.633 | 13.167 | 35.530 | 1.00 | 21.14 | B | C |
| ATOM | 2413 | SD | MET | B | 261 | 61.883 | 14.191 | 34.673 | 1.00 | 23.17 | B | S |
| ATOM | 2414 | CE | MET | B | 261 | 63.035 | 12.931 | 34.246 | 1.00 | 22.43 | B | C |
| ATOM | 2415 | C | MET | B | 261 | 59.276 | 14.047 | 32.861 | 1.00 | 23.53 | B | C |
| ATOM | 2416 | O | MET | B | 261 | 59.611 | 13.619 | 31.750 | 1.00 | 22.96 | B | O |
| ATOM | 2417 | N | GLY | B | 262 | 59.388 | 15.325 | 33.200 | 1.00 | 24.00 | B | N |
| ATOM | 2418 | CA | GLY | B | 262 | 59.963 | 16.289 | 32.287 | 1.00 | 25.22 | B | C |
| ATOM | 2419 | C | GLY | B | 262 | 60.469 | 17.502 | 33.035 | 1.00 | 26.90 | B | C |
| ATOM | 2420 | O | GLY | B | 262 | 60.504 | 17.515 | 34.266 | 1.00 | 27.14 | B | O |
| ATOM | 2421 | N | TYR | B | 263 | 60.902 | 18.511 | 32.290 | 1.00 | 28.25 | B | N |
| ATOM | 2422 | CA | TYR | B | 263 | 61.398 | 19.741 | 32.886 | 1.00 | 29.24 | B | C |
| ATOM | 2423 | CB | TYR | B | 263 | 62.913 | 19.874 | 32.681 | 1.00 | 27.57 | B | C |
| ATOM | 2424 | CG | TYR | B | 263 | 63.698 | 18.867 | 33.497 | 1.00 | 25.16 | B | C |
| ATOM | 2425 | CD1 | TYR | B | 263 | 64.040 | 19.133 | 34.826 | 1.00 | 23.59 | B | C |
| ATOM | 2426 | CE1 | TYR | B | 263 | 64.682 | 18.182 | 35.608 | 1.00 | 23.22 | B | C |
| ATOM | 2427 | CD2 | TYR | B | 263 | 64.031 | 17.613 | 32.966 | 1.00 | 24.93 | B | C |
| ATOM | 2428 | CE2 | TYR | B | 263 | 64.678 | 16.645 | 33.745 | 1.00 | 23.43 | B | C |
| ATOM | 2429 | CZ | TYR | B | 263 | 64.993 | 16.942 | 35.062 | 1.00 | 22.91 | B | C |
| ATOM | 2430 | OH | TYR | B | 263 | 65.585 | 15.985 | 35.843 | 1.00 | 24.64 | B | O |
| ATOM | 2431 | C | TYR | B | 263 | 60.641 | 20.916 | 32.293 | 1.00 | 30.73 | B | C |
| ATOM | 2432 | O | TYR | B | 263 | 60.470 | 21.010 | 31.081 | 1.00 | 31.22 | B | O |
| ATOM | 2433 | N | TYR | B | 264 | 60.136 | 21.770 | 33.174 | 1.00 | 32.93 | B | N |
| ATOM | 2434 | CA | TYR | B | 264 | 59.362 | 22.946 | 32.803 | 1.00 | 36.10 | B | C |
| ATOM | 2435 | CB | TYR | B | 264 | 58.146 | 23.063 | 33.737 | 1.00 | 35.76 | B | C |
| ATOM | 2436 | CG | TYR | B | 264 | 57.178 | 24.172 | 33.403 | 1.00 | 35.57 | B | C |
| ATOM | 2437 | CD1 | TYR | B | 264 | 56.723 | 24.366 | 32.092 | 1.00 | 35.13 | B | C |
| ATOM | 2438 | CE1 | TYR | B | 264 | 55.850 | 25.400 | 31.781 | 1.00 | 34.83 | B | C |
| ATOM | 2439 | CD2 | TYR | B | 264 | 56.727 | 25.040 | 34.396 | 1.00 | 35.70 | B | C |
| ATOM | 2440 | CE2 | TYR | B | 264 | 55.852 | 26.076 | 34.094 | 1.00 | 36.52 | B | C |
| ATOM | 2441 | CZ | TYR | B | 264 | 55.419 | 26.251 | 32.786 | 1.00 | 35.76 | B | C |
| ATOM | 2442 | OH | TYR | B | 264 | 54.573 | 27.294 | 32.502 | 1.00 | 35.63 | B | O |
| ATOM | 2443 | C | TYR | B | 264 | 60.273 | 24.166 | 32.916 | 1.00 | 38.16 | B | C |
| ATOM | 2444 | O | TYR | B | 264 | 60.749 | 24.498 | 34.003 | 1.00 | 38.58 | B | O |
| ATOM | 2445 | N | ASN | B | 265 | 60.510 | 24.823 | 31.781 | 1.00 | 40.61 | B | N |
| ATOM | 2446 | CA | ASN | B | 265 | 61.400 | 25.978 | 31.711 | 1.00 | 42.82 | B | C |
| ATOM | 2447 | CB | ASN | B | 265 | 60.955 | 27.090 | 32.664 | 1.00 | 42.76 | B | C |
| ATOM | 2448 | CG | ASN | B | 265 | 59.625 | 27.704 | 32.264 | 1.00 | 42.69 | B | C |
| ATOM | 2449 | OD1 | ASN | B | 265 | 59.270 | 27.752 | 31.084 | 1.00 | 41.57 | B | O |
| ATOM | 2450 | ND2 | ASN | B | 265 | 58.885 | 28.180 | 33.251 | 1.00 | 42.52 | B | N |
| ATOM | 2451 | C | ASN | B | 265 | 62.831 | 25.541 | 32.030 | 1.00 | 44.49 | B | C |
| ATOM | 2452 | O | ASN | B | 265 | 63.518 | 26.169 | 32.837 | 1.00 | 44.67 | B | O |
| ATOM | 2453 | N | GLY | B | 266 | 63.233 | 24.411 | 31.444 | 1.00 | 46.21 | B | N |
| ATOM | 2454 | CA | GLY | B | 266 | 64.573 | 23.882 | 31.633 | 1.00 | 47.23 | B | C |
| ATOM | 2455 | C | GLY | B | 266 | 64.973 | 23.296 | 32.981 | 1.00 | 47.91 | B | C |
| ATOM | 2456 | O | GLY | B | 266 | 65.681 | 22.277 | 33.016 | 1.00 | 48.44 | B | O |
| ATOM | 2457 | N | HIS | B | 267 | 64.507 | 23.885 | 34.084 | 1.00 | 48.14 | B | N |
| ATOM | 2458 | CA | HIS | B | 267 | 64.908 | 23.393 | 35.403 | 1.00 | 48.77 | B | C |
| ATOM | 2459 | CB | HIS | B | 267 | 65.855 | 24.408 | 36.070 | 1.00 | 53.36 | B | C |
| ATOM | 2460 | CG | HIS | B | 267 | 67.193 | 24.505 | 35.392 | 1.00 | 58.69 | B | C |
| ATOM | 2461 | CD2 | HIS | B | 267 | 68.160 | 23.571 | 35.195 | 1.00 | 60.48 | B | C |
| ATOM | 2462 | ND1 | HIS | B | 267 | 67.641 | 25.653 | 34.769 | 1.00 | 59.77 | B | N |
| ATOM | 2463 | CE1 | HIS | B | 267 | 68.821 | 25.422 | 34.216 | 1.00 | 61.08 | B | C |
| ATOM | 2464 | NE2 | HIS | B | 267 | 69.158 | 24.167 | 34.460 | 1.00 | 61.46 | B | N |
| ATOM | 2465 | C | HIS | B | 267 | 63.884 | 22.843 | 36.411 | 1.00 | 46.06 | B | C |

Figure 9

| ATOM | 2466 | O | HIS | B | 267 | 64.270 | 22.132 | 37.341 | 1.00 | 46.21 | B | O |
|------|------|-----|-----|---|-----|--------|--------|--------|------|-------|---|---|
| ATOM | 2467 | N | THR | B | 268 | 62.598 | 23.134 | 36.232 | 1.00 | 42.64 | B | N |
| ATOM | 2468 | CA | THR | B | 268 | 61.572 | 22.626 | 37.151 | 1.00 | 38.53 | B | C |
| ATOM | 2469 | CB | THR | B | 268 | 60.317 | 23.522 | 37.144 | 1.00 | 39.68 | B | C |
| ATOM | 2470 | OG1 | THR | B | 268 | 60.701 | 24.874 | 37.428 | 1.00 | 41.54 | B | O |
| ATOM | 2471 | CG2 | THR | B | 268 | 59.307 | 23.049 | 38.186 | 1.00 | 38.28 | B | C |
| ATOM | 2472 | C | THR | B | 268 | 61.156 | 21.213 | 36.763 | 1.00 | 34.98 | B | C |
| ATOM | 2473 | O | THR | B | 268 | 60.674 | 20.989 | 35.664 | 1.00 | 34.28 | B | O |
| ATOM | 2474 | N | LYS | B | 269 | 61.360 | 20.255 | 37.661 | 1.00 | 32.23 | B | N |
| ATOM | 2475 | CA | LYS | B | 269 | 60.991 | 18.865 | 37.392 | 1.00 | 29.66 | B | C |
| ATOM | 2476 | CB | LYS | B | 269 | 61.693 | 17.937 | 38.377 | 1.00 | 28.41 | B | C |
| ATOM | 2477 | CG | LYS | B | 269 | 61.757 | 16.504 | 37.938 | 1.00 | 26.00 | B | C |
| ATOM | 2478 | CD | LYS | B | 269 | 62.653 | 15.727 | 38.866 | 1.00 | 26.10 | B | C |
| ATOM | 2479 | CE | LYS | B | 269 | 63.201 | 14.514 | 38.165 | 1.00 | 26.45 | B | C |
| ATOM | 2480 | NZ | LYS | B | 269 | 64.114 | 13.737 | 39.028 | 1.00 | 28.31 | B | N |
| ATOM | 2481 | C | LYS | B | 269 | 59.459 | 18.752 | 37.515 | 1.00 | 28.98 | B | C |
| ATOM | 2482 | O | LYS | B | 269 | 58.868 | 19.164 | 38.526 | 1.00 | 28.63 | B | O |
| ATOM | 2483 | N | VAL | B | 270 | 58.828 | 18.213 | 36.476 | 1.00 | 27.45 | B | N |
| ATOM | 2484 | CA | VAL | B | 270 | 57.373 | 18.101 | 36.426 | 1.00 | 24.96 | B | C |
| ATOM | 2485 | CB | VAL | B | 270 | 56.765 | 19.209 | 35.491 | 1.00 | 23.72 | B | C |
| ATOM | 2486 | CG1 | VAL | B | 270 | 57.062 | 20.607 | 36.015 | 1.00 | 21.44 | B | C |
| ATOM | 2487 | CG2 | VAL | B | 270 | 57.271 | 19.054 | 34.070 | 1.00 | 22.14 | B | C |
| ATOM | 2488 | C | VAL | B | 270 | 56.852 | 16.752 | 35.926 | 1.00 | 24.95 | B | C |
| ATOM | 2489 | O | VAL | B | 270 | 57.604 | 15.930 | 35.405 | 1.00 | 23.75 | B | O |
| ATOM | 2490 | N | ALA | B | 271 | 55.563 | 16.506 | 36.175 | 1.00 | 24.96 | B | N |
| ATOM | 2491 | CA | ALA | B | 271 | 54.887 | 15.316 | 35.679 | 1.00 | 24.79 | B | C |
| ATOM | 2492 | CB | ALA | B | 271 | 54.027 | 14.678 | 36.755 | 1.00 | 23.54 | B | C |
| ATOM | 2493 | C | ALA | B | 271 | 54.018 | 15.875 | 34.547 | 1.00 | 25.02 | B | C |
| ATOM | 2494 | O | ALA | B | 271 | 53.515 | 17.004 | 34.631 | 1.00 | 25.92 | B | O |
| ATOM | 2495 | N | VAL | B | 272 | 53.911 | 15.138 | 33.454 | 1.00 | 24.93 | B | N |
| ATOM | 2496 | CA | VAL | B | 272 | 53.121 | 15.609 | 32.330 | 1.00 | 25.06 | B | C |
| ATOM | 2497 | CB | VAL | B | 272 | 54.004 | 15.955 | 31.078 | 1.00 | 25.12 | B | C |
| ATOM | 2498 | CG1 | VAL | B | 272 | 53.152 | 16.658 | 30.010 | 1.00 | 23.91 | B | C |
| ATOM | 2499 | CG2 | VAL | B | 272 | 55.186 | 16.839 | 31.462 | 1.00 | 23.80 | B | C |
| ATOM | 2500 | C | VAL | B | 272 | 52.134 | 14.529 | 31.953 | 1.00 | 25.12 | B | C |
| ATOM | 2501 | O | VAL | B | 272 | 52.511 | 13.383 | 31.702 | 1.00 | 25.06 | B | O |
| ATOM | 2502 | N | LYS | B | 273 | 50.857 | 14.887 | 31.955 | 1.00 | 25.92 | B | N |
| ATOM | 2503 | CA | LYS | B | 273 | 49.813 | 13.951 | 31.579 | 1.00 | 26.61 | B | C |
| ATOM | 2504 | CB | LYS | B | 273 | 48.617 | 14.139 | 32.505 | 1.00 | 27.50 | B | C |
| ATOM | 2505 | CG | LYS | B | 273 | 47.920 | 12.855 | 32.846 | 1.00 | 29.99 | B | C |
| ATOM | 2506 | CD | LYS | B | 273 | 46.881 | 13.081 | 33.915 | 1.00 | 30.78 | B | C |
| ATOM | 2507 | CE | LYS | B | 273 | 46.798 | 11.862 | 34.780 | 1.00 | 31.99 | B | C |
| ATOM | 2508 | NZ | LYS | B | 273 | 45.619 | 11.904 | 35.676 | 1.00 | 32.68 | B | N |
| ATOM | 2509 | C | LYS | B | 273 | 49.434 | 14.268 | 30.125 | 1.00 | 26.76 | B | C |
| ATOM | 2510 | O | LYS | B | 273 | 49.164 | 15.416 | 29.800 | 1.00 | 25.91 | B | O |
| ATOM | 2511 | N | SER | B | 274 | 49.482 | 13.276 | 29.243 | 1.00 | 28.31 | B | N |
| ATOM | 2512 | CA | SER | B | 274 | 49.132 | 13.500 | 27.836 | 1.00 | 30.74 | B | C |
| ATOM | 2513 | CB | SER | B | 274 | 50.323 | 13.223 | 26.904 | 1.00 | 30.23 | B | C |
| ATOM | 2514 | OG | SER | B | 274 | 50.651 | 11.847 | 26.894 | 1.00 | 32.44 | B | O |
| ATOM | 2515 | C | SER | B | 274 | 47.936 | 12.645 | 27.419 | 1.00 | 31.74 | B | C |
| ATOM | 2516 | O | SER | B | 274 | 47.806 | 11.483 | 27.830 | 1.00 | 32.77 | B | O |
| ATOM | 2517 | N | LEU | B | 275 | 47.094 | 13.213 | 26.561 | 1.00 | 31.56 | B | N |
| ATOM | 2518 | CA | LEU | B | 275 | 45.897 | 12.527 | 26.099 | 1.00 | 30.84 | B | C |
| ATOM | 2519 | CB | LEU | B | 275 | 44.803 | 13.560 | 25.825 | 1.00 | 29.51 | B | C |
| ATOM | 2520 | CG | LEU | B | 275 | 43.458 | 13.051 | 25.287 | 1.00 | 28.99 | B | C |
| ATOM | 2521 | CD1 | LEU | B | 275 | 42.783 | 12.143 | 26.306 | 1.00 | 26.71 | B | C |
| ATOM | 2522 | CD2 | LEU | B | 275 | 42.569 | 14.243 | 24.938 | 1.00 | 28.73 | B | C |
| ATOM | 2523 | C | LEU | B | 275 | 46.057 | 11.640 | 24.864 | 1.00 | 31.54 | B | C |
| ATOM | 2524 | O | LEU | B | 275 | 46.514 | 12.102 | 23.821 | 1.00 | 31.38 | B | O |

Figure 9

| | | | | | | | | | | | |
|---|---|---|---|---|---|---|---|---|---|---|---|
| ATOM | 2525 | N | LYS | B | 276 | 45.695 | 10.365 | 24.987 | 1.00 | 32.44 | B | N |
| ATOM | 2526 | CA | LYS | B | 276 | 45.725 | 9.471 | 23.838 | 1.00 | 34.28 | B | C |
| ATOM | 2527 | CB | LYS | B | 276 | 45.529 | 8.017 | 24.264 | 1.00 | 33.13 | B | C |
| ATOM | 2528 | CG | LYS | B | 276 | 45.339 | 7.045 | 23.096 | 1.00 | 34.49 | B | C |
| ATOM | 2529 | CD | LYS | B | 276 | 45.082 | 5.605 | 23.573 | 1.00 | 37.14 | B | C |
| ATOM | 2530 | CE | LYS | B | 276 | 46.214 | 5.109 | 24.484 | 1.00 | 39.39 | B | C |
| ATOM | 2531 | NZ | LYS | B | 276 | 46.070 | 3.704 | 24.986 | 1.00 | 40.05 | B | N |
| ATOM | 2532 | C | LYS | B | 276 | 44.500 | 9.946 | 23.056 | 1.00 | 36.66 | B | C |
| ATOM | 2533 | O | LYS | B | 276 | 43.382 | 9.892 | 23.570 | 1.00 | 37.28 | B | O |
| ATOM | 2534 | N | GLN | B | 277 | 44.711 | 10.487 | 21.860 | 1.00 | 38.47 | B | N |
| ATOM | 2535 | CA | GLN | B | 277 | 43.608 | 10.992 | 21.046 | 1.00 | 40.06 | B | C |
| ATOM | 2536 | CB | GLN | B | 277 | 44.124 | 11.446 | 19.688 | 1.00 | 43.65 | B | C |
| ATOM | 2537 | CG | GLN | B | 277 | 43.042 | 11.955 | 18.753 | 1.00 | 49.13 | B | C |
| ATOM | 2538 | CD | GLN | B | 277 | 43.566 | 12.196 | 17.357 | 1.00 | 53.12 | B | C |
| ATOM | 2539 | OE1 | GLN | B | 277 | 44.613 | 11.655 | 16.969 | 1.00 | 54.85 | B | O |
| ATOM | 2540 | NE2 | GLN | B | 277 | 42.847 | 13.002 | 16.584 | 1.00 | 55.37 | B | N |
| ATOM | 2541 | C | GLN | B | 277 | 42.472 | 9.987 | 20.859 | 1.00 | 39.10 | B | C |
| ATOM | 2542 | O | GLN | B | 277 | 42.705 | 8.814 | 20.562 | 1.00 | 38.17 | B | O |
| ATOM | 2543 | N | GLY | B | 278 | 41.248 | 10.451 | 21.081 | 1.00 | 38.74 | B | N |
| ATOM | 2544 | CA | GLY | B | 278 | 40.104 | 9.580 | 20.926 | 1.00 | 38.67 | B | C |
| ATOM | 2545 | C | GLY | B | 278 | 39.551 | 9.034 | 22.230 | 1.00 | 38.95 | B | C |
| ATOM | 2546 | O | GLY | B | 278 | 38.380 | 8.652 | 22.290 | 1.00 | 40.16 | B | O |
| ATOM | 2547 | N | SER | B | 279 | 40.383 | 8.970 | 23.264 | 1.00 | 37.86 | B | N |
| ATOM | 2548 | CA | SER | B | 279 | 39.950 | 8.467 | 24.569 | 1.00 | 37.52 | B | C |
| ATOM | 2549 | CB | SER | B | 279 | 41.111 | 8.518 | 25.566 | 1.00 | 37.65 | B | C |
| ATOM | 2550 | OG | SER | B | 279 | 42.132 | 7.630 | 25.168 | 1.00 | 38.16 | B | O |
| ATOM | 2551 | C | SER | B | 279 | 38.786 | 9.293 | 25.100 | 1.00 | 36.27 | B | C |
| ATOM | 2552 | O | SER | B | 279 | 37.816 | 8.760 | 25.656 | 1.00 | 36.28 | B | O |
| ATOM | 2553 | N | MET | B | 280 | 38.927 | 10.605 | 24.940 | 1.00 | 34.66 | B | N |
| ATOM | 2554 | CA | MET | B | 280 | 37.926 | 11.581 | 25.349 | 1.00 | 33.28 | B | C |
| ATOM | 2555 | CB | MET | B | 280 | 37.955 | 11.814 | 26.875 | 1.00 | 33.28 | B | C |
| ATOM | 2556 | CG | MET | B | 280 | 39.133 | 12.639 | 27.413 | 1.00 | 31.82 | B | C |
| ATOM | 2557 | SD | MET | B | 280 | 39.371 | 12.466 | 29.206 | 1.00 | 30.03 | B | S |
| ATOM | 2558 | CE | MET | B | 280 | 38.225 | 13.529 | 29.778 | 1.00 | 32.18 | B | C |
| ATOM | 2559 | C | MET | B | 280 | 38.254 | 12.860 | 24.579 | 1.00 | 32.56 | B | C |
| ATOM | 2560 | O | MET | B | 280 | 39.347 | 12.980 | 24.007 | 1.00 | 32.68 | B | O |
| ATOM | 2561 | N | SER | B | 281 | 37.302 | 13.788 | 24.527 | 1.00 | 31.42 | B | N |
| ATOM | 2562 | CA | SER | B | 281 | 37.504 | 15.035 | 23.807 | 1.00 | 29.77 | B | C |
| ATOM | 2563 | CB | SER | B | 281 | 36.180 | 15.799 | 23.651 | 1.00 | 28.29 | B | C |
| ATOM | 2564 | OG | SER | B | 281 | 35.905 | 16.623 | 24.770 | 1.00 | 25.29 | B | O |
| ATOM | 2565 | C | SER | B | 281 | 38.516 | 15.927 | 24.514 | 1.00 | 30.71 | B | C |
| ATOM | 2566 | O | SER | B | 281 | 38.681 | 15.867 | 25.736 | 1.00 | 30.09 | B | O |
| ATOM | 2567 | N | PRO | B | 282 | 39.249 | 16.738 | 23.728 | 1.00 | 31.11 | B | N |
| ATOM | 2568 | CD | PRO | B | 282 | 39.345 | 16.703 | 22.261 | 1.00 | 30.59 | B | C |
| ATOM | 2569 | CA | PRO | B | 282 | 40.251 | 17.650 | 24.295 | 1.00 | 31.00 | B | C |
| ATOM | 2570 | CB | PRO | B | 282 | 40.715 | 18.427 | 23.069 | 1.00 | 30.45 | B | C |
| ATOM | 2571 | CG | PRO | B | 282 | 40.685 | 17.380 | 22.009 | 1.00 | 30.09 | B | C |
| ATOM | 2572 | C | PRO | B | 282 | 39.648 | 18.571 | 25.350 | 1.00 | 31.21 | B | C |
| ATOM | 2573 | O | PRO | B | 282 | 40.250 | 18.784 | 26.393 | 1.00 | 31.55 | B | O |
| ATOM | 2574 | N | ASP | B | 283 | 38.453 | 19.106 | 25.087 | 1.00 | 31.64 | B | N |
| ATOM | 2575 | CA | ASP | B | 283 | 37.786 | 20.004 | 26.029 | 1.00 | 31.86 | B | C |
| ATOM | 2576 | CB | ASP | B | 283 | 36.490 | 20.579 | 25.426 | 1.00 | 34.05 | B | C |
| ATOM | 2577 | CG | ASP | B | 283 | 36.749 | 21.733 | 24.435 | 1.00 | 36.94 | B | C |
| ATOM | 2578 | OD1 | ASP | B | 283 | 37.924 | 22.112 | 24.246 | 1.00 | 39.48 | B | O |
| ATOM | 2579 | OD2 | ASP | B | 283 | 35.787 | 22.272 | 23.847 | 1.00 | 38.07 | B | O |
| ATOM | 2580 | C | ASP | B | 283 | 37.511 | 19.358 | 27.386 | 1.00 | 30.96 | B | C |
| ATOM | 2581 | O | ASP | B | 283 | 37.636 | 20.011 | 28.416 | 1.00 | 30.80 | B | O |
| ATOM | 2582 | N | ALA | B | 284 | 37.142 | 18.081 | 27.386 | 1.00 | 30.51 | B | N |
| ATOM | 2583 | CA | ALA | B | 284 | 36.876 | 17.353 | 28.626 | 1.00 | 29.89 | B | C |

Figure 9

| | | | | | | | | | | | |
|---|---|---|---|---|---|---|---|---|---|---|---|
| ATOM | 2584 | CB | ALA | B | 284 | 36.218 | 16.016 | 28.312 | 1.00 | 27.44 | B C |
| ATOM | 2585 | C | ALA | B | 284 | 38.176 | 17.128 | 29.427 | 1.00 | 30.02 | B C |
| ATOM | 2586 | O | ALA | B | 284 | 38.191 | 17.279 | 30.658 | 1.00 | 29.96 | B O |
| ATOM | 2587 | N | PHE | B | 285 | 39.246 | 16.743 | 28.718 | 1.00 | 29.71 | B N |
| ATOM | 2588 | CA | PHE | B | 285 | 40.570 | 16.489 | 29.313 | 1.00 | 29.30 | B C |
| ATOM | 2589 | CB | PHE | B | 285 | 41.548 | 15.995 | 28.233 | 1.00 | 30.08 | B C |
| ATOM | 2590 | CG | PHE | B | 285 | 42.924 | 15.613 | 28.753 | 1.00 | 30.46 | B C |
| ATOM | 2591 | CD1 | PHE | B | 285 | 43.117 | 14.431 | 29.476 | 1.00 | 30.87 | B C |
| ATOM | 2592 | CD2 | PHE | B | 285 | 44.031 | 16.411 | 28.475 | 1.00 | 30.12 | B C |
| ATOM | 2593 | CE1 | PHE | B | 285 | 44.391 | 14.049 | 29.909 | 1.00 | 30.58 | B C |
| ATOM | 2594 | CE2 | PHE | B | 285 | 45.309 | 16.035 | 28.904 | 1.00 | 30.23 | B C |
| ATOM | 2595 | CZ | PHE | B | 285 | 45.486 | 14.853 | 29.621 | 1.00 | 30.21 | B C |
| ATOM | 2596 | C | PHE | B | 285 | 41.116 | 17.751 | 29.969 | 1.00 | 28.50 | B C |
| ATOM | 2597 | O | PHE | B | 285 | 41.579 | 17.714 | 31.105 | 1.00 | 28.31 | B O |
| ATOM | 2598 | N | LEU | B | 286 | 41.040 | 18.867 | 29.252 | 1.00 | 28.56 | B N |
| ATOM | 2599 | CA | LEU | B | 286 | 41.507 | 20.146 | 29.762 | 1.00 | 29.44 | B C |
| ATOM | 2600 | CB | LEU | B | 286 | 41.575 | 21.181 | 28.635 | 1.00 | 30.24 | B C |
| ATOM | 2601 | CG | LEU | B | 286 | 42.732 | 21.034 | 27.628 | 1.00 | 31.05 | B C |
| ATOM | 2602 | CD1 | LEU | B | 286 | 42.525 | 21.941 | 26.414 | 1.00 | 29.86 | B C |
| ATOM | 2603 | CD2 | LEU | B | 286 | 44.054 | 21.351 | 28.320 | 1.00 | 29.36 | B C |
| ATOM | 2604 | C | LEU | B | 286 | 40.604 | 20.649 | 30.872 | 1.00 | 30.53 | B C |
| ATOM | 2605 | O | LEU | B | 286 | 41.042 | 21.409 | 31.736 | 1.00 | 30.10 | B O |
| ATOM | 2606 | N | ALA | B | 287 | 39.337 | 20.225 | 30.832 | 1.00 | 32.28 | B N |
| ATOM | 2607 | CA | ALA | B | 287 | 38.336 | 20.611 | 31.830 | 1.00 | 33.22 | B C |
| ATOM | 2608 | CB | ALA | B | 287 | 36.937 | 20.230 | 31.364 | 1.00 | 32.63 | B C |
| ATOM | 2609 | C | ALA | B | 287 | 38.646 | 19.968 | 33.180 | 1.00 | 34.08 | B C |
| ATOM | 2610 | O | ALA | B | 287 | 38.418 | 20.583 | 34.228 | 1.00 | 34.56 | B O |
| ATOM | 2611 | N | GLU | B | 288 | 39.165 | 18.736 | 33.147 | 1.00 | 34.20 | B N |
| ATOM | 2612 | CA | GLU | B | 288 | 39.551 | 18.020 | 34.365 | 1.00 | 35.20 | B C |
| ATOM | 2613 | CB | GLU | B | 288 | 40.019 | 16.596 | 34.061 | 1.00 | 35.99 | B C |
| ATOM | 2614 | CG | GLU | B | 288 | 38.936 | 15.651 | 33.567 | 1.00 | 37.93 | B C |
| ATOM | 2615 | CD | GLU | B | 288 | 39.412 | 14.203 | 33.451 | 1.00 | 40.15 | B C |
| ATOM | 2616 | OE1 | GLU | B | 288 | 40.643 | 13.955 | 33.462 | 1.00 | 41.10 | B O |
| ATOM | 2617 | OE2 | GLU | B | 288 | 38.543 | 13.303 | 33.356 | 1.00 | 41.28 | B O |
| ATOM | 2618 | C | GLU | B | 288 | 40.690 | 18.770 | 35.052 | 1.00 | 35.32 | B C |
| ATOM | 2619 | O | GLU | B | 288 | 40.792 | 18.752 | 36.269 | 1.00 | 35.91 | B O |
| ATOM | 2620 | N | ALA | B | 289 | 41.534 | 19.434 | 34.264 | 1.00 | 35.48 | B N |
| ATOM | 2621 | CA | ALA | B | 289 | 42.654 | 20.201 | 34.794 | 1.00 | 35.15 | B C |
| ATOM | 2622 | CB | ALA | B | 289 | 43.696 | 20.441 | 33.717 | 1.00 | 35.85 | B C |
| ATOM | 2623 | C | ALA | B | 289 | 42.216 | 21.525 | 35.389 | 1.00 | 35.16 | B C |
| ATOM | 2624 | O | ALA | B | 289 | 42.989 | 22.147 | 36.112 | 1.00 | 35.24 | B O |
| ATOM | 2625 | N | ASN | B | 290 | 41.008 | 21.984 | 35.052 | 1.00 | 35.07 | B N |
| ATOM | 2626 | CA | ASN | B | 290 | 40.474 | 23.234 | 35.612 | 1.00 | 35.54 | B C |
| ATOM | 2627 | CB | ASN | B | 290 | 39.139 | 23.613 | 34.951 | 1.00 | 38.38 | B C |
| ATOM | 2628 | CG | ASN | B | 290 | 39.297 | 24.137 | 33.542 | 1.00 | 40.64 | B C |
| ATOM | 2629 | OD1 | ASN | B | 290 | 38.360 | 24.058 | 32.738 | 1.00 | 42.05 | B O |
| ATOM | 2630 | ND2 | ASN | B | 290 | 40.462 | 24.708 | 33.236 | 1.00 | 40.76 | B N |
| ATOM | 2631 | C | ASN | B | 290 | 40.246 | 23.064 | 37.119 | 1.00 | 34.33 | B C |
| ATOM | 2632 | O | ASN | B | 290 | 40.218 | 24.035 | 37.868 | 1.00 | 33.24 | B O |
| ATOM | 2633 | N | LEU | B | 291 | 40.030 | 21.815 | 37.526 | 1.00 | 33.60 | B N |
| ATOM | 2634 | CA | LEU | B | 291 | 39.814 | 21.473 | 38.928 | 1.00 | 33.21 | B C |
| ATOM | 2635 | CB | LEU | B | 291 | 39.474 | 19.984 | 39.055 | 1.00 | 32.87 | B C |
| ATOM | 2636 | CG | LEU | B | 291 | 38.137 | 19.683 | 38.377 | 1.00 | 33.66 | B C |
| ATOM | 2637 | CD1 | LEU | B | 291 | 37.893 | 18.201 | 38.268 | 1.00 | 32.55 | B C |
| ATOM | 2638 | CD2 | LEU | B | 291 | 37.009 | 20.371 | 39.125 | 1.00 | 33.78 | B C |
| ATOM | 2639 | C | LEU | B | 291 | 41.028 | 21.866 | 39.788 | 1.00 | 32.98 | B C |
| ATOM | 2640 | O | LEU | B | 291 | 40.827 | 22.345 | 40.915 | 1.00 | 32.67 | B O |
| ATOM | 2641 | N | MET | B | 292 | 42.239 | 21.721 | 39.244 | 1.00 | 32.86 | B N |
| ATOM | 2642 | CA | MET | B | 292 | 43.453 | 22.114 | 39.977 | 1.00 | 32.55 | B C |

Figure 9

| ATOM | 2643 | CB | MET B 292 | 44.713 | 21.536 | 39.340 | 1.00 | 30.76 | B | C |
|------|------|-----|-----------|--------|--------|--------|------|-------|---|---|
| ATOM | 2644 | CG | MET B 292 | 44.892 | 20.078 | 39.601 | 1.00 | 29.27 | B | C |
| ATOM | 2645 | SD | MET B 292 | 46.472 | 19.538 | 38.962 | 1.00 | 26.76 | B | S |
| ATOM | 2646 | CE | MET B 292 | 46.127 | 19.694 | 37.243 | 1.00 | 29.26 | B | C |
| ATOM | 2647 | C | MET B 292 | 43.577 | 23.641 | 40.077 | 1.00 | 33.84 | B | C |
| ATOM | 2648 | O | MET B 292 | 44.165 | 24.137 | 41.027 | 1.00 | 33.71 | B | O |
| ATOM | 2649 | N | LYS B 293 | 43.027 | 24.358 | 39.112 | 1.00 | 35.94 | B | N |
| ATOM | 2650 | CA | LYS B 293 | 43.062 | 25.826 | 39.106 | 1.00 | 38.06 | B | C |
| ATOM | 2651 | CB | LYS B 293 | 42.551 | 26.396 | 37.780 | 1.00 | 38.18 | B | C |
| ATOM | 2652 | CG | LYS B 293 | 43.263 | 25.924 | 36.542 | 1.00 | 40.34 | B | C |
| ATOM | 2653 | CD | LYS B 293 | 42.668 | 26.605 | 35.298 | 1.00 | 41.84 | B | C |
| ATOM | 2654 | CE | LYS B 293 | 43.330 | 26.130 | 34.006 | 1.00 | 42.42 | B | C |
| ATOM | 2655 | NZ | LYS B 293 | 42.762 | 26.855 | 32.835 | 1.00 | 44.04 | B | N |
| ATOM | 2656 | C | LYS B 293 | 42.135 | 26.323 | 40.237 | 1.00 | 39.74 | B | C |
| ATOM | 2657 | O | LYS B 293 | 42.486 | 27.211 | 41.019 | 1.00 | 40.47 | B | O |
| ATOM | 2658 | N | GLN B 294 | 40.950 | 25.721 | 40.324 | 1.00 | 41.05 | B | N |
| ATOM | 2659 | CA | GLN B 294 | 39.943 | 26.103 | 41.315 | 1.00 | 42.57 | B | C |
| ATOM | 2660 | CB | GLN B 294 | 38.564 | 25.551 | 40.904 | 1.00 | 45.80 | B | C |
| ATOM | 2661 | CG | GLN B 294 | 38.078 | 25.933 | 39.479 | 1.00 | 51.68 | B | C |
| ATOM | 2662 | CD | GLN B 294 | 38.176 | 27.442 | 39.146 | 1.00 | 56.04 | B | C |
| ATOM | 2663 | OE1 | GLN B 294 | 38.785 | 27.829 | 38.131 | 1.00 | 57.21 | B | O |
| ATOM | 2664 | NE2 | GLN B 294 | 37.547 | 28.289 | 39.973 | 1.00 | 56.60 | B | N |
| ATOM | 2665 | C | GLN B 294 | 40.267 | 25.718 | 42.776 | 1.00 | 41.42 | B | C |
| ATOM | 2666 | O | GLN B 294 | 39.799 | 26.376 | 43.704 | 1.00 | 41.87 | B | O |
| ATOM | 2667 | N | LEU B 295 | 41.054 | 24.658 | 42.974 | 1.00 | 39.51 | B | N |
| ATOM | 2668 | CA | LEU B 295 | 41.421 | 24.213 | 44.337 | 1.00 | 36.77 | B | C |
| ATOM | 2669 | CB | LEU B 295 | 40.810 | 22.832 | 44.624 | 1.00 | 36.26 | B | C |
| ATOM | 2670 | CG | LEU B 295 | 39.296 | 22.672 | 44.655 | 1.00 | 34.83 | B | C |
| ATOM | 2671 | CD1 | LEU B 295 | 38.931 | 21.205 | 44.828 | 1.00 | 33.74 | B | C |
| ATOM | 2672 | CD2 | LEU B 295 | 38.722 | 23.497 | 45.792 | 1.00 | 35.11 | B | C |
| ATOM | 2673 | C | LEU B 295 | 42.935 | 24.128 | 44.519 | 1.00 | 35.18 | B | C |
| ATOM | 2674 | O | LEU B 295 | 43.556 | 23.153 | 44.091 | 1.00 | 34.49 | B | O |
| ATOM | 2675 | N | GLN B 296 | 43.521 | 25.131 | 45.170 | 1.00 | 34.01 | B | N |
| ATOM | 2676 | CA | GLN B 296 | 44.969 | 25.156 | 45.403 | 1.00 | 32.63 | B | C |
| ATOM | 2677 | CB | GLN B 296 | 45.575 | 26.444 | 44.861 | 1.00 | 33.48 | B | C |
| ATOM | 2678 | CG | GLN B 296 | 45.230 | 26.731 | 43.424 | 1.00 | 35.63 | B | C |
| ATOM | 2679 | CD | GLN B 296 | 45.851 | 28.021 | 42.945 | 1.00 | 37.32 | B | C |
| ATOM | 2680 | OE1 | GLN B 296 | 46.492 | 28.744 | 43.720 | 1.00 | 39.13 | B | O |
| ATOM | 2681 | NE2 | GLN B 296 | 45.696 | 28.312 | 41.661 | 1.00 | 37.65 | B | N |
| ATOM | 2682 | C | GLN B 296 | 45.297 | 25.037 | 46.882 | 1.00 | 31.37 | B | C |
| ATOM | 2683 | O | GLN B 296 | 44.849 | 25.846 | 47.694 | 1.00 | 30.69 | B | O |
| ATOM | 2684 | N | HIS B 297 | 46.162 | 24.079 | 47.196 | 1.00 | 30.10 | B | N |
| ATOM | 2685 | CA | HIS B 297 | 46.561 | 23.814 | 48.565 | 1.00 | 29.31 | B | C |
| ATOM | 2686 | CB | HIS B 297 | 45.437 | 23.044 | 49.251 | 1.00 | 27.21 | B | C |
| ATOM | 2687 | CG | HIS B 297 | 45.528 | 23.051 | 50.748 | 1.00 | 24.99 | B | C |
| ATOM | 2688 | CD2 | HIS B 297 | 45.009 | 23.897 | 51.663 | 1.00 | 22.26 | B | C |
| ATOM | 2689 | ND1 | HIS B 297 | 46.210 | 22.088 | 51.454 | 1.00 | 24.04 | B | N |
| ATOM | 2690 | CE1 | HIS B 297 | 46.107 | 22.341 | 52.743 | 1.00 | 23.02 | B | C |
| ATOM | 2691 | NE2 | HIS B 297 | 45.382 | 23.436 | 52.895 | 1.00 | 22.62 | B | N |
| ATOM | 2692 | C | HIS B 297 | 47.850 | 22.981 | 48.600 | 1.00 | 29.90 | B | C |
| ATOM | 2693 | O | HIS B 297 | 48.145 | 22.240 | 47.651 | 1.00 | 29.26 | B | O |
| ATOM | 2694 | N | GLN B 298 | 48.607 | 23.090 | 49.697 | 1.00 | 30.77 | B | N |
| ATOM | 2695 | CA | GLN B 298 | 49.853 | 22.333 | 49.841 | 1.00 | 31.84 | B | C |
| ATOM | 2696 | CB | GLN B 298 | 50.564 | 22.672 | 51.159 | 1.00 | 36.02 | B | C |
| ATOM | 2697 | CG | GLN B 298 | 51.423 | 23.942 | 51.134 | 1.00 | 43.20 | B | C |
| ATOM | 2698 | CD | GLN B 298 | 52.508 | 23.934 | 50.042 | 1.00 | 46.94 | B | C |
| ATOM | 2699 | OE1 | GLN B 298 | 52.696 | 24.933 | 49.329 | 1.00 | 48.72 | B | O |
| ATOM | 2700 | NE2 | GLN B 298 | 53.223 | 22.807 | 49.909 | 1.00 | 48.22 | B | N |
| ATOM | 2701 | C | GLN B 298 | 49.632 | 20.832 | 49.790 | 1.00 | 30.04 | B | C |

Figure 9

| | | | | | | | | | | | |
|---|---|---|---|---|---|---|---|---|---|---|---|
| ATOM | 2702 | O | GLN | B | 298 | 50.526 | 20.084 | 49.419 | 1.00 | 29.55 | B | O |
| ATOM | 2703 | N | ARG | B | 299 | 48.438 | 20.401 | 50.184 | 1.00 | 28.30 | B | N |
| ATOM | 2704 | CA | ARG | B | 299 | 48.086 | 18.984 | 50.220 | 1.00 | 26.67 | B | C |
| ATOM | 2705 | CB | ARG | B | 299 | 47.153 | 18.714 | 51.395 | 1.00 | 27.57 | B | C |
| ATOM | 2706 | CG | ARG | B | 299 | 47.819 | 18.936 | 52.712 | 1.00 | 29.79 | B | C |
| ATOM | 2707 | CD | ARG | B | 299 | 48.949 | 17.963 | 52.837 | 1.00 | 31.67 | B | C |
| ATOM | 2708 | NE | ARG | B | 299 | 50.000 | 18.483 | 53.692 | 1.00 | 35.80 | B | N |
| ATOM | 2709 | CZ | ARG | B | 299 | 51.291 | 18.446 | 53.379 | 1.00 | 35.89 | B | C |
| ATOM | 2710 | NH1 | ARG | B | 299 | 51.692 | 17.922 | 52.216 | 1.00 | 34.25 | B | N |
| ATOM | 2711 | NH2 | ARG | B | 299 | 52.178 | 18.869 | 54.268 | 1.00 | 35.97 | B | N |
| ATOM | 2712 | C | ARG | B | 299 | 47.471 | 18.430 | 48.949 | 1.00 | 24.95 | B | C |
| ATOM | 2713 | O | ARG | B | 299 | 47.134 | 17.253 | 48.883 | 1.00 | 24.36 | B | O |
| ATOM | 2714 | N | LEU | B | 300 | 47.313 | 19.292 | 47.956 | 1.00 | 23.78 | B | N |
| ATOM | 2715 | CA | LEU | B | 300 | 46.740 | 18.922 | 46.675 | 1.00 | 22.98 | B | C |
| ATOM | 2716 | CB | LEU | B | 300 | 45.478 | 19.757 | 46.390 | 1.00 | 21.22 | B | C |
| ATOM | 2717 | CG | LEU | B | 300 | 44.087 | 19.396 | 46.939 | 1.00 | 18.38 | B | C |
| ATOM | 2718 | CD1 | LEU | B | 300 | 44.100 | 19.049 | 48.397 | 1.00 | 16.12 | B | C |
| ATOM | 2719 | CD2 | LEU | B | 300 | 43.175 | 20.572 | 46.677 | 1.00 | 18.38 | B | C |
| ATOM | 2720 | C | LEU | B | 300 | 47.762 | 19.187 | 45.586 | 1.00 | 23.06 | B | C |
| ATOM | 2721 | O | LEU | B | 300 | 48.440 | 20.212 | 45.620 | 1.00 | 23.36 | B | O |
| ATOM | 2722 | N | VAL | B | 301 | 47.829 | 18.277 | 44.614 | 1.00 | 24.10 | B | N |
| ATOM | 2723 | CA | VAL | B | 301 | 48.732 | 18.378 | 43.461 | 1.00 | 24.83 | B | C |
| ATOM | 2724 | CB | VAL | B | 301 | 48.577 | 17.154 | 42.534 | 1.00 | 24.72 | B | C |
| ATOM | 2725 | CG1 | VAL | B | 301 | 49.282 | 17.376 | 41.198 | 1.00 | 25.27 | B | C |
| ATOM | 2726 | CG2 | VAL | B | 301 | 49.149 | 15.925 | 43.221 | 1.00 | 23.54 | B | C |
| ATOM | 2727 | C | VAL | B | 301 | 48.474 | 19.679 | 42.694 | 1.00 | 25.80 | B | C |
| ATOM | 2728 | O | VAL | B | 301 | 47.354 | 19.978 | 42.283 | 1.00 | 25.65 | B | O |
| ATOM | 2729 | N | ARG | B | 302 | 49.539 | 20.458 | 42.558 | 1.00 | 27.20 | B | N |
| ATOM | 2730 | CA | ARG | B | 302 | 49.529 | 21.763 | 41.908 | 1.00 | 28.35 | B | C |
| ATOM | 2731 | CB | ARG | B | 302 | 50.629 | 22.620 | 42.559 | 1.00 | 30.00 | B | C |
| ATOM | 2732 | CG | ARG | B | 302 | 50.803 | 24.031 | 42.052 | 1.00 | 33.86 | B | C |
| ATOM | 2733 | CD | ARG | B | 302 | 51.871 | 24.091 | 40.976 | 1.00 | 37.21 | B | C |
| ATOM | 2734 | NE | ARG | B | 302 | 52.380 | 25.444 | 40.742 | 1.00 | 40.15 | B | N |
| ATOM | 2735 | CZ | ARG | B | 302 | 53.332 | 26.019 | 41.471 | 1.00 | 40.97 | B | C |
| ATOM | 2736 | NH1 | ARG | B | 302 | 53.882 | 25.367 | 42.492 | 1.00 | 42.47 | B | N |
| ATOM | 2737 | NH2 | ARG | B | 302 | 53.767 | 27.229 | 41.156 | 1.00 | 41.25 | B | N |
| ATOM | 2738 | C | ARG | B | 302 | 49.687 | 21.696 | 40.386 | 1.00 | 28.07 | B | C |
| ATOM | 2739 | O | ARG | B | 302 | 50.441 | 20.878 | 39.846 | 1.00 | 27.12 | B | O |
| ATOM | 2740 | N | LEU | B | 303 | 48.936 | 22.551 | 39.706 | 1.00 | 28.35 | B | N |
| ATOM | 2741 | CA | LEU | B | 303 | 48.983 | 22.633 | 38.251 | 1.00 | 29.42 | B | C |
| ATOM | 2742 | CB | LEU | B | 303 | 47.584 | 22.890 | 37.673 | 1.00 | 28.11 | B | C |
| ATOM | 2743 | CG | LEU | B | 303 | 47.507 | 23.172 | 36.167 | 1.00 | 28.29 | B | C |
| ATOM | 2744 | CD1 | LEU | B | 303 | 47.882 | 21.939 | 35.358 | 1.00 | 27.44 | B | C |
| ATOM | 2745 | CD2 | LEU | B | 303 | 46.108 | 23.629 | 35.804 | 1.00 | 29.37 | B | C |
| ATOM | 2746 | C | LEU | B | 303 | 49.907 | 23.781 | 37.852 | 1.00 | 29.85 | B | C |
| ATOM | 2747 | O | LEU | B | 303 | 49.797 | 24.886 | 38.393 | 1.00 | 30.05 | B | O |
| ATOM | 2748 | N | TYR | B | 304 | 50.860 | 23.500 | 36.965 | 1.00 | 30.13 | B | N |
| ATOM | 2749 | CA | TYR | B | 304 | 51.760 | 24.541 | 36.486 | 1.00 | 31.00 | B | C |
| ATOM | 2750 | CB | TYR | B | 304 | 53.164 | 23.991 | 36.202 | 1.00 | 31.38 | B | C |
| ATOM | 2751 | CG | TYR | B | 304 | 54.022 | 23.769 | 37.425 | 1.00 | 31.64 | B | C |
| ATOM | 2752 | CD1 | TYR | B | 304 | 54.290 | 22.480 | 37.885 | 1.00 | 31.30 | B | C |
| ATOM | 2753 | CE1 | TYR | B | 304 | 55.100 | 22.257 | 38.995 | 1.00 | 30.79 | B | C |
| ATOM | 2754 | CD2 | TYR | B | 304 | 54.590 | 24.845 | 38.111 | 1.00 | 32.82 | B | C |
| ATOM | 2755 | CE2 | TYR | B | 304 | 55.414 | 24.628 | 39.234 | 1.00 | 32.72 | B | C |
| ATOM | 2756 | CZ | TYR | B | 304 | 55.657 | 23.328 | 39.660 | 1.00 | 31.97 | B | C |
| ATOM | 2757 | OH | TYR | B | 304 | 56.454 | 23.088 | 40.748 | 1.00 | 33.18 | B | O |
| ATOM | 2758 | C | TYR | B | 304 | 51.173 | 25.144 | 35.213 | 1.00 | 30.94 | B | C |
| ATOM | 2759 | O | TYR | B | 304 | 51.059 | 26.362 | 35.100 | 1.00 | 31.17 | B | O |
| ATOM | 2760 | N | ALA | B | 305 | 50.771 | 24.279 | 34.279 | 1.00 | 31.65 | B | N |

Figure 9

| ATOM | 2761 | CA  | ALA | B | 305 | 50.204 | 24.721 | 33.012 | 1.00 | 32.14 | B | C |
|------|------|-----|-----|---|-----|--------|--------|--------|------|-------|---|---|
| ATOM | 2762 | CB  | ALA | B | 305 | 51.240 | 25.542 | 32.250 | 1.00 | 33.51 | B | C |
| ATOM | 2763 | C   | ALA | B | 305 | 49.686 | 23.575 | 32.135 | 1.00 | 32.79 | B | C |
| ATOM | 2764 | O   | ALA | B | 305 | 49.773 | 22.409 | 32.499 | 1.00 | 31.87 | B | O |
| ATOM | 2765 | N   | VAL | B | 306 | 49.141 | 23.937 | 30.976 | 1.00 | 34.27 | B | N |
| ATOM | 2766 | CA  | VAL | B | 306 | 48.599 | 22.991 | 30.001 | 1.00 | 35.61 | B | C |
| ATOM | 2767 | CB  | VAL | B | 306 | 47.031 | 22.953 | 30.038 | 1.00 | 36.17 | B | C |
| ATOM | 2768 | CG1 | VAL | B | 306 | 46.530 | 22.282 | 31.303 | 1.00 | 36.44 | B | C |
| ATOM | 2769 | CG2 | VAL | B | 306 | 46.453 | 24.354 | 29.944 | 1.00 | 35.79 | B | C |
| ATOM | 2770 | C   | VAL | B | 306 | 49.014 | 23.393 | 28.578 | 1.00 | 36.86 | B | C |
| ATOM | 2771 | O   | VAL | B | 306 | 49.239 | 24.565 | 28.307 | 1.00 | 36.92 | B | O |
| ATOM | 2772 | N   | VAL | B | 307 | 49.153 | 22.415 | 27.686 | 1.00 | 38.52 | B | N |
| ATOM | 2773 | CA  | VAL | B | 307 | 49.495 | 22.686 | 26.294 | 1.00 | 40.20 | B | C |
| ATOM | 2774 | CB  | VAL | B | 307 | 50.737 | 21.918 | 25.826 | 1.00 | 39.88 | B | C |
| ATOM | 2775 | CG1 | VAL | B | 307 | 50.909 | 22.090 | 24.320 | 1.00 | 39.69 | B | C |
| ATOM | 2776 | CG2 | VAL | B | 307 | 51.983 | 22.417 | 26.573 | 1.00 | 38.94 | B | C |
| ATOM | 2777 | C   | VAL | B | 307 | 48.286 | 22.211 | 25.510 | 1.00 | 42.04 | B | C |
| ATOM | 2778 | O   | VAL | B | 307 | 47.995 | 21.011 | 25.475 | 1.00 | 41.47 | B | O |
| ATOM | 2779 | N   | THR | B | 308 | 47.605 | 23.164 | 24.872 | 1.00 | 44.55 | B | N |
| ATOM | 2780 | CA  | THR | B | 308 | 46.382 | 22.895 | 24.119 | 1.00 | 46.71 | B | C |
| ATOM | 2781 | CB  | THR | B | 308 | 45.477 | 24.138 | 24.071 | 1.00 | 46.12 | B | C |
| ATOM | 2782 | OG1 | THR | B | 308 | 46.136 | 25.193 | 23.367 | 1.00 | 47.40 | B | O |
| ATOM | 2783 | CG2 | THR | B | 308 | 45.163 | 24.605 | 25.476 | 1.00 | 45.60 | B | C |
| ATOM | 2784 | C   | THR | B | 308 | 46.415 | 22.248 | 22.737 | 1.00 | 48.46 | B | C |
| ATOM | 2785 | O   | THR | B | 308 | 45.391 | 21.732 | 22.295 | 1.00 | 49.38 | B | O |
| ATOM | 2786 | N   | GLN | B | 309 | 47.538 | 22.276 | 22.029 | 1.00 | 50.58 | B | N |
| ATOM | 2787 | CA  | GLN | B | 309 | 47.558 | 21.627 | 20.718 | 1.00 | 53.18 | B | C |
| ATOM | 2788 | CB  | GLN | B | 309 | 48.446 | 22.382 | 19.724 | 1.00 | 56.95 | B | C |
| ATOM | 2789 | CG  | GLN | B | 309 | 47.965 | 23.824 | 19.420 | 1.00 | 62.35 | B | C |
| ATOM | 2790 | CD  | GLN | B | 309 | 46.517 | 23.913 | 18.884 | 1.00 | 64.47 | B | C |
| ATOM | 2791 | OE1 | GLN | B | 309 | 45.829 | 22.895 | 18.702 | 1.00 | 65.42 | B | O |
| ATOM | 2792 | NE2 | GLN | B | 309 | 46.063 | 25.138 | 18.619 | 1.00 | 65.19 | B | N |
| ATOM | 2793 | C   | GLN | B | 309 | 47.994 | 20.179 | 20.852 | 1.00 | 53.31 | B | C |
| ATOM | 2794 | O   | GLN | B | 309 | 48.893 | 19.881 | 21.635 | 1.00 | 53.76 | B | O |
| ATOM | 2795 | N   | GLU | B | 310 | 47.341 | 19.282 | 20.113 | 1.00 | 53.25 | B | N |
| ATOM | 2796 | CA  | GLU | B | 310 | 47.649 | 17.845 | 20.168 | 1.00 | 53.97 | B | C |
| ATOM | 2797 | CB  | GLU | B | 310 | 46.653 | 17.012 | 19.324 | 1.00 | 56.42 | B | C |
| ATOM | 2798 | CG  | GLU | B | 310 | 46.469 | 17.429 | 17.846 | 1.00 | 60.14 | B | C |
| ATOM | 2799 | CD  | GLU | B | 310 | 45.404 | 18.523 | 17.634 | 1.00 | 62.58 | B | C |
| ATOM | 2800 | OE1 | GLU | B | 310 | 44.203 | 18.243 | 17.870 | 1.00 | 63.40 | B | O |
| ATOM | 2801 | OE2 | GLU | B | 310 | 45.766 | 19.653 | 17.216 | 1.00 | 63.02 | B | O |
| ATOM | 2802 | C   | GLU | B | 310 | 49.098 | 17.459 | 19.825 | 1.00 | 53.05 | B | C |
| ATOM | 2803 | O   | GLU | B | 310 | 49.668 | 17.958 | 18.848 | 1.00 | 53.67 | B | O |
| ATOM | 2804 | N   | PRO | B | 311 | 49.726 | 16.583 | 20.651 | 1.00 | 51.51 | B | N |
| ATOM | 2805 | CD  | PRO | B | 311 | 51.076 | 16.066 | 20.369 | 1.00 | 51.42 | B | C |
| ATOM | 2806 | CA  | PRO | B | 311 | 49.180 | 15.941 | 21.862 | 1.00 | 49.03 | B | C |
| ATOM | 2807 | CB  | PRO | B | 311 | 50.299 | 14.976 | 22.275 | 1.00 | 49.78 | B | C |
| ATOM | 2808 | CG  | PRO | B | 311 | 51.021 | 14.699 | 20.995 | 1.00 | 50.65 | B | C |
| ATOM | 2809 | C   | PRO | B | 311 | 48.905 | 16.960 | 22.972 | 1.00 | 46.32 | B | C |
| ATOM | 2810 | O   | PRO | B | 311 | 49.673 | 17.908 | 23.151 | 1.00 | 46.11 | B | O |
| ATOM | 2811 | N   | ILE | B | 312 | 47.808 | 16.771 | 23.707 | 1.00 | 42.90 | B | N |
| ATOM | 2812 | CA  | ILE | B | 312 | 47.460 | 17.703 | 24.777 | 1.00 | 38.55 | B | C |
| ATOM | 2813 | CB  | ILE | B | 312 | 45.941 | 17.658 | 25.139 | 1.00 | 39.23 | B | C |
| ATOM | 2814 | CG2 | ILE | B | 312 | 45.512 | 19.007 | 25.726 | 1.00 | 38.20 | B | C |
| ATOM | 2815 | CG1 | ILE | B | 312 | 45.078 | 17.344 | 23.905 | 1.00 | 39.98 | B | C |
| ATOM | 2816 | CD1 | ILE | B | 312 | 44.930 | 18.490 | 22.925 | 1.00 | 40.11 | B | C |
| ATOM | 2817 | C   | ILE | B | 312 | 48.262 | 17.322 | 26.008 | 1.00 | 34.65 | B | C |
| ATOM | 2818 | O   | ILE | B | 312 | 48.426 | 16.133 | 26.290 | 1.00 | 33.09 | B | O |
| ATOM | 2819 | N   | TYR | B | 313 | 48.743 | 18.337 | 26.729 | 1.00 | 31.93 | B | N |

Figure 9

```
ATOM   2820  CA   TYR B 313      49.540  18.153  27.956  1.00 30.67      B    C
ATOM   2821  CB   TYR B 313      50.989  18.651  27.751  1.00 30.06      B    C
ATOM   2822  CG   TYR B 313      51.867  17.834  26.827  1.00 29.91      B    C
ATOM   2823  CD1  TYR B 313      51.611  16.489  26.590  1.00 30.43      B    C
ATOM   2824  CE1  TYR B 313      52.409  15.746  25.729  1.00 31.20      B    C
ATOM   2825  CD2  TYR B 313      52.955  18.420  26.179  1.00 30.36      B    C
ATOM   2826  CE2  TYR B 313      53.760  17.688  25.316  1.00 29.85      B    C
ATOM   2827  CZ   TYR B 313      53.482  16.355  25.091  1.00 31.08      B    C
ATOM   2828  OH   TYR B 313      54.255  15.621  24.217  1.00 32.07      B    O
ATOM   2829  C    TYR B 313      49.012  18.876  29.211  1.00 28.77      B    C
ATOM   2830  O    TYR B 313      48.616  20.033  29.143  1.00 28.38      B    O
ATOM   2831  N    ILE B 314      49.025  18.191  30.352  1.00 27.22      B    N
ATOM   2832  CA   ILE B 314      48.653  18.806  31.623  1.00 26.26      B    C
ATOM   2833  CB   ILE B 314      47.520  18.055  32.391  1.00 27.70      B    C
ATOM   2834  CG2  ILE B 314      47.329  18.675  33.772  1.00 25.55      B    C
ATOM   2835  CG1  ILE B 314      46.188  18.135  31.632  1.00 28.30      B    C
ATOM   2836  CD1  ILE B 314      45.096  17.288  32.260  1.00 29.44      B    C
ATOM   2837  C    ILE B 314      49.944  18.694  32.428  1.00 25.16      B    C
ATOM   2838  O    ILE B 314      50.434  17.597  32.686  1.00 25.82      B    O
ATOM   2839  N    ILE B 315      50.493  19.825  32.830  1.00 24.71      B    N
ATOM   2840  CA   ILE B 315      51.746  19.830  33.575  1.00 24.74      B    C
ATOM   2841  CB   ILE B 315      52.729  20.873  32.979  1.00 25.17      B    C
ATOM   2842  CG2  ILE B 315      54.008  20.987  33.828  1.00 23.48      B    C
ATOM   2843  CG1  ILE B 315      53.063  20.484  31.546  1.00 25.32      B    C
ATOM   2844  CD1  ILE B 315      52.947  21.645  30.588  1.00 27.57      B    C
ATOM   2845  C    ILE B 315      51.545  20.089  35.057  1.00 24.01      B    C
ATOM   2846  O    ILE B 315      51.164  21.185  35.458  1.00 24.17      B    O
ATOM   2847  N    THR B 316      51.820  19.067  35.858  1.00 24.24      B    N
ATOM   2848  CA   THR B 316      51.681  19.154  37.307  1.00 23.65      B    C
ATOM   2849  CB   THR B 316      50.722  18.074  37.841  1.00 22.81      B    C
ATOM   2850  OG1  THR B 316      51.262  16.776  37.572  1.00 21.70      B    O
ATOM   2851  CG2  THR B 316      49.367  18.191  37.184  1.00 22.19      B    C
ATOM   2852  C    THR B 316      53.029  18.981  38.024  1.00 23.62      B    C
ATOM   2853  O    THR B 316      54.034  18.611  37.411  1.00 21.20      B    O
ATOM   2854  N    GLU B 317      53.031  19.228  39.331  1.00 24.27      B    N
ATOM   2855  CA   GLU B 317      54.243  19.084  40.115  1.00 24.80      B    C
ATOM   2856  CB   GLU B 317      54.060  19.619  41.537  1.00 26.47      B    C
ATOM   2857  CG   GLU B 317      53.199  18.780  42.451  1.00 26.49      B    C
ATOM   2858  CD   GLU B 317      53.014  19.441  43.796  1.00 28.75      B    C
ATOM   2859  OE1  GLU B 317      51.868  19.844  44.105  1.00 28.59      B    O
ATOM   2860  OE2  GLU B 317      54.012  19.577  44.546  1.00 29.74      B    O
ATOM   2861  C    GLU B 317      54.623  17.626  40.124  1.00 24.09      B    C
ATOM   2862  O    GLU B 317      53.767  16.746  40.017  1.00 25.17      B    O
ATOM   2863  N    TYR B 318      55.922  17.378  40.182  1.00 23.15      B    N
ATOM   2864  CA   TYR B 318      56.444  16.031  40.172  1.00 21.87      B    C
ATOM   2865  CB   TYR B 318      57.893  16.070  39.672  1.00 22.07      B    C
ATOM   2866  CG   TYR B 318      58.574  14.735  39.619  1.00 23.12      B    C
ATOM   2867  CD1  TYR B 318      58.244  13.810  38.645  1.00 24.06      B    C
ATOM   2868  CE1  TYR B 318      58.858  12.570  38.594  1.00 24.31      B    C
ATOM   2869  CD2  TYR B 318      59.544  14.388  40.555  1.00 23.42      B    C
ATOM   2870  CE2  TYR B 318      60.167  13.148  40.515  1.00 23.60      B    C
ATOM   2871  CZ   TYR B 318      59.817  12.244  39.529  1.00 24.11      B    C
ATOM   2872  OH   TYR B 318      60.404  10.997  39.473  1.00 25.72      B    O
ATOM   2873  C    TYR B 318      56.372  15.428  41.568  1.00 21.63      B    C
ATOM   2874  O    TYR B 318      56.650  16.103  42.557  1.00 21.38      B    O
ATOM   2875  N    MET B 319      55.948  14.175  41.649  1.00 21.96      B    N
ATOM   2876  CA   MET B 319      55.874  13.486  42.931  1.00 24.21      B    C
ATOM   2877  CB   MET B 319      54.435  13.133  43.305  1.00 24.17      B    C
ATOM   2878  CG   MET B 319      53.542  14.348  43.569  1.00 24.38      B    C
```

Figure 9

| | | | | | | | | | | | |
|---|---|---|---|---|---|---|---|---|---|---|---|
| ATOM | 2879 | SD | MET | B | 319 | 54.064 | 15.381 | 44.958 | 1.00 | 25.82 | B | S |
| ATOM | 2880 | CE | MET | B | 319 | 53.370 | 14.480 | 46.350 | 1.00 | 23.79 | B | C |
| ATOM | 2881 | C | MET | B | 319 | 56.742 | 12.243 | 42.834 | 1.00 | 25.48 | B | C |
| ATOM | 2882 | O | MET | B | 319 | 56.348 | 11.218 | 42.263 | 1.00 | 25.65 | B | O |
| ATOM | 2883 | N | GLU | B | 320 | 57.967 | 12.406 | 43.331 | 1.00 | 27.68 | B | N |
| ATOM | 2884 | CA | GLU | B | 320 | 59.033 | 11.396 | 43.357 | 1.00 | 28.80 | B | C |
| ATOM | 2885 | CB | GLU | B | 320 | 60.051 | 11.807 | 44.424 | 1.00 | 32.86 | B | C |
| ATOM | 2886 | CG | GLU | B | 320 | 61.180 | 10.818 | 44.670 | 1.00 | 36.83 | B | C |
| ATOM | 2887 | CD | GLU | B | 320 | 62.261 | 10.952 | 43.644 | 1.00 | 38.61 | B | C |
| ATOM | 2888 | OE1 | GLU | B | 320 | 62.916 | 12.015 | 43.633 | 1.00 | 40.28 | B | O |
| ATOM | 2889 | OE2 | GLU | B | 320 | 62.437 | 10.011 | 42.844 | 1.00 | 39.53 | B | O |
| ATOM | 2890 | C | GLU | B | 320 | 58.649 | 9.934 | 43.588 | 1.00 | 27.56 | B | C |
| ATOM | 2891 | O | GLU | B | 320 | 58.935 | 9.059 | 42.753 | 1.00 | 26.81 | B | O |
| ATOM | 2892 | N | ASN | B | 321 | 58.034 | 9.663 | 44.733 | 1.00 | 25.64 | B | N |
| ATOM | 2893 | CA | ASN | B | 321 | 57.656 | 8.298 | 45.062 | 1.00 | 25.37 | B | C |
| ATOM | 2894 | CB | ASN | B | 321 | 57.743 | 8.086 | 46.565 | 1.00 | 25.44 | B | C |
| ATOM | 2895 | CG | ASN | B | 321 | 59.171 | 8.134 | 47.041 | 1.00 | 24.46 | B | C |
| ATOM | 2896 | OD1 | ASN | B | 321 | 59.976 | 7.303 | 46.639 | 1.00 | 25.62 | B | O |
| ATOM | 2897 | ND2 | ASN | B | 321 | 59.513 | 9.136 | 47.833 | 1.00 | 25.00 | B | N |
| ATOM | 2898 | C | ASN | B | 321 | 56.360 | 7.769 | 44.467 | 1.00 | 24.58 | B | C |
| ATOM | 2899 | O | ASN | B | 321 | 55.863 | 6.705 | 44.854 | 1.00 | 24.16 | B | O |
| ATOM | 2900 | N | GLY | B | 322 | 55.857 | 8.504 | 43.484 | 1.00 | 24.06 | B | N |
| ATOM | 2901 | CA | GLY | B | 322 | 54.659 | 8.103 | 42.782 | 1.00 | 24.40 | B | C |
| ATOM | 2902 | C | GLY | B | 322 | 53.418 | 7.987 | 43.630 | 1.00 | 23.64 | B | C |
| ATOM | 2903 | O | GLY | B | 322 | 53.184 | 8.789 | 44.524 | 1.00 | 23.10 | B | O |
| ATOM | 2904 | N | SER | B | 323 | 52.651 | 6.947 | 43.345 | 1.00 | 23.76 | B | N |
| ATOM | 2905 | CA | SER | B | 323 | 51.391 | 6.662 | 44.014 | 1.00 | 24.24 | B | C |
| ATOM | 2906 | CB | SER | B | 323 | 50.534 | 5.832 | 43.072 | 1.00 | 24.14 | B | C |
| ATOM | 2907 | OG | SER | B | 323 | 49.426 | 5.290 | 43.728 | 1.00 | 26.00 | B | O |
| ATOM | 2908 | C | SER | B | 323 | 51.545 | 5.929 | 45.335 | 1.00 | 23.87 | B | C |
| ATOM | 2909 | O | SER | B | 323 | 52.227 | 4.913 | 45.408 | 1.00 | 24.72 | B | O |
| ATOM | 2910 | N | LEU | B | 324 | 50.867 | 6.425 | 46.366 | 1.00 | 23.93 | B | N |
| ATOM | 2911 | CA | LEU | B | 324 | 50.907 | 5.819 | 47.703 | 1.00 | 23.07 | B | C |
| ATOM | 2912 | CB | LEU | B | 324 | 49.908 | 6.527 | 48.649 | 1.00 | 22.18 | B | C |
| ATOM | 2913 | CG | LEU | B | 324 | 49.829 | 6.082 | 50.123 | 1.00 | 20.86 | B | C |
| ATOM | 2914 | CD1 | LEU | B | 324 | 51.159 | 6.429 | 50.840 | 1.00 | 19.78 | B | C |
| ATOM | 2915 | CD2 | LEU | B | 324 | 48.649 | 6.745 | 50.821 | 1.00 | 17.32 | B | C |
| ATOM | 2916 | C | LEU | B | 324 | 50.632 | 4.310 | 47.718 | 1.00 | 22.90 | B | C |
| ATOM | 2917 | O | LEU | B | 324 | 51.262 | 3.574 | 48.474 | 1.00 | 22.52 | B | O |
| ATOM | 2918 | N | VAL | B | 325 | 49.680 | 3.848 | 46.911 | 1.00 | 23.17 | B | N |
| ATOM | 2919 | CA | VAL | B | 325 | 49.360 | 2.431 | 46.892 | 1.00 | 23.19 | B | C |
| ATOM | 2920 | CB | VAL | B | 325 | 48.069 | 2.146 | 46.086 | 1.00 | 22.26 | B | C |
| ATOM | 2921 | CG1 | VAL | B | 325 | 48.348 | 2.117 | 44.602 | 1.00 | 21.98 | B | C |
| ATOM | 2922 | CG2 | VAL | B | 325 | 47.421 | 0.863 | 46.573 | 1.00 | 21.31 | B | C |
| ATOM | 2923 | C | VAL | B | 325 | 50.546 | 1.580 | 46.420 | 1.00 | 24.75 | B | C |
| ATOM | 2924 | O | VAL | B | 325 | 50.669 | 0.418 | 46.794 | 1.00 | 24.50 | B | O |
| ATOM | 2925 | N | ASP | B | 326 | 51.433 | 2.172 | 45.624 | 1.00 | 26.49 | B | N |
| ATOM | 2926 | CA | ASP | B | 326 | 52.622 | 1.460 | 45.137 | 1.00 | 28.05 | B | C |
| ATOM | 2927 | CB | ASP | B | 326 | 53.033 | 1.959 | 43.750 | 1.00 | 28.62 | B | C |
| ATOM | 2928 | CG | ASP | B | 326 | 51.955 | 1.745 | 42.704 | 1.00 | 29.35 | B | C |
| ATOM | 2929 | OD1 | ASP | B | 326 | 51.373 | 0.638 | 42.644 | 1.00 | 28.94 | B | O |
| ATOM | 2930 | OD2 | ASP | B | 326 | 51.709 | 2.692 | 41.926 | 1.00 | 30.99 | B | O |
| ATOM | 2931 | C | ASP | B | 326 | 53.788 | 1.641 | 46.111 | 1.00 | 28.53 | B | C |
| ATOM | 2932 | O | ASP | B | 326 | 54.469 | 0.672 | 46.464 | 1.00 | 29.01 | B | O |
| ATOM | 2933 | N | PHE | B | 327 | 53.978 | 2.880 | 46.569 | 1.00 | 27.78 | B | N |
| ATOM | 2934 | CA | PHE | B | 327 | 55.044 | 3.216 | 47.503 | 1.00 | 27.96 | B | C |
| ATOM | 2935 | CB | PHE | B | 327 | 55.013 | 4.706 | 47.859 | 1.00 | 28.42 | B | C |
| ATOM | 2936 | CG | PHE | B | 327 | 56.051 | 5.097 | 48.872 | 1.00 | 29.28 | B | C |
| ATOM | 2937 | CD1 | PHE | B | 327 | 57.410 | 5.015 | 48.561 | 1.00 | 30.08 | B | C |

Figure 9

| ATOM | 2938 | CD2 | PHE | B | 327 | 55.681 | 5.473 | 50.158 | 1.00 | 29.95 | B | C |
| ATOM | 2939 | CE1 | PHE | B | 327 | 58.381 | 5.291 | 49.514 | 1.00 | 29.65 | B | C |
| ATOM | 2940 | CE2 | PHE | B | 327 | 56.642 | 5.752 | 51.118 | 1.00 | 30.44 | B | C |
| ATOM | 2941 | CZ | PHE | B | 327 | 57.999 | 5.660 | 50.797 | 1.00 | 30.07 | B | C |
| ATOM | 2942 | C | PHE | B | 327 | 55.020 | 2.400 | 48.788 | 1.00 | 28.55 | B | C |
| ATOM | 2943 | O | PHE | B | 327 | 56.071 | 2.042 | 49.309 | 1.00 | 28.99 | B | O |
| ATOM | 2944 | N | LEU | B | 328 | 53.829 | 2.138 | 49.316 | 1.00 | 28.98 | B | N |
| ATOM | 2945 | CA | LEU | B | 328 | 53.682 | 1.371 | 50.552 | 1.00 | 29.38 | B | C |
| ATOM | 2946 | CB | LEU | B | 328 | 52.215 | 1.344 | 50.996 | 1.00 | 28.14 | B | C |
| ATOM | 2947 | CG | LEU | B | 328 | 51.595 | 2.664 | 51.452 | 1.00 | 27.88 | B | C |
| ATOM | 2948 | CD1 | LEU | B | 328 | 50.078 | 2.489 | 51.606 | 1.00 | 27.73 | B | C |
| ATOM | 2949 | CD2 | LEU | B | 328 | 52.249 | 3.156 | 52.753 | 1.00 | 25.81 | B | C |
| ATOM | 2950 | C | LEU | B | 328 | 54.215 | -0.054 | 50.439 | 1.00 | 30.15 | B | C |
| ATOM | 2951 | O | LEU | B | 328 | 54.592 | -0.648 | 51.444 | 1.00 | 29.89 | B | O |
| ATOM | 2952 | N | LYS | B | 329 | 54.244 | -0.593 | 49.218 | 1.00 | 32.06 | B | N |
| ATOM | 2953 | CA | LYS | B | 329 | 54.736 | -1.953 | 48.974 | 1.00 | 33.94 | B | C |
| ATOM | 2954 | CB | LYS | B | 329 | 53.967 | -2.622 | 47.833 | 1.00 | 34.07 | B | C |
| ATOM | 2955 | CG | LYS | B | 329 | 52.462 | -2.658 | 48.004 | 1.00 | 35.82 | B | C |
| ATOM | 2956 | CD | LYS | B | 329 | 51.835 | -3.532 | 46.929 | 1.00 | 37.56 | B | C |
| ATOM | 2957 | CE | LYS | B | 329 | 50.334 | -3.353 | 46.847 | 1.00 | 38.23 | B | C |
| ATOM | 2958 | NZ | LYS | B | 329 | 49.989 | -2.015 | 46.309 | 1.00 | 39.31 | B | N |
| ATOM | 2959 | C | LYS | B | 329 | 56.245 | -2.060 | 48.692 | 1.00 | 34.93 | B | C |
| ATOM | 2960 | O | LYS | B | 329 | 56.766 | -3.175 | 48.592 | 1.00 | 35.69 | B | O |
| ATOM | 2961 | N | THR | B | 330 | 56.924 | -0.918 | 48.521 | 1.00 | 35.80 | B | N |
| ATOM | 2962 | CA | THR | B | 330 | 58.379 | -0.874 | 48.270 | 1.00 | 35.98 | B | C |
| ATOM | 2963 | CB | THR | B | 330 | 58.858 | 0.533 | 47.779 | 1.00 | 34.79 | B | C |
| ATOM | 2964 | OG1 | THR | B | 330 | 58.684 | 1.499 | 48.821 | 1.00 | 33.55 | B | O |
| ATOM | 2965 | CG2 | THR | B | 330 | 58.107 | 0.986 | 46.539 | 1.00 | 34.41 | B | C |
| ATOM | 2966 | C | THR | B | 330 | 59.124 | -1.160 | 49.580 | 1.00 | 37.14 | B | C |
| ATOM | 2967 | O | THR | B | 330 | 58.563 | -0.972 | 50.651 | 1.00 | 36.95 | B | O |
| ATOM | 2968 | N | PRO | B | 331 | 60.391 | -1.624 | 49.508 | 1.00 | 38.38 | B | N |
| ATOM | 2969 | CD | PRO | B | 331 | 61.138 | -2.060 | 48.309 | 1.00 | 39.28 | B | C |
| ATOM | 2970 | CA | PRO | B | 331 | 61.171 | -1.915 | 50.713 | 1.00 | 39.17 | B | C |
| ATOM | 2971 | CB | PRO | B | 331 | 62.577 | -2.109 | 50.151 | 1.00 | 38.66 | B | C |
| ATOM | 2972 | CG | PRO | B | 331 | 62.287 | -2.871 | 48.903 | 1.00 | 37.84 | B | C |
| ATOM | 2973 | C | PRO | B | 331 | 61.112 | -0.806 | 51.767 | 1.00 | 39.94 | B | C |
| ATOM | 2974 | O | PRO | B | 331 | 60.937 | -1.099 | 52.945 | 1.00 | 40.11 | B | O |
| ATOM | 2975 | N | SER | B | 332 | 61.205 | 0.454 | 51.332 | 1.00 | 40.87 | B | N |
| ATOM | 2976 | CA | SER | B | 332 | 61.147 | 1.624 | 52.227 | 1.00 | 41.94 | B | C |
| ATOM | 2977 | CB | SER | B | 332 | 61.520 | 2.905 | 51.476 | 1.00 | 42.67 | B | C |
| ATOM | 2978 | OG | SER | B | 332 | 62.609 | 2.704 | 50.600 | 1.00 | 45.94 | B | O |
| ATOM | 2979 | C | SER | B | 332 | 59.736 | 1.830 | 52.800 | 1.00 | 42.09 | B | C |
| ATOM | 2980 | O | SER | B | 332 | 59.578 | 2.324 | 53.925 | 1.00 | 42.21 | B | O |
| ATOM | 2981 | N | GLY | B | 333 | 58.724 | 1.529 | 51.985 | 1.00 | 41.55 | B | N |
| ATOM | 2982 | CA | GLY | B | 333 | 57.341 | 1.676 | 52.411 | 1.00 | 41.03 | B | C |
| ATOM | 2983 | C | GLY | B | 333 | 56.997 | 0.681 | 53.498 | 1.00 | 40.72 | B | C |
| ATOM | 2984 | O | GLY | B | 333 | 56.438 | 1.051 | 54.531 | 1.00 | 40.36 | B | O |
| ATOM | 2985 | N | ILE | B | 334 | 57.351 | -0.581 | 53.257 | 1.00 | 40.80 | B | N |
| ATOM | 2986 | CA | ILE | B | 334 | 57.115 | -1.674 | 54.202 | 1.00 | 41.16 | B | C |
| ATOM | 2987 | CB | ILE | B | 334 | 57.730 | -3.014 | 53.680 | 1.00 | 41.71 | B | C |
| ATOM | 2988 | CG2 | ILE | B | 334 | 57.760 | -4.069 | 54.780 | 1.00 | 41.96 | B | C |
| ATOM | 2989 | CG1 | ILE | B | 334 | 56.972 | -3.517 | 52.440 | 1.00 | 42.52 | B | C |
| ATOM | 2990 | CD1 | ILE | B | 334 | 55.515 | -3.926 | 52.686 | 1.00 | 43.68 | B | C |
| ATOM | 2991 | C | ILE | B | 334 | 57.726 | -1.339 | 55.559 | 1.00 | 41.00 | B | C |
| ATOM | 2992 | O | ILE | B | 334 | 57.139 | -1.642 | 56.594 | 1.00 | 41.98 | B | O |
| ATOM | 2993 | N | LYS | B | 335 | 58.866 | -0.652 | 55.541 | 1.00 | 40.64 | B | N |
| ATOM | 2994 | CA | LYS | B | 335 | 59.590 | -0.271 | 56.754 | 1.00 | 40.41 | B | C |
| ATOM | 2995 | CB | LYS | B | 335 | 61.066 | 0.009 | 56.425 | 1.00 | 42.34 | B | C |
| ATOM | 2996 | CG | LYS | B | 335 | 61.894 | -1.216 | 55.983 | 1.00 | 45.46 | B | C |

Figure 9

| | | | | | | | | | | | |
|---|---|---|---|---|---|---|---|---|---|---|---|
| ATOM | 2997 | CD | LYS | B | 335 | 63.315 | -0.798 | 55.536 | 1.00 48.04 | B | C |
| ATOM | 2998 | CE | LYS | B | 335 | 63.998 | -1.881 | 54.673 | 1.00 50.01 | B | C |
| ATOM | 2999 | NZ | LYS | B | 335 | 64.744 | -1.305 | 53.497 | 1.00 50.56 | B | N |
| ATOM | 3000 | C | LYS | B | 335 | 59.035 | 0.904 | 57.567 | 1.00 39.31 | B | C |
| ATOM | 3001 | O | LYS | B | 335 | 59.462 | 1.112 | 58.704 | 1.00 38.87 | B | O |
| ATOM | 3002 | N | LEU | B | 336 | 58.097 | 1.669 | 57.004 | 1.00 38.49 | B | N |
| ATOM | 3003 | CA | LEU | B | 336 | 57.532 | 2.839 | 57.706 | 1.00 36.93 | B | C |
| ATOM | 3004 | CB | LEU | B | 336 | 56.520 | 3.593 | 56.825 | 1.00 36.49 | B | C |
| ATOM | 3005 | CG | LEU | B | 336 | 56.983 | 4.328 | 55.560 | 1.00 35.40 | B | C |
| ATOM | 3006 | CD1 | LEU | B | 336 | 55.773 | 4.902 | 54.847 | 1.00 34.28 | B | C |
| ATOM | 3007 | CD2 | LEU | B | 336 | 57.965 | 5.439 | 55.903 | 1.00 33.98 | B | C |
| ATOM | 3008 | C | LEU | B | 336 | 56.877 | 2.524 | 59.052 | 1.00 35.85 | B | C |
| ATOM | 3009 | O | LEU | B | 336 | 56.174 | 1.521 | 59.201 | 1.00 35.02 | B | O |
| ATOM | 3010 | N | THR | B | 337 | 57.102 | 3.407 | 60.019 | 1.00 35.38 | B | N |
| ATOM | 3011 | CA | THR | B | 337 | 56.543 | 3.256 | 61.360 | 1.00 34.97 | B | C |
| ATOM | 3012 | CB | THR | B | 337 | 57.337 | 4.067 | 62.415 | 1.00 35.07 | B | C |
| ATOM | 3013 | OG1 | THR | B | 337 | 57.163 | 5.471 | 62.187 | 1.00 34.97 | B | O |
| ATOM | 3014 | CG2 | THR | B | 337 | 58.827 | 3.729 | 62.353 | 1.00 35.37 | B | C |
| ATOM | 3015 | C | THR | B | 337 | 55.088 | 3.726 | 61.387 | 1.00 35.13 | B | C |
| ATOM | 3016 | O | THR | B | 337 | 54.660 | 4.498 | 60.521 | 1.00 35.24 | B | O |
| ATOM | 3017 | N | ILE | B | 338 | 54.345 | 3.276 | 62.398 | 1.00 34.05 | B | N |
| ATOM | 3018 | CA | ILE | B | 338 | 52.944 | 3.649 | 62.545 | 1.00 32.22 | B | C |
| ATOM | 3019 | CB | ILE | B | 338 | 52.270 | 2.895 | 63.736 | 1.00 32.23 | B | C |
| ATOM | 3020 | CG2 | ILE | B | 338 | 52.967 | 3.225 | 65.054 | 1.00 32.03 | B | C |
| ATOM | 3021 | CG1 | ILE | B | 338 | 50.779 | 3.247 | 63.821 | 1.00 32.74 | B | C |
| ATOM | 3022 | CD1 | ILE | B | 338 | 49.916 | 2.665 | 62.704 | 1.00 31.06 | B | C |
| ATOM | 3023 | C | ILE | B | 338 | 52.822 | 5.162 | 62.710 | 1.00 30.88 | B | C |
| ATOM | 3024 | O | ILE | B | 338 | 51.879 | 5.767 | 62.219 | 1.00 30.60 | B | O |
| ATOM | 3025 | N | ASN | B | 339 | 53.833 | 5.773 | 63.314 | 1.00 30.21 | B | N |
| ATOM | 3026 | CA | ASN | B | 339 | 53.855 | 7.218 | 63.537 | 1.00 30.02 | B | C |
| ATOM | 3027 | CB | ASN | B | 339 | 55.081 | 7.595 | 64.371 | 1.00 30.62 | B | C |
| ATOM | 3028 | CG | ASN | B | 339 | 55.144 | 6.834 | 65.677 | 1.00 31.42 | B | C |
| ATOM | 3029 | OD1 | ASN | B | 339 | 54.876 | 7.395 | 66.734 | 1.00 32.82 | B | O |
| ATOM | 3030 | ND2 | ASN | B | 339 | 55.485 | 5.548 | 65.612 | 1.00 31.05 | B | N |
| ATOM | 3031 | C | ASN | B | 339 | 53.898 | 7.979 | 62.221 | 1.00 29.99 | B | C |
| ATOM | 3032 | O | ASN | B | 339 | 53.307 | 9.061 | 62.092 | 1.00 30.52 | B | O |
| ATOM | 3033 | N | LYS | B | 340 | 54.654 | 7.436 | 61.270 | 1.00 28.94 | B | N |
| ATOM | 3034 | CA | LYS | B | 340 | 54.782 | 8.040 | 59.952 | 1.00 28.52 | B | C |
| ATOM | 3035 | CB | LYS | B | 340 | 56.022 | 7.510 | 59.226 | 1.00 28.87 | B | C |
| ATOM | 3036 | CG | LYS | B | 340 | 56.153 | 7.997 | 57.801 | 1.00 28.98 | B | C |
| ATOM | 3037 | CD | LYS | B | 340 | 56.194 | 9.518 | 57.697 | 1.00 29.57 | B | C |
| ATOM | 3038 | CE | LYS | B | 340 | 56.218 | 9.927 | 56.223 | 1.00 31.49 | B | C |
| ATOM | 3039 | NZ | LYS | B | 340 | 56.292 | 11.400 | 55.996 | 1.00 33.98 | B | N |
| ATOM | 3040 | C | LYS | B | 340 | 53.525 | 7.761 | 59.130 | 1.00 27.10 | B | C |
| ATOM | 3041 | O | LYS | B | 340 | 53.024 | 8.653 | 58.452 | 1.00 27.37 | B | O |
| ATOM | 3042 | N | LEU | B | 341 | 53.020 | 6.532 | 59.207 | 1.00 26.17 | B | N |
| ATOM | 3043 | CA | LEU | B | 341 | 51.808 | 6.146 | 58.496 | 1.00 26.36 | B | C |
| ATOM | 3044 | CB | LEU | B | 341 | 51.472 | 4.678 | 58.764 | 1.00 25.26 | B | C |
| ATOM | 3045 | CG | LEU | B | 341 | 52.390 | 3.650 | 58.098 | 1.00 24.68 | B | C |
| ATOM | 3046 | CD1 | LEU | B | 341 | 51.930 | 2.255 | 58.438 | 1.00 23.72 | B | C |
| ATOM | 3047 | CD2 | LEU | B | 341 | 52.404 | 3.853 | 56.591 | 1.00 23.91 | B | C |
| ATOM | 3048 | C | LEU | B | 341 | 50.630 | 7.041 | 58.889 | 1.00 26.44 | B | C |
| ATOM | 3049 | O | LEU | B | 341 | 49.820 | 7.416 | 58.038 | 1.00 27.13 | B | O |
| ATOM | 3050 | N | LEU | B | 342 | 50.546 | 7.397 | 60.168 | 1.00 26.29 | B | N |
| ATOM | 3051 | CA | LEU | B | 342 | 49.481 | 8.267 | 60.648 | 1.00 26.25 | B | C |
| ATOM | 3052 | CB | LEU | B | 342 | 49.293 | 8.129 | 62.152 | 1.00 28.25 | B | C |
| ATOM | 3053 | CG | LEU | B | 342 | 48.848 | 6.727 | 62.567 | 1.00 30.90 | B | C |
| ATOM | 3054 | CD1 | LEU | B | 342 | 48.440 | 6.761 | 63.989 | 1.00 32.59 | B | C |
| ATOM | 3055 | CD2 | LEU | B | 342 | 47.685 | 6.222 | 61.727 | 1.00 32.43 | B | C |

Figure 9

| ATOM | 3056 | C | LEU | B | 342 | 49.683 | 9.724 | 60.263 | 1.00 | 25.62 | B | C |
|------|------|-----|-----|---|-----|--------|--------|--------|------|-------|---|---|
| ATOM | 3057 | O | LEU | B | 342 | 48.703 | 10.460 | 60.102 | 1.00 | 25.08 | B | O |
| ATOM | 3058 | N | ASP | B | 343 | 50.939 | 10.151 | 60.124 | 1.00 | 24.95 | B | N |
| ATOM | 3059 | CA | ASP | B | 343 | 51.204 | 11.521 | 59.704 | 1.00 | 25.27 | B | C |
| ATOM | 3060 | CB | ASP | B | 343 | 52.673 | 11.882 | 59.860 | 1.00 | 29.26 | B | C |
| ATOM | 3061 | CG | ASP | B | 343 | 52.939 | 13.347 | 59.538 | 1.00 | 33.43 | B | C |
| ATOM | 3062 | OD1 | ASP | B | 343 | 52.164 | 14.221 | 60.010 | 1.00 | 36.05 | B | O |
| ATOM | 3063 | OD2 | ASP | B | 343 | 53.906 | 13.630 | 58.794 | 1.00 | 36.37 | B | O |
| ATOM | 3064 | C | ASP | B | 343 | 50.787 | 11.679 | 58.240 | 1.00 | 23.52 | B | C |
| ATOM | 3065 | O | ASP | B | 343 | 50.276 | 12.718 | 57.830 | 1.00 | 22.10 | B | O |
| ATOM | 3066 | N | MET | B | 344 | 51.022 | 10.638 | 57.453 | 1.00 | 22.83 | B | N |
| ATOM | 3067 | CA | MET | B | 344 | 50.629 | 10.641 | 56.052 | 1.00 | 23.12 | B | C |
| ATOM | 3068 | CB | MET | B | 344 | 51.160 | 9.388 | 55.370 | 1.00 | 23.05 | B | C |
| ATOM | 3069 | CG | MET | B | 344 | 52.661 | 9.328 | 55.332 | 1.00 | 24.94 | B | C |
| ATOM | 3070 | SD | MET | B | 344 | 53.196 | 7.791 | 54.639 | 1.00 | 27.67 | B | S |
| ATOM | 3071 | CE | MET | B | 344 | 53.804 | 8.289 | 53.062 | 1.00 | 27.49 | B | C |
| ATOM | 3072 | C | MET | B | 344 | 49.089 | 10.696 | 55.951 | 1.00 | 22.62 | B | C |
| ATOM | 3073 | O | MET | B | 344 | 48.539 | 11.435 | 55.134 | 1.00 | 22.28 | B | O |
| ATOM | 3074 | N | ALA | B | 345 | 48.421 | 9.894 | 56.787 | 1.00 | 22.00 | B | N |
| ATOM | 3075 | CA | ALA | B | 345 | 46.958 | 9.833 | 56.861 | 1.00 | 21.05 | B | C |
| ATOM | 3076 | CB | ALA | B | 345 | 46.533 | 8.801 | 57.919 | 1.00 | 20.28 | B | C |
| ATOM | 3077 | C | ALA | B | 345 | 46.414 | 11.217 | 57.224 | 1.00 | 20.45 | B | C |
| ATOM | 3078 | O | ALA | B | 345 | 45.446 | 11.677 | 56.633 | 1.00 | 18.96 | B | O |
| ATOM | 3079 | N | ALA | B | 346 | 47.089 | 11.883 | 58.165 | 1.00 | 20.36 | B | N |
| ATOM | 3080 | CA | ALA | B | 346 | 46.722 | 13.217 | 58.622 | 1.00 | 20.00 | B | C |
| ATOM | 3081 | CB | ALA | B | 346 | 47.561 | 13.597 | 59.818 | 1.00 | 19.73 | B | C |
| ATOM | 3082 | C | ALA | B | 346 | 46.886 | 14.267 | 57.528 | 1.00 | 21.16 | B | C |
| ATOM | 3083 | O | ALA | B | 346 | 46.159 | 15.263 | 57.502 | 1.00 | 21.48 | B | O |
| ATOM | 3084 | N | GLN | B | 347 | 47.882 | 14.082 | 56.666 | 1.00 | 21.30 | B | N |
| ATOM | 3085 | CA | GLN | B | 347 | 48.114 | 15.014 | 55.562 | 1.00 | 20.85 | B | C |
| ATOM | 3086 | CB | GLN | B | 347 | 49.441 | 14.726 | 54.851 | 1.00 | 20.78 | B | C |
| ATOM | 3087 | CG | GLN | B | 347 | 50.632 | 14.970 | 55.737 | 1.00 | 22.55 | B | C |
| ATOM | 3088 | CD | GLN | B | 347 | 51.941 | 14.722 | 55.043 | 1.00 | 24.40 | B | C |
| ATOM | 3089 | OE1 | GLN | B | 347 | 52.797 | 15.597 | 55.031 | 1.00 | 27.31 | B | O |
| ATOM | 3090 | NE2 | GLN | B | 347 | 52.122 | 13.526 | 54.483 | 1.00 | 23.42 | B | N |
| ATOM | 3091 | C | GLN | B | 347 | 46.986 | 14.897 | 54.562 | 1.00 | 19.33 | B | C |
| ATOM | 3092 | O | GLN | B | 347 | 46.543 | 15.902 | 54.007 | 1.00 | 18.81 | B | O |
| ATOM | 3093 | N | ILE | B | 348 | 46.545 | 13.660 | 54.337 | 1.00 | 19.32 | B | N |
| ATOM | 3094 | CA | ILE | B | 348 | 45.461 | 13.360 | 53.401 | 1.00 | 20.12 | B | C |
| ATOM | 3095 | CB | ILE | B | 348 | 45.349 | 11.831 | 53.134 | 1.00 | 19.47 | B | C |
| ATOM | 3096 | CG2 | ILE | B | 348 | 44.237 | 11.537 | 52.123 | 1.00 | 19.85 | B | C |
| ATOM | 3097 | CG1 | ILE | B | 348 | 46.678 | 11.308 | 52.581 | 1.00 | 19.71 | B | C |
| ATOM | 3098 | CD1 | ILE | B | 348 | 46.758 | 9.810 | 52.443 | 1.00 | 18.76 | B | C |
| ATOM | 3099 | C | ILE | B | 348 | 44.137 | 13.930 | 53.934 | 1.00 | 20.36 | B | C |
| ATOM | 3100 | O | ILE | B | 348 | 43.367 | 14.540 | 53.176 | 1.00 | 20.42 | B | O |
| ATOM | 3101 | N | ALA | B | 349 | 43.907 | 13.759 | 55.237 | 1.00 | 19.77 | B | N |
| ATOM | 3102 | CA | ALA | B | 349 | 42.710 | 14.279 | 55.893 | 1.00 | 19.46 | B | C |
| ATOM | 3103 | CB | ALA | B | 349 | 42.670 | 13.836 | 57.359 | 1.00 | 17.97 | B | C |
| ATOM | 3104 | C | ALA | B | 349 | 42.709 | 15.808 | 55.801 | 1.00 | 19.92 | B | C |
| ATOM | 3105 | O | ALA | B | 349 | 41.666 | 16.421 | 55.574 | 1.00 | 20.73 | B | O |
| ATOM | 3106 | N | GLU | B | 350 | 43.889 | 16.414 | 55.940 | 1.00 | 20.82 | B | N |
| ATOM | 3107 | CA | GLU | B | 350 | 44.052 | 17.872 | 55.869 | 1.00 | 20.61 | B | C |
| ATOM | 3108 | CB | GLU | B | 350 | 45.496 | 18.254 | 56.213 | 1.00 | 22.25 | B | C |
| ATOM | 3109 | CG | GLU | B | 350 | 45.765 | 19.748 | 56.259 | 1.00 | 24.56 | B | C |
| ATOM | 3110 | CD | GLU | B | 350 | 47.263 | 20.096 | 56.233 | 1.00 | 26.48 | B | C |
| ATOM | 3111 | OE1 | GLU | B | 350 | 48.125 | 19.197 | 56.408 | 1.00 | 25.97 | B | O |
| ATOM | 3112 | OE2 | GLU | B | 350 | 47.575 | 21.290 | 56.035 | 1.00 | 27.65 | B | O |
| ATOM | 3113 | C | GLU | B | 350 | 43.677 | 18.402 | 54.482 | 1.00 | 20.05 | B | C |
| ATOM | 3114 | O | GLU | B | 350 | 43.055 | 19.462 | 54.355 | 1.00 | 20.48 | B | O |

Figure 9

| | | | | | | | | | | | |
|---|---|---|---|---|---|---|---|---|---|---|---|
| ATOM | 3115 | N | GLY | B | 351 | 44.060 | 17.661 | 53.445 | 1.00 | 19.00 | B N |
| ATOM | 3116 | CA | GLY | B | 351 | 43.727 | 18.052 | 52.087 | 1.00 | 17.16 | B C |
| ATOM | 3117 | C | GLY | B | 351 | 42.230 | 17.883 | 51.857 | 1.00 | 16.64 | B C |
| ATOM | 3118 | O | GLY | B | 351 | 41.607 | 18.714 | 51.216 | 1.00 | 16.32 | B O |
| ATOM | 3119 | N | MET | B | 352 | 41.653 | 16.817 | 52.404 | 1.00 | 16.33 | B N |
| ATOM | 3120 | CA | MET | B | 352 | 40.227 | 16.567 | 52.266 | 1.00 | 16.89 | B C |
| ATOM | 3121 | CB | MET | B | 352 | 39.881 | 15.145 | 52.675 | 1.00 | 16.19 | B C |
| ATOM | 3122 | CG | MET | B | 352 | 40.288 | 14.084 | 51.653 | 1.00 | 17.59 | B C |
| ATOM | 3123 | SD | MET | B | 352 | 39.712 | 14.407 | 49.948 | 1.00 | 18.20 | B S |
| ATOM | 3124 | CE | MET | B | 352 | 37.887 | 14.599 | 50.187 | 1.00 | 16.22 | B C |
| ATOM | 3125 | C | MET | B | 352 | 39.423 | 17.556 | 53.088 | 1.00 | 17.74 | B C |
| ATOM | 3126 | O | MET | B | 352 | 38.273 | 17.858 | 52.755 | 1.00 | 18.81 | B O |
| ATOM | 3127 | N | ALA | B | 353 | 40.032 | 18.077 | 54.153 | 1.00 | 18.00 | B N |
| ATOM | 3128 | CA | ALA | B | 353 | 39.367 | 19.052 | 55.000 | 1.00 | 18.74 | B C |
| ATOM | 3129 | CB | ALA | B | 353 | 40.125 | 19.247 | 56.281 | 1.00 | 17.04 | B C |
| ATOM | 3130 | C | ALA | B | 353 | 39.263 | 20.363 | 54.222 | 1.00 | 19.97 | B C |
| ATOM | 3131 | O | ALA | B | 353 | 38.344 | 21.160 | 54.443 | 1.00 | 21.46 | B O |
| ATOM | 3132 | N | PHE | B | 354 | 40.209 | 20.590 | 53.313 | 1.00 | 20.20 | B N |
| ATOM | 3133 | CA | PHE | B | 354 | 40.193 | 21.791 | 52.492 | 1.00 | 19.20 | B C |
| ATOM | 3134 | CB | PHE | B | 354 | 41.548 | 22.011 | 51.836 | 1.00 | 18.23 | B C |
| ATOM | 3135 | CG | PHE | B | 354 | 41.548 | 23.108 | 50.810 | 1.00 | 19.46 | B C |
| ATOM | 3136 | CD1 | PHE | B | 354 | 41.500 | 24.446 | 51.203 | 1.00 | 20.22 | B C |
| ATOM | 3137 | CD2 | PHE | B | 354 | 41.596 | 22.805 | 49.448 | 1.00 | 20.27 | B C |
| ATOM | 3138 | CE1 | PHE | B | 354 | 41.502 | 25.472 | 50.259 | 1.00 | 21.12 | B C |
| ATOM | 3139 | CE2 | PHE | B | 354 | 41.599 | 23.822 | 48.489 | 1.00 | 21.18 | B C |
| ATOM | 3140 | CZ | PHE | B | 354 | 41.552 | 25.159 | 48.895 | 1.00 | 21.60 | B C |
| ATOM | 3141 | C | PHE | B | 354 | 39.120 | 21.641 | 51.424 | 1.00 | 19.06 | B C |
| ATOM | 3142 | O | PHE | B | 354 | 38.385 | 22.580 | 51.137 | 1.00 | 18.96 | B O |
| ATOM | 3143 | N | ILE | B | 355 | 39.062 | 20.458 | 50.812 | 1.00 | 20.48 | B N |
| ATOM | 3144 | CA | ILE | B | 355 | 38.079 | 20.153 | 49.775 | 1.00 | 20.33 | B C |
| ATOM | 3145 | CB | ILE | B | 355 | 38.332 | 18.741 | 49.180 | 1.00 | 19.06 | B C |
| ATOM | 3146 | CG2 | ILE | B | 355 | 37.143 | 18.261 | 48.353 | 1.00 | 18.22 | B C |
| ATOM | 3147 | CG1 | ILE | B | 355 | 39.606 | 18.779 | 48.317 | 1.00 | 18.16 | B C |
| ATOM | 3148 | CD1 | ILE | B | 355 | 40.018 | 17.449 | 47.721 | 1.00 | 16.47 | B C |
| ATOM | 3149 | C | ILE | B | 355 | 36.682 | 20.295 | 50.389 | 1.00 | 21.92 | B C |
| ATOM | 3150 | O | ILE | B | 355 | 35.793 | 20.912 | 49.797 | 1.00 | 22.61 | B O |
| ATOM | 3151 | N | GLU | B | 356 | 36.546 | 19.813 | 51.620 | 1.00 | 22.70 | B N |
| ATOM | 3152 | CA | GLU | B | 356 | 35.306 | 19.887 | 52.390 | 1.00 | 24.16 | B C |
| ATOM | 3153 | CB | GLU | B | 356 | 35.532 | 19.168 | 53.712 | 1.00 | 22.56 | B C |
| ATOM | 3154 | CG | GLU | B | 356 | 34.358 | 19.139 | 54.672 | 1.00 | 20.20 | B C |
| ATOM | 3155 | CD | GLU | B | 356 | 34.665 | 18.269 | 55.866 | 1.00 | 18.46 | B C |
| ATOM | 3156 | OE1 | GLU | B | 356 | 35.303 | 18.753 | 56.824 | 1.00 | 20.94 | B O |
| ATOM | 3157 | OE2 | GLU | B | 356 | 34.306 | 17.081 | 55.831 | 1.00 | 19.17 | B O |
| ATOM | 3158 | C | GLU | B | 356 | 34.896 | 21.355 | 52.637 | 1.00 | 26.20 | B C |
| ATOM | 3159 | O | GLU | B | 356 | 33.779 | 21.762 | 52.334 | 1.00 | 27.28 | B O |
| ATOM | 3160 | N | GLU | B | 357 | 35.823 | 22.131 | 53.182 | 1.00 | 28.20 | B N |
| ATOM | 3161 | CA | GLU | B | 357 | 35.659 | 23.554 | 53.478 | 1.00 | 30.08 | B C |
| ATOM | 3162 | CB | GLU | B | 357 | 37.026 | 24.083 | 53.971 | 1.00 | 32.89 | B C |
| ATOM | 3163 | CG | GLU | B | 357 | 37.223 | 25.585 | 54.040 | 1.00 | 37.69 | B C |
| ATOM | 3164 | CD | GLU | B | 357 | 36.460 | 26.228 | 55.184 | 1.00 | 42.70 | B C |
| ATOM | 3165 | OE1 | GLU | B | 357 | 36.490 | 25.693 | 56.319 | 1.00 | 45.24 | B O |
| ATOM | 3166 | OE2 | GLU | B | 357 | 35.832 | 27.283 | 54.950 | 1.00 | 45.67 | B O |
| ATOM | 3167 | C | GLU | B | 357 | 35.197 | 24.338 | 52.239 | 1.00 | 30.27 | B C |
| ATOM | 3168 | O | GLU | B | 357 | 34.398 | 25.269 | 52.338 | 1.00 | 30.24 | B O |
| ATOM | 3169 | N | ARG | B | 358 | 35.690 | 23.940 | 51.070 | 1.00 | 30.44 | B N |
| ATOM | 3170 | CA | ARG | B | 358 | 35.357 | 24.616 | 49.826 | 1.00 | 31.47 | B C |
| ATOM | 3171 | CB | ARG | B | 358 | 36.570 | 24.596 | 48.891 | 1.00 | 34.23 | B C |
| ATOM | 3172 | CG | ARG | B | 358 | 37.840 | 25.220 | 49.492 | 1.00 | 38.73 | B C |
| ATOM | 3173 | CD | ARG | B | 358 | 37.716 | 26.742 | 49.725 | 1.00 | 42.43 | B C |

Figure 9

| | | | | | | | | | | | |
|---|---|---|---|---|---|---|---|---|---|---|---|
| ATOM | 3174 | NE | ARG | B | 358 | 37.464 | 27.455 | 48.474 | 1.00 | 47.26 | B | N |
| ATOM | 3175 | CZ | ARG | B | 358 | 38.328 | 27.521 | 47.461 | 1.00 | 50.35 | B | C |
| ATOM | 3176 | NH1 | ARG | B | 358 | 39.519 | 26.941 | 47.547 | 1.00 | 51.95 | B | N |
| ATOM | 3177 | NH2 | ARG | B | 358 | 37.979 | 28.103 | 46.327 | 1.00 | 52.44 | B | N |
| ATOM | 3178 | C | ARG | B | 358 | 34.132 | 24.053 | 49.110 | 1.00 | 30.76 | B | C |
| ATOM | 3179 | O | ARG | B | 358 | 33.842 | 24.440 | 47.974 | 1.00 | 30.65 | B | O |
| ATOM | 3180 | N | ASN | B | 359 | 33.404 | 23.176 | 49.802 | 1.00 | 29.83 | B | N |
| ATOM | 3181 | CA | ASN | B | 359 | 32.201 | 22.514 | 49.295 | 1.00 | 29.51 | B | C |
| ATOM | 3182 | CB | ASN | B | 359 | 30.995 | 23.449 | 49.285 | 1.00 | 32.41 | B | C |
| ATOM | 3183 | CG | ASN | B | 359 | 30.687 | 24.000 | 50.669 | 1.00 | 36.67 | B | C |
| ATOM | 3184 | OD1 | ASN | B | 359 | 30.310 | 23.257 | 51.590 | 1.00 | 38.64 | B | O |
| ATOM | 3185 | ND2 | ASN | B | 359 | 30.895 | 25.308 | 50.839 | 1.00 | 38.54 | B | N |
| ATOM | 3186 | C | ASN | B | 359 | 32.346 | 21.785 | 47.974 | 1.00 | 28.21 | B | C |
| ATOM | 3187 | O | ASN | B | 359 | 31.522 | 21.901 | 47.068 | 1.00 | 27.59 | B | O |
| ATOM | 3188 | N | TYR | B | 360 | 33.416 | 21.010 | 47.897 | 1.00 | 27.28 | B | N |
| ATOM | 3189 | CA | TYR | B | 360 | 33.711 | 20.178 | 46.749 | 1.00 | 25.95 | B | C |
| ATOM | 3190 | CB | TYR | B | 360 | 35.104 | 20.516 | 46.197 | 1.00 | 27.03 | B | C |
| ATOM | 3191 | CG | TYR | B | 360 | 35.151 | 21.595 | 45.139 | 1.00 | 27.19 | B | C |
| ATOM | 3192 | CD1 | TYR | B | 360 | 35.165 | 22.942 | 45.486 | 1.00 | 28.63 | B | C |
| ATOM | 3193 | CE1 | TYR | B | 360 | 35.251 | 23.934 | 44.520 | 1.00 | 29.58 | B | C |
| ATOM | 3194 | CD2 | TYR | B | 360 | 35.223 | 21.262 | 43.787 | 1.00 | 28.49 | B | C |
| ATOM | 3195 | CE2 | TYR | B | 360 | 35.310 | 22.249 | 42.800 | 1.00 | 29.68 | B | C |
| ATOM | 3196 | CZ | TYR | B | 360 | 35.325 | 23.580 | 43.176 | 1.00 | 30.60 | B | C |
| ATOM | 3197 | OH | TYR | B | 360 | 35.435 | 24.562 | 42.215 | 1.00 | 33.18 | B | O |
| ATOM | 3198 | C | TYR | B | 360 | 33.736 | 18.754 | 47.315 | 1.00 | 25.29 | B | C |
| ATOM | 3199 | O | TYR | B | 360 | 33.496 | 18.534 | 48.504 | 1.00 | 25.26 | B | O |
| ATOM | 3200 | N | ILE | B | 361 | 33.969 | 17.784 | 46.445 | 1.00 | 24.54 | B | N |
| ATOM | 3201 | CA | ILE | B | 361 | 34.094 | 16.397 | 46.851 | 1.00 | 24.06 | B | C |
| ATOM | 3202 | CB | ILE | B | 361 | 32.781 | 15.560 | 46.650 | 1.00 | 23.90 | B | C |
| ATOM | 3203 | CG2 | ILE | B | 361 | 31.608 | 16.204 | 47.392 | 1.00 | 24.83 | B | C |
| ATOM | 3204 | CG1 | ILE | B | 361 | 32.456 | 15.382 | 45.170 | 1.00 | 23.65 | B | C |
| ATOM | 3205 | CD1 | ILE | B | 361 | 31.510 | 14.242 | 44.893 | 1.00 | 21.90 | B | C |
| ATOM | 3206 | C | ILE | B | 361 | 35.234 | 15.837 | 45.988 | 1.00 | 23.71 | B | C |
| ATOM | 3207 | O | ILE | B | 361 | 35.678 | 16.478 | 45.035 | 1.00 | 23.99 | B | O |
| ATOM | 3208 | N | HIS | B | 362 | 35.725 | 14.662 | 46.334 | 1.00 | 22.45 | B | N |
| ATOM | 3209 | CA | HIS | B | 362 | 36.789 | 14.051 | 45.576 | 1.00 | 22.31 | B | C |
| ATOM | 3210 | CB | HIS | B | 362 | 37.755 | 13.349 | 46.532 | 1.00 | 20.50 | B | C |
| ATOM | 3211 | CG | HIS | B | 362 | 39.022 | 12.891 | 45.886 | 1.00 | 18.32 | B | C |
| ATOM | 3212 | CD2 | HIS | B | 362 | 40.312 | 13.214 | 46.133 | 1.00 | 18.10 | B | C |
| ATOM | 3213 | ND1 | HIS | B | 362 | 39.045 | 11.980 | 44.856 | 1.00 | 18.25 | B | N |
| ATOM | 3214 | CE1 | HIS | B | 362 | 40.298 | 11.760 | 44.493 | 1.00 | 17.29 | B | C |
| ATOM | 3215 | NE2 | HIS | B | 362 | 41.086 | 12.500 | 45.252 | 1.00 | 17.14 | B | N |
| ATOM | 3216 | C | HIS | B | 362 | 36.187 | 13.037 | 44.612 | 1.00 | 22.91 | B | C |
| ATOM | 3217 | O | HIS | B | 362 | 36.409 | 13.117 | 43.406 | 1.00 | 23.62 | B | O |
| ATOM | 3218 | N | ARG | B | 363 | 35.389 | 12.136 | 45.189 | 1.00 | 23.00 | B | N |
| ATOM | 3219 | CA | ARG | B | 363 | 34.687 | 10.997 | 44.574 | 1.00 | 22.69 | B | C |
| ATOM | 3220 | CB | ARG | B | 363 | 33.614 | 11.384 | 43.545 | 1.00 | 27.15 | B | C |
| ATOM | 3221 | CG | ARG | B | 363 | 34.035 | 12.196 | 42.363 | 1.00 | 31.67 | B | C |
| ATOM | 3222 | CD | ARG | B | 363 | 32.800 | 12.725 | 41.639 | 1.00 | 33.96 | B | C |
| ATOM | 3223 | NE | ARG | B | 363 | 32.046 | 11.644 | 41.029 | 1.00 | 35.08 | B | N |
| ATOM | 3224 | CZ | ARG | B | 363 | 30.719 | 11.600 | 41.001 | 1.00 | 37.48 | B | C |
| ATOM | 3225 | NH1 | ARG | B | 363 | 30.009 | 12.592 | 41.539 | 1.00 | 33.87 | B | N |
| ATOM | 3226 | NH2 | ARG | B | 363 | 30.106 | 10.543 | 40.469 | 1.00 | 39.50 | B | N |
| ATOM | 3227 | C | ARG | B | 363 | 35.496 | 9.805 | 44.109 | 1.00 | 21.26 | B | C |
| ATOM | 3228 | O | ARG | B | 363 | 34.934 | 8.762 | 43.772 | 1.00 | 19.90 | B | O |
| ATOM | 3229 | N | ASP | B | 364 | 36.816 | 9.930 | 44.156 | 1.00 | 20.28 | B | N |
| ATOM | 3230 | CA | ASP | B | 364 | 37.698 | 8.837 | 43.754 | 1.00 | 19.86 | B | C |
| ATOM | 3231 | CB | ASP | B | 364 | 38.276 | 9.105 | 42.352 | 1.00 | 19.46 | B | C |
| ATOM | 3232 | CG | ASP | B | 364 | 37.247 | 8.897 | 41.242 | 1.00 | 18.99 | B | C |

Figure 9

| | | | | | | | | | | | |
|---|---|---|---|---|---|---|---|---|---|---|---|
| ATOM | 3233 | OD1 | ASP | B | 364 | 36.827 | 7.733 | 41.024 | 1.00 | 18.35 | B | O |
| ATOM | 3234 | OD2 | ASP | B | 364 | 36.881 | 9.898 | 40.584 | 1.00 | 19.88 | B | O |
| ATOM | 3235 | C | ASP | B | 364 | 38.816 | 8.665 | 44.773 | 1.00 | 19.31 | B | C |
| ATOM | 3236 | O | ASP | B | 364 | 39.894 | 8.183 | 44.445 | 1.00 | 18.40 | B | O |
| ATOM | 3237 | N | LEU | B | 365 | 38.532 | 9.044 | 46.020 | 1.00 | 18.66 | B | N |
| ATOM | 3238 | CA | LEU | B | 365 | 39.512 | 8.961 | 47.088 | 1.00 | 18.26 | B | C |
| ATOM | 3239 | CB | LEU | B | 365 | 39.018 | 9.727 | 48.331 | 1.00 | 17.89 | B | C |
| ATOM | 3240 | CG | LEU | B | 365 | 39.959 | 9.780 | 49.551 | 1.00 | 19.11 | B | C |
| ATOM | 3241 | CD1 | LEU | B | 365 | 41.283 | 10.475 | 49.197 | 1.00 | 18.18 | B | C |
| ATOM | 3242 | CD2 | LEU | B | 365 | 39.290 | 10.489 | 50.728 | 1.00 | 18.30 | B | C |
| ATOM | 3243 | C | LEU | B | 365 | 39.955 | 7.533 | 47.448 | 1.00 | 18.91 | B | C |
| ATOM | 3244 | O | LEU | B | 365 | 39.147 | 6.682 | 47.833 | 1.00 | 19.70 | B | O |
| ATOM | 3245 | N | ARG | B | 366 | 41.243 | 7.268 | 47.258 | 1.00 | 17.78 | B | N |
| ATOM | 3246 | CA | ARG | B | 366 | 41.832 | 5.976 | 47.579 | 1.00 | 18.08 | B | C |
| ATOM | 3247 | CB | ARG | B | 366 | 41.332 | 4.869 | 46.648 | 1.00 | 20.03 | B | C |
| ATOM | 3248 | CG | ARG | B | 366 | 41.553 | 5.071 | 45.176 | 1.00 | 22.64 | B | C |
| ATOM | 3249 | CD | ARG | B | 366 | 40.863 | 3.950 | 44.422 | 1.00 | 25.82 | B | C |
| ATOM | 3250 | NE | ARG | B | 366 | 40.668 | 4.275 | 43.013 | 1.00 | 31.25 | B | N |
| ATOM | 3251 | CZ | ARG | B | 366 | 39.595 | 4.898 | 42.518 | 1.00 | 30.66 | B | C |
| ATOM | 3252 | NH1 | ARG | B | 366 | 38.588 | 5.270 | 43.308 | 1.00 | 30.75 | B | N |
| ATOM | 3253 | NH2 | ARG | B | 366 | 39.553 | 5.186 | 41.226 | 1.00 | 31.39 | B | N |
| ATOM | 3254 | C | ARG | B | 366 | 43.333 | 6.140 | 47.511 | 1.00 | 17.49 | B | C |
| ATOM | 3255 | O | ARG | B | 366 | 43.812 | 7.156 | 47.002 | 1.00 | 16.59 | B | O |
| ATOM | 3256 | N | ALA | B | 367 | 44.066 | 5.183 | 48.079 | 1.00 | 16.80 | B | N |
| ATOM | 3257 | CA | ALA | B | 367 | 45.532 | 5.247 | 48.119 | 1.00 | 17.55 | B | C |
| ATOM | 3258 | CB | ALA | B | 367 | 46.103 | 4.017 | 48.824 | 1.00 | 16.47 | B | C |
| ATOM | 3259 | C | ALA | B | 367 | 46.177 | 5.424 | 46.743 | 1.00 | 18.06 | B | C |
| ATOM | 3260 | O | ALA | B | 367 | 47.155 | 6.143 | 46.613 | 1.00 | 18.25 | B | O |
| ATOM | 3261 | N | ALA | B | 368 | 45.600 | 4.787 | 45.722 | 1.00 | 18.36 | B | N |
| ATOM | 3262 | CA | ALA | B | 368 | 46.098 | 4.864 | 44.356 | 1.00 | 18.23 | B | C |
| ATOM | 3263 | CB | ALA | B | 368 | 45.282 | 3.943 | 43.441 | 1.00 | 17.93 | B | C |
| ATOM | 3264 | C | ALA | B | 368 | 46.096 | 6.295 | 43.823 | 1.00 | 18.77 | B | C |
| ATOM | 3265 | O | ALA | B | 368 | 46.900 | 6.641 | 42.962 | 1.00 | 19.54 | B | O |
| ATOM | 3266 | N | ASN | B | 369 | 45.227 | 7.139 | 44.370 | 1.00 | 18.64 | B | N |
| ATOM | 3267 | CA | ASN | B | 369 | 45.139 | 8.526 | 43.942 | 1.00 | 18.62 | B | C |
| ATOM | 3268 | CB | ASN | B | 369 | 43.686 | 8.891 | 43.617 | 1.00 | 20.85 | B | C |
| ATOM | 3269 | CG | ASN | B | 369 | 43.157 | 8.130 | 42.414 | 1.00 | 22.16 | B | C |
| ATOM | 3270 | OD1 | ASN | B | 369 | 43.850 | 7.976 | 41.401 | 1.00 | 24.04 | B | O |
| ATOM | 3271 | ND2 | ASN | B | 369 | 41.935 | 7.639 | 42.519 | 1.00 | 20.54 | B | N |
| ATOM | 3272 | C | ASN | B | 369 | 45.779 | 9.532 | 44.893 | 1.00 | 17.98 | B | C |
| ATOM | 3273 | O | ASN | B | 369 | 45.459 | 10.718 | 44.881 | 1.00 | 19.28 | B | O |
| ATOM | 3274 | N | ILE | B | 370 | 46.640 | 9.035 | 45.772 | 1.00 | 17.24 | B | N |
| ATOM | 3275 | CA | ILE | B | 370 | 47.384 | 9.890 | 46.688 | 1.00 | 15.93 | B | C |
| ATOM | 3276 | CB | ILE | B | 370 | 47.339 | 9.380 | 48.157 | 1.00 | 15.05 | B | C |
| ATOM | 3277 | CG2 | ILE | B | 370 | 48.276 | 10.218 | 49.025 | 1.00 | 14.28 | B | C |
| ATOM | 3278 | CG1 | ILE | B | 370 | 45.908 | 9.445 | 48.701 | 1.00 | 13.28 | B | C |
| ATOM | 3279 | CD1 | ILE | B | 370 | 45.310 | 10.859 | 48.672 | 1.00 | 10.80 | B | C |
| ATOM | 3280 | C | ILE | B | 370 | 48.820 | 9.786 | 46.163 | 1.00 | 14.72 | B | C |
| ATOM | 3281 | O | ILE | B | 370 | 49.260 | 8.709 | 45.797 | 1.00 | 13.16 | B | O |
| ATOM | 3282 | N | LEU | B | 371 | 49.497 | 10.914 | 46.035 | 1.00 | 15.89 | B | N |
| ATOM | 3283 | CA | LEU | B | 371 | 50.870 | 10.906 | 45.545 | 1.00 | 17.53 | B | C |
| ATOM | 3284 | CB | LEU | B | 371 | 51.036 | 11.885 | 44.373 | 1.00 | 17.12 | B | C |
| ATOM | 3285 | CG | LEU | B | 371 | 50.122 | 11.605 | 43.162 | 1.00 | 17.03 | B | C |
| ATOM | 3286 | CD1 | LEU | B | 371 | 50.312 | 12.699 | 42.130 | 1.00 | 17.73 | B | C |
| ATOM | 3287 | CD2 | LEU | B | 371 | 50.379 | 10.227 | 42.548 | 1.00 | 15.47 | B | C |
| ATOM | 3288 | C | LEU | B | 371 | 51.857 | 11.186 | 46.676 | 1.00 | 17.84 | B | C |
| ATOM | 3289 | O | LEU | B | 371 | 51.520 | 11.872 | 47.641 | 1.00 | 17.45 | B | O |
| ATOM | 3290 | N | VAL | B | 372 | 53.052 | 10.602 | 46.571 | 1.00 | 18.62 | B | N |
| ATOM | 3291 | CA | VAL | B | 372 | 54.097 | 10.734 | 47.592 | 1.00 | 18.89 | B | C |

Figure 9

| | | | | | | | | | | |
|---|---|---|---|---|---|---|---|---|---|---|
| ATOM | 3292 | CB  | VAL B 372 | 54.512 |  9.329 | 48.138 | 1.00 | 19.12 | B | C |
| ATOM | 3293 | CG1 | VAL B 372 | 55.376 |  9.480 | 49.366 | 1.00 | 20.07 | B | C |
| ATOM | 3294 | CG2 | VAL B 372 | 53.294 |  8.479 | 48.479 | 1.00 | 17.28 | B | C |
| ATOM | 3295 | C   | VAL B 372 | 55.353 | 11.450 | 47.058 | 1.00 | 19.66 | B | C |
| ATOM | 3296 | O   | VAL B 372 | 55.938 | 11.033 | 46.060 | 1.00 | 18.63 | B | O |
| ATOM | 3297 | N   | SER B 373 | 55.782 | 12.506 | 47.740 | 1.00 | 20.99 | B | N |
| ATOM | 3298 | CA  | SER B 373 | 56.965 | 13.248 | 47.312 | 1.00 | 23.85 | B | C |
| ATOM | 3299 | CB  | SER B 373 | 56.931 | 14.669 | 47.857 | 1.00 | 23.46 | B | C |
| ATOM | 3300 | OG  | SER B 373 | 57.206 | 14.670 | 49.242 | 1.00 | 24.28 | B | O |
| ATOM | 3301 | C   | SER B 373 | 58.285 | 12.590 | 47.731 | 1.00 | 25.72 | B | C |
| ATOM | 3302 | O   | SER B 373 | 58.295 | 11.540 | 48.369 | 1.00 | 24.83 | B | O |
| ATOM | 3303 | N   | ASP B 374 | 59.395 | 13.208 | 47.326 | 1.00 | 29.11 | B | N |
| ATOM | 3304 | CA  | ASP B 374 | 60.740 | 12.730 | 47.658 | 1.00 | 31.52 | B | C |
| ATOM | 3305 | CB  | ASP B 374 | 61.803 | 13.552 | 46.907 | 1.00 | 33.89 | B | C |
| ATOM | 3306 | CG  | ASP B 374 | 61.622 | 15.051 | 47.084 | 1.00 | 36.53 | B | C |
| ATOM | 3307 | OD1 | ASP B 374 | 60.579 | 15.600 | 46.671 | 1.00 | 38.65 | B | O |
| ATOM | 3308 | OD2 | ASP B 374 | 62.538 | 15.691 | 47.637 | 1.00 | 39.99 | B | O |
| ATOM | 3309 | C   | ASP B 374 | 60.957 | 12.822 | 49.160 | 1.00 | 32.12 | B | C |
| ATOM | 3310 | O   | ASP B 374 | 61.653 | 12.000 | 49.750 | 1.00 | 32.39 | B | O |
| ATOM | 3311 | N   | THR B 375 | 60.310 | 13.811 | 49.771 | 1.00 | 33.45 | B | N |
| ATOM | 3312 | CA  | THR B 375 | 60.387 | 14.030 | 51.212 | 1.00 | 34.21 | B | C |
| ATOM | 3313 | CB  | THR B 375 | 60.178 | 15.521 | 51.578 | 1.00 | 34.97 | B | C |
| ATOM | 3314 | OG1 | THR B 375 | 58.840 | 15.917 | 51.250 | 1.00 | 36.79 | B | O |
| ATOM | 3315 | CG2 | THR B 375 | 61.154 | 16.407 | 50.816 | 1.00 | 34.81 | B | C |
| ATOM | 3316 | C   | THR B 375 | 59.333 | 13.192 | 51.942 | 1.00 | 33.85 | B | C |
| ATOM | 3317 | O   | THR B 375 | 59.123 | 13.359 | 53.139 | 1.00 | 34.83 | B | O |
| ATOM | 3318 | N   | LEU B 376 | 58.654 | 12.321 | 51.200 | 1.00 | 33.54 | B | N |
| ATOM | 3319 | CA  | LEU B 376 | 57.614 | 11.431 | 51.728 | 1.00 | 33.18 | B | C |
| ATOM | 3320 | CB  | LEU B 376 | 58.190 | 10.497 | 52.797 | 1.00 | 33.75 | B | C |
| ATOM | 3321 | CG  | LEU B 376 | 59.454 |  9.742 | 52.368 | 1.00 | 34.84 | B | C |
| ATOM | 3322 | CD1 | LEU B 376 | 59.889 |  8.794 | 53.466 | 1.00 | 35.50 | B | C |
| ATOM | 3323 | CD2 | LEU B 376 | 59.206 |  8.993 | 51.073 | 1.00 | 34.15 | B | C |
| ATOM | 3324 | C   | LEU B 376 | 56.320 | 12.098 | 52.229 | 1.00 | 32.73 | B | C |
| ATOM | 3325 | O   | LEU B 376 | 55.653 | 11.579 | 53.132 | 1.00 | 32.90 | B | O |
| ATOM | 3326 | N   | SER B 377 | 55.986 | 13.261 | 51.664 | 1.00 | 31.93 | B | N |
| ATOM | 3327 | CA  | SER B 377 | 54.755 | 13.963 | 52.036 | 1.00 | 31.02 | B | C |
| ATOM | 3328 | CB  | SER B 377 | 54.960 | 15.488 | 52.128 | 1.00 | 31.29 | B | C |
| ATOM | 3329 | OG  | SER B 377 | 55.215 | 16.073 | 50.864 | 1.00 | 34.88 | B | O |
| ATOM | 3330 | C   | SER B 377 | 53.655 | 13.600 | 51.033 | 1.00 | 29.11 | B | C |
| ATOM | 3331 | O   | SER B 377 | 53.920 | 13.418 | 49.837 | 1.00 | 28.53 | B | O |
| ATOM | 3332 | N   | CYS B 378 | 52.432 | 13.459 | 51.539 | 1.00 | 27.20 | B | N |
| ATOM | 3333 | CA  | CYS B 378 | 51.297 | 13.088 | 50.707 | 1.00 | 25.33 | B | C |
| ATOM | 3334 | CB  | CYS B 378 | 50.398 | 12.094 | 51.453 | 1.00 | 24.62 | B | C |
| ATOM | 3335 | SG  | CYS B 378 | 51.197 | 10.514 | 51.790 | 1.00 | 23.79 | B | S |
| ATOM | 3336 | C   | CYS B 378 | 50.482 | 14.266 | 50.183 | 1.00 | 23.62 | B | C |
| ATOM | 3337 | O   | CYS B 378 | 50.280 | 15.256 | 50.884 | 1.00 | 22.93 | B | O |
| ATOM | 3338 | N   | LYS B 379 | 50.117 | 14.179 | 48.903 | 1.00 | 22.80 | B | N |
| ATOM | 3339 | CA  | LYS B 379 | 49.301 | 15.185 | 48.229 | 1.00 | 22.21 | B | C |
| ATOM | 3340 | CB  | LYS B 379 | 50.140 | 16.009 | 47.245 | 1.00 | 22.70 | B | C |
| ATOM | 3341 | CG  | LYS B 379 | 50.940 | 17.145 | 47.915 | 1.00 | 23.90 | B | C |
| ATOM | 3342 | CD  | LYS B 379 | 52.027 | 17.696 | 47.009 | 1.00 | 24.84 | B | C |
| ATOM | 3343 | CE  | LYS B 379 | 52.714 | 18.927 | 47.584 | 1.00 | 26.98 | B | C |
| ATOM | 3344 | NZ  | LYS B 379 | 52.056 | 20.191 | 47.082 | 1.00 | 32.26 | B | N |
| ATOM | 3345 | C   | LYS B 379 | 48.163 | 14.446 | 47.522 | 1.00 | 21.65 | B | C |
| ATOM | 3346 | O   | LYS B 379 | 48.316 | 13.300 | 47.088 | 1.00 | 21.22 | B | O |
| ATOM | 3347 | N   | ILE B 380 | 47.000 | 15.079 | 47.467 | 1.00 | 21.77 | B | N |
| ATOM | 3348 | CA  | ILE B 380 | 45.826 | 14.479 | 46.847 | 1.00 | 21.91 | B | C |
| ATOM | 3349 | CB  | ILE B 380 | 44.506 | 15.048 | 47.470 | 1.00 | 23.11 | B | C |
| ATOM | 3350 | CG2 | ILE B 380 | 43.284 | 14.374 | 46.864 | 1.00 | 22.13 | B | C |

Figure 9

| ATOM | 3351 | CG1 | ILE | B | 380 | 44.507 | 14.849 | 48.984 | 1.00 | 24.27 | B | C |
|------|------|-----|-----|---|-----|--------|--------|--------|------|-------|---|---|
| ATOM | 3352 | CD1 | ILE | B | 380 | 43.276 | 15.373 | 49.631 | 1.00 | 23.78 | B | C |
| ATOM | 3353 | C   | ILE | B | 380 | 45.803 | 14.743 | 45.344 | 1.00 | 21.20 | B | C |
| ATOM | 3354 | O   | ILE | B | 380 | 45.926 | 15.889 | 44.904 | 1.00 | 20.60 | B | O |
| ATOM | 3355 | N   | ALA | B | 381 | 45.612 | 13.677 | 44.571 | 1.00 | 21.04 | B | N |
| ATOM | 3356 | CA  | ALA | B | 381 | 45.546 | 13.793 | 43.117 | 1.00 | 20.87 | B | C |
| ATOM | 3357 | CB  | ALA | B | 381 | 46.590 | 12.904 | 42.476 | 1.00 | 19.64 | B | C |
| ATOM | 3358 | C   | ALA | B | 381 | 44.165 | 13.391 | 42.622 | 1.00 | 20.33 | B | C |
| ATOM | 3359 | O   | ALA | B | 381 | 43.402 | 12.751 | 43.348 | 1.00 | 19.52 | B | O |
| ATOM | 3360 | N   | ASP | B | 382 | 43.867 | 13.787 | 41.384 | 1.00 | 20.28 | B | N |
| ATOM | 3361 | CA  | ASP | B | 382 | 42.613 | 13.468 | 40.684 | 1.00 | 20.30 | B | C |
| ATOM | 3362 | CB  | ASP | B | 382 | 42.661 | 12.041 | 40.155 | 1.00 | 20.57 | B | C |
| ATOM | 3363 | CG  | ASP | B | 382 | 43.666 | 11.867 | 39.028 | 1.00 | 21.10 | B | C |
| ATOM | 3364 | OD1 | ASP | B | 382 | 43.818 | 12.795 | 38.214 | 1.00 | 20.70 | B | O |
| ATOM | 3365 | OD2 | ASP | B | 382 | 44.289 | 10.792 | 38.956 | 1.00 | 21.71 | B | O |
| ATOM | 3366 | C   | ASP | B | 382 | 41.331 | 13.672 | 41.458 | 1.00 | 19.48 | B | C |
| ATOM | 3367 | O   | ASP | B | 382 | 40.446 | 12.820 | 41.441 | 1.00 | 19.20 | B | O |
| ATOM | 3368 | N   | PHE | B | 383 | 41.243 | 14.818 | 42.111 | 1.00 | 20.37 | B | N |
| ATOM | 3369 | CA  | PHE | B | 383 | 40.096 | 15.195 | 42.913 | 1.00 | 22.59 | B | C |
| ATOM | 3370 | CB  | PHE | B | 383 | 40.575 | 16.007 | 44.129 | 1.00 | 21.67 | B | C |
| ATOM | 3371 | CG  | PHE | B | 383 | 41.509 | 17.145 | 43.778 | 1.00 | 21.87 | B | C |
| ATOM | 3372 | CD1 | PHE | B | 383 | 41.018 | 18.352 | 43.279 | 1.00 | 21.53 | B | C |
| ATOM | 3373 | CD2 | PHE | B | 383 | 42.892 | 16.991 | 43.917 | 1.00 | 22.38 | B | C |
| ATOM | 3374 | CE1 | PHE | B | 383 | 41.888 | 19.398 | 42.916 | 1.00 | 21.05 | B | C |
| ATOM | 3375 | CE2 | PHE | B | 383 | 43.773 | 18.024 | 43.559 | 1.00 | 21.77 | B | C |
| ATOM | 3376 | CZ  | PHE | B | 383 | 43.269 | 19.229 | 43.057 | 1.00 | 22.42 | B | C |
| ATOM | 3377 | C   | PHE | B | 383 | 39.069 | 16.023 | 42.134 | 1.00 | 24.01 | B | C |
| ATOM | 3378 | O   | PHE | B | 383 | 39.425 | 16.803 | 41.244 | 1.00 | 24.21 | B | O |
| ATOM | 3379 | N   | GLY | B | 384 | 37.803 | 15.857 | 42.501 | 1.00 | 25.26 | B | N |
| ATOM | 3380 | CA  | GLY | B | 384 | 36.736 | 16.630 | 41.895 | 1.00 | 27.08 | B | C |
| ATOM | 3381 | C   | GLY | B | 384 | 36.292 | 16.268 | 40.498 | 1.00 | 27.93 | B | C |
| ATOM | 3382 | O   | GLY | B | 384 | 35.616 | 17.065 | 39.862 | 1.00 | 29.12 | B | O |
| ATOM | 3383 | N   | LEU | B | 385 | 36.689 | 15.101 | 40.009 | 1.00 | 28.53 | B | N |
| ATOM | 3384 | CA  | LEU | B | 385 | 36.288 | 14.671 | 38.680 | 1.00 | 29.45 | B | C |
| ATOM | 3385 | CB  | LEU | B | 385 | 37.089 | 13.443 | 38.245 | 1.00 | 27.62 | B | C |
| ATOM | 3386 | CG  | LEU | B | 385 | 38.611 | 13.624 | 38.170 | 1.00 | 28.14 | B | C |
| ATOM | 3387 | CD1 | LEU | B | 385 | 39.251 | 12.360 | 37.646 | 1.00 | 27.39 | B | C |
| ATOM | 3388 | CD2 | LEU | B | 385 | 38.975 | 14.796 | 37.286 | 1.00 | 26.90 | B | C |
| ATOM | 3389 | C   | LEU | B | 385 | 34.802 | 14.339 | 38.739 | 1.00 | 31.13 | B | C |
| ATOM | 3390 | O   | LEU | B | 385 | 34.318 | 13.870 | 39.754 | 1.00 | 31.06 | B | O |
| ATOM | 3391 | N   | ALA | B | 386 | 34.068 | 14.666 | 37.680 | 1.00 | 32.66 | B | N |
| ATOM | 3392 | CA  | ALA | B | 386 | 32.632 | 14.399 | 37.612 | 1.00 | 33.96 | B | C |
| ATOM | 3393 | CB  | ALA | B | 386 | 32.031 | 15.115 | 36.395 | 1.00 | 35.36 | B | C |
| ATOM | 3394 | C   | ALA | B | 386 | 32.361 | 12.907 | 37.502 | 1.00 | 34.42 | B | C |
| ATOM | 3395 | O   | ALA | B | 386 | 31.259 | 12.436 | 37.780 | 1.00 | 34.00 | B | O |
| ATOM | 3396 | N   | ARG | B | 387 | 33.382 | 12.168 | 37.099 | 1.00 | 35.23 | B | N |
| ATOM | 3397 | CA  | ARG | B | 387 | 33.250 | 10.735 | 36.906 | 1.00 | 35.46 | B | C |
| ATOM | 3398 | CB  | ARG | B | 387 | 33.677 | 10.397 | 35.475 | 1.00 | 36.36 | B | C |
| ATOM | 3399 | CG  | ARG | B | 387 | 35.093 | 10.877 | 35.131 | 1.00 | 37.12 | B | C |
| ATOM | 3400 | CD  | ARG | B | 387 | 35.524 | 10.422 | 33.759 | 1.00 | 37.31 | B | C |
| ATOM | 3401 | NE  | ARG | B | 387 | 36.937 | 10.689 | 33.504 | 1.00 | 38.55 | B | N |
| ATOM | 3402 | CZ  | ARG | B | 387 | 37.878 |  9.750 | 33.473 | 1.00 | 39.68 | B | C |
| ATOM | 3403 | NH1 | ARG | B | 387 | 37.553 |  8.476 | 33.685 | 1.00 | 40.14 | B | N |
| ATOM | 3404 | NH2 | ARG | B | 387 | 39.150 | 10.079 | 33.239 | 1.00 | 41.78 | B | N |
| ATOM | 3405 | C   | ARG | B | 387 | 34.024 |  9.849 | 37.879 | 1.00 | 34.80 | B | C |
| ATOM | 3406 | O   | ARG | B | 387 | 34.878 | 10.298 | 38.632 | 1.00 | 34.59 | B | O |
| ATOM | 3407 | N   | LEU | B | 388 | 33.701 |  8.570 | 37.836 | 1.00 | 34.07 | B | N |
| ATOM | 3408 | CA  | LEU | B | 388 | 34.373 |  7.586 | 38.645 | 1.00 | 33.84 | B | C |
| ATOM | 3409 | CB  | LEU | B | 388 | 33.412 |  6.466 | 39.000 | 1.00 | 35.19 | B | C |

Figure 9

```
ATOM   3410  CG   LEU B 388      32.193   6.909  39.802  1.00 37.34      B    C
ATOM   3411  CD1  LEU B 388      31.572   5.679  40.434  1.00 37.78      B    C
ATOM   3412  CD2  LEU B 388      32.607   7.886  40.889  1.00 38.11      B    C
ATOM   3413  C    LEU B 388      35.494   7.046  37.767  1.00 33.47      B    C
ATOM   3414  O    LEU B 388      35.230   6.529  36.673  1.00 33.35      B    O
ATOM   3415  N    ILE B 389      36.739   7.202  38.221  1.00 32.09      B    N
ATOM   3416  CA   ILE B 389      37.898   6.747  37.459  1.00 30.58      B    C
ATOM   3417  CB   ILE B 389      39.049   7.808  37.441  1.00 27.88      B    C
ATOM   3418  CG2  ILE B 389      38.497   9.186  37.101  1.00 26.93      B    C
ATOM   3419  CG1  ILE B 389      39.807   7.830  38.767  1.00 24.73      B    C
ATOM   3420  CD1  ILE B 389      40.774   8.970  38.878  1.00 21.80      B    C
ATOM   3421  C    ILE B 389      38.448   5.402  37.893  1.00 31.62      B    C
ATOM   3422  O    ILE B 389      38.116   4.894  38.953  1.00 31.08      B    O
ATOM   3423  N    GLU B 390      39.241   4.814  37.008  1.00 33.79      B    N
ATOM   3424  CA   GLU B 390      39.895   3.533  37.218  1.00 36.46      B    C
ATOM   3425  CB   GLU B 390      39.479   2.540  36.139  1.00 36.83      B    C
ATOM   3426  CG   GLU B 390      38.053   2.063  36.288  1.00 38.91      B    C
ATOM   3427  CD   GLU B 390      37.567   1.260  35.103  1.00 40.01      B    C
ATOM   3428  OE1  GLU B 390      36.346   1.313  34.832  1.00 42.61      B    O
ATOM   3429  OE2  GLU B 390      38.388   0.582  34.444  1.00 39.98      B    O
ATOM   3430  C    GLU B 390      41.399   3.778  37.175  1.00 38.29      B    C
ATOM   3431  O    GLU B 390      41.896   4.651  36.446  1.00 38.90      B    O
ATOM   3432  N    ASP B 391      42.131   2.955  37.910  1.00 39.80      B    N
ATOM   3433  CA   ASP B 391      43.576   3.111  38.024  1.00 41.52      B    C
ATOM   3434  CB   ASP B 391      44.047   2.381  39.289  1.00 43.20      B    C
ATOM   3435  CG   ASP B 391      43.280   2.830  40.543  1.00 45.14      B    C
ATOM   3436  OD1  ASP B 391      42.986   4.052  40.696  1.00 43.76      B    O
ATOM   3437  OD2  ASP B 391      42.955   1.946  41.368  1.00 46.30      B    O
ATOM   3438  C    ASP B 391      44.434   2.730  36.815  1.00 41.30      B    C
ATOM   3439  O    ASP B 391      45.646   2.992  36.810  1.00 40.95      B    O
ATOM   3440  N    ASN B 392      43.793   2.166  35.789  1.00 40.78      B    N
ATOM   3441  CA   ASN B 392      44.468   1.720  34.572  1.00 39.99      B    C
ATOM   3442  CB   ASN B 392      43.876   0.374  34.118  1.00 41.20      B    C
ATOM   3443  CG   ASN B 392      42.430   0.498  33.607  1.00 42.13      B    C
ATOM   3444  OD1  ASN B 392      41.789   1.546  33.752  1.00 41.81      B    O
ATOM   3445  ND2  ASN B 392      41.919  -0.571  32.997  1.00 42.88      B    N
ATOM   3446  C    ASN B 392      44.388   2.725  33.412  1.00 39.48      B    C
ATOM   3447  O    ASN B 392      44.697   2.379  32.266  1.00 39.63      B    O
ATOM   3448  N    GLU B 393      44.006   3.964  33.706  1.00 37.97      B    N
ATOM   3449  CA   GLU B 393      43.863   4.967  32.655  1.00 37.63      B    C
ATOM   3450  CB   GLU B 393      42.788   5.962  33.042  1.00 37.39      B    C
ATOM   3451  CG   GLU B 393      41.432   5.307  33.103  1.00 37.59      B    C
ATOM   3452  CD   GLU B 393      40.450   6.072  33.933  1.00 37.73      B    C
ATOM   3453  OE1  GLU B 393      40.715   7.246  34.249  1.00 38.65      B    O
ATOM   3454  OE2  GLU B 393      39.396   5.497  34.259  1.00 40.22      B    O
ATOM   3455  C    GLU B 393      45.105   5.687  32.132  1.00 37.58      B    C
ATOM   3456  O    GLU B 393      45.114   6.157  30.993  1.00 36.88      B    O
ATOM   3457  N    TYR B 394      46.136   5.803  32.962  1.00 37.61      B    N
ATOM   3458  CA   TYR B 394      47.375   6.443  32.535  1.00 37.62      B    C
ATOM   3459  CB   TYR B 394      47.487   7.860  33.086  1.00 36.62      B    C
ATOM   3460  CG   TYR B 394      46.400   8.784  32.594  1.00 36.36      B    C
ATOM   3461  CD1  TYR B 394      45.187   8.885  33.275  1.00 36.62      B    C
ATOM   3462  CE1  TYR B 394      44.170   9.723  32.821  1.00 35.66      B    C
ATOM   3463  CD2  TYR B 394      46.570   9.550  31.442  1.00 36.67      B    C
ATOM   3464  CE2  TYR B 394      45.557  10.398  30.978  1.00 35.42      B    C
ATOM   3465  CZ   TYR B 394      44.361  10.475  31.673  1.00 36.10      B    C
ATOM   3466  OH   TYR B 394      43.344  11.291  31.225  1.00 36.25      B    O
ATOM   3467  C    TYR B 394      48.587   5.588  32.909  1.00 38.47      B    C
ATOM   3468  O    TYR B 394      49.723   5.996  32.694  1.00 37.38      B    O
```

Figure 9

| ATOM | 3469 | N | THR | B | 395 | 48.315 | 4.406 | 33.474 | 1.00 | 40.43 | B | N |
|------|------|-----|-----|---|-----|--------|--------|--------|------|-------|---|---|
| ATOM | 3470 | CA | THR | B | 395 | 49.322 | 3.409 | 33.865 | 1.00 | 43.18 | B | C |
| ATOM | 3471 | CB | THR | B | 395 | 49.773 | 3.511 | 35.341 | 1.00 | 44.01 | B | C |
| ATOM | 3472 | OG1 | THR | B | 395 | 48.640 | 3.571 | 36.222 | 1.00 | 45.23 | B | O |
| ATOM | 3473 | CG2 | THR | B | 395 | 50.615 | 4.719 | 35.514 | 1.00 | 44.52 | B | C |
| ATOM | 3474 | C | THR | B | 395 | 48.765 | 2.022 | 33.610 | 1.00 | 44.64 | B | C |
| ATOM | 3475 | O | THR | B | 395 | 47.667 | 1.892 | 33.083 | 1.00 | 44.86 | B | O |
| ATOM | 3476 | N | ALA | B | 396 | 49.485 | 0.988 | 34.033 | 1.00 | 47.06 | B | N |
| ATOM | 3477 | CA | ALA | B | 396 | 49.042 | -0.378 | 33.768 | 1.00 | 49.78 | B | C |
| ATOM | 3478 | CB | ALA | B | 396 | 50.060 | -1.077 | 32.851 | 1.00 | 49.00 | B | C |
| ATOM | 3479 | C | ALA | B | 396 | 48.680 | -1.280 | 34.961 | 1.00 | 51.62 | B | C |
| ATOM | 3480 | O | ALA | B | 396 | 49.103 | -2.437 | 35.018 | 1.00 | 53.45 | B | O |
| ATOM | 3481 | N | ARG | B | 397 | 47.869 | -0.780 | 35.888 | 1.00 | 52.68 | B | N |
| ATOM | 3482 | CA | ARG | B | 397 | 47.457 | -1.592 | 37.028 | 1.00 | 53.54 | B | C |
| ATOM | 3483 | CB | ARG | B | 397 | 46.855 | -0.706 | 38.119 | 1.00 | 54.42 | B | C |
| ATOM | 3484 | CG | ARG | B | 397 | 47.795 | 0.378 | 38.640 | 1.00 | 54.78 | B | C |
| ATOM | 3485 | CD | ARG | B | 397 | 47.979 | 0.253 | 40.147 | 1.00 | 55.24 | B | C |
| ATOM | 3486 | NE | ARG | B | 397 | 48.714 | 1.375 | 40.728 | 1.00 | 54.73 | B | N |
| ATOM | 3487 | CZ | ARG | B | 397 | 48.329 | 2.645 | 40.643 | 1.00 | 53.85 | B | C |
| ATOM | 3488 | NH1 | ARG | B | 397 | 47.221 | 2.969 | 39.992 | 1.00 | 53.22 | B | N |
| ATOM | 3489 | NH2 | ARG | B | 397 | 49.031 | 3.590 | 41.246 | 1.00 | 54.22 | B | N |
| ATOM | 3490 | C | ARG | B | 397 | 46.434 | -2.648 | 36.587 | 1.00 | 54.23 | B | C |
| ATOM | 3491 | O | ARG | B | 397 | 46.796 | -3.848 | 36.571 | 1.00 | 54.68 | B | O |
| ATOM | 3492 | CB | PRO | B | 403 | 36.361 | 1.958 | 41.194 | 1.00 | 35.60 | B | C |
| ATOM | 3493 | CG | PRO | B | 403 | 37.023 | 1.383 | 39.905 | 1.00 | 35.93 | B | C |
| ATOM | 3494 | C | PRO | B | 403 | 35.286 | 0.778 | 43.163 | 1.00 | 33.43 | B | C |
| ATOM | 3495 | O | PRO | B | 403 | 35.250 | 1.720 | 43.992 | 1.00 | 33.48 | B | O |
| ATOM | 3496 | N | PRO | B | 403 | 36.021 | -0.420 | 41.078 | 1.00 | 34.69 | B | N |
| ATOM | 3497 | CD | PRO | B | 403 | 36.358 | -0.022 | 39.704 | 1.00 | 35.76 | B | C |
| ATOM | 3498 | CA | PRO | B | 403 | 36.321 | 0.702 | 42.031 | 1.00 | 34.39 | B | C |
| ATOM | 3499 | N | ILE | B | 404 | 34.531 | -0.307 | 43.244 | 1.00 | 30.88 | B | N |
| ATOM | 3500 | CA | ILE | B | 404 | 33.466 | -0.512 | 44.210 | 1.00 | 28.31 | B | C |
| ATOM | 3501 | CB | ILE | B | 404 | 32.676 | -1.801 | 43.789 | 1.00 | 28.25 | B | C |
| ATOM | 3502 | CG2 | ILE | B | 404 | 32.070 | -2.522 | 44.973 | 1.00 | 28.01 | B | C |
| ATOM | 3503 | CG1 | ILE | B | 404 | 31.649 | -1.440 | 42.725 | 1.00 | 28.13 | B | C |
| ATOM | 3504 | CD1 | ILE | B | 404 | 30.642 | -0.404 | 43.211 | 1.00 | 29.17 | B | C |
| ATOM | 3505 | C | ILE | B | 404 | 33.919 | -0.576 | 45.687 | 1.00 | 26.26 | B | C |
| ATOM | 3506 | O | ILE | B | 404 | 33.199 | -0.113 | 46.562 | 1.00 | 25.93 | B | O |
| ATOM | 3507 | N | LYS | B | 405 | 35.123 | -1.078 | 45.958 | 1.00 | 23.95 | B | N |
| ATOM | 3508 | CA | LYS | B | 405 | 35.595 | -1.216 | 47.335 | 1.00 | 22.46 | B | C |
| ATOM | 3509 | CB | LYS | B | 405 | 36.816 | -2.140 | 47.398 | 1.00 | 22.34 | B | C |
| ATOM | 3510 | CG | LYS | B | 405 | 36.486 | -3.590 | 47.029 | 1.00 | 22.94 | B | C |
| ATOM | 3511 | CD | LYS | B | 405 | 37.704 | -4.500 | 47.178 | 1.00 | 24.78 | B | C |
| ATOM | 3512 | CE | LYS | B | 405 | 37.388 | -5.950 | 46.830 | 1.00 | 25.04 | B | C |
| ATOM | 3513 | NZ | LYS | B | 405 | 38.446 | -6.898 | 47.324 | 1.00 | 26.05 | B | N |
| ATOM | 3514 | C | LYS | B | 405 | 35.808 | 0.047 | 48.173 | 1.00 | 20.83 | B | C |
| ATOM | 3515 | O | LYS | B | 405 | 36.030 | -0.050 | 49.382 | 1.00 | 21.14 | B | O |
| ATOM | 3516 | N | TRP | B | 406 | 35.736 | 1.220 | 47.544 | 1.00 | 19.62 | B | N |
| ATOM | 3517 | CA | TRP | B | 406 | 35.883 | 2.489 | 48.252 | 1.00 | 19.96 | B | C |
| ATOM | 3518 | CB | TRP | B | 406 | 36.965 | 3.363 | 47.606 | 1.00 | 20.28 | B | C |
| ATOM | 3519 | CG | TRP | B | 406 | 38.362 | 2.814 | 47.759 | 1.00 | 21.33 | B | C |
| ATOM | 3520 | CD2 | TRP | B | 406 | 38.962 | 1.793 | 46.957 | 1.00 | 20.51 | B | C |
| ATOM | 3521 | CE2 | TRP | B | 406 | 40.233 | 1.517 | 47.515 | 1.00 | 20.53 | B | C |
| ATOM | 3522 | CE3 | TRP | B | 406 | 38.544 | 1.080 | 45.822 | 1.00 | 19.32 | B | C |
| ATOM | 3523 | CD1 | TRP | B | 406 | 39.276 | 3.127 | 48.738 | 1.00 | 20.95 | B | C |
| ATOM | 3524 | NE1 | TRP | B | 406 | 40.395 | 2.343 | 48.600 | 1.00 | 20.63 | B | N |
| ATOM | 3525 | CZ2 | TRP | B | 406 | 41.088 | 0.555 | 46.976 | 1.00 | 19.78 | B | C |
| ATOM | 3526 | CZ3 | TRP | B | 406 | 39.386 | 0.128 | 45.289 | 1.00 | 19.72 | B | C |
| ATOM | 3527 | CH2 | TRP | B | 406 | 40.649 | -0.130 | 45.866 | 1.00 | 20.81 | B | C |

Figure 9

| ATOM | 3528 | C | TRP | B | 406 | 34.580 | 3.289 | 48.267 | 1.00 | 20.59 | B | C |
|------|------|-----|-----|---|-----|--------|-------|--------|------|-------|---|---|
| ATOM | 3529 | O | TRP | B | 406 | 34.501 | 4.346 | 48.901 | 1.00 | 21.22 | B | O |
| ATOM | 3530 | N | THR | B | 407 | 33.557 | 2.769 | 47.596 | 1.00 | 20.39 | B | N |
| ATOM | 3531 | CA | THR | B | 407 | 32.281 | 3.467 | 47.447 | 1.00 | 20.15 | B | C |
| ATOM | 3532 | CB | THR | B | 407 | 31.670 | 3.116 | 46.073 | 1.00 | 20.87 | B | C |
| ATOM | 3533 | OG1 | THR | B | 407 | 32.693 | 3.197 | 45.076 | 1.00 | 22.37 | B | O |
| ATOM | 3534 | CG2 | THR | B | 407 | 30.575 | 4.096 | 45.711 | 1.00 | 20.38 | B | C |
| ATOM | 3535 | C | THR | B | 407 | 31.266 | 3.243 | 48.565 | 1.00 | 18.70 | B | C |
| ATOM | 3536 | O | THR | B | 407 | 30.948 | 2.102 | 48.900 | 1.00 | 18.70 | B | O |
| ATOM | 3537 | N | ALA | B | 408 | 30.770 | 4.346 | 49.130 | 1.00 | 18.11 | B | N |
| ATOM | 3538 | CA | ALA | B | 408 | 29.787 | 4.313 | 50.221 | 1.00 | 18.84 | B | C |
| ATOM | 3539 | CB | ALA | B | 408 | 29.501 | 5.712 | 50.706 | 1.00 | 16.41 | B | C |
| ATOM | 3540 | C | ALA | B | 408 | 28.499 | 3.655 | 49.762 | 1.00 | 19.41 | B | C |
| ATOM | 3541 | O | ALA | B | 408 | 28.108 | 3.831 | 48.612 | 1.00 | 20.29 | B | O |
| ATOM | 3542 | N | PRO | B | 409 | 27.766 | 2.975 | 50.679 | 1.00 | 20.15 | B | N |
| ATOM | 3543 | CD | PRO | B | 409 | 27.986 | 2.861 | 52.130 | 1.00 | 18.77 | B | C |
| ATOM | 3544 | CA | PRO | B | 409 | 26.510 | 2.301 | 50.317 | 1.00 | 20.33 | B | C |
| ATOM | 3545 | CB | PRO | B | 409 | 25.985 | 1.800 | 51.665 | 1.00 | 20.84 | B | C |
| ATOM | 3546 | CG | PRO | B | 409 | 27.228 | 1.615 | 52.462 | 1.00 | 18.93 | B | C |
| ATOM | 3547 | C | PRO | B | 409 | 25.496 | 3.172 | 49.577 | 1.00 | 20.07 | B | C |
| ATOM | 3548 | O | PRO | B | 409 | 24.897 | 2.708 | 48.612 | 1.00 | 19.70 | B | O |
| ATOM | 3549 | N | GLU | B | 410 | 25.334 | 4.429 | 49.988 | 1.00 | 19.36 | B | N |
| ATOM | 3550 | CA | GLU | B | 410 | 24.391 | 5.314 | 49.311 | 1.00 | 20.87 | B | C |
| ATOM | 3551 | CB | GLU | B | 410 | 24.072 | 6.562 | 50.156 | 1.00 | 20.06 | B | C |
| ATOM | 3552 | CG | GLU | B | 410 | 25.178 | 7.623 | 50.265 | 1.00 | 20.00 | B | C |
| ATOM | 3553 | CD | GLU | B | 410 | 26.279 | 7.327 | 51.295 | 1.00 | 18.27 | B | C |
| ATOM | 3554 | OE1 | GLU | B | 410 | 26.248 | 6.286 | 51.988 | 1.00 | 18.54 | B | O |
| ATOM | 3555 | OE2 | GLU | B | 410 | 27.178 | 8.177 | 51.413 | 1.00 | 17.59 | B | O |
| ATOM | 3556 | C | GLU | B | 410 | 24.861 | 5.703 | 47.894 | 1.00 | 22.65 | B | C |
| ATOM | 3557 | O | GLU | B | 410 | 24.041 | 5.993 | 47.007 | 1.00 | 23.21 | B | O |
| ATOM | 3558 | N | ALA | B | 411 | 26.176 | 5.694 | 47.673 | 1.00 | 23.21 | B | N |
| ATOM | 3559 | CA | ALA | B | 411 | 26.719 | 6.025 | 46.365 | 1.00 | 22.95 | B | C |
| ATOM | 3560 | CB | ALA | B | 411 | 28.146 | 6.462 | 46.494 | 1.00 | 23.12 | B | C |
| ATOM | 3561 | C | ALA | B | 411 | 26.596 | 4.820 | 45.436 | 1.00 | 23.81 | B | C |
| ATOM | 3562 | O | ALA | B | 411 | 26.488 | 4.966 | 44.223 | 1.00 | 24.48 | B | O |
| ATOM | 3563 | N | ILE | B | 412 | 26.592 | 3.625 | 46.008 | 1.00 | 24.72 | B | N |
| ATOM | 3564 | CA | ILE | B | 412 | 26.458 | 2.409 | 45.222 | 1.00 | 26.06 | B | C |
| ATOM | 3565 | CB | ILE | B | 412 | 26.906 | 1.164 | 46.008 | 1.00 | 25.55 | B | C |
| ATOM | 3566 | CG2 | ILE | B | 412 | 26.514 | -0.096 | 45.248 | 1.00 | 26.24 | B | C |
| ATOM | 3567 | CG1 | ILE | B | 412 | 28.418 | 1.192 | 46.235 | 1.00 | 25.51 | B | C |
| ATOM | 3568 | CD1 | ILE | B | 412 | 28.931 | 0.058 | 47.078 | 1.00 | 23.45 | B | C |
| ATOM | 3569 | C | ILE | B | 412 | 25.005 | 2.187 | 44.785 | 1.00 | 28.11 | B | C |
| ATOM | 3570 | O | ILE | B | 412 | 24.745 | 1.922 | 43.610 | 1.00 | 28.43 | B | O |
| ATOM | 3571 | N | ASN | B | 413 | 24.078 | 2.306 | 45.741 | 1.00 | 28.85 | B | N |
| ATOM | 3572 | CA | ASN | B | 413 | 22.643 | 2.096 | 45.521 | 1.00 | 29.69 | B | C |
| ATOM | 3573 | CB | ASN | B | 413 | 21.936 | 1.850 | 46.857 | 1.00 | 29.63 | B | C |
| ATOM | 3574 | CG | ASN | B | 413 | 22.512 | 0.681 | 47.614 | 1.00 | 31.41 | B | C |
| ATOM | 3575 | OD1 | ASN | B | 413 | 23.003 | -0.271 | 47.016 | 1.00 | 32.92 | B | O |
| ATOM | 3576 | ND2 | ASN | B | 413 | 22.471 | 0.750 | 48.940 | 1.00 | 31.93 | B | N |
| ATOM | 3577 | C | ASN | B | 413 | 21.882 | 3.194 | 44.790 | 1.00 | 29.67 | B | C |
| ATOM | 3578 | O | ASN | B | 413 | 20.982 | 2.900 | 44.017 | 1.00 | 30.79 | B | O |
| ATOM | 3579 | N | TYR | B | 414 | 22.211 | 4.454 | 45.065 | 1.00 | 30.30 | B | N |
| ATOM | 3580 | CA | TYR | B | 414 | 21.500 | 5.579 | 44.455 | 1.00 | 29.92 | B | C |
| ATOM | 3581 | CB | TYR | B | 414 | 20.658 | 6.278 | 45.531 | 1.00 | 30.91 | B | C |
| ATOM | 3582 | CG | TYR | B | 414 | 19.822 | 5.310 | 46.326 | 1.00 | 33.99 | B | C |
| ATOM | 3583 | CD1 | TYR | B | 414 | 18.732 | 4.665 | 45.742 | 1.00 | 35.69 | B | C |
| ATOM | 3584 | CE1 | TYR | B | 414 | 18.006 | 3.697 | 46.439 | 1.00 | 36.71 | B | C |
| ATOM | 3585 | CD2 | TYR | B | 414 | 20.163 | 4.974 | 47.643 | 1.00 | 35.55 | B | C |
| ATOM | 3586 | CE2 | TYR | B | 414 | 19.443 | 4.006 | 48.354 | 1.00 | 35.70 | B | C |

Figure 9

| | | | | | | | | | | |
|---|---|---|---|---|---|---|---|---|---|---|
| ATOM | 3587 | CZ | TYR | B | 414 | 18.370 | 3.371 | 47.740 | 1.00 37.57 | B C |
| ATOM | 3588 | OH | TYR | B | 414 | 17.680 | 2.379 | 48.401 | 1.00 40.06 | B O |
| ATOM | 3589 | C | TYR | B | 414 | 22.378 | 6.608 | 43.732 | 1.00 28.59 | B C |
| ATOM | 3590 | O | TYR | B | 414 | 21.868 | 7.591 | 43.188 | 1.00 28.33 | B O |
| ATOM | 3591 | N | GLY | B | 415 | 23.689 | 6.390 | 43.734 | 1.00 27.16 | B N |
| ATOM | 3592 | CA | GLY | B | 415 | 24.583 | 7.325 | 43.079 | 1.00 25.41 | B C |
| ATOM | 3593 | C | GLY | B | 415 | 24.688 | 8.660 | 43.789 | 1.00 24.76 | B C |
| ATOM | 3594 | O | GLY | B | 415 | 25.052 | 9.674 | 43.183 | 1.00 25.17 | B O |
| ATOM | 3595 | N | THR | B | 416 | 24.375 | 8.685 | 45.078 | 1.00 24.51 | B N |
| ATOM | 3596 | CA | THR | B | 416 | 24.469 | 9.935 | 45.812 | 1.00 23.94 | B C |
| ATOM | 3597 | CB | THR | B | 416 | 23.262 | 10.138 | 46.800 | 1.00 23.95 | B C |
| ATOM | 3598 | OG1 | THR | B | 416 | 23.710 | 10.718 | 48.028 | 1.00 27.71 | B O |
| ATOM | 3599 | CG2 | THR | B | 416 | 22.520 | 8.854 | 47.057 | 1.00 21.71 | B C |
| ATOM | 3600 | C | THR | B | 416 | 25.870 | 10.109 | 46.428 | 1.00 23.05 | B C |
| ATOM | 3601 | O | THR | B | 416 | 26.217 | 9.508 | 47.436 | 1.00 23.30 | B O |
| ATOM | 3602 | N | PHE | B | 417 | 26.687 | 10.882 | 45.717 | 1.00 22.52 | B N |
| ATOM | 3603 | CA | PHE | B | 417 | 28.066 | 11.179 | 46.078 | 1.00 20.91 | B C |
| ATOM | 3604 | CB | PHE | B | 417 | 28.965 | 11.174 | 44.826 | 1.00 20.23 | B C |
| ATOM | 3605 | CG | PHE | B | 417 | 29.214 | 9.806 | 44.238 | 1.00 20.96 | B C |
| ATOM | 3606 | CD1 | PHE | B | 417 | 28.335 | 9.256 | 43.302 | 1.00 21.29 | B C |
| ATOM | 3607 | CD2 | PHE | B | 417 | 30.326 | 9.057 | 44.630 | 1.00 20.64 | B C |
| ATOM | 3608 | CE1 | PHE | B | 417 | 28.564 | 7.978 | 42.772 | 1.00 20.61 | B C |
| ATOM | 3609 | CE2 | PHE | B | 417 | 30.560 | 7.786 | 44.108 | 1.00 18.76 | B C |
| ATOM | 3610 | CZ | PHE | B | 417 | 29.686 | 7.244 | 43.185 | 1.00 19.70 | B C |
| ATOM | 3611 | C | PHE | B | 417 | 28.165 | 12.536 | 46.745 | 1.00 19.85 | B C |
| ATOM | 3612 | O | PHE | B | 417 | 27.759 | 13.543 | 46.176 | 1.00 20.66 | B O |
| ATOM | 3613 | N | THR | B | 418 | 28.717 | 12.559 | 47.955 | 1.00 19.64 | B N |
| ATOM | 3614 | CA | THR | B | 418 | 28.901 | 13.801 | 48.719 | 1.00 18.28 | B C |
| ATOM | 3615 | CB | THR | B | 418 | 27.751 | 14.017 | 49.756 | 1.00 17.70 | B C |
| ATOM | 3616 | OG1 | THR | B | 418 | 27.839 | 13.032 | 50.799 | 1.00 18.02 | B O |
| ATOM | 3617 | CG2 | THR | B | 418 | 26.370 | 13.898 | 49.068 | 1.00 17.98 | B C |
| ATOM | 3618 | C | THR | B | 418 | 30.234 | 13.708 | 49.473 | 1.00 16.87 | B C |
| ATOM | 3619 | O | THR | B | 418 | 30.964 | 12.738 | 49.317 | 1.00 17.36 | B O |
| ATOM | 3620 | N | ILE | B | 419 | 30.537 | 14.705 | 50.293 | 1.00 17.29 | B N |
| ATOM | 3621 | CA | ILE | B | 419 | 31.770 | 14.713 | 51.083 | 1.00 17.84 | B C |
| ATOM | 3622 | CB | ILE | B | 419 | 31.984 | 16.082 | 51.817 | 1.00 18.88 | B C |
| ATOM | 3623 | CG2 | ILE | B | 419 | 31.013 | 16.242 | 52.996 | 1.00 17.41 | B C |
| ATOM | 3624 | CG1 | ILE | B | 419 | 33.431 | 16.201 | 52.323 | 1.00 18.45 | B C |
| ATOM | 3625 | CD1 | ILE | B | 419 | 34.473 | 16.278 | 51.210 | 1.00 17.15 | B C |
| ATOM | 3626 | C | ILE | B | 419 | 31.706 | 13.563 | 52.093 | 1.00 18.23 | B C |
| ATOM | 3627 | O | ILE | B | 419 | 32.739 | 13.028 | 52.512 | 1.00 18.37 | B O |
| ATOM | 3628 | N | LYS | B | 420 | 30.486 | 13.153 | 52.445 | 1.00 17.09 | B N |
| ATOM | 3629 | CA | LYS | B | 420 | 30.301 | 12.047 | 53.377 | 1.00 16.49 | B C |
| ATOM | 3630 | CB | LYS | B | 420 | 28.887 | 12.032 | 53.972 | 1.00 16.30 | B C |
| ATOM | 3631 | CG | LYS | B | 420 | 28.604 | 13.200 | 54.899 | 1.00 14.54 | B C |
| ATOM | 3632 | CD | LYS | B | 420 | 29.570 | 13.206 | 56.055 | 1.00 13.93 | B C |
| ATOM | 3633 | CE | LYS | B | 420 | 29.255 | 14.336 | 56.980 | 1.00 13.19 | B C |
| ATOM | 3634 | NZ | LYS | B | 420 | 30.297 | 14.455 | 57.998 | 1.00 14.18 | B N |
| ATOM | 3635 | C | LYS | B | 420 | 30.648 | 10.708 | 52.739 | 1.00 15.57 | B C |
| ATOM | 3636 | O | LYS | B | 420 | 31.092 | 9.800 | 53.441 | 1.00 16.46 | B O |
| ATOM | 3637 | N | SER | B | 421 | 30.449 | 10.573 | 51.424 | 1.00 15.25 | B N |
| ATOM | 3638 | CA | SER | B | 421 | 30.822 | 9.335 | 50.752 | 1.00 14.94 | B C |
| ATOM | 3639 | CB | SER | B | 421 | 30.036 | 9.074 | 49.452 | 1.00 14.48 | B C |
| ATOM | 3640 | OG | SER | B | 421 | 29.922 | 10.199 | 48.616 | 1.00 16.41 | B O |
| ATOM | 3641 | C | SER | B | 421 | 32.345 | 9.304 | 50.588 | 1.00 14.70 | B C |
| ATOM | 3642 | O | SER | B | 421 | 32.937 | 8.236 | 50.488 | 1.00 15.78 | B O |
| ATOM | 3643 | N | ASP | B | 422 | 32.979 | 10.475 | 50.619 | 1.00 15.02 | B N |
| ATOM | 3644 | CA | ASP | B | 422 | 34.445 | 10.546 | 50.577 | 1.00 15.59 | B C |
| ATOM | 3645 | CB | ASP | B | 422 | 34.970 | 11.953 | 50.300 | 1.00 14.50 | B C |

Figure 9

| | | | | | | | | | | | |
|---|---|---|---|---|---|---|---|---|---|---|---|
| ATOM | 3646 | CG  | ASP | B | 422 | 34.752 | 12.409 | 48.888 | 1.00 | 14.41 | B | C |
| ATOM | 3647 | OD1 | ASP | B | 422 | 34.698 | 11.580 | 47.960 | 1.00 | 16.52 | B | O |
| ATOM | 3648 | OD2 | ASP | B | 422 | 34.671 | 13.633 | 48.720 | 1.00 | 15.07 | B | O |
| ATOM | 3649 | C   | ASP | B | 422 | 34.950 | 10.170 | 51.973 | 1.00 | 15.53 | B | C |
| ATOM | 3650 | O   | ASP | B | 422 | 36.047 |  9.639 | 52.096 | 1.00 | 16.83 | B | O |
| ATOM | 3651 | N   | VAL | B | 423 | 34.200 | 10.529 | 53.024 | 1.00 | 15.56 | B | N |
| ATOM | 3652 | CA  | VAL | B | 423 | 34.599 | 10.196 | 54.394 | 1.00 | 15.53 | B | C |
| ATOM | 3653 | CB  | VAL | B | 423 | 33.674 | 10.827 | 55.499 | 1.00 | 15.51 | B | C |
| ATOM | 3654 | CG1 | VAL | B | 423 | 34.043 | 10.260 | 56.904 | 1.00 | 14.88 | B | C |
| ATOM | 3655 | CG2 | VAL | B | 423 | 33.837 | 12.334 | 55.534 | 1.00 | 14.19 | B | C |
| ATOM | 3656 | C   | VAL | B | 423 | 34.630 |  8.684 | 54.522 | 1.00 | 15.68 | B | C |
| ATOM | 3657 | O   | VAL | B | 423 | 35.522 |  8.133 | 55.169 | 1.00 | 16.43 | B | O |
| ATOM | 3658 | N   | TRP | B | 424 | 33.686 |  8.021 | 53.851 | 1.00 | 15.20 | B | N |
| ATOM | 3659 | CA  | TRP | B | 424 | 33.603 |  6.562 | 53.834 | 1.00 | 13.73 | B | C |
| ATOM | 3660 | CB  | TRP | B | 424 | 32.345 |  6.112 | 53.070 | 1.00 | 12.03 | B | C |
| ATOM | 3661 | CG  | TRP | B | 424 | 32.258 |  4.620 | 52.869 | 1.00 | 11.60 | B | C |
| ATOM | 3662 | CD2 | TRP | B | 424 | 31.400 |  3.703 | 53.568 | 1.00 | 12.28 | B | C |
| ATOM | 3663 | CE2 | TRP | B | 424 | 31.716 |  2.398 | 53.106 | 1.00 | 13.62 | B | C |
| ATOM | 3664 | CE3 | TRP | B | 424 | 30.399 |  3.850 | 54.542 | 1.00 | 12.06 | B | C |
| ATOM | 3665 | CD1 | TRP | B | 424 | 33.027 |  3.853 | 52.027 | 1.00 | 10.91 | B | C |
| ATOM | 3666 | NE1 | TRP | B | 424 | 32.715 |  2.521 | 52.174 | 1.00 | 11.15 | B | N |
| ATOM | 3667 | CZ2 | TRP | B | 424 | 31.063 |  1.251 | 53.590 | 1.00 | 14.76 | B | C |
| ATOM | 3668 | CZ3 | TRP | B | 424 | 29.755 |  2.718 | 55.020 | 1.00 | 11.78 | B | C |
| ATOM | 3669 | CH2 | TRP | B | 424 | 30.089 |  1.433 | 54.547 | 1.00 | 13.59 | B | C |
| ATOM | 3670 | C   | TRP | B | 424 | 34.869 |  6.021 | 53.153 | 1.00 | 13.97 | B | C |
| ATOM | 3671 | O   | TRP | B | 424 | 35.502 |  5.102 | 53.657 | 1.00 | 13.19 | B | O |
| ATOM | 3672 | N   | SER | B | 425 | 35.225 |  6.610 | 52.008 | 1.00 | 15.55 | B | N |
| ATOM | 3673 | CA  | SER | B | 425 | 36.419 |  6.218 | 51.232 | 1.00 | 17.99 | B | C |
| ATOM | 3674 | CB  | SER | B | 425 | 36.520 |  7.033 | 49.942 | 1.00 | 17.88 | B | C |
| ATOM | 3675 | OG  | SER | B | 425 | 35.496 |  6.686 | 49.038 | 1.00 | 20.80 | B | O |
| ATOM | 3676 | C   | SER | B | 425 | 37.717 |  6.402 | 52.016 | 1.00 | 17.52 | B | C |
| ATOM | 3677 | O   | SER | B | 425 | 38.622 |  5.579 | 51.938 | 1.00 | 19.83 | B | O |
| ATOM | 3678 | N   | PHE | B | 426 | 37.808 |  7.503 | 52.744 | 1.00 | 16.92 | B | N |
| ATOM | 3679 | CA  | PHE | B | 426 | 38.972 |  7.802 | 53.559 | 1.00 | 17.13 | B | C |
| ATOM | 3680 | CB  | PHE | B | 426 | 38.796 |  9.152 | 54.260 | 1.00 | 16.49 | B | C |
| ATOM | 3681 | CG  | PHE | B | 426 | 39.951 |  9.523 | 55.125 | 1.00 | 16.60 | B | C |
| ATOM | 3682 | CD1 | PHE | B | 426 | 41.109 | 10.044 | 54.563 | 1.00 | 15.95 | B | C |
| ATOM | 3683 | CD2 | PHE | B | 426 | 39.903 |  9.293 | 56.493 | 1.00 | 16.40 | B | C |
| ATOM | 3684 | CE1 | PHE | B | 426 | 42.211 | 10.327 | 55.338 | 1.00 | 17.25 | B | C |
| ATOM | 3685 | CE2 | PHE | B | 426 | 41.001 |  9.570 | 57.294 | 1.00 | 18.63 | B | C |
| ATOM | 3686 | CZ  | PHE | B | 426 | 42.166 | 10.090 | 56.711 | 1.00 | 18.95 | B | C |
| ATOM | 3687 | C   | PHE | B | 426 | 39.191 |  6.704 | 54.590 | 1.00 | 17.37 | B | C |
| ATOM | 3688 | O   | PHE | B | 426 | 40.335 |  6.383 | 54.931 | 1.00 | 19.14 | B | O |
| ATOM | 3689 | N   | GLY | B | 427 | 38.090 |  6.185 | 55.137 | 1.00 | 16.39 | B | N |
| ATOM | 3690 | CA  | GLY | B | 427 | 38.164 |  5.104 | 56.103 | 1.00 | 14.68 | B | C |
| ATOM | 3691 | C   | GLY | B | 427 | 38.708 |  3.838 | 55.459 | 1.00 | 14.40 | B | C |
| ATOM | 3692 | O   | GLY | B | 427 | 39.392 |  3.054 | 56.117 | 1.00 | 14.17 | B | O |
| ATOM | 3693 | N   | ILE | B | 428 | 38.347 |  3.603 | 54.196 | 1.00 | 14.67 | B | N |
| ATOM | 3694 | CA  | ILE | B | 428 | 38.841 |  2.434 | 53.447 | 1.00 | 15.74 | B | C |
| ATOM | 3695 | CB  | ILE | B | 428 | 38.085 |  2.230 | 52.096 | 1.00 | 15.25 | B | C |
| ATOM | 3696 | CG2 | ILE | B | 428 | 38.621 |  1.004 | 51.366 | 1.00 | 14.38 | B | C |
| ATOM | 3697 | CG1 | ILE | B | 428 | 36.586 |  2.067 | 52.334 | 1.00 | 14.19 | B | C |
| ATOM | 3698 | CD1 | ILE | B | 428 | 36.197 |  0.779 | 53.064 | 1.00 | 12.56 | B | C |
| ATOM | 3699 | C   | ILE | B | 428 | 40.334 |  2.669 | 53.140 | 1.00 | 16.50 | B | C |
| ATOM | 3700 | O   | ILE | B | 428 | 41.150 |  1.747 | 53.210 | 1.00 | 16.80 | B | O |
| ATOM | 3701 | N   | LEU | B | 429 | 40.671 |  3.920 | 52.830 | 1.00 | 16.81 | B | N |
| ATOM | 3702 | CA  | LEU | B | 429 | 42.039 |  4.319 | 52.537 | 1.00 | 17.61 | B | C |
| ATOM | 3703 | CB  | LEU | B | 429 | 42.073 |  5.806 | 52.132 | 1.00 | 17.70 | B | C |
| ATOM | 3704 | CG  | LEU | B | 429 | 43.290 |  6.428 | 51.422 | 1.00 | 17.48 | B | C |

Figure 9

| ATOM | 3705 | CD1 | LEU | B | 429 | 42.954 | 7.792 | 50.879 | 1.00 | 17.06 | B | C |
|------|------|-----|-----|---|-----|--------|-------|--------|------|-------|---|---|
| ATOM | 3706 | CD2 | LEU | B | 429 | 44.443 | 6.551 | 52.344 | 1.00 | 17.93 | B | C |
| ATOM | 3707 | C   | LEU | B | 429 | 42.927 | 4.071 | 53.773 | 1.00 | 18.22 | B | C |
| ATOM | 3708 | O   | LEU | B | 429 | 44.078 | 3.671 | 53.627 | 1.00 | 18.13 | B | O |
| ATOM | 3709 | N   | LEU | B | 430 | 42.388 | 4.297 | 54.977 | 1.00 | 18.41 | B | N |
| ATOM | 3710 | CA  | LEU | B | 430 | 43.139 | 4.083 | 56.224 | 1.00 | 18.31 | B | C |
| ATOM | 3711 | CB  | LEU | B | 430 | 42.338 | 4.528 | 57.458 | 1.00 | 16.26 | B | C |
| ATOM | 3712 | CG  | LEU | B | 430 | 42.163 | 6.009 | 57.796 | 1.00 | 13.87 | B | C |
| ATOM | 3713 | CD1 | LEU | B | 430 | 41.244 | 6.145 | 58.991 | 1.00 | 13.72 | B | C |
| ATOM | 3714 | CD2 | LEU | B | 430 | 43.501 | 6.664 | 58.087 | 1.00 | 13.07 | B | C |
| ATOM | 3715 | C   | LEU | B | 430 | 43.584 | 2.620 | 56.389 | 1.00 | 19.22 | B | C |
| ATOM | 3716 | O   | LEU | B | 430 | 44.644 | 2.360 | 56.962 | 1.00 | 19.75 | B | O |
| ATOM | 3717 | N   | THR | B | 431 | 42.761 | 1.672 | 55.924 | 1.00 | 20.01 | B | N |
| ATOM | 3718 | CA  | THR | B | 431 | 43.111 | 0.246 | 55.986 | 1.00 | 20.57 | B | C |
| ATOM | 3719 | CB  | THR | B | 431 | 41.897 | -0.702 | 55.653 | 1.00 | 19.56 | B | C |
| ATOM | 3720 | OG1 | THR | B | 431 | 41.520 | -0.583 | 54.269 | 1.00 | 20.73 | B | O |
| ATOM | 3721 | CG2 | THR | B | 431 | 40.701 | -0.373 | 56.523 | 1.00 | 20.54 | B | C |
| ATOM | 3722 | C   | THR | B | 431 | 44.285 | -0.021 | 55.014 | 1.00 | 21.34 | B | C |
| ATOM | 3723 | O   | THR | B | 431 | 45.186 | -0.804 | 55.315 | 1.00 | 21.38 | B | O |
| ATOM | 3724 | N   | GLU | B | 432 | 44.267 | 0.655 | 53.860 | 1.00 | 21.16 | B | N |
| ATOM | 3725 | CA  | GLU | B | 432 | 45.326 | 0.542 | 52.859 | 1.00 | 21.03 | B | C |
| ATOM | 3726 | CB  | GLU | B | 432 | 45.014 | 1.412 | 51.641 | 1.00 | 19.95 | B | C |
| ATOM | 3727 | CG  | GLU | B | 432 | 43.921 | 0.886 | 50.757 | 1.00 | 19.58 | B | C |
| ATOM | 3728 | CD  | GLU | B | 432 | 43.742 | 1.723 | 49.509 | 1.00 | 19.58 | B | C |
| ATOM | 3729 | OE1 | GLU | B | 432 | 43.166 | 2.825 | 49.598 | 1.00 | 18.89 | B | O |
| ATOM | 3730 | OE2 | GLU | B | 432 | 44.168 | 1.270 | 48.430 | 1.00 | 19.49 | B | O |
| ATOM | 3731 | C   | GLU | B | 432 | 46.647 | 1.019 | 53.447 | 1.00 | 21.56 | B | C |
| ATOM | 3732 | O   | GLU | B | 432 | 47.693 | 0.444 | 53.174 | 1.00 | 22.26 | B | O |
| ATOM | 3733 | N   | ILE | B | 433 | 46.591 | 2.101 | 54.220 | 1.00 | 22.19 | B | N |
| ATOM | 3734 | CA  | ILE | B | 433 | 47.773 | 2.676 | 54.848 | 1.00 | 21.74 | B | C |
| ATOM | 3735 | CB  | ILE | B | 433 | 47.472 | 4.072 | 55.419 | 1.00 | 20.42 | B | C |
| ATOM | 3736 | CG2 | ILE | B | 433 | 48.616 | 4.557 | 56.295 | 1.00 | 21.42 | B | C |
| ATOM | 3737 | CG1 | ILE | B | 433 | 47.261 | 5.064 | 54.282 | 1.00 | 20.57 | B | C |
| ATOM | 3738 | CD1 | ILE | B | 433 | 47.011 | 6.501 | 54.744 | 1.00 | 19.15 | B | C |
| ATOM | 3739 | C   | ILE | B | 433 | 48.383 | 1.795 | 55.940 | 1.00 | 23.03 | B | C |
| ATOM | 3740 | O   | ILE | B | 433 | 49.603 | 1.667 | 56.015 | 1.00 | 23.95 | B | O |
| ATOM | 3741 | N   | VAL | B | 434 | 47.555 | 1.160 | 56.765 | 1.00 | 23.38 | B | N |
| ATOM | 3742 | CA  | VAL | B | 434 | 48.089 | 0.333 | 57.843 | 1.00 | 25.23 | B | C |
| ATOM | 3743 | CB  | VAL | B | 434 | 47.202 | 0.383 | 59.118 | 1.00 | 24.82 | B | C |
| ATOM | 3744 | CG1 | VAL | B | 434 | 47.144 | 1.813 | 59.630 | 1.00 | 23.79 | B | C |
| ATOM | 3745 | CG2 | VAL | B | 434 | 45.787 | -0.173 | 58.843 | 1.00 | 24.50 | B | C |
| ATOM | 3746 | C   | VAL | B | 434 | 48.440 | -1.100 | 57.456 | 1.00 | 26.45 | B | C |
| ATOM | 3747 | O   | VAL | B | 434 | 49.049 | -1.828 | 58.237 | 1.00 | 28.89 | B | O |
| ATOM | 3748 | N   | THR | B | 435 | 48.069 | -1.499 | 56.245 | 1.00 | 27.18 | B | N |
| ATOM | 3749 | CA  | THR | B | 435 | 48.376 | -2.837 | 55.763 | 1.00 | 28.41 | B | C |
| ATOM | 3750 | CB  | THR | B | 435 | 47.117 | -3.542 | 55.256 | 1.00 | 27.96 | B | C |
| ATOM | 3751 | OG1 | THR | B | 435 | 46.551 | -2.780 | 54.190 | 1.00 | 27.56 | B | O |
| ATOM | 3752 | CG2 | THR | B | 435 | 46.090 | -3.699 | 56.383 | 1.00 | 26.58 | B | C |
| ATOM | 3753 | C   | THR | B | 435 | 49.379 | -2.760 | 54.608 | 1.00 | 29.63 | B | C |
| ATOM | 3754 | O   | THR | B | 435 | 49.589 | -3.738 | 53.898 | 1.00 | 30.12 | B | O |
| ATOM | 3755 | N   | HIS | B | 436 | 49.959 | -1.577 | 54.414 | 1.00 | 31.55 | B | N |
| ATOM | 3756 | CA  | HIS | B | 436 | 50.932 | -1.304 | 53.357 | 1.00 | 33.05 | B | C |
| ATOM | 3757 | CB  | HIS | B | 436 | 52.251 | -2.030 | 53.645 | 1.00 | 36.74 | B | C |
| ATOM | 3758 | CG  | HIS | B | 436 | 52.802 | -1.762 | 55.017 | 1.00 | 40.72 | B | C |
| ATOM | 3759 | CD2 | HIS | B | 436 | 53.176 | -2.609 | 56.007 | 1.00 | 41.98 | B | C |
| ATOM | 3760 | ND1 | HIS | B | 436 | 53.019 | -0.488 | 55.504 | 1.00 | 42.13 | B | N |
| ATOM | 3761 | CE1 | HIS | B | 436 | 53.503 | -0.558 | 56.732 | 1.00 | 40.88 | B | C |
| ATOM | 3762 | NE2 | HIS | B | 436 | 53.606 | -1.834 | 57.061 | 1.00 | 42.79 | B | N |
| ATOM | 3763 | C   | HIS | B | 436 | 50.444 | -1.597 | 51.927 | 1.00 | 32.62 | B | C |

Figure 9

| ATOM | 3764 | O | HIS | B | 436 | 51.104 | -2.318 | 51.171 | 1.00 | 32.88 | B | O |
|---|---|---|---|---|---|---|---|---|---|---|---|---|
| ATOM | 3765 | N | GLY | B | 437 | 49.296 | -1.024 | 51.566 | 1.00 | 31.42 | B | N |
| ATOM | 3766 | CA | GLY | B | 437 | 48.744 | -1.188 | 50.228 | 1.00 | 31.57 | B | C |
| ATOM | 3767 | C | GLY | B | 437 | 47.900 | -2.410 | 49.898 | 1.00 | 31.34 | B | C |
| ATOM | 3768 | O | GLY | B | 437 | 47.588 | -2.654 | 48.727 | 1.00 | 30.17 | B | O |
| ATOM | 3769 | N | ARG | B | 438 | 47.513 | -3.165 | 50.917 | 1.00 | 31.87 | B | N |
| ATOM | 3770 | CA | ARG | B | 438 | 46.694 | -4.362 | 50.718 | 1.00 | 33.16 | B | C |
| ATOM | 3771 | CB | ARG | B | 438 | 46.599 | -5.134 | 52.032 | 1.00 | 36.36 | B | C |
| ATOM | 3772 | CG | ARG | B | 438 | 46.210 | -6.604 | 51.914 | 1.00 | 41.08 | B | C |
| ATOM | 3773 | CD | ARG | B | 438 | 44.705 | -6.813 | 51.733 | 1.00 | 45.15 | B | C |
| ATOM | 3774 | NE | ARG | B | 438 | 43.891 | -6.174 | 52.775 | 1.00 | 48.58 | B | N |
| ATOM | 3775 | CZ | ARG | B | 438 | 43.897 | -6.524 | 54.061 | 1.00 | 50.61 | B | C |
| ATOM | 3776 | NH1 | ARG | B | 438 | 44.680 | -7.519 | 54.476 | 1.00 | 51.48 | B | N |
| ATOM | 3777 | NH2 | ARG | B | 438 | 43.140 | -5.864 | 54.937 | 1.00 | 50.52 | B | N |
| ATOM | 3778 | C | ARG | B | 438 | 45.300 | -3.965 | 50.233 | 1.00 | 31.82 | B | C |
| ATOM | 3779 | O | ARG | B | 438 | 44.734 | -2.980 | 50.704 | 1.00 | 31.39 | B | O |
| ATOM | 3780 | N | ILE | B | 439 | 44.771 | -4.721 | 49.277 | 1.00 | 30.86 | B | N |
| ATOM | 3781 | CA | ILE | B | 439 | 43.444 | -4.466 | 48.706 | 1.00 | 30.76 | B | C |
| ATOM | 3782 | CB | ILE | B | 439 | 43.197 | -5.383 | 47.471 | 1.00 | 31.20 | B | C |
| ATOM | 3783 | CG2 | ILE | B | 439 | 41.725 | -5.413 | 47.070 | 1.00 | 30.49 | B | C |
| ATOM | 3784 | CG1 | ILE | B | 439 | 44.036 | -4.888 | 46.289 | 1.00 | 32.91 | B | C |
| ATOM | 3785 | CD1 | ILE | B | 439 | 44.002 | -5.815 | 45.081 | 1.00 | 34.12 | B | C |
| ATOM | 3786 | C | ILE | B | 439 | 42.339 | -4.660 | 49.753 | 1.00 | 30.22 | B | C |
| ATOM | 3787 | O | ILE | B | 439 | 42.362 | -5.620 | 50.525 | 1.00 | 30.34 | B | O |
| ATOM | 3788 | N | PRO | B | 440 | 41.371 | -3.727 | 49.808 | 1.00 | 29.33 | B | N |
| ATOM | 3789 | CD | PRO | B | 440 | 41.300 | -2.477 | 49.035 | 1.00 | 28.40 | B | C |
| ATOM | 3790 | CA | PRO | B | 440 | 40.263 | -3.807 | 50.770 | 1.00 | 29.05 | B | C |
| ATOM | 3791 | CB | PRO | B | 440 | 39.448 | -2.559 | 50.443 | 1.00 | 28.95 | B | C |
| ATOM | 3792 | CG | PRO | B | 440 | 40.504 | -1.600 | 49.941 | 1.00 | 28.71 | B | C |
| ATOM | 3793 | C | PRO | B | 440 | 39.452 | -5.071 | 50.567 | 1.00 | 28.67 | B | C |
| ATOM | 3794 | O | PRO | B | 440 | 39.447 | -5.625 | 49.479 | 1.00 | 28.48 | B | O |
| ATOM | 3795 | N | TYR | B | 441 | 38.815 | -5.549 | 51.634 | 1.00 | 29.12 | B | N |
| ATOM | 3796 | CA | TYR | B | 441 | 37.990 | -6.760 | 51.591 | 1.00 | 29.51 | B | C |
| ATOM | 3797 | CB | TYR | B | 441 | 36.653 | -6.487 | 50.881 | 1.00 | 27.24 | B | C |
| ATOM | 3798 | CG | TYR | B | 441 | 35.888 | -5.287 | 51.401 | 1.00 | 25.75 | B | C |
| ATOM | 3799 | CD1 | TYR | B | 441 | 34.935 | -5.420 | 52.416 | 1.00 | 25.67 | B | C |
| ATOM | 3800 | CE1 | TYR | B | 441 | 34.218 | -4.324 | 52.880 | 1.00 | 25.21 | B | C |
| ATOM | 3801 | CD2 | TYR | B | 441 | 36.103 | -4.023 | 50.867 | 1.00 | 23.86 | B | C |
| ATOM | 3802 | CE2 | TYR | B | 441 | 35.398 | -2.927 | 51.317 | 1.00 | 24.49 | B | C |
| ATOM | 3803 | CZ | TYR | B | 441 | 34.456 | -3.076 | 52.325 | 1.00 | 24.95 | B | C |
| ATOM | 3804 | OH | TYR | B | 441 | 33.759 | -1.973 | 52.774 | 1.00 | 25.37 | B | O |
| ATOM | 3805 | C | TYR | B | 441 | 38.735 | -7.905 | 50.898 | 1.00 | 31.54 | B | C |
| ATOM | 3806 | O | TYR | B | 441 | 38.289 | -8.426 | 49.867 | 1.00 | 30.84 | B | O |
| ATOM | 3807 | N | PRO | B | 442 | 39.896 | -8.300 | 51.450 | 1.00 | 33.77 | B | N |
| ATOM | 3808 | CD | PRO | B | 442 | 40.487 | -7.864 | 52.730 | 1.00 | 33.27 | B | C |
| ATOM | 3809 | CA | PRO | B | 442 | 40.678 | -9.385 | 50.851 | 1.00 | 36.11 | B | C |
| ATOM | 3810 | CB | PRO | B | 442 | 41.838 | -9.541 | 51.838 | 1.00 | 35.88 | B | C |
| ATOM | 3811 | CG | PRO | B | 442 | 41.244 | -9.076 | 53.159 | 1.00 | 34.64 | B | C |
| ATOM | 3812 | C | PRO | B | 442 | 39.832 | -10.656 | 50.739 | 1.00 | 38.39 | B | C |
| ATOM | 3813 | O | PRO | B | 442 | 39.152 | -11.034 | 51.693 | 1.00 | 39.87 | B | O |
| ATOM | 3814 | N | GLY | B | 443 | 39.833 | -11.285 | 49.565 | 1.00 | 39.88 | B | N |
| ATOM | 3815 | CA | GLY | B | 443 | 39.044 | -12.495 | 49.376 | 1.00 | 40.75 | B | C |
| ATOM | 3816 | C | GLY | B | 443 | 37.614 | -12.249 | 48.920 | 1.00 | 41.27 | B | C |
| ATOM | 3817 | O | GLY | B | 443 | 36.812 | -13.182 | 48.826 | 1.00 | 43.01 | B | O |
| ATOM | 3818 | N | MET | B | 444 | 37.281 | -10.996 | 48.640 | 1.00 | 40.40 | B | N |
| ATOM | 3819 | CA | MET | B | 444 | 35.944 | -10.657 | 48.179 | 1.00 | 39.01 | B | C |
| ATOM | 3820 | CB | MET | B | 444 | 35.228 | -9.733 | 49.176 | 1.00 | 38.42 | B | C |
| ATOM | 3821 | CG | MET | B | 444 | 34.836 | -10.407 | 50.488 | 1.00 | 37.10 | B | C |
| ATOM | 3822 | SD | MET | B | 444 | 33.963 | -9.356 | 51.677 | 1.00 | 34.64 | B | S |

Figure 9

| ATOM | 3823 | CE  | MET B 444 | 32.961 | -8.514  | 50.660 | 1.00 | 34.84 | B | C |
|------|------|-----|-----------|--------|---------|--------|------|-------|---|---|
| ATOM | 3824 | C   | MET B 444 | 36.038 | -9.982  | 46.820 | 1.00 | 39.20 | B | C |
| ATOM | 3825 | O   | MET B 444 | 36.953 | -9.194  | 46.561 | 1.00 | 39.66 | B | O |
| ATOM | 3826 | N   | THR B 445 | 35.118 | -10.346 | 45.939 | 1.00 | 38.75 | B | N |
| ATOM | 3827 | CA  | THR B 445 | 35.055 | -9.776  | 44.602 | 1.00 | 38.66 | B | C |
| ATOM | 3828 | CB  | THR B 445 | 34.544 | -10.829 | 43.598 | 1.00 | 39.54 | B | C |
| ATOM | 3829 | OG1 | THR B 445 | 33.149 | -11.084 | 43.832 | 1.00 | 39.63 | B | O |
| ATOM | 3830 | CG2 | THR B 445 | 35.326 | -12.141 | 43.779 | 1.00 | 38.88 | B | C |
| ATOM | 3831 | C   | THR B 445 | 34.069 | -8.615  | 44.674 | 1.00 | 38.22 | B | C |
| ATOM | 3832 | O   | THR B 445 | 33.319 | -8.508  | 45.644 | 1.00 | 38.38 | B | O |
| ATOM | 3833 | N   | ASN B 446 | 34.059 | -7.744  | 43.667 | 1.00 | 38.00 | B | N |
| ATOM | 3834 | CA  | ASN B 446 | 33.125 | -6.618  | 43.678 | 1.00 | 37.86 | B | C |
| ATOM | 3835 | CB  | ASN B 446 | 33.201 | -5.809  | 42.381 | 1.00 | 37.86 | B | C |
| ATOM | 3836 | CG  | ASN B 446 | 34.443 | -4.937  | 42.321 | 1.00 | 38.32 | B | C |
| ATOM | 3837 | OD1 | ASN B 446 | 35.348 | -5.064  | 43.155 | 1.00 | 37.65 | B | O |
| ATOM | 3838 | ND2 | ASN B 446 | 34.489 | -4.035  | 41.342 | 1.00 | 39.14 | B | N |
| ATOM | 3839 | C   | ASN B 446 | 31.684 | -7.011  | 44.016 | 1.00 | 37.47 | B | C |
| ATOM | 3840 | O   | ASN B 446 | 31.123 | -6.480  | 44.978 | 1.00 | 36.13 | B | O |
| ATOM | 3841 | N   | PRO B 447 | 31.084 | -7.977  | 43.267 | 1.00 | 37.92 | B | N |
| ATOM | 3842 | CD  | PRO B 447 | 31.577 | -8.702  | 42.078 | 1.00 | 37.20 | B | C |
| ATOM | 3843 | CA  | PRO B 447 | 29.701 | -8.390  | 43.567 | 1.00 | 36.47 | B | C |
| ATOM | 3844 | CB  | PRO B 447 | 29.442 | -9.521  | 42.556 | 1.00 | 36.28 | B | C |
| ATOM | 3845 | CG  | PRO B 447 | 30.834 | -10.005 | 42.181 | 1.00 | 36.69 | B | C |
| ATOM | 3846 | C   | PRO B 447 | 29.498 | -8.852  | 45.015 | 1.00 | 34.52 | B | C |
| ATOM | 3847 | O   | PRO B 447 | 28.453 | -8.582  | 45.607 | 1.00 | 33.97 | B | O |
| ATOM | 3848 | N   | GLU B 448 | 30.512 | -9.503  | 45.586 | 1.00 | 32.62 | B | N |
| ATOM | 3849 | CA  | GLU B 448 | 30.442 | -9.992  | 46.955 | 1.00 | 31.49 | B | C |
| ATOM | 3850 | CB  | GLU B 448 | 31.581 | -10.950 | 47.243 | 1.00 | 32.13 | B | C |
| ATOM | 3851 | CG  | GLU B 448 | 31.366 | -12.306 | 46.645 | 1.00 | 35.46 | B | C |
| ATOM | 3852 | CD  | GLU B 448 | 32.565 | -13.207 | 46.808 | 1.00 | 37.08 | B | C |
| ATOM | 3853 | OE1 | GLU B 448 | 33.530 | -12.826 | 47.507 | 1.00 | 37.76 | B | O |
| ATOM | 3854 | OE2 | GLU B 448 | 32.536 | -14.310 | 46.227 | 1.00 | 38.91 | B | O |
| ATOM | 3855 | C   | GLU B 448 | 30.459 | -8.889  | 47.990 | 1.00 | 30.46 | B | C |
| ATOM | 3856 | O   | GLU B 448 | 29.831 | -9.015  | 49.037 | 1.00 | 30.59 | B | O |
| ATOM | 3857 | N   | VAL B 449 | 31.221 | -7.835  | 47.711 | 1.00 | 29.22 | B | N |
| ATOM | 3858 | CA  | VAL B 449 | 31.330 | -6.689  | 48.609 | 1.00 | 26.79 | B | C |
| ATOM | 3859 | CB  | VAL B 449 | 32.432 | -5.696  | 48.135 | 1.00 | 25.99 | B | C |
| ATOM | 3860 | CG1 | VAL B 449 | 32.323 | -4.368  | 48.874 | 1.00 | 23.57 | B | C |
| ATOM | 3861 | CG2 | VAL B 449 | 33.820 | -6.320  | 48.349 | 1.00 | 22.87 | B | C |
| ATOM | 3862 | C   | VAL B 449 | 29.979 | -6.022  | 48.659 | 1.00 | 26.10 | B | C |
| ATOM | 3863 | O   | VAL B 449 | 29.494 | -5.665  | 49.722 | 1.00 | 25.38 | B | O |
| ATOM | 3864 | N   | ILE B 450 | 29.342 | -5.946  | 47.499 | 1.00 | 26.46 | B | N |
| ATOM | 3865 | CA  | ILE B 450 | 28.025 | -5.348  | 47.371 | 1.00 | 27.23 | B | C |
| ATOM | 3866 | CB  | ILE B 450 | 27.498 | -5.440  | 45.927 | 1.00 | 27.34 | B | C |
| ATOM | 3867 | CG2 | ILE B 450 | 26.065 | -4.905  | 45.861 | 1.00 | 26.69 | B | C |
| ATOM | 3868 | CG1 | ILE B 450 | 28.450 | -4.735  | 44.947 | 1.00 | 27.82 | B | C |
| ATOM | 3869 | CD1 | ILE B 450 | 28.573 | -3.254  | 45.134 | 1.00 | 25.99 | B | C |
| ATOM | 3870 | C   | ILE B 450 | 27.025 | -6.077  | 48.257 | 1.00 | 27.25 | B | C |
| ATOM | 3871 | O   | ILE B 450 | 26.324 | -5.445  | 49.042 | 1.00 | 28.20 | B | O |
| ATOM | 3872 | N   | GLN B 451 | 26.960 | -7.399  | 48.124 | 1.00 | 27.18 | B | N |
| ATOM | 3873 | CA  | GLN B 451 | 26.018 | -8.187  | 48.912 | 1.00 | 27.14 | B | C |
| ATOM | 3874 | CB  | GLN B 451 | 25.848 | -9.599  | 48.337 | 1.00 | 29.72 | B | C |
| ATOM | 3875 | CG  | GLN B 451 | 27.082 | -10.473 | 48.364 | 1.00 | 35.19 | B | C |
| ATOM | 3876 | CD  | GLN B 451 | 27.038 | -11.548 | 47.291 | 1.00 | 37.91 | B | C |
| ATOM | 3877 | OE1 | GLN B 451 | 27.542 | -12.661 | 47.477 | 1.00 | 39.97 | B | O |
| ATOM | 3878 | NE2 | GLN B 451 | 26.446 | -11.211 | 46.150 | 1.00 | 38.98 | B | N |
| ATOM | 3879 | C   | GLN B 451 | 26.347 | -8.217  | 50.393 | 1.00 | 24.87 | B | C |
| ATOM | 3880 | O   | GLN B 451 | 25.469 | -8.423  | 51.212 | 1.00 | 23.56 | B | O |
| ATOM | 3881 | N   | ASN B 452 | 27.608 | -8.002  | 50.738 | 1.00 | 24.11 | B | N |

Figure 9

| ATOM | 3882 | CA | ASN B 452 | 27.979 | -7.970 | 52.142 | 1.00 | 23.33 | B | C |
| ATOM | 3883 | CB | ASN B 452 | 29.466 | -8.254 | 52.342 | 1.00 | 24.18 | B | C |
| ATOM | 3884 | CG | ASN B 452 | 29.739 | -9.724 | 52.613 | 1.00 | 26.01 | B | C |
| ATOM | 3885 | OD1 | ASN B 452 | 29.772 | -10.152 | 53.764 | 1.00 | 27.33 | B | O |
| ATOM | 3886 | ND2 | ASN B 452 | 29.915 | -10.511 | 51.546 | 1.00 | 27.40 | B | N |
| ATOM | 3887 | C | ASN B 452 | 27.601 | -6.626 | 52.731 | 1.00 | 22.60 | B | C |
| ATOM | 3888 | O | ASN B 452 | 27.189 | -6.555 | 53.885 | 1.00 | 21.73 | B | O |
| ATOM | 3889 | N | LEU B 453 | 27.688 | -5.570 | 51.922 | 1.00 | 22.06 | B | N |
| ATOM | 3890 | CA | LEU B 453 | 27.324 | -4.243 | 52.392 | 1.00 | 21.95 | B | C |
| ATOM | 3891 | CB | LEU B 453 | 27.832 | -3.149 | 51.467 | 1.00 | 22.96 | B | C |
| ATOM | 3892 | CG | LEU B 453 | 29.329 | -2.877 | 51.386 | 1.00 | 23.63 | B | C |
| ATOM | 3893 | CD1 | LEU B 453 | 29.503 | -1.720 | 50.400 | 1.00 | 23.05 | B | C |
| ATOM | 3894 | CD2 | LEU B 453 | 29.917 | -2.541 | 52.757 | 1.00 | 22.87 | B | C |
| ATOM | 3895 | C | LEU B 453 | 25.819 | -4.125 | 52.534 | 1.00 | 21.68 | B | C |
| ATOM | 3896 | O | LEU B 453 | 25.356 | -3.332 | 53.339 | 1.00 | 21.51 | B | O |
| ATOM | 3897 | N | GLU B 454 | 25.056 | -4.864 | 51.727 | 1.00 | 21.35 | B | N |
| ATOM | 3898 | CA | GLU B 454 | 23.595 | -4.841 | 51.864 | 1.00 | 22.99 | B | C |
| ATOM | 3899 | CB | GLU B 454 | 22.917 | -5.748 | 50.849 | 1.00 | 26.70 | B | C |
| ATOM | 3900 | CG | GLU B 454 | 23.174 | -5.422 | 49.398 | 1.00 | 33.86 | B | C |
| ATOM | 3901 | CD | GLU B 454 | 22.759 | -6.564 | 48.463 | 1.00 | 38.74 | B | C |
| ATOM | 3902 | OE1 | GLU B 454 | 22.973 | -6.422 | 47.236 | 1.00 | 41.00 | B | O |
| ATOM | 3903 | OE2 | GLU B 454 | 22.234 | -7.606 | 48.949 | 1.00 | 41.16 | B | O |
| ATOM | 3904 | C | GLU B 454 | 23.249 | -5.388 | 53.255 | 1.00 | 21.57 | B | C |
| ATOM | 3905 | O | GLU B 454 | 22.326 | -4.899 | 53.896 | 1.00 | 21.06 | B | O |
| ATOM | 3906 | N | ARG B 455 | 23.999 | -6.406 | 53.697 | 1.00 | 20.50 | B | N |
| ATOM | 3907 | CA | ARG B 455 | 23.800 | -7.036 | 55.005 | 1.00 | 20.31 | B | C |
| ATOM | 3908 | CB | ARG B 455 | 24.286 | -8.490 | 54.987 | 1.00 | 20.98 | B | C |
| ATOM | 3909 | CG | ARG B 455 | 23.638 | -9.393 | 53.934 | 1.00 | 26.90 | B | C |
| ATOM | 3910 | CD | ARG B 455 | 24.266 | -10.815 | 53.889 | 1.00 | 31.73 | B | C |
| ATOM | 3911 | NE | ARG B 455 | 25.700 | -10.750 | 54.156 | 1.00 | 40.08 | B | N |
| ATOM | 3912 | CZ | ARG B 455 | 26.259 | -10.971 | 55.355 | 1.00 | 43.39 | B | C |
| ATOM | 3913 | NH1 | ARG B 455 | 25.512 | -11.325 | 56.399 | 1.00 | 42.97 | B | N |
| ATOM | 3914 | NH2 | ARG B 455 | 27.530 | -10.633 | 55.574 | 1.00 | 43.77 | B | N |
| ATOM | 3915 | C | ARG B 455 | 24.497 | -6.262 | 56.149 | 1.00 | 19.22 | B | C |
| ATOM | 3916 | O | ARG B 455 | 24.518 | -6.712 | 57.289 | 1.00 | 19.01 | B | O |
| ATOM | 3917 | N | GLY B 456 | 25.090 | -5.113 | 55.829 | 1.00 | 18.89 | B | N |
| ATOM | 3918 | CA | GLY B 456 | 25.758 | -4.295 | 56.830 | 1.00 | 17.09 | B | C |
| ATOM | 3919 | C | GLY B 456 | 27.149 | -4.713 | 57.260 | 1.00 | 16.49 | B | C |
| ATOM | 3920 | O | GLY B 456 | 27.598 | -4.350 | 58.341 | 1.00 | 16.89 | B | O |
| ATOM | 3921 | N | TYR B 457 | 27.852 | -5.448 | 56.414 | 1.00 | 17.05 | B | N |
| ATOM | 3922 | CA | TYR B 457 | 29.203 | -5.904 | 56.721 | 1.00 | 15.88 | B | C |
| ATOM | 3923 | CB | TYR B 457 | 29.656 | -6.880 | 55.637 | 1.00 | 14.94 | B | C |
| ATOM | 3924 | CG | TYR B 457 | 31.053 | -7.412 | 55.815 | 1.00 | 15.15 | B | C |
| ATOM | 3925 | CD1 | TYR B 457 | 31.281 | -8.586 | 56.517 | 1.00 | 15.20 | B | C |
| ATOM | 3926 | CE1 | TYR B 457 | 32.563 | -9.082 | 56.688 | 1.00 | 16.78 | B | C |
| ATOM | 3927 | CD2 | TYR B 457 | 32.154 | -6.737 | 55.280 | 1.00 | 16.05 | B | C |
| ATOM | 3928 | CE2 | TYR B 457 | 33.446 | -7.227 | 55.441 | 1.00 | 15.85 | B | C |
| ATOM | 3929 | CZ | TYR B 457 | 33.643 | -8.397 | 56.146 | 1.00 | 17.62 | B | C |
| ATOM | 3930 | OH | TYR B 457 | 34.923 | -8.877 | 56.334 | 1.00 | 20.82 | B | O |
| ATOM | 3931 | C | TYR B 457 | 30.236 | -4.776 | 56.871 | 1.00 | 16.84 | B | C |
| ATOM | 3932 | O | TYR B 457 | 30.173 | -3.744 | 56.181 | 1.00 | 17.93 | B | O |
| ATOM | 3933 | N | ARG B 458 | 31.161 | -4.967 | 57.809 | 1.00 | 17.12 | B | N |
| ATOM | 3934 | CA | ARG B 458 | 32.254 | -4.024 | 58.031 | 1.00 | 17.73 | B | C |
| ATOM | 3935 | CB | ARG B 458 | 32.017 | -3.133 | 59.256 | 1.00 | 16.55 | B | C |
| ATOM | 3936 | CG | ARG B 458 | 30.835 | -2.171 | 59.155 | 1.00 | 13.92 | B | C |
| ATOM | 3937 | CD | ARG B 458 | 30.945 | -1.242 | 57.953 | 1.00 | 14.90 | B | C |
| ATOM | 3938 | NE | ARG B 458 | 29.882 | -0.245 | 57.943 | 1.00 | 13.42 | B | N |
| ATOM | 3939 | CZ | ARG B 458 | 28.752 | -0.343 | 57.243 | 1.00 | 13.61 | B | C |
| ATOM | 3940 | NH1 | ARG B 458 | 28.515 | -1.397 | 56.466 | 1.00 | 12.92 | B | N |

Figure 9

| ATOM | 3941 | NH2 | ARG | B | 458 | 27.843 | 0.615 | 57.346 | 1.00 | 13.56 | B | N |
|------|------|-----|-----|---|-----|--------|-------|--------|------|-------|---|---|
| ATOM | 3942 | C | ARG | B | 458 | 33.528 | -4.842 | 58.225 | 1.00 | 18.64 | B | C |
| ATOM | 3943 | O | ARG | B | 458 | 33.498 | -5.898 | 58.871 | 1.00 | 18.55 | B | O |
| ATOM | 3944 | N | MET | B | 459 | 34.621 | -4.399 | 57.602 | 1.00 | 19.17 | B | N |
| ATOM | 3945 | CA | MET | B | 459 | 35.904 | -5.084 | 57.734 | 1.00 | 20.58 | B | C |
| ATOM | 3946 | CB | MET | B | 459 | 36.999 | -4.330 | 56.984 | 1.00 | 21.53 | B | C |
| ATOM | 3947 | CG | MET | B | 459 | 37.027 | -4.528 | 55.488 | 1.00 | 24.62 | B | C |
| ATOM | 3948 | SD | MET | B | 459 | 38.514 | -3.745 | 54.795 | 1.00 | 26.28 | B | S |
| ATOM | 3949 | CE | MET | B | 459 | 37.837 | -2.215 | 54.215 | 1.00 | 24.47 | B | C |
| ATOM | 3950 | C | MET | B | 459 | 36.323 | -5.128 | 59.197 | 1.00 | 21.27 | B | C |
| ATOM | 3951 | O | MET | B | 459 | 36.071 | -4.177 | 59.953 | 1.00 | 20.91 | B | O |
| ATOM | 3952 | N | VAL | B | 460 | 36.982 | -6.213 | 59.596 | 1.00 | 22.66 | B | N |
| ATOM | 3953 | CA | VAL | B | 460 | 37.472 | -6.334 | 60.972 | 1.00 | 23.87 | B | C |
| ATOM | 3954 | CB | VAL | B | 460 | 37.760 | -7.808 | 61.370 | 1.00 | 24.02 | B | C |
| ATOM | 3955 | CG1 | VAL | B | 460 | 36.526 | -8.659 | 61.142 | 1.00 | 24.02 | B | C |
| ATOM | 3956 | CG2 | VAL | B | 460 | 38.945 | -8.357 | 60.588 | 1.00 | 23.84 | B | C |
| ATOM | 3957 | C | VAL | B | 460 | 38.749 | -5.479 | 61.115 | 1.00 | 24.93 | B | C |
| ATOM | 3958 | O | VAL | B | 460 | 39.193 | -4.852 | 60.142 | 1.00 | 24.10 | B | O |
| ATOM | 3959 | N | ARG | B | 461 | 39.325 | -5.437 | 62.317 | 1.00 | 25.60 | B | N |
| ATOM | 3960 | CA | ARG | B | 461 | 40.533 | -4.648 | 62.550 | 1.00 | 27.14 | B | C |
| ATOM | 3961 | CB | ARG | B | 461 | 40.826 | -4.541 | 64.044 | 1.00 | 28.24 | B | C |
| ATOM | 3962 | CG | ARG | B | 461 | 41.889 | -3.503 | 64.395 | 1.00 | 30.84 | B | C |
| ATOM | 3963 | CD | ARG | B | 461 | 42.173 | -3.476 | 65.885 | 1.00 | 34.64 | B | C |
| ATOM | 3964 | NE | ARG | B | 461 | 42.547 | -4.801 | 66.365 | 1.00 | 40.71 | B | N |
| ATOM | 3965 | CZ | ARG | B | 461 | 43.704 | -5.405 | 66.096 | 1.00 | 43.85 | B | C |
| ATOM | 3966 | NH1 | ARG | B | 461 | 44.636 | -4.800 | 65.362 | 1.00 | 45.66 | B | N |
| ATOM | 3967 | NH2 | ARG | B | 461 | 43.887 | -6.665 | 66.470 | 1.00 | 45.41 | B | N |
| ATOM | 3968 | C | ARG | B | 461 | 41.697 | -5.309 | 61.821 | 1.00 | 27.77 | B | C |
| ATOM | 3969 | O | ARG | B | 461 | 41.963 | -6.494 | 62.018 | 1.00 | 27.14 | B | O |
| ATOM | 3970 | N | PRO | B | 462 | 42.350 | -4.571 | 60.903 | 1.00 | 29.27 | B | N |
| ATOM | 3971 | CD | PRO | B | 462 | 42.042 | -3.196 | 60.465 | 1.00 | 28.49 | B | C |
| ATOM | 3972 | CA | PRO | B | 462 | 43.486 | -5.109 | 60.144 | 1.00 | 30.90 | B | C |
| ATOM | 3973 | CB | PRO | B | 462 | 43.857 | -3.947 | 59.219 | 1.00 | 29.97 | B | C |
| ATOM | 3974 | CG | PRO | B | 462 | 42.569 | -3.195 | 59.056 | 1.00 | 29.12 | B | C |
| ATOM | 3975 | C | PRO | B | 462 | 44.637 | -5.421 | 61.090 | 1.00 | 32.35 | B | C |
| ATOM | 3976 | O | PRO | B | 462 | 44.741 | -4.818 | 62.158 | 1.00 | 31.09 | B | O |
| ATOM | 3977 | N | ASP | B | 463 | 45.485 | -6.375 | 60.715 | 1.00 | 35.53 | B | N |
| ATOM | 3978 | CA | ASP | B | 463 | 46.631 | -6.717 | 61.562 | 1.00 | 38.31 | B | C |
| ATOM | 3979 | CB | ASP | B | 463 | 47.433 | -7.905 | 61.000 | 1.00 | 40.26 | B | C |
| ATOM | 3980 | CG | ASP | B | 463 | 46.624 | -9.214 | 60.949 | 1.00 | 42.82 | B | C |
| ATOM | 3981 | OD1 | ASP | B | 463 | 45.716 | -9.425 | 61.790 | 1.00 | 42.80 | B | O |
| ATOM | 3982 | OD2 | ASP | B | 463 | 46.910 | -10.040 | 60.051 | 1.00 | 44.33 | B | O |
| ATOM | 3983 | C | ASP | B | 463 | 47.530 | -5.486 | 61.681 | 1.00 | 38.90 | B | C |
| ATOM | 3984 | O | ASP | B | 463 | 47.731 | -4.742 | 60.705 | 1.00 | 38.76 | B | O |
| ATOM | 3985 | N | ASN | B | 464 | 47.997 | -5.248 | 62.905 | 1.00 | 40.16 | B | N |
| ATOM | 3986 | CA | ASN | B | 464 | 48.876 | -4.126 | 63.237 | 1.00 | 40.92 | B | C |
| ATOM | 3987 | CB | ASN | B | 464 | 50.195 | -4.224 | 62.465 | 1.00 | 44.27 | B | C |
| ATOM | 3988 | CG | ASN | B | 464 | 51.006 | -5.444 | 62.864 | 1.00 | 47.01 | B | C |
| ATOM | 3989 | OD1 | ASN | B | 464 | 51.356 | -5.615 | 64.038 | 1.00 | 48.68 | B | O |
| ATOM | 3990 | ND2 | ASN | B | 464 | 51.277 | -6.322 | 61.896 | 1.00 | 49.12 | B | N |
| ATOM | 3991 | C | ASN | B | 464 | 48.218 | -2.768 | 63.041 | 1.00 | 39.73 | B | C |
| ATOM | 3992 | O | ASN | B | 464 | 48.794 | -1.839 | 62.463 | 1.00 | 40.05 | B | O |
| ATOM | 3993 | N | CYS | B | 465 | 47.001 | -2.670 | 63.556 | 1.00 | 37.76 | B | N |
| ATOM | 3994 | CA | CYS | B | 465 | 46.224 | -1.446 | 63.484 | 1.00 | 35.26 | B | C |
| ATOM | 3995 | CB | CYS | B | 465 | 45.050 | -1.630 | 62.517 | 1.00 | 33.59 | B | C |
| ATOM | 3996 | SG | CYS | B | 465 | 43.919 | -0.247 | 62.482 | 1.00 | 29.27 | B | S |
| ATOM | 3997 | C | CYS | B | 465 | 45.701 | -1.124 | 64.879 | 1.00 | 33.74 | B | C |
| ATOM | 3998 | O | CYS | B | 465 | 45.032 | -1.952 | 65.491 | 1.00 | 33.81 | B | O |
| ATOM | 3999 | N | PRO | B | 466 | 46.049 | 0.057 | 65.420 | 1.00 | 32.33 | B | N |

Figure 9

| ATOM | 4000 | CD | PRO B 466 | 46.944 | 1.057 | 64.804 | 1.00 | 31.62 | B | C |
|------|------|-----|-----------|--------|--------|--------|------|-------|---|---|
| ATOM | 4001 | CA | PRO B 466 | 45.607 | 0.492 | 66.754 | 1.00 | 31.81 | B | C |
| ATOM | 4002 | CB | PRO B 466 | 46.095 | 1.942 | 66.814 | 1.00 | 31.22 | B | C |
| ATOM | 4003 | CG | PRO B 466 | 47.340 | 1.919 | 65.982 | 1.00 | 31.60 | B | C |
| ATOM | 4004 | C | PRO B 466 | 44.075 | 0.424 | 66.876 | 1.00 | 31.67 | B | C |
| ATOM | 4005 | O | PRO B 466 | 43.371 | 0.646 | 65.886 | 1.00 | 31.84 | B | O |
| ATOM | 4006 | N | GLU B 467 | 43.559 | 0.102 | 68.066 | 1.00 | 31.18 | B | N |
| ATOM | 4007 | CA | GLU B 467 | 42.109 | 0.014 | 68.273 | 1.00 | 30.44 | B | C |
| ATOM | 4008 | CB | GLU B 467 | 41.760 | -0.570 | 69.638 | 1.00 | 31.41 | B | C |
| ATOM | 4009 | CG | GLU B 467 | 41.118 | -1.961 | 69.576 | 1.00 | 34.16 | B | C |
| ATOM | 4010 | CD | GLU B 467 | 39.740 | -1.999 | 68.899 | 1.00 | 34.80 | B | C |
| ATOM | 4011 | OE1 | GLU B 467 | 39.555 | -2.850 | 68.000 | 1.00 | 35.45 | B | O |
| ATOM | 4012 | OE2 | GLU B 467 | 38.834 | -1.226 | 69.297 | 1.00 | 35.55 | B | O |
| ATOM | 4013 | C | GLU B 467 | 41.420 | 1.352 | 68.123 | 1.00 | 29.43 | B | C |
| ATOM | 4014 | O | GLU B 467 | 40.290 | 1.418 | 67.654 | 1.00 | 29.31 | B | O |
| ATOM | 4015 | N | GLU B 468 | 42.092 | 2.416 | 68.539 | 1.00 | 28.51 | B | N |
| ATOM | 4016 | CA | GLU B 468 | 41.535 | 3.753 | 68.416 | 1.00 | 28.23 | B | C |
| ATOM | 4017 | CB | GLU B 468 | 42.345 | 4.765 | 69.240 | 1.00 | 31.65 | B | C |
| ATOM | 4018 | CG | GLU B 468 | 42.535 | 4.401 | 70.726 | 1.00 | 37.89 | B | C |
| ATOM | 4019 | CD | GLU B 468 | 43.668 | 3.366 | 70.981 | 1.00 | 42.15 | B | C |
| ATOM | 4020 | OE1 | GLU B 468 | 44.668 | 3.330 | 70.215 | 1.00 | 42.26 | B | O |
| ATOM | 4021 | OE2 | GLU B 468 | 43.560 | 2.587 | 71.962 | 1.00 | 44.97 | B | O |
| ATOM | 4022 | C | GLU B 468 | 41.469 | 4.174 | 66.937 | 1.00 | 26.64 | B | C |
| ATOM | 4023 | O | GLU B 468 | 40.634 | 4.990 | 66.565 | 1.00 | 26.78 | B | O |
| ATOM | 4024 | N | LEU B 469 | 42.353 | 3.632 | 66.098 | 1.00 | 24.42 | B | N |
| ATOM | 4025 | CA | LEU B 469 | 42.340 | 3.948 | 64.668 | 1.00 | 22.93 | B | C |
| ATOM | 4026 | CB | LEU B 469 | 43.697 | 3.652 | 63.995 | 1.00 | 21.28 | B | C |
| ATOM | 4027 | CG | LEU B 469 | 43.768 | 3.894 | 62.475 | 1.00 | 19.94 | B | C |
| ATOM | 4028 | CD1 | LEU B 469 | 43.608 | 5.360 | 62.167 | 1.00 | 19.58 | B | C |
| ATOM | 4029 | CD2 | LEU B 469 | 45.067 | 3.395 | 61.910 | 1.00 | 18.00 | B | C |
| ATOM | 4030 | C | LEU B 469 | 41.236 | 3.121 | 64.000 | 1.00 | 22.59 | B | C |
| ATOM | 4031 | O | LEU B 469 | 40.581 | 3.584 | 63.062 | 1.00 | 21.96 | B | O |
| ATOM | 4032 | N | TYR B 470 | 41.041 | 1.894 | 64.475 | 1.00 | 21.33 | B | N |
| ATOM | 4033 | CA | TYR B 470 | 39.995 | 1.054 | 63.919 | 1.00 | 21.48 | B | C |
| ATOM | 4034 | CB | TYR B 470 | 40.058 | -0.376 | 64.470 | 1.00 | 21.24 | B | C |
| ATOM | 4035 | CG | TYR B 470 | 38.949 | -1.269 | 63.936 | 1.00 | 21.65 | B | C |
| ATOM | 4036 | CD1 | TYR B 470 | 38.772 | -1.452 | 62.557 | 1.00 | 20.43 | B | C |
| ATOM | 4037 | CE1 | TYR B 470 | 37.725 | -2.241 | 62.062 | 1.00 | 19.68 | B | C |
| ATOM | 4038 | CD2 | TYR B 470 | 38.051 | -1.901 | 64.806 | 1.00 | 21.32 | B | C |
| ATOM | 4039 | CE2 | TYR B 470 | 37.006 | -2.691 | 64.318 | 1.00 | 20.19 | B | C |
| ATOM | 4040 | CZ | TYR B 470 | 36.852 | -2.854 | 62.954 | 1.00 | 19.82 | B | C |
| ATOM | 4041 | OH | TYR B 470 | 35.821 | -3.629 | 62.489 | 1.00 | 19.03 | B | O |
| ATOM | 4042 | C | TYR B 470 | 38.626 | 1.668 | 64.237 | 1.00 | 21.44 | B | C |
| ATOM | 4043 | O | TYR B 470 | 37.695 | 1.574 | 63.435 | 1.00 | 21.57 | B | O |
| ATOM | 4044 | N | GLN B 471 | 38.507 | 2.285 | 65.410 | 1.00 | 20.86 | B | N |
| ATOM | 4045 | CA | GLN B 471 | 37.254 | 2.905 | 65.800 | 1.00 | 20.84 | B | C |
| ATOM | 4046 | CB | GLN B 471 | 37.226 | 3.186 | 67.306 | 1.00 | 21.20 | B | C |
| ATOM | 4047 | CG | GLN B 471 | 37.054 | 1.923 | 68.143 | 1.00 | 23.19 | B | C |
| ATOM | 4048 | CD | GLN B 471 | 35.879 | 1.033 | 67.666 | 1.00 | 26.21 | B | C |
| ATOM | 4049 | OE1 | GLN B 471 | 34.807 | 1.536 | 67.292 | 1.00 | 27.08 | B | O |
| ATOM | 4050 | NE2 | GLN B 471 | 36.088 | -0.292 | 67.673 | 1.00 | 23.64 | B | N |
| ATOM | 4051 | C | GLN B 471 | 36.992 | 4.150 | 64.959 | 1.00 | 20.32 | B | C |
| ATOM | 4052 | O | GLN B 471 | 35.850 | 4.488 | 64.666 | 1.00 | 20.75 | B | O |
| ATOM | 4053 | N | LEU B 472 | 38.060 | 4.796 | 64.517 | 1.00 | 20.41 | B | N |
| ATOM | 4054 | CA | LEU B 472 | 37.941 | 5.965 | 63.662 | 1.00 | 20.53 | B | C |
| ATOM | 4055 | CB | LEU B 472 | 39.312 | 6.622 | 63.513 | 1.00 | 22.54 | B | C |
| ATOM | 4056 | CG | LEU B 472 | 39.316 | 8.107 | 63.174 | 1.00 | 24.73 | B | C |
| ATOM | 4057 | CD1 | LEU B 472 | 38.492 | 8.888 | 64.205 | 1.00 | 24.02 | B | C |
| ATOM | 4058 | CD2 | LEU B 472 | 40.770 | 8.591 | 63.121 | 1.00 | 26.05 | B | C |

Figure 9

| | | | | | | | | | | | |
|---|---|---|---|---|---|---|---|---|---|---|---|
| ATOM | 4059 | C | LEU | B | 472 | 37.409 | 5.493 | 62.291 | 1.00 | 19.34 | B | C |
| ATOM | 4060 | O | LEU | B | 472 | 36.566 | 6.156 | 61.695 | 1.00 | 20.16 | B | O |
| ATOM | 4061 | N | MET | B | 473 | 37.891 | 4.340 | 61.823 | 1.00 | 17.26 | B | N |
| ATOM | 4062 | CA | MET | B | 473 | 37.448 | 3.746 | 60.563 | 1.00 | 16.96 | B | C |
| ATOM | 4063 | CB | MET | B | 473 | 38.196 | 2.447 | 60.284 | 1.00 | 16.26 | B | C |
| ATOM | 4064 | CG | MET | B | 473 | 39.676 | 2.581 | 60.053 | 1.00 | 16.45 | B | C |
| ATOM | 4065 | SD | MET | B | 473 | 40.420 | 0.944 | 59.929 | 1.00 | 17.70 | B | S |
| ATOM | 4066 | CE | MET | B | 473 | 42.108 | 1.387 | 59.532 | 1.00 | 16.31 | B | C |
| ATOM | 4067 | C | MET | B | 473 | 35.958 | 3.411 | 60.654 | 1.00 | 17.56 | B | C |
| ATOM | 4068 | O | MET | B | 473 | 35.194 | 3.661 | 59.721 | 1.00 | 15.95 | B | O |
| ATOM | 4069 | N | ARG | B | 474 | 35.559 | 2.843 | 61.790 | 1.00 | 18.23 | B | N |
| ATOM | 4070 | CA | ARG | B | 474 | 34.166 | 2.460 | 62.014 | 1.00 | 19.01 | B | C |
| ATOM | 4071 | CB | ARG | B | 474 | 34.021 | 1.664 | 63.317 | 1.00 | 18.61 | B | C |
| ATOM | 4072 | CG | ARG | B | 474 | 34.771 | 0.343 | 63.316 | 1.00 | 19.29 | B | C |
| ATOM | 4073 | CD | ARG | B | 474 | 34.280 | -0.587 | 62.212 | 1.00 | 23.46 | B | C |
| ATOM | 4074 | NE | ARG | B | 474 | 32.848 | -0.897 | 62.335 | 1.00 | 24.61 | B | N |
| ATOM | 4075 | CZ | ARG | B | 474 | 32.338 | -2.027 | 62.834 | 1.00 | 23.26 | B | C |
| ATOM | 4076 | NH1 | ARG | B | 474 | 33.115 | -3.015 | 63.271 | 1.00 | 20.27 | B | N |
| ATOM | 4077 | NH2 | ARG | B | 474 | 31.023 | -2.137 | 62.950 | 1.00 | 22.94 | B | N |
| ATOM | 4078 | C | ARG | B | 474 | 33.241 | 3.674 | 61.999 | 1.00 | 18.63 | B | C |
| ATOM | 4079 | O | ARG | B | 474 | 32.074 | 3.569 | 61.625 | 1.00 | 18.74 | B | O |
| ATOM | 4080 | N | LEU | B | 475 | 33.772 | 4.823 | 62.397 | 1.00 | 19.09 | B | N |
| ATOM | 4081 | CA | LEU | B | 475 | 33.002 | 6.054 | 62.380 | 1.00 | 19.09 | B | C |
| ATOM | 4082 | CB | LEU | B | 475 | 33.687 | 7.137 | 63.195 | 1.00 | 20.12 | B | C |
| ATOM | 4083 | CG | LEU | B | 475 | 33.498 | 7.011 | 64.704 | 1.00 | 21.43 | B | C |
| ATOM | 4084 | CD1 | LEU | B | 475 | 34.243 | 8.139 | 65.400 | 1.00 | 20.67 | B | C |
| ATOM | 4085 | CD2 | LEU | B | 475 | 31.998 | 7.035 | 65.040 | 1.00 | 20.98 | B | C |
| ATOM | 4086 | C | LEU | B | 475 | 32.843 | 6.507 | 60.940 | 1.00 | 19.22 | B | C |
| ATOM | 4087 | O | LEU | B | 475 | 31.791 | 7.019 | 60.556 | 1.00 | 19.47 | B | O |
| ATOM | 4088 | N | CYS | B | 476 | 33.899 | 6.324 | 60.146 | 1.00 | 18.28 | B | N |
| ATOM | 4089 | CA | CYS | B | 476 | 33.868 | 6.675 | 58.725 | 1.00 | 16.97 | B | C |
| ATOM | 4090 | CB | CYS | B | 476 | 35.265 | 6.527 | 58.094 | 1.00 | 16.93 | B | C |
| ATOM | 4091 | SG | CYS | B | 476 | 36.519 | 7.678 | 58.704 | 1.00 | 16.71 | B | S |
| ATOM | 4092 | C | CYS | B | 476 | 32.889 | 5.759 | 57.972 | 1.00 | 15.98 | B | C |
| ATOM | 4093 | O | CYS | B | 476 | 32.355 | 6.144 | 56.934 | 1.00 | 14.59 | B | O |
| ATOM | 4094 | N | TRP | B | 477 | 32.676 | 4.550 | 58.495 | 1.00 | 15.43 | B | N |
| ATOM | 4095 | CA | TRP | B | 477 | 31.784 | 3.590 | 57.860 | 1.00 | 16.11 | B | C |
| ATOM | 4096 | CB | TRP | B | 477 | 32.372 | 2.179 | 57.904 | 1.00 | 14.59 | B | C |
| ATOM | 4097 | CG | TRP | B | 477 | 33.707 | 2.068 | 57.285 | 1.00 | 15.49 | B | C |
| ATOM | 4098 | CD2 | TRP | B | 477 | 34.738 | 1.138 | 57.638 | 1.00 | 15.39 | B | C |
| ATOM | 4099 | CE2 | TRP | B | 477 | 35.860 | 1.439 | 56.837 | 1.00 | 15.99 | B | C |
| ATOM | 4100 | CE3 | TRP | B | 477 | 34.821 | 0.085 | 58.561 | 1.00 | 16.03 | B | C |
| ATOM | 4101 | CD1 | TRP | B | 477 | 34.227 | 2.863 | 56.300 | 1.00 | 14.61 | B | C |
| ATOM | 4102 | NE1 | TRP | B | 477 | 35.515 | 2.494 | 56.031 | 1.00 | 16.03 | B | N |
| ATOM | 4103 | CZ2 | TRP | B | 477 | 37.069 | 0.725 | 56.930 | 1.00 | 15.63 | B | C |
| ATOM | 4104 | CZ3 | TRP | B | 477 | 36.010 | -0.623 | 58.656 | 1.00 | 16.55 | B | C |
| ATOM | 4105 | CH2 | TRP | B | 477 | 37.126 | -0.297 | 57.839 | 1.00 | 16.05 | B | C |
| ATOM | 4106 | C | TRP | B | 477 | 30.355 | 3.544 | 58.396 | 1.00 | 16.16 | B | C |
| ATOM | 4107 | O | TRP | B | 477 | 29.655 | 2.568 | 58.157 | 1.00 | 17.18 | B | O |
| ATOM | 4108 | N | LYS | B | 478 | 29.920 | 4.574 | 59.117 | 1.00 | 17.35 | B | N |
| ATOM | 4109 | CA | LYS | B | 478 | 28.549 | 4.591 | 59.643 | 1.00 | 18.44 | B | C |
| ATOM | 4110 | CB | LYS | B | 478 | 28.260 | 5.864 | 60.464 | 1.00 | 19.14 | B | C |
| ATOM | 4111 | CG | LYS | B | 478 | 28.964 | 5.938 | 61.850 | 1.00 | 22.21 | B | C |
| ATOM | 4112 | CD | LYS | B | 478 | 28.600 | 4.781 | 62.779 | 1.00 | 23.38 | B | C |
| ATOM | 4113 | CE | LYS | B | 478 | 27.268 | 4.985 | 63.461 | 1.00 | 25.84 | B | C |
| ATOM | 4114 | NZ | LYS | B | 478 | 26.820 | 3.741 | 64.157 | 1.00 | 29.85 | B | N |
| ATOM | 4115 | C | LYS | B | 478 | 27.608 | 4.518 | 58.459 | 1.00 | 17.86 | B | C |
| ATOM | 4116 | O | LYS | B | 478 | 27.868 | 5.135 | 57.435 | 1.00 | 17.40 | B | O |
| ATOM | 4117 | N | GLU | B | 479 | 26.533 | 3.743 | 58.593 | 1.00 | 18.59 | B | N |

Figure 9

| ATOM | 4118 | CA  | GLU | B | 479 | 25.556 | 3.572  | 57.522 | 1.00 | 18.59 | B | C |
| ---- | ---- | --- | --- | - | --- | ------ | ------ | ------ | ---- | ----- | - | - |
| ATOM | 4119 | CB  | GLU | B | 479 | 24.438 | 2.641  | 57.985 | 1.00 | 19.04 | B | C |
| ATOM | 4120 | CG  | GLU | B | 479 | 23.489 | 2.175  | 56.865 | 1.00 | 19.72 | B | C |
| ATOM | 4121 | CD  | GLU | B | 479 | 24.174 | 1.336  | 55.790 | 1.00 | 20.82 | B | C |
| ATOM | 4122 | OE1 | GLU | B | 479 | 25.103 | 0.572  | 56.113 | 1.00 | 21.21 | B | O |
| ATOM | 4123 | OE2 | GLU | B | 479 | 23.780 | 1.438  | 54.611 | 1.00 | 21.32 | B | O |
| ATOM | 4124 | C   | GLU | B | 479 | 24.974 | 4.889  | 56.998 | 1.00 | 18.32 | B | C |
| ATOM | 4125 | O   | GLU | B | 479 | 24.879 | 5.105  | 55.792 | 1.00 | 17.51 | B | O |
| ATOM | 4126 | N   | ARG | B | 480 | 24.563 | 5.753  | 57.915 | 1.00 | 18.95 | B | N |
| ATOM | 4127 | CA  | ARG | B | 480 | 24.008 | 7.046  | 57.547 | 1.00 | 19.39 | B | C |
| ATOM | 4128 | CB  | ARG | B | 480 | 23.064 | 7.532  | 58.636 | 1.00 | 22.37 | B | C |
| ATOM | 4129 | CG  | ARG | B | 480 | 21.838 | 6.698  | 58.819 | 1.00 | 26.34 | B | C |
| ATOM | 4130 | CD  | ARG | B | 480 | 21.115 | 7.248  | 59.992 | 1.00 | 32.03 | B | C |
| ATOM | 4131 | NE  | ARG | B | 480 | 19.866 | 6.559  | 60.262 | 1.00 | 38.75 | B | N |
| ATOM | 4132 | CZ  | ARG | B | 480 | 19.450 | 6.222  | 61.484 | 1.00 | 42.24 | B | C |
| ATOM | 4133 | NH1 | ARG | B | 480 | 20.187 | 6.505  | 62.560 | 1.00 | 42.97 | B | N |
| ATOM | 4134 | NH2 | ARG | B | 480 | 18.276 | 5.616  | 61.629 | 1.00 | 43.49 | B | N |
| ATOM | 4135 | C   | ARG | B | 480 | 25.138 | 8.053  | 57.385 | 1.00 | 17.76 | B | C |
| ATOM | 4136 | O   | ARG | B | 480 | 25.964 | 8.210  | 58.279 | 1.00 | 16.81 | B | O |
| ATOM | 4137 | N   | PRO | B | 481 | 25.132 | 8.812  | 56.282 | 1.00 | 17.35 | B | N |
| ATOM | 4138 | CD  | PRO | B | 481 | 24.168 | 8.789  | 55.167 | 1.00 | 17.29 | B | C |
| ATOM | 4139 | CA  | PRO | B | 481 | 26.175 | 9.805  | 56.028 | 1.00 | 16.23 | B | C |
| ATOM | 4140 | CB  | PRO | B | 481 | 25.706 | 10.463 | 54.713 | 1.00 | 16.83 | B | C |
| ATOM | 4141 | CG  | PRO | B | 481 | 24.977 | 9.391  | 54.037 | 1.00 | 16.73 | B | C |
| ATOM | 4142 | C   | PRO | B | 481 | 26.351 | 10.841 | 57.131 | 1.00 | 15.98 | B | C |
| ATOM | 4143 | O   | PRO | B | 481 | 27.466 | 11.286 | 57.398 | 1.00 | 14.94 | B | O |
| ATOM | 4144 | N   | GLU | B | 482 | 25.256 | 11.238 | 57.762 | 1.00 | 15.54 | B | N |
| ATOM | 4145 | CA  | GLU | B | 482 | 25.324 | 12.250 | 58.801 | 1.00 | 15.76 | B | C |
| ATOM | 4146 | CB  | GLU | B | 482 | 23.922 | 12.780 | 59.139 | 1.00 | 18.21 | B | C |
| ATOM | 4147 | CG  | GLU | B | 482 | 23.004 | 11.801 | 59.884 | 1.00 | 20.45 | B | C |
| ATOM | 4148 | CD  | GLU | B | 482 | 22.157 | 10.909 | 58.989 | 1.00 | 21.20 | B | C |
| ATOM | 4149 | OE1 | GLU | B | 482 | 22.297 | 10.914 | 57.745 | 1.00 | 20.62 | B | O |
| ATOM | 4150 | OE2 | GLU | B | 482 | 21.321 | 10.195 | 59.559 | 1.00 | 23.85 | B | O |
| ATOM | 4151 | C   | GLU | B | 482 | 26.050 | 11.801 | 60.059 | 1.00 | 15.38 | B | C |
| ATOM | 4152 | O   | GLU | B | 482 | 26.563 | 12.626 | 60.819 | 1.00 | 15.99 | B | O |
| ATOM | 4153 | N   | ASP | B | 483 | 26.136 | 10.492 | 60.258 | 1.00 | 15.45 | B | N |
| ATOM | 4154 | CA  | ASP | B | 483 | 26.804 | 9.945  | 61.429 | 1.00 | 15.40 | B | C |
| ATOM | 4155 | CB  | ASP | B | 483 | 26.202 | 8.591  | 61.802 | 1.00 | 17.09 | B | C |
| ATOM | 4156 | CG  | ASP | B | 483 | 24.776 | 8.707  | 62.312 | 1.00 | 18.21 | B | C |
| ATOM | 4157 | OD1 | ASP | B | 483 | 24.444 | 9.753  | 62.889 | 1.00 | 18.84 | B | O |
| ATOM | 4158 | OD2 | ASP | B | 483 | 23.991 | 7.758  | 62.129 | 1.00 | 19.12 | B | O |
| ATOM | 4159 | C   | ASP | B | 483 | 28.307 | 9.800  | 61.259 | 1.00 | 16.05 | B | C |
| ATOM | 4160 | O   | ASP | B | 483 | 28.996 | 9.408  | 62.204 | 1.00 | 16.50 | B | O |
| ATOM | 4161 | N   | ARG | B | 484 | 28.801 | 10.068 | 60.049 | 1.00 | 14.92 | B | N |
| ATOM | 4162 | CA  | ARG | B | 484 | 30.229 | 9.991  | 59.748 | 1.00 | 14.65 | B | C |
| ATOM | 4163 | CB  | ARG | B | 484 | 30.435 | 9.699  | 58.263 | 1.00 | 13.50 | B | C |
| ATOM | 4164 | CG  | ARG | B | 484 | 29.876 | 8.373  | 57.825 | 1.00 | 11.84 | B | C |
| ATOM | 4165 | CD  | ARG | B | 484 | 29.845 | 8.279  | 56.318 | 1.00 | 12.21 | B | C |
| ATOM | 4166 | NE  | ARG | B | 484 | 28.976 | 7.190  | 55.896 | 1.00 | 13.36 | B | N |
| ATOM | 4167 | CZ  | ARG | B | 484 | 28.459 | 7.060  | 54.681 | 1.00 | 13.15 | B | C |
| ATOM | 4168 | NH1 | ARG | B | 484 | 28.737 | 7.952  | 53.733 | 1.00 | 11.61 | B | N |
| ATOM | 4169 | NH2 | ARG | B | 484 | 27.594 | 6.079  | 54.444 | 1.00 | 13.09 | B | N |
| ATOM | 4170 | C   | ARG | B | 484 | 30.892 | 11.318 | 60.128 | 1.00 | 15.08 | B | C |
| ATOM | 4171 | O   | ARG | B | 484 | 30.302 | 12.388 | 59.920 | 1.00 | 15.06 | B | O |
| ATOM | 4172 | N   | PRO | B | 485 | 32.145 | 11.272 | 60.655 | 1.00 | 15.75 | B | N |
| ATOM | 4173 | CD  | PRO | B | 485 | 32.976 | 10.071 | 60.834 | 1.00 | 15.32 | B | C |
| ATOM | 4174 | CA  | PRO | B | 485 | 32.880 | 12.480 | 61.065 | 1.00 | 15.60 | B | C |
| ATOM | 4175 | CB  | PRO | B | 485 | 34.193 | 11.918 | 61.630 | 1.00 | 16.31 | B | C |
| ATOM | 4176 | CG  | PRO | B | 485 | 33.890 | 10.500 | 61.942 | 1.00 | 17.65 | B | C |

Figure 9

| | | | | | | | | | | | |
|---|---|---|---|---|---|---|---|---|---|---|---|
| ATOM | 4177 | C | PRO | B | 485 | 33.197 | 13.418 | 59.904 | 1.00 | 15.23 | B | C |
| ATOM | 4178 | O | PRO | B | 485 | 33.079 | 13.038 | 58.731 | 1.00 | 15.73 | B | O |
| ATOM | 4179 | N | THR | B | 486 | 33.572 | 14.651 | 60.229 | 1.00 | 15.50 | B | N |
| ATOM | 4180 | CA | THR | B | 486 | 33.975 | 15.601 | 59.200 | 1.00 | 16.07 | B | C |
| ATOM | 4181 | CB | THR | B | 486 | 33.775 | 17.082 | 59.614 | 1.00 | 15.46 | B | C |
| ATOM | 4182 | OG1 | THR | B | 486 | 34.491 | 17.348 | 60.823 | 1.00 | 18.22 | B | O |
| ATOM | 4183 | CG2 | THR | B | 486 | 32.318 | 17.408 | 59.798 | 1.00 | 15.24 | B | C |
| ATOM | 4184 | C | THR | B | 486 | 35.484 | 15.390 | 59.011 | 1.00 | 16.49 | B | C |
| ATOM | 4185 | O | THR | B | 486 | 36.158 | 14.828 | 59.890 | 1.00 | 15.91 | B | O |
| ATOM | 4186 | N | PHE | B | 487 | 35.990 | 15.796 | 57.853 | 1.00 | 16.91 | B | N |
| ATOM | 4187 | CA | PHE | B | 487 | 37.417 | 15.705 | 57.561 | 1.00 | 18.27 | B | C |
| ATOM | 4188 | CB | PHE | B | 487 | 37.683 | 16.026 | 56.095 | 1.00 | 16.51 | B | C |
| ATOM | 4189 | CG | PHE | B | 487 | 37.495 | 14.846 | 55.192 | 1.00 | 16.65 | B | C |
| ATOM | 4190 | CD1 | PHE | B | 487 | 38.338 | 13.738 | 55.302 | 1.00 | 15.10 | B | C |
| ATOM | 4191 | CD2 | PHE | B | 487 | 36.471 | 14.821 | 54.249 | 1.00 | 16.74 | B | C |
| ATOM | 4192 | CE1 | PHE | B | 487 | 38.163 | 12.632 | 54.491 | 1.00 | 14.94 | B | C |
| ATOM | 4193 | CE2 | PHE | B | 487 | 36.290 | 13.713 | 53.433 | 1.00 | 15.28 | B | C |
| ATOM | 4194 | CZ | PHE | B | 487 | 37.139 | 12.616 | 53.553 | 1.00 | 14.74 | B | C |
| ATOM | 4195 | C | PHE | B | 487 | 38.154 | 16.666 | 58.478 | 1.00 | 19.93 | B | C |
| ATOM | 4196 | O | PHE | B | 487 | 39.298 | 16.421 | 58.860 | 1.00 | 20.02 | B | O |
| ATOM | 4197 | N | ASP | B | 488 | 37.459 | 17.731 | 58.876 | 1.00 | 21.18 | B | N |
| ATOM | 4198 | CA | ASP | B | 488 | 38.005 | 18.713 | 59.803 | 1.00 | 22.31 | B | C |
| ATOM | 4199 | CB | ASP | B | 488 | 36.968 | 19.823 | 60.018 | 1.00 | 25.55 | B | C |
| ATOM | 4200 | CG | ASP | B | 488 | 37.354 | 20.810 | 61.119 | 1.00 | 29.61 | B | C |
| ATOM | 4201 | OD1 | ASP | B | 488 | 38.554 | 20.926 | 61.463 | 1.00 | 31.02 | B | O |
| ATOM | 4202 | OD2 | ASP | B | 488 | 36.429 | 21.477 | 61.647 | 1.00 | 31.64 | B | O |
| ATOM | 4203 | C | ASP | B | 488 | 38.325 | 17.961 | 61.108 | 1.00 | 22.27 | B | C |
| ATOM | 4204 | O | ASP | B | 488 | 39.422 | 18.084 | 61.661 | 1.00 | 22.49 | B | O |
| ATOM | 4205 | N | TYR | B | 489 | 37.391 | 17.127 | 61.553 | 1.00 | 20.93 | B | N |
| ATOM | 4206 | CA | TYR | B | 489 | 37.586 | 16.344 | 62.760 | 1.00 | 20.19 | B | C |
| ATOM | 4207 | CB | TYR | B | 489 | 36.274 | 15.692 | 63.179 | 1.00 | 18.15 | B | C |
| ATOM | 4208 | CG | TYR | B | 489 | 36.486 | 14.674 | 64.257 | 1.00 | 17.78 | B | C |
| ATOM | 4209 | CD1 | TYR | B | 489 | 36.771 | 15.073 | 65.556 | 1.00 | 17.66 | B | C |
| ATOM | 4210 | CE1 | TYR | B | 489 | 37.043 | 14.147 | 66.547 | 1.00 | 19.70 | B | C |
| ATOM | 4211 | CD2 | TYR | B | 489 | 36.468 | 13.309 | 63.965 | 1.00 | 16.89 | B | C |
| ATOM | 4212 | CE2 | TYR | B | 489 | 36.732 | 12.365 | 64.936 | 1.00 | 17.82 | B | C |
| ATOM | 4213 | CZ | TYR | B | 489 | 37.026 | 12.788 | 66.239 | 1.00 | 21.60 | B | C |
| ATOM | 4214 | OH | TYR | B | 489 | 37.320 | 11.872 | 67.237 | 1.00 | 21.74 | B | O |
| ATOM | 4215 | C | TYR | B | 489 | 38.672 | 15.264 | 62.583 | 1.00 | 21.20 | B | C |
| ATOM | 4216 | O | TYR | B | 489 | 39.512 | 15.073 | 63.466 | 1.00 | 21.38 | B | O |
| ATOM | 4217 | N | LEU | B | 490 | 38.620 | 14.530 | 61.469 | 1.00 | 21.45 | B | N |
| ATOM | 4218 | CA | LEU | B | 490 | 39.595 | 13.473 | 61.180 | 1.00 | 22.07 | B | C |
| ATOM | 4219 | CB | LEU | B | 490 | 39.269 | 12.779 | 59.847 | 1.00 | 21.29 | B | C |
| ATOM | 4220 | CG | LEU | B | 490 | 38.001 | 11.911 | 59.755 | 1.00 | 20.08 | B | C |
| ATOM | 4221 | CD1 | LEU | B | 490 | 37.612 | 11.665 | 58.316 | 1.00 | 17.47 | B | C |
| ATOM | 4222 | CD2 | LEU | B | 490 | 38.198 | 10.602 | 60.495 | 1.00 | 17.59 | B | C |
| ATOM | 4223 | C | LEU | B | 490 | 41.040 | 13.996 | 61.168 | 1.00 | 23.40 | B | C |
| ATOM | 4224 | O | LEU | B | 490 | 41.937 | 13.312 | 61.646 | 1.00 | 22.04 | B | O |
| ATOM | 4225 | N | ARG | B | 491 | 41.259 | 15.199 | 60.626 | 1.00 | 25.91 | B | N |
| ATOM | 4226 | CA | ARG | B | 491 | 42.597 | 15.806 | 60.591 | 1.00 | 28.51 | B | C |
| ATOM | 4227 | CB | ARG | B | 491 | 42.618 | 17.106 | 59.769 | 1.00 | 29.46 | B | C |
| ATOM | 4228 | CG | ARG | B | 491 | 43.964 | 17.847 | 59.850 | 1.00 | 33.10 | B | C |
| ATOM | 4229 | CD | ARG | B | 491 | 43.839 | 19.338 | 59.532 | 1.00 | 37.84 | B | C |
| ATOM | 4230 | NE | ARG | B | 491 | 42.667 | 19.949 | 60.171 | 1.00 | 43.28 | B | N |
| ATOM | 4231 | CZ | ARG | B | 491 | 42.581 | 20.285 | 61.460 | 1.00 | 45.45 | B | C |
| ATOM | 4232 | NH1 | ARG | B | 491 | 43.609 | 20.095 | 62.290 | 1.00 | 45.66 | B | N |
| ATOM | 4233 | NH2 | ARG | B | 491 | 41.431 | 20.756 | 61.940 | 1.00 | 45.52 | B | N |
| ATOM | 4234 | C | ARG | B | 491 | 43.098 | 16.090 | 62.017 | 1.00 | 29.69 | B | C |
| ATOM | 4235 | O | ARG | B | 491 | 44.244 | 15.779 | 62.341 | 1.00 | 30.38 | B | O |

Figure 9

| | | | | | | | | | | | |
|---|---|---|---|---|---|---|---|---|---|---|---|
| ATOM | 4236 | N | SER | B | 492 | 42.246 | 16.687 | 62.856 | 1.00 | 29.88 | B N |
| ATOM | 4237 | CA | SER | B | 492 | 42.610 | 16.983 | 64.248 | 1.00 | 30.09 | B C |
| ATOM | 4238 | CB | SER | B | 492 | 41.437 | 17.620 | 65.001 | 1.00 | 29.92 | B C |
| ATOM | 4239 | OG | SER | B | 492 | 41.058 | 18.823 | 64.385 | 1.00 | 32.35 | B O |
| ATOM | 4240 | C | SER | B | 492 | 43.028 | 15.720 | 64.996 | 1.00 | 29.84 | B C |
| ATOM | 4241 | O | SER | B | 492 | 44.106 | 15.675 | 65.588 | 1.00 | 29.39 | B O |
| ATOM | 4242 | N | VAL | B | 493 | 42.177 | 14.693 | 64.946 | 1.00 | 29.39 | B N |
| ATOM | 4243 | CA | VAL | B | 493 | 42.439 | 13.438 | 65.637 | 1.00 | 29.29 | B C |
| ATOM | 4244 | CB | VAL | B | 493 | 41.165 | 12.540 | 65.684 | 1.00 | 30.21 | B C |
| ATOM | 4245 | CG1 | VAL | B | 493 | 40.645 | 12.263 | 64.295 | 1.00 | 32.50 | B C |
| ATOM | 4246 | CG2 | VAL | B | 493 | 41.454 | 11.234 | 66.395 | 1.00 | 31.64 | B C |
| ATOM | 4247 | C | VAL | B | 493 | 43.667 | 12.675 | 65.119 | 1.00 | 29.06 | B C |
| ATOM | 4248 | O | VAL | B | 493 | 44.383 | 12.046 | 65.903 | 1.00 | 27.82 | B O |
| ATOM | 4249 | N | LEU | B | 494 | 43.942 | 12.777 | 63.820 | 1.00 | 28.66 | B N |
| ATOM | 4250 | CA | LEU | B | 494 | 45.094 | 12.101 | 63.231 | 1.00 | 29.07 | B C |
| ATOM | 4251 | CB | LEU | B | 494 | 44.907 | 11.940 | 61.724 | 1.00 | 26.90 | B C |
| ATOM | 4252 | CG | LEU | B | 494 | 43.868 | 10.879 | 61.346 | 1.00 | 27.92 | B C |
| ATOM | 4253 | CD1 | LEU | B | 494 | 43.538 | 10.912 | 59.858 | 1.00 | 25.90 | B C |
| ATOM | 4254 | CD2 | LEU | B | 494 | 44.361 | 9.492 | 61.777 | 1.00 | 26.79 | B C |
| ATOM | 4255 | C | LEU | B | 494 | 46.389 | 12.840 | 63.562 | 1.00 | 30.21 | B C |
| ATOM | 4256 | O | LEU | B | 494 | 47.418 | 12.220 | 63.781 | 1.00 | 30.77 | B O |
| ATOM | 4257 | N | GLU | B | 495 | 46.319 | 14.164 | 63.636 | 1.00 | 32.47 | B N |
| ATOM | 4258 | CA | GLU | B | 495 | 47.469 | 14.996 | 63.980 | 1.00 | 35.43 | B C |
| ATOM | 4259 | CB | GLU | B | 495 | 47.096 | 16.475 | 63.879 | 1.00 | 35.93 | B C |
| ATOM | 4260 | CG | GLU | B | 495 | 47.457 | 17.127 | 62.566 | 1.00 | 38.99 | B C |
| ATOM | 4261 | CD | GLU | B | 495 | 47.056 | 18.594 | 62.496 | 1.00 | 40.48 | B C |
| ATOM | 4262 | OE1 | GLU | B | 495 | 46.911 | 19.239 | 63.562 | 1.00 | 40.76 | B O |
| ATOM | 4263 | OE2 | GLU | B | 495 | 46.889 | 19.096 | 61.358 | 1.00 | 42.06 | B O |
| ATOM | 4264 | C | GLU | B | 495 | 47.937 | 14.734 | 65.407 | 1.00 | 37.32 | B C |
| ATOM | 4265 | O | GLU | B | 495 | 49.134 | 14.718 | 65.694 | 1.00 | 37.86 | B O |
| ATOM | 4266 | N | ASP | B | 496 | 46.979 | 14.543 | 66.305 | 1.00 | 39.67 | B N |
| ATOM | 4267 | CA | ASP | B | 496 | 47.274 | 14.321 | 67.715 | 1.00 | 42.17 | B C |
| ATOM | 4268 | CB | ASP | B | 496 | 46.296 | 15.138 | 68.578 | 1.00 | 43.55 | B C |
| ATOM | 4269 | CG | ASP | B | 496 | 46.148 | 16.593 | 68.102 | 1.00 | 45.81 | B C |
| ATOM | 4270 | OD1 | ASP | B | 496 | 47.132 | 17.183 | 67.599 | 1.00 | 47.00 | B O |
| ATOM | 4271 | OD2 | ASP | B | 496 | 45.030 | 17.151 | 68.236 | 1.00 | 47.27 | B O |
| ATOM | 4272 | C | ASP | B | 496 | 47.236 | 12.856 | 68.165 | 1.00 | 43.61 | B C |
| ATOM | 4273 | O | ASP | B | 496 | 47.201 | 12.596 | 69.367 | 1.00 | 44.48 | B O |
| ATOM | 4274 | N | PHE | B | 497 | 47.318 | 11.909 | 67.228 | 1.00 | 44.60 | B N |
| ATOM | 4275 | CA | PHE | B | 497 | 47.238 | 10.488 | 67.575 | 1.00 | 45.97 | B C |
| ATOM | 4276 | CB | PHE | B | 497 | 47.344 | 9.608 | 66.335 | 1.00 | 45.15 | B C |
| ATOM | 4277 | CG | PHE | B | 497 | 46.603 | 8.307 | 66.461 | 1.00 | 44.45 | B C |
| ATOM | 4278 | CD1 | PHE | B | 497 | 45.242 | 8.238 | 66.161 | 1.00 | 44.53 | B C |
| ATOM | 4279 | CD2 | PHE | B | 497 | 47.257 | 7.150 | 66.882 | 1.00 | 44.12 | B C |
| ATOM | 4280 | CE1 | PHE | B | 497 | 44.544 | 7.036 | 66.277 | 1.00 | 44.19 | B C |
| ATOM | 4281 | CE2 | PHE | B | 497 | 46.574 | 5.940 | 67.001 | 1.00 | 44.20 | B C |
| ATOM | 4282 | CZ | PHE | B | 497 | 45.214 | 5.883 | 66.698 | 1.00 | 44.34 | B C |
| ATOM | 4283 | C | PHE | B | 497 | 48.198 | 9.999 | 68.661 | 1.00 | 47.65 | B C |
| ATOM | 4284 | O | PHE | B | 497 | 47.830 | 9.140 | 69.468 | 1.00 | 48.11 | B O |
| ATOM | 4285 | N | PHE | B | 498 | 49.431 | 10.503 | 68.645 | 1.00 | 49.38 | B N |
| ATOM | 4286 | CA | PHE | B | 498 | 50.449 | 10.167 | 69.661 | 1.00 | 51.16 | B C |
| ATOM | 4287 | CB | PHE | B | 498 | 50.740 | 8.648 | 69.768 | 1.00 | 50.95 | B C |
| ATOM | 4288 | CG | PHE | B | 498 | 50.895 | 7.924 | 68.437 | 1.00 | 50.16 | B C |
| ATOM | 4289 | CD1 | PHE | B | 498 | 51.294 | 8.591 | 67.280 | 1.00 | 49.29 | B C |
| ATOM | 4290 | CD2 | PHE | B | 498 | 50.625 | 6.560 | 68.360 | 1.00 | 49.21 | B C |
| ATOM | 4291 | CE1 | PHE | B | 498 | 51.414 | 7.907 | 66.077 | 1.00 | 49.87 | B C |
| ATOM | 4292 | CE2 | PHE | B | 498 | 50.742 | 5.869 | 67.166 | 1.00 | 48.82 | B C |
| ATOM | 4293 | CZ | PHE | B | 498 | 51.136 | 6.539 | 66.023 | 1.00 | 49.19 | B C |
| ATOM | 4294 | C | PHE | B | 498 | 51.751 | 10.952 | 69.503 | 1.00 | 52.07 | B C |

Figure 9

| | | | | | | | | | | | |
|---|---|---|---|---|---|---|---|---|---|---|---|
| ATOM | 4295 | O | PHE | B | 498 | 51.639 | 12.197 | 69.423 | 1.00 53.11 | B | O |
| ATOM | 4296 | N1 | LIG | B | 500 | 52.487 | 14.138 | 39.514 | 1.00 22.83 | B | N |
| ATOM | 4297 | C1 | LIG | B | 500 | 53.155 | 12.934 | 39.393 | 1.00 24.37 | B | C |
| ATOM | 4298 | N2 | LIG | B | 500 | 54.470 | 12.862 | 39.699 | 1.00 25.37 | B | N |
| ATOM | 4299 | C2 | LIG | B | 500 | 55.153 | 11.720 | 39.612 | 1.00 25.10 | B | C |
| ATOM | 4300 | N3 | LIG | B | 500 | 54.570 | 10.596 | 39.218 | 1.00 24.75 | B | N |
| ATOM | 4301 | C3 | LIG | B | 500 | 53.256 | 10.556 | 38.886 | 1.00 24.66 | B | C |
| ATOM | 4302 | N4 | LIG | B | 500 | 52.416 | 9.536 | 38.456 | 1.00 25.33 | B | N |
| ATOM | 4303 | C4 | LIG | B | 500 | 52.690 | 8.070 | 38.215 | 1.00 25.51 | B | C |
| ATOM | 4304 | C5 | LIG | B | 500 | 52.405 | 7.729 | 36.754 | 1.00 25.51 | B | C |
| ATOM | 4305 | C6 | LIG | B | 500 | 52.612 | 6.228 | 36.507 | 1.00 26.08 | B | C |
| ATOM | 4306 | C7 | LIG | B | 500 | 53.039 | 5.527 | 37.810 | 1.00 26.88 | B | C |
| ATOM | 4307 | N5 | LIG | B | 500 | 53.217 | 4.309 | 37.580 | 0.00 20.00 | B | N |
| ATOM | 4308 | C8 | LIG | B | 500 | 54.267 | 4.150 | 36.568 | 0.00 20.00 | B | C |
| ATOM | 4309 | C9 | LIG | B | 500 | 54.657 | 2.673 | 36.461 | 0.00 20.00 | B | C |
| ATOM | 4310 | N6 | LIG | B | 500 | 55.220 | 2.220 | 37.738 | 0.00 20.00 | B | N |
| ATOM | 4311 | C10 | LIG | B | 500 | 55.459 | 0.776 | 37.605 | 0.00 20.00 | B | C |
| ATOM | 4312 | C11 | LIG | B | 500 | 54.168 | 2.380 | 38.751 | 0.00 20.00 | B | C |
| ATOM | 4313 | C12 | LIG | B | 500 | 53.779 | 3.857 | 38.857 | 0.00 20.00 | B | C |
| ATOM | 4314 | C13 | LIG | B | 500 | 51.941 | 5.717 | 38.874 | 1.00 26.67 | B | C |
| ATOM | 4315 | C14 | LIG | B | 500 | 51.772 | 7.215 | 39.132 | 1.00 26.03 | B | C |
| ATOM | 4316 | N8 | LIG | B | 500 | 51.164 | 10.025 | 38.257 | 1.00 24.56 | B | N |
| ATOM | 4317 | C16 | LIG | B | 500 | 51.148 | 11.364 | 38.543 | 1.00 23.95 | B | C |
| ATOM | 4318 | C17 | LIG | B | 500 | 49.891 | 12.151 | 38.409 | 1.00 24.06 | B | C |
| ATOM | 4319 | C18 | LIG | B | 500 | 48.666 | 11.539 | 38.717 | 1.00 24.03 | B | C |
| ATOM | 4320 | C19 | LIG | B | 500 | 47.509 | 12.261 | 38.618 | 1.00 24.31 | B | C |
| ATOM | 4321 | C21 | LIG | B | 500 | 47.536 | 13.583 | 38.189 | 1.00 24.98 | B | C |
| ATOM | 4322 | N7 | LIG | B | 500 | 46.327 | 14.246 | 38.139 | 1.00 25.94 | B | N |
| ATOM | 4323 | C22 | LIG | B | 500 | 46.184 | 15.637 | 37.760 | 1.00 26.26 | B | C |
| ATOM | 4324 | C23 | LIG | B | 500 | 44.717 | 15.993 | 37.917 | 1.00 26.19 | B | C |
| ATOM | 4325 | C24 | LIG | B | 500 | 44.279 | 16.439 | 39.163 | 1.00 25.78 | B | C |
| ATOM | 4326 | CL1 | LIG | B | 500 | 45.461 | 16.552 | 40.534 | 1.00 22.71 | B | CL |
| ATOM | 4327 | C26 | LIG | B | 500 | 42.939 | 16.781 | 39.348 | 1.00 25.83 | B | C |
| ATOM | 4328 | C27 | LIG | B | 500 | 42.040 | 16.694 | 38.291 | 1.00 26.26 | B | C |
| ATOM | 4329 | C28 | LIG | B | 500 | 42.465 | 16.251 | 37.032 | 1.00 26.61 | B | C |
| ATOM | 4330 | C29 | LIG | B | 500 | 43.798 | 15.906 | 36.830 | 1.00 26.31 | B | C |
| ATOM | 4331 | F1 | LIG | B | 500 | 44.197 | 15.486 | 35.599 | 1.00 27.47 | B | F |
| ATOM | 4332 | C30 | LIG | B | 500 | 48.756 | 14.214 | 37.891 | 1.00 24.82 | B | C |
| ATOM | 4333 | C31 | LIG | B | 500 | 49.934 | 13.484 | 37.993 | 1.00 23.67 | B | C |
| ATOM | 4334 | C32 | LIG | B | 500 | 52.512 | 11.740 | 38.964 | 1.00 24.56 | B | C |
| ATOM | 4335 | OH2 | H2O | B | 600 | 33.769 | 0.103 | 51.034 | 1.00 15.82 | B | O |
| ATOM | 4336 | OH2 | H2O | B | 601 | 29.497 | 19.109 | 61.269 | 1.00 67.78 | B | O |
| ATOM | 4337 | OH2 | H2O | B | 602 | 26.976 | -1.907 | 59.640 | 1.00 14.55 | B | O |
| ATOM | 4338 | OH2 | H2O | B | 604 | 34.240 | 19.731 | 63.045 | 1.00 37.63 | B | O |
| ATOM | 4339 | OH2 | H2O | B | 605 | 22.533 | -3.309 | 58.113 | 1.00 43.08 | B | O |
| ATOM | 4340 | OH2 | H2O | B | 606 | 35.787 | 9.245 | 47.279 | 1.00 12.42 | B | O |
| ATOM | 4341 | OH2 | H2O | B | 607 | 24.588 | 5.364 | 60.780 | 1.00 16.10 | B | O |
| ATOM | 4342 | OH2 | H2O | B | 608 | 28.882 | 13.002 | 63.526 | 1.00 30.32 | B | O |
| ATOM | 4343 | OH2 | H2O | B | 609 | 27.360 | -8.372 | 57.930 | 1.00 21.05 | B | O |
| ATOM | 4344 | OH2 | H2O | B | 610 | 34.389 | -2.185 | 55.822 | 1.00 14.80 | B | O |
| ATOM | 4345 | OH2 | H2O | B | 611 | 33.845 | 3.667 | 66.307 | 1.00 17.36 | B | O |
| ATOM | 4346 | OH2 | H2O | B | 612 | 28.735 | 16.603 | 59.789 | 1.00 25.67 | B | O |
| ATOM | 4347 | OH2 | H2O | B | 613 | 27.911 | -6.310 | 60.535 | 1.00 69.35 | B | O |
| ATOM | 4348 | OH2 | H2O | B | 614 | 37.693 | 12.523 | 41.217 | 1.00 19.11 | B | O |
| ATOM | 4349 | OH2 | H2O | B | 615 | 18.824 | 14.140 | 62.814 | 1.00 39.60 | B | O |
| ATOM | 4350 | OH2 | H2O | B | 616 | 26.344 | 15.545 | 60.698 | 1.00 32.98 | B | O |
| ATOM | 4351 | OH2 | H2O | B | 617 | 30.606 | -7.665 | 60.351 | 1.00 54.23 | B | O |
| ATOM | 4352 | OH2 | H2O | B | 618 | 36.659 | -2.414 | 43.944 | 1.00 21.86 | B | O |
| ATOM | 4353 | OH2 | H2O | B | 619 | 27.299 | 17.067 | 55.908 | 1.00 74.08 | B | O |

Figure 9

| | | | | | | | | | | | |
|---|---|---|---|---|---|---|---|---|---|---|---|
| ATOM | 4354 | OH2 | H2O | B | 620 | 29.422 | -4.591 | 62.867 | 1.00 24.54 | B | O |
| ATOM | 4355 | OH2 | H2O | B | 621 | 58.174 | 8.842 | 39.814 | 1.00 41.57 | B | O |
| ATOM | 4356 | OH2 | H2O | B | 622 | 32.115 | 21.817 | 62.038 | 1.00 50.67 | B | O |
| ATOM | 4357 | OH2 | H2O | B | 623 | 24.589 | -1.176 | 58.370 | 1.00 41.14 | B | O |
| ATOM | 4358 | OH2 | H2O | B | 624 | 64.358 | 11.112 | 38.444 | 1.00 38.73 | B | O |
| ATOM | 4359 | OH2 | H2O | B | 625 | 48.341 | 17.274 | 58.831 | 1.00 40.50 | B | O |
| ATOM | 4360 | OH2 | H2O | B | 626 | 43.754 | 2.496 | 45.939 | 1.00 22.97 | B | O |
| ATOM | 4361 | OH2 | H2O | B | 627 | 31.893 | 16.206 | 56.496 | 1.00 16.95 | B | O |
| ATOM | 4362 | OH2 | H2O | B | 628 | 32.302 | 6.870 | 48.385 | 1.00 22.71 | B | O |
| ATOM | 4363 | OH2 | H2O | B | 630 | 36.975 | 7.170 | 67.565 | 1.00 72.13 | B | O |
| ATOM | 4364 | OH2 | H2O | B | 631 | 62.384 | 23.303 | 27.218 | 1.00 50.17 | B | O |
| ATOM | 4365 | OH2 | H2O | B | 632 | 33.516 | -5.658 | 61.683 | 1.00 18.83 | B | O |
| ATOM | 4366 | OH2 | H2O | B | 633 | 45.811 | 9.347 | 36.970 | 1.00 49.68 | B | O |
| ATOM | 4367 | OH2 | H2O | B | 634 | 45.303 | 23.104 | 55.570 | 1.00 26.46 | B | O |
| ATOM | 4368 | OH2 | H2O | B | 635 | 26.771 | 10.530 | 50.313 | 1.00 27.44 | B | O |
| ATOM | 4369 | OH2 | H2O | B | 636 | 26.134 | 10.125 | 65.039 | 1.00 22.82 | B | O |
| ATOM | 4370 | OH2 | H2O | B | 638 | 20.062 | 13.974 | 65.554 | 1.00 33.85 | B | O |
| ATOM | 4371 | OH2 | H2O | B | 639 | 43.879 | 11.954 | 68.591 | 1.00 41.80 | B | O |
| ATOM | 4372 | OH2 | H2O | B | 640 | 26.432 | -1.253 | 54.634 | 1.00 23.41 | B | O |
| ATOM | 4373 | OH2 | H2O | B | 641 | 25.569 | 15.856 | 57.742 | 1.00 20.76 | B | O |
| ATOM | 4374 | OH2 | H2O | B | 642 | 47.670 | 22.911 | 44.864 | 1.00 27.66 | B | O |
| ATOM | 4375 | OH2 | H2O | B | 643 | 55.138 | 0.103 | 27.222 | 1.00 78.33 | B | O |
| ATOM | 4376 | OH2 | H2O | B | 644 | 31.105 | 1.048 | 60.925 | 1.00 15.84 | B | O |
| ATOM | 4377 | OH2 | H2O | B | 645 | 24.019 | -1.612 | 50.388 | 1.00 26.48 | B | O |
| ATOM | 4378 | OH2 | H2O | B | 646 | 56.879 | 21.942 | 18.687 | 1.00 68.91 | B | O |
| ATOM | 4379 | OH2 | H2O | B | 647 | 32.535 | -13.346 | 53.131 | 1.00 48.08 | B | O |
| ATOM | 4380 | OH2 | H2O | B | 648 | 29.203 | 17.256 | 49.709 | 1.00 24.34 | B | O |
| ATOM | 4381 | OH2 | H2O | B | 649 | 14.712 | 16.398 | 62.566 | 1.00 72.20 | B | O |
| ATOM | 4382 | OH2 | H2O | B | 650 | 40.274 | -6.151 | 57.611 | 1.00 31.75 | B | O |
| ATOM | 4383 | OH2 | H2O | B | 651 | 30.788 | 24.731 | 59.077 | 1.00 22.45 | B | O |
| ATOM | 4384 | OH2 | H2O | B | 652 | 26.800 | 1.695 | 61.166 | 1.00 34.66 | B | O |
| ATOM | 4385 | OH2 | H2O | B | 653 | 32.135 | -0.310 | 49.118 | 1.00 18.57 | B | O |
| ATOM | 4386 | OH2 | H2O | B | 654 | 31.765 | -8.430 | 64.250 | 1.00 23.62 | B | O |
| ATOM | 4387 | OH2 | H2O | B | 655 | 52.411 | 2.125 | 33.190 | 1.00 48.74 | B | O |
| ATOM | 4388 | OH2 | H2O | B | 656 | 33.117 | 18.430 | 43.732 | 1.00 24.89 | B | O |
| ATOM | 4389 | OH2 | H2O | B | 657 | 29.549 | 19.077 | 53.695 | 1.00 85.14 | B | O |
| ATOM | 4390 | OH2 | H2O | B | 658 | 26.313 | -2.374 | 65.757 | 1.00 43.47 | B | O |
| ATOM | 4391 | OH2 | H2O | B | 659 | 37.831 | -6.058 | 64.639 | 1.00 17.83 | B | O |
| ATOM | 4392 | OH2 | H2O | B | 660 | 52.153 | 1.479 | 38.625 | 0.00 25.86 | B | O |
| ATOM | 4393 | OH2 | H2O | B | 661 | 43.147 | 7.473 | 36.234 | 1.00 39.95 | B | O |
| ATOM | 4394 | OH2 | H2O | B | 662 | 21.921 | 11.360 | 63.087 | 1.00 63.27 | B | O |
| ATOM | 4395 | OH2 | H2O | B | 663 | 34.859 | -12.283 | 56.759 | 1.00 29.30 | B | O |
| ATOM | 4396 | OH2 | H2O | B | 664 | 58.870 | 14.766 | 44.712 | 1.00 76.87 | B | O |
| ATOM | 4397 | OH2 | H2O | B | 665 | 30.811 | 19.649 | 56.800 | 1.00 66.81 | B | O |
| ATOM | 4398 | OH2 | H2O | B | 666 | 25.754 | -2.104 | 62.128 | 1.00 32.49 | B | O |
| ATOM | 4399 | OH2 | H2O | B | 667 | 36.859 | 21.497 | 56.671 | 1.00 26.59 | B | O |
| ATOM | 4400 | OH2 | H2O | B | 668 | 50.829 | -1.053 | 60.537 | 1.00 36.36 | B | O |
| ATOM | 4401 | OH2 | H2O | B | 669 | 33.389 | 21.289 | 57.823 | 1.00 28.13 | B | O |
| ATOM | 4402 | OH2 | H2O | B | 670 | 22.749 | -2.113 | 62.040 | 1.00 77.32 | B | O |
| ATOM | 4403 | OH2 | H2O | B | 671 | 26.085 | 14.078 | 53.112 | 1.00 30.39 | B | O |
| ATOM | 4404 | OH2 | H2O | B | 672 | 34.663 | 19.408 | 41.154 | 1.00 37.24 | B | O |
| ATOM | 4405 | OH2 | H2O | B | 673 | 62.114 | 1.101 | 48.396 | 1.00 41.74 | B | O |
| ATOM | 4406 | OH2 | H2O | B | 674 | 42.581 | 21.747 | 55.740 | 1.00 31.06 | B | O |
| ATOM | 4407 | OH2 | H2O | B | 675 | 25.729 | -2.748 | 48.704 | 1.00 27.39 | B | O |
| ATOM | 4408 | OH2 | H2O | B | 676 | 59.954 | 18.270 | 42.002 | 1.00 48.11 | B | O |
| ATOM | 4409 | OH2 | H2O | B | 677 | 34.007 | 6.983 | 45.953 | 1.00 35.18 | B | O |
| ATOM | 4410 | OH2 | H2O | B | 678 | 22.943 | 3.492 | 53.056 | 1.00 37.60 | B | O |
| ATOM | 4411 | OH2 | H2O | B | 679 | 43.375 | 1.106 | 43.730 | 1.00 43.89 | B | O |
| ATOM | 4412 | OH2 | H2O | B | 680 | 60.457 | 6.895 | 28.130 | 1.00 28.24 | B | O |

Figure 9

```
ATOM   4413  OH2 H2O B 681      22.006   3.100  50.450  1.00 40.86      B    O
ATOM   4414  OH2 H2O B 682      57.327  19.677  40.742  1.00 28.56      B    O
ATOM   4415  OH2 H2O B 683      45.840   6.168  35.878  1.00 52.78      B    O
ATOM   4416  OH2 H2O B 684      42.825  -2.935  52.929  1.00 31.87      B    O
ATOM   4417  OH2 H2O B 685      23.675  -0.955  53.219  1.00 30.17      B    O
ATOM   4418  OH2 H2O B 686      45.178  -1.896  69.627  1.00 49.40      B    O
ATOM   4419  OH2 H2O B 687      26.553  -4.717  64.068  1.00 29.75      B    O
ATOM   4420  OH2 H2O B 688      62.143   9.677  48.952  1.00 40.77      B    O
ATOM   4421  OH2 H2O B 689      23.636  -2.940  46.750  1.00 37.31      B    O
ATOM   4422  OH2 H2O B 690      32.495  17.435  27.289  1.00 38.88      B    O
ATOM   4423  OH2 H2O B 691      46.978  24.479  40.913  1.00 26.80      B    O
ATOM   4424  OH2 H2O B 692      40.638   0.204  41.952  1.00 35.73      B    O
ATOM   4425  OH2 H2O B 693      44.626  -1.336  47.988  1.00 32.02      B    O
ATOM   4426  OH2 H2O B 694      46.013  22.158  42.975  1.00 31.19      B    O
ATOM   4427  OH2 H2O B 695      18.817  11.728  66.594  1.00 26.71      B    O
ATOM   4428  OH2 H2O B 696      58.830   5.597  59.147  1.00 35.28      B    O
ATOM   4429  OH2 H2O B 697      39.343   5.968  68.631  1.00 68.09      B    O
ATOM   4430  OH2 H2O B 698      53.467  10.885  25.336  1.00 62.56      B    O
ATOM   4431  OH2 H2O B 699      23.112   0.344  60.268  1.00 25.89      B    O
ATOM   4432  OH2 H2O B 700      34.251  10.721  67.452  1.00 71.81      B    O
ATOM   4433  OH2 H2O B 701      62.289  10.203  36.826  1.00 34.22      B    O
ATOM   4434  OH2 H2O B 702      43.711  13.732  33.285  1.00 30.00      B    O
END
```

Figure 9

| | | | | | | | | | |
|---|---|---|---|---|---|---|---|---|---|
| CRYST1 | | 57.376 | 44.680 | 119.821 | 90.00 | 90.02 | 90.00 | P21 | 1 |
| SCALE1 | | 0.017429 | 0.000000 | 0.000006 | | 0.00000 | | | |
| SCALE2 | | 0.000000 | 0.022381 | 0.000000 | | 0.00000 | | | |
| SCALE3 | | 0.000000 | 0.000000 | 0.008346 | | 0.00000 | | | |
| ATOM | 1 | CB | TRP | A | 238 | 18.301 | -5.819 | 27.976 | 1.00 60.42 |
| ATOM | 2 | CG | TRP | A | 238 | 17.828 | -6.469 | 26.657 | 1.00 63.55 |
| ATOM | 3 | CD2 | TRP | A | 238 | 18.306 | -6.194 | 25.320 | 1.00 64.99 |
| ATOM | 4 | CE2 | TRP | A | 238 | 17.559 | -7.014 | 24.428 | 1.00 65.08 |
| ATOM | 5 | CE3 | TRP | A | 238 | 19.286 | -5.339 | 24.789 | 1.00 65.24 |
| ATOM | 6 | CD1 | TRP | A | 238 | 16.841 | -7.419 | 26.513 | 1.00 63.98 |
| ATOM | 7 | NE1 | TRP | A | 238 | 16.679 | -7.745 | 25.182 | 1.00 64.74 |
| ATOM | 8 | CZ2 | TRP | A | 238 | 17.764 | -7.003 | 23.036 | 1.00 64.42 |
| ATOM | 9 | CZ3 | TRP | A | 238 | 19.489 | -5.333 | 23.392 | 1.00 64.91 |
| ATOM | 10 | CH2 | TRP | A | 238 | 18.727 | -6.160 | 22.540 | 1.00 64.51 |
| ATOM | 11 | C | TRP | A | 238 | 19.978 | -5.720 | 29.886 | 1.00 57.41 |
| ATOM | 12 | O | TRP | A | 238 | 20.607 | -4.676 | 29.722 | 1.00 57.02 |
| ATOM | 13 | N | TRP | A | 238 | 19.153 | -7.943 | 28.992 | 1.00 58.41 |
| ATOM | 14 | CA | TRP | A | 238 | 19.494 | -6.525 | 28.662 | 1.00 58.48 |
| ATOM | 15 | N | GLU | A | 239 | 19.674 | -6.186 | 31.103 | 1.00 56.50 |
| ATOM | 16 | CA | GLU | A | 239 | 20.124 | -5.499 | 32.328 | 1.00 54.93 |
| ATOM | 17 | CB | GLU | A | 239 | 19.351 | -5.941 | 33.575 | 1.00 57.18 |
| ATOM | 18 | CG | GLU | A | 239 | 18.349 | -4.942 | 34.102 | 1.00 62.17 |
| ATOM | 19 | CD | GLU | A | 239 | 16.986 | -5.083 | 33.423 | 1.00 66.81 |
| ATOM | 20 | OE1 | GLU | A | 239 | 16.870 | -4.727 | 32.223 | 1.00 68.35 |
| ATOM | 21 | OE2 | GLU | A | 239 | 16.031 | -5.560 | 34.087 | 1.00 68.72 |
| ATOM | 22 | C | GLU | A | 239 | 21.583 | -5.822 | 32.579 | 1.00 52.55 |
| ATOM | 23 | O | GLU | A | 239 | 22.005 | -6.978 | 32.464 | 1.00 52.29 |
| ATOM | 24 | N | VAL | A | 240 | 22.354 | -4.800 | 32.923 | 1.00 49.30 |
| ATOM | 25 | CA | VAL | A | 240 | 23.766 | -4.992 | 33.215 | 1.00 46.50 |
| ATOM | 26 | CB | VAL | A | 240 | 24.708 | -4.439 | 32.103 | 1.00 45.19 |
| ATOM | 27 | CG1 | VAL | A | 240 | 24.553 | -5.231 | 30.821 | 1.00 44.21 |
| ATOM | 28 | CG2 | VAL | A | 240 | 24.451 | -2.959 | 31.873 | 1.00 44.61 |
| ATOM | 29 | C | VAL | A | 240 | 24.109 | -4.293 | 34.511 | 1.00 44.94 |
| ATOM | 30 | O | VAL | A | 240 | 23.407 | -3.378 | 34.949 | 1.00 44.46 |
| ATOM | 31 | N | PRO | A | 241 | 25.130 | -4.797 | 35.202 | 1.00 43.75 |
| ATOM | 32 | CD | PRO | A | 241 | 25.807 | -6.095 | 35.035 | 1.00 43.22 |
| ATOM | 33 | CA | PRO | A | 241 | 25.522 | -4.161 | 36.449 | 1.00 42.97 |
| ATOM | 34 | CB | PRO | A | 241 | 26.520 | -5.162 | 37.025 | 1.00 43.08 |
| ATOM | 35 | CG | PRO | A | 241 | 26.064 | -6.485 | 36.444 | 1.00 42.67 |
| ATOM | 36 | C | PRO | A | 241 | 26.197 | -2.833 | 36.092 | 1.00 43.29 |
| ATOM | 37 | O | PRO | A | 241 | 26.948 | -2.736 | 35.116 | 1.00 42.74 |
| ATOM | 38 | N | ARG | A | 242 | 25.898 | -1.803 | 36.863 | 1.00 43.73 |
| ATOM | 39 | CA | ARG | A | 242 | 26.477 | -0.485 | 36.649 | 1.00 44.86 |
| ATOM | 40 | CB | ARG | A | 242 | 26.025 | 0.423 | 37.781 | 1.00 45.33 |
| ATOM | 41 | CG | ARG | A | 242 | 26.741 | 1.741 | 37.866 | 1.00 47.01 |
| ATOM | 42 | CD | ARG | A | 242 | 26.118 | 2.721 | 36.934 | 1.00 47.54 |
| ATOM | 43 | NE | ARG | A | 242 | 24.664 | 2.797 | 37.104 | 1.00 49.94 |
| ATOM | 44 | CZ | ARG | A | 242 | 24.038 | 3.180 | 38.218 | 1.00 48.19 |
| ATOM | 45 | NH1 | ARG | A | 242 | 24.732 | 3.518 | 39.299 | 1.00 48.30 |
| ATOM | 46 | NH2 | ARG | A | 242 | 22.713 | 3.271 | 38.232 | 1.00 45.40 |

Figure 10

| | | | | | | | | |
|---|---|---|---|---|---|---|---|---|
| ATOM | 47 | C | ARG | A 242 | 28.018 | -0.481 | 36.563 | 1.00 45.72 |
| ATOM | 48 | O | ARG | A 242 | 28.596 | 0.397 | 35.920 | 1.00 45.33 |
| ATOM | 49 | N | GLU | A 243 | 28.666 | -1.451 | 37.219 | 1.00 46.38 |
| ATOM | 50 | CA | GLU | A 243 | 30.134 | -1.585 | 37.248 | 1.00 45.85 |
| ATOM | 51 | CB | GLU | A 243 | 30.568 | -2.857 | 37.999 | 1.00 49.57 |
| ATOM | 52 | CG | GLU | A 243 | 30.381 | -2.839 | 39.509 | 1.00 53.39 |
| ATOM | 53 | CD | GLU | A 243 | 28.908 | -2.858 | 39.937 | 1.00 55.78 |
| ATOM | 54 | OE1 | GLU | A 243 | 28.413 | -3.939 | 40.344 | 1.00 55.41 |
| ATOM | 55 | OE2 | GLU | A 243 | 28.252 | -1.787 | 39.876 | 1.00 56.38 |
| ATOM | 56 | C | GLU | A 243 | 30.726 | -1.664 | 35.857 | 1.00 43.54 |
| ATOM | 57 | O | GLU | A 243 | 31.787 | -1.112 | 35.607 | 1.00 42.99 |
| ATOM | 58 | N | THR | A 244 | 30.053 | -2.391 | 34.969 | 1.00 41.78 |
| ATOM | 59 | CA | THR | A 244 | 30.510 | -2.574 | 33.587 | 1.00 39.93 |
| ATOM | 60 | CB | THR | A 244 | 29.652 | -3.651 | 32.851 | 1.00 38.81 |
| ATOM | 61 | OG1 | THR | A 244 | 28.313 | -3.168 | 32.655 | 1.00 36.99 |
| ATOM | 62 | CG2 | THR | A 244 | 29.611 | -4.931 | 33.654 | 1.00 36.96 |
| ATOM | 63 | C | THR | A 244 | 30.483 | -1.293 | 32.744 | 1.00 38.20 |
| ATOM | 64 | O | THR | A 244 | 30.890 | -1.301 | 31.583 | 1.00 37.83 |
| ATOM | 65 | N | LEU | A 245 | 30.122 | -0.183 | 33.371 | 1.00 36.97 |
| ATOM | 66 | CA | LEU | A 245 | 29.969 | 1.075 | 32.667 | 1.00 36.26 |
| ATOM | 67 | CB | LEU | A 245 | 28.476 | 1.345 | 32.597 | 1.00 37.19 |
| ATOM | 68 | CG | LEU | A 245 | 27.775 | 1.721 | 31.307 | 1.00 40.03 |
| ATOM | 69 | CD1 | LEU | A 245 | 28.113 | 0.756 | 30.181 | 1.00 40.49 |
| ATOM | 70 | CD2 | LEU | A 245 | 26.281 | 1.704 | 31.607 | 1.00 40.33 |
| ATOM | 71 | C | LEU | A 245 | 30.676 | 2.292 | 33.278 | 1.00 35.38 |
| ATOM | 72 | O | LEU | A 245 | 30.376 | 2.691 | 34.402 | 1.00 34.97 |
| ATOM | 73 | N | LYS | A 246 | 31.611 | 2.881 | 32.532 | 1.00 34.84 |
| ATOM | 74 | CA | LYS | A 246 | 32.326 | 4.073 | 32.996 | 1.00 33.96 |
| ATOM | 75 | CB | LYS | A 246 | 33.857 | 3.846 | 33.010 | 1.00 35.05 |
| ATOM | 76 | CG | LYS | A 246 | 34.699 | 5.104 | 33.356 | 1.00 35.90 |
| ATOM | 77 | CD | LYS | A 246 | 36.230 | 4.854 | 33.418 | 1.00 39.04 |
| ATOM | 78 | CE | LYS | A 246 | 36.824 | 4.278 | 32.112 | 1.00 41.18 |
| ATOM | 79 | NZ | LYS | A 246 | 38.263 | 3.794 | 32.230 | 1.00 42.52 |
| ATOM | 80 | C | LYS | A 246 | 31.954 | 5.292 | 32.131 | 1.00 32.29 |
| ATOM | 81 | O | LYS | A 246 | 32.218 | 5.329 | 30.926 | 1.00 32.03 |
| ATOM | 82 | N | LEU | A 247 | 31.277 | 6.253 | 32.751 | 1.00 30.28 |
| ATOM | 83 | CA | LEU | A 247 | 30.877 | 7.485 | 32.080 | 1.00 28.78 |
| ATOM | 84 | CB | LEU | A 247 | 29.653 | 8.100 | 32.757 | 1.00 27.13 |
| ATOM | 85 | CG | LEU | A 247 | 28.306 | 7.467 | 32.412 | 1.00 26.36 |
| ATOM | 86 | CD1 | LEU | A 247 | 28.291 | 5.967 | 32.684 | 1.00 25.84 |
| ATOM | 87 | CD2 | LEU | A 247 | 27.227 | 8.169 | 33.211 | 1.00 25.30 |
| ATOM | 88 | C | LEU | A 247 | 32.044 | 8.468 | 32.089 | 1.00 28.95 |
| ATOM | 89 | O | LEU | A 247 | 32.512 | 8.917 | 33.141 | 1.00 29.14 |
| ATOM | 90 | N | VAL | A 248 | 32.497 | 8.813 | 30.895 | 1.00 29.27 |
| ATOM | 91 | CA | VAL | A 248 | 33.638 | 9.697 | 30.728 | 1.00 29.03 |
| ATOM | 92 | CB | VAL | A 248 | 34.577 | 9.132 | 29.632 | 1.00 27.45 |
| ATOM | 93 | CG1 | VAL | A 248 | 35.899 | 9.849 | 29.635 | 1.00 27.25 |
| ATOM | 94 | CG2 | VAL | A 248 | 34.774 | 7.645 | 29.841 | 1.00 26.05 |
| ATOM | 95 | C | VAL | A 248 | 33.325 | 11.157 | 30.411 | 1.00 29.80 |
| ATOM | 96 | O | VAL | A 248 | 33.743 | 12.069 | 31.131 | 1.00 30.03 |
| ATOM | 97 | N | GLU | A 249 | 32.564 | 11.372 | 29.346 | 1.00 30.61 |
| ATOM | 98 | CA | GLU | A 249 | 32.258 | 12.721 | 28.894 | 1.00 31.34 |
| ATOM | 99 | CB | GLU | A 249 | 32.884 | 12.893 | 27.519 | 1.00 33.29 |
| ATOM | 100 | CG | GLU | A 249 | 32.856 | 14.295 | 26.993 | 1.00 36.85 |
| ATOM | 101 | CD | GLU | A 249 | 33.617 | 14.415 | 25.697 | 1.00 39.34 |
| ATOM | 102 | OE1 | GLU | A 249 | 34.490 | 13.555 | 25.449 | 1.00 40.34 |
| ATOM | 103 | OE2 | GLU | A 249 | 33.345 | 15.366 | 24.928 | 1.00 42.40 |
| ATOM | 104 | C | GLU | A 249 | 30.775 | 13.029 | 28.791 | 1.00 31.02 |
| ATOM | 105 | O | GLU | A 249 | 30.008 | 12.208 | 28.302 | 1.00 31.78 |

Figure 10

| ATOM | 106 | N   | ARG A 250 | 30.364 | 14.207 | 29.243 | 1.00 | 30.31 |
|------|-----|-----|-----------|--------|--------|--------|------|-------|
| ATOM | 107 | CA  | ARG A 250 | 28.958 | 14.561 | 29.140 | 1.00 | 30.38 |
| ATOM | 108 | CB  | ARG A 250 | 28.484 | 15.414 | 30.300 | 1.00 | 30.15 |
| ATOM | 109 | CG  | ARG A 250 | 26.974 | 15.302 | 30.444 | 1.00 | 34.20 |
| ATOM | 110 | CD  | ARG A 250 | 26.471 | 16.106 | 31.589 | 1.00 | 36.55 |
| ATOM | 111 | NE  | ARG A 250 | 26.743 | 17.517 | 31.360 | 1.00 | 41.33 |
| ATOM | 112 | CZ  | ARG A 250 | 26.635 | 18.468 | 32.285 | 1.00 | 42.89 |
| ATOM | 113 | NH1 | ARG A 250 | 26.266 | 18.168 | 33.522 | 1.00 | 42.39 |
| ATOM | 114 | NH2 | ARG A 250 | 26.876 | 19.728 | 31.956 | 1.00 | 44.19 |
| ATOM | 115 | C   | ARG A 250 | 28.730 | 15.284 | 27.827 | 1.00 | 30.40 |
| ATOM | 116 | O   | ARG A 250 | 29.299 | 16.355 | 27.591 | 1.00 | 31.81 |
| ATOM | 117 | N   | LEU A 251 | 27.909 | 14.679 | 26.973 | 1.00 | 28.28 |
| ATOM | 118 | CA  | LEU A 251 | 27.625 | 15.218 | 25.659 | 1.00 | 26.88 |
| ATOM | 119 | CB  | LEU A 251 | 27.309 | 14.076 | 24.696 | 1.00 | 25.23 |
| ATOM | 120 | CG  | LEU A 251 | 28.351 | 12.946 | 24.719 | 1.00 | 23.40 |
| ATOM | 121 | CD1 | LEU A 251 | 27.875 | 11.779 | 23.881 | 1.00 | 24.02 |
| ATOM | 122 | CD2 | LEU A 251 | 29.708 | 13.427 | 24.247 | 1.00 | 22.81 |
| ATOM | 123 | C   | LEU A 251 | 26.510 | 16.241 | 25.697 | 1.00 | 26.32 |
| ATOM | 124 | O   | LEU A 251 | 26.436 | 17.128 | 24.851 | 1.00 | 27.17 |
| ATOM | 125 | N   | GLY A 252 | 25.663 | 16.132 | 26.706 | 1.00 | 26.25 |
| ATOM | 126 | CA  | GLY A 252 | 24.569 | 17.068 | 26.859 | 1.00 | 24.89 |
| ATOM | 127 | C   | GLY A 252 | 23.759 | 16.848 | 28.129 | 1.00 | 25.29 |
| ATOM | 128 | O   | GLY A 252 | 23.661 | 15.730 | 28.656 | 1.00 | 24.58 |
| ATOM | 129 | N   | ALA A 253 | 23.131 | 17.924 | 28.589 | 1.00 | 25.71 |
| ATOM | 130 | CA  | ALA A 253 | 22.289 | 17.904 | 29.778 | 1.00 | 26.10 |
| ATOM | 131 | CB  | ALA A 253 | 23.064 | 18.416 | 30.978 | 1.00 | 27.01 |
| ATOM | 132 | C   | ALA A 253 | 21.030 | 18.758 | 29.553 | 1.00 | 26.19 |
| ATOM | 133 | O   | ALA A 253 | 21.114 | 19.921 | 29.115 | 1.00 | 25.00 |
| ATOM | 134 | N   | GLY A 254 | 19.871 | 18.175 | 29.864 | 1.00 | 26.90 |
| ATOM | 135 | CA  | GLY A 254 | 18.609 | 18.875 | 29.689 | 1.00 | 27.31 |
| ATOM | 136 | C   | GLY A 254 | 17.659 | 18.722 | 30.855 | 1.00 | 28.83 |
| ATOM | 137 | O   | GLY A 254 | 18.032 | 18.248 | 31.920 | 1.00 | 29.42 |
| ATOM | 138 | N   | GLN A 255 | 16.409 | 19.088 | 30.626 | 1.00 | 30.68 |
| ATOM | 139 | CA  | GLN A 255 | 15.374 | 19.038 | 31.647 | 1.00 | 32.43 |
| ATOM | 140 | CB  | GLN A 255 | 14.075 | 19.644 | 31.097 | 1.00 | 36.11 |
| ATOM | 141 | CG  | GLN A 255 | 13.093 | 20.108 | 32.182 | 1.00 | 41.65 |
| ATOM | 142 | CD  | GLN A 255 | 11.636 | 20.205 | 31.710 | 1.00 | 45.59 |
| ATOM | 143 | OE1 | GLN A 255 | 10.723 | 20.351 | 32.535 | 1.00 | 45.95 |
| ATOM | 144 | NE2 | GLN A 255 | 11.409 | 20.113 | 30.389 | 1.00 | 46.66 |
| ATOM | 145 | C   | GLN A 255 | 15.075 | 17.657 | 32.219 | 1.00 | 32.42 |
| ATOM | 146 | O   | GLN A 255 | 14.767 | 17.527 | 33.407 | 1.00 | 33.65 |
| ATOM | 147 | N   | PHE A 256 | 15.139 | 16.628 | 31.379 | 1.00 | 31.44 |
| ATOM | 148 | CA  | PHE A 256 | 14.841 | 15.272 | 31.824 | 1.00 | 30.26 |
| ATOM | 149 | CB  | PHE A 256 | 14.005 | 14.544 | 30.771 | 1.00 | 30.80 |
| ATOM | 150 | CG  | PHE A 256 | 12.594 | 15.058 | 30.648 | 1.00 | 31.19 |
| ATOM | 151 | CD1 | PHE A 256 | 12.157 | 16.138 | 31.416 | 1.00 | 31.93 |
| ATOM | 152 | CD2 | PHE A 256 | 11.702 | 14.468 | 29.758 | 1.00 | 30.27 |
| ATOM | 153 | CE1 | PHE A 256 | 10.857 | 16.630 | 31.291 | 1.00 | 31.07 |
| ATOM | 154 | CE2 | PHE A 256 | 10.404 | 14.955 | 29.629 | 1.00 | 29.92 |
| ATOM | 155 | CZ  | PHE A 256 |  9.982 | 16.038 | 30.400 | 1.00 | 29.68 |
| ATOM | 156 | C   | PHE A 256 | 16.015 | 14.386 | 32.218 | 1.00 | 30.35 |
| ATOM | 157 | O   | PHE A 256 | 15.799 | 13.252 | 32.680 | 1.00 | 30.28 |
| ATOM | 158 | N   | GLY A 257 | 17.244 | 14.873 | 32.012 | 1.00 | 29.40 |
| ATOM | 159 | CA  | GLY A 257 | 18.415 | 14.077 | 32.343 | 1.00 | 27.92 |
| ATOM | 160 | C   | GLY A 257 | 19.637 | 14.445 | 31.527 | 1.00 | 27.70 |
| ATOM | 161 | O   | GLY A 257 | 19.778 | 15.590 | 31.095 | 1.00 | 26.79 |
| ATOM | 162 | N   | GLU A 258 | 20.494 | 13.460 | 31.257 | 1.00 | 27.89 |
| ATOM | 163 | CA  | GLU A 258 | 21.739 | 13.709 | 30.536 | 1.00 | 28.60 |
| ATOM | 164 | CB  | GLU A 258 | 22.869 | 13.903 | 31.549 | 1.00 | 30.05 |

Figure 10

```
ATOM    165  CG   GLU A 258      22.501  14.758  32.757  1.00 33.66
ATOM    166  CD   GLU A 258      23.704  15.137  33.613  1.00 37.53
ATOM    167  OE1  GLU A 258      24.510  14.251  33.973  1.00 40.01
ATOM    168  OE2  GLU A 258      23.845  16.332  33.940  1.00 39.46
ATOM    169  C    GLU A 258      22.165  12.618  29.563  1.00 27.55
ATOM    170  O    GLU A 258      21.635  11.514  29.570  1.00 28.12
ATOM    171  N    VAL A 259      23.129  12.950  28.713  1.00 27.20
ATOM    172  CA   VAL A 259      23.663  11.995  27.734  1.00 26.84
ATOM    173  CB   VAL A 259      23.269  12.311  26.252  1.00 25.41
ATOM    174  CG1  VAL A 259      23.697  11.149  25.352  1.00 22.06
ATOM    175  CG2  VAL A 259      21.771  12.578  26.115  1.00 23.18
ATOM    176  C    VAL A 259      25.177  12.089  27.863  1.00 27.07
ATOM    177  O    VAL A 259      25.736  13.193  27.856  1.00 26.91
ATOM    178  N    TRP A 260      25.822  10.931  27.983  1.00 27.36
ATOM    179  CA   TRP A 260      27.267  10.841  28.158  1.00 27.64
ATOM    180  CB   TRP A 260      27.606  10.300  29.560  1.00 26.43
ATOM    181  CG   TRP A 260      27.404  11.227  30.715  1.00 27.38
ATOM    182  CD2  TRP A 260      28.430  11.781  31.563  1.00 28.57
ATOM    183  CE2  TRP A 260      27.788  12.603  32.513  1.00 28.33
ATOM    184  CE3  TRP A 260      29.831  11.668  31.605  1.00 29.30
ATOM    185  CD1  TRP A 260      26.216  11.717  31.183  1.00 26.81
ATOM    186  NE1  TRP A 260      26.440  12.544  32.259  1.00 27.57
ATOM    187  CZ2  TRP A 260      28.502  13.316  33.496  1.00 27.48
ATOM    188  CZ3  TRP A 260      30.539  12.379  32.581  1.00 27.48
ATOM    189  CH2  TRP A 260      29.871  13.191  33.508  1.00 25.02
ATOM    190  C    TRP A 260      27.905   9.868  27.181  1.00 28.75
ATOM    191  O    TRP A 260      27.244   8.975  26.633  1.00 28.10
ATOM    192  N    MET A 261      29.205  10.056  26.971  1.00 28.82
ATOM    193  CA   MET A 261      29.990   9.150  26.153  1.00 28.63
ATOM    194  CB   MET A 261      31.081   9.884  25.372  1.00 27.16
ATOM    195  CG   MET A 261      31.998   8.948  24.583  1.00 27.50
ATOM    196  SD   MET A 261      33.322   8.094  25.522  1.00 25.76
ATOM    197  CE   MET A 261      34.366   9.493  25.884  1.00 24.37
ATOM    198  C    MET A 261      30.623   8.303  27.243  1.00 29.46
ATOM    199  O    MET A 261      30.911   8.808  28.327  1.00 30.24
ATOM    200  N    GLY A 262      30.820   7.023  26.974  1.00 30.29
ATOM    201  CA   GLY A 262      31.424   6.174  27.974  1.00 30.02
ATOM    202  C    GLY A 262      31.933   4.879  27.397  1.00 30.98
ATOM    203  O    GLY A 262      31.920   4.657  26.184  1.00 29.81
ATOM    204  N    TYR A 263      32.408   4.024  28.290  1.00 32.48
ATOM    205  CA   TYR A 263      32.938   2.741  27.894  1.00 34.65
ATOM    206  CB   TYR A 263      34.456   2.708  28.145  1.00 31.72
ATOM    207  CG   TYR A 263      35.215   3.674  27.241  1.00 30.94
ATOM    208  CD1  TYR A 263      35.686   3.268  25.985  1.00 30.04
ATOM    209  CE1  TYR A 263      36.319   4.171  25.122  1.00 28.73
ATOM    210  CD2  TYR A 263      35.401   5.016  27.609  1.00 29.78
ATOM    211  CE2  TYR A 263      36.028   5.929  26.744  1.00 29.02
ATOM    212  CZ   TYR A 263      36.483   5.495  25.503  1.00 29.00
ATOM    213  OH   TYR A 263      37.095   6.389  24.646  1.00 29.42
ATOM    214  C    TYR A 263      32.195   1.613  28.596  1.00 37.36
ATOM    215  O    TYR A 263      31.839   1.717  29.771  1.00 37.93
ATOM    216  N    TYR A 264      31.911   0.568  27.831  1.00 41.00
ATOM    217  CA   TYR A 264      31.196  -0.619  28.291  1.00 45.10
ATOM    218  CB   TYR A 264      30.040  -0.886  27.312  1.00 47.99
ATOM    219  CG   TYR A 264      29.130  -2.089  27.533  1.00 51.28
ATOM    220  CD1  TYR A 264      28.887  -2.614  28.811  1.00 52.09
ATOM    221  CE1  TYR A 264      27.967  -3.658  28.990  1.00 53.85
ATOM    222  CD2  TYR A 264      28.433  -2.647  26.438  1.00 52.28
ATOM    223  CE2  TYR A 264      27.518  -3.678  26.601  1.00 53.00
```

Figure 10

| ATOM | 224 | CZ | TYR A 264 | 27.283 | -4.181 | 27.873 | 1.00 | 55.13 |
| ATOM | 225 | OH | TYR A 264 | 26.344 | -5.183 | 28.017 | 1.00 | 57.15 |
| ATOM | 226 | C | TYR A 264 | 32.205 | -1.750 | 28.254 | 1.00 | 46.45 |
| ATOM | 227 | O | TYR A 264 | 32.826 | -2.005 | 27.218 | 1.00 | 47.08 |
| ATOM | 228 | N | ASN A 265 | 32.394 | -2.401 | 29.393 | 1.00 | 48.10 |
| ATOM | 229 | CA | ASN A 265 | 33.337 | -3.505 | 29.491 | 1.00 | 50.51 |
| ATOM | 230 | CB | ASN A 265 | 32.940 | -4.629 | 28.520 | 1.00 | 52.25 |
| ATOM | 231 | CG | ASN A 265 | 31.510 | -5.135 | 28.746 | 1.00 | 54.64 |
| ATOM | 232 | OD1 | ASN A 265 | 31.128 | -5.488 | 29.871 | 1.00 | 54.35 |
| ATOM | 233 | ND2 | ASN A 265 | 30.719 | -5.184 | 27.666 | 1.00 | 54.52 |
| ATOM | 234 | C | ASN A 265 | 34.742 | -2.982 | 29.180 | 1.00 | 51.27 |
| ATOM | 235 | O | ASN A 265 | 35.563 | -3.665 | 28.549 | 1.00 | 51.95 |
| ATOM | 236 | N | GLY A 266 | 34.977 | -1.733 | 29.573 | 1.00 | 51.58 |
| ATOM | 237 | CA | GLY A 266 | 36.267 | -1.097 | 29.373 | 1.00 | 52.55 |
| ATOM | 238 | C | GLY A 266 | 36.702 | -0.689 | 27.973 | 1.00 | 53.51 |
| ATOM | 239 | O | GLY A 266 | 37.428 | 0.302 | 27.838 | 1.00 | 54.02 |
| ATOM | 240 | N | HIS A 267 | 36.275 | -1.420 | 26.939 | 1.00 | 53.90 |
| ATOM | 241 | CA | HIS A 267 | 36.691 | -1.099 | 25.569 | 1.00 | 53.72 |
| ATOM | 242 | CB | HIS A 267 | 37.601 | -2.199 | 25.028 | 1.00 | 57.23 |
| ATOM | 243 | CG | HIS A 267 | 38.986 | -2.152 | 25.596 | 1.00 | 61.29 |
| ATOM | 244 | CD2 | HIS A 267 | 39.911 | -1.160 | 25.611 | 1.00 | 62.84 |
| ATOM | 245 | ND1 | HIS A 267 | 39.559 | -3.214 | 26.266 | 1.00 | 63.33 |
| ATOM | 246 | CE1 | HIS A 267 | 40.771 | -2.880 | 26.671 | 1.00 | 62.93 |
| ATOM | 247 | NE2 | HIS A 267 | 41.010 | -1.638 | 26.285 | 1.00 | 64.05 |
| ATOM | 248 | C | HIS A 267 | 35.657 | -0.698 | 24.522 | 1.00 | 51.41 |
| ATOM | 249 | O | HIS A 267 | 36.010 | -0.036 | 23.541 | 1.00 | 51.73 |
| ATOM | 250 | N | THR A 268 | 34.406 | -1.119 | 24.701 | 1.00 | 48.27 |
| ATOM | 251 | CA | THR A 268 | 33.339 | -0.754 | 23.766 | 1.00 | 44.94 |
| ATOM | 252 | CB | THR A 268 | 32.155 | -1.740 | 23.852 | 1.00 | 46.12 |
| ATOM | 253 | OG1 | THR A 268 | 32.645 | -3.083 | 23.755 | 1.00 | 47.78 |
| ATOM | 254 | CG2 | THR A 268 | 31.146 | -1.481 | 22.726 | 1.00 | 45.09 |
| ATOM | 255 | C | THR A 268 | 32.824 | 0.656 | 24.081 | 1.00 | 42.20 |
| ATOM | 256 | O | THR A 268 | 32.270 | 0.905 | 25.148 | 1.00 | 41.07 |
| ATOM | 257 | N | LYS A 269 | 33.014 | 1.581 | 23.149 | 1.00 | 40.13 |
| ATOM | 258 | CA | LYS A 269 | 32.552 | 2.955 | 23.340 | 1.00 | 37.91 |
| ATOM | 259 | CB | LYS A 269 | 33.207 | 3.875 | 22.307 | 1.00 | 36.79 |
| ATOM | 260 | CG | LYS A 269 | 33.380 | 5.309 | 22.761 | 1.00 | 36.20 |
| ATOM | 261 | CD | LYS A 269 | 34.153 | 6.108 | 21.733 | 1.00 | 35.22 |
| ATOM | 262 | CE | LYS A 269 | 34.681 | 7.395 | 22.318 | 1.00 | 36.11 |
| ATOM | 263 | NZ | LYS A 269 | 35.600 | 8.091 | 21.377 | 1.00 | 36.74 |
| ATOM | 264 | C | LYS A 269 | 31.023 | 2.989 | 23.198 | 1.00 | 36.66 |
| ATOM | 265 | O | LYS A 269 | 30.469 | 2.419 | 22.255 | 1.00 | 36.03 |
| ATOM | 266 | N | VAL A 270 | 30.344 | 3.626 | 24.154 | 1.00 | 34.80 |
| ATOM | 267 | CA | VAL A 270 | 28.883 | 3.729 | 24.135 | 1.00 | 32.28 |
| ATOM | 268 | CB | VAL A 270 | 28.244 | 2.714 | 25.132 | 1.00 | 31.24 |
| ATOM | 269 | CG1 | VAL A 270 | 28.600 | 1.304 | 24.757 | 1.00 | 29.22 |
| ATOM | 270 | CG2 | VAL A 270 | 28.696 | 2.995 | 26.541 | 1.00 | 28.45 |
| ATOM | 271 | C | VAL A 270 | 28.354 | 5.134 | 24.480 | 1.00 | 32.49 |
| ATOM | 272 | O | VAL A 270 | 29.123 | 6.036 | 24.831 | 1.00 | 31.87 |
| ATOM | 273 | N | ALA A 271 | 27.042 | 5.324 | 24.306 | 1.00 | 32.11 |
| ATOM | 274 | CA | ALA A 271 | 26.364 | 6.572 | 24.659 | 1.00 | 30.62 |
| ATOM | 275 | CB | ALA A 271 | 25.603 | 7.148 | 23.478 | 1.00 | 30.24 |
| ATOM | 276 | C | ALA A 271 | 25.397 | 6.164 | 25.769 | 1.00 | 30.44 |
| ATOM | 277 | O | ALA A 271 | 24.672 | 5.173 | 25.643 | 1.00 | 31.55 |
| ATOM | 278 | N | VAL A 272 | 25.423 | 6.890 | 26.876 | 1.00 | 29.22 |
| ATOM | 279 | CA | VAL A 272 | 24.559 | 6.563 | 27.999 | 1.00 | 29.60 |
| ATOM | 280 | CB | VAL A 272 | 25.386 | 6.261 | 29.287 | 1.00 | 30.55 |
| ATOM | 281 | CG1 | VAL A 272 | 24.511 | 5.577 | 30.320 | 1.00 | 30.23 |
| ATOM | 282 | CG2 | VAL A 272 | 26.620 | 5.422 | 28.970 | 1.00 | 29.58 |

Figure 10

| | | | | | | | | | |
|---|---|---|---|---|---|---|---|---|---|
| ATOM | 283 | C | VAL | A | 272 | 23.635 | 7.723 | 28.318 | 1.00 28.53 |
| ATOM | 284 | O | VAL | A | 272 | 24.092 | 8.850 | 28.488 | 1.00 28.20 |
| ATOM | 285 | N | LYS | A | 273 | 22.336 | 7.442 | 28.366 | 1.00 27.85 |
| ATOM | 286 | CA | LYS | A | 273 | 21.334 | 8.454 | 28.695 | 1.00 26.79 |
| ATOM | 287 | CB | LYS | A | 273 | 20.200 | 8.459 | 27.669 | 1.00 26.43 |
| ATOM | 288 | CG | LYS | A | 273 | 19.131 | 9.521 | 27.920 | 1.00 25.15 |
| ATOM | 289 | CD | LYS | A | 273 | 18.044 | 9.458 | 26.851 | 1.00 24.46 |
| ATOM | 290 | CE | LYS | A | 273 | 18.427 | 10.199 | 25.573 | 1.00 21.47 |
| ATOM | 291 | NZ | LYS | A | 273 | 17.239 | 10.319 | 24.662 | 1.00 20.86 |
| ATOM | 292 | C | LYS | A | 273 | 20.779 | 8.126 | 30.076 | 1.00 26.66 |
| ATOM | 293 | O | LYS | A | 273 | 20.248 | 7.036 | 30.301 | 1.00 24.17 |
| ATOM | 294 | N | SER | A | 274 | 20.924 | 9.075 | 30.994 | 1.00 27.64 |
| ATOM | 295 | CA | SER | A | 274 | 20.466 | 8.911 | 32.372 | 1.00 29.26 |
| ATOM | 296 | CB | SER | A | 274 | 21.578 | 9.294 | 33.357 | 1.00 30.32 |
| ATOM | 297 | OG | SER | A | 274 | 22.020 | 10.627 | 33.155 | 1.00 30.94 |
| ATOM | 298 | C | SER | A | 274 | 19.224 | 9.724 | 32.682 | 1.00 29.26 |
| ATOM | 299 | O | SER | A | 274 | 19.084 | 10.846 | 32.215 | 1.00 29.61 |
| ATOM | 300 | N | LEU | A | 275 | 18.337 | 9.154 | 33.489 | 1.00 30.42 |
| ATOM | 301 | CA | LEU | A | 275 | 17.092 | 9.815 | 33.881 | 1.00 31.56 |
| ATOM | 302 | CB | LEU | A | 275 | 15.995 | 8.779 | 34.147 | 1.00 30.12 |
| ATOM | 303 | CG | LEU | A | 275 | 14.650 | 9.297 | 34.689 | 1.00 31.40 |
| ATOM | 304 | CD1 | LEU | A | 275 | 13.986 | 10.206 | 33.644 | 1.00 31.81 |
| ATOM | 305 | CD2 | LEU | A | 275 | 13.714 | 8.137 | 35.059 | 1.00 28.87 |
| ATOM | 306 | C | LEU | A | 275 | 17.251 | 10.676 | 35.129 | 1.00 33.44 |
| ATOM | 307 | O | LEU | A | 275 | 17.798 | 10.222 | 36.138 | 1.00 34.45 |
| ATOM | 308 | N | LYS | A | 276 | 16.814 | 11.931 | 35.035 | 1.00 34.36 |
| ATOM | 309 | CA | LYS | A | 276 | 16.847 | 12.840 | 36.166 | 1.00 36.19 |
| ATOM | 310 | CB | LYS | A | 276 | 16.697 | 14.288 | 35.707 | 1.00 37.40 |
| ATOM | 311 | CG | LYS | A | 276 | 16.556 | 15.308 | 36.844 | 1.00 40.20 |
| ATOM | 312 | CD | LYS | A | 276 | 16.542 | 16.740 | 36.303 | 1.00 43.73 |
| ATOM | 313 | CE | LYS | A | 276 | 17.811 | 17.025 | 35.477 | 1.00 47.01 |
| ATOM | 314 | NZ | LYS | A | 276 | 17.888 | 18.407 | 34.909 | 1.00 48.52 |
| ATOM | 315 | C | LYS | A | 276 | 15.607 | 12.426 | 36.919 | 1.00 37.33 |
| ATOM | 316 | O | LYS | A | 276 | 14.499 | 12.544 | 36.386 | 1.00 37.92 |
| ATOM | 317 | N | GLN | A | 277 | 15.801 | 11.863 | 38.109 | 1.00 37.81 |
| ATOM | 318 | CA | GLN | A | 277 | 14.694 | 11.397 | 38.958 | 1.00 37.57 |
| ATOM | 319 | CB | GLN | A | 277 | 15.241 | 10.984 | 40.321 | 1.00 42.06 |
| ATOM | 320 | CG | GLN | A | 277 | 14.208 | 10.474 | 41.309 | 1.00 47.50 |
| ATOM | 321 | CD | GLN | A | 277 | 14.832 | 10.199 | 42.657 | 1.00 52.28 |
| ATOM | 322 | OE1 | GLN | A | 277 | 15.822 | 10.839 | 43.036 | 1.00 56.08 |
| ATOM | 323 | NE2 | GLN | A | 277 | 14.258 | 9.260 | 43.402 | 1.00 53.75 |
| ATOM | 324 | C | GLN | A | 277 | 13.596 | 12.432 | 39.151 | 1.00 35.13 |
| ATOM | 325 | O | GLN | A | 277 | 13.862 | 13.582 | 39.480 | 1.00 33.44 |
| ATOM | 326 | N | GLY | A | 278 | 12.358 | 12.024 | 38.929 | 1.00 34.34 |
| ATOM | 327 | CA | GLY | A | 278 | 11.265 | 12.961 | 39.098 | 1.00 34.02 |
| ATOM | 328 | C | GLY | A | 278 | 10.713 | 13.530 | 37.800 | 1.00 34.55 |
| ATOM | 329 | O | GLY | A | 278 | 9.595 | 14.055 | 37.779 | 1.00 34.69 |
| ATOM | 330 | N | SER | A | 279 | 11.485 | 13.432 | 36.719 | 1.00 34.40 |
| ATOM | 331 | CA | SER | A | 279 | 11.050 | 13.936 | 35.416 | 1.00 34.53 |
| ATOM | 332 | CB | SER | A | 279 | 12.226 | 13.921 | 34.447 | 1.00 33.75 |
| ATOM | 333 | OG | SER | A | 279 | 13.281 | 14.703 | 34.963 | 1.00 34.49 |
| ATOM | 334 | C | SER | A | 279 | 9.903 | 13.067 | 34.879 | 1.00 34.21 |
| ATOM | 335 | O | SER | A | 279 | 8.976 | 13.548 | 34.214 | 1.00 33.91 |
| ATOM | 336 | N | MET | A | 280 | 10.006 | 11.780 | 35.167 | 1.00 33.04 |
| ATOM | 337 | CA | MET | A | 280 | 9.024 | 10.792 | 34.778 | 1.00 33.71 |
| ATOM | 338 | CB | MET | A | 280 | 9.011 | 10.565 | 33.257 | 1.00 34.54 |
| ATOM | 339 | CG | MET | A | 280 | 10.315 | 10.031 | 32.649 | 1.00 35.96 |
| ATOM | 340 | SD | MET | A | 280 | 10.475 | 10.190 | 30.837 | 1.00 35.31 |
| ATOM | 341 | CE | MET | A | 280 | 9.346 | 8.959 | 30.303 | 1.00 34.04 |

Figure 10

| | | | | | | | | |
|---|---|---|---|---|---|---|---|---|
| ATOM | 342 | C | MET | A | 280 | 9.449 | 9.533 | 35.547 | 1.00 | 34.35 |
| ATOM | 343 | O | MET | A | 280 | 10.543 | 9.488 | 36.110 | 1.00 | 34.25 |
| ATOM | 344 | N | SER | A | 281 | 8.589 | 8.516 | 35.574 | 1.00 | 34.60 |
| ATOM | 345 | CA | SER | A | 281 | 8.884 | 7.292 | 36.303 | 1.00 | 35.57 |
| ATOM | 346 | CB | SER | A | 281 | 7.610 | 6.476 | 36.483 | 1.00 | 34.76 |
| ATOM | 347 | OG | SER | A | 281 | 7.261 | 5.755 | 35.320 | 1.00 | 34.99 |
| ATOM | 348 | C | SER | A | 281 | 9.923 | 6.473 | 35.554 | 1.00 | 38.19 |
| ATOM | 349 | O | SER | A | 281 | 10.155 | 6.652 | 34.369 | 1.00 | 38.35 |
| ATOM | 350 | N | PRO | A | 282 | 10.550 | 5.516 | 36.215 | 1.00 | 38.89 |
| ATOM | 351 | CD | PRO | A | 282 | 10.596 | 5.392 | 37.677 | 1.00 | 38.28 |
| ATOM | 352 | CA | PRO | A | 282 | 11.573 | 4.674 | 35.594 | 1.00 | 39.66 |
| ATOM | 353 | CB | PRO | A | 282 | 11.995 | 3.784 | 36.756 | 1.00 | 39.26 |
| ATOM | 354 | CG | PRO | A | 282 | 11.883 | 4.764 | 37.865 | 1.00 | 37.97 |
| ATOM | 355 | C | PRO | A | 282 | 10.949 | 3.876 | 34.442 | 1.00 | 41.11 |
| ATOM | 356 | O | PRO | A | 282 | 11.588 | 3.670 | 33.393 | 1.00 | 41.12 |
| ATOM | 357 | N | ASP | A | 283 | 9.743 | 3.358 | 34.618 | 1.00 | 41.70 |
| ATOM | 358 | CA | ASP | A | 283 | 9.045 | 2.581 | 33.586 | 1.00 | 42.50 |
| ATOM | 359 | CB | ASP | A | 283 | 7.658 | 2.141 | 34.066 | 1.00 | 44.72 |
| ATOM | 360 | CG | ASP | A | 283 | 7.693 | 0.885 | 34.944 | 1.00 | 47.82 |
| ATOM | 361 | OD1 | ASP | A | 283 | 8.777 | 0.244 | 35.039 | 1.00 | 48.00 |
| ATOM | 362 | OD2 | ASP | A | 283 | 6.654 | 0.542 | 35.561 | 1.00 | 49.79 |
| ATOM | 363 | C | ASP | A | 283 | 8.786 | 3.411 | 32.333 | 1.00 | 42.60 |
| ATOM | 364 | O | ASP | A | 283 | 8.849 | 2.902 | 31.183 | 1.00 | 43.49 |
| ATOM | 365 | N | ALA | A | 284 | 8.400 | 4.662 | 32.540 | 1.00 | 41.47 |
| ATOM | 366 | CA | ALA | A | 284 | 8.099 | 5.572 | 31.444 | 1.00 | 41.11 |
| ATOM | 367 | CB | ALA | A | 284 | 7.607 | 6.940 | 31.976 | 1.00 | 39.43 |
| ATOM | 368 | C | ALA | A | 284 | 9.334 | 5.774 | 30.585 | 1.00 | 40.83 |
| ATOM | 369 | O | ALA | A | 284 | 9.211 | 5.759 | 29.364 | 1.00 | 41.29 |
| ATOM | 370 | N | PHE | A | 285 | 10.491 | 5.861 | 31.249 | 1.00 | 39.98 |
| ATOM | 371 | CA | PHE | A | 285 | 11.813 | 6.033 | 30.613 | 1.00 | 37.14 |
| ATOM | 372 | CB | PHE | A | 285 | 12.774 | 6.631 | 31.674 | 1.00 | 34.26 |
| ATOM | 373 | CG | PHE | A | 285 | 14.173 | 6.889 | 31.156 | 1.00 | 31.34 |
| ATOM | 374 | CD1 | PHE | A | 285 | 14.472 | 8.058 | 30.476 | 1.00 | 29.73 |
| ATOM | 375 | CD2 | PHE | A | 285 | 15.202 | 5.979 | 31.389 | 1.00 | 30.95 |
| ATOM | 376 | CE1 | PHE | A | 285 | 15.753 | 8.320 | 30.060 | 1.00 | 27.91 |
| ATOM | 377 | CE2 | PHE | A | 285 | 16.484 | 6.238 | 30.975 | 1.00 | 28.35 |
| ATOM | 378 | CZ | PHE | A | 285 | 16.761 | 7.417 | 30.320 | 1.00 | 26.47 |
| ATOM | 379 | C | PHE | A | 285 | 12.276 | 4.648 | 30.109 | 1.00 | 36.57 |
| ATOM | 380 | O | PHE | A | 285 | 12.609 | 4.524 | 28.926 | 1.00 | 36.95 |
| ATOM | 381 | N | LEU | A | 286 | 12.419 | 3.633 | 30.855 | 0.00 | 47.33 |
| ATOM | 382 | CA | LEU | A | 286 | 12.893 | 2.325 | 30.394 | 0.00 | 49.77 |
| ATOM | 383 | CB | LEU | A | 286 | 13.109 | 1.366 | 31.580 | 0.00 | 50.36 |
| ATOM | 384 | CG | LEU | A | 286 | 14.374 | 1.611 | 32.413 | 0.00 | 51.61 |
| ATOM | 385 | CD1 | LEU | A | 286 | 14.241 | 1.013 | 33.823 | 0.00 | 52.80 |
| ATOM | 386 | CD2 | LEU | A | 286 | 15.615 | 1.072 | 31.700 | 0.00 | 51.49 |
| ATOM | 387 | C | LEU | A | 286 | 11.867 | 1.745 | 29.423 | 0.00 | 52.20 |
| ATOM | 388 | O | LEU | A | 286 | 12.186 | 0.874 | 28.598 | 0.00 | 53.32 |
| ATOM | 389 | N | ALA | A | 287 | 10.629 | 2.227 | 29.544 | 0.00 | 54.04 |
| ATOM | 390 | CA | ALA | A | 287 | 9.541 | 1.786 | 28.669 | 0.00 | 55.32 |
| ATOM | 391 | CB | ALA | A | 287 | 8.215 | 2.349 | 29.173 | 0.00 | 54.54 |
| ATOM | 392 | C | ALA | A | 287 | 9.841 | 2.268 | 27.234 | 0.00 | 56.28 |
| ATOM | 393 | O | ALA | A | 287 | 9.435 | 1.645 | 26.230 | 0.00 | 56.51 |
| ATOM | 394 | N | GLU | A | 288 | 10.658 | 3.316 | 27.161 | 0.00 | 57.65 |
| ATOM | 395 | CA | GLU | A | 288 | 11.083 | 3.920 | 25.883 | 0.00 | 58.84 |
| ATOM | 396 | CB | GLU | A | 288 | 11.479 | 5.397 | 26.111 | 0.00 | 60.54 |
| ATOM | 397 | CG | GLU | A | 288 | 10.486 | 6.232 | 26.962 | 0.00 | 61.51 |
| ATOM | 398 | CD | GLU | A | 288 | 10.887 | 7.708 | 27.101 | 0.00 | 61.54 |
| ATOM | 399 | OE1 | GLU | A | 288 | 12.109 | 8.009 | 27.198 | 0.00 | 61.14 |
| ATOM | 400 | OE2 | GLU | A | 288 | 9.970 | 8.563 | 27.111 | 0.00 | 60.04 |

Figure 10

| | | | | | | | | | |
|---|---|---|---|---|---|---|---|---|---|
| ATOM | 401 | C | GLU | A | 288 | 12.268 | 3.171 | 25.224 | 0.00 58.30 |
| ATOM | 402 | O | GLU | A | 288 | 12.747 | 3.551 | 24.140 | 0.00 56.41 |
| ATOM | 403 | N | ALA | A | 289 | 12.786 | 2.159 | 25.925 | 0.00 58.94 |
| ATOM | 404 | CA | ALA | A | 289 | 13.906 | 1.357 | 25.422 | 0.00 58.86 |
| ATOM | 405 | CB | ALA | A | 289 | 14.969 | 1.159 | 26.516 | 0.00 59.43 |
| ATOM | 406 | C | ALA | A | 289 | 13.444 | 0.008 | 24.906 | 0.00 58.67 |
| ATOM | 407 | O | ALA | A | 289 | 14.118 | -0.633 | 24.094 | 0.00 58.08 |
| ATOM | 408 | N | ASN | A | 290 | 12.305 | -0.442 | 25.408 | 0.00 59.48 |
| ATOM | 409 | CA | ASN | A | 290 | 11.748 | -1.727 | 25.012 | 0.00 60.28 |
| ATOM | 410 | CB | ASN | A | 290 | 10.542 | -2.052 | 25.894 | 0.00 61.94 |
| ATOM | 411 | CG | ASN | A | 290 | 10.935 | -2.205 | 27.360 | 0.00 63.63 |
| ATOM | 412 | OD1 | ASN | A | 290 | 10.268 | -1.690 | 28.266 | 0.00 63.33 |
| ATOM | 413 | ND2 | ASN | A | 290 | 12.059 | -2.891 | 27.594 | 0.00 65.24 |
| ATOM | 414 | C | ASN | A | 290 | 11.392 | -1.798 | 23.535 | 0.00 60.83 |
| ATOM | 415 | O | ASN | A | 290 | 11.230 | -2.897 | 22.991 | 0.00 61.21 |
| ATOM | 416 | N | LEU | A | 291 | 11.275 | -0.626 | 22.897 | 0.00 60.49 |
| ATOM | 417 | CA | LEU | A | 291 | 10.988 | -0.531 | 21.464 | 0.00 60.22 |
| ATOM | 418 | CB | LEU | A | 291 | 10.495 | 0.878 | 21.122 | 0.00 61.42 |
| ATOM | 419 | CG | LEU | A | 291 | 9.936 | 1.082 | 19.713 | 0.00 63.34 |
| ATOM | 420 | CD1 | LEU | A | 291 | 8.596 | 0.379 | 19.564 | 0.00 62.49 |
| ATOM | 421 | CD2 | LEU | A | 291 | 9.801 | 2.564 | 19.398 | 0.00 64.10 |
| ATOM | 422 | C | LEU | A | 291 | 12.222 | -0.879 | 20.634 | 0.00 59.37 |
| ATOM | 423 | O | LEU | A | 291 | 12.161 | -1.667 | 19.727 | 0.00 58.58 |
| ATOM | 424 | N | MET | A | 292 | 13.343 | -0.301 | 21.077 | 0.00 59.54 |
| ATOM | 425 | CA | MET | A | 292 | 14.673 | -0.499 | 20.496 | 0.00 59.23 |
| ATOM | 426 | CB | MET | A | 292 | 15.689 | 0.272 | 21.354 | 0.00 59.24 |
| ATOM | 427 | CG | MET | A | 292 | 16.763 | 0.992 | 20.579 | 0.00 60.17 |
| ATOM | 428 | SD | MET | A | 292 | 17.720 | 2.099 | 21.623 | 0.00 60.45 |
| ATOM | 429 | CE | MET | A | 292 | 16.946 | 3.744 | 21.175 | 0.00 61.37 |
| ATOM | 430 | C | MET | A | 292 | 15.047 | -1.999 | 20.431 | 0.00 58.45 |
| ATOM | 431 | O | MET | A | 292 | 15.627 | -2.476 | 19.455 | 0.00 58.16 |
| ATOM | 432 | N | LYS | A | 293 | 14.715 | -2.733 | 21.487 | 0.00 58.33 |
| ATOM | 433 | CA | LYS | A | 293 | 14.982 | -4.164 | 21.555 | 0.00 58.20 |
| ATOM | 434 | CB | LYS | A | 293 | 14.397 | -4.749 | 22.846 | 0.00 57.89 |
| ATOM | 435 | CG | LYS | A | 293 | 14.897 | -4.086 | 24.116 | 0.00 57.87 |
| ATOM | 436 | CD | LYS | A | 293 | 14.282 | -4.692 | 25.362 | 0.00 58.31 |
| ATOM | 437 | CE | LYS | A | 293 | 14.970 | -4.142 | 26.608 | 0.00 58.75 |
| ATOM | 438 | NZ | LYS | A | 293 | 14.498 | -4.818 | 27.840 | 0.00 59.26 |
| ATOM | 439 | C | LYS | A | 293 | 14.265 | -4.779 | 20.365 | 0.00 58.44 |
| ATOM | 440 | O | LYS | A | 293 | 14.847 | -5.541 | 19.581 | 0.00 59.24 |
| ATOM | 441 | N | GLN | A | 294 | 13.012 | -4.373 | 20.198 | 0.00 58.04 |
| ATOM | 442 | CA | GLN | A | 294 | 12.162 | -4.856 | 19.116 | 0.00 57.58 |
| ATOM | 443 | CB | GLN | A | 294 | 10.764 | -4.210 | 19.235 | 0.00 59.70 |
| ATOM | 444 | CG | GLN | A | 294 | 10.149 | -4.305 | 20.631 | 0.00 62.76 |
| ATOM | 445 | CD | GLN | A | 294 | 10.164 | -5.724 | 21.171 | 0.00 65.30 |
| ATOM | 446 | OE1 | GLN | A | 294 | 10.923 | -6.049 | 22.092 | 0.00 66.69 |
| ATOM | 447 | NE2 | GLN | A | 294 | 9.336 | -6.585 | 20.587 | 0.00 66.25 |
| ATOM | 448 | C | GLN | A | 294 | 12.711 | -4.650 | 17.683 | 0.00 55.70 |
| ATOM | 449 | O | GLN | A | 294 | 12.927 | -5.626 | 16.956 | 0.00 56.07 |
| ATOM | 450 | N | LEU | A | 295 | 12.979 | -3.397 | 17.302 | 0.00 52.54 |
| ATOM | 451 | CA | LEU | A | 295 | 13.444 | -3.082 | 15.951 | 0.00 48.98 |
| ATOM | 452 | CB | LEU | A | 295 | 12.716 | -1.843 | 15.425 | 0.00 48.19 |
| ATOM | 453 | CG | LEU | A | 295 | 11.198 | -1.839 | 15.397 | 0.00 47.55 |
| ATOM | 454 | CD1 | LEU | A | 295 | 10.706 | -0.475 | 14.913 | 0.00 46.77 |
| ATOM | 455 | CD2 | LEU | A | 295 | 10.699 | -2.966 | 14.504 | 0.00 46.45 |
| ATOM | 456 | C | LEU | A | 295 | 14.934 | -2.864 | 15.758 | 0.00 47.04 |
| ATOM | 457 | O | LEU | A | 295 | 15.473 | -1.834 | 16.167 | 0.00 47.58 |
| ATOM | 458 | N | GLN | A | 296 | 15.544 | -3.590 | 15.170 | 1.00 34.19 |
| ATOM | 459 | CA | GLN | A | 296 | 16.959 | -3.560 | 14.796 | 1.00 36.47 |

Figure 10

| | | | | | | | | |
|---|---|---|---|---|---|---|---|---|
| ATOM | 460 | CB | GLN | A | 296 | 17.688 | -4.785 | 15.359 | 1.00 38.23 |
| ATOM | 461 | CG | GLN | A | 296 | 17.920 | -4.741 | 16.868 | 1.00 42.71 |
| ATOM | 462 | CD | GLN | A | 296 | 18.359 | -6.085 | 17.437 | 1.00 45.60 |
| ATOM | 463 | OE1 | GLN | A | 296 | 18.951 | -6.915 | 16.728 | 1.00 47.49 |
| ATOM | 464 | NE2 | GLN | A | 296 | 18.076 | -6.305 | 18.725 | 1.00 44.96 |
| ATOM | 465 | C | GLN | A | 296 | 17.221 | -3.426 | 13.278 | 1.00 36.13 |
| ATOM | 466 | O | GLN | A | 296 | 16.593 | -4.104 | 12.452 | 1.00 37.50 |
| ATOM | 467 | N | HIS | A | 297 | 18.197 | -2.594 | 12.918 | 1.00 34.44 |
| ATOM | 468 | CA | HIS | A | 297 | 18.498 | -2.351 | 11.511 | 1.00 33.39 |
| ATOM | 469 | CB | HIS | A | 297 | 17.290 | -1.641 | 10.891 | 1.00 31.53 |
| ATOM | 470 | CG | HIS | A | 297 | 17.357 | -1.492 | 9.398 | 1.00 28.58 |
| ATOM | 471 | CD2 | HIS | A | 297 | 16.933 | -2.309 | 8.416 | 1.00 26.86 |
| ATOM | 472 | ND1 | HIS | A | 297 | 17.866 | -0.368 | 8.791 | 1.00 28.25 |
| ATOM | 473 | CE1 | HIS | A | 297 | 17.749 | -0.502 | 7.478 | 1.00 26.94 |
| ATOM | 474 | NE2 | HIS | A | 297 | 17.191 | -1.659 | 7.222 | 1.00 26.01 |
| ATOM | 475 | C | HIS | A | 297 | 19.727 | -1.459 | 11.399 | 1.00 33.48 |
| ATOM | 476 | O | HIS | A | 297 | 20.008 | -0.679 | 12.302 | 1.00 34.04 |
| ATOM | 477 | N | GLN | A | 298 | 20.439 | -1.545 | 10.282 | 1.00 34.79 |
| ATOM | 478 | CA | GLN | A | 298 | 21.635 | -0.726 | 10.097 | 1.00 35.96 |
| ATOM | 479 | CB | GLN | A | 298 | 22.426 | -1.139 | 8.836 | 1.00 39.47 |
| ATOM | 480 | CG | GLN | A | 298 | 23.468 | -2.277 | 9.088 | 1.00 45.69 |
| ATOM | 481 | CD | GLN | A | 298 | 24.293 | -2.085 | 10.388 | 1.00 48.66 |
| ATOM | 482 | OE1 | GLN | A | 298 | 24.156 | -2.856 | 11.352 | 1.00 50.58 |
| ATOM | 483 | NE2 | GLN | A | 298 | 25.117 | -1.039 | 10.424 | 1.00 49.19 |
| ATOM | 484 | C | GLN | A | 298 | 21.393 | 0.777 | 10.105 | 1.00 34.53 |
| ATOM | 485 | O | GLN | A | 298 | 22.303 | 1.558 | 10.366 | 1.00 34.78 |
| ATOM | 486 | N | ARG | A | 299 | 20.160 | 1.187 | 9.866 | 1.00 33.60 |
| ATOM | 487 | CA | ARG | A | 299 | 19.836 | 2.609 | 9.858 | 1.00 32.50 |
| ATOM | 488 | CB | ARG | A | 299 | 18.953 | 2.917 | 8.653 | 1.00 33.39 |
| ATOM | 489 | CG | ARG | A | 299 | 19.629 | 2.609 | 7.347 | 1.00 33.59 |
| ATOM | 490 | CD | ARG | A | 299 | 20.782 | 3.548 | 7.175 | 1.00 35.67 |
| ATOM | 491 | NE | ARG | A | 299 | 21.777 | 3.026 | 6.258 | 1.00 36.86 |
| ATOM | 492 | CZ | ARG | A | 299 | 23.083 | 3.141 | 6.460 | 1.00 39.14 |
| ATOM | 493 | NH1 | ARG | A | 299 | 23.559 | 3.757 | 7.548 | 1.00 41.02 |
| ATOM | 494 | NH2 | ARG | A | 299 | 23.916 | 2.655 | 5.560 | 1.00 39.98 |
| ATOM | 495 | C | ARG | A | 299 | 19.145 | 3.056 | 11.149 | 1.00 32.04 |
| ATOM | 496 | O | ARG | A | 299 | 18.611 | 4.158 | 11.217 | 1.00 31.52 |
| ATOM | 497 | N | LEU | A | 300 | 19.132 | 2.176 | 12.153 | 1.00 31.45 |
| ATOM | 498 | CA | LEU | A | 300 | 18.511 | 2.447 | 13.446 | 1.00 30.64 |
| ATOM | 499 | CB | LEU | A | 300 | 17.347 | 1.476 | 13.676 | 1.00 29.67 |
| ATOM | 500 | CG | LEU | A | 300 | 15.943 | 1.917 | 13.225 | 1.00 29.97 |
| ATOM | 501 | CD1 | LEU | A | 300 | 15.893 | 2.274 | 11.749 | 1.00 26.94 |
| ATOM | 502 | CD2 | LEU | A | 300 | 14.961 | 0.800 | 13.536 | 1.00 30.53 |
| ATOM | 503 | C | LEU | A | 300 | 19.529 | 2.330 | 14.577 | 1.00 30.44 |
| ATOM | 504 | O | LEU | A | 300 | 20.341 | 1.414 | 14.595 | 1.00 30.90 |
| ATOM | 505 | N | VAL | A | 301 | 19.491 | 3.265 | 15.517 | 1.00 31.60 |
| ATOM | 506 | CA | VAL | A | 301 | 20.416 | 3.249 | 16.646 | 1.00 33.65 |
| ATOM | 507 | CB | VAL | A | 301 | 20.241 | 4.505 | 17.539 | 1.00 32.38 |
| ATOM | 508 | CG1 | VAL | A | 301 | 20.951 | 4.332 | 18.867 | 1.00 32.63 |
| ATOM | 509 | CG2 | VAL | A | 301 | 20.797 | 5.730 | 16.822 | 1.00 31.72 |
| ATOM | 510 | C | VAL | A | 301 | 20.187 | 1.983 | 17.451 | 1.00 35.59 |
| ATOM | 511 | O | VAL | A | 301 | 19.068 | 1.714 | 17.899 | 1.00 36.26 |
| ATOM | 512 | N | ARG | A | 302 | 21.244 | 1.193 | 17.612 | 1.00 37.99 |
| ATOM | 513 | CA | ARG | A | 302 | 21.168 | -0.063 | 18.358 | 1.00 40.26 |
| ATOM | 514 | CB | ARG | A | 302 | 22.291 | -1.007 | 17.931 | 1.00 44.36 |
| ATOM | 515 | CG | ARG | A | 302 | 22.119 | -2.428 | 18.381 | 1.00 51.67 |
| ATOM | 516 | CD | ARG | A | 302 | 23.398 | -3.199 | 18.107 | 1.00 59.94 |
| ATOM | 517 | NE | ARG | A | 302 | 23.361 | -4.558 | 18.649 | 1.00 66.22 |
| ATOM | 518 | CZ | ARG | A | 302 | 24.351 | -5.445 | 18.540 | 1.00 69.09 |

Figure 10

```
ATOM    519  NH1 ARG A 302      25.485  -5.125  17.912  1.00 70.28
ATOM    520  NH2 ARG A 302      24.192  -6.669  19.036  1.00 70.33
ATOM    521  C   ARG A 302      21.228   0.225  19.857  1.00 39.47
ATOM    522  O   ARG A 302      22.033   1.031  20.315  1.00 38.43
ATOM    523  N   LEU A 303      20.323  -0.402  20.599  1.00 39.54
ATOM    524  CA  LEU A 303      20.219  -0.219  22.032  1.00 40.21
ATOM    525  CB  LEU A 303      18.728  -0.052  22.399  1.00 41.07
ATOM    526  CG  LEU A 303      17.883   0.962  21.576  1.00 41.54
ATOM    527  CD1 LEU A 303      16.389   0.892  21.870  1.00 40.75
ATOM    528  CD2 LEU A 303      18.362   2.352  21.824  1.00 40.75
ATOM    529  C   LEU A 303      20.887  -1.378  22.789  1.00 40.03
ATOM    530  O   LEU A 303      20.268  -2.405  22.994  1.00 41.22
ATOM    531  N   TYR A 304      22.161  -1.219  23.164  1.00 40.04
ATOM    532  CA  TYR A 304      22.925  -2.257  23.880  1.00 39.93
ATOM    533  CB  TYR A 304      24.382  -1.817  24.092  1.00 40.82
ATOM    534  CG  TYR A 304      25.191  -1.565  22.826  1.00 42.51
ATOM    535  CD1 TYR A 304      26.293  -0.709  22.847  1.00 43.38
ATOM    536  CE1 TYR A 304      27.054  -0.476  21.702  1.00 45.01
ATOM    537  CD2 TYR A 304      24.867  -2.187  21.616  1.00 43.07
ATOM    538  CE2 TYR A 304      25.624  -1.962  20.463  1.00 44.78
ATOM    539  CZ  TYR A 304      26.719  -1.102  20.514  1.00 45.35
ATOM    540  OH  TYR A 304      27.481  -0.864  19.390  1.00 44.33
ATOM    541  C   TYR A 304      22.366  -2.786  25.219  1.00 39.92
ATOM    542  O   TYR A 304      22.031  -3.967  25.325  1.00 39.95
ATOM    543  N   ALA A 305      22.297  -1.943  26.244  1.00 40.32
ATOM    544  CA  ALA A 305      21.805  -2.413  27.532  1.00 39.84
ATOM    545  CB  ALA A 305      22.964  -2.969  28.335  1.00 40.69
ATOM    546  C   ALA A 305      21.075  -1.353  28.334  1.00 40.35
ATOM    547  O   ALA A 305      20.851  -0.247  27.847  1.00 39.81
ATOM    548  N   VAL A 306      20.668  -1.722  29.553  1.00 40.42
ATOM    549  CA  VAL A 306      19.955  -0.829  30.495  1.00 41.16
ATOM    550  CB  VAL A 306      18.390  -0.933  30.390  1.00 41.40
ATOM    551  CG1 VAL A 306      17.870  -0.193  29.165  1.00 42.50
ATOM    552  CG2 VAL A 306      17.946  -2.388  30.371  1.00 41.14
ATOM    553  C   VAL A 306      20.314  -1.102  31.971  1.00 40.77
ATOM    554  O   VAL A 306      20.569  -2.242  32.359  1.00 40.94
ATOM    555  N   VAL A 307      20.344  -0.046  32.781  1.00 39.96
ATOM    556  CA  VAL A 307      20.624  -0.180  34.205  1.00 39.89
ATOM    557  CB  VAL A 307      21.852   0.681  34.652  1.00 39.20
ATOM    558  CG1 VAL A 307      22.121   0.526  36.158  1.00 37.38
ATOM    559  CG2 VAL A 307      23.083   0.271  33.856  1.00 38.22
ATOM    560  C   VAL A 307      19.340   0.267  34.897  1.00 40.13
ATOM    561  O   VAL A 307      18.979   1.447  34.872  1.00 38.32
ATOM    562  N   THR A 308      18.636  -0.705  35.470  1.00 41.85
ATOM    563  CA  THR A 308      17.361  -0.459  36.140  1.00 44.00
ATOM    564  CB  THR A 308      16.516  -1.739  36.193  1.00 43.18
ATOM    565  OG1 THR A 308      17.368  -2.855  36.459  1.00 44.86
ATOM    566  CG2 THR A 308      15.817  -1.971  34.863  1.00 41.38
ATOM    567  C   THR A 308      17.380   0.224  37.510  1.00 46.19
ATOM    568  O   THR A 308      16.363   0.756  37.938  1.00 46.91
ATOM    569  N   GLN A 309      18.506   0.190  38.217  1.00 48.55
ATOM    570  CA  GLN A 309      18.592   0.855  39.514  1.00 50.28
ATOM    571  CB  GLN A 309      19.637   0.174  40.409  1.00 54.72
ATOM    572  CG  GLN A 309      19.257  -1.226  40.893  1.00 61.05
ATOM    573  CD  GLN A 309      18.009  -1.251  41.795  1.00 64.96
ATOM    574  OE1 GLN A 309      17.387  -0.219  42.071  1.00 66.54
ATOM    575  NE2 GLN A 309      17.645  -2.446  42.255  1.00 67.10
ATOM    576  C   GLN A 309      18.966   2.322  39.308  1.00 49.63
ATOM    577  O   GLN A 309      19.800   2.632  38.464  1.00 48.70
```

Figure 10

| | | | | | | | | | |
|---|---|---|---|---|---|---|---|---|---|
| ATOM | 578 | N | GLU | A | 310 | 18.394 | 3.206 | 40.122 | 1.00 50.10 |
| ATOM | 579 | CA | GLU | A | 310 | 18.653 | 4.647 | 40.039 | 1.00 51.07 |
| ATOM | 580 | CB | GLU | A | 310 | 17.680 | 5.429 | 40.938 | 1.00 55.43 |
| ATOM | 581 | CG | GLU | A | 310 | 17.696 | 5.039 | 42.432 | 1.00 63.18 |
| ATOM | 582 | CD | GLU | A | 310 | 16.687 | 3.939 | 42.796 | 1.00 67.47 |
| ATOM | 583 | OE1 | GLU | A | 310 | 15.469 | 4.170 | 42.589 | 1.00 69.84 |
| ATOM | 584 | OE2 | GLU | A | 310 | 17.112 | 2.859 | 43.296 | 1.00 68.72 |
| ATOM | 585 | C | GLU | A | 310 | 20.093 | 5.067 | 40.363 | 1.00 49.88 |
| ATOM | 586 | O | GLU | A | 310 | 20.674 | 4.605 | 41.354 | 1.00 50.33 |
| ATOM | 587 | N | PRO | A | 311 | 20.705 | 5.920 | 39.505 | 1.00 48.13 |
| ATOM | 588 | CD | PRO | A | 311 | 21.981 | 6.566 | 39.869 | 1.00 48.27 |
| ATOM | 589 | CA | PRO | A | 311 | 20.168 | 6.522 | 38.264 | 1.00 45.19 |
| ATOM | 590 | CB | PRO | A | 311 | 21.229 | 7.572 | 37.898 | 1.00 45.19 |
| ATOM | 591 | CG | PRO | A | 311 | 21.842 | 7.924 | 39.221 | 1.00 46.84 |
| ATOM | 592 | C | PRO | A | 311 | 19.941 | 5.520 | 37.106 | 1.00 42.21 |
| ATOM | 593 | O | PRO | A | 311 | 20.799 | 4.677 | 36.794 | 1.00 42.73 |
| ATOM | 594 | N | ILE | A | 312 | 18.774 | 5.638 | 36.473 | 1.00 38.42 |
| ATOM | 595 | CA | ILE | A | 312 | 18.359 | 4.766 | 35.367 | 1.00 33.68 |
| ATOM | 596 | CB | ILE | A | 312 | 16.854 | 4.980 | 35.024 | 1.00 33.04 |
| ATOM | 597 | CG2 | ILE | A | 312 | 16.336 | 3.828 | 34.172 | 1.00 33.27 |
| ATOM | 598 | CG1 | ILE | A | 312 | 16.009 | 5.056 | 36.296 | 1.00 31.95 |
| ATOM | 599 | CD1 | ILE | A | 312 | 16.026 | 3.784 | 37.111 | 1.00 30.63 |
| ATOM | 600 | C | ILE | A | 312 | 19.168 | 5.096 | 34.122 | 1.00 30.83 |
| ATOM | 601 | O | ILE | A | 312 | 19.308 | 6.267 | 33.769 | 1.00 29.04 |
| ATOM | 602 | N | TYR | A | 313 | 19.706 | 4.071 | 33.469 | 1.00 28.83 |
| ATOM | 603 | CA | TYR | A | 313 | 20.494 | 4.273 | 32.254 | 1.00 28.06 |
| ATOM | 604 | CB | TYR | A | 313 | 21.935 | 3.771 | 32.427 | 1.00 26.96 |
| ATOM | 605 | CG | TYR | A | 313 | 22.872 | 4.547 | 33.321 | 1.00 28.24 |
| ATOM | 606 | CD1 | TYR | A | 313 | 22.530 | 5.799 | 33.838 | 1.00 27.09 |
| ATOM | 607 | CE1 | TYR | A | 313 | 23.395 | 6.480 | 34.697 | 1.00 28.06 |
| ATOM | 608 | CD2 | TYR | A | 313 | 24.109 | 3.999 | 33.679 | 1.00 27.91 |
| ATOM | 609 | CE2 | TYR | A | 313 | 24.979 | 4.670 | 34.532 | 1.00 28.66 |
| ATOM | 610 | CZ | TYR | A | 313 | 24.621 | 5.904 | 35.042 | 1.00 29.56 |
| ATOM | 611 | OH | TYR | A | 313 | 25.482 | 6.552 | 35.905 | 1.00 30.63 |
| ATOM | 612 | C | TYR | A | 313 | 19.964 | 3.528 | 31.035 | 1.00 28.31 |
| ATOM | 613 | O | TYR | A | 313 | 19.366 | 2.455 | 31.147 | 1.00 28.43 |
| ATOM | 614 | N | ILE | A | 314 | 20.231 | 4.094 | 29.863 | 1.00 28.71 |
| ATOM | 615 | CA | ILE | A | 314 | 19.913 | 3.443 | 28.598 | 1.00 29.08 |
| ATOM | 616 | CB | ILE | A | 314 | 18.726 | 4.086 | 27.819 | 1.00 30.88 |
| ATOM | 617 | CG2 | ILE | A | 314 | 18.597 | 3.470 | 26.406 | 1.00 28.24 |
| ATOM | 618 | CG1 | ILE | A | 314 | 17.422 | 3.804 | 28.555 | 1.00 32.26 |
| ATOM | 619 | CD1 | ILE | A | 314 | 16.218 | 4.400 | 27.886 | 1.00 35.77 |
| ATOM | 620 | C | ILE | A | 314 | 21.219 | 3.589 | 27.838 | 1.00 28.13 |
| ATOM | 621 | O | ILE | A | 314 | 21.756 | 4.690 | 27.727 | 1.00 27.82 |
| ATOM | 622 | N | ILE | A | 315 | 21.786 | 2.456 | 27.439 | 1.00 28.08 |
| ATOM | 623 | CA | ILE | A | 315 | 23.044 | 2.435 | 26.716 | 1.00 27.98 |
| ATOM | 624 | CB | ILE | A | 315 | 24.054 | 1.424 | 27.351 | 1.00 29.80 |
| ATOM | 625 | CG2 | ILE | A | 315 | 25.342 | 1.341 | 26.536 | 1.00 29.91 |
| ATOM | 626 | CG1 | ILE | A | 315 | 24.372 | 1.815 | 28.796 | 1.00 29.19 |
| ATOM | 627 | CD1 | ILE | A | 315 | 23.328 | 1.362 | 29.789 | 1.00 29.67 |
| ATOM | 628 | C | ILE | A | 315 | 22.789 | 2.039 | 25.284 | 1.00 26.93 |
| ATOM | 629 | O | ILE | A | 315 | 22.143 | 1.032 | 25.013 | 1.00 27.03 |
| ATOM | 630 | N | THR | A | 316 | 23.287 | 2.862 | 24.372 | 1.00 26.83 |
| ATOM | 631 | CA | THR | A | 316 | 23.159 | 2.623 | 22.942 | 1.00 25.81 |
| ATOM | 632 | CB | THR | A | 316 | 22.299 | 3.709 | 22.280 | 1.00 24.09 |
| ATOM | 633 | OG1 | THR | A | 316 | 22.982 | 4.964 | 22.360 | 1.00 24.93 |
| ATOM | 634 | CG2 | THR | A | 316 | 20.985 | 3.839 | 22.960 | 1.00 22.77 |
| ATOM | 635 | C | THR | A | 316 | 24.560 | 2.749 | 22.333 | 1.00 26.64 |
| ATOM | 636 | O | THR | A | 316 | 25.526 | 3.105 | 23.015 | 1.00 26.93 |

Figure 10

| | | | | | | | | |
|---|---|---|---|---|---|---|---|---|
| ATOM | 637 | N | GLU | A | 317 | 24.676 | 2.466 | 21.043 | 1.00 26.84 |
| ATOM | 638 | CA | GLU | A | 317 | 25.952 | 2.627 | 20.388 | 1.00 26.95 |
| ATOM | 639 | CB | GLU | A | 317 | 25.900 | 2.093 | 18.958 | 1.00 27.77 |
| ATOM | 640 | CG | GLU | A | 317 | 24.868 | 2.741 | 18.073 | 1.00 28.55 |
| ATOM | 641 | CD | GLU | A | 317 | 24.887 | 2.166 | 16.693 | 1.00 29.87 |
| ATOM | 642 | OE1 | GLU | A | 317 | 23.845 | 1.628 | 16.273 | 1.00 30.99 |
| ATOM | 643 | OE2 | GLU | A | 317 | 25.947 | 2.237 | 16.032 | 1.00 31.60 |
| ATOM | 644 | C | GLU | A | 317 | 26.261 | 4.126 | 20.393 | 1.00 27.29 |
| ATOM | 645 | O | GLU | A | 317 | 25.379 | 4.968 | 20.571 | 1.00 27.22 |
| ATOM | 646 | N | TYR | A | 318 | 27.527 | 4.451 | 20.233 | 1.00 27.00 |
| ATOM | 647 | CA | TYR | A | 318 | 27.952 | 5.824 | 20.224 | 1.00 27.07 |
| ATOM | 648 | CB | TYR | A | 318 | 29.293 | 5.932 | 20.938 | 1.00 26.75 |
| ATOM | 649 | CG | TYR | A | 318 | 29.918 | 7.299 | 20.888 | 1.00 28.52 |
| ATOM | 650 | CD1 | TYR | A | 318 | 29.395 | 8.368 | 21.632 | 1.00 29.36 |
| ATOM | 651 | CE1 | TYR | A | 318 | 29.967 | 9.645 | 21.558 | 1.00 29.76 |
| ATOM | 652 | CD2 | TYR | A | 318 | 31.030 | 7.541 | 20.075 | 1.00 29.33 |
| ATOM | 653 | CE2 | TYR | A | 318 | 31.607 | 8.803 | 19.996 | 1.00 28.03 |
| ATOM | 654 | CZ | TYR | A | 318 | 31.074 | 9.847 | 20.732 | 1.00 29.23 |
| ATOM | 655 | OH | TYR | A | 318 | 31.631 | 11.095 | 20.621 | 1.00 31.13 |
| ATOM | 656 | C | TYR | A | 318 | 28.082 | 6.261 | 18.780 | 1.00 28.09 |
| ATOM | 657 | O | TYR | A | 318 | 28.565 | 5.496 | 17.947 | 1.00 28.72 |
| ATOM | 658 | N | MET | A | 319 | 27.572 | 7.454 | 18.477 | 1.00 28.91 |
| ATOM | 659 | CA | MET | A | 319 | 27.637 | 8.044 | 17.135 | 1.00 29.41 |
| ATOM | 660 | CB | MET | A | 319 | 26.266 | 8.527 | 16.676 | 1.00 27.96 |
| ATOM | 661 | CG | MET | A | 319 | 25.255 | 7.420 | 16.554 | 1.00 27.66 |
| ATOM | 662 | SD | MET | A | 319 | 25.804 | 6.199 | 15.388 | 1.00 30.11 |
| ATOM | 663 | CE | MET | A | 319 | 25.187 | 6.896 | 13.837 | 1.00 28.47 |
| ATOM | 664 | C | MET | A | 319 | 28.572 | 9.233 | 17.222 | 1.00 30.96 |
| ATOM | 665 | O | MET | A | 319 | 28.191 | 10.286 | 17.724 | 1.00 31.91 |
| ATOM | 666 | N | GLU | A | 320 | 29.800 | 9.032 | 16.754 | 1.00 32.50 |
| ATOM | 667 | CA | GLU | A | 320 | 30.873 | 10.027 | 16.747 | 1.00 33.01 |
| ATOM | 668 | CB | GLU | A | 320 | 31.918 | 9.589 | 15.714 | 1.00 38.13 |
| ATOM | 669 | CG | GLU | A | 320 | 33.082 | 10.555 | 15.487 | 1.00 45.19 |
| ATOM | 670 | CD | GLU | A | 320 | 34.133 | 10.496 | 16.594 | 1.00 49.30 |
| ATOM | 671 | OE1 | GLU | A | 320 | 34.284 | 9.415 | 17.219 | 1.00 50.25 |
| ATOM | 672 | OE2 | GLU | A | 320 | 34.816 | 11.527 | 16.825 | 1.00 51.20 |
| ATOM | 673 | C | GLU | A | 320 | 30.473 | 11.488 | 16.498 | 1.00 31.19 |
| ATOM | 674 | O | GLU | A | 320 | 30.827 | 12.382 | 17.272 | 1.00 31.03 |
| ATOM | 675 | N | ASN | A | 321 | 29.719 | 11.728 | 15.432 | 1.00 29.48 |
| ATOM | 676 | CA | ASN | A | 321 | 29.312 | 13.082 | 15.087 | 1.00 27.28 |
| ATOM | 677 | CB | ASN | A | 321 | 29.378 | 13.262 | 13.586 | 1.00 26.64 |
| ATOM | 678 | CG | ASN | A | 321 | 30.791 | 13.347 | 13.102 | 1.00 27.03 |
| ATOM | 679 | OD1 | ASN | A | 321 | 31.552 | 14.175 | 13.581 | 1.00 27.48 |
| ATOM | 680 | ND2 | ASN | A | 321 | 31.175 | 12.461 | 12.203 | 1.00 27.86 |
| ATOM | 681 | C | ASN | A | 321 | 28.003 | 13.611 | 15.618 | 1.00 26.06 |
| ATOM | 682 | O | ASN | A | 321 | 27.493 | 14.607 | 15.112 | 1.00 26.68 |
| ATOM | 683 | N | GLY | A | 322 | 27.466 | 12.950 | 16.631 | 1.00 25.42 |
| ATOM | 684 | CA | GLY | A | 322 | 26.224 | 13.379 | 17.240 | 1.00 24.88 |
| ATOM | 685 | C | GLY | A | 322 | 24.992 | 13.590 | 16.382 | 1.00 25.68 |
| ATOM | 686 | O | GLY | A | 322 | 24.657 | 12.810 | 15.495 | 1.00 25.14 |
| ATOM | 687 | N | SER | A | 323 | 24.305 | 14.682 | 16.672 | 1.00 26.58 |
| ATOM | 688 | CA | SER | A | 323 | 23.076 | 15.033 | 15.988 | 1.00 27.62 |
| ATOM | 689 | CB | SER | A | 323 | 22.370 | 16.103 | 16.799 | 1.00 26.87 |
| ATOM | 690 | OG | SER | A | 323 | 21.063 | 16.300 | 16.333 | 1.00 31.61 |
| ATOM | 691 | C | SER | A | 323 | 23.338 | 15.555 | 14.584 | 1.00 29.70 |
| ATOM | 692 | O | SER | A | 323 | 24.305 | 16.293 | 14.377 | 1.00 31.24 |
| ATOM | 693 | N | LEU | A | 324 | 22.486 | 15.175 | 13.623 | 1.00 29.52 |
| ATOM | 694 | CA | LEU | A | 324 | 22.619 | 15.633 | 12.233 | 1.00 28.23 |
| ATOM | 695 | CB | LEU | A | 324 | 21.660 | 14.862 | 11.311 | 1.00 26.66 |

Figure 10

| | | | | | | | | |
|---|---|---|---|---|---|---|---|---|
| ATOM | 696 | CG | LEU | A | 324 | 21.550 | 15.263 | 9.823 | 1.00 | 27.29 |
| ATOM | 697 | CD1 | LEU | A | 324 | 22.833 | 14.965 | 9.060 | 1.00 | 25.32 |
| ATOM | 698 | CD2 | LEU | A | 324 | 20.375 | 14.547 | 9.175 | 1.00 | 26.12 |
| ATOM | 699 | C | LEU | A | 324 | 22.370 | 17.151 | 12.116 | 1.00 | 29.00 |
| ATOM | 700 | O | LEU | A | 324 | 23.082 | 17.839 | 11.397 | 1.00 | 28.52 |
| ATOM | 701 | N | VAL | A | 325 | 21.390 | 17.668 | 12.858 | 1.00 | 29.75 |
| ATOM | 702 | CA | VAL | A | 325 | 21.061 | 19.087 | 12.833 | 1.00 | 30.75 |
| ATOM | 703 | CB | VAL | A | 325 | 19.762 | 19.385 | 13.664 | 1.00 | 31.11 |
| ATOM | 704 | CG1 | VAL | A | 325 | 20.033 | 19.405 | 15.173 | 1.00 | 31.12 |
| ATOM | 705 | CG2 | VAL | A | 325 | 19.106 | 20.667 | 13.194 | 1.00 | 29.41 |
| ATOM | 706 | C | VAL | A | 325 | 22.247 | 19.950 | 13.286 | 1.00 | 32.70 |
| ATOM | 707 | O | VAL | A | 325 | 22.405 | 21.088 | 12.823 | 1.00 | 32.99 |
| ATOM | 708 | N | ASP | A | 326 | 23.073 | 19.414 | 14.188 | 1.00 | 33.76 |
| ATOM | 709 | CA | ASP | A | 326 | 24.270 | 20.128 | 14.662 | 1.00 | 34.90 |
| ATOM | 710 | CB | ASP | A | 326 | 24.712 | 19.652 | 16.052 | 1.00 | 33.50 |
| ATOM | 711 | CG | ASP | A | 326 | 23.752 | 20.049 | 17.143 | 1.00 | 33.74 |
| ATOM | 712 | OD1 | ASP | A | 326 | 23.141 | 21.139 | 17.087 | 1.00 | 33.84 |
| ATOM | 713 | OD2 | ASP | A | 326 | 23.626 | 19.260 | 18.092 | 1.00 | 36.49 |
| ATOM | 714 | C | ASP | A | 326 | 25.435 | 19.910 | 13.692 | 1.00 | 35.82 |
| ATOM | 715 | O | ASP | A | 326 | 26.185 | 20.842 | 13.378 | 1.00 | 36.94 |
| ATOM | 716 | N | PHE | A | 327 | 25.592 | 18.670 | 13.234 | 1.00 | 35.94 |
| ATOM | 717 | CA | PHE | A | 327 | 26.662 | 18.321 | 12.312 | 1.00 | 35.94 |
| ATOM | 718 | CB | PHE | A | 327 | 26.634 | 16.822 | 12.011 | 1.00 | 34.53 |
| ATOM | 719 | CG | PHE | A | 327 | 27.660 | 16.396 | 11.004 | 1.00 | 33.55 |
| ATOM | 720 | CD1 | PHE | A | 327 | 29.009 | 16.324 | 11.353 | 1.00 | 32.82 |
| ATOM | 721 | CD2 | PHE | A | 327 | 27.286 | 16.093 | 9.700 | 1.00 | 32.91 |
| ATOM | 722 | CE1 | PHE | A | 327 | 29.967 | 15.962 | 10.423 | 1.00 | 29.38 |
| ATOM | 723 | CE2 | PHE | A | 327 | 28.244 | 15.727 | 8.756 | 1.00 | 32.49 |
| ATOM | 724 | CZ | PHE | A | 327 | 29.587 | 15.662 | 9.123 | 1.00 | 31.40 |
| ATOM | 725 | C | PHE | A | 327 | 26.624 | 19.113 | 11.000 | 1.00 | 37.48 |
| ATOM | 726 | O | PHE | A | 327 | 27.672 | 19.515 | 10.473 | 1.00 | 38.38 |
| ATOM | 727 | N | LEU | A | 328 | 25.422 | 19.327 | 10.469 | 1.00 | 37.45 |
| ATOM | 728 | CA | LEU | A | 328 | 25.258 | 20.064 | 9.214 | 1.00 | 36.84 |
| ATOM | 729 | CB | LEU | A | 328 | 23.792 | 20.064 | 8.754 | 1.00 | 35.56 |
| ATOM | 730 | CG | LEU | A | 328 | 23.174 | 18.728 | 8.334 | 1.00 | 32.62 |
| ATOM | 731 | CD1 | LEU | A | 328 | 21.667 | 18.820 | 8.333 | 1.00 | 32.52 |
| ATOM | 732 | CD2 | LEU | A | 328 | 23.698 | 18.317 | 6.991 | 1.00 | 31.79 |
| ATOM | 733 | C | LEU | A | 328 | 25.754 | 21.491 | 9.342 | 1.00 | 36.88 |
| ATOM | 734 | O | LEU | A | 328 | 26.198 | 22.062 | 8.358 | 1.00 | 36.71 |
| ATOM | 735 | N | LYS | A | 329 | 25.691 | 22.045 | 10.555 | 1.00 | 38.66 |
| ATOM | 736 | CA | LYS | A | 329 | 26.139 | 23.415 | 10.825 | 1.00 | 40.50 |
| ATOM | 737 | CB | LYS | A | 329 | 25.457 | 24.006 | 12.065 | 1.00 | 38.73 |
| ATOM | 738 | CG | LYS | A | 329 | 23.959 | 24.193 | 11.983 | 1.00 | 38.07 |
| ATOM | 739 | CD | LYS | A | 329 | 23.448 | 24.908 | 13.235 | 1.00 | 39.00 |
| ATOM | 740 | CE | LYS | A | 329 | 21.928 | 24.934 | 13.322 | 1.00 | 39.41 |
| ATOM | 741 | NZ | LYS | A | 329 | 21.388 | 23.571 | 13.569 | 1.00 | 41.23 |
| ATOM | 742 | C | LYS | A | 329 | 27.650 | 23.532 | 11.018 | 1.00 | 42.30 |
| ATOM | 743 | O | LYS | A | 329 | 28.198 | 24.631 | 10.875 | 1.00 | 43.22 |
| ATOM | 744 | N | THR | A | 330 | 28.316 | 22.418 | 11.347 | 1.00 | 43.32 |
| ATOM | 745 | CA | THR | A | 330 | 29.771 | 22.410 | 11.579 | 1.00 | 44.52 |
| ATOM | 746 | CB | THR | A | 330 | 30.283 | 21.041 | 12.142 | 1.00 | 44.63 |
| ATOM | 747 | OG1 | THR | A | 330 | 30.193 | 20.032 | 11.125 | 1.00 | 45.24 |
| ATOM | 748 | CG2 | THR | A | 330 | 29.505 | 20.615 | 13.391 | 1.00 | 42.60 |
| ATOM | 749 | C | THR | A | 330 | 30.536 | 22.691 | 10.284 | 1.00 | 45.47 |
| ATOM | 750 | O | THR | A | 330 | 29.963 | 22.571 | 9.203 | 1.00 | 45.24 |
| ATOM | 751 | N | PRO | A | 331 | 31.834 | 23.080 | 10.383 | 1.00 | 45.88 |
| ATOM | 752 | CD | PRO | A | 331 | 32.572 | 23.381 | 11.628 | 1.00 | 46.28 |
| ATOM | 753 | CA | PRO | A | 331 | 32.671 | 23.372 | 9.211 | 1.00 | 45.79 |
| ATOM | 754 | CB | PRO | A | 331 | 34.059 | 23.563 | 9.830 | 1.00 | 46.29 |

Figure 10

| | | | | | | | | |
|---|---|---|---|---|---|---|---|---|
| ATOM | 755 | CG | PRO | A | 331 | 33.748 | 24.197 | 11.133 | 1.00 46.33 |
| ATOM | 756 | C | PRO | A | 331 | 32.665 | 22.231 | 8.183 | 1.00 45.89 |
| ATOM | 757 | O | PRO | A | 331 | 32.679 | 22.475 | 6.979 | 1.00 45.87 |
| ATOM | 758 | N | SER | A | 332 | 32.627 | 20.990 | 8.662 | 1.00 45.78 |
| ATOM | 759 | CA | SER | A | 332 | 32.610 | 19.823 | 7.776 | 1.00 46.06 |
| ATOM | 760 | CB | SER | A | 332 | 33.067 | 18.574 | 8.535 | 1.00 47.42 |
| ATOM | 761 | OG | SER | A | 332 | 34.292 | 18.811 | 9.210 | 1.00 49.46 |
| ATOM | 762 | C | SER | A | 332 | 31.210 | 19.578 | 7.223 | 1.00 45.29 |
| ATOM | 763 | O | SER | A | 332 | 31.047 | 19.080 | 6.102 | 1.00 43.73 |
| ATOM | 764 | N | GLY | A | 333 | 30.207 | 19.913 | 8.031 | 1.00 45.23 |
| ATOM | 765 | CA | GLY | A | 333 | 28.829 | 19.729 | 7.623 | 1.00 46.09 |
| ATOM | 766 | C | GLY | A | 333 | 28.449 | 20.751 | 6.581 | 1.00 46.78 |
| ATOM | 767 | O | GLY | A | 333 | 27.720 | 20.450 | 5.638 | 1.00 46.40 |
| ATOM | 768 | N | ILE | A | 334 | 28.980 | 21.958 | 6.749 | 1.00 47.63 |
| ATOM | 769 | CA | ILE | A | 334 | 28.731 | 23.063 | 5.836 | 1.00 48.30 |
| ATOM | 770 | CB | ILE | A | 334 | 29.340 | 24.380 | 6.396 | 1.00 48.96 |
| ATOM | 771 | CG2 | ILE | A | 334 | 29.462 | 25.437 | 5.312 | 1.00 49.78 |
| ATOM | 772 | CG1 | ILE | A | 334 | 28.499 | 24.896 | 7.569 | 1.00 49.14 |
| ATOM | 773 | CD1 | ILE | A | 334 | 27.110 | 25.391 | 7.199 | 1.00 49.37 |
| ATOM | 774 | C | ILE | A | 334 | 29.317 | 22.749 | 4.458 | 1.00 48.32 |
| ATOM | 775 | O | ILE | A | 334 | 28.680 | 23.033 | 3.444 | 1.00 49.63 |
| ATOM | 776 | N | LYS | A | 335 | 30.483 | 22.102 | 4.429 | 1.00 47.88 |
| ATOM | 777 | CA | LYS | A | 335 | 31.168 | 21.755 | 3.180 | 1.00 47.63 |
| ATOM | 778 | CB | LYS | A | 335 | 32.676 | 21.585 | 3.430 | 1.00 49.57 |
| ATOM | 779 | CG | LYS | A | 335 | 33.432 | 22.817 | 3.963 | 1.00 52.27 |
| ATOM | 780 | CD | LYS | A | 335 | 34.853 | 22.411 | 4.436 | 1.00 54.38 |
| ATOM | 781 | CE | LYS | A | 335 | 35.540 | 23.504 | 5.273 | 1.00 55.66 |
| ATOM | 782 | NZ | LYS | A | 335 | 36.369 | 22.915 | 6.383 | 1.00 56.14 |
| ATOM | 783 | C | LYS | A | 335 | 30.661 | 20.520 | 2.414 | 1.00 46.39 |
| ATOM | 784 | O | LYS | A | 335 | 31.188 | 20.208 | 1.350 | 1.00 47.12 |
| ATOM | 785 | N | LEU | A | 336 | 29.681 | 19.794 | 2.951 | 1.00 45.37 |
| ATOM | 786 | CA | LEU | A | 336 | 29.145 | 18.589 | 2.274 | 1.00 43.20 |
| ATOM | 787 | CB | LEU | A | 336 | 28.133 | 17.850 | 3.169 | 1.00 42.95 |
| ATOM | 788 | CG | LEU | A | 336 | 28.566 | 17.174 | 4.475 | 1.00 41.26 |
| ATOM | 789 | CD1 | LEU | A | 336 | 27.351 | 16.645 | 5.187 | 1.00 39.35 |
| ATOM | 790 | CD2 | LEU | A | 336 | 29.533 | 16.043 | 4.189 | 1.00 40.70 |
| ATOM | 791 | C | LEU | A | 336 | 28.471 | 18.871 | 0.929 | 1.00 42.20 |
| ATOM | 792 | O | LEU | A | 336 | 27.702 | 19.831 | 0.800 | 1.00 42.64 |
| ATOM | 793 | N | THR | A | 337 | 28.719 | 17.999 | -0.050 | 1.00 41.01 |
| ATOM | 794 | CA | THR | A | 337 | 28.139 | 18.141 | -1.390 | 1.00 40.30 |
| ATOM | 795 | CB | THR | A | 337 | 28.932 | 17.329 | -2.492 | 1.00 38.89 |
| ATOM | 796 | OG1 | THR | A | 337 | 28.563 | 15.947 | -2.457 | 1.00 37.79 |
| ATOM | 797 | CG2 | THR | A | 337 | 30.437 | 17.434 | -2.282 | 1.00 39.09 |
| ATOM | 798 | C | THR | A | 337 | 26.653 | 17.727 | -1.430 | 1.00 40.40 |
| ATOM | 799 | O | THR | A | 337 | 26.144 | 17.077 | -0.512 | 1.00 40.54 |
| ATOM | 800 | N | ILE | A | 338 | 25.967 | 18.109 | -2.506 | 1.00 39.51 |
| ATOM | 801 | CA | ILE | A | 338 | 24.560 | 17.778 | -2.674 | 1.00 37.44 |
| ATOM | 802 | CB | ILE | A | 338 | 23.961 | 18.459 | -3.942 | 1.00 37.64 |
| ATOM | 803 | CG2 | ILE | A | 338 | 24.659 | 17.948 | -5.231 | 1.00 36.26 |
| ATOM | 804 | CG1 | ILE | A | 338 | 22.442 | 18.232 | -4.003 | 1.00 37.74 |
| ATOM | 805 | CD1 | ILE | A | 338 | 21.635 | 18.887 | -2.874 | 1.00 36.86 |
| ATOM | 806 | C | ILE | A | 338 | 24.399 | 16.264 | -2.757 | 1.00 36.65 |
| ATOM | 807 | O | ILE | A | 338 | 23.416 | 15.717 | -2.274 | 1.00 36.93 |
| ATOM | 808 | N | ASN | A | 339 | 25.390 | 15.590 | -3.333 | 1.00 36.23 |
| ATOM | 809 | CA | ASN | A | 339 | 25.360 | 14.133 | -3.477 | 1.00 35.09 |
| ATOM | 810 | CB | ASN | A | 339 | 26.538 | 13.649 | -4.317 | 1.00 34.98 |
| ATOM | 811 | CG | ASN | A | 339 | 26.570 | 14.293 | -5.671 | 1.00 36.29 |
| ATOM | 812 | OD1 | ASN | A | 339 | 26.196 | 13.671 | -6.668 | 1.00 36.99 |
| ATOM | 813 | ND2 | ASN | A | 339 | 26.976 | 15.569 | -5.719 | 1.00 35.43 |

Figure 10

| ATOM | 814 | C | ASN | A | 339 | 25.420 | 13.455 | -2.130 | 1.00 | 34.50 |
| ATOM | 815 | O | ASN | A | 339 | 24.762 | 12.432 | -1.911 | 1.00 | 35.28 |
| ATOM | 816 | N | LYS | A | 340 | 26.233 | 14.010 | -1.237 | 1.00 | 33.61 |
| ATOM | 817 | CA | LYS | A | 340 | 26.382 | 13.444 | 0.092 | 1.00 | 32.85 |
| ATOM | 818 | CB | LYS | A | 340 | 27.631 | 14.024 | 0.763 | 1.00 | 33.96 |
| ATOM | 819 | CG | LYS | A | 340 | 27.928 | 13.442 | 2.135 | 1.00 | 36.92 |
| ATOM | 820 | CD | LYS | A | 340 | 27.937 | 11.907 | 2.151 | 1.00 | 39.02 |
| ATOM | 821 | CE | LYS | A | 340 | 27.777 | 11.379 | 3.592 | 1.00 | 41.03 |
| ATOM | 822 | NZ | LYS | A | 340 | 27.812 | 9.882 | 3.720 | 1.00 | 42.83 |
| ATOM | 823 | C | LYS | A | 340 | 25.101 | 13.666 | 0.917 | 1.00 | 30.68 |
| ATOM | 824 | O | LYS | A | 340 | 24.586 | 12.731 | 1.532 | 1.00 | 29.74 |
| ATOM | 825 | N | LEU | A | 341 | 24.544 | 14.873 | 0.837 | 1.00 | 29.14 |
| ATOM | 826 | CA | LEU | A | 341 | 23.311 | 15.206 | 1.546 | 1.00 | 27.94 |
| ATOM | 827 | CB | LEU | A | 341 | 22.911 | 16.668 | 1.291 | 1.00 | 26.38 |
| ATOM | 828 | CG | LEU | A | 341 | 23.859 | 17.741 | 1.843 | 1.00 | 25.51 |
| ATOM | 829 | CD1 | LEU | A | 341 | 23.310 | 19.129 | 1.585 | 1.00 | 23.48 |
| ATOM | 830 | CD2 | LEU | A | 341 | 24.073 | 17.531 | 3.324 | 1.00 | 24.19 |
| ATOM | 831 | C | LEU | A | 341 | 22.188 | 14.270 | 1.118 | 1.00 | 28.04 |
| ATOM | 832 | O | LEU | A | 341 | 21.466 | 13.731 | 1.956 | 1.00 | 27.65 |
| ATOM | 833 | N | LEU | A | 342 | 22.083 | 14.027 | -0.186 | 1.00 | 28.85 |
| ATOM | 834 | CA | LEU | A | 342 | 21.048 | 13.146 | -0.706 | 1.00 | 29.79 |
| ATOM | 835 | CB | LEU | A | 342 | 20.896 | 13.271 | -2.227 | 1.00 | 31.86 |
| ATOM | 836 | CG | LEU | A | 342 | 20.383 | 14.651 | -2.686 | 1.00 | 33.94 |
| ATOM | 837 | CD1 | LEU | A | 342 | 20.109 | 14.644 | -4.145 | 1.00 | 35.04 |
| ATOM | 838 | CD2 | LEU | A | 342 | 19.121 | 15.034 | -1.968 | 1.00 | 34.35 |
| ATOM | 839 | C | LEU | A | 342 | 21.257 | 11.707 | -0.296 | 1.00 | 30.32 |
| ATOM | 840 | O | LEU | A | 342 | 20.284 | 10.979 | -0.079 | 1.00 | 30.54 |
| ATOM | 841 | N | ASP | A | 343 | 22.508 | 11.286 | -0.155 | 1.00 | 30.08 |
| ATOM | 842 | CA | ASP | A | 343 | 22.712 | 9.921 | 0.278 | 1.00 | 31.39 |
| ATOM | 843 | CB | ASP | A | 343 | 24.138 | 9.435 | 0.061 | 1.00 | 34.87 |
| ATOM | 844 | CG | ASP | A | 343 | 24.240 | 7.914 | 0.207 | 1.00 | 40.54 |
| ATOM | 845 | OD1 | ASP | A | 343 | 23.505 | 7.203 | -0.539 | 1.00 | 43.42 |
| ATOM | 846 | OD2 | ASP | A | 343 | 24.997 | 7.431 | 1.092 | 1.00 | 40.91 |
| ATOM | 847 | C | ASP | A | 343 | 22.330 | 9.771 | 1.752 | 1.00 | 30.54 |
| ATOM | 848 | O | ASP | A | 343 | 21.893 | 8.703 | 2.184 | 1.00 | 29.64 |
| ATOM | 849 | N | MET | A | 344 | 22.501 | 10.841 | 2.522 | 1.00 | 29.53 |
| ATOM | 850 | CA | MET | A | 344 | 22.148 | 10.810 | 3.935 | 1.00 | 28.69 |
| ATOM | 851 | CB | MET | A | 344 | 22.692 | 12.047 | 4.653 | 1.00 | 30.71 |
| ATOM | 852 | CG | MET | A | 344 | 24.218 | 12.129 | 4.742 | 1.00 | 32.04 |
| ATOM | 853 | SD | MET | A | 344 | 24.749 | 13.660 | 5.559 | 1.00 | 36.81 |
| ATOM | 854 | CE | MET | A | 344 | 25.261 | 13.110 | 7.182 | 1.00 | 33.65 |
| ATOM | 855 | C | MET | A | 344 | 20.621 | 10.741 | 4.060 | 1.00 | 26.69 |
| ATOM | 856 | O | MET | A | 344 | 20.090 | 10.052 | 4.937 | 1.00 | 26.20 |
| ATOM | 857 | N | ALA | A | 345 | 19.935 | 11.454 | 3.163 | 1.00 | 25.01 |
| ATOM | 858 | CA | ALA | A | 345 | 18.473 | 11.487 | 3.111 | 1.00 | 23.31 |
| ATOM | 859 | CB | ALA | A | 345 | 17.997 | 12.508 | 2.057 | 1.00 | 22.83 |
| ATOM | 860 | C | ALA | A | 345 | 17.945 | 10.100 | 2.759 | 1.00 | 21.98 |
| ATOM | 861 | O | ALA | A | 345 | 16.918 | 9.671 | 3.277 | 1.00 | 21.04 |
| ATOM | 862 | N | ALA | A | 346 | 18.652 | 9.417 | 1.861 | 1.00 | 21.20 |
| ATOM | 863 | CA | ALA | A | 346 | 18.287 | 8.084 | 1.435 | 1.00 | 20.17 |
| ATOM | 864 | CB | ALA | A | 346 | 19.089 | 7.709 | 0.230 | 1.00 | 19.07 |
| ATOM | 865 | C | ALA | A | 346 | 18.487 | 7.060 | 2.563 | 1.00 | 21.46 |
| ATOM | 866 | O | ALA | A | 346 | 17.786 | 6.051 | 2.613 | 1.00 | 22.66 |
| ATOM | 867 | N | GLN | A | 347 | 19.429 | 7.315 | 3.471 | 1.00 | 22.56 |
| ATOM | 868 | CA | GLN | A | 347 | 19.677 | 6.410 | 4.599 | 1.00 | 23.39 |
| ATOM | 869 | CB | GLN | A | 347 | 21.017 | 6.711 | 5.265 | 1.00 | 26.01 |
| ATOM | 870 | CG | GLN | A | 347 | 22.205 | 6.467 | 4.366 | 1.00 | 29.67 |
| ATOM | 871 | CD | GLN | A | 347 | 23.507 | 6.735 | 5.055 | 1.00 | 32.36 |
| ATOM | 872 | OE1 | GLN | A | 347 | 24.357 | 5.853 | 5.136 | 1.00 | 35.18 |

Figure 10

| | | | | | | | | |
|---|---|---|---|---|---|---|---|---|
|ATOM|873|NE2|GLN|A|347|23.685|7.952|5.552|1.00 31.80|
|ATOM|874|C|GLN|A|347|18.579|6.545|5.633|1.00 22.78|
|ATOM|875|O|GLN|A|347|18.149|5.568|6.247|1.00 23.50|
|ATOM|876|N|ILE|A|348|18.150|7.779|5.845|1.00 22.24|
|ATOM|877|CA|ILE|A|348|17.087|8.067|6.790|1.00 20.97|
|ATOM|878|CB|ILE|A|348|16.922|9.613|6.979|1.00 20.02|
|ATOM|879|CG2|ILE|A|348|15.796|9.937|7.968|1.00 18.85|
|ATOM|880|CG1|ILE|A|348|18.241|10.206|7.488|1.00 19.03|
|ATOM|881|CD1|ILE|A|348|18.211|11.701|7.633|1.00 20.39|
|ATOM|882|C|ILE|A|348|15.805|7.446|6.258|1.00 20.58|
|ATOM|883|O|ILE|A|348|15.023|6.856|7.015|1.00 20.74|
|ATOM|884|N|ALA|A|349|15.603|7.572|4.947|1.00 19.80|
|ATOM|885|CA|ALA|A|349|14.411|7.029|4.304|1.00 20.27|
|ATOM|886|CB|ALA|A|349|14.323|7.502|2.889|1.00 19.48|
|ATOM|887|C|ALA|A|349|14.422|5.506|4.354|1.00 21.48|
|ATOM|888|O|ALA|A|349|13.363|4.878|4.416|1.00 23.63|
|ATOM|889|N|GLU|A|350|15.620|4.921|4.314|1.00 21.46|
|ATOM|890|CA|GLU|A|350|15.798|3.479|4.374|1.00 20.94|
|ATOM|891|CB|GLU|A|350|17.256|3.132|4.116|1.00 23.49|
|ATOM|892|CG|GLU|A|350|17.562|1.655|4.224|1.00 26.11|
|ATOM|893|CD|GLU|A|350|19.031|1.328|4.008|1.00 28.16|
|ATOM|894|OE1|GLU|A|350|19.822|2.225|3.639|1.00 26.91|
|ATOM|895|OE2|GLU|A|350|19.392|0.154|4.215|1.00 30.70|
|ATOM|896|C|GLU|A|350|15.377|2.978|5.748|1.00 21.22|
|ATOM|897|O|GLU|A|350|14.639|2.002|5.851|1.00 21.58|
|ATOM|898|N|GLY|A|351|15.817|3.676|6.799|1.00 21.22|
|ATOM|899|CA|GLY|A|351|15.456|3.301|8.160|1.00 19.71|
|ATOM|900|C|GLY|A|351|13.958|3.426|8.400|1.00 19.33|
|ATOM|901|O|GLY|A|351|13.339|2.567|9.042|1.00 19.64|
|ATOM|902|N|MET|A|352|13.371|4.507|7.891|1.00 18.82|
|ATOM|903|CA|MET|A|352|11.934|4.740|8.031|1.00 17.98|
|ATOM|904|CB|MET|A|352|11.570|6.159|7.592|1.00 16.87|
|ATOM|905|CG|MET|A|352|11.976|7.232|8.586|1.00 17.04|
|ATOM|906|SD|MET|A|352|11.316|7.003|10.252|1.00 18.64|
|ATOM|907|CE|MET|A|352|9.560|6.696|9.941|1.00 14.53|
|ATOM|908|C|MET|A|352|11.142|3.731|7.216|1.00 19.05|
|ATOM|909|O|MET|A|352|10.011|3.391|7.570|1.00 19.70|
|ATOM|910|N|ALA|A|353|11.732|3.289|6.104|1.00 19.98|
|ATOM|911|CA|ALA|A|353|11.123|2.307|5.222|1.00 21.41|
|ATOM|912|CB|ALA|A|353|11.978|2.150|3.975|1.00 20.58|
|ATOM|913|C|ALA|A|353|10.980|0.964|5.976|1.00 23.42|
|ATOM|914|O|ALA|A|353|9.986|0.240|5.823|1.00 24.10|
|ATOM|915|N|PHE|A|354|11.975|0.645|6.799|1.00 24.15|
|ATOM|916|CA|PHE|A|354|11.948|-0.562|7.610|1.00 25.19|
|ATOM|917|CB|PHE|A|354|13.330|-0.817|8.198|1.00 26.95|
|ATOM|918|CG|PHE|A|354|13.376|-1.955|9.164|1.00 28.33|
|ATOM|919|CD1|PHE|A|354|13.225|-3.262|8.725|1.00 29.32|
|ATOM|920|CD2|PHE|A|354|13.625|-1.716|10.515|1.00 29.70|
|ATOM|921|CE1|PHE|A|354|13.325|-4.327|9.618|1.00 31.39|
|ATOM|922|CE2|PHE|A|354|13.727|-2.764|11.420|1.00 32.36|
|ATOM|923|CZ|PHE|A|354|13.581|-4.079|10.973|1.00 32.07|
|ATOM|924|C|PHE|A|354|10.931|-0.380|8.735|1.00 25.06|
|ATOM|925|O|PHE|A|354|10.226|-1.322|9.094|1.00 25.54|
|ATOM|926|N|ILE|A|355|10.878|0.825|9.305|1.00 24.80|
|ATOM|927|CA|ILE|A|355|9.921|1.128|10.376|1.00 25.30|
|ATOM|928|CB|ILE|A|355|10.200|2.549|10.981|1.00 25.44|
|ATOM|929|CG2|ILE|A|355|8.985|3.090|11.756|1.00 22.51|
|ATOM|930|CG1|ILE|A|355|11.477|2.484|11.839|1.00 26.53|
|ATOM|931|CD1|ILE|A|355|11.988|3.810|12.374|1.00 25.31|

Figure 10

| | | | | | | | | | |
|---|---|---|---|---|---|---|---|---|---|
| ATOM | 932 | C | ILE | A | 355 | 8.486 | 1.005 | 9.836 | 1.00 25.91 |
| ATOM | 933 | O | ILE | A | 355 | 7.588 | 0.497 | 10.501 | 1.00 25.33 |
| ATOM | 934 | N | GLU | A | 356 | 8.298 | 1.449 | 8.602 | 1.00 26.96 |
| ATOM | 935 | CA | GLU | A | 356 | 7.013 | 1.377 | 7.918 | 1.00 27.80 |
| ATOM | 936 | CB | GLU | A | 356 | 7.151 | 2.141 | 6.624 | 1.00 26.00 |
| ATOM | 937 | CG | GLU | A | 356 | 5.987 | 2.081 | 5.679 | 1.00 22.69 |
| ATOM | 938 | CD | GLU | A | 356 | 6.260 | 2.964 | 4.476 | 1.00 22.26 |
| ATOM | 939 | OE1 | GLU | A | 356 | 6.935 | 2.519 | 3.520 | 1.00 23.34 |
| ATOM | 940 | OE2 | GLU | A | 356 | 5.862 | 4.136 | 4.507 | 1.00 23.65 |
| ATOM | 941 | C | GLU | A | 356 | 6.687 | -0.081 | 7.630 | 1.00 30.24 |
| ATOM | 942 | O | GLU | A | 356 | 5.574 | -0.549 | 7.850 | 1.00 31.85 |
| ATOM | 943 | N | GLU | A | 357 | 7.691 | -0.787 | 7.136 | 1.00 31.79 |
| ATOM | 944 | CA | GLU | A | 357 | 7.599 | -2.203 | 6.815 | 1.00 33.76 |
| ATOM | 945 | CB | GLU | A | 357 | 8.981 | -2.667 | 6.321 | 1.00 35.68 |
| ATOM | 946 | CG | GLU | A | 357 | 9.282 | -4.145 | 6.477 | 1.00 41.23 |
| ATOM | 947 | CD | GLU | A | 357 | 8.480 | -5.004 | 5.525 | 1.00 45.10 |
| ATOM | 948 | OE1 | GLU | A | 357 | 8.403 | -4.633 | 4.323 | 1.00 47.00 |
| ATOM | 949 | OE2 | GLU | A | 357 | 7.937 | -6.045 | 5.984 | 1.00 45.46 |
| ATOM | 950 | C | GLU | A | 357 | 7.128 | -3.047 | 7.994 | 1.00 33.61 |
| ATOM | 951 | O | GLU | A | 357 | 6.303 | -3.955 | 7.833 | 1.00 33.84 |
| ATOM | 952 | N | ARG | A | 358 | 7.512 | -2.660 | 9.194 | 1.00 33.99 |
| ATOM | 953 | CA | ARG | A | 358 | 7.192 | -3.403 | 10.371 | 1.00 34.91 |
| ATOM | 954 | CB | ARG | A | 358 | 8.429 | -3.491 | 11.273 | 1.00 36.56 |
| ATOM | 955 | CG | ARG | A | 358 | 9.630 | -4.216 | 10.621 | 1.00 41.02 |
| ATOM | 956 | CD | ARG | A | 358 | 9.411 | -5.732 | 10.597 | 1.00 44.66 |
| ATOM | 957 | NE | ARG | A | 358 | 9.541 | -6.234 | 11.958 | 1.00 50.60 |
| ATOM | 958 | CZ | ARG | A | 358 | 10.695 | -6.622 | 12.502 | 1.00 53.67 |
| ATOM | 959 | NH1 | ARG | A | 358 | 11.818 | -6.600 | 11.784 | 1.00 54.51 |
| ATOM | 960 | NH2 | ARG | A | 358 | 10.760 | -6.890 | 13.806 | 1.00 54.23 |
| ATOM | 961 | C | ARG | A | 358 | 6.011 | -2.819 | 11.108 | 1.00 35.48 |
| ATOM | 962 | O | ARG | A | 358 | 5.791 | -3.128 | 12.260 | 1.00 35.92 |
| ATOM | 963 | N | ASN | A | 359 | 5.312 | -1.946 | 10.394 | 1.00 35.79 |
| ATOM | 964 | CA | ASN | A | 359 | 4.115 | -1.263 | 10.897 | 1.00 35.62 |
| ATOM | 965 | CB | ASN | A | 359 | 2.932 | -2.222 | 10.894 | 1.00 40.05 |
| ATOM | 966 | CG | ASN | A | 359 | 2.781 | -2.956 | 9.561 | 1.00 45.32 |
| ATOM | 967 | OD1 | ASN | A | 359 | 2.336 | -2.374 | 8.561 | 1.00 47.95 |
| ATOM | 968 | ND2 | ASN | A | 359 | 3.174 | -4.231 | 9.537 | 1.00 47.65 |
| ATOM | 969 | C | ASN | A | 359 | 4.275 | -0.554 | 12.221 | 1.00 34.67 |
| ATOM | 970 | O | ASN | A | 359 | 3.531 | -0.779 | 13.178 | 1.00 34.28 |
| ATOM | 971 | N | TYR | A | 360 | 5.288 | 0.301 | 12.272 | 1.00 34.20 |
| ATOM | 972 | CA | TYR | A | 360 | 5.571 | 1.135 | 13.436 | 1.00 33.60 |
| ATOM | 973 | CB | TYR | A | 360 | 6.975 | 0.863 | 13.983 | 1.00 36.02 |
| ATOM | 974 | CG | TYR | A | 360 | 7.044 | -0.292 | 14.936 | 1.00 38.98 |
| ATOM | 975 | CD1 | TYR | A | 360 | 7.371 | -1.565 | 14.489 | 1.00 40.16 |
| ATOM | 976 | CE1 | TYR | A | 360 | 7.424 | -2.641 | 15.359 | 1.00 40.64 |
| ATOM | 977 | CD2 | TYR | A | 360 | 6.771 | -0.116 | 16.285 | 1.00 40.99 |
| ATOM | 978 | CE2 | TYR | A | 360 | 6.820 | -1.183 | 17.168 | 1.00 42.04 |
| ATOM | 979 | CZ | TYR | A | 360 | 7.147 | -2.446 | 16.701 | 1.00 42.02 |
| ATOM | 980 | OH | TYR | A | 360 | 7.207 | -3.508 | 17.588 | 1.00 43.32 |
| ATOM | 981 | C | TYR | A | 360 | 5.521 | 2.562 | 12.926 | 1.00 32.16 |
| ATOM | 982 | O | TYR | A | 360 | 5.301 | 2.792 | 11.735 | 1.00 30.63 |
| ATOM | 983 | N | ILE | A | 361 | 5.621 | 3.512 | 13.851 | 1.00 30.98 |
| ATOM | 984 | CA | ILE | A | 361 | 5.670 | 4.929 | 13.513 | 1.00 29.93 |
| ATOM | 985 | CB | ILE | A | 361 | 4.317 | 5.678 | 13.694 | 1.00 29.25 |
| ATOM | 986 | CG2 | ILE | A | 361 | 3.238 | 4.993 | 12.871 | 1.00 28.95 |
| ATOM | 987 | CG1 | ILE | A | 361 | 3.930 | 5.807 | 15.175 | 1.00 30.19 |
| ATOM | 988 | CD1 | ILE | A | 361 | 2.834 | 6.851 | 15.457 | 1.00 27.24 |
| ATOM | 989 | C | ILE | A | 361 | 6.759 | 5.540 | 14.392 | 1.00 30.53 |
| ATOM | 990 | O | ILE | A | 361 | 7.168 | 4.938 | 15.389 | 1.00 32.21 |

Figure 10

| ATOM | 991  | N   | HIS A 362 | 7.306  | 6.674  | 13.964 | 1.00 | 29.75 |
| ATOM | 992  | CA  | HIS A 362 | 8.351  | 7.356  | 14.713 | 1.00 | 27.43 |
| ATOM | 993  | CB  | HIS A 362 | 9.319  | 8.015  | 13.745 | 1.00 | 24.89 |
| ATOM | 994  | CG  | HIS A 362 | 10.580 | 8.507  | 14.385 | 1.00 | 22.21 |
| ATOM | 995  | CD2 | HIS A 362 | 11.876 | 8.215  | 14.132 | 1.00 | 22.10 |
| ATOM | 996  | ND1 | HIS A 362 | 10.592 | 9.430  | 15.402 | 1.00 | 21.94 |
| ATOM | 997  | CE1 | HIS A 362 | 11.841 | 9.691  | 15.751 | 1.00 | 19.02 |
| ATOM | 998  | NE2 | HIS A 362 | 12.638 | 8.967  | 14.996 | 1.00 | 20.64 |
| ATOM | 999  | C   | HIS A 362 | 7.717  | 8.408  | 15.608 | 1.00 | 27.87 |
| ATOM | 1000 | O   | HIS A 362 | 7.871  | 8.369  | 16.819 | 1.00 | 29.15 |
| ATOM | 1001 | N   | ARG A 363 | 6.918  | 9.267  | 14.983 | 1.00 | 27.92 |
| ATOM | 1002 | CA  | ARG A 363 | 6.201  | 10.404 | 15.571 | 1.00 | 28.36 |
| ATOM | 1003 | CB  | ARG A 363 | 5.097  | 10.022 | 16.583 | 1.00 | 29.35 |
| ATOM | 1004 | CG  | ARG A 363 | 5.517  | 9.328  | 17.851 | 1.00 | 35.49 |
| ATOM | 1005 | CD  | ARG A 363 | 4.309  | 8.828  | 18.672 | 1.00 | 38.82 |
| ATOM | 1006 | NE  | ARG A 363 | 3.621  | 9.907  | 19.371 | 1.00 | 40.41 |
| ATOM | 1007 | CZ  | ARG A 363 | 2.304  | 10.062 | 19.384 | 1.00 | 42.08 |
| ATOM | 1008 | NH1 | ARG A 363 | 1.530  | 9.200  | 18.742 | 1.00 | 41.74 |
| ATOM | 1009 | NH2 | ARG A 363 | 1.760  | 11.098 | 20.018 | 1.00 | 42.43 |
| ATOM | 1010 | C   | ARG A 363 | 7.058  | 11.559 | 16.046 | 1.00 | 27.33 |
| ATOM | 1011 | O   | ARG A 363 | 6.530  | 12.624 | 16.367 | 1.00 | 27.68 |
| ATOM | 1012 | N   | ASP A 364 | 8.377  | 11.394 | 15.952 | 1.00 | 25.52 |
| ATOM | 1013 | CA  | ASP A 364 | 9.325  | 12.432 | 16.354 | 1.00 | 24.44 |
| ATOM | 1014 | CB  | ASP A 364 | 9.894  | 12.124 | 17.747 | 1.00 | 25.09 |
| ATOM | 1015 | CG  | ASP A 364 | 8.869  | 12.319 | 18.848 | 1.00 | 25.46 |
| ATOM | 1016 | OD1 | ASP A 364 | 8.442  | 13.466 | 19.056 | 1.00 | 28.98 |
| ATOM | 1017 | OD2 | ASP A 364 | 8.487  | 11.336 | 19.508 | 1.00 | 26.55 |
| ATOM | 1018 | C   | ASP A 364 | 10.451 | 12.581 | 15.328 | 1.00 | 23.46 |
| ATOM | 1019 | O   | ASP A 364 | 11.596 | 12.878 | 15.664 | 1.00 | 23.59 |
| ATOM | 1020 | N   | LEU A 365 | 10.104 | 12.413 | 14.061 | 1.00 | 23.01 |
| ATOM | 1021 | CA  | LEU A 365 | 11.079 | 12.508 | 12.986 | 1.00 | 22.35 |
| ATOM | 1022 | CB  | LEU A 365 | 10.573 | 11.758 | 11.746 | 1.00 | 18.58 |
| ATOM | 1023 | CG  | LEU A 365 | 11.593 | 11.575 | 10.612 | 1.00 | 19.10 |
| ATOM | 1024 | CD1 | LEU A 365 | 12.890 | 10.867 | 11.108 | 1.00 | 17.62 |
| ATOM | 1025 | CD2 | LEU A 365 | 10.923 | 10.793 | 9.491  | 1.00 | 16.31 |
| ATOM | 1026 | C   | LEU A 365 | 11.495 | 13.946 | 12.623 | 1.00 | 22.90 |
| ATOM | 1027 | O   | LEU A 365 | 10.672 | 14.774 | 12.209 | 1.00 | 23.64 |
| ATOM | 1028 | N   | ARG A 366 | 12.782 | 14.228 | 12.817 | 1.00 | 22.31 |
| ATOM | 1029 | CA  | ARG A 366 | 13.394 | 15.515 | 12.501 | 1.00 | 22.74 |
| ATOM | 1030 | CB  | ARG A 366 | 13.031 | 16.600 | 13.528 | 1.00 | 24.00 |
| ATOM | 1031 | CG  | ARG A 366 | 13.076 | 16.242 | 15.003 | 1.00 | 25.73 |
| ATOM | 1032 | CD  | ARG A 366 | 12.805 | 17.507 | 15.794 | 1.00 | 29.46 |
| ATOM | 1033 | NE  | ARG A 366 | 12.579 | 17.284 | 17.217 | 1.00 | 35.33 |
| ATOM | 1034 | CZ  | ARG A 366 | 11.467 | 16.763 | 17.736 | 1.00 | 37.83 |
| ATOM | 1035 | NH1 | ARG A 366 | 10.454 | 16.385 | 16.952 | 1.00 | 40.30 |
| ATOM | 1036 | NH2 | ARG A 366 | 11.357 | 16.648 | 19.050 | 1.00 | 37.32 |
| ATOM | 1037 | C   | ARG A 366 | 14.893 | 15.290 | 12.446 | 1.00 | 21.92 |
| ATOM | 1038 | O   | ARG A 366 | 15.358 | 14.217 | 12.807 | 1.00 | 21.39 |
| ATOM | 1039 | N   | ALA A 367 | 15.654 | 16.268 | 11.969 | 1.00 | 21.42 |
| ATOM | 1040 | CA  | ALA A 367 | 17.100 | 16.093 | 11.903 | 1.00 | 21.30 |
| ATOM | 1041 | CB  | ALA A 367 | 17.731 | 17.176 | 11.063 | 1.00 | 20.49 |
| ATOM | 1042 | C   | ALA A 367 | 17.749 | 16.016 | 13.297 | 1.00 | 21.94 |
| ATOM | 1043 | O   | ALA A 367 | 18.786 | 15.381 | 13.465 | 1.00 | 21.86 |
| ATOM | 1044 | N   | ALA A 368 | 17.116 | 16.621 | 14.303 | 1.00 | 22.49 |
| ATOM | 1045 | CA  | ALA A 368 | 17.636 | 16.578 | 15.673 | 1.00 | 22.13 |
| ATOM | 1046 | CB  | ALA A 368 | 16.762 | 17.384 | 16.595 | 1.00 | 20.38 |
| ATOM | 1047 | C   | ALA A 368 | 17.688 | 15.146 | 16.164 | 1.00 | 22.83 |
| ATOM | 1048 | O   | ALA A 368 | 18.569 | 14.781 | 16.944 | 1.00 | 23.85 |
| ATOM | 1049 | N   | ASN A 369 | 16.768 | 14.325 | 15.665 | 1.00 | 23.06 |

Figure 10

| ATOM | 1050 | CA  | ASN A 369 | 16.688 | 12.935 | 16.079 | 1.00 | 22.73 |
|------|------|-----|-----------|--------|--------|--------|------|-------|
| ATOM | 1051 | CB  | ASN A 369 | 15.248 | 12.592 | 16.406 | 1.00 | 22.21 |
| ATOM | 1052 | CG  | ASN A 369 | 14.735 | 13.415 | 17.554 | 1.00 | 23.02 |
| ATOM | 1053 | OD1 | ASN A 369 | 15.418 | 13.560 | 18.570 | 1.00 | 23.73 |
| ATOM | 1054 | ND2 | ASN A 369 | 13.553 | 13.996 | 17.396 | 1.00 | 23.88 |
| ATOM | 1055 | C   | ASN A 369 | 17.333 | 11.903 | 15.166 | 1.00 | 23.24 |
| ATOM | 1056 | O   | ASN A 369 | 16.971 | 10.722 | 15.196 | 1.00 | 24.79 |
| ATOM | 1057 | N   | ILE A 370 | 18.260 | 12.371 | 14.332 | 1.00 | 22.61 |
| ATOM | 1058 | CA  | ILE A 370 | 19.045 | 11.517 | 13.443 | 1.00 | 22.33 |
| ATOM | 1059 | CB  | ILE A 370 | 19.051 | 12.000 | 11.965 | 1.00 | 21.73 |
| ATOM | 1060 | CG2 | ILE A 370 | 19.910 | 11.057 | 11.128 | 1.00 | 18.36 |
| ATOM | 1061 | CG1 | ILE A 370 | 17.626 | 12.081 | 11.403 | 1.00 | 19.68 |
| ATOM | 1062 | CD1 | ILE A 370 | 16.887 | 10.759 | 11.425 | 1.00 | 19.34 |
| ATOM | 1063 | C   | ILE A 370 | 20.471 | 11.680 | 13.970 | 1.00 | 22.82 |
| ATOM | 1064 | O   | ILE A 370 | 20.892 | 12.792 | 14.279 | 1.00 | 22.72 |
| ATOM | 1065 | N   | LEU A 371 | 21.214 | 10.581 | 14.065 | 1.00 | 24.39 |
| ATOM | 1066 | CA  | LEU A 371 | 22.589 | 10.616 | 14.575 | 1.00 | 24.85 |
| ATOM | 1067 | CB  | LEU A 371 | 22.736 | 9.638  | 15.754 | 1.00 | 23.61 |
| ATOM | 1068 | CG  | LEU A 371 | 21.883 | 9.913  | 17.008 | 1.00 | 22.45 |
| ATOM | 1069 | CD1 | LEU A 371 | 22.072 | 8.816  | 18.029 | 1.00 | 20.98 |
| ATOM | 1070 | CD2 | LEU A 371 | 22.263 | 11.253 | 17.615 | 1.00 | 22.92 |
| ATOM | 1071 | C   | LEU A 371 | 23.588 | 10.298 | 13.462 | 1.00 | 26.06 |
| ATOM | 1072 | O   | LEU A 371 | 23.314 | 9.471  | 12.601 | 1.00 | 26.91 |
| ATOM | 1073 | N   | VAL A 372 | 24.727 | 10.986 | 13.476 | 1.00 | 27.77 |
| ATOM | 1074 | CA  | VAL A 372 | 25.783 | 10.816 | 12.467 | 1.00 | 30.21 |
| ATOM | 1075 | CB  | VAL A 372 | 26.200 | 12.188 | 11.849 | 1.00 | 30.13 |
| ATOM | 1076 | CG1 | VAL A 372 | 27.124 | 11.988 | 10.667 | 1.00 | 29.97 |
| ATOM | 1077 | CG2 | VAL A 372 | 24.971 | 12.959 | 11.415 | 1.00 | 28.60 |
| ATOM | 1078 | C   | VAL A 372 | 27.028 | 10.116 | 13.031 | 1.00 | 31.56 |
| ATOM | 1079 | O   | VAL A 372 | 27.569 | 10.507 | 14.071 | 1.00 | 32.68 |
| ATOM | 1080 | N   | SER A 373 | 27.478 | 9.079  | 12.337 | 1.00 | 32.55 |
| ATOM | 1081 | CA  | SER A 373 | 28.633 | 8.309  | 12.772 | 1.00 | 35.71 |
| ATOM | 1082 | CB  | SER A 373 | 28.535 | 6.887  | 12.226 | 1.00 | 36.20 |
| ATOM | 1083 | OG  | SER A 373 | 28.772 | 6.878  | 10.822 | 1.00 | 38.07 |
| ATOM | 1084 | C   | SER A 373 | 29.931 | 8.931  | 12.280 | 1.00 | 37.65 |
| ATOM | 1085 | O   | SER A 373 | 29.913 | 9.844  | 11.462 | 1.00 | 38.38 |
| ATOM | 1086 | N   | ASP A 374 | 31.058 | 8.396  | 12.741 | 1.00 | 39.47 |
| ATOM | 1087 | CA  | ASP A 374 | 32.372 | 8.882  | 12.322 | 1.00 | 41.23 |
| ATOM | 1088 | CB  | ASP A 374 | 33.473 | 8.099  | 13.027 | 1.00 | 43.17 |
| ATOM | 1089 | CG  | ASP A 374 | 33.294 | 6.606  | 12.890 | 1.00 | 46.88 |
| ATOM | 1090 | OD1 | ASP A 374 | 32.339 | 6.067  | 13.496 | 1.00 | 50.35 |
| ATOM | 1091 | OD2 | ASP A 374 | 34.094 | 5.973  | 12.170 | 1.00 | 48.63 |
| ATOM | 1092 | C   | ASP A 374 | 32.536 | 8.742  | 10.809 | 1.00 | 41.57 |
| ATOM | 1093 | O   | ASP A 374 | 33.258 | 9.517  | 10.182 | 1.00 | 41.77 |
| ATOM | 1094 | N   | THR A 375 | 31.850 | 7.758  | 10.231 | 1.00 | 41.19 |
| ATOM | 1095 | CA  | THR A 375 | 31.902 | 7.516  | 8.792  | 1.00 | 41.30 |
| ATOM | 1096 | CB  | THR A 375 | 31.716 | 6.029  | 8.473  | 1.00 | 41.83 |
| ATOM | 1097 | OG1 | THR A 375 | 30.470 | 5.572  | 9.015  | 1.00 | 41.14 |
| ATOM | 1098 | CG2 | THR A 375 | 32.853 | 5.221  | 9.080  | 1.00 | 42.87 |
| ATOM | 1099 | C   | THR A 375 | 30.848 | 8.328  | 8.035  | 1.00 | 41.29 |
| ATOM | 1100 | O   | THR A 375 | 30.617 | 8.115  | 6.834  | 1.00 | 41.63 |
| ATOM | 1101 | N   | LEU A 376 | 30.222 | 9.262  | 8.751  | 1.00 | 39.97 |
| ATOM | 1102 | CA  | LEU A 376 | 29.193 | 10.149 | 8.210  | 1.00 | 38.76 |
| ATOM | 1103 | CB  | LEU A 376 | 29.786 | 11.088 | 7.152  | 1.00 | 37.94 |
| ATOM | 1104 | CG  | LEU A 376 | 31.098 | 11.819 | 7.499  | 1.00 | 37.69 |
| ATOM | 1105 | CD1 | LEU A 376 | 31.214 | 13.088 | 6.662  | 1.00 | 38.53 |
| ATOM | 1106 | CD2 | LEU A 376 | 31.158 | 12.192 | 8.966  | 1.00 | 37.72 |
| ATOM | 1107 | C   | LEU A 376 | 27.933 | 9.449  | 7.681  | 1.00 | 38.81 |
| ATOM | 1108 | O   | LEU A 376 | 27.284 | 9.942  | 6.753  | 1.00 | 38.86 |

Figure 10

| ATOM | 1109 | N   | SER | A | 377 | 27.614 | 8.284  | 8.253  | 1.00 | 38.19 |
| ATOM | 1110 | CA  | SER | A | 377 | 26.413 | 7.541  | 7.880  | 1.00 | 37.56 |
| ATOM | 1111 | CB  | SER | A | 377 | 26.659 | 6.025  | 7.866  | 1.00 | 39.69 |
| ATOM | 1112 | OG  | SER | A | 377 | 26.619 | 5.480  | 9.177  | 1.00 | 42.09 |
| ATOM | 1113 | C   | SER | A | 377 | 25.347 | 7.887  | 8.923  | 1.00 | 35.63 |
| ATOM | 1114 | O   | SER | A | 377 | 25.654 | 8.048  | 10.100 | 1.00 | 34.31 |
| ATOM | 1115 | N   | CYS | A | 378 | 24.094 | 7.967  | 8.485  | 1.00 | 34.65 |
| ATOM | 1116 | CA  | CYS | A | 378 | 23.004 | 8.328  | 9.369  | 1.00 | 32.10 |
| ATOM | 1117 | CB  | CYS | A | 378 | 22.043 | 9.263  | 8.638  | 1.00 | 32.07 |
| ATOM | 1118 | SG  | CYS | A | 378 | 22.776 | 10.818 | 8.135  | 1.00 | 30.35 |
| ATOM | 1119 | C   | CYS | A | 378 | 22.237 | 7.139  | 9.923  | 1.00 | 30.78 |
| ATOM | 1120 | O   | CYS | A | 378 | 22.039 | 6.143  | 9.217  | 1.00 | 30.18 |
| ATOM | 1121 | N   | LYS | A | 379 | 21.854 | 7.265  | 11.203 | 1.00 | 29.13 |
| ATOM | 1122 | CA  | LYS | A | 379 | 21.061 | 6.287  | 11.960 | 1.00 | 27.46 |
| ATOM | 1123 | CB  | LYS | A | 379 | 21.927 | 5.527  | 12.975 | 1.00 | 25.51 |
| ATOM | 1124 | CG  | LYS | A | 379 | 22.503 | 4.212  | 12.442 | 1.00 | 24.89 |
| ATOM | 1125 | CD  | LYS | A | 379 | 23.681 | 3.716  | 13.278 | 1.00 | 25.83 |
| ATOM | 1126 | CE  | LYS | A | 379 | 24.264 | 2.384  | 12.791 | 1.00 | 25.30 |
| ATOM | 1127 | NZ  | LYS | A | 379 | 23.479 | 1.208  | 13.332 | 1.00 | 28.60 |
| ATOM | 1128 | C   | LYS | A | 379 | 19.915 | 7.032  | 12.666 | 1.00 | 27.15 |
| ATOM | 1129 | O   | LYS | A | 379 | 20.091 | 8.145  | 13.168 | 1.00 | 27.17 |
| ATOM | 1130 | N   | ILE | A | 380 | 18.740 | 6.414  | 12.688 | 1.00 | 26.94 |
| ATOM | 1131 | CA  | ILE | A | 380 | 17.545 | 7.006  | 13.292 | 1.00 | 27.18 |
| ATOM | 1132 | CB  | ILE | A | 380 | 16.243 | 6.477  | 12.584 | 1.00 | 25.98 |
| ATOM | 1133 | CG2 | ILE | A | 380 | 15.006 | 7.095  | 13.198 | 1.00 | 24.46 |
| ATOM | 1134 | CG1 | ILE | A | 380 | 16.284 | 6.789  | 11.087 | 1.00 | 26.21 |
| ATOM | 1135 | CD1 | ILE | A | 380 | 15.093 | 6.309  | 10.354 | 1.00 | 25.27 |
| ATOM | 1136 | C   | ILE | A | 380 | 17.457 | 6.704  | 14.789 | 1.00 | 27.18 |
| ATOM | 1137 | O   | ILE | A | 380 | 17.589 | 5.550  | 15.201 | 1.00 | 28.36 |
| ATOM | 1138 | N   | ALA | A | 381 | 17.229 | 7.733  | 15.601 | 1.00 | 26.77 |
| ATOM | 1139 | CA  | ALA | A | 381 | 17.109 | 7.541  | 17.041 | 1.00 | 26.33 |
| ATOM | 1140 | CB  | ALA | A | 381 | 18.174 | 8.340  | 17.776 | 1.00 | 25.38 |
| ATOM | 1141 | C   | ALA | A | 381 | 15.732 | 7.952  | 17.521 | 1.00 | 26.94 |
| ATOM | 1142 | O   | ALA | A | 381 | 14.970 | 8.600  | 16.784 | 1.00 | 27.32 |
| ATOM | 1143 | N   | ASP | A | 382 | 15.440 | 7.569  | 18.767 | 1.00 | 27.04 |
| ATOM | 1144 | CA  | ASP | A | 382 | 14.189 | 7.875  | 19.471 | 1.00 | 27.16 |
| ATOM | 1145 | CB  | ASP | A | 382 | 14.240 | 9.293  | 20.028 | 1.00 | 25.60 |
| ATOM | 1146 | CG  | ASP | A | 382 | 15.162 | 9.400  | 21.188 | 1.00 | 25.51 |
| ATOM | 1147 | OD1 | ASP | A | 382 | 15.094 | 8.518  | 22.057 | 1.00 | 26.71 |
| ATOM | 1148 | OD2 | ASP | A | 382 | 15.976 | 10.332 | 21.239 | 1.00 | 26.26 |
| ATOM | 1149 | C   | ASP | A | 382 | 12.886 | 7.644  | 18.730 | 1.00 | 27.85 |
| ATOM | 1150 | O   | ASP | A | 382 | 11.986 | 8.494  | 18.752 | 1.00 | 27.11 |
| ATOM | 1151 | N   | PHE | A | 383 | 12.757 | 6.449  | 18.162 | 1.00 | 28.81 |
| ATOM | 1152 | CA  | PHE | A | 383 | 11.572 | 6.078  | 17.392 | 1.00 | 30.20 |
| ATOM | 1153 | CB  | PHE | A | 383 | 12.018 | 5.400  | 16.096 | 1.00 | 30.03 |
| ATOM | 1154 | CG  | PHE | A | 383 | 12.969 | 4.270  | 16.314 | 1.00 | 30.31 |
| ATOM | 1155 | CD1 | PHE | A | 383 | 12.486 | 3.007  | 16.646 | 1.00 | 32.45 |
| ATOM | 1156 | CD2 | PHE | A | 383 | 14.343 | 4.467  | 16.231 | 1.00 | 28.77 |
| ATOM | 1157 | CE1 | PHE | A | 383 | 13.349 | 1.958  | 16.898 | 1.00 | 32.57 |
| ATOM | 1158 | CE2 | PHE | A | 383 | 15.228 | 3.421  | 16.480 | 1.00 | 30.47 |
| ATOM | 1159 | CZ  | PHE | A | 383 | 14.727 | 2.160  | 16.818 | 1.00 | 32.40 |
| ATOM | 1160 | C   | PHE | A | 383 | 10.562 | 5.202  | 18.136 | 1.00 | 30.83 |
| ATOM | 1161 | O   | PHE | A | 383 | 10.917 | 4.471  | 19.052 | 1.00 | 31.57 |
| ATOM | 1162 | N   | GLY | A | 384 | 9.295  | 5.326  | 17.762 | 1.00 | 32.14 |
| ATOM | 1163 | CA  | GLY | A | 384 | 8.255  | 4.533  | 18.380 | 1.00 | 34.02 |
| ATOM | 1164 | C   | GLY | A | 384 | 7.871  | 4.950  | 19.786 | 1.00 | 35.85 |
| ATOM | 1165 | O   | GLY | A | 384 | 7.176  | 4.205  | 20.469 | 1.00 | 36.82 |
| ATOM | 1166 | N   | LEU | A | 385 | 8.300  | 6.131  | 20.224 | 1.00 | 36.10 |
| ATOM | 1167 | CA  | LEU | A | 385 | 7.974  | 6.603  | 21.567 | 1.00 | 36.05 |

Figure 10

| | | | | | | | | | |
|---|---|---|---|---|---|---|---|---|---|
| ATOM | 1168 | CB | LEU | A | 385 | 8.810 | 7.838 | 21.930 | 1.00 34.80 |
| ATOM | 1169 | CG | LEU | A | 385 | 10.331 | 7.707 | 21.773 | 1.00 33.73 |
| ATOM | 1170 | CD1 | LEU | A | 385 | 11.008 | 9.008 | 22.136 | 1.00 32.13 |
| ATOM | 1171 | CD2 | LEU | A | 385 | 10.857 | 6.577 | 22.619 | 1.00 34.21 |
| ATOM | 1172 | C | LEU | A | 385 | 6.492 | 6.930 | 21.652 | 1.00 37.09 |
| ATOM | 1173 | O | LEU | A | 385 | 5.892 | 7.368 | 20.673 | 1.00 37.29 |
| ATOM | 1174 | N | ALA | A | 386 | 5.909 | 6.686 | 22.825 | 1.00 38.65 |
| ATOM | 1175 | CA | ALA | A | 386 | 4.490 | 6.929 | 23.082 | 1.00 39.23 |
| ATOM | 1176 | CB | ALA | A | 386 | 4.088 | 6.257 | 24.383 | 1.00 40.24 |
| ATOM | 1177 | C | ALA | A | 386 | 4.146 | 8.396 | 23.170 | 1.00 38.90 |
| ATOM | 1178 | O | ALA | A | 386 | 2.975 | 8.782 | 23.066 | 1.00 40.32 |
| ATOM | 1179 | N | ARG | A | 387 | 5.172 | 9.211 | 23.367 | 1.00 37.25 |
| ATOM | 1180 | CA | ARG | A | 387 | 4.984 | 10.638 | 23.533 | 1.00 34.26 |
| ATOM | 1181 | CB | ARG | A | 387 | 5.418 | 11.017 | 24.944 | 1.00 32.40 |
| ATOM | 1182 | CG | ARG | A | 387 | 6.868 | 10.663 | 25.198 | 1.00 31.46 |
| ATOM | 1183 | CD | ARG | A | 387 | 7.292 | 11.011 | 26.585 | 1.00 31.65 |
| ATOM | 1184 | NE | ARG | A | 387 | 8.741 | 11.010 | 26.748 | 1.00 30.64 |
| ATOM | 1185 | CZ | ARG | A | 387 | 9.495 | 12.097 | 26.638 | 1.00 31.24 |
| ATOM | 1186 | NH1 | ARG | A | 387 | 8.936 | 13.274 | 26.354 | 1.00 30.62 |
| ATOM | 1187 | NH2 | ARG | A | 387 | 10.801 | 12.010 | 26.853 | 1.00 30.95 |
| ATOM | 1188 | C | ARG | A | 387 | 5.753 | 11.484 | 22.549 | 1.00 33.08 |
| ATOM | 1189 | O | ARG | A | 387 | 6.612 | 10.997 | 21.815 | 1.00 33.34 |
| ATOM | 1190 | N | LEU | A | 388 | 5.430 | 12.773 | 22.573 | 1.00 32.62 |
| ATOM | 1191 | CA | LEU | A | 388 | 6.075 | 13.782 | 21.746 | 1.00 31.59 |
| ATOM | 1192 | CB | LEU | A | 388 | 5.049 | 14.840 | 21.359 | 1.00 32.12 |
| ATOM | 1193 | CG | LEU | A | 388 | 3.803 | 14.203 | 20.725 | 1.00 33.86 |
| ATOM | 1194 | CD1 | LEU | A | 388 | 2.770 | 15.263 | 20.386 | 1.00 33.82 |
| ATOM | 1195 | CD2 | LEU | A | 388 | 4.203 | 13.437 | 19.479 | 1.00 33.25 |
| ATOM | 1196 | C | LEU | A | 388 | 7.232 | 14.389 | 22.557 | 1.00 30.10 |
| ATOM | 1197 | O | LEU | A | 388 | 7.020 | 14.988 | 23.616 | 1.00 30.90 |
| ATOM | 1198 | N | ILE | A | 389 | 8.455 | 14.155 | 22.092 | 1.00 28.18 |
| ATOM | 1199 | CA | ILE | A | 389 | 9.657 | 14.635 | 22.762 | 1.00 26.62 |
| ATOM | 1200 | CB | ILE | A | 389 | 10.817 | 13.607 | 22.637 | 1.00 23.96 |
| ATOM | 1201 | CG2 | ILE | A | 389 | 10.343 | 12.241 | 23.089 | 1.00 24.04 |
| ATOM | 1202 | CG1 | ILE | A | 389 | 11.354 | 13.542 | 21.203 | 1.00 21.70 |
| ATOM | 1203 | CD1 | ILE | A | 389 | 12.466 | 12.550 | 21.016 | 1.00 17.64 |
| ATOM | 1204 | C | ILE | A | 389 | 10.156 | 15.994 | 22.294 | 1.00 27.92 |
| ATOM | 1205 | O | ILE | A | 389 | 9.889 | 16.424 | 21.177 | 1.00 28.32 |
| ATOM | 1206 | N | GLU | A | 390 | 10.868 | 16.677 | 23.179 | 1.00 29.64 |
| ATOM | 1207 | CA | GLU | A | 390 | 11.439 | 17.980 | 22.864 | 1.00 31.72 |
| ATOM | 1208 | CB | GLU | A | 390 | 10.966 | 19.050 | 23.849 | 1.00 31.76 |
| ATOM | 1209 | CG | GLU | A | 390 | 9.467 | 19.227 | 23.900 | 1.00 34.91 |
| ATOM | 1210 | CD | GLU | A | 390 | 9.038 | 20.407 | 24.748 | 1.00 36.35 |
| ATOM | 1211 | OE1 | GLU | A | 390 | 7.834 | 20.705 | 24.779 | 1.00 39.90 |
| ATOM | 1212 | OE2 | GLU | A | 390 | 9.889 | 21.048 | 25.383 | 1.00 38.61 |
| ATOM | 1213 | C | GLU | A | 390 | 12.953 | 17.887 | 22.932 | 1.00 32.04 |
| ATOM | 1214 | O | GLU | A | 390 | 13.508 | 17.087 | 23.693 | 1.00 31.77 |
| ATOM | 1215 | N | ASP | A | 391 | 13.612 | 18.769 | 22.192 | 1.00 33.33 |
| ATOM | 1216 | CA | ASP | A | 391 | 15.069 | 18.811 | 22.143 | 1.00 34.96 |
| ATOM | 1217 | CB | ASP | A | 391 | 15.506 | 19.703 | 20.985 | 1.00 36.72 |
| ATOM | 1218 | CG | ASP | A | 391 | 15.154 | 19.121 | 19.639 | 1.00 38.49 |
| ATOM | 1219 | OD1 | ASP | A | 391 | 14.590 | 17.994 | 19.558 | 1.00 37.58 |
| ATOM | 1220 | OD2 | ASP | A | 391 | 15.469 | 19.807 | 18.651 | 1.00 42.01 |
| ATOM | 1221 | C | ASP | A | 391 | 15.791 | 19.254 | 23.427 | 1.00 34.31 |
| ATOM | 1222 | O | ASP | A | 391 | 16.979 | 18.987 | 23.605 | 1.00 34.69 |
| ATOM | 1223 | N | ASN | A | 392 | 15.076 | 19.928 | 24.314 | 1.00 33.65 |
| ATOM | 1224 | CA | ASN | A | 392 | 15.680 | 20.412 | 25.542 | 1.00 33.99 |
| ATOM | 1225 | CB | ASN | A | 392 | 14.986 | 21.715 | 25.993 | 1.00 33.60 |
| ATOM | 1226 | CG | ASN | A | 392 | 13.553 | 21.500 | 26.503 | 1.00 35.43 |

Figure 10

| | | | | | | | | |
|---|---|---|---|---|---|---|---|---|
| ATOM | 1227 | OD1 | ASN | A | 392 | 12.966 | 20.410 | 26.406 | 1.00 34.21 |
| ATOM | 1228 | ND2 | ASN | A | 392 | 12.987 | 22.559 | 27.060 | 1.00 36.49 |
| ATOM | 1229 | C | ASN | A | 392 | 15.714 | 19.382 | 26.677 | 1.00 33.68 |
| ATOM | 1230 | O | ASN | A | 392 | 16.204 | 19.668 | 27.780 | 1.00 35.86 |
| ATOM | 1231 | N | GLU | A | 393 | 15.260 | 18.170 | 26.391 | 1.00 31.05 |
| ATOM | 1232 | CA | GLU | A | 393 | 15.214 | 17.137 | 27.407 | 1.00 30.50 |
| ATOM | 1233 | CB | GLU | A | 393 | 14.222 | 16.047 | 26.972 | 1.00 27.47 |
| ATOM | 1234 | CG | GLU | A | 393 | 12.786 | 16.581 | 26.838 | 1.00 23.48 |
| ATOM | 1235 | CD | GLU | A | 393 | 11.815 | 15.617 | 26.202 | 1.00 19.99 |
| ATOM | 1236 | OE1 | GLU | A | 393 | 12.198 | 14.477 | 25.875 | 1.00 20.29 |
| ATOM | 1237 | OE2 | GLU | A | 393 | 10.646 | 16.008 | 26.023 | 1.00 21.76 |
| ATOM | 1238 | C | GLU | A | 393 | 16.559 | 16.541 | 27.867 | 1.00 32.12 |
| ATOM | 1239 | O | GLU | A | 393 | 16.729 | 16.242 | 29.051 | 1.00 32.69 |
| ATOM | 1240 | N | TYR | A | 394 | 17.512 | 16.388 | 26.948 | 1.00 32.82 |
| ATOM | 1241 | CA | TYR | A | 394 | 18.807 | 15.802 | 27.283 | 1.00 34.20 |
| ATOM | 1242 | CB | TYR | A | 394 | 18.887 | 14.370 | 26.758 | 1.00 32.25 |
| ATOM | 1243 | CG | TYR | A | 394 | 17.815 | 13.519 | 27.363 | 1.00 30.39 |
| ATOM | 1244 | CD1 | TYR | A | 394 | 16.527 | 13.519 | 26.839 | 1.00 30.42 |
| ATOM | 1245 | CE1 | TYR | A | 394 | 15.493 | 12.795 | 27.444 | 1.00 33.39 |
| ATOM | 1246 | CD2 | TYR | A | 394 | 18.064 | 12.768 | 28.505 | 1.00 32.48 |
| ATOM | 1247 | CE2 | TYR | A | 394 | 17.043 | 12.028 | 29.129 | 1.00 34.00 |
| ATOM | 1248 | CZ | TYR | A | 394 | 15.756 | 12.049 | 28.595 | 1.00 34.76 |
| ATOM | 1249 | OH | TYR | A | 394 | 14.739 | 11.356 | 29.216 | 1.00 33.32 |
| ATOM | 1250 | C | TYR | A | 394 | 20.000 | 16.645 | 26.837 | 1.00 36.59 |
| ATOM | 1251 | O | TYR | A | 394 | 21.148 | 16.249 | 27.016 | 1.00 37.17 |
| ATOM | 1252 | N | THR | A | 395 | 19.709 | 17.775 | 26.198 | 1.00 38.88 |
| ATOM | 1253 | CA | THR | A | 395 | 20.717 | 18.746 | 25.791 | 1.00 41.78 |
| ATOM | 1254 | CB | THR | A | 395 | 21.083 | 18.670 | 24.335 | 1.00 41.48 |
| ATOM | 1255 | OG1 | THR | A | 395 | 19.932 | 18.309 | 23.559 | 1.00 43.33 |
| ATOM | 1256 | CG2 | THR | A | 395 | 22.189 | 17.699 | 24.159 | 1.00 40.69 |
| ATOM | 1257 | C | THR | A | 395 | 20.147 | 20.112 | 26.071 | 1.00 44.81 |
| ATOM | 1258 | O | THR | A | 395 | 19.048 | 20.236 | 26.619 | 1.00 45.55 |
| ATOM | 1259 | N | ALA | A | 396 | 20.857 | 21.152 | 25.667 | 1.00 49.15 |
| ATOM | 1260 | CA | ALA | A | 396 | 20.356 | 22.485 | 25.960 | 1.00 53.25 |
| ATOM | 1261 | CB | ALA | A | 396 | 21.289 | 23.188 | 26.963 | 1.00 53.26 |
| ATOM | 1262 | C | ALA | A | 396 | 20.095 | 23.359 | 24.735 | 1.00 56.09 |
| ATOM | 1263 | O | ALA | A | 396 | 20.497 | 24.526 | 24.705 | 1.00 57.31 |
| ATOM | 1264 | N | ARG | A | 397 | 19.363 | 22.815 | 23.759 | 1.00 58.76 |
| ATOM | 1265 | CA | ARG | A | 397 | 19.043 | 23.553 | 22.535 | 1.00 60.20 |
| ATOM | 1266 | CB | ARG | A | 397 | 18.526 | 22.610 | 21.448 | 1.00 61.05 |
| ATOM | 1267 | CG | ARG | A | 397 | 19.555 | 21.625 | 20.935 | 1.00 62.28 |
| ATOM | 1268 | CD | ARG | A | 397 | 19.559 | 21.590 | 19.404 | 1.00 63.02 |
| ATOM | 1269 | NE | ARG | A | 397 | 20.349 | 20.477 | 18.875 | 1.00 61.91 |
| ATOM | 1270 | CZ | ARG | A | 397 | 19.981 | 19.202 | 18.956 | 1.00 60.54 |
| ATOM | 1271 | NH1 | ARG | A | 397 | 18.836 | 18.872 | 19.553 | 1.00 59.16 |
| ATOM | 1272 | NH2 | ARG | A | 397 | 20.734 | 18.262 | 18.402 | 1.00 58.52 |
| ATOM | 1273 | C | ARG | A | 397 | 18.024 | 24.668 | 22.776 | 1.00 60.98 |
| ATOM | 1274 | O | ARG | A | 397 | 18.327 | 25.818 | 22.371 | 1.00 61.55 |
| ATOM | 1275 | CB | PRO | A | 403 | 8.423 | 19.632 | 18.707 | 1.00 31.47 |
| ATOM | 1276 | CG | PRO | A | 403 | 8.923 | 20.218 | 20.036 | 1.00 32.68 |
| ATOM | 1277 | C | PRO | A | 403 | 7.075 | 20.735 | 16.868 | 1.00 31.08 |
| ATOM | 1278 | O | PRO | A | 403 | 7.082 | 19.754 | 16.088 | 1.00 31.50 |
| ATOM | 1279 | N | PRO | A | 403 | 7.725 | 21.951 | 18.980 | 1.00 31.52 |
| ATOM | 1280 | CD | PRO | A | 403 | 8.035 | 21.464 | 20.332 | 1.00 32.16 |
| ATOM | 1281 | CA | PRO | A | 403 | 8.143 | 20.919 | 17.956 | 1.00 31.18 |
| ATOM | 1282 | N | ILE | A | 404 | 6.255 | 21.780 | 16.751 | 1.00 28.66 |
| ATOM | 1283 | CA | ILE | A | 404 | 5.158 | 21.884 | 15.802 | 1.00 25.62 |
| ATOM | 1284 | CB | ILE | A | 404 | 4.316 | 23.138 | 16.179 | 1.00 25.03 |
| ATOM | 1285 | CG2 | ILE | A | 404 | 3.476 | 23.621 | 15.033 | 1.00 24.34 |

Figure 10

| ATOM | 1286 | CG1 | ILE | A | 404 | 3.464 | 22.813 | 17.404 | 1.00 | 24.95 |
| ATOM | 1287 | CD1 | ILE | A | 404 | 2.646 | 21.541 | 17.219 | 1.00 | 26.77 |
| ATOM | 1288 | C | ILE | A | 404 | 5.570 | 21.907 | 14.315 | 1.00 | 22.96 |
| ATOM | 1289 | O | ILE | A | 404 | 4.876 | 21.355 | 13.467 | 1.00 | 22.29 |
| ATOM | 1290 | N | LYS | A | 405 | 6.742 | 22.448 | 14.019 | 1.00 | 20.18 |
| ATOM | 1291 | CA | LYS | A | 405 | 7.217 | 22.556 | 12.636 | 1.00 | 20.17 |
| ATOM | 1292 | CB | LYS | A | 405 | 8.452 | 23.464 | 12.560 | 1.00 | 18.19 |
| ATOM | 1293 | CG | LYS | A | 405 | 8.076 | 24.907 | 12.872 | 1.00 | 18.32 |
| ATOM | 1294 | CD | LYS | A | 405 | 9.251 | 25.844 | 12.845 | 1.00 | 19.59 |
| ATOM | 1295 | CE | LYS | A | 405 | 8.774 | 27.282 | 13.004 | 1.00 | 20.59 |
| ATOM | 1296 | NZ | LYS | A | 405 | 9.804 | 28.233 | 12.489 | 1.00 | 22.16 |
| ATOM | 1297 | C | LYS | A | 405 | 7.394 | 21.292 | 11.789 | 1.00 | 19.83 |
| ATOM | 1298 | O | LYS | A | 405 | 7.572 | 21.385 | 10.573 | 1.00 | 20.93 |
| ATOM | 1299 | N | TRP | A | 406 | 7.294 | 20.121 | 12.415 | 1.00 | 19.84 |
| ATOM | 1300 | CA | TRP | A | 406 | 7.423 | 18.841 | 11.711 | 1.00 | 19.17 |
| ATOM | 1301 | CB | TRP | A | 406 | 8.541 | 17.982 | 12.327 | 1.00 | 18.90 |
| ATOM | 1302 | CG | TRP | A | 406 | 9.900 | 18.555 | 12.173 | 1.00 | 19.08 |
| ATOM | 1303 | CD2 | TRP | A | 406 | 10.483 | 19.585 | 12.982 | 1.00 | 18.54 |
| ATOM | 1304 | CE2 | TRP | A | 406 | 11.768 | 19.850 | 12.459 | 1.00 | 18.03 |
| ATOM | 1305 | CE3 | TRP | A | 406 | 10.037 | 20.309 | 14.095 | 1.00 | 18.58 |
| ATOM | 1306 | CD1 | TRP | A | 406 | 10.833 | 18.237 | 11.215 | 1.00 | 17.80 |
| ATOM | 1307 | NE1 | TRP | A | 406 | 11.957 | 19.019 | 11.383 | 1.00 | 19.40 |
| ATOM | 1308 | CZ2 | TRP | A | 406 | 12.610 | 20.807 | 13.010 | 1.00 | 18.08 |
| ATOM | 1309 | CZ3 | TRP | A | 406 | 10.870 | 21.260 | 14.639 | 1.00 | 20.14 |
| ATOM | 1310 | CH2 | TRP | A | 406 | 12.148 | 21.502 | 14.095 | 1.00 | 19.68 |
| ATOM | 1311 | C | TRP | A | 406 | 6.137 | 18.034 | 11.785 | 1.00 | 19.70 |
| ATOM | 1312 | O | TRP | A | 406 | 6.079 | 16.902 | 11.309 | 1.00 | 20.93 |
| ATOM | 1313 | N | THR | A | 407 | 5.113 | 18.602 | 12.401 | 1.00 | 19.56 |
| ATOM | 1314 | CA | THR | A | 407 | 3.852 | 17.900 | 12.573 | 1.00 | 19.45 |
| ATOM | 1315 | CB | THR | A | 407 | 3.157 | 18.374 | 13.860 | 1.00 | 19.61 |
| ATOM | 1316 | OG1 | THR | A | 407 | 4.108 | 18.394 | 14.928 | 1.00 | 21.86 |
| ATOM | 1317 | CG2 | THR | A | 407 | 2.013 | 17.438 | 14.238 | 1.00 | 20.35 |
| ATOM | 1318 | C | THR | A | 407 | 2.890 | 18.055 | 11.402 | 1.00 | 19.50 |
| ATOM | 1319 | O | THR | A | 407 | 2.630 | 19.171 | 10.953 | 1.00 | 19.01 |
| ATOM | 1320 | N | ALA | A | 408 | 2.360 | 16.929 | 10.922 | 1.00 | 19.27 |
| ATOM | 1321 | CA | ALA | A | 408 | 1.400 | 16.916 | 9.815 | 1.00 | 19.82 |
| ATOM | 1322 | CB | ALA | A | 408 | 1.120 | 15.489 | 9.394 | 1.00 | 18.59 |
| ATOM | 1323 | C | ALA | A | 408 | 0.104 | 17.587 | 10.256 | 1.00 | 19.66 |
| ATOM | 1324 | O | ALA | A | 408 | -0.267 | 17.522 | 11.420 | 1.00 | 21.37 |
| ATOM | 1325 | N | PRO | A | 409 | -0.641 | 18.165 | 9.316 | 1.00 | 20.09 |
| ATOM | 1326 | CD | PRO | A | 409 | -0.387 | 18.120 | 7.874 | 1.00 | 19.34 |
| ATOM | 1327 | CA | PRO | A | 409 | -1.904 | 18.850 | 9.592 | 1.00 | 21.53 |
| ATOM | 1328 | CB | PRO | A | 409 | -2.436 | 19.132 | 8.197 | 1.00 | 22.71 |
| ATOM | 1329 | CG | PRO | A | 409 | -1.191 | 19.265 | 7.389 | 1.00 | 21.18 |
| ATOM | 1330 | C | PRO | A | 409 | -2.917 | 18.062 | 10.406 | 1.00 | 23.68 |
| ATOM | 1331 | O | PRO | A | 409 | -3.579 | 18.628 | 11.279 | 1.00 | 25.10 |
| ATOM | 1332 | N | GLU | A | 410 | -3.061 | 16.773 | 10.100 | 1.00 | 23.99 |
| ATOM | 1333 | CA | GLU | A | 410 | -4.013 | 15.923 | 10.802 | 1.00 | 23.93 |
| ATOM | 1334 | CB | GLU | A | 410 | -4.280 | 14.636 | 10.016 | 1.00 | 21.85 |
| ATOM | 1335 | CG | GLU | A | 410 | -3.142 | 13.595 | 9.987 | 1.00 | 20.01 |
| ATOM | 1336 | CD | GLU | A | 410 | -2.041 | 13.884 | 8.987 | 1.00 | 19.62 |
| ATOM | 1337 | OE1 | GLU | A | 410 | -2.184 | 14.800 | 8.151 | 1.00 | 19.25 |
| ATOM | 1338 | OE2 | GLU | A | 410 | -1.023 | 13.171 | 9.037 | 1.00 | 19.20 |
| ATOM | 1339 | C | GLU | A | 410 | -3.583 | 15.597 | 12.225 | 1.00 | 25.69 |
| ATOM | 1340 | O | GLU | A | 410 | -4.429 | 15.300 | 13.081 | 1.00 | 26.74 |
| ATOM | 1341 | N | ALA | A | 411 | -2.273 | 15.628 | 12.474 | 1.00 | 26.79 |
| ATOM | 1342 | CA | ALA | A | 411 | -1.728 | 15.350 | 13.812 | 1.00 | 27.61 |
| ATOM | 1343 | CB | ALA | A | 411 | -0.265 | 14.976 | 13.723 | 1.00 | 24.61 |
| ATOM | 1344 | C | ALA | A | 411 | -1.917 | 16.579 | 14.707 | 1.00 | 28.77 |

Figure 10

```
ATOM   1345  O    ALA A 411      -1.995  16.483  15.931  1.00 29.17
ATOM   1346  N    ILE A 412      -1.989  17.741  14.079  1.00 30.31
ATOM   1347  CA   ILE A 412      -2.207  18.988  14.794  1.00 31.17
ATOM   1348  CB   ILE A 412      -1.681  20.183  13.963  1.00 30.04
ATOM   1349  CG2  ILE A 412      -2.203  21.514  14.510  1.00 30.74
ATOM   1350  CG1  ILE A 412      -0.155  20.143  13.921  1.00 28.61
ATOM   1351  CD1  ILE A 412       0.459  21.155  12.999  1.00 25.03
ATOM   1352  C    ILE A 412      -3.700  19.172  15.055  1.00 31.85
ATOM   1353  O    ILE A 412      -4.095  19.517  16.166  1.00 33.58
ATOM   1354  N    ASN A 413      -4.516  18.874  14.043  1.00 32.71
ATOM   1355  CA   ASN A 413      -5.968  19.037  14.111  1.00 34.24
ATOM   1356  CB   ASN A 413      -6.548  19.188  12.701  1.00 34.95
ATOM   1357  CG   ASN A 413      -6.153  20.496  12.050  1.00 38.19
ATOM   1358  OD1  ASN A 413      -6.035  21.529  12.731  1.00 40.18
ATOM   1359  ND2  ASN A 413      -5.964  20.475  10.728  1.00 38.68
ATOM   1360  C    ASN A 413      -6.771  17.988  14.862  1.00 34.53
ATOM   1361  O    ASN A 413      -7.825  18.299  15.431  1.00 34.67
ATOM   1362  N    TYR A 414      -6.316  16.742  14.825  1.00 34.60
ATOM   1363  CA   TYR A 414      -7.053  15.676  15.503  1.00 35.07
ATOM   1364  CB   TYR A 414      -7.905  14.885  14.493  1.00 35.74
ATOM   1365  CG   TYR A 414      -8.790  15.749  13.633  1.00 37.15
ATOM   1366  CD1  TYR A 414      -9.895  16.404  14.175  1.00 38.30
ATOM   1367  CE1  TYR A 414     -10.688  17.255  13.387  1.00 39.63
ATOM   1368  CD2  TYR A 414      -8.491  15.956  12.279  1.00 38.77
ATOM   1369  CE2  TYR A 414      -9.272  16.801  11.482  1.00 39.29
ATOM   1370  CZ   TYR A 414     -10.367  17.448  12.041  1.00 39.55
ATOM   1371  OH   TYR A 414     -11.135  18.280  11.250  1.00 40.53
ATOM   1372  C    TYR A 414      -6.158  14.730  16.291  1.00 33.76
ATOM   1373  O    TYR A 414      -6.621  13.721  16.825  1.00 33.63
ATOM   1374  N    GLY A 415      -4.879  15.069  16.386  1.00 32.96
ATOM   1375  CA   GLY A 415      -3.958  14.217  17.111  1.00 33.62
ATOM   1376  C    GLY A 415      -3.800  12.829  16.490  1.00 33.65
ATOM   1377  O    GLY A 415      -3.404  11.880  17.171  1.00 33.75
ATOM   1378  N    THR A 416      -4.124  12.697  15.203  1.00 33.05
ATOM   1379  CA   THR A 416      -3.979  11.410  14.526  1.00 31.46
ATOM   1380  CB   THR A 416      -5.131  11.129  13.495  1.00 31.43
ATOM   1381  OG1  THR A 416      -4.602  10.432  12.357  1.00 31.22
ATOM   1382  CG2  THR A 416      -5.826  12.405  13.050  1.00 30.10
ATOM   1383  C    THR A 416      -2.589  11.274  13.881  1.00 29.51
ATOM   1384  O    THR A 416      -2.222  12.038  12.988  1.00 27.85
ATOM   1385  N    PHE A 417      -1.827  10.310  14.390  1.00 27.83
ATOM   1386  CA   PHE A 417      -0.478  10.020  13.932  1.00 26.59
ATOM   1387  CB   PHE A 417       0.501  10.077  15.109  1.00 27.49
ATOM   1388  CG   PHE A 417       0.759  11.461  15.637  1.00 28.51
ATOM   1389  CD1  PHE A 417      -0.076  12.023  16.616  1.00 28.28
ATOM   1390  CD2  PHE A 417       1.869  12.191  15.192  1.00 27.91
ATOM   1391  CE1  PHE A 417       0.198  13.294  17.162  1.00 28.54
ATOM   1392  CE2  PHE A 417       2.159  13.464  15.724  1.00 28.55
ATOM   1393  CZ   PHE A 417       1.320  14.021  16.711  1.00 29.51
ATOM   1394  C    PHE A 417      -0.320   8.655  13.278  1.00 24.60
ATOM   1395  O    PHE A 417      -0.633   7.640  13.882  1.00 24.74
ATOM   1396  N    THR A 418       0.228   8.643  12.066  1.00 23.18
ATOM   1397  CA   THR A 418       0.482   7.407  11.313  1.00 20.48
ATOM   1398  CB   THR A 418      -0.581   7.140  10.193  1.00 19.35
ATOM   1399  OG1  THR A 418      -0.407   8.079   9.132  1.00 20.17
ATOM   1400  CG2  THR A 418      -1.989   7.278  10.728  1.00 17.19
ATOM   1401  C    THR A 418       1.852   7.536  10.639  1.00 19.22
ATOM   1402  O    THR A 418       2.578   8.501  10.866  1.00 17.22
ATOM   1403  N    ILE A 419       2.190   6.551   9.812  1.00 18.53
```

Figure 10

| | | | | | | | | | |
|---|---|---|---|---|---|---|---|---|---|
| ATOM | 1404 | CA | ILE | A | 419 | 3.443 | 6.536 | 9.073 | 1.00 17.14 |
| ATOM | 1405 | CB | ILE | A | 419 | 3.668 | 5.166 | 8.377 | 1.00 17.31 |
| ATOM | 1406 | CG2 | ILE | A | 419 | 2.727 | 4.982 | 7.206 | 1.00 14.65 |
| ATOM | 1407 | CG1 | ILE | A | 419 | 5.110 | 5.053 | 7.911 | 1.00 18.95 |
| ATOM | 1408 | CD1 | ILE | A | 419 | 6.139 | 5.106 | 9.066 | 1.00 19.61 |
| ATOM | 1409 | C | ILE | A | 419 | 3.371 | 7.645 | 8.028 | 1.00 16.46 |
| ATOM | 1410 | O | ILE | A | 419 | 4.383 | 8.144 | 7.567 | 1.00 15.73 |
| ATOM | 1411 | N | LYS | A | 420 | 2.154 | 8.043 | 7.682 | 1.00 15.64 |
| ATOM | 1412 | CA | LYS | A | 420 | 1.968 | 9.102 | 6.714 | 1.00 15.60 |
| ATOM | 1413 | CB | LYS | A | 420 | 0.539 | 9.092 | 6.148 | 1.00 14.44 |
| ATOM | 1414 | CG | LYS | A | 420 | 0.266 | 7.940 | 5.202 | 1.00 11.94 |
| ATOM | 1415 | CD | LYS | A | 420 | 1.275 | 7.922 | 4.078 | 1.00 12.47 |
| ATOM | 1416 | CE | LYS | A | 420 | 0.963 | 6.808 | 3.139 | 1.00 13.84 |
| ATOM | 1417 | NZ | LYS | A | 420 | 2.001 | 6.702 | 2.127 | 1.00 16.61 |
| ATOM | 1418 | C | LYS | A | 420 | 2.332 | 10.461 | 7.305 | 1.00 16.10 |
| ATOM | 1419 | O | LYS | A | 420 | 2.755 | 11.351 | 6.584 | 1.00 15.74 |
| ATOM | 1420 | N | SER | A | 421 | 2.146 | 10.641 | 8.611 | 1.00 16.90 |
| ATOM | 1421 | CA | SER | A | 421 | 2.533 | 11.909 | 9.208 | 1.00 16.80 |
| ATOM | 1422 | CB | SER | A | 421 | 1.818 | 12.215 | 10.546 | 1.00 18.81 |
| ATOM | 1423 | OG | SER | A | 421 | 1.093 | 11.141 | 11.112 | 1.00 18.65 |
| ATOM | 1424 | C | SER | A | 421 | 4.050 | 11.944 | 9.345 | 1.00 16.25 |
| ATOM | 1425 | O | SER | A | 421 | 4.643 | 13.018 | 9.367 | 1.00 17.52 |
| ATOM | 1426 | N | ASP | A | 422 | 4.680 | 10.771 | 9.411 | 1.00 15.71 |
| ATOM | 1427 | CA | ASP | A | 422 | 6.144 | 10.708 | 9.481 | 1.00 16.35 |
| ATOM | 1428 | CB | ASP | A | 422 | 6.670 | 9.290 | 9.773 | 1.00 15.95 |
| ATOM | 1429 | CG | ASP | A | 422 | 6.529 | 8.866 | 11.232 | 1.00 17.12 |
| ATOM | 1430 | OD1 | ASP | A | 422 | 6.419 | 9.708 | 12.151 | 1.00 18.56 |
| ATOM | 1431 | OD2 | ASP | A | 422 | 6.546 | 7.645 | 11.461 | 1.00 18.58 |
| ATOM | 1432 | C | ASP | A | 422 | 6.683 | 11.135 | 8.117 | 1.00 15.48 |
| ATOM | 1433 | O | ASP | A | 422 | 7.742 | 11.726 | 8.050 | 1.00 18.02 |
| ATOM | 1434 | N | VAL | A | 423 | 5.995 | 10.743 | 7.039 | 1.00 15.09 |
| ATOM | 1435 | CA | VAL | A | 423 | 6.377 | 11.105 | 5.669 | 1.00 14.06 |
| ATOM | 1436 | CB | VAL | A | 423 | 5.430 | 10.460 | 4.582 | 1.00 13.46 |
| ATOM | 1437 | CG1 | VAL | A | 423 | 5.799 | 10.947 | 3.167 | 1.00 12.03 |
| ATOM | 1438 | CG2 | VAL | A | 423 | 5.511 | 8.923 | 4.625 | 1.00 9.41 |
| ATOM | 1439 | C | VAL | A | 423 | 6.361 | 12.635 | 5.603 | 1.00 14.97 |
| ATOM | 1440 | O | VAL | A | 423 | 7.315 | 13.240 | 5.098 | 1.00 16.63 |
| ATOM | 1441 | N | TRP | A | 424 | 5.346 | 13.259 | 6.211 | 1.00 14.84 |
| ATOM | 1442 | CA | TRP | A | 424 | 5.258 | 14.724 | 6.263 | 1.00 14.25 |
| ATOM | 1443 | CB | TRP | A | 424 | 3.982 | 15.166 | 6.984 | 1.00 12.33 |
| ATOM | 1444 | CG | TRP | A | 424 | 3.877 | 16.654 | 7.117 | 1.00 11.97 |
| ATOM | 1445 | CD2 | TRP | A | 424 | 2.979 | 17.532 | 6.422 | 1.00 12.29 |
| ATOM | 1446 | CE2 | TRP | A | 424 | 3.235 | 18.845 | 6.888 | 1.00 13.67 |
| ATOM | 1447 | CE3 | TRP | A | 424 | 1.982 | 17.339 | 5.451 | 1.00 13.54 |
| ATOM | 1448 | CD1 | TRP | A | 424 | 4.617 | 17.446 | 7.939 | 1.00 13.70 |
| ATOM | 1449 | NE1 | TRP | A | 424 | 4.239 | 18.758 | 7.814 | 1.00 13.57 |
| ATOM | 1450 | CZ2 | TRP | A | 424 | 2.530 | 19.968 | 6.424 | 1.00 13.11 |
| ATOM | 1451 | CZ3 | TRP | A | 424 | 1.271 | 18.465 | 4.981 | 1.00 15.60 |
| ATOM | 1452 | CH2 | TRP | A | 424 | 1.556 | 19.762 | 5.473 | 1.00 13.85 |
| ATOM | 1453 | C | TRP | A | 424 | 6.511 | 15.242 | 6.996 | 1.00 16.14 |
| ATOM | 1454 | O | TRP | A | 424 | 7.255 | 16.072 | 6.473 | 1.00 16.87 |
| ATOM | 1455 | N | SER | A | 425 | 6.781 | 14.704 | 8.185 | 1.00 17.24 |
| ATOM | 1456 | CA | SER | A | 425 | 7.968 | 15.093 | 8.944 | 1.00 17.45 |
| ATOM | 1457 | CB | SER | A | 425 | 8.073 | 14.268 | 10.228 | 1.00 19.09 |
| ATOM | 1458 | OG | SER | A | 425 | 6.945 | 14.470 | 11.062 | 1.00 19.43 |
| ATOM | 1459 | C | SER | A | 425 | 9.253 | 14.894 | 8.129 | 1.00 18.00 |
| ATOM | 1460 | O | SER | A | 425 | 10.191 | 15.673 | 8.259 | 1.00 19.23 |
| ATOM | 1461 | N | PHE | A | 426 | 9.308 | 13.838 | 7.317 | 1.00 17.34 |
| ATOM | 1462 | CA | PHE | A | 426 | 10.485 | 13.566 | 6.490 | 1.00 17.65 |

Figure 10

| ATOM | 1463 | CB  | PHE | A | 426 | 10.362 | 12.218 | 5.762  | 1.00 | 16.00 |
| ---- | ---- | --- | --- | - | --- | ------ | ------ | ------ | ---- | ----- |
| ATOM | 1464 | CG  | PHE | A | 426 | 11.594 | 11.842 | 4.980  | 1.00 | 16.00 |
| ATOM | 1465 | CD1 | PHE | A | 426 | 12.750 | 11.410 | 5.636  | 1.00 | 16.10 |
| ATOM | 1466 | CD2 | PHE | A | 426 | 11.619 | 11.944 | 3.598  | 1.00 | 15.10 |
| ATOM | 1467 | CE1 | PHE | A | 426 | 13.901 | 11.091 | 4.931  | 1.00 | 14.49 |
| ATOM | 1468 | CE2 | PHE | A | 426 | 12.778 | 11.625 | 2.883  | 1.00 | 15.26 |
| ATOM | 1469 | CZ  | PHE | A | 426 | 13.919 | 11.197 | 3.556  | 1.00 | 15.14 |
| ATOM | 1470 | C   | PHE | A | 426 | 10.687 | 14.689 | 5.476  | 1.00 | 16.99 |
| ATOM | 1471 | O   | PHE | A | 426 | 11.811 | 15.126 | 5.241  | 1.00 | 18.03 |
| ATOM | 1472 | N   | GLY | A | 427 | 9.588  | 15.149 | 4.882  | 1.00 | 16.98 |
| ATOM | 1473 | CA  | GLY | A | 427 | 9.662  | 16.243 | 3.932  | 1.00 | 17.32 |
| ATOM | 1474 | C   | GLY | A | 427 | 10.294 | 17.459 | 4.588  | 1.00 | 17.68 |
| ATOM | 1475 | O   | GLY | A | 427 | 11.174 | 18.075 | 4.001  | 1.00 | 18.27 |
| ATOM | 1476 | N   | ILE | A | 428 | 9.850  | 17.787 | 5.805  | 1.00 | 18.19 |
| ATOM | 1477 | CA  | ILE | A | 428 | 10.379 | 18.913 | 6.584  | 1.00 | 18.05 |
| ATOM | 1478 | CB  | ILE | A | 428 | 9.648  | 19.050 | 7.944  | 1.00 | 18.13 |
| ATOM | 1479 | CG2 | ILE | A | 428 | 10.180 | 20.243 | 8.721  | 1.00 | 17.50 |
| ATOM | 1480 | CG1 | ILE | A | 428 | 8.148  | 19.223 | 7.718  | 1.00 | 19.18 |
| ATOM | 1481 | CD1 | ILE | A | 428 | 7.780  | 20.417 | 6.863  | 1.00 | 19.66 |
| ATOM | 1482 | C   | ILE | A | 428 | 11.854 | 18.686 | 6.868  | 1.00 | 18.25 |
| ATOM | 1483 | O   | ILE | A | 428 | 12.646 | 19.622 | 6.862  | 1.00 | 18.68 |
| ATOM | 1484 | N   | LEU | A | 429 | 12.213 | 17.431 | 7.116  | 1.00 | 18.48 |
| ATOM | 1485 | CA  | LEU | A | 429 | 13.591 | 17.051 | 7.401  | 1.00 | 18.27 |
| ATOM | 1486 | CB  | LEU | A | 429 | 13.613 | 15.596 | 7.899  | 1.00 | 17.55 |
| ATOM | 1487 | CG  | LEU | A | 429 | 14.857 | 14.984 | 8.538  | 1.00 | 18.60 |
| ATOM | 1488 | CD1 | LEU | A | 429 | 14.434 | 13.708 | 9.225  | 1.00 | 17.72 |
| ATOM | 1489 | CD2 | LEU | A | 429 | 15.981 | 14.720 | 7.523  | 1.00 | 16.97 |
| ATOM | 1490 | C   | LEU | A | 429 | 14.486 | 17.238 | 6.153  | 1.00 | 18.66 |
| ATOM | 1491 | O   | LEU | A | 429 | 15.684 | 17.556 | 6.270  | 1.00 | 19.27 |
| ATOM | 1492 | N   | LEU | A | 430 | 13.920 | 17.020 | 4.965  | 1.00 | 17.55 |
| ATOM | 1493 | CA  | LEU | A | 430 | 14.683 | 17.196 | 3.744  | 1.00 | 16.25 |
| ATOM | 1494 | CB  | LEU | A | 430 | 13.889 | 16.768 | 2.527  | 1.00 | 15.34 |
| ATOM | 1495 | CG  | LEU | A | 430 | 13.688 | 15.270 | 2.323  | 1.00 | 13.88 |
| ATOM | 1496 | CD1 | LEU | A | 430 | 12.734 | 15.041 | 1.160  | 1.00 | 9.97  |
| ATOM | 1497 | CD2 | LEU | A | 430 | 15.034 | 14.566 | 2.101  | 1.00 | 10.56 |
| ATOM | 1498 | C   | LEU | A | 430 | 15.093 | 18.644 | 3.597  | 1.00 | 17.49 |
| ATOM | 1499 | O   | LEU | A | 430 | 16.138 | 18.924 | 3.030  | 1.00 | 20.09 |
| ATOM | 1500 | N   | THR | A | 431 | 14.259 | 19.570 | 4.071  | 1.00 | 18.18 |
| ATOM | 1501 | CA  | THR | A | 431 | 14.592 | 20.999 | 4.003  | 1.00 | 19.46 |
| ATOM | 1502 | CB  | THR | A | 431 | 13.397 | 21.937 | 4.371  | 1.00 | 17.46 |
| ATOM | 1503 | OG1 | THR | A | 431 | 13.108 | 21.821 | 5.768  | 1.00 | 19.55 |
| ATOM | 1504 | CG2 | THR | A | 431 | 12.154 | 21.599 | 3.557  | 1.00 | 16.36 |
| ATOM | 1505 | C   | THR | A | 431 | 15.771 | 21.304 | 4.936  | 1.00 | 20.76 |
| ATOM | 1506 | O   | THR | A | 431 | 16.620 | 22.131 | 4.607  | 1.00 | 21.68 |
| ATOM | 1507 | N   | GLU | A | 432 | 15.795 | 20.652 | 6.102  | 1.00 | 21.72 |
| ATOM | 1508 | CA  | GLU | A | 432 | 16.874 | 20.804 | 7.071  | 1.00 | 21.08 |
| ATOM | 1509 | CB  | GLU | A | 432 | 16.604 | 19.958 | 8.312  | 1.00 | 19.77 |
| ATOM | 1510 | CG  | GLU | A | 432 | 15.374 | 20.352 | 9.083  | 1.00 | 20.30 |
| ATOM | 1511 | CD  | GLU | A | 432 | 15.295 | 19.625 | 10.401 | 1.00 | 20.68 |
| ATOM | 1512 | OE1 | GLU | A | 432 | 14.611 | 18.587 | 10.509 | 1.00 | 21.45 |
| ATOM | 1513 | OE2 | GLU | A | 432 | 15.952 | 20.085 | 11.341 | 1.00 | 23.19 |
| ATOM | 1514 | C   | GLU | A | 432 | 18.176 | 20.329 | 6.444  | 1.00 | 22.31 |
| ATOM | 1515 | O   | GLU | A | 432 | 19.211 | 20.979 | 6.570  | 1.00 | 24.29 |
| ATOM | 1516 | N   | ILE | A | 433 | 18.131 | 19.188 | 5.772  | 1.00 | 22.17 |
| ATOM | 1517 | CA  | ILE | A | 433 | 19.326 | 18.653 | 5.152  | 1.00 | 23.37 |
| ATOM | 1518 | CB  | ILE | A | 433 | 19.067 | 17.257 | 4.556  | 1.00 | 24.14 |
| ATOM | 1519 | CG2 | ILE | A | 433 | 20.179 | 16.869 | 3.589  | 1.00 | 23.11 |
| ATOM | 1520 | CG1 | ILE | A | 433 | 18.913 | 16.220 | 5.675  | 1.00 | 23.00 |
| ATOM | 1521 | CD1 | ILE | A | 433 | 18.679 | 14.785 | 5.182  | 1.00 | 19.87 |

Figure 10

| ATOM | 1522 | C   | ILE A 433 | 19.946 | 19.573 | 4.086  | 1.00 | 25.40 |
|------|------|-----|-----------|--------|--------|--------|------|-------|
| ATOM | 1523 | O   | ILE A 433 | 21.157 | 19.808 | 4.111  | 1.00 | 26.43 |
| ATOM | 1524 | N   | VAL A 434 | 19.135 | 20.102 | 3.167  | 1.00 | 26.01 |
| ATOM | 1525 | CA  | VAL A 434 | 19.666 | 20.962 | 2.112  | 1.00 | 27.08 |
| ATOM | 1526 | CB  | VAL A 434 | 18.787 | 20.948 | 0.825  | 1.00 | 26.70 |
| ATOM | 1527 | CG1 | VAL A 434 | 18.695 | 19.558 | 0.279  | 1.00 | 27.18 |
| ATOM | 1528 | CG2 | VAL A 434 | 17.405 | 21.500 | 1.103  | 1.00 | 26.67 |
| ATOM | 1529 | C   | VAL A 434 | 19.949 | 22.413 | 2.491  | 1.00 | 28.06 |
| ATOM | 1530 | O   | VAL A 434 | 20.405 | 23.174 | 1.649  | 1.00 | 31.07 |
| ATOM | 1531 | N   | THR A 435 | 19.652 | 22.814 | 3.723  | 1.00 | 28.30 |
| ATOM | 1532 | CA  | THR A 435 | 19.913 | 24.189 | 4.149  | 1.00 | 29.44 |
| ATOM | 1533 | CB  | THR A 435 | 18.637 | 24.931 | 4.597  | 1.00 | 28.24 |
| ATOM | 1534 | OG1 | THR A 435 | 18.012 | 24.202 | 5.654  | 1.00 | 27.81 |
| ATOM | 1535 | CG2 | THR A 435 | 17.664 | 25.112 | 3.452  | 1.00 | 26.11 |
| ATOM | 1536 | C   | THR A 435 | 20.872 | 24.168 | 5.328  | 1.00 | 31.93 |
| ATOM | 1537 | O   | THR A 435 | 20.976 | 25.143 | 6.084  | 1.00 | 32.17 |
| ATOM | 1538 | N   | HIS A 436 | 21.505 | 23.015 | 5.521  | 1.00 | 34.63 |
| ATOM | 1539 | CA  | HIS A 436 | 22.475 | 22.796 | 6.590  | 1.00 | 37.45 |
| ATOM | 1540 | CB  | HIS A 436 | 23.717 | 23.641 | 6.322  | 1.00 | 42.57 |
| ATOM | 1541 | CG  | HIS A 436 | 24.265 | 23.484 | 4.937  | 1.00 | 47.43 |
| ATOM | 1542 | CD2 | HIS A 436 | 24.718 | 24.401 | 4.048  | 1.00 | 49.86 |
| ATOM | 1543 | ND1 | HIS A 436 | 24.429 | 22.254 | 4.334  | 1.00 | 48.86 |
| ATOM | 1544 | CE1 | HIS A 436 | 24.965 | 22.416 | 3.138  | 1.00 | 49.49 |
| ATOM | 1545 | NE2 | HIS A 436 | 25.149 | 23.711 | 2.941  | 1.00 | 51.96 |
| ATOM | 1546 | C   | HIS A 436 | 21.968 | 23.030 | 8.022  | 1.00 | 36.48 |
| ATOM | 1547 | O   | HIS A 436 | 22.609 | 23.728 | 8.811  | 1.00 | 36.13 |
| ATOM | 1548 | N   | GLY A 437 | 20.833 | 22.428 | 8.359  | 1.00 | 35.34 |
| ATOM | 1549 | CA  | GLY A 437 | 20.286 | 22.581 | 9.694  | 1.00 | 35.48 |
| ATOM | 1550 | C   | GLY A 437 | 19.502 | 23.855 | 9.975  | 1.00 | 36.05 |
| ATOM | 1551 | O   | GLY A 437 | 19.337 | 24.257 | 11.134 | 1.00 | 36.50 |
| ATOM | 1552 | N   | ARG A 438 | 19.032 | 24.511 | 8.923  | 1.00 | 36.50 |
| ATOM | 1553 | CA  | ARG A 438 | 18.242 | 25.725 | 9.098  | 1.00 | 36.72 |
| ATOM | 1554 | CB  | ARG A 438 | 18.134 | 26.475 | 7.765  | 1.00 | 40.75 |
| ATOM | 1555 | CG  | ARG A 438 | 17.777 | 27.958 | 7.852  | 1.00 | 44.89 |
| ATOM | 1556 | CD  | ARG A 438 | 16.290 | 28.183 | 7.967  | 1.00 | 48.70 |
| ATOM | 1557 | NE  | ARG A 438 | 15.520 | 27.531 | 6.902  | 1.00 | 52.98 |
| ATOM | 1558 | CZ  | ARG A 438 | 15.538 | 27.899 | 5.622  | 1.00 | 55.71 |
| ATOM | 1559 | NH1 | ARG A 438 | 16.306 | 28.918 | 5.230  | 1.00 | 56.88 |
| ATOM | 1560 | NH2 | ARG A 438 | 14.753 | 27.279 | 4.739  | 1.00 | 55.19 |
| ATOM | 1561 | C   | ARG A 438 | 16.857 | 25.306 | 9.603  | 1.00 | 34.85 |
| ATOM | 1562 | O   | ARG A 438 | 16.317 | 24.278 | 9.180  | 1.00 | 33.27 |
| ATOM | 1563 | N   | ILE A 439 | 16.314 | 26.087 | 10.536 | 1.00 | 32.62 |
| ATOM | 1564 | CA  | ILE A 439 | 15.000 | 25.817 | 11.111 | 1.00 | 30.60 |
| ATOM | 1565 | CB  | ILE A 439 | 14.715 | 26.751 | 12.316 | 1.00 | 30.99 |
| ATOM | 1566 | CG2 | ILE A 439 | 13.321 | 26.507 | 12.873 | 1.00 | 30.87 |
| ATOM | 1567 | CG1 | ILE A 439 | 15.736 | 26.468 | 13.425 | 1.00 | 34.15 |
| ATOM | 1568 | CD1 | ILE A 439 | 15.611 | 27.338 | 14.696 | 1.00 | 37.25 |
| ATOM | 1569 | C   | ILE A 439 | 13.919 | 25.987 | 10.044 | 1.00 | 29.26 |
| ATOM | 1570 | O   | ILE A 439 | 13.976 | 26.912 | 9.242  | 1.00 | 29.19 |
| ATOM | 1571 | N   | PRO A 440 | 12.952 | 25.054 | 9.983  | 1.00 | 27.16 |
| ATOM | 1572 | CD  | PRO A 440 | 12.864 | 23.796 | 10.741 | 1.00 | 25.45 |
| ATOM | 1573 | CA  | PRO A 440 | 11.874 | 25.140 | 8.993  | 1.00 | 25.40 |
| ATOM | 1574 | CB  | PRO A 440 | 11.069 | 23.866 | 9.266  | 1.00 | 25.37 |
| ATOM | 1575 | CG  | PRO A 440 | 12.094 | 22.924 | 9.802  | 1.00 | 25.69 |
| ATOM | 1576 | C   | PRO A 440 | 11.045 | 26.408 | 9.233  | 1.00 | 24.44 |
| ATOM | 1577 | O   | PRO A 440 | 11.081 | 26.972 | 10.329 | 1.00 | 23.65 |
| ATOM | 1578 | N   | TYR A 441 | 10.319 | 26.857 | 8.209  | 1.00 | 23.90 |
| ATOM | 1579 | CA  | TYR A 441 | 9.481  | 28.063 | 8.297  | 1.00 | 24.23 |
| ATOM | 1580 | CB  | TYR A 441 | 8.176  | 27.775 | 9.056  | 1.00 | 22.00 |

Figure 10

| | | | | | | | | |
|---|---|---|---|---|---|---|---|---|
| ATOM | 1581 | CG | TYR | A | 441 | 7.420 | 26.576 | 8.550 | 1.00 20.98 |
| ATOM | 1582 | CD1 | TYR | A | 441 | 6.553 | 26.685 | 7.465 | 1.00 22.24 |
| ATOM | 1583 | CE1 | TYR | A | 441 | 5.868 | 25.580 | 6.980 | 1.00 22.09 |
| ATOM | 1584 | CD2 | TYR | A | 441 | 7.580 | 25.327 | 9.144 | 1.00 19.00 |
| ATOM | 1585 | CE2 | TYR | A | 441 | 6.903 | 24.223 | 8.675 | 1.00 21.20 |
| ATOM | 1586 | CZ | TYR | A | 441 | 6.045 | 24.351 | 7.590 | 1.00 24.05 |
| ATOM | 1587 | OH | TYR | A | 441 | 5.362 | 23.247 | 7.111 | 1.00 27.58 |
| ATOM | 1588 | C | TYR | A | 441 | 10.263 | 29.155 | 9.021 | 1.00 25.33 |
| ATOM | 1589 | O | TYR | A | 441 | 9.870 | 29.601 | 10.100 | 1.00 24.82 |
| ATOM | 1590 | N | PRO | A | 442 | 11.411 | 29.568 | 8.457 | 1.00 27.20 |
| ATOM | 1591 | CD | PRO | A | 442 | 11.951 | 29.249 | 7.118 | 1.00 26.82 |
| ATOM | 1592 | CA | PRO | A | 442 | 12.201 | 30.610 | 9.125 | 1.00 28.70 |
| ATOM | 1593 | CB | PRO | A | 442 | 13.444 | 30.718 | 8.235 | 1.00 27.88 |
| ATOM | 1594 | CG | PRO | A | 442 | 12.896 | 30.404 | 6.854 | 1.00 28.04 |
| ATOM | 1595 | C | PRO | A | 442 | 11.415 | 31.921 | 9.231 | 1.00 30.74 |
| ATOM | 1596 | O | PRO | A | 442 | 10.719 | 32.323 | 8.306 | 1.00 32.79 |
| ATOM | 1597 | N | GLY | A | 443 | 11.453 | 32.546 | 10.394 | 1.00 32.08 |
| ATOM | 1598 | CA | GLY | A | 443 | 10.741 | 33.796 | 10.543 | 1.00 32.96 |
| ATOM | 1599 | C | GLY | A | 443 | 9.288 | 33.594 | 10.869 | 1.00 33.19 |
| ATOM | 1600 | O | GLY | A | 443 | 8.489 | 34.514 | 10.733 | 1.00 34.95 |
| ATOM | 1601 | N | MET | A | 444 | 8.933 | 32.378 | 11.250 | 1.00 32.53 |
| ATOM | 1602 | CA | MET | A | 444 | 7.560 | 32.077 | 11.622 | 1.00 32.66 |
| ATOM | 1603 | CB | MET | A | 444 | 6.897 | 31.142 | 10.607 | 1.00 33.27 |
| ATOM | 1604 | CG | MET | A | 444 | 6.135 | 31.848 | 9.520 | 1.00 33.26 |
| ATOM | 1605 | SD | MET | A | 444 | 5.526 | 30.698 | 8.313 | 1.00 33.67 |
| ATOM | 1606 | CE | MET | A | 444 | 4.177 | 30.181 | 9.069 | 1.00 35.80 |
| ATOM | 1607 | C | MET | A | 444 | 7.571 | 31.402 | 12.966 | 1.00 32.59 |
| ATOM | 1608 | O | MET | A | 444 | 8.424 | 30.550 | 13.211 | 1.00 33.34 |
| ATOM | 1609 | N | THR | A | 445 | 6.666 | 31.820 | 13.851 | 1.00 31.11 |
| ATOM | 1610 | CA | THR | A | 445 | 6.564 | 31.210 | 15.171 | 1.00 30.01 |
| ATOM | 1611 | CB | THR | A | 445 | 6.042 | 32.210 | 16.227 | 1.00 30.49 |
| ATOM | 1612 | OG1 | THR | A | 445 | 4.642 | 32.428 | 16.036 | 1.00 31.41 |
| ATOM | 1613 | CG2 | THR | A | 445 | 6.760 | 33.550 | 16.094 | 1.00 31.09 |
| ATOM | 1614 | C | THR | A | 445 | 5.601 | 30.023 | 15.048 | 1.00 29.52 |
| ATOM | 1615 | O | THR | A | 445 | 4.952 | 29.846 | 14.015 | 1.00 29.75 |
| ATOM | 1616 | N | ASN | A | 446 | 5.505 | 29.210 | 16.091 | 1.00 28.47 |
| ATOM | 1617 | CA | ASN | A | 446 | 4.613 | 28.059 | 16.050 | 1.00 28.05 |
| ATOM | 1618 | CB | ASN | A | 446 | 4.665 | 27.258 | 17.358 | 1.00 28.89 |
| ATOM | 1619 | CG | ASN | A | 446 | 5.882 | 26.349 | 17.447 | 1.00 29.55 |
| ATOM | 1620 | OD1 | ASN | A | 446 | 6.825 | 26.471 | 16.666 | 1.00 30.54 |
| ATOM | 1621 | ND2 | ASN | A | 446 | 5.855 | 25.420 | 18.393 | 1.00 29.66 |
| ATOM | 1622 | C | ASN | A | 446 | 3.170 | 28.396 | 15.715 | 1.00 27.30 |
| ATOM | 1623 | O | ASN | A | 446 | 2.549 | 27.706 | 14.905 | 1.00 24.96 |
| ATOM | 1624 | N | PRO | A | 447 | 2.588 | 29.401 | 16.400 | 1.00 28.01 |
| ATOM | 1625 | CD | PRO | A | 447 | 3.015 | 30.010 | 17.676 | 1.00 27.48 |
| ATOM | 1626 | CA | PRO | A | 447 | 1.193 | 29.748 | 16.093 | 1.00 27.46 |
| ATOM | 1627 | CB | PRO | A | 447 | 0.812 | 30.725 | 17.217 | 1.00 27.36 |
| ATOM | 1628 | CG | PRO | A | 447 | 2.137 | 31.206 | 17.768 | 1.00 28.11 |
| ATOM | 1629 | C | PRO | A | 447 | 0.974 | 30.298 | 14.679 | 1.00 27.19 |
| ATOM | 1630 | O | PRO | A | 447 | -0.121 | 30.171 | 14.109 | 1.00 27.64 |
| ATOM | 1631 | N | GLU | A | 448 | 2.021 | 30.858 | 14.092 | 1.00 25.76 |
| ATOM | 1632 | CA | GLU | A | 448 | 1.914 | 31.357 | 12.737 | 1.00 26.14 |
| ATOM | 1633 | CB | GLU | A | 448 | 3.021 | 32.362 | 12.457 | 1.00 28.12 |
| ATOM | 1634 | CG | GLU | A | 448 | 2.800 | 33.671 | 13.190 | 1.00 30.08 |
| ATOM | 1635 | CD | GLU | A | 448 | 4.036 | 34.532 | 13.273 | 1.00 31.15 |
| ATOM | 1636 | OE1 | GLU | A | 448 | 5.073 | 34.191 | 12.661 | 1.00 32.34 |
| ATOM | 1637 | OE2 | GLU | A | 448 | 3.958 | 35.563 | 13.971 | 1.00 32.56 |
| ATOM | 1638 | C | GLU | A | 448 | 1.965 | 30.194 | 11.746 | 1.00 25.59 |
| ATOM | 1639 | O | GLU | A | 448 | 1.305 | 30.248 | 10.712 | 1.00 25.08 |

Figure 10

```
ATOM   1640  N    VAL A 449       2.763  29.164  12.059  1.00 25.09
ATOM   1641  CA   VAL A 449       2.878  27.960  11.223  1.00 24.93
ATOM   1642  CB   VAL A 449       3.974  26.980  11.748  1.00 24.20
ATOM   1643  CG1  VAL A 449       3.877  25.626  11.051  1.00 20.39
ATOM   1644  CG2  VAL A 449       5.337  27.568  11.542  1.00 21.56
ATOM   1645  C    VAL A 449       1.527  27.249  11.237  1.00 26.14
ATOM   1646  O    VAL A 449       1.092  26.679  10.234  1.00 27.97
ATOM   1647  N    ILE A 450       0.842  27.332  12.371  1.00 26.21
ATOM   1648  CA   ILE A 450      -0.465  26.707  12.515  1.00 26.77
ATOM   1649  CB   ILE A 450      -0.955  26.764  13.972  1.00 27.08
ATOM   1650  CG2  ILE A 450      -2.300  26.070  14.095  1.00 28.06
ATOM   1651  CG1  ILE A 450       0.068  26.128  14.903  1.00 28.79
ATOM   1652  CD1  ILE A 450       0.282  24.671  14.676  1.00 29.40
ATOM   1653  C    ILE A 450      -1.512  27.382  11.629  1.00 26.23
ATOM   1654  O    ILE A 450      -2.260  26.706  10.918  1.00 25.70
ATOM   1655  N    GLN A 451      -1.565  28.711  11.673  1.00 26.40
ATOM   1656  CA   GLN A 451      -2.542  29.439  10.873  1.00 27.23
ATOM   1657  CB   GLN A 451      -2.776  30.855  11.411  1.00 30.30
ATOM   1658  CG   GLN A 451      -1.548  31.712  11.486  1.00 36.65
ATOM   1659  CD   GLN A 451      -1.691  32.863  12.468  1.00 40.20
ATOM   1660  OE1  GLN A 451      -1.314  33.998  12.164  1.00 43.95
ATOM   1661  NE2  GLN A 451      -2.197  32.572  13.663  1.00 40.26
ATOM   1662  C    GLN A 451      -2.180  29.441   9.405  1.00 24.60
ATOM   1663  O    GLN A 451      -3.051  29.537   8.559  1.00 25.08
ATOM   1664  N    ASN A 452      -0.897  29.322   9.097  1.00 23.67
ATOM   1665  CA   ASN A 452      -0.480  29.260   7.710  1.00 22.13
ATOM   1666  CB   ASN A 452       1.019  29.515   7.578  1.00 23.95
ATOM   1667  CG   ASN A 452       1.341  30.988   7.310  1.00 25.79
ATOM   1668  OD1  ASN A 452       1.330  31.434   6.158  1.00 25.15
ATOM   1669  ND2  ASN A 452       1.612  31.748   8.375  1.00 22.95
ATOM   1670  C    ASN A 452      -0.870  27.877   7.183  1.00 21.38
ATOM   1671  O    ASN A 452      -1.413  27.769   6.089  1.00 22.40
ATOM   1672  N    LEU A 453      -0.665  26.824   7.970  1.00 19.34
ATOM   1673  CA   LEU A 453      -1.054  25.497   7.506  1.00 19.89
ATOM   1674  CB   LEU A 453      -0.537  24.388   8.419  1.00 20.64
ATOM   1675  CG   LEU A 453       0.926  23.948   8.354  1.00 21.11
ATOM   1676  CD1  LEU A 453       1.002  22.710   9.203  1.00 23.08
ATOM   1677  CD2  LEU A 453       1.427  23.652   6.939  1.00 18.49
ATOM   1678  C    LEU A 453      -2.575  25.383   7.371  1.00 20.98
ATOM   1679  O    LEU A 453      -3.075  24.604   6.546  1.00 19.80
ATOM   1680  N    GLU A 454      -3.317  26.145   8.173  1.00 20.65
ATOM   1681  CA   GLU A 454      -4.766  26.109   8.054  1.00 22.76
ATOM   1682  CB   GLU A 454      -5.421  27.036   9.050  1.00 27.08
ATOM   1683  CG   GLU A 454      -5.336  26.639  10.493  1.00 37.54
ATOM   1684  CD   GLU A 454      -5.781  27.780  11.405  1.00 44.10
ATOM   1685  OE1  GLU A 454      -5.524  27.691  12.629  1.00 48.07
ATOM   1686  OE2  GLU A 454      -6.360  28.779  10.897  1.00 46.31
ATOM   1687  C    GLU A 454      -5.147  26.628   6.672  1.00 22.48
ATOM   1688  O    GLU A 454      -6.145  26.200   6.086  1.00 22.34
ATOM   1689  N    ARG A 455      -4.376  27.603   6.192  1.00 21.33
ATOM   1690  CA   ARG A 455      -4.613  28.220   4.895  1.00 20.72
ATOM   1691  CB   ARG A 455      -4.129  29.669   4.894  1.00 21.51
ATOM   1692  CG   ARG A 455      -4.765  30.569   5.959  1.00 24.90
ATOM   1693  CD   ARG A 455      -4.232  32.027   5.886  1.00 29.26
ATOM   1694  NE   ARG A 455      -2.793  32.065   5.625  1.00 36.13
ATOM   1695  CZ   ARG A 455      -2.246  32.387   4.447  1.00 40.21
ATOM   1696  NH1  ARG A 455      -3.012  32.734   3.411  1.00 40.99
ATOM   1697  NH2  ARG A 455      -0.942  32.209   4.249  1.00 41.74
ATOM   1698  C    ARG A 455      -3.967  27.444   3.745  1.00 19.88
```

Figure 10

| ATOM | 1699 | O   | ARG A 455 | -4.097  | 27.838 | 2.599  | 1.00 | 20.49 |
|------|------|-----|-----------|---------|--------|--------|------|-------|
| ATOM | 1700 | N   | GLY A 456 | -3.278  | 26.342 | 4.051  | 1.00 | 19.14 |
| ATOM | 1701 | CA  | GLY A 456 | -2.647  | 25.535 | 3.013  | 1.00 | 16.91 |
| ATOM | 1702 | C   | GLY A 456 | -1.238  | 25.920 | 2.611  | 1.00 | 15.44 |
| ATOM | 1703 | O   | GLY A 456 | -0.716  | 25.490 | 1.582  | 1.00 | 15.46 |
| ATOM | 1704 | N   | TYR A 457 | -0.583  | 26.692 | 3.454  | 1.00 | 13.73 |
| ATOM | 1705 | CA  | TYR A 457 | 0.763   | 27.134 | 3.162  | 1.00 | 14.65 |
| ATOM | 1706 | CB  | TYR A 457 | 1.200   | 28.098 | 4.262  | 1.00 | 14.06 |
| ATOM | 1707 | CG  | TYR A 457 | 2.578   | 28.665 | 4.083  | 1.00 | 14.28 |
| ATOM | 1708 | CD1 | TYR A 457 | 2.781   | 29.869 | 3.383  | 1.00 | 12.32 |
| ATOM | 1709 | CE1 | TYR A 457 | 4.063   | 30.390 | 3.223  | 1.00 | 13.17 |
| ATOM | 1710 | CD2 | TYR A 457 | 3.689   | 28.001 | 4.618  | 1.00 | 12.93 |
| ATOM | 1711 | CE2 | TYR A 457 | 4.967   | 28.510 | 4.460  | 1.00 | 13.73 |
| ATOM | 1712 | CZ  | TYR A 457 | 5.153   | 29.701 | 3.763  | 1.00 | 14.69 |
| ATOM | 1713 | OH  | TYR A 457 | 6.441   | 30.166 | 3.594  | 1.00 | 16.19 |
| ATOM | 1714 | C   | TYR A 457 | 1.802   | 26.016 | 2.991  | 1.00 | 15.77 |
| ATOM | 1715 | O   | TYR A 457 | 1.758   | 25.008 | 3.685  | 1.00 | 16.22 |
| ATOM | 1716 | N   | ARG A 458 | 2.719   | 26.199 | 2.040  | 1.00 | 15.92 |
| ATOM | 1717 | CA  | ARG A 458 | 3.819   | 25.252 | 1.804  | 1.00 | 17.35 |
| ATOM | 1718 | CB  | ARG A 458 | 3.587   | 24.366 | 0.563  | 1.00 | 15.85 |
| ATOM | 1719 | CG  | ARG A 458 | 2.448   | 23.357 | 0.683  | 1.00 | 13.07 |
| ATOM | 1720 | CD  | ARG A 458 | 2.635   | 22.460 | 1.886  | 1.00 | 12.20 |
| ATOM | 1721 | NE  | ARG A 458 | 1.592   | 21.435 | 1.966  | 1.00 | 12.53 |
| ATOM | 1722 | CZ  | ARG A 458 | 0.486   | 21.539 | 2.693  | 1.00 | 10.32 |
| ATOM | 1723 | NH1 | ARG A 458 | 0.251   | 22.621 | 3.424  | 1.00 | 11.80 |
| ATOM | 1724 | NH2 | ARG A 458 | -0.402  | 20.572 | 2.670  | 1.00 | 8.76  |
| ATOM | 1725 | C   | ARG A 458 | 5.083   | 26.091 | 1.599  | 1.00 | 18.59 |
| ATOM | 1726 | O   | ARG A 458 | 5.035   | 27.159 | 0.972  | 1.00 | 17.59 |
| ATOM | 1727 | N   | MET A 459 | 6.188   | 25.659 | 2.200  | 1.00 | 19.10 |
| ATOM | 1728 | CA  | MET A 459 | 7.445   | 26.381 | 2.049  | 1.00 | 19.50 |
| ATOM | 1729 | CB  | MET A 459 | 8.576   | 25.705 | 2.843  | 1.00 | 18.64 |
| ATOM | 1730 | CG  | MET A 459 | 8.468   | 25.811 | 4.358  | 1.00 | 19.91 |
| ATOM | 1731 | SD  | MET A 459 | 9.956   | 25.176 | 5.146  | 1.00 | 22.40 |
| ATOM | 1732 | CE  | MET A 459 | 9.416   | 23.529 | 5.637  | 1.00 | 24.68 |
| ATOM | 1733 | C   | MET A 459 | 7.840   | 26.390 | 0.585  | 1.00 | 19.58 |
| ATOM | 1734 | O   | MET A 459 | 7.541   | 25.458 | -0.154 | 1.00 | 19.32 |
| ATOM | 1735 | N   | VAL A 460 | 8.554   | 27.434 | 0.185  | 1.00 | 20.91 |
| ATOM | 1736 | CA  | VAL A 460 | 9.049   | 27.546 | -1.178 | 1.00 | 21.50 |
| ATOM | 1737 | CB  | VAL A 460 | 9.364   | 29.005 | -1.536 | 1.00 | 21.30 |
| ATOM | 1738 | CG1 | VAL A 460 | 8.156   | 29.856 | -1.243 | 1.00 | 22.78 |
| ATOM | 1739 | CG2 | VAL A 460 | 10.554  | 29.506 | -0.735 | 1.00 | 21.29 |
| ATOM | 1740 | C   | VAL A 460 | 10.338  | 26.731 | -1.245 | 1.00 | 21.83 |
| ATOM | 1741 | O   | VAL A 460 | 10.854  | 26.293 | -0.216 | 1.00 | 19.47 |
| ATOM | 1742 | N   | ARG A 461 | 10.831  | 26.511 | -2.460 | 1.00 | 22.80 |
| ATOM | 1743 | CA  | ARG A 461 | 12.067  | 25.762 | -2.688 | 1.00 | 24.89 |
| ATOM | 1744 | CB  | ARG A 461 | 12.320  | 25.647 | -4.195 | 1.00 | 25.63 |
| ATOM | 1745 | CG  | ARG A 461 | 13.443  | 24.741 | -4.610 | 1.00 | 28.55 |
| ATOM | 1746 | CD  | ARG A 461 | 13.566  | 24.699 | -6.132 | 1.00 | 35.37 |
| ATOM | 1747 | NE  | ARG A 461 | 14.020  | 25.975 | -6.679 | 1.00 | 41.66 |
| ATOM | 1748 | CZ  | ARG A 461 | 15.240  | 26.488 | -6.491 | 1.00 | 46.26 |
| ATOM | 1749 | NH1 | ARG A 461 | 16.159  | 25.833 | -5.780 | 1.00 | 46.65 |
| ATOM | 1750 | NH2 | ARG A 461 | 15.520  | 27.709 | -6.934 | 1.00 | 48.77 |
| ATOM | 1751 | C   | ARG A 461 | 13.263  | 26.438 | -1.975 | 1.00 | 27.22 |
| ATOM | 1752 | O   | ARG A 461 | 13.583  | 27.612 | -2.221 | 1.00 | 26.47 |
| ATOM | 1753 | N   | PRO A 462 | 13.908  | 25.714 | -1.037 | 1.00 | 28.69 |
| ATOM | 1754 | CD  | PRO A 462 | 13.594  | 24.350 | -0.560 | 1.00 | 27.59 |
| ATOM | 1755 | CA  | PRO A 462 | 15.050  | 26.279 | -0.310 | 1.00 | 29.80 |
| ATOM | 1756 | CB  | PRO A 462 | 15.421  | 25.158 | 0.673  | 1.00 | 29.53 |
| ATOM | 1757 | CG  | PRO A 462 | 14.129  | 24.366 | 0.843  | 1.00 | 27.17 |

Figure 10

| ATOM | 1758 | C | PRO | A | 462 | 16.208 | 26.571 | -1.250 | 1.00 | 32.31 |
| --- | --- | --- | --- | --- | --- | --- | --- | --- | --- | --- |
| ATOM | 1759 | O | PRO | A | 462 | 16.335 | 25.951 | -2.308 | 1.00 | 31.39 |
| ATOM | 1760 | N | ASP | A | 463 | 17.052 | 27.521 | -0.866 | 1.00 | 35.90 |
| ATOM | 1761 | CA | ASP | A | 463 | 18.212 | 27.839 | -1.684 | 1.00 | 38.76 |
| ATOM | 1762 | CB | ASP | A | 463 | 19.005 | 29.005 | -1.091 | 1.00 | 40.30 |
| ATOM | 1763 | CG | ASP | A | 463 | 18.263 | 30.315 | -1.184 | 1.00 | 42.08 |
| ATOM | 1764 | OD1 | ASP | A | 463 | 17.628 | 30.565 | -2.231 | 1.00 | 41.92 |
| ATOM | 1765 | OD2 | ASP | A | 463 | 18.318 | 31.093 | -0.206 | 1.00 | 44.48 |
| ATOM | 1766 | C | ASP | A | 463 | 19.101 | 26.610 | -1.760 | 1.00 | 39.67 |
| ATOM | 1767 | O | ASP | A | 463 | 19.318 | 25.913 | -0.750 | 1.00 | 39.94 |
| ATOM | 1768 | N | ASN | A | 464 | 19.576 | 26.349 | -2.975 | 1.00 | 40.75 |
| ATOM | 1769 | CA | ASN | A | 464 | 20.458 | 25.231 | -3.282 | 1.00 | 41.67 |
| ATOM | 1770 | CB | ASN | A | 464 | 21.759 | 25.331 | -2.476 | 1.00 | 45.55 |
| ATOM | 1771 | CG | ASN | A | 464 | 22.672 | 26.454 | -2.976 | 1.00 | 49.49 |
| ATOM | 1772 | OD1 | ASN | A | 464 | 23.203 | 26.393 | -4.099 | 1.00 | 50.83 |
| ATOM | 1773 | ND2 | ASN | A | 464 | 22.844 | 27.491 | -2.154 | 1.00 | 50.35 |
| ATOM | 1774 | C | ASN | A | 464 | 19.788 | 23.883 | -3.079 | 1.00 | 40.76 |
| ATOM | 1775 | O | ASN | A | 464 | 20.333 | 22.994 | -2.419 | 1.00 | 41.27 |
| ATOM | 1776 | N | CYS | A | 465 | 18.613 | 23.739 | -3.690 | 1.00 | 37.52 |
| ATOM | 1777 | CA | CYS | A | 465 | 17.819 | 22.521 | -3.616 | 1.00 | 34.14 |
| ATOM | 1778 | CB | CYS | A | 465 | 16.632 | 22.744 | -2.668 | 1.00 | 33.01 |
| ATOM | 1779 | SG | CYS | A | 465 | 15.380 | 21.419 | -2.636 | 1.00 | 29.34 |
| ATOM | 1780 | C | CYS | A | 465 | 17.310 | 22.206 | -5.021 | 1.00 | 33.48 |
| ATOM | 1781 | O | CYS | A | 465 | 16.660 | 23.046 | -5.640 | 1.00 | 33.73 |
| ATOM | 1782 | N | PRO | A | 466 | 17.637 | 21.015 | -5.568 | 1.00 | 32.50 |
| ATOM | 1783 | CD | PRO | A | 466 | 18.516 | 19.976 | -5.001 | 1.00 | 31.28 |
| ATOM | 1784 | CA | PRO | A | 466 | 17.183 | 20.633 | -6.918 | 1.00 | 31.72 |
| ATOM | 1785 | CB | PRO | A | 466 | 17.671 | 19.190 | -7.045 | 1.00 | 30.19 |
| ATOM | 1786 | CG | PRO | A | 466 | 18.922 | 19.195 | -6.243 | 1.00 | 30.60 |
| ATOM | 1787 | C | PRO | A | 466 | 15.656 | 20.705 | -7.027 | 1.00 | 32.73 |
| ATOM | 1788 | O | PRO | A | 466 | 14.965 | 20.480 | -6.033 | 1.00 | 34.82 |
| ATOM | 1789 | N | GLU | A | 467 | 15.124 | 21.024 | -8.208 | 1.00 | 31.65 |
| ATOM | 1790 | CA | GLU | A | 467 | 13.676 | 21.110 | -8.360 | 1.00 | 30.08 |
| ATOM | 1791 | CB | GLU | A | 467 | 13.286 | 21.695 | -9.716 | 1.00 | 31.59 |
| ATOM | 1792 | CG | GLU | A | 467 | 12.641 | 23.091 | -9.626 | 1.00 | 35.33 |
| ATOM | 1793 | CD | GLU | A | 467 | 11.256 | 23.118 | -8.941 | 1.00 | 36.63 |
| ATOM | 1794 | OE1 | GLU | A | 467 | 11.058 | 23.978 | -8.045 | 1.00 | 37.62 |
| ATOM | 1795 | OE2 | GLU | A | 467 | 10.364 | 22.311 | -9.312 | 1.00 | 35.62 |
| ATOM | 1796 | C | GLU | A | 467 | 12.986 | 19.770 | -8.137 | 1.00 | 28.48 |
| ATOM | 1797 | O | GLU | A | 467 | 11.889 | 19.720 | -7.591 | 1.00 | 27.69 |
| ATOM | 1798 | N | GLU | A | 468 | 13.644 | 18.683 | -8.524 | 1.00 | 28.25 |
| ATOM | 1799 | CA | GLU | A | 468 | 13.077 | 17.343 | -8.335 | 1.00 | 29.16 |
| ATOM | 1800 | CB | GLU | A | 468 | 13.927 | 16.259 | -9.016 | 1.00 | 32.73 |
| ATOM | 1801 | CG | GLU | A | 468 | 14.173 | 16.467 | -10.508 | 1.00 | 38.92 |
| ATOM | 1802 | CD | GLU | A | 468 | 15.127 | 17.648 | -10.793 | 1.00 | 44.21 |
| ATOM | 1803 | OE1 | GLU | A | 468 | 16.187 | 17.748 | -10.113 | 1.00 | 42.47 |
| ATOM | 1804 | OE2 | GLU | A | 468 | 14.804 | 18.481 | -11.689 | 1.00 | 47.31 |
| ATOM | 1805 | C | GLU | A | 468 | 12.962 | 17.023 | -6.848 | 1.00 | 27.49 |
| ATOM | 1806 | O | GLU | A | 468 | 12.029 | 16.346 | -6.433 | 1.00 | 27.47 |
| ATOM | 1807 | N | LEU | A | 469 | 13.936 | 17.481 | -6.061 | 1.00 | 25.61 |
| ATOM | 1808 | CA | LEU | A | 469 | 13.918 | 17.255 | -4.628 | 1.00 | 24.16 |
| ATOM | 1809 | CB | LEU | A | 469 | 15.250 | 17.648 | -3.978 | 1.00 | 23.57 |
| ATOM | 1810 | CG | LEU | A | 469 | 15.403 | 17.431 | -2.463 | 1.00 | 23.37 |
| ATOM | 1811 | CD1 | LEU | A | 469 | 15.057 | 16.017 | -2.070 | 1.00 | 24.15 |
| ATOM | 1812 | CD2 | LEU | A | 469 | 16.815 | 17.731 | -2.047 | 1.00 | 24.56 |
| ATOM | 1813 | C | LEU | A | 469 | 12.767 | 18.044 | -4.018 | 1.00 | 23.65 |
| ATOM | 1814 | O | LEU | A | 469 | 12.028 | 17.509 | -3.190 | 1.00 | 24.23 |
| ATOM | 1815 | N | TYR | A | 470 | 12.570 | 19.283 | -4.469 | 1.00 | 22.27 |
| ATOM | 1816 | CA | TYR | A | 470 | 11.478 | 20.104 | -3.948 | 1.00 | 22.11 |

Figure 10

| | | | | | | | | | |
|---|---|---|---|---|---|---|---|---|---|
| ATOM | 1817 | CB | TYR | A | 470 | 11.507 | 21.515 | -4.529 | 1.00 21.05 |
| ATOM | 1818 | CG | TYR | A | 470 | 10.383 | 22.408 | -4.010 | 1.00 20.50 |
| ATOM | 1819 | CD1 | TYR | A | 470 | 10.239 | 22.686 | -2.641 | 1.00 16.74 |
| ATOM | 1820 | CE1 | TYR | A | 470 | 9.215 | 23.522 | -2.179 | 1.00 17.75 |
| ATOM | 1821 | CD2 | TYR | A | 470 | 9.476 | 22.985 | -4.895 | 1.00 20.46 |
| ATOM | 1822 | CE2 | TYR | A | 470 | 8.451 | 23.820 | -4.438 | 1.00 18.92 |
| ATOM | 1823 | CZ | TYR | A | 470 | 8.323 | 24.080 | -3.089 | 1.00 18.62 |
| ATOM | 1824 | OH | TYR | A | 470 | 7.275 | 24.861 | -2.668 | 1.00 16.80 |
| ATOM | 1825 | C | TYR | A | 470 | 10.119 | 19.473 | -4.219 | 1.00 21.58 |
| ATOM | 1826 | O | TYR | A | 470 | 9.226 | 19.508 | -3.364 | 1.00 22.16 |
| ATOM | 1827 | N | GLN | A | 471 | 9.963 | 18.914 | -5.414 | 1.00 20.55 |
| ATOM | 1828 | CA | GLN | A | 471 | 8.719 | 18.256 | -5.782 | 1.00 20.94 |
| ATOM | 1829 | CB | GLN | A | 471 | 8.682 | 17.992 | -7.290 | 1.00 20.24 |
| ATOM | 1830 | CG | GLN | A | 471 | 8.665 | 19.282 | -8.141 | 1.00 22.01 |
| ATOM | 1831 | CD | GLN | A | 471 | 7.547 | 20.258 | -7.751 | 1.00 23.04 |
| ATOM | 1832 | OE1 | GLN | A | 471 | 6.425 | 19.856 | -7.436 | 1.00 24.47 |
| ATOM | 1833 | NE2 | GLN | A | 471 | 7.863 | 21.549 | -7.756 | 1.00 23.15 |
| ATOM | 1834 | C | GLN | A | 471 | 8.506 | 16.970 | -4.956 | 1.00 20.48 |
| ATOM | 1835 | O | GLN | A | 471 | 7.373 | 16.506 | -4.770 | 1.00 19.16 |
| ATOM | 1836 | N | LEU | A | 472 | 9.607 | 16.417 | -4.448 | 1.00 21.02 |
| ATOM | 1837 | CA | LEU | A | 472 | 9.556 | 15.227 | -3.606 | 1.00 20.88 |
| ATOM | 1838 | CB | LEU | A | 472 | 10.953 | 14.642 | -3.437 | 1.00 21.87 |
| ATOM | 1839 | CG | LEU | A | 472 | 11.079 | 13.120 | -3.356 | 1.00 25.39 |
| ATOM | 1840 | CD1 | LEU | A | 472 | 10.550 | 12.478 | -4.629 | 1.00 25.84 |
| ATOM | 1841 | CD2 | LEU | A | 472 | 12.550 | 12.759 | -3.173 | 1.00 27.21 |
| ATOM | 1842 | C | LEU | A | 472 | 9.012 | 15.712 | -2.268 | 1.00 19.85 |
| ATOM | 1843 | O | LEU | A | 472 | 8.121 | 15.088 | -1.695 | 1.00 21.86 |
| ATOM | 1844 | N | MET | A | 473 | 9.527 | 16.851 | -1.805 | 1.00 17.81 |
| ATOM | 1845 | CA | MET | A | 473 | 9.088 | 17.469 | -0.566 | 1.00 16.37 |
| ATOM | 1846 | CB | MET | A | 473 | 9.840 | 18.772 | -0.335 | 1.00 16.12 |
| ATOM | 1847 | CG | MET | A | 473 | 11.257 | 18.670 | 0.138 | 1.00 14.40 |
| ATOM | 1848 | SD | MET | A | 473 | 11.993 | 20.307 | -0.082 | 1.00 16.54 |
| ATOM | 1849 | CE | MET | A | 473 | 13.720 | 19.976 | 0.329 | 1.00 14.92 |
| ATOM | 1850 | C | MET | A | 473 | 7.593 | 17.799 | -0.628 | 1.00 16.02 |
| ATOM | 1851 | O | MET | A | 473 | 6.856 | 17.575 | 0.339 | 1.00 14.95 |
| ATOM | 1852 | N | ARG | A | 474 | 7.159 | 18.349 | -1.762 | 1.00 16.32 |
| ATOM | 1853 | CA | ARG | A | 474 | 5.759 | 18.723 | -1.952 | 1.00 16.26 |
| ATOM | 1854 | CB | ARG | A | 474 | 5.558 | 19.465 | -3.289 | 1.00 17.91 |
| ATOM | 1855 | CG | ARG | A | 474 | 6.267 | 20.827 | -3.362 | 1.00 19.60 |
| ATOM | 1856 | CD | ARG | A | 474 | 5.815 | 21.779 | -2.235 | 1.00 20.87 |
| ATOM | 1857 | NE | ARG | A | 474 | 4.385 | 22.068 | -2.331 | 1.00 23.02 |
| ATOM | 1858 | CZ | ARG | A | 474 | 3.864 | 23.180 | -2.842 | 1.00 24.04 |
| ATOM | 1859 | NH1 | ARG | A | 474 | 4.651 | 24.150 | -3.301 | 1.00 22.49 |
| ATOM | 1860 | NH2 | ARG | A | 474 | 2.544 | 23.299 | -2.931 | 1.00 24.53 |
| ATOM | 1861 | C | ARG | A | 474 | 4.842 | 17.516 | -1.865 | 1.00 15.87 |
| ATOM | 1862 | O | ARG | A | 474 | 3.705 | 17.634 | -1.422 | 1.00 15.77 |
| ATOM | 1863 | N | LEU | A | 475 | 5.346 | 16.355 | -2.280 | 1.00 16.10 |
| ATOM | 1864 | CA | LEU | A | 475 | 4.584 | 15.107 | -2.227 | 1.00 17.19 |
| ATOM | 1865 | CB | LEU | A | 475 | 5.279 | 14.007 | -3.023 | 1.00 18.56 |
| ATOM | 1866 | CG | LEU | A | 475 | 5.086 | 14.031 | -4.535 | 1.00 20.75 |
| ATOM | 1867 | CD1 | LEU | A | 475 | 5.937 | 12.930 | -5.166 | 1.00 19.90 |
| ATOM | 1868 | CD2 | LEU | A | 475 | 3.597 | 13.859 | -4.858 | 1.00 20.43 |
| ATOM | 1869 | C | LEU | A | 475 | 4.431 | 14.654 | -0.790 | 1.00 16.74 |
| ATOM | 1870 | O | LEU | A | 475 | 3.418 | 14.088 | -0.423 | 1.00 17.62 |
| ATOM | 1871 | N | CYS | A | 476 | 5.461 | 14.900 | 0.011 | 1.00 17.80 |
| ATOM | 1872 | CA | CYS | A | 476 | 5.462 | 14.554 | 1.431 | 1.00 17.15 |
| ATOM | 1873 | CB | CYS | A | 476 | 6.888 | 14.704 | 2.014 | 1.00 16.14 |
| ATOM | 1874 | SG | CYS | A | 476 | 8.214 | 13.591 | 1.328 | 1.00 16.99 |
| ATOM | 1875 | C | CYS | A | 476 | 4.478 | 15.466 | 2.193 | 1.00 16.85 |

Figure 10

| | | | | | | | | |
|---|---|---|---|---|---|---|---|---|
| ATOM | 1876 | O | CYS | A | 476 | 4.004 | 15.110 | 3.274 | 1.00 16.60 |
| ATOM | 1877 | N | TRP | A | 477 | 4.184 | 16.639 | 1.622 | 1.00 16.74 |
| ATOM | 1878 | CA | TRP | A | 477 | 3.281 | 17.618 | 2.236 | 1.00 16.42 |
| ATOM | 1879 | CB | TRP | A | 477 | 3.881 | 19.043 | 2.182 | 1.00 14.68 |
| ATOM | 1880 | CG | TRP | A | 477 | 5.272 | 19.164 | 2.752 | 1.00 13.36 |
| ATOM | 1881 | CD2 | TRP | A | 477 | 6.287 | 20.107 | 2.365 | 1.00 13.02 |
| ATOM | 1882 | CE2 | TRP | A | 477 | 7.434 | 19.823 | 3.137 | 1.00 12.90 |
| ATOM | 1883 | CE3 | TRP | A | 477 | 6.339 | 21.161 | 1.444 | 1.00 13.75 |
| ATOM | 1884 | CD1 | TRP | A | 477 | 5.832 | 18.380 | 3.719 | 1.00 12.17 |
| ATOM | 1885 | NE1 | TRP | A | 477 | 7.122 | 18.765 | 3.951 | 1.00 12.74 |
| ATOM | 1886 | CZ2 | TRP | A | 477 | 8.627 | 20.559 | 3.018 | 1.00 12.42 |
| ATOM | 1887 | CZ3 | TRP | A | 477 | 7.519 | 21.889 | 1.325 | 1.00 13.09 |
| ATOM | 1888 | CH2 | TRP | A | 477 | 8.647 | 21.581 | 2.110 | 1.00 13.47 |
| ATOM | 1889 | C | TRP | A | 477 | 1.889 | 17.641 | 1.597 | 1.00 16.66 |
| ATOM | 1890 | O | TRP | A | 477 | 1.198 | 18.670 | 1.646 | 1.00 17.24 |
| ATOM | 1891 | N | LYS | A | 478 | 1.469 | 16.536 | 0.988 | 1.00 14.64 |
| ATOM | 1892 | CA | LYS | A | 478 | 0.150 | 16.537 | 0.399 | 1.00 14.87 |
| ATOM | 1893 | CB | LYS | A | 478 | -0.129 | 15.268 | -0.409 | 1.00 14.76 |
| ATOM | 1894 | CG | LYS | A | 478 | 0.651 | 15.156 | -1.719 | 1.00 16.65 |
| ATOM | 1895 | CD | LYS | A | 478 | 0.312 | 16.221 | -2.740 | 1.00 17.12 |
| ATOM | 1896 | CE | LYS | A | 478 | -1.101 | 16.091 | -3.203 | 1.00 21.46 |
| ATOM | 1897 | NZ | LYS | A | 478 | -1.514 | 17.275 | -4.002 | 1.00 24.73 |
| ATOM | 1898 | C | LYS | A | 478 | -0.775 | 16.636 | 1.577 | 1.00 15.59 |
| ATOM | 1899 | O | LYS | A | 478 | -0.507 | 16.051 | 2.616 | 1.00 16.20 |
| ATOM | 1900 | N | GLU | A | 479 | -1.827 | 17.431 | 1.441 | 1.00 16.53 |
| ATOM | 1901 | CA | GLU | A | 479 | -2.784 | 17.611 | 2.519 | 1.00 17.85 |
| ATOM | 1902 | CB | GLU | A | 479 | -3.957 | 18.478 | 2.059 | 1.00 16.00 |
| ATOM | 1903 | CG | GLU | A | 479 | -4.887 | 18.900 | 3.192 | 1.00 16.68 |
| ATOM | 1904 | CD | GLU | A | 479 | -4.198 | 19.785 | 4.230 | 1.00 20.30 |
| ATOM | 1905 | OE1 | GLU | A | 479 | -3.258 | 20.529 | 3.881 | 1.00 20.75 |
| ATOM | 1906 | OE2 | GLU | A | 479 | -4.599 | 19.748 | 5.408 | 1.00 21.49 |
| ATOM | 1907 | C | GLU | A | 479 | -3.276 | 16.259 | 3.002 | 1.00 18.25 |
| ATOM | 1908 | O | GLU | A | 479 | -3.107 | 15.923 | 4.167 | 1.00 19.57 |
| ATOM | 1909 | N | ARG | A | 480 | -3.836 | 15.469 | 2.093 | 1.00 19.12 |
| ATOM | 1910 | CA | ARG | A | 480 | -4.337 | 14.142 | 2.438 | 1.00 19.83 |
| ATOM | 1911 | CB | ARG | A | 480 | -5.243 | 13.638 | 1.338 | 1.00 23.23 |
| ATOM | 1912 | CG | ARG | A | 480 | -6.505 | 14.416 | 1.134 | 1.00 27.34 |
| ATOM | 1913 | CD | ARG | A | 480 | -7.089 | 13.885 | -0.130 | 1.00 34.14 |
| ATOM | 1914 | NE | ARG | A | 480 | -8.435 | 14.357 | -0.396 | 1.00 42.99 |
| ATOM | 1915 | CZ | ARG | A | 480 | -8.949 | 14.467 | -1.620 | 1.00 45.74 |
| ATOM | 1916 | NH1 | ARG | A | 480 | -8.211 | 14.148 | -2.688 | 1.00 46.42 |
| ATOM | 1917 | NH2 | ARG | A | 480 | -10.209 | 14.868 | -1.768 | 1.00 46.62 |
| ATOM | 1918 | C | ARG | A | 480 | -3.207 | 13.139 | 2.626 | 1.00 18.26 |
| ATOM | 1919 | O | ARG | A | 480 | -2.372 | 12.984 | 1.752 | 1.00 19.76 |
| ATOM | 1920 | N | PRO | A | 481 | -3.181 | 12.426 | 3.767 | 1.00 17.26 |
| ATOM | 1921 | CD | PRO | A | 481 | -4.139 | 12.519 | 4.884 | 1.00 15.35 |
| ATOM | 1922 | CA | PRO | A | 481 | -2.148 | 11.429 | 4.068 | 1.00 15.71 |
| ATOM | 1923 | CB | PRO | A | 481 | -2.685 | 10.765 | 5.336 | 1.00 14.01 |
| ATOM | 1924 | CG | PRO | A | 481 | -3.391 | 11.863 | 6.001 | 1.00 14.55 |
| ATOM | 1925 | C | PRO | A | 481 | -1.953 | 10.395 | 2.965 | 1.00 15.61 |
| ATOM | 1926 | O | PRO | A | 481 | -0.829 | 10.063 | 2.632 | 1.00 15.62 |
| ATOM | 1927 | N | GLU | A | 482 | -3.059 | 9.902 | 2.404 | 1.00 16.65 |
| ATOM | 1928 | CA | GLU | A | 482 | -3.048 | 8.886 | 1.346 | 1.00 16.81 |
| ATOM | 1929 | CB | GLU | A | 482 | -4.496 | 8.484 | 1.016 | 1.00 17.18 |
| ATOM | 1930 | CG | GLU | A | 482 | -5.301 | 9.542 | 0.234 | 1.00 20.95 |
| ATOM | 1931 | CD | GLU | A | 482 | -6.363 | 10.299 | 1.047 | 1.00 20.82 |
| ATOM | 1932 | OE1 | GLU | A | 482 | -6.170 | 10.542 | 2.254 | 1.00 21.26 |
| ATOM | 1933 | OE2 | GLU | A | 482 | -7.401 | 10.679 | 0.450 | 1.00 24.62 |
| ATOM | 1934 | C | GLU | A | 482 | -2.295 | 9.322 | 0.073 | 1.00 17.54 |

Figure 10

```
ATOM   1935  O    GLU A 482      -1.779   8.491  -0.691  1.00 17.99
ATOM   1936  N    ASP A 483      -2.213  10.634  -0.144  1.00 17.84
ATOM   1937  CA   ASP A 483      -1.524  11.180  -1.310  1.00 16.45
ATOM   1938  CB   ASP A 483      -2.102  12.535  -1.702  1.00 16.44
ATOM   1939  CG   ASP A 483      -3.535  12.433  -2.150  1.00 16.40
ATOM   1940  OD1  ASP A 483      -3.897  11.398  -2.728  1.00 17.95
ATOM   1941  OD2  ASP A 483      -4.312  13.363  -1.912  1.00 17.36
ATOM   1942  C    ASP A 483      -0.048  11.298  -1.125  1.00 15.53
ATOM   1943  O    ASP A 483       0.645  11.692  -2.062  1.00 15.99
ATOM   1944  N    ARG A 484       0.428  10.965   0.076  1.00 14.42
ATOM   1945  CA   ARG A 484       1.858  11.020   0.389  1.00 14.65
ATOM   1946  CB   ARG A 484       2.080  11.362   1.862  1.00 13.11
ATOM   1947  CG   ARG A 484       1.441  12.656   2.265  1.00 11.87
ATOM   1948  CD   ARG A 484       1.582  12.926   3.751  1.00 13.72
ATOM   1949  NE   ARG A 484       0.644  13.971   4.168  1.00 15.01
ATOM   1950  CZ   ARG A 484       0.134  14.110   5.392  1.00 13.78
ATOM   1951  NH1  ARG A 484       0.475  13.275   6.357  1.00 12.19
ATOM   1952  NH2  ARG A 484      -0.763  15.058   5.631  1.00 12.92
ATOM   1953  C    ARG A 484       2.541   9.694   0.046  1.00 15.15
ATOM   1954  O    ARG A 484       1.978   8.620   0.267  1.00 14.30
ATOM   1955  N    PRO A 485       3.783   9.756  -0.466  1.00 15.57
ATOM   1956  CD   PRO A 485       4.647  10.943  -0.493  1.00 13.89
ATOM   1957  CA   PRO A 485       4.533   8.556  -0.839  1.00 15.89
ATOM   1958  CB   PRO A 485       5.846   9.118  -1.406  1.00 17.12
ATOM   1959  CG   PRO A 485       5.619  10.588  -1.541  1.00 17.22
ATOM   1960  C    PRO A 485       4.854   7.652   0.342  1.00 17.03
ATOM   1961  O    PRO A 485       4.815   8.053   1.500  1.00 17.93
ATOM   1962  N    THR A 486       5.230   6.430   0.028  1.00 16.55
ATOM   1963  CA   THR A 486       5.636   5.493   1.046  1.00 15.80
ATOM   1964  CB   THR A 486       5.443   4.036   0.566  1.00 14.24
ATOM   1965  OG1  THR A 486       6.188   3.845  -0.644  1.00 16.13
ATOM   1966  CG2  THR A 486       3.968   3.732   0.322  1.00 11.81
ATOM   1967  C    THR A 486       7.142   5.742   1.203  1.00 15.57
ATOM   1968  O    THR A 486       7.790   6.223   0.282  1.00 15.66
ATOM   1969  N    PHE A 487       7.693   5.411   2.363  1.00 16.60
ATOM   1970  CA   PHE A 487       9.125   5.560   2.586  1.00 18.21
ATOM   1971  CB   PHE A 487       9.472   5.292   4.045  1.00 16.35
ATOM   1972  CG   PHE A 487       9.204   6.453   4.942  1.00 15.48
ATOM   1973  CD1  PHE A 487       9.958   7.617   4.826  1.00 12.78
ATOM   1974  CD2  PHE A 487       8.200   6.392   5.904  1.00 15.07
ATOM   1975  CE1  PHE A 487       9.718   8.701   5.651  1.00 12.01
ATOM   1976  CE2  PHE A 487       7.953   7.488   6.743  1.00 12.82
ATOM   1977  CZ   PHE A 487       8.716   8.639   6.611  1.00  9.76
ATOM   1978  C    PHE A 487       9.868   4.593   1.679  1.00 20.26
ATOM   1979  O    PHE A 487      11.036   4.807   1.364  1.00 20.95
ATOM   1980  N    ASP A 488       9.178   3.529   1.261  1.00 22.81
ATOM   1981  CA   ASP A 488       9.734   2.538   0.337  1.00 24.76
ATOM   1982  CB   ASP A 488       8.743   1.374   0.173  1.00 28.25
ATOM   1983  CG   ASP A 488       9.206   0.329  -0.841  1.00 31.36
ATOM   1984  OD1  ASP A 488      10.400  -0.037  -0.849  1.00 34.01
ATOM   1985  OD2  ASP A 488       8.356  -0.134  -1.630  1.00 32.45
ATOM   1986  C    ASP A 488       9.994   3.250  -1.011  1.00 24.34
ATOM   1987  O    ASP A 488      11.013   3.031  -1.656  1.00 24.43
ATOM   1988  N    TYR A 489       9.085   4.139  -1.404  1.00 23.76
ATOM   1989  CA   TYR A 489       9.257   4.896  -2.634  1.00 22.83
ATOM   1990  CB   TYR A 489       7.955   5.575  -3.050  1.00 21.05
ATOM   1991  CG   TYR A 489       8.169   6.605  -4.136  1.00 19.09
ATOM   1992  CD1  TYR A 489       8.434   6.217  -5.454  1.00 20.63
ATOM   1993  CE1  TYR A 489       8.658   7.162  -6.458  1.00 19.77
```

Figure 10

| | | | | | | | | |
|---|---|---|---|---|---|---|---|---|
| ATOM | 1994 | CD2 | TYR | A | 489 | 8.132 | 7.968 | -3.842 | 1.00 19.11 |
| ATOM | 1995 | CE2 | TYR | A | 489 | 8.355 | 8.928 | -4.825 | 1.00 18.30 |
| ATOM | 1996 | CZ | TYR | A | 489 | 8.618 | 8.523 | -6.136 | 1.00 22.19 |
| ATOM | 1997 | OH | TYR | A | 489 | 8.857 | 9.466 | -7.121 | 1.00 21.09 |
| ATOM | 1998 | C | TYR | A | 489 | 10.332 | 5.966 | -2.423 | 1.00 23.70 |
| ATOM | 1999 | O | TYR | A | 489 | 11.210 | 6.140 | -3.272 | 1.00 23.74 |
| ATOM | 2000 | N | LEU | A | 490 | 10.265 | 6.665 | -1.285 | 1.00 22.96 |
| ATOM | 2001 | CA | LEU | A | 490 | 11.227 | 7.715 | -0.964 | 1.00 21.65 |
| ATOM | 2002 | CB | LEU | A | 490 | 10.861 | 8.389 | 0.356 | 1.00 20.91 |
| ATOM | 2003 | CG | LEU | A | 490 | 9.637 | 9.305 | 0.302 | 1.00 20.54 |
| ATOM | 2004 | CD1 | LEU | A | 490 | 9.226 | 9.716 | 1.722 | 1.00 17.74 |
| ATOM | 2005 | CD2 | LEU | A | 490 | 9.931 | 10.520 | -0.567 | 1.00 18.48 |
| ATOM | 2006 | C | LEU | A | 490 | 12.678 | 7.223 | -0.947 | 1.00 22.12 |
| ATOM | 2007 | O | LEU | A | 490 | 13.575 | 7.926 | -1.403 | 1.00 20.34 |
| ATOM | 2008 | N | ARG | A | 491 | 12.911 | 6.023 | -0.421 | 1.00 24.26 |
| ATOM | 2009 | CA | ARG | A | 491 | 14.257 | 5.441 | -0.392 | 1.00 27.09 |
| ATOM | 2010 | CB | ARG | A | 491 | 14.258 | 4.147 | 0.412 | 1.00 30.17 |
| ATOM | 2011 | CG | ARG | A | 491 | 15.534 | 3.340 | 0.243 | 1.00 36.39 |
| ATOM | 2012 | CD | ARG | A | 491 | 15.344 | 1.901 | 0.672 | 1.00 42.21 |
| ATOM | 2013 | NE | ARG | A | 491 | 14.196 | 1.275 | 0.006 | 1.00 47.62 |
| ATOM | 2014 | CZ | ARG | A | 491 | 14.148 | 0.952 | -1.290 | 1.00 50.08 |
| ATOM | 2015 | NH1 | ARG | A | 491 | 15.189 | 1.191 | -2.094 | 1.00 49.64 |
| ATOM | 2016 | NH2 | ARG | A | 491 | 13.051 | 0.381 | -1.784 | 1.00 50.33 |
| ATOM | 2017 | C | ARG | A | 491 | 14.744 | 5.140 | -1.818 | 1.00 27.99 |
| ATOM | 2018 | O | ARG | A | 491 | 15.893 | 5.415 | -2.162 | 1.00 27.57 |
| ATOM | 2019 | N | SER | A | 492 | 13.858 | 4.565 | -2.632 | 1.00 28.89 |
| ATOM | 2020 | CA | SER | A | 492 | 14.161 | 4.232 | -4.027 | 1.00 28.99 |
| ATOM | 2021 | CB | SER | A | 492 | 12.947 | 3.611 | -4.710 | 1.00 28.87 |
| ATOM | 2022 | OG | SER | A | 492 | 12.885 | 2.223 | -4.453 | 1.00 34.11 |
| ATOM | 2023 | C | SER | A | 492 | 14.564 | 5.452 | -4.822 | 1.00 29.41 |
| ATOM | 2024 | O | SER | A | 492 | 15.617 | 5.470 | -5.456 | 1.00 28.96 |
| ATOM | 2025 | N | VAL | A | 493 | 13.714 | 6.475 | -4.777 | 1.00 30.48 |
| ATOM | 2026 | CA | VAL | A | 493 | 13.956 | 7.707 | -5.516 | 1.00 31.09 |
| ATOM | 2027 | CB | VAL | A | 493 | 12.632 | 8.571 | -5.654 | 1.00 29.94 |
| ATOM | 2028 | CG1 | VAL | A | 493 | 12.219 | 9.178 | -4.341 | 1.00 28.64 |
| ATOM | 2029 | CG2 | VAL | A | 493 | 12.790 | 9.644 | -6.715 | 1.00 30.73 |
| ATOM | 2030 | C | VAL | A | 493 | 15.177 | 8.509 | -5.019 | 1.00 31.77 |
| ATOM | 2031 | O | VAL | A | 493 | 15.917 | 9.084 | -5.832 | 1.00 31.64 |
| ATOM | 2032 | N | LEU | A | 494 | 15.464 | 8.435 | -3.719 | 1.00 32.61 |
| ATOM | 2033 | CA | LEU | A | 494 | 16.595 | 9.168 | -3.152 | 1.00 33.35 |
| ATOM | 2034 | CB | LEU | A | 494 | 16.378 | 9.438 | -1.662 | 1.00 32.08 |
| ATOM | 2035 | CG | LEU | A | 494 | 15.299 | 10.481 | -1.335 | 1.00 30.85 |
| ATOM | 2036 | CD1 | LEU | A | 494 | 15.020 | 10.511 | 0.156 | 1.00 28.55 |
| ATOM | 2037 | CD2 | LEU | A | 494 | 15.728 | 11.863 | -1.835 | 1.00 30.22 |
| ATOM | 2038 | C | LEU | A | 494 | 17.951 | 8.521 | -3.402 | 1.00 34.58 |
| ATOM | 2039 | O | LEU | A | 494 | 18.953 | 9.217 | -3.498 | 1.00 34.25 |
| ATOM | 2040 | N | GLU | A | 495 | 17.981 | 7.194 | -3.498 | 1.00 38.15 |
| ATOM | 2041 | CA | GLU | A | 495 | 19.220 | 6.462 | -3.767 | 1.00 42.45 |
| ATOM | 2042 | CB | GLU | A | 495 | 18.988 | 4.955 | -3.622 | 1.00 43.33 |
| ATOM | 2043 | CG | GLU | A | 495 | 19.352 | 4.395 | -2.258 | 1.00 46.75 |
| ATOM | 2044 | CD | GLU | A | 495 | 18.846 | 2.984 | -2.043 | 1.00 47.96 |
| ATOM | 2045 | OE1 | GLU | A | 495 | 18.622 | 2.268 | -3.052 | 1.00 48.32 |
| ATOM | 2046 | OE2 | GLU | A | 495 | 18.671 | 2.605 | -0.857 | 1.00 48.49 |
| ATOM | 2047 | C | GLU | A | 495 | 19.669 | 6.747 | -5.190 | 1.00 44.92 |
| ATOM | 2048 | O | GLU | A | 495 | 20.807 | 7.159 | -5.436 | 1.00 45.76 |
| ATOM | 2049 | N | ASP | A | 496 | 18.727 | 6.562 | -6.110 | 1.00 47.24 |
| ATOM | 2050 | CA | ASP | A | 496 | 18.936 | 6.749 | -7.538 | 1.00 49.31 |
| ATOM | 2051 | CB | ASP | A | 496 | 17.957 | 5.847 | -8.316 | 1.00 51.67 |
| ATOM | 2052 | CG | ASP | A | 496 | 18.084 | 4.353 | -7.937 | 1.00 54.75 |

Figure 10

| | | | | | | | | |
|---|---|---|---|---|---|---|---|---|
| ATOM | 2053 | OD1 | ASP | A | 496 | 19.225 | 3.854 | -7.708 | 1.00 55.50 |
| ATOM | 2054 | OD2 | ASP | A | 496 | 17.033 | 3.670 | -7.879 | 1.00 55.96 |
| ATOM | 2055 | C | ASP | A | 496 | 18.770 | 8.191 | -8.004 | 1.00 49.51 |
| ATOM | 2056 | O | ASP | A | 496 | 18.532 | 8.427 | -9.184 | 1.00 49.33 |
| ATOM | 2057 | N | PHE | A | 497 | 18.911 | 9.153 | -7.097 | 1.00 50.47 |
| ATOM | 2058 | CA | PHE | A | 497 | 18.741 | 10.554 | -7.467 | 1.00 51.89 |
| ATOM | 2059 | CB | PHE | A | 497 | 18.760 | 11.449 | -6.235 | 1.00 49.93 |
| ATOM | 2060 | CG | PHE | A | 497 | 17.976 | 12.713 | -6.406 | 1.00 47.88 |
| ATOM | 2061 | CD1 | PHE | A | 497 | 16.616 | 12.741 | -6.130 | 1.00 46.31 |
| ATOM | 2062 | CD2 | PHE | A | 497 | 18.599 | 13.879 | -6.850 | 1.00 48.76 |
| ATOM | 2063 | CE1 | PHE | A | 497 | 15.887 | 13.905 | -6.290 | 1.00 45.79 |
| ATOM | 2064 | CE2 | PHE | A | 497 | 17.878 | 15.057 | -7.013 | 1.00 47.16 |
| ATOM | 2065 | CZ | PHE | A | 497 | 16.519 | 15.068 | -6.731 | 1.00 46.88 |
| ATOM | 2066 | C | PHE | A | 497 | 19.755 | 11.037 | -8.497 | 1.00 54.13 |
| ATOM | 2067 | O | PHE | A | 497 | 19.407 | 11.801 | -9.405 | 1.00 53.79 |
| ATOM | 2068 | N | PHE | A | 498 | 21.011 | 10.629 | -8.326 | 1.00 57.26 |
| ATOM | 2069 | CA | PHE | A | 498 | 22.097 | 10.971 | -9.258 | 1.00 59.91 |
| ATOM | 2070 | CB | PHE | A | 498 | 22.205 | 12.495 | -9.526 | 1.00 60.99 |
| ATOM | 2071 | CG | PHE | A | 498 | 22.333 | 13.359 | -8.281 | 1.00 60.96 |
| ATOM | 2072 | CD1 | PHE | A | 498 | 22.789 | 12.840 | -7.076 | 1.00 60.69 |
| ATOM | 2073 | CD2 | PHE | A | 498 | 22.009 | 14.716 | -8.340 | 1.00 60.43 |
| ATOM | 2074 | CE1 | PHE | A | 498 | 22.914 | 13.656 | -5.956 | 1.00 61.55 |
| ATOM | 2075 | CE2 | PHE | A | 498 | 22.131 | 15.535 | -7.225 | 1.00 59.91 |
| ATOM | 2076 | CZ | PHE | A | 498 | 22.588 | 15.005 | -6.034 | 1.00 60.43 |
| ATOM | 2077 | C | PHE | A | 498 | 23.448 | 10.404 | -8.824 | 1.00 60.93 |
| ATOM | 2078 | O | PHE | A | 498 | 23.565 | 9.160 | -8.842 | 1.00 62.03 |
| ATOM | 2079 | N1 | LIG | A | 500 | 23.576 | 17.850 | 21.851 | 1.00 42.19 |
| ATOM | 2080 | C1 | LIG | A | 500 | 23.243 | 16.391 | 21.712 | 1.00 40.68 |
| ATOM | 2081 | C2 | LIG | A | 500 | 23.501 | 15.752 | 20.299 | 1.00 39.30 |
| ATOM | 2082 | C3 | LIG | A | 500 | 23.099 | 14.254 | 20.277 | 1.00 37.20 |
| ATOM | 2083 | C4 | LIG | A | 500 | 23.889 | 13.529 | 21.532 | 1.00 35.88 |
| ATOM | 2084 | C5 | LIG | A | 500 | 23.641 | 14.052 | 22.712 | 1.00 36.81 |
| ATOM | 2085 | C6 | LIG | A | 500 | 24.015 | 15.543 | 22.790 | 1.00 39.27 |
| ATOM | 2086 | N2 | LIG | A | 500 | 23.484 | 12.094 | 21.500 | 1.00 34.49 |
| ATOM | 2087 | N3 | LIG | A | 500 | 22.347 | 11.499 | 21.834 | 1.00 33.20 |
| ATOM | 2088 | C7 | LIG | A | 500 | 22.467 | 10.186 | 21.630 | 1.00 33.39 |
| ATOM | 2089 | C8 | LIG | A | 500 | 23.798 | 9.902 | 21.122 | 1.00 32.47 |
| ATOM | 2090 | C9 | LIG | A | 500 | 24.485 | 8.778 | 20.752 | 1.00 31.47 |
| ATOM | 2091 | N4 | LIG | A | 500 | 25.786 | 8.914 | 20.298 | 1.00 30.75 |
| ATOM | 2092 | C10 | LIG | A | 500 | 26.404 | 10.126 | 20.221 | 1.00 29.50 |
| ATOM | 2093 | N5 | LIG | A | 500 | 25.753 | 11.267 | 20.589 | 1.00 31.40 |
| ATOM | 2094 | C11 | LIG | A | 500 | 24.433 | 11.107 | 21.041 | 1.00 34.00 |
| ATOM | 2095 | N6 | LIG | A | 500 | 23.947 | 7.446 | 20.799 | 1.00 30.98 |
| ATOM | 2096 | C12 | LIG | A | 500 | 21.316 | 9.372 | 21.957 | 1.00 34.56 |
| ATOM | 2097 | C13 | LIG | A | 500 | 20.053 | 9.668 | 21.350 | 1.00 35.75 |
| ATOM | 2098 | C14 | LIG | A | 500 | 18.955 | 8.868 | 21.717 | 1.00 37.63 |
| ATOM | 2099 | C15 | LIG | A | 500 | 19.064 | 7.785 | 22.676 | 1.00 39.13 |
| ATOM | 2100 | C16 | LIG | A | 500 | 20.348 | 7.511 | 23.251 | 1.00 38.05 |
| ATOM | 2101 | C17 | LIG | A | 500 | 21.438 | 8.323 | 22.876 | 1.00 36.52 |
| ATOM | 2102 | C18 | LIG | A | 500 | 25.015 | 18.310 | 21.894 | 1.00 43.43 |
| ATOM | 2103 | C19 | LIG | A | 500 | 25.174 | 19.855 | 22.044 | 1.00 43.88 |
| ATOM | 2104 | N7 | LIG | A | 500 | 24.518 | 20.562 | 20.908 | 1.00 44.55 |
| ATOM | 2105 | C20 | LIG | A | 500 | 24.685 | 22.053 | 21.025 | 1.00 45.33 |
| ATOM | 2106 | C21 | LIG | A | 500 | 23.075 | 20.197 | 20.927 | 1.00 44.40 |
| ATOM | 2107 | C22 | LIG | A | 500 | 22.824 | 18.657 | 20.807 | 1.00 43.24 |
| ATOM | 2108 | O1 | LIG | A | 500 | 20.407 | 6.518 | 24.111 | 1.00 39.33 |
| ATOM | 2109 | C23 | LIG | A | 500 | 21.445 | 6.541 | 25.127 | 1.00 38.77 |
| ATOM | 2110 | C24 | LIG | A | 500 | 17.081 | 6.298 | 22.262 | 1.00 44.35 |
| ATOM | 2111 | O2 | LIG | A | 500 | 17.209 | 6.229 | 21.021 | 1.00 43.83 |

Figure 10

| | | | | | | | | |
|---|---|---|---|---|---|---|---|---|
| ATOM | 2112 | N8  | LIG A 500 | 17.914 | 6.981  | 23.077 | 1.00 | 41.95 |
| ATOM | 2113 | C25 | LIG A 500 | 15.972 | 5.621  | 22.850 | 1.00 | 46.74 |
| ATOM | 2114 | C26 | LIG A 500 | 15.591 | 5.553  | 24.205 | 1.00 | 47.08 |
| ATOM | 2115 | N9  | LIG A 500 | 15.082 | 4.899  | 22.064 | 1.00 | 47.32 |
| ATOM | 2116 | C27 | LIG A 500 | 13.488 | 4.287  | 25.257 | 1.00 | 46.55 |
| ATOM | 2117 | C28 | LIG A 500 | 14.379 | 4.743  | 24.237 | 1.00 | 47.01 |
| ATOM | 2118 | C29 | LIG A 500 | 14.095 | 4.355  | 22.909 | 1.00 | 47.46 |
| ATOM | 2119 | C30 | LIG A 500 | 12.971 | 3.536  | 22.617 | 1.00 | 47.54 |
| ATOM | 2120 | C31 | LIG A 500 | 12.106 | 3.100  | 23.662 | 1.00 | 46.97 |
| ATOM | 2121 | C32 | LIG A 500 | 12.368 | 3.476  | 24.984 | 1.00 | 45.93 |
| ATOM | 2122 | OH2 | H2O A 600 |  5.113 | 21.175 |  8.959 | 1.00 | 20.24 |
| ATOM | 2123 | OH2 | H2O A 601 |  1.271 |  1.918 | -1.102 | 1.00 | 91.33 |
| ATOM | 2124 | OH2 | H2O A 602 | -1.364 | 23.088 |  0.168 | 1.00 | 12.63 |
| ATOM | 2125 | OH2 | H2O A 604 |  6.344 |  1.391 | -3.303 | 1.00 | 37.37 |
| ATOM | 2126 | OH2 | H2O A 605 | -5.808 | 24.408 |  1.798 | 1.00 | 35.55 |
| ATOM | 2127 | OH2 | H2O A 606 |  7.447 | 12.252 | 12.889 | 1.00 | 12.59 |
| ATOM | 2128 | OH2 | H2O A 607 | -3.682 | 15.731 | -0.658 | 1.00 | 23.88 |
| ATOM | 2129 | OH2 | H2O A 608 |  0.493 |  7.701 | -2.714 | 1.00 | 58.00 |
| ATOM | 2130 | OH2 | H2O A 609 | -0.937 | 29.608 |  1.668 | 1.00 | 20.46 |
| ATOM | 2131 | OH2 | H2O A 610 |  5.825 | 23.370 |  4.105 | 1.00 | 17.17 |
| ATOM | 2132 | OH2 | H2O A 611 |  5.275 | 17.420 | -6.129 | 1.00 | 20.20 |
| ATOM | 2133 | OH2 | H2O A 612 |  0.553 |  4.725 |  0.462 | 1.00 | 31.73 |
| ATOM | 2134 | OH2 | H2O A 613 | -0.542 | 27.444 | -0.789 | 1.00 | 65.78 |
| ATOM | 2135 | OH2 | H2O A 614 |  9.461 |  8.702 | 18.761 | 1.00 | 16.99 |
| ATOM | 2136 | OH2 | H2O A 615 | -9.629 |  6.738 | -2.790 | 1.00 | 33.35 |
| ATOM | 2137 | OH2 | H2O A 616 | -1.824 |  5.618 | -0.434 | 1.00 | 29.17 |
| ATOM | 2138 | OH2 | H2O A 617 |  2.148 | 28.498 | -0.672 | 1.00 | 73.25 |
| ATOM | 2139 | OH2 | H2O A 618 |  8.228 | 23.719 | 15.861 | 1.00 | 26.94 |
| ATOM | 2140 | OH2 | H2O A 619 | -0.989 |  3.952 |  4.095 | 1.00 | 80.29 |
| ATOM | 2141 | OH2 | H2O A 620 |  0.960 | 25.756 | -3.228 | 1.00 | 26.48 |
| ATOM | 2142 | OH2 | H2O A 621 | 29.724 | 12.973 | 20.379 | 1.00 | 54.04 |
| ATOM | 2143 | OH2 | H2O A 622 |  4.060 | -0.523 | -1.796 | 1.00 | 50.90 |
| ATOM | 2144 | OH2 | H2O A 623 | -3.885 | 22.314 |  1.723 | 1.00 | 35.56 |
| ATOM | 2145 | OH2 | H2O A 624 | 35.909 | 11.165 | 21.972 | 1.00 | 36.55 |
| ATOM | 2146 | OH2 | H2O A 625 | 20.132 |  4.043 |  1.525 | 1.00 | 34.98 |
| ATOM | 2147 | OH2 | H2O A 626 | 15.542 | 18.884 | 14.070 | 1.00 | 25.07 |
| ATOM | 2148 | OH2 | H2O A 627 |  3.435 |  5.153 |  3.769 | 1.00 | 20.36 |
| ATOM | 2149 | OH2 | H2O A 628 |  3.926 | 14.654 | 11.620 | 1.00 | 29.35 |
| ATOM | 2150 | OH2 | H2O A 630 |  8.413 | 13.659 | -7.765 | 1.00 | 61.82 |
| ATOM | 2151 | OH2 | H2O A 631 | 33.720 | -1.644 | 33.675 | 1.00 | 60.06 |
| ATOM | 2152 | OH2 | H2O A 632 |  5.228 | 27.101 | -1.846 | 1.00 | 21.78 |
| ATOM | 2153 | OH2 | H2O A 633 | 17.210 | 11.700 | 19.178 | 1.00 | 37.35 |
| ATOM | 2154 | OH2 | H2O A 634 | 17.202 | -1.716 |  4.458 | 1.00 | 30.58 |
| ATOM | 2155 | OH2 | H2O A 635 | -1.466 | 10.610 |  9.608 | 1.00 | 24.01 |
| ATOM | 2156 | OH2 | H2O A 636 | -2.286 | 11.221 | -4.925 | 1.00 | 28.26 |
| ATOM | 2157 | OH2 | H2O A 638 | -8.171 |  7.246 | -5.677 | 1.00 | 36.61 |
| ATOM | 2158 | OH2 | H2O A 639 | 15.603 |  9.290 | -8.613 | 1.00 | 50.48 |
| ATOM | 2159 | OH2 | H2O A 640 | -2.010 | 22.552 |  5.176 | 1.00 | 21.29 |
| ATOM | 2160 | OH2 | H2O A 641 | -2.783 |  5.308 |  2.538 | 1.00 | 16.69 |
| ATOM | 2161 | OH2 | H2O A 642 | 19.115 | -1.083 | 15.457 | 1.00 | 36.19 |
| ATOM | 2162 | OH2 | H2O A 643 | 26.085 | 22.164 | 33.067 | 1.00 | 84.90 |
| ATOM | 2163 | OH2 | H2O A 644 |  2.785 | 19.997 | -0.746 | 1.00 | 17.34 |
| ATOM | 2164 | OH2 | H2O A 645 | -4.441 | 22.646 |  9.419 | 1.00 | 33.91 |
| ATOM | 2165 | OH2 | H2O A 646 | 28.369 |  1.076 | 40.733 | 1.00 | 67.79 |
| ATOM | 2166 | OH2 | H2O A 647 |  4.122 | 34.970 |  6.137 | 1.00 | 47.14 |
| ATOM | 2167 | OH2 | H2O A 648 |  0.913 |  3.948 | 10.372 | 1.00 | 32.77 |
| ATOM | 2168 | OH2 | H2O A 649 |-13.300 |  4.722 | -2.569 | 1.00 | 71.58 |
| ATOM | 2169 | OH2 | H2O A 650 | 11.767 | 27.243 |  2.152 | 1.00 | 36.69 |
| ATOM | 2170 | OH2 | H2O A 651 |  2.824 | -3.721 |  0.994 | 1.00 | 30.88 |

Figure 10

| | | | | | | | | |
|---|---|---|---|---|---|---|---|---|
| ATOM | 2171 | OH2 | H2O | A | 652 | -1.508 | 19.554 | -0.933 | 1.00 25.65 |
| ATOM | 2172 | OH2 | H2O | A | 653 | 3.533 | 21.781 | 10.976 | 1.00 12.24 |
| ATOM | 2173 | OH2 | H2O | A | 654 | 3.150 | 29.918 | -4.611 | 1.00 46.21 |
| ATOM | 2174 | OH2 | H2O | A | 655 | 23.900 | 20.176 | 26.511 | 1.00 40.75 |
| ATOM | 2175 | OH2 | H2O | A | 656 | 4.871 | 2.572 | 16.500 | 1.00 31.91 |
| ATOM | 2176 | OH2 | H2O | A | 657 | 1.364 | 2.139 | 6.580 | 1.00 99.94 |
| ATOM | 2177 | OH2 | H2O | A | 658 | -1.817 | 23.296 | -6.246 | 1.00 47.13 |
| ATOM | 2178 | OH2 | H2O | A | 659 | 9.038 | 27.154 | -4.797 | 1.00 19.32 |
| ATOM | 2179 | OH2 | H2O | A | 660 | 20.433 | 13.360 | 21.756 | 1.00 39.58 |
| ATOM | 2180 | OH2 | H2O | A | 661 | 15.055 | 14.510 | 23.460 | 1.00 47.45 |
| ATOM | 2181 | OH2 | H2O | A | 662 | -6.201 | 9.438 | -3.118 | 1.00 80.90 |
| ATOM | 2182 | OH2 | H2O | A | 663 | 6.545 | 33.239 | 3.020 | 1.00 39.89 |
| ATOM | 2183 | OH2 | H2O | A | 664 | 17.257 | 16.044 | 24.052 | 1.00 25.82 |
| ATOM | 2184 | OH2 | H2O | A | 665 | 2.674 | 1.931 | 3.388 | 1.00 75.57 |
| ATOM | 2185 | OH2 | H2O | A | 666 | -2.608 | 23.542 | -2.234 | 1.00 32.52 |
| ATOM | 2186 | OH2 | H2O | A | 667 | 8.412 | 0.098 | 3.792 | 1.00 27.76 |
| ATOM | 2187 | OH2 | H2O | A | 668 | 22.341 | 22.314 | -0.603 | 1.00 31.76 |
| ATOM | 2188 | OH2 | H2O | A | 669 | 4.932 | 0.185 | 2.044 | 1.00 77.36 |
| ATOM | 2189 | OH2 | H2O | A | 670 | -6.067 | 23.472 | -2.418 | 1.00 73.40 |
| ATOM | 2190 | OH2 | H2O | A | 671 | -2.273 | 7.148 | 6.851 | 1.00 25.43 |
| ATOM | 2191 | OH2 | H2O | A | 672 | 6.365 | 1.591 | 19.293 | 1.00 48.04 |
| ATOM | 2192 | OH2 | H2O | A | 673 | 33.679 | 20.463 | 11.563 | 1.00 49.67 |
| ATOM | 2193 | OH2 | H2O | A | 674 | 14.227 | -0.470 | 4.628 | 1.00 39.13 |
| ATOM | 2194 | OH2 | H2O | A | 675 | -3.192 | 24.178 | 11.022 | 1.00 26.60 |
| ATOM | 2195 | OH2 | H2O | A | 676 | 31.527 | 3.907 | 18.652 | 1.00 42.32 |
| ATOM | 2196 | OH2 | H2O | A | 677 | 5.443 | 14.362 | 14.042 | 1.00 27.55 |
| ATOM | 2197 | OH2 | H2O | A | 678 | -5.329 | 17.619 | 6.735 | 1.00 36.81 |
| ATOM | 2198 | OH2 | H2O | A | 679 | 14.861 | 20.428 | 16.185 | 1.00 32.66 |
| ATOM | 2199 | OH2 | H2O | A | 680 | 31.834 | 15.706 | 31.291 | 1.00 33.21 |
| ATOM | 2200 | OH2 | H2O | A | 681 | -6.557 | 17.901 | 9.554 | 1.00 57.06 |
| ATOM | 2201 | OH2 | H2O | A | 682 | 28.952 | 2.041 | 19.840 | 1.00 39.07 |
| ATOM | 2202 | OH2 | H2O | A | 683 | 19.139 | 16.117 | 19.968 | 1.00 60.45 |
| ATOM | 2203 | OH2 | H2O | A | 684 | 14.156 | 24.120 | 7.101 | 1.00 25.28 |
| ATOM | 2204 | OH2 | H2O | A | 685 | -4.672 | 22.078 | 6.901 | 1.00 25.87 |
| ATOM | 2205 | OH2 | H2O | A | 686 | 17.115 | 22.597 | -9.679 | 1.00 41.47 |
| ATOM | 2206 | OH2 | H2O | A | 687 | -1.880 | 26.078 | -4.559 | 1.00 49.47 |
| ATOM | 2207 | OH2 | H2O | A | 688 | 33.776 | 11.973 | 11.030 | 1.00 38.65 |
| ATOM | 2208 | OH2 | H2O | A | 689 | -4.842 | 24.075 | 13.135 | 1.00 37.90 |
| ATOM | 2209 | OH2 | H2O | A | 690 | 4.389 | 4.901 | 33.302 | 1.00 48.19 |
| ATOM | 2210 | OH2 | H2O | A | 691 | 13.712 | -6.842 | 14.825 | 1.00 61.23 |
| ATOM | 2211 | OH2 | H2O | A | 692 | 12.233 | 21.062 | 17.943 | 1.00 43.07 |
| ATOM | 2212 | OH2 | H2O | A | 693 | 16.269 | 22.727 | 11.887 | 1.00 29.52 |
| ATOM | 2213 | OH2 | H2O | A | 694 | 17.253 | -0.487 | 17.440 | 1.00 48.47 |
| ATOM | 2214 | OH2 | H2O | A | 695 | -9.994 | 9.286 | -6.290 | 1.00 36.82 |
| ATOM | 2215 | OH2 | H2O | A | 696 | 30.647 | 15.525 | 1.082 | 1.00 51.25 |
| ATOM | 2216 | OH2 | H2O | A | 697 | 10.799 | 15.129 | -8.399 | 1.00 52.22 |
| ATOM | 2217 | OH2 | H2O | A | 698 | 24.469 | 11.243 | 34.722 | 1.00 48.05 |
| ATOM | 2218 | OH2 | H2O | A | 699 | -5.070 | 20.788 | -0.401 | 1.00 35.49 |
| ATOM | 2219 | OH2 | H2O | A | 700 | 6.191 | 10.144 | -8.492 | 1.00 45.28 |
| ATOM | 2220 | OH2 | H2O | A | 701 | 33.436 | 11.587 | 23.330 | 1.00 48.74 |
| ATOM | 2221 | OH2 | H2O | A | 702 | 14.386 | 4.177 | 19.801 | 1.00 27.64 |
| ATOM | 2222 | CB | TRP | B | 238 | 47.020 | 28.204 | 31.942 | 1.00 60.42 |
| ATOM | 2223 | CG | TRP | B | 238 | 46.547 | 28.852 | 33.262 | 1.00 63.55 |
| ATOM | 2224 | CD2 | TRP | B | 238 | 47.023 | 28.574 | 34.599 | 1.00 64.99 |
| ATOM | 2225 | CE2 | TRP | B | 238 | 46.276 | 29.392 | 35.492 | 1.00 65.08 |
| ATOM | 2226 | CE3 | TRP | B | 238 | 48.002 | 27.717 | 35.129 | 1.00 65.24 |
| ATOM | 2227 | CD1 | TRP | B | 238 | 45.560 | 29.802 | 33.407 | 1.00 63.98 |
| ATOM | 2228 | NE1 | TRP | B | 238 | 45.397 | 30.126 | 34.739 | 1.00 64.74 |
| ATOM | 2229 | CZ2 | TRP | B | 238 | 46.480 | 29.378 | 36.884 | 1.00 64.42 |

Figure 10

| | | | | | | | | | |
|---|---|---|---|---|---|---|---|---|---|
| ATOM | 2230 | CZ3 | TRP | B | 238 | 48.204 | 27.708 | 36.526 | 1.00 64.91 |
| ATOM | 2231 | CH2 | TRP | B | 238 | 47.442 | 28.533 | 37.379 | 1.00 64.51 |
| ATOM | 2232 | C | TRP | B | 238 | 48.699 | 28.108 | 30.033 | 1.00 57.41 |
| ATOM | 2233 | O | TRP | B | 238 | 49.327 | 27.063 | 30.195 | 1.00 57.02 |
| ATOM | 2234 | N | TRP | B | 238 | 47.875 | 30.330 | 30.931 | 1.00 58.41 |
| ATOM | 2235 | CA | TRP | B | 238 | 48.214 | 28.911 | 31.258 | 1.00 58.48 |
| ATOM | 2236 | N | GLU | B | 239 | 48.396 | 28.577 | 28.817 | 1.00 56.50 |
| ATOM | 2237 | CA | GLU | B | 239 | 48.846 | 27.892 | 27.591 | 1.00 54.93 |
| ATOM | 2238 | CB | GLU | B | 239 | 48.075 | 28.337 | 26.344 | 1.00 57.18 |
| ATOM | 2239 | CG | GLU | B | 239 | 47.072 | 27.340 | 25.814 | 1.00 62.17 |
| ATOM | 2240 | CD | GLU | B | 239 | 45.709 | 27.481 | 26.492 | 1.00 66.81 |
| ATOM | 2241 | OE1 | GLU | B | 239 | 45.592 | 27.123 | 27.691 | 1.00 68.35 |
| ATOM | 2242 | OE2 | GLU | B | 239 | 44.755 | 27.960 | 25.828 | 1.00 68.72 |
| ATOM | 2243 | C | GLU | B | 239 | 50.306 | 28.214 | 27.342 | 1.00 52.55 |
| ATOM | 2244 | O | GLU | B | 239 | 50.729 | 29.370 | 27.459 | 1.00 52.29 |
| ATOM | 2245 | N | VAL | B | 240 | 51.076 | 27.192 | 26.996 | 1.00 49.30 |
| ATOM | 2246 | CA | VAL | B | 240 | 52.489 | 27.384 | 26.706 | 1.00 46.50 |
| ATOM | 2247 | CB | VAL | B | 240 | 53.429 | 26.828 | 27.817 | 1.00 45.19 |
| ATOM | 2248 | CG1 | VAL | B | 240 | 53.274 | 27.617 | 29.101 | 1.00 44.21 |
| ATOM | 2249 | CG2 | VAL | B | 240 | 53.171 | 25.347 | 28.044 | 1.00 44.61 |
| ATOM | 2250 | C | VAL | B | 240 | 52.832 | 26.687 | 25.408 | 1.00 44.94 |
| ATOM | 2251 | O | VAL | B | 240 | 52.130 | 25.774 | 24.968 | 1.00 44.46 |
| ATOM | 2252 | N | PRO | B | 241 | 53.854 | 27.192 | 24.719 | 1.00 43.75 |
| ATOM | 2253 | CD | PRO | B | 241 | 54.532 | 28.489 | 24.890 | 1.00 43.22 |
| ATOM | 2254 | CA | PRO | B | 241 | 54.247 | 26.558 | 23.471 | 1.00 42.97 |
| ATOM | 2255 | CB | PRO | B | 241 | 55.246 | 27.559 | 22.898 | 1.00 43.08 |
| ATOM | 2256 | CG | PRO | B | 241 | 54.791 | 28.882 | 23.482 | 1.00 42.67 |
| ATOM | 2257 | C | PRO | B | 241 | 54.920 | 25.229 | 23.826 | 1.00 43.29 |
| ATOM | 2258 | O | PRO | B | 241 | 55.670 | 25.129 | 24.802 | 1.00 42.74 |
| ATOM | 2259 | N | ARG | B | 242 | 54.621 | 24.201 | 23.053 | 1.00 43.73 |
| ATOM | 2260 | CA | ARG | B | 242 | 55.199 | 22.882 | 23.264 | 1.00 44.86 |
| ATOM | 2261 | CB | ARG | B | 242 | 54.747 | 21.976 | 22.130 | 1.00 45.33 |
| ATOM | 2262 | CG | ARG | B | 242 | 55.462 | 20.658 | 22.043 | 1.00 47.01 |
| ATOM | 2263 | CD | ARG | B | 242 | 54.837 | 19.677 | 22.972 | 1.00 47.54 |
| ATOM | 2264 | NE | ARG | B | 242 | 53.383 | 19.602 | 22.801 | 1.00 49.94 |
| ATOM | 2265 | CZ | ARG | B | 242 | 52.758 | 19.222 | 21.685 | 1.00 48.19 |
| ATOM | 2266 | NH1 | ARG | B | 242 | 53.452 | 18.886 | 20.604 | 1.00 48.30 |
| ATOM | 2267 | NH2 | ARG | B | 242 | 51.433 | 19.132 | 21.670 | 1.00 45.40 |
| ATOM | 2268 | C | ARG | B | 242 | 56.740 | 22.876 | 23.351 | 1.00 45.72 |
| ATOM | 2269 | O | ARG | B | 242 | 57.316 | 21.996 | 23.993 | 1.00 45.33 |
| ATOM | 2270 | N | GLU | B | 243 | 57.389 | 23.847 | 22.698 | 1.00 46.38 |
| ATOM | 2271 | CA | GLU | B | 243 | 58.857 | 23.980 | 22.671 | 1.00 45.85 |
| ATOM | 2272 | CB | GLU | B | 243 | 59.293 | 25.253 | 21.923 | 1.00 49.57 |
| ATOM | 2273 | CG | GLU | B | 243 | 59.107 | 25.238 | 20.412 | 1.00 53.39 |
| ATOM | 2274 | CD | GLU | B | 243 | 57.634 | 25.260 | 19.983 | 1.00 55.78 |
| ATOM | 2275 | OE1 | GLU | B | 243 | 57.141 | 26.342 | 19.578 | 1.00 55.41 |
| ATOM | 2276 | OE2 | GLU | B | 243 | 56.977 | 24.189 | 20.041 | 1.00 56.38 |
| ATOM | 2277 | C | GLU | B | 243 | 59.448 | 24.055 | 24.062 | 1.00 43.54 |
| ATOM | 2278 | O | GLU | B | 243 | 60.508 | 23.502 | 24.312 | 1.00 42.99 |
| ATOM | 2279 | N | THR | B | 244 | 58.775 | 24.781 | 24.951 | 1.00 41.78 |
| ATOM | 2280 | CA | THR | B | 244 | 59.231 | 24.961 | 26.334 | 1.00 39.93 |
| ATOM | 2281 | CB | THR | B | 244 | 58.373 | 26.037 | 27.072 | 1.00 38.81 |
| ATOM | 2282 | OG1 | THR | B | 244 | 57.034 | 25.555 | 27.265 | 1.00 36.99 |
| ATOM | 2283 | CG2 | THR | B | 244 | 58.334 | 27.319 | 26.271 | 1.00 36.96 |
| ATOM | 2284 | C | THR | B | 244 | 59.202 | 23.678 | 27.174 | 1.00 38.20 |
| ATOM | 2285 | O | THR | B | 244 | 59.608 | 23.683 | 28.336 | 1.00 37.83 |
| ATOM | 2286 | N | LEU | B | 245 | 58.841 | 22.570 | 26.545 | 1.00 36.97 |
| ATOM | 2287 | CA | LEU | B | 245 | 58.686 | 21.310 | 27.246 | 1.00 36.26 |
| ATOM | 2288 | CB | LEU | B | 245 | 57.193 | 21.041 | 27.314 | 1.00 37.19 |

Figure 10

| | | | | | | | | | |
|---|---|---|---|---|---|---|---|---|---|
| ATOM | 2289 | CG | LEU | B | 245 | 56.490 | 20.663 | 28.603 | 1.00 40.03 |
| ATOM | 2290 | CD1 | LEU | B | 245 | 56.828 | 21.626 | 29.731 | 1.00 40.49 |
| ATOM | 2291 | CD2 | LEU | B | 245 | 54.997 | 20.682 | 28.301 | 1.00 40.33 |
| ATOM | 2292 | C | LEU | B | 245 | 59.392 | 20.094 | 26.633 | 1.00 35.38 |
| ATOM | 2293 | O | LEU | B | 245 | 59.093 | 19.698 | 25.508 | 1.00 34.97 |
| ATOM | 2294 | N | LYS | B | 246 | 60.326 | 19.503 | 27.378 | 1.00 34.84 |
| ATOM | 2295 | CA | LYS | B | 246 | 61.041 | 18.311 | 26.912 | 1.00 33.96 |
| ATOM | 2296 | CB | LYS | B | 246 | 62.572 | 18.537 | 26.900 | 1.00 35.05 |
| ATOM | 2297 | CG | LYS | B | 246 | 63.413 | 17.279 | 26.552 | 1.00 35.90 |
| ATOM | 2298 | CD | LYS | B | 246 | 64.944 | 17.527 | 26.492 | 1.00 39.04 |
| ATOM | 2299 | CE | LYS | B | 246 | 65.538 | 18.100 | 27.800 | 1.00 41.18 |
| ATOM | 2300 | NZ | LYS | B | 246 | 66.977 | 18.583 | 27.684 | 1.00 42.52 |
| ATOM | 2301 | C | LYS | B | 246 | 60.667 | 17.090 | 27.774 | 1.00 32.29 |
| ATOM | 2302 | O | LYS | B | 246 | 60.930 | 17.051 | 28.980 | 1.00 32.03 |
| ATOM | 2303 | N | LEU | B | 247 | 59.990 | 16.131 | 27.152 | 1.00 30.28 |
| ATOM | 2304 | CA | LEU | B | 247 | 59.588 | 14.898 | 27.820 | 1.00 28.78 |
| ATOM | 2305 | CB | LEU | B | 247 | 58.364 | 14.286 | 27.141 | 1.00 27.13 |
| ATOM | 2306 | CG | LEU | B | 247 | 57.017 | 14.919 | 27.486 | 1.00 26.36 |
| ATOM | 2307 | CD1 | LEU | B | 247 | 57.004 | 16.420 | 27.217 | 1.00 25.84 |
| ATOM | 2308 | CD2 | LEU | B | 247 | 55.938 | 14.220 | 26.684 | 1.00 25.30 |
| ATOM | 2309 | C | LEU | B | 247 | 60.754 | 13.914 | 27.810 | 1.00 28.95 |
| ATOM | 2310 | O | LEU | B | 247 | 61.223 | 13.467 | 26.757 | 1.00 29.14 |
| ATOM | 2311 | N | VAL | B | 248 | 61.206 | 13.566 | 29.003 | 1.00 29.27 |
| ATOM | 2312 | CA | VAL | B | 248 | 62.346 | 12.681 | 29.169 | 1.00 29.03 |
| ATOM | 2313 | CB | VAL | B | 248 | 63.285 | 13.243 | 30.267 | 1.00 27.45 |
| ATOM | 2314 | CG1 | VAL | B | 248 | 64.606 | 12.525 | 30.264 | 1.00 27.25 |
| ATOM | 2315 | CG2 | VAL | B | 248 | 63.483 | 14.730 | 30.062 | 1.00 26.05 |
| ATOM | 2316 | C | VAL | B | 248 | 62.031 | 11.221 | 29.483 | 1.00 29.80 |
| ATOM | 2317 | O | VAL | B | 248 | 62.449 | 10.310 | 28.761 | 1.00 30.03 |
| ATOM | 2318 | N | GLU | B | 249 | 61.269 | 11.004 | 30.547 | 1.00 30.61 |
| ATOM | 2319 | CA | GLU | B | 249 | 60.962 | 9.654 | 30.996 | 1.00 31.34 |
| ATOM | 2320 | CB | GLU | B | 249 | 61.587 | 9.479 | 32.371 | 1.00 33.29 |
| ATOM | 2321 | CG | GLU | B | 249 | 61.557 | 8.076 | 32.894 | 1.00 36.85 |
| ATOM | 2322 | CD | GLU | B | 249 | 62.317 | 7.952 | 34.190 | 1.00 39.34 |
| ATOM | 2323 | OE1 | GLU | B | 249 | 63.190 | 8.811 | 34.441 | 1.00 40.34 |
| ATOM | 2324 | OE2 | GLU | B | 249 | 62.043 | 7.000 | 34.957 | 1.00 42.40 |
| ATOM | 2325 | C | GLU | B | 249 | 59.479 | 9.347 | 31.097 | 1.00 31.02 |
| ATOM | 2326 | O | GLU | B | 249 | 58.712 | 10.168 | 31.587 | 1.00 31.78 |
| ATOM | 2327 | N | ARG | B | 250 | 59.067 | 8.171 | 30.642 | 1.00 30.31 |
| ATOM | 2328 | CA | ARG | B | 250 | 57.660 | 7.818 | 30.743 | 1.00 30.38 |
| ATOM | 2329 | CB | ARG | B | 250 | 57.187 | 6.968 | 29.581 | 1.00 30.15 |
| ATOM | 2330 | CG | ARG | B | 250 | 55.677 | 7.081 | 29.436 | 1.00 34.20 |
| ATOM | 2331 | CD | ARG | B | 250 | 55.174 | 6.280 | 28.289 | 1.00 36.55 |
| ATOM | 2332 | NE | ARG | B | 250 | 55.445 | 4.868 | 28.515 | 1.00 41.33 |
| ATOM | 2333 | CZ | ARG | B | 250 | 55.337 | 3.919 | 27.588 | 1.00 42.89 |
| ATOM | 2334 | NH1 | ARG | B | 250 | 54.969 | 4.222 | 26.351 | 1.00 42.39 |
| ATOM | 2335 | NH2 | ARG | B | 250 | 55.576 | 2.658 | 27.915 | 1.00 44.19 |
| ATOM | 2336 | C | ARG | B | 250 | 57.431 | 7.092 | 32.055 | 1.00 30.40 |
| ATOM | 2337 | O | ARG | B | 250 | 57.999 | 6.020 | 32.289 | 1.00 31.81 |
| ATOM | 2338 | N | LEU | B | 251 | 56.610 | 7.696 | 32.909 | 1.00 28.28 |
| ATOM | 2339 | CA | LEU | B | 251 | 56.324 | 7.154 | 34.222 | 1.00 26.88 |
| ATOM | 2340 | CB | LEU | B | 251 | 56.008 | 8.295 | 35.187 | 1.00 25.23 |
| ATOM | 2341 | CG | LEU | B | 251 | 57.051 | 9.424 | 35.167 | 1.00 23.40 |
| ATOM | 2342 | CD1 | LEU | B | 251 | 56.576 | 10.589 | 36.007 | 1.00 24.02 |
| ATOM | 2343 | CD2 | LEU | B | 251 | 58.407 | 8.941 | 35.639 | 1.00 22.81 |
| ATOM | 2344 | C | LEU | B | 251 | 55.208 | 6.132 | 34.181 | 1.00 26.32 |
| ATOM | 2345 | O | LEU | B | 251 | 55.133 | 5.244 | 35.025 | 1.00 27.17 |
| ATOM | 2346 | N | GLY | B | 252 | 54.362 | 6.244 | 33.171 | 1.00 26.25 |
| ATOM | 2347 | CA | GLY | B | 252 | 53.267 | 5.310 | 33.015 | 1.00 24.89 |

Figure 10

| | | | | | | | | |
|---|---|---|---|---|---|---|---|---|
| ATOM | 2348 | C | GLY | B | 252 | 52.459 | 5.533 | 31.745 | 1.00 25.29 |
| ATOM | 2349 | O | GLY | B | 252 | 52.362 | 6.652 | 31.220 | 1.00 24.58 |
| ATOM | 2350 | N | ALA | B | 253 | 51.830 | 4.459 | 31.282 | 1.00 25.71 |
| ATOM | 2351 | CA | ALA | B | 253 | 50.989 | 4.482 | 30.093 | 1.00 26.10 |
| ATOM | 2352 | CB | ALA | B | 253 | 51.765 | 3.972 | 28.892 | 1.00 27.01 |
| ATOM | 2353 | C | ALA | B | 253 | 49.729 | 3.628 | 30.315 | 1.00 26.19 |
| ATOM | 2354 | O | ALA | B | 253 | 49.812 | 2.464 | 30.750 | 1.00 25.00 |
| ATOM | 2355 | N | GLY | B | 254 | 48.571 | 4.213 | 30.004 | 1.00 26.90 |
| ATOM | 2356 | CA | GLY | B | 254 | 47.308 | 3.514 | 30.177 | 1.00 27.31 |
| ATOM | 2357 | C | GLY | B | 254 | 46.359 | 3.670 | 29.010 | 1.00 28.83 |
| ATOM | 2358 | O | GLY | B | 254 | 46.734 | 4.146 | 27.947 | 1.00 29.42 |
| ATOM | 2359 | N | GLN | B | 255 | 45.109 | 3.305 | 29.237 | 1.00 30.68 |
| ATOM | 2360 | CA | GLN | B | 255 | 44.075 | 3.358 | 28.216 | 1.00 32.43 |
| ATOM | 2361 | CB | GLN | B | 255 | 42.775 | 2.752 | 28.763 | 1.00 36.11 |
| ATOM | 2362 | CG | GLN | B | 255 | 41.793 | 2.291 | 27.677 | 1.00 41.65 |
| ATOM | 2363 | CD | GLN | B | 255 | 40.336 | 2.194 | 28.147 | 1.00 45.59 |
| ATOM | 2364 | OE1 | GLN | B | 255 | 39.423 | 2.051 | 27.321 | 1.00 45.95 |
| ATOM | 2365 | NE2 | GLN | B | 255 | 40.108 | 2.283 | 29.468 | 1.00 46.66 |
| ATOM | 2366 | C | GLN | B | 255 | 43.777 | 4.740 | 27.646 | 1.00 32.42 |
| ATOM | 2367 | O | GLN | B | 255 | 43.470 | 4.873 | 26.458 | 1.00 33.65 |
| ATOM | 2368 | N | PHE | B | 256 | 43.842 | 5.767 | 28.489 | 1.00 31.44 |
| ATOM | 2369 | CA | PHE | B | 256 | 43.545 | 7.125 | 28.046 | 1.00 30.26 |
| ATOM | 2370 | CB | PHE | B | 256 | 42.709 | 7.851 | 29.100 | 1.00 30.80 |
| ATOM | 2371 | CG | PHE | B | 256 | 41.297 | 7.338 | 29.221 | 1.00 31.19 |
| ATOM | 2372 | CD1 | PHE | B | 256 | 40.860 | 6.260 | 28.450 | 1.00 31.93 |
| ATOM | 2373 | CD2 | PHE | B | 256 | 40.405 | 7.927 | 30.111 | 1.00 30.27 |
| ATOM | 2374 | CE1 | PHE | B | 256 | 39.559 | 5.769 | 28.573 | 1.00 31.07 |
| ATOM | 2375 | CE2 | PHE | B | 256 | 39.107 | 7.441 | 30.238 | 1.00 29.92 |
| ATOM | 2376 | CZ | PHE | B | 256 | 38.684 | 6.360 | 29.465 | 1.00 29.68 |
| ATOM | 2377 | C | PHE | B | 256 | 44.720 | 8.010 | 27.655 | 1.00 30.35 |
| ATOM | 2378 | O | PHE | B | 256 | 44.506 | 9.146 | 27.195 | 1.00 30.28 |
| ATOM | 2379 | N | GLY | B | 257 | 45.949 | 7.522 | 27.861 | 1.00 29.40 |
| ATOM | 2380 | CA | GLY | B | 257 | 47.121 | 8.318 | 27.533 | 1.00 27.92 |
| ATOM | 2381 | C | GLY | B | 257 | 48.342 | 7.947 | 28.349 | 1.00 27.70 |
| ATOM | 2382 | O | GLY | B | 257 | 48.481 | 6.801 | 28.779 | 1.00 26.79 |
| ATOM | 2383 | N | GLU | B | 258 | 49.199 | 8.930 | 28.622 | 1.00 27.89 |
| ATOM | 2384 | CA | GLU | B | 258 | 50.443 | 8.679 | 29.343 | 1.00 28.60 |
| ATOM | 2385 | CB | GLU | B | 258 | 51.574 | 8.486 | 28.331 | 1.00 30.05 |
| ATOM | 2386 | CG | GLU | B | 258 | 51.206 | 7.634 | 27.121 | 1.00 33.66 |
| ATOM | 2387 | CD | GLU | B | 258 | 52.410 | 7.256 | 26.265 | 1.00 37.53 |
| ATOM | 2388 | OE1 | GLU | B | 258 | 53.217 | 8.142 | 25.907 | 1.00 40.01 |
| ATOM | 2389 | OE2 | GLU | B | 258 | 52.550 | 6.061 | 25.935 | 1.00 39.46 |
| ATOM | 2390 | C | GLU | B | 258 | 50.870 | 9.767 | 30.319 | 1.00 27.55 |
| ATOM | 2391 | O | GLU | B | 258 | 50.340 | 10.872 | 30.314 | 1.00 28.12 |
| ATOM | 2392 | N | VAL | B | 259 | 51.833 | 9.433 | 31.169 | 1.00 27.20 |
| ATOM | 2393 | CA | VAL | B | 259 | 52.367 | 10.385 | 32.150 | 1.00 26.84 |
| ATOM | 2394 | CB | VAL | B | 259 | 51.971 | 10.066 | 33.631 | 1.00 25.41 |
| ATOM | 2395 | CG1 | VAL | B | 259 | 52.399 | 11.226 | 34.534 | 1.00 22.06 |
| ATOM | 2396 | CG2 | VAL | B | 259 | 50.473 | 9.800 | 33.767 | 1.00 23.18 |
| ATOM | 2397 | C | VAL | B | 259 | 53.881 | 10.290 | 32.022 | 1.00 27.07 |
| ATOM | 2398 | O | VAL | B | 259 | 54.439 | 9.186 | 32.028 | 1.00 26.91 |
| ATOM | 2399 | N | TRP | B | 260 | 54.527 | 11.448 | 31.905 | 1.00 27.36 |
| ATOM | 2400 | CA | TRP | B | 260 | 55.972 | 11.537 | 31.732 | 1.00 27.64 |
| ATOM | 2401 | CB | TRP | B | 260 | 56.312 | 12.081 | 30.331 | 1.00 26.43 |
| ATOM | 2402 | CG | TRP | B | 260 | 56.111 | 11.156 | 29.174 | 1.00 27.38 |
| ATOM | 2403 | CD2 | TRP | B | 260 | 57.137 | 10.603 | 28.326 | 1.00 28.57 |
| ATOM | 2404 | CE2 | TRP | B | 260 | 56.495 | 9.784 | 27.373 | 1.00 28.33 |
| ATOM | 2405 | CE3 | TRP | B | 260 | 58.538 | 10.715 | 28.285 | 1.00 29.30 |
| ATOM | 2406 | CD1 | TRP | B | 260 | 54.923 | 10.668 | 28.704 | 1.00 26.81 |

Figure 10

| | | | | | | | | |
|---|---|---|---|---|---|---|---|---|
| ATOM | 2407 | NE1 | TRP | B | 260 | 55.147 | 9.843 | 27.627 | 1.00 27.57 |
| ATOM | 2408 | CZ2 | TRP | B | 260 | 57.209 | 9.072 | 26.390 | 1.00 27.48 |
| ATOM | 2409 | CZ3 | TRP | B | 260 | 59.246 | 10.006 | 27.308 | 1.00 27.48 |
| ATOM | 2410 | CH2 | TRP | B | 260 | 58.578 | 9.196 | 26.379 | 1.00 25.02 |
| ATOM | 2411 | C | TRP | B | 260 | 56.610 | 12.507 | 32.711 | 1.00 28.75 |
| ATOM | 2412 | O | TRP | B | 260 | 55.949 | 13.400 | 33.261 | 1.00 28.10 |
| ATOM | 2413 | N | MET | B | 261 | 57.910 | 12.318 | 32.922 | 1.00 28.82 |
| ATOM | 2414 | CA | MET | B | 261 | 58.695 | 13.221 | 33.743 | 1.00 28.63 |
| ATOM | 2415 | CB | MET | B | 261 | 59.784 | 12.485 | 34.523 | 1.00 27.16 |
| ATOM | 2416 | CG | MET | B | 261 | 60.702 | 13.418 | 35.315 | 1.00 27.50 |
| ATOM | 2417 | SD | MET | B | 261 | 62.027 | 14.273 | 34.379 | 1.00 25.76 |
| ATOM | 2418 | CE | MET | B | 261 | 63.070 | 12.874 | 34.014 | 1.00 24.37 |
| ATOM | 2419 | C | MET | B | 261 | 59.329 | 14.070 | 32.655 | 1.00 29.46 |
| ATOM | 2420 | O | MET | B | 261 | 59.618 | 13.567 | 31.570 | 1.00 30.24 |
| ATOM | 2421 | N | GLY | B | 262 | 59.527 | 15.349 | 32.927 | 1.00 30.29 |
| ATOM | 2422 | CA | GLY | B | 262 | 60.133 | 16.200 | 31.929 | 1.00 30.02 |
| ATOM | 2423 | C | GLY | B | 262 | 60.642 | 17.493 | 32.509 | 1.00 30.98 |
| ATOM | 2424 | O | GLY | B | 262 | 60.629 | 17.713 | 33.723 | 1.00 29.81 |
| ATOM | 2425 | N | TYR | B | 263 | 61.119 | 18.350 | 31.618 | 1.00 32.48 |
| ATOM | 2426 | CA | TYR | B | 263 | 61.650 | 19.632 | 32.018 | 1.00 34.65 |
| ATOM | 2427 | CB | TYR | B | 263 | 63.168 | 19.664 | 31.768 | 1.00 31.72 |
| ATOM | 2428 | CG | TYR | B | 263 | 63.925 | 18.695 | 32.671 | 1.00 30.94 |
| ATOM | 2429 | CD1 | TYR | B | 263 | 64.396 | 19.098 | 33.928 | 1.00 30.04 |
| ATOM | 2430 | CE1 | TYR | B | 263 | 65.027 | 18.193 | 34.789 | 1.00 28.73 |
| ATOM | 2431 | CD2 | TYR | B | 263 | 64.110 | 17.354 | 32.300 | 1.00 29.78 |
| ATOM | 2432 | CE2 | TYR | B | 263 | 64.736 | 16.438 | 33.163 | 1.00 29.02 |
| ATOM | 2433 | CZ | TYR | B | 263 | 65.190 | 16.869 | 34.406 | 1.00 29.00 |
| ATOM | 2434 | OH | TYR | B | 263 | 65.801 | 15.973 | 35.261 | 1.00 29.42 |
| ATOM | 2435 | C | TYR | B | 263 | 60.908 | 20.762 | 31.317 | 1.00 37.36 |
| ATOM | 2436 | O | TYR | B | 263 | 60.553 | 20.660 | 30.142 | 1.00 37.93 |
| ATOM | 2437 | N | TYR | B | 264 | 60.624 | 21.805 | 32.084 | 1.00 41.00 |
| ATOM | 2438 | CA | TYR | B | 264 | 59.911 | 22.994 | 31.626 | 1.00 45.10 |
| ATOM | 2439 | CB | TYR | B | 264 | 58.754 | 23.260 | 32.605 | 1.00 47.99 |
| ATOM | 2440 | CG | TYR | B | 264 | 57.846 | 24.464 | 32.386 | 1.00 51.28 |
| ATOM | 2441 | CD1 | TYR | B | 264 | 57.604 | 24.992 | 31.109 | 1.00 52.09 |
| ATOM | 2442 | CE1 | TYR | B | 264 | 56.685 | 26.037 | 30.931 | 1.00 53.85 |
| ATOM | 2443 | CD2 | TYR | B | 264 | 57.148 | 25.020 | 33.481 | 1.00 52.28 |
| ATOM | 2444 | CE2 | TYR | B | 264 | 56.234 | 26.052 | 33.320 | 1.00 53.00 |
| ATOM | 2445 | CZ | TYR | B | 264 | 56.001 | 26.558 | 32.049 | 1.00 55.13 |
| ATOM | 2446 | OH | TYR | B | 264 | 55.063 | 27.561 | 31.906 | 1.00 57.15 |
| ATOM | 2447 | C | TYR | B | 264 | 60.921 | 24.124 | 31.667 | 1.00 46.45 |
| ATOM | 2448 | O | TYR | B | 264 | 61.541 | 24.376 | 32.704 | 1.00 47.08 |
| ATOM | 2449 | N | ASN | B | 265 | 61.111 | 24.777 | 30.529 | 1.00 48.10 |
| ATOM | 2450 | CA | ASN | B | 265 | 62.055 | 25.881 | 30.434 | 1.00 50.51 |
| ATOM | 2451 | CB | ASN | B | 265 | 61.659 | 27.003 | 31.407 | 1.00 52.25 |
| ATOM | 2452 | CG | ASN | B | 265 | 60.229 | 27.511 | 31.181 | 1.00 54.64 |
| ATOM | 2453 | OD1 | ASN | B | 265 | 59.848 | 27.866 | 30.057 | 1.00 54.35 |
| ATOM | 2454 | ND2 | ASN | B | 265 | 59.437 | 27.558 | 32.261 | 1.00 54.52 |
| ATOM | 2455 | C | ASN | B | 265 | 63.460 | 25.356 | 30.745 | 1.00 51.27 |
| ATOM | 2456 | O | ASN | B | 265 | 64.281 | 26.037 | 31.378 | 1.00 51.95 |
| ATOM | 2457 | N | GLY | B | 266 | 63.694 | 24.107 | 30.350 | 1.00 51.58 |
| ATOM | 2458 | CA | GLY | B | 266 | 64.983 | 23.470 | 30.550 | 1.00 52.55 |
| ATOM | 2459 | C | GLY | B | 266 | 65.417 | 23.058 | 31.949 | 1.00 53.51 |
| ATOM | 2460 | O | GLY | B | 266 | 66.142 | 22.067 | 32.082 | 1.00 54.02 |
| ATOM | 2461 | N | HIS | B | 267 | 64.989 | 23.788 | 32.984 | 1.00 53.90 |
| ATOM | 2462 | CA | HIS | B | 267 | 65.404 | 23.463 | 34.354 | 1.00 53.72 |
| ATOM | 2463 | CB | HIS | B | 267 | 66.315 | 24.561 | 34.898 | 1.00 57.23 |
| ATOM | 2464 | CG | HIS | B | 267 | 67.700 | 24.514 | 34.331 | 1.00 61.29 |
| ATOM | 2465 | CD2 | HIS | B | 267 | 68.624 | 23.522 | 34.315 | 1.00 62.84 |

Figure 10

| ATOM | 2466 | ND1 | HIS | B | 267 | 68.274 | 25.577 | 33.664 | 1.00 | 63.33 |
| --- | --- | --- | --- | --- | --- | --- | --- | --- | --- | --- |
| ATOM | 2467 | CE1 | HIS | B | 267 | 69.486 | 25.243 | 33.259 | 1.00 | 62.93 |
| ATOM | 2468 | NE2 | HIS | B | 267 | 69.724 | 24.000 | 33.643 | 1.00 | 64.05 |
| ATOM | 2469 | C | HIS | B | 267 | 64.369 | 23.061 | 35.399 | 1.00 | 51.41 |
| ATOM | 2470 | O | HIS | B | 267 | 64.720 | 22.397 | 36.379 | 1.00 | 51.73 |
| ATOM | 2471 | N | THR | B | 268 | 63.118 | 23.483 | 35.220 | 1.00 | 48.27 |
| ATOM | 2472 | CA | THR | B | 268 | 62.050 | 23.117 | 36.153 | 1.00 | 44.94 |
| ATOM | 2473 | CB | THR | B | 268 | 60.867 | 24.105 | 36.068 | 1.00 | 46.12 |
| ATOM | 2474 | OG1 | THR | B | 268 | 61.358 | 25.447 | 36.169 | 1.00 | 47.78 |
| ATOM | 2475 | CG2 | THR | B | 268 | 59.857 | 23.844 | 37.193 | 1.00 | 45.09 |
| ATOM | 2476 | C | THR | B | 268 | 61.534 | 21.709 | 35.835 | 1.00 | 42.20 |
| ATOM | 2477 | O | THR | B | 268 | 60.981 | 21.462 | 34.767 | 1.00 | 41.07 |
| ATOM | 2478 | N | LYS | B | 269 | 61.723 | 20.781 | 36.765 | 1.00 | 40.13 |
| ATOM | 2479 | CA | LYS | B | 269 | 61.260 | 19.408 | 36.571 | 1.00 | 37.91 |
| ATOM | 2480 | CB | LYS | B | 269 | 61.913 | 18.485 | 37.602 | 1.00 | 36.79 |
| ATOM | 2481 | CG | LYS | B | 269 | 62.085 | 17.052 | 37.146 | 1.00 | 36.20 |
| ATOM | 2482 | CD | LYS | B | 269 | 62.857 | 16.250 | 38.172 | 1.00 | 35.22 |
| ATOM | 2483 | CE | LYS | B | 269 | 63.384 | 14.964 | 37.585 | 1.00 | 36.11 |
| ATOM | 2484 | NZ | LYS | B | 269 | 64.302 | 14.265 | 38.525 | 1.00 | 36.74 |
| ATOM | 2485 | C | LYS | B | 269 | 59.731 | 19.375 | 36.712 | 1.00 | 36.66 |
| ATOM | 2486 | O | LYS | B | 269 | 59.176 | 19.944 | 37.655 | 1.00 | 36.03 |
| ATOM | 2487 | N | VAL | B | 270 | 59.052 | 18.741 | 35.754 | 1.00 | 34.80 |
| ATOM | 2488 | CA | VAL | B | 270 | 57.591 | 18.639 | 35.771 | 1.00 | 32.28 |
| ATOM | 2489 | CB | VAL | B | 270 | 56.953 | 19.657 | 34.776 | 1.00 | 31.24 |
| ATOM | 2490 | CG1 | VAL | B | 270 | 57.310 | 21.066 | 35.154 | 1.00 | 29.22 |
| ATOM | 2491 | CG2 | VAL | B | 270 | 57.406 | 19.378 | 33.367 | 1.00 | 28.45 |
| ATOM | 2492 | C | VAL | B | 270 | 57.061 | 17.235 | 35.423 | 1.00 | 32.49 |
| ATOM | 2493 | O | VAL | B | 270 | 57.829 | 16.333 | 35.070 | 1.00 | 31.87 |
| ATOM | 2494 | N | ALA | B | 271 | 55.748 | 17.046 | 35.595 | 1.00 | 32.11 |
| ATOM | 2495 | CA | ALA | B | 271 | 55.070 | 15.799 | 35.239 | 1.00 | 30.62 |
| ATOM | 2496 | CB | ALA | B | 271 | 54.307 | 15.222 | 36.418 | 1.00 | 30.24 |
| ATOM | 2497 | C | ALA | B | 271 | 54.104 | 16.211 | 34.129 | 1.00 | 30.44 |
| ATOM | 2498 | O | ALA | B | 271 | 53.380 | 17.202 | 34.257 | 1.00 | 31.55 |
| ATOM | 2499 | N | VAL | B | 272 | 54.130 | 15.487 | 33.021 | 1.00 | 29.22 |
| ATOM | 2500 | CA | VAL | B | 272 | 53.267 | 15.817 | 31.898 | 1.00 | 29.60 |
| ATOM | 2501 | CB | VAL | B | 272 | 54.096 | 16.121 | 30.611 | 1.00 | 30.55 |
| ATOM | 2502 | CG1 | VAL | B | 272 | 53.222 | 16.808 | 29.579 | 1.00 | 30.23 |
| ATOM | 2503 | CG2 | VAL | B | 272 | 55.330 | 16.958 | 30.931 | 1.00 | 29.58 |
| ATOM | 2504 | C | VAL | B | 272 | 52.343 | 14.658 | 31.575 | 1.00 | 28.53 |
| ATOM | 2505 | O | VAL | B | 272 | 52.799 | 13.531 | 31.403 | 1.00 | 28.20 |
| ATOM | 2506 | N | LYS | B | 273 | 51.044 | 14.941 | 31.527 | 1.00 | 27.85 |
| ATOM | 2507 | CA | LYS | B | 273 | 50.041 | 13.930 | 31.195 | 1.00 | 26.79 |
| ATOM | 2508 | CB | LYS | B | 273 | 48.907 | 13.924 | 32.220 | 1.00 | 26.43 |
| ATOM | 2509 | CG | LYS | B | 273 | 47.837 | 12.864 | 31.966 | 1.00 | 25.15 |
| ATOM | 2510 | CD | LYS | B | 273 | 46.749 | 12.925 | 33.034 | 1.00 | 24.46 |
| ATOM | 2511 | CE | LYS | B | 273 | 47.130 | 12.181 | 34.311 | 1.00 | 21.47 |
| ATOM | 2512 | NZ | LYS | B | 273 | 45.941 | 12.060 | 35.221 | 1.00 | 20.86 |
| ATOM | 2513 | C | LYS | B | 273 | 49.488 | 14.262 | 29.814 | 1.00 | 26.66 |
| ATOM | 2514 | O | LYS | B | 273 | 48.958 | 15.353 | 29.591 | 1.00 | 24.17 |
| ATOM | 2515 | N | SER | B | 274 | 49.633 | 13.315 | 28.894 | 1.00 | 27.64 |
| ATOM | 2516 | CA | SER | B | 274 | 49.176 | 13.482 | 27.516 | 1.00 | 29.26 |
| ATOM | 2517 | CB | SER | B | 274 | 50.288 | 13.100 | 26.531 | 1.00 | 30.32 |
| ATOM | 2518 | OG | SER | B | 274 | 50.729 | 11.766 | 26.731 | 1.00 | 30.94 |
| ATOM | 2519 | C | SER | B | 274 | 47.934 | 12.671 | 27.204 | 1.00 | 29.26 |
| ATOM | 2520 | O | SER | B | 274 | 47.792 | 11.548 | 27.668 | 1.00 | 29.61 |
| ATOM | 2521 | N | LEU | B | 275 | 47.048 | 13.243 | 26.397 | 1.00 | 30.42 |
| ATOM | 2522 | CA | LEU | B | 275 | 45.802 | 12.584 | 26.003 | 1.00 | 31.56 |
| ATOM | 2523 | CB | LEU | B | 275 | 44.707 | 13.621 | 25.738 | 1.00 | 30.12 |
| ATOM | 2524 | CG | LEU | B | 275 | 43.362 | 13.106 | 25.194 | 1.00 | 31.40 |

Figure 10

```
ATOM   2525  CD1 LEU B 275      42.696  12.195  26.236  1.00 31.81
ATOM   2526  CD2 LEU B 275      42.427  14.267  24.825  1.00 28.87
ATOM   2527  C   LEU B 275      45.962  11.725  24.753  1.00 33.44
ATOM   2528  O   LEU B 275      46.510  12.181  23.745  1.00 34.45
ATOM   2529  N   LYS B 276      45.524  10.471  24.844  1.00 34.36
ATOM   2530  CA  LYS B 276      45.557   9.564  23.711  1.00 36.19
ATOM   2531  CB  LYS B 276      45.405   8.115  24.167  1.00 37.40
ATOM   2532  CG  LYS B 276      45.264   7.098  23.028  1.00 40.20
ATOM   2533  CD  LYS B 276      45.248   5.665  23.566  1.00 43.73
ATOM   2534  CE  LYS B 276      46.517   5.377  24.392  1.00 47.01
ATOM   2535  NZ  LYS B 276      46.592   3.993  24.957  1.00 48.52
ATOM   2536  C   LYS B 276      44.318   9.981  22.958  1.00 37.33
ATOM   2537  O   LYS B 276      43.209   9.863  23.490  1.00 37.92
ATOM   2538  N   GLN B 277      44.513  10.546  21.769  1.00 37.81
ATOM   2539  CA  GLN B 277      43.407  11.015  20.920  1.00 37.57
ATOM   2540  CB  GLN B 277      43.956  11.430  19.559  1.00 42.06
ATOM   2541  CG  GLN B 277      42.924  11.943  18.571  1.00 47.50
ATOM   2542  CD  GLN B 277      43.549  12.221  17.224  1.00 52.28
ATOM   2543  OE1 GLN B 277      44.539  11.580  16.844  1.00 56.08
ATOM   2544  NE2 GLN B 277      42.977  13.162  16.481  1.00 53.75
ATOM   2545  C   GLN B 277      42.309   9.981  20.724  1.00 35.13
ATOM   2546  O   GLN B 277      42.574   8.832  20.393  1.00 33.44
ATOM   2547  N   GLY B 278      41.071  10.390  20.946  1.00 34.34
ATOM   2548  CA  GLY B 278      39.977   9.454  20.774  1.00 34.02
ATOM   2549  C   GLY B 278      39.423   8.883  22.071  1.00 34.55
ATOM   2550  O   GLY B 278      38.305   8.359  22.090  1.00 34.69
ATOM   2551  N   SER B 279      40.195   8.978  23.152  1.00 34.40
ATOM   2552  CA  SER B 279      39.758   8.471  24.454  1.00 34.53
ATOM   2553  CB  SER B 279      40.933   8.483  25.424  1.00 33.75
ATOM   2554  OG  SER B 279      41.988   7.702  24.907  1.00 34.49
ATOM   2555  C   SER B 279      38.611   9.340  24.992  1.00 34.21
ATOM   2556  O   SER B 279      37.684   8.859  25.655  1.00 33.91
ATOM   2557  N   MET B 280      38.716  10.628  24.707  1.00 33.04
ATOM   2558  CA  MET B 280      37.734  11.616  25.097  1.00 33.71
ATOM   2559  CB  MET B 280      37.720  11.840  26.618  1.00 34.54
ATOM   2560  CG  MET B 280      39.024  12.371  27.229  1.00 35.96
ATOM   2561  SD  MET B 280      39.183  12.208  29.040  1.00 35.31
ATOM   2562  CE  MET B 280      38.054  13.439  29.576  1.00 34.04
ATOM   2563  C   MET B 280      38.161  12.876  24.331  1.00 34.35
ATOM   2564  O   MET B 280      39.256  12.921  23.769  1.00 34.25
ATOM   2565  N   SER B 281      37.302  13.894  24.305  1.00 34.60
ATOM   2566  CA  SER B 281      37.599  15.119  23.579  1.00 35.57
ATOM   2567  CB  SER B 281      36.325  15.937  23.400  1.00 34.76
ATOM   2568  OG  SER B 281      35.976  16.655  24.564  1.00 34.99
ATOM   2569  C   SER B 281      38.638  15.936  24.331  1.00 38.19
ATOM   2570  O   SER B 281      38.869  15.754  25.516  1.00 38.35
ATOM   2571  N   PRO B 282      39.266  16.894  23.672  1.00 38.89
ATOM   2572  CD  PRO B 282      39.313  17.021  22.211  1.00 38.28
ATOM   2573  CA  PRO B 282      40.289  17.733  24.296  1.00 39.66
ATOM   2574  CB  PRO B 282      40.713  18.625  23.136  1.00 39.26
ATOM   2575  CG  PRO B 282      40.601  17.648  22.025  1.00 37.97
ATOM   2576  C   PRO B 282      39.665  18.529  25.449  1.00 41.11
ATOM   2577  O   PRO B 282      40.303  18.733  26.499  1.00 41.12
ATOM   2578  N   ASP B 283      38.460  19.049  25.273  1.00 41.70
ATOM   2579  CA  ASP B 283      37.761  19.824  26.306  1.00 42.50
ATOM   2580  CB  ASP B 283      36.375  20.266  25.826  1.00 44.72
ATOM   2581  CG  ASP B 283      36.412  21.524  24.951  1.00 47.82
ATOM   2582  OD1 ASP B 283      37.497  22.165  24.858  1.00 48.00
ATOM   2583  OD2 ASP B 283      35.374  21.870  24.334  1.00 49.79
```

Figure 10

| | | | | | | | | | |
|---|---|---|---|---|---|---|---|---|---|
| ATOM | 2584 | C | ASP | B | 283 | 37.501 | 18.992 | 27.557 | 1.00 42.60 |
| ATOM | 2585 | O | ASP | B | 283 | 37.563 | 19.498 | 28.709 | 1.00 43.49 |
| ATOM | 2586 | N | ALA | B | 284 | 37.114 | 17.742 | 27.347 | 1.00 41.47 |
| ATOM | 2587 | CA | ALA | B | 284 | 36.811 | 16.830 | 28.441 | 1.00 41.11 |
| ATOM | 2588 | CB | ALA | B | 284 | 36.318 | 15.463 | 27.906 | 1.00 39.43 |
| ATOM | 2589 | C | ALA | B | 284 | 38.045 | 16.625 | 29.301 | 1.00 40.83 |
| ATOM | 2590 | O | ALA | B | 284 | 37.921 | 16.637 | 30.522 | 1.00 41.29 |
| ATOM | 2591 | N | PHE | B | 285 | 39.203 | 16.538 | 28.638 | 1.00 39.98 |
| ATOM | 2592 | CA | PHE | B | 285 | 40.524 | 16.364 | 29.274 | 1.00 37.14 |
| ATOM | 2593 | CB | PHE | B | 285 | 41.485 | 15.767 | 28.213 | 1.00 34.26 |
| ATOM | 2594 | CG | PHE | B | 285 | 42.884 | 15.507 | 28.731 | 1.00 31.34 |
| ATOM | 2595 | CD1 | PHE | B | 285 | 43.181 | 14.336 | 29.409 | 1.00 29.73 |
| ATOM | 2596 | CD2 | PHE | B | 285 | 43.914 | 16.416 | 28.501 | 1.00 30.95 |
| ATOM | 2597 | CE1 | PHE | B | 285 | 44.462 | 14.072 | 29.826 | 1.00 27.91 |
| ATOM | 2598 | CE2 | PHE | B | 285 | 45.195 | 16.155 | 28.916 | 1.00 28.35 |
| ATOM | 2599 | CZ | PHE | B | 285 | 45.471 | 14.975 | 29.568 | 1.00 26.47 |
| ATOM | 2600 | C | PHE | B | 285 | 40.988 | 17.747 | 29.782 | 1.00 36.57 |
| ATOM | 2601 | O | PHE | B | 285 | 41.320 | 17.868 | 30.965 | 1.00 36.95 |
| ATOM | 2602 | N | LEU | B | 286 | 41.132 | 18.764 | 29.038 | 0.00 47.33 |
| ATOM | 2603 | CA | LEU | B | 286 | 41.607 | 20.070 | 29.502 | 0.00 49.77 |
| ATOM | 2604 | CB | LEU | B | 286 | 41.825 | 21.031 | 28.318 | 0.00 50.36 |
| ATOM | 2605 | CG | LEU | B | 286 | 43.090 | 20.787 | 27.486 | 0.00 51.61 |
| ATOM | 2606 | CD1 | LEU | B | 286 | 42.959 | 21.388 | 26.077 | 0.00 52.80 |
| ATOM | 2607 | CD2 | LEU | B | 286 | 44.331 | 21.324 | 28.201 | 0.00 51.49 |
| ATOM | 2608 | C | LEU | B | 286 | 40.581 | 20.649 | 30.473 | 0.00 52.20 |
| ATOM | 2609 | O | LEU | B | 286 | 40.900 | 21.518 | 31.301 | 0.00 53.32 |
| ATOM | 2610 | N | ALA | B | 287 | 39.342 | 20.168 | 30.350 | 0.00 54.04 |
| ATOM | 2611 | CA | ALA | B | 287 | 38.254 | 20.608 | 31.226 | 0.00 55.32 |
| ATOM | 2612 | CB | ALA | B | 287 | 36.928 | 20.048 | 30.719 | 0.00 54.54 |
| ATOM | 2613 | C | ALA | B | 287 | 38.553 | 20.123 | 32.660 | 0.00 56.28 |
| ATOM | 2614 | O | ALA | B | 287 | 38.146 | 20.744 | 33.665 | 0.00 56.51 |
| ATOM | 2615 | N | GLU | B | 288 | 39.369 | 19.074 | 32.731 | 0.00 57.65 |
| ATOM | 2616 | CA | GLU | B | 288 | 39.792 | 18.467 | 34.008 | 0.00 58.84 |
| ATOM | 2617 | CB | GLU | B | 288 | 40.187 | 16.990 | 33.777 | 0.00 60.54 |
| ATOM | 2618 | CG | GLU | B | 288 | 39.194 | 16.158 | 32.924 | 0.00 61.51 |
| ATOM | 2619 | CD | GLU | B | 288 | 39.594 | 14.682 | 32.782 | 0.00 61.54 |
| ATOM | 2620 | OE1 | GLU | B | 288 | 40.816 | 14.380 | 32.685 | 0.00 61.14 |
| ATOM | 2621 | OE2 | GLU | B | 288 | 38.676 | 13.828 | 32.769 | 0.00 60.04 |
| ATOM | 2622 | C | GLU | B | 288 | 40.977 | 19.214 | 34.670 | 0.00 58.30 |
| ATOM | 2623 | O | GLU | B | 288 | 41.455 | 18.831 | 35.753 | 0.00 56.41 |
| ATOM | 2624 | N | ALA | B | 289 | 41.497 | 20.227 | 33.971 | 0.00 58.94 |
| ATOM | 2625 | CA | ALA | B | 289 | 42.617 | 21.027 | 34.477 | 0.00 58.86 |
| ATOM | 2626 | CB | ALA | B | 289 | 43.681 | 21.226 | 33.384 | 0.00 59.43 |
| ATOM | 2627 | C | ALA | B | 289 | 42.156 | 22.375 | 34.995 | 0.00 58.67 |
| ATOM | 2628 | O | ALA | B | 289 | 42.829 | 23.014 | 35.809 | 0.00 58.08 |
| ATOM | 2629 | N | ASN | B | 290 | 41.017 | 22.827 | 34.493 | 0.00 59.48 |
| ATOM | 2630 | CA | ASN | B | 290 | 40.461 | 24.112 | 34.892 | 0.00 60.28 |
| ATOM | 2631 | CB | ASN | B | 290 | 39.256 | 24.440 | 34.009 | 0.00 61.94 |
| ATOM | 2632 | CG | ASN | B | 290 | 39.650 | 24.595 | 32.544 | 0.00 63.63 |
| ATOM | 2633 | OD1 | ASN | B | 290 | 38.984 | 24.083 | 31.636 | 0.00 63.33 |
| ATOM | 2634 | ND2 | ASN | B | 290 | 40.775 | 25.281 | 32.312 | 0.00 65.24 |
| ATOM | 2635 | C | ASN | B | 290 | 40.104 | 24.180 | 36.369 | 0.00 60.83 |
| ATOM | 2636 | O | ASN | B | 290 | 39.942 | 25.278 | 36.915 | 0.00 61.21 |
| ATOM | 2637 | N | LEU | B | 291 | 39.985 | 23.007 | 37.004 | 0.00 60.49 |
| ATOM | 2638 | CA | LEU | B | 291 | 39.697 | 22.909 | 38.437 | 0.00 60.22 |
| ATOM | 2639 | CB | LEU | B | 291 | 39.203 | 21.500 | 38.775 | 0.00 61.42 |
| ATOM | 2640 | CG | LEU | B | 291 | 38.642 | 21.293 | 40.183 | 0.00 63.34 |
| ATOM | 2641 | CD1 | LEU | B | 291 | 37.303 | 21.997 | 40.333 | 0.00 62.49 |
| ATOM | 2642 | CD2 | LEU | B | 291 | 38.506 | 19.810 | 40.495 | 0.00 64.10 |

Figure 10

| | | | | | | | | |
|---|---|---|---|---|---|---|---|---|
| ATOM | 2643 | C | LEU | B | 291 | 40.931 | 23.254 | 39.268 | 0.00 59.37 |
| ATOM | 2644 | O | LEU | B | 291 | 40.870 | 24.040 | 40.177 | 0.00 58.58 |
| ATOM | 2645 | N | MET | B | 292 | 42.052 | 22.676 | 38.825 | 0.00 59.54 |
| ATOM | 2646 | CA | MET | B | 292 | 43.381 | 22.872 | 39.408 | 0.00 59.23 |
| ATOM | 2647 | CB | MET | B | 292 | 44.397 | 22.102 | 38.549 | 0.00 59.24 |
| ATOM | 2648 | CG | MET | B | 292 | 45.470 | 21.379 | 39.323 | 0.00 60.17 |
| ATOM | 2649 | SD | MET | B | 292 | 46.427 | 20.273 | 38.278 | 0.00 60.45 |
| ATOM | 2650 | CE | MET | B | 292 | 45.651 | 18.628 | 38.721 | 0.00 61.37 |
| ATOM | 2651 | C | MET | B | 292 | 43.757 | 24.371 | 39.476 | 0.00 58.45 |
| ATOM | 2652 | O | MET | B | 292 | 44.336 | 24.846 | 40.454 | 0.00 58.16 |
| ATOM | 2653 | N | LYS | B | 293 | 43.426 | 25.108 | 38.421 | 0.00 58.33 |
| ATOM | 2654 | CA | LYS | B | 293 | 43.694 | 26.539 | 38.357 | 0.00 58.20 |
| ATOM | 2655 | CB | LYS | B | 293 | 43.111 | 27.127 | 37.066 | 0.00 57.89 |
| ATOM | 2656 | CG | LYS | B | 293 | 43.611 | 26.466 | 35.795 | 0.00 57.87 |
| ATOM | 2657 | CD | LYS | B | 293 | 42.998 | 27.075 | 34.550 | 0.00 58.31 |
| ATOM | 2658 | CE | LYS | B | 293 | 43.687 | 26.527 | 33.304 | 0.00 58.75 |
| ATOM | 2659 | NZ | LYS | B | 293 | 43.216 | 27.206 | 32.073 | 0.00 59.26 |
| ATOM | 2660 | C | LYS | B | 293 | 42.977 | 27.152 | 39.547 | 0.00 58.44 |
| ATOM | 2661 | O | LYS | B | 293 | 43.559 | 27.912 | 40.333 | 0.00 59.24 |
| ATOM | 2662 | N | GLN | B | 294 | 41.723 | 26.746 | 39.712 | 0.00 58.04 |
| ATOM | 2663 | CA | GLN | B | 294 | 40.873 | 27.228 | 40.795 | 0.00 57.58 |
| ATOM | 2664 | CB | GLN | B | 294 | 39.475 | 26.583 | 40.673 | 0.00 59.70 |
| ATOM | 2665 | CG | GLN | B | 294 | 38.861 | 26.682 | 39.277 | 0.00 62.76 |
| ATOM | 2666 | CD | GLN | B | 294 | 38.877 | 28.102 | 38.740 | 0.00 65.30 |
| ATOM | 2667 | OE1 | GLN | B | 294 | 39.637 | 28.428 | 37.820 | 0.00 66.69 |
| ATOM | 2668 | NE2 | GLN | B | 294 | 38.050 | 28.962 | 39.325 | 0.00 66.25 |
| ATOM | 2669 | C | GLN | B | 294 | 41.421 | 27.018 | 42.228 | 0.00 55.70 |
| ATOM | 2670 | O | GLN | B | 294 | 41.637 | 27.993 | 42.957 | 0.00 56.07 |
| ATOM | 2671 | N | LEU | B | 295 | 41.687 | 25.764 | 42.606 | 0.00 52.54 |
| ATOM | 2672 | CA | LEU | B | 295 | 42.151 | 25.446 | 43.957 | 0.00 48.98 |
| ATOM | 2673 | CB | LEU | B | 295 | 41.421 | 24.207 | 44.480 | 0.00 48.19 |
| ATOM | 2674 | CG | LEU | B | 295 | 39.903 | 24.204 | 44.507 | 0.00 47.55 |
| ATOM | 2675 | CD1 | LEU | B | 295 | 39.410 | 22.839 | 44.987 | 0.00 46.77 |
| ATOM | 2676 | CD2 | LEU | B | 295 | 39.405 | 25.329 | 45.402 | 0.00 46.45 |
| ATOM | 2677 | C | LEU | B | 295 | 43.641 | 25.226 | 44.151 | 0.00 47.04 |
| ATOM | 2678 | O | LEU | B | 295 | 44.179 | 24.197 | 43.740 | 0.00 47.58 |
| ATOM | 2679 | N | GLN | B | 296 | 44.251 | 25.951 | 44.741 | 1.00 34.19 |
| ATOM | 2680 | CA | GLN | B | 296 | 45.665 | 25.919 | 45.116 | 1.00 36.47 |
| ATOM | 2681 | CB | GLN | B | 296 | 46.396 | 27.144 | 44.556 | 1.00 38.23 |
| ATOM | 2682 | CG | GLN | B | 296 | 46.629 | 27.103 | 43.047 | 1.00 42.71 |
| ATOM | 2683 | CD | GLN | B | 296 | 47.070 | 28.448 | 42.481 | 1.00 45.60 |
| ATOM | 2684 | OE1 | GLN | B | 296 | 47.662 | 29.276 | 43.193 | 1.00 47.49 |
| ATOM | 2685 | NE2 | GLN | B | 296 | 46.788 | 28.671 | 41.194 | 1.00 44.96 |
| ATOM | 2686 | C | GLN | B | 296 | 45.926 | 25.781 | 46.634 | 1.00 36.13 |
| ATOM | 2687 | O | GLN | B | 296 | 45.298 | 26.458 | 47.461 | 1.00 37.50 |
| ATOM | 2688 | N | HIS | B | 297 | 46.901 | 24.947 | 46.993 | 1.00 34.44 |
| ATOM | 2689 | CA | HIS | B | 297 | 47.201 | 24.701 | 48.400 | 1.00 33.39 |
| ATOM | 2690 | CB | HIS | B | 297 | 45.991 | 23.991 | 49.017 | 1.00 31.53 |
| ATOM | 2691 | CG | HIS | B | 297 | 46.057 | 23.839 | 50.510 | 1.00 28.58 |
| ATOM | 2692 | CD2 | HIS | B | 297 | 45.633 | 24.654 | 51.493 | 1.00 26.86 |
| ATOM | 2693 | ND1 | HIS | B | 297 | 46.565 | 22.713 | 51.115 | 1.00 28.25 |
| ATOM | 2694 | CE1 | HIS | B | 297 | 46.447 | 22.844 | 52.428 | 1.00 26.94 |
| ATOM | 2695 | NE2 | HIS | B | 297 | 45.889 | 24.001 | 52.686 | 1.00 26.01 |
| ATOM | 2696 | C | HIS | B | 297 | 48.429 | 23.808 | 48.511 | 1.00 33.48 |
| ATOM | 2697 | O | HIS | B | 297 | 48.710 | 23.030 | 47.606 | 1.00 34.04 |
| ATOM | 2698 | N | GLN | B | 298 | 49.140 | 23.891 | 49.628 | 1.00 34.79 |
| ATOM | 2699 | CA | GLN | B | 298 | 50.335 | 23.071 | 49.813 | 1.00 35.96 |
| ATOM | 2700 | CB | GLN | B | 298 | 51.125 | 23.480 | 51.075 | 1.00 39.47 |
| ATOM | 2701 | CG | GLN | B | 298 | 52.169 | 24.618 | 50.826 | 1.00 45.69 |

Figure 10

| | | | | | | | | | |
|---|---|---|---|---|---|---|---|---|---|
| ATOM | 2702 | CD | GLN | B | 298 | 52.994 | 24.428 | 49.527 | 1.00 48.66 |
| ATOM | 2703 | OE1 | GLN | B | 298 | 52.859 | 25.201 | 48.564 | 1.00 50.58 |
| ATOM | 2704 | NE2 | GLN | B | 298 | 53.818 | 23.381 | 49.489 | 1.00 49.19 |
| ATOM | 2705 | C | GLN | B | 298 | 50.092 | 21.568 | 49.801 | 1.00 34.53 |
| ATOM | 2706 | O | GLN | B | 298 | 51.001 | 20.787 | 49.539 | 1.00 34.78 |
| ATOM | 2707 | N | ARG | B | 299 | 48.858 | 21.158 | 50.038 | 1.00 33.60 |
| ATOM | 2708 | CA | ARG | B | 299 | 48.533 | 19.737 | 50.043 | 1.00 32.50 |
| ATOM | 2709 | CB | ARG | B | 299 | 47.649 | 19.427 | 51.247 | 1.00 33.39 |
| ATOM | 2710 | CG | ARG | B | 299 | 48.324 | 19.731 | 52.554 | 1.00 33.59 |
| ATOM | 2711 | CD | ARG | B | 299 | 49.476 | 18.791 | 52.725 | 1.00 35.67 |
| ATOM | 2712 | NE | ARG | B | 299 | 50.471 | 19.310 | 53.644 | 1.00 36.86 |
| ATOM | 2713 | CZ | ARG | B | 299 | 51.777 | 19.195 | 53.443 | 1.00 39.14 |
| ATOM | 2714 | NH1 | ARG | B | 299 | 52.253 | 18.580 | 52.354 | 1.00 41.02 |
| ATOM | 2715 | NH2 | ARG | B | 299 | 52.609 | 19.678 | 54.344 | 1.00 39.98 |
| ATOM | 2716 | C | ARG | B | 299 | 47.843 | 19.293 | 48.751 | 1.00 32.04 |
| ATOM | 2717 | O | ARG | B | 299 | 47.308 | 18.192 | 48.680 | 1.00 31.52 |
| ATOM | 2718 | N | LEU | B | 300 | 47.831 | 20.175 | 47.748 | 1.00 31.45 |
| ATOM | 2719 | CA | LEU | B | 300 | 47.211 | 19.907 | 46.454 | 1.00 30.64 |
| ATOM | 2720 | CB | LEU | B | 300 | 46.048 | 20.880 | 46.226 | 1.00 29.67 |
| ATOM | 2721 | CG | LEU | B | 300 | 44.643 | 20.439 | 46.674 | 1.00 29.97 |
| ATOM | 2722 | CD1 | LEU | B | 300 | 44.592 | 20.079 | 48.150 | 1.00 26.94 |
| ATOM | 2723 | CD2 | LEU | B | 300 | 43.663 | 21.558 | 46.365 | 1.00 30.53 |
| ATOM | 2724 | C | LEU | B | 300 | 48.230 | 20.026 | 45.324 | 1.00 30.44 |
| ATOM | 2725 | O | LEU | B | 300 | 49.043 | 20.941 | 45.309 | 1.00 30.90 |
| ATOM | 2726 | N | VAL | B | 301 | 48.192 | 19.093 | 44.382 | 1.00 31.60 |
| ATOM | 2727 | CA | VAL | B | 301 | 49.118 | 19.110 | 43.254 | 1.00 33.65 |
| ATOM | 2728 | CB | VAL | B | 301 | 48.943 | 17.857 | 42.358 | 1.00 32.38 |
| ATOM | 2729 | CG1 | VAL | B | 301 | 49.654 | 18.032 | 41.031 | 1.00 32.63 |
| ATOM | 2730 | CG2 | VAL | B | 301 | 49.497 | 16.630 | 43.073 | 1.00 31.72 |
| ATOM | 2731 | C | VAL | B | 301 | 48.891 | 20.378 | 42.452 | 1.00 35.59 |
| ATOM | 2732 | O | VAL | B | 301 | 47.772 | 20.649 | 42.003 | 1.00 36.26 |
| ATOM | 2733 | N | ARG | B | 302 | 49.949 | 21.168 | 42.293 | 1.00 37.99 |
| ATOM | 2734 | CA | ARG | B | 302 | 49.874 | 22.425 | 41.550 | 1.00 40.26 |
| ATOM | 2735 | CB | ARG | B | 302 | 50.998 | 23.368 | 41.980 | 1.00 44.36 |
| ATOM | 2736 | CG | ARG | B | 302 | 50.827 | 24.790 | 41.533 | 1.00 51.67 |
| ATOM | 2737 | CD | ARG | B | 302 | 52.107 | 25.559 | 41.809 | 1.00 59.94 |
| ATOM | 2738 | NE | ARG | B | 302 | 52.071 | 26.919 | 41.270 | 1.00 66.22 |
| ATOM | 2739 | CZ | ARG | B | 302 | 53.062 | 27.805 | 41.382 | 1.00 69.09 |
| ATOM | 2740 | NH1 | ARG | B | 302 | 54.195 | 27.483 | 42.010 | 1.00 70.28 |
| ATOM | 2741 | NH2 | ARG | B | 302 | 52.904 | 29.030 | 40.888 | 1.00 70.33 |
| ATOM | 2742 | C | ARG | B | 302 | 49.935 | 22.141 | 40.050 | 1.00 39.47 |
| ATOM | 2743 | O | ARG | B | 302 | 50.740 | 21.335 | 39.591 | 1.00 38.43 |
| ATOM | 2744 | N | LEU | B | 303 | 49.031 | 22.770 | 39.309 | 1.00 39.54 |
| ATOM | 2745 | CA | LEU | B | 303 | 48.928 | 22.590 | 37.875 | 1.00 40.21 |
| ATOM | 2746 | CB | LEU | B | 303 | 47.438 | 22.425 | 37.507 | 1.00 41.07 |
| ATOM | 2747 | CG | LEU | B | 303 | 46.591 | 21.410 | 38.327 | 1.00 41.54 |
| ATOM | 2748 | CD1 | LEU | B | 303 | 45.097 | 21.482 | 38.032 | 1.00 40.75 |
| ATOM | 2749 | CD2 | LEU | B | 303 | 47.069 | 20.020 | 38.077 | 1.00 40.75 |
| ATOM | 2750 | C | LEU | B | 303 | 49.598 | 23.750 | 37.121 | 1.00 40.03 |
| ATOM | 2751 | O | LEU | B | 303 | 48.980 | 24.778 | 36.918 | 1.00 41.22 |
| ATOM | 2752 | N | TYR | B | 304 | 50.872 | 23.591 | 36.747 | 1.00 40.04 |
| ATOM | 2753 | CA | TYR | B | 304 | 51.638 | 24.630 | 36.034 | 1.00 39.93 |
| ATOM | 2754 | CB | TYR | B | 304 | 53.094 | 24.189 | 35.822 | 1.00 40.82 |
| ATOM | 2755 | CG | TYR | B | 304 | 53.902 | 23.933 | 37.088 | 1.00 42.51 |
| ATOM | 2756 | CD1 | TYR | B | 304 | 55.003 | 23.077 | 37.066 | 1.00 43.38 |
| ATOM | 2757 | CE1 | TYR | B | 304 | 55.763 | 22.840 | 38.212 | 1.00 45.01 |
| ATOM | 2758 | CD2 | TYR | B | 304 | 53.578 | 24.553 | 38.299 | 1.00 43.07 |
| ATOM | 2759 | CE2 | TYR | B | 304 | 54.334 | 24.325 | 39.453 | 1.00 44.78 |
| ATOM | 2760 | CZ | TYR | B | 304 | 55.428 | 23.464 | 39.401 | 1.00 45.35 |

Figure 10

| ATOM | 2761 | OH | TYR | B | 304 | 56.189 | 23.223 | 40.525 | 1.00 | 44.33 |
| ATOM | 2762 | C | TYR | B | 304 | 51.080 | 25.162 | 34.696 | 1.00 | 39.92 |
| ATOM | 2763 | O | TYR | B | 304 | 50.746 | 26.343 | 34.592 | 1.00 | 39.95 |
| ATOM | 2764 | N | ALA | B | 305 | 51.011 | 24.321 | 33.669 | 1.00 | 40.32 |
| ATOM | 2765 | CA | ALA | B | 305 | 50.521 | 24.794 | 32.381 | 1.00 | 39.84 |
| ATOM | 2766 | CB | ALA | B | 305 | 51.681 | 25.351 | 31.581 | 1.00 | 40.69 |
| ATOM | 2767 | C | ALA | B | 305 | 49.791 | 23.737 | 31.577 | 1.00 | 40.35 |
| ATOM | 2768 | O | ALA | B | 305 | 49.565 | 22.630 | 32.061 | 1.00 | 39.81 |
| ATOM | 2769 | N | VAL | B | 306 | 49.385 | 24.109 | 30.358 | 1.00 | 40.42 |
| ATOM | 2770 | CA | VAL | B | 306 | 48.672 | 23.218 | 29.414 | 1.00 | 41.16 |
| ATOM | 2771 | CB | VAL | B | 306 | 47.107 | 23.323 | 29.518 | 1.00 | 41.40 |
| ATOM | 2772 | CG1 | VAL | B | 306 | 46.585 | 22.581 | 30.741 | 1.00 | 42.50 |
| ATOM | 2773 | CG2 | VAL | B | 306 | 46.664 | 24.779 | 29.539 | 1.00 | 41.14 |
| ATOM | 2774 | C | VAL | B | 306 | 49.032 | 23.494 | 27.938 | 1.00 | 40.77 |
| ATOM | 2775 | O | VAL | B | 306 | 49.289 | 24.635 | 27.553 | 1.00 | 40.94 |
| ATOM | 2776 | N | VAL | B | 307 | 49.062 | 22.440 | 27.126 | 1.00 | 39.96 |
| ATOM | 2777 | CA | VAL | B | 307 | 49.343 | 22.577 | 25.703 | 1.00 | 39.89 |
| ATOM | 2778 | CB | VAL | B | 307 | 50.571 | 21.715 | 25.255 | 1.00 | 39.20 |
| ATOM | 2779 | CG1 | VAL | B | 307 | 50.841 | 21.873 | 23.749 | 1.00 | 37.38 |
| ATOM | 2780 | CG2 | VAL | B | 307 | 51.802 | 22.123 | 26.053 | 1.00 | 38.22 |
| ATOM | 2781 | C | VAL | B | 307 | 48.060 | 22.132 | 25.009 | 1.00 | 40.13 |
| ATOM | 2782 | O | VAL | B | 307 | 47.697 | 20.952 | 25.031 | 1.00 | 38.32 |
| ATOM | 2783 | N | THR | B | 308 | 47.357 | 23.106 | 24.437 | 1.00 | 41.85 |
| ATOM | 2784 | CA | THR | B | 308 | 46.082 | 22.862 | 23.766 | 1.00 | 44.00 |
| ATOM | 2785 | CB | THR | B | 308 | 45.238 | 24.143 | 23.715 | 1.00 | 43.18 |
| ATOM | 2786 | OG1 | THR | B | 308 | 46.091 | 25.259 | 23.452 | 1.00 | 44.86 |
| ATOM | 2787 | CG2 | THR | B | 308 | 44.538 | 24.373 | 25.045 | 1.00 | 41.38 |
| ATOM | 2788 | C | THR | B | 308 | 46.102 | 22.182 | 22.394 | 1.00 | 46.19 |
| ATOM | 2789 | O | THR | B | 308 | 45.085 | 21.652 | 21.964 | 1.00 | 46.91 |
| ATOM | 2790 | N | GLN | B | 309 | 47.228 | 22.217 | 21.688 | 1.00 | 48.55 |
| ATOM | 2791 | CA | GLN | B | 309 | 47.315 | 21.555 | 20.390 | 1.00 | 50.28 |
| ATOM | 2792 | CB | GLN | B | 309 | 48.361 | 22.237 | 19.497 | 1.00 | 54.72 |
| ATOM | 2793 | CG | GLN | B | 309 | 47.983 | 23.638 | 19.016 | 1.00 | 61.05 |
| ATOM | 2794 | CD | GLN | B | 309 | 46.735 | 23.666 | 18.113 | 1.00 | 64.96 |
| ATOM | 2795 | OE1 | GLN | B | 309 | 46.113 | 22.635 | 17.834 | 1.00 | 66.54 |
| ATOM | 2796 | NE2 | GLN | B | 309 | 46.373 | 24.862 | 17.655 | 1.00 | 67.10 |
| ATOM | 2797 | C | GLN | B | 309 | 47.687 | 20.087 | 20.593 | 1.00 | 49.63 |
| ATOM | 2798 | O | GLN | B | 309 | 48.520 | 19.774 | 21.437 | 1.00 | 48.70 |
| ATOM | 2799 | N | GLU | B | 310 | 47.115 | 19.205 | 19.777 | 1.00 | 50.10 |
| ATOM | 2800 | CA | GLU | B | 310 | 47.373 | 17.764 | 19.857 | 1.00 | 51.07 |
| ATOM | 2801 | CB | GLU | B | 310 | 46.400 | 16.984 | 18.955 | 1.00 | 55.43 |
| ATOM | 2802 | CG | GLU | B | 310 | 46.418 | 17.378 | 17.462 | 1.00 | 63.18 |
| ATOM | 2803 | CD | GLU | B | 310 | 45.410 | 18.479 | 17.100 | 1.00 | 67.47 |
| ATOM | 2804 | OE1 | GLU | B | 310 | 44.191 | 18.249 | 17.305 | 1.00 | 69.84 |
| ATOM | 2805 | OE2 | GLU | B | 310 | 45.836 | 19.560 | 16.602 | 1.00 | 68.72 |
| ATOM | 2806 | C | GLU | B | 310 | 48.813 | 17.343 | 19.533 | 1.00 | 49.88 |
| ATOM | 2807 | O | GLU | B | 310 | 49.395 | 17.807 | 18.544 | 1.00 | 50.33 |
| ATOM | 2808 | N | PRO | B | 311 | 49.423 | 16.488 | 20.390 | 1.00 | 48.13 |
| ATOM | 2809 | CD | PRO | B | 311 | 50.699 | 15.841 | 20.026 | 1.00 | 48.27 |
| ATOM | 2810 | CA | PRO | B | 311 | 48.885 | 15.884 | 21.629 | 1.00 | 45.19 |
| ATOM | 2811 | CB | PRO | B | 311 | 49.945 | 14.832 | 21.994 | 1.00 | 45.19 |
| ATOM | 2812 | CG | PRO | B | 311 | 50.558 | 14.482 | 20.671 | 1.00 | 46.84 |
| ATOM | 2813 | C | PRO | B | 311 | 48.658 | 16.883 | 22.789 | 1.00 | 42.21 |
| ATOM | 2814 | O | PRO | B | 311 | 49.516 | 17.725 | 23.104 | 1.00 | 42.73 |
| ATOM | 2815 | N | ILE | B | 312 | 47.490 | 16.765 | 23.421 | 1.00 | 38.42 |
| ATOM | 2816 | CA | ILE | B | 312 | 47.075 | 17.635 | 24.528 | 1.00 | 33.68 |
| ATOM | 2817 | CB | ILE | B | 312 | 45.570 | 17.422 | 24.870 | 1.00 | 33.04 |
| ATOM | 2818 | CG2 | ILE | B | 312 | 45.052 | 18.572 | 25.724 | 1.00 | 33.27 |
| ATOM | 2819 | CG1 | ILE | B | 312 | 44.726 | 17.349 | 23.597 | 1.00 | 31.95 |

Figure 10

```
ATOM   2820  CD1 ILE B 312      44.744  18.623  22.785  1.00 30.63
ATOM   2821  C   ILE B 312      47.883  17.302  25.773  1.00 30.83
ATOM   2822  O   ILE B 312      48.021  16.130  26.124  1.00 29.04
ATOM   2823  N   TYR B 313      48.421  18.325  26.429  1.00 28.83
ATOM   2824  CA  TYR B 313      49.208  18.120  27.644  1.00 28.06
ATOM   2825  CB  TYR B 313      50.649  18.621  27.473  1.00 26.96
ATOM   2826  CG  TYR B 313      51.587  17.846  26.579  1.00 28.24
ATOM   2827  CD1 TYR B 313      51.244  16.595  26.059  1.00 27.09
ATOM   2828  CE1 TYR B 313      52.109  15.915  25.199  1.00 28.06
ATOM   2829  CD2 TYR B 313      52.824  18.393  26.223  1.00 27.91
ATOM   2830  CE2 TYR B 313      53.694  17.724  25.369  1.00 28.66
ATOM   2831  CZ  TYR B 313      53.336  16.491  24.856  1.00 29.56
ATOM   2832  OH  TYR B 313      54.197  15.844  23.992  1.00 30.63
ATOM   2833  C   TYR B 313      48.678  18.862  28.864  1.00 28.31
ATOM   2834  O   TYR B 313      48.081  19.936  28.754  1.00 28.43
ATOM   2835  N   ILE B 314      48.943  18.294  30.035  1.00 28.71
ATOM   2836  CA  ILE B 314      48.625  18.942  31.301  1.00 29.08
ATOM   2837  CB  ILE B 314      47.436  18.299  32.078  1.00 30.88
ATOM   2838  CG2 ILE B 314      47.307  18.912  33.492  1.00 28.24
ATOM   2839  CG1 ILE B 314      46.133  18.583  31.342  1.00 32.26
ATOM   2840  CD1 ILE B 314      44.928  17.987  32.008  1.00 35.77
ATOM   2841  C   ILE B 314      49.930  18.794  32.062  1.00 28.13
ATOM   2842  O   ILE B 314      50.466  17.692  32.171  1.00 27.82
ATOM   2843  N   ILE B 315      50.498  19.925  32.464  1.00 28.08
ATOM   2844  CA  ILE B 315      51.755  19.944  33.188  1.00 27.98
ATOM   2845  CB  ILE B 315      52.766  20.955  32.556  1.00 29.80
ATOM   2846  CG2 ILE B 315      54.054  21.035  33.372  1.00 29.91
ATOM   2847  CG1 ILE B 315      53.085  20.567  31.111  1.00 29.19
ATOM   2848  CD1 ILE B 315      52.042  21.023  30.118  1.00 29.67
ATOM   2849  C   ILE B 315      51.499  20.337  34.621  1.00 26.93
ATOM   2850  O   ILE B 315      50.854  21.344  34.893  1.00 27.03
ATOM   2851  N   THR B 316      51.996  19.511  35.531  1.00 26.83
ATOM   2852  CA  THR B 316      51.867  19.747  36.962  1.00 25.81
ATOM   2853  CB  THR B 316      51.005  18.661  37.621  1.00 24.09
ATOM   2854  OG1 THR B 316      51.687  17.405  37.539  1.00 24.93
ATOM   2855  CG2 THR B 316      49.692  18.533  36.939  1.00 22.77
ATOM   2856  C   THR B 316      53.267  19.619  37.572  1.00 26.64
ATOM   2857  O   THR B 316      54.233  19.264  36.890  1.00 26.93
ATOM   2858  N   GLU B 317      53.382  19.899  38.862  1.00 26.84
ATOM   2859  CA  GLU B 317      54.658  19.736  39.518  1.00 26.95
ATOM   2860  CB  GLU B 317      54.605  20.267  40.949  1.00 27.77
ATOM   2861  CG  GLU B 317      53.572  19.618  41.832  1.00 28.55
ATOM   2862  CD  GLU B 317      53.590  20.190  43.213  1.00 29.87
ATOM   2863  OE1 GLU B 317      52.548  20.728  43.634  1.00 30.99
ATOM   2864  OE2 GLU B 317      54.649  20.116  43.875  1.00 31.60
ATOM   2865  C   GLU B 317      54.965  18.236  39.510  1.00 27.29
ATOM   2866  O   GLU B 317      54.083  17.396  39.330  1.00 27.22
ATOM   2867  N   TYR B 318      56.231  17.910  39.671  1.00 27.00
ATOM   2868  CA  TYR B 318      56.655  16.537  39.677  1.00 27.07
ATOM   2869  CB  TYR B 318      57.996  16.429  38.964  1.00 26.75
ATOM   2870  CG  TYR B 318      58.620  15.061  39.011  1.00 28.52
ATOM   2871  CD1 TYR B 318      58.097  13.994  38.265  1.00 29.36
ATOM   2872  CE1 TYR B 318      58.667  12.717  38.337  1.00 29.76
ATOM   2873  CD2 TYR B 318      59.731  14.817  39.825  1.00 29.33
ATOM   2874  CE2 TYR B 318      60.307  13.554  39.902  1.00 28.03
ATOM   2875  CZ  TYR B 318      59.774  12.512  39.163  1.00 29.23
ATOM   2876  OH  TYR B 318      60.329  11.263  39.272  1.00 31.13
ATOM   2877  C   TYR B 318      56.783  16.096  41.120  1.00 28.09
ATOM   2878  O   TYR B 318      57.266  16.859  41.955  1.00 28.72
```

Figure 10.

| | | | | | | | | |
|---|---|---|---|---|---|---|---|---|
| ATOM | 2879 | N   | MET | B 319 | 56.272 | 14.903 | 41.420 | 1.00 28.91 |
| ATOM | 2880 | CA  | MET | B 319 | 56.335 | 14.310 | 42.761 | 1.00 29.41 |
| ATOM | 2881 | CB  | MET | B 319 | 54.963 | 13.828 | 43.218 | 1.00 27.96 |
| ATOM | 2882 | CG  | MET | B 319 | 53.953 | 14.935 | 43.341 | 1.00 27.66 |
| ATOM | 2883 | SD  | MET | B 319 | 54.502 | 16.153 | 44.510 | 1.00 30.11 |
| ATOM | 2884 | CE  | MET | B 319 | 53.884 | 15.453 | 46.059 | 1.00 28.47 |
| ATOM | 2885 | C   | MET | B 319 | 57.269 | 13.121 | 42.672 | 1.00 30.96 |
| ATOM | 2886 | O   | MET | B 319 | 56.888 | 12.069 | 42.168 | 1.00 31.91 |
| ATOM | 2887 | N   | GLU | B 320 | 58.497 | 13.320 | 43.142 | 1.00 32.50 |
| ATOM | 2888 | CA  | GLU | B 320 | 59.569 | 12.324 | 43.147 | 1.00 33.01 |
| ATOM | 2889 | CB  | GLU | B 320 | 60.614 | 12.759 | 44.182 | 1.00 38.13 |
| ATOM | 2890 | CG  | GLU | B 320 | 61.777 | 11.791 | 44.408 | 1.00 45.19 |
| ATOM | 2891 | CD  | GLU | B 320 | 62.829 | 11.852 | 43.302 | 1.00 49.30 |
| ATOM | 2892 | OE1 | GLU | B 320 | 62.981 | 12.934 | 42.680 | 1.00 50.25 |
| ATOM | 2893 | OE2 | GLU | B 320 | 63.511 | 10.820 | 43.069 | 1.00 51.20 |
| ATOM | 2894 | C   | GLU | B 320 | 59.168 | 10.863 | 43.393 | 1.00 31.19 |
| ATOM | 2895 | O   | GLU | B 320 | 59.522 | 9.970  | 42.617 | 1.00 31.03 |
| ATOM | 2896 | N   | ASN | B 321 | 58.413 | 10.621 | 44.458 | 1.00 29.48 |
| ATOM | 2897 | CA  | ASN | B 321 | 58.004 | 9.267  | 44.800 | 1.00 27.28 |
| ATOM | 2898 | CB  | ASN | B 321 | 58.069 | 9.083  | 46.300 | 1.00 26.64 |
| ATOM | 2899 | CG  | ASN | B 321 | 59.481 | 8.996  | 46.785 | 1.00 27.03 |
| ATOM | 2900 | OD1 | ASN | B 321 | 60.242 | 8.168  | 46.305 | 1.00 27.48 |
| ATOM | 2901 | ND2 | ASN | B 321 | 59.865 | 9.880  | 47.687 | 1.00 27.86 |
| ATOM | 2902 | C   | ASN | B 321 | 56.695 | 8.740  | 44.266 | 1.00 26.06 |
| ATOM | 2903 | O   | ASN | B 321 | 56.184 | 7.743  | 44.770 | 1.00 26.68 |
| ATOM | 2904 | N   | GLY | B 322 | 56.160 | 9.403  | 43.254 | 1.00 25.42 |
| ATOM | 2905 | CA  | GLY | B 322 | 54.918 | 8.977  | 42.644 | 1.00 24.88 |
| ATOM | 2906 | C   | GLY | B 322 | 53.685 | 8.765  | 43.500 | 1.00 25.68 |
| ATOM | 2907 | O   | GLY | B 322 | 53.350 | 9.543  | 44.388 | 1.00 25.14 |
| ATOM | 2908 | N   | SER | B 323 | 52.997 | 7.674  | 43.207 | 1.00 26.58 |
| ATOM | 2909 | CA  | SER | B 323 | 51.767 | 7.323  | 43.889 | 1.00 27.62 |
| ATOM | 2910 | CB  | SER | B 323 | 51.061 | 6.255  | 43.076 | 1.00 26.87 |
| ATOM | 2911 | OG  | SER | B 323 | 49.753 | 6.058  | 43.540 | 1.00 31.61 |
| ATOM | 2912 | C   | SER | B 323 | 52.028 | 6.798  | 45.293 | 1.00 29.70 |
| ATOM | 2913 | O   | SER | B 323 | 52.994 | 6.058  | 45.499 | 1.00 31.24 |
| ATOM | 2914 | N   | LEU | B 324 | 51.175 | 7.176  | 46.254 | 1.00 29.52 |
| ATOM | 2915 | CA  | LEU | B 324 | 51.307 | 6.715  | 47.643 | 1.00 28.23 |
| ATOM | 2916 | CB  | LEU | B 324 | 50.348 | 7.485  | 48.566 | 1.00 26.66 |
| ATOM | 2917 | CG  | LEU | B 324 | 50.236 | 7.081  | 50.053 | 1.00 27.29 |
| ATOM | 2918 | CD1 | LEU | B 324 | 51.519 | 7.376  | 50.817 | 1.00 25.32 |
| ATOM | 2919 | CD2 | LEU | B 324 | 49.061 | 7.797  | 50.701 | 1.00 26.12 |
| ATOM | 2920 | C   | LEU | B 324 | 51.056 | 5.197  | 47.756 | 1.00 29.00 |
| ATOM | 2921 | O   | LEU | B 324 | 51.767 | 4.507  | 48.474 | 1.00 28.52 |
| ATOM | 2922 | N   | VAL | B 325 | 50.076 | 4.683  | 47.012 | 1.00 29.75 |
| ATOM | 2923 | CA  | VAL | B 325 | 49.746 | 3.264  | 47.034 | 1.00 30.75 |
| ATOM | 2924 | CB  | VAL | B 325 | 48.448 | 2.969  | 46.201 | 1.00 31.11 |
| ATOM | 2925 | CG1 | VAL | B 325 | 48.720 | 2.952  | 44.693 | 1.00 31.12 |
| ATOM | 2926 | CG2 | VAL | B 325 | 47.790 | 1.686  | 46.668 | 1.00 29.41 |
| ATOM | 2927 | C   | VAL | B 325 | 50.932 | 2.401  | 46.580 | 1.00 32.70 |
| ATOM | 2928 | O   | VAL | B 325 | 51.088 | 1.262  | 47.041 | 1.00 32.99 |
| ATOM | 2929 | N   | ASP | B 326 | 51.759 | 2.938  | 45.680 | 1.00 33.76 |
| ATOM | 2930 | CA  | ASP | B 326 | 52.956 | 2.224  | 45.206 | 1.00 34.90 |
| ATOM | 2931 | CB  | ASP | B 326 | 53.399 | 2.703  | 43.817 | 1.00 33.50 |
| ATOM | 2932 | CG  | ASP | B 326 | 52.440 | 2.309  | 42.724 | 1.00 33.74 |
| ATOM | 2933 | OD1 | ASP | B 326 | 51.828 | 1.219  | 42.778 | 1.00 33.84 |
| ATOM | 2934 | OD2 | ASP | B 326 | 52.315 | 3.100  | 41.777 | 1.00 36.49 |
| ATOM | 2935 | C   | ASP | B 326 | 54.120 | 2.439  | 46.177 | 1.00 35.82 |
| ATOM | 2936 | O   | ASP | B 326 | 54.869 | 1.506  | 46.490 | 1.00 36.94 |
| ATOM | 2937 | N   | PHE | B 327 | 54.278 | 3.678  | 46.638 | 1.00 35.94 |

Figure 10

| | | | | | | | | | |
|---|---|---|---|---|---|---|---|---|---|
| ATOM | 2938 | CA  | PHE | B | 327 | 55.347 | 4.024  | 47.561 | 1.00 35.94 |
| ATOM | 2939 | CB  | PHE | B | 327 | 55.320 | 5.522  | 47.866 | 1.00 34.53 |
| ATOM | 2940 | CG  | PHE | B | 327 | 56.346 | 5.945  | 48.874 | 1.00 33.55 |
| ATOM | 2941 | CD1 | PHE | B | 327 | 57.695 | 6.017  | 48.527 | 1.00 32.82 |
| ATOM | 2942 | CD2 | PHE | B | 327 | 55.971 | 6.246  | 50.179 | 1.00 32.91 |
| ATOM | 2943 | CE1 | PHE | B | 327 | 58.653 | 6.376  | 49.458 | 1.00 29.38 |
| ATOM | 2944 | CE2 | PHE | B | 327 | 56.929 | 6.609  | 51.124 | 1.00 32.49 |
| ATOM | 2945 | CZ  | PHE | B | 327 | 58.272 | 6.674  | 50.758 | 1.00 31.40 |
| ATOM | 2946 | C   | PHE | B | 327 | 55.308 | 3.229  | 48.872 | 1.00 37.48 |
| ATOM | 2947 | O   | PHE | B | 327 | 56.355 | 2.825  | 49.399 | 1.00 38.38 |
| ATOM | 2948 | N   | LEU | B | 328 | 54.105 | 3.015  | 49.401 | 1.00 37.45 |
| ATOM | 2949 | CA  | LEU | B | 328 | 53.939 | 2.276  | 50.655 | 1.00 36.84 |
| ATOM | 2950 | CB  | LEU | B | 328 | 52.473 | 2.276  | 51.113 | 1.00 35.56 |
| ATOM | 2951 | CG  | LEU | B | 328 | 51.856 | 3.612  | 51.536 | 1.00 32.62 |
| ATOM | 2952 | CD1 | LEU | B | 328 | 50.349 | 3.521  | 51.535 | 1.00 32.52 |
| ATOM | 2953 | CD2 | LEU | B | 328 | 52.379 | 4.019  | 52.880 | 1.00 31.79 |
| ATOM | 2954 | C   | LEU | B | 328 | 54.434 | 0.848  | 50.524 | 1.00 36.88 |
| ATOM | 2955 | O   | LEU | B | 328 | 54.877 | 0.275  | 51.507 | 1.00 36.71 |
| ATOM | 2956 | N   | LYS | B | 329 | 54.372 | 0.297  | 49.310 | 1.00 38.66 |
| ATOM | 2957 | CA  | LYS | B | 329 | 54.819 | -1.073 | 49.037 | 1.00 40.50 |
| ATOM | 2958 | CB  | LYS | B | 329 | 54.137 | -1.661 | 47.795 | 1.00 38.73 |
| ATOM | 2959 | CG  | LYS | B | 329 | 52.639 | -1.846 | 47.876 | 1.00 38.07 |
| ATOM | 2960 | CD  | LYS | B | 329 | 52.129 | -2.558 | 46.622 | 1.00 39.00 |
| ATOM | 2961 | CE  | LYS | B | 329 | 50.609 | -2.583 | 46.533 | 1.00 39.41 |
| ATOM | 2962 | NZ  | LYS | B | 329 | 50.070 | -1.219 | 46.289 | 1.00 41.23 |
| ATOM | 2963 | C   | LYS | B | 329 | 56.330 | -1.191 | 48.845 | 1.00 42.30 |
| ATOM | 2964 | O   | LYS | B | 329 | 56.877 | -2.290 | 48.986 | 1.00 43.22 |
| ATOM | 2965 | N   | THR | B | 330 | 56.997 | -0.077 | 48.519 | 1.00 43.32 |
| ATOM | 2966 | CA  | THR | B | 330 | 58.452 | -0.069 | 48.288 | 1.00 44.52 |
| ATOM | 2967 | CB  | THR | B | 330 | 58.966 | 1.300  | 47.729 | 1.00 44.63 |
| ATOM | 2968 | OG1 | THR | B | 330 | 58.876 | 2.307  | 48.748 | 1.00 45.24 |
| ATOM | 2969 | CG2 | THR | B | 330 | 58.189 | 1.730  | 46.480 | 1.00 42.60 |
| ATOM | 2970 | C   | THR | B | 330 | 59.216 | -0.354 | 49.583 | 1.00 45.47 |
| ATOM | 2971 | O   | THR | B | 330 | 58.642 | -0.236 | 50.664 | 1.00 45.24 |
| ATOM | 2972 | N   | PRO | B | 331 | 60.514 | -0.744 | 49.484 | 1.00 45.88 |
| ATOM | 2973 | CD  | PRO | B | 331 | 61.252 | -1.043 | 48.239 | 1.00 46.28 |
| ATOM | 2974 | CA  | PRO | B | 331 | 61.350 | -1.039 | 50.657 | 1.00 45.79 |
| ATOM | 2975 | CB  | PRO | B | 331 | 62.738 | -1.230 | 50.038 | 1.00 46.29 |
| ATOM | 2976 | CG  | PRO | B | 331 | 62.427 | -1.861 | 48.734 | 1.00 46.33 |
| ATOM | 2977 | C   | PRO | B | 331 | 61.344 | 0.100  | 51.687 | 1.00 45.89 |
| ATOM | 2978 | O   | PRO | B | 331 | 61.356 | -0.147 | 52.890 | 1.00 45.87 |
| ATOM | 2979 | N   | SER | B | 332 | 61.307 | 1.342  | 51.211 | 1.00 45.78 |
| ATOM | 2980 | CA  | SER | B | 332 | 61.290 | 2.507  | 52.099 | 1.00 46.06 |
| ATOM | 2981 | CB  | SER | B | 332 | 61.749 | 3.757  | 51.343 | 1.00 47.42 |
| ATOM | 2982 | OG  | SER | B | 332 | 62.974 | 3.521  | 50.669 | 1.00 49.46 |
| ATOM | 2983 | C   | SER | B | 332 | 59.890 | 2.752  | 52.651 | 1.00 45.29 |
| ATOM | 2984 | O   | SER | B | 332 | 59.727 | 3.248  | 53.773 | 1.00 43.73 |
| ATOM | 2985 | N   | GLY | B | 333 | 58.888 | 2.420  | 51.842 | 1.00 45.23 |
| ATOM | 2986 | CA  | GLY | B | 333 | 57.509 | 2.604  | 52.249 | 1.00 46.09 |
| ATOM | 2987 | C   | GLY | B | 333 | 57.128 | 1.580  | 53.289 | 1.00 46.78 |
| ATOM | 2988 | O   | GLY | B | 333 | 56.398 | 1.880  | 54.232 | 1.00 46.40 |
| ATOM | 2989 | N   | ILE | B | 334 | 57.658 | 0.373  | 53.119 | 1.00 47.63 |
| ATOM | 2990 | CA  | ILE | B | 334 | 57.407 | -0.734 | 54.029 | 1.00 48.30 |
| ATOM | 2991 | CB  | ILE | B | 334 | 58.015 | -2.050 | 53.467 | 1.00 48.96 |
| ATOM | 2992 | CG2 | ILE | B | 334 | 58.136 | -3.109 | 54.549 | 1.00 49.78 |
| ATOM | 2993 | CG1 | ILE | B | 334 | 57.175 | -2.563 | 52.292 | 1.00 49.14 |
| ATOM | 2994 | CD1 | ILE | B | 334 | 55.785 | -3.057 | 52.660 | 1.00 49.37 |
| ATOM | 2995 | C   | ILE | B | 334 | 57.992 | -0.423 | 55.408 | 1.00 48.32 |
| ATOM | 2996 | O   | ILE | B | 334 | 57.354 | -0.709 | 56.421 | 1.00 49.63 |

Figure 10

```
ATOM   2997  N    LYS B 335      59.159   0.223  55.439  1.00 47.88
ATOM   2998  CA   LYS B 335      59.843   0.567  56.690  1.00 47.63
ATOM   2999  CB   LYS B 335      61.351   0.736  56.441  1.00 49.57
ATOM   3000  CG   LYS B 335      62.107  -0.496  55.906  1.00 52.27
ATOM   3001  CD   LYS B 335      63.528  -0.090  55.435  1.00 54.38
ATOM   3002  CE   LYS B 335      64.215  -1.182  54.597  1.00 55.66
ATOM   3003  NZ   LYS B 335      65.046  -0.591  53.489  1.00 56.14
ATOM   3004  C    LYS B 335      59.336   1.800  57.458  1.00 46.39
ATOM   3005  O    LYS B 335      59.863   2.110  58.523  1.00 47.12
ATOM   3006  N    LEU B 336      58.357   2.528  56.922  1.00 45.37
ATOM   3007  CA   LEU B 336      57.822   3.732  57.601  1.00 43.20
ATOM   3008  CB   LEU B 336      56.811   4.474  56.707  1.00 42.95
ATOM   3009  CG   LEU B 336      57.246   5.153  55.402  1.00 41.26
ATOM   3010  CD1  LEU B 336      56.032   5.684  54.690  1.00 39.35
ATOM   3011  CD2  LEU B 336      58.214   6.282  55.692  1.00 40.70
ATOM   3012  C    LEU B 336      57.147   3.448  58.945  1.00 42.20
ATOM   3013  O    LEU B 336      56.377   2.489  59.071  1.00 42.64
ATOM   3014  N    THR B 337      57.395   4.318  59.926  1.00 41.01
ATOM   3015  CA   THR B 337      56.813   4.174  61.265  1.00 40.30
ATOM   3016  CB   THR B 337      57.606   4.983  62.369  1.00 38.89
ATOM   3017  OG1  THR B 337      57.238   6.365  62.337  1.00 37.79
ATOM   3018  CG2  THR B 337      59.111   4.877  62.160  1.00 39.09
ATOM   3019  C    THR B 337      55.328   4.589  61.305  1.00 40.40
ATOM   3020  O    THR B 337      54.820   5.241  60.388  1.00 40.54
ATOM   3021  N    ILE B 338      54.640   4.205  62.379  1.00 39.51
ATOM   3022  CA   ILE B 338      53.234   4.537  62.547  1.00 37.44
ATOM   3023  CB   ILE B 338      52.633   3.854  63.813  1.00 37.64
ATOM   3024  CG2  ILE B 338      53.330   4.361  65.103  1.00 36.26
ATOM   3025  CG1  ILE B 338      51.114   4.082  63.873  1.00 37.74
ATOM   3026  CD1  ILE B 338      50.307   3.430  62.742  1.00 36.86
ATOM   3027  C    ILE B 338      53.074   6.051  62.633  1.00 36.65
ATOM   3028  O    ILE B 338      52.092   6.600  62.150  1.00 36.93
ATOM   3029  N    ASN B 339      54.065   6.723  63.211  1.00 36.23
ATOM   3030  CA   ASN B 339      54.036   8.180  63.358  1.00 35.09
ATOM   3031  CB   ASN B 339      55.214   8.661  64.200  1.00 34.98
ATOM   3032  CG   ASN B 339      55.244   8.014  65.553  1.00 36.29
ATOM   3033  OD1  ASN B 339      54.870   8.634  66.551  1.00 36.99
ATOM   3034  ND2  ASN B 339      55.649   6.737  65.598  1.00 35.43
ATOM   3035  C    ASN B 339      54.098   8.860  62.013  1.00 34.50
ATOM   3036  O    ASN B 339      53.441   9.884  61.795  1.00 35.28
ATOM   3037  N    LYS B 340      54.911   8.307  61.119  1.00 33.61
ATOM   3038  CA   LYS B 340      55.062   8.875  59.791  1.00 32.85
ATOM   3039  CB   LYS B 340      56.311   8.296  59.120  1.00 33.96
ATOM   3040  CG   LYS B 340      56.609   8.880  57.750  1.00 36.92
ATOM   3041  CD   LYS B 340      56.620  10.415  57.737  1.00 39.02
ATOM   3042  CE   LYS B 340      56.461  10.946  56.297  1.00 41.03
ATOM   3043  NZ   LYS B 340      56.498  12.444  56.172  1.00 42.83
ATOM   3044  C    LYS B 340      53.781   8.656  58.965  1.00 30.68
ATOM   3045  O    LYS B 340      53.267   9.593  58.352  1.00 29.74
ATOM   3046  N    LEU B 341      53.223   7.449  59.042  1.00 29.14
ATOM   3047  CA   LEU B 341      51.990   7.119  58.331  1.00 27.94
ATOM   3048  CB   LEU B 341      51.589   5.657  58.583  1.00 26.38
ATOM   3049  CG   LEU B 341      52.536   4.584  58.029  1.00 25.51
ATOM   3050  CD1  LEU B 341      51.986   3.196  58.284  1.00 23.48
ATOM   3051  CD2  LEU B 341      52.752   4.797  56.549  1.00 24.19
ATOM   3052  C    LEU B 341      50.868   8.055  58.760  1.00 28.04
ATOM   3053  O    LEU B 341      50.147   8.596  57.923  1.00 27.65
ATOM   3054  N    LEU B 342      50.762   8.295  60.065  1.00 28.85
ATOM   3055  CA   LEU B 342      49.727   9.176  60.586  1.00 29.79
```

Figure 10

| | | | | | | | | | |
|---|---|---|---|---|---|---|---|---|---|
| ATOM | 3056 | CB  | LEU | B | 342 | 49.574 |  9.048 | 62.106 | 1.00 31.86 |
| ATOM | 3057 | CG  | LEU | B | 342 | 49.059 |  7.668 | 62.562 | 1.00 33.94 |
| ATOM | 3058 | CD1 | LEU | B | 342 | 48.784 |  7.672 | 64.021 | 1.00 35.04 |
| ATOM | 3059 | CD2 | LEU | B | 342 | 47.798 |  7.287 | 61.842 | 1.00 34.35 |
| ATOM | 3060 | C   | LEU | B | 342 | 49.938 | 10.616 | 60.179 | 1.00 30.32 |
| ATOM | 3061 | O   | LEU | B | 342 | 48.966 | 11.345 | 59.963 | 1.00 30.54 |
| ATOM | 3062 | N   | ASP | B | 343 | 51.189 | 11.036 | 60.040 | 1.00 30.08 |
| ATOM | 3063 | CA  | ASP | B | 343 | 51.395 | 12.402 | 59.610 | 1.00 31.39 |
| ATOM | 3064 | CB  | ASP | B | 343 | 52.821 | 12.886 | 59.829 | 1.00 34.87 |
| ATOM | 3065 | CG  | ASP | B | 343 | 52.924 | 14.407 | 59.686 | 1.00 40.54 |
| ATOM | 3066 | OD1 | ASP | B | 343 | 52.189 | 15.117 | 60.433 | 1.00 43.42 |
| ATOM | 3067 | OD2 | ASP | B | 343 | 53.683 | 14.892 | 58.803 | 1.00 40.91 |
| ATOM | 3068 | C   | ASP | B | 343 | 51.014 | 12.555 | 58.136 | 1.00 30.54 |
| ATOM | 3069 | O   | ASP | B | 343 | 50.578 | 13.625 | 57.706 | 1.00 29.64 |
| ATOM | 3070 | N   | MET | B | 344 | 51.185 | 11.487 | 57.364 | 1.00 29.53 |
| ATOM | 3071 | CA  | MET | B | 344 | 50.833 | 11.521 | 55.951 | 1.00 28.69 |
| ATOM | 3072 | CB  | MET | B | 344 | 51.377 | 10.285 | 55.230 | 1.00 30.71 |
| ATOM | 3073 | CG  | MET | B | 344 | 52.903 | 10.202 | 55.142 | 1.00 32.04 |
| ATOM | 3074 | SD  | MET | B | 344 | 53.433 |  8.672 | 54.323 | 1.00 36.81 |
| ATOM | 3075 | CE  | MET | B | 344 | 53.947 |  9.225 | 52.701 | 1.00 33.65 |
| ATOM | 3076 | C   | MET | B | 344 | 49.306 | 11.592 | 55.824 | 1.00 26.69 |
| ATOM | 3077 | O   | MET | B | 344 | 48.777 | 12.283 | 54.949 | 1.00 26.20 |
| ATOM | 3078 | N   | ALA | B | 345 | 48.619 | 10.877 | 56.719 | 1.00 25.01 |
| ATOM | 3079 | CA  | ALA | B | 345 | 47.157 | 10.845 | 56.770 | 1.00 23.31 |
| ATOM | 3080 | CB  | ALA | B | 345 | 46.679 |  9.823 | 57.822 | 1.00 22.83 |
| ATOM | 3081 | C   | ALA | B | 345 | 46.630 | 12.232 | 57.125 | 1.00 21.98 |
| ATOM | 3082 | O   | ALA | B | 345 | 45.603 | 12.663 | 56.607 | 1.00 21.04 |
| ATOM | 3083 | N   | ALA | B | 346 | 47.337 | 12.913 | 58.025 | 1.00 21.20 |
| ATOM | 3084 | CA  | ALA | B | 346 | 46.972 | 14.245 | 58.453 | 1.00 20.17 |
| ATOM | 3085 | CB  | ALA | B | 346 | 47.774 | 14.617 | 59.660 | 1.00 19.07 |
| ATOM | 3086 | C   | ALA | B | 346 | 47.174 | 15.271 | 57.328 | 1.00 21.46 |
| ATOM | 3087 | O   | ALA | B | 346 | 46.474 | 16.281 | 57.279 | 1.00 22.66 |
| ATOM | 3088 | N   | GLN | B | 347 | 48.117 | 15.017 | 56.420 | 1.00 22.56 |
| ATOM | 3089 | CA  | GLN | B | 347 | 48.366 | 15.925 | 55.294 | 1.00 23.39 |
| ATOM | 3090 | CB  | GLN | B | 347 | 49.707 | 15.624 | 54.628 | 1.00 26.01 |
| ATOM | 3091 | CG  | GLN | B | 347 | 50.894 | 15.865 | 55.529 | 1.00 29.67 |
| ATOM | 3092 | CD  | GLN | B | 347 | 52.196 | 15.597 | 54.840 | 1.00 32.36 |
| ATOM | 3093 | OE1 | GLN | B | 347 | 53.047 | 16.479 | 54.762 | 1.00 35.18 |
| ATOM | 3094 | NE2 | GLN | B | 347 | 52.374 | 14.381 | 54.341 | 1.00 31.80 |
| ATOM | 3095 | C   | GLN | B | 347 | 47.269 | 15.793 | 54.259 | 1.00 22.78 |
| ATOM | 3096 | O   | GLN | B | 347 | 46.840 | 16.771 | 53.646 | 1.00 23.50 |
| ATOM | 3097 | N   | ILE | B | 348 | 46.839 | 14.560 | 54.044 | 1.00 22.24 |
| ATOM | 3098 | CA  | ILE | B | 348 | 45.777 | 14.274 | 53.097 | 1.00 20.97 |
| ATOM | 3099 | CB  | ILE | B | 348 | 45.611 | 12.729 | 52.905 | 1.00 20.02 |
| ATOM | 3100 | CG2 | ILE | B | 348 | 44.485 | 12.408 | 51.914 | 1.00 18.85 |
| ATOM | 3101 | CG1 | ILE | B | 348 | 46.929 | 12.136 | 52.396 | 1.00 19.03 |
| ATOM | 3102 | CD1 | ILE | B | 348 | 46.898 | 10.641 | 52.247 | 1.00 20.39 |
| ATOM | 3103 | C   | ILE | B | 348 | 44.495 | 14.895 | 53.630 | 1.00 20.58 |
| ATOM | 3104 | O   | ILE | B | 348 | 43.714 | 15.488 | 52.873 | 1.00 20.74 |
| ATOM | 3105 | N   | ALA | B | 349 | 44.292 | 14.767 | 54.940 | 1.00 19.80 |
| ATOM | 3106 | CA  | ALA | B | 349 | 43.100 | 15.309 | 55.583 | 1.00 20.27 |
| ATOM | 3107 | CB  | ALA | B | 349 | 43.010 | 14.834 | 56.997 | 1.00 19.48 |
| ATOM | 3108 | C   | ALA | B | 349 | 43.112 | 16.833 | 55.537 | 1.00 21.48 |
| ATOM | 3109 | O   | ALA | B | 349 | 42.054 | 17.462 | 55.475 | 1.00 23.63 |
| ATOM | 3110 | N   | GLU | B | 350 | 44.310 | 17.416 | 55.579 | 1.00 21.46 |
| ATOM | 3111 | CA  | GLU | B | 350 | 44.490 | 18.858 | 55.522 | 1.00 20.94 |
| ATOM | 3112 | CB  | GLU | B | 350 | 45.948 | 19.204 | 55.782 | 1.00 23.49 |
| ATOM | 3113 | CG  | GLU | B | 350 | 46.255 | 20.681 | 55.677 | 1.00 26.11 |
| ATOM | 3114 | CD  | GLU | B | 350 | 47.724 | 21.006 | 55.895 | 1.00 28.16 |

Figure 10

```
ATOM   3115  OE1 GLU B 350      48.514  20.107  56.263  1.00 26.91
ATOM   3116  OE2 GLU B 350      48.086  22.180  55.691  1.00 30.70
ATOM   3117  C   GLU B 350      44.070  19.363  54.149  1.00 21.22
ATOM   3118  O   GLU B 350      43.333  20.340  54.047  1.00 21.58
ATOM   3119  N   GLY B 351      44.511  18.667  53.097  1.00 21.22
ATOM   3120  CA  GLY B 351      44.151  19.045  51.736  1.00 19.71
ATOM   3121  C   GLY B 351      42.653  18.922  51.495  1.00 19.33
ATOM   3122  O   GLY B 351      42.035  19.782  50.854  1.00 19.64
ATOM   3123  N   MET B 352      42.065  17.840  52.001  1.00 18.82
ATOM   3124  CA  MET B 352      40.628  17.609  51.859  1.00 17.98
ATOM   3125  CB  MET B 352      40.262  16.189  52.295  1.00 16.87
ATOM   3126  CG  MET B 352      40.668  15.118  51.299  1.00 17.04
ATOM   3127  SD  MET B 352      40.010  15.351  49.633  1.00 18.64
ATOM   3128  CE  MET B 352      38.254  15.659  49.943  1.00 14.53
ATOM   3129  C   MET B 352      39.836  18.616  52.676  1.00 19.05
ATOM   3130  O   MET B 352      38.705  18.958  52.321  1.00 19.70
ATOM   3131  N   ALA B 353      40.425  19.056  53.789  1.00 19.98
ATOM   3132  CA  ALA B 353      39.816  20.036  54.673  1.00 21.41
ATOM   3133  CB  ALA B 353      40.671  20.190  55.921  1.00 20.58
ATOM   3134  C   ALA B 353      39.675  21.381  53.921  1.00 23.42
ATOM   3135  O   ALA B 353      38.682  22.106  54.075  1.00 24.10
ATOM   3136  N   PHE B 354      40.671  21.701  53.100  1.00 24.15
ATOM   3137  CA  PHE B 354      40.646  22.910  52.291  1.00 25.19
ATOM   3138  CB  PHE B 354      42.029  23.165  51.705  1.00 26.95
ATOM   3139  CG  PHE B 354      42.076  24.305  50.742  1.00 28.33
ATOM   3140  CD1 PHE B 354      41.926  25.611  51.183  1.00 29.32
ATOM   3141  CD2 PHE B 354      42.326  24.068  49.390  1.00 29.70
ATOM   3142  CE1 PHE B 354      42.028  26.678  50.293  1.00 31.39
ATOM   3143  CE2 PHE B 354      42.430  25.118  48.488  1.00 32.36
ATOM   3144  CZ  PHE B 354      42.285  26.432  48.937  1.00 32.07
ATOM   3145  C   PHE B 354      39.630  22.731  51.165  1.00 25.06
ATOM   3146  O   PHE B 354      38.926  23.674  50.808  1.00 25.54
ATOM   3147  N   ILE B 355      39.576  21.527  50.593  1.00 24.80
ATOM   3148  CA  ILE B 355      38.620  21.227  49.520  1.00 25.30
ATOM   3149  CB  ILE B 355      38.898  19.807  48.912  1.00 25.44
ATOM   3150  CG2 ILE B 355      37.683  19.269  48.135  1.00 22.51
ATOM   3151  CG1 ILE B 355      40.176  19.873  48.056  1.00 26.53
ATOM   3152  CD1 ILE B 355      40.686  18.548  47.518  1.00 25.31
ATOM   3153  C   ILE B 355      37.184  21.350  50.059  1.00 25.91
ATOM   3154  O   ILE B 355      36.287  21.861  49.395  1.00 25.33
ATOM   3155  N   GLU B 356      36.995  20.904  51.292  1.00 26.96
ATOM   3156  CA  GLU B 356      35.709  20.976  51.975  1.00 27.80
ATOM   3157  CB  GLU B 356      35.846  20.209  53.268  1.00 26.00
ATOM   3158  CG  GLU B 356      34.681  20.268  54.212  1.00 22.69
ATOM   3159  CD  GLU B 356      34.952  19.382  55.413  1.00 22.26
ATOM   3160  OE1 GLU B 356      35.627  19.824  56.371  1.00 23.34
ATOM   3161  OE2 GLU B 356      34.553  18.210  55.379  1.00 23.65
ATOM   3162  C   GLU B 356      35.384  22.433  52.266  1.00 30.24
ATOM   3163  O   GLU B 356      34.272  22.903  52.046  1.00 31.85
ATOM   3164  N   GLU B 357      36.389  23.137  52.762  1.00 31.79
ATOM   3165  CA  GLU B 357      36.298  24.553  53.086  1.00 33.76
ATOM   3166  CB  GLU B 357      37.680  25.014  53.582  1.00 35.68
ATOM   3167  CG  GLU B 357      37.982  26.493  53.430  1.00 41.23
ATOM   3168  CD  GLU B 357      37.180  27.350  54.383  1.00 45.10
ATOM   3169  OE1 GLU B 357      37.102  26.977  55.584  1.00 47.00
ATOM   3170  OE2 GLU B 357      36.638  28.393  53.926  1.00 45.46
ATOM   3171  C   GLU B 357      35.828  25.400  51.909  1.00 33.61
ATOM   3172  O   GLU B 357      35.004  26.308  52.071  1.00 33.84
ATOM   3173  N   ARG B 358      36.213  25.015  50.708  1.00 33.99
```

Figure 10

| | | | | | | | | | |
|---|---|---|---|---|---|---|---|---|---|
| ATOM | 3174 | CA | ARG | B | 358 | 35.895 | 25.761 | 49.533 | 1.00 34.91 |
| ATOM | 3175 | CB | ARG | B | 358 | 37.132 | 25.849 | 48.632 | 1.00 36.56 |
| ATOM | 3176 | CG | ARG | B | 358 | 38.333 | 26.572 | 49.286 | 1.00 41.02 |
| ATOM | 3177 | CD | ARG | B | 358 | 38.116 | 28.088 | 49.313 | 1.00 44.66 |
| ATOM | 3178 | NE | ARG | B | 358 | 38.247 | 28.593 | 47.953 | 1.00 50.60 |
| ATOM | 3179 | CZ | ARG | B | 358 | 39.402 | 28.981 | 47.411 | 1.00 53.67 |
| ATOM | 3180 | NH1 | ARG | B | 358 | 40.524 | 28.957 | 48.130 | 1.00 54.51 |
| ATOM | 3181 | NH2 | ARG | B | 358 | 39.468 | 29.252 | 46.108 | 1.00 54.23 |
| ATOM | 3182 | C | ARG | B | 358 | 34.714 | 25.179 | 48.793 | 1.00 35.48 |
| ATOM | 3183 | O | ARG | B | 358 | 34.495 | 25.491 | 47.642 | 1.00 35.92 |
| ATOM | 3184 | N | ASN | B | 359 | 34.013 | 24.305 | 49.505 | 1.00 35.79 |
| ATOM | 3185 | CA | ASN | B | 359 | 32.816 | 23.624 | 48.999 | 1.00 35.62 |
| ATOM | 3186 | CB | ASN | B | 359 | 31.634 | 24.584 | 49.004 | 1.00 40.05 |
| ATOM | 3187 | CG | ASN | B | 359 | 31.483 | 25.316 | 50.338 | 1.00 45.32 |
| ATOM | 3188 | OD1 | ASN | B | 359 | 31.036 | 24.732 | 51.336 | 1.00 47.95 |
| ATOM | 3189 | ND2 | ASN | B | 359 | 31.877 | 26.590 | 50.365 | 1.00 47.65 |
| ATOM | 3190 | C | ASN | B | 359 | 32.977 | 22.918 | 47.674 | 1.00 34.67 |
| ATOM | 3191 | O | ASN | B | 359 | 32.234 | 23.146 | 46.717 | 1.00 34.28 |
| ATOM | 3192 | N | TYR | B | 360 | 33.989 | 22.062 | 47.622 | 1.00 34.20 |
| ATOM | 3193 | CA | TYR | B | 360 | 34.272 | 21.230 | 46.457 | 1.00 33.60 |
| ATOM | 3194 | CB | TYR | B | 360 | 35.677 | 21.502 | 45.911 | 1.00 36.02 |
| ATOM | 3195 | CG | TYR | B | 360 | 35.748 | 22.659 | 44.961 | 1.00 38.98 |
| ATOM | 3196 | CD1 | TYR | B | 360 | 36.075 | 23.931 | 45.411 | 1.00 40.16 |
| ATOM | 3197 | CE1 | TYR | B | 360 | 36.130 | 25.009 | 44.543 | 1.00 40.64 |
| ATOM | 3198 | CD2 | TYR | B | 360 | 35.476 | 22.486 | 43.611 | 1.00 40.99 |
| ATOM | 3199 | CE2 | TYR | B | 360 | 35.526 | 23.555 | 42.731 | 1.00 42.04 |
| ATOM | 3200 | CZ | TYR | B | 360 | 35.854 | 24.817 | 43.200 | 1.00 42.02 |
| ATOM | 3201 | OH | TYR | B | 360 | 35.916 | 25.881 | 42.316 | 1.00 43.32 |
| ATOM | 3202 | C | TYR | B | 360 | 34.221 | 19.802 | 46.964 | 1.00 32.16 |
| ATOM | 3203 | O | TYR | B | 360 | 33.999 | 19.570 | 48.154 | 1.00 30.63 |
| ATOM | 3204 | N | ILE | B | 361 | 34.320 | 18.854 | 46.037 | 1.00 30.98 |
| ATOM | 3205 | CA | ILE | B | 361 | 34.368 | 17.437 | 46.372 | 1.00 29.93 |
| ATOM | 3206 | CB | ILE | B | 361 | 33.014 | 16.689 | 46.188 | 1.00 29.25 |
| ATOM | 3207 | CG2 | ILE | B | 361 | 31.935 | 17.373 | 47.011 | 1.00 28.95 |
| ATOM | 3208 | CG1 | ILE | B | 361 | 32.629 | 16.564 | 44.706 | 1.00 30.19 |
| ATOM | 3209 | CD1 | ILE | B | 361 | 31.532 | 15.521 | 44.421 | 1.00 27.24 |
| ATOM | 3210 | C | ILE | B | 361 | 35.457 | 16.827 | 45.492 | 1.00 30.53 |
| ATOM | 3211 | O | ILE | B | 361 | 35.868 | 17.430 | 44.497 | 1.00 32.21 |
| ATOM | 3212 | N | HIS | B | 362 | 36.003 | 15.691 | 45.918 | 1.00 29.75 |
| ATOM | 3213 | CA | HIS | B | 362 | 37.048 | 15.010 | 45.169 | 1.00 27.43 |
| ATOM | 3214 | CB | HIS | B | 362 | 38.014 | 14.348 | 46.136 | 1.00 24.89 |
| ATOM | 3215 | CG | HIS | B | 362 | 39.276 | 13.856 | 45.496 | 1.00 22.21 |
| ATOM | 3216 | CD2 | HIS | B | 362 | 40.572 | 14.147 | 45.751 | 1.00 22.10 |
| ATOM | 3217 | ND1 | HIS | B | 362 | 39.288 | 12.935 | 44.477 | 1.00 21.94 |
| ATOM | 3218 | CE1 | HIS | B | 362 | 40.537 | 12.674 | 44.129 | 1.00 19.02 |
| ATOM | 3219 | NE2 | HIS | B | 362 | 41.334 | 13.396 | 44.886 | 1.00 20.64 |
| ATOM | 3220 | C | HIS | B | 362 | 36.414 | 13.960 | 44.271 | 1.00 27.87 |
| ATOM | 3221 | O | HIS | B | 362 | 36.569 | 14.002 | 43.060 | 1.00 29.15 |
| ATOM | 3222 | N | ARG | B | 363 | 35.613 | 13.101 | 44.893 | 1.00 27.92 |
| ATOM | 3223 | CA | ARG | B | 363 | 34.896 | 11.966 | 44.302 | 1.00 28.36 |
| ATOM | 3224 | CB | ARG | B | 363 | 33.793 | 12.351 | 43.290 | 1.00 29.35 |
| ATOM | 3225 | CG | ARG | B | 363 | 34.215 | 13.047 | 42.024 | 1.00 35.49 |
| ATOM | 3226 | CD | ARG | B | 363 | 33.008 | 13.550 | 41.203 | 1.00 38.82 |
| ATOM | 3227 | NE | ARG | B | 363 | 32.319 | 12.473 | 40.501 | 1.00 40.41 |
| ATOM | 3228 | CZ | ARG | B | 363 | 31.002 | 12.319 | 40.487 | 1.00 42.08 |
| ATOM | 3229 | NH1 | ARG | B | 363 | 30.229 | 13.180 | 41.130 | 1.00 41.74 |
| ATOM | 3230 | NH2 | ARG | B | 363 | 30.458 | 11.285 | 39.850 | 1.00 42.43 |
| ATOM | 3231 | C | ARG | B | 363 | 35.752 | 10.811 | 43.826 | 1.00 27.33 |
| ATOM | 3232 | O | ARG | B | 363 | 35.224 | 9.747 | 43.502 | 1.00 27.68 |

Figure 10

| ATOM | 3233 | N | ASP | B | 364 | 37.071 | 10.974 | 43.921 | 1.00 | 25.52 |
| ATOM | 3234 | CA | ASP | B | 364 | 38.019 | 9.936 | 43.518 | 1.00 | 24.44 |
| ATOM | 3235 | CB | ASP | B | 364 | 38.589 | 10.247 | 42.126 | 1.00 | 25.09 |
| ATOM | 3236 | CG | ASP | B | 364 | 37.565 | 10.055 | 41.024 | 1.00 | 25.46 |
| ATOM | 3237 | OD1 | ASP | B | 364 | 37.137 | 8.909 | 40.813 | 1.00 | 28.98 |
| ATOM | 3238 | OD2 | ASP | B | 364 | 37.184 | 11.040 | 40.365 | 1.00 | 26.55 |
| ATOM | 3239 | C | ASP | B | 364 | 39.144 | 9.784 | 44.544 | 1.00 | 23.46 |
| ATOM | 3240 | O | ASP | B | 364 | 40.289 | 9.487 | 44.209 | 1.00 | 23.59 |
| ATOM | 3241 | N | LEU | B | 365 | 38.796 | 9.950 | 45.811 | 1.00 | 23.01 |
| ATOM | 3242 | CA | LEU | B | 365 | 39.770 | 9.852 | 46.887 | 1.00 | 22.35 |
| ATOM | 3243 | CB | LEU | B | 365 | 39.264 | 10.600 | 48.128 | 1.00 | 18.58 |
| ATOM | 3244 | CG | LEU | B | 365 | 40.283 | 10.779 | 49.263 | 1.00 | 19.10 |
| ATOM | 3245 | CD1 | LEU | B | 365 | 41.581 | 11.487 | 48.770 | 1.00 | 17.62 |
| ATOM | 3246 | CD2 | LEU | B | 365 | 39.613 | 11.560 | 50.385 | 1.00 | 16.31 |
| ATOM | 3247 | C | LEU | B | 365 | 40.184 | 8.413 | 47.247 | 1.00 | 22.90 |
| ATOM | 3248 | O | LEU | B | 365 | 39.360 | 7.585 | 47.659 | 1.00 | 23.64 |
| ATOM | 3249 | N | ARG | B | 366 | 41.471 | 8.130 | 47.054 | 1.00 | 22.31 |
| ATOM | 3250 | CA | ARG | B | 366 | 42.082 | 6.842 | 47.367 | 1.00 | 22.74 |
| ATOM | 3251 | CB | ARG | B | 366 | 41.719 | 5.759 | 46.338 | 1.00 | 24.00 |
| ATOM | 3252 | CG | ARG | B | 366 | 41.765 | 6.120 | 44.864 | 1.00 | 25.73 |
| ATOM | 3253 | CD | ARG | B | 366 | 41.494 | 4.857 | 44.070 | 1.00 | 29.46 |
| ATOM | 3254 | NE | ARG | B | 366 | 41.269 | 5.084 | 42.647 | 1.00 | 35.33 |
| ATOM | 3255 | CZ | ARG | B | 366 | 40.158 | 5.607 | 42.128 | 1.00 | 37.83 |
| ATOM | 3256 | NH1 | ARG | B | 366 | 39.145 | 5.984 | 42.912 | 1.00 | 40.30 |
| ATOM | 3257 | NH2 | ARG | B | 366 | 40.049 | 5.724 | 40.814 | 1.00 | 37.32 |
| ATOM | 3258 | C | ARG | B | 366 | 43.581 | 7.065 | 47.424 | 1.00 | 21.92 |
| ATOM | 3259 | O | ARG | B | 366 | 44.047 | 8.139 | 47.066 | 1.00 | 21.39 |
| ATOM | 3260 | N | ALA | B | 367 | 44.341 | 6.086 | 47.900 | 1.00 | 21.42 |
| ATOM | 3261 | CA | ALA | B | 367 | 45.787 | 6.259 | 47.967 | 1.00 | 21.30 |
| ATOM | 3262 | CB | ALA | B | 367 | 46.416 | 5.174 | 48.805 | 1.00 | 20.49 |
| ATOM | 3263 | C | ALA | B | 367 | 46.437 | 6.339 | 46.574 | 1.00 | 21.94 |
| ATOM | 3264 | O | ALA | B | 367 | 47.475 | 6.973 | 46.408 | 1.00 | 21.86 |
| ATOM | 3265 | N | ALA | B | 368 | 45.805 | 5.736 | 45.566 | 1.00 | 22.49 |
| ATOM | 3266 | CA | ALA | B | 368 | 46.326 | 5.782 | 44.197 | 1.00 | 22.13 |
| ATOM | 3267 | CB | ALA | B | 368 | 45.452 | 4.979 | 43.272 | 1.00 | 20.38 |
| ATOM | 3268 | C | ALA | B | 368 | 46.379 | 7.215 | 43.709 | 1.00 | 22.83 |
| ATOM | 3269 | O | ALA | B | 368 | 47.261 | 7.581 | 42.930 | 1.00 | 23.85 |
| ATOM | 3270 | N | ASN | B | 369 | 45.460 | 8.036 | 44.209 | 1.00 | 23.06 |
| ATOM | 3271 | CA | ASN | B | 369 | 45.381 | 9.427 | 43.798 | 1.00 | 22.73 |
| ATOM | 3272 | CB | ASN | B | 369 | 43.942 | 9.771 | 43.470 | 1.00 | 22.21 |
| ATOM | 3273 | CG | ASN | B | 369 | 43.429 | 8.951 | 42.320 | 1.00 | 23.02 |
| ATOM | 3274 | OD1 | ASN | B | 369 | 44.113 | 8.808 | 41.304 | 1.00 | 23.73 |
| ATOM | 3275 | ND2 | ASN | B | 369 | 42.246 | 8.371 | 42.476 | 1.00 | 23.88 |
| ATOM | 3276 | C | ASN | B | 369 | 46.026 | 10.456 | 44.713 | 1.00 | 23.24 |
| ATOM | 3277 | O | ASN | B | 369 | 45.665 | 11.637 | 44.686 | 1.00 | 24.79 |
| ATOM | 3278 | N | ILE | B | 370 | 46.952 | 9.985 | 45.547 | 1.00 | 22.61 |
| ATOM | 3279 | CA | ILE | B | 370 | 47.737 | 10.837 | 46.439 | 1.00 | 22.33 |
| ATOM | 3280 | CB | ILE | B | 370 | 47.742 | 10.351 | 47.916 | 1.00 | 21.73 |
| ATOM | 3281 | CG2 | ILE | B | 370 | 48.601 | 11.291 | 48.755 | 1.00 | 18.36 |
| ATOM | 3282 | CG1 | ILE | B | 370 | 46.316 | 10.270 | 48.476 | 1.00 | 19.68 |
| ATOM | 3283 | CD1 | ILE | B | 370 | 45.578 | 11.592 | 48.456 | 1.00 | 19.34 |
| ATOM | 3284 | C | ILE | B | 370 | 49.164 | 10.674 | 45.912 | 1.00 | 22.82 |
| ATOM | 3285 | O | ILE | B | 370 | 49.584 | 9.562 | 45.601 | 1.00 | 22.72 |
| ATOM | 3286 | N | LEU | B | 371 | 49.908 | 11.772 | 45.820 | 1.00 | 24.39 |
| ATOM | 3287 | CA | LEU | B | 371 | 51.283 | 11.737 | 45.311 | 1.00 | 24.85 |
| ATOM | 3288 | CB | LEU | B | 371 | 51.432 | 12.718 | 44.135 | 1.00 | 23.61 |
| ATOM | 3289 | CG | LEU | B | 371 | 50.580 | 12.446 | 42.879 | 1.00 | 22.45 |
| ATOM | 3290 | CD1 | LEU | B | 371 | 50.770 | 13.545 | 41.861 | 1.00 | 20.98 |
| ATOM | 3291 | CD2 | LEU | B | 371 | 50.959 | 11.107 | 42.270 | 1.00 | 22.92 |

Figure 10

| ATOM | 3292 | C   | LEU | B | 371 | 52.281 | 12.052 | 46.426 | 1.00 | 26.06 |
| ---- | ---- | --- | --- | - | --- | ------ | ------ | ------ | ---- | ----- |
| ATOM | 3293 | O   | LEU | B | 371 | 52.007 | 12.877 | 47.288 | 1.00 | 26.91 |
| ATOM | 3294 | N   | VAL | B | 372 | 53.420 | 11.363 | 46.411 | 1.00 | 27.77 |
| ATOM | 3295 | CA  | VAL | B | 372 | 54.475 | 11.530 | 47.422 | 1.00 | 30.21 |
| ATOM | 3296 | CB  | VAL | B | 372 | 54.890 | 10.156 | 48.037 | 1.00 | 30.13 |
| ATOM | 3297 | CG1 | VAL | B | 372 | 55.814 | 10.353 | 49.220 | 1.00 | 29.97 |
| ATOM | 3298 | CG2 | VAL | B | 372 | 53.660 | 9.385  | 48.468 | 1.00 | 28.60 |
| ATOM | 3299 | C   | VAL | B | 372 | 55.721 | 12.230 | 46.860 | 1.00 | 31.56 |
| ATOM | 3300 | O   | VAL | B | 372 | 56.263 | 11.841 | 45.820 | 1.00 | 32.68 |
| ATOM | 3301 | N   | SER | B | 373 | 56.171 | 13.265 | 47.557 | 1.00 | 32.55 |
| ATOM | 3302 | CA  | SER | B | 373 | 57.327 | 14.035 | 47.124 | 1.00 | 35.71 |
| ATOM | 3303 | CB  | SER | B | 373 | 57.230 | 15.456 | 47.673 | 1.00 | 36.20 |
| ATOM | 3304 | OG  | SER | B | 373 | 57.466 | 15.462 | 49.077 | 1.00 | 38.07 |
| ATOM | 3305 | C   | SER | B | 373 | 58.624 | 13.411 | 47.616 | 1.00 | 37.65 |
| ATOM | 3306 | O   | SER | B | 373 | 58.605 | 12.496 | 48.432 | 1.00 | 38.38 |
| ATOM | 3307 | N   | ASP | B | 374 | 59.752 | 13.946 | 47.157 | 1.00 | 39.47 |
| ATOM | 3308 | CA  | ASP | B | 374 | 61.066 | 13.458 | 47.576 | 1.00 | 41.23 |
| ATOM | 3309 | CB  | ASP | B | 374 | 62.168 | 14.242 | 46.874 | 1.00 | 43.17 |
| ATOM | 3310 | CG  | ASP | B | 374 | 61.990 | 15.734 | 47.014 | 1.00 | 46.88 |
| ATOM | 3311 | OD1 | ASP | B | 374 | 61.036 | 16.276 | 46.408 | 1.00 | 50.35 |
| ATOM | 3312 | OD2 | ASP | B | 374 | 62.790 | 16.365 | 47.736 | 1.00 | 48.63 |
| ATOM | 3313 | C   | ASP | B | 374 | 61.228 | 13.595 | 49.090 | 1.00 | 41.57 |
| ATOM | 3314 | O   | ASP | B | 374 | 61.949 | 12.818 | 49.715 | 1.00 | 41.77 |
| ATOM | 3315 | N   | THR | B | 375 | 60.543 | 14.578 | 49.669 | 1.00 | 41.19 |
| ATOM | 3316 | CA  | THR | B | 375 | 60.594 | 14.817 | 51.109 | 1.00 | 41.30 |
| ATOM | 3317 | CB  | THR | B | 375 | 60.409 | 16.303 | 51.431 | 1.00 | 41.83 |
| ATOM | 3318 | OG1 | THR | B | 375 | 59.164 | 16.763 | 50.889 | 1.00 | 41.14 |
| ATOM | 3319 | CG2 | THR | B | 375 | 61.547 | 17.112 | 50.826 | 1.00 | 42.87 |
| ATOM | 3320 | C   | THR | B | 375 | 59.539 | 14.004 | 51.863 | 1.00 | 41.29 |
| ATOM | 3321 | O   | THR | B | 375 | 59.307 | 14.215 | 53.064 | 1.00 | 41.63 |
| ATOM | 3322 | N   | LEU | B | 376 | 58.912 | 13.072 | 51.145 | 1.00 | 39.97 |
| ATOM | 3323 | CA  | LEU | B | 376 | 57.882 | 12.185 | 51.683 | 1.00 | 38.76 |
| ATOM | 3324 | CB  | LEU | B | 376 | 58.473 | 11.243 | 52.739 | 1.00 | 37.94 |
| ATOM | 3325 | CG  | LEU | B | 376 | 59.785 | 10.512 | 52.392 | 1.00 | 37.69 |
| ATOM | 3326 | CD1 | LEU | B | 376 | 59.899 | 9.241  | 53.226 | 1.00 | 38.53 |
| ATOM | 3327 | CD2 | LEU | B | 376 | 59.846 | 10.142 | 50.924 | 1.00 | 37.72 |
| ATOM | 3328 | C   | LEU | B | 376 | 56.622 | 12.885 | 52.212 | 1.00 | 38.81 |
| ATOM | 3329 | O   | LEU | B | 376 | 55.972 | 12.391 | 53.139 | 1.00 | 38.86 |
| ATOM | 3330 | N   | SER | B | 377 | 56.305 | 14.051 | 51.642 | 1.00 | 38.19 |
| ATOM | 3331 | CA  | SER | B | 377 | 55.104 | 14.795 | 52.016 | 1.00 | 37.56 |
| ATOM | 3332 | CB  | SER | B | 377 | 55.351 | 16.310 | 52.033 | 1.00 | 39.69 |
| ATOM | 3333 | OG  | SER | B | 377 | 55.313 | 16.858 | 50.724 | 1.00 | 42.09 |
| ATOM | 3334 | C   | SER | B | 377 | 54.039 | 14.452 | 50.971 | 1.00 | 35.63 |
| ATOM | 3335 | O   | SER | B | 377 | 54.346 | 14.293 | 49.794 | 1.00 | 34.31 |
| ATOM | 3336 | N   | CYS | B | 378 | 52.785 | 14.372 | 51.408 | 1.00 | 34.65 |
| ATOM | 3337 | CA  | CYS | B | 378 | 51.696 | 14.014 | 50.523 | 1.00 | 32.10 |
| ATOM | 3338 | CB  | CYS | B | 378 | 50.733 | 13.078 | 51.251 | 1.00 | 32.07 |
| ATOM | 3339 | SG  | CYS | B | 378 | 51.464 | 11.521 | 51.751 | 1.00 | 30.35 |
| ATOM | 3340 | C   | CYS | B | 378 | 50.930 | 15.205 | 49.970 | 1.00 | 30.78 |
| ATOM | 3341 | O   | CYS | B | 378 | 50.732 | 16.199 | 50.678 | 1.00 | 30.18 |
| ATOM | 3342 | N   | LYS | B | 379 | 50.548 | 15.082 | 48.690 | 1.00 | 29.13 |
| ATOM | 3343 | CA  | LYS | B | 379 | 49.757 | 16.062 | 47.934 | 1.00 | 27.46 |
| ATOM | 3344 | CB  | LYS | B | 379 | 50.624 | 16.823 | 46.922 | 1.00 | 25.51 |
| ATOM | 3345 | CG  | LYS | B | 379 | 51.201 | 18.137 | 47.458 | 1.00 | 24.89 |
| ATOM | 3346 | CD  | LYS | B | 379 | 52.380 | 18.634 | 46.624 | 1.00 | 25.83 |
| ATOM | 3347 | CE  | LYS | B | 379 | 52.964 | 19.964 | 47.114 | 1.00 | 25.30 |
| ATOM | 3348 | NZ  | LYS | B | 379 | 52.180 | 21.142 | 46.575 | 1.00 | 28.60 |
| ATOM | 3349 | C   | LYS | B | 379 | 48.610 | 15.319 | 47.226 | 1.00 | 27.15 |
| ATOM | 3350 | O   | LYS | B | 379 | 48.786 | 14.207 | 46.722 | 1.00 | 27.17 |

Figure 10

| ATOM | 3351 | N   | ILE | B | 380 | 47.436 | 15.939 | 47.204 | 1.00 | 26.94 |
| ATOM | 3352 | CA  | ILE | B | 380 | 46.241 | 15.349 | 46.598 | 1.00 | 27.18 |
| ATOM | 3353 | CB  | ILE | B | 380 | 44.939 | 15.877 | 47.306 | 1.00 | 25.98 |
| ATOM | 3354 | CG2 | ILE | B | 380 | 43.702 | 15.262 | 46.690 | 1.00 | 24.46 |
| ATOM | 3355 | CG1 | ILE | B | 380 | 44.978 | 15.562 | 48.802 | 1.00 | 26.21 |
| ATOM | 3356 | CD1 | ILE | B | 380 | 43.787 | 16.042 | 49.535 | 1.00 | 25.27 |
| ATOM | 3357 | C   | ILE | B | 380 | 46.154 | 15.654 | 45.102 | 1.00 | 27.18 |
| ATOM | 3358 | O   | ILE | B | 380 | 46.288 | 16.809 | 44.692 | 1.00 | 28.36 |
| ATOM | 3359 | N   | ALA | B | 381 | 45.926 | 14.627 | 44.287 | 1.00 | 26.77 |
| ATOM | 3360 | CA  | ALA | B | 381 | 45.808 | 14.822 | 42.847 | 1.00 | 26.33 |
| ATOM | 3361 | CB  | ALA | B | 381 | 46.873 | 14.024 | 42.112 | 1.00 | 25.38 |
| ATOM | 3362 | C   | ALA | B | 381 | 44.431 | 14.413 | 42.365 | 1.00 | 26.94 |
| ATOM | 3363 | O   | ALA | B | 381 | 43.667 | 13.765 | 43.100 | 1.00 | 27.32 |
| ATOM | 3364 | N   | ASP | B | 382 | 44.140 | 14.799 | 41.120 | 1.00 | 27.04 |
| ATOM | 3365 | CA  | ASP | B | 382 | 42.889 | 14.496 | 40.414 | 1.00 | 27.16 |
| ATOM | 3366 | CB  | ASP | B | 382 | 42.940 | 13.079 | 39.854 | 1.00 | 25.60 |
| ATOM | 3367 | CG  | ASP | B | 382 | 43.862 | 12.974 | 38.695 | 1.00 | 25.51 |
| ATOM | 3368 | OD1 | ASP | B | 382 | 43.796 | 13.858 | 37.828 | 1.00 | 26.71 |
| ATOM | 3369 | OD2 | ASP | B | 382 | 44.676 | 12.041 | 38.643 | 1.00 | 26.26 |
| ATOM | 3370 | C   | ASP | B | 382 | 41.586 | 14.726 | 41.155 | 1.00 | 27.85 |
| ATOM | 3371 | O   | ASP | B | 382 | 40.685 | 13.877 | 41.130 | 1.00 | 27.11 |
| ATOM | 3372 | N   | PHE | B | 383 | 41.457 | 15.920 | 41.725 | 1.00 | 28.81 |
| ATOM | 3373 | CA  | PHE | B | 383 | 40.272 | 16.291 | 42.495 | 1.00 | 30.20 |
| ATOM | 3374 | CB  | PHE | B | 383 | 40.718 | 16.966 | 43.793 | 1.00 | 30.03 |
| ATOM | 3375 | CG  | PHE | B | 383 | 41.670 | 18.095 | 43.578 | 1.00 | 30.31 |
| ATOM | 3376 | CD1 | PHE | B | 383 | 41.188 | 19.359 | 43.248 | 1.00 | 32.45 |
| ATOM | 3377 | CD2 | PHE | B | 383 | 43.044 | 17.897 | 43.662 | 1.00 | 28.77 |
| ATOM | 3378 | CE1 | PHE | B | 383 | 42.052 | 20.408 | 42.999 | 1.00 | 32.57 |
| ATOM | 3379 | CE2 | PHE | B | 383 | 43.930 | 18.943 | 43.416 | 1.00 | 30.47 |
| ATOM | 3380 | CZ  | PHE | B | 383 | 43.430 | 20.205 | 43.080 | 1.00 | 32.40 |
| ATOM | 3381 | C   | PHE | B | 383 | 39.264 | 17.169 | 41.752 | 1.00 | 30.83 |
| ATOM | 3382 | O   | PHE | B | 383 | 39.620 | 17.902 | 40.838 | 1.00 | 31.57 |
| ATOM | 3383 | N   | GLY | B | 384 | 37.996 | 17.045 | 42.125 | 1.00 | 32.14 |
| ATOM | 3384 | CA  | GLY | B | 384 | 36.957 | 17.841 | 41.508 | 1.00 | 34.02 |
| ATOM | 3385 | C   | GLY | B | 384 | 36.574 | 17.427 | 40.100 | 1.00 | 35.85 |
| ATOM | 3386 | O   | GLY | B | 384 | 35.880 | 18.174 | 39.418 | 1.00 | 36.82 |
| ATOM | 3387 | N   | LEU | B | 385 | 37.002 | 16.247 | 39.660 | 1.00 | 36.10 |
| ATOM | 3388 | CA  | LEU | B | 385 | 36.677 | 15.778 | 38.316 | 1.00 | 36.05 |
| ATOM | 3389 | CB  | LEU | B | 385 | 37.512 | 14.543 | 37.951 | 1.00 | 34.80 |
| ATOM | 3390 | CG  | LEU | B | 385 | 39.033 | 14.672 | 38.110 | 1.00 | 33.73 |
| ATOM | 3391 | CD1 | LEU | B | 385 | 39.710 | 13.371 | 37.744 | 1.00 | 32.13 |
| ATOM | 3392 | CD2 | LEU | B | 385 | 39.561 | 15.803 | 37.266 | 1.00 | 34.21 |
| ATOM | 3393 | C   | LEU | B | 385 | 35.195 | 15.452 | 38.229 | 1.00 | 37.09 |
| ATOM | 3394 | O   | LEU | B | 385 | 34.594 | 15.013 | 39.207 | 1.00 | 37.29 |
| ATOM | 3395 | N   | ALA | B | 386 | 34.613 | 15.699 | 37.056 | 1.00 | 38.65 |
| ATOM | 3396 | CA  | ALA | B | 386 | 33.194 | 15.458 | 36.797 | 1.00 | 39.23 |
| ATOM | 3397 | CB  | ALA | B | 386 | 32.794 | 16.133 | 35.498 | 1.00 | 40.24 |
| ATOM | 3398 | C   | ALA | B | 386 | 32.849 | 13.991 | 36.706 | 1.00 | 38.90 |
| ATOM | 3399 | O   | ALA | B | 386 | 31.677 | 13.606 | 36.808 | 1.00 | 40.32 |
| ATOM | 3400 | N   | ARG | B | 387 | 33.874 | 13.176 | 36.508 | 1.00 | 37.25 |
| ATOM | 3401 | CA  | ARG | B | 387 | 33.685 | 11.749 | 36.339 | 1.00 | 34.26 |
| ATOM | 3402 | CB  | ARG | B | 387 | 34.120 | 11.373 | 34.928 | 1.00 | 32.40 |
| ATOM | 3403 | CG  | ARG | B | 387 | 35.571 | 11.726 | 34.675 | 1.00 | 31.46 |
| ATOM | 3404 | CD  | ARG | B | 387 | 35.995 | 11.381 | 33.288 | 1.00 | 31.65 |
| ATOM | 3405 | NE  | ARG | B | 387 | 37.445 | 11.381 | 33.126 | 1.00 | 30.64 |
| ATOM | 3406 | CZ  | ARG | B | 387 | 38.198 | 10.293 | 33.235 | 1.00 | 31.24 |
| ATOM | 3407 | NH1 | ARG | B | 387 | 37.637 |  9.116 | 33.516 | 1.00 | 30.62 |
| ATOM | 3408 | NH2 | ARG | B | 387 | 39.504 | 10.379 | 33.021 | 1.00 | 30.95 |
| ATOM | 3409 | C   | ARG | B | 387 | 34.453 | 10.901 | 37.322 | 1.00 | 33.08 |

Figure 10

| | | | | | | | | | |
|---|---|---|---|---|---|---|---|---|---|
| ATOM | 3410 | O | ARG | B | 387 | 35.312 | 11.385 | 38.058 | 1.00 33.34 |
| ATOM | 3411 | N | LEU | B | 388 | 34.129 | 9.612 | 37.295 | 1.00 32.62 |
| ATOM | 3412 | CA | LEU | B | 388 | 34.772 | 8.601 | 38.120 | 1.00 31.59 |
| ATOM | 3413 | CB | LEU | B | 388 | 33.745 | 7.543 | 38.504 | 1.00 32.12 |
| ATOM | 3414 | CG | LEU | B | 388 | 32.499 | 8.180 | 39.138 | 1.00 33.86 |
| ATOM | 3415 | CD1 | LEU | B | 388 | 31.465 | 7.120 | 39.474 | 1.00 33.82 |
| ATOM | 3416 | CD2 | LEU | B | 388 | 32.899 | 8.943 | 40.386 | 1.00 33.25 |
| ATOM | 3417 | C | LEU | B | 388 | 35.929 | 7.994 | 37.309 | 1.00 30.10 |
| ATOM | 3418 | O | LEU | B | 388 | 35.718 | 7.398 | 36.248 | 1.00 30.90 |
| ATOM | 3419 | N | ILE | B | 389 | 37.152 | 8.226 | 37.775 | 1.00 28.18 |
| ATOM | 3420 | CA | ILE | B | 389 | 38.354 | 7.747 | 37.105 | 1.00 26.62 |
| ATOM | 3421 | CB | ILE | B | 389 | 39.515 | 8.774 | 37.233 | 1.00 23.96 |
| ATOM | 3422 | CG2 | ILE | B | 389 | 39.043 | 10.141 | 36.784 | 1.00 24.04 |
| ATOM | 3423 | CG1 | ILE | B | 389 | 40.051 | 8.835 | 38.668 | 1.00 21.70 |
| ATOM | 3424 | CD1 | ILE | B | 389 | 41.164 | 9.826 | 38.858 | 1.00 17.64 |
| ATOM | 3425 | C | ILE | B | 389 | 38.852 | 6.386 | 37.571 | 1.00 27.92 |
| ATOM | 3426 | O | ILE | B | 389 | 38.583 | 5.954 | 38.687 | 1.00 28.32 |
| ATOM | 3427 | N | GLU | B | 390 | 39.564 | 5.705 | 36.685 | 1.00 29.64 |
| ATOM | 3428 | CA | GLU | B | 390 | 40.133 | 4.400 | 36.998 | 1.00 31.72 |
| ATOM | 3429 | CB | GLU | B | 390 | 39.660 | 3.333 | 36.010 | 1.00 31.76 |
| ATOM | 3430 | CG | GLU | B | 390 | 38.161 | 3.157 | 35.957 | 1.00 34.91 |
| ATOM | 3431 | CD | GLU | B | 390 | 37.732 | 1.980 | 35.107 | 1.00 36.35 |
| ATOM | 3432 | OE1 | GLU | B | 390 | 36.528 | 1.683 | 35.074 | 1.00 39.90 |
| ATOM | 3433 | OE2 | GLU | B | 390 | 38.583 | 1.339 | 34.471 | 1.00 38.61 |
| ATOM | 3434 | C | GLU | B | 390 | 41.648 | 4.492 | 36.931 | 1.00 32.04 |
| ATOM | 3435 | O | GLU | B | 390 | 42.204 | 5.293 | 36.172 | 1.00 31.77 |
| ATOM | 3436 | N | ASP | B | 391 | 42.305 | 3.608 | 37.670 | 1.00 33.33 |
| ATOM | 3437 | CA | ASP | B | 391 | 43.762 | 3.565 | 37.720 | 1.00 34.96 |
| ATOM | 3438 | CB | ASP | B | 391 | 44.197 | 2.670 | 38.876 | 1.00 36.72 |
| ATOM | 3439 | CG | ASP | B | 391 | 43.845 | 3.249 | 40.223 | 1.00 38.49 |
| ATOM | 3440 | OD1 | ASP | B | 391 | 43.282 | 4.377 | 40.306 | 1.00 37.58 |
| ATOM | 3441 | OD2 | ASP | B | 391 | 44.158 | 2.561 | 41.210 | 1.00 42.01 |
| ATOM | 3442 | C | ASP | B | 391 | 44.485 | 3.124 | 36.436 | 1.00 34.31 |
| ATOM | 3443 | O | ASP | B | 391 | 45.673 | 3.390 | 36.259 | 1.00 34.69 |
| ATOM | 3444 | N | ASN | B | 392 | 43.770 | 2.452 | 35.547 | 1.00 33.65 |
| ATOM | 3445 | CA | ASN | B | 392 | 44.374 | 1.971 | 34.318 | 1.00 33.99 |
| ATOM | 3446 | CB | ASN | B | 392 | 43.680 | 0.669 | 33.864 | 1.00 33.60 |
| ATOM | 3447 | CG | ASN | B | 392 | 42.247 | 0.886 | 33.353 | 1.00 35.43 |
| ATOM | 3448 | OD1 | ASN | B | 392 | 41.661 | 1.977 | 33.452 | 1.00 34.21 |
| ATOM | 3449 | ND2 | ASN | B | 392 | 41.681 | -0.171 | 32.793 | 1.00 36.49 |
| ATOM | 3450 | C | ASN | B | 392 | 44.410 | 3.003 | 33.185 | 1.00 33.68 |
| ATOM | 3451 | O | ASN | B | 392 | 44.901 | 2.719 | 32.082 | 1.00 35.86 |
| ATOM | 3452 | N | GLU | B | 393 | 43.957 | 4.215 | 33.473 | 1.00 31.05 |
| ATOM | 3453 | CA | GLU | B | 393 | 43.913 | 5.250 | 32.460 | 1.00 30.50 |
| ATOM | 3454 | CB | GLU | B | 393 | 42.921 | 6.340 | 32.896 | 1.00 27.47 |
| ATOM | 3455 | CG | GLU | B | 393 | 41.485 | 5.807 | 33.028 | 1.00 23.48 |
| ATOM | 3456 | CD | GLU | B | 393 | 40.514 | 6.770 | 33.665 | 1.00 19.99 |
| ATOM | 3457 | OE1 | GLU | B | 393 | 40.898 | 7.909 | 33.995 | 1.00 20.29 |
| ATOM | 3458 | OE2 | GLU | B | 393 | 39.345 | 6.380 | 33.842 | 1.00 21.76 |
| ATOM | 3459 | C | GLU | B | 393 | 45.259 | 5.846 | 32.002 | 1.00 32.12 |
| ATOM | 3460 | O | GLU | B | 393 | 45.430 | 6.147 | 30.819 | 1.00 32.69 |
| ATOM | 3461 | N | TYR | B | 394 | 46.211 | 5.996 | 32.922 | 1.00 32.82 |
| ATOM | 3462 | CA | TYR | B | 394 | 47.507 | 6.581 | 32.589 | 1.00 34.20 |
| ATOM | 3463 | CB | TYR | B | 394 | 47.588 | 8.012 | 33.117 | 1.00 32.25 |
| ATOM | 3464 | CG | TYR | B | 394 | 46.517 | 8.866 | 32.513 | 1.00 30.39 |
| ATOM | 3465 | CD1 | TYR | B | 394 | 45.228 | 8.866 | 33.036 | 1.00 30.42 |
| ATOM | 3466 | CE1 | TYR | B | 394 | 44.196 | 9.592 | 32.432 | 1.00 33.39 |
| ATOM | 3467 | CD2 | TYR | B | 394 | 46.768 | 9.619 | 31.373 | 1.00 32.48 |
| ATOM | 3468 | CE2 | TYR | B | 394 | 45.748 | 10.361 | 30.750 | 1.00 34.00 |

Figure 10 /Page 59/76

| ATOM | 3469 | CZ  | TYR | B | 394 | 44.460 | 10.340 | 31.283 | 1.00 | 34.76 |
| ATOM | 3470 | OH  | TYR | B | 394 | 43.444 | 11.035 | 30.662 | 1.00 | 33.32 |
| ATOM | 3471 | C   | TYR | B | 394 | 48.699 | 5.737  | 33.035 | 1.00 | 36.59 |
| ATOM | 3472 | O   | TYR | B | 394 | 49.847 | 6.132  | 32.857 | 1.00 | 37.17 |
| ATOM | 3473 | N   | THR | B | 395 | 48.406 | 4.605  | 33.671 | 1.00 | 38.88 |
| ATOM | 3474 | CA  | THR | B | 395 | 49.413 | 3.633  | 34.077 | 1.00 | 41.78 |
| ATOM | 3475 | CB  | THR | B | 395 | 49.778 | 3.705  | 35.533 | 1.00 | 41.48 |
| ATOM | 3476 | OG1 | THR | B | 395 | 48.627 | 4.066  | 36.309 | 1.00 | 43.33 |
| ATOM | 3477 | CG2 | THR | B | 395 | 50.885 | 4.675  | 35.712 | 1.00 | 40.69 |
| ATOM | 3478 | C   | THR | B | 395 | 48.842 | 2.268  | 33.793 | 1.00 | 44.81 |
| ATOM | 3479 | O   | THR | B | 395 | 47.744 | 2.146  | 33.244 | 1.00 | 45.55 |
| ATOM | 3480 | N   | ALA | B | 396 | 49.551 | 1.226  | 34.196 | 1.00 | 49.15 |
| ATOM | 3481 | CA  | ALA | B | 396 | 49.049 | -0.106 | 33.899 | 1.00 | 53.25 |
| ATOM | 3482 | CB  | ALA | B | 396 | 49.982 | -0.807 | 32.896 | 1.00 | 53.26 |
| ATOM | 3483 | C   | ALA | B | 396 | 48.786 | -0.982 | 35.122 | 1.00 | 56.09 |
| ATOM | 3484 | O   | ALA | B | 396 | 49.187 | -2.149 | 35.150 | 1.00 | 57.31 |
| ATOM | 3485 | N   | ARG | B | 397 | 48.054 | -0.439 | 36.099 | 1.00 | 58.76 |
| ATOM | 3486 | CA  | ARG | B | 397 | 47.732 | -1.180 | 37.321 | 1.00 | 60.20 |
| ATOM | 3487 | CB  | ARG | B | 397 | 47.215 | -0.239 | 38.410 | 1.00 | 61.05 |
| ATOM | 3488 | CG  | ARG | B | 397 | 48.245 | 0.744  | 38.926 | 1.00 | 62.28 |
| ATOM | 3489 | CD  | ARG | B | 397 | 48.247 | 0.776  | 40.457 | 1.00 | 63.02 |
| ATOM | 3490 | NE  | ARG | B | 397 | 49.038 | 1.887  | 40.989 | 1.00 | 61.91 |
| ATOM | 3491 | CZ  | ARG | B | 397 | 48.671 | 3.163  | 40.910 | 1.00 | 60.54 |
| ATOM | 3492 | NH1 | ARG | B | 397 | 47.527 | 3.495  | 40.313 | 1.00 | 59.16 |
| ATOM | 3493 | NH2 | ARG | B | 397 | 49.424 | 4.101  | 41.467 | 1.00 | 58.52 |
| ATOM | 3494 | C   | ARG | B | 397 | 46.713 | -2.293 | 37.077 | 1.00 | 60.98 |
| ATOM | 3495 | O   | ARG | B | 397 | 47.014 | -3.444 | 37.480 | 1.00 | 61.55 |
| ATOM | 3496 | CB  | PRO | B | 403 | 37.113 | 2.742  | 41.149 | 1.00 | 31.47 |
| ATOM | 3497 | CG  | PRO | B | 403 | 37.613 | 2.159  | 39.819 | 1.00 | 32.68 |
| ATOM | 3498 | C   | PRO | B | 403 | 35.762 | 1.637  | 42.984 | 1.00 | 31.08 |
| ATOM | 3499 | O   | PRO | B | 403 | 35.769 | 2.616  | 43.766 | 1.00 | 31.50 |
| ATOM | 3500 | N   | PRO | B | 403 | 36.413 | 0.424  | 40.870 | 1.00 | 31.52 |
| ATOM | 3501 | CD  | PRO | B | 403 | 36.724 | 0.914  | 39.519 | 1.00 | 32.16 |
| ATOM | 3502 | CA  | PRO | B | 403 | 36.831 | 1.454  | 41.897 | 1.00 | 31.18 |
| ATOM | 3503 | N   | ILE | B | 404 | 34.941 | 0.592  | 43.098 | 1.00 | 28.66 |
| ATOM | 3504 | CA  | ILE | B | 404 | 33.843 | 0.487  | 44.046 | 1.00 | 25.62 |
| ATOM | 3505 | CB  | ILE | B | 404 | 33.000 | -0.766 | 43.666 | 1.00 | 25.03 |
| ATOM | 3506 | CG2 | ILE | B | 404 | 32.159 | -1.250 | 44.810 | 1.00 | 24.34 |
| ATOM | 3507 | CG1 | ILE | B | 404 | 32.150 | -0.437 | 42.441 | 1.00 | 24.95 |
| ATOM | 3508 | CD1 | ILE | B | 404 | 31.333 | 0.835  | 42.628 | 1.00 | 26.77 |
| ATOM | 3509 | C   | ILE | B | 404 | 34.254 | 0.460  | 45.533 | 1.00 | 22.96 |
| ATOM | 3510 | O   | ILE | B | 404 | 33.560 | 1.011  | 46.382 | 1.00 | 22.29 |
| ATOM | 3511 | N   | LYS | B | 405 | 35.425 | -0.082 | 45.829 | 1.00 | 20.18 |
| ATOM | 3512 | CA  | LYS | B | 405 | 35.899 | -0.194 | 47.212 | 1.00 | 20.17 |
| ATOM | 3513 | CB  | LYS | B | 405 | 37.133 | -1.103 | 47.288 | 1.00 | 18.19 |
| ATOM | 3514 | CG  | LYS | B | 405 | 36.756 | -2.545 | 46.972 | 1.00 | 18.32 |
| ATOM | 3515 | CD  | LYS | B | 405 | 37.930 | -3.483 | 46.998 | 1.00 | 19.59 |
| ATOM | 3516 | CE  | LYS | B | 405 | 37.452 | -4.920 | 46.836 | 1.00 | 20.59 |
| ATOM | 3517 | NZ  | LYS | B | 405 | 38.481 | -5.873 | 47.350 | 1.00 | 22.16 |
| ATOM | 3518 | C   | LYS | B | 405 | 36.076 | 1.068  | 48.062 | 1.00 | 19.83 |
| ATOM | 3519 | O   | LYS | B | 405 | 36.253 | 0.973  | 49.278 | 1.00 | 20.93 |
| ATOM | 3520 | N   | TRP | B | 406 | 35.978 | 2.241  | 47.439 | 1.00 | 19.84 |
| ATOM | 3521 | CA  | TRP | B | 406 | 36.108 | 3.519  | 48.146 | 1.00 | 19.17 |
| ATOM | 3522 | CB  | TRP | B | 406 | 37.227 | 4.379  | 47.532 | 1.00 | 18.90 |
| ATOM | 3523 | CG  | TRP | B | 406 | 38.585 | 3.804  | 47.686 | 1.00 | 19.08 |
| ATOM | 3524 | CD2 | TRP | B | 406 | 39.168 | 2.775  | 46.875 | 1.00 | 18.54 |
| ATOM | 3525 | CE2 | TRP | B | 406 | 40.452 | 2.508  | 47.399 | 1.00 | 18.03 |
| ATOM | 3526 | CE3 | TRP | B | 406 | 38.722 | 2.054  | 45.761 | 1.00 | 18.58 |
| ATOM | 3527 | CD1 | TRP | B | 406 | 39.518 | 4.119  | 48.646 | 1.00 | 17.80 |

Figure 10

| ATOM | 3528 | NE1 | TRP | B | 406 | 40.641 | 3.337 | 48.477 | 1.00 | 19.40 |
| ATOM | 3529 | CZ2 | TRP | B | 406 | 41.294 | 1.552 | 46.847 | 1.00 | 18.08 |
| ATOM | 3530 | CZ3 | TRP | B | 406 | 39.555 | 1.104 | 45.215 | 1.00 | 20.14 |
| ATOM | 3531 | CH2 | TRP | B | 406 | 40.832 | 0.859 | 45.760 | 1.00 | 19.68 |
| ATOM | 3532 | C | TRP | B | 406 | 34.822 | 4.328 | 48.072 | 1.00 | 19.70 |
| ATOM | 3533 | O | TRP | B | 406 | 34.765 | 5.459 | 48.551 | 1.00 | 20.93 |
| ATOM | 3534 | N | THR | B | 407 | 33.798 | 3.762 | 47.454 | 1.00 | 19.56 |
| ATOM | 3535 | CA | THR | B | 407 | 32.538 | 4.465 | 47.283 | 1.00 | 19.45 |
| ATOM | 3536 | CB | THR | B | 407 | 31.844 | 3.995 | 45.994 | 1.00 | 19.61 |
| ATOM | 3537 | OG1 | THR | B | 407 | 32.796 | 3.976 | 44.927 | 1.00 | 21.86 |
| ATOM | 3538 | CG2 | THR | B | 407 | 30.701 | 4.932 | 45.617 | 1.00 | 20.35 |
| ATOM | 3539 | C | THR | B | 407 | 31.575 | 4.309 | 48.452 | 1.00 | 19.50 |
| ATOM | 3540 | O | THR | B | 407 | 31.314 | 3.192 | 48.899 | 1.00 | 19.01 |
| ATOM | 3541 | N | ALA | B | 408 | 31.046 | 5.434 | 48.934 | 1.00 | 19.27 |
| ATOM | 3542 | CA | ALA | B | 408 | 30.085 | 5.445 | 50.041 | 1.00 | 19.82 |
| ATOM | 3543 | CB | ALA | B | 408 | 29.805 | 6.872 | 50.464 | 1.00 | 18.59 |
| ATOM | 3544 | C | ALA | B | 408 | 28.788 | 4.777 | 49.597 | 1.00 | 19.66 |
| ATOM | 3545 | O | ALA | B | 408 | 28.418 | 4.844 | 48.433 | 1.00 | 21.37 |
| ATOM | 3546 | N | PRO | B | 409 | 28.042 | 4.197 | 50.535 | 1.00 | 20.09 |
| ATOM | 3547 | CD | PRO | B | 409 | 28.295 | 4.239 | 51.978 | 1.00 | 19.34 |
| ATOM | 3548 | CA | PRO | B | 409 | 26.779 | 3.514 | 50.257 | 1.00 | 21.53 |
| ATOM | 3549 | CB | PRO | B | 409 | 26.245 | 3.229 | 51.651 | 1.00 | 22.71 |
| ATOM | 3550 | CG | PRO | B | 409 | 27.490 | 3.094 | 52.460 | 1.00 | 21.18 |
| ATOM | 3551 | C | PRO | B | 409 | 25.767 | 4.304 | 49.444 | 1.00 | 23.68 |
| ATOM | 3552 | O | PRO | B | 409 | 25.105 | 3.741 | 48.569 | 1.00 | 25.10 |
| ATOM | 3553 | N | GLU | B | 410 | 25.624 | 5.593 | 49.752 | 1.00 | 23.99 |
| ATOM | 3554 | CA | GLU | B | 410 | 24.673 | 6.445 | 49.051 | 1.00 | 23.93 |
| ATOM | 3555 | CB | GLU | B | 410 | 24.407 | 7.731 | 49.840 | 1.00 | 21.85 |
| ATOM | 3556 | CG | GLU | B | 410 | 25.546 | 8.771 | 49.872 | 1.00 | 20.01 |
| ATOM | 3557 | CD | GLU | B | 410 | 26.646 | 8.479 | 50.872 | 1.00 | 19.62 |
| ATOM | 3558 | OE1 | GLU | B | 410 | 26.501 | 7.561 | 51.706 | 1.00 | 19.25 |
| ATOM | 3559 | OE2 | GLU | B | 410 | 27.664 | 9.191 | 50.825 | 1.00 | 19.20 |
| ATOM | 3560 | C | GLU | B | 410 | 25.105 | 6.774 | 47.629 | 1.00 | 25.69 |
| ATOM | 3561 | O | GLU | B | 410 | 24.260 | 7.073 | 46.773 | 1.00 | 26.74 |
| ATOM | 3562 | N | ALA | B | 411 | 26.415 | 6.742 | 47.381 | 1.00 | 26.79 |
| ATOM | 3563 | CA | ALA | B | 411 | 26.961 | 7.023 | 46.044 | 1.00 | 27.61 |
| ATOM | 3564 | CB | ALA | B | 411 | 28.424 | 7.395 | 46.135 | 1.00 | 24.61 |
| ATOM | 3565 | C | ALA | B | 411 | 26.772 | 5.796 | 45.147 | 1.00 | 28.77 |
| ATOM | 3566 | O | ALA | B | 411 | 26.695 | 5.894 | 43.923 | 1.00 | 29.17 |
| ATOM | 3567 | N | ILE | B | 412 | 26.698 | 4.632 | 45.772 | 1.00 | 30.31 |
| ATOM | 3568 | CA | ILE | B | 412 | 26.480 | 3.387 | 45.054 | 1.00 | 31.17 |
| ATOM | 3569 | CB | ILE | B | 412 | 27.004 | 2.190 | 45.883 | 1.00 | 30.04 |
| ATOM | 3570 | CG2 | ILE | B | 412 | 26.482 | 0.861 | 45.333 | 1.00 | 30.74 |
| ATOM | 3571 | CG1 | ILE | B | 412 | 28.530 | 2.229 | 45.927 | 1.00 | 28.61 |
| ATOM | 3572 | CD1 | ILE | B | 412 | 29.143 | 1.214 | 46.847 | 1.00 | 25.03 |
| ATOM | 3573 | C | ILE | B | 412 | 24.987 | 3.205 | 44.792 | 1.00 | 31.85 |
| ATOM | 3574 | O | ILE | B | 412 | 24.593 | 2.863 | 43.680 | 1.00 | 33.58 |
| ATOM | 3575 | N | ASN | B | 413 | 24.170 | 3.502 | 45.804 | 1.00 | 32.71 |
| ATOM | 3576 | CA | ASN | B | 413 | 22.718 | 3.340 | 45.734 | 1.00 | 34.24 |
| ATOM | 3577 | CB | ASN | B | 413 | 22.137 | 3.186 | 47.143 | 1.00 | 34.95 |
| ATOM | 3578 | CG | ASN | B | 413 | 22.530 | 1.877 | 47.792 | 1.00 | 38.19 |
| ATOM | 3579 | OD1 | ASN | B | 413 | 22.648 | 0.845 | 47.109 | 1.00 | 40.18 |
| ATOM | 3580 | ND2 | ASN | B | 413 | 22.718 | 1.895 | 49.114 | 1.00 | 38.68 |
| ATOM | 3581 | C | ASN | B | 413 | 21.917 | 4.391 | 44.985 | 1.00 | 34.53 |
| ATOM | 3582 | O | ASN | B | 413 | 20.863 | 4.082 | 44.414 | 1.00 | 34.67 |
| ATOM | 3583 | N | TYR | B | 414 | 22.373 | 5.637 | 45.025 | 1.00 | 34.60 |
| ATOM | 3584 | CA | TYR | B | 414 | 21.637 | 6.705 | 44.348 | 1.00 | 35.07 |
| ATOM | 3585 | CB | TYR | B | 414 | 20.785 | 7.494 | 45.359 | 1.00 | 35.74 |
| ATOM | 3586 | CG | TYR | B | 414 | 19.899 | 6.629 | 46.217 | 1.00 | 37.15 |

Figure 10

| | | | | | | | | |
|---|---|---|---|---|---|---|---|---|
| ATOM | 3587 | CD1 | TYR | B | 414 | 18.794 | 5.976 | 45.673 | 1.00 38.30 |
| ATOM | 3588 | CE1 | TYR | B | 414 | 17.999 | 5.124 | 46.458 | 1.00 39.63 |
| ATOM | 3589 | CD2 | TYR | B | 414 | 20.196 | 6.419 | 47.571 | 1.00 38.77 |
| ATOM | 3590 | CE2 | TYR | B | 414 | 19.414 | 5.573 | 48.365 | 1.00 39.29 |
| ATOM | 3591 | CZ | TYR | B | 414 | 18.319 | 4.928 | 47.804 | 1.00 39.55 |
| ATOM | 3592 | OH | TYR | B | 414 | 17.550 | 4.095 | 48.593 | 1.00 40.53 |
| ATOM | 3593 | C | TYR | B | 414 | 22.534 | 7.652 | 43.563 | 1.00 33.76 |
| ATOM | 3594 | O | TYR | B | 414 | 22.072 | 8.662 | 43.031 | 1.00 33.63 |
| ATOM | 3595 | N | GLY | B | 415 | 23.813 | 7.312 | 43.468 | 1.00 32.96 |
| ATOM | 3596 | CA | GLY | B | 415 | 24.735 | 8.165 | 42.746 | 1.00 33.62 |
| ATOM | 3597 | C | GLY | B | 415 | 24.894 | 9.551 | 43.370 | 1.00 33.65 |
| ATOM | 3598 | O | GLY | B | 415 | 25.291 | 10.501 | 42.691 | 1.00 33.75 |
| ATOM | 3599 | N | THR | B | 416 | 24.569 | 9.681 | 44.657 | 1.00 33.05 |
| ATOM | 3600 | CA | THR | B | 416 | 24.714 | 10.966 | 45.337 | 1.00 31.46 |
| ATOM | 3601 | CB | THR | B | 416 | 23.562 | 11.246 | 46.368 | 1.00 31.43 |
| ATOM | 3602 | OG1 | THR | B | 416 | 24.090 | 11.940 | 47.508 | 1.00 31.22 |
| ATOM | 3603 | CG2 | THR | B | 416 | 22.865 | 9.970 | 46.809 | 1.00 30.10 |
| ATOM | 3604 | C | THR | B | 416 | 26.104 | 11.100 | 45.983 | 1.00 29.51 |
| ATOM | 3605 | O | THR | B | 416 | 26.469 | 10.333 | 46.875 | 1.00 27.85 |
| ATOM | 3606 | N | PHE | B | 417 | 26.867 | 12.064 | 45.477 | 1.00 27.83 |
| ATOM | 3607 | CA | PHE | B | 417 | 28.216 | 12.352 | 45.937 | 1.00 26.59 |
| ATOM | 3608 | CB | PHE | B | 417 | 29.196 | 12.296 | 44.760 | 1.00 27.49 |
| ATOM | 3609 | CG | PHE | B | 417 | 29.453 | 10.913 | 44.230 | 1.00 28.51 |
| ATOM | 3610 | CD1 | PHE | B | 417 | 28.618 | 10.354 | 43.249 | 1.00 28.28 |
| ATOM | 3611 | CD2 | PHE | B | 417 | 30.562 | 10.181 | 44.674 | 1.00 27.91 |
| ATOM | 3612 | CE1 | PHE | B | 417 | 28.892 | 9.084 | 42.700 | 1.00 28.54 |
| ATOM | 3613 | CE2 | PHE | B | 417 | 30.851 | 8.909 | 44.140 | 1.00 28.55 |
| ATOM | 3614 | CZ | PHE | B | 417 | 30.013 | 8.355 | 43.151 | 1.00 29.51 |
| ATOM | 3615 | C | PHE | B | 417 | 28.375 | 13.715 | 46.594 | 1.00 24.60 |
| ATOM | 3616 | O | PHE | B | 417 | 28.063 | 14.732 | 45.992 | 1.00 24.74 |
| ATOM | 3617 | N | THR | B | 418 | 28.922 | 13.724 | 47.806 | 1.00 23.18 |
| ATOM | 3618 | CA | THR | B | 418 | 29.176 | 14.958 | 48.562 | 1.00 20.48 |
| ATOM | 3619 | CB | THR | B | 418 | 28.112 | 15.224 | 49.682 | 1.00 19.35 |
| ATOM | 3620 | OG1 | THR | B | 418 | 28.285 | 14.283 | 50.741 | 1.00 20.17 |
| ATOM | 3621 | CG2 | THR | B | 418 | 26.705 | 15.088 | 49.145 | 1.00 17.19 |
| ATOM | 3622 | C | THR | B | 418 | 30.545 | 14.827 | 49.237 | 1.00 19.22 |
| ATOM | 3623 | O | THR | B | 418 | 31.271 | 13.862 | 49.008 | 1.00 17.22 |
| ATOM | 3624 | N | ILE | B | 419 | 30.884 | 15.810 | 50.066 | 1.00 18.53 |
| ATOM | 3625 | CA | ILE | B | 419 | 32.136 | 15.822 | 50.806 | 1.00 17.14 |
| ATOM | 3626 | CB | ILE | B | 419 | 32.362 | 17.190 | 51.505 | 1.00 17.31 |
| ATOM | 3627 | CG2 | ILE | B | 419 | 31.420 | 17.373 | 52.676 | 1.00 14.65 |
| ATOM | 3628 | CG1 | ILE | B | 419 | 33.803 | 17.301 | 51.973 | 1.00 18.95 |
| ATOM | 3629 | CD1 | ILE | B | 419 | 34.833 | 17.250 | 50.819 | 1.00 19.61 |
| ATOM | 3630 | C | ILE | B | 419 | 32.062 | 14.711 | 51.849 | 1.00 16.46 |
| ATOM | 3631 | O | ILE | B | 419 | 33.073 | 14.210 | 52.310 | 1.00 15.73 |
| ATOM | 3632 | N | LYS | B | 420 | 30.845 | 14.313 | 52.193 | 1.00 15.64 |
| ATOM | 3633 | CA | LYS | B | 420 | 30.657 | 13.252 | 53.159 | 1.00 15.60 |
| ATOM | 3634 | CB | LYS | B | 420 | 29.227 | 13.262 | 53.724 | 1.00 14.44 |
| ATOM | 3635 | CG | LYS | B | 420 | 28.955 | 14.413 | 54.672 | 1.00 11.94 |
| ATOM | 3636 | CD | LYS | B | 420 | 29.963 | 14.427 | 55.797 | 1.00 12.47 |
| ATOM | 3637 | CE | LYS | B | 420 | 29.651 | 15.540 | 56.738 | 1.00 13.84 |
| ATOM | 3638 | NZ | LYS | B | 420 | 30.688 | 15.643 | 57.751 | 1.00 16.61 |
| ATOM | 3639 | C | LYS | B | 420 | 31.020 | 11.894 | 52.565 | 1.00 16.10 |
| ATOM | 3640 | O | LYS | B | 420 | 31.442 | 11.002 | 53.285 | 1.00 15.74 |
| ATOM | 3641 | N | SER | B | 421 | 30.835 | 11.717 | 51.259 | 1.00 16.90 |
| ATOM | 3642 | CA | SER | B | 421 | 31.221 | 10.450 | 50.659 | 1.00 16.80 |
| ATOM | 3643 | CB | SER | B | 421 | 30.507 | 10.148 | 49.320 | 1.00 18.81 |
| ATOM | 3644 | OG | SER | B | 421 | 29.784 | 11.223 | 48.756 | 1.00 18.65 |
| ATOM | 3645 | C | SER | B | 421 | 32.739 | 10.414 | 50.523 | 1.00 16.25 |

Figure 10

```
ATOM   3646  O    SER B 421      33.331   9.340  50.500  1.00 17.52
ATOM   3647  N    ASP B 422      33.370  11.587  50.460  1.00 15.71
ATOM   3648  CA   ASP B 422      34.834  11.649  50.392  1.00 16.35
ATOM   3649  CB   ASP B 422      35.361  13.067  50.103  1.00 15.95
ATOM   3650  CG   ASP B 422      35.222  13.494  48.645  1.00 17.12
ATOM   3651  OD1  ASP B 422      35.112  12.654  47.724  1.00 18.56
ATOM   3652  OD2  ASP B 422      35.240  14.715  48.419  1.00 18.58
ATOM   3653  C    ASP B 422      35.371  11.218  51.755  1.00 15.48
ATOM   3654  O    ASP B 422      36.430  10.626  51.822  1.00 18.02
ATOM   3655  N    VAL B 423      34.683  11.609  52.834  1.00 15.09
ATOM   3656  CA   VAL B 423      35.063  11.243  54.203  1.00 14.06
ATOM   3657  CB   VAL B 423      34.116  11.887  55.291  1.00 13.46
ATOM   3658  CG1  VAL B 423      34.483  11.397  56.705  1.00 12.03
ATOM   3659  CG2  VAL B 423      34.198  13.424  55.251  1.00  9.41
ATOM   3660  C    VAL B 423      35.046   9.713  54.266  1.00 14.97
ATOM   3661  O    VAL B 423      35.999   9.106  54.770  1.00 16.63
ATOM   3662  N    TRP B 424      34.031   9.091  53.656  1.00 14.84
ATOM   3663  CA   TRP B 424      33.942   7.627  53.600  1.00 14.25
ATOM   3664  CB   TRP B 424      32.666   7.187  52.877  1.00 12.33
ATOM   3665  CG   TRP B 424      32.560   5.700  52.741  1.00 11.97
ATOM   3666  CD2  TRP B 424      31.660   4.821  53.434  1.00 12.29
ATOM   3667  CE2  TRP B 424      31.916   3.509  52.965  1.00 13.67
ATOM   3668  CE3  TRP B 424      30.663   5.013  54.404  1.00 13.54
ATOM   3669  CD1  TRP B 424      33.300   4.909  51.918  1.00 13.70
ATOM   3670  NE1  TRP B 424      32.920   3.597  52.040  1.00 13.57
ATOM   3671  CZ2  TRP B 424      31.209   2.385  53.426  1.00 13.11
ATOM   3672  CZ3  TRP B 424      29.950   3.886  54.871  1.00 15.60
ATOM   3673  CH2  TRP B 424      30.235   2.590  54.377  1.00 13.85
ATOM   3674  C    TRP B 424      35.195   7.109  52.867  1.00 16.14
ATOM   3675  O    TRP B 424      35.938   6.277  53.389  1.00 16.87
ATOM   3676  N    SER B 425      35.466   7.649  51.680  1.00 17.24
ATOM   3677  CA   SER B 425      36.653   7.261  50.921  1.00 17.45
ATOM   3678  CB   SER B 425      36.760   8.089  49.639  1.00 19.09
ATOM   3679  OG   SER B 425      35.633   7.889  48.803  1.00 19.43
ATOM   3680  C    SER B 425      37.938   7.457  51.737  1.00 18.00
ATOM   3681  O    SER B 425      38.875   6.678  51.606  1.00 19.23
ATOM   3682  N    PHE B 426      37.993   8.511  52.552  1.00 17.34
ATOM   3683  CA   PHE B 426      39.170   8.781  53.380  1.00 17.65
ATOM   3684  CB   PHE B 426      39.047  10.127  54.111  1.00 16.00
ATOM   3685  CG   PHE B 426      40.279  10.500  54.895  1.00 16.00
ATOM   3686  CD1  PHE B 426      41.436  10.933  54.241  1.00 16.10
ATOM   3687  CD2  PHE B 426      40.303  10.395  56.277  1.00 15.10
ATOM   3688  CE1  PHE B 426      42.587  11.249  54.947  1.00 14.49
ATOM   3689  CE2  PHE B 426      41.461  10.712  56.993  1.00 15.26
ATOM   3690  CZ   PHE B 426      42.603  11.140  56.322  1.00 15.14
ATOM   3691  C    PHE B 426      39.370   7.655  54.392  1.00 16.99
ATOM   3692  O    PHE B 426      40.493   7.217  54.627  1.00 18.03
ATOM   3693  N    GLY B 427      38.270   7.195  54.984  1.00 16.98
ATOM   3694  CA   GLY B 427      38.342   6.099  55.932  1.00 17.32
ATOM   3695  C    GLY B 427      38.974   4.884  55.274  1.00 17.68
ATOM   3696  O    GLY B 427      39.853   4.266  55.860  1.00 18.27
ATOM   3697  N    ILE B 428      38.531   4.559  54.056  1.00 18.19
ATOM   3698  CA   ILE B 428      39.059   3.434  53.275  1.00 18.05
ATOM   3699  CB   ILE B 428      38.329   3.300  51.914  1.00 18.13
ATOM   3700  CG2  ILE B 428      38.861   2.109  51.135  1.00 17.50
ATOM   3701  CG1  ILE B 428      36.829   3.128  52.138  1.00 19.18
ATOM   3702  CD1  ILE B 428      36.459   1.933  52.990  1.00 19.66
ATOM   3703  C    ILE B 428      40.535   3.660  52.992  1.00 18.25
ATOM   3704  O    ILE B 428      41.326   2.723  52.997  1.00 18.68
```

Figure 10

```
ATOM   3705  N   LEU B 429      40.895   4.915  52.747  1.00 18.48
ATOM   3706  CA  LEU B 429      42.274   5.295  52.464  1.00 18.27
ATOM   3707  CB  LEU B 429      42.297   6.751  51.969  1.00 17.55
ATOM   3708  CG  LEU B 429      43.542   7.363  51.333  1.00 18.60
ATOM   3709  CD1 LEU B 429      43.121   8.641  50.648  1.00 17.72
ATOM   3710  CD2 LEU B 429      44.666   7.624  52.349  1.00 16.97
ATOM   3711  C   LEU B 429      43.167   5.104  53.713  1.00 18.66
ATOM   3712  O   LEU B 429      44.365   4.786  53.596  1.00 19.27
ATOM   3713  N   LEU B 430      42.601   5.320  54.901  1.00 17.55
ATOM   3714  CA  LEU B 430      43.362   5.141  56.122  1.00 16.25
ATOM   3715  CB  LEU B 430      42.568   5.567  57.339  1.00 15.34
ATOM   3716  CG  LEU B 430      42.368   7.065  57.546  1.00 13.88
ATOM   3717  CD1 LEU B 430      41.413   7.292  58.709  1.00  9.97
ATOM   3718  CD2 LEU B 430      43.714   7.767  57.771  1.00 10.56
ATOM   3719  C   LEU B 430      43.771   3.692  56.266  1.00 17.49
ATOM   3720  O   LEU B 430      44.815   3.410  56.833  1.00 20.09
ATOM   3721  N   THR B 431      42.937   2.768  55.790  1.00 18.18
ATOM   3722  CA  THR B 431      43.268   1.339  55.855  1.00 19.46
ATOM   3723  CB  THR B 431      42.073   0.403  55.484  1.00 17.46
ATOM   3724  OG1 THR B 431      41.785   0.522  54.087  1.00 19.55
ATOM   3725  CG2 THR B 431      40.829   0.740  56.298  1.00 16.36
ATOM   3726  C   THR B 431      44.448   1.035  54.922  1.00 20.76
ATOM   3727  O   THR B 431      45.296   0.206  55.250  1.00 21.68
ATOM   3728  N   GLU B 432      44.473   1.689  53.758  1.00 21.72
ATOM   3729  CA  GLU B 432      45.553   1.538  52.789  1.00 21.08
ATOM   3730  CB  GLU B 432      45.285   2.387  51.550  1.00 19.77
ATOM   3731  CG  GLU B 432      44.055   1.996  50.777  1.00 20.30
ATOM   3732  CD  GLU B 432      43.978   2.726  49.460  1.00 20.68
ATOM   3733  OE1 GLU B 432      43.295   3.765  49.354  1.00 21.45
ATOM   3734  OE2 GLU B 432      44.635   2.267  48.520  1.00 23.19
ATOM   3735  C   GLU B 432      46.855   2.011  53.418  1.00 22.31
ATOM   3736  O   GLU B 432      47.889   1.360  53.292  1.00 24.29
ATOM   3737  N   ILE B 433      46.810   3.150  54.093  1.00 22.17
ATOM   3738  CA  ILE B 433      48.005   3.683  54.715  1.00 23.37
ATOM   3739  CB  ILE B 433      47.747   5.078  55.313  1.00 24.14
ATOM   3740  CG2 ILE B 433      48.859   5.463  56.282  1.00 23.11
ATOM   3741  CG1 ILE B 433      47.595   6.118  54.196  1.00 23.00
ATOM   3742  CD1 ILE B 433      47.362   7.552  54.692  1.00 19.87
ATOM   3743  C   ILE B 433      48.624   2.760  55.779  1.00 25.40
ATOM   3744  O   ILE B 433      49.834   2.524  55.755  1.00 26.43
ATOM   3745  N   VAL B 434      47.811   2.230  56.696  1.00 26.01
ATOM   3746  CA  VAL B 434      48.341   1.367  57.750  1.00 27.08
ATOM   3747  CB  VAL B 434      47.461   1.379  59.036  1.00 26.70
ATOM   3748  CG1 VAL B 434      47.369   2.768  59.585  1.00 27.18
ATOM   3749  CG2 VAL B 434      46.078   0.829  58.756  1.00 26.67
ATOM   3750  C   VAL B 434      48.623  -0.083  57.368  1.00 28.06
ATOM   3751  O   VAL B 434      49.078  -0.846  58.209  1.00 31.07
ATOM   3752  N   THR B 435      48.327  -0.481  56.135  1.00 28.30
ATOM   3753  CA  THR B 435      48.587  -1.856  55.706  1.00 29.44
ATOM   3754  CB  THR B 435      47.310  -2.595  55.256  1.00 28.24
ATOM   3755  OG1 THR B 435      46.687  -1.864  54.200  1.00 27.81
ATOM   3756  CG2 THR B 435      46.336  -2.778  56.400  1.00 26.11
ATOM   3757  C   THR B 435      49.547  -1.833  54.528  1.00 31.93
ATOM   3758  O   THR B 435      49.650  -2.806  53.770  1.00 32.17
ATOM   3759  N   HIS B 436      50.181  -0.680  54.338  1.00 34.63
ATOM   3760  CA  HIS B 436      51.152  -0.460  53.270  1.00 37.45
ATOM   3761  CB  HIS B 436      52.393  -1.306  53.538  1.00 42.57
ATOM   3762  CG  HIS B 436      52.940  -1.153  54.923  1.00 47.43
ATOM   3763  CD2 HIS B 436      53.391  -2.072  55.811  1.00 49.86
```

Figure 10

| | | | | | | | | | |
|---|---|---|---|---|---|---|---|---|---|
| ATOM | 3764 | ND1 | HIS | B | 436 | 53.104 | 0.076 | 55.529 | 1.00 48.86 |
| ATOM | 3765 | CE1 | HIS | B | 436 | 53.639 | -0.089 | 56.725 | 1.00 49.49 |
| ATOM | 3766 | NE2 | HIS | B | 436 | 53.822 | -1.385 | 56.920 | 1.00 51.96 |
| ATOM | 3767 | C | HIS | B | 436 | 50.646 | -0.690 | 51.838 | 1.00 36.48 |
| ATOM | 3768 | O | HIS | B | 436 | 51.287 | -1.387 | 51.048 | 1.00 36.13 |
| ATOM | 3769 | N | GLY | B | 437 | 49.512 | -0.086 | 51.501 | 1.00 35.34 |
| ATOM | 3770 | CA | GLY | B | 437 | 48.966 | -0.236 | 50.165 | 1.00 35.48 |
| ATOM | 3771 | C | GLY | B | 437 | 48.181 | -1.509 | 49.881 | 1.00 36.05 |
| ATOM | 3772 | O | GLY | B | 437 | 48.016 | -1.908 | 48.721 | 1.00 36.50 |
| ATOM | 3773 | N | ARG | B | 438 | 47.709 | -2.167 | 50.931 | 1.00 36.50 |
| ATOM | 3774 | CA | ARG | B | 438 | 46.918 | -3.380 | 50.753 | 1.00 36.72 |
| ATOM | 3775 | CB | ARG | B | 438 | 46.809 | -4.132 | 52.084 | 1.00 40.75 |
| ATOM | 3776 | CG | ARG | B | 438 | 46.450 | -5.615 | 51.994 | 1.00 44.89 |
| ATOM | 3777 | CD | ARG | B | 438 | 44.963 | -5.838 | 51.877 | 1.00 48.70 |
| ATOM | 3778 | NE | ARG | B | 438 | 44.193 | -5.188 | 52.943 | 1.00 52.98 |
| ATOM | 3779 | CZ | ARG | B | 438 | 44.210 | -5.559 | 54.222 | 1.00 55.71 |
| ATOM | 3780 | NH1 | ARG | B | 438 | 44.976 | -6.579 | 54.612 | 1.00 56.88 |
| ATOM | 3781 | NH2 | ARG | B | 438 | 43.425 | -4.940 | 55.106 | 1.00 55.19 |
| ATOM | 3782 | C | ARG | B | 438 | 45.534 | -2.958 | 50.248 | 1.00 34.85 |
| ATOM | 3783 | O | ARG | B | 438 | 44.995 | -1.931 | 50.672 | 1.00 33.27 |
| ATOM | 3784 | N | ILE | B | 439 | 44.991 | -3.737 | 49.312 | 1.00 32.62 |
| ATOM | 3785 | CA | ILE | B | 439 | 43.678 | -3.465 | 48.737 | 1.00 30.60 |
| ATOM | 3786 | CB | ILE | B | 439 | 43.393 | -4.396 | 47.530 | 1.00 30.99 |
| ATOM | 3787 | CG2 | ILE | B | 439 | 42.000 | -4.149 | 46.972 | 1.00 30.87 |
| ATOM | 3788 | CG1 | ILE | B | 439 | 44.415 | -4.111 | 46.422 | 1.00 34.15 |
| ATOM | 3789 | CD1 | ILE | B | 439 | 44.291 | -4.978 | 45.149 | 1.00 37.25 |
| ATOM | 3790 | C | ILE | B | 439 | 42.596 | -3.636 | 49.803 | 1.00 29.26 |
| ATOM | 3791 | O | ILE | B | 439 | 42.652 | -4.563 | 50.603 | 1.00 29.19 |
| ATOM | 3792 | N | PRO | B | 440 | 41.630 | -2.702 | 49.865 | 1.00 27.16 |
| ATOM | 3793 | CD | PRO | B | 440 | 41.543 | -1.442 | 49.109 | 1.00 25.45 |
| ATOM | 3794 | CA | PRO | B | 440 | 40.551 | -2.789 | 50.854 | 1.00 25.40 |
| ATOM | 3795 | CB | PRO | B | 440 | 39.747 | -1.514 | 50.583 | 1.00 25.37 |
| ATOM | 3796 | CG | PRO | B | 440 | 40.773 | -0.572 | 50.050 | 1.00 25.69 |
| ATOM | 3797 | C | PRO | B | 440 | 39.721 | -4.056 | 50.610 | 1.00 24.44 |
| ATOM | 3798 | O | PRO | B | 440 | 39.757 | -4.618 | 49.513 | 1.00 23.65 |
| ATOM | 3799 | N | TYR | B | 441 | 38.994 | -4.507 | 51.633 | 1.00 23.90 |
| ATOM | 3800 | CA | TYR | B | 441 | 38.155 | -5.712 | 51.542 | 1.00 24.23 |
| ATOM | 3801 | CB | TYR | B | 441 | 36.851 | -5.421 | 50.782 | 1.00 22.00 |
| ATOM | 3802 | CG | TYR | B | 441 | 36.095 | -4.222 | 51.290 | 1.00 20.98 |
| ATOM | 3803 | CD1 | TYR | B | 441 | 35.227 | -4.333 | 52.374 | 1.00 22.24 |
| ATOM | 3804 | CE1 | TYR | B | 441 | 34.543 | -3.228 | 52.861 | 1.00 22.09 |
| ATOM | 3805 | CD2 | TYR | B | 441 | 36.257 | -2.972 | 50.699 | 1.00 19.00 |
| ATOM | 3806 | CE2 | TYR | B | 441 | 35.580 | -1.869 | 51.170 | 1.00 21.20 |
| ATOM | 3807 | CZ | TYR | B | 441 | 34.721 | -1.998 | 52.254 | 1.00 24.05 |
| ATOM | 3808 | OH | TYR | B | 441 | 34.039 | -0.895 | 52.734 | 1.00 27.58 |
| ATOM | 3809 | C | TYR | B | 441 | 38.936 | -6.803 | 50.816 | 1.00 25.33 |
| ATOM | 3810 | O | TYR | B | 441 | 38.544 | -7.246 | 49.736 | 1.00 24.82 |
| ATOM | 3811 | N | PRO | B | 442 | 40.084 | -7.218 | 51.380 | 1.00 27.20 |
| ATOM | 3812 | CD | PRO | B | 442 | 40.623 | -6.902 | 52.720 | 1.00 26.82 |
| ATOM | 3813 | CA | PRO | B | 442 | 40.873 | -8.259 | 50.710 | 1.00 28.70 |
| ATOM | 3814 | CB | PRO | B | 442 | 42.115 | -8.370 | 51.601 | 1.00 27.88 |
| ATOM | 3815 | CG | PRO | B | 442· | 41.567 | -8.059 | 52.982 | 1.00 28.04 |
| ATOM | 3816 | C | PRO | B | 442 | 40.086 | -9.569 | 50.601 | 1.00 30.74 |
| ATOM | 3817 | O | PRO | B | 442 | 39.389 | -9.973 | 51.525 | 1.00 32.79 |
| ATOM | 3818 | N | GLY | B | 443 | 40.125 | -10.192 | 49.437 | 1.00 32.08 |
| ATOM | 3819 | CA | GLY | B | 443 | 39.412 | -11.441 | 49.284 | 1.00 32.96 |
| ATOM | 3820 | C | GLY | B | 443 | 37.959 | -11.237 | 48.958 | 1.00 33.19 |
| ATOM | 3821 | O | GLY | B | 443 | 37.159 | -12.157 | 49.091 | 1.00 34.95 |
| ATOM | 3822 | N | MET | B | 444 | 37.605 | -10.020 | 48.579 | 1.00 32.53 |

Figure 10

| | | | | | | | | | |
|---|---|---|---|---|---|---|---|---|---|
| ATOM | 3823 | CA | MET | B | 444 | 36.233 | -9.717 | 48.207 | 1.00 32.66 |
| ATOM | 3824 | CB | MET | B | 444 | 35.570 | -8.784 | 49.223 | 1.00 33.27 |
| ATOM | 3825 | CG | MET | B | 444 | 34.806 | -9.491 | 50.308 | 1.00 33.26 |
| ATOM | 3826 | SD | MET | B | 444 | 34.197 | -8.343 | 51.517 | 1.00 33.67 |
| ATOM | 3827 | CE | MET | B | 444 | 32.850 | -7.823 | 50.761 | 1.00 35.80 |
| ATOM | 3828 | C | MET | B | 444 | 36.246 | -9.039 | 46.864 | 1.00 32.59 |
| ATOM | 3829 | O | MET | B | 444 | 37.100 | -8.187 | 46.621 | 1.00 33.34 |
| ATOM | 3830 | N | THR | B | 445 | 35.341 | -9.454 | 45.977 | 1.00 31.11 |
| ATOM | 3831 | CA | THR | B | 445 | 35.241 | -8.842 | 44.659 | 1.00 30.01 |
| ATOM | 3832 | CB | THR | B | 445 | 34.719 | -9.839 | 43.600 | 1.00 30.49 |
| ATOM | 3833 | OG1 | THR | B | 445 | 33.318 | -10.056 | 43.789 | 1.00 31.41 |
| ATOM | 3834 | CG2 | THR | B | 445 | 35.435 | -11.180 | 43.731 | 1.00 31.09 |
| ATOM | 3835 | C | THR | B | 445 | 34.279 | -7.654 | 44.783 | 1.00 29.52 |
| ATOM | 3836 | O | THR | B | 445 | 33.629 | -7.479 | 45.816 | 1.00 29.75 |
| ATOM | 3837 | N | ASN | B | 446 | 34.184 | -6.839 | 43.742 | 1.00 28.47 |
| ATOM | 3838 | CA | ASN | B | 446 | 33.293 | -5.687 | 43.785 | 1.00 28.05 |
| ATOM | 3839 | CB | ASN | B | 446 | 33.347 | -4.883 | 42.478 | 1.00 28.89 |
| ATOM | 3840 | CG | ASN | B | 446 | 34.565 | -3.975 | 42.392 | 1.00 29.55 |
| ATOM | 3841 | OD1 | ASN | B | 446 | 35.507 | -4.100 | 43.174 | 1.00 30.54 |
| ATOM | 3842 | ND2 | ASN | B | 446 | 34.539 | -3.044 | 41.448 | 1.00 29.66 |
| ATOM | 3843 | C | ASN | B | 446 | 31.850 | -6.024 | 44.118 | 1.00 27.30 |
| ATOM | 3844 | O | ASN | B | 446 | 31.228 | -5.335 | 44.929 | 1.00 24.96 |
| ATOM | 3845 | N | PRO | B | 447 | 31.267 | -7.027 | 43.430 | 1.00 28.01 |
| ATOM | 3846 | CD | PRO | B | 447 | 31.695 | -7.633 | 42.153 | 1.00 27.48 |
| ATOM | 3847 | CA | PRO | B | 447 | 29.872 | -7.373 | 43.735 | 1.00 27.46 |
| ATOM | 3848 | CB | PRO | B | 447 | 29.491 | -8.347 | 42.609 | 1.00 27.36 |
| ATOM | 3849 | CG | PRO | B | 447 | 30.816 | -8.828 | 42.058 | 1.00 28.11 |
| ATOM | 3850 | C | PRO | B | 447 | 29.651 | -7.926 | 45.148 | 1.00 27.19 |
| ATOM | 3851 | O | PRO | B | 447 | 28.556 | -7.799 | 45.717 | 1.00 27.64 |
| ATOM | 3852 | N | GLU | B | 448 | 30.697 | -8.488 | 45.735 | 1.00 25.76 |
| ATOM | 3853 | CA | GLU | B | 448 | 30.589 | -8.990 | 47.088 | 1.00 26.14 |
| ATOM | 3854 | CB | GLU | B | 448 | 31.694 | -9.996 | 47.367 | 1.00 28.12 |
| ATOM | 3855 | CG | GLU | B | 448 | 31.473 | -11.304 | 46.631 | 1.00 30.08 |
| ATOM | 3856 | CD | GLU | B | 448 | 32.708 | -12.165 | 46.547 | 1.00 31.15 |
| ATOM | 3857 | OE1 | GLU | B | 448 | 33.745 | -11.827 | 47.161 | 1.00 32.34 |
| ATOM | 3858 | OE2 | GLU | B | 448 | 32.630 | -13.195 | 45.847 | 1.00 32.56 |
| ATOM | 3859 | C | GLU | B | 448 | 30.640 | -7.829 | 48.082 | 1.00 25.59 |
| ATOM | 3860 | O | GLU | B | 448 | 29.979 | -7.885 | 49.115 | 1.00 25.08 |
| ATOM | 3861 | N | VAL | B | 449 | 31.439 | -6.799 | 47.772 | 1.00 25.09 |
| ATOM | 3862 | CA | VAL | B | 449 | 31.554 | -5.597 | 48.610 | 1.00 24.93 |
| ATOM | 3863 | CB | VAL | B | 449 | 32.652 | -4.617 | 48.088 | 1.00 24.20 |
| ATOM | 3864 | CG1 | VAL | B | 449 | 32.555 | -3.264 | 48.788 | 1.00 20.39 |
| ATOM | 3865 | CG2 | VAL | B | 449 | 34.014 | -5.206 | 48.294 | 1.00 21.56 |
| ATOM | 3866 | C | VAL | B | 449 | 30.204 | -4.885 | 48.597 | 1.00 26.14 |
| ATOM | 3867 | O | VAL | B | 449 | 29.769 | -4.316 | 49.601 | 1.00 27.97 |
| ATOM | 3868 | N | ILE | B | 450 | 29.520 | -4.965 | 47.462 | 1.00 26.21 |
| ATOM | 3869 | CA | ILE | B | 450 | 28.213 | -4.338 | 47.318 | 1.00 26.77 |
| ATOM | 3870 | CB | ILE | B | 450 | 27.725 | -4.392 | 45.861 | 1.00 27.08 |
| ATOM | 3871 | CG2 | ILE | B | 450 | 26.380 | -3.696 | 45.738 | 1.00 28.06 |
| ATOM | 3872 | CG1 | ILE | B | 450 | 28.749 | -3.755 | 44.932 | 1.00 28.79 |
| ATOM | 3873 | CD1 | ILE | B | 450 | 28.964 | -2.298 | 45.162 | 1.00 29.40 |
| ATOM | 3874 | C | ILE | B | 450 | 27.165 | -5.014 | 48.202 | 1.00 26.23 |
| ATOM | 3875 | O | ILE | B | 450 | 26.417 | -4.339 | 48.914 | 1.00 25.70 |
| ATOM | 3876 | N | GLN | B | 451 | 27.111 | -6.343 | 48.155 | 1.00 26.40 |
| ATOM | 3877 | CA | GLN | B | 451 | 26.133 | -7.072 | 48.953 | 1.00 27.23 |
| ATOM | 3878 | CB | GLN | B | 451 | 25.898 | -8.487 | 48.412 | 1.00 30.30 |
| ATOM | 3879 | CG | GLN | B | 451 | 27.125 | -9.344 | 48.336 | 1.00 36.65 |
| ATOM | 3880 | CD | GLN | B | 451 | 26.982 | -10.493 | 47.351 | 1.00 40.20 |
| ATOM | 3881 | OE1 | GLN | B | 451 | 27.358 | -11.629 | 47.653 | 1.00 43.95 |

Figure 10

| | | | | | | | | | |
|---|---|---|---|---|---|---|---|---|---|
| ATOM | 3882 | NE2 | GLN | B | 451 | 26.477 | -10.199 | 46.156 | 1.00 40.26 |
| ATOM | 3883 | C | GLN | B | 451 | 26.493 | -7.077 | 50.421 | 1.00 24.60 |
| ATOM | 3884 | O | GLN | B | 451 | 25.622 | -7.174 | 51.266 | 1.00 25.08 |
| ATOM | 3885 | N | ASN | B | 452 | 27.776 | -6.960 | 50.730 | 1.00 23.67 |
| ATOM | 3886 | CA | ASN | B | 452 | 28.192 | -6.901 | 52.118 | 1.00 22.13 |
| ATOM | 3887 | CB | ASN | B | 452 | 29.691 | -7.158 | 52.251 | 1.00 23.95 |
| ATOM | 3888 | CG | ASN | B | 452 | 30.011 | -8.632 | 52.516 | 1.00 25.79 |
| ATOM | 3889 | OD1 | ASN | B | 452 | 29.999 | -9.080 | 53.667 | 1.00 25.15 |
| ATOM | 3890 | ND2 | ASN | B | 452 | 30.283 | -9.390 | 51.449 | 1.00 22.95 |
| ATOM | 3891 | C | ASN | B | 452 | 27.803 | -5.519 | 52.648 | 1.00 21.38 |
| ATOM | 3892 | O | ASN | B | 452 | 27.259 | -5.413 | 53.741 | 1.00 22.40 |
| ATOM | 3893 | N | LEU | B | 453 | 28.010 | -4.465 | 51.863 | 1.00 19.34 |
| ATOM | 3894 | CA | LEU | B | 453 | 27.621 | -3.138 | 52.329 | 1.00 19.89 |
| ATOM | 3895 | CB | LEU | B | 453 | 28.140 | -2.028 | 51.419 | 1.00 20.64 |
| ATOM | 3896 | CG | LEU | B | 453 | 29.603 | -1.589 | 51.486 | 1.00 21.11 |
| ATOM | 3897 | CD1 | LEU | B | 453 | 29.681 | -0.349 | 50.640 | 1.00 23.08 |
| ATOM | 3898 | CD2 | LEU | B | 453 | 30.103 | -1.297 | 52.902 | 1.00 18.49 |
| ATOM | 3899 | C | LEU | B | 453 | 26.100 | -3.023 | 52.463 | 1.00 20.98 |
| ATOM | 3900 | O | LEU | B | 453 | 25.600 | -2.246 | 53.290 | 1.00 19.80 |
| ATOM | 3901 | N | GLU | B | 454 | 25.358 | -3.783 | 51.659 | 1.00 20.65 |
| ATOM | 3902 | CA | GLU | B | 454 | 23.909 | -3.746 | 51.777 | 1.00 22.76 |
| ATOM | 3903 | CB | GLU | B | 454 | 23.254 | -4.670 | 50.779 | 1.00 27.08 |
| ATOM | 3904 | CG | GLU | B | 454 | 23.341 | -4.270 | 49.337 | 1.00 37.54 |
| ATOM | 3905 | CD | GLU | B | 454 | 22.896 | -5.409 | 48.422 | 1.00 44.10 |
| ATOM | 3906 | OE1 | GLU | B | 454 | 23.154 | -5.318 | 47.198 | 1.00 48.07 |
| ATOM | 3907 | OE2 | GLU | B | 454 | 22.315 | -6.409 | 48.927 | 1.00 46.31 |
| ATOM | 3908 | C | GLU | B | 454 | 23.527 | -4.268 | 53.158 | 1.00 22.48 |
| ATOM | 3909 | O | GLU | B | 454 | 22.529 | -3.840 | 53.744 | 1.00 22.34 |
| ATOM | 3910 | N | ARG | B | 455 | 24.296 | -5.244 | 53.636 | 1.00 21.33 |
| ATOM | 3911 | CA | ARG | B | 455 | 24.058 | -5.864 | 54.932 | 1.00 20.72 |
| ATOM | 3912 | CB | ARG | B | 455 | 24.541 | -7.313 | 54.930 | 1.00 21.51 |
| ATOM | 3913 | CG | ARG | B | 455 | 23.905 | -8.210 | 53.863 | 1.00 24.90 |
| ATOM | 3914 | CD | ARG | B | 455 | 24.436 | -9.669 | 53.933 | 1.00 29.26 |
| ATOM | 3915 | NE | ARG | B | 455 | 25.875 | -9.709 | 54.195 | 1.00 36.13 |
| ATOM | 3916 | CZ | ARG | B | 455 | 26.421 | -10.034 | 55.373 | 1.00 40.21 |
| ATOM | 3917 | NH1 | ARG | B | 455 | 25.654 | -10.382 | 56.407 | 1.00 40.99 |
| ATOM | 3918 | NH2 | ARG | B | 455 | 27.725 | -9.857 | 55.572 | 1.00 41.74 |
| ATOM | 3919 | C | ARG | B | 455 | 24.704 | -5.091 | 56.084 | 1.00 19.88 |
| ATOM | 3920 | O | ARG | B | 455 | 24.572 | -5.487 | 57.229 | 1.00 20.49 |
| ATOM | 3921 | N | GLY | B | 456 | 25.394 | -3.989 | 55.781 | 1.00 19.14 |
| ATOM | 3922 | CA | GLY | B | 456 | 26.025 | -3.184 | 56.821 | 1.00 16.91 |
| ATOM | 3923 | C | GLY | B | 456 | 27.433 | -3.572 | 57.223 | 1.00 15.44 |
| ATOM | 3924 | O | GLY | B | 456 | 27.954 | -3.144 | 58.254 | 1.00 15.46 |
| ATOM | 3925 | N | TYR | B | 457 | 28.088 | -4.342 | 56.379 | 1.00 13.73 |
| ATOM | 3926 | CA | TYR | B | 457 | 29.433 | -4.786 | 56.671 | 1.00 14.65 |
| ATOM | 3927 | CB | TYR | B | 457 | 29.870 | -5.748 | 55.570 | 1.00 14.06 |
| ATOM | 3928 | CG | TYR | B | 457 | 31.248 | -6.317 | 55.749 | 1.00 14.28 |
| ATOM | 3929 | CD1 | TYR | B | 457 | 31.449 | -7.522 | 56.446 | 1.00 12.32 |
| ATOM | 3930 | CE1 | TYR | B | 457 | 32.731 | -8.045 | 56.606 | 1.00 13.17 |
| ATOM | 3931 | CD2 | TYR | B | 457 | 32.360 | -5.653 | 55.216 | 1.00 12.93 |
| ATOM | 3932 | CE2 | TYR | B | 457 | 33.637 | -6.163 | 55.374 | 1.00 13.73 |
| ATOM | 3933 | CZ | TYR | B | 457 | 33.822 | -7.356 | 56.069 | 1.00 14.69 |
| ATOM | 3934 | OH | TYR | B | 457 | 35.109 | -7.822 | 56.238 | 1.00 16.19 |
| ATOM | 3935 | C | TYR | B | 457 | 30.473 | -3.669 | 56.846 | 1.00 15.77 |
| ATOM | 3936 | O | TYR | B | 457 | 30.431 | -2.660 | 56.154 | 1.00 16.22 |
| ATOM | 3937 | N | ARG | B | 458 | 31.389 | -3.855 | 57.797 | 1.00 15.92 |
| ATOM | 3938 | CA | ARG | B | 458 | 32.490 | -2.910 | 58.036 | 1.00 17.35 |
| ATOM | 3939 | CB | ARG | B | 458 | 32.258 | -2.026 | 59.279 | 1.00 15.85 |
| ATOM | 3940 | CG | ARG | B | 458 | 31.120 | -1.016 | 59.160 | 1.00 13.07 |

Figure 10

| | | | | | | | | | |
|---|---|---|---|---|---|---|---|---|---|
| ATOM | 3941 | CD | ARG | B | 458 | 31.308 | -0.116 | 57.959 | 1.00 12.20 |
| ATOM | 3942 | NE | ARG | B | 458 | 30.266 | 0.910 | 57.880 | 1.00 12.53 |
| ATOM | 3943 | CZ | ARG | B | 458 | 29.161 | 0.808 | 57.152 | 1.00 10.32 |
| ATOM | 3944 | NH1 | ARG | B | 458 | 28.925 | -0.272 | 56.419 | 1.00 11.80 |
| ATOM | 3945 | NH2 | ARG | B | 458 | 28.274 | 1.776 | 57.176 | 1.00 8.76 |
| ATOM | 3946 | C | ARG | B | 458 | 33.753 | -3.750 | 58.240 | 1.00 18.59 |
| ATOM | 3947 | O | ARG | B | 458 | 33.704 | -4.819 | 58.865 | 1.00 17.59 |
| ATOM | 3948 | N | MET | B | 459 | 34.859 | -3.318 | 57.641 | 1.00 19.10 |
| ATOM | 3949 | CA | MET | B | 459 | 36.115 | -4.041 | 57.791 | 1.00 19.50 |
| ATOM | 3950 | CB | MET | B | 459 | 37.247 | -3.365 | 57.000 | 1.00 18.64 |
| ATOM | 3951 | CG | MET | B | 459 | 37.140 | -3.467 | 55.485 | 1.00 19.91 |
| ATOM | 3952 | SD | MET | B | 459 | 38.630 | -2.832 | 54.699 | 1.00 22.40 |
| ATOM | 3953 | CE | MET | B | 459 | 38.091 | -1.183 | 54.211 | 1.00 24.68 |
| ATOM | 3954 | C | MET | B | 459 | 36.509 | -4.054 | 59.256 | 1.00 19.58 |
| ATOM | 3955 | O | MET | B | 459 | 36.210 | -3.123 | 59.997 | 1.00 19.32 |
| ATOM | 3956 | N | VAL | B | 460 | 37.222 | -5.099 | 59.654 | 1.00 20.91 |
| ATOM | 3957 | CA | VAL | B | 460 | 37.715 | -5.214 | 61.017 | 1.00 21.50 |
| ATOM | 3958 | CB | VAL | B | 460 | 38.029 | -6.674 | 61.372 | 1.00 21.30 |
| ATOM | 3959 | CG1 | VAL | B | 460 | 36.820 | -7.524 | 61.077 | 1.00 22.78 |
| ATOM | 3960 | CG2 | VAL | B | 460 | 39.219 | -7.175 | 60.571 | 1.00 21.29 |
| ATOM | 3961 | C | VAL | B | 460 | 39.005 | -4.401 | 61.087 | 1.00 21.83 |
| ATOM | 3962 | O | VAL | B | 460 | 39.522 | -3.961 | 60.059 | 1.00 19.47 |
| ATOM | 3963 | N | ARG | B | 461 | 39.497 | -4.184 | 62.303 | 1.00 22.80 |
| ATOM | 3964 | CA | ARG | B | 461 | 40.734 | -3.436 | 62.534 | 1.00 24.89 |
| ATOM | 3965 | CB | ARG | B | 461 | 40.986 | -3.325 | 64.041 | 1.00 25.63 |
| ATOM | 3966 | CG | ARG | B | 461 | 42.109 | -2.421 | 64.459 | 1.00 28.55 |
| ATOM | 3967 | CD | ARG | B | 461 | 42.231 | -2.382 | 65.981 | 1.00 35.37 |
| ATOM | 3968 | NE | ARG | B | 461 | 42.683 | -3.659 | 66.526 | 1.00 41.66 |
| ATOM | 3969 | CZ | ARG | B | 461 | 43.903 | -4.173 | 66.338 | 1.00 46.26 |
| ATOM | 3970 | NH1 | ARG | B | 461 | 44.823 | -3.517 | 65.629 | 1.00 46.65 |
| ATOM | 3971 | NH2 | ARG | B | 461 | 44.182 | -5.395 | 66.778 | 1.00 48.77 |
| ATOM | 3972 | C | ARG | B | 461 | 41.930 | -4.112 | 61.820 | 1.00 27.22 |
| ATOM | 3973 | O | ARG | B | 461 | 42.249 | -5.287 | 62.064 | 1.00 26.47 |
| ATOM | 3974 | N | PRO | B | 462 | 42.576 | -3.386 | 60.884 | 1.00 28.69 |
| ATOM | 3975 | CD | PRO | B | 462 | 42.264 | -2.021 | 60.410 | 1.00 27.59 |
| ATOM | 3976 | CA | PRO | B | 462 | 43.718 | -3.951 | 60.157 | 1.00 29.80 |
| ATOM | 3977 | CB | PRO | B | 462 | 44.091 | -2.828 | 59.177 | 1.00 29.53 |
| ATOM | 3978 | CG | PRO | B | 462 | 42.800 | -2.035 | 59.007 | 1.00 27.17 |
| ATOM | 3979 | C | PRO | B | 462 | 44.875 | -4.246 | 61.097 | 1.00 32.31 |
| ATOM | 3980 | O | PRO | B | 462 | 45.002 | -3.628 | 62.157 | 1.00 31.39 |
| ATOM | 3981 | N | ASP | B | 463 | 45.719 | -5.196 | 60.712 | 1.00 35.90 |
| ATOM | 3982 | CA | ASP | B | 463 | 46.878 | -5.516 | 61.530 | 1.00 38.76 |
| ATOM | 3983 | CB | ASP | B | 463 | 47.670 | -6.682 | 60.935 | 1.00 40.30 |
| ATOM | 3984 | CG | ASP | B | 463 | 46.927 | -7.991 | 61.025 | 1.00 42.08 |
| ATOM | 3985 | OD1 | ASP | B | 463 | 46.291 | -8.243 | 62.071 | 1.00 41.92 |
| ATOM | 3986 | OD2 | ASP | B | 463 | 46.982 | -8.767 | 60.045 | 1.00 44.48 |
| ATOM | 3987 | C | ASP | B | 463 | 47.768 | -4.288 | 61.610 | 1.00 39.67 |
| ATOM | 3988 | O | ASP | B | 463 | 47.986 | -3.589 | 60.601 | 1.00 39.94 |
| ATOM | 3989 | N | ASN | B | 464 | 48.242 | -4.030 | 62.825 | 1.00 40.75 |
| ATOM | 3990 | CA | ASN | B | 464 | 49.125 | -2.914 | 63.136 | 1.00 41.67 |
| ATOM | 3991 | CB | ASN | B | 464 | 50.426 | -3.013 | 62.330 | 1.00 45.55 |
| ATOM | 3992 | CG | ASN | B | 464 | 51.338 | -4.138 | 62.829 | 1.00 49.49 |
| ATOM | 3993 | OD1 | ASN | B | 464 | 51.868 | -4.080 | 63.952 | 1.00 50.83 |
| ATOM | 3994 | ND2 | ASN | B | 464 | 51.510 | -5.173 | 62.005 | 1.00 50.35 |
| ATOM | 3995 | C | ASN | B | 464 | 48.456 | -1.565 | 62.935 | 1.00 40.76 |
| ATOM | 3996 | O | ASN | B | 464 | 49.002 | -0.675 | 62.277 | 1.00 41.27 |
| ATOM | 3997 | N | CYS | B | 465 | 47.281 | -1.421 | 63.545 | 1.00 37.52 |
| ATOM | 3998 | CA | CYS | B | 465 | 46.488 | -0.202 | 63.473 | 1.00 34.14 |
| ATOM | 3999 | CB | CYS | B | 465 | 45.301 | -0.422 | 62.524 | 1.00 33.01 |

Figure 10

| ATOM | 4000 | SG  | CYS | B | 465 | 44.051 | 0.904  | 62.494 | 1.00 | 29.34 |
| ---- | ---- | --- | --- | - | --- | ------ | ------ | ------ | ---- | ----- |
| ATOM | 4001 | C   | CYS | B | 465 | 45.978 | 0.110  | 64.878 | 1.00 | 33.48 |
| ATOM | 4002 | O   | CYS | B | 465 | 45.327 | -0.731 | 65.495 | 1.00 | 33.73 |
| ATOM | 4003 | N   | PRO | B | 466 | 46.305 | 1.300  | 65.428 | 1.00 | 32.50 |
| ATOM | 4004 | CD  | PRO | B | 466 | 47.186 | 2.339  | 64.864 | 1.00 | 31.28 |
| ATOM | 4005 | CA  | PRO | B | 466 | 45.851 | 1.679  | 66.779 | 1.00 | 31.72 |
| ATOM | 4006 | CB  | PRO | B | 466 | 46.340 | 3.122  | 66.909 | 1.00 | 30.19 |
| ATOM | 4007 | CG  | PRO | B | 466 | 47.591 | 3.117  | 66.108 | 1.00 | 30.60 |
| ATOM | 4008 | C   | PRO | B | 466 | 44.324 | 1.608  | 66.886 | 1.00 | 32.73 |
| ATOM | 4009 | O   | PRO | B | 466 | 43.634 | 1.836  | 65.892 | 1.00 | 34.82 |
| ATOM | 4010 | N   | GLU | B | 467 | 43.790 | 1.287  | 68.066 | 1.00 | 31.65 |
| ATOM | 4011 | CA  | GLU | B | 467 | 42.342 | 1.202  | 68.217 | 1.00 | 30.08 |
| ATOM | 4012 | CB  | GLU | B | 467 | 41.950 | 0.615  | 69.571 | 1.00 | 31.59 |
| ATOM | 4013 | CG  | GLU | B | 467 | 41.304 | -0.781 | 69.478 | 1.00 | 35.33 |
| ATOM | 4014 | CD  | GLU | B | 467 | 39.920 | -0.805 | 68.792 | 1.00 | 36.63 |
| ATOM | 4015 | OE1 | GLU | B | 467 | 39.722 | -1.663 | 67.894 | 1.00 | 37.62 |
| ATOM | 4016 | OE2 | GLU | B | 467 | 39.028 | 0.002  | 69.163 | 1.00 | 35.62 |
| ATOM | 4017 | C   | GLU | B | 467 | 41.653 | 2.543  | 67.996 | 1.00 | 28.48 |
| ATOM | 4018 | O   | GLU | B | 467 | 40.557 | 2.595  | 67.449 | 1.00 | 27.69 |
| ATOM | 4019 | N   | GLU | B | 468 | 42.312 | 3.629  | 68.386 | 1.00 | 28.25 |
| ATOM | 4020 | CA  | GLU | B | 468 | 41.746 | 4.970  | 68.199 | 1.00 | 29.16 |
| ATOM | 4021 | CB  | GLU | B | 468 | 42.597 | 6.052  | 68.883 | 1.00 | 32.73 |
| ATOM | 4022 | CG  | GLU | B | 468 | 42.841 | 5.840  | 70.375 | 1.00 | 38.92 |
| ATOM | 4023 | CD  | GLU | B | 468 | 43.794 | 4.658  | 70.658 | 1.00 | 44.21 |
| ATOM | 4024 | OE1 | GLU | B | 468 | 44.855 | 4.558  | 69.979 | 1.00 | 42.47 |
| ATOM | 4025 | OE2 | GLU | B | 468 | 43.470 | 3.823  | 71.552 | 1.00 | 47.31 |
| ATOM | 4026 | C   | GLU | B | 468 | 41.633 | 5.293  | 66.713 | 1.00 | 27.49 |
| ATOM | 4027 | O   | GLU | B | 468 | 40.701 | 5.972  | 66.299 | 1.00 | 27.47 |
| ATOM | 4028 | N   | LEU | B | 469 | 42.607 | 4.836  | 65.926 | 1.00 | 25.61 |
| ATOM | 4029 | CA  | LEU | B | 469 | 42.590 | 5.065  | 64.493 | 1.00 | 24.16 |
| ATOM | 4030 | CB  | LEU | B | 469 | 43.923 | 4.672  | 63.843 | 1.00 | 23.57 |
| ATOM | 4031 | CG  | LEU | B | 469 | 44.077 | 4.892  | 62.329 | 1.00 | 23.37 |
| ATOM | 4032 | CD1 | LEU | B | 469 | 43.733 | 6.307  | 61.939 | 1.00 | 24.15 |
| ATOM | 4033 | CD2 | LEU | B | 469 | 45.489 | 4.592  | 61.914 | 1.00 | 24.56 |
| ATOM | 4034 | C   | LEU | B | 469 | 41.439 | 4.278  | 63.881 | 1.00 | 23.65 |
| ATOM | 4035 | O   | LEU | B | 469 | 40.701 | 4.816  | 63.053 | 1.00 | 24.23 |
| ATOM | 4036 | N   | TYR | B | 470 | 41.241 | 3.038  | 64.329 | 1.00 | 22.27 |
| ATOM | 4037 | CA  | TYR | B | 470 | 40.149 | 2.220  | 63.805 | 1.00 | 22.11 |
| ATOM | 4038 | CB  | TYR | B | 470 | 40.176 | 0.807  | 64.383 | 1.00 | 21.05 |
| ATOM | 4039 | CG  | TYR | B | 470 | 39.052 | -0.084 | 63.861 | 1.00 | 20.50 |
| ATOM | 4040 | CD1 | TYR | B | 470 | 38.908 | -0.359 | 62.492 | 1.00 | 16.74 |
| ATOM | 4041 | CE1 | TYR | B | 470 | 37.884 | -1.193 | 62.027 | 1.00 | 17.75 |
| ATOM | 4042 | CD2 | TYR | B | 470 | 38.143 | -0.662 | 64.744 | 1.00 | 20.46 |
| ATOM | 4043 | CE2 | TYR | B | 470 | 37.118 | -1.495 | 64.285 | 1.00 | 18.92 |
| ATOM | 4044 | CZ  | TYR | B | 470 | 36.991 | -1.752 | 62.935 | 1.00 | 18.62 |
| ATOM | 4045 | OH  | TYR | B | 470 | 35.943 | -2.531 | 62.512 | 1.00 | 16.80 |
| ATOM | 4046 | C   | TYR | B | 470 | 38.790 | 2.851  | 64.076 | 1.00 | 21.58 |
| ATOM | 4047 | O   | TYR | B | 470 | 37.898 | 2.819  | 63.221 | 1.00 | 22.16 |
| ATOM | 4048 | N   | GLN | B | 471 | 38.633 | 3.408  | 65.272 | 1.00 | 20.55 |
| ATOM | 4049 | CA  | GLN | B | 471 | 37.390 | 4.066  | 65.641 | 1.00 | 20.94 |
| ATOM | 4050 | CB  | GLN | B | 471 | 37.352 | 4.327  | 67.149 | 1.00 | 20.24 |
| ATOM | 4051 | CG  | GLN | B | 471 | 37.333 | 3.035  | 67.998 | 1.00 | 22.01 |
| ATOM | 4052 | CD  | GLN | B | 471 | 36.214 | 2.061  | 67.605 | 1.00 | 23.04 |
| ATOM | 4053 | OE1 | GLN | B | 471 | 35.093 | 2.465  | 67.289 | 1.00 | 24.47 |
| ATOM | 4054 | NE2 | GLN | B | 471 | 36.529 | 0.770  | 67.607 | 1.00 | 23.15 |
| ATOM | 4055 | C   | GLN | B | 471 | 37.178 | 5.354  | 64.817 | 1.00 | 20.48 |
| ATOM | 4056 | O   | GLN | B | 471 | 36.046 | 5.819  | 64.631 | 1.00 | 19.16 |
| ATOM | 4057 | N   | LEU | B | 472 | 38.280 | 5.907  | 64.311 | 1.00 | 21.02 |
| ATOM | 4058 | CA  | LEU | B | 472 | 38.231 | 7.099  | 63.472 | 1.00 | 20.88 |

Figure 10

| | | | | | | | | |
|---|---|---|---|---|---|---|---|---|
| ATOM | 4059 | CB | LEU | B | 472 | 39.629 | 7.683 | 63.305 | 1.00 | 21.87 |
| ATOM | 4060 | CG | LEU | B | 472 | 39.756 | 9.205 | 63.228 | 1.00 | 25.39 |
| ATOM | 4061 | CD1 | LEU | B | 472 | 39.227 | 9.845 | 64.502 | 1.00 | 25.84 |
| ATOM | 4062 | CD2 | LEU | B | 472 | 41.228 | 9.565 | 63.047 | 1.00 | 27.21 |
| ATOM | 4063 | C | LEU | B | 472 | 37.688 | 6.617 | 62.132 | 1.00 | 19.85 |
| ATOM | 4064 | O | LEU | B | 472 | 36.798 | 7.243 | 61.560 | 1.00 | 21.86 |
| ATOM | 4065 | N | MET | B | 473 | 38.202 | 5.479 | 61.667 | 1.00 | 17.81 |
| ATOM | 4066 | CA | MET | B | 473 | 37.764 | 4.864 | 60.427 | 1.00 | 16.37 |
| ATOM | 4067 | CB | MET | B | 473 | 38.515 | 3.561 | 60.194 | 1.00 | 16.12 |
| ATOM | 4068 | CG | MET | B | 473 | 39.932 | 3.662 | 59.722 | 1.00 | 14.40 |
| ATOM | 4069 | SD | MET | B | 473 | 40.667 | 2.024 | 59.939 | 1.00 | 16.54 |
| ATOM | 4070 | CE | MET | B | 473 | 42.394 | 2.355 | 59.530 | 1.00 | 14.92 |
| ATOM | 4071 | C | MET | B | 473 | 36.268 | 4.535 | 60.487 | 1.00 | 16.02 |
| ATOM | 4072 | O | MET | B | 473 | 35.532 | 4.762 | 59.520 | 1.00 | 14.95 |
| ATOM | 4073 | N | ARG | B | 474 | 35.833 | 3.983 | 61.619 | 1.00 | 16.32 |
| ATOM | 4074 | CA | ARG | B | 474 | 34.432 | 3.610 | 61.807 | 1.00 | 16.26 |
| ATOM | 4075 | CB | ARG | B | 474 | 34.230 | 2.865 | 63.143 | 1.00 | 17.91 |
| ATOM | 4076 | CG | ARG | B | 474 | 34.937 | 1.502 | 63.213 | 1.00 | 19.60 |
| ATOM | 4077 | CD | ARG | B | 474 | 34.486 | 0.553 | 62.084 | 1.00 | 20.87 |
| ATOM | 4078 | NE | ARG | B | 474 | 33.055 | 0.265 | 62.178 | 1.00 | 23.02 |
| ATOM | 4079 | CZ | ARG | B | 474 | 32.533 | -0.848 | 62.686 | 1.00 | 24.04 |
| ATOM | 4080 | NH1 | ARG | B | 474 | 33.319 | -1.819 | 63.144 | 1.00 | 22.49 |
| ATOM | 4081 | NH2 | ARG | B | 474 | 31.213 | -0.966 | 62.774 | 1.00 | 24.53 |
| ATOM | 4082 | C | ARG | B | 474 | 33.517 | 4.818 | 61.722 | 1.00 | 15.87 |
| ATOM | 4083 | O | ARG | B | 474 | 32.380 | 4.702 | 61.278 | 1.00 | 15.77 |
| ATOM | 4084 | N | LEU | B | 475 | 34.021 | 5.977 | 62.140 | 1.00 | 16.10 |
| ATOM | 4085 | CA | LEU | B | 475 | 33.260 | 7.226 | 62.089 | 1.00 | 17.19 |
| ATOM | 4086 | CB | LEU | B | 475 | 33.956 | 8.324 | 62.888 | 1.00 | 18.56 |
| ATOM | 4087 | CG | LEU | B | 475 | 33.761 | 8.297 | 64.400 | 1.00 | 20.75 |
| ATOM | 4088 | CD1 | LEU | B | 475 | 34.613 | 9.396 | 65.034 | 1.00 | 19.90 |
| ATOM | 4089 | CD2 | LEU | B | 475 | 32.272 | 8.469 | 64.722 | 1.00 | 20.43 |
| ATOM | 4090 | C | LEU | B | 475 | 33.109 | 7.682 | 60.653 | 1.00 | 16.74 |
| ATOM | 4091 | O | LEU | B | 475 | 32.097 | 8.250 | 60.286 | 1.00 | 17.62 |
| ATOM | 4092 | N | CYS | B | 476 | 34.139 | 7.437 | 59.852 | 1.00 | 17.80 |
| ATOM | 4093 | CA | CYS | B | 476 | 34.142 | 7.786 | 58.433 | 1.00 | 17.15 |
| ATOM | 4094 | CB | CYS | B | 476 | 35.568 | 7.636 | 57.851 | 1.00 | 16.14 |
| ATOM | 4095 | SG | CYS | B | 476 | 36.895 | 8.747 | 58.540 | 1.00 | 16.99 |
| ATOM | 4096 | C | CYS | B | 476 | 33.158 | 6.877 | 57.668 | 1.00 | 16.85 |
| ATOM | 4097 | O | CYS | B | 476 | 32.685 | 7.235 | 56.588 | 1.00 | 16.60 |
| ATOM | 4098 | N | TRP | B | 477 | 32.862 | 5.703 | 58.237 | 1.00 | 16.74 |
| ATOM | 4099 | CA | TRP | B | 477 | 31.959 | 4.726 | 57.620 | 1.00 | 16.42 |
| ATOM | 4100 | CB | TRP | B | 477 | 32.558 | 3.300 | 57.671 | 1.00 | 14.68 |
| ATOM | 4101 | CG | TRP | B | 477 | 33.949 | 3.179 | 57.102 | 1.00 | 13.36 |
| ATOM | 4102 | CD2 | TRP | B | 477 | 34.963 | 2.234 | 57.488 | 1.00 | 13.02 |
| ATOM | 4103 | CE2 | TRP | B | 477 | 36.111 | 2.519 | 56.717 | 1.00 | 12.90 |
| ATOM | 4104 | CE3 | TRP | B | 477 | 35.013 | 1.178 | 58.407 | 1.00 | 13.75 |
| ATOM | 4105 | CD1 | TRP | B | 477 | 34.510 | 3.965 | 56.137 | 1.00 | 12.17 |
| ATOM | 4106 | NE1 | TRP | B | 477 | 35.800 | 3.579 | 55.905 | 1.00 | 12.74 |
| ATOM | 4107 | CZ2 | TRP | B | 477 | 37.303 | 1.782 | 56.836 | 1.00 | 12.42 |
| ATOM | 4108 | CZ3 | TRP | B | 477 | 36.192 | 0.449 | 58.525 | 1.00 | 13.09 |
| ATOM | 4109 | CH2 | TRP | B | 477 | 37.321 | 0.758 | 57.742 | 1.00 | 13.47 |
| ATOM | 4110 | C | TRP | B | 477 | 30.566 | 4.703 | 58.258 | 1.00 | 16.66 |
| ATOM | 4111 | O | TRP | B | 477 | 29.874 | 3.674 | 58.206 | 1.00 | 17.24 |
| ATOM | 4112 | N | LYS | B | 478 | 30.147 | 5.807 | 58.869 | 1.00 | 14.64 |
| ATOM | 4113 | CA | LYS | B | 478 | 28.827 | 5.806 | 59.456 | 1.00 | 14.87 |
| ATOM | 4114 | CB | LYS | B | 478 | 28.549 | 7.073 | 60.267 | 1.00 | 14.76 |
| ATOM | 4115 | CG | LYS | B | 478 | 29.328 | 7.182 | 61.578 | 1.00 | 16.65 |
| ATOM | 4116 | CD | LYS | B | 478 | 28.987 | 6.115 | 62.596 | 1.00 | 17.12 |
| ATOM | 4117 | CE | LYS | B | 478 | 27.574 | 6.245 | 63.058 | 1.00 | 21.46 |

Figure 10

```
ATOM   4118  NZ   LYS B 478      27.159   5.060  63.854  1.00 24.73
ATOM   4119  C    LYS B 478      27.903   5.710  58.277  1.00 15.59
ATOM   4120  O    LYS B 478      28.172   6.297  57.240  1.00 16.20
ATOM   4121  N    GLU B 479      26.850   4.915  58.411  1.00 16.53
ATOM   4122  CA   GLU B 479      25.894   4.739  57.332  1.00 17.85
ATOM   4123  CB   GLU B 479      24.720   3.872  57.789  1.00 16.00
ATOM   4124  CG   GLU B 479      23.790   3.453  56.654  1.00 16.68
ATOM   4125  CD   GLU B 479      24.480   2.569  55.615  1.00 20.30
ATOM   4126  OE1  GLU B 479      25.419   1.824  55.963  1.00 20.75
ATOM   4127  OE2  GLU B 479      24.080   2.609  54.437  1.00 21.49
ATOM   4128  C    GLU B 479      25.404   6.092  56.851  1.00 18.25
ATOM   4129  O    GLU B 479      25.574   6.430  55.687  1.00 19.57
ATOM   4130  N    ARG B 480      24.844   6.881  57.761  1.00 19.12
ATOM   4131  CA   ARG B 480      24.344   8.209  57.419  1.00 19.83
ATOM   4132  CB   ARG B 480      23.437   8.711  58.519  1.00 23.23
ATOM   4133  CG   ARG B 480      22.175   7.934  58.720  1.00 27.34
ATOM   4134  CD   ARG B 480      21.590   8.463  59.985  1.00 34.14
ATOM   4135  NE   ARG B 480      20.243   7.991  60.249  1.00 42.99
ATOM   4136  CZ   ARG B 480      19.728   7.879  61.472  1.00 45.74
ATOM   4137  NH1  ARG B 480      20.466   8.195  62.542  1.00 46.42
ATOM   4138  NH2  ARG B 480      18.468   7.479  61.618  1.00 46.62
ATOM   4139  C    ARG B 480      25.475   9.211  57.234  1.00 18.26
ATOM   4140  O    ARG B 480      26.309   9.364  58.109  1.00 19.76
ATOM   4141  N    PRO B 481      25.503   9.927  56.094  1.00 17.26
ATOM   4142  CD   PRO B 481      24.545   9.837  54.976  1.00 15.35
ATOM   4143  CA   PRO B 481      26.537  10.923  55.796  1.00 15.71
ATOM   4144  CB   PRO B 481      26.001  11.590  54.529  1.00 14.01
ATOM   4145  CG   PRO B 481      25.295  10.494  53.861  1.00 14.55
ATOM   4146  C    PRO B 481      26.732  11.955  56.902  1.00 15.61
ATOM   4147  O    PRO B 481      27.856  12.285  57.236  1.00 15.62
ATOM   4148  N    GLU B 482      25.626  12.448  57.463  1.00 16.65
ATOM   4149  CA   GLU B 482      25.637  13.461  58.523  1.00 16.81
ATOM   4150  CB   GLU B 482      24.189  13.864  58.853  1.00 17.18
ATOM   4151  CG   GLU B 482      23.382  12.805  59.632  1.00 20.95
ATOM   4152  CD   GLU B 482      22.320  12.051  58.816  1.00 20.82
ATOM   4153  OE1  GLU B 482      22.514  11.810  57.609  1.00 21.26
ATOM   4154  OE2  GLU B 482      21.281  11.670  59.412  1.00 24.62
ATOM   4155  C    GLU B 482      26.388  13.022  59.796  1.00 17.54
ATOM   4156  O    GLU B 482      26.904  13.851  60.562  1.00 17.99
ATOM   4157  N    ASP B 483      26.469  11.709  60.010  1.00 17.84
ATOM   4158  CA   ASP B 483      27.156  11.160  61.175  1.00 16.45
ATOM   4159  CB   ASP B 483      26.577   9.805  61.564  1.00 16.44
ATOM   4160  CG   ASP B 483      25.144   9.907  62.011  1.00 16.40
ATOM   4161  OD1  ASP B 483      24.782  10.941  62.591  1.00 17.95
ATOM   4162  OD2  ASP B 483      24.366   8.978  61.771  1.00 17.36
ATOM   4163  C    ASP B 483      28.632  11.041  60.991  1.00 15.53
ATOM   4164  O    ASP B 483      29.324  10.645  61.928  1.00 15.99
ATOM   4165  N    ARG B 484      29.110  11.377  59.791  1.00 14.42
ATOM   4166  CA   ARG B 484      30.540  11.321  59.480  1.00 14.65
ATOM   4167  CB   ARG B 484      30.763  10.982  58.006  1.00 13.11
ATOM   4168  CG   ARG B 484      30.123   9.689  57.600  1.00 11.87
ATOM   4169  CD   ARG B 484      30.265   9.422  56.113  1.00 13.72
ATOM   4170  NE   ARG B 484      29.327   8.379  55.693  1.00 15.01
ATOM   4171  CZ   ARG B 484      28.817   8.243  54.469  1.00 13.78
ATOM   4172  NH1  ARG B 484      29.160   9.080  53.506  1.00 12.19
ATOM   4173  NH2  ARG B 484      27.920   7.296  54.227  1.00 12.92
ATOM   4174  C    ARG B 484      31.224  12.646  59.826  1.00 15.15
ATOM   4175  O    ARG B 484      30.662  13.721  59.607  1.00 14.30
ATOM   4176  N    PRO B 485      32.465  12.582  60.339  1.00 15.57
```

Figure 10

| | | | | | | | | | |
|---|---|---|---|---|---|---|---|---|---|
| ATOM | 4177 | CD | PRO | B | 485 | 33.328 | 11.394 | 60.364 | 1.00 13.89 |
| ATOM | 4178 | CA | PRO | B | 485 | 33.216 | 13.780 | 60.715 | 1.00 15.89 |
| ATOM | 4179 | CB | PRO | B | 485 | 34.528 | 13.216 | 61.282 | 1.00 17.12 |
| ATOM | 4180 | CG | PRO | B | 485 | 34.300 | 11.746 | 61.414 | 1.00 17.22 |
| ATOM | 4181 | C | PRO | B | 485 | 33.539 | 14.686 | 59.536 | 1.00 17.03 |
| ATOM | 4182 | O | PRO | B | 485 | 33.500 | 14.288 | 58.377 | 1.00 17.93 |
| ATOM | 4183 | N | THR | B | 486 | 33.916 | 15.907 | 59.853 | 1.00 16.55 |
| ATOM | 4184 | CA | THR | B | 486 | 34.323 | 16.846 | 58.837 | 1.00 15.80 |
| ATOM | 4185 | CB | THR | B | 486 | 34.131 | 18.302 | 59.320 | 1.00 14.24 |
| ATOM | 4186 | OG1 | THR | B | 486 | 34.875 | 18.490 | 60.531 | 1.00 16.13 |
| ATOM | 4187 | CG2 | THR | B | 486 | 32.656 | 18.607 | 59.564 | 1.00 11.81 |
| ATOM | 4188 | C | THR | B | 486 | 35.829 | 16.596 | 58.681 | 1.00 15.57 |
| ATOM | 4189 | O | THR | B | 486 | 36.476 | 16.113 | 59.602 | 1.00 15.66 |
| ATOM | 4190 | N | PHE | B | 487 | 36.381 | 16.929 | 57.522 | 1.00 16.60 |
| ATOM | 4191 | CA | PHE | B | 487 | 37.813 | 16.779 | 57.300 | 1.00 18.21 |
| ATOM | 4192 | CB | PHE | B | 487 | 38.162 | 17.050 | 55.842 | 1.00 16.35 |
| ATOM | 4193 | CG | PHE | B | 487 | 37.894 | 15.891 | 54.942 | 1.00 15.48 |
| ATOM | 4194 | CD1 | PHE | B | 487 | 38.647 | 14.726 | 55.056 | 1.00 12.78 |
| ATOM | 4195 | CD2 | PHE | B | 487 | 36.890 | 15.955 | 53.980 | 1.00 15.07 |
| ATOM | 4196 | CE1 | PHE | B | 487 | 38.406 | 13.644 | 54.229 | 1.00 12.01 |
| ATOM | 4197 | CE2 | PHE | B | 487 | 36.643 | 14.861 | 53.138 | 1.00 12.82 |
| ATOM | 4198 | CZ | PHE | B | 487 | 37.405 | 13.709 | 53.268 | 1.00 9.76 |
| ATOM | 4199 | C | PHE | B | 487 | 38.557 | 17.744 | 58.210 | 1.00 20.26 |
| ATOM | 4200 | O | PHE | B | 487 | 39.724 | 17.528 | 58.525 | 1.00 20.95 |
| ATOM | 4201 | N | ASP | B | 488 | 37.867 | 18.808 | 58.629 | 1.00 22.81 |
| ATOM | 4202 | CA | ASP | B | 488 | 38.423 | 19.796 | 59.556 | 1.00 24.76 |
| ATOM | 4203 | CB | ASP | B | 488 | 37.433 | 20.961 | 59.722 | 1.00 28.25 |
| ATOM | 4204 | CG | ASP | B | 488 | 37.896 | 22.003 | 60.738 | 1.00 31.36 |
| ATOM | 4205 | OD1 | ASP | B | 488 | 39.090 | 22.368 | 60.748 | 1.00 34.01 |
| ATOM | 4206 | OD2 | ASP | B | 488 | 37.046 | 22.465 | 61.528 | 1.00 32.45 |
| ATOM | 4207 | C | ASP | B | 488 | 38.682 | 19.081 | 60.903 | 1.00 24.34 |
| ATOM | 4208 | O | ASP | B | 488 | 39.700 | 19.298 | 61.549 | 1.00 24.43 |
| ATOM | 4209 | N | TYR | B | 489 | 37.771 | 18.192 | 61.293 | 1.00 23.76 |
| ATOM | 4210 | CA | TYR | B | 489 | 37.942 | 17.432 | 62.522 | 1.00 22.83 |
| ATOM | 4211 | CB | TYR | B | 489 | 36.639 | 16.753 | 62.935 | 1.00 21.05 |
| ATOM | 4212 | CG | TYR | B | 489 | 36.851 | 15.721 | 64.019 | 1.00 19.09 |
| ATOM | 4213 | CD1 | TYR | B | 489 | 37.115 | 16.106 | 65.338 | 1.00 20.63 |
| ATOM | 4214 | CE1 | TYR | B | 489 | 37.338 | 15.159 | 66.340 | 1.00 19.77 |
| ATOM | 4215 | CD2 | TYR | B | 489 | 36.813 | 14.359 | 63.722 | 1.00 19.11 |
| ATOM | 4216 | CE2 | TYR | B | 489 | 37.034 | 13.396 | 64.703 | 1.00 18.30 |
| ATOM | 4217 | CZ | TYR | B | 489 | 37.297 | 13.798 | 66.015 | 1.00 22.19 |
| ATOM | 4218 | OH | TYR | B | 489 | 37.534 | 12.853 | 66.999 | 1.00 21.09 |
| ATOM | 4219 | C | TYR | B | 489 | 39.016 | 16.362 | 62.309 | 1.00 23.70 |
| ATOM | 4220 | O | TYR | B | 489 | 39.893 | 16.185 | 63.159 | 1.00 23.74 |
| ATOM | 4221 | N | LEU | B | 490 | 38.949 | 15.665 | 61.170 | 1.00 22.96 |
| ATOM | 4222 | CA | LEU | B | 490 | 39.911 | 14.615 | 60.847 | 1.00 21.65 |
| ATOM | 4223 | CB | LEU | B | 490 | 39.545 | 13.944 | 59.525 | 1.00 20.91 |
| ATOM | 4224 | CG | LEU | B | 490 | 38.320 | 13.029 | 59.577 | 1.00 20.54 |
| ATOM | 4225 | CD1 | LEU | B | 490 | 37.910 | 12.621 | 58.155 | 1.00 17.74 |
| ATOM | 4226 | CD2 | LEU | B | 490 | 38.613 | 11.812 | 60.443 | 1.00 18.48 |
| ATOM | 4227 | C | LEU | B | 490 | 41.362 | 15.106 | 60.832 | 1.00 22.12 |
| ATOM | 4228 | O | LEU | B | 490 | 42.258 | 14.401 | 61.288 | 1.00 20.34 |
| ATOM | 4229 | N | ARG | B | 491 | 41.597 | 16.307 | 60.309 | 1.00 24.26 |
| ATOM | 4230 | CA | ARG | B | 491 | 42.943 | 16.888 | 60.283 | 1.00 27.09 |
| ATOM | 4231 | CB | ARG | B | 491 | 42.946 | 18.183 | 59.481 | 1.00 30.17 |
| ATOM | 4232 | CG | ARG | B | 491 | 44.222 | 18.989 | 59.653 | 1.00 36.39 |
| ATOM | 4233 | CD | ARG | B | 491 | 44.034 | 20.429 | 59.227 | 1.00 42.21 |
| ATOM | 4234 | NE | ARG | B | 491 | 42.886 | 21.055 | 59.893 | 1.00 47.62 |
| ATOM | 4235 | CZ | ARG | B | 491 | 42.837 | 21.375 | 61.190 | 1.00 50.08 |

Figure 10

| | | | | | | | | |
|---|---|---|---|---|---|---|---|---|
| ATOM | 4236 | NH1 | ARG B 491 | 43.877 | 21.133 | 61.994 | 1.00 | 49.64 |
| ATOM | 4237 | NH2 | ARG B 491 | 41.740 | 21.946 | 61.684 | 1.00 | 50.33 |
| ATOM | 4238 | C | ARG B 491 | 43.429 | 17.185 | 61.710 | 1.00 | 27.99 |
| ATOM | 4239 | O | ARG B 491 | 44.578 | 16.908 | 62.054 | 1.00 | 27.57 |
| ATOM | 4240 | N | SER B 492 | 42.543 | 17.759 | 62.524 | 1.00 | 28.89 |
| ATOM | 4241 | CA | SER B 492 | 42.845 | 18.089 | 63.920 | 1.00 | 28.99 |
| ATOM | 4242 | CB | SER B 492 | 41.631 | 18.710 | 64.603 | 1.00 | 28.87 |
| ATOM | 4243 | OG | SER B 492 | 41.571 | 20.098 | 64.349 | 1.00 | 34.11 |
| ATOM | 4244 | C | SER B 492 | 43.246 | 16.867 | 64.713 | 1.00 | 29.41 |
| ATOM | 4245 | O | SER B 492 | 44.299 | 16.847 | 65.348 | 1.00 | 28.96 |
| ATOM | 4246 | N | VAL B 493 | 42.396 | 15.845 | 64.665 | 1.00 | 30.48 |
| ATOM | 4247 | CA | VAL B 493 | 42.636 | 14.611 | 65.401 | 1.00 | 31.09 |
| ATOM | 4248 | CB | VAL B 493 | 41.311 | 13.748 | 65.537 | 1.00 | 29.94 |
| ATOM | 4249 | CG1 | VAL B 493 | 40.899 | 13.144 | 64.222 | 1.00 | 28.64 |
| ATOM | 4250 | CG2 | VAL B 493 | 41.467 | 12.673 | 66.595 | 1.00 | 30.73 |
| ATOM | 4251 | C | VAL B 493 | 43.857 | 13.809 | 64.904 | 1.00 | 31.77 |
| ATOM | 4252 | O | VAL B 493 | 44.596 | 13.232 | 65.716 | 1.00 | 31.64 |
| ATOM | 4253 | N | LEU B 494 | 44.145 | 13.886 | 63.604 | 1.00 | 32.61 |
| ATOM | 4254 | CA | LEU B 494 | 45.276 | 13.153 | 63.037 | 1.00 | 33.35 |
| ATOM | 4255 | CB | LEU B 494 | 45.060 | 12.886 | 61.546 | 1.00 | 32.08 |
| ATOM | 4256 | CG | LEU B 494 | 43.980 | 11.845 | 61.216 | 1.00 | 30.85 |
| ATOM | 4257 | CD1 | LEU B 494 | 43.702 | 11.818 | 59.724 | 1.00 | 28.55 |
| ATOM | 4258 | CD2 | LEU B 494 | 44.407 | 10.461 | 61.713 | 1.00 | 30.22 |
| ATOM | 4259 | C | LEU B 494 | 46.632 | 13.798 | 63.289 | 1.00 | 34.58 |
| ATOM | 4260 | O | LEU B 494 | 47.633 | 13.101 | 63.384 | 1.00 | 34.25 |
| ATOM | 4261 | N | GLU B 495 | 46.663 | 15.125 | 63.388 | 1.00 | 38.15 |
| ATOM | 4262 | CA | GLU B 495 | 47.902 | 15.855 | 63.659 | 1.00 | 42.45 |
| ATOM | 4263 | CB | GLU B 495 | 47.672 | 17.363 | 63.517 | 1.00 | 43.33 |
| ATOM | 4264 | CG | GLU B 495 | 48.037 | 17.925 | 62.155 | 1.00 | 46.75 |
| ATOM | 4265 | CD | GLU B 495 | 47.533 | 19.337 | 61.942 | 1.00 | 47.96 |
| ATOM | 4266 | OE1 | GLU B 495 | 47.309 | 20.051 | 62.953 | 1.00 | 48.32 |
| ATOM | 4267 | OE2 | GLU B 495 | 47.359 | 19.719 | 60.757 | 1.00 | 48.49 |
| ATOM | 4268 | C | GLU B 495 | 48.350 | 15.567 | 65.082 | 1.00 | 44.92 |
| ATOM | 4269 | O | GLU B 495 | 49.487 | 15.153 | 65.328 | 1.00 | 45.76 |
| ATOM | 4270 | N | ASP B 496 | 47.407 | 15.751 | 66.002 | 1.00 | 47.24 |
| ATOM | 4271 | CA | ASP B 496 | 47.615 | 15.560 | 67.430 | 1.00 | 49.31 |
| ATOM | 4272 | CB | ASP B 496 | 46.636 | 16.462 | 68.209 | 1.00 | 51.67 |
| ATOM | 4273 | CG | ASP B 496 | 46.765 | 17.956 | 67.833 | 1.00 | 54.75 |
| ATOM | 4274 | OD1 | ASP B 496 | 47.906 | 18.455 | 67.606 | 1.00 | 55.50 |
| ATOM | 4275 | OD2 | ASP B 496 | 45.715 | 18.640 | 67.776 | 1.00 | 55.96 |
| ATOM | 4276 | C | ASP B 496 | 47.448 | 14.118 | 67.892 | 1.00 | 49.51 |
| ATOM | 4277 | O | ASP B 496 | 47.208 | 13.879 | 69.072 | 1.00 | 49.33 |
| ATOM | 4278 | N | PHE B 497 | 47.588 | 13.157 | 66.983 | 1.00 | 50.47 |
| ATOM | 4279 | CA | PHE B 497 | 47.417 | 11.756 | 67.350 | 1.00 | 51.89 |
| ATOM | 4280 | CB | PHE B 497 | 47.436 | 10.863 | 66.116 | 1.00 | 49.93 |
| ATOM | 4281 | CG | PHE B 497 | 46.651 | 9.600 | 66.284 | 1.00 | 47.88 |
| ATOM | 4282 | CD1 | PHE B 497 | 45.291 | 9.573 | 66.007 | 1.00 | 46.31 |
| ATOM | 4283 | CD2 | PHE B 497 | 47.273 | 8.432 | 66.726 | 1.00 | 48.76 |
| ATOM | 4284 | CE1 | PHE B 497 | 44.561 | 8.410 | 66.164 | 1.00 | 45.79 |
| ATOM | 4285 | CE2 | PHE B 497 | 46.550 | 7.254 | 66.886 | 1.00 | 47.16 |
| ATOM | 4286 | CZ | PHE B 497 | 45.192 | 7.245 | 66.603 | 1.00 | 46.88 |
| ATOM | 4287 | C | PHE B 497 | 48.430 | 11.270 | 68.380 | 1.00 | 54.13 |
| ATOM | 4288 | O | PHE B 497 | 48.080 | 10.504 | 69.286 | 1.00 | 53.79 |
| ATOM | 4289 | N | PHE B 498 | 49.686 | 11.677 | 68.211 | 1.00 | 57.26 |
| ATOM | 4290 | CA | PHE B 498 | 50.771 | 11.332 | 69.143 | 1.00 | 59.91 |
| ATOM | 4291 | CB | PHE B 498 | 50.878 | 9.807 | 69.408 | 1.00 | 60.99 |
| ATOM | 4292 | CG | PHE B 498 | 51.006 | 8.946 | 68.161 | 1.00 | 60.96 |
| ATOM | 4293 | CD1 | PHE B 498 | 51.463 | 9.467 | 66.958 | 1.00 | 60.69 |
| ATOM | 4294 | CD2 | PHE B 498 | 50.681 | 7.589 | 68.217 | 1.00 | 60.43 |

Figure 10

| | | | | | | | | |
|---|---|---|---|---|---|---|---|---|
| ATOM | 4295 | CE1 | PHE | B | 498 | 51.588 | 8.653 | 65.836 | 1.00 61.55 |
| ATOM | 4296 | CE2 | PHE | B | 498 | 50.803 | 6.772 | 67.101 | 1.00 59.91 |
| ATOM | 4297 | CZ | PHE | B | 498 | 51.261 | 7.305 | 65.911 | 1.00 60.43 |
| ATOM | 4298 | C | PHE | B | 498 | 52.123 | 11.899 | 68.711 | 1.00 60.93 |
| ATOM | 4299 | O | PHE | B | 498 | 52.241 | 13.143 | 68.732 | 1.00 62.03 |
| ATOM | 4300 | N1 | LIG | B | 500 | 52.270 | 4.518 | 38.021 | 1.00 42.19 |
| ATOM | 4301 | C1 | LIG | B | 500 | 51.938 | 5.977 | 38.163 | 1.00 40.68 |
| ATOM | 4302 | C2 | LIG | B | 500 | 52.195 | 6.613 | 39.577 | 1.00 39.30 |
| ATOM | 4303 | C3 | LIG | B | 500 | 51.794 | 8.111 | 39.602 | 1.00 37.20 |
| ATOM | 4304 | C4 | LIG | B | 500 | 52.586 | 8.838 | 38.349 | 1.00 35.88 |
| ATOM | 4305 | C5 | LIG | B | 500 | 52.339 | 8.318 | 37.168 | 1.00 36.81 |
| ATOM | 4306 | C6 | LIG | B | 500 | 52.711 | 6.826 | 37.087 | 1.00 39.27 |
| ATOM | 4307 | N2 | LIG | B | 500 | 52.182 | 10.273 | 38.384 | 1.00 34.49 |
| ATOM | 4308 | N3 | LIG | B | 500 | 51.046 | 10.870 | 38.050 | 1.00 33.20 |
| ATOM | 4309 | C7 | LIG | B | 500 | 51.167 | 12.182 | 38.257 | 1.00 33.39 |
| ATOM | 4310 | C8 | LIG | B | 500 | 52.498 | 12.464 | 38.767 | 1.00 32.47 |
| ATOM | 4311 | C9 | LIG | B | 500. | 53.186 | 13.587 | 39.140 | 1.00 31.47 |
| ATOM | 4312 | N4 | LIG | B | 500 | 54.486 | 13.449 | 39.595 | 1.00 30.75 |
| ATOM | 4313 | C10 | LIG | B | 500 | 55.103 | 12.236 | 39.670 | 1.00 29.50 |
| ATOM | 4314 | N5 | LIG | B | 500 | 54.451 | 11.096 | 39.299 | 1.00 31.40 |
| ATOM | 4315 | C11 | LIG | B | 500 | 53.132 | 11.258 | 38.846 | 1.00 34.00 |
| ATOM | 4316 | N6 | LIG | B | 500 | 52.649 | 14.919 | 39.095 | 1.00 30.98 |
| ATOM | 4317 | C12 | LIG | B | 500 | 50.017 | 12.998 | 37.931 | 1.00 34.56 |
| ATOM | 4318 | C13 | LIG | B | 500 | 48.753 | 12.702 | 38.536 | 1.00 35.75 |
| ATOM | 4319 | C14 | LIG | B | 500 | 47.656 | 13.504 | 38.170 | 1.00 37.63 |
| ATOM | 4320 | C15 | LIG | B | 500 | 47.767 | 14.588 | 37.214 | 1.00 39.13 |
| ATOM | 4321 | C16 | LIG | B | 500 | 49.052 | 14.863 | 36.640 | 1.00 38.05 |
| ATOM | 4322 | C17 | LIG | B | 500 | 50.141 | 14.049 | 37.014 | 1.00 36.52 |
| ATOM | 4323 | C18 | LIG | B | 500 | 53.708 | 4.057 | 37.978 | 1.00 43.43 |
| ATOM | 4324 | C19 | LIG | B | 500 | 53.866 | 2.512 | 37.825 | 1.00 43.88 |
| ATOM | 4325 | N7 | LIG | B | 500 | 53.209 | 1.803 | 38.959 | 1.00 44.55 |
| ATOM | 4326 | C20 | LIG | B | 500 | 53.374 | 0.312 | 38.839 | 1.00 45.33 |
| ATOM | 4327 | C21 | LIG | B | 500 | 51.766 | 2.169 | 38.939 | 1.00 44.40 |
| ATOM | 4328 | C22 | LIG | B | 500 | 51.516 | 3.709 | 39.063 | 1.00 43.24 |
| ATOM | 4329 | O1 | LIG | B | 500 | 49.112 | 15.857 | 35.782 | 1.00 39.33 |
| ATOM | 4330 | C23 | LIG | B | 500 | 50.151 | 15.836 | 34.767 | 1.00 38.77 |
| ATOM | 4331 | C24 | LIG | B | 500 | 45.785 | 16.076 | 37.629 | 1.00 44.35 |
| ATOM | 4332 | O2 | LIG | B | 500 | 45.912 | 16.143 | 38.870 | 1.00 43.83 |
| ATOM | 4333 | N8 | LIG | B | 500 | 46.618 | 15.394 | 36.813 | 1.00 41.95 |
| ATOM | 4334 | C25 | LIG | B | 500 | 44.677 | 16.756 | 37.042 | 1.00 46.74 |
| ATOM | 4335 | C26 | LIG | B | 500 | 44.297 | 16.827 | 35.686 | 1.00 47.08 |
| ATOM | 4336 | N9 | LIG | B | 500 | 43.787 | 17.477 | 37.828 | 1.00 47.32 |
| ATOM | 4337 | C27 | LIG | B | 500 | 42.196 | 18.097 | 34.635 | 1.00 46.55 |
| ATOM | 4338 | C28 | LIG | B | 500 | 43.086 | 17.638 | 35.655 | 1.00 47.01 |
| ATOM | 4339 | C29 | LIG | B | 500 | 42.801 | 18.023 | 36.984 | 1.00 47.46 |
| ATOM | 4340 | C30 | LIG | B | 500 | 41.678 | 18.843 | 37.277 | 1.00 47.54 |
| ATOM | 4341 | C31 | LIG | B | 500 | 40.814 | 19.282 | 36.232 | 1.00 46.97 |
| ATOM | 4342 | C32 | LIG | B | 500 | 41.077 | 18.908 | 34.909 | 1.00 45.93 |
| ATOM | 4343 | OH2 | H2O | B | 600 | 33.793 | 1.181 | 50.891 | 1.00 20.24 |
| ATOM | 4344 | OH2 | H2O | B | 601 | 29.960 | 20.420 | 60.989 | 1.00 91.33 |
| ATOM | 4345 | OH2 | H2O | B | 602 | 27.307 | -0.745 | 59.672 | 1.00 12.63 |
| ATOM | 4346 | OH2 | H2O | B | 604 | 35.031 | 20.938 | 63.196 | 1.00 37.37 |
| ATOM | 4347 | OH2 | H2O | B | 605 | 22.864 | -2.057 | 58.036 | 1.00 35.55 |
| ATOM | 4348 | OH2 | H2O | B | 606 | 36.138 | 10.111 | 46.982 | 1.00 12.59 |
| ATOM | 4349 | OH2 | H2O | B | 607 | 24.995 | 6.613 | 60.512 | 1.00 23.88 |
| ATOM | 4350 | OH2 | H2O | B | 608 | 29.175 | 14.635 | 62.588 | 1.00 58.00 |
| ATOM | 4351 | OH2 | H2O | B | 609 | 27.730 | -7.262 | 58.159 | 1.00 20.46 |
| ATOM | 4352 | OH2 | H2O | B | 610 | 34.499 | -1.024 | 55.741 | 1.00 17.17 |
| ATOM | 4353 | OH2 | H2O | B | 611 | 33.946 | 4.904 | 65.987 | 1.00 20.20 |

Figure 10

```
ATOM   4354  OH2 H2O B 612      29.240   17.617   59.419  1.00 31.73
ATOM   4355  OH2 H2O B 613      28.125   -5.103   60.621  1.00 65.78
ATOM   4356  OH2 H2O B 614      38.160   13.671   41.119  1.00 16.99
ATOM   4357  OH2 H2O B 615      19.054   15.606   62.658  1.00 33.35
ATOM   4358  OH2 H2O B 616      26.862   16.724   60.311  1.00 29.17
ATOM   4359  OH2 H2O B 617      30.814   -6.159   60.504  1.00 73.25
ATOM   4360  OH2 H2O B 618      36.912   -1.351   43.986  1.00 26.94
ATOM   4361  OH2 H2O B 619      27.702   18.399   55.786  1.00 80.29
ATOM   4362  OH2 H2O B 620      29.626   -3.422   63.065  1.00 26.48
ATOM   4363  OH2 H2O B 621      58.421    9.386   39.508  1.00 54.04
ATOM   4364  OH2 H2O B 622      32.750   22.857   61.691  1.00 50.90
ATOM   4365  OH2 H2O B 623      24.788    0.035   58.117  1.00 35.56
ATOM   4366  OH2 H2O B 624      64.609   11.192   37.924  1.00 36.55
ATOM   4367  OH2 H2O B 625      48.821   18.285   58.373  1.00 34.98
ATOM   4368  OH2 H2O B 626      44.228    3.474   45.793  1.00 25.07
ATOM   4369  OH2 H2O B 627      32.125   17.194   56.113  1.00 20.36
ATOM   4370  OH2 H2O B 628      32.614    7.709   48.243  1.00 29.35
ATOM   4371  OH2 H2O B 630      37.086    8.659   67.633  1.00 61.82
ATOM   4372  OH2 H2O B 631      62.440   24.028   26.247  1.00 60.06
ATOM   4373  OH2 H2O B 632      33.894   -4.768   61.683  1.00 21.78
ATOM   4374  OH2 H2O B 633      45.907   10.668   40.702  1.00 37.35
ATOM   4375  OH2 H2O B 634      45.898   24.052   55.450  1.00 30.58
ATOM   4376  OH2 H2O B 635      27.224   11.753   50.259  1.00 24.01
ATOM   4377  OH2 H2O B 636      26.391   11.112   64.790  1.00 28.26
ATOM   4378  OH2 H2O B 638      20.509   15.091   65.545  1.00 36.61
ATOM   4379  OH2 H2O B 639      44.279   13.020   68.496  1.00 50.48
ATOM   4380  OH2 H2O B 640      26.666   -0.197   54.665  1.00 21.29
ATOM   4381  OH2 H2O B 641      25.906   17.042   57.339  1.00 16.69
ATOM   4382  OH2 H2O B 642      47.820   23.441   44.451  1.00 36.19
ATOM   4383  OH2 H2O B 643      54.784    0.225   26.798  1.00 84.90
ATOM   4384  OH2 H2O B 644      31.458    2.341   60.596  1.00 17.34
ATOM   4385  OH2 H2O B 645      24.238   -0.280   50.420  1.00 33.91
ATOM   4386  OH2 H2O B 646      57.093   21.328   19.178  1.00 67.79
ATOM   4387  OH2 H2O B 647      32.788  -12.619   53.683  1.00 47.14
ATOM   4388  OH2 H2O B 648      29.609   18.415   49.511  1.00 32.77
ATOM   4389  OH2 H2O B 649      15.385   17.626   62.438  1.00 71.58
ATOM   4390  OH2 H2O B 650      40.436   -4.907   57.690  1.00 36.69
ATOM   4391  OH2 H2O B 651      31.519   26.062   58.907  1.00 30.88
ATOM   4392  OH2 H2O B 652      27.166    2.787   60.781  1.00 25.65
ATOM   4393  OH2 H2O B 653      32.214    0.581   48.871  1.00 12.24
ATOM   4394  OH2 H2O B 654      31.812   -7.589   64.440  1.00 46.21
ATOM   4395  OH2 H2O B 655      52.595    2.201   33.356  1.00 40.75
ATOM   4396  OH2 H2O B 656      33.573   19.801   43.389  1.00 31.91
ATOM   4397  OH2 H2O B 657      30.059   20.216   53.307  1.00 99.94
ATOM   4398  OH2 H2O B 658      26.849   -0.966   66.085  1.00 47.13
ATOM   4399  OH2 H2O B 659      37.702   -4.830   64.637  1.00 19.32
ATOM   4400  OH2 H2O B 660      49.130    9.010   38.123  1.00 39.58
ATOM   4401  OH2 H2O B 661      43.753    7.869   36.412  1.00 47.45
ATOM   4402  OH2 H2O B 662      22.479   12.903   62.983  1.00 80.90
ATOM   4403  OH2 H2O B 663      35.210  -10.896   56.805  1.00 39.89
ATOM   4404  OH2 H2O B 664      45.954    6.334   35.819  1.00 25.82
ATOM   4405  OH2 H2O B 665      31.366   20.416   56.501  1.00 75.57
ATOM   4406  OH2 H2O B 666      26.061   -1.203   62.072  1.00 32.52
ATOM   4407  OH2 H2O B 667      37.106   22.245   56.105  1.00 27.76
ATOM   4408  OH2 H2O B 668      51.012    0.007   60.464  1.00 31.76
ATOM   4409  OH2 H2O B 669      33.625   22.157   57.850  1.00 77.36
ATOM   4410  OH2 H2O B 670      22.602   -1.130   62.254  1.00 73.40
ATOM   4411  OH2 H2O B 671      26.418   15.210   53.022  1.00 25.43
ATOM   4412  OH2 H2O B 672      35.071   20.786   40.599  1.00 48.04
```

Figure 10

```
ATOM   4413  OH2 H2O B 673      62.362    1.874   48.312  1.00 49.67
ATOM   4414  OH2 H2O B 674      42.922   22.809   55.275  1.00 39.13
ATOM   4415  OH2 H2O B 675      25.487   -1.810   48.814  1.00 26.60
ATOM   4416  OH2 H2O B 676      60.230   18.447   41.256  1.00 42.32
ATOM   4417  OH2 H2O B 677      34.133    8.005   45.822  1.00 27.55
ATOM   4418  OH2 H2O B 678      23.352    4.742   53.114  1.00 36.81
ATOM   4419  OH2 H2O B 679      43.548    1.935   43.674  1.00 32.66
ATOM   4420  OH2 H2O B 680      60.537    6.675   28.592  1.00 33.21
ATOM   4421  OH2 H2O B 681      22.127    4.467   50.293  1.00 57.06
ATOM   4422  OH2 H2O B 682      57.658   20.318   40.070  1.00 39.07
ATOM   4423  OH2 H2O B 683      47.833    6.251   39.904  1.00 60.45
ATOM   4424  OH2 H2O B 684      42.832   -1.775   52.750  1.00 25.28
ATOM   4425  OH2 H2O B 685      24.006    0.283   52.939  1.00 25.87
ATOM   4426  OH2 H2O B 686      45.779   -0.290   69.535  1.00 41.47
ATOM   4427  OH2 H2O B 687      26.785   -3.744   64.392  1.00 49.47
ATOM   4428  OH2 H2O B 688      62.466   10.363   48.863  1.00 38.65
ATOM   4429  OH2 H2O B 689      23.839   -1.701   46.700  1.00 37.90
ATOM   4430  OH2 H2O B 690      33.103   17.508   26.582  1.00 48.19
ATOM   4431  OH2 H2O B 691      42.421   29.203   45.091  1.00 61.23
ATOM   4432  OH2 H2O B 692      40.921    1.307   41.913  1.00 43.07
ATOM   4433  OH2 H2O B 693      44.950   -0.374   47.969  1.00 29.52
ATOM   4434  OH2 H2O B 694      45.959   22.851   42.466  1.00 48.47
ATOM   4435  OH2 H2O B 695      18.684   13.051   66.152  1.00 36.82
ATOM   4436  OH2 H2O B 696      59.326    6.793   58.801  1.00 51.25
ATOM   4437  OH2 H2O B 697      39.470    7.186   68.266  1.00 52.22
ATOM   4438  OH2 H2O B 698      53.179   11.151   25.165  1.00 48.05
ATOM   4439  OH2 H2O B 699      23.603    1.557   60.243  1.00 35.49
ATOM   4440  OH2 H2O B 700      34.866   12.174   68.366  1.00 45.28
ATOM   4441  OH2 H2O B 701      62.136   10.775   36.563  1.00 48.74
ATOM   4442  OH2 H2O B 702      43.090   18.194   40.092  1.00 27.64
END
```

Figure 10

```
CRYST1   57.139   44.371  120.732  90.00  89.99  90.00 P21          1
SCALE1      0.017501  0.000000 -0.000003         0.00000
SCALE2      0.000000  0.022537  0.000000         0.00000
SCALE3      0.000000  0.000000  0.008283         0.00000
ATOM      1  CB  TRP A 238      18.075  -5.615  27.753  1.00 60.95      A    C
ATOM      2  CG  TRP A 238      17.621  -6.180  26.405  1.00 62.85      A    C
ATOM      3  CD2 TRP A 238      18.096  -5.803  25.092  1.00 63.75      A    C
ATOM      4  CE2 TRP A 238      17.404  -6.602  24.151  1.00 64.15      A    C
ATOM      5  CE3 TRP A 238      19.042  -4.873  24.624  1.00 64.16      A    C
ATOM      6  CD1 TRP A 238      16.683  -7.156  26.200  1.00 63.38      A    C
ATOM      7  NE1 TRP A 238      16.547  -7.410  24.851  1.00 64.16      A    N
ATOM      8  CZ2 TRP A 238      17.623  -6.492  22.762  1.00 64.62      A    C
ATOM      9  CZ3 TRP A 238      19.257  -4.765  23.234  1.00 64.01      A    C
ATOM     10  CH2 TRP A 238      18.554  -5.572  22.328  1.00 63.94      A    C
ATOM     11  C   TRP A 238      19.825  -5.566  29.595  1.00 58.75      A    C
ATOM     12  O   TRP A 238      20.424  -4.505  29.474  1.00 59.17      A    O
ATOM     13  N   TRP A 238      19.076  -7.753  28.559  1.00 59.61      A    N
ATOM     14  CA  TRP A 238      19.329  -6.302  28.337  1.00 59.48      A    C
ATOM     15  N   GLU A 239      19.549  -6.094  30.795  1.00 57.27      A    N
ATOM     16  CA  GLU A 239      20.016  -5.469  32.044  1.00 55.38      A    C
ATOM     17  CB  GLU A 239      19.162  -5.849  33.256  1.00 57.33      A    C
ATOM     18  CG  GLU A 239      18.013  -4.927  33.552  1.00 59.81      A    C
ATOM     19  CD  GLU A 239      16.711  -5.369  32.888  1.00 61.91      A    C
ATOM     20  OE1 GLU A 239      16.506  -5.040  31.694  1.00 63.06      A    O
ATOM     21  OE2 GLU A 239      15.889  -6.036  33.564  1.00 61.98      A    O
ATOM     22  C   GLU A 239      21.442  -5.921  32.323  1.00 53.17      A    C
ATOM     23  O   GLU A 239      21.794  -7.080  32.121  1.00 53.33      A    O
ATOM     24  N   VAL A 240      22.248  -5.005  32.830  1.00 50.21      A    N
ATOM     25  CA  VAL A 240      23.637  -5.291  33.121  1.00 46.93      A    C
ATOM     26  CB  VAL A 240      24.558  -4.869  31.932  1.00 46.00      A    C
ATOM     27  CG1 VAL A 240      24.220  -5.676  30.675  1.00 43.05      A    C
ATOM     28  CG2 VAL A 240      24.430  -3.368  31.665  1.00 44.91      A    C
ATOM     29  C   VAL A 240      24.016  -4.523  34.373  1.00 45.83      A    C
ATOM     30  O   VAL A 240      23.338  -3.564  34.754  1.00 44.77      A    O
ATOM     31  N   PRO A 241      25.035  -5.007  35.097  1.00 45.15      A    N
ATOM     32  CD  PRO A 241      25.649  -6.341  34.975  1.00 45.35      A    C
ATOM     33  CA  PRO A 241      25.488  -4.344  36.317  1.00 44.85      A    C
ATOM     34  CB  PRO A 241      26.477  -5.357  36.898  1.00 44.94      A    C
ATOM     35  CG  PRO A 241      25.941  -6.671  36.409  1.00 44.73      A    C
ATOM     36  C   PRO A 241      26.175  -3.015  35.990  1.00 45.19      A    C
ATOM     37  O   PRO A 241      26.828  -2.883  34.955  1.00 45.18      A    O
ATOM     38  N   ARG A 242      25.983  -2.029  36.858  1.00 45.25      A    N
ATOM     39  CA  ARG A 242      26.577  -0.709  36.705  1.00 46.42      A    C
ATOM     40  CB  ARG A 242      26.273   0.076  37.973  1.00 48.04      A    C
ATOM     41  CG  ARG A 242      26.889   1.437  38.068  1.00 50.38      A    C
ATOM     42  CD  ARG A 242      26.267   2.370  37.080  1.00 53.18      A    C
ATOM     43  NE  ARG A 242      24.808   2.478  37.217  1.00 55.59      A    N
ATOM     44  CZ  ARG A 242      24.186   2.987  38.272  1.00 55.79      A    C
ATOM     45  NH1 ARG A 242      24.885   3.434  39.312  1.00 56.23      A    N
ATOM     46  NH2 ARG A 242      22.864   3.073  38.272  1.00 56.39      A    N
```

Figure 11

```
ATOM     47  C   ARG A 242      28.100  -0.774  36.466  1.00 46.68      A  C
ATOM     48  O   ARG A 242      28.665   0.038  35.722  1.00 46.41      A  O
ATOM     49  N   GLU A 243      28.726  -1.785  37.065  1.00 46.74      A  N
ATOM     50  CA  GLU A 243      30.167  -2.047  36.991  1.00 46.92      A  C
ATOM     51  CB  GLU A 243      30.520  -3.277  37.845  1.00 49.48      A  C
ATOM     52  CG  GLU A 243      30.309  -3.092  39.349  1.00 54.05      A  C
ATOM     53  CD  GLU A 243      28.845  -2.794  39.729  1.00 56.35      A  C
ATOM     54  OE1 GLU A 243      27.982  -3.667  39.456  1.00 57.03      A  O
ATOM     55  OE2 GLU A 243      28.570  -1.701  40.303  1.00 56.14      A  O
ATOM     56  C   GLU A 243      30.711  -2.282  35.577  1.00 45.19      A  C
ATOM     57  O   GLU A 243      31.879  -1.999  35.305  1.00 45.04      A  O
ATOM     58  N   THR A 244      29.879  -2.820  34.692  1.00 42.82      A  N
ATOM     59  CA  THR A 244      30.288  -3.089  33.311  1.00 40.69      A  C
ATOM     60  CB  THR A 244      29.247  -3.993  32.591  1.00 40.56      A  C
ATOM     61  OG1 THR A 244      27.978  -3.306  32.495  1.00 40.56      A  O
ATOM     62  CG2 THR A 244      29.060  -5.279  33.343  1.00 40.28      A  C
ATOM     63  C   THR A 244      30.402  -1.805  32.491  1.00 38.56      A  C
ATOM     64  O   THR A 244      30.672  -1.844  31.300  1.00 37.50      A  O
ATOM     65  N   LEU A 245      30.316  -0.671  33.159  1.00 37.86      A  N
ATOM     66  CA  LEU A 245      30.318   0.588  32.463  1.00 38.16      A  C
ATOM     67  CB  LEU A 245      28.848   0.983  32.289  1.00 38.43      A  C
ATOM     68  CG  LEU A 245      28.440   1.989  31.230  1.00 40.05      A  C
ATOM     69  CD1 LEU A 245      28.643   1.366  29.854  1.00 39.80      A  C
ATOM     70  CD2 LEU A 245      26.969   2.366  31.431  1.00 40.27      A  C
ATOM     71  C   LEU A 245      31.057   1.735  33.151  1.00 38.36      A  C
ATOM     72  O   LEU A 245      30.895   1.968  34.362  1.00 38.65      A  O
ATOM     73  N   LYS A 246      31.809   2.497  32.358  1.00 37.27      A  N
ATOM     74  CA  LYS A 246      32.511   3.662  32.878  1.00 37.44      A  C
ATOM     75  CB  LYS A 246      34.052   3.514  32.783  1.00 38.89      A  C
ATOM     76  CG  LYS A 246      34.822   4.741  33.377  1.00 40.38      A  C
ATOM     77  CD  LYS A 246      36.339   4.511  33.608  1.00 42.20      A  C
ATOM     78  CE  LYS A 246      37.000   3.903  32.372  1.00 43.46      A  C
ATOM     79  NZ  LYS A 246      38.473   3.889  32.455  1.00 44.47      A  N
ATOM     80  C   LYS A 246      32.054   4.911  32.119  1.00 36.66      A  C
ATOM     81  O   LYS A 246      32.146   4.975  30.899  1.00 36.34      A  O
ATOM     82  N   LEU A 247      31.531   5.892  32.845  1.00 35.79      A  N
ATOM     83  CA  LEU A 247      31.071   7.126  32.234  1.00 34.73      A  C
ATOM     84  CB  LEU A 247      29.893   7.728  33.020  1.00 33.02      A  C
ATOM     85  CG  LEU A 247      28.524   7.205  32.515  1.00 33.14      A  C
ATOM     86  CD1 LEU A 247      28.388   5.696  32.697  1.00 32.48      A  C
ATOM     87  CD2 LEU A 247      27.376   7.967  33.149  1.00 32.57      A  C
ATOM     88  C   LEU A 247      32.281   8.038  32.196  1.00 34.44      A  C
ATOM     89  O   LEU A 247      32.928   8.268  33.224  1.00 34.42      A  O
ATOM     90  N   VAL A 248      32.604   8.533  31.003  1.00 33.62      A  N
ATOM     91  CA  VAL A 248      33.790   9.369  30.828  1.00 32.66      A  C
ATOM     92  CB  VAL A 248      34.636   8.798  29.709  1.00 31.85      A  C
ATOM     93  CG1 VAL A 248      35.931   9.567  29.572  1.00 32.52      A  C
ATOM     94  CG2 VAL A 248      34.893   7.358  29.982  1.00 31.12      A  C
ATOM     95  C   VAL A 248      33.621  10.859  30.606  1.00 32.20      A  C
ATOM     96  O   VAL A 248      34.282  11.688  31.248  1.00 32.93      A  O
ATOM     97  N   GLU A 249      32.658  11.221  29.788  1.00 31.08      A  N
ATOM     98  CA  GLU A 249      32.491  12.619  29.478  1.00 30.02      A  C
ATOM     99  CB  GLU A 249      33.380  12.898  28.259  1.00 30.55      A  C
ATOM    100  CG  GLU A 249      33.030  14.057  27.407  1.00 31.41      A  C
ATOM    101  CD  GLU A 249      34.034  14.247  26.271  1.00 32.02      A  C
ATOM    102  OE1 GLU A 249      34.854  13.332  25.998  1.00 29.73      A  O
ATOM    103  OE2 GLU A 249      33.982  15.323  25.651  1.00 34.12      A  O
ATOM    104  C   GLU A 249      31.036  12.985  29.204  1.00 29.56      A  C
ATOM    105  O   GLU A 249      30.347  12.294  28.472  1.00 28.25      A  O
```

Figure 11

```
ATOM    106  N   ARG A 250      30.579  14.072  29.808  1.00 30.27           A  N
ATOM    107  CA  ARG A 250      29.223  14.503  29.593  1.00 31.51           A  C
ATOM    108  CB  ARG A 250      28.749  15.440  30.694  1.00 32.43           A  C
ATOM    109  CG  ARG A 250      27.214  15.408  30.801  1.00 35.16           A  C
ATOM    110  CD  ARG A 250      26.750  16.163  32.002  1.00 36.38           A  C
ATOM    111  NE  ARG A 250      27.093  17.554  31.798  1.00 39.15           A  N
ATOM    112  CZ  ARG A 250      26.961  18.502  32.707  1.00 40.58           A  C
ATOM    113  NH1 ARG A 250      26.481  18.211  33.914  1.00 40.96           A  N
ATOM    114  NH2 ARG A 250      27.286  19.749  32.386  1.00 41.26           A  N
ATOM    115  C   ARG A 250      29.094  15.224  28.274  1.00 31.03           A  C
ATOM    116  O   ARG A 250      29.735  16.249  28.059  1.00 31.34           A  O
ATOM    117  N   LEU A 251      28.246  14.686  27.404  1.00 30.23           A  N
ATOM    118  CA  LEU A 251      27.994  15.289  26.100  1.00 28.62           A  C
ATOM    119  CB  LEU A 251      27.612  14.211  25.083  1.00 27.24           A  C
ATOM    120  CG  LEU A 251      28.619  13.077  24.990  1.00 25.62           A  C
ATOM    121  CD1 LEU A 251      28.069  11.979  24.127  1.00 23.63           A  C
ATOM    122  CD2 LEU A 251      29.961  13.619  24.463  1.00 24.62           A  C
ATOM    123  C   LEU A 251      26.910  16.350  26.190  1.00 28.80           A  C
ATOM    124  O   LEU A 251      26.925  17.338  25.432  1.00 29.48           A  O
ATOM    125  N   GLY A 252      25.946  16.146  27.085  1.00 28.32           A  N
ATOM    126  CA  GLY A 252      24.876  17.128  27.249  1.00 26.69           A  C
ATOM    127  C   GLY A 252      24.076  16.999  28.546  1.00 26.43           A  C
ATOM    128  O   GLY A 252      23.993  15.929  29.133  1.00 25.43           A  O
ATOM    129  N   ALA A 253      23.477  18.102  28.989  1.00 27.68           A  N
ATOM    130  CA  ALA A 253      22.659  18.101  30.215  1.00 28.42           A  C
ATOM    131  CB  ALA A 253      23.419  18.773  31.365  1.00 28.61           A  C
ATOM    132  C   ALA A 253      21.352  18.847  29.955  1.00 27.48           A  C
ATOM    133  O   ALA A 253      21.353  20.007  29.528  1.00 26.17           A  O
ATOM    134  N   GLY A 254      20.239  18.156  30.169  1.00 28.69           A  N
ATOM    135  CA  GLY A 254      18.927  18.766  29.951  1.00 30.21           A  C
ATOM    136  C   GLY A 254      17.934  18.657  31.102  1.00 30.44           A  C
ATOM    137  O   GLY A 254      18.258  18.126  32.172  1.00 29.64           A  O
ATOM    138  N   GLN A 255      16.698  19.101  30.843  1.00 32.22           A  N
ATOM    139  CA  GLN A 255      15.589  19.108  31.830  1.00 32.84           A  C
ATOM    140  CB  GLN A 255      14.307  19.735  31.201  1.00 35.90           A  C
ATOM    141  CG  GLN A 255      13.467  20.692  32.127  1.00 41.21           A  C
ATOM    142  CD  GLN A 255      11.909  20.417  32.142  1.00 43.70           A  C
ATOM    143  OE1 GLN A 255      11.300  20.177  33.219  1.00 43.99           A  O
ATOM    144  NE2 GLN A 255      11.282  20.457  30.947  1.00 44.00           A  N
ATOM    145  C   GLN A 255      15.282  17.713  32.394  1.00 32.42           A  C
ATOM    146  O   GLN A 255      14.928  17.585  33.574  1.00 33.55           A  O
ATOM    147  N   PHE A 256      15.473  16.669  31.576  1.00 31.04           A  N
ATOM    148  CA  PHE A 256      15.185  15.280  31.980  1.00 29.81           A  C
ATOM    149  CB  PHE A 256      14.372  14.553  30.895  1.00 30.17           A  C
ATOM    150  CG  PHE A 256      12.970  15.064  30.730  1.00 31.63           A  C
ATOM    151  CD1 PHE A 256      12.515  16.160  31.459  1.00 31.86           A  C
ATOM    152  CD2 PHE A 256      12.097  14.439  29.850  1.00 33.09           A  C
ATOM    153  CE1 PHE A 256      11.205  16.630  31.317  1.00 32.96           A  C
ATOM    154  CE2 PHE A 256      10.773  14.907  29.697  1.00 32.79           A  C
ATOM    155  CZ  PHE A 256      10.340  16.004  30.440  1.00 32.96           A  C
ATOM    156  C   PHE A 256      16.377  14.373  32.350  1.00 28.90           A  C
ATOM    157  O   PHE A 256      16.183  13.229  32.792  1.00 27.20           A  O
ATOM    158  N   GLY A 257      17.589  14.833  32.072  1.00 28.16           A  N
ATOM    159  CA  GLY A 257      18.746  14.017  32.382  1.00 27.82           A  C
ATOM    160  C   GLY A 257      19.953  14.452  31.599  1.00 26.49           A  C
ATOM    161  O   GLY A 257      20.026  15.586  31.192  1.00 25.91           A  O
ATOM    162  N   GLU A 258      20.883  13.536  31.363  1.00 27.62           A  N
ATOM    163  CA  GLU A 258      22.112  13.870  30.642  1.00 28.97           A  C
ATOM    164  CB  GLU A 258      23.236  14.148  31.667  1.00 30.24           A  C
```

Figure 11

| ATOM | 165 | CG | GLU | A | 258 | 22.830 | 15.046 | 32.856 | 1.00 | 32.46 | A | C |
|------|-----|-----|-----|---|-----|--------|--------|--------|------|-------|---|---|
| ATOM | 166 | CD | GLU | A | 258 | 23.953 | 15.224 | 33.880 | 1.00 | 36.15 | A | C |
| ATOM | 167 | OE1 | GLU | A | 258 | 24.609 | 14.206 | 34.227 | 1.00 | 37.61 | A | O |
| ATOM | 168 | OE2 | GLU | A | 258 | 24.178 | 16.376 | 34.330 | 1.00 | 36.04 | A | O |
| ATOM | 169 | C | GLU | A | 258 | 22.567 | 12.723 | 29.738 | 1.00 | 27.80 | A | C |
| ATOM | 170 | O | GLU | A | 258 | 22.138 | 11.583 | 29.890 | 1.00 | 28.31 | A | O |
| ATOM | 171 | N | VAL | A | 259 | 23.423 | 13.048 | 28.779 | 1.00 | 27.13 | A | N |
| ATOM | 172 | CA | VAL | A | 259 | 24.002 | 12.030 | 27.891 | 1.00 | 26.39 | A | C |
| ATOM | 173 | CB | VAL | A | 259 | 23.634 | 12.232 | 26.419 | 1.00 | 26.40 | A | C |
| ATOM | 174 | CG1 | VAL | A | 259 | 24.111 | 11.038 | 25.607 | 1.00 | 24.84 | A | C |
| ATOM | 175 | CG2 | VAL | A | 259 | 22.117 | 12.421 | 26.287 | 1.00 | 27.26 | A | C |
| ATOM | 176 | C | VAL | A | 259 | 25.527 | 12.089 | 28.067 | 1.00 | 25.63 | A | C |
| ATOM | 177 | O | VAL | A | 259 | 26.110 | 13.165 | 28.169 | 1.00 | 24.95 | A | O |
| ATOM | 178 | N | TRP | A | 260 | 26.130 | 10.916 | 28.191 | 1.00 | 25.98 | A | N |
| ATOM | 179 | CA | TRP | A | 260 | 27.569 | 10.780 | 28.402 | 1.00 | 26.43 | A | C |
| ATOM | 180 | CB | TRP | A | 260 | 27.854 | 10.177 | 29.786 | 1.00 | 27.04 | A | C |
| ATOM | 181 | CG | TRP | A | 260 | 27.622 | 11.074 | 30.937 | 1.00 | 28.94 | A | C |
| ATOM | 182 | CD2 | TRP | A | 260 | 28.621 | 11.618 | 31.800 | 1.00 | 31.21 | A | C |
| ATOM | 183 | CE2 | TRP | A | 260 | 27.970 | 12.481 | 32.702 | 1.00 | 31.97 | A | C |
| ATOM | 184 | CE3 | TRP | A | 260 | 30.014 | 11.457 | 31.897 | 1.00 | 30.55 | A | C |
| ATOM | 185 | CD1 | TRP | A | 260 | 26.427 | 11.599 | 31.352 | 1.00 | 30.85 | A | C |
| ATOM | 186 | NE1 | TRP | A | 260 | 26.630 | 12.460 | 32.402 | 1.00 | 31.67 | A | N |
| ATOM | 187 | CZ2 | TRP | A | 260 | 28.657 | 13.189 | 33.679 | 1.00 | 32.23 | A | C |
| ATOM | 188 | CZ3 | TRP | A | 260 | 30.690 | 12.167 | 32.872 | 1.00 | 31.65 | A | C |
| ATOM | 189 | CH2 | TRP | A | 260 | 30.012 | 13.019 | 33.745 | 1.00 | 32.29 | A | C |
| ATOM | 190 | C | TRP | A | 260 | 28.200 | 9.811 | 27.439 | 1.00 | 26.01 | A | C |
| ATOM | 191 | O | TRP | A | 260 | 27.566 | 8.831 | 27.032 | 1.00 | 25.71 | A | O |
| ATOM | 192 | N | MET | A | 261 | 29.451 | 10.090 | 27.077 | 1.00 | 24.91 | A | N |
| ATOM | 193 | CA | MET | A | 261 | 30.213 | 9.151 | 26.268 | 1.00 | 25.07 | A | C |
| ATOM | 194 | CB | MET | A | 261 | 31.309 | 9.877 | 25.492 | 1.00 | 25.93 | A | C |
| ATOM | 195 | CG | MET | A | 261 | 32.160 | 8.938 | 24.627 | 1.00 | 27.63 | A | C |
| ATOM | 196 | SD | MET | A | 261 | 33.506 | 8.059 | 25.516 | 1.00 | 28.15 | A | S |
| ATOM | 197 | CE | MET | A | 261 | 34.433 | 9.472 | 26.184 | 1.00 | 28.19 | A | C |
| ATOM | 198 | C | MET | A | 261 | 30.854 | 8.234 | 27.332 | 1.00 | 24.83 | A | C |
| ATOM | 199 | O | MET | A | 261 | 31.224 | 8.713 | 28.391 | 1.00 | 24.81 | A | O |
| ATOM | 200 | N | GLY | A | 262 | 30.990 | 6.945 | 27.057 | 1.00 | 24.64 | A | N |
| ATOM | 201 | CA | GLY | A | 262 | 31.606 | 6.057 | 28.018 | 1.00 | 26.16 | A | C |
| ATOM | 202 | C | GLY | A | 262 | 32.125 | 4.788 | 27.368 | 1.00 | 28.74 | A | C |
| ATOM | 203 | O | GLY | A | 262 | 32.149 | 4.701 | 26.136 | 1.00 | 28.45 | A | O |
| ATOM | 204 | N | TYR | A | 263 | 32.563 | 3.814 | 28.175 | 1.00 | 29.84 | A | N |
| ATOM | 205 | CA | TYR | A | 263 | 33.021 | 2.535 | 27.633 | 1.00 | 32.11 | A | C |
| ATOM | 206 | CB | TYR | A | 263 | 34.546 | 2.370 | 27.760 | 1.00 | 31.20 | A | C |
| ATOM | 207 | CG | TYR | A | 263 | 35.282 | 3.432 | 26.965 | 1.00 | 29.16 | A | C |
| ATOM | 208 | CD1 | TYR | A | 263 | 35.640 | 3.213 | 25.628 | 1.00 | 27.31 | A | C |
| ATOM | 209 | CE1 | TYR | A | 263 | 36.296 | 4.197 | 24.880 | 1.00 | 27.74 | A | C |
| ATOM | 210 | CD2 | TYR | A | 263 | 35.594 | 4.673 | 27.543 | 1.00 | 29.55 | A | C |
| ATOM | 211 | CE2 | TYR | A | 263 | 36.247 | 5.677 | 26.798 | 1.00 | 29.00 | A | C |
| ATOM | 212 | CZ | TYR | A | 263 | 36.601 | 5.423 | 25.460 | 1.00 | 27.91 | A | C |
| ATOM | 213 | OH | TYR | A | 263 | 37.223 | 6.419 | 24.715 | 1.00 | 29.15 | A | O |
| ATOM | 214 | C | TYR | A | 263 | 32.270 | 1.392 | 28.267 | 1.00 | 33.92 | A | C |
| ATOM | 215 | O | TYR | A | 263 | 32.016 | 1.382 | 29.462 | 1.00 | 34.49 | A | O |
| ATOM | 216 | N | TYR | A | 264 | 31.845 | 0.461 | 27.432 | 1.00 | 35.87 | A | N |
| ATOM | 217 | CA | TYR | A | 264 | 31.067 | -0.679 | 27.862 | 1.00 | 38.92 | A | C |
| ATOM | 218 | CB | TYR | A | 264 | 29.797 | -0.747 | 26.992 | 1.00 | 38.95 | A | C |
| ATOM | 219 | CG | TYR | A | 264 | 28.847 | -1.892 | 27.235 | 1.00 | 39.88 | A | C |
| ATOM | 220 | CD1 | TYR | A | 264 | 28.313 | -2.144 | 28.504 | 1.00 | 39.55 | A | C |
| ATOM | 221 | CE1 | TYR | A | 264 | 27.413 | -3.209 | 28.710 | 1.00 | 39.97 | A | C |
| ATOM | 222 | CD2 | TYR | A | 264 | 28.465 | -2.723 | 26.177 | 1.00 | 40.72 | A | C |
| ATOM | 223 | CE2 | TYR | A | 264 | 27.574 | -3.782 | 26.367 | 1.00 | 41.54 | A | C |

Figure 11

| | | | | | | | | | | | |
|---|---|---|---|---|---|---|---|---|---|---|---|
| ATOM | 224 | CZ | TYR | A | 264 | 27.048 | -4.023 | 27.631 | 1.00 | 40.84 | A | C |
| ATOM | 225 | OH | TYR | A | 264 | 26.154 | -5.064 | 27.782 | 1.00 | 40.54 | A | O |
| ATOM | 226 | C | TYR | A | 264 | 31.977 | -1.901 | 27.708 | 1.00 | 41.37 | A | C |
| ATOM | 227 | O | TYR | A | 264 | 32.514 | -2.174 | 26.619 | 1.00 | 41.33 | A | O |
| ATOM | 228 | N | ASN | A | 265 | 32.182 | -2.593 | 28.830 | 1.00 | 43.33 | A | N |
| ATOM | 229 | CA | ASN | A | 265 | 33.060 | -3.755 | 28.895 | 1.00 | 45.31 | A | C |
| ATOM | 230 | CB | ASN | A | 265 | 32.635 | -4.837 | 27.917 | 1.00 | 44.53 | A | C |
| ATOM | 231 | CG | ASN | A | 265 | 31.263 | -5.396 | 28.233 | 1.00 | 44.85 | A | C |
| ATOM | 232 | OD1 | ASN | A | 265 | 30.931 | -5.651 | 29.394 | 1.00 | 43.17 | A | O |
| ATOM | 233 | ND2 | ASN | A | 265 | 30.451 | -5.567 | 27.202 | 1.00 | 43.80 | A | N |
| ATOM | 234 | C | ASN | A | 265 | 34.494 | -3.318 | 28.612 | 1.00 | 47.06 | A | C |
| ATOM | 235 | O | ASN | A | 265 | 35.253 | -4.037 | 27.973 | 1.00 | 47.43 | A | O |
| ATOM | 236 | N | GLY | A | 266 | 34.831 | -2.104 | 29.043 | 1.00 | 48.77 | A | N |
| ATOM | 237 | CA | GLY | A | 266 | 36.175 | -1.595 | 28.861 | 1.00 | 50.26 | A | C |
| ATOM | 238 | C | GLY | A | 266 | 36.591 | -1.098 | 27.492 | 1.00 | 51.14 | A | C |
| ATOM | 239 | O | GLY | A | 266 | 37.358 | -0.121 | 27.409 | 1.00 | 52.03 | A | O |
| ATOM | 240 | N | HIS | A | 267 | 36.090 | -1.715 | 26.420 | 1.00 | 51.31 | A | N |
| ATOM | 241 | CA | HIS | A | 267 | 36.497 | -1.285 | 25.078 | 1.00 | 51.27 | A | C |
| ATOM | 242 | CB | HIS | A | 267 | 37.493 | -2.299 | 24.481 | 1.00 | 54.79 | A | C |
| ATOM | 243 | CG | HIS | A | 267 | 38.842 | -2.260 | 25.142 | 1.00 | 58.84 | A | C |
| ATOM | 244 | CD2 | HIS | A | 267 | 39.754 | -1.260 | 25.250 | 1.00 | 60.15 | A | C |
| ATOM | 245 | ND1 | HIS | A | 267 | 39.339 | -3.309 | 25.895 | 1.00 | 60.61 | A | N |
| ATOM | 246 | CE1 | HIS | A | 267 | 40.488 | -2.952 | 26.443 | 1.00 | 61.67 | A | C |
| ATOM | 247 | NE2 | HIS | A | 267 | 40.763 | -1.713 | 26.066 | 1.00 | 61.46 | A | N |
| ATOM | 248 | C | HIS | A | 267 | 35.471 | -0.830 | 24.029 | 1.00 | 49.13 | A | C |
| ATOM | 249 | O | HIS | A | 267 | 35.861 | -0.277 | 22.989 | 1.00 | 49.38 | A | O |
| ATOM | 250 | N | THR | A | 268 | 34.180 | -1.041 | 24.275 | 1.00 | 46.06 | A | N |
| ATOM | 251 | CA | THR | A | 268 | 33.161 | -0.604 | 23.304 | 1.00 | 42.54 | A | C |
| ATOM | 252 | CB | THR | A | 268 | 31.900 | -1.533 | 23.315 | 1.00 | 42.95 | A | C |
| ATOM | 253 | OG1 | THR | A | 268 | 32.290 | -2.883 | 23.010 | 1.00 | 43.71 | A | O |
| ATOM | 254 | CG2 | THR | A | 268 | 30.873 | -1.090 | 22.272 | 1.00 | 41.95 | A | C |
| ATOM | 255 | C | THR | A | 268 | 32.783 | 0.827 | 23.673 | 1.00 | 39.46 | A | C |
| ATOM | 256 | O | THR | A | 268 | 32.389 | 1.091 | 24.806 | 1.00 | 39.61 | A | O |
| ATOM | 257 | N | LYS | A | 269 | 32.966 | 1.762 | 22.751 | 1.00 | 36.13 | A | N |
| ATOM | 258 | CA | LYS | A | 269 | 32.625 | 3.139 | 23.039 | 1.00 | 33.59 | A | C |
| ATOM | 259 | CB | LYS | A | 269 | 33.352 | 4.078 | 22.072 | 1.00 | 33.83 | A | C |
| ATOM | 260 | CG | LYS | A | 269 | 33.335 | 5.517 | 22.495 | 1.00 | 34.04 | A | C |
| ATOM | 261 | CD | LYS | A | 269 | 34.099 | 6.357 | 21.520 | 1.00 | 33.77 | A | C |
| ATOM | 262 | CE | LYS | A | 269 | 34.655 | 7.564 | 22.226 | 1.00 | 35.44 | A | C |
| ATOM | 263 | NZ | LYS | A | 269 | 35.868 | 8.135 | 21.534 | 1.00 | 36.81 | A | N |
| ATOM | 264 | C | LYS | A | 269 | 31.104 | 3.228 | 22.913 | 1.00 | 32.49 | A | C |
| ATOM | 265 | O | LYS | A | 269 | 30.524 | 2.685 | 21.968 | 1.00 | 32.27 | A | O |
| ATOM | 266 | N | VAL | A | 270 | 30.456 | 3.858 | 23.899 | 1.00 | 30.71 | A | N |
| ATOM | 267 | CA | VAL | A | 270 | 28.995 | 3.952 | 23.939 | 1.00 | 28.40 | A | C |
| ATOM | 268 | CB | VAL | A | 270 | 28.361 | 2.854 | 24.887 | 1.00 | 27.70 | A | C |
| ATOM | 269 | CG1 | VAL | A | 270 | 28.650 | 1.429 | 24.388 | 1.00 | 26.36 | A | C |
| ATOM | 270 | CG2 | VAL | A | 270 | 28.845 | 3.049 | 26.316 | 1.00 | 25.08 | A | C |
| ATOM | 271 | C | VAL | A | 270 | 28.504 | 5.288 | 24.471 | 1.00 | 28.12 | A | C |
| ATOM | 272 | O | VAL | A | 270 | 29.273 | 6.075 | 25.018 | 1.00 | 26.99 | A | O |
| ATOM | 273 | N | ALA | A | 271 | 27.231 | 5.577 | 24.188 | 1.00 | 28.20 | A | N |
| ATOM | 274 | CA | ALA | A | 271 | 26.555 | 6.774 | 24.690 | 1.00 | 26.92 | A | C |
| ATOM | 275 | CB | ALA | A | 271 | 25.665 | 7.407 | 23.624 | 1.00 | 26.12 | A | C |
| ATOM | 276 | C | ALA | A | 271 | 25.703 | 6.238 | 25.846 | 1.00 | 26.93 | A | C |
| ATOM | 277 | O | ALA | A | 271 | 25.167 | 5.137 | 25.772 | 1.00 | 26.48 | A | O |
| ATOM | 278 | N | VAL | A | 272 | 25.585 | 7.019 | 26.914 | 1.00 | 27.44 | A | N |
| ATOM | 279 | CA | VAL | A | 272 | 24.801 | 6.598 | 28.075 | 1.00 | 27.79 | A | C |
| ATOM | 280 | CB | VAL | A | 272 | 25.704 | 6.258 | 29.321 | 1.00 | 27.85 | A | C |
| ATOM | 281 | CG1 | VAL | A | 272 | 24.863 | 5.673 | 30.446 | 1.00 | 26.88 | A | C |
| ATOM | 282 | CG2 | VAL | A | 272 | 26.770 | 5.241 | 28.946 | 1.00 | 28.00 | A | C |

Figure 11

| | | | | | | | | | | | |
|---|---|---|---|---|---|---|---|---|---|---|---|
| ATOM | 283 | C | VAL | A | 272 | 23.861 | 7.731 | 28.450 | 1.00 | 27.54 | A | C |
| ATOM | 284 | O | VAL | A | 272 | 24.294 | 8.835 | 28.780 | 1.00 | 26.83 | A | O |
| ATOM | 285 | N | LYS | A | 273 | 22.565 | 7.464 | 28.358 | 1.00 | 28.59 | A | N |
| ATOM | 286 | CA | LYS | A | 273 | 21.581 | 8.481 | 28.710 | 1.00 | 29.02 | A | C |
| ATOM | 287 | CB | LYS | A | 273 | 20.406 | 8.416 | 27.723 | 1.00 | 30.17 | A | C |
| ATOM | 288 | CG | LYS | A | 273 | 19.252 | 9.369 | 28.001 | 1.00 | 32.04 | A | C |
| ATOM | 289 | CD | LYS | A | 273 | 18.171 | 9.199 | 26.943 | 1.00 | 33.70 | A | C |
| ATOM | 290 | CE | LYS | A | 273 | 18.490 | 10.094 | 25.750 | 1.00 | 34.40 | A | C |
| ATOM | 291 | NZ | LYS | A | 273 | 17.359 | 10.115 | 24.780 | 1.00 | 35.39 | A | N |
| ATOM | 292 | C | LYS | A | 273 | 21.133 | 8.152 | 30.130 | 1.00 | 30.03 | A | C |
| ATOM | 293 | O | LYS | A | 273 | 20.736 | 7.022 | 30.400 | 1.00 | 30.19 | A | O |
| ATOM | 294 | N | SER | A | 274 | 21.231 | 9.107 | 31.054 | 1.00 | 31.13 | A | N |
| ATOM | 295 | CA | SER | A | 274 | 20.816 | 8.831 | 32.423 | 1.00 | 32.56 | A | C |
| ATOM | 296 | CB | SER | A | 274 | 21.953 | 9.074 | 33.413 | 1.00 | 32.49 | A | C |
| ATOM | 297 | OG | SER | A | 274 | 22.364 | 10.422 | 33.306 | 1.00 | 34.10 | A | O |
| ATOM | 298 | C | SER | A | 274 | 19.653 | 9.736 | 32.776 | 1.00 | 33.16 | A | C |
| ATOM | 299 | O | SER | A | 274 | 19.631 | 10.910 | 32.423 | 1.00 | 33.42 | A | O |
| ATOM | 300 | N | LEU | A | 275 | 18.705 | 9.182 | 33.515 | 1.00 | 34.05 | A | N |
| ATOM | 301 | CA | LEU | A | 275 | 17.518 | 9.923 | 33.906 | 1.00 | 34.13 | A | C |
| ATOM | 302 | CB | LEU | A | 275 | 16.399 | 8.919 | 34.189 | 1.00 | 32.22 | A | C |
| ATOM | 303 | CG | LEU | A | 275 | 15.183 | 9.405 | 34.984 | 1.00 | 30.93 | A | C |
| ATOM | 304 | CD1 | LEU | A | 275 | 14.407 | 10.428 | 34.162 | 1.00 | 30.76 | A | C |
| ATOM | 305 | CD2 | LEU | A | 275 | 14.306 | 8.226 | 35.341 | 1.00 | 28.85 | A | C |
| ATOM | 306 | C | LEU | A | 275 | 17.721 | 10.824 | 35.128 | 1.00 | 36.07 | A | C |
| ATOM | 307 | O | LEU | A | 275 | 18.404 | 10.440 | 36.089 | 1.00 | 37.01 | A | O |
| ATOM | 308 | N | LYS | A | 276 | 17.205 | 12.047 | 35.067 | 1.00 | 36.08 | A | N |
| ATOM | 309 | CA | LYS | A | 276 | 17.257 | 12.926 | 36.226 | 1.00 | 37.42 | A | C |
| ATOM | 310 | CB | LYS | A | 276 | 17.116 | 14.389 | 35.830 | 1.00 | 37.82 | A | C |
| ATOM | 311 | CG | LYS | A | 276 | 16.880 | 15.295 | 37.030 | 1.00 | 39.86 | A | C |
| ATOM | 312 | CD | LYS | A | 276 | 16.706 | 16.728 | 36.626 | 1.00 | 43.22 | A | C |
| ATOM | 313 | CE | LYS | A | 276 | 17.904 | 17.186 | 35.814 | 1.00 | 45.01 | A | C |
| ATOM | 314 | NZ | LYS | A | 276 | 17.709 | 18.544 | 35.215 | 1.00 | 47.73 | A | N |
| ATOM | 315 | C | LYS | A | 276 | 16.010 | 12.537 | 37.041 | 1.00 | 38.56 | A | C |
| ATOM | 316 | O | LYS | A | 276 | 14.882 | 12.746 | 36.585 | 1.00 | 38.08 | A | O |
| ATOM | 317 | N | GLN | A | 277 | 16.214 | 11.965 | 38.225 | 1.00 | 39.38 | A | N |
| ATOM | 318 | CA | GLN | A | 277 | 15.117 | 11.535 | 39.095 | 1.00 | 41.06 | A | C |
| ATOM | 319 | CB | GLN | A | 277 | 15.652 | 11.200 | 40.486 | 1.00 | 43.37 | A | C |
| ATOM | 320 | CG | GLN | A | 277 | 14.594 | 10.617 | 41.406 | 1.00 | 47.78 | A | C |
| ATOM | 321 | CD | GLN | A | 277 | 15.160 | 10.312 | 42.780 | 1.00 | 51.05 | A | C |
| ATOM | 322 | OE1 | GLN | A | 277 | 16.075 | 10.988 | 43.255 | 1.00 | 53.35 | A | O |
| ATOM | 323 | NE2 | GLN | A | 277 | 14.594 | 9.306 | 43.449 | 1.00 | 52.45 | A | N |
| ATOM | 324 | C | GLN | A | 277 | 13.964 | 12.529 | 39.223 | 1.00 | 40.20 | A | C |
| ATOM | 325 | O | GLN | A | 277 | 14.170 | 13.722 | 39.440 | 1.00 | 39.49 | A | O |
| ATOM | 326 | N | GLY | A | 278 | 12.748 | 12.025 | 39.050 | 1.00 | 40.36 | A | N |
| ATOM | 327 | CA | GLY | A | 278 | 11.579 | 12.873 | 39.147 | 1.00 | 40.36 | A | C |
| ATOM | 328 | C | GLY | A | 278 | 11.133 | 13.549 | 37.862 | 1.00 | 41.05 | A | C |
| ATOM | 329 | O | GLY | A | 278 | 10.075 | 14.187 | 37.834 | 1.00 | 42.05 | A | O |
| ATOM | 330 | N | SER | A | 279 | 11.929 | 13.450 | 36.803 | 1.00 | 40.08 | A | N |
| ATOM | 331 | CA | SER | A | 279 | 11.563 | 14.081 | 35.537 | 1.00 | 39.99 | A | C |
| ATOM | 332 | CB | SER | A | 279 | 12.754 | 14.058 | 34.580 | 1.00 | 40.38 | A | C |
| ATOM | 333 | OG | SER | A | 279 | 13.745 | 14.953 | 35.020 | 1.00 | 40.96 | A | O |
| ATOM | 334 | C | SER | A | 279 | 10.418 | 13.251 | 34.973 | 1.00 | 39.31 | A | C |
| ATOM | 335 | O | SER | A | 279 | 9.483 | 13.760 | 34.356 | 1.00 | 38.52 | A | O |
| ATOM | 336 | N | MET | A | 280 | 10.561 | 11.951 | 35.167 | 1.00 | 38.57 | A | N |
| ATOM | 337 | CA | MET | A | 280 | 9.590 | 10.955 | 34.768 | 1.00 | 38.12 | A | C |
| ATOM | 338 | CB | MET | A | 280 | 9.616 | 10.721 | 33.253 | 1.00 | 38.33 | A | C |
| ATOM | 339 | CG | MET | A | 280 | 10.730 | 9.826 | 32.716 | 1.00 | 38.89 | A | C |
| ATOM | 340 | SD | MET | A | 280 | 10.790 | 9.938 | 30.877 | 1.00 | 40.04 | A | S |
| ATOM | 341 | CE | MET | A | 280 | 10.046 | 8.523 | 30.476 | 1.00 | 40.38 | A | C |

Figure 11

| | | | | | | | | | | |
|---|---|---|---|---|---|---|---|---|---|---|
| ATOM | 342 | C | MET | A | 280 | 9.972 | 9.717 | 35.570 | 1.00 37.52 | A | C |
| ATOM | 343 | O | MET | A | 280 | 11.046 | 9.680 | 36.186 | 1.00 37.55 | A | O |
| ATOM | 344 | N | SER | A | 281 | 9.084 | 8.731 | 35.601 | 1.00 36.56 | A | N |
| ATOM | 345 | CA | SER | A | 281 | 9.362 | 7.527 | 36.364 | 1.00 36.70 | A | C |
| ATOM | 346 | CB | SER | A | 281 | 8.060 | 6.791 | 36.681 | 1.00 33.88 | A | C |
| ATOM | 347 | OG | SER | A | 281 | 7.694 | 5.910 | 35.636 | 1.00 33.48 | A | O |
| ATOM | 348 | C | SER | A | 281 | 10.349 | 6.586 | 35.660 | 1.00 38.39 | A | C |
| ATOM | 349 | O | SER | A | 281 | 10.485 | 6.620 | 34.427 | 1.00 38.35 | A | O |
| ATOM | 350 | N | PRO | A | 282 | 11.083 | 5.775 | 36.436 | 1.00 39.17 | A | N |
| ATOM | 351 | CD | PRO | A | 282 | 11.216 | 5.907 | 37.899 | 1.00 40.13 | A | C |
| ATOM | 352 | CA | PRO | A | 282 | 12.060 | 4.814 | 35.934 | 1.00 40.59 | A | C |
| ATOM | 353 | CB | PRO | A | 282 | 12.452 | 4.059 | 37.205 | 1.00 39.52 | A | C |
| ATOM | 354 | CG | PRO | A | 282 | 12.513 | 5.155 | 38.184 | 1.00 39.21 | A | C |
| ATOM | 355 | C | PRO | A | 282 | 11.437 | 3.875 | 34.917 | 1.00 42.29 | A | C |
| ATOM | 356 | O | PRO | A | 282 | 12.028 | 3.638 | 33.868 | 1.00 42.63 | A | O |
| ATOM | 357 | N | ASP | A | 283 | 10.249 | 3.363 | 35.207 | 1.00 43.49 | A | N |
| ATOM | 358 | CA | ASP | A | 283 | 9.575 | 2.453 | 34.281 | 1.00 44.67 | A | C |
| ATOM | 359 | CB | ASP | A | 283 | 8.324 | 1.798 | 34.915 | 1.00 47.45 | A | C |
| ATOM | 360 | CG | ASP | A | 283 | 8.670 | 0.514 | 35.701 | 1.00 50.68 | A | C |
| ATOM | 361 | OD1 | ASP | A | 283 | 9.790 | -0.034 | 35.577 | 1.00 53.16 | A | O |
| ATOM | 362 | OD2 | ASP | A | 283 | 7.789 | 0.033 | 36.457 | 1.00 51.97 | A | O |
| ATOM | 363 | C | ASP | A | 283 | 9.226 | 3.118 | 32.937 | 1.00 43.51 | A | C |
| ATOM | 364 | O | ASP | A | 283 | 9.385 | 2.512 | 31.885 | 1.00 43.06 | A | O |
| ATOM | 365 | N | ALA | A | 284 | 8.792 | 4.375 | 32.993 | 1.00 42.80 | A | N |
| ATOM | 366 | CA | ALA | A | 284 | 8.462 | 5.120 | 31.772 | 1.00 42.14 | A | C |
| ATOM | 367 | CB | ALA | A | 284 | 7.869 | 6.487 | 32.141 | 1.00 40.49 | A | C |
| ATOM | 368 | C | ALA | A | 284 | 9.729 | 5.311 | 30.920 | 1.00 41.46 | A | C |
| ATOM | 369 | O | ALA | A | 284 | 9.699 | 5.123 | 29.699 | 1.00 42.01 | A | O |
| ATOM | 370 | N | PHE | A | 285 | 10.832 | 5.693 | 31.568 | 1.00 40.44 | A | N |
| ATOM | 371 | CA | PHE | A | 285 | 12.119 | 5.934 | 30.909 | 1.00 38.85 | A | C |
| ATOM | 372 | CB | PHE | A | 285 | 13.101 | 6.528 | 31.935 | 1.00 37.97 | A | C |
| ATOM | 373 | CG | PHE | A | 285 | 14.491 | 6.775 | 31.401 | 1.00 36.87 | A | C |
| ATOM | 374 | CD1 | PHE | A | 285 | 14.770 | 7.889 | 30.606 | 1.00 36.77 | A | C |
| ATOM | 375 | CD2 | PHE | A | 285 | 15.534 | 5.930 | 31.742 | 1.00 35.50 | A | C |
| ATOM | 376 | CE1 | PHE | A | 285 | 16.077 | 8.141 | 30.168 | 1.00 36.88 | A | C |
| ATOM | 377 | CE2 | PHE | A | 285 | 16.842 | 6.177 | 31.308 | 1.00 35.11 | A | C |
| ATOM | 378 | CZ | PHE | A | 285 | 17.112 | 7.283 | 30.529 | 1.00 35.72 | A | C |
| ATOM | 379 | C | PHE | A | 285 | 12.668 | 4.657 | 30.281 | 1.00 38.61 | A | C |
| ATOM | 380 | O | PHE | A | 285 | 13.083 | 4.641 | 29.124 | 1.00 37.93 | A | O |
| ATOM | 381 | N | LEU | A | 286 | 12.628 | 3.574 | 31.037 | 1.00 38.75 | A | N |
| ATOM | 382 | CA | LEU | A | 286 | 13.121 | 2.296 | 30.556 | 1.00 39.67 | A | C |
| ATOM | 383 | CB | LEU | A | 286 | 13.246 | 1.309 | 31.721 | 1.00 40.71 | A | C |
| ATOM | 384 | CG | LEU | A | 286 | 14.304 | 1.707 | 32.758 | 1.00 40.84 | A | C |
| ATOM | 385 | CD1 | LEU | A | 286 | 14.291 | 0.763 | 33.955 | 1.00 42.11 | A | C |
| ATOM | 386 | CD2 | LEU | A | 286 | 15.649 | 1.692 | 32.071 | 1.00 41.94 | A | C |
| ATOM | 387 | C | LEU | A | 286 | 12.194 | 1.751 | 29.497 | 1.00 40.23 | A | C |
| ATOM | 388 | O | LEU | A | 286 | 12.628 | 1.046 | 28.597 | 1.00 39.83 | A | O |
| ATOM | 389 | N | ALA | A | 287 | 10.910 | 2.097 | 29.603 | 1.00 41.52 | A | N |
| ATOM | 390 | CA | ALA | A | 287 | 9.892 | 1.649 | 28.650 | 1.00 42.64 | A | C |
| ATOM | 391 | CB | ALA | A | 287 | 8.488 | 2.060 | 29.115 | 1.00 42.62 | A | C |
| ATOM | 392 | C | ALA | A | 287 | 10.188 | 2.183 | 27.249 | 1.00 42.14 | A | C |
| ATOM | 393 | O | ALA | A | 287 | 9.992 | 1.484 | 26.267 | 1.00 42.17 | A | O |
| ATOM | 394 | N | GLU | A | 288 | 10.681 | 3.411 | 27.172 | 1.00 42.90 | A | N |
| ATOM | 395 | CA | GLU | A | 288 | 11.041 | 3.995 | 25.885 | 1.00 44.38 | A | C |
| ATOM | 396 | CB | GLU | A | 288 | 11.486 | 5.446 | 26.063 | 1.00 45.03 | A | C |
| ATOM | 397 | CG | GLU | A | 288 | 10.412 | 6.384 | 26.629 | 1.00 47.09 | A | C |
| ATOM | 398 | CD | GLU | A | 288 | 10.884 | 7.829 | 26.776 | 1.00 47.74 | A | C |
| ATOM | 399 | OE1 | GLU | A | 288 | 12.104 | 8.053 | 26.923 | 1.00 50.08 | A | O |
| ATOM | 400 | OE2 | GLU | A | 288 | 10.042 | 8.750 | 26.737 | 1.00 47.50 | A | O |

Figure 11

| | | | | | | | | | | | |
|---|---|---|---|---|---|---|---|---|---|---|---|
| ATOM | 401 | C | GLU | A | 288 | 12.159 | 3.167 | 25.225 | 1.00 | 45.24 | A | C |
| ATOM | 402 | O | GLU | A | 288 | 12.168 | 2.988 | 24.006 | 1.00 | 45.70 | A | O |
| ATOM | 403 | N | ALA | A | 289 | 13.068 | 2.632 | 26.044 | 1.00 | 45.42 | A | N |
| ATOM | 404 | CA | ALA | A | 289 | 14.176 | 1.818 | 25.558 | 1.00 | 45.42 | A | C |
| ATOM | 405 | CB | ALA | A | 289 | 15.147 | 1.534 | 26.686 | 1.00 | 45.43 | A | C |
| ATOM | 406 | C | ALA | A | 289 | 13.715 | 0.516 | 24.932 | 1.00 | 46.35 | A | C |
| ATOM | 407 | O | ALA | A | 289 | 14.423 | -0.057 | 24.119 | 1.00 | 45.07 | A | O |
| ATOM | 408 | N | ASN | A | 290 | 12.535 | 0.051 | 25.335 | 1.00 | 48.71 | A | N |
| ATOM | 409 | CA | ASN | A | 290 | 11.954 | -1.194 | 24.815 | 1.00 | 51.27 | A | C |
| ATOM | 410 | CB | ASN | A | 290 | 10.632 | -1.508 | 25.523 | 1.00 | 52.82 | A | C |
| ATOM | 411 | CG | ASN | A | 290 | 10.820 | -1.935 | 26.969 | 1.00 | 53.13 | A | C |
| ATOM | 412 | OD1 | ASN | A | 290 | 9.946 | -1.710 | 27.807 | 1.00 | 54.05 | A | O |
| ATOM | 413 | ND2 | ASN | A | 290 | 11.947 | -2.570 | 27.263 | 1.00 | 53.25 | A | N |
| ATOM | 414 | C | ASN | A | 290 | 11.729 | -1.229 | 23.290 | 1.00 | 52.67 | A | C |
| ATOM | 415 | O | ASN | A | 290 | 11.870 | -2.287 | 22.668 | 1.00 | 52.64 | A | O |
| ATOM | 416 | N | LEU | A | 291 | 11.372 | -0.077 | 22.715 | 1.00 | 53.85 | A | N |
| ATOM | 417 | CA | LEU | A | 291 | 11.137 | 0.083 | 21.279 | 1.00 | 54.95 | A | C |
| ATOM | 418 | CB | LEU | A | 291 | 10.654 | 1.506 | 20.995 | 1.00 | 55.98 | A | C |
| ATOM | 419 | CG | LEU | A | 291 | 9.471 | 1.983 | 21.843 | 1.00 | 56.67 | A | C |
| ATOM | 420 | CD1 | LEU | A | 291 | 9.360 | 3.485 | 21.803 | 1.00 | 56.86 | A | C |
| ATOM | 421 | CD2 | LEU | A | 291 | 8.186 | 1.328 | 21.375 | 1.00 | 57.86 | A | C |
| ATOM | 422 | C | LEU | A | 291 | 12.407 | -0.173 | 20.473 | 1.00 | 55.71 | A | C |
| ATOM | 423 | O | LEU | A | 291 | 12.352 | -0.627 | 19.325 | 1.00 | 56.19 | A | O |
| ATOM | 424 | N | MET | A | 292 | 13.545 | 0.190 | 21.050 | 1.00 | 55.58 | A | N |
| ATOM | 425 | CA | MET | A | 292 | 14.840 | -0.024 | 20.404 | 1.00 | 55.34 | A | C |
| ATOM | 426 | CB | MET | A | 292 | 15.937 | 0.717 | 21.181 | 1.00 | 55.52 | A | C |
| ATOM | 427 | CG | MET | A | 292 | 16.715 | 1.741 | 20.355 | 1.00 | 55.60 | A | C |
| ATOM | 428 | SD | MET | A | 292 | 17.787 | 2.762 | 21.362 | 1.00 | 53.53 | A | S |
| ATOM | 429 | CE | MET | A | 292 | 17.186 | 4.474 | 20.946 | 1.00 | 55.92 | A | C |
| ATOM | 430 | C | MET | A | 292 | 15.156 | -1.525 | 20.331 | 1.00 | 55.34 | A | C |
| ATOM | 431 | O | MET | A | 292 | 15.821 | -1.990 | 19.408 | 1.00 | 54.78 | A | O |
| ATOM | 432 | N | LYS | A | 293 | 14.688 | -2.278 | 21.319 | 1.00 | 55.35 | A | N |
| ATOM | 433 | CA | LYS | A | 293 | 14.911 | -3.717 | 21.330 | 1.00 | 55.72 | A | C |
| ATOM | 434 | CB | LYS | A | 293 | 14.417 | -4.325 | 22.639 | 1.00 | 57.22 | A | C |
| ATOM | 435 | CG | LYS | A | 293 | 14.974 | -3.721 | 23.918 | 1.00 | 59.08 | A | C |
| ATOM | 436 | CD | LYS | A | 293 | 14.388 | -4.460 | 25.137 | 1.00 | 60.21 | A | C |
| ATOM | 437 | CE | LYS | A | 293 | 14.911 | -3.904 | 26.459 | 1.00 | 61.66 | A | C |
| ATOM | 438 | NZ | LYS | A | 293 | 14.372 | -4.659 | 27.627 | 1.00 | 62.12 | A | N |
| ATOM | 439 | C | LYS | A | 293 | 14.085 | -4.330 | 20.195 | 1.00 | 55.38 | A | C |
| ATOM | 440 | O | LYS | A | 293 | 14.541 | -5.232 | 19.484 | 1.00 | 56.12 | A | O |
| ATOM | 441 | N | GLN | A | 294 | 12.868 | -3.815 | 20.036 | 1.00 | 53.76 | A | N |
| ATOM | 442 | CA | GLN | A | 294 | 11.936 | -4.301 | 19.032 | 1.00 | 52.19 | A | C |
| ATOM | 443 | CB | GLN | A | 294 | 10.540 | -3.716 | 19.294 | 1.00 | 53.18 | A | C |
| ATOM | 444 | CG | GLN | A | 294 | 10.050 | -3.935 | 20.718 | 1.00 | 55.75 | A | C |
| ATOM | 445 | CD | GLN | A | 294 | 10.251 | -5.375 | 21.198 | 1.00 | 58.46 | A | C |
| ATOM | 446 | OE1 | GLN | A | 294 | 11.072 | -5.646 | 22.088 | 1.00 | 58.23 | A | O |
| ATOM | 447 | NE2 | GLN | A | 294 | 9.501 | -6.308 | 20.599 | 1.00 | 59.76 | A | N |
| ATOM | 448 | C | GLN | A | 294 | 12.345 | -4.070 | 17.580 | 1.00 | 50.29 | A | C |
| ATOM | 449 | O | GLN | A | 294 | 12.320 | -5.006 | 16.774 | 1.00 | 50.50 | A | O |
| ATOM | 450 | N | LEU | A | 295 | 12.698 | -2.833 | 17.242 | 1.00 | 47.79 | A | N |
| ATOM | 451 | CA | LEU | A | 295 | 13.103 | -2.484 | 15.887 | 1.00 | 45.60 | A | C |
| ATOM | 452 | CB | LEU | A | 295 | 12.390 | -1.219 | 15.411 | 1.00 | 46.51 | A | C |
| ATOM | 453 | CG | LEU | A | 295 | 10.937 | -1.257 | 14.992 | 1.00 | 46.58 | A | C |
| ATOM | 454 | CD1 | LEU | A | 295 | 10.647 | 0.036 | 14.242 | 1.00 | 46.86 | A | C |
| ATOM | 455 | CD2 | LEU | A | 295 | 10.693 | -2.439 | 14.072 | 1.00 | 47.04 | A | C |
| ATOM | 456 | C | LEU | A | 295 | 14.596 | -2.223 | 15.772 | 1.00 | 43.43 | A | C |
| ATOM | 457 | O | LEU | A | 295 | 15.085 | -1.204 | 16.221 | 1.00 | 42.40 | A | O |
| ATOM | 458 | N | GLN | A | 296 | 15.303 | -3.125 | 15.110 | 1.00 | 41.97 | A | N |
| ATOM | 459 | CA | GLN | A | 296 | 16.734 | -2.974 | 14.929 | 1.00 | 40.82 | A | C |

Figure 11

| ATOM | 460 | CB | GLN A 296 | 17.481 | -4.154 | 15.527 | 1.00 | 42.28 | A | C |
|------|-----|-----|-----------|--------|--------|--------|------|-------|---|---|
| ATOM | 461 | CG | GLN A 296 | 17.255 | -4.346 | 17.004 | 1.00 | 44.69 | A | C |
| ATOM | 462 | CD | GLN A 296 | 17.446 | -5.785 | 17.405 | 1.00 | 47.36 | A | C |
| ATOM | 463 | OE1 | GLN A 296 | 17.310 | -6.695 | 16.595 | 1.00 | 49.19 | A | O |
| ATOM | 464 | NE2 | GLN A 296 | 17.742 | -6.006 | 18.676 | 1.00 | 46.96 | A | N |
| ATOM | 465 | C | GLN A 296 | 17.039 | -2.850 | 13.451 | 1.00 | 39.21 | A | C |
| ATOM | 466 | O | GLN A 296 | 16.531 | -3.615 | 12.636 | 1.00 | 38.86 | A | O |
| ATOM | 467 | N | HIS A 297 | 17.889 | -1.889 | 13.118 | 1.00 | 37.13 | A | N |
| ATOM | 468 | CA | HIS A 297 | 18.244 | -1.673 | 11.735 | 1.00 | 35.41 | A | C |
| ATOM | 469 | CB | HIS A 297 | 17.100 | -0.927 | 11.048 | 1.00 | 33.78 | A | C |
| ATOM | 470 | CG | HIS A 297 | 17.199 | -0.945 | 9.543 | 1.00 | 32.70 | A | C |
| ATOM | 471 | CD2 | HIS A 297 | 16.643 | -1.764 | 8.631 | 1.00 | 31.06 | A | C |
| ATOM | 472 | ND1 | HIS A 297 | 17.979 | -0.062 | 8.859 | 1.00 | 32.27 | A | N |
| ATOM | 473 | CE1 | HIS A 297 | 17.912 | -0.330 | 7.561 | 1.00 | 30.85 | A | C |
| ATOM | 474 | NE2 | HIS A 297 | 17.100 | -1.360 | 7.404 | 1.00 | 29.74 | A | N |
| ATOM | 475 | C | HIS A 297 | 19.510 | -0.831 | 11.669 | 1.00 | 35.30 | A | C |
| ATOM | 476 | O | HIS A 297 | 19.818 | -0.078 | 12.609 | 1.00 | 34.28 | A | O |
| ATOM | 477 | N | GLN A 298 | 20.239 | -0.964 | 10.558 | 1.00 | 35.20 | A | N |
| ATOM | 478 | CA | GLN A 298 | 21.465 | -0.204 | 10.364 | 1.00 | 35.55 | A | C |
| ATOM | 479 | CB | GLN A 298 | 22.171 | -0.597 | 9.058 | 1.00 | 37.76 | A | C |
| ATOM | 480 | CG | GLN A 298 | 23.142 | -1.815 | 9.187 | 1.00 | 43.86 | A | C |
| ATOM | 481 | CD | GLN A 298 | 24.207 | -1.677 | 10.324 | 1.00 | 46.03 | A | C |
| ATOM | 482 | OE1 | GLN A 298 | 24.435 | -2.616 | 11.101 | 1.00 | 47.09 | A | O |
| ATOM | 483 | NE2 | GLN A 298 | 24.839 | -0.504 | 10.421 | 1.00 | 46.67 | A | N |
| ATOM | 484 | C | GLN A 298 | 21.219 | 1.292 | 10.385 | 1.00 | 33.92 | A | C |
| ATOM | 485 | O | GLN A 298 | 22.115 | 2.063 | 10.725 | 1.00 | 33.17 | A | O |
| ATOM | 486 | N | ARG A 299 | 20.004 | 1.701 | 10.028 | 1.00 | 32.31 | A | N |
| ATOM | 487 | CA | ARG A 299 | 19.654 | 3.124 | 10.002 | 1.00 | 31.06 | A | C |
| ATOM | 488 | CB | ARG A 299 | 18.743 | 3.406 | 8.818 | 1.00 | 32.67 | A | C |
| ATOM | 489 | CG | ARG A 299 | 19.464 | 3.249 | 7.529 | 1.00 | 35.98 | A | C |
| ATOM | 490 | CD | ARG A 299 | 20.596 | 4.215 | 7.502 | 1.00 | 38.28 | A | C |
| ATOM | 491 | NE | ARG A 299 | 21.617 | 3.692 | 6.634 | 1.00 | 42.82 | A | N |
| ATOM | 492 | CZ | ARG A 299 | 22.918 | 3.786 | 6.879 | 1.00 | 45.32 | A | C |
| ATOM | 493 | NH1 | ARG A 299 | 23.366 | 4.395 | 7.994 | 1.00 | 46.01 | A | N |
| ATOM | 494 | NH2 | ARG A 299 | 23.761 | 3.295 | 5.976 | 1.00 | 46.15 | A | N |
| ATOM | 495 | C | ARG A 299 | 19.019 | 3.689 | 11.272 | 1.00 | 29.57 | A | C |
| ATOM | 496 | O | ARG A 299 | 18.710 | 4.891 | 11.347 | 1.00 | 28.60 | A | O |
| ATOM | 497 | N | LEU A 300 | 18.814 | 2.807 | 12.245 | 1.00 | 26.96 | A | N |
| ATOM | 498 | CA | LEU A 300 | 18.217 | 3.149 | 13.534 | 1.00 | 27.54 | A | C |
| ATOM | 499 | CB | LEU A 300 | 17.041 | 2.191 | 13.819 | 1.00 | 25.87 | A | C |
| ATOM | 500 | CG | LEU A 300 | 15.670 | 2.517 | 13.223 | 1.00 | 26.13 | A | C |
| ATOM | 501 | CD1 | LEU A 300 | 15.776 | 2.874 | 11.772 | 1.00 | 25.49 | A | C |
| ATOM | 502 | CD2 | LEU A 300 | 14.719 | 1.357 | 13.444 | 1.00 | 27.33 | A | C |
| ATOM | 503 | C | LEU A 300 | 19.266 | 3.020 | 14.639 | 1.00 | 26.86 | A | C |
| ATOM | 504 | O | LEU A 300 | 20.026 | 2.089 | 14.623 | 1.00 | 27.12 | A | O |
| ATOM | 505 | N | VAL A 301 | 19.286 | 3.939 | 15.599 | 1.00 | 27.48 | A | N |
| ATOM | 506 | CA | VAL A 301 | 20.242 | 3.877 | 16.716 | 1.00 | 28.23 | A | C |
| ATOM | 507 | CB | VAL A 301 | 20.097 | 5.096 | 17.641 | 1.00 | 28.00 | A | C |
| ATOM | 508 | CG1 | VAL A 301 | 20.941 | 4.891 | 18.907 | 1.00 | 27.80 | A | C |
| ATOM | 509 | CG2 | VAL A 301 | 20.526 | 6.359 | 16.909 | 1.00 | 25.59 | A | C |
| ATOM | 510 | C | VAL A 301 | 20.040 | 2.597 | 17.543 | 1.00 | 29.65 | A | C |
| ATOM | 511 | O | VAL A 301 | 18.950 | 2.349 | 18.045 | 1.00 | 29.93 | A | O |
| ATOM | 512 | N | ARG A 302 | 21.092 | 1.789 | 17.645 | 1.00 | 30.83 | A | N |
| ATOM | 513 | CA | ARG A 302 | 21.077 | 0.511 | 18.346 | 1.00 | 33.54 | A | C |
| ATOM | 514 | CB | ARG A 302 | 22.130 | -0.418 | 17.724 | 1.00 | 37.01 | A | C |
| ATOM | 515 | CG | ARG A 302 | 22.258 | -1.813 | 18.318 | 1.00 | 42.77 | A | C |
| ATOM | 516 | CD | ARG A 302 | 23.476 | -1.867 | 19.238 | 1.00 | 48.82 | A | C |
| ATOM | 517 | NE | ARG A 302 | 23.996 | -3.224 | 19.471 | 1.00 | 53.86 | A | N |
| ATOM | 518 | CZ | ARG A 302 | 24.937 | -3.807 | 18.724 | 1.00 | 55.22 | A | C |

Figure 11

| | | | | | | | | | | |
|---|---|---|---|---|---|---|---|---|---|---|
| ATOM | 519 | NH1 | ARG | A | 302 | 25.461 | -3.161 | 17.686 | 1.00 56.26 | A N |
| ATOM | 520 | NH2 | ARG | A | 302 | 25.435 | -4.985 | 19.083 | 1.00 56.05 | A N |
| ATOM | 521 | C | ARG | A | 302 | 21.249 | 0.579 | 19.859 | 1.00 33.84 | A C |
| ATOM | 522 | O | ARG | A | 302 | 22.058 | 1.350 | 20.393 | 1.00 32.02 | A O |
| ATOM | 523 | N | LEU | A | 303 | 20.462 | -0.244 | 20.538 | 1.00 34.87 | A N |
| ATOM | 524 | CA | LEU | A | 303 | 20.503 | -0.329 | 21.987 | 1.00 36.11 | A C |
| ATOM | 525 | CB | LEU | A | 303 | 19.107 | -0.560 | 22.549 | 1.00 36.40 | A C |
| ATOM | 526 | CG | LEU | A | 303 | 19.144 | -0.882 | 24.036 | 1.00 37.28 | A C |
| ATOM | 527 | CD1 | LEU | A | 303 | 19.326 | 0.405 | 24.817 | 1.00 38.26 | A C |
| ATOM | 528 | CD2 | LEU | A | 303 | 17.896 | -1.614 | 24.469 | 1.00 38.04 | A C |
| ATOM | 529 | C | LEU | A | 303 | 21.402 | -1.479 | 22.413 | 1.00 36.28 | A C |
| ATOM | 530 | O | LEU | A | 303 | 21.335 | -2.563 | 21.833 | 1.00 36.05 | A O |
| ATOM | 531 | N | TYR | A | 304 | 22.284 | -1.218 | 23.378 | 1.00 36.52 | A N |
| ATOM | 532 | CA | TYR | A | 304 | 23.158 | -2.264 | 23.901 | 1.00 37.25 | A C |
| ATOM | 533 | CB | TYR | A | 304 | 24.569 | -1.740 | 24.180 | 1.00 39.42 | A C |
| ATOM | 534 | CG | TYR | A | 304 | 25.425 | -1.563 | 22.954 | 1.00 42.19 | A C |
| ATOM | 535 | CD1 | TYR | A | 304 | 25.961 | -0.322 | 22.631 | 1.00 43.17 | A C |
| ATOM | 536 | CE1 | TYR | A | 304 | 26.706 | -0.128 | 21.483 | 1.00 43.54 | A C |
| ATOM | 537 | CD2 | TYR | A | 304 | 25.667 | -2.623 | 22.092 | 1.00 44.95 | A C |
| ATOM | 538 | CE2 | TYR | A | 304 | 26.426 | -2.432 | 20.930 | 1.00 46.27 | A C |
| ATOM | 539 | CZ | TYR | A | 304 | 26.932 | -1.178 | 20.640 | 1.00 45.01 | A C |
| ATOM | 540 | OH | TYR | A | 304 | 27.655 | -0.977 | 19.491 | 1.00 47.09 | A O |
| ATOM | 541 | C | TYR | A | 304 | 22.582 | -2.832 | 25.189 | 1.00 36.49 | A C |
| ATOM | 542 | O | TYR | A | 304 | 22.425 | -4.028 | 25.310 | 1.00 36.84 | A O |
| ATOM | 543 | N | ALA | A | 305 | 22.201 | -1.964 | 26.121 | 1.00 36.47 | A N |
| ATOM | 544 | CA | ALA | A | 305 | 21.686 | -2.419 | 27.407 | 1.00 36.09 | A C |
| ATOM | 545 | CB | ALA | A | 305 | 22.852 | -3.055 | 28.195 | 1.00 36.40 | A C |
| ATOM | 546 | C | ALA | A | 305 | 21.047 | -1.310 | 28.238 | 1.00 35.71 | A C |
| ATOM | 547 | O | ALA | A | 305 | 20.920 | -0.168 | 27.792 | 1.00 34.89 | A O |
| ATOM | 548 | N | VAL | A | 306 | 20.666 | -1.668 | 29.463 | 1.00 35.95 | A N |
| ATOM | 549 | CA | VAL | A | 306 | 20.063 | -0.748 | 30.431 | 1.00 36.69 | A C |
| ATOM | 550 | CB | VAL | A | 306 | 18.485 | -0.812 | 30.431 | 1.00 36.55 | A C |
| ATOM | 551 | CG1 | VAL | A | 306 | 17.888 | -0.314 | 29.090 | 1.00 35.49 | A C |
| ATOM | 552 | CG2 | VAL | A | 306 | 18.018 | -2.229 | 30.722 | 1.00 35.89 | A C |
| ATOM | 553 | C | VAL | A | 306 | 20.511 | -1.086 | 31.873 | 1.00 37.71 | A C |
| ATOM | 554 | O | VAL | A | 306 | 20.843 | -2.240 | 32.177 | 1.00 37.67 | A O |
| ATOM | 555 | N | VAL | A | 307 | 20.524 | -0.075 | 32.739 | 1.00 37.72 | A N |
| ATOM | 556 | CA | VAL | A | 307 | 20.847 | -0.256 | 34.147 | 1.00 39.55 | A C |
| ATOM | 557 | CB | VAL | A | 307 | 22.086 | 0.577 | 34.585 | 1.00 38.99 | A C |
| ATOM | 558 | CG1 | VAL | A | 307 | 22.254 | 0.576 | 36.119 | 1.00 37.73 | A C |
| ATOM | 559 | CG2 | VAL | A | 307 | 23.335 | -0.005 | 33.914 | 1.00 37.28 | A C |
| ATOM | 560 | C | VAL | A | 307 | 19.563 | 0.164 | 34.862 | 1.00 41.34 | A C |
| ATOM | 561 | O | VAL | A | 307 | 19.115 | 1.306 | 34.759 | 1.00 40.53 | A O |
| ATOM | 562 | N | THR | A | 308 | 18.940 | -0.804 | 35.526 | 1.00 43.71 | A N |
| ATOM | 563 | CA | THR | A | 308 | 17.677 | -0.581 | 36.223 | 1.00 46.25 | A C |
| ATOM | 564 | CB | THR | A | 308 | 16.855 | -1.875 | 36.229 | 1.00 45.81 | A C |
| ATOM | 565 | OG1 | THR | A | 308 | 17.630 | -2.932 | 36.793 | 1.00 46.20 | A O |
| ATOM | 566 | CG2 | THR | A | 308 | 16.528 | -2.261 | 34.822 | 1.00 45.71 | A C |
| ATOM | 567 | C | THR | A | 308 | 17.687 | 0.072 | 37.613 | 1.00 48.09 | A C |
| ATOM | 568 | O | THR | A | 308 | 16.643 | 0.480 | 38.112 | 1.00 47.97 | A O |
| ATOM | 569 | N | GLN | A | 309 | 18.847 | 0.191 | 38.245 | 1.00 49.87 | A N |
| ATOM | 570 | CA | GLN | A | 309 | 18.889 | 0.844 | 39.551 | 1.00 51.77 | A C |
| ATOM | 571 | CB | GLN | A | 309 | 19.809 | 0.106 | 40.527 | 1.00 54.47 | A C |
| ATOM | 572 | CG | GLN | A | 309 | 19.349 | -1.323 | 40.846 | 1.00 59.08 | A C |
| ATOM | 573 | CD | GLN | A | 309 | 17.960 | -1.400 | 41.520 | 1.00 60.94 | A C |
| ATOM | 574 | OE1 | GLN | A | 309 | 17.294 | -0.393 | 41.792 | 1.00 61.40 | A O |
| ATOM | 575 | NE2 | GLN | A | 309 | 17.535 | -2.630 | 41.811 | 1.00 62.76 | A N |
| ATOM | 576 | C | GLN | A | 309 | 19.315 | 2.292 | 39.426 | 1.00 51.53 | A C |
| ATOM | 577 | O | GLN | A | 309 | 20.199 | 2.610 | 38.648 | 1.00 51.43 | A O |

Figure 11

| ATOM | 578 | N   | GLU | A | 310 | 18.695 | 3.152 | 40.225 | 1.00 | 51.43 | A | N |
|------|-----|-----|-----|---|-----|--------|-------|--------|------|-------|---|---|
| ATOM | 579 | CA  | GLU | A | 310 | 18.966 | 4.588 | 40.233 | 1.00 | 51.62 | A | C |
| ATOM | 580 | CB  | GLU | A | 310 | 18.020 | 5.280 | 41.237 | 1.00 | 54.05 | A | C |
| ATOM | 581 | CG  | GLU | A | 310 | 17.897 | 4.591 | 42.643 | 1.00 | 57.76 | A | C |
| ATOM | 582 | CD  | GLU | A | 310 | 16.615 | 3.740 | 42.854 | 1.00 | 59.79 | A | C |
| ATOM | 583 | OE1 | GLU | A | 310 | 15.498 | 4.237 | 42.577 | 1.00 | 60.93 | A | O |
| ATOM | 584 | OE2 | GLU | A | 310 | 16.722 | 2.586 | 43.343 | 1.00 | 60.05 | A | O |
| ATOM | 585 | C   | GLU | A | 310 | 20.442 | 4.956 | 40.516 | 1.00 | 50.45 | A | C |
| ATOM | 586 | O   | GLU | A | 310 | 21.048 | 4.427 | 41.440 | 1.00 | 50.30 | A | O |
| ATOM | 587 | N   | PRO | A | 311 | 21.065 | 5.806 | 39.652 | 1.00 | 49.14 | A | N |
| ATOM | 588 | CD  | PRO | A | 311 | 22.442 | 6.266 | 39.885 | 1.00 | 49.28 | A | C |
| ATOM | 589 | CA  | PRO | A | 311 | 20.521 | 6.451 | 38.444 | 1.00 | 47.31 | A | C |
| ATOM | 590 | CB  | PRO | A | 311 | 21.601 | 7.486 | 38.077 | 1.00 | 48.32 | A | C |
| ATOM | 591 | CG  | PRO | A | 311 | 22.401 | 7.659 | 39.331 | 1.00 | 49.35 | A | C |
| ATOM | 592 | C   | PRO | A | 311 | 20.328 | 5.446 | 37.299 | 1.00 | 44.47 | A | C |
| ATOM | 593 | O   | PRO | A | 311 | 21.192 | 4.607 | 37.053 | 1.00 | 44.45 | A | O |
| ATOM | 594 | N   | ILE | A | 312 | 19.192 | 5.543 | 36.613 | 1.00 | 41.83 | A | N |
| ATOM | 595 | CA  | ILE | A | 312 | 18.849 | 4.657 | 35.495 | 1.00 | 38.24 | A | C |
| ATOM | 596 | CB  | ILE | A | 312 | 17.358 | 4.817 | 35.114 | 1.00 | 39.46 | A | C |
| ATOM | 597 | CG2 | ILE | A | 312 | 16.940 | 3.696 | 34.198 | 1.00 | 38.89 | A | C |
| ATOM | 598 | CG1 | ILE | A | 312 | 16.457 | 4.901 | 36.368 | 1.00 | 39.99 | A | C |
| ATOM | 599 | CD1 | ILE | A | 312 | 16.398 | 3.628 | 37.202 | 1.00 | 39.87 | A | C |
| ATOM | 600 | C   | ILE | A | 312 | 19.671 | 5.019 | 34.252 | 1.00 | 35.63 | A | C |
| ATOM | 601 | O   | ILE | A | 312 | 19.824 | 6.193 | 33.927 | 1.00 | 34.66 | A | O |
| ATOM | 602 | N   | TYR | A | 313 | 20.172 | 4.008 | 33.551 | 1.00 | 32.94 | A | N |
| ATOM | 603 | CA  | TYR | A | 313 | 20.949 | 4.223 | 32.324 | 1.00 | 31.10 | A | C |
| ATOM | 604 | CB  | TYR | A | 313 | 22.396 | 3.687 | 32.455 | 1.00 | 28.74 | A | C |
| ATOM | 605 | CG  | TYR | A | 313 | 23.353 | 4.399 | 33.391 | 1.00 | 27.13 | A | C |
| ATOM | 606 | CD1 | TYR | A | 313 | 23.058 | 5.642 | 33.916 | 1.00 | 27.03 | A | C |
| ATOM | 607 | CE1 | TYR | A | 313 | 23.940 | 6.293 | 34.765 | 1.00 | 27.85 | A | C |
| ATOM | 608 | CD2 | TYR | A | 313 | 24.578 | 3.812 | 33.740 | 1.00 | 27.84 | A | C |
| ATOM | 609 | CE2 | TYR | A | 313 | 25.475 | 4.459 | 34.586 | 1.00 | 26.48 | A | C |
| ATOM | 610 | CZ  | TYR | A | 313 | 25.147 | 5.697 | 35.100 | 1.00 | 27.57 | A | C |
| ATOM | 611 | OH  | TYR | A | 313 | 25.981 | 6.367 | 35.971 | 1.00 | 28.03 | A | O |
| ATOM | 612 | C   | TYR | A | 313 | 20.372 | 3.473 | 31.116 | 1.00 | 30.10 | A | C |
| ATOM | 613 | O   | TYR | A | 313 | 19.845 | 2.359 | 31.242 | 1.00 | 28.93 | A | O |
| ATOM | 614 | N   | ILE | A | 314 | 20.449 | 4.118 | 29.955 | 1.00 | 29.26 | A | N |
| ATOM | 615 | CA  | ILE | A | 314 | 20.121 | 3.454 | 28.700 | 1.00 | 28.97 | A | C |
| ATOM | 616 | CB  | ILE | A | 314 | 19.049 | 4.194 | 27.843 | 1.00 | 29.98 | A | C |
| ATOM | 617 | CG2 | ILE | A | 314 | 18.993 | 3.565 | 26.448 | 1.00 | 28.02 | A | C |
| ATOM | 618 | CG1 | ILE | A | 314 | 17.669 | 4.124 | 28.521 | 1.00 | 30.38 | A | C |
| ATOM | 619 | CD1 | ILE | A | 314 | 16.671 | 5.096 | 27.911 | 1.00 | 34.31 | A | C |
| ATOM | 620 | C   | ILE | A | 314 | 21.473 | 3.525 | 27.980 | 1.00 | 28.00 | A | C |
| ATOM | 621 | O   | ILE | A | 314 | 22.044 | 4.595 | 27.870 | 1.00 | 28.39 | A | O |
| ATOM | 622 | N   | ILE | A | 315 | 21.983 | 2.400 | 27.508 | 1.00 | 28.17 | A | N |
| ATOM | 623 | CA  | ILE | A | 315 | 23.263 | 2.385 | 26.834 | 1.00 | 29.00 | A | C |
| ATOM | 624 | CB  | ILE | A | 315 | 24.241 | 1.312 | 27.440 | 1.00 | 29.83 | A | C |
| ATOM | 625 | CG2 | ILE | A | 315 | 25.547 | 1.241 | 26.639 | 1.00 | 28.45 | A | C |
| ATOM | 626 | CG1 | ILE | A | 315 | 24.613 | 1.689 | 28.873 | 1.00 | 30.82 | A | C |
| ATOM | 627 | CD1 | ILE | A | 315 | 23.930 | 0.866 | 29.940 | 1.00 | 32.58 | A | C |
| ATOM | 628 | C   | ILE | A | 315 | 23.054 | 2.110 | 25.363 | 1.00 | 28.62 | A | C |
| ATOM | 629 | O   | ILE | A | 315 | 22.445 | 1.117 | 25.007 | 1.00 | 29.62 | A | O |
| ATOM | 630 | N   | THR | A | 316 | 23.552 | 3.003 | 24.510 | 1.00 | 28.05 | A | N |
| ATOM | 631 | CA  | THR | A | 316 | 23.412 | 2.819 | 23.068 | 1.00 | 27.84 | A | C |
| ATOM | 632 | CB  | THR | A | 316 | 22.476 | 3.860 | 22.476 | 1.00 | 27.00 | A | C |
| ATOM | 633 | OG1 | THR | A | 316 | 23.121 | 5.142 | 22.457 | 1.00 | 23.70 | A | O |
| ATOM | 634 | CG2 | THR | A | 316 | 21.176 | 3.949 | 23.263 | 1.00 | 26.75 | A | C |
| ATOM | 635 | C   | THR | A | 316 | 24.753 | 3.022 | 22.347 | 1.00 | 28.83 | A | C |
| ATOM | 636 | O   | THR | A | 316 | 25.721 | 3.516 | 22.939 | 1.00 | 29.51 | A | O |

Figure 11

| | | | | | | | | | | | |
|---|---|---|---|---|---|---|---|---|---|---|---|
| ATOM | 637 | N | GLU | A | 317 | 24.804 | 2.647 | 21.072 | 1.00 | 28.16 | A | N |
| ATOM | 638 | CA | GLU | A | 317 | 25.991 | 2.888 | 20.269 | 1.00 | 27.56 | A | C |
| ATOM | 639 | CB | GLU | A | 317 | 25.786 | 2.460 | 18.803 | 1.00 | 27.86 | A | C |
| ATOM | 640 | CG | GLU | A | 317 | 24.775 | 3.295 | 17.986 | 1.00 | 27.54 | A | C |
| ATOM | 641 | CD | GLU | A | 317 | 24.629 | 2.786 | 16.560 | 1.00 | 29.08 | A | C |
| ATOM | 642 | OE1 | GLU | A | 317 | 23.540 | 2.308 | 16.180 | 1.00 | 29.12 | A | O |
| ATOM | 643 | OE2 | GLU | A | 317 | 25.634 | 2.812 | 15.816 | 1.00 | 31.47 | A | O |
| ATOM | 644 | C | GLU | A | 317 | 26.288 | 4.388 | 20.329 | 1.00 | 27.06 | A | C |
| ATOM | 645 | O | GLU | A | 317 | 25.398 | 5.223 | 20.562 | 1.00 | 26.44 | A | O |
| ATOM | 646 | N | TYR | A | 318 | 27.557 | 4.719 | 20.132 | 1.00 | 26.95 | A | N |
| ATOM | 647 | CA | TYR | A | 318 | 27.992 | 6.096 | 20.187 | 1.00 | 26.66 | A | C |
| ATOM | 648 | CB | TYR | A | 318 | 29.372 | 6.172 | 20.889 | 1.00 | 26.15 | A | C |
| ATOM | 649 | CG | TYR | A | 318 | 29.973 | 7.556 | 20.964 | 1.00 | 25.50 | A | C |
| ATOM | 650 | CD1 | TYR | A | 318 | 29.419 | 8.533 | 21.781 | 1.00 | 26.47 | A | C |
| ATOM | 651 | CE1 | TYR | A | 318 | 29.970 | 9.848 | 21.827 | 1.00 | 26.87 | A | C |
| ATOM | 652 | CD2 | TYR | A | 318 | 31.088 | 7.901 | 20.190 | 1.00 | 25.61 | A | C |
| ATOM | 653 | CE2 | TYR | A | 318 | 31.636 | 9.181 | 20.228 | 1.00 | 25.46 | A | C |
| ATOM | 654 | CZ | TYR | A | 318 | 31.076 | 10.143 | 21.042 | 1.00 | 26.50 | A | C |
| ATOM | 655 | OH | TYR | A | 318 | 31.613 | 11.398 | 21.086 | 1.00 | 28.43 | A | O |
| ATOM | 656 | C | TYR | A | 318 | 28.013 | 6.735 | 18.794 | 1.00 | 25.84 | A | C |
| ATOM | 657 | O | TYR | A | 318 | 28.451 | 6.125 | 17.811 | 1.00 | 25.28 | A | O |
| ATOM | 658 | N | MET | A | 319 | 27.451 | 7.933 | 18.711 | 1.00 | 25.65 | A | N |
| ATOM | 659 | CA | MET | A | 319 | 27.383 | 8.673 | 17.451 | 1.00 | 25.82 | A | C |
| ATOM | 660 | CB | MET | A | 319 | 25.938 | 9.029 | 17.105 | 1.00 | 25.61 | A | C |
| ATOM | 661 | CG | MET | A | 319 | 25.040 | 7.825 | 16.946 | 1.00 | 24.69 | A | C |
| ATOM | 662 | SD | MET | A | 319 | 25.470 | 6.737 | 15.571 | 1.00 | 28.29 | A | S |
| ATOM | 663 | CE | MET | A | 319 | 24.941 | 7.791 | 14.179 | 1.00 | 22.23 | A | C |
| ATOM | 664 | C | MET | A | 319 | 28.225 | 9.920 | 17.628 | 1.00 | 26.50 | A | C |
| ATOM | 665 | O | MET | A | 319 | 27.800 | 10.916 | 18.207 | 1.00 | 24.50 | A | O |
| ATOM | 666 | N | GLU | A | 320 | 29.457 | 9.776 | 17.157 | 1.00 | 27.78 | A | N |
| ATOM | 667 | CA | GLU | A | 320 | 30.522 | 10.762 | 17.195 | 1.00 | 29.02 | A | C |
| ATOM | 668 | CB | GLU | A | 320 | 31.648 | 10.264 | 16.271 | 1.00 | 31.45 | A | C |
| ATOM | 669 | CG | GLU | A | 320 | 32.754 | 11.260 | 15.963 | 1.00 | 37.93 | A | C |
| ATOM | 670 | CD | GLU | A | 320 | 33.975 | 11.155 | 16.884 | 1.00 | 40.21 | A | C |
| ATOM | 671 | OE1 | GLU | A | 320 | 34.181 | 10.109 | 17.556 | 1.00 | 40.49 | A | O |
| ATOM | 672 | OE2 | GLU | A | 320 | 34.743 | 12.143 | 16.903 | 1.00 | 42.86 | A | O |
| ATOM | 673 | C | GLU | A | 320 | 30.133 | 12.210 | 16.905 | 1.00 | 27.64 | A | C |
| ATOM | 674 | O | GLU | A | 320 | 30.491 | 13.122 | 17.665 | 1.00 | 27.26 | A | O |
| ATOM | 675 | N | ASN | A | 321 | 29.369 | 12.433 | 15.849 | 1.00 | 26.14 | A | N |
| ATOM | 676 | CA | ASN | A | 321 | 28.993 | 13.789 | 15.501 | 1.00 | 25.84 | A | C |
| ATOM | 677 | CB | ASN | A | 321 | 29.124 | 14.003 | 13.986 | 1.00 | 27.44 | A | C |
| ATOM | 678 | CG | ASN | A | 321 | 30.604 | 14.036 | 13.522 | 1.00 | 27.65 | A | C |
| ATOM | 679 | OD1 | ASN | A | 321 | 31.317 | 14.995 | 13.794 | 1.00 | 27.82 | A | O |
| ATOM | 680 | ND2 | ASN | A | 321 | 31.041 | 12.996 | 12.828 | 1.00 | 27.00 | A | N |
| ATOM | 681 | C | ASN | A | 321 | 27.667 | 14.308 | 16.068 | 1.00 | 26.75 | A | C |
| ATOM | 682 | O | ASN | A | 321 | 27.118 | 15.324 | 15.589 | 1.00 | 26.70 | A | O |
| ATOM | 683 | N | GLY | A | 322 | 27.153 | 13.608 | 17.087 | 1.00 | 26.18 | A | N |
| ATOM | 684 | CA | GLY | A | 322 | 25.939 | 14.041 | 17.758 | 1.00 | 25.99 | A | C |
| ATOM | 685 | C | GLY | A | 322 | 24.713 | 14.264 | 16.882 | 1.00 | 26.03 | A | C |
| ATOM | 686 | O | GLY | A | 322 | 24.502 | 13.541 | 15.910 | 1.00 | 24.47 | A | O |
| ATOM | 687 | N | SER | A | 323 | 23.948 | 15.304 | 17.199 | 1.00 | 25.45 | A | N |
| ATOM | 688 | CA | SER | A | 323 | 22.739 | 15.600 | 16.451 | 1.00 | 26.62 | A | C |
| ATOM | 689 | CB | SER | A | 323 | 21.792 | 16.443 | 17.303 | 1.00 | 27.17 | A | C |
| ATOM | 690 | OG | SER | A | 323 | 20.648 | 16.789 | 16.554 | 1.00 | 30.77 | A | O |
| ATOM | 691 | C | SER | A | 323 | 22.955 | 16.286 | 15.114 | 1.00 | 26.01 | A | C |
| ATOM | 692 | O | SER | A | 323 | 23.676 | 17.258 | 15.029 | 1.00 | 24.32 | A | O |
| ATOM | 693 | N | LEU | A | 324 | 22.219 | 15.824 | 14.103 | 1.00 | 26.52 | A | N |
| ATOM | 694 | CA | LEU | A | 324 | 22.295 | 16.377 | 12.753 | 1.00 | 26.47 | A | C |
| ATOM | 695 | CB | LEU | A | 324 | 21.366 | 15.603 | 11.796 | 1.00 | 27.38 | A | C |

Figure 11

| | | | | | | | | | | | |
|---|---|---|---|---|---|---|---|---|---|---|---|
| ATOM | 696 | CG | LEU | A | 324 | 21.253 | 16.051 | 10.326 | 1.00 | 27.14 | A C |
| ATOM | 697 | CD1 | LEU | A | 324 | 22.605 | 15.873 | 9.597 | 1.00 | 25.64 | A C |
| ATOM | 698 | CD2 | LEU | A | 324 | 20.108 | 15.264 | 9.606 | 1.00 | 25.45 | A C |
| ATOM | 699 | C | LEU | A | 324 | 22.005 | 17.871 | 12.671 | 1.00 | 26.34 | A C |
| ATOM | 700 | O | LEU | A | 324 | 22.727 | 18.590 | 11.980 | 1.00 | 26.90 | A O |
| ATOM | 701 | N | VAL | A | 325 | 20.988 | 18.358 | 13.386 | 1.00 | 25.75 | A N |
| ATOM | 702 | CA | VAL | A | 325 | 20.675 | 19.775 | 13.328 | 1.00 | 24.65 | A C |
| ATOM | 703 | CB | VAL | A | 325 | 19.315 | 20.108 | 14.037 | 1.00 | 24.12 | A C |
| ATOM | 704 | CG1 | VAL | A | 325 | 19.462 | 20.209 | 15.505 | 1.00 | 21.26 | A C |
| ATOM | 705 | CG2 | VAL | A | 325 | 18.706 | 21.397 | 13.457 | 1.00 | 23.50 | A C |
| ATOM | 706 | C | VAL | A | 325 | 21.846 | 20.623 | 13.825 | 1.00 | 25.65 | A C |
| ATOM | 707 | O | VAL | A | 325 | 22.052 | 21.744 | 13.367 | 1.00 | 25.07 | A O |
| ATOM | 708 | N | ASP | A | 326 | 22.630 | 20.068 | 14.744 | 1.00 | 26.73 | A N |
| ATOM | 709 | CA | ASP | A | 326 | 23.817 | 20.762 | 15.262 | 1.00 | 28.09 | A C |
| ATOM | 710 | CB | ASP | A | 326 | 24.237 | 20.191 | 16.609 | 1.00 | 27.54 | A C |
| ATOM | 711 | CG | ASP | A | 326 | 23.237 | 20.464 | 17.701 | 1.00 | 27.17 | A C |
| ATOM | 712 | OD1 | ASP | A | 326 | 22.656 | 21.569 | 17.739 | 1.00 | 27.97 | A O |
| ATOM | 713 | OD2 | ASP | A | 326 | 23.083 | 19.578 | 18.550 | 1.00 | 26.61 | A O |
| ATOM | 714 | C | ASP | A | 326 | 24.997 | 20.569 | 14.308 | 1.00 | 28.13 | A C |
| ATOM | 715 | O | ASP | A | 326 | 25.723 | 21.516 | 14.021 | 1.00 | 28.36 | A O |
| ATOM | 716 | N | PHE | A | 327 | 25.161 | 19.344 | 13.805 | 1.00 | 28.42 | A N |
| ATOM | 717 | CA | PHE | A | 327 | 26.269 | 19.023 | 12.916 | 1.00 | 29.98 | A C |
| ATOM | 718 | CB | PHE | A | 327 | 26.322 | 17.539 | 12.591 | 1.00 | 30.18 | A C |
| ATOM | 719 | CG | PHE | A | 327 | 27.418 | 17.192 | 11.625 | 1.00 | 33.25 | A C |
| ATOM | 720 | CD1 | PHE | A | 327 | 28.757 | 17.285 | 12.013 | 1.00 | 32.77 | A C |
| ATOM | 721 | CD2 | PHE | A | 327 | 27.124 | 16.846 | 10.308 | 1.00 | 32.96 | A C |
| ATOM | 722 | CE1 | PHE | A | 327 | 29.781 | 17.048 | 11.105 | 1.00 | 33.03 | A C |
| ATOM | 723 | CE2 | PHE | A | 327 | 28.150 | 16.604 | 9.395 | 1.00 | 34.31 | A C |
| ATOM | 724 | CZ | PHE | A | 327 | 29.477 | 16.707 | 9.793 | 1.00 | 33.09 | A C |
| ATOM | 725 | C | PHE | A | 327 | 26.298 | 19.825 | 11.619 | 1.00 | 31.18 | A C |
| ATOM | 726 | O | PHE | A | 327 | 27.365 | 20.228 | 11.159 | 1.00 | 31.75 | A O |
| ATOM | 727 | N | LEU | A | 328 | 25.123 | 20.042 | 11.033 | 1.00 | 30.79 | A N |
| ATOM | 728 | CA | LEU | A | 328 | 25.005 | 20.791 | 9.803 | 1.00 | 30.84 | A C |
| ATOM | 729 | CB | LEU | A | 328 | 23.542 | 20.852 | 9.363 | 1.00 | 30.06 | A C |
| ATOM | 730 | CG | LEU | A | 328 | 22.894 | 19.544 | 8.917 | 1.00 | 28.88 | A C |
| ATOM | 731 | CD1 | LEU | A | 328 | 21.429 | 19.760 | 8.650 | 1.00 | 29.07 | A C |
| ATOM | 732 | CD2 | LEU | A | 328 | 23.608 | 19.014 | 7.705 | 1.00 | 28.70 | A C |
| ATOM | 733 | C | LEU | A | 328 | 25.535 | 22.202 | 9.967 | 1.00 | 31.99 | A C |
| ATOM | 734 | O | LEU | A | 328 | 26.005 | 22.795 | 9.000 | 1.00 | 32.18 | A O |
| ATOM | 735 | N | LYS | A | 329 | 25.455 | 22.729 | 11.193 | 1.00 | 33.22 | A N |
| ATOM | 736 | CA | LYS | A | 329 | 25.894 | 24.088 | 11.492 | 1.00 | 34.33 | A C |
| ATOM | 737 | CB | LYS | A | 329 | 25.072 | 24.671 | 12.648 | 1.00 | 34.79 | A C |
| ATOM | 738 | CG | LYS | A | 329 | 23.599 | 24.869 | 12.359 | 1.00 | 35.10 | A C |
| ATOM | 739 | CD | LYS | A | 329 | 22.979 | 25.776 | 13.417 | 1.00 | 34.82 | A C |
| ATOM | 740 | CE | LYS | A | 329 | 21.490 | 25.586 | 13.523 | 1.00 | 34.35 | A C |
| ATOM | 741 | NZ | LYS | A | 329 | 21.212 | 24.173 | 13.874 | 1.00 | 36.19 | A N |
| ATOM | 742 | C | LYS | A | 329 | 27.396 | 24.280 | 11.771 | 1.00 | 34.73 | A C |
| ATOM | 743 | O | LYS | A | 329 | 27.870 | 25.423 | 11.822 | 1.00 | 34.93 | A O |
| ATOM | 744 | N | THR | A | 330 | 28.133 | 23.177 | 11.913 | 1.00 | 34.94 | A N |
| ATOM | 745 | CA | THR | A | 330 | 29.575 | 23.216 | 12.181 | 1.00 | 35.57 | A C |
| ATOM | 746 | CB | THR | A | 330 | 30.109 | 21.862 | 12.729 | 1.00 | 34.05 | A C |
| ATOM | 747 | OG1 | THR | A | 330 | 30.053 | 20.862 | 11.707 | 1.00 | 33.94 | A O |
| ATOM | 748 | CG2 | THR | A | 330 | 29.341 | 21.389 | 13.939 | 1.00 | 34.84 | A C |
| ATOM | 749 | C | THR | A | 330 | 30.368 | 23.493 | 10.907 | 1.00 | 36.52 | A C |
| ATOM | 750 | O | THR | A | 330 | 29.870 | 23.288 | 9.809 | 1.00 | 36.94 | A O |
| ATOM | 751 | N | PRO | A | 331 | 31.613 | 23.979 | 11.039 | 1.00 | 37.63 | A N |
| ATOM | 752 | CD | PRO | A | 331 | 32.232 | 24.567 | 12.248 | 1.00 | 38.09 | A C |
| ATOM | 753 | CA | PRO | A | 331 | 32.424 | 24.251 | 9.851 | 1.00 | 38.08 | A C |
| ATOM | 754 | CB | PRO | A | 331 | 33.819 | 24.485 | 10.445 | 1.00 | 38.24 | A C |

Figure 11

| | | | | | | | | | | | |
|---|---|---|---|---|---|---|---|---|---|---|---|
| ATOM | 755 | CG | PRO | A | 331 | 33.490 | 25.297 | 11.685 | 1.00 | 37.26 | A | C |
| ATOM | 756 | C | PRO | A | 331 | 32.394 | 23.081 | 8.867 | 1.00 | 39.24 | A | C |
| ATOM | 757 | O | PRO | A | 331 | 32.245 | 23.303 | 7.671 | 1.00 | 39.73 | A | O |
| ATOM | 758 | N | SER | A | 332 | 32.476 | 21.842 | 9.365 | 1.00 | 39.87 | A | N |
| ATOM | 759 | CA | SER | A | 332 | 32.425 | 20.649 | 8.503 | 1.00 | 41.43 | A | C |
| ATOM | 760 | CB | SER | A | 332 | 32.677 | 19.355 | 9.291 | 1.00 | 42.10 | A | C |
| ATOM | 761 | OG | SER | A | 332 | 33.958 | 19.325 | 9.864 | 1.00 | 44.13 | A | O |
| ATOM | 762 | C | SER | A | 332 | 31.053 | 20.492 | 7.837 | 1.00 | 41.59 | A | C |
| ATOM | 763 | O | SER | A | 332 | 30.957 | 20.123 | 6.656 | 1.00 | 41.87 | A | O |
| ATOM | 764 | N | GLY | A | 333 | 30.008 | 20.684 | 8.646 | 1.00 | 41.10 | A | N |
| ATOM | 765 | CA | GLY | A | 333 | 28.640 | 20.566 | 8.177 | 1.00 | 40.99 | A | C |
| ATOM | 766 | C | GLY | A | 333 | 28.334 | 21.581 | 7.105 | 1.00 | 40.32 | A | C |
| ATOM | 767 | O | GLY | A | 333 | 27.834 | 21.227 | 6.049 | 1.00 | 40.07 | A | O |
| ATOM | 768 | N | ILE | A | 334 | 28.723 | 22.822 | 7.352 | 1.00 | 40.61 | A | N |
| ATOM | 769 | CA | ILE | A | 334 | 28.527 | 23.927 | 6.419 | 1.00 | 41.13 | A | C |
| ATOM | 770 | CB | ILE | A | 334 | 29.141 | 25.219 | 6.998 | 1.00 | 41.74 | A | C |
| ATOM | 771 | CG2 | ILE | A | 334 | 29.301 | 26.298 | 5.928 | 1.00 | 42.17 | A | C |
| ATOM | 772 | CG1 | ILE | A | 334 | 28.273 | 25.723 | 8.150 | 1.00 | 42.52 | A | C |
| ATOM | 773 | CD1 | ILE | A | 334 | 26.879 | 26.184 | 7.748 | 1.00 | 44.13 | A | C |
| ATOM | 774 | C | ILE | A | 334 | 29.131 | 23.642 | 5.045 | 1.00 | 41.23 | A | C |
| ATOM | 775 | O | ILE | A | 334 | 28.600 | 24.094 | 4.029 | 1.00 | 41.33 | A | O |
| ATOM | 776 | N | LYS | A | 335 | 30.207 | 22.853 | 5.021 | 1.00 | 40.80 | A | N |
| ATOM | 777 | CA | LYS | A | 335 | 30.911 | 22.509 | 3.784 | 1.00 | 40.26 | A | C |
| ATOM | 778 | CB | LYS | A | 335 | 32.396 | 22.238 | 4.073 | 1.00 | 42.30 | A | C |
| ATOM | 779 | CG | LYS | A | 335 | 33.186 | 23.440 | 4.570 | 1.00 | 44.83 | A | C |
| ATOM | 780 | CD | LYS | A | 335 | 34.527 | 22.950 | 5.173 | 1.00 | 47.87 | A | C |
| ATOM | 781 | CE | LYS | A | 335 | 35.209 | 24.040 | 6.017 | 1.00 | 49.52 | A | C |
| ATOM | 782 | NZ | LYS | A | 335 | 36.016 | 23.429 | 7.143 | 1.00 | 51.07 | A | N |
| ATOM | 783 | C | LYS | A | 335 | 30.366 | 21.305 | 3.031 | 1.00 | 38.96 | A | C |
| ATOM | 784 | O | LYS | A | 335 | 30.865 | 20.986 | 1.947 | 1.00 | 38.38 | A | O |
| ATOM | 785 | N | LEU | A | 336 | 29.398 | 20.594 | 3.613 | 1.00 | 37.03 | A | N |
| ATOM | 786 | CA | LEU | A | 336 | 28.834 | 19.414 | 2.939 | 1.00 | 35.36 | A | C |
| ATOM | 787 | CB | LEU | A | 336 | 27.805 | 18.708 | 3.831 | 1.00 | 34.99 | A | C |
| ATOM | 788 | CG | LEU | A | 336 | 28.408 | 18.022 | 5.069 | 1.00 | 33.42 | A | C |
| ATOM | 789 | CD1 | LEU | A | 336 | 27.311 | 17.292 | 5.808 | 1.00 | 32.84 | A | C |
| ATOM | 790 | CD2 | LEU | A | 336 | 29.518 | 17.054 | 4.676 | 1.00 | 32.63 | A | C |
| ATOM | 791 | C | LEU | A | 336 | 28.242 | 19.711 | 1.558 | 1.00 | 34.10 | A | C |
| ATOM | 792 | O | LEU | A | 336 | 27.582 | 20.744 | 1.350 | 1.00 | 33.29 | A | O |
| ATOM | 793 | N | THR | A | 337 | 28.524 | 18.821 | 0.608 | 1.00 | 33.89 | A | N |
| ATOM | 794 | CA | THR | A | 337 | 28.035 | 18.977 | -0.767 | 1.00 | 33.54 | A | C |
| ATOM | 795 | CB | THR | A | 337 | 28.906 | 18.183 | -1.842 | 1.00 | 34.08 | A | C |
| ATOM | 796 | OG1 | THR | A | 337 | 28.728 | 16.767 | -1.708 | 1.00 | 32.82 | A | O |
| ATOM | 797 | CG2 | THR | A | 337 | 30.404 | 18.537 | -1.727 | 1.00 | 33.91 | A | C |
| ATOM | 798 | C | THR | A | 337 | 26.583 | 18.523 | -0.868 | 1.00 | 33.51 | A | C |
| ATOM | 799 | O | THR | A | 337 | 26.121 | 17.709 | -0.046 | 1.00 | 33.06 | A | O |
| ATOM | 800 | N | ILE | A | 338 | 25.881 | 19.015 | -1.896 | 1.00 | 33.60 | A | N |
| ATOM | 801 | CA | ILE | A | 338 | 24.485 | 18.651 | -2.117 | 1.00 | 32.47 | A | C |
| ATOM | 802 | CB | ILE | A | 338 | 23.858 | 19.406 | -3.326 | 1.00 | 33.36 | A | C |
| ATOM | 803 | CG2 | ILE | A | 338 | 24.622 | 19.082 | -4.620 | 1.00 | 34.37 | A | C |
| ATOM | 804 | CG1 | ILE | A | 338 | 22.380 | 19.014 | -3.506 | 1.00 | 33.99 | A | C |
| ATOM | 805 | CD1 | ILE | A | 338 | 21.454 | 19.391 | -2.355 | 1.00 | 31.86 | A | C |
| ATOM | 806 | C | ILE | A | 338 | 24.419 | 17.160 | -2.320 | 1.00 | 31.58 | A | C |
| ATOM | 807 | O | ILE | A | 338 | 23.466 | 16.514 | -1.911 | 1.00 | 31.48 | A | O |
| ATOM | 808 | N | ASN | A | 339 | 25.469 | 16.603 | -2.905 | 1.00 | 32.16 | A | N |
| ATOM | 809 | CA | ASN | A | 339 | 25.537 | 15.161 | -3.133 | 1.00 | 32.24 | A | C |
| ATOM | 810 | CB | ASN | A | 339 | 26.807 | 14.822 | -3.906 | 1.00 | 33.20 | A | C |
| ATOM | 811 | CG | ASN | A | 339 | 26.814 | 15.445 | -5.266 | 1.00 | 34.07 | A | C |
| ATOM | 812 | OD1 | ASN | A | 339 | 26.487 | 14.791 | -6.256 | 1.00 | 34.17 | A | O |
| ATOM | 813 | ND2 | ASN | A | 339 | 27.121 | 16.730 | -5.322 | 1.00 | 32.91 | A | N |

Figure 11

| ATOM | 814 | C | ASN A 339 | 25.538 | 14.385 | -1.826 | 1.00 | 31.06 | A | C |
| ATOM | 815 | O | ASN A 339 | 24.948 | 13.306 | -1.730 | 1.00 | 30.09 | A | O |
| ATOM | 816 | N | LYS A 340 | 26.299 | 14.896 | -0.862 | 1.00 | 31.01 | A | N |
| ATOM | 817 | CA | LYS A 340 | 26.391 | 14.256 | 0.453 | 1.00 | 30.61 | A | C |
| ATOM | 818 | CB | LYS A 340 | 27.599 | 14.816 | 1.232 | 1.00 | 31.44 | A | C |
| ATOM | 819 | CG | LYS A 340 | 27.712 | 14.357 | 2.682 | 1.00 | 33.52 | A | C |
| ATOM | 820 | CD | LYS A 340 | 28.035 | 12.857 | 2.806 | 1.00 | 34.71 | A | C |
| ATOM | 821 | CE | LYS A 340 | 27.691 | 12.340 | 4.226 | 1.00 | 36.49 | A | C |
| ATOM | 822 | NZ | LYS A 340 | 27.844 | 10.850 | 4.392 | 1.00 | 37.36 | A | N |
| ATOM | 823 | C | LYS A 340 | 25.073 | 14.507 | 1.235 | 1.00 | 28.96 | A | C |
| ATOM | 824 | O | LYS A 340 | 24.588 | 13.634 | 1.932 | 1.00 | 28.15 | A | O |
| ATOM | 825 | N | LEU A 341 | 24.495 | 15.691 | 1.081 | 1.00 | 28.09 | A | N |
| ATOM | 826 | CA | LEU A 341 | 23.260 | 16.040 | 1.775 | 1.00 | 28.79 | A | C |
| ATOM | 827 | CB | LEU A 341 | 22.900 | 17.489 | 1.487 | 1.00 | 27.67 | A | C |
| ATOM | 828 | CG | LEU A 341 | 23.904 | 18.493 | 2.035 | 1.00 | 27.17 | A | C |
| ATOM | 829 | CD1 | LEU A 341 | 23.451 | 19.910 | 1.721 | 1.00 | 25.23 | A | C |
| ATOM | 830 | CD2 | LEU A 341 | 24.045 | 18.267 | 3.536 | 1.00 | 26.50 | A | C |
| ATOM | 831 | C | LEU A 341 | 22.122 | 15.105 | 1.367 | 1.00 | 28.96 | A | C |
| ATOM | 832 | O | LEU A 341 | 21.407 | 14.570 | 2.205 | 1.00 | 29.31 | A | O |
| ATOM | 833 | N | LEU A 342 | 22.025 | 14.830 | 0.077 | 1.00 | 29.67 | A | N |
| ATOM | 834 | CA | LEU A 342 | 20.995 | 13.939 | -0.393 | 1.00 | 29.85 | A | C |
| ATOM | 835 | CB | LEU A 342 | 20.797 | 14.097 | -1.901 | 1.00 | 31.05 | A | C |
| ATOM | 836 | CG | LEU A 342 | 20.317 | 15.541 | -2.151 | 1.00 | 32.75 | A | C |
| ATOM | 837 | CD1 | LEU A 342 | 19.583 | 15.663 | -3.444 | 1.00 | 33.63 | A | C |
| ATOM | 838 | CD2 | LEU A 342 | 19.388 | 15.997 | -1.026 | 1.00 | 33.96 | A | C |
| ATOM | 839 | C | LEU A 342 | 21.263 | 12.511 | 0.021 | 1.00 | 30.25 | A | C |
| ATOM | 840 | O | LEU A 342 | 20.326 | 11.758 | 0.259 | 1.00 | 30.49 | A | O |
| ATOM | 841 | N | ASP A 343 | 22.533 | 12.120 | 0.129 | 1.00 | 29.91 | A | N |
| ATOM | 842 | CA | ASP A 343 | 22.810 | 10.761 | 0.550 | 1.00 | 29.61 | A | C |
| ATOM | 843 | CB | ASP A 343 | 24.267 | 10.367 | 0.404 | 1.00 | 32.29 | A | C |
| ATOM | 844 | CG | ASP A 343 | 24.438 | 8.860 | 0.484 | 1.00 | 36.57 | A | C |
| ATOM | 845 | OD1 | ASP A 343 | 23.789 | 8.145 | -0.339 | 1.00 | 41.28 | A | O |
| ATOM | 846 | OD2 | ASP A 343 | 25.143 | 8.369 | 1.392 | 1.00 | 37.27 | A | O |
| ATOM | 847 | C | ASP A 343 | 22.395 | 10.596 | 1.994 | 1.00 | 28.13 | A | C |
| ATOM | 848 | O | ASP A 343 | 21.986 | 9.522 | 2.400 | 1.00 | 27.64 | A | O |
| ATOM | 849 | N | MET A 344 | 22.574 | 11.652 | 2.780 | 1.00 | 27.89 | A | N |
| ATOM | 850 | CA | MET A 344 | 22.162 | 11.631 | 4.173 | 1.00 | 27.55 | A | C |
| ATOM | 851 | CB | MET A 344 | 22.704 | 12.863 | 4.892 | 1.00 | 28.68 | A | C |
| ATOM | 852 | CG | MET A 344 | 24.214 | 12.835 | 5.027 | 1.00 | 30.23 | A | C |
| ATOM | 853 | SD | MET A 344 | 24.819 | 14.376 | 5.679 | 1.00 | 35.73 | A | S |
| ATOM | 854 | CE | MET A 344 | 25.257 | 13.906 | 7.394 | 1.00 | 33.95 | A | C |
| ATOM | 855 | C | MET A 344 | 20.626 | 11.535 | 4.285 | 1.00 | 26.22 | A | C |
| ATOM | 856 | O | MET A 344 | 20.102 | 10.754 | 5.077 | 1.00 | 26.43 | A | O |
| ATOM | 857 | N | ALA A 345 | 19.924 | 12.320 | 3.472 | 1.00 | 25.08 | A | N |
| ATOM | 858 | CA | ALA A 345 | 18.464 | 12.307 | 3.427 | 1.00 | 24.03 | A | C |
| ATOM | 859 | CB | ALA A 345 | 17.967 | 13.359 | 2.423 | 1.00 | 23.54 | A | C |
| ATOM | 860 | C | ALA A 345 | 17.975 | 10.909 | 3.040 | 1.00 | 23.14 | A | C |
| ATOM | 861 | O | ALA A 345 | 17.020 | 10.411 | 3.629 | 1.00 | 23.31 | A | O |
| ATOM | 862 | N | ALA A 346 | 18.705 | 10.239 | 2.142 | 1.00 | 22.94 | A | N |
| ATOM | 863 | CA | ALA A 346 | 18.380 | 8.892 | 1.678 | 1.00 | 23.43 | A | C |
| ATOM | 864 | CB | ALA A 346 | 19.305 | 8.505 | 0.521 | 1.00 | 23.44 | A | C |
| ATOM | 865 | C | ALA A 346 | 18.529 | 7.880 | 2.798 | 1.00 | 24.01 | A | C |
| ATOM | 866 | O | ALA A 346 | 17.818 | 6.870 | 2.874 | 1.00 | 23.11 | A | O |
| ATOM | 867 | N | GLN A 347 | 19.560 | 8.072 | 3.604 | 1.00 | 24.81 | A | N |
| ATOM | 868 | CA | GLN A 347 | 19.753 | 7.180 | 4.731 | 1.00 | 24.61 | A | C |
| ATOM | 869 | CB | GLN A 347 | 21.059 | 7.533 | 5.457 | 1.00 | 26.77 | A | C |
| ATOM | 870 | CG | GLN A 347 | 22.291 | 7.130 | 4.661 | 1.00 | 29.62 | A | C |
| ATOM | 871 | CD | GLN A 347 | 23.581 | 7.411 | 5.392 | 1.00 | 32.50 | A | C |
| ATOM | 872 | OE1 | GLN A 347 | 24.352 | 6.485 | 5.660 | 1.00 | 34.38 | A | O |

Figure 11

| | | | | | | | | | | | |
|---|---|---|---|---|---|---|---|---|---|---|---|
| ATOM | 873 | NE2 | GLN | A | 347 | 23.822 | 8.677 | 5.733 | 1.00 | 32.87 | A | N |
| ATOM | 874 | C | GLN | A | 347 | 18.568 | 7.275 | 5.697 | 1.00 | 22.11 | A | C |
| ATOM | 875 | O | GLN | A | 347 | 18.111 | 6.258 | 6.171 | 1.00 | 22.62 | A | O |
| ATOM | 876 | N | ILE | A | 348 | 18.116 | 8.488 | 5.994 | 1.00 | 20.18 | A | N |
| ATOM | 877 | CA | ILE | A | 348 | 17.007 | 8.710 | 6.934 | 1.00 | 20.70 | A | C |
| ATOM | 878 | CB | ILE | A | 348 | 16.858 | 10.220 | 7.259 | 1.00 | 19.76 | A | C |
| ATOM | 879 | CG2 | ILE | A | 348 | 15.743 | 10.440 | 8.254 | 1.00 | 18.73 | A | C |
| ATOM | 880 | CG1 | ILE | A | 348 | 18.163 | 10.746 | 7.855 | 1.00 | 19.17 | A | C |
| ATOM | 881 | CD1 | ILE | A | 348 | 18.317 | 12.251 | 7.866 | 1.00 | 18.21 | A | C |
| ATOM | 882 | C | ILE | A | 348 | 15.707 | 8.149 | 6.344 | 1.00 | 21.24 | A | C |
| ATOM | 883 | O | ILE | A | 348 | 14.918 | 7.501 | 7.029 | 1.00 | 21.25 | A | O |
| ATOM | 884 | N | ALA | A | 349 | 15.524 | 8.347 | 5.038 | 1.00 | 22.30 | A | N |
| ATOM | 885 | CA | ALA | A | 349 | 14.345 | 7.830 | 4.357 | 1.00 | 21.54 | A | C |
| ATOM | 886 | CB | ALA | A | 349 | 14.328 | 8.313 | 2.957 | 1.00 | 21.54 | A | C |
| ATOM | 887 | C | ALA | A | 349 | 14.406 | 6.298 | 4.409 | 1.00 | 21.70 | A | C |
| ATOM | 888 | O | ALA | A | 349 | 13.392 | 5.642 | 4.619 | 1.00 | 21.14 | A | O |
| ATOM | 889 | N | GLU | A | 350 | 15.605 | 5.724 | 4.304 | 1.00 | 21.99 | A | N |
| ATOM | 890 | CA | GLU | A | 350 | 15.737 | 4.268 | 4.365 | 1.00 | 22.46 | A | C |
| ATOM | 891 | CB | GLU | A | 350 | 17.177 | 3.831 | 4.035 | 1.00 | 23.50 | A | C |
| ATOM | 892 | CG | GLU | A | 350 | 17.395 | 2.345 | 4.160 | 1.00 | 24.57 | A | C |
| ATOM | 893 | CD | GLU | A | 350 | 18.841 | 1.900 | 3.981 | 1.00 | 25.14 | A | C |
| ATOM | 894 | OE1 | GLU | A | 350 | 19.734 | 2.733 | 3.748 | 1.00 | 25.55 | A | O |
| ATOM | 895 | OE2 | GLU | A | 350 | 19.083 | 0.688 | 4.102 | 1.00 | 26.87 | A | O |
| ATOM | 896 | C | GLU | A | 350 | 15.284 | 3.736 | 5.738 | 1.00 | 22.48 | A | C |
| ATOM | 897 | O | GLU | A | 350 | 14.554 | 2.743 | 5.838 | 1.00 | 21.50 | A | O |
| ATOM | 898 | N | GLY | A | 351 | 15.699 | 4.424 | 6.799 | 1.00 | 22.85 | A | N |
| ATOM | 899 | CA | GLY | A | 351 | 15.292 | 4.022 | 8.139 | 1.00 | 21.18 | A | C |
| ATOM | 900 | C | GLY | A | 351 | 13.797 | 4.194 | 8.299 | 1.00 | 19.83 | A | C |
| ATOM | 901 | O | GLY | A | 351 | 13.131 | 3.319 | 8.871 | 1.00 | 19.88 | A | O |
| ATOM | 902 | N | MET | A | 352 | 13.262 | 5.290 | 7.766 | 1.00 | 19.98 | A | N |
| ATOM | 903 | CA | MET | A | 352 | 11.811 | 5.552 | 7.836 | 1.00 | 21.29 | A | C |
| ATOM | 904 | CB | MET | A | 352 | 11.470 | 6.967 | 7.380 | 1.00 | 20.74 | A | C |
| ATOM | 905 | CG | MET | A | 352 | 11.844 | 8.060 | 8.434 | 1.00 | 21.87 | A | C |
| ATOM | 906 | SD | MET | A | 352 | 11.159 | 7.798 | 10.150 | 1.00 | 22.93 | A | S |
| ATOM | 907 | CE | MET | A | 352 | 9.439 | 7.256 | 9.821 | 1.00 | 21.09 | A | C |
| ATOM | 908 | C | MET | A | 352 | 11.059 | 4.522 | 7.005 | 1.00 | 23.24 | A | C |
| ATOM | 909 | O | MET | A | 352 | 9.954 | 4.091 | 7.390 | 1.00 | 23.68 | A | O |
| ATOM | 910 | N | ALA | A | 353 | 11.690 | 4.048 | 5.922 | 1.00 | 23.10 | A | N |
| ATOM | 911 | CA | ALA | A | 353 | 11.057 | 3.025 | 5.125 | 1.00 | 24.51 | A | C |
| ATOM | 912 | CB | ALA | A | 353 | 11.815 | 2.800 | 3.822 | 1.00 | 24.95 | A | C |
| ATOM | 913 | C | ALA | A | 353 | 10.967 | 1.725 | 5.953 | 1.00 | 25.05 | A | C |
| ATOM | 914 | O | ALA | A | 353 | 10.004 | 0.966 | 5.825 | 1.00 | 23.90 | A | O |
| ATOM | 915 | N | PHE | A | 354 | 11.954 | 1.464 | 6.817 | 1.00 | 26.03 | A | N |
| ATOM | 916 | CA | PHE | A | 354 | 11.879 | 0.267 | 7.648 | 1.00 | 26.98 | A | C |
| ATOM | 917 | CB | PHE | A | 354 | 13.179 | 0.006 | 8.381 | 1.00 | 29.54 | A | C |
| ATOM | 918 | CG | PHE | A | 354 | 13.181 | -1.276 | 9.186 | 1.00 | 31.91 | A | C |
| ATOM | 919 | CD1 | PHE | A | 354 | 12.922 | -2.499 | 8.573 | 1.00 | 32.93 | A | C |
| ATOM | 920 | CD2 | PHE | A | 354 | 13.563 | -1.269 | 10.529 | 1.00 | 32.25 | A | C |
| ATOM | 921 | CE1 | PHE | A | 354 | 13.062 | -3.689 | 9.277 | 1.00 | 33.49 | A | C |
| ATOM | 922 | CE2 | PHE | A | 354 | 13.707 | -2.453 | 11.236 | 1.00 | 32.58 | A | C |
| ATOM | 923 | CZ | PHE | A | 354 | 13.457 | -3.666 | 10.608 | 1.00 | 33.82 | A | C |
| ATOM | 924 | C | PHE | A | 354 | 10.779 | 0.448 | 8.673 | 1.00 | 27.20 | A | C |
| ATOM | 925 | O | PHE | A | 354 | 10.035 | -0.469 | 8.928 | 1.00 | 28.03 | A | O |
| ATOM | 926 | N | ILE | A | 355 | 10.709 | 1.626 | 9.285 | 1.00 | 27.11 | A | N |
| ATOM | 927 | CA | ILE | A | 355 | 9.663 | 1.940 | 10.272 | 1.00 | 27.48 | A | C |
| ATOM | 928 | CB | ILE | A | 355 | 9.897 | 3.364 | 10.868 | 1.00 | 24.81 | A | C |
| ATOM | 929 | CG2 | ILE | A | 355 | 8.655 | 3.912 | 11.592 | 1.00 | 25.87 | A | C |
| ATOM | 930 | CG1 | ILE | A | 355 | 11.128 | 3.308 | 11.788 | 1.00 | 23.32 | A | C |
| ATOM | 931 | CD1 | ILE | A | 355 | 11.690 | 4.599 | 12.171 | 1.00 | 21.87 | A | C |

Figure 11

| ATOM | 932 | C | ILE | A | 355 | 8.257 | 1.752 | 9.638 | 1.00 | 28.56 | A | C |
|------|-----|------|-----|---|-----|--------|--------|--------|------|-------|---|---|
| ATOM | 933 | O | ILE | A | 355 | 7.423 | 1.056 | 10.201 | 1.00 | 28.87 | A | O |
| ATOM | 934 | N | GLU | A | 356 | 8.063 | 2.267 | 8.426 | 1.00 | 29.70 | A | N |
| ATOM | 935 | CA | GLU | A | 356 | 6.798 | 2.146 | 7.674 | 1.00 | 31.09 | A | C |
| ATOM | 936 | CB | GLU | A | 356 | 6.999 | 2.847 | 6.327 | 1.00 | 30.75 | A | C |
| ATOM | 937 | CG | GLU | A | 356 | 5.824 | 2.889 | 5.333 | 1.00 | 29.68 | A | C |
| ATOM | 938 | CD | GLU | A | 356 | 6.156 | 3.820 | 4.175 | 1.00 | 29.76 | A | C |
| ATOM | 939 | OE1 | GLU | A | 356 | 6.874 | 3.397 | 3.225 | 1.00 | 31.33 | A | O |
| ATOM | 940 | OE2 | GLU | A | 356 | 5.818 | 5.015 | 4.262 | 1.00 | 27.55 | A | O |
| ATOM | 941 | C | GLU | A | 356 | 6.423 | 0.663 | 7.448 | 1.00 | 32.36 | A | C |
| ATOM | 942 | O | GLU | A | 356 | 5.321 | 0.197 | 7.772 | 1.00 | 32.91 | A | O |
| ATOM | 943 | N | GLU | A | 357 | 7.375 | -0.069 | 6.898 | 1.00 | 33.57 | A | N |
| ATOM | 944 | CA | GLU | A | 357 | 7.270 | -1.485 | 6.603 | 1.00 | 34.52 | A | C |
| ATOM | 945 | CB | GLU | A | 357 | 8.654 | -1.908 | 6.110 | 1.00 | 36.89 | A | C |
| ATOM | 946 | CG | GLU | A | 357 | 9.057 | -3.310 | 6.414 | 1.00 | 41.56 | A | C |
| ATOM | 947 | CD | GLU | A | 357 | 8.496 | -4.233 | 5.422 | 1.00 | 44.36 | A | C |
| ATOM | 948 | OE1 | GLU | A | 357 | 8.730 | -3.976 | 4.225 | 1.00 | 47.90 | A | O |
| ATOM | 949 | OE2 | GLU | A | 357 | 7.828 | -5.202 | 5.823 | 1.00 | 46.86 | A | O |
| ATOM | 950 | C | GLU | A | 357 | 6.822 | -2.322 | 7.817 | 1.00 | 34.66 | A | C |
| ATOM | 951 | O | GLU | A | 357 | 5.955 | -3.213 | 7.709 | 1.00 | 33.63 | A | O |
| ATOM | 952 | N | ARG | A | 358 | 7.367 | -1.991 | 8.980 | 1.00 | 34.81 | A | N |
| ATOM | 953 | CA | ARG | A | 358 | 7.043 | -2.716 | 10.201 | 1.00 | 36.50 | A | C |
| ATOM | 954 | CB | ARG | A | 358 | 8.290 | -2.787 | 11.079 | 1.00 | 39.16 | A | C |
| ATOM | 955 | CG | ARG | A | 358 | 9.511 | -3.421 | 10.384 | 1.00 | 43.64 | A | C |
| ATOM | 956 | CD | ARG | A | 358 | 9.400 | -4.951 | 10.161 | 1.00 | 47.24 | A | C |
| ATOM | 957 | NE | ARG | A | 358 | 9.247 | -5.660 | 11.433 | 1.00 | 52.52 | A | N |
| ATOM | 958 | CZ | ARG | A | 358 | 10.157 | -5.670 | 12.413 | 1.00 | 55.90 | A | C |
| ATOM | 959 | NH1 | ARG | A | 358 | 11.313 | -5.021 | 12.274 | 1.00 | 58.08 | A | N |
| ATOM | 960 | NH2 | ARG | A | 358 | 9.877 | -6.236 | 13.585 | 1.00 | 57.36 | A | N |
| ATOM | 961 | C | ARG | A | 358 | 5.846 | -2.143 | 10.975 | 1.00 | 35.80 | A | C |
| ATOM | 962 | O | ARG | A | 358 | 5.609 | -2.518 | 12.114 | 1.00 | 35.36 | A | O |
| ATOM | 963 | N | ASN | A | 359 | 5.094 | -1.253 | 10.325 | 1.00 | 35.24 | A | N |
| ATOM | 964 | CA | ASN | A | 359 | 3.902 | -0.597 | 10.874 | 1.00 | 35.04 | A | C |
| ATOM | 965 | CB | ASN | A | 359 | 2.691 | -1.551 | 10.873 | 1.00 | 36.43 | A | C |
| ATOM | 966 | CG | ASN | A | 359 | 2.512 | -2.292 | 9.508 | 1.00 | 39.78 | A | C |
| ATOM | 967 | OD1 | ASN | A | 359 | 2.286 | -1.667 | 8.443 | 1.00 | 40.57 | A | O |
| ATOM | 968 | ND2 | ASN | A | 359 | 2.648 | -3.625 | 9.540 | 1.00 | 39.55 | A | N |
| ATOM | 969 | C | ASN | A | 359 | 4.064 | 0.146 | 12.211 | 1.00 | 34.05 | A | C |
| ATOM | 970 | O | ASN | A | 359 | 3.230 | 0.086 | 13.118 | 1.00 | 33.05 | A | O |
| ATOM | 971 | N | TYR | A | 360 | 5.140 | 0.904 | 12.290 | 1.00 | 33.19 | A | N |
| ATOM | 972 | CA | TYR | A | 360 | 5.423 | 1.716 | 13.456 | 1.00 | 32.84 | A | C |
| ATOM | 973 | CB | TYR | A | 360 | 6.866 | 1.484 | 13.935 | 1.00 | 35.14 | A | C |
| ATOM | 974 | CG | TYR | A | 360 | 7.060 | 0.365 | 14.929 | 1.00 | 37.27 | A | C |
| ATOM | 975 | CD1 | TYR | A | 360 | 7.033 | -0.973 | 14.526 | 1.00 | 38.05 | A | C |
| ATOM | 976 | CE1 | TYR | A | 360 | 7.226 | -1.999 | 15.438 | 1.00 | 38.93 | A | C |
| ATOM | 977 | CD2 | TYR | A | 360 | 7.288 | 0.649 | 16.276 | 1.00 | 38.72 | A | C |
| ATOM | 978 | CE2 | TYR | A | 360 | 7.478 | -0.371 | 17.205 | 1.00 | 39.73 | A | C |
| ATOM | 979 | CZ | TYR | A | 360 | 7.441 | -1.687 | 16.783 | 1.00 | 40.43 | A | C |
| ATOM | 980 | OH | TYR | A | 360 | 7.551 | -2.687 | 17.728 | 1.00 | 42.35 | A | O |
| ATOM | 981 | C | TYR | A | 360 | 5.379 | 3.135 | 12.955 | 1.00 | 31.63 | A | C |
| ATOM | 982 | O | TYR | A | 360 | 5.338 | 3.363 | 11.754 | 1.00 | 30.34 | A | O |
| ATOM | 983 | N | ILE | A | 361 | 5.367 | 4.095 | 13.872 | 1.00 | 30.78 | A | N |
| ATOM | 984 | CA | ILE | A | 361 | 5.475 | 5.480 | 13.450 | 1.00 | 31.22 | A | C |
| ATOM | 985 | CB | ILE | A | 361 | 4.140 | 6.283 | 13.433 | 1.00 | 31.80 | A | C |
| ATOM | 986 | CG2 | ILE | A | 361 | 3.151 | 5.612 | 12.442 | 1.00 | 32.06 | A | C |
| ATOM | 987 | CG1 | ILE | A | 361 | 3.571 | 6.431 | 14.840 | 1.00 | 31.46 | A | C |
| ATOM | 988 | CD1 | ILE | A | 361 | 2.373 | 7.401 | 14.925 | 1.00 | 33.54 | A | C |
| ATOM | 989 | C | ILE | A | 361 | 6.496 | 6.133 | 14.363 | 1.00 | 31.25 | A | C |
| ATOM | 990 | O | ILE | A | 361 | 6.843 | 5.608 | 15.418 | 1.00 | 32.22 | A | O |

Figure 11

| ATOM | 991 | N | HIS | A | 362 | 6.986 | 7.280 | 13.944 | 1.00 | 30.31 | A | N |
|------|------|-----|-----|---|-----|--------|--------|--------|------|-------|---|---|
| ATOM | 992 | CA | HIS | A | 362 | 7.970 | 7.997 | 14.710 | 1.00 | 28.32 | A | C |
| ATOM | 993 | CB | HIS | A | 362 | 8.946 | 8.667 | 13.764 | 1.00 | 26.35 | A | C |
| ATOM | 994 | CG | HIS | A | 362 | 10.206 | 9.138 | 14.426 | 1.00 | 23.97 | A | C |
| ATOM | 995 | CD2 | HIS | A | 362 | 11.501 | 8.815 | 14.217 | 1.00 | 24.21 | A | C |
| ATOM | 996 | ND1 | HIS | A | 362 | 10.210 | 10.116 | 15.388 | 1.00 | 21.84 | A | N |
| ATOM | 997 | CE1 | HIS | A | 362 | 11.453 | 10.388 | 15.741 | 1.00 | 23.58 | A | C |
| ATOM | 998 | NE2 | HIS | A | 362 | 12.261 | 9.608 | 15.045 | 1.00 | 22.37 | A | N |
| ATOM | 999 | C | HIS | A | 362 | 7.335 | 9.029 | 15.633 | 1.00 | 28.89 | A | C |
| ATOM | 1000 | O | HIS | A | 362 | 7.506 | 8.922 | 16.836 | 1.00 | 28.69 | A | O |
| ATOM | 1001 | N | ARG | A | 363 | 6.648 | 10.015 | 15.030 | 1.00 | 27.90 | A | N |
| ATOM | 1002 | CA | ARG | A | 363 | 5.973 | 11.169 | 15.633 | 1.00 | 27.07 | A | C |
| ATOM | 1003 | CB | ARG | A | 363 | 4.908 | 10.790 | 16.704 | 1.00 | 31.04 | A | C |
| ATOM | 1004 | CG | ARG | A | 363 | 5.374 | 9.917 | 17.865 | 1.00 | 36.49 | A | C |
| ATOM | 1005 | CD | ARG | A | 363 | 4.225 | 9.252 | 18.660 | 1.00 | 40.86 | A | C |
| ATOM | 1006 | NE | ARG | A | 363 | 3.515 | 10.235 | 19.463 | 1.00 | 43.30 | A | N |
| ATOM | 1007 | CZ | ARG | A | 363 | 2.200 | 10.388 | 19.432 | 1.00 | 45.19 | A | C |
| ATOM | 1008 | NH1 | ARG | A | 363 | 1.468 | 9.591 | 18.672 | 1.00 | 45.88 | A | N |
| ATOM | 1009 | NH2 | ARG | A | 363 | 1.645 | 11.470 | 19.961 | 1.00 | 46.28 | A | N |
| ATOM | 1010 | C | ARG | A | 363 | 6.902 | 12.290 | 16.089 | 1.00 | 25.66 | A | C |
| ATOM | 1011 | O | ARG | A | 363 | 6.468 | 13.408 | 16.370 | 1.00 | 24.80 | A | O |
| ATOM | 1012 | N | ASP | A | 364 | 8.197 | 12.026 | 16.100 | 1.00 | 23.10 | A | N |
| ATOM | 1013 | CA | ASP | A | 364 | 9.153 | 13.048 | 16.512 | 1.00 | 23.23 | A | C |
| ATOM | 1014 | CB | ASP | A | 364 | 9.804 | 12.670 | 17.857 | 1.00 | 22.13 | A | C |
| ATOM | 1015 | CG | ASP | A | 364 | 8.862 | 12.822 | 19.033 | 1.00 | 20.78 | A | C |
| ATOM | 1016 | OD1 | ASP | A | 364 | 8.428 | 13.942 | 19.320 | 1.00 | 21.21 | A | O |
| ATOM | 1017 | OD2 | ASP | A | 364 | 8.549 | 11.802 | 19.652 | 1.00 | 22.36 | A | O |
| ATOM | 1018 | C | ASP | A | 364 | 10.255 | 13.316 | 15.481 | 1.00 | 23.00 | A | C |
| ATOM | 1019 | O | ASP | A | 364 | 11.328 | 13.790 | 15.835 | 1.00 | 22.24 | A | O |
| ATOM | 1020 | N | LEU | A | 365 | 9.989 | 12.989 | 14.224 | 1.00 | 21.60 | A | N |
| ATOM | 1021 | CA | LEU | A | 365 | 10.978 | 13.155 | 13.162 | 1.00 | 20.65 | A | C |
| ATOM | 1022 | CB | LEU | A | 365 | 10.538 | 12.392 | 11.918 | 1.00 | 20.10 | A | C |
| ATOM | 1023 | CG | LEU | A | 365 | 11.540 | 12.216 | 10.777 | 1.00 | 19.99 | A | C |
| ATOM | 1024 | CD1 | LEU | A | 365 | 12.698 | 11.325 | 11.250 | 1.00 | 19.16 | A | C |
| ATOM | 1025 | CD2 | LEU | A | 365 | 10.811 | 11.594 | 9.543 | 1.00 | 18.91 | A | C |
| ATOM | 1026 | C | LEU | A | 365 | 11.305 | 14.607 | 12.817 | 1.00 | 20.49 | A | C |
| ATOM | 1027 | O | LEU | A | 365 | 10.430 | 15.394 | 12.474 | 1.00 | 20.21 | A | O |
| ATOM | 1028 | N | ARG | A | 366 | 12.574 | 14.940 | 12.995 | 1.00 | 20.37 | A | N |
| ATOM | 1029 | CA | ARG | A | 366 | 13.131 | 16.258 | 12.710 | 1.00 | 20.01 | A | C |
| ATOM | 1030 | CB | ARG | A | 366 | 12.644 | 17.320 | 13.697 | 1.00 | 20.62 | A | C |
| ATOM | 1031 | CG | ARG | A | 366 | 12.938 | 17.097 | 15.151 | 1.00 | 20.42 | A | C |
| ATOM | 1032 | CD | ARG | A | 366 | 12.562 | 18.379 | 15.903 | 1.00 | 23.99 | A | C |
| ATOM | 1033 | NE | ARG | A | 366 | 12.350 | 18.178 | 17.336 | 1.00 | 27.07 | A | N |
| ATOM | 1034 | CZ | ARG | A | 366 | 11.341 | 17.477 | 17.861 | 1.00 | 29.69 | A | C |
| ATOM | 1035 | NH1 | ARG | A | 366 | 10.417 | 16.904 | 17.082 | 1.00 | 28.51 | A | N |
| ATOM | 1036 | NH2 | ARG | A | 366 | 11.282 | 17.313 | 19.171 | 1.00 | 29.56 | A | N |
| ATOM | 1037 | C | ARG | A | 366 | 14.637 | 16.066 | 12.809 | 1.00 | 20.33 | A | C |
| ATOM | 1038 | O | ARG | A | 366 | 15.095 | 15.083 | 13.389 | 1.00 | 19.55 | A | O |
| ATOM | 1039 | N | ALA | A | 367 | 15.402 | 16.972 | 12.213 | 1.00 | 19.73 | A | N |
| ATOM | 1040 | CA | ALA | A | 367 | 16.852 | 16.829 | 12.230 | 1.00 | 19.66 | A | C |
| ATOM | 1041 | CB | ALA | A | 367 | 17.512 | 17.949 | 11.442 | 1.00 | 19.43 | A | C |
| ATOM | 1042 | C | ALA | A | 367 | 17.505 | 16.673 | 13.615 | 1.00 | 20.67 | A | C |
| ATOM | 1043 | O | ALA | A | 367 | 18.505 | 15.962 | 13.739 | 1.00 | 21.15 | A | O |
| ATOM | 1044 | N | ALA | A | 368 | 16.944 | 17.316 | 14.648 | 1.00 | 20.89 | A | N |
| ATOM | 1045 | CA | ALA | A | 368 | 17.480 | 17.216 | 16.010 | 1.00 | 20.67 | A | C |
| ATOM | 1046 | CB | ALA | A | 368 | 16.640 | 18.029 | 16.979 | 1.00 | 21.84 | A | C |
| ATOM | 1047 | C | ALA | A | 368 | 17.531 | 15.775 | 16.471 | 1.00 | 22.50 | A | C |
| ATOM | 1048 | O | ALA | A | 368 | 18.385 | 15.407 | 17.267 | 1.00 | 22.99 | A | O |
| ATOM | 1049 | N | ASN | A | 369 | 16.619 | 14.946 | 15.954 | 1.00 | 22.73 | A | N |

Figure 11

| ATOM | 1050 | CA  | ASN A 369 | 16.559 | 13.547 | 16.337 | 1.00 | 23.55 | A | C |
|------|------|-----|-----------|--------|--------|--------|------|-------|---|---|
| ATOM | 1051 | CB  | ASN A 369 | 15.115 | 13.140 | 16.677 | 1.00 | 24.82 | A | C |
| ATOM | 1052 | CG  | ASN A 369 | 14.517 | 14.001 | 17.801 | 1.00 | 24.96 | A | C |
| ATOM | 1053 | OD1 | ASN A 369 | 15.212 | 14.351 | 18.769 | 1.00 | 24.33 | A | O |
| ATOM | 1054 | ND2 | ASN A 369 | 13.256 | 14.389 | 17.649 | 1.00 | 21.90 | A | N |
| ATOM | 1055 | C   | ASN A 369 | 17.243 | 12.543 | 15.402 | 1.00 | 22.47 | A | C |
| ATOM | 1056 | O   | ASN A 369 | 16.930 | 11.361 | 15.404 | 1.00 | 24.59 | A | O |
| ATOM | 1057 | N   | ILE A 370 | 18.094 | 13.027 | 14.524 | 1.00 | 21.91 | A | N |
| ATOM | 1058 | CA  | ILE A 370 | 18.876 | 12.125 | 13.669 | 1.00 | 20.56 | A | C |
| ATOM | 1059 | CB  | ILE A 370 | 18.886 | 12.594 | 12.206 | 1.00 | 19.47 | A | C |
| ATOM | 1060 | CG2 | ILE A 370 | 19.879 | 11.706 | 11.377 | 1.00 | 17.69 | A | C |
| ATOM | 1061 | CG1 | ILE A 370 | 17.452 | 12.610 | 11.642 | 1.00 | 17.92 | A | C |
| ATOM | 1062 | CD1 | ILE A 370 | 16.711 | 11.266 | 11.716 | 1.00 | 14.03 | A | C |
| ATOM | 1063 | C   | ILE A 370 | 20.309 | 12.285 | 14.246 | 1.00 | 20.60 | A | C |
| ATOM | 1064 | O   | ILE A 370 | 20.705 | 13.388 | 14.596 | 1.00 | 19.74 | A | O |
| ATOM | 1065 | N   | LEU A 371 | 21.036 | 11.191 | 14.403 | 1.00 | 21.70 | A | N |
| ATOM | 1066 | CA  | LEU A 371 | 22.388 | 11.252 | 14.921 | 1.00 | 22.86 | A | C |
| ATOM | 1067 | CB  | LEU A 371 | 22.553 | 10.276 | 16.105 | 1.00 | 21.48 | A | C |
| ATOM | 1068 | CG  | LEU A 371 | 21.580 | 10.522 | 17.284 | 1.00 | 18.24 | A | C |
| ATOM | 1069 | CD1 | LEU A 371 | 21.841 |  9.572 | 18.450 | 1.00 | 20.02 | A | C |
| ATOM | 1070 | CD2 | LEU A 371 | 21.744 | 11.937 | 17.740 | 1.00 | 18.09 | A | C |
| ATOM | 1071 | C   | LEU A 371 | 23.367 | 10.938 | 13.779 | 1.00 | 23.96 | A | C |
| ATOM | 1072 | O   | LEU A 371 | 23.051 | 10.138 | 12.897 | 1.00 | 24.62 | A | O |
| ATOM | 1073 | N   | VAL A 372 | 24.516 | 11.609 | 13.779 | 1.00 | 24.01 | A | N |
| ATOM | 1074 | CA  | VAL A 372 | 25.547 | 11.441 | 12.748 | 1.00 | 24.77 | A | C |
| ATOM | 1075 | CB  | VAL A 372 | 26.000 | 12.817 | 12.212 | 1.00 | 25.55 | A | C |
| ATOM | 1076 | CG1 | VAL A 372 | 26.858 | 12.659 | 10.966 | 1.00 | 24.92 | A | C |
| ATOM | 1077 | CG2 | VAL A 372 | 24.777 | 13.687 | 11.911 | 1.00 | 24.82 | A | C |
| ATOM | 1078 | C   | VAL A 372 | 26.754 | 10.725 | 13.322 | 1.00 | 25.36 | A | C |
| ATOM | 1079 | O   | VAL A 372 | 27.320 | 11.164 | 14.315 | 1.00 | 25.05 | A | O |
| ATOM | 1080 | N   | SER A 373 | 27.177 |  9.640 | 12.696 | 1.00 | 26.45 | A | N |
| ATOM | 1081 | CA  | SER A 373 | 28.330 |  8.901 | 13.206 | 1.00 | 28.78 | A | C |
| ATOM | 1082 | CB  | SER A 373 | 28.310 |  7.464 | 12.705 | 1.00 | 28.55 | A | C |
| ATOM | 1083 | OG  | SER A 373 | 28.716 |  7.408 | 11.351 | 1.00 | 30.35 | A | O |
| ATOM | 1084 | C   | SER A 373 | 29.675 |  9.551 | 12.857 | 1.00 | 30.33 | A | C |
| ATOM | 1085 | O   | SER A 373 | 29.731 | 10.669 | 12.338 | 1.00 | 28.95 | A | O |
| ATOM | 1086 | N   | ASP A 374 | 30.757 |  8.844 | 13.186 | 1.00 | 33.23 | A | N |
| ATOM | 1087 | CA  | ASP A 374 | 32.118 |  9.319 | 12.914 | 1.00 | 35.16 | A | C |
| ATOM | 1088 | CB  | ASP A 374 | 33.152 |  8.423 | 13.613 | 1.00 | 36.60 | A | C |
| ATOM | 1089 | CG  | ASP A 374 | 33.073 |  6.984 | 13.161 | 1.00 | 38.06 | A | C |
| ATOM | 1090 | OD1 | ASP A 374 | 32.014 |  6.347 | 13.299 | 1.00 | 40.10 | A | O |
| ATOM | 1091 | OD2 | ASP A 374 | 34.072 |  6.474 | 12.650 | 1.00 | 40.70 | A | O |
| ATOM | 1092 | C   | ASP A 374 | 32.367 |  9.351 | 11.404 | 1.00 | 35.60 | A | C |
| ATOM | 1093 | O   | ASP A 374 | 33.062 | 10.235 | 10.903 | 1.00 | 35.27 | A | O |
| ATOM | 1094 | N   | THR A 375 | 31.757 |  8.408 | 10.685 | 1.00 | 35.59 | A | N |
| ATOM | 1095 | CA  | THR A 375 | 31.929 |  8.355 |  9.246 | 1.00 | 36.63 | A | C |
| ATOM | 1096 | CB  | THR A 375 | 31.814 |  6.946 |  8.689 | 1.00 | 37.58 | A | C |
| ATOM | 1097 | OG1 | THR A 375 | 30.462 |  6.483 |  8.841 | 1.00 | 39.64 | A | O |
| ATOM | 1098 | CG2 | THR A 375 | 32.777 |  6.003 |  9.391 | 1.00 | 37.69 | A | C |
| ATOM | 1099 | C   | THR A 375 | 30.878 |  9.181 |  8.541 | 1.00 | 36.81 | A | C |
| ATOM | 1100 | O   | THR A 375 | 30.725 |  9.055 |  7.336 | 1.00 | 38.39 | A | O |
| ATOM | 1101 | N   | LEU A 376 | 30.147 | 10.002 |  9.289 | 1.00 | 35.51 | A | N |
| ATOM | 1102 | CA  | LEU A 376 | 29.098 | 10.863 |  8.744 | 1.00 | 35.27 | A | C |
| ATOM | 1103 | CB  | LEU A 376 | 29.636 | 11.800 |  7.660 | 1.00 | 35.42 | A | C |
| ATOM | 1104 | CG  | LEU A 376 | 30.846 | 12.680 |  7.988 | 1.00 | 35.91 | A | C |
| ATOM | 1105 | CD1 | LEU A 376 | 31.047 | 13.662 |  6.846 | 1.00 | 36.55 | A | C |
| ATOM | 1106 | CD2 | LEU A 376 | 30.648 | 13.420 |  9.298 | 1.00 | 36.18 | A | C |
| ATOM | 1107 | C   | LEU A 376 | 27.839 | 10.164 |  8.235 | 1.00 | 34.38 | A | C |
| ATOM | 1108 | O   | LEU A 376 | 27.123 | 10.705 |  7.395 | 1.00 | 35.26 | A | O |

Figure 11

| ATOM | 1109 | N | SER | A | 377 | 27.586 | 8.953 | 8.712 | 1.00 | 33.34 | A | N |
| --- | --- | --- | --- | --- | --- | --- | --- | --- | --- | --- | --- | --- |
| ATOM | 1110 | CA | SER | A | 377 | 26.379 | 8.243 | 8.328 | 1.00 | 33.13 | A | C |
| ATOM | 1111 | CB | SER | A | 377 | 26.618 | 6.744 | 8.305 | 1.00 | 33.77 | A | C |
| ATOM | 1112 | OG | SER | A | 377 | 26.716 | 6.215 | 9.608 | 1.00 | 36.96 | A | O |
| ATOM | 1113 | C | SER | A | 377 | 25.262 | 8.615 | 9.325 | 1.00 | 32.15 | A | C |
| ATOM | 1114 | O | SER | A | 377 | 25.520 | 8.779 | 10.517 | 1.00 | 31.05 | A | O |
| ATOM | 1115 | N | CYS | A | 378 | 24.030 | 8.765 | 8.825 | 1.00 | 31.45 | A | N |
| ATOM | 1116 | CA | CYS | A | 378 | 22.879 | 9.164 | 9.669 | 1.00 | 29.18 | A | C |
| ATOM | 1117 | CB | CYS | A | 378 | 21.951 | 10.104 | 8.900 | 1.00 | 27.65 | A | C |
| ATOM | 1118 | SG | CYS | A | 378 | 22.647 | 11.698 | 8.490 | 1.00 | 29.16 | A | S |
| ATOM | 1119 | C | CYS | A | 378 | 22.065 | 7.991 | 10.184 | 1.00 | 27.71 | A | C |
| ATOM | 1120 | O | CYS | A | 378 | 21.924 | 6.997 | 9.478 | 1.00 | 28.42 | A | O |
| ATOM | 1121 | N | LYS | A | 379 | 21.561 | 8.115 | 11.420 | 1.00 | 25.84 | A | N |
| ATOM | 1122 | CA | LYS | A | 379 | 20.724 | 7.100 | 12.072 | 1.00 | 25.25 | A | C |
| ATOM | 1123 | CB | LYS | A | 379 | 21.543 | 6.182 | 13.026 | 1.00 | 26.00 | A | C |
| ATOM | 1124 | CG | LYS | A | 379 | 22.571 | 5.220 | 12.346 | 1.00 | 25.12 | A | C |
| ATOM | 1125 | CD | LYS | A | 379 | 23.239 | 4.281 | 13.371 | 1.00 | 25.98 | A | C |
| ATOM | 1126 | CE | LYS | A | 379 | 24.259 | 3.253 | 12.791 | 1.00 | 26.49 | A | C |
| ATOM | 1127 | NZ | LYS | A | 379 | 23.914 | 1.861 | 13.363 | 1.00 | 31.72 | A | N |
| ATOM | 1128 | C | LYS | A | 379 | 19.562 | 7.774 | 12.833 | 1.00 | 24.65 | A | C |
| ATOM | 1129 | O | LYS | A | 379 | 19.701 | 8.854 | 13.403 | 1.00 | 25.28 | A | O |
| ATOM | 1130 | N | ILE | A | 380 | 18.411 | 7.121 | 12.831 | 1.00 | 24.28 | A | N |
| ATOM | 1131 | CA | ILE | A | 380 | 17.190 | 7.638 | 13.467 | 1.00 | 23.87 | A | C |
| ATOM | 1132 | CB | ILE | A | 380 | 15.925 | 7.056 | 12.746 | 1.00 | 25.01 | A | C |
| ATOM | 1133 | CG2 | ILE | A | 380 | 14.651 | 7.559 | 13.411 | 1.00 | 25.42 | A | C |
| ATOM | 1134 | CG1 | ILE | A | 380 | 15.948 | 7.393 | 11.250 | 1.00 | 24.42 | A | C |
| ATOM | 1135 | CD1 | ILE | A | 380 | 14.917 | 6.669 | 10.514 | 1.00 | 25.04 | A | C |
| ATOM | 1136 | C | ILE | A | 380 | 17.105 | 7.237 | 14.939 | 1.00 | 23.40 | A | C |
| ATOM | 1137 | O | ILE | A | 380 | 17.236 | 6.068 | 15.272 | 1.00 | 23.95 | A | O |
| ATOM | 1138 | N | ALA | A | 381 | 16.824 | 8.196 | 15.808 | 1.00 | 23.78 | A | N |
| ATOM | 1139 | CA | ALA | A | 381 | 16.711 | 7.909 | 17.226 | 1.00 | 23.09 | A | C |
| ATOM | 1140 | CB | ALA | A | 381 | 17.753 | 8.731 | 17.992 | 1.00 | 23.29 | A | C |
| ATOM | 1141 | C | ALA | A | 381 | 15.338 | 8.348 | 17.668 | 1.00 | 22.71 | A | C |
| ATOM | 1142 | O | ALA | A | 381 | 14.696 | 9.139 | 16.996 | 1.00 | 20.55 | A | O |
| ATOM | 1143 | N | ASP | A | 382 | 14.951 | 7.871 | 18.849 | 1.00 | 23.68 | A | N |
| ATOM | 1144 | CA | ASP | A | 382 | 13.715 | 8.258 | 19.509 | 1.00 | 24.01 | A | C |
| ATOM | 1145 | CB | ASP | A | 382 | 13.867 | 9.676 | 20.036 | 1.00 | 23.14 | A | C |
| ATOM | 1146 | CG | ASP | A | 382 | 14.821 | 9.742 | 21.222 | 1.00 | 24.46 | A | C |
| ATOM | 1147 | OD1 | ASP | A | 382 | 14.942 | 8.720 | 21.920 | 1.00 | 27.45 | A | O |
| ATOM | 1148 | OD2 | ASP | A | 382 | 15.436 | 10.789 | 21.465 | 1.00 | 24.34 | A | O |
| ATOM | 1149 | C | ASP | A | 382 | 12.451 | 8.114 | 18.699 | 1.00 | 24.20 | A | C |
| ATOM | 1150 | O | ASP | A | 382 | 11.644 | 9.035 | 18.602 | 1.00 | 23.82 | A | O |
| ATOM | 1151 | N | PHE | A | 383 | 12.319 | 6.956 | 18.090 | 1.00 | 25.47 | A | N |
| ATOM | 1152 | CA | PHE | A | 383 | 11.158 | 6.646 | 17.279 | 1.00 | 27.97 | A | C |
| ATOM | 1153 | CB | PHE | A | 383 | 11.620 | 5.867 | 16.030 | 1.00 | 29.11 | A | C |
| ATOM | 1154 | CG | PHE | A | 383 | 12.469 | 4.671 | 16.351 | 1.00 | 30.72 | A | C |
| ATOM | 1155 | CD1 | PHE | A | 383 | 11.888 | 3.476 | 16.750 | 1.00 | 31.70 | A | C |
| ATOM | 1156 | CD2 | PHE | A | 383 | 13.863 | 4.766 | 16.331 | 1.00 | 30.88 | A | C |
| ATOM | 1157 | CE1 | PHE | A | 383 | 12.681 | 2.387 | 17.136 | 1.00 | 31.51 | A | C |
| ATOM | 1158 | CE2 | PHE | A | 383 | 14.670 | 3.679 | 16.713 | 1.00 | 31.61 | A | C |
| ATOM | 1159 | CZ | PHE | A | 383 | 14.072 | 2.490 | 17.118 | 1.00 | 30.59 | A | C |
| ATOM | 1160 | C | PHE | A | 383 | 10.151 | 5.793 | 18.064 | 1.00 | 28.25 | A | C |
| ATOM | 1161 | O | PHE | A | 383 | 10.518 | 5.093 | 19.003 | 1.00 | 27.72 | A | O |
| ATOM | 1162 | N | GLY | A | 384 | 8.897 | 5.833 | 17.624 | 1.00 | 29.33 | A | N |
| ATOM | 1163 | CA | GLY | A | 384 | 7.845 | 5.030 | 18.221 | 1.00 | 30.66 | A | C |
| ATOM | 1164 | C | GLY | A | 384 | 7.459 | 5.349 | 19.638 | 1.00 | 31.69 | A | C |
| ATOM | 1165 | O | GLY | A | 384 | 6.766 | 4.550 | 20.244 | 1.00 | 31.91 | A | O |
| ATOM | 1166 | N | LEU | A | 385 | 7.945 | 6.477 | 20.165 | 1.00 | 32.98 | A | N |
| ATOM | 1167 | CA | LEU | A | 385 | 7.643 | 6.911 | 21.531 | 1.00 | 33.99 | A | C |

Figure 11

| | | | | | | | | | | |
|---|---|---|---|---|---|---|---|---|---|---|
| ATOM | 1168 | CB | LEU | A | 385 | 8.471 | 8.136 | 21.974 | 1.00 33.43 | A | C |
| ATOM | 1169 | CG | LEU | A | 385 | 10.001 | 8.153 | 21.864 | 1.00 34.05 | A | C |
| ATOM | 1170 | CD1 | LEU | A | 385 | 10.574 | 9.321 | 22.632 | 1.00 33.83 | A | C |
| ATOM | 1171 | CD2 | LEU | A | 385 | 10.601 | 6.822 | 22.322 | 1.00 34.96 | A | C |
| ATOM | 1172 | C | LEU | A | 385 | 6.193 | 7.313 | 21.648 | 1.00 35.38 | A | C |
| ATOM | 1173 | O | LEU | A | 385 | 5.579 | 7.842 | 20.702 | 1.00 33.99 | A | O |
| ATOM | 1174 | N | ALA | A | 386 | 5.668 | 7.104 | 22.848 | 1.00 36.88 | A | N |
| ATOM | 1175 | CA | ALA | A | 386 | 4.292 | 7.466 | 23.150 | 1.00 37.93 | A | C |
| ATOM | 1176 | CB | ALA | A | 386 | 3.847 | 6.788 | 24.475 | 1.00 38.85 | A | C |
| ATOM | 1177 | C | ALA | A | 386 | 4.140 | 8.986 | 23.246 | 1.00 37.23 | A | C |
| ATOM | 1178 | O | ALA | A | 386 | 3.080 | 9.520 | 22.963 | 1.00 38.06 | A | O |
| ATOM | 1179 | N | ARG | A | 387 | 5.217 | 9.694 | 23.564 | 1.00 36.98 | A | N |
| ATOM | 1180 | CA | ARG | A | 387 | 5.111 | 11.149 | 23.715 | 1.00 36.15 | A | C |
| ATOM | 1181 | CB | ARG | A | 387 | 5.558 | 11.525 | 25.129 | 1.00 36.90 | A | C |
| ATOM | 1182 | CG | ARG | A | 387 | 7.020 | 11.185 | 25.385 | 1.00 38.78 | A | C |
| ATOM | 1183 | CD | ARG | A | 387 | 7.465 | 11.536 | 26.791 | 1.00 39.07 | A | C |
| ATOM | 1184 | NE | ARG | A | 387 | 8.912 | 11.391 | 26.928 | 1.00 39.82 | A | N |
| ATOM | 1185 | CZ | ARG | A | 387 | 9.781 | 12.384 | 26.765 | 1.00 40.31 | A | C |
| ATOM | 1186 | NH1 | ARG | A | 387 | 9.351 | 13.607 | 26.481 | 1.00 40.70 | A | N |
| ATOM | 1187 | NH2 | ARG | A | 387 | 11.087 | 12.136 | 26.789 | 1.00 40.79 | A | N |
| ATOM | 1188 | C | ARG | A | 387 | 5.854 | 12.017 | 22.691 | 1.00 35.16 | A | C |
| ATOM | 1189 | O | ARG | A | 387 | 6.723 | 11.542 | 21.957 | 1.00 35.64 | A | O |
| ATOM | 1190 | N | LEU | A | 388 | 5.501 | 13.293 | 22.655 | 1.00 32.63 | A | N |
| ATOM | 1191 | CA | LEU | A | 388 | 6.138 | 14.244 | 21.782 | 1.00 31.40 | A | C |
| ATOM | 1192 | CB | LEU | A | 388 | 5.138 | 15.300 | 21.357 | 1.00 31.86 | A | C |
| ATOM | 1193 | CG | LEU | A | 388 | 3.917 | 14.757 | 20.638 | 1.00 34.04 | A | C |
| ATOM | 1194 | CD1 | LEU | A | 388 | 3.066 | 15.962 | 20.237 | 1.00 34.27 | A | C |
| ATOM | 1195 | CD2 | LEU | A | 388 | 4.371 | 13.999 | 19.385 | 1.00 34.86 | A | C |
| ATOM | 1196 | C | LEU | A | 388 | 7.241 | 14.896 | 22.612 | 1.00 29.98 | A | C |
| ATOM | 1197 | O | LEU | A | 388 | 6.964 | 15.547 | 23.609 | 1.00 29.44 | A | O |
| ATOM | 1198 | N | ILE | A | 389 | 8.480 | 14.737 | 22.160 | 1.00 28.87 | A | N |
| ATOM | 1199 | CA | ILE | A | 389 | 9.675 | 15.242 | 22.847 | 1.00 27.78 | A | C |
| ATOM | 1200 | CB | ILE | A | 389 | 10.854 | 14.199 | 22.764 | 1.00 26.61 | A | C |
| ATOM | 1201 | CG2 | ILE | A | 389 | 10.395 | 12.813 | 23.222 | 1.00 25.89 | A | C |
| ATOM | 1202 | CG1 | ILE | A | 389 | 11.422 | 14.103 | 21.351 | 1.00 25.32 | A | C |
| ATOM | 1203 | CD1 | ILE | A | 389 | 12.470 | 13.048 | 21.231 | 1.00 24.57 | A | C |
| ATOM | 1204 | C | ILE | A | 389 | 10.182 | 16.624 | 22.438 | 1.00 28.19 | A | C |
| ATOM | 1205 | O | ILE | A | 389 | 9.823 | 17.158 | 21.388 | 1.00 26.63 | A | O |
| ATOM | 1206 | N | GLU | A | 390 | 11.010 | 17.203 | 23.303 | 1.00 29.96 | A | N |
| ATOM | 1207 | CA | GLU | A | 390 | 11.610 | 18.509 | 23.074 | 1.00 32.27 | A | C |
| ATOM | 1208 | CB | GLU | A | 390 | 11.135 | 19.521 | 24.124 | 1.00 34.37 | A | C |
| ATOM | 1209 | CG | GLU | A | 390 | 9.756 | 20.045 | 23.789 | 1.00 38.20 | A | C |
| ATOM | 1210 | CD | GLU | A | 390 | 9.070 | 20.820 | 24.898 | 1.00 41.90 | A | C |
| ATOM | 1211 | OE1 | GLU | A | 390 | 7.828 | 20.719 | 24.952 | 1.00 46.31 | A | O |
| ATOM | 1212 | OE2 | GLU | A | 390 | 9.713 | 21.544 | 25.689 | 1.00 43.08 | A | O |
| ATOM | 1213 | C | GLU | A | 390 | 13.130 | 18.433 | 23.015 | 1.00 32.95 | A | C |
| ATOM | 1214 | O | GLU | A | 390 | 13.756 | 17.588 | 23.654 | 1.00 33.32 | A | O |
| ATOM | 1215 | N | ASP | A | 391 | 13.723 | 19.361 | 22.281 | 1.00 33.18 | A | N |
| ATOM | 1216 | CA | ASP | A | 391 | 15.175 | 19.364 | 22.073 | 1.00 34.33 | A | C |
| ATOM | 1217 | CB | ASP | A | 391 | 15.497 | 20.280 | 20.876 | 1.00 34.54 | A | C |
| ATOM | 1218 | CG | ASP | A | 391 | 14.725 | 19.886 | 19.617 | 1.00 35.30 | A | C |
| ATOM | 1219 | OD1 | ASP | A | 391 | 14.330 | 18.697 | 19.490 | 1.00 35.27 | A | O |
| ATOM | 1220 | OD2 | ASP | A | 391 | 14.506 | 20.761 | 18.761 | 1.00 36.52 | A | O |
| ATOM | 1221 | C | ASP | A | 391 | 16.097 | 19.675 | 23.286 | 1.00 34.26 | A | C |
| ATOM | 1222 | O | ASP | A | 391 | 17.316 | 19.382 | 23.253 | 1.00 34.49 | A | O |
| ATOM | 1223 | N | ASN | A | 392 | 15.490 | 20.215 | 24.346 | 1.00 33.06 | A | N |
| ATOM | 1224 | CA | ASN | A | 392 | 16.184 | 20.605 | 25.572 | 1.00 32.11 | A | C |
| ATOM | 1225 | CB | ASN | A | 392 | 15.626 | 21.955 | 26.087 | 1.00 30.79 | A | C |
| ATOM | 1226 | CG | ASN | A | 392 | 14.157 | 21.861 | 26.549 | 1.00 30.59 | A | C |

Figure 11

| ATOM | 1227 | OD1 | ASN A 392 | 13.509 | 20.829 | 26.413 | 1.00 | 29.93 | A | O |
|------|------|-----|-----------|--------|--------|--------|------|-------|---|---|
| ATOM | 1228 | ND2 | ASN A 392 | 13.651 | 22.936 | 27.119 | 1.00 | 29.69 | A | N |
| ATOM | 1229 | C   | ASN A 392 | 16.088 | 19.560 | 26.693 | 1.00 | 31.59 | A | C |
| ATOM | 1230 | O   | ASN A 392 | 16.291 | 19.891 | 27.844 | 1.00 | 31.28 | A | O |
| ATOM | 1231 | N   | GLU A 393 | 15.755 | 18.321 | 26.364 | 1.00 | 31.56 | A | N |
| ATOM | 1232 | CA  | GLU A 393 | 15.603 | 17.311 | 27.396 | 1.00 | 32.97 | A | C |
| ATOM | 1233 | CB  | GLU A 393 | 14.576 | 16.264 | 26.960 | 1.00 | 33.34 | A | C |
| ATOM | 1234 | CG  | GLU A 393 | 13.154 | 16.831 | 26.977 | 1.00 | 32.29 | A | C |
| ATOM | 1235 | CD  | GLU A 393 | 12.145 | 15.967 | 26.274 | 1.00 | 32.43 | A | C |
| ATOM | 1236 | OE1 | GLU A 393 | 12.462 | 14.824 | 25.886 | 1.00 | 31.57 | A | O |
| ATOM | 1237 | OE2 | GLU A 393 | 11.006 | 16.456 | 26.109 | 1.00 | 33.27 | A | O |
| ATOM | 1238 | C   | GLU A 393 | 16.878 | 16.658 | 27.913 | 1.00 | 34.10 | A | C |
| ATOM | 1239 | O   | GLU A 393 | 16.982 | 16.329 | 29.088 | 1.00 | 33.29 | A | O |
| ATOM | 1240 | N   | TYR A 394 | 17.848 | 16.493 | 27.029 | 1.00 | 34.92 | A | N |
| ATOM | 1241 | CA  | TYR A 394 | 19.107 | 15.891 | 27.404 | 1.00 | 36.27 | A | C |
| ATOM | 1242 | CB  | TYR A 394 | 19.181 | 14.487 | 26.813 | 1.00 | 35.18 | A | C |
| ATOM | 1243 | CG  | TYR A 394 | 18.133 | 13.581 | 27.411 | 1.00 | 34.76 | A | C |
| ATOM | 1244 | CD1 | TYR A 394 | 16.919 | 13.337 | 26.752 | 1.00 | 33.95 | A | C |
| ATOM | 1245 | CE1 | TYR A 394 | 15.931 | 12.559 | 27.333 | 1.00 | 33.21 | A | C |
| ATOM | 1246 | CD2 | TYR A 394 | 18.323 | 13.014 | 28.661 | 1.00 | 33.63 | A | C |
| ATOM | 1247 | CE2 | TYR A 394 | 17.336 | 12.237 | 29.252 | 1.00 | 33.90 | A | C |
| ATOM | 1248 | CZ  | TYR A 394 | 16.143 | 12.015 | 28.586 | 1.00 | 33.89 | A | C |
| ATOM | 1249 | OH  | TYR A 394 | 15.171 | 11.249 | 29.187 | 1.00 | 33.76 | A | O |
| ATOM | 1250 | C   | TYR A 394 | 20.309 | 16.765 | 27.036 | 1.00 | 37.48 | A | C |
| ATOM | 1251 | O   | TYR A 394 | 21.449 | 16.339 | 27.210 | 1.00 | 38.43 | A | O |
| ATOM | 1252 | N   | THR A 395 | 20.032 | 17.965 | 26.514 | 1.00 | 38.40 | A | N |
| ATOM | 1253 | CA  | THR A 395 | 21.027 | 18.982 | 26.136 | 1.00 | 40.45 | A | C |
| ATOM | 1254 | CB  | THR A 395 | 21.525 | 18.867 | 24.654 | 1.00 | 40.63 | A | C |
| ATOM | 1255 | OG1 | THR A 395 | 20.409 | 18.758 | 23.751 | 1.00 | 41.04 | A | O |
| ATOM | 1256 | CG2 | THR A 395 | 22.413 | 17.661 | 24.493 | 1.00 | 41.89 | A | C |
| ATOM | 1257 | C   | THR A 395 | 20.391 | 20.357 | 26.353 | 1.00 | 41.87 | A | C |
| ATOM | 1258 | O   | THR A 395 | 19.212 | 20.445 | 26.603 | 1.00 | 41.57 | A | O |
| ATOM | 1259 | N   | ALA A 396 | 21.123 | 21.437 | 26.129 | 1.00 | 44.35 | A | N |
| ATOM | 1260 | CA  | ALA A 396 | 20.563 | 22.751 | 26.399 | 1.00 | 46.70 | A | C |
| ATOM | 1261 | CB  | ALA A 396 | 21.545 | 23.547 | 27.261 | 1.00 | 46.54 | A | C |
| ATOM | 1262 | C   | ALA A 396 | 20.009 | 23.639 | 25.267 | 1.00 | 48.71 | A | C |
| ATOM | 1263 | O   | ALA A 396 | 19.889 | 24.848 | 25.466 | 1.00 | 49.30 | A | O |
| ATOM | 1264 | N   | ARG A 397 | 19.503 | 23.058 | 24.179 | 1.00 | 50.30 | A | N |
| ATOM | 1265 | CA  | ARG A 397 | 18.979 | 23.862 | 23.063 | 1.00 | 50.98 | A | C |
| ATOM | 1266 | CB  | ARG A 397 | 18.258 | 22.977 | 22.059 | 1.00 | 50.72 | A | C |
| ATOM | 1267 | CG  | ARG A 397 | 19.077 | 21.819 | 21.586 | 1.00 | 50.14 | A | C |
| ATOM | 1268 | CD  | ARG A 397 | 19.905 | 22.133 | 20.370 | 1.00 | 50.98 | A | C |
| ATOM | 1269 | NE  | ARG A 397 | 20.531 | 20.942 | 19.809 | 1.00 | 51.58 | A | N |
| ATOM | 1270 | CZ  | ARG A 397 | 20.010 | 19.716 | 19.820 | 1.00 | 52.14 | A | C |
| ATOM | 1271 | NH1 | ARG A 397 | 18.832 | 19.452 | 20.367 | 1.00 | 52.99 | A | N |
| ATOM | 1272 | NH2 | ARG A 397 | 20.637 | 18.739 | 19.188 | 1.00 | 53.05 | A | N |
| ATOM | 1273 | C   | ARG A 397 | 18.018 | 24.944 | 23.543 | 1.00 | 52.19 | A | C |
| ATOM | 1274 | O   | ARG A 397 | 18.504 | 26.079 | 23.782 | 1.00 | 53.63 | A | O |
| ATOM | 1275 | CB  | PRO A 403 | 7.896  | 20.096 | 19.037 | 1.00 | 35.83 | A | C |
| ATOM | 1276 | CG  | PRO A 403 | 8.296  | 20.668 | 20.429 | 1.00 | 35.40 | A | C |
| ATOM | 1277 | C   | PRO A 403 | 6.864  | 21.275 | 17.085 | 1.00 | 35.10 | A | C |
| ATOM | 1278 | O   | PRO A 403 | 6.745  | 20.301 | 16.285 | 1.00 | 36.68 | A | O |
| ATOM | 1279 | N   | PRO A 403 | 7.676  | 22.514 | 19.079 | 1.00 | 35.60 | A | N |
| ATOM | 1280 | CD  | PRO A 403 | 7.993  | 22.189 | 20.478 | 1.00 | 35.72 | A | C |
| ATOM | 1281 | CA  | PRO A 403 | 7.939  | 21.335 | 18.183 | 1.00 | 35.45 | A | C |
| ATOM | 1282 | N   | ILE A 404 | 6.196  | 22.413 | 16.966 | 1.00 | 32.60 | A | N |
| ATOM | 1283 | CA  | ILE A 404 | 5.093  | 22.618 | 16.051 | 1.00 | 30.68 | A | C |
| ATOM | 1284 | CB  | ILE A 404 | 4.322  | 23.907 | 16.505 | 1.00 | 31.84 | A | C |
| ATOM | 1285 | CG2 | ILE A 404 | 4.128  | 24.925 | 15.383 | 1.00 | 31.37 | A | C |

Figure 11

| | | | | | | | | | | | |
|---|---|---|---|---|---|---|---|---|---|---|---|
| ATOM | 1286 | CG1 | ILE | A | 404 | 3.088 | 23.515 | 17.282 | 1.00 | 32.94 | A | C |
| ATOM | 1287 | CD1 | ILE | A | 404 | 2.473 | 22.215 | 16.805 | 1.00 | 35.65 | A | C |
| ATOM | 1288 | C | ILE | A | 404 | 5.446 | 22.656 | 14.554 | 1.00 | 29.04 | A | C |
| ATOM | 1289 | O | ILE | A | 404 | 4.680 | 22.188 | 13.732 | 1.00 | 28.66 | A | O |
| ATOM | 1290 | N | LYS | A | 405 | 6.634 | 23.138 | 14.214 | 1.00 | 26.02 | A | N |
| ATOM | 1291 | CA | LYS | A | 405 | 7.051 | 23.284 | 12.839 | 1.00 | 24.48 | A | C |
| ATOM | 1292 | CB | LYS | A | 405 | 8.297 | 24.185 | 12.758 | 1.00 | 24.51 | A | C |
| ATOM | 1293 | CG | LYS | A | 405 | 8.003 | 25.591 | 13.197 | 1.00 | 23.35 | A | C |
| ATOM | 1294 | CD | LYS | A | 405 | 9.188 | 26.516 | 13.011 | 1.00 | 23.66 | A | C |
| ATOM | 1295 | CE | LYS | A | 405 | 8.776 | 27.943 | 13.281 | 1.00 | 23.47 | A | C |
| ATOM | 1296 | NZ | LYS | A | 405 | 9.786 | 28.938 | 12.830 | 1.00 | 27.48 | A | N |
| ATOM | 1297 | C | LYS | A | 405 | 7.226 | 22.061 | 11.974 | 1.00 | 21.68 | A | C |
| ATOM | 1298 | O | LYS | A | 405 | 7.409 | 22.204 | 10.774 | 1.00 | 20.87 | A | O |
| ATOM | 1299 | N | TRP | A | 406 | 7.181 | 20.876 | 12.573 | 1.00 | 20.49 | A | N |
| ATOM | 1300 | CA | TRP | A | 406 | 7.325 | 19.604 | 11.859 | 1.00 | 19.61 | A | C |
| ATOM | 1301 | CB | TRP | A | 406 | 8.406 | 18.725 | 12.511 | 1.00 | 19.93 | A | C |
| ATOM | 1302 | CG | TRP | A | 406 | 9.820 | 19.281 | 12.430 | 1.00 | 22.03 | A | C |
| ATOM | 1303 | CD2 | TRP | A | 406 | 10.384 | 20.323 | 13.250 | 1.00 | 22.17 | A | C |
| ATOM | 1304 | CE2 | TRP | A | 406 | 11.673 | 20.614 | 12.731 | 1.00 | 22.08 | A | C |
| ATOM | 1305 | CE3 | TRP | A | 406 | 9.928 | 21.027 | 14.372 | 1.00 | 21.66 | A | C |
| ATOM | 1306 | CD1 | TRP | A | 406 | 10.775 | 18.967 | 11.503 | 1.00 | 22.34 | A | C |
| ATOM | 1307 | NE1 | TRP | A | 406 | 11.886 | 19.779 | 11.666 | 1.00 | 22.80 | A | N |
| ATOM | 1308 | CZ2 | TRP | A | 406 | 12.504 | 21.583 | 13.293 | 1.00 | 22.40 | A | C |
| ATOM | 1309 | CZ3 | TRP | A | 406 | 10.752 | 21.985 | 14.936 | 1.00 | 23.26 | A | C |
| ATOM | 1310 | CH2 | TRP | A | 406 | 12.034 | 22.262 | 14.391 | 1.00 | 23.08 | A | C |
| ATOM | 1311 | C | TRP | A | 406 | 6.042 | 18.775 | 11.827 | 1.00 | 20.27 | A | C |
| ATOM | 1312 | O | TRP | A | 406 | 6.001 | 17.704 | 11.227 | 1.00 | 20.21 | A | O |
| ATOM | 1313 | N | THR | A | 407 | 5.021 | 19.223 | 12.544 | 1.00 | 21.05 | A | N |
| ATOM | 1314 | CA | THR | A | 407 | 3.776 | 18.466 | 12.660 | 1.00 | 21.82 | A | C |
| ATOM | 1315 | CB | THR | A | 407 | 3.180 | 18.736 | 14.070 | 1.00 | 23.33 | A | C |
| ATOM | 1316 | OG1 | THR | A | 407 | 4.198 | 18.464 | 15.042 | 1.00 | 26.00 | A | O |
| ATOM | 1317 | CG2 | THR | A | 407 | 1.959 | 17.809 | 14.391 | 1.00 | 22.48 | A | C |
| ATOM | 1318 | C | THR | A | 407 | 2.742 | 18.708 | 11.531 | 1.00 | 21.21 | A | C |
| ATOM | 1319 | O | THR | A | 407 | 2.417 | 19.859 | 11.198 | 1.00 | 20.77 | A | O |
| ATOM | 1320 | N | ALA | A | 408 | 2.305 | 17.616 | 10.899 | 1.00 | 22.14 | A | N |
| ATOM | 1321 | CA | ALA | A | 408 | 1.296 | 17.686 | 9.811 | 1.00 | 22.93 | A | C |
| ATOM | 1322 | CB | ALA | A | 408 | 0.942 | 16.327 | 9.320 | 1.00 | 22.78 | A | C |
| ATOM | 1323 | C | ALA | A | 408 | 0.049 | 18.336 | 10.343 | 1.00 | 23.62 | A | C |
| ATOM | 1324 | O | ALA | A | 408 | -0.245 | 18.225 | 11.524 | 1.00 | 23.33 | A | O |
| ATOM | 1325 | N | PRO | A | 409 | -0.763 | 18.924 | 9.451 | 1.00 | 24.75 | A | N |
| ATOM | 1326 | CD | PRO | A | 409 | -0.527 | 18.993 | 7.995 | 1.00 | 25.26 | A | C |
| ATOM | 1327 | CA | PRO | A | 409 | -2.016 | 19.612 | 9.806 | 1.00 | 25.49 | A | C |
| ATOM | 1328 | CB | PRO | A | 409 | -2.541 | 20.076 | 8.453 | 1.00 | 25.54 | A | C |
| ATOM | 1329 | CG | PRO | A | 409 | -1.250 | 20.237 | 7.630 | 1.00 | 25.68 | A | C |
| ATOM | 1330 | C | PRO | A | 409 | -3.031 | 18.754 | 10.559 | 1.00 | 25.91 | A | C |
| ATOM | 1331 | O | PRO | A | 409 | -3.635 | 19.209 | 11.514 | 1.00 | 25.58 | A | O |
| ATOM | 1332 | N | GLU | A | 410 | -3.201 | 17.515 | 10.126 | 1.00 | 26.07 | A | N |
| ATOM | 1333 | CA | GLU | A | 410 | -4.149 | 16.618 | 10.769 | 1.00 | 26.49 | A | C |
| ATOM | 1334 | CB | GLU | A | 410 | -4.440 | 15.368 | 9.904 | 1.00 | 24.30 | A | C |
| ATOM | 1335 | CG | GLU | A | 410 | -3.325 | 14.303 | 9.790 | 1.00 | 24.37 | A | C |
| ATOM | 1336 | CD | GLU | A | 410 | -2.173 | 14.675 | 8.827 | 1.00 | 21.29 | A | C |
| ATOM | 1337 | OE1 | GLU | A | 410 | -2.252 | 15.689 | 8.137 | 1.00 | 19.12 | A | O |
| ATOM | 1338 | OE2 | GLU | A | 410 | -1.189 | 13.902 | 8.767 | 1.00 | 22.43 | A | O |
| ATOM | 1339 | C | GLU | A | 410 | -3.687 | 16.228 | 12.180 | 1.00 | 26.86 | A | C |
| ATOM | 1340 | O | GLU | A | 410 | -4.516 | 15.899 | 13.054 | 1.00 | 26.84 | A | O |
| ATOM | 1341 | N | ALA | A | 411 | -2.382 | 16.296 | 12.418 | 1.00 | 26.65 | A | N |
| ATOM | 1342 | CA | ALA | A | 411 | -1.875 | 15.968 | 13.736 | 1.00 | 28.02 | A | C |
| ATOM | 1343 | CB | ALA | A | 411 | -0.445 | 15.462 | 13.667 | 1.00 | 26.61 | A | C |
| ATOM | 1344 | C | ALA | A | 411 | -2.027 | 17.201 | 14.640 | 1.00 | 29.01 | A | C |

Figure 11

| | | | | | | | | | | |
|---|---|---|---|---|---|---|---|---|---|---|
| ATOM | 1345 | O | ALA | A | 411 | -2.321 | 17.078 | 15.830 | 1.00 29.72 | A O |
| ATOM | 1346 | N | ILE | A | 412 | -1.915 | 18.392 | 14.065 | 1.00 29.86 | A N |
| ATOM | 1347 | CA | ILE | A | 412 | -2.118 | 19.606 | 14.841 | 1.00 31.13 | A C |
| ATOM | 1348 | CB | ILE | A | 412 | -1.755 | 20.844 | 14.064 | 1.00 30.47 | A C |
| ATOM | 1349 | CG2 | ILE | A | 412 | -2.103 | 22.116 | 14.889 | 1.00 32.27 | A C |
| ATOM | 1350 | CG1 | ILE | A | 412 | -0.287 | 20.834 | 13.697 | 1.00 30.04 | A C |
| ATOM | 1351 | CD1 | ILE | A | 412 | 0.087 | 22.012 | 12.898 | 1.00 29.14 | A C |
| ATOM | 1352 | C | ILE | A | 412 | -3.605 | 19.796 | 15.197 | 1.00 33.23 | A C |
| ATOM | 1353 | O | ILE | A | 412 | -3.946 | 20.112 | 16.345 | 1.00 34.68 | A O |
| ATOM | 1354 | N | ASN | A | 413 | -4.488 | 19.596 | 14.217 | 1.00 33.47 | A N |
| ATOM | 1355 | CA | ASN | A | 413 | -5.920 | 19.822 | 14.420 | 1.00 34.14 | A C |
| ATOM | 1356 | CB | ASN | A | 413 | -6.609 | 20.063 | 13.082 | 1.00 35.16 | A C |
| ATOM | 1357 | CG | ASN | A | 413 | -6.031 | 21.239 | 12.340 | 1.00 37.68 | A C |
| ATOM | 1358 | OD1 | ASN | A | 413 | -5.461 | 22.155 | 12.952 | 1.00 39.13 | A O |
| ATOM | 1359 | ND2 | ASN | A | 413 | -6.177 | 21.235 | 11.007 | 1.00 37.63 | A N |
| ATOM | 1360 | C | ASN | A | 413 | -6.708 | 18.756 | 15.166 | 1.00 34.07 | A C |
| ATOM | 1361 | O | ASN | A | 413 | -7.699 | 19.071 | 15.837 | 1.00 34.55 | A O |
| ATOM | 1362 | N | TYR | A | 414 | -6.299 | 17.501 | 15.017 | 1.00 33.11 | A N |
| ATOM | 1363 | CA | TYR | A | 414 | -7.028 | 16.388 | 15.613 | 1.00 33.09 | A C |
| ATOM | 1364 | CB | TYR | A | 414 | -7.823 | 15.652 | 14.515 | 1.00 34.76 | A C |
| ATOM | 1365 | CG | TYR | A | 414 | -8.690 | 16.566 | 13.685 | 1.00 38.54 | A C |
| ATOM | 1366 | CD1 | TYR | A | 414 | -9.929 | 17.004 | 14.161 | 1.00 40.22 | A C |
| ATOM | 1367 | CE1 | TYR | A | 414 | -10.710 | 17.906 | 13.433 | 1.00 41.43 | A C |
| ATOM | 1368 | CD2 | TYR | A | 414 | -8.255 | 17.046 | 12.447 | 1.00 40.46 | A C |
| ATOM | 1369 | CE2 | TYR | A | 414 | -9.043 | 17.955 | 11.704 | 1.00 42.79 | A C |
| ATOM | 1370 | CZ | TYR | A | 414 | -10.266 | 18.375 | 12.219 | 1.00 43.47 | A C |
| ATOM | 1371 | OH | TYR | A | 414 | -11.046 | 19.279 | 11.524 | 1.00 47.33 | A O |
| ATOM | 1372 | C | TYR | A | 414 | -6.172 | 15.362 | 16.355 | 1.00 31.06 | A C |
| ATOM | 1373 | O | TYR | A | 414 | -6.700 | 14.348 | 16.801 | 1.00 29.33 | A O |
| ATOM | 1374 | N | GLY | A | 415 | -4.866 | 15.600 | 16.463 | 1.00 29.22 | A N |
| ATOM | 1375 | CA | GLY | A | 415 | -4.016 | 14.618 | 17.125 | 1.00 28.29 | A C |
| ATOM | 1376 | C | GLY | A | 415 | -3.898 | 13.276 | 16.390 | 1.00 27.67 | A C |
| ATOM | 1377 | O | GLY | A | 415 | -3.546 | 12.258 | 16.985 | 1.00 27.55 | A O |
| ATOM | 1378 | N | THR | A | 416 | -4.168 | 13.265 | 15.088 | 1.00 26.83 | A N |
| ATOM | 1379 | CA | THR | A | 416 | -4.062 | 12.023 | 14.345 | 1.00 26.72 | A C |
| ATOM | 1380 | CB | THR | A | 416 | -5.288 | 11.789 | 13.389 | 1.00 27.36 | A C |
| ATOM | 1381 | OG1 | THR | A | 416 | -4.865 | 11.107 | 12.196 | 1.00 31.17 | A O |
| ATOM | 1382 | CG2 | THR | A | 416 | -5.987 | 13.062 | 13.079 | 1.00 24.90 | A C |
| ATOM | 1383 | C | THR | A | 416 | -2.680 | 11.872 | 13.692 | 1.00 26.52 | A C |
| ATOM | 1384 | O | THR | A | 416 | -2.305 | 12.569 | 12.732 | 1.00 25.64 | A O |
| ATOM | 1385 | N | PHE | A | 417 | -1.904 | 10.995 | 14.314 | 1.00 26.29 | A N |
| ATOM | 1386 | CA | PHE | A | 417 | -0.535 | 10.714 | 13.907 | 1.00 25.34 | A C |
| ATOM | 1387 | CB | PHE | A | 417 | 0.404 | 10.688 | 15.134 | 1.00 23.89 | A C |
| ATOM | 1388 | CG | PHE | A | 417 | 0.709 | 12.053 | 15.736 | 1.00 24.32 | A C |
| ATOM | 1389 | CD1 | PHE | A | 417 | -0.127 | 12.615 | 16.707 | 1.00 24.82 | A C |
| ATOM | 1390 | CD2 | PHE | A | 417 | 1.858 | 12.762 | 15.356 | 1.00 22.74 | A C |
| ATOM | 1391 | CE1 | PHE | A | 417 | 0.188 | 13.874 | 17.294 | 1.00 24.96 | A C |
| ATOM | 1392 | CE2 | PHE | A | 417 | 2.181 | 14.006 | 15.928 | 1.00 23.30 | A C |
| ATOM | 1393 | CZ | PHE | A | 417 | 1.353 | 14.571 | 16.891 | 1.00 24.04 | A C |
| ATOM | 1394 | C | PHE | A | 417 | -0.463 | 9.369 | 13.231 | 1.00 24.78 | A C |
| ATOM | 1395 | O | PHE | A | 417 | -0.812 | 8.369 | 13.815 | 1.00 24.69 | A O |
| ATOM | 1396 | N | THR | A | 418 | 0.076 | 9.352 | 12.018 | 1.00 24.73 | A N |
| ATOM | 1397 | CA | THR | A | 418 | 0.268 | 8.128 | 11.252 | 1.00 22.71 | A C |
| ATOM | 1398 | CB | THR | A | 418 | -0.789 | 7.990 | 10.153 | 1.00 23.00 | A C |
| ATOM | 1399 | OG1 | THR | A | 418 | -0.559 | 9.002 | 9.170 | 1.00 22.44 | A O |
| ATOM | 1400 | CG2 | THR | A | 418 | -2.205 | 8.163 | 10.729 | 1.00 23.53 | A C |
| ATOM | 1401 | C | THR | A | 418 | 1.640 | 8.259 | 10.558 | 1.00 21.82 | A C |
| ATOM | 1402 | O | THR | A | 418 | 2.331 | 9.260 | 10.682 | 1.00 21.08 | A O |
| ATOM | 1403 | N | ILE | A | 419 | 1.986 | 7.268 | 9.773 | 1.00 21.18 | A N |

Figure 11

```
ATOM   1404  CA   ILE A 419       3.225   7.287   9.053  1.00 22.90      A    C
ATOM   1405  CB   ILE A 419       3.471   5.931   8.353  1.00 24.16      A    C
ATOM   1406  CG2  ILE A 419       2.400   5.680   7.268  1.00 23.36      A    C
ATOM   1407  CG1  ILE A 419       4.926   5.863   7.832  1.00 23.69      A    C
ATOM   1408  CD1  ILE A 419       5.961   5.933   8.929  1.00 21.95      A    C
ATOM   1409  C    ILE A 419       3.191   8.427   8.025  1.00 23.05      A    C
ATOM   1410  O    ILE A 419       4.244   8.903   7.629  1.00 23.81      A    O
ATOM   1411  N    LYS A 420       1.991   8.849   7.604  1.00 22.09      A    N
ATOM   1412  CA   LYS A 420       1.839   9.949   6.655  1.00 20.54      A    C
ATOM   1413  CB   LYS A 420       0.451   9.964   5.993  1.00 20.51      A    C
ATOM   1414  CG   LYS A 420       0.194   8.734   5.116  1.00 20.29      A    C
ATOM   1415  CD   LYS A 420       1.094   8.788   3.863  1.00 21.38      A    C
ATOM   1416  CE   LYS A 420       0.988   7.513   3.050  1.00 21.38      A    C
ATOM   1417  NZ   LYS A 420       1.893   7.615   1.876  1.00 25.15      A    N
ATOM   1418  C    LYS A 420       2.159  11.281   7.308  1.00 19.42      A    C
ATOM   1419  O    LYS A 420       2.575  12.208   6.617  1.00 19.04      A    O
ATOM   1420  N    SER A 421       1.873  11.437   8.602  1.00 19.51      A    N
ATOM   1421  CA   SER A 421       2.267  12.677   9.245  1.00 19.25      A    C
ATOM   1422  CB   SER A 421       1.483  12.983  10.552  1.00 19.41      A    C
ATOM   1423  OG   SER A 421       1.247  11.853  11.371  1.00 21.89      A    O
ATOM   1424  C    SER A 421       3.812  12.624   9.407  1.00 18.62      A    C
ATOM   1425  O    SER A 421       4.457  13.636   9.401  1.00 19.01      A    O
ATOM   1426  N    ASP A 422       4.411  11.446   9.496  1.00 19.04      A    N
ATOM   1427  CA   ASP A 422       5.885  11.397   9.552  1.00 19.85      A    C
ATOM   1428  CB   ASP A 422       6.418   9.996   9.849  1.00 18.80      A    C
ATOM   1429  CG   ASP A 422       6.238   9.589  11.297  1.00 20.15      A    C
ATOM   1430  OD1  ASP A 422       6.148  10.461  12.195  1.00 21.73      A    O
ATOM   1431  OD2  ASP A 422       6.172   8.377  11.543  1.00 21.85      A    O
ATOM   1432  C    ASP A 422       6.418  11.829   8.187  1.00 20.15      A    C
ATOM   1433  O    ASP A 422       7.449  12.520   8.110  1.00 19.63      A    O
ATOM   1434  N    VAL A 423       5.738  11.414   7.108  1.00 20.05      A    N
ATOM   1435  CA   VAL A 423       6.156  11.822   5.755  1.00 18.80      A    C
ATOM   1436  CB   VAL A 423       5.270  11.213   4.601  1.00 18.60      A    C
ATOM   1437  CG1  VAL A 423       5.613  11.872   3.231  1.00 14.70      A    C
ATOM   1438  CG2  VAL A 423       5.542   9.705   4.483  1.00 17.01      A    C
ATOM   1439  C    VAL A 423       6.156  13.349   5.674  1.00 18.72      A    C
ATOM   1440  O    VAL A 423       7.076  13.942   5.081  1.00 19.12      A    O
ATOM   1441  N    TRP A 424       5.161  13.986   6.300  1.00 18.19      A    N
ATOM   1442  CA   TRP A 424       5.080  15.444   6.315  1.00 16.48      A    C
ATOM   1443  CB   TRP A 424       3.787  15.923   7.015  1.00 16.24      A    C
ATOM   1444  CG   TRP A 424       3.705  17.411   7.256  1.00 16.46      A    C
ATOM   1445  CD2  TRP A 424       2.892  18.387   6.550  1.00 16.61      A    C
ATOM   1446  CE2  TRP A 424       3.211  19.648   7.081  1.00 17.74      A    C
ATOM   1447  CE3  TRP A 424       1.924  18.302   5.525  1.00 19.42      A    C
ATOM   1448  CD1  TRP A 424       4.441  18.122   8.156  1.00 15.46      A    C
ATOM   1449  NE1  TRP A 424       4.164  19.451   8.051  1.00 17.06      A    N
ATOM   1450  CZ2  TRP A 424       2.594  20.854   6.630  1.00 18.27      A    C
ATOM   1451  CZ3  TRP A 424       1.302  19.489   5.065  1.00 17.87      A    C
ATOM   1452  CH2  TRP A 424       1.644  20.750   5.621  1.00 19.71      A    C
ATOM   1453  C    TRP A 424       6.339  15.967   7.015  1.00 17.33      A    C
ATOM   1454  O    TRP A 424       7.015  16.865   6.495  1.00 14.50      A    O
ATOM   1455  N    SER A 425       6.649  15.390   8.183  1.00 18.17      A    N
ATOM   1456  CA   SER A 425       7.829  15.793   8.948  1.00 20.32      A    C
ATOM   1457  CB   SER A 425       7.951  15.013  10.266  1.00 21.20      A    C
ATOM   1458  OG   SER A 425       6.899  15.296  11.161  1.00 22.43      A    O
ATOM   1459  C    SER A 425       9.137  15.619   8.154  1.00 20.13      A    C
ATOM   1460  O    SER A 425      10.030  16.431   8.290  1.00 21.15      A    O
ATOM   1461  N    PHE A 426       9.257  14.539   7.392  1.00 20.35      A    N
ATOM   1462  CA   PHE A 426      10.448  14.284   6.589  1.00 21.40      A    C
```

Figure 11

```
ATOM  1463  CB   PHE A 426     10.365  12.931   5.885  1.00 21.76      A  C
ATOM  1464  CG   PHE A 426     11.606  12.575   5.101  1.00 22.05      A  C
ATOM  1465  CD1  PHE A 426     12.770  12.153   5.758  1.00 22.55      A  C
ATOM  1466  CD2  PHE A 426     11.609  12.650   3.705  1.00 22.76      A  C
ATOM  1467  CE1  PHE A 426     13.920  11.804   5.046  1.00 22.30      A  C
ATOM  1468  CE2  PHE A 426     12.755  12.304   2.957  1.00 20.94      A  C
ATOM  1469  CZ   PHE A 426     13.916  11.878   3.637  1.00 24.23      A  C
ATOM  1470  C    PHE A 426     10.654  15.414   5.585  1.00 21.61      A  C
ATOM  1471  O    PHE A 426     11.780  15.899   5.418  1.00 21.97      A  O
ATOM  1472  N    GLY A 427      9.566  15.849   4.933  1.00 20.36      A  N
ATOM  1473  CA   GLY A 427      9.673  16.953   4.006  1.00 17.76      A  C
ATOM  1474  C    GLY A 427     10.247  18.174   4.727  1.00 18.61      A  C
ATOM  1475  O    GLY A 427     11.068  18.886   4.173  1.00 18.16      A  O
ATOM  1476  N    ILE A 428      9.759  18.475   5.930  1.00 18.32      A  N
ATOM  1477  CA   ILE A 428     10.268  19.614   6.666  1.00 18.67      A  C
ATOM  1478  CB   ILE A 428      9.508  19.845   7.998  1.00 18.34      A  C
ATOM  1479  CG2  ILE A 428     10.055  21.033   8.681  1.00 14.84      A  C
ATOM  1480  CG1  ILE A 428      7.979  19.969   7.768  1.00 17.05      A  C
ATOM  1481  CD1  ILE A 428      7.533  21.284   7.053  1.00 17.21      A  C
ATOM  1482  C    ILE A 428     11.759  19.334   6.991  1.00 20.35      A  C
ATOM  1483  O    ILE A 428     12.606  20.226   6.863  1.00 21.14      A  O
ATOM  1484  N    LEU A 429     12.078  18.087   7.330  1.00 20.02      A  N
ATOM  1485  CA   LEU A 429     13.437  17.694   7.650  1.00 21.42      A  C
ATOM  1486  CB   LEU A 429     13.476  16.216   8.047  1.00 20.76      A  C
ATOM  1487  CG   LEU A 429     14.638  15.715   8.923  1.00 21.90      A  C
ATOM  1488  CD1  LEU A 429     14.366  14.286   9.334  1.00 22.87      A  C
ATOM  1489  CD2  LEU A 429     15.982  15.809   8.233  1.00 22.78      A  C
ATOM  1490  C    LEU A 429     14.362  17.956   6.441  1.00 21.52      A  C
ATOM  1491  O    LEU A 429     15.508  18.352   6.619  1.00 22.12      A  O
ATOM  1492  N    LEU A 430     13.844  17.780   5.223  1.00 20.98      A  N
ATOM  1493  CA   LEU A 430     14.628  17.994   4.003  1.00 20.80      A  C
ATOM  1494  CB   LEU A 430     13.853  17.558   2.753  1.00 20.11      A  C
ATOM  1495  CG   LEU A 430     13.661  16.052   2.464  1.00 20.53      A  C
ATOM  1496  CD1  LEU A 430     12.757  15.829   1.226  1.00 19.66      A  C
ATOM  1497  CD2  LEU A 430     15.005  15.352   2.232  1.00 19.81      A  C
ATOM  1498  C    LEU A 430     15.058  19.453   3.889  1.00 21.15      A  C
ATOM  1499  O    LEU A 430     16.146  19.740   3.416  1.00 20.54      A  O
ATOM  1500  N    THR A 431     14.207  20.384   4.320  1.00 22.23      A  N
ATOM  1501  CA   THR A 431     14.587  21.791   4.270  1.00 22.80      A  C
ATOM  1502  CB   THR A 431     13.411  22.725   4.550  1.00 23.06      A  C
ATOM  1503  OG1  THR A 431     13.035  22.626   5.931  1.00 24.67      A  O
ATOM  1504  CG2  THR A 431     12.218  22.409   3.616  1.00 21.41      A  C
ATOM  1505  C    THR A 431     15.741  22.084   5.259  1.00 24.09      A  C
ATOM  1506  O    THR A 431     16.659  22.876   4.949  1.00 23.59      A  O
ATOM  1507  N    GLU A 432     15.685  21.461   6.446  1.00 23.29      A  N
ATOM  1508  CA   GLU A 432     16.756  21.620   7.435  1.00 22.76      A  C
ATOM  1509  CB   GLU A 432     16.470  20.805   8.691  1.00 22.20      A  C
ATOM  1510  CG   GLU A 432     15.296  21.285   9.502  1.00 22.42      A  C
ATOM  1511  CD   GLU A 432     15.109  20.418  10.732  1.00 22.47      A  C
ATOM  1512  OE1  GLU A 432     14.618  19.276  10.618  1.00 20.55      A  O
ATOM  1513  OE2  GLU A 432     15.468  20.894  11.817  1.00 22.03      A  O
ATOM  1514  C    GLU A 432     18.075  21.109   6.828  1.00 22.82      A  C
ATOM  1515  O    GLU A 432     19.116  21.723   6.993  1.00 22.56      A  O
ATOM  1516  N    ILE A 433     18.010  19.981   6.125  1.00 23.15      A  N
ATOM  1517  CA   ILE A 433     19.173  19.391   5.492  1.00 24.24      A  C
ATOM  1518  CB   ILE A 433     18.837  18.016   4.901  1.00 23.43      A  C
ATOM  1519  CG2  ILE A 433     19.916  17.597   3.905  1.00 24.38      A  C
ATOM  1520  CG1  ILE A 433     18.736  16.969   6.021  1.00 22.15      A  C
ATOM  1521  CD1  ILE A 433     18.425  15.566   5.565  1.00 20.11      A  C
```

Figure 11

| ATOM | 1522 | C   | ILE | A | 433 | 19.861 | 20.258 | 4.421  | 1.00 | 26.80 | A | C |
|------|------|-----|-----|---|-----|--------|--------|--------|------|-------|---|---|
| ATOM | 1523 | O   | ILE | A | 433 | 21.078 | 20.445 | 4.472  | 1.00 | 26.82 | A | O |
| ATOM | 1524 | N   | VAL | A | 434 | 19.087 | 20.829 | 3.486  | 1.00 | 28.09 | A | N |
| ATOM | 1525 | CA  | VAL | A | 434 | 19.693 | 21.611 | 2.411  | 1.00 | 28.17 | A | C |
| ATOM | 1526 | CB  | VAL | A | 434 | 18.870 | 21.564 | 1.122  | 1.00 | 27.78 | A | C |
| ATOM | 1527 | CG1 | VAL | A | 434 | 18.677 | 20.124 | 0.735  | 1.00 | 27.00 | A | C |
| ATOM | 1528 | CG2 | VAL | A | 434 | 17.523 | 22.320 | 1.293  | 1.00 | 27.87 | A | C |
| ATOM | 1529 | C   | VAL | A | 434 | 20.068 | 23.032 | 2.733  | 1.00 | 28.22 | A | C |
| ATOM | 1530 | O   | VAL | A | 434 | 20.791 | 23.656 | 1.973  | 1.00 | 28.31 | A | O |
| ATOM | 1531 | N   | THR | A | 435 | 19.591 | 23.526 | 3.860  | 1.00 | 28.89 | A | N |
| ATOM | 1532 | CA  | THR | A | 435 | 19.918 | 24.873 | 4.298  | 1.00 | 29.95 | A | C |
| ATOM | 1533 | CB  | THR | A | 435 | 18.674 | 25.561 | 4.833  | 1.00 | 31.25 | A | C |
| ATOM | 1534 | OG1 | THR | A | 435 | 18.149 | 24.793 | 5.936  | 1.00 | 31.64 | A | O |
| ATOM | 1535 | CG2 | THR | A | 435 | 17.608 | 25.717 | 3.707  | 1.00 | 28.76 | A | C |
| ATOM | 1536 | C   | THR | A | 435 | 20.975 | 24.829 | 5.434  | 1.00 | 30.87 | A | C |
| ATOM | 1537 | O   | THR | A | 435 | 21.196 | 25.821 | 6.141  | 1.00 | 30.60 | A | O |
| ATOM | 1538 | N   | HIS | A | 436 | 21.543 | 23.643 | 5.652  | 1.00 | 31.25 | A | N |
| ATOM | 1539 | CA  | HIS | A | 436 | 22.536 | 23.383 | 6.691  | 1.00 | 32.57 | A | C |
| ATOM | 1540 | CB  | HIS | A | 436 | 23.852 | 24.112 | 6.390  | 1.00 | 35.13 | A | C |
| ATOM | 1541 | CG  | HIS | A | 436 | 24.459 | 23.754 | 5.064  | 1.00 | 36.40 | A | C |
| ATOM | 1542 | CD2 | HIS | A | 436 | 24.783 | 24.525 | 4.003  | 1.00 | 37.80 | A | C |
| ATOM | 1543 | ND1 | HIS | A | 436 | 24.845 | 22.473 | 4.728  | 1.00 | 37.74 | A | N |
| ATOM | 1544 | CE1 | HIS | A | 436 | 25.394 | 22.471 | 3.528  | 1.00 | 34.89 | A | C |
| ATOM | 1545 | NE2 | HIS | A | 436 | 25.367 | 23.704 | 3.067  | 1.00 | 37.58 | A | N |
| ATOM | 1546 | C   | HIS | A | 436 | 22.029 | 23.711 | 8.107  | 1.00 | 32.29 | A | C |
| ATOM | 1547 | O   | HIS | A | 436 | 22.667 | 24.439 | 8.861  | 1.00 | 31.94 | A | O |
| ATOM | 1548 | N   | GLY | A | 437 | 20.862 | 23.180 | 8.451  | 1.00 | 31.55 | A | N |
| ATOM | 1549 | CA  | GLY | A | 437 | 20.313 | 23.399 | 9.774  | 1.00 | 31.47 | A | C |
| ATOM | 1550 | C   | GLY | A | 437 | 19.427 | 24.598 | 10.052 | 1.00 | 31.46 | A | C |
| ATOM | 1551 | O   | GLY | A | 437 | 19.111 | 24.867 | 11.211 | 1.00 | 32.15 | A | O |
| ATOM | 1552 | N   | ARG | A | 438 | 18.985 | 25.311 | 9.028  | 1.00 | 30.80 | A | N |
| ATOM | 1553 | CA  | ARG | A | 438 | 18.125 | 26.459 | 9.282  | 1.00 | 31.26 | A | C |
| ATOM | 1554 | CB  | ARG | A | 438 | 17.999 | 27.262 | 8.002  | 1.00 | 34.08 | A | C |
| ATOM | 1555 | CG  | ARG | A | 438 | 17.573 | 28.711 | 8.184  | 1.00 | 38.13 | A | C |
| ATOM | 1556 | CD  | ARG | A | 438 | 16.081 | 28.851 | 8.332  | 1.00 | 41.47 | A | C |
| ATOM | 1557 | NE  | ARG | A | 438 | 15.325 | 28.165 | 7.268  | 1.00 | 45.56 | A | N |
| ATOM | 1558 | CZ  | ARG | A | 438 | 15.372 | 28.503 | 5.980  | 1.00 | 46.96 | A | C |
| ATOM | 1559 | NH1 | ARG | A | 438 | 16.155 | 29.518 | 5.604  | 1.00 | 48.58 | A | N |
| ATOM | 1560 | NH2 | ARG | A | 438 | 14.609 | 27.874 | 5.087  | 1.00 | 45.60 | A | N |
| ATOM | 1561 | C   | ARG | A | 438 | 16.742 | 26.011 | 9.820  | 1.00 | 30.67 | A | C |
| ATOM | 1562 | O   | ARG | A | 438 | 16.219 | 24.960 | 9.426  | 1.00 | 29.40 | A | O |
| ATOM | 1563 | N   | ILE | A | 439 | 16.192 | 26.779 | 10.759 | 1.00 | 29.32 | A | N |
| ATOM | 1564 | CA  | ILE | A | 439 | 14.886 | 26.466 | 11.355 | 1.00 | 29.98 | A | C |
| ATOM | 1565 | CB  | ILE | A | 439 | 14.573 | 27.385 | 12.593 | 1.00 | 32.00 | A | C |
| ATOM | 1566 | CG2 | ILE | A | 439 | 13.321 | 26.890 | 13.351 | 1.00 | 32.32 | A | C |
| ATOM | 1567 | CG1 | ILE | A | 439 | 15.715 | 27.274 | 13.616 | 1.00 | 35.84 | A | C |
| ATOM | 1568 | CD1 | ILE | A | 439 | 15.768 | 28.422 | 14.682 | 1.00 | 38.00 | A | C |
| ATOM | 1569 | C   | ILE | A | 439 | 13.776 | 26.627 | 10.297 | 1.00 | 28.98 | A | C |
| ATOM | 1570 | O   | ILE | A | 439 | 13.823 | 27.531 | 9.442  | 1.00 | 27.65 | A | O |
| ATOM | 1571 | N   | PRO | A | 440 | 12.807 | 25.701 | 10.284 | 1.00 | 27.94 | A | N |
| ATOM | 1572 | CD  | PRO | A | 440 | 12.747 | 24.385 | 10.934 | 1.00 | 27.27 | A | C |
| ATOM | 1573 | CA  | PRO | A | 440 | 11.737 | 25.840 | 9.286  | 1.00 | 27.81 | A | C |
| ATOM | 1574 | CB  | PRO | A | 440 | 10.920 | 24.572 | 9.500  | 1.00 | 27.03 | A | C |
| ATOM | 1575 | CG  | PRO | A | 440 | 11.975 | 23.588 | 9.924  | 1.00 | 27.81 | A | C |
| ATOM | 1576 | C   | PRO | A | 440 | 10.944 | 27.124 | 9.550  | 1.00 | 27.32 | A | C |
| ATOM | 1577 | O   | PRO | A | 440 | 11.084 | 27.720 | 10.625 | 1.00 | 27.31 | A | O |
| ATOM | 1578 | N   | TYR | A | 441 | 10.248 | 27.616 | 8.520  | 1.00 | 27.39 | A | N |
| ATOM | 1579 | CA  | TYR | A | 441 | 9.426  | 28.838 | 8.607  | 1.00 | 27.40 | A | C |
| ATOM | 1580 | CB  | TYR | A | 441 | 8.113  | 28.556 | 9.355  | 1.00 | 25.48 | A | C |

Figure 11

| ATOM | 1581 | CG | TYR | A | 441 | 7.347 | 27.349 | 8.866 | 1.00 | 22.81 | A | C |
| ATOM | 1582 | CD1 | TYR | A | 441 | 6.472 | 27.439 | 7.775 | 1.00 | 22.23 | A | C |
| ATOM | 1583 | CE1 | TYR | A | 441 | 5.784 | 26.320 | 7.301 | 1.00 | 20.14 | A | C |
| ATOM | 1584 | CD2 | TYR | A | 441 | 7.504 | 26.115 | 9.481 | 1.00 | 21.09 | A | C |
| ATOM | 1585 | CE2 | TYR | A | 441 | 6.821 | 24.988 | 9.024 | 1.00 | 22.09 | A | C |
| ATOM | 1586 | CZ | TYR | A | 441 | 5.961 | 25.105 | 7.925 | 1.00 | 21.49 | A | C |
| ATOM | 1587 | OH | TYR | A | 441 | 5.341 | 23.995 | 7.436 | 1.00 | 21.16 | A | O |
| ATOM | 1588 | C | TYR | A | 441 | 10.171 | 29.973 | 9.315 | 1.00 | 29.22 | A | C |
| ATOM | 1589 | O | TYR | A | 441 | 9.695 | 30.519 | 10.312 | 1.00 | 29.64 | A | O |
| ATOM | 1590 | N | PRO | A | 442 | 11.343 | 30.356 | 8.803 | 1.00 | 31.23 | A | N |
| ATOM | 1591 | CD | PRO | A | 442 | 11.973 | 29.908 | 7.545 | 1.00 | 31.64 | A | C |
| ATOM | 1592 | CA | PRO | A | 442 | 12.110 | 31.435 | 9.448 | 1.00 | 32.70 | A | C |
| ATOM | 1593 | CB | PRO | A | 442 | 13.357 | 31.531 | 8.580 | 1.00 | 33.21 | A | C |
| ATOM | 1594 | CG | PRO | A | 442 | 12.863 | 31.058 | 7.202 | 1.00 | 32.52 | A | C |
| ATOM | 1595 | C | PRO | A | 442 | 11.336 | 32.739 | 9.536 | 1.00 | 34.64 | A | C |
| ATOM | 1596 | O | PRO | A | 442 | 10.651 | 33.137 | 8.595 | 1.00 | 35.12 | A | O |
| ATOM | 1597 | N | GLY | A | 443 | 11.356 | 33.360 | 10.710 | 1.00 | 36.43 | A | N |
| ATOM | 1598 | CA | GLY | A | 443 | 10.614 | 34.595 | 10.885 | 1.00 | 37.74 | A | C |
| ATOM | 1599 | C | GLY | A | 443 | 9.161 | 34.365 | 11.278 | 1.00 | 38.88 | A | C |
| ATOM | 1600 | O | GLY | A | 443 | 8.391 | 35.322 | 11.382 | 1.00 | 40.25 | A | O |
| ATOM | 1601 | N | MET | A | 444 | 8.755 | 33.108 | 11.461 | 1.00 | 38.51 | A | N |
| ATOM | 1602 | CA | MET | A | 444 | 7.382 | 32.814 | 11.901 | 1.00 | 37.51 | A | C |
| ATOM | 1603 | CB | MET | A | 444 | 6.675 | 31.842 | 10.933 | 1.00 | 36.58 | A | C |
| ATOM | 1604 | CG | MET | A | 444 | 6.009 | 32.506 | 9.739 | 1.00 | 36.39 | A | C |
| ATOM | 1605 | SD | MET | A | 444 | 5.306 | 31.371 | 8.517 | 1.00 | 35.81 | A | S |
| ATOM | 1606 | CE | MET | A | 444 | 4.412 | 30.490 | 9.445 | 1.00 | 33.29 | A | C |
| ATOM | 1607 | C | MET | A | 444 | 7.433 | 32.190 | 13.301 | 1.00 | 37.75 | A | C |
| ATOM | 1608 | O | MET | A | 444 | 8.310 | 31.377 | 13.573 | 1.00 | 38.25 | A | O |
| ATOM | 1609 | N | THR | A | 445 | 6.546 | 32.602 | 14.206 | 1.00 | 37.89 | A | N |
| ATOM | 1610 | CA | THR | A | 445 | 6.506 | 32.014 | 15.554 | 1.00 | 37.77 | A | C |
| ATOM | 1611 | CB | THR | A | 445 | 5.782 | 32.914 | 16.567 | 1.00 | 38.97 | A | C |
| ATOM | 1612 | OG1 | THR | A | 445 | 4.450 | 33.148 | 16.099 | 1.00 | 38.28 | A | O |
| ATOM | 1613 | CG2 | THR | A | 445 | 6.504 | 34.254 | 16.740 | 1.00 | 39.50 | A | C |
| ATOM | 1614 | C | THR | A | 445 | 5.641 | 30.768 | 15.427 | 1.00 | 37.15 | A | C |
| ATOM | 1615 | O | THR | A | 445 | 5.044 | 30.544 | 14.384 | 1.00 | 38.02 | A | O |
| ATOM | 1616 | N | ASN | A | 446 | 5.520 | 29.982 | 16.484 | 1.00 | 36.37 | A | N |
| ATOM | 1617 | CA | ASN | A | 446 | 4.678 | 28.794 | 16.404 | 1.00 | 35.68 | A | C |
| ATOM | 1618 | CB | ASN | A | 446 | 4.740 | 27.963 | 17.688 | 1.00 | 34.56 | A | C |
| ATOM | 1619 | CG | ASN | A | 446 | 5.927 | 27.007 | 17.716 | 1.00 | 33.94 | A | C |
| ATOM | 1620 | OD1 | ASN | A | 446 | 6.787 | 27.046 | 16.842 | 1.00 | 33.43 | A | O |
| ATOM | 1621 | ND2 | ASN | A | 446 | 5.957 | 26.125 | 18.716 | 1.00 | 33.50 | A | N |
| ATOM | 1622 | C | ASN | A | 446 | 3.215 | 29.115 | 16.048 | 1.00 | 35.84 | A | C |
| ATOM | 1623 | O | ASN | A | 446 | 2.663 | 28.511 | 15.126 | 1.00 | 34.20 | A | O |
| ATOM | 1624 | N | PRO | A | 447 | 2.565 | 30.056 | 16.781 | 1.00 | 36.78 | A | N |
| ATOM | 1625 | CD | PRO | A | 447 | 2.970 | 30.744 | 18.025 | 1.00 | 37.05 | A | C |
| ATOM | 1626 | CA | PRO | A | 447 | 1.165 | 30.372 | 16.452 | 1.00 | 36.65 | A | C |
| ATOM | 1627 | CB | PRO | A | 447 | 0.752 | 31.360 | 17.557 | 1.00 | 36.94 | A | C |
| ATOM | 1628 | CG | PRO | A | 447 | 2.063 | 31.930 | 18.039 | 1.00 | 37.22 | A | C |
| ATOM | 1629 | C | PRO | A | 447 | 0.946 | 30.919 | 15.032 | 1.00 | 35.64 | A | C |
| ATOM | 1630 | O | PRO | A | 447 | -0.117 | 30.702 | 14.442 | 1.00 | 35.11 | A | O |
| ATOM | 1631 | N | GLU | A | 448 | 1.973 | 31.552 | 14.468 | 1.00 | 34.36 | A | N |
| ATOM | 1632 | CA | GLU | A | 448 | 1.892 | 32.093 | 13.117 | 1.00 | 32.88 | A | C |
| ATOM | 1633 | CB | GLU | A | 448 | 3.051 | 33.036 | 12.843 | 1.00 | 33.86 | A | C |
| ATOM | 1634 | CG | GLU | A | 448 | 3.033 | 34.252 | 13.700 | 1.00 | 35.92 | A | C |
| ATOM | 1635 | CD | GLU | A | 448 | 4.113 | 35.244 | 13.316 | 1.00 | 37.83 | A | C |
| ATOM | 1636 | OE1 | GLU | A | 448 | 5.201 | 34.833 | 12.863 | 1.00 | 38.33 | A | O |
| ATOM | 1637 | OE2 | GLU | A | 448 | 3.866 | 36.454 | 13.465 | 1.00 | 38.78 | A | O |
| ATOM | 1638 | C | GLU | A | 448 | 1.938 | 30.964 | 12.111 | 1.00 | 32.02 | A | C |
| ATOM | 1639 | O | GLU | A | 448 | 1.338 | 31.043 | 11.041 | 1.00 | 31.51 | A | O |

Figure 11

```
ATOM   1640  N    VAL A 449       2.698  29.927  12.443  1.00 30.13      A    N
ATOM   1641  CA   VAL A 449       2.808  28.770  11.570  1.00 28.76      A    C
ATOM   1642  CB   VAL A 449       3.884  27.767  12.064  1.00 27.75      A    C
ATOM   1643  CG1  VAL A 449       3.727  26.430  11.379  1.00 26.85      A    C
ATOM   1644  CG2  VAL A 449       5.276  28.325  11.815  1.00 25.05      A    C
ATOM   1645  C    VAL A 449       1.448  28.104  11.505  1.00 28.46      A    C
ATOM   1646  O    VAL A 449       0.970  27.792  10.410  1.00 28.78      A    O
ATOM   1647  N    ILE A 450       0.813  27.957  12.673  1.00 27.73      A    N
ATOM   1648  CA   ILE A 450      -0.502  27.331  12.779  1.00 28.08      A    C
ATOM   1649  CB   ILE A 450      -1.064  27.351  14.222  1.00 28.25      A    C
ATOM   1650  CG2  ILE A 450      -2.393  26.645  14.268  1.00 27.15      A    C
ATOM   1651  CG1  ILE A 450      -0.074  26.761  15.240  1.00 29.65      A    C
ATOM   1652  CD1  ILE A 450       0.335  25.365  14.977  1.00 29.18      A    C
ATOM   1653  C    ILE A 450      -1.511  28.082  11.910  1.00 27.48      A    C
ATOM   1654  O    ILE A 450      -2.327  27.467  11.231  1.00 27.51      A    O
ATOM   1655  N    GLN A 451      -1.479  29.408  11.973  1.00 27.73      A    N
ATOM   1656  CA   GLN A 451      -2.416  30.186  11.172  1.00 29.12      A    C
ATOM   1657  CB   GLN A 451      -2.663  31.596  11.735  1.00 31.52      A    C
ATOM   1658  CG   GLN A 451      -1.486  32.530  11.876  1.00 37.79      A    C
ATOM   1659  CD   GLN A 451      -1.693  33.536  13.025  1.00 39.82      A    C
ATOM   1660  OE1  GLN A 451      -1.144  34.636  13.024  1.00 40.75      A    O
ATOM   1661  NE2  GLN A 451      -2.449  33.118  14.041  1.00 41.61      A    N
ATOM   1662  C    GLN A 451      -2.130  30.203   9.687  1.00 27.39      A    C
ATOM   1663  O    GLN A 451      -3.045  30.304   8.904  1.00 26.56      A    O
ATOM   1664  N    ASN A 452      -0.865  30.106   9.303  1.00 26.18      A    N
ATOM   1665  CA   ASN A 452      -0.513  30.068   7.887  1.00 26.01      A    C
ATOM   1666  CB   ASN A 452       0.985  30.337   7.683  1.00 27.38      A    C
ATOM   1667  CG   ASN A 452       1.289  31.810   7.407  1.00 31.85      A    C
ATOM   1668  OD1  ASN A 452       1.304  32.249   6.240  1.00 34.13      A    O
ATOM   1669  ND2  ASN A 452       1.508  32.594   8.474  1.00 31.09      A    N
ATOM   1670  C    ASN A 452      -0.920  28.689   7.333  1.00 23.97      A    C
ATOM   1671  O    ASN A 452      -1.424  28.584   6.217  1.00 23.04      A    O
ATOM   1672  N    LEU A 453      -0.737  27.645   8.126  1.00 23.47      A    N
ATOM   1673  CA   LEU A 453      -1.117  26.310   7.718  1.00 24.49      A    C
ATOM   1674  CB   LEU A 453      -0.577  25.263   8.688  1.00 25.46      A    C
ATOM   1675  CG   LEU A 453       0.919  24.925   8.601  1.00 26.10      A    C
ATOM   1676  CD1  LEU A 453       1.245  23.773   9.581  1.00 24.71      A    C
ATOM   1677  CD2  LEU A 453       1.298  24.532   7.182  1.00 25.27      A    C
ATOM   1678  C    LEU A 453      -2.642  26.183   7.611  1.00 24.74      A    C
ATOM   1679  O    LEU A 453      -3.128  25.314   6.891  1.00 24.66      A    O
ATOM   1680  N    GLU A 454      -3.384  26.983   8.377  1.00 25.03      A    N
ATOM   1681  CA   GLU A 454      -4.835  26.964   8.290  1.00 27.32      A    C
ATOM   1682  CB   GLU A 454      -5.472  27.940   9.268  1.00 30.53      A    C
ATOM   1683  CG   GLU A 454      -5.472  27.553  10.705  1.00 37.02      A    C
ATOM   1684  CD   GLU A 454      -5.757  28.761  11.593  1.00 41.23      A    C
ATOM   1685  OE1  GLU A 454      -5.632  28.626  12.843  1.00 45.04      A    O
ATOM   1686  OE2  GLU A 454      -6.063  29.851  11.041  1.00 43.08      A    O
ATOM   1687  C    GLU A 454      -5.198  27.479   6.891  1.00 25.90      A    C
ATOM   1688  O    GLU A 454      -6.184  27.059   6.320  1.00 24.48      A    O
ATOM   1689  N    ARG A 455      -4.394  28.423   6.397  1.00 25.13      A    N
ATOM   1690  CA   ARG A 455      -4.589  29.034   5.081  1.00 24.68      A    C
ATOM   1691  CB   ARG A 455      -4.153  30.504   5.120  1.00 25.27      A    C
ATOM   1692  CG   ARG A 455      -4.748  31.386   6.232  1.00 27.43      A    C
ATOM   1693  CD   ARG A 455      -4.141  32.814   6.201  1.00 30.26      A    C
ATOM   1694  NE   ARG A 455      -2.720  32.718   5.874  1.00 36.71      A    N
ATOM   1695  CZ   ARG A 455      -2.187  32.975   4.665  1.00 38.07      A    C
ATOM   1696  NH1  ARG A 455      -2.943  33.409   3.658  1.00 37.04      A    N
ATOM   1697  NH2  ARG A 455      -0.964  32.528   4.371  1.00 35.64      A    N
ATOM   1698  C    ARG A 455      -3.849  28.279   3.946  1.00 23.91      A    C
```

Figure 11

```
ATOM   1699  O    ARG A 455      -3.754  28.784   2.823  1.00 23.72           A   O
ATOM   1700  N    GLY A 456      -3.304  27.098   4.269  1.00 23.27           A   N
ATOM   1701  CA   GLY A 456      -2.604  26.241   3.317  1.00 22.26           A   C
ATOM   1702  C    GLY A 456      -1.222  26.661   2.848  1.00 21.79           A   C
ATOM   1703  O    GLY A 456      -0.760  26.272   1.772  1.00 21.19           A   O
ATOM   1704  N    TYR A 457      -0.535  27.417   3.684  1.00 21.73           A   N
ATOM   1705  CA   TYR A 457       0.786  27.914   3.361  1.00 20.68           A   C
ATOM   1706  CB   TYR A 457       1.211  28.931   4.425  1.00 20.04           A   C
ATOM   1707  CG   TYR A 457       2.610  29.475   4.267  1.00 20.47           A   C
ATOM   1708  CD1  TYR A 457       2.839  30.663   3.578  1.00 20.69           A   C
ATOM   1709  CE1  TYR A 457       4.133  31.171   3.423  1.00 22.37           A   C
ATOM   1710  CD2  TYR A 457       3.716  28.789   4.804  1.00 20.83           A   C
ATOM   1711  CE2  TYR A 457       5.012  29.279   4.644  1.00 20.06           A   C
ATOM   1712  CZ   TYR A 457       5.216  30.461   3.955  1.00 22.76           A   C
ATOM   1713  OH   TYR A 457       6.512  30.911   3.741  1.00 25.92           A   O
ATOM   1714  C    TYR A 457       1.840  26.811   3.217  1.00 20.75           A   C
ATOM   1715  O    TYR A 457       1.791  25.778   3.885  1.00 20.12           A   O
ATOM   1716  N    ARG A 458       2.773  27.027   2.292  1.00 21.00           A   N
ATOM   1717  CA   ARG A 458       3.858  26.085   2.067  1.00 21.90           A   C
ATOM   1718  CB   ARG A 458       3.610  25.198   0.843  1.00 21.47           A   C
ATOM   1719  CG   ARG A 458       2.374  24.252   0.956  1.00 20.07           A   C
ATOM   1720  CD   ARG A 458       2.503  23.296   2.124  1.00 20.55           A   C
ATOM   1721  NE   ARG A 458       1.464  22.265   2.128  1.00 20.94           A   N
ATOM   1722  CZ   ARG A 458       0.334  22.328   2.840  1.00 21.72           A   C
ATOM   1723  NH1  ARG A 458       0.081  23.372   3.628  1.00 19.05           A   N
ATOM   1724  NH2  ARG A 458      -0.559  21.346   2.743  1.00 20.59           A   N
ATOM   1725  C    ARG A 458       5.116  26.902   1.904  1.00 22.81           A   C
ATOM   1726  O    ARG A 458       5.074  28.009   1.354  1.00 22.93           A   O
ATOM   1727  N    MET A 459       6.207  26.436   2.507  1.00 22.65           A   N
ATOM   1728  CA   MET A 459       7.473  27.150   2.382  1.00 23.11           A   C
ATOM   1729  CB   MET A 459       8.571  26.453   3.167  1.00 22.96           A   C
ATOM   1730  CG   MET A 459       8.543  26.627   4.665  1.00 24.67           A   C
ATOM   1731  SD   MET A 459      10.053  25.861   5.365  1.00 24.76           A   S
ATOM   1732  CE   MET A 459       9.487  24.219   5.769  1.00 23.05           A   C
ATOM   1733  C    MET A 459       7.902  27.184   0.917  1.00 23.61           A   C
ATOM   1734  O    MET A 459       7.568  26.284   0.139  1.00 23.01           A   O
ATOM   1735  N    VAL A 460       8.609  28.243   0.538  1.00 25.48           A   N
ATOM   1736  CA   VAL A 460       9.119  28.367  -0.827  1.00 26.17           A   C
ATOM   1737  CB   VAL A 460       9.392  29.831  -1.181  1.00 26.31           A   C
ATOM   1738  CG1  VAL A 460       8.184  30.656  -0.849  1.00 24.73           A   C
ATOM   1739  CG2  VAL A 460      10.628  30.361  -0.426  1.00 27.06           A   C
ATOM   1740  C    VAL A 460      10.418  27.518  -0.954  1.00 27.50           A   C
ATOM   1741  O    VAL A 460      10.903  26.944   0.037  1.00 26.22           A   O
ATOM   1742  N    ARG A 461      10.934  27.390  -2.178  1.00 27.70           A   N
ATOM   1743  CA   ARG A 461      12.140  26.621  -2.407  1.00 28.72           A   C
ATOM   1744  CB   ARG A 461      12.412  26.487  -3.912  1.00 29.62           A   C
ATOM   1745  CG   ARG A 461      13.583  25.556  -4.271  1.00 32.85           A   C
ATOM   1746  CD   ARG A 461      13.848  25.503  -5.771  1.00 35.32           A   C
ATOM   1747  NE   ARG A 461      14.205  26.818  -6.267  1.00 40.27           A   N
ATOM   1748  CZ   ARG A 461      15.401  27.377  -6.100  1.00 43.72           A   C
ATOM   1749  NH1  ARG A 461      16.381  26.709  -5.478  1.00 44.41           A   N
ATOM   1750  NH2  ARG A 461      15.568  28.668  -6.378  1.00 44.24           A   N
ATOM   1751  C    ARG A 461      13.301  27.335  -1.685  1.00 28.00           A   C
ATOM   1752  O    ARG A 461      13.514  28.533  -1.865  1.00 28.18           A   O
ATOM   1753  N    PRO A 462      13.977  26.634  -0.759  1.00 27.94           A   N
ATOM   1754  CD   PRO A 462      13.752  25.238  -0.350  1.00 25.83           A   C
ATOM   1755  CA   PRO A 462      15.103  27.239  -0.020  1.00 28.89           A   C
ATOM   1756  CB   PRO A 462      15.501  26.145   0.968  1.00 27.68           A   C
ATOM   1757  CG   PRO A 462      14.262  25.250   1.035  1.00 27.59           A   C
```

Figure 11

| | | | | | | | | | | |
|---|---|---|---|---|---|---|---|---|---|---|
| ATOM | 1758 | C | PRO | A | 462 | 16.264 | 27.489 | -0.970 | 1.00 30.52 | A C |
| ATOM | 1759 | O | PRO | A | 462 | 16.476 | 26.720 | -1.915 | 1.00 29.14 | A O |
| ATOM | 1760 | N | ASP | A | 463 | 17.041 | 28.526 | -0.687 | 1.00 33.39 | A N |
| ATOM | 1761 | CA | ASP | A | 463 | 18.191 | 28.850 | -1.517 | 1.00 36.78 | A C |
| ATOM | 1762 | CB | ASP | A | 463 | 18.954 | 30.067 | -0.953 | 1.00 38.38 | A C |
| ATOM | 1763 | CG | ASP | A | 463 | 18.117 | 31.362 | -0.954 | 1.00 41.14 | A C |
| ATOM | 1764 | OD1 | ASP | A | 463 | 17.243 | 31.551 | -1.841 | 1.00 42.48 | A O |
| ATOM | 1765 | OD2 | ASP | A | 463 | 18.345 | 32.218 | -0.063 | 1.00 43.54 | A O |
| ATOM | 1766 | C | ASP | A | 463 | 19.101 | 27.621 | -1.601 | 1.00 37.93 | A C |
| ATOM | 1767 | O | ASP | A | 463 | 19.290 | 26.889 | -0.621 | 1.00 38.27 | A O |
| ATOM | 1768 | N | ASN | A | 464 | 19.531 | 27.330 | -2.826 | 1.00 39.85 | A N |
| ATOM | 1769 | CA | ASN | A | 464 | 20.428 | 26.211 | -3.128 | 1.00 41.10 | A C |
| ATOM | 1770 | CB | ASN | A | 464 | 21.764 | 26.370 | -2.384 | 1.00 43.90 | A C |
| ATOM | 1771 | CG | ASN | A | 464 | 22.506 | 27.654 | -2.782 | 1.00 45.40 | A C |
| ATOM | 1772 | OD1 | ASN | A | 464 | 22.664 | 27.943 | -3.977 | 1.00 46.40 | A O |
| ATOM | 1773 | ND2 | ASN | A | 464 | 22.926 | 28.446 | -1.783 | 1.00 45.95 | A N |
| ATOM | 1774 | C | ASN | A | 464 | 19.838 | 24.820 | -2.910 | 1.00 41.03 | A C |
| ATOM | 1775 | O | ASN | A | 464 | 20.467 | 23.919 | -2.347 | 1.00 41.91 | A O |
| ATOM | 1776 | N | CYS | A | 465 | 18.629 | 24.640 | -3.422 | 1.00 40.16 | A N |
| ATOM | 1777 | CA | CYS | A | 465 | 17.923 | 23.367 | -3.322 | 1.00 38.16 | A C |
| ATOM | 1778 | CB | CYS | A | 465 | 16.740 | 23.515 | -2.337 | 1.00 36.65 | A C |
| ATOM | 1779 | SG | CYS | A | 465 | 15.482 | 22.197 | -2.348 | 1.00 32.25 | A S |
| ATOM | 1780 | C | CYS | A | 465 | 17.436 | 23.003 | -4.732 | 1.00 37.36 | A C |
| ATOM | 1781 | O | CYS | A | 465 | 16.815 | 23.810 | -5.400 | 1.00 37.68 | A O |
| ATOM | 1782 | N | PRO | A | 466 | 17.795 | 21.819 | -5.232 | 1.00 36.45 | A N |
| ATOM | 1783 | CD | PRO | A | 466 | 18.630 | 20.766 | -4.624 | 1.00 37.13 | A C |
| ATOM | 1784 | CA | PRO | A | 466 | 17.337 | 21.432 | -6.571 | 1.00 35.92 | A C |
| ATOM | 1785 | CB | PRO | A | 466 | 17.787 | 19.976 | -6.678 | 1.00 35.65 | A C |
| ATOM | 1786 | CG | PRO | A | 466 | 19.014 | 19.929 | -5.839 | 1.00 36.89 | A C |
| ATOM | 1787 | C | PRO | A | 466 | 15.801 | 21.517 | -6.648 | 1.00 35.96 | A C |
| ATOM | 1788 | O | PRO | A | 466 | 15.125 | 21.279 | -5.642 | 1.00 34.95 | A O |
| ATOM | 1789 | N | GLU | A | 467 | 15.261 | 21.867 | -7.823 | 1.00 35.00 | A N |
| ATOM | 1790 | CA | GLU | A | 467 | 13.807 | 21.973 | -8.016 | 1.00 34.86 | A C |
| ATOM | 1791 | CB | GLU | A | 467 | 13.455 | 22.442 | -9.437 | 1.00 35.99 | A C |
| ATOM | 1792 | CG | GLU | A | 467 | 12.719 | 23.812 | -9.537 | 1.00 39.28 | A C |
| ATOM | 1793 | CD | GLU | A | 467 | 11.432 | 23.939 | -8.710 | 1.00 40.12 | A C |
| ATOM | 1794 | OE1 | GLU | A | 467 | 11.371 | 24.866 | -7.875 | 1.00 40.26 | A O |
| ATOM | 1795 | OE2 | GLU | A | 467 | 10.469 | 23.167 | -8.933 | 1.00 41.93 | A O |
| ATOM | 1796 | C | GLU | A | 467 | 13.106 | 20.642 | -7.793 | 1.00 33.66 | A C |
| ATOM | 1797 | O | GLU | A | 467 | 11.990 | 20.590 | -7.290 | 1.00 32.77 | A O |
| ATOM | 1798 | N | GLU | A | 468 | 13.754 | 19.582 | -8.252 | 1.00 33.00 | A N |
| ATOM | 1799 | CA | GLU | A | 468 | 13.219 | 18.248 | -8.140 | 1.00 33.28 | A C |
| ATOM | 1800 | CB | GLU | A | 468 | 14.115 | 17.244 | -8.873 | 1.00 37.37 | A C |
| ATOM | 1801 | CG | GLU | A | 468 | 14.300 | 17.483 | -10.380 | 1.00 41.83 | A C |
| ATOM | 1802 | CD | GLU | A | 468 | 15.323 | 18.598 | -10.720 | 1.00 45.44 | A C |
| ATOM | 1803 | OE1 | GLU | A | 468 | 16.224 | 18.913 | -9.881 | 1.00 45.68 | A O |
| ATOM | 1804 | OE2 | GLU | A | 468 | 15.223 | 19.152 | -11.855 | 1.00 46.32 | A O |
| ATOM | 1805 | C | GLU | A | 468 | 13.093 | 17.875 | -6.671 | 1.00 31.37 | A C |
| ATOM | 1806 | O | GLU | A | 468 | 12.134 | 17.204 | -6.292 | 1.00 31.50 | A O |
| ATOM | 1807 | N | LEU | A | 469 | 14.041 | 18.331 | -5.844 | 1.00 29.33 | A N |
| ATOM | 1808 | CA | LEU | A | 469 | 14.020 | 18.056 | -4.401 | 1.00 27.10 | A C |
| ATOM | 1809 | CB | LEU | A | 469 | 15.317 | 18.470 | -3.695 | 1.00 26.54 | A C |
| ATOM | 1810 | CG | LEU | A | 469 | 15.362 | 18.001 | -2.228 | 1.00 24.20 | A C |
| ATOM | 1811 | CD1 | LEU | A | 469 | 15.314 | 16.490 | -2.180 | 1.00 23.39 | A C |
| ATOM | 1812 | CD2 | LEU | A | 469 | 16.662 | 18.481 | -1.609 | 1.00 25.77 | A C |
| ATOM | 1813 | C | LEU | A | 469 | 12.878 | 18.815 | -3.759 | 1.00 25.63 | A C |
| ATOM | 1814 | O | LEU | A | 469 | 12.230 | 18.291 | -2.856 | 1.00 25.49 | A O |
| ATOM | 1815 | N | TYR | A | 470 | 12.686 | 20.066 | -4.184 | 1.00 23.98 | A N |
| ATOM | 1816 | CA | TYR | A | 470 | 11.588 | 20.904 | -3.687 | 1.00 23.42 | A C |

Figure 11

| ATOM | 1817 | CB  | TYR A 470 | 11.653 | 22.315 | -4.242 | 1.00 | 21.07 | A | C |
| ATOM | 1818 | CG  | TYR A 470 | 10.512 | 23.207 | -3.774 | 1.00 | 22.48 | A | C |
| ATOM | 1819 | CD1 | TYR A 470 | 10.385 | 23.558 | -2.428 | 1.00 | 22.13 | A | C |
| ATOM | 1820 | CE1 | TYR A 470 |  9.333 | 24.369 | -1.983 | 1.00 | 23.15 | A | C |
| ATOM | 1821 | CD2 | TYR A 470 |  9.545 | 23.696 | -4.680 | 1.00 | 22.47 | A | C |
| ATOM | 1822 | CE2 | TYR A 470 |  8.494 | 24.511 | -4.243 | 1.00 | 22.32 | A | C |
| ATOM | 1823 | CZ  | TYR A 470 |  8.397 | 24.843 | -2.895 | 1.00 | 23.03 | A | C |
| ATOM | 1824 | OH  | TYR A 470 |  7.389 | 25.663 | -2.453 | 1.00 | 22.54 | A | O |
| ATOM | 1825 | C   | TYR A 470 | 10.225 | 20.338 | -4.075 | 1.00 | 23.98 | A | C |
| ATOM | 1826 | O   | TYR A 470 |  9.265 | 20.478 | -3.326 | 1.00 | 23.87 | A | O |
| ATOM | 1827 | N   | GLN A 471 | 10.130 | 19.719 | -5.251 | 1.00 | 24.02 | A | N |
| ATOM | 1828 | CA  | GLN A 471 |  8.854 | 19.167 | -5.661 | 1.00 | 24.77 | A | C |
| ATOM | 1829 | CB  | GLN A 471 |  8.812 | 18.918 | -7.184 | 1.00 | 26.59 | A | C |
| ATOM | 1830 | CG  | GLN A 471 |  8.683 | 20.248 | -7.990 | 1.00 | 27.68 | A | C |
| ATOM | 1831 | CD  | GLN A 471 |  7.478 | 21.093 | -7.539 | 1.00 | 30.30 | A | C |
| ATOM | 1832 | OE1 | GLN A 471 |  6.378 | 20.552 | -7.239 | 1.00 | 30.33 | A | O |
| ATOM | 1833 | NE2 | GLN A 471 |  7.671 | 22.410 | -7.475 | 1.00 | 28.70 | A | N |
| ATOM | 1834 | C   | GLN A 471 |  8.600 | 17.925 | -4.838 | 1.00 | 24.45 | A | C |
| ATOM | 1835 | O   | GLN A 471 |  7.462 | 17.582 | -4.539 | 1.00 | 24.77 | A | O |
| ATOM | 1836 | N   | LEU A 472 |  9.677 | 17.290 | -4.409 | 1.00 | 24.24 | A | N |
| ATOM | 1837 | CA  | LEU A 472 |  9.556 | 16.120 | -3.573 | 1.00 | 24.02 | A | C |
| ATOM | 1838 | CB  | LEU A 472 | 10.927 | 15.482 | -3.398 | 1.00 | 26.46 | A | C |
| ATOM | 1839 | CG  | LEU A 472 | 10.942 | 13.977 | -3.249 | 1.00 | 29.13 | A | C |
| ATOM | 1840 | CD1 | LEU A 472 | 10.338 | 13.325 | -4.507 | 1.00 | 28.41 | A | C |
| ATOM | 1841 | CD2 | LEU A 472 | 12.399 | 13.535 | -3.014 | 1.00 | 30.92 | A | C |
| ATOM | 1842 | C   | LEU A 472 |  8.996 | 16.596 | -2.214 | 1.00 | 22.76 | A | C |
| ATOM | 1843 | O   | LEU A 472 |  8.130 | 15.932 | -1.647 | 1.00 | 22.08 | A | O |
| ATOM | 1844 | N   | MET A 473 |  9.538 | 17.706 | -1.697 | 1.00 | 21.21 | A | N |
| ATOM | 1845 | CA  | MET A 473 |  9.066 | 18.311 | -0.451 | 1.00 | 21.55 | A | C |
| ATOM | 1846 | CB  | MET A 473 |  9.786 | 19.631 | -0.190 | 1.00 | 21.02 | A | C |
| ATOM | 1847 | CG  | MET A 473 | 11.306 | 19.507 |  0.131 | 1.00 | 20.69 | A | C |
| ATOM | 1848 | SD  | MET A 473 | 12.075 | 21.098 |  0.136 | 1.00 | 23.46 | A | S |
| ATOM | 1849 | CE  | MET A 473 | 13.654 | 20.634 |  0.769 | 1.00 | 22.96 | A | C |
| ATOM | 1850 | C   | MET A 473 |  7.561 | 18.623 | -0.563 | 1.00 | 22.26 | A | C |
| ATOM | 1851 | O   | MET A 473 |  6.783 | 18.323 |  0.353 | 1.00 | 21.43 | A | O |
| ATOM | 1852 | N   | ARG A 474 |  7.157 | 19.203 | -1.697 | 1.00 | 22.38 | A | N |
| ATOM | 1853 | CA  | ARG A 474 |  5.762 | 19.566 | -1.907 | 1.00 | 23.33 | A | C |
| ATOM | 1854 | CB  | ARG A 474 |  5.547 | 20.334 | -3.213 | 1.00 | 24.01 | A | C |
| ATOM | 1855 | CG  | ARG A 474 |  6.251 | 21.677 | -3.256 | 1.00 | 23.92 | A | C |
| ATOM | 1856 | CD  | ARG A 474 |  5.839 | 22.584 | -2.112 | 1.00 | 25.93 | A | C |
| ATOM | 1857 | NE  | ARG A 474 |  4.425 | 22.939 | -2.178 | 1.00 | 26.56 | A | N |
| ATOM | 1858 | CZ  | ARG A 474 |  3.937 | 24.081 | -2.665 | 1.00 | 25.45 | A | C |
| ATOM | 1859 | NH1 | ARG A 474 |  4.744 | 25.027 | -3.121 | 1.00 | 22.66 | A | N |
| ATOM | 1860 | NH2 | ARG A 474 |  2.621 | 24.215 | -2.811 | 1.00 | 25.13 | A | N |
| ATOM | 1861 | C   | ARG A 474 |  4.866 | 18.349 | -1.840 | 1.00 | 23.15 | A | C |
| ATOM | 1862 | O   | ARG A 474 |  3.769 | 18.431 | -1.307 | 1.00 | 24.13 | A | O |
| ATOM | 1863 | N   | LEU A 475 |  5.339 | 17.210 | -2.325 | 1.00 | 22.46 | A | N |
| ATOM | 1864 | CA  | LEU A 475 |  4.535 | 16.011 | -2.246 | 1.00 | 22.61 | A | C |
| ATOM | 1865 | CB  | LEU A 475 |  5.101 | 14.901 | -3.133 | 1.00 | 23.45 | A | C |
| ATOM | 1866 | CG  | LEU A 475 |  4.887 | 15.056 | -4.664 | 1.00 | 25.21 | A | C |
| ATOM | 1867 | CD1 | LEU A 475 |  5.695 | 13.987 | -5.399 | 1.00 | 23.39 | A | C |
| ATOM | 1868 | CD2 | LEU A 475 |  3.397 | 14.959 | -5.068 | 1.00 | 25.75 | A | C |
| ATOM | 1869 | C   | LEU A 475 |  4.393 | 15.544 | -0.788 | 1.00 | 22.08 | A | C |
| ATOM | 1870 | O   | LEU A 475 |  3.353 | 15.014 | -0.420 | 1.00 | 20.49 | A | O |
| ATOM | 1871 | N   | CYS A 476 |  5.456 | 15.703 |  0.012 | 1.00 | 20.97 | A | N |
| ATOM | 1872 | CA  | CYS A 476 |  5.435 | 15.317 |  1.427 | 1.00 | 20.54 | A | C |
| ATOM | 1873 | CB  | CYS A 476 |  6.830 | 15.457 |  2.076 | 1.00 | 19.86 | A | C |
| ATOM | 1874 | SG  | CYS A 476 |  8.122 | 14.311 |  1.441 | 1.00 | 22.10 | A | S |
| ATOM | 1875 | C   | CYS A 476 |  4.441 | 16.192 |  2.197 | 1.00 | 20.14 | A | C |

Figure 11

```
ATOM   1876  O   CYS A 476       3.907  15.750   3.199  1.00 19.89      A    O
ATOM   1877  N   TRP A 477       4.213  17.421   1.715  1.00 19.91      A    N
ATOM   1878  CA  TRP A 477       3.304  18.370   2.355  1.00 20.99      A    C
ATOM   1879  CB  TRP A 477       3.906  19.786   2.357  1.00 20.70      A    C
ATOM   1880  CG  TRP A 477       5.284  19.885   2.912  1.00 20.52      A    C
ATOM   1881  CD2 TRP A 477       6.290  20.843   2.547  1.00 19.85      A    C
ATOM   1882  CE2 TRP A 477       7.448  20.548   3.317  1.00 20.71      A    C
ATOM   1883  CE3 TRP A 477       6.331  21.922   1.641  1.00 19.94      A    C
ATOM   1884  CD1 TRP A 477       5.859  19.073   3.871  1.00 20.69      A    C
ATOM   1885  NE1 TRP A 477       7.150  19.466   4.113  1.00 21.37      A    N
ATOM   1886  CZ2 TRP A 477       8.641  21.289   3.206  1.00 19.66      A    C
ATOM   1887  CZ3 TRP A 477       7.526  22.671   1.529  1.00 20.01      A    C
ATOM   1888  CH2 TRP A 477       8.664  22.343   2.316  1.00 21.07      A    C
ATOM   1889  C   TRP A 477       1.903  18.444   1.712  1.00 21.10      A    C
ATOM   1890  O   TRP A 477       1.231  19.468   1.835  1.00 21.58      A    O
ATOM   1891  N   LYS A 478       1.487  17.411   0.978  1.00 21.56      A    N
ATOM   1892  CA  LYS A 478       0.137  17.438   0.410  1.00 23.42      A    C
ATOM   1893  CB  LYS A 478      -0.174  16.171  -0.411  1.00 23.38      A    C
ATOM   1894  CG  LYS A 478       0.594  16.059  -1.755  1.00 27.04      A    C
ATOM   1895  CD  LYS A 478       0.288  17.208  -2.672  1.00 30.05      A    C
ATOM   1896  CE  LYS A 478      -1.033  16.964  -3.416  1.00 33.98      A    C
ATOM   1897  NZ  LYS A 478      -1.469  18.252  -4.098  1.00 37.92      A    N
ATOM   1898  C   LYS A 478      -0.809  17.515   1.610  1.00 22.96      A    C
ATOM   1899  O   LYS A 478      -0.580  16.854   2.641  1.00 21.88      A    O
ATOM   1900  N   GLU A 479      -1.849  18.325   1.480  1.00 22.95      A    N
ATOM   1901  CA  GLU A 479      -2.811  18.494   2.558  1.00 23.21      A    C
ATOM   1902  CB  GLU A 479      -3.970  19.407   2.116  1.00 23.15      A    C
ATOM   1903  CG  GLU A 479      -4.944  19.801   3.284  1.00 22.44      A    C
ATOM   1904  CD  GLU A 479      -4.238  20.630   4.387  1.00 24.18      A    C
ATOM   1905  OE1 GLU A 479      -3.359  21.451   4.082  1.00 24.99      A    O
ATOM   1906  OE2 GLU A 479      -4.563  20.477   5.569  1.00 23.84      A    O
ATOM   1907  C   GLU A 479      -3.361  17.146   3.045  1.00 22.71      A    C
ATOM   1908  O   GLU A 479      -3.431  16.893   4.243  1.00 21.64      A    O
ATOM   1909  N   ARG A 480      -3.791  16.306   2.106  1.00 23.05      A    N
ATOM   1910  CA  ARG A 480      -4.336  14.994   2.435  1.00 23.86      A    C
ATOM   1911  CB  ARG A 480      -5.248  14.520   1.339  1.00 25.65      A    C
ATOM   1912  CG  ARG A 480      -6.529  15.275   1.287  1.00 30.85      A    C
ATOM   1913  CD  ARG A 480      -7.169  14.863   0.008  1.00 36.93      A    C
ATOM   1914  NE  ARG A 480      -8.455  15.506  -0.212  1.00 42.27      A    N
ATOM   1915  CZ  ARG A 480      -8.971  15.722  -1.419  1.00 44.60      A    C
ATOM   1916  NH1 ARG A 480      -8.293  15.352  -2.511  1.00 45.80      A    N
ATOM   1917  NH2 ARG A 480     -10.191  16.242  -1.529  1.00 45.43      A    N
ATOM   1918  C   ARG A 480      -3.231  13.983   2.619  1.00 22.57      A    C
ATOM   1919  O   ARG A 480      -2.406  13.800   1.733  1.00 23.15      A    O
ATOM   1920  N   PRO A 481      -3.295  13.212   3.699  1.00 21.51      A    N
ATOM   1921  CD  PRO A 481      -4.425  13.133   4.640  1.00 20.81      A    C
ATOM   1922  CA  PRO A 481      -2.293  12.201   4.011  1.00 20.58      A    C
ATOM   1923  CB  PRO A 481      -2.894  11.506   5.250  1.00 21.52      A    C
ATOM   1924  CG  PRO A 481      -3.786  12.524   5.837  1.00 21.97      A    C
ATOM   1925  C   PRO A 481      -2.107  11.208   2.885  1.00 20.87      A    C
ATOM   1926  O   PRO A 481      -0.982  10.823   2.574  1.00 20.25      A    O
ATOM   1927  N   GLU A 482      -3.220  10.762   2.298  1.00 21.93      A    N
ATOM   1928  CA  GLU A 482      -3.183   9.772   1.214  1.00 22.13      A    C
ATOM   1929  CB  GLU A 482      -4.615   9.251   0.881  1.00 22.98      A    C
ATOM   1930  CG  GLU A 482      -5.569  10.239   0.197  1.00 24.88      A    C
ATOM   1931  CD  GLU A 482      -6.389  11.090   1.161  1.00 26.67      A    C
ATOM   1932  OE1 GLU A 482      -6.050  11.196   2.375  1.00 29.25      A    O
ATOM   1933  OE2 GLU A 482      -7.361  11.690   0.694  1.00 27.78      A    O
ATOM   1934  C   GLU A 482      -2.436  10.218  -0.052  1.00 20.97      A    C
```

Figure 11

| ATOM | 1935 | O   | GLU A 482 | -1.974 | 9.394  | -0.813 | 1.00 | 22.77 | A | O |
|------|------|-----|-----------|--------|--------|--------|------|-------|---|---|
| ATOM | 1936 | N   | ASP A 483 | -2.279 | 11.520 | -0.246 | 1.00 | 21.21 | A | N |
| ATOM | 1937 | CA  | ASP A 483 | -1.569 | 12.043 | -1.402 | 1.00 | 20.99 | A | C |
| ATOM | 1938 | CB  | ASP A 483 | -2.127 | 13.400 | -1.801 | 1.00 | 20.33 | A | C |
| ATOM | 1939 | CG  | ASP A 483 | -3.570 | 13.321 | -2.212 | 1.00 | 21.44 | A | C |
| ATOM | 1940 | OD1 | ASP A 483 | -4.007 | 12.233 | -2.600 | 1.00 | 23.60 | A | O |
| ATOM | 1941 | OD2 | ASP A 483 | -4.274 | 14.330 | -2.138 | 1.00 | 23.17 | A | O |
| ATOM | 1942 | C   | ASP A 483 | -0.076 | 12.179 | -1.156 | 1.00 | 21.52 | A | C |
| ATOM | 1943 | O   | ASP A 483 | 0.667  | 12.609 | -2.049 | 1.00 | 22.15 | A | O |
| ATOM | 1944 | N   | ARG A 484 | 0.357  | 11.903 | 0.066  | 1.00 | 20.80 | A | N |
| ATOM | 1945 | CA  | ARG A 484 | 1.783  | 11.996 | 0.368  | 1.00 | 20.41 | A | C |
| ATOM | 1946 | CB  | ARG A 484 | 2.015  | 12.327 | 1.851  | 1.00 | 21.68 | A | C |
| ATOM | 1947 | CG  | ARG A 484 | 1.398  | 13.654 | 2.287  | 1.00 | 20.10 | A | C |
| ATOM | 1948 | CD  | ARG A 484 | 1.426  | 13.764 | 3.800  | 1.00 | 18.34 | A | C |
| ATOM | 1949 | NE  | ARG A 484 | 0.518  | 14.815 | 4.239  | 1.00 | 19.42 | A | N |
| ATOM | 1950 | CZ  | ARG A 484 | 0.006  | 14.960 | 5.464  | 1.00 | 17.99 | A | C |
| ATOM | 1951 | NH1 | ARG A 484 | 0.307  | 14.128 | 6.456  | 1.00 | 16.87 | A | N |
| ATOM | 1952 | NH2 | ARG A 484 | -0.850 | 15.950 | 5.667  | 1.00 | 15.36 | A | N |
| ATOM | 1953 | C   | ARG A 484 | 2.435  | 10.677 | -0.015 | 1.00 | 19.50 | A | C |
| ATOM | 1954 | O   | ARG A 484 | 1.844  | 9.615  | 0.156  | 1.00 | 18.96 | A | O |
| ATOM | 1955 | N   | PRO A 485 | 3.681  | 10.726 | -0.520 | 1.00 | 20.63 | A | N |
| ATOM | 1956 | CD  | PRO A 485 | 4.510  | 11.917 | -0.784 | 1.00 | 19.48 | A | C |
| ATOM | 1957 | CA  | PRO A 485 | 4.369  | 9.496  | -0.918 | 1.00 | 19.40 | A | C |
| ATOM | 1958 | CB  | PRO A 485 | 5.571  | 10.030 | -1.702 | 1.00 | 20.93 | A | C |
| ATOM | 1959 | CG  | PRO A 485 | 5.880  | 11.312 | -1.038 | 1.00 | 20.38 | A | C |
| ATOM | 1960 | C   | PRO A 485 | 4.770  | 8.592  | 0.260  | 1.00 | 20.77 | A | C |
| ATOM | 1961 | O   | PRO A 485 | 4.675  | 8.996  | 1.412  | 1.00 | 21.20 | A | O |
| ATOM | 1962 | N   | THR A 486 | 5.029  | 7.320  | -0.031 | 1.00 | 19.96 | A | N |
| ATOM | 1963 | CA  | THR A 486 | 5.473  | 6.375  | 0.983  | 1.00 | 21.11 | A | C |
| ATOM | 1964 | CB  | THR A 486 | 5.397  | 4.925  | 0.458  | 1.00 | 20.55 | A | C |
| ATOM | 1965 | OG1 | THR A 486 | 6.008  | 4.903  | -0.839 | 1.00 | 23.65 | A | O |
| ATOM | 1966 | CG2 | THR A 486 | 3.963  | 4.395  | 0.359  | 1.00 | 19.91 | A | C |
| ATOM | 1967 | C   | THR A 486 | 6.998  | 6.664  | 1.181  | 1.00 | 22.11 | A | C |
| ATOM | 1968 | O   | THR A 486 | 7.643  | 7.255  | 0.308  | 1.00 | 22.06 | A | O |
| ATOM | 1969 | N   | PHE A 487 | 7.574  | 6.181  | 2.280  | 1.00 | 21.28 | A | N |
| ATOM | 1970 | CA  | PHE A 487 | 8.990  | 6.364  | 2.536  | 1.00 | 21.80 | A | C |
| ATOM | 1971 | CB  | PHE A 487 | 9.348  | 6.103  | 3.999  | 1.00 | 20.18 | A | C |
| ATOM | 1972 | CG  | PHE A 487 | 9.102  | 7.273  | 4.892  | 1.00 | 18.81 | A | C |
| ATOM | 1973 | CD1 | PHE A 487 | 9.903  | 8.410  | 4.807  | 1.00 | 19.23 | A | C |
| ATOM | 1974 | CD2 | PHE A 487 | 8.083  | 7.236  | 5.840  | 1.00 | 20.27 | A | C |
| ATOM | 1975 | CE1 | PHE A 487 | 9.700  | 9.499  | 5.654  | 1.00 | 17.45 | A | C |
| ATOM | 1976 | CE2 | PHE A 487 | 7.861  | 8.316  | 6.697  | 1.00 | 18.45 | A | C |
| ATOM | 1977 | CZ  | PHE A 487 | 8.677  | 9.459  | 6.604  | 1.00 | 19.53 | A | C |
| ATOM | 1978 | C   | PHE A 487 | 9.740  | 5.408  | 1.632  | 1.00 | 22.93 | A | C |
| ATOM | 1979 | O   | PHE A 487 | 10.890 | 5.656  | 1.293  | 1.00 | 24.31 | A | O |
| ATOM | 1980 | N   | ASP A 488 | 9.079  | 4.327  | 1.232  | 1.00 | 23.81 | A | N |
| ATOM | 1981 | CA  | ASP A 488 | 9.655  | 3.339  | 0.331  | 1.00 | 24.99 | A | C |
| ATOM | 1982 | CB  | ASP A 488 | 8.645  | 2.190  | 0.133  | 1.00 | 28.23 | A | C |
| ATOM | 1983 | CG  | ASP A 488 | 9.064  | 1.176  | -0.939 | 1.00 | 32.43 | A | C |
| ATOM | 1984 | OD1 | ASP A 488 | 10.273 | 1.032  | -1.217 | 1.00 | 34.73 | A | O |
| ATOM | 1985 | OD2 | ASP A 488 | 8.158  | 0.521  | -1.513 | 1.00 | 34.03 | A | O |
| ATOM | 1986 | C   | ASP A 488 | 9.994  | 4.079  | -0.971 | 1.00 | 25.44 | A | C |
| ATOM | 1987 | O   | ASP A 488 | 11.101 | 3.923  | -1.478 | 1.00 | 26.44 | A | O |
| ATOM | 1988 | N   | TYR A 489 | 9.104  | 4.973  | -1.427 | 1.00 | 24.53 | A | N |
| ATOM | 1989 | CA  | TYR A 489 | 9.335  | 5.786  | -2.644 | 1.00 | 24.78 | A | C |
| ATOM | 1990 | CB  | TYR A 489 | 8.035  | 6.465  | -3.140 | 1.00 | 24.59 | A | C |
| ATOM | 1991 | CG  | TYR A 489 | 8.239  | 7.468  | -4.271 | 1.00 | 25.20 | A | C |
| ATOM | 1992 | CD1 | TYR A 489 | 8.497  | 7.043  | -5.580 | 1.00 | 25.30 | A | C |
| ATOM | 1993 | CE1 | TYR A 489 | 8.699  | 7.966  | -6.620 | 1.00 | 25.59 | A | C |

Figure 11

| | | | | | | | | | | | |
|---|---|---|---|---|---|---|---|---|---|---|---|
|ATOM|1994|CD2|TYR|A|489|8.186|8.840|-4.025|1.00 26.16|A|C|
|ATOM|1995|CE2|TYR|A|489|8.387|9.779|-5.034|1.00 26.06|A|C|
|ATOM|1996|CZ|TYR|A|489|8.646|9.344|-6.341|1.00 28.33|A|C|
|ATOM|1997|OH|TYR|A|489|8.873|10.298|-7.337|1.00 28.42|A|O|
|ATOM|1998|C|TYR|A|489|10.410|6.873|-2.425|1.00 24.15|A|C|
|ATOM|1999|O|TYR|A|489|11.301|7.035|-3.260|1.00 22.45|A|O|
|ATOM|2000|N|LEU|A|490|10.271|7.647|-1.344|1.00 23.61|A|N|
|ATOM|2001|CA|LEU|A|490|11.237|8.702|-1.013|1.00 24.07|A|C|
|ATOM|2002|CB|LEU|A|490|10.881|9.381|0.317|1.00 22.93|A|C|
|ATOM|2003|CG|LEU|A|490|9.549|10.171|0.341|1.00 23.10|A|C|
|ATOM|2004|CD1|LEU|A|490|9.168|10.533|1.744|1.00 22.96|A|C|
|ATOM|2005|CD2|LEU|A|490|9.658|11.415|-0.480|1.00 22.87|A|C|
|ATOM|2006|C|LEU|A|490|12.665|8.130|-0.971|1.00 25.17|A|C|
|ATOM|2007|O|LEU|A|490|13.579|8.734|-1.502|1.00 24.73|A|O|
|ATOM|2008|N|ARG|A|491|12.840|6.939|-0.393|1.00 26.49|A|N|
|ATOM|2009|CA|ARG|A|491|14.161|6.327|-0.361|1.00 28.93|A|C|
|ATOM|2010|CB|ARG|A|491|14.166|5.033|0.456|1.00 30.45|A|C|
|ATOM|2011|CG|ARG|A|491|15.465|4.238|0.285|1.00 34.38|A|C|
|ATOM|2012|CD|ARG|A|491|15.301|2.757|0.570|1.00 38.21|A|C|
|ATOM|2013|NE|ARG|A|491|14.133|2.186|-0.097|1.00 43.85|A|N|
|ATOM|2014|CZ|ARG|A|491|14.083|1.847|-1.389|1.00 46.22|A|C|
|ATOM|2015|NH1|ARG|A|491|15.145|2.012|-2.179|1.00 47.01|A|N|
|ATOM|2016|NH2|ARG|A|491|12.965|1.332|-1.890|1.00 46.85|A|N|
|ATOM|2017|C|ARG|A|491|14.688|6.071|-1.800|1.00 30.47|A|C|
|ATOM|2018|O|ARG|A|491|15.851|6.405|-2.113|1.00 30.37|A|O|
|ATOM|2019|N|SER|A|492|13.827|5.524|-2.670|1.00 30.80|A|N|
|ATOM|2020|CA|SER|A|492|14.175|5.239|-4.068|1.00 31.66|A|C|
|ATOM|2021|CB|SER|A|492|12.984|4.646|-4.813|1.00 31.93|A|C|
|ATOM|2022|OG|SER|A|492|12.742|3.334|-4.373|1.00 35.33|A|O|
|ATOM|2023|C|SER|A|492|14.637|6.469|-4.823|1.00 31.57|A|C|
|ATOM|2024|O|SER|A|492|15.668|6.431|-5.478|1.00 31.92|A|O|
|ATOM|2025|N|VAL|A|493|13.866|7.554|-4.730|1.00 31.43|A|N|
|ATOM|2026|CA|VAL|A|493|14.191|8.801|-5.409|1.00 31.63|A|C|
|ATOM|2027|CB|VAL|A|493|12.964|9.798|-5.442|1.00 33.10|A|C|
|ATOM|2028|CG1|VAL|A|493|12.321|9.891|-4.093|1.00 33.93|A|C|
|ATOM|2029|CG2|VAL|A|493|13.401|11.229|-5.858|1.00 33.07|A|C|
|ATOM|2030|C|VAL|A|493|15.426|9.476|-4.830|1.00 32.04|A|C|
|ATOM|2031|O|VAL|A|493|16.247|10.010|-5.578|1.00 32.08|A|O|
|ATOM|2032|N|LEU|A|494|15.582|9.447|-3.512|1.00 31.78|A|N|
|ATOM|2033|CA|LEU|A|494|16.755|10.077|-2.907|1.00 31.96|A|C|
|ATOM|2034|CB|LEU|A|494|16.545|10.296|-1.405|1.00 29.26|A|C|
|ATOM|2035|CG|LEU|A|494|15.426|11.320|-1.119|1.00 28.48|A|C|
|ATOM|2036|CD1|LEU|A|494|15.049|11.356|0.351|1.00 25.52|A|C|
|ATOM|2037|CD2|LEU|A|494|15.831|12.714|-1.624|1.00 26.82|A|C|
|ATOM|2038|C|LEU|A|494|18.052|9.319|-3.236|1.00 32.72|A|C|
|ATOM|2039|O|LEU|A|494|19.052|9.941|-3.517|1.00 33.15|A|O|
|ATOM|2040|N|GLU|A|495|18.007|7.991|-3.295|1.00 34.90|A|N|
|ATOM|2041|CA|GLU|A|495|19.184|7.193|-3.636|1.00 37.82|A|C|
|ATOM|2042|CB|GLU|A|495|18.881|5.702|-3.512|1.00 39.98|A|C|
|ATOM|2043|CG|GLU|A|495|19.008|5.161|-2.097|1.00 44.29|A|C|
|ATOM|2044|CD|GLU|A|495|18.509|3.735|-1.955|1.00 47.20|A|C|
|ATOM|2045|OE1|GLU|A|495|18.182|3.096|-2.998|1.00 48.36|A|O|
|ATOM|2046|OE2|GLU|A|495|18.447|3.256|-0.785|1.00 48.89|A|O|
|ATOM|2047|C|GLU|A|495|19.650|7.455|-5.062|1.00 38.93|A|C|
|ATOM|2048|O|GLU|A|495|20.834|7.689|-5.289|1.00 38.50|A|O|
|ATOM|2049|N|ASP|A|496|18.692|7.438|-5.997|1.00 39.97|A|N|
|ATOM|2050|CA|ASP|A|496|18.929|7.622|-7.428|1.00 40.91|A|C|
|ATOM|2051|CB|ASP|A|496|17.901|6.792|-8.228|1.00 42.10|A|C|
|ATOM|2052|CG|ASP|A|496|17.987|5.276|-7.932|1.00 44.21|A|C|

Figure 11

| | | | | | | | | | | | |
|---|---|---|---|---|---|---|---|---|---|---|---|
| ATOM | 2053 | OD1 | ASP | A | 496 | 19.104 | 4.711 | -7.904 | 1.00 43.43 | A | O |
| ATOM | 2054 | OD2 | ASP | A | 496 | 16.927 | 4.636 | -7.736 | 1.00 46.00 | A | O |
| ATOM | 2055 | C | ASP | A | 496 | 18.907 | 9.066 | -7.924 | 1.00 41.53 | A | C |
| ATOM | 2056 | O | ASP | A | 496 | 18.962 | 9.293 | -9.123 | 1.00 41.88 | A | O |
| ATOM | 2057 | N | PHE | A | 497 | 18.917 | 10.035 | -7.010 | 1.00 42.27 | A | N |
| ATOM | 2058 | CA | PHE | A | 497 | 18.839 | 11.465 | -7.352 | 1.00 42.84 | A | C |
| ATOM | 2059 | CB | PHE | A | 497 | 18.732 | 12.295 | -6.075 | 1.00 40.78 | A | C |
| ATOM | 2060 | CG | PHE | A | 497 | 18.037 | 13.612 | -6.260 | 1.00 39.09 | A | C |
| ATOM | 2061 | CD1 | PHE | A | 497 | 16.656 | 13.698 | -6.215 | 1.00 39.58 | A | C |
| ATOM | 2062 | CD2 | PHE | A | 497 | 18.770 | 14.777 | -6.471 | 1.00 38.65 | A | C |
| ATOM | 2063 | CE1 | PHE | A | 497 | 16.020 | 14.931 | -6.377 | 1.00 38.82 | A | C |
| ATOM | 2064 | CE2 | PHE | A | 497 | 18.149 | 16.001 | -6.635 | 1.00 37.48 | A | C |
| ATOM | 2065 | CZ | PHE | A | 497 | 16.781 | 16.083 | -6.589 | 1.00 38.25 | A | C |
| ATOM | 2066 | C | PHE | A | 497 | 19.879 | 12.055 | -8.326 | 1.00 44.32 | A | C |
| ATOM | 2067 | O | PHE | A | 497 | 19.571 | 12.974 | -9.080 | 1.00 43.67 | A | O |
| ATOM | 2068 | N | PHE | A | 498 | 21.122 | 11.600 | -8.241 | 1.00 46.80 | A | N |
| ATOM | 2069 | CA | PHE | A | 498 | 22.189 | 12.032 | -9.164 | 1.00 49.10 | A | C |
| ATOM | 2070 | CB | PHE | A | 498 | 22.319 | 13.564 | -9.334 | 1.00 49.60 | A | C |
| ATOM | 2071 | CG | PHE | A | 498 | 22.459 | 14.354 | -8.041 | 1.00 49.40 | A | C |
| ATOM | 2072 | CD1 | PHE | A | 498 | 22.774 | 13.740 | -6.830 | 1.00 49.13 | A | C |
| ATOM | 2073 | CD2 | PHE | A | 498 | 22.230 | 15.732 | -8.054 | 1.00 48.86 | A | C |
| ATOM | 2074 | CE1 | PHE | A | 498 | 22.846 | 14.495 | -5.651 | 1.00 49.76 | A | C |
| ATOM | 2075 | CE2 | PHE | A | 498 | 22.302 | 16.494 | -6.888 | 1.00 49.37 | A | C |
| ATOM | 2076 | CZ | PHE | A | 498 | 22.609 | 15.876 | -5.682 | 1.00 49.09 | A | C |
| ATOM | 2077 | C | PHE | A | 498 | 23.532 | 11.409 | -8.867 | 1.00 50.32 | A | C |
| ATOM | 2078 | O | PHE | A | 498 | 23.697 | 10.304 | -9.423 | 1.00 51.52 | A | O |
| ATOM | 2079 | N1 | LIG | A | 500 | 25.265 | 9.284 | 20.729 | 1.00 20.00 | A | N |
| ATOM | 2080 | C1 | LIG | A | 500 | 24.372 | 8.351 | 20.881 | 1.00 20.00 | A | C |
| ATOM | 2081 | N2 | LIG | A | 500 | 23.218 | 8.888 | 21.372 | 1.00 20.00 | A | N |
| ATOM | 2082 | C2 | LIG | A | 500 | 21.983 | 8.158 | 21.676 | 1.00 20.00 | A | C |
| ATOM | 2083 | C3 | LIG | A | 500 | 21.848 | 7.995 | 23.191 | 1.00 20.00 | A | C |
| ATOM | 2084 | C4 | LIG | A | 500 | 23.425 | 10.235 | 21.527 | 1.00 20.00 | A | C |
| ATOM | 2085 | N3 | LIG | A | 500 | 22.684 | 11.253 | 21.955 | 1.00 20.00 | A | N |
| ATOM | 2086 | C5 | LIG | A | 500 | 23.180 | 12.479 | 21.990 | 1.00 20.00 | A | C |
| ATOM | 2087 | N4 | LIG | A | 500 | 22.378 | 13.513 | 22.442 | 1.00 20.00 | A | N |
| ATOM | 2088 | C6 | LIG | A | 500 | 22.771 | 14.903 | 22.201 | 1.00 20.00 | A | C |
| ATOM | 2089 | C7 | LIG | A | 500 | 23.828 | 15.320 | 23.226 | 1.00 20.00 | A | C |
| ATOM | 2090 | C8 | LIG | A | 500 | 23.349 | 15.034 | 20.791 | 1.00 20.00 | A | C |
| ATOM | 2091 | C9 | LIG | A | 500 | 21.546 | 15.810 | 22.336 | 1.00 20.00 | A | C |
| ATOM | 2092 | O1 | LIG | A | 500 | 20.534 | 15.136 | 23.087 | 1.00 20.00 | A | O |
| ATOM | 2093 | N5 | LIG | A | 500 | 24.421 | 12.751 | 21.605 | 1.00 20.00 | A | N |
| ATOM | 2094 | C10 | LIG | A | 500 | 25.230 | 11.793 | 21.164 | 1.00 20.00 | A | C |
| ATOM | 2095 | N6 | LIG | A | 500 | 26.523 | 12.087 | 20.766 | 1.00 20.00 | A | N |
| ATOM | 2096 | C11 | LIG | A | 500 | 27.047 | 13.367 | 20.981 | 1.00 20.00 | A | C |
| ATOM | 2097 | C12 | LIG | A | 500 | 26.231 | 14.381 | 21.466 | 1.00 20.00 | A | C |
| ATOM | 2098 | C13 | LIG | A | 500 | 26.748 | 15.643 | 21.678 | 1.00 20.00 | A | C |
| ATOM | 2099 | C14 | LIG | A | 500 | 28.085 | 15.899 | 21.408 | 1.00 20.00 | A | C |
| ATOM | 2100 | O2 | LIG | A | 500 | 28.595 | 17.142 | 21.617 | 1.00 20.00 | A | O |
| ATOM | 2101 | C15 | LIG | A | 500 | 29.975 | 17.090 | 21.250 | 1.00 20.00 | A | C |
| ATOM | 2102 | C16 | LIG | A | 500 | 30.611 | 18.465 | 21.465 | 0.00 20.00 | A | C |
| ATOM | 2103 | N7 | LIG | A | 500 | 30.495 | 18.844 | 22.879 | 0.00 20.00 | A | N |
| ATOM | 2104 | C17 | LIG | A | 500 | 31.122 | 20.165 | 23.014 | 0.00 20.00 | A | C |
| ATOM | 2105 | C18 | LIG | A | 500 | 31.036 | 20.623 | 24.472 | 0.00 20.00 | A | C |
| ATOM | 2106 | O3 | LIG | A | 500 | 31.717 | 19.685 | 25.307 | 0.00 20.00 | A | O |
| ATOM | 2107 | C19 | LIG | A | 500 | 31.601 | 20.166 | 26.648 | 0.00 20.00 | A | C |
| ATOM | 2108 | C20 | LIG | A | 500 | 28.901 | 14.888 | 20.922 | 1.00 20.00 | A | C |
| ATOM | 2109 | C21 | LIG | A | 500 | 28.386 | 13.623 | 20.715 | 1.00 20.00 | A | C |
| ATOM | 2110 | C22 | LIG | A | 500 | 24.743 | 10.475 | 21.110 | 1.00 20.00 | A | C |
| ATOM | 2111 | OH2 | H2O | A | 600 | 5.213 | 22.008 | 9.219 | 1.00 18.49 | A | O |

Figure 11

```
ATOM   2112  OH2  H2O A 601     1.155   2.902  -1.263  1.00 71.12      A    O
ATOM   2113  OH2  H2O A 602    -1.451  23.903   0.420  1.00 17.19      A    O
ATOM   2114  OH2  H2O A 604     6.164   2.245  -2.870  1.00 47.16      A    O
ATOM   2115  OH2  H2O A 605    -5.726  25.215   1.850  1.00 30.69      A    O
ATOM   2116  OH2  H2O A 606     7.142  12.928  13.017  1.00 16.53      A    O
ATOM   2117  OH2  H2O A 607    -3.855  16.560  -0.831  1.00 23.22      A    O
ATOM   2118  OH2  H2O A 608     0.550   9.502  -3.389  1.00 48.64      A    O
ATOM   2119  OH2  H2O A 609    -0.607  30.406   1.862  1.00 26.25      A    O
ATOM   2120  OH2  H2O A 610     5.716  23.962   4.300  1.00 17.98      A    O
ATOM   2121  OH2  H2O A 611     5.518  18.363  -6.347  1.00 29.59      A    O
ATOM   2122  OH2  H2O A 612     0.411   5.473   0.340  1.00 30.24      A    O
ATOM   2123  OH2  H2O A 613    -0.509  28.313  -0.264  1.00 62.00      A    O
ATOM   2124  OH2  H2O A 614     9.072   9.080  18.750  1.00 26.69      A    O
ATOM   2125  OH2  H2O A 615    -9.778   7.817  -3.172  1.00 24.79      A    O
ATOM   2126  OH2  H2O A 616    -1.876   6.537  -0.247  1.00 29.35      A    O
ATOM   2127  OH2  H2O A 617     2.573  29.890   0.177  1.00 66.03      A    O
ATOM   2128  OH2  H2O A 618     8.102  24.555  16.178  1.00 24.76      A    O
ATOM   2129  OH2  H2O A 619    -1.287   4.920   4.173  1.00 74.17      A    O
ATOM   2130  OH2  H2O A 620     1.149  26.551  -2.823  1.00 35.15      A    O
ATOM   2131  OH2  H2O A 621    30.296   7.248  15.438  1.00 49.05      A    O
ATOM   2132  OH2  H2O A 622     3.619   0.402  -2.014  1.00 43.84      A    O
ATOM   2133  OH2  H2O A 623    -3.617  23.307   1.944  1.00 34.31      A    O
ATOM   2134  OH2  H2O A 624    35.566  11.002  21.971  1.00 49.24      A    O
ATOM   2135  OH2  H2O A 625    20.241   5.027   1.835  1.00 55.55      A    O
ATOM   2136  OH2  H2O A 626    15.222  19.511  14.272  1.00 21.72      A    O
ATOM   2137  OH2  H2O A 627     3.323   5.946   3.692  1.00 18.71      A    O
ATOM   2138  OH2  H2O A 628     3.775  15.100  11.656  1.00 27.89      A    O
ATOM   2139  OH2  H2O A 630     8.612  14.798  -7.338  1.00 58.83      A    O
ATOM   2140  OH2  H2O A 631    33.799  -1.398  33.522  1.00 39.00      A    O
ATOM   2141  OH2  H2O A 632     5.365  27.559  -1.428  1.00 21.57      A    O
ATOM   2142  OH2  H2O A 633    16.379  12.260  19.564  1.00 52.29      A    O
ATOM   2143  OH2  H2O A 634    16.808  -1.298   4.686  1.00 28.52      A    O
ATOM   2144  OH2  H2O A 635    -1.687  11.284   9.672  1.00 35.24      A    O
ATOM   2145  OH2  H2O A 636    -2.493  11.981  -5.052  1.00 27.66      A    O
ATOM   2146  OH2  H2O A 638    -8.385   7.995  -5.500  1.00 32.07      A    O
ATOM   2147  OH2  H2O A 639    15.737  10.754  -8.476  1.00 35.38      A    O
ATOM   2148  OH2  H2O A 640    -2.114  23.240   5.415  1.00 18.73      A    O
ATOM   2149  OH2  H2O A 641    -2.791   6.341   2.351  1.00 22.40      A    O
ATOM   2150  OH2  H2O A 642    19.240  -0.522  15.587  1.00 31.18      A    O
ATOM   2151  OH2  H2O A 643    26.505  22.262  33.413  1.00 75.84      A    O
ATOM   2152  OH2  H2O A 644     2.717  20.839  -0.733  1.00 20.37      A    O
ATOM   2153  OH2  H2O A 645    -4.692  23.532   9.539  1.00 38.79      A    O
ATOM   2154  OH2  H2O A 646    27.887   0.742  40.887  1.00 50.42      A    O
ATOM   2155  OH2  H2O A 647     3.975  35.570   6.941  1.00 55.14      A    O
ATOM   2156  OH2  H2O A 648     0.572   4.774  10.149  1.00 22.44      A    O
ATOM   2157  OH2  H2O A 649   -13.016   5.457  -2.267  1.00 63.23      A    O
ATOM   2158  OH2  H2O A 650    11.908  27.916   2.647  1.00 44.49      A    O
ATOM   2159  OH2  H2O A 651     2.388  -2.807   1.045  1.00 27.30      A    O
ATOM   2160  OH2  H2O A 652    -1.897  20.548  -0.939  1.00 30.95      A    O
ATOM   2161  OH2  H2O A 653     3.608  22.382  11.420  1.00 17.69      A    O
ATOM   2162  OH2  H2O A 654     3.448  30.699  -4.294  1.00 23.79      A    O
ATOM   2163  OH2  H2O A 655    24.075  20.695  27.394  1.00 31.72      A    O
ATOM   2164  OH2  H2O A 656     4.779   3.147  16.603  1.00 29.86      A    O
ATOM   2165  OH2  H2O A 657     1.167   3.040   6.808  1.00 77.86      A    O
ATOM   2166  OH2  H2O A 658    -1.606  24.263  -5.637  1.00 40.84      A    O
ATOM   2167  OH2  H2O A 659     9.531  27.859  -4.594  1.00 25.25      A    O
ATOM   2168  OH2  H2O A 660    23.919  20.967  20.848  1.00 37.70      A    O
ATOM   2169  OH2  H2O A 661    14.852  14.179  23.890  1.00 41.08      A    O
ATOM   2170  OH2  H2O A 662    -6.195  10.629  -3.214  1.00 54.90      A    O
```

Figure 11

| | | | | | | | | | | |
|---|---|---|---|---|---|---|---|---|---|---|
| ATOM | 2171 | OH2 | H2O | A | 663 | 6.486 | 34.162 | 3.463 | 1.00 26.80 | A | O |
| ATOM | 2172 | OH2 | H2O | A | 664 | 26.252 | 21.995 | 20.427 | 1.00 56.68 | A | O |
| ATOM | 2173 | OH2 | H2O | A | 665 | 2.592 | 2.606 | 3.379 | 1.00 63.66 | A | O |
| ATOM | 2174 | OH2 | H2O | A | 666 | -2.282 | 24.209 | -2.035 | 1.00 37.81 | A | O |
| ATOM | 2175 | OH2 | H2O | A | 667 | 8.445 | 0.934 | 3.338 | 1.00 23.54 | A | O |
| ATOM | 2176 | OH2 | H2O | A | 668 | 22.679 | 23.168 | -0.296 | 1.00 43.05 | A | O |
| ATOM | 2177 | OH2 | H2O | A | 669 | 4.995 | 0.728 | 2.090 | 1.00 51.01 | A | O |
| ATOM | 2178 | OH2 | H2O | A | 670 | -5.763 | 23.840 | -2.034 | 1.00 60.71 | A | O |
| ATOM | 2179 | OH2 | H2O | A | 671 | -2.600 | 7.950 | 6.921 | 1.00 31.89 | A | O |
| ATOM | 2180 | OH2 | H2O | A | 672 | 6.302 | 2.283 | 18.942 | 1.00 37.13 | A | O |
| ATOM | 2181 | OH2 | H2O | A | 673 | 33.574 | 21.128 | 11.982 | 1.00 47.15 | A | O |
| ATOM | 2182 | OH2 | H2O | A | 674 | 14.262 | 0.283 | 4.496 | 1.00 30.15 | A | O |
| ATOM | 2183 | OH2 | H2O | A | 675 | -3.130 | 24.755 | 11.302 | 1.00 26.74 | A | O |
| ATOM | 2184 | OH2 | H2O | A | 676 | 31.477 | 4.042 | 18.563 | 1.00 48.81 | A | O |
| ATOM | 2185 | OH2 | H2O | A | 677 | 5.166 | 14.858 | 14.082 | 1.00 29.38 | A | O |
| ATOM | 2186 | OH2 | H2O | A | 678 | -5.634 | 18.687 | 7.001 | 1.00 40.48 | A | O |
| ATOM | 2187 | OH2 | H2O | A | 679 | 15.268 | 21.253 | 16.264 | 1.00 36.20 | A | O |
| ATOM | 2188 | OH2 | H2O | A | 680 | 32.356 | 15.583 | 31.666 | 1.00 35.59 | A | O |
| ATOM | 2189 | OH2 | H2O | A | 681 | -6.574 | 18.891 | 9.587 | 1.00 35.22 | A | O |
| ATOM | 2190 | OH2 | H2O | A | 682 | 29.263 | 2.427 | 19.800 | 1.00 31.51 | A | O |
| ATOM | 2191 | OH2 | H2O | A | 683 | 19.273 | 16.718 | 20.009 | 1.00 57.11 | A | O |
| ATOM | 2192 | OH2 | H2O | A | 684 | 14.396 | 24.662 | 7.223 | 1.00 23.46 | A | O |
| ATOM | 2193 | OH2 | H2O | A | 685 | -4.820 | 22.722 | 6.997 | 1.00 33.37 | A | O |
| ATOM | 2194 | OH2 | H2O | A | 686 | 17.065 | 23.778 | -9.169 | 1.00 45.39 | A | O |
| ATOM | 2195 | OH2 | H2O | A | 687 | -1.647 | 26.574 | -4.093 | 1.00 32.66 | A | O |
| ATOM | 2196 | OH2 | H2O | A | 688 | 33.609 | 12.657 | 11.565 | 1.00 50.15 | A | O |
| ATOM | 2197 | OH2 | H2O | A | 689 | -5.133 | 24.979 | 13.273 | 1.00 43.10 | A | O |
| ATOM | 2198 | OH2 | H2O | A | 690 | 4.491 | 5.039 | 32.970 | 1.00 36.16 | A | O |
| ATOM | 2199 | OH2 | H2O | A | 691 | 18.236 | -1.653 | 19.258 | 1.00 26.07 | A | O |
| ATOM | 2200 | OH2 | H2O | A | 692 | 11.978 | 21.947 | 18.446 | 1.00 34.22 | A | O |
| ATOM | 2201 | OH2 | H2O | A | 693 | 16.366 | 23.500 | 11.995 | 1.00 29.09 | A | O |
| ATOM | 2202 | OH2 | H2O | A | 694 | 17.371 | 0.042 | 17.307 | 1.00 40.19 | A | O |
| ATOM | 2203 | OH2 | H2O | A | 695 | -9.996 | 10.282 | -6.612 | 1.00 40.82 | A | O |
| ATOM | 2204 | OH2 | H2O | A | 696 | 30.642 | 16.316 | 1.397 | 1.00 50.57 | A | O |
| ATOM | 2205 | OH2 | H2O | A | 697 | 10.792 | 16.218 | -8.243 | 1.00 57.76 | A | O |
| ATOM | 2206 | OH2 | H2O | A | 698 | 24.877 | 11.659 | 34.860 | 1.00 50.50 | A | O |
| ATOM | 2207 | OH2 | H2O | A | 699 | -5.409 | 21.662 | 0.006 | 1.00 36.35 | A | O |
| ATOM | 2208 | OH2 | H2O | A | 700 | 6.324 | 11.124 | -8.071 | 1.00 65.02 | A | O |
| ATOM | 2209 | OH2 | H2O | A | 701 | 33.740 | 11.806 | 23.642 | 1.00 34.41 | A | O |
| ATOM | 2210 | CB | TRP | B | 238 | 46.645 | 27.982 | 32.580 | 1.00 60.95 | B | C |
| ATOM | 2211 | CG | TRP | B | 238 | 46.190 | 28.548 | 33.927 | 1.00 62.85 | B | C |
| ATOM | 2212 | CD2 | TRP | B | 238 | 46.665 | 28.173 | 35.241 | 1.00 63.75 | B | C |
| ATOM | 2213 | CE2 | TRP | B | 238 | 45.972 | 28.972 | 36.181 | 1.00 64.15 | B | C |
| ATOM | 2214 | CE3 | TRP | B | 238 | 47.612 | 27.244 | 35.710 | 1.00 64.16 | B | C |
| ATOM | 2215 | CD1 | TRP | B | 238 | 45.251 | 29.523 | 34.131 | 1.00 63.38 | B | C |
| ATOM | 2216 | NE1 | TRP | B | 238 | 45.115 | 29.778 | 35.480 | 1.00 64.16 | B | N |
| ATOM | 2217 | CZ2 | TRP | B | 238 | 46.191 | 28.864 | 37.570 | 1.00 64.62 | B | C |
| ATOM | 2218 | CZ3 | TRP | B | 238 | 47.827 | 27.138 | 37.100 | 1.00 64.01 | B | C |
| ATOM | 2219 | CH2 | TRP | B | 238 | 47.123 | 27.945 | 38.005 | 1.00 63.94 | B | C |
| ATOM | 2220 | C | TRP | B | 238 | 48.396 | 27.933 | 30.739 | 1.00 58.75 | B | C |
| ATOM | 2221 | O | TRP | B | 238 | 48.996 | 26.873 | 30.861 | 1.00 59.17 | B | O |
| ATOM | 2222 | N | TRP | B | 238 | 47.644 | 30.120 | 31.772 | 1.00 59.61 | B | N |
| ATOM | 2223 | CA | TRP | B | 238 | 47.899 | 28.670 | 31.996 | 1.00 59.48 | B | C |
| ATOM | 2224 | N | GLU | B | 239 | 48.120 | 28.459 | 29.538 | 1.00 57.27 | B | N |
| ATOM | 2225 | CA | GLU | B | 239 | 48.588 | 27.833 | 28.290 | 1.00 55.38 | B | C |
| ATOM | 2226 | CB | GLU | B | 239 | 47.734 | 28.211 | 27.077 | 1.00 57.33 | B | C |
| ATOM | 2227 | CG | GLU | B | 239 | 46.586 | 27.288 | 26.782 | 1.00 59.81 | B | C |
| ATOM | 2228 | CD | GLU | B | 239 | 45.283 | 27.729 | 27.445 | 1.00 61.91 | B | C |
| ATOM | 2229 | OE1 | GLU | B | 239 | 45.078 | 27.401 | 28.639 | 1.00 63.06 | B | O |

Figure 11

| | | | | | | | | | | |
|---|---|---|---|---|---|---|---|---|---|---|
| ATOM | 2230 | OE2 | GLU | B | 239 | 44.461 | 28.395 | 26.768 | 1.00 61.98 | B | O |
| ATOM | 2231 | C | GLU | B | 239 | 50.014 | 28.287 | 28.011 | 1.00 53.17 | B | C |
| ATOM | 2232 | O | GLU | B | 239 | 50.364 | 29.446 | 28.212 | 1.00 53.33 | B | O |
| ATOM | 2233 | N | VAL | B | 240 | 50.821 | 27.371 | 27.505 | 1.00 50.21 | B | N |
| ATOM | 2234 | CA | VAL | B | 240 | 52.209 | 27.658 | 27.214 | 1.00 46.93 | B | C |
| ATOM | 2235 | CB | VAL | B | 240 | 53.130 | 27.238 | 28.404 | 1.00 46.00 | B | C |
| ATOM | 2236 | CG1 | VAL | B | 240 | 52.791 | 28.046 | 29.660 | 1.00 43.05 | B | C |
| ATOM | 2237 | CG2 | VAL | B | 240 | 53.004 | 25.737 | 28.673 | 1.00 44.91 | B | C |
| ATOM | 2238 | C | VAL | B | 240 | 52.590 | 26.889 | 25.963 | 1.00 45.83 | B | C |
| ATOM | 2239 | O | VAL | B | 240 | 51.913 | 25.929 | 25.583 | 1.00 44.77 | B | O |
| ATOM | 2240 | N | PRO | B | 241 | 53.608 | 27.373 | 25.239 | 1.00 45.15 | B | N |
| ATOM | 2241 | CD | PRO | B | 241 | 54.221 | 28.708 | 25.360 | 1.00 45.35 | B | C |
| ATOM | 2242 | CA | PRO | B | 241 | 54.062 | 26.710 | 24.020 | 1.00 44.85 | B | C |
| ATOM | 2243 | CB | PRO | B | 241 | 55.051 | 27.723 | 23.438 | 1.00 44.94 | B | C |
| ATOM | 2244 | CG | PRO | B | 241 | 54.513 | 29.037 | 23.926 | 1.00 44.73 | B | C |
| ATOM | 2245 | C | PRO | B | 241 | 54.751 | 25.382 | 24.348 | 1.00 45.19 | B | C |
| ATOM | 2246 | O | PRO | B | 241 | 55.404 | 25.251 | 25.384 | 1.00 45.18 | B | O |
| ATOM | 2247 | N | ARG | B | 242 | 54.560 | 24.395 | 23.481 | 1.00 45.25 | B | N |
| ATOM | 2248 | CA | ARG | B | 242 | 55.155 | 23.075 | 23.636 | 1.00 46.42 | B | C |
| ATOM | 2249 | CB | ARG | B | 242 | 54.853 | 22.289 | 22.369 | 1.00 48.04 | B | C |
| ATOM | 2250 | CG | ARG | B | 242 | 55.470 | 20.928 | 22.275 | 1.00 50.38 | B | C |
| ATOM | 2251 | CD | ARG | B | 242 | 54.849 | 19.996 | 23.264 | 1.00 53.18 | B | C |
| ATOM | 2252 | NE | ARG | B | 242 | 53.390 | 19.886 | 23.127 | 1.00 55.59 | B | N |
| ATOM | 2253 | CZ | ARG | B | 242 | 52.769 | 19.375 | 22.072 | 1.00 55.79 | B | C |
| ATOM | 2254 | NH1 | ARG | B | 242 | 53.469 | 18.928 | 21.033 | 1.00 56.23 | B | N |
| ATOM | 2255 | NH2 | ARG | B | 242 | 51.447 | 19.288 | 22.072 | 1.00 56.39 | B | N |
| ATOM | 2256 | C | ARG | B | 242 | 56.678 | 23.142 | 23.875 | 1.00 46.68 | B | C |
| ATOM | 2257 | O | ARG | B | 242 | 57.244 | 22.332 | 24.620 | 1.00 46.41 | B | O |
| ATOM | 2258 | N | GLU | B | 243 | 57.303 | 24.153 | 23.276 | 1.00 46.74 | B | N |
| ATOM | 2259 | CA | GLU | B | 243 | 58.744 | 24.417 | 23.350 | 1.00 46.92 | B | C |
| ATOM | 2260 | CB | GLU | B | 243 | 59.096 | 25.646 | 22.495 | 1.00 49.48 | B | C |
| ATOM | 2261 | CG | GLU | B | 243 | 58.886 | 25.460 | 20.991 | 1.00 54.05 | B | C |
| ATOM | 2262 | CD | GLU | B | 243 | 57.422 | 25.160 | 20.611 | 1.00 56.35 | B | C |
| ATOM | 2263 | OE1 | GLU | B | 243 | 56.558 | 26.032 | 20.882 | 1.00 57.03 | B | O |
| ATOM | 2264 | OE2 | GLU | B | 243 | 57.148 | 24.066 | 20.038 | 1.00 56.14 | B | O |
| ATOM | 2265 | C | GLU | B | 243 | 59.287 | 24.654 | 24.764 | 1.00 45.19 | B | C |
| ATOM | 2266 | O | GLU | B | 243 | 60.456 | 24.372 | 25.036 | 1.00 45.04 | B | O |
| ATOM | 2267 | N | THR | B | 244 | 58.455 | 25.192 | 25.648 | 1.00 42.82 | B | N |
| ATOM | 2268 | CA | THR | B | 244 | 58.863 | 25.463 | 27.029 | 1.00 40.69 | B | C |
| ATOM | 2269 | CB | THR | B | 244 | 57.821 | 26.366 | 27.747 | 1.00 40.56 | B | C |
| ATOM | 2270 | OG1 | THR | B | 244 | 56.552 | 25.678 | 27.844 | 1.00 40.56 | B | O |
| ATOM | 2271 | CG2 | THR | B | 244 | 57.633 | 27.651 | 26.994 | 1.00 40.28 | B | C |
| ATOM | 2272 | C | THR | B | 244 | 58.978 | 24.180 | 27.850 | 1.00 38.56 | B | C |
| ATOM | 2273 | O | THR | B | 244 | 59.247 | 24.220 | 29.041 | 1.00 37.50 | B | O |
| ATOM | 2274 | N | LEU | B | 245 | 58.893 | 23.045 | 27.183 | 1.00 37.86 | B | N |
| ATOM | 2275 | CA | LEU | B | 245 | 58.896 | 21.787 | 27.881 | 1.00 38.16 | B | C |
| ATOM | 2276 | CB | LEU | B | 245 | 57.427 | 21.390 | 28.054 | 1.00 38.43 | B | C |
| ATOM | 2277 | CG | LEU | B | 245 | 57.019 | 20.385 | 29.114 | 1.00 40.05 | B | C |
| ATOM | 2278 | CD1 | LEU | B | 245 | 57.221 | 21.010 | 30.490 | 1.00 39.80 | B | C |
| ATOM | 2279 | CD2 | LEU | B | 245 | 55.549 | 20.006 | 28.913 | 1.00 40.27 | B | C |
| ATOM | 2280 | C | LEU | B | 245 | 59.637 | 20.640 | 27.194 | 1.00 38.36 | B | C |
| ATOM | 2281 | O | LEU | B | 245 | 59.475 | 20.405 | 25.983 | 1.00 38.65 | B | O |
| ATOM | 2282 | N | LYS | B | 246 | 60.389 | 19.879 | 27.988 | 1.00 37.27 | B | N |
| ATOM | 2283 | CA | LYS | B | 246 | 61.093 | 18.715 | 27.469 | 1.00 37.44 | B | C |
| ATOM | 2284 | CB | LYS | B | 246 | 62.634 | 18.864 | 27.565 | 1.00 38.89 | B | C |
| ATOM | 2285 | CG | LYS | B | 246 | 63.405 | 17.637 | 26.972 | 1.00 40.38 | B | C |
| ATOM | 2286 | CD | LYS | B | 246 | 64.922 | 17.869 | 26.742 | 1.00 42.20 | B | C |
| ATOM | 2287 | CE | LYS | B | 246 | 65.582 | 18.479 | 27.977 | 1.00 43.46 | B | C |
| ATOM | 2288 | NZ | LYS | B | 246 | 67.055 | 18.494 | 27.895 | 1.00 44.47 | B | N |

Figure 11

```
ATOM   2289  C    LYS B 246      60.637  17.466  28.230  1.00 36.66      B    C
ATOM   2290  O    LYS B 246      60.728  17.403  29.450  1.00 36.34      B    O
ATOM   2291  N    LEU B 247      60.115  16.484  27.504  1.00 35.79      B    N
ATOM   2292  CA   LEU B 247      59.656  15.250  28.117  1.00 34.73      B    C
ATOM   2293  CB   LEU B 247      58.479  14.646  27.331  1.00 33.02      B    C
ATOM   2294  CG   LEU B 247      57.109  15.168  27.835  1.00 33.14      B    C
ATOM   2295  CD1  LEU B 247      56.972  16.676  27.651  1.00 32.48      B    C
ATOM   2296  CD2  LEU B 247      55.962  14.404  27.201  1.00 32.57      B    C
ATOM   2297  C    LEU B 247      60.867  14.339  28.156  1.00 34.44      B    C
ATOM   2298  O    LEU B 247      61.515  14.109  27.128  1.00 34.42      B    O
ATOM   2299  N    VAL B 248      61.190  13.846  29.350  1.00 33.62      B    N
ATOM   2300  CA   VAL B 248      62.377  13.011  29.526  1.00 32.66      B    C
ATOM   2301  CB   VAL B 248      63.222  13.584  30.645  1.00 31.85      B    C
ATOM   2302  CG1  VAL B 248      64.518  12.817  30.783  1.00 32.52      B    C
ATOM   2303  CG2  VAL B 248      63.478  15.024  30.370  1.00 31.12      B    C
ATOM   2304  C    VAL B 248      62.209  11.521  29.749  1.00 32.20      B    C
ATOM   2305  O    VAL B 248      62.872  10.692  29.108  1.00 32.93      B    O
ATOM   2306  N    GLU B 249      61.247  11.159  30.567  1.00 31.08      B    N
ATOM   2307  CA   GLU B 249      61.081   9.761  30.879  1.00 30.02      B    C
ATOM   2308  CB   GLU B 249      61.970   9.484  32.098  1.00 30.55      B    C
ATOM   2309  CG   GLU B 249      61.621   8.326  32.952  1.00 31.41      B    C
ATOM   2310  CD   GLU B 249      62.625   8.138  34.088  1.00 32.02      B    C
ATOM   2311  OE1  GLU B 249      63.444   9.054  34.360  1.00 29.73      B    O
ATOM   2312  OE2  GLU B 249      62.574   7.063  34.709  1.00 34.12      B    O
ATOM   2313  C    GLU B 249      59.626   9.394  31.153  1.00 29.56      B    C
ATOM   2314  O    GLU B 249      58.936  10.085  31.884  1.00 28.25      B    O
ATOM   2315  N    ARG B 250      59.171   8.306  30.550  1.00 30.27      B    N
ATOM   2316  CA   ARG B 250      57.815   7.874  30.765  1.00 31.51      B    C
ATOM   2317  CB   ARG B 250      57.342   6.935  29.665  1.00 32.43      B    C
ATOM   2318  CG   ARG B 250      55.807   6.965  29.557  1.00 35.16      B    C
ATOM   2319  CD   ARG B 250      55.344   6.209  28.357  1.00 36.38      B    C
ATOM   2320  NE   ARG B 250      55.689   4.818  28.562  1.00 39.15      B    N
ATOM   2321  CZ   ARG B 250      55.558   3.869  27.654  1.00 40.58      B    C
ATOM   2322  NH1  ARG B 250      55.078   4.158  26.447  1.00 40.96      B    N
ATOM   2323  NH2  ARG B 250      55.884   2.623  27.977  1.00 41.26      B    N
ATOM   2324  C    ARG B 250      57.686   7.154  32.085  1.00 31.03      B    C
ATOM   2325  O    ARG B 250      58.328   6.130  32.301  1.00 31.34      B    O
ATOM   2326  N    LEU B 251      56.837   7.692  32.954  1.00 30.23      B    N
ATOM   2327  CA   LEU B 251      56.586   7.090  34.258  1.00 28.62      B    C
ATOM   2328  CB   LEU B 251      56.202   8.169  35.274  1.00 27.24      B    C
ATOM   2329  CG   LEU B 251      57.208   9.304  35.366  1.00 25.62      B    C
ATOM   2330  CD1  LEU B 251      56.657  10.402  36.228  1.00 23.63      B    C
ATOM   2331  CD2  LEU B 251      58.550   8.764  35.894  1.00 24.62      B    C
ATOM   2332  C    LEU B 251      55.503   6.028  34.169  1.00 28.80      B    C
ATOM   2333  O    LEU B 251      55.519   5.041  34.928  1.00 29.48      B    O
ATOM   2334  N    GLY B 252      54.539   6.230  33.273  1.00 28.32      B    N
ATOM   2335  CA   GLY B 252      53.470   5.247  33.110  1.00 26.69      B    C
ATOM   2336  C    GLY B 252      52.670   5.373  31.813  1.00 26.43      B    C
ATOM   2337  O    GLY B 252      52.586   6.443  31.225  1.00 25.43      B    O
ATOM   2338  N    ALA B 253      52.073   4.269  31.371  1.00 27.68      B    N
ATOM   2339  CA   ALA B 253      51.255   4.268  30.144  1.00 28.42      B    C
ATOM   2340  CB   ALA B 253      52.016   3.596  28.995  1.00 28.61      B    C
ATOM   2341  C    ALA B 253      49.949   3.521  30.405  1.00 27.48      B    C
ATOM   2342  O    ALA B 253      49.951   2.361  30.833  1.00 26.17      B    O
ATOM   2343  N    GLY B 254      48.835   4.211  30.190  1.00 28.69      B    N
ATOM   2344  CA   GLY B 254      47.524   3.600  30.408  1.00 30.21      B    C
ATOM   2345  C    GLY B 254      46.531   3.706  29.257  1.00 30.44      B    C
ATOM   2346  O    GLY B 254      46.855   4.236  28.186  1.00 29.64      B    O
ATOM   2347  N    GLN B 255      45.295   3.261  29.516  1.00 32.22      B    N
```

Figure 11

| ATOM | 2348 | CA | GLN | B | 255 | 44.186 | 3.252 | 28.528 | 1.00 | 32.84 | B | C |
|------|------|-----|------|---|-----|--------|--------|--------|------|-------|---|---|
| ATOM | 2349 | CB | GLN | B | 255 | 42.905 | 2.624 | 29.158 | 1.00 | 35.90 | B | C |
| ATOM | 2350 | CG | GLN | B | 255 | 42.066 | 1.666 | 28.232 | 1.00 | 41.21 | B | C |
| ATOM | 2351 | CD | GLN | B | 255 | 40.508 | 1.939 | 28.216 | 1.00 | 43.70 | B | C |
| ATOM | 2352 | OE1 | GLN | B | 255 | 39.899 | 2.177 | 27.139 | 1.00 | 43.99 | B | O |
| ATOM | 2353 | NE2 | GLN | B | 255 | 39.881 | 1.899 | 29.411 | 1.00 | 44.00 | B | N |
| ATOM | 2354 | C | GLN | B | 255 | 43.878 | 4.646 | 27.963 | 1.00 | 32.42 | B | C |
| ATOM | 2355 | O | GLN | B | 255 | 43.524 | 4.773 | 26.782 | 1.00 | 33.55 | B | O |
| ATOM | 2356 | N | PHE | B | 256 | 44.068 | 5.691 | 28.780 | 1.00 | 31.04 | B | N |
| ATOM | 2357 | CA | PHE | B | 256 | 43.779 | 7.079 | 28.374 | 1.00 | 29.81 | B | C |
| ATOM | 2358 | CB | PHE | B | 256 | 42.964 | 7.807 | 29.458 | 1.00 | 30.17 | B | C |
| ATOM | 2359 | CG | PHE | B | 256 | 41.563 | 7.294 | 29.623 | 1.00 | 31.63 | B | C |
| ATOM | 2360 | CD1 | PHE | B | 256 | 41.109 | 6.197 | 28.895 | 1.00 | 31.86 | B | C |
| ATOM | 2361 | CD2 | PHE | B | 256 | 40.689 | 7.919 | 30.502 | 1.00 | 33.09 | B | C |
| ATOM | 2362 | CE1 | PHE | B | 256 | 39.800 | 5.726 | 29.037 | 1.00 | 32.96 | B | C |
| ATOM | 2363 | CE2 | PHE | B | 256 | 39.365 | 7.450 | 30.655 | 1.00 | 32.79 | B | C |
| ATOM | 2364 | CZ | PHE | B | 256 | 38.934 | 6.352 | 29.913 | 1.00 | 32.96 | B | C |
| ATOM | 2365 | C | PHE | B | 256 | 44.970 | 7.987 | 28.004 | 1.00 | 28.90 | B | C |
| ATOM | 2366 | O | PHE | B | 256 | 44.775 | 9.131 | 27.560 | 1.00 | 27.20 | B | O |
| ATOM | 2367 | N | GLY | B | 257 | 46.182 | 7.529 | 28.282 | 1.00 | 28.16 | B | N |
| ATOM | 2368 | CA | GLY | B | 257 | 47.338 | 8.346 | 27.972 | 1.00 | 27.82 | B | C |
| ATOM | 2369 | C | GLY | B | 257 | 48.546 | 7.913 | 28.756 | 1.00 | 26.49 | B | C |
| ATOM | 2370 | O | GLY | B | 257 | 48.620 | 6.779 | 29.164 | 1.00 | 25.91 | B | O |
| ATOM | 2371 | N | GLU | B | 258 | 49.475 | 8.830 | 28.991 | 1.00 | 27.62 | B | N |
| ATOM | 2372 | CA | GLU | B | 258 | 50.704 | 8.498 | 29.713 | 1.00 | 28.97 | B | C |
| ATOM | 2373 | CB | GLU | B | 258 | 51.828 | 8.220 | 28.689 | 1.00 | 30.24 | B | C |
| ATOM | 2374 | CG | GLU | B | 258 | 51.424 | 7.321 | 27.500 | 1.00 | 32.46 | B | C |
| ATOM | 2375 | CD | GLU | B | 258 | 52.547 | 7.143 | 26.477 | 1.00 | 36.15 | B | C |
| ATOM | 2376 | OE1 | GLU | B | 258 | 53.202 | 8.161 | 26.129 | 1.00 | 37.61 | B | O |
| ATOM | 2377 | OE2 | GLU | B | 258 | 52.773 | 5.990 | 26.028 | 1.00 | 36.04 | B | O |
| ATOM | 2378 | C | GLU | B | 258 | 51.157 | 9.647 | 30.616 | 1.00 | 27.80 | B | C |
| ATOM | 2379 | O | GLU | B | 258 | 50.727 | 10.786 | 30.462 | 1.00 | 28.31 | B | O |
| ATOM | 2380 | N | VAL | B | 259 | 52.013 | 9.323 | 31.575 | 1.00 | 27.13 | B | N |
| ATOM | 2381 | CA | VAL | B | 259 | 52.591 | 10.343 | 32.463 | 1.00 | 26.39 | B | C |
| ATOM | 2382 | CB | VAL | B | 259 | 52.223 | 10.142 | 33.935 | 1.00 | 26.40 | B | C |
| ATOM | 2383 | CG1 | VAL | B | 259 | 52.698 | 11.337 | 34.746 | 1.00 | 24.84 | B | C |
| ATOM | 2384 | CG2 | VAL | B | 259 | 50.706 | 9.952 | 34.066 | 1.00 | 27.26 | B | C |
| ATOM | 2385 | C | VAL | B | 259 | 54.116 | 10.285 | 32.287 | 1.00 | 25.63 | B | C |
| ATOM | 2386 | O | VAL | B | 259 | 54.700 | 9.210 | 32.186 | 1.00 | 24.95 | B | O |
| ATOM | 2387 | N | TRP | B | 260 | 54.718 | 11.459 | 32.162 | 1.00 | 25.98 | B | N |
| ATOM | 2388 | CA | TRP | B | 260 | 56.157 | 11.596 | 31.951 | 1.00 | 26.43 | B | C |
| ATOM | 2389 | CB | TRP | B | 260 | 56.442 | 12.198 | 30.567 | 1.00 | 27.04 | B | C |
| ATOM | 2390 | CG | TRP | B | 260 | 56.211 | 11.300 | 29.417 | 1.00 | 28.94 | B | C |
| ATOM | 2391 | CD2 | TRP | B | 260 | 57.211 | 10.756 | 28.555 | 1.00 | 31.21 | B | C |
| ATOM | 2392 | CE2 | TRP | B | 260 | 56.561 | 9.891 | 27.653 | 1.00 | 31.97 | B | C |
| ATOM | 2393 | CE3 | TRP | B | 260 | 58.604 | 10.918 | 28.458 | 1.00 | 30.55 | B | C |
| ATOM | 2394 | CD1 | TRP | B | 260 | 55.016 | 10.773 | 29.002 | 1.00 | 30.85 | B | C |
| ATOM | 2395 | NE1 | TRP | B | 260 | 55.221 | 9.911 | 27.953 | 1.00 | 31.67 | B | N |
| ATOM | 2396 | CZ2 | TRP | B | 260 | 57.249 | 9.183 | 26.677 | 1.00 | 32.23 | B | C |
| ATOM | 2397 | CZ3 | TRP | B | 260 | 59.281 | 10.208 | 27.484 | 1.00 | 31.65 | B | C |
| ATOM | 2398 | CH2 | TRP | B | 260 | 58.604 | 9.354 | 26.611 | 1.00 | 32.29 | B | C |
| ATOM | 2399 | C | TRP | B | 260 | 56.786 | 12.567 | 32.914 | 1.00 | 26.01 | B | C |
| ATOM | 2400 | O | TRP | B | 260 | 56.151 | 13.547 | 33.319 | 1.00 | 25.71 | B | O |
| ATOM | 2401 | N | MET | B | 261 | 58.038 | 12.289 | 33.276 | 1.00 | 24.91 | B | N |
| ATOM | 2402 | CA | MET | B | 261 | 58.798 | 13.230 | 34.084 | 1.00 | 25.07 | B | C |
| ATOM | 2403 | CB | MET | B | 261 | 59.895 | 12.506 | 34.862 | 1.00 | 25.93 | B | C |
| ATOM | 2404 | CG | MET | B | 261 | 60.745 | 13.447 | 35.726 | 1.00 | 27.63 | B | C |
| ATOM | 2405 | SD | MET | B | 261 | 62.090 | 14.326 | 34.836 | 1.00 | 28.15 | B | S |
| ATOM | 2406 | CE | MET | B | 261 | 63.019 | 12.914 | 34.170 | 1.00 | 28.19 | B | C |

Figure 11

| ATOM | 2407 | C | MET | B | 261 | 59.439 | 14.147 | 33.020 | 1.00 | 24.83 | B | C |
|------|------|------|------|---|-----|--------|--------|--------|------|-------|---|---|
| ATOM | 2408 | O | MET | B | 261 | 59.810 | 13.667 | 31.961 | 1.00 | 24.81 | B | O |
| ATOM | 2409 | N | GLY | B | 262 | 59.573 | 15.436 | 33.293 | 1.00 | 24.64 | B | N |
| ATOM | 2410 | CA | GLY | B | 262 | 60.189 | 16.324 | 32.332 | 1.00 | 26.16 | B | C |
| ATOM | 2411 | C | GLY | B | 262 | 60.706 | 17.594 | 32.981 | 1.00 | 28.74 | B | C |
| ATOM | 2412 | O | GLY | B | 262 | 60.730 | 17.682 | 34.212 | 1.00 | 28.45 | B | O |
| ATOM | 2413 | N | TYR | B | 263 | 61.143 | 18.568 | 32.173 | 1.00 | 29.84 | B | N |
| ATOM | 2414 | CA | TYR | B | 263 | 61.600 | 19.848 | 32.713 | 1.00 | 32.11 | B | C |
| ATOM | 2415 | CB | TYR | B | 263 | 63.125 | 20.014 | 32.587 | 1.00 | 31.20 | B | C |
| ATOM | 2416 | CG | TYR | B | 263 | 63.862 | 18.954 | 33.383 | 1.00 | 29.16 | B | C |
| ATOM | 2417 | CD1 | TYR | B | 263 | 64.219 | 19.174 | 34.720 | 1.00 | 27.31 | B | C |
| ATOM | 2418 | CE1 | TYR | B | 263 | 64.876 | 18.192 | 35.469 | 1.00 | 27.74 | B | C |
| ATOM | 2419 | CD2 | TYR | B | 263 | 64.175 | 17.712 | 32.807 | 1.00 | 29.55 | B | C |
| ATOM | 2420 | CE2 | TYR | B | 263 | 64.829 | 16.710 | 33.553 | 1.00 | 29.00 | B | C |
| ATOM | 2421 | CZ | TYR | B | 263 | 65.182 | 16.966 | 34.891 | 1.00 | 27.91 | B | C |
| ATOM | 2422 | OH | TYR | B | 263 | 65.805 | 15.971 | 35.637 | 1.00 | 29.15 | B | O |
| ATOM | 2423 | C | TYR | B | 263 | 60.848 | 20.989 | 32.078 | 1.00 | 33.92 | B | C |
| ATOM | 2424 | O | TYR | B | 263 | 60.594 | 20.998 | 30.883 | 1.00 | 34.49 | B | O |
| ATOM | 2425 | N | TYR | B | 264 | 60.422 | 21.921 | 32.912 | 1.00 | 35.87 | B | N |
| ATOM | 2426 | CA | TYR | B | 264 | 59.643 | 23.059 | 32.480 | 1.00 | 38.92 | B | C |
| ATOM | 2427 | CB | TYR | B | 264 | 58.372 | 23.127 | 33.350 | 1.00 | 38.95 | B | C |
| ATOM | 2428 | CG | TYR | B | 264 | 57.421 | 24.271 | 33.105 | 1.00 | 39.88 | B | C |
| ATOM | 2429 | CD1 | TYR | B | 264 | 56.887 | 24.521 | 31.836 | 1.00 | 39.55 | B | C |
| ATOM | 2430 | CE1 | TYR | B | 264 | 55.986 | 25.585 | 31.629 | 1.00 | 39.97 | B | C |
| ATOM | 2431 | CD2 | TYR | B | 264 | 57.038 | 25.102 | 34.162 | 1.00 | 40.72 | B | C |
| ATOM | 2432 | CE2 | TYR | B | 264 | 56.146 | 26.160 | 33.971 | 1.00 | 41.54 | B | C |
| ATOM | 2433 | CZ | TYR | B | 264 | 55.620 | 26.399 | 32.707 | 1.00 | 40.84 | B | C |
| ATOM | 2434 | OH | TYR | B | 264 | 54.725 | 27.439 | 32.554 | 1.00 | 40.54 | B | O |
| ATOM | 2435 | C | TYR | B | 264 | 60.551 | 24.282 | 32.633 | 1.00 | 41.37 | B | C |
| ATOM | 2436 | O | TYR | B | 264 | 61.088 | 24.557 | 33.722 | 1.00 | 41.33 | B | O |
| ATOM | 2437 | N | ASN | B | 265 | 60.756 | 24.973 | 31.511 | 1.00 | 43.33 | B | N |
| ATOM | 2438 | CA | ASN | B | 265 | 61.633 | 26.136 | 31.445 | 1.00 | 45.31 | B | C |
| ATOM | 2439 | CB | ASN | B | 265 | 61.206 | 27.219 | 32.422 | 1.00 | 44.53 | B | C |
| ATOM | 2440 | CG | ASN | B | 265 | 59.834 | 27.776 | 32.105 | 1.00 | 44.85 | B | C |
| ATOM | 2441 | OD1 | ASN | B | 265 | 59.502 | 28.030 | 30.943 | 1.00 | 43.17 | B | O |
| ATOM | 2442 | ND2 | ASN | B | 265 | 59.021 | 27.947 | 33.135 | 1.00 | 43.80 | B | N |
| ATOM | 2443 | C | ASN | B | 265 | 63.067 | 25.701 | 31.729 | 1.00 | 47.06 | B | C |
| ATOM | 2444 | O | ASN | B | 265 | 63.825 | 26.422 | 32.367 | 1.00 | 47.43 | B | O |
| ATOM | 2445 | N | GLY | B | 266 | 63.405 | 24.487 | 31.299 | 1.00 | 48.77 | B | N |
| ATOM | 2446 | CA | GLY | B | 266 | 64.750 | 23.980 | 31.482 | 1.00 | 50.26 | B | C |
| ATOM | 2447 | C | GLY | B | 266 | 65.166 | 23.485 | 32.852 | 1.00 | 51.14 | B | C |
| ATOM | 2448 | O | GLY | B | 266 | 65.934 | 22.508 | 32.936 | 1.00 | 52.03 | B | O |
| ATOM | 2449 | N | HIS | B | 267 | 64.664 | 24.102 | 33.923 | 1.00 | 51.31 | B | N |
| ATOM | 2450 | CA | HIS | B | 267 | 65.071 | 23.674 | 35.266 | 1.00 | 51.27 | B | C |
| ATOM | 2451 | CB | HIS | B | 267 | 66.066 | 24.690 | 35.862 | 1.00 | 54.79 | B | C |
| ATOM | 2452 | CG | HIS | B | 267 | 67.415 | 24.651 | 35.201 | 1.00 | 58.84 | B | C |
| ATOM | 2453 | CD2 | HIS | B | 267 | 68.328 | 23.652 | 35.095 | 1.00 | 60.15 | B | C |
| ATOM | 2454 | ND1 | HIS | B | 267 | 67.911 | 25.700 | 34.447 | 1.00 | 60.61 | B | N |
| ATOM | 2455 | CE1 | HIS | B | 267 | 69.061 | 25.344 | 33.900 | 1.00 | 61.67 | B | C |
| ATOM | 2456 | NE2 | HIS | B | 267 | 69.337 | 24.105 | 34.278 | 1.00 | 61.46 | B | N |
| ATOM | 2457 | C | HIS | B | 267 | 64.045 | 23.219 | 36.315 | 1.00 | 49.13 | B | C |
| ATOM | 2458 | O | HIS | B | 267 | 64.435 | 22.667 | 37.355 | 1.00 | 49.38 | B | O |
| ATOM | 2459 | N | THR | B | 268 | 62.754 | 23.428 | 36.068 | 1.00 | 46.06 | B | N |
| ATOM | 2460 | CA | THR | B | 268 | 61.735 | 22.991 | 37.039 | 1.00 | 42.54 | B | C |
| ATOM | 2461 | CB | THR | B | 268 | 60.473 | 23.919 | 37.027 | 1.00 | 42.95 | B | C |
| ATOM | 2462 | OG1 | THR | B | 268 | 60.862 | 25.270 | 37.331 | 1.00 | 43.71 | B | O |
| ATOM | 2463 | CG2 | THR | B | 268 | 59.446 | 23.476 | 38.070 | 1.00 | 41.95 | B | C |
| ATOM | 2464 | C | THR | B | 268 | 61.359 | 21.560 | 36.672 | 1.00 | 39.46 | B | C |
| ATOM | 2465 | O | THR | B | 268 | 60.965 | 21.294 | 35.539 | 1.00 | 39.61 | B | O |

Figure 11

| ATOM | 2466 | N | LYS B 269 | 61.542 | 20.626 | 37.595 | 1.00 | 36.13 | B | N |
|------|------|-----|-----------|--------|--------|--------|------|-------|---|---|
| ATOM | 2467 | CA | LYS B 269 | 61.203 | 19.248 | 37.308 | 1.00 | 33.59 | B | C |
| ATOM | 2468 | CB | LYS B 269 | 61.931 | 18.311 | 38.276 | 1.00 | 33.83 | B | C |
| ATOM | 2469 | CG | LYS B 269 | 61.915 | 16.871 | 37.855 | 1.00 | 34.04 | B | C |
| ATOM | 2470 | CD | LYS B 269 | 62.680 | 16.033 | 38.831 | 1.00 | 33.77 | B | C |
| ATOM | 2471 | CE | LYS B 269 | 63.237 | 14.826 | 38.126 | 1.00 | 35.44 | B | C |
| ATOM | 2472 | NZ | LYS B 269 | 64.451 | 14.257 | 38.819 | 1.00 | 36.81 | B | N |
| ATOM | 2473 | C | LYS B 269 | 59.682 | 19.158 | 37.434 | 1.00 | 32.49 | B | C |
| ATOM | 2474 | O | LYS B 269 | 59.101 | 19.701 | 38.378 | 1.00 | 32.27 | B | O |
| ATOM | 2475 | N | VAL B 270 | 59.035 | 18.526 | 36.448 | 1.00 | 30.71 | B | N |
| ATOM | 2476 | CA | VAL B 270 | 57.574 | 18.430 | 36.408 | 1.00 | 28.40 | B | C |
| ATOM | 2477 | CB | VAL B 270 | 56.939 | 19.527 | 35.458 | 1.00 | 27.70 | B | C |
| ATOM | 2478 | CG1 | VAL B 270 | 57.227 | 20.952 | 35.956 | 1.00 | 26.36 | B | C |
| ATOM | 2479 | CG2 | VAL B 270 | 57.424 | 19.331 | 34.030 | 1.00 | 25.08 | B | C |
| ATOM | 2480 | C | VAL B 270 | 57.085 | 17.093 | 35.877 | 1.00 | 28.12 | B | C |
| ATOM | 2481 | O | VAL B 270 | 57.855 | 16.306 | 35.331 | 1.00 | 26.99 | B | O |
| ATOM | 2482 | N | ALA B 271 | 55.812 | 16.803 | 36.160 | 1.00 | 28.20 | B | N |
| ATOM | 2483 | CA | ALA B 271 | 55.137 | 15.605 | 35.659 | 1.00 | 26.92 | B | C |
| ATOM | 2484 | CB | ALA B 271 | 54.248 | 14.972 | 36.725 | 1.00 | 26.12 | B | C |
| ATOM | 2485 | C | ALA B 271 | 54.285 | 16.139 | 34.502 | 1.00 | 26.93 | B | C |
| ATOM | 2486 | O | ALA B 271 | 53.748 | 17.239 | 34.575 | 1.00 | 26.48 | B | O |
| ATOM | 2487 | N | VAL B 272 | 54.168 | 15.357 | 33.435 | 1.00 | 27.44 | B | N |
| ATOM | 2488 | CA | VAL B 272 | 53.384 | 15.776 | 32.273 | 1.00 | 27.79 | B | C |
| ATOM | 2489 | CB | VAL B 272 | 54.287 | 16.115 | 31.027 | 1.00 | 27.85 | B | C |
| ATOM | 2490 | CG1 | VAL B 272 | 53.446 | 16.698 | 29.901 | 1.00 | 26.88 | B | C |
| ATOM | 2491 | CG2 | VAL B 272 | 55.352 | 17.134 | 31.401 | 1.00 | 28.00 | B | C |
| ATOM | 2492 | C | VAL B 272 | 52.446 | 14.641 | 31.899 | 1.00 | 27.54 | B | C |
| ATOM | 2493 | O | VAL B 272 | 52.880 | 13.537 | 31.570 | 1.00 | 26.83 | B | O |
| ATOM | 2494 | N | LYS B 273 | 51.149 | 14.907 | 31.990 | 1.00 | 28.59 | B | N |
| ATOM | 2495 | CA | LYS B 273 | 50.166 | 13.889 | 31.639 | 1.00 | 29.02 | B | C |
| ATOM | 2496 | CB | LYS B 273 | 48.991 | 13.953 | 32.626 | 1.00 | 30.17 | B | C |
| ATOM | 2497 | CG | LYS B 273 | 47.838 | 12.999 | 32.348 | 1.00 | 32.04 | B | C |
| ATOM | 2498 | CD | LYS B 273 | 46.757 | 13.169 | 33.406 | 1.00 | 33.70 | B | C |
| ATOM | 2499 | CE | LYS B 273 | 47.076 | 12.275 | 34.600 | 1.00 | 34.40 | B | C |
| ATOM | 2500 | NZ | LYS B 273 | 45.945 | 12.254 | 35.569 | 1.00 | 35.39 | B | N |
| ATOM | 2501 | C | LYS B 273 | 49.719 | 14.216 | 30.219 | 1.00 | 30.03 | B | C |
| ATOM | 2502 | O | LYS B 273 | 49.320 | 15.345 | 29.947 | 1.00 | 30.19 | B | O |
| ATOM | 2503 | N | SER B 274 | 49.818 | 13.260 | 29.296 | 1.00 | 31.13 | B | N |
| ATOM | 2504 | CA | SER B 274 | 49.403 | 13.534 | 27.926 | 1.00 | 32.56 | B | C |
| ATOM | 2505 | CB | SER B 274 | 50.541 | 13.291 | 26.937 | 1.00 | 32.49 | B | C |
| ATOM | 2506 | OG | SER B 274 | 50.953 | 11.944 | 27.045 | 1.00 | 34.10 | B | O |
| ATOM | 2507 | C | SER B 274 | 48.241 | 12.627 | 27.574 | 1.00 | 33.16 | B | C |
| ATOM | 2508 | O | SER B 274 | 48.220 | 11.454 | 27.928 | 1.00 | 33.42 | B | O |
| ATOM | 2509 | N | LEU B 275 | 47.293 | 13.180 | 26.834 | 1.00 | 34.05 | B | N |
| ATOM | 2510 | CA | LEU B 275 | 46.107 | 12.437 | 26.443 | 1.00 | 34.13 | B | C |
| ATOM | 2511 | CB | LEU B 275 | 44.987 | 13.439 | 26.159 | 1.00 | 32.22 | B | C |
| ATOM | 2512 | CG | LEU B 275 | 43.771 | 12.951 | 25.364 | 1.00 | 30.93 | B | C |
| ATOM | 2513 | CD1 | LEU B 275 | 42.996 | 11.928 | 26.187 | 1.00 | 30.76 | B | C |
| ATOM | 2514 | CD2 | LEU B 275 | 42.893 | 14.129 | 25.005 | 1.00 | 28.85 | B | C |
| ATOM | 2515 | C | LEU B 275 | 46.311 | 11.535 | 25.222 | 1.00 | 36.07 | B | C |
| ATOM | 2516 | O | LEU B 275 | 46.994 | 11.919 | 24.261 | 1.00 | 37.01 | B | O |
| ATOM | 2517 | N | LYS B 276 | 45.796 | 10.311 | 25.284 | 1.00 | 36.08 | B | N |
| ATOM | 2518 | CA | LYS B 276 | 45.849 | 9.431 | 24.126 | 1.00 | 37.42 | B | C |
| ATOM | 2519 | CB | LYS B 276 | 45.710 | 7.968 | 24.524 | 1.00 | 37.82 | B | C |
| ATOM | 2520 | CG | LYS B 276 | 45.475 | 7.061 | 23.325 | 1.00 | 39.86 | B | C |
| ATOM | 2521 | CD | LYS B 276 | 45.303 | 5.628 | 23.730 | 1.00 | 43.22 | B | C |
| ATOM | 2522 | CE | LYS B 276 | 46.501 | 5.172 | 24.543 | 1.00 | 45.01 | B | C |
| ATOM | 2523 | NZ | LYS B 276 | 46.307 | 3.815 | 25.143 | 1.00 | 47.73 | B | N |
| ATOM | 2524 | C | LYS B 276 | 44.602 | 9.818 | 23.311 | 1.00 | 38.56 | B | C |

Figure 11

| | | | | | | | | | | | |
|---|---|---|---|---|---|---|---|---|---|---|---|
| ATOM | 2525 | O | LYS | B | 276 | 43.474 | 9.608 | 23.766 | 1.00 | 38.08 | B O |
| ATOM | 2526 | N | GLN | B | 277 | 44.806 | 10.389 | 22.126 | 1.00 | 39.38 | B N |
| ATOM | 2527 | CA | GLN | B | 277 | 43.709 | 10.817 | 21.255 | 1.00 | 41.06 | B C |
| ATOM | 2528 | CB | GLN | B | 277 | 44.244 | 11.151 | 19.864 | 1.00 | 43.37 | B C |
| ATOM | 2529 | CG | GLN | B | 277 | 43.186 | 11.732 | 18.943 | 1.00 | 47.78 | B C |
| ATOM | 2530 | CD | GLN | B | 277 | 43.752 | 12.036 | 17.569 | 1.00 | 51.05 | B C |
| ATOM | 2531 | OE1 | GLN | B | 277 | 44.668 | 11.361 | 17.095 | 1.00 | 53.35 | B O |
| ATOM | 2532 | NE2 | GLN | B | 277 | 43.185 | 13.041 | 16.899 | 1.00 | 52.45 | B N |
| ATOM | 2533 | C | GLN | B | 277 | 42.557 | 9.822 | 21.128 | 1.00 | 40.20 | B C |
| ATOM | 2534 | O | GLN | B | 277 | 42.764 | 8.629 | 20.912 | 1.00 | 39.49 | B O |
| ATOM | 2535 | N | GLY | B | 278 | 41.340 | 10.325 | 21.300 | 1.00 | 40.36 | B N |
| ATOM | 2536 | CA | GLY | B | 278 | 40.172 | 9.475 | 21.203 | 1.00 | 40.36 | B C |
| ATOM | 2537 | C | GLY | B | 278 | 39.727 | 8.800 | 22.489 | 1.00 | 41.05 | B C |
| ATOM | 2538 | O | GLY | B | 278 | 38.669 | 8.161 | 22.517 | 1.00 | 42.05 | B O |
| ATOM | 2539 | N | SER | B | 279 | 40.522 | 8.901 | 23.548 | 1.00 | 40.08 | B N |
| ATOM | 2540 | CA | SER | B | 279 | 40.156 | 8.271 | 24.815 | 1.00 | 39.99 | B C |
| ATOM | 2541 | CB | SER | B | 279 | 41.347 | 8.296 | 25.772 | 1.00 | 40.38 | B C |
| ATOM | 2542 | OG | SER | B | 279 | 42.339 | 7.402 | 25.333 | 1.00 | 40.96 | B O |
| ATOM | 2543 | C | SER | B | 279 | 39.010 | 9.100 | 25.377 | 1.00 | 39.31 | B C |
| ATOM | 2544 | O | SER | B | 279 | 38.076 | 8.591 | 25.995 | 1.00 | 38.52 | B O |
| ATOM | 2545 | N | MET | B | 280 | 39.152 | 10.400 | 25.182 | 1.00 | 38.57 | B N |
| ATOM | 2546 | CA | MET | B | 280 | 38.180 | 11.396 | 25.580 | 1.00 | 38.12 | B C |
| ATOM | 2547 | CB | MET | B | 280 | 38.205 | 11.631 | 27.095 | 1.00 | 38.33 | B C |
| ATOM | 2548 | CG | MET | B | 280 | 39.318 | 12.528 | 27.631 | 1.00 | 38.89 | B C |
| ATOM | 2549 | SD | MET | B | 280 | 39.378 | 12.418 | 29.470 | 1.00 | 40.04 | B S |
| ATOM | 2550 | CE | MET | B | 280 | 38.632 | 13.833 | 29.869 | 1.00 | 40.38 | B C |
| ATOM | 2551 | C | MET | B | 280 | 38.561 | 12.633 | 24.777 | 1.00 | 37.52 | B C |
| ATOM | 2552 | O | MET | B | 280 | 39.635 | 12.671 | 24.161 | 1.00 | 37.55 | B O |
| ATOM | 2553 | N | SER | B | 281 | 37.672 | 13.618 | 24.744 | 1.00 | 36.56 | B N |
| ATOM | 2554 | CA | SER | B | 281 | 37.949 | 14.822 | 23.980 | 1.00 | 36.70 | B C |
| ATOM | 2555 | CB | SER | B | 281 | 36.646 | 15.556 | 23.662 | 1.00 | 33.88 | B C |
| ATOM | 2556 | OG | SER | B | 281 | 36.279 | 16.438 | 24.706 | 1.00 | 33.48 | B O |
| ATOM | 2557 | C | SER | B | 281 | 38.935 | 15.765 | 24.683 | 1.00 | 38.39 | B C |
| ATOM | 2558 | O | SER | B | 281 | 39.070 | 15.732 | 25.917 | 1.00 | 38.35 | B O |
| ATOM | 2559 | N | PRO | B | 282 | 39.668 | 16.576 | 23.907 | 1.00 | 39.17 | B N |
| ATOM | 2560 | CD | PRO | B | 282 | 39.802 | 16.442 | 22.444 | 1.00 | 40.13 | B C |
| ATOM | 2561 | CA | PRO | B | 282 | 40.644 | 17.538 | 24.408 | 1.00 | 40.59 | B C |
| ATOM | 2562 | CB | PRO | B | 282 | 41.036 | 18.292 | 23.136 | 1.00 | 39.52 | B C |
| ATOM | 2563 | CG | PRO | B | 282 | 41.098 | 17.195 | 22.159 | 1.00 | 39.21 | B C |
| ATOM | 2564 | C | PRO | B | 282 | 40.020 | 18.477 | 25.424 | 1.00 | 42.29 | B C |
| ATOM | 2565 | O | PRO | B | 282 | 40.610 | 18.716 | 26.473 | 1.00 | 42.63 | B O |
| ATOM | 2566 | N | ASP | B | 283 | 38.831 | 18.988 | 25.133 | 1.00 | 43.49 | B N |
| ATOM | 2567 | CA | ASP | B | 283 | 38.156 | 19.898 | 26.058 | 1.00 | 44.67 | B C |
| ATOM | 2568 | CB | ASP | B | 283 | 36.904 | 20.551 | 25.423 | 1.00 | 47.45 | B C |
| ATOM | 2569 | CG | ASP | B | 283 | 37.249 | 21.835 | 24.636 | 1.00 | 50.68 | B C |
| ATOM | 2570 | OD1 | ASP | B | 283 | 38.369 | 22.384 | 24.759 | 1.00 | 53.16 | B O |
| ATOM | 2571 | OD2 | ASP | B | 283 | 36.368 | 22.314 | 23.879 | 1.00 | 51.97 | B O |
| ATOM | 2572 | C | ASP | B | 283 | 37.807 | 19.234 | 27.402 | 1.00 | 43.51 | B C |
| ATOM | 2573 | O | ASP | B | 283 | 37.965 | 19.842 | 28.454 | 1.00 | 43.06 | B O |
| ATOM | 2574 | N | ALA | B | 284 | 37.374 | 17.977 | 27.348 | 1.00 | 42.80 | B N |
| ATOM | 2575 | CA | ALA | B | 284 | 37.045 | 17.233 | 28.569 | 1.00 | 42.14 | B C |
| ATOM | 2576 | CB | ALA | B | 284 | 36.453 | 15.865 | 28.202 | 1.00 | 40.49 | B C |
| ATOM | 2577 | C | ALA | B | 284 | 38.312 | 17.044 | 29.422 | 1.00 | 41.46 | B C |
| ATOM | 2578 | O | ALA | B | 284 | 38.281 | 17.233 | 30.643 | 1.00 | 42.01 | B O |
| ATOM | 2579 | N | PHE | B | 285 | 39.415 | 16.662 | 28.775 | 1.00 | 40.44 | B N |
| ATOM | 2580 | CA | PHE | B | 285 | 40.702 | 16.423 | 29.434 | 1.00 | 38.85 | B C |
| ATOM | 2581 | CB | PHE | B | 285 | 41.685 | 15.829 | 28.409 | 1.00 | 37.97 | B C |
| ATOM | 2582 | CG | PHE | B | 285 | 43.075 | 15.584 | 28.944 | 1.00 | 36.87 | B C |
| ATOM | 2583 | CD1 | PHE | B | 285 | 43.355 | 14.471 | 29.740 | 1.00 | 36.77 | B C |

Figure 11

| | | | | | | | | | | | |
|---|---|---|---|---|---|---|---|---|---|---|---|
| ATOM | 2584 | CD2 | PHE | B | 285 | 44.118 | 16.430 | 28.602 | 1.00 35.50 | B | C |
| ATOM | 2585 | CE1 | PHE | B | 285 | 44.663 | 14.221 | 30.179 | 1.00 36.88 | B | C |
| ATOM | 2586 | CE2 | PHE | B | 285 | 45.426 | 16.185 | 29.037 | 1.00 35.11 | B | C |
| ATOM | 2587 | CZ | PHE | B | 285 | 45.697 | 15.080 | 29.817 | 1.00 35.72 | B | C |
| ATOM | 2588 | C | PHE | B | 285 | 41.250 | 17.702 | 30.061 | 1.00 38.61 | B | C |
| ATOM | 2589 | O | PHE | B | 285 | 41.665 | 17.719 | 31.218 | 1.00 37.93 | B | O |
| ATOM | 2590 | N | LEU | B | 286 | 41.209 | 18.784 | 29.304 | 1.00 38.75 | B | N |
| ATOM | 2591 | CA | LEU | B | 286 | 41.701 | 20.063 | 29.784 | 1.00 39.67 | B | C |
| ATOM | 2592 | CB | LEU | B | 286 | 41.825 | 21.049 | 28.618 | 1.00 40.71 | B | C |
| ATOM | 2593 | CG | LEU | B | 286 | 42.884 | 20.651 | 27.582 | 1.00 40.84 | B | C |
| ATOM | 2594 | CD1 | LEU | B | 286 | 42.870 | 21.593 | 26.384 | 1.00 42.11 | B | C |
| ATOM | 2595 | CD2 | LEU | B | 286 | 44.228 | 20.668 | 28.269 | 1.00 41.94 | B | C |
| ATOM | 2596 | C | LEU | B | 286 | 40.773 | 20.608 | 30.842 | 1.00 40.23 | B | C |
| ATOM | 2597 | O | LEU | B | 286 | 41.206 | 21.314 | 31.741 | 1.00 39.83 | B | O |
| ATOM | 2598 | N | ALA | B | 287 | 39.489 | 20.260 | 30.736 | 1.00 41.52 | B | N |
| ATOM | 2599 | CA | ALA | B | 287 | 38.470 | 20.708 | 31.688 | 1.00 42.64 | B | C |
| ATOM | 2600 | CB | ALA | B | 287 | 37.067 | 20.295 | 31.223 | 1.00 42.62 | B | C |
| ATOM | 2601 | C | ALA | B | 287 | 38.766 | 20.176 | 33.090 | 1.00 42.14 | B | C |
| ATOM | 2602 | O | ALA | B | 287 | 38.569 | 20.876 | 34.071 | 1.00 42.17 | B | O |
| ATOM | 2603 | N | GLU | B | 288 | 39.261 | 18.949 | 33.168 | 1.00 42.90 | B | N |
| ATOM | 2604 | CA | GLU | B | 288 | 39.621 | 18.367 | 34.456 | 1.00 44.38 | B | C |
| ATOM | 2605 | CB | GLU | B | 288 | 40.067 | 16.916 | 34.280 | 1.00 45.03 | B | C |
| ATOM | 2606 | CG | GLU | B | 288 | 38.995 | 15.976 | 33.714 | 1.00 47.09 | B | C |
| ATOM | 2607 | CD | GLU | B | 288 | 39.468 | 14.531 | 33.569 | 1.00 47.74 | B | C |
| ATOM | 2608 | OE1 | GLU | B | 288 | 40.688 | 14.309 | 33.423 | 1.00 50.08 | B | O |
| ATOM | 2609 | OE2 | GLU | B | 288 | 38.627 | 13.610 | 33.609 | 1.00 47.50 | B | O |
| ATOM | 2610 | C | GLU | B | 288 | 40.738 | 19.196 | 35.115 | 1.00 45.24 | B | C |
| ATOM | 2611 | O | GLU | B | 288 | 40.746 | 19.377 | 36.334 | 1.00 45.70 | B | O |
| ATOM | 2612 | N | ALA | B | 289 | 41.646 | 19.731 | 34.296 | 1.00 45.42 | B | N |
| ATOM | 2613 | CA | ALA | B | 289 | 42.753 | 20.547 | 34.782 | 1.00 45.42 | B | C |
| ATOM | 2614 | CB | ALA | B | 289 | 43.725 | 20.831 | 33.654 | 1.00 45.43 | B | C |
| ATOM | 2615 | C | ALA | B | 289 | 42.291 | 21.849 | 35.406 | 1.00 46.35 | B | C |
| ATOM | 2616 | O | ALA | B | 289 | 42.998 | 22.424 | 36.219 | 1.00 45.07 | B | O |
| ATOM | 2617 | N | ASN | B | 290 | 41.111 | 22.313 | 35.002 | 1.00 48.71 | B | N |
| ATOM | 2618 | CA | ASN | B | 290 | 40.528 | 23.558 | 35.521 | 1.00 51.27 | B | C |
| ATOM | 2619 | CB | ASN | B | 290 | 39.206 | 23.869 | 34.812 | 1.00 52.82 | B | C |
| ATOM | 2620 | CG | ASN | B | 290 | 39.394 | 24.295 | 33.366 | 1.00 53.13 | B | C |
| ATOM | 2621 | OD1 | ASN | B | 290 | 38.520 | 24.068 | 32.528 | 1.00 54.05 | B | O |
| ATOM | 2622 | ND2 | ASN | B | 290 | 40.520 | 24.931 | 33.071 | 1.00 53.25 | B | N |
| ATOM | 2623 | C | ASN | B | 290 | 40.303 | 23.594 | 37.046 | 1.00 52.67 | B | C |
| ATOM | 2624 | O | ASN | B | 290 | 40.442 | 24.653 | 37.667 | 1.00 52.64 | B | O |
| ATOM | 2625 | N | LEU | B | 291 | 39.947 | 22.442 | 37.622 | 1.00 53.85 | B | N |
| ATOM | 2626 | CA | LEU | B | 291 | 39.711 | 22.283 | 39.058 | 1.00 54.95 | B | C |
| ATOM | 2627 | CB | LEU | B | 291 | 39.230 | 20.860 | 39.343 | 1.00 55.98 | B | C |
| ATOM | 2628 | CG | LEU | B | 291 | 38.047 | 20.381 | 38.495 | 1.00 56.67 | B | C |
| ATOM | 2629 | CD1 | LEU | B | 291 | 37.938 | 18.879 | 38.537 | 1.00 56.86 | B | C |
| ATOM | 2630 | CD2 | LEU | B | 291 | 36.762 | 21.035 | 38.962 | 1.00 57.86 | B | C |
| ATOM | 2631 | C | LEU | B | 291 | 40.981 | 22.542 | 39.864 | 1.00 55.71 | B | C |
| ATOM | 2632 | O | LEU | B | 291 | 40.925 | 22.997 | 41.012 | 1.00 56.19 | B | O |
| ATOM | 2633 | N | MET | B | 292 | 42.119 | 22.179 | 39.288 | 1.00 55.58 | B | N |
| ATOM | 2634 | CA | MET | B | 292 | 43.414 | 22.395 | 39.934 | 1.00 55.34 | B | C |
| ATOM | 2635 | CB | MET | B | 292 | 44.512 | 21.655 | 39.158 | 1.00 55.52 | B | C |
| ATOM | 2636 | CG | MET | B | 292 | 45.291 | 20.632 | 39.985 | 1.00 55.60 | B | C |
| ATOM | 2637 | SD | MET | B | 292 | 46.364 | 19.611 | 38.980 | 1.00 53.53 | B | S |
| ATOM | 2638 | CE | MET | B | 292 | 45.765 | 17.899 | 39.397 | 1.00 55.92 | B | C |
| ATOM | 2639 | C | MET | B | 292 | 43.728 | 23.897 | 40.005 | 1.00 55.34 | B | C |
| ATOM | 2640 | O | MET | B | 292 | 44.393 | 24.363 | 40.928 | 1.00 54.78 | B | O |
| ATOM | 2641 | N | LYS | B | 293 | 43.260 | 24.648 | 39.017 | 1.00 55.35 | B | N |
| ATOM | 2642 | CA | LYS | B | 293 | 43.481 | 26.087 | 39.004 | 1.00 55.72 | B | C |

Figure 11

| | | | | | | | | | | | |
|---|---|---|---|---|---|---|---|---|---|---|---|
| ATOM | 2643 | CB | LYS | B | 293 | 42.987 | 26.693 | 37.694 | 1.00 | 57.22 | B C |
| ATOM | 2644 | CG | LYS | B | 293 | 43.545 | 26.089 | 36.416 | 1.00 | 59.08 | B C |
| ATOM | 2645 | CD | LYS | B | 293 | 42.959 | 26.826 | 35.196 | 1.00 | 60.21 | B C |
| ATOM | 2646 | CE | LYS | B | 293 | 43.483 | 26.269 | 33.875 | 1.00 | 61.66 | B C |
| ATOM | 2647 | NZ | LYS | B | 293 | 42.943 | 27.022 | 32.706 | 1.00 | 62.12 | B N |
| ATOM | 2648 | C | LYS | B | 293 | 42.654 | 26.701 | 40.138 | 1.00 | 55.38 | B C |
| ATOM | 2649 | O | LYS | B | 293 | 43.109 | 27.604 | 40.848 | 1.00 | 56.12 | B O |
| ATOM | 2650 | N | GLN | B | 294 | 41.438 | 26.185 | 40.297 | 1.00 | 53.76 | B N |
| ATOM | 2651 | CA | GLN | B | 294 | 40.505 | 26.671 | 41.301 | 1.00 | 52.19 | B C |
| ATOM | 2652 | CB | GLN | B | 294 | 39.110 | 26.084 | 41.039 | 1.00 | 53.18 | B C |
| ATOM | 2653 | CG | GLN | B | 294 | 38.620 | 26.301 | 39.614 | 1.00 | 55.75 | B C |
| ATOM | 2654 | CD | GLN | B | 294 | 38.820 | 27.741 | 39.133 | 1.00 | 58.46 | B C |
| ATOM | 2655 | OE1 | GLN | B | 294 | 39.641 | 28.012 | 38.243 | 1.00 | 58.23 | B O |
| ATOM | 2656 | NE2 | GLN | B | 294 | 38.068 | 28.673 | 39.731 | 1.00 | 59.76 | B N |
| ATOM | 2657 | C | GLN | B | 294 | 40.914 | 26.442 | 42.753 | 1.00 | 50.29 | B C |
| ATOM | 2658 | O | GLN | B | 294 | 40.888 | 27.378 | 43.558 | 1.00 | 50.50 | B O |
| ATOM | 2659 | N | LEU | B | 295 | 41.268 | 25.205 | 43.092 | 1.00 | 47.79 | B N |
| ATOM | 2660 | CA | LEU | B | 295 | 41.673 | 24.858 | 44.448 | 1.00 | 45.60 | B C |
| ATOM | 2661 | CB | LEU | B | 295 | 40.961 | 23.593 | 44.925 | 1.00 | 46.51 | B C |
| ATOM | 2662 | CG | LEU | B | 295 | 39.508 | 23.630 | 45.343 | 1.00 | 46.58 | B C |
| ATOM | 2663 | CD1 | LEU | B | 295 | 39.219 | 22.337 | 46.095 | 1.00 | 46.86 | B C |
| ATOM | 2664 | CD2 | LEU | B | 295 | 39.262 | 24.813 | 46.262 | 1.00 | 47.04 | B C |
| ATOM | 2665 | C | LEU | B | 295 | 43.166 | 24.599 | 44.564 | 1.00 | 43.43 | B C |
| ATOM | 2666 | O | LEU | B | 295 | 43.656 | 23.580 | 44.116 | 1.00 | 42.40 | B O |
| ATOM | 2667 | N | GLN | B | 296 | 43.872 | 25.502 | 45.225 | 1.00 | 41.97 | B N |
| ATOM | 2668 | CA | GLN | B | 296 | 45.303 | 25.353 | 45.406 | 1.00 | 40.82 | B C |
| ATOM | 2669 | CB | GLN | B | 296 | 46.049 | 26.533 | 44.807 | 1.00 | 42.28 | B C |
| ATOM | 2670 | CG | GLN | B | 296 | 45.823 | 26.723 | 43.330 | 1.00 | 44.69 | B C |
| ATOM | 2671 | CD | GLN | B | 296 | 46.013 | 28.162 | 42.928 | 1.00 | 47.36 | B C |
| ATOM | 2672 | OE1 | GLN | B | 296 | 45.876 | 29.073 | 43.737 | 1.00 | 49.19 | B O |
| ATOM | 2673 | NE2 | GLN | B | 296 | 46.309 | 28.382 | 41.657 | 1.00 | 46.96 | B N |
| ATOM | 2674 | C | GLN | B | 296 | 45.608 | 25.231 | 46.885 | 1.00 | 39.21 | B C |
| ATOM | 2675 | O | GLN | B | 296 | 45.099 | 25.996 | 47.699 | 1.00 | 38.86 | B O |
| ATOM | 2676 | N | HIS | B | 297 | 46.459 | 24.271 | 47.219 | 1.00 | 37.13 | B N |
| ATOM | 2677 | CA | HIS | B | 297 | 46.813 | 24.057 | 48.602 | 1.00 | 35.41 | B C |
| ATOM | 2678 | CB | HIS | B | 297 | 45.670 | 23.310 | 49.290 | 1.00 | 33.78 | B C |
| ATOM | 2679 | CG | HIS | B | 297 | 45.768 | 23.330 | 50.795 | 1.00 | 32.70 | B C |
| ATOM | 2680 | CD2 | HIS | B | 297 | 45.211 | 24.149 | 51.706 | 1.00 | 31.06 | B C |
| ATOM | 2681 | ND1 | HIS | B | 297 | 46.549 | 22.449 | 51.480 | 1.00 | 32.27 | B N |
| ATOM | 2682 | CE1 | HIS | B | 297 | 46.481 | 22.718 | 52.778 | 1.00 | 30.85 | B C |
| ATOM | 2683 | NE2 | HIS | B | 297 | 45.668 | 23.747 | 52.933 | 1.00 | 29.74 | B N |
| ATOM | 2684 | C | HIS | B | 297 | 48.080 | 23.216 | 48.670 | 1.00 | 35.30 | B C |
| ATOM | 2685 | O | HIS | B | 297 | 48.389 | 22.463 | 47.730 | 1.00 | 34.28 | B O |
| ATOM | 2686 | N | GLN | B | 298 | 48.809 | 23.351 | 49.781 | 1.00 | 35.20 | B N |
| ATOM | 2687 | CA | GLN | B | 298 | 50.035 | 22.593 | 49.976 | 1.00 | 35.55 | B C |
| ATOM | 2688 | CB | GLN | B | 298 | 50.741 | 22.988 | 51.282 | 1.00 | 37.76 | B C |
| ATOM | 2689 | CG | GLN | B | 298 | 51.710 | 24.207 | 51.152 | 1.00 | 43.86 | B C |
| ATOM | 2690 | CD | GLN | B | 298 | 52.776 | 24.069 | 50.015 | 1.00 | 46.03 | B C |
| ATOM | 2691 | OE1 | GLN | B | 298 | 53.003 | 25.007 | 49.237 | 1.00 | 47.09 | B O |
| ATOM | 2692 | NE2 | GLN | B | 298 | 53.409 | 22.896 | 49.920 | 1.00 | 46.67 | B N |
| ATOM | 2693 | C | GLN | B | 298 | 49.791 | 21.096 | 49.956 | 1.00 | 33.92 | B C |
| ATOM | 2694 | O | GLN | B | 298 | 50.688 | 20.326 | 49.617 | 1.00 | 33.17 | B O |
| ATOM | 2695 | N | ARG | B | 299 | 48.576 | 20.687 | 50.313 | 1.00 | 32.31 | B N |
| ATOM | 2696 | CA | ARG | B | 299 | 48.228 | 19.263 | 50.341 | 1.00 | 31.06 | B C |
| ATOM | 2697 | CB | ARG | B | 299 | 47.317 | 18.981 | 51.525 | 1.00 | 32.67 | B C |
| ATOM | 2698 | CG | ARG | B | 299 | 48.037 | 19.141 | 52.814 | 1.00 | 35.98 | B C |
| ATOM | 2699 | CD | ARG | B | 299 | 49.170 | 18.176 | 52.842 | 1.00 | 38.28 | B C |
| ATOM | 2700 | NE | ARG | B | 299 | 50.190 | 18.701 | 53.710 | 1.00 | 42.82 | B N |
| ATOM | 2701 | CZ | ARG | B | 299 | 51.492 | 18.608 | 53.466 | 1.00 | 45.32 | B C |

Figure 11

| | | | | | | | | | | | |
|---|---|---|---|---|---|---|---|---|---|---|---|
| ATOM | 2702 | NH1 | ARG | B | 299 | 51.941 | 17.998 | 52.351 | 1.00 | 46.01 | B | N |
| ATOM | 2703 | NH2 | ARG | B | 299 | 52.334 | 19.101 | 54.368 | 1.00 | 46.15 | B | N |
| ATOM | 2704 | C | ARG | B | 299 | 47.594 | 18.696 | 49.071 | 1.00 | 29.57 | B | C |
| ATOM | 2705 | O | ARG | B | 299 | 47.286 | 17.494 | 48.997 | 1.00 | 28.60 | B | O |
| ATOM | 2706 | N | LEU | B | 300 | 47.388 | 19.577 | 48.097 | 1.00 | 26.96 | B | N |
| ATOM | 2707 | CA | LEU | B | 300 | 46.792 | 19.233 | 46.808 | 1.00 | 27.54 | B | C |
| ATOM | 2708 | CB | LEU | B | 300 | 45.615 | 20.189 | 46.522 | 1.00 | 25.87 | B | C |
| ATOM | 2709 | CG | LEU | B | 300 | 44.244 | 19.863 | 47.118 | 1.00 | 26.13 | B | C |
| ATOM | 2710 | CD1 | LEU | B | 300 | 44.350 | 19.507 | 48.569 | 1.00 | 25.49 | B | C |
| ATOM | 2711 | CD2 | LEU | B | 300 | 43.292 | 21.021 | 46.895 | 1.00 | 27.33 | B | C |
| ATOM | 2712 | C | LEU | B | 300 | 47.841 | 19.362 | 45.704 | 1.00 | 26.86 | B | C |
| ATOM | 2713 | O | LEU | B | 300 | 48.600 | 20.294 | 45.719 | 1.00 | 27.12 | B | O |
| ATOM | 2714 | N | VAL | B | 301 | 47.862 | 18.442 | 44.745 | 1.00 | 27.48 | B | N |
| ATOM | 2715 | CA | VAL | B | 301 | 48.819 | 18.504 | 43.628 | 1.00 | 28.23 | B | C |
| ATOM | 2716 | CB | VAL | B | 301 | 48.675 | 17.284 | 42.704 | 1.00 | 28.00 | B | C |
| ATOM | 2717 | CG1 | VAL | B | 301 | 49.520 | 17.488 | 41.438 | 1.00 | 27.80 | B | C |
| ATOM | 2718 | CG2 | VAL | B | 301 | 49.105 | 16.022 | 43.437 | 1.00 | 25.59 | B | C |
| ATOM | 2719 | C | VAL | B | 301 | 48.616 | 19.783 | 42.799 | 1.00 | 29.65 | B | C |
| ATOM | 2720 | O | VAL | B | 301 | 47.526 | 20.029 | 42.297 | 1.00 | 29.93 | B | O |
| ATOM | 2721 | N | ARG | B | 302 | 49.667 | 20.592 | 42.697 | 1.00 | 30.83 | B | N |
| ATOM | 2722 | CA | ARG | B | 302 | 49.651 | 21.869 | 41.995 | 1.00 | 33.54 | B | C |
| ATOM | 2723 | CB | ARG | B | 302 | 50.703 | 22.800 | 42.616 | 1.00 | 37.01 | B | C |
| ATOM | 2724 | CG | ARG | B | 302 | 50.829 | 24.194 | 42.020 | 1.00 | 42.77 | B | C |
| ATOM | 2725 | CD | ARG | B | 302 | 52.048 | 24.248 | 41.101 | 1.00 | 48.82 | B | C |
| ATOM | 2726 | NE | ARG | B | 302 | 52.566 | 25.606 | 40.867 | 1.00 | 53.86 | B | N |
| ATOM | 2727 | CZ | ARG | B | 302 | 53.506 | 26.191 | 41.613 | 1.00 | 55.22 | B | C |
| ATOM | 2728 | NH1 | ARG | B | 302 | 54.031 | 25.546 | 42.652 | 1.00 | 56.26 | B | N |
| ATOM | 2729 | NH2 | ARG | B | 302 | 54.003 | 27.369 | 41.253 | 1.00 | 56.05 | B | N |
| ATOM | 2730 | C | ARG | B | 302 | 49.823 | 21.799 | 40.482 | 1.00 | 33.84 | B | C |
| ATOM | 2731 | O | ARG | B | 302 | 50.633 | 21.029 | 39.949 | 1.00 | 32.02 | B | O |
| ATOM | 2732 | N | LEU | B | 303 | 49.036 | 22.621 | 39.802 | 1.00 | 34.87 | B | N |
| ATOM | 2733 | CA | LEU | B | 303 | 49.077 | 22.704 | 38.352 | 1.00 | 36.11 | B | C |
| ATOM | 2734 | CB | LEU | B | 303 | 47.681 | 22.933 | 37.790 | 1.00 | 37.28 | B | C |
| ATOM | 2735 | CG | LEU | B | 303 | 47.718 | 23.254 | 36.302 | 1.00 | 38.26 | B | C |
| ATOM | 2736 | CD1 | LEU | B | 303 | 47.902 | 21.966 | 35.523 | 1.00 | 38.26 | B | C |
| ATOM | 2737 | CD2 | LEU | B | 303 | 46.470 | 23.984 | 35.868 | 1.00 | 38.04 | B | C |
| ATOM | 2738 | C | LEU | B | 303 | 49.975 | 23.855 | 37.926 | 1.00 | 36.28 | B | C |
| ATOM | 2739 | O | LEU | B | 303 | 49.907 | 24.940 | 38.504 | 1.00 | 36.05 | B | O |
| ATOM | 2740 | N | TYR | B | 304 | 50.858 | 23.594 | 36.961 | 1.00 | 36.52 | B | N |
| ATOM | 2741 | CA | TYR | B | 304 | 51.731 | 24.640 | 36.437 | 1.00 | 37.25 | B | C |
| ATOM | 2742 | CB | TYR | B | 304 | 53.142 | 24.117 | 36.159 | 1.00 | 39.42 | B | C |
| ATOM | 2743 | CG | TYR | B | 304 | 53.998 | 23.943 | 37.386 | 1.00 | 42.19 | B | C |
| ATOM | 2744 | CD1 | TYR | B | 304 | 54.535 | 22.703 | 37.710 | 1.00 | 43.17 | B | C |
| ATOM | 2745 | CE1 | TYR | B | 304 | 55.280 | 22.510 | 38.859 | 1.00 | 43.54 | B | C |
| ATOM | 2746 | CD2 | TYR | B | 304 | 54.239 | 25.004 | 38.247 | 1.00 | 44.95 | B | C |
| ATOM | 2747 | CE2 | TYR | B | 304 | 54.998 | 24.815 | 39.409 | 1.00 | 46.27 | B | C |
| ATOM | 2748 | CZ | TYR | B | 304 | 55.505 | 23.562 | 39.701 | 1.00 | 45.01 | B | C |
| ATOM | 2749 | OH | TYR | B | 304 | 56.228 | 23.363 | 40.850 | 1.00 | 47.09 | B | O |
| ATOM | 2750 | C | TYR | B | 304 | 51.154 | 25.206 | 35.148 | 1.00 | 36.49 | B | C |
| ATOM | 2751 | O | TYR | B | 304 | 50.996 | 26.402 | 35.026 | 1.00 | 36.84 | B | O |
| ATOM | 2752 | N | ALA | B | 305 | 50.775 | 24.337 | 34.217 | 1.00 | 36.47 | B | N |
| ATOM | 2753 | CA | ALA | B | 305 | 50.260 | 24.790 | 32.931 | 1.00 | 36.09 | B | C |
| ATOM | 2754 | CB | ALA | B | 305 | 51.425 | 25.426 | 32.142 | 1.00 | 36.40 | B | C |
| ATOM | 2755 | C | ALA | B | 305 | 49.622 | 23.679 | 32.101 | 1.00 | 35.71 | B | C |
| ATOM | 2756 | O | ALA | B | 305 | 49.496 | 22.538 | 32.548 | 1.00 | 34.89 | B | O |
| ATOM | 2757 | N | VAL | B | 306 | 49.241 | 24.036 | 30.875 | 1.00 | 35.95 | B | N |
| ATOM | 2758 | CA | VAL | B | 306 | 48.639 | 23.114 | 29.908 | 1.00 | 36.69 | B | C |
| ATOM | 2759 | CB | VAL | B | 306 | 47.061 | 23.177 | 29.907 | 1.00 | 36.55 | B | C |
| ATOM | 2760 | CG1 | VAL | B | 306 | 46.464 | 22.679 | 31.249 | 1.00 | 35.49 | B | C |

Figure 11

| | | | | | | | | | | |
|---|---|---|---|---|---|---|---|---|---|---|
| ATOM | 2761 | CG2 | VAL | B | 306 | 46.593 | 24.593 | 29.615 | 1.00 35.89 | B C |
| ATOM | 2762 | C | VAL | B | 306 | 49.087 | 23.451 | 28.466 | 1.00 37.71 | B C |
| ATOM | 2763 | O | VAL | B | 306 | 49.418 | 24.605 | 28.161 | 1.00 37.67 | B O |
| ATOM | 2764 | N | VAL | B | 307 | 49.102 | 22.439 | 27.601 | 1.00 37.72 | B N |
| ATOM | 2765 | CA | VAL | B | 307 | 49.425 | 22.619 | 26.193 | 1.00 39.55 | B C |
| ATOM | 2766 | CB | VAL | B | 307 | 50.665 | 21.787 | 25.756 | 1.00 38.99 | B C |
| ATOM | 2767 | CG1 | VAL | B | 307 | 50.834 | 21.786 | 24.222 | 1.00 37.73 | B C |
| ATOM | 2768 | CG2 | VAL | B | 307 | 51.913 | 22.371 | 26.427 | 1.00 37.28 | B C |
| ATOM | 2769 | C | VAL | B | 307 | 48.142 | 22.197 | 25.478 | 1.00 41.34 | B C |
| ATOM | 2770 | O | VAL | B | 307 | 47.695 | 21.055 | 25.582 | 1.00 40.53 | B O |
| ATOM | 2771 | N | THR | B | 308 | 47.518 | 23.164 | 24.812 | 1.00 43.71 | B N |
| ATOM | 2772 | CA | THR | B | 308 | 46.255 | 22.939 | 24.115 | 1.00 46.25 | B C |
| ATOM | 2773 | CB | THR | B | 308 | 45.432 | 24.232 | 24.108 | 1.00 45.81 | B C |
| ATOM | 2774 | OG1 | THR | B | 308 | 46.206 | 25.289 | 23.543 | 1.00 46.20 | B O |
| ATOM | 2775 | CG2 | THR | B | 308 | 45.104 | 24.619 | 25.514 | 1.00 45.71 | B C |
| ATOM | 2776 | C | THR | B | 308 | 46.266 | 22.284 | 22.726 | 1.00 48.09 | B C |
| ATOM | 2777 | O | THR | B | 308 | 45.223 | 21.875 | 22.227 | 1.00 47.97 | B O |
| ATOM | 2778 | N | GLN | B | 309 | 47.427 | 22.166 | 22.094 | 1.00 49.87 | B N |
| ATOM | 2779 | CA | GLN | B | 309 | 47.470 | 21.511 | 20.789 | 1.00 51.77 | B C |
| ATOM | 2780 | CB | GLN | B | 309 | 48.389 | 22.249 | 19.813 | 1.00 54.47 | B C |
| ATOM | 2781 | CG | GLN | B | 309 | 47.928 | 23.677 | 19.492 | 1.00 59.08 | B C |
| ATOM | 2782 | CD | GLN | B | 309 | 46.539 | 23.752 | 18.818 | 1.00 60.94 | B C |
| ATOM | 2783 | OE1 | GLN | B | 309 | 45.874 | 22.744 | 18.546 | 1.00 61.40 | B O |
| ATOM | 2784 | NE2 | GLN | B | 309 | 46.113 | 24.982 | 18.525 | 1.00 62.76 | B N |
| ATOM | 2785 | C | GLN | B | 309 | 47.897 | 20.064 | 20.916 | 1.00 51.53 | B C |
| ATOM | 2786 | O | GLN | B | 309 | 48.781 | 19.748 | 21.694 | 1.00 51.43 | B O |
| ATOM | 2787 | N | GLU | B | 310 | 47.279 | 19.202 | 20.118 | 1.00 51.43 | B N |
| ATOM | 2788 | CA | GLU | B | 310 | 47.551 | 17.767 | 20.111 | 1.00 51.62 | B C |
| ATOM | 2789 | CB | GLU | B | 310 | 46.606 | 17.073 | 19.108 | 1.00 54.05 | B C |
| ATOM | 2790 | CG | GLU | B | 310 | 46.483 | 17.760 | 17.701 | 1.00 57.76 | B C |
| ATOM | 2791 | CD | GLU | B | 310 | 45.200 | 18.610 | 17.488 | 1.00 59.79 | B C |
| ATOM | 2792 | OE1 | GLU | B | 310 | 44.083 | 18.112 | 17.766 | 1.00 60.93 | B O |
| ATOM | 2793 | OE2 | GLU | B | 310 | 45.306 | 19.763 | 16.998 | 1.00 60.05 | B O |
| ATOM | 2794 | C | GLU | B | 310 | 49.027 | 17.400 | 19.829 | 1.00 50.45 | B C |
| ATOM | 2795 | O | GLU | B | 310 | 49.633 | 17.929 | 18.905 | 1.00 50.30 | B O |
| ATOM | 2796 | N | PRO | B | 311 | 49.651 | 16.552 | 20.694 | 1.00 49.14 | B N |
| ATOM | 2797 | CD | PRO | B | 311 | 51.029 | 16.093 | 20.462 | 1.00 49.28 | B C |
| ATOM | 2798 | CA | PRO | B | 311 | 49.107 | 15.907 | 21.903 | 1.00 47.31 | B C |
| ATOM | 2799 | CB | PRO | B | 311 | 50.188 | 14.874 | 22.271 | 1.00 48.32 | B C |
| ATOM | 2800 | CG | PRO | B | 311 | 50.989 | 14.700 | 21.017 | 1.00 49.35 | B C |
| ATOM | 2801 | C | PRO | B | 311 | 48.913 | 16.913 | 23.046 | 1.00 44.47 | B C |
| ATOM | 2802 | O | PRO | B | 311 | 49.776 | 17.753 | 23.292 | 1.00 44.45 | B O |
| ATOM | 2803 | N | ILE | B | 312 | 47.777 | 16.816 | 23.732 | 1.00 41.83 | B N |
| ATOM | 2804 | CA | ILE | B | 312 | 47.433 | 17.703 | 24.849 | 1.00 38.24 | B C |
| ATOM | 2805 | CB | ILE | B | 312 | 45.942 | 17.541 | 25.230 | 1.00 39.46 | B C |
| ATOM | 2806 | CG2 | ILE | B | 312 | 45.522 | 18.663 | 26.145 | 1.00 38.89 | B C |
| ATOM | 2807 | CG1 | ILE | B | 312 | 45.041 | 17.455 | 23.976 | 1.00 39.99 | B C |
| ATOM | 2808 | CD1 | ILE | B | 312 | 44.981 | 18.727 | 23.140 | 1.00 39.87 | B C |
| ATOM | 2809 | C | ILE | B | 312 | 48.255 | 17.343 | 26.093 | 1.00 35.63 | B C |
| ATOM | 2810 | O | ILE | B | 312 | 48.409 | 16.169 | 26.419 | 1.00 34.66 | B O |
| ATOM | 2811 | N | TYR | B | 313 | 48.754 | 18.355 | 26.793 | 1.00 32.94 | B N |
| ATOM | 2812 | CA | TYR | B | 313 | 49.531 | 18.142 | 28.020 | 1.00 31.10 | B C |
| ATOM | 2813 | CB | TYR | B | 313 | 50.978 | 18.679 | 27.889 | 1.00 28.74 | B C |
| ATOM | 2814 | CG | TYR | B | 313 | 51.936 | 17.968 | 26.954 | 1.00 27.13 | B C |
| ATOM | 2815 | CD1 | TYR | B | 313 | 51.642 | 16.724 | 26.431 | 1.00 27.03 | B C |
| ATOM | 2816 | CE1 | TYR | B | 313 | 52.525 | 16.073 | 25.583 | 1.00 27.85 | B C |
| ATOM | 2817 | CD2 | TYR | B | 313 | 53.160 | 18.555 | 26.605 | 1.00 27.84 | B C |
| ATOM | 2818 | CE2 | TYR | B | 313 | 54.058 | 17.908 | 25.760 | 1.00 26.48 | B C |
| ATOM | 2819 | CZ | TYR | B | 313 | 53.732 | 16.670 | 25.247 | 1.00 27.57 | B C |

Figure 11

| ATOM | 2820 | OH  | TYR | B | 313 | 54.567 | 16.000 | 24.377 | 1.00 | 28.03 | B | O |
|------|------|-----|-----|---|-----|--------|--------|--------|------|-------|---|---|
| ATOM | 2821 | C   | TYR | B | 313 | 48.953 | 18.893 | 29.227 | 1.00 | 30.10 | B | C |
| ATOM | 2822 | O   | TYR | B | 313 | 48.425 | 20.006 | 29.100 | 1.00 | 28.93 | B | O |
| ATOM | 2823 | N   | ILE | B | 314 | 49.030 | 18.249 | 30.389 | 1.00 | 29.26 | B | N |
| ATOM | 2824 | CA  | ILE | B | 314 | 48.701 | 18.914 | 31.643 | 1.00 | 28.97 | B | C |
| ATOM | 2825 | CB  | ILE | B | 314 | 47.630 | 18.174 | 32.501 | 1.00 | 29.98 | B | C |
| ATOM | 2826 | CG2 | ILE | B | 314 | 47.573 | 18.804 | 33.895 | 1.00 | 28.02 | B | C |
| ATOM | 2827 | CG1 | ILE | B | 314 | 46.250 | 18.242 | 31.822 | 1.00 | 30.38 | B | C |
| ATOM | 2828 | CD1 | ILE | B | 314 | 45.253 | 17.269 | 32.433 | 1.00 | 34.31 | B | C |
| ATOM | 2829 | C   | ILE | B | 314 | 50.053 | 18.845 | 32.364 | 1.00 | 28.00 | B | C |
| ATOM | 2830 | O   | ILE | B | 314 | 50.625 | 17.776 | 32.475 | 1.00 | 28.39 | B | O |
| ATOM | 2831 | N   | ILE | B | 315 | 50.562 | 19.971 | 32.835 | 1.00 | 28.17 | B | N |
| ATOM | 2832 | CA  | ILE | B | 315 | 51.841 | 19.988 | 33.509 | 1.00 | 29.00 | B | C |
| ATOM | 2833 | CB  | ILE | B | 315 | 52.819 | 21.062 | 32.902 | 1.00 | 29.83 | B | C |
| ATOM | 2834 | CG2 | ILE | B | 315 | 54.124 | 21.135 | 33.704 | 1.00 | 28.45 | B | C |
| ATOM | 2835 | CG1 | ILE | B | 315 | 53.191 | 20.684 | 31.470 | 1.00 | 30.82 | B | C |
| ATOM | 2836 | CD1 | ILE | B | 315 | 52.508 | 21.505 | 30.402 | 1.00 | 32.58 | B | C |
| ATOM | 2837 | C   | ILE | B | 315 | 51.632 | 20.265 | 34.980 | 1.00 | 28.62 | B | C |
| ATOM | 2838 | O   | ILE | B | 315 | 51.022 | 21.257 | 35.335 | 1.00 | 29.62 | B | O |
| ATOM | 2839 | N   | THR | B | 316 | 52.130 | 19.373 | 35.834 | 1.00 | 28.05 | B | N |
| ATOM | 2840 | CA  | THR | B | 316 | 51.990 | 19.558 | 37.276 | 1.00 | 27.84 | B | C |
| ATOM | 2841 | CB  | THR | B | 316 | 51.055 | 18.517 | 37.868 | 1.00 | 27.00 | B | C |
| ATOM | 2842 | OG1 | THR | B | 316 | 51.701 | 17.236 | 37.889 | 1.00 | 23.70 | B | O |
| ATOM | 2843 | CG2 | THR | B | 316 | 49.755 | 18.426 | 37.081 | 1.00 | 26.75 | B | C |
| ATOM | 2844 | C   | THR | B | 316 | 53.331 | 19.358 | 37.997 | 1.00 | 28.83 | B | C |
| ATOM | 2845 | O   | THR | B | 316 | 54.299 | 18.864 | 37.406 | 1.00 | 29.51 | B | O |
| ATOM | 2846 | N   | GLU | B | 317 | 53.381 | 19.734 | 39.272 | 1.00 | 28.16 | B | N |
| ATOM | 2847 | CA  | GLU | B | 317 | 54.568 | 19.495 | 40.076 | 1.00 | 27.56 | B | C |
| ATOM | 2848 | CB  | GLU | B | 317 | 54.362 | 19.924 | 41.541 | 1.00 | 27.86 | B | C |
| ATOM | 2849 | CG  | GLU | B | 317 | 53.352 | 19.089 | 42.359 | 1.00 | 27.54 | B | C |
| ATOM | 2850 | CD  | GLU | B | 317 | 53.205 | 19.599 | 43.784 | 1.00 | 29.08 | B | C |
| ATOM | 2851 | OE1 | GLU | B | 317 | 52.115 | 20.077 | 44.163 | 1.00 | 29.12 | B | O |
| ATOM | 2852 | OE2 | GLU | B | 317 | 54.209 | 19.575 | 44.528 | 1.00 | 31.47 | B | O |
| ATOM | 2853 | C   | GLU | B | 317 | 54.866 | 17.995 | 40.017 | 1.00 | 27.06 | B | C |
| ATOM | 2854 | O   | GLU | B | 317 | 53.977 | 17.159 | 39.785 | 1.00 | 26.44 | B | O |
| ATOM | 2855 | N   | TYR | B | 318 | 56.136 | 17.666 | 40.215 | 1.00 | 26.95 | B | N |
| ATOM | 2856 | CA  | TYR | B | 318 | 56.572 | 16.289 | 40.162 | 1.00 | 26.66 | B | C |
| ATOM | 2857 | CB  | TYR | B | 318 | 57.952 | 16.214 | 39.460 | 1.00 | 26.15 | B | C |
| ATOM | 2858 | CG  | TYR | B | 318 | 58.555 | 14.830 | 39.387 | 1.00 | 25.50 | B | C |
| ATOM | 2859 | CD1 | TYR | B | 318 | 58.002 | 13.852 | 38.571 | 1.00 | 26.47 | B | C |
| ATOM | 2860 | CE1 | TYR | B | 318 | 58.555 | 12.538 | 38.526 | 1.00 | 26.87 | B | C |
| ATOM | 2861 | CD2 | TYR | B | 318 | 59.670 | 14.487 | 40.161 | 1.00 | 25.61 | B | C |
| ATOM | 2862 | CE2 | TYR | B | 318 | 60.219 | 13.208 | 40.125 | 1.00 | 25.46 | B | C |
| ATOM | 2863 | CZ  | TYR | B | 318 | 59.661 | 12.245 | 39.312 | 1.00 | 26.50 | B | C |
| ATOM | 2864 | OH  | TYR | B | 318 | 60.199 | 10.990 | 39.269 | 1.00 | 28.43 | B | O |
| ATOM | 2865 | C   | TYR | B | 318 | 56.593 | 15.652 | 41.555 | 1.00 | 25.84 | B | C |
| ATOM | 2866 | O   | TYR | B | 318 | 57.030 | 16.263 | 42.538 | 1.00 | 25.28 | B | O |
| ATOM | 2867 | N   | MET | B | 319 | 56.033 | 14.453 | 41.639 | 1.00 | 25.65 | B | N |
| ATOM | 2868 | CA  | MET | B | 319 | 55.965 | 13.714 | 42.900 | 1.00 | 25.82 | B | C |
| ATOM | 2869 | CB  | MET | B | 319 | 54.520 | 13.357 | 43.246 | 1.00 | 25.61 | B | C |
| ATOM | 2870 | CG  | MET | B | 319 | 53.621 | 14.561 | 43.403 | 1.00 | 24.69 | B | C |
| ATOM | 2871 | SD  | MET | B | 319 | 54.049 | 15.650 | 44.777 | 1.00 | 28.29 | B | S |
| ATOM | 2872 | CE  | MET | B | 319 | 53.521 | 14.597 | 46.170 | 1.00 | 22.23 | B | C |
| ATOM | 2873 | C   | MET | B | 319 | 56.808 | 12.468 | 42.725 | 1.00 | 26.50 | B | C |
| ATOM | 2874 | O   | MET | B | 319 | 56.385 | 11.471 | 42.147 | 1.00 | 24.50 | B | O |
| ATOM | 2875 | N   | GLU | B | 320 | 58.040 | 12.614 | 43.196 | 1.00 | 27.78 | B | N |
| ATOM | 2876 | CA  | GLU | B | 320 | 59.106 | 11.629 | 43.159 | 1.00 | 29.02 | B | C |
| ATOM | 2877 | CB  | GLU | B | 320 | 60.231 | 12.129 | 44.083 | 1.00 | 31.45 | B | C |
| ATOM | 2878 | CG  | GLU | B | 320 | 61.338 | 11.135 | 44.393 | 1.00 | 37.93 | B | C |

Figure 11

| | | | | | | | | | | | |
|---|---|---|---|---|---|---|---|---|---|---|---|
| ATOM | 2879 | CD | GLU | B | 320 | 62.559 | 11.240 | 43.472 | 1.00 | 40.21 | B C |
| ATOM | 2880 | OE1 | GLU | B | 320 | 62.765 | 12.285 | 42.799 | 1.00 | 40.49 | B O |
| ATOM | 2881 | OE2 | GLU | B | 320 | 63.328 | 10.253 | 43.454 | 1.00 | 42.86 | B O |
| ATOM | 2882 | C | GLU | B | 320 | 58.719 | 10.181 | 43.451 | 1.00 | 27.64 | B C |
| ATOM | 2883 | O | GLU | B | 320 | 59.078 | 9.268 | 42.692 | 1.00 | 27.26 | B O |
| ATOM | 2884 | N | ASN | B | 321 | 57.954 | 9.958 | 44.507 | 1.00 | 26.14 | B N |
| ATOM | 2885 | CA | ASN | B | 321 | 57.580 | 8.602 | 44.856 | 1.00 | 25.84 | B C |
| ATOM | 2886 | CB | ASN | B | 321 | 57.710 | 8.390 | 46.371 | 1.00 | 27.44 | B C |
| ATOM | 2887 | CG | ASN | B | 321 | 59.190 | 8.359 | 46.836 | 1.00 | 27.65 | B C |
| ATOM | 2888 | OD1 | ASN | B | 321 | 59.904 | 7.400 | 46.565 | 1.00 | 27.82 | B O |
| ATOM | 2889 | ND2 | ASN | B | 321 | 59.626 | 9.400 | 47.529 | 1.00 | 27.00 | B N |
| ATOM | 2890 | C | ASN | B | 321 | 56.254 | 8.081 | 44.289 | 1.00 | 26.75 | B C |
| ATOM | 2891 | O | ASN | B | 321 | 55.706 | 7.065 | 44.769 | 1.00 | 26.70 | B O |
| ATOM | 2892 | N | GLY | B | 322 | 55.740 | 8.780 | 43.269 | 1.00 | 26.18 | B N |
| ATOM | 2893 | CA | GLY | B | 322 | 54.527 | 8.345 | 42.598 | 1.00 | 25.99 | B C |
| ATOM | 2894 | C | GLY | B | 322 | 53.301 | 8.121 | 43.474 | 1.00 | 26.03 | B C |
| ATOM | 2895 | O | GLY | B | 322 | 53.089 | 8.845 | 44.445 | 1.00 | 24.47 | B O |
| ATOM | 2896 | N | SER | B | 323 | 52.537 | 7.080 | 43.158 | 1.00 | 25.45 | B N |
| ATOM | 2897 | CA | SER | B | 323 | 51.328 | 6.784 | 43.906 | 1.00 | 26.62 | B C |
| ATOM | 2898 | CB | SER | B | 323 | 50.382 | 5.939 | 43.054 | 1.00 | 27.17 | B C |
| ATOM | 2899 | OG | SER | B | 323 | 49.238 | 5.592 | 43.803 | 1.00 | 30.77 | B O |
| ATOM | 2900 | C | SER | B | 323 | 51.544 | 6.099 | 45.244 | 1.00 | 26.01 | B C |
| ATOM | 2901 | O | SER | B | 323 | 52.266 | 5.128 | 45.330 | 1.00 | 24.32 | B O |
| ATOM | 2902 | N | LEU | B | 324 | 50.807 | 6.562 | 46.254 | 1.00 | 26.52 | B N |
| ATOM | 2903 | CA | LEU | B | 324 | 50.884 | 6.010 | 47.605 | 1.00 | 26.47 | B C |
| ATOM | 2904 | CB | LEU | B | 324 | 49.953 | 6.784 | 48.560 | 1.00 | 27.38 | B C |
| ATOM | 2905 | CG | LEU | B | 324 | 49.840 | 6.338 | 50.031 | 1.00 | 27.14 | B C |
| ATOM | 2906 | CD1 | LEU | B | 324 | 51.192 | 6.518 | 50.760 | 1.00 | 25.64 | B C |
| ATOM | 2907 | CD2 | LEU | B | 324 | 48.694 | 7.124 | 50.750 | 1.00 | 25.45 | B C |
| ATOM | 2908 | C | LEU | B | 324 | 50.595 | 4.516 | 47.688 | 1.00 | 26.34 | B C |
| ATOM | 2909 | O | LEU | B | 324 | 51.318 | 3.798 | 48.380 | 1.00 | 26.90 | B O |
| ATOM | 2910 | N | VAL | B | 325 | 49.579 | 4.027 | 46.973 | 1.00 | 25.75 | B N |
| ATOM | 2911 | CA | VAL | B | 325 | 49.267 | 2.610 | 47.033 | 1.00 | 24.65 | B C |
| ATOM | 2912 | CB | VAL | B | 325 | 47.908 | 2.275 | 46.324 | 1.00 | 24.12 | B C |
| ATOM | 2913 | CG1 | VAL | B | 325 | 48.055 | 2.172 | 44.856 | 1.00 | 21.26 | B C |
| ATOM | 2914 | CG2 | VAL | B | 325 | 47.300 | 0.986 | 46.905 | 1.00 | 23.50 | B C |
| ATOM | 2915 | C | VAL | B | 325 | 50.439 | 1.762 | 46.537 | 1.00 | 25.65 | B C |
| ATOM | 2916 | O | VAL | B | 325 | 50.646 | 0.642 | 46.996 | 1.00 | 25.07 | B O |
| ATOM | 2917 | N | ASP | B | 326 | 51.223 | 2.317 | 45.618 | 1.00 | 26.73 | B N |
| ATOM | 2918 | CA | ASP | B | 326 | 52.411 | 1.624 | 45.101 | 1.00 | 28.09 | B C |
| ATOM | 2919 | CB | ASP | B | 326 | 52.831 | 2.194 | 43.753 | 1.00 | 27.54 | B C |
| ATOM | 2920 | CG | ASP | B | 326 | 51.831 | 1.919 | 42.661 | 1.00 | 27.17 | B C |
| ATOM | 2921 | OD1 | ASP | B | 326 | 51.252 | 0.813 | 42.624 | 1.00 | 27.97 | B O |
| ATOM | 2922 | OD2 | ASP | B | 326 | 51.677 | 2.804 | 41.811 | 1.00 | 26.61 | B O |
| ATOM | 2923 | C | ASP | B | 326 | 53.590 | 1.819 | 46.055 | 1.00 | 28.13 | B C |
| ATOM | 2924 | O | ASP | B | 326 | 54.317 | 0.873 | 46.343 | 1.00 | 28.36 | B O |
| ATOM | 2925 | N | PHE | B | 327 | 53.753 | 3.045 | 46.557 | 1.00 | 28.42 | B N |
| ATOM | 2926 | CA | PHE | B | 327 | 54.860 | 3.368 | 47.446 | 1.00 | 29.98 | B C |
| ATOM | 2927 | CB | PHE | B | 327 | 54.912 | 4.852 | 47.769 | 1.00 | 30.18 | B C |
| ATOM | 2928 | CG | PHE | B | 327 | 56.007 | 5.202 | 48.735 | 1.00 | 33.25 | B C |
| ATOM | 2929 | CD1 | PHE | B | 327 | 57.346 | 5.110 | 48.348 | 1.00 | 32.77 | B C |
| ATOM | 2930 | CD2 | PHE | B | 327 | 55.712 | 5.549 | 50.052 | 1.00 | 32.96 | B C |
| ATOM | 2931 | CE1 | PHE | B | 327 | 58.370 | 5.349 | 49.256 | 1.00 | 33.03 | B C |
| ATOM | 2932 | CE2 | PHE | B | 327 | 56.738 | 5.793 | 50.965 | 1.00 | 34.31 | B C |
| ATOM | 2933 | CZ | PHE | B | 327 | 58.065 | 5.691 | 50.567 | 1.00 | 33.09 | B C |
| ATOM | 2934 | C | PHE | B | 327 | 54.890 | 2.567 | 48.743 | 1.00 | 31.18 | B C |
| ATOM | 2935 | O | PHE | B | 327 | 55.957 | 2.166 | 49.204 | 1.00 | 31.75 | B O |
| ATOM | 2936 | N | LEU | B | 328 | 53.715 | 2.350 | 49.329 | 1.00 | 30.79 | B N |
| ATOM | 2937 | CA | LEU | B | 328 | 53.597 | 1.602 | 50.560 | 1.00 | 30.84 | B C |

Figure 11

| | | | | | | | | | | | |
|---|---|---|---|---|---|---|---|---|---|---|---|
| ATOM | 2938 | CB  | LEU | B | 328 | 52.134 | 1.540  | 51.000 | 1.00 | 30.06 | B C |
| ATOM | 2939 | CG  | LEU | B | 328 | 51.485 | 2.848  | 51.444 | 1.00 | 28.88 | B C |
| ATOM | 2940 | CD1 | LEU | B | 328 | 50.020 | 2.630  | 51.711 | 1.00 | 29.07 | B C |
| ATOM | 2941 | CD2 | LEU | B | 328 | 52.198 | 3.380  | 52.656 | 1.00 | 28.70 | B C |
| ATOM | 2942 | C   | LEU | B | 328 | 54.129 | 0.191  | 50.398 | 1.00 | 31.99 | B C |
| ATOM | 2943 | O   | LEU | B | 328 | 54.599 | -0.400 | 51.365 | 1.00 | 32.18 | B O |
| ATOM | 2944 | N   | LYS | B | 329 | 54.050 | -0.337 | 49.172 | 1.00 | 33.22 | B N |
| ATOM | 2945 | CA  | LYS | B | 329 | 54.490 | -1.696 | 48.875 | 1.00 | 34.33 | B C |
| ATOM | 2946 | CB  | LYS | B | 329 | 53.669 | -2.281 | 47.719 | 1.00 | 34.79 | B C |
| ATOM | 2947 | CG  | LYS | B | 329 | 52.196 | -2.480 | 48.008 | 1.00 | 35.10 | B C |
| ATOM | 2948 | CD  | LYS | B | 329 | 51.578 | -3.389 | 46.951 | 1.00 | 34.82 | B C |
| ATOM | 2949 | CE  | LYS | B | 329 | 50.088 | -3.201 | 46.844 | 1.00 | 34.35 | B C |
| ATOM | 2950 | NZ  | LYS | B | 329 | 49.809 | -1.788 | 46.491 | 1.00 | 36.19 | B N |
| ATOM | 2951 | C   | LYS | B | 329 | 55.992 | -1.887 | 48.596 | 1.00 | 34.73 | B C |
| ATOM | 2952 | O   | LYS | B | 329 | 56.468 | -3.029 | 48.547 | 1.00 | 34.93 | B O |
| ATOM | 2953 | N   | THR | B | 330 | 56.728 | -0.783 | 48.454 | 1.00 | 34.94 | B N |
| ATOM | 2954 | CA  | THR | B | 330 | 58.170 | -0.821 | 48.186 | 1.00 | 35.57 | B C |
| ATOM | 2955 | CB  | THR | B | 330 | 58.703 | 0.533  | 47.637 | 1.00 | 34.05 | B C |
| ATOM | 2956 | OG1 | THR | B | 330 | 58.646 | 1.534  | 48.658 | 1.00 | 33.94 | B O |
| ATOM | 2957 | CG2 | THR | B | 330 | 57.935 | 1.004  | 46.426 | 1.00 | 34.84 | B C |
| ATOM | 2958 | C   | THR | B | 330 | 58.963 | -1.096 | 49.461 | 1.00 | 36.52 | B C |
| ATOM | 2959 | O   | THR | B | 330 | 58.465 | -0.890 | 50.558 | 1.00 | 36.94 | B O |
| ATOM | 2960 | N   | PRO | B | 331 | 60.209 | -1.580 | 49.329 | 1.00 | 37.63 | B N |
| ATOM | 2961 | CD  | PRO | B | 331 | 60.829 | -2.169 | 48.121 | 1.00 | 38.09 | B C |
| ATOM | 2962 | CA  | PRO | B | 331 | 61.020 | -1.850 | 50.518 | 1.00 | 38.08 | B C |
| ATOM | 2963 | CB  | PRO | B | 331 | 62.415 | -2.083 | 49.925 | 1.00 | 38.24 | B C |
| ATOM | 2964 | CG  | PRO | B | 331 | 62.087 | -2.897 | 48.685 | 1.00 | 37.26 | B C |
| ATOM | 2965 | C   | PRO | B | 331 | 60.988 | -0.679 | 51.501 | 1.00 | 39.24 | B C |
| ATOM | 2966 | O   | PRO | B | 331 | 60.839 | -0.900 | 52.697 | 1.00 | 39.73 | B O |
| ATOM | 2967 | N   | SER | B | 332 | 61.069 | 0.559  | 51.002 | 1.00 | 39.87 | B N |
| ATOM | 2968 | CA  | SER | B | 332 | 61.017 | 1.753  | 51.862 | 1.00 | 41.43 | B C |
| ATOM | 2969 | CB  | SER | B | 332 | 61.268 | 3.047  | 51.073 | 1.00 | 42.10 | B C |
| ATOM | 2970 | OG  | SER | B | 332 | 62.549 | 3.077  | 50.500 | 1.00 | 44.13 | B O |
| ATOM | 2971 | C   | SER | B | 332 | 59.644 | 1.909  | 52.528 | 1.00 | 41.59 | B C |
| ATOM | 2972 | O   | SER | B | 332 | 59.547 | 2.279  | 53.708 | 1.00 | 41.87 | B O |
| ATOM | 2973 | N   | GLY | B | 333 | 58.600 | 1.715  | 51.719 | 1.00 | 41.10 | B N |
| ATOM | 2974 | CA  | GLY | B | 333 | 57.231 | 1.832  | 52.187 | 1.00 | 40.99 | B C |
| ATOM | 2975 | C   | GLY | B | 333 | 56.926 | 0.818  | 53.260 | 1.00 | 40.32 | B C |
| ATOM | 2976 | O   | GLY | B | 333 | 56.425 | 1.173  | 54.315 | 1.00 | 40.07 | B O |
| ATOM | 2977 | N   | ILE | B | 334 | 57.317 | -0.423 | 53.014 | 1.00 | 40.61 | B N |
| ATOM | 2978 | CA  | ILE | B | 334 | 57.121 | -1.527 | 53.948 | 1.00 | 41.13 | B C |
| ATOM | 2979 | CB  | ILE | B | 334 | 57.737 | -2.819 | 53.371 | 1.00 | 41.74 | B C |
| ATOM | 2980 | CG2 | ILE | B | 334 | 57.898 | -3.896 | 54.442 | 1.00 | 42.17 | B C |
| ATOM | 2981 | CG1 | ILE | B | 334 | 56.870 | -3.325 | 52.219 | 1.00 | 42.52 | B C |
| ATOM | 2982 | CD1 | ILE | B | 334 | 55.476 | -3.787 | 52.621 | 1.00 | 44.13 | B C |
| ATOM | 2983 | C   | ILE | B | 334 | 57.725 | -1.240 | 55.322 | 1.00 | 41.23 | B C |
| ATOM | 2984 | O   | ILE | B | 334 | 57.194 | -1.691 | 56.339 | 1.00 | 41.33 | B O |
| ATOM | 2985 | N   | LYS | B | 335 | 58.800 | -0.450 | 55.346 | 1.00 | 40.80 | B N |
| ATOM | 2986 | CA  | LYS | B | 335 | 59.503 | -0.104 | 56.583 | 1.00 | 40.26 | B C |
| ATOM | 2987 | CB  | LYS | B | 335 | 60.988 | 0.169  | 56.294 | 1.00 | 42.30 | B C |
| ATOM | 2988 | CG  | LYS | B | 335 | 61.779 | -1.033 | 55.798 | 1.00 | 44.83 | B C |
| ATOM | 2989 | CD  | LYS | B | 335 | 63.120 | -0.542 | 55.195 | 1.00 | 47.87 | B C |
| ATOM | 2990 | CE  | LYS | B | 335 | 63.803 | -1.632 | 54.353 | 1.00 | 49.52 | B C |
| ATOM | 2991 | NZ  | LYS | B | 335 | 64.610 | -1.022 | 53.226 | 1.00 | 51.07 | B N |
| ATOM | 2992 | C   | LYS | B | 335 | 58.957 | 1.101  | 57.334 | 1.00 | 38.96 | B C |
| ATOM | 2993 | O   | LYS | B | 335 | 59.455 | 1.421  | 58.418 | 1.00 | 38.38 | B O |
| ATOM | 2994 | N   | LEU | B | 336 | 57.988 | 1.810  | 56.751 | 1.00 | 37.03 | B N |
| ATOM | 2995 | CA  | LEU | B | 336 | 57.423 | 2.990  | 57.424 | 1.00 | 35.36 | B C |
| ATOM | 2996 | CB  | LEU | B | 336 | 56.393 | 3.694  | 56.531 | 1.00 | 34.99 | B C |

Figure 11

| | | | | | | | | | | | |
|---|---|---|---|---|---|---|---|---|---|---|---|
| ATOM | 2997 | CG | LEU | B | 336 | 56.996 | 4.380 | 55.292 | 1.00 | 33.42 | B C |
| ATOM | 2998 | CD1 | LEU | B | 336 | 55.898 | 5.108 | 54.552 | 1.00 | 32.84 | B C |
| ATOM | 2999 | CD2 | LEU | B | 336 | 58.105 | 5.349 | 55.685 | 1.00 | 32.63 | B C |
| ATOM | 3000 | C | LEU | B | 336 | 56.830 | 2.694 | 58.805 | 1.00 | 34.10 | B C |
| ATOM | 3001 | O | LEU | B | 336 | 56.171 | 1.661 | 59.014 | 1.00 | 33.29 | B O |
| ATOM | 3002 | N | THR | B | 337 | 57.111 | 3.585 | 59.754 | 1.00 | 33.89 | B N |
| ATOM | 3003 | CA | THR | B | 337 | 56.622 | 3.430 | 61.129 | 1.00 | 33.54 | B C |
| ATOM | 3004 | CB | THR | B | 337 | 57.492 | 4.226 | 62.204 | 1.00 | 34.08 | B C |
| ATOM | 3005 | OG1 | THR | B | 337 | 57.312 | 5.642 | 62.068 | 1.00 | 32.82 | B O |
| ATOM | 3006 | CG2 | THR | B | 337 | 58.990 | 3.874 | 62.089 | 1.00 | 33.91 | B C |
| ATOM | 3007 | C | THR | B | 337 | 55.169 | 3.883 | 61.229 | 1.00 | 33.51 | B C |
| ATOM | 3008 | O | THR | B | 337 | 54.707 | 4.695 | 60.406 | 1.00 | 33.06 | B O |
| ATOM | 3009 | N | ILE | B | 338 | 54.468 | 3.391 | 62.257 | 1.00 | 33.60 | B N |
| ATOM | 3010 | CA | ILE | B | 338 | 53.071 | 3.754 | 62.478 | 1.00 | 32.47 | B C |
| ATOM | 3011 | CB | ILE | B | 338 | 52.445 | 3.000 | 63.687 | 1.00 | 33.36 | B C |
| ATOM | 3012 | CG2 | ILE | B | 338 | 53.208 | 3.326 | 64.981 | 1.00 | 34.37 | B C |
| ATOM | 3013 | CG1 | ILE | B | 338 | 50.966 | 3.390 | 63.866 | 1.00 | 33.99 | B C |
| ATOM | 3014 | CD1 | ILE | B | 338 | 50.041 | 3.011 | 62.715 | 1.00 | 31.86 | B C |
| ATOM | 3015 | C | ILE | B | 338 | 53.004 | 5.245 | 62.679 | 1.00 | 31.58 | B C |
| ATOM | 3016 | O | ILE | B | 338 | 52.050 | 5.890 | 62.269 | 1.00 | 31.48 | B O |
| ATOM | 3017 | N | ASN | B | 339 | 54.053 | 5.804 | 63.264 | 1.00 | 32.16 | B N |
| ATOM | 3018 | CA | ASN | B | 339 | 54.119 | 7.246 | 63.490 | 1.00 | 32.24 | B C |
| ATOM | 3019 | CB | ASN | B | 339 | 55.389 | 7.587 | 64.263 | 1.00 | 33.20 | B C |
| ATOM | 3020 | CG | ASN | B | 339 | 55.396 | 6.966 | 65.624 | 1.00 | 34.07 | B C |
| ATOM | 3021 | OD1 | ASN | B | 339 | 55.068 | 7.620 | 66.613 | 1.00 | 34.17 | B O |
| ATOM | 3022 | ND2 | ASN | B | 339 | 55.704 | 5.681 | 65.681 | 1.00 | 32.91 | B N |
| ATOM | 3023 | C | ASN | B | 339 | 54.120 | 8.021 | 62.182 | 1.00 | 31.06 | B C |
| ATOM | 3024 | O | ASN | B | 339 | 53.529 | 9.099 | 62.085 | 1.00 | 30.09 | B O |
| ATOM | 3025 | N | LYS | B | 340 | 54.882 | 7.510 | 61.219 | 1.00 | 31.01 | B N |
| ATOM | 3026 | CA | LYS | B | 340 | 54.973 | 8.148 | 59.904 | 1.00 | 30.61 | B C |
| ATOM | 3027 | CB | LYS | B | 340 | 56.182 | 7.589 | 59.126 | 1.00 | 31.44 | B C |
| ATOM | 3028 | CG | LYS | B | 340 | 56.295 | 8.046 | 57.675 | 1.00 | 33.52 | B C |
| ATOM | 3029 | CD | LYS | B | 340 | 56.617 | 9.546 | 57.550 | 1.00 | 34.71 | B C |
| ATOM | 3030 | CE | LYS | B | 340 | 56.273 | 10.062 | 56.129 | 1.00 | 36.49 | B C |
| ATOM | 3031 | NZ | LYS | B | 340 | 56.424 | 11.552 | 55.962 | 1.00 | 37.36 | B N |
| ATOM | 3032 | C | LYS | B | 340 | 53.656 | 7.895 | 59.121 | 1.00 | 28.96 | B C |
| ATOM | 3033 | O | LYS | B | 340 | 53.170 | 8.767 | 58.423 | 1.00 | 28.15 | B O |
| ATOM | 3034 | N | LEU | B | 341 | 53.079 | 6.711 | 59.277 | 1.00 | 28.09 | B N |
| ATOM | 3035 | CA | LEU | B | 341 | 51.845 | 6.360 | 58.582 | 1.00 | 28.79 | B C |
| ATOM | 3036 | CB | LEU | B | 341 | 51.486 | 4.911 | 58.872 | 1.00 | 27.67 | B C |
| ATOM | 3037 | CG | LEU | B | 341 | 52.491 | 3.907 | 58.325 | 1.00 | 27.17 | B C |
| ATOM | 3038 | CD1 | LEU | B | 341 | 52.040 | 2.490 | 58.641 | 1.00 | 25.23 | B C |
| ATOM | 3039 | CD2 | LEU | B | 341 | 52.633 | 4.132 | 56.824 | 1.00 | 26.50 | B C |
| ATOM | 3040 | C | LEU | B | 341 | 50.706 | 7.294 | 58.989 | 1.00 | 28.96 | B C |
| ATOM | 3041 | O | LEU | B | 341 | 49.990 | 7.827 | 58.150 | 1.00 | 29.31 | B O |
| ATOM | 3042 | N | LEU | B | 342 | 50.608 | 7.570 | 60.279 | 1.00 | 29.67 | B N |
| ATOM | 3043 | CA | LEU | B | 342 | 49.577 | 8.460 | 60.748 | 1.00 | 29.85 | B C |
| ATOM | 3044 | CB | LEU | B | 342 | 49.378 | 8.304 | 62.256 | 1.00 | 31.05 | B C |
| ATOM | 3045 | CG | LEU | B | 342 | 48.900 | 6.860 | 62.507 | 1.00 | 32.75 | B C |
| ATOM | 3046 | CD1 | LEU | B | 342 | 48.166 | 6.738 | 63.800 | 1.00 | 33.63 | B C |
| ATOM | 3047 | CD2 | LEU | B | 342 | 47.972 | 6.401 | 61.382 | 1.00 | 33.96 | B C |
| ATOM | 3048 | C | LEU | B | 342 | 49.843 | 9.888 | 60.332 | 1.00 | 30.25 | B C |
| ATOM | 3049 | O | LEU | B | 342 | 48.906 | 10.640 | 60.093 | 1.00 | 30.49 | B O |
| ATOM | 3050 | N | ASP | B | 343 | 51.113 | 10.281 | 60.224 | 1.00 | 29.91 | B N |
| ATOM | 3051 | CA | ASP | B | 343 | 51.389 | 11.639 | 59.802 | 1.00 | 29.61 | B C |
| ATOM | 3052 | CB | ASP | B | 343 | 52.845 | 12.035 | 59.948 | 1.00 | 32.29 | B C |
| ATOM | 3053 | CG | ASP | B | 343 | 53.015 | 13.542 | 59.866 | 1.00 | 36.57 | B C |
| ATOM | 3054 | OD1 | ASP | B | 343 | 52.365 | 14.257 | 60.688 | 1.00 | 41.28 | B O |
| ATOM | 3055 | OD2 | ASP | B | 343 | 53.720 | 14.033 | 58.958 | 1.00 | 37.27 | B O |

Figure 11

| ATOM | 3056 | C | ASP | B | 343 | 50.974 | 11.802 | 58.358 | 1.00 | 28.13 | B | C |
| ATOM | 3057 | O | ASP | B | 343 | 50.564 | 12.876 | 57.950 | 1.00 | 27.64 | B | O |
| ATOM | 3058 | N | MET | B | 344 | 51.154 | 10.746 | 57.573 | 1.00 | 27.89 | B | N |
| ATOM | 3059 | CA | MET | B | 344 | 50.743 | 10.765 | 56.180 | 1.00 | 27.55 | B | C |
| ATOM | 3060 | CB | MET | B | 344 | 51.286 | 9.533 | 55.462 | 1.00 | 28.68 | B | C |
| ATOM | 3061 | CG | MET | B | 344 | 52.796 | 9.562 | 55.327 | 1.00 | 30.23 | B | C |
| ATOM | 3062 | SD | MET | B | 344 | 53.403 | 8.021 | 54.677 | 1.00 | 35.73 | B | S |
| ATOM | 3063 | CE | MET | B | 344 | 53.841 | 8.490 | 52.962 | 1.00 | 33.95 | B | C |
| ATOM | 3064 | C | MET | B | 344 | 49.207 | 10.859 | 56.067 | 1.00 | 26.22 | B | C |
| ATOM | 3065 | O | MET | B | 344 | 48.682 | 11.639 | 55.274 | 1.00 | 26.43 | B | O |
| ATOM | 3066 | N | ALA | B | 345 | 48.505 | 10.074 | 56.881 | 1.00 | 25.08 | B | N |
| ATOM | 3067 | CA | ALA | B | 345 | 47.045 | 10.086 | 56.925 | 1.00 | 24.03 | B | C |
| ATOM | 3068 | CB | ALA | B | 345 | 46.549 | 9.034 | 57.930 | 1.00 | 23.54 | B | C |
| ATOM | 3069 | C | ALA | B | 345 | 46.555 | 11.484 | 57.310 | 1.00 | 23.14 | B | C |
| ATOM | 3070 | O | ALA | B | 345 | 45.599 | 11.980 | 56.721 | 1.00 | 23.31 | B | O |
| ATOM | 3071 | N | ALA | B | 346 | 47.284 | 12.155 | 58.208 | 1.00 | 22.94 | B | N |
| ATOM | 3072 | CA | ALA | B | 346 | 46.957 | 13.503 | 58.670 | 1.00 | 23.43 | B | C |
| ATOM | 3073 | CB | ALA | B | 346 | 47.881 | 13.892 | 59.827 | 1.00 | 23.44 | B | C |
| ATOM | 3074 | C | ALA | B | 346 | 47.105 | 14.514 | 57.549 | 1.00 | 24.01 | B | C |
| ATOM | 3075 | O | ALA | B | 346 | 46.393 | 15.523 | 57.472 | 1.00 | 23.11 | B | O |
| ATOM | 3076 | N | GLN | B | 347 | 48.137 | 14.322 | 56.744 | 1.00 | 24.81 | B | N |
| ATOM | 3077 | CA | GLN | B | 347 | 48.329 | 15.213 | 55.616 | 1.00 | 24.61 | B | C |
| ATOM | 3078 | CB | GLN | B | 347 | 49.636 | 14.860 | 54.891 | 1.00 | 26.77 | B | C |
| ATOM | 3079 | CG | GLN | B | 347 | 50.867 | 15.266 | 55.687 | 1.00 | 29.62 | B | C |
| ATOM | 3080 | CD | GLN | B | 347 | 52.158 | 14.985 | 54.957 | 1.00 | 32.50 | B | C |
| ATOM | 3081 | OE1 | GLN | B | 347 | 52.928 | 15.912 | 54.688 | 1.00 | 34.38 | B | O |
| ATOM | 3082 | NE2 | GLN | B | 347 | 52.400 | 13.719 | 54.617 | 1.00 | 32.87 | B | N |
| ATOM | 3083 | C | GLN | B | 347 | 47.145 | 15.116 | 54.650 | 1.00 | 22.11 | B | C |
| ATOM | 3084 | O | GLN | B | 347 | 46.687 | 16.132 | 54.175 | 1.00 | 22.62 | B | O |
| ATOM | 3085 | N | ILE | B | 348 | 46.694 | 13.902 | 54.354 | 1.00 | 20.18 | B | N |
| ATOM | 3086 | CA | ILE | B | 348 | 45.586 | 13.678 | 53.414 | 1.00 | 20.70 | B | C |
| ATOM | 3087 | CB | ILE | B | 348 | 45.438 | 12.167 | 53.090 | 1.00 | 19.76 | B | C |
| ATOM | 3088 | CG2 | ILE | B | 348 | 44.324 | 11.945 | 52.095 | 1.00 | 18.73 | B | C |
| ATOM | 3089 | CG1 | ILE | B | 348 | 46.744 | 11.642 | 52.495 | 1.00 | 19.17 | B | C |
| ATOM | 3090 | CD1 | ILE | B | 348 | 46.900 | 10.137 | 52.486 | 1.00 | 18.21 | B | C |
| ATOM | 3091 | C | ILE | B | 348 | 44.285 | 14.238 | 54.003 | 1.00 | 21.24 | B | C |
| ATOM | 3092 | O | ILE | B | 348 | 43.495 | 14.884 | 53.317 | 1.00 | 21.25 | B | O |
| ATOM | 3093 | N | ALA | B | 349 | 44.102 | 14.041 | 55.309 | 1.00 | 22.30 | B | N |
| ATOM | 3094 | CA | ALA | B | 349 | 42.922 | 14.558 | 55.989 | 1.00 | 21.54 | B | C |
| ATOM | 3095 | CB | ALA | B | 349 | 42.905 | 14.076 | 57.390 | 1.00 | 21.54 | B | C |
| ATOM | 3096 | C | ALA | B | 349 | 42.981 | 16.090 | 55.935 | 1.00 | 21.70 | B | C |
| ATOM | 3097 | O | ALA | B | 349 | 41.967 | 16.744 | 55.724 | 1.00 | 21.14 | B | O |
| ATOM | 3098 | N | GLU | B | 350 | 44.180 | 16.665 | 56.040 | 1.00 | 21.99 | B | N |
| ATOM | 3099 | CA | GLU | B | 350 | 44.310 | 18.121 | 55.978 | 1.00 | 22.46 | B | C |
| ATOM | 3100 | CB | GLU | B | 350 | 45.750 | 18.560 | 56.308 | 1.00 | 23.50 | B | C |
| ATOM | 3101 | CG | GLU | B | 350 | 45.966 | 20.046 | 56.181 | 1.00 | 24.57 | B | C |
| ATOM | 3102 | CD | GLU | B | 350 | 47.412 | 20.493 | 56.360 | 1.00 | 25.14 | B | C |
| ATOM | 3103 | OE1 | GLU | B | 350 | 48.305 | 19.661 | 56.594 | 1.00 | 25.55 | B | O |
| ATOM | 3104 | OE2 | GLU | B | 350 | 47.652 | 21.705 | 56.238 | 1.00 | 26.87 | B | O |
| ATOM | 3105 | C | GLU | B | 350 | 43.857 | 18.651 | 54.604 | 1.00 | 22.48 | B | C |
| ATOM | 3106 | O | GLU | B | 350 | 43.126 | 19.643 | 54.503 | 1.00 | 21.50 | B | O |
| ATOM | 3107 | N | GLY | B | 351 | 44.273 | 17.962 | 53.544 | 1.00 | 22.85 | B | N |
| ATOM | 3108 | CA | GLY | B | 351 | 43.866 | 18.363 | 52.203 | 1.00 | 21.18 | B | C |
| ATOM | 3109 | C | GLY | B | 351 | 42.371 | 18.189 | 52.043 | 1.00 | 19.83 | B | C |
| ATOM | 3110 | O | GLY | B | 351 | 41.705 | 19.063 | 51.470 | 1.00 | 19.88 | B | O |
| ATOM | 3111 | N | MET | B | 352 | 41.837 | 17.093 | 52.577 | 1.00 | 19.98 | B | N |
| ATOM | 3112 | CA | MET | B | 352 | 40.387 | 16.829 | 52.507 | 1.00 | 21.29 | B | C |
| ATOM | 3113 | CB | MET | B | 352 | 40.047 | 15.414 | 52.964 | 1.00 | 20.74 | B | C |
| ATOM | 3114 | CG | MET | B | 352 | 40.422 | 14.321 | 51.911 | 1.00 | 21.87 | B | C |

Figure 11

```
ATOM   3115  SD   MET B 352      39.738  14.580  50.195  1.00 22.93      B    S
ATOM   3116  CE   MET B 352      38.017  15.121  50.523  1.00 21.09      B    C
ATOM   3117  C    MET B 352      39.633  17.859  53.337  1.00 23.24      B    C
ATOM   3118  O    MET B 352      38.528  18.289  52.951  1.00 23.68      B    O
ATOM   3119  N    ALA B 353      40.263  18.335  54.419  1.00 23.10      B    N
ATOM   3120  CA   ALA B 353      39.629  19.358  55.215  1.00 24.51      B    C
ATOM   3121  CB   ALA B 353      40.387  19.585  56.518  1.00 24.95      B    C
ATOM   3122  C    ALA B 353      39.538  20.657  54.386  1.00 25.05      B    C
ATOM   3123  O    ALA B 353      38.574  21.415  54.512  1.00 23.90      B    O
ATOM   3124  N    PHE B 354      40.525  20.918  53.522  1.00 26.03      B    N
ATOM   3125  CA   PHE B 354      40.449  22.115  52.689  1.00 26.98      B    C
ATOM   3126  CB   PHE B 354      41.749  22.376  51.956  1.00 29.54      B    C
ATOM   3127  CG   PHE B 354      41.750  23.657  51.150  1.00 31.91      B    C
ATOM   3128  CD1  PHE B 354      41.490  24.881  51.762  1.00 32.93      B    C
ATOM   3129  CD2  PHE B 354      42.132  23.649  49.807  1.00 32.25      B    C
ATOM   3130  CE1  PHE B 354      41.628  26.070  51.057  1.00 33.49      B    C
ATOM   3131  CE2  PHE B 354      42.275  24.833  49.099  1.00 32.58      B    C
ATOM   3132  CZ   PHE B 354      42.024  26.046  49.726  1.00 33.82      B    C
ATOM   3133  C    PHE B 354      39.350  21.931  51.664  1.00 27.20      B    C
ATOM   3134  O    PHE B 354      38.605  22.847  51.408  1.00 28.03      B    O
ATOM   3135  N    ILE B 355      39.281  20.753  51.053  1.00 27.11      B    N
ATOM   3136  CA   ILE B 355      38.236  20.436  50.066  1.00 27.48      B    C
ATOM   3137  CB   ILE B 355      38.471  19.012  49.472  1.00 24.81      B    C
ATOM   3138  CG2  ILE B 355      37.230  18.462  48.748  1.00 25.87      B    C
ATOM   3139  CG1  ILE B 355      39.703  19.068  48.552  1.00 23.32      B    C
ATOM   3140  CD1  ILE B 355      40.266  17.778  48.171  1.00 21.87      B    C
ATOM   3141  C    ILE B 355      36.829  20.624  50.700  1.00 28.56      B    C
ATOM   3142  O    ILE B 355      35.995  21.318  50.136  1.00 28.87      B    O
ATOM   3143  N    GLU B 356      36.635  20.110  51.912  1.00 29.70      B    N
ATOM   3144  CA   GLU B 356      35.370  20.230  52.664  1.00 31.09      B    C
ATOM   3145  CB   GLU B 356      35.571  19.531  54.011  1.00 30.75      B    C
ATOM   3146  CG   GLU B 356      34.396  19.489  55.005  1.00 29.68      B    C
ATOM   3147  CD   GLU B 356      34.729  18.559  56.164  1.00 29.76      B    C
ATOM   3148  OE1  GLU B 356      35.446  18.984  57.114  1.00 31.33      B    O
ATOM   3149  OE2  GLU B 356      34.392  17.364  56.078  1.00 27.55      B    O
ATOM   3150  C    GLU B 356      34.993  21.713  52.888  1.00 32.36      B    C
ATOM   3151  O    GLU B 356      33.891  22.178  52.563  1.00 32.91      B    O
ATOM   3152  N    GLU B 357      35.945  22.447  53.438  1.00 33.57      B    N
ATOM   3153  CA   GLU B 357      35.838  23.863  53.731  1.00 34.52      B    C
ATOM   3154  CB   GLU B 357      37.221  24.288  54.224  1.00 36.89      B    C
ATOM   3155  CG   GLU B 357      37.623  25.690  53.919  1.00 41.56      B    C
ATOM   3156  CD   GLU B 357      37.061  26.613  54.910  1.00 44.36      B    C
ATOM   3157  OE1  GLU B 357      37.295  26.358  56.107  1.00 47.90      B    O
ATOM   3158  OE2  GLU B 357      36.392  27.581  54.507  1.00 46.86      B    O
ATOM   3159  C    GLU B 357      35.389  24.698  52.516  1.00 34.66      B    C
ATOM   3160  O    GLU B 357      34.521  25.588  52.623  1.00 33.63      B    O
ATOM   3161  N    ARG B 358      35.935  24.366  51.354  1.00 34.81      B    N
ATOM   3162  CA   ARG B 358      35.611  25.090  50.132  1.00 36.50      B    C
ATOM   3163  CB   ARG B 358      36.858  25.161  49.254  1.00 39.16      B    C
ATOM   3164  CG   ARG B 358      38.078  25.797  49.949  1.00 43.64      B    C
ATOM   3165  CD   ARG B 358      37.965  27.327  50.170  1.00 47.24      B    C
ATOM   3166  NE   ARG B 358      37.812  28.035  48.897  1.00 52.52      B    N
ATOM   3167  CZ   ARG B 358      38.722  28.045  47.918  1.00 55.90      B    C
ATOM   3168  NH1  ARG B 358      39.879  27.397  48.058  1.00 58.08      B    N
ATOM   3169  NH2  ARG B 358      38.442  28.609  46.745  1.00 57.36      B    N
ATOM   3170  C    ARG B 358      34.415  24.515  49.358  1.00 35.80      B    C
ATOM   3171  O    ARG B 358      34.178  24.888  48.218  1.00 35.36      B    O
ATOM   3172  N    ASN B 359      33.663  23.625  50.009  1.00 35.24      B    N
ATOM   3173  CA   ASN B 359      32.472  22.967  49.460  1.00 35.04      B    C
```

Figure 11

```
ATOM  3174  CB   ASN B 359    31.260  23.920  49.459  1.00 36.43      B  C
ATOM  3175  CG   ASN B 359    31.080  24.662  50.824  1.00 39.78      B  C
ATOM  3176  OD1  ASN B 359    30.854  24.038  51.889  1.00 40.57      B  O
ATOM  3177  ND2  ASN B 359    31.215  25.995  50.790  1.00 39.55      B  N
ATOM  3178  C    ASN B 359    32.635  22.223  48.124  1.00 34.05      B  C
ATOM  3179  O    ASN B 359    31.802  22.281  47.216  1.00 33.05      B  O
ATOM  3180  N    TYR B 360    33.712  21.466  48.046  1.00 33.19      B  N
ATOM  3181  CA   TYR B 360    33.996  20.653  46.881  1.00 32.84      B  C
ATOM  3182  CB   TYR B 360    35.439  20.886  46.402  1.00 35.14      B  C
ATOM  3183  CG   TYR B 360    35.633  22.004  45.407  1.00 37.27      B  C
ATOM  3184  CD1  TYR B 360    35.604  23.342  45.808  1.00 38.05      B  C
ATOM  3185  CE1  TYR B 360    35.796  24.367  44.895  1.00 38.93      B  C
ATOM  3186  CD2  TYR B 360    35.861  21.719  44.060  1.00 38.72      B  C
ATOM  3187  CE2  TYR B 360    36.050  22.738  43.130  1.00 39.73      B  C
ATOM  3188  CZ   TYR B 360    36.012  24.054  43.551  1.00 40.43      B  C
ATOM  3189  OH   TYR B 360    36.121  25.053  42.605  1.00 42.35      B  O
ATOM  3190  C    TYR B 360    33.954  19.234  47.383  1.00 31.63      B  C
ATOM  3191  O    TYR B 360    33.913  19.007  48.584  1.00 30.34      B  O
ATOM  3192  N    ILE B 361    33.943  18.273  46.467  1.00 30.78      B  N
ATOM  3193  CA   ILE B 361    34.052  16.889  46.891  1.00 31.22      B  C
ATOM  3194  CB   ILE B 361    32.718  16.084  46.908  1.00 31.80      B  C
ATOM  3195  CG2  ILE B 361    31.728  16.755  47.898  1.00 32.06      B  C
ATOM  3196  CG1  ILE B 361    32.150  15.934  45.501  1.00 31.46      B  C
ATOM  3197  CD1  ILE B 361    30.953  14.963  45.417  1.00 33.54      B  C
ATOM  3198  C    ILE B 361    35.074  16.236  45.979  1.00 31.25      B  C
ATOM  3199  O    ILE B 361    35.421  16.760  44.923  1.00 32.22      B  O
ATOM  3200  N    HIS B 362    35.565  15.090  46.399  1.00 30.31      B  N
ATOM  3201  CA   HIS B 362    36.550  14.373  45.634  1.00 28.32      B  C
ATOM  3202  CB   HIS B 362    37.527  13.705  46.581  1.00 26.35      B  C
ATOM  3203  CG   HIS B 362    38.788  13.235  45.920  1.00 23.97      B  C
ATOM  3204  CD2  HIS B 362    40.082  13.559  46.129  1.00 24.21      B  C
ATOM  3205  ND1  HIS B 362    38.793  12.256  44.959  1.00 21.84      B  N
ATOM  3206  CE1  HIS B 362    40.036  11.985  44.607  1.00 23.58      B  C
ATOM  3207  NE2  HIS B 362    40.843  12.766  45.302  1.00 22.37      B  N
ATOM  3208  C    HIS B 362    35.917  13.339  44.712  1.00 28.89      B  C
ATOM  3209  O    HIS B 362    36.088  13.445  43.509  1.00 28.69      B  O
ATOM  3210  N    ARG B 363    35.231  12.353  45.316  1.00 27.90      B  N
ATOM  3211  CA   ARG B 363    34.557  11.198  44.714  1.00 27.07      B  C
ATOM  3212  CB   ARG B 363    33.492  11.575  43.642  1.00 31.04      B  C
ATOM  3213  CG   ARG B 363    33.957  12.447  42.480  1.00 36.49      B  C
ATOM  3214  CD   ARG B 363    32.808  13.110  41.684  1.00 40.86      B  C
ATOM  3215  NE   ARG B 363    32.099  12.125  40.882  1.00 43.30      B  N
ATOM  3216  CZ   ARG B 363    30.784  11.971  40.913  1.00 45.19      B  C
ATOM  3217  NH1  ARG B 363    30.051  12.768  41.672  1.00 45.88      B  N
ATOM  3218  NH2  ARG B 363    30.231  10.888  40.385  1.00 46.28      B  N
ATOM  3219  C    ARG B 363    35.487  10.077  44.259  1.00 25.66      B  C
ATOM  3220  O    ARG B 363    35.055   8.959  43.979  1.00 24.80      B  O
ATOM  3221  N    ASP B 364    36.782  10.343  44.248  1.00 23.10      B  N
ATOM  3222  CA   ASP B 364    37.739   9.321  43.838  1.00 23.23      B  C
ATOM  3223  CB   ASP B 364    38.390   9.699  42.493  1.00 22.13      B  C
ATOM  3224  CG   ASP B 364    37.449   9.544  41.317  1.00 20.78      B  C
ATOM  3225  OD1  ASP B 364    37.016   8.424  41.031  1.00 21.21      B  O
ATOM  3226  OD2  ASP B 364    37.135  10.563  40.696  1.00 22.36      B  O
ATOM  3227  C    ASP B 364    38.841   9.056  44.869  1.00 23.00      B  C
ATOM  3228  O    ASP B 364    39.915   8.582  44.516  1.00 22.24      B  O
ATOM  3229  N    LEU B 365    38.574   9.384  46.126  1.00 21.60      B  N
ATOM  3230  CA   LEU B 365    39.563   9.220  47.189  1.00 20.65      B  C
ATOM  3231  CB   LEU B 365    39.122   9.984  48.432  1.00 20.10      B  C
ATOM  3232  CG   LEU B 365    40.124  10.162  49.573  1.00 19.99      B  C
```

Figure 11

| ATOM | 3233 | CD1 | LEU | B | 365 | 41.281 | 11.054 | 49.099 | 1.00 | 19.16 | B | C |
|------|------|-----|-----|---|-----|--------|--------|--------|------|-------|---|---|
| ATOM | 3234 | CD2 | LEU | B | 365 | 39.394 | 10.784 | 50.806 | 1.00 | 18.91 | B | C |
| ATOM | 3235 | C   | LEU | B | 365 | 39.892 | 7.769  | 47.535 | 1.00 | 20.49 | B | C |
| ATOM | 3236 | O   | LEU | B | 365 | 39.017 | 6.981  | 47.879 | 1.00 | 20.21 | B | O |
| ATOM | 3237 | N   | ARG | B | 366 | 41.161 | 7.437  | 47.358 | 1.00 | 20.37 | B | N |
| ATOM | 3238 | CA  | ARG | B | 366 | 41.719 | 6.120  | 47.644 | 1.00 | 20.01 | B | C |
| ATOM | 3239 | CB  | ARG | B | 366 | 41.234 | 5.056  | 46.658 | 1.00 | 20.62 | B | C |
| ATOM | 3240 | CG  | ARG | B | 366 | 41.528 | 5.278  | 45.204 | 1.00 | 20.42 | B | C |
| ATOM | 3241 | CD  | ARG | B | 366 | 41.154 | 3.995  | 44.454 | 1.00 | 23.99 | B | C |
| ATOM | 3242 | NE  | ARG | B | 366 | 40.942 | 4.194  | 43.020 | 1.00 | 27.07 | B | N |
| ATOM | 3243 | CZ  | ARG | B | 366 | 39.932 | 4.893  | 42.494 | 1.00 | 29.69 | B | C |
| ATOM | 3244 | NH1 | ARG | B | 366 | 39.007 | 5.466  | 43.272 | 1.00 | 28.51 | B | N |
| ATOM | 3245 | NH2 | ARG | B | 366 | 39.874 | 5.056  | 41.184 | 1.00 | 29.56 | B | N |
| ATOM | 3246 | C   | ARG | B | 366 | 43.225 | 6.313  | 47.546 | 1.00 | 20.33 | B | C |
| ATOM | 3247 | O   | ARG | B | 366 | 43.682 | 7.296  | 46.965 | 1.00 | 19.55 | B | O |
| ATOM | 3248 | N   | ALA | B | 367 | 43.991 | 5.408  | 48.143 | 1.00 | 19.73 | B | N |
| ATOM | 3249 | CA  | ALA | B | 367 | 45.441 | 5.553  | 48.126 | 1.00 | 19.66 | B | C |
| ATOM | 3250 | CB  | ALA | B | 367 | 46.102 | 4.434  | 48.916 | 1.00 | 19.43 | B | C |
| ATOM | 3251 | C   | ALA | B | 367 | 46.094 | 5.708  | 46.741 | 1.00 | 20.67 | B | C |
| ATOM | 3252 | O   | ALA | B | 367 | 47.093 | 6.420  | 46.617 | 1.00 | 21.15 | B | O |
| ATOM | 3253 | N   | ALA | B | 368 | 45.534 | 5.063  | 45.709 | 1.00 | 20.89 | B | N |
| ATOM | 3254 | CA  | ALA | B | 368 | 46.070 | 5.163  | 44.347 | 1.00 | 20.67 | B | C |
| ATOM | 3255 | CB  | ALA | B | 368 | 45.232 | 4.348  | 43.378 | 1.00 | 21.84 | B | C |
| ATOM | 3256 | C   | ALA | B | 368 | 46.120 | 6.603  | 43.884 | 1.00 | 22.50 | B | C |
| ATOM | 3257 | O   | ALA | B | 368 | 46.974 | 6.971  | 43.088 | 1.00 | 22.99 | B | O |
| ATOM | 3258 | N   | ASN | B | 369 | 45.207 | 7.432  | 44.400 | 1.00 | 22.73 | B | N |
| ATOM | 3259 | CA  | ASN | B | 369 | 45.146 | 8.830  | 44.016 | 1.00 | 23.55 | B | C |
| ATOM | 3260 | CB  | ASN | B | 369 | 43.701 | 9.235  | 43.675 | 1.00 | 24.82 | B | C |
| ATOM | 3261 | CG  | ASN | B | 369 | 43.105 | 8.373  | 42.552 | 1.00 | 24.96 | B | C |
| ATOM | 3262 | OD1 | ASN | B | 369 | 43.800 | 8.022  | 41.584 | 1.00 | 24.33 | B | O |
| ATOM | 3263 | ND2 | ASN | B | 369 | 41.844 | 7.983  | 42.704 | 1.00 | 21.90 | B | N |
| ATOM | 3264 | C   | ASN | B | 369 | 45.828 | 9.836  | 44.950 | 1.00 | 22.47 | B | C |
| ATOM | 3265 | O   | ASN | B | 369 | 45.514 | 11.018 | 44.947 | 1.00 | 24.59 | B | O |
| ATOM | 3266 | N   | ILE | B | 370 | 46.680 | 9.354  | 45.829 | 1.00 | 21.91 | B | N |
| ATOM | 3267 | CA  | ILE | B | 370 | 47.460 | 10.258 | 46.683 | 1.00 | 20.56 | B | C |
| ATOM | 3268 | CB  | ILE | B | 370 | 47.470 | 9.790  | 48.146 | 1.00 | 19.47 | B | C |
| ATOM | 3269 | CG2 | ILE | B | 370 | 48.462 | 10.680 | 48.975 | 1.00 | 17.69 | B | C |
| ATOM | 3270 | CG1 | ILE | B | 370 | 46.036 | 9.773  | 48.710 | 1.00 | 17.92 | B | C |
| ATOM | 3271 | CD1 | ILE | B | 370 | 45.294 | 11.116 | 48.634 | 1.00 | 14.03 | B | C |
| ATOM | 3272 | C   | ILE | B | 370 | 48.894 | 10.098 | 46.107 | 1.00 | 20.60 | B | C |
| ATOM | 3273 | O   | ILE | B | 370 | 49.291 | 8.995  | 45.758 | 1.00 | 19.74 | B | O |
| ATOM | 3274 | N   | LEU | B | 371 | 49.620 | 11.193 | 45.949 | 1.00 | 21.70 | B | N |
| ATOM | 3275 | CA  | LEU | B | 371 | 50.972 | 11.133 | 45.431 | 1.00 | 22.86 | B | C |
| ATOM | 3276 | CB  | LEU | B | 371 | 51.136 | 12.108 | 44.246 | 1.00 | 21.48 | B | C |
| ATOM | 3277 | CG  | LEU | B | 371 | 50.164 | 11.860 | 43.067 | 1.00 | 18.24 | B | C |
| ATOM | 3278 | CD1 | LEU | B | 371 | 50.424 | 12.809 | 41.900 | 1.00 | 20.02 | B | C |
| ATOM | 3279 | CD2 | LEU | B | 371 | 50.329 | 10.444 | 42.613 | 1.00 | 18.09 | B | C |
| ATOM | 3280 | C   | LEU | B | 371 | 51.950 | 11.449 | 46.573 | 1.00 | 23.96 | B | C |
| ATOM | 3281 | O   | LEU | B | 371 | 51.633 | 12.250 | 47.454 | 1.00 | 24.62 | B | O |
| ATOM | 3282 | N   | VAL | B | 372 | 53.100 | 10.779 | 46.574 | 1.00 | 24.01 | B | N |
| ATOM | 3283 | CA  | VAL | B | 372 | 54.130 | 10.949 | 47.605 | 1.00 | 24.77 | B | C |
| ATOM | 3284 | CB  | VAL | B | 372 | 54.585 | 9.574  | 48.143 | 1.00 | 25.55 | B | C |
| ATOM | 3285 | CG1 | VAL | B | 372 | 55.442 | 9.735  | 49.389 | 1.00 | 24.92 | B | C |
| ATOM | 3286 | CG2 | VAL | B | 372 | 53.362 | 8.704  | 48.445 | 1.00 | 24.82 | B | C |
| ATOM | 3287 | C   | VAL | B | 372 | 55.337 | 11.666 | 47.031 | 1.00 | 25.36 | B | C |
| ATOM | 3288 | O   | VAL | B | 372 | 55.904 | 11.227 | 46.039 | 1.00 | 25.05 | B | O |
| ATOM | 3289 | N   | SER | B | 373 | 55.758 | 12.752 | 47.656 | 1.00 | 26.45 | B | N |
| ATOM | 3290 | CA  | SER | B | 373 | 56.911 | 13.492 | 47.146 | 1.00 | 28.78 | B | C |
| ATOM | 3291 | CB  | SER | B | 373 | 56.889 | 14.929 | 47.645 | 1.00 | 28.55 | B | C |

Figure 11

| | | | | | | | | | | | |
|---|---|---|---|---|---|---|---|---|---|---|---|
| ATOM | 3292 | OG | SER | B | 373 | 57.295 | 14.987 | 48.999 | 1.00 | 30.35 | B | O |
| ATOM | 3293 | C | SER | B | 373 | 58.256 | 12.844 | 47.496 | 1.00 | 30.33 | B | C |
| ATOM | 3294 | O | SER | B | 373 | 58.313 | 11.726 | 48.016 | 1.00 | 28.95 | B | O |
| ATOM | 3295 | N | ASP | B | 374 | 59.338 | 13.551 | 47.166 | 1.00 | 33.23 | B | N |
| ATOM | 3296 | CA | ASP | B | 374 | 60.699 | 13.078 | 47.439 | 1.00 | 35.16 | B | C |
| ATOM | 3297 | CB | ASP | B | 374 | 61.732 | 13.974 | 46.740 | 1.00 | 36.60 | B | C |
| ATOM | 3298 | CG | ASP | B | 374 | 61.652 | 15.414 | 47.190 | 1.00 | 38.06 | B | C |
| ATOM | 3299 | OD1 | ASP | B | 374 | 60.592 | 16.050 | 47.051 | 1.00 | 40.10 | B | O |
| ATOM | 3300 | OD2 | ASP | B | 374 | 62.650 | 15.925 | 47.701 | 1.00 | 40.70 | B | O |
| ATOM | 3301 | C | ASP | B | 374 | 60.948 | 13.048 | 48.949 | 1.00 | 35.60 | B | C |
| ATOM | 3302 | O | ASP | B | 374 | 61.644 | 12.165 | 49.452 | 1.00 | 35.27 | B | O |
| ATOM | 3303 | N | THR | B | 375 | 60.337 | 13.991 | 49.667 | 1.00 | 35.59 | B | N |
| ATOM | 3304 | CA | THR | B | 375 | 60.508 | 14.046 | 51.106 | 1.00 | 36.63 | B | C |
| ATOM | 3305 | CB | THR | B | 375 | 60.391 | 15.455 | 51.662 | 1.00 | 37.58 | B | C |
| ATOM | 3306 | OG1 | THR | B | 375 | 59.039 | 15.917 | 51.509 | 1.00 | 39.64 | B | O |
| ATOM | 3307 | CG2 | THR | B | 375 | 61.354 | 16.399 | 50.959 | 1.00 | 37.69 | B | C |
| ATOM | 3308 | C | THR | B | 375 | 59.458 | 13.219 | 51.812 | 1.00 | 36.81 | B | C |
| ATOM | 3309 | O | THR | B | 375 | 59.304 | 13.347 | 53.017 | 1.00 | 38.39 | B | O |
| ATOM | 3310 | N | LEU | B | 376 | 58.728 | 12.397 | 51.064 | 1.00 | 35.51 | B | N |
| ATOM | 3311 | CA | LEU | B | 376 | 57.679 | 11.535 | 51.610 | 1.00 | 35.27 | B | C |
| ATOM | 3312 | CB | LEU | B | 376 | 58.218 | 10.600 | 52.695 | 1.00 | 35.42 | B | C |
| ATOM | 3313 | CG | LEU | B | 376 | 59.429 | 9.721 | 52.368 | 1.00 | 35.91 | B | C |
| ATOM | 3314 | CD1 | LEU | B | 376 | 59.631 | 8.740 | 53.511 | 1.00 | 36.55 | B | C |
| ATOM | 3315 | CD2 | LEU | B | 376 | 59.232 | 8.979 | 51.059 | 1.00 | 36.18 | B | C |
| ATOM | 3316 | C | LEU | B | 376 | 56.420 | 12.234 | 52.118 | 1.00 | 34.38 | B | C |
| ATOM | 3317 | O | LEU | B | 376 | 55.704 | 11.693 | 52.958 | 1.00 | 35.26 | B | O |
| ATOM | 3318 | N | SER | B | 377 | 56.165 | 13.444 | 51.639 | 1.00 | 33.34 | B | N |
| ATOM | 3319 | CA | SER | B | 377 | 54.958 | 14.153 | 52.022 | 1.00 | 33.13 | B | C |
| ATOM | 3320 | CB | SER | B | 377 | 55.195 | 15.652 | 52.044 | 1.00 | 33.77 | B | C |
| ATOM | 3321 | OG | SER | B | 377 | 55.293 | 16.180 | 50.740 | 1.00 | 36.96 | B | O |
| ATOM | 3322 | C | SER | B | 377 | 53.841 | 13.779 | 51.025 | 1.00 | 32.15 | B | C |
| ATOM | 3323 | O | SER | B | 377 | 54.100 | 13.614 | 49.834 | 1.00 | 31.05 | B | O |
| ATOM | 3324 | N | CYS | B | 378 | 52.609 | 13.628 | 51.525 | 1.00 | 31.45 | B | N |
| ATOM | 3325 | CA | CYS | B | 378 | 51.459 | 13.227 | 50.681 | 1.00 | 29.18 | B | C |
| ATOM | 3326 | CB | CYS | B | 378 | 50.532 | 12.287 | 51.451 | 1.00 | 27.65 | B | C |
| ATOM | 3327 | SG | CYS | B | 378 | 51.229 | 10.694 | 51.863 | 1.00 | 29.16 | B | S |
| ATOM | 3328 | C | CYS | B | 378 | 50.644 | 14.399 | 50.165 | 1.00 | 27.71 | B | C |
| ATOM | 3329 | O | CYS | B | 378 | 50.502 | 15.393 | 50.870 | 1.00 | 28.42 | B | O |
| ATOM | 3330 | N | LYS | B | 379 | 50.140 | 14.273 | 48.929 | 1.00 | 25.84 | B | N |
| ATOM | 3331 | CA | LYS | B | 379 | 49.303 | 15.286 | 48.275 | 1.00 | 25.25 | B | C |
| ATOM | 3332 | CB | LYS | B | 379 | 50.121 | 16.204 | 47.321 | 1.00 | 26.00 | B | C |
| ATOM | 3333 | CG | LYS | B | 379 | 51.148 | 17.168 | 48.000 | 1.00 | 25.12 | B | C |
| ATOM | 3334 | CD | LYS | B | 379 | 51.815 | 18.106 | 46.974 | 1.00 | 25.98 | B | C |
| ATOM | 3335 | CE | LYS | B | 379 | 52.834 | 19.136 | 47.553 | 1.00 | 26.49 | B | C |
| ATOM | 3336 | NZ | LYS | B | 379 | 52.488 | 20.527 | 46.980 | 1.00 | 31.72 | B | N |
| ATOM | 3337 | C | LYS | B | 379 | 48.142 | 14.610 | 47.515 | 1.00 | 24.65 | B | C |
| ATOM | 3338 | O | LYS | B | 379 | 48.282 | 13.530 | 46.946 | 1.00 | 25.28 | B | O |
| ATOM | 3339 | N | ILE | B | 380 | 46.990 | 15.262 | 47.516 | 1.00 | 24.28 | B | N |
| ATOM | 3340 | CA | ILE | B | 380 | 45.770 | 14.743 | 46.880 | 1.00 | 23.87 | B | C |
| ATOM | 3341 | CB | ILE | B | 380 | 44.504 | 15.324 | 47.600 | 1.00 | 25.01 | B | C |
| ATOM | 3342 | CG2 | ILE | B | 380 | 43.231 | 14.819 | 46.935 | 1.00 | 25.42 | B | C |
| ATOM | 3343 | CG1 | ILE | B | 380 | 44.527 | 14.989 | 49.096 | 1.00 | 24.42 | B | C |
| ATOM | 3344 | CD1 | ILE | B | 380 | 43.495 | 15.713 | 49.831 | 1.00 | 25.04 | B | C |
| ATOM | 3345 | C | ILE | B | 380 | 45.685 | 15.142 | 45.407 | 1.00 | 23.40 | B | C |
| ATOM | 3346 | O | ILE | B | 380 | 45.815 | 16.311 | 45.073 | 1.00 | 23.95 | B | O |
| ATOM | 3347 | N | ALA | B | 381 | 45.405 | 14.182 | 44.539 | 1.00 | 23.78 | B | N |
| ATOM | 3348 | CA | ALA | B | 381 | 45.292 | 14.468 | 43.121 | 1.00 | 23.09 | B | C |
| ATOM | 3349 | CB | ALA | B | 381 | 46.335 | 13.646 | 42.356 | 1.00 | 23.29 | B | C |
| ATOM | 3350 | C | ALA | B | 381 | 43.920 | 14.027 | 42.679 | 1.00 | 22.71 | B | C |

Figure 11

| ATOM | 3351 | O   | ALA | B | 381 | 43.278 | 13.236 | 43.352 | 1.00 | 20.55 | B | O |
| ATOM | 3352 | N   | ASP | B | 382 | 43.533 | 14.502 | 41.497 | 1.00 | 23.68 | B | N |
| ATOM | 3353 | CA  | ASP | B | 382 | 42.297 | 14.113 | 40.837 | 1.00 | 24.01 | B | C |
| ATOM | 3354 | CB  | ASP | B | 382 | 42.451 | 12.695 | 40.312 | 1.00 | 23.14 | B | C |
| ATOM | 3355 | CG  | ASP | B | 382 | 43.405 | 12.628 | 39.126 | 1.00 | 24.46 | B | C |
| ATOM | 3356 | OD1 | ASP | B | 382 | 43.525 | 13.650 | 38.427 | 1.00 | 27.45 | B | O |
| ATOM | 3357 | OD2 | ASP | B | 382 | 44.021 | 11.582 | 38.884 | 1.00 | 24.34 | B | O |
| ATOM | 3358 | C   | ASP | B | 382 | 41.033 | 14.257 | 41.647 | 1.00 | 24.20 | B | C |
| ATOM | 3359 | O   | ASP | B | 382 | 40.227 | 13.335 | 41.744 | 1.00 | 23.82 | B | O |
| ATOM | 3360 | N   | PHE | B | 383 | 40.899 | 15.415 | 42.254 | 1.00 | 25.47 | B | N |
| ATOM | 3361 | CA  | PHE | B | 383 | 39.738 | 15.725 | 43.065 | 1.00 | 27.97 | B | C |
| ATOM | 3362 | CB  | PHE | B | 383 | 40.199 | 16.505 | 44.313 | 1.00 | 29.11 | B | C |
| ATOM | 3363 | CG  | PHE | B | 383 | 41.046 | 17.702 | 43.991 | 1.00 | 30.72 | B | C |
| ATOM | 3364 | CD1 | PHE | B | 383 | 40.464 | 18.896 | 43.591 | 1.00 | 31.70 | B | C |
| ATOM | 3365 | CD2 | PHE | B | 383 | 42.441 | 17.608 | 44.012 | 1.00 | 30.88 | B | C |
| ATOM | 3366 | CE1 | PHE | B | 383 | 41.256 | 19.985 | 43.204 | 1.00 | 31.51 | B | C |
| ATOM | 3367 | CE2 | PHE | B | 383 | 43.247 | 18.696 | 43.629 | 1.00 | 31.61 | B | C |
| ATOM | 3368 | CZ  | PHE | B | 383 | 42.647 | 19.884 | 43.222 | 1.00 | 30.59 | B | C |
| ATOM | 3369 | C   | PHE | B | 383 | 38.730 | 16.576 | 42.279 | 1.00 | 28.25 | B | C |
| ATOM | 3370 | O   | PHE | B | 383 | 39.097 | 17.275 | 41.339 | 1.00 | 27.72 | B | O |
| ATOM | 3371 | N   | GLY | B | 384 | 37.476 | 16.535 | 42.718 | 1.00 | 29.33 | B | N |
| ATOM | 3372 | CA  | GLY | B | 384 | 36.423 | 17.336 | 42.120 | 1.00 | 30.66 | B | C |
| ATOM | 3373 | C   | GLY | B | 384 | 36.038 | 17.015 | 40.703 | 1.00 | 31.69 | B | C |
| ATOM | 3374 | O   | GLY | B | 384 | 35.345 | 17.813 | 40.096 | 1.00 | 31.91 | B | O |
| ATOM | 3375 | N   | LEU | B | 385 | 36.526 | 15.887 | 40.178 | 1.00 | 32.98 | B | N |
| ATOM | 3376 | CA  | LEU | B | 385 | 36.224 | 15.452 | 38.812 | 1.00 | 33.99 | B | C |
| ATOM | 3377 | CB  | LEU | B | 385 | 37.054 | 14.227 | 38.370 | 1.00 | 33.43 | B | C |
| ATOM | 3378 | CG  | LEU | B | 385 | 38.584 | 14.212 | 38.481 | 1.00 | 34.05 | B | C |
| ATOM | 3379 | CD1 | LEU | B | 385 | 39.158 | 13.043 | 37.714 | 1.00 | 33.83 | B | C |
| ATOM | 3380 | CD2 | LEU | B | 385 | 39.183 | 15.543 | 38.022 | 1.00 | 34.96 | B | C |
| ATOM | 3381 | C   | LEU | B | 385 | 34.775 | 15.048 | 38.695 | 1.00 | 35.38 | B | C |
| ATOM | 3382 | O   | LEU | B | 385 | 34.161 | 14.519 | 39.641 | 1.00 | 33.99 | B | O |
| ATOM | 3383 | N   | ALA | B | 386 | 34.250 | 15.255 | 37.495 | 1.00 | 36.88 | B | N |
| ATOM | 3384 | CA  | ALA | B | 386 | 32.875 | 14.891 | 37.192 | 1.00 | 37.93 | B | C |
| ATOM | 3385 | CB  | ALA | B | 386 | 32.429 | 15.568 | 35.867 | 1.00 | 38.85 | B | C |
| ATOM | 3386 | C   | ALA | B | 386 | 32.724 | 13.371 | 37.098 | 1.00 | 37.23 | B | C |
| ATOM | 3387 | O   | ALA | B | 386 | 31.665 | 12.836 | 37.381 | 1.00 | 38.06 | B | O |
| ATOM | 3388 | N   | ARG | B | 387 | 33.802 | 12.664 | 36.781 | 1.00 | 36.98 | B | N |
| ATOM | 3389 | CA  | ARG | B | 387 | 33.698 | 11.209 | 36.632 | 1.00 | 36.15 | B | C |
| ATOM | 3390 | CB  | ARG | B | 387 | 34.145 | 10.832 | 35.218 | 1.00 | 36.90 | B | C |
| ATOM | 3391 | CG  | ARG | B | 387 | 35.607 | 11.173 | 34.962 | 1.00 | 38.78 | B | C |
| ATOM | 3392 | CD  | ARG | B | 387 | 36.053 | 10.821 | 33.557 | 1.00 | 39.07 | B | C |
| ATOM | 3393 | NE  | ARG | B | 387 | 37.500 | 10.967 | 33.420 | 1.00 | 39.82 | B | N |
| ATOM | 3394 | CZ  | ARG | B | 387 | 38.370 | 9.975  | 33.584 | 1.00 | 40.31 | B | C |
| ATOM | 3395 | NH1 | ARG | B | 387 | 37.941 | 8.752  | 33.870 | 1.00 | 40.70 | B | N |
| ATOM | 3396 | NH2 | ARG | B | 387 | 39.676 | 10.225 | 33.561 | 1.00 | 40.79 | B | N |
| ATOM | 3397 | C   | ARG | B | 387 | 34.441 | 10.342 | 37.657 | 1.00 | 35.16 | B | C |
| ATOM | 3398 | O   | ARG | B | 387 | 35.309 | 10.819 | 38.391 | 1.00 | 35.64 | B | O |
| ATOM | 3399 | N   | LEU | B | 388 | 34.089 | 9.066  | 37.694 | 1.00 | 32.63 | B | N |
| ATOM | 3400 | CA  | LEU | B | 388 | 34.727 | 8.117  | 38.568 | 1.00 | 31.40 | B | C |
| ATOM | 3401 | CB  | LEU | B | 388 | 33.728 | 7.060  | 38.994 | 1.00 | 31.86 | B | C |
| ATOM | 3402 | CG  | LEU | B | 388 | 32.506 | 7.603  | 39.712 | 1.00 | 34.04 | B | C |
| ATOM | 3403 | CD1 | LEU | B | 388 | 31.656 | 6.397  | 40.114 | 1.00 | 34.27 | B | C |
| ATOM | 3404 | CD2 | LEU | B | 388 | 32.959 | 8.362  | 40.964 | 1.00 | 34.86 | B | C |
| ATOM | 3405 | C   | LEU | B | 388 | 35.831 | 7.465  | 37.739 | 1.00 | 29.98 | B | C |
| ATOM | 3406 | O   | LEU | B | 388 | 35.555 | 6.813  | 36.743 | 1.00 | 29.44 | B | O |
| ATOM | 3407 | N   | ILE | B | 389 | 37.070 | 7.626  | 38.191 | 1.00 | 28.87 | B | N |
| ATOM | 3408 | CA  | ILE | B | 389 | 38.266 | 7.121  | 37.505 | 1.00 | 27.78 | B | C |
| ATOM | 3409 | CB  | ILE | B | 389 | 39.443 | 8.166  | 37.588 | 1.00 | 26.61 | B | C |

Figure 11

```
ATOM   3410  CG2 ILE B 389      38.983   9.551  37.128  1.00 25.89      B    C
ATOM   3411  CG1 ILE B 389      40.011   8.264  39.001  1.00 25.32      B    C
ATOM   3412  CD1 ILE B 389      41.058   9.320  39.120  1.00 24.57      B    C
ATOM   3413  C   ILE B 389      38.774   5.740  37.916  1.00 28.19      B    C
ATOM   3414  O   ILE B 389      38.415   5.207  38.966  1.00 26.63      B    O
ATOM   3415  N   GLU B 390      39.603   5.161  37.052  1.00 29.96      B    N
ATOM   3416  CA  GLU B 390      40.204   3.856  37.282  1.00 32.27      B    C
ATOM   3417  CB  GLU B 390      39.730   2.842  36.233  1.00 34.37      B    C
ATOM   3418  CG  GLU B 390      38.352   2.317  36.568  1.00 38.20      B    C
ATOM   3419  CD  GLU B 390      37.667   1.541  35.460  1.00 41.90      B    C
ATOM   3420  OE1 GLU B 390      36.425   1.640  35.405  1.00 46.31      B    O
ATOM   3421  OE2 GLU B 390      38.311   0.816  34.670  1.00 43.08      B    O
ATOM   3422  C   GLU B 390      41.724   3.934  37.342  1.00 32.95      B    C
ATOM   3423  O   GLU B 390      42.349   4.779  36.702  1.00 33.32      B    O
ATOM   3424  N   ASP B 391      42.318   3.007  38.077  1.00 33.18      B    N
ATOM   3425  CA  ASP B 391      43.770   3.006  38.285  1.00 34.33      B    C
ATOM   3426  CB  ASP B 391      44.092   2.091  39.483  1.00 34.54      B    C
ATOM   3427  CG  ASP B 391      43.319   2.486  40.742  1.00 35.30      B    C
ATOM   3428  OD1 ASP B 391      42.923   3.675  40.867  1.00 35.27      B    O
ATOM   3429  OD2 ASP B 391      43.101   1.612  41.599  1.00 36.52      B    O
ATOM   3430  C   ASP B 391      44.692   2.695  37.073  1.00 34.26      B    C
ATOM   3431  O   ASP B 391      45.911   2.989  37.106  1.00 34.49      B    O
ATOM   3432  N   ASN B 392      44.086   2.153  36.013  1.00 33.06      B    N
ATOM   3433  CA  ASN B 392      44.781   1.762  34.788  1.00 32.11      B    C
ATOM   3434  CB  ASN B 392      44.225   0.411  34.274  1.00 30.79      B    C
ATOM   3435  CG  ASN B 392      42.756   0.503  33.812  1.00 30.59      B    C
ATOM   3436  OD1 ASN B 392      42.107   1.535  33.946  1.00 29.93      B    O
ATOM   3437  ND2 ASN B 392      42.251  -0.573  33.243  1.00 29.69      B    N
ATOM   3438  C   ASN B 392      44.684   2.806  33.666  1.00 31.59      B    C
ATOM   3439  O   ASN B 392      44.888   2.474  32.515  1.00 31.28      B    O
ATOM   3440  N   GLU B 393      44.350   4.045  33.994  1.00 31.56      B    N
ATOM   3441  CA  GLU B 393      44.197   5.054  32.960  1.00 32.97      B    C
ATOM   3442  CB  GLU B 393      43.169   6.100  33.395  1.00 33.34      B    C
ATOM   3443  CG  GLU B 393      41.748   5.532  33.378  1.00 32.29      B    C
ATOM   3444  CD  GLU B 393      40.737   6.395  34.080  1.00 32.43      B    C
ATOM   3445  OE1 GLU B 393      41.053   7.539  34.467  1.00 31.57      B    O
ATOM   3446  OE2 GLU B 393      39.599   5.905  34.245  1.00 33.27      B    O
ATOM   3447  C   GLU B 393      45.472   5.708  32.443  1.00 34.10      B    C
ATOM   3448  O   GLU B 393      45.576   6.035  31.268  1.00 33.29      B    O
ATOM   3449  N   TYR B 394      46.441   5.874  33.327  1.00 34.92      B    N
ATOM   3450  CA  TYR B 394      47.700   6.477  32.952  1.00 36.27      B    C
ATOM   3451  CB  TYR B 394      47.772   7.882  33.542  1.00 35.18      B    C
ATOM   3452  CG  TYR B 394      46.723   8.786  32.942  1.00 34.76      B    C
ATOM   3453  CD1 TYR B 394      45.509   9.030  33.601  1.00 33.95      B    C
ATOM   3454  CE1 TYR B 394      44.520   9.806  33.019  1.00 33.21      B    C
ATOM   3455  CD2 TYR B 394      46.913   9.352  31.692  1.00 33.63      B    C
ATOM   3456  CE2 TYR B 394      45.925  10.128  31.100  1.00 33.90      B    C
ATOM   3457  CZ  TYR B 394      44.732  10.349  31.765  1.00 33.89      B    C
ATOM   3458  OH  TYR B 394      43.759  11.113  31.163  1.00 33.76      B    O
ATOM   3459  C   TYR B 394      48.903   5.605  33.321  1.00 37.48      B    C
ATOM   3460  O   TYR B 394      50.042   6.032  33.147  1.00 38.43      B    O
ATOM   3461  N   THR B 395      48.627   4.405  33.844  1.00 38.40      B    N
ATOM   3462  CA  THR B 395      49.623   3.390  34.224  1.00 40.45      B    C
ATOM   3463  CB  THR B 395      50.120   3.507  35.706  1.00 40.63      B    C
ATOM   3464  OG1 THR B 395      49.004   3.616  36.608  1.00 41.04      B    O
ATOM   3465  CG2 THR B 395      51.007   4.714  35.866  1.00 41.89      B    C
ATOM   3466  C   THR B 395      48.988   2.014  34.008  1.00 41.87      B    C
ATOM   3467  O   THR B 395      47.809   1.924  33.758  1.00 41.57      B    O
ATOM   3468  N   ALA B 396      49.721   0.935  34.233  1.00 44.35      B    N
```

Figure 11

| ATOM | 3469 | CA | ALA | B | 396 | 49.163 | -0.380 | 33.965 | 1.00 | 46.70 | B | C |
| ATOM | 3470 | CB | ALA | B | 396 | 50.146 | -1.176 | 33.104 | 1.00 | 46.54 | B | C |
| ATOM | 3471 | C | ALA | B | 396 | 48.609 | -1.267 | 35.097 | 1.00 | 48.71 | B | C |
| ATOM | 3472 | O | ALA | B | 396 | 48.490 | -2.477 | 34.900 | 1.00 | 49.30 | B | O |
| ATOM | 3473 | N | ARG | B | 397 | 48.102 | -0.686 | 36.185 | 1.00 | 50.30 | B | N |
| ATOM | 3474 | CA | ARG | B | 397 | 47.579 | -1.489 | 37.301 | 1.00 | 50.98 | B | C |
| ATOM | 3475 | CB | ARG | B | 397 | 46.856 | -0.604 | 38.304 | 1.00 | 50.72 | B | C |
| ATOM | 3476 | CG | ARG | B | 397 | 47.674 | 0.555 | 38.776 | 1.00 | 50.14 | B | C |
| ATOM | 3477 | CD | ARG | B | 397 | 48.502 | 0.244 | 39.993 | 1.00 | 50.98 | B | C |
| ATOM | 3478 | NE | ARG | B | 397 | 49.127 | 1.436 | 40.553 | 1.00 | 51.58 | B | N |
| ATOM | 3479 | CZ | ARG | B | 397 | 48.604 | 2.661 | 40.540 | 1.00 | 52.14 | B | C |
| ATOM | 3480 | NH1 | ARG | B | 397 | 47.426 | 2.923 | 39.993 | 1.00 | 52.99 | B | N |
| ATOM | 3481 | NH2 | ARG | B | 397 | 49.230 | 3.640 | 41.172 | 1.00 | 53.05 | B | N |
| ATOM | 3482 | C | ARG | B | 397 | 46.619 | -2.573 | 36.822 | 1.00 | 52.19 | B | C |
| ATOM | 3483 | O | ARG | B | 397 | 47.106 | -3.707 | 36.585 | 1.00 | 53.63 | B | O |
| ATOM | 3484 | CB | PRO | B | 403 | 36.490 | 2.269 | 41.320 | 1.00 | 35.83 | B | C |
| ATOM | 3485 | CG | PRO | B | 403 | 36.891 | 1.696 | 39.929 | 1.00 | 35.40 | B | C |
| ATOM | 3486 | C | PRO | B | 403 | 35.459 | 1.091 | 43.273 | 1.00 | 35.10 | B | C |
| ATOM | 3487 | O | PRO | B | 403 | 35.339 | 2.066 | 44.072 | 1.00 | 36.68 | B | O |
| ATOM | 3488 | N | PRO | B | 403 | 36.273 | -0.149 | 41.280 | 1.00 | 35.60 | B | N |
| ATOM | 3489 | CD | PRO | B | 403 | 36.590 | 0.175 | 39.881 | 1.00 | 35.72 | B | C |
| ATOM | 3490 | CA | PRO | B | 403 | 36.534 | 1.031 | 42.175 | 1.00 | 35.45 | B | C |
| ATOM | 3491 | N | ILE | B | 404 | 34.792 | -0.047 | 43.393 | 1.00 | 32.60 | B | N |
| ATOM | 3492 | CA | ILE | B | 404 | 33.689 | -0.252 | 44.308 | 1.00 | 30.68 | B | C |
| ATOM | 3493 | CB | ILE | B | 404 | 32.920 | -1.543 | 43.855 | 1.00 | 31.84 | B | C |
| ATOM | 3494 | CG2 | ILE | B | 404 | 32.726 | -2.560 | 44.978 | 1.00 | 31.37 | B | C |
| ATOM | 3495 | CG1 | ILE | B | 404 | 31.685 | -1.153 | 43.077 | 1.00 | 32.94 | B | C |
| ATOM | 3496 | CD1 | ILE | B | 404 | 31.069 | 0.147 | 43.552 | 1.00 | 35.65 | B | C |
| ATOM | 3497 | C | ILE | B | 404 | 34.042 | -0.288 | 45.805 | 1.00 | 29.04 | B | C |
| ATOM | 3498 | O | ILE | B | 404 | 33.275 | 0.180 | 46.626 | 1.00 | 28.66 | B | O |
| ATOM | 3499 | N | LYS | B | 405 | 35.230 | -0.769 | 46.146 | 1.00 | 26.02 | B | N |
| ATOM | 3500 | CA | LYS | B | 405 | 35.647 | -0.913 | 47.521 | 1.00 | 24.48 | B | C |
| ATOM | 3501 | CB | LYS | B | 405 | 36.894 | -1.813 | 47.603 | 1.00 | 24.51 | B | C |
| ATOM | 3502 | CG | LYS | B | 405 | 36.601 | -3.219 | 47.166 | 1.00 | 23.35 | B | C |
| ATOM | 3503 | CD | LYS | B | 405 | 37.787 | -4.143 | 47.353 | 1.00 | 23.66 | B | C |
| ATOM | 3504 | CE | LYS | B | 405 | 37.377 | -5.571 | 47.084 | 1.00 | 23.47 | B | C |
| ATOM | 3505 | NZ | LYS | B | 405 | 38.388 | -6.564 | 47.537 | 1.00 | 27.48 | B | N |
| ATOM | 3506 | C | LYS | B | 405 | 35.820 | 0.311 | 48.385 | 1.00 | 21.68 | B | C |
| ATOM | 3507 | O | LYS | B | 405 | 36.003 | 0.170 | 49.585 | 1.00 | 20.87 | B | O |
| ATOM | 3508 | N | TRP | B | 406 | 35.774 | 1.495 | 47.784 | 1.00 | 20.49 | B | N |
| ATOM | 3509 | CA | TRP | B | 406 | 35.917 | 2.768 | 48.497 | 1.00 | 19.61 | B | C |
| ATOM | 3510 | CB | TRP | B | 406 | 36.997 | 3.648 | 47.845 | 1.00 | 19.93 | B | C |
| ATOM | 3511 | CG | TRP | B | 406 | 38.411 | 3.093 | 47.927 | 1.00 | 22.03 | B | C |
| ATOM | 3512 | CD2 | TRP | B | 406 | 38.977 | 2.051 | 47.108 | 1.00 | 22.17 | B | C |
| ATOM | 3513 | CE2 | TRP | B | 406 | 40.266 | 1.762 | 47.628 | 1.00 | 22.08 | B | C |
| ATOM | 3514 | CE3 | TRP | B | 406 | 38.522 | 1.345 | 45.986 | 1.00 | 21.66 | B | C |
| ATOM | 3515 | CD1 | TRP | B | 406 | 39.366 | 3.409 | 48.854 | 1.00 | 22.34 | B | C |
| ATOM | 3516 | NE1 | TRP | B | 406 | 40.478 | 2.598 | 48.692 | 1.00 | 22.80 | B | N |
| ATOM | 3517 | CZ2 | TRP | B | 406 | 41.098 | 0.793 | 47.067 | 1.00 | 22.40 | B | C |
| ATOM | 3518 | CZ3 | TRP | B | 406 | 39.347 | 0.388 | 45.424 | 1.00 | 23.26 | B | C |
| ATOM | 3519 | CH2 | TRP | B | 406 | 40.629 | 0.113 | 45.969 | 1.00 | 23.08 | B | C |
| ATOM | 3520 | C | TRP | B | 406 | 34.633 | 3.596 | 48.528 | 1.00 | 20.27 | B | C |
| ATOM | 3521 | O | TRP | B | 406 | 34.590 | 4.668 | 49.127 | 1.00 | 20.21 | B | O |
| ATOM | 3522 | N | THR | B | 407 | 33.612 | 3.146 | 47.811 | 1.00 | 21.05 | B | N |
| ATOM | 3523 | CA | THR | B | 407 | 32.367 | 3.902 | 47.694 | 1.00 | 21.82 | B | C |
| ATOM | 3524 | CB | THR | B | 407 | 31.771 | 3.630 | 46.284 | 1.00 | 23.33 | B | C |
| ATOM | 3525 | OG1 | THR | B | 407 | 32.789 | 3.902 | 45.312 | 1.00 | 26.00 | B | O |
| ATOM | 3526 | CG2 | THR | B | 407 | 30.550 | 4.555 | 45.962 | 1.00 | 22.48 | B | C |
| ATOM | 3527 | C | THR | B | 407 | 31.333 | 3.660 | 48.823 | 1.00 | 21.21 | B | C |

Figure 11

| | | | | | | | | | | | |
|---|---|---|---|---|---|---|---|---|---|---|---|
| ATOM | 3528 | O | THR | B | 407 | 31.009 | 2.509 | 49.157 | 1.00 | 20.77 | B | O |
| ATOM | 3529 | N | ALA | B | 408 | 30.894 | 4.752 | 49.453 | 1.00 | 22.14 | B | N |
| ATOM | 3530 | CA | ALA | B | 408 | 29.885 | 4.682 | 50.541 | 1.00 | 22.93 | B | C |
| ATOM | 3531 | CB | ALA | B | 408 | 29.529 | 6.041 | 51.031 | 1.00 | 22.78 | B | C |
| ATOM | 3532 | C | ALA | B | 408 | 28.639 | 4.030 | 50.010 | 1.00 | 23.62 | B | C |
| ATOM | 3533 | O | ALA | B | 408 | 28.345 | 4.140 | 48.828 | 1.00 | 23.33 | B | O |
| ATOM | 3534 | N | PRO | B | 409 | 27.827 | 3.442 | 50.902 | 1.00 | 24.75 | B | N |
| ATOM | 3535 | CD | PRO | B | 409 | 28.063 | 3.375 | 52.358 | 1.00 | 25.26 | B | C |
| ATOM | 3536 | CA | PRO | B | 409 | 26.575 | 2.753 | 50.547 | 1.00 | 25.49 | B | C |
| ATOM | 3537 | CB | PRO | B | 409 | 26.050 | 2.290 | 51.901 | 1.00 | 25.54 | B | C |
| ATOM | 3538 | CG | PRO | B | 409 | 27.341 | 2.131 | 52.724 | 1.00 | 25.68 | B | C |
| ATOM | 3539 | C | PRO | B | 409 | 25.559 | 3.609 | 49.793 | 1.00 | 25.91 | B | C |
| ATOM | 3540 | O | PRO | B | 409 | 24.956 | 3.152 | 48.838 | 1.00 | 25.58 | B | O |
| ATOM | 3541 | N | GLU | B | 410 | 25.388 | 4.848 | 50.225 | 1.00 | 26.07 | B | N |
| ATOM | 3542 | CA | GLU | B | 410 | 24.439 | 5.744 | 49.580 | 1.00 | 26.49 | B | C |
| ATOM | 3543 | CB | GLU | B | 410 | 24.147 | 6.994 | 50.444 | 1.00 | 24.30 | B | C |
| ATOM | 3544 | CG | GLU | B | 410 | 25.260 | 8.060 | 50.557 | 1.00 | 24.37 | B | C |
| ATOM | 3545 | CD | GLU | B | 410 | 26.413 | 7.691 | 51.521 | 1.00 | 21.29 | B | C |
| ATOM | 3546 | OE1 | GLU | B | 410 | 26.334 | 6.677 | 52.212 | 1.00 | 19.12 | B | O |
| ATOM | 3547 | OE2 | GLU | B | 410 | 27.396 | 8.465 | 51.580 | 1.00 | 22.43 | B | O |
| ATOM | 3548 | C | GLU | B | 410 | 24.901 | 6.133 | 48.169 | 1.00 | 26.86 | B | C |
| ATOM | 3549 | O | GLU | B | 410 | 24.072 | 6.460 | 47.294 | 1.00 | 26.84 | B | O |
| ATOM | 3550 | N | ALA | B | 411 | 26.206 | 6.066 | 47.932 | 1.00 | 26.65 | B | N |
| ATOM | 3551 | CA | ALA | B | 411 | 26.713 | 6.393 | 46.613 | 1.00 | 28.02 | B | C |
| ATOM | 3552 | CB | ALA | B | 411 | 28.143 | 6.900 | 46.682 | 1.00 | 26.61 | B | C |
| ATOM | 3553 | C | ALA | B | 411 | 26.563 | 5.159 | 45.711 | 1.00 | 29.01 | B | C |
| ATOM | 3554 | O | ALA | B | 411 | 26.269 | 5.280 | 44.520 | 1.00 | 29.72 | B | O |
| ATOM | 3555 | N | ILE | B | 412 | 26.676 | 3.968 | 46.287 | 1.00 | 29.86 | B | N |
| ATOM | 3556 | CA | ILE | B | 412 | 26.475 | 2.753 | 45.512 | 1.00 | 31.13 | B | C |
| ATOM | 3557 | CB | ILE | B | 412 | 26.839 | 1.517 | 46.291 | 1.00 | 30.47 | B | C |
| ATOM | 3558 | CG2 | ILE | B | 412 | 26.492 | 0.243 | 45.467 | 1.00 | 32.27 | B | C |
| ATOM | 3559 | CG1 | ILE | B | 412 | 28.306 | 1.529 | 46.658 | 1.00 | 30.04 | B | C |
| ATOM | 3560 | CD1 | ILE | B | 412 | 28.681 | 0.352 | 47.458 | 1.00 | 29.14 | B | C |
| ATOM | 3561 | C | ILE | B | 412 | 24.988 | 2.561 | 45.156 | 1.00 | 33.23 | B | C |
| ATOM | 3562 | O | ILE | B | 412 | 24.648 | 2.244 | 44.008 | 1.00 | 34.68 | B | O |
| ATOM | 3563 | N | ASN | B | 413 | 24.104 | 2.762 | 46.135 | 1.00 | 33.47 | B | N |
| ATOM | 3564 | CA | ASN | B | 413 | 22.673 | 2.534 | 45.932 | 1.00 | 34.14 | B | C |
| ATOM | 3565 | CB | ASN | B | 413 | 21.983 | 2.294 | 47.270 | 1.00 | 35.16 | B | C |
| ATOM | 3566 | CG | ASN | B | 413 | 22.562 | 1.119 | 48.014 | 1.00 | 37.68 | B | C |
| ATOM | 3567 | OD1 | ASN | B | 413 | 23.134 | 0.203 | 47.403 | 1.00 | 39.13 | B | O |
| ATOM | 3568 | ND2 | ASN | B | 413 | 22.416 | 1.124 | 49.347 | 1.00 | 37.63 | B | N |
| ATOM | 3569 | C | ASN | B | 413 | 21.884 | 3.598 | 45.185 | 1.00 | 34.07 | B | C |
| ATOM | 3570 | O | ASN | B | 413 | 20.893 | 3.282 | 44.514 | 1.00 | 34.55 | B | O |
| ATOM | 3571 | N | TYR | B | 414 | 22.291 | 4.854 | 45.333 | 1.00 | 33.11 | B | N |
| ATOM | 3572 | CA | TYR | B | 414 | 21.561 | 5.965 | 44.735 | 1.00 | 33.09 | B | C |
| ATOM | 3573 | CB | TYR | B | 414 | 20.765 | 6.702 | 45.832 | 1.00 | 34.76 | B | C |
| ATOM | 3574 | CG | TYR | B | 414 | 19.899 | 5.788 | 46.663 | 1.00 | 38.54 | B | C |
| ATOM | 3575 | CD1 | TYR | B | 414 | 18.661 | 5.348 | 46.187 | 1.00 | 40.22 | B | C |
| ATOM | 3576 | CE1 | TYR | B | 414 | 17.880 | 4.446 | 46.916 | 1.00 | 41.43 | B | C |
| ATOM | 3577 | CD2 | TYR | B | 414 | 20.334 | 5.310 | 47.902 | 1.00 | 40.46 | B | C |
| ATOM | 3578 | CE2 | TYR | B | 414 | 19.547 | 4.400 | 48.645 | 1.00 | 42.79 | B | C |
| ATOM | 3579 | CZ | TYR | B | 414 | 18.324 | 3.979 | 48.130 | 1.00 | 43.47 | B | C |
| ATOM | 3580 | OH | TYR | B | 414 | 17.545 | 3.075 | 48.826 | 1.00 | 47.33 | B | O |
| ATOM | 3581 | C | TYR | B | 414 | 22.417 | 6.992 | 43.992 | 1.00 | 31.06 | B | C |
| ATOM | 3582 | O | TYR | B | 414 | 21.888 | 8.005 | 43.545 | 1.00 | 29.33 | B | O |
| ATOM | 3583 | N | GLY | B | 415 | 23.723 | 6.755 | 43.885 | 1.00 | 29.22 | B | N |
| ATOM | 3584 | CA | GLY | B | 415 | 24.572 | 7.737 | 43.222 | 1.00 | 28.29 | B | C |
| ATOM | 3585 | C | GLY | B | 415 | 24.688 | 9.080 | 43.956 | 1.00 | 27.67 | B | C |
| ATOM | 3586 | O | GLY | B | 415 | 25.040 | 10.098 | 43.360 | 1.00 | 27.55 | B | O |

Figure 11

| ATOM | 3587 | N | THR | B | 416 | 24.418 | 9.092 | 45.258 | 1.00 | 26.83 | B | N |
| --- | --- | --- | --- | --- | --- | --- | --- | --- | --- | --- | --- | --- |
| ATOM | 3588 | CA | THR | B | 416 | 24.523 | 10.335 | 46.000 | 1.00 | 26.72 | B | C |
| ATOM | 3589 | CB | THR | B | 416 | 23.296 | 10.569 | 46.955 | 1.00 | 27.36 | B | C |
| ATOM | 3590 | OG1 | THR | B | 416 | 23.718 | 11.252 | 48.147 | 1.00 | 31.17 | B | O |
| ATOM | 3591 | CG2 | THR | B | 416 | 22.598 | 9.295 | 47.266 | 1.00 | 24.90 | B | C |
| ATOM | 3592 | C | THR | B | 416 | 25.904 | 10.488 | 46.653 | 1.00 | 26.52 | B | C |
| ATOM | 3593 | O | THR | B | 416 | 26.280 | 9.792 | 47.614 | 1.00 | 25.64 | B | O |
| ATOM | 3594 | N | PHE | B | 417 | 26.679 | 11.365 | 46.030 | 1.00 | 26.29 | B | N |
| ATOM | 3595 | CA | PHE | B | 417 | 28.048 | 11.648 | 46.437 | 1.00 | 25.34 | B | C |
| ATOM | 3596 | CB | PHE | B | 417 | 28.987 | 11.674 | 45.211 | 1.00 | 23.89 | B | C |
| ATOM | 3597 | CG | PHE | B | 417 | 29.294 | 10.308 | 44.610 | 1.00 | 24.32 | B | C |
| ATOM | 3598 | CD1 | PHE | B | 417 | 28.459 | 9.745 | 43.639 | 1.00 | 24.82 | B | C |
| ATOM | 3599 | CD2 | PHE | B | 417 | 30.444 | 9.601 | 44.991 | 1.00 | 22.74 | B | C |
| ATOM | 3600 | CE1 | PHE | B | 417 | 28.775 | 8.485 | 43.054 | 1.00 | 24.96 | B | C |
| ATOM | 3601 | CE2 | PHE | B | 417 | 30.768 | 8.357 | 44.421 | 1.00 | 23.30 | B | C |
| ATOM | 3602 | CZ | PHE | B | 417 | 29.941 | 7.790 | 43.458 | 1.00 | 24.04 | B | C |
| ATOM | 3603 | C | PHE | B | 417 | 28.118 | 12.994 | 47.112 | 1.00 | 24.78 | B | C |
| ATOM | 3604 | O | PHE | B | 417 | 27.769 | 13.993 | 46.527 | 1.00 | 24.69 | B | O |
| ATOM | 3605 | N | THR | B | 418 | 28.657 | 13.013 | 48.325 | 1.00 | 24.73 | B | N |
| ATOM | 3606 | CA | THR | B | 418 | 28.847 | 14.238 | 49.090 | 1.00 | 22.71 | B | C |
| ATOM | 3607 | CB | THR | B | 418 | 27.790 | 14.376 | 50.188 | 1.00 | 23.00 | B | C |
| ATOM | 3608 | OG1 | THR | B | 418 | 28.021 | 13.365 | 51.173 | 1.00 | 22.44 | B | O |
| ATOM | 3609 | CG2 | THR | B | 418 | 26.374 | 14.201 | 49.612 | 1.00 | 23.53 | B | C |
| ATOM | 3610 | C | THR | B | 418 | 30.219 | 14.109 | 49.784 | 1.00 | 21.82 | B | C |
| ATOM | 3611 | O | THR | B | 418 | 30.911 | 13.108 | 49.662 | 1.00 | 21.08 | B | O |
| ATOM | 3612 | N | ILE | B | 419 | 30.564 | 15.101 | 50.569 | 1.00 | 21.18 | B | N |
| ATOM | 3613 | CA | ILE | B | 419 | 31.803 | 15.084 | 51.289 | 1.00 | 22.90 | B | C |
| ATOM | 3614 | CB | ILE | B | 419 | 32.047 | 16.441 | 51.988 | 1.00 | 24.16 | B | C |
| ATOM | 3615 | CG2 | ILE | B | 419 | 30.976 | 16.692 | 53.072 | 1.00 | 23.36 | B | C |
| ATOM | 3616 | CG1 | ILE | B | 419 | 33.502 | 16.511 | 52.509 | 1.00 | 23.69 | B | C |
| ATOM | 3617 | CD1 | ILE | B | 419 | 34.537 | 16.441 | 51.412 | 1.00 | 21.95 | B | C |
| ATOM | 3618 | C | ILE | B | 419 | 31.770 | 13.945 | 52.318 | 1.00 | 23.05 | B | C |
| ATOM | 3619 | O | ILE | B | 419 | 32.823 | 13.471 | 52.715 | 1.00 | 23.81 | B | O |
| ATOM | 3620 | N | LYS | B | 420 | 30.570 | 13.522 | 52.739 | 1.00 | 22.09 | B | N |
| ATOM | 3621 | CA | LYS | B | 420 | 30.419 | 12.423 | 53.689 | 1.00 | 20.54 | B | C |
| ATOM | 3622 | CB | LYS | B | 420 | 29.031 | 12.407 | 54.351 | 1.00 | 20.51 | B | C |
| ATOM | 3623 | CG | LYS | B | 420 | 28.772 | 13.638 | 55.226 | 1.00 | 20.29 | B | C |
| ATOM | 3624 | CD | LYS | B | 420 | 29.672 | 13.586 | 56.480 | 1.00 | 21.38 | B | C |
| ATOM | 3625 | CE | LYS | B | 420 | 29.564 | 14.862 | 57.291 | 1.00 | 21.38 | B | C |
| ATOM | 3626 | NZ | LYS | B | 420 | 30.469 | 14.762 | 58.466 | 1.00 | 25.15 | B | N |
| ATOM | 3627 | C | LYS | B | 420 | 30.740 | 11.091 | 53.038 | 1.00 | 19.42 | B | C |
| ATOM | 3628 | O | LYS | B | 420 | 31.157 | 10.165 | 53.730 | 1.00 | 19.04 | B | O |
| ATOM | 3629 | N | SER | B | 421 | 30.455 | 10.933 | 51.744 | 1.00 | 19.51 | B | N |
| ATOM | 3630 | CA | SER | B | 421 | 30.851 | 9.693 | 51.102 | 1.00 | 19.25 | B | C |
| ATOM | 3631 | CB | SER | B | 421 | 30.067 | 9.385 | 49.795 | 1.00 | 19.41 | B | C |
| ATOM | 3632 | OG | SER | B | 421 | 29.830 | 10.514 | 48.975 | 1.00 | 21.89 | B | O |
| ATOM | 3633 | C | SER | B | 421 | 32.396 | 9.747 | 50.941 | 1.00 | 18.62 | B | C |
| ATOM | 3634 | O | SER | B | 421 | 33.042 | 8.736 | 50.948 | 1.00 | 19.01 | B | O |
| ATOM | 3635 | N | ASP | B | 422 | 32.993 | 10.926 | 50.851 | 1.00 | 19.04 | B | N |
| ATOM | 3636 | CA | ASP | B | 422 | 34.467 | 10.976 | 50.795 | 1.00 | 19.85 | B | C |
| ATOM | 3637 | CB | ASP | B | 422 | 34.999 | 12.378 | 50.497 | 1.00 | 18.80 | B | C |
| ATOM | 3638 | CG | ASP | B | 422 | 34.819 | 12.783 | 49.048 | 1.00 | 20.15 | B | C |
| ATOM | 3639 | OD1 | ASP | B | 422 | 34.730 | 11.910 | 48.151 | 1.00 | 21.73 | B | O |
| ATOM | 3640 | OD2 | ASP | B | 422 | 34.752 | 13.994 | 48.801 | 1.00 | 21.85 | B | O |
| ATOM | 3641 | C | ASP | B | 422 | 35.000 | 10.546 | 52.161 | 1.00 | 20.15 | B | C |
| ATOM | 3642 | O | ASP | B | 422 | 36.032 | 9.856 | 52.239 | 1.00 | 19.63 | B | O |
| ATOM | 3643 | N | VAL | B | 423 | 34.320 | 10.962 | 53.239 | 1.00 | 20.05 | B | N |
| ATOM | 3644 | CA | VAL | B | 423 | 34.738 | 10.556 | 54.593 | 1.00 | 18.80 | B | C |
| ATOM | 3645 | CB | VAL | B | 423 | 33.851 | 11.165 | 55.746 | 1.00 | 18.60 | B | C |

Figure 11

| ATOM | 3646 | CG1 | VAL | B | 423 | 34.194 | 10.508 | 57.116 | 1.00 | 14.70 | B | C |
|------|------|-----|-----|---|-----|--------|--------|--------|------|-------|---|---|
| ATOM | 3647 | CG2 | VAL | B | 423 | 34.121 | 12.673 | 55.862 | 1.00 | 17.01 | B | C |
| ATOM | 3648 | C   | VAL | B | 423 | 34.739 | 9.029  | 54.675 | 1.00 | 18.72 | B | C |
| ATOM | 3649 | O   | VAL | B | 423 | 35.660 | 8.437  | 55.269 | 1.00 | 19.12 | B | O |
| ATOM | 3650 | N   | TRP | B | 424 | 33.745 | 8.390  | 54.050 | 1.00 | 18.19 | B | N |
| ATOM | 3651 | CA  | TRP | B | 424 | 33.666 | 6.932  | 54.036 | 1.00 | 16.48 | B | C |
| ATOM | 3652 | CB  | TRP | B | 424 | 32.373 | 6.451  | 53.336 | 1.00 | 16.24 | B | C |
| ATOM | 3653 | CG  | TRP | B | 424 | 32.293 | 4.962  | 53.097 | 1.00 | 16.46 | B | C |
| ATOM | 3654 | CD2 | TRP | B | 424 | 31.481 | 3.986  | 53.803 | 1.00 | 16.61 | B | C |
| ATOM | 3655 | CE2 | TRP | B | 424 | 31.801 | 2.725  | 53.274 | 1.00 | 17.74 | B | C |
| ATOM | 3656 | CE3 | TRP | B | 424 | 30.512 | 4.071  | 54.828 | 1.00 | 19.42 | B | C |
| ATOM | 3657 | CD1 | TRP | B | 424 | 33.030 | 4.251  | 52.198 | 1.00 | 15.46 | B | C |
| ATOM | 3658 | NE1 | TRP | B | 424 | 32.754 | 2.922  | 52.304 | 1.00 | 17.06 | B | N |
| ATOM | 3659 | CZ2 | TRP | B | 424 | 31.185 | 1.519  | 53.726 | 1.00 | 18.27 | B | C |
| ATOM | 3660 | CZ3 | TRP | B | 424 | 29.891 | 2.884  | 55.289 | 1.00 | 17.87 | B | C |
| ATOM | 3661 | CH2 | TRP | B | 424 | 30.235 | 1.623  | 54.735 | 1.00 | 19.71 | B | C |
| ATOM | 3662 | C   | TRP | B | 424 | 34.925 | 6.409  | 53.337 | 1.00 | 17.33 | B | C |
| ATOM | 3663 | O   | TRP | B | 424 | 35.602 | 5.513  | 53.858 | 1.00 | 14.50 | B | O |
| ATOM | 3664 | N   | SER | B | 425 | 35.235 | 6.986  | 52.169 | 1.00 | 18.17 | B | N |
| ATOM | 3665 | CA  | SER | B | 425 | 36.416 | 6.583  | 51.404 | 1.00 | 20.32 | B | C |
| ATOM | 3666 | CB  | SER | B | 425 | 36.537 | 7.362  | 50.086 | 1.00 | 21.20 | B | C |
| ATOM | 3667 | OG  | SER | B | 425 | 35.486 | 7.077  | 49.191 | 1.00 | 22.43 | B | O |
| ATOM | 3668 | C   | SER | B | 425 | 37.723 | 6.759  | 52.199 | 1.00 | 20.13 | B | C |
| ATOM | 3669 | O   | SER | B | 425 | 38.617 | 5.948  | 52.064 | 1.00 | 21.15 | B | O |
| ATOM | 3670 | N   | PHE | B | 426 | 37.842 | 7.840  | 52.959 | 1.00 | 20.35 | B | N |
| ATOM | 3671 | CA  | PHE | B | 426 | 39.032 | 8.097  | 53.763 | 1.00 | 21.40 | B | C |
| ATOM | 3672 | CB  | PHE | B | 426 | 38.948 | 9.451  | 54.465 | 1.00 | 21.76 | B | C |
| ATOM | 3673 | CG  | PHE | B | 426 | 40.188 | 9.809  | 55.249 | 1.00 | 22.05 | B | C |
| ATOM | 3674 | CD1 | PHE | B | 426 | 41.352 | 10.231 | 54.592 | 1.00 | 22.55 | B | C |
| ATOM | 3675 | CD2 | PHE | B | 426 | 40.191 | 9.735  | 56.645 | 1.00 | 22.76 | B | C |
| ATOM | 3676 | CE1 | PHE | B | 426 | 42.501 | 10.582 | 55.304 | 1.00 | 22.30 | B | C |
| ATOM | 3677 | CE2 | PHE | B | 426 | 41.336 | 10.083 | 57.393 | 1.00 | 20.94 | B | C |
| ATOM | 3678 | CZ  | PHE | B | 426 | 42.497 | 10.510 | 56.713 | 1.00 | 24.23 | B | C |
| ATOM | 3679 | C   | PHE | B | 426 | 39.239 | 6.968  | 54.768 | 1.00 | 21.61 | B | C |
| ATOM | 3680 | O   | PHE | B | 426 | 40.366 | 6.485  | 54.936 | 1.00 | 21.97 | B | O |
| ATOM | 3681 | N   | GLY | B | 427 | 38.151 | 6.533  | 55.420 | 1.00 | 20.36 | B | N |
| ATOM | 3682 | CA  | GLY | B | 427 | 38.259 | 5.430  | 56.348 | 1.00 | 17.76 | B | C |
| ATOM | 3683 | C   | GLY | B | 427 | 38.835 | 4.209  | 55.629 | 1.00 | 18.61 | B | C |
| ATOM | 3684 | O   | GLY | B | 427 | 39.656 | 3.498  | 56.184 | 1.00 | 18.16 | B | O |
| ATOM | 3685 | N   | ILE | B | 428 | 38.348 | 3.906  | 54.426 | 1.00 | 18.32 | B | N |
| ATOM | 3686 | CA  | ILE | B | 428 | 38.858 | 2.767  | 53.691 | 1.00 | 18.67 | B | C |
| ATOM | 3687 | CB  | ILE | B | 428 | 38.099 | 2.534  | 52.359 | 1.00 | 18.34 | B | C |
| ATOM | 3688 | CG2 | ILE | B | 428 | 38.647 | 1.346  | 51.678 | 1.00 | 14.84 | B | C |
| ATOM | 3689 | CG1 | ILE | B | 428 | 36.570 | 2.408  | 52.589 | 1.00 | 17.05 | B | C |
| ATOM | 3690 | CD1 | ILE | B | 428 | 36.125 | 1.094  | 53.305 | 1.00 | 17.21 | B | C |
| ATOM | 3691 | C   | ILE | B | 428 | 40.349 | 3.048  | 53.366 | 1.00 | 20.35 | B | C |
| ATOM | 3692 | O   | ILE | B | 428 | 41.197 | 2.157  | 53.495 | 1.00 | 21.14 | B | O |
| ATOM | 3693 | N   | LEU | B | 429 | 40.667 | 4.295  | 53.026 | 1.00 | 20.02 | B | N |
| ATOM | 3694 | CA  | LEU | B | 429 | 42.025 | 4.689  | 52.706 | 1.00 | 21.42 | B | C |
| ATOM | 3695 | CB  | LEU | B | 429 | 42.063 | 6.167  | 52.308 | 1.00 | 20.76 | B | C |
| ATOM | 3696 | CG  | LEU | B | 429 | 43.225 | 6.668  | 51.431 | 1.00 | 21.90 | B | C |
| ATOM | 3697 | CD1 | LEU | B | 429 | 42.951 | 8.096  | 51.019 | 1.00 | 22.87 | B | C |
| ATOM | 3698 | CD2 | LEU | B | 429 | 44.568 | 6.576  | 52.122 | 1.00 | 22.78 | B | C |
| ATOM | 3699 | C   | LEU | B | 429 | 42.950 | 4.429  | 53.916 | 1.00 | 21.52 | B | C |
| ATOM | 3700 | O   | LEU | B | 429 | 44.097 | 4.034  | 53.738 | 1.00 | 22.12 | B | O |
| ATOM | 3701 | N   | LEU | B | 430 | 42.432 | 4.606  | 55.133 | 1.00 | 20.98 | B | N |
| ATOM | 3702 | CA  | LEU | B | 430 | 43.215 | 4.394  | 56.354 | 1.00 | 20.80 | B | C |
| ATOM | 3703 | CB  | LEU | B | 430 | 42.440 | 4.831  | 57.603 | 1.00 | 20.11 | B | C |
| ATOM | 3704 | CG  | LEU | B | 430 | 42.246 | 6.337  | 57.890 | 1.00 | 20.53 | B | C |

Figure 11

| ATOM | 3705 | CD1 | LEU | B | 430 | 41.341 | 6.560 | 59.128 | 1.00 | 19.66 | B | C |
|------|------|-----|-----|---|-----|--------|-------|--------|------|-------|---|---|
| ATOM | 3706 | CD2 | LEU | B | 430 | 43.589 | 7.038 | 58.122 | 1.00 | 19.81 | B | C |
| ATOM | 3707 | C | LEU | B | 430 | 43.647 | 2.936 | 56.469 | 1.00 | 21.15 | B | C |
| ATOM | 3708 | O | LEU | B | 430 | 44.735 | 2.650 | 56.943 | 1.00 | 20.54 | B | O |
| ATOM | 3709 | N | THR | B | 431 | 42.797 | 2.003 | 56.039 | 1.00 | 22.23 | B | N |
| ATOM | 3710 | CA | THR | B | 431 | 43.178 | 0.597 | 56.091 | 1.00 | 22.80 | B | C |
| ATOM | 3711 | CB | THR | B | 431 | 42.004 | -0.339 | 55.811 | 1.00 | 23.06 | B | C |
| ATOM | 3712 | OG1 | THR | B | 431 | 41.628 | -0.241 | 54.430 | 1.00 | 24.67 | B | O |
| ATOM | 3713 | CG2 | THR | B | 431 | 40.810 | -0.023 | 56.745 | 1.00 | 21.41 | B | C |
| ATOM | 3714 | C | THR | B | 431 | 44.333 | 0.304 | 55.102 | 1.00 | 24.09 | B | C |
| ATOM | 3715 | O | THR | B | 431 | 45.252 | -0.487 | 55.414 | 1.00 | 23.59 | B | O |
| ATOM | 3716 | N | GLU | B | 432 | 44.277 | 0.926 | 53.915 | 1.00 | 23.29 | B | N |
| ATOM | 3717 | CA | GLU | B | 432 | 45.348 | 0.767 | 52.926 | 1.00 | 22.76 | B | C |
| ATOM | 3718 | CB | GLU | B | 432 | 45.062 | 1.580 | 51.669 | 1.00 | 22.20 | B | C |
| ATOM | 3719 | CG | GLU | B | 432 | 43.889 | 1.098 | 50.858 | 1.00 | 22.42 | B | C |
| ATOM | 3720 | CD | GLU | B | 432 | 43.701 | 1.964 | 49.627 | 1.00 | 22.47 | B | C |
| ATOM | 3721 | OE1 | GLU | B | 432 | 43.209 | 3.105 | 49.740 | 1.00 | 20.55 | B | O |
| ATOM | 3722 | OE2 | GLU | B | 432 | 44.061 | 1.487 | 48.543 | 1.00 | 22.03 | B | O |
| ATOM | 3723 | C | GLU | B | 432 | 46.667 | 1.280 | 53.533 | 1.00 | 22.82 | B | C |
| ATOM | 3724 | O | GLU | B | 432 | 47.708 | 0.667 | 53.369 | 1.00 | 22.56 | B | O |
| ATOM | 3725 | N | ILE | B | 433 | 46.600 | 2.409 | 54.235 | 1.00 | 23.15 | B | N |
| ATOM | 3726 | CA | ILE | B | 433 | 47.762 | 3.000 | 54.868 | 1.00 | 24.24 | B | C |
| ATOM | 3727 | CB | ILE | B | 433 | 47.425 | 4.376 | 55.457 | 1.00 | 23.43 | B | C |
| ATOM | 3728 | CG2 | ILE | B | 433 | 48.503 | 4.797 | 56.453 | 1.00 | 24.38 | B | C |
| ATOM | 3729 | CG1 | ILE | B | 433 | 47.323 | 5.421 | 54.336 | 1.00 | 22.15 | B | C |
| ATOM | 3730 | CD1 | ILE | B | 433 | 47.010 | 6.825 | 54.790 | 1.00 | 20.11 | B | C |
| ATOM | 3731 | C | ILE | B | 433 | 48.451 | 2.135 | 55.940 | 1.00 | 26.80 | B | C |
| ATOM | 3732 | O | ILE | B | 433 | 49.668 | 1.949 | 55.889 | 1.00 | 26.82 | B | O |
| ATOM | 3733 | N | VAL | B | 434 | 47.677 | 1.564 | 56.875 | 1.00 | 28.09 | B | N |
| ATOM | 3734 | CA | VAL | B | 434 | 48.284 | 0.784 | 57.951 | 1.00 | 28.17 | B | C |
| ATOM | 3735 | CB | VAL | B | 434 | 47.460 | 0.832 | 59.240 | 1.00 | 27.78 | B | C |
| ATOM | 3736 | CG1 | VAL | B | 434 | 47.266 | 2.272 | 59.625 | 1.00 | 27.00 | B | C |
| ATOM | 3737 | CG2 | VAL | B | 434 | 46.114 | 0.074 | 59.069 | 1.00 | 27.87 | B | C |
| ATOM | 3738 | C | VAL | B | 434 | 48.660 | -0.637 | 57.631 | 1.00 | 28.22 | B | C |
| ATOM | 3739 | O | VAL | B | 434 | 49.384 | -1.259 | 58.392 | 1.00 | 28.31 | B | O |
| ATOM | 3740 | N | THR | B | 435 | 48.184 | -1.132 | 56.504 | 1.00 | 28.89 | B | N |
| ATOM | 3741 | CA | THR | B | 435 | 48.513 | -2.480 | 56.068 | 1.00 | 29.95 | B | C |
| ATOM | 3742 | CB | THR | B | 435 | 47.270 | -3.169 | 55.533 | 1.00 | 31.25 | B | C |
| ATOM | 3743 | OG1 | THR | B | 435 | 46.744 | -2.403 | 54.429 | 1.00 | 31.64 | B | O |
| ATOM | 3744 | CG2 | THR | B | 435 | 46.203 | -3.325 | 56.659 | 1.00 | 28.76 | B | C |
| ATOM | 3745 | C | THR | B | 435 | 49.570 | -2.436 | 54.932 | 1.00 | 30.87 | B | C |
| ATOM | 3746 | O | THR | B | 435 | 49.792 | -3.428 | 54.226 | 1.00 | 30.60 | B | O |
| ATOM | 3747 | N | HIS | B | 436 | 50.137 | -1.249 | 54.713 | 1.00 | 31.25 | B | N |
| ATOM | 3748 | CA | HIS | B | 436 | 51.130 | -0.989 | 53.674 | 1.00 | 32.57 | B | C |
| ATOM | 3749 | CB | HIS | B | 436 | 52.447 | -1.717 | 53.976 | 1.00 | 35.13 | B | C |
| ATOM | 3750 | CG | HIS | B | 436 | 53.053 | -1.357 | 55.302 | 1.00 | 36.40 | B | C |
| ATOM | 3751 | CD2 | HIS | B | 436 | 53.377 | -2.126 | 56.364 | 1.00 | 37.80 | B | C |
| ATOM | 3752 | ND1 | HIS | B | 436 | 53.437 | -0.075 | 55.637 | 1.00 | 37.74 | B | N |
| ATOM | 3753 | CE1 | HIS | B | 436 | 53.986 | -0.071 | 56.837 | 1.00 | 34.89 | B | C |
| ATOM | 3754 | NE2 | HIS | B | 436 | 53.960 | -1.304 | 57.299 | 1.00 | 37.58 | B | N |
| ATOM | 3755 | C | HIS | B | 436 | 50.624 | -1.319 | 52.258 | 1.00 | 32.29 | B | C |
| ATOM | 3756 | O | HIS | B | 436 | 51.263 | -2.047 | 51.505 | 1.00 | 31.94 | B | O |
| ATOM | 3757 | N | GLY | B | 437 | 49.456 | -0.790 | 51.913 | 1.00 | 31.55 | B | N |
| ATOM | 3758 | CA | GLY | B | 437 | 48.908 | -1.011 | 50.590 | 1.00 | 31.47 | B | C |
| ATOM | 3759 | C | GLY | B | 437 | 48.023 | -2.211 | 50.313 | 1.00 | 31.46 | B | C |
| ATOM | 3760 | O | GLY | B | 437 | 47.708 | -2.482 | 49.154 | 1.00 | 32.15 | B | O |
| ATOM | 3761 | N | ARG | B | 438 | 47.582 | -2.923 | 51.338 | 1.00 | 30.80 | B | N |
| ATOM | 3762 | CA | ARG | B | 438 | 46.723 | -4.073 | 51.085 | 1.00 | 31.26 | B | C |
| ATOM | 3763 | CB | ARG | B | 438 | 46.597 | -4.874 | 52.366 | 1.00 | 34.08 | B | C |

Figure 11

| ATOM | 3764 | CG | ARG | B | 438 | 46.173 | -6.324 | 52.185 | 1.00 | 38.13 | B | C |
|------|------|-----|-----|---|-----|--------|--------|--------|------|-------|---|---|
| ATOM | 3765 | CD | ARG | B | 438 | 44.681 | -6.466 | 52.037 | 1.00 | 41.47 | B | C |
| ATOM | 3766 | NE | ARG | B | 438 | 43.924 | -5.779 | 53.100 | 1.00 | 45.56 | B | N |
| ATOM | 3767 | CZ | ARG | B | 438 | 43.971 | -6.116 | 54.388 | 1.00 | 46.96 | B | C |
| ATOM | 3768 | NH1 | ARG | B | 438 | 44.755 | -7.130 | 54.765 | 1.00 | 48.58 | B | N |
| ATOM | 3769 | NH2 | ARG | B | 438 | 43.207 | -5.487 | 55.280 | 1.00 | 45.60 | B | N |
| ATOM | 3770 | C | ARG | B | 438 | 45.340 | -3.627 | 50.546 | 1.00 | 30.67 | B | C |
| ATOM | 3771 | O | ARG | B | 438 | 44.815 | -2.576 | 50.939 | 1.00 | 29.40 | B | O |
| ATOM | 3772 | N | ILE | B | 439 | 44.791 | -4.396 | 49.608 | 1.00 | 29.32 | B | N |
| ATOM | 3773 | CA | ILE | B | 439 | 43.485 | -4.085 | 49.011 | 1.00 | 29.98 | B | C |
| ATOM | 3774 | CB | ILE | B | 439 | 43.173 | -5.006 | 47.774 | 1.00 | 32.00 | B | C |
| ATOM | 3775 | CG2 | ILE | B | 439 | 41.921 | -4.513 | 47.015 | 1.00 | 32.32 | B | C |
| ATOM | 3776 | CG1 | ILE | B | 439 | 44.315 | -4.895 | 46.751 | 1.00 | 35.84 | B | C |
| ATOM | 3777 | CD1 | ILE | B | 439 | 44.370 | -6.044 | 45.686 | 1.00 | 38.00 | B | C |
| ATOM | 3778 | C | ILE | B | 439 | 42.374 | -4.246 | 50.069 | 1.00 | 28.98 | B | C |
| ATOM | 3779 | O | ILE | B | 439 | 42.422 | -5.149 | 50.925 | 1.00 | 27.65 | B | O |
| ATOM | 3780 | N | PRO | B | 440 | 41.404 | -3.321 | 50.080 | 1.00 | 27.94 | B | N |
| ATOM | 3781 | CD | PRO | B | 440 | 41.343 | -2.006 | 49.429 | 1.00 | 27.27 | B | C |
| ATOM | 3782 | CA | PRO | B | 440 | 40.334 | -3.460 | 51.078 | 1.00 | 27.81 | B | C |
| ATOM | 3783 | CB | PRO | B | 440 | 39.516 | -2.193 | 50.863 | 1.00 | 27.03 | B | C |
| ATOM | 3784 | CG | PRO | B | 440 | 40.570 | -1.209 | 50.438 | 1.00 | 27.81 | B | C |
| ATOM | 3785 | C | PRO | B | 440 | 39.543 | -4.745 | 50.815 | 1.00 | 27.32 | B | C |
| ATOM | 3786 | O | PRO | B | 440 | 39.684 | -5.342 | 49.741 | 1.00 | 27.31 | B | O |
| ATOM | 3787 | N | TYR | B | 441 | 38.847 | -5.237 | 51.845 | 1.00 | 27.39 | B | N |
| ATOM | 3788 | CA | TYR | B | 441 | 38.026 | -6.460 | 51.760 | 1.00 | 27.40 | B | C |
| ATOM | 3789 | CB | TYR | B | 441 | 36.713 | -6.180 | 51.011 | 1.00 | 25.48 | B | C |
| ATOM | 3790 | CG | TYR | B | 441 | 35.946 | -4.973 | 51.498 | 1.00 | 22.81 | B | C |
| ATOM | 3791 | CD1 | TYR | B | 441 | 35.070 | -5.063 | 52.589 | 1.00 | 22.23 | B | C |
| ATOM | 3792 | CE1 | TYR | B | 441 | 34.381 | -3.944 | 53.062 | 1.00 | 20.14 | B | C |
| ATOM | 3793 | CD2 | TYR | B | 441 | 36.102 | -3.740 | 50.882 | 1.00 | 21.09 | B | C |
| ATOM | 3794 | CE2 | TYR | B | 441 | 35.417 | -2.613 | 51.338 | 1.00 | 22.09 | B | C |
| ATOM | 3795 | CZ | TYR | B | 441 | 34.557 | -2.730 | 52.436 | 1.00 | 21.49 | B | C |
| ATOM | 3796 | OH | TYR | B | 441 | 33.936 | -1.620 | 52.924 | 1.00 | 21.16 | B | O |
| ATOM | 3797 | C | TYR | B | 441 | 38.773 | -7.595 | 51.053 | 1.00 | 29.22 | B | C |
| ATOM | 3798 | O | TYR | B | 441 | 38.298 | -8.143 | 50.056 | 1.00 | 29.64 | B | O |
| ATOM | 3799 | N | PRO | B | 442 | 39.945 | -7.976 | 51.566 | 1.00 | 31.23 | B | N |
| ATOM | 3800 | CD | PRO | B | 442 | 40.574 | -7.526 | 52.823 | 1.00 | 31.64 | B | C |
| ATOM | 3801 | CA | PRO | B | 442 | 40.713 | -9.055 | 50.922 | 1.00 | 32.70 | B | C |
| ATOM | 3802 | CB | PRO | B | 442 | 41.960 | -9.149 | 51.791 | 1.00 | 33.21 | B | C |
| ATOM | 3803 | CG | PRO | B | 442 | 41.465 | -8.675 | 53.168 | 1.00 | 32.52 | B | C |
| ATOM | 3804 | C | PRO | B | 442 | 39.941 | -10.360 | 50.835 | 1.00 | 34.64 | B | C |
| ATOM | 3805 | O | PRO | B | 442 | 39.256 | -10.758 | 51.776 | 1.00 | 35.12 | B | O |
| ATOM | 3806 | N | GLY | B | 443 | 39.962 | -10.982 | 49.662 | 1.00 | 36.43 | B | N |
| ATOM | 3807 | CA | GLY | B | 443 | 39.221 | -12.218 | 49.488 | 1.00 | 37.74 | B | C |
| ATOM | 3808 | C | GLY | B | 443 | 37.768 | -11.990 | 49.094 | 1.00 | 38.88 | B | C |
| ATOM | 3809 | O | GLY | B | 443 | 36.999 | -12.948 | 48.991 | 1.00 | 40.25 | B | O |
| ATOM | 3810 | N | MET | B | 444 | 37.361 | -10.734 | 48.910 | 1.00 | 38.51 | B | N |
| ATOM | 3811 | CA | MET | B | 444 | 35.987 | -10.442 | 48.469 | 1.00 | 37.51 | B | C |
| ATOM | 3812 | CB | MET | B | 444 | 35.279 | -9.469 | 49.436 | 1.00 | 36.58 | B | C |
| ATOM | 3813 | CG | MET | B | 444 | 34.613 | -10.133 | 50.630 | 1.00 | 36.39 | B | C |
| ATOM | 3814 | SD | MET | B | 444 | 33.909 | -8.997 | 51.851 | 1.00 | 35.81 | B | S |
| ATOM | 3815 | CE | MET | B | 444 | 33.014 | -8.118 | 50.922 | 1.00 | 33.29 | B | C |
| ATOM | 3816 | C | MET | B | 444 | 36.038 | -9.819 | 47.068 | 1.00 | 37.75 | B | C |
| ATOM | 3817 | O | MET | B | 444 | 36.914 | -9.005 | 46.796 | 1.00 | 38.25 | B | O |
| ATOM | 3818 | N | THR | B | 445 | 35.152 | -10.233 | 46.164 | 1.00 | 37.89 | B | N |
| ATOM | 3819 | CA | THR | B | 445 | 35.112 | -9.646 | 44.815 | 1.00 | 37.77 | B | C |
| ATOM | 3820 | CB | THR | B | 445 | 34.389 | -10.548 | 43.803 | 1.00 | 38.97 | B | C |
| ATOM | 3821 | OG1 | THR | B | 445 | 33.057 | -10.783 | 44.270 | 1.00 | 38.28 | B | O |
| ATOM | 3822 | CG2 | THR | B | 445 | 35.112 | -11.888 | 43.631 | 1.00 | 39.50 | B | C |

Figure 11

| ATOM | 3823 | C   | THR B 445 | 34.245 | -8.401  | 44.940 | 1.00 | 37.15 | B | C |
| ATOM | 3824 | O   | THR B 445 | 33.648 | -8.177  | 45.983 | 1.00 | 38.02 | B | O |
| ATOM | 3825 | N   | ASN B 446 | 34.124 | -7.616  | 43.882 | 1.00 | 36.37 | B | N |
| ATOM | 3826 | CA  | ASN B 446 | 33.281 | -6.429  | 43.961 | 1.00 | 35.68 | B | C |
| ATOM | 3827 | CB  | ASN B 446 | 33.342 | -5.599  | 42.676 | 1.00 | 34.56 | B | C |
| ATOM | 3828 | CG  | ASN B 446 | 34.528 | -4.642  | 42.647 | 1.00 | 33.94 | B | C |
| ATOM | 3829 | OD1 | ASN B 446 | 35.388 | -4.679  | 43.522 | 1.00 | 33.43 | B | O |
| ATOM | 3830 | ND2 | ASN B 446 | 34.558 | -3.761  | 41.647 | 1.00 | 33.50 | B | N |
| ATOM | 3831 | C   | ASN B 446 | 31.818 | -6.751  | 44.317 | 1.00 | 35.84 | B | C |
| ATOM | 3832 | O   | ASN B 446 | 31.265 | -6.147  | 45.238 | 1.00 | 34.20 | B | O |
| ATOM | 3833 | N   | PRO B 447 | 31.169 | -7.694  | 43.585 | 1.00 | 36.78 | B | N |
| ATOM | 3834 | CD  | PRO B 447 | 31.575 | -8.383  | 42.341 | 1.00 | 37.05 | B | C |
| ATOM | 3835 | CA  | PRO B 447 | 29.769 | -8.011  | 43.913 | 1.00 | 36.65 | B | C |
| ATOM | 3836 | CB  | PRO B 447 | 29.358 | -9.000  | 42.809 | 1.00 | 36.94 | B | C |
| ATOM | 3837 | CG  | PRO B 447 | 30.669 | -9.570  | 42.328 | 1.00 | 37.22 | B | C |
| ATOM | 3838 | C   | PRO B 447 | 29.550 | -8.557  | 45.334 | 1.00 | 35.64 | B | C |
| ATOM | 3839 | O   | PRO B 447 | 28.487 | -8.340  | 45.923 | 1.00 | 35.11 | B | O |
| ATOM | 3840 | N   | GLU B 448 | 30.578 | -9.188  | 45.899 | 1.00 | 34.36 | B | N |
| ATOM | 3841 | CA  | GLU B 448 | 30.497 | -9.728  | 47.251 | 1.00 | 32.88 | B | C |
| ATOM | 3842 | CB  | GLU B 448 | 31.657 | -10.669 | 47.526 | 1.00 | 33.86 | B | C |
| ATOM | 3843 | CG  | GLU B 448 | 31.640 | -11.886 | 46.670 | 1.00 | 35.92 | B | C |
| ATOM | 3844 | CD  | GLU B 448 | 32.721 | -12.876 | 47.056 | 1.00 | 37.83 | B | C |
| ATOM | 3845 | OE1 | GLU B 448 | 33.809 | -12.464 | 47.508 | 1.00 | 38.33 | B | O |
| ATOM | 3846 | OE2 | GLU B 448 | 32.476 | -14.087 | 46.908 | 1.00 | 38.78 | B | O |
| ATOM | 3847 | C   | GLU B 448 | 30.542 | -8.597  | 48.255 | 1.00 | 32.02 | B | C |
| ATOM | 3848 | O   | GLU B 448 | 29.941 | -8.676  | 49.325 | 1.00 | 31.51 | B | O |
| ATOM | 3849 | N   | VAL B 449 | 31.301 | -7.560  | 47.923 | 1.00 | 30.13 | B | N |
| ATOM | 3850 | CA  | VAL B 449 | 31.409 | -6.402  | 48.794 | 1.00 | 28.76 | B | C |
| ATOM | 3851 | CB  | VAL B 449 | 32.484 | -5.398  | 48.300 | 1.00 | 27.75 | B | C |
| ATOM | 3852 | CG1 | VAL B 449 | 32.326 | -4.061  | 48.983 | 1.00 | 26.85 | B | C |
| ATOM | 3853 | CG2 | VAL B 449 | 33.877 | -5.955  | 48.550 | 1.00 | 25.05 | B | C |
| ATOM | 3854 | C   | VAL B 449 | 30.048 | -5.737  | 48.858 | 1.00 | 28.46 | B | C |
| ATOM | 3855 | O   | VAL B 449 | 29.570 | -5.425  | 49.953 | 1.00 | 28.78 | B | O |
| ATOM | 3856 | N   | ILE B 450 | 29.414 | -5.592  | 47.690 | 1.00 | 27.73 | B | N |
| ATOM | 3857 | CA  | ILE B 450 | 28.098 | -4.968  | 47.583 | 1.00 | 28.08 | B | C |
| ATOM | 3858 | CB  | ILE B 450 | 27.536 | -4.990  | 46.140 | 1.00 | 28.25 | B | C |
| ATOM | 3859 | CG2 | ILE B 450 | 26.207 | -4.285  | 46.092 | 1.00 | 27.15 | B | C |
| ATOM | 3860 | CG1 | ILE B 450 | 28.526 | -4.400  | 45.121 | 1.00 | 29.65 | B | C |
| ATOM | 3861 | CD1 | ILE B 450 | 28.934 | -3.003  | 45.383 | 1.00 | 29.18 | B | C |
| ATOM | 3862 | C   | ILE B 450 | 27.089 | -5.719  | 48.452 | 1.00 | 27.48 | B | C |
| ATOM | 3863 | O   | ILE B 450 | 26.273 | -5.104  | 49.130 | 1.00 | 27.51 | B | O |
| ATOM | 3864 | N   | GLN B 451 | 27.123 | -7.045  | 48.391 | 1.00 | 27.73 | B | N |
| ATOM | 3865 | CA  | GLN B 451 | 26.186 | -7.823  | 49.192 | 1.00 | 29.12 | B | C |
| ATOM | 3866 | CB  | GLN B 451 | 25.941 | -9.234  | 48.631 | 1.00 | 31.52 | B | C |
| ATOM | 3867 | CG  | GLN B 451 | 27.119 | -10.167 | 48.491 | 1.00 | 37.79 | B | C |
| ATOM | 3868 | CD  | GLN B 451 | 26.914 | -11.174 | 47.343 | 1.00 | 39.82 | B | C |
| ATOM | 3869 | OE1 | GLN B 451 | 27.464 | -12.274 | 47.345 | 1.00 | 40.75 | B | O |
| ATOM | 3870 | NE2 | GLN B 451 | 26.157 | -10.758 | 46.326 | 1.00 | 41.61 | B | N |
| ATOM | 3871 | C   | GLN B 451 | 26.472 | -7.838  | 50.677 | 1.00 | 27.39 | B | C |
| ATOM | 3872 | O   | GLN B 451 | 25.557 | -7.939  | 51.460 | 1.00 | 26.56 | B | O |
| ATOM | 3873 | N   | ASN B 452 | 27.737 | -7.739  | 51.062 | 1.00 | 26.18 | B | N |
| ATOM | 3874 | CA  | ASN B 452 | 28.088 | -7.700  | 52.478 | 1.00 | 26.01 | B | C |
| ATOM | 3875 | CB  | ASN B 452 | 29.586 | -7.967  | 52.682 | 1.00 | 27.38 | B | C |
| ATOM | 3876 | CG  | ASN B 452 | 29.892 | -9.439  | 52.960 | 1.00 | 31.85 | B | C |
| ATOM | 3877 | OD1 | ASN B 452 | 29.907 | -9.877  | 54.128 | 1.00 | 34.13 | B | O |
| ATOM | 3878 | ND2 | ASN B 452 | 30.112 | -10.224 | 51.894 | 1.00 | 31.09 | B | N |
| ATOM | 3879 | C   | ASN B 452 | 27.680 | -6.320  | 53.030 | 1.00 | 23.97 | B | C |
| ATOM | 3880 | O   | ASN B 452 | 27.175 | -6.215  | 54.146 | 1.00 | 23.04 | B | O |
| ATOM | 3881 | N   | LEU B 453 | 27.862 | -5.277  | 52.236 | 1.00 | 23.47 | B | N |

Figure 11

| | | | | | | | | | | | |
|---|---|---|---|---|---|---|---|---|---|---|---|
| ATOM | 3882 | CA | LEU | B | 453 | 27.480 | -3.942 | 52.643 | 1.00 | 24.49 | B C |
| ATOM | 3883 | CB | LEU | B | 453 | 28.020 | -2.896 | 51.672 | 1.00 | 25.46 | B C |
| ATOM | 3884 | CG | LEU | B | 453 | 29.515 | -2.556 | 51.759 | 1.00 | 26.10 | B C |
| ATOM | 3885 | CD1 | LEU | B | 453 | 29.840 | -1.405 | 50.778 | 1.00 | 24.71 | B C |
| ATOM | 3886 | CD2 | LEU | B | 453 | 29.893 | -2.161 | 53.177 | 1.00 | 25.27 | B C |
| ATOM | 3887 | C | LEU | B | 453 | 25.955 | -3.817 | 52.749 | 1.00 | 24.74 | B C |
| ATOM | 3888 | O | LEU | B | 453 | 25.468 | -2.947 | 53.468 | 1.00 | 24.66 | B O |
| ATOM | 3889 | N | GLU | B | 454 | 25.214 | -4.618 | 51.983 | 1.00 | 25.03 | B N |
| ATOM | 3890 | CA | GLU | B | 454 | 23.763 | -4.601 | 52.070 | 1.00 | 27.32 | B C |
| ATOM | 3891 | CB | GLU | B | 454 | 23.127 | -5.578 | 51.093 | 1.00 | 30.53 | B C |
| ATOM | 3892 | CG | GLU | B | 454 | 23.128 | -5.193 | 49.655 | 1.00 | 37.02 | B C |
| ATOM | 3893 | CD | GLU | B | 454 | 22.844 | -6.402 | 48.769 | 1.00 | 41.23 | B C |
| ATOM | 3894 | OE1 | GLU | B | 454 | 22.969 | -6.268 | 47.518 | 1.00 | 45.04 | B O |
| ATOM | 3895 | OE2 | GLU | B | 454 | 22.539 | -7.492 | 49.322 | 1.00 | 43.08 | B O |
| ATOM | 3896 | C | GLU | B | 454 | 23.400 | -5.114 | 53.469 | 1.00 | 25.90 | B C |
| ATOM | 3897 | O | GLU | B | 454 | 22.414 | -4.695 | 54.040 | 1.00 | 24.48 | B O |
| ATOM | 3898 | N | ARG | B | 455 | 24.205 | -6.057 | 53.965 | 1.00 | 25.13 | B N |
| ATOM | 3899 | CA | ARG | B | 455 | 24.010 | -6.667 | 55.281 | 1.00 | 24.68 | B C |
| ATOM | 3900 | CB | ARG | B | 455 | 24.448 | -8.137 | 55.244 | 1.00 | 25.27 | B C |
| ATOM | 3901 | CG | ARG | B | 455 | 23.854 | -9.020 | 54.133 | 1.00 | 27.43 | B C |
| ATOM | 3902 | CD | ARG | B | 455 | 24.463 | -10.448 | 54.165 | 1.00 | 30.26 | B C |
| ATOM | 3903 | NE | ARG | B | 455 | 25.883 | -10.350 | 54.493 | 1.00 | 36.71 | B N |
| ATOM | 3904 | CZ | ARG | B | 455 | 26.416 | -10.605 | 55.702 | 1.00 | 38.07 | B C |
| ATOM | 3905 | NH1 | ARG | B | 455 | 25.660 | -11.039 | 56.709 | 1.00 | 37.04 | B N |
| ATOM | 3906 | NH2 | ARG | B | 455 | 27.639 | -10.156 | 55.996 | 1.00 | 35.64 | B N |
| ATOM | 3907 | C | ARG | B | 455 | 24.749 | -5.910 | 56.416 | 1.00 | 23.91 | B C |
| ATOM | 3908 | O | ARG | B | 455 | 24.844 | -6.414 | 57.539 | 1.00 | 23.72 | B O |
| ATOM | 3909 | N | GLY | B | 456 | 25.293 | -4.729 | 56.092 | 1.00 | 23.27 | B N |
| ATOM | 3910 | CA | GLY | B | 456 | 25.992 | -3.870 | 57.043 | 1.00 | 22.26 | B C |
| ATOM | 3911 | C | GLY | B | 456 | 27.374 | -4.288 | 57.513 | 1.00 | 21.79 | B C |
| ATOM | 3912 | O | GLY | B | 456 | 27.835 | -3.897 | 58.589 | 1.00 | 21.19 | B O |
| ATOM | 3913 | N | TYR | B | 457 | 28.062 | -5.044 | 56.678 | 1.00 | 21.73 | B N |
| ATOM | 3914 | CA | TYR | B | 457 | 29.384 | -5.540 | 57.002 | 1.00 | 20.68 | B C |
| ATOM | 3915 | CB | TYR | B | 457 | 29.810 | -6.557 | 55.939 | 1.00 | 20.04 | B C |
| ATOM | 3916 | CG | TYR | B | 457 | 31.209 | -7.100 | 56.098 | 1.00 | 20.47 | B C |
| ATOM | 3917 | CD1 | TYR | B | 457 | 31.440 | -8.287 | 56.788 | 1.00 | 20.69 | B C |
| ATOM | 3918 | CE1 | TYR | B | 457 | 32.734 | -8.793 | 56.944 | 1.00 | 22.37 | B C |
| ATOM | 3919 | CD2 | TYR | B | 457 | 32.315 | -6.413 | 55.561 | 1.00 | 20.83 | B C |
| ATOM | 3920 | CE2 | TYR | B | 457 | 33.611 | -6.901 | 55.722 | 1.00 | 20.06 | B C |
| ATOM | 3921 | CZ | TYR | B | 457 | 33.816 | -8.083 | 56.412 | 1.00 | 22.76 | B C |
| ATOM | 3922 | OH | TYR | B | 457 | 35.113 | -8.531 | 56.627 | 1.00 | 25.92 | B O |
| ATOM | 3923 | C | TYR | B | 457 | 30.436 | -4.435 | 57.145 | 1.00 | 20.75 | B C |
| ATOM | 3924 | O | TYR | B | 457 | 30.387 | -3.403 | 56.476 | 1.00 | 20.12 | B O |
| ATOM | 3925 | N | ARG | B | 458 | 31.369 | -4.649 | 58.070 | 1.00 | 21.00 | B N |
| ATOM | 3926 | CA | ARG | B | 458 | 32.453 | -3.706 | 58.295 | 1.00 | 21.90 | B C |
| ATOM | 3927 | CB | ARG | B | 458 | 32.204 | -2.818 | 59.518 | 1.00 | 21.47 | B C |
| ATOM | 3928 | CG | ARG | B | 458 | 30.967 | -1.873 | 59.403 | 1.00 | 20.07 | B C |
| ATOM | 3929 | CD | ARG | B | 458 | 31.095 | -0.918 | 58.234 | 1.00 | 20.55 | B C |
| ATOM | 3930 | NE | ARG | B | 458 | 30.055 | 0.111 | 58.229 | 1.00 | 20.94 | B N |
| ATOM | 3931 | CZ | ARG | B | 458 | 28.926 | 0.047 | 57.517 | 1.00 | 21.72 | B C |
| ATOM | 3932 | NH1 | ARG | B | 458 | 28.674 | -0.999 | 56.730 | 1.00 | 19.05 | B N |
| ATOM | 3933 | NH2 | ARG | B | 458 | 28.032 | 1.028 | 57.612 | 1.00 | 20.59 | B N |
| ATOM | 3934 | C | ARG | B | 458 | 33.712 | -4.521 | 58.459 | 1.00 | 22.81 | B C |
| ATOM | 3935 | O | ARG | B | 458 | 33.671 | -5.628 | 59.010 | 1.00 | 22.93 | B O |
| ATOM | 3936 | N | MET | B | 459 | 34.803 | -4.055 | 57.856 | 1.00 | 22.65 | B N |
| ATOM | 3937 | CA | MET | B | 459 | 36.069 | -4.768 | 57.982 | 1.00 | 23.11 | B C |
| ATOM | 3938 | CB | MET | B | 459 | 37.167 | -4.070 | 57.197 | 1.00 | 22.96 | B C |
| ATOM | 3939 | CG | MET | B | 459 | 37.140 | -4.246 | 55.699 | 1.00 | 24.67 | B C |
| ATOM | 3940 | SD | MET | B | 459 | 38.649 | -3.479 | 54.999 | 1.00 | 24.76 | B S |

Figure 11

| ATOM | 3941 | CE | MET | B | 459 | 38.081 | -1.838 | 54.593 | 1.00 | 23.05 | B | C |
|------|------|------|-----|---|-----|--------|--------|--------|------|-------|---|---|
| ATOM | 3942 | C | MET | B | 459 | 36.498 | -4.800 | 59.447 | 1.00 | 23.61 | B | C |
| ATOM | 3943 | O | MET | B | 459 | 36.163 | -3.899 | 60.224 | 1.00 | 23.01 | B | O |
| ATOM | 3944 | N | VAL | B | 460 | 37.206 | -5.857 | 59.828 | 1.00 | 25.48 | B | N |
| ATOM | 3945 | CA | VAL | B | 460 | 37.716 | -5.979 | 61.193 | 1.00 | 26.17 | B | C |
| ATOM | 3946 | CB | VAL | B | 460 | 37.990 | -7.443 | 61.549 | 1.00 | 26.31 | B | C |
| ATOM | 3947 | CG1 | VAL | B | 460 | 36.783 | -8.269 | 61.217 | 1.00 | 24.73 | B | C |
| ATOM | 3948 | CG2 | VAL | B | 460 | 39.227 | -7.972 | 60.794 | 1.00 | 27.06 | B | C |
| ATOM | 3949 | C | VAL | B | 460 | 39.014 | -5.129 | 61.319 | 1.00 | 27.50 | B | C |
| ATOM | 3950 | O | VAL | B | 460 | 39.498 | -4.555 | 60.328 | 1.00 | 26.22 | B | O |
| ATOM | 3951 | N | ARG | B | 461 | 39.529 | -4.999 | 62.543 | 1.00 | 27.70 | B | N |
| ATOM | 3952 | CA | ARG | B | 461 | 40.734 | -4.229 | 62.772 | 1.00 | 28.72 | B | C |
| ATOM | 3953 | CB | ARG | B | 461 | 41.006 | -4.093 | 64.277 | 1.00 | 29.62 | B | C |
| ATOM | 3954 | CG | ARG | B | 461 | 42.176 | -3.160 | 64.635 | 1.00 | 32.85 | B | C |
| ATOM | 3955 | CD | ARG | B | 461 | 42.440 | -3.105 | 66.135 | 1.00 | 35.32 | B | C |
| ATOM | 3956 | NE | ARG | B | 461 | 42.798 | -4.419 | 66.633 | 1.00 | 40.27 | B | N |
| ATOM | 3957 | CZ | ARG | B | 461 | 43.995 | -4.977 | 66.467 | 1.00 | 43.72 | B | C |
| ATOM | 3958 | NH1 | ARG | B | 461 | 44.974 | -4.309 | 65.844 | 1.00 | 44.41 | B | N |
| ATOM | 3959 | NH2 | ARG | B | 461 | 44.163 | -6.268 | 66.746 | 1.00 | 44.24 | B | N |
| ATOM | 3960 | C | ARG | B | 461 | 41.896 | -4.942 | 62.051 | 1.00 | 28.00 | B | C |
| ATOM | 3961 | O | ARG | B | 461 | 42.111 | -6.140 | 62.232 | 1.00 | 28.18 | B | O |
| ATOM | 3962 | N | PRO | B | 462 | 42.572 | -4.241 | 61.125 | 1.00 | 27.94 | B | N |
| ATOM | 3963 | CD | PRO | B | 462 | 42.346 | -2.846 | 60.714 | 1.00 | 25.83 | B | C |
| ATOM | 3964 | CA | PRO | B | 462 | 43.699 | -4.846 | 60.387 | 1.00 | 28.89 | B | C |
| ATOM | 3965 | CB | PRO | B | 462 | 44.096 | -3.753 | 59.398 | 1.00 | 27.68 | B | C |
| ATOM | 3966 | CG | PRO | B | 462 | 42.856 | -2.859 | 59.329 | 1.00 | 27.59 | B | C |
| ATOM | 3967 | C | PRO | B | 462 | 44.860 | -5.094 | 61.337 | 1.00 | 30.52 | B | C |
| ATOM | 3968 | O | PRO | B | 462 | 45.071 | -4.324 | 62.282 | 1.00 | 29.14 | B | O |
| ATOM | 3969 | N | ASP | B | 463 | 45.638 | -6.130 | 61.056 | 1.00 | 33.39 | B | N |
| ATOM | 3970 | CA | ASP | B | 463 | 46.788 | -6.452 | 61.886 | 1.00 | 36.78 | B | C |
| ATOM | 3971 | CB | ASP | B | 463 | 47.552 | -7.669 | 61.324 | 1.00 | 38.38 | B | C |
| ATOM | 3972 | CG | ASP | B | 463 | 46.717 | -8.965 | 61.326 | 1.00 | 41.14 | B | C |
| ATOM | 3973 | OD1 | ASP | B | 463 | 45.843 | -9.154 | 62.213 | 1.00 | 42.48 | B | O |
| ATOM | 3974 | OD2 | ASP | B | 463 | 46.946 | -9.822 | 60.436 | 1.00 | 43.54 | B | O |
| ATOM | 3975 | C | ASP | B | 463 | 47.697 | -5.222 | 61.969 | 1.00 | 37.93 | B | C |
| ATOM | 3976 | O | ASP | B | 463 | 47.885 | -4.491 | 60.989 | 1.00 | 38.27 | B | O |
| ATOM | 3977 | N | ASN | B | 464 | 48.126 | -4.929 | 63.194 | 1.00 | 39.85 | B | N |
| ATOM | 3978 | CA | ASN | B | 464 | 49.022 | -3.809 | 63.495 | 1.00 | 41.10 | B | C |
| ATOM | 3979 | CB | ASN | B | 464 | 50.358 | -3.968 | 62.752 | 1.00 | 43.90 | B | C |
| ATOM | 3980 | CG | ASN | B | 464 | 51.101 | -5.250 | 63.151 | 1.00 | 45.40 | B | C |
| ATOM | 3981 | OD1 | ASN | B | 464 | 51.259 | -5.538 | 64.347 | 1.00 | 46.40 | B | O |
| ATOM | 3982 | ND2 | ASN | B | 464 | 51.522 | -6.043 | 62.153 | 1.00 | 45.95 | B | N |
| ATOM | 3983 | C | ASN | B | 464 | 48.430 | -2.419 | 63.276 | 1.00 | 41.03 | B | C |
| ATOM | 3984 | O | ASN | B | 464 | 49.059 | -1.518 | 62.712 | 1.00 | 41.91 | B | O |
| ATOM | 3985 | N | CYS | B | 465 | 47.221 | -2.240 | 63.787 | 1.00 | 40.16 | B | N |
| ATOM | 3986 | CA | CYS | B | 465 | 46.514 | -0.968 | 63.685 | 1.00 | 38.16 | B | C |
| ATOM | 3987 | CB | CYS | B | 465 | 45.331 | -1.118 | 62.700 | 1.00 | 36.65 | B | C |
| ATOM | 3988 | SG | CYS | B | 465 | 44.072 | 0.199 | 62.709 | 1.00 | 32.25 | B | S |
| ATOM | 3989 | C | CYS | B | 465 | 46.026 | -0.603 | 65.095 | 1.00 | 37.36 | B | C |
| ATOM | 3990 | O | CYS | B | 465 | 45.405 | -1.410 | 65.764 | 1.00 | 37.68 | B | O |
| ATOM | 3991 | N | PRO | B | 466 | 46.383 | 0.582 | 65.594 | 1.00 | 36.45 | B | N |
| ATOM | 3992 | CD | PRO | B | 466 | 47.218 | 1.635 | 64.985 | 1.00 | 37.13 | B | C |
| ATOM | 3993 | CA | PRO | B | 466 | 45.925 | 0.970 | 66.932 | 1.00 | 35.92 | B | C |
| ATOM | 3994 | CB | PRO | B | 466 | 46.373 | 2.427 | 67.038 | 1.00 | 35.65 | B | C |
| ATOM | 3995 | CG | PRO | B | 466 | 47.600 | 2.474 | 66.199 | 1.00 | 36.89 | B | C |
| ATOM | 3996 | C | PRO | B | 466 | 44.389 | 0.884 | 67.009 | 1.00 | 35.96 | B | C |
| ATOM | 3997 | O | PRO | B | 466 | 43.713 | 1.120 | 66.002 | 1.00 | 34.95 | B | O |
| ATOM | 3998 | N | GLU | B | 467 | 43.849 | 0.534 | 68.184 | 1.00 | 35.00 | B | N |
| ATOM | 3999 | CA | GLU | B | 467 | 42.395 | 0.427 | 68.377 | 1.00 | 34.86 | B | C |

Figure 11

```
ATOM   4000  CB   GLU B 467      42.043   -0.041   69.798  1.00 35.99      B    C
ATOM   4001  CG   GLU B 467      41.308   -1.412   69.899  1.00 39.28      B    C
ATOM   4002  CD   GLU B 467      40.022   -1.541   69.072  1.00 40.12      B    C
ATOM   4003  OE1  GLU B 467      39.962   -2.469   68.238  1.00 40.26      B    O
ATOM   4004  OE2  GLU B 467      39.058   -0.770   69.294  1.00 41.93      B    O
ATOM   4005  C    GLU B 467      41.692    1.757   68.152  1.00 33.66      B    C
ATOM   4006  O    GLU B 467      40.577    1.807   67.649  1.00 32.77      B    O
ATOM   4007  N    GLU B 468      42.339    2.818   68.610  1.00 33.00      B    N
ATOM   4008  CA   GLU B 468      41.803    4.152   68.497  1.00 33.28      B    C
ATOM   4009  CB   GLU B 468      42.698    5.157   69.229  1.00 37.37      B    C
ATOM   4010  CG   GLU B 468      42.882    4.920   70.736  1.00 41.83      B    C
ATOM   4011  CD   GLU B 468      43.906    3.806   71.078  1.00 45.44      B    C
ATOM   4012  OE1  GLU B 468      44.808    3.491   70.239  1.00 45.68      B    O
ATOM   4013  OE2  GLU B 468      43.807    3.253   72.213  1.00 46.32      B    O
ATOM   4014  C    GLU B 468      41.677    4.523   67.027  1.00 31.37      B    C
ATOM   4015  O    GLU B 468      40.717    5.192   66.647  1.00 31.50      B    O
ATOM   4016  N    LEU B 469      42.626    4.067   66.201  1.00 29.33      B    N
ATOM   4017  CA   LEU B 469      42.605    4.340   64.758  1.00 27.10      B    C
ATOM   4018  CB   LEU B 469      43.902    3.927   64.053  1.00 26.54      B    C
ATOM   4019  CG   LEU B 469      43.947    4.395   62.585  1.00 24.20      B    C
ATOM   4020  CD1  LEU B 469      43.898    5.905   62.535  1.00 23.39      B    C
ATOM   4021  CD2  LEU B 469      45.248    3.915   61.967  1.00 25.77      B    C
ATOM   4022  C    LEU B 469      41.464    3.580   64.116  1.00 25.63      B    C
ATOM   4023  O    LEU B 469      40.816    4.102   63.212  1.00 25.49      B    O
ATOM   4024  N    TYR B 470      41.273    2.329   64.542  1.00 23.98      B    N
ATOM   4025  CA   TYR B 470      40.176    1.489   64.046  1.00 23.42      B    C
ATOM   4026  CB   TYR B 470      40.242    0.079   64.602  1.00 21.07      B    C
ATOM   4027  CG   TYR B 470      39.102   -0.815   64.135  1.00 22.48      B    C
ATOM   4028  CD1  TYR B 470      38.976   -1.167   62.789  1.00 22.13      B    C
ATOM   4029  CE1  TYR B 470      37.925   -1.980   62.345  1.00 23.15      B    C
ATOM   4030  CD2  TYR B 470      38.136   -1.304   65.041  1.00 22.47      B    C
ATOM   4031  CE2  TYR B 470      37.086   -2.121   64.605  1.00 22.32      B    C
ATOM   4032  CZ   TYR B 470      36.989   -2.454   63.257  1.00 23.03      B    C
ATOM   4033  OH   TYR B 470      35.982   -3.276   62.816  1.00 22.54      B    O
ATOM   4034  C    TYR B 470      38.812    2.054   64.433  1.00 23.98      B    C
ATOM   4035  O    TYR B 470      37.853    1.912   63.684  1.00 23.87      B    O
ATOM   4036  N    GLN B 471      38.716    2.674   65.608  1.00 24.02      B    N
ATOM   4037  CA   GLN B 471      37.440    3.225   66.017  1.00 24.77      B    C
ATOM   4038  CB   GLN B 471      37.397    3.476   67.540  1.00 26.59      B    C
ATOM   4039  CG   GLN B 471      37.269    2.147   68.347  1.00 27.68      B    C
ATOM   4040  CD   GLN B 471      36.065    1.300   67.897  1.00 30.30      B    C
ATOM   4041  OE1  GLN B 471      34.964    1.839   67.596  1.00 30.33      B    O
ATOM   4042  NE2  GLN B 471      36.259   -0.017   67.834  1.00 28.70      B    N
ATOM   4043  C    GLN B 471      37.185    4.466   65.193  1.00 24.45      B    C
ATOM   4044  O    GLN B 471      36.046    4.808   64.893  1.00 24.77      B    O
ATOM   4045  N    LEU B 472      38.261    5.102   64.763  1.00 24.24      B    N
ATOM   4046  CA   LEU B 472      38.139    6.271   63.926  1.00 24.02      B    C
ATOM   4047  CB   LEU B 472      39.509    6.910   63.751  1.00 26.46      B    C
ATOM   4048  CG   LEU B 472      39.523    8.415   63.600  1.00 29.13      B    C
ATOM   4049  CD1  LEU B 472      38.918    9.068   64.858  1.00 28.41      B    C
ATOM   4050  CD2  LEU B 472      40.980    8.858   63.365  1.00 30.92      B    C
ATOM   4051  C    LEU B 472      37.580    5.793   62.568  1.00 22.76      B    C
ATOM   4052  O    LEU B 472      36.713    6.455   62.000  1.00 22.08      B    O
ATOM   4053  N    MET B 473      38.123    4.683   62.052  1.00 21.21      B    N
ATOM   4054  CA   MET B 473      37.652    4.076   60.806  1.00 21.55      B    C
ATOM   4055  CB   MET B 473      38.374    2.757   60.547  1.00 21.02      B    C
ATOM   4056  CG   MET B 473      39.894    2.882   60.226  1.00 20.69      B    C
ATOM   4057  SD   MET B 473      40.664    1.292   60.223  1.00 23.46      B    S
ATOM   4058  CE   MET B 473      42.243    1.757   59.590  1.00 22.96      B    C
```

Figure 11

| | | | | | | | | | | |
|---|---|---|---|---|---|---|---|---|---|---|
|ATOM|4059|C|MET|B|473|36.148|3.763|60.918|1.00 22.26|B C|
|ATOM|4060|O|MET|B|473|35.370|4.061|60.002|1.00 21.43|B O|
|ATOM|4061|N|ARG|B|474|35.744|3.183|62.053|1.00 22.38|B N|
|ATOM|4062|CA|ARG|B|474|34.349|2.819|62.263|1.00 23.33|B C|
|ATOM|4063|CB|ARG|B|474|34.135|2.052|63.569|1.00 24.01|B C|
|ATOM|4064|CG|ARG|B|474|34.840|0.710|63.614|1.00 23.92|B C|
|ATOM|4065|CD|ARG|B|474|34.429|-0.199|62.471|1.00 25.93|B C|
|ATOM|4066|NE|ARG|B|474|33.016|-0.555|62.537|1.00 26.56|B N|
|ATOM|4067|CZ|ARG|B|474|32.529|-1.697|63.025|1.00 25.45|B C|
|ATOM|4068|NH1|ARG|B|474|33.336|-2.642|63.482|1.00 22.66|B N|
|ATOM|4069|NH2|ARG|B|474|31.213|-1.832|63.170|1.00 25.13|B N|
|ATOM|4070|C|ARG|B|474|33.452|4.035|62.194|1.00 23.15|B C|
|ATOM|4071|O|ARG|B|474|32.355|3.951|61.661|1.00 24.13|B O|
|ATOM|4072|N|LEU|B|475|33.924|5.175|62.678|1.00 22.46|B N|
|ATOM|4073|CA|LEU|B|475|33.118|6.373|62.597|1.00 22.61|B C|
|ATOM|4074|CB|LEU|B|475|33.683|7.485|63.484|1.00 23.45|B C|
|ATOM|4075|CG|LEU|B|475|33.469|7.331|65.015|1.00 25.21|B C|
|ATOM|4076|CD1|LEU|B|475|34.275|8.402|65.749|1.00 23.39|B C|
|ATOM|4077|CD2|LEU|B|475|31.978|7.427|65.418|1.00 25.75|B C|
|ATOM|4078|C|LEU|B|475|32.976|6.839|61.139|1.00 22.08|B C|
|ATOM|4079|O|LEU|B|475|31.936|7.367|60.770|1.00 20.49|B O|
|ATOM|4080|N|CYS|B|476|34.040|6.680|60.339|1.00 20.97|B N|
|ATOM|4081|CA|CYS|B|476|34.019|7.064|58.924|1.00 20.54|B C|
|ATOM|4082|CB|CYS|B|476|35.414|6.925|58.276|1.00 19.86|B C|
|ATOM|4083|SG|CYS|B|476|36.705|8.073|58.910|1.00 22.10|B S|
|ATOM|4084|C|CYS|B|476|33.026|6.188|58.155|1.00 20.14|B C|
|ATOM|4085|O|CYS|B|476|32.492|6.628|57.152|1.00 19.89|B O|
|ATOM|4086|N|TRP|B|477|32.799|4.959|58.638|1.00 19.91|B N|
|ATOM|4087|CA|TRP|B|477|31.891|4.008|57.999|1.00 20.99|B C|
|ATOM|4088|CB|TRP|B|477|32.495|2.593|57.998|1.00 20.70|B C|
|ATOM|4089|CG|TRP|B|477|33.873|2.495|57.444|1.00 20.52|B C|
|ATOM|4090|CD2|TRP|B|477|34.880|1.538|57.810|1.00 19.85|B C|
|ATOM|4091|CE2|TRP|B|477|36.038|1.833|57.040|1.00 20.71|B C|
|ATOM|4092|CE3|TRP|B|477|34.922|0.460|58.717|1.00 19.94|B C|
|ATOM|4093|CD1|TRP|B|477|34.448|3.306|56.484|1.00 20.69|B C|
|ATOM|4094|NE1|TRP|B|477|35.739|2.914|56.243|1.00 21.37|B N|
|ATOM|4095|CZ2|TRP|B|477|37.232|1.094|57.152|1.00 19.66|B C|
|ATOM|4096|CZ3|TRP|B|477|36.118|-0.288|58.830|1.00 20.01|B C|
|ATOM|4097|CH2|TRP|B|477|37.255|0.041|58.043|1.00 21.07|B C|
|ATOM|4098|C|TRP|B|477|30.490|3.933|58.641|1.00 21.10|B C|
|ATOM|4099|O|TRP|B|477|29.819|2.909|58.519|1.00 21.58|B O|
|ATOM|4100|N|LYS|B|478|30.073|4.967|59.374|1.00 21.56|B N|
|ATOM|4101|CA|LYS|B|478|28.723|4.939|59.942|1.00 23.42|B C|
|ATOM|4102|CB|LYS|B|478|28.410|6.206|60.761|1.00 23.38|B C|
|ATOM|4103|CG|LYS|B|478|29.178|6.321|62.105|1.00 27.04|B C|
|ATOM|4104|CD|LYS|B|478|28.872|5.172|63.023|1.00 30.05|B C|
|ATOM|4105|CE|LYS|B|478|27.551|5.416|63.767|1.00 33.98|B C|
|ATOM|4106|NZ|LYS|B|478|27.116|4.128|64.450|1.00 37.92|B N|
|ATOM|4107|C|LYS|B|478|27.777|4.860|58.741|1.00 22.96|B C|
|ATOM|4108|O|LYS|B|478|28.006|5.520|57.710|1.00 21.88|B O|
|ATOM|4109|N|GLU|B|479|26.738|4.049|58.872|1.00 22.95|B N|
|ATOM|4110|CA|GLU|B|479|25.776|3.878|57.794|1.00 23.21|B C|
|ATOM|4111|CB|GLU|B|479|24.618|2.964|58.236|1.00 23.15|B C|
|ATOM|4112|CG|GLU|B|479|23.645|2.568|57.068|1.00 22.44|B C|
|ATOM|4113|CD|GLU|B|479|24.352|1.738|55.967|1.00 24.18|B C|
|ATOM|4114|OE1|GLU|B|479|25.232|0.918|56.273|1.00 24.99|B O|
|ATOM|4115|OE2|GLU|B|479|24.028|1.890|54.784|1.00 23.84|B O|
|ATOM|4116|C|GLU|B|479|25.225|5.224|57.305|1.00 22.71|B C|
|ATOM|4117|O|GLU|B|479|25.155|5.476|56.107|1.00 21.64|B O|

Figure 11

| | | | | | | | | | | |
|---|---|---|---|---|---|---|---|---|---|---|
| ATOM | 4118 | N | ARG | B | 480 | 24.794 | 6.065 | 58.243 | 1.00 23.05 | B N |
| ATOM | 4119 | CA | ARG | B | 480 | 24.248 | 7.376 | 57.913 | 1.00 23.86 | B C |
| ATOM | 4120 | CB | ARG | B | 480 | 23.335 | 7.850 | 59.008 | 1.00 25.65 | B C |
| ATOM | 4121 | CG | ARG | B | 480 | 22.055 | 7.094 | 59.060 | 1.00 30.85 | B C |
| ATOM | 4122 | CD | ARG | B | 480 | 21.414 | 7.507 | 60.339 | 1.00 36.93 | B C |
| ATOM | 4123 | NE | ARG | B | 480 | 20.128 | 6.863 | 60.559 | 1.00 42.27 | B N |
| ATOM | 4124 | CZ | ARG | B | 480 | 19.612 | 6.647 | 61.766 | 1.00 44.60 | B C |
| ATOM | 4125 | NH1 | ARG | B | 480 | 20.290 | 7.019 | 62.858 | 1.00 45.80 | B N |
| ATOM | 4126 | NH2 | ARG | B | 480 | 18.393 | 6.126 | 61.876 | 1.00 45.43 | B N |
| ATOM | 4127 | C | ARG | B | 480 | 25.352 | 8.388 | 57.728 | 1.00 22.57 | B C |
| ATOM | 4128 | O | ARG | B | 480 | 26.176 | 8.573 | 58.614 | 1.00 23.15 | B O |
| ATOM | 4129 | N | PRO | B | 481 | 25.287 | 9.158 | 56.647 | 1.00 21.51 | B N |
| ATOM | 4130 | CD | PRO | B | 481 | 24.158 | 9.235 | 55.706 | 1.00 20.81 | B C |
| ATOM | 4131 | CA | PRO | B | 481 | 26.288 | 10.170 | 56.334 | 1.00 20.58 | B C |
| ATOM | 4132 | CB | PRO | B | 481 | 25.687 | 10.863 | 55.094 | 1.00 21.52 | B C |
| ATOM | 4133 | CG | PRO | B | 481 | 24.796 | 9.843 | 54.508 | 1.00 21.97 | B C |
| ATOM | 4134 | C | PRO | B | 481 | 26.473 | 11.164 | 57.459 | 1.00 20.87 | B C |
| ATOM | 4135 | O | PRO | B | 481 | 27.597 | 11.550 | 57.770 | 1.00 20.25 | B O |
| ATOM | 4136 | N | GLU | B | 482 | 25.359 | 11.609 | 58.046 | 1.00 21.93 | B N |
| ATOM | 4137 | CA | GLU | B | 482 | 25.395 | 12.601 | 59.128 | 1.00 22.13 | B C |
| ATOM | 4138 | CB | GLU | B | 482 | 23.962 | 13.120 | 59.460 | 1.00 22.98 | B C |
| ATOM | 4139 | CG | GLU | B | 482 | 23.009 | 12.132 | 60.145 | 1.00 24.88 | B C |
| ATOM | 4140 | CD | GLU | B | 482 | 22.190 | 11.279 | 59.182 | 1.00 26.67 | B C |
| ATOM | 4141 | OE1 | GLU | B | 482 | 22.530 | 11.172 | 57.968 | 1.00 29.25 | B O |
| ATOM | 4142 | OE2 | GLU | B | 482 | 21.219 | 10.679 | 59.649 | 1.00 27.78 | B O |
| ATOM | 4143 | C | GLU | B | 482 | 26.142 | 12.157 | 60.395 | 1.00 20.97 | B C |
| ATOM | 4144 | O | GLU | B | 482 | 26.603 | 12.982 | 61.155 | 1.00 22.77 | B O |
| ATOM | 4145 | N | ASP | B | 483 | 26.300 | 10.855 | 60.591 | 1.00 21.21 | B N |
| ATOM | 4146 | CA | ASP | B | 483 | 27.010 | 10.334 | 61.747 | 1.00 20.99 | B C |
| ATOM | 4147 | CB | ASP | B | 483 | 26.454 | 8.977 | 62.148 | 1.00 20.33 | B C |
| ATOM | 4148 | CG | ASP | B | 483 | 25.011 | 9.055 | 62.558 | 1.00 21.44 | B C |
| ATOM | 4149 | OD1 | ASP | B | 483 | 24.572 | 10.143 | 62.945 | 1.00 23.60 | B O |
| ATOM | 4150 | OD2 | ASP | B | 483 | 24.308 | 8.045 | 62.485 | 1.00 23.17 | B O |
| ATOM | 4151 | C | ASP | B | 483 | 28.504 | 10.199 | 61.502 | 1.00 21.52 | B C |
| ATOM | 4152 | O | ASP | B | 483 | 29.247 | 9.771 | 62.396 | 1.00 22.15 | B O |
| ATOM | 4153 | N | ARG | B | 484 | 28.937 | 10.474 | 60.280 | 1.00 20.80 | B N |
| ATOM | 4154 | CA | ARG | B | 484 | 30.363 | 10.383 | 59.978 | 1.00 20.41 | B C |
| ATOM | 4155 | CB | ARG | B | 484 | 30.596 | 10.050 | 58.496 | 1.00 21.68 | B C |
| ATOM | 4156 | CG | ARG | B | 484 | 29.980 | 8.722 | 58.061 | 1.00 20.10 | B C |
| ATOM | 4157 | CD | ARG | B | 484 | 30.009 | 8.611 | 56.548 | 1.00 18.34 | B C |
| ATOM | 4158 | NE | ARG | B | 484 | 29.102 | 7.558 | 56.110 | 1.00 19.42 | B N |
| ATOM | 4159 | CZ | ARG | B | 484 | 28.591 | 7.411 | 54.885 | 1.00 17.99 | B C |
| ATOM | 4160 | NH1 | ARG | B | 484 | 28.891 | 8.243 | 53.892 | 1.00 16.87 | B N |
| ATOM | 4161 | NH2 | ARG | B | 484 | 27.736 | 6.420 | 54.683 | 1.00 15.36 | B N |
| ATOM | 4162 | C | ARG | B | 484 | 31.014 | 11.703 | 60.360 | 1.00 19.50 | B C |
| ATOM | 4163 | O | ARG | B | 484 | 30.421 | 12.764 | 60.188 | 1.00 18.96 | B O |
| ATOM | 4164 | N | PRO | B | 485 | 32.259 | 11.656 | 60.866 | 1.00 20.63 | B N |
| ATOM | 4165 | CD | PRO | B | 485 | 33.090 | 10.466 | 61.131 | 1.00 19.48 | B C |
| ATOM | 4166 | CA | PRO | B | 485 | 32.946 | 12.887 | 61.263 | 1.00 19.40 | B C |
| ATOM | 4167 | CB | PRO | B | 485 | 34.148 | 12.355 | 62.048 | 1.00 20.93 | B C |
| ATOM | 4168 | CG | PRO | B | 485 | 34.459 | 11.072 | 61.385 | 1.00 20.38 | B C |
| ATOM | 4169 | C | PRO | B | 485 | 33.346 | 13.790 | 60.084 | 1.00 20.77 | B C |
| ATOM | 4170 | O | PRO | B | 485 | 33.252 | 13.385 | 58.932 | 1.00 21.20 | B O |
| ATOM | 4171 | N | THR | B | 486 | 33.604 | 15.062 | 60.374 | 1.00 19.96 | B N |
| ATOM | 4172 | CA | THR | B | 486 | 34.047 | 16.007 | 59.359 | 1.00 21.11 | B C |
| ATOM | 4173 | CB | THR | B | 486 | 33.970 | 17.457 | 59.882 | 1.00 20.55 | B C |
| ATOM | 4174 | OG1 | THR | B | 486 | 34.580 | 17.481 | 61.179 | 1.00 23.65 | B O |
| ATOM | 4175 | CG2 | THR | B | 486 | 32.535 | 17.986 | 59.980 | 1.00 19.91 | B C |
| ATOM | 4176 | C | THR | B | 486 | 35.573 | 15.719 | 59.161 | 1.00 22.11 | B C |

Figure 11

| | | | | | | | | | | | |
|---|---|---|---|---|---|---|---|---|---|---|---|
| ATOM | 4177 | O | THR | B | 486 | 36.218 | 15.130 | 60.035 | 1.00 | 22.06 | B O |
| ATOM | 4178 | N | PHE | B | 487 | 36.149 | 16.202 | 58.062 | 1.00 | 21.28 | B N |
| ATOM | 4179 | CA | PHE | B | 487 | 37.565 | 16.020 | 57.807 | 1.00 | 21.80 | B C |
| ATOM | 4180 | CB | PHE | B | 487 | 37.923 | 16.280 | 56.344 | 1.00 | 20.18 | B C |
| ATOM | 4181 | CG | PHE | B | 487 | 37.679 | 15.109 | 55.452 | 1.00 | 18.81 | B C |
| ATOM | 4182 | CD1 | PHE | B | 487 | 38.481 | 13.972 | 55.538 | 1.00 | 19.23 | B C |
| ATOM | 4183 | CD2 | PHE | B | 487 | 36.660 | 15.143 | 54.503 | 1.00 | 20.27 | B C |
| ATOM | 4184 | CE1 | PHE | B | 487 | 38.279 | 12.882 | 54.692 | 1.00 | 17.45 | B C |
| ATOM | 4185 | CE2 | PHE | B | 487 | 36.439 | 14.062 | 53.647 | 1.00 | 18.45 | B C |
| ATOM | 4186 | CZ | PHE | B | 487 | 37.256 | 12.920 | 53.742 | 1.00 | 19.53 | B C |
| ATOM | 4187 | C | PHE | B | 487 | 38.314 | 16.978 | 58.710 | 1.00 | 22.93 | B C |
| ATOM | 4188 | O | PHE | B | 487 | 39.464 | 16.731 | 59.050 | 1.00 | 24.31 | B O |
| ATOM | 4189 | N | ASP | B | 488 | 37.651 | 18.058 | 59.109 | 1.00 | 23.81 | B N |
| ATOM | 4190 | CA | ASP | B | 488 | 38.226 | 19.048 | 60.009 | 1.00 | 24.99 | B C |
| ATOM | 4191 | CB | ASP | B | 488 | 37.215 | 20.196 | 60.205 | 1.00 | 28.23 | B C |
| ATOM | 4192 | CG | ASP | B | 488 | 37.632 | 21.212 | 61.276 | 1.00 | 32.43 | B C |
| ATOM | 4193 | OD1 | ASP | B | 488 | 38.841 | 21.357 | 61.555 | 1.00 | 34.73 | B O |
| ATOM | 4194 | OD2 | ASP | B | 488 | 36.725 | 21.866 | 61.849 | 1.00 | 34.03 | B O |
| ATOM | 4195 | C | ASP | B | 488 | 38.565 | 18.310 | 61.312 | 1.00 | 25.44 | B C |
| ATOM | 4196 | O | ASP | B | 488 | 39.672 | 18.467 | 61.819 | 1.00 | 26.44 | B O |
| ATOM | 4197 | N | TYR | B | 489 | 37.676 | 17.415 | 61.768 | 1.00 | 24.53 | B N |
| ATOM | 4198 | CA | TYR | B | 489 | 37.908 | 16.604 | 62.986 | 1.00 | 24.78 | B C |
| ATOM | 4199 | CB | TYR | B | 489 | 36.608 | 15.924 | 63.483 | 1.00 | 24.59 | B C |
| ATOM | 4200 | CG | TYR | B | 489 | 36.813 | 14.922 | 64.615 | 1.00 | 25.20 | B C |
| ATOM | 4201 | CD1 | TYR | B | 489 | 37.070 | 15.349 | 65.923 | 1.00 | 25.30 | B C |
| ATOM | 4202 | CE1 | TYR | B | 489 | 37.273 | 14.427 | 66.964 | 1.00 | 25.59 | B C |
| ATOM | 4203 | CD2 | TYR | B | 489 | 36.761 | 13.550 | 64.370 | 1.00 | 26.16 | B C |
| ATOM | 4204 | CE2 | TYR | B | 489 | 36.963 | 12.612 | 65.380 | 1.00 | 26.06 | B C |
| ATOM | 4205 | CZ | TYR | B | 489 | 37.221 | 13.049 | 66.687 | 1.00 | 28.33 | B C |
| ATOM | 4206 | OH | TYR | B | 489 | 37.449 | 12.096 | 67.684 | 1.00 | 28.42 | B O |
| ATOM | 4207 | C | TYR | B | 489 | 38.984 | 15.518 | 62.769 | 1.00 | 24.15 | B C |
| ATOM | 4208 | O | TYR | B | 489 | 39.875 | 15.357 | 63.604 | 1.00 | 22.45 | B O |
| ATOM | 4209 | N | LEU | B | 490 | 38.846 | 14.742 | 61.689 | 1.00 | 23.61 | B N |
| ATOM | 4210 | CA | LEU | B | 490 | 39.813 | 13.688 | 61.359 | 1.00 | 24.07 | B C |
| ATOM | 4211 | CB | LEU | B | 490 | 39.458 | 13.007 | 60.030 | 1.00 | 22.93 | B C |
| ATOM | 4212 | CG | LEU | B | 490 | 38.127 | 12.216 | 60.006 | 1.00 | 23.10 | B C |
| ATOM | 4213 | CD1 | LEU | B | 490 | 37.747 | 11.852 | 58.603 | 1.00 | 22.96 | B C |
| ATOM | 4214 | CD2 | LEU | B | 490 | 38.237 | 10.973 | 60.828 | 1.00 | 22.87 | B C |
| ATOM | 4215 | C | LEU | B | 490 | 41.241 | 14.261 | 61.317 | 1.00 | 25.17 | B C |
| ATOM | 4216 | O | LEU | B | 490 | 42.155 | 13.659 | 61.849 | 1.00 | 24.73 | B O |
| ATOM | 4217 | N | ARG | B | 491 | 41.414 | 15.452 | 60.738 | 1.00 | 26.49 | B N |
| ATOM | 4218 | CA | ARG | B | 491 | 42.735 | 16.065 | 60.705 | 1.00 | 28.93 | B C |
| ATOM | 4219 | CB | ARG | B | 491 | 42.739 | 17.358 | 59.887 | 1.00 | 30.45 | B C |
| ATOM | 4220 | CG | ARG | B | 491 | 44.037 | 18.155 | 60.058 | 1.00 | 34.38 | B C |
| ATOM | 4221 | CD | ARG | B | 491 | 43.871 | 19.636 | 59.771 | 1.00 | 38.21 | B C |
| ATOM | 4222 | NE | ARG | B | 491 | 42.703 | 20.206 | 60.437 | 1.00 | 43.85 | B N |
| ATOM | 4223 | CZ | ARG | B | 491 | 42.652 | 20.546 | 61.729 | 1.00 | 46.22 | B C |
| ATOM | 4224 | NH1 | ARG | B | 491 | 43.714 | 20.383 | 62.519 | 1.00 | 47.01 | B N |
| ATOM | 4225 | NH2 | ARG | B | 491 | 41.533 | 21.061 | 62.229 | 1.00 | 46.85 | B N |
| ATOM | 4226 | C | ARG | B | 491 | 43.261 | 16.323 | 62.144 | 1.00 | 30.47 | B C |
| ATOM | 4227 | O | ARG | B | 491 | 44.424 | 15.991 | 62.458 | 1.00 | 30.37 | B O |
| ATOM | 4228 | N | SER | B | 492 | 42.399 | 16.870 | 63.013 | 1.00 | 30.80 | B N |
| ATOM | 4229 | CA | SER | B | 492 | 42.747 | 17.157 | 64.411 | 1.00 | 31.66 | B C |
| ATOM | 4230 | CB | SER | B | 492 | 41.555 | 17.750 | 65.155 | 1.00 | 31.93 | B C |
| ATOM | 4231 | OG | SER | B | 492 | 41.311 | 19.061 | 64.714 | 1.00 | 35.33 | B O |
| ATOM | 4232 | C | SER | B | 492 | 43.210 | 15.928 | 65.168 | 1.00 | 31.57 | B C |
| ATOM | 4233 | O | SER | B | 492 | 44.240 | 15.968 | 65.823 | 1.00 | 31.92 | B O |
| ATOM | 4234 | N | VAL | B | 493 | 42.440 | 14.843 | 65.076 | 1.00 | 31.43 | B N |
| ATOM | 4235 | CA | VAL | B | 493 | 42.766 | 13.597 | 65.756 | 1.00 | 31.63 | B C |

Figure 11

| ATOM | 4236 | CB  | VAL | B | 493 | 41.540 | 12.598 | 65.790 | 1.00 | 33.10 | B | C |
| ATOM | 4237 | CG1 | VAL | B | 493 | 40.897 | 12.503 | 64.441 | 1.00 | 33.93 | B | C |
| ATOM | 4238 | CG2 | VAL | B | 493 | 41.978 | 11.168 | 66.207 | 1.00 | 33.07 | B | C |
| ATOM | 4239 | C   | VAL | B | 493 | 44.002 | 12.922 | 65.178 | 1.00 | 32.04 | B | C |
| ATOM | 4240 | O   | VAL | B | 493 | 44.823 | 12.390 | 65.927 | 1.00 | 32.08 | B | O |
| ATOM | 4241 | N   | LEU | B | 494 | 44.158 | 12.950 | 63.860 | 1.00 | 31.78 | B | N |
| ATOM | 4242 | CA  | LEU | B | 494 | 45.332 | 12.321 | 63.256 | 1.00 | 31.96 | B | C |
| ATOM | 4243 | CB  | LEU | B | 494 | 45.123 | 12.100 | 61.754 | 1.00 | 29.26 | B | C |
| ATOM | 4244 | CG  | LEU | B | 494 | 44.005 | 11.074 | 61.469 | 1.00 | 28.48 | B | C |
| ATOM | 4245 | CD1 | LEU | B | 494 | 43.628 | 11.037 | 59.999 | 1.00 | 25.52 | B | C |
| ATOM | 4246 | CD2 | LEU | B | 494 | 44.411 |  9.681 | 61.976 | 1.00 | 26.82 | B | C |
| ATOM | 4247 | C   | LEU | B | 494 | 46.628 | 13.080 | 63.585 | 1.00 | 32.72 | B | C |
| ATOM | 4248 | O   | LEU | B | 494 | 47.629 | 12.460 | 63.867 | 1.00 | 33.15 | B | O |
| ATOM | 4249 | N   | GLU | B | 495 | 46.582 | 14.408 | 63.642 | 1.00 | 34.90 | B | N |
| ATOM | 4250 | CA  | GLU | B | 495 | 47.758 | 15.208 | 63.983 | 1.00 | 37.82 | B | C |
| ATOM | 4251 | CB  | GLU | B | 495 | 47.453 | 16.699 | 63.857 | 1.00 | 39.98 | B | C |
| ATOM | 4252 | CG  | GLU | B | 495 | 47.580 | 17.238 | 62.442 | 1.00 | 44.29 | B | C |
| ATOM | 4253 | CD  | GLU | B | 495 | 47.080 | 18.664 | 62.298 | 1.00 | 47.20 | B | C |
| ATOM | 4254 | OE1 | GLU | B | 495 | 46.752 | 19.303 | 63.340 | 1.00 | 48.36 | B | O |
| ATOM | 4255 | OE2 | GLU | B | 495 | 47.018 | 19.141 | 61.128 | 1.00 | 48.89 | B | O |
| ATOM | 4256 | C   | GLU | B | 495 | 48.224 | 14.948 | 65.409 | 1.00 | 38.93 | B | C |
| ATOM | 4257 | O   | GLU | B | 495 | 49.408 | 14.715 | 65.637 | 1.00 | 38.50 | B | O |
| ATOM | 4258 | N   | ASP | B | 496 | 47.265 | 14.965 | 66.344 | 1.00 | 39.97 | B | N |
| ATOM | 4259 | CA  | ASP | B | 496 | 47.502 | 14.783 | 67.775 | 1.00 | 40.91 | B | C |
| ATOM | 4260 | CB  | ASP | B | 496 | 46.473 | 15.612 | 68.574 | 1.00 | 42.10 | B | C |
| ATOM | 4261 | CG  | ASP | B | 496 | 46.557 | 17.128 | 68.277 | 1.00 | 44.21 | B | C |
| ATOM | 4262 | OD1 | ASP | B | 496 | 47.674 | 17.694 | 68.248 | 1.00 | 43.43 | B | O |
| ATOM | 4263 | OD2 | ASP | B | 496 | 45.497 | 17.767 | 68.080 | 1.00 | 46.00 | B | O |
| ATOM | 4264 | C   | ASP | B | 496 | 47.481 | 13.339 | 68.273 | 1.00 | 41.53 | B | C |
| ATOM | 4265 | O   | ASP | B | 496 | 47.536 | 13.114 | 69.472 | 1.00 | 41.88 | B | O |
| ATOM | 4266 | N   | PHE | B | 497 | 47.493 | 12.369 | 67.360 | 1.00 | 42.27 | B | N |
| ATOM | 4267 | CA  | PHE | B | 497 | 47.416 | 10.940 | 67.703 | 1.00 | 42.84 | B | C |
| ATOM | 4268 | CB  | PHE | B | 497 | 47.310 | 10.108 | 66.427 | 1.00 | 40.78 | B | C |
| ATOM | 4269 | CG  | PHE | B | 497 | 46.617 |  8.791 | 66.613 | 1.00 | 39.09 | B | C |
| ATOM | 4270 | CD1 | PHE | B | 497 | 45.236 |  8.703 | 66.568 | 1.00 | 39.58 | B | C |
| ATOM | 4271 | CD2 | PHE | B | 497 | 47.351 |  7.627 | 66.826 | 1.00 | 38.65 | B | C |
| ATOM | 4272 | CE1 | PHE | B | 497 | 44.601 |  7.470 | 66.731 | 1.00 | 38.82 | B | C |
| ATOM | 4273 | CE2 | PHE | B | 497 | 46.731 |  6.402 | 66.991 | 1.00 | 37.48 | B | C |
| ATOM | 4274 | CZ  | PHE | B | 497 | 45.363 |  6.319 | 66.944 | 1.00 | 38.25 | B | C |
| ATOM | 4275 | C   | PHE | B | 497 | 48.456 | 10.352 | 68.678 | 1.00 | 44.32 | B | C |
| ATOM | 4276 | O   | PHE | B | 497 | 48.149 |  9.433 | 69.433 | 1.00 | 43.67 | B | O |
| ATOM | 4277 | N   | PHE | B | 498 | 49.699 | 10.808 | 68.593 | 1.00 | 46.80 | B | N |
| ATOM | 4278 | CA  | PHE | B | 498 | 50.766 | 10.378 | 69.517 | 1.00 | 49.10 | B | C |
| ATOM | 4279 | CB  | PHE | B | 498 | 50.898 |  8.846 | 69.689 | 1.00 | 49.60 | B | C |
| ATOM | 4280 | CG  | PHE | B | 498 | 51.039 |  8.055 | 68.396 | 1.00 | 49.40 | B | C |
| ATOM | 4281 | CD1 | PHE | B | 498 | 51.354 |  8.668 | 67.185 | 1.00 | 49.13 | B | C |
| ATOM | 4282 | CD2 | PHE | B | 498 | 50.811 |  6.677 | 68.411 | 1.00 | 48.86 | B | C |
| ATOM | 4283 | CE1 | PHE | B | 498 | 51.427 |  7.912 | 66.007 | 1.00 | 49.76 | B | C |
| ATOM | 4284 | CE2 | PHE | B | 498 | 50.884 |  5.914 | 67.246 | 1.00 | 49.37 | B | C |
| ATOM | 4285 | CZ  | PHE | B | 498 | 51.191 |  6.531 | 66.039 | 1.00 | 49.09 | B | C |
| ATOM | 4286 | C   | PHE | B | 498 | 52.108 | 11.002 | 69.220 | 1.00 | 50.32 | B | C |
| ATOM | 4287 | O   | PHE | B | 498 | 52.272 | 12.108 | 69.775 | 1.00 | 51.52 | B | O |
| ATOM | 4288 | N1  | LIG | B | 500 | 53.849 | 13.098 | 39.622 | 1.00 | 20.00 | B | N |
| ATOM | 4289 | C1  | LIG | B | 500 | 52.955 | 14.030 | 39.469 | 1.00 | 20.00 | B | C |
| ATOM | 4290 | N2  | LIG | B | 500 | 51.801 | 13.491 | 38.978 | 1.00 | 20.00 | B | N |
| ATOM | 4291 | C2  | LIG | B | 500 | 50.566 | 14.219 | 38.673 | 1.00 | 20.00 | B | C |
| ATOM | 4292 | C3  | LIG | B | 500 | 50.431 | 14.381 | 37.158 | 1.00 | 20.00 | B | C |
| ATOM | 4293 | C4  | LIG | B | 500 | 52.010 | 12.144 | 38.824 | 1.00 | 20.00 | B | C |
| ATOM | 4294 | N3  | LIG | B | 500 | 51.270 | 11.125 | 38.397 | 1.00 | 20.00 | B | N |

Figure 11

```
ATOM   4295  C5   LIG B 500      51.767    9.899   38.364  1.00 20.00      B    C
ATOM   4296  N4   LIG B 500      50.967    8.864   37.913  1.00 20.00      B    N
ATOM   4297  C6   LIG B 500      51.361    7.475   38.155  1.00 20.00      B    C
ATOM   4298  C7   LIG B 500      52.419    7.058   37.131  1.00 20.00      B    C
ATOM   4299  C8   LIG B 500      51.939    7.346   39.565  1.00 20.00      B    C
ATOM   4300  C9   LIG B 500      50.137    6.566   38.021  1.00 20.00      B    C
ATOM   4301  O1   LIG B 500      49.125    7.238   37.269  1.00 20.00      B    O
ATOM   4302  N5   LIG B 500      53.009    9.629   38.749  1.00 20.00      B    N
ATOM   4303  C10  LIG B 500      53.816   10.588   39.190  1.00 20.00      B    C
ATOM   4304  N6   LIG B 500      55.110   10.296   39.588  1.00 20.00      B    N
ATOM   4305  C11  LIG B 500      55.635    9.016   39.375  1.00 20.00      B    C
ATOM   4306  C12  LIG B 500      54.820    8.001   38.891  1.00 20.00      B    C
ATOM   4307  C13  LIG B 500      55.339    6.739   38.680  1.00 20.00      B    C
ATOM   4308  C14  LIG B 500      56.676    6.485   38.951  1.00 20.00      B    C
ATOM   4309  O2   LIG B 500      57.187    5.242   38.743  1.00 20.00      B    O
ATOM   4310  C15  LIG B 500      58.567    5.296   39.111  1.00 20.00      B    C
ATOM   4311  C16  LIG B 500      59.204    3.922   38.897  0.00 20.00      B    C
ATOM   4312  N7   LIG B 500      59.089    3.541   37.484  0.00 20.00      B    N
ATOM   4313  C17  LIG B 500      59.718    2.221   37.350  0.00 20.00      B    C
ATOM   4314  C18  LIG B 500      59.633    1.761   35.893  0.00 20.00      B    C
ATOM   4315  O3   LIG B 500      60.313    2.699   35.057  0.00 20.00      B    O
ATOM   4316  C19  LIG B 500      60.198    2.216   33.716  0.00 20.00      B    C
ATOM   4317  C20  LIG B 500      57.491    7.497   39.436  1.00 20.00      B    C
ATOM   4318  C21  LIG B 500      56.974    8.762   39.642  1.00 20.00      B    C
ATOM   4319  C22  LIG B 500      53.328   11.906   39.242  1.00 20.00      B    C
ATOM   4320  OH2  H2O B 600      33.806    0.365   51.139  1.00 18.49      B    O
ATOM   4321  OH2  H2O B 601      29.725   19.478   61.600  1.00 71.12      B    O
ATOM   4322  OH2  H2O B 602      27.141   -1.528   59.938  1.00 17.19      B    O
ATOM   4323  OH2  H2O B 604      34.733   20.142   63.208  1.00 47.16      B    O
ATOM   4324  OH2  H2O B 605      22.868   -2.846   58.508  1.00 30.69      B    O
ATOM   4325  OH2  H2O B 606      35.727    9.443   47.332  1.00 16.53      B    O
ATOM   4326  OH2  H2O B 607      24.729    5.814   61.180  1.00 23.22      B    O
ATOM   4327  OH2  H2O B 608      29.126   12.879   63.732  1.00 48.64      B    O
ATOM   4328  OH2  H2O B 609      27.993   -8.031   58.503  1.00 26.25      B    O
ATOM   4329  OH2  H2O B 610      34.310   -1.583   56.060  1.00 17.98      B    O
ATOM   4330  OH2  H2O B 611      34.103    4.027   66.701  1.00 29.59      B    O
ATOM   4331  OH2  H2O B 612      28.984   16.904   59.999  1.00 30.24      B    O
ATOM   4332  OH2  H2O B 613      28.088   -5.936   60.627  1.00 62.00      B    O
ATOM   4333  OH2  H2O B 614      37.655   13.287   41.596  1.00 26.69      B    O
ATOM   4334  OH2  H2O B 615      18.797   14.553   63.510  1.00 24.79      B    O
ATOM   4335  OH2  H2O B 616      26.698   15.838   60.587  1.00 29.35      B    O
ATOM   4336  OH2  H2O B 617      31.172   -7.510   60.188  1.00 66.03      B    O
ATOM   4337  OH2  H2O B 618      36.700   -2.186   44.184  1.00 24.76      B    O
ATOM   4338  OH2  H2O B 619      27.287   17.451   56.165  1.00 74.17      B    O
ATOM   4339  OH2  H2O B 620      29.743   -4.170   63.184  1.00 35.15      B    O
ATOM   4340  OH2  H2O B 621      58.876   15.145   44.913  1.00 49.05      B    O
ATOM   4341  OH2  H2O B 622      32.186   21.981   62.349  1.00 43.84      B    O
ATOM   4342  OH2  H2O B 623      24.975   -0.936   58.413  1.00 34.31      B    O
ATOM   4343  OH2  H2O B 624      64.152   11.389   38.385  1.00 49.24      B    O
ATOM   4344  OH2  H2O B 625      48.814   17.369   58.510  1.00 55.55      B    O
ATOM   4345  OH2  H2O B 626      43.814    2.867   46.087  1.00 21.72      B    O
ATOM   4346  OH2  H2O B 627      31.898   16.431   56.649  1.00 18.71      B    O
ATOM   4347  OH2  H2O B 628      32.362    7.269   48.694  1.00 27.89      B    O
ATOM   4348  OH2  H2O B 630      37.192    7.596   67.690  1.00 58.83      B    O
ATOM   4349  OH2  H2O B 631      62.376   23.775   26.821  1.00 39.00      B    O
ATOM   4350  OH2  H2O B 632      33.961   -5.175   61.792  1.00 21.57      B    O
ATOM   4351  OH2  H2O B 633      44.965   10.114   40.787  1.00 52.29      B    O
ATOM   4352  OH2  H2O B 634      45.376   23.688   55.651  1.00 28.52      B    O
ATOM   4353  OH2  H2O B 635      26.895   11.081   50.673  1.00 35.24      B    O
```

Figure 11

| | | | | | | | | | | | |
|---|---|---|---|---|---|---|---|---|---|---|---|
| ATOM | 4354 | OH2 | H2O | B | 636 | 26.085 | 10.399 | 65.397 | 1.00 | 27.66 | B | O |
| ATOM | 4355 | OH2 | H2O | B | 638 | 20.189 | 14.379 | 65.839 | 1.00 | 32.07 | B | O |
| ATOM | 4356 | OH2 | H2O | B | 639 | 44.313 | 11.648 | 68.826 | 1.00 | 35.38 | B | O |
| ATOM | 4357 | OH2 | H2O | B | 640 | 26.479 | -0.871 | 54.942 | 1.00 | 18.73 | B | O |
| ATOM | 4358 | OH2 | H2O | B | 641 | 25.784 | 16.031 | 57.988 | 1.00 | 22.40 | B | O |
| ATOM | 4359 | OH2 | H2O | B | 642 | 47.812 | 22.903 | 44.752 | 1.00 | 31.18 | B | O |
| ATOM | 4360 | OH2 | H2O | B | 643 | 55.106 | 0.108 | 26.952 | 1.00 | 75.84 | B | O |
| ATOM | 4361 | OH2 | H2O | B | 644 | 31.306 | 1.542 | 61.089 | 1.00 | 20.37 | B | O |
| ATOM | 4362 | OH2 | H2O | B | 645 | 23.903 | -1.170 | 50.817 | 1.00 | 38.79 | B | O |
| ATOM | 4363 | OH2 | H2O | B | 646 | 56.468 | 21.621 | 19.456 | 1.00 | 50.42 | B | O |
| ATOM | 4364 | OH2 | H2O | B | 647 | 32.582 | -13.196 | 53.431 | 1.00 | 55.14 | B | O |
| ATOM | 4365 | OH2 | H2O | B | 648 | 29.148 | 17.593 | 50.189 | 1.00 | 22.44 | B | O |
| ATOM | 4366 | OH2 | H2O | B | 649 | 15.556 | 16.909 | 62.602 | 1.00 | 63.23 | B | O |
| ATOM | 4367 | OH2 | H2O | B | 650 | 40.505 | -5.529 | 57.719 | 1.00 | 44.49 | B | O |
| ATOM | 4368 | OH2 | H2O | B | 651 | 30.953 | 25.186 | 59.286 | 1.00 | 27.30 | B | O |
| ATOM | 4369 | OH2 | H2O | B | 652 | 26.692 | 1.828 | 61.293 | 1.00 | 30.95 | B | O |
| ATOM | 4370 | OH2 | H2O | B | 653 | 32.202 | -0.013 | 48.938 | 1.00 | 17.69 | B | O |
| ATOM | 4371 | OH2 | H2O | B | 654 | 32.046 | -8.314 | 64.661 | 1.00 | 23.79 | B | O |
| ATOM | 4372 | OH2 | H2O | B | 655 | 52.673 | 1.679 | 32.969 | 1.00 | 31.72 | B | O |
| ATOM | 4373 | OH2 | H2O | B | 656 | 33.355 | 19.218 | 43.735 | 1.00 | 29.86 | B | O |
| ATOM | 4374 | OH2 | H2O | B | 657 | 29.740 | 19.331 | 53.529 | 1.00 | 77.86 | B | O |
| ATOM | 4375 | OH2 | H2O | B | 658 | 26.985 | -1.882 | 65.995 | 1.00 | 40.84 | B | O |
| ATOM | 4376 | OH2 | H2O | B | 659 | 38.126 | -5.467 | 64.960 | 1.00 | 25.25 | B | O |
| ATOM | 4377 | OH2 | H2O | B | 660 | 52.515 | 1.413 | 39.515 | 1.00 | 37.70 | B | O |
| ATOM | 4378 | OH2 | H2O | B | 661 | 43.442 | 8.189 | 36.463 | 1.00 | 41.08 | B | O |
| ATOM | 4379 | OH2 | H2O | B | 662 | 22.382 | 11.745 | 63.556 | 1.00 | 54.90 | B | O |
| ATOM | 4380 | OH2 | H2O | B | 663 | 35.090 | -11.782 | 56.908 | 1.00 | 26.80 | B | O |
| ATOM | 4381 | OH2 | H2O | B | 664 | 54.849 | 0.388 | 39.938 | 1.00 | 56.68 | B | O |
| ATOM | 4382 | OH2 | H2O | B | 665 | 31.163 | 19.770 | 56.958 | 1.00 | 63.66 | B | O |
| ATOM | 4383 | OH2 | H2O | B | 666 | 26.310 | -1.832 | 62.393 | 1.00 | 37.81 | B | O |
| ATOM | 4384 | OH2 | H2O | B | 667 | 37.014 | 21.448 | 56.999 | 1.00 | 23.54 | B | O |
| ATOM | 4385 | OH2 | H2O | B | 668 | 51.270 | -0.767 | 60.661 | 1.00 | 43.05 | B | O |
| ATOM | 4386 | OH2 | H2O | B | 669 | 33.564 | 21.652 | 58.246 | 1.00 | 51.01 | B | O |
| ATOM | 4387 | OH2 | H2O | B | 670 | 22.829 | -1.467 | 62.390 | 1.00 | 60.71 | B | O |
| ATOM | 4388 | OH2 | H2O | B | 671 | 25.978 | 14.417 | 53.420 | 1.00 | 31.89 | B | O |
| ATOM | 4389 | OH2 | H2O | B | 672 | 34.878 | 20.081 | 41.396 | 1.00 | 37.13 | B | O |
| ATOM | 4390 | OH2 | H2O | B | 673 | 62.167 | 1.272 | 48.384 | 1.00 | 47.15 | B | O |
| ATOM | 4391 | OH2 | H2O | B | 674 | 42.831 | 22.104 | 55.842 | 1.00 | 30.15 | B | O |
| ATOM | 4392 | OH2 | H2O | B | 675 | 25.467 | -2.393 | 49.056 | 1.00 | 26.74 | B | O |
| ATOM | 4393 | OH2 | H2O | B | 676 | 60.055 | 18.349 | 41.785 | 1.00 | 48.81 | B | O |
| ATOM | 4394 | OH2 | H2O | B | 677 | 33.753 | 7.510 | 46.268 | 1.00 | 29.38 | B | O |
| ATOM | 4395 | OH2 | H2O | B | 678 | 22.955 | 3.677 | 53.350 | 1.00 | 40.48 | B | O |
| ATOM | 4396 | OH2 | H2O | B | 679 | 43.863 | 1.123 | 44.096 | 1.00 | 36.20 | B | O |
| ATOM | 4397 | OH2 | H2O | B | 680 | 60.950 | 6.795 | 28.694 | 1.00 | 35.59 | B | O |
| ATOM | 4398 | OH2 | H2O | B | 681 | 22.016 | 3.469 | 50.764 | 1.00 | 35.22 | B | O |
| ATOM | 4399 | OH2 | H2O | B | 682 | 57.839 | 19.960 | 40.545 | 1.00 | 31.51 | B | O |
| ATOM | 4400 | OH2 | H2O | B | 683 | 47.864 | 5.658 | 40.348 | 1.00 | 57.11 | B | O |
| ATOM | 4401 | OH2 | H2O | B | 684 | 42.991 | -2.277 | 53.141 | 1.00 | 23.46 | B | O |
| ATOM | 4402 | OH2 | H2O | B | 685 | 23.773 | -0.357 | 53.359 | 1.00 | 33.37 | B | O |
| ATOM | 4403 | OH2 | H2O | B | 686 | 45.654 | -1.373 | 69.533 | 1.00 | 45.39 | B | O |
| ATOM | 4404 | OH2 | H2O | B | 687 | 26.947 | -4.194 | 64.454 | 1.00 | 32.66 | B | O |
| ATOM | 4405 | OH2 | H2O | B | 688 | 62.193 | 9.743 | 48.792 | 1.00 | 50.15 | B | O |
| ATOM | 4406 | OH2 | H2O | B | 689 | 23.465 | -2.621 | 47.085 | 1.00 | 43.10 | B | O |
| ATOM | 4407 | OH2 | H2O | B | 690 | 33.074 | 17.308 | 27.370 | 1.00 | 36.16 | B | O |
| ATOM | 4408 | OH2 | H2O | B | 691 | 46.808 | 24.029 | 41.079 | 1.00 | 26.07 | B | O |
| ATOM | 4409 | OH2 | H2O | B | 692 | 40.574 | 0.423 | 41.914 | 1.00 | 34.22 | B | O |
| ATOM | 4410 | OH2 | H2O | B | 693 | 44.962 | -1.118 | 48.368 | 1.00 | 29.09 | B | O |
| ATOM | 4411 | OH2 | H2O | B | 694 | 45.944 | 22.335 | 43.032 | 1.00 | 40.19 | B | O |
| ATOM | 4412 | OH2 | H2O | B | 695 | 18.580 | 12.092 | 66.953 | 1.00 | 40.82 | B | O |

Figure 11

| ATOM | 4413 | OH2 | H2O | B | 696 | 59.227 | 6.092 | 58.963 | 1.00 | 50.57 | B | O |
| ATOM | 4414 | OH2 | H2O | B | 697 | 39.374 | 6.179 | 68.597 | 1.00 | 57.76 | B | O |
| ATOM | 4415 | OH2 | H2O | B | 698 | 53.468 | 10.708 | 25.493 | 1.00 | 50.50 | B | O |
| ATOM | 4416 | OH2 | H2O | B | 699 | 23.181 | 0.710 | 60.348 | 1.00 | 36.35 | B | O |
| ATOM | 4417 | OH2 | H2O | B | 700 | 34.900 | 11.268 | 68.418 | 1.00 | 65.02 | B | O |
| ATOM | 4418 | OH2 | H2O | B | 701 | 62.327 | 10.582 | 36.714 | 1.00 | 34.41 | B | O |
| END | | | | | | | | | | | | |

Figure 11

```
CRYST1   57.098   44.249  118.323  90.00   89.95   90.00 P21              1
SCALE1      0.017514  0.000000 -0.000015        0.00000
SCALE2      0.000000  0.022599  0.000000        0.00000
SCALE3      0.000000  0.000000  0.008451        0.00000
ATOM      1  CB  TRP A 238      18.785  -5.698  26.958  1.00 57.87      A    C
ATOM      2  CG  TRP A 238      18.272  -6.193  25.616  1.00 59.24      A    C
ATOM      3  CD2 TRP A 238      18.805  -5.881  24.323  1.00 59.57      A    C
ATOM      4  CE2 TRP A 238      18.018  -6.577  23.365  1.00 59.71      A    C
ATOM      5  CE3 TRP A 238      19.863  -5.086  23.855  1.00 59.62      A    C
ATOM      6  CD1 TRP A 238      17.216  -7.033  25.407  1.00 59.78      A    C
ATOM      7  NE1 TRP A 238      17.059  -7.270  24.063  1.00 60.17      A    N
ATOM      8  CZ2 TRP A 238      18.257  -6.500  21.987  1.00 59.54      A    C
ATOM      9  CZ3 TRP A 238      20.103  -5.006  22.475  1.00 59.54      A    C
ATOM     10  CH2 TRP A 238      19.299  -5.712  21.562  1.00 59.14      A    C
ATOM     11  C   TRP A 238      20.514  -5.783  28.782  1.00 55.92      A    C
ATOM     12  O   TRP A 238      21.152  -4.733  28.674  1.00 56.05      A    O
ATOM     13  N   TRP A 238      19.638  -7.911  27.788  1.00 56.14      A    N
ATOM     14  CA  TRP A 238      19.987  -6.484  27.527  0.00 56.50      A    C
ATOM     15  N   GLU A 239      20.209  -6.316  29.971  1.00 54.78      A    N
ATOM     16  CA  GLU A 239      20.711  -5.704  31.201  0.00 53.77      A    C
ATOM     17  CB  GLU A 239      19.975  -6.178  32.459  1.00 56.06      A    C
ATOM     18  CG  GLU A 239      19.003  -5.149  33.045  1.00 59.67      A    C
ATOM     19  CD  GLU A 239      17.556  -5.380  32.573  1.00 62.55      A    C
ATOM     20  OE1 GLU A 239      17.295  -5.289  31.336  1.00 63.25      A    O
ATOM     21  OE2 GLU A 239      16.688  -5.673  33.445  1.00 63.20      A    O
ATOM     22  C   GLU A 239      22.192  -6.001  31.355  1.00 51.59      A    C
ATOM     23  O   GLU A 239      22.684  -7.049  30.923  1.00 51.64      A    O
ATOM     24  N   VAL A 240      22.918  -5.020  31.866  1.00 48.53      A    N
ATOM     25  CA  VAL A 240      24.338  -5.192  32.085  0.00 46.35      A    C
ATOM     26  CB  VAL A 240      25.190  -4.669  30.916  1.00 46.39      A    C
ATOM     27  CG1 VAL A 240      24.976  -5.541  29.671  1.00 46.08      A    C
ATOM     28  CG2 VAL A 240      24.885  -3.192  30.669  1.00 45.92      A    C
ATOM     29  C   VAL A 240      24.738  -4.467  33.341  1.00 44.08      A    C
ATOM     30  O   VAL A 240      24.071  -3.511  33.765  1.00 42.79      A    O
ATOM     31  N   PRO A 241      25.787  -4.968  34.000  1.00 42.81      A    N
ATOM     32  CD  PRO A 241      26.465  -6.246  33.726  1.00 42.39      A    C
ATOM     33  CA  PRO A 241      26.287  -4.367  35.229  0.00 41.95      A    C
ATOM     34  CB  PRO A 241      27.294  -5.410  35.737  1.00 41.80      A    C
ATOM     35  CG  PRO A 241      26.828  -6.695  35.110  1.00 41.36      A    C
ATOM     36  C   PRO A 241      26.966  -3.029  34.935  1.00 41.24      A    C
ATOM     37  O   PRO A 241      27.654  -2.871  33.942  1.00 40.63      A    O
ATOM     38  N   ARG A 242      26.704  -2.066  35.795  1.00 40.97      A    N
ATOM     39  CA  ARG A 242      27.273  -0.741  35.709  0.00 41.94      A    C
ATOM     40  CB  ARG A 242      26.858   0.008  36.952  1.00 41.90      A    C
ATOM     41  CG  ARG A 242      27.484   1.338  37.086  1.00 45.26      A    C
ATOM     42  CD  ARG A 242      26.827   2.303  36.198  1.00 45.28      A    C
ATOM     43  NE  ARG A 242      25.378   2.289  36.370  1.00 48.14      A    N
ATOM     44  CZ  ARG A 242      24.745   2.647  37.479  1.00 46.67      A    C
ATOM     45  NH1 ARG A 242      25.444   3.029  38.523  1.00 48.28      A    N
ATOM     46  NH2 ARG A 242      23.428   2.752  37.496  1.00 45.48      A    N
```

Figure 12

```
ATOM    47  C   ARG A 242      28.808  -0.757  35.586  1.00 41.83      A    C
ATOM    48  O   ARG A 242      29.381   0.116  34.918  1.00 41.60      A    O
ATOM    49  N   GLU A 243      29.434  -1.777  36.187  1.00 42.39      A    N
ATOM    50  CA  GLU A 243      30.903  -2.005  36.201  0.00 43.13      A    C
ATOM    51  CB  GLU A 243      31.305  -3.284  36.979  1.00 44.01      A    C
ATOM    52  CG  GLU A 243      31.162  -3.216  38.483  1.00 47.78      A    C
ATOM    53  CD  GLU A 243      29.696  -3.290  38.947  1.00 49.81      A    C
ATOM    54  OE1 GLU A 243      29.201  -4.422  39.174  1.00 49.15      A    O
ATOM    55  OE2 GLU A 243      29.043  -2.218  39.081  1.00 50.30      A    O
ATOM    56  C   GLU A 243      31.481  -2.155  34.805  1.00 42.05      A    C
ATOM    57  O   GLU A 243      32.658  -1.889  34.597  1.00 41.87      A    O
ATOM    58  N   THR A 244      30.689  -2.698  33.885  1.00 41.32      A    N
ATOM    59  CA  THR A 244      31.139  -2.866  32.508  0.00 40.16      A    C
ATOM    60  CB  THR A 244      30.220  -3.814  31.716  1.00 40.73      A    C
ATOM    61  OG1 THR A 244      28.898  -3.257  31.640  1.00 40.67      A    O
ATOM    62  CG2 THR A 244      30.149  -5.178  32.363  1.00 40.05      A    C
ATOM    63  C   THR A 244      31.102  -1.517  31.797  1.00 39.57      A    C
ATOM    64  O   THR A 244      31.367  -1.446  30.620  1.00 39.94      A    O
ATOM    65  N   LEU A 245      30.863  -0.439  32.526  1.00 38.83      A    N
ATOM    66  CA  LEU A 245      30.753   0.850  31.900  0.00 38.47      A    C
ATOM    67  CB  LEU A 245      29.279   1.182  31.829  1.00 40.12      A    C
ATOM    68  CG  LEU A 245      28.629   1.674  30.555  1.00 41.83      A    C
ATOM    69  CD1 LEU A 245      28.870   0.680  29.436  1.00 42.46      A    C
ATOM    70  CD2 LEU A 245      27.119   1.781  30.838  1.00 43.75      A    C
ATOM    71  C   LEU A 245      31.457   2.026  32.559  1.00 38.13      A    C
ATOM    72  O   LEU A 245      31.196   2.352  33.712  1.00 38.85      A    O
ATOM    73  N   LYS A 246      32.272   2.726  31.778  1.00 36.95      A    N
ATOM    74  CA  LYS A 246      32.948   3.916  32.252  0.00 35.65      A    C
ATOM    75  CB  LYS A 246      34.487   3.766  32.218  1.00 37.34      A    C
ATOM    76  CG  LYS A 246      35.311   5.017  32.748  1.00 38.27      A    C
ATOM    77  CD  LYS A 246      36.845   4.791  32.834  1.00 39.24      A    C
ATOM    78  CE  LYS A 246      37.429   4.044  31.589  1.00 40.66      A    C
ATOM    79  NZ  LYS A 246      38.896   3.695  31.677  1.00 41.55      A    N
ATOM    80  C   LYS A 246      32.491   5.078  31.373  1.00 34.80      A    C
ATOM    81  O   LYS A 246      32.631   5.054  30.151  1.00 34.17      A    O
ATOM    82  N   LEU A 247      31.901   6.082  31.999  1.00 34.37      A    N
ATOM    83  CA  LEU A 247      31.441   7.252  31.318  0.00 33.97      A    C
ATOM    84  CB  LEU A 247      30.217   7.848  32.035  1.00 33.48      A    C
ATOM    85  CG  LEU A 247      28.850   7.255  31.649  1.00 33.23      A    C
ATOM    86  CD1 LEU A 247      28.756   5.776  31.946  1.00 32.65      A    C
ATOM    87  CD2 LEU A 247      27.725   8.004  32.335  1.00 33.04      A    C
ATOM    88  C   LEU A 247      32.628   8.190  31.354  1.00 34.95      A    C
ATOM    89  O   LEU A 247      33.150   8.526  32.427  1.00 35.75      A    O
ATOM    90  N   VAL A 248      33.062   8.619  30.176  1.00 34.49      A    N
ATOM    91  CA  VAL A 248      34.214   9.481  30.078  0.00 33.58      A    C
ATOM    92  CB  VAL A 248      35.122   8.950  29.011  1.00 33.39      A    C
ATOM    93  CG1 VAL A 248      36.370   9.787  28.879  1.00 33.94      A    C
ATOM    94  CG2 VAL A 248      35.451   7.511  29.357  1.00 33.82      A    C
ATOM    95  C   VAL A 248      33.960  10.952  29.896  1.00 33.85      A    C
ATOM    96  O   VAL A 248      34.430  11.758  30.681  1.00 34.82      A    O
ATOM    97  N   GLU A 249      33.158  11.316  28.912  1.00 33.88      A    N
ATOM    98  CA  GLU A 249      32.912  12.728  28.677  0.00 33.42      A    C
ATOM    99  CB  GLU A 249      33.755  13.121  27.470  1.00 33.97      A    C
ATOM   100  CG  GLU A 249      33.359  14.350  26.703  1.00 34.50      A    C
ATOM   101  CD  GLU A 249      34.182  14.520  25.439  1.00 36.74      A    C
ATOM   102  OE1 GLU A 249      35.014  13.624  25.116  1.00 36.77      A    O
ATOM   103  OE2 GLU A 249      33.964  15.532  24.733  1.00 37.82      A    O
ATOM   104  C   GLU A 249      31.430  13.050  28.428  1.00 33.49      A    C
ATOM   105  O   GLU A 249      30.735  12.356  27.674  1.00 33.15      A    O
```

Figure 12

| ATOM | 106 | N | ARG | A | 250 | 30.963 | 14.152 | 28.984 | 1.00 | 32.89 | A | N |
| ATOM | 107 | CA | ARG | A | 250 | 29.591 | 14.513 | 28.767 | 0.00 | 33.33 | A | C |
| ATOM | 108 | CB | ARG | A | 250 | 29.092 | 15.463 | 29.824 | 1.00 | 34.50 | A | C |
| ATOM | 109 | CG | ARG | A | 250 | 27.604 | 15.366 | 29.919 | 1.00 | 36.76 | A | C |
| ATOM | 110 | CD | ARG | A | 250 | 27.139 | 16.097 | 31.117 | 1.00 | 39.09 | A | C |
| ATOM | 111 | NE | ARG | A | 250 | 27.338 | 17.505 | 30.892 | 1.00 | 40.86 | A | N |
| ATOM | 112 | CZ | ARG | A | 250 | 27.166 | 18.430 | 31.820 | 1.00 | 43.27 | A | C |
| ATOM | 113 | NH1 | ARG | A | 250 | 26.801 | 18.067 | 33.048 | 1.00 | 44.54 | A | N |
| ATOM | 114 | NH2 | ARG | A | 250 | 27.294 | 19.717 | 31.508 | 1.00 | 43.21 | A | N |
| ATOM | 115 | C | ARG | A | 250 | 29.443 | 15.213 | 27.448 | 1.00 | 33.30 | A | C |
| ATOM | 116 | O | ARG | A | 250 | 30.179 | 16.172 | 27.185 | 1.00 | 32.97 | A | O |
| ATOM | 117 | N | LEU | A | 251 | 28.446 | 14.774 | 26.667 | 1.00 | 31.29 | A | N |
| ATOM | 118 | CA | LEU | A | 251 | 28.159 | 15.368 | 25.368 | 0.00 | 29.56 | A | C |
| ATOM | 119 | CB | LEU | A | 251 | 27.671 | 14.310 | 24.403 | 1.00 | 27.75 | A | C |
| ATOM | 120 | CG | LEU | A | 251 | 28.700 | 13.191 | 24.276 | 1.00 | 28.72 | A | C |
| ATOM | 121 | CD1 | LEU | A | 251 | 28.092 | 12.081 | 23.438 | 1.00 | 29.06 | A | C |
| ATOM | 122 | CD2 | LEU | A | 251 | 30.034 | 13.708 | 23.614 | 1.00 | 28.00 | A | C |
| ATOM | 123 | C | LEU | A | 251 | 27.088 | 16.414 | 25.582 | 1.00 | 29.30 | A | C |
| ATOM | 124 | O | LEU | A | 251 | 27.016 | 17.402 | 24.875 | 1.00 | 28.79 | A | O |
| ATOM | 125 | N | GLY | A | 252 | 26.252 | 16.208 | 26.597 | 1.00 | 28.86 | A | N |
| ATOM | 126 | CA | GLY | A | 252 | 25.209 | 17.183 | 26.849 | 0.00 | 27.78 | A | C |
| ATOM | 127 | C | GLY | A | 252 | 24.399 | 16.904 | 28.098 | 1.00 | 26.94 | A | C |
| ATOM | 128 | O | GLY | A | 252 | 24.346 | 15.775 | 28.580 | 1.00 | 25.89 | A | O |
| ATOM | 129 | N | ALA | A | 253 | 23.728 | 17.955 | 28.574 | 1.00 | 26.76 | A | N |
| ATOM | 130 | CA | ALA | A | 253 | 22.884 | 17.918 | 29.761 | 0.00 | 27.41 | A | C |
| ATOM | 131 | CB | ALA | A | 253 | 23.627 | 18.493 | 30.970 | 1.00 | 26.48 | A | C |
| ATOM | 132 | C | ALA | A | 253 | 21.650 | 18.774 | 29.481 | 1.00 | 27.58 | A | C |
| ATOM | 133 | O | ALA | A | 253 | 21.743 | 19.948 | 29.102 | 1.00 | 25.24 | A | O |
| ATOM | 134 | N | GLY | A | 254 | 20.495 | 18.155 | 29.725 | 1.00 | 28.70 | A | N |
| ATOM | 135 | CA | GLY | A | 254 | 19.215 | 18.811 | 29.516 | 0.00 | 30.55 | A | C |
| ATOM | 136 | C | GLY | A | 254 | 18.286 | 18.657 | 30.701 | 1.00 | 31.39 | A | C |
| ATOM | 137 | O | GLY | A | 254 | 18.678 | 18.188 | 31.772 | 1.00 | 31.67 | A | O |
| ATOM | 138 | N | GLN | A | 255 | 17.017 | 18.940 | 30.459 | 1.00 | 32.27 | A | N |
| ATOM | 139 | CA | GLN | A | 255 | 16.015 | 18.892 | 31.516 | 0.00 | 32.57 | A | C |
| ATOM | 140 | CB | GLN | A | 255 | 14.724 | 19.557 | 31.002 | 1.00 | 35.76 | A | C |
| ATOM | 141 | CG | GLN | A | 255 | 13.814 | 20.131 | 32.103 | 1.00 | 41.64 | A | C |
| ATOM | 142 | CD | GLN | A | 255 | 12.316 | 20.300 | 31.690 | 1.00 | 45.30 | A | C |
| ATOM | 143 | OE1 | GLN | A | 255 | 11.429 | 20.455 | 32.578 | 1.00 | 46.00 | A | O |
| ATOM | 144 | NE2 | GLN | A | 255 | 12.027 | 20.251 | 30.356 | 1.00 | 46.59 | A | N |
| ATOM | 145 | C | GLN | A | 255 | 15.746 | 17.491 | 32.055 | 1.00 | 30.91 | A | C |
| ATOM | 146 | O | GLN | A | 255 | 15.382 | 17.346 | 33.207 | 1.00 | 31.26 | A | O |
| ATOM | 147 | N | PHE | A | 256 | 15.951 | 16.445 | 31.257 | 1.00 | 28.94 | A | N |
| ATOM | 148 | CA | PHE | A | 256 | 15.632 | 15.100 | 31.724 | 0.00 | 27.56 | A | C |
| ATOM | 149 | CB | PHE | A | 256 | 14.674 | 14.369 | 30.752 | 1.00 | 27.01 | A | C |
| ATOM | 150 | CG | PHE | A | 256 | 13.348 | 15.034 | 30.569 | 1.00 | 26.95 | A | C |
| ATOM | 151 | CD1 | PHE | A | 256 | 12.915 | 16.003 | 31.445 | 1.00 | 26.06 | A | C |
| ATOM | 152 | CD2 | PHE | A | 256 | 12.495 | 14.651 | 29.513 | 1.00 | 28.03 | A | C |
| ATOM | 153 | CE1 | PHE | A | 256 | 11.655 | 16.598 | 31.310 | 1.00 | 28.13 | A | C |
| ATOM | 154 | CE2 | PHE | A | 256 | 11.210 | 15.258 | 29.361 | 1.00 | 27.48 | A | C |
| ATOM | 155 | CZ | PHE | A | 256 | 10.803 | 16.223 | 30.263 | 1.00 | 27.70 | A | C |
| ATOM | 156 | C | PHE | A | 256 | 16.814 | 14.173 | 31.964 | 1.00 | 27.01 | A | C |
| ATOM | 157 | O | PHE | A | 256 | 16.627 | 12.996 | 32.262 | 1.00 | 25.56 | A | O |
| ATOM | 158 | N | GLY | A | 257 | 18.029 | 14.680 | 31.778 | 1.00 | 27.01 | A | N |
| ATOM | 159 | CA | GLY | A | 257 | 19.184 | 13.816 | 31.971 | 0.00 | 26.96 | A | C |
| ATOM | 160 | C | GLY | A | 257 | 20.382 | 14.264 | 31.147 | 1.00 | 27.28 | A | C |
| ATOM | 161 | O | GLY | A | 257 | 20.479 | 15.421 | 30.729 | 1.00 | 26.29 | A | O |
| ATOM | 162 | N | GLU | A | 258 | 21.269 | 13.310 | 30.855 | 1.00 | 27.16 | A | N |
| ATOM | 163 | CA | GLU | A | 258 | 22.472 | 13.648 | 30.111 | 0.00 | 26.19 | A | C |
| ATOM | 164 | CB | GLU | A | 258 | 23.623 | 13.836 | 31.122 | 1.00 | 27.74 | A | C |

Figure 12

| | | | | | | | | | | |
|---|---|---|---|---|---|---|---|---|---|---|
| ATOM | 165 | CG | GLU A 258 | 23.326 | 14.889 | 32.206 | 1.00 | 31.44 | A | C |
| ATOM | 166 | CD | GLU A 258 | 24.387 | 14.963 | 33.274 | 1.00 | 33.92 | A | C |
| ATOM | 167 | OE1 | GLU A 258 | 25.054 | 13.932 | 33.490 | 1.00 | 35.52 | A | O |
| ATOM | 168 | OE2 | GLU A 258 | 24.542 | 16.040 | 33.911 | 1.00 | 34.94 | A | O |
| ATOM | 169 | C | GLU A 258 | 22.847 | 12.575 | 29.136 | 1.00 | 24.47 | A | C |
| ATOM | 170 | O | GLU A 258 | 22.337 | 11.462 | 29.192 | 1.00 | 24.18 | A | O |
| ATOM | 171 | N | VAL A 259 | 23.758 | 12.920 | 28.238 | 1.00 | 23.88 | A | N |
| ATOM | 172 | CA | VAL A 259 | 24.301 | 11.958 | 27.285 | 0.00 | 24.27 | A | C |
| ATOM | 173 | CB | VAL A 259 | 23.981 | 12.274 | 25.830 | 1.00 | 23.57 | A | C |
| ATOM | 174 | CG1 | VAL A 259 | 24.486 | 11.095 | 24.925 | 1.00 | 22.40 | A | C |
| ATOM | 175 | CG2 | VAL A 259 | 22.462 | 12.531 | 25.637 | 1.00 | 25.46 | A | C |
| ATOM | 176 | C | VAL A 259 | 25.839 | 12.021 | 27.456 | 1.00 | 24.38 | A | C |
| ATOM | 177 | O | VAL A 259 | 26.438 | 13.086 | 27.467 | 1.00 | 23.84 | A | O |
| ATOM | 178 | N | TRP A 260 | 26.467 | 10.873 | 27.453 | 1.00 | 25.29 | A | N |
| ATOM | 179 | CA | TRP A 260 | 27.919 | 10.821 | 27.664 | 0.00 | 26.63 | A | C |
| ATOM | 180 | CB | TRP A 260 | 28.203 | 10.213 | 29.065 | 1.00 | 27.02 | A | C |
| ATOM | 181 | CG | TRP A 260 | 27.955 | 11.107 | 30.258 | 1.00 | 29.61 | A | C |
| ATOM | 182 | CD2 | TRP A 260 | 28.950 | 11.669 | 31.125 | 1.00 | 31.41 | A | C |
| ATOM | 183 | CE2 | TRP A 260 | 28.291 | 12.540 | 32.019 | 1.00 | 33.19 | A | C |
| ATOM | 184 | CE3 | TRP A 260 | 30.345 | 11.508 | 31.220 | 1.00 | 31.18 | A | C |
| ATOM | 185 | CD1 | TRP A 260 | 26.750 | 11.632 | 30.683 | 1.00 | 31.48 | A | C |
| ATOM | 186 | NE1 | TRP A 260 | 26.949 | 12.506 | 31.729 | 1.00 | 31.73 | A | N |
| ATOM | 187 | CZ2 | TRP A 260 | 28.989 | 13.264 | 33.009 | 1.00 | 33.96 | A | C |
| ATOM | 188 | CZ3 | TRP A 260 | 31.034 | 12.226 | 32.195 | 1.00 | 31.80 | A | C |
| ATOM | 189 | CH2 | TRP A 260 | 30.364 | 13.093 | 33.073 | 1.00 | 33.73 | A | C |
| ATOM | 190 | C | TRP A 260 | 28.568 | 9.866 | 26.686 | 1.00 | 26.21 | A | C |
| ATOM | 191 | O | TRP A 260 | 27.953 | 8.889 | 26.315 | 1.00 | 25.09 | A | O |
| ATOM | 192 | N | MET A 261 | 29.826 | 10.171 | 26.301 | 1.00 | 26.84 | A | N |
| ATOM | 193 | CA | MET A 261 | 30.647 | 9.267 | 25.497 | 0.00 | 26.89 | A | C |
| ATOM | 194 | CB | MET A 261 | 31.759 | 9.998 | 24.763 | 1.00 | 28.85 | A | C |
| ATOM | 195 | CG | MET A 261 | 32.670 | 9.034 | 23.935 | 1.00 | 30.34 | A | C |
| ATOM | 196 | SD | MET A 261 | 34.085 | 8.160 | 24.796 | 1.00 | 32.89 | A | S |
| ATOM | 197 | CE | MET A 261 | 35.010 | 9.708 | 25.248 | 1.00 | 29.95 | A | C |
| ATOM | 198 | C | MET A 261 | 31.312 | 8.432 | 26.571 | 1.00 | 26.76 | A | C |
| ATOM | 199 | O | MET A 261 | 31.577 | 8.928 | 27.669 | 1.00 | 26.01 | A | O |
| ATOM | 200 | N | GLY A 262 | 31.573 | 7.169 | 26.289 | 1.00 | 27.19 | A | N |
| ATOM | 201 | CA | GLY A 262 | 32.205 | 6.333 | 27.269 | 0.00 | 27.99 | A | C |
| ATOM | 202 | C | GLY A 262 | 32.637 | 5.059 | 26.609 | 1.00 | 29.65 | A | C |
| ATOM | 203 | O | GLY A 262 | 32.520 | 4.934 | 25.394 | 1.00 | 30.42 | A | O |
| ATOM | 204 | N | TYR A 263 | 33.100 | 4.110 | 27.417 | 1.00 | 31.08 | A | N |
| ATOM | 205 | CA | TYR A 263 | 33.550 | 2.812 | 26.946 | 0.00 | 33.49 | A | C |
| ATOM | 206 | CB | TYR A 263 | 35.068 | 2.681 | 27.146 | 1.00 | 32.03 | A | C |
| ATOM | 207 | CG | TYR A 263 | 35.806 | 3.700 | 26.332 | 1.00 | 29.02 | A | C |
| ATOM | 208 | CD1 | TYR A 263 | 36.132 | 3.446 | 24.995 | 1.00 | 27.66 | A | C |
| ATOM | 209 | CE1 | TYR A 263 | 36.729 | 4.443 | 24.221 | 1.00 | 27.51 | A | C |
| ATOM | 210 | CD2 | TYR A 263 | 36.095 | 4.962 | 26.871 | 1.00 | 27.35 | A | C |
| ATOM | 211 | CE2 | TYR A 263 | 36.678 | 5.955 | 26.118 | 1.00 | 26.30 | A | C |
| ATOM | 212 | CZ | TYR A 263 | 37.000 | 5.691 | 24.789 | 1.00 | 26.94 | A | C |
| ATOM | 213 | OH | TYR A 263 | 37.633 | 6.688 | 24.073 | 1.00 | 26.84 | A | O |
| ATOM | 214 | C | TYR A 263 | 32.822 | 1.633 | 27.584 | 1.00 | 35.91 | A | C |
| ATOM | 215 | O | TYR A 263 | 32.522 | 1.637 | 28.785 | 1.00 | 36.17 | A | O |
| ATOM | 216 | N | TYR A 264 | 32.529 | 0.644 | 26.757 | 1.00 | 38.84 | A | N |
| ATOM | 217 | CA | TYR A 264 | 31.786 | -0.548 | 27.151 | 0.00 | 43.08 | A | C |
| ATOM | 218 | CB | TYR A 264 | 30.578 | -0.723 | 26.188 | 1.00 | 44.11 | A | C |
| ATOM | 219 | CG | TYR A 264 | 29.643 | -1.930 | 26.378 | 1.00 | 46.30 | A | C |
| ATOM | 220 | CD1 | TYR A 264 | 29.132 | -2.292 | 27.642 | 1.00 | 47.13 | A | C |
| ATOM | 221 | CE1 | TYR A 264 | 28.224 | -3.389 | 27.786 | 1.00 | 47.85 | A | C |
| ATOM | 222 | CD2 | TYR A 264 | 29.235 | -2.687 | 25.261 | 1.00 | 47.44 | A | C |
| ATOM | 223 | CE2 | TYR A 264 | 28.342 | -3.776 | 25.386 | 1.00 | 48.37 | A | C |

Figure 12

| ATOM | 224 | CZ | TYR A 264 | 27.834 | -4.131 | 26.647 | 1.00 | 48.59 | A | C |
|------|-----|-----|-----------|--------|--------|--------|------|-------|---|---|
| ATOM | 225 | OH | TYR A 264 | 26.962 | -5.223 | 26.745 | 1.00 | 48.12 | A | O |
| ATOM | 226 | C | TYR A 264 | 32.741 | -1.731 | 27.056 | 1.00 | 45.15 | A | C |
| ATOM | 227 | O | TYR A 264 | 33.338 | -1.985 | 25.992 | 1.00 | 45.57 | A | O |
| ATOM | 228 | N | ASN A 265 | 32.873 | -2.463 | 28.160 | 1.00 | 46.77 | A | N |
| ATOM | 229 | CA | ASN A 265 | 33.769 | -3.616 | 28.185 | 0.00 | 48.37 | A | C |
| ATOM | 230 | CB | ASN A 265 | 33.331 | -4.659 | 27.141 | 1.00 | 49.33 | A | C |
| ATOM | 231 | CG | ASN A 265 | 31.931 | -5.196 | 27.417 | 1.00 | 50.97 | A | C |
| ATOM | 232 | OD1 | ASN A 265 | 31.485 | -5.237 | 28.571 | 1.00 | 51.19 | A | O |
| ATOM | 233 | ND2 | ASN A 265 | 31.228 | -5.596 | 26.360 | 1.00 | 51.60 | A | N |
| ATOM | 234 | C | ASN A 265 | 35.189 | -3.129 | 27.901 | 1.00 | 48.64 | A | C |
| ATOM | 235 | O | ASN A 265 | 35.970 | -3.807 | 27.226 | 1.00 | 48.49 | A | O |
| ATOM | 236 | N | GLY A 266 | 35.475 | -1.905 | 28.350 | 1.00 | 48.88 | A | N |
| ATOM | 237 | CA | GLY A 266 | 36.806 | -1.335 | 28.174 | 0.00 | 49.28 | A | C |
| ATOM | 238 | C | GLY A 266 | 37.234 | -0.779 | 26.815 | 1.00 | 49.27 | A | C |
| ATOM | 239 | O | GLY A 266 | 37.969 | 0.224 | 26.756 | 1.00 | 48.72 | A | O |
| ATOM | 240 | N | HIS A 267 | 36.809 | -1.421 | 25.728 | 1.00 | 49.84 | A | N |
| ATOM | 241 | CA | HIS A 267 | 37.199 | -0.943 | 24.397 | 0.00 | 50.49 | A | C |
| ATOM | 242 | CB | HIS A 267 | 38.135 | -1.946 | 23.696 | 1.00 | 53.53 | A | C |
| ATOM | 243 | CG | HIS A 267 | 39.507 | -2.001 | 24.304 | 1.00 | 57.03 | A | C |
| ATOM | 244 | CD2 | HIS A 267 | 40.422 | -1.022 | 24.536 | 1.00 | 57.96 | A | C |
| ATOM | 245 | ND1 | HIS A 267 | 40.053 | -3.166 | 24.813 | 1.00 | 58.22 | A | N |
| ATOM | 246 | CE1 | HIS A 267 | 41.240 | -2.900 | 25.335 | 1.00 | 58.80 | A | C |
| ATOM | 247 | NE2 | HIS A 267 | 41.485 | -1.607 | 25.181 | 1.00 | 58.74 | A | N |
| ATOM | 248 | C | HIS A 267 | 36.133 | -0.473 | 23.419 | 1.00 | 48.76 | A | C |
| ATOM | 249 | O | HIS A 267 | 36.475 | 0.156 | 22.425 | 1.00 | 49.23 | A | O |
| ATOM | 250 | N | THR A 268 | 34.865 | -0.790 | 23.647 | 1.00 | 46.22 | A | N |
| ATOM | 251 | CA | THR A 268 | 33.863 | -0.324 | 22.695 | 0.00 | 43.48 | A | C |
| ATOM | 252 | CB | THR A 268 | 32.688 | -1.254 | 22.596 | 1.00 | 43.80 | A | C |
| ATOM | 253 | OG1 | THR A 268 | 33.177 | -2.593 | 22.403 | 1.00 | 45.18 | A | O |
| ATOM | 254 | CG2 | THR A 268 | 31.811 | -0.837 | 21.410 | 1.00 | 43.00 | A | C |
| ATOM | 255 | C | THR A 268 | 33.376 | 1.047 | 23.062 | 1.00 | 41.15 | A | C |
| ATOM | 256 | O | THR A 268 | 32.874 | 1.240 | 24.162 | 1.00 | 41.65 | A | O |
| ATOM | 257 | N | LYS A 269 | 33.579 | 2.011 | 22.170 | 1.00 | 38.25 | A | N |
| ATOM | 258 | CA | LYS A 269 | 33.144 | 3.376 | 22.424 | 0.00 | 36.14 | A | C |
| ATOM | 259 | CB | LYS A 269 | 33.823 | 4.344 | 21.476 | 1.00 | 35.49 | A | C |
| ATOM | 260 | CG | LYS A 269 | 33.676 | 5.791 | 21.846 | 1.00 | 35.05 | A | C |
| ATOM | 261 | CD | LYS A 269 | 34.474 | 6.605 | 20.858 | 1.00 | 35.93 | A | C |
| ATOM | 262 | CE | LYS A 269 | 34.794 | 7.971 | 21.385 | 1.00 | 36.07 | A | C |
| ATOM | 263 | NZ | LYS A 269 | 36.028 | 8.442 | 20.710 | 1.00 | 37.96 | A | N |
| ATOM | 264 | C | LYS A 269 | 31.614 | 3.375 | 22.242 | 1.00 | 34.39 | A | C |
| ATOM | 265 | O | LYS A 269 | 31.096 | 2.749 | 21.324 | 1.00 | 34.03 | A | O |
| ATOM | 266 | N | VAL A 270 | 30.909 | 3.992 | 23.184 | 1.00 | 32.08 | A | N |
| ATOM | 267 | CA | VAL A 270 | 29.440 | 4.020 | 23.171 | 0.00 | 29.66 | A | C |
| ATOM | 268 | CB | VAL A 270 | 28.877 | 2.999 | 24.176 | 1.00 | 28.22 | A | C |
| ATOM | 269 | CG1 | VAL A 270 | 29.207 | 1.608 | 23.756 | 1.00 | 26.08 | A | C |
| ATOM | 270 | CG2 | VAL A 270 | 29.419 | 3.313 | 25.593 | 1.00 | 26.07 | A | C |
| ATOM | 271 | C | VAL A 270 | 28.935 | 5.372 | 23.645 | 1.00 | 28.91 | A | C |
| ATOM | 272 | O | VAL A 270 | 29.703 | 6.195 | 24.144 | 1.00 | 28.64 | A | O |
| ATOM | 273 | N | ALA A 271 | 27.638 | 5.607 | 23.431 | 1.00 | 27.35 | A | N |
| ATOM | 274 | CA | ALA A 271 | 26.986 | 6.820 | 23.921 | 0.00 | 25.79 | A | C |
| ATOM | 275 | CB | ALA A 271 | 26.149 | 7.475 | 22.854 | 1.00 | 24.94 | A | C |
| ATOM | 276 | C | ALA A 271 | 26.105 | 6.267 | 25.010 | 1.00 | 24.87 | A | C |
| ATOM | 277 | O | ALA A 271 | 25.574 | 5.150 | 24.889 | 1.00 | 25.51 | A | O |
| ATOM | 278 | N | VAL A 272 | 25.972 | 7.006 | 26.098 | 1.00 | 24.31 | A | N |
| ATOM | 279 | CA | VAL A 272 | 25.142 | 6.553 | 27.215 | 0.00 | 23.65 | A | C |
| ATOM | 280 | CB | VAL A 272 | 25.956 | 6.240 | 28.540 | 1.00 | 23.63 | A | C |
| ATOM | 281 | CG1 | VAL A 272 | 24.991 | 5.733 | 29.636 | 1.00 | 20.83 | A | C |
| ATOM | 282 | CG2 | VAL A 272 | 27.032 | 5.166 | 28.302 | 1.00 | 21.65 | A | C |

Figure 12

| ATOM | 283 | C | VAL | A | 272 | 24.224 | 7.683 | 27.525 | 1.00 | 24.21 | A | C |
|------|-----|-----|-----|---|-----|--------|-------|--------|------|-------|---|---|
| ATOM | 284 | O | VAL | A | 272 | 24.680 | 8.815 | 27.677 | 1.00 | 24.66 | A | O |
| ATOM | 285 | N | LYS | A | 273 | 22.921 | 7.402 | 27.532 | 1.00 | 24.93 | A | N |
| ATOM | 286 | CA | LYS | A | 273 | 21.948 | 8.430 | 27.905 | 0.00 | 25.70 | A | C |
| ATOM | 287 | CB | LYS | A | 273 | 20.752 | 8.471 | 26.934 | 1.00 | 25.65 | A | C |
| ATOM | 288 | CG | LYS | A | 273 | 19.709 | 9.531 | 27.351 | 1.00 | 26.86 | A | C |
| ATOM | 289 | CD | LYS | A | 273 | 18.594 | 9.673 | 26.359 | 1.00 | 27.97 | A | C |
| ATOM | 290 | CE | LYS | A | 273 | 19.076 | 10.303 | 25.061 | 1.00 | 29.09 | A | C |
| ATOM | 291 | NZ | LYS | A | 273 | 17.944 | 10.448 | 24.047 | 1.00 | 31.13 | A | N |
| ATOM | 292 | C | LYS | A | 273 | 21.485 | 8.097 | 29.336 | 1.00 | 25.59 | A | C |
| ATOM | 293 | O | LYS | A | 273 | 21.118 | 6.971 | 29.624 | 1.00 | 24.51 | A | O |
| ATOM | 294 | N | SER | A | 274 | 21.574 | 9.047 | 30.260 | 1.00 | 27.07 | A | N |
| ATOM | 295 | CA | SER | A | 274 | 21.138 | 8.744 | 31.624 | 0.00 | 28.23 | A | C |
| ATOM | 296 | CB | SER | A | 274 | 22.287 | 8.882 | 32.622 | 1.00 | 29.13 | A | C |
| ATOM | 297 | OG | SER | A | 274 | 22.597 | 10.239 | 32.769 | 1.00 | 32.34 | A | O |
| ATOM | 298 | C | SER | A | 274 | 19.985 | 9.650 | 32.038 | 1.00 | 28.79 | A | C |
| ATOM | 299 | O | SER | A | 274 | 19.940 | 10.865 | 31.729 | 1.00 | 29.30 | A | O |
| ATOM | 300 | N | LEU | A | 275 | 19.074 | 9.042 | 32.786 | 1.00 | 29.37 | A | N |
| ATOM | 301 | CA | LEU | A | 275 | 17.879 | 9.721 | 33.287 | 0.00 | 29.74 | A | C |
| ATOM | 302 | CB | LEU | A | 275 | 16.770 | 8.686 | 33.466 | 1.00 | 26.77 | A | C |
| ATOM | 303 | CG | LEU | A | 275 | 15.537 | 9.255 | 34.157 | 1.00 | 26.84 | A | C |
| ATOM | 304 | CD1 | LEU | A | 275 | 14.718 | 10.145 | 33.208 | 1.00 | 23.62 | A | C |
| ATOM | 305 | CD2 | LEU | A | 275 | 14.738 | 8.086 | 34.640 | 1.00 | 25.93 | A | C |
| ATOM | 306 | C | LEU | A | 275 | 18.060 | 10.512 | 34.591 | 1.00 | 30.61 | A | C |
| ATOM | 307 | O | LEU | A | 275 | 18.631 | 10.014 | 35.551 | 1.00 | 31.05 | A | O |
| ATOM | 308 | N | LYS | A | 276 | 17.635 | 11.767 | 34.614 | 1.00 | 32.03 | A | N |
| ATOM | 309 | CA | LYS | A | 276 | 17.700 | 12.560 | 35.832 | 0.00 | 34.32 | A | C |
| ATOM | 310 | CB | LYS | A | 276 | 17.565 | 14.052 | 35.496 | 1.00 | 35.03 | A | C |
| ATOM | 311 | CG | LYS | A | 276 | 17.263 | 14.970 | 36.674 | 1.00 | 37.30 | A | C |
| ATOM | 312 | CD | LYS | A | 276 | 17.065 | 16.426 | 36.241 | 1.00 | 40.31 | A | C |
| ATOM | 313 | CE | LYS | A | 276 | 18.311 | 16.930 | 35.469 | 1.00 | 42.85 | A | C |
| ATOM | 314 | NZ | LYS | A | 276 | 18.342 | 18.392 | 35.069 | 1.00 | 44.21 | A | N |
| ATOM | 315 | C | LYS | A | 276 | 16.461 | 12.090 | 36.615 | 1.00 | 36.14 | A | C |
| ATOM | 316 | O | LYS | A | 276 | 15.344 | 12.264 | 36.137 | 1.00 | 35.60 | A | O |
| ATOM | 317 | N | GLN | A | 277 | 16.661 | 11.416 | 37.754 | 1.00 | 37.83 | A | N |
| ATOM | 318 | CA | GLN | A | 277 | 15.560 | 10.922 | 38.608 | 0.00 | 39.07 | A | C |
| ATOM | 319 | CB | GLN | A | 277 | 16.085 | 10.465 | 39.985 | 1.00 | 42.56 | A | C |
| ATOM | 320 | CG | GLN | A | 277 | 14.989 | 10.110 | 41.034 | 1.00 | 46.50 | A | C |
| ATOM | 321 | CD | GLN | A | 277 | 15.560 | 9.946 | 42.464 | 1.00 | 50.22 | A | C |
| ATOM | 322 | OE1 | GLN | A | 277 | 16.479 | 10.692 | 42.870 | 1.00 | 52.16 | A | O |
| ATOM | 323 | NE2 | GLN | A | 277 | 15.023 | 8.981 | 43.223 | 1.00 | 49.99 | A | N |
| ATOM | 324 | C | GLN | A | 277 | 14.470 | 11.971 | 38.828 | 1.00 | 38.18 | A | C |
| ATOM | 325 | O | GLN | A | 277 | 14.752 | 13.162 | 39.009 | 1.00 | 36.09 | A | O |
| ATOM | 326 | N | GLY | A | 278 | 13.219 | 11.500 | 38.791 | 1.00 | 38.31 | A | N |
| ATOM | 327 | CA | GLY | A | 278 | 12.082 | 12.382 | 38.975 | 0.00 | 39.29 | A | C |
| ATOM | 328 | C | GLY | A | 278 | 11.564 | 13.075 | 37.716 | 1.00 | 40.16 | A | C |
| ATOM | 329 | O | GLY | A | 278 | 10.506 | 13.715 | 37.755 | 1.00 | 41.43 | A | O |
| ATOM | 330 | N | SER | A | 279 | 12.299 | 12.971 | 36.609 | 1.00 | 39.46 | A | N |
| ATOM | 331 | CA | SER | A | 279 | 11.904 | 13.590 | 35.346 | 0.00 | 39.03 | A | C |
| ATOM | 332 | CB | SER | A | 279 | 13.054 | 13.493 | 34.345 | 1.00 | 39.11 | A | C |
| ATOM | 333 | OG | SER | A | 279 | 14.041 | 14.428 | 34.686 | 1.00 | 41.08 | A | O |
| ATOM | 334 | C | SER | A | 279 | 10.732 | 12.807 | 34.815 | 1.00 | 38.34 | A | C |
| ATOM | 335 | O | SER | A | 279 | 9.767 | 13.344 | 34.264 | 1.00 | 38.62 | A | O |
| ATOM | 336 | N | MET | A | 280 | 10.901 | 11.504 | 34.885 | 1.00 | 37.74 | A | N |
| ATOM | 337 | CA | MET | A | 280 | 9.885 | 10.582 | 34.451 | 0.00 | 36.75 | A | C |
| ATOM | 338 | CB | MET | A | 280 | 9.853 | 10.487 | 32.914 | 1.00 | 36.54 | A | C |
| ATOM | 339 | CG | MET | A | 280 | 10.977 | 9.672 | 32.293 | 1.00 | 34.50 | A | C |
| ATOM | 340 | SD | MET | A | 280 | 11.198 | 10.062 | 30.546 | 1.00 | 35.85 | A | S |
| ATOM | 341 | CE | MET | A | 280 | 10.625 | 8.703 | 29.887 | 1.00 | 34.53 | A | C |

Figure 12

| | | | | | | | | | | | |
|---|---|---|---|---|---|---|---|---|---|---|---|
| ATOM | 342 | C   | MET | A | 280 | 10.263 |  9.275 | 35.093 | 1.00 | 36.89 | A C |
| ATOM | 343 | O   | MET | A | 280 | 11.342 |  9.138 | 35.670 | 1.00 | 37.48 | A O |
| ATOM | 344 | N   | SER | A | 281 |  9.374 |  8.310 | 34.994 | 1.00 | 37.31 | A N |
| ATOM | 345 | CA  | SER | A | 281 |  9.609 |  7.034 | 35.605 | 0.00 | 37.60 | A C |
| ATOM | 346 | CB  | SER | A | 281 |  8.286 |  6.250 | 35.775 | 1.00 | 36.76 | A C |
| ATOM | 347 | OG  | SER | A | 281 |  7.996 |  5.369 | 34.702 | 1.00 | 34.83 | A O |
| ATOM | 348 | C   | SER | A | 281 | 10.608 |  6.222 | 34.841 | 1.00 | 39.19 | A C |
| ATOM | 349 | O   | SER | A | 281 | 10.851 |  6.444 | 33.666 | 1.00 | 39.08 | A O |
| ATOM | 350 | N   | PRO | A | 282 | 11.287 |  5.326 | 35.555 | 1.00 | 40.47 | A N |
| ATOM | 351 | CD  | PRO | A | 282 | 11.443 |  5.330 | 37.028 | 1.00 | 41.00 | A C |
| ATOM | 352 | CA  | PRO | A | 282 | 12.273 |  4.471 | 34.942 | 0.00 | 41.25 | A C |
| ATOM | 353 | CB  | PRO | A | 282 | 12.633 |  3.533 | 36.089 | 1.00 | 40.91 | A C |
| ATOM | 354 | CG  | PRO | A | 282 | 12.708 |  4.510 | 37.242 | 1.00 | 41.50 | A C |
| ATOM | 355 | C   | PRO | A | 282 | 11.650 |  3.741 | 33.788 | 1.00 | 42.20 | A C |
| ATOM | 356 | O   | PRO | A | 282 | 12.134 |  3.826 | 32.672 | 1.00 | 42.08 | A O |
| ATOM | 357 | N   | ASP | A | 283 | 10.541 |  3.056 | 34.060 | 1.00 | 43.64 | A N |
| ATOM | 358 | CA  | ASP | A | 283 |  9.861 |  2.261 | 33.032 | 0.00 | 44.13 | A C |
| ATOM | 359 | CB  | ASP | A | 283 |  8.686 |  1.457 | 33.650 | 1.00 | 47.14 | A C |
| ATOM | 360 | CG  | ASP | A | 283 |  9.160 |  0.359 | 34.630 | 1.00 | 50.04 | A C |
| ATOM | 361 | OD1 | ASP | A | 283 | 10.261 | -0.234 | 34.411 | 1.00 | 52.16 | A O |
| ATOM | 362 | OD2 | ASP | A | 283 |  8.431 |  0.086 | 35.612 | 1.00 | 51.45 | A O |
| ATOM | 363 | C   | ASP | A | 283 |  9.452 |  3.056 | 31.775 | 1.00 | 42.77 | A C |
| ATOM | 364 | O   | ASP | A | 283 |  9.405 |  2.515 | 30.683 | 1.00 | 42.43 | A O |
| ATOM | 365 | N   | ALA | A | 284 |  9.258 |  4.360 | 31.915 | 1.00 | 41.58 | A N |
| ATOM | 366 | CA  | ALA | A | 284 |  8.898 |  5.227 | 30.798 | 0.00 | 40.46 | A C |
| ATOM | 367 | CB  | ALA | A | 284 |  8.213 |  6.485 | 31.307 | 1.00 | 39.62 | A C |
| ATOM | 368 | C   | ALA | A | 284 | 10.148 |  5.628 | 29.994 | 1.00 | 40.43 | A C |
| ATOM | 369 | O   | ALA | A | 284 | 10.069 |  5.859 | 28.791 | 1.00 | 39.26 | A O |
| ATOM | 370 | N   | PHE | A | 285 | 11.267 |  5.833 | 30.702 | 1.00 | 39.85 | A N |
| ATOM | 371 | CA  | PHE | A | 285 | 12.545 |  6.195 | 30.091 | 0.00 | 39.03 | A C |
| ATOM | 372 | CB  | PHE | A | 285 | 13.557 |  6.548 | 31.187 | 1.00 | 38.01 | A C |
| ATOM | 373 | CG  | PHE | A | 285 | 14.947 |  6.835 | 30.685 | 1.00 | 36.66 | A C |
| ATOM | 374 | CD1 | PHE | A | 285 | 15.231 |  8.033 | 30.016 | 1.00 | 34.75 | A C |
| ATOM | 375 | CD2 | PHE | A | 285 | 15.978 |  5.926 | 30.906 | 1.00 | 35.58 | A C |
| ATOM | 376 | CE1 | PHE | A | 285 | 16.516 |  8.322 | 29.595 | 1.00 | 33.77 | A C |
| ATOM | 377 | CE2 | PHE | A | 285 | 17.278 |  6.208 | 30.486 | 1.00 | 34.61 | A C |
| ATOM | 378 | CZ  | PHE | A | 285 | 17.542 |  7.414 | 29.826 | 1.00 | 34.30 | A C |
| ATOM | 379 | C   | PHE | A | 285 | 13.006 |  4.975 | 29.333 | 1.00 | 39.58 | A C |
| ATOM | 380 | O   | PHE | A | 285 | 13.350 |  5.065 | 28.161 | 1.00 | 38.94 | A O |
| ATOM | 381 | N   | LEU | A | 286 | 12.952 |  3.824 | 29.996 | 1.00 | 40.92 | A N |
| ATOM | 382 | CA  | LEU | A | 286 | 13.357 |  2.552 | 29.401 | 0.00 | 43.69 | A C |
| ATOM | 383 | CB  | LEU | A | 286 | 13.354 |  1.463 | 30.454 | 1.00 | 43.78 | A C |
| ATOM | 384 | CG  | LEU | A | 286 | 14.560 |  1.559 | 31.381 | 1.00 | 43.80 | A C |
| ATOM | 385 | CD1 | LEU | A | 286 | 14.252 |  0.859 | 32.732 | 1.00 | 43.88 | A C |
| ATOM | 386 | CD2 | LEU | A | 286 | 15.758 |  0.961 | 30.649 | 1.00 | 43.18 | A C |
| ATOM | 387 | C   | LEU | A | 286 | 12.480 |  2.097 | 28.272 | 1.00 | 46.06 | A C |
| ATOM | 388 | O   | LEU | A | 286 | 12.948 |  1.523 | 27.297 | 1.00 | 46.09 | A O |
| ATOM | 389 | N   | ALA | A | 287 | 11.180 |  2.244 | 28.468 | 1.00 | 49.24 | A N |
| ATOM | 390 | CA  | ALA | A | 287 | 10.187 |  1.845 | 27.471 | 0.00 | 51.25 | A C |
| ATOM | 391 | CB  | ALA | A | 287 |  8.798 |  2.386 | 27.869 | 1.00 | 52.31 | A C |
| ATOM | 392 | C   | ALA | A | 287 | 10.613 |  2.370 | 26.101 | 1.00 | 52.11 | A C |
| ATOM | 393 | O   | ALA | A | 287 | 10.420 |  1.719 | 25.058 | 1.00 | 51.90 | A O |
| ATOM | 394 | N   | GLU | A | 288 | 11.315 |  3.492 | 26.136 | 1.00 | 53.06 | A N |
| ATOM | 395 | CA  | GLU | A | 288 | 11.837 |  4.132 | 24.923 | 0.00 | 53.65 | A C |
| ATOM | 396 | CB  | GLU | A | 288 | 12.256 |  5.579 | 25.261 | 1.00 | 55.19 | A C |
| ATOM | 397 | CG  | GLU | A | 288 | 11.142 |  6.428 | 25.999 | 1.00 | 56.75 | A C |
| ATOM | 398 | CD  | GLU | A | 288 | 11.589 |  7.852 | 26.393 | 1.00 | 57.66 | A C |
| ATOM | 399 | OE1 | GLU | A | 288 | 12.830 |  8.069 | 26.522 | 1.00 | 59.52 | A O |
| ATOM | 400 | OE2 | GLU | A | 288 | 10.703 |  8.747 | 26.549 | 1.00 | 57.46 | A O |

Figure 12

| | | | | | | | | | | | |
|---|---|---|---|---|---|---|---|---|---|---|---|
| ATOM | 401 | C | GLU | A | 288 | 12.994 | 3.345 | 24.223 | 1.00 | 53.05 | A | C |
| ATOM | 402 | O | GLU | A | 288 | 13.287 | 3.544 | 23.043 | 1.00 | 52.66 | A | O |
| ATOM | 403 | N | ALA | A | 289 | 13.646 | 2.447 | 24.963 | 1.00 | 52.84 | A | N |
| ATOM | 404 | CA | ALA | A | 289 | 14.723 | 1.624 | 24.435 | 0.00 | 52.03 | A | C |
| ATOM | 405 | CB | ALA | A | 289 | 15.832 | 1.508 | 25.430 | 1.00 | 52.86 | A | C |
| ATOM | 406 | C | ALA | A | 289 | 14.243 | 0.248 | 24.050 | 1.00 | 52.32 | A | C |
| ATOM | 407 | O | ALA | A | 289 | 14.989 | -0.512 | 23.454 | 1.00 | 51.33 | A | O |
| ATOM | 408 | N | ASN | A | 290 | 13.013 | -0.100 | 24.425 | 1.00 | 53.34 | A | N |
| ATOM | 409 | CA | ASN | A | 290 | 12.469 | -1.408 | 24.049 | 0.00 | 54.20 | A | C |
| ATOM | 410 | CB | ASN | A | 290 | 11.190 | -1.730 | 24.820 | 1.00 | 55.61 | A | C |
| ATOM | 411 | CG | ASN | A | 290 | 11.443 | -1.883 | 26.299 | 1.00 | 56.80 | A | C |
| ATOM | 412 | OD1 | ASN | A | 290 | 10.716 | -1.326 | 27.129 | 1.00 | 57.54 | A | O |
| ATOM | 413 | ND2 | ASN | A | 290 | 12.505 | -2.609 | 26.641 | 1.00 | 57.01 | A | N |
| ATOM | 414 | C | ASN | A | 290 | 12.192 | -1.408 | 22.548 | 1.00 | 54.21 | A | C |
| ATOM | 415 | O | ASN | A | 290 | 12.246 | -2.449 | 21.901 | 1.00 | 53.84 | A | O |
| ATOM | 416 | N | LEU | A | 291 | 11.928 | -0.212 | 22.013 | 1.00 | 54.12 | A | N |
| ATOM | 417 | CA | LEU | A | 291 | 11.682 | 0.010 | 20.585 | 0.00 | 53.85 | A | C |
| ATOM | 418 | CB | LEU | A | 291 | 11.328 | 1.479 | 20.348 | 1.00 | 53.25 | A | C |
| ATOM | 419 | CG | LEU | A | 291 | 9.972 | 1.927 | 20.884 | 1.00 | 53.50 | A | C |
| ATOM | 420 | CD1 | LEU | A | 291 | 9.980 | 3.430 | 21.096 | 1.00 | 53.17 | A | C |
| ATOM | 421 | CD2 | LEU | A | 291 | 8.865 | 1.492 | 19.910 | 1.00 | 52.72 | A | C |
| ATOM | 422 | C | LEU | A | 291 | 12.947 | -0.311 | 19.797 | 1.00 | 54.01 | A | C |
| ATOM | 423 | O | LEU | A | 291 | 12.903 | -0.891 | 18.712 | 1.00 | 53.96 | A | O |
| ATOM | 424 | N | MET | A | 292 | 14.078 | 0.125 | 20.336 | 1.00 | 54.16 | A | N |
| ATOM | 425 | CA | MET | A | 292 | 15.368 | -0.130 | 19.713 | 0.00 | 54.12 | A | C |
| ATOM | 426 | CB | MET | A | 292 | 16.453 | 0.608 | 20.499 | 1.00 | 53.54 | A | C |
| ATOM | 427 | CG | MET | A | 292 | 17.223 | 1.617 | 19.687 | 1.00 | 53.61 | A | C |
| ATOM | 428 | SD | MET | A | 292 | 18.052 | 2.872 | 20.677 | 1.00 | 51.90 | A | S |
| ATOM | 429 | CE | MET | A | 292 | 17.014 | 4.433 | 20.174 | 1.00 | 53.93 | A | C |
| ATOM | 430 | C | MET | A | 292 | 15.633 | -1.650 | 19.651 | 1.00 | 54.48 | A | C |
| ATOM | 431 | O | MET | A | 292 | 16.235 | -2.158 | 18.702 | 1.00 | 54.44 | A | O |
| ATOM | 432 | N | LYS | A | 293 | 15.149 | -2.378 | 20.645 | 1.00 | 55.12 | A | N |
| ATOM | 433 | CA | LYS | A | 293 | 15.319 | -3.827 | 20.676 | 0.00 | 56.20 | A | C |
| ATOM | 434 | CB | LYS | A | 293 | 14.721 | -4.405 | 21.964 | 1.00 | 57.21 | A | C |
| ATOM | 435 | CG | LYS | A | 293 | 15.287 | -3.830 | 23.261 | 1.00 | 59.08 | A | C |
| ATOM | 436 | CD | LYS | A | 293 | 14.679 | -4.509 | 24.502 | 1.00 | 60.27 | A | C |
| ATOM | 437 | CE | LYS | A | 293 | 15.387 | -4.022 | 25.767 | 1.00 | 61.15 | A | C |
| ATOM | 438 | NZ | LYS | A | 293 | 14.994 | -4.805 | 26.965 | 1.00 | 60.68 | A | N |
| ATOM | 439 | C | LYS | A | 293 | 14.546 | -4.407 | 19.494 | 1.00 | 56.18 | A | C |
| ATOM | 440 | O | LYS | A | 293 | 15.069 | -5.182 | 18.686 | 1.00 | 56.36 | A | O |
| ATOM | 441 | N | GLN | A | 294 | 13.300 | -3.953 | 19.377 | 1.00 | 55.84 | A | N |
| ATOM | 442 | CA | GLN | A | 294 | 12.386 | -4.400 | 18.337 | 0.00 | 55.22 | A | C |
| ATOM | 443 | CB | GLN | A | 294 | 10.979 | -3.863 | 18.637 | 1.00 | 57.02 | A | C |
| ATOM | 444 | CG | GLN | A | 294 | 10.514 | -4.115 | 20.104 | 1.00 | 59.28 | A | C |
| ATOM | 445 | CD | GLN | A | 294 | 10.709 | -5.588 | 20.569 | 1.00 | 61.26 | A | C |
| ATOM | 446 | OE1 | GLN | A | 294 | 11.508 | -5.892 | 21.480 | 1.00 | 61.57 | A | O |
| ATOM | 447 | NE2 | GLN | A | 294 | 9.964 | -6.503 | 19.943 | 1.00 | 61.66 | A | N |
| ATOM | 448 | C | GLN | A | 294 | 12.793 | -4.103 | 16.887 | 1.00 | 53.80 | A | C |
| ATOM | 449 | O | GLN | A | 294 | 12.752 | -4.996 | 16.033 | 1.00 | 53.64 | A | O |
| ATOM | 450 | N | LEU | A | 295 | 13.211 | -2.870 | 16.611 | 1.00 | 51.94 | A | N |
| ATOM | 451 | CA | LEU | A | 295 | 13.603 | -2.476 | 15.252 | 0.00 | 50.06 | A | C |
| ATOM | 452 | CB | LEU | A | 295 | 12.922 | -1.173 | 14.886 | 1.00 | 50.30 | A | C |
| ATOM | 453 | CG | LEU | A | 295 | 11.419 | -1.239 | 14.785 | 1.00 | 49.64 | A | C |
| ATOM | 454 | CD1 | LEU | A | 295 | 10.897 | 0.156 | 14.524 | 1.00 | 50.30 | A | C |
| ATOM | 455 | CD2 | LEU | A | 295 | 11.072 | -2.195 | 13.648 | 1.00 | 49.99 | A | C |
| ATOM | 456 | C | LEU | A | 295 | 15.084 | -2.287 | 15.026 | 1.00 | 48.71 | A | C |
| ATOM | 457 | O | LEU | A | 295 | 15.644 | -1.282 | 15.464 | 1.00 | 49.27 | A | O |
| ATOM | 458 | N | GLN | A | 296 | 15.690 | -3.183 | 14.254 | 1.00 | 46.67 | A | N |
| ATOM | 459 | CA | GLN | A | 296 | 17.109 | -3.096 | 13.945 | 0.00 | 44.65 | A | C |

Figure 12

| | | | | | | | | | | |
|---|---|---|---|---|---|---|---|---|---|---|
| ATOM | 460 | CB | GLN | A | 296 | 17.853 | -4.309 | 14.485 | 1.00 45.83 | A C |
| ATOM | 461 | CG | GLN | A | 296 | 17.645 | -4.507 | 15.962 | 1.00 47.70 | A C |
| ATOM | 462 | CD | GLN | A | 296 | 18.333 | -5.751 | 16.485 | 1.00 49.77 | A C |
| ATOM | 463 | OE1 | GLN | A | 296 | 19.141 | -6.381 | 15.776 | 1.00 49.33 | A O |
| ATOM | 464 | NE2 | GLN | A | 296 | 18.054 | -6.091 | 17.744 | 1.00 50.20 | A N |
| ATOM | 465 | C | GLN | A | 296 | 17.368 | -2.931 | 12.460 | 1.00 43.02 | A C |
| ATOM | 466 | O | GLN | A | 296 | 16.760 | -3.629 | 11.633 | 1.00 42.40 | A O |
| ATOM | 467 | N | HIS | A | 297 | 18.313 | -2.044 | 12.121 | 1.00 40.60 | A N |
| ATOM | 468 | CA | HIS | A | 297 | 18.621 | -1.752 | 10.727 | 0.00 38.83 | A C |
| ATOM | 469 | CB | HIS | A | 297 | 17.403 | -1.032 | 10.118 | 1.00 36.64 | A C |
| ATOM | 470 | CG | HIS | A | 297 | 17.418 | -0.934 | 8.619 | 1.00 32.55 | A C |
| ATOM | 471 | CD2 | HIS | A | 297 | 16.835 | -1.697 | 7.674 | 1.00 31.45 | A C |
| ATOM | 472 | ND1 | HIS | A | 297 | 18.097 | 0.069 | 7.948 | 1.00 32.58 | A N |
| ATOM | 473 | CE1 | HIS | A | 297 | 17.926 | -0.093 | 6.645 | 1.00 32.02 | A C |
| ATOM | 474 | NE2 | HIS | A | 297 | 17.163 | -1.153 | 6.450 | 1.00 32.44 | A N |
| ATOM | 475 | C | HIS | A | 297 | 19.881 | -0.868 | 10.619 | 1.00 38.86 | A C |
| ATOM | 476 | O | HIS | A | 297 | 20.195 | -0.105 | 11.534 | 1.00 39.06 | A O |
| ATOM | 477 | N | GLN | A | 298 | 20.591 | -0.959 | 9.502 | 1.00 38.99 | A N |
| ATOM | 478 | CA | GLN | A | 298 | 21.794 | -0.161 | 9.322 | 0.00 39.58 | A C |
| ATOM | 479 | CB | GLN | A | 298 | 22.551 | -0.507 | 8.020 | 1.00 42.13 | A C |
| ATOM | 480 | CG | GLN | A | 298 | 23.566 | -1.715 | 8.144 | 1.00 46.25 | A C |
| ATOM | 481 | CD | GLN | A | 298 | 24.458 | -1.685 | 9.426 | 1.00 48.71 | A C |
| ATOM | 482 | OE1 | GLN | A | 298 | 24.417 | -2.622 | 10.247 | 1.00 49.55 | A O |
| ATOM | 483 | NE2 | GLN | A | 298 | 25.221 | -0.593 | 9.612 | 1.00 49.64 | A N |
| ATOM | 484 | C | GLN | A | 298 | 21.574 | 1.333 | 9.374 | 1.00 38.81 | A C |
| ATOM | 485 | O | GLN | A | 298 | 22.514 | 2.086 | 9.660 | 1.00 39.14 | A O |
| ATOM | 486 | N | ARG | A | 299 | 20.350 | 1.768 | 9.072 | 1.00 36.74 | A N |
| ATOM | 487 | CA | ARG | A | 299 | 20.046 | 3.192 | 9.084 | 0.00 35.47 | A C |
| ATOM | 488 | CB | ARG | A | 299 | 19.084 | 3.536 | 7.958 | 1.00 37.03 | A C |
| ATOM | 489 | CG | ARG | A | 299 | 19.719 | 3.426 | 6.627 | 1.00 40.01 | A C |
| ATOM | 490 | CD | ARG | A | 299 | 20.868 | 4.384 | 6.530 | 1.00 42.62 | A C |
| ATOM | 491 | NE | ARG | A | 299 | 21.833 | 3.886 | 5.575 | 1.00 45.72 | A N |
| ATOM | 492 | CZ | ARG | A | 299 | 23.147 | 3.891 | 5.784 | 1.00 48.62 | A C |
| ATOM | 493 | NH1 | ARG | A | 299 | 23.672 | 4.391 | 6.933 | 1.00 49.40 | A N |
| ATOM | 494 | NH2 | ARG | A | 299 | 23.931 | 3.376 | 4.842 | 1.00 48.18 | A N |
| ATOM | 495 | C | ARG | A | 299 | 19.471 | 3.676 | 10.398 | 1.00 33.93 | A C |
| ATOM | 496 | O | ARG | A | 299 | 19.056 | 4.830 | 10.525 | 1.00 33.58 | A O |
| ATOM | 497 | N | LEU | A | 300 | 19.437 | 2.787 | 11.380 | 1.00 32.16 | A N |
| ATOM | 498 | CA | LEU | A | 300 | 18.893 | 3.125 | 12.686 | 0.00 30.60 | A C |
| ATOM | 499 | CB | LEU | A | 300 | 17.711 | 2.198 | 12.996 | 1.00 28.58 | A C |
| ATOM | 500 | CG | LEU | A | 300 | 16.268 | 2.572 | 12.576 | 1.00 28.02 | A C |
| ATOM | 501 | CD1 | LEU | A | 300 | 16.169 | 2.981 | 11.117 | 1.00 24.37 | A C |
| ATOM | 502 | CD2 | LEU | A | 300 | 15.376 | 1.376 | 12.839 | 1.00 25.82 | A C |
| ATOM | 503 | C | LEU | A | 300 | 19.946 | 2.990 | 13.776 | 1.00 30.83 | A C |
| ATOM | 504 | O | LEU | A | 300 | 20.711 | 2.036 | 13.761 | 1.00 31.52 | A O |
| ATOM | 505 | N | VAL | A | 301 | 20.003 | 3.952 | 14.685 | 1.00 31.35 | A N |
| ATOM | 506 | CA | VAL | A | 301 | 20.920 | 3.910 | 15.821 | 0.00 32.93 | A C |
| ATOM | 507 | CB | VAL | A | 301 | 20.782 | 5.198 | 16.675 | 1.00 32.05 | A C |
| ATOM | 508 | CG1 | VAL | A | 301 | 21.300 | 5.005 | 18.091 | 1.00 32.99 | A C |
| ATOM | 509 | CG2 | VAL | A | 301 | 21.570 | 6.321 | 16.018 | 1.00 30.41 | A C |
| ATOM | 510 | C | VAL | A | 301 | 20.621 | 2.621 | 16.633 | 1.00 34.87 | A C |
| ATOM | 511 | O | VAL | A | 301 | 19.493 | 2.368 | 17.036 | 1.00 35.07 | A O |
| ATOM | 512 | N | ARG | A | 302 | 21.644 | 1.774 | 16.777 | 1.00 36.74 | A N |
| ATOM | 513 | CA | ARG | A | 302 | 21.548 | 0.491 | 17.474 | 0.00 39.02 | A C |
| ATOM | 514 | CB | ARG | A | 302 | 22.581 | -0.458 | 16.850 | 1.00 42.92 | A C |
| ATOM | 515 | CG | ARG | A | 302 | 22.711 | -1.829 | 17.482 | 1.00 48.53 | A C |
| ATOM | 516 | CD | ARG | A | 302 | 23.934 | -1.844 | 18.416 | 1.00 53.83 | A C |
| ATOM | 517 | NE | ARG | A | 302 | 24.514 | -3.183 | 18.644 | 1.00 57.60 | A N |
| ATOM | 518 | CZ | ARG | A | 302 | 25.367 | -3.782 | 17.808 | 1.00 59.66 | A C |

Figure 12

| | | | | | | | | | | | |
|---|---|---|---|---|---|---|---|---|---|---|---|
| ATOM | 519 | NH1 | ARG | A | 302 | 25.733 | -3.173 | 16.679 | 1.00 | 61.12 | A N |
| ATOM | 520 | NH2 | ARG | A | 302 | 25.963 | -4.921 | 18.154 | 1.00 | 60.15 | A N |
| ATOM | 521 | C | ARG | A | 302 | 21.707 | 0.562 | 18.998 | 1.00 | 38.55 | A C |
| ATOM | 522 | O | ARG | A | 302 | 22.491 | 1.353 | 19.534 | 1.00 | 38.91 | A O |
| ATOM | 523 | N | LEU | A | 303 | 20.949 | -0.271 | 19.693 | 1.00 | 38.09 | A N |
| ATOM | 524 | CA | LEU | A | 303 | 20.988 | -0.350 | 21.159 | 0.00 | 38.80 | A C |
| ATOM | 525 | CB | LEU | A | 303 | 19.593 | -0.719 | 21.731 | 1.00 | 37.17 | A C |
| ATOM | 526 | CG | LEU | A | 303 | 19.605 | -0.962 | 23.246 | 1.00 | 37.51 | A C |
| ATOM | 527 | CD1 | LEU | A | 303 | 19.659 | 0.373 | 23.992 | 1.00 | 35.43 | A C |
| ATOM | 528 | CD2 | LEU | A | 303 | 18.424 | -1.848 | 23.721 | 1.00 | 36.11 | A C |
| ATOM | 529 | C | LEU | A | 303 | 21.967 | -1.443 | 21.610 | 1.00 | 39.39 | A C |
| ATOM | 530 | O | LEU | A | 303 | 21.911 | -2.550 | 21.109 | 1.00 | 40.05 | A O |
| ATOM | 531 | N | TYR | A | 304 | 22.868 | -1.121 | 22.537 | 1.00 | 39.69 | A N |
| ATOM | 532 | CA | TYR | A | 304 | 23.800 | -2.124 | 23.069 | 0.00 | 40.01 | A C |
| ATOM | 533 | CB | TYR | A | 304 | 25.202 | -1.531 | 23.331 | 1.00 | 42.18 | A C |
| ATOM | 534 | CG | TYR | A | 304 | 26.000 | -1.297 | 22.083 | 1.00 | 44.11 | A C |
| ATOM | 535 | CD1 | TYR | A | 304 | 26.590 | -0.062 | 21.825 | 1.00 | 45.61 | A C |
| ATOM | 536 | CE1 | TYR | A | 304 | 27.256 | 0.187 | 20.618 | 1.00 | 46.52 | A C |
| ATOM | 537 | CD2 | TYR | A | 304 | 26.103 | -2.280 | 21.116 | 1.00 | 45.95 | A C |
| ATOM | 538 | CE2 | TYR | A | 304 | 26.779 | -2.030 | 19.902 | 1.00 | 47.37 | A C |
| ATOM | 539 | CZ | TYR | A | 304 | 27.339 | -0.804 | 19.669 | 1.00 | 46.83 | A C |
| ATOM | 540 | OH | TYR | A | 304 | 27.951 | -0.582 | 18.473 | 1.00 | 47.99 | A O |
| ATOM | 541 | C | TYR | A | 304 | 23.278 | -2.724 | 24.385 | 1.00 | 38.51 | A C |
| ATOM | 542 | O | TYR | A | 304 | 23.207 | -3.938 | 24.537 | 1.00 | 38.27 | A O |
| ATOM | 543 | N | ALA | A | 305 | 22.911 | -1.859 | 25.324 | 1.00 | 37.28 | A N |
| ATOM | 544 | CA | ALA | A | 305 | 22.451 | -2.302 | 26.634 | 0.00 | 35.96 | A C |
| ATOM | 545 | CB | ALA | A | 305 | 23.683 | -2.783 | 27.446 | 1.00 | 35.43 | A C |
| ATOM | 546 | C | ALA | A | 305 | 21.692 | -1.227 | 27.434 | 1.00 | 35.35 | A C |
| ATOM | 547 | O | ALA | A | 305 | 21.540 | -0.067 | 26.992 | 1.00 | 35.13 | A O |
| ATOM | 548 | N | VAL | A | 306 | 21.238 | -1.634 | 28.624 | 1.00 | 34.64 | A N |
| ATOM | 549 | CA | VAL | A | 306 | 20.534 | -0.770 | 29.575 | 0.00 | 33.65 | A C |
| ATOM | 550 | CB | VAL | A | 306 | 19.006 | -1.048 | 29.573 | 1.00 | 34.03 | A C |
| ATOM | 551 | CG1 | VAL | A | 306 | 18.340 | -0.539 | 28.262 | 1.00 | 33.77 | A C |
| ATOM | 552 | CG2 | VAL | A | 306 | 18.742 | -2.556 | 29.753 | 1.00 | 32.80 | A C |
| ATOM | 553 | C | VAL | A | 306 | 21.016 | -1.058 | 31.008 | 1.00 | 34.17 | A C |
| ATOM | 554 | O | VAL | A | 306 | 21.503 | -2.150 | 31.309 | 1.00 | 33.52 | A O |
| ATOM | 555 | N | VAL | A | 307 | 20.945 | -0.059 | 31.880 | 1.00 | 34.46 | A N |
| ATOM | 556 | CA | VAL | A | 307 | 21.270 | -0.280 | 33.285 | 0.00 | 35.16 | A C |
| ATOM | 557 | CB | VAL | A | 307 | 22.466 | 0.565 | 33.784 | 1.00 | 35.04 | A C |
| ATOM | 558 | CG1 | VAL | A | 307 | 22.542 | 0.515 | 35.314 | 1.00 | 33.99 | A C |
| ATOM | 559 | CG2 | VAL | A | 307 | 23.753 | 0.042 | 33.156 | 1.00 | 33.75 | A C |
| ATOM | 560 | C | VAL | A | 307 | 19.973 | 0.117 | 33.964 | 1.00 | 36.31 | A C |
| ATOM | 561 | O | VAL | A | 307 | 19.535 | 1.267 | 33.877 | 1.00 | 33.74 | A O |
| ATOM | 562 | N | THR | A | 308 | 19.331 | -0.879 | 34.577 | 1.00 | 38.88 | A N |
| ATOM | 563 | CA | THR | A | 308 | 18.057 | -0.683 | 35.243 | 0.00 | 41.18 | A C |
| ATOM | 564 | CB | THR | A | 308 | 17.223 | -1.950 | 35.197 | 1.00 | 40.48 | A C |
| ATOM | 565 | OG1 | THR | A | 308 | 18.019 | -3.064 | 35.609 | 1.00 | 40.90 | A O |
| ATOM | 566 | CG2 | THR | A | 308 | 16.767 | -2.197 | 33.782 | 1.00 | 39.42 | A C |
| ATOM | 567 | C | THR | A | 308 | 18.079 | -0.083 | 36.634 | 1.00 | 43.46 | A C |
| ATOM | 568 | O | THR | A | 308 | 17.047 | 0.384 | 37.104 | 1.00 | 44.35 | A O |
| ATOM | 569 | N | GLN | A | 309 | 19.236 | -0.058 | 37.289 | 1.00 | 45.60 | A N |
| ATOM | 570 | CA | GLN | A | 309 | 19.329 | 0.552 | 38.622 | 0.00 | 47.85 | A C |
| ATOM | 571 | CB | GLN | A | 309 | 20.455 | -0.074 | 39.453 | 1.00 | 51.48 | A C |
| ATOM | 572 | CG | GLN | A | 309 | 20.184 | -1.510 | 39.918 | 1.00 | 58.16 | A C |
| ATOM | 573 | CD | GLN | A | 309 | 18.910 | -1.643 | 40.782 | 1.00 | 61.65 | A C |
| ATOM | 574 | OE1 | GLN | A | 309 | 18.371 | -0.636 | 41.294 | 1.00 | 63.69 | A O |
| ATOM | 575 | NE2 | GLN | A | 309 | 18.436 | -2.883 | 40.950 | 1.00 | 63.41 | A N |
| ATOM | 576 | C | GLN | A | 309 | 19.636 | 2.011 | 38.439 | 1.00 | 47.28 | A C |
| ATOM | 577 | O | GLN | A | 309 | 20.434 | 2.353 | 37.574 | 1.00 | 47.30 | A O |

Figure 12

| ATOM | 578 | N   | GLU | A | 310 | 19.054 | 2.863 | 39.272 | 1.00 | 46.58 | A | N |
|------|-----|-----|-----|---|-----|--------|-------|--------|------|-------|---|---|
| ATOM | 579 | CA  | GLU | A | 310 | 19.288 | 4.298 | 39.174 | 0.00 | 46.97 | A | C |
| ATOM | 580 | CB  | GLU | A | 310 | 18.298 | 5.101 | 40.050 | 1.00 | 49.87 | A | C |
| ATOM | 581 | CG  | GLU | A | 310 | 18.146 | 4.606 | 41.496 | 1.00 | 55.41 | A | C |
| ATOM | 582 | CD  | GLU | A | 310 | 17.163 | 3.416 | 41.671 | 1.00 | 58.36 | A | C |
| ATOM | 583 | OE1 | GLU | A | 310 | 15.940 | 3.695 | 41.753 | 1.00 | 59.13 | A | O |
| ATOM | 584 | OE2 | GLU | A | 310 | 17.611 | 2.229 | 41.767 | 1.00 | 59.10 | A | O |
| ATOM | 585 | C   | GLU | A | 310 | 20.724 | 4.716 | 39.494 | 1.00 | 45.06 | A | C |
| ATOM | 586 | O   | GLU | A | 310 | 21.343 | 4.177 | 40.424 | 1.00 | 45.12 | A | O |
| ATOM | 587 | N   | PRO | A | 311 | 21.298 | 5.634 | 38.685 | 1.00 | 42.89 | A | N |
| ATOM | 588 | CD  | PRO | A | 311 | 22.672 | 6.112 | 38.917 | 1.00 | 42.71 | A | C |
| ATOM | 589 | CA  | PRO | A | 311 | 20.719 | 6.323 | 37.517 | 0.00 | 40.48 | A | C |
| ATOM | 590 | CB  | PRO | A | 311 | 21.808 | 7.347 | 37.155 | 1.00 | 41.85 | A | C |
| ATOM | 591 | CG  | PRO | A | 311 | 22.590 | 7.517 | 38.429 | 1.00 | 42.40 | A | C |
| ATOM | 592 | C   | PRO | A | 311 | 20.470 | 5.382 | 36.323 | 1.00 | 37.91 | A | C |
| ATOM | 593 | O   | PRO | A | 311 | 21.356 | 4.612 | 35.948 | 1.00 | 37.75 | A | O |
| ATOM | 594 | N   | ILE | A | 312 | 19.271 | 5.456 | 35.724 | 1.00 | 35.66 | A | N |
| ATOM | 595 | CA  | ILE | A | 312 | 18.945 | 4.582 | 34.578 | 0.00 | 32.09 | A | C |
| ATOM | 596 | CB  | ILE | A | 312 | 17.449 | 4.636 | 34.188 | 1.00 | 32.70 | A | C |
| ATOM | 597 | CG2 | ILE | A | 312 | 17.111 | 3.422 | 33.328 | 1.00 | 32.11 | A | C |
| ATOM | 598 | CG1 | ILE | A | 312 | 16.550 | 4.630 | 35.428 | 1.00 | 32.97 | A | C |
| ATOM | 599 | CD1 | ILE | A | 312 | 16.307 | 3.235 | 36.014 | 1.00 | 33.15 | A | C |
| ATOM | 600 | C   | ILE | A | 312 | 19.776 | 4.989 | 33.364 | 1.00 | 29.29 | A | C |
| ATOM | 601 | O   | ILE | A | 312 | 19.944 | 6.181 | 33.078 | 1.00 | 27.45 | A | O |
| ATOM | 602 | N   | TYR | A | 313 | 20.308 | 3.984 | 32.687 | 1.00 | 27.47 | A | N |
| ATOM | 603 | CA  | TYR | A | 313 | 21.149 | 4.179 | 31.498 | 0.00 | 27.16 | A | C |
| ATOM | 604 | CB  | TYR | A | 313 | 22.572 | 3.551 | 31.695 | 1.00 | 27.32 | A | C |
| ATOM | 605 | CG  | TYR | A | 313 | 23.600 | 4.291 | 32.537 | 1.00 | 26.62 | A | C |
| ATOM | 606 | CD1 | TYR | A | 313 | 23.329 | 5.552 | 33.077 | 1.00 | 25.67 | A | C |
| ATOM | 607 | CE1 | TYR | A | 313 | 24.256 | 6.213 | 33.893 | 1.00 | 26.63 | A | C |
| ATOM | 608 | CD2 | TYR | A | 313 | 24.855 | 3.694 | 32.827 | 1.00 | 27.78 | A | C |
| ATOM | 609 | CE2 | TYR | A | 313 | 25.805 | 4.353 | 33.673 | 1.00 | 26.79 | A | C |
| ATOM | 610 | CZ  | TYR | A | 313 | 25.486 | 5.607 | 34.201 | 1.00 | 27.30 | A | C |
| ATOM | 611 | OH  | TYR | A | 313 | 26.356 | 6.246 | 35.084 | 1.00 | 27.78 | A | O |
| ATOM | 612 | C   | TYR | A | 313 | 20.612 | 3.468 | 30.275 | 1.00 | 26.39 | A | C |
| ATOM | 613 | O   | TYR | A | 313 | 20.088 | 2.368 | 30.390 | 1.00 | 25.26 | A | O |
| ATOM | 614 | N   | ILE | A | 314 | 20.866 | 4.066 | 29.103 | 1.00 | 25.54 | A | N |
| ATOM | 615 | CA  | ILE | A | 314 | 20.553 | 3.458 | 27.799 | 0.00 | 25.28 | A | C |
| ATOM | 616 | CB  | ILE | A | 314 | 19.406 | 4.188 | 26.977 | 1.00 | 26.05 | A | C |
| ATOM | 617 | CG2 | ILE | A | 314 | 19.236 | 3.529 | 25.608 | 1.00 | 24.02 | A | C |
| ATOM | 618 | CG1 | ILE | A | 314 | 18.068 | 4.121 | 27.714 | 1.00 | 26.10 | A | C |
| ATOM | 619 | CD1 | ILE | A | 314 | 16.874 | 4.854 | 26.985 | 1.00 | 25.77 | A | C |
| ATOM | 620 | C   | ILE | A | 314 | 21.892 | 3.603 | 27.049 | 1.00 | 25.04 | A | C |
| ATOM | 621 | O   | ILE | A | 314 | 22.447 | 4.708 | 26.888 | 1.00 | 24.32 | A | O |
| ATOM | 622 | N   | ILE | A | 315 | 22.384 | 2.496 | 26.526 | 1.00 | 25.33 | A | N |
| ATOM | 623 | CA  | ILE | A | 315 | 23.668 | 2.534 | 25.847 | 0.00 | 24.87 | A | C |
| ATOM | 624 | CB  | ILE | A | 315 | 24.667 | 1.512 | 26.492 | 1.00 | 25.35 | A | C |
| ATOM | 625 | CG2 | ILE | A | 315 | 26.032 | 1.537 | 25.784 | 1.00 | 25.81 | A | C |
| ATOM | 626 | CG1 | ILE | A | 315 | 24.849 | 1.834 | 27.968 | 1.00 | 24.15 | A | C |
| ATOM | 627 | CD1 | ILE | A | 315 | 23.872 | 1.067 | 28.858 | 1.00 | 25.62 | A | C |
| ATOM | 628 | C   | ILE | A | 315 | 23.502 | 2.221 | 24.388 | 1.00 | 25.39 | A | C |
| ATOM | 629 | O   | ILE | A | 315 | 22.979 | 1.182 | 24.008 | 1.00 | 26.13 | A | O |
| ATOM | 630 | N   | THR | A | 316 | 24.033 | 3.087 | 23.546 | 1.00 | 26.15 | A | N |
| ATOM | 631 | CA  | THR | A | 316 | 23.909 | 2.851 | 22.103 | 0.00 | 27.02 | A | C |
| ATOM | 632 | CB  | THR | A | 316 | 22.908 | 3.850 | 21.471 | 1.00 | 26.52 | A | C |
| ATOM | 633 | OG1 | THR | A | 316 | 23.528 | 5.150 | 21.396 | 1.00 | 23.98 | A | O |
| ATOM | 634 | CG2 | THR | A | 316 | 21.645 | 3.962 | 22.306 | 1.00 | 24.61 | A | C |
| ATOM | 635 | C   | THR | A | 316 | 25.251 | 3.095 | 21.441 | 1.00 | 27.92 | A | C |
| ATOM | 636 | O   | THR | A | 316 | 26.152 | 3.670 | 22.046 | 1.00 | 27.50 | A | O |

Figure 12

| ATOM | 637 | N | GLU | A | 317 | 25.362 | 2.697 | 20.181 | 1.00 | 28.72 | A | N |
|------|-----|-----|-----|---|-----|--------|--------|--------|------|-------|---|---|
| ATOM | 638 | CA | GLU | A | 317 | 26.573 | 2.931 | 19.421 | 0.00 | 28.87 | A | C |
| ATOM | 639 | CB | GLU | A | 317 | 26.378 | 2.490 | 17.974 | 1.00 | 30.89 | A | C |
| ATOM | 640 | CG | GLU | A | 317 | 25.388 | 3.304 | 17.122 | 1.00 | 31.80 | A | C |
| ATOM | 641 | CD | GLU | A | 317 | 25.261 | 2.710 | 15.718 | 1.00 | 33.09 | A | C |
| ATOM | 642 | OE1 | GLU | A | 317 | 24.152 | 2.237 | 15.363 | 1.00 | 34.82 | A | O |
| ATOM | 643 | OE2 | GLU | A | 317 | 26.267 | 2.669 | 14.980 | 1.00 | 33.03 | A | O |
| ATOM | 644 | C | GLU | A | 317 | 26.871 | 4.419 | 19.490 | 1.00 | 29.15 | A | C |
| ATOM | 645 | O | GLU | A | 317 | 25.978 | 5.232 | 19.711 | 1.00 | 29.53 | A | O |
| ATOM | 646 | N | TYR | A | 318 | 28.142 | 4.766 | 19.398 | 1.00 | 28.34 | A | N |
| ATOM | 647 | CA | TYR | A | 318 | 28.535 | 6.151 | 19.480 | 0.00 | 28.69 | A | C |
| ATOM | 648 | CB | TYR | A | 318 | 29.927 | 6.226 | 20.148 | 1.00 | 28.11 | A | C |
| ATOM | 649 | CG | TYR | A | 318 | 30.508 | 7.588 | 20.186 | 1.00 | 26.70 | A | C |
| ATOM | 650 | CD1 | TYR | A | 318 | 30.000 | 8.561 | 21.022 | 1.00 | 26.71 | A | C |
| ATOM | 651 | CE1 | TYR | A | 318 | 30.532 | 9.853 | 21.011 | 1.00 | 27.34 | A | C |
| ATOM | 652 | CD2 | TYR | A | 318 | 31.554 | 7.939 | 19.338 | 1.00 | 27.17 | A | C |
| ATOM | 653 | CE2 | TYR | A | 318 | 32.069 | 9.206 | 19.334 | 1.00 | 26.25 | A | C |
| ATOM | 654 | CZ | TYR | A | 318 | 31.562 | 10.137 | 20.163 | 1.00 | 27.11 | A | C |
| ATOM | 655 | OH | TYR | A | 318 | 32.111 | 11.396 | 20.133 | 1.00 | 32.99 | A | O |
| ATOM | 656 | C | TYR | A | 318 | 28.555 | 6.733 | 18.071 | 1.00 | 29.03 | A | C |
| ATOM | 657 | O | TYR | A | 318 | 28.918 | 6.033 | 17.139 | 1.00 | 29.52 | A | O |
| ATOM | 658 | N | MET | A | 319 | 28.108 | 7.980 | 17.904 | 1.00 | 29.76 | A | N |
| ATOM | 659 | CA | MET | A | 319 | 28.108 | 8.620 | 16.578 | 0.00 | 31.80 | A | C |
| ATOM | 660 | CB | MET | A | 319 | 26.679 | 9.018 | 16.142 | 1.00 | 32.69 | A | C |
| ATOM | 661 | CG | MET | A | 319 | 25.740 | 7.797 | 15.897 | 1.00 | 32.46 | A | C |
| ATOM | 662 | SD | MET | A | 319 | 26.149 | 6.735 | 14.474 | 1.00 | 34.16 | A | S |
| ATOM | 663 | CE | MET | A | 319 | 25.174 | 7.557 | 13.221 | 1.00 | 33.02 | A | C |
| ATOM | 664 | C | MET | A | 319 | 29.042 | 9.822 | 16.610 | 1.00 | 32.63 | A | C |
| ATOM | 665 | O | MET | A | 319 | 28.678 | 10.908 | 17.102 | 1.00 | 31.98 | A | O |
| ATOM | 666 | N | GLU | A | 320 | 30.229 | 9.596 | 16.042 | 1.00 | 33.75 | A | N |
| ATOM | 667 | CA | GLU | A | 320 | 31.329 | 10.556 | 16.013 | 0.00 | 34.75 | A | C |
| ATOM | 668 | CB | GLU | A | 320 | 32.384 | 10.061 | 15.024 | 1.00 | 38.13 | A | C |
| ATOM | 669 | CG | GLU | A | 320 | 33.641 | 10.922 | 14.930 | 1.00 | 43.01 | A | C |
| ATOM | 670 | CD | GLU | A | 320 | 34.470 | 10.890 | 16.217 | 1.00 | 45.30 | A | C |
| ATOM | 671 | OE1 | GLU | A | 320 | 34.916 | 9.783 | 16.622 | 1.00 | 45.84 | A | O |
| ATOM | 672 | OE2 | GLU | A | 320 | 34.654 | 11.968 | 16.831 | 1.00 | 46.00 | A | O |
| ATOM | 673 | C | GLU | A | 320 | 30.959 | 12.015 | 15.754 | 1.00 | 33.58 | A | C |
| ATOM | 674 | O | GLU | A | 320 | 31.397 | 12.918 | 16.478 | 1.00 | 33.87 | A | O |
| ATOM | 675 | N | ASN | A | 321 | 30.120 | 12.249 | 14.761 | 1.00 | 31.42 | A | N |
| ATOM | 676 | CA | ASN | A | 321 | 29.725 | 13.609 | 14.439 | 0.00 | 30.44 | A | C |
| ATOM | 677 | CB | ASN | A | 321 | 29.783 | 13.800 | 12.932 | 1.00 | 31.35 | A | C |
| ATOM | 678 | CG | ASN | A | 321 | 31.199 | 13.877 | 12.432 | 1.00 | 32.29 | A | C |
| ATOM | 679 | OD1 | ASN | A | 321 | 31.990 | 14.690 | 12.931 | 1.00 | 33.02 | A | O |
| ATOM | 680 | ND2 | ASN | A | 321 | 31.540 | 13.044 | 11.459 | 1.00 | 32.09 | A | N |
| ATOM | 681 | C | ASN | A | 321 | 28.433 | 14.166 | 15.051 | 1.00 | 28.98 | A | C |
| ATOM | 682 | O | ASN | A | 321 | 27.964 | 15.261 | 14.689 | 1.00 | 28.40 | A | O |
| ATOM | 683 | N | GLY | A | 322 | 27.900 | 13.453 | 16.034 | 1.00 | 28.56 | A | N |
| ATOM | 684 | CA | GLY | A | 322 | 26.697 | 13.910 | 16.716 | 0.00 | 28.22 | A | C |
| ATOM | 685 | C | GLY | A | 322 | 25.404 | 14.121 | 15.913 | 1.00 | 28.49 | A | C |
| ATOM | 686 | O | GLY | A | 322 | 25.073 | 13.375 | 14.994 | 1.00 | 27.87 | A | O |
| ATOM | 687 | N | SER | A | 323 | 24.682 | 15.165 | 16.293 | 1.00 | 28.31 | A | N |
| ATOM | 688 | CA | SER | A | 323 | 23.405 | 15.523 | 15.691 | 0.00 | 28.56 | A | C |
| ATOM | 689 | CB | SER | A | 323 | 22.684 | 16.430 | 16.674 | 1.00 | 28.80 | A | C |
| ATOM | 690 | OG | SER | A | 323 | 21.463 | 16.844 | 16.154 | 1.00 | 32.38 | A | O |
| ATOM | 691 | C | SER | A | 323 | 23.517 | 16.210 | 14.320 | 1.00 | 27.91 | A | C |
| ATOM | 692 | O | SER | A | 323 | 24.243 | 17.201 | 14.170 | 1.00 | 26.96 | A | O |
| ATOM | 693 | N | LEU | A | 324 | 22.790 | 15.693 | 13.331 | 1.00 | 27.39 | A | N |
| ATOM | 694 | CA | LEU | A | 324 | 22.830 | 16.298 | 11.997 | 0.00 | 26.70 | A | C |
| ATOM | 695 | CB | LEU | A | 324 | 21.941 | 15.543 | 11.000 | 1.00 | 24.99 | A | C |

Figure 12

| | | | | | | | | | | |
|---|---|---|---|---|---|---|---|---|---|---|
| ATOM | 696 | CG | LEU | A | 324 | 21.824 | 16.095 | 9.565 | 1.00 23.72 | A C |
| ATOM | 697 | CD1 | LEU | A | 324 | 23.037 | 15.659 | 8.720 | 1.00 21.12 | A C |
| ATOM | 698 | CD2 | LEU | A | 324 | 20.544 | 15.522 | 8.925 | 1.00 24.93 | A C |
| ATOM | 699 | C | LEU | A | 324 | 22.499 | 17.791 | 11.969 | 1.00 26.28 | A C |
| ATOM | 700 | O | LEU | A | 324 | 23.129 | 18.542 | 11.244 | 1.00 26.48 | A O |
| ATOM | 701 | N | VAL | A | 325 | 21.556 | 18.253 | 12.778 | 1.00 27.14 | A N |
| ATOM | 702 | CA | VAL | A | 325 | 21.238 | 19.663 | 12.730 | 0.00 27.72 | A C |
| ATOM | 703 | CB | VAL | A | 325 | 19.992 | 20.020 | 13.551 | 1.00 27.90 | A C |
| ATOM | 704 | CG1 | VAL | A | 325 | 20.286 | 19.975 | 15.061 | 1.00 27.41 | A C |
| ATOM | 705 | CG2 | VAL | A | 325 | 19.478 | 21.394 | 13.155 | 1.00 26.16 | A C |
| ATOM | 706 | C | VAL | A | 325 | 22.451 | 20.528 | 13.107 | 1.00 29.63 | A C |
| ATOM | 707 | O | VAL | A | 325 | 22.606 | 21.616 | 12.533 | 1.00 29.92 | A O |
| ATOM | 708 | N | ASP | A | 326 | 23.296 | 20.038 | 14.044 | 1.00 29.89 | A N |
| ATOM | 709 | CA | ASP | A | 326 | 24.525 | 20.737 | 14.486 | 0.00 31.08 | A C |
| ATOM | 710 | CB | ASP | A | 326 | 25.067 | 20.147 | 15.791 | 1.00 31.94 | A C |
| ATOM | 711 | CG | ASP | A | 326 | 24.140 | 20.344 | 16.955 | 1.00 31.91 | A C |
| ATOM | 712 | OD1 | ASP | A | 326 | 23.503 | 21.406 | 17.064 | 1.00 31.73 | A O |
| ATOM | 713 | OD2 | ASP | A | 326 | 24.090 | 19.417 | 17.792 | 1.00 33.05 | A O |
| ATOM | 714 | C | ASP | A | 326 | 25.667 | 20.565 | 13.446 | 1.00 31.96 | A C |
| ATOM | 715 | O | ASP | A | 326 | 26.383 | 21.526 | 13.102 | 1.00 32.00 | A O |
| ATOM | 716 | N | PHE | A | 327 | 25.839 | 19.332 | 12.976 | 1.00 30.83 | A N |
| ATOM | 717 | CA | PHE | A | 327 | 26.875 | 19.028 | 12.016 | 0.00 31.80 | A C |
| ATOM | 718 | CB | PHE | A | 327 | 26.844 | 17.550 | 11.651 | 1.00 31.17 | A C |
| ATOM | 719 | CG | PHE | A | 327 | 27.859 | 17.177 | 10.623 | 1.00 32.10 | A C |
| ATOM | 720 | CD1 | PHE | A | 327 | 29.221 | 17.271 | 10.908 | 1.00 32.54 | A C |
| ATOM | 721 | CD2 | PHE | A | 327 | 27.461 | 16.760 | 9.354 | 1.00 32.23 | A C |
| ATOM | 722 | CE1 | PHE | A | 327 | 30.166 | 16.960 | 9.948 | 1.00 33.10 | A C |
| ATOM | 723 | CE2 | PHE | A | 327 | 28.386 | 16.448 | 8.389 | 1.00 32.25 | A C |
| ATOM | 724 | CZ | PHE | A | 327 | 29.749 | 16.546 | 8.676 | 1.00 32.94 | A C |
| ATOM | 725 | C | PHE | A | 327 | 26.823 | 19.862 | 10.743 | 1.00 32.71 | A C |
| ATOM | 726 | O | PHE | A | 327 | 27.865 | 20.301 | 10.223 | 1.00 32.57 | A O |
| ATOM | 727 | N | LEU | A | 328 | 25.617 | 20.038 | 10.219 | 1.00 32.99 | A N |
| ATOM | 728 | CA | LEU | A | 328 | 25.422 | 20.815 | 9.007 | 0.00 33.85 | A C |
| ATOM | 729 | CB | LEU | A | 328 | 23.943 | 20.858 | 8.630 | 1.00 33.69 | A C |
| ATOM | 730 | CG | LEU | A | 328 | 23.284 | 19.546 | 8.196 | 1.00 34.37 | A C |
| ATOM | 731 | CD1 | LEU | A | 328 | 21.806 | 19.720 | 8.113 | 1.00 35.63 | A C |
| ATOM | 732 | CD2 | LEU | A | 328 | 23.815 | 19.099 | 6.859 | 1.00 33.69 | A C |
| ATOM | 733 | C | LEU | A | 328 | 25.956 | 22.232 | 9.177 | 1.00 34.45 | A C |
| ATOM | 734 | O | LEU | A | 328 | 26.359 | 22.858 | 8.201 | 1.00 33.40 | A O |
| ATOM | 735 | N | LYS | A | 329 | 25.951 | 22.727 | 10.415 | 1.00 36.43 | A N |
| ATOM | 736 | CA | LYS | A | 329 | 26.419 | 24.080 | 10.712 | 0.00 38.42 | A C |
| ATOM | 737 | CB | LYS | A | 329 | 25.708 | 24.668 | 11.936 | 1.00 38.65 | A C |
| ATOM | 738 | CG | LYS | A | 329 | 24.198 | 24.709 | 11.867 | 1.00 39.36 | A C |
| ATOM | 739 | CD | LYS | A | 329 | 23.657 | 25.584 | 12.983 | 1.00 40.95 | A C |
| ATOM | 740 | CE | LYS | A | 329 | 22.121 | 25.533 | 13.103 | 1.00 41.95 | A C |
| ATOM | 741 | NZ | LYS | A | 329 | 21.643 | 24.149 | 13.379 | 1.00 43.13 | A N |
| ATOM | 742 | C | LYS | A | 329 | 27.941 | 24.169 | 10.920 | 1.00 39.42 | A C |
| ATOM | 743 | O | LYS | A | 329 | 28.476 | 25.276 | 10.960 | 1.00 39.68 | A O |
| ATOM | 744 | N | THR | A | 330 | 28.623 | 23.025 | 11.039 | 1.00 40.44 | A N |
| ATOM | 745 | CA | THR | A | 330 | 30.073 | 23.030 | 11.252 | 0.00 41.57 | A C |
| ATOM | 746 | CB | THR | A | 330 | 30.640 | 21.654 | 11.689 | 1.00 40.87 | A C |
| ATOM | 747 | OG1 | THR | A | 330 | 30.543 | 20.730 | 10.612 | 1.00 41.17 | A O |
| ATOM | 748 | CG2 | THR | A | 330 | 29.941 | 21.115 | 12.898 | 1.00 40.10 | A C |
| ATOM | 749 | C | THR | A | 330 | 30.829 | 23.408 | 9.986 | 1.00 42.88 | A C |
| ATOM | 750 | O | THR | A | 330 | 30.243 | 23.518 | 8.912 | 1.00 43.35 | A O |
| ATOM | 751 | N | PRO | A | 331 | 32.130 | 23.721 | 10.122 | 1.00 43.97 | A N |
| ATOM | 752 | CD | PRO | A | 331 | 32.814 | 24.195 | 11.352 | 1.00 43.94 | A C |
| ATOM | 753 | CA | PRO | A | 331 | 32.916 | 24.079 | 8.938 | 0.00 44.30 | A C |
| ATOM | 754 | CB | PRO | A | 331 | 34.305 | 24.361 | 9.541 | 1.00 43.91 | A C |

Figure 12

| | | | | | | | | | | | |
|---|---|---|---|---|---|---|---|---|---|---|---|
| ATOM | 755 | CG | PRO | A | 331 | 33.922 | 25.103 | 10.794 | 1.00 | 43.74 | A | C |
| ATOM | 756 | C | PRO | A | 331 | 32.930 | 22.962 | 7.894 | 1.00 | 44.02 | A | C |
| ATOM | 757 | O | PRO | A | 331 | 32.847 | 23.232 | 6.701 | 1.00 | 44.17 | A | O |
| ATOM | 758 | N | SER | A | 332 | 32.994 | 21.717 | 8.340 | 1.00 | 44.08 | A | N |
| ATOM | 759 | CA | SER | A | 332 | 33.012 | 20.587 | 7.410 | 0.00 | 45.23 | A | C |
| ATOM | 760 | CB | SER | A | 332 | 33.546 | 19.323 | 8.100 | 1.00 | 46.47 | A | C |
| ATOM | 761 | OG | SER | A | 332 | 34.916 | 19.448 | 8.418 | 1.00 | 48.55 | A | O |
| ATOM | 762 | C | SER | A | 332 | 31.635 | 20.259 | 6.791 | 1.00 | 44.62 | A | C |
| ATOM | 763 | O | SER | A | 332 | 31.550 | 19.696 | 5.699 | 1.00 | 44.39 | A | O |
| ATOM | 764 | N | GLY | A | 333 | 30.565 | 20.568 | 7.522 | 1.00 | 44.17 | A | N |
| ATOM | 765 | CA | GLY | A | 333 | 29.230 | 20.299 | 7.031 | 0.00 | 43.62 | A | C |
| ATOM | 766 | C | GLY | A | 333 | 28.826 | 21.357 | 6.044 | 1.00 | 43.13 | A | C |
| ATOM | 767 | O | GLY | A | 333 | 28.186 | 21.058 | 5.048 | 1.00 | 42.61 | A | O |
| ATOM | 768 | N | ILE | A | 334 | 29.210 | 22.598 | 6.319 | 1.00 | 43.58 | A | N |
| ATOM | 769 | CA | ILE | A | 334 | 28.906 | 23.716 | 5.429 | 0.00 | 44.00 | A | C |
| ATOM | 770 | CB | ILE | A | 334 | 29.437 | 25.053 | 6.005 | 1.00 | 44.92 | A | C |
| ATOM | 771 | CG2 | ILE | A | 334 | 29.495 | 26.155 | 4.900 | 1.00 | 45.13 | A | C |
| ATOM | 772 | CG1 | ILE | A | 334 | 28.535 | 25.533 | 7.142 | 1.00 | 45.86 | A | C |
| ATOM | 773 | CD1 | ILE | A | 334 | 27.283 | 26.307 | 6.681 | 1.00 | 45.93 | A | C |
| ATOM | 774 | C | ILE | A | 334 | 29.525 | 23.500 | 4.038 | 1.00 | 44.05 | A | C |
| ATOM | 775 | O | ILE | A | 334 | 28.990 | 23.989 | 3.027 | 1.00 | 44.22 | A | O |
| ATOM | 776 | N | LYS | A | 335 | 30.613 | 22.735 | 3.977 | 1.00 | 43.72 | A | N |
| ATOM | 777 | CA | LYS | A | 335 | 31.308 | 22.484 | 2.708 | 0.00 | 43.26 | A | C |
| ATOM | 778 | CB | LYS | A | 335 | 32.816 | 22.363 | 2.963 | 1.00 | 45.41 | A | C |
| ATOM | 779 | CG | LYS | A | 335 | 33.448 | 23.588 | 3.656 | 1.00 | 47.82 | A | C |
| ATOM | 780 | CD | LYS | A | 335 | 34.943 | 23.304 | 3.970 | 1.00 | 50.81 | A | C |
| ATOM | 781 | CE | LYS | A | 335 | 35.546 | 24.375 | 4.905 | 1.00 | 53.10 | A | C |
| ATOM | 782 | NZ | LYS | A | 335 | 36.452 | 23.800 | 5.974 | 1.00 | 54.73 | A | N |
| ATOM | 783 | C | LYS | A | 335 | 30.806 | 21.277 | 1.905 | 1.00 | 41.85 | A | C |
| ATOM | 784 | O | LYS | A | 335 | 31.352 | 20.952 | 0.852 | 1.00 | 41.41 | A | O |
| ATOM | 785 | N | LEU | A | 336 | 29.793 | 20.587 | 2.421 | 1.00 | 41.00 | A | N |
| ATOM | 786 | CA | LEU | A | 336 | 29.209 | 19.418 | 1.743 | 0.00 | 39.87 | A | C |
| ATOM | 787 | CB | LEU | A | 336 | 28.183 | 18.714 | 2.650 | 1.00 | 40.00 | A | C |
| ATOM | 788 | CG | LEU | A | 336 | 28.658 | 18.109 | 3.976 | 1.00 | 40.78 | A | C |
| ATOM | 789 | CD1 | LEU | A | 336 | 27.503 | 17.394 | 4.709 | 1.00 | 39.06 | A | C |
| ATOM | 790 | CD2 | LEU | A | 336 | 29.754 | 17.123 | 3.699 | 1.00 | 39.73 | A | C |
| ATOM | 791 | C | LEU | A | 336 | 28.508 | 19.809 | 0.437 | 1.00 | 38.87 | A | C |
| ATOM | 792 | O | LEU | A | 336 | 27.812 | 20.834 | 0.373 | 1.00 | 37.21 | A | O |
| ATOM | 793 | N | THR | A | 337 | 28.709 | 18.976 | -0.583 | 1.00 | 38.72 | A | N |
| ATOM | 794 | CA | THR | A | 337 | 28.117 | 19.162 | -1.906 | 0.00 | 38.63 | A | C |
| ATOM | 795 | CB | THR | A | 337 | 28.816 | 18.262 | -3.007 | 1.00 | 38.22 | A | C |
| ATOM | 796 | OG1 | THR | A | 337 | 28.692 | 16.881 | -2.653 | 1.00 | 37.03 | A | O |
| ATOM | 797 | CG2 | THR | A | 337 | 30.314 | 18.608 | -3.182 | 1.00 | 39.02 | A | C |
| ATOM | 798 | C | THR | A | 337 | 26.640 | 18.737 | -1.842 | 1.00 | 38.35 | A | C |
| ATOM | 799 | O | THR | A | 337 | 26.250 | 17.946 | -0.960 | 1.00 | 38.65 | A | O |
| ATOM | 800 | N | ILE | A | 338 | 25.853 | 19.231 | -2.804 | 1.00 | 37.41 | A | N |
| ATOM | 801 | CA | ILE | A | 338 | 24.435 | 18.896 | -2.889 | 0.00 | 36.38 | A | C |
| ATOM | 802 | CB | ILE | A | 338 | 23.709 | 19.706 | -4.007 | 1.00 | 36.96 | A | C |
| ATOM | 803 | CG2 | ILE | A | 338 | 24.349 | 19.427 | -5.390 | 1.00 | 36.31 | A | C |
| ATOM | 804 | CG1 | ILE | A | 338 | 22.198 | 19.402 | -3.982 | 1.00 | 36.10 | A | C |
| ATOM | 805 | CD1 | ILE | A | 338 | 21.448 | 19.952 | -2.753 | 1.00 | 34.68 | A | C |
| ATOM | 806 | C | ILE | A | 338 | 24.348 | 17.403 | -3.127 | 1.00 | 35.51 | A | C |
| ATOM | 807 | O | ILE | A | 338 | 23.470 | 16.750 | -2.608 | 1.00 | 35.73 | A | O |
| ATOM | 808 | N | ASN | A | 339 | 25.343 | 16.846 | -3.800 | 1.00 | 35.31 | A | N |
| ATOM | 809 | CA | ASN | A | 339 | 25.387 | 15.400 | -4.036 | 0.00 | 35.27 | A | C |
| ATOM | 810 | CB | ASN | A | 339 | 26.637 | 15.034 | -4.818 | 1.00 | 36.29 | A | C |
| ATOM | 811 | CG | ASN | A | 339 | 26.635 | 15.619 | -6.194 | 1.00 | 36.95 | A | C |
| ATOM | 812 | OD1 | ASN | A | 339 | 26.380 | 14.905 | -7.167 | 1.00 | 37.83 | A | O |
| ATOM | 813 | ND2 | ASN | A | 339 | 26.889 | 16.924 | -6.295 | 1.00 | 35.90 | A | N |

Figure 12

| | | | | | | | | | | | |
|---|---|---|---|---|---|---|---|---|---|---|---|
| ATOM | 814 | C | ASN | A | 339 | 25.432 | 14.610 | -2.730 | 1.00 | 34.59 | A C |
| ATOM | 815 | O | ASN | A | 339 | 24.814 | 13.551 | -2.625 | 1.00 | 34.61 | A O |
| ATOM | 816 | N | LYS | A | 340 | 26.312 | 15.034 | -1.824 | 1.00 | 33.46 | A N |
| ATOM | 817 | CA | LYS | A | 340 | 26.470 | 14.399 | -0.517 | 0.00 | 32.95 | A C |
| ATOM | 818 | CB | LYS | A | 340 | 27.713 | 14.978 | 0.176 | 1.00 | 33.24 | A C |
| ATOM | 819 | CG | LYS | A | 340 | 27.934 | 14.485 | 1.570 | 1.00 | 34.53 | A C |
| ATOM | 820 | CD | LYS | A | 340 | 28.014 | 12.952 | 1.571 | 1.00 | 36.42 | A C |
| ATOM | 821 | CE | LYS | A | 340 | 28.080 | 12.426 | 3.006 | 1.00 | 38.25 | A C |
| ATOM | 822 | NZ | LYS | A | 340 | 28.192 | 10.932 | 3.132 | 1.00 | 39.16 | A N |
| ATOM | 823 | C | LYS | A | 340 | 25.183 | 14.647 | 0.342 | 1.00 | 31.97 | A C |
| ATOM | 824 | O | LYS | A | 340 | 24.663 | 13.733 | 0.976 | 1.00 | 32.39 | A O |
| ATOM | 825 | N | LEU | A | 341 | 24.707 | 15.888 | 0.384 | 1.00 | 30.23 | A N |
| ATOM | 826 | CA | LEU | A | 341 | 23.483 | 16.223 | 1.107 | 0.00 | 28.59 | A C |
| ATOM | 827 | CB | LEU | A | 341 | 23.128 | 17.686 | 0.843 | 1.00 | 25.89 | A C |
| ATOM | 828 | CG | LEU | A | 341 | 24.126 | 18.589 | 1.556 | 1.00 | 25.21 | A C |
| ATOM | 829 | CD1 | LEU | A | 341 | 23.844 | 20.047 | 1.258 | 1.00 | 22.67 | A C |
| ATOM | 830 | CD2 | LEU | A | 341 | 24.049 | 18.304 | 3.063 | 1.00 | 23.62 | A C |
| ATOM | 831 | C | LEU | A | 341 | 22.320 | 15.312 | 0.673 | 1.00 | 28.49 | A C |
| ATOM | 832 | O | LEU | A | 341 | 21.562 | 14.803 | 1.500 | 1.00 | 28.77 | A O |
| ATOM | 833 | N | LEU | A | 342 | 22.205 | 15.078 | -0.619 | 1.00 | 28.50 | A N |
| ATOM | 834 | CA | LEU | A | 342 | 21.164 | 14.211 | -1.148 | 0.00 | 29.13 | A C |
| ATOM | 835 | CB | LEU | A | 342 | 20.988 | 14.406 | -2.657 | 1.00 | 29.21 | A C |
| ATOM | 836 | CG | LEU | A | 342 | 20.417 | 15.806 | -2.938 | 1.00 | 30.80 | A C |
| ATOM | 837 | CD1 | LEU | A | 342 | 19.679 | 15.810 | -4.207 | 1.00 | 31.55 | A C |
| ATOM | 838 | CD2 | LEU | A | 342 | 19.438 | 16.270 | -1.856 | 1.00 | 32.34 | A C |
| ATOM | 839 | C | LEU | A | 342 | 21.373 | 12.763 | -0.812 | 1.00 | 30.22 | A C |
| ATOM | 840 | O | LEU | A | 342 | 20.396 | 12.028 | -0.715 | 1.00 | 30.70 | A O |
| ATOM | 841 | N | ASP | A | 343 | 22.627 | 12.312 | -0.674 | 1.00 | 30.93 | A N |
| ATOM | 842 | CA | ASP | A | 343 | 22.867 | 10.906 | -0.279 | 0.00 | 32.20 | A C |
| ATOM | 843 | CB | ASP | A | 343 | 24.316 | 10.462 | -0.485 | 1.00 | 35.65 | A C |
| ATOM | 844 | CG | ASP | A | 343 | 24.525 | 8.984 | -0.078 | 1.00 | 40.00 | A C |
| ATOM | 845 | OD1 | ASP | A | 343 | 24.172 | 8.055 | -0.846 | 1.00 | 41.58 | A O |
| ATOM | 846 | OD2 | ASP | A | 343 | 25.019 | 8.737 | 1.045 | 1.00 | 43.64 | A O |
| ATOM | 847 | C | ASP | A | 343 | 22.484 | 10.720 | 1.210 | 1.00 | 30.95 | A C |
| ATOM | 848 | O | ASP | A | 343 | 21.956 | 9.691 | 1.607 | 1.00 | 30.06 | A O |
| ATOM | 849 | N | MET | A | 344 | 22.790 | 11.716 | 2.028 | 1.00 | 30.23 | A N |
| ATOM | 850 | CA | MET | A | 344 | 22.437 | 11.678 | 3.442 | 0.00 | 29.53 | A C |
| ATOM | 851 | CB | MET | A | 344 | 22.975 | 12.948 | 4.106 | 1.00 | 30.34 | A C |
| ATOM | 852 | CG | MET | A | 344 | 24.487 | 12.976 | 4.255 | 1.00 | 31.76 | A C |
| ATOM | 853 | SD | MET | A | 344 | 24.986 | 14.476 | 5.075 | 1.00 | 34.25 | A S |
| ATOM | 854 | CE | MET | A | 344 | 25.591 | 13.840 | 6.586 | 1.00 | 33.65 | A C |
| ATOM | 855 | C | MET | A | 344 | 20.873 | 11.610 | 3.579 | 1.00 | 29.42 | A C |
| ATOM | 856 | O | MET | A | 344 | 20.313 | 10.796 | 4.355 | 1.00 | 28.09 | A O |
| ATOM | 857 | N | ALA | A | 345 | 20.195 | 12.440 | 2.772 | 1.00 | 27.92 | A N |
| ATOM | 858 | CA | ALA | A | 345 | 18.744 | 12.497 | 2.759 | 0.00 | 26.53 | A C |
| ATOM | 859 | CB | ALA | A | 345 | 18.297 | 13.577 | 1.817 | 1.00 | 24.73 | A C |
| ATOM | 860 | C | ALA | A | 345 | 18.216 | 11.123 | 2.324 | 1.00 | 25.86 | A C |
| ATOM | 861 | O | ALA | A | 345 | 17.291 | 10.588 | 2.914 | 1.00 | 25.78 | A O |
| ATOM | 862 | N | ALA | A | 346 | 18.859 | 10.528 | 1.335 | 1.00 | 25.15 | A N |
| ATOM | 863 | CA | ALA | A | 346 | 18.481 | 9.227 | 0.856 | 0.00 | 25.16 | A C |
| ATOM | 864 | CB | ALA | A | 346 | 19.356 | 8.873 | -0.343 | 1.00 | 25.95 | A C |
| ATOM | 865 | C | ALA | A | 346 | 18.617 | 8.154 | 1.931 | 1.00 | 26.26 | A C |
| ATOM | 866 | O | ALA | A | 346 | 17.862 | 7.171 | 1.980 | 1.00 | 27.13 | A O |
| ATOM | 867 | N | GLN | A | 347 | 19.656 | 8.280 | 2.744 | 1.00 | 26.71 | A N |
| ATOM | 868 | CA | GLN | A | 347 | 19.862 | 7.305 | 3.806 | 0.00 | 27.33 | A C |
| ATOM | 869 | CB | GLN | A | 347 | 21.223 | 7.542 | 4.473 | 1.00 | 28.78 | A C |
| ATOM | 870 | CG | GLN | A | 347 | 22.425 | 7.117 | 3.687 | 1.00 | 32.25 | A C |
| ATOM | 871 | CD | GLN | A | 347 | 23.736 | 7.397 | 4.490 | 1.00 | 36.24 | A C |
| ATOM | 872 | OE1 | GLN | A | 347 | 24.470 | 6.465 | 4.817 | 1.00 | 37.98 | A O |

Figure 12

| | | | | | | | | | | | |
|---|---|---|---|---|---|---|---|---|---|---|---|
|ATOM|873|NE2|GLN|A|347|23.967|8.662|4.872|1.00 36.20|A|N|
|ATOM|874|C|GLN|A|347|18.778|7.380|4.878|1.00 25.48|A|C|
|ATOM|875|O|GLN|A|347|18.421|6.365|5.471|1.00 25.69|A|O|
|ATOM|876|N|ILE|A|348|18.361|8.592|5.218|1.00 23.83|A|N|
|ATOM|877|CA|ILE|A|348|17.319|8.816|6.207|0.00 23.90|A|C|
|ATOM|878|CB|ILE|A|348|17.184|10.327|6.485|1.00 24.81|A|C|
|ATOM|879|CG2|ILE|A|348|15.996|10.598|7.393|1.00 24.56|A|C|
|ATOM|880|CG1|ILE|A|348|18.489|10.830|7.123|1.00 25.08|A|C|
|ATOM|881|CD1|ILE|A|348|18.600|12.330|7.218|1.00 24.93|A|C|
|ATOM|882|C|ILE|A|348|15.986|8.250|5.692|1.00 24.28|A|C|
|ATOM|883|O|ILE|A|348|15.220|7.600|6.447|1.00 23.11|A|O|
|ATOM|884|N|ALA|A|349|15.720|8.501|4.404|1.00 23.45|A|N|
|ATOM|885|CA|ALA|A|349|14.527|8.035|3.772|0.00 23.82|A|C|
|ATOM|886|CB|ALA|A|349|14.439|8.547|2.320|1.00 23.82|A|C|
|ATOM|887|C|ALA|A|349|14.542|6.534|3.793|1.00 24.79|A|C|
|ATOM|888|O|ALA|A|349|13.490|5.913|3.970|1.00 25.73|A|O|
|ATOM|889|N|GLU|A|350|15.729|5.938|3.608|1.00 25.23|A|N|
|ATOM|890|CA|GLU|A|350|15.868|4.475|3.593|0.00 25.23|A|C|
|ATOM|891|CB|GLU|A|350|17.273|4.044|3.150|1.00 26.74|A|C|
|ATOM|892|CG|GLU|A|350|17.513|2.525|3.213|1.00 28.59|A|C|
|ATOM|893|CD|GLU|A|350|18.995|2.103|3.108|1.00 30.94|A|C|
|ATOM|894|OE1|GLU|A|350|19.883|2.915|2.717|1.00 32.31|A|O|
|ATOM|895|OE2|GLU|A|350|19.271|0.921|3.385|1.00 31.99|A|O|
|ATOM|896|C|GLU|A|350|15.541|3.871|4.931|1.00 24.72|A|C|
|ATOM|897|O|GLU|A|350|14.939|2.801|5.017|1.00 25.89|A|O|
|ATOM|898|N|GLY|A|351|15.939|4.550|5.990|1.00 24.46|A|N|
|ATOM|899|CA|GLY|A|351|15.621|4.053|7.324|0.00 23.33|A|C|
|ATOM|900|C|GLY|A|351|14.144|4.247|7.618|1.00 22.93|A|C|
|ATOM|901|O|GLY|A|351|13.532|3.385|8.235|1.00 23.10|A|O|
|ATOM|902|N|MET|A|352|13.577|5.387|7.222|1.00 21.62|A|N|
|ATOM|903|CA|MET|A|352|12.148|5.620|7.438|0.00 21.18|A|C|
|ATOM|904|CB|MET|A|352|11.713|7.031|7.080|1.00 20.22|A|C|
|ATOM|905|CG|MET|A|352|12.208|8.066|7.990|1.00 19.97|A|C|
|ATOM|906|SD|MET|A|352|11.664|7.802|9.670|1.00 23.61|A|S|
|ATOM|907|CE|MET|A|352|9.847|7.273|9.456|1.00 19.52|A|C|
|ATOM|908|C|MET|A|352|11.342|4.643|6.606|1.00 21.98|A|C|
|ATOM|909|O|MET|A|352|10.234|4.286|7.009|1.00 22.27|A|O|
|ATOM|910|N|ALA|A|353|11.907|4.171|5.487|1.00 21.44|A|N|
|ATOM|911|CA|ALA|A|353|11.230|3.185|4.665|0.00 23.51|A|C|
|ATOM|912|CB|ALA|A|353|11.969|2.996|3.322|1.00 22.75|A|C|
|ATOM|913|C|ALA|A|353|11.147|1.836|5.424|1.00 24.38|A|C|
|ATOM|914|O|ALA|A|353|10.241|1.051|5.191|1.00 24.26|A|O|
|ATOM|915|N|PHE|A|354|12.096|1.573|6.330|1.00 25.75|A|N|
|ATOM|916|CA|PHE|A|354|12.095|0.333|7.117|0.00 25.54|A|C|
|ATOM|917|CB|PHE|A|354|13.489|0.043|7.698|1.00 26.84|A|C|
|ATOM|918|CG|PHE|A|354|13.564|-1.221|8.539|1.00 27.38|A|C|
|ATOM|919|CD1|PHE|A|354|13.485|-2.489|7.949|1.00 29.62|A|C|
|ATOM|920|CD2|PHE|A|354|13.728|-1.141|9.916|1.00 27.75|A|C|
|ATOM|921|CE1|PHE|A|354|13.571|-3.678|8.758|1.00 29.25|A|C|
|ATOM|922|CE2|PHE|A|354|13.816|-2.317|10.713|1.00 28.47|A|C|
|ATOM|923|CZ|PHE|A|354|13.735|-3.571|10.134|1.00 27.34|A|C|
|ATOM|924|C|PHE|A|354|11.089|0.554|8.212|1.00 25.34|A|C|
|ATOM|925|O|PHE|A|354|10.269|-0.304|8.471|1.00 26.27|A|O|
|ATOM|926|N|ILE|A|355|11.087|1.725|8.827|1.00 25.39|A|N|
|ATOM|927|CA|ILE|A|355|10.086|1.989|9.861|0.00 25.40|A|C|
|ATOM|928|CB|ILE|A|355|10.309|3.346|10.540|1.00 24.57|A|C|
|ATOM|929|CG2|ILE|A|355|9.067|3.747|11.401|1.00 23.68|A|C|
|ATOM|930|CG1|ILE|A|355|11.582|3.304|11.409|1.00 23.36|A|C|
|ATOM|931|CD1|ILE|A|355|12.112|4.706|11.810|1.00 21.35|A|C|

Figure 12

| | | | | | | | | | | | |
|---|---|---|---|---|---|---|---|---|---|---|---|
| ATOM | 932 | C | ILE | A | 355 | 8.653 | 1.858 | 9.267 | 1.00 | 26.47 | A | C |
| ATOM | 933 | O | ILE | A | 355 | 7.820 | 1.165 | 9.836 | 1.00 | 25.84 | A | O |
| ATOM | 934 | N | GLU | A | 356 | 8.418 | 2.461 | 8.096 | 1.00 | 27.83 | A | N |
| ATOM | 935 | CA | GLU | A | 356 | 7.136 | 2.395 | 7.360 | 0.00 | 29.20 | A | C |
| ATOM | 936 | CB | GLU | A | 356 | 7.294 | 3.163 | 6.061 | 1.00 | 28.67 | A | C |
| ATOM | 937 | CG | GLU | A | 356 | 6.126 | 3.062 | 5.058 | 1.00 | 29.02 | A | C |
| ATOM | 938 | CD | GLU | A | 356 | 6.329 | 4.000 | 3.865 | 1.00 | 28.34 | A | C |
| ATOM | 939 | OE1 | GLU | A | 356 | 6.998 | 3.657 | 2.867 | 1.00 | 30.00 | A | O |
| ATOM | 940 | OE2 | GLU | A | 356 | 5.868 | 5.130 | 3.947 | 1.00 | 29.70 | A | O |
| ATOM | 941 | C | GLU | A | 356 | 6.738 | 0.924 | 7.051 | 1.00 | 30.28 | A | C |
| ATOM | 942 | O | GLU | A | 356 | 5.643 | 0.475 | 7.324 | 1.00 | 30.28 | A | O |
| ATOM | 943 | N | GLU | A | 357 | 7.682 | 0.181 | 6.526 | 1.00 | 32.59 | A | N |
| ATOM | 944 | CA | GLU | A | 357 | 7.536 | -1.225 | 6.199 | 0.00 | 35.68 | A | C |
| ATOM | 945 | CB | GLU | A | 357 | 8.926 | -1.679 | 5.771 | 1.00 | 39.41 | A | C |
| ATOM | 946 | CG | GLU | A | 357 | 9.286 | -3.117 | 6.085 | 1.00 | 44.60 | A | C |
| ATOM | 947 | CD | GLU | A | 357 | 8.719 | -4.062 | 5.067 | 1.00 | 48.77 | A | C |
| ATOM | 948 | OE1 | GLU | A | 357 | 8.451 | -3.604 | 3.914 | 1.00 | 50.91 | A | O |
| ATOM | 949 | OE2 | GLU | A | 357 | 8.565 | -5.260 | 5.424 | 1.00 | 51.16 | A | O |
| ATOM | 950 | C | GLU | A | 357 | 7.061 | -2.093 | 7.388 | 1.00 | 36.30 | A | C |
| ATOM | 951 | O | GLU | A | 357 | 6.216 | -2.986 | 7.244 | 1.00 | 36.17 | A | O |
| ATOM | 952 | N | ARG | A | 358 | 7.643 | -1.833 | 8.558 | 1.00 | 36.45 | A | N |
| ATOM | 953 | CA | ARG | A | 358 | 7.341 | -2.590 | 9.756 | 0.00 | 35.88 | A | C |
| ATOM | 954 | CB | ARG | A | 358 | 8.580 | -2.652 | 10.664 | 1.00 | 37.87 | A | C |
| ATOM | 955 | CG | ARG | A | 358 | 9.836 | -3.167 | 9.969 | 1.00 | 39.91 | A | C |
| ATOM | 956 | CD | ARG | A | 358 | 9.761 | -4.658 | 9.622 | 1.00 | 43.83 | A | C |
| ATOM | 957 | NE | ARG | A | 358 | 9.577 | -5.476 | 10.822 | 1.00 | 49.04 | A | N |
| ATOM | 958 | CZ | ARG | A | 358 | 10.481 | -5.600 | 11.803 | 1.00 | 52.10 | A | C |
| ATOM | 959 | NH1 | ARG | A | 358 | 11.646 | -4.965 | 11.726 | 1.00 | 55.36 | A | N |
| ATOM | 960 | NH2 | ARG | A | 358 | 10.218 | -6.309 | 12.893 | 1.00 | 52.40 | A | N |
| ATOM | 961 | C | ARG | A | 358 | 6.144 | -2.031 | 10.468 | 1.00 | 34.72 | A | C |
| ATOM | 962 | O | ARG | A | 358 | 5.770 | -2.494 | 11.537 | 1.00 | 34.40 | A | O |
| ATOM | 963 | N | ASN | A | 359 | 5.511 | -1.038 | 9.859 | 1.00 | 33.87 | A | N |
| ATOM | 964 | CA | ASN | A | 359 | 4.294 | -0.450 | 10.410 | 0.00 | 33.01 | A | C |
| ATOM | 965 | CB | ASN | A | 359 | 3.176 | -1.502 | 10.507 | 1.00 | 36.08 | A | C |
| ATOM | 966 | CG | ASN | A | 359 | 2.877 | -2.183 | 9.161 | 1.00 | 39.32 | A | C |
| ATOM | 967 | OD1 | ASN | A | 359 | 2.310 | -1.567 | 8.224 | 1.00 | 41.43 | A | O |
| ATOM | 968 | ND2 | ASN | A | 359 | 3.275 | -3.458 | 9.047 | 1.00 | 40.37 | A | N |
| ATOM | 969 | C | ASN | A | 359 | 4.412 | 0.298 | 11.717 | 1.00 | 31.28 | A | C |
| ATOM | 970 | O | ASN | A | 359 | 3.506 | 0.252 | 12.557 | 1.00 | 30.51 | A | O |
| ATOM | 971 | N | TYR | A | 360 | 5.508 | 1.040 | 11.857 | 1.00 | 30.19 | A | N |
| ATOM | 972 | CA | TYR | A | 360 | 5.760 | 1.886 | 13.014 | 0.00 | 29.48 | A | C |
| ATOM | 973 | CB | TYR | A | 360 | 7.157 | 1.653 | 13.541 | 1.00 | 30.87 | A | C |
| ATOM | 974 | CG | TYR | A | 360 | 7.285 | 0.450 | 14.400 | 1.00 | 32.57 | A | C |
| ATOM | 975 | CD1 | TYR | A | 360 | 7.658 | -0.760 | 13.849 | 1.00 | 34.51 | A | C |
| ATOM | 976 | CE1 | TYR | A | 360 | 7.778 | -1.901 | 14.631 | 1.00 | 35.70 | A | C |
| ATOM | 977 | CD2 | TYR | A | 360 | 7.032 | 0.521 | 15.773 | 1.00 | 34.41 | A | C |
| ATOM | 978 | CE2 | TYR | A | 360 | 7.151 | -0.607 | 16.578 | 1.00 | 35.71 | A | C |
| ATOM | 979 | CZ | TYR | A | 360 | 7.523 | -1.819 | 15.989 | 1.00 | 36.82 | A | C |
| ATOM | 980 | OH | TYR | A | 360 | 7.619 | -2.969 | 16.746 | 1.00 | 39.56 | A | O |
| ATOM | 981 | C | TYR | A | 360 | 5.742 | 3.300 | 12.524 | 1.00 | 28.92 | A | C |
| ATOM | 982 | O | TYR | A | 360 | 5.651 | 3.532 | 11.350 | 1.00 | 29.36 | A | O |
| ATOM | 983 | N | ILE | A | 361 | 5.798 | 4.275 | 13.414 | 1.00 | 28.99 | A | N |
| ATOM | 984 | CA | ILE | A | 361 | 5.920 | 5.651 | 12.978 | 0.00 | 29.41 | A | C |
| ATOM | 985 | CB | ILE | A | 361 | 4.611 | 6.461 | 13.104 | 1.00 | 29.32 | A | C |
| ATOM | 986 | CG2 | ILE | A | 361 | 3.524 | 5.805 | 12.270 | 1.00 | 31.66 | A | C |
| ATOM | 987 | CG1 | ILE | A | 361 | 4.134 | 6.544 | 14.537 | 1.00 | 30.04 | A | C |
| ATOM | 988 | CD1 | ILE | A | 361 | 3.051 | 7.550 | 14.722 | 1.00 | 31.52 | A | C |
| ATOM | 989 | C | ILE | A | 361 | 7.085 | 6.235 | 13.794 | 1.00 | 29.49 | A | C |
| ATOM | 990 | O | ILE | A | 361 | 7.550 | 5.613 | 14.751 | 1.00 | 30.68 | A | O |

Figure 12

| ATOM | 991 | N | HIS | A | 362 | 7.630 | 7.370 | 13.383 | 1.00 | 28.71 | A | N |
|------|------|------|------|---|-----|--------|--------|--------|------|-------|---|---|
| ATOM | 992 | CA | HIS | A | 362 | 8.732 | 7.964 | 14.127 | 0.00 | 27.54 | A | C |
| ATOM | 993 | CB | HIS | A | 362 | 9.684 | 8.688 | 13.176 | 1.00 | 25.70 | A | C |
| ATOM | 994 | CG | HIS | A | 362 | 10.947 | 9.156 | 13.836 | 1.00 | 24.73 | A | C |
| ATOM | 995 | CD2 | HIS | A | 362 | 12.194 | 8.651 | 13.806 | 1.00 | 22.30 | A | C |
| ATOM | 996 | ND1 | HIS | A | 362 | 10.975 | 10.180 | 14.756 | 1.00 | 23.63 | A | N |
| ATOM | 997 | CE1 | HIS | A | 362 | 12.175 | 10.279 | 15.278 | 1.00 | 20.62 | A | C |
| ATOM | 998 | NE2 | HIS | A | 362 | 12.934 | 9.358 | 14.723 | 1.00 | 22.80 | A | N |
| ATOM | 999 | C | HIS | A | 362 | 8.169 | 8.960 | 15.129 | 1.00 | 27.51 | A | C |
| ATOM | 1000 | O | HIS | A | 362 | 8.402 | 8.848 | 16.325 | 1.00 | 29.09 | A | O |
| ATOM | 1001 | N | ARG | A | 363 | 7.303 | 9.821 | 14.622 | 1.00 | 26.99 | A | N |
| ATOM | 1002 | CA | ARG | A | 363 | 6.664 | 10.929 | 15.301 | 0.00 | 26.86 | A | C |
| ATOM | 1003 | CB | ARG | A | 363 | 5.602 | 10.553 | 16.335 | 1.00 | 30.10 | A | C |
| ATOM | 1004 | CG | ARG | A | 363 | 5.996 | 9.617 | 17.405 | 1.00 | 35.00 | A | C |
| ATOM | 1005 | CD | ARG | A | 363 | 4.728 | 9.182 | 18.162 | 1.00 | 37.77 | A | C |
| ATOM | 1006 | NE | ARG | A | 363 | 4.067 | 10.330 | 18.751 | 1.00 | 38.66 | A | N |
| ATOM | 1007 | CZ | ARG | A | 363 | 2.746 | 10.432 | 18.887 | 1.00 | 40.20 | A | C |
| ATOM | 1008 | NH1 | ARG | A | 363 | 1.957 | 9.446 | 18.467 | 1.00 | 37.55 | A | N |
| ATOM | 1009 | NH2 | ARG | A | 363 | 2.219 | 11.532 | 19.422 | 1.00 | 40.65 | A | N |
| ATOM | 1010 | C | ARG | A | 363 | 7.552 | 12.060 | 15.757 | 1.00 | 26.16 | A | C |
| ATOM | 1011 | O | ARG | A | 363 | 7.057 | 13.144 | 16.026 | 1.00 | 25.63 | A | O |
| ATOM | 1012 | N | ASP | A | 364 | 8.876 | 11.853 | 15.776 | 1.00 | 24.38 | A | N |
| ATOM | 1013 | CA | ASP | A | 364 | 9.783 | 12.961 | 16.135 | 0.00 | 24.49 | A | C |
| ATOM | 1014 | CB | ASP | A | 364 | 10.395 | 12.737 | 17.513 | 1.00 | 23.77 | A | C |
| ATOM | 1015 | CG | ASP | A | 364 | 9.388 | 12.897 | 18.613 | 1.00 | 24.42 | A | C |
| ATOM | 1016 | OD1 | ASP | A | 364 | 8.962 | 14.062 | 18.876 | 1.00 | 23.67 | A | O |
| ATOM | 1017 | OD2 | ASP | A | 364 | 8.999 | 11.845 | 19.167 | 1.00 | 24.30 | A | O |
| ATOM | 1018 | C | ASP | A | 364 | 10.891 | 13.223 | 15.080 | 1.00 | 24.48 | A | C |
| ATOM | 1019 | O | ASP | A | 364 | 11.981 | 13.670 | 15.400 | 1.00 | 24.09 | A | O |
| ATOM | 1020 | N | LEU | A | 365 | 10.588 | 12.934 | 13.815 | 1.00 | 22.63 | A | N |
| ATOM | 1021 | CA | LEU | A | 365 | 11.525 | 13.076 | 12.737 | 0.00 | 22.53 | A | C |
| ATOM | 1022 | CB | LEU | A | 365 | 10.950 | 12.387 | 11.496 | 1.00 | 21.09 | A | C |
| ATOM | 1023 | CG | LEU | A | 365 | 11.774 | 12.356 | 10.193 | 1.00 | 21.59 | A | C |
| ATOM | 1024 | CD1 | LEU | A | 365 | 13.088 | 11.581 | 10.522 | 1.00 | 19.75 | A | C |
| ATOM | 1025 | CD2 | LEU | A | 365 | 10.960 | 11.683 | 8.991 | 1.00 | 15.89 | A | C |
| ATOM | 1026 | C | LEU | A | 365 | 11.914 | 14.516 | 12.374 | 1.00 | 24.01 | A | C |
| ATOM | 1027 | O | LEU | A | 365 | 11.083 | 15.283 | 11.884 | 1.00 | 25.29 | A | O |
| ATOM | 1028 | N | ARG | A | 366 | 13.168 | 14.874 | 12.620 | 1.00 | 23.90 | A | N |
| ATOM | 1029 | CA | ARG | A | 366 | 13.691 | 16.175 | 12.276 | 0.00 | 24.69 | A | C |
| ATOM | 1030 | CB | ARG | A | 366 | 13.173 | 17.242 | 13.224 | 1.00 | 26.13 | A | C |
| ATOM | 1031 | CG | ARG | A | 366 | 13.394 | 16.975 | 14.719 | 1.00 | 28.49 | A | C |
| ATOM | 1032 | CD | ARG | A | 366 | 13.036 | 18.206 | 15.525 | 1.00 | 29.28 | A | C |
| ATOM | 1033 | NE | ARG | A | 366 | 12.992 | 17.937 | 16.960 | 1.00 | 33.28 | A | N |
| ATOM | 1034 | CZ | ARG | A | 366 | 11.999 | 17.286 | 17.585 | 1.00 | 32.37 | A | C |
| ATOM | 1035 | NH1 | ARG | A | 366 | 10.937 | 16.820 | 16.932 | 1.00 | 30.41 | A | N |
| ATOM | 1036 | NH2 | ARG | A | 366 | 12.086 | 17.128 | 18.896 | 1.00 | 32.92 | A | N |
| ATOM | 1037 | C | ARG | A | 366 | 15.220 | 16.076 | 12.291 | 1.00 | 24.45 | A | C |
| ATOM | 1038 | O | ARG | A | 366 | 15.762 | 15.064 | 12.736 | 1.00 | 24.55 | A | O |
| ATOM | 1039 | N | ALA | A | 367 | 15.924 | 17.060 | 11.730 | 1.00 | 23.21 | A | N |
| ATOM | 1040 | CA | ALA | A | 367 | 17.400 | 16.978 | 11.726 | 0.00 | 22.83 | A | C |
| ATOM | 1041 | CB | ALA | A | 367 | 18.013 | 18.219 | 11.085 | 1.00 | 23.20 | A | C |
| ATOM | 1042 | C | ALA | A | 367 | 18.050 | 16.729 | 13.096 | 1.00 | 22.48 | A | C |
| ATOM | 1043 | O | ALA | A | 367 | 19.062 | 16.051 | 13.185 | 1.00 | 22.07 | A | O |
| ATOM | 1044 | N | ALA | A | 368 | 17.491 | 17.288 | 14.165 | 1.00 | 22.63 | A | N |
| ATOM | 1045 | CA | ALA | A | 368 | 18.043 | 17.091 | 15.507 | 0.00 | 22.41 | A | C |
| ATOM | 1046 | CB | ALA | A | 368 | 17.232 | 17.886 | 16.533 | 1.00 | 22.30 | A | C |
| ATOM | 1047 | C | ALA | A | 368 | 18.057 | 15.618 | 15.907 | 1.00 | 23.56 | A | C |
| ATOM | 1048 | O | ALA | A | 368 | 18.936 | 15.186 | 16.663 | 1.00 | 23.33 | A | O |
| ATOM | 1049 | N | ASN | A | 369 | 17.109 | 14.833 | 15.382 | 1.00 | 24.06 | A | N |

Figure 12

| ATOM | 1050 | CA  | ASN | A | 369 | 17.030 | 13.421 | 15.752 | 0.00 | 23.89 | A | C |
|------|------|-----|-----|---|-----|--------|--------|--------|------|-------|---|---|
| ATOM | 1051 | CB  | ASN | A | 369 | 15.581 | 13.050 | 16.147 | 1.00 | 24.44 | A | C |
| ATOM | 1052 | CG  | ASN | A | 369 | 15.093 | 13.866 | 17.349 | 1.00 | 25.17 | A | C |
| ATOM | 1053 | OD1 | ASN | A | 369 | 15.813 | 14.000 | 18.320 | 1.00 | 28.21 | A | O |
| ATOM | 1054 | ND2 | ASN | A | 369 | 13.897 | 14.431 | 17.289 | 1.00 | 23.28 | A | N |
| ATOM | 1055 | C   | ASN | A | 369 | 17.700 | 12.465 | 14.794 | 1.00 | 23.40 | A | C |
| ATOM | 1056 | O   | ASN | A | 369 | 17.432 | 11.281 | 14.796 | 1.00 | 24.02 | A | O |
| ATOM | 1057 | N   | ILE | A | 370 | 18.552 | 13.013 | 13.916 | 1.00 | 23.58 | A | N |
| ATOM | 1058 | CA  | ILE | A | 370 | 19.341 | 12.191 | 12.993 | 0.00 | 22.46 | A | C |
| ATOM | 1059 | CB  | ILE | A | 370 | 19.336 | 12.734 | 11.546 | 1.00 | 21.07 | A | C |
| ATOM | 1060 | CG2 | ILE | A | 370 | 20.176 | 11.806 | 10.667 | 1.00 | 18.07 | A | C |
| ATOM | 1061 | CG1 | ILE | A | 370 | 17.910 | 12.797 | 10.996 | 1.00 | 18.39 | A | C |
| ATOM | 1062 | CD1 | ILE | A | 370 | 17.190 | 11.432 | 11.011 | 1.00 | 18.16 | A | C |
| ATOM | 1063 | C   | ILE | A | 370 | 20.788 | 12.232 | 13.522 | 1.00 | 22.97 | A | C |
| ATOM | 1064 | O   | ILE | A | 370 | 21.236 | 13.256 | 13.982 | 1.00 | 21.95 | A | O |
| ATOM | 1065 | N   | LEU | A | 371 | 21.492 | 11.112 | 13.531 | 1.00 | 24.86 | A | N |
| ATOM | 1066 | CA  | LEU | A | 371 | 22.902 | 11.123 | 14.032 | 0.00 | 25.23 | A | C |
| ATOM | 1067 | CB  | LEU | A | 371 | 23.115 | 10.072 | 15.125 | 1.00 | 24.56 | A | C |
| ATOM | 1068 | CG  | LEU | A | 371 | 22.380 | 10.415 | 16.424 | 1.00 | 25.56 | A | C |
| ATOM | 1069 | CD1 | LEU | A | 371 | 22.732 |  9.443 | 17.528 | 1.00 | 25.83 | A | C |
| ATOM | 1070 | CD2 | LEU | A | 371 | 22.661 | 11.831 | 16.868 | 1.00 | 25.42 | A | C |
| ATOM | 1071 | C   | LEU | A | 371 | 23.854 | 10.885 | 12.863 | 1.00 | 25.98 | A | C |
| ATOM | 1072 | O   | LEU | A | 371 | 23.532 | 10.123 | 11.946 | 1.00 | 25.72 | A | O |
| ATOM | 1073 | N   | VAL | A | 372 | 24.993 | 11.579 | 12.874 | 1.00 | 27.01 | A | N |
| ATOM | 1074 | CA  | VAL | A | 372 | 26.014 | 11.480 | 11.806 | 0.00 | 28.22 | A | C |
| ATOM | 1075 | CB  | VAL | A | 372 | 26.429 | 12.870 | 11.302 | 1.00 | 28.13 | A | C |
| ATOM | 1076 | CG1 | VAL | A | 372 | 27.413 | 12.736 | 10.150 | 1.00 | 28.65 | A | C |
| ATOM | 1077 | CG2 | VAL | A | 372 | 25.208 | 13.682 | 10.914 | 1.00 | 27.89 | A | C |
| ATOM | 1078 | C   | VAL | A | 372 | 27.266 | 10.794 | 12.335 | 1.00 | 28.62 | A | C |
| ATOM | 1079 | O   | VAL | A | 372 | 27.822 | 11.191 | 13.361 | 1.00 | 27.51 | A | O |
| ATOM | 1080 | N   | SER | A | 373 | 27.687 |  9.760 | 11.622 | 1.00 | 30.17 | A | N |
| ATOM | 1081 | CA  | SER | A | 373 | 28.846 |  8.981 | 11.996 | 0.00 | 32.73 | A | C |
| ATOM | 1082 | CB  | SER | A | 373 | 28.699 |  7.567 | 11.433 | 1.00 | 31.47 | A | C |
| ATOM | 1083 | OG  | SER | A | 373 | 29.271 |  7.466 | 10.146 | 1.00 | 31.46 | A | O |
| ATOM | 1084 | C   | SER | A | 373 | 30.192 |  9.631 | 11.548 | 1.00 | 35.13 | A | C |
| ATOM | 1085 | O   | SER | A | 373 | 30.226 | 10.709 | 10.929 | 1.00 | 34.10 | A | O |
| ATOM | 1086 | N   | ASP | A | 374 | 31.297 |  8.987 | 11.922 | 1.00 | 38.13 | A | N |
| ATOM | 1087 | CA  | ASP | A | 374 | 32.630 |  9.490 | 11.565 | 0.00 | 41.00 | A | C |
| ATOM | 1088 | CB  | ASP | A | 374 | 33.735 |  8.628 | 12.185 | 1.00 | 43.73 | A | C |
| ATOM | 1089 | CG  | ASP | A | 374 | 33.424 |  7.147 | 12.135 | 1.00 | 46.68 | A | C |
| ATOM | 1090 | OD1 | ASP | A | 374 | 32.499 |  6.723 | 12.865 | 1.00 | 48.83 | A | O |
| ATOM | 1091 | OD2 | ASP | A | 374 | 34.094 |  6.407 | 11.381 | 1.00 | 48.43 | A | O |
| ATOM | 1092 | C   | ASP | A | 374 | 32.756 |  9.488 | 10.069 | 1.00 | 41.44 | A | C |
| ATOM | 1093 | O   | ASP | A | 374 | 33.291 | 10.427 |  9.480 | 1.00 | 41.69 | A | O |
| ATOM | 1094 | N   | THR | A | 375 | 32.149 |  8.479 |  9.455 | 1.00 | 41.41 | A | N |
| ATOM | 1095 | CA  | THR | A | 375 | 32.192 |  8.340 |  8.015 | 0.00 | 41.50 | A | C |
| ATOM | 1096 | CB  | THR | A | 375 | 32.044 |  6.875 |  7.637 | 1.00 | 42.39 | A | C |
| ATOM | 1097 | OG1 | THR | A | 375 | 30.750 |  6.404 |  8.033 | 1.00 | 42.01 | A | O |
| ATOM | 1098 | CG2 | THR | A | 375 | 33.110 |  6.051 |  8.386 | 1.00 | 43.28 | A | C |
| ATOM | 1099 | C   | THR | A | 375 | 31.147 |  9.190 |  7.274 | 1.00 | 41.22 | A | C |
| ATOM | 1100 | O   | THR | A | 375 | 31.052 |  9.151 |  6.048 | 1.00 | 40.44 | A | O |
| ATOM | 1101 | N   | LEU | A | 376 | 30.388 |  9.968 |  8.040 | 1.00 | 41.14 | A | N |
| ATOM | 1102 | CA  | LEU | A | 376 | 29.325 | 10.845 |  7.526 | 0.00 | 41.23 | A | C |
| ATOM | 1103 | CB  | LEU | A | 376 | 29.807 | 11.818 |  6.435 | 1.00 | 41.72 | A | C |
| ATOM | 1104 | CG  | LEU | A | 376 | 30.949 | 12.802 |  6.709 | 1.00 | 43.17 | A | C |
| ATOM | 1105 | CD1 | LEU | A | 376 | 30.751 | 14.027 |  5.827 | 1.00 | 43.35 | A | C |
| ATOM | 1106 | CD2 | LEU | A | 376 | 31.010 | 13.228 |  8.176 | 1.00 | 43.14 | A | C |
| ATOM | 1107 | C   | LEU | A | 376 | 28.060 | 10.136 |  7.055 | 1.00 | 40.47 | A | C |
| ATOM | 1108 | O   | LEU | A | 376 | 27.372 | 10.647 |  6.176 | 1.00 | 41.11 | A | O |

Figure 12

```
ATOM   1109  N    SER A 377      27.811   8.924   7.564  1.00 39.31      A   N
ATOM   1110  CA   SER A 377      26.590   8.200   7.241  0.00 37.88      A   C
ATOM   1111  CB   SER A 377      26.820   6.684   7.133  1.00 39.21      A   C
ATOM   1112  OG   SER A 377      27.031   6.053   8.387  1.00 42.88      A   O
ATOM   1113  C    SER A 377      25.565   8.562   8.336  1.00 36.33      A   C
ATOM   1114  O    SER A 377      25.910   8.779   9.504  1.00 35.98      A   O
ATOM   1115  N    CYS A 378      24.300   8.658   7.936  1.00 34.78      A   N
ATOM   1116  CA   CYS A 378      23.217   9.048   8.830  0.00 31.77      A   C
ATOM   1117  CB   CYS A 378      22.258   9.976   8.084  1.00 32.21      A   C
ATOM   1118  SG   CYS A 378      22.986  11.571   7.673  1.00 33.25      A   S
ATOM   1119  C    CYS A 378      22.471   7.870   9.397  1.00 29.81      A   C
ATOM   1120  O    CYS A 378      22.403   6.834   8.765  1.00 29.48      A   O
ATOM   1121  N    LYS A 379      22.017   8.014  10.639  1.00 28.33      A   N
ATOM   1122  CA   LYS A 379      21.247   6.979  11.336  0.00 28.32      A   C
ATOM   1123  CB   LYS A 379      22.089   6.095  12.280  1.00 28.34      A   C
ATOM   1124  CG   LYS A 379      22.892   4.956  11.597  1.00 29.98      A   C
ATOM   1125  CD   LYS A 379      23.965   4.310  12.539  1.00 32.39      A   C
ATOM   1126  CE   LYS A 379      24.671   3.039  11.959  1.00 33.11      A   C
ATOM   1127  NZ   LYS A 379      23.937   1.743  12.374  1.00 38.98      A   N
ATOM   1128  C    LYS A 379      20.157   7.684  12.117  1.00 27.72      A   C
ATOM   1129  O    LYS A 379      20.351   8.779  12.675  1.00 27.16      A   O
ATOM   1130  N    ILE A 380      18.988   7.070  12.078  1.00 27.24      A   N
ATOM   1131  CA   ILE A 380      17.802   7.592  12.729  0.00 28.10      A   C
ATOM   1132  CB   ILE A 380      16.497   7.017  12.084  1.00 26.99      A   C
ATOM   1133  CG2  ILE A 380      15.313   7.536  12.794  1.00 24.38      A   C
ATOM   1134  CG1  ILE A 380      16.408   7.385  10.601  1.00 27.55      A   C
ATOM   1135  CD1  ILE A 380      15.268   6.681   9.895  1.00 26.57      A   C
ATOM   1136  C    ILE A 380      17.804   7.249  14.219  1.00 28.13      A   C
ATOM   1137  O    ILE A 380      18.067   6.100  14.597  1.00 27.94      A   O
ATOM   1138  N    ALA A 381      17.417   8.215  15.048  1.00 28.09      A   N
ATOM   1139  CA   ALA A 381      17.364   7.973  16.482  0.00 29.48      A   C
ATOM   1140  CB   ALA A 381      18.480   8.783  17.203  1.00 28.66      A   C
ATOM   1141  C    ALA A 381      16.023   8.376  17.051  1.00 29.00      A   C
ATOM   1142  O    ALA A 381      15.270   9.120  16.434  1.00 28.06      A   O
ATOM   1143  N    ASP A 382      15.725   7.841  18.222  1.00 30.03      A   N
ATOM   1144  CA   ASP A 382      14.531   8.245  18.948  0.00 31.56      A   C
ATOM   1145  CB   ASP A 382      14.732   9.683  19.476  1.00 32.87      A   C
ATOM   1146  CG   ASP A 382      15.510   9.723  20.822  1.00 34.65      A   C
ATOM   1147  OD1  ASP A 382      15.598   8.676  21.529  1.00 35.68      A   O
ATOM   1148  OD2  ASP A 382      16.002  10.807  21.192  1.00 34.92      A   O
ATOM   1149  C    ASP A 382      13.228   8.114  18.210  1.00 31.45      A   C
ATOM   1150  O    ASP A 382      12.347   8.975  18.278  1.00 31.26      A   O
ATOM   1151  N    PHE A 383      13.101   6.972  17.564  1.00 32.04      A   N
ATOM   1152  CA   PHE A 383      11.937   6.633  16.784  0.00 33.89      A   C
ATOM   1153  CB   PHE A 383      12.393   5.849  15.556  1.00 34.36      A   C
ATOM   1154  CG   PHE A 383      13.305   4.691  15.889  1.00 35.47      A   C
ATOM   1155  CD1  PHE A 383      12.776   3.467  16.303  1.00 36.35      A   C
ATOM   1156  CD2  PHE A 383      14.691   4.833  15.809  1.00 35.68      A   C
ATOM   1157  CE1  PHE A 383      13.611   2.386  16.639  1.00 36.28      A   C
ATOM   1158  CE2  PHE A 383      15.557   3.742  16.144  1.00 36.69      A   C
ATOM   1159  CZ   PHE A 383      15.005   2.517  16.560  1.00 36.13      A   C
ATOM   1160  C    PHE A 383      10.975   5.764  17.579  1.00 34.83      A   C
ATOM   1161  O    PHE A 383      11.390   4.995  18.452  1.00 34.78      A   O
ATOM   1162  N    GLY A 384       9.698   5.874  17.245  1.00 35.69      A   N
ATOM   1163  CA   GLY A 384       8.688   5.042  17.860  0.00 37.20      A   C
ATOM   1164  C    GLY A 384       8.170   5.417  19.220  1.00 38.57      A   C
ATOM   1165  O    GLY A 384       7.371   4.680  19.779  1.00 39.70      A   O
ATOM   1166  N    LEU A 385       8.608   6.543  19.769  1.00 39.78      A   N
ATOM   1167  CA   LEU A 385       8.172   6.941  21.102  0.00 40.61      A   C
```

Figure 12

| ATOM | 1168 | CB  | LEU | A | 385 | 8.970  | 8.153  | 21.632 | 1.00 | 40.48 | A | C |
| ATOM | 1169 | CG  | LEU | A | 385 | 10.500 | 8.238  | 21.446 | 1.00 | 40.66 | A | C |
| ATOM | 1170 | CD1 | LEU | A | 385 | 11.074 | 9.426  | 22.219 | 1.00 | 40.28 | A | C |
| ATOM | 1171 | CD2 | LEU | A | 385 | 11.188 | 6.954  | 21.867 | 1.00 | 41.55 | A | C |
| ATOM | 1172 | C   | LEU | A | 385 | 6.705  | 7.310  | 21.048 | 1.00 | 41.68 | A | C |
| ATOM | 1173 | O   | LEU | A | 385 | 6.209  | 7.763  | 20.013 | 1.00 | 41.59 | A | O |
| ATOM | 1174 | N   | ALA | A | 386 | 6.027  | 7.136  | 22.180 | 1.00 | 42.23 | A | N |
| ATOM | 1175 | CA  | ALA | A | 386 | 4.607  | 7.469  | 22.284 | 0.00 | 42.86 | A | C |
| ATOM | 1176 | CB  | ALA | A | 386 | 3.963  | 6.729  | 23.500 | 1.00 | 42.98 | A | C |
| ATOM | 1177 | C   | ALA | A | 386 | 4.472  | 8.960  | 22.482 | 1.00 | 42.40 | A | C |
| ATOM | 1178 | O   | ALA | A | 386 | 3.376  | 9.516  | 22.394 | 1.00 | 42.85 | A | O |
| ATOM | 1179 | N   | ARG | A | 387 | 5.592  | 9.610  | 22.766 | 1.00 | 41.73 | A | N |
| ATOM | 1180 | CA  | ARG | A | 387 | 5.549  | 11.035 | 23.041 | 0.00 | 40.48 | A | C |
| ATOM | 1181 | CB  | ARG | A | 387 | 5.986  | 11.280 | 24.484 | 1.00 | 40.04 | A | C |
| ATOM | 1182 | CG  | ARG | A | 387 | 7.441  | 10.919 | 24.755 | 1.00 | 40.50 | A | C |
| ATOM | 1183 | CD  | ARG | A | 387 | 7.826  | 11.261 | 26.183 | 1.00 | 40.48 | A | C |
| ATOM | 1184 | NE  | ARG | A | 387 | 9.271  | 11.224 | 26.406 | 1.00 | 40.27 | A | N |
| ATOM | 1185 | CZ  | ARG | A | 387 | 10.062 | 12.291 | 26.300 | 1.00 | 39.00 | A | C |
| ATOM | 1186 | NH1 | ARG | A | 387 | 9.554  | 13.478 | 25.981 | 1.00 | 37.56 | A | N |
| ATOM | 1187 | NH2 | ARG | A | 387 | 11.372 | 12.154 | 26.494 | 1.00 | 39.87 | A | N |
| ATOM | 1188 | C   | ARG | A | 387 | 6.344  | 11.922 | 22.105 | 1.00 | 39.86 | A | C |
| ATOM | 1189 | O   | ARG | A | 387 | 7.188  | 11.473 | 21.335 | 1.00 | 40.68 | A | O |
| ATOM | 1190 | N   | LEU | A | 388 | 6.048  | 13.200 | 22.200 | 1.00 | 38.61 | A | N |
| ATOM | 1191 | CA  | LEU | A | 388 | 6.679  | 14.225 | 21.432 | 0.00 | 37.44 | A | C |
| ATOM | 1192 | CB  | LEU | A | 388 | 5.619  | 15.246 | 21.102 | 1.00 | 38.10 | A | C |
| ATOM | 1193 | CG  | LEU | A | 388 | 4.448  | 14.415 | 20.528 | 1.00 | 40.87 | A | C |
| ATOM | 1194 | CD1 | LEU | A | 388 | 3.133  | 15.178 | 20.576 | 1.00 | 41.66 | A | C |
| ATOM | 1195 | CD2 | LEU | A | 388 | 4.776  | 13.977 | 19.096 | 1.00 | 40.79 | A | C |
| ATOM | 1196 | C   | LEU | A | 388 | 7.799  | 14.826 | 22.289 | 1.00 | 36.09 | A | C |
| ATOM | 1197 | O   | LEU | A | 388 | 7.521  | 15.440 | 23.311 | 1.00 | 36.96 | A | O |
| ATOM | 1198 | N   | ILE | A | 389 | 9.052  | 14.669 | 21.846 | 1.00 | 33.94 | A | N |
| ATOM | 1199 | CA  | ILE | A | 389 | 10.234 | 15.168 | 22.553 | 0.00 | 31.70 | A | C |
| ATOM | 1200 | CB  | ILE | A | 389 | 11.388 | 14.147 | 22.481 | 1.00 | 30.88 | A | C |
| ATOM | 1201 | CG2 | ILE | A | 389 | 10.917 | 12.786 | 22.951 | 1.00 | 29.25 | A | C |
| ATOM | 1202 | CG1 | ILE | A | 389 | 11.969 | 14.023 | 21.064 | 1.00 | 29.97 | A | C |
| ATOM | 1203 | CD1 | ILE | A | 389 | 12.806 | 12.732 | 20.860 | 1.00 | 27.43 | A | C |
| ATOM | 1204 | C   | ILE | A | 389 | 10.762 | 16.527 | 22.129 | 1.00 | 31.62 | A | C |
| ATOM | 1205 | O   | ILE | A | 389 | 10.487 | 16.989 | 21.029 | 1.00 | 30.46 | A | O |
| ATOM | 1206 | N   | GLU | A | 390 | 11.404 | 17.233 | 23.064 | 1.00 | 32.01 | A | N |
| ATOM | 1207 | CA  | GLU | A | 390 | 12.028 | 18.522 | 22.772 | 0.00 | 33.78 | A | C |
| ATOM | 1208 | CB  | GLU | A | 390 | 11.695 | 19.556 | 23.828 | 1.00 | 34.42 | A | C |
| ATOM | 1209 | CG  | GLU | A | 390 | 10.277 | 20.035 | 23.749 | 1.00 | 39.86 | A | C |
| ATOM | 1210 | CD  | GLU | A | 390 | 9.834  | 20.760 | 24.992 | 1.00 | 41.47 | A | C |
| ATOM | 1211 | OE1 | GLU | A | 390 | 8.762  | 20.431 | 25.481 | 1.00 | 44.54 | A | O |
| ATOM | 1212 | OE2 | GLU | A | 390 | 10.535 | 21.644 | 25.505 | 1.00 | 44.60 | A | O |
| ATOM | 1213 | C   | GLU | A | 390 | 13.552 | 18.316 | 22.682 | 1.00 | 33.94 | A | C |
| ATOM | 1214 | O   | GLU | A | 390 | 14.085 | 17.351 | 23.221 | 1.00 | 33.84 | A | O |
| ATOM | 1215 | N   | ASP | A | 391 | 14.261 | 19.227 | 22.033 | 1.00 | 35.17 | A | N |
| ATOM | 1216 | CA  | ASP | A | 391 | 15.724 | 19.037 | 21.887 | 0.00 | 36.86 | A | C |
| ATOM | 1217 | CB  | ASP | A | 391 | 16.300 | 19.896 | 20.762 | 1.00 | 38.82 | A | C |
| ATOM | 1218 | CG  | ASP | A | 391 | 15.608 | 19.683 | 19.435 | 1.00 | 40.10 | A | C |
| ATOM | 1219 | OD1 | ASP | A | 391 | 15.221 | 18.527 | 19.075 | 1.00 | 41.07 | A | O |
| ATOM | 1220 | OD2 | ASP | A | 391 | 15.463 | 20.712 | 18.751 | 1.00 | 42.45 | A | O |
| ATOM | 1221 | C   | ASP | A | 391 | 16.522 | 19.336 | 23.122 | 1.00 | 36.83 | A | C |
| ATOM | 1222 | O   | ASP | A | 391 | 17.692 | 18.951 | 23.212 | 1.00 | 37.66 | A | O |
| ATOM | 1223 | N   | ASN | A | 392 | 15.888 | 20.048 | 24.046 | 1.00 | 36.05 | A | N |
| ATOM | 1224 | CA  | ASN | A | 392 | 16.498 | 20.464 | 25.289 | 0.00 | 35.17 | A | C |
| ATOM | 1225 | CB  | ASN | A | 392 | 15.910 | 21.824 | 25.697 | 1.00 | 35.42 | A | C |
| ATOM | 1226 | CG  | ASN | A | 392 | 14.513 | 21.701 | 26.293 | 1.00 | 36.94 | A | C |

Figure 12

```
ATOM   1227  OD1 ASN A 392      13.834  20.672  26.148  1.00 36.47      A    O
ATOM   1228  ND2 ASN A 392      14.086  22.741  26.998  1.00 37.77      A    N
ATOM   1229  C   ASN A 392      16.355  19.463  26.447  1.00 33.93      A    C
ATOM   1230  O   ASN A 392      16.492  19.831  27.611  1.00 33.70      A    O
ATOM   1231  N   GLU A 393      16.061  18.214  26.142  1.00 33.31      A    N
ATOM   1232  CA  GLU A 393      15.885  17.224  27.183  0.00 32.78      A    C
ATOM   1233  CB  GLU A 393      14.980  16.098  26.718  1.00 31.03      A    C
ATOM   1234  CG  GLU A 393      13.554  16.425  27.019  1.00 30.87      A    C
ATOM   1235  CD  GLU A 393      12.552  15.744  26.121  1.00 29.09      A    C
ATOM   1236  OE1 GLU A 393      12.723  14.568  25.742  1.00 28.94      A    O
ATOM   1237  OE2 GLU A 393      11.561  16.407  25.838  1.00 30.23      A    O
ATOM   1238  C   GLU A 393      17.165  16.629  27.675  1.00 33.73      A    C
ATOM   1239  O   GLU A 393      17.284  16.334  28.860  1.00 32.80      A    O
ATOM   1240  N   TYR A 394      18.087  16.414  26.746  1.00 34.59      A    N
ATOM   1241  CA  TYR A 394      19.361  15.808  27.066  0.00 36.43      A    C
ATOM   1242  CB  TYR A 394      19.398  14.387  26.501  1.00 34.84      A    C
ATOM   1243  CG  TYR A 394      18.276  13.533  27.045  1.00 34.14      A    C
ATOM   1244  CD1 TYR A 394      17.036  13.464  26.399  1.00 33.06      A    C
ATOM   1245  CE1 TYR A 394      15.979  12.721  26.936  1.00 32.60      A    C
ATOM   1246  CD2 TYR A 394      18.432  12.829  28.238  1.00 34.07      A    C
ATOM   1247  CE2 TYR A 394      17.391  12.080  28.789  1.00 33.33      A    C
ATOM   1248  CZ  TYR A 394      16.155  12.028  28.139  1.00 33.26      A    C
ATOM   1249  OH  TYR A 394      15.128  11.312  28.723  1.00 29.99      A    O
ATOM   1250  C   TYR A 394      20.583  16.650  26.651  1.00 38.14      A    C
ATOM   1251  O   TYR A 394      21.722  16.212  26.841  1.00 38.27      A    O
ATOM   1252  N   THR A 395      20.328  17.843  26.106  1.00 39.72      A    N
ATOM   1253  CA  THR A 395      21.364  18.782  25.693  0.00 42.69      A    C
ATOM   1254  CB  THR A 395      21.726  18.690  24.195  1.00 43.60      A    C
ATOM   1255  OG1 THR A 395      20.566  18.933  23.384  1.00 43.58      A    O
ATOM   1256  CG2 THR A 395      22.354  17.332  23.877  1.00 44.08      A    C
ATOM   1257  C   THR A 395      20.837  20.164  25.981  1.00 44.65      A    C
ATOM   1258  O   THR A 395      19.731  20.299  26.488  1.00 45.10      A    O
ATOM   1259  N   ALA A 396      21.570  21.204  25.613  1.00 47.14      A    N
ATOM   1260  CA  ALA A 396      21.107  22.541  25.939  0.00 50.17      A    C
ATOM   1261  CB  ALA A 396      22.119  23.243  26.865  1.00 49.88      A    C
ATOM   1262  C   ALA A 396      20.640  23.494  24.835  1.00 52.54      A    C
ATOM   1263  O   ALA A 396      20.711  24.719  25.023  1.00 53.55      A    O
ATOM   1264  N   ARG A 397      20.079  22.958  23.744  1.00 54.64      A    N
ATOM   1265  CA  ARG A 397      19.579  23.808  22.650  0.00 55.78      A    C
ATOM   1266  CB  ARG A 397      19.142  22.958  21.452  1.00 55.96      A    C
ATOM   1267  CG  ARG A 397      20.209  22.012  20.927  1.00 56.33      A    C
ATOM   1268  CD  ARG A 397      20.192  21.967  19.408  1.00 56.71      A    C
ATOM   1269  NE  ARG A 397      20.911  20.811  18.872  1.00 56.32      A    N
ATOM   1270  CZ  ARG A 397      20.465  19.559  18.950  1.00 55.91      A    C
ATOM   1271  NH1 ARG A 397      19.312  19.299  19.549  1.00 55.69      A    N
ATOM   1272  NH2 ARG A 397      21.141  18.573  18.387  1.00 55.32      A    N
ATOM   1273  C   ARG A 397      18.397  24.674  23.136  1.00 56.53      A    C
ATOM   1274  O   ARG A 397      18.613  25.894  23.382  1.00 57.38      A    O
ATOM   1275  CB  PRO A 403       8.858  20.423  18.667  1.00 32.96      A    C
ATOM   1276  CG  PRO A 403       9.219  20.962  20.073  1.00 33.39      A    C
ATOM   1277  C   PRO A 403       7.406  21.517  16.883  1.00 31.94      A    C
ATOM   1278  O   PRO A 403       7.284  20.507  16.122  1.00 32.02      A    O
ATOM   1279  N   PRO A 403       8.178  22.737  18.981  1.00 32.61      A    N
ATOM   1280  CD  PRO A 403       8.272  22.162  20.313  1.00 34.00      A    C
ATOM   1281  CA  PRO A 403       8.546  21.701  17.929  0.00 32.44      A    C
ATOM   1282  N   ILE A 404       6.681  22.617  16.752  1.00 30.23      A    N
ATOM   1283  CA  ILE A 404       5.541  22.725  15.885  0.00 28.69      A    C
ATOM   1284  CB  ILE A 404       4.760  23.969  16.363  1.00 29.68      A    C
ATOM   1285  CG2 ILE A 404       4.163  24.737  15.221 -1.00 29.69      A    C
```

Figure 12

```
ATOM   1286  CG1 ILE A 404       3.729  23.515  17.374  1.00 32.20      A    C
ATOM   1287  CD1 ILE A 404       2.787  22.463  16.792  1.00 32.65      A    C
ATOM   1288  C   ILE A 404       5.878  22.740  14.377  1.00 26.67      A    C
ATOM   1289  O   ILE A 404       5.186  22.130  13.567  1.00 25.67      A    O
ATOM   1290  N   LYS A 405       7.027  23.318  14.040  1.00 24.58      A    N
ATOM   1291  CA  LYS A 405       7.458  23.470  12.657  0.00 21.64      A    C
ATOM   1292  CB  LYS A 405       8.673  24.395  12.573  1.00 19.69      A    C
ATOM   1293  CG  LYS A 405       8.403  25.754  13.149  1.00 19.14      A    C
ATOM   1294  CD  LYS A 405       9.547  26.700  12.904  1.00 18.84      A    C
ATOM   1295  CE  LYS A 405       9.231  28.138  13.278  1.00 19.86      A    C
ATOM   1296  NZ  LYS A 405      10.281  29.111  12.760  1.00 23.48      A    N
ATOM   1297  C   LYS A 405       7.656  22.236  11.816  1.00 20.29      A    C
ATOM   1298  O   LYS A 405       7.870  22.377  10.630  1.00 20.05      A    O
ATOM   1299  N   TRP A 406       7.650  21.050  12.428  1.00 19.55      A    N
ATOM   1300  CA  TRP A 406       7.784  19.772  11.707  0.00 19.82      A    C
ATOM   1301  CB  TRP A 406       8.894  18.867  12.319  1.00 19.51      A    C
ATOM   1302  CG  TRP A 406      10.323  19.417  12.145  1.00 19.75      A    C
ATOM   1303  CD2 TRP A 406      10.958  20.435  12.950  1.00 20.04      A    C
ATOM   1304  CE2 TRP A 406      12.264  20.640  12.405  1.00 21.00      A    C
ATOM   1305  CE3 TRP A 406      10.559  21.188  14.054  1.00 21.07      A    C
ATOM   1306  CD1 TRP A 406      11.239  19.044  11.180  1.00 19.28      A    C
ATOM   1307  NE1 TRP A 406      12.404  19.795  11.335  1.00 21.28      A    N
ATOM   1308  CZ2 TRP A 406      13.175  21.583  12.953  1.00 22.01      A    C
ATOM   1309  CZ3 TRP A 406      11.470  22.135  14.607  1.00 22.62      A    C
ATOM   1310  CH2 TRP A 406      12.771  22.316  14.043  1.00 21.92      A    C
ATOM   1311  C   TRP A 406       6.494  18.948  11.739  1.00 19.92      A    C
ATOM   1312  O   TRP A 406       6.455  17.833  11.197  1.00 19.72      A    O
ATOM   1313  N   THR A 407       5.444  19.486  12.369  1.00 18.96      A    N
ATOM   1314  CA  THR A 407       4.182  18.747  12.543  0.00 18.99      A    C
ATOM   1315  CB  THR A 407       3.547  19.160  13.886  1.00 20.73      A    C
ATOM   1316  OG1 THR A 407       4.528  19.052  14.923  1.00 23.19      A    O
ATOM   1317  CG2 THR A 407       2.358  18.252  14.249  1.00 21.49      A    C
ATOM   1318  C   THR A 407       3.167  18.964  11.405  1.00 17.85      A    C
ATOM   1319  O   THR A 407       2.915  20.110  11.030  1.00 16.47      A    O
ATOM   1320  N   ALA A 408       2.651  17.870  10.836  1.00 16.70      A    N
ATOM   1321  CA  ALA A 408       1.659  17.928   9.751  0.00 18.55      A    C
ATOM   1322  CB  ALA A 408       1.347  16.537   9.269  1.00 18.39      A    C
ATOM   1323  C   ALA A 408       0.382  18.584  10.229  1.00 19.42      A    C
ATOM   1324  O   ALA A 408       0.065  18.492  11.413  1.00 19.52      A    O
ATOM   1325  N   PRO A 409      -0.418  19.203   9.322  1.00 20.38      A    N
ATOM   1326  CD  PRO A 409      -0.204  19.354   7.877  1.00 20.51      A    C
ATOM   1327  CA  PRO A 409      -1.673  19.856   9.743  0.00 21.37      A    C
ATOM   1328  CB  PRO A 409      -2.258  20.390   8.424  1.00 21.67      A    C
ATOM   1329  CG  PRO A 409      -1.064  20.536   7.548  1.00 21.50      A    C
ATOM   1330  C   PRO A 409      -2.687  18.974  10.492  1.00 21.59      A    C
ATOM   1331  O   PRO A 409      -3.292  19.426  11.453  1.00 21.00      A    O
ATOM   1332  N   GLU A 410      -2.914  17.746  10.044  1.00 21.93      A    N
ATOM   1333  CA  GLU A 410      -3.863  16.886  10.733  0.00 23.32      A    C
ATOM   1334  CB  GLU A 410      -4.159  15.615   9.910  1.00 21.89      A    C
ATOM   1335  CG  GLU A 410      -2.996  14.566   9.831  1.00 21.78      A    C
ATOM   1336  CD  GLU A 410      -1.832  14.908   8.827  1.00 20.37      A    C
ATOM   1337  OE1 GLU A 410      -1.881  15.954   8.153  1.00 19.87      A    O
ATOM   1338  OE2 GLU A 410      -0.910  14.074   8.666  1.00 17.33      A    O
ATOM   1339  C   GLU A 410      -3.344  16.492  12.125  1.00 25.07      A    C
ATOM   1340  O   GLU A 410      -4.109  16.037  13.001  1.00 26.18      A    O
ATOM   1341  N   ALA A 411      -2.049  16.627  12.348  1.00 24.78      A    N
ATOM   1342  CA  ALA A 411      -1.536  16.277  13.663  0.00 25.03      A    C
ATOM   1343  CB  ALA A 411      -0.096  15.840  13.581  1.00 24.13      A    C
ATOM   1344  C   ALA A 411      -1.713  17.493  14.550  1.00 24.87      A    C
```

Figure 12

| | | | | | | | | | | |
|---|---|---|---|---|---|---|---|---|---|---|
| ATOM | 1345 | O | ALA | A | 411 | -2.019 | 17.391 | 15.744 | 1.00 25.02 | A O |
| ATOM | 1346 | N | ILE | A | 412 | -1.595 | 18.667 | 13.959 | 1.00 25.02 | A N |
| ATOM | 1347 | CA | ILE | A | 412 | -1.798 | 19.870 | 14.738 | 0.00 26.99 | A C |
| ATOM | 1348 | CB | ILE | A | 412 | -1.410 | 21.125 | 13.967 | 1.00 26.12 | A C |
| ATOM | 1349 | CG2 | ILE | A | 412 | -1.805 | 22.376 | 14.747 | 1.00 25.29 | A C |
| ATOM | 1350 | CG1 | ILE | A | 412 | 0.090 | 21.137 | 13.730 | 1.00 25.10 | A C |
| ATOM | 1351 | CD1 | ILE | A | 412 | 0.544 | 22.285 | 12.897 | 1.00 25.60 | A C |
| ATOM | 1352 | C | ILE | A | 412 | -3.253 | 20.048 | 15.140 | 1.00 28.51 | A C |
| ATOM | 1353 | O | ILE | A | 412 | -3.525 | 20.416 | 16.265 | 1.00 29.70 | A O |
| ATOM | 1354 | N | ASN | A | 413 | -4.163 | 19.775 | 14.208 | 1.00 29.88 | A N |
| ATOM | 1355 | CA | ASN | A | 413 | -5.605 | 19.966 | 14.374 | 0.00 30.84 | A C |
| ATOM | 1356 | CB | ASN | A | 413 | -6.248 | 20.204 | 13.008 | 1.00 31.05 | A C |
| ATOM | 1357 | CG | ASN | A | 413 | -5.730 | 21.467 | 12.344 | 1.00 32.66 | A C |
| ATOM | 1358 | OD1 | ASN | A | 413 | -5.511 | 22.484 | 13.011 | 1.00 34.72 | A O |
| ATOM | 1359 | ND2 | ASN | A | 413 | -5.507 | 21.411 | 11.036 | 1.00 31.55 | A N |
| ATOM | 1360 | C | ASN | A | 413 | -6.399 | 18.923 | 15.117 | 1.00 31.13 | A C |
| ATOM | 1361 | O | ASN | A | 413 | -7.331 | 19.271 | 15.799 | 1.00 31.49 | A O |
| ATOM | 1362 | N | TYR | A | 414 | -5.984 | 17.664 | 15.011 | 1.00 31.96 | A N |
| ATOM | 1363 | CA | TYR | A | 414 | -6.656 | 16.532 | 15.625 | 0.00 32.42 | A C |
| ATOM | 1364 | CB | TYR | A | 414 | -7.384 | 15.748 | 14.537 | 1.00 34.81 | A C |
| ATOM | 1365 | CG | TYR | A | 414 | -8.263 | 16.623 | 13.679 | 1.00 38.31 | A C |
| ATOM | 1366 | CD1 | TYR | A | 414 | -9.463 | 17.141 | 14.176 | 1.00 38.34 | A C |
| ATOM | 1367 | CE1 | TYR | A | 414 | -10.268 | 17.972 | 13.371 | 1.00 40.07 | A C |
| ATOM | 1368 | CD2 | TYR | A | 414 | -7.884 | 16.951 | 12.364 | 1.00 39.21 | A C |
| ATOM | 1369 | CE2 | TYR | A | 414 | -8.688 | 17.776 | 11.561 | 1.00 40.34 | A C |
| ATOM | 1370 | CZ | TYR | A | 414 | -9.870 | 18.274 | 12.074 | 1.00 39.59 | A C |
| ATOM | 1371 | OH | TYR | A | 414 | -10.676 | 19.045 | 11.280 | 1.00 42.14 | A O |
| ATOM | 1372 | C | TYR | A | 414 | -5.730 | 15.551 | 16.377 | 1.00 31.79 | A C |
| ATOM | 1373 | O | TYR | A | 414 | -6.203 | 14.529 | 16.912 | 1.00 31.50 | A O |
| ATOM | 1374 | N | GLY | A | 415 | -4.426 | 15.812 | 16.379 | 1.00 30.45 | A N |
| ATOM | 1375 | CA | GLY | A | 415 | -3.524 | 14.902 | 17.073 | 0.00 30.58 | A C |
| ATOM | 1376 | C | GLY | A | 415 | -3.427 | 13.501 | 16.478 | 1.00 30.44 | A C |
| ATOM | 1377 | O | GLY | A | 415 | -3.159 | 12.521 | 17.187 | 1.00 30.28 | A O |
| ATOM | 1378 | N | THR | A | 416 | -3.684 | 13.395 | 15.172 | 1.00 30.49 | A N |
| ATOM | 1379 | CA | THR | A | 416 | -3.589 | 12.129 | 14.452 | 0.00 29.64 | A C |
| ATOM | 1380 | CB | THR | A | 416 | -4.796 | 11.987 | 13.399 | 1.00 30.46 | A C |
| ATOM | 1381 | OG1 | THR | A | 416 | -4.351 | 11.423 | 12.155 | 1.00 31.36 | A O |
| ATOM | 1382 | CG2 | THR | A | 416 | -5.438 | 13.286 | 13.123 | 1.00 28.02 | A C |
| ATOM | 1383 | C | THR | A | 416 | -2.187 | 12.074 | 13.813 | 1.00 29.12 | A C |
| ATOM | 1384 | O | THR | A | 416 | -1.856 | 12.906 | 12.991 | 1.00 29.74 | A O |
| ATOM | 1385 | N | PHE | A | 417 | -1.348 | 11.138 | 14.269 | 1.00 27.98 | A N |
| ATOM | 1386 | CA | PHE | A | 417 | 0.007 | 10.950 | 13.763 | 0.00 26.40 | A C |
| ATOM | 1387 | CB | PHE | A | 417 | 1.075 | 10.964 | 14.905 | 1.00 25.65 | A C |
| ATOM | 1388 | CG | PHE | A | 417 | 1.272 | 12.320 | 15.579 | 1.00 25.80 | A C |
| ATOM | 1389 | CD1 | PHE | A | 417 | 0.338 | 12.806 | 16.508 | 1.00 24.48 | A C |
| ATOM | 1390 | CD2 | PHE | A | 417 | 2.362 | 13.141 | 15.239 | 1.00 24.55 | A C |
| ATOM | 1391 | CE1 | PHE | A | 417 | 0.490 | 14.085 | 17.067 | 1.00 23.83 | A C |
| ATOM | 1392 | CE2 | PHE | A | 417 | 2.517 | 14.423 | 15.796 | 1.00 21.93 | A C |
| ATOM | 1393 | CZ | PHE | A | 417 | 1.599 | 14.891 | 16.692 | 1.00 23.51 | A C |
| ATOM | 1394 | C | PHE | A | 417 | 0.048 | 9.587 | 13.133 | 1.00 25.36 | A C |
| ATOM | 1395 | O | PHE | A | 417 | -0.311 | 8.607 | 13.763 | 1.00 25.49 | A O |
| ATOM | 1396 | N | THR | A | 418 | 0.542 | 9.522 | 11.904 | 1.00 25.37 | A N |
| ATOM | 1397 | CA | THR | A | 418 | 0.688 | 8.268 | 11.152 | 0.00 24.52 | A C |
| ATOM | 1398 | CB | THR | A | 418 | -0.433 | 8.125 | 10.095 | 1.00 25.10 | A C |
| ATOM | 1399 | OG1 | THR | A | 418 | -0.276 | 9.143 | 9.112 | 1.00 25.10 | A O |
| ATOM | 1400 | CG2 | THR | A | 418 | -1.849 | 8.266 | 10.739 | 1.00 23.71 | A C |
| ATOM | 1401 | C | THR | A | 418 | 2.035 | 8.407 | 10.405 | 1.00 23.84 | A C |
| ATOM | 1402 | O | THR | A | 418 | 2.740 | 9.413 | 10.559 | 1.00 23.43 | A O |
| ATOM | 1403 | N | ILE | A | 419 | 2.357 | 7.453 | 9.551 | 1.00 23.58 | A N |

Figure 12

| ATOM | 1404 | CA  | ILE | A | 419 | 3.589  | 7.546  | 8.770  | 0.00 | 23.47 | A | C |
| ATOM | 1405 | CB  | ILE | A | 419 | 3.882  | 6.217  | 8.033  | 1.00 | 24.50 | A | C |
| ATOM | 1406 | CG2 | ILE | A | 419 | 2.880  | 5.967  | 6.887  | 1.00 | 24.62 | A | C |
| ATOM | 1407 | CG1 | ILE | A | 419 | 5.324  | 6.207  | 7.529  | 1.00 | 25.39 | A | C |
| ATOM | 1408 | CD1 | ILE | A | 419 | 6.358  | 5.859  | 8.622  | 1.00 | 25.31 | A | C |
| ATOM | 1409 | C   | ILE | A | 419 | 3.512  | 8.713  | 7.775  | 1.00 | 23.38 | A | C |
| ATOM | 1410 | O   | ILE | A | 419 | 4.529  | 9.283  | 7.378  | 1.00 | 23.50 | A | O |
| ATOM | 1411 | N   | LYS | A | 420 | 2.290  | 9.130  | 7.428  | 1.00 | 22.80 | A | N |
| ATOM | 1412 | CA  | LYS | A | 420 | 2.106  | 10.242 | 6.494  | 0.00 | 20.73 | A | C |
| ATOM | 1413 | CB  | LYS | A | 420 | 0.684  | 10.251 | 5.913  | 1.00 | 20.25 | A | C |
| ATOM | 1414 | CG  | LYS | A | 420 | 0.378  | 9.021  | 5.130  | 1.00 | 18.49 | A | C |
| ATOM | 1415 | CD  | LYS | A | 420 | 1.144  | 9.056  | 3.867  | 1.00 | 20.58 | A | C |
| ATOM | 1416 | CE  | LYS | A | 420 | 0.846  | 7.849  | 3.046  | 1.00 | 19.31 | A | C |
| ATOM | 1417 | NZ  | LYS | A | 420 | 1.847  | 7.820  | 1.968  | 1.00 | 18.51 | A | N |
| ATOM | 1418 | C   | LYS | A | 420 | 2.480  | 11.550 | 7.160  | 1.00 | 19.78 | A | C |
| ATOM | 1419 | O   | LYS | A | 420 | 2.947  | 12.468 | 6.502  | 1.00 | 19.02 | A | O |
| ATOM | 1420 | N   | SER | A | 421 | 2.277  | 11.677 | 8.469  | 1.00 | 19.91 | A | N |
| ATOM | 1421 | CA  | SER | A | 421 | 2.751  | 12.903 | 9.096  | 0.00 | 19.47 | A | C |
| ATOM | 1422 | CB  | SER | A | 421 | 2.030  | 13.231 | 10.402 | 1.00 | 20.55 | A | C |
| ATOM | 1423 | OG  | SER | A | 421 | 1.614  | 12.072 | 11.082 | 1.00 | 22.44 | A | O |
| ATOM | 1424 | C   | SER | A | 421 | 4.286  | 12.835 | 9.252  | 1.00 | 19.57 | A | C |
| ATOM | 1425 | O   | SER | A | 421 | 4.935  | 13.874 | 9.379  | 1.00 | 20.50 | A | O |
| ATOM | 1426 | N   | ASP | A | 422 | 4.892  | 11.645 | 9.255  | 1.00 | 19.16 | A | N |
| ATOM | 1427 | CA  | ASP | A | 422 | 6.367  | 11.584 | 9.305  | 0.00 | 18.87 | A | C |
| ATOM | 1428 | CB  | ASP | A | 422 | 6.915  | 10.151 | 9.546  | 1.00 | 17.85 | A | C |
| ATOM | 1429 | CG  | ASP | A | 422 | 6.641  | 9.635  | 10.935 | 1.00 | 18.46 | A | C |
| ATOM | 1430 | OD1 | ASP | A | 422 | 6.634  | 10.417 | 11.896 | 1.00 | 21.83 | A | O |
| ATOM | 1431 | OD2 | ASP | A | 422 | 6.452  | 8.418  | 11.100 | 1.00 | 21.39 | A | O |
| ATOM | 1432 | C   | ASP | A | 422 | 6.852  | 12.041 | 7.928  | 1.00 | 19.45 | A | C |
| ATOM | 1433 | O   | ASP | A | 422 | 7.868  | 12.721 | 7.827  | 1.00 | 21.83 | A | O |
| ATOM | 1434 | N   | VAL | A | 423 | 6.147  | 11.657 | 6.858  | 1.00 | 18.40 | A | N |
| ATOM | 1435 | CA  | VAL | A | 423 | 6.493  | 12.057 | 5.504  | 0.00 | 16.26 | A | C |
| ATOM | 1436 | CB  | VAL | A | 423 | 5.523  | 11.450 | 4.405  | 1.00 | 17.52 | A | C |
| ATOM | 1437 | CG1 | VAL | A | 423 | 5.741  | 12.151 | 2.991  | 1.00 | 13.79 | A | C |
| ATOM | 1438 | CG2 | VAL | A | 423 | 5.823  | 9.943  | 4.264  | 1.00 | 15.99 | A | C |
| ATOM | 1439 | C   | VAL | A | 423 | 6.466  | 13.551 | 5.434  | 1.00 | 15.62 | A | C |
| ATOM | 1440 | O   | VAL | A | 423 | 7.304  | 14.169 | 4.766  | 1.00 | 15.38 | A | O |
| ATOM | 1441 | N   | TRP | A | 424 | 5.537  | 14.173 | 6.144  | 1.00 | 15.88 | A | N |
| ATOM | 1442 | CA  | TRP | A | 424 | 5.456  | 15.620 | 6.126  | 0.00 | 14.99 | A | C |
| ATOM | 1443 | CB  | TRP | A | 424 | 4.149  | 16.102 | 6.798  | 1.00 | 14.04 | A | C |
| ATOM | 1444 | CG  | TRP | A | 424 | 4.096  | 17.597 | 7.103  | 1.00 | 11.69 | A | C |
| ATOM | 1445 | CD2 | TRP | A | 424 | 3.272  | 18.596 | 6.467  | 1.00 | 13.14 | A | C |
| ATOM | 1446 | CE2 | TRP | A | 424 | 3.673  | 19.843 | 6.986  | 1.00 | 13.58 | A | C |
| ATOM | 1447 | CE3 | TRP | A | 424 | 2.244  | 18.542 | 5.517  | 1.00 | 14.21 | A | C |
| ATOM | 1448 | CD1 | TRP | A | 424 | 4.876  | 18.259 | 7.971  | 1.00 | 12.01 | A | C |
| ATOM | 1449 | NE1 | TRP | A | 424 | 4.640  | 19.617 | 7.901  | 1.00 | 11.03 | A | N |
| ATOM | 1450 | CZ2 | TRP | A | 424 | 3.063  | 21.094 | 6.572  | 1.00 | 15.12 | A | C |
| ATOM | 1451 | CZ3 | TRP | A | 424 | 1.639  | 19.778 | 5.114  | 1.00 | 14.08 | A | C |
| ATOM | 1452 | CH2 | TRP | A | 424 | 2.055  | 21.024 | 5.636  | 1.00 | 14.06 | A | C |
| ATOM | 1453 | C   | TRP | A | 424 | 6.699  | 16.138 | 6.842  | 1.00 | 15.77 | A | C |
| ATOM | 1454 | O   | TRP | A | 424 | 7.319  | 17.093 | 6.395  | 1.00 | 15.76 | A | O |
| ATOM | 1455 | N   | SER | A | 425 | 7.076  | 15.499 | 7.952  | 1.00 | 16.58 | A | N |
| ATOM | 1456 | CA  | SER | A | 425 | 8.270  | 15.892 | 8.707  | 0.00 | 18.59 | A | C |
| ATOM | 1457 | CB  | SER | A | 425 | 8.435  | 15.046 | 9.960  | 1.00 | 20.01 | A | C |
| ATOM | 1458 | OG  | SER | A | 425 | 7.473  | 15.444 | 10.887 | 1.00 | 23.15 | A | O |
| ATOM | 1459 | C   | SER | A | 425 | 9.536  | 15.754 | 7.862  | 1.00 | 18.75 | A | C |
| ATOM | 1460 | O   | SER | A | 425 | 10.403 | 16.607 | 7.904  | 1.00 | 18.80 | A | O |
| ATOM | 1461 | N   | PHE | A | 426 | 9.621  | 14.674 | 7.123  | 1.00 | 18.33 | A | N |
| ATOM | 1462 | CA  | PHE | A | 426 | 10.760 | 14.460 | 6.249  | 0.00 | 19.58 | A | C |

Figure 12

```
ATOM   1463  CB  PHE A 426      10.659  13.110   5.555  1.00 18.36      A    C
ATOM   1464  CG  PHE A 426      11.853  12.784   4.739  1.00 20.55      A    C
ATOM   1465  CD1 PHE A 426      12.998  12.278   5.352  1.00 21.58      A    C
ATOM   1466  CD2 PHE A 426      11.837  12.960   3.350  1.00 20.22      A    C
ATOM   1467  CE1 PHE A 426      14.123  11.940   4.588  1.00 23.56      A    C
ATOM   1468  CE2 PHE A 426      12.955  12.634   2.563  1.00 20.44      A    C
ATOM   1469  CZ  PHE A 426      14.103  12.121   3.181  1.00 23.77      A    C
ATOM   1470  C   PHE A 426      10.944  15.620   5.250  1.00 20.14      A    C
ATOM   1471  O   PHE A 426      12.078  16.103   5.048  1.00 20.74      A    O
ATOM   1472  N   GLY A 427       9.854  16.080   4.637  1.00 19.15      A    N
ATOM   1473  CA  GLY A 427       9.962  17.212   3.751  0.00 17.45      A    C
ATOM   1474  C   GLY A 427      10.527  18.416   4.516  1.00 18.69      A    C
ATOM   1475  O   GLY A 427      11.348  19.147   3.971  1.00 19.43      A    O
ATOM   1476  N   ILE A 428      10.057  18.698   5.741  1.00 18.40      A    N
ATOM   1477  CA  ILE A 428      10.627  19.827   6.502  0.00 17.94      A    C
ATOM   1478  CB  ILE A 428       9.939  20.042   7.887  1.00 16.67      A    C
ATOM   1479  CG2 ILE A 428      10.552  21.245   8.599  1.00 14.30      A    C
ATOM   1480  CG1 ILE A 428       8.417  20.224   7.727  1.00 16.55      A    C
ATOM   1481  CD1 ILE A 428       7.969  21.565   7.083  1.00 16.13      A    C
ATOM   1482  C   ILE A 428      12.145  19.534   6.744  1.00 18.74      A    C
ATOM   1483  O   ILE A 428      13.006  20.416   6.561  1.00 17.41      A    O
ATOM   1484  N   LEU A 429      12.454  18.289   7.097  1.00 17.61      A    N
ATOM   1485  CA  LEU A 429      13.839  17.879   7.311  0.00 19.41      A    C
ATOM   1486  CB  LEU A 429      13.875  16.369   7.608  1.00 19.02      A    C
ATOM   1487  CG  LEU A 429      15.133  15.878   8.316  1.00 21.06      A    C
ATOM   1488  CD1 LEU A 429      14.872  14.529   8.937  1.00 19.91      A    C
ATOM   1489  CD2 LEU A 429      16.294  15.812   7.403  1.00 20.85      A    C
ATOM   1490  C   LEU A 429      14.768  18.216   6.092  1.00 19.40      A    C
ATOM   1491  O   LEU A 429      15.911  18.642   6.279  1.00 20.47      A    O
ATOM   1492  N   LEU A 430      14.294  17.951   4.871  1.00 19.83      A    N
ATOM   1493  CA  LEU A 430      15.032  18.221   3.625  0.00 20.06      A    C
ATOM   1494  CB  LEU A 430      14.211  17.800   2.390  1.00 20.60      A    C
ATOM   1495  CG  LEU A 430      14.002  16.302   2.154  1.00 20.34      A    C
ATOM   1496  CD1 LEU A 430      12.951  16.085   1.101  1.00 21.28      A    C
ATOM   1497  CD2 LEU A 430      15.322  15.672   1.714  1.00 20.38      A    C
ATOM   1498  C   LEU A 430      15.375  19.683   3.513  1.00 19.93      A    C
ATOM   1499  O   LEU A 430      16.400  20.019   2.970  1.00 20.85      A    O
ATOM   1500  N   THR A 431      14.564  20.576   4.084  1.00 20.70      A    N
ATOM   1501  CA  THR A 431      14.889  21.977   4.010  0.00 21.16      A    C
ATOM   1502  CB  THR A 431      13.713  22.939   4.319  1.00 19.97      A    C
ATOM   1503  OG1 THR A 431      13.394  22.932   5.734  1.00 20.92      A    O
ATOM   1504  CG2 THR A 431      12.523  22.635   3.457  1.00 20.96      A    C
ATOM   1505  C   THR A 431      16.066  22.252   4.949  1.00 22.96      A    C
ATOM   1506  O   THR A 431      16.938  23.082   4.645  1.00 22.59      A    O
ATOM   1507  N   GLU A 432      16.049  21.599   6.109  1.00 23.48      A    N
ATOM   1508  CA  GLU A 432      17.131  21.733   7.063  0.00 24.03      A    C
ATOM   1509  CB  GLU A 432      16.899  20.891   8.305  1.00 23.93      A    C
ATOM   1510  CG  GLU A 432      15.831  21.409   9.218  1.00 24.39      A    C
ATOM   1511  CD  GLU A 432      15.698  20.497  10.400  1.00 24.58      A    C
ATOM   1512  OE1 GLU A 432      15.188  19.354  10.248  1.00 23.02      A    O
ATOM   1513  OE2 GLU A 432      16.150  20.915  11.473  1.00 24.70      A    O
ATOM   1514  C   GLU A 432      18.402  21.243   6.414  1.00 23.74      A    C
ATOM   1515  O   GLU A 432      19.447  21.838   6.606  1.00 23.89      A    O
ATOM   1516  N   ILE A 433      18.304  20.144   5.668  1.00 23.30      A    N
ATOM   1517  CA  ILE A 433      19.449  19.549   5.014  0.00 24.00      A    C
ATOM   1518  CB  ILE A 433      19.099  18.186   4.431  1.00 22.44      A    C
ATOM   1519  CG2 ILE A 433      20.098  17.751   3.373  1.00 22.81      A    C
ATOM   1520  CG1 ILE A 433      18.990  17.150   5.557  1.00 23.67      A    C
ATOM   1521  CD1 ILE A 433      18.620  15.749   5.059  1.00 23.80      A    C
```

Figure 12

| ATOM | 1522 | C   | ILE | A | 433 | 20.109 | 20.401 | 3.916  | 1.00 | 25.78 | A | C |
|------|------|-----|-----|---|-----|--------|--------|--------|------|-------|---|---|
| ATOM | 1523 | O   | ILE | A | 433 | 21.328 | 20.412 | 3.818  | 1.00 | 25.87 | A | O |
| ATOM | 1524 | N   | VAL | A | 434 | 19.309 | 21.086 | 3.088  | 1.00 | 27.28 | A | N |
| ATOM | 1525 | CA  | VAL | A | 434 | 19.866 | 21.878 | 2.013  | 0.00 | 28.80 | A | C |
| ATOM | 1526 | CB  | VAL | A | 434 | 19.048 | 21.786 | 0.678  | 1.00 | 29.09 | A | C |
| ATOM | 1527 | CG1 | VAL | A | 434 | 18.841 | 20.323 | 0.287  | 1.00 | 29.34 | A | C |
| ATOM | 1528 | CG2 | VAL | A | 434 | 17.735 | 22.569 | 0.773  | 1.00 | 27.43 | A | C |
| ATOM | 1529 | C   | VAL | A | 434 | 20.192 | 23.315 | 2.381  | 1.00 | 29.82 | A | C |
| ATOM | 1530 | O   | VAL | A | 434 | 20.804 | 24.029 | 1.585  | 1.00 | 30.57 | A | O |
| ATOM | 1531 | N   | THR | A | 435 | 19.785 | 23.758 | 3.559  | 1.00 | 30.55 | A | N |
| ATOM | 1532 | CA  | THR | A | 435 | 20.128 | 25.097 | 4.003  | 0.00 | 32.17 | A | C |
| ATOM | 1533 | CB  | THR | A | 435 | 18.890 | 25.856 | 4.524  | 1.00 | 32.52 | A | C |
| ATOM | 1534 | OG1 | THR | A | 435 | 18.336 | 25.163 | 5.661  | 1.00 | 33.28 | A | O |
| ATOM | 1535 | CG2 | THR | A | 435 | 17.866 | 26.060 | 3.407  | 1.00 | 29.56 | A | C |
| ATOM | 1536 | C   | THR | A | 435 | 21.153 | 25.007 | 5.157  | 1.00 | 33.70 | A | C |
| ATOM | 1537 | O   | THR | A | 435 | 21.330 | 25.964 | 5.918  | 1.00 | 34.12 | A | O |
| ATOM | 1538 | N   | HIS | A | 436 | 21.787 | 23.845 | 5.304  | 1.00 | 35.28 | A | N |
| ATOM | 1539 | CA  | HIS | A | 436 | 22.753 | 23.561 | 6.374  | 0.00 | 36.88 | A | C |
| ATOM | 1540 | CB  | HIS | A | 436 | 24.095 | 24.264 | 6.125  | 1.00 | 40.50 | A | C |
| ATOM | 1541 | CG  | HIS | A | 436 | 24.684 | 23.976 | 4.769  | 1.00 | 42.95 | A | C |
| ATOM | 1542 | CD2 | HIS | A | 436 | 24.957 | 24.801 | 3.732  | 1.00 | 44.08 | A | C |
| ATOM | 1543 | ND1 | HIS | A | 436 | 24.966 | 22.699 | 4.318  | 1.00 | 43.80 | A | N |
| ATOM | 1544 | CE1 | HIS | A | 436 | 25.372 | 22.743 | 3.058  | 1.00 | 43.02 | A | C |
| ATOM | 1545 | NE2 | HIS | A | 436 | 25.369 | 24.008 | 2.679  | 1.00 | 44.96 | A | N |
| ATOM | 1546 | C   | HIS | A | 436 | 22.264 | 23.811 | 7.805  | 1.00 | 36.66 | A | C |
| ATOM | 1547 | O   | HIS | A | 436 | 22.887 | 24.532 | 8.559  | 1.00 | 36.55 | A | O |
| ATOM | 1548 | N   | GLY | A | 437 | 21.131 | 23.214 | 8.172  | 1.00 | 36.39 | A | N |
| ATOM | 1549 | CA  | GLY | A | 437 | 20.615 | 23.344 | 9.524  | 0.00 | 35.95 | A | C |
| ATOM | 1550 | C   | GLY | A | 437 | 19.838 | 24.582 | 9.894  | 1.00 | 35.72 | A | C |
| ATOM | 1551 | O   | GLY | A | 437 | 19.700 | 24.901 | 11.069 | 1.00 | 36.45 | A | O |
| ATOM | 1552 | N   | ARG | A | 438 | 19.350 | 25.298 | 8.898  | 1.00 | 35.15 | A | N |
| ATOM | 1553 | CA  | ARG | A | 438 | 18.567 | 26.487 | 9.135  | 0.00 | 34.74 | A | C |
| ATOM | 1554 | CB  | ARG | A | 438 | 18.460 | 27.248 | 7.835  | 1.00 | 37.21 | A | C |
| ATOM | 1555 | CG  | ARG | A | 438 | 18.046 | 28.690 | 7.977  | 1.00 | 41.57 | A | C |
| ATOM | 1556 | CD  | ARG | A | 438 | 16.527 | 28.865 | 8.070  | 1.00 | 45.79 | A | C |
| ATOM | 1557 | NE  | ARG | A | 438 | 15.761 | 28.261 | 6.956  | 1.00 | 48.34 | A | N |
| ATOM | 1558 | CZ  | ARG | A | 438 | 15.827 | 28.679 | 5.693  | 1.00 | 50.07 | A | C |
| ATOM | 1559 | NH1 | ARG | A | 438 | 16.641 | 29.702 | 5.383  | 1.00 | 49.91 | A | N |
| ATOM | 1560 | NH2 | ARG | A | 438 | 15.040 | 28.124 | 4.756  | 1.00 | 49.24 | A | N |
| ATOM | 1561 | C   | ARG | A | 438 | 17.176 | 26.070 | 9.634  | 1.00 | 33.94 | A | C |
| ATOM | 1562 | O   | ARG | A | 438 | 16.641 | 25.024 | 9.230  | 1.00 | 32.88 | A | O |
| ATOM | 1563 | N   | ILE | A | 439 | 16.648 | 26.849 | 10.569 | 1.00 | 32.92 | A | N |
| ATOM | 1564 | CA  | ILE | A | 439 | 15.343 | 26.603 | 11.155 | 0.00 | 32.61 | A | C |
| ATOM | 1565 | CB  | ILE | A | 439 | 15.126 | 27.520 | 12.387 | 1.00 | 32.89 | A | C |
| ATOM | 1566 | CG2 | ILE | A | 439 | 13.670 | 27.464 | 12.890 | 1.00 | 34.50 | A | C |
| ATOM | 1567 | CG1 | ILE | A | 439 | 16.027 | 27.013 | 13.527 | 1.00 | 35.41 | A | C |
| ATOM | 1568 | CD1 | ILE | A | 439 | 16.186 | 27.971 | 14.738 | 1.00 | 36.57 | A | C |
| ATOM | 1569 | C   | ILE | A | 439 | 14.226 | 26.796 | 10.111 | 1.00 | 31.45 | A | C |
| ATOM | 1570 | O   | ILE | A | 439 | 14.331 | 27.661 | 9.247  | 1.00 | 31.25 | A | O |
| ATOM | 1571 | N   | PRO | A | 440 | 13.256 | 25.871 | 10.072 | 1.00 | 30.10 | A | N |
| ATOM | 1572 | CD  | PRO | A | 440 | 13.372 | 24.529 | 10.677 | 1.00 | 28.52 | A | C |
| ATOM | 1573 | CA  | PRO | A | 440 | 12.121 | 25.942 | 9.132  | 0.00 | 28.41 | A | C |
| ATOM | 1574 | CB  | PRO | A | 440 | 11.336 | 24.698 | 9.501  | 1.00 | 28.76 | A | C |
| ATOM | 1575 | CG  | PRO | A | 440 | 12.457 | 23.708 | 9.822  | 1.00 | 29.08 | A | C |
| ATOM | 1576 | C   | PRO | A | 440 | 11.321 | 27.222 | 9.403  | 1.00 | 27.78 | A | C |
| ATOM | 1577 | O   | PRO | A | 440 | 11.392 | 27.770 | 10.502 | 1.00 | 26.62 | A | O |
| ATOM | 1578 | N   | TYR | A | 441 | 10.600 | 27.729 | 8.392  | 1.00 | 27.67 | A | N |
| ATOM | 1579 | CA  | TYR | A | 441 | 9.783  | 28.960 | 8.491  | 0.00 | 26.62 | A | C |
| ATOM | 1580 | CB  | TYR | A | 441 | 8.453  | 28.680 | 9.197  | 1.00 | 24.39 | A | C |

Figure 12

| | | | | | | | | | | | |
|---|---|---|---|---|---|---|---|---|---|---|---|
| ATOM | 1581 | CG | TYR | A | 441 | 7.705 | 27.504 | 8.625 | 1.00 | 22.84 | A C |
| ATOM | 1582 | CD1 | TYR | A | 441 | 6.740 | 27.683 | 7.593 | 1.00 | 23.73 | A C |
| ATOM | 1583 | CE1 | TYR | A | 441 | 5.995 | 26.566 | 7.104 | 1.00 | 22.10 | A C |
| ATOM | 1584 | CD2 | TYR | A | 441 | 7.907 | 26.231 | 9.111 | 1.00 | 19.50 | A C |
| ATOM | 1585 | CE2 | TYR | A | 441 | 7.185 | 25.150 | 8.635 | 1.00 | 21.10 | A C |
| ATOM | 1586 | CZ | TYR | A | 441 | 6.231 | 25.323 | 7.642 | 1.00 | 21.01 | A C |
| ATOM | 1587 | OH | TYR | A | 441 | 5.507 | 24.234 | 7.214 | 1.00 | 23.36 | A O |
| ATOM | 1588 | C | TYR | A | 441 | 10.514 | 30.090 | 9.215 | 1.00 | 28.42 | A C |
| ATOM | 1589 | O | TYR | A | 441 | 10.067 | 30.564 | 10.272 | 1.00 | 27.72 | A O |
| ATOM | 1590 | N | PRO | A | 442 | 11.674 | 30.509 | 8.677 | 1.00 | 30.14 | A N |
| ATOM | 1591 | CD | PRO | A | 442 | 12.386 | 29.979 | 7.494 | 1.00 | 29.69 | A C |
| ATOM | 1592 | CA | PRO | A | 442 | 12.431 | 31.591 | 9.320 | 0.00 | 32.41 | A C |
| ATOM | 1593 | CB | PRO | A | 442 | 13.675 | 31.723 | 8.419 | 1.00 | 31.66 | A C |
| ATOM | 1594 | CG | PRO | A | 442 | 13.238 | 31.148 | 7.085 | 1.00 | 30.99 | A C |
| ATOM | 1595 | C | PRO | A | 442 | 11.633 | 32.898 | 9.492 | 1.00 | 34.72 | A C |
| ATOM | 1596 | O | PRO | A | 442 | 10.869 | 33.325 | 8.628 | 1.00 | 35.88 | A O |
| ATOM | 1597 | N | GLY | A | 443 | 11.768 | 33.532 | 10.637 | 1.00 | 36.81 | A N |
| ATOM | 1598 | CA | GLY | A | 443 | 11.003 | 34.749 | 10.837 | 0.00 | 38.70 | A C |
| ATOM | 1599 | C | GLY | A | 443 | 9.542 | 34.467 | 11.144 | 1.00 | 39.90 | A C |
| ATOM | 1600 | O | GLY | A | 443 | 8.693 | 35.336 | 10.963 | 1.00 | 41.62 | A O |
| ATOM | 1601 | N | MET | A | 444 | 9.228 | 33.242 | 11.556 | 1.00 | 39.25 | A N |
| ATOM | 1602 | CA | MET | A | 444 | 7.858 | 32.888 | 11.943 | 0.00 | 38.38 | A C |
| ATOM | 1603 | CB | MET | A | 444 | 7.182 | 31.965 | 10.908 | 1.00 | 37.73 | A C |
| ATOM | 1604 | CG | MET | A | 444 | 6.338 | 32.665 | 9.857 | 1.00 | 36.38 | A C |
| ATOM | 1605 | SD | MET | A | 444 | 5.660 | 31.617 | 8.548 | 1.00 | 34.46 | A S |
| ATOM | 1606 | CE | MET | A | 444 | 4.790 | 30.638 | 9.315 | 1.00 | 35.68 | A C |
| ATOM | 1607 | C | MET | A | 444 | 7.859 | 32.190 | 13.298 | 1.00 | 37.92 | A C |
| ATOM | 1608 | O | MET | A | 444 | 8.587 | 31.231 | 13.491 | 1.00 | 38.62 | A O |
| ATOM | 1609 | N | THR | A | 445 | 7.059 | 32.682 | 14.240 | 1.00 | 37.08 | A N |
| ATOM | 1610 | CA | THR | A | 445 | 6.966 | 32.044 | 15.551 | 0.00 | 36.13 | A C |
| ATOM | 1611 | CB | THR | A | 445 | 6.329 | 33.010 | 16.587 | 1.00 | 37.30 | A C |
| ATOM | 1612 | OG1 | THR | A | 445 | 4.916 | 33.144 | 16.336 | 1.00 | 36.80 | A O |
| ATOM | 1613 | CG2 | THR | A | 445 | 7.027 | 34.417 | 16.494 | 1.00 | 36.82 | A C |
| ATOM | 1614 | C | THR | A | 445 | 6.092 | 30.799 | 15.427 | 1.00 | 35.19 | A C |
| ATOM | 1615 | O | THR | A | 445 | 5.443 | 30.605 | 14.416 | 1.00 | 34.96 | A O |
| ATOM | 1616 | N | ASN | A | 446 | 6.061 | 29.946 | 16.433 | 1.00 | 34.51 | A N |
| ATOM | 1617 | CA | ASN | A | 446 | 5.215 | 28.778 | 16.344 | 0.00 | 34.03 | A C |
| ATOM | 1618 | CB | ASN | A | 446 | 5.349 | 27.913 | 17.589 | 1.00 | 33.54 | A C |
| ATOM | 1619 | CG | ASN | A | 446 | 6.590 | 27.044 | 17.555 | 1.00 | 32.95 | A C |
| ATOM | 1620 | OD1 | ASN | A | 446 | 7.393 | 27.101 | 16.616 | 1.00 | 31.35 | A O |
| ATOM | 1621 | ND2 | ASN | A | 446 | 6.729 | 26.190 | 18.555 | 1.00 | 32.55 | A N |
| ATOM | 1622 | C | ASN | A | 446 | 3.743 | 29.107 | 16.040 | 1.00 | 34.37 | A C |
| ATOM | 1623 | O | ASN | A | 446 | 3.150 | 28.476 | 15.147 | 1.00 | 33.70 | A O |
| ATOM | 1624 | N | PRO | A | 447 | 3.120 | 30.068 | 16.784 | 1.00 | 34.25 | A N |
| ATOM | 1625 | CD | PRO | A | 447 | 3.538 | 30.664 | 18.063 | 1.00 | 34.27 | A C |
| ATOM | 1626 | CA | PRO | A | 447 | 1.720 | 30.406 | 16.499 | 0.00 | 34.05 | A C |
| ATOM | 1627 | CB | PRO | A | 447 | 1.339 | 31.385 | 17.624 | 1.00 | 34.33 | A C |
| ATOM | 1628 | CG | PRO | A | 447 | 2.646 | 31.859 | 18.161 | 1.00 | 34.67 | A C |
| ATOM | 1629 | C | PRO | A | 447 | 1.483 | 30.983 | 15.097 | 1.00 | 33.20 | A C |
| ATOM | 1630 | O | PRO | A | 447 | 0.423 | 30.755 | 14.515 | 1.00 | 33.41 | A O |
| ATOM | 1631 | N | GLU | A | 448 | 2.463 | 31.706 | 14.563 | 1.00 | 32.41 | A N |
| ATOM | 1632 | CA | GLU | A | 448 | 2.372 | 32.263 | 13.221 | 0.00 | 31.01 | A C |
| ATOM | 1633 | CB | GLU | A | 448 | 3.591 | 33.108 | 12.917 | 1.00 | 33.02 | A C |
| ATOM | 1634 | CG | GLU | A | 448 | 3.453 | 34.522 | 13.340 | 1.00 | 37.66 | A C |
| ATOM | 1635 | CD | GLU | A | 448 | 4.778 | 35.232 | 13.320 | 1.00 | 41.44 | A C |
| ATOM | 1636 | OE1 | GLU | A | 448 | 5.550 | 35.077 | 12.327 | 1.00 | 45.29 | A O |
| ATOM | 1637 | OE2 | GLU | A | 448 | 5.053 | 35.953 | 14.296 | 1.00 | 43.22 | A O |
| ATOM | 1638 | C | GLU | A | 448 | 2.311 | 31.116 | 12.221 | 1.00 | 29.89 | A C |
| ATOM | 1639 | O | GLU | A | 448 | 1.501 | 31.128 | 11.305 | 1.00 | 29.39 | A O |

Figure 12

| | | | | | | | | | | |
|---|---|---|---|---|---|---|---|---|---|---|
| ATOM | 1640 | N | VAL | A | 449 | 3.199 | 30.136 | 12.407 | 1.00 28.53 | A N |
| ATOM | 1641 | CA | VAL | A | 449 | 3.255 | 28.943 | 11.573 | 0.00 27.07 | A C |
| ATOM | 1642 | CB | VAL | A | 449 | 4.400 | 27.946 | 12.012 | 1.00 26.38 | A C |
| ATOM | 1643 | CG1 | VAL | A | 449 | 4.239 | 26.552 | 11.335 | 1.00 23.17 | A C |
| ATOM | 1644 | CG2 | VAL | A | 449 | 5.731 | 28.531 | 11.613 | 1.00 21.27 | A C |
| ATOM | 1645 | C | VAL | A | 449 | 1.930 | 28.241 | 11.553 | 1.00 26.68 | A C |
| ATOM | 1646 | O | VAL | A | 449 | 1.436 | 27.902 | 10.484 | 1.00 27.22 | A O |
| ATOM | 1647 | N | ILE | A | 450 | 1.311 | 28.114 | 12.719 | 1.00 27.54 | A N |
| ATOM | 1648 | CA | ILE | A | 450 | 0.011 | 27.457 | 12.866 | 0.00 27.71 | A C |
| ATOM | 1649 | CB | ILE | A | 450 | -0.454 | 27.492 | 14.339 | 1.00 29.33 | A C |
| ATOM | 1650 | CG2 | ILE | A | 450 | -1.850 | 26.890 | 14.473 | 1.00 27.71 | A C |
| ATOM | 1651 | CG1 | ILE | A | 450 | 0.530 | 26.763 | 15.255 | 1.00 29.57 | A C |
| ATOM | 1652 | CD1 | ILE | A | 450 | 0.381 | 25.298 | 15.233 | 1.00 30.88 | A C |
| ATOM | 1653 | C | ILE | A | 450 | -1.059 | 28.162 | 12.015 | 1.00 27.96 | A C |
| ATOM | 1654 | O | ILE | A | 450 | -1.773 | 27.527 | 11.258 | 1.00 26.97 | A O |
| ATOM | 1655 | N | GLN | A | 451 | -1.131 | 29.478 | 12.104 | 1.00 29.09 | A N |
| ATOM | 1656 | CA | GLN | A | 451 | -2.136 | 30.191 | 11.345 | 0.00 29.79 | A C |
| ATOM | 1657 | CB | GLN | A | 451 | -2.405 | 31.562 | 11.957 | 1.00 33.20 | A C |
| ATOM | 1658 | CG | GLN | A | 451 | -1.353 | 32.569 | 11.771 | 1.00 37.87 | A C |
| ATOM | 1659 | CD | GLN | A | 451 | -1.454 | 33.690 | 12.799 | 1.00 41.76 | A C |
| ATOM | 1660 | OE1 | GLN | A | 451 | -1.067 | 34.833 | 12.520 | 1.00 44.53 | A O |
| ATOM | 1661 | NE2 | GLN | A | 451 | -1.910 | 33.354 | 14.009 | 1.00 43.00 | A N |
| ATOM | 1662 | C | GLN | A | 451 | -1.840 | 30.272 | 9.867 | 1.00 28.86 | A C |
| ATOM | 1663 | O | GLN | A | 451 | -2.763 | 30.326 | 9.053 | 1.00 28.84 | A O |
| ATOM | 1664 | N | ASN | A | 452 | -0.559 | 30.283 | 9.501 | 1.00 26.78 | A N |
| ATOM | 1665 | CA | ASN | A | 452 | -0.232 | 30.289 | 8.086 | 0.00 24.91 | A C |
| ATOM | 1666 | CB | ASN | A | 452 | 1.263 | 30.548 | 7.863 | 1.00 24.79 | A C |
| ATOM | 1667 | CG | ASN | A | 452 | 1.589 | 32.033 | 7.718 | 1.00 25.73 | A C |
| ATOM | 1668 | OD1 | ASN | A | 452 | 1.592 | 32.564 | 6.620 | 1.00 26.38 | A O |
| ATOM | 1669 | ND2 | ASN | A | 452 | 1.867 | 32.709 | 8.824 | 1.00 25.54 | A N |
| ATOM | 1670 | C | ASN | A | 452 | -0.643 | 28.923 | 7.501 | 1.00 23.61 | A C |
| ATOM | 1671 | O | ASN | A | 452 | -1.101 | 28.858 | 6.366 | 1.00 22.46 | A O |
| ATOM | 1672 | N | LEU | A | 453 | -0.459 | 27.831 | 8.244 | 1.00 22.97 | A N |
| ATOM | 1673 | CA | LEU | A | 453 | -0.846 | 26.505 | 7.727 | 0.00 23.29 | A C |
| ATOM | 1674 | CB | LEU | A | 453 | -0.296 | 25.384 | 8.603 | 1.00 24.54 | A C |
| ATOM | 1675 | CG | LEU | A | 453 | 1.195 | 25.082 | 8.616 | 1.00 24.61 | A C |
| ATOM | 1676 | CD1 | LEU | A | 453 | 1.372 | 23.921 | 9.554 | 1.00 24.86 | A C |
| ATOM | 1677 | CD2 | LEU | A | 453 | 1.739 | 24.718 | 7.216 | 1.00 24.35 | A C |
| ATOM | 1678 | C | LEU | A | 453 | -2.364 | 26.361 | 7.678 | 1.00 23.73 | A C |
| ATOM | 1679 | O | LEU | A | 453 | -2.908 | 25.520 | 6.961 | 1.00 22.98 | A O |
| ATOM | 1680 | N | GLU | A | 454 | -3.059 | 27.105 | 8.524 | 1.00 23.55 | A N |
| ATOM | 1681 | CA | GLU | A | 454 | -4.511 | 27.056 | 8.453 | 0.00 25.63 | A C |
| ATOM | 1682 | CB | GLU | A | 454 | -5.116 | 27.970 | 9.492 | 1.00 28.37 | A C |
| ATOM | 1683 | CG | GLU | A | 454 | -5.050 | 27.444 | 10.861 | 1.00 36.00 | A C |
| ATOM | 1684 | CD | GLU | A | 454 | -5.560 | 28.460 | 11.853 | 1.00 40.12 | A C |
| ATOM | 1685 | OE1 | GLU | A | 454 | -5.065 | 28.425 | 13.018 | 1.00 42.27 | A O |
| ATOM | 1686 | OE2 | GLU | A | 454 | -6.444 | 29.279 | 11.447 | 1.00 42.59 | A O |
| ATOM | 1687 | C | GLU | A | 454 | -4.937 | 27.586 | 7.059 | 1.00 24.34 | A C |
| ATOM | 1688 | O | GLU | A | 454 | -5.953 | 27.177 | 6.497 | 1.00 23.07 | A O |
| ATOM | 1689 | N | ARG | A | 455 | -4.174 | 28.568 | 6.592 | 1.00 22.53 | A N |
| ATOM | 1690 | CA | ARG | A | 455 | -4.373 | 29.234 | 5.334 | 0.00 22.22 | A C |
| ATOM | 1691 | CB | ARG | A | 455 | -3.851 | 30.652 | 5.456 | 1.00 24.09 | A C |
| ATOM | 1692 | CG | ARG | A | 455 | -4.459 | 31.523 | 6.552 | 1.00 26.08 | A C |
| ATOM | 1693 | CD | ARG | A | 455 | -3.927 | 33.030 | 6.406 | 1.00 30.68 | A C |
| ATOM | 1694 | NE | ARG | A | 455 | -2.479 | 33.007 | 6.080 | 1.00 35.96 | A N |
| ATOM | 1695 | CZ | ARG | A | 455 | -1.940 | 33.173 | 4.839 | 1.00 37.32 | A C |
| ATOM | 1696 | NH1 | ARG | A | 455 | -2.691 | 33.467 | 3.776 | 1.00 34.74 | A N |
| ATOM | 1697 | NH2 | ARG | A | 455 | -0.693 | 32.726 | 4.588 | 1.00 37.72 | A N |
| ATOM | 1698 | C | ARG | A | 455 | -3.709 | 28.504 | 4.144 | 1.00 21.52 | A C |

Figure 12

| ATOM | 1699 | O   | ARG A 455 | -3.796 | 28.961 | 3.022  | 1.00 | 20.80 | A | O |
| ATOM | 1700 | N   | GLY A 456 | -3.054 | 27.359 | 4.403  | 1.00 | 20.65 | A | N |
| ATOM | 1701 | CA  | GLY A 456 | -2.434 | 26.585 | 3.330  | 0.00 | 18.97 | A | C |
| ATOM | 1702 | C   | GLY A 456 | -1.026 | 26.982 | 2.896  | 1.00 | 18.72 | A | C |
| ATOM | 1703 | O   | GLY A 456 | -0.562 | 26.620 | 1.813  | 1.00 | 18.28 | A | O |
| ATOM | 1704 | N   | TYR A 457 | -0.363 | 27.774 | 3.715  | 1.00 | 18.47 | A | N |
| ATOM | 1705 | CA  | TYR A 457 | 0.969  | 28.216 | 3.430  | 0.00 | 18.79 | A | C |
| ATOM | 1706 | CB  | TYR A 457 | 1.410  | 29.160 | 4.545  | 1.00 | 17.26 | A | C |
| ATOM | 1707 | CG  | TYR A 457 | 2.758  | 29.728 | 4.313  | 1.00 | 16.71 | A | C |
| ATOM | 1708 | CD1 | TYR A 457 | 2.930  | 30.932 | 3.663  | 1.00 | 15.01 | A | C |
| ATOM | 1709 | CE1 | TYR A 457 | 4.212  | 31.446 | 3.428  | 1.00 | 17.38 | A | C |
| ATOM | 1710 | CD2 | TYR A 457 | 3.907  | 29.024 | 4.731  | 1.00 | 18.93 | A | C |
| ATOM | 1711 | CE2 | TYR A 457 | 5.171  | 29.509 | 4.499  | 1.00 | 18.16 | A | C |
| ATOM | 1712 | CZ  | TYR A 457 | 5.329  | 30.711 | 3.857  | 1.00 | 18.61 | A | C |
| ATOM | 1713 | OH  | TYR A 457 | 6.622  | 31.180 | 3.694  | 1.00 | 20.06 | A | O |
| ATOM | 1714 | C   | TYR A 457 | 1.989  | 27.073 | 3.276  | 1.00 | 19.04 | A | C |
| ATOM | 1715 | O   | TYR A 457 | 1.898  | 26.031 | 3.926  | 1.00 | 19.53 | A | O |
| ATOM | 1716 | N   | ARG A 458 | 2.919  | 27.254 | 2.344  | 1.00 | 19.22 | A | N |
| ATOM | 1717 | CA  | ARG A 458 | 4.014  | 26.300 | 2.136  | 0.00 | 20.29 | A | C |
| ATOM | 1718 | CB  | ARG A 458 | 3.791  | 25.412 | 0.910  | 1.00 | 19.00 | A | C |
| ATOM | 1719 | CG  | ARG A 458 | 2.610  | 24.449 | 1.030  | 1.00 | 19.75 | A | C |
| ATOM | 1720 | CD  | ARG A 458 | 2.759  | 23.539 | 2.205  | 1.00 | 17.04 | A | C |
| ATOM | 1721 | NE  | ARG A 458 | 1.758  | 22.481 | 2.182  | 1.00 | 16.18 | A | N |
| ATOM | 1722 | CZ  | ARG A 458 | 0.586  | 22.555 | 2.796  | 1.00 | 15.85 | A | C |
| ATOM | 1723 | NH1 | ARG A 458 | 0.259  | 23.641 | 3.501  | 1.00 | 16.01 | A | N |
| ATOM | 1724 | NH2 | ARG A 458 | -0.260 | 21.547 | 2.719  | 1.00 | 14.46 | A | N |
| ATOM | 1725 | C   | ARG A 458 | 5.282  | 27.127 | 1.926  | 1.00 | 20.59 | A | C |
| ATOM | 1726 | O   | ARG A 458 | 5.225  | 28.206 | 1.302  | 1.00 | 21.00 | A | O |
| ATOM | 1727 | N   | MET A 459 | 6.407  | 26.683 | 2.523  | 1.00 | 20.39 | A | N |
| ATOM | 1728 | CA  | MET A 459 | 7.700  | 27.372 | 2.328  | 0.00 | 20.97 | A | C |
| ATOM | 1729 | CB  | MET A 459 | 8.835  | 26.667 | 3.074  | 1.00 | 20.97 | A | C |
| ATOM | 1730 | CG  | MET A 459 | 8.883  | 26.931 | 4.556  | 1.00 | 23.07 | A | C |
| ATOM | 1731 | SD  | MET A 459 | 10.321 | 26.066 | 5.230  | 1.00 | 25.33 | A | S |
| ATOM | 1732 | CE  | MET A 459 | 9.532  | 24.593 | 5.699  | 1.00 | 21.45 | A | C |
| ATOM | 1733 | C   | MET A 459 | 8.083  | 27.372 | 0.854  | 1.00 | 20.61 | A | C |
| ATOM | 1734 | O   | MET A 459 | 7.798  | 26.414 | 0.120  | 1.00 | 18.93 | A | O |
| ATOM | 1735 | N   | VAL A 460 | 8.728  | 28.452 | 0.413  | 1.00 | 21.68 | A | N |
| ATOM | 1736 | CA  | VAL A 460 | 9.181  | 28.533 | -0.970 | 0.00 | 23.77 | A | C |
| ATOM | 1737 | CB  | VAL A 460 | 9.383  | 29.994 | -1.375 | 1.00 | 25.06 | A | C |
| ATOM | 1738 | CG1 | VAL A 460 | 8.092  | 30.782 | -1.112 | 1.00 | 24.50 | A | C |
| ATOM | 1739 | CG2 | VAL A 460 | 10.579 | 30.643 | -0.549 | 1.00 | 26.04 | A | C |
| ATOM | 1740 | C   | VAL A 460 | 10.522 | 27.771 | -1.122 | 1.00 | 25.72 | A | C |
| ATOM | 1741 | O   | VAL A 460 | 11.165 | 27.403 | -0.124 | 1.00 | 24.58 | A | O |
| ATOM | 1742 | N   | ARG A 461 | 10.933 | 27.523 | -2.361 | 1.00 | 27.49 | A | N |
| ATOM | 1743 | CA  | ARG A 461 | 12.205 | 26.858 | -2.640 | 0.00 | 29.85 | A | C |
| ATOM | 1744 | CB  | ARG A 461 | 12.494 | 26.854 | -4.137 | 1.00 | 31.96 | A | C |
| ATOM | 1745 | CG  | ARG A 461 | 13.626 | 25.885 | -4.592 | 1.00 | 34.48 | A | C |
| ATOM | 1746 | CD  | ARG A 461 | 13.819 | 25.869 | -6.153 | 1.00 | 37.27 | A | C |
| ATOM | 1747 | NE  | ARG A 461 | 14.175 | 27.191 | -6.665 | 1.00 | 40.46 | A | N |
| ATOM | 1748 | CZ  | ARG A 461 | 15.360 | 27.766 | -6.483 | 1.00 | 43.22 | A | C |
| ATOM | 1749 | NH1 | ARG A 461 | 16.331 | 27.122 | -5.839 | 1.00 | 44.26 | A | N |
| ATOM | 1750 | NH2 | ARG A 461 | 15.512 | 29.059 | -6.735 | 1.00 | 43.71 | A | N |
| ATOM | 1751 | C   | ARG A 461 | 13.361 | 27.559 | -1.920 | 1.00 | 31.31 | A | C |
| ATOM | 1752 | O   | ARG A 461 | 13.598 | 28.762 | -2.114 | 1.00 | 31.29 | A | O |
| ATOM | 1753 | N   | PRO A 462 | 14.045 | 26.828 | -1.006 | 1.00 | 32.28 | A | N |
| ATOM | 1754 | CD  | PRO A 462 | 13.775 | 25.417 | -0.666 | 1.00 | 31.32 | A | C |
| ATOM | 1755 | CA  | PRO A 462 | 15.187 | 27.343 | -0.234 | 0.00 | 33.25 | A | C |
| ATOM | 1756 | CB  | PRO A 462 | 15.591 | 26.140 | 0.623  | 1.00 | 32.95 | A | C |
| ATOM | 1757 | CG  | PRO A 462 | 14.336 | 25.333 | 0.724  | 1.00 | 32.48 | A | C |

Figure 12

| ATOM | 1758 | C   | PRO A 462 | 16.322 | 27.724 | -1.210  | 1.00 | 34.82 | A | C |
| ATOM | 1759 | O   | PRO A 462 | 16.440 | 27.144 | -2.301  | 1.00 | 33.72 | A | O |
| ATOM | 1760 | N   | ASP A 463 | 17.120 | 28.722 | -0.845  | 1.00 | 36.64 | A | N |
| ATOM | 1761 | CA  | ASP A 463 | 18.199 | 29.129 | -1.732  | 0.00 | 39.77 | A | C |
| ATOM | 1762 | CB  | ASP A 463 | 18.967 | 30.350 | -1.173  | 1.00 | 41.51 | A | C |
| ATOM | 1763 | CG  | ASP A 463 | 18.122 | 31.638 | -1.182  | 1.00 | 43.75 | A | C |
| ATOM | 1764 | OD1 | ASP A 463 | 17.459 | 31.917 | -2.208  | 1.00 | 44.61 | A | O |
| ATOM | 1765 | OD2 | ASP A 463 | 18.125 | 32.379 | -0.164  | 1.00 | 45.42 | A | O |
| ATOM | 1766 | C   | ASP A 463 | 19.115 | 27.921 | -1.971  | 1.00 | 40.76 | A | C |
| ATOM | 1767 | O   | ASP A 463 | 19.349 | 27.111 | -1.073  | 1.00 | 41.32 | A | O |
| ATOM | 1768 | N   | ASN A 464 | 19.505 | 27.742 | -3.230  | 1.00 | 41.99 | A | N |
| ATOM | 1769 | CA  | ASN A 464 | 20.368 | 26.631 | -3.661  | 0.00 | 42.67 | A | C |
| ATOM | 1770 | CB  | ASN A 464 | 21.753 | 26.734 | -3.019  | 1.00 | 44.67 | A | C |
| ATOM | 1771 | CG  | ASN A 464 | 22.536 | 27.931 | -3.532  | 1.00 | 46.48 | A | C |
| ATOM | 1772 | OD1 | ASN A 464 | 22.548 | 28.193 | -4.741  | 1.00 | 48.10 | A | O |
| ATOM | 1773 | ND2 | ASN A 464 | 23.110 | 28.714 | -2.619  | 1.00 | 45.93 | A | N |
| ATOM | 1774 | C   | ASN A 464 | 19.744 | 25.256 | -3.466  | 1.00 | 42.33 | A | C |
| ATOM | 1775 | O   | ASN A 464 | 20.357 | 24.302 | -2.954  | 1.00 | 44.39 | A | O |
| ATOM | 1776 | N   | CYS A 465 | 18.508 | 25.143 | -3.908  | 1.00 | 39.92 | A | N |
| ATOM | 1777 | CA  | CYS A 465 | 17.832 | 23.891 | -3.788  | 0.00 | 37.10 | A | C |
| ATOM | 1778 | CB  | CYS A 465 | 16.647 | 24.065 | -2.833  | 1.00 | 35.45 | A | C |
| ATOM | 1779 | SG  | CYS A 465 | 15.619 | 22.636 | -2.710  | 1.00 | 32.86 | A | S |
| ATOM | 1780 | C   | CYS A 465 | 17.379 | 23.537 | -5.187  | 1.00 | 35.34 | A | C |
| ATOM | 1781 | O   | CYS A 465 | 16.858 | 24.386 | -5.865  | 1.00 | 36.35 | A | O |
| ATOM | 1782 | N   | PRO A 466 | 17.702 | 22.339 | -5.682  | 1.00 | 33.92 | A | N |
| ATOM | 1783 | CD  | PRO A 466 | 18.543 | 21.316 | -5.040  | 1.00 | 33.74 | A | C |
| ATOM | 1784 | CA  | PRO A 466 | 17.280 | 21.930 | -7.024  | 0.00 | 34.07 | A | C |
| ATOM | 1785 | CB  | PRO A 466 | 17.732 | 20.465 | -7.095  | 1.00 | 33.33 | A | C |
| ATOM | 1786 | CG  | PRO A 466 | 18.899 | 20.415 | -6.194  | 1.00 | 34.29 | A | C |
| ATOM | 1787 | C   | PRO A 466 | 15.735 | 21.986 | -7.095  | 1.00 | 34.32 | A | C |
| ATOM | 1788 | O   | PRO A 466 | 15.074 | 21.594 | -6.131  | 1.00 | 34.47 | A | O |
| ATOM | 1789 | N   | GLU A 467 | 15.170 | 22.439 | -8.221  | 1.00 | 34.58 | A | N |
| ATOM | 1790 | CA  | GLU A 467 | 13.704 | 22.510 | -8.407  | 0.00 | 34.52 | A | C |
| ATOM | 1791 | CB  | GLU A 467 | 13.334 | 22.953 | -9.831  | 1.00 | 35.80 | A | C |
| ATOM | 1792 | CG  | GLU A 467 | 12.538 | 24.292 | -9.908  | 1.00 | 38.71 | A | C |
| ATOM | 1793 | CD  | GLU A 467 | 11.254 | 24.350 | -9.062  | 1.00 | 39.98 | A | C |
| ATOM | 1794 | OE1 | GLU A 467 | 11.189 | 25.209 | -8.131  | 1.00 | 41.68 | A | O |
| ATOM | 1795 | OE2 | GLU A 467 | 10.303 | 23.580 | -9.367  | 1.00 | 40.50 | A | O |
| ATOM | 1796 | C   | GLU A 467 | 13.004 | 21.170 | -8.140  | 1.00 | 33.48 | A | C |
| ATOM | 1797 | O   | GLU A 467 | 11.935 | 21.131 | -7.549  | 1.00 | 32.44 | A | O |
| ATOM | 1798 | N   | GLU A 468 | 13.606 | 20.096 | -8.634  | 1.00 | 33.18 | A | N |
| ATOM | 1799 | CA  | GLU A 468 | 13.093 | 18.750 | -8.465  | 0.00 | 32.78 | A | C |
| ATOM | 1800 | CB  | GLU A 468 | 13.956 | 17.768 | -9.264  | 1.00 | 36.09 | A | C |
| ATOM | 1801 | CG  | GLU A 468 | 14.183 | 18.173 | -10.728 | 1.00 | 42.76 | A | C |
| ATOM | 1802 | CD  | GLU A 468 | 15.115 | 19.424 | -10.908 | 1.00 | 46.68 | A | C |
| ATOM | 1803 | OE1 | GLU A 468 | 16.140 | 19.562 | -10.180 | 1.00 | 48.16 | A | O |
| ATOM | 1804 | OE2 | GLU A 468 | 14.811 | 20.290 | -11.781 | 1.00 | 49.10 | A | O |
| ATOM | 1805 | C   | GLU A 468 | 13.096 | 18.368 | -6.987  | 1.00 | 30.62 | A | C |
| ATOM | 1806 | O   | GLU A 468 | 12.232 | 17.611 | -6.539  | 1.00 | 30.17 | A | O |
| ATOM | 1807 | N   | LEU A 469 | 14.075 | 18.844 | -6.213  | 1.00 | 28.77 | A | N |
| ATOM | 1808 | CA  | LEU A 469 | 14.069 | 18.501 | -4.781  | 0.00 | 26.51 | A | C |
| ATOM | 1809 | CB  | LEU A 469 | 15.394 | 18.809 | -4.062  | 1.00 | 24.49 | A | C |
| ATOM | 1810 | CG  | LEU A 469 | 15.387 | 18.381 | -2.580  | 1.00 | 23.61 | A | C |
| ATOM | 1811 | CD1 | LEU A 469 | 15.270 | 16.876 | -2.485  | 1.00 | 22.55 | A | C |
| ATOM | 1812 | CD2 | LEU A 469 | 16.637 | 18.812 | -1.879  | 1.00 | 23.09 | A | C |
| ATOM | 1813 | C   | LEU A 469 | 12.939 | 19.307 | -4.165  | 1.00 | 24.65 | A | C |
| ATOM | 1814 | O   | LEU A 469 | 12.204 | 18.806 | -3.314  | 1.00 | 25.44 | A | O |
| ATOM | 1815 | N   | TYR A 470 | 12.766 | 20.526 | -4.642  | 1.00 | 22.91 | A | N |
| ATOM | 1816 | CA  | TYR A 470 | 11.699 | 21.362 | -4.135  | 0.00 | 23.58 | A | C |

Figure 12

| ATOM | 1817 | CB  | TYR | A | 470 | 11.770 | 22.787 | -4.653 | 1.00 | 23.30 | A | C |
| ATOM | 1818 | CG  | TYR | A | 470 | 10.664 | 23.666 | -4.074 | 1.00 | 25.22 | A | C |
| ATOM | 1819 | CD1 | TYR | A | 470 | 10.570 | 23.903 | -2.700 | 1.00 | 24.55 | A | C |
| ATOM | 1820 | CE1 | TYR | A | 470 |  9.525 | 24.667 | -2.140 | 1.00 | 25.01 | A | C |
| ATOM | 1821 | CD2 | TYR | A | 470 |  9.669 | 24.231 | -4.909 | 1.00 | 26.13 | A | C |
| ATOM | 1822 | CE2 | TYR | A | 470 |  8.601 | 25.020 | -4.362 | 1.00 | 25.71 | A | C |
| ATOM | 1823 | CZ  | TYR | A | 470 |  8.538 | 25.226 | -2.982 | 1.00 | 26.00 | A | C |
| ATOM | 1824 | OH  | TYR | A | 470 |  7.502 | 25.966 | -2.460 | 1.00 | 22.32 | A | O |
| ATOM | 1825 | C   | TYR | A | 470 | 10.324 | 20.771 | -4.421 | 1.00 | 23.68 | A | C |
| ATOM | 1826 | O   | TYR | A | 470 |  9.467 | 20.853 | -3.576 | 1.00 | 23.93 | A | O |
| ATOM | 1827 | N   | GLN | A | 471 | 10.143 | 20.103 | -5.566 | 1.00 | 24.13 | A | N |
| ATOM | 1828 | CA  | GLN | A | 471 |  8.858 | 19.513 | -5.915 | 0.00 | 25.15 | A | C |
| ATOM | 1829 | CB  | GLN | A | 471 |  8.754 | 19.189 | -7.425 | 1.00 | 25.54 | A | C |
| ATOM | 1830 | CG  | GLN | A | 471 |  8.645 | 20.460 | -8.271 | 1.00 | 26.98 | A | C |
| ATOM | 1831 | CD  | GLN | A | 471 |  7.471 | 21.379 | -7.830 | 1.00 | 29.13 | A | C |
| ATOM | 1832 | OE1 | GLN | A | 471 |  6.381 | 20.904 | -7.502 | 1.00 | 29.63 | A | O |
| ATOM | 1833 | NE2 | GLN | A | 471 |  7.702 | 22.693 | -7.836 | 1.00 | 29.50 | A | N |
| ATOM | 1834 | C   | GLN | A | 471 |  8.593 | 18.294 | -5.062 | 1.00 | 24.79 | A | C |
| ATOM | 1835 | O   | GLN | A | 471 |  7.438 | 17.978 | -4.758 | 1.00 | 24.41 | A | O |
| ATOM | 1836 | N   | LEU | A | 472 |  9.671 | 17.620 | -4.678 | 1.00 | 24.58 | A | N |
| ATOM | 1837 | CA  | LEU | A | 472 |  9.570 | 16.462 | -3.800 | 0.00 | 23.75 | A | C |
| ATOM | 1838 | CB  | LEU | A | 472 | 10.922 | 15.815 | -3.666 | 1.00 | 24.65 | A | C |
| ATOM | 1839 | CG  | LEU | A | 472 | 10.901 | 14.301 | -3.505 | 1.00 | 26.54 | A | C |
| ATOM | 1840 | CD1 | LEU | A | 472 | 10.203 | 13.652 | -4.714 | 1.00 | 25.70 | A | C |
| ATOM | 1841 | CD2 | LEU | A | 472 | 12.379 | 13.815 | -3.387 | 1.00 | 27.00 | A | C |
| ATOM | 1842 | C   | LEU | A | 472 |  9.068 | 16.965 | -2.413 | 1.00 | 22.54 | A | C |
| ATOM | 1843 | O   | LEU | A | 472 |  8.160 | 16.370 | -1.840 | 1.00 | 22.82 | A | O |
| ATOM | 1844 | N   | MET | A | 473 |  9.620 | 18.066 | -1.921 | 1.00 | 21.08 | A | N |
| ATOM | 1845 | CA  | MET | A | 473 |  9.174 | 18.627 | -0.649 | 0.00 | 21.61 | A | C |
| ATOM | 1846 | CB  | MET | A | 473 |  9.975 | 19.876 | -0.266 | 1.00 | 21.20 | A | C |
| ATOM | 1847 | CG  | MET | A | 473 | 11.489 | 19.701 | -0.237 | 1.00 | 22.39 | A | C |
| ATOM | 1848 | SD  | MET | A | 473 | 12.280 | 21.335 | -0.134 | 1.00 | 25.11 | A | S |
| ATOM | 1849 | CE  | MET | A | 473 | 13.935 | 20.884 |  0.373 | 1.00 | 24.34 | A | C |
| ATOM | 1850 | C   | MET | A | 473 |  7.673 | 18.996 | -0.751 | 1.00 | 21.08 | A | C |
| ATOM | 1851 | O   | MET | A | 473 |  6.897 | 18.682 |  0.153 | 1.00 | 20.14 | A | O |
| ATOM | 1852 | N   | ARG | A | 474 |  7.256 | 19.578 | -1.877 | 1.00 | 21.73 | A | N |
| ATOM | 1853 | CA  | ARG | A | 474 |  5.845 | 19.937 | -2.070 | 0.00 | 21.20 | A | C |
| ATOM | 1854 | CB  | ARG | A | 474 |  5.622 | 20.728 | -3.369 | 1.00 | 21.11 | A | C |
| ATOM | 1855 | CG  | ARG | A | 474 |  6.422 | 22.024 | -3.409 | 1.00 | 20.86 | A | C |
| ATOM | 1856 | CD  | ARG | A | 474 |  6.005 | 22.954 | -2.278 | 1.00 | 22.30 | A | C |
| ATOM | 1857 | NE  | ARG | A | 474 |  4.563 | 23.217 | -2.365 | 1.00 | 22.94 | A | N |
| ATOM | 1858 | CZ  | ARG | A | 474 |  3.999 | 24.350 | -2.783 | 1.00 | 22.32 | A | C |
| ATOM | 1859 | NH1 | ARG | A | 474 |  4.728 | 25.413 | -3.131 | 1.00 | 18.87 | A | N |
| ATOM | 1860 | NH2 | ARG | A | 474 |  2.679 | 24.362 | -2.950 | 1.00 | 21.56 | A | N |
| ATOM | 1861 | C   | ARG | A | 474 |  5.028 | 18.661 | -2.063 | 1.00 | 21.03 | A | C |
| ATOM | 1862 | O   | ARG | A | 474 |  3.906 | 18.654 | -1.590 | 1.00 | 21.50 | A | O |
| ATOM | 1863 | N   | LEU | A | 475 |  5.592 | 17.564 | -2.537 | 1.00 | 20.49 | A | N |
| ATOM | 1864 | CA  | LEU | A | 475 |  4.839 | 16.310 | -2.478 | 0.00 | 21.11 | A | C |
| ATOM | 1865 | CB  | LEU | A | 475 |  5.502 | 15.204 | -3.299 | 1.00 | 20.21 | A | C |
| ATOM | 1866 | CG  | LEU | A | 475 |  5.179 | 15.281 | -4.799 | 1.00 | 22.74 | A | C |
| ATOM | 1867 | CD1 | LEU | A | 475 |  5.775 | 14.055 | -5.541 | 1.00 | 19.92 | A | C |
| ATOM | 1868 | CD2 | LEU | A | 475 |  3.618 | 15.428 | -5.090 | 1.00 | 20.07 | A | C |
| ATOM | 1869 | C   | LEU | A | 475 |  4.693 | 15.867 | -1.028 | 1.00 | 21.64 | A | C |
| ATOM | 1870 | O   | LEU | A | 475 |  3.647 | 15.334 | -0.639 | 1.00 | 21.82 | A | O |
| ATOM | 1871 | N   | CYS | A | 476 |  5.725 | 16.120 | -0.211 | 1.00 | 20.75 | A | N |
| ATOM | 1872 | CA  | CYS | A | 476 |  5.668 | 15.694 |  1.196 | 0.00 | 19.55 | A | C |
| ATOM | 1873 | CB  | CYS | A | 476 |  7.065 | 15.774 |  1.879 | 1.00 | 16.82 | A | C |
| ATOM | 1874 | SG  | CYS | A | 476 |  8.329 | 14.673 |  1.197 | 1.00 | 19.75 | A | S |
| ATOM | 1875 | C   | CYS | A | 476 |  4.647 | 16.563 |  1.957 | 1.00 | 18.57 | A | C |

Figure 12

```
ATOM   1876  O    CYS A 476       4.125  16.139   2.970  1.00 18.87      A    O
ATOM   1877  N    TRP A 477       4.441  17.800   1.506  1.00 17.19      A    N
ATOM   1878  CA   TRP A 477       3.517  18.742   2.156  0.00 17.63      A    C
ATOM   1879  CB   TRP A 477       4.088  20.172   2.081  1.00 15.67      A    C
ATOM   1880  CG   TRP A 477       5.441  20.256   2.704  1.00 18.21      A    C
ATOM   1881  CD2  TRP A 477       6.484  21.186   2.373  1.00 17.90      A    C
ATOM   1882  CE2  TRP A 477       7.618  20.836   3.145  1.00 18.17      A    C
ATOM   1883  CE3  TRP A 477       6.572  22.266   1.498  1.00 18.87      A    C
ATOM   1884  CD1  TRP A 477       5.976  19.400   3.661  1.00 17.04      A    C
ATOM   1885  NE1  TRP A 477       7.276  19.748   3.910  1.00 18.59      A    N
ATOM   1886  CZ2  TRP A 477       8.832  21.539   3.068  1.00 19.01      A    C
ATOM   1887  CZ3  TRP A 477       7.776  22.970   1.417  1.00 20.03      A    C
ATOM   1888  CH2  TRP A 477       8.896  22.598   2.201  1.00 18.94      A    C
ATOM   1889  C    TRP A 477       2.090  18.769   1.627  1.00 17.46      A    C
ATOM   1890  O    TRP A 477       1.397  19.779   1.792  1.00 18.00      A    O
ATOM   1891  N    LYS A 478       1.686  17.730   0.907  1.00 18.34      A    N
ATOM   1892  CA   LYS A 478       0.326  17.673   0.393  0.00 19.73      A    C
ATOM   1893  CB   LYS A 478       0.020  16.359  -0.333  1.00 19.71      A    C
ATOM   1894  CG   LYS A 478       0.661  16.241  -1.732  1.00 24.49      A    C
ATOM   1895  CD   LYS A 478       0.323  17.411  -2.666  1.00 27.43      A    C
ATOM   1896  CE   LYS A 478      -0.924  17.114  -3.478  1.00 30.17      A    C
ATOM   1897  NZ   LYS A 478      -1.451  18.339  -4.152  1.00 35.13      A    N
ATOM   1898  C    LYS A 478      -0.546  17.780   1.612  1.00 19.36      A    C
ATOM   1899  O    LYS A 478      -0.216  17.214   2.632  1.00 18.43      A    O
ATOM   1900  N    GLU A 479      -1.622  18.553   1.507  1.00 20.89      A    N
ATOM   1901  CA   GLU A 479      -2.567  18.760   2.599  0.00 21.59      A    C
ATOM   1902  CB   GLU A 479      -3.691  19.715   2.172  1.00 20.67      A    C
ATOM   1903  CG   GLU A 479      -4.659  20.084   3.330  1.00 21.50      A    C
ATOM   1904  CD   GLU A 479      -4.017  20.941   4.453  1.00 22.29      A    C
ATOM   1905  OE1  GLU A 479      -3.130  21.781   4.192  1.00 22.67      A    O
ATOM   1906  OE2  GLU A 479      -4.432  20.815   5.624  1.00 24.01      A    O
ATOM   1907  C    GLU A 479      -3.183  17.435   3.063  1.00 22.47      A    C
ATOM   1908  O    GLU A 479      -3.278  17.168   4.252  1.00 23.17      A    O
ATOM   1909  N    ARG A 480      -3.586  16.604   2.127  1.00 23.20      A    N
ATOM   1910  CA   ARG A 480      -4.179  15.318   2.496  0.00 24.24      A    C
ATOM   1911  CB   ARG A 480      -5.088  14.846   1.383  1.00 27.41      A    C
ATOM   1912  CG   ARG A 480      -6.298  15.662   1.198  1.00 32.58      A    C
ATOM   1913  CD   ARG A 480      -6.936  15.053   0.041  1.00 37.63      A    C
ATOM   1914  NE   ARG A 480      -8.222  15.643  -0.235  1.00 43.64      A    N
ATOM   1915  CZ   ARG A 480      -8.703  15.818  -1.469  1.00 46.04      A    C
ATOM   1916  NH1  ARG A 480      -7.977  15.445  -2.530  1.00 46.90      A    N
ATOM   1917  NH2  ARG A 480      -9.918  16.340  -1.629  1.00 46.64      A    N
ATOM   1918  C    ARG A 480      -3.088  14.300   2.666  1.00 22.60      A    C
ATOM   1919  O    ARG A 480      -2.240  14.163   1.812  1.00 21.78      A    O
ATOM   1920  N    PRO A 481      -3.145  13.519   3.734  1.00 22.01      A    N
ATOM   1921  CD   PRO A 481      -4.094  13.588   4.862  1.00 22.58      A    C
ATOM   1922  CA   PRO A 481      -2.116  12.509   3.993  0.00 21.20      A    C
ATOM   1923  CB   PRO A 481      -2.636  11.793   5.255  1.00 21.48      A    C
ATOM   1924  CG   PRO A 481      -3.331  12.849   5.991  1.00 20.60      A    C
ATOM   1925  C    PRO A 481      -1.953  11.538   2.871  1.00 20.86      A    C
ATOM   1926  O    PRO A 481      -0.834  11.268   2.478  1.00 19.51      A    O
ATOM   1927  N    GLU A 482      -3.079  11.094   2.289  1.00 21.43      A    N
ATOM   1928  CA   GLU A 482      -3.061  10.094   1.205  0.00 20.48      A    C
ATOM   1929  CB   GLU A 482      -4.480   9.610   0.881  1.00 22.16      A    C
ATOM   1930  CG   GLU A 482      -5.426  10.679   0.247  1.00 22.96      A    C
ATOM   1931  CD   GLU A 482      -6.215  11.485   1.275  1.00 24.82      A    C
ATOM   1932  OE1  GLU A 482      -5.900  11.519   2.485  1.00 25.20      A    O
ATOM   1933  OE2  GLU A 482      -7.202  12.086   0.874  1.00 27.81      A    O
ATOM   1934  C    GLU A 482      -2.317  10.526  -0.040  1.00 20.11      A    C
```

Figure 12

| ATOM | 1935 | O | GLU | A | 482 | -1.784 | 9.678 | -0.774 | 1.00 | 19.56 | A | O |
|------|------|-----|-----|---|-----|--------|--------|--------|------|-------|---|---|
| ATOM | 1936 | N | ASP | A | 483 | -2.187 | 11.833 | -0.245 | 1.00 | 19.54 | A | N |
| ATOM | 1937 | CA | ASP | A | 483 | -1.488 | 12.332 | -1.421 | 0.00 | 20.26 | A | C |
| ATOM | 1938 | CB | ASP | A | 483 | -2.024 | 13.715 | -1.836 | 1.00 | 21.30 | A | C |
| ATOM | 1939 | CG | ASP | A | 483 | -3.511 | 13.659 | -2.230 | 1.00 | 23.56 | A | C |
| ATOM | 1940 | OD1 | ASP | A | 483 | -3.945 | 12.612 | -2.745 | 1.00 | 22.77 | A | O |
| ATOM | 1941 | OD2 | ASP | A | 483 | -4.238 | 14.663 | -2.023 | 1.00 | 25.38 | A | O |
| ATOM | 1942 | C | ASP | A | 483 | 0.014 | 12.408 | -1.240 | 1.00 | 20.54 | A | C |
| ATOM | 1943 | O | ASP | A | 483 | 0.736 | 12.715 | -2.167 | 1.00 | 21.29 | A | O |
| ATOM | 1944 | N | ARG | A | 484 | 0.492 | 12.245 | -0.009 | 1.00 | 20.31 | A | N |
| ATOM | 1945 | CA | ARG | A | 484 | 1.926 | 12.295 | 0.232 | 0.00 | 18.99 | A | C |
| ATOM | 1946 | CB | ARG | A | 484 | 2.213 | 12.584 | 1.716 | 1.00 | 18.01 | A | C |
| ATOM | 1947 | CG | ARG | A | 484 | 1.625 | 13.867 | 2.201 | 1.00 | 16.80 | A | C |
| ATOM | 1948 | CD | ARG | A | 484 | 1.708 | 13.982 | 3.708 | 1.00 | 16.98 | A | C |
| ATOM | 1949 | NE | ARG | A | 484 | 0.864 | 15.085 | 4.137 | 1.00 | 17.57 | A | N |
| ATOM | 1950 | CZ | ARG | A | 484 | 0.291 | 15.170 | 5.325 | 1.00 | 17.25 | A | C |
| ATOM | 1951 | NH1 | ARG | A | 484 | 0.502 | 14.261 | 6.227 | 1.00 | 17.81 | A | N |
| ATOM | 1952 | NH2 | ARG | A | 484 | -0.651 | 16.086 | 5.540 | 1.00 | 17.35 | A | N |
| ATOM | 1953 | C | ARG | A | 484 | 2.485 | 10.936 | -0.166 | 1.00 | 18.18 | A | C |
| ATOM | 1954 | O | ARG | A | 484 | 1.828 | 9.901 | -0.016 | 1.00 | 15.55 | A | O |
| ATOM | 1955 | N | PRO | A | 485 | 3.714 | 10.934 | -0.720 | 1.00 | 18.58 | A | N |
| ATOM | 1956 | CD | PRO | A | 485 | 4.401 | 12.182 | -1.112 | 1.00 | 18.05 | A | C |
| ATOM | 1957 | CA | PRO | A | 485 | 4.453 | 9.757 | -1.186 | 0.00 | 17.72 | A | C |
| ATOM | 1958 | CB | PRO | A | 485 | 5.713 | 10.383 | -1.821 | 1.00 | 19.58 | A | C |
| ATOM | 1959 | CG | PRO | A | 485 | 5.822 | 11.727 | -1.193 | 1.00 | 17.96 | A | C |
| ATOM | 1960 | C | PRO | A | 485 | 4.855 | 8.841 | -0.057 | 1.00 | 18.33 | A | C |
| ATOM | 1961 | O | PRO | A | 485 | 4.933 | 9.277 | 1.078 | 1.00 | 19.38 | A | O |
| ATOM | 1962 | N | THR | A | 486 | 5.094 | 7.560 | -0.340 | 1.00 | 17.72 | A | N |
| ATOM | 1963 | CA | THR | A | 486 | 5.572 | 6.644 | 0.691 | 0.00 | 17.64 | A | C |
| ATOM | 1964 | CB | THR | A | 486 | 5.483 | 5.197 | 0.220 | 1.00 | 17.32 | A | C |
| ATOM | 1965 | OG1 | THR | A | 486 | 6.231 | 5.093 | -1.006 | 1.00 | 18.38 | A | O |
| ATOM | 1966 | CG2 | THR | A | 486 | 3.993 | 4.725 | 0.003 | 1.00 | 17.91 | A | C |
| ATOM | 1967 | C | THR | A | 486 | 7.103 | 6.921 | 0.870 | 1.00 | 19.05 | A | C |
| ATOM | 1968 | O | THR | A | 486 | 7.725 | 7.556 | 0.014 | 1.00 | 18.75 | A | O |
| ATOM | 1969 | N | PHE | A | 487 | 7.706 | 6.468 | 1.977 | 1.00 | 19.69 | A | N |
| ATOM | 1970 | CA | PHE | A | 487 | 9.138 | 6.611 | 2.170 | 0.00 | 20.78 | A | C |
| ATOM | 1971 | CB | PHE | A | 487 | 9.565 | 6.307 | 3.622 | 1.00 | 18.44 | A | C |
| ATOM | 1972 | CG | PHE | A | 487 | 9.368 | 7.474 | 4.536 | 1.00 | 15.57 | A | C |
| ATOM | 1973 | CD1 | PHE | A | 487 | 10.153 | 8.606 | 4.396 | 1.00 | 15.34 | A | C |
| ATOM | 1974 | CD2 | PHE | A | 487 | 8.357 | 7.461 | 5.488 | 1.00 | 16.19 | A | C |
| ATOM | 1975 | CE1 | PHE | A | 487 | 9.935 | 9.726 | 5.198 | 1.00 | 14.42 | A | C |
| ATOM | 1976 | CE2 | PHE | A | 487 | 8.118 | 8.553 | 6.299 | 1.00 | 14.97 | A | C |
| ATOM | 1977 | CZ | PHE | A | 487 | 8.909 | 9.703 | 6.162 | 1.00 | 14.91 | A | C |
| ATOM | 1978 | C | PHE | A | 487 | 9.827 | 5.680 | 1.185 | 1.00 | 22.41 | A | C |
| ATOM | 1979 | O | PHE | A | 487 | 10.908 | 5.969 | 0.711 | 1.00 | 21.58 | A | O |
| ATOM | 1980 | N | ASP | A | 488 | 9.184 | 4.574 | 0.842 | 1.00 | 25.25 | A | N |
| ATOM | 1981 | CA | ASP | A | 488 | 9.769 | 3.657 | -0.141 | 0.00 | 27.45 | A | C |
| ATOM | 1982 | CB | ASP | A | 488 | 8.772 | 2.536 | -0.381 | 1.00 | 31.96 | A | C |
| ATOM | 1983 | CG | ASP | A | 488 | 9.243 | 1.520 | -1.424 | 1.00 | 35.61 | A | C |
| ATOM | 1984 | OD1 | ASP | A | 488 | 10.463 | 1.416 | -1.732 | 1.00 | 37.71 | A | O |
| ATOM | 1985 | OD2 | ASP | A | 488 | 8.349 | 0.800 | -1.942 | 1.00 | 38.73 | A | O |
| ATOM | 1986 | C | ASP | A | 488 | 10.056 | 4.411 | -1.454 | 1.00 | 28.12 | A | C |
| ATOM | 1987 | O | ASP | A | 488 | 11.087 | 4.207 | -2.089 | 1.00 | 30.15 | A | O |
| ATOM | 1988 | N | TYR | A | 489 | 9.162 | 5.313 | -1.856 | 1.00 | 26.94 | A | N |
| ATOM | 1989 | CA | TYR | A | 489 | 9.337 | 6.083 | -3.076 | 0.00 | 24.66 | A | C |
| ATOM | 1990 | CB | TYR | A | 489 | 7.987 | 6.647 | -3.515 | 1.00 | 23.33 | A | C |
| ATOM | 1991 | CG | TYR | A | 489 | 8.105 | 7.711 | -4.566 | 1.00 | 22.22 | A | C |
| ATOM | 1992 | CD1 | TYR | A | 489 | 8.213 | 7.381 | -5.909 | 1.00 | 23.18 | A | C |
| ATOM | 1993 | CE1 | TYR | A | 489 | 8.277 | 8.381 | -6.906 | 1.00 | 23.37 | A | C |

Figure 12

| | | | | | | | | | | | |
|---|---|---|---|---|---|---|---|---|---|---|---|
| ATOM | 1994 | CD2 | TYR | A | 489 | 8.074 | 9.050 | -4.214 | 1.00 | 23.21 | A | C |
| ATOM | 1995 | CE2 | TYR | A | 489 | 8.137 | 10.058 | -5.165 | 1.00 | 24.25 | A | C |
| ATOM | 1996 | CZ | TYR | A | 489 | 8.242 | 9.726 | -6.518 | 1.00 | 25.10 | A | C |
| ATOM | 1997 | OH | TYR | A | 489 | 8.383 | 10.742 | -7.442 | 1.00 | 25.76 | A | O |
| ATOM | 1998 | C | TYR | A | 489 | 10.333 | 7.236 | -2.882 | 1.00 | 24.22 | A | C |
| ATOM | 1999 | O | TYR | A | 489 | 11.050 | 7.599 | -3.816 | 1.00 | 23.85 | A | O |
| ATOM | 2000 | N | LEU | A | 490 | 10.301 | 7.880 | -1.718 | 1.00 | 23.21 | A | N |
| ATOM | 2001 | CA | LEU | A | 490 | 11.236 | 8.972 | -1.403 | 0.00 | 23.59 | A | C |
| ATOM | 2002 | CB | LEU | A | 490 | 10.909 | 9.577 | -0.037 | 1.00 | 21.27 | A | C |
| ATOM | 2003 | CG | LEU | A | 490 | 9.661 | 10.497 | -0.019 | 1.00 | 21.85 | A | C |
| ATOM | 2004 | CD1 | LEU | A | 490 | 9.281 | 10.910 | 1.374 | 1.00 | 17.86 | A | C |
| ATOM | 2005 | CD2 | LEU | A | 490 | 9.911 | 11.733 | -0.817 | 1.00 | 21.77 | A | C |
| ATOM | 2006 | C | LEU | A | 490 | 12.726 | 8.482 | -1.481 | 1.00 | 24.25 | A | C |
| ATOM | 2007 | O | LEU | A | 490 | 13.609 | 9.198 | -1.965 | 1.00 | 22.57 | A | O |
| ATOM | 2008 | N | ARG | A | 491 | 12.973 | 7.261 | -1.021 | 1.00 | 25.48 | A | N |
| ATOM | 2009 | CA | ARG | A | 491 | 14.307 | 6.692 | -1.072 | 0.00 | 28.37 | A | C |
| ATOM | 2010 | CB | ARG | A | 491 | 14.347 | 5.384 | -0.292 | 1.00 | 30.22 | A | C |
| ATOM | 2011 | CG | ARG | A | 491 | 15.547 | 4.579 | -0.599 | 1.00 | 34.23 | A | C |
| ATOM | 2012 | CD | ARG | A | 491 | 15.420 | 3.177 | -0.078 | 1.00 | 39.77 | A | C |
| ATOM | 2013 | NE | ARG | A | 491 | 14.270 | 2.473 | -0.644 | 1.00 | 44.26 | A | N |
| ATOM | 2014 | CZ | ARG | A | 491 | 14.169 | 2.104 | -1.923 | 1.00 | 46.81 | A | C |
| ATOM | 2015 | NH1 | ARG | A | 491 | 15.155 | 2.356 | -2.795 | 1.00 | 47.08 | A | N |
| ATOM | 2016 | NH2 | ARG | A | 491 | 13.044 | 1.527 | -2.343 | 1.00 | 48.73 | A | N |
| ATOM | 2017 | C | ARG | A | 491 | 14.790 | 6.495 | -2.534 | 1.00 | 28.93 | A | C |
| ATOM | 2018 | O | ARG | A | 491 | 15.867 | 6.967 | -2.876 | 1.00 | 29.72 | A | O |
| ATOM | 2019 | N | SER | A | 492 | 13.975 | 5.881 | -3.415 | 1.00 | 29.25 | A | N |
| ATOM | 2020 | CA | SER | A | 492 | 14.355 | 5.671 | -4.825 | 0.00 | 29.12 | A | C |
| ATOM | 2021 | CB | SER | A | 492 | 13.255 | 4.938 | -5.596 | 1.00 | 29.15 | A | C |
| ATOM | 2022 | OG | SER | A | 492 | 12.796 | 3.834 | -4.854 | 1.00 | 31.79 | A | O |
| ATOM | 2023 | C | SER | A | 492 | 14.632 | 6.946 | -5.572 | 1.00 | 28.84 | A | C |
| ATOM | 2024 | O | SER | A | 492 | 15.525 | 7.010 | -6.427 | 1.00 | 30.77 | A | O |
| ATOM | 2025 | N | VAL | A | 493 | 13.869 | 7.975 | -5.325 | 1.00 | 28.80 | A | N |
| ATOM | 2026 | CA | VAL | A | 493 | 14.106 | 9.201 | -6.070 | 0.00 | 30.05 | A | C |
| ATOM | 2027 | CB | VAL | A | 493 | 12.810 | 10.088 | -6.248 | 1.00 | 30.95 | A | C |
| ATOM | 2028 | CG1 | VAL | A | 493 | 11.883 | 9.887 | -5.108 | 1.00 | 31.73 | A | C |
| ATOM | 2029 | CG2 | VAL | A | 493 | 13.157 | 11.578 | -6.360 | 1.00 | 30.53 | A | C |
| ATOM | 2030 | C | VAL | A | 493 | 15.308 | 9.950 | -5.561 | 1.00 | 30.82 | A | C |
| ATOM | 2031 | O | VAL | A | 493 | 16.038 | 10.574 | -6.345 | 1.00 | 30.03 | A | O |
| ATOM | 2032 | N | LEU | A | 494 | 15.564 | 9.818 | -4.253 | 1.00 | 32.36 | A | N |
| ATOM | 2033 | CA | LEU | A | 494 | 16.713 | 10.460 | -3.634 | 0.00 | 33.17 | A | C |
| ATOM | 2034 | CB | LEU | A | 494 | 16.523 | 10.583 | -2.106 | 1.00 | 30.65 | A | C |
| ATOM | 2035 | CG | LEU | A | 494 | 15.572 | 11.725 | -1.689 | 1.00 | 29.88 | A | C |
| ATOM | 2036 | CD1 | LEU | A | 494 | 15.318 | 11.639 | -0.210 | 1.00 | 27.17 | A | C |
| ATOM | 2037 | CD2 | LEU | A | 494 | 16.081 | 13.130 | -2.097 | 1.00 | 28.03 | A | C |
| ATOM | 2038 | C | LEU | A | 494 | 18.014 | 9.703 | -4.026 | 1.00 | 34.52 | A | C |
| ATOM | 2039 | O | LEU | A | 494 | 19.020 | 10.318 | -4.317 | 1.00 | 34.61 | A | O |
| ATOM | 2040 | N | GLU | A | 495 | 17.967 | 8.385 | -4.117 | 1.00 | 36.40 | A | N |
| ATOM | 2041 | CA | GLU | A | 495 | 19.143 | 7.615 | -4.496 | 0.00 | 38.96 | A | C |
| ATOM | 2042 | CB | GLU | A | 495 | 18.850 | 6.132 | -4.380 | 1.00 | 38.84 | A | C |
| ATOM | 2043 | CG | GLU | A | 495 | 19.281 | 5.528 | -3.100 | 1.00 | 40.36 | A | C |
| ATOM | 2044 | CD | GLU | A | 495 | 18.803 | 4.116 | -2.977 | 1.00 | 42.40 | A | C |
| ATOM | 2045 | OE1 | GLU | A | 495 | 18.840 | 3.412 | -4.013 | 1.00 | 43.98 | A | O |
| ATOM | 2046 | OE2 | GLU | A | 495 | 18.397 | 3.717 | -1.853 | 1.00 | 43.62 | A | O |
| ATOM | 2047 | C | GLU | A | 495 | 19.568 | 7.878 | -5.939 | 1.00 | 41.29 | A | C |
| ATOM | 2048 | O | GLU | A | 495 | 20.754 | 8.007 | -6.224 | 1.00 | 42.08 | A | O |
| ATOM | 2049 | N | ASP | A | 496 | 18.601 | 7.891 | -6.852 | 1.00 | 43.16 | A | N |
| ATOM | 2050 | CA | ASP | A | 496 | 18.890 | 8.112 | -8.250 | 0.00 | 44.98 | A | C |
| ATOM | 2051 | CB | ASP | A | 496 | 17.961 | 7.268 | -9.145 | 1.00 | 47.36 | A | C |
| ATOM | 2052 | CG | ASP | A | 496 | 17.895 | 5.770 | -8.729 | 1.00 | 50.65 | A | C |

Figure 12

| ATOM | 2053 | OD1 | ASP | A | 496 | 18.954 | 5.127 | -8.472 | 1.00 | 51.38 | A | O |
|------|------|-----|-----|---|-----|--------|-------|--------|------|-------|---|---|
| ATOM | 2054 | OD2 | ASP | A | 496 | 16.752 | 5.224 | -8.682 | 1.00 | 52.66 | A | O |
| ATOM | 2055 | C   | ASP | A | 496 | 18.731 | 9.577 | -8.615 | 1.00 | 45.69 | A | C |
| ATOM | 2056 | O   | ASP | A | 496 | 18.402 | 9.882 | -9.760 | 1.00 | 46.08 | A | O |
| ATOM | 2057 | N   | PHE | A | 497 | 19.015 | 10.496 | -7.690 | 1.00 | 46.28 | A | N |
| ATOM | 2058 | CA  | PHE | A | 497 | 18.844 | 11.917 | -7.995 | 0.00 | 46.97 | A | C |
| ATOM | 2059 | CB  | PHE | A | 497 | 18.898 | 12.766 | -6.733 | 1.00 | 45.68 | A | C |
| ATOM | 2060 | CG  | PHE | A | 497 | 18.138 | 14.060 | -6.839 | 1.00 | 45.95 | A | C |
| ATOM | 2061 | CD1 | PHE | A | 497 | 16.798 | 14.140 | -6.448 | 1.00 | 46.29 | A | C |
| ATOM | 2062 | CD2 | PHE | A | 497 | 18.764 | 15.218 | -7.310 | 1.00 | 46.19 | A | C |
| ATOM | 2063 | CE1 | PHE | A | 497 | 16.088 | 15.367 | -6.518 | 1.00 | 46.73 | A | C |
| ATOM | 2064 | CE2 | PHE | A | 497 | 18.069 | 16.453 | -7.389 | 1.00 | 46.89 | A | C |
| ATOM | 2065 | CZ  | PHE | A | 497 | 16.731 | 16.528 | -6.990 | 1.00 | 46.36 | A | C |
| ATOM | 2066 | C   | PHE | A | 497 | 19.818 | 12.397 | -9.084 | 1.00 | 48.31 | A | C |
| ATOM | 2067 | O   | PHE | A | 497 | 19.450 | 13.195 | -9.960 | 1.00 | 47.78 | A | O |
| ATOM | 2068 | N   | PHE | A | 498 | 21.062 | 11.928 | -9.003 | 1.00 | 49.79 | A | N |
| ATOM | 2069 | CA  | PHE | A | 498 | 22.092 | 12.222 | -10.014 | 0.00 | 51.06 | A | C |
| ATOM | 2070 | CB  | PHE | A | 498 | 22.320 | 13.730 | -10.255 | 1.00 | 50.99 | A | C |
| ATOM | 2071 | CG  | PHE | A | 498 | 22.498 | 14.564 | -9.005 | 1.00 | 51.02 | A | C |
| ATOM | 2072 | CD1 | PHE | A | 498 | 22.956 | 14.010 | -7.818 | 1.00 | 50.85 | A | C |
| ATOM | 2073 | CD2 | PHE | A | 498 | 22.166 | 15.921 | -9.030 | 1.00 | 50.74 | A | C |
| ATOM | 2074 | CE1 | PHE | A | 498 | 23.071 | 14.799 | -6.688 | 1.00 | 51.38 | A | C |
| ATOM | 2075 | CE2 | PHE | A | 498 | 22.276 | 16.718 | -7.911 | 1.00 | 50.78 | A | C |
| ATOM | 2076 | CZ  | PHE | A | 498 | 22.724 | 16.164 | -6.736 | 1.00 | 51.40 | A | C |
| ATOM | 2077 | C   | PHE | A | 498 | 23.419 | 11.499 | -9.794 | 1.00 | 52.05 | A | C |
| ATOM | 2078 | O   | PHE | A | 498 | 23.677 | 10.548 | -10.574 | 1.00 | 52.87 | A | O |
| ATOM | 2079 | N1  | LIG | A | 500 | 24.383 | 17.945 | 21.401 | 1.00 | 42.19 | A | N |
| ATOM | 2080 | C1  | LIG | A | 500 | 23.996 | 16.500 | 21.257 | 1.00 | 40.68 | A | C |
| ATOM | 2081 | C2  | LIG | A | 500 | 24.261 | 15.848 | 19.850 | 1.00 | 39.30 | A | C |
| ATOM | 2082 | C3  | LIG | A | 500 | 23.799 | 14.367 | 19.821 | 1.00 | 37.20 | A | C |
| ATOM | 2083 | C4  | LIG | A | 500 | 24.455 | 13.709 | 21.029 | 1.00 | 29.73 | A | C |
| ATOM | 2084 | C5  | LIG | A | 500 | 24.275 | 14.149 | 22.269 | 1.00 | 36.81 | A | C |
| ATOM | 2085 | C6  | LIG | A | 500 | 24.707 | 15.624 | 22.353 | 1.00 | 39.27 | A | C |
| ATOM | 2086 | N2  | LIG | A | 500 | 24.058 | 12.241 | 20.991 | 1.00 | 29.80 | A | N |
| ATOM | 2087 | N3  | LIG | A | 500 | 22.923 | 11.661 | 21.353 | 1.00 | 30.08 | A | N |
| ATOM | 2088 | C7  | LIG | A | 500 | 22.990 | 10.337 | 21.152 | 1.00 | 29.89 | A | C |
| ATOM | 2089 | C8  | LIG | A | 500 | 24.292 | 10.015 | 20.603 | 1.00 | 29.14 | A | C |
| ATOM | 2090 | C9  | LIG | A | 500 | 24.921 | 8.868 | 20.196 | 1.00 | 28.60 | A | C |
| ATOM | 2091 | N4  | LIG | A | 500 | 26.211 | 8.966 | 19.715 | 1.00 | 28.62 | A | N |
| ATOM | 2092 | C10 | LIG | A | 500 | 26.865 | 10.153 | 19.635 | 1.00 | 28.54 | A | C |
| ATOM | 2093 | N5  | LIG | A | 500 | 26.274 | 11.310 | 20.028 | 1.00 | 28.66 | A | N |
| ATOM | 2094 | C11 | LIG | A | 500 | 24.968 | 11.208 | 20.508 | 1.00 | 28.92 | A | C |
| ATOM | 2095 | N6  | LIG | A | 500 | 24.340 | 7.554 | 20.226 | 1.00 | 28.39 | A | N |
| ATOM | 2096 | C12 | LIG | A | 500 | 21.799 | 9.565 | 21.507 | 1.00 | 31.62 | A | C |
| ATOM | 2097 | C13 | LIG | A | 500 | 20.539 | 9.887 | 20.843 | 1.00 | 32.55 | A | C |
| ATOM | 2098 | C14 | LIG | A | 500 | 19.383 | 9.131 | 21.197 | 1.00 | 33.35 | A | C |
| ATOM | 2099 | C15 | LIG | A | 500 | 19.424 | 8.044 | 22.203 | 1.00 | 33.61 | A | C |
| ATOM | 2100 | C16 | LIG | A | 500 | 20.706 | 7.734 | 22.855 | 1.00 | 33.38 | A | C |
| ATOM | 2101 | C17 | LIG | A | 500 | 21.861 | 8.505 | 22.485 | 1.00 | 32.68 | A | C |
| ATOM | 2102 | C18 | LIG | A | 500 | 25.700 | 18.446 | 20.854 | 1.00 | 43.43 | A | C |
| ATOM | 2103 | C19 | LIG | A | 500 | 25.939 | 19.969 | 21.094 | 1.00 | 43.88 | A | C |
| ATOM | 2104 | N7  | LIG | A | 500 | 24.861 | 20.776 | 20.458 | 1.00 | 44.55 | A | N |
| ATOM | 2105 | C20 | LIG | A | 500 | 25.091 | 22.250 | 20.660 | 1.00 | 45.33 | A | C |
| ATOM | 2106 | C21 | LIG | A | 500 | 23.570 | 20.362 | 21.073 | 1.00 | 44.40 | A | C |
| ATOM | 2107 | C22 | LIG | A | 500 | 23.261 | 18.838 | 20.900 | 1.00 | 43.24 | A | C |
| ATOM | 2108 | O1  | LIG | A | 500 | 20.709 | 6.755 | 23.601 | 1.00 | 39.33 | A | O |
| ATOM | 2109 | C23 | LIG | A | 500 | 21.722 | 6.738 | 24.641 | 1.00 | 38.77 | A | C |
| ATOM | 2110 | C24 | LIG | A | 500 | 17.421 | 6.665 | 21.673 | 1.00 | 44.35 | A | C |
| ATOM | 2111 | O2  | LIG | A | 500 | 17.576 | 6.587 | 20.436 | 1.00 | 43.83 | A | O |

Figure 12

```
ATOM   2112  N8  LIG A 500      18.261   7.315  22.507  1.00 41.95      A    N
ATOM   2113  C25 LIG A 500      16.271   6.035  22.236  0.00 46.74      A    C
ATOM   2114  C26 LIG A 500      15.857   5.984  23.582  0.00 47.08      A    C
ATOM   2115  N9  LIG A 500      15.373   5.347  21.431  0.00 47.32      A    N
ATOM   2116  C27 LIG A 500      13.680   4.806  24.585  0.00 46.55      A    C
ATOM   2117  C28 LIG A 500      14.612   5.224  23.585  0.00 47.01      A    C
ATOM   2118  C29 LIG A 500      14.345   4.845  22.252  0.00 47.46      A    C
ATOM   2119  C30 LIG A 500      13.195   4.071  21.934  0.00 47.54      A    C
ATOM   2120  C31 LIG A 500      12.289   3.673  22.960  0.00 46.97      A    C
ATOM   2121  C32 LIG A 500      12.535   4.041  24.287  0.00 45.93      A    C
ATOM   2122  N10 LIG A 500      15.386   5.420  27.644  0.00 40.00      A    N
ATOM   2123  C33 LIG A 500      15.481   5.167  19.993  0.00 27.64      A    C
ATOM   2124  OH2 H2O A 600       5.668  22.047   9.199  1.00 15.57      A    O
ATOM   2125  OH2 H2O A 601       1.072   3.494  -1.678  1.00 68.55      A    O
ATOM   2126  OH2 H2O A 602      -1.327  24.063   0.472  1.00 18.10      A    O
ATOM   2127  OH2 H2O A 604       5.733   2.626  -3.205  1.00 43.74      A    O
ATOM   2128  OH2 H2O A 605      -5.942  25.276   2.051  1.00 49.35      A    O
ATOM   2129  OH2 H2O A 606       7.551  13.066  12.704  1.00 16.41      A    O
ATOM   2130  OH2 H2O A 607      -3.512  17.115  -0.859  1.00 20.11      A    O
ATOM   2131  OH2 H2O A 608       0.343   9.544  -3.101  1.00 46.99      A    O
ATOM   2132  OH2 H2O A 609      -0.929  30.586   2.041  1.00 29.09      A    O
ATOM   2133  OH2 H2O A 610       6.105  24.318   4.047  1.00 21.25      A    O
ATOM   2134  OH2 H2O A 611       5.217  18.854  -6.410  1.00 27.69      A    O
ATOM   2135  OH2 H2O A 612       0.544   5.860   0.044  1.00 32.72      A    O
ATOM   2136  OH2 H2O A 613      -0.603  28.557  -0.403  1.00 61.22      A    O
ATOM   2137  OH2 H2O A 614       9.620   9.268  18.598  1.00 21.35      A    O
ATOM   2138  OH2 H2O A 615      -9.652   8.169  -2.768  1.00 38.20      A    O
ATOM   2139  OH2 H2O A 616      -1.777   7.009  -0.267  1.00 28.53      A    O
ATOM   2140  OH2 H2O A 617       2.411  30.246  -0.182  1.00 62.20      A    O
ATOM   2141  OH2 H2O A 618       8.657  24.734  16.231  1.00 23.17      A    O
ATOM   2142  OH2 H2O A 619      -0.993   4.924   3.908  1.00 79.42      A    O
ATOM   2143  OH2 H2O A 620       1.314  26.666  -2.947  1.00 32.45      A    O
ATOM   2144  OH2 H2O A 621      30.124  13.571  19.590  0.00 44.73      A    O
ATOM   2145  OH2 H2O A 622       3.581   0.626  -2.093  1.00 58.74      A    O
ATOM   2146  OH2 H2O A 623      -3.581  23.596   1.701  1.00 40.20      A    O
ATOM   2147  OH2 H2O A 624      35.801  10.923  21.320  1.00 40.42      A    O
ATOM   2148  OH2 H2O A 625      20.427   5.120   0.846  1.00 45.92      A    O
ATOM   2149  OH2 H2O A 626      15.975  19.613  13.852  1.00 25.70      A    O
ATOM   2150  OH2 H2O A 627       3.578   6.245   3.386  1.00 20.03      A    O
ATOM   2151  OH2 H2O A 628       4.122  15.461  11.429  1.00 23.67      A    O
ATOM   2152  OH2 H2O A 630       8.526  15.362  -7.695  1.00 62.29      A    O
ATOM   2153  OH2 H2O A 631      34.458  -1.518  32.216  1.00 52.06      A    O
ATOM   2154  OH2 H2O A 632       5.189  28.136  -1.691  1.00 23.79      A    O
ATOM   2155  OH2 H2O A 633      17.361  11.982  18.919  1.00 59.43      A    O
ATOM   2156  OH2 H2O A 634      16.993  -0.881   3.798  1.00 36.60      A    O
ATOM   2157  OH2 H2O A 635      -0.929  11.703   9.777  1.00 37.89      A    O
ATOM   2158  OH2 H2O A 636      -2.614  12.467  -5.143  1.00 24.08      A    O
ATOM   2159  OH2 H2O A 638      -8.945   8.371  -5.305  1.00 25.58      A    O
ATOM   2160  OH2 H2O A 639      15.501  10.826  -8.945  1.00 41.87      A    O
ATOM   2161  OH2 H2O A 640      -1.813  23.537   5.386  1.00 26.97      A    O
ATOM   2162  OH2 H2O A 641      -2.846   6.628   2.192  1.00 25.46      A    O
ATOM   2163  OH2 H2O A 642      19.753  -0.626  14.753  1.00 49.57      A    O
ATOM   2164  OH2 H2O A 643      27.138  22.315  32.659  1.00 86.97      A    O
ATOM   2165  OH2 H2O A 644       2.872  21.298  -0.989  1.00 22.75      A    O
ATOM   2166  OH2 H2O A 645      -4.134  23.761   9.593  1.00 44.34      A    O
ATOM   2167  OH2 H2O A 646      29.019   0.458  39.786  1.00 72.15      A    O
ATOM   2168  OH2 H2O A 647       3.997  35.800   6.694  1.00 57.40      A    O
ATOM   2169  OH2 H2O A 648       1.103   4.953   9.987  1.00 25.30      A    O
ATOM   2170  OH2 H2O A 649     -13.768   5.765  -3.047  1.00 57.59      A    O
```

Figure 12

```
ATOM   2171  OH2  H2O  A  650      12.280   27.882    2.154  1.00 26.12      A    O
ATOM   2172  OH2  H2O  A  651       2.418   -2.441    0.797  1.00 33.57      A    O
ATOM   2173  OH2  H2O  A  652      -1.460   20.769   -1.077  1.00 29.60      A    O
ATOM   2174  OH2  H2O  A  653       3.916   22.524   11.060  1.00 15.04      A    O
ATOM   2175  OH2  H2O  A  654       2.876   30.734   -4.236  1.00 26.25      A    O
ATOM   2176  OH2  H2O  A  655      24.299   20.451   27.164  1.00 34.42      A    O
ATOM   2177  OH2  H2O  A  656       5.280    3.455   16.170  1.00 39.90      A    O
ATOM   2178  OH2  H2O  A  657       1.561    3.307    6.590  1.00 84.40      A    O
ATOM   2179  OH2  H2O  A  658      -1.839   24.527   -5.423  1.00 58.11      A    O
ATOM   2180  OH2  H2O  A  659       9.570   28.349   -4.828  1.00 24.10      A    O
ATOM   2181  OH2  H2O  A  660      33.901   12.129   22.654  1.00 41.88      A    O
ATOM   2182  OH2  H2O  A  661      17.902   16.275   24.068  0.00 40.85      A    O
ATOM   2183  OH2  H2O  A  662      -6.231   10.612   -3.355  1.00 83.08      A    O
ATOM   2184  OH2  H2O  A  663       6.490   34.521    3.397  1.00 33.48      A    O
ATOM   2185  OH2  H2O  A  664       6.011   11.790   -8.295  1.00 73.39      A    O
ATOM   2186  OH2  H2O  A  665       2.461    2.686    2.383  1.00 77.12      A    O
ATOM   2187  OH2  H2O  A  666      -2.164   24.614   -1.835  1.00 54.27      A    O
ATOM   2188  OH2  H2O  A  667       8.377    1.051    3.048  1.00 29.19      A    O
ATOM   2189  OH2  H2O  A  668      22.652   23.587   -0.888  1.00 35.22      A    O
ATOM   2190  OH2  H2O  A  669       4.674    0.684    2.029  1.00 64.54      A    O
ATOM   2191  OH2  H2O  A  670      -5.288   24.541   -2.034  1.00 83.90      A    O
ATOM   2192  OH2  H2O  A  671      -2.158    8.232    7.014  1.00 32.13      A    O
ATOM   2193  OH2  H2O  A  672       6.783    2.693   18.089  1.00 75.45      A    O
ATOM   2194  OH2  H2O  A  673      34.070   21.145   10.675  1.00 47.54      A    O
ATOM   2195  OH2  H2O  A  674      14.506    0.359    3.470  1.00 30.59      A    O
ATOM   2196  OH2  H2O  A  675      -2.632   25.122   11.424  1.00 23.83      A    O
ATOM   2197  OH2  H2O  A  676      32.117    4.524   17.418  1.00 54.57      A    O
ATOM   2198  OH2  H2O  A  677       6.093   15.359   14.119  1.00 34.38      A    O
ATOM   2199  OH2  H2O  A  678      -5.054   18.632    6.866  1.00 59.48      A    O
ATOM   2200  OH2  H2O  A  679      15.314   20.957   16.194  1.00 50.02      A    O
ATOM   2201  OH2  H2O  A  680      32.760   15.457   31.198  1.00 37.76      A    O
ATOM   2202  OH2  H2O  A  681      -6.160   19.178    9.374  1.00 47.10      A    O
ATOM   2203  OH2  H2O  A  682      29.839    2.778   19.006  1.00 33.56      A    O
ATOM   2204  OH2  H2O  A  683      19.814   16.633   19.804  0.00 58.45      A    O
ATOM   2205  OH2  H2O  A  684      14.745   24.897    6.910  1.00 22.10      A    O
ATOM   2206  OH2  H2O  A  685      -4.508   23.112    6.944  1.00 29.80      A    O
ATOM   2207  OH2  H2O  A  686      16.865   23.956  -10.187  1.00 30.49      A    O
ATOM   2208  OH2  H2O  A  687      -2.139   26.692   -3.812  1.00 56.66      A    O
ATOM   2209  OH2  H2O  A  688      34.212   12.796   10.191  1.00 65.71      A    O
ATOM   2210  OH2  H2O  A  689      -4.705   25.133   13.505  1.00 39.47      A    O
ATOM   2211  OH2  H2O  A  690       4.860    4.983   32.337  1.00 62.38      A    O
ATOM   2212  OH2  H2O  A  691      18.735   -1.851   18.646  1.00 42.26      A    O
ATOM   2213  OH2  H2O  A  692      12.821   21.500   17.546  1.00 40.03      A    O
ATOM   2214  OH2  H2O  A  693      16.767   23.455   11.854  1.00 34.31      A    O
ATOM   2215  OH2  H2O  A  694      17.773   -0.088   16.521  1.00 52.39      A    O
ATOM   2216  OH2  H2O  A  695      -9.862   10.390   -6.731  1.00 32.58      A    O
ATOM   2217  OH2  H2O  A  696      30.929   16.797    0.342  1.00 64.51      A    O
ATOM   2218  OH2  H2O  A  697      10.848   16.671   -8.401  1.00 71.89      A    O
ATOM   2219  OH2  H2O  A  698      25.042   11.322   34.167  1.00 52.53      A    O
ATOM   2220  OH2  H2O  A  699      -5.074   21.889   -0.139  1.00 33.11      A    O
ATOM   2221  CB   TRP  B  238      47.356   28.064   32.181  1.00 57.87      B    C
ATOM   2222  CG   TRP  B  238      46.842   28.558   33.523  1.00 59.24      B    C
ATOM   2223  CD2  TRP  B  238      47.375   28.247   34.816  1.00 59.57      B    C
ATOM   2224  CE2  TRP  B  238      46.587   28.942   35.773  1.00 59.71      B    C
ATOM   2225  CE3  TRP  B  238      48.434   27.454   35.284  1.00 59.62      B    C
ATOM   2226  CD1  TRP  B  238      45.784   29.397   33.731  1.00 59.78      B    C
ATOM   2227  NE1  TRP  B  238      45.627   29.634   35.075  1.00 60.17      B    N
ATOM   2228  CZ2  TRP  B  238      46.826   28.866   37.151  1.00 59.54      B    C
ATOM   2229  CZ3  TRP  B  238      48.674   27.374   36.664  1.00 59.54      B    C
```

Figure 12

```
ATOM   2230  CH2  TRP B 238      47.869  28.079  37.577  1.00 59.14       B    C
ATOM   2231  C    TRP B 238      49.085  28.151  30.357  1.00 55.92       B    C
ATOM   2232  O    TRP B 238      49.724  27.102  30.465  1.00 56.05       B    O
ATOM   2233  N    TRP B 238      48.206  30.278  31.350  1.00 56.14       B    N
ATOM   2234  CA   TRP B 238      48.557  28.851  31.612  0.00 56.50       B    C
ATOM   2235  N    GLU B 239      48.779  28.683  29.168  1.00 54.78       B    N
ATOM   2236  CA   GLU B 239      49.282  28.072  27.938  0.00 53.77       B    C
ATOM   2237  CB   GLU B 239      48.546  28.545  26.680  1.00 56.06       B    C
ATOM   2238  CG   GLU B 239      47.575  27.514  26.094  1.00 59.67       B    C
ATOM   2239  CD   GLU B 239      46.128  27.743  26.566  1.00 62.55       B    C
ATOM   2240  OE1  GLU B 239      45.867  27.652  27.803  1.00 63.25       B    O
ATOM   2241  OE2  GLU B 239      45.260  28.035  25.693  1.00 63.20       B    O
ATOM   2242  C    GLU B 239      50.763  28.371  27.784  1.00 51.59       B    C
ATOM   2243  O    GLU B 239      51.253  29.420  28.216  1.00 51.64       B    O
ATOM   2244  N    VAL B 240      51.490  27.391  27.273  1.00 48.53       B    N
ATOM   2245  CA   VAL B 240      52.910  27.565  27.055  0.00 46.35       B    C
ATOM   2246  CB   VAL B 240      53.763  27.043  28.224  1.00 46.39       B    C
ATOM   2247  CG1  VAL B 240      53.547  27.915  29.469  1.00 46.08       B    C
ATOM   2248  CG2  VAL B 240      53.460  25.566  28.471  1.00 45.92       B    C
ATOM   2249  C    VAL B 240      53.311  26.840  25.799  1.00 44.08       B    C
ATOM   2250  O    VAL B 240      52.646  25.883  25.375  1.00 42.79       B    O
ATOM   2251  N    PRO B 241      54.360  27.343  25.140  1.00 42.81       B    N
ATOM   2252  CD   PRO B 241      55.036  28.622  25.414  1.00 42.39       B    C
ATOM   2253  CA   PRO B 241      54.861  26.742  23.911  0.00 41.95       B    C
ATOM   2254  CB   PRO B 241      55.866  27.787  23.403  1.00 41.80       B    C
ATOM   2255  CG   PRO B 241      55.398  29.071  24.030  1.00 41.36       B    C
ATOM   2256  C    PRO B 241      55.542  25.405  24.205  1.00 41.24       B    C
ATOM   2257  O    PRO B 241      56.230  25.248  25.199  1.00 40.63       B    O
ATOM   2258  N    ARG B 242      55.281  24.442  23.346  1.00 40.97       B    N
ATOM   2259  CA   ARG B 242      55.852  23.118  23.432  0.00 41.94       B    C
ATOM   2260  CB   ARG B 242      55.438  22.368  22.189  1.00 41.90       B    C
ATOM   2261  CG   ARG B 242      56.066  21.039  22.055  1.00 45.26       B    C
ATOM   2262  CD   ARG B 242      55.410  20.073  22.943  1.00 45.28       B    C
ATOM   2263  NE   ARG B 242      53.961  20.085  22.771  1.00 48.14       B    N
ATOM   2264  CZ   ARG B 242      53.329  19.726  21.662  1.00 46.67       B    C
ATOM   2265  NH1  ARG B 242      54.029  19.344  20.618  1.00 48.28       B    N
ATOM   2266  NH2  ARG B 242      52.012  19.619  21.645  1.00 45.48       B    N
ATOM   2267  C    ARG B 242      57.387  23.136  23.555  1.00 41.83       B    C
ATOM   2268  O    ARG B 242      57.961  22.264  24.223  1.00 41.60       B    O
ATOM   2269  N    GLU B 243      58.012  24.157  22.954  1.00 42.39       B    N
ATOM   2270  CA   GLU B 243      59.480  24.387  22.940  0.00 43.13       B    C
ATOM   2271  CB   GLU B 243      59.881  25.666  22.162  1.00 44.01       B    C
ATOM   2272  CG   GLU B 243      59.738  25.598  20.658  1.00 47.78       B    C
ATOM   2273  CD   GLU B 243      58.272  25.669  20.194  1.00 49.81       B    C
ATOM   2274  OE1  GLU B 243      57.775  26.801  19.967  1.00 49.15       B    O
ATOM   2275  OE2  GLU B 243      57.620  24.596  20.060  1.00 50.30       B    O
ATOM   2276  C    GLU B 243      60.058  24.538  24.336  1.00 42.05       B    C
ATOM   2277  O    GLU B 243      61.235  24.273  24.544  1.00 41.87       B    O
ATOM   2278  N    THR B 244      59.265  25.080  25.256  1.00 41.32       B    N
ATOM   2279  CA   THR B 244      59.714  25.248  26.633  0.00 40.16       B    C
ATOM   2280  CB   THR B 244      58.794  26.195  27.425  1.00 40.73       B    C
ATOM   2281  OG1  THR B 244      57.473  25.636  27.501  1.00 40.67       B    O
ATOM   2282  CG2  THR B 244      58.721  27.559  26.778  1.00 40.05       B    C
ATOM   2283  C    THR B 244      59.679  23.900  27.344  1.00 39.57       B    C
ATOM   2284  O    THR B 244      59.944  23.829  28.521  1.00 39.94       B    O
ATOM   2285  N    LEU B 245      59.442  22.821  26.615  1.00 38.83       B    N
ATOM   2286  CA   LEU B 245      59.334  21.532  27.242  0.00 38.47       B    C
ATOM   2287  CB   LEU B 245      57.860  21.198  27.312  1.00 40.12       B    C
ATOM   2288  CG   LEU B 245      57.211  20.705  28.586  1.00 41.83       B    C
```

Figure 12

| ATOM | 2289 | CD1 | LEU | B | 245 | 57.450 | 21.700 | 29.705 | 1.00 | 42.46 | B | C |
| ATOM | 2290 | CD2 | LEU | B | 245 | 55.701 | 20.596 | 28.303 | 1.00 | 43.75 | B | C |
| ATOM | 2291 | C | LEU | B | 245 | 60.039 | 20.357 | 26.583 | 1.00 | 38.13 | B | C |
| ATOM | 2292 | O | LEU | B | 245 | 59.779 | 20.030 | 25.430 | 1.00 | 38.85 | B | O |
| ATOM | 2293 | N | LYS | B | 246 | 60.855 | 19.658 | 27.364 | 1.00 | 36.95 | B | N |
| ATOM | 2294 | CA | LYS | B | 246 | 61.533 | 18.469 | 26.890 | 0.00 | 35.65 | B | C |
| ATOM | 2295 | CB | LYS | B | 246 | 63.072 | 18.621 | 26.925 | 1.00 | 37.34 | B | C |
| ATOM | 2296 | CG | LYS | B | 246 | 63.898 | 17.371 | 26.395 | 1.00 | 38.27 | B | C |
| ATOM | 2297 | CD | LYS | B | 246 | 65.431 | 17.600 | 26.309 | 1.00 | 39.24 | B | C |
| ATOM | 2298 | CE | LYS | B | 246 | 66.014 | 18.348 | 27.554 | 1.00 | 40.66 | B | C |
| ATOM | 2299 | NZ | LYS | B | 246 | 67.481 | 18.699 | 27.466 | 1.00 | 41.55 | B | N |
| ATOM | 2300 | C | LYS | B | 246 | 61.077 | 17.307 | 27.770 | 1.00 | 34.80 | B | C |
| ATOM | 2301 | O | LYS | B | 246 | 61.217 | 17.331 | 28.992 | 1.00 | 34.17 | B | O |
| ATOM | 2302 | N | LEU | B | 247 | 60.489 | 16.302 | 27.144 | 1.00 | 34.37 | B | N |
| ATOM | 2303 | CA | LEU | B | 247 | 60.031 | 15.131 | 27.825 | 0.00 | 33.97 | B | C |
| ATOM | 2304 | CB | LEU | B | 247 | 58.807 | 14.533 | 27.108 | 1.00 | 33.48 | B | C |
| ATOM | 2305 | CG | LEU | B | 247 | 57.440 | 15.124 | 27.493 | 1.00 | 33.23 | B | C |
| ATOM | 2306 | CD1 | LEU | B | 247 | 57.344 | 16.603 | 27.196 | 1.00 | 32.65 | B | C |
| ATOM | 2307 | CD2 | LEU | B | 247 | 56.316 | 14.374 | 26.807 | 1.00 | 33.04 | B | C |
| ATOM | 2308 | C | LEU | B | 247 | 61.219 | 14.195 | 27.789 | 1.00 | 34.95 | B | C |
| ATOM | 2309 | O | LEU | B | 247 | 61.742 | 13.859 | 26.716 | 1.00 | 35.75 | B | O |
| ATOM | 2310 | N | VAL | B | 248 | 61.653 | 13.767 | 28.967 | 1.00 | 34.49 | B | N |
| ATOM | 2311 | CA | VAL | B | 248 | 62.806 | 12.906 | 29.066 | 0.00 | 33.58 | B | C |
| ATOM | 2312 | CB | VAL | B | 248 | 63.714 | 13.439 | 30.133 | 1.00 | 33.39 | B | C |
| ATOM | 2313 | CG1 | VAL | B | 248 | 64.963 | 12.603 | 30.265 | 1.00 | 33.94 | B | C |
| ATOM | 2314 | CG2 | VAL | B | 248 | 64.041 | 14.878 | 29.786 | 1.00 | 33.82 | B | C |
| ATOM | 2315 | C | VAL | B | 248 | 62.555 | 11.435 | 29.248 | 1.00 | 33.85 | B | C |
| ATOM | 2316 | O | VAL | B | 248 | 63.026 | 10.629 | 28.463 | 1.00 | 34.82 | B | O |
| ATOM | 2317 | N | GLU | B | 249 | 61.753 | 11.070 | 30.232 | 1.00 | 33.88 | B | N |
| ATOM | 2318 | CA | GLU | B | 249 | 61.509 | 9.658 | 30.467 | 0.00 | 33.42 | B | C |
| ATOM | 2319 | CB | GLU | B | 249 | 62.352 | 9.266 | 31.674 | 1.00 | 33.97 | B | C |
| ATOM | 2320 | CG | GLU | B | 249 | 61.958 | 8.037 | 32.441 | 1.00 | 34.50 | B | C |
| ATOM | 2321 | CD | GLU | B | 249 | 62.781 | 7.868 | 33.705 | 1.00 | 36.74 | B | C |
| ATOM | 2322 | OE1 | GLU | B | 249 | 63.612 | 8.765 | 34.028 | 1.00 | 36.77 | B | O |
| ATOM | 2323 | OE2 | GLU | B | 249 | 62.564 | 6.856 | 34.411 | 1.00 | 37.82 | B | O |
| ATOM | 2324 | C | GLU | B | 249 | 60.027 | 9.334 | 30.716 | 1.00 | 33.49 | B | C |
| ATOM | 2325 | O | GLU | B | 249 | 59.331 | 10.027 | 31.469 | 1.00 | 33.15 | B | O |
| ATOM | 2326 | N | ARG | B | 250 | 59.562 | 8.231 | 30.160 | 1.00 | 32.89 | B | N |
| ATOM | 2327 | CA | ARG | B | 250 | 58.190 | 7.868 | 30.377 | 0.00 | 33.33 | B | C |
| ATOM | 2328 | CB | ARG | B | 250 | 57.693 | 6.917 | 29.320 | 1.00 | 34.50 | B | C |
| ATOM | 2329 | CG | ARG | B | 250 | 56.205 | 7.012 | 29.224 | 1.00 | 36.76 | B | C |
| ATOM | 2330 | CD | ARG | B | 250 | 55.741 | 6.280 | 28.026 | 1.00 | 39.09 | B | C |
| ATOM | 2331 | NE | ARG | B | 250 | 55.942 | 4.872 | 28.252 | 1.00 | 40.86 | B | N |
| ATOM | 2332 | CZ | ARG | B | 250 | 55.771 | 3.947 | 27.324 | 1.00 | 43.27 | B | C |
| ATOM | 2333 | NH1 | ARG | B | 250 | 55.406 | 4.309 | 26.096 | 1.00 | 44.54 | B | N |
| ATOM | 2334 | NH2 | ARG | B | 250 | 55.901 | 2.660 | 27.636 | 1.00 | 43.21 | B | N |
| ATOM | 2335 | C | ARG | B | 250 | 58.043 | 7.168 | 31.696 | 1.00 | 33.30 | B | C |
| ATOM | 2336 | O | ARG | B | 250 | 58.781 | 6.210 | 31.959 | 1.00 | 32.97 | B | O |
| ATOM | 2337 | N | LEU | B | 251 | 57.045 | 7.606 | 32.476 | 1.00 | 31.29 | B | N |
| ATOM | 2338 | CA | LEU | B | 251 | 56.759 | 7.011 | 33.775 | 0.00 | 29.56 | B | C |
| ATOM | 2339 | CB | LEU | B | 251 | 56.269 | 8.069 | 34.740 | 1.00 | 27.75 | B | C |
| ATOM | 2340 | CG | LEU | B | 251 | 57.297 | 9.189 | 34.867 | 1.00 | 28.72 | B | C |
| ATOM | 2341 | CD1 | LEU | B | 251 | 56.687 | 10.299 | 35.705 | 1.00 | 29.06 | B | C |
| ATOM | 2342 | CD2 | LEU | B | 251 | 58.631 | 8.674 | 35.530 | 1.00 | 28.00 | B | C |
| ATOM | 2343 | C | LEU | B | 251 | 55.690 | 5.964 | 33.561 | 1.00 | 29.30 | B | C |
| ATOM | 2344 | O | LEU | B | 251 | 55.619 | 4.976 | 34.269 | 1.00 | 28.79 | B | O |
| ATOM | 2345 | N | GLY | B | 252 | 54.853 | 6.169 | 32.546 | 1.00 | 28.86 | B | N |
| ATOM | 2346 | CA | GLY | B | 252 | 53.812 | 5.192 | 32.294 | 0.00 | 27.78 | B | C |
| ATOM | 2347 | C | GLY | B | 252 | 53.002 | 5.470 | 31.045 | 1.00 | 26.94 | B | C |

Figure 12

| ATOM | 2348 | O | GLY | B | 252 | 52.947 | 6.599 | 30.563 | 1.00 | 25.89 | B | O |
| ATOM | 2349 | N | ALA | B | 253 | 52.332 | 4.418 | 30.569 | 1.00 | 26.76 | B | N |
| ATOM | 2350 | CA | ALA | B | 253 | 51.488 | 4.453 | 29.382 | 0.00 | 27.41 | B | C |
| ATOM | 2351 | CB | ALA | B | 253 | 52.232 | 3.879 | 28.173 | 1.00 | 26.48 | B | C |
| ATOM | 2352 | C | ALA | B | 253 | 50.256 | 3.596 | 29.662 | 1.00 | 27.58 | B | C |
| ATOM | 2353 | O | ALA | B | 253 | 50.350 | 2.422 | 30.041 | 1.00 | 25.24 | B | O |
| ATOM | 2354 | N | GLY | B | 254 | 49.100 | 4.213 | 29.418 | 1.00 | 28.70 | B | N |
| ATOM | 2355 | CA | GLY | B | 254 | 47.821 | 3.555 | 29.627 | 0.00 | 30.55 | B | C |
| ATOM | 2356 | C | GLY | B | 254 | 46.892 | 3.708 | 28.441 | 1.00 | 31.39 | B | C |
| ATOM | 2357 | O | GLY | B | 254 | 47.283 | 4.177 | 27.370 | 1.00 | 31.67 | B | O |
| ATOM | 2358 | N | GLN | B | 255 | 45.623 | 3.423 | 28.683 | 1.00 | 32.27 | B | N |
| ATOM | 2359 | CA | GLN | B | 255 | 44.621 | 3.469 | 27.626 | 0.00 | 32.57 | B | C |
| ATOM | 2360 | CB | GLN | B | 255 | 43.331 | 2.803 | 28.140 | 1.00 | 35.76 | B | C |
| ATOM | 2361 | CG | GLN | B | 255 | 42.422 | 2.227 | 27.039 | 1.00 | 41.64 | B | C |
| ATOM | 2362 | CD | GLN | B | 255 | 40.924 | 2.056 | 27.452 | 1.00 | 45.30 | B | C |
| ATOM | 2363 | OE1 | GLN | B | 255 | 40.037 | 1.900 | 26.564 | 1.00 | 46.00 | B | O |
| ATOM | 2364 | NE2 | GLN | B | 255 | 40.635 | 2.105 | 28.786 | 1.00 | 46.59 | B | N |
| ATOM | 2365 | C | GLN | B | 255 | 44.350 | 4.870 | 27.087 | 1.00 | 30.91 | B | C |
| ATOM | 2366 | O | GLN | B | 255 | 43.986 | 5.014 | 25.935 | 1.00 | 31.26 | B | O |
| ATOM | 2367 | N | PHE | B | 256 | 44.554 | 5.916 | 27.885 | 1.00 | 28.94 | B | N |
| ATOM | 2368 | CA | PHE | B | 256 | 44.233 | 7.261 | 27.417 | 0.00 | 27.56 | B | C |
| ATOM | 2369 | CB | PHE | B | 256 | 43.274 | 7.990 | 28.389 | 1.00 | 27.01 | B | C |
| ATOM | 2370 | CG | PHE | B | 256 | 41.948 | 7.324 | 28.572 | 1.00 | 26.95 | B | C |
| ATOM | 2371 | CD1 | PHE | B | 256 | 41.517 | 6.354 | 27.696 | 1.00 | 26.06 | B | C |
| ATOM | 2372 | CD2 | PHE | B | 256 | 41.095 | 7.706 | 29.628 | 1.00 | 28.03 | B | C |
| ATOM | 2373 | CE1 | PHE | B | 256 | 40.258 | 5.757 | 27.831 | 1.00 | 28.13 | B | C |
| ATOM | 2374 | CE2 | PHE | B | 256 | 39.811 | 7.097 | 29.780 | 1.00 | 27.48 | B | C |
| ATOM | 2375 | CZ | PHE | B | 256 | 39.405 | 6.131 | 28.878 | 1.00 | 27.70 | B | C |
| ATOM | 2376 | C | PHE | B | 256 | 45.413 | 8.189 | 27.178 | 1.00 | 27.01 | B | C |
| ATOM | 2377 | O | PHE | B | 256 | 45.225 | 9.366 | 26.879 | 1.00 | 25.56 | B | O |
| ATOM | 2378 | N | GLY | B | 257 | 46.629 | 7.684 | 27.364 | 1.00 | 27.01 | B | N |
| ATOM | 2379 | CA | GLY | B | 257 | 47.783 | 8.550 | 27.171 | 0.00 | 26.96 | B | C |
| ATOM | 2380 | C | GLY | B | 257 | 48.981 | 8.104 | 27.995 | 1.00 | 27.28 | B | C |
| ATOM | 2381 | O | GLY | B | 257 | 49.080 | 6.947 | 28.413 | 1.00 | 26.29 | B | O |
| ATOM | 2382 | N | GLU | B | 258 | 49.867 | 9.059 | 28.287 | 1.00 | 27.16 | B | N |
| ATOM | 2383 | CA | GLU | B | 258 | 51.070 | 8.723 | 29.031 | 0.00 | 26.19 | B | C |
| ATOM | 2384 | CB | GLU | B | 258 | 52.222 | 8.536 | 28.021 | 1.00 | 27.74 | B | C |
| ATOM | 2385 | CG | GLU | B | 258 | 51.926 | 7.483 | 26.937 | 1.00 | 31.44 | B | C |
| ATOM | 2386 | CD | GLU | B | 258 | 52.988 | 7.410 | 25.869 | 1.00 | 33.92 | B | C |
| ATOM | 2387 | OE1 | GLU | B | 258 | 53.653 | 8.442 | 25.653 | 1.00 | 35.52 | B | O |
| ATOM | 2388 | OE2 | GLU | B | 258 | 53.144 | 6.333 | 25.232 | 1.00 | 34.94 | B | O |
| ATOM | 2389 | C | GLU | B | 258 | 51.444 | 9.796 | 30.006 | 1.00 | 24.47 | B | C |
| ATOM | 2390 | O | GLU | B | 258 | 50.932 | 10.909 | 29.950 | 1.00 | 24.18 | B | O |
| ATOM | 2391 | N | VAL | B | 259 | 52.355 | 9.453 | 30.904 | 1.00 | 23.88 | B | N |
| ATOM | 2392 | CA | VAL | B | 259 | 52.897 | 10.416 | 31.857 | 0.00 | 24.27 | B | C |
| ATOM | 2393 | CB | VAL | B | 259 | 52.577 | 10.099 | 33.312 | 1.00 | 23.57 | B | C |
| ATOM | 2394 | CG1 | VAL | B | 259 | 53.080 | 11.279 | 34.217 | 1.00 | 22.40 | B | C |
| ATOM | 2395 | CG2 | VAL | B | 259 | 51.058 | 9.840 | 33.505 | 1.00 | 25.46 | B | C |
| ATOM | 2396 | C | VAL | B | 259 | 54.435 | 10.355 | 31.687 | 1.00 | 24.38 | B | C |
| ATOM | 2397 | O | VAL | B | 259 | 55.035 | 9.291 | 31.676 | 1.00 | 23.84 | B | O |
| ATOM | 2398 | N | TRP | B | 260 | 55.061 | 11.504 | 31.690 | 1.00 | 25.29 | B | N |
| ATOM | 2399 | CA | TRP | B | 260 | 56.513 | 11.558 | 31.479 | 0.00 | 26.63 | B | C |
| ATOM | 2400 | CB | TRP | B | 260 | 56.796 | 12.166 | 30.078 | 1.00 | 27.02 | B | C |
| ATOM | 2401 | CG | TRP | B | 260 | 56.550 | 11.271 | 28.885 | 1.00 | 29.61 | B | C |
| ATOM | 2402 | CD2 | TRP | B | 260 | 57.546 | 10.711 | 28.018 | 1.00 | 31.41 | B | C |
| ATOM | 2403 | CE2 | TRP | B | 260 | 56.888 | 9.839 | 27.124 | 1.00 | 33.19 | B | C |
| ATOM | 2404 | CE3 | TRP | B | 260 | 58.941 | 10.874 | 27.923 | 1.00 | 31.18 | B | C |
| ATOM | 2405 | CD1 | TRP | B | 260 | 55.346 | 10.745 | 28.460 | 1.00 | 31.48 | B | C |
| ATOM | 2406 | NE1 | TRP | B | 260 | 55.546 | 9.871 | 27.414 | 1.00 | 31.73 | B | N |

Figure 12

| | | | | | | | | | | | |
|---|---|---|---|---|---|---|---|---|---|---|---|
| ATOM | 2407 | CZ2 | TRP | B | 260 | 57.587 | 9.115 | 26.134 | 1.00 33.96 | B | C |
| ATOM | 2408 | CZ3 | TRP | B | 260 | 59.631 | 10.156 | 26.948 | 1.00 31.80 | B | C |
| ATOM | 2409 | CH2 | TRP | B | 260 | 58.962 | 9.288 | 26.070 | 1.00 33.73 | B | C |
| ATOM | 2410 | C | TRP | B | 260 | 57.161 | 12.514 | 32.457 | 1.00 26.21 | B | C |
| ATOM | 2411 | O | TRP | B | 260 | 56.544 | 13.490 | 32.827 | 1.00 25.09 | B | O |
| ATOM | 2412 | N | MET | B | 261 | 58.419 | 12.211 | 32.842 | 1.00 26.84 | B | N |
| ATOM | 2413 | CA | MET | B | 261 | 59.238 | 13.116 | 33.646 | 0.00 26.89 | B | C |
| ATOM | 2414 | CB | MET | B | 261 | 60.351 | 12.387 | 34.380 | 1.00 28.85 | B | C |
| ATOM | 2415 | CG | MET | B | 261 | 61.261 | 13.352 | 35.208 | 1.00 30.34 | B | C |
| ATOM | 2416 | SD | MET | B | 261 | 62.675 | 14.228 | 34.347 | 1.00 32.89 | B | S |
| ATOM | 2417 | CE | MET | B | 261 | 63.602 | 12.681 | 33.896 | 1.00 29.95 | B | C |
| ATOM | 2418 | C | MET | B | 261 | 59.902 | 13.952 | 32.572 | 1.00 26.76 | B | C |
| ATOM | 2419 | O | MET | B | 261 | 60.168 | 13.456 | 31.474 | 1.00 26.01 | B | O |
| ATOM | 2420 | N | GLY | B | 262 | 60.162 | 15.215 | 32.854 | 1.00 27.19 | B | N |
| ATOM | 2421 | CA | GLY | B | 262 | 60.793 | 16.052 | 31.874 | 0.00 27.99 | B | C |
| ATOM | 2422 | C | GLY | B | 262 | 61.223 | 17.327 | 32.534 | 1.00 29.65 | B | C |
| ATOM | 2423 | O | GLY | B | 262 | 61.105 | 17.452 | 33.749 | 1.00 30.42 | B | O |
| ATOM | 2424 | N | TYR | B | 263 | 61.684 | 18.276 | 31.725 | 1.00 31.08 | B | N |
| ATOM | 2425 | CA | TYR | B | 263 | 62.133 | 19.575 | 32.196 | 0.00 33.49 | B | C |
| ATOM | 2426 | CB | TYR | B | 263 | 63.650 | 19.708 | 31.997 | 1.00 32.03 | B | C |
| ATOM | 2427 | CG | TYR | B | 263 | 64.390 | 18.690 | 32.811 | 1.00 29.02 | B | C |
| ATOM | 2428 | CD1 | TYR | B | 263 | 64.715 | 18.945 | 34.148 | 1.00 27.66 | B | C |
| ATOM | 2429 | CE1 | TYR | B | 263 | 65.313 | 17.949 | 34.922 | 1.00 27.51 | B | C |
| ATOM | 2430 | CD2 | TYR | B | 263 | 64.681 | 17.428 | 32.272 | 1.00 27.35 | B | C |
| ATOM | 2431 | CE2 | TYR | B | 263 | 65.265 | 16.436 | 33.025 | 1.00 26.30 | B | C |
| ATOM | 2432 | CZ | TYR | B | 263 | 65.586 | 16.701 | 34.354 | 1.00 26.94 | B | C |
| ATOM | 2433 | OH | TYR | B | 263 | 66.221 | 15.705 | 35.071 | 1.00 26.84 | B | O |
| ATOM | 2434 | C | TYR | B | 263 | 61.403 | 20.753 | 31.558 | 1.00 35.91 | B | C |
| ATOM | 2435 | O | TYR | B | 263 | 61.103 | 20.748 | 30.357 | 1.00 36.17 | B | O |
| ATOM | 2436 | N | TYR | B | 264 | 61.108 | 21.741 | 32.385 | 1.00 38.84 | B | N |
| ATOM | 2437 | CA | TYR | B | 264 | 60.364 | 22.932 | 31.991 | 0.00 43.08 | B | C |
| ATOM | 2438 | CB | TYR | B | 264 | 59.155 | 23.106 | 32.953 | 1.00 44.11 | B | C |
| ATOM | 2439 | CG | TYR | B | 264 | 58.219 | 24.311 | 32.763 | 1.00 46.30 | B | C |
| ATOM | 2440 | CD1 | TYR | B | 264 | 57.707 | 24.672 | 31.499 | 1.00 47.13 | B | C |
| ATOM | 2441 | CE1 | TYR | B | 264 | 56.798 | 25.768 | 31.355 | 1.00 47.85 | B | C |
| ATOM | 2442 | CD2 | TYR | B | 264 | 57.810 | 25.068 | 33.880 | 1.00 47.44 | B | C |
| ATOM | 2443 | CE2 | TYR | B | 264 | 56.915 | 26.156 | 33.754 | 1.00 48.37 | B | C |
| ATOM | 2444 | CZ | TYR | B | 264 | 56.407 | 26.510 | 32.493 | 1.00 48.59 | B | C |
| ATOM | 2445 | OH | TYR | B | 264 | 55.533 | 27.600 | 32.395 | 1.00 48.12 | B | O |
| ATOM | 2446 | C | TYR | B | 264 | 61.317 | 24.117 | 32.086 | 1.00 45.15 | B | C |
| ATOM | 2447 | O | TYR | B | 264 | 61.914 | 24.372 | 33.150 | 1.00 45.57 | B | O |
| ATOM | 2448 | N | ASN | B | 265 | 61.448 | 24.849 | 30.981 | 1.00 46.77 | B | N |
| ATOM | 2449 | CA | ASN | B | 265 | 62.343 | 26.003 | 30.956 | 0.00 48.37 | B | C |
| ATOM | 2450 | CB | ASN | B | 265 | 61.903 | 27.045 | 32.000 | 1.00 49.33 | B | C |
| ATOM | 2451 | CG | ASN | B | 265 | 60.502 | 27.580 | 31.724 | 1.00 50.97 | B | C |
| ATOM | 2452 | OD1 | ASN | B | 265 | 60.056 | 27.621 | 30.570 | 1.00 51.19 | B | O |
| ATOM | 2453 | ND2 | ASN | B | 265 | 59.799 | 27.980 | 32.781 | 1.00 51.60 | B | N |
| ATOM | 2454 | C | ASN | B | 265 | 63.763 | 25.518 | 31.241 | 1.00 48.64 | B | C |
| ATOM | 2455 | O | ASN | B | 265 | 64.543 | 26.197 | 31.916 | 1.00 48.49 | B | O |
| ATOM | 2456 | N | GLY | B | 266 | 64.051 | 24.294 | 30.792 | 1.00 48.88 | B | N |
| ATOM | 2457 | CA | GLY | B | 266 | 65.383 | 23.726 | 30.968 | 0.00 49.28 | B | C |
| ATOM | 2458 | C | GLY | B | 266 | 65.811 | 23.171 | 32.327 | 1.00 49.27 | B | C |
| ATOM | 2459 | O | GLY | B | 266 | 66.548 | 22.169 | 32.387 | 1.00 48.72 | B | O |
| ATOM | 2460 | N | HIS | B | 267 | 65.385 | 23.813 | 33.414 | 1.00 49.84 | B | N |
| ATOM | 2461 | CA | HIS | B | 267 | 65.776 | 23.335 | 34.745 | 0.00 50.49 | B | C |
| ATOM | 2462 | CB | HIS | B | 267 | 66.710 | 24.340 | 35.446 | 1.00 53.53 | B | C |
| ATOM | 2463 | CG | HIS | B | 267 | 68.082 | 24.397 | 34.839 | 1.00 57.03 | B | C |
| ATOM | 2464 | CD2 | HIS | B | 267 | 68.999 | 23.419 | 34.607 | 1.00 57.96 | B | C |
| ATOM | 2465 | ND1 | HIS | B | 267 | 68.627 | 25.562 | 34.329 | 1.00 58.22 | B | N |

Figure 12

| | | | | | | | | | | | |
|---|---|---|---|---|---|---|---|---|---|---|---|
| ATOM | 2466 | CE1 | HIS | B | 267 | 69.814 | 25.298 | 33.808 | 1.00 | 58.80 | B | C |
| ATOM | 2467 | NE2 | HIS | B | 267 | 70.061 | 24.005 | 33.962 | 1.00 | 58.74 | B | N |
| ATOM | 2468 | C | HIS | B | 267 | 64.710 | 22.864 | 35.723 | 1.00 | 48.76 | B | C |
| ATOM | 2469 | O | HIS | B | 267 | 65.053 | 22.236 | 36.717 | 1.00 | 49.23 | B | O |
| ATOM | 2470 | N | THR | B | 268 | 63.442 | 23.179 | 35.495 | 1.00 | 46.22 | B | N |
| ATOM | 2471 | CA | THR | B | 268 | 62.440 | 22.712 | 36.447 | 0.00 | 43.48 | B | C |
| ATOM | 2472 | CB | THR | B | 268 | 61.264 | 23.640 | 36.546 | 1.00 | 43.80 | B | C |
| ATOM | 2473 | OG1 | THR | B | 268 | 61.751 | 24.980 | 36.738 | 1.00 | 45.18 | B | O |
| ATOM | 2474 | CG2 | THR | B | 268 | 60.388 | 23.222 | 37.732 | 1.00 | 43.00 | B | C |
| ATOM | 2475 | C | THR | B | 268 | 61.955 | 21.340 | 36.080 | 1.00 | 41.15 | B | C |
| ATOM | 2476 | O | THR | B | 268 | 61.454 | 21.146 | 34.980 | 1.00 | 41.65 | B | O |
| ATOM | 2477 | N | LYS | B | 269 | 62.160 | 20.377 | 36.972 | 1.00 | 38.25 | B | N |
| ATOM | 2478 | CA | LYS | B | 269 | 61.727 | 19.011 | 36.718 | 0.00 | 36.14 | B | C |
| ATOM | 2479 | CB | LYS | B | 269 | 62.407 | 18.044 | 37.667 | 1.00 | 35.49 | B | C |
| ATOM | 2480 | CG | LYS | B | 269 | 62.262 | 16.597 | 37.297 | 1.00 | 35.05 | B | C |
| ATOM | 2481 | CD | LYS | B | 269 | 63.061 | 15.784 | 38.285 | 1.00 | 35.93 | B | C |
| ATOM | 2482 | CE | LYS | B | 269 | 63.383 | 14.418 | 37.758 | 1.00 | 36.07 | B | C |
| ATOM | 2483 | NZ | LYS | B | 269 | 64.618 | 13.949 | 38.434 | 1.00 | 37.96 | B | N |
| ATOM | 2484 | C | LYS | B | 269 | 60.197 | 19.010 | 36.900 | 1.00 | 34.39 | B | C |
| ATOM | 2485 | O | LYS | B | 269 | 59.678 | 19.635 | 37.818 | 1.00 | 34.03 | B | O |
| ATOM | 2486 | N | VAL | B | 270 | 59.493 | 18.392 | 35.958 | 1.00 | 32.08 | B | N |
| ATOM | 2487 | CA | VAL | B | 270 | 58.024 | 18.362 | 35.971 | 0.00 | 29.66 | B | C |
| ATOM | 2488 | CB | VAL | B | 270 | 57.459 | 19.382 | 34.966 | 1.00 | 28.22 | B | C |
| ATOM | 2489 | CG1 | VAL | B | 270 | 57.787 | 20.773 | 35.385 | 1.00 | 26.08 | B | C |
| ATOM | 2490 | CG2 | VAL | B | 270 | 58.002 | 19.068 | 33.549 | 1.00 | 26.07 | B | C |
| ATOM | 2491 | C | VAL | B | 270 | 57.521 | 17.009 | 35.497 | 1.00 | 28.91 | B | C |
| ATOM | 2492 | O | VAL | B | 270 | 58.290 | 16.187 | 34.998 | 1.00 | 28.64 | B | O |
| ATOM | 2493 | N | ALA | B | 271 | 56.224 | 16.772 | 35.711 | 1.00 | 27.35 | B | N |
| ATOM | 2494 | CA | ALA | B | 271 | 55.574 | 15.558 | 35.221 | 0.00 | 25.79 | B | C |
| ATOM | 2495 | CB | ALA | B | 271 | 54.738 | 14.902 | 36.288 | 1.00 | 24.94 | B | C |
| ATOM | 2496 | C | ALA | B | 271 | 54.692 | 16.110 | 34.132 | 1.00 | 24.87 | B | C |
| ATOM | 2497 | O | ALA | B | 271 | 54.160 | 17.226 | 34.252 | 1.00 | 25.51 | B | O |
| ATOM | 2498 | N | VAL | B | 272 | 54.560 | 15.370 | 33.044 | 1.00 | 24.31 | B | N |
| ATOM | 2499 | CA | VAL | B | 272 | 53.730 | 15.822 | 31.927 | 0.00 | 23.65 | B | C |
| ATOM | 2500 | CB | VAL | B | 272 | 54.544 | 16.136 | 30.602 | 1.00 | 23.63 | B | C |
| ATOM | 2501 | CG1 | VAL | B | 272 | 53.578 | 16.641 | 29.505 | 1.00 | 20.83 | B | C |
| ATOM | 2502 | CG2 | VAL | B | 272 | 55.618 | 17.211 | 30.840 | 1.00 | 21.65 | B | C |
| ATOM | 2503 | C | VAL | B | 272 | 52.814 | 14.691 | 31.617 | 1.00 | 24.21 | B | C |
| ATOM | 2504 | O | VAL | B | 272 | 53.271 | 13.559 | 31.465 | 1.00 | 24.66 | B | O |
| ATOM | 2505 | N | LYS | B | 273 | 51.510 | 14.970 | 31.609 | 1.00 | 24.93 | B | N |
| ATOM | 2506 | CA | LYS | B | 273 | 50.539 | 13.940 | 31.236 | 0.00 | 25.70 | B | C |
| ATOM | 2507 | CB | LYS | B | 273 | 49.343 | 13.898 | 32.207 | 1.00 | 25.65 | B | C |
| ATOM | 2508 | CG | LYS | B | 273 | 48.301 | 12.836 | 31.790 | 1.00 | 26.86 | B | C |
| ATOM | 2509 | CD | LYS | B | 273 | 47.186 | 12.693 | 32.782 | 1.00 | 27.97 | B | C |
| ATOM | 2510 | CE | LYS | B | 273 | 47.669 | 12.064 | 34.080 | 1.00 | 29.09 | B | C |
| ATOM | 2511 | NZ | LYS | B | 273 | 46.537 | 11.917 | 35.094 | 1.00 | 31.13 | B | N |
| ATOM | 2512 | C | LYS | B | 273 | 50.075 | 14.272 | 29.805 | 1.00 | 25.59 | B | C |
| ATOM | 2513 | O | LYS | B | 273 | 49.707 | 15.398 | 29.517 | 1.00 | 24.51 | B | O |
| ATOM | 2514 | N | SER | B | 274 | 50.166 | 13.322 | 28.881 | 1.00 | 27.07 | B | N |
| ATOM | 2515 | CA | SER | B | 274 | 49.730 | 13.624 | 27.517 | 0.00 | 28.23 | B | C |
| ATOM | 2516 | CB | SER | B | 274 | 50.879 | 13.488 | 26.520 | 1.00 | 29.13 | B | C |
| ATOM | 2517 | OG | SER | B | 274 | 51.191 | 12.131 | 26.373 | 1.00 | 32.34 | B | O |
| ATOM | 2518 | C | SER | B | 274 | 48.578 | 12.717 | 27.103 | 1.00 | 28.79 | B | C |
| ATOM | 2519 | O | SER | B | 274 | 48.535 | 11.502 | 27.412 | 1.00 | 29.30 | B | O |
| ATOM | 2520 | N | LEU | B | 275 | 47.666 | 13.323 | 26.355 | 1.00 | 29.37 | B | N |
| ATOM | 2521 | CA | LEU | B | 275 | 46.472 | 12.643 | 25.854 | 0.00 | 29.74 | B | C |
| ATOM | 2522 | CB | LEU | B | 275 | 45.362 | 13.676 | 25.675 | 1.00 | 26.77 | B | C |
| ATOM | 2523 | CG | LEU | B | 275 | 44.130 | 13.105 | 24.984 | 1.00 | 26.84 | B | C |
| ATOM | 2524 | CD1 | LEU | B | 275 | 43.312 | 12.214 | 25.933 | 1.00 | 23.62 | B | C |

Figure 12

| ATOM | 2525 | CD2 | LEU | B | 275 | 43.329 | 14.273 | 24.500 | 1.00 | 25.93 | B | C |
| ATOM | 2526 | C | LEU | B | 275 | 46.655 | 11.852 | 24.550 | 1.00 | 30.61 | B | C |
| ATOM | 2527 | O | LEU | B | 275 | 47.225 | 12.350 | 23.590 | 1.00 | 31.05 | B | O |
| ATOM | 2528 | N | LYS | B | 276 | 46.231 | 10.596 | 24.527 | 1.00 | 32.03 | B | N |
| ATOM | 2529 | CA | LYS | B | 276 | 46.298 | 9.803 | 23.309 | 0.00 | 34.32 | B | C |
| ATOM | 2530 | CB | LYS | B | 276 | 46.165 | 8.311 | 23.646 | 1.00 | 35.03 | B | C |
| ATOM | 2531 | CG | LYS | B | 276 | 45.864 | 7.392 | 22.468 | 1.00 | 37.30 | B | C |
| ATOM | 2532 | CD | LYS | B | 276 | 45.668 | 5.936 | 22.901 | 1.00 | 40.31 | B | C |
| ATOM | 2533 | CE | LYS | B | 276 | 46.915 | 5.434 | 23.673 | 1.00 | 42.85 | B | C |
| ATOM | 2534 | NZ | LYS | B | 276 | 46.948 | 3.972 | 24.073 | 1.00 | 44.21 | B | N |
| ATOM | 2535 | C | LYS | B | 276 | 45.058 | 10.271 | 22.526 | 1.00 | 36.14 | B | C |
| ATOM | 2536 | O | LYS | B | 276 | 43.941 | 10.096 | 23.004 | 1.00 | 35.60 | B | O |
| ATOM | 2537 | N | GLN | B | 277 | 45.257 | 10.945 | 21.387 | 1.00 | 37.83 | B | N |
| ATOM | 2538 | CA | GLN | B | 277 | 44.156 | 11.438 | 20.533 | 0.00 | 39.07 | B | C |
| ATOM | 2539 | CB | GLN | B | 277 | 44.680 | 11.895 | 19.156 | 1.00 | 42.56 | B | C |
| ATOM | 2540 | CG | GLN | B | 277 | 43.584 | 12.248 | 18.107 | 1.00 | 46.50 | B | C |
| ATOM | 2541 | CD | GLN | B | 277 | 44.155 | 12.413 | 16.677 | 1.00 | 50.22 | B | C |
| ATOM | 2542 | OE1 | GLN | B | 277 | 45.075 | 11.668 | 16.271 | 1.00 | 52.16 | B | O |
| ATOM | 2543 | NE2 | GLN | B | 277 | 43.617 | 13.377 | 15.917 | 1.00 | 49.99 | B | N |
| ATOM | 2544 | C | GLN | B | 277 | 43.067 | 10.387 | 20.313 | 1.00 | 38.18 | B | C |
| ATOM | 2545 | O | GLN | B | 277 | 43.351 | 9.196 | 20.132 | 1.00 | 36.09 | B | O |
| ATOM | 2546 | N | GLY | B | 278 | 41.816 | 10.856 | 20.350 | 1.00 | 38.31 | B | N |
| ATOM | 2547 | CA | GLY | B | 278 | 40.680 | 9.973 | 20.165 | 0.00 | 39.29 | B | C |
| ATOM | 2548 | C | GLY | B | 278 | 40.163 | 9.279 | 21.425 | 1.00 | 40.16 | B | C |
| ATOM | 2549 | O | GLY | B | 278 | 39.106 | 8.637 | 21.385 | 1.00 | 41.43 | B | O |
| ATOM | 2550 | N | SER | B | 279 | 40.897 | 9.384 | 22.532 | 1.00 | 39.46 | B | N |
| ATOM | 2551 | CA | SER | B | 279 | 40.503 | 8.765 | 23.795 | 0.00 | 39.03 | B | C |
| ATOM | 2552 | CB | SER | B | 279 | 41.653 | 8.864 | 24.796 | 1.00 | 39.11 | B | C |
| ATOM | 2553 | OG | SER | B | 279 | 42.641 | 7.930 | 24.455 | 1.00 | 41.08 | B | O |
| ATOM | 2554 | C | SER | B | 279 | 39.330 | 9.546 | 24.325 | 1.00 | 38.34 | B | C |
| ATOM | 2555 | O | SER | B | 279 | 38.366 | 9.008 | 24.876 | 1.00 | 38.62 | B | O |
| ATOM | 2556 | N | MET | B | 280 | 39.497 | 10.849 | 24.255 | 1.00 | 37.74 | B | N |
| ATOM | 2557 | CA | MET | B | 280 | 38.480 | 11.770 | 24.689 | 0.00 | 36.75 | B | C |
| ATOM | 2558 | CB | MET | B | 280 | 38.447 | 11.865 | 26.226 | 1.00 | 36.54 | B | C |
| ATOM | 2559 | CG | MET | B | 280 | 39.570 | 12.682 | 26.847 | 1.00 | 34.50 | B | C |
| ATOM | 2560 | SD | MET | B | 280 | 39.791 | 12.293 | 28.594 | 1.00 | 35.85 | B | S |
| ATOM | 2561 | CE | MET | B | 280 | 39.216 | 13.651 | 29.253 | 1.00 | 34.53 | B | C |
| ATOM | 2562 | C | MET | B | 280 | 38.856 | 13.078 | 24.047 | 1.00 | 36.89 | B | C |
| ATOM | 2563 | O | MET | B | 280 | 39.935 | 13.216 | 23.470 | 1.00 | 37.48 | B | O |
| ATOM | 2564 | N | SER | B | 281 | 37.966 | 14.041 | 24.145 | 1.00 | 37.31 | B | N |
| ATOM | 2565 | CA | SER | B | 281 | 38.199 | 15.318 | 23.534 | 0.00 | 37.60 | B | C |
| ATOM | 2566 | CB | SER | B | 281 | 36.875 | 16.100 | 23.364 | 1.00 | 36.76 | B | C |
| ATOM | 2567 | OG | SER | B | 281 | 36.583 | 16.980 | 24.437 | 1.00 | 34.83 | B | O |
| ATOM | 2568 | C | SER | B | 281 | 39.197 | 16.131 | 24.298 | 1.00 | 39.19 | B | C |
| ATOM | 2569 | O | SER | B | 281 | 39.440 | 15.910 | 25.473 | 1.00 | 39.08 | B | O |
| ATOM | 2570 | N | PRO | B | 282 | 39.874 | 17.028 | 23.584 | 1.00 | 40.47 | B | N |
| ATOM | 2571 | CD | PRO | B | 282 | 40.031 | 17.024 | 22.111 | 1.00 | 41.00 | B | C |
| ATOM | 2572 | CA | PRO | B | 282 | 40.859 | 17.884 | 24.197 | 0.00 | 41.25 | B | C |
| ATOM | 2573 | CB | PRO | B | 282 | 41.218 | 18.823 | 23.050 | 1.00 | 40.91 | B | C |
| ATOM | 2574 | CG | PRO | B | 282 | 41.295 | 17.846 | 21.897 | 1.00 | 41.50 | B | C |
| ATOM | 2575 | C | PRO | B | 282 | 40.235 | 18.614 | 25.351 | 1.00 | 42.20 | B | C |
| ATOM | 2576 | O | PRO | B | 282 | 40.719 | 18.530 | 26.467 | 1.00 | 42.08 | B | O |
| ATOM | 2577 | N | ASP | B | 283 | 39.125 | 19.297 | 25.079 | 1.00 | 43.64 | B | N |
| ATOM | 2578 | CA | ASP | B | 283 | 38.444 | 20.091 | 26.107 | 0.00 | 44.13 | B | C |
| ATOM | 2579 | CB | ASP | B | 283 | 37.268 | 20.894 | 25.488 | 1.00 | 47.14 | B | C |
| ATOM | 2580 | CG | ASP | B | 283 | 37.740 | 21.992 | 24.508 | 1.00 | 50.04 | B | C |
| ATOM | 2581 | OD1 | ASP | B | 283 | 38.840 | 22.587 | 24.727 | 1.00 | 52.16 | B | O |
| ATOM | 2582 | OD2 | ASP | B | 283 | 37.011 | 22.264 | 23.526 | 1.00 | 51.45 | B | O |
| ATOM | 2583 | C | ASP | B | 283 | 38.036 | 19.296 | 27.364 | 1.00 | 42.77 | B | C |

Figure 12

| ATOM | 2584 | O | ASP | B | 283 | 37.988 | 19.837 | 28.456 | 1.00 | 42.43 | B | O |
|------|------|------|-----|---|-----|--------|--------|--------|------|-------|---|---|
| ATOM | 2585 | N | ALA | B | 284 | 37.844 | 17.992 | 27.224 | 1.00 | 41.58 | B | N |
| ATOM | 2586 | CA | ALA | B | 284 | 37.485 | 17.124 | 28.341 | 0.00 | 40.46 | B | C |
| ATOM | 2587 | CB | ALA | B | 284 | 36.801 | 15.865 | 27.832 | 1.00 | 39.62 | B | C |
| ATOM | 2588 | C | ALA | B | 284 | 38.735 | 16.725 | 29.145 | 1.00 | 40.43 | B | C |
| ATOM | 2589 | O | ALA | B | 284 | 38.656 | 16.494 | 30.348 | 1.00 | 39.26 | B | O |
| ATOM | 2590 | N | PHE | B | 285 | 39.854 | 16.522 | 28.437 | 1.00 | 39.85 | B | N |
| ATOM | 2591 | CA | PHE | B | 285 | 41.133 | 16.162 | 29.049 | 0.00 | 39.03 | B | C |
| ATOM | 2592 | CB | PHE | B | 285 | 42.146 | 15.810 | 27.953 | 1.00 | 38.01 | B | C |
| ATOM | 2593 | CG | PHE | B | 285 | 43.536 | 15.525 | 28.455 | 1.00 | 36.66 | B | C |
| ATOM | 2594 | CD1 | PHE | B | 285 | 43.821 | 14.327 | 29.124 | 1.00 | 34.75 | B | C |
| ATOM | 2595 | CD2 | PHE | B | 285 | 44.566 | 16.435 | 28.234 | 1.00 | 35.58 | B | C |
| ATOM | 2596 | CE1 | PHE | B | 285 | 45.107 | 14.040 | 29.546 | 1.00 | 33.77 | B | C |
| ATOM | 2597 | CE2 | PHE | B | 285 | 45.866 | 16.155 | 28.654 | 1.00 | 34.61 | B | C |
| ATOM | 2598 | CZ | PHE | B | 285 | 46.132 | 14.950 | 29.315 | 1.00 | 34.30 | B | C |
| ATOM | 2599 | C | PHE | B | 285 | 41.592 | 17.382 | 29.806 | 1.00 | 39.58 | B | C |
| ATOM | 2600 | O | PHE | B | 285 | 41.936 | 17.293 | 30.979 | 1.00 | 38.94 | B | O |
| ATOM | 2601 | N | LEU | B | 286 | 41.536 | 18.533 | 29.143 | 1.00 | 40.92 | B | N |
| ATOM | 2602 | CA | LEU | B | 286 | 41.940 | 19.806 | 29.738 | 0.00 | 43.69 | B | C |
| ATOM | 2603 | CB | LEU | B | 286 | 41.935 | 20.895 | 28.685 | 1.00 | 43.78 | B | C |
| ATOM | 2604 | CG | LEU | B | 286 | 43.142 | 20.800 | 27.758 | 1.00 | 43.80 | B | C |
| ATOM | 2605 | CD1 | LEU | B | 286 | 42.833 | 21.500 | 26.407 | 1.00 | 43.88 | B | C |
| ATOM | 2606 | CD2 | LEU | B | 286 | 44.339 | 21.400 | 28.490 | 1.00 | 43.18 | B | C |
| ATOM | 2607 | C | LEU | B | 286 | 41.062 | 20.260 | 30.867 | 1.00 | 46.06 | B | C |
| ATOM | 2608 | O | LEU | B | 286 | 41.529 | 20.835 | 31.842 | 1.00 | 46.09 | B | O |
| ATOM | 2609 | N | ALA | B | 287 | 39.762 | 20.111 | 30.671 | 1.00 | 49.24 | B | N |
| ATOM | 2610 | CA | ALA | B | 287 | 38.768 | 20.509 | 31.668 | 0.00 | 51.25 | B | C |
| ATOM | 2611 | CB | ALA | B | 287 | 37.380 | 19.966 | 31.269 | 1.00 | 52.31 | B | C |
| ATOM | 2612 | C | ALA | B | 287 | 39.195 | 19.984 | 33.038 | 1.00 | 52.11 | B | C |
| ATOM | 2613 | O | ALA | B | 287 | 39.001 | 20.635 | 34.081 | 1.00 | 51.90 | B | O |
| ATOM | 2614 | N | GLU | B | 288 | 39.898 | 18.863 | 33.003 | 1.00 | 53.06 | B | N |
| ATOM | 2615 | CA | GLU | B | 288 | 40.421 | 18.224 | 34.216 | 0.00 | 53.65 | B | C |
| ATOM | 2616 | CB | GLU | B | 288 | 40.842 | 16.778 | 33.878 | 1.00 | 55.19 | B | C |
| ATOM | 2617 | CG | GLU | B | 288 | 39.730 | 15.927 | 33.140 | 1.00 | 56.75 | B | C |
| ATOM | 2618 | CD | GLU | B | 288 | 40.179 | 14.504 | 32.747 | 1.00 | 57.66 | B | C |
| ATOM | 2619 | OE1 | GLU | B | 288 | 41.420 | 14.289 | 32.618 | 1.00 | 59.52 | B | O |
| ATOM | 2620 | OE2 | GLU | B | 288 | 39.294 | 13.608 | 32.591 | 1.00 | 57.46 | B | O |
| ATOM | 2621 | C | GLU | B | 288 | 41.577 | 19.013 | 34.916 | 1.00 | 53.05 | B | C |
| ATOM | 2622 | O | GLU | B | 288 | 41.870 | 18.815 | 36.096 | 1.00 | 52.66 | B | O |
| ATOM | 2623 | N | ALA | B | 289 | 42.228 | 19.912 | 34.176 | 1.00 | 52.84 | B | N |
| ATOM | 2624 | CA | ALA | B | 289 | 43.303 | 20.737 | 34.704 | 0.00 | 52.03 | B | C |
| ATOM | 2625 | CB | ALA | B | 289 | 44.412 | 20.854 | 33.709 | 1.00 | 52.86 | B | C |
| ATOM | 2626 | C | ALA | B | 289 | 42.821 | 22.112 | 35.089 | 1.00 | 52.32 | B | C |
| ATOM | 2627 | O | ALA | B | 289 | 43.566 | 22.873 | 35.685 | 1.00 | 51.33 | B | O |
| ATOM | 2628 | N | ASN | B | 290 | 41.591 | 22.458 | 34.714 | 1.00 | 53.34 | B | N |
| ATOM | 2629 | CA | ASN | B | 290 | 41.045 | 23.765 | 35.089 | 0.00 | 54.20 | B | C |
| ATOM | 2630 | CB | ASN | B | 290 | 39.766 | 24.085 | 34.318 | 1.00 | 55.61 | B | C |
| ATOM | 2631 | CG | ASN | B | 290 | 40.019 | 24.239 | 32.839 | 1.00 | 56.80 | B | C |
| ATOM | 2632 | OD1 | ASN | B | 290 | 39.293 | 23.680 | 32.009 | 1.00 | 57.54 | B | O |
| ATOM | 2633 | ND2 | ASN | B | 290 | 41.080 | 24.966 | 32.497 | 1.00 | 57.01 | B | N |
| ATOM | 2634 | C | ASN | B | 290 | 40.768 | 23.765 | 36.590 | 1.00 | 54.21 | B | C |
| ATOM | 2635 | O | ASN | B | 290 | 40.820 | 24.806 | 37.237 | 1.00 | 53.84 | B | O |
| ATOM | 2636 | N | LEU | B | 291 | 40.506 | 22.569 | 37.125 | 1.00 | 54.12 | B | N |
| ATOM | 2637 | CA | LEU | B | 291 | 40.260 | 22.347 | 38.553 | 0.00 | 53.85 | B | C |
| ATOM | 2638 | CB | LEU | B | 291 | 39.908 | 20.877 | 38.791 | 1.00 | 53.25 | B | C |
| ATOM | 2639 | CG | LEU | B | 291 | 38.552 | 20.427 | 38.255 | 1.00 | 53.50 | B | C |
| ATOM | 2640 | CD1 | LEU | B | 291 | 38.563 | 18.924 | 38.043 | 1.00 | 53.17 | B | C |
| ATOM | 2641 | CD2 | LEU | B | 291 | 37.445 | 20.861 | 39.228 | 1.00 | 52.72 | B | C |
| ATOM | 2642 | C | LEU | B | 291 | 41.524 | 22.670 | 39.342 | 1.00 | 54.01 | B | C |

Figure 12

| ATOM | 2643 | O | LEU | B | 291 | 41.479 | 23.250 | 40.427 | 1.00 | 53.96 | B | O |
| ATOM | 2644 | N | MET | B | 292 | 42.656 | 22.235 | 38.803 | 1.00 | 54.16 | B | N |
| ATOM | 2645 | CA | MET | B | 292 | 43.945 | 22.492 | 39.426 | 0.00 | 54.12 | B | C |
| ATOM | 2646 | CB | MET | B | 292 | 45.031 | 21.756 | 38.640 | 1.00 | 53.54 | B | C |
| ATOM | 2647 | CG | MET | B | 292 | 45.803 | 20.748 | 39.453 | 1.00 | 53.61 | B | C |
| ATOM | 2648 | SD | MET | B | 292 | 46.634 | 19.494 | 38.463 | 1.00 | 51.90 | B | S |
| ATOM | 2649 | CE | MET | B | 292 | 45.598 | 17.931 | 38.966 | 1.00 | 53.93 | B | C |
| ATOM | 2650 | C | MET | B | 292 | 44.208 | 24.013 | 39.488 | 1.00 | 54.48 | B | C |
| ATOM | 2651 | O | MET | B | 292 | 44.809 | 24.522 | 40.437 | 1.00 | 54.44 | B | O |
| ATOM | 2652 | N | LYS | B | 293 | 43.723 | 24.740 | 38.494 | 1.00 | 55.12 | B | N |
| ATOM | 2653 | CA | LYS | B | 293 | 43.891 | 26.189 | 38.462 | 0.00 | 56.20 | B | C |
| ATOM | 2654 | CB | LYS | B | 293 | 43.293 | 26.766 | 37.174 | 1.00 | 57.21 | B | C |
| ATOM | 2655 | CG | LYS | B | 293 | 43.860 | 26.192 | 35.877 | 1.00 | 59.08 | B | C |
| ATOM | 2656 | CD | LYS | B | 293 | 43.251 | 26.869 | 34.636 | 1.00 | 60.27 | B | C |
| ATOM | 2657 | CE | LYS | B | 293 | 43.960 | 26.383 | 33.371 | 1.00 | 61.15 | B | C |
| ATOM | 2658 | NZ | LYS | B | 293 | 43.566 | 27.166 | 32.173 | 1.00 | 60.68 | B | N |
| ATOM | 2659 | C | LYS | B | 293 | 43.117 | 26.768 | 39.644 | 1.00 | 56.18 | B | C |
| ATOM | 2660 | O | LYS | B | 293 | 43.639 | 27.544 | 40.452 | 1.00 | 56.36 | B | O |
| ATOM | 2661 | N | GLN | B | 294 | 41.872 | 26.312 | 39.761 | 1.00 | 55.84 | B | N |
| ATOM | 2662 | CA | GLN | B | 294 | 40.957 | 26.758 | 40.801 | 0.00 | 55.22 | B | C |
| ATOM | 2663 | CB | GLN | B | 294 | 39.551 | 26.219 | 40.501 | 1.00 | 57.02 | B | C |
| ATOM | 2664 | CG | GLN | B | 294 | 39.086 | 26.470 | 39.034 | 1.00 | 59.28 | B | C |
| ATOM | 2665 | CD | GLN | B | 294 | 39.279 | 27.943 | 38.568 | 1.00 | 61.26 | B | C |
| ATOM | 2666 | OE1 | GLN | B | 294 | 40.077 | 28.248 | 37.658 | 1.00 | 61.57 | B | O |
| ATOM | 2667 | NE2 | GLN | B | 294 | 38.532 | 28.858 | 39.194 | 1.00 | 61.66 | B | N |
| ATOM | 2668 | C | GLN | B | 294 | 41.364 | 26.462 | 42.251 | 1.00 | 53.80 | B | C |
| ATOM | 2669 | O | GLN | B | 294 | 41.322 | 27.355 | 43.105 | 1.00 | 53.64 | B | O |
| ATOM | 2670 | N | LEU | B | 295 | 41.784 | 25.230 | 42.527 | 1.00 | 51.94 | B | N |
| ATOM | 2671 | CA | LEU | B | 295 | 42.176 | 24.836 | 43.886 | 0.00 | 50.06 | B | C |
| ATOM | 2672 | CB | LEU | B | 295 | 41.497 | 23.532 | 44.252 | 1.00 | 50.30 | B | C |
| ATOM | 2673 | CG | LEU | B | 295 | 39.994 | 23.596 | 44.353 | 1.00 | 49.64 | B | C |
| ATOM | 2674 | CD1 | LEU | B | 295 | 39.474 | 22.201 | 44.614 | 1.00 | 50.30 | B | C |
| ATOM | 2675 | CD2 | LEU | B | 295 | 39.645 | 24.552 | 45.490 | 1.00 | 49.99 | B | C |
| ATOM | 2676 | C | LEU | B | 295 | 43.657 | 24.650 | 44.113 | 1.00 | 48.71 | B | C |
| ATOM | 2677 | O | LEU | B | 295 | 44.219 | 23.645 | 43.675 | 1.00 | 49.27 | B | O |
| ATOM | 2678 | N | GLN | B | 296 | 44.262 | 25.547 | 44.885 | 1.00 | 46.67 | B | N |
| ATOM | 2679 | CA | GLN | B | 296 | 45.681 | 25.462 | 45.194 | 0.00 | 44.65 | B | C |
| ATOM | 2680 | CB | GLN | B | 296 | 46.424 | 26.676 | 44.654 | 1.00 | 45.83 | B | C |
| ATOM | 2681 | CG | GLN | B | 296 | 46.215 | 26.873 | 43.177 | 1.00 | 47.70 | B | C |
| ATOM | 2682 | CD | GLN | B | 296 | 46.902 | 28.118 | 42.654 | 1.00 | 49.77 | B | C |
| ATOM | 2683 | OE1 | GLN | B | 296 | 47.709 | 28.749 | 43.363 | 1.00 | 49.33 | B | O |
| ATOM | 2684 | NE2 | GLN | B | 296 | 46.623 | 28.457 | 41.395 | 1.00 | 50.20 | B | N |
| ATOM | 2685 | C | GLN | B | 296 | 45.940 | 25.297 | 46.679 | 1.00 | 43.02 | B | C |
| ATOM | 2686 | O | GLN | B | 296 | 45.331 | 25.994 | 47.506 | 1.00 | 42.40 | B | O |
| ATOM | 2687 | N | HIS | B | 297 | 46.886 | 24.412 | 47.018 | 1.00 | 40.60 | B | N |
| ATOM | 2688 | CA | HIS | B | 297 | 47.195 | 24.120 | 48.412 | 0.00 | 38.83 | B | C |
| ATOM | 2689 | CB | HIS | B | 297 | 45.977 | 23.399 | 49.021 | 1.00 | 36.64 | B | C |
| ATOM | 2690 | CG | HIS | B | 297 | 45.992 | 23.301 | 50.520 | 1.00 | 32.55 | B | C |
| ATOM | 2691 | CD2 | HIS | B | 297 | 45.408 | 24.063 | 51.465 | 1.00 | 31.45 | B | C |
| ATOM | 2692 | ND1 | HIS | B | 297 | 46.673 | 22.299 | 51.191 | 1.00 | 32.58 | B | N |
| ATOM | 2693 | CE1 | HIS | B | 297 | 46.501 | 22.461 | 52.494 | 1.00 | 32.02 | B | C |
| ATOM | 2694 | NE2 | HIS | B | 297 | 45.737 | 23.520 | 52.689 | 1.00 | 32.44 | B | N |
| ATOM | 2695 | C | HIS | B | 297 | 48.456 | 23.238 | 48.521 | 1.00 | 38.86 | B | C |
| ATOM | 2696 | O | HIS | B | 297 | 48.771 | 22.475 | 47.606 | 1.00 | 39.06 | B | O |
| ATOM | 2697 | N | GLN | B | 298 | 49.165 | 23.330 | 49.638 | 1.00 | 38.99 | B | N |
| ATOM | 2698 | CA | GLN | B | 298 | 50.370 | 22.534 | 49.818 | 0.00 | 39.58 | B | C |
| ATOM | 2699 | CB | GLN | B | 298 | 51.126 | 22.881 | 51.120 | 1.00 | 42.13 | B | C |
| ATOM | 2700 | CG | GLN | B | 298 | 52.139 | 24.091 | 50.996 | 1.00 | 46.25 | B | C |
| ATOM | 2701 | CD | GLN | B | 298 | 53.031 | 24.062 | 49.714 | 1.00 | 48.71 | B | C |

Figure 12

| ATOM | 2702 | OE1 | GLN | B | 298 | 52.989 | 24.998 | 48.893 | 1.00 | 49.55 | B | O |
| --- | --- | --- | --- | --- | --- | --- | --- | --- | --- | --- | --- | --- |
| ATOM | 2703 | NE2 | GLN | B | 298 | 53.796 | 22.971 | 49.529 | 1.00 | 49.64 | B | N |
| ATOM | 2704 | C | GLN | B | 298 | 50.152 | 21.040 | 49.766 | 1.00 | 38.81 | B | C |
| ATOM | 2705 | O | GLN | B | 298 | 51.093 | 20.288 | 49.480 | 1.00 | 39.14 | B | O |
| ATOM | 2706 | N | ARG | B | 299 | 48.928 | 20.603 | 50.068 | 1.00 | 36.74 | B | N |
| ATOM | 2707 | CA | ARG | B | 299 | 48.626 | 19.178 | 50.056 | 0.00 | 35.47 | B | C |
| ATOM | 2708 | CB | ARG | B | 299 | 47.665 | 18.833 | 51.182 | 1.00 | 37.03 | B | C |
| ATOM | 2709 | CG | ARG | B | 299 | 48.299 | 18.944 | 52.513 | 1.00 | 40.01 | B | C |
| ATOM | 2710 | CD | ARG | B | 299 | 49.450 | 17.988 | 52.611 | 1.00 | 42.62 | B | C |
| ATOM | 2711 | NE | ARG | B | 299 | 50.414 | 18.488 | 53.566 | 1.00 | 45.72 | B | N |
| ATOM | 2712 | CZ | ARG | B | 299 | 51.728 | 18.484 | 53.357 | 1.00 | 48.62 | B | C |
| ATOM | 2713 | NH1 | ARG | B | 299 | 52.254 | 17.985 | 52.208 | 1.00 | 49.40 | B | N |
| ATOM | 2714 | NH2 | ARG | B | 299 | 52.511 | 19.001 | 54.299 | 1.00 | 48.18 | B | N |
| ATOM | 2715 | C | ARG | B | 299 | 48.052 | 18.693 | 48.742 | 1.00 | 33.93 | B | C |
| ATOM | 2716 | O | ARG | B | 299 | 47.639 | 17.539 | 48.615 | 1.00 | 33.58 | B | O |
| ATOM | 2717 | N | LEU | B | 300 | 48.017 | 19.582 | 47.760 | 1.00 | 32.16 | B | N |
| ATOM | 2718 | CA | LEU | B | 300 | 47.474 | 19.243 | 46.454 | 0.00 | 30.60 | B | C |
| ATOM | 2719 | CB | LEU | B | 300 | 46.291 | 20.169 | 46.144 | 1.00 | 28.58 | B | C |
| ATOM | 2720 | CG | LEU | B | 300 | 44.848 | 19.793 | 46.564 | 1.00 | 28.02 | B | C |
| ATOM | 2721 | CD1 | LEU | B | 300 | 44.749 | 19.384 | 48.023 | 1.00 | 24.37 | B | C |
| ATOM | 2722 | CD2 | LEU | B | 300 | 43.954 | 20.987 | 46.300 | 1.00 | 25.82 | B | C |
| ATOM | 2723 | C | LEU | B | 300 | 48.527 | 19.380 | 45.364 | 1.00 | 30.83 | B | C |
| ATOM | 2724 | O | LEU | B | 300 | 49.290 | 20.335 | 45.379 | 1.00 | 31.52 | B | O |
| ATOM | 2725 | N | VAL | B | 301 | 48.585 | 18.418 | 44.455 | 1.00 | 31.35 | B | N |
| ATOM | 2726 | CA | VAL | B | 301 | 49.502 | 18.461 | 43.320 | 0.00 | 32.93 | B | C |
| ATOM | 2727 | CB | VAL | B | 301 | 49.366 | 17.172 | 42.466 | 1.00 | 32.05 | B | C |
| ATOM | 2728 | CG1 | VAL | B | 301 | 49.884 | 17.366 | 41.050 | 1.00 | 32.99 | B | C |
| ATOM | 2729 | CG2 | VAL | B | 301 | 50.156 | 16.051 | 43.123 | 1.00 | 30.41 | B | C |
| ATOM | 2730 | C | VAL | B | 301 | 49.202 | 19.749 | 42.507 | 1.00 | 34.87 | B | C |
| ATOM | 2731 | O | VAL | B | 301 | 48.073 | 20.000 | 42.104 | 1.00 | 35.07 | B | O |
| ATOM | 2732 | N | ARG | B | 302 | 50.223 | 20.598 | 42.363 | 1.00 | 36.74 | B | N |
| ATOM | 2733 | CA | ARG | B | 302 | 50.126 | 21.880 | 41.666 | 0.00 | 39.02 | B | C |
| ATOM | 2734 | CB | ARG | B | 302 | 51.157 | 22.831 | 42.290 | 1.00 | 42.92 | B | C |
| ATOM | 2735 | CG | ARG | B | 302 | 51.286 | 24.202 | 41.658 | 1.00 | 48.53 | B | C |
| ATOM | 2736 | CD | ARG | B | 302 | 52.509 | 24.219 | 40.724 | 1.00 | 53.83 | B | C |
| ATOM | 2737 | NE | ARG | B | 302 | 53.087 | 25.558 | 40.496 | 1.00 | 57.60 | B | N |
| ATOM | 2738 | CZ | ARG | B | 302 | 53.939 | 26.159 | 41.332 | 1.00 | 59.66 | B | C |
| ATOM | 2739 | NH1 | ARG | B | 302 | 54.305 | 25.550 | 42.461 | 1.00 | 61.12 | B | N |
| ATOM | 2740 | NH2 | ARG | B | 302 | 54.533 | 27.298 | 40.986 | 1.00 | 60.15 | B | N |
| ATOM | 2741 | C | ARG | B | 302 | 50.285 | 21.809 | 40.142 | 1.00 | 38.55 | B | C |
| ATOM | 2742 | O | ARG | B | 302 | 51.070 | 21.019 | 39.606 | 1.00 | 38.91 | B | O |
| ATOM | 2743 | N | LEU | B | 303 | 49.526 | 22.641 | 39.447 | 1.00 | 38.09 | B | N |
| ATOM | 2744 | CA | LEU | B | 303 | 49.565 | 22.720 | 37.981 | 0.00 | 38.80 | B | C |
| ATOM | 2745 | CB | LEU | B | 303 | 48.170 | 23.087 | 37.409 | 1.00 | 37.17 | B | C |
| ATOM | 2746 | CG | LEU | B | 303 | 48.182 | 23.330 | 35.894 | 1.00 | 37.51 | B | C |
| ATOM | 2747 | CD1 | LEU | B | 303 | 48.238 | 21.995 | 35.148 | 1.00 | 35.43 | B | C |
| ATOM | 2748 | CD2 | LEU | B | 303 | 46.999 | 24.214 | 35.418 | 1.00 | 36.11 | B | C |
| ATOM | 2749 | C | LEU | B | 303 | 50.543 | 23.814 | 37.530 | 1.00 | 39.39 | B | C |
| ATOM | 2750 | O | LEU | B | 303 | 50.485 | 24.921 | 38.031 | 1.00 | 40.05 | B | O |
| ATOM | 2751 | N | TYR | B | 304 | 51.444 | 23.493 | 36.603 | 1.00 | 39.69 | B | N |
| ATOM | 2752 | CA | TYR | B | 304 | 52.375 | 24.498 | 36.071 | 0.00 | 40.01 | B | C |
| ATOM | 2753 | CB | TYR | B | 304 | 53.778 | 23.907 | 35.809 | 1.00 | 42.18 | B | C |
| ATOM | 2754 | CG | TYR | B | 304 | 54.576 | 23.674 | 37.058 | 1.00 | 44.11 | B | C |
| ATOM | 2755 | CD1 | TYR | B | 304 | 55.168 | 22.440 | 37.316 | 1.00 | 45.61 | B | C |
| ATOM | 2756 | CE1 | TYR | B | 304 | 55.834 | 22.192 | 38.523 | 1.00 | 46.52 | B | C |
| ATOM | 2757 | CD2 | TYR | B | 304 | 54.677 | 24.657 | 38.024 | 1.00 | 45.95 | B | C |
| ATOM | 2758 | CE2 | TYR | B | 304 | 55.354 | 24.408 | 39.239 | 1.00 | 47.37 | B | C |
| ATOM | 2759 | CZ | TYR | B | 304 | 55.915 | 23.183 | 39.472 | 1.00 | 46.83 | B | C |
| ATOM | 2760 | OH | TYR | B | 304 | 56.527 | 22.962 | 40.668 | 1.00 | 47.99 | B | O |

Figure 12

| ATOM | 2761 | C   | TYR | B | 304 | 51.852 | 25.097 | 34.755 | 1.00 | 38.51 | B | C |
|------|------|-----|-----|---|-----|--------|--------|--------|------|-------|---|---|
| ATOM | 2762 | O   | TYR | B | 304 | 51.780 | 26.311 | 34.603 | 1.00 | 38.27 | B | O |
| ATOM | 2763 | N   | ALA | B | 305 | 51.487 | 24.231 | 33.816 | 1.00 | 37.28 | B | N |
| ATOM | 2764 | CA  | ALA | B | 305 | 51.026 | 24.673 | 32.506 | 0.00 | 35.96 | B | C |
| ATOM | 2765 | CB  | ALA | B | 305 | 52.258 | 25.156 | 31.694 | 1.00 | 35.43 | B | C |
| ATOM | 2766 | C   | ALA | B | 305 | 50.269 | 23.597 | 31.706 | 1.00 | 35.35 | B | C |
| ATOM | 2767 | O   | ALA | B | 305 | 50.119 | 22.437 | 32.148 | 1.00 | 35.13 | B | O |
| ATOM | 2768 | N   | VAL | B | 306 | 49.815 | 24.003 | 30.516 | 1.00 | 34.64 | B | N |
| ATOM | 2769 | CA  | VAL | B | 306 | 49.112 | 23.138 | 29.565 | 0.00 | 33.65 | B | C |
| ATOM | 2770 | CB  | VAL | B | 306 | 47.584 | 23.414 | 29.566 | 1.00 | 34.03 | B | C |
| ATOM | 2771 | CG1 | VAL | B | 306 | 46.918 | 22.904 | 30.877 | 1.00 | 33.77 | B | C |
| ATOM | 2772 | CG2 | VAL | B | 306 | 47.317 | 24.921 | 29.386 | 1.00 | 32.80 | B | C |
| ATOM | 2773 | C   | VAL | B | 306 | 49.594 | 23.426 | 28.132 | 1.00 | 34.17 | B | C |
| ATOM | 2774 | O   | VAL | B | 306 | 50.079 | 24.519 | 27.831 | 1.00 | 33.52 | B | O |
| ATOM | 2775 | N   | VAL | B | 307 | 49.524 | 22.427 | 27.260 | 1.00 | 34.46 | B | N |
| ATOM | 2776 | CA  | VAL | B | 307 | 49.849 | 22.648 | 25.855 | 0.00 | 35.16 | B | C |
| ATOM | 2777 | CB  | VAL | B | 307 | 51.046 | 21.805 | 25.356 | 1.00 | 35.04 | B | C |
| ATOM | 2778 | CG1 | VAL | B | 307 | 51.123 | 21.855 | 23.826 | 1.00 | 33.99 | B | C |
| ATOM | 2779 | CG2 | VAL | B | 307 | 52.333 | 22.330 | 25.984 | 1.00 | 33.75 | B | C |
| ATOM | 2780 | C   | VAL | B | 307 | 48.553 | 22.249 | 25.176 | 1.00 | 36.31 | B | C |
| ATOM | 2781 | O   | VAL | B | 307 | 48.116 | 21.099 | 25.263 | 1.00 | 33.74 | B | O |
| ATOM | 2782 | N   | THR | B | 308 | 47.910 | 23.244 | 24.563 | 1.00 | 38.88 | B | N |
| ATOM | 2783 | CA  | THR | B | 308 | 46.636 | 23.047 | 23.896 | 0.00 | 41.18 | B | C |
| ATOM | 2784 | CB  | THR | B | 308 | 45.800 | 24.312 | 23.942 | 1.00 | 40.48 | B | C |
| ATOM | 2785 | OG1 | THR | B | 308 | 46.595 | 25.427 | 23.530 | 1.00 | 40.90 | B | O |
| ATOM | 2786 | CG2 | THR | B | 308 | 45.344 | 24.559 | 25.357 | 1.00 | 39.42 | B | C |
| ATOM | 2787 | C   | THR | B | 308 | 46.659 | 22.446 | 22.505 | 1.00 | 43.46 | B | C |
| ATOM | 2788 | O   | THR | B | 308 | 45.628 | 21.978 | 22.035 | 1.00 | 44.35 | B | O |
| ATOM | 2789 | N   | GLN | B | 309 | 47.816 | 22.423 | 21.851 | 1.00 | 45.60 | B | N |
| ATOM | 2790 | CA  | GLN | B | 309 | 47.910 | 21.813 | 20.518 | 0.00 | 47.85 | B | C |
| ATOM | 2791 | CB  | GLN | B | 309 | 49.035 | 22.440 | 19.687 | 1.00 | 51.48 | B | C |
| ATOM | 2792 | CG  | GLN | B | 309 | 48.763 | 23.876 | 19.222 | 1.00 | 58.16 | B | C |
| ATOM | 2793 | CD  | GLN | B | 309 | 47.488 | 24.007 | 18.357 | 1.00 | 61.65 | B | C |
| ATOM | 2794 | OE1 | GLN | B | 309 | 46.951 | 22.999 | 17.845 | 1.00 | 63.69 | B | O |
| ATOM | 2795 | NE2 | GLN | B | 309 | 47.013 | 25.246 | 18.189 | 1.00 | 63.41 | B | N |
| ATOM | 2796 | C   | GLN | B | 309 | 48.219 | 20.354 | 20.701 | 1.00 | 47.28 | B | C |
| ATOM | 2797 | O   | GLN | B | 309 | 49.018 | 20.014 | 21.566 | 1.00 | 47.30 | B | O |
| ATOM | 2798 | N   | GLU | B | 310 | 47.639 | 19.501 | 19.868 | 1.00 | 46.58 | B | N |
| ATOM | 2799 | CA  | GLU | B | 310 | 47.875 | 18.067 | 19.966 | 0.00 | 46.97 | B | C |
| ATOM | 2800 | CB  | GLU | B | 310 | 46.886 | 17.262 | 19.090 | 1.00 | 49.87 | B | C |
| ATOM | 2801 | CG  | GLU | B | 310 | 46.733 | 17.757 | 17.644 | 1.00 | 55.41 | B | C |
| ATOM | 2802 | CD  | GLU | B | 310 | 45.749 | 18.945 | 17.469 | 1.00 | 58.36 | B | C |
| ATOM | 2803 | OE1 | GLU | B | 310 | 44.526 | 18.665 | 17.387 | 1.00 | 59.13 | B | O |
| ATOM | 2804 | OE2 | GLU | B | 310 | 46.195 | 20.133 | 17.373 | 1.00 | 59.10 | B | O |
| ATOM | 2805 | C   | GLU | B | 310 | 49.311 | 17.651 | 19.647 | 1.00 | 45.06 | B | C |
| ATOM | 2806 | O   | GLU | B | 310 | 49.930 | 18.190 | 18.717 | 1.00 | 45.12 | B | O |
| ATOM | 2807 | N   | PRO | B | 311 | 49.886 | 16.734 | 20.456 | 1.00 | 42.89 | B | N |
| ATOM | 2808 | CD  | PRO | B | 311 | 51.261 | 16.258 | 20.224 | 1.00 | 42.71 | B | C |
| ATOM | 2809 | CA  | PRO | B | 311 | 49.308 | 16.044 | 21.624 | 0.00 | 40.48 | B | C |
| ATOM | 2810 | CB  | PRO | B | 311 | 50.399 | 15.022 | 21.986 | 1.00 | 41.85 | B | C |
| ATOM | 2811 | CG  | PRO | B | 311 | 51.181 | 14.852 | 20.712 | 1.00 | 42.40 | B | C |
| ATOM | 2812 | C   | PRO | B | 311 | 49.058 | 16.985 | 22.818 | 1.00 | 37.91 | B | C |
| ATOM | 2813 | O   | PRO | B | 311 | 49.943 | 17.756 | 23.193 | 1.00 | 37.75 | B | O |
| ATOM | 2814 | N   | ILE | B | 312 | 47.859 | 16.909 | 23.417 | 1.00 | 35.66 | B | N |
| ATOM | 2815 | CA  | ILE | B | 312 | 47.531 | 17.783 | 24.562 | 0.00 | 32.09 | B | C |
| ATOM | 2816 | CB  | ILE | B | 312 | 46.035 | 17.727 | 24.952 | 1.00 | 32.70 | B | C |
| ATOM | 2817 | CG2 | ILE | B | 312 | 45.695 | 18.941 | 25.812 | 1.00 | 32.11 | B | C |
| ATOM | 2818 | CG1 | ILE | B | 312 | 45.136 | 17.731 | 23.712 | 1.00 | 32.97 | B | C |
| ATOM | 2819 | CD1 | ILE | B | 312 | 44.892 | 19.126 | 23.126 | 1.00 | 33.15 | B | C |

Figure 12

| | | | | | | | | | | | |
|---|---|---|---|---|---|---|---|---|---|---|---|
| ATOM | 2820 | C   | ILE | B | 312 | 48.363 | 17.377 | 25.777 | 1.00 | 29.29 | B | C |
| ATOM | 2821 | O   | ILE | B | 312 | 48.532 | 16.186 | 26.063 | 1.00 | 27.45 | B | O |
| ATOM | 2822 | N   | TYR | B | 313 | 48.893 | 18.383 | 26.453 | 1.00 | 27.47 | B | N |
| ATOM | 2823 | CA  | TYR | B | 313 | 49.734 | 18.190 | 27.643 | 0.00 | 27.16 | B | C |
| ATOM | 2824 | CB  | TYR | B | 313 | 51.156 | 18.820 | 27.446 | 1.00 | 27.32 | B | C |
| ATOM | 2825 | CG  | TYR | B | 313 | 52.186 | 18.081 | 26.604 | 1.00 | 26.62 | B | C |
| ATOM | 2826 | CD1 | TYR | B | 313 | 51.916 | 16.819 | 26.064 | 1.00 | 25.67 | B | C |
| ATOM | 2827 | CE1 | TYR | B | 313 | 52.844 | 16.160 | 25.248 | 1.00 | 26.63 | B | C |
| ATOM | 2828 | CD2 | TYR | B | 313 | 53.440 | 18.680 | 26.314 | 1.00 | 27.78 | B | C |
| ATOM | 2829 | CE2 | TYR | B | 313 | 54.391 | 18.022 | 25.468 | 1.00 | 26.79 | B | C |
| ATOM | 2830 | CZ  | TYR | B | 313 | 54.074 | 16.767 | 24.941 | 1.00 | 27.30 | B | C |
| ATOM | 2831 | OH  | TYR | B | 313 | 54.945 | 16.129 | 24.058 | 1.00 | 27.78 | B | O |
| ATOM | 2832 | C   | TYR | B | 313 | 49.196 | 18.900 | 28.865 | 1.00 | 26.39 | B | C |
| ATOM | 2833 | O   | TYR | B | 313 | 48.670 | 19.999 | 28.750 | 1.00 | 25.26 | B | O |
| ATOM | 2834 | N   | ILE | B | 314 | 49.451 | 18.302 | 30.038 | 1.00 | 25.54 | B | N |
| ATOM | 2835 | CA  | ILE | B | 314 | 49.137 | 18.910 | 31.341 | 0.00 | 25.28 | B | C |
| ATOM | 2836 | CB  | ILE | B | 314 | 47.991 | 18.179 | 32.163 | 1.00 | 26.05 | B | C |
| ATOM | 2837 | CG2 | ILE | B | 314 | 47.819 | 18.838 | 33.532 | 1.00 | 24.02 | B | C |
| ATOM | 2838 | CG1 | ILE | B | 314 | 46.653 | 18.244 | 31.426 | 1.00 | 26.10 | B | C |
| ATOM | 2839 | CD1 | ILE | B | 314 | 45.459 | 17.509 | 32.155 | 1.00 | 25.77 | B | C |
| ATOM | 2840 | C   | ILE | B | 314 | 50.476 | 18.767 | 32.092 | 1.00 | 25.04 | B | C |
| ATOM | 2841 | O   | ILE | B | 314 | 51.032 | 17.663 | 32.253 | 1.00 | 24.32 | B | O |
| ATOM | 2842 | N   | ILE | B | 315 | 50.966 | 19.875 | 32.615 | 1.00 | 25.33 | B | N |
| ATOM | 2843 | CA  | ILE | B | 315 | 52.250 | 19.839 | 33.294 | 0.00 | 24.87 | B | C |
| ATOM | 2844 | CB  | ILE | B | 315 | 53.248 | 20.862 | 32.649 | 1.00 | 25.35 | B | C |
| ATOM | 2845 | CG2 | ILE | B | 315 | 54.613 | 20.839 | 33.357 | 1.00 | 25.81 | B | C |
| ATOM | 2846 | CG1 | ILE | B | 315 | 53.430 | 20.540 | 31.173 | 1.00 | 24.15 | B | C |
| ATOM | 2847 | CD1 | ILE | B | 315 | 52.452 | 21.306 | 30.283 | 1.00 | 25.62 | B | C |
| ATOM | 2848 | C   | ILE | B | 315 | 52.083 | 20.152 | 34.753 | 1.00 | 25.39 | B | C |
| ATOM | 2849 | O   | ILE | B | 315 | 51.559 | 21.190 | 35.132 | 1.00 | 26.13 | B | O |
| ATOM | 2850 | N   | THR | B | 316 | 52.615 | 19.287 | 35.595 | 1.00 | 26.15 | B | N |
| ATOM | 2851 | CA  | THR | B | 316 | 52.491 | 19.523 | 37.038 | 0.00 | 27.02 | B | C |
| ATOM | 2852 | CB  | THR | B | 316 | 51.491 | 18.523 | 37.670 | 1.00 | 26.52 | B | C |
| ATOM | 2853 | OG1 | THR | B | 316 | 52.113 | 17.223 | 37.745 | 1.00 | 23.98 | B | O |
| ATOM | 2854 | CG2 | THR | B | 316 | 50.228 | 18.409 | 36.835 | 1.00 | 24.61 | B | C |
| ATOM | 2855 | C   | THR | B | 316 | 53.833 | 19.281 | 37.700 | 1.00 | 27.92 | B | C |
| ATOM | 2856 | O   | THR | B | 316 | 54.735 | 18.707 | 37.095 | 1.00 | 27.50 | B | O |
| ATOM | 2857 | N   | GLU | B | 317 | 53.943 | 19.679 | 38.960 | 1.00 | 28.72 | B | N |
| ATOM | 2858 | CA  | GLU | B | 317 | 55.155 | 19.447 | 39.720 | 0.00 | 28.87 | B | C |
| ATOM | 2859 | CB  | GLU | B | 317 | 54.959 | 19.888 | 41.167 | 1.00 | 30.89 | B | C |
| ATOM | 2860 | CG  | GLU | B | 317 | 53.970 | 19.073 | 42.019 | 1.00 | 31.80 | B | C |
| ATOM | 2861 | CD  | GLU | B | 317 | 53.842 | 19.667 | 43.423 | 1.00 | 33.09 | B | C |
| ATOM | 2862 | OE1 | GLU | B | 317 | 52.732 | 20.138 | 43.778 | 1.00 | 34.82 | B | O |
| ATOM | 2863 | OE2 | GLU | B | 317 | 54.847 | 19.709 | 44.161 | 1.00 | 33.03 | B | O |
| ATOM | 2864 | C   | GLU | B | 317 | 55.455 | 17.960 | 39.652 | 1.00 | 29.15 | B | C |
| ATOM | 2865 | O   | GLU | B | 317 | 54.563 | 17.145 | 39.431 | 1.00 | 29.53 | B | O |
| ATOM | 2866 | N   | TYR | B | 318 | 56.726 | 17.614 | 39.744 | 1.00 | 28.34 | B | N |
| ATOM | 2867 | CA  | TYR | B | 318 | 57.121 | 16.230 | 39.662 | 0.00 | 28.69 | B | C |
| ATOM | 2868 | CB  | TYR | B | 318 | 58.513 | 16.157 | 38.994 | 1.00 | 28.11 | B | C |
| ATOM | 2869 | CG  | TYR | B | 318 | 59.096 | 14.796 | 38.957 | 1.00 | 26.70 | B | C |
| ATOM | 2870 | CD1 | TYR | B | 318 | 58.590 | 13.822 | 38.121 | 1.00 | 26.71 | B | C |
| ATOM | 2871 | CE1 | TYR | B | 318 | 59.124 | 12.530 | 38.132 | 1.00 | 27.34 | B | C |
| ATOM | 2872 | CD2 | TYR | B | 318 | 60.143 | 14.446 | 39.805 | 1.00 | 27.17 | B | C |
| ATOM | 2873 | CE2 | TYR | B | 318 | 60.659 | 13.180 | 39.809 | 1.00 | 26.25 | B | C |
| ATOM | 2874 | CZ  | TYR | B | 318 | 60.154 | 12.248 | 38.980 | 1.00 | 27.11 | B | C |
| ATOM | 2875 | OH  | TYR | B | 318 | 60.705 | 10.990 | 39.010 | 1.00 | 32.99 | B | O |
| ATOM | 2876 | C   | TYR | B | 318 | 57.142 | 15.648 | 41.071 | 1.00 | 29.03 | B | C |
| ATOM | 2877 | O   | TYR | B | 318 | 57.504 | 16.349 | 42.003 | 1.00 | 29.52 | B | O |
| ATOM | 2878 | N   | MET | B | 319 | 56.696 | 14.401 | 41.238 | 1.00 | 29.76 | B | N |

Figure 12

| ATOM | 2879 | CA  | MET B 319 | 56.697 | 13.761 | 42.564 | 0.00 | 31.80 | B | C |
|------|------|-----|-----------|--------|--------|--------|------|-------|---|---|
| ATOM | 2880 | CB  | MET B 319 | 55.269 | 13.361 | 43.000 | 1.00 | 32.69 | B | C |
| ATOM | 2881 | CG  | MET B 319 | 54.328 | 14.580 | 43.245 | 1.00 | 32.46 | B | C |
| ATOM | 2882 | SD  | MET B 319 | 54.735 | 15.643 | 44.668 | 1.00 | 34.16 | B | S |
| ATOM | 2883 | CE  | MET B 319 | 53.761 | 14.820 | 45.921 | 1.00 | 33.02 | B | C |
| ATOM | 2884 | C   | MET B 319 | 57.633 | 12.560 | 42.533 | 1.00 | 32.63 | B | C |
| ATOM | 2885 | O   | MET B 319 | 57.270 | 11.473 | 42.041 | 1.00 | 31.98 | B | O |
| ATOM | 2886 | N   | GLU B 320 | 58.819 | 12.788 | 43.101 | 1.00 | 33.75 | B | N |
| ATOM | 2887 | CA  | GLU B 320 | 59.921 | 11.829 | 43.130 | 0.00 | 34.75 | B | C |
| ATOM | 2888 | CB  | GLU B 320 | 60.975 | 12.326 | 44.119 | 1.00 | 38.13 | B | C |
| ATOM | 2889 | CG  | GLU B 320 | 62.233 | 11.467 | 44.214 | 1.00 | 43.01 | B | C |
| ATOM | 2890 | CD  | GLU B 320 | 63.062 | 11.500 | 42.927 | 1.00 | 45.30 | B | C |
| ATOM | 2891 | OE1 | GLU B 320 | 63.507 | 12.607 | 42.522 | 1.00 | 45.84 | B | O |
| ATOM | 2892 | OE2 | GLU B 320 | 63.248 | 10.422 | 42.313 | 1.00 | 46.00 | B | O |
| ATOM | 2893 | C   | GLU B 320 | 59.553 | 10.370 | 43.389 | 1.00 | 33.58 | B | C |
| ATOM | 2894 | O   | GLU B 320 | 59.992 |  9.467 | 42.666 | 1.00 | 33.87 | B | O |
| ATOM | 2895 | N   | ASN B 321 | 58.714 | 10.135 | 44.382 | 1.00 | 31.42 | B | N |
| ATOM | 2896 | CA  | ASN B 321 | 58.321 |  8.774 | 44.704 | 0.00 | 30.44 | B | C |
| ATOM | 2897 | CB  | ASN B 321 | 58.379 |  8.584 | 46.211 | 1.00 | 31.35 | B | C |
| ATOM | 2898 | CG  | ASN B 321 | 59.795 |  8.509 | 46.712 | 1.00 | 32.29 | B | C |
| ATOM | 2899 | OD1 | ASN B 321 | 60.587 |  7.697 | 46.213 | 1.00 | 33.02 | B | O |
| ATOM | 2900 | ND2 | ASN B 321 | 60.135 |  9.342 | 47.685 | 1.00 | 32.09 | B | N |
| ATOM | 2901 | C   | ASN B 321 | 57.030 |  8.215 | 44.092 | 1.00 | 28.98 | B | C |
| ATOM | 2902 | O   | ASN B 321 | 56.562 |  7.120 | 44.454 | 1.00 | 28.40 | B | O |
| ATOM | 2903 | N   | GLY B 322 | 56.496 |  8.928 | 43.109 | 1.00 | 28.56 | B | N |
| ATOM | 2904 | CA  | GLY B 322 | 55.294 |  8.469 | 42.427 | 0.00 | 28.22 | B | C |
| ATOM | 2905 | C   | GLY B 322 | 54.001 |  8.256 | 43.230 | 1.00 | 28.49 | B | C |
| ATOM | 2906 | O   | GLY B 322 | 53.669 |  9.002 | 44.149 | 1.00 | 27.87 | B | O |
| ATOM | 2907 | N   | SER B 323 | 53.280 |  7.211 | 42.850 | 1.00 | 28.31 | B | N |
| ATOM | 2908 | CA  | SER B 323 | 52.004 |  6.851 | 43.452 | 0.00 | 28.56 | B | C |
| ATOM | 2909 | CB  | SER B 323 | 51.284 |  5.943 | 42.469 | 1.00 | 28.80 | B | C |
| ATOM | 2910 | OG  | SER B 323 | 50.064 |  5.527 | 42.989 | 1.00 | 32.38 | B | O |
| ATOM | 2911 | C   | SER B 323 | 52.117 |  6.165 | 44.823 | 1.00 | 27.91 | B | C |
| ATOM | 2912 | O   | SER B 323 | 52.844 |  5.175 | 44.973 | 1.00 | 26.96 | B | O |
| ATOM | 2913 | N   | LEU B 324 | 51.389 |  6.681 | 45.812 | 1.00 | 27.39 | B | N |
| ATOM | 2914 | CA  | LEU B 324 | 51.429 |  6.076 | 47.146 | 0.00 | 26.70 | B | C |
| ATOM | 2915 | CB  | LEU B 324 | 50.539 |  6.830 | 48.143 | 1.00 | 24.99 | B | C |
| ATOM | 2916 | CG  | LEU B 324 | 50.423 |  6.278 | 49.578 | 1.00 | 23.72 | B | C |
| ATOM | 2917 | CD1 | LEU B 324 | 51.635 |  6.716 | 50.423 | 1.00 | 21.12 | B | C |
| ATOM | 2918 | CD2 | LEU B 324 | 49.142 |  6.849 | 50.217 | 1.00 | 24.93 | B | C |
| ATOM | 2919 | C   | LEU B 324 | 51.100 |  4.583 | 47.174 | 1.00 | 26.28 | B | C |
| ATOM | 2920 | O   | LEU B 324 | 51.731 |  3.833 | 47.899 | 1.00 | 26.48 | B | O |
| ATOM | 2921 | N   | VAL B 325 | 50.158 |  4.119 | 46.365 | 1.00 | 27.14 | B | N |
| ATOM | 2922 | CA  | VAL B 325 | 49.842 |  2.709 | 46.413 | 0.00 | 27.72 | B | C |
| ATOM | 2923 | CB  | VAL B 325 | 48.597 |  2.350 | 45.592 | 1.00 | 27.90 | B | C |
| ATOM | 2924 | CG1 | VAL B 325 | 48.891 |  2.395 | 44.082 | 1.00 | 27.41 | B | C |
| ATOM | 2925 | CG2 | VAL B 325 | 48.085 |  0.975 | 45.988 | 1.00 | 26.16 | B | C |
| ATOM | 2926 | C   | VAL B 325 | 51.056 |  1.845 | 46.036 | 1.00 | 29.63 | B | C |
| ATOM | 2927 | O   | VAL B 325 | 51.213 |  0.758 | 46.611 | 1.00 | 29.92 | B | O |
| ATOM | 2928 | N   | ASP B 326 | 51.901 |  2.336 | 45.099 | 1.00 | 29.89 | B | N |
| ATOM | 2929 | CA  | ASP B 326 | 53.131 |  1.639 | 44.658 | 0.00 | 31.08 | B | C |
| ATOM | 2930 | CB  | ASP B 326 | 53.672 |  2.230 | 43.353 | 1.00 | 31.94 | B | C |
| ATOM | 2931 | CG  | ASP B 326 | 52.746 |  2.031 | 42.189 | 1.00 | 31.91 | B | C |
| ATOM | 2932 | OD1 | ASP B 326 | 52.110 |  0.968 | 42.080 | 1.00 | 31.73 | B | O |
| ATOM | 2933 | OD2 | ASP B 326 | 52.695 |  2.958 | 41.351 | 1.00 | 33.05 | B | O |
| ATOM | 2934 | C   | ASP B 326 | 54.273 |  1.813 | 45.698 | 1.00 | 31.96 | B | C |
| ATOM | 2935 | O   | ASP B 326 | 54.990 |  0.853 | 46.042 | 1.00 | 32.00 | B | O |
| ATOM | 2936 | N   | PHE B 327 | 54.443 |  3.046 | 46.168 | 1.00 | 30.83 | B | N |
| ATOM | 2937 | CA  | PHE B 327 | 55.478 |  3.352 | 47.128 | 0.00 | 31.80 | B | C |

Figure 12

| | | | | | | | | | | | |
|---|---|---|---|---|---|---|---|---|---|---|---|
| ATOM | 2938 | CB | PHE | B | 327 | 55.445 | 4.830 | 47.493 | 1.00 | 31.17 | B C |
| ATOM | 2939 | CG | PHE | B | 327 | 56.459 | 5.204 | 48.521 | 1.00 | 32.10 | B C |
| ATOM | 2940 | CD1 | PHE | B | 327 | 57.821 | 5.112 | 48.236 | 1.00 | 32.54 | B C |
| ATOM | 2941 | CD2 | PHE | B | 327 | 56.061 | 5.621 | 49.790 | 1.00 | 32.23 | B C |
| ATOM | 2942 | CE1 | PHE | B | 327 | 58.766 | 5.425 | 49.196 | 1.00 | 33.10 | B C |
| ATOM | 2943 | CE2 | PHE | B | 327 | 56.985 | 5.934 | 50.755 | 1.00 | 32.25 | B C |
| ATOM | 2944 | CZ | PHE | B | 327 | 58.348 | 5.838 | 50.468 | 1.00 | 32.94 | B C |
| ATOM | 2945 | C | PHE | B | 327 | 55.427 | 2.518 | 48.401 | 1.00 | 32.71 | B C |
| ATOM | 2946 | O | PHE | B | 327 | 56.470 | 2.080 | 48.921 | 1.00 | 32.57 | B O |
| ATOM | 2947 | N | LEU | B | 328 | 54.221 | 2.340 | 48.925 | 1.00 | 32.99 | B N |
| ATOM | 2948 | CA | LEU | B | 328 | 54.027 | 1.563 | 50.137 | 0.00 | 33.85 | B C |
| ATOM | 2949 | CB | LEU | B | 328 | 52.548 | 1.518 | 50.514 | 1.00 | 33.69 | B C |
| ATOM | 2950 | CG | LEU | B | 328 | 51.887 | 2.829 | 50.947 | 1.00 | 34.37 | B C |
| ATOM | 2951 | CD1 | LEU | B | 328 | 50.410 | 2.653 | 51.030 | 1.00 | 35.63 | B C |
| ATOM | 2952 | CD2 | LEU | B | 328 | 52.417 | 3.277 | 52.284 | 1.00 | 33.69 | B C |
| ATOM | 2953 | C | LEU | B | 328 | 54.563 | 0.147 | 49.967 | 1.00 | 34.45 | B C |
| ATOM | 2954 | O | LEU | B | 328 | 54.967 | -0.478 | 50.943 | 1.00 | 33.40 | B O |
| ATOM | 2955 | N | LYS | B | 329 | 54.559 | -0.348 | 48.729 | 1.00 | 36.43 | B N |
| ATOM | 2956 | CA | LYS | B | 329 | 55.029 | -1.701 | 48.433 | 0.00 | 38.42 | B C |
| ATOM | 2957 | CB | LYS | B | 329 | 54.319 | -2.290 | 47.209 | 1.00 | 38.65 | B C |
| ATOM | 2958 | CG | LYS | B | 329 | 52.809 | -2.333 | 47.277 | 1.00 | 39.36 | B C |
| ATOM | 2959 | CD | LYS | B | 329 | 52.270 | -3.209 | 46.161 | 1.00 | 40.95 | B C |
| ATOM | 2960 | CE | LYS | B | 329 | 50.734 | -3.160 | 46.041 | 1.00 | 41.95 | B C |
| ATOM | 2961 | NZ | LYS | B | 329 | 50.254 | -1.777 | 45.765 | 1.00 | 43.13 | B N |
| ATOM | 2962 | C | LYS | B | 329 | 56.551 | -1.788 | 48.225 | 1.00 | 39.42 | B C |
| ATOM | 2963 | O | LYS | B | 329 | 57.088 | -2.894 | 48.185 | 1.00 | 39.68 | B O |
| ATOM | 2964 | N | THR | B | 330 | 57.232 | -0.643 | 48.106 | 1.00 | 40.44 | B N |
| ATOM | 2965 | CA | THR | B | 330 | 58.682 | -0.646 | 47.893 | 0.00 | 41.57 | B C |
| ATOM | 2966 | CB | THR | B | 330 | 59.247 | 0.731 | 47.456 | 1.00 | 40.87 | B C |
| ATOM | 2967 | OG1 | THR | B | 330 | 59.148 | 1.655 | 48.533 | 1.00 | 41.17 | B O |
| ATOM | 2968 | CG2 | THR | B | 330 | 58.547 | 1.269 | 46.247 | 1.00 | 40.10 | B C |
| ATOM | 2969 | C | THR | B | 330 | 59.438 | -1.022 | 49.159 | 1.00 | 42.88 | B C |
| ATOM | 2970 | O | THR | B | 330 | 58.852 | -1.133 | 50.233 | 1.00 | 43.35 | B O |
| ATOM | 2971 | N | PRO | B | 331 | 60.739 | -1.334 | 49.023 | 1.00 | 43.97 | B N |
| ATOM | 2972 | CD | PRO | B | 331 | 61.424 | -1.807 | 47.794 | 1.00 | 43.94 | B C |
| ATOM | 2973 | CA | PRO | B | 331 | 61.526 | -1.690 | 50.208 | 0.00 | 44.30 | B C |
| ATOM | 2974 | CB | PRO | B | 331 | 62.915 | -1.970 | 49.605 | 1.00 | 43.91 | B C |
| ATOM | 2975 | CG | PRO | B | 331 | 62.534 | -2.713 | 48.352 | 1.00 | 43.74 | B C |
| ATOM | 2976 | C | PRO | B | 331 | 61.538 | -0.573 | 51.251 | 1.00 | 44.02 | B C |
| ATOM | 2977 | O | PRO | B | 331 | 61.455 | -0.843 | 52.444 | 1.00 | 44.17 | B O |
| ATOM | 2978 | N | SER | B | 332 | 61.600 | 0.672 | 50.805 | 1.00 | 44.08 | B N |
| ATOM | 2979 | CA | SER | B | 332 | 61.617 | 1.802 | 51.735 | 0.00 | 45.23 | B C |
| ATOM | 2980 | CB | SER | B | 332 | 62.149 | 3.067 | 51.045 | 1.00 | 46.47 | B C |
| ATOM | 2981 | OG | SER | B | 332 | 63.519 | 2.944 | 50.727 | 1.00 | 48.55 | B O |
| ATOM | 2982 | C | SER | B | 332 | 60.239 | 2.128 | 52.354 | 1.00 | 44.62 | B C |
| ATOM | 2983 | O | SER | B | 332 | 60.153 | 2.691 | 53.446 | 1.00 | 44.39 | B O |
| ATOM | 2984 | N | GLY | B | 333 | 59.170 | 1.818 | 51.623 | 1.00 | 44.17 | B N |
| ATOM | 2985 | CA | GLY | B | 333 | 57.834 | 2.085 | 52.113 | 0.00 | 43.62 | B C |
| ATOM | 2986 | C | GLY | B | 333 | 57.432 | 1.026 | 53.101 | 1.00 | 43.13 | B C |
| ATOM | 2987 | O | GLY | B | 333 | 56.791 | 1.325 | 54.096 | 1.00 | 42.61 | B O |
| ATOM | 2988 | N | ILE | B | 334 | 57.817 | -0.214 | 52.826 | 1.00 | 43.58 | B N |
| ATOM | 2989 | CA | ILE | B | 334 | 57.515 | -1.332 | 53.716 | 0.00 | 44.00 | B C |
| ATOM | 2990 | CB | ILE | B | 334 | 58.048 | -2.669 | 53.140 | 1.00 | 44.92 | B C |
| ATOM | 2991 | CG2 | ILE | B | 334 | 58.107 | -3.770 | 54.245 | 1.00 | 45.13 | B C |
| ATOM | 2992 | CG1 | ILE | B | 334 | 57.147 | -3.150 | 52.003 | 1.00 | 45.86 | B C |
| ATOM | 2993 | CD1 | ILE | B | 334 | 55.896 | -3.926 | 52.464 | 1.00 | 45.93 | B C |
| ATOM | 2994 | C | ILE | B | 334 | 58.133 | -1.115 | 55.107 | 1.00 | 44.05 | B C |
| ATOM | 2995 | O | ILE | B | 334 | 57.599 | -1.605 | 56.118 | 1.00 | 44.22 | B O |
| ATOM | 2996 | N | LYS | B | 335 | 59.220 | -0.349 | 55.168 | 1.00 | 43.72 | B N |

Figure 12

| | | | | | | | | | | | |
|---|---|---|---|---|---|---|---|---|---|---|---|
| ATOM | 2997 | CA | LYS | B | 335 | 59.915 | -0.097 | 56.437 | 0.00 | 43.26 | B | C |
| ATOM | 2998 | CB | LYS | B | 335 | 61.422 | 0.027 | 56.182 | 1.00 | 45.41 | B | C |
| ATOM | 2999 | CG | LYS | B | 335 | 62.056 | -1.198 | 55.490 | 1.00 | 47.82 | B | C |
| ATOM | 3000 | CD | LYS | B | 335 | 63.551 | -0.912 | 55.176 | 1.00 | 50.81 | B | C |
| ATOM | 3001 | CE | LYS | B | 335 | 64.156 | -1.982 | 54.241 | 1.00 | 53.10 | B | C |
| ATOM | 3002 | NZ | LYS | B | 335 | 65.061 | -1.406 | 53.172 | 1.00 | 54.73 | B | N |
| ATOM | 3003 | C | LYS | B | 335 | 59.411 | 1.110 | 57.240 | 1.00 | 41.85 | B | C |
| ATOM | 3004 | O | LYS | B | 335 | 59.956 | 1.436 | 58.293 | 1.00 | 41.41 | B | O |
| ATOM | 3005 | N | LEU | B | 336 | 58.397 | 1.798 | 56.724 | 1.00 | 41.00 | B | N |
| ATOM | 3006 | CA | LEU | B | 336 | 57.811 | 2.967 | 57.401 | 0.00 | 39.87 | B | C |
| ATOM | 3007 | CB | LEU | B | 336 | 56.784 | 3.669 | 56.494 | 1.00 | 40.00 | B | C |
| ATOM | 3008 | CG | LEU | B | 336 | 57.259 | 4.274 | 55.168 | 1.00 | 40.78 | B | C |
| ATOM | 3009 | CD1 | LEU | B | 336 | 56.103 | 4.988 | 54.435 | 1.00 | 39.06 | B | C |
| ATOM | 3010 | CD2 | LEU | B | 336 | 58.353 | 5.262 | 55.445 | 1.00 | 39.73 | B | C |
| ATOM | 3011 | C | LEU | B | 336 | 57.110 | 2.575 | 58.707 | 1.00 | 38.87 | B | C |
| ATOM | 3012 | O | LEU | B | 336 | 56.416 | 1.549 | 58.771 | 1.00 | 37.21 | B | O |
| ATOM | 3013 | N | THR | B | 337 | 57.310 | 3.408 | 59.727 | 1.00 | 38.72 | B | N |
| ATOM | 3014 | CA | THR | B | 337 | 56.718 | 3.222 | 61.050 | 0.00 | 38.63 | B | C |
| ATOM | 3015 | CB | THR | B | 337 | 57.416 | 4.123 | 62.151 | 1.00 | 38.22 | B | C |
| ATOM | 3016 | OG1 | THR | B | 337 | 57.290 | 5.504 | 61.797 | 1.00 | 37.03 | B | O |
| ATOM | 3017 | CG2 | THR | B | 337 | 58.914 | 3.779 | 62.326 | 1.00 | 39.02 | B | C |
| ATOM | 3018 | C | THR | B | 337 | 55.241 | 3.645 | 60.986 | 1.00 | 38.35 | B | C |
| ATOM | 3019 | O | THR | B | 337 | 54.850 | 4.435 | 60.104 | 1.00 | 38.65 | B | O |
| ATOM | 3020 | N | ILE | B | 338 | 54.454 | 3.150 | 61.948 | 1.00 | 37.41 | B | N |
| ATOM | 3021 | CA | ILE | B | 338 | 53.036 | 3.483 | 62.032 | 0.00 | 36.38 | B | C |
| ATOM | 3022 | CB | ILE | B | 338 | 52.311 | 2.672 | 63.150 | 1.00 | 36.96 | B | C |
| ATOM | 3023 | CG2 | ILE | B | 338 | 52.950 | 2.952 | 64.534 | 1.00 | 36.31 | B | C |
| ATOM | 3024 | CG1 | ILE | B | 338 | 50.799 | 2.974 | 63.125 | 1.00 | 36.10 | B | C |
| ATOM | 3025 | CD1 | ILE | B | 338 | 50.050 | 2.422 | 61.896 | 1.00 | 34.68 | B | C |
| ATOM | 3026 | C | ILE | B | 338 | 52.946 | 4.976 | 62.270 | 1.00 | 35.51 | B | C |
| ATOM | 3027 | O | ILE | B | 338 | 52.068 | 5.627 | 61.751 | 1.00 | 35.73 | B | O |
| ATOM | 3028 | N | ASN | B | 339 | 53.941 | 5.534 | 62.943 | 1.00 | 35.31 | B | N |
| ATOM | 3029 | CA | ASN | B | 339 | 53.982 | 6.980 | 63.179 | 0.00 | 35.27 | B | C |
| ATOM | 3030 | CB | ASN | B | 339 | 55.232 | 7.348 | 63.961 | 1.00 | 36.29 | B | C |
| ATOM | 3031 | CG | ASN | B | 339 | 55.230 | 6.763 | 65.337 | 1.00 | 36.95 | B | C |
| ATOM | 3032 | OD1 | ASN | B | 339 | 54.974 | 7.477 | 66.310 | 1.00 | 37.83 | B | O |
| ATOM | 3033 | ND2 | ASN | B | 339 | 55.486 | 5.459 | 65.439 | 1.00 | 35.90 | B | N |
| ATOM | 3034 | C | ASN | B | 339 | 54.027 | 7.770 | 61.873 | 1.00 | 34.59 | B | C |
| ATOM | 3035 | O | ASN | B | 339 | 53.407 | 8.828 | 61.768 | 1.00 | 34.61 | B | O |
| ATOM | 3036 | N | LYS | B | 340 | 54.907 | 7.347 | 60.967 | 1.00 | 33.46 | B | N |
| ATOM | 3037 | CA | LYS | B | 340 | 55.065 | 7.982 | 59.660 | 0.00 | 32.95 | B | C |
| ATOM | 3038 | CB | LYS | B | 340 | 56.309 | 7.405 | 58.967 | 1.00 | 33.24 | B | C |
| ATOM | 3039 | CG | LYS | B | 340 | 56.529 | 7.898 | 57.573 | 1.00 | 34.53 | B | C |
| ATOM | 3040 | CD | LYS | B | 340 | 56.607 | 9.431 | 57.572 | 1.00 | 36.42 | B | C |
| ATOM | 3041 | CE | LYS | B | 340 | 56.672 | 9.957 | 56.137 | 1.00 | 38.25 | B | C |
| ATOM | 3042 | NZ | LYS | B | 340 | 56.782 | 11.451 | 56.011 | 1.00 | 39.16 | B | N |
| ATOM | 3043 | C | LYS | B | 340 | 53.778 | 7.732 | 58.801 | 1.00 | 31.97 | B | C |
| ATOM | 3044 | O | LYS | B | 340 | 53.257 | 8.645 | 58.167 | 1.00 | 32.39 | B | O |
| ATOM | 3045 | N | LEU | B | 341 | 53.304 | 6.490 | 58.759 | 1.00 | 30.23 | B | N |
| ATOM | 3046 | CA | LEU | B | 341 | 52.080 | 6.154 | 58.036 | 0.00 | 28.59 | B | C |
| ATOM | 3047 | CB | LEU | B | 341 | 51.728 | 4.690 | 58.300 | 1.00 | 25.89 | B | C |
| ATOM | 3048 | CG | LEU | B | 341 | 52.727 | 3.788 | 57.587 | 1.00 | 25.21 | B | C |
| ATOM | 3049 | CD1 | LEU | B | 341 | 52.447 | 2.330 | 57.886 | 1.00 | 22.67 | B | C |
| ATOM | 3050 | CD2 | LEU | B | 341 | 52.650 | 4.073 | 56.080 | 1.00 | 23.62 | B | C |
| ATOM | 3051 | C | LEU | B | 341 | 50.916 | 7.063 | 58.470 | 1.00 | 28.49 | B | C |
| ATOM | 3052 | O | LEU | B | 341 | 50.158 | 7.571 | 57.642 | 1.00 | 28.77 | B | O |
| ATOM | 3053 | N | LEU | B | 342 | 50.801 | 7.297 | 59.761 | 1.00 | 28.50 | B | N |
| ATOM | 3054 | CA | LEU | B | 342 | 49.758 | 8.163 | 60.290 | 0.00 | 29.13 | B | C |
| ATOM | 3055 | CB | LEU | B | 342 | 49.582 | 7.968 | 61.799 | 1.00 | 29.21 | B | C |

Figure 12

| | | | | | | | | | | | |
|---|---|---|---|---|---|---|---|---|---|---|---|
| ATOM | 3056 | CG | LEU | B | 342 | 49.013 | 6.567 | 62.080 | 1.00 | 30.80 | B C |
| ATOM | 3057 | CD1 | LEU | B | 342 | 48.275 | 6.562 | 63.349 | 1.00 | 31.55 | B C |
| ATOM | 3058 | CD2 | LEU | B | 342 | 48.035 | 6.101 | 60.998 | 1.00 | 32.34 | B C |
| ATOM | 3059 | C | LEU | B | 342 | 49.965 | 9.611 | 59.954 | 1.00 | 30.22 | B C |
| ATOM | 3060 | O | LEU | B | 342 | 48.987 | 10.345 | 59.857 | 1.00 | 30.70 | B O |
| ATOM | 3061 | N | ASP | B | 343 | 51.219 | 10.064 | 59.816 | 1.00 | 30.93 | B N |
| ATOM | 3062 | CA | ASP | B | 343 | 51.457 | 11.470 | 59.421 | 0.00 | 32.20 | B C |
| ATOM | 3063 | CB | ASP | B | 343 | 52.905 | 11.916 | 59.627 | 1.00 | 35.65 | B C |
| ATOM | 3064 | CG | ASP | B | 343 | 53.112 | 13.394 | 59.220 | 1.00 | 40.00 | B C |
| ATOM | 3065 | OD1 | ASP | B | 343 | 52.758 | 14.323 | 59.988 | 1.00 | 41.58 | B O |
| ATOM | 3066 | OD2 | ASP | B | 343 | 53.606 | 13.642 | 58.097 | 1.00 | 43.64 | B O |
| ATOM | 3067 | C | ASP | B | 343 | 51.074 | 11.655 | 57.932 | 1.00 | 30.95 | B C |
| ATOM | 3068 | O | ASP | B | 343 | 50.544 | 12.683 | 57.535 | 1.00 | 30.06 | B O |
| ATOM | 3069 | N | MET | B | 344 | 51.381 | 10.659 | 57.114 | 1.00 | 30.23 | B N |
| ATOM | 3070 | CA | MET | B | 344 | 51.028 | 10.697 | 55.700 | 0.00 | 29.53 | B C |
| ATOM | 3071 | CB | MET | B | 344 | 51.568 | 9.427 | 55.036 | 1.00 | 30.34 | B C |
| ATOM | 3072 | CG | MET | B | 344 | 53.080 | 9.402 | 54.888 | 1.00 | 31.76 | B C |
| ATOM | 3073 | SD | MET | B | 344 | 53.582 | 7.902 | 54.068 | 1.00 | 34.25 | B S |
| ATOM | 3074 | CE | MET | B | 344 | 54.186 | 8.539 | 52.557 | 1.00 | 33.65 | B C |
| ATOM | 3075 | C | MET | B | 344 | 49.464 | 10.763 | 55.563 | 1.00 | 29.42 | B C |
| ATOM | 3076 | O | MET | B | 344 | 48.903 | 11.576 | 54.787 | 1.00 | 28.09 | B O |
| ATOM | 3077 | N | ALA | B | 345 | 48.787 | 9.932 | 56.370 | 1.00 | 27.92 | B N |
| ATOM | 3078 | CA | ALA | B | 345 | 47.336 | 9.873 | 56.383 | 0.00 | 26.53 | B C |
| ATOM | 3079 | CB | ALA | B | 345 | 46.891 | 8.792 | 57.325 | 1.00 | 24.73 | B C |
| ATOM | 3080 | C | ALA | B | 345 | 46.806 | 11.246 | 56.817 | 1.00 | 25.86 | B C |
| ATOM | 3081 | O | ALA | B | 345 | 45.881 | 11.780 | 56.227 | 1.00 | 25.78 | B O |
| ATOM | 3082 | N | ALA | B | 346 | 47.448 | 11.842 | 57.806 | 1.00 | 25.15 | B N |
| ATOM | 3083 | CA | ALA | B | 346 | 47.069 | 13.143 | 58.285 | 0.00 | 25.16 | B C |
| ATOM | 3084 | CB | ALA | B | 346 | 47.943 | 13.498 | 59.484 | 1.00 | 25.95 | B C |
| ATOM | 3085 | C | ALA | B | 346 | 47.203 | 14.216 | 57.210 | 1.00 | 26.26 | B C |
| ATOM | 3086 | O | ALA | B | 346 | 46.447 | 15.198 | 57.161 | 1.00 | 27.13 | B O |
| ATOM | 3087 | N | GLN | B | 347 | 48.242 | 14.091 | 56.397 | 1.00 | 26.71 | B N |
| ATOM | 3088 | CA | GLN | B | 347 | 48.447 | 15.066 | 55.335 | 0.00 | 27.33 | B C |
| ATOM | 3089 | CB | GLN | B | 347 | 49.809 | 14.831 | 54.668 | 1.00 | 28.78 | B C |
| ATOM | 3090 | CG | GLN | B | 347 | 51.010 | 15.258 | 55.454 | 1.00 | 32.25 | B C |
| ATOM | 3091 | CD | GLN | B | 347 | 52.322 | 14.979 | 54.652 | 1.00 | 36.24 | B C |
| ATOM | 3092 | OE1 | GLN | B | 347 | 53.054 | 15.912 | 54.324 | 1.00 | 37.98 | B O |
| ATOM | 3093 | NE2 | GLN | B | 347 | 52.554 | 13.715 | 54.270 | 1.00 | 36.20 | B N |
| ATOM | 3094 | C | GLN | B | 347 | 47.364 | 14.989 | 54.263 | 1.00 | 25.48 | B C |
| ATOM | 3095 | O | GLN | B | 347 | 47.005 | 16.004 | 53.670 | 1.00 | 25.69 | B O |
| ATOM | 3096 | N | ILE | B | 348 | 46.948 | 13.777 | 53.923 | 1.00 | 23.83 | B N |
| ATOM | 3097 | CA | ILE | B | 348 | 45.907 | 13.551 | 52.934 | 0.00 | 23.90 | B C |
| ATOM | 3098 | CB | ILE | B | 348 | 45.774 | 12.040 | 52.656 | 1.00 | 24.81 | B C |
| ATOM | 3099 | CG2 | ILE | B | 348 | 44.587 | 11.767 | 51.748 | 1.00 | 24.56 | B C |
| ATOM | 3100 | CG1 | ILE | B | 348 | 47.080 | 11.539 | 52.018 | 1.00 | 25.08 | B C |
| ATOM | 3101 | CD1 | ILE | B | 348 | 47.193 | 10.039 | 51.924 | 1.00 | 24.93 | B C |
| ATOM | 3102 | C | ILE | B | 348 | 44.573 | 14.115 | 53.448 | 1.00 | 24.28 | B C |
| ATOM | 3103 | O | ILE | B | 348 | 43.806 | 14.764 | 52.693 | 1.00 | 23.11 | B O |
| ATOM | 3104 | N | ALA | B | 349 | 44.307 | 13.864 | 54.736 | 1.00 | 23.45 | B N |
| ATOM | 3105 | CA | ALA | B | 349 | 43.113 | 14.329 | 55.368 | 0.00 | 23.82 | B C |
| ATOM | 3106 | CB | ALA | B | 349 | 43.026 | 13.817 | 56.820 | 1.00 | 23.82 | B C |
| ATOM | 3107 | C | ALA | B | 349 | 43.126 | 15.830 | 55.347 | 1.00 | 24.79 | B C |
| ATOM | 3108 | O | ALA | B | 349 | 42.073 | 16.449 | 55.170 | 1.00 | 25.73 | B O |
| ATOM | 3109 | N | GLU | B | 350 | 44.312 | 16.427 | 55.532 | 1.00 | 25.23 | B N |
| ATOM | 3110 | CA | GLU | B | 350 | 44.449 | 17.890 | 55.547 | 0.00 | 25.23 | B C |
| ATOM | 3111 | CB | GLU | B | 350 | 45.854 | 18.323 | 55.990 | 1.00 | 26.74 | B C |
| ATOM | 3112 | CG | GLU | B | 350 | 46.091 | 19.843 | 55.927 | 1.00 | 28.59 | B C |
| ATOM | 3113 | CD | GLU | B | 350 | 47.573 | 20.267 | 56.032 | 1.00 | 30.94 | B C |
| ATOM | 3114 | OE1 | GLU | B | 350 | 48.462 | 19.456 | 56.423 | 1.00 | 32.31 | B O |

Figure 12

| ATOM | 3115 | OE2 | GLU | B | 350 | 47.847 | 21.449 | 55.755 | 1.00 | 31.99 | B | O |
| ---- | ---- | --- | --- | - | --- | ------ | ------ | ------ | ---- | ----- | - | - |
| ATOM | 3116 | C   | GLU | B | 350 | 44.122 | 18.494 | 54.209 | 1.00 | 24.72 | B | C |
| ATOM | 3117 | O   | GLU | B | 350 | 43.518 | 19.563 | 54.122 | 1.00 | 25.89 | B | O |
| ATOM | 3118 | N   | GLY | B | 351 | 44.521 | 17.815 | 53.150 | 1.00 | 24.46 | B | N |
| ATOM | 3119 | CA  | GLY | B | 351 | 44.202 | 18.312 | 51.816 | 0.00 | 23.33 | B | C |
| ATOM | 3120 | C   | GLY | B | 351 | 42.726 | 18.115 | 51.522 | 1.00 | 22.93 | B | C |
| ATOM | 3121 | O   | GLY | B | 351 | 42.112 | 18.976 | 50.904 | 1.00 | 23.10 | B | O |
| ATOM | 3122 | N   | MET | B | 352 | 42.160 | 16.975 | 51.918 | 1.00 | 21.62 | B | N |
| ATOM | 3123 | CA  | MET | B | 352 | 40.731 | 16.740 | 51.701 | 0.00 | 21.18 | B | C |
| ATOM | 3124 | CB  | MET | B | 352 | 40.298 | 15.328 | 52.060 | 1.00 | 20.22 | B | C |
| ATOM | 3125 | CG  | MET | B | 352 | 40.795 | 14.294 | 51.150 | 1.00 | 19.97 | B | C |
| ATOM | 3126 | SD  | MET | B | 352 | 40.251 | 14.557 | 49.470 | 1.00 | 23.61 | B | S |
| ATOM | 3127 | CE  | MET | B | 352 | 38.433 | 15.083 | 49.683 | 1.00 | 19.52 | B | C |
| ATOM | 3128 | C   | MET | B | 352 | 39.924 | 17.716 | 52.533 | 1.00 | 21.98 | B | C |
| ATOM | 3129 | O   | MET | B | 352 | 38.816 | 18.071 | 52.130 | 1.00 | 22.27 | B | O |
| ATOM | 3130 | N   | ALA | B | 353 | 40.488 | 18.189 | 53.652 | 1.00 | 21.44 | B | N |
| ATOM | 3131 | CA  | ALA | B | 353 | 39.810 | 19.174 | 54.474 | 0.00 | 23.51 | B | C |
| ATOM | 3132 | CB  | ALA | B | 353 | 40.548 | 19.364 | 55.817 | 1.00 | 22.75 | B | C |
| ATOM | 3133 | C   | ALA | B | 353 | 39.725 | 20.522 | 53.715 | 1.00 | 24.38 | B | C |
| ATOM | 3134 | O   | ALA | B | 353 | 38.818 | 21.306 | 53.947 | 1.00 | 24.26 | B | O |
| ATOM | 3135 | N   | PHE | B | 354 | 40.674 | 20.787 | 52.809 | 1.00 | 25.75 | B | N |
| ATOM | 3136 | CA  | PHE | B | 354 | 40.671 | 22.027 | 52.022 | 0.00 | 25.54 | B | C |
| ATOM | 3137 | CB  | PHE | B | 354 | 42.065 | 22.318 | 51.441 | 1.00 | 26.84 | B | C |
| ATOM | 3138 | CG  | PHE | B | 354 | 42.138 | 23.582 | 50.600 | 1.00 | 27.38 | B | C |
| ATOM | 3139 | CD1 | PHE | B | 354 | 42.057 | 24.850 | 51.189 | 1.00 | 29.62 | B | C |
| ATOM | 3140 | CD2 | PHE | B | 354 | 42.302 | 23.502 | 49.223 | 1.00 | 27.75 | B | C |
| ATOM | 3141 | CE1 | PHE | B | 354 | 42.142 | 26.039 | 50.380 | 1.00 | 29.25 | B | C |
| ATOM | 3142 | CE2 | PHE | B | 354 | 42.389 | 24.678 | 48.425 | 1.00 | 28.47 | B | C |
| ATOM | 3143 | CZ  | PHE | B | 354 | 42.306 | 25.932 | 49.004 | 1.00 | 27.34 | B | C |
| ATOM | 3144 | C   | PHE | B | 354 | 39.665 | 21.804 | 50.926 | 1.00 | 25.34 | B | C |
| ATOM | 3145 | O   | PHE | B | 354 | 38.844 | 22.661 | 50.667 | 1.00 | 26.27 | B | O |
| ATOM | 3146 | N   | ILE | B | 355 | 39.665 | 20.633 | 50.312 | 1.00 | 25.39 | B | N |
| ATOM | 3147 | CA  | ILE | B | 355 | 38.665 | 20.367 | 49.278 | 0.00 | 25.40 | B | C |
| ATOM | 3148 | CB  | ILE | B | 355 | 38.890 | 19.010 | 48.599 | 1.00 | 24.57 | B | C |
| ATOM | 3149 | CG2 | ILE | B | 355 | 37.648 | 18.608 | 47.738 | 1.00 | 23.68 | B | C |
| ATOM | 3150 | CG1 | ILE | B | 355 | 40.163 | 19.054 | 47.730 | 1.00 | 23.36 | B | C |
| ATOM | 3151 | CD1 | ILE | B | 355 | 40.695 | 17.653 | 47.329 | 1.00 | 21.35 | B | C |
| ATOM | 3152 | C   | ILE | B | 355 | 37.231 | 20.496 | 49.871 | 1.00 | 26.47 | B | C |
| ATOM | 3153 | O   | ILE | B | 355 | 36.398 | 21.188 | 49.302 | 1.00 | 25.84 | B | O |
| ATOM | 3154 | N   | GLU | B | 356 | 36.997 | 19.893 | 51.042 | 1.00 | 27.83 | B | N |
| ATOM | 3155 | CA  | GLU | B | 356 | 35.715 | 19.957 | 51.778 | 0.00 | 29.20 | B | C |
| ATOM | 3156 | CB  | GLU | B | 356 | 35.874 | 19.190 | 53.077 | 1.00 | 28.67 | B | C |
| ATOM | 3157 | CG  | GLU | B | 356 | 34.705 | 19.289 | 54.080 | 1.00 | 29.02 | B | C |
| ATOM | 3158 | CD  | GLU | B | 356 | 34.910 | 18.352 | 55.273 | 1.00 | 28.34 | B | C |
| ATOM | 3159 | OE1 | GLU | B | 356 | 35.578 | 18.696 | 56.271 | 1.00 | 30.00 | B | O |
| ATOM | 3160 | OE2 | GLU | B | 356 | 34.450 | 17.221 | 55.191 | 1.00 | 29.70 | B | O |
| ATOM | 3161 | C   | GLU | B | 356 | 35.315 | 21.428 | 52.087 | 1.00 | 30.28 | B | C |
| ATOM | 3162 | O   | GLU | B | 356 | 34.219 | 21.875 | 51.814 | 1.00 | 30.28 | B | O |
| ATOM | 3163 | N   | GLU | B | 357 | 36.258 | 22.172 | 52.612 | 1.00 | 32.59 | B | N |
| ATOM | 3164 | CA  | GLU | B | 357 | 36.110 | 23.578 | 52.939 | 0.00 | 35.68 | B | C |
| ATOM | 3165 | CB  | GLU | B | 357 | 37.499 | 24.034 | 53.367 | 1.00 | 39.41 | B | C |
| ATOM | 3166 | CG  | GLU | B | 357 | 37.857 | 25.473 | 53.053 | 1.00 | 44.60 | B | C |
| ATOM | 3167 | CD  | GLU | B | 357 | 37.288 | 26.417 | 54.070 | 1.00 | 48.77 | B | C |
| ATOM | 3168 | OE1 | GLU | B | 357 | 37.021 | 25.959 | 55.223 | 1.00 | 50.91 | B | O |
| ATOM | 3169 | OE2 | GLU | B | 357 | 37.133 | 27.615 | 53.713 | 1.00 | 51.16 | B | O |
| ATOM | 3170 | C   | GLU | B | 357 | 35.634 | 24.445 | 51.749 | 1.00 | 36.30 | B | C |
| ATOM | 3171 | O   | GLU | B | 357 | 34.787 | 25.337 | 51.893 | 1.00 | 36.17 | B | O |
| ATOM | 3172 | N   | ARG | B | 358 | 36.216 | 24.186 | 50.580 | 1.00 | 36.45 | B | N |
| ATOM | 3173 | CA  | ARG | B | 358 | 35.913 | 24.942 | 49.381 | 0.00 | 35.88 | B | C |

Figure 12

| ATOM | 3174 | CB | ARG | B | 358 | 37.152 | 25.006 | 48.474 | 1.00 | 37.87 | B | C |
| --- | --- | --- | --- | --- | --- | --- | --- | --- | --- | --- | --- | --- |
| ATOM | 3175 | CG | ARG | B | 358 | 38.407 | 25.523 | 49.169 | 1.00 | 39.91 | B | C |
| ATOM | 3176 | CD | ARG | B | 358 | 38.330 | 27.014 | 49.515 | 1.00 | 43.83 | B | C |
| ATOM | 3177 | NE | ARG | B | 358 | 38.145 | 27.831 | 48.315 | 1.00 | 49.04 | B | N |
| ATOM | 3178 | CZ | ARG | B | 358 | 39.049 | 27.957 | 47.334 | 1.00 | 52.10 | B | C |
| ATOM | 3179 | NH1 | ARG | B | 358 | 40.215 | 27.323 | 47.412 | 1.00 | 55.36 | B | N |
| ATOM | 3180 | NH2 | ARG | B | 358 | 38.785 | 28.665 | 46.244 | 1.00 | 52.40 | B | N |
| ATOM | 3181 | C | ARG | B | 358 | 34.717 | 24.382 | 48.669 | 1.00 | 34.72 | B | C |
| ATOM | 3182 | O | ARG | B | 358 | 34.343 | 24.844 | 47.600 | 1.00 | 34.40 | B | O |
| ATOM | 3183 | N | ASN | B | 359 | 34.085 | 23.388 | 49.278 | 1.00 | 33.87 | B | N |
| ATOM | 3184 | CA | ASN | B | 359 | 32.869 | 22.798 | 48.727 | 0.00 | 33.01 | B | C |
| ATOM | 3185 | CB | ASN | B | 359 | 31.750 | 23.848 | 48.630 | 1.00 | 36.08 | B | C |
| ATOM | 3186 | CG | ASN | B | 359 | 31.450 | 24.529 | 49.976 | 1.00 | 39.32 | B | C |
| ATOM | 3187 | OD1 | ASN | B | 359 | 30.883 | 23.913 | 50.913 | 1.00 | 41.43 | B | O |
| ATOM | 3188 | ND2 | ASN | B | 359 | 31.846 | 25.805 | 50.090 | 1.00 | 40.37 | B | N |
| ATOM | 3189 | C | ASN | B | 359 | 32.989 | 22.050 | 47.420 | 1.00 | 31.28 | B | C |
| ATOM | 3190 | O | ASN | B | 359 | 32.083 | 22.095 | 46.580 | 1.00 | 30.51 | B | O |
| ATOM | 3191 | N | TYR | B | 360 | 34.086 | 21.309 | 47.281 | 1.00 | 30.19 | B | N |
| ATOM | 3192 | CA | TYR | B | 360 | 34.339 | 20.464 | 46.124 | 0.00 | 29.48 | B | C |
| ATOM | 3193 | CB | TYR | B | 360 | 35.736 | 20.699 | 45.597 | 1.00 | 30.87 | B | C |
| ATOM | 3194 | CG | TYR | B | 360 | 35.862 | 21.902 | 44.738 | 1.00 | 32.57 | B | C |
| ATOM | 3195 | CD1 | TYR | B | 360 | 36.233 | 23.112 | 45.289 | 1.00 | 34.51 | B | C |
| ATOM | 3196 | CE1 | TYR | B | 360 | 36.352 | 24.253 | 44.507 | 1.00 | 35.70 | B | C |
| ATOM | 3197 | CD2 | TYR | B | 360 | 35.610 | 21.830 | 43.365 | 1.00 | 34.41 | B | C |
| ATOM | 3198 | CE2 | TYR | B | 360 | 35.727 | 22.958 | 42.560 | 1.00 | 35.71 | B | C |
| ATOM | 3199 | CZ | TYR | B | 360 | 36.097 | 24.171 | 43.149 | 1.00 | 36.82 | B | C |
| ATOM | 3200 | OH | TYR | B | 360 | 36.192 | 25.321 | 42.391 | 1.00 | 39.56 | B | O |
| ATOM | 3201 | C | TYR | B | 360 | 34.323 | 19.050 | 46.614 | 1.00 | 28.92 | B | C |
| ATOM | 3202 | O | TYR | B | 360 | 34.232 | 18.818 | 47.788 | 1.00 | 29.36 | B | O |
| ATOM | 3203 | N | ILE | B | 361 | 34.381 | 18.075 | 45.724 | 1.00 | 28.99 | B | N |
| ATOM | 3204 | CA | ILE | B | 361 | 34.504 | 16.699 | 46.160 | 0.00 | 29.41 | B | C |
| ATOM | 3205 | CB | ILE | B | 361 | 33.197 | 15.887 | 46.034 | 1.00 | 29.32 | B | C |
| ATOM | 3206 | CG2 | ILE | B | 361 | 32.109 | 16.542 | 46.868 | 1.00 | 31.66 | B | C |
| ATOM | 3207 | CG1 | ILE | B | 361 | 32.720 | 15.803 | 44.601 | 1.00 | 30.04 | B | C |
| ATOM | 3208 | CD1 | ILE | B | 361 | 31.638 | 14.796 | 44.416 | 1.00 | 31.52 | B | C |
| ATOM | 3209 | C | ILE | B | 361 | 35.670 | 16.116 | 45.345 | 1.00 | 29.49 | B | C |
| ATOM | 3210 | O | ILE | B | 361 | 36.135 | 16.739 | 44.388 | 1.00 | 30.68 | B | O |
| ATOM | 3211 | N | HIS | B | 362 | 36.217 | 14.982 | 45.756 | 1.00 | 28.71 | B | N |
| ATOM | 3212 | CA | HIS | B | 362 | 37.320 | 14.390 | 45.012 | 0.00 | 27.54 | B | C |
| ATOM | 3213 | CB | HIS | B | 362 | 38.273 | 13.667 | 45.964 | 1.00 | 25.70 | B | C |
| ATOM | 3214 | CG | HIS | B | 362 | 39.536 | 13.201 | 45.304 | 1.00 | 24.73 | B | C |
| ATOM | 3215 | CD2 | HIS | B | 362 | 40.783 | 13.708 | 45.334 | 1.00 | 22.30 | B | C |
| ATOM | 3216 | ND1 | HIS | B | 362 | 39.566 | 12.177 | 44.384 | 1.00 | 23.63 | B | N |
| ATOM | 3217 | CE1 | HIS | B | 362 | 40.766 | 12.079 | 43.862 | 1.00 | 20.62 | B | C |
| ATOM | 3218 | NE2 | HIS | B | 362 | 41.524 | 13.002 | 44.417 | 1.00 | 22.80 | B | N |
| ATOM | 3219 | C | HIS | B | 362 | 36.758 | 13.393 | 44.010 | 1.00 | 27.51 | B | C |
| ATOM | 3220 | O | HIS | B | 362 | 36.991 | 13.505 | 42.814 | 1.00 | 29.09 | B | O |
| ATOM | 3221 | N | ARG | B | 363 | 35.894 | 12.531 | 44.517 | 1.00 | 26.99 | B | N |
| ATOM | 3222 | CA | ARG | B | 363 | 35.256 | 11.422 | 43.838 | 0.00 | 26.86 | B | C |
| ATOM | 3223 | CB | ARG | B | 363 | 34.194 | 11.796 | 42.804 | 1.00 | 30.10 | B | C |
| ATOM | 3224 | CG | ARG | B | 363 | 34.587 | 12.732 | 41.734 | 1.00 | 35.00 | B | C |
| ATOM | 3225 | CD | ARG | B | 363 | 33.318 | 13.165 | 40.977 | 1.00 | 37.77 | B | C |
| ATOM | 3226 | NE | ARG | B | 363 | 32.659 | 12.016 | 40.388 | 1.00 | 38.66 | B | N |
| ATOM | 3227 | CZ | ARG | B | 363 | 31.338 | 11.912 | 40.252 | 1.00 | 40.20 | B | C |
| ATOM | 3228 | NH1 | ARG | B | 363 | 30.548 | 12.897 | 40.671 | 1.00 | 37.55 | B | N |
| ATOM | 3229 | NH2 | ARG | B | 363 | 30.813 | 10.812 | 39.717 | 1.00 | 40.65 | B | N |
| ATOM | 3230 | C | ARG | B | 363 | 36.146 | 10.292 | 43.383 | 1.00 | 26.16 | B | C |
| ATOM | 3231 | O | ARG | B | 363 | 35.652 | 9.207 | 43.114 | 1.00 | 25.63 | B | O |
| ATOM | 3232 | N | ASP | B | 364 | 37.470 | 10.501 | 43.364 | 1.00 | 24.38 | B | N |

Figure 12

| | | | | | | | | | | | |
|---|---|---|---|---|---|---|---|---|---|---|---|
| ATOM | 3233 | CA | ASP | B | 364 | 38.378 | 9.394 | 43.005 | 0.00 24.49 | B | C |
| ATOM | 3234 | CB | ASP | B | 364 | 38.990 | 9.619 | 41.627 | 1.00 23.77 | B | C |
| ATOM | 3235 | CG | ASP | B | 364 | 37.984 | 9.457 | 40.527 | 1.00 24.42 | B | C |
| ATOM | 3236 | OD1 | ASP | B | 364 | 37.559 | 8.291 | 40.264 | 1.00 23.67 | B | O |
| ATOM | 3237 | OD2 | ASP | B | 364 | 37.593 | 10.508 | 39.973 | 1.00 24.30 | B | O |
| ATOM | 3238 | C | ASP | B | 364 | 39.486 | 9.134 | 44.060 | 1.00 24.48 | B | C |
| ATOM | 3239 | O | ASP | B | 364 | 40.577 | 8.688 | 43.741 | 1.00 24.09 | B | O |
| ATOM | 3240 | N | LEU | B | 365 | 39.183 | 9.422 | 45.325 | 1.00 22.63 | B | N |
| ATOM | 3241 | CA | LEU | B | 365 | 40.120 | 9.282 | 46.403 | 0.00 22.53 | B | C |
| ATOM | 3242 | CB | LEU | B | 365 | 39.544 | 9.970 | 47.644 | 1.00 21.09 | B | C |
| ATOM | 3243 | CG | LEU | B | 365 | 40.367 | 10.003 | 48.947 | 1.00 21.59 | B | C |
| ATOM | 3244 | CD1 | LEU | B | 365 | 41.680 | 10.779 | 48.619 | 1.00 19.75 | B | C |
| ATOM | 3245 | CD2 | LEU | B | 365 | 39.552 | 10.675 | 50.149 | 1.00 15.89 | B | C |
| ATOM | 3246 | C | LEU | B | 365 | 40.511 | 7.842 | 46.767 | 1.00 24.01 | B | C |
| ATOM | 3247 | O | LEU | B | 365 | 39.681 | 7.074 | 47.257 | 1.00 25.29 | B | O |
| ATOM | 3248 | N | ARG | B | 366 | 41.765 | 7.486 | 46.521 | 1.00 23.90 | B | N |
| ATOM | 3249 | CA | ARG | B | 366 | 42.290 | 6.186 | 46.865 | 0.00 24.69 | B | C |
| ATOM | 3250 | CB | ARG | B | 366 | 41.774 | 5.118 | 45.917 | 1.00 26.13 | B | C |
| ATOM | 3251 | CG | ARG | B | 366 | 41.995 | 5.385 | 44.422 | 1.00 28.49 | B | C |
| ATOM | 3252 | CD | ARG | B | 366 | 41.639 | 4.154 | 43.617 | 1.00 29.28 | B | C |
| ATOM | 3253 | NE | ARG | B | 366 | 41.594 | 4.422 | 42.181 | 1.00 33.28 | B | N |
| ATOM | 3254 | CZ | ARG | B | 366 | 40.601 | 5.072 | 41.556 | 1.00 32.37 | B | C |
| ATOM | 3255 | NH1 | ARG | B | 366 | 39.538 | 5.536 | 42.209 | 1.00 30.41 | B | N |
| ATOM | 3256 | NH2 | ARG | B | 366 | 40.688 | 5.230 | 40.245 | 1.00 32.92 | B | N |
| ATOM | 3257 | C | ARG | B | 366 | 43.819 | 6.287 | 46.851 | 1.00 24.45 | B | C |
| ATOM | 3258 | O | ARG | B | 366 | 44.360 | 7.300 | 46.405 | 1.00 24.55 | B | O |
| ATOM | 3259 | N | ALA | B | 367 | 44.524 | 5.304 | 47.412 | 1.00 23.21 | B | N |
| ATOM | 3260 | CA | ALA | B | 367 | 46.000 | 5.388 | 47.416 | 0.00 22.83 | B | C |
| ATOM | 3261 | CB | ALA | B | 367 | 46.615 | 4.148 | 48.057 | 1.00 23.20 | B | C |
| ATOM | 3262 | C | ALA | B | 367 | 46.650 | 5.638 | 46.046 | 1.00 22.48 | B | C |
| ATOM | 3263 | O | ALA | B | 367 | 47.661 | 6.317 | 45.957 | 1.00 22.07 | B | O |
| ATOM | 3264 | N | ALA | B | 368 | 46.092 | 5.078 | 44.977 | 1.00 22.63 | B | N |
| ATOM | 3265 | CA | ALA | B | 368 | 46.644 | 5.276 | 43.635 | 0.00 22.41 | B | C |
| ATOM | 3266 | CB | ALA | B | 368 | 45.834 | 4.479 | 42.609 | 1.00 22.30 | B | C |
| ATOM | 3267 | C | ALA | B | 368 | 46.656 | 6.749 | 43.235 | 1.00 23.56 | B | C |
| ATOM | 3268 | O | ALA | B | 368 | 47.534 | 7.182 | 42.479 | 1.00 23.33 | B | O |
| ATOM | 3269 | N | ASN | B | 369 | 45.707 | 7.532 | 43.760 | 1.00 24.06 | B | N |
| ATOM | 3270 | CA | ASN | B | 369 | 45.626 | 8.944 | 43.389 | 0.00 23.89 | B | C |
| ATOM | 3271 | CB | ASN | B | 369 | 44.176 | 9.313 | 42.994 | 1.00 24.44 | B | C |
| ATOM | 3272 | CG | ASN | B | 369 | 43.690 | 8.496 | 41.792 | 1.00 25.17 | B | C |
| ATOM | 3273 | OD1 | ASN | B | 369 | 44.410 | 8.363 | 40.821 | 1.00 28.21 | B | O |
| ATOM | 3274 | ND2 | ASN | B | 369 | 42.494 | 7.930 | 41.852 | 1.00 23.28 | B | N |
| ATOM | 3275 | C | ASN | B | 369 | 46.294 | 9.901 | 44.347 | 1.00 23.40 | B | C |
| ATOM | 3276 | O | ASN | B | 369 | 46.025 | 11.085 | 44.345 | 1.00 24.02 | B | O |
| ATOM | 3277 | N | ILE | B | 370 | 47.147 | 9.355 | 45.226 | 1.00 23.58 | B | N |
| ATOM | 3278 | CA | ILE | B | 370 | 47.935 | 10.178 | 46.149 | 0.00 22.46 | B | C |
| ATOM | 3279 | CB | ILE | B | 370 | 47.930 | 9.635 | 47.596 | 1.00 21.07 | B | C |
| ATOM | 3280 | CG2 | ILE | B | 370 | 48.769 | 10.564 | 48.475 | 1.00 18.07 | B | C |
| ATOM | 3281 | CG1 | ILE | B | 370 | 46.504 | 9.570 | 48.145 | 1.00 18.39 | B | C |
| ATOM | 3282 | CD1 | ILE | B | 370 | 45.782 | 10.934 | 48.130 | 1.00 18.16 | B | C |
| ATOM | 3283 | C | ILE | B | 370 | 49.382 | 10.139 | 45.620 | 1.00 22.97 | B | C |
| ATOM | 3284 | O | ILE | B | 370 | 49.831 | 9.115 | 45.160 | 1.00 21.95 | B | O |
| ATOM | 3285 | N | LEU | B | 371 | 50.084 | 11.260 | 45.611 | 1.00 24.86 | B | N |
| ATOM | 3286 | CA | LEU | B | 371 | 51.494 | 11.251 | 45.110 | 0.00 25.23 | B | C |
| ATOM | 3287 | CB | LEU | B | 371 | 51.706 | 12.302 | 44.017 | 1.00 24.56 | B | C |
| ATOM | 3288 | CG | LEU | B | 371 | 50.972 | 11.958 | 42.718 | 1.00 25.56 | B | C |
| ATOM | 3289 | CD1 | LEU | B | 371 | 51.322 | 12.930 | 41.614 | 1.00 25.83 | B | C |
| ATOM | 3290 | CD2 | LEU | B | 371 | 51.255 | 10.542 | 42.274 | 1.00 25.42 | B | C |
| ATOM | 3291 | C | LEU | B | 371 | 52.446 | 11.490 | 46.279 | 1.00 25.98 | B | C |

Figure 12

| | | | | | | | | | | | |
|---|---|---|---|---|---|---|---|---|---|---|---|
| ATOM | 3292 | O   | LEU | B | 371 | 52.123 | 12.252 | 47.196 | 1.00 | 25.72 | B | O |
| ATOM | 3293 | N   | VAL | B | 372 | 53.586 | 10.798 | 46.268 | 1.00 | 27.01 | B | N |
| ATOM | 3294 | CA  | VAL | B | 372 | 54.606 | 10.899 | 47.337 | 0.00 | 28.22 | B | C |
| ATOM | 3295 | CB  | VAL | B | 372 | 55.023 | 9.509  | 47.841 | 1.00 | 28.13 | B | C |
| ATOM | 3296 | CG1 | VAL | B | 372 | 56.007 | 9.645  | 48.993 | 1.00 | 28.65 | B | C |
| ATOM | 3297 | CG2 | VAL | B | 372 | 53.803 | 8.696  | 48.229 | 1.00 | 27.89 | B | C |
| ATOM | 3298 | C   | VAL | B | 372 | 55.858 | 11.586 | 46.808 | 1.00 | 28.62 | B | C |
| ATOM | 3299 | O   | VAL | B | 372 | 56.414 | 11.190 | 45.782 | 1.00 | 27.51 | B | O |
| ATOM | 3300 | N   | SER | B | 373 | 56.277 | 12.621 | 47.521 | 1.00 | 30.17 | B | N |
| ATOM | 3301 | CA  | SER | B | 373 | 57.435 | 13.401 | 47.147 | 0.00 | 32.73 | B | C |
| ATOM | 3302 | CB  | SER | B | 373 | 57.286 | 14.815 | 47.709 | 1.00 | 31.47 | B | C |
| ATOM | 3303 | OG  | SER | B | 373 | 57.857 | 14.917 | 48.996 | 1.00 | 31.46 | B | O |
| ATOM | 3304 | C   | SER | B | 373 | 58.782 | 12.753 | 47.595 | 1.00 | 35.13 | B | C |
| ATOM | 3305 | O   | SER | B | 373 | 58.817 | 11.676 | 48.214 | 1.00 | 34.10 | B | O |
| ATOM | 3306 | N   | ASP | B | 374 | 59.886 | 13.399 | 47.221 | 1.00 | 38.13 | B | N |
| ATOM | 3307 | CA  | ASP | B | 374 | 61.220 | 12.898 | 47.578 | 0.00 | 41.00 | B | C |
| ATOM | 3308 | CB  | ASP | B | 374 | 62.323 | 13.761 | 46.958 | 1.00 | 43.73 | B | C |
| ATOM | 3309 | CG  | ASP | B | 374 | 62.010 | 15.242 | 47.008 | 1.00 | 46.68 | B | C |
| ATOM | 3310 | OD1 | ASP | B | 374 | 61.085 | 15.665 | 46.278 | 1.00 | 48.83 | B | O |
| ATOM | 3311 | OD2 | ASP | B | 374 | 62.679 | 15.983 | 47.762 | 1.00 | 48.43 | B | O |
| ATOM | 3312 | C   | ASP | B | 374 | 61.345 | 12.900 | 49.074 | 1.00 | 41.44 | B | C |
| ATOM | 3313 | O   | ASP | B | 374 | 61.882 | 11.962 | 49.664 | 1.00 | 41.69 | B | O |
| ATOM | 3314 | N   | THR | B | 375 | 60.737 | 13.909 | 49.688 | 1.00 | 41.41 | B | N |
| ATOM | 3315 | CA  | THR | B | 375 | 60.779 | 14.048 | 51.128 | 0.00 | 41.50 | B | C |
| ATOM | 3316 | CB  | THR | B | 375 | 60.629 | 15.513 | 51.506 | 1.00 | 42.39 | B | C |
| ATOM | 3317 | OG1 | THR | B | 375 | 59.335 | 15.982 | 51.109 | 1.00 | 42.01 | B | O |
| ATOM | 3318 | CG2 | THR | B | 375 | 61.694 | 16.338 | 50.757 | 1.00 | 43.28 | B | C |
| ATOM | 3319 | C   | THR | B | 375 | 59.735 | 13.196 | 51.869 | 1.00 | 41.22 | B | C |
| ATOM | 3320 | O   | THR | B | 375 | 59.640 | 13.236 | 53.095 | 1.00 | 40.44 | B | O |
| ATOM | 3321 | N   | LEU | B | 376 | 58.978 | 12.417 | 51.103 | 1.00 | 41.14 | B | N |
| ATOM | 3322 | CA  | LEU | B | 376 | 57.916 | 11.539 | 51.617 | 0.00 | 41.23 | B | C |
| ATOM | 3323 | CB  | LEU | B | 376 | 58.399 | 10.567 | 52.708 | 1.00 | 41.72 | B | C |
| ATOM | 3324 | CG  | LEU | B | 376 | 59.543 | 9.584  | 52.435 | 1.00 | 43.17 | B | C |
| ATOM | 3325 | CD1 | LEU | B | 376 | 59.346 | 8.359  | 53.317 | 1.00 | 43.35 | B | C |
| ATOM | 3326 | CD2 | LEU | B | 376 | 59.604 | 9.158  | 50.968 | 1.00 | 43.14 | B | C |
| ATOM | 3327 | C   | LEU | B | 376 | 56.650 | 12.246 | 52.088 | 1.00 | 40.47 | B | C |
| ATOM | 3328 | O   | LEU | B | 376 | 55.962 | 11.734 | 52.967 | 1.00 | 41.11 | B | O |
| ATOM | 3329 | N   | SER | B | 377 | 56.399 | 13.458 | 51.578 | 1.00 | 39.31 | B | N |
| ATOM | 3330 | CA  | SER | B | 377 | 55.177 | 14.180 | 51.901 | 0.00 | 37.88 | B | C |
| ATOM | 3331 | CB  | SER | B | 377 | 55.405 | 15.696 | 52.009 | 1.00 | 39.21 | B | C |
| ATOM | 3332 | OG  | SER | B | 377 | 55.615 | 16.327 | 50.755 | 1.00 | 42.88 | B | O |
| ATOM | 3333 | C   | SER | B | 377 | 54.153 | 13.816 | 50.806 | 1.00 | 36.33 | B | C |
| ATOM | 3334 | O   | SER | B | 377 | 54.498 | 13.600 | 49.638 | 1.00 | 35.98 | B | O |
| ATOM | 3335 | N   | CYS | B | 378 | 52.888 | 13.719 | 51.206 | 1.00 | 34.78 | B | N |
| ATOM | 3336 | CA  | CYS | B | 378 | 51.806 | 13.327 | 50.312 | 0.00 | 31.77 | B | C |
| ATOM | 3337 | CB  | CYS | B | 378 | 50.848 | 12.398 | 51.058 | 1.00 | 32.21 | B | C |
| ATOM | 3338 | SG  | CYS | B | 378 | 51.578 | 10.804 | 51.469 | 1.00 | 33.25 | B | S |
| ATOM | 3339 | C   | CYS | B | 378 | 51.058 | 14.504 | 49.744 | 1.00 | 29.81 | B | C |
| ATOM | 3340 | O   | CYS | B | 378 | 50.988 | 15.540 | 50.376 | 1.00 | 29.48 | B | O |
| ATOM | 3341 | N   | LYS | B | 379 | 50.604 | 14.359 | 48.502 | 1.00 | 28.33 | B | N |
| ATOM | 3342 | CA  | LYS | B | 379 | 49.833 | 15.393 | 47.805 | 0.00 | 28.32 | B | C |
| ATOM | 3343 | CB  | LYS | B | 379 | 50.674 | 16.278 | 46.861 | 1.00 | 28.34 | B | C |
| ATOM | 3344 | CG  | LYS | B | 379 | 51.475 | 17.418 | 47.544 | 1.00 | 29.98 | B | C |
| ATOM | 3345 | CD  | LYS | B | 379 | 52.547 | 18.065 | 46.602 | 1.00 | 32.39 | B | C |
| ATOM | 3346 | CE  | LYS | B | 379 | 53.252 | 19.338 | 47.182 | 1.00 | 33.11 | B | C |
| ATOM | 3347 | NZ  | LYS | B | 379 | 52.516 | 20.632 | 46.767 | 1.00 | 38.98 | B | N |
| ATOM | 3348 | C   | LYS | B | 379 | 48.744 | 14.686 | 47.024 | 1.00 | 27.72 | B | C |
| ATOM | 3349 | O   | LYS | B | 379 | 48.940 | 13.591 | 46.466 | 1.00 | 27.16 | B | O |
| ATOM | 3350 | N   | ILE | B | 380 | 47.574 | 15.299 | 47.063 | 1.00 | 27.24 | B | N |

Figure 12

```
ATOM   3351  CA   ILE B 380      46.389  14.775  46.412  0.00 28.10      B    C
ATOM   3352  CB   ILE B 380      45.083  15.348  47.056  1.00 26.99      B    C
ATOM   3353  CG2  ILE B 380      43.900  14.827  46.346  1.00 24.38      B    C
ATOM   3354  CG1  ILE B 380      44.994  14.980  48.539  1.00 27.55      B    C
ATOM   3355  CD1  ILE B 380      43.853  15.683  49.245  1.00 26.57      B    C
ATOM   3356  C    ILE B 380      46.391  15.118  44.922  1.00 28.13      B    C
ATOM   3357  O    ILE B 380      46.652  16.267  44.543  1.00 27.94      B    O
ATOM   3358  N    ALA B 381      46.005  14.151  44.093  1.00 28.09      B    N
ATOM   3359  CA   ALA B 381      45.952  14.393  42.659  0.00 29.48      B    C
ATOM   3360  CB   ALA B 381      47.069  13.584  41.938  1.00 28.66      B    C
ATOM   3361  C    ALA B 381      44.612  13.988  42.089  1.00 29.00      B    C
ATOM   3362  O    ALA B 381      43.860  13.243  42.706  1.00 28.06      B    O
ATOM   3363  N    ASP B 382      44.313  14.522  40.918  1.00 30.03      B    N
ATOM   3364  CA   ASP B 382      43.120  14.116  40.192  0.00 31.56      B    C
ATOM   3365  CB   ASP B 382      43.323  12.678  39.664  1.00 32.87      B    C
ATOM   3366  CG   ASP B 382      44.101  12.639  38.319  1.00 34.65      B    C
ATOM   3367  OD1  ASP B 382      44.188  13.686  37.611  1.00 35.68      B    O
ATOM   3368  OD2  ASP B 382      44.595  11.556  37.949  1.00 34.92      B    O
ATOM   3369  C    ASP B 382      41.817  14.245  40.930  1.00 31.45      B    C
ATOM   3370  O    ASP B 382      40.937  13.383  40.862  1.00 31.26      B    O
ATOM   3371  N    PHE B 383      41.688  15.387  41.576  1.00 32.04      B    N
ATOM   3372  CA   PHE B 383      40.523  15.725  42.356  0.00 33.89      B    C
ATOM   3373  CB   PHE B 383      40.978  16.510  43.583  1.00 34.36      B    C
ATOM   3374  CG   PHE B 383      41.888  17.669  43.250  1.00 35.47      B    C
ATOM   3375  CD1  PHE B 383      41.358  18.892  42.836  1.00 36.35      B    C
ATOM   3376  CD2  PHE B 383      43.275  17.529  43.331  1.00 35.68      B    C
ATOM   3377  CE1  PHE B 383      42.191  19.974  42.500  1.00 36.28      B    C
ATOM   3378  CE2  PHE B 383      44.139  18.621  42.996  1.00 36.69      B    C
ATOM   3379  CZ   PHE B 383      43.586  19.845  42.579  1.00 36.13      B    C
ATOM   3380  C    PHE B 383      39.560  16.592  41.560  1.00 34.83      B    C
ATOM   3381  O    PHE B 383      39.974  17.362  40.687  1.00 34.78      B    O
ATOM   3382  N    GLY B 384      38.283  16.481  41.894  1.00 35.69      B    N
ATOM   3383  CA   GLY B 384      37.272  17.311  41.279  0.00 37.20      B    C
ATOM   3384  C    GLY B 384      36.755  16.935  39.919  1.00 38.57      B    C
ATOM   3385  O    GLY B 384      35.955  17.671  39.360  1.00 39.70      B    O
ATOM   3386  N    LEU B 385      37.195  15.810  39.370  1.00 39.78      B    N
ATOM   3387  CA   LEU B 385      36.760  15.411  38.037  0.00 40.61      B    C
ATOM   3388  CB   LEU B 385      37.559  14.200  37.507  1.00 40.48      B    C
ATOM   3389  CG   LEU B 385      39.089  14.117  37.694  1.00 40.66      B    C
ATOM   3390  CD1  LEU B 385      39.665  12.930  36.921  1.00 40.28      B    C
ATOM   3391  CD2  LEU B 385      39.776  15.402  37.272  1.00 41.55      B    C
ATOM   3392  C    LEU B 385      35.293  15.040  38.091  1.00 41.68      B    C
ATOM   3393  O    LEU B 385      34.797  14.586  39.126  1.00 41.59      B    O
ATOM   3394  N    ALA B 386      34.615  15.213  36.959  1.00 42.23      B    N
ATOM   3395  CA   ALA B 386      33.195  14.878  36.855  0.00 42.86      B    C
ATOM   3396  CB   ALA B 386      32.551  15.616  35.638  1.00 42.98      B    C
ATOM   3397  C    ALA B 386      33.063  13.386  36.657  1.00 42.40      B    C
ATOM   3398  O    ALA B 386      31.967  12.829  36.745  1.00 42.85      B    O
ATOM   3399  N    ARG B 387      34.184  12.738  36.373  1.00 41.73      B    N
ATOM   3400  CA   ARG B 387      34.143  11.313  36.098  0.00 40.48      B    C
ATOM   3401  CB   ARG B 387      34.580  11.068  34.655  1.00 40.04      B    C
ATOM   3402  CG   ARG B 387      36.035  11.431  34.385  1.00 40.50      B    C
ATOM   3403  CD   ARG B 387      36.420  11.090  32.957  1.00 40.48      B    C
ATOM   3404  NE   ARG B 387      37.865  11.129  32.734  1.00 40.27      B    N
ATOM   3405  CZ   ARG B 387      38.658  10.063  32.840  1.00 39.00      B    C
ATOM   3406  NH1  ARG B 387      38.152   8.875  33.159  1.00 37.56      B    N
ATOM   3407  NH2  ARG B 387      39.968  10.201  32.646  1.00 39.87      B    N
ATOM   3408  C    ARG B 387      34.939  10.427  37.035  1.00 39.86      B    C
ATOM   3409  O    ARG B 387      35.782  10.877  37.805  1.00 40.68      B    O
```

Figure 12

| | | | | | | | | | | | |
|---|---|---|---|---|---|---|---|---|---|---|---|
| ATOM | 3410 | N | LEU | B | 388 | 34.645 | 9.149 | 36.940 | 1.00 | 38.61 | B N |
| ATOM | 3411 | CA | LEU | B | 388 | 35.277 | 8.125 | 37.708 | 0.00 | 37.44 | B C |
| ATOM | 3412 | CB | LEU | B | 388 | 34.218 | 7.102 | 38.038 | 1.00 | 38.10 | B C |
| ATOM | 3413 | CG | LEU | B | 388 | 33.046 | 7.932 | 38.612 | 1.00 | 40.87 | B C |
| ATOM | 3414 | CD1 | LEU | B | 388 | 31.732 | 7.167 | 38.564 | 1.00 | 41.66 | B C |
| ATOM | 3415 | CD2 | LEU | B | 388 | 33.373 | 8.370 | 40.044 | 1.00 | 40.79 | B C |
| ATOM | 3416 | C | LEU | B | 388 | 36.398 | 7.525 | 36.851 | 1.00 | 36.09 | B C |
| ATOM | 3417 | O | LEU | B | 388 | 36.121 | 6.911 | 35.829 | 1.00 | 36.96 | B O |
| ATOM | 3418 | N | ILE | B | 389 | 37.651 | 7.684 | 37.294 | 1.00 | 33.94 | B N |
| ATOM | 3419 | CA | ILE | B | 389 | 38.833 | 7.186 | 36.588 | 0.00 | 31.70 | B C |
| ATOM | 3420 | CB | ILE | B | 389 | 39.986 | 8.209 | 36.660 | 1.00 | 30.88 | B C |
| ATOM | 3421 | CG2 | ILE | B | 389 | 39.513 | 9.569 | 36.189 | 1.00 | 29.25 | B C |
| ATOM | 3422 | CG1 | ILE | B | 389 | 40.567 | 8.334 | 38.077 | 1.00 | 29.97 | B C |
| ATOM | 3423 | CD1 | ILE | B | 389 | 41.402 | 9.626 | 38.281 | 1.00 | 27.43 | B C |
| ATOM | 3424 | C | ILE | B | 389 | 39.363 | 5.828 | 37.012 | 1.00 | 31.62 | B C |
| ATOM | 3425 | O | ILE | B | 389 | 39.089 | 5.366 | 38.112 | 1.00 | 30.46 | B O |
| ATOM | 3426 | N | GLU | B | 390 | 40.006 | 5.123 | 36.077 | 1.00 | 32.01 | B N |
| ATOM | 3427 | CA | GLU | B | 390 | 40.632 | 3.835 | 36.369 | 0.00 | 33.78 | B C |
| ATOM | 3428 | CB | GLU | B | 390 | 40.301 | 2.800 | 35.314 | 1.00 | 34.42 | B C |
| ATOM | 3429 | CG | GLU | B | 390 | 38.883 | 2.319 | 35.392 | 1.00 | 39.86 | B C |
| ATOM | 3430 | CD | GLU | B | 390 | 38.442 | 1.594 | 34.149 | 1.00 | 41.47 | B C |
| ATOM | 3431 | OE1 | GLU | B | 390 | 37.369 | 1.921 | 33.660 | 1.00 | 44.54 | B O |
| ATOM | 3432 | OE2 | GLU | B | 390 | 39.144 | 0.710 | 33.637 | 1.00 | 44.60 | B O |
| ATOM | 3433 | C | GLU | B | 390 | 42.156 | 4.043 | 36.460 | 1.00 | 33.94 | B C |
| ATOM | 3434 | O | GLU | B | 390 | 42.688 | 5.009 | 35.921 | 1.00 | 33.84 | B O |
| ATOM | 3435 | N | ASP | B | 391 | 42.866 | 3.133 | 37.109 | 1.00 | 35.17 | B N |
| ATOM | 3436 | CA | ASP | B | 391 | 44.329 | 3.325 | 37.255 | 0.00 | 36.86 | B C |
| ATOM | 3437 | CB | ASP | B | 391 | 44.906 | 2.467 | 38.380 | 1.00 | 38.82 | B C |
| ATOM | 3438 | CG | ASP | B | 391 | 44.213 | 2.680 | 39.707 | 1.00 | 40.10 | B C |
| ATOM | 3439 | OD1 | ASP | B | 391 | 43.825 | 3.835 | 40.067 | 1.00 | 41.07 | B O |
| ATOM | 3440 | OD2 | ASP | B | 391 | 44.070 | 1.650 | 40.391 | 1.00 | 42.45 | B O |
| ATOM | 3441 | C | ASP | B | 391 | 45.127 | 3.027 | 36.020 | 1.00 | 36.83 | B C |
| ATOM | 3442 | O | ASP | B | 391 | 46.297 | 3.414 | 35.930 | 1.00 | 37.66 | B O |
| ATOM | 3443 | N | ASN | B | 392 | 44.495 | 2.314 | 35.096 | 1.00 | 36.05 | B N |
| ATOM | 3444 | CA | ASN | B | 392 | 45.105 | 1.899 | 33.853 | 0.00 | 35.17 | B C |
| ATOM | 3445 | CB | ASN | B | 392 | 44.519 | 0.538 | 33.446 | 1.00 | 35.42 | B C |
| ATOM | 3446 | CG | ASN | B | 392 | 43.122 | 0.659 | 32.849 | 1.00 | 36.94 | B C |
| ATOM | 3447 | OD1 | ASN | B | 392 | 42.442 | 1.687 | 32.994 | 1.00 | 36.47 | B O |
| ATOM | 3448 | ND2 | ASN | B | 392 | 42.697 | -0.382 | 32.144 | 1.00 | 37.77 | B N |
| ATOM | 3449 | C | ASN | B | 392 | 44.961 | 2.900 | 32.695 | 1.00 | 33.93 | B C |
| ATOM | 3450 | O | ASN | B | 392 | 45.099 | 2.532 | 31.531 | 1.00 | 33.70 | B O |
| ATOM | 3451 | N | GLU | B | 393 | 44.665 | 4.148 | 33.000 | 1.00 | 33.31 | B N |
| ATOM | 3452 | CA | GLU | B | 393 | 44.488 | 5.138 | 31.959 | 0.00 | 32.78 | B C |
| ATOM | 3453 | CB | GLU | B | 393 | 43.581 | 6.263 | 32.424 | 1.00 | 31.03 | B C |
| ATOM | 3454 | CG | GLU | B | 393 | 42.156 | 5.933 | 32.122 | 1.00 | 30.87 | B C |
| ATOM | 3455 | CD | GLU | B | 393 | 41.153 | 6.613 | 33.020 | 1.00 | 29.09 | B C |
| ATOM | 3456 | OE1 | GLU | B | 393 | 41.322 | 7.790 | 33.399 | 1.00 | 28.94 | B O |
| ATOM | 3457 | OE2 | GLU | B | 393 | 40.163 | 5.949 | 33.303 | 1.00 | 30.23 | B O |
| ATOM | 3458 | C | GLU | B | 393 | 45.767 | 5.735 | 31.467 | 1.00 | 33.73 | B C |
| ATOM | 3459 | O | GLU | B | 393 | 45.886 | 6.029 | 30.282 | 1.00 | 32.80 | B O |
| ATOM | 3460 | N | TYR | B | 394 | 46.689 | 5.951 | 32.396 | 1.00 | 34.59 | B N |
| ATOM | 3461 | CA | TYR | B | 394 | 47.962 | 6.559 | 32.076 | 0.00 | 36.43 | B C |
| ATOM | 3462 | CB | TYR | B | 394 | 47.997 | 7.980 | 32.641 | 1.00 | 34.84 | B C |
| ATOM | 3463 | CG | TYR | B | 394 | 46.874 | 8.832 | 32.097 | 1.00 | 34.14 | B C |
| ATOM | 3464 | CD1 | TYR | B | 394 | 45.634 | 8.900 | 32.742 | 1.00 | 33.06 | B C |
| ATOM | 3465 | CE1 | TYR | B | 394 | 44.576 | 9.641 | 32.205 | 1.00 | 32.60 | B C |
| ATOM | 3466 | CD2 | TYR | B | 394 | 47.029 | 9.536 | 30.904 | 1.00 | 34.07 | B C |
| ATOM | 3467 | CE2 | TYR | B | 394 | 45.987 | 10.284 | 30.352 | 1.00 | 33.33 | B C |
| ATOM | 3468 | CZ | TYR | B | 394 | 44.751 | 10.334 | 31.002 | 1.00 | 33.26 | B C |

Figure 12

```
ATOM   3469  OH  TYR B 394      43.723  11.048  30.418  1.00 29.99      B  O
ATOM   3470  C   TYR B 394      49.185   5.718  32.491  1.00 38.14      B  C
ATOM   3471  O   TYR B 394      50.324   6.158  32.302  1.00 38.27      B  O
ATOM   3472  N   THR B 395      48.932   4.525  33.037  1.00 39.72      B  N
ATOM   3473  CA  THR B 395      49.969   3.588  33.450  0.00 42.69      B  C
ATOM   3474  CB  THR B 395      50.331   3.681  34.948  1.00 43.60      B  C
ATOM   3475  OG1 THR B 395      49.171   3.436  35.759  1.00 43.58      B  O
ATOM   3476  CG2 THR B 395      50.957   5.039  35.266  1.00 44.08      B  C
ATOM   3477  C   THR B 395      49.444   2.205  33.162  1.00 44.65      B  C
ATOM   3478  O   THR B 395      48.338   2.068  32.655  1.00 45.10      B  O
ATOM   3479  N   ALA B 396      50.178   1.166  33.530  1.00 47.14      B  N
ATOM   3480  CA  ALA B 396      49.717  -0.172  33.204  0.00 50.17      B  C
ATOM   3481  CB  ALA B 396      50.730  -0.872  32.279  1.00 49.88      B  C
ATOM   3482  C   ALA B 396      49.252  -1.125  34.309  1.00 52.54      B  C
ATOM   3483  O   ALA B 396      49.324  -2.350  34.121  1.00 53.55      B  O
ATOM   3484  N   ARG B 397      48.690  -0.590  35.399  1.00 54.64      B  N
ATOM   3485  CA  ARG B 397      48.191  -1.440  36.493  0.00 55.78      B  C
ATOM   3486  CB  ARG B 397      47.752  -0.591  37.691  1.00 55.96      B  C
ATOM   3487  CG  ARG B 397      48.818   0.357  38.216  1.00 56.33      B  C
ATOM   3488  CD  ARG B 397      48.800   0.402  39.735  1.00 56.71      B  C
ATOM   3489  NE  ARG B 397      49.518   1.559  40.271  1.00 56.32      B  N
ATOM   3490  CZ  ARG B 397      49.070   2.811  40.193  1.00 55.91      B  C
ATOM   3491  NH1 ARG B 397      47.917   3.069  39.594  1.00 55.69      B  N
ATOM   3492  NH2 ARG B 397      49.745   3.798  40.756  1.00 55.32      B  N
ATOM   3493  C   ARG B 397      47.010  -2.308  36.007  1.00 56.53      B  C
ATOM   3494  O   ARG B 397      47.228  -3.528  35.762  1.00 57.38      B  O
ATOM   3495  CB  PRO B 403      37.464   1.930  40.474  1.00 32.96      B  C
ATOM   3496  CG  PRO B 403      37.826   1.391  39.068  1.00 33.39      B  C
ATOM   3497  C   PRO B 403      36.013   0.834  42.258  1.00 31.94      B  C
ATOM   3498  O   PRO B 403      35.890   1.844  43.019  1.00 32.02      B  O
ATOM   3499  N   PRO B 403      36.788  -0.385  40.160  1.00 32.61      B  N
ATOM   3500  CD  PRO B 403      36.881   0.190  38.828  1.00 34.00      B  C
ATOM   3501  CA  PRO B 403      37.154   0.652  41.212  0.00 32.44      B  C
ATOM   3502  N   ILE B 404      35.290  -0.267  42.389  1.00 30.23      B  N
ATOM   3503  CA  ILE B 404      34.150  -0.376  43.256  0.00 28.69      B  C
ATOM   3504  CB  ILE B 404      33.371  -1.621  42.778  1.00 29.68      B  C
ATOM   3505  CG2 ILE B 404      32.775  -2.390  43.920  1.00 29.69      B  C
ATOM   3506  CG1 ILE B 404      32.339  -1.169  41.767  1.00 32.20      B  C
ATOM   3507  CD1 ILE B 404      31.396  -0.118  42.349  1.00 32.65      B  C
ATOM   3508  C   ILE B 404      34.487  -0.390  44.764  1.00 26.67      B  C
ATOM   3509  O   ILE B 404      33.794   0.219  45.574  1.00 25.67      B  O
ATOM   3510  N   LYS B 405      35.637  -0.967  45.101  1.00 24.58      B  N
ATOM   3511  CA  LYS B 405      36.068  -1.118  46.484  0.00 21.64      B  C
ATOM   3512  CB  LYS B 405      37.284  -2.041  46.569  1.00 19.69      B  C
ATOM   3513  CG  LYS B 405      37.016  -3.401  45.993  1.00 19.14      B  C
ATOM   3514  CD  LYS B 405      38.161  -4.345  46.238  1.00 18.84      B  C
ATOM   3515  CE  LYS B 405      37.847  -5.783  45.865  1.00 19.86      B  C
ATOM   3516  NZ  LYS B 405      38.899  -6.755  46.383  1.00 23.48      B  N
ATOM   3517  C   LYS B 405      36.264   0.117  47.325  1.00 20.29      B  C
ATOM   3518  O   LYS B 405      36.478  -0.024  48.511  1.00 20.05      B  O
ATOM   3519  N   TRP B 406      36.256   1.302  46.713  1.00 19.55      B  N
ATOM   3520  CA  TRP B 406      36.388   2.581  47.434  0.00 19.82      B  C
ATOM   3521  CB  TRP B 406      37.497   3.487  46.822  1.00 19.51      B  C
ATOM   3522  CG  TRP B 406      38.927   2.939  46.996  1.00 19.75      B  C
ATOM   3523  CD2 TRP B 406      39.563   1.922  46.192  1.00 20.04      B  C
ATOM   3524  CE2 TRP B 406      40.870   1.719  46.737  1.00 21.00      B  C
ATOM   3525  CE3 TRP B 406      39.166   1.168  45.088  1.00 21.07      B  C
ATOM   3526  CD1 TRP B 406      39.842   3.314  47.961  1.00 19.28      B  C
ATOM   3527  NE1 TRP B 406      41.008   2.564  47.807  1.00 21.28      B  N
```

Figure 12

```
ATOM   3528  CZ2  TRP  B  406     41.782   0.777  46.189  1.00 22.01      B  C
ATOM   3529  CZ3  TRP  B  406     40.078   0.223  44.535  1.00 22.62      B  C
ATOM   3530  CH2  TRP  B  406     41.379   0.043  45.099  1.00 21.92      B  C
ATOM   3531  C    TRP  B  406     35.097   3.403  47.402  1.00 19.92      B  C
ATOM   3532  O    TRP  B  406     35.056   4.518  47.943  1.00 19.72      B  O
ATOM   3533  N    THR  B  407     34.048   2.863  46.772  1.00 18.96      B  N
ATOM   3534  CA   THR  B  407     32.785   3.601  46.597  0.00 18.99      B  C
ATOM   3535  CB   THR  B  407     32.151   3.186  45.254  1.00 20.73      B  C
ATOM   3536  OG1  THR  B  407     33.132   3.296  44.217  1.00 23.19      B  O
ATOM   3537  CG2  THR  B  407     30.960   4.093  44.891  1.00 21.49      B  C
ATOM   3538  C    THR  B  407     31.770   3.382  47.735  1.00 17.85      B  C
ATOM   3539  O    THR  B  407     31.520   2.236  48.110  1.00 16.47      B  O
ATOM   3540  N    ALA  B  408     31.252   4.476  48.304  1.00 16.70      B  N
ATOM   3541  CA   ALA  B  408     30.260   4.416  49.389  0.00 18.55      B  C
ATOM   3542  CB   ALA  B  408     29.946   5.807  49.870  1.00 18.39      B  C
ATOM   3543  C    ALA  B  408     28.984   3.758  48.911  1.00 19.42      B  C
ATOM   3544  O    ALA  B  408     28.667   3.850  47.727  1.00 19.52      B  O
ATOM   3545  N    PRO  B  409     28.185   3.139  49.818  1.00 20.38      B  N
ATOM   3546  CD   PRO  B  409     28.399   2.988  51.263  1.00 20.51      B  C
ATOM   3547  CA   PRO  B  409     26.931   2.484  49.396  0.00 21.37      B  C
ATOM   3548  CB   PRO  B  409     26.347   1.949  50.715  1.00 21.67      B  C
ATOM   3549  CG   PRO  B  409     27.541   1.805  51.592  1.00 21.50      B  C
ATOM   3550  C    PRO  B  409     25.916   3.364  48.647  1.00 21.59      B  C
ATOM   3551  O    PRO  B  409     25.312   2.911  47.686  1.00 21.00      B  O
ATOM   3552  N    GLU  B  410     25.687   4.592  49.095  1.00 21.93      B  N
ATOM   3553  CA   GLU  B  410     24.737   5.450  48.406  0.00 23.32      B  C
ATOM   3554  CB   GLU  B  410     24.439   6.721  49.228  1.00 21.89      B  C
ATOM   3555  CG   GLU  B  410     25.601   7.772  49.307  1.00 21.78      B  C
ATOM   3556  CD   GLU  B  410     26.765   7.432  50.312  1.00 20.37      B  C
ATOM   3557  OE1  GLU  B  410     26.717   6.386  50.986  1.00 19.87      B  O
ATOM   3558  OE2  GLU  B  410     27.686   8.267  50.473  1.00 17.33      B  O
ATOM   3559  C    GLU  B  410     25.256   5.845  47.014  1.00 25.07      B  C
ATOM   3560  O    GLU  B  410     24.490   6.299  46.138  1.00 26.18      B  O
ATOM   3561  N    ALA  B  411     26.551   5.712  46.791  1.00 24.78      B  N
ATOM   3562  CA   ALA  B  411     27.064   6.062  45.476  0.00 25.03      B  C
ATOM   3563  CB   ALA  B  411     28.503   6.501  45.558  1.00 24.13      B  C
ATOM   3564  C    ALA  B  411     26.888   4.846  44.589  1.00 24.87      B  C
ATOM   3565  O    ALA  B  411     26.582   4.947  43.395  1.00 25.02      B  O
ATOM   3566  N    ILE  B  412     27.008   3.672  45.180  1.00 25.02      B  N
ATOM   3567  CA   ILE  B  412     26.807   2.469  44.401  0.00 26.99      B  C
ATOM   3568  CB   ILE  B  412     27.196   1.214  45.173  1.00 26.12      B  C
ATOM   3569  CG2  ILE  B  412     26.803  -0.037  44.393  1.00 25.29      B  C
ATOM   3570  CG1  ILE  B  412     28.696   1.205  45.410  1.00 25.10      B  C
ATOM   3571  CD1  ILE  B  412     29.152   0.057  46.243  1.00 25.60      B  C
ATOM   3572  C    ILE  B  412     25.352   2.289  43.999  1.00 28.51      B  C
ATOM   3573  O    ILE  B  412     25.081   1.920  42.874  1.00 29.70      B  O
ATOM   3574  N    ASN  B  413     24.442   2.560  44.931  1.00 29.88      B  N
ATOM   3575  CA   ASN  B  413     23.000   2.367  44.765  0.00 30.84      B  C
ATOM   3576  CB   ASN  B  413     22.357   2.129  46.131  1.00 31.05      B  C
ATOM   3577  CG   ASN  B  413     22.877   0.867  46.795  1.00 32.66      B  C
ATOM   3578  OD1  ASN  B  413     23.097  -0.150  46.128  1.00 34.72      B  O
ATOM   3579  ND2  ASN  B  413     23.099   0.923  48.103  1.00 31.55      B  N
ATOM   3580  C    ASN  B  413     22.205   3.409  44.022  1.00 31.13      B  C
ATOM   3581  O    ASN  B  413     21.273   3.060  43.340  1.00 31.49      B  O
ATOM   3582  N    TYR  B  414     22.618   4.669  44.127  1.00 31.96      B  N
ATOM   3583  CA   TYR  B  414     21.944   5.800  43.513  0.00 32.42      B  C
ATOM   3584  CB   TYR  B  414     21.215   6.583  44.601  1.00 34.81      B  C
ATOM   3585  CG   TYR  B  414     20.337   5.707  45.459  1.00 38.31      B  C
ATOM   3586  CD1  TYR  B  414     19.138   5.187  44.962  1.00 38.34      B  C
```

Figure 12

```
ATOM   3587  CE1 TYR B 414      18.334   4.355  45.767  1.00 40.07      B    C
ATOM   3588  CD2 TYR B 414      20.716   5.379  46.774  1.00 39.21      B    C
ATOM   3589  CE2 TYR B 414      19.913   4.553  47.577  1.00 40.34      B    C
ATOM   3590  CZ  TYR B 414      18.732   4.054  47.064  1.00 39.59      B    C
ATOM   3591  OH  TYR B 414      17.927   3.282  47.858  1.00 42.14      B    O
ATOM   3592  C   TYR B 414      22.869   6.782  42.761  1.00 31.79      B    C
ATOM   3593  O   TYR B 414      22.395   7.803  42.226  1.00 31.50      B    O
ATOM   3594  N   GLY B 415      24.173   6.523  42.759  1.00 30.45      B    N
ATOM   3595  CA  GLY B 415      25.074   7.434  42.065  0.00 30.58      B    C
ATOM   3596  C   GLY B 415      25.169   8.835  42.660  1.00 30.44      B    C
ATOM   3597  O   GLY B 415      25.436   9.815  41.951  1.00 30.28      B    O
ATOM   3598  N   THR B 416      24.912   8.941  43.966  1.00 30.49      B    N
ATOM   3599  CA  THR B 416      25.005  10.207  44.686  0.00 29.64      B    C
ATOM   3600  CB  THR B 416      23.797  10.348  45.739  1.00 30.46      B    C
ATOM   3601  OG1 THR B 416      24.241  10.912  46.983  1.00 31.36      B    O
ATOM   3602  CG2 THR B 416      23.157   9.048  46.015  1.00 28.02      B    C
ATOM   3603  C   THR B 416      26.407  10.264  45.325  1.00 29.12      B    C
ATOM   3604  O   THR B 416      26.739   9.433  46.147  1.00 29.74      B    O
ATOM   3605  N   PHE B 417      27.244  11.201  44.869  1.00 27.98      B    N
ATOM   3606  CA  PHE B 417      28.599  11.391  45.375  0.00 26.40      B    C
ATOM   3607  CB  PHE B 417      29.667  11.379  44.234  1.00 25.65      B    C
ATOM   3608  CG  PHE B 417      29.866  10.023  43.560  1.00 25.80      B    C
ATOM   3609  CD1 PHE B 417      28.933   9.535  42.631  1.00 24.48      B    C
ATOM   3610  CD2 PHE B 417      30.957   9.204  43.900  1.00 24.55      B    C
ATOM   3611  CE1 PHE B 417      29.087   8.257  42.072  1.00 23.83      B    C
ATOM   3612  CE2 PHE B 417      31.114   7.922  43.343  1.00 21.93      B    C
ATOM   3613  CZ  PHE B 417      30.197   7.452  42.447  1.00 23.51      B    C
ATOM   3614  C   PHE B 417      28.638  12.755  46.005  1.00 25.36      B    C
ATOM   3615  O   PHE B 417      28.278  13.734  45.375  1.00 25.49      B    O
ATOM   3616  N   THR B 418      29.132  12.820  47.234  1.00 25.37      B    N
ATOM   3617  CA  THR B 418      29.276  14.075  47.986  0.00 24.52      B    C
ATOM   3618  CB  THR B 418      28.154  14.216  49.043  1.00 25.10      B    C
ATOM   3619  OG1 THR B 418      28.313  13.199  50.026  1.00 25.10      B    O
ATOM   3620  CG2 THR B 418      26.739  14.073  48.399  1.00 23.71      B    C
ATOM   3621  C   THR B 418      30.623  13.938  48.733  1.00 23.84      B    C
ATOM   3622  O   THR B 418      31.329  12.933  48.580  1.00 23.43      B    O
ATOM   3623  N   ILE B 419      30.943  14.892  49.587  1.00 23.58      B    N
ATOM   3624  CA  ILE B 419      32.175  14.801  50.368  0.00 23.47      B    C
ATOM   3625  CB  ILE B 419      32.466  16.131  51.105  1.00 24.50      B    C
ATOM   3626  CG2 ILE B 419      31.464  16.380  52.251  1.00 24.62      B    C
ATOM   3627  CG1 ILE B 419      33.908  16.143  51.609  1.00 25.39      B    C
ATOM   3628  CD1 ILE B 419      34.942  16.492  50.517  1.00 25.31      B    C
ATOM   3629  C   ILE B 419      32.100  13.634  51.364  1.00 23.38      B    C
ATOM   3630  O   ILE B 419      33.118  13.066  51.761  1.00 23.50      B    O
ATOM   3631  N   LYS B 420      30.878  13.216  51.710  1.00 22.80      B    N
ATOM   3632  CA  LYS B 420      30.696  12.104  52.645  0.00 20.73      B    C
ATOM   3633  CB  LYS B 420      29.274  12.093  53.225  1.00 20.25      B    C
ATOM   3634  CG  LYS B 420      28.966  13.322  54.008  1.00 18.49      B    C
ATOM   3635  CD  LYS B 420      29.732  13.289  55.271  1.00 20.58      B    C
ATOM   3636  CE  LYS B 420      29.432  14.495  56.092  1.00 19.31      B    C
ATOM   3637  NZ  LYS B 420      30.433  14.526  57.170  1.00 18.51      B    N
ATOM   3638  C   LYS B 420      31.072  10.796  51.979  1.00 19.78      B    C
ATOM   3639  O   LYS B 420      31.540   9.879  52.637  1.00 19.02      B    O
ATOM   3640  N   SER B 421      30.869  10.668  50.670  1.00 19.91      B    N
ATOM   3641  CA  SER B 421      31.345   9.443  50.043  0.00 19.47      B    C
ATOM   3642  CB  SER B 421      30.625   9.114  48.737  1.00 20.55      B    C
ATOM   3643  OG  SER B 421      30.207  10.272  48.057  1.00 22.44      B    O
ATOM   3644  C   SER B 421      32.880   9.513  49.887  1.00 19.57      B    C
ATOM   3645  O   SER B 421      33.530   8.475  49.761  1.00 20.50      B    O
```

Figure 12

```
ATOM   3646  N    ASP B 422      33.484  10.704  49.884  1.00 19.16      B    N
ATOM   3647  CA   ASP B 422      34.959  10.767  49.834  0.00 18.87      B    C
ATOM   3648  CB   ASP B 422      35.505  12.201  49.593  1.00 17.85      B    C
ATOM   3649  CG   ASP B 422      35.231  12.716  48.204  1.00 18.46      B    C
ATOM   3650  OD1  ASP B 422      35.225  11.934  47.243  1.00 21.83      B    O
ATOM   3651  OD2  ASP B 422      35.040  13.933  48.039  1.00 21.39      B    O
ATOM   3652  C    ASP B 422      35.445  10.311  51.212  1.00 19.45      B    C
ATOM   3653  O    ASP B 422      36.462   9.632  51.313  1.00 21.83      B    O
ATOM   3654  N    VAL B 423      34.739  10.694  52.281  1.00 18.40      B    N
ATOM   3655  CA   VAL B 423      35.085  10.295  53.636  0.00 16.26      B    C
ATOM   3656  CB   VAL B 423      34.114  10.901  54.734  1.00 17.52      B    C
ATOM   3657  CG1  VAL B 423      34.333  10.200  56.148  1.00 13.79      B    C
ATOM   3658  CG2  VAL B 423      34.412  12.408  54.875  1.00 15.99      B    C
ATOM   3659  C    VAL B 423      35.060   8.801  53.706  1.00 15.62      B    C
ATOM   3660  O    VAL B 423      35.899   8.184  54.374  1.00 15.38      B    O
ATOM   3661  N    TRP B 424      34.132   8.177  52.996  1.00 15.88      B    N
ATOM   3662  CA   TRP B 424      34.053   6.730  53.014  0.00 14.99      B    C
ATOM   3663  CB   TRP B 424      32.747   6.246  52.342  1.00 14.04      B    C
ATOM   3664  CG   TRP B 424      32.696   4.751  52.037  1.00 11.69      B    C
ATOM   3665  CD2  TRP B 424      31.874   3.751  52.673  1.00 13.14      B    C
ATOM   3666  CE2  TRP B 424      32.277   2.505  52.154  1.00 13.58      B    C
ATOM   3667  CE3  TRP B 424      30.845   3.804  53.623  1.00 14.21      B    C
ATOM   3668  CD1  TRP B 424      33.477   4.090  51.169  1.00 12.01      B    C
ATOM   3669  NE1  TRP B 424      33.243   2.732  51.239  1.00 11.03      B    N
ATOM   3670  CZ2  TRP B 424      31.668   1.253  52.568  1.00 15.12      B    C
ATOM   3671  CZ3  TRP B 424      30.242   2.567  54.026  1.00 14.08      B    C
ATOM   3672  CH2  TRP B 424      30.660   1.322  53.504  1.00 14.06      B    C
ATOM   3673  C    TRP B 424      35.297   6.214  52.298  1.00 15.77      B    C
ATOM   3674  O    TRP B 424      35.919   5.260  52.745  1.00 15.76      B    O
ATOM   3675  N    SER B 425      35.674   6.853  51.188  1.00 16.58      B    N
ATOM   3676  CA   SER B 425      36.868   6.462  50.433  0.00 18.59      B    C
ATOM   3677  CB   SER B 425      37.032   7.308  49.180  1.00 20.01      B    C
ATOM   3678  OG   SER B 425      36.071   6.908  48.253  1.00 23.15      B    O
ATOM   3679  C    SER B 425      38.134   6.602  51.279  1.00 18.75      B    C
ATOM   3680  O    SER B 425      39.002   5.750  51.237  1.00 18.80      B    O
ATOM   3681  N    PHE B 426      38.217   7.682  52.017  1.00 18.33      B    N
ATOM   3682  CA   PHE B 426      39.356   7.898  52.892  0.00 19.58      B    C
ATOM   3683  CB   PHE B 426      39.253   9.248  53.585  1.00 18.36      B    C
ATOM   3684  CG   PHE B 426      40.446   9.576  54.402  1.00 20.55      B    C
ATOM   3685  CD1  PHE B 426      41.591  10.083  53.789  1.00 21.58      B    C
ATOM   3686  CD2  PHE B 426      40.430   9.400  55.791  1.00 20.22      B    C
ATOM   3687  CE1  PHE B 426      42.715  10.423  54.553  1.00 23.56      B    C
ATOM   3688  CE2  PHE B 426      41.548   9.727  56.578  1.00 20.44      B    C
ATOM   3689  CZ   PHE B 426      42.695  10.242  55.960  1.00 23.77      B    C
ATOM   3690  C    PHE B 426      39.541   6.738  53.891  1.00 20.14      B    C
ATOM   3691  O    PHE B 426      40.676   6.257  54.093  1.00 20.74      B    O
ATOM   3692  N    GLY B 427      38.452   6.277  54.504  1.00 19.15      B    N
ATOM   3693  CA   GLY B 427      38.561   5.145  55.390  0.00 17.45      B    C
ATOM   3694  C    GLY B 427      39.128   3.942  54.625  1.00 18.69      B    C
ATOM   3695  O    GLY B 427      39.950   3.212  55.170  1.00 19.43      B    O
ATOM   3696  N    ILE B 428      38.659   3.659  53.400  1.00 18.40      B    N
ATOM   3697  CA   ILE B 428      39.230   2.531  52.639  0.00 17.94      B    C
ATOM   3698  CB   ILE B 428      38.543   2.314  51.254  1.00 16.67      B    C
ATOM   3699  CG2  ILE B 428      39.158   1.112  50.543  1.00 14.30      B    C
ATOM   3700  CG1  ILE B 428      37.021   2.130  51.414  1.00 16.55      B    C
ATOM   3701  CD1  ILE B 428      36.575   0.789  52.058  1.00 16.13      B    C
ATOM   3702  C    ILE B 428      40.748   2.826  52.398  1.00 18.74      B    C
ATOM   3703  O    ILE B 428      41.610   1.945  52.581  1.00 17.41      B    O
ATOM   3704  N    LEU B 429      41.055   4.071  52.044  1.00 17.61      B    N
```

Figure 12

| | | | | | | | | | | | |
|---|---|---|---|---|---|---|---|---|---|---|---|
| ATOM | 3705 | CA  | LEU | B | 429 | 42.440 | 4.483  | 51.831 | 0.00 | 19.41 | B | C |
| ATOM | 3706 | CB  | LEU | B | 429 | 42.474 | 5.993  | 51.533 | 1.00 | 19.02 | B | C |
| ATOM | 3707 | CG  | LEU | B | 429 | 43.731 | 6.486  | 50.826 | 1.00 | 21.06 | B | C |
| ATOM | 3708 | CD1 | LEU | B | 429 | 43.468 | 7.834  | 50.204 | 1.00 | 19.91 | B | C |
| ATOM | 3709 | CD2 | LEU | B | 429 | 44.892 | 6.553  | 51.739 | 1.00 | 20.85 | B | C |
| ATOM | 3710 | C   | LEU | B | 429 | 43.369 | 4.148  | 53.050 | 1.00 | 19.40 | B | C |
| ATOM | 3711 | O   | LEU | B | 429 | 44.513 | 3.723  | 52.863 | 1.00 | 20.47 | B | O |
| ATOM | 3712 | N   | LEU | B | 430 | 42.895 | 4.412  | 54.271 | 1.00 | 19.83 | B | N |
| ATOM | 3713 | CA  | LEU | B | 430 | 43.633 | 4.143  | 55.517 | 0.00 | 20.06 | B | C |
| ATOM | 3714 | CB  | LEU | B | 430 | 42.811 | 4.563  | 56.752 | 1.00 | 20.60 | B | C |
| ATOM | 3715 | CG  | LEU | B | 430 | 42.600 | 6.061  | 56.987 | 1.00 | 20.34 | B | C |
| ATOM | 3716 | CD1 | LEU | B | 430 | 41.548 | 6.277  | 58.040 | 1.00 | 21.28 | B | C |
| ATOM | 3717 | CD2 | LEU | B | 430 | 43.919 | 6.693  | 57.428 | 1.00 | 20.38 | B | C |
| ATOM | 3718 | C   | LEU | B | 430 | 43.978 | 2.682  | 55.629 | 1.00 | 19.93 | B | C |
| ATOM | 3719 | O   | LEU | B | 430 | 45.003 | 2.347  | 56.172 | 1.00 | 20.85 | B | O |
| ATOM | 3720 | N   | THR | B | 431 | 43.168 | 1.788  | 55.058 | 1.00 | 20.70 | B | N |
| ATOM | 3721 | CA  | THR | B | 431 | 43.495 | 0.387  | 55.132 | 0.00 | 21.16 | B | C |
| ATOM | 3722 | CB  | THR | B | 431 | 42.320 | -0.577 | 54.823 | 1.00 | 19.97 | B | C |
| ATOM | 3723 | OG1 | THR | B | 431 | 42.002 | -0.570 | 53.408 | 1.00 | 20.92 | B | O |
| ATOM | 3724 | CG2 | THR | B | 431 | 41.130 | -0.274 | 55.685 | 1.00 | 20.96 | B | C |
| ATOM | 3725 | C   | THR | B | 431 | 44.673 | 0.114  | 54.194 | 1.00 | 22.96 | B | C |
| ATOM | 3726 | O   | THR | B | 431 | 45.546 | -0.715 | 54.498 | 1.00 | 22.59 | B | O |
| ATOM | 3727 | N   | GLU | B | 432 | 44.655 | 0.766  | 53.034 | 1.00 | 23.48 | B | N |
| ATOM | 3728 | CA  | GLU | B | 432 | 45.737 | 0.634  | 52.080 | 0.00 | 24.03 | B | C |
| ATOM | 3729 | CB  | GLU | B | 432 | 45.504 | 1.475  | 50.838 | 1.00 | 23.93 | B | C |
| ATOM | 3730 | CG  | GLU | B | 432 | 44.437 | 0.956  | 49.924 | 1.00 | 24.39 | B | C |
| ATOM | 3731 | CD  | GLU | B | 432 | 44.303 | 1.867  | 48.742 | 1.00 | 24.58 | B | C |
| ATOM | 3732 | OE1 | GLU | B | 432 | 43.791 | 3.009  | 48.894 | 1.00 | 23.02 | B | O |
| ATOM | 3733 | OE2 | GLU | B | 432 | 44.756 | 1.450  | 47.669 | 1.00 | 24.70 | B | O |
| ATOM | 3734 | C   | GLU | B | 432 | 47.007 | 1.126  | 52.729 | 1.00 | 23.74 | B | C |
| ATOM | 3735 | O   | GLU | B | 432 | 48.053 | 0.532  | 52.537 | 1.00 | 23.89 | B | O |
| ATOM | 3736 | N   | ILE | B | 433 | 46.908 | 2.225  | 53.475 | 1.00 | 23.30 | B | N |
| ATOM | 3737 | CA  | ILE | B | 433 | 48.052 | 2.821  | 54.129 | 0.00 | 24.00 | B | C |
| ATOM | 3738 | CB  | ILE | B | 433 | 47.700 | 4.184  | 54.711 | 1.00 | 22.44 | B | C |
| ATOM | 3739 | CG2 | ILE | B | 433 | 48.698 | 4.620  | 55.770 | 1.00 | 22.81 | B | C |
| ATOM | 3740 | CG1 | ILE | B | 433 | 47.589 | 5.220  | 53.585 | 1.00 | 23.67 | B | C |
| ATOM | 3741 | CD1 | ILE | B | 433 | 47.217 | 6.620  | 54.083 | 1.00 | 23.80 | B | C |
| ATOM | 3742 | C   | ILE | B | 433 | 48.713 | 1.970  | 55.227 | 1.00 | 25.78 | B | C |
| ATOM | 3743 | O   | ILE | B | 433 | 49.932 | 1.961  | 55.325 | 1.00 | 25.87 | B | O |
| ATOM | 3744 | N   | VAL | B | 434 | 47.914 | 1.284  | 56.055 | 1.00 | 27.28 | B | N |
| ATOM | 3745 | CA  | VAL | B | 434 | 48.472 | 0.493  | 57.130 | 0.00 | 28.80 | B | C |
| ATOM | 3746 | CB  | VAL | B | 434 | 47.653 | 0.584  | 58.465 | 1.00 | 29.09 | B | C |
| ATOM | 3747 | CG1 | VAL | B | 434 | 47.444 | 2.047  | 58.856 | 1.00 | 29.34 | B | C |
| ATOM | 3748 | CG2 | VAL | B | 434 | 46.341 | -0.200 | 58.370 | 1.00 | 27.43 | B | C |
| ATOM | 3749 | C   | VAL | B | 434 | 48.800 | -0.943 | 56.762 | 1.00 | 29.82 | B | C |
| ATOM | 3750 | O   | VAL | B | 434 | 49.413 | -1.656 | 57.559 | 1.00 | 30.57 | B | O |
| ATOM | 3751 | N   | THR | B | 435 | 48.394 | -1.387 | 55.584 | 1.00 | 30.55 | B | N |
| ATOM | 3752 | CA  | THR | B | 435 | 48.738 | -2.726 | 55.141 | 0.00 | 32.17 | B | C |
| ATOM | 3753 | CB  | THR | B | 435 | 47.502 | -3.486 | 54.620 | 1.00 | 32.52 | B | C |
| ATOM | 3754 | OG1 | THR | B | 435 | 46.947 | -2.794 | 53.482 | 1.00 | 33.28 | B | O |
| ATOM | 3755 | CG2 | THR | B | 435 | 46.478 | -3.692 | 55.737 | 1.00 | 29.56 | B | C |
| ATOM | 3756 | C   | THR | B | 435 | 49.764 | -2.634 | 53.987 | 1.00 | 33.70 | B | C |
| ATOM | 3757 | O   | THR | B | 435 | 49.942 | -3.591 | 53.226 | 1.00 | 34.12 | B | O |
| ATOM | 3758 | N   | HIS | B | 436 | 50.396 | -1.471 | 53.840 | 1.00 | 35.28 | B | N |
| ATOM | 3759 | CA  | HIS | B | 436 | 51.362 | -1.186 | 52.770 | 0.00 | 36.88 | B | C |
| ATOM | 3760 | CB  | HIS | B | 436 | 52.705 | -1.887 | 53.019 | 1.00 | 40.50 | B | C |
| ATOM | 3761 | CG  | HIS | B | 436 | 53.293 | -1.598 | 54.375 | 1.00 | 42.95 | B | C |
| ATOM | 3762 | CD2 | HIS | B | 436 | 53.567 | -2.423 | 55.412 | 1.00 | 44.08 | B | C |
| ATOM | 3763 | ND1 | HIS | B | 436 | 53.573 | -0.321 | 54.826 | 1.00 | 43.80 | B | N |

Figure 12

| | | | | | | | | | | |
|---|---|---|---|---|---|---|---|---|---|---|
| ATOM | 3764 | CE1 | HIS | B | 436 | 53.979 | -0.364 | 56.086 | 1.00 43.02 | B C |
| ATOM | 3765 | NE2 | HIS | B | 436 | 53.978 | -1.629 | 56.465 | 1.00 44.96 | B N |
| ATOM | 3766 | C | HIS | B | 436 | 50.873 | -1.437 | 51.339 | 1.00 36.66 | B C |
| ATOM | 3767 | O | HIS | B | 436 | 51.497 | -2.157 | 50.585 | 1.00 36.55 | B O |
| ATOM | 3768 | N | GLY | B | 437 | 49.739 | -0.842 | 50.972 | 1.00 36.39 | B N |
| ATOM | 3769 | CA | GLY | B | 437 | 49.224 | -0.973 | 49.620 | 0.00 35.95 | B C |
| ATOM | 3770 | C | GLY | B | 437 | 48.449 | -2.212 | 49.250 | 1.00 35.72 | B C |
| ATOM | 3771 | O | GLY | B | 437 | 48.311 | -2.531 | 48.075 | 1.00 36.45 | B O |
| ATOM | 3772 | N | ARG | B | 438 | 47.962 | -2.928 | 50.246 | 1.00 35.15 | B N |
| ATOM | 3773 | CA | ARG | B | 438 | 47.180 | -4.119 | 50.009 | 0.00 34.74 | B C |
| ATOM | 3774 | CB | ARG | B | 438 | 47.074 | -4.880 | 51.309 | 1.00 37.21 | B C |
| ATOM | 3775 | CG | ARG | B | 438 | 46.662 | -6.322 | 51.167 | 1.00 41.57 | B C |
| ATOM | 3776 | CD | ARG | B | 438 | 45.143 | -6.499 | 51.074 | 1.00 45.79 | B C |
| ATOM | 3777 | NE | ARG | B | 438 | 44.376 | -5.896 | 52.188 | 1.00 48.34 | B N |
| ATOM | 3778 | CZ | ARG | B | 438 | 44.443 | -6.314 | 53.451 | 1.00 50.07 | B C |
| ATOM | 3779 | NH1 | ARG | B | 438 | 45.258 | -7.336 | 53.761 | 1.00 49.91 | B N |
| ATOM | 3780 | NH2 | ARG | B | 438 | 43.655 | -5.760 | 54.387 | 1.00 49.24 | B N |
| ATOM | 3781 | C | ARG | B | 438 | 45.789 | -3.704 | 49.509 | 1.00 33.94 | B C |
| ATOM | 3782 | O | ARG | B | 438 | 45.252 | -2.658 | 49.913 | 1.00 32.88 | B O |
| ATOM | 3783 | N | ILE | B | 439 | 45.262 | -4.484 | 48.574 | 1.00 32.92 | B N |
| ATOM | 3784 | CA | ILE | B | 439 | 43.957 | -4.239 | 47.988 | 0.00 32.61 | B C |
| ATOM | 3785 | CB | ILE | B | 439 | 43.741 | -5.157 | 46.756 | 1.00 32.89 | B C |
| ATOM | 3786 | CG2 | ILE | B | 439 | 42.285 | -5.103 | 46.253 | 1.00 34.50 | B C |
| ATOM | 3787 | CG1 | ILE | B | 439 | 44.642 | -4.649 | 45.616 | 1.00 35.41 | B C |
| ATOM | 3788 | CD1 | ILE | B | 439 | 44.802 | -5.607 | 44.406 | 1.00 36.57 | B C |
| ATOM | 3789 | C | ILE | B | 439 | 42.840 | -4.434 | 49.032 | 1.00 31.45 | B C |
| ATOM | 3790 | O | ILE | B | 439 | 42.946 | -5.299 | 49.896 | 1.00 31.25 | B O |
| ATOM | 3791 | N | PRO | B | 440 | 41.869 | -3.510 | 49.071 | 1.00 30.10 | B N |
| ATOM | 3792 | CD | PRO | B | 440 | 41.983 | -2.168 | 48.466 | 1.00 28.52 | B C |
| ATOM | 3793 | CA | PRO | B | 440 | 40.734 | -3.583 | 50.011 | 0.00 28.41 | B C |
| ATOM | 3794 | CB | PRO | B | 440 | 39.947 | -2.340 | 49.641 | 1.00 28.76 | B C |
| ATOM | 3795 | CG | PRO | B | 440 | 41.066 | -1.348 | 49.320 | 1.00 29.08 | B C |
| ATOM | 3796 | C | PRO | B | 440 | 39.935 | -4.864 | 49.740 | 1.00 27.78 | B C |
| ATOM | 3797 | O | PRO | B | 440 | 40.007 | -5.412 | 48.641 | 1.00 26.62 | B O |
| ATOM | 3798 | N | TYR | B | 441 | 39.215 | -5.372 | 50.751 | 1.00 27.67 | B N |
| ATOM | 3799 | CA | TYR | B | 441 | 38.400 | -6.604 | 50.652 | 0.00 26.62 | B C |
| ATOM | 3800 | CB | TYR | B | 441 | 37.069 | -6.326 | 49.945 | 1.00 24.39 | B C |
| ATOM | 3801 | CG | TYR | B | 441 | 36.320 | -5.151 | 50.517 | 1.00 22.84 | B C |
| ATOM | 3802 | CD1 | TYR | B | 441 | 35.355 | -5.331 | 51.549 | 1.00 23.73 | B C |
| ATOM | 3803 | CE1 | TYR | B | 441 | 34.608 | -4.215 | 52.038 | 1.00 22.10 | B C |
| ATOM | 3804 | CD2 | TYR | B | 441 | 36.520 | -3.878 | 50.031 | 1.00 19.50 | B C |
| ATOM | 3805 | CE2 | TYR | B | 441 | 35.796 | -2.798 | 50.507 | 1.00 21.10 | B C |
| ATOM | 3806 | CZ | TYR | B | 441 | 34.842 | -2.972 | 51.500 | 1.00 21.01 | B C |
| ATOM | 3807 | OH | TYR | B | 441 | 34.117 | -1.884 | 51.927 | 1.00 23.36 | B O |
| ATOM | 3808 | C | TYR | B | 441 | 39.132 | -7.733 | 49.928 | 1.00 28.42 | B C |
| ATOM | 3809 | O | TYR | B | 441 | 38.686 | -8.208 | 48.871 | 1.00 27.72 | B O |
| ATOM | 3810 | N | PRO | B | 442 | 40.293 | -8.150 | 50.466 | 1.00 30.14 | B N |
| ATOM | 3811 | CD | PRO | B | 442 | 41.004 | -7.619 | 51.649 | 1.00 29.69 | B C |
| ATOM | 3812 | CA | PRO | B | 442 | 41.052 | -9.231 | 49.824 | 0.00 32.41 | B C |
| ATOM | 3813 | CB | PRO | B | 442 | 42.296 | -9.361 | 50.725 | 1.00 31.66 | B C |
| ATOM | 3814 | CG | PRO | B | 442 | 41.858 | -8.787 | 52.059 | 1.00 30.99 | B C |
| ATOM | 3815 | C | PRO | B | 442 | 40.255 | -10.539 | 49.652 | 1.00 34.72 | B C |
| ATOM | 3816 | O | PRO | B | 442 | 39.492 | -10.967 | 50.516 | 1.00 35.88 | B O |
| ATOM | 3817 | N | GLY | B | 443 | 40.391 | -11.173 | 48.507 | 1.00 36.81 | B N |
| ATOM | 3818 | CA | GLY | B | 443 | 39.628 | -12.392 | 48.307 | 0.00 38.70 | B C |
| ATOM | 3819 | C | GLY | B | 443 | 38.167 | -12.112 | 48.000 | 1.00 39.90 | B C |
| ATOM | 3820 | O | GLY | B | 443 | 37.319 | -12.982 | 48.181 | 1.00 41.62 | B O |
| ATOM | 3821 | N | MET | B | 444 | 37.851 | -10.887 | 47.587 | 1.00 39.25 | B N |
| ATOM | 3822 | CA | MET | B | 444 | 36.481 | -10.535 | 47.200 | 0.00 38.38 | B C |

Figure 12

```
ATOM   3823  CB   MET B 444      35.803  -9.613  48.235  1.00 37.73      B    C
ATOM   3824  CG   MET B 444      34.960 -10.314  49.286  1.00 36.38      B    C
ATOM   3825  SD   MET B 444      34.280  -9.267  50.594  1.00 34.46      B    S
ATOM   3826  CE   MET B 444      33.409  -8.289  49.827  1.00 35.68      B    C
ATOM   3827  C    MET B 444      36.481  -9.837  45.845  1.00 37.92      B    C
ATOM   3828  O    MET B 444      37.208  -8.877  45.652  1.00 38.62      B    O
ATOM   3829  N    THR B 445      35.682 -10.331  44.903  1.00 37.08      B    N
ATOM   3830  CA   THR B 445      35.588  -9.693  43.592  0.00 36.13      B    C
ATOM   3831  CB   THR B 445      34.953 -10.660  42.556  1.00 37.30      B    C
ATOM   3832  OG1  THR B 445      33.540 -10.796  42.807  1.00 36.80      B    O
ATOM   3833  CG2  THR B 445      35.653 -12.066  42.649  1.00 36.82      B    C
ATOM   3834  C    THR B 445      34.712  -8.449  43.715  1.00 35.19      B    C
ATOM   3835  O    THR B 445      34.063  -8.256  44.726  1.00 34.96      B    O
ATOM   3836  N    ASN B 446      34.680  -7.596  42.709  1.00 34.51      B    N
ATOM   3837  CA   ASN B 446      33.833  -6.430  42.798  0.00 34.03      B    C
ATOM   3838  CB   ASN B 446      33.966  -5.565  41.553  1.00 33.54      B    C
ATOM   3839  CG   ASN B 446      35.205  -4.694  41.587  1.00 32.95      B    C
ATOM   3840  OD1  ASN B 446      36.008  -4.750  42.526  1.00 31.35      B    O
ATOM   3841  ND2  ASN B 446      35.343  -3.840  40.587  1.00 32.55      B    N
ATOM   3842  C    ASN B 446      32.361  -6.761  43.102  1.00 34.37      B    C
ATOM   3843  O    ASN B 446      31.767  -6.130  43.995  1.00 33.70      B    O
ATOM   3844  N    PRO B 447      31.740  -7.723  42.358  1.00 34.25      B    N
ATOM   3845  CD   PRO B 447      32.159  -8.318  41.079  1.00 34.27      B    C
ATOM   3846  CA   PRO B 447      30.340  -8.063  42.643  0.00 34.05      B    C
ATOM   3847  CB   PRO B 447      29.961  -9.042  41.518  1.00 34.33      B    C
ATOM   3848  CG   PRO B 447      31.268  -9.515  40.981  1.00 34.67      B    C
ATOM   3849  C    PRO B 447      30.104  -8.640  44.045  1.00 33.20      B    C
ATOM   3850  O    PRO B 447      29.043  -8.413  44.627  1.00 33.41      B    O
ATOM   3851  N    GLU B 448      31.085  -9.361  44.579  1.00 32.41      B    N
ATOM   3852  CA   GLU B 448      30.994  -9.918  45.921  0.00 31.01      B    C
ATOM   3853  CB   GLU B 448      32.214 -10.761  46.225  1.00 33.02      B    C
ATOM   3854  CG   GLU B 448      32.078 -12.176  45.803  1.00 37.66      B    C
ATOM   3855  CD   GLU B 448      33.404 -12.884  45.823  1.00 41.44      B    C
ATOM   3856  OE1  GLU B 448      34.176 -12.728  46.816  1.00 45.29      B    O
ATOM   3857  OE2  GLU B 448      33.680 -13.605  44.847  1.00 43.22      B    O
ATOM   3858  C    GLU B 448      30.931  -8.771  46.921  1.00 29.89      B    C
ATOM   3859  O    GLU B 448      30.121  -8.784  47.837  1.00 29.39      B    O
ATOM   3860  N    VAL B 449      31.818  -7.790  46.735  1.00 28.53      B    N
ATOM   3861  CA   VAL B 449      31.872  -6.597  47.569  0.00 27.07      B    C
ATOM   3862  CB   VAL B 449      33.016  -5.598  47.130  1.00 26.38      B    C
ATOM   3863  CG1  VAL B 449      32.853  -4.204  47.806  1.00 23.17      B    C
ATOM   3864  CG2  VAL B 449      34.348  -6.181  47.529  1.00 21.27      B    C
ATOM   3865  C    VAL B 449      30.546  -5.897  47.588  1.00 26.68      B    C
ATOM   3866  O    VAL B 449      30.052  -5.558  48.657  1.00 27.22      B    O
ATOM   3867  N    ILE B 450      29.927  -5.771  46.422  1.00 27.54      B    N
ATOM   3868  CA   ILE B 450      28.626  -5.115  46.275  0.00 27.71      B    C
ATOM   3869  CB   ILE B 450      28.162  -5.151  44.802  1.00 29.33      B    C
ATOM   3870  CG2  ILE B 450      26.765  -4.551  44.668  1.00 27.71      B    C
ATOM   3871  CG1  ILE B 450      29.145  -4.421  43.886  1.00 29.57      B    C
ATOM   3872  CD1  ILE B 450      28.994  -2.956  43.908  1.00 30.88      B    C
ATOM   3873  C    ILE B 450      27.557  -5.822  47.126  1.00 27.96      B    C
ATOM   3874  O    ILE B 450      26.842  -5.188  47.883  1.00 26.97      B    O
ATOM   3875  N    GLN B 451      27.487  -7.138  47.037  1.00 29.09      B    N
ATOM   3876  CA   GLN B 451      26.483  -7.852  47.796  0.00 29.79      B    C
ATOM   3877  CB   GLN B 451      26.216  -9.224  47.184  1.00 33.20      B    C
ATOM   3878  CG   GLN B 451      27.269 -10.229  47.371  1.00 37.87      B    C
ATOM   3879  CD   GLN B 451      27.170 -11.350  46.343  1.00 41.76      B    C
ATOM   3880  OE1  GLN B 451      27.559 -12.493  46.622  1.00 44.53      B    O
ATOM   3881  NE2  GLN B 451      26.714 -11.015  45.133  1.00 43.00      B    N
```

Figure 12

| | | | | | | | | | | |
|---|---|---|---|---|---|---|---|---|---|---|
| ATOM | 3882 | C | GLN | B | 451 | 26.779 | -7.933 | 49.274 | 1.00 28.86 | B C |
| ATOM | 3883 | O | GLN | B | 451 | 25.856 | -7.988 | 50.088 | 1.00 28.84 | B O |
| ATOM | 3884 | N | ASN | B | 452 | 28.060 | -7.942 | 49.640 | 1.00 26.78 | B N |
| ATOM | 3885 | CA | ASN | B | 452 | 28.386 | -7.947 | 51.055 | 0.00 24.91 | B C |
| ATOM | 3886 | CB | ASN | B | 452 | 29.882 | -8.204 | 51.279 | 1.00 24.79 | B C |
| ATOM | 3887 | CG | ASN | B | 452 | 30.210 | -9.688 | 51.424 | 1.00 25.73 | B C |
| ATOM | 3888 | OD1 | ASN | B | 452 | 30.213 | -10.219 | 52.522 | 1.00 26.38 | B O |
| ATOM | 3889 | ND2 | ASN | B | 452 | 30.489 | -10.364 | 50.318 | 1.00 25.54 | B N |
| ATOM | 3890 | C | ASN | B | 452 | 27.973 | -6.582 | 51.640 | 1.00 23.61 | B C |
| ATOM | 3891 | O | ASN | B | 452 | 27.515 | -6.517 | 52.775 | 1.00 22.46 | B O |
| ATOM | 3892 | N | LEU | B | 453 | 28.156 | -5.489 | 50.897 | 1.00 22.97 | B N |
| ATOM | 3893 | CA | LEU | B | 453 | 27.767 | -4.164 | 51.414 | 0.00 23.29 | B C |
| ATOM | 3894 | CB | LEU | B | 453 | 28.316 | -3.042 | 50.538 | 1.00 24.54 | B C |
| ATOM | 3895 | CG | LEU | B | 453 | 29.806 | -2.738 | 50.525 | 1.00 24.61 | B C |
| ATOM | 3896 | CD1 | LEU | B | 453 | 29.982 | -1.577 | 49.587 | 1.00 24.86 | B C |
| ATOM | 3897 | CD2 | LEU | B | 453 | 30.349 | -2.373 | 51.925 | 1.00 24.35 | B C |
| ATOM | 3898 | C | LEU | B | 453 | 26.249 | -4.022 | 51.462 | 1.00 23.73 | B C |
| ATOM | 3899 | O | LEU | B | 453 | 25.704 | -3.182 | 52.179 | 1.00 22.98 | B O |
| ATOM | 3900 | N | GLU | B | 454 | 25.555 | -4.767 | 50.616 | 1.00 23.55 | B N |
| ATOM | 3901 | CA | GLU | B | 454 | 24.103 | -4.720 | 50.687 | 0.00 25.63 | B C |
| ATOM | 3902 | CB | GLU | B | 454 | 23.499 | -5.635 | 49.648 | 1.00 28.37 | B C |
| ATOM | 3903 | CG | GLU | B | 454 | 23.565 | -5.109 | 48.279 | 1.00 36.00 | B C |
| ATOM | 3904 | CD | GLU | B | 454 | 23.057 | -6.126 | 47.287 | 1.00 40.12 | B C |
| ATOM | 3905 | OE1 | GLU | B | 454 | 23.552 | -6.091 | 46.122 | 1.00 42.27 | B O |
| ATOM | 3906 | OE2 | GLU | B | 454 | 22.174 | -6.946 | 47.693 | 1.00 42.59 | B O |
| ATOM | 3907 | C | GLU | B | 454 | 23.678 | -5.251 | 52.081 | 1.00 24.34 | B C |
| ATOM | 3908 | O | GLU | B | 454 | 22.661 | -4.843 | 52.643 | 1.00 23.07 | B O |
| ATOM | 3909 | N | ARG | B | 455 | 24.442 | -6.231 | 52.548 | 1.00 22.53 | B N |
| ATOM | 3910 | CA | ARG | B | 455 | 24.244 | -6.897 | 53.807 | 0.00 22.22 | B C |
| ATOM | 3911 | CB | ARG | B | 455 | 24.768 | -8.315 | 53.685 | 1.00 24.09 | B C |
| ATOM | 3912 | CG | ARG | B | 455 | 24.161 | -9.187 | 52.589 | 1.00 26.08 | B C |
| ATOM | 3913 | CD | ARG | B | 455 | 24.695 | -10.693 | 52.735 | 1.00 30.68 | B C |
| ATOM | 3914 | NE | ARG | B | 455 | 26.143 | -10.668 | 53.061 | 1.00 35.96 | B N |
| ATOM | 3915 | CZ | ARG | B | 455 | 26.682 | -10.833 | 54.303 | 1.00 37.32 | B C |
| ATOM | 3916 | NH1 | ARG | B | 455 | 25.931 | -11.128 | 55.365 | 1.00 34.74 | B N |
| ATOM | 3917 | NH2 | ARG | B | 455 | 27.928 | -10.384 | 54.554 | 1.00 37.72 | B N |
| ATOM | 3918 | C | ARG | B | 455 | 24.906 | -6.166 | 54.997 | 1.00 21.52 | B C |
| ATOM | 3919 | O | ARG | B | 455 | 24.820 | -6.623 | 56.119 | 1.00 20.80 | B O |
| ATOM | 3920 | N | GLY | B | 456 | 25.560 | -5.020 | 54.737 | 1.00 20.65 | B N |
| ATOM | 3921 | CA | GLY | B | 456 | 26.179 | -4.245 | 55.810 | 0.00 18.97 | B C |
| ATOM | 3922 | C | GLY | B | 456 | 27.587 | -4.640 | 56.245 | 1.00 18.72 | B C |
| ATOM | 3923 | O | GLY | B | 456 | 28.050 | -4.278 | 57.328 | 1.00 18.28 | B O |
| ATOM | 3924 | N | TYR | B | 457 | 28.251 | -5.432 | 55.426 | 1.00 18.47 | B N |
| ATOM | 3925 | CA | TYR | B | 457 | 29.584 | -5.872 | 55.711 | 0.00 18.79 | B C |
| ATOM | 3926 | CB | TYR | B | 457 | 30.026 | -6.815 | 54.596 | 1.00 17.26 | B C |
| ATOM | 3927 | CG | TYR | B | 457 | 31.375 | -7.381 | 54.829 | 1.00 16.71 | B C |
| ATOM | 3928 | CD1 | TYR | B | 457 | 31.549 | -8.585 | 55.479 | 1.00 15.01 | B C |
| ATOM | 3929 | CE1 | TYR | B | 457 | 32.831 | -9.097 | 55.714 | 1.00 17.38 | B C |
| ATOM | 3930 | CD2 | TYR | B | 457 | 32.523 | -6.676 | 54.411 | 1.00 18.93 | B C |
| ATOM | 3931 | CE2 | TYR | B | 457 | 33.788 | -7.159 | 54.643 | 1.00 18.16 | B C |
| ATOM | 3932 | CZ | TYR | B | 457 | 33.947 | -8.360 | 55.285 | 1.00 18.61 | B C |
| ATOM | 3933 | OH | TYR | B | 457 | 35.241 | -8.828 | 55.449 | 1.00 20.06 | B O |
| ATOM | 3934 | C | TYR | B | 457 | 30.602 | -4.727 | 55.865 | 1.00 19.04 | B C |
| ATOM | 3935 | O | TYR | B | 457 | 30.510 | -3.685 | 55.215 | 1.00 19.53 | B O |
| ATOM | 3936 | N | ARG | B | 458 | 31.532 | -4.907 | 56.797 | 1.00 19.22 | B N |
| ATOM | 3937 | CA | ARG | B | 458 | 32.626 | -3.951 | 57.005 | 0.00 20.29 | B C |
| ATOM | 3938 | CB | ARG | B | 458 | 32.401 | -3.063 | 58.231 | 1.00 19.00 | B C |
| ATOM | 3939 | CG | ARG | B | 458 | 31.219 | -2.102 | 58.111 | 1.00 19.75 | B C |
| ATOM | 3940 | CD | ARG | B | 458 | 31.367 | -1.192 | 56.936 | 1.00 17.04 | B C |

Figure 12

| | | | | | | | | | | | |
|---|---|---|---|---|---|---|---|---|---|---|---|
| ATOM | 3941 | NE | ARG | B | 458 | 30.365 | -0.135 | 56.958 | 1.00 | 16.18 | B N |
| ATOM | 3942 | CZ | ARG | B | 458 | 29.193 | -0.211 | 56.344 | 1.00 | 15.85 | B C |
| ATOM | 3943 | NH1 | ARG | B | 458 | 28.867 | -1.298 | 55.639 | 1.00 | 16.01 | B N |
| ATOM | 3944 | NH2 | ARG | B | 458 | 28.345 | 0.796 | 56.421 | 1.00 | 14.46 | B N |
| ATOM | 3945 | C | ARG | B | 458 | 33.895 | -4.776 | 57.216 | 1.00 | 20.59 | B C |
| ATOM | 3946 | O | ARG | B | 458 | 33.839 | -5.855 | 57.840 | 1.00 | 21.00 | B O |
| ATOM | 3947 | N | MET | B | 459 | 35.020 | -4.331 | 56.619 | 1.00 | 20.39 | B N |
| ATOM | 3948 | CA | MET | B | 459 | 36.313 | -5.018 | 56.814 | 0.00 | 20.97 | B C |
| ATOM | 3949 | CB | MET | B | 459 | 37.448 | -4.311 | 56.068 | 1.00 | 20.97 | B C |
| ATOM | 3950 | CG | MET | B | 459 | 37.496 | -4.576 | 54.586 | 1.00 | 23.07 | B C |
| ATOM | 3951 | SD | MET | B | 459 | 38.933 | -3.709 | 53.912 | 1.00 | 25.33 | B S |
| ATOM | 3952 | CE | MET | B | 459 | 38.142 | -2.237 | 53.443 | 1.00 | 21.45 | B C |
| ATOM | 3953 | C | MET | B | 459 | 36.696 | -5.017 | 58.288 | 1.00 | 20.61 | B C |
| ATOM | 3954 | O | MET | B | 459 | 36.410 | -4.059 | 59.022 | 1.00 | 18.93 | B O |
| ATOM | 3955 | N | VAL | B | 460 | 37.343 | -6.096 | 58.729 | 1.00 | 21.68 | B N |
| ATOM | 3956 | CA | VAL | B | 460 | 37.796 | -6.176 | 60.113 | 0.00 | 23.77 | B C |
| ATOM | 3957 | CB | VAL | B | 460 | 38.000 | -7.637 | 60.518 | 1.00 | 25.06 | B C |
| ATOM | 3958 | CG1 | VAL | B | 460 | 36.710 | -8.427 | 60.255 | 1.00 | 24.50 | B C |
| ATOM | 3959 | CG2 | VAL | B | 460 | 39.197 | -8.284 | 59.692 | 1.00 | 26.04 | B C |
| ATOM | 3960 | C | VAL | B | 460 | 39.135 | -5.412 | 60.265 | 1.00 | 25.72 | B C |
| ATOM | 3961 | O | VAL | B | 460 | 39.778 | -5.044 | 59.267 | 1.00 | 24.58 | B O |
| ATOM | 3962 | N | ARG | B | 461 | 39.546 | -5.164 | 61.504 | 1.00 | 27.49 | B N |
| ATOM | 3963 | CA | ARG | B | 461 | 40.817 | -4.497 | 61.783 | 0.00 | 29.85 | B C |
| ATOM | 3964 | CB | ARG | B | 461 | 41.106 | -4.492 | 63.280 | 1.00 | 31.96 | B C |
| ATOM | 3965 | CG | ARG | B | 461 | 42.236 | -3.521 | 63.735 | 1.00 | 34.48 | B C |
| ATOM | 3966 | CD | ARG | B | 461 | 42.429 | -3.505 | 65.296 | 1.00 | 37.27 | B C |
| ATOM | 3967 | NE | ARG | B | 461 | 42.787 | -4.826 | 65.808 | 1.00 | 40.46 | B N |
| ATOM | 3968 | CZ | ARG | B | 461 | 43.973 | -5.400 | 65.626 | 1.00 | 43.22 | B C |
| ATOM | 3969 | NH1 | ARG | B | 461 | 44.943 | -4.754 | 64.982 | 1.00 | 44.26 | B N |
| ATOM | 3970 | NH2 | ARG | B | 461 | 44.126 | -6.692 | 65.879 | 1.00 | 43.71 | B N |
| ATOM | 3971 | C | ARG | B | 461 | 41.974 | -5.196 | 61.063 | 1.00 | 31.31 | B C |
| ATOM | 3972 | O | ARG | B | 461 | 42.213 | -6.399 | 61.257 | 1.00 | 31.29 | B O |
| ATOM | 3973 | N | PRO | B | 462 | 42.657 | -4.464 | 60.149 | 1.00 | 32.28 | B N |
| ATOM | 3974 | CD | PRO | B | 462 | 42.385 | -3.054 | 59.809 | 1.00 | 31.32 | B C |
| ATOM | 3975 | CA | PRO | B | 462 | 43.800 | -4.978 | 59.377 | 0.00 | 33.25 | B C |
| ATOM | 3976 | CB | PRO | B | 462 | 44.202 | -3.774 | 58.520 | 1.00 | 32.95 | B C |
| ATOM | 3977 | CG | PRO | B | 462 | 42.946 | -2.969 | 58.419 | 1.00 | 32.48 | B C |
| ATOM | 3978 | C | PRO | B | 462 | 44.935 | -5.357 | 60.354 | 1.00 | 34.82 | B C |
| ATOM | 3979 | O | PRO | B | 462 | 45.052 | -4.777 | 61.444 | 1.00 | 33.72 | B O |
| ATOM | 3980 | N | ASP | B | 463 | 45.735 | -6.354 | 59.989 | 1.00 | 36.64 | B N |
| ATOM | 3981 | CA | ASP | B | 463 | 46.814 | -6.759 | 60.876 | 0.00 | 39.77 | B C |
| ATOM | 3982 | CB | ASP | B | 463 | 47.584 | -7.979 | 60.317 | 1.00 | 41.51 | B C |
| ATOM | 3983 | CG | ASP | B | 463 | 46.741 | -9.269 | 60.326 | 1.00 | 43.75 | B C |
| ATOM | 3984 | OD1 | ASP | B | 463 | 46.078 | -9.548 | 61.352 | 1.00 | 44.61 | B O |
| ATOM | 3985 | OD2 | ASP | B | 463 | 46.745 | -10.010 | 59.309 | 1.00 | 45.42 | B O |
| ATOM | 3986 | C | ASP | B | 463 | 47.729 | -5.550 | 61.115 | 1.00 | 40.76 | B C |
| ATOM | 3987 | O | ASP | B | 463 | 47.962 | -4.740 | 60.217 | 1.00 | 41.32 | B O |
| ATOM | 3988 | N | ASN | B | 464 | 48.118 | -5.370 | 62.374 | 1.00 | 41.99 | B N |
| ATOM | 3989 | CA | ASN | B | 464 | 48.979 | -4.258 | 62.805 | 0.00 | 42.67 | B C |
| ATOM | 3990 | CB | ASN | B | 464 | 50.365 | -4.359 | 62.163 | 1.00 | 44.67 | B C |
| ATOM | 3991 | CG | ASN | B | 464 | 51.149 | -5.555 | 62.677 | 1.00 | 46.48 | B C |
| ATOM | 3992 | OD1 | ASN | B | 464 | 51.161 | -5.817 | 63.886 | 1.00 | 48.10 | B O |
| ATOM | 3993 | ND2 | ASN | B | 464 | 51.725 | -6.337 | 61.764 | 1.00 | 45.93 | B N |
| ATOM | 3994 | C | ASN | B | 464 | 48.354 | -2.884 | 62.610 | 1.00 | 42.33 | B C |
| ATOM | 3995 | O | ASN | B | 464 | 48.965 | -1.929 | 62.098 | 1.00 | 44.39 | B O |
| ATOM | 3996 | N | CYS | B | 465 | 47.117 | -2.773 | 63.051 | 1.00 | 39.92 | B N |
| ATOM | 3997 | CA | CYS | B | 465 | 46.440 | -1.522 | 62.931 | 0.00 | 37.10 | B C |
| ATOM | 3998 | CB | CYS | B | 465 | 45.255 | -1.697 | 61.976 | 1.00 | 35.45 | B C |
| ATOM | 3999 | SG | CYS | B | 465 | 44.225 | -0.270 | 61.853 | 1.00 | 32.86 | B S |

Figure 12

| ATOM | 4000 | C   | CYS B 465 | 45.986 | -1.168 | 64.330 | 1.00 | 35.34 | B | C |
| ATOM | 4001 | O   | CYS B 465 | 45.466 | -2.018 | 65.008 | 1.00 | 36.35 | B | O |
| ATOM | 4002 | N   | PRO B 466 | 46.307 | 0.031  | 64.825 | 1.00 | 33.92 | B | N |
| ATOM | 4003 | CD  | PRO B 466 | 47.147 | 1.055  | 64.183 | 1.00 | 33.74 | B | C |
| ATOM | 4004 | CA  | PRO B 466 | 45.884 | 0.439  | 66.167 | 0.00 | 34.07 | B | C |
| ATOM | 4005 | CB  | PRO B 466 | 46.334 | 1.905  | 66.238 | 1.00 | 33.33 | B | C |
| ATOM | 4006 | CG  | PRO B 466 | 47.501 | 1.956  | 65.337 | 1.00 | 34.29 | B | C |
| ATOM | 4007 | C   | PRO B 466 | 44.339 | 0.381  | 66.238 | 1.00 | 34.32 | B | C |
| ATOM | 4008 | O   | PRO B 466 | 43.678 | 0.772  | 65.273 | 1.00 | 34.47 | B | O |
| ATOM | 4009 | N   | GLU B 467 | 43.775 | -0.073 | 67.364 | 1.00 | 34.58 | B | N |
| ATOM | 4010 | CA  | GLU B 467 | 42.309 | -0.146 | 67.549 | 0.00 | 34.52 | B | C |
| ATOM | 4011 | CB  | GLU B 467 | 41.939 | -0.589 | 68.973 | 1.00 | 35.80 | B | C |
| ATOM | 4012 | CG  | GLU B 467 | 41.145 | -1.929 | 69.050 | 1.00 | 38.71 | B | C |
| ATOM | 4013 | CD  | GLU B 467 | 39.861 | -1.989 | 68.204 | 1.00 | 39.98 | B | C |
| ATOM | 4014 | OE1 | GLU B 467 | 39.798 | -2.848 | 67.273 | 1.00 | 41.68 | B | O |
| ATOM | 4015 | OE2 | GLU B 467 | 38.909 | -1.220 | 68.509 | 1.00 | 40.50 | B | O |
| ATOM | 4016 | C   | GLU B 467 | 41.607 | 1.193  | 67.282 | 1.00 | 33.48 | B | C |
| ATOM | 4017 | O   | GLU B 467 | 40.538 | 1.231  | 66.691 | 1.00 | 32.44 | B | O |
| ATOM | 4018 | N   | GLU B 468 | 42.207 | 2.268  | 67.776 | 1.00 | 33.18 | B | N |
| ATOM | 4019 | CA  | GLU B 468 | 41.693 | 3.613  | 67.607 | 0.00 | 32.78 | B | C |
| ATOM | 4020 | CB  | GLU B 468 | 42.554 | 4.597  | 68.406 | 1.00 | 36.09 | B | C |
| ATOM | 4021 | CG  | GLU B 468 | 42.781 | 4.192  | 69.870 | 1.00 | 42.76 | B | C |
| ATOM | 4022 | CD  | GLU B 468 | 43.715 | 2.943  | 70.050 | 1.00 | 46.68 | B | C |
| ATOM | 4023 | OE1 | GLU B 468 | 44.740 | 2.806  | 69.322 | 1.00 | 48.16 | B | O |
| ATOM | 4024 | OE2 | GLU B 468 | 43.412 | 2.076  | 70.923 | 1.00 | 49.10 | B | O |
| ATOM | 4025 | C   | GLU B 468 | 41.695 | 3.995  | 66.129 | 1.00 | 30.62 | B | C |
| ATOM | 4026 | O   | GLU B 468 | 40.830 | 4.751  | 65.680 | 1.00 | 30.17 | B | O |
| ATOM | 4027 | N   | LEU B 469 | 42.675 | 3.520  | 65.355 | 1.00 | 28.77 | B | N |
| ATOM | 4028 | CA  | LEU B 469 | 42.669 | 3.863  | 63.923 | 0.00 | 26.51 | B | C |
| ATOM | 4029 | CB  | LEU B 469 | 43.994 | 3.557  | 63.204 | 1.00 | 24.49 | B | C |
| ATOM | 4030 | CG  | LEU B 469 | 43.987 | 3.985  | 61.722 | 1.00 | 23.61 | B | C |
| ATOM | 4031 | CD1 | LEU B 469 | 43.868 | 5.490  | 61.627 | 1.00 | 22.55 | B | C |
| ATOM | 4032 | CD2 | LEU B 469 | 45.238 | 3.555  | 61.021 | 1.00 | 23.09 | B | C |
| ATOM | 4033 | C   | LEU B 469 | 41.540 | 3.056  | 63.307 | 1.00 | 24.65 | B | C |
| ATOM | 4034 | O   | LEU B 469 | 40.804 | 3.555  | 62.456 | 1.00 | 25.44 | B | O |
| ATOM | 4035 | N   | TYR B 470 | 41.369 | 1.836  | 63.784 | 1.00 | 22.91 | B | N |
| ATOM | 4036 | CA  | TYR B 470 | 40.303 | 0.999  | 63.277 | 0.00 | 23.58 | B | C |
| ATOM | 4037 | CB  | TYR B 470 | 40.376 | -0.426 | 63.795 | 1.00 | 23.30 | B | C |
| ATOM | 4038 | CG  | TYR B 470 | 39.271 | -1.307 | 63.216 | 1.00 | 25.22 | B | C |
| ATOM | 4039 | CD1 | TYR B 470 | 39.178 | -1.544 | 61.842 | 1.00 | 24.55 | B | C |
| ATOM | 4040 | CE1 | TYR B 470 | 38.134 | -2.310 | 61.282 | 1.00 | 25.01 | B | C |
| ATOM | 4041 | CD2 | TYR B 470 | 38.277 | -1.873 | 64.051 | 1.00 | 26.13 | B | C |
| ATOM | 4042 | CE2 | TYR B 470 | 37.210 | -2.664 | 63.504 | 1.00 | 25.71 | B | C |
| ATOM | 4043 | CZ  | TYR B 470 | 37.148 | -2.870 | 62.124 | 1.00 | 26.00 | B | C |
| ATOM | 4044 | OH  | TYR B 470 | 36.113 | -3.611 | 61.602 | 1.00 | 22.32 | B | O |
| ATOM | 4045 | C   | TYR B 470 | 38.927 | 1.588  | 63.563 | 1.00 | 23.68 | B | C |
| ATOM | 4046 | O   | TYR B 470 | 38.070 | 1.505  | 62.717 | 1.00 | 23.93 | B | O |
| ATOM | 4047 | N   | GLN B 471 | 38.745 | 2.256  | 64.707 | 1.00 | 24.13 | B | N |
| ATOM | 4048 | CA  | GLN B 471 | 37.459 | 2.844  | 65.056 | 0.00 | 25.15 | B | C |
| ATOM | 4049 | CB  | GLN B 471 | 37.354 | 3.168  | 66.566 | 1.00 | 25.54 | B | C |
| ATOM | 4050 | CG  | GLN B 471 | 37.247 | 1.897  | 67.412 | 1.00 | 26.98 | B | C |
| ATOM | 4051 | CD  | GLN B 471 | 36.074 | 0.976  | 66.971 | 1.00 | 29.13 | B | C |
| ATOM | 4052 | OE1 | GLN B 471 | 34.984 | 1.450  | 66.643 | 1.00 | 29.63 | B | O |
| ATOM | 4053 | NE2 | GLN B 471 | 36.307 | -0.337 | 66.977 | 1.00 | 29.50 | B | N |
| ATOM | 4054 | C   | GLN B 471 | 37.192 | 4.063  | 64.203 | 1.00 | 24.79 | B | C |
| ATOM | 4055 | O   | GLN B 471 | 36.037 | 4.377  | 63.899 | 1.00 | 24.41 | B | O |
| ATOM | 4056 | N   | LEU B 472 | 38.270 | 4.738  | 63.819 | 1.00 | 24.58 | B | N |
| ATOM | 4057 | CA  | LEU B 472 | 38.167 | 5.896  | 62.941 | 0.00 | 23.75 | B | C |
| ATOM | 4058 | CB  | LEU B 472 | 39.518 | 6.545  | 62.807 | 1.00 | 24.65 | B | C |

Figure 12

| ATOM | 4059 | CG | LEU | B | 472 | 39.495 | 8.059 | 62.646 | 1.00 | 26.54 | B | C |
|------|------|-----|-----|---|-----|--------|-------|--------|------|-------|---|---|
| ATOM | 4060 | CD1 | LEU | B | 472 | 38.796 | 8.707 | 63.854 | 1.00 | 25.70 | B | C |
| ATOM | 4061 | CD2 | LEU | B | 472 | 40.972 | 8.547 | 62.528 | 1.00 | 27.00 | B | C |
| ATOM | 4062 | C | LEU | B | 472 | 37.666 | 5.392 | 61.554 | 1.00 | 22.54 | B | C |
| ATOM | 4063 | O | LEU | B | 472 | 36.757 | 5.985 | 60.980 | 1.00 | 22.82 | B | O |
| ATOM | 4064 | N | MET | B | 473 | 38.220 | 4.291 | 61.062 | 1.00 | 21.08 | B | N |
| ATOM | 4065 | CA | MET | B | 473 | 37.775 | 3.730 | 59.790 | 0.00 | 21.61 | B | C |
| ATOM | 4066 | CB | MET | B | 473 | 38.577 | 2.482 | 59.407 | 1.00 | 21.20 | B | C |
| ATOM | 4067 | CG | MET | B | 473 | 40.091 | 2.659 | 59.379 | 1.00 | 22.39 | B | C |
| ATOM | 4068 | SD | MET | B | 473 | 40.885 | 1.026 | 59.276 | 1.00 | 25.11 | B | S |
| ATOM | 4069 | CE | MET | B | 473 | 42.539 | 1.479 | 58.769 | 1.00 | 24.34 | B | C |
| ATOM | 4070 | C | MET | B | 473 | 36.274 | 3.359 | 59.892 | 1.00 | 21.08 | B | C |
| ATOM | 4071 | O | MET | B | 473 | 35.498 | 3.671 | 58.988 | 1.00 | 20.14 | B | O |
| ATOM | 4072 | N | ARG | B | 474 | 35.858 | 2.776 | 61.018 | 1.00 | 21.73 | B | N |
| ATOM | 4073 | CA | ARG | B | 474 | 34.447 | 2.415 | 61.211 | 0.00 | 21.20 | B | C |
| ATOM | 4074 | CB | ARG | B | 474 | 34.225 | 1.624 | 62.510 | 1.00 | 21.11 | B | C |
| ATOM | 4075 | CG | ARG | B | 474 | 35.027 | 0.329 | 62.550 | 1.00 | 20.86 | B | C |
| ATOM | 4076 | CD | ARG | B | 474 | 34.611 | -0.602 | 61.419 | 1.00 | 22.30 | B | C |
| ATOM | 4077 | NE | ARG | B | 474 | 33.170 | -0.867 | 61.506 | 1.00 | 22.94 | B | N |
| ATOM | 4078 | CZ | ARG | B | 474 | 32.607 | -2.000 | 61.924 | 1.00 | 22.32 | B | C |
| ATOM | 4079 | NH1 | ARG | B | 474 | 33.338 | -3.062 | 62.272 | 1.00 | 18.87 | B | N |
| ATOM | 4080 | NH2 | ARG | B | 474 | 31.287 | -2.014 | 62.091 | 1.00 | 21.56 | B | N |
| ATOM | 4081 | C | ARG | B | 474 | 33.628 | 3.690 | 61.203 | 1.00 | 21.03 | B | C |
| ATOM | 4082 | O | ARG | B | 474 | 32.507 | 3.695 | 60.730 | 1.00 | 21.50 | B | O |
| ATOM | 4083 | N | LEU | B | 475 | 34.191 | 4.788 | 61.677 | 1.00 | 20.49 | B | N |
| ATOM | 4084 | CA | LEU | B | 475 | 33.436 | 6.041 | 61.618 | 0.00 | 21.11 | B | C |
| ATOM | 4085 | CB | LEU | B | 475 | 34.097 | 7.148 | 62.439 | 1.00 | 20.21 | B | C |
| ATOM | 4086 | CG | LEU | B | 475 | 33.774 | 7.071 | 63.939 | 1.00 | 22.74 | B | C |
| ATOM | 4087 | CD1 | LEU | B | 475 | 34.368 | 8.298 | 64.681 | 1.00 | 19.92 | B | C |
| ATOM | 4088 | CD2 | LEU | B | 475 | 32.213 | 6.921 | 64.230 | 1.00 | 20.07 | B | C |
| ATOM | 4089 | C | LEU | B | 475 | 33.290 | 6.483 | 60.168 | 1.00 | 21.64 | B | C |
| ATOM | 4090 | O | LEU | B | 475 | 32.243 | 7.015 | 59.779 | 1.00 | 21.82 | B | O |
| ATOM | 4091 | N | CYS | B | 476 | 34.322 | 6.232 | 59.351 | 1.00 | 20.75 | B | N |
| ATOM | 4092 | CA | CYS | B | 476 | 34.265 | 6.657 | 57.944 | 0.00 | 19.55 | B | C |
| ATOM | 4093 | CB | CYS | B | 476 | 35.662 | 6.579 | 57.261 | 1.00 | 16.82 | B | C |
| ATOM | 4094 | SG | CYS | B | 476 | 36.924 | 7.682 | 57.943 | 1.00 | 19.75 | B | S |
| ATOM | 4095 | C | CYS | B | 476 | 33.245 | 5.787 | 57.183 | 1.00 | 18.57 | B | C |
| ATOM | 4096 | O | CYS | B | 476 | 32.723 | 6.210 | 56.170 | 1.00 | 18.87 | B | O |
| ATOM | 4097 | N | TRP | B | 477 | 33.041 | 4.550 | 57.634 | 1.00 | 17.19 | B | N |
| ATOM | 4098 | CA | TRP | B | 477 | 32.118 | 3.606 | 56.984 | 0.00 | 17.63 | B | C |
| ATOM | 4099 | CB | TRP | B | 477 | 32.691 | 2.177 | 57.059 | 1.00 | 15.67 | B | C |
| ATOM | 4100 | CG | TRP | B | 477 | 34.044 | 2.095 | 56.437 | 1.00 | 18.21 | B | C |
| ATOM | 4101 | CD2 | TRP | B | 477 | 35.089 | 1.166 | 56.768 | 1.00 | 17.90 | B | C |
| ATOM | 4102 | CE2 | TRP | B | 477 | 36.222 | 1.518 | 55.996 | 1.00 | 18.17 | B | C |
| ATOM | 4103 | CE3 | TRP | B | 477 | 35.178 | 0.087 | 57.643 | 1.00 | 18.87 | B | C |
| ATOM | 4104 | CD1 | TRP | B | 477 | 34.578 | 2.951 | 55.480 | 1.00 | 17.04 | B | C |
| ATOM | 4105 | NE1 | TRP | B | 477 | 35.879 | 2.605 | 55.231 | 1.00 | 18.59 | B | N |
| ATOM | 4106 | CZ2 | TRP | B | 477 | 37.437 | 0.817 | 56.073 | 1.00 | 19.01 | B | C |
| ATOM | 4107 | CZ3 | TRP | B | 477 | 36.383 | -0.616 | 57.724 | 1.00 | 20.03 | B | C |
| ATOM | 4108 | CH2 | TRP | B | 477 | 37.503 | -0.242 | 56.941 | 1.00 | 18.94 | B | C |
| ATOM | 4109 | C | TRP | B | 477 | 30.691 | 3.577 | 57.513 | 1.00 | 17.46 | B | C |
| ATOM | 4110 | O | TRP | B | 477 | 30.000 | 2.566 | 57.348 | 1.00 | 18.00 | B | O |
| ATOM | 4111 | N | LYS | B | 478 | 30.286 | 4.616 | 58.233 | 1.00 | 18.34 | B | N |
| ATOM | 4112 | CA | LYS | B | 478 | 28.925 | 4.671 | 58.746 | 0.00 | 19.73 | B | C |
| ATOM | 4113 | CB | LYS | B | 478 | 28.617 | 5.985 | 59.472 | 1.00 | 19.71 | B | C |
| ATOM | 4114 | CG | LYS | B | 478 | 29.258 | 6.104 | 60.871 | 1.00 | 24.49 | B | C |
| ATOM | 4115 | CD | LYS | B | 478 | 28.922 | 4.933 | 61.805 | 1.00 | 27.43 | B | C |
| ATOM | 4116 | CE | LYS | B | 478 | 27.674 | 5.229 | 62.617 | 1.00 | 30.17 | B | C |
| ATOM | 4117 | NZ | LYS | B | 478 | 27.149 | 4.003 | 63.291 | 1.00 | 35.13 | B | N |

Figure 12

| | | | | | | | | | | | |
|---|---|---|---|---|---|---|---|---|---|---|---|
| ATOM | 4118 | C | LYS | B | 478 | 28.054 | 4.563 | 57.527 | 1.00 | 19.36 | B | C |
| ATOM | 4119 | O | LYS | B | 478 | 28.383 | 5.129 | 56.507 | 1.00 | 18.43 | B | O |
| ATOM | 4120 | N | GLU | B | 479 | 26.979 | 3.788 | 57.632 | 1.00 | 20.89 | B | N |
| ATOM | 4121 | CA | GLU | B | 479 | 26.034 | 3.580 | 56.540 | 0.00 | 21.59 | B | C |
| ATOM | 4122 | CB | GLU | B | 479 | 24.912 | 2.623 | 56.967 | 1.00 | 20.67 | B | C |
| ATOM | 4123 | CG | GLU | B | 479 | 23.944 | 2.252 | 55.809 | 1.00 | 21.50 | B | C |
| ATOM | 4124 | CD | GLU | B | 479 | 24.588 | 1.396 | 54.686 | 1.00 | 22.29 | B | C |
| ATOM | 4125 | OE1 | GLU | B | 479 | 25.476 | 0.557 | 54.948 | 1.00 | 22.67 | B | O |
| ATOM | 4126 | OE2 | GLU | B | 479 | 24.173 | 1.521 | 53.515 | 1.00 | 24.01 | B | O |
| ATOM | 4127 | C | GLU | B | 479 | 25.417 | 4.904 | 56.076 | 1.00 | 22.47 | B | C |
| ATOM | 4128 | O | GLU | B | 479 | 25.321 | 5.170 | 54.887 | 1.00 | 23.17 | B | O |
| ATOM | 4129 | N | ARG | B | 480 | 25.012 | 5.734 | 57.012 | 1.00 | 23.20 | B | N |
| ATOM | 4130 | CA | ARG | B | 480 | 24.417 | 7.019 | 56.642 | 0.00 | 24.24 | B | C |
| ATOM | 4131 | CB | ARG | B | 480 | 23.508 | 7.490 | 57.755 | 1.00 | 27.41 | B | C |
| ATOM | 4132 | CG | ARG | B | 480 | 22.299 | 6.672 | 57.940 | 1.00 | 32.58 | B | C |
| ATOM | 4133 | CD | ARG | B | 480 | 21.660 | 7.281 | 59.097 | 1.00 | 37.63 | B | C |
| ATOM | 4134 | NE | ARG | B | 480 | 20.374 | 6.689 | 59.373 | 1.00 | 43.64 | B | N |
| ATOM | 4135 | CZ | ARG | B | 480 | 19.894 | 6.513 | 60.607 | 1.00 | 46.04 | B | C |
| ATOM | 4136 | NH1 | ARG | B | 480 | 20.619 | 6.888 | 61.668 | 1.00 | 46.90 | B | N |
| ATOM | 4137 | NH2 | ARG | B | 480 | 18.679 | 5.990 | 60.767 | 1.00 | 46.64 | B | N |
| ATOM | 4138 | C | ARG | B | 480 | 25.507 | 8.039 | 56.472 | 1.00 | 22.60 | B | C |
| ATOM | 4139 | O | ARG | B | 480 | 26.355 | 8.177 | 57.327 | 1.00 | 21.78 | B | O |
| ATOM | 4140 | N | PRO | B | 481 | 25.449 | 8.820 | 55.404 | 1.00 | 22.01 | B | N |
| ATOM | 4141 | CD | PRO | B | 481 | 24.500 | 8.749 | 54.276 | 1.00 | 22.58 | B | C |
| ATOM | 4142 | CA | PRO | B | 481 | 26.477 | 9.831 | 55.145 | 0.00 | 21.20 | B | C |
| ATOM | 4143 | CB | PRO | B | 481 | 25.956 | 10.546 | 53.883 | 1.00 | 21.48 | B | C |
| ATOM | 4144 | CG | PRO | B | 481 | 25.262 | 9.489 | 53.147 | 1.00 | 20.60 | B | C |
| ATOM | 4145 | C | PRO | B | 481 | 26.638 | 10.802 | 56.267 | 1.00 | 20.86 | B | C |
| ATOM | 4146 | O | PRO | B | 481 | 27.757 | 11.074 | 56.660 | 1.00 | 19.51 | B | O |
| ATOM | 4147 | N | GLU | B | 482 | 25.511 | 11.245 | 56.849 | 1.00 | 21.43 | B | N |
| ATOM | 4148 | CA | GLU | B | 482 | 25.528 | 12.245 | 57.933 | 0.00 | 20.48 | B | C |
| ATOM | 4149 | CB | GLU | B | 482 | 24.108 | 12.727 | 58.256 | 1.00 | 22.16 | B | C |
| ATOM | 4150 | CG | GLU | B | 482 | 23.164 | 11.657 | 58.890 | 1.00 | 22.96 | B | C |
| ATOM | 4151 | CD | GLU | B | 482 | 22.376 | 10.850 | 57.862 | 1.00 | 24.82 | B | C |
| ATOM | 4152 | OE1 | GLU | B | 482 | 22.691 | 10.816 | 56.653 | 1.00 | 25.20 | B | O |
| ATOM | 4153 | OE2 | GLU | B | 482 | 21.390 | 10.247 | 58.263 | 1.00 | 27.81 | B | O |
| ATOM | 4154 | C | GLU | B | 482 | 26.272 | 11.814 | 59.178 | 1.00 | 20.11 | B | C |
| ATOM | 4155 | O | GLU | B | 482 | 26.804 | 12.663 | 59.912 | 1.00 | 19.56 | B | O |
| ATOM | 4156 | N | ASP | B | 483 | 26.404 | 10.507 | 59.383 | 1.00 | 19.54 | B | N |
| ATOM | 4157 | CA | ASP | B | 483 | 27.104 | 10.010 | 60.559 | 0.00 | 20.26 | B | C |
| ATOM | 4158 | CB | ASP | B | 483 | 26.569 | 8.626 | 60.974 | 1.00 | 21.30 | B | C |
| ATOM | 4159 | CG | ASP | B | 483 | 25.082 | 8.680 | 61.368 | 1.00 | 23.56 | B | C |
| ATOM | 4160 | OD1 | ASP | B | 483 | 24.647 | 9.726 | 61.883 | 1.00 | 22.77 | B | O |
| ATOM | 4161 | OD2 | ASP | B | 483 | 24.357 | 7.675 | 61.161 | 1.00 | 25.38 | B | O |
| ATOM | 4162 | C | ASP | B | 483 | 28.606 | 9.936 | 60.379 | 1.00 | 20.54 | B | C |
| ATOM | 4163 | O | ASP | B | 483 | 29.328 | 9.630 | 61.306 | 1.00 | 21.29 | B | O |
| ATOM | 4164 | N | ARG | B | 484 | 29.084 | 10.099 | 59.148 | 1.00 | 20.31 | B | N |
| ATOM | 4165 | CA | ARG | B | 484 | 30.518 | 10.051 | 58.907 | 0.00 | 18.99 | B | C |
| ATOM | 4166 | CB | ARG | B | 484 | 30.805 | 9.762 | 57.423 | 1.00 | 18.01 | B | C |
| ATOM | 4167 | CG | ARG | B | 484 | 30.219 | 8.479 | 56.938 | 1.00 | 16.80 | B | C |
| ATOM | 4168 | CD | ARG | B | 484 | 30.303 | 8.363 | 55.431 | 1.00 | 16.98 | B | C |
| ATOM | 4169 | NE | ARG | B | 484 | 29.460 | 7.259 | 55.002 | 1.00 | 17.57 | B | N |
| ATOM | 4170 | CZ | ARG | B | 484 | 28.888 | 7.173 | 53.814 | 1.00 | 17.25 | B | C |
| ATOM | 4171 | NH1 | ARG | B | 484 | 29.098 | 8.082 | 52.912 | 1.00 | 17.81 | B | N |
| ATOM | 4172 | NH2 | ARG | B | 484 | 27.947 | 6.256 | 53.599 | 1.00 | 17.35 | B | N |
| ATOM | 4173 | C | ARG | B | 484 | 31.075 | 11.411 | 59.305 | 1.00 | 18.18 | B | C |
| ATOM | 4174 | O | ARG | B | 484 | 30.416 | 12.445 | 59.154 | 1.00 | 15.55 | B | O |
| ATOM | 4175 | N | PRO | B | 485 | 32.304 | 11.415 | 59.859 | 1.00 | 18.58 | B | N |
| ATOM | 4176 | CD | PRO | B | 485 | 32.992 | 10.168 | 60.251 | 1.00 | 18.05 | B | C |

Figure 12

| | | | | | | | | | | | | |
|---|---|---|---|---|---|---|---|---|---|---|---|---|
| ATOM | 4177 | CA | PRO | B | 485 | 33.041 | 12.593 | 60.325 | 0.00 | 17.72 | B | C |
| ATOM | 4178 | CB | PRO | B | 485 | 34.302 | 11.969 | 60.960 | 1.00 | 19.58 | B | C |
| ATOM | 4179 | CG | PRO | B | 485 | 34.413 | 10.625 | 60.332 | 1.00 | 17.96 | B | C |
| ATOM | 4180 | C | PRO | B | 485 | 33.442 | 13.509 | 59.196 | 1.00 | 18.33 | B | C |
| ATOM | 4181 | O | PRO | B | 485 | 33.521 | 13.073 | 58.061 | 1.00 | 19.38 | B | O |
| ATOM | 4182 | N | THR | B | 486 | 33.679 | 14.791 | 59.479 | 1.00 | 17.72 | B | N |
| ATOM | 4183 | CA | THR | B | 486 | 34.156 | 15.707 | 58.448 | 0.00 | 17.64 | B | C |
| ATOM | 4184 | CB | THR | B | 486 | 34.065 | 17.154 | 58.918 | 1.00 | 17.32 | B | C |
| ATOM | 4185 | OG1 | THR | B | 486 | 34.812 | 17.260 | 60.144 | 1.00 | 18.38 | B | O |
| ATOM | 4186 | CG2 | THR | B | 486 | 32.574 | 17.624 | 59.135 | 1.00 | 17.91 | B | C |
| ATOM | 4187 | C | THR | B | 486 | 35.687 | 15.432 | 58.269 | 1.00 | 19.05 | B | C |
| ATOM | 4188 | O | THR | B | 486 | 36.310 | 14.798 | 59.125 | 1.00 | 18.75 | B | O |
| ATOM | 4189 | N | PHE | B | 487 | 36.290 | 15.886 | 57.162 | 1.00 | 19.69 | B | N |
| ATOM | 4190 | CA | PHE | B | 487 | 37.722 | 15.745 | 56.969 | 0.00 | 20.78 | B | C |
| ATOM | 4191 | CB | PHE | B | 487 | 38.149 | 16.050 | 55.517 | 1.00 | 18.44 | B | C |
| ATOM | 4192 | CG | PHE | B | 487 | 37.954 | 14.882 | 54.603 | 1.00 | 15.57 | B | C |
| ATOM | 4193 | CD1 | PHE | B | 487 | 38.740 | 13.751 | 54.744 | 1.00 | 15.34 | B | C |
| ATOM | 4194 | CD2 | PHE | B | 487 | 36.943 | 14.894 | 53.651 | 1.00 | 16.19 | B | C |
| ATOM | 4195 | CE1 | PHE | B | 487 | 38.524 | 12.631 | 53.942 | 1.00 | 14.42 | B | C |
| ATOM | 4196 | CE2 | PHE | B | 487 | 36.705 | 13.801 | 52.840 | 1.00 | 14.97 | B | C |
| ATOM | 4197 | CZ | PHE | B | 487 | 37.498 | 12.652 | 52.978 | 1.00 | 14.91 | B | C |
| ATOM | 4198 | C | PHE | B | 487 | 38.410 | 16.677 | 57.954 | 1.00 | 22.41 | B | C |
| ATOM | 4199 | O | PHE | B | 487 | 39.491 | 16.390 | 58.428 | 1.00 | 21.58 | B | O |
| ATOM | 4200 | N | ASP | B | 488 | 37.765 | 17.782 | 58.297 | 1.00 | 25.25 | B | N |
| ATOM | 4201 | CA | ASP | B | 488 | 38.349 | 18.700 | 59.280 | 0.00 | 27.45 | B | C |
| ATOM | 4202 | CB | ASP | B | 488 | 37.350 | 19.820 | 59.519 | 1.00 | 31.96 | B | C |
| ATOM | 4203 | CG | ASP | B | 488 | 37.819 | 20.837 | 60.562 | 1.00 | 35.61 | B | C |
| ATOM | 4204 | OD1 | ASP | B | 488 | 39.039 | 20.943 | 60.870 | 1.00 | 37.71 | B | O |
| ATOM | 4205 | OD2 | ASP | B | 488 | 36.924 | 21.556 | 61.080 | 1.00 | 38.73 | B | O |
| ATOM | 4206 | C | ASP | B | 488 | 38.636 | 17.947 | 60.593 | 1.00 | 28.12 | B | C |
| ATOM | 4207 | O | ASP | B | 488 | 39.667 | 18.153 | 61.228 | 1.00 | 30.15 | B | O |
| ATOM | 4208 | N | TYR | B | 489 | 37.744 | 17.044 | 60.995 | 1.00 | 26.94 | B | N |
| ATOM | 4209 | CA | TYR | B | 489 | 37.919 | 16.274 | 62.215 | 0.00 | 24.66 | B | C |
| ATOM | 4210 | CB | TYR | B | 489 | 36.570 | 15.708 | 62.654 | 1.00 | 23.33 | B | C |
| ATOM | 4211 | CG | TYR | B | 489 | 36.690 | 14.645 | 63.705 | 1.00 | 22.22 | B | C |
| ATOM | 4212 | CD1 | TYR | B | 489 | 36.797 | 14.975 | 65.048 | 1.00 | 23.18 | B | C |
| ATOM | 4213 | CE1 | TYR | B | 489 | 36.862 | 13.975 | 66.045 | 1.00 | 23.37 | B | C |
| ATOM | 4214 | CD2 | TYR | B | 489 | 36.660 | 13.306 | 63.353 | 1.00 | 23.21 | B | C |
| ATOM | 4215 | CE2 | TYR | B | 489 | 36.725 | 12.298 | 64.304 | 1.00 | 24.25 | B | C |
| ATOM | 4216 | CZ | TYR | B | 489 | 36.829 | 12.630 | 65.657 | 1.00 | 25.10 | B | C |
| ATOM | 4217 | OH | TYR | B | 489 | 36.971 | 11.615 | 66.582 | 1.00 | 25.76 | B | O |
| ATOM | 4218 | C | TYR | B | 489 | 38.917 | 15.123 | 62.021 | 1.00 | 24.22 | B | C |
| ATOM | 4219 | O | TYR | B | 489 | 39.635 | 14.761 | 62.956 | 1.00 | 23.85 | B | O |
| ATOM | 4220 | N | LEU | B | 490 | 38.886 | 14.478 | 60.857 | 1.00 | 23.21 | B | N |
| ATOM | 4221 | CA | LEU | B | 490 | 39.823 | 13.388 | 60.543 | 0.00 | 23.59 | B | C |
| ATOM | 4222 | CB | LEU | B | 490 | 39.497 | 12.782 | 59.177 | 1.00 | 21.27 | B | C |
| ATOM | 4223 | CG | LEU | B | 490 | 38.250 | 11.860 | 59.159 | 1.00 | 21.85 | B | C |
| ATOM | 4224 | CD1 | LEU | B | 490 | 37.871 | 11.446 | 57.766 | 1.00 | 17.86 | B | C |
| ATOM | 4225 | CD2 | LEU | B | 490 | 38.502 | 10.625 | 59.957 | 1.00 | 21.77 | B | C |
| ATOM | 4226 | C | LEU | B | 490 | 41.312 | 13.880 | 60.621 | 1.00 | 24.25 | B | C |
| ATOM | 4227 | O | LEU | B | 490 | 42.196 | 13.165 | 61.105 | 1.00 | 22.57 | B | O |
| ATOM | 4228 | N | ARG | B | 491 | 41.557 | 15.101 | 60.161 | 1.00 | 25.48 | B | N |
| ATOM | 4229 | CA | ARG | B | 491 | 42.891 | 15.672 | 60.212 | 0.00 | 28.37 | B | C |
| ATOM | 4230 | CB | ARG | B | 491 | 42.929 | 16.980 | 59.432 | 1.00 | 30.22 | B | C |
| ATOM | 4231 | CG | ARG | B | 491 | 44.128 | 17.787 | 59.739 | 1.00 | 34.23 | B | C |
| ATOM | 4232 | CD | ARG | B | 491 | 43.999 | 19.188 | 59.218 | 1.00 | 39.77 | B | C |
| ATOM | 4233 | NE | ARG | B | 491 | 42.848 | 19.891 | 59.783 | 1.00 | 44.26 | B | N |
| ATOM | 4234 | CZ | ARG | B | 491 | 42.746 | 20.260 | 61.062 | 1.00 | 46.81 | B | C |
| ATOM | 4235 | NH1 | ARG | B | 491 | 43.732 | 20.009 | 61.934 | 1.00 | 47.08 | B | N |

Figure 12

| ATOM | 4236 | NH2 | ARG | B | 491 | 41.620 | 20.835 | 61.482 | 1.00 | 48.73 | B | N |
|------|------|-----|-----|---|-----|--------|--------|--------|------|-------|---|---|
| ATOM | 4237 | C | ARG | B | 491 | 43.373 | 15.870 | 61.674 | 1.00 | 28.93 | B | C |
| ATOM | 4238 | O | ARG | B | 491 | 44.451 | 15.399 | 62.016 | 1.00 | 29.72 | B | O |
| ATOM | 4239 | N | SER | B | 492 | 42.557 | 16.483 | 62.555 | 1.00 | 29.25 | B | N |
| ATOM | 4240 | CA | SER | B | 492 | 42.937 | 16.694 | 63.965 | 0.00 | 29.12 | B | C |
| ATOM | 4241 | CB | SER | B | 492 | 41.835 | 17.425 | 64.735 | 1.00 | 29.15 | B | C |
| ATOM | 4242 | OG | SER | B | 492 | 41.375 | 18.528 | 63.993 | 1.00 | 31.79 | B | O |
| ATOM | 4243 | C | SER | B | 492 | 43.215 | 15.419 | 64.712 | 1.00 | 28.84 | B | C |
| ATOM | 4244 | O | SER | B | 492 | 44.108 | 15.357 | 65.567 | 1.00 | 30.77 | B | O |
| ATOM | 4245 | N | VAL | B | 493 | 42.454 | 14.389 | 64.465 | 1.00 | 28.80 | B | N |
| ATOM | 4246 | CA | VAL | B | 493 | 42.692 | 13.163 | 65.210 | 0.00 | 30.05 | B | C |
| ATOM | 4247 | CB | VAL | B | 493 | 41.398 | 12.275 | 65.388 | 1.00 | 30.95 | B | C |
| ATOM | 4248 | CG1 | VAL | B | 493 | 40.471 | 12.474 | 64.248 | 1.00 | 31.73 | B | C |
| ATOM | 4249 | CG2 | VAL | B | 493 | 41.747 | 10.785 | 65.501 | 1.00 | 30.53 | B | C |
| ATOM | 4250 | C | VAL | B | 493 | 43.896 | 12.416 | 64.702 | 1.00 | 30.82 | B | C |
| ATOM | 4251 | O | VAL | B | 493 | 44.626 | 11.793 | 65.486 | 1.00 | 30.03 | B | O |
| ATOM | 4252 | N | LEU | B | 494 | 44.152 | 12.548 | 63.394 | 1.00 | 32.36 | B | N |
| ATOM | 4253 | CA | LEU | B | 494 | 45.302 | 11.908 | 62.775 | 0.00 | 33.17 | B | C |
| ATOM | 4254 | CB | LEU | B | 494 | 45.112 | 11.784 | 61.247 | 1.00 | 30.65 | B | C |
| ATOM | 4255 | CG | LEU | B | 494 | 44.163 | 10.641 | 60.830 | 1.00 | 29.88 | B | C |
| ATOM | 4256 | CD1 | LEU | B | 494 | 43.909 | 10.726 | 59.351 | 1.00 | 27.17 | B | C |
| ATOM | 4257 | CD2 | LEU | B | 494 | 44.674 | 9.237 | 61.238 | 1.00 | 28.03 | B | C |
| ATOM | 4258 | C | LEU | B | 494 | 46.601 | 12.667 | 63.167 | 1.00 | 34.52 | B | C |
| ATOM | 4259 | O | LEU | B | 494 | 47.608 | 12.053 | 63.458 | 1.00 | 34.61 | B | O |
| ATOM | 4260 | N | GLU | B | 495 | 46.553 | 13.985 | 63.258 | 1.00 | 36.40 | B | N |
| ATOM | 4261 | CA | GLU | B | 495 | 47.727 | 14.756 | 63.637 | 0.00 | 38.96 | B | C |
| ATOM | 4262 | CB | GLU | B | 495 | 47.432 | 16.239 | 63.521 | 1.00 | 38.84 | B | C |
| ATOM | 4263 | CG | GLU | B | 495 | 47.863 | 16.843 | 62.241 | 1.00 | 40.36 | B | C |
| ATOM | 4264 | CD | GLU | B | 495 | 47.383 | 18.255 | 62.117 | 1.00 | 42.40 | B | C |
| ATOM | 4265 | OE1 | GLU | B | 495 | 47.419 | 18.959 | 63.153 | 1.00 | 43.98 | B | O |
| ATOM | 4266 | OE2 | GLU | B | 495 | 46.976 | 18.653 | 60.993 | 1.00 | 43.62 | B | O |
| ATOM | 4267 | C | GLU | B | 495 | 48.153 | 14.494 | 65.080 | 1.00 | 41.29 | B | C |
| ATOM | 4268 | O | GLU | B | 495 | 49.339 | 14.367 | 65.365 | 1.00 | 42.08 | B | O |
| ATOM | 4269 | N | ASP | B | 496 | 47.185 | 14.480 | 65.993 | 1.00 | 43.16 | B | N |
| ATOM | 4270 | CA | ASP | B | 496 | 47.475 | 14.260 | 67.391 | 0.00 | 44.98 | B | C |
| ATOM | 4271 | CB | ASP | B | 496 | 46.544 | 15.102 | 68.286 | 1.00 | 47.36 | B | C |
| ATOM | 4272 | CG | ASP | B | 496 | 46.476 | 16.600 | 67.869 | 1.00 | 50.65 | B | C |
| ATOM | 4273 | OD1 | ASP | B | 496 | 47.534 | 17.245 | 67.612 | 1.00 | 51.38 | B | O |
| ATOM | 4274 | OD2 | ASP | B | 496 | 45.332 | 17.145 | 67.822 | 1.00 | 52.66 | B | O |
| ATOM | 4275 | C | ASP | B | 496 | 47.318 | 12.794 | 67.756 | 1.00 | 45.69 | B | C |
| ATOM | 4276 | O | ASP | B | 496 | 46.989 | 12.489 | 68.901 | 1.00 | 46.08 | B | O |
| ATOM | 4277 | N | PHE | B | 497 | 47.603 | 11.876 | 66.831 | 1.00 | 46.28 | B | N |
| ATOM | 4278 | CA | PHE | B | 497 | 47.434 | 10.454 | 67.136 | 0.00 | 46.97 | B | C |
| ATOM | 4279 | CB | PHE | B | 497 | 47.489 | 9.605 | 65.875 | 1.00 | 45.68 | B | C |
| ATOM | 4280 | CG | PHE | B | 497 | 46.731 | 8.310 | 65.981 | 1.00 | 45.95 | B | C |
| ATOM | 4281 | CD1 | PHE | B | 497 | 45.391 | 8.228 | 65.589 | 1.00 | 46.29 | B | C |
| ATOM | 4282 | CD2 | PHE | B | 497 | 47.359 | 7.153 | 66.452 | 1.00 | 46.19 | B | C |
| ATOM | 4283 | CE1 | PHE | B | 497 | 44.683 | 7.000 | 65.660 | 1.00 | 46.73 | B | C |
| ATOM | 4284 | CE2 | PHE | B | 497 | 46.665 | 5.917 | 66.531 | 1.00 | 46.89 | B | C |
| ATOM | 4285 | CZ | PHE | B | 497 | 45.328 | 5.840 | 66.132 | 1.00 | 46.36 | B | C |
| ATOM | 4286 | C | PHE | B | 497 | 48.408 | 9.976 | 68.226 | 1.00 | 48.31 | B | C |
| ATOM | 4287 | O | PHE | B | 497 | 48.041 | 9.178 | 69.102 | 1.00 | 47.78 | B | O |
| ATOM | 4288 | N | PHE | B | 498 | 49.652 | 10.447 | 68.145 | 1.00 | 49.79 | B | N |
| ATOM | 4289 | CA | PHE | B | 498 | 50.682 | 10.154 | 69.156 | 0.00 | 51.06 | B | C |
| ATOM | 4290 | CB | PHE | B | 498 | 50.912 | 8.647 | 69.397 | 1.00 | 50.99 | B | C |
| ATOM | 4291 | CG | PHE | B | 498 | 51.092 | 7.813 | 68.147 | 1.00 | 51.02 | B | C |
| ATOM | 4292 | CD1 | PHE | B | 498 | 51.549 | 8.367 | 66.960 | 1.00 | 50.85 | B | C |
| ATOM | 4293 | CD2 | PHE | B | 498 | 50.761 | 6.455 | 68.173 | 1.00 | 50.74 | B | C |
| ATOM | 4294 | CE1 | PHE | B | 498 | 51.665 | 7.578 | 65.831 | 1.00 | 51.38 | B | C |

Figure 12

| ATOM | 4295 | CE2 | PHE | B | 498 | 50.873 | 5.658 | 67.054 | 1.00 | 50.78 | B | C |
|------|------|-----|-----|---|-----|--------|-------|--------|------|-------|---|---|
| ATOM | 4296 | CZ  | PHE | B | 498 | 51.320 | 6.213 | 65.879 | 1.00 | 51.40 | B | C |
| ATOM | 4297 | C   | PHE | B | 498 | 52.008 | 10.879 | 68.936 | 1.00 | 52.05 | B | C |
| ATOM | 4298 | O   | PHE | B | 498 | 52.265 | 11.831 | 69.716 | 1.00 | 52.87 | B | O |
| ATOM | 4299 | N1  | LIG | B | 500 | 52.986 | 4.430 | 37.742 | 1.00 | 42.19 | B | N |
| ATOM | 4300 | C1  | LIG | B | 500 | 52.597 | 5.874 | 37.886 | 1.00 | 40.68 | B | C |
| ATOM | 4301 | C2  | LIG | B | 500 | 52.861 | 6.527 | 39.293 | 1.00 | 39.30 | B | C |
| ATOM | 4302 | C3  | LIG | B | 500 | 52.397 | 8.007 | 39.322 | 1.00 | 37.20 | B | C |
| ATOM | 4303 | C4  | LIG | B | 500 | 53.052 | 8.666 | 38.114 | 1.00 | 29.73 | B | C |
| ATOM | 4304 | C5  | LIG | B | 500 | 52.873 | 8.225 | 36.874 | 1.00 | 36.81 | B | C |
| ATOM | 4305 | C6  | LIG | B | 500 | 53.307 | 6.751 | 36.790 | 1.00 | 39.27 | B | C |
| ATOM | 4306 | N2  | LIG | B | 500 | 52.653 | 10.133 | 38.151 | 1.00 | 29.80 | B | N |
| ATOM | 4307 | N3  | LIG | B | 500 | 51.517 | 10.712 | 37.789 | 1.00 | 30.08 | B | N |
| ATOM | 4308 | C7  | LIG | B | 500 | 51.582 | 12.036 | 37.990 | 1.00 | 29.89 | B | C |
| ATOM | 4309 | C8  | LIG | B | 500 | 52.884 | 12.360 | 38.539 | 1.00 | 29.14 | B | C |
| ATOM | 4310 | C9  | LIG | B | 500 | 53.511 | 13.508 | 38.946 | 1.00 | 28.60 | B | C |
| ATOM | 4311 | N4  | LIG | B | 500 | 54.801 | 13.412 | 39.427 | 1.00 | 28.62 | B | N |
| ATOM | 4312 | C10 | LIG | B | 500 | 55.457 | 12.225 | 39.507 | 1.00 | 28.54 | B | C |
| ATOM | 4313 | N5  | LIG | B | 500 | 54.868 | 11.068 | 39.115 | 1.00 | 28.66 | B | N |
| ATOM | 4314 | C11 | LIG | B | 500 | 53.561 | 11.168 | 38.634 | 1.00 | 28.92 | B | C |
| ATOM | 4315 | N6  | LIG | B | 500 | 52.928 | 14.821 | 38.916 | 1.00 | 28.39 | B | N |
| ATOM | 4316 | C12 | LIG | B | 500 | 50.390 | 12.806 | 37.635 | 1.00 | 31.62 | B | C |
| ATOM | 4317 | C13 | LIG | B | 500 | 49.131 | 12.482 | 38.298 | 1.00 | 32.55 | B | C |
| ATOM | 4318 | C14 | LIG | B | 500 | 47.974 | 13.237 | 37.944 | 1.00 | 33.35 | B | C |
| ATOM | 4319 | C15 | LIG | B | 500 | 48.013 | 14.324 | 36.938 | 1.00 | 33.61 | B | C |
| ATOM | 4320 | C16 | LIG | B | 500 | 49.295 | 14.635 | 36.286 | 1.00 | 33.38 | B | C |
| ATOM | 4321 | C17 | LIG | B | 500 | 50.451 | 13.866 | 36.656 | 1.00 | 32.68 | B | C |
| ATOM | 4322 | C18 | LIG | B | 500 | 54.304 | 3.931 | 38.290 | 1.00 | 43.43 | B | C |
| ATOM | 4323 | C19 | LIG | B | 500 | 54.545 | 2.408 | 38.050 | 1.00 | 43.88 | B | C |
| ATOM | 4324 | N7  | LIG | B | 500 | 53.468 | 1.600 | 38.686 | 1.00 | 44.55 | B | N |
| ATOM | 4325 | C20 | LIG | B | 500 | 53.700 | 0.126 | 38.484 | 1.00 | 45.33 | B | C |
| ATOM | 4326 | C21 | LIG | B | 500 | 52.176 | 2.012 | 38.071 | 1.00 | 44.40 | B | C |
| ATOM | 4327 | C22 | LIG | B | 500 | 51.865 | 3.535 | 38.243 | 1.00 | 43.24 | B | C |
| ATOM | 4328 | O1  | LIG | B | 500 | 49.297 | 15.614 | 35.540 | 1.00 | 39.33 | B | O |
| ATOM | 4329 | C23 | LIG | B | 500 | 50.310 | 15.632 | 34.500 | 1.00 | 38.77 | B | C |
| ATOM | 4330 | C24 | LIG | B | 500 | 46.008 | 15.700 | 37.467 | 1.00 | 44.35 | B | C |
| ATOM | 4331 | O2  | LIG | B | 500 | 46.163 | 15.778 | 38.704 | 1.00 | 43.83 | B | O |
| ATOM | 4332 | N8  | LIG | B | 500 | 46.849 | 15.051 | 36.634 | 1.00 | 41.95 | B | N |
| ATOM | 4333 | C25 | LIG | B | 500 | 44.857 | 16.328 | 36.904 | 0.00 | 46.74 | B | C |
| ATOM | 4334 | C26 | LIG | B | 500 | 44.444 | 16.378 | 35.558 | 0.00 | 47.08 | B | C |
| ATOM | 4335 | N9  | LIG | B | 500 | 43.958 | 17.015 | 37.709 | 0.00 | 47.32 | B | N |
| ATOM | 4336 | C27 | LIG | B | 500 | 42.265 | 17.553 | 34.555 | 0.00 | 46.55 | B | C |
| ATOM | 4337 | C28 | LIG | B | 500 | 43.197 | 17.137 | 35.555 | 0.00 | 47.01 | B | C |
| ATOM | 4338 | C29 | LIG | B | 500 | 42.930 | 17.515 | 36.888 | 0.00 | 47.46 | B | C |
| ATOM | 4339 | C30 | LIG | B | 500 | 41.779 | 18.288 | 37.205 | 0.00 | 47.54 | B | C |
| ATOM | 4340 | C31 | LIG | B | 500 | 40.872 | 18.684 | 36.179 | 0.00 | 46.97 | B | C |
| ATOM | 4341 | C32 | LIG | B | 500 | 41.119 | 18.316 | 34.852 | 0.00 | 45.93 | B | C |
| ATOM | 4342 | N10 | LIG | B | 500 | 43.972 | 16.941 | 31.496 | 0.00 | 40.00 | B | N |
| ATOM | 4343 | C33 | LIG | B | 500 | 44.066 | 17.195 | 39.147 | 0.00 | 27.64 | B | C |
| ATOM | 4344 | OH2 | H2O | B | 600 | 34.275 | 0.303 | 49.942 | 1.00 | 15.57 | B | O |
| ATOM | 4345 | OH2 | H2O | B | 601 | 29.651 | 18.851 | 60.815 | 1.00 | 68.55 | B | O |
| ATOM | 4346 | OH2 | H2O | B | 602 | 27.281 | -1.721 | 58.668 | 1.00 | 18.10 | B | O |
| ATOM | 4347 | OH2 | H2O | B | 604 | 34.311 | 19.726 | 62.343 | 1.00 | 43.74 | B | O |
| ATOM | 4348 | OH2 | H2O | B | 605 | 22.668 | -2.941 | 57.089 | 1.00 | 49.35 | B | O |
| ATOM | 4349 | OH2 | H2O | B | 606 | 36.146 | 9.286 | 46.436 | 1.00 | 16.41 | B | O |
| ATOM | 4350 | OH2 | H2O | B | 607 | 25.086 | 5.224 | 59.998 | 1.00 | 20.11 | B | O |
| ATOM | 4351 | OH2 | H2O | B | 608 | 28.930 | 12.801 | 62.239 | 1.00 | 46.99 | B | O |
| ATOM | 4352 | OH2 | H2O | B | 609 | 27.689 | -8.244 | 57.100 | 1.00 | 29.09 | B | O |
| ATOM | 4353 | OH2 | H2O | B | 610 | 34.714 | -1.966 | 55.094 | 1.00 | 21.25 | B | O |

Figure 12

| | | | | | | | | | | |
|---|---|---|---|---|---|---|---|---|---|---|
| ATOM | 4354 | OH2 | H2O | B | 611 | 33.817 | 3.498 | 65.550 | 1.00 27.69 | B | O |
| ATOM | 4355 | OH2 | H2O | B | 612 | 29.127 | 16.484 | 59.094 | 1.00 32.72 | B | O |
| ATOM | 4356 | OH2 | H2O | B | 613 | 28.012 | -6.214 | 59.544 | 1.00 61.22 | B | O |
| ATOM | 4357 | OH2 | H2O | B | 614 | 38.210 | 13.086 | 40.542 | 1.00 21.35 | B | O |
| ATOM | 4358 | OH2 | H2O | B | 615 | 18.933 | 14.161 | 61.904 | 1.00 38.20 | B | O |
| ATOM | 4359 | OH2 | H2O | B | 616 | 26.807 | 15.332 | 59.404 | 1.00 28.53 | B | O |
| ATOM | 4360 | OH2 | H2O | B | 617 | 31.028 | -7.899 | 59.324 | 1.00 62.20 | B | O |
| ATOM | 4361 | OH2 | H2O | B | 618 | 37.269 | -2.381 | 42.911 | 1.00 23.17 | B | O |
| ATOM | 4362 | OH2 | H2O | B | 619 | 27.589 | 17.418 | 55.229 | 1.00 79.42 | B | O |
| ATOM | 4363 | OH2 | H2O | B | 620 | 29.926 | -4.320 | 62.088 | 1.00 32.45 | B | O |
| ATOM | 4364 | OH2 | H2O | B | 621 | 58.721 | 8.812 | 39.554 | 0.00 44.73 | B | O |
| ATOM | 4365 | OH2 | H2O | B | 622 | 32.156 | 21.723 | 61.230 | 1.00 58.74 | B | O |
| ATOM | 4366 | OH2 | H2O | B | 623 | 25.027 | -1.258 | 57.439 | 1.00 40.20 | B | O |
| ATOM | 4367 | OH2 | H2O | B | 624 | 64.394 | 11.468 | 37.824 | 1.00 40.42 | B | O |
| ATOM | 4368 | OH2 | H2O | B | 625 | 49.009 | 17.252 | 58.295 | 1.00 45.92 | B | O |
| ATOM | 4369 | OH2 | H2O | B | 626 | 44.579 | 2.751 | 45.290 | 1.00 25.70 | B | O |
| ATOM | 4370 | OH2 | H2O | B | 627 | 32.162 | 16.103 | 55.752 | 1.00 20.03 | B | O |
| ATOM | 4371 | OH2 | H2O | B | 628 | 32.720 | 6.887 | 47.711 | 1.00 23.67 | B | O |
| ATOM | 4372 | OH2 | H2O | B | 630 | 37.121 | 6.995 | 66.835 | 1.00 62.29 | B | O |
| ATOM | 4373 | OH2 | H2O | B | 631 | 63.035 | 23.905 | 26.926 | 1.00 52.06 | B | O |
| ATOM | 4374 | OH2 | H2O | B | 632 | 33.803 | -5.785 | 60.833 | 1.00 23.79 | B | O |
| ATOM | 4375 | OH2 | H2O | B | 633 | 45.955 | 10.383 | 40.222 | 1.00 59.43 | B | O |
| ATOM | 4376 | OH2 | H2O | B | 634 | 45.567 | 23.248 | 55.341 | 1.00 36.60 | B | O |
| ATOM | 4377 | OH2 | H2O | B | 635 | 27.663 | 10.638 | 49.361 | 1.00 37.89 | B | O |
| ATOM | 4378 | OH2 | H2O | B | 636 | 25.977 | 9.874 | 64.281 | 1.00 24.08 | B | O |
| ATOM | 4379 | OH2 | H2O | B | 638 | 19.640 | 13.961 | 64.442 | 1.00 25.58 | B | O |
| ATOM | 4380 | OH2 | H2O | B | 639 | 44.089 | 11.541 | 68.086 | 1.00 41.87 | B | O |
| ATOM | 4381 | OH2 | H2O | B | 640 | 26.796 | -1.197 | 53.754 | 1.00 26.97 | B | O |
| ATOM | 4382 | OH2 | H2O | B | 641 | 25.738 | 15.711 | 56.945 | 1.00 25.46 | B | O |
| ATOM | 4383 | OH2 | H2O | B | 642 | 48.329 | 22.995 | 44.387 | 1.00 49.57 | B | O |
| ATOM | 4384 | OH2 | H2O | B | 643 | 55.749 | 0.062 | 26.485 | 1.00 86.97 | B | O |
| ATOM | 4385 | OH2 | H2O | B | 644 | 31.476 | 1.050 | 60.129 | 1.00 22.75 | B | O |
| ATOM | 4386 | OH2 | H2O | B | 645 | 24.476 | -1.425 | 49.547 | 1.00 44.34 | B | O |
| ATOM | 4387 | OH2 | H2O | B | 646 | 57.600 | 21.920 | 19.355 | 1.00 72.15 | B | O |
| ATOM | 4388 | OH2 | H2O | B | 647 | 32.623 | -13.452 | 52.449 | 1.00 57.40 | B | O |
| ATOM | 4389 | OH2 | H2O | B | 648 | 29.686 | 17.391 | 49.151 | 1.00 25.30 | B | O |
| ATOM | 4390 | OH2 | H2O | B | 649 | 14.814 | 16.560 | 62.182 | 1.00 57.59 | B | O |
| ATOM | 4391 | OH2 | H2O | B | 650 | 40.894 | -5.521 | 56.989 | 1.00 26.12 | B | O |
| ATOM | 4392 | OH2 | H2O | B | 651 | 30.989 | 24.788 | 58.340 | 1.00 33.57 | B | O |
| ATOM | 4393 | OH2 | H2O | B | 652 | 27.144 | 1.573 | 60.217 | 1.00 29.60 | B | O |
| ATOM | 4394 | OH2 | H2O | B | 653 | 32.524 | -0.177 | 48.081 | 1.00 15.04 | B | O |
| ATOM | 4395 | OH2 | H2O | B | 654 | 31.493 | -8.386 | 63.378 | 1.00 26.25 | B | O |
| ATOM | 4396 | OH2 | H2O | B | 655 | 52.907 | 1.923 | 31.980 | 1.00 34.42 | B | O |
| ATOM | 4397 | OH2 | H2O | B | 656 | 33.862 | 18.893 | 42.968 | 1.00 39.90 | B | O |
| ATOM | 4398 | OH2 | H2O | B | 657 | 30.141 | 19.038 | 52.547 | 1.00 84.40 | B | O |
| ATOM | 4399 | OH2 | H2O | B | 658 | 26.769 | -2.185 | 64.563 | 1.00 58.11 | B | O |
| ATOM | 4400 | OH2 | H2O | B | 659 | 38.184 | -5.991 | 63.971 | 1.00 24.10 | B | O |
| ATOM | 4401 | OH2 | H2O | B | 660 | 62.496 | 10.259 | 36.490 | 1.00 41.88 | B | O |
| ATOM | 4402 | OH2 | H2O | B | 661 | 46.503 | 6.090 | 35.074 | 0.00 40.85 | B | O |
| ATOM | 4403 | OH2 | H2O | B | 662 | 22.358 | 11.723 | 62.492 | 1.00 83.08 | B | O |
| ATOM | 4404 | OH2 | H2O | B | 663 | 35.114 | -12.169 | 55.746 | 1.00 33.48 | B | O |
| ATOM | 4405 | OH2 | H2O | B | 664 | 34.601 | 10.563 | 67.434 | 1.00 73.39 | B | O |
| ATOM | 4406 | OH2 | H2O | B | 665 | 31.040 | 19.661 | 56.754 | 1.00 77.12 | B | O |
| ATOM | 4407 | OH2 | H2O | B | 666 | 26.445 | -2.273 | 60.975 | 1.00 54.27 | B | O |
| ATOM | 4408 | OH2 | H2O | B | 667 | 36.953 | 21.304 | 56.090 | 1.00 29.19 | B | O |
| ATOM | 4409 | OH2 | H2O | B | 668 | 51.260 | -1.211 | 60.032 | 1.00 35.22 | B | O |
| ATOM | 4410 | OH2 | H2O | B | 669 | 33.250 | 21.666 | 57.108 | 1.00 64.54 | B | O |
| ATOM | 4411 | OH2 | H2O | B | 670 | 23.321 | -2.205 | 61.174 | 1.00 83.90 | B | O |
| ATOM | 4412 | OH2 | H2O | B | 671 | 26.429 | 14.107 | 52.124 | 1.00 32.13 | B | O |

Figure 12

| | | | | | | | | | | | |
|---|---|---|---|---|---|---|---|---|---|---|---|
| ATOM | 4413 | OH2 | H2O | B | 672 | 35.364 | 19.657 | 41.049 | 1.00 75.45 | B | O |
| ATOM | 4414 | OH2 | H2O | B | 673 | 62.676 | 1.245 | 48.470 | 1.00 47.54 | B | O |
| ATOM | 4415 | OH2 | H2O | B | 674 | 43.081 | 22.005 | 55.669 | 1.00 30.59 | B | O |
| ATOM | 4416 | OH2 | H2O | B | 675 | 25.980 | -2.784 | 47.716 | 1.00 23.83 | B | O |
| ATOM | 4417 | OH2 | H2O | B | 676 | 60.700 | 17.862 | 41.724 | 1.00 54.57 | B | O |
| ATOM | 4418 | OH2 | H2O | B | 677 | 34.691 | 6.991 | 45.021 | 1.00 34.38 | B | O |
| ATOM | 4419 | OH2 | H2O | B | 678 | 23.548 | 3.703 | 52.273 | 1.00 59.48 | B | O |
| ATOM | 4420 | OH2 | H2O | B | 679 | 43.921 | 1.406 | 42.948 | 1.00 50.02 | B | O |
| ATOM | 4421 | OH2 | H2O | B | 680 | 61.361 | 6.928 | 27.946 | 1.00 37.76 | B | O |
| ATOM | 4422 | OH2 | H2O | B | 681 | 22.443 | 3.155 | 49.765 | 1.00 47.10 | B | O |
| ATOM | 4423 | OH2 | H2O | B | 682 | 58.420 | 19.605 | 40.136 | 1.00 33.56 | B | O |
| ATOM | 4424 | OH2 | H2O | B | 683 | 48.415 | 5.735 | 39.338 | 0.00 58.45 | B | O |
| ATOM | 4425 | OH2 | H2O | B | 684 | 43.356 | -2.534 | 52.233 | 1.00 22.10 | B | O |
| ATOM | 4426 | OH2 | H2O | B | 685 | 24.100 | -0.776 | 52.196 | 1.00 29.80 | B | O |
| ATOM | 4427 | OH2 | H2O | B | 686 | 45.472 | -1.587 | 69.330 | 1.00 30.49 | B | O |
| ATOM | 4428 | OH2 | H2O | B | 687 | 26.473 | -4.351 | 62.952 | 1.00 56.66 | B | O |
| ATOM | 4429 | OH2 | H2O | B | 688 | 62.806 | 9.594 | 48.953 | 1.00 65.71 | B | O |
| ATOM | 4430 | OH2 | H2O | B | 689 | 23.907 | -2.798 | 45.635 | 1.00 39.47 | B | O |
| ATOM | 4431 | OH2 | H2O | B | 690 | 33.447 | 17.362 | 26.801 | 1.00 62.38 | B | O |
| ATOM | 4432 | OH2 | H2O | B | 691 | 47.310 | 24.218 | 40.493 | 1.00 42.26 | B | O |
| ATOM | 4433 | OH2 | H2O | B | 692 | 41.429 | 0.859 | 41.596 | 1.00 40.03 | B | O |
| ATOM | 4434 | OH2 | H2O | B | 693 | 45.376 | -1.090 | 47.289 | 1.00 34.31 | B | O |
| ATOM | 4435 | OH2 | H2O | B | 694 | 46.350 | 22.454 | 42.618 | 1.00 52.39 | B | O |
| ATOM | 4436 | OH2 | H2O | B | 695 | 18.726 | 11.941 | 65.868 | 1.00 32.58 | B | O |
| ATOM | 4437 | OH2 | H2O | B | 696 | 59.527 | 5.590 | 58.802 | 1.00 64.51 | B | O |
| ATOM | 4438 | OH2 | H2O | B | 697 | 39.445 | 5.689 | 67.542 | 1.00 71.89 | B | O |
| ATOM | 4439 | OH2 | H2O | B | 698 | 53.638 | 11.052 | 24.975 | 1.00 52.53 | B | O |
| ATOM | 4440 | OH2 | H2O | B | 699 | 23.531 | 0.447 | 59.278 | 1.00 33.11 | B | O |
| END | | | | | | | | | | | |

Figure 12

```
CRYST1   57.602   44.452  119.769  90.00  89.89  90.00 P21           1
SCALE1      0.017361  0.000000 -0.000033        0.00000
SCALE2      0.000000  0.022496  0.000000        0.00000
SCALE3      0.000000  0.000000  0.008349        0.00000
ATOM      1  CB  TRP A 238      18.435  -5.680  27.796  1.00 59.87      A    C
ATOM      2  CG  TRP A 238      17.960  -6.284  26.487  1.00 60.00      A    C
ATOM      3  CD2 TRP A 238      18.529  -6.058  25.198  1.00 59.55      A    C
ATOM      4  CE2 TRP A 238      17.736  -6.771  24.260  1.00 60.62      A    C
ATOM      5  CE3 TRP A 238      19.613  -5.317  24.742  1.00 58.21      A    C
ATOM      6  CD1 TRP A 238      16.876  -7.111  26.290  1.00 60.88      A    C
ATOM      7  NE1 TRP A 238      16.742  -7.404  24.943  1.00 61.19      A    N
ATOM      8  CZ2 TRP A 238      18.017  -6.741  22.886  1.00 61.03      A    C
ATOM      9  CZ3 TRP A 238      19.881  -5.291  23.378  1.00 58.41      A    C
ATOM     10  CH2 TRP A 238      19.086  -5.996  22.469  1.00 59.39      A    C
ATOM     11  C   TRP A 238      20.131  -5.621  29.673  1.00 57.85      A    C
ATOM     12  O   TRP A 238      20.705  -4.543  29.552  1.00 57.36      A    O
ATOM     13  N   TRP A 238      19.317  -7.833  28.701  1.00 59.99      A    N
ATOM     14  CA  TRP A 238      19.650  -6.392  28.422  1.00 59.05      A    C
ATOM     15  N   GLU A 239      19.843  -6.141  30.868  1.00 57.23      A    N
ATOM     16  CA  GLU A 239      20.267  -5.486  32.107  1.00 55.32      A    C
ATOM     17  CB  GLU A 239      19.454  -5.942  33.331  1.00 57.73      A    C
ATOM     18  CG  GLU A 239      18.262  -5.065  33.715  1.00 61.08      A    C
ATOM     19  CD  GLU A 239      17.034  -5.269  32.802  1.00 62.40      A    C
ATOM     20  OE1 GLU A 239      17.071  -4.801  31.637  1.00 63.20      A    O
ATOM     21  OE2 GLU A 239      16.029  -5.876  33.258  1.00 62.28      A    O
ATOM     22  C   GLU A 239      21.706  -5.866  32.336  1.00 52.68      A    C
ATOM     23  O   GLU A 239      22.117  -7.012  32.108  1.00 52.60      A    O
ATOM     24  N   VAL A 240      22.483  -4.882  32.739  1.00 49.99      A    N
ATOM     25  CA  VAL A 240      23.873  -5.121  33.029  1.00 46.23      A    C
ATOM     26  CB  VAL A 240      24.803  -4.703  31.884  1.00 45.56      A    C
ATOM     27  CG1 VAL A 240      24.482  -5.488  30.642  1.00 44.36      A    C
ATOM     28  CG2 VAL A 240      24.760  -3.213  31.669  1.00 44.48      A    C
ATOM     29  C   VAL A 240      24.256  -4.365  34.266  1.00 44.38      A    C
ATOM     30  O   VAL A 240      23.559  -3.464  34.713  1.00 42.88      A    O
ATOM     31  N   PRO A 241      25.334  -4.801  34.894  1.00 43.28      A    N
ATOM     32  CD  PRO A 241      25.932  -6.130  34.736  1.00 41.10      A    C
ATOM     33  CA  PRO A 241      25.817  -4.149  36.104  1.00 43.15      A    C
ATOM     34  CB  PRO A 241      26.860  -5.138  36.601  1.00 42.50      A    C
ATOM     35  CG  PRO A 241      26.307  -6.446  36.142  1.00 41.49      A    C
ATOM     36  C   PRO A 241      26.425  -2.742  35.835  1.00 43.53      A    C
ATOM     37  O   PRO A 241      27.033  -2.462  34.777  1.00 42.15      A    O
ATOM     38  N   ARG A 242      26.225  -1.846  36.792  1.00 44.04      A    N
ATOM     39  CA  ARG A 242      26.768  -0.491  36.685  1.00 45.13      A    C
ATOM     40  CB  ARG A 242      26.360   0.308  37.927  1.00 47.04      A    C
ATOM     41  CG  ARG A 242      26.986   1.702  38.061  1.00 49.23      A    C
ATOM     42  CD  ARG A 242      26.358   2.649  37.086  1.00 50.31      A    C
ATOM     43  NE  ARG A 242      24.904   2.652  37.160  1.00 52.13      A    N
ATOM     44  CZ  ARG A 242      24.214   3.095  38.202  1.00 52.88      A    C
ATOM     45  NH1 ARG A 242      24.863   3.560  39.265  1.00 54.71      A    N
ATOM     46  NH2 ARG A 242      22.886   3.109  38.169  1.00 51.38      A    N
ATOM     47  C   ARG A 242      28.306  -0.502  36.532  1.00 44.65      A    C
```

Figure 13

| | | | | | | | | | | | |
|---|---|---|---|---|---|---|---|---|---|---|---|
| ATOM | 48 | O | ARG | A | 242 | 28.871 | 0.351 | 35.853 | 1.00 | 44.58 | A O |
| ATOM | 49 | N | GLU | A | 243 | 28.945 | -1.529 | 37.096 | 1.00 | 44.79 | A N |
| ATOM | 50 | CA | GLU | A | 243 | 30.405 | -1.747 | 37.085 | 1.00 | 44.61 | A C |
| ATOM | 51 | CB | GLU | A | 243 | 30.735 | -3.084 | 37.799 | 1.00 | 49.07 | A C |
| ATOM | 52 | CG | GLU | A | 243 | 30.283 | -3.213 | 39.283 | 1.00 | 53.35 | A C |
| ATOM | 53 | CD | GLU | A | 243 | 28.869 | -2.642 | 39.569 | 1.00 | 53.57 | A C |
| ATOM | 54 | OE1 | GLU | A | 243 | 27.861 | -3.316 | 39.268 | 1.00 | 52.95 | A O |
| ATOM | 55 | OE2 | GLU | A | 243 | 28.782 | -1.511 | 40.099 | 1.00 | 52.40 | A O |
| ATOM | 56 | C | GLU | A | 243 | 30.968 | -1.841 | 35.667 | 1.00 | 42.55 | A C |
| ATOM | 57 | O | GLU | A | 243 | 32.042 | -1.331 | 35.374 | 1.00 | 41.18 | A O |
| ATOM | 58 | N | THR | A | 244 | 30.233 | -2.532 | 34.803 | 1.00 | 41.03 | A N |
| ATOM | 59 | CA | THR | A | 244 | 30.617 | -2.746 | 33.416 | 1.00 | 39.50 | A C |
| ATOM | 60 | CB | THR | A | 244 | 29.584 | -3.654 | 32.721 | 1.00 | 38.97 | A C |
| ATOM | 61 | OG1 | THR | A | 244 | 28.314 | -2.989 | 32.629 | 1.00 | 35.92 | A O |
| ATOM | 62 | CG2 | THR | A | 244 | 29.429 | -4.957 | 33.502 | 1.00 | 39.39 | A C |
| ATOM | 63 | C | THR | A | 244 | 30.667 | -1.475 | 32.611 | 1.00 | 39.29 | A C |
| ATOM | 64 | O | THR | A | 244 | 31.068 | -1.502 | -31.451 | 1.00 | 39.60 | A O |
| ATOM | 65 | N | LEU | A | 245 | 30.387 | -0.356 | 33.269 | 1.00 | 38.60 | A N |
| ATOM | 66 | CA | LEU | A | 245 | 30.280 | 0.908 | 32.592 | 1.00 | 38.59 | A C |
| ATOM | 67 | CB | LEU | A | 245 | 28.786 | 1.169 | 32.494 | 1.00 | 38.08 | A C |
| ATOM | 68 | CG | LEU | A | 245 | 28.167 | 1.836 | 31.283 | 1.00 | 38.49 | A C |
| ATOM | 69 | CD1 | LEU | A | 245 | 28.343 | 1.018 | 30.057 | 1.00 | 37.64 | A C |
| ATOM | 70 | CD2 | LEU | A | 245 | 26.666 | 2.027 | 31.597 | 1.00 | 39.42 | A C |
| ATOM | 71 | C | LEU | A | 245 | 31.013 | 2.134 | 33.180 | 1.00 | 39.42 | A C |
| ATOM | 72 | O | LEU | A | 245 | 30.805 | 2.540 | 34.335 | 1.00 | 39.23 | A O |
| ATOM | 73 | N | LYS | A | 246 | 31.844 | 2.755 | 32.353 | 1.00 | 39.13 | A N |
| ATOM | 74 | CA | LYS | A | 246 | 32.582 | 3.934 | 32.784 | 1.00 | 39.58 | A C |
| ATOM | 75 | CB | LYS | A | 246 | 34.111 | 3.697 | 32.713 | 1.00 | 43.48 | A C |
| ATOM | 76 | CG | LYS | A | 246 | 34.945 | 4.922 | 33.149 | 1.00 | 47.88 | A C |
| ATOM | 77 | CD | LYS | A | 246 | 36.468 | 4.680 | 33.206 | 1.00 | 52.58 | A C |
| ATOM | 78 | CE | LYS | A | 246 | 37.098 | 4.164 | 31.876 | 1.00 | 56.31 | A C |
| ATOM | 79 | NZ | LYS | A | 246 | 38.583 | 3.932 | 32.030 | 1.00 | 59.76 | A N |
| ATOM | 80 | C | LYS | A | 246 | 32.152 | 5.153 | 31.951 | 1.00 | 38.24 | A C |
| ATOM | 81 | O | LYS | A | 246 | 32.240 | 5.190 | 30.723 | 1.00 | 38.33 | A O |
| ATOM | 82 | N | LEU | A | 247 | 31.596 | 6.109 | 32.657 | 1.00 | 36.61 | A N |
| ATOM | 83 | CA | LEU | A | 247 | 31.095 | 7.308 | 32.074 | 1.00 | 35.50 | A C |
| ATOM | 84 | CB | LEU | A | 247 | 29.961 | 7.800 | 32.947 | 1.00 | 34.19 | A C |
| ATOM | 85 | CG | LEU | A | 247 | 28.563 | 7.489 | 32.414 | 1.00 | 32.52 | A C |
| ATOM | 86 | CD1 | LEU | A | 247 | 28.259 | 5.977 | 32.428 | 1.00 | 34.04 | A C |
| ATOM | 87 | CD2 | LEU | A | 247 | 27.569 | 8.256 | 33.224 | 1.00 | 30.26 | A C |
| ATOM | 88 | C | LEU | A | 247 | 32.187 | 8.346 | 32.032 | 1.00 | 36.42 | A C |
| ATOM | 89 | O | LEU | A | 247 | 32.516 | 8.931 | 33.077 | 1.00 | 37.21 | A O |
| ATOM | 90 | N | VAL | A | 248 | 32.661 | 8.680 | 30.824 | 1.00 | 36.12 | A N |
| ATOM | 91 | CA | VAL | A | 248 | 33.764 | 9.642 | 30.686 | 1.00 | 35.81 | A C |
| ATOM | 92 | CB | VAL | A | 248 | 34.771 | 9.230 | 29.590 | 1.00 | 34.58 | A C |
| ATOM | 93 | CG1 | VAL | A | 248 | 36.069 | 10.064 | 29.716 | 1.00 | 32.41 | A C |
| ATOM | 94 | CG2 | VAL | A | 248 | 35.080 | 7.794 | 29.688 | 1.00 | 35.35 | A C |
| ATOM | 95 | C | VAL | A | 248 | 33.477 | 11.135 | 30.490 | 1.00 | 35.85 | A C |
| ATOM | 96 | O | VAL | A | 248 | 33.897 | 11.988 | 31.278 | 1.00 | 35.78 | A O |
| ATOM | 97 | N | GLU | A | 249 | 32.770 | 11.460 | 29.428 | 1.00 | 35.94 | A N |
| ATOM | 98 | CA | GLU | A | 249 | 32.523 | 12.855 | 29.134 | 1.00 | 35.77 | A C |
| ATOM | 99 | CB | GLU | A | 249 | 33.411 | 13.215 | 27.962 | 1.00 | 38.12 | A C |
| ATOM | 100 | CG | GLU | A | 249 | 33.163 | 14.519 | 27.298 | 1.00 | 41.96 | A C |
| ATOM | 101 | CD | GLU | A | 249 | 33.774 | 14.547 | 25.884 | 1.00 | 45.56 | A C |
| ATOM | 102 | OE1 | GLU | A | 249 | 34.586 | 13.613 | 25.552 | 1.00 | 46.87 | A O |
| ATOM | 103 | OE2 | GLU | A | 249 | 33.440 | 15.501 | 25.113 | 1.00 | 47.37 | A O |
| ATOM | 104 | C | GLU | A | 249 | 31.063 | 13.154 | 28.835 | 1.00 | 34.67 | A C |
| ATOM | 105 | O | GLU | A | 249 | 30.385 | 12.400 | 28.131 | 1.00 | 34.64 | A O |
| ATOM | 106 | N | ARG | A | 250 | 30.573 | 14.233 | 29.433 | 1.00 | 33.96 | A N |
| ATOM | 107 | CA | ARG | A | 250 | 29.188 | 14.624 | 29.262 | 1.00 | 32.83 | A C |

Figure 13

| | | | | | | | | | | | |
|---|---|---|---|---|---|---|---|---|---|---|---|
| ATOM | 108 | CB  | ARG | A | 250 | 28.722 | 15.560 | 30.352 | 1.00 | 31.64 | A C |
| ATOM | 109 | CG  | ARG | A | 250 | 27.231 | 15.462 | 30.409 | 1.00 | 33.26 | A C |
| ATOM | 110 | CD  | ARG | A | 250 | 26.649 | 16.246 | 31.552 | 1.00 | 35.62 | A C |
| ATOM | 111 | NE  | ARG | A | 250 | 26.716 | 17.688 | 31.309 | 1.00 | 37.11 | A N |
| ATOM | 112 | CZ  | ARG | A | 250 | 26.489 | 18.619 | 32.229 | 1.00 | 37.53 | A C |
| ATOM | 113 | NH1 | ARG | A | 250 | 26.172 | 18.274 | 33.461 | 1.00 | 37.06 | A N |
| ATOM | 114 | NH2 | ARG | A | 250 | 26.715 | 19.884 | 31.941 | 1.00 | 37.57 | A N |
| ATOM | 115 | C   | ARG | A | 250 | 28.922 | 15.266 | 27.930 | 1.00 | 32.11 | A C |
| ATOM | 116 | O   | ARG | A | 250 | 29.479 | 16.304 | 27.643 | 1.00 | 32.77 | A O |
| ATOM | 117 | N   | LEU | A | 251 | 28.075 | 14.658 | 27.111 | 1.00 | 31.46 | A N |
| ATOM | 118 | CA  | LEU | A | 251 | 27.801 | 15.238 | 25.811 | 1.00 | 30.06 | A C |
| ATOM | 119 | CB  | LEU | A | 251 | 27.424 | 14.169 | 24.795 | 1.00 | 26.93 | A C |
| ATOM | 120 | CG  | LEU | A | 251 | 28.600 | 13.199 | 24.582 | 1.00 | 25.27 | A C |
| ATOM | 121 | CD1 | LEU | A | 251 | 28.219 | 12.085 | 23.640 | 1.00 | 24.97 | A C |
| ATOM | 122 | CD2 | LEU | A | 251 | 29.828 | 13.897 | 24.055 | 1.00 | 23.50 | A C |
| ATOM | 123 | C   | LEU | A | 251 | 26.749 | 16.320 | 25.910 | 1.00 | 30.40 | A C |
| ATOM | 124 | O   | LEU | A | 251 | 26.802 | 17.311 | 25.208 | 1.00 | 31.27 | A O |
| ATOM | 125 | N   | GLY | A | 252 | 25.810 | 16.155 | 26.816 | 1.00 | 30.42 | A N |
| ATOM | 126 | CA  | GLY | A | 252 | 24.771 | 17.167 | 26.973 | 1.00 | 29.76 | A C |
| ATOM | 127 | C   | GLY | A | 252 | 23.885 | 16.903 | 28.188 | 1.00 | 29.48 | A C |
| ATOM | 128 | O   | GLY | A | 252 | 23.768 | 15.786 | 28.726 | 1.00 | 28.56 | A O |
| ATOM | 129 | N   | ALA | A | 253 | 23.226 | 17.956 | 28.612 | 1.00 | 30.46 | A N |
| ATOM | 130 | CA  | ALA | A | 253 | 22.347 | 17.881 | 29.772 | 1.00 | 31.61 | A C |
| ATOM | 131 | CB  | ALA | A | 253 | 23.084 | 18.398 | 31.035 | 1.00 | 32.92 | A C |
| ATOM | 132 | C   | ALA | A | 253 | 21.083 | 18.699 | 29.533 | 1.00 | 31.04 | A C |
| ATOM | 133 | O   | ALA | A | 253 | 21.114 | 19.838 | 29.029 | 1.00 | 30.30 | A O |
| ATOM | 134 | N   | GLY | A | 254 | 19.974 | 18.098 | 29.933 | 1.00 | 32.31 | A N |
| ATOM | 135 | CA  | GLY | A | 254 | 18.682 | 18.730 | 29.776 | 1.00 | 32.58 | A C |
| ATOM | 136 | C   | GLY | A | 254 | 17.744 | 18.591 | 30.960 | 1.00 | 33.09 | A C |
| ATOM | 137 | O   | GLY | A | 254 | 18.120 | 18.100 | 32.019 | 1.00 | 32.83 | A O |
| ATOM | 138 | N   | GLN | A | 255 | 16.517 | 19.047 | 30.758 | 1.00 | 34.64 | A N |
| ATOM | 139 | CA  | GLN | A | 255 | 15.464 | 19.039 | 31.756 | 1.00 | 36.58 | A C |
| ATOM | 140 | CB  | GLN | A | 255 | 14.161 | 19.597 | 31.141 | 1.00 | 39.96 | A C |
| ATOM | 141 | CG  | GLN | A | 255 | 13.183 | 20.220 | 32.179 | 1.00 | 44.27 | A C |
| ATOM | 142 | CD  | GLN | A | 255 | 11.692 | 20.220 | 31.802 | 1.00 | 46.12 | A C |
| ATOM | 143 | OE1 | GLN | A | 255 | 10.815 | 20.326 | 32.689 | 1.00 | 45.56 | A O |
| ATOM | 144 | NE2 | GLN | A | 255 | 11.400 | 20.117 | 30.505 | 1.00 | 47.65 | A N |
| ATOM | 145 | C   | GLN | A | 255 | 15.187 | 17.684 | 32.336 | 1.00 | 36.38 | A C |
| ATOM | 146 | O   | GLN | A | 255 | 15.001 | 17.568 | 33.531 | 1.00 | 36.48 | A O |
| ATOM | 147 | N   | PHE | A | 256 | 15.217 | 16.659 | 31.486 | 1.00 | 36.19 | A N |
| ATOM | 148 | CA  | PHE | A | 256 | 14.932 | 15.268 | 31.885 | 1.00 | 35.34 | A C |
| ATOM | 149 | CB  | PHE | A | 256 | 14.141 | 14.538 | 30.786 | 1.00 | 35.25 | A C |
| ATOM | 150 | CG  | PHE | A | 256 | 12.725 | 14.993 | 30.644 | 1.00 | 35.46 | A C |
| ATOM | 151 | CD1 | PHE | A | 256 | 12.205 | 15.954 | 31.472 | 1.00 | 35.57 | A C |
| ATOM | 152 | CD2 | PHE | A | 256 | 11.903 | 14.422 | 29.679 | 1.00 | 36.71 | A C |
| ATOM | 153 | CE1 | PHE | A | 256 | 10.884 | 16.369 | 31.348 | 1.00 | 36.85 | A C |
| ATOM | 154 | CE2 | PHE | A | 256 | 10.568 | 14.820 | 29.534 | 1.00 | 37.74 | A C |
| ATOM | 155 | CZ  | PHE | A | 256 | 10.056 | 15.794 | 30.376 | 1.00 | 37.87 | A C |
| ATOM | 156 | C   | PHE | A | 256 | 16.093 | 14.360 | 32.255 | 1.00 | 34.90 | A C |
| ATOM | 157 | O   | PHE | A | 256 | 15.856 | 13.262 | 32.761 | 1.00 | 34.71 | A O |
| ATOM | 158 | N   | GLY | A | 257 | 17.327 | 14.758 | 31.925 | 1.00 | 35.07 | A N |
| ATOM | 159 | CA  | GLY | A | 257 | 18.466 | 13.906 | 32.223 | 1.00 | 33.45 | A C |
| ATOM | 160 | C   | GLY | A | 257 | 19.695 | 14.348 | 31.478 | 1.00 | 33.03 | A C |
| ATOM | 161 | O   | GLY | A | 257 | 19.772 | 15.510 | 31.131 | 1.00 | 33.19 | A O |
| ATOM | 162 | N   | GLU | A | 258 | 20.627 | 13.429 | 31.206 | 1.00 | 33.13 | A N |
| ATOM | 163 | CA  | GLU | A | 258 | 21.881 | 13.751 | 30.537 | 1.00 | 33.25 | A C |
| ATOM | 164 | CB  | GLU | A | 258 | 22.947 | 13.960 | 31.598 | 1.00 | 32.79 | A C |
| ATOM | 165 | CG  | GLU | A | 258 | 22.582 | 14.937 | 32.684 | 1.00 | 32.05 | A C |
| ATOM | 166 | CD  | GLU | A | 258 | 23.686 | 15.041 | 33.729 | 1.00 | 33.34 | A C |
| ATOM | 167 | OE1 | GLU | A | 258 | 24.225 | 13.983 | 34.118 | 1.00 | 31.94 | A O |

Figure 13

| | | | | | | | | | | |
|---|---|---|---|---|---|---|---|---|---|---|
| ATOM | 168 | OE2 | GLU | A | 258 | 24.038 | 16.178 | 34.141 | 1.00 32.85 | A | O |
| ATOM | 169 | C | GLU | A | 258 | 22.341 | 12.622 | 29.646 | 1.00 33.37 | A | C |
| ATOM | 170 | O | GLU | A | 258 | 21.962 | 11.483 | 29.866 | 1.00 34.94 | A | O |
| ATOM | 171 | N | VAL | A | 259 | 23.243 | 12.921 | 28.709 | 1.00 32.59 | A | N |
| ATOM | 172 | CA | VAL | A | 259 | 23.799 | 11.925 | 27.765 | 1.00 31.48 | A | C |
| ATOM | 173 | CB | VAL | A | 259 | 23.464 | 12.261 | 26.302 | 1.00 30.76 | A | C |
| ATOM | 174 | CG1 | VAL | A | 259 | 23.885 | 11.105 | 25.383 | 1.00 31.78 | A | C |
| ATOM | 175 | CG2 | VAL | A | 259 | 22.034 | 12.640 | 26.156 | 1.00 29.16 | A | C |
| ATOM | 176 | C | VAL | A | 259 | 25.318 | 12.062 | 27.867 | 1.00 31.27 | A | C |
| ATOM | 177 | O | VAL | A | 259 | 25.833 | 13.191 | 27.829 | 1.00 32.54 | A | O |
| ATOM | 178 | N | TRP | A | 260 | 26.025 | 10.941 | 28.018 | 1.00 29.94 | A | N |
| ATOM | 179 | CA | TRP | A | 260 | 27.483 | 10.922 | 28.163 | 1.00 28.31 | A | C |
| ATOM | 180 | CB | TRP | A | 260 | 27.857 | 10.416 | 29.558 | 1.00 27.07 | A | C |
| ATOM | 181 | CG | TRP | A | 260 | 27.601 | 11.309 | 30.696 | 1.00 27.00 | A | C |
| ATOM | 182 | CD2 | TRP | A | 260 | 28.581 | 11.915 | 31.538 | 1.00 28.61 | A | C |
| ATOM | 183 | CE2 | TRP | A | 260 | 27.905 | 12.668 | 32.510 | 1.00 28.72 | A | C |
| ATOM | 184 | CE3 | TRP | A | 260 | 29.992 | 11.895 | 31.574 | 1.00 30.07 | A | C |
| ATOM | 185 | CD1 | TRP | A | 260 | 26.389 | 11.706 | 31.176 | 1.00 26.19 | A | C |
| ATOM | 186 | NE1 | TRP | A | 260 | 26.558 | 12.531 | 32.254 | 1.00 27.05 | A | N |
| ATOM | 187 | CZ2 | TRP | A | 260 | 28.571 | 13.387 | 33.504 | 1.00 28.96 | A | C |
| ATOM | 188 | CZ3 | TRP | A | 260 | 30.654 | 12.616 | 32.571 | 1.00 29.29 | A | C |
| ATOM | 189 | CH2 | TRP | A | 260 | 29.947 | 13.342 | 33.515 | 1.00 29.51 | A | C |
| ATOM | 190 | C | TRP | A | 260 | 28.145 | 9.949 | 27.212 | 1.00 28.46 | A | C |
| ATOM | 191 | O | TRP | A | 260 | 27.525 | 8.999 | 26.721 | 1.00 28.43 | A | O |
| ATOM | 192 | N | MET | A | 261 | 29.420 | 10.200 | 26.938 | 1.00 28.87 | A | N |
| ATOM | 193 | CA | MET | A | 261 | 30.207 | 9.264 | 26.151 | 1.00 29.06 | A | C |
| ATOM | 194 | CB | MET | A | 261 | 31.165 | 9.971 | 25.192 | 1.00 27.28 | A | C |
| ATOM | 195 | CG | MET | A | 261 | 32.138 | 9.020 | 24.499 | 1.00 26.57 | A | C |
| ATOM | 196 | SD | MET | A | 261 | 33.609 | 8.449 | 25.536 | 1.00 26.44 | A | S |
| ATOM | 197 | CE | MET | A | 261 | 34.460 | 10.139 | 25.675 | 1.00 24.68 | A | C |
| ATOM | 198 | C | MET | A | 261 | 30.968 | 8.481 | 27.234 | 1.00 29.30 | A | C |
| ATOM | 199 | O | MET | A | 261 | 31.296 | 9.032 | 28.291 | 1.00 29.45 | A | O |
| ATOM | 200 | N | GLY | A | 262 | 31.212 | 7.201 | 27.006 | 1.00 29.38 | A | N |
| ATOM | 201 | CA | GLY | A | 262 | 31.920 | 6.441 | 28.004 | 1.00 30.10 | A | C |
| ATOM | 202 | C | GLY | A | 262 | 32.453 | 5.196 | 27.386 | 1.00 30.97 | A | C |
| ATOM | 203 | O | GLY | A | 262 | 32.757 | 5.200 | 26.198 | 1.00 31.80 | A | O |
| ATOM | 204 | N | TYR | A | 263 | 32.630 | 4.158 | 28.196 | 1.00 31.59 | A | N |
| ATOM | 205 | CA | TYR | A | 263 | 33.122 | 2.894 | 27.680 | 1.00 33.65 | A | C |
| ATOM | 206 | CB | TYR | A | 263 | 34.644 | 2.826 | 27.857 | 1.00 31.68 | A | C |
| ATOM | 207 | CG | TYR | A | 263 | 35.375 | 3.826 | 26.991 | 1.00 28.40 | A | C |
| ATOM | 208 | CD1 | TYR | A | 263 | 35.785 | 3.471 | 25.717 | 1.00 27.16 | A | C |
| ATOM | 209 | CE1 | TYR | A | 263 | 36.406 | 4.375 | 24.896 | 1.00 26.68 | A | C |
| ATOM | 210 | CD2 | TYR | A | 263 | 35.608 | 5.141 | 27.433 | 1.00 25.96 | A | C |
| ATOM | 211 | CE2 | TYR | A | 263 | 36.231 | 6.076 | 26.613 | 1.00 24.86 | A | C |
| ATOM | 212 | CZ | TYR | A | 263 | 36.638 | 5.676 | 25.329 | 1.00 26.92 | A | C |
| ATOM | 213 | OH | TYR | A | 263 | 37.317 | 6.508 | 24.445 | 1.00 27.06 | A | O |
| ATOM | 214 | C | TYR | A | 263 | 32.385 | 1.736 | 28.337 | 1.00 36.00 | A | C |
| ATOM | 215 | O | TYR | A | 263 | 31.969 | 1.852 | 29.493 | 1.00 36.93 | A | O |
| ATOM | 216 | N | TYR | A | 264 | 32.105 | 0.695 | 27.547 | 1.00 37.66 | A | N |
| ATOM | 217 | CA | TYR | A | 264 | 31.357 | -0.483 | 27.997 | 1.00 40.65 | A | C |
| ATOM | 218 | CB | TYR | A | 264 | 30.095 | -0.665 | 27.082 | 1.00 40.29 | A | C |
| ATOM | 219 | CG | TYR | A | 264 | 29.115 | -1.795 | 27.368 | 1.00 41.72 | A | C |
| ATOM | 220 | CD1 | TYR | A | 264 | 28.739 | -2.132 | 28.672 | 1.00 42.37 | A | C |
| ATOM | 221 | CE1 | TYR | A | 264 | 27.920 | -3.235 | 28.931 | 1.00 44.10 | A | C |
| ATOM | 222 | CD2 | TYR | A | 264 | 28.628 | -2.577 | 26.321 | 1.00 42.66 | A | C |
| ATOM | 223 | CE2 | TYR | A | 264 | 27.814 | -3.679 | 26.557 | 1.00 44.36 | A | C |
| ATOM | 224 | CZ | TYR | A | 264 | 27.468 | -4.027 | 27.862 | 1.00 44.95 | A | C |
| ATOM | 225 | OH | TYR | A | 264 | 26.774 | -5.219 | 28.074 | 1.00 44.13 | A | O |
| ATOM | 226 | C | TYR | A | 264 | 32.338 | -1.643 | 27.932 | 1.00 42.17 | A | C |
| ATOM | 227 | O | TYR | A | 264 | 32.904 | -1.923 | 26.878 | 1.00 43.38 | A | O |

Figure 13

| | | | | | | | | | | | |
|---|---|---|---|---|---|---|---|---|---|---|---|
| ATOM | 228 | N | ASN | A | 265 | 32.583 | -2.277 | 29.072 | 1.00 | 43.09 | A N |
| ATOM | 229 | CA | ASN | A | 265 | 33.523 | -3.395 | 29.124 | 1.00 | 44.36 | A C |
| ATOM | 230 | CB | ASN | A | 265 | 33.072 | -4.517 | 28.163 | 1.00 | 44.07 | A C |
| ATOM | 231 | CG | ASN | A | 265 | 31.665 | -5.075 | 28.509 | 1.00 | 44.10 | A C |
| ATOM | 232 | OD1 | ASN | A | 265 | 31.361 | -5.310 | 29.682 | 1.00 | 42.00 | A O |
| ATOM | 233 | ND2 | ASN | A | 265 | 30.821 | -5.296 | 27.484 | 1.00 | 43.59 | A N |
| ATOM | 234 | C | ASN | A | 265 | 34.922 | -2.844 | 28.772 | 1.00 | 45.49 | A C |
| ATOM | 235 | O | ASN | A | 265 | 35.703 | -3.439 | 28.013 | 1.00 | 45.25 | A O |
| ATOM | 236 | N | GLY | A | 266 | 35.161 | -1.631 | 29.266 | 1.00 | 47.13 | A N |
| ATOM | 237 | CA | GLY | A | 266 | 36.413 | -0.934 | 29.048 | 1.00 | 48.96 | A C |
| ATOM | 238 | C | GLY | A | 266 | 36.779 | -0.501 | 27.637 | 1.00 | 50.97 | A C |
| ATOM | 239 | O | GLY | A | 266 | 37.429 | 0.547 | 27.483 | 1.00 | 51.57 | A O |
| ATOM | 240 | N | HIS | A | 267 | 36.346 | -1.242 | 26.607 | 1.00 | 52.34 | A N |
| ATOM | 241 | CA | HIS | A | 267 | 36.729 | -0.908 | 25.221 | 1.00 | 53.41 | A C |
| ATOM | 242 | CB | HIS | A | 267 | 37.675 | -1.972 | 24.673 | 1.00 | 57.43 | A C |
| ATOM | 243 | CG | HIS | A | 267 | 39.029 | -1.940 | 25.314 | 1.00 | 62.41 | A C |
| ATOM | 244 | CD2 | HIS | A | 267 | 39.922 | -0.926 | 25.473 | 1.00 | 63.06 | A C |
| ATOM | 245 | ND1 | HIS | A | 267 | 39.596 | -3.046 | 25.917 | 1.00 | 64.77 | A N |
| ATOM | 246 | CE1 | HIS | A | 267 | 40.778 | -2.718 | 26.417 | 1.00 | 64.98 | A C |
| ATOM | 247 | NE2 | HIS | A | 267 | 40.996 | -1.438 | 26.160 | 1.00 | 64.01 | A N |
| ATOM | 248 | C | HIS | A | 267 | 35.709 | -0.523 | 24.145 | 1.00 | 51.67 | A C |
| ATOM | 249 | O | HIS | A | 267 | 36.102 | -0.024 | 23.089 | 1.00 | 51.68 | A O |
| ATOM | 250 | N | THR | A | 268 | 34.434 | -0.838 | 24.347 | 1.00 | 48.83 | A N |
| ATOM | 251 | CA | THR | A | 268 | 33.417 | -0.425 | 23.389 | 1.00 | 45.48 | A C |
| ATOM | 252 | CB | THR | A | 268 | 32.219 | -1.341 | 23.452 | 1.00 | 44.70 | A C |
| ATOM | 253 | OG1 | THR | A | 268 | 32.651 | -2.665 | 23.139 | 1.00 | 45.51 | A O |
| ATOM | 254 | CG2 | THR | A | 268 | 31.138 | -0.906 | 22.464 | 1.00 | 43.61 | A C |
| ATOM | 255 | C | THR | A | 268 | 32.981 | 0.994 | 23.748 | 1.00 | 43.42 | A C |
| ATOM | 256 | O | THR | A | 268 | 32.537 | 1.249 | 24.877 | 1.00 | 42.40 | A O |
| ATOM | 257 | N | LYS | A | 269 | 33.147 | 1.929 | 22.811 | 1.00 | 41.01 | A N |
| ATOM | 258 | CA | LYS | A | 269 | 32.756 | 3.315 | 23.056 | 1.00 | 38.59 | A C |
| ATOM | 259 | CB | LYS | A | 269 | 33.381 | 4.221 | 22.018 | 1.00 | 39.16 | A C |
| ATOM | 260 | CG | LYS | A | 269 | 33.446 | 5.662 | 22.416 | 1.00 | 39.77 | A C |
| ATOM | 261 | CD | LYS | A | 269 | 34.423 | 6.385 | 21.499 | 1.00 | 39.48 | A C |
| ATOM | 262 | CE | LYS | A | 269 | 34.897 | 7.678 | 22.123 | 1.00 | 39.87 | A C |
| ATOM | 263 | NZ | LYS | A | 269 | 35.662 | 8.475 | 21.114 | 1.00 | 41.19 | A N |
| ATOM | 264 | C | LYS | A | 269 | 31.225 | 3.393 | 22.963 | 1.00 | 36.52 | A C |
| ATOM | 265 | O | LYS | A | 269 | 30.658 | 2.889 | 21.995 | 1.00 | 35.16 | A O |
| ATOM | 266 | N | VAL | A | 270 | 30.590 | 4.058 | 23.923 | 1.00 | 34.73 | A N |
| ATOM | 267 | CA | VAL | A | 270 | 29.122 | 4.179 | 23.971 | 1.00 | 32.08 | A C |
| ATOM | 268 | CB | VAL | A | 270 | 28.540 | 3.282 | 25.110 | 1.00 | 29.40 | A C |
| ATOM | 269 | CG1 | VAL | A | 270 | 28.593 | 1.850 | 24.756 | 1.00 | 26.01 | A C |
| ATOM | 270 | CG2 | VAL | A | 270 | 29.292 | 3.595 | 26.428 | 1.00 | 27.70 | A C |
| ATOM | 271 | C | VAL | A | 270 | 28.595 | 5.593 | 24.306 | 1.00 | 32.46 | A C |
| ATOM | 272 | O | VAL | A | 270 | 29.355 | 6.540 | 24.601 | 1.00 | 32.33 | A O |
| ATOM | 273 | N | ALA | A | 271 | 27.264 | 5.706 | 24.236 | 1.00 | 32.13 | A N |
| ATOM | 274 | CA | ALA | A | 271 | 26.515 | 6.912 | 24.606 | 1.00 | 30.91 | A C |
| ATOM | 275 | CB | ALA | A | 271 | 25.694 | 7.414 | 23.427 | 1.00 | 31.24 | A C |
| ATOM | 276 | C | ALA | A | 271 | 25.622 | 6.292 | 25.669 | 1.00 | 30.00 | A C |
| ATOM | 277 | O | ALA | A | 271 | 25.057 | 5.217 | 25.457 | 1.00 | 29.45 | A O |
| ATOM | 278 | N | VAL | A | 272 | 25.514 | 6.962 | 26.805 | 1.00 | 29.05 | A N |
| ATOM | 279 | CA | VAL | A | 272 | 24.750 | 6.468 | 27.930 | 1.00 | 28.61 | A C |
| ATOM | 280 | CB | VAL | A | 272 | 25.660 | 6.283 | 29.176 | 1.00 | 28.49 | A C |
| ATOM | 281 | CG1 | VAL | A | 272 | 24.858 | 5.845 | 30.422 | 1.00 | 27.67 | A C |
| ATOM | 282 | CG2 | VAL | A | 272 | 26.815 | 5.355 | 28.855 | 1.00 | 27.24 | A C |
| ATOM | 283 | C | VAL | A | 272 | 23.847 | 7.581 | 28.298 | 1.00 | 28.69 | A C |
| ATOM | 284 | O | VAL | A | 272 | 24.357 | 8.623 | 28.681 | 1.00 | 29.52 | A O |
| ATOM | 285 | N | LYS | A | 273 | 22.526 | 7.396 | 28.220 | 1.00 | 28.95 | A N |
| ATOM | 286 | CA | LYS | A | 273 | 21.599 | 8.486 | 28.602 | 1.00 | 28.54 | A C |
| ATOM | 287 | CB | LYS | A | 273 | 20.542 | 8.643 | 27.508 | 1.00 | 27.84 | A C |

Figure 13

| | | | | | | | | | | | |
|---|---|---|---|---|---|---|---|---|---|---|---|
| ATOM | 288 | CG | LYS | A | 273 | 19.317 | 9.488 | 27.833 | 1.00 | 26.39 | A C |
| ATOM | 289 | CD | LYS | A | 273 | 18.310 | 9.338 | 26.706 | 1.00 | 26.00 | A C |
| ATOM | 290 | CE | LYS | A | 273 | 18.695 | 10.254 | 25.502 | 1.00 | 27.56 | A C |
| ATOM | 291 | NZ | LYS | A | 273 | 17.553 | 10.491 | 24.498 | 1.00 | 25.70 | A N |
| ATOM | 292 | C | LYS | A | 273 | 21.006 | 8.223 | 29.991 | 1.00 | 29.07 | A C |
| ATOM | 293 | O | LYS | A | 273 | 20.375 | 7.197 | 30.231 | 1.00 | 28.77 | A O |
| ATOM | 294 | N | SER | A | 274 | 21.169 | 9.163 | 30.897 | 1.00 | 30.33 | A N |
| ATOM | 295 | CA | SER | A | 274 | 20.668 | 8.933 | 32.236 | 1.00 | 32.46 | A C |
| ATOM | 296 | CB | SER | A | 274 | 21.769 | 9.181 | 33.246 | 1.00 | 32.30 | A C |
| ATOM | 297 | OG | SER | A | 274 | 22.175 | 10.534 | 33.189 | 1.00 | 35.15 | A O |
| ATOM | 298 | C | SER | A | 274 | 19.445 | 9.776 | 32.588 | 1.00 | 33.68 | A C |
| ATOM | 299 | O | SER | A | 274 | 19.328 | 10.910 | 32.158 | 1.00 | 33.60 | A O |
| ATOM | 300 | N | LEU | A | 275 | 18.557 | 9.212 | 33.405 | 1.00 | 36.15 | A N |
| ATOM | 301 | CA | LEU | A | 275 | 17.322 | 9.883 | 33.812 | 1.00 | 37.86 | A C |
| ATOM | 302 | CB | LEU | A | 275 | 16.181 | 8.857 | 33.978 | 1.00 | 36.42 | A C |
| ATOM | 303 | CG | LEU | A | 275 | 14.872 | 9.344 | 34.626 | 1.00 | 37.62 | A C |
| ATOM | 304 | CD1 | LEU | A | 275 | 14.071 | 10.295 | 33.684 | 1.00 | 37.63 | A C |
| ATOM | 305 | CD2 | LEU | A | 275 | 14.029 | 8.154 | 35.024 | 1.00 | 37.33 | A C |
| ATOM | 306 | C | LEU | A | 275 | 17.448 | 10.723 | 35.094 | 1.00 | 39.41 | A C |
| ATOM | 307 | O | LEU | A | 275 | 17.878 | 10.228 | 36.139 | 1.00 | 39.89 | A O |
| ATOM | 308 | N | LYS | A | 276 | 17.047 | 11.992 | 35.014 | 1.00 | 40.78 | A N |
| ATOM | 309 | CA | LYS | A | 276 | 17.050 | 12.875 | 36.169 | 1.00 | 43.10 | A C |
| ATOM | 310 | CB | LYS | A | 276 | 16.820 | 14.325 | 35.716 | 1.00 | 42.88 | A C |
| ATOM | 311 | CG | LYS | A | 276 | 16.623 | 15.370 | 36.839 | 1.00 | 44.77 | A C |
| ATOM | 312 | CD | LYS | A | 276 | 16.527 | 16.821 | 36.306 | 1.00 | 47.66 | A C |
| ATOM | 313 | CE | LYS | A | 276 | 17.768 | 17.170 | 35.443 | 1.00 | 51.35 | A C |
| ATOM | 314 | NZ | LYS | A | 276 | 17.789 | 18.573 | 34.842 | 1.00 | 53.53 | A N |
| ATOM | 315 | C | LYS | A | 276 | 15.831 | 12.378 | 36.959 | 1.00 | 44.90 | A C |
| ATOM | 316 | O | LYS | A | 276 | 14.710 | 12.423 | 36.460 | 1.00 | 45.79 | A O |
| ATOM | 317 | N | GLN | A | 277 | 16.066 | 11.828 | 38.148 | 1.00 | 45.98 | A N |
| ATOM | 318 | CA | GLN | A | 277 | 15.001 | 11.319 | 39.035 | 1.00 | 47.08 | A C |
| ATOM | 319 | CB | GLN | A | 277 | 15.582 | 10.946 | 40.398 | 1.00 | 51.07 | A C |
| ATOM | 320 | CG | GLN | A | 277 | 14.601 | 10.389 | 41.440 | 1.00 | 55.83 | A C |
| ATOM | 321 | CD | GLN | A | 277 | 15.322 | 10.119 | 42.804 | 1.00 | 59.71 | A C |
| ATOM | 322 | OE1 | GLN | A | 277 | 16.436 | 10.655 | 43.027 | 1.00 | 61.83 | A O |
| ATOM | 323 | NE2 | GLN | A | 277 | 14.693 | 9.364 | 43.708 | 1.00 | 60.00 | A N |
| ATOM | 324 | C | GLN | A | 277 | 13.862 | 12.329 | 39.234 | 1.00 | 46.85 | A C |
| ATOM | 325 | O | GLN | A | 277 | 14.109 | 13.506 | 39.527 | 1.00 | 45.58 | A O |
| ATOM | 326 | N | GLY | A | 278 | 12.629 | 11.868 | 38.988 | 1.00 | 46.19 | A N |
| ATOM | 327 | CA | GLY | A | 278 | 11.466 | 12.715 | 39.106 | 1.00 | 45.12 | A C |
| ATOM | 328 | C | GLY | A | 278 | 10.962 | 13.246 | 37.770 | 1.00 | 45.04 | A C |
| ATOM | 329 | O | GLY | A | 278 | 9.816 | 13.722 | 37.719 | 1.00 | 45.91 | A O |
| ATOM | 330 | N | SER | A | 279 | 11.783 | 13.238 | 36.713 | 1.00 | 43.80 | A N |
| ATOM | 331 | CA | SER | A | 279 | 11.359 | 13.747 | 35.394 | 1.00 | 43.51 | A C |
| ATOM | 332 | CB | SER | A | 279 | 12.526 | 13.714 | 34.403 | 1.00 | 44.59 | A C |
| ATOM | 333 | OG | SER | A | 279 | 13.585 | 14.549 | 34.827 | 1.00 | 45.85 | A O |
| ATOM | 334 | C | SER | A | 279 | 10.180 | 12.924 | 34.831 | 1.00 | 42.32 | A C |
| ATOM | 335 | O | SER | A | 279 | 9.305 | 13.421 | 34.117 | 1.00 | 40.81 | A O |
| ATOM | 336 | N | MET | A | 280 | 10.219 | 11.642 | 35.158 | 1.00 | 41.14 | A N |
| ATOM | 337 | CA | MET | A | 280 | 9.230 | 10.658 | 34.771 | 1.00 | 40.89 | A C |
| ATOM | 338 | CB | MET | A | 280 | 9.232 | 10.412 | 33.250 | 1.00 | 38.88 | A C |
| ATOM | 339 | CG | MET | A | 280 | 10.495 | 9.781 | 32.716 | 1.00 | 38.71 | A C |
| ATOM | 340 | SD | MET | A | 280 | 10.557 | 9.908 | 30.938 | 1.00 | 36.14 | A S |
| ATOM | 341 | CE | MET | A | 280 | 9.993 | 8.473 | 30.519 | 1.00 | 39.80 | A C |
| ATOM | 342 | C | MET | A | 280 | 9.609 | 9.402 | 35.512 | 1.00 | 41.35 | A C |
| ATOM | 343 | O | MET | A | 280 | 10.721 | 9.258 | 36.017 | 1.00 | 41.97 | A O |
| ATOM | 344 | N | SER | A | 281 | 8.698 | 8.457 | 35.553 | 1.00 | 41.80 | A N |
| ATOM | 345 | CA | SER | A | 281 | 9.000 | 7.245 | 36.287 | 1.00 | 42.17 | A C |
| ATOM | 346 | CB | SER | A | 281 | 7.745 | 6.420 | 36.570 | 1.00 | 41.35 | A C |
| ATOM | 347 | OG | SER | A | 281 | 7.373 | 5.676 | 35.423 | 1.00 | 38.37 | A O |

Figure 13

| | | | | | | | | | | | | |
|---|---|---|---|---|---|---|---|---|---|---|---|---|
| ATOM | 348 | C | SER | A | 281 | 10.035 | 6.377 | 35.566 | 1.00 | 43.35 | A | C |
| ATOM | 349 | O | SER | A | 281 | 10.212 | 6.445 | 34.352 | 1.00 | 42.54 | A | O |
| ATOM | 350 | N | PRO | A | 282 | 10.811 | 5.611 | 36.364 | 1.00 | 44.10 | A | N |
| ATOM | 351 | CD | PRO | A | 282 | 10.993 | 5.903 | 37.799 | 1.00 | 45.04 | A | C |
| ATOM | 352 | CA | PRO | A | 282 | 11.862 | 4.697 | 35.904 | 1.00 | 44.08 | A | C |
| ATOM | 353 | CB | PRO | A | 282 | 12.238 | 3.971 | 37.171 | 1.00 | 43.66 | A | C |
| ATOM | 354 | CG | PRO | A | 282 | 12.263 | 5.068 | 38.161 | 1.00 | 44.70 | A | C |
| ATOM | 355 | C | PRO | A | 282 | 11.337 | 3.724 | 34.886 | 1.00 | 45.33 | A | C |
| ATOM | 356 | O | PRO | A | 282 | 11.796 | 3.686 | 33.787 | 1.00 | 44.47 | A | O |
| ATOM | 357 | N | ASP | A | 283 | 10.225 | 3.048 | 35.206 | 1.00 | 48.43 | A | N |
| ATOM | 358 | CA | ASP | A | 283 | 9.625 | 2.113 | 34.236 | 1.00 | 51.69 | A | C |
| ATOM | 359 | CB | ASP | A | 283 | 8.523 | 1.242 | 34.903 | 1.00 | 53.18 | A | C |
| ATOM | 360 | CG | ASP | A | 283 | 9.061 | 0.283 | 36.020 | 1.00 | 57.00 | A | C |
| ATOM | 361 | OD1 | ASP | A | 283 | 10.320 | 0.072 | 36.148 | 1.00 | 58.62 | A | O |
| ATOM | 362 | OD2 | ASP | A | 283 | 8.230 | -0.311 | 36.761 | 1.00 | 58.82 | A | O |
| ATOM | 363 | C | ASP | A | 283 | 9.124 | 2.802 | 32.943 | 1.00 | 51.65 | A | C |
| ATOM | 364 | O | ASP | A | 283 | 8.847 | 2.128 | 31.952 | 1.00 | 51.64 | A | O |
| ATOM | 365 | N | ALA | A | 284 | 8.920 | 4.114 | 32.962 | 1.00 | 51.84 | A | N |
| ATOM | 366 | CA | ALA | A | 284 | 8.458 | 4.896 | 31.825 | 1.00 | 51.86 | A | C |
| ATOM | 367 | CB | ALA | A | 284 | 7.804 | 6.215 | 32.285 | 1.00 | 51.20 | A | C |
| ATOM | 368 | C | ALA | A | 284 | 9.648 | 5.207 | 30.911 | 1.00 | 52.03 | A | C |
| ATOM | 369 | O | ALA | A | 284 | 9.499 | 5.306 | 29.687 | 1.00 | 51.94 | A | O |
| ATOM | 370 | N | PHE | A | 285 | 10.801 | 5.461 | 31.541 | 1.00 | 51.42 | A | N |
| ATOM | 371 | CA | PHE | A | 285 | 12.047 | 5.751 | 30.851 | 1.00 | 50.22 | A | C |
| ATOM | 372 | CB | PHE | A | 285 | 13.053 | 6.375 | 31.843 | 1.00 | 47.82 | A | C |
| ATOM | 373 | CG | PHE | A | 285 | 14.409 | 6.652 | 31.261 | 1.00 | 44.18 | A | C |
| ATOM | 374 | CD1 | PHE | A | 285 | 14.618 | 7.763 | 30.472 | 1.00 | 43.56 | A | C |
| ATOM | 375 | CD2 | PHE | A | 285 | 15.494 | 5.862 | 31.578 | 1.00 | 42.76 | A | C |
| ATOM | 376 | CE1 | PHE | A | 285 | 15.914 | 8.097 | 30.019 | 1.00 | 42.84 | A | C |
| ATOM | 377 | CE2 | PHE | A | 285 | 16.785 | 6.185 | 31.132 | 1.00 | 41.82 | A | C |
| ATOM | 378 | CZ | PHE | A | 285 | 16.990 | 7.301 | 30.344 | 1.00 | 41.76 | A | C |
| ATOM | 379 | C | PHE | A | 285 | 12.586 | 4.453 | 30.239 | 1.00 | 50.24 | A | C |
| ATOM | 380 | O | PHE | A | 285 | 12.957 | 4.405 | 29.062 | 1.00 | 49.99 | A | O |
| ATOM | 381 | N | LEU | A | 286 | 12.697 | 3.419 | 31.064 | 1.00 | 50.29 | A | N |
| ATOM | 382 | CA | LEU | A | 286 | 13.213 | 2.145 | 30.611 | 1.00 | 50.74 | A | C |
| ATOM | 383 | CB | LEU | A | 286 | 13.305 | 1.153 | 31.761 | 1.00 | 49.70 | A | C |
| ATOM | 384 | CG | LEU | A | 286 | 14.469 | 1.543 | 32.669 | 1.00 | 49.98 | A | C |
| ATOM | 385 | CD1 | LEU | A | 286 | 14.309 | 0.901 | 34.048 | 1.00 | 50.75 | A | C |
| ATOM | 386 | CD2 | LEU | A | 286 | 15.785 | 1.168 | 31.997 | 1.00 | 48.15 | A | C |
| ATOM | 387 | C | LEU | A | 286 | 12.245 | 1.684 | 29.550 | 1.00 | 51.78 | A | C |
| ATOM | 388 | O | LEU | A | 286 | 12.634 | 1.063 | 28.557 | 1.00 | 51.33 | A | O |
| ATOM | 389 | N | ALA | A | 287 | 10.974 | 2.051 | 29.735 | 1.00 | 53.98 | A | N |
| ATOM | 390 | CA | ALA | A | 287 | 9.911 | 1.679 | 28.767 | 1.00 | 55.29 | A | C |
| ATOM | 391 | CB | ALA | A | 287 | 8.546 | 2.201 | 29.208 | 1.00 | 53.64 | A | C |
| ATOM | 392 | C | ALA | A | 287 | 10.267 | 2.216 | 27.356 | 1.00 | 55.72 | A | C |
| ATOM | 393 | O | ALA | A | 287 | 10.032 | 1.568 | 26.312 | 1.00 | 57.03 | A | O |
| ATOM | 394 | N | GLU | A | 288 | 10.886 | 3.374 | 27.341 | 1.00 | 55.20 | A | N |
| ATOM | 395 | CA | GLU | A | 288 | 11.296 | 3.957 | 26.077 | 1.00 | 56.42 | A | C |
| ATOM | 396 | CB | GLU | A | 288 | 11.698 | 5.464 | 26.262 | 1.00 | 56.93 | A | C |
| ATOM | 397 | CG | GLU | A | 288 | 10.599 | 6.365 | 26.950 | 1.00 | 57.26 | A | C |
| ATOM | 398 | CD | GLU | A | 288 | 10.809 | 7.913 | 26.812 | 1.00 | 57.06 | A | C |
| ATOM | 399 | OE1 | GLU | A | 288 | 11.952 | 8.406 | 27.046 | 1.00 | 56.89 | A | O |
| ATOM | 400 | OE2 | GLU | A | 288 | 9.822 | 8.620 | 26.467 | 1.00 | 52.95 | A | O |
| ATOM | 401 | C | GLU | A | 288 | 12.427 | 3.096 | 25.377 | 1.00 | 56.32 | A | C |
| ATOM | 402 | O | GLU | A | 288 | 12.502 | 3.014 | 24.132 | 1.00 | 55.66 | A | O |
| ATOM | 403 | N | ALA | A | 289 | 13.209 | 2.350 | 26.169 | 1.00 | 55.99 | A | N |
| ATOM | 404 | CA | ALA | A | 289 | 14.307 | 1.507 | 25.622 | 1.00 | 54.96 | A | C |
| ATOM | 405 | CB | ALA | A | 289 | 15.367 | 1.222 | 26.681 | 1.00 | 53.69 | A | C |
| ATOM | 406 | C | ALA | A | 289 | 13.847 | 0.195 | 25.010 | 1.00 | 54.65 | A | C |
| ATOM | 407 | O | ALA | A | 289 | 14.533 | -0.391 | 24.169 | 1.00 | 54.54 | A | O |

Figure 13

| | | | | | | | | | | | |
|---|---|---|---|---|---|---|---|---|---|---|---|
| ATOM | 408 | N | ASN | A | 290 | 12.690 | -0.271 | 25.459 | 1.00 | 54.46 | A | N |
| ATOM | 409 | CA | ASN | A | 290 | 12.122 | -1.519 | 24.960 | 1.00 | 54.92 | A | C |
| ATOM | 410 | CB | ASN | A | 290 | 10.860 | -1.888 | 25.767 | 1.00 | 55.71 | A | C |
| ATOM | 411 | CG | ASN | A | 290 | 11.157 | -2.203 | 27.236 | 1.00 | 55.19 | A | C |
| ATOM | 412 | OD1 | ASN | A | 290 | 10.360 | -1.887 | 28.124 | 1.00 | 54.53 | A | O |
| ATOM | 413 | ND2 | ASN | A | 290 | 12.292 | -2.856 | 27.489 | 1.00 | 54.82 | A | N |
| ATOM | 414 | C | ASN | A | 290 | 11.836 | -1.540 | 23.429 | 1.00 | 54.74 | A | C |
| ATOM | 415 | O | ASN | A | 290 | 11.925 | -2.588 | 22.804 | 1.00 | 54.48 | A | O |
| ATOM | 416 | N | LEU | A | 291 | 11.567 | -0.370 | 22.834 | 1.00 | 55.08 | A | N |
| ATOM | 417 | CA | LEU | A | 291 | 11.295 | -0.243 | 21.389 | 1.00 | 54.54 | A | C |
| ATOM | 418 | CB | LEU | A | 291 | 10.807 | 1.155 | 21.062 | 1.00 | 54.68 | A | C |
| ATOM | 419 | CG | LEU | A | 291 | 9.554 | 1.533 | 21.839 | 1.00 | 55.67 | A | C |
| ATOM | 420 | CD1 | LEU | A | 291 | 9.312 | 3.037 | 21.796 | 1.00 | 56.36 | A | C |
| ATOM | 421 | CD2 | LEU | A | 291 | 8.370 | 0.703 | 21.332 | 1.00 | 55.37 | A | C |
| ATOM | 422 | C | LEU | A | 291 | 12.530 | -0.493 | 20.564 | 1.00 | 54.29 | A | C |
| ATOM | 423 | O | LEU | A | 291 | 12.456 | -1.030 | 19.466 | 1.00 | 53.50 | A | O |
| ATOM | 424 | N | MET | A | 292 | 13.638 | 0.053 | 21.055 | 1.00 | 54.42 | A | N |
| ATOM | 425 | CA | MET | A | 292 | 14.939 | -0.103 | 20.426 | 1.00 | 54.09 | A | C |
| ATOM | 426 | CB | MET | A | 292 | 15.955 | 0.692 | 21.233 | 1.00 | 53.82 | A | C |
| ATOM | 427 | CG | MET | A | 292 | 16.956 | 1.481 | 20.432 | 1.00 | 53.05 | A | C |
| ATOM | 428 | SD | MET | A | 292 | 17.725 | 2.682 | 21.530 | 1.00 | 49.85 | A | S |
| ATOM | 429 | CE | MET | A | 292 | 17.138 | 4.160 | 20.718 | 1.00 | 53.66 | A | C |
| ATOM | 430 | C | MET | A | 292 | 15.280 | -1.607 | 20.424 | 1.00 | 54.16 | A | C |
| ATOM | 431 | O | MET | A | 292 | 15.911 | -2.096 | 19.491 | 1.00 | 53.85 | A | O |
| ATOM | 432 | N | LYS | A | 293 | 14.828 | -2.348 | 21.441 | 1.00 | 54.34 | A | N |
| ATOM | 433 | CA | LYS | A | 293 | 15.080 | -3.806 | 21.478 | 1.00 | 54.44 | A | C |
| ATOM | 434 | CB | LYS | A | 293 | 14.507 | -4.476 | 22.748 | 1.00 | 54.18 | A | C |
| ATOM | 435 | CG | LYS | A | 293 | 15.113 | -4.000 | 24.052 | 1.00 | 54.44 | A | C |
| ATOM | 436 | CD | LYS | A | 293 | 14.586 | -4.742 | 25.252 | 1.00 | 53.59 | A | C |
| ATOM | 437 | CE | LYS | A | 293 | 15.121 | -4.106 | 26.523 | 1.00 | 53.74 | A | C |
| ATOM | 438 | NZ | LYS | A | 293 | 14.595 | -4.734 | 27.742 | 1.00 | 53.93 | A | N |
| ATOM | 439 | C | LYS | A | 293 | 14.357 | -4.418 | 20.292 | 1.00 | 54.37 | A | C |
| ATOM | 440 | O | LYS | A | 293 | 14.953 | -5.117 | 19.475 | 1.00 | 55.26 | A | O |
| ATOM | 441 | N | GLN | A | 294 | 13.088 | -4.052 | 20.163 | 1.00 | 53.98 | A | N |
| ATOM | 442 | CA | GLN | A | 294 | 12.209 | -4.566 | 19.126 | 1.00 | 53.16 | A | C |
| ATOM | 443 | CB | GLN | A | 294 | 10.798 | -3.957 | 19.288 | 1.00 | 56.45 | A | C |
| ATOM | 444 | CG | GLN | A | 294 | 10.130 | -4.195 | 20.667 | 1.00 | 59.95 | A | C |
| ATOM | 445 | CD | GLN | A | 294 | 10.247 | -5.648 | 21.138 | 1.00 | 62.75 | A | C |
| ATOM | 446 | OE1 | GLN | A | 294 | 11.052 | -5.964 | 22.024 | 1.00 | 64.54 | A | O |
| ATOM | 447 | NE2 | GLN | A | 294 | 9.477 | -6.540 | 20.520 | 1.00 | 62.25 | A | N |
| ATOM | 448 | C | GLN | A | 294 | 12.700 | -4.352 | 17.706 | 1.00 | 51.14 | A | C |
| ATOM | 449 | O | GLN | A | 294 | 12.817 | -5.310 | 16.928 | 1.00 | 50.54 | A | O |
| ATOM | 450 | N | LEU | A | 295 | 13.002 | -3.091 | 17.387 | 1.00 | 48.74 | A | N |
| ATOM | 451 | CA | LEU | A | 295 | 13.438 | -2.694 | 16.054 | 1.00 | 45.85 | A | C |
| ATOM | 452 | CB | LEU | A | 295 | 12.754 | -1.414 | 15.637 | 1.00 | 45.40 | A | C |
| ATOM | 453 | CG | LEU | A | 295 | 11.277 | -1.441 | 15.285 | 1.00 | 44.05 | A | C |
| ATOM | 454 | CD1 | LEU | A | 295 | 10.912 | -0.083 | 14.668 | 1.00 | 43.90 | A | C |
| ATOM | 455 | CD2 | LEU | A | 295 | 11.026 | -2.549 | 14.284 | 1.00 | 44.28 | A | C |
| ATOM | 456 | C | LEU | A | 295 | 14.916 | -2.480 | 15.885 | 1.00 | 43.60 | A | C |
| ATOM | 457 | O | LEU | A | 295 | 15.446 | -1.497 | 16.374 | 1.00 | 43.91 | A | O |
| ATOM | 458 | N | GLN | A | 296 | 15.568 | -3.352 | 15.122 | 1.00 | 42.04 | A | N |
| ATOM | 459 | CA | GLN | A | 296 | 17.012 | -3.239 | 14.848 | 1.00 | 40.82 | A | C |
| ATOM | 460 | CB | GLN | A | 296 | 17.787 | -4.390 | 15.498 | 1.00 | 42.46 | A | C |
| ATOM | 461 | CG | GLN | A | 296 | 17.571 | -4.551 | 16.983 | 1.00 | 45.60 | A | C |
| ATOM | 462 | CD | GLN | A | 296 | 17.895 | -5.966 | 17.408 | 1.00 | 49.45 | A | C |
| ATOM | 463 | OE1 | GLN | A | 296 | 18.076 | -6.852 | 16.534 | 1.00 | 52.58 | A | O |
| ATOM | 464 | NE2 | GLN | A | 296 | 18.017 | -6.210 | 18.703 | 1.00 | 49.50 | A | N |
| ATOM | 465 | C | GLN | A | 296 | 17.246 | -3.181 | 13.359 | 1.00 | 38.75 | A | C |
| ATOM | 466 | O | GLN | A | 296 | 16.773 | -4.049 | 12.641 | 1.00 | 38.11 | A | O |
| ATOM | 467 | N | HIS | A | 297 | 18.104 | -2.256 | 12.941 | 1.00 | 37.11 | A | N |

Figure 13

| | | | | | | | | | | |
|---|---|---|---|---|---|---|---|---|---|---|
| ATOM | 468 | CA | HIS | A | 297 | 18.403 | -1.996 | 11.545 | 1.00 35.04 | A | C |
| ATOM | 469 | CB | HIS | A | 297 | 17.219 | -1.267 | 10.941 | 1.00 33.32 | A | C |
| ATOM | 470 | CG | HIS | A | 297 | 17.235 | -1.206 | 9.419 | 1.00 31.02 | A | C |
| ATOM | 471 | CD2 | HIS | A | 297 | 16.665 | -2.006 | 8.476 | 1.00 27.85 | A | C |
| ATOM | 472 | ND1 | HIS | A | 297 | 17.854 | -0.195 | 8.733 | 1.00 30.85 | A | N |
| ATOM | 473 | CE1 | HIS | A | 297 | 17.681 | -0.370 | 7.420 | 1.00 27.49 | A | C |
| ATOM | 474 | NE2 | HIS | A | 297 | 16.962 | -1.470 | 7.257 | 1.00 26.63 | A | N |
| ATOM | 475 | C | HIS | A | 297 | 19.638 | -1.091 | 11.539 | 1.00 34.94 | A | C |
| ATOM | 476 | O | HIS | A | 297 | 19.842 | -0.351 | 12.496 | 1.00 34.31 | A | O |
| ATOM | 477 | N | GLN | A | 298 | 20.463 | -1.157 | 10.484 | 1.00 35.91 | A | N |
| ATOM | 478 | CA | GLN | A | 298 | 21.678 | -0.330 | 10.367 | 1.00 37.01 | A | C |
| ATOM | 479 | CB | GLN | A | 298 | 22.438 | -0.655 | 9.077 | 1.00 40.01 | A | C |
| ATOM | 480 | CG | GLN | A | 298 | 23.351 | -1.888 | 9.193 | 1.00 46.53 | A | C |
| ATOM | 481 | CD | GLN | A | 298 | 24.322 | -1.844 | 10.389 | 1.00 48.63 | A | C |
| ATOM | 482 | OE1 | GLN | A | 298 | 24.434 | -2.830 | 11.132 | 1.00 48.58 | A | O |
| ATOM | 483 | NE2 | GLN | A | 298 | 25.011 | -0.698 | 10.583 | 1.00 48.90 | A | N |
| ATOM | 484 | C | GLN | A | 298 | 21.373 | 1.141 | 10.380 | 1.00 36.35 | A | C |
| ATOM | 485 | O | GLN | A | 298 | 22.208 | 1.975 | 10.725 | 1.00 37.26 | A | O |
| ATOM | 486 | N | ARG | A | 299 | 20.179 | 1.472 | 9.947 | 1.00 35.08 | A | N |
| ATOM | 487 | CA | ARG | A | 299 | 19.804 | 2.854 | 9.902 | 1.00 34.29 | A | C |
| ATOM | 488 | CB | ARG | A | 299 | 18.951 | 3.066 | 8.667 | 1.00 35.92 | A | C |
| ATOM | 489 | CG | ARG | A | 299 | 19.727 | 2.764 | 7.408 | 1.00 35.19 | A | C |
| ATOM | 490 | CD | ARG | A | 299 | 20.755 | 3.821 | 7.173 | 1.00 36.32 | A | C |
| ATOM | 491 | NE | ARG | A | 299 | 21.797 | 3.304 | 6.311 | 1.00 38.15 | A | N |
| ATOM | 492 | CZ | ARG | A | 299 | 23.096 | 3.475 | 6.511 | 1.00 39.67 | A | C |
| ATOM | 493 | NH1 | ARG | A | 299 | 23.559 | 4.181 | 7.564 | 1.00 41.79 | A | N |
| ATOM | 494 | NH2 | ARG | A | 299 | 23.935 | 2.865 | 5.692 | 1.00 39.61 | A | N |
| ATOM | 495 | C | ARG | A | 299 | 19.132 | 3.333 | 11.183 | 1.00 33.20 | A | C |
| ATOM | 496 | O | ARG | A | 299 | 18.758 | 4.501 | 11.296 | 1.00 33.57 | A | O |
| ATOM | 497 | N | LEU | A | 300 | 19.117 | 2.451 | 12.184 | 1.00 31.47 | A | N |
| ATOM | 498 | CA | LEU | A | 300 | 18.495 | 2.714 | 13.477 | 1.00 30.32 | A | C |
| ATOM | 499 | CB | LEU | A | 300 | 17.411 | 1.649 | 13.763 | 1.00 28.85 | A | C |
| ATOM | 500 | CG | LEU | A | 300 | 15.969 | 2.079 | 13.499 | 1.00 27.12 | A | C |
| ATOM | 501 | CD1 | LEU | A | 300 | 15.779 | 2.595 | 12.086 | 1.00 27.88 | A | C |
| ATOM | 502 | CD2 | LEU | A | 300 | 15.058 | 0.931 | 13.758 | 1.00 28.22 | A | C |
| ATOM | 503 | C | LEU | A | 300 | 19.537 | 2.710 | 14.564 | 1.00 30.04 | A | C |
| ATOM | 504 | O | LEU | A | 300 | 20.482 | 1.968 | 14.452 | 1.00 31.06 | A | O |
| ATOM | 505 | N | VAL | A | 301 | 19.408 | 3.539 | 15.595 | 1.00 31.48 | A | N |
| ATOM | 506 | CA | VAL | A | 301 | 20.413 | 3.501 | 16.662 | 1.00 33.00 | A | C |
| ATOM | 507 | CB | VAL | A | 301 | 20.207 | 4.656 | 17.667 | 1.00 32.54 | A | C |
| ATOM | 508 | CG1 | VAL | A | 301 | 20.973 | 4.382 | 18.957 | 1.00 31.33 | A | C |
| ATOM | 509 | CG2 | VAL | A | 301 | 20.674 | 5.946 | 17.049 | 1.00 29.51 | A | C |
| ATOM | 510 | C | VAL | A | 301 | 20.323 | 2.140 | 17.373 | 1.00 34.83 | A | C |
| ATOM | 511 | O | VAL | A | 301 | 19.232 | 1.664 | 17.660 | 1.00 34.85 | A | O |
| ATOM | 512 | N | ARG | A | 302 | 21.443 | 1.458 | 17.567 | 1.00 36.98 | A | N |
| ATOM | 513 | CA | ARG | A | 302 | 21.394 | 0.148 | 18.250 | 1.00 39.35 | A | C |
| ATOM | 514 | CB | ARG | A | 302 | 22.398 | -0.834 | 17.657 | 1.00 42.75 | A | C |
| ATOM | 515 | CG | ARG | A | 302 | 22.528 | -2.159 | 18.384 | 1.00 48.39 | A | C |
| ATOM | 516 | CD | ARG | A | 302 | 23.594 | -2.042 | 19.487 | 1.00 54.07 | A | C |
| ATOM | 517 | NE | ARG | A | 302 | 24.226 | -3.327 | 19.772 | 1.00 58.04 | A | N |
| ATOM | 518 | CZ | ARG | A | 302 | 25.163 | -3.877 | 19.000 | 1.00 60.38 | A | C |
| ATOM | 519 | NH1 | ARG | A | 302 | 25.599 | -3.249 | 17.903 | 1.00 61.05 | A | N |
| ATOM | 520 | NH2 | ARG | A | 302 | 25.619 | -5.081 | 19.295 | .1.00 61.26 | A | N |
| ATOM | 521 | C | ARG | A | 302 | 21.609 | 0.270 | 19.745 | 1.00 39.15 | A | C |
| ATOM | 522 | O | ARG | A | 302 | 22.449 | 1.036 | 20.213 | 1.00 38.31 | A | O |
| ATOM | 523 | N | LEU | A | 303 | 20.788 | -0.452 | 20.488 | 1.00 38.52 | A | N |
| ATOM | 524 | CA | LEU | A | 303 | 20.853 | -0.461 | 21.936 | 1.00 38.38 | A | C |
| ATOM | 525 | CB | LEU | A | 303 | 19.463 | -0.688 | 22.535 | 1.00 37.09 | A | C |
| ATOM | 526 | CG | LEU | A | 303 | 19.492 | -0.745 | 24.055 | 1.00 37.19 | A | C |
| ATOM | 527 | CD1 | LEU | A | 303 | 19.097 | 0.620 | 24.590 | 1.00 36.99 | A | C |

Figure 13

| ATOM | 528 | CD2 | LEU | A | 303 | 18.560 | -1.818 | 24.543 | 1.00 | 36.37 | A | C |
| ATOM | 529 | C | LEU | A | 303 | 21.774 | -1.584 | 22.394 | 1.00 | 38.37 | A | C |
| ATOM | 530 | O | LEU | A | 303 | 21.780 | -2.648 | 21.787 | 1.00 | 37.98 | A | O |
| ATOM | 531 | N | TYR | A | 304 | 22.625 | -1.310 | 23.379 | 1.00 | 38.43 | A | N |
| ATOM | 532 | CA | TYR | A | 304 | 23.479 | -2.356 | 23.908 | 1.00 | 39.43 | A | C |
| ATOM | 533 | CB | TYR | A | 304 | 24.921 | -1.917 | 24.137 | 1.00 | 42.52 | A | C |
| ATOM | 534 | CG | TYR | A | 304 | 25.753 | -1.691 | 22.920 | 1.00 | 45.04 | A | C |
| ATOM | 535 | CD1 | TYR | A | 304 | 25.727 | -0.474 | 22.296 | 1.00 | 47.45 | A | C |
| ATOM | 536 | CE1 | TYR | A | 304 | 26.524 | -0.183 | 21.232 | 1.00 | 48.62 | A | C |
| ATOM | 537 | CD2 | TYR | A | 304 | 26.629 | -2.659 | 22.433 | 1.00 | 49.10 | A | C |
| ATOM | 538 | CE2 | TYR | A | 304 | 27.462 | -2.367 | 21.326 | 1.00 | 51.38 | A | C |
| ATOM | 539 | CZ | TYR | A | 304 | 27.381 | -1.100 | 20.741 | 1.00 | 50.09 | A | C |
| ATOM | 540 | OH | TYR | A | 304 | 28.135 | -0.718 | 19.656 | 1.00 | 50.37 | A | O |
| ATOM | 541 | C | TYR | A | 304 | 22.946 | -2.861 | 25.247 | 1.00 | 38.44 | A | C |
| ATOM | 542 | O | TYR | A | 304 | 22.863 | -4.054 | 25.419 | 1.00 | 40.18 | A | O |
| ATOM | 543 | N | ALA | A | 305 | 22.590 | -1.971 | 26.178 | 1.00 | 37.62 | A | N |
| ATOM | 544 | CA | ALA | A | 305 | 22.111 | -2.362 | 27.506 | 1.00 | 36.96 | A | C |
| ATOM | 545 | CB | ALA | A | 305 | 23.299 | -2.845 | 28.322 | 1.00 | 37.71 | A | C |
| ATOM | 546 | C | ALA | A | 305 | 21.377 | -1.289 | 28.302 | 1.00 | 37.25 | A | C |
| ATOM | 547 | O | ALA | A | 305 | 21.263 | -0.142 | 27.879 | 1.00 | 37.41 | A | O |
| ATOM | 548 | N | VAL | A | 306 | 20.911 | -1.667 | 29.484 | 1.00 | 37.55 | A | N |
| ATOM | 549 | CA | VAL | A | 306 | 20.233 | -0.726 | 30.373 | 1.00 | 39.10 | A | C |
| ATOM | 550 | CB | VAL | A | 306 | 18.689 | -0.794 | 30.232 | 1.00 | 39.62 | A | C |
| ATOM | 551 | CG1 | VAL | A | 306 | 18.234 | -0.106 | 28.970 | 1.00 | 39.81 | A | C |
| ATOM | 552 | CG2 | VAL | A | 306 | 18.248 | -2.195 | 30.191 | 1.00 | 40.66 | A | C |
| ATOM | 553 | C | VAL | A | 306 | 20.612 | -1.079 | 31.799 | 1.00 | 39.60 | A | C |
| ATOM | 554 | O | VAL | A | 306 | 20.958 | -2.226 | 32.064 | 1.00 | 40.45 | A | O |
| ATOM | 555 | N | VAL | A | 307 | 20.631 | -0.087 | 32.684 | 1.00 | 39.34 | A | N |
| ATOM | 556 | CA | VAL | A | 307 | 20.943 | -0.289 | 34.097 | 1.00 | 40.26 | A | C |
| ATOM | 557 | CB | VAL | A | 307 | 22.243 | 0.465 | 34.497 | 1.00 | 38.50 | A | C |
| ATOM | 558 | CG1 | VAL | A | 307 | 22.496 | 0.387 | 36.011 | 1.00 | 35.41 | A | C |
| ATOM | 559 | CG2 | VAL | A | 307 | 23.379 | -0.088 | 33.708 | 1.00 | 36.01 | A | C |
| ATOM | 560 | C | VAL | A | 307 | 19.699 | 0.222 | 34.860 | 1.00 | 42.80 | A | C |
| ATOM | 561 | O | VAL | A | 307 | 19.426 | 1.429 | 34.897 | 1.00 | 42.90 | A | O |
| ATOM | 562 | N | THR | A | 308 | 18.957 | -0.701 | 35.472 | 1.00 | 45.25 | A | N |
| ATOM | 563 | CA | THR | A | 308 | 17.713 | -0.366 | 36.183 | 1.00 | 47.72 | A | C |
| ATOM | 564 | CB | THR | A | 308 | 16.825 | -1.583 | 36.298 | 1.00 | 48.03 | A | C |
| ATOM | 565 | OG1 | THR | A | 308 | 17.536 | -2.609 | 37.005 | 1.00 | 50.04 | A | O |
| ATOM | 566 | CG2 | THR | A | 308 | 16.425 | -2.046 | 34.911 | 1.00 | 46.98 | A | C |
| ATOM | 567 | C | THR | A | 308 | 17.760 | 0.296 | 37.553 | 1.00 | 49.21 | A | C |
| ATOM | 568 | O | THR | A | 308 | 16.726 | 0.753 | 38.033 | 1.00 | 48.58 | A | O |
| ATOM | 569 | N | GLN | A | 309 | 18.866 | 0.142 | 38.269 | 1.00 | 51.47 | A | N |
| ATOM | 570 | CA | GLN | A | 309 | 18.981 | 0.803 | 39.566 | 1.00 | 54.05 | A | C |
| ATOM | 571 | CB | GLN | A | 309 | 20.020 | 0.098 | 40.486 | 1.00 | 56.25 | A | C |
| ATOM | 572 | CG | GLN | A | 309 | 19.638 | -1.311 | 40.974 | 1.00 | 60.42 | A | C |
| ATOM | 573 | CD | GLN | A | 309 | 18.203 | -1.407 | 41.628 | 1.00 | 62.36 | A | C |
| ATOM | 574 | OE1 | GLN | A | 309 | 17.491 | -0.383 | 41.791 | 1.00 | 62.67 | A | O |
| ATOM | 575 | NE2 | GLN | A | 309 | 17.799 | -2.620 | 41.999 | 1.00 | 63.24 | A | N |
| ATOM | 576 | C | GLN | A | 309 | 19.322 | 2.285 | 39.349 | 1.00 | 54.15 | A | C |
| ATOM | 577 | O | GLN | A | 309 | 20.030 | 2.645 | 38.410 | 1.00 | 53.81 | A | O |
| ATOM | 578 | N | GLU | A | 310 | 18.783 | 3.130 | 40.207 | 1.00 | 54.29 | A | N |
| ATOM | 579 | CA | GLU | A | 310 | 19.016 | 4.559 | 40.112 | 1.00 | 55.51 | A | C |
| ATOM | 580 | CB | GLU | A | 310 | 18.044 | 5.302 | 41.030 | 1.00 | 59.09 | A | C |
| ATOM | 581 | CG | GLU | A | 310 | 17.926 | 4.714 | 42.449 | 1.00 | 65.01 | A | C |
| ATOM | 582 | CD | GLU | A | 310 | 16.663 | 3.828 | 42.684 | 1.00 | 67.45 | A | C |
| ATOM | 583 | OE1 | GLU | A | 310 | 15.544 | 4.247 | 42.262 | 1.00 | 68.92 | A | O |
| ATOM | 584 | OE2 | GLU | A | 310 | 16.798 | 2.744 | 43.328 | 1.00 | 66.89 | A | O |
| ATOM | 585 | C | GLU | A | 310 | 20.478 | 4.977 | 40.386 | 1.00 | 54.21 | A | C |
| ATOM | 586 | O | GLU | A | 310 | 21.113 | 4.494 | 41.330 | 1.00 | 54.51 | A | O |
| ATOM | 587 | N | PRO | A | 311 | 21.018 | 5.869 | 39.526 | 1.00 | 52.67 | A | N |

Figure 13

| ATOM | 588 | CD  | PRO | A | 311 | 22.383 | 6.426 | 39.800 | 1.00 | 52.30 | A | C |
| ATOM | 589 | CA  | PRO | A | 311 | 20.451 | 6.504 | 38.348 | 1.00 | 50.28 | A | C |
| ATOM | 590 | CB  | PRO | A | 311 | 21.464 | 7.605 | 37.999 | 1.00 | 49.62 | A | C |
| ATOM | 591 | CG  | PRO | A | 311 | 22.205 | 7.831 | 39.302 | 1.00 | 50.51 | A | C |
| ATOM | 592 | C   | PRO | A | 311 | 20.240 | 5.517 | 37.148 | 1.00 | 48.22 | A | C |
| ATOM | 593 | O   | PRO | A | 311 | 21.117 | 4.691 | 36.841 | 1.00 | 48.25 | A | O |
| ATOM | 594 | N   | ILE | A | 312 | 19.075 | 5.585 | 36.531 | 1.00 | 45.34 | A | N |
| ATOM | 595 | CA  | ILE | A | 312 | 18.725 | 4.707 | 35.399 | 1.00 | 41.47 | A | C |
| ATOM | 596 | CB  | ILE | A | 312 | 17.221 | 4.868 | 35.000 | 1.00 | 42.48 | A | C |
| ATOM | 597 | CG2 | ILE | A | 312 | 16.793 | 3.710 | 34.092 | 1.00 | 42.71 | A | C |
| ATOM | 598 | CG1 | ILE | A | 312 | 16.305 | 4.997 | 36.240 | 1.00 | 42.88 | A | C |
| ATOM | 599 | CD1 | ILE | A | 312 | 15.842 | 3.696 | 36.880 | 1.00 | 40.14 | A | C |
| ATOM | 600 | C   | ILE | A | 312 | 19.554 | 5.081 | 34.159 | 1.00 | 37.62 | A | C |
| ATOM | 601 | O   | ILE | A | 312 | 19.718 | 6.265 | 33.851 | 1.00 | 36.65 | A | O |
| ATOM | 602 | N   | TYR | A | 313 | 20.015 | 4.080 | 33.420 | 1.00 | 34.22 | A | N |
| ATOM | 603 | CA  | TYR | A | 313 | 20.816 | 4.348 | 32.234 | 1.00 | 32.02 | A | C |
| ATOM | 604 | CB  | TYR | A | 313 | 22.281 | 3.894 | 32.406 | 1.00 | 32.27 | A | C |
| ATOM | 605 | CG  | TYR | A | 313 | 23.184 | 4.597 | 33.407 | 1.00 | 32.94 | A | C |
| ATOM | 606 | CD1 | TYR | A | 313 | 22.879 | 5.853 | 33.925 | 1.00 | 33.25 | A | C |
| ATOM | 607 | CE1 | TYR | A | 313 | 23.773 | 6.501 | 34.796 | 1.00 | 35.16 | A | C |
| ATOM | 608 | CD2 | TYR | A | 313 | 24.400 | 4.004 | 33.784 | 1.00 | 33.96 | A | C |
| ATOM | 609 | CE2 | TYR | A | 313 | 25.300 | 4.640 | 34.642 | 1.00 | 34.56 | A | C |
| ATOM | 610 | CZ  | TYR | A | 313 | 24.993 | 5.889 | 35.149 | 1.00 | 35.29 | A | C |
| ATOM | 611 | OH  | TYR | A | 313 | 25.882 | 6.552 | 35.981 | 1.00 | 34.79 | A | O |
| ATOM | 612 | C   | TYR | A | 313 | 20.326 | 3.589 | 31.022 | 1.00 | 30.28 | A | C |
| ATOM | 613 | O   | TYR | A | 313 | 19.853 | 2.476 | 31.147 | 1.00 | 29.74 | A | O |
| ATOM | 614 | N   | ILE | A | 314 | 20.460 | 4.173 | 29.835 | 1.00 | 29.06 | A | N |
| ATOM | 615 | CA  | ILE | A | 314 | 20.124 | 3.429 | 28.603 | 1.00 | 27.92 | A | C |
| ATOM | 616 | CB  | ILE | A | 314 | 18.962 | 4.049 | 27.799 | 1.00 | 26.78 | A | C |
| ATOM | 617 | CG2 | ILE | A | 314 | 18.827 | 3.395 | 26.459 | 1.00 | 22.58 | A | C |
| ATOM | 618 | CG1 | ILE | A | 314 | 17.675 | 3.923 | 28.569 | 1.00 | 25.54 | A | C |
| ATOM | 619 | CD1 | ILE | A | 314 | 16.624 | 4.745 | 28.034 | 1.00 | 27.59 | A | C |
| ATOM | 620 | C   | ILE | A | 314 | 21.426 | 3.556 | 27.815 | 1.00 | 27.76 | A | C |
| ATOM | 621 | O   | ILE | A | 314 | 21.904 | 4.676 | 27.612 | 1.00 | 29.10 | A | O |
| ATOM | 622 | N   | ILE | A | 315 | 22.071 | 2.437 | 27.511 | 1.00 | 26.20 | A | N |
| ATOM | 623 | CA  | ILE | A | 315 | 23.344 | 2.459 | 26.774 | 1.00 | 26.34 | A | C |
| ATOM | 624 | CB  | ILE | A | 315 | 24.468 | 1.491 | 27.424 | 1.00 | 28.44 | A | C |
| ATOM | 625 | CG2 | ILE | A | 315 | 25.719 | 1.353 | 26.545 | 1.00 | 25.47 | A | C |
| ATOM | 626 | CG1 | ILE | A | 315 | 24.912 | 1.998 | 28.800 | 1.00 | 28.38 | A | C |
| ATOM | 627 | CD1 | ILE | A | 315 | 23.966 | 1.627 | 29.935 | 1.00 | 28.73 | A | C |
| ATOM | 628 | C   | ILE | A | 315 | 23.146 | 2.063 | 25.323 | 1.00 | 25.80 | A | C |
| ATOM | 629 | O   | ILE | A | 315 | 22.637 | 0.982 | 25.038 | 1.00 | 24.83 | A | O |
| ATOM | 630 | N   | THR | A | 316 | 23.557 | 2.945 | 24.417 | 1.00 | 24.77 | A | N |
| ATOM | 631 | CA  | THR | A | 316 | 23.459 | 2.711 | 22.980 | 1.00 | 24.18 | A | C |
| ATOM | 632 | CB  | THR | A | 316 | 22.604 | 3.763 | 22.321 | 1.00 | 23.41 | A | C |
| ATOM | 633 | OG1 | THR | A | 316 | 23.260 | 5.038 | 22.443 | 1.00 | 22.95 | A | O |
| ATOM | 634 | CG2 | THR | A | 316 | 21.263 | 3.860 | 23.004 | 1.00 | 24.04 | A | C |
| ATOM | 635 | C   | THR | A | 316 | 24.814 | 2.942 | 22.359 | 1.00 | 24.18 | A | C |
| ATOM | 636 | O   | THR | A | 316 | 25.712 | 3.468 | 22.997 | 1.00 | 24.33 | A | O |
| ATOM | 637 | N   | GLU | A | 317 | 24.898 | 2.689 | 21.064 | 1.00 | 25.03 | A | N |
| ATOM | 638 | CA  | GLU | A | 317 | 26.132 | 2.917 | 20.336 | 1.00 | 25.94 | A | C |
| ATOM | 639 | CB  | GLU | A | 317 | 25.999 | 2.375 | 18.920 | 1.00 | 26.06 | A | C |
| ATOM | 640 | CG  | GLU | A | 317 | 25.048 | 3.162 | 18.050 | 1.00 | 24.64 | A | C |
| ATOM | 641 | CD  | GLU | A | 317 | 25.018 | 2.647 | 16.646 | 1.00 | 24.59 | A | C |
| ATOM | 642 | OE1 | GLU | A | 317 | 23.935 | 2.212 | 16.220 | 1.00 | 25.02 | A | O |
| ATOM | 643 | OE2 | GLU | A | 317 | 26.065 | 2.684 | 15.954 | 1.00 | 23.42 | A | O |
| ATOM | 644 | C   | GLU | A | 317 | 26.479 | 4.425 | 20.302 | 1.00 | 26.91 | A | C |
| ATOM | 645 | O   | GLU | A | 317 | 25.613 | 5.301 | 20.377 | 1.00 | 26.21 | A | O |
| ATOM | 646 | N   | TYR | A | 318 | 27.766 | 4.705 | 20.176 | 1.00 | 27.88 | A | N |
| ATOM | 647 | CA  | TYR | A | 318 | 28.258 | 6.058 | 20.154 | 1.00 | 28.04 | A | C |

Figure 13

| ATOM | 648 | CB | TYR A 318 | 29.631 | 6.141 | 20.782 | 1.00 | 25.93 | A | C |
| ATOM | 649 | CG | TYR A 318 | 30.201 | 7.544 | 20.714 | 1.00 | 28.09 | A | C |
| ATOM | 650 | CD1 | TYR A 318 | 29.616 | 8.599 | 21.409 | 1.00 | 28.77 | A | C |
| ATOM | 651 | CE1 | TYR A 318 | 30.158 | 9.895 | 21.333 | 1.00 | 28.46 | A | C |
| ATOM | 652 | CD2 | TYR A 318 | 31.343 | 7.837 | 19.942 | 1.00 | 28.56 | A | C |
| ATOM | 653 | CE2 | TYR A 318 | 31.880 | 9.138 | 19.874 | 1.00 | 26.57 | A | C |
| ATOM | 654 | CZ | TYR A 318 | 31.273 | 10.136 | 20.576 | 1.00 | 26.76 | A | C |
| ATOM | 655 | OH | TYR A 318 | 31.771 | 11.386 | 20.555 | 1.00 | 26.77 | A | O |
| ATOM | 656 | C | TYR A 318 | 28.323 | 6.564 | 18.739 | 1.00 | 29.08 | A | C |
| ATOM | 657 | O | TYR A 318 | 28.872 | 5.920 | 17.872 | 1.00 | 28.71 | A | O |
| ATOM | 658 | N | MET A 319 | 27.761 | 7.751 | 18.546 | 1.00 | 31.24 | A | N |
| ATOM | 659 | CA | MET A 319 | 27.695 | 8.467 | 17.283 | 1.00 | 32.96 | A | C |
| ATOM | 660 | CB | MET A 319 | 26.234 | 8.826 | 16.994 | 1.00 | 33.40 | A | C |
| ATOM | 661 | CG | MET A 319 | 25.322 | 7.620 | 16.799 | 1.00 | 31.72 | A | C |
| ATOM | 662 | SD | MET A 319 | 25.873 | 6.450 | 15.468 | 1.00 | 31.83 | A | S |
| ATOM | 663 | CE | MET A 319 | 25.303 | 7.187 | 14.115 | 1.00 | 29.97 | A | C |
| ATOM | 664 | C | MET A 319 | 28.542 | 9.742 | 17.449 | 1.00 | 33.42 | A | C |
| ATOM | 665 | O | MET A 319 | 28.117 | 10.730 | 18.021 | 1.00 | 33.73 | A | O |
| ATOM | 666 | N | GLU A 320 | 29.771 | 9.634 | 16.990 | 1.00 | 34.27 | A | N |
| ATOM | 667 | CA | GLU A 320 | 30.771 | 10.674 | 17.010 | 1.00 | 35.00 | A | C |
| ATOM | 668 | CB | GLU A 320 | 31.827 | 10.254 | 15.984 | 1.00 | 37.04 | A | C |
| ATOM | 669 | CG | GLU A 320 | 32.871 | 11.260 | 15.628 | 1.00 | 40.04 | A | C |
| ATOM | 670 | CD | GLU A 320 | 34.167 | 11.050 | 16.375 | 1.00 | 41.83 | A | C |
| ATOM | 671 | OE1 | GLU A 320 | 34.568 | 9.873 | 16.555 | 1.00 | 41.04 | A | O |
| ATOM | 672 | OE2 | GLU A 320 | 34.788 | 12.077 | 16.758 | 1.00 | 43.90 | A | O |
| ATOM | 673 | C | GLU A 320 | 30.217 | 12.061 | 16.669 | 1.00 | 34.88 | A | C |
| ATOM | 674 | O | GLU A 320 | 30.248 | 12.989 | 17.485 | 1.00 | 36.11 | A | O |
| ATOM | 675 | N | ASN A 321 | 29.638 | 12.209 | 15.491 | 1.00 | 33.36 | A | N |
| ATOM | 676 | CA | ASN A 321 | 29.174 | 13.515 | 15.163 | 1.00 | 32.12 | A | C |
| ATOM | 677 | CB | ASN A 321 | 29.192 | 13.684 | 13.667 | 1.00 | 32.12 | A | C |
| ATOM | 678 | CG | ASN A 321 | 30.621 | 13.838 | 13.150 | 1.00 | 30.76 | A | C |
| ATOM | 679 | OD1 | ASN A 321 | 31.317 | 14.815 | 13.484 | 1.00 | 28.97 | A | O |
| ATOM | 680 | ND2 | ASN A 321 | 31.079 | 12.864 | 12.389 | 1.00 | 29.40 | A | N |
| ATOM | 681 | C | ASN A 321 | 27.912 | 13.994 | 15.805 | 1.00 | 31.75 | A | C |
| ATOM | 682 | O | ASN A 321 | 27.473 | 15.096 | 15.504 | 1.00 | 34.05 | A | O |
| ATOM | 683 | N | GLY A 322 | 27.373 | 13.233 | 16.751 | 1.00 | 31.26 | A | N |
| ATOM | 684 | CA | GLY A 322 | 26.162 | 13.645 | 17.437 | 1.00 | 29.43 | A | C |
| ATOM | 685 | C | GLY A 322 | 24.916 | 13.784 | 16.574 | 1.00 | 28.78 | A | C |
| ATOM | 686 | O | GLY A 322 | 24.653 | 12.975 | 15.681 | 1.00 | 27.67 | A | O |
| ATOM | 687 | N | SER A 323 | 24.187 | 14.864 | 16.837 | 1.00 | 28.16 | A | N |
| ATOM | 688 | CA | SER A 323 | 22.923 | 15.199 | 16.191 | 1.00 | 28.17 | A | C |
| ATOM | 689 | CB | SER A 323 | 22.125 | 16.083 | 17.156 | 1.00 | 27.40 | A | C |
| ATOM | 690 | OG | SER A 323 | 20.778 | 16.242 | 16.772 | 1.00 | 28.68 | A | O |
| ATOM | 691 | C | SER A 323 | 23.091 | 15.895 | 14.847 | 1.00 | 27.79 | A | C |
| ATOM | 692 | O | SER A 323 | 23.821 | 16.855 | 14.752 | 1.00 | 28.45 | A | O |
| ATOM | 693 | N | LEU A 324 | 22.341 | 15.455 | 13.841 | 1.00 | 26.89 | A | N |
| ATOM | 694 | CA | LEU A 324 | 22.420 | 16.035 | 12.506 | 1.00 | 25.99 | A | C |
| ATOM | 695 | CB | LEU A 324 | 21.544 | 15.242 | 11.558 | 1.00 | 23.48 | A | C |
| ATOM | 696 | CG | LEU A 324 | 21.418 | 15.688 | 10.114 | 1.00 | 21.02 | A | C |
| ATOM | 697 | CD1 | LEU A 324 | 22.727 | 15.489 | 9.406 | 1.00 | 20.67 | A | C |
| ATOM | 698 | CD2 | LEU A 324 | 20.301 | 14.905 | 9.442 | 1.00 | 19.45 | A | C |
| ATOM | 699 | C | LEU A 324 | 22.033 | 17.530 | 12.464 | 1.00 | 26.74 | A | C |
| ATOM | 700 | O | LEU A 324 | 22.592 | 18.287 | 11.680 | 1.00 | 27.74 | A | O |
| ATOM | 701 | N | VAL A 325 | 21.115 | 17.982 | 13.311 | 1.00 | 27.62 | A | N |
| ATOM | 702 | CA | VAL A 325 | 20.757 | 19.394 | 13.261 | 1.00 | 28.42 | A | C |
| ATOM | 703 | CB | VAL A 325 | 19.456 | 19.654 | 14.088 | 1.00 | 27.24 | A | C |
| ATOM | 704 | CG1 | VAL A 325 | 19.722 | 19.710 | 15.597 | 1.00 | 26.29 | A | C |
| ATOM | 705 | CG2 | VAL A 325 | 18.726 | 20.883 | 13.573 | 1.00 | 26.09 | A | C |
| ATOM | 706 | C | VAL A 325 | 21.968 | 20.248 | 13.704 | 1.00 | 29.35 | A | C |
| ATOM | 707 | O | VAL A 325 | 22.229 | 21.323 | 13.159 | 1.00 | 29.22 | A | O |

Figure 13

| | | | | | | | | | | | |
|---|---|---|---|---|---|---|---|---|---|---|---|
| ATOM | 708 | N | ASP | A | 326 | 22.766 | 19.690 | 14.613 | 1.00 | 30.77 | A N |
| ATOM | 709 | CA | ASP | A | 326 | 23.961 | 20.343 | 15.133 | 1.00 | 31.35 | A C |
| ATOM | 710 | CB | ASP | A | 326 | 24.298 | 19.741 | 16.486 | 1.00 | 32.71 | A C |
| ATOM | 711 | CG | ASP | A | 326 | 23.271 | 20.108 | 17.536 | 1.00 | 35.28 | A C |
| ATOM | 712 | OD1 | ASP | A | 326 | 22.562 | 21.113 | 17.318 | 1.00 | 34.86 | A O |
| ATOM | 713 | OD2 | ASP | A | 326 | 23.162 | 19.392 | 18.560 | 1.00 | 37.05 | A O |
| ATOM | 714 | C | ASP | A | 326 | 25.163 | 20.256 | 14.200 | 1.00 | 31.84 | A C |
| ATOM | 715 | O | ASP | A | 326 | 25.845 | 21.250 | 13.934 | 1.00 | 31.79 | A O |
| ATOM | 716 | N | PHE | A | 327 | 25.369 | 19.076 | 13.652 | 1.00 | 32.04 | A N |
| ATOM | 717 | CA | PHE | A | 327 | 26.475 | 18.829 | 12.754 | 1.00 | 32.68 | A C |
| ATOM | 718 | CB | PHE | A | 327 | 26.466 | 17.398 | 12.346 | 1.00 | 32.89 | A C |
| ATOM | 719 | CG | PHE | A | 327 | 27.527 | 17.055 | 11.364 | 1.00 | 34.31 | A C |
| ATOM | 720 | CD1 | PHE | A | 327 | 28.861 | 17.090 | 11.749 | 1.00 | 34.82 | A C |
| ATOM | 721 | CD2 | PHE | A | 327 | 27.199 | 16.563 | 10.095 | 1.00 | 33.94 | A C |
| ATOM | 722 | CE1 | PHE | A | 327 | 29.848 | 16.629 | 10.894 | 1.00 | 34.20 | A C |
| ATOM | 723 | CE2 | PHE | A | 327 | 28.185 | 16.100 | 9.236 | 1.00 | 33.51 | A C |
| ATOM | 724 | CZ | PHE | A | 327 | 29.504 | 16.130 | 9.636 | 1.00 | 33.83 | A C |
| ATOM | 725 | C | PHE | A | 327 | 26.391 | 19.595 | 11.474 | 1.00 | 33.29 | A C |
| ATOM | 726 | O | PHE | A | 327 | 27.408 | 19.940 | 10.875 | 1.00 | 34.06 | A O |
| ATOM | 727 | N | LEU | A | 328 | 25.177 | 19.728 | 10.969 | 1.00 | 32.68 | A N |
| ATOM | 728 | CA | LEU | A | 328 | 25.005 | 20.416 | 9.722 | 1.00 | 32.32 | A C |
| ATOM | 729 | CB | LEU | A | 328 | 23.536 | 20.442 | 9.344 | 1.00 | 29.92 | A C |
| ATOM | 730 | CG | LEU | A | 328 | 22.960 | 19.203 | 8.716 | 1.00 | 27.05 | A C |
| ATOM | 731 | CD1 | LEU | A | 328 | 21.553 | 19.501 | 8.375 | 1.00 | 26.60 | A C |
| ATOM | 732 | CD2 | LEU | A | 328 | 23.771 | 18.832 | 7.477 | 1.00 | 27.25 | A C |
| ATOM | 733 | C | LEU | A | 328 | 25.513 | 21.834 | 9.827 | 1.00 | 34.24 | A C |
| ATOM | 734 | O | LEU | A | 328 | 25.808 | 22.435 | 8.805 | 1.00 | 35.35 | A O |
| ATOM | 735 | N | LYS | A | 329 | 25.606 | 22.370 | 11.052 | 1.00 | 35.93 | A N |
| ATOM | 736 | CA | LYS | A | 329 | 26.034 | 23.757 | 11.273 | 1.00 | 37.08 | A C |
| ATOM | 737 | CB | LYS | A | 329 | 25.285 | 24.379 | 12.454 | 1.00 | 35.70 | A C |
| ATOM | 738 | CG | LYS | A | 329 | 23.750 | 24.464 | 12.338 | 1.00 | 33.77 | A C |
| ATOM | 739 | CD | LYS | A | 329 | 23.185 | 25.218 | 13.527 | 1.00 | 31.47 | A C |
| ATOM | 740 | CE | LYS | A | 329 | 21.698 | 25.223 | 13.565 | 1.00 | 32.40 | A C |
| ATOM | 741 | NZ | LYS | A | 329 | 21.202 | 23.888 | 13.826 | 1.00 | 34.15 | A N |
| ATOM | 742 | C | LYS | A | 329 | 27.521 | 23.910 | 11.498 | 1.00 | 38.63 | A C |
| ATOM | 743 | O | LYS | A | 329 | 28.037 | 25.018 | 11.419 | 1.00 | 40.81 | A O |
| ATOM | 744 | N | THR | A | 330 | 28.204 | 22.811 | 11.783 | 1.00 | 39.71 | A N |
| ATOM | 745 | CA | THR | A | 330 | 29.653 | 22.829 | 12.004 | 1.00 | 40.50 | A C |
| ATOM | 746 | CB | THR | A | 330 | 30.141 | 21.458 | 12.505 | 1.00 | 40.75 | A C |
| ATOM | 747 | OG1 | THR | A | 330 | 29.954 | 20.453 | 11.486 | 1.00 | 40.95 | A O |
| ATOM | 748 | CG2 | THR | A | 330 | 29.370 | 21.082 | 13.798 | 1.00 | 40.56 | A C |
| ATOM | 749 | C | THR | A | 330 | 30.382 | 23.113 | 10.699 | 1.00 | 41.23 | A C |
| ATOM | 750 | O | THR | A | 330 | 29.854 | 22.822 | 9.624 | 1.00 | 41.84 | A O |
| ATOM | 751 | N | PRO | A | 331 | 31.608 | 23.662 | 10.775 | 1.00 | 41.46 | A N |
| ATOM | 752 | CD | PRO | A | 331 | 32.357 | 23.892 | 12.024 | 1.00 | 42.61 | A C |
| ATOM | 753 | CA | PRO | A | 331 | 32.444 | 23.993 | 9.617 | 1.00 | 40.80 | A C |
| ATOM | 754 | CB | PRO | A | 331 | 33.823 | 24.161 | 10.243 | 1.00 | 42.04 | A C |
| ATOM | 755 | CG | PRO | A | 331 | 33.475 | 24.778 | 11.566 | 1.00 | 43.05 | A C |
| ATOM | 756 | C | PRO | A | 331 | 32.437 | 22.859 | 8.597 | 1.00 | 39.86 | A C |
| ATOM | 757 | O | PRO | A | 331 | 32.250 | 23.098 | 7.410 | 1.00 | 38.80 | A O |
| ATOM | 758 | N | SER | A | 332 | 32.571 | 21.621 | 9.079 | 1.00 | 39.31 | A N |
| ATOM | 759 | CA | SER | A | 332 | 32.557 | 20.454 | 8.195 | 1.00 | 40.15 | A C |
| ATOM | 760 | CB | SER | A | 332 | 32.933 | 19.169 | 8.946 | 1.00 | 40.00 | A C |
| ATOM | 761 | OG | SER | A | 332 | 34.186 | 19.274 | 9.583 | 1.00 | 39.67 | A O |
| ATOM | 762 | C | SER | A | 332 | 31.167 | 20.263 | 7.593 | 1.00 | 40.41 | A C |
| ATOM | 763 | O | SER | A | 332 | 31.037 | 19.910 | 6.409 | 1.00 | 41.24 | A O |
| ATOM | 764 | N | GLY | A | 333 | 30.145 | 20.437 | 8.435 | 1.00 | 39.80 | A N |
| ATOM | 765 | CA | GLY | A | 333 | 28.774 | 20.264 | 7.999 | 1.00 | 39.32 | A C |
| ATOM | 766 | C | GLY | A | 333 | 28.373 | 21.244 | 6.919 | 1.00 | 39.59 | A C |
| ATOM | 767 | O | GLY | A | 333 | 27.770 | 20.861 | 5.905 | 1.00 | 38.97 | A O |

Figure 13

| ATOM | 768 | N | ILE | A | 334 | 28.800 | 22.496 | 7.091 | 1.00 | 40.69 | A | N |
| ATOM | 769 | CA | ILE | A | 334 | 28.501 | 23.576 | 6.139 | 1.00 | 41.72 | A | C |
| ATOM | 770 | CB | ILE | A | 334 | 29.081 | 24.921 | 6.623 | 1.00 | 42.35 | A | C |
| ATOM | 771 | CG2 | ILE | A | 334 | 29.127 | 25.914 | 5.477 | 1.00 | 43.77 | A | C |
| ATOM | 772 | CG1 | ILE | A | 334 | 28.333 | 25.451 | 7.868 | 1.00 | 44.10 | A | C |
| ATOM | 773 | CD1 | ILE | A | 334 | 26.837 | 25.899 | 7.684 | 1.00 | 44.42 | A | C |
| ATOM | 774 | C | ILE | A | 334 | 29.100 | 23.277 | 4.756 | 1.00 | 42.30 | A | C |
| ATOM | 775 | O | ILE | A | 334 | 28.514 | 23.621 | 3.729 | 1.00 | 42.66 | A | O |
| ATOM | 776 | N | LYS | A | 335 | 30.268 | 22.644 | 4.751 | 1.00 | 42.99 | A | N |
| ATOM | 777 | CA | LYS | A | 335 | 30.988 | 22.284 | 3.528 | 1.00 | 44.14 | A | C |
| ATOM | 778 | CB | LYS | A | 335 | 32.470 | 21.997 | 3.851 | 1.00 | 46.99 | A | C |
| ATOM | 779 | CG | LYS | A | 335 | 33.303 | 23.251 | 4.240 | 1.00 | 50.23 | A | C |
| ATOM | 780 | CD | LYS | A | 335 | 34.620 | 22.845 | 4.890 | 1.00 | 53.92 | A | C |
| ATOM | 781 | CE | LYS | A | 335 | 35.241 | 23.988 | 5.754 | 1.00 | 55.97 | A | C |
| ATOM | 782 | NZ | LYS | A | 335 | 36.033 | 23.342 | 6.909 | 1.00 | 58.47 | A | N |
| ATOM | 783 | C | LYS | A | 335 | 30.422 | 21.105 | 2.749 | 1.00 | 42.91 | A | C |
| ATOM | 784 | O | LYS | A | 335 | 30.715 | 20.971 | 1.560 | 1.00 | 43.57 | A | O |
| ATOM | 785 | N | LEU | A | 336 | 29.598 | 20.280 | 3.391 | 1.00 | 41.45 | A | N |
| ATOM | 786 | CA | LEU | A | 336 | 29.013 | 19.125 | 2.719 | 1.00 | 40.75 | A | C |
| ATOM | 787 | CB | LEU | A | 336 | 27.948 | 18.442 | 3.607 | 1.00 | 39.35 | A | C |
| ATOM | 788 | CG | LEU | A | 336 | 28.450 | 17.772 | 4.888 | 1.00 | 37.93 | A | C |
| ATOM | 789 | CD1 | LEU | A | 336 | 27.287 | 17.309 | 5.676 | 1.00 | 36.41 | A | C |
| ATOM | 790 | CD2 | LEU | A | 336 | 29.400 | 16.631 | 4.568 | 1.00 | 37.69 | A | C |
| ATOM | 791 | C | LEU | A | 336 | 28.393 | 19.448 | 1.353 | 1.00 | 40.67 | A | C |
| ATOM | 792 | O | LEU | A | 336 | 27.728 | 20.482 | 1.172 | 1.00 | 39.47 | A | O |
| ATOM | 793 | N | THR | A | 337 | 28.616 | 18.544 | 0.398 | 1.00 | 41.03 | A | N |
| ATOM | 794 | CA | THR | A | 337 | 28.075 | 18.696 | -0.937 | 1.00 | 41.02 | A | C |
| ATOM | 795 | CB | THR | A | 337 | 28.931 | 17.898 | -2.000 | 1.00 | 42.60 | A | C |
| ATOM | 796 | OG1 | THR | A | 337 | 28.855 | 16.477 | -1.782 | 1.00 | 44.04 | A | O |
| ATOM | 797 | CG2 | THR | A | 337 | 30.390 | 18.353 | -1.950 | 1.00 | 43.16 | A | C |
| ATOM | 798 | C | THR | A | 337 | 26.592 | 18.267 | -0.961 | 1.00 | 40.31 | A | C |
| ATOM | 799 | O | THR | A | 337 | 26.093 | 17.618 | -0.030 | 1.00 | 39.72 | A | O |
| ATOM | 800 | N | ILE | A | 338 | 25.873 | 18.714 | -1.987 | 1.00 | 39.66 | A | N |
| ATOM | 801 | CA | ILE | A | 338 | 24.475 | 18.361 | -2.151 | 1.00 | 37.59 | A | C |
| ATOM | 802 | CB | ILE | A | 338 | 23.867 | 19.069 | -3.376 | 1.00 | 35.77 | A | C |
| ATOM | 803 | CG2 | ILE | A | 338 | 24.465 | 18.495 | -4.642 | 1.00 | 34.89 | A | C |
| ATOM | 804 | CG1 | ILE | A | 338 | 22.346 | 18.844 | -3.468 | 1.00 | 35.73 | A | C |
| ATOM | 805 | CD1 | ILE | A | 338 | 21.503 | 19.289 | -2.279 | 1.00 | 33.36 | A | C |
| ATOM | 806 | C | ILE | A | 338 | 24.422 | 16.837 | -2.350 | 1.00 | 38.08 | A | C |
| ATOM | 807 | O | ILE | A | 338 | 23.445 | 16.195 | -1.964 | 1.00 | 39.06 | A | O |
| ATOM | 808 | N | ASN | A | 339 | 25.479 | 16.256 | -2.924 | 1.00 | 38.08 | A | N |
| ATOM | 809 | CA | ASN | A | 339 | 25.505 | 14.809 | -3.151 | 1.00 | 37.62 | A | C |
| ATOM | 810 | CB | ASN | A | 339 | 26.728 | 14.386 | -3.963 | 1.00 | 38.69 | A | C |
| ATOM | 811 | CG | ASN | A | 339 | 26.710 | 14.906 | -5.398 | 1.00 | 39.65 | A | C |
| ATOM | 812 | OD1 | ASN | A | 339 | 26.480 | 14.128 | -6.348 | 1.00 | 38.86 | A | O |
| ATOM | 813 | ND2 | ASN | A | 339 | 27.010 | 16.217 | -5.574 | 1.00 | 39.67 | A | N |
| ATOM | 814 | C | ASN | A | 339 | 25.545 | 14.074 | -1.835 | 1.00 | 36.89 | A | C |
| ATOM | 815 | O | ASN | A | 339 | 24.890 | 13.053 | -1.668 | 1.00 | 36.38 | A | O |
| ATOM | 816 | N | LYS | A | 340 | 26.377 | 14.561 | -0.923 | 1.00 | 36.89 | A | N |
| ATOM | 817 | CA | LYS | A | 340 | 26.501 | 13.961 | 0.400 | 1.00 | 37.11 | A | C |
| ATOM | 818 | CB | LYS | A | 340 | 27.669 | 14.616 | 1.148 | 1.00 | 39.00 | A | C |
| ATOM | 819 | CG | LYS | A | 340 | 27.946 | 14.031 | 2.521 | 1.00 | 41.35 | A | C |
| ATOM | 820 | CD | LYS | A | 340 | 28.079 | 12.504 | 2.463 | 1.00 | 41.23 | A | C |
| ATOM | 821 | CE | LYS | A | 340 | 28.016 | 11.970 | 3.883 | 1.00 | 43.00 | A | C |
| ATOM | 822 | NZ | LYS | A | 340 | 28.124 | 10.490 | 3.990 | 1.00 | 41.68 | A | N |
| ATOM | 823 | C | LYS | A | 340 | 25.189 | 14.139 | 1.197 | 1.00 | 36.01 | A | C |
| ATOM | 824 | O | LYS | A | 340 | 24.682 | 13.202 | 1.832 | 1.00 | 36.20 | A | O |
| ATOM | 825 | N | LEU | A | 341 | 24.617 | 15.330 | 1.098 | 1.00 | 34.47 | A | N |
| ATOM | 826 | CA | LEU | A | 341 | 23.385 | 15.650 | 1.796 | 1.00 | 33.24 | A | C |
| ATOM | 827 | CB | LEU | A | 341 | 23.029 | 17.123 | 1.555 | 1.00 | 29.99 | A | C |

Figure 13

| | | | | | | | | | | | |
|---|---|---|---|---|---|---|---|---|---|---|---|
| ATOM | 828 | CG | LEU | A | 341 | 23.958 | 18.225 | 2.083 | 1.00 | 24.84 | A | C |
| ATOM | 829 | CD1 | LEU | A | 341 | 23.460 | 19.519 | 1.553 | 1.00 | 24.69 | A | C |
| ATOM | 830 | CD2 | LEU | A | 341 | 24.035 | 18.264 | 3.598 | 1.00 | 22.91 | A | C |
| ATOM | 831 | C | LEU | A | 341 | 22.260 | 14.704 | 1.363 | 1.00 | 33.87 | A | C |
| ATOM | 832 | O | LEU | A | 341 | 21.573 | 14.146 | 2.207 | 1.00 | 34.89 | A | O |
| ATOM | 833 | N | LEU | A | 342 | 22.112 | 14.466 | 0.061 | 1.00 | 34.90 | A | N |
| ATOM | 834 | CA | LEU | A | 342 | 21.085 | 13.552 | -0.430 | 1.00 | 35.64 | A | C |
| ATOM | 835 | CB | LEU | A | 342 | 20.972 | 13.626 | -1.940 | 1.00 | 36.42 | A | C |
| ATOM | 836 | CG | LEU | A | 342 | 20.370 | 14.955 | -2.360 | 1.00 | 37.37 | A | C |
| ATOM | 837 | CD1 | LEU | A | 342 | 20.023 | 14.966 | -3.798 | 1.00 | 38.64 | A | C |
| ATOM | 838 | CD2 | LEU | A | 342 | 19.149 | 15.190 | -1.552 | 1.00 | 36.65 | A | C |
| ATOM | 839 | C | LEU | A | 342 | 21.303 | 12.117 | -0.020 | 1.00 | 36.20 | A | C |
| ATOM | 840 | O | LEU | A | 342 | 20.340 | 11.384 | 0.166 | 1.00 | 36.61 | A | O |
| ATOM | 841 | N | ASP | A | 343 | 22.553 | 11.667 | 0.053 | 1.00 | 37.02 | A | N |
| ATOM | 842 | CA | ASP | A | 343 | 22.755 | 10.291 | 0.475 | 1.00 | 37.34 | A | C |
| ATOM | 843 | CB | ASP | A | 343 | 24.139 | 9.721 | 0.135 | 1.00 | 42.05 | A | C |
| ATOM | 844 | CG | ASP | A | 343 | 24.172 | 8.156 | 0.235 | 1.00 | 47.50 | A | C |
| ATOM | 845 | OD1 | ASP | A | 343 | 23.590 | 7.455 | -0.643 | 1.00 | 50.57 | A | O |
| ATOM | 846 | OD2 | ASP | A | 343 | 24.753 | 7.617 | 1.211 | 1.00 | 50.46 | A | O |
| ATOM | 847 | C | ASP | A | 343 | 22.450 | 10.198 | 1.973 | 1.00 | 35.27 | A | C |
| ATOM | 848 | O | ASP | A | 343 | 21.961 | 9.162 | 2.417 | 1.00 | 34.96 | A | O |
| ATOM | 849 | N | MET | A | 344 | 22.648 | 11.289 | 2.731 | 1.00 | 32.31 | A | N |
| ATOM | 850 | CA | MET | A | 344 | 22.310 | 11.240 | 4.152 | 1.00 | 29.99 | A | C |
| ATOM | 851 | CB | MET | A | 344 | 22.750 | 12.492 | 4.948 | 1.00 | 30.21 | A | C |
| ATOM | 852 | CG | MET | A | 344 | 24.213 | 12.632 | 5.161 | 1.00 | 31.84 | A | C |
| ATOM | 853 | SD | MET | A | 344 | 24.688 | 14.165 | 6.058 | 1.00 | 35.05 | A | S |
| ATOM | 854 | CE | MET | A | 344 | 25.597 | 13.554 | 7.456 | 1.00 | 33.89 | A | C |
| ATOM | 855 | C | MET | A | 344 | 20.774 | 11.098 | 4.211 | 1.00 | 27.77 | A | C |
| ATOM | 856 | O | MET | A | 344 | 20.242 | 10.223 | 4.896 | 1.00 | 26.41 | A | O |
| ATOM | 857 | N | ALA | A | 345 | 20.083 | 11.956 | 3.465 | 1.00 | 25.31 | A | N |
| ATOM | 858 | CA | ALA | A | 345 | 18.626 | 11.964 | 3.401 | 1.00 | 23.67 | A | C |
| ATOM | 859 | CB | ALA | A | 345 | 18.187 | 12.925 | 2.317 | 1.00 | 23.36 | A | C |
| ATOM | 860 | C | ALA | A | 345 | 18.057 | 10.574 | 3.107 | 1.00 | 23.29 | A | C |
| ATOM | 861 | O | ALA | A | 345 | 17.076 | 10.171 | 3.707 | 1.00 | 22.88 | A | O |
| ATOM | 862 | N | ALA | A | 346 | 18.664 | 9.895 | 2.125 | 1.00 | 22.65 | A | N |
| ATOM | 863 | CA | ALA | A | 346 | 18.315 | 8.563 | 1.640 | 1.00 | 22.06 | A | C |
| ATOM | 864 | CB | ALA | A | 346 | 19.187 | 8.217 | 0.435 | 1.00 | 20.34 | A | C |
| ATOM | 865 | C | ALA | A | 346 | 18.477 | 7.494 | 2.700 | 1.00 | 22.91 | A | C |
| ATOM | 866 | O | ALA | A | 346 | 17.772 | 6.480 | 2.655 | 1.00 | 24.33 | A | O |
| ATOM | 867 | N | GLN | A | 347 | 19.436 | 7.695 | 3.608 | 1.00 | 23.78 | A | N |
| ATOM | 868 | CA | GLN | A | 347 | 19.748 | 6.769 | 4.702 | 1.00 | 23.29 | A | C |
| ATOM | 869 | CB | GLN | A | 347 | 21.078 | 7.138 | 5.393 | 1.00 | 24.46 | A | C |
| ATOM | 870 | CG | GLN | A | 347 | 22.396 | 6.859 | 4.652 | 1.00 | 24.65 | A | C |
| ATOM | 871 | CD | GLN | A | 347 | 23.587 | 7.266 | 5.477 | 1.00 | 23.57 | A | C |
| ATOM | 872 | OE1 | GLN | A | 347 | 24.370 | 6.443 | 5.918 | 1.00 | 23.19 | A | O |
| ATOM | 873 | NE2 | GLN | A | 347 | 23.741 | 8.547 | 5.668 | 1.00 | 24.14 | A | N |
| ATOM | 874 | C | GLN | A | 347 | 18.662 | 6.893 | 5.755 | 1.00 | 22.96 | A | C |
| ATOM | 875 | O | GLN | A | 347 | 18.298 | 5.901 | 6.392 | 1.00 | 24.09 | A | O |
| ATOM | 876 | N | ILE | A | 348 | 18.226 | 8.123 | 6.020 | 1.00 | 22.27 | A | N |
| ATOM | 877 | CA | ILE | A | 348 | 17.169 | 8.347 | 6.988 | 1.00 | 21.72 | A | C |
| ATOM | 878 | CB | ILE | A | 348 | 17.001 | 9.841 | 7.310 | 1.00 | 20.78 | A | C |
| ATOM | 879 | CG2 | ILE | A | 348 | 15.763 | 10.036 | 8.150 | 1.00 | 21.47 | A | C |
| ATOM | 880 | CG1 | ILE | A | 348 | 18.253 | 10.378 | 8.002 | 1.00 | 19.72 | A | C |
| ATOM | 881 | CD1 | ILE | A | 348 | 18.406 | 11.866 | 7.901 | 1.00 | 19.49 | A | C |
| ATOM | 882 | C | ILE | A | 348 | 15.874 | 7.785 | 6.407 | 1.00 | 21.82 | A | C |
| ATOM | 883 | O | ILE | A | 348 | 15.084 | 7.156 | 7.111 | 1.00 | 20.19 | A | O |
| ATOM | 884 | N | ALA | A | 349 | 15.686 | 8.009 | 5.110 | 1.00 | 22.37 | A | N |
| ATOM | 885 | CA | ALA | A | 349 | 14.518 | 7.514 | 4.371 | 1.00 | 23.53 | A | C |
| ATOM | 886 | CB | ALA | A | 349 | 14.621 | 7.955 | 2.931 | 1.00 | 22.52 | A | C |
| ATOM | 887 | C | ALA | A | 349 | 14.482 | 5.991 | 4.419 | 1.00 | 23.77 | A | C |

Figure 13

| | | | | | | | | | | | |
|---|---|---|---|---|---|---|---|---|---|---|---|
| ATOM | 888 | O | ALA | A | 349 | 13.419 | 5.384 | 4.336 | 1.00 | 24.58 | A | O |
| ATOM | 889 | N | GLU | A | 350 | 15.671 | 5.400 | 4.415 | 1.00 | 23.07 | A | N |
| ATOM | 890 | CA | GLU | A | 350 | 15.809 | 3.974 | 4.449 | 1.00 | 23.17 | A | C |
| ATOM | 891 | CB | GLU | A | 350 | 17.254 | 3.575 | 4.206 | 1.00 | 23.89 | A | C |
| ATOM | 892 | CG | GLU | A | 350 | 17.418 | 2.093 | 4.096 | 1.00 | 24.21 | A | C |
| ATOM | 893 | CD | GLU | A | 350 | 18.826 | 1.653 | 3.908 | 1.00 | 25.93 | A | C |
| ATOM | 894 | OE1 | GLU | A | 350 | 19.713 | 2.462 | 3.591 | 1.00 | 27.34 | A | O |
| ATOM | 895 | OE2 | GLU | A | 350 | 19.073 | 0.458 | 4.097 | 1.00 | 28.90 | A | O |
| ATOM | 896 | C | GLU | A | 350 | 15.347 | 3.451 | 5.790 | 1.00 | 23.43 | A | C |
| ATOM | 897 | O | GLU | A | 350 | 14.623 | 2.466 | 5.851 | 1.00 | 24.23 | A | O |
| ATOM | 898 | N | GLY | A | 351 | 15.768 | 4.126 | 6.857 | 1.00 | 23.09 | A | N |
| ATOM | 899 | CA | GLY | A | 351 | 15.418 | 3.705 | 8.205 | 1.00 | 22.77 | A | C |
| ATOM | 900 | C | GLY | A | 351 | 13.922 | 3.721 | 8.386 | 1.00 | 22.98 | A | C |
| ATOM | 901 | O | GLY | A | 351 | 13.331 | 2.749 | 8.864 | 1.00 | 23.36 | A | O |
| ATOM | 902 | N | MET | A | 352 | 13.324 | 4.816 | 7.935 | 1.00 | 23.48 | A | N |
| ATOM | 903 | CA | MET | A | 352 | 11.888 | 5.022 | 7.985 | 1.00 | 23.95 | A | C |
| ATOM | 904 | CB | MET | A | 352 | 11.522 | 6.423 | 7.538 | 1.00 | 22.63 | A | C |
| ATOM | 905 | CG | MET | A | 352 | 11.888 | 7.490 | 8.517 | 1.00 | 23.86 | A | C |
| ATOM | 906 | SD | MET | A | 352 | 11.339 | 7.174 | 10.225 | 1.00 | 23.49 | A | S |
| ATOM | 907 | CE | MET | A | 352 | 9.608 | 7.020 | 9.969 | 1.00 | 22.80 | A | C |
| ATOM | 908 | C | MET | A | 352 | 11.170 | 4.017 | 7.101 | 1.00 | 25.58 | A | C |
| ATOM | 909 | O | MET | A | 352 | 9.974 | 3.669 | 7.335 | 1.00 | 27.24 | A | O |
| ATOM | 910 | N | ALA | A | 353 | 11.853 | 3.612 | 6.038 | 1.00 | 24.64 | A | N |
| ATOM | 911 | CA | ALA | A | 353 | 11.254 | 2.625 | 5.154 | 1.00 | 25.49 | A | C |
| ATOM | 912 | CB | ALA | A | 353 | 12.081 | 2.448 | 3.904 | 1.00 | 25.02 | A | C |
| ATOM | 913 | C | ALA | A | 353 | 11.120 | 1.291 | 5.939 | 1.00 | 26.36 | A | C |
| ATOM | 914 | O | ALA | A | 353 | 10.161 | 0.525 | 5.781 | 1.00 | 26.58 | A | O |
| ATOM | 915 | N | PHE | A | 354 | 12.070 | 1.049 | 6.827 | 1.00 | 26.78 | A | N |
| ATOM | 916 | CA | PHE | A | 354 | 12.048 | -0.139 | 7.664 | 1.00 | 26.78 | A | C |
| ATOM | 917 | CB | PHE | A | 354 | 13.398 | -0.302 | 8.359 | 1.00 | 25.78 | A | C |
| ATOM | 918 | CG | PHE | A | 354 | 13.439 | -1.434 | 9.329 | 1.00 | 24.34 | A | C |
| ATOM | 919 | CD1 | PHE | A | 354 | 13.373 | -2.748 | 8.868 | 1.00 | 23.08 | A | C |
| ATOM | 920 | CD2 | PHE | A | 354 | 13.508 | -1.193 | 10.705 | 1.00 | 23.03 | A | C |
| ATOM | 921 | CE1 | PHE | A | 354 | 13.380 | -3.802 | 9.757 | 1.00 | 20.05 | A | C |
| ATOM | 922 | CE2 | PHE | A | 354 | 13.514 | -2.235 | 11.595 | 1.00 | 21.09 | A | C |
| ATOM | 923 | CZ | PHE | A | 354 | 13.450 | -3.544 | 11.123 | 1.00 | 20.72 | A | C |
| ATOM | 924 | C | PHE | A | 354 | 10.964 | 0.036 | 8.703 | 1.00 | 26.83 | A | C |
| ATOM | 925 | O | PHE | A | 354 | 10.196 | -0.858 | 8.968 | 1.00 | 27.26 | A | O |
| ATOM | 926 | N | ILE | A | 355 | 10.907 | 1.219 | 9.287 | 1.00 | 27.48 | A | N |
| ATOM | 927 | CA | ILE | A | 355 | 9.907 | 1.532 | 10.301 | 1.00 | 27.65 | A | C |
| ATOM | 928 | CB | ILE | A | 355 | 10.187 | 2.908 | 10.877 | 1.00 | 25.69 | A | C |
| ATOM | 929 | CG2 | ILE | A | 355 | 9.024 | 3.359 | 11.779 | 1.00 | 24.77 | A | C |
| ATOM | 930 | CG1 | ILE | A | 355 | 11.585 | 2.865 | 11.548 | 1.00 | 25.38 | A | C |
| ATOM | 931 | CD1 | ILE | A | 355 | 12.254 | 4.199 | 11.937 | 1.00 | 21.15 | A | C |
| ATOM | 932 | C | ILE | A | 355 | 8.497 | 1.470 | 9.713 | 1.00 | 29.24 | A | C |
| ATOM | 933 | O | ILE | A | 355 | 7.559 | 1.083 | 10.385 | 1.00 | 29.31 | A | O |
| ATOM | 934 | N | GLU | A | 356 | 8.357 | 1.842 | 8.448 | 1.00 | 31.08 | A | N |
| ATOM | 935 | CA | GLU | A | 356 | 7.072 | 1.821 | 7.786 | 1.00 | 32.48 | A | C |
| ATOM | 936 | CB | GLU | A | 356 | 7.198 | 2.512 | 6.468 | 1.00 | 32.63 | A | C |
| ATOM | 937 | CG | GLU | A | 356 | 5.932 | 2.609 | 5.627 | 1.00 | 32.87 | A | C |
| ATOM | 938 | CD | GLU | A | 356 | 6.263 | 3.242 | 4.275 | 1.00 | 34.64 | A | C |
| ATOM | 939 | OE1 | GLU | A | 356 | 6.958 | 2.557 | 3.460 | 1.00 | 35.57 | A | O |
| ATOM | 940 | OE2 | GLU | A | 356 | 6.013 | 4.472 | 4.104 | 1.00 | 35.10 | A | O |
| ATOM | 941 | C | GLU | A | 356 | 6.642 | 0.419 | 7.507 | 1.00 | 34.07 | A | C |
| ATOM | 942 | O | GLU | A | 356 | 5.470 | 0.106 | 7.631 | 1.00 | 35.49 | A | O |
| ATOM | 943 | N | GLU | A | 357 | 7.603 | -0.392 | 7.082 | 1.00 | 35.89 | A | N |
| ATOM | 944 | CA | GLU | A | 357 | 7.463 | -1.796 | 6.728 | 1.00 | 36.84 | A | C |
| ATOM | 945 | CB | GLU | A | 357 | 8.852 | -2.270 | 6.337 | 1.00 | 40.39 | A | C |
| ATOM | 946 | CG | GLU | A | 357 | 9.088 | -3.741 | 6.457 | 1.00 | 44.96 | A | C |
| ATOM | 947 | CD | GLU | A | 357 | 8.625 | -4.428 | 5.234 | 1.00 | 48.37 | A | C |

Figure 13

| | | | | | | | | | | |
|---|---|---|---|---|---|---|---|---|---|---|
| ATOM | 948 | OE1 | GLU | A | 357 | 9.106 | -3.995 | 4.157 | 1.00 50.06 | A | O |
| ATOM | 949 | OE2 | GLU | A | 357 | 7.781 | -5.356 | 5.331 | 1.00 51.64 | A | O |
| ATOM | 950 | C | GLU | A | 357 | 6.990 | -2.646 | 7.869 | 1.00 36.17 | A | C |
| ATOM | 951 | O | GLU | A | 357 | 6.222 | -3.593 | 7.671 | 1.00 35.93 | A | O |
| ATOM | 952 | N | ARG | A | 358 | 7.564 | -2.358 | 9.034 | 1.00 35.62 | A | N |
| ATOM | 953 | CA | ARG | A | 358 | 7.283 | -3.065 | 10.256 | 1.00 35.11 | A | C |
| ATOM | 954 | CB | ARG | A | 358 | 8.469 | -2.939 | 11.209 | 1.00 36.84 | A | C |
| ATOM | 955 | CG | ARG | A | 358 | 9.758 | -3.624 | 10.707 | 1.00 41.56 | A | C |
| ATOM | 956 | CD | ARG | A | 358 | 9.612 | -5.165 | 10.509 | 1.00 46.45 | A | C |
| ATOM | 957 | NE | ARG | A | 358 | 9.466 | -5.889 | 11.774 | 1.00 51.80 | A | N |
| ATOM | 958 | CZ | ARG | A | 358 | 10.356 | -5.844 | 12.764 | 1.00 55.09 | A | C |
| ATOM | 959 | NH1 | ARG | A | 358 | 11.460 | -5.129 | 12.640 | 1.00 57.98 | A | N |
| ATOM | 960 | NH2 | ARG | A | 358 | 10.103 | -6.421 | 13.926 | 1.00 57.33 | A | N |
| ATOM | 961 | C | ARG | A | 358 | 6.024 | -2.565 | 10.931 | 1.00 35.00 | A | C |
| ATOM | 962 | O | ARG | A | 358 | 5.664 | -3.067 | 11.986 | 1.00 36.14 | A | O |
| ATOM | 963 | N | ASN | A | 359 | 5.335 | -1.617 | 10.301 | 1.00 34.32 | A | N |
| ATOM | 964 | CA | ASN | A | 359 | 4.105 | -1.001 | 10.823 | 1.00 34.30 | A | C |
| ATOM | 965 | CB | ASN | A | 359 | 2.884 | -1.965 | 10.912 | 1.00 36.98 | A | C |
| ATOM | 966 | CG | ASN | A | 359 | 2.579 | -2.709 | 9.583 | 1.00 40.70 | A | C |
| ATOM | 967 | OD1 | ASN | A | 359 | 1.888 | -2.157 | 8.689 | 1.00 38.16 | A | O |
| ATOM | 968 | ND2 | ASN | A | 359 | 3.029 | -4.013 | 9.488 | 1.00 41.35 | A | N |
| ATOM | 969 | C | ASN | A | 359 | 4.287 | -0.244 | 12.148 | 1.00 32.76 | A | C |
| ATOM | 970 | O | ASN | A | 359 | 3.578 | -0.471 | 13.125 | 1.00 33.04 | A | O |
| ATOM | 971 | N | TYR | A | 360 | 5.317 | 0.582 | 12.197 | 1.00 30.99 | A | N |
| ATOM | 972 | CA | TYR | A | 360 | 5.539 | 1.461 | 13.344 | 1.00 30.28 | A | C |
| ATOM | 973 | CB | TYR | A | 360 | 6.952 | 1.311 | 13.907 | 1.00 30.05 | A | C |
| ATOM | 974 | CG | TYR | A | 360 | 7.127 | 0.194 | 14.870 | 1.00 30.59 | A | C |
| ATOM | 975 | CD1 | TYR | A | 360 | 7.346 | -1.104 | 14.413 | 1.00 31.62 | A | C |
| ATOM | 976 | CE1 | TYR | A | 360 | 7.515 | -2.151 | 15.283 | 1.00 31.37 | A | C |
| ATOM | 977 | CD2 | TYR | A | 360 | 7.082 | 0.418 | 16.244 | 1.00 31.03 | A | C |
| ATOM | 978 | CE2 | TYR | A | 360 | 7.256 | -0.636 | 17.140 | 1.00 32.15 | A | C |
| ATOM | 979 | CZ | TYR | A | 360 | 7.472 | -1.920 | 16.641 | 1.00 32.98 | A | C |
| ATOM | 980 | OH | TYR | A | 360 | 7.647 | -2.981 | 17.492 | 1.00 33.94 | A | O |
| ATOM | 981 | C | TYR | A | 360 | 5.436 | 2.886 | 12.756 | 1.00 28.92 | A | C |
| ATOM | 982 | O | TYR | A | 360 | 5.154 | 3.066 | 11.562 | 1.00 28.61 | A | O |
| ATOM | 983 | N | ILE | A | 361 | 5.563 | 3.877 | 13.630 | 1.00 27.81 | A | N |
| ATOM | 984 | CA | ILE | A | 361 | 5.603 | 5.288 | 13.261 | 1.00 27.11 | A | C |
| ATOM | 985 | CB | ILE | A | 361 | 4.280 | 6.059 | 13.498 | 1.00 25.54 | A | C |
| ATOM | 986 | CG2 | ILE | A | 361 | 3.182 | 5.472 | 12.661 | 1.00 25.02 | A | C |
| ATOM | 987 | CG1 | ILE | A | 361 | 3.910 | 6.139 | 14.988 | 1.00 25.62 | A | C |
| ATOM | 988 | CD1 | ILE | A | 361 | 2.800 | 7.195 | 15.252 | 1.00 23.99 | A | C |
| ATOM | 989 | C | ILE | A | 361 | 6.727 | 5.893 | 14.130 | 1.00 27.75 | A | C |
| ATOM | 990 | O | ILE | A | 361 | 7.176 | 5.281 | 15.105 | 1.00 28.31 | A | O |
| ATOM | 991 | N | HIS | A | 362 | 7.226 | 7.067 | 13.762 | 1.00 27.08 | A | N |
| ATOM | 992 | CA | HIS | A | 362 | 8.271 | 7.695 | 14.552 | 1.00 25.89 | A | C |
| ATOM | 993 | CB | HIS | A | 362 | 9.295 | 8.375 | 13.655 | 1.00 25.01 | A | C |
| ATOM | 994 | CG | HIS | A | 362 | 10.540 | 8.823 | 14.368 | 1.00 24.65 | A | C |
| ATOM | 995 | CD2 | HIS | A | 362 | 11.844 | 8.673 | 14.045 | 1.00 23.26 | A | C |
| ATOM | 996 | ND1 | HIS | A | 362 | 10.520 | 9.530 | 15.549 | 1.00 24.95 | A | N |
| ATOM | 997 | CE1 | HIS | A | 362 | 11.759 | 9.784 | 15.937 | 1.00 22.50 | A | C |
| ATOM | 998 | NE2 | HIS | A | 362 | 12.580 | 9.270 | 15.041 | 1.00 21.78 | A | N |
| ATOM | 999 | C | HIS | A | 362 | 7.613 | 8.709 | 15.466 | 1.00 26.53 | A | C |
| ATOM | 1000 | O | HIS | A | 362 | 7.711 | 8.590 | 16.678 | 1.00 27.08 | A | O |
| ATOM | 1001 | N | ARG | A | 363 | 6.827 | 9.598 | 14.863 | 1.00 26.74 | A | N |
| ATOM | 1002 | CA | ARG | A | 363 | 6.136 | 10.706 | 15.510 | 1.00 27.89 | A | C |
| ATOM | 1003 | CB | ARG | A | 363 | 5.065 | 10.276 | 16.528 | 1.00 31.86 | A | C |
| ATOM | 1004 | CG | ARG | A | 363 | 5.539 | 9.736 | 17.830 | 1.00 38.65 | A | C |
| ATOM | 1005 | CD | ARG | A | 363 | 4.391 | 9.106 | 18.640 | 1.00 45.04 | A | C |
| ATOM | 1006 | NE | ARG | A | 363 | 3.636 | 10.136 | 19.311 | 1.00 48.28 | A | N |
| ATOM | 1007 | CZ | ARG | A | 363 | 2.327 | 10.283 | 19.196 | 1.00 50.91 | A | C |

Figure 13

| ATOM | 1008 | NH1 | ARG A 363 | 1.620  | 9.442  | 18.446 | 1.00 50.64 | A | N |
| ATOM | 1009 | NH2 | ARG A 363 | 1.739  | 11.315 | 19.797 | 1.00 52.64 | A | N |
| ATOM | 1010 | C   | ARG A 363 | 7.059  | 11.830 | 16.013 | 1.00 26.74 | A | C |
| ATOM | 1011 | O   | ARG A 363 | 6.599  | 12.957 | 16.193 | 1.00 26.90 | A | O |
| ATOM | 1012 | N   | ASP A 364 | 8.370  | 11.549 | 16.087 | 1.00 24.68 | A | N |
| ATOM | 1013 | CA  | ASP A 364 | 9.367  | 12.526 | 16.489 | 1.00 22.74 | A | C |
| ATOM | 1014 | CB  | ASP A 364 | 9.949  | 12.222 | 17.869 | 1.00 23.37 | A | C |
| ATOM | 1015 | CG  | ASP A 364 | 8.966  | 12.527 | 18.985 | 1.00 25.17 | A | C |
| ATOM | 1016 | OD1 | ASP A 364 | 8.857  | 13.720 | 19.399 | 1.00 25.83 | A | O |
| ATOM | 1017 | OD2 | ASP A 364 | 8.244  | 11.583 | 19.411 | 1.00 27.85 | A | O |
| ATOM | 1018 | C   | ASP A 364 | 10.451 | 12.735 | 15.405 | 1.00 22.16 | A | C |
| ATOM | 1019 | O   | ASP A 364 | 11.619 | 13.045 | 15.679 | 1.00 22.47 | A | O |
| ATOM | 1020 | N   | LEU A 365 | 10.040 | 12.595 | 14.153 | 1.00 19.82 | A | N |
| ATOM | 1021 | CA  | LEU A 365 | 10.957 | 12.762 | 13.054 | 1.00 18.18 | A | C |
| ATOM | 1022 | CB  | LEU A 365 | 10.443 | 12.076 | 11.789 | 1.00 15.59 | A | C |
| ATOM | 1023 | CG  | LEU A 365 | 11.461 | 12.041 | 10.666 | 1.00 12.64 | A | C |
| ATOM | 1024 | CD1 | LEU A 365 | 12.701 | 11.299 | 11.086 | 1.00 12.47 | A | C |
| ATOM | 1025 | CD2 | LEU A 365 | 10.861 | 11.448 | 9.484  | 1.00 12.76 | A | C |
| ATOM | 1026 | C   | LEU A 365 | 11.342 | 14.195 | 12.754 | 1.00 19.64 | A | C |
| ATOM | 1027 | O   | LEU A 365 | 10.517 | 15.036 | 12.390 | 1.00 18.87 | A | O |
| ATOM | 1028 | N   | ARG A 366 | 12.617 | 14.475 | 13.006 | 1.00 22.12 | A | N |
| ATOM | 1029 | CA  | ARG A 366 | 13.238 | 15.764 | 12.728 | 1.00 23.68 | A | C |
| ATOM | 1030 | CB  | ARG A 366 | 12.783 | 16.870 | 13.699 | 1.00 24.69 | A | C |
| ATOM | 1031 | CG  | ARG A 366 | 13.109 | 16.719 | 15.171 | 1.00 27.35 | A | C |
| ATOM | 1032 | CD  | ARG A 366 | 12.815 | 18.030 | 15.937 | 1.00 28.44 | A | C |
| ATOM | 1033 | NE  | ARG A 366 | 12.491 | 17.766 | 17.339 | 1.00 31.06 | A | N |
| ATOM | 1034 | CZ  | ARG A 366 | 11.400 | 17.127 | 17.745 | 1.00 32.14 | A | C |
| ATOM | 1035 | NH1 | ARG A 366 | 10.501 | 16.664 | 16.860 | 1.00 32.35 | A | N |
| ATOM | 1036 | NH2 | ARG A 366 | 11.238 | 16.905 | 19.041 | 1.00 32.03 | A | N |
| ATOM | 1037 | C   | ARG A 366 | 14.742 | 15.575 | 12.722 | 1.00 24.22 | A | C |
| ATOM | 1038 | O   | ARG A 366 | 15.240 | 14.572 | 13.175 | 1.00 24.57 | A | O |
| ATOM | 1039 | N   | ALA A 367 | 15.478 | 16.518 | 12.170 | 1.00 25.47 | A | N |
| ATOM | 1040 | CA  | ALA A 367 | 16.893 | 16.348 | 12.134 | 1.00 26.37 | A | C |
| ATOM | 1041 | CB  | ALA A 367 | 17.517 | 17.388 | 11.266 | 1.00 25.94 | A | C |
| ATOM | 1042 | C   | ALA A 367 | 17.524 | 16.318 | 13.537 | 1.00 27.76 | A | C |
| ATOM | 1043 | O   | ALA A 367 | 18.629 | 15.781 | 13.681 | 1.00 28.72 | A | O |
| ATOM | 1044 | N   | ALA A 368 | 16.861 | 16.886 | 14.555 | 1.00 27.17 | A | N |
| ATOM | 1045 | CA  | ALA A 368 | 17.407 | 16.864 | 15.919 | 1.00 26.20 | A | C |
| ATOM | 1046 | CB  | ALA A 368 | 16.528 | 17.659 | 16.836 | 1.00 27.06 | A | C |
| ATOM | 1047 | C   | ALA A 368 | 17.543 | 15.450 | 16.458 | 1.00 26.56 | A | C |
| ATOM | 1048 | O   | ALA A 368 | 18.411 | 15.150 | 17.287 | 1.00 28.16 | A | O |
| ATOM | 1049 | N   | ASN A 369 | 16.662 | 14.581 | 15.988 | 1.00 25.94 | A | N |
| ATOM | 1050 | CA  | ASN A 369 | 16.609 | 13.201 | 16.419 | 1.00 24.40 | A | C |
| ATOM | 1051 | CB  | ASN A 369 | 15.164 | 12.834 | 16.713 | 1.00 24.28 | A | C |
| ATOM | 1052 | CG  | ASN A 369 | 14.550 | 13.733 | 17.766 | 1.00 24.11 | A | C |
| ATOM | 1053 | OD1 | ASN A 369 | 15.159 | 13.969 | 18.823 | 1.00 23.14 | A | O |
| ATOM | 1054 | ND2 | ASN A 369 | 13.339 | 14.252 | 17.483 | 1.00 23.25 | A | N |
| ATOM | 1055 | C   | ASN A 369 | 17.232 | 12.218 | 15.473 | 1.00 23.36 | A | C |
| ATOM | 1056 | O   | ASN A 369 | 16.794 | 11.099 | 15.412 | 1.00 24.46 | A | O |
| ATOM | 1057 | N   | ILE A 370 | 18.152 | 12.691 | 14.647 | 1.00 23.12 | A | N |
| ATOM | 1058 | CA  | ILE A 370 | 18.926 | 11.830 | 13.752 | 1.00 22.45 | A | C |
| ATOM | 1059 | CB  | ILE A 370 | 18.901 | 12.318 | 12.290 | 1.00 21.87 | A | C |
| ATOM | 1060 | CG2 | ILE A 370 | 20.000 | 11.598 | 11.447 | 1.00 18.85 | A | C |
| ATOM | 1061 | CG1 | ILE A 370 | 17.490 | 12.255 | 11.709 | 1.00 18.98 | A | C |
| ATOM | 1062 | CD1 | ILE A 370 | 16.874 | 10.897 | 11.773 | 1.00 20.58 | A | C |
| ATOM | 1063 | C   | ILE A 370 | 20.400 | 11.990 | 14.256 | 1.00 22.98 | A | C |
| ATOM | 1064 | O   | ILE A 370 | 20.830 | 13.103 | 14.590 | 1.00 21.58 | A | O |
| ATOM | 1065 | N   | LEU A 371 | 21.141 | 10.875 | 14.338 | 1.00 24.40 | A | N |
| ATOM | 1066 | CA  | LEU A 371 | 22.529 | 10.870 | 14.807 | 1.00 24.70 | A | C |
| ATOM | 1067 | CB  | LEU A 371 | 22.699 | 9.854  | 15.957 | 1.00 25.12 | A | C |

Figure 13

| | | | | | | | | | | | |
|---|---|---|---|---|---|---|---|---|---|---|---|
| ATOM | 1068 | CG | LEU | A | 371 | 21.929 | 10.105 | 17.263 | 1.00 | 23.93 | A | C |
| ATOM | 1069 | CD1 | LEU | A | 371 | 22.312 | 9.082 | 18.339 | 1.00 | 22.07 | A | C |
| ATOM | 1070 | CD2 | LEU | A | 371 | 22.217 | 11.498 | 17.773 | 1.00 | 23.74 | A | C |
| ATOM | 1071 | C | LEU | A | 371 | 23.523 | 10.597 | 13.678 | 1.00 | 24.70 | A | C |
| ATOM | 1072 | O | LEU | A | 371 | 23.231 | 9.823 | 12.775 | 1.00 | 24.13 | A | O |
| ATOM | 1073 | N | VAL | A | 372 | 24.686 | 11.241 | 13.741 | 1.00 | 24.86 | A | N |
| ATOM | 1074 | CA | VAL | A | 372 | 25.725 | 11.108 | 12.716 | 1.00 | 25.71 | A | C |
| ATOM | 1075 | CB | VAL | A | 372 | 26.083 | 12.500 | 12.078 | 1.00 | 26.49 | A | C |
| ATOM | 1076 | CG1 | VAL | A | 372 | 26.775 | 12.303 | 10.716 | 1.00 | 26.16 | A | C |
| ATOM | 1077 | CG2 | VAL | A | 372 | 24.809 | 13.355 | 11.900 | 1.00 | 25.26 | A | C |
| ATOM | 1078 | C | VAL | A | 372 | 27.001 | 10.435 | 13.223 | 1.00 | 26.52 | A | C |
| ATOM | 1079 | O | VAL | A | 372 | 27.541 | 10.789 | 14.282 | 1.00 | 26.44 | A | O |
| ATOM | 1080 | N | SER | A | 373 | 27.437 | 9.414 | 12.495 | 1.00 | 26.97 | A | N |
| ATOM | 1081 | CA | SER | A | 373 | 28.638 | 8.702 | 12.886 | 1.00 | 27.73 | A | C |
| ATOM | 1082 | CB | SER | A | 373 | 28.644 | 7.300 | 12.345 | 1.00 | 26.24 | A | C |
| ATOM | 1083 | OG | SER | A | 373 | 28.978 | 7.348 | 10.977 | 1.00 | 25.86 | A | O |
| ATOM | 1084 | C | SER | A | 373 | 29.880 | 9.381 | 12.374 | 1.00 | 28.99 | A | C |
| ATOM | 1085 | O | SER | A | 373 | 29.818 | 10.272 | 11.519 | 1.00 | 28.87 | A | O |
| ATOM | 1086 | N | ASP | A | 374 | 31.008 | 8.846 | 12.834 | 1.00 | 30.68 | A | N |
| ATOM | 1087 | CA | ASP | A | 374 | 32.325 | 9.329 | 12.453 | 1.00 | 31.99 | A | C |
| ATOM | 1088 | CB | ASP | A | 374 | 33.415 | 8.600 | 13.269 | 1.00 | 32.06 | A | C |
| ATOM | 1089 | CG | ASP | A | 374 | 33.303 | 7.076 | 13.203 | 1.00 | 32.42 | A | C |
| ATOM | 1090 | OD1 | ASP | A | 374 | 32.467 | 6.488 | 13.922 | 1.00 | 34.48 | A | O |
| ATOM | 1091 | OD2 | ASP | A | 374 | 34.099 | 6.471 | 12.463 | 1.00 | 33.17 | A | O |
| ATOM | 1092 | C | ASP | A | 374 | 32.533 | 9.217 | 10.924 | 1.00 | 32.97 | A | C |
| ATOM | 1093 | O | ASP | A | 374 | 33.181 | 10.067 | 10.327 | 1.00 | 32.11 | A | O |
| ATOM | 1094 | N | THR | A | 375 | 31.929 | 8.217 | 10.283 | 1.00 | 33.04 | A | N |
| ATOM | 1095 | CA | THR | A | 375 | 32.037 | 8.106 | 8.834 | 1.00 | 34.32 | A | C |
| ATOM | 1096 | CB | THR | A | 375 | 32.012 | 6.642 | 8.325 | 1.00 | 35.59 | A | C |
| ATOM | 1097 | OG1 | THR | A | 375 | 30.668 | 6.134 | 8.343 | 1.00 | 34.59 | A | O |
| ATOM | 1098 | CG2 | THR | A | 375 | 32.886 | 5.771 | 9.214 | 1.00 | 38.64 | A | C |
| ATOM | 1099 | C | THR | A | 375 | 30.877 | 8.860 | 8.174 | 1.00 | 34.70 | A | C |
| ATOM | 1100 | O | THR | A | 375 | 30.606 | 8.681 | 6.984 | 1.00 | 35.01 | A | O |
| ATOM | 1101 | N | LEU | A | 376 | 30.214 | 9.708 | 8.953 | 1.00 | 34.20 | A | N |
| ATOM | 1102 | CA | LEU | A | 376 | 29.111 | 10.523 | 8.483 | 1.00 | 34.66 | A | C |
| ATOM | 1103 | CB | LEU | A | 376 | 29.611 | 11.492 | 7.413 | 1.00 | 35.38 | A | C |
| ATOM | 1104 | CG | LEU | A | 376 | 30.825 | 12.381 | 7.748 | 1.00 | 36.25 | A | C |
| ATOM | 1105 | CD1 | LEU | A | 376 | 31.051 | 13.340 | 6.585 | 1.00 | 36.98 | A | C |
| ATOM | 1106 | CD2 | LEU | A | 376 | 30.622 | 13.145 | 9.067 | 1.00 | 36.06 | A | C |
| ATOM | 1107 | C | LEU | A | 376 | 27.831 | 9.820 | 8.022 | 1.00 | 35.18 | A | C |
| ATOM | 1108 | O | LEU | A | 376 | 27.019 | 10.399 | 7.297 | 1.00 | 35.11 | A | O |
| ATOM | 1109 | N | SER | A | 377 | 27.635 | 8.584 | 8.463 | 1.00 | 34.90 | A | N |
| ATOM | 1110 | CA | SER | A | 377 | 26.437 | 7.849 | 8.124 | 1.00 | 34.28 | A | C |
| ATOM | 1111 | CB | SER | A | 377 | 26.716 | 6.341 | 8.103 | 1.00 | 35.73 | A | C |
| ATOM | 1112 | OG | SER | A | 377 | 26.883 | 5.830 | 9.410 | 1.00 | 35.66 | A | O |
| ATOM | 1113 | C | SER | A | 377 | 25.382 | 8.194 | 9.188 | 1.00 | 34.00 | A | C |
| ATOM | 1114 | O | SER | A | 377 | 25.708 | 8.263 | 10.382 | 1.00 | 33.18 | A | O |
| ATOM | 1115 | N | CYS | A | 378 | 24.120 | 8.362 | 8.764 | 1.00 | 34.20 | A | N |
| ATOM | 1116 | CA | CYS | A | 378 | 23.017 | 8.739 | 9.662 | 1.00 | 32.90 | A | C |
| ATOM | 1117 | CB | CYS | A | 378 | 22.052 | 9.706 | 8.959 | 1.00 | 32.75 | A | C |
| ATOM | 1118 | SG | CYS | A | 378 | 22.777 | 11.135 | 8.185 | 1.00 | 33.19 | A | S |
| ATOM | 1119 | C | CYS | A | 378 | 22.202 | 7.548 | 10.137 | 1.00 | 32.17 | A | C |
| ATOM | 1120 | O | CYS | A | 378 | 21.846 | 6.669 | 9.338 | 1.00 | 33.84 | A | O |
| ATOM | 1121 | N | LYS | A | 379 | 21.802 | 7.620 | 11.405 | 1.00 | 30.96 | A | N |
| ATOM | 1122 | CA | LYS | A | 379 | 20.975 | 6.606 | 12.114 | 1.00 | 29.36 | A | C |
| ATOM | 1123 | CB | LYS | A | 379 | 21.837 | 5.830 | 13.139 | 1.00 | 29.66 | A | C |
| ATOM | 1124 | CG | LYS | A | 379 | 22.412 | 4.496 | 12.630 | 1.00 | 32.52 | A | C |
| ATOM | 1125 | CD | LYS | A | 379 | 23.838 | 4.244 | 13.136 | 1.00 | 36.02 | A | C |
| ATOM | 1126 | CE | LYS | A | 379 | 24.418 | 2.840 | 12.709 | 1.00 | 34.85 | A | C |
| ATOM | 1127 | NZ | LYS | A | 379 | 23.596 | 1.631 | 13.323 | 1.00 | 39.95 | A | N |

Figure 13

```
ATOM   1128  C    LYS A 379      19.808   7.360  12.843  1.00 27.82      A    C
ATOM   1129  O    LYS A 379      20.003   8.467  13.394  1.00 26.85      A    O
ATOM   1130  N    ILE A 380      18.614   6.770  12.819  1.00 25.33      A    N
ATOM   1131  CA   ILE A 380      17.397   7.330  13.433  1.00 24.31      A    C
ATOM   1132  CB   ILE A 380      16.114   6.761  12.779  1.00 23.89      A    C
ATOM   1133  CG2  ILE A 380      14.856   7.324  13.451  1.00 20.17      A    C
ATOM   1134  CG1  ILE A 380      16.158   7.026  11.275  1.00 24.47      A    C
ATOM   1135  CD1  ILE A 380      15.101   6.303  10.519  1.00 27.19      A    C
ATOM   1136  C    ILE A 380      17.289   6.973  14.886  1.00 24.18      A    C
ATOM   1137  O    ILE A 380      17.306   5.776  15.248  1.00 25.59      A    O
ATOM   1138  N    ALA A 381      17.102   7.986  15.723  1.00 23.83      A    N
ATOM   1139  CA   ALA A 381      16.948   7.721  17.154  1.00 23.94      A    C
ATOM   1140  CB   ALA A 381      17.933   8.496  18.005  1.00 23.72      A    C
ATOM   1141  C    ALA A 381      15.546   8.088  17.529  1.00 23.27      A    C
ATOM   1142  O    ALA A 381      14.757   8.497  16.666  1.00 22.59      A    O
ATOM   1143  N    ASP A 382      15.234   7.780  18.784  1.00 23.34      A    N
ATOM   1144  CA   ASP A 382      13.971   8.065  19.444  1.00 24.13      A    C
ATOM   1145  CB   ASP A 382      14.059   9.420  20.156  1.00 23.53      A    C
ATOM   1146  CG   ASP A 382      15.104   9.416  21.279  1.00 22.71      A    C
ATOM   1147  OD1  ASP A 382      15.226   8.368  21.966  1.00 22.69      A    O
ATOM   1148  OD2  ASP A 382      15.781  10.455  21.505  1.00 23.07      A    O
ATOM   1149  C    ASP A 382      12.675   7.891  18.676  1.00 25.52      A    C
ATOM   1150  O    ASP A 382      11.777   8.748  18.700  1.00 25.64      A    O
ATOM   1151  N    PHE A 383      12.579   6.731  18.041  1.00 26.67      A    N
ATOM   1152  CA   PHE A 383      11.412   6.371  17.254  1.00 29.99      A    C
ATOM   1153  CB   PHE A 383      11.844   5.586  16.024  1.00 30.83      A    C
ATOM   1154  CG   PHE A 383      12.608   4.373  16.345  1.00 33.80      A    C
ATOM   1155  CD1  PHE A 383      11.971   3.146  16.434  1.00 35.02      A    C
ATOM   1156  CD2  PHE A 383      13.967   4.462  16.604  1.00 36.25      A    C
ATOM   1157  CE1  PHE A 383      12.673   2.004  16.783  1.00 36.39      A    C
ATOM   1158  CE2  PHE A 383      14.705   3.323  16.961  1.00 38.05      A    C
ATOM   1159  CZ   PHE A 383      14.050   2.085  17.049  1.00 37.89      A    C
ATOM   1160  C    PHE A 383      10.382   5.555  18.063  1.00 30.84      A    C
ATOM   1161  O    PHE A 383      10.719   4.910  19.053  1.00 32.07      A    O
ATOM   1162  N    GLY A 384       9.123   5.602  17.646  1.00 30.77      A    N
ATOM   1163  CA   GLY A 384       8.099   4.828  18.318  1.00 30.88      A    C
ATOM   1164  C    GLY A 384       7.722   5.216  19.723  1.00 31.46      A    C
ATOM   1165  O    GLY A 384       6.997   4.458  20.343  1.00 32.58      A    O
ATOM   1166  N    LEU A 385       8.188   6.354  20.233  1.00 31.83      A    N
ATOM   1167  CA   LEU A 385       7.833   6.755  21.589  1.00 33.55      A    C
ATOM   1168  CB   LEU A 385       8.558   8.019  22.022  1.00 34.22      A    C
ATOM   1169  CG   LEU A 385      10.070   7.889  21.975  1.00 36.16      A    C
ATOM   1170  CD1  LEU A 385      10.713   9.126  22.552  1.00 34.67      A    C
ATOM   1171  CD2  LEU A 385      10.489   6.644  22.750  1.00 37.15      A    C
ATOM   1172  C    LEU A 385       6.358   7.021  21.673  1.00 35.72      A    C
ATOM   1173  O    LEU A 385       5.732   7.412  20.687  1.00 35.93      A    O
ATOM   1174  N    ALA A 386       5.785   6.788  22.850  1.00 37.61      A    N
ATOM   1175  CA   ALA A 386       4.360   7.029  22.999  1.00 39.42      A    C
ATOM   1176  CB   ALA A 386       3.797   6.214  24.141  1.00 40.52      A    C
ATOM   1177  C    ALA A 386       4.061   8.501  23.207  1.00 39.99      A    C
ATOM   1178  O    ALA A 386       2.913   8.905  23.136  1.00 41.51      A    O
ATOM   1179  N    ARG A 387       5.102   9.300  23.398  1.00 39.53      A    N
ATOM   1180  CA   ARG A 387       4.946  10.735  23.666  1.00 39.74      A    C
ATOM   1181  CB   ARG A 387       5.454  11.025  25.080  1.00 40.46      A    C
ATOM   1182  CG   ARG A 387       6.936  10.670  25.267  1.00 41.49      A    C
ATOM   1183  CD   ARG A 387       7.391  10.984  26.676  1.00 44.87      A    C
ATOM   1184  NE   ARG A 387       8.848  10.990  26.800  1.00 47.81      A    N
ATOM   1185  CZ   ARG A 387       9.647  12.056  26.657  1.00 49.72      A    C
ATOM   1186  NH1  ARG A 387       9.136  13.250  26.396  1.00 48.44      A    N
ATOM   1187  NH2  ARG A 387      10.983  11.899  26.712  1.00 51.39      A    N
```

Figure 13

| ATOM | 1188 | C | ARG | A | 387 | 5.715 | 11.631 | 22.697 | 1.00 | 39.31 | A | C |
| --- | --- | --- | --- | --- | --- | --- | --- | --- | --- | --- | --- | --- |
| ATOM | 1189 | O | ARG | A | 387 | 6.603 | 11.146 | 21.976 | 1.00 | 39.30 | A | O |
| ATOM | 1190 | N | LEU | A | 388 | 5.385 | 12.933 | 22.701 | 1.00 | 36.90 | A | N |
| ATOM | 1191 | CA | LEU | A | 388 | 6.084 | 13.898 | 21.849 | 1.00 | 34.92 | A | C |
| ATOM | 1192 | CB | LEU | A | 388 | 5.164 | 15.017 | 21.370 | 1.00 | 35.34 | A | C |
| ATOM | 1193 | CG | LEU | A | 388 | 3.924 | 14.461 | 20.671 | 1.00 | 36.82 | A | C |
| ATOM | 1194 | CD1 | LEU | A | 388 | 2.888 | 15.580 | 20.491 | 1.00 | 37.22 | A | C |
| ATOM | 1195 | CD2 | LEU | A | 388 | 4.286 | 13.827 | 19.331 | 1.00 | 37.85 | A | C |
| ATOM | 1196 | C | LEU | A | 388 | 7.232 | 14.474 | 22.639 | 1.00 | 33.11 | A | C |
| ATOM | 1197 | O | LEU | A | 388 | 7.021 | 15.048 | 23.699 | 1.00 | 31.91 | A | O |
| ATOM | 1198 | N | ILE | A | 389 | 8.451 | 14.278 | 22.134 | 1.00 | 31.69 | A | N |
| ATOM | 1199 | CA | ILE | A | 389 | 9.648 | 14.765 | 22.814 | 1.00 | 30.43 | A | C |
| ATOM | 1200 | CB | ILE | A | 389 | 10.833 | 13.796 | 22.671 | 1.00 | 28.78 | A | C |
| ATOM | 1201 | CG2 | ILE | A | 389 | 10.470 | 12.424 | 23.265 | 1.00 | 27.33 | A | C |
| ATOM | 1202 | CG1 | ILE | A | 389 | 11.263 | 13.707 | 21.210 | 1.00 | 28.35 | A | C |
| ATOM | 1203 | CD1 | ILE | A | 389 | 12.483 | 12.804 | 20.975 | 1.00 | 30.17 | A | C |
| ATOM | 1204 | C | ILE | A | 389 | 10.120 | 16.126 | 22.358 | 1.00 | 31.23 | A | C |
| ATOM | 1205 | O | ILE | A | 389 | 9.793 | 16.619 | 21.266 | 1.00 | 32.33 | A | O |
| ATOM | 1206 | N | GLU | A | 390 | 10.909 | 16.748 | 23.221 | 1.00 | 31.17 | A | N |
| ATOM | 1207 | CA | GLU | A | 390 | 11.457 | 18.047 | 22.905 | 1.00 | 31.03 | A | C |
| ATOM | 1208 | CB | GLU | A | 390 | 10.976 | 19.082 | 23.915 | 1.00 | 32.45 | A | C |
| ATOM | 1209 | CG | GLU | A | 390 | 9.498 | 19.130 | 24.076 | 1.00 | 32.78 | A | C |
| ATOM | 1210 | CD | GLU | A | 390 | 9.064 | 20.355 | 24.831 | 1.00 | 34.66 | A | C |
| ATOM | 1211 | OE1 | GLU | A | 390 | 7.849 | 20.620 | 24.912 | 1.00 | 39.79 | A | O |
| ATOM | 1212 | OE2 | GLU | A | 390 | 9.932 | 21.083 | 25.335 | 1.00 | 33.97 | A | O |
| ATOM | 1213 | C | GLU | A | 390 | 12.987 | 18.001 | 22.901 | 1.00 | 30.44 | A | C |
| ATOM | 1214 | O | GLU | A | 390 | 13.609 | 17.132 | 23.510 | 1.00 | 28.72 | A | O |
| ATOM | 1215 | N | ASP | A | 391 | 13.589 | 18.992 | 22.257 | 1.00 | 30.97 | A | N |
| ATOM | 1216 | CA | ASP | A | 391 | 15.046 | 19.047 | 22.194 | 1.00 | 32.32 | A | C |
| ATOM | 1217 | CB | ASP | A | 391 | 15.467 | 20.040 | 21.132 | 1.00 | 33.65 | A | C |
| ATOM | 1218 | CG | ASP | A | 391 | 14.997 | 19.626 | 19.763 | 1.00 | 37.42 | A | C |
| ATOM | 1219 | OD1 | ASP | A | 391 | 14.497 | 18.472 | 19.623 | 1.00 | 38.99 | A | O |
| ATOM | 1220 | OD2 | ASP | A | 391 | 15.156 | 20.437 | 18.827 | 1.00 | 38.55 | A | O |
| ATOM | 1221 | C | ASP | A | 391 | 15.775 | 19.347 | 23.484 | 1.00 | 32.02 | A | C |
| ATOM | 1222 | O | ASP | A | 391 | 16.842 | 18.804 | 23.714 | 1.00 | 31.92 | A | O |
| ATOM | 1223 | N | ASN | A | 392 | 15.163 | 20.182 | 24.320 | 1.00 | 32.63 | A | N |
| ATOM | 1224 | CA | ASN | A | 392 | 15.723 | 20.625 | 25.583 | 1.00 | 31.83 | A | C |
| ATOM | 1225 | CB | ASN | A | 392 | 14.981 | 21.912 | 25.982 | 1.00 | 31.58 | A | C |
| ATOM | 1226 | CG | ASN | A | 392 | 13.549 | 21.666 | 26.422 | 1.00 | 32.30 | A | C |
| ATOM | 1227 | OD1 | ASN | A | 392 | 12.938 | 20.629 | 26.143 | 1.00 | 31.00 | A | O |
| ATOM | 1228 | ND2 | ASN | A | 392 | 13.009 | 22.633 | 27.125 | 1.00 | 33.39 | A | N |
| ATOM | 1229 | C | ASN | A | 392 | 15.727 | 19.598 | 26.726 | 1.00 | 31.30 | A | C |
| ATOM | 1230 | O | ASN | A | 392 | 16.154 | 19.923 | 27.827 | 1.00 | 31.32 | A | O |
| ATOM | 1231 | N | GLU | A | 393 | 15.294 | 18.369 | 26.441 | 1.00 | 30.81 | A | N |
| ATOM | 1232 | CA | GLU | A | 393 | 15.209 | 17.290 | 27.433 | 1.00 | 32.06 | A | C |
| ATOM | 1233 | CB | GLU | A | 393 | 14.237 | 16.205 | 26.925 | 1.00 | 32.19 | A | C |
| ATOM | 1234 | CG | GLU | A | 393 | 12.776 | 16.733 | 26.791 | 1.00 | 31.25 | A | C |
| ATOM | 1235 | CD | GLU | A | 393 | 11.752 | 15.701 | 26.391 | 1.00 | 29.59 | A | C |
| ATOM | 1236 | OE1 | GLU | A | 393 | 12.117 | 14.533 | 26.156 | 1.00 | 29.56 | A | O |
| ATOM | 1237 | OE2 | GLU | A | 393 | 10.567 | 16.081 | 26.323 | 1.00 | 29.09 | A | O |
| ATOM | 1238 | C | GLU | A | 393 | 16.524 | 16.670 | 27.928 | 1.00 | 33.14 | A | C |
| ATOM | 1239 | O | GLU | A | 393 | 16.725 | 16.466 | 29.134 | 1.00 | 31.51 | A | O |
| ATOM | 1240 | N | TYR | A | 394 | 17.442 | 16.459 | 26.987 | 1.00 | 35.05 | A | N |
| ATOM | 1241 | CA | TYR | A | 394 | 18.748 | 15.901 | 27.284 | 1.00 | 37.35 | A | C |
| ATOM | 1242 | CB | TYR | A | 394 | 18.834 | 14.460 | 26.782 | 1.00 | 36.59 | A | C |
| ATOM | 1243 | CG | TYR | A | 394 | 17.748 | 13.591 | 27.382 | 1.00 | 36.53 | A | C |
| ATOM | 1244 | CD1 | TYR | A | 394 | 16.536 | 13.417 | 26.730 | 1.00 | 36.66 | A | C |
| ATOM | 1245 | CE1 | TYR | A | 394 | 15.491 | 12.698 | 27.308 | 1.00 | 37.05 | A | C |
| ATOM | 1246 | CD2 | TYR | A | 394 | 17.898 | 13.010 | 28.641 | 1.00 | 36.90 | A | C |
| ATOM | 1247 | CE2 | TYR | A | 394 | 16.849 | 12.277 | 29.247 | 1.00 | 37.43 | A | C |

Figure 13

| | | | | | | | | | | |
|---|---|---|---|---|---|---|---|---|---|---|
| ATOM | 1248 | CZ | TYR A 394 | 15.630 | 12.123 | 28.566 | 1.00 | 38.25 | A | C |
| ATOM | 1249 | OH | TYR A 394 | 14.549 | 11.408 | 29.126 | 1.00 | 38.93 | A | O |
| ATOM | 1250 | C | TYR A 394 | 19.912 | 16.785 | 26.782 | 1.00 | 39.36 | A | C |
| ATOM | 1251 | O | TYR A 394 | 21.079 | 16.444 | 26.938 | 1.00 | 39.73 | A | O |
| ATOM | 1252 | N | THR A 395 | 19.589 | 17.921 | 26.173 | 1.00 | 41.44 | A | N |
| ATOM | 1253 | CA | THR A 395 | 20.608 | 18.865 | 25.726 | 1.00 | 43.93 | A | C |
| ATOM | 1254 | CB | THR A 395 | 20.918 | 18.813 | 24.223 | 1.00 | 44.34 | A | C |
| ATOM | 1255 | OG1 | THR A 395 | 19.719 | 18.582 | 23.482 | 1.00 | 44.41 | A | O |
| ATOM | 1256 | CG2 | THR A 395 | 21.929 | 17.724 | 23.936 | 1.00 | 45.21 | A | C |
| ATOM | 1257 | C | THR A 395 | 20.104 | 20.221 | 26.058 | 1.00 | 46.21 | A | C |
| ATOM | 1258 | O | THR A 395 | 19.032 | 20.350 | 26.624 | 1.00 | 47.09 | A | O |
| ATOM | 1259 | N | ALA A 396 | 20.822 | 21.252 | 25.640 | 1.00 | 49.11 | A | N |
| ATOM | 1260 | CA | ALA A 396 | 20.400 | 22.591 | 26.000 | 1.00 | 51.44 | A | C |
| ATOM | 1261 | CB | ALA A 396 | 21.412 | 23.191 | 26.963 | 1.00 | 50.47 | A | C |
| ATOM | 1262 | C | ALA A 396 | 20.099 | 23.542 | 24.843 | 1.00 | 53.50 | A | C |
| ATOM | 1263 | O | ALA A 396 | 20.526 | 24.707 | 24.866 | 1.00 | 54.26 | A | O |
| ATOM | 1264 | N | ARG A 397 | 19.283 | 23.065 | 23.897 | 1.00 | 55.09 | A | N |
| ATOM | 1265 | CA | ARG A 397 | 18.879 | 23.822 | 22.712 | 1.00 | 56.56 | A | C |
| ATOM | 1266 | CB | ARG A 397 | 18.394 | 22.856 | 21.618 | 1.00 | 57.00 | A | C |
| ATOM | 1267 | CG | ARG A 397 | 19.472 | 21.890 | 21.115 | 1.00 | 58.18 | A | C |
| ATOM | 1268 | CD | ARG A 397 | 19.521 | 21.779 | 19.582 | 1.00 | 58.66 | A | C |
| ATOM | 1269 | NE | ARG A 397 | 20.341 | 20.642 | 19.174 | 1.00 | 59.24 | A | N |
| ATOM | 1270 | CZ | ARG A 397 | 19.940 | 19.380 | 19.286 | 1.00 | 59.68 | A | C |
| ATOM | 1271 | NH1 | ARG A 397 | 18.745 | 19.106 | 19.784 | 1.00 | 59.64 | A | N |
| ATOM | 1272 | NH2 | ARG A 397 | 20.709 | 18.393 | 18.858 | 1.00 | 59.94 | A | N |
| ATOM | 1273 | C | ARG A 397 | 17.827 | 24.923 | 22.953 | 1.00 | 57.41 | A | C |
| ATOM | 1274 | O | ARG A 397 | 18.013 | 26.070 | 22.445 | 1.00 | 58.57 | A | O |
| ATOM | 1275 | CB | PRO A 403 | 8.165 | 19.919 | 18.754 | 1.00 | 35.43 | A | C |
| ATOM | 1276 | CG | PRO A 403 | 8.640 | 20.517 | 20.079 | 1.00 | 35.73 | A | C |
| ATOM | 1277 | C | PRO A 403 | 6.781 | 21.030 | 16.947 | 1.00 | 35.19 | A | C |
| ATOM | 1278 | O | PRO A 403 | 6.632 | 20.013 | 16.232 | 1.00 | 34.75 | A | O |
| ATOM | 1279 | N | PRO A 403 | 7.527 | 22.255 | 18.971 | 1.00 | 35.30 | A | N |
| ATOM | 1280 | CD | PRO A 403 | 8.228 | 22.050 | 20.233 | 1.00 | 35.29 | A | C |
| ATOM | 1281 | CA | PRO A 403 | 7.911 | 21.184 | 17.971 | 1.00 | 35.81 | A | C |
| ATOM | 1282 | N | ILE A 404 | 6.085 | 22.147 | 16.793 | 1.00 | 34.55 | A | N |
| ATOM | 1283 | CA | ILE A 404 | 4.953 | 22.278 | 15.898 | 1.00 | 33.56 | A | C |
| ATOM | 1284 | CB | ILE A 404 | 4.155 | 23.493 | 16.237 | 1.00 | 34.63 | A | C |
| ATOM | 1285 | CG2 | ILE A 404 | 3.512 | 24.107 | 15.006 | 1.00 | 35.33 | A | C |
| ATOM | 1286 | CG1 | ILE A 404 | 3.110 | 23.110 | 17.218 | 1.00 | 35.93 | A | C |
| ATOM | 1287 | CD1 | ILE A 404 | 2.178 | 22.075 | 16.593 | 1.00 | 40.50 | A | C |
| ATOM | 1288 | C | ILE A 404 | 5.315 | 22.280 | 14.429 | 1.00 | 32.12 | A | C |
| ATOM | 1289 | O | ILE A 404 | 4.572 | 21.726 | 13.619 | 1.00 | 32.41 | A | O |
| ATOM | 1290 | N | LYS A 405 | 6.477 | 22.836 | 14.094 | 1.00 | 29.61 | A | N |
| ATOM | 1291 | CA | LYS A 405 | 6.962 | 22.940 | 12.713 | 1.00 | 28.89 | A | C |
| ATOM | 1292 | CB | LYS A 405 | 8.184 | 23.876 | 12.615 | 1.00 | 30.34 | A | C |
| ATOM | 1293 | CG | LYS A 405 | 7.855 | 25.342 | 12.792 | 1.00 | 31.61 | A | C |
| ATOM | 1294 | CD | LYS A 405 | 9.093 | 26.214 | 12.753 | 1.00 | 33.06 | A | C |
| ATOM | 1295 | CE | LYS A 405 | 8.690 | 27.639 | 13.108 | 1.00 | 36.50 | A | C |
| ATOM | 1296 | NZ | LYS A 405 | 9.523 | 28.679 | 12.459 | 1.00 | 37.22 | A | N |
| ATOM | 1297 | C | LYS A 405 | 7.251 | 21.661 | 11.967 | 1.00 | 27.19 | A | C |
| ATOM | 1298 | O | LYS A 405 | 7.712 | 21.726 | 10.836 | 1.00 | 27.40 | A | O |
| ATOM | 1299 | N | TRP A 406 | 7.140 | 20.500 | 12.601 | 1.00 | 25.06 | A | N |
| ATOM | 1300 | CA | TRP A 406 | 7.328 | 19.269 | 11.824 | 1.00 | 23.22 | A | C |
| ATOM | 1301 | CB | TRP A 406 | 8.449 | 18.387 | 12.322 | 1.00 | 22.48 | A | C |
| ATOM | 1302 | CG | TRP A 406 | 9.826 | 18.977 | 12.185 | 1.00 | 19.92 | A | C |
| ATOM | 1303 | CD2 | TRP A 406 | 10.415 | 19.954 | 13.052 | 1.00 | 18.33 | A | C |
| ATOM | 1304 | CE2 | TRP A 406 | 11.721 | 20.151 | 12.625 | 1.00 | 16.73 | A | C |
| ATOM | 1305 | CE3 | TRP A 406 | 9.960 | 20.657 | 14.176 | 1.00 | 18.02 | A | C |
| ATOM | 1306 | CD1 | TRP A 406 | 10.785 | 18.646 | 11.266 | 1.00 | 16.40 | A | C |
| ATOM | 1307 | NE1 | TRP A 406 | 11.922 | 19.352 | 11.532 | 1.00 | 17.92 | A | N |

Figure 13

| | | | | | | | | | | | |
|---|---|---|---|---|---|---|---|---|---|---|---|
| ATOM | 1308 | CZ2 | TRP | A | 406 | 12.563 | 21.029 | 13.260 | 1.00 | 17.61 | A | C |
| ATOM | 1309 | CZ3 | TRP | A | 406 | 10.810 | 21.533 | 14.796 | 1.00 | 16.16 | A | C |
| ATOM | 1310 | CH2 | TRP | A | 406 | 12.084 | 21.704 | 14.351 | 1.00 | 16.99 | A | C |
| ATOM | 1311 | C | TRP | A | 406 | 6.095 | 18.420 | 11.857 | 1.00 | 23.31 | A | C |
| ATOM | 1312 | O | TRP | A | 406 | 6.130 | 17.291 | 11.392 | 1.00 | 23.08 | A | O |
| ATOM | 1313 | N | THR | A | 407 | 5.023 | 18.936 | 12.466 | 1.00 | 23.11 | A | N |
| ATOM | 1314 | CA | THR | A | 407 | 3.764 | 18.196 | 12.578 | 1.00 | 22.54 | A | C |
| ATOM | 1315 | CB | THR | A | 407 | 2.957 | 18.506 | 13.877 | 1.00 | 22.53 | A | C |
| ATOM | 1316 | OG1 | THR | A | 407 | 3.829 | 18.649 | 14.992 | 1.00 | 24.74 | A | O |
| ATOM | 1317 | CG2 | THR | A | 407 | 2.051 | 17.375 | 14.217 | 1.00 | 23.52 | A | C |
| ATOM | 1318 | C | THR | A | 407 | 2.824 | 18.468 | 11.419 | 1.00 | 21.94 | A | C |
| ATOM | 1319 | O | THR | A | 407 | 2.502 | 19.606 | 11.097 | 1.00 | 21.80 | A | O |
| ATOM | 1320 | N | ALA | A | 408 | 2.307 | 17.390 | 10.856 | 1.00 | 21.19 | A | N |
| ATOM | 1321 | CA | ALA | A | 408 | 1.377 | 17.411 | 9.742 | 1.00 | 20.12 | A | C |
| ATOM | 1322 | CB | ALA | A | 408 | 1.106 | 15.964 | 9.320 | 1.00 | 21.24 | A | C |
| ATOM | 1323 | C | ALA | A | 408 | 0.088 | 18.020 | 10.226 | 1.00 | 18.83 | A | C |
| ATOM | 1324 | O | ALA | A | 408 | -0.283 | 17.863 | 11.378 | 1.00 | 18.15 | A | O |
| ATOM | 1325 | N | PRO | A | 409 | -0.642 | 18.658 | 9.317 | 1.00 | 18.93 | A | N |
| ATOM | 1326 | CD | PRO | A | 409 | -0.384 | 18.618 | 7.873 | 1.00 | 17.97 | A | C |
| ATOM | 1327 | CA | PRO | A | 409 | -1.936 | 19.305 | 9.646 | 1.00 | 19.59 | A | C |
| ATOM | 1328 | CB | PRO | A | 409 | -2.488 | 19.725 | 8.277 | 1.00 | 19.64 | A | C |
| ATOM | 1329 | CG | PRO | A | 409 | -1.257 | 19.711 | 7.375 | 1.00 | 19.73 | A | C |
| ATOM | 1330 | C | PRO | A | 409 | -2.973 | 18.449 | 10.394 | 1.00 | 20.52 | A | C |
| ATOM | 1331 | O | PRO | A | 409 | -3.602 | 18.933 | 11.331 | 1.00 | 20.96 | A | O |
| ATOM | 1332 | N | GLU | A | 410 | -3.160 | 17.196 | 9.960 | 1.00 | 20.28 | A | N |
| ATOM | 1333 | CA | GLU | A | 410 | -4.088 | 16.286 | 10.605 | 1.00 | 20.96 | A | C |
| ATOM | 1334 | CB | GLU | A | 410 | -4.255 | 14.957 | 9.843 | 1.00 | 22.57 | A | C |
| ATOM | 1335 | CG | GLU | A | 410 | -3.074 | 13.918 | 9.874 | 1.00 | 24.75 | A | C |
| ATOM | 1336 | CD | GLU | A | 410 | -2.071 | 14.201 | 8.774 | 1.00 | 26.44 | A | C |
| ATOM | 1337 | OE1 | GLU | A | 410 | -2.229 | 15.232 | 8.077 | 1.00 | 28.70 | A | O |
| ATOM | 1338 | OE2 | GLU | A | 410 | -1.118 | 13.420 | 8.601 | 1.00 | 25.83 | A | O |
| ATOM | 1339 | C | GLU | A | 410 | -3.665 | 15.962 | 12.030 | 1.00 | 21.73 | A | C |
| ATOM | 1340 | O | GLU | A | 410 | -4.504 | 15.801 | 12.896 | 1.00 | 22.38 | A | O |
| ATOM | 1341 | N | ALA | A | 411 | -2.365 | 15.877 | 12.270 | 1.00 | 22.32 | A | N |
| ATOM | 1342 | CA | ALA | A | 411 | -1.855 | 15.546 | 13.575 | 1.00 | 23.71 | A | C |
| ATOM | 1343 | CB | ALA | A | 411 | -0.401 | 15.212 | 13.468 | 1.00 | 24.04 | A | C |
| ATOM | 1344 | C | ALA | A | 411 | -2.064 | 16.708 | 14.524 | 1.00 | 25.28 | A | C |
| ATOM | 1345 | O | ALA | A | 411 | -2.248 | 16.510 | 15.720 | 1.00 | 25.63 | A | O |
| ATOM | 1346 | N | ILE | A | 412 | -1.963 | 17.926 | 13.988 | 1.00 | 27.37 | A | N |
| ATOM | 1347 | CA | ILE | A | 412 | -2.136 | 19.146 | 14.766 | 1.00 | 29.03 | A | C |
| ATOM | 1348 | CB | ILE | A | 412 | -1.676 | 20.367 | 13.975 | 1.00 | 28.48 | A | C |
| ATOM | 1349 | CG2 | ILE | A | 412 | -2.018 | 21.640 | 14.714 | 1.00 | 29.65 | A | C |
| ATOM | 1350 | CG1 | ILE | A | 412 | -0.178 | 20.355 | 13.726 | 1.00 | 28.61 | A | C |
| ATOM | 1351 | CD1 | ILE | A | 412 | 0.241 | 21.533 | 12.823 | 1.00 | 27.85 | A | C |
| ATOM | 1352 | C | ILE | A | 412 | -3.621 | 19.335 | 15.108 | 1.00 | 31.18 | A | C |
| ATOM | 1353 | O | ILE | A | 412 | -3.955 | 19.587 | 16.273 | 1.00 | 31.27 | A | O |
| ATOM | 1354 | N | ASN | A | 413 | -4.496 | 19.112 | 14.111 | 1.00 | 32.63 | A | N |
| ATOM | 1355 | CA | ASN | A | 413 | -5.939 | 19.317 | 14.247 | 1.00 | 33.97 | A | C |
| ATOM | 1356 | CB | ASN | A | 413 | -6.585 | 19.446 | 12.867 | 1.00 | 34.44 | A | C |
| ATOM | 1357 | CG | ASN | A | 413 | -6.302 | 20.770 | 12.221 | 1.00 | 36.34 | A | C |
| ATOM | 1358 | OD1 | ASN | A | 413 | -6.193 | 21.817 | 12.907 | 1.00 | 38.86 | A | O |
| ATOM | 1359 | ND2 | ASN | A | 413 | -6.142 | 20.752 | 10.906 | 1.00 | 34.86 | A | N |
| ATOM | 1360 | C | ASN | A | 413 | -6.758 | 18.328 | 15.004 | 1.00 | 34.87 | A | C |
| ATOM | 1361 | O | ASN | A | 413 | -7.816 | 18.652 | 15.563 | 1.00 | 34.90 | A | O |
| ATOM | 1362 | N | TYR | A | 414 | -6.373 | 17.077 | 14.845 | 1.00 | 36.01 | A | N |
| ATOM | 1363 | CA | TYR | A | 414 | -7.103 | 15.991 | 15.468 | 1.00 | 37.13 | A | C |
| ATOM | 1364 | CB | TYR | A | 414 | -7.859 | 15.233 | 14.391 | 1.00 | 38.35 | A | C |
| ATOM | 1365 | CG | TYR | A | 414 | -8.708 | 16.114 | 13.546 | 1.00 | 40.65 | A | C |
| ATOM | 1366 | CD1 | TYR | A | 414 | -9.930 | 16.581 | 14.022 | 1.00 | 42.43 | A | C |
| ATOM | 1367 | CE1 | TYR | A | 414 | -10.734 | 17.417 | 13.248 | 1.00 | 43.82 | A | C |

Figure 13

| ATOM | 1368 | CD2 | TYR | A | 414 | -8.296 | 16.500 | 12.266 | 1.00 | 41.67 | A | C |
| --- | --- | --- | --- | --- | --- | --- | --- | --- | --- | --- | --- | --- |
| ATOM | 1369 | CE2 | TYR | A | 414 | -9.096 | 17.346 | 11.475 | 1.00 | 42.96 | A | C |
| ATOM | 1370 | CZ | TYR | A | 414 | -10.311 | 17.796 | 11.979 | 1.00 | 43.92 | A | C |
| ATOM | 1371 | OH | TYR | A | 414 | -11.121 | 18.615 | 11.230 | 1.00 | 44.88 | A | O |
| ATOM | 1372 | C | TYR | A | 414 | -6.220 | 15.042 | 16.241 | 1.00 | 36.22 | A | C |
| ATOM | 1373 | O | TYR | A | 414 | -6.706 | 14.057 | 16.792 | 1.00 | 36.50 | A | O |
| ATOM | 1374 | N | GLY | A | 415 | -4.918 | 15.289 | 16.233 | 1.00 | 35.26 | A | N |
| ATOM | 1375 | CA | GLY | A | 415 | -4.050 | 14.388 | 16.970 | 1.00 | 33.55 | A | C |
| ATOM | 1376 | C | GLY | A | 415 | -3.789 | 13.034 | 16.312 | 1.00 | 32.91 | A | C |
| ATOM | 1377 | O | GLY | A | 415 | -3.204 | 12.161 | 16.952 | 1.00 | 33.79 | A | O |
| ATOM | 1378 | N | THR | A | 416 | -4.150 | 12.899 | 15.030 | 1.00 | 31.57 | A | N |
| ATOM | 1379 | CA | THR | A | 416 | -3.969 | 11.675 | 14.277 | 1.00 | 30.31 | A | C |
| ATOM | 1380 | CB | THR | A | 416 | -5.173 | 11.393 | 13.282 | 1.00 | 30.26 | A | C |
| ATOM | 1381 | OG1 | THR | A | 416 | -4.697 | 10.770 | 12.075 | 1.00 | 30.13 | A | O |
| ATOM | 1382 | CG2 | THR | A | 416 | -5.975 | 12.629 | 12.974 | 1.00 | 29.61 | A | C |
| ATOM | 1383 | C | THR | A | 416 | -2.575 | 11.574 | 13.644 | 1.00 | 28.91 | A | C |
| ATOM | 1384 | O | THR | A | 416 | -2.195 | 12.347 | 12.773 | 1.00 | 27.94 | A | O |
| ATOM | 1385 | N | PHE | A | 417 | -1.796 | 10.655 | 14.212 | 1.00 | 28.45 | A | N |
| ATOM | 1386 | CA | PHE | A | 417 | -0.411 | 10.356 | 13.845 | 1.00 | 27.52 | A | C |
| ATOM | 1387 | CB | PHE | A | 417 | 0.493 | 10.353 | 15.097 | 1.00 | 29.49 | A | C |
| ATOM | 1388 | CG | PHE | A | 417 | 0.767 | 11.720 | 15.677 | 1.00 | 31.69 | A | C |
| ATOM | 1389 | CD1 | PHE | A | 417 | -0.091 | 12.264 | 16.649 | 1.00 | 33.84 | A | C |
| ATOM | 1390 | CD2 | PHE | A | 417 | 1.877 | 12.476 | 15.247 | 1.00 | 31.07 | A | C |
| ATOM | 1391 | CE1 | PHE | A | 417 | 0.146 | 13.574 | 17.204 | 1.00 | 35.60 | A | C |
| ATOM | 1392 | CE2 | PHE | A | 417 | 2.137 | 13.770 | 15.772 | 1.00 | 31.80 | A | C |
| ATOM | 1393 | CZ | PHE | A | 417 | 1.272 | 14.335 | 16.754 | 1.00 | 33.63 | A | C |
| ATOM | 1394 | C | PHE | A | 417 | -0.310 | 8.975 | 13.193 | 1.00 | 25.96 | A | C |
| ATOM | 1395 | O | PHE | A | 417 | -0.641 | 7.947 | 13.798 | 1.00 | 26.06 | A | O |
| ATOM | 1396 | N | THR | A | 418 | 0.183 | 8.976 | 11.961 | 1.00 | 23.25 | A | N |
| ATOM | 1397 | CA | THR | A | 418 | 0.396 | 7.790 | 11.171 | 1.00 | 20.87 | A | C |
| ATOM | 1398 | CB | THR | A | 418 | -0.654 | 7.579 | 10.082 | 1.00 | 20.78 | A | C |
| ATOM | 1399 | OG1 | THR | A | 418 | -0.552 | 8.616 | 9.107 | 1.00 | 20.26 | A | O |
| ATOM | 1400 | CG2 | THR | A | 418 | -1.999 | 7.600 | 10.682 | 1.00 | 21.23 | A | C |
| ATOM | 1401 | C | THR | A | 418 | 1.729 | 7.980 | 10.505 | 1.00 | 19.90 | A | C |
| ATOM | 1402 | O | THR | A | 418 | 2.399 | 9.011 | 10.671 | 1.00 | 19.48 | A | O |
| ATOM | 1403 | N | ILE | A | 419 | 2.102 | 6.964 | 9.740 | 1.00 | 18.16 | A | N |
| ATOM | 1404 | CA | ILE | A | 419 | 3.356 | 6.945 | 9.048 | 1.00 | 17.06 | A | C |
| ATOM | 1405 | CB | ILE | A | 419 | 3.577 | 5.548 | 8.358 | 1.00 | 14.72 | A | C |
| ATOM | 1406 | CG2 | ILE | A | 419 | 2.608 | 5.403 | 7.160 | 1.00 | 14.03 | A | C |
| ATOM | 1407 | CG1 | ILE | A | 419 | 5.027 | 5.406 | 7.918 | 1.00 | 11.51 | A | C |
| ATOM | 1408 | CD1 | ILE | A | 419 | 5.979 | 5.664 | 9.017 | 1.00 | 10.59 | A | C |
| ATOM | 1409 | C | ILE | A | 419 | 3.319 | 8.114 | 8.042 | 1.00 | 16.36 | A | C |
| ATOM | 1410 | O | ILE | A | 419 | 4.323 | 8.754 | 7.769 | 1.00 | 17.11 | A | O |
| ATOM | 1411 | N | LYS | A | 420 | 2.119 | 8.465 | 7.626 | 1.00 | 16.68 | A | N |
| ATOM | 1412 | CA | LYS | A | 420 | 1.916 | 9.522 | 6.663 | 1.00 | 17.62 | A | C |
| ATOM | 1413 | CB | LYS | A | 420 | 0.480 | 9.472 | 6.151 | 1.00 | 17.44 | A | C |
| ATOM | 1414 | CG | LYS | A | 420 | 0.208 | 8.274 | 5.235 | 1.00 | 17.84 | A | C |
| ATOM | 1415 | CD | LYS | A | 420 | 1.188 | 8.252 | 4.052 | 1.00 | 17.85 | A | C |
| ATOM | 1416 | CE | LYS | A | 420 | 0.950 | 7.095 | 3.149 | 1.00 | 16.69 | A | C |
| ATOM | 1417 | NZ | LYS | A | 420 | 1.885 | 7.145 | 2.017 | 1.00 | 16.83 | A | N |
| ATOM | 1418 | C | LYS | A | 420 | 2.228 | 10.879 | 7.263 | 1.00 | 19.05 | A | C |
| ATOM | 1419 | O | LYS | A | 420 | 2.511 | 11.821 | 6.526 | 1.00 | 19.89 | A | O |
| ATOM | 1420 | N | SER | A | 421 | 2.092 | 10.999 | 8.586 | 1.00 | 20.43 | A | N |
| ATOM | 1421 | CA | SER | A | 421 | 2.406 | 12.234 | 9.238 | 1.00 | 21.96 | A | C |
| ATOM | 1422 | CB | SER | A | 421 | 1.470 | 12.565 | 10.444 | 1.00 | 22.17 | A | C |
| ATOM | 1423 | OG | SER | A | 421 | 1.270 | 11.549 | 11.398 | 1.00 | 20.98 | A | O |
| ATOM | 1424 | C | SER | A | 421 | 3.912 | 12.329 | 9.466 | 1.00 | 22.87 | A | C |
| ATOM | 1425 | O | SER | A | 421 | 4.472 | 13.414 | 9.560 | 1.00 | 23.25 | A | O |
| ATOM | 1426 | N | ASP | A | 422 | 4.587 | 11.189 | 9.397 | 1.00 | 24.64 | A | N |
| ATOM | 1427 | CA | ASP | A | 422 | 6.048 | 11.170 | 9.489 | 1.00 | 25.10 | A | C |

Figure 13

```
ATOM   1428  CB   ASP A 422       6.608   9.775   9.773  1.00 25.65           A    C
ATOM   1429  CG   ASP A 422       6.423   9.318  11.216  1.00 25.78           A    C
ATOM   1430  OD1  ASP A 422       6.143  10.152  12.132  1.00 25.02           A    O
ATOM   1431  OD2  ASP A 422       6.611   8.096  11.387  1.00 24.81           A    O
ATOM   1432  C    ASP A 422       6.544  11.518   8.096  1.00 25.20           A    C
ATOM   1433  O    ASP A 422       7.644  12.009   7.961  1.00 26.04           A    O
ATOM   1434  N    VAL A 423       5.810  11.134   7.055  1.00 25.01           A    N
ATOM   1435  CA   VAL A 423       6.278  11.462   5.721  1.00 24.83           A    C
ATOM   1436  CB   VAL A 423       5.401  10.903   4.583  1.00 25.57           A    C
ATOM   1437  CG1  VAL A 423       5.834  11.521   3.234  1.00 25.44           A    C
ATOM   1438  CG2  VAL A 423       5.540   9.372   4.494  1.00 23.68           A    C
ATOM   1439  C    VAL A 423       6.304  12.953   5.629  1.00 24.63           A    C
ATOM   1440  O    VAL A 423       7.265  13.523   5.095  1.00 25.74           A    O
ATOM   1441  N    TRP A 424       5.290  13.597   6.209  1.00 24.35           A    N
ATOM   1442  CA   TRP A 424       5.222  15.075   6.213  1.00 23.49           A    C
ATOM   1443  CB   TRP A 424       3.954  15.589   6.939  1.00 21.58           A    C
ATOM   1444  CG   TRP A 424       3.876  17.042   7.124  1.00 19.10           A    C
ATOM   1445  CD2  TRP A 424       3.050  17.962   6.401  1.00 19.11           A    C
ATOM   1446  CE2  TRP A 424       3.267  19.240   6.961  1.00 21.78           A    C
ATOM   1447  CE3  TRP A 424       2.124  17.827   5.364  1.00 19.52           A    C
ATOM   1448  CD1  TRP A 424       4.543  17.773   8.044  1.00 19.84           A    C
ATOM   1449  NE1  TRP A 424       4.196  19.102   7.959  1.00 19.63           A    N
ATOM   1450  CZ2  TRP A 424       2.584  20.401   6.497  1.00 19.75           A    C
ATOM   1451  CZ3  TRP A 424       1.440  18.968   4.911  1.00 18.71           A    C
ATOM   1452  CH2  TRP A 424       1.672  20.234   5.483  1.00 20.33           A    C
ATOM   1453  C    TRP A 424       6.491  15.503   6.949  1.00 24.48           A    C
ATOM   1454  O    TRP A 424       7.352  16.148   6.335  1.00 24.88           A    O
ATOM   1455  N    SER A 425       6.677  15.026   8.195  1.00 25.63           A    N
ATOM   1456  CA   SER A 425       7.897  15.370   8.986  1.00 26.28           A    C
ATOM   1457  CB   SER A 425       7.978  14.531  10.267  1.00 28.14           A    C
ATOM   1458  OG   SER A 425       7.085  15.008  11.265  1.00 29.82           A    O
ATOM   1459  C    SER A 425       9.206  15.163   8.188  1.00 25.11           A    C
ATOM   1460  O    SER A 425      10.152  15.898   8.370  1.00 25.75           A    O
ATOM   1461  N    PHE A 426       9.268  14.141   7.340  1.00 24.16           A    N
ATOM   1462  CA   PHE A 426      10.443  13.906   6.521  1.00 23.75           A    C
ATOM   1463  CB   PHE A 426      10.365  12.539   5.868  1.00 21.99           A    C
ATOM   1464  CG   PHE A 426      11.607  12.153   5.110  1.00 21.80           A    C
ATOM   1465  CD1  PHE A 426      12.794  11.812   5.781  1.00 20.48           A    C
ATOM   1466  CD2  PHE A 426      11.610  12.175   3.717  1.00 21.90           A    C
ATOM   1467  CE1  PHE A 426      13.947  11.509   5.081  1.00 19.16           A    C
ATOM   1468  CE2  PHE A 426      12.776  11.870   3.008  1.00 21.64           A    C
ATOM   1469  CZ   PHE A 426      13.946  11.540   3.697  1.00 19.84           A    C
ATOM   1470  C    PHE A 426      10.645  15.006   5.463  1.00 23.86           A    C
ATOM   1471  O    PHE A 426      11.790  15.367   5.139  1.00 23.85           A    O
ATOM   1472  N    GLY A 427       9.533  15.571   4.978  1.00 23.73           A    N
ATOM   1473  CA   GLY A 427       9.568  16.651   3.980  1.00 22.50           A    C
ATOM   1474  C    GLY A 427      10.188  17.898   4.601  1.00 21.92           A    C
ATOM   1475  O    GLY A 427      11.005  18.570   3.982  1.00 22.86           A    O
ATOM   1476  N    ILE A 428       9.775  18.200   5.836  1.00 21.71           A    N
ATOM   1477  CA   ILE A 428      10.261  19.338   6.624  1.00 19.33           A    C
ATOM   1478  CB   ILE A 428       9.472  19.478   7.983  1.00 18.72           A    C
ATOM   1479  CG2  ILE A 428      10.010  20.602   8.803  1.00 18.88           A    C
ATOM   1480  CG1  ILE A 428       7.981  19.679   7.750  1.00 16.60           A    C
ATOM   1481  CD1  ILE A 428       7.642  20.833   6.828  1.00 16.69           A    C
ATOM   1482  C    ILE A 428      11.724  19.015   6.942  1.00 17.80           A    C
ATOM   1483  O    ILE A 428      12.540  19.898   6.925  1.00 18.29           A    O
ATOM   1484  N    LEU A 429      12.054  17.749   7.202  1.00 17.89           A    N
ATOM   1485  CA   LEU A 429      13.437  17.384   7.502  1.00 17.49           A    C
ATOM   1486  CB   LEU A 429      13.510  15.942   7.990  1.00 15.11           A    C
ATOM   1487  CG   LEU A 429      14.751  15.448   8.745  1.00 14.04           A    C
```

Figure 13

| | | | | | | | | | | | |
|---|---|---|---|---|---|---|---|---|---|---|---|
| ATOM | 1488 | CD1 | LEU | A | 429 | 14.391 | 14.073 | 9.236 | 1.00 | 13.20 | A C |
| ATOM | 1489 | CD2 | LEU | A | 429 | 16.030 | 15.382 | 7.950 | 1.00 | 8.46 | A C |
| ATOM | 1490 | C | LEU | A | 429 | 14.409 | 17.596 | 6.315 | 1.00 | 18.25 | A C |
| ATOM | 1491 | O | LEU | A | 429 | 15.588 | 17.895 | 6.502 | 1.00 | 18.07 | A O |
| ATOM | 1492 | N | LEU | A | 430 | 13.912 | 17.389 | 5.109 | 1.00 | 18.36 | A N |
| ATOM | 1493 | CA | LEU | A | 430 | 14.709 | 17.572 | 3.925 | 1.00 | 19.06 | A C |
| ATOM | 1494 | CB | LEU | A | 430 | 13.976 | 17.081 | 2.683 | 1.00 | 18.67 | A C |
| ATOM | 1495 | CG | LEU | A | 430 | 13.742 | 15.587 | 2.373 | 1.00 | 19.42 | A C |
| ATOM | 1496 | CD1 | LEU | A | 430 | 12.773 | 15.464 | 1.176 | 1.00 | 14.54 | A C |
| ATOM | 1497 | CD2 | LEU | A | 430 | 15.092 | 14.863 | 2.100 | 1.00 | 15.53 | A C |
| ATOM | 1498 | C | LEU | A | 430 | 15.024 | 19.064 | 3.783 | 1.00 | 20.60 | A C |
| ATOM | 1499 | O | LEU | A | 430 | 16.050 | 19.411 | 3.184 | 1.00 | 21.03 | A O |
| ATOM | 1500 | N | THR | A | 431 | 14.182 | 19.961 | 4.320 | 1.00 | 20.91 | A N |
| ATOM | 1501 | CA | THR | A | 431 | 14.522 | 21.396 | 4.233 | 1.00 | 22.32 | A C |
| ATOM | 1502 | CB | THR | A | 431 | 13.359 | 22.398 | 4.465 | 1.00 | 19.97 | A C |
| ATOM | 1503 | OG1 | THR | A | 431 | 12.940 | 22.351 | 5.834 | 1.00 | 19.17 | A O |
| ATOM | 1504 | CG2 | THR | A | 431 | 12.219 | 22.175 | 3.478 | 1.00 | 16.27 | A C |
| ATOM | 1505 | C | THR | A | 431 | 15.638 | 21.717 | 5.227 | 1.00 | 24.32 | A C |
| ATOM | 1506 | O | THR | A | 431 | 16.409 | 22.634 | 4.980 | 1.00 | 25.84 | A O |
| ATOM | 1507 | N | GLU | A | 432 | 15.695 | 21.017 | 6.368 | 1.00 | 24.85 | A N |
| ATOM | 1508 | CA | GLU | A | 432 | 16.794 | 21.210 | 7.339 | 1.00 | 24.40 | A C |
| ATOM | 1509 | CB | GLU | A | 432 | 16.619 | 20.336 | 8.601 | 1.00 | 23.27 | A C |
| ATOM | 1510 | CG | GLU | A | 432 | 15.480 | 20.772 | 9.474 | 1.00 | 24.98 | A C |
| ATOM | 1511 | CD | GLU | A | 432 | 15.350 | 19.993 | 10.752 | 1.00 | 25.40 | A C |
| ATOM | 1512 | OE1 | GLU | A | 432 | 14.736 | 18.913 | 10.750 | 1.00 | 26.27 | A O |
| ATOM | 1513 | OE2 | GLU | A | 432 | 15.772 | 20.500 | 11.802 | 1.00 | 27.07 | A O |
| ATOM | 1514 | C | GLU | A | 432 | 18.074 | 20.732 | 6.660 | 1.00 | 25.33 | A C |
| ATOM | 1515 | O | GLU | A | 432 | 19.067 | 21.420 | 6.664 | 1.00 | 26.24 | A O |
| ATOM | 1516 | N | ILE | A | 433 | 18.012 | 19.536 | 6.088 | 1.00 | 25.46 | A N |
| ATOM | 1517 | CA | ILE | A | 433 | 19.152 | 18.938 | 5.458 | 1.00 | 25.69 | A C |
| ATOM | 1518 | CB | ILE | A | 433 | 18.826 | 17.547 | 4.849 | 1.00 | 24.96 | A C |
| ATOM | 1519 | CG2 | ILE | A | 433 | 19.920 | 17.158 | 3.856 | 1.00 | 24.31 | A C |
| ATOM | 1520 | CG1 | ILE | A | 433 | 18.774 | 16.470 | 5.962 | 1.00 | 25.02 | A C |
| ATOM | 1521 | CD1 | ILE | A | 433 | 18.670 | 15.026 | 5.461 | 1.00 | 21.59 | A C |
| ATOM | 1522 | C | ILE | A | 433 | 19.789 | 19.782 | 4.382 | 1.00 | 27.61 | A C |
| ATOM | 1523 | O | ILE | A | 433 | 21.006 | 19.766 | 4.267 | 1.00 | 29.87 | A O |
| ATOM | 1524 | N | VAL | A | 434 | 19.016 | 20.611 | 3.692 | 1.00 | 27.56 | A N |
| ATOM | 1525 | CA | VAL | A | 434 | 19.591 | 21.380 | 2.602 | 1.00 | 26.77 | A C |
| ATOM | 1526 | CB | VAL | A | 434 | 18.645 | 21.487 | 1.410 | 1.00 | 27.60 | A C |
| ATOM | 1527 | CG1 | VAL | A | 434 | 18.618 | 20.169 | 0.686 | 1.00 | 26.54 | A C |
| ATOM | 1528 | CG2 | VAL | A | 434 | 17.216 | 21.948 | 1.851 | 1.00 | 25.75 | A C |
| ATOM | 1529 | C | VAL | A | 434 | 20.023 | 22.755 | 2.951 | 1.00 | 27.82 | A C |
| ATOM | 1530 | O | VAL | A | 434 | 20.868 | 23.314 | 2.274 | 1.00 | 28.87 | A O |
| ATOM | 1531 | N | THR | A | 435 | 19.504 | 23.295 | 4.054 | 1.00 | 29.35 | A N |
| ATOM | 1532 | CA | THR | A | 435 | 19.829 | 24.645 | 4.424 | 1.00 | 30.99 | A C |
| ATOM | 1533 | CB | THR | A | 435 | 18.577 | 25.348 | 4.899 | 1.00 | 30.99 | A C |
| ATOM | 1534 | OG1 | THR | A | 435 | 18.037 | 24.613 | 5.999 | 1.00 | 32.27 | A O |
| ATOM | 1535 | CG2 | THR | A | 435 | 17.541 | 25.455 | 3.763 | 1.00 | 27.84 | A C |
| ATOM | 1536 | C | THR | A | 435 | 20.777 | 24.618 | 5.609 | 1.00 | 33.09 | A C |
| ATOM | 1537 | O | THR | A | 435 | 20.863 | 25.598 | 6.334 | 1.00 | 34.49 | A O |
| ATOM | 1538 | N | HIS | A | 436 | 21.408 | 23.472 | 5.836 | 1.00 | 35.43 | A N |
| ATOM | 1539 | CA | HIS | A | 436 | 22.351 | 23.281 | 6.920 | 1.00 | 37.91 | A C |
| ATOM | 1540 | CB | HIS | A | 436 | 23.558 | 24.153 | 6.664 | 1.00 | 42.00 | A C |
| ATOM | 1541 | CG | HIS | A | 436 | 24.185 | 23.907 | 5.333 | 1.00 | 46.29 | A C |
| ATOM | 1542 | CD2 | HIS | A | 436 | 24.697 | 24.767 | 4.422 | 1.00 | 48.78 | A C |
| ATOM | 1543 | ND1 | HIS | A | 436 | 24.342 | 22.642 | 4.803 | 1.00 | 47.46 | A N |
| ATOM | 1544 | CE1 | HIS | A | 436 | 24.933 | 22.734 | 3.623 | 1.00 | 48.79 | A C |
| ATOM | 1545 | NE2 | HIS | A | 436 | 25.154 | 24.013 | 3.370 | 1.00 | 51.17 | A N |
| ATOM | 1546 | C | HIS | A | 436 | 21.833 | 23.490 | 8.344 | 1.00 | 38.22 | A C |
| ATOM | 1547 | O | HIS | A | 436 | 22.516 | 24.095 | 9.183 | 1.00 | 38.40 | A O |

Figure 13

| | | | | | | | | | | | |
|---|---|---|---|---|---|---|---|---|---|---|---|
| ATOM | 1548 | N | GLY | A | 437 | 20.711 | 22.843 | 8.638 | 1.00 | 37.30 | A N |
| ATOM | 1549 | CA | GLY | A | 437 | 20.136 | 22.941 | 9.963 | 1.00 | 36.98 | A C |
| ATOM | 1550 | C | GLY | A | 437 | 19.385 | 24.197 | 10.275 | 1.00 | 36.91 | A C |
| ATOM | 1551 | O | GLY | A | 437 | 19.310 | 24.612 | 11.437 | 1.00 | 36.93 | A O |
| ATOM | 1552 | N | ARG | A | 438 | 18.919 | 24.848 | 9.221 | 1.00 | 36.85 | A N |
| ATOM | 1553 | CA | ARG | A | 438 | 18.146 | 26.058 | 9.380 | 1.00 | 37.29 | A C |
| ATOM | 1554 | CB | ARG | A | 438 | 17.992 | 26.738 | 8.031 | 1.00 | 39.53 | A C |
| ATOM | 1555 | CG | ARG | A | 438 | 17.632 | 28.205 | 8.101 | 1.00 | 43.53 | A C |
| ATOM | 1556 | CD | ARG | A | 438 | 16.136 | 28.361 | 8.218 | 1.00 | 47.24 | A C |
| ATOM | 1557 | NE | ARG | A | 438 | 15.401 | 27.765 | 7.092 | 1.00 | 48.54 | A N |
| ATOM | 1558 | CZ | ARG | A | 438 | 15.470 | 28.207 | 5.839 | 1.00 | 49.01 | A C |
| ATOM | 1559 | NH1 | ARG | A | 438 | 16.250 | 29.249 | 5.526 | 1.00 | 48.71 | A N |
| ATOM | 1560 | NH2 | ARG | A | 438 | 14.685 | 27.658 | 4.922 | 1.00 | 47.62 | A N |
| ATOM | 1561 | C | ARG | A | 438 | 16.779 | 25.646 | 9.897 | 1.00 | 36.55 | A C |
| ATOM | 1562 | O | ARG | A | 438 | 16.304 | 24.560 | 9.572 | 1.00 | 36.22 | A O |
| ATOM | 1563 | N | ILE | A | 439 | 16.180 | 26.478 | 10.756 | 1.00 | 35.94 | A N |
| ATOM | 1564 | CA | ILE | A | 439 | 14.853 | 26.198 | 11.319 | 1.00 | 34.58 | A C |
| ATOM | 1565 | CB | ILE | A | 439 | 14.499 | 27.111 | 12.561 | 1.00 | 35.59 | A C |
| ATOM | 1566 | CG2 | ILE | A | 439 | 13.057 | 26.949 | 12.940 | 1.00 | 35.94 | A C |
| ATOM | 1567 | CG1 | ILE | A | 439 | 15.289 | 26.661 | 13.801 | 1.00 | 38.32 | A C |
| ATOM | 1568 | CD1 | ILE | A | 439 | 15.386 | 27.737 | 14.929 | 1.00 | 39.32 | A C |
| ATOM | 1569 | C | ILE | A | 439 | 13.782 | 26.345 | 10.261 | 1.00 | 32.41 | A C |
| ATOM | 1570 | O | ILE | A | 439 | 13.795 | 27.291 | 9.484 | 1.00 | 31.80 | A O |
| ATOM | 1571 | N | PRO | A | 440 | 12.863 | 25.368 | 10.189 | 1.00 | 30.46 | A N |
| ATOM | 1572 | CD | PRO | A | 440 | 12.810 | 24.183 | 11.059 | 1.00 | 29.50 | A C |
| ATOM | 1573 | CA | PRO | A | 440 | 11.755 | 25.364 | 9.229 | 1.00 | 29.42 | A C |
| ATOM | 1574 | CB | PRO | A | 440 | 10.957 | 24.124 | 9.653 | 1.00 | 30.95 | A C |
| ATOM | 1575 | CG | PRO | A | 440 | 12.005 | 23.222 | 10.241 | 1.00 | 30.77 | A C |
| ATOM | 1576 | C | PRO | A | 440 | 10.915 | 26.627 | 9.408 | 1.00 | 28.42 | A C |
| ATOM | 1577 | O | PRO | A | 440 | 10.823 | 27.154 | 10.515 | 1.00 | 28.20 | A O |
| ATOM | 1578 | N | TYR | A | 441 | 10.276 | 27.094 | 8.335 | 1.00 | 27.00 | A N |
| ATOM | 1579 | CA | TYR | A | 441 | 9.442 | 28.317 | 8.363 | 1.00 | 26.60 | A C |
| ATOM | 1580 | CB | TYR | A | 441 | 8.092 | 28.081 | 9.049 | 1.00 | 24.87 | A C |
| ATOM | 1581 | CG | TYR | A | 441 | 7.340 | 26.894 | 8.518 | 1.00 | 23.84 | A C |
| ATOM | 1582 | CD1 | TYR | A | 441 | 6.381 | 27.027 | 7.495 | 1.00 | 22.39 | A C |
| ATOM | 1583 | CE1 | TYR | A | 441 | 5.673 | 25.909 | 7.051 | 1.00 | 21.71 | A C |
| ATOM | 1584 | CD2 | TYR | A | 441 | 7.567 | 25.614 | 9.064 | 1.00 | 23.30 | A C |
| ATOM | 1585 | CE2 | TYR | A | 441 | 6.861 | 24.499 | 8.628 | 1.00 | 22.71 | A C |
| ATOM | 1586 | CZ | TYR | A | 441 | 5.924 | 24.665 | 7.632 | 1.00 | 21.82 | A C |
| ATOM | 1587 | OH | TYR | A | 441 | 5.264 | 23.578 | 7.222 | 1.00 | 20.84 | A O |
| ATOM | 1588 | C | TYR | A | 441 | 10.145 | 29.440 | 9.078 | 1.00 | 26.40 | A C |
| ATOM | 1589 | O | TYR | A | 441 | 9.683 | 29.918 | 10.117 | 1.00 | 26.78 | A O |
| ATOM | 1590 | N | PRO | A | 442 | 11.288 | 29.867 | 8.540 | 1.00 | 26.70 | A N |
| ATOM | 1591 | CD | PRO | A | 442 | 11.988 | 29.393 | 7.337 | 1.00 | 25.35 | A C |
| ATOM | 1592 | CA | PRO | A | 442 | 12.004 | 30.950 | 9.203 | 1.00 | 27.69 | A C |
| ATOM | 1593 | CB | PRO | A | 442 | 13.305 | 31.012 | 8.414 | 1.00 | 27.23 | A C |
| ATOM | 1594 | CG | PRO | A | 442 | 12.891 | 30.495 | 7.041 | 1.00 | 26.31 | A C |
| ATOM | 1595 | C | PRO | A | 442 | 11.198 | 32.251 | 9.212 | 1.00 | 29.25 | A C |
| ATOM | 1596 | O | PRO | A | 442 | 10.575 | 32.627 | 8.217 | 1.00 | 29.77 | A O |
| ATOM | 1597 | N | GLY | A | 443 | 11.194 | 32.916 | 10.358 | 1.00 | 30.11 | A N |
| ATOM | 1598 | CA | GLY | A | 443 | 10.441 | 34.136 | 10.481 | 1.00 | 31.53 | A C |
| ATOM | 1599 | C | GLY | A | 443 | 8.995 | 33.913 | 10.854 | 1.00 | 32.93 | A C |
| ATOM | 1600 | O | GLY | A | 443 | 8.163 | 34.829 | 10.740 | 1.00 | 35.45 | A O |
| ATOM | 1601 | N | MET | A | 444 | 8.674 | 32.682 | 11.218 | 1.00 | 32.59 | A N |
| ATOM | 1602 | CA | MET | A | 444 | 7.317 | 32.328 | 11.660 | 1.00 | 33.07 | A C |
| ATOM | 1603 | CB | MET | A | 444 | 6.652 | 31.276 | 10.735 | 1.00 | 32.96 | A C |
| ATOM | 1604 | CG | MET | A | 444 | 5.854 | 31.937 | 9.642 | 1.00 | 33.78 | A C |
| ATOM | 1605 | SD | MET | A | 444 | 5.261 | 31.035 | 8.264 | 1.00 | 31.11 | A S |
| ATOM | 1606 | CE | MET | A | 444 | 3.980 | 30.345 | 9.051 | 1.00 | 29.95 | A C |
| ATOM | 1607 | C | MET | A | 444 | 7.428 | 31.802 | 13.071 | 1.00 | 33.10 | A C |

Figure 13

| ATOM | 1608 | O   | MET A 444 | 8.495  | 31.357 | 13.465 | 1.00 | 32.84 | A | O |
|------|------|-----|-----------|--------|--------|--------|------|-------|---|---|
| ATOM | 1609 | N   | THR A 445 | 6.407  | 32.022 | 13.882 | 1.00 | 32.79 | A | N |
| ATOM | 1610 | CA  | THR A 445 | 6.416  | 31.469 | 15.236 | 1.00 | 33.68 | A | C |
| ATOM | 1611 | CB  | THR A 445 | 5.850  | 32.452 | 16.281 | 1.00 | 33.63 | A | C |
| ATOM | 1612 | OG1 | THR A 445 | 4.490  | 32.753 | 15.958 | 1.00 | 34.91 | A | O |
| ATOM | 1613 | CG2 | THR A 445 | 6.650  | 33.716 | 16.323 | 1.00 | 32.89 | A | C |
| ATOM | 1614 | C   | THR A 445 | 5.456  | 30.286 | 15.134 | 1.00 | 33.91 | A | C |
| ATOM | 1615 | O   | THR A 445 | 4.745  | 30.160 | 14.137 | 1.00 | 34.30 | A | O |
| ATOM | 1616 | N   | ASN A 446 | 5.398  | 29.449 | 16.161 | 1.00 | 33.29 | A | N |
| ATOM | 1617 | CA  | ASN A 446 | 4.496  | 28.288 | 16.154 | 1.00 | 33.35 | A | C |
| ATOM | 1618 | CB  | ASN A 446 | 4.552  | 27.525 | 17.486 | 1.00 | 32.70 | A | C |
| ATOM | 1619 | CG  | ASN A 446 | 5.737  | 26.587 | 17.571 | 1.00 | 31.66 | A | C |
| ATOM | 1620 | OD1 | ASN A 446 | 6.688  | 26.683 | 16.817 | 1.00 | 30.06 | A | O |
| ATOM | 1621 | ND2 | ASN A 446 | 5.687  | 25.692 | 18.515 | 1.00 | 31.44 | A | N |
| ATOM | 1622 | C   | ASN A 446 | 3.052  | 28.637 | 15.807 | 1.00 | 32.96 | A | C |
| ATOM | 1623 | O   | ASN A 446 | 2.452  | 27.972 | 14.966 | 1.00 | 33.62 | A | O |
| ATOM | 1624 | N   | PRO A 447 | 2.448  | 29.634 | 16.498 | 1.00 | 32.62 | A | N |
| ATOM | 1625 | CD  | PRO A 447 | 2.891  | 30.370 | 17.690 | 1.00 | 31.78 | A | C |
| ATOM | 1626 | CA  | PRO A 447 | 1.070  | 30.003 | 16.185 | 1.00 | 31.66 | A | C |
| ATOM | 1627 | CB  | PRO A 447 | 0.759  | 31.057 | 17.250 | 1.00 | 31.74 | A | C |
| ATOM | 1628 | CG  | PRO A 447 | 2.093  | 31.585 | 17.602 | 1.00 | 33.21 | A | C |
| ATOM | 1629 | C   | PRO A 447 | 0.917  | 30.515 | 14.757 | 1.00 | 30.73 | A | C |
| ATOM | 1630 | O   | PRO A 447 | -0.149 | 30.367 | 14.155 | 1.00 | 31.11 | A | O |
| ATOM | 1631 | N   | GLU A 448 | 1.972  | 31.106 | 14.210 | 1.00 | 28.72 | A | N |
| ATOM | 1632 | CA  | GLU A 448 | 1.927  | 31.592 | 12.834 | 1.00 | 28.57 | A | C |
| ATOM | 1633 | CB  | GLU A 448 | 3.086  | 32.572 | 12.546 | 1.00 | 30.99 | A | C |
| ATOM | 1634 | CG  | GLU A 448 | 2.879  | 33.962 | 13.170 | 1.00 | 33.06 | A | C |
| ATOM | 1635 | CD  | GLU A 448 | 4.154  | 34.832 | 13.282 | 1.00 | 36.08 | A | C |
| ATOM | 1636 | OE1 | GLU A 448 | 5.271  | 34.401 | 12.903 | 1.00 | 36.67 | A | O |
| ATOM | 1637 | OE2 | GLU A 448 | 4.026  | 35.981 | 13.766 | 1.00 | 38.01 | A | O |
| ATOM | 1638 | C   | GLU A 448 | 1.926  | 30.438 | 11.834 | 1.00 | 26.75 | A | C |
| ATOM | 1639 | O   | GLU A 448 | 1.340  | 30.536 | 10.759 | 1.00 | 26.20 | A | O |
| ATOM | 1640 | N   | VAL A 449 | 2.635  | 29.363 | 12.174 | 1.00 | 25.55 | A | N |
| ATOM | 1641 | CA  | VAL A 449 | 2.710  | 28.173 | 11.312 | 1.00 | 24.36 | A | C |
| ATOM | 1642 | CB  | VAL A 449 | 3.765  | 27.142 | 11.802 | 1.00 | 23.81 | A | C |
| ATOM | 1643 | CG1 | VAL A 449 | 3.768  | 25.889 | 10.935 | 1.00 | 20.94 | A | C |
| ATOM | 1644 | CG2 | VAL A 449 | 5.149  | 27.766 | 11.790 | 1.00 | 24.68 | A | C |
| ATOM | 1645 | C   | VAL A 449 | 1.357  | 27.527 | 11.251 | 1.00 | 24.60 | A | C |
| ATOM | 1646 | O   | VAL A 449 | 0.922  | 27.078 | 10.183 | 1.00 | 24.94 | A | O |
| ATOM | 1647 | N   | ILE A 450 | 0.685  | 27.527 | 12.399 | 1.00 | 24.86 | A | N |
| ATOM | 1648 | CA  | ILE A 450 | -0.649 | 26.980 | 12.517 | 1.00 | 25.23 | A | C |
| ATOM | 1649 | CB  | ILE A 450 | -1.175 | 26.992 | 13.932 | 1.00 | 25.00 | A | C |
| ATOM | 1650 | CG2 | ILE A 450 | -2.426 | 26.156 | 14.004 | 1.00 | 23.89 | A | C |
| ATOM | 1651 | CG1 | ILE A 450 | -0.178 | 26.351 | 14.851 | 1.00 | 24.40 | A | C |
| ATOM | 1652 | CD1 | ILE A 450 | -0.096 | 24.910 | 14.644 | 1.00 | 27.73 | A | C |
| ATOM | 1653 | C   | ILE A 450 | -1.629 | 27.766 | 11.687 | 1.00 | 26.12 | A | C |
| ATOM | 1654 | O   | ILE A 450 | -2.401 | 27.150 | 10.965 | 1.00 | 26.42 | A | O |
| ATOM | 1655 | N   | GLN A 451 | -1.604 | 29.109 | 11.763 | 1.00 | 26.73 | A | N |
| ATOM | 1656 | CA  | GLN A 451 | -2.559 | 29.865 | 10.971 | 1.00 | 27.94 | A | C |
| ATOM | 1657 | CB  | GLN A 451 | -2.843 | 31.272 | 11.504 | 1.00 | 31.34 | A | C |
| ATOM | 1658 | CG  | GLN A 451 | -1.679 | 32.210 | 11.637 | 1.00 | 37.43 | A | C |
| ATOM | 1659 | CD  | GLN A 451 | -1.896 | 33.204 | 12.752 | 1.00 | 40.52 | A | C |
| ATOM | 1660 | OE1 | GLN A 451 | -1.591 | 34.401 | 12.623 | 1.00 | 43.57 | A | O |
| ATOM | 1661 | NE2 | GLN A 451 | -2.379 | 32.704 | 13.883 | 1.00 | 39.95 | A | N |
| ATOM | 1662 | C   | GLN A 451 | -2.237 | 29.841 | 9.509  | 1.00 | 25.95 | A | C |
| ATOM | 1663 | O   | GLN A 451 | -3.148 | 29.874 | 8.703  | 1.00 | 26.55 | A | O |
| ATOM | 1664 | N   | ASN A 452 | -0.970 | 29.642 | 9.166  | 1.00 | 25.09 | A | N |
| ATOM | 1665 | CA  | ASN A 452 | -0.585 | 29.538 | 7.768  | 1.00 | 24.50 | A | C |
| ATOM | 1666 | CB  | ASN A 452 | 0.910  | 29.765 | 7.610  | 1.00 | 25.64 | A | C |
| ATOM | 1667 | CG  | ASN A 452 | 1.235  | 31.202 | 7.302  | 1.00 | 27.64 | A | C |

Figure 13

| | | | | | | | | | | | |
|---|---|---|---|---|---|---|---|---|---|---|---|
| ATOM | 1668 | OD1 | ASN | A | 452 | 1.371 | 31.574 | 6.143 | 1.00 | 29.21 | A | O |
| ATOM | 1669 | ND2 | ASN | A | 452 | 1.325 | 32.028 | 8.333 | 1.00 | 26.10 | A | N |
| ATOM | 1670 | C | ASN | A | 452 | -0.996 | 28.164 | 7.215 | 1.00 | 23.74 | A | C |
| ATOM | 1671 | O | ASN | A | 452 | -1.540 | 28.078 | 6.124 | 1.00 | 22.38 | A | O |
| ATOM | 1672 | N | LEU | A | 453 | -0.766 | 27.098 | 7.987 | 1.00 | 25.07 | A | N |
| ATOM | 1673 | CA | LEU | A | 453 | -1.165 | 25.767 | 7.552 | 1.00 | 25.34 | A | C |
| ATOM | 1674 | CB | LEU | A | 453 | -0.664 | 24.693 | 8.485 | 1.00 | 24.08 | A | C |
| ATOM | 1675 | CG | LEU | A | 453 | 0.853 | 24.458 | 8.398 | 1.00 | 24.10 | A | C |
| ATOM | 1676 | CD1 | LEU | A | 453 | 1.201 | 23.408 | 9.399 | 1.00 | 21.55 | A | C |
| ATOM | 1677 | CD2 | LEU | A | 453 | 1.332 | 24.079 | 6.991 | 1.00 | 22.94 | A | C |
| ATOM | 1678 | C | LEU | A | 453 | -2.675 | 25.703 | 7.356 | 1.00 | 26.47 | A | C |
| ATOM | 1679 | O | LEU | A | 453 | -3.096 | 25.082 | 6.357 | 1.00 | 27.18 | A | O |
| ATOM | 1680 | N | GLU | A | 454 | -3.462 | 26.447 | 8.171 | 1.00 | 26.84 | A | N |
| ATOM | 1681 | CA | GLU | A | 454 | -4.929 | 26.455 | 8.032 | 1.00 | 28.29 | A | C |
| ATOM | 1682 | CB | GLU | A | 454 | -5.656 | 27.362 | 9.047 | 1.00 | 32.35 | A | C |
| ATOM | 1683 | CG | GLU | A | 454 | -5.678 | 27.005 | 10.575 | 1.00 | 39.47 | A | C |
| ATOM | 1684 | CD | GLU | A | 454 | -5.840 | 28.262 | 11.502 | 1.00 | 43.78 | A | C |
| ATOM | 1685 | OE1 | GLU | A | 454 | -5.455 | 28.196 | 12.698 | 1.00 | 45.61 | A | O |
| ATOM | 1686 | OE2 | GLU | A | 454 | -6.323 | 29.320 | 11.029 | 1.00 | 46.03 | A | O |
| ATOM | 1687 | C | GLU | A | 454 | -5.247 | 27.017 | 6.646 | 1.00 | 27.23 | A | C |
| ATOM | 1688 | O | GLU | A | 454 | -6.208 | 26.586 | 6.044 | 1.00 | 27.03 | A | O |
| ATOM | 1689 | N | ARG | A | 455 | -4.431 | 27.960 | 6.137 | 1.00 | 26.72 | A | N |
| ATOM | 1690 | CA | ARG | A | 455 | -4.630 | 28.588 | 4.815 | 1.00 | 25.68 | A | C |
| ATOM | 1691 | CB | ARG | A | 455 | -4.167 | 30.075 | 4.813 | 1.00 | 27.59 | A | C |
| ATOM | 1692 | CG | ARG | A | 455 | -4.775 | 31.051 | 5.870 | 1.00 | 31.15 | A | C |
| ATOM | 1693 | CD | ARG | A | 455 | -4.255 | 32.524 | 5.725 | 1.00 | 35.34 | A | C |
| ATOM | 1694 | NE | ARG | A | 455 | -2.816 | 32.526 | 5.430 | 1.00 | 42.36 | A | N |
| ATOM | 1695 | CZ | ARG | A | 455 | -2.247 | 32.841 | 4.249 | 1.00 | 45.49 | A | C |
| ATOM | 1696 | NH1 | ARG | A | 455 | -2.983 | 33.238 | 3.205 | 1.00 | 46.79 | A | N |
| ATOM | 1697 | NH2 | ARG | A | 455 | -0.982 | 32.481 | 4.013 | 1.00 | 45.82 | A | N |
| ATOM | 1698 | C | ARG | A | 455 | -3.906 | 27.837 | 3.684 | 1.00 | 23.40 | A | C |
| ATOM | 1699 | O | ARG | A | 455 | -3.911 | 28.301 | 2.556 | 1.00 | 23.12 | A | O |
| ATOM | 1700 | N | GLY | A | 456 | -3.307 | 26.681 | 3.986 | 1.00 | 22.49 | A | N |
| ATOM | 1701 | CA | GLY | A | 456 | -2.605 | 25.859 | 2.999 | 1.00 | 19.03 | A | C |
| ATOM | 1702 | C | GLY | A | 456 | -1.185 | 26.263 | 2.668 | 1.00 | 18.57 | A | C |
| ATOM | 1703 | O | GLY | A | 456 | -0.663 | 25.891 | 1.631 | 1.00 | 18.55 | A | O |
| ATOM | 1704 | N | TYR | A | 457 | -0.556 | 27.005 | 3.552 | 1.00 | 18.08 | A | N |
| ATOM | 1705 | CA | TYR | A | 457 | 0.777 | 27.471 | 3.280 | 1.00 | 19.95 | A | C |
| ATOM | 1706 | CB | TYR | A | 457 | 1.170 | 28.552 | 4.297 | 1.00 | 19.86 | A | C |
| ATOM | 1707 | CG | TYR | A | 457 | 2.568 | 29.124 | 4.132 | 1.00 | 19.61 | A | C |
| ATOM | 1708 | CD1 | TYR | A | 457 | 2.797 | 30.336 | 3.445 | 1.00 | 19.68 | A | C |
| ATOM | 1709 | CE1 | TYR | A | 457 | 4.095 | 30.849 | 3.275 | 1.00 | 17.82 | A | C |
| ATOM | 1710 | CD2 | TYR | A | 457 | 3.673 | 28.450 | 4.647 | 1.00 | 21.21 | A | C |
| ATOM | 1711 | CE2 | TYR | A | 457 | 4.971 | 28.958 | 4.485 | 1.00 | 21.51 | A | C |
| ATOM | 1712 | CZ | TYR | A | 457 | 5.174 | 30.135 | 3.808 | 1.00 | 20.05 | A | C |
| ATOM | 1713 | OH | TYR | A | 457 | 6.498 | 30.494 | 3.688 | 1.00 | 22.61 | A | O |
| ATOM | 1714 | C | TYR | A | 457 | 1.862 | 26.415 | 3.128 | 1.00 | 21.33 | A | C |
| ATOM | 1715 | O | TYR | A | 457 | 1.849 | 25.404 | 3.836 | 1.00 | 24.31 | A | O |
| ATOM | 1716 | N | ARG | A | 458 | 2.712 | 26.589 | 2.114 | 1.00 | 20.64 | A | N |
| ATOM | 1717 | CA | ARG | A | 458 | 3.844 | 25.699 | 1.880 | 1.00 | 20.60 | A | C |
| ATOM | 1718 | CB | ARG | A | 458 | 3.643 | 24.850 | 0.632 | 1.00 | 20.92 | A | C |
| ATOM | 1719 | CG | ARG | A | 458 | 2.458 | 23.909 | 0.737 | 1.00 | 21.24 | A | C |
| ATOM | 1720 | CD | ARG | A | 458 | 2.575 | 23.013 | 1.982 | 1.00 | 21.32 | A | C |
| ATOM | 1721 | NE | ARG | A | 458 | 1.553 | 21.969 | 1.983 | 1.00 | 20.58 | A | N |
| ATOM | 1722 | CZ | ARG | A | 458 | 0.506 | 21.977 | 2.794 | 1.00 | 19.55 | A | C |
| ATOM | 1723 | NH1 | ARG | A | 458 | 0.373 | 22.954 | 3.650 | 1.00 | 20.05 | A | N |
| ATOM | 1724 | NH2 | ARG | A | 458 | -0.418 | 21.047 | 2.718 | 1.00 | 19.77 | A | N |
| ATOM | 1725 | C | ARG | A | 458 | 5.077 | 26.558 | 1.719 | 1.00 | 20.99 | A | C |
| ATOM | 1726 | O | ARG | A | 458 | 5.043 | 27.633 | 1.095 | 1.00 | 19.75 | A | O |
| ATOM | 1727 | N | MET | A | 459 | 6.163 | 26.103 | 2.334 | 1.00 | 21.54 | A | N |

Figure 13

| ATOM | 1728 | CA | MET A 459 | 7.434 | 26.806 | 2.236 | 1.00 | 21.19 | A | C |
|---|---|---|---|---|---|---|---|---|---|---|
| ATOM | 1729 | CB | MET A 459 | 8.494 | 26.174 | 3.120 | 1.00 | 22.59 | A | C |
| ATOM | 1730 | CG | MET A 459 | 8.322 | 26.318 | 4.625 | 1.00 | 23.70 | A | C |
| ATOM | 1731 | SD | MET A 459 | 9.862 | 25.692 | 5.372 | 1.00 | 27.52 | A | S |
| ATOM | 1732 | CE | MET A 459 | 9.470 | 24.020 | 5.598 | 1.00 | 24.48 | A | C |
| ATOM | 1733 | C | MET A 459 | 7.896 | 26.702 | 0.799 | 1.00 | 20.21 | A | C |
| ATOM | 1734 | O | MET A 459 | 7.651 | 25.712 | 0.116 | 1.00 | 17.58 | A | O |
| ATOM | 1735 | N | VAL A 460 | 8.527 | 27.775 | 0.357 | 1.00 | 20.98 | A | N |
| ATOM | 1736 | CA | VAL A 460 | 9.067 | 27.925 | -0.991 | 1.00 | 21.43 | A | C |
| ATOM | 1737 | CB | VAL A 460 | 9.463 | 29.398 | -1.223 | 1.00 | 19.37 | A | C |
| ATOM | 1738 | CG1 | VAL A 460 | 8.297 | 30.281 | -0.982 | 1.00 | 16.97 | A | C |
| ATOM | 1739 | CG2 | VAL A 460 | 10.551 | 29.790 | -0.291 | 1.00 | 17.42 | A | C |
| ATOM | 1740 | C | VAL A 460 | 10.314 | 27.042 | -1.130 | 1.00 | 23.06 | A | C |
| ATOM | 1741 | O | VAL A 460 | 10.787 | 26.479 | -0.143 | 1.00 | 23.02 | A | O |
| ATOM | 1742 | N | ARG A 461 | 10.848 | 26.938 | -2.338 | 1.00 | 25.26 | A | N |
| ATOM | 1743 | CA | ARG A 461 | 12.068 | 26.163 | -2.542 | 1.00 | 28.75 | A | C |
| ATOM | 1744 | CB | ARG A 461 | 12.392 | 26.019 | -4.032 | 1.00 | 30.07 | A | C |
| ATOM | 1745 | CG | ARG A 461 | 13.480 | 25.031 | -4.397 | 1.00 | 31.89 | A | C |
| ATOM | 1746 | CD | ARG A 461 | 13.751 | 25.042 | -5.898 | 1.00 | 34.59 | A | C |
| ATOM | 1747 | NE | ARG A 461 | 14.142 | 26.393 | -6.307 | 1.00 | 39.30 | A | N |
| ATOM | 1748 | CZ | ARG A 461 | 15.312 | 26.972 | -6.001 | 1.00 | 41.64 | A | C |
| ATOM | 1749 | NH1 | ARG A 461 | 16.249 | 26.316 | -5.304 | 1.00 | 41.77 | A | N |
| ATOM | 1750 | NH2 | ARG A 461 | 15.493 | 28.264 | -6.255 | 1.00 | 40.87 | A | N |
| ATOM | 1751 | C | ARG A 461 | 13.196 | 26.915 | -1.811 | 1.00 | 30.69 | A | C |
| ATOM | 1752 | O | ARG A 461 | 13.312 | 28.150 | -1.871 | 1.00 | 30.50 | A | O |
| ATOM | 1753 | N | PRO A 462 | 13.919 | 26.192 | -0.955 | 1.00 | 33.03 | A | N |
| ATOM | 1754 | CD | PRO A 462 | 13.590 | 24.837 | -0.472 | 1.00 | 32.03 | A | C |
| ATOM | 1755 | CA | PRO A 462 | 15.028 | 26.762 | -0.180 | 1.00 | 34.54 | A | C |
| ATOM | 1756 | CB | PRO A 462 | 15.402 | 25.604 | 0.755 | 1.00 | 32.71 | A | C |
| ATOM | 1757 | CG | PRO A 462 | 14.114 | 24.868 | 0.923 | 1.00 | 31.70 | A | C |
| ATOM | 1758 | C | PRO A 462 | 16.223 | 27.134 | -1.058 | 1.00 | 35.92 | A | C |
| ATOM | 1759 | O | PRO A 462 | 16.408 | 26.539 | -2.125 | 1.00 | 36.57 | A | O |
| ATOM | 1760 | N | ASP A 463 | 17.016 | 28.122 | -0.631 | 1.00 | 37.21 | A | N |
| ATOM | 1761 | CA | ASP A 463 | 18.203 | 28.470 | -1.401 | 1.00 | 38.71 | A | C |
| ATOM | 1762 | CB | ASP A 463 | 18.966 | 29.666 | -0.803 | 1.00 | 40.11 | A | C |
| ATOM | 1763 | CG | ASP A 463 | 18.229 | 30.996 | -0.949 | 1.00 | 42.06 | A | C |
| ATOM | 1764 | OD1 | ASP A 463 | 17.393 | 31.190 | -1.858 | 1.00 | 42.79 | A | O |
| ATOM | 1765 | OD2 | ASP A 463 | 18.515 | 31.891 | -0.140 | 1.00 | 44.26 | A | O |
| ATOM | 1766 | C | ASP A 463 | 19.137 | 27.255 | -1.444 | 1.00 | 39.10 | A | C |
| ATOM | 1767 | O | ASP A 463 | 19.504 | 26.701 | -0.398 | 1.00 | 38.71 | A | O |
| ATOM | 1768 | N | ASN A 464 | 19.535 | 26.890 | -2.663 | 1.00 | 39.90 | A | N |
| ATOM | 1769 | CA | ASN A 464 | 20.439 | 25.778 | -2.955 | 1.00 | 41.37 | A | C |
| ATOM | 1770 | CB | ASN A 464 | 21.818 | 26.000 | -2.305 | 1.00 | 45.18 | A | C |
| ATOM | 1771 | CG | ASN A 464 | 22.508 | 27.320 | -2.818 | 1.00 | 48.63 | A | C |
| ATOM | 1772 | OD1 | ASN A 464 | 22.781 | 27.482 | -4.029 | 1.00 | 48.85 | A | O |
| ATOM | 1773 | ND2 | ASN A 464 | 22.762 | 28.259 | -1.898 | 1.00 | 48.59 | A | N |
| ATOM | 1774 | C | ASN A 464 | 19.853 | 24.401 | -2.676 | 1.00 | 41.49 | A | C |
| ATOM | 1775 | O | ASN A 464 | 20.472 | 23.537 | -2.046 | 1.00 | 41.72 | A | O |
| ATOM | 1776 | N | CYS A 465 | 18.699 | 24.196 | -3.313 | 1.00 | 40.09 | A | N |
| ATOM | 1777 | CA | CYS A 465 | 17.886 | 22.991 | -3.242 | 1.00 | 37.14 | A | C |
| ATOM | 1778 | CB | CYS A 465 | 16.618 | 23.258 | -2.388 | 1.00 | 36.73 | A | C |
| ATOM | 1779 | SG | CYS A 465 | 15.389 | 21.936 | -2.464 | 1.00 | 35.47 | A | S |
| ATOM | 1780 | C | CYS A 465 | 17.458 | 22.704 | -4.667 | 1.00 | 35.21 | A | C |
| ATOM | 1781 | O | CYS A 465 | 16.955 | 23.599 | -5.331 | 1.00 | 35.56 | A | O |
| ATOM | 1782 | N | PRO A 466 | 17.645 | 21.462 | -5.148 | 1.00 | 33.00 | A | N |
| ATOM | 1783 | CD | PRO A 466 | 18.423 | 20.370 | -4.542 | 1.00 | 31.93 | A | C |
| ATOM | 1784 | CA | PRO A 466 | 17.242 | 21.132 | -6.521 | 1.00 | 31.56 | A | C |
| ATOM | 1785 | CB | PRO A 466 | 17.816 | 19.720 | -6.716 | 1.00 | 31.03 | A | C |
| ATOM | 1786 | CG | PRO A 466 | 18.925 | 19.658 | -5.744 | 1.00 | 30.65 | A | C |
| ATOM | 1787 | C | PRO A 466 | 15.704 | 21.150 | -6.692 | 1.00 | 32.03 | A | C |

Figure 13

| ATOM | 1788 | O   | PRO A 466 | 14.961 | 20.871 | -5.746  | 1.00 | 31.10 | A | O |
| ATOM | 1789 | N   | GLU A 467 | 15.223 | 21.426 | -7.906  | 1.00 | 32.85 | A | N |
| ATOM | 1790 | CA  | GLU A 467 | 13.768 | 21.471 | -8.130  | 1.00 | 32.63 | A | C |
| ATOM | 1791 | CB  | GLU A 467 | 13.382 | 21.970 | -9.529  | 1.00 | 32.81 | A | C |
| ATOM | 1792 | CG  | GLU A 467 | 12.705 | 23.366 | -9.515  | 1.00 | 35.68 | A | C |
| ATOM | 1793 | CD  | GLU A 467 | 11.265 | 23.442 | -8.943  | 1.00 | 36.31 | A | C |
| ATOM | 1794 | OE1 | GLU A 467 | 11.013 | 24.309 | -8.058  | 1.00 | 36.30 | A | O |
| ATOM | 1795 | OE2 | GLU A 467 | 10.373 | 22.701 | -9.436  | 1.00 | 37.23 | A | O |
| ATOM | 1796 | C   | GLU A 467 | 13.090 | 20.153 | -7.908  | 1.00 | 31.82 | A | C |
| ATOM | 1797 | O   | GLU A 467 | 11.973 | 20.113 | -7.414  | 1.00 | 31.65 | A | O |
| ATOM | 1798 | N   | GLU A 468 | 13.730 | 19.083 | -8.347  | 1.00 | 31.64 | A | N |
| ATOM | 1799 | CA  | GLU A 468 | 13.155 | 17.766 | -8.176  | 1.00 | 32.01 | A | C |
| ATOM | 1800 | CB  | GLU A 468 | 13.959 | 16.725 | -8.958  | 1.00 | 37.37 | A | C |
| ATOM | 1801 | CG  | GLU A 468 | 14.196 | 17.056 | -10.457 | 1.00 | 44.00 | A | C |
| ATOM | 1802 | CD  | GLU A 468 | 15.251 | 18.202 | -10.723 | 1.00 | 48.84 | A | C |
| ATOM | 1803 | OE1 | GLU A 468 | 16.174 | 18.459 | -9.875  | 1.00 | 49.06 | A | O |
| ATOM | 1804 | OE2 | GLU A 468 | 15.150 | 18.847 | -11.810 | 1.00 | 51.46 | A | O |
| ATOM | 1805 | C   | GLU A 468 | 13.120 | 17.459 | -6.657  | 1.00 | 29.42 | A | C |
| ATOM | 1806 | O   | GLU A 468 | 12.136 | 16.911 | -6.176  | 1.00 | 28.02 | A | O |
| ATOM | 1807 | N   | LEU A 469 | 14.124 | 17.907 | -5.891  | 1.00 | 27.26 | A | N |
| ATOM | 1808 | CA  | LEU A 469 | 14.101 | 17.682 | -4.452  | 1.00 | 25.83 | A | C |
| ATOM | 1809 | CB  | LEU A 469 | 15.416 | 18.068 | -3.786  | 1.00 | 24.84 | A | C |
| ATOM | 1810 | CG  | LEU A 469 | 15.446 | 17.836 | -2.267  | 1.00 | 23.76 | A | C |
| ATOM | 1811 | CD1 | LEU A 469 | 15.030 | 16.398 | -1.929  | 1.00 | 23.84 | A | C |
| ATOM | 1812 | CD2 | LEU A 469 | 16.796 | 18.129 | -1.722  | 1.00 | 20.98 | A | C |
| ATOM | 1813 | C   | LEU A 469 | 12.941 | 18.474 | -3.832  | 1.00 | 25.33 | A | C |
| ATOM | 1814 | O   | LEU A 469 | 12.274 | 17.993 | -2.920  | 1.00 | 25.46 | A | O |
| ATOM | 1815 | N   | TYR A 470 | 12.668 | 19.672 | -4.349  | 1.00 | 25.53 | A | N |
| ATOM | 1816 | CA  | TYR A 470 | 11.548 | 20.476 | -3.836  | 1.00 | 24.77 | A | C |
| ATOM | 1817 | CB  | TYR A 470 | 11.608 | 21.921 | -4.378  | 1.00 | 23.23 | A | C |
| ATOM | 1818 | CG  | TYR A 470 | 10.479 | 22.803 | -3.917  | 1.00 | 21.69 | A | C |
| ATOM | 1819 | CD1 | TYR A 470 | 10.364 | 23.169 | -2.573  | 1.00 | 23.11 | A | C |
| ATOM | 1820 | CE1 | TYR A 470 | 9.334  | 23.987 | -2.109  | 1.00 | 23.17 | A | C |
| ATOM | 1821 | CD2 | TYR A 470 | 9.538  | 23.267 | -4.810  | 1.00 | 21.28 | A | C |
| ATOM | 1822 | CE2 | TYR A 470 | 8.498  | 24.085 | -4.380  | 1.00 | 22.80 | A | C |
| ATOM | 1823 | CZ  | TYR A 470 | 8.387  | 24.450 | -3.008  | 1.00 | 23.75 | A | C |
| ATOM | 1824 | OH  | TYR A 470 | 7.318  | 25.218 | -2.532  | 1.00 | 22.93 | A | O |
| ATOM | 1825 | C   | TYR A 470 | 10.180 | 19.817 | -4.164  | 1.00 | 24.73 | A | C |
| ATOM | 1826 | O   | TYR A 470 | 9.260  | 19.843 | -3.342  | 1.00 | 23.63 | A | O |
| ATOM | 1827 | N   | GLN A 471 | 10.051 | 19.251 | -5.364  | 1.00 | 24.36 | A | N |
| ATOM | 1828 | CA  | GLN A 471 | 8.804  | 18.622 | -5.737  | 1.00 | 24.82 | A | C |
| ATOM | 1829 | CB  | GLN A 471 | 8.730  | 18.317 | -7.232  | 1.00 | 26.31 | A | C |
| ATOM | 1830 | CG  | GLN A 471 | 8.659  | 19.561 | -8.106  | 1.00 | 29.43 | A | C |
| ATOM | 1831 | CD  | GLN A 471 | 7.583  | 20.606 | -7.664  | 1.00 | 31.73 | A | C |
| ATOM | 1832 | OE1 | GLN A 471 | 6.389  | 20.281 | -7.442  | 1.00 | 34.76 | A | O |
| ATOM | 1833 | NE2 | GLN A 471 | 7.994  | 21.870 | -7.604  | 1.00 | 29.75 | A | N |
| ATOM | 1834 | C   | GLN A 471 | 8.564  | 17.392 | -4.859  | 1.00 | 24.55 | A | C |
| ATOM | 1835 | O   | GLN A 471 | 7.410  | 17.045 | -4.568  | 1.00 | 24.41 | A | O |
| ATOM | 1836 | N   | LEU A 472 | 9.652  | 16.799 | -4.361  | 1.00 | 22.55 | A | N |
| ATOM | 1837 | CA  | LEU A 472 | 9.527  | 15.672 | -3.445  | 1.00 | 21.16 | A | C |
| ATOM | 1838 | CB  | LEU A 472 | 10.852 | 14.940 | -3.235  | 1.00 | 20.65 | A | C |
| ATOM | 1839 | CG  | LEU A 472 | 10.873 | 13.417 | -3.438  | 1.00 | 22.34 | A | C |
| ATOM | 1840 | CD1 | LEU A 472 | 10.168 | 13.014 | -4.753  | 1.00 | 20.02 | A | C |
| ATOM | 1841 | CD2 | LEU A 472 | 12.322 | 12.930 | -3.416  | 1.00 | 20.89 | A | C |
| ATOM | 1842 | C   | LEU A 472 | 9.032  | 16.256 | -2.106  | 1.00 | 21.46 | A | C |
| ATOM | 1843 | O   | LEU A 472 | 8.119  | 15.696 | -1.493  | 1.00 | 22.94 | A | O |
| ATOM | 1844 | N   | MET A 473 | 9.527  | 17.430 | -1.705  | 1.00 | 20.36 | A | N |
| ATOM | 1845 | CA  | MET A 473 | 9.074  | 17.998 | -0.442  | 1.00 | 19.91 | A | C |
| ATOM | 1846 | CB  | MET A 473 | 9.790  | 19.295 | -0.139  | 1.00 | 18.92 | A | C |
| ATOM | 1847 | CG  | MET A 473 | 11.247 | 19.112 | 0.108   | 1.00 | 16.09 | A | C |

Figure 13

| | | | | | | | | | | |
|---|---|---|---|---|---|---|---|---|---|---|
| ATOM | 1848 | SD | MET | A | 473 | 12.028 | 20.637 | 0.001 | 1.00 17.40 | A S |
| ATOM | 1849 | CE | MET | A | 473 | 13.659 | 20.342 | 0.618 | 1.00  9.53 | A C |
| ATOM | 1850 | C | MET | A | 473 | 7.580 | 18.278 | -0.531 | 1.00 20.36 | A C |
| ATOM | 1851 | O | MET | A | 473 | 6.828 | 18.102 | 0.433 | 1.00 20.00 | A O |
| ATOM | 1852 | N | ARG | A | 474 | 7.145 | 18.716 | -1.711 | 1.00 21.95 | A N |
| ATOM | 1853 | CA | ARG | A | 474 | 5.729 | 19.018 | -1.943 | 1.00 21.19 | A C |
| ATOM | 1854 | CB | ARG | A | 474 | 5.562 | 19.796 | -3.254 | 1.00 21.73 | A C |
| ATOM | 1855 | CG | ARG | A | 474 | 6.210 | 21.233 | -3.151 | 1.00 23.02 | A C |
| ATOM | 1856 | CD | ARG | A | 474 | 5.658 | 22.075 | -1.970 | 1.00 20.84 | A C |
| ATOM | 1857 | NE | ARG | A | 474 | 4.260 | 22.412 | -2.209 | 1.00 22.69 | A N |
| ATOM | 1858 | CZ | ARG | A | 474 | 3.820 | 23.508 | -2.810 | 1.00 24.01 | A C |
| ATOM | 1859 | NH1 | ARG | A | 474 | 4.641 | 24.454 | -3.256 | 1.00 23.80 | A N |
| ATOM | 1860 | NH2 | ARG | A | 474 | 2.533 | 23.584 | -3.089 | 1.00 24.80 | A N |
| ATOM | 1861 | C | ARG | A | 474 | 4.840 | 17.799 | -1.837 | 1.00 21.94 | A C |
| ATOM | 1862 | O | ARG | A | 474 | 3.745 | 17.895 | -1.281 | 1.00 23.25 | A O |
| ATOM | 1863 | N | LEU | A | 475 | 5.337 | 16.644 | -2.295 | 1.00 22.68 | A N |
| ATOM | 1864 | CA | LEU | A | 475 | 4.575 | 15.390 | -2.217 | 1.00 21.91 | A C |
| ATOM | 1865 | CB | LEU | A | 475 | 5.242 | 14.274 | -3.041 | 1.00 22.22 | A C |
| ATOM | 1866 | CG | LEU | A | 475 | 5.128 | 14.571 | -4.540 | 1.00 23.83 | A C |
| ATOM | 1867 | CD1 | LEU | A | 475 | 6.002 | 13.720 | -5.446 | 1.00 22.21 | A C |
| ATOM | 1868 | CD2 | LEU | A | 475 | 3.632 | 14.466 | -4.913 | 1.00 22.73 | A C |
| ATOM | 1869 | C | LEU | A | 475 | 4.551 | 14.988 | -0.755 | 1.00 20.67 | A C |
| ATOM | 1870 | O | LEU | A | 475 | 3.596 | 14.402 | -0.290 | 1.00 20.48 | A O |
| ATOM | 1871 | N | CYS | A | 476 | 5.596 | 15.325 | -0.006 | 1.00 20.34 | A N |
| ATOM | 1872 | CA | CYS | A | 476 | 5.569 | 14.949 | 1.410 | 1.00 19.42 | A C |
| ATOM | 1873 | CB | CYS | A | 476 | 6.960 | 14.965 | 2.038 | 1.00 19.51 | A C |
| ATOM | 1874 | SG | CYS | A | 476 | 8.232 | 13.982 | 1.238 | 1.00 21.99 | A S |
| ATOM | 1875 | C | CYS | A | 476 | 4.576 | 15.845 | 2.210 | 1.00 18.84 | A C |
| ATOM | 1876 | O | CYS | A | 476 | 4.055 | 15.432 | 3.253 | 1.00 17.92 | A O |
| ATOM | 1877 | N | TRP | A | 477 | 4.252 | 17.024 | 1.659 | 1.00 17.93 | A N |
| ATOM | 1878 | CA | TRP | A | 477 | 3.337 | 17.975 | 2.291 | 1.00 16.78 | A C |
| ATOM | 1879 | CB | TRP | A | 477 | 3.912 | 19.414 | 2.283 | 1.00 17.13 | A C |
| ATOM | 1880 | CG | TRP | A | 477 | 5.276 | 19.540 | 2.906 | 1.00 17.25 | A C |
| ATOM | 1881 | CD2 | TRP | A | 477 | 6.329 | 20.423 | 2.498 | 1.00 17.01 | A C |
| ATOM | 1882 | CE2 | TRP | A | 477 | 7.436 | 20.152 | 3.312 | 1.00 18.41 | A C |
| ATOM | 1883 | CE3 | TRP | A | 477 | 6.455 | 21.413 | 1.519 | 1.00 18.70 | A C |
| ATOM | 1884 | CD1 | TRP | A | 477 | 5.776 | 18.805 | 3.935 | 1.00 17.25 | A C |
| ATOM | 1885 | NE1 | TRP | A | 477 | 7.072 | 19.151 | 4.181 | 1.00 16.59 | A N |
| ATOM | 1886 | CZ2 | TRP | A | 477 | 8.647 | 20.851 | 3.187 | 1.00 16.56 | A C |
| ATOM | 1887 | CZ3 | TRP | A | 477 | 7.675 | 22.106 | 1.403 | 1.00 17.52 | A C |
| ATOM | 1888 | CH2 | TRP | A | 477 | 8.737 | 21.812 | 2.226 | 1.00 15.99 | A C |
| ATOM | 1889 | C | TRP | A | 477 | 1.930 | 17.994 | 1.712 | 1.00 17.47 | A C |
| ATOM | 1890 | O | TRP | A | 477 | 1.172 | 18.931 | 1.986 | 1.00 18.09 | A O |
| ATOM | 1891 | N | LYS | A | 478 | 1.540 | 16.977 | 0.943 | 1.00 17.54 | A N |
| ATOM | 1892 | CA | LYS | A | 478 | 0.169 | 16.973 | 0.408 | 1.00 17.31 | A C |
| ATOM | 1893 | CB | LYS | A | 478 | -0.112 | 15.713 | -0.394 | 1.00 16.48 | A C |
| ATOM | 1894 | CG | LYS | A | 478 | 0.599 | 15.655 | -1.710 | 1.00 17.99 | A C |
| ATOM | 1895 | CD | LYS | A | 478 | 0.238 | 16.767 | -2.632 | 1.00 17.82 | A C |
| ATOM | 1896 | CE | LYS | A | 478 | -0.967 | 16.468 | -3.447 | 1.00 19.06 | A C |
| ATOM | 1897 | NZ | LYS | A | 478 | -1.494 | 17.719 | -4.172 | 1.00 22.08 | A N |
| ATOM | 1898 | C | LYS | A | 478 | -0.783 | 17.094 | 1.582 | 1.00 17.12 | A C |
| ATOM | 1899 | O | LYS | A | 478 | -0.516 | 16.551 | 2.657 | 1.00 17.46 | A O |
| ATOM | 1900 | N | GLU | A | 479 | -1.861 | 17.836 | 1.398 | 1.00 18.36 | A N |
| ATOM | 1901 | CA | GLU | A | 479 | -2.786 | 18.059 | 2.498 | 1.00 20.09 | A C |
| ATOM | 1902 | CB | GLU | A | 479 | -3.903 | 19.018 | 2.038 | 1.00 18.78 | A C |
| ATOM | 1903 | CG | GLU | A | 479 | -4.822 | 19.507 | 3.130 | 1.00 18.26 | A C |
| ATOM | 1904 | CD | GLU | A | 479 | -4.062 | 20.184 | 4.270 | 1.00 19.42 | A C |
| ATOM | 1905 | OE1 | GLU | A | 479 | -2.979 | 20.794 | 4.102 | 1.00 20.02 | A O |
| ATOM | 1906 | OE2 | GLU | A | 479 | -4.597 | 20.145 | 5.362 | 1.00 16.75 | A O |
| ATOM | 1907 | C | GLU | A | 479 | -3.370 | 16.768 | 3.080 | 1.00 21.90 | A C |

Figure 13

```
ATOM   1908  O    GLU A 479      -3.571  16.606   4.302  1.00 22.62           A    O
ATOM   1909  N    ARG A 480      -3.690  15.861   2.163  1.00 22.58           A    N
ATOM   1910  CA   ARG A 480      -4.285  14.596   2.517  1.00 22.59           A    C
ATOM   1911  CB   ARG A 480      -5.264  14.160   1.452  1.00 24.22           A    C
ATOM   1912  CG   ARG A 480      -6.448  14.989   1.260  1.00 25.65           A    C
ATOM   1913  CD   ARG A 480      -6.864  14.698  -0.137  1.00 32.57           A    C
ATOM   1914  NE   ARG A 480      -8.229  15.122  -0.394  1.00 40.11           A    N
ATOM   1915  CZ   ARG A 480      -8.811  15.093  -1.588  1.00 43.47           A    C
ATOM   1916  NH1  ARG A 480      -8.149  14.621  -2.662  1.00 42.62           A    N
ATOM   1917  NH2  ARG A 480     -10.064  15.527  -1.687  1.00 44.99           A    N
ATOM   1918  C    ARG A 480      -3.176  13.566   2.552  1.00 22.68           A    C
ATOM   1919  O    ARG A 480      -2.452  13.418   1.575  1.00 22.75           A    O
ATOM   1920  N    PRO A 481      -3.122  12.754   3.622  1.00 23.12           A    N
ATOM   1921  CD   PRO A 481      -4.092  12.807   4.727  1.00 23.12           A    C
ATOM   1922  CA   PRO A 481      -2.156  11.688   3.888  1.00 22.71           A    C
ATOM   1923  CB   PRO A 481      -2.750  11.016   5.119  1.00 22.55           A    C
ATOM   1924  CG   PRO A 481      -3.335  12.123   5.840  1.00 22.97           A    C
ATOM   1925  C    PRO A 481      -1.962  10.669   2.770  1.00 22.92           A    C
ATOM   1926  O    PRO A 481      -0.831  10.386   2.345  1.00 23.13           A    O
ATOM   1927  N    GLU A 482      -3.074  10.156   2.273  1.00 21.96           A    N
ATOM   1928  CA   GLU A 482      -3.055   9.146   1.226  1.00 21.57           A    C
ATOM   1929  CB   GLU A 482      -4.495   8.765   0.854  1.00 21.67           A    C
ATOM   1930  CG   GLU A 482      -5.276   9.851   0.121  1.00 22.21           A    C
ATOM   1931  CD   GLU A 482      -6.353  10.558   0.980  1.00 23.51           A    C
ATOM   1932  OE1  GLU A 482      -6.105  10.827   2.181  1.00 23.54           A    O
ATOM   1933  OE2  GLU A 482      -7.449  10.866   0.438  1.00 23.32           A    O
ATOM   1934  C    GLU A 482      -2.272   9.548  -0.029  1.00 21.81           A    C
ATOM   1935  O    GLU A 482      -1.851   8.693  -0.811  1.00 22.17           A    O
ATOM   1936  N    ASP A 483      -2.083  10.859  -0.206  1.00 21.50           A    N
ATOM   1937  CA   ASP A 483      -1.408  11.467  -1.351  1.00 21.16           A    C
ATOM   1938  CB   ASP A 483      -2.067  12.817  -1.637  1.00 20.75           A    C
ATOM   1939  CG   ASP A 483      -3.441  12.685  -2.262  1.00 22.46           A    C
ATOM   1940  OD1  ASP A 483      -3.719  11.697  -2.954  1.00 22.62           A    O
ATOM   1941  OD2  ASP A 483      -4.252  13.602  -2.106  1.00 25.80           A    O
ATOM   1942  C    ASP A 483       0.088  11.653   1.197  1.00 21.63           A    C
ATOM   1943  O    ASP A 483       0.762  12.140  -2.134  1.00 20.73           A    O
ATOM   1944  N    ARG A 484       0.576  11.388   0.014  1.00 21.55           A    N
ATOM   1945  CA   ARG A 484       2.009  11.517   0.339  1.00 21.08           A    C
ATOM   1946  CB   ARG A 484       2.227  11.927   1.816  1.00 20.58           A    C
ATOM   1947  CG   ARG A 484       1.262  12.964   2.322  1.00 19.10           A    C
ATOM   1948  CD   ARG A 484       1.544  13.293   3.768  1.00 20.40           A    C
ATOM   1949  NE   ARG A 484       0.739  14.445   4.183  1.00 21.38           A    N
ATOM   1950  CZ   ARG A 484       0.113  14.550   5.350  1.00 21.64           A    C
ATOM   1951  NH1  ARG A 484       0.222  13.567   6.240  1.00 19.64           A    N
ATOM   1952  NH2  ARG A 484      -0.723  15.567   5.565  1.00 19.02           A    N
ATOM   1953  C    ARG A 484       2.644  10.162   0.045  1.00 22.02           A    C
ATOM   1954  O    ARG A 484       2.054   9.127   0.332  1.00 21.90           A    O
ATOM   1955  N    PRO A 485       3.892  10.155  -0.441  1.00 24.17           A    N
ATOM   1956  CD   PRO A 485       4.842  11.254  -0.281  1.00 22.33           A    C
ATOM   1957  CA   PRO A 485       4.609   8.922  -0.792  1.00 22.90           A    C
ATOM   1958  CB   PRO A 485       5.891   9.436  -1.471  1.00 23.00           A    C
ATOM   1959  CG   PRO A 485       5.783  10.955  -1.358  1.00 24.00           A    C
ATOM   1960  C    PRO A 485       4.977   8.034   0.383  1.00 24.46           A    C
ATOM   1961  O    PRO A 485       5.028   8.468   1.545  1.00 24.67           A    O
ATOM   1962  N    THR A 486       5.305   6.793   0.041  1.00 24.42           A    N
ATOM   1963  CA   THR A 486       5.723   5.821   1.040  1.00 22.66           A    C
ATOM   1964  CB   THR A 486       5.550   4.392   0.543  1.00 20.48           A    C
ATOM   1965  OG1  THR A 486       6.210   4.255  -0.707  1.00 23.35           A    O
ATOM   1966  CG2  THR A 486       4.152   4.056   0.394  1.00 16.60           A    C
ATOM   1967  C    THR A 486       7.225   6.106   1.244  1.00 22.72           A    C
```

Figure 13

| | | | | | | | | | | | |
|---|---|---|---|---|---|---|---|---|---|---|---|
| ATOM | 1968 | O | THR | A | 486 | 7.885 | 6.583 | 0.332 | 1.00 | 21.67 | A O |
| ATOM | 1969 | N | PHE | A | 487 | 7.771 | 5.810 | 2.419 | 1.00 | 21.72 | A N |
| ATOM | 1970 | CA | PHE | A | 487 | 9.174 | 6.077 | 2.656 | 1.00 | 21.08 | A C |
| ATOM | 1971 | CB | PHE | A | 487 | 9.519 | 5.812 | 4.086 | 1.00 | 19.77 | A C |
| ATOM | 1972 | CG | PHE | A | 487 | 9.274 | 6.958 | 4.973 | 1.00 | 18.71 | A C |
| ATOM | 1973 | CD1 | PHE | A | 487 | 10.005 | 8.132 | 4.844 | 1.00 | 16.00 | A C |
| ATOM | 1974 | CD2 | PHE | A | 487 | 8.336 | 6.856 | 5.976 | 1.00 | 18.70 | A C |
| ATOM | 1975 | CE1 | PHE | A | 487 | 9.801 | 9.174 | 5.705 | 1.00 | 14.82 | A C |
| ATOM | 1976 | CE2 | PHE | A | 487 | 8.130 | 7.900 | 6.842 | 1.00 | 18.31 | A C |
| ATOM | 1977 | CZ | PHE | A | 487 | 8.863 | 9.061 | 6.710 | 1.00 | 17.45 | A C |
| ATOM | 1978 | C | PHE | A | 487 | 9.943 | 5.129 | 1.791 | 1.00 | 23.30 | A C |
| ATOM | 1979 | O | PHE | A | 487 | 11.124 | 5.286 | 1.612 | 1.00 | 24.95 | A O |
| ATOM | 1980 | N | ASP | A | 488 | 9.262 | 4.099 | 1.278 | 1.00 | 25.33 | A N |
| ATOM | 1981 | CA | ASP | A | 488 | 9.847 | 3.105 | 0.373 | 1.00 | 24.28 | A C |
| ATOM | 1982 | CB | ASP | A | 488 | 8.901 | 1.895 | 0.281 | 1.00 | 25.59 | A C |
| ATOM | 1983 | CG | ASP | A | 488 | 9.339 | 0.854 | -0.762 | 1.00 | 29.12 | A C |
| ATOM | 1984 | OD1 | ASP | A | 488 | 10.569 | 0.590 | -0.896 | 1.00 | 29.70 | A O |
| ATOM | 1985 | OD2 | ASP | A | 488 | 8.439 | 0.305 | -1.459 | 1.00 | 28.10 | A O |
| ATOM | 1986 | C | ASP | A | 488 | 10.045 | 3.825 | -0.974 | 1.00 | 23.86 | A C |
| ATOM | 1987 | O | ASP | A | 488 | 11.065 | 3.674 | -1.615 | 1.00 | 23.15 | A O |
| ATOM | 1988 | N | TYR | A | 489 | 9.103 | 4.669 | -1.378 | 1.00 | 23.96 | A N |
| ATOM | 1989 | CA | TYR | A | 489 | 9.295 | 5.441 | -2.610 | 1.00 | 23.54 | A C |
| ATOM | 1990 | CB | TYR | A | 489 | 8.015 | 6.092 | -3.063 | 1.00 | 20.90 | A C |
| ATOM | 1991 | CG | TYR | A | 489 | 8.220 | 7.076 | -4.179 | 1.00 | 18.14 | A C |
| ATOM | 1992 | CD1 | TYR | A | 489 | 8.489 | 6.651 | -5.456 | 1.00 | 17.39 | A C |
| ATOM | 1993 | CE1 | TYR | A | 489 | 8.689 | 7.561 | -6.487 | 1.00 | 16.70 | A C |
| ATOM | 1994 | CD2 | TYR | A | 489 | 8.159 | 8.439 | -3.957 | 1.00 | 17.34 | A C |
| ATOM | 1995 | CE2 | TYR | A | 489 | 8.361 | 9.347 | -4.987 | 1.00 | 15.86 | A C |
| ATOM | 1996 | CZ | TYR | A | 489 | 8.621 | 8.903 | -6.244 | 1.00 | 16.30 | A C |
| ATOM | 1997 | OH | TYR | A | 489 | 8.799 | 9.775 | -7.278 | 1.00 | 15.99 | A O |
| ATOM | 1998 | C | TYR | A | 489 | 10.343 | 6.529 | -2.396 | 1.00 | 25.79 | A C |
| ATOM | 1999 | O | TYR | A | 489 | 11.200 | 6.727 | -3.257 | 1.00 | 27.79 | A O |
| ATOM | 2000 | N | LEU | A | 490 | 10.296 | 7.195 | -1.237 | 1.00 | 26.21 | A N |
| ATOM | 2001 | CA | LEU | A | 490 | 11.249 | 8.244 | -0.903 | 1.00 | 27.31 | A C |
| ATOM | 2002 | CB | LEU | A | 490 | 10.937 | 8.866 | 0.458 | 1.00 | 28.51 | A C |
| ATOM | 2003 | CG | LEU | A | 490 | 9.747 | 9.835 | 0.419 | 1.00 | 29.74 | A C |
| ATOM | 2004 | CD1 | LEU | A | 490 | 9.326 | 10.198 | 1.856 | 1.00 | 29.89 | A C |
| ATOM | 2005 | CD2 | LEU | A | 490 | 10.088 | 11.082 | -0.408 | 1.00 | 29.87 | A C |
| ATOM | 2006 | C | LEU | A | 490 | 12.672 | 7.719 | -0.904 | 1.00 | 28.17 | A C |
| ATOM | 2007 | O | LEU | A | 490 | 13.561 | 8.374 | -1.454 | 1.00 | 28.22 | A O |
| ATOM | 2008 | N | ARG | A | 491 | 12.881 | 6.530 | -0.332 | 1.00 | 28.39 | A N |
| ATOM | 2009 | CA | ARG | A | 491 | 14.209 | 5.927 | -0.292 | 1.00 | 30.74 | A C |
| ATOM | 2010 | CB | ARG | A | 491 | 14.245 | 4.588 | 0.441 | 1.00 | 30.82 | A C |
| ATOM | 2011 | CG | ARG | A | 491 | 15.573 | 3.850 | 0.183 | 1.00 | 33.67 | A C |
| ATOM | 2012 | CD | ARG | A | 491 | 15.543 | 2.350 | 0.616 | 1.00 | 40.17 | A C |
| ATOM | 2013 | NE | ARG | A | 491 | 14.370 | 1.687 | 0.037 | 1.00 | 44.94 | A N |
| ATOM | 2014 | CZ | ARG | A | 491 | 14.264 | 1.359 | -1.246 | 1.00 | 45.68 | A C |
| ATOM | 2015 | NH1 | ARG | A | 491 | 15.279 | 1.608 | -2.080 | 1.00 | 44.49 | A N |
| ATOM | 2016 | NH2 | ARG | A | 491 | 13.112 | 0.881 | -1.702 | 1.00 | 44.34 | A N |
| ATOM | 2017 | C | ARG | A | 491 | 14.708 | 5.679 | -1.692 | 1.00 | 31.94 | A C |
| ATOM | 2018 | O | ARG | A | 491 | 15.888 | 5.845 | -1.969 | 1.00 | 32.63 | A O |
| ATOM | 2019 | N | SER | A | 492 | 13.828 | 5.143 | -2.523 | 1.00 | 32.57 | A N |
| ATOM | 2020 | CA | SER | A | 492 | 14.168 | 4.825 | -3.893 | 1.00 | 33.72 | A C |
| ATOM | 2021 | CB | SER | A | 492 | 12.940 | 4.294 | -4.627 | 1.00 | 35.24 | A C |
| ATOM | 2022 | OG | SER | A | 492 | 12.724 | 2.956 | -4.231 | 1.00 | 37.26 | A O |
| ATOM | 2023 | C | SER | A | 492 | 14.718 | 5.987 | -4.638 | 1.00 | 33.61 | A C |
| ATOM | 2024 | O | SER | A | 492 | 15.844 | 5.952 | -5.120 | 1.00 | 33.77 | A O |
| ATOM | 2025 | N | VAL | A | 493 | 13.909 | 7.029 | -4.693 | 1.00 | 33.97 | A N |
| ATOM | 2026 | CA | VAL | A | 493 | 14.227 | 8.242 | -5.409 | 1.00 | 33.97 | A C |
| ATOM | 2027 | CB | VAL | A | 493 | 12.902 | 9.041 | -5.615 | 1.00 | 34.85 | A C |

Figure 13

```
ATOM   2028  CG1 VAL A 493     12.206   9.323  -4.266  1.00 36.00      A  C
ATOM   2029  CG2 VAL A 493     13.162  10.318  -6.400  1.00 35.59      A  C
ATOM   2030  C   VAL A 493     15.404   9.044  -4.800  1.00 33.93      A  C
ATOM   2031  O   VAL A 493     16.197   9.632  -5.535  1.00 33.52      A  O
ATOM   2032  N   LEU A 494     15.593   8.974  -3.482  1.00 34.31      A  N
ATOM   2033  CA  LEU A 494     16.715   9.682  -2.861  1.00 34.96      A  C
ATOM   2034  CB  LEU A 494     16.511   9.825  -1.361  1.00 32.40      A  C
ATOM   2035  CG  LEU A 494     15.453  10.875  -1.112  1.00 30.25      A  C
ATOM   2036  CD1 LEU A 494     15.143  10.925   0.320  1.00 28.20      A  C
ATOM   2037  CD2 LEU A 494     15.927  12.226  -1.654  1.00 30.54      A  C
ATOM   2038  C   LEU A 494     18.046   9.000  -3.129  1.00 36.52      A  C
ATOM   2039  O   LEU A 494     19.061   9.658  -3.228  1.00 36.52      A  O
ATOM   2040  N   GLU A 495     18.042   7.682  -3.261  1.00 39.25      A  N
ATOM   2041  CA  GLU A 495     19.274   6.940  -3.540  1.00 42.40      A  C
ATOM   2042  CB  GLU A 495     19.024   5.450  -3.437  1.00 43.53      A  C
ATOM   2043  CG  GLU A 495     19.107   4.905  -2.047  1.00 46.37      A  C
ATOM   2044  CD  GLU A 495     18.941   3.424  -2.007  1.00 48.24      A  C
ATOM   2045  OE1 GLU A 495     18.910   2.795  -3.090  1.00 50.76      A  O
ATOM   2046  OE2 GLU A 495     18.840   2.887  -0.885  1.00 49.02      A  O
ATOM   2047  C   GLU A 495     19.767   7.193  -4.945  1.00 43.59      A  C
ATOM   2048  O   GLU A 495     20.966   7.379  -5.154  1.00 44.07      A  O
ATOM   2049  N   ASP A 496     18.826   7.120  -5.893  1.00 44.64      A  N
ATOM   2050  CA  ASP A 496     19.075   7.304  -7.316  1.00 45.94      A  C
ATOM   2051  CB  ASP A 496     18.079   6.433  -8.126  1.00 45.49      A  C
ATOM   2052  CG  ASP A 496     18.338   4.887  -7.961  1.00 46.39      A  C
ATOM   2053  OD1 ASP A 496     19.485   4.472  -7.614  1.00 46.15      A  O
ATOM   2054  OD2 ASP A 496     17.382   4.086  -8.180  1.00 46.26      A  O
ATOM   2055  C   ASP A 496     19.056   8.762  -7.806  1.00 47.19      A  C
ATOM   2056  O   ASP A 496     19.218   9.018  -8.997  1.00 48.37      A  O
ATOM   2057  N   PHE A 497     18.968   9.720  -6.891  1.00 48.00      A  N
ATOM   2058  CA  PHE A 497     18.890  11.140  -7.269  1.00 48.48      A  C
ATOM   2059  CB  PHE A 497     18.863  12.013  -6.024  1.00 47.63      A  C
ATOM   2060  CG  PHE A 497     18.185  13.323  -6.243  1.00 48.06      A  C
ATOM   2061  CD1 PHE A 497     16.802  13.433  -6.104  1.00 48.49      A  C
ATOM   2062  CD2 PHE A 497     18.922  14.451  -6.613  1.00 48.47      A  C
ATOM   2063  CE1 PHE A 497     16.167  14.640  -6.330  1.00 48.47      A  C
ATOM   2064  CE2 PHE A 497     18.307  15.664  -6.840  1.00 48.06      A  C
ATOM   2065  CZ  PHE A 497     16.922  15.767  -6.703  1.00 48.63      A  C
ATOM   2066  C   PHE A 497     19.915  11.681  -8.291  1.00 48.97      A  C
ATOM   2067  O   PHE A 497     19.587  12.551  -9.093  1.00 48.23      A  O
ATOM   2068  N   PHE A 498     21.163  11.218  -8.206  1.00 50.79      A  N
ATOM   2069  CA  PHE A 498     22.240  11.596  -9.155  1.00 52.12      A  C
ATOM   2070  CB  PHE A 498     22.379  13.118  -9.396  1.00 52.63      A  C
ATOM   2071  CG  PHE A 498     22.529  13.936  -8.151  1.00 52.99      A  C
ATOM   2072  CD1 PHE A 498     23.038  13.390  -6.982  1.00 52.50      A  C
ATOM   2073  CD2 PHE A 498     22.084  15.250  -8.141  1.00 53.16      A  C
ATOM   2074  CE1 PHE A 498     23.082  14.143  -5.820  1.00 53.30      A  C
ATOM   2075  CE2 PHE A 498     22.126  16.012  -6.980  1.00 53.47      A  C
ATOM   2076  CZ  PHE A 498     22.626  15.459  -5.818  1.00 53.59      A  C
ATOM   2077  C   PHE A 498     23.600  11.023  -8.819  1.00 52.18      A  C
ATOM   2078  O   PHE A 498     23.740   9.808  -9.042  1.00 52.66      A  O
ATOM   2079  OH2 H2O A 600      5.253  21.600   9.242  1.00 32.30      A  O
ATOM   2080  OH2 H2O A 601      1.429   2.313  -0.770  1.00 67.52      A  O
ATOM   2081  OH2 H2O A 602     -1.543  23.232   0.187  1.00 20.40      A  O
ATOM   2082  OH2 H2O A 604      6.308   1.605  -2.953  1.00 29.07      A  O
ATOM   2083  OH2 H2O A 605     -6.007  24.400   2.085  1.00 52.64      A  O
ATOM   2084  OH2 H2O A 606      7.074  12.693  12.926  1.00 40.53      A  O
ATOM   2085  OH2 H2O A 607     -3.424  16.054  -0.838  1.00 18.38      A  O
ATOM   2086  OH2 H2O A 608      0.562   8.692  -2.817  1.00 51.08      A  O
ATOM   2087  OH2 H2O A 609     -1.281  29.617   1.367  1.00 30.73      A  O
```

Figure 13

| | | | | | | | | | | | |
|---|---|---|---|---|---|---|---|---|---|---|---|
| ATOM | 2088 | OH2 | H2O | A | 610 | 5.997 | 23.757 | 4.253 | 1.00 | 11.40 | A | O |
| ATOM | 2089 | OH2 | H2O | A | 611 | 5.348 | 17.742 | -6.042 | 1.00 | 22.90 | A | O |
| ATOM | 2090 | OH2 | H2O | A | 612 | 0.645 | 4.974 | 0.336 | 1.00 | 32.20 | A | O |
| ATOM | 2091 | OH2 | H2O | A | 613 | -0.535 | 27.571 | -0.655 | 1.00 | 50.44 | A | O |
| ATOM | 2092 | OH2 | H2O | A | 614 | 9.059 | 8.947 | 18.696 | 1.00 | 19.15 | A | O |
| ATOM | 2093 | OH2 | H2O | A | 615 | -9.899 | 7.243 | -3.084 | 1.00 | 27.60 | A | O |
| ATOM | 2094 | OH2 | H2O | A | 616 | -1.701 | 5.953 | -0.294 | 1.00 | 34.19 | A | O |
| ATOM | 2095 | OH2 | H2O | A | 617 | 2.110 | 29.142 | -0.314 | 1.00 | 60.13 | A | O |
| ATOM | 2096 | OH2 | H2O | A | 618 | 8.110 | 24.120 | 15.806 | 1.00 | 24.19 | A | O |
| ATOM | 2097 | OH2 | H2O | A | 619 | -1.173 | 4.290 | 3.976 | 1.00 | 69.77 | A | O |
| ATOM | 2098 | OH2 | H2O | A | 620 | 1.123 | 25.997 | -3.288 | 1.00 | 30.76 | A | O |
| ATOM | 2099 | OH2 | H2O | A | 621 | 29.899 | 13.657 | 20.260 | 1.00 | 42.86 | A | O |
| ATOM | 2100 | OH2 | H2O | A | 622 | 3.996 | 0.092 | -1.856 | 1.00 | 45.32 | A | O |
| ATOM | 2101 | OH2 | H2O | A | 623 | -3.812 | 22.949 | 1.907 | 1.00 | 41.82 | A | O |
| ATOM | 2102 | OH2 | H2O | A | 624 | 35.799 | 11.534 | 21.619 | 1.00 | 35.91 | A | O |
| ATOM | 2103 | OH2 | H2O | A | 625 | 20.149 | 4.367 | 1.601 | 1.00 | 27.47 | A | O |
| ATOM | 2104 | OH2 | H2O | A | 626 | 15.227 | 19.371 | 14.149 | 1.00 | 26.16 | A | O |
| ATOM | 2105 | OH2 | H2O | A | 627 | 3.802 | 5.267 | 3.790 | 1.00 | 17.67 | A | O |
| ATOM | 2106 | OH2 | H2O | A | 628 | 3.898 | 14.890 | 11.477 | 1.00 | 19.51 | A | O |
| ATOM | 2107 | OH2 | H2O | A | 630 | 8.320 | 14.209 | -7.436 | 1.00 | 54.24 | A | O |
| ATOM | 2108 | OH2 | H2O | A | 631 | 33.742 | -1.158 | 33.341 | 1.00 | 28.69 | A | O |
| ATOM | 2109 | OH2 | H2O | A | 632 | 5.295 | 27.288 | -1.803 | 1.00 | 30.51 | A | O |
| ATOM | 2110 | OH2 | H2O | A | 633 | 17.171 | 12.310 | 19.690 | 1.00 | 34.78 | A | O |
| ATOM | 2111 | OH2 | H2O | A | 634 | 17.153 | -1.506 | 4.648 | 1.00 | 18.81 | A | O |
| ATOM | 2112 | OH2 | H2O | A | 635 | -1.540 | 10.776 | 9.688 | 1.00 | 34.84 | A | O |
| ATOM | 2113 | OH2 | H2O | A | 636 | -2.222 | 11.746 | -5.358 | 1.00 | 21.34 | A | O |
| ATOM | 2114 | OH2 | H2O | A | 638 | -8.356 | 7.795 | -5.497 | 1.00 | 31.15 | A | O |
| ATOM | 2115 | OH2 | H2O | A | 639 | 15.806 | 10.228 | -8.335 | 1.00 | 52.23 | A | O |
| ATOM | 2116 | OH2 | H2O | A | 640 | -1.740 | 22.753 | 5.469 | 1.00 | 32.58 | A | O |
| ATOM | 2117 | OH2 | H2O | A | 641 | -3.003 | 5.578 | 2.348 | 1.00 | 23.59 | A | O |
| ATOM | 2118 | OH2 | H2O | A | 642 | 19.170 | -0.840 | 15.319 | 1.00 | 30.89 | A | O |
| ATOM | 2119 | OH2 | H2O | A | 643 | 26.461 | 22.211 | 33.195 | 1.00 | 76.79 | A | O |
| ATOM | 2120 | OH2 | H2O | A | 644 | 2.677 | 20.651 | -0.558 | 1.00 | 43.07 | A | O |
| ATOM | 2121 | OH2 | H2O | A | 645 | -4.618 | 23.001 | 9.358 | 1.00 | 31.79 | A | O |
| ATOM | 2122 | OH2 | H2O | A | 646 | 28.735 | 1.184 | 41.171 | 1.00 | 54.89 | A | O |
| ATOM | 2123 | OH2 | H2O | A | 647 | 3.892 | 35.231 | 6.412 | 1.00 | 33.57 | A | O |
| ATOM | 2124 | OH2 | H2O | A | 648 | 0.701 | 4.224 | 10.748 | 1.00 | 22.27 | A | O |
| ATOM | 2125 | OH2 | H2O | A | 649 | -13.296 | 5.097 | -2.601 | 1.00 | 26.39 | A | O |
| ATOM | 2126 | OH2 | H2O | A | 650 | 11.820 | 27.583 | 2.418 | 1.00 | 24.71 | A | O |
| ATOM | 2127 | OH2 | H2O | A | 651 | 2.959 | -3.136 | 1.305 | 1.00 | 37.90 | A | O |
| ATOM | 2128 | OH2 | H2O | A | 652 | -1.586 | 20.249 | -1.104 | 1.00 | 42.59 | A | O |
| ATOM | 2129 | OH2 | H2O | A | 653 | 3.433 | 21.939 | 11.117 | 1.00 | 16.29 | A | O |
| ATOM | 2130 | OH2 | H2O | A | 654 | 3.428 | 30.350 | -4.761 | 1.00 | 25.11 | A | O |
| ATOM | 2131 | OH2 | H2O | A | 655 | 24.069 | 20.397 | 26.979 | 1.00 | 44.22 | A | O |
| ATOM | 2132 | OH2 | H2O | A | 656 | 4.803 | 2.819 | 16.336 | 1.00 | 41.01 | A | O |
| ATOM | 2133 | OH2 | H2O | A | 657 | 1.392 | 2.584 | 6.452 | 1.00 | 74.47 | A | O |
| ATOM | 2134 | OH2 | H2O | A | 658 | -1.714 | 23.967 | -5.907 | 1.00 | 45.60 | A | O |
| ATOM | 2135 | OH2 | H2O | A | 659 | 9.389 | 27.388 | -4.652 | 1.00 | 15.49 | A | O |
| ATOM | 2136 | OH2 | H2O | A | 660 | 23.708 | 21.062 | 21.167 | 1.00 | 52.22 | A | O |
| ATOM | 2137 | OH2 | H2O | A | 661 | 14.397 | 14.613 | 23.562 | 1.00 | 28.66 | A | O |
| ATOM | 2138 | OH2 | H2O | A | 662 | -6.281 | 9.971 | -3.308 | 1.00 | 55.06 | A | O |
| ATOM | 2139 | OH2 | H2O | A | 663 | 6.335 | 33.637 | 3.305 | 1.00 | 52.17 | A | O |
| ATOM | 2140 | OH2 | H2O | A | 664 | 26.209 | 21.278 | 20.447 | 1.00 | 44.42 | A | O |
| ATOM | 2141 | OH2 | H2O | A | 665 | 2.599 | 2.099 | 3.090 | 1.00 | 59.71 | A | O |
| ATOM | 2142 | OH2 | H2O | A | 666 | -2.652 | 23.912 | -2.249 | 1.00 | 46.80 | A | O |
| ATOM | 2143 | OH2 | H2O | A | 667 | 8.537 | 0.236 | 3.659 | 1.00 | 33.68 | A | O |
| ATOM | 2144 | OH2 | H2O | A | 668 | 22.513 | 22.794 | -0.445 | 1.00 | 54.61 | A | O |
| ATOM | 2145 | OH2 | H2O | A | 669 | 5.007 | 0.596 | 2.071 | 1.00 | 39.96 | A | O |
| ATOM | 2146 | OH2 | H2O | A | 670 | -5.613 | 23.453 | -2.385 | 1.00 | 57.85 | A | O |
| ATOM | 2147 | OH2 | H2O | A | 671 | -2.243 | 7.404 | 6.787 | 1.00 | 28.46 | A | O |

Figure 13

| ATOM | 2148 | OH2 | H2O | A | 672 | 6.038 | 2.082 | 19.351 | 1.00 | 44.06 | A | O |
|------|------|-----|-----|---|-----|-------|-------|--------|------|-------|---|---|
| ATOM | 2149 | OH2 | H2O | A | 673 | 33.397 | 20.499 | 11.931 | 1.00 | 33.88 | A | O |
| ATOM | 2150 | OH2 | H2O | A | 674 | 14.416 | 0.175 | 4.224 | 1.00 | 36.86 | A | O |
| ATOM | 2151 | OH2 | H2O | A | 675 | -2.972 | 24.117 | 11.509 | 1.00 | 23.16 | A | O |
| ATOM | 2152 | OH2 | H2O | A | 676 | 31.338 | 3.860 | 18.333 | 1.00 | 35.60 | A | O |
| ATOM | 2153 | OH2 | H2O | A | 677 | 5.295 | 14.434 | 14.046 | 1.00 | 29.03 | A | O |
| ATOM | 2154 | OH2 | H2O | A | 678 | -5.669 | 17.962 | 6.825 | 1.00 | 41.98 | A | O |
| ATOM | 2155 | OH2 | H2O | A | 679 | 14.579 | 20.709 | 16.325 | 1.00 | 52.43 | A | O |
| ATOM | 2156 | OH2 | H2O | A | 680 | 31.914 | 15.657 | 31.527 | 1.00 | 64.52 | A | O |
| ATOM | 2157 | OH2 | H2O | A | 681 | -6.560 | 18.381 | 9.550 | 1.00 | 35.96 | A | O |
| ATOM | 2158 | OH2 | H2O | A | 682 | 29.395 | 2.454 | 19.405 | 1.00 | 41.64 | A | O |
| ATOM | 2159 | OH2 | H2O | A | 683 | 19.040 | 16.527 | 19.698 | 1.00 | 32.00 | A | O |
| ATOM | 2160 | OH2 | H2O | A | 684 | 14.371 | 24.553 | 7.305 | 1.00 | 23.70 | A | O |
| ATOM | 2161 | OH2 | H2O | A | 685 | -4.764 | 22.133 | 7.088 | 1.00 | 11.58 | A | O |
| ATOM | 2162 | OH2 | H2O | A | 686 | 17.010 | 23.470 | -9.280 | 1.00 | 62.32 | A | O |
| ATOM | 2163 | OH2 | H2O | A | 687 | -2.062 | 25.910 | -4.121 | 1.00 | 34.69 | A | O |
| ATOM | 2164 | OH2 | H2O | A | 688 | 33.706 | 12.870 | 11.415 | 1.00 | 45.23 | A | O |
| ATOM | 2165 | OH2 | H2O | A | 689 | -5.049 | 24.423 | 13.259 | 1.00 | 33.34 | A | O |
| ATOM | 2166 | OH2 | H2O | A | 690 | 4.560 | 4.896 | 33.021 | 1.00 | 27.16 | A | O |
| ATOM | 2167 | OH2 | H2O | A | 691 | 18.894 | -1.802 | 19.601 | 1.00 | 55.12 | A | O |
| ATOM | 2168 | OH2 | H2O | A | 692 | 12.269 | 21.494 | 18.331 | 1.00 | 23.92 | A | O |
| ATOM | 2169 | OH2 | H2O | A | 693 | 16.237 | 23.003 | 12.269 | 1.00 | 24.59 | A | O |
| ATOM | 2170 | OH2 | H2O | A | 694 | 17.227 | -0.129 | 17.629 | 1.00 | 54.01 | A | O |
| ATOM | 2171 | OH2 | H2O | A | 695 | -9.746 | 9.671 | -6.585 | 1.00 | 52.53 | A | O |
| ATOM | 2172 | OH2 | H2O | A | 696 | 30.853 | 16.500 | 1.355 | 1.00 | 45.63 | A | O |
| ATOM | 2173 | OH2 | H2O | A | 697 | 10.872 | 15.449 | -8.152 | 1.00 | 55.70 | A | O |
| ATOM | 2174 | OH2 | H2O | A | 698 | 24.752 | 11.393 | 34.463 | 1.00 | 33.68 | A | O |
| ATOM | 2175 | OH2 | H2O | A | 699 | -5.253 | 21.276 | -0.314 | 1.00 | 35.59 | A | O |
| ATOM | 2176 | OH2 | H2O | A | 700 | 6.318 | 10.550 | -8.253 | 1.00 | 61.25 | A | O |
| ATOM | 2177 | OH2 | H2O | A | 701 | 33.366 | 11.802 | 23.550 | 1.00 | 55.55 | A | O |
| ATOM | 2178 | CB | TRP | B | 238 | 47.249 | 28.041 | 32.086 | 1.00 | 59.87 | B | C |
| ATOM | 2179 | CG | TRP | B | 238 | 46.778 | 28.645 | 33.396 | 1.00 | 60.00 | B | C |
| ATOM | 2180 | CD2 | TRP | B | 238 | 47.350 | 28.418 | 34.684 | 1.00 | 59.55 | B | C |
| ATOM | 2181 | CE2 | TRP | B | 238 | 46.560 | 29.131 | 35.624 | 1.00 | 60.62 | B | C |
| ATOM | 2182 | CE3 | TRP | B | 238 | 48.435 | 27.677 | 35.137 | 1.00 | 58.21 | B | C |
| ATOM | 2183 | CD1 | TRP | B | 238 | 45.694 | 29.472 | 33.596 | 1.00 | 60.88 | B | C |
| ATOM | 2184 | NE1 | TRP | B | 238 | 45.564 | 29.764 | 34.944 | 1.00 | 61.19 | B | N |
| ATOM | 2185 | CZ2 | TRP | B | 238 | 46.845 | 29.101 | 36.997 | 1.00 | 61.03 | B | C |
| ATOM | 2186 | CZ3 | TRP | B | 238 | 48.707 | 27.651 | 36.500 | 1.00 | 58.41 | B | C |
| ATOM | 2187 | CH2 | TRP | B | 238 | 47.915 | 28.356 | 37.411 | 1.00 | 59.39 | B | C |
| ATOM | 2188 | C | TRP | B | 238 | 48.940 | 27.982 | 30.204 | 1.00 | 57.85 | B | C |
| ATOM | 2189 | O | TRP | B | 238 | 49.514 | 26.904 | 30.324 | 1.00 | 57.36 | B | O |
| ATOM | 2190 | N | TRP | B | 238 | 48.129 | 30.194 | 31.179 | 1.00 | 59.99 | B | N |
| ATOM | 2191 | CA | TRP | B | 238 | 48.462 | 28.753 | 31.457 | 1.00 | 59.05 | B | C |
| ATOM | 2192 | N | GLU | B | 239 | 48.649 | 28.502 | 29.010 | 1.00 | 57.23 | B | N |
| ATOM | 2193 | CA | GLU | B | 239 | 49.069 | 27.847 | 27.770 | 1.00 | 55.32 | B | C |
| ATOM | 2194 | CB | GLU | B | 239 | 48.253 | 28.303 | 26.548 | 1.00 | 57.73 | B | C |
| ATOM | 2195 | CG | GLU | B | 239 | 47.060 | 27.426 | 26.167 | 1.00 | 61.08 | B | C |
| ATOM | 2196 | CD | GLU | B | 239 | 45.834 | 27.630 | 27.084 | 1.00 | 62.40 | B | C |
| ATOM | 2197 | OE1 | GLU | B | 239 | 45.875 | 27.162 | 28.249 | 1.00 | 63.20 | B | O |
| ATOM | 2198 | OE2 | GLU | B | 239 | 44.828 | 28.237 | 26.631 | 1.00 | 62.28 | B | O |
| ATOM | 2199 | C | GLU | B | 239 | 50.508 | 28.227 | 27.537 | 1.00 | 52.68 | B | C |
| ATOM | 2200 | O | GLU | B | 239 | 50.919 | 29.373 | 27.764 | 1.00 | 52.60 | B | O |
| ATOM | 2201 | N | VAL | B | 240 | 51.284 | 27.243 | 27.132 | 1.00 | 49.99 | B | N |
| ATOM | 2202 | CA | VAL | B | 240 | 52.673 | 27.482 | 26.838 | 1.00 | 46.23 | B | C |
| ATOM | 2203 | CB | VAL | B | 240 | 53.606 | 27.064 | 27.980 | 1.00 | 45.56 | B | C |
| ATOM | 2204 | CG1 | VAL | B | 240 | 53.288 | 27.848 | 29.223 | 1.00 | 44.36 | B | C |
| ATOM | 2205 | CG2 | VAL | B | 240 | 53.563 | 25.574 | 28.195 | 1.00 | 44.48 | B | C |
| ATOM | 2206 | C | VAL | B | 240 | 53.052 | 26.726 | 25.600 | 1.00 | 44.38 | B | C |
| ATOM | 2207 | O | VAL | B | 240 | 52.354 | 25.825 | 25.155 | 1.00 | 42.88 | B | O |

Figure 13

| ATOM | 2208 | N | PRO | B | 241 | 54.129 | 27.162 | 24.969 | 1.00 | 43.28 | B | N |
|------|------|------|------|---|-----|--------|--------|--------|------|-------|---|---|
| ATOM | 2209 | CD | PRO | B | 241 | 54.727 | 28.491 | 25.125 | 1.00 | 41.10 | B | C |
| ATOM | 2210 | CA | PRO | B | 241 | 54.608 | 26.510 | 23.758 | 1.00 | 43.15 | B | C |
| ATOM | 2211 | CB | PRO | B | 241 | 55.650 | 27.499 | 23.258 | 1.00 | 42.50 | B | C |
| ATOM | 2212 | CG | PRO | B | 241 | 55.098 | 28.807 | 23.719 | 1.00 | 41.49 | B | C |
| ATOM | 2213 | C | PRO | B | 241 | 55.217 | 25.103 | 24.025 | 1.00 | 43.53 | B | C |
| ATOM | 2214 | O | PRO | B | 241 | 55.828 | 24.823 | 25.081 | 1.00 | 42.15 | B | O |
| ATOM | 2215 | N | ARG | B | 242 | 55.014 | 24.207 | 23.068 | 1.00 | 44.04 | B | N |
| ATOM | 2216 | CA | ARG | B | 242 | 55.557 | 22.852 | 23.174 | 1.00 | 45.13 | B | C |
| ATOM | 2217 | CB | ARG | B | 242 | 55.146 | 22.053 | 21.933 | 1.00 | 47.04 | B | C |
| ATOM | 2218 | CG | ARG | B | 242 | 55.772 | 20.659 | 21.797 | 1.00 | 49.23 | B | C |
| ATOM | 2219 | CD | ARG | B | 242 | 55.146 | 19.712 | 22.774 | 1.00 | 50.31 | B | C |
| ATOM | 2220 | NE | ARG | B | 242 | 53.692 | 19.709 | 22.704 | 1.00 | 52.13 | B | N |
| ATOM | 2221 | CZ | ARG | B | 242 | 52.999 | 19.266 | 21.663 | 1.00 | 52.88 | B | C |
| ATOM | 2222 | NH1 | ARG | B | 242 | 53.645 | 18.801 | 20.599 | 1.00 | 54.71 | B | N |
| ATOM | 2223 | NH2 | ARG | B | 242 | 51.671 | 19.252 | 21.700 | 1.00 | 51.38 | B | N |
| ATOM | 2224 | C | ARG | B | 242 | 57.096 | 22.863 | 23.323 | 1.00 | 44.65 | B | C |
| ATOM | 2225 | O | ARG | B | 242 | 57.663 | 22.010 | 24.000 | 1.00 | 44.58 | B | O |
| ATOM | 2226 | N | GLU | B | 243 | 57.733 | 23.890 | 22.757 | 1.00 | 44.79 | B | N |
| ATOM | 2227 | CA | GLU | B | 243 | 59.193 | 24.108 | 22.764 | 1.00 | 44.61 | B | C |
| ATOM | 2228 | CB | GLU | B | 243 | 59.522 | 25.445 | 22.049 | 1.00 | 49.07 | B | C |
| ATOM | 2229 | CG | GLU | B | 243 | 59.066 | 25.574 | 20.566 | 1.00 | 53.35 | B | C |
| ATOM | 2230 | CD | GLU | B | 243 | 57.651 | 25.003 | 20.284 | 1.00 | 53.57 | B | C |
| ATOM | 2231 | OE1 | GLU | B | 243 | 56.644 | 25.677 | 20.588 | 1.00 | 52.95 | B | O |
| ATOM | 2232 | OE2 | GLU | B | 243 | 57.562 | 23.872 | 19.754 | 1.00 | 52.40 | B | O |
| ATOM | 2233 | C | GLU | B | 243 | 59.760 | 24.201 | 24.180 | 1.00 | 42.55 | B | C |
| ATOM | 2234 | O | GLU | B | 243 | 60.835 | 23.691 | 24.470 | 1.00 | 41.18 | B | O |
| ATOM | 2235 | N | THR | B | 244 | 59.028 | 24.892 | 25.046 | 1.00 | 41.03 | B | N |
| ATOM | 2236 | CA | THR | B | 244 | 59.416 | 25.106 | 26.432 | 1.00 | 39.50 | B | C |
| ATOM | 2237 | CB | THR | B | 244 | 58.384 | 26.014 | 27.130 | 1.00 | 38.97 | B | C |
| ATOM | 2238 | OG1 | THR | B | 244 | 57.115 | 25.349 | 27.226 | 1.00 | 35.92 | B | O |
| ATOM | 2239 | CG2 | THR | B | 244 | 58.227 | 27.317 | 26.350 | 1.00 | 39.39 | B | C |
| ATOM | 2240 | C | THR | B | 244 | 59.468 | 23.835 | 27.237 | 1.00 | 39.29 | B | C |
| ATOM | 2241 | O | THR | B | 244 | 59.872 | 23.862 | 28.396 | 1.00 | 39.60 | B | O |
| ATOM | 2242 | N | LEU | B | 245 | 59.186 | 22.716 | 26.580 | 1.00 | 38.60 | B | N |
| ATOM | 2243 | CA | LEU | B | 245 | 59.081 | 21.452 | 27.257 | 1.00 | 38.59 | B | C |
| ATOM | 2244 | CB | LEU | B | 245 | 57.587 | 21.191 | 27.359 | 1.00 | 38.08 | B | C |
| ATOM | 2245 | CG | LEU | B | 245 | 56.971 | 20.524 | 28.572 | 1.00 | 38.49 | B | C |
| ATOM | 2246 | CD1 | LEU | B | 245 | 57.150 | 21.342 | 29.797 | 1.00 | 37.64 | B | C |
| ATOM | 2247 | CD2 | LEU | B | 245 | 55.469 | 20.333 | 28.262 | 1.00 | 39.42 | B | C |
| ATOM | 2248 | C | LEU | B | 245 | 59.812 | 20.226 | 26.667 | 1.00 | 39.42 | B | C |
| ATOM | 2249 | O | LEU | B | 245 | 59.601 | 19.820 | 25.512 | 1.00 | 39.23 | B | O |
| ATOM | 2250 | N | LYS | B | 246 | 60.645 | 19.605 | 27.492 | 1.00 | 39.13 | B | N |
| ATOM | 2251 | CA | LYS | B | 246 | 61.382 | 18.426 | 27.059 | 1.00 | 39.58 | B | C |
| ATOM | 2252 | CB | LYS | B | 246 | 62.911 | 18.663 | 27.125 | 1.00 | 43.48 | B | C |
| ATOM | 2253 | CG | LYS | B | 246 | 63.744 | 17.438 | 26.687 | 1.00 | 47.88 | B | C |
| ATOM | 2254 | CD | LYS | B | 246 | 65.267 | 17.680 | 26.626 | 1.00 | 52.58 | B | C |
| ATOM | 2255 | CE | LYS | B | 246 | 65.900 | 18.196 | 27.954 | 1.00 | 56.31 | B | C |
| ATOM | 2256 | NZ | LYS | B | 246 | 67.385 | 18.428 | 27.796 | 1.00 | 59.76 | B | N |
| ATOM | 2257 | C | LYS | B | 246 | 60.954 | 17.207 | 27.893 | 1.00 | 38.24 | B | C |
| ATOM | 2258 | O | LYS | B | 246 | 61.045 | 17.170 | 29.120 | 1.00 | 38.33 | B | O |
| ATOM | 2259 | N | LEU | B | 247 | 60.396 | 16.251 | 27.188 | 1.00 | 36.61 | B | N |
| ATOM | 2260 | CA | LEU | B | 247 | 59.897 | 15.052 | 27.772 | 1.00 | 35.50 | B | C |
| ATOM | 2261 | CB | LEU | B | 247 | 58.760 | 14.560 | 26.902 | 1.00 | 34.19 | B | C |
| ATOM | 2262 | CG | LEU | B | 247 | 57.364 | 14.871 | 27.439 | 1.00 | 32.52 | B | C |
| ATOM | 2263 | CD1 | LEU | B | 247 | 57.060 | 16.383 | 27.426 | 1.00 | 34.04 | B | C |
| ATOM | 2264 | CD2 | LEU | B | 247 | 56.367 | 14.104 | 26.632 | 1.00 | 30.26 | B | C |
| ATOM | 2265 | C | LEU | B | 247 | 60.989 | 14.014 | 27.811 | 1.00 | 36.42 | B | C |
| ATOM | 2266 | O | LEU | B | 247 | 61.315 | 13.429 | 26.765 | 1.00 | 37.21 | B | O |
| ATOM | 2267 | N | VAL | B | 248 | 61.466 | 13.680 | 29.018 | 1.00 | 36.12 | B | N |

Figure 13

| ATOM | 2268 | CA  | VAL | B | 248 | 62.569 | 12.718 | 29.153 | 1.00 | 35.81 | B | C |
| ATOM | 2269 | CB  | VAL | B | 248 | 63.579 | 13.130 | 30.246 | 1.00 | 34.58 | B | C |
| ATOM | 2270 | CG1 | VAL | B | 248 | 64.877 | 12.296 | 30.116 | 1.00 | 32.41 | B | C |
| ATOM | 2271 | CG2 | VAL | B | 248 | 63.888 | 14.566 | 30.147 | 1.00 | 35.35 | B | C |
| ATOM | 2272 | C   | VAL | B | 248 | 62.283 | 11.225 | 29.349 | 1.00 | 35.85 | B | C |
| ATOM | 2273 | O   | VAL | B | 248 | 62.700 | 10.372 | 28.560 | 1.00 | 35.78 | B | O |
| ATOM | 2274 | N   | GLU | B | 249 | 61.578 | 10.900 | 30.413 | 1.00 | 35.94 | B | N |
| ATOM | 2275 | CA  | GLU | B | 249 | 61.332 | 9.505  | 30.708 | 1.00 | 35.77 | B | C |
| ATOM | 2276 | CB  | GLU | B | 249 | 62.223 | 9.145  | 31.877 | 1.00 | 38.12 | B | C |
| ATOM | 2277 | CG  | GLU | B | 249 | 61.977 | 7.841  | 32.542 | 1.00 | 41.96 | B | C |
| ATOM | 2278 | CD  | GLU | B | 249 | 62.592 | 7.812  | 33.954 | 1.00 | 45.56 | B | C |
| ATOM | 2279 | OE1 | GLU | B | 249 | 63.405 | 8.746  | 34.284 | 1.00 | 46.87 | B | O |
| ATOM | 2280 | OE2 | GLU | B | 249 | 62.260 | 6.858  | 34.726 | 1.00 | 47.37 | B | O |
| ATOM | 2281 | C   | GLU | B | 249 | 59.873 | 9.206  | 31.011 | 1.00 | 34.67 | B | C |
| ATOM | 2282 | O   | GLU | B | 249 | 59.197 | 9.960  | 31.717 | 1.00 | 34.64 | B | O |
| ATOM | 2283 | N   | ARG | B | 250 | 59.381 | 8.127  | 30.414 | 1.00 | 33.96 | B | N |
| ATOM | 2284 | CA  | ARG | B | 250 | 57.997 | 7.736  | 30.589 | 1.00 | 32.83 | B | C |
| ATOM | 2285 | CB  | ARG | B | 250 | 57.528 | 6.800  | 29.500 | 1.00 | 31.64 | B | C |
| ATOM | 2286 | CG  | ARG | B | 250 | 56.037 | 6.898  | 29.447 | 1.00 | 33.26 | B | C |
| ATOM | 2287 | CD  | ARG | B | 250 | 55.451 | 6.114  | 28.306 | 1.00 | 35.62 | B | C |
| ATOM | 2288 | NE  | ARG | B | 250 | 55.519 | 4.672  | 28.548 | 1.00 | 37.11 | B | N |
| ATOM | 2289 | CZ  | ARG | B | 250 | 55.289 | 3.741  | 27.629 | 1.00 | 37.53 | B | C |
| ATOM | 2290 | NH1 | ARG | B | 250 | 54.969 | 4.087  | 26.398 | 1.00 | 37.06 | B | N |
| ATOM | 2291 | NH2 | ARG | B | 250 | 55.516 | 2.476  | 27.916 | 1.00 | 37.57 | B | N |
| ATOM | 2292 | C   | ARG | B | 250 | 57.734 | 7.094  | 31.922 | 1.00 | 32.11 | B | C |
| ATOM | 2293 | O   | ARG | B | 250 | 58.292 | 6.056  | 32.207 | 1.00 | 32.77 | B | O |
| ATOM | 2294 | N   | LEU | B | 251 | 56.890 | 7.702  | 32.743 | 1.00 | 31.46 | B | N |
| ATOM | 2295 | CA  | LEU | B | 251 | 56.619 | 7.122  | 34.044 | 1.00 | 30.06 | B | C |
| ATOM | 2296 | CB  | LEU | B | 251 | 56.245 | 8.191  | 35.061 | 1.00 | 26.93 | B | C |
| ATOM | 2297 | CG  | LEU | B | 251 | 57.422 | 9.161  | 35.271 | 1.00 | 25.27 | B | C |
| ATOM | 2298 | CD1 | LEU | B | 251 | 57.043 | 10.275 | 36.214 | 1.00 | 24.97 | B | C |
| ATOM | 2299 | CD2 | LEU | B | 251 | 58.651 | 8.463  | 35.794 | 1.00 | 23.50 | B | C |
| ATOM | 2300 | C   | LEU | B | 251 | 55.567 | 6.040  | 33.947 | 1.00 | 30.40 | B | C |
| ATOM | 2301 | O   | LEU | B | 251 | 55.622 | 5.049  | 34.649 | 1.00 | 31.27 | B | O |
| ATOM | 2302 | N   | GLY | B | 252 | 54.625 | 6.205  | 33.044 | 1.00 | 30.42 | B | N |
| ATOM | 2303 | CA  | GLY | B | 252 | 53.586 | 5.193  | 32.890 | 1.00 | 29.76 | B | C |
| ATOM | 2304 | C   | GLY | B | 252 | 52.697 | 5.457  | 31.677 | 1.00 | 29.48 | B | C |
| ATOM | 2305 | O   | GLY | B | 252 | 52.578 | 6.574  | 31.140 | 1.00 | 28.56 | B | O |
| ATOM | 2306 | N   | ALA | B | 253 | 52.036 | 4.404  | 31.255 | 1.00 | 30.46 | B | N |
| ATOM | 2307 | CA  | ALA | B | 253 | 51.154 | 4.480  | 30.097 | 1.00 | 31.61 | B | C |
| ATOM | 2308 | CB  | ALA | B | 253 | 51.888 | 3.963  | 28.832 | 1.00 | 32.92 | B | C |
| ATOM | 2309 | C   | ALA | B | 253 | 49.891 | 3.662  | 30.340 | 1.00 | 31.04 | B | C |
| ATOM | 2310 | O   | ALA | B | 253 | 49.923 | 2.523  | 30.844 | 1.00 | 30.30 | B | O |
| ATOM | 2311 | N   | GLY | B | 254 | 48.781 | 4.263  | 29.943 | 1.00 | 32.31 | B | N |
| ATOM | 2312 | CA  | GLY | B | 254 | 47.489 | 3.631  | 30.103 | 1.00 | 32.58 | B | C |
| ATOM | 2313 | C   | GLY | B | 254 | 46.548 | 3.770  | 28.922 | 1.00 | 33.09 | B | C |
| ATOM | 2314 | O   | GLY | B | 254 | 46.921 | 4.261  | 27.862 | 1.00 | 32.83 | B | O |
| ATOM | 2315 | N   | GLN | B | 255 | 45.321 | 3.314  | 29.127 | 1.00 | 34.64 | B | N |
| ATOM | 2316 | CA  | GLN | B | 255 | 44.266 | 3.322  | 28.132 | 1.00 | 36.58 | B | C |
| ATOM | 2317 | CB  | GLN | B | 255 | 42.964 | 2.764  | 28.751 | 1.00 | 39.96 | B | C |
| ATOM | 2318 | CG  | GLN | B | 255 | 41.983 | 2.141  | 27.715 | 1.00 | 44.27 | B | C |
| ATOM | 2319 | CD  | GLN | B | 255 | 40.494 | 2.141  | 28.096 | 1.00 | 46.12 | B | C |
| ATOM | 2320 | OE1 | GLN | B | 255 | 39.614 | 2.036  | 27.212 | 1.00 | 45.56 | B | O |
| ATOM | 2321 | NE2 | GLN | B | 255 | 40.205 | 2.244  | 29.394 | 1.00 | 47.65 | B | N |
| ATOM | 2322 | C   | GLN | B | 255 | 43.987 | 4.677  | 27.553 | 1.00 | 36.38 | B | C |
| ATOM | 2323 | O   | GLN | B | 255 | 43.798 | 4.793  | 26.358 | 1.00 | 36.48 | B | O |
| ATOM | 2324 | N   | PHE | B | 256 | 44.020 | 5.702  | 28.403 | 1.00 | 36.19 | B | N |
| ATOM | 2325 | CA  | PHE | B | 256 | 43.734 | 7.093  | 28.005 | 1.00 | 35.34 | B | C |
| ATOM | 2326 | CB  | PHE | B | 256 | 42.946 | 7.823  | 29.106 | 1.00 | 35.25 | B | C |
| ATOM | 2327 | CG  | PHE | B | 256 | 41.530 | 7.368  | 29.252 | 1.00 | 35.46 | B | C |

Figure 13

| ATOM | 2328 | CD1 | PHE | B | 256 | 41.008 | 6.407 | 28.425 | 1.00 | 35.57 | B | C |
| ATOM | 2329 | CD2 | PHE | B | 256 | 40.711 | 7.939 | 30.219 | 1.00 | 36.71 | B | C |
| ATOM | 2330 | CE1 | PHE | B | 256 | 39.687 | 5.992 | 28.553 | 1.00 | 36.85 | B | C |
| ATOM | 2331 | CE2 | PHE | B | 256 | 39.376 | 7.541 | 30.368 | 1.00 | 37.74 | B | C |
| ATOM | 2332 | CZ | PHE | B | 256 | 38.862 | 6.567 | 29.527 | 1.00 | 37.87 | B | C |
| ATOM | 2333 | C | PHE | B | 256 | 44.894 | 8.001 | 27.632 | 1.00 | 34.90 | B | C |
| ATOM | 2334 | O | PHE | B | 256 | 44.655 | 9.099 | 27.126 | 1.00 | 34.71 | B | O |
| ATOM | 2335 | N | GLY | B | 257 | 46.129 | 7.603 | 27.958 | 1.00 | 35.07 | B | N |
| ATOM | 2336 | CA | GLY | B | 257 | 47.267 | 8.455 | 27.657 | 1.00 | 33.45 | B | C |
| ATOM | 2337 | C | GLY | B | 257 | 48.498 | 8.013 | 28.399 | 1.00 | 33.03 | B | C |
| ATOM | 2338 | O | GLY | B | 257 | 48.576 | 6.851 | 28.746 | 1.00 | 33.19 | B | O |
| ATOM | 2339 | N | GLU | B | 258 | 49.431 | 8.932 | 28.668 | 1.00 | 33.13 | B | N |
| ATOM | 2340 | CA | GLU | B | 258 | 50.686 | 8.610 | 29.334 | 1.00 | 33.25 | B | C |
| ATOM | 2341 | CB | GLU | B | 258 | 51.749 | 8.401 | 28.270 | 1.00 | 32.79 | B | C |
| ATOM | 2342 | CG | GLU | B | 258 | 51.381 | 7.424 | 27.185 | 1.00 | 32.05 | B | C |
| ATOM | 2343 | CD | GLU | B | 258 | 52.483 | 7.320 | 26.137 | 1.00 | 33.34 | B | C |
| ATOM | 2344 | OE1 | GLU | B | 258 | 53.021 | 8.378 | 25.747 | 1.00 | 31.94 | B | O |
| ATOM | 2345 | OE2 | GLU | B | 258 | 52.833 | 6.183 | 25.724 | 1.00 | 32.85 | B | O |
| ATOM | 2346 | C | GLU | B | 258 | 51.149 | 9.739 | 30.224 | 1.00 | 33.37 | B | C |
| ATOM | 2347 | O | GLU | B | 258 | 50.769 | 10.878 | 30.005 | 1.00 | 34.94 | B | O |
| ATOM | 2348 | N | VAL | B | 259 | 52.053 | 9.439 | 31.158 | 1.00 | 32.59 | B | N |
| ATOM | 2349 | CA | VAL | B | 259 | 52.612 | 10.435 | 32.101 | 1.00 | 31.48 | B | C |
| ATOM | 2350 | CB | VAL | B | 259 | 52.281 | 10.099 | 33.565 | 1.00 | 30.76 | B | C |
| ATOM | 2351 | CG1 | VAL | B | 259 | 52.705 | 11.255 | 34.483 | 1.00 | 31.78 | B | C |
| ATOM | 2352 | CG2 | VAL | B | 259 | 50.851 | 9.720 | 33.715 | 1.00 | 29.16 | B | C |
| ATOM | 2353 | C | VAL | B | 259 | 54.131 | 10.298 | 31.995 | 1.00 | 31.27 | B | C |
| ATOM | 2354 | O | VAL | B | 259 | 54.646 | 9.169 | 32.031 | 1.00 | 32.54 | B | O |
| ATOM | 2355 | N | TRP | B | 260 | 54.837 | 11.419 | 31.842 | 1.00 | 29.94 | B | N |
| ATOM | 2356 | CA | TRP | B | 260 | 56.295 | 11.438 | 31.693 | 1.00 | 28.31 | B | C |
| ATOM | 2357 | CB | TRP | B | 260 | 56.665 | 11.944 | 30.297 | 1.00 | 27.07 | B | C |
| ATOM | 2358 | CG | TRP | B | 260 | 56.406 | 11.051 | 29.160 | 1.00 | 27.00 | B | C |
| ATOM | 2359 | CD2 | TRP | B | 260 | 57.384 | 10.445 | 28.315 | 1.00 | 28.61 | B | C |
| ATOM | 2360 | CE2 | TRP | B | 260 | 56.705 | 9.692 | 27.345 | 1.00 | 28.72 | B | C |
| ATOM | 2361 | CE3 | TRP | B | 260 | 58.795 | 10.465 | 28.275 | 1.00 | 30.07 | B | C |
| ATOM | 2362 | CD1 | TRP | B | 260 | 55.193 | 10.654 | 28.683 | 1.00 | 26.19 | B | C |
| ATOM | 2363 | NE1 | TRP | B | 260 | 55.359 | 9.829 | 27.604 | 1.00 | 27.05 | B | N |
| ATOM | 2364 | CZ2 | TRP | B | 260 | 57.368 | 8.973 | 26.349 | 1.00 | 28.96 | B | C |
| ATOM | 2365 | CZ3 | TRP | B | 260 | 59.454 | 9.744 | 27.276 | 1.00 | 29.29 | B | C |
| ATOM | 2366 | CH2 | TRP | B | 260 | 58.744 | 9.018 | 26.334 | 1.00 | 29.51 | B | C |
| ATOM | 2367 | C | TRP | B | 260 | 56.960 | 12.411 | 32.642 | 1.00 | 28.46 | B | C |
| ATOM | 2368 | O | TRP | B | 260 | 56.341 | 13.361 | 33.135 | 1.00 | 28.43 | B | O |
| ATOM | 2369 | N | MET | B | 261 | 58.235 | 12.160 | 32.913 | 1.00 | 28.87 | B | N |
| ATOM | 2370 | CA | MET | B | 261 | 59.025 | 13.096 | 33.698 | 1.00 | 29.06 | B | C |
| ATOM | 2371 | CB | MET | B | 261 | 59.985 | 12.389 | 34.654 | 1.00 | 27.28 | B | C |
| ATOM | 2372 | CG | MET | B | 261 | 60.960 | 13.339 | 35.344 | 1.00 | 26.57 | B | C |
| ATOM | 2373 | SD | MET | B | 261 | 62.428 | 13.910 | 34.303 | 1.00 | 26.44 | B | S |
| ATOM | 2374 | CE | MET | B | 261 | 63.279 | 12.220 | 34.162 | 1.00 | 24.68 | B | C |
| ATOM | 2375 | C | MET | B | 261 | 59.783 | 13.879 | 32.613 | 1.00 | 29.30 | B | C |
| ATOM | 2376 | O | MET | B | 261 | 60.108 | 13.328 | 31.555 | 1.00 | 29.45 | B | O |
| ATOM | 2377 | N | GLY | B | 262 | 60.027 | 15.159 | 32.840 | 1.00 | 29.38 | B | N |
| ATOM | 2378 | CA | GLY | B | 262 | 60.733 | 15.919 | 31.840 | 1.00 | 30.10 | B | C |
| ATOM | 2379 | C | GLY | B | 262 | 61.267 | 17.164 | 32.457 | 1.00 | 30.97 | B | C |
| ATOM | 2380 | O | GLY | B | 262 | 61.575 | 17.160 | 33.644 | 1.00 | 31.80 | B | O |
| ATOM | 2381 | N | TYR | B | 263 | 61.442 | 18.202 | 31.646 | 1.00 | 31.59 | B | N |
| ATOM | 2382 | CA | TYR | B | 263 | 61.936 | 19.466 | 32.161 | 1.00 | 33.65 | B | C |
| ATOM | 2383 | CB | TYR | B | 263 | 63.457 | 19.534 | 31.980 | 1.00 | 31.68 | B | C |
| ATOM | 2384 | CG | TYR | B | 263 | 64.191 | 18.533 | 32.844 | 1.00 | 28.40 | B | C |
| ATOM | 2385 | CD1 | TYR | B | 263 | 64.604 | 18.888 | 34.117 | 1.00 | 27.16 | B | C |
| ATOM | 2386 | CE1 | TYR | B | 263 | 65.227 | 17.984 | 34.936 | 1.00 | 26.68 | B | C |
| ATOM | 2387 | CD2 | TYR | B | 263 | 64.422 | 17.219 | 32.401 | 1.00 | 25.96 | B | C |

Figure 13

```
ATOM  2388  CE2  TYR B 263      65.047  16.283  33.219  1.00 24.86      B    C
ATOM  2389  CZ   TYR B 263      65.458  16.683  34.502  1.00 26.92      B    C
ATOM  2390  OH   TYR B 263      66.139  15.851  35.384  1.00 27.06      B    O
ATOM  2391  C    TYR B 263      61.197  20.624  31.506  1.00 36.00      B    C
ATOM  2392  O    TYR B 263      60.778  20.508  30.351  1.00 36.93      B    O
ATOM  2393  N    TYR B 264      60.919  21.665  32.297  1.00 37.66      B    N
ATOM  2394  CA   TYR B 264      60.170  22.843  31.849  1.00 40.65      B    C
ATOM  2395  CB   TYR B 264      58.911  23.025  32.768  1.00 40.29      B    C
ATOM  2396  CG   TYR B 264      57.930  24.155  32.484  1.00 41.72      B    C
ATOM  2397  CD1  TYR B 264      57.550  24.492  31.181  1.00 42.37      B    C
ATOM  2398  CE1  TYR B 264      56.731  25.595  30.925  1.00 44.10      B    C
ATOM  2399  CD2  TYR B 264      57.446  24.937  33.533  1.00 42.66      B    C
ATOM  2400  CE2  TYR B 264      56.631  26.039  33.299  1.00 44.36      B    C
ATOM  2401  CZ   TYR B 264      56.282  26.387  31.995  1.00 44.95      B    C
ATOM  2402  OH   TYR B 264      55.587  27.579  31.785  1.00 44.13      B    O
ATOM  2403  C    TYR B 264      61.151  24.003  31.912  1.00 42.17      B    C
ATOM  2404  O    TYR B 264      61.720  24.283  32.964  1.00 43.38      B    O
ATOM  2405  N    ASN B 265      61.393  24.637  30.771  1.00 43.09      B    N
ATOM  2406  CA   ASN B 265      62.333  25.755  30.717  1.00 44.36      B    C
ATOM  2407  CB   ASN B 265      61.885  26.877  31.679  1.00 44.07      B    C
ATOM  2408  CG   ASN B 265      60.477  27.435  31.337  1.00 44.10      B    C
ATOM  2409  OD1  ASN B 265      60.170  27.670  30.165  1.00 42.00      B    O
ATOM  2410  ND2  ASN B 265      59.636  27.656  32.364  1.00 43.59      B    N
ATOM  2411  C    ASN B 265      63.733  25.204  31.065  1.00 45.49      B    C
ATOM  2412  O    ASN B 265      64.516  25.799  31.822  1.00 45.25      B    O
ATOM  2413  N    GLY B 266      63.971  23.991  30.570  1.00 47.13      B    N
ATOM  2414  CA   GLY B 266      65.223  23.294  30.784  1.00 48.96      B    C
ATOM  2415  C    GLY B 266      65.593  22.860  32.194  1.00 50.97      B    C
ATOM  2416  O    GLY B 266      66.243  21.812  32.347  1.00 51.57      B    O
ATOM  2417  N    HIS B 267      65.163  23.601  33.226  1.00 52.34      B    N
ATOM  2418  CA   HIS B 267      65.550  23.267  34.611  1.00 53.41      B    C
ATOM  2419  CB   HIS B 267      66.497  24.331  35.156  1.00 57.43      B    C
ATOM  2420  CG   HIS B 267      67.850  24.299  34.511  1.00 62.41      B    C
ATOM  2421  CD2  HIS B 267      68.742  23.285  34.350  1.00 63.06      B    C
ATOM  2422  ND1  HIS B 267      68.415  25.405  33.907  1.00 64.77      B    N
ATOM  2423  CE1  HIS B 267      69.596  25.077  33.404  1.00 64.98      B    C
ATOM  2424  NE2  HIS B 267      69.814  23.797  33.660  1.00 64.01      B    N
ATOM  2425  C    HIS B 267      64.533  22.882  35.689  1.00 51.67      B    C
ATOM  2426  O    HIS B 267      64.929  22.383  36.744  1.00 51.68      B    O
ATOM  2427  N    THR B 268      63.257  23.197  35.491  1.00 48.83      B    N
ATOM  2428  CA   THR B 268      62.243  22.784  36.452  1.00 45.48      B    C
ATOM  2429  CB   THR B 268      61.045  23.700  36.392  1.00 44.70      B    C
ATOM  2430  OG1  THR B 268      61.478  25.024  36.704  1.00 45.51      B    O
ATOM  2431  CG2  THR B 268      59.966  23.265  37.383  1.00 43.61      B    C
ATOM  2432  C    THR B 268      61.806  21.365  36.094  1.00 43.42      B    C
ATOM  2433  O    THR B 268      61.359  21.110  34.966  1.00 42.40      B    O
ATOM  2434  N    LYS B 269      61.974  20.430  37.030  1.00 41.01      B    N
ATOM  2435  CA   LYS B 269      61.582  19.044  36.786  1.00 38.59      B    C
ATOM  2436  CB   LYS B 269      62.210  18.138  37.822  1.00 39.16      B    C
ATOM  2437  CG   LYS B 269      62.274  16.697  37.424  1.00 39.77      B    C
ATOM  2438  CD   LYS B 269      63.253  15.974  38.338  1.00 39.48      B    C
ATOM  2439  CE   LYS B 269      63.726  14.681  37.713  1.00 39.87      B    C
ATOM  2440  NZ   LYS B 269      64.493  13.884  38.720  1.00 41.19      B    N
ATOM  2441  C    LYS B 269      60.052  18.966  36.883  1.00 36.52      B    C
ATOM  2442  O    LYS B 269      59.487  19.470  37.853  1.00 35.16      B    O
ATOM  2443  N    VAL B 270      59.414  18.302  35.925  1.00 34.73      B    N
ATOM  2444  CA   VAL B 270      57.946  18.181  35.881  1.00 32.08      B    C
ATOM  2445  CB   VAL B 270      57.361  19.078  34.744  1.00 29.40      B    C
ATOM  2446  CG1  VAL B 270      57.415  20.510  35.098  1.00 26.01      B    C
ATOM  2447  CG2  VAL B 270      58.109  18.765  33.424  1.00 27.70      B    C
```

Figure 13

```
ATOM   2448  C    VAL B 270      57.418  16.767  35.547  1.00 32.46      B  C
ATOM   2449  O    VAL B 270      58.177  15.820  35.250  1.00 32.33      B  O
ATOM   2450  N    ALA B 271      56.087  16.654  35.621  1.00 32.13      B  N
ATOM   2451  CA   ALA B 271      55.337  15.448  35.253  1.00 30.91      B  C
ATOM   2452  CB   ALA B 271      54.519  14.946  36.434  1.00 31.24      B  C
ATOM   2453  C    ALA B 271      54.441  16.068  34.192  1.00 30.00      B  C
ATOM   2454  O    ALA B 271      53.877  17.143  34.406  1.00 29.45      B  O
ATOM   2455  N    VAL B 272      54.330  15.398  33.057  1.00 29.05      B  N
ATOM   2456  CA   VAL B 272      53.563  15.892  31.934  1.00 28.61      B  C
ATOM   2457  CB   VAL B 272      54.470  16.077  30.685  1.00 28.49      B  C
ATOM   2458  CG1  VAL B 272      53.664  16.515  29.441  1.00 27.67      B  C
ATOM   2459  CG2  VAL B 272      55.625  17.005  31.003  1.00 27.24      B  C
ATOM   2460  C    VAL B 272      52.659  14.779  31.568  1.00 28.69      B  C
ATOM   2461  O    VAL B 272      53.168  13.737  31.184  1.00 29.52      B  O
ATOM   2462  N    LYS B 273      51.338  14.964  31.650  1.00 28.95      B  N
ATOM   2463  CA   LYS B 273      50.410  13.874  31.270  1.00 28.54      B  C
ATOM   2464  CB   LYS B 273      49.356  13.717  32.367  1.00 27.84      B  C
ATOM   2465  CG   LYS B 273      48.130  12.873  32.045  1.00 26.39      B  C
ATOM   2466  CD   LYS B 273      47.126  13.023  33.175  1.00 26.00      B  C
ATOM   2467  CE   LYS B 273      47.514  12.106  34.378  1.00 27.56      B  C
ATOM   2468  NZ   LYS B 273      46.375  11.869  35.385  1.00 25.70      B  N
ATOM   2469  C    LYS B 273      49.813  14.138  29.883  1.00 29.07      B  C
ATOM   2470  O    LYS B 273      49.182  15.164  29.645  1.00 28.77      B  O
ATOM   2471  N    SER B 274      49.974  13.198  28.976  1.00 30.33      B  N
ATOM   2472  CA   SER B 274      49.469  13.428  27.639  1.00 32.46      B  C
ATOM   2473  CB   SER B 274      50.567  13.180  26.626  1.00 32.30      B  C
ATOM   2474  OG   SER B 274      50.973  11.827  26.681  1.00 35.15      B  O
ATOM   2475  C    SER B 274      48.245  12.585  27.290  1.00 33.68      B  C
ATOM   2476  O    SER B 274      48.129  11.451  27.720  1.00 33.60      B  O
ATOM   2477  N    LEU B 275      47.355  13.149  26.475  1.00 36.15      B  N
ATOM   2478  CA   LEU B 275      46.119  12.478  26.072  1.00 37.86      B  C
ATOM   2479  CB   LEU B 275      44.977  13.504  25.909  1.00 36.42      B  C
ATOM   2480  CG   LEU B 275      43.666  13.017  25.264  1.00 37.62      B  C
ATOM   2481  CD1  LEU B 275      42.868  12.066  26.209  1.00 37.63      B  C
ATOM   2482  CD2  LEU B 275      42.822  14.207  24.869  1.00 37.33      B  C
ATOM   2483  C    LEU B 275      46.241  11.638  24.789  1.00 39.41      B  C
ATOM   2484  O    LEU B 275      46.668  12.133  23.743  1.00 39.89      B  O
ATOM   2485  N    LYS B 276      45.840  10.369  24.870  1.00 40.78      B  N
ATOM   2486  CA   LYS B 276      45.840   9.486  23.715  1.00 43.10      B  C
ATOM   2487  CB   LYS B 276      45.611   8.036  24.169  1.00 42.88      B  C
ATOM   2488  CG   LYS B 276      45.411   6.991  23.046  1.00 44.77      B  C
ATOM   2489  CD   LYS B 276      45.316   5.540  23.579  1.00 47.66      B  C
ATOM   2490  CE   LYS B 276      46.560   5.191  24.439  1.00 51.35      B  C
ATOM   2491  NZ   LYS B 276      46.582   3.788  25.040  1.00 53.53      B  N
ATOM   2492  C    LYS B 276      44.619   9.984  22.929  1.00 44.90      B  C
ATOM   2493  O    LYS B 276      43.499   9.939  23.431  1.00 45.79      B  O
ATOM   2494  N    GLN B 277      44.851  10.534  21.739  1.00 45.98      B  N
ATOM   2495  CA   GLN B 277      43.783  11.043  20.855  1.00 47.08      B  C
ATOM   2496  CB   GLN B 277      44.361  11.416  19.490  1.00 51.07      B  C
ATOM   2497  CG   GLN B 277      43.377  11.973  18.451  1.00 55.83      B  C
ATOM   2498  CD   GLN B 277      44.094  12.243  17.085  1.00 59.71      B  C
ATOM   2499  OE1  GLN B 277      45.207  11.707  16.859  1.00 61.83      B  O
ATOM   2500  NE2  GLN B 277      43.463  12.998  16.183  1.00 60.00      B  N
ATOM   2501  C    GLN B 277      42.644  10.033  20.659  1.00 46.85      B  C
ATOM   2502  O    GLN B 277      42.890   8.856  20.365  1.00 45.58      B  O
ATOM   2503  N    GLY B 278      41.411  10.494  20.908  1.00 46.19      B  N
ATOM   2504  CA   GLY B 278      40.248   9.647  20.793  1.00 45.12      B  C
ATOM   2505  C    GLY B 278      39.748   9.116  22.131  1.00 45.04      B  C
ATOM   2506  O    GLY B 278      38.602   8.640  22.185  1.00 45.91      B  O
ATOM   2507  N    SER B 279      40.572   9.124  23.186  1.00 43.80      B  N
```

Figure 13

| | | | | | | | | | | | |
|---|---|---|---|---|---|---|---|---|---|---|---|
| ATOM | 2508 | CA | SER | B | 279 | 40.151 | 8.615 | 24.506 | 1.00 | 43.51 | B C |
| ATOM | 2509 | CB | SER | B | 279 | 41.321 | 8.648 | 25.493 | 1.00 | 44.59 | B C |
| ATOM | 2510 | OG | SER | B | 279 | 42.379 | 7.813 | 25.067 | 1.00 | 45.85 | B O |
| ATOM | 2511 | C | SER | B | 279 | 38.974 | 9.438 | 25.072 | 1.00 | 42.32 | B C |
| ATOM | 2512 | O | SER | B | 279 | 38.101 | 8.941 | 25.788 | 1.00 | 40.81 | B O |
| ATOM | 2513 | N | MET | B | 280 | 39.012 | 10.720 | 24.745 | 1.00 | 41.14 | B N |
| ATOM | 2514 | CA | MET | B | 280 | 38.024 | 11.704 | 25.135 | 1.00 | 40.89 | B C |
| ATOM | 2515 | CB | MET | B | 280 | 38.030 | 11.950 | 26.656 | 1.00 | 38.88 | B C |
| ATOM | 2516 | CG | MET | B | 280 | 39.295 | 12.581 | 27.186 | 1.00 | 38.71 | B C |
| ATOM | 2517 | SD | MET | B | 280 | 39.362 | 12.453 | 28.964 | 1.00 | 36.14 | B S |
| ATOM | 2518 | CE | MET | B | 280 | 38.799 | 13.888 | 29.385 | 1.00 | 39.80 | B C |
| ATOM | 2519 | C | MET | B | 280 | 38.401 | 12.960 | 24.393 | 1.00 | 41.35 | B C |
| ATOM | 2520 | O | MET | B | 280 | 39.512 | 13.104 | 23.885 | 1.00 | 41.97 | B O |
| ATOM | 2521 | N | SER | B | 281 | 37.490 | 13.905 | 24.354 | 1.00 | 41.80 | B N |
| ATOM | 2522 | CA | SER | B | 281 | 37.790 | 15.117 | 23.620 | 1.00 | 42.17 | B C |
| ATOM | 2523 | CB | SER | B | 281 | 36.534 | 15.942 | 23.340 | 1.00 | 41.35 | B C |
| ATOM | 2524 | OG | SER | B | 281 | 36.166 | 16.686 | 24.488 | 1.00 | 38.37 | B O |
| ATOM | 2525 | C | SER | B | 281 | 38.827 | 15.985 | 24.338 | 1.00 | 43.35 | B C |
| ATOM | 2526 | O | SER | B | 281 | 39.007 | 15.917 | 25.551 | 1.00 | 42.54 | B O |
| ATOM | 2527 | N | PRO | B | 282 | 39.601 | 16.751 | 23.538 | 1.00 | 44.10 | B N |
| ATOM | 2528 | CD | PRO | B | 282 | 39.779 | 16.459 | 22.102 | 1.00 | 45.04 | B C |
| ATOM | 2529 | CA | PRO | B | 282 | 40.653 | 17.665 | 23.995 | 1.00 | 44.08 | B C |
| ATOM | 2530 | CB | PRO | B | 282 | 41.026 | 18.391 | 22.727 | 1.00 | 43.66 | B C |
| ATOM | 2531 | CG | PRO | B | 282 | 41.048 | 17.294 | 21.737 | 1.00 | 44.70 | B C |
| ATOM | 2532 | C | PRO | B | 282 | 40.131 | 18.638 | 25.015 | 1.00 | 45.33 | B C |
| ATOM | 2533 | O | PRO | B | 282 | 40.593 | 18.676 | 26.112 | 1.00 | 44.47 | B O |
| ATOM | 2534 | N | ASP | B | 283 | 39.018 | 19.314 | 24.698 | 1.00 | 48.43 | B N |
| ATOM | 2535 | CA | ASP | B | 283 | 38.421 | 20.249 | 25.669 | 1.00 | 51.69 | B C |
| ATOM | 2536 | CB | ASP | B | 283 | 37.317 | 21.120 | 25.005 | 1.00 | 53.18 | B C |
| ATOM | 2537 | CG | ASP | B | 283 | 37.852 | 22.079 | 23.887 | 1.00 | 57.00 | B C |
| ATOM | 2538 | OD1 | ASP | B | 283 | 39.111 | 22.290 | 23.756 | 1.00 | 58.62 | B O |
| ATOM | 2539 | OD2 | ASP | B | 283 | 37.019 | 22.673 | 23.148 | 1.00 | 58.82 | B O |
| ATOM | 2540 | C | ASP | B | 283 | 37.924 | 19.560 | 26.964 | 1.00 | 51.65 | B C |
| ATOM | 2541 | O | ASP | B | 283 | 37.649 | 20.234 | 27.955 | 1.00 | 51.64 | B O |
| ATOM | 2542 | N | ALA | B | 284 | 37.719 | 18.248 | 26.945 | 1.00 | 51.84 | B N |
| ATOM | 2543 | CA | ALA | B | 284 | 37.260 | 17.466 | 28.083 | 1.00 | 51.86 | B C |
| ATOM | 2544 | CB | ALA | B | 284 | 36.605 | 16.147 | 27.625 | 1.00 | 51.20 | B C |
| ATOM | 2545 | C | ALA | B | 284 | 38.453 | 17.154 | 28.994 | 1.00 | 52.03 | B C |
| ATOM | 2546 | O | ALA | B | 284 | 38.307 | 17.055 | 30.218 | 1.00 | 51.94 | B O |
| ATOM | 2547 | N | PHE | B | 285 | 39.604 | 16.900 | 28.361 | 1.00 | 51.42 | B N |
| ATOM | 2548 | CA | PHE | B | 285 | 40.852 | 16.610 | 29.047 | 1.00 | 50.22 | B C |
| ATOM | 2549 | CB | PHE | B | 285 | 41.855 | 15.986 | 28.053 | 1.00 | 47.82 | B C |
| ATOM | 2550 | CG | PHE | B | 285 | 43.213 | 15.709 | 28.631 | 1.00 | 44.18 | B C |
| ATOM | 2551 | CD1 | PHE | B | 285 | 43.424 | 14.598 | 29.419 | 1.00 | 43.56 | B C |
| ATOM | 2552 | CD2 | PHE | B | 285 | 44.297 | 16.499 | 28.311 | 1.00 | 42.76 | B C |
| ATOM | 2553 | CE1 | PHE | B | 285 | 44.721 | 14.264 | 29.869 | 1.00 | 42.84 | B C |
| ATOM | 2554 | CE2 | PHE | B | 285 | 45.589 | 16.176 | 28.753 | 1.00 | 41.82 | B C |
| ATOM | 2555 | CZ | PHE | B | 285 | 45.796 | 15.060 | 29.541 | 1.00 | 41.76 | B C |
| ATOM | 2556 | C | PHE | B | 285 | 41.393 | 17.908 | 29.658 | 1.00 | 50.24 | B C |
| ATOM | 2557 | O | PHE | B | 285 | 41.767 | 17.956 | 30.834 | 1.00 | 49.99 | B O |
| ATOM | 2558 | N | LEU | B | 286 | 41.502 | 18.942 | 28.833 | 1.00 | 50.29 | B N |
| ATOM | 2559 | CA | LEU | B | 286 | 42.019 | 20.216 | 29.285 | 1.00 | 50.74 | B C |
| ATOM | 2560 | CB | LEU | B | 286 | 42.108 | 21.208 | 28.134 | 1.00 | 49.70 | B C |
| ATOM | 2561 | CG | LEU | B | 286 | 43.269 | 20.818 | 27.223 | 1.00 | 49.98 | B C |
| ATOM | 2562 | CD1 | LEU | B | 286 | 43.106 | 21.460 | 25.845 | 1.00 | 50.75 | B C |
| ATOM | 2563 | CD2 | LEU | B | 286 | 44.587 | 21.193 | 27.892 | 1.00 | 48.15 | B C |
| ATOM | 2564 | C | LEU | B | 286 | 41.054 | 20.677 | 30.348 | 1.00 | 51.78 | B C |
| ATOM | 2565 | O | LEU | B | 286 | 41.446 | 21.298 | 31.340 | 1.00 | 51.33 | B O |
| ATOM | 2566 | N | ALA | B | 287 | 39.782 | 20.310 | 30.167 | 1.00 | 53.98 | B N |
| ATOM | 2567 | CA | ALA | B | 287 | 38.722 | 20.682 | 31.138 | 1.00 | 55.29 | B C |

Figure 13

| ATOM | 2568 | CB  | ALA | B | 287 | 37.356 | 20.160 | 30.700 | 1.00 | 53.64 | B | C |
| ATOM | 2569 | C   | ALA | B | 287 | 39.082 | 20.145 | 32.548 | 1.00 | 55.72 | B | C |
| ATOM | 2570 | O   | ALA | B | 287 | 38.850 | 20.793 | 33.592 | 1.00 | 57.03 | B | O |
| ATOM | 2571 | N   | GLU | B | 288 | 39.701 | 18.987 | 32.561 | 1.00 | 55.20 | B | N |
| ATOM | 2572 | CA  | GLU | B | 288 | 40.114 | 18.404 | 33.824 | 1.00 | 56.42 | B | C |
| ATOM | 2573 | CB  | GLU | B | 288 | 40.516 | 16.897 | 33.637 | 1.00 | 56.93 | B | C |
| ATOM | 2574 | CG  | GLU | B | 288 | 39.415 | 15.996 | 32.952 | 1.00 | 57.26 | B | C |
| ATOM | 2575 | CD  | GLU | B | 288 | 39.625 | 14.448 | 33.090 | 1.00 | 57.06 | B | C |
| ATOM | 2576 | OE1 | GLU | B | 288 | 40.767 | 13.955 | 32.852 | 1.00 | 56.89 | B | O |
| ATOM | 2577 | OE2 | GLU | B | 288 | 38.639 | 13.741 | 33.437 | 1.00 | 52.95 | B | O |
| ATOM | 2578 | C   | GLU | B | 288 | 41.247 | 19.265 | 34.521 | 1.00 | 56.32 | B | C |
| ATOM | 2579 | O   | GLU | B | 288 | 41.326 | 19.347 | 35.765 | 1.00 | 55.66 | B | O |
| ATOM | 2580 | N   | ALA | B | 289 | 42.027 | 20.011 | 33.727 | 1.00 | 55.99 | B | N |
| ATOM | 2581 | CA  | ALA | B | 289 | 43.127 | 20.854 | 34.271 | 1.00 | 54.96 | B | C |
| ATOM | 2582 | CB  | ALA | B | 289 | 44.184 | 21.139 | 33.209 | 1.00 | 53.69 | B | C |
| ATOM | 2583 | C   | ALA | B | 289 | 42.668 | 22.166 | 34.884 | 1.00 | 54.65 | B | C |
| ATOM | 2584 | O   | ALA | B | 289 | 43.357 | 22.752 | 35.723 | 1.00 | 54.54 | B | O |
| ATOM | 2585 | N   | ASN | B | 290 | 41.510 | 22.632 | 34.438 | 1.00 | 54.46 | B | N |
| ATOM | 2586 | CA  | ASN | B | 290 | 40.944 | 23.880 | 34.939 | 1.00 | 54.92 | B | C |
| ATOM | 2587 | CB  | ASN | B | 290 | 39.679 | 24.249 | 34.135 | 1.00 | 55.71 | B | C |
| ATOM | 2588 | CG  | ASN | B | 290 | 39.972 | 24.564 | 32.665 | 1.00 | 55.19 | B | C |
| ATOM | 2589 | OD1 | ASN | B | 290 | 39.173 | 24.248 | 31.780 | 1.00 | 54.53 | B | O |
| ATOM | 2590 | ND2 | ASN | B | 290 | 41.107 | 25.217 | 32.409 | 1.00 | 54.82 | B | N |
| ATOM | 2591 | C   | ASN | B | 290 | 40.662 | 23.901 | 36.471 | 1.00 | 54.74 | B | C |
| ATOM | 2592 | O   | ASN | B | 290 | 40.753 | 24.949 | 37.095 | 1.00 | 54.48 | B | O |
| ATOM | 2593 | N   | LEU | B | 291 | 40.394 | 22.731 | 37.066 | 1.00 | 55.08 | B | N |
| ATOM | 2594 | CA  | LEU | B | 291 | 40.126 | 22.604 | 38.512 | 1.00 | 54.54 | B | C |
| ATOM | 2595 | CB  | LEU | B | 291 | 39.639 | 21.206 | 38.840 | 1.00 | 54.68 | B | C |
| ATOM | 2596 | CG  | LEU | B | 291 | 38.384 | 20.828 | 38.067 | 1.00 | 55.67 | B | C |
| ATOM | 2597 | CD1 | LEU | B | 291 | 38.142 | 19.324 | 38.110 | 1.00 | 56.36 | B | C |
| ATOM | 2598 | CD2 | LEU | B | 291 | 37.201 | 21.658 | 38.577 | 1.00 | 55.37 | B | C |
| ATOM | 2599 | C   | LEU | B | 291 | 41.364 | 22.853 | 39.334 | 1.00 | 54.29 | B | C |
| ATOM | 2600 | O   | LEU | B | 291 | 41.293 | 23.390 | 40.432 | 1.00 | 53.50 | B | O |
| ATOM | 2601 | N   | MET | B | 292 | 42.470 | 22.307 | 38.840 | 1.00 | 54.42 | B | N |
| ATOM | 2602 | CA  | MET | B | 292 | 43.773 | 22.463 | 39.465 | 1.00 | 54.09 | B | C |
| ATOM | 2603 | CB  | MET | B | 292 | 44.787 | 21.668 | 38.655 | 1.00 | 53.82 | B | C |
| ATOM | 2604 | CG  | MET | B | 292 | 45.790 | 20.879 | 39.453 | 1.00 | 53.05 | B | C |
| ATOM | 2605 | SD  | MET | B | 292 | 46.556 | 19.678 | 38.353 | 1.00 | 49.85 | B | S |
| ATOM | 2606 | CE  | MET | B | 292 | 45.971 | 18.200 | 39.167 | 1.00 | 53.66 | B | C |
| ATOM | 2607 | C   | MET | B | 292 | 44.114 | 23.967 | 39.466 | 1.00 | 54.16 | B | C |
| ATOM | 2608 | O   | MET | B | 292 | 44.748 | 24.456 | 40.397 | 1.00 | 53.85 | B | O |
| ATOM | 2609 | N   | LYS | B | 293 | 43.659 | 24.708 | 38.450 | 1.00 | 54.34 | B | N |
| ATOM | 2610 | CA  | LYS | B | 293 | 43.911 | 26.166 | 38.413 | 1.00 | 54.44 | B | C |
| ATOM | 2611 | CB  | LYS | B | 293 | 43.335 | 26.836 | 37.145 | 1.00 | 54.18 | B | C |
| ATOM | 2612 | CG  | LYS | B | 293 | 43.937 | 26.361 | 35.839 | 1.00 | 54.44 | B | C |
| ATOM | 2613 | CD  | LYS | B | 293 | 43.407 | 27.103 | 34.640 | 1.00 | 53.59 | B | C |
| ATOM | 2614 | CE  | LYS | B | 293 | 43.938 | 26.467 | 33.368 | 1.00 | 53.74 | B | C |
| ATOM | 2615 | NZ  | LYS | B | 293 | 43.409 | 27.095 | 32.150 | 1.00 | 53.93 | B | N |
| ATOM | 2616 | C   | LYS | B | 293 | 43.191 | 26.778 | 39.601 | 1.00 | 54.37 | B | C |
| ATOM | 2617 | O   | LYS | B | 293 | 43.790 | 27.477 | 40.416 | 1.00 | 55.26 | B | O |
| ATOM | 2618 | N   | GLN | B | 294 | 41.923 | 26.412 | 39.733 | 1.00 | 53.98 | B | N |
| ATOM | 2619 | CA  | GLN | B | 294 | 41.047 | 26.926 | 40.773 | 1.00 | 53.16 | B | C |
| ATOM | 2620 | CB  | GLN | B | 294 | 39.635 | 26.317 | 40.615 | 1.00 | 56.45 | B | C |
| ATOM | 2621 | CG  | GLN | B | 294 | 38.963 | 26.556 | 39.237 | 1.00 | 59.95 | B | C |
| ATOM | 2622 | CD  | GLN | B | 294 | 39.079 | 28.009 | 38.766 | 1.00 | 62.75 | B | C |
| ATOM | 2623 | OE1 | GLN | B | 294 | 39.882 | 28.325 | 37.878 | 1.00 | 64.54 | B | O |
| ATOM | 2624 | NE2 | GLN | B | 294 | 38.311 | 28.901 | 39.386 | 1.00 | 62.25 | B | N |
| ATOM | 2625 | C   | GLN | B | 294 | 41.542 | 26.712 | 42.191 | 1.00 | 51.14 | B | C |
| ATOM | 2626 | O   | GLN | B | 294 | 41.661 | 27.670 | 42.969 | 1.00 | 50.54 | B | O |
| ATOM | 2627 | N   | LEU | B | 295 | 41.844 | 25.451 | 42.509 | 1.00 | 48.74 | B | N |

Figure 13

| | | | | | | | | | | | |
|---|---|---|---|---|---|---|---|---|---|---|---|
| ATOM | 2628 | CA | LEU | B | 295 | 42.284 | 25.054 | 43.841 | 1.00 45.85 | B | C |
| ATOM | 2629 | CB | LEU | B | 295 | 41.601 | 23.774 | 44.260 | 1.00 45.40 | B | C |
| ATOM | 2630 | CG | LEU | B | 295 | 40.125 | 23.801 | 44.616 | 1.00 44.05 | B | C |
| ATOM | 2631 | CD1 | LEU | B | 295 | 39.762 | 22.443 | 45.234 | 1.00 43.90 | B | C |
| ATOM | 2632 | CD2 | LEU | B | 295 | 39.877 | 24.909 | 45.618 | 1.00 44.28 | B | C |
| ATOM | 2633 | C | LEU | B | 295 | 43.762 | 24.840 | 44.006 | 1.00 43.60 | B | C |
| ATOM | 2634 | O | LEU | B | 295 | 44.291 | 23.857 | 43.516 | 1.00 43.91 | B | O |
| ATOM | 2635 | N | GLN | B | 296 | 44.417 | 25.712 | 44.767 | 1.00 42.04 | B | N |
| ATOM | 2636 | CA | GLN | B | 296 | 45.861 | 25.599 | 45.038 | 1.00 40.82 | B | C |
| ATOM | 2637 | CB | GLN | B | 296 | 46.635 | 26.750 | 44.386 | 1.00 42.46 | B | C |
| ATOM | 2638 | CG | GLN | B | 296 | 46.415 | 26.911 | 42.901 | 1.00 45.60 | B | C |
| ATOM | 2639 | CD | GLN | B | 296 | 46.737 | 28.326 | 42.475 | 1.00 49.45 | B | C |
| ATOM | 2640 | OE1 | GLN | B | 296 | 46.921 | 29.212 | 43.349 | 1.00 52.58 | B | O |
| ATOM | 2641 | NE2 | GLN | B | 296 | 46.856 | 28.570 | 41.180 | 1.00 49.50 | B | N |
| ATOM | 2642 | C | GLN | B | 296 | 46.099 | 25.541 | 46.526 | 1.00 38.75 | B | C |
| ATOM | 2643 | O | GLN | B | 296 | 45.628 | 26.408 | 47.245 | 1.00 38.11 | B | O |
| ATOM | 2644 | N | HIS | B | 297 | 46.958 | 24.615 | 46.941 | 1.00 37.11 | B | N |
| ATOM | 2645 | CA | HIS | B | 297 | 47.261 | 24.355 | 48.337 | 1.00 35.04 | B | C |
| ATOM | 2646 | CB | HIS | B | 297 | 46.079 | 23.626 | 48.944 | 1.00 33.32 | B | C |
| ATOM | 2647 | CG | HIS | B | 297 | 46.099 | 23.565 | 50.466 | 1.00 31.02 | B | C |
| ATOM | 2648 | CD2 | HIS | B | 297 | 45.532 | 24.365 | 51.410 | 1.00 27.85 | B | C |
| ATOM | 2649 | ND1 | HIS | B | 297 | 46.720 | 22.554 | 51.150 | 1.00 30.85 | B | N |
| ATOM | 2650 | CE1 | HIS | B | 297 | 46.550 | 22.729 | 52.463 | 1.00 27.49 | B | C |
| ATOM | 2651 | NE2 | HIS | B | 297 | 45.832 | 23.829 | 52.628 | 1.00 26.63 | B | N |
| ATOM | 2652 | C | HIS | B | 297 | 48.496 | 23.450 | 48.339 | 1.00 34.94 | B | C |
| ATOM | 2653 | O | HIS | B | 297 | 48.698 | 22.710 | 47.382 | 1.00 34.31 | B | O |
| ATOM | 2654 | N | GLN | B | 298 | 49.324 | 23.516 | 49.392 | 1.00 35.91 | B | N |
| ATOM | 2655 | CA | GLN | B | 298 | 50.539 | 22.689 | 49.506 | 1.00 37.01 | B | C |
| ATOM | 2656 | CB | GLN | B | 298 | 51.303 | 23.014 | 50.793 | 1.00 40.01 | B | C |
| ATOM | 2657 | CG | GLN | B | 298 | 52.216 | 24.247 | 50.675 | 1.00 46.53 | B | C |
| ATOM | 2658 | CD | GLN | B | 298 | 53.183 | 24.203 | 49.476 | 1.00 48.63 | B | C |
| ATOM | 2659 | OE1 | GLN | B | 298 | 53.293 | 25.189 | 48.733 | 1.00 48.58 | B | O |
| ATOM | 2660 | NE2 | GLN | B | 298 | 53.872 | 23.057 | 49.280 | 1.00 48.90 | B | N |
| ATOM | 2661 | C | GLN | B | 298 | 50.234 | 21.218 | 49.493 | 1.00 36.35 | B | C |
| ATOM | 2662 | O | GLN | B | 298 | 51.068 | 20.384 | 49.146 | 1.00 37.26 | B | O |
| ATOM | 2663 | N | ARG | B | 299 | 49.041 | 20.887 | 49.929 | 1.00 35.08 | B | N |
| ATOM | 2664 | CA | ARG | B | 299 | 48.666 | 19.505 | 49.975 | 1.00 34.29 | B | C |
| ATOM | 2665 | CB | ARG | B | 299 | 47.817 | 19.293 | 51.213 | 1.00 35.92 | B | C |
| ATOM | 2666 | CG | ARG | B | 299 | 48.596 | 19.595 | 52.470 | 1.00 35.19 | B | C |
| ATOM | 2667 | CD | ARG | B | 299 | 49.625 | 18.538 | 52.702 | 1.00 36.32 | B | C |
| ATOM | 2668 | NE | ARG | B | 299 | 50.669 | 19.055 | 53.561 | 1.00 38.15 | B | N |
| ATOM | 2669 | CZ | ARG | B | 299 | 51.968 | 18.884 | 53.357 | 1.00 39.67 | B | C |
| ATOM | 2670 | NH1 | ARG | B | 299 | 52.428 | 18.178 | 52.303 | 1.00 41.79 | B | N |
| ATOM | 2671 | NH2 | ARG | B | 299 | 52.809 | 19.493 | 54.174 | 1.00 39.61 | B | N |
| ATOM | 2672 | C | ARG | B | 299 | 47.991 | 19.026 | 48.696 | 1.00 33.20 | B | C |
| ATOM | 2673 | O | ARG | B | 299 | 47.616 | 17.858 | 48.584 | 1.00 33.57 | B | O |
| ATOM | 2674 | N | LEU | B | 300 | 47.973 | 19.908 | 47.695 | 1.00 31.47 | B | N |
| ATOM | 2675 | CA | LEU | B | 300 | 47.348 | 19.645 | 46.404 | 1.00 30.32 | B | C |
| ATOM | 2676 | CB | LEU | B | 300 | 46.263 | 20.711 | 46.121 | 1.00 28.85 | B | C |
| ATOM | 2677 | CG | LEU | B | 300 | 44.822 | 20.281 | 46.389 | 1.00 27.12 | B | C |
| ATOM | 2678 | CD1 | LEU | B | 300 | 44.635 | 19.765 | 47.802 | 1.00 27.88 | B | C |
| ATOM | 2679 | CD2 | LEU | B | 300 | 43.910 | 21.429 | 46.133 | 1.00 28.22 | B | C |
| ATOM | 2680 | C | LEU | B | 300 | 48.387 | 19.649 | 45.314 | 1.00 30.04 | B | C |
| ATOM | 2681 | O | LEU | B | 300 | 49.332 | 20.391 | 45.424 | 1.00 31.06 | B | O |
| ATOM | 2682 | N | VAL | B | 301 | 48.255 | 18.821 | 44.283 | 1.00 31.48 | B | N |
| ATOM | 2683 | CA | VAL | B | 301 | 49.257 | 18.859 | 43.214 | 1.00 33.00 | B | C |
| ATOM | 2684 | CB | VAL | B | 301 | 49.048 | 17.704 | 42.209 | 1.00 32.54 | B | C |
| ATOM | 2685 | CG1 | VAL | B | 301 | 49.811 | 17.978 | 40.917 | 1.00 31.33 | B | C |
| ATOM | 2686 | CG2 | VAL | B | 301 | 49.517 | 16.414 | 42.826 | 1.00 29.51 | B | C |
| ATOM | 2687 | C | VAL | B | 301 | 49.165 | 20.220 | 42.503 | 1.00 34.83 | B | C |

Figure 13

| | | | | | | | | | | | |
|---|---|---|---|---|---|---|---|---|---|---|---|
| ATOM | 2688 | O | VAL | B | 301 | 48.073 | 20.696 | 42.219 | 1.00 | 34.85 | B | O |
| ATOM | 2689 | N | ARG | B | 302 | 50.285 | 20.902 | 42.306 | 1.00 | 36.98 | B | N |
| ATOM | 2690 | CA | ARG | B | 302 | 50.234 | 22.212 | 41.623 | 1.00 | 39.35 | B | C |
| ATOM | 2691 | CB | ARG | B | 302 | 51.239 | 23.194 | 42.214 | 1.00 | 42.75 | B | C |
| ATOM | 2692 | CG | ARG | B | 302 | 51.368 | 24.519 | 41.486 | 1.00 | 48.39 | B | C |
| ATOM | 2693 | CD | ARG | B | 302 | 52.431 | 24.402 | 40.380 | 1.00 | 54.07 | B | C |
| ATOM | 2694 | NE | ARG | B | 302 | 53.062 | 25.687 | 40.094 | 1.00 | 58.04 | B | N |
| ATOM | 2695 | CZ | ARG | B | 302 | 54.001 | 26.236 | 40.863 | 1.00 | 60.38 | B | C |
| ATOM | 2696 | NH1 | ARG | B | 302 | 54.440 | 25.608 | 41.959 | 1.00 | 61.05 | B | N |
| ATOM | 2697 | NH2 | ARG | B | 302 | 54.456 | 27.440 | 40.567 | 1.00 | 61.26 | B | N |
| ATOM | 2698 | C | ARG | B | 302 | 50.445 | 22.090 | 40.128 | 1.00 | 39.15 | B | C |
| ATOM | 2699 | O | ARG | B | 302 | 51.283 | 21.324 | 39.657 | 1.00 | 38.31 | B | O |
| ATOM | 2700 | N | LEU | B | 303 | 49.622 | 22.812 | 39.387 | 1.00 | 38.52 | B | N |
| ATOM | 2701 | CA | LEU | B | 303 | 49.683 | 22.821 | 37.939 | 1.00 | 38.38 | B | C |
| ATOM | 2702 | CB | LEU | B | 303 | 48.291 | 23.048 | 37.344 | 1.00 | 37.09 | B | C |
| ATOM | 2703 | CG | LEU | B | 303 | 48.316 | 23.105 | 35.824 | 1.00 | 37.19 | B | C |
| ATOM | 2704 | CD1 | LEU | B | 303 | 47.919 | 21.740 | 35.290 | 1.00 | 36.99 | B | C |
| ATOM | 2705 | CD2 | LEU | B | 303 | 47.383 | 24.178 | 35.338 | 1.00 | 36.37 | B | C |
| ATOM | 2706 | C | LEU | B | 303 | 50.603 | 23.944 | 37.478 | 1.00 | 38.37 | B | C |
| ATOM | 2707 | O | LEU | B | 303 | 50.610 | 25.008 | 38.085 | 1.00 | 37.98 | B | O |
| ATOM | 2708 | N | TYR | B | 304 | 51.451 | 23.670 | 36.491 | 1.00 | 38.43 | B | N |
| ATOM | 2709 | CA | TYR | B | 304 | 52.303 | 24.716 | 35.960 | 1.00 | 39.43 | B | C |
| ATOM | 2710 | CB | TYR | B | 304 | 53.745 | 24.277 | 35.727 | 1.00 | 42.52 | B | C |
| ATOM | 2711 | CG | TYR | B | 304 | 54.580 | 24.051 | 36.942 | 1.00 | 45.04 | B | C |
| ATOM | 2712 | CD1 | TYR | B | 304 | 54.556 | 22.834 | 37.566 | 1.00 | 47.45 | B | C |
| ATOM | 2713 | CE1 | TYR | B | 304 | 55.356 | 22.543 | 38.627 | 1.00 | 48.62 | B | C |
| ATOM | 2714 | CD2 | TYR | B | 304 | 55.457 | 25.019 | 37.426 | 1.00 | 49.10 | B | C |
| ATOM | 2715 | CE2 | TYR | B | 304 | 56.293 | 24.727 | 38.531 | 1.00 | 51.38 | B | C |
| ATOM | 2716 | CZ | TYR | B | 304 | 56.214 | 23.459 | 39.116 | 1.00 | 50.09 | B | C |
| ATOM | 2717 | OH | TYR | B | 304 | 56.971 | 23.077 | 40.199 | 1.00 | 50.37 | B | O |
| ATOM | 2718 | C | TYR | B | 304 | 51.767 | 25.221 | 34.622 | 1.00 | 38.44 | B | C |
| ATOM | 2719 | O | TYR | B | 304 | 51.683 | 26.414 | 34.451 | 1.00 | 40.18 | B | O |
| ATOM | 2720 | N | ALA | B | 305 | 51.408 | 24.331 | 33.692 | 1.00 | 37.62 | B | N |
| ATOM | 2721 | CA | ALA | B | 305 | 50.926 | 24.722 | 32.366 | 1.00 | 36.96 | B | C |
| ATOM | 2722 | CB | ALA | B | 305 | 52.111 | 25.205 | 31.546 | 1.00 | 37.71 | B | C |
| ATOM | 2723 | C | ALA | B | 305 | 50.189 | 23.649 | 31.572 | 1.00 | 37.25 | B | C |
| ATOM | 2724 | O | ALA | B | 305 | 50.076 | 22.502 | 31.995 | 1.00 | 37.41 | B | O |
| ATOM | 2725 | N | VAL | B | 306 | 49.720 | 24.028 | 30.391 | 1.00 | 37.55 | B | N |
| ATOM | 2726 | CA | VAL | B | 306 | 49.040 | 23.087 | 29.504 | 1.00 | 39.10 | B | C |
| ATOM | 2727 | CB | VAL | B | 306 | 47.496 | 23.155 | 29.649 | 1.00 | 39.62 | B | C |
| ATOM | 2728 | CG1 | VAL | B | 306 | 47.045 | 22.467 | 30.912 | 1.00 | 39.81 | B | C |
| ATOM | 2729 | CG2 | VAL | B | 306 | 47.055 | 24.556 | 29.691 | 1.00 | 40.66 | B | C |
| ATOM | 2730 | C | VAL | B | 306 | 49.415 | 23.440 | 28.077 | 1.00 | 39.60 | B | C |
| ATOM | 2731 | O | VAL | B | 306 | 49.760 | 24.587 | 27.811 | 1.00 | 40.45 | B | O |
| ATOM | 2732 | N | VAL | B | 307 | 49.431 | 22.448 | 27.191 | 1.00 | 39.34 | B | N |
| ATOM | 2733 | CA | VAL | B | 307 | 49.740 | 22.650 | 25.778 | 1.00 | 40.26 | B | C |
| ATOM | 2734 | CB | VAL | B | 307 | 51.038 | 21.896 | 25.374 | 1.00 | 38.50 | B | C |
| ATOM | 2735 | CG1 | VAL | B | 307 | 51.287 | 21.974 | 23.859 | 1.00 | 35.41 | B | C |
| ATOM | 2736 | CG2 | VAL | B | 307 | 52.177 | 22.449 | 26.160 | 1.00 | 36.01 | B | C |
| ATOM | 2737 | C | VAL | B | 307 | 48.493 | 22.139 | 25.018 | 1.00 | 42.80 | B | C |
| ATOM | 2738 | O | VAL | B | 307 | 48.220 | 20.932 | 24.982 | 1.00 | 42.90 | B | O |
| ATOM | 2739 | N | THR | B | 308 | 47.750 | 23.062 | 24.408 | 1.00 | 45.25 | B | N |
| ATOM | 2740 | CA | THR | B | 308 | 46.504 | 22.727 | 23.700 | 1.00 | 47.72 | B | C |
| ATOM | 2741 | CB | THR | B | 308 | 45.616 | 23.944 | 23.588 | 1.00 | 48.03 | B | C |
| ATOM | 2742 | OG1 | THR | B | 308 | 46.325 | 24.970 | 22.879 | 1.00 | 50.04 | B | O |
| ATOM | 2743 | CG2 | THR | B | 308 | 45.219 | 24.407 | 24.976 | 1.00 | 46.98 | B | C |
| ATOM | 2744 | C | THR | B | 308 | 46.547 | 22.065 | 22.330 | 1.00 | 49.21 | B | C |
| ATOM | 2745 | O | THR | B | 308 | 45.512 | 21.609 | 21.853 | 1.00 | 48.58 | B | O |
| ATOM | 2746 | N | GLN | B | 309 | 47.651 | 22.219 | 21.611 | 1.00 | 51.47 | B | N |
| ATOM | 2747 | CA | GLN | B | 309 | 47.763 | 21.559 | 20.314 | 1.00 | 54.05 | B | C |

Figure 13

| | | | | | | | | | | | |
|---|---|---|---|---|---|---|---|---|---|---|---|
| ATOM | 2748 | CB | GLN | B | 309 | 48.799 | 22.264 | 19.391 | 1.00 56.25 | B | C |
| ATOM | 2749 | CG | GLN | B | 309 | 48.416 | 23.673 | 18.904 | 1.00 60.42 | B | C |
| ATOM | 2750 | CD | GLN | B | 309 | 46.979 | 23.769 | 18.254 | 1.00 62.36 | B | C |
| ATOM | 2751 | OE1 | GLN | B | 309 | 46.267 | 22.745 | 18.093 | 1.00 62.67 | B | O |
| ATOM | 2752 | NE2 | GLN | B | 309 | 46.574 | 24.982 | 17.884 | 1.00 63.24 | B | N |
| ATOM | 2753 | C | GLN | B | 309 | 48.104 | 20.077 | 20.530 | 1.00 54.15 | B | C |
| ATOM | 2754 | O | GLN | B | 309 | 48.815 | 19.716 | 21.467 | 1.00 53.81 | B | O |
| ATOM | 2755 | N | GLU | B | 310 | 47.563 | 19.232 | 19.673 | 1.00 54.29 | B | N |
| ATOM | 2756 | CA | GLU | B | 310 | 47.796 | 17.803 | 19.768 | 1.00 55.51 | B | C |
| ATOM | 2757 | CB | GLU | B | 310 | 46.821 | 17.060 | 18.852 | 1.00 59.09 | B | C |
| ATOM | 2758 | CG | GLU | B | 310 | 46.699 | 17.648 | 17.433 | 1.00 65.01 | B | C |
| ATOM | 2759 | CD | GLU | B | 310 | 45.436 | 18.534 | 17.202 | 1.00 67.45 | B | C |
| ATOM | 2760 | OE1 | GLU | B | 310 | 44.318 | 18.115 | 17.627 | 1.00 68.92 | B | O |
| ATOM | 2761 | OE2 | GLU | B | 310 | 45.569 | 19.618 | 16.558 | 1.00 66.89 | B | O |
| ATOM | 2762 | C | GLU | B | 310 | 49.257 | 17.385 | 19.490 | 1.00 54.21 | B | C |
| ATOM | 2763 | O | GLU | B | 310 | 49.889 | 17.868 | 18.544 | 1.00 54.51 | B | O |
| ATOM | 2764 | N | PRO | B | 311 | 49.799 | 16.492 | 20.348 | 1.00 52.67 | B | N |
| ATOM | 2765 | CD | PRO | B | 311 | 51.164 | 15.935 | 20.070 | 1.00 52.30 | B | C |
| ATOM | 2766 | CA | PRO | B | 311 | 49.235 | 15.857 | 21.527 | 1.00 50.28 | B | C |
| ATOM | 2767 | CB | PRO | B | 311 | 50.249 | 14.756 | 21.874 | 1.00 49.62 | B | C |
| ATOM | 2768 | CG | PRO | B | 311 | 50.987 | 14.530 | 20.569 | 1.00 50.51 | B | C |
| ATOM | 2769 | C | PRO | B | 311 | 49.028 | 16.844 | 22.728 | 1.00 48.22 | B | C |
| ATOM | 2770 | O | PRO | B | 311 | 49.906 | 17.670 | 23.033 | 1.00 48.25 | B | O |
| ATOM | 2771 | N | ILE | B | 312 | 47.865 | 16.776 | 23.348 | 1.00 45.34 | B | N |
| ATOM | 2772 | CA | ILE | B | 312 | 47.518 | 17.654 | 24.481 | 1.00 41.47 | B | C |
| ATOM | 2773 | CB | ILE | B | 312 | 46.015 | 17.493 | 24.884 | 1.00 42.48 | B | C |
| ATOM | 2774 | CG2 | ILE | B | 312 | 45.589 | 18.651 | 25.794 | 1.00 42.71 | B | C |
| ATOM | 2775 | CG1 | ILE | B | 312 | 45.095 | 17.364 | 23.647 | 1.00 42.88 | B | C |
| ATOM | 2776 | CD1 | ILE | B | 312 | 44.631 | 18.666 | 23.008 | 1.00 40.14 | B | C |
| ATOM | 2777 | C | ILE | B | 312 | 48.350 | 17.280 | 25.719 | 1.00 37.62 | B | C |
| ATOM | 2778 | O | ILE | B | 312 | 48.515 | 16.096 | 26.026 | 1.00 36.65 | B | O |
| ATOM | 2779 | N | TYR | B | 313 | 48.813 | 18.281 | 26.457 | 1.00 34.22 | B | N |
| ATOM | 2780 | CA | TYR | B | 313 | 49.617 | 18.013 | 27.641 | 1.00 32.02 | B | C |
| ATOM | 2781 | CB | TYR | B | 313 | 51.082 | 18.467 | 27.465 | 1.00 32.27 | B | C |
| ATOM | 2782 | CG | TYR | B | 313 | 51.982 | 17.764 | 26.461 | 1.00 32.94 | B | C |
| ATOM | 2783 | CD1 | TYR | B | 313 | 51.676 | 16.508 | 25.944 | 1.00 33.25 | B | C |
| ATOM | 2784 | CE1 | TYR | B | 313 | 52.567 | 15.860 | 25.070 | 1.00 35.16 | B | C |
| ATOM | 2785 | CD2 | TYR | B | 313 | 53.197 | 18.357 | 26.081 | 1.00 33.96 | B | C |
| ATOM | 2786 | CE2 | TYR | B | 313 | 54.095 | 17.721 | 25.220 | 1.00 34.56 | B | C |
| ATOM | 2787 | CZ | TYR | B | 313 | 53.786 | 16.472 | 24.714 | 1.00 35.29 | B | C |
| ATOM | 2788 | OH | TYR | B | 313 | 54.673 | 15.809 | 23.880 | 1.00 34.79 | B | O |
| ATOM | 2789 | C | TYR | B | 313 | 49.131 | 18.772 | 28.854 | 1.00 30.28 | B | C |
| ATOM | 2790 | O | TYR | B | 313 | 48.657 | 19.885 | 28.730 | 1.00 29.74 | B | O |
| ATOM | 2791 | N | ILE | B | 314 | 49.268 | 18.188 | 30.041 | 1.00 29.06 | B | N |
| ATOM | 2792 | CA | ILE | B | 314 | 48.935 | 18.932 | 31.274 | 1.00 27.92 | B | C |
| ATOM | 2793 | CB | ILE | B | 314 | 47.775 | 18.312 | 32.081 | 1.00 26.78 | B | C |
| ATOM | 2794 | CG2 | ILE | B | 314 | 47.644 | 18.965 | 33.421 | 1.00 22.58 | B | C |
| ATOM | 2795 | CG1 | ILE | B | 314 | 46.486 | 18.438 | 31.314 | 1.00 25.54 | B | C |
| ATOM | 2796 | CD1 | ILE | B | 314 | 45.437 | 17.616 | 31.852 | 1.00 27.59 | B | C |
| ATOM | 2797 | C | ILE | B | 314 | 50.239 | 18.804 | 32.058 | 1.00 27.76 | B | C |
| ATOM | 2798 | O | ILE | B | 314 | 50.718 | 17.684 | 32.260 | 1.00 29.10 | B | O |
| ATOM | 2799 | N | ILE | B | 315 | 50.885 | 19.923 | 32.360 | 1.00 26.20 | B | N |
| ATOM | 2800 | CA | ILE | B | 315 | 52.160 | 19.901 | 33.094 | 1.00 26.34 | B | C |
| ATOM | 2801 | CB | ILE | B | 315 | 53.283 | 20.869 | 32.441 | 1.00 28.44 | B | C |
| ATOM | 2802 | CG2 | ILE | B | 315 | 54.536 | 21.007 | 33.316 | 1.00 25.47 | B | C |
| ATOM | 2803 | CG1 | ILE | B | 315 | 53.723 | 20.362 | 31.064 | 1.00 28.38 | B | C |
| ATOM | 2804 | CD1 | ILE | B | 315 | 52.774 | 20.733 | 29.931 | 1.00 28.73 | B | C |
| ATOM | 2805 | C | ILE | B | 315 | 51.966 | 20.297 | 34.545 | 1.00 25.80 | B | C |
| ATOM | 2806 | O | ILE | B | 315 | 51.458 | 21.378 | 34.832 | 1.00 24.83 | B | O |
| ATOM | 2807 | N | THR | B | 316 | 52.380 | 19.415 | 35.450 | 1.00 24.77 | B | N |

Figure 13

| ATOM | 2808 | CA | THR | B | 316 | 52.286 | 19.649 | 36.887 | 1.00 | 24.18 | B | C |
|------|------|------|-----|---|-----|--------|--------|--------|------|-------|---|---|
| ATOM | 2809 | CB | THR | B | 316 | 51.432 | 18.597 | 37.549 | 1.00 | 23.41 | B | C |
| ATOM | 2810 | OG1 | THR | B | 316 | 52.088 | 17.322 | 37.425 | 1.00 | 22.95 | B | O |
| ATOM | 2811 | CG2 | THR | B | 316 | 50.090 | 18.500 | 36.869 | 1.00 | 24.04 | B | C |
| ATOM | 2812 | C | THR | B | 316 | 53.642 | 19.418 | 37.505 | 1.00 | 24.18 | B | C |
| ATOM | 2813 | O | THR | B | 316 | 54.539 | 18.892 | 36.864 | 1.00 | 24.33 | B | O |
| ATOM | 2814 | N | GLU | B | 317 | 53.730 | 19.671 | 38.800 | 1.00 | 25.03 | B | N |
| ATOM | 2815 | CA | GLU | B | 317 | 54.966 | 19.443 | 39.524 | 1.00 | 25.94 | B | C |
| ATOM | 2816 | CB | GLU | B | 317 | 54.837 | 19.984 | 40.941 | 1.00 | 26.06 | B | C |
| ATOM | 2817 | CG | GLU | B | 317 | 53.888 | 19.197 | 41.813 | 1.00 | 24.64 | B | C |
| ATOM | 2818 | CD | GLU | B | 317 | 53.862 | 19.712 | 43.217 | 1.00 | 24.59 | B | C |
| ATOM | 2819 | OE1 | GLU | B | 317 | 52.780 | 20.147 | 43.646 | 1.00 | 25.02 | B | O |
| ATOM | 2820 | OE2 | GLU | B | 317 | 54.911 | 19.675 | 43.906 | 1.00 | 23.42 | B | O |
| ATOM | 2821 | C | GLU | B | 317 | 55.313 | 17.935 | 39.557 | 1.00 | 26.91 | B | C |
| ATOM | 2822 | O | GLU | B | 317 | 54.447 | 17.059 | 39.484 | 1.00 | 26.21 | B | O |
| ATOM | 2823 | N | TYR | B | 318 | 56.600 | 17.654 | 39.680 | 1.00 | 27.88 | B | N |
| ATOM | 2824 | CA | TYR | B | 318 | 57.092 | 16.301 | 39.700 | 1.00 | 28.04 | B | C |
| ATOM | 2825 | CB | TYR | B | 318 | 58.463 | 16.218 | 39.068 | 1.00 | 25.93 | B | C |
| ATOM | 2826 | CG | TYR | B | 318 | 59.034 | 14.815 | 39.135 | 1.00 | 28.09 | B | C |
| ATOM | 2827 | CD1 | TYR | B | 318 | 58.447 | 13.760 | 38.441 | 1.00 | 28.77 | B | C |
| ATOM | 2828 | CE1 | TYR | B | 318 | 58.989 | 12.464 | 38.516 | 1.00 | 28.46 | B | C |
| ATOM | 2829 | CD2 | TYR | B | 318 | 60.178 | 14.522 | 39.904 | 1.00 | 28.56 | B | C |
| ATOM | 2830 | CE2 | TYR | B | 318 | 60.715 | 13.221 | 39.970 | 1.00 | 26.57 | B | C |
| ATOM | 2831 | CZ | TYR | B | 318 | 60.106 | 12.223 | 39.270 | 1.00 | 26.76 | B | C |
| ATOM | 2832 | OH | TYR | B | 318 | 60.604 | 10.973 | 39.289 | 1.00 | 26.77 | B | O |
| ATOM | 2833 | C | TYR | B | 318 | 57.161 | 15.795 | 41.115 | 1.00 | 29.08 | B | C |
| ATOM | 2834 | O | TYR | B | 318 | 57.712 | 16.439 | 41.980 | 1.00 | 28.71 | B | O |
| ATOM | 2835 | N | MET | B | 319 | 56.599 | 14.608 | 41.309 | 1.00 | 31.24 | B | N |
| ATOM | 2836 | CA | MET | B | 319 | 56.537 | 13.892 | 42.572 | 1.00 | 32.96 | B | C |
| ATOM | 2837 | CB | MET | B | 319 | 55.077 | 13.533 | 42.865 | 1.00 | 33.40 | B | C |
| ATOM | 2838 | CG | MET | B | 319 | 54.165 | 14.739 | 43.063 | 1.00 | 31.72 | B | C |
| ATOM | 2839 | SD | MET | B | 319 | 54.720 | 15.909 | 44.393 | 1.00 | 31.83 | B | S |
| ATOM | 2840 | CE | MET | B | 319 | 54.154 | 15.172 | 45.747 | 1.00 | 29.97 | B | C |
| ATOM | 2841 | C | MET | B | 319 | 57.383 | 12.617 | 42.404 | 1.00 | 33.42 | B | C |
| ATOM | 2842 | O | MET | B | 319 | 56.957 | 11.629 | 41.833 | 1.00 | 33.73 | B | O |
| ATOM | 2843 | N | GLU | B | 320 | 58.614 | 12.725 | 42.860 | 1.00 | 34.27 | B | N |
| ATOM | 2844 | CA | GLU | B | 320 | 59.613 | 11.685 | 42.837 | 1.00 | 35.00 | B | C |
| ATOM | 2845 | CB | GLU | B | 320 | 60.672 | 12.105 | 43.860 | 1.00 | 37.04 | B | C |
| ATOM | 2846 | CG | GLU | B | 320 | 61.717 | 11.099 | 44.213 | 1.00 | 40.04 | B | C |
| ATOM | 2847 | CD | GLU | B | 320 | 63.011 | 11.309 | 43.463 | 1.00 | 41.83 | B | C |
| ATOM | 2848 | OE1 | GLU | B | 320 | 63.412 | 12.486 | 43.282 | 1.00 | 41.04 | B | O |
| ATOM | 2849 | OE2 | GLU | B | 320 | 63.631 | 10.282 | 43.078 | 1.00 | 43.90 | B | O |
| ATOM | 2850 | C | GLU | B | 320 | 59.060 | 10.298 | 43.179 | 1.00 | 34.88 | B | C |
| ATOM | 2851 | O | GLU | B | 320 | 59.089 | 9.370 | 42.363 | 1.00 | 36.11 | B | O |
| ATOM | 2852 | N | ASN | B | 321 | 58.484 | 10.150 | 44.359 | 1.00 | 33.36 | B | N |
| ATOM | 2853 | CA | ASN | B | 321 | 58.021 | 8.844 | 44.688 | 1.00 | 32.12 | B | C |
| ATOM | 2854 | CB | ASN | B | 321 | 58.043 | 8.675 | 46.184 | 1.00 | 32.12 | B | C |
| ATOM | 2855 | CG | ASN | B | 321 | 59.474 | 8.521 | 46.697 | 1.00 | 30.76 | B | C |
| ATOM | 2856 | OD1 | ASN | B | 321 | 60.169 | 7.544 | 46.361 | 1.00 | 28.97 | B | O |
| ATOM | 2857 | ND2 | ASN | B | 321 | 59.934 | 9.495 | 47.457 | 1.00 | 29.40 | B | N |
| ATOM | 2858 | C | ASN | B | 321 | 56.758 | 8.365 | 44.049 | 1.00 | 31.75 | B | C |
| ATOM | 2859 | O | ASN | B | 321 | 56.319 | 7.263 | 44.351 | 1.00 | 34.05 | B | O |
| ATOM | 2860 | N | GLY | B | 322 | 56.216 | 9.126 | 43.105 | 1.00 | 31.26 | B | N |
| ATOM | 2861 | CA | GLY | B | 322 | 55.003 | 8.714 | 42.422 | 1.00 | 29.43 | B | C |
| ATOM | 2862 | C | GLY | B | 322 | 53.759 | 8.575 | 43.289 | 1.00 | 28.78 | B | C |
| ATOM | 2863 | O | GLY | B | 322 | 53.499 | 9.384 | 44.182 | 1.00 | 27.67 | B | O |
| ATOM | 2864 | N | SER | B | 323 | 53.030 | 7.495 | 43.027 | 1.00 | 28.16 | B | N |
| ATOM | 2865 | CA | SER | B | 323 | 51.767 | 7.160 | 43.677 | 1.00 | 28.17 | B | C |
| ATOM | 2866 | CB | SER | B | 323 | 50.967 | 6.277 | 42.714 | 1.00 | 27.40 | B | C |
| ATOM | 2867 | OG | SER | B | 323 | 49.621 | 6.118 | 43.102 | 1.00 | 28.68 | B | O |

Figure 13

| | | | | | | | | | | | |
|---|---|---|---|---|---|---|---|---|---|---|---|
| ATOM | 2868 | C | SER | B | 323 | 51.939 | 6.464 | 45.020 | 1.00 | 27.79 | B C |
| ATOM | 2869 | O | SER | B | 323 | 52.669 | 5.504 | 45.113 | 1.00 | 28.45 | B O |
| ATOM | 2870 | N | LEU | B | 324 | 51.192 | 6.904 | 46.028 | 1.00 | 26.89 | B N |
| ATOM | 2871 | CA | LEU | B | 324 | 51.274 | 6.324 | 47.363 | 1.00 | 25.99 | B C |
| ATOM | 2872 | CB | LEU | B | 324 | 50.401 | 7.117 | 48.314 | 1.00 | 23.48 | B C |
| ATOM | 2873 | CG | LEU | B | 324 | 50.279 | 6.671 | 49.758 | 1.00 | 21.02 | B C |
| ATOM | 2874 | CD1 | LEU | B | 324 | 51.590 | 6.870 | 50.462 | 1.00 | 20.67 | B C |
| ATOM | 2875 | CD2 | LEU | B | 324 | 49.164 | 7.454 | 50.433 | 1.00 | 19.45 | B C |
| ATOM | 2876 | C | LEU | B | 324 | 50.887 | 4.829 | 47.406 | 1.00 | 26.74 | B C |
| ATOM | 2877 | O | LEU | B | 324 | 51.449 | 4.072 | 48.189 | 1.00 | 27.74 | B O |
| ATOM | 2878 | N | VAL | B | 325 | 49.967 | 4.377 | 46.562 | 1.00 | 27.62 | B N |
| ATOM | 2879 | CA | VAL | B | 325 | 49.609 | 2.965 | 46.612 | 1.00 | 28.42 | B C |
| ATOM | 2880 | CB | VAL | B | 325 | 48.306 | 2.705 | 45.789 | 1.00 | 27.24 | B C |
| ATOM | 2881 | CG1 | VAL | B | 325 | 48.568 | 2.650 | 44.279 | 1.00 | 26.29 | B C |
| ATOM | 2882 | CG2 | VAL | B | 325 | 47.577 | 1.476 | 46.306 | 1.00 | 26.09 | B C |
| ATOM | 2883 | C | VAL | B | 325 | 50.819 | 2.111 | 46.166 | 1.00 | 29.35 | B C |
| ATOM | 2884 | O | VAL | B | 325 | 51.081 | 1.036 | 46.710 | 1.00 | 29.22 | B O |
| ATOM | 2885 | N | ASP | B | 326 | 51.614 | 2.669 | 45.255 | 1.00 | 30.77 | B N |
| ATOM | 2886 | CA | ASP | B | 326 | 52.808 | 2.016 | 44.732 | 1.00 | 31.35 | B C |
| ATOM | 2887 | CB | ASP | B | 326 | 53.141 | 2.618 | 43.378 | 1.00 | 32.71 | B C |
| ATOM | 2888 | CG | ASP | B | 326 | 52.111 | 2.251 | 42.331 | 1.00 | 35.28 | B C |
| ATOM | 2889 | OD1 | ASP | B | 326 | 51.403 | 1.247 | 42.550 | 1.00 | 34.86 | B O |
| ATOM | 2890 | OD2 | ASP | B | 326 | 52.000 | 2.968 | 41.307 | 1.00 | 37.05 | B O |
| ATOM | 2891 | C | ASP | B | 326 | 54.013 | 2.103 | 45.661 | 1.00 | 31.84 | B C |
| ATOM | 2892 | O | ASP | B | 326 | 54.695 | 1.109 | 45.925 | 1.00 | 31.79 | B O |
| ATOM | 2893 | N | PHE | B | 327 | 54.220 | 3.283 | 46.209 | 1.00 | 32.04 | B N |
| ATOM | 2894 | CA | PHE | B | 327 | 55.329 | 3.530 | 47.104 | 1.00 | 32.68 | B C |
| ATOM | 2895 | CB | PHE | B | 327 | 55.321 | 4.961 | 47.512 | 1.00 | 32.89 | B C |
| ATOM | 2896 | CG | PHE | B | 327 | 56.384 | 5.304 | 48.491 | 1.00 | 34.31 | B C |
| ATOM | 2897 | CD1 | PHE | B | 327 | 57.717 | 5.269 | 48.103 | 1.00 | 34.82 | B C |
| ATOM | 2898 | CD2 | PHE | B | 327 | 56.060 | 5.796 | 49.761 | 1.00 | 33.94 | B C |
| ATOM | 2899 | CE1 | PHE | B | 327 | 58.707 | 5.730 | 48.955 | 1.00 | 34.20 | B C |
| ATOM | 2900 | CE2 | PHE | B | 327 | 57.048 | 6.259 | 50.617 | 1.00 | 33.51 | B C |
| ATOM | 2901 | CZ | PHE | B | 327 | 58.366 | 6.228 | 50.214 | 1.00 | 33.83 | B C |
| ATOM | 2902 | C | PHE | B | 327 | 55.248 | 2.764 | 48.384 | 1.00 | 33.29 | B C |
| ATOM | 2903 | O | PHE | B | 327 | 56.267 | 2.419 | 48.980 | 1.00 | 34.06 | B O |
| ATOM | 2904 | N | LEU | B | 328 | 54.035 | 2.631 | 48.892 | 1.00 | 32.68 | B N |
| ATOM | 2905 | CA | LEU | B | 328 | 53.867 | 1.943 | 50.140 | 1.00 | 32.32 | B C |
| ATOM | 2906 | CB | LEU | B | 328 | 52.399 | 1.917 | 50.522 | 1.00 | 29.92 | B C |
| ATOM | 2907 | CG | LEU | B | 328 | 51.825 | 3.156 | 51.151 | 1.00 | 27.05 | B C |
| ATOM | 2908 | CD1 | LEU | B | 328 | 50.418 | 2.858 | 51.496 | 1.00 | 26.60 | B C |
| ATOM | 2909 | CD2 | LEU | B | 328 | 52.639 | 3.527 | 52.388 | 1.00 | 27.25 | B C |
| ATOM | 2910 | C | LEU | B | 328 | 54.374 | 0.525 | 50.033 | 1.00 | 34.24 | B C |
| ATOM | 2911 | O | LEU | B | 328 | 54.672 | -0.076 | 51.054 | 1.00 | 35.35 | B O |
| ATOM | 2912 | N | LYS | B | 329 | 54.464 | -0.011 | 48.808 | 1.00 | 35.93 | B N |
| ATOM | 2913 | CA | LYS | B | 329 | 54.891 | -1.398 | 48.586 | 1.00 | 37.08 | B C |
| ATOM | 2914 | CB | LYS | B | 329 | 54.139 | -2.020 | 47.407 | 1.00 | 35.70 | B C |
| ATOM | 2915 | CG | LYS | B | 329 | 52.604 | -2.105 | 47.527 | 1.00 | 33.77 | B C |
| ATOM | 2916 | CD | LYS | B | 329 | 52.036 | -2.859 | 46.339 | 1.00 | 31.47 | B C |
| ATOM | 2917 | CE | LYS | B | 329 | 50.549 | -2.864 | 46.305 | 1.00 | 32.40 | B C |
| ATOM | 2918 | NZ | LYS | B | 329 | 50.052 | -1.529 | 46.046 | 1.00 | 34.15 | B N |
| ATOM | 2919 | C | LYS | B | 329 | 56.378 | -1.551 | 48.357 | 1.00 | 38.63 | B C |
| ATOM | 2920 | O | LYS | B | 329 | 56.894 | -2.659 | 48.434 | 1.00 | 40.81 | B O |
| ATOM | 2921 | N | THR | B | 330 | 57.060 | -0.452 | 48.070 | 1.00 | 39.71 | B N |
| ATOM | 2922 | CA | THR | B | 330 | 58.508 | -0.470 | 47.845 | 1.00 | 40.50 | B C |
| ATOM | 2923 | CB | THR | B | 330 | 58.995 | 0.901 | 47.343 | 1.00 | 40.75 | B C |
| ATOM | 2924 | OG1 | THR | B | 330 | 58.811 | 1.906 | 48.362 | 1.00 | 40.95 | B O |
| ATOM | 2925 | CG2 | THR | B | 330 | 58.221 | 1.277 | 46.052 | 1.00 | 40.56 | B C |
| ATOM | 2926 | C | THR | B | 330 | 59.241 | -0.755 | 49.148 | 1.00 | 41.23 | B C |
| ATOM | 2927 | O | THR | B | 330 | 58.716 | -0.464 | 50.224 | 1.00 | 41.84 | B O |

Figure 13

| ATOM | 2928 | N   | PRO | B | 331 | 60.467 | -1.304 | 49.068 | 1.00 | 41.46 | B | N |
|------|------|-----|-----|---|-----|--------|--------|--------|------|-------|---|---|
| ATOM | 2929 | CD  | PRO | B | 331 | 61.212 | -1.534 | 47.817 | 1.00 | 42.61 | B | C |
| ATOM | 2930 | CA  | PRO | B | 331 | 61.306 | -1.635 | 50.224 | 1.00 | 40.80 | B | C |
| ATOM | 2931 | CB  | PRO | B | 331 | 62.683 | -1.803 | 49.594 | 1.00 | 42.04 | B | C |
| ATOM | 2932 | CG  | PRO | B | 331 | 62.331 | -2.420 | 48.272 | 1.00 | 43.05 | B | C |
| ATOM | 2933 | C   | PRO | B | 331 | 61.302 | -0.501 | 51.244 | 1.00 | 39.86 | B | C |
| ATOM | 2934 | O   | PRO | B | 331 | 61.118 | -0.740 | 52.432 | 1.00 | 38.80 | B | O |
| ATOM | 2935 | N   | SER | B | 332 | 61.434 | 0.737  | 50.762 | 1.00 | 39.31 | B | N |
| ATOM | 2936 | CA  | SER | B | 332 | 61.423 | 1.904  | 51.646 | 1.00 | 40.15 | B | C |
| ATOM | 2937 | CB  | SER | B | 332 | 61.797 | 3.189  | 50.894 | 1.00 | 40.00 | B | C |
| ATOM | 2938 | OG  | SER | B | 332 | 63.048 | 3.084  | 50.254 | 1.00 | 39.67 | B | O |
| ATOM | 2939 | C   | SER | B | 332 | 60.035 | 2.095  | 52.252 | 1.00 | 40.41 | B | C |
| ATOM | 2940 | O   | SER | B | 332 | 59.908 | 2.448  | 53.436 | 1.00 | 41.24 | B | O |
| ATOM | 2941 | N   | GLY | B | 333 | 59.010 | 1.921  | 51.413 | 1.00 | 39.80 | B | N |
| ATOM | 2942 | CA  | GLY | B | 333 | 57.640 | 2.094  | 51.852 | 1.00 | 39.32 | B | C |
| ATOM | 2943 | C   | GLY | B | 333 | 57.242 | 1.114  | 52.934 | 1.00 | 39.59 | B | C |
| ATOM | 2944 | O   | GLY | B | 333 | 56.642 | 1.497  | 53.949 | 1.00 | 38.97 | B | O |
| ATOM | 2945 | N   | ILE | B | 334 | 57.669 | -0.138 | 52.760 | 1.00 | 40.69 | B | N |
| ATOM | 2946 | CA  | ILE | B | 334 | 57.372 | -1.218 | 53.713 | 1.00 | 41.72 | B | C |
| ATOM | 2947 | CB  | ILE | B | 334 | 57.951 | -2.563 | 53.227 | 1.00 | 42.35 | B | C |
| ATOM | 2948 | CG2 | ILE | B | 334 | 58.000 | -3.556 | 54.373 | 1.00 | 43.77 | B | C |
| ATOM | 2949 | CG1 | ILE | B | 334 | 57.199 | -3.093 | 51.984 | 1.00 | 44.10 | B | C |
| ATOM | 2950 | CD1 | ILE | B | 334 | 55.704 | -3.541 | 52.172 | 1.00 | 44.42 | B | C |
| ATOM | 2951 | C   | ILE | B | 334 | 57.975 | -0.919 | 55.094 | 1.00 | 42.30 | B | C |
| ATOM | 2952 | O   | ILE | B | 334 | 57.392 | -1.263 | 56.123 | 1.00 | 42.66 | B | O |
| ATOM | 2953 | N   | LYS | B | 335 | 59.143 | -0.286 | 55.096 | 1.00 | 42.99 | B | N |
| ATOM | 2954 | CA  | LYS | B | 335 | 59.867 | 0.074  | 56.317 | 1.00 | 44.14 | B | C |
| ATOM | 2955 | CB  | LYS | B | 335 | 61.348 | 0.361  | 55.990 | 1.00 | 46.99 | B | C |
| ATOM | 2956 | CG  | LYS | B | 335 | 62.180 | -0.893 | 55.599 | 1.00 | 50.23 | B | C |
| ATOM | 2957 | CD  | LYS | B | 335 | 63.495 | -0.487 | 54.945 | 1.00 | 53.92 | B | C |
| ATOM | 2958 | CE  | LYS | B | 335 | 64.113 | -1.630 | 54.080 | 1.00 | 55.97 | B | C |
| ATOM | 2959 | NZ  | LYS | B | 335 | 64.902 | -0.984 | 52.922 | 1.00 | 58.47 | B | N |
| ATOM | 2960 | C   | LYS | B | 335 | 59.303 | 1.253  | 57.098 | 1.00 | 42.91 | B | C |
| ATOM | 2961 | O   | LYS | B | 335 | 59.599 | 1.387  | 58.286 | 1.00 | 43.57 | B | O |
| ATOM | 2962 | N   | LEU | B | 336 | 58.477 | 2.078  | 56.458 | 1.00 | 41.45 | B | N |
| ATOM | 2963 | CA  | LEU | B | 336 | 57.894 | 3.233  | 57.132 | 1.00 | 40.75 | B | C |
| ATOM | 2964 | CB  | LEU | B | 336 | 56.827 | 3.916  | 56.247 | 1.00 | 39.35 | B | C |
| ATOM | 2965 | CG  | LEU | B | 336 | 57.325 | 4.586  | 54.965 | 1.00 | 37.93 | B | C |
| ATOM | 2966 | CD1 | LEU | B | 336 | 56.160 | 5.049  | 54.180 | 1.00 | 36.41 | B | C |
| ATOM | 2967 | CD2 | LEU | B | 336 | 58.276 | 5.727  | 55.282 | 1.00 | 37.69 | B | C |
| ATOM | 2968 | C   | LEU | B | 336 | 57.278 | 2.910  | 58.500 | 1.00 | 40.67 | B | C |
| ATOM | 2969 | O   | LEU | B | 336 | 56.613 | 1.876  | 58.682 | 1.00 | 39.47 | B | O |
| ATOM | 2970 | N   | THR | B | 337 | 57.503 | 3.814  | 59.454 | 1.00 | 41.03 | B | N |
| ATOM | 2971 | CA  | THR | B | 337 | 56.966 | 3.662  | 60.790 | 1.00 | 41.02 | B | C |
| ATOM | 2972 | CB  | THR | B | 337 | 57.825 | 4.460  | 61.851 | 1.00 | 42.60 | B | C |
| ATOM | 2973 | OG1 | THR | B | 337 | 57.748 | 5.881  | 61.634 | 1.00 | 44.04 | B | O |
| ATOM | 2974 | CG2 | THR | B | 337 | 59.284 | 4.004  | 61.797 | 1.00 | 43.16 | B | C |
| ATOM | 2975 | C   | THR | B | 337 | 55.483 | 4.091  | 60.819 | 1.00 | 40.31 | B | C |
| ATOM | 2976 | O   | THR | B | 337 | 54.982 | 4.740  | 59.889 | 1.00 | 39.72 | B | O |
| ATOM | 2977 | N   | ILE | B | 338 | 54.767 | 3.644  | 61.847 | 1.00 | 39.66 | B | N |
| ATOM | 2978 | CA  | ILE | B | 338 | 53.369 | 3.997  | 62.014 | 1.00 | 37.59 | B | C |
| ATOM | 2979 | CB  | ILE | B | 338 | 52.765 | 3.289  | 63.241 | 1.00 | 35.77 | B | C |
| ATOM | 2980 | CG2 | ILE | B | 338 | 53.366 | 3.863  | 64.505 | 1.00 | 34.89 | B | C |
| ATOM | 2981 | CG1 | ILE | B | 338 | 51.244 | 3.514  | 63.337 | 1.00 | 35.73 | B | C |
| ATOM | 2982 | CD1 | ILE | B | 338 | 50.398 | 3.069  | 62.150 | 1.00 | 33.36 | B | C |
| ATOM | 2983 | C   | ILE | B | 338 | 53.317 | 5.521  | 62.214 | 1.00 | 38.08 | B | C |
| ATOM | 2984 | O   | ILE | B | 338 | 52.339 | 6.163  | 61.830 | 1.00 | 39.06 | B | O |
| ATOM | 2985 | N   | ASN | B | 339 | 54.376 | 6.102  | 62.785 | 1.00 | 38.08 | B | N |
| ATOM | 2986 | CA  | ASN | B | 339 | 54.402 | 7.549  | 63.012 | 1.00 | 37.62 | B | C |
| ATOM | 2987 | CB  | ASN | B | 339 | 55.627 | 7.972  | 63.821 | 1.00 | 38.69 | B | C |

Figure 13

| | | | | | | | | | | |
|---|---|---|---|---|---|---|---|---|---|---|
| ATOM | 2988 | CG | ASN | B | 339 | 55.613 | 7.451 | 65.256 | 1.00 39.65 | B C |
| ATOM | 2989 | OD1 | ASN | B | 339 | 55.386 | 8.229 | 66.206 | 1.00 38.86 | B O |
| ATOM | 2990 | ND2 | ASN | B | 339 | 55.914 | 6.140 | 65.431 | 1.00 39.67 | B N |
| ATOM | 2991 | C | ASN | B | 339 | 54.439 | 8.284 | 61.696 | 1.00 36.89 | B C |
| ATOM | 2992 | O | ASN | B | 339 | 53.783 | 9.305 | 61.531 | 1.00 36.38 | B O |
| ATOM | 2993 | N | LYS | B | 340 | 55.268 | 7.797 | 60.781 | 1.00 36.89 | B N |
| ATOM | 2994 | CA | LYS | B | 340 | 55.389 | 8.397 | 59.458 | 1.00 37.11 | B C |
| ATOM | 2995 | CB | LYS | B | 340 | 56.555 | 7.742 | 58.707 | 1.00 39.00 | B C |
| ATOM | 2996 | CG | LYS | B | 340 | 56.828 | 8.327 | 57.333 | 1.00 41.35 | B C |
| ATOM | 2997 | CD | LYS | B | 340 | 56.961 | 9.854 | 57.391 | 1.00 41.23 | B C |
| ATOM | 2998 | CE | LYS | B | 340 | 56.894 | 10.388 | 55.971 | 1.00 43.00 | B C |
| ATOM | 2999 | NZ | LYS | B | 340 | 57.002 | 11.868 | 55.864 | 1.00 41.68 | B N |
| ATOM | 3000 | C | LYS | B | 340 | 54.074 | 8.219 | 58.665 | 1.00 36.01 | B C |
| ATOM | 3001 | O | LYS | B | 340 | 53.566 | 9.156 | 58.031 | 1.00 36.20 | B O |
| ATOM | 3002 | N | LEU | B | 341 | 53.503 | 7.028 | 58.765 | 1.00 34.47 | B N |
| ATOM | 3003 | CA | LEU | B | 341 | 52.269 | 6.708 | 58.071 | 1.00 33.24 | B C |
| ATOM | 3004 | CB | LEU | B | 341 | 51.913 | 5.235 | 58.312 | 1.00 29.99 | B C |
| ATOM | 3005 | CG | LEU | B | 341 | 52.841 | 4.133 | 57.782 | 1.00 24.84 | B C |
| ATOM | 3006 | CD1 | LEU | B | 341 | 52.344 | 2.839 | 58.313 | 1.00 24.69 | B C |
| ATOM | 3007 | CD2 | LEU | B | 341 | 52.914 | 4.094 | 56.267 | 1.00 22.91 | B C |
| ATOM | 3008 | C | LEU | B | 341 | 51.145 | 7.654 | 58.507 | 1.00 33.87 | B C |
| ATOM | 3009 | O | LEU | B | 341 | 50.456 | 8.212 | 57.665 | 1.00 34.89 | B O |
| ATOM | 3010 | N | LEU | B | 342 | 51.001 | 7.892 | 59.809 | 1.00 34.90 | B N |
| ATOM | 3011 | CA | LEU | B | 342 | 49.975 | 8.806 | 60.303 | 1.00 35.64 | B C |
| ATOM | 3012 | CB | LEU | B | 342 | 49.866 | 8.732 | 61.813 | 1.00 36.42 | B C |
| ATOM | 3013 | CG | LEU | B | 342 | 49.265 | 7.403 | 62.235 | 1.00 37.37 | B C |
| ATOM | 3014 | CD1 | LEU | B | 342 | 48.922 | 7.392 | 63.674 | 1.00 38.64 | B C |
| ATOM | 3015 | CD2 | LEU | B | 342 | 48.042 | 7.168 | 61.430 | 1.00 36.65 | B C |
| ATOM | 3016 | C | LEU | B | 342 | 50.192 | 10.241 | 59.893 | 1.00 36.20 | B C |
| ATOM | 3017 | O | LEU | B | 342 | 49.228 | 10.974 | 59.709 | 1.00 36.61 | B O |
| ATOM | 3018 | N | ASP | B | 343 | 51.442 | 10.691 | 59.816 | 1.00 37.02 | B N |
| ATOM | 3019 | CA | ASP | B | 343 | 51.643 | 12.067 | 59.394 | 1.00 37.34 | B C |
| ATOM | 3020 | CB | ASP | B | 343 | 53.028 | 12.637 | 59.730 | 1.00 42.05 | B C |
| ATOM | 3021 | CG | ASP | B | 343 | 53.060 | 14.202 | 59.630 | 1.00 47.50 | B C |
| ATOM | 3022 | OD1 | ASP | B | 343 | 52.481 | 14.903 | 60.510 | 1.00 50.57 | B O |
| ATOM | 3023 | OD2 | ASP | B | 343 | 53.639 | 14.741 | 58.652 | 1.00 50.46 | B O |
| ATOM | 3024 | C | ASP | B | 343 | 51.334 | 12.160 | 57.897 | 1.00 35.27 | B C |
| ATOM | 3025 | O | ASP | B | 343 | 50.843 | 13.196 | 57.454 | 1.00 34.96 | B O |
| ATOM | 3026 | N | MET | B | 344 | 51.529 | 11.069 | 57.138 | 1.00 32.31 | B N |
| ATOM | 3027 | CA | MET | B | 344 | 51.188 | 11.118 | 55.718 | 1.00 29.99 | B C |
| ATOM | 3028 | CB | MET | B | 344 | 51.625 | 9.866 | 54.921 | 1.00 30.21 | B C |
| ATOM | 3029 | CG | MET | B | 344 | 53.088 | 9.726 | 54.704 | 1.00 31.84 | B C |
| ATOM | 3030 | SD | MET | B | 344 | 53.560 | 8.193 | 53.805 | 1.00 35.05 | B S |
| ATOM | 3031 | CE | MET | B | 344 | 54.465 | 8.805 | 52.405 | 1.00 33.89 | B C |
| ATOM | 3032 | C | MET | B | 344 | 49.651 | 11.261 | 55.663 | 1.00 27.77 | B C |
| ATOM | 3033 | O | MET | B | 344 | 49.118 | 12.136 | 54.980 | 1.00 26.41 | B O |
| ATOM | 3034 | N | ALA | B | 345 | 48.962 | 10.403 | 56.411 | 1.00 25.31 | B N |
| ATOM | 3035 | CA | ALA | B | 345 | 47.506 | 10.395 | 56.479 | 1.00 23.67 | B C |
| ATOM | 3036 | CB | ALA | B | 345 | 47.069 | 9.434 | 57.564 | 1.00 23.36 | B C |
| ATOM | 3037 | C | ALA | B | 345 | 46.937 | 11.785 | 56.775 | 1.00 23.29 | B C |
| ATOM | 3038 | O | ALA | B | 345 | 45.955 | 12.188 | 56.177 | 1.00 22.88 | B O |
| ATOM | 3039 | N | ALA | B | 346 | 47.547 | 12.464 | 57.755 | 1.00 22.65 | B N |
| ATOM | 3040 | CA | ALA | B | 346 | 47.200 | 13.796 | 58.241 | 1.00 22.06 | B C |
| ATOM | 3041 | CB | ALA | B | 346 | 48.075 | 14.141 | 59.444 | 1.00 20.34 | B C |
| ATOM | 3042 | C | ALA | B | 346 | 47.359 | 14.865 | 57.181 | 1.00 22.91 | B C |
| ATOM | 3043 | O | ALA | B | 346 | 46.654 | 15.879 | 57.228 | 1.00 24.33 | B O |
| ATOM | 3044 | N | GLN | B | 347 | 48.315 | 14.664 | 56.270 | 1.00 23.78 | B N |
| ATOM | 3045 | CA | GLN | B | 347 | 48.624 | 15.590 | 55.175 | 1.00 23.29 | B C |
| ATOM | 3046 | CB | GLN | B | 347 | 49.952 | 15.221 | 54.481 | 1.00 24.46 | B C |
| ATOM | 3047 | CG | GLN | B | 347 | 51.272 | 15.499 | 55.218 | 1.00 24.65 | B C |

Figure 13

| | | | | | | | | | | | |
|---|---|---|---|---|---|---|---|---|---|---|---|
| ATOM | 3048 | CD | GLN | B | 347 | 52.461 | 15.092 | 54.390 | 1.00 | 23.57 | B | C |
| ATOM | 3049 | OE1 | GLN | B | 347 | 53.243 | 15.915 | 53.947 | 1.00 | 23.19 | B | O |
| ATOM | 3050 | NE2 | GLN | B | 347 | 52.615 | 13.811 | 54.198 | 1.00 | 24.14 | B | N |
| ATOM | 3051 | C | GLN | B | 347 | 47.535 | 15.466 | 54.125 | 1.00 | 22.96 | B | C |
| ATOM | 3052 | O | GLN | B | 347 | 47.170 | 16.458 | 53.489 | 1.00 | 24.09 | B | O |
| ATOM | 3053 | N | ILE | B | 348 | 47.099 | 14.236 | 53.861 | 1.00 | 22.27 | B | N |
| ATOM | 3054 | CA | ILE | B | 348 | 46.039 | 14.012 | 52.896 | 1.00 | 21.72 | B | C |
| ATOM | 3055 | CB | ILE | B | 348 | 45.870 | 12.518 | 52.574 | 1.00 | 20.78 | B | C |
| ATOM | 3056 | CG2 | ILE | B | 348 | 44.630 | 12.323 | 51.738 | 1.00 | 21.47 | B | C |
| ATOM | 3057 | CG1 | ILE | B | 348 | 47.120 | 11.981 | 51.879 | 1.00 | 19.72 | B | C |
| ATOM | 3058 | CD1 | ILE | B | 348 | 47.273 | 10.493 | 51.979 | 1.00 | 19.49 | B | C |
| ATOM | 3059 | C | ILE | B | 348 | 44.746 | 14.574 | 53.481 | 1.00 | 21.82 | B | C |
| ATOM | 3060 | O | ILE | B | 348 | 43.954 | 15.203 | 52.779 | 1.00 | 20.19 | B | O |
| ATOM | 3061 | N | ALA | B | 349 | 44.561 | 14.350 | 54.778 | 1.00 | 22.37 | B | N |
| ATOM | 3062 | CA | ALA | B | 349 | 43.395 | 14.845 | 55.520 | 1.00 | 23.53 | B | C |
| ATOM | 3063 | CB | ALA | B | 349 | 43.502 | 14.404 | 56.960 | 1.00 | 22.52 | B | C |
| ATOM | 3064 | C | ALA | B | 349 | 43.359 | 16.368 | 55.473 | 1.00 | 23.77 | B | C |
| ATOM | 3065 | O | ALA | B | 349 | 42.296 | 16.975 | 55.559 | 1.00 | 24.58 | B | O |
| ATOM | 3066 | N | GLU | B | 350 | 44.548 | 16.959 | 55.473 | 1.00 | 23.07 | B | N |
| ATOM | 3067 | CA | GLU | B | 350 | 44.686 | 18.385 | 55.439 | 1.00 | 23.17 | B | C |
| ATOM | 3068 | CB | GLU | B | 350 | 46.132 | 18.784 | 55.678 | 1.00 | 23.89 | B | C |
| ATOM | 3069 | CG | GLU | B | 350 | 46.296 | 20.266 | 55.788 | 1.00 | 24.21 | B | C |
| ATOM | 3070 | CD | GLU | B | 350 | 47.705 | 20.706 | 55.972 | 1.00 | 25.93 | B | C |
| ATOM | 3071 | OE1 | GLU | B | 350 | 48.593 | 19.897 | 56.287 | 1.00 | 27.34 | B | O |
| ATOM | 3072 | OE2 | GLU | B | 350 | 47.951 | 21.901 | 55.783 | 1.00 | 28.90 | B | O |
| ATOM | 3073 | C | GLU | B | 350 | 44.221 | 18.908 | 54.100 | 1.00 | 23.43 | B | C |
| ATOM | 3074 | O | GLU | B | 350 | 43.496 | 19.893 | 54.041 | 1.00 | 24.23 | B | O |
| ATOM | 3075 | N | GLY | B | 351 | 44.639 | 18.233 | 53.031 | 1.00 | 23.09 | B | N |
| ATOM | 3076 | CA | GLY | B | 351 | 44.285 | 18.654 | 51.684 | 1.00 | 22.77 | B | C |
| ATOM | 3077 | C | GLY | B | 351 | 42.788 | 18.638 | 51.507 | 1.00 | 22.98 | B | C |
| ATOM | 3078 | O | GLY | B | 351 | 42.196 | 19.610 | 51.031 | 1.00 | 23.36 | B | O |
| ATOM | 3079 | N | MET | B | 352 | 42.192 | 17.543 | 51.960 | 1.00 | 23.48 | B | N |
| ATOM | 3080 | CA | MET | B | 352 | 40.756 | 17.337 | 51.914 | 1.00 | 23.95 | B | C |
| ATOM | 3081 | CB | MET | B | 352 | 40.391 | 15.936 | 52.362 | 1.00 | 22.63 | B | C |
| ATOM | 3082 | CG | MET | B | 352 | 40.754 | 14.869 | 51.382 | 1.00 | 23.86 | B | C |
| ATOM | 3083 | SD | MET | B | 352 | 40.200 | 15.186 | 49.675 | 1.00 | 23.49 | B | S |
| ATOM | 3084 | CE | MET | B | 352 | 38.470 | 15.340 | 49.936 | 1.00 | 22.80 | B | C |
| ATOM | 3085 | C | MET | B | 352 | 40.040 | 18.342 | 52.800 | 1.00 | 25.58 | B | C |
| ATOM | 3086 | O | MET | B | 352 | 38.843 | 18.690 | 52.569 | 1.00 | 27.24 | B | O |
| ATOM | 3087 | N | ALA | B | 353 | 40.726 | 18.747 | 53.861 | 1.00 | 24.64 | B | N |
| ATOM | 3088 | CA | ALA | B | 353 | 40.129 | 19.734 | 54.747 | 1.00 | 25.49 | B | C |
| ATOM | 3089 | CB | ALA | B | 353 | 40.960 | 19.911 | 55.994 | 1.00 | 25.02 | B | C |
| ATOM | 3090 | C | ALA | B | 353 | 39.993 | 21.068 | 53.962 | 1.00 | 26.36 | B | C |
| ATOM | 3091 | O | ALA | B | 353 | 39.035 | 21.834 | 54.123 | 1.00 | 26.58 | B | O |
| ATOM | 3092 | N | PHE | B | 354 | 40.941 | 21.310 | 53.072 | 1.00 | 26.78 | B | N |
| ATOM | 3093 | CA | PHE | B | 354 | 40.917 | 22.498 | 52.235 | 1.00 | 26.78 | B | C |
| ATOM | 3094 | CB | PHE | B | 354 | 42.265 | 22.661 | 51.536 | 1.00 | 25.78 | B | C |
| ATOM | 3095 | CG | PHE | B | 354 | 42.303 | 23.793 | 50.566 | 1.00 | 24.34 | B | C |
| ATOM | 3096 | CD1 | PHE | B | 354 | 42.239 | 25.107 | 51.027 | 1.00 | 23.08 | B | C |
| ATOM | 3097 | CD2 | PHE | B | 354 | 42.368 | 23.553 | 49.190 | 1.00 | 23.03 | B | C |
| ATOM | 3098 | CE1 | PHE | B | 354 | 42.243 | 26.161 | 50.138 | 1.00 | 20.05 | B | C |
| ATOM | 3099 | CE2 | PHE | B | 354 | 42.372 | 24.595 | 48.300 | 1.00 | 21.09 | B | C |
| ATOM | 3100 | CZ | PHE | B | 354 | 42.309 | 25.904 | 48.772 | 1.00 | 20.72 | B | C |
| ATOM | 3101 | C | PHE | B | 354 | 39.830 | 22.324 | 51.199 | 1.00 | 26.83 | B | C |
| ATOM | 3102 | O | PHE | B | 354 | 39.061 | 23.218 | 50.936 | 1.00 | 27.26 | B | O |
| ATOM | 3103 | N | ILE | B | 355 | 39.771 | 21.141 | 50.615 | 1.00 | 27.48 | B | N |
| ATOM | 3104 | CA | ILE | B | 355 | 38.768 | 20.828 | 49.604 | 1.00 | 27.65 | B | C |
| ATOM | 3105 | CB | ILE | B | 355 | 39.047 | 19.452 | 49.027 | 1.00 | 25.69 | B | C |
| ATOM | 3106 | CG2 | ILE | B | 355 | 37.881 | 19.001 | 48.128 | 1.00 | 24.77 | B | C |
| ATOM | 3107 | CG1 | ILE | B | 355 | 40.443 | 19.495 | 48.352 | 1.00 | 25.38 | B | C |

Figure 13

| | | | | | | | | | | |
|---|---|---|---|---|---|---|---|---|---|---|
| ATOM | 3108 | CD1 | ILE | B | 355 | 41.111 | 18.161 | 47.961 | 1.00 21.15 | B C |
| ATOM | 3109 | C | ILE | B | 355 | 37.360 | 20.890 | 50.195 | 1.00 29.24 | B C |
| ATOM | 3110 | O | ILE | B | 355 | 36.420 | 21.277 | 49.526 | 1.00 29.31 | B O |
| ATOM | 3111 | N | GLU | B | 356 | 37.223 | 20.518 | 51.461 | 1.00 31.08 | B N |
| ATOM | 3112 | CA | GLU | B | 356 | 35.940 | 20.539 | 52.126 | 1.00 32.48 | B C |
| ATOM | 3113 | CB | GLU | B | 356 | 36.070 | 19.848 | 53.444 | 1.00 32.63 | B C |
| ATOM | 3114 | CG | GLU | B | 356 | 34.806 | 19.751 | 54.288 | 1.00 32.87 | B C |
| ATOM | 3115 | CD | GLU | B | 356 | 35.141 | 19.117 | 55.639 | 1.00 34.64 | B C |
| ATOM | 3116 | OE1 | GLU | B | 356 | 35.838 | 19.802 | 56.452 | 1.00 35.57 | B O |
| ATOM | 3117 | OE2 | GLU | B | 356 | 34.891 | 17.887 | 55.811 | 1.00 35.10 | B O |
| ATOM | 3118 | C | GLU | B | 356 | 35.511 | 21.941 | 52.407 | 1.00 34.07 | B C |
| ATOM | 3119 | O | GLU | B | 356 | 34.339 | 22.254 | 52.286 | 1.00 35.49 | B O |
| ATOM | 3120 | N | GLU | B | 357 | 36.473 | 22.752 | 52.829 | 1.00 35.89 | B N |
| ATOM | 3121 | CA | GLU | B | 357 | 36.334 | 24.156 | 53.183 | 1.00 36.84 | B C |
| ATOM | 3122 | CB | GLU | B | 357 | 37.724 | 24.629 | 53.571 | 1.00 40.39 | B C |
| ATOM | 3123 | CG | GLU | B | 357 | 37.960 | 26.100 | 53.450 | 1.00 44.96 | B C |
| ATOM | 3124 | CD | GLU | B | 357 | 37.501 | 26.787 | 54.674 | 1.00 48.37 | B C |
| ATOM | 3125 | OE1 | GLU | B | 357 | 37.985 | 26.354 | 55.750 | 1.00 50.06 | B O |
| ATOM | 3126 | OE2 | GLU | B | 357 | 36.656 | 27.715 | 54.580 | 1.00 51.64 | B O |
| ATOM | 3127 | C | GLU | B | 357 | 35.858 | 25.006 | 52.044 | 1.00 36.17 | B C |
| ATOM | 3128 | O | GLU | B | 357 | 35.091 | 25.953 | 52.244 | 1.00 35.93 | B O |
| ATOM | 3129 | N | ARG | B | 358 | 36.429 | 24.718 | 50.877 | 1.00 35.62 | B N |
| ATOM | 3130 | CA | ARG | B | 358 | 36.145 | 25.425 | 49.656 | 1.00 35.11 | B C |
| ATOM | 3131 | CB | ARG | B | 358 | 37.328 | 25.299 | 48.700 | 1.00 36.84 | B C |
| ATOM | 3132 | CG | ARG | B | 358 | 38.619 | 25.984 | 49.198 | 1.00 41.56 | B C |
| ATOM | 3133 | CD | ARG | B | 358 | 38.473 | 27.525 | 49.397 | 1.00 46.45 | B C |
| ATOM | 3134 | NE | ARG | B | 358 | 38.324 | 28.249 | 48.132 | 1.00 51.80 | B N |
| ATOM | 3135 | CZ | ARG | B | 358 | 39.211 | 28.204 | 47.140 | 1.00 55.09 | B C |
| ATOM | 3136 | NH1 | ARG | B | 358 | 40.315 | 27.489 | 47.261 | 1.00 57.98 | B N |
| ATOM | 3137 | NH2 | ARG | B | 358 | 38.955 | 28.781 | 45.979 | 1.00 57.33 | B N |
| ATOM | 3138 | C | ARG | B | 358 | 34.884 | 24.925 | 48.984 | 1.00 35.00 | B C |
| ATOM | 3139 | O | ARG | B | 358 | 34.521 | 25.427 | 47.930 | 1.00 36.14 | B O |
| ATOM | 3140 | N | ASN | B | 359 | 34.197 | 23.977 | 49.616 | 1.00 34.32 | B N |
| ATOM | 3141 | CA | ASN | B | 359 | 32.965 | 23.361 | 49.098 | 1.00 34.30 | B C |
| ATOM | 3142 | CB | ASN | B | 359 | 31.744 | 24.325 | 49.012 | 1.00 36.98 | B C |
| ATOM | 3143 | CG | ASN | B | 359 | 31.443 | 25.069 | 50.342 | 1.00 40.70 | B C |
| ATOM | 3144 | OD1 | ASN | B | 359 | 30.754 | 24.517 | 51.238 | 1.00 38.16 | B O |
| ATOM | 3145 | ND2 | ASN | B | 359 | 31.893 | 26.373 | 50.436 | 1.00 41.35 | B N |
| ATOM | 3146 | C | ASN | B | 359 | 33.144 | 22.604 | 47.772 | 1.00 32.76 | B C |
| ATOM | 3147 | O | ASN | B | 359 | 32.432 | 22.831 | 46.797 | 1.00 33.04 | B O |
| ATOM | 3148 | N | TYR | B | 360 | 34.173 | 21.778 | 47.720 | 1.00 30.99 | B N |
| ATOM | 3149 | CA | TYR | B | 360 | 34.392 | 20.899 | 46.572 | 1.00 30.28 | B C |
| ATOM | 3150 | CB | TYR | B | 360 | 35.804 | 21.049 | 46.006 | 1.00 30.05 | B C |
| ATOM | 3151 | CG | TYR | B | 360 | 35.976 | 22.166 | 45.042 | 1.00 30.59 | B C |
| ATOM | 3152 | CD1 | TYR | B | 360 | 36.196 | 23.464 | 45.499 | 1.00 31.62 | B C |
| ATOM | 3153 | CE1 | TYR | B | 360 | 36.363 | 24.511 | 44.628 | 1.00 31.37 | B C |
| ATOM | 3154 | CD2 | TYR | B | 360 | 35.927 | 21.942 | 43.668 | 1.00 31.03 | B C |
| ATOM | 3155 | CE2 | TYR | B | 360 | 36.099 | 22.996 | 42.772 | 1.00 32.15 | B C |
| ATOM | 3156 | CZ | TYR | B | 360 | 36.316 | 24.280 | 43.270 | 1.00 32.98 | B C |
| ATOM | 3157 | OH | TYR | B | 360 | 36.489 | 25.341 | 42.419 | 1.00 33.94 | B O |
| ATOM | 3158 | C | TYR | B | 360 | 34.291 | 19.474 | 47.161 | 1.00 28.92 | B C |
| ATOM | 3159 | O | TYR | B | 360 | 34.012 | 19.294 | 48.355 | 1.00 28.61 | B O |
| ATOM | 3160 | N | ILE | B | 361 | 34.415 | 18.483 | 46.286 | 1.00 27.81 | B N |
| ATOM | 3161 | CA | ILE | B | 361 | 34.456 | 17.072 | 46.655 | 1.00 27.11 | B C |
| ATOM | 3162 | CB | ILE | B | 361 | 33.132 | 16.301 | 46.422 | 1.00 25.54 | B C |
| ATOM | 3163 | CG2 | ILE | B | 361 | 32.037 | 16.888 | 47.262 | 1.00 25.02 | B C |
| ATOM | 3164 | CG1 | ILE | B | 361 | 32.758 | 16.222 | 44.933 | 1.00 25.62 | B C |
| ATOM | 3165 | CD1 | ILE | B | 361 | 31.648 | 15.166 | 44.671 | 1.00 23.99 | B C |
| ATOM | 3166 | C | ILE | B | 361 | 35.578 | 16.467 | 45.783 | 1.00 27.75 | B C |
| ATOM | 3167 | O | ILE | B | 361 | 36.024 | 17.079 | 44.807 | 1.00 28.31 | B O |

Figure 13

| | | | | | | | | | | | |
|---|---|---|---|---|---|---|---|---|---|---|---|
| ATOM | 3168 | N | HIS | B | 362 | 36.078 | 15.293 | 46.149 | 1.00 | 27.08 | B N |
| ATOM | 3169 | CA | HIS | B | 362 | 37.120 | 14.665 | 45.357 | 1.00 | 25.89 | B C |
| ATOM | 3170 | CB | HIS | B | 362 | 38.147 | 13.985 | 46.251 | 1.00 | 25.01 | B C |
| ATOM | 3171 | CG | HIS | B | 362 | 39.390 | 13.537 | 45.534 | 1.00 | 24.65 | B C |
| ATOM | 3172 | CD2 | HIS | B | 362 | 40.695 | 13.687 | 45.854 | 1.00 | 23.26 | B C |
| ATOM | 3173 | ND1 | HIS | B | 362 | 39.367 | 12.830 | 44.353 | 1.00 | 24.95 | B N |
| ATOM | 3174 | CE1 | HIS | B | 362 | 40.604 | 12.576 | 43.962 | 1.00 | 22.50 | B C |
| ATOM | 3175 | NE2 | HIS | B | 362 | 41.428 | 13.090 | 44.856 | 1.00 | 21.78 | B N |
| ATOM | 3176 | C | HIS | B | 362 | 36.460 | 13.651 | 44.444 | 1.00 | 26.53 | B C |
| ATOM | 3177 | O | HIS | B | 362 | 36.555 | 13.770 | 43.232 | 1.00 | 27.08 | B O |
| ATOM | 3178 | N | ARG | B | 363 | 35.675 | 12.762 | 45.049 | 1.00 | 26.74 | B N |
| ATOM | 3179 | CA | ARG | B | 363 | 34.983 | 11.654 | 44.404 | 1.00 | 27.89 | B C |
| ATOM | 3180 | CB | ARG | B | 363 | 33.909 | 12.085 | 43.389 | 1.00 | 31.86 | B C |
| ATOM | 3181 | CG | ARG | B | 363 | 34.379 | 12.625 | 42.086 | 1.00 | 38.65 | B C |
| ATOM | 3182 | CD | ARG | B | 363 | 33.229 | 13.255 | 41.279 | 1.00 | 45.04 | B C |
| ATOM | 3183 | NE | ARG | B | 363 | 32.472 | 12.225 | 40.610 | 1.00 | 48.28 | B N |
| ATOM | 3184 | CZ | ARG | B | 363 | 31.164 | 12.078 | 40.729 | 1.00 | 50.91 | B C |
| ATOM | 3185 | NH1 | ARG | B | 363 | 30.459 | 12.919 | 41.481 | 1.00 | 50.64 | B N |
| ATOM | 3186 | NH2 | ARG | B | 363 | 30.574 | 11.046 | 40.129 | 1.00 | 52.64 | B N |
| ATOM | 3187 | C | ARG | B | 363 | 35.904 | 10.530 | 43.898 | 1.00 | 26.74 | B C |
| ATOM | 3188 | O | ARG | B | 363 | 35.444 | 9.403 | 43.720 | 1.00 | 26.90 | B O |
| ATOM | 3189 | N | ASP | B | 364 | 37.215 | 10.811 | 43.821 | 1.00 | 24.68 | B N |
| ATOM | 3190 | CA | ASP | B | 364 | 38.211 | 9.834 | 43.416 | 1.00 | 22.74 | B C |
| ATOM | 3191 | CB | ASP | B | 364 | 38.789 | 10.138 | 42.035 | 1.00 | 23.37 | B C |
| ATOM | 3192 | CG | ASP | B | 364 | 37.803 | 9.834 | 40.921 | 1.00 | 25.17 | B C |
| ATOM | 3193 | OD1 | ASP | B | 364 | 37.693 | 8.641 | 40.507 | 1.00 | 25.83 | B O |
| ATOM | 3194 | OD2 | ASP | B | 364 | 37.080 | 10.778 | 40.497 | 1.00 | 27.85 | B O |
| ATOM | 3195 | C | ASP | B | 364 | 39.298 | 9.625 | 44.497 | 1.00 | 22.16 | B C |
| ATOM | 3196 | O | ASP | B | 364 | 40.465 | 9.315 | 44.220 | 1.00 | 22.47 | B O |
| ATOM | 3197 | N | LEU | B | 365 | 38.890 | 9.765 | 45.750 | 1.00 | 19.82 | B N |
| ATOM | 3198 | CA | LEU | B | 365 | 39.810 | 9.598 | 46.847 | 1.00 | 18.18 | B C |
| ATOM | 3199 | CB | LEU | B | 365 | 39.300 | 10.284 | 48.113 | 1.00 | 15.59 | B C |
| ATOM | 3200 | CG | LEU | B | 365 | 40.321 | 10.319 | 49.233 | 1.00 | 12.64 | B C |
| ATOM | 3201 | CD1 | LEU | B | 365 | 41.560 | 11.061 | 48.810 | 1.00 | 12.47 | B C |
| ATOM | 3202 | CD2 | LEU | B | 365 | 39.724 | 10.912 | 50.417 | 1.00 | 12.76 | B C |
| ATOM | 3203 | C | LEU | B | 365 | 40.196 | 8.165 | 47.146 | 1.00 | 19.64 | B C |
| ATOM | 3204 | O | LEU | B | 365 | 39.372 | 7.324 | 47.512 | 1.00 | 18.87 | B O |
| ATOM | 3205 | N | ARG | B | 366 | 41.470 | 7.885 | 46.890 | 1.00 | 22.12 | B N |
| ATOM | 3206 | CA | ARG | B | 366 | 42.092 | 6.596 | 47.166 | 1.00 | 23.68 | B C |
| ATOM | 3207 | CB | ARG | B | 366 | 41.634 | 5.490 | 46.196 | 1.00 | 24.69 | B C |
| ATOM | 3208 | CG | ARG | B | 366 | 41.956 | 5.641 | 44.724 | 1.00 | 27.35 | B C |
| ATOM | 3209 | CD | ARG | B | 366 | 41.660 | 4.330 | 43.958 | 1.00 | 28.44 | B C |
| ATOM | 3210 | NE | ARG | B | 366 | 41.332 | 4.594 | 42.557 | 1.00 | 31.06 | B N |
| ATOM | 3211 | CZ | ARG | B | 366 | 40.240 | 5.233 | 42.154 | 1.00 | 32.14 | B C |
| ATOM | 3212 | NH1 | ARG | B | 366 | 39.344 | 5.696 | 43.042 | 1.00 | 32.35 | B N |
| ATOM | 3213 | NH2 | ARG | B | 366 | 40.075 | 5.455 | 40.859 | 1.00 | 32.03 | B N |
| ATOM | 3214 | C | ARG | B | 366 | 43.596 | 6.785 | 47.168 | 1.00 | 24.22 | B C |
| ATOM | 3215 | O | ARG | B | 366 | 44.093 | 7.788 | 46.714 | 1.00 | 24.57 | B O |
| ATOM | 3216 | N | ALA | B | 367 | 44.333 | 5.842 | 47.718 | 1.00 | 25.47 | B N |
| ATOM | 3217 | CA | ALA | B | 367 | 45.748 | 6.011 | 47.750 | 1.00 | 26.37 | B C |
| ATOM | 3218 | CB | ALA | B | 367 | 46.375 | 4.971 | 48.616 | 1.00 | 25.94 | B C |
| ATOM | 3219 | C | ALA | B | 367 | 46.376 | 6.042 | 46.346 | 1.00 | 27.76 | B C |
| ATOM | 3220 | O | ALA | B | 367 | 47.480 | 6.578 | 46.199 | 1.00 | 28.72 | B O |
| ATOM | 3221 | N | ALA | B | 368 | 45.710 | 5.474 | 45.329 | 1.00 | 27.17 | B N |
| ATOM | 3222 | CA | ALA | B | 368 | 46.252 | 5.496 | 43.964 | 1.00 | 26.20 | B C |
| ATOM | 3223 | CB | ALA | B | 368 | 45.371 | 4.701 | 43.049 | 1.00 | 27.06 | B C |
| ATOM | 3224 | C | ALA | B | 368 | 46.387 | 6.910 | 43.425 | 1.00 | 26.56 | B C |
| ATOM | 3225 | O | ALA | B | 368 | 47.252 | 7.210 | 42.593 | 1.00 | 28.16 | B O |
| ATOM | 3226 | N | ASN | B | 369 | 45.507 | 7.779 | 43.897 | 1.00 | 25.94 | B N |
| ATOM | 3227 | CA | ASN | B | 369 | 45.453 | 9.159 | 43.466 | 1.00 | 24.40 | B C |

Figure 13

| ATOM | 3228 | CB | ASN | B | 369 | 44.007 | 9.526 | 43.176 | 1.00 | 24.28 | B | C |
| ATOM | 3229 | CG | ASN | B | 369 | 43.390 | 8.627 | 42.125 | 1.00 | 24.11 | B | C |
| ATOM | 3230 | OD1 | ASN | B | 369 | 43.996 | 8.391 | 41.066 | 1.00 | 23.14 | B | O |
| ATOM | 3231 | ND2 | ASN | B | 369 | 42.180 | 8.108 | 42.411 | 1.00 | 23.25 | B | N |
| ATOM | 3232 | C | ASN | B | 369 | 46.079 | 10.142 | 44.411 | 1.00 | 23.36 | B | C |
| ATOM | 3233 | O | ASN | B | 369 | 45.641 | 11.261 | 44.473 | 1.00 | 24.46 | B | O |
| ATOM | 3234 | N | ILE | B | 370 | 47.001 | 9.669 | 45.234 | 1.00 | 23.12 | B | N |
| ATOM | 3235 | CA | ILE | B | 370 | 47.777 | 10.529 | 46.127 | 1.00 | 22.45 | B | C |
| ATOM | 3236 | CB | ILE | B | 370 | 47.756 | 10.041 | 47.589 | 1.00 | 21.87 | B | C |
| ATOM | 3237 | CG2 | ILE | B | 370 | 48.858 | 10.761 | 48.429 | 1.00 | 18.85 | B | C |
| ATOM | 3238 | CG1 | ILE | B | 370 | 46.347 | 10.104 | 48.174 | 1.00 | 18.98 | B | C |
| ATOM | 3239 | CD1 | ILE | B | 370 | 45.731 | 11.462 | 48.112 | 1.00 | 20.58 | B | C |
| ATOM | 3240 | C | ILE | B | 370 | 49.250 | 10.369 | 45.619 | 1.00 | 22.98 | B | C |
| ATOM | 3241 | O | ILE | B | 370 | 49.679 | 9.256 | 45.284 | 1.00 | 21.58 | B | O |
| ATOM | 3242 | N | LEU | B | 371 | 49.991 | 11.484 | 45.535 | 1.00 | 24.40 | B | N |
| ATOM | 3243 | CA | LEU | B | 371 | 51.377 | 11.489 | 45.062 | 1.00 | 24.70 | B | C |
| ATOM | 3244 | CB | LEU | B | 371 | 51.544 | 12.505 | 43.912 | 1.00 | 25.12 | B | C |
| ATOM | 3245 | CG | LEU | B | 371 | 50.771 | 12.255 | 42.608 | 1.00 | 23.93 | B | C |
| ATOM | 3246 | CD1 | LEU | B | 371 | 51.151 | 13.278 | 41.531 | 1.00 | 22.07 | B | C |
| ATOM | 3247 | CD2 | LEU | B | 371 | 51.057 | 10.862 | 42.097 | 1.00 | 23.74 | B | C |
| ATOM | 3248 | C | LEU | B | 371 | 52.375 | 11.762 | 46.189 | 1.00 | 24.70 | B | C |
| ATOM | 3249 | O | LEU | B | 371 | 52.085 | 12.536 | 47.092 | 1.00 | 24.13 | B | O |
| ATOM | 3250 | N | VAL | B | 372 | 53.537 | 11.118 | 46.122 | 1.00 | 24.86 | B | N |
| ATOM | 3251 | CA | VAL | B | 372 | 54.579 | 11.251 | 47.145 | 1.00 | 25.71 | B | C |
| ATOM | 3252 | CB | VAL | B | 372 | 54.939 | 9.859 | 47.781 | 1.00 | 26.49 | B | C |
| ATOM | 3253 | CG1 | VAL | B | 372 | 55.635 | 10.056 | 49.142 | 1.00 | 26.16 | B | C |
| ATOM | 3254 | CG2 | VAL | B | 372 | 53.665 | 9.004 | 47.963 | 1.00 | 25.26 | B | C |
| ATOM | 3255 | C | VAL | B | 372 | 55.854 | 11.924 | 46.634 | 1.00 | 26.52 | B | C |
| ATOM | 3256 | O | VAL | B | 372 | 56.391 | 11.570 | 45.574 | 1.00 | 26.44 | B | O |
| ATOM | 3257 | N | SER | B | 373 | 56.292 | 12.945 | 47.361 | 1.00 | 26.97 | B | N |
| ATOM | 3258 | CA | SER | B | 373 | 57.492 | 13.657 | 46.967 | 1.00 | 27.73 | B | C |
| ATOM | 3259 | CB | SER | B | 373 | 57.499 | 15.059 | 47.508 | 1.00 | 26.24 | B | C |
| ATOM | 3260 | OG | SER | B | 373 | 57.837 | 15.011 | 48.875 | 1.00 | 25.86 | B | O |
| ATOM | 3261 | C | SER | B | 373 | 58.735 | 12.978 | 47.475 | 1.00 | 28.99 | B | C |
| ATOM | 3262 | O | SER | B | 373 | 58.675 | 12.087 | 48.330 | 1.00 | 28.87 | B | O |
| ATOM | 3263 | N | ASP | B | 374 | 59.862 | 13.513 | 47.012 | 1.00 | 30.68 | B | N |
| ATOM | 3264 | CA | ASP | B | 374 | 61.180 | 13.030 | 47.390 | 1.00 | 31.99 | B | C |
| ATOM | 3265 | CB | ASP | B | 374 | 62.268 | 13.758 | 46.571 | 1.00 | 32.06 | B | C |
| ATOM | 3266 | CG | ASP | B | 374 | 62.156 | 15.282 | 46.637 | 1.00 | 32.42 | B | C |
| ATOM | 3267 | OD1 | ASP | B | 374 | 61.318 | 15.871 | 45.921 | 1.00 | 34.48 | B | O |
| ATOM | 3268 | OD2 | ASP | B | 374 | 62.954 | 15.887 | 47.375 | 1.00 | 33.17 | B | O |
| ATOM | 3269 | C | ASP | B | 374 | 61.392 | 13.141 | 48.918 | 1.00 | 32.97 | B | C |
| ATOM | 3270 | O | ASP | B | 374 | 62.042 | 12.291 | 49.513 | 1.00 | 32.11 | B | O |
| ATOM | 3271 | N | THR | B | 375 | 60.790 | 14.141 | 49.561 | 1.00 | 33.04 | B | N |
| ATOM | 3272 | CA | THR | B | 375 | 60.902 | 14.252 | 51.010 | 1.00 | 34.32 | B | C |
| ATOM | 3273 | CB | THR | B | 375 | 60.878 | 15.716 | 51.519 | 1.00 | 35.59 | B | C |
| ATOM | 3274 | OG1 | THR | B | 375 | 59.534 | 16.224 | 51.504 | 1.00 | 34.59 | B | O |
| ATOM | 3275 | CG2 | THR | B | 375 | 61.750 | 16.587 | 50.627 | 1.00 | 38.64 | B | C |
| ATOM | 3276 | C | THR | B | 375 | 59.744 | 13.498 | 51.673 | 1.00 | 34.70 | B | C |
| ATOM | 3277 | O | THR | B | 375 | 59.476 | 13.677 | 52.863 | 1.00 | 35.01 | B | O |
| ATOM | 3278 | N | LEU | B | 376 | 59.079 | 12.650 | 50.895 | 1.00 | 34.20 | B | N |
| ATOM | 3279 | CA | LEU | B | 376 | 57.977 | 11.835 | 51.368 | 1.00 | 34.66 | B | C |
| ATOM | 3280 | CB | LEU | B | 376 | 58.480 | 10.866 | 52.437 | 1.00 | 35.38 | B | C |
| ATOM | 3281 | CG | LEU | B | 376 | 59.693 | 9.977 | 52.099 | 1.00 | 36.25 | B | C |
| ATOM | 3282 | CD1 | LEU | B | 376 | 59.922 | 9.018 | 53.261 | 1.00 | 36.98 | B | C |
| ATOM | 3283 | CD2 | LEU | B | 376 | 59.486 | 9.213 | 50.780 | 1.00 | 36.06 | B | C |
| ATOM | 3284 | C | LEU | B | 376 | 56.698 | 12.538 | 51.833 | 1.00 | 35.18 | B | C |
| ATOM | 3285 | O | LEU | B | 376 | 55.888 | 11.959 | 52.560 | 1.00 | 35.11 | B | O |
| ATOM | 3286 | N | SER | B | 377 | 56.501 | 13.774 | 51.393 | 1.00 | 34.90 | B | N |
| ATOM | 3287 | CA | SER | B | 377 | 55.304 | 14.510 | 51.735 | 1.00 | 34.28 | B | C |

Figure 13

```
ATOM   3288  CB   SER B 377      55.583  16.018  51.755  1.00 35.73      B    C
ATOM   3289  OG   SER B 377      55.747  16.529  50.448  1.00 35.66      B    O
ATOM   3290  C    SER B 377      54.246  14.165  50.674  1.00 34.00      B    C
ATOM   3291  O    SER B 377      54.569  14.096  49.479  1.00 33.18      B    O
ATOM   3292  N    CYS B 378      52.985  13.997  51.101  1.00 34.20      B    N
ATOM   3293  CA   CYS B 378      51.880  13.620  50.206  1.00 32.90      B    C
ATOM   3294  CB   CYS B 378      50.917  12.653  50.912  1.00 32.75      B    C
ATOM   3295  SG   CYS B 378      51.644  11.224  51.684  1.00 33.19      B    S
ATOM   3296  C    CYS B 378      51.063  14.811  49.733  1.00 32.17      B    C
ATOM   3297  O    CYS B 378      50.710  15.690  50.534  1.00 33.84      B    O
ATOM   3298  N    LYS B 379      50.660  14.739  48.467  1.00 30.96      B    N
ATOM   3299  CA   LYS B 379      49.831  15.753  47.760  1.00 29.36      B    C
ATOM   3300  CB   LYS B 379      50.690  16.529  46.733  1.00 29.66      B    C
ATOM   3301  CG   LYS B 379      51.267  17.863  47.240  1.00 32.52      B    C
ATOM   3302  CD   LYS B 379      52.691  18.115  46.730  1.00 36.02      B    C
ATOM   3303  CE   LYS B 379      53.273  19.519  47.156  1.00 34.85      B    C
ATOM   3304  NZ   LYS B 379      52.449  20.728  46.544  1.00 39.95      B    N
ATOM   3305  C    LYS B 379      48.662  14.999  47.034  1.00 27.82      B    C
ATOM   3306  O    LYS B 379      48.855  13.892  46.482  1.00 26.85      B    O
ATOM   3307  N    ILE B 380      47.468  15.589  47.061  1.00 25.33      B    N
ATOM   3308  CA   ILE B 380      46.249  15.030  46.451  1.00 24.31      B    C
ATOM   3309  CB   ILE B 380      44.968  15.599  47.108  1.00 23.89      B    C
ATOM   3310  CG2  ILE B 380      43.708  15.036  46.440  1.00 20.17      B    C
ATOM   3311  CG1  ILE B 380      45.016  15.333  48.612  1.00 24.47      B    C
ATOM   3312  CD1  ILE B 380      43.962  16.056  49.371  1.00 27.19      B    C
ATOM   3313  C    ILE B 380      46.138  15.387  44.998  1.00 24.18      B    C
ATOM   3314  O    ILE B 380      46.154  16.584  44.636  1.00 25.59      B    O
ATOM   3315  N    ALA B 381      45.948  14.374  44.161  1.00 23.83      B    N
ATOM   3316  CA   ALA B 381      45.790  14.639  42.731  1.00 23.94      B    C
ATOM   3317  CB   ALA B 381      46.773  13.864  41.877  1.00 23.72      B    C
ATOM   3318  C    ALA B 381      44.387  14.272  42.360  1.00 23.27      B    C
ATOM   3319  O    ALA B 381      43.601  13.863  43.225  1.00 22.59      B    O
ATOM   3320  N    ASP B 382      44.072  14.580  41.106  1.00 23.34      B    N
ATOM   3321  CA   ASP B 382      42.807  14.295  40.449  1.00 24.13      B    C
ATOM   3322  CB   ASP B 382      42.893  12.940  39.737  1.00 23.53      B    C
ATOM   3323  CG   ASP B 382      43.935  12.944  38.611  1.00 22.71      B    C
ATOM   3324  OD1  ASP B 382      44.055  13.992  37.924  1.00 22.69      B    O
ATOM   3325  OD2  ASP B 382      44.611  11.905  38.383  1.00 23.07      B    O
ATOM   3326  C    ASP B 382      41.513  14.469  41.220  1.00 25.52      B    C
ATOM   3327  O    ASP B 382      40.615  13.612  41.199  1.00 25.64      B    O
ATOM   3328  N    PHE B 383      41.419  15.629  41.856  1.00 26.67      B    N
ATOM   3329  CA   PHE B 383      40.254  15.989  42.646  1.00 29.99      B    C
ATOM   3330  CB   PHE B 383      40.690  16.774  43.875  1.00 30.83      B    C
ATOM   3331  CG   PHE B 383      41.453  17.987  43.552  1.00 33.80      B    C
ATOM   3332  CD1  PHE B 383      40.816  19.214  43.465  1.00 35.02      B    C
ATOM   3333  CD2  PHE B 383      42.811  17.898  43.289  1.00 36.25      B    C
ATOM   3334  CE1  PHE B 383      41.517  20.356  43.114  1.00 36.39      B    C
ATOM   3335  CE2  PHE B 383      43.548  19.037  42.930  1.00 38.05      B    C
ATOM   3336  CZ   PHE B 383      42.893  20.275  42.844  1.00 37.89      B    C
ATOM   3337  C    PHE B 383      39.222  16.805  41.840  1.00 30.84      B    C
ATOM   3338  O    PHE B 383      39.556  17.450  40.849  1.00 32.07      B    O
ATOM   3339  N    GLY B 384      37.964  16.758  42.260  1.00 30.77      B    N
ATOM   3340  CA   GLY B 384      36.938  17.533  41.591  1.00 30.88      B    C
ATOM   3341  C    GLY B 384      36.557  17.145  40.187  1.00 31.46      B    C
ATOM   3342  O    GLY B 384      35.831  17.903  39.569  1.00 32.58      B    O
ATOM   3343  N    LEU B 385      37.022  16.007  39.676  1.00 31.83      B    N
ATOM   3344  CA   LEU B 385      36.663  15.606  38.321  1.00 33.55      B    C
ATOM   3345  CB   LEU B 385      37.387  14.342  37.886  1.00 34.22      B    C
ATOM   3346  CG   LEU B 385      38.899  14.472  37.929  1.00 36.16      B    C
ATOM   3347  CD1  LEU B 385      39.540  13.235  37.350  1.00 34.67      B    C
```

Figure 13

| | | | | | | | | | | |
|---|---|---|---|---|---|---|---|---|---|---|
| ATOM | 3348 | CD2 | LEU | B | 385 | 39.316 | 15.717 | 37.153 | 1.00 37.15 | B C |
| ATOM | 3349 | C | LEU | B | 385 | 35.188 | 15.340 | 38.241 | 1.00 35.72 | B C |
| ATOM | 3350 | O | LEU | B | 385 | 34.565 | 14.949 | 39.228 | 1.00 35.93 | B O |
| ATOM | 3351 | N | ALA | B | 386 | 34.612 | 15.573 | 37.065 | 1.00 37.61 | B N |
| ATOM | 3352 | CA | ALA | B | 386 | 33.186 | 15.332 | 36.920 | 1.00 39.42 | B C |
| ATOM | 3353 | CB | ALA | B | 386 | 32.620 | 16.147 | 35.780 | 1.00 40.52 | B C |
| ATOM | 3354 | C | ALA | B | 386 | 32.887 | 13.860 | 36.713 | 1.00 39.99 | B C |
| ATOM | 3355 | O | ALA | B | 386 | 31.739 | 13.456 | 36.787 | 1.00 41.51 | B O |
| ATOM | 3356 | N | ARG | B | 387 | 33.927 | 13.061 | 36.519 | 1.00 39.53 | B N |
| ATOM | 3357 | CA | ARG | B | 387 | 33.770 | 11.626 | 36.251 | 1.00 39.74 | B C |
| ATOM | 3358 | CB | ARG | B | 387 | 34.274 | 11.336 | 34.836 | 1.00 40.46 | B C |
| ATOM | 3359 | CG | ARG | B | 387 | 35.756 | 11.691 | 34.645 | 1.00 41.49 | B C |
| ATOM | 3360 | CD | ARG | B | 387 | 36.207 | 11.377 | 33.235 | 1.00 44.87 | B C |
| ATOM | 3361 | NE | ARG | B | 387 | 37.664 | 11.371 | 33.107 | 1.00 47.81 | B N |
| ATOM | 3362 | CZ | ARG | B | 387 | 38.463 | 10.305 | 33.247 | 1.00 49.72 | B C |
| ATOM | 3363 | NH1 | ARG | B | 387 | 37.953 | 9.111 | 33.510 | 1.00 48.44 | B N |
| ATOM | 3364 | NH2 | ARG | B | 387 | 39.799 | 10.462 | 33.189 | 1.00 51.39 | B N |
| ATOM | 3365 | C | ARG | B | 387 | 34.542 | 10.730 | 37.218 | 1.00 39.31 | B C |
| ATOM | 3366 | O | ARG | B | 387 | 35.432 | 11.215 | 37.937 | 1.00 39.30 | B O |
| ATOM | 3367 | N | LEU | B | 388 | 34.212 | 9.428 | 37.215 | 1.00 36.90 | B N |
| ATOM | 3368 | CA | LEU | B | 388 | 34.913 | 8.463 | 38.065 | 1.00 34.92 | B C |
| ATOM | 3369 | CB | LEU | B | 388 | 33.994 | 7.344 | 38.546 | 1.00 35.34 | B C |
| ATOM | 3370 | CG | LEU | B | 388 | 32.756 | 7.900 | 39.249 | 1.00 36.82 | B C |
| ATOM | 3371 | CD1 | LEU | B | 388 | 31.721 | 6.781 | 39.432 | 1.00 37.22 | B C |
| ATOM | 3372 | CD2 | LEU | B | 388 | 33.122 | 8.534 | 40.588 | 1.00 37.85 | B C |
| ATOM | 3373 | C | LEU | B | 388 | 36.059 | 7.887 | 37.272 | 1.00 33.11 | B C |
| ATOM | 3374 | O | LEU | B | 388 | 35.845 | 7.313 | 36.212 | 1.00 31.91 | B O |
| ATOM | 3375 | N | ILE | B | 389 | 37.279 | 8.083 | 37.774 | 1.00 31.69 | B N |
| ATOM | 3376 | CA | ILE | B | 389 | 38.474 | 7.596 | 37.090 | 1.00 30.43 | B C |
| ATOM | 3377 | CB | ILE | B | 389 | 39.660 | 8.565 | 37.230 | 1.00 28.78 | B C |
| ATOM | 3378 | CG2 | ILE | B | 389 | 39.295 | 9.937 | 36.637 | 1.00 27.33 | B C |
| ATOM | 3379 | CG1 | ILE | B | 389 | 40.094 | 8.654 | 38.690 | 1.00 28.35 | B C |
| ATOM | 3380 | CD1 | ILE | B | 389 | 41.315 | 9.556 | 38.922 | 1.00 30.17 | B C |
| ATOM | 3381 | C | ILE | B | 389 | 38.948 | 6.235 | 37.545 | 1.00 31.23 | B C |
| ATOM | 3382 | O | ILE | B | 389 | 38.624 | 5.742 | 38.638 | 1.00 32.33 | B O |
| ATOM | 3383 | N | GLU | B | 390 | 39.734 | 5.613 | 36.680 | 1.00 31.17 | B N |
| ATOM | 3384 | CA | GLU | B | 390 | 40.283 | 4.314 | 36.994 | 1.00 31.03 | B C |
| ATOM | 3385 | CB | GLU | B | 390 | 39.799 | 3.279 | 35.985 | 1.00 32.45 | B C |
| ATOM | 3386 | CG | GLU | B | 390 | 38.321 | 3.231 | 35.828 | 1.00 32.78 | B C |
| ATOM | 3387 | CD | GLU | B | 390 | 37.885 | 2.006 | 35.074 | 1.00 34.66 | B C |
| ATOM | 3388 | OE1 | GLU | B | 390 | 36.669 | 1.741 | 34.997 | 1.00 39.79 | B O |
| ATOM | 3389 | OE2 | GLU | B | 390 | 38.751 | 1.278 | 34.568 | 1.00 33.97 | B O |
| ATOM | 3390 | C | GLU | B | 390 | 41.813 | 4.360 | 36.994 | 1.00 30.44 | B C |
| ATOM | 3391 | O | GLU | B | 390 | 42.433 | 5.229 | 36.383 | 1.00 28.72 | B O |
| ATOM | 3392 | N | ASP | B | 391 | 42.417 | 3.368 | 37.636 | 1.00 30.97 | B N |
| ATOM | 3393 | CA | ASP | B | 391 | 43.874 | 3.313 | 37.695 | 1.00 32.32 | B C |
| ATOM | 3394 | CB | ASP | B | 391 | 44.298 | 2.320 | 38.756 | 1.00 33.65 | B C |
| ATOM | 3395 | CG | ASP | B | 391 | 43.831 | 2.734 | 40.126 | 1.00 37.42 | B C |
| ATOM | 3396 | OD1 | ASP | B | 391 | 43.332 | 3.888 | 40.268 | 1.00 38.99 | B O |
| ATOM | 3397 | OD2 | ASP | B | 391 | 43.993 | 1.923 | 41.062 | 1.00 38.55 | B O |
| ATOM | 3398 | C | ASP | B | 391 | 44.599 | 3.013 | 36.403 | 1.00 32.02 | B C |
| ATOM | 3399 | O | ASP | B | 391 | 45.666 | 3.556 | 36.170 | 1.00 31.92 | B O |
| ATOM | 3400 | N | ASN | B | 392 | 43.985 | 2.179 | 35.569 | 1.00 32.63 | B N |
| ATOM | 3401 | CA | ASN | B | 392 | 44.541 | 1.736 | 34.304 | 1.00 31.83 | B C |
| ATOM | 3402 | CB | ASN | B | 392 | 43.798 | 0.449 | 33.907 | 1.00 31.58 | B C |
| ATOM | 3403 | CG | ASN | B | 392 | 42.365 | 0.695 | 33.471 | 1.00 32.30 | B C |
| ATOM | 3404 | OD1 | ASN | B | 392 | 41.755 | 1.732 | 33.752 | 1.00 31.00 | B O |
| ATOM | 3405 | ND2 | ASN | B | 392 | 41.823 | -0.272 | 32.769 | 1.00 33.39 | B N |
| ATOM | 3406 | C | ASN | B | 392 | 44.542 | 2.763 | 33.161 | 1.00 31.30 | B C |
| ATOM | 3407 | O | ASN | B | 392 | 44.966 | 2.438 | 32.059 | 1.00 31.32 | B O |

Figure 13

| ATOM | 3408 | N | GLU | B | 393 | 44.110 | 3.992 | 33.448 | 1.00 | 30.81 | B | N |
|------|------|------|------|---|-----|--------|-------|--------|------|-------|---|---|
| ATOM | 3409 | CA | GLU | B | 393 | 44.023 | 5.071 | 32.456 | 1.00 | 32.06 | B | C |
| ATOM | 3410 | CB | GLU | B | 393 | 43.052 | 6.156 | 32.967 | 1.00 | 32.19 | B | C |
| ATOM | 3411 | CG | GLU | B | 393 | 41.591 | 5.628 | 33.105 | 1.00 | 31.25 | B | C |
| ATOM | 3412 | CD | GLU | B | 393 | 40.569 | 6.660 | 33.507 | 1.00 | 29.59 | B | C |
| ATOM | 3413 | OE1 | GLU | B | 393 | 40.934 | 7.828 | 33.742 | 1.00 | 29.56 | B | O |
| ATOM | 3414 | OE2 | GLU | B | 393 | 39.384 | 6.280 | 33.579 | 1.00 | 29.09 | B | O |
| ATOM | 3415 | C | GLU | B | 393 | 45.336 | 5.691 | 31.957 | 1.00 | 33.14 | B | C |
| ATOM | 3416 | O | GLU | B | 393 | 45.534 | 5.895 | 30.751 | 1.00 | 31.51 | B | O |
| ATOM | 3417 | N | TYR | B | 394 | 46.257 | 5.902 | 32.896 | 1.00 | 35.05 | B | N |
| ATOM | 3418 | CA | TYR | B | 394 | 47.562 | 6.460 | 32.595 | 1.00 | 37.35 | B | C |
| ATOM | 3419 | CB | TYR | B | 394 | 47.650 | 7.901 | 33.097 | 1.00 | 36.59 | B | C |
| ATOM | 3420 | CG | TYR | B | 394 | 46.562 | 8.770 | 32.500 | 1.00 | 36.53 | B | C |
| ATOM | 3421 | CD1 | TYR | B | 394 | 45.352 | 8.944 | 33.156 | 1.00 | 36.66 | B | C |
| ATOM | 3422 | CE1 | TYR | B | 394 | 44.305 | 9.663 | 32.580 | 1.00 | 37.05 | B | C |
| ATOM | 3423 | CD2 | TYR | B | 394 | 46.709 | 9.351 | 31.241 | 1.00 | 36.90 | B | C |
| ATOM | 3424 | CE2 | TYR | B | 394 | 45.658 | 10.084 | 30.638 | 1.00 | 37.43 | B | C |
| ATOM | 3425 | CZ | TYR | B | 394 | 44.441 | 10.238 | 31.322 | 1.00 | 38.25 | B | C |
| ATOM | 3426 | OH | TYR | B | 394 | 43.358 | 10.953 | 30.765 | 1.00 | 38.93 | B | O |
| ATOM | 3427 | C | TYR | B | 394 | 48.727 | 5.575 | 33.094 | 1.00 | 39.36 | B | C |
| ATOM | 3428 | O | TYR | B | 394 | 49.894 | 5.916 | 32.935 | 1.00 | 39.73 | B | O |
| ATOM | 3429 | N | THR | B | 395 | 48.406 | 4.439 | 33.704 | 1.00 | 41.44 | B | N |
| ATOM | 3430 | CA | THR | B | 395 | 49.426 | 3.495 | 34.148 | 1.00 | 43.93 | B | C |
| ATOM | 3431 | CB | THR | B | 395 | 49.740 | 3.547 | 35.650 | 1.00 | 44.34 | B | C |
| ATOM | 3432 | OG1 | THR | B | 395 | 48.543 | 3.778 | 36.394 | 1.00 | 44.41 | B | O |
| ATOM | 3433 | CG2 | THR | B | 395 | 50.752 | 4.636 | 35.934 | 1.00 | 45.21 | B | C |
| ATOM | 3434 | C | THR | B | 395 | 48.921 | 2.139 | 33.817 | 1.00 | 46.21 | B | C |
| ATOM | 3435 | O | THR | B | 395 | 47.848 | 2.010 | 33.254 | 1.00 | 47.09 | B | O |
| ATOM | 3436 | N | ALA | B | 396 | 49.640 | 1.108 | 34.233 | 1.00 | 49.11 | B | N |
| ATOM | 3437 | CA | ALA | B | 396 | 49.217 | -0.231 | 33.874 | 1.00 | 51.44 | B | C |
| ATOM | 3438 | CB | ALA | B | 396 | 50.227 | -0.831 | 32.908 | 1.00 | 50.47 | B | C |
| ATOM | 3439 | C | ALA | B | 396 | 48.919 | -1.182 | 35.032 | 1.00 | 53.50 | B | C |
| ATOM | 3440 | O | ALA | B | 396 | 49.346 | -2.347 | 35.008 | 1.00 | 54.26 | B | O |
| ATOM | 3441 | N | ARG | B | 397 | 48.106 | -0.705 | 35.980 | 1.00 | 55.09 | B | N |
| ATOM | 3442 | CA | ARG | B | 397 | 47.705 | -1.462 | 37.166 | 1.00 | 56.56 | B | C |
| ATOM | 3443 | CB | ARG | B | 397 | 47.223 | -0.496 | 38.262 | 1.00 | 57.00 | B | C |
| ATOM | 3444 | CG | ARG | B | 397 | 48.303 | 0.470 | 38.762 | 1.00 | 58.18 | B | C |
| ATOM | 3445 | CD | ARG | B | 397 | 48.356 | 0.581 | 40.295 | 1.00 | 58.66 | B | C |
| ATOM | 3446 | NE | ARG | B | 397 | 49.177 | 1.718 | 40.701 | 1.00 | 59.24 | B | N |
| ATOM | 3447 | CZ | ARG | B | 397 | 48.776 | 2.980 | 40.590 | 1.00 | 59.68 | B | C |
| ATOM | 3448 | NH1 | ARG | B | 397 | 47.579 | 3.254 | 40.095 | 1.00 | 59.64 | B | N |
| ATOM | 3449 | NH2 | ARG | B | 397 | 49.546 | 3.967 | 41.016 | 1.00 | 59.94 | B | N |
| ATOM | 3450 | C | ARG | B | 397 | 46.652 | -2.563 | 36.928 | 1.00 | 57.41 | B | C |
| ATOM | 3451 | O | ARG | B | 397 | 46.840 | -3.710 | 37.435 | 1.00 | 58.57 | B | O |
| ATOM | 3452 | CB | PRO | B | 403 | 37.002 | 2.442 | 41.154 | 1.00 | 35.43 | B | C |
| ATOM | 3453 | CG | PRO | B | 403 | 37.474 | 1.844 | 39.827 | 1.00 | 35.73 | B | C |
| ATOM | 3454 | C | PRO | B | 403 | 35.623 | 1.330 | 42.965 | 1.00 | 35.19 | B | C |
| ATOM | 3455 | O | PRO | B | 403 | 35.476 | 2.347 | 43.680 | 1.00 | 34.75 | B | O |
| ATOM | 3456 | N | PRO | B | 403 | 36.363 | 0.106 | 40.938 | 1.00 | 35.30 | B | N |
| ATOM | 3457 | CD | PRO | B | 403 | 37.061 | 0.311 | 39.674 | 1.00 | 35.29 | B | C |
| ATOM | 3458 | CA | PRO | B | 403 | 36.750 | 1.176 | 41.937 | 1.00 | 35.81 | B | C |
| ATOM | 3459 | N | ILE | B | 404 | 34.927 | 0.214 | 43.120 | 1.00 | 34.55 | B | N |
| ATOM | 3460 | CA | ILE | B | 404 | 33.798 | 0.083 | 44.018 | 1.00 | 33.56 | B | C |
| ATOM | 3461 | CB | ILE | B | 404 | 32.999 | -1.132 | 43.681 | 1.00 | 34.63 | B | C |
| ATOM | 3462 | CG2 | ILE | B | 404 | 32.359 | -1.746 | 44.914 | 1.00 | 35.33 | B | C |
| ATOM | 3463 | CG1 | ILE | B | 404 | 31.951 | -0.749 | 42.703 | 1.00 | 35.93 | B | C |
| ATOM | 3464 | CD1 | ILE | B | 404 | 31.021 | 0.286 | 43.331 | 1.00 | 40.50 | B | C |
| ATOM | 3465 | C | ILE | B | 404 | 34.164 | 0.080 | 45.486 | 1.00 | 32.12 | B | C |
| ATOM | 3466 | O | ILE | B | 404 | 33.423 | 0.634 | 46.298 | 1.00 | 32.41 | B | O |
| ATOM | 3467 | N | LYS | B | 405 | 35.327 | -0.476 | 45.818 | 1.00 | 29.61 | B | N |

Figure 13

| ATOM | 3468 | CA  | LYS | B | 405 | 35.815 | -0.580 | 47.198 | 1.00 | 28.89 | B | C |
| ATOM | 3469 | CB  | LYS | B | 405 | 37.038 | -1.516 | 47.292 | 1.00 | 30.34 | B | C |
| ATOM | 3470 | CG  | LYS | B | 405 | 36.708 | -2.982 | 47.116 | 1.00 | 31.61 | B | C |
| ATOM | 3471 | CD  | LYS | B | 405 | 37.946 | -3.854 | 47.152 | 1.00 | 33.06 | B | C |
| ATOM | 3472 | CE  | LYS | B | 405 | 37.542 | -5.279 | 46.798 | 1.00 | 36.50 | B | C |
| ATOM | 3473 | NZ  | LYS | B | 405 | 38.377 | -6.319 | 47.444 | 1.00 | 37.22 | B | N |
| ATOM | 3474 | C   | LYS | B | 405 | 36.107 |  0.699 | 47.943 | 1.00 | 27.19 | B | C |
| ATOM | 3475 | O   | LYS | B | 405 | 36.571 |  0.634 | 49.073 | 1.00 | 27.40 | B | O |
| ATOM | 3476 | N   | TRP | B | 406 | 35.994 |  1.860 | 47.310 | 1.00 | 25.06 | B | N |
| ATOM | 3477 | CA  | TRP | B | 406 | 36.184 |  3.091 | 48.086 | 1.00 | 23.22 | B | C |
| ATOM | 3478 | CB  | TRP | B | 406 | 37.304 |  3.973 | 47.585 | 1.00 | 22.48 | B | C |
| ATOM | 3479 | CG  | TRP | B | 406 | 38.681 |  3.383 | 47.718 | 1.00 | 19.92 | B | C |
| ATOM | 3480 | CD2 | TRP | B | 406 | 39.268 |  2.406 | 46.850 | 1.00 | 18.33 | B | C |
| ATOM | 3481 | CE2 | TRP | B | 406 | 40.575 |  2.209 | 47.273 | 1.00 | 16.73 | B | C |
| ATOM | 3482 | CE3 | TRP | B | 406 | 38.810 |  1.703 | 45.727 | 1.00 | 18.02 | B | C |
| ATOM | 3483 | CD1 | TRP | B | 406 | 39.643 |  3.714 | 48.635 | 1.00 | 16.40 | B | C |
| ATOM | 3484 | NE1 | TRP | B | 406 | 40.779 |  3.008 | 48.366 | 1.00 | 17.92 | B | N |
| ATOM | 3485 | CZ2 | TRP | B | 406 | 41.415 |  1.331 | 46.636 | 1.00 | 17.61 | B | C |
| ATOM | 3486 | CZ3 | TRP | B | 406 | 39.658 |  0.827 | 45.104 | 1.00 | 16.16 | B | C |
| ATOM | 3487 | CH2 | TRP | B | 406 | 40.933 |  0.656 | 45.546 | 1.00 | 16.99 | B | C |
| ATOM | 3488 | C   | TRP | B | 406 | 34.951 |  3.940 | 48.057 | 1.00 | 23.31 | B | C |
| ATOM | 3489 | O   | TRP | B | 406 | 34.987 |  5.069 | 48.522 | 1.00 | 23.08 | B | O |
| ATOM | 3490 | N   | THR | B | 407 | 33.877 |  3.424 | 47.450 | 1.00 | 23.11 | B | N |
| ATOM | 3491 | CA  | THR | B | 407 | 32.618 |  4.164 | 47.342 | 1.00 | 22.54 | B | C |
| ATOM | 3492 | CB  | THR | B | 407 | 31.808 |  3.854 | 46.045 | 1.00 | 22.53 | B | C |
| ATOM | 3493 | OG1 | THR | B | 407 | 32.677 |  3.712 | 44.928 | 1.00 | 24.74 | B | O |
| ATOM | 3494 | CG2 | THR | B | 407 | 30.901 |  4.986 | 45.708 | 1.00 | 23.52 | B | C |
| ATOM | 3495 | C   | THR | B | 407 | 31.681 |  3.892 | 48.504 | 1.00 | 21.94 | B | C |
| ATOM | 3496 | O   | THR | B | 407 | 31.360 |  2.754 | 48.826 | 1.00 | 21.80 | B | O |
| ATOM | 3497 | N   | ALA | B | 408 | 31.166 |  4.970 | 49.068 | 1.00 | 21.19 | B | N |
| ATOM | 3498 | CA  | ALA | B | 408 | 30.239 |  4.949 | 50.185 | 1.00 | 20.12 | B | C |
| ATOM | 3499 | CB  | ALA | B | 408 | 29.969 |  6.396 | 50.607 | 1.00 | 21.24 | B | C |
| ATOM | 3500 | C   | ALA | B | 408 | 28.949 |  4.340 | 49.704 | 1.00 | 18.83 | B | C |
| ATOM | 3501 | O   | ALA | B | 408 | 28.574 |  4.497 | 48.553 | 1.00 | 18.15 | B | O |
| ATOM | 3502 | N   | PRO | B | 409 | 28.221 |  3.702 | 50.615 | 1.00 | 18.93 | B | N |
| ATOM | 3503 | CD  | PRO | B | 409 | 28.483 |  3.742 | 52.058 | 1.00 | 17.97 | B | C |
| ATOM | 3504 | CA  | PRO | B | 409 | 26.926 |  3.055 | 50.289 | 1.00 | 19.59 | B | C |
| ATOM | 3505 | CB  | PRO | B | 409 | 26.378 |  2.635 | 51.660 | 1.00 | 19.64 | B | C |
| ATOM | 3506 | CG  | PRO | B | 409 | 27.611 |  2.649 | 52.559 | 1.00 | 19.73 | B | C |
| ATOM | 3507 | C   | PRO | B | 409 | 25.887 |  3.912 | 49.544 | 1.00 | 20.52 | B | C |
| ATOM | 3508 | O   | PRO | B | 409 | 25.256 |  3.428 | 48.609 | 1.00 | 20.96 | B | O |
| ATOM | 3509 | N   | GLU | B | 410 | 25.701 |  5.165 | 49.979 | 1.00 | 20.28 | B | N |
| ATOM | 3510 | CA  | GLU | B | 410 | 24.772 |  6.075 | 49.337 | 1.00 | 20.96 | B | C |
| ATOM | 3511 | CB  | GLU | B | 410 | 24.607 |  7.404 | 50.099 | 1.00 | 22.57 | B | C |
| ATOM | 3512 | CG  | GLU | B | 410 | 25.788 |  8.443 | 50.065 | 1.00 | 24.75 | B | C |
| ATOM | 3513 | CD  | GLU | B | 410 | 26.794 |  8.159 | 51.162 | 1.00 | 26.44 | B | C |
| ATOM | 3514 | OE1 | GLU | B | 410 | 26.638 |  7.128 | 51.860 | 1.00 | 28.70 | B | O |
| ATOM | 3515 | OE2 | GLU | B | 410 | 27.747 |  8.940 | 51.333 | 1.00 | 25.83 | B | O |
| ATOM | 3516 | C   | GLU | B | 410 | 25.191 |  6.399 | 47.910 | 1.00 | 21.73 | B | C |
| ATOM | 3517 | O   | GLU | B | 410 | 24.349 |  6.560 | 47.047 | 1.00 | 22.38 | B | O |
| ATOM | 3518 | N   | ALA | B | 411 | 26.490 |  6.484 | 47.667 | 1.00 | 22.32 | B | N |
| ATOM | 3519 | CA  | ALA | B | 411 | 26.997 |  6.815 | 46.361 | 1.00 | 23.71 | B | C |
| ATOM | 3520 | CB  | ALA | B | 411 | 28.451 |  7.149 | 46.464 | 1.00 | 24.04 | B | C |
| ATOM | 3521 | C   | ALA | B | 411 | 26.785 |  5.653 | 45.412 | 1.00 | 25.28 | B | C |
| ATOM | 3522 | O   | ALA | B | 411 | 26.598 |  5.851 | 44.217 | 1.00 | 25.63 | B | O |
| ATOM | 3523 | N   | ILE | B | 412 | 26.887 |  4.435 | 45.948 | 1.00 | 27.37 | B | N |
| ATOM | 3524 | CA  | ILE | B | 412 | 26.712 |  3.215 | 45.170 | 1.00 | 29.03 | B | C |
| ATOM | 3525 | CB  | ILE | B | 412 | 27.174 |  1.994 | 45.960 | 1.00 | 28.48 | B | C |
| ATOM | 3526 | CG2 | ILE | B | 412 | 26.830 |  0.721 | 45.221 | 1.00 | 29.65 | B | C |
| ATOM | 3527 | CG1 | ILE | B | 412 | 28.673 |  2.006 | 46.205 | 1.00 | 28.61 | B | C |

Figure 13

| ATOM | 3528 | CD1 | ILE | B | 412 | 29.094 | 0.828 | 47.106 | 1.00 | 27.85 | B | C |
| ATOM | 3529 | C | ILE | B | 412 | 25.226 | 3.026 | 44.832 | 1.00 | 31.18 | B | C |
| ATOM | 3530 | O | ILE | B | 412 | 24.889 | 2.774 | 43.668 | 1.00 | 31.27 | B | O |
| ATOM | 3531 | N | ASN | B | 413 | 24.354 | 3.249 | 45.831 | 1.00 | 32.63 | B | N |
| ATOM | 3532 | CA | ASN | B | 413 | 22.911 | 3.044 | 45.699 | 1.00 | 33.97 | B | C |
| ATOM | 3533 | CB | ASN | B | 413 | 22.268 | 2.915 | 47.081 | 1.00 | 34.44 | B | C |
| ATOM | 3534 | CG | ASN | B | 413 | 22.553 | 1.591 | 47.726 | 1.00 | 36.34 | B | C |
| ATOM | 3535 | OD1 | ASN | B | 413 | 22.660 | 0.544 | 47.040 | 1.00 | 38.86 | B | O |
| ATOM | 3536 | ND2 | ASN | B | 413 | 22.717 | 1.609 | 49.041 | 1.00 | 34.86 | B | N |
| ATOM | 3537 | C | ASN | B | 413 | 22.090 | 4.033 | 44.945 | 1.00 | 34.87 | B | C |
| ATOM | 3538 | O | ASN | B | 413 | 21.030 | 3.709 | 44.389 | 1.00 | 34.90 | B | O |
| ATOM | 3539 | N | TYR | B | 414 | 22.475 | 5.284 | 45.103 | 1.00 | 36.01 | B | N |
| ATOM | 3540 | CA | TYR | B | 414 | 21.743 | 6.370 | 44.482 | 1.00 | 37.13 | B | C |
| ATOM | 3541 | CB | TYR | B | 414 | 20.990 | 7.128 | 45.561 | 1.00 | 38.35 | B | C |
| ATOM | 3542 | CG | TYR | B | 414 | 20.144 | 6.247 | 46.408 | 1.00 | 40.65 | B | C |
| ATOM | 3543 | CD1 | TYR | B | 414 | 18.920 | 5.780 | 45.935 | 1.00 | 42.43 | B | C |
| ATOM | 3544 | CE1 | TYR | B | 414 | 18.118 | 4.944 | 46.712 | 1.00 | 43.82 | B | C |
| ATOM | 3545 | CD2 | TYR | B | 414 | 20.559 | 5.861 | 47.687 | 1.00 | 41.67 | B | C |
| ATOM | 3546 | CE2 | TYR | B | 414 | 19.761 | 5.015 | 48.480 | 1.00 | 42.96 | B | C |
| ATOM | 3547 | CZ | TYR | B | 414 | 18.545 | 4.565 | 47.979 | 1.00 | 43.92 | B | C |
| ATOM | 3548 | OH | TYR | B | 414 | 17.737 | 3.746 | 48.731 | 1.00 | 44.88 | B | O |
| ATOM | 3549 | C | TYR | B | 414 | 22.624 | 7.319 | 43.706 | 1.00 | 36.22 | B | C |
| ATOM | 3550 | O | TYR | B | 414 | 22.137 | 8.304 | 43.157 | 1.00 | 36.50 | B | O |
| ATOM | 3551 | N | GLY | B | 415 | 23.926 | 7.072 | 43.711 | 1.00 | 35.26 | B | N |
| ATOM | 3552 | CA | GLY | B | 415 | 24.792 | 7.973 | 42.972 | 1.00 | 33.55 | B | C |
| ATOM | 3553 | C | GLY | B | 415 | 25.055 | 9.327 | 43.629 | 1.00 | 32.91 | B | C |
| ATOM | 3554 | O | GLY | B | 415 | 25.639 | 10.200 | 42.987 | 1.00 | 33.79 | B | O |
| ATOM | 3555 | N | THR | B | 416 | 24.698 | 9.462 | 44.912 | 1.00 | 31.57 | B | N |
| ATOM | 3556 | CA | THR | B | 416 | 24.881 | 10.686 | 45.665 | 1.00 | 30.31 | B | C |
| ATOM | 3557 | CB | THR | B | 416 | 23.680 | 10.968 | 46.663 | 1.00 | 30.26 | B | C |
| ATOM | 3558 | OG1 | THR | B | 416 | 24.159 | 11.591 | 47.869 | 1.00 | 30.13 | B | O |
| ATOM | 3559 | CG2 | THR | B | 416 | 22.878 | 9.732 | 46.973 | 1.00 | 29.61 | B | C |
| ATOM | 3560 | C | THR | B | 416 | 26.277 | 10.787 | 46.294 | 1.00 | 28.91 | B | C |
| ATOM | 3561 | O | THR | B | 416 | 26.659 | 10.014 | 47.164 | 1.00 | 27.94 | B | O |
| ATOM | 3562 | N | PHE | B | 417 | 27.054 | 11.706 | 45.724 | 1.00 | 28.45 | B | N |
| ATOM | 3563 | CA | PHE | B | 417 | 28.440 | 12.005 | 46.087 | 1.00 | 27.52 | B | C |
| ATOM | 3564 | CB | PHE | B | 417 | 29.341 | 12.008 | 44.833 | 1.00 | 29.49 | B | C |
| ATOM | 3565 | CG | PHE | B | 417 | 29.613 | 10.641 | 44.252 | 1.00 | 31.69 | B | C |
| ATOM | 3566 | CD1 | PHE | B | 417 | 28.752 | 10.097 | 43.282 | 1.00 | 33.84 | B | C |
| ATOM | 3567 | CD2 | PHE | B | 417 | 30.724 | 9.885 | 44.679 | 1.00 | 31.07 | B | C |
| ATOM | 3568 | CE1 | PHE | B | 417 | 28.988 | 8.787 | 42.726 | 1.00 | 35.60 | B | C |
| ATOM | 3569 | CE2 | PHE | B | 417 | 30.983 | 8.591 | 44.153 | 1.00 | 31.80 | B | C |
| ATOM | 3570 | CZ | PHE | B | 417 | 30.115 | 8.026 | 43.173 | 1.00 | 33.63 | B | C |
| ATOM | 3571 | C | PHE | B | 417 | 28.543 | 13.386 | 46.739 | 1.00 | 25.96 | B | C |
| ATOM | 3572 | O | PHE | B | 417 | 28.211 | 14.414 | 46.135 | 1.00 | 26.06 | B | O |
| ATOM | 3573 | N | THR | B | 418 | 29.039 | 13.384 | 47.969 | 1.00 | 23.25 | B | N |
| ATOM | 3574 | CA | THR | B | 418 | 29.255 | 14.570 | 48.759 | 1.00 | 20.87 | B | C |
| ATOM | 3575 | CB | THR | B | 418 | 28.208 | 14.781 | 49.851 | 1.00 | 20.78 | B | C |
| ATOM | 3576 | OG1 | THR | B | 418 | 28.312 | 13.744 | 50.826 | 1.00 | 20.26 | B | O |
| ATOM | 3577 | CG2 | THR | B | 418 | 26.861 | 14.761 | 49.255 | 1.00 | 21.23 | B | C |
| ATOM | 3578 | C | THR | B | 418 | 30.589 | 14.380 | 49.421 | 1.00 | 19.90 | B | C |
| ATOM | 3579 | O | THR | B | 418 | 31.259 | 13.349 | 49.253 | 1.00 | 19.48 | B | O |
| ATOM | 3580 | N | ILE | B | 419 | 30.965 | 15.396 | 50.185 | 1.00 | 18.16 | B | N |
| ATOM | 3581 | CA | ILE | B | 419 | 32.221 | 15.415 | 50.874 | 1.00 | 17.06 | B | C |
| ATOM | 3582 | CB | ILE | B | 419 | 32.443 | 16.812 | 51.563 | 1.00 | 14.72 | B | C |
| ATOM | 3583 | CG2 | ILE | B | 419 | 31.478 | 16.957 | 52.764 | 1.00 | 14.03 | B | C |
| ATOM | 3584 | CG1 | ILE | B | 419 | 33.895 | 16.954 | 52.000 | 1.00 | 11.51 | B | C |
| ATOM | 3585 | CD1 | ILE | B | 419 | 34.844 | 16.696 | 50.898 | 1.00 | 10.59 | B | C |
| ATOM | 3586 | C | ILE | B | 419 | 32.186 | 14.246 | 51.880 | 1.00 | 16.36 | B | C |
| ATOM | 3587 | O | ILE | B | 419 | 33.191 | 13.606 | 52.150 | 1.00 | 17.11 | B | O |

Figure 13

| ATOM | 3588 | N | LYS | B | 420 | 30.987 | 13.895 | 52.299 | 1.00 | 16.68 | B | N |
|------|------|---|-----|---|-----|--------|--------|--------|------|-------|---|---|
| ATOM | 3589 | CA | LYS | B | 420 | 30.787 | 12.838 | 53.263 | 1.00 | 17.62 | B | C |
| ATOM | 3590 | CB | LYS | B | 420 | 29.352 | 12.888 | 53.779 | 1.00 | 17.44 | B | C |
| ATOM | 3591 | CG | LYS | B | 420 | 29.083 | 14.086 | 54.695 | 1.00 | 17.84 | B | C |
| ATOM | 3592 | CD | LYS | B | 420 | 30.066 | 14.108 | 55.876 | 1.00 | 17.85 | B | C |
| ATOM | 3593 | CE | LYS | B | 420 | 29.831 | 15.265 | 56.780 | 1.00 | 16.69 | B | C |
| ATOM | 3594 | NZ | LYS | B | 420 | 30.769 | 15.215 | 57.909 | 1.00 | 16.83 | B | N |
| ATOM | 3595 | C | LYS | B | 420 | 31.097 | 11.481 | 52.662 | 1.00 | 19.05 | B | C |
| ATOM | 3596 | O | LYS | B | 420 | 31.382 | 10.539 | 53.398 | 1.00 | 19.89 | B | O |
| ATOM | 3597 | N | SER | B | 421 | 30.958 | 11.361 | 51.339 | 1.00 | 20.43 | B | N |
| ATOM | 3598 | CA | SER | B | 421 | 31.270 | 10.126 | 50.686 | 1.00 | 21.96 | B | C |
| ATOM | 3599 | CB | SER | B | 421 | 30.330 | 9.795 | 49.483 | 1.00 | 22.17 | B | C |
| ATOM | 3600 | OG | SER | B | 421 | 30.128 | 10.811 | 48.529 | 1.00 | 20.98 | B | O |
| ATOM | 3601 | C | SER | B | 421 | 32.775 | 10.031 | 50.454 | 1.00 | 22.87 | B | C |
| ATOM | 3602 | O | SER | B | 421 | 33.335 | 8.946 | 50.358 | 1.00 | 23.25 | B | O |
| ATOM | 3603 | N | ASP | B | 422 | 33.450 | 11.171 | 50.521 | 1.00 | 24.64 | B | N |
| ATOM | 3604 | CA | ASP | B | 422 | 34.911 | 11.190 | 50.425 | 1.00 | 25.10 | B | C |
| ATOM | 3605 | CB | ASP | B | 422 | 35.470 | 12.585 | 50.140 | 1.00 | 25.65 | B | C |
| ATOM | 3606 | CG | ASP | B | 422 | 35.281 | 13.042 | 48.697 | 1.00 | 25.78 | B | C |
| ATOM | 3607 | OD1 | ASP | B | 422 | 34.999 | 12.208 | 47.782 | 1.00 | 25.02 | B | O |
| ATOM | 3608 | OD2 | ASP | B | 422 | 35.469 | 14.264 | 48.526 | 1.00 | 24.81 | B | O |
| ATOM | 3609 | C | ASP | B | 422 | 35.411 | 10.842 | 51.817 | 1.00 | 25.20 | B | C |
| ATOM | 3610 | O | ASP | B | 422 | 36.511 | 10.351 | 51.949 | 1.00 | 26.04 | B | O |
| ATOM | 3611 | N | VAL | B | 423 | 34.680 | 11.226 | 52.860 | 1.00 | 25.01 | B | N |
| ATOM | 3612 | CA | VAL | B | 423 | 35.151 | 10.898 | 54.193 | 1.00 | 24.83 | B | C |
| ATOM | 3613 | CB | VAL | B | 423 | 34.277 | 11.457 | 55.333 | 1.00 | 25.57 | B | C |
| ATOM | 3614 | CG1 | VAL | B | 423 | 34.714 | 10.838 | 56.681 | 1.00 | 25.44 | B | C |
| ATOM | 3615 | CG2 | VAL | B | 423 | 34.417 | 12.988 | 55.422 | 1.00 | 23.68 | B | C |
| ATOM | 3616 | C | VAL | B | 423 | 35.177 | 9.407 | 54.284 | 1.00 | 24.63 | B | C |
| ATOM | 3617 | O | VAL | B | 423 | 36.140 | 8.836 | 54.816 | 1.00 | 25.74 | B | O |
| ATOM | 3618 | N | TRP | B | 424 | 34.162 | 8.763 | 53.707 | 1.00 | 24.35 | B | N |
| ATOM | 3619 | CA | TRP | B | 424 | 34.094 | 7.285 | 53.703 | 1.00 | 23.49 | B | C |
| ATOM | 3620 | CB | TRP | B | 424 | 32.824 | 6.771 | 52.981 | 1.00 | 21.58 | B | C |
| ATOM | 3621 | CG | TRP | B | 424 | 32.745 | 5.318 | 52.796 | 1.00 | 19.10 | B | C |
| ATOM | 3622 | CD2 | TRP | B | 424 | 31.921 | 4.398 | 53.521 | 1.00 | 19.11 | B | C |
| ATOM | 3623 | CE2 | TRP | B | 424 | 32.136 | 3.120 | 52.960 | 1.00 | 21.78 | B | C |
| ATOM | 3624 | CE3 | TRP | B | 424 | 30.998 | 4.533 | 54.560 | 1.00 | 19.52 | B | C |
| ATOM | 3625 | CD1 | TRP | B | 424 | 33.410 | 4.587 | 51.874 | 1.00 | 19.84 | B | C |
| ATOM | 3626 | NE1 | TRP | B | 424 | 33.063 | 3.258 | 51.960 | 1.00 | 19.63 | B | N |
| ATOM | 3627 | CZ2 | TRP | B | 424 | 31.455 | 1.959 | 53.426 | 1.00 | 19.75 | B | C |
| ATOM | 3628 | CZ3 | TRP | B | 424 | 30.315 | 3.392 | 55.015 | 1.00 | 18.71 | B | C |
| ATOM | 3629 | CH2 | TRP | B | 424 | 30.545 | 2.126 | 54.442 | 1.00 | 20.33 | B | C |
| ATOM | 3630 | C | TRP | B | 424 | 35.361 | 6.857 | 52.964 | 1.00 | 24.48 | B | C |
| ATOM | 3631 | O | TRP | B | 424 | 36.223 | 6.212 | 53.575 | 1.00 | 24.88 | B | O |
| ATOM | 3632 | N | SER | B | 425 | 35.543 | 7.334 | 51.717 | 1.00 | 25.63 | B | N |
| ATOM | 3633 | CA | SER | B | 425 | 36.761 | 6.990 | 50.923 | 1.00 | 26.28 | B | C |
| ATOM | 3634 | CB | SER | B | 425 | 36.839 | 7.829 | 49.642 | 1.00 | 28.14 | B | C |
| ATOM | 3635 | OG | SER | B | 425 | 35.943 | 7.352 | 48.646 | 1.00 | 29.82 | B | O |
| ATOM | 3636 | C | SER | B | 425 | 38.072 | 7.197 | 51.717 | 1.00 | 25.11 | B | C |
| ATOM | 3637 | O | SER | B | 425 | 39.018 | 6.462 | 51.533 | 1.00 | 25.75 | B | O |
| ATOM | 3638 | N | PHE | B | 426 | 38.137 | 8.219 | 52.565 | 1.00 | 24.16 | B | N |
| ATOM | 3639 | CA | PHE | B | 426 | 39.314 | 8.453 | 53.381 | 1.00 | 23.75 | B | C |
| ATOM | 3640 | CB | PHE | B | 426 | 39.238 | 9.820 | 54.034 | 1.00 | 21.99 | B | C |
| ATOM | 3641 | CG | PHE | B | 426 | 40.482 | 10.206 | 54.789 | 1.00 | 21.80 | B | C |
| ATOM | 3642 | CD1 | PHE | B | 426 | 41.667 | 10.547 | 54.115 | 1.00 | 20.48 | B | C |
| ATOM | 3643 | CD2 | PHE | B | 426 | 40.489 | 10.184 | 56.182 | 1.00 | 21.90 | B | C |
| ATOM | 3644 | CE1 | PHE | B | 426 | 42.822 | 10.850 | 54.812 | 1.00 | 19.16 | B | C |
| ATOM | 3645 | CE2 | PHE | B | 426 | 41.657 | 10.489 | 56.888 | 1.00 | 21.64 | B | C |
| ATOM | 3646 | CZ | PHE | B | 426 | 42.825 | 10.819 | 56.196 | 1.00 | 19.84 | B | C |
| ATOM | 3647 | C | PHE | B | 426 | 39.519 | 7.353 | 54.438 | 1.00 | 23.86 | B | C |

Figure 13

| | | | | | | | | | | | |
|---|---|---|---|---|---|---|---|---|---|---|---|
| ATOM | 3648 | O | PHE | B | 426 | 40.665 | 6.992 | 54.759 | 1.00 | 23.85 | B | O |
| ATOM | 3649 | N | GLY | B | 427 | 38.408 | 6.788 | 54.926 | 1.00 | 23.73 | B | N |
| ATOM | 3650 | CA | GLY | B | 427 | 38.446 | 5.708 | 55.924 | 1.00 | 22.50 | B | C |
| ATOM | 3651 | C | GLY | B | 427 | 39.064 | 4.461 | 55.301 | 1.00 | 21.92 | B | C |
| ATOM | 3652 | O | GLY | B | 427 | 39.883 | 3.789 | 55.918 | 1.00 | 22.86 | B | O |
| ATOM | 3653 | N | ILE | B | 428 | 38.648 | 4.159 | 54.068 | 1.00 | 21.71 | B | N |
| ATOM | 3654 | CA | ILE | B | 428 | 39.131 | 3.021 | 53.278 | 1.00 | 19.33 | B | C |
| ATOM | 3655 | CB | ILE | B | 428 | 38.339 | 2.882 | 51.921 | 1.00 | 18.72 | B | C |
| ATOM | 3656 | CG2 | ILE | B | 428 | 38.874 | 1.758 | 51.100 | 1.00 | 18.88 | B | C |
| ATOM | 3657 | CG1 | ILE | B | 428 | 36.848 | 2.681 | 52.158 | 1.00 | 16.60 | B | C |
| ATOM | 3658 | CD1 | ILE | B | 428 | 36.512 | 1.527 | 53.081 | 1.00 | 16.69 | B | C |
| ATOM | 3659 | C | ILE | B | 428 | 40.593 | 3.344 | 52.956 | 1.00 | 17.80 | B | C |
| ATOM | 3660 | O | ILE | B | 428 | 41.409 | 2.461 | 52.971 | 1.00 | 18.29 | B | O |
| ATOM | 3661 | N | LEU | B | 429 | 40.923 | 4.610 | 52.695 | 1.00 | 17.89 | B | N |
| ATOM | 3662 | CA | LEU | B | 429 | 42.305 | 4.975 | 52.392 | 1.00 | 17.49 | B | C |
| ATOM | 3663 | CB | LEU | B | 429 | 42.377 | 6.417 | 51.904 | 1.00 | 15.11 | B | C |
| ATOM | 3664 | CG | LEU | B | 429 | 43.616 | 6.911 | 51.145 | 1.00 | 14.04 | B | C |
| ATOM | 3665 | CD1 | LEU | B | 429 | 43.255 | 8.286 | 50.655 | 1.00 | 13.20 | B | C |
| ATOM | 3666 | CD2 | LEU | B | 429 | 44.897 | 6.977 | 51.937 | 1.00 | 8.46 | B | C |
| ATOM | 3667 | C | LEU | B | 429 | 43.280 | 4.763 | 53.576 | 1.00 | 18.25 | B | C |
| ATOM | 3668 | O | LEU | B | 429 | 44.459 | 4.464 | 53.386 | 1.00 | 18.07 | B | O |
| ATOM | 3669 | N | LEU | B | 430 | 42.787 | 4.970 | 54.783 | 1.00 | 18.36 | B | N |
| ATOM | 3670 | CA | LEU | B | 430 | 43.587 | 4.787 | 55.965 | 1.00 | 19.06 | B | C |
| ATOM | 3671 | CB | LEU | B | 430 | 42.857 | 5.278 | 57.209 | 1.00 | 18.67 | B | C |
| ATOM | 3672 | CG | LEU | B | 430 | 42.624 | 6.772 | 57.520 | 1.00 | 19.42 | B | C |
| ATOM | 3673 | CD1 | LEU | B | 430 | 41.658 | 6.895 | 58.720 | 1.00 | 14.54 | B | C |
| ATOM | 3674 | CD2 | LEU | B | 430 | 43.975 | 7.496 | 57.789 | 1.00 | 15.53 | B | C |
| ATOM | 3675 | C | LEU | B | 430 | 43.902 | 3.295 | 56.106 | 1.00 | 20.60 | B | C |
| ATOM | 3676 | O | LEU | B | 430 | 44.930 | 2.948 | 56.702 | 1.00 | 21.03 | B | O |
| ATOM | 3677 | N | THR | B | 431 | 43.059 | 2.398 | 55.571 | 1.00 | 20.91 | B | N |
| ATOM | 3678 | CA | THR | B | 431 | 43.399 | 0.963 | 55.657 | 1.00 | 22.32 | B | C |
| ATOM | 3679 | CB | THR | B | 431 | 42.235 | -0.039 | 55.428 | 1.00 | 19.97 | B | O |
| ATOM | 3680 | OG1 | THR | B | 431 | 41.812 | 0.008 | 54.061 | 1.00 | 19.17 | B | O |
| ATOM | 3681 | CG2 | THR | B | 431 | 41.098 | 0.184 | 56.419 | 1.00 | 16.27 | B | C |
| ATOM | 3682 | C | THR | B | 431 | 44.512 | 0.642 | 54.660 | 1.00 | 24.32 | B | C |
| ATOM | 3683 | O | THR | B | 431 | 45.284 | -0.275 | 54.905 | 1.00 | 25.84 | B | O |
| ATOM | 3684 | N | GLU | B | 432 | 44.566 | 1.342 | 53.519 | 1.00 | 24.85 | B | N |
| ATOM | 3685 | CA | GLU | B | 432 | 45.662 | 1.149 | 52.545 | 1.00 | 24.40 | B | C |
| ATOM | 3686 | CB | GLU | B | 432 | 45.484 | 2.023 | 51.284 | 1.00 | 23.27 | B | C |
| ATOM | 3687 | CG | GLU | B | 432 | 44.342 | 1.587 | 50.414 | 1.00 | 24.98 | B | C |
| ATOM | 3688 | CD | GLU | B | 432 | 44.209 | 2.366 | 49.136 | 1.00 | 25.40 | B | C |
| ATOM | 3689 | OE1 | GLU | B | 432 | 43.595 | 3.446 | 49.140 | 1.00 | 26.27 | B | O |
| ATOM | 3690 | OE2 | GLU | B | 432 | 44.628 | 1.859 | 48.085 | 1.00 | 27.07 | B | O |
| ATOM | 3691 | C | GLU | B | 432 | 46.944 | 1.627 | 53.221 | 1.00 | 25.33 | B | C |
| ATOM | 3692 | O | GLU | B | 432 | 47.937 | 0.939 | 53.214 | 1.00 | 26.24 | B | O |
| ATOM | 3693 | N | ILE | B | 433 | 46.884 | 2.823 | 53.793 | 1.00 | 25.46 | B | N |
| ATOM | 3694 | CA | ILE | B | 433 | 48.026 | 3.421 | 54.420 | 1.00 | 25.69 | B | C |
| ATOM | 3695 | CB | ILE | B | 433 | 47.701 | 4.812 | 55.030 | 1.00 | 24.96 | B | C |
| ATOM | 3696 | CG2 | ILE | B | 433 | 48.798 | 5.201 | 56.020 | 1.00 | 24.31 | B | C |
| ATOM | 3697 | CG1 | ILE | B | 433 | 47.646 | 5.889 | 53.917 | 1.00 | 25.02 | B | C |
| ATOM | 3698 | CD1 | ILE | B | 433 | 47.544 | 7.333 | 54.418 | 1.00 | 21.59 | B | C |
| ATOM | 3699 | C | ILE | B | 433 | 48.665 | 2.577 | 55.494 | 1.00 | 27.61 | B | C |
| ATOM | 3700 | O | ILE | B | 433 | 49.883 | 2.593 | 55.606 | 1.00 | 29.87 | B | O |
| ATOM | 3701 | N | VAL | B | 434 | 47.894 | 1.748 | 56.186 | 1.00 | 27.56 | B | N |
| ATOM | 3702 | CA | VAL | B | 434 | 48.472 | 0.979 | 57.274 | 1.00 | 26.77 | B | C |
| ATOM | 3703 | CB | VAL | B | 434 | 47.529 | 0.871 | 58.469 | 1.00 | 27.60 | B | C |
| ATOM | 3704 | CG1 | VAL | B | 434 | 47.504 | 2.189 | 59.193 | 1.00 | 26.54 | B | C |
| ATOM | 3705 | CG2 | VAL | B | 434 | 46.099 | 0.411 | 58.032 | 1.00 | 25.75 | B | C |
| ATOM | 3706 | C | VAL | B | 434 | 48.903 | -0.396 | 56.924 | 1.00 | 27.82 | B | C |
| ATOM | 3707 | O | VAL | B | 434 | 49.750 | -0.956 | 57.599 | 1.00 | 28.87 | B | O |

Figure 13

| ATOM | 3708 | N | THR | B | 435 | 48.381 | -0.936 | 55.823 | 1.00 | 29.35 | B | N |
|------|------|------|------|---|-----|--------|--------|--------|------|-------|---|---|
| ATOM | 3709 | CA | THR | B | 435 | 48.705 | -2.286 | 55.452 | 1.00 | 30.99 | B | C |
| ATOM | 3710 | CB | THR | B | 435 | 47.452 | -2.989 | 54.980 | 1.00 | 30.99 | B | C |
| ATOM | 3711 | OG1 | THR | B | 435 | 46.909 | -2.254 | 53.881 | 1.00 | 32.27 | B | O |
| ATOM | 3712 | CG2 | THR | B | 435 | 46.419 | -3.096 | 56.119 | 1.00 | 27.84 | B | C |
| ATOM | 3713 | C | THR | B | 435 | 49.650 | -2.259 | 54.264 | 1.00 | 33.09 | B | C |
| ATOM | 3714 | O | THR | B | 435 | 49.734 | -3.239 | 53.539 | 1.00 | 34.49 | B | O |
| ATOM | 3715 | N | HIS | B | 436 | 50.280 | -1.113 | 54.035 | 1.00 | 35.43 | B | N |
| ATOM | 3716 | CA | HIS | B | 436 | 51.220 | -0.922 | 52.949 | 1.00 | 37.91 | B | C |
| ATOM | 3717 | CB | HIS | B | 436 | 52.428 | -1.794 | 53.201 | 1.00 | 42.00 | B | C |
| ATOM | 3718 | CG | HIS | B | 436 | 53.059 | -1.549 | 54.531 | 1.00 | 46.29 | B | C |
| ATOM | 3719 | CD2 | HIS | B | 436 | 53.573 | -2.409 | 55.440 | 1.00 | 48.78 | B | C |
| ATOM | 3720 | ND1 | HIS | B | 436 | 53.217 | -0.284 | 55.060 | 1.00 | 47.46 | B | N |
| ATOM | 3721 | CE1 | HIS | B | 436 | 53.811 | -0.376 | 56.239 | 1.00 | 48.79 | B | C |
| ATOM | 3722 | NE2 | HIS | B | 436 | 54.033 | -1.655 | 56.491 | 1.00 | 51.17 | B | N |
| ATOM | 3723 | C | HIS | B | 436 | 50.698 | -1.131 | 51.526 | 1.00 | 38.22 | B | C |
| ATOM | 3724 | O | HIS | B | 436 | 51.379 | -1.736 | 50.685 | 1.00 | 38.40 | B | O |
| ATOM | 3725 | N | GLY | B | 437 | 49.576 | -0.484 | 51.235 | 1.00 | 37.30 | B | N |
| ATOM | 3726 | CA | GLY | B | 437 | 48.997 | -0.582 | 49.912 | 1.00 | 36.98 | B | C |
| ATOM | 3727 | C | GLY | B | 437 | 48.245 | -1.838 | 49.602 | 1.00 | 36.91 | B | C |
| ATOM | 3728 | O | GLY | B | 437 | 48.167 | -2.253 | 48.440 | 1.00 | 36.93 | B | O |
| ATOM | 3729 | N | ARG | B | 438 | 47.782 | -2.489 | 50.657 | 1.00 | 36.85 | B | N |
| ATOM | 3730 | CA | ARG | B | 438 | 47.008 | -3.699 | 50.500 | 1.00 | 37.29 | B | C |
| ATOM | 3731 | CB | ARG | B | 438 | 46.858 | -4.379 | 51.849 | 1.00 | 39.53 | B | C |
| ATOM | 3732 | CG | ARG | B | 438 | 46.498 | -5.846 | 51.780 | 1.00 | 43.53 | B | C |
| ATOM | 3733 | CD | ARG | B | 438 | 45.001 | -6.002 | 51.667 | 1.00 | 47.24 | B | C |
| ATOM | 3734 | NE | ARG | B | 438 | 44.269 | -5.406 | 52.795 | 1.00 | 48.54 | B | N |
| ATOM | 3735 | CZ | ARG | B | 438 | 44.342 | -5.848 | 54.048 | 1.00 | 49.01 | B | C |
| ATOM | 3736 | NH1 | ARG | B | 438 | 45.123 | -6.890 | 54.359 | 1.00 | 48.71 | B | N |
| ATOM | 3737 | NH2 | ARG | B | 438 | 43.559 | -5.299 | 54.967 | 1.00 | 47.62 | B | N |
| ATOM | 3738 | C | ARG | B | 438 | 45.640 | -3.287 | 49.987 | 1.00 | 36.55 | B | C |
| ATOM | 3739 | O | ARG | B | 438 | 45.166 | -2.201 | 50.313 | 1.00 | 36.22 | B | O |
| ATOM | 3740 | N | ILE | B | 439 | 45.039 | -4.119 | 49.129 | 1.00 | 35.94 | B | N |
| ATOM | 3741 | CA | ILE | B | 439 | 43.710 | -3.838 | 48.570 | 1.00 | 34.58 | B | C |
| ATOM | 3742 | CB | ILE | B | 439 | 43.353 | -4.751 | 47.329 | 1.00 | 35.59 | B | C |
| ATOM | 3743 | CG2 | ILE | B | 439 | 41.910 | -4.589 | 46.954 | 1.00 | 35.94 | B | C |
| ATOM | 3744 | CG1 | ILE | B | 439 | 44.139 | -4.301 | 46.087 | 1.00 | 38.32 | B | C |
| ATOM | 3745 | CD1 | ILE | B | 439 | 44.233 | -5.377 | 44.958 | 1.00 | 39.32 | B | C |
| ATOM | 3746 | C | ILE | B | 439 | 42.642 | -3.986 | 49.631 | 1.00 | 32.41 | B | C |
| ATOM | 3747 | O | ILE | B | 439 | 42.657 | -4.932 | 50.408 | 1.00 | 31.80 | B | O |
| ATOM | 3748 | N | PRO | B | 440 | 41.723 | -3.008 | 49.706 | 1.00 | 30.46 | B | N |
| ATOM | 3749 | CD | PRO | B | 440 | 41.668 | -1.823 | 48.836 | 1.00 | 29.50 | B | C |
| ATOM | 3750 | CA | PRO | B | 440 | 40.618 | -3.004 | 50.669 | 1.00 | 29.42 | B | C |
| ATOM | 3751 | CB | PRO | B | 440 | 39.819 | -1.764 | 50.247 | 1.00 | 30.95 | B | C |
| ATOM | 3752 | CG | PRO | B | 440 | 40.865 | -0.862 | 49.656 | 1.00 | 30.77 | B | C |
| ATOM | 3753 | C | PRO | B | 440 | 39.777 | -4.267 | 50.492 | 1.00 | 28.42 | B | C |
| ATOM | 3754 | O | PRO | B | 440 | 39.682 | -4.794 | 49.385 | 1.00 | 28.20 | B | O |
| ATOM | 3755 | N | TYR | B | 441 | 39.141 | -4.734 | 51.566 | 1.00 | 27.00 | B | N |
| ATOM | 3756 | CA | TYR | B | 441 | 38.307 | -5.957 | 51.541 | 1.00 | 26.60 | B | C |
| ATOM | 3757 | CB | TYR | B | 441 | 36.955 | -5.721 | 50.858 | 1.00 | 24.87 | B | C |
| ATOM | 3758 | CG | TYR | B | 441 | 36.205 | -4.534 | 51.391 | 1.00 | 23.84 | B | C |
| ATOM | 3759 | CD1 | TYR | B | 441 | 35.248 | -4.667 | 52.417 | 1.00 | 22.39 | B | C |
| ATOM | 3760 | CE1 | TYR | B | 441 | 34.542 | -3.549 | 52.863 | 1.00 | 21.71 | B | C |
| ATOM | 3761 | CD2 | TYR | B | 441 | 36.430 | -3.254 | 50.845 | 1.00 | 23.30 | B | C |
| ATOM | 3762 | CE2 | TYR | B | 441 | 35.726 | -2.139 | 51.283 | 1.00 | 22.71 | B | C |
| ATOM | 3763 | CZ | TYR | B | 441 | 34.791 | -2.305 | 52.282 | 1.00 | 21.82 | B | C |
| ATOM | 3764 | OH | TYR | B | 441 | 34.132 | -1.218 | 52.693 | 1.00 | 20.84 | B | O |
| ATOM | 3765 | C | TYR | B | 441 | 39.008 | -7.080 | 50.824 | 1.00 | 26.40 | B | C |
| ATOM | 3766 | O | TYR | B | 441 | 38.543 | -7.558 | 49.786 | 1.00 | 26.78 | B | O |
| ATOM | 3767 | N | PRO | B | 442 | 40.152 | -7.507 | 51.358 | 1.00 | 26.70 | B | N |

Figure 13

| ATOM | 3768 | CD | PRO | B | 442 | 40.856 | -7.034 | 52.560 | 1.00 | 25.35 | B | C |
|------|------|-----|-----|---|-----|--------|---------|--------|------|-------|---|---|
| ATOM | 3769 | CA | PRO | B | 442 | 40.867 | -8.590 | 50.693 | 1.00 | 27.69 | B | C |
| ATOM | 3770 | CB | PRO | B | 442 | 42.170 | -8.653 | 51.479 | 1.00 | 27.23 | B | C |
| ATOM | 3771 | CG | PRO | B | 442 | 41.759 | -8.136 | 52.853 | 1.00 | 26.31 | B | C |
| ATOM | 3772 | C | PRO | B | 442 | 40.060 | -9.891 | 50.687 | 1.00 | 29.25 | B | C |
| ATOM | 3773 | O | PRO | B | 442 | 39.440 | -10.267 | 51.683 | 1.00 | 29.77 | B | O |
| ATOM | 3774 | N | GLY | B | 443 | 40.053 | -10.556 | 49.540 | 1.00 | 30.11 | B | N |
| ATOM | 3775 | CA | GLY | B | 443 | 39.300 | -11.776 | 49.419 | 1.00 | 31.53 | B | C |
| ATOM | 3776 | C | GLY | B | 443 | 37.853 | -11.553 | 49.050 | 1.00 | 32.93 | B | C |
| ATOM | 3777 | O | GLY | B | 443 | 37.021 | -12.469 | 49.167 | 1.00 | 35.45 | B | O |
| ATOM | 3778 | N | MET | B | 444 | 37.531 | -10.322 | 48.687 | 1.00 | 32.59 | B | N |
| ATOM | 3779 | CA | MET | B | 444 | 36.173 | -9.968 | 48.249 | 1.00 | 33.07 | B | C |
| ATOM | 3780 | CB | MET | B | 444 | 35.510 | -8.916 | 49.176 | 1.00 | 32.96 | B | C |
| ATOM | 3781 | CG | MET | B | 444 | 34.715 | -9.577 | 50.271 | 1.00 | 33.78 | B | C |
| ATOM | 3782 | SD | MET | B | 444 | 34.126 | -8.675 | 51.651 | 1.00 | 31.11 | B | S |
| ATOM | 3783 | CE | MET | B | 444 | 32.843 | -7.985 | 50.867 | 1.00 | 29.95 | B | C |
| ATOM | 3784 | C | MET | B | 444 | 36.280 | -9.442 | 46.838 | 1.00 | 33.10 | B | C |
| ATOM | 3785 | O | MET | B | 444 | 37.346 | -8.997 | 46.441 | 1.00 | 32.84 | B | O |
| ATOM | 3786 | N | THR | B | 445 | 35.257 | -9.662 | 46.030 | 1.00 | 32.79 | B | N |
| ATOM | 3787 | CA | THR | B | 445 | 35.262 | -9.109 | 44.676 | 1.00 | 33.68 | B | C |
| ATOM | 3788 | CB | THR | B | 445 | 34.693 | -10.092 | 43.632 | 1.00 | 33.63 | B | C |
| ATOM | 3789 | OG1 | THR | B | 445 | 33.334 | -10.392 | 43.959 | 1.00 | 34.91 | B | O |
| ATOM | 3790 | CG2 | THR | B | 445 | 35.493 | -11.356 | 43.588 | 1.00 | 32.89 | B | C |
| ATOM | 3791 | C | THR | B | 445 | 34.302 | -7.926 | 44.780 | 1.00 | 33.91 | B | C |
| ATOM | 3792 | O | THR | B | 445 | 33.594 | -7.800 | 45.779 | 1.00 | 34.30 | B | O |
| ATOM | 3793 | N | ASN | B | 446 | 34.242 | -7.088 | 43.754 | 1.00 | 33.29 | B | N |
| ATOM | 3794 | CA | ASN | B | 446 | 33.340 | -5.927 | 43.763 | 1.00 | 33.35 | B | C |
| ATOM | 3795 | CB | ASN | B | 446 | 33.392 | -5.164 | 42.431 | 1.00 | 32.70 | B | C |
| ATOM | 3796 | CG | ASN | B | 446 | 34.577 | -4.226 | 42.343 | 1.00 | 31.66 | B | C |
| ATOM | 3797 | OD1 | ASN | B | 446 | 35.530 | -4.323 | 43.094 | 1.00 | 30.06 | B | O |
| ATOM | 3798 | ND2 | ASN | B | 446 | 34.524 | -3.331 | 41.399 | 1.00 | 31.44 | B | N |
| ATOM | 3799 | C | ASN | B | 446 | 31.897 | -6.276 | 44.114 | 1.00 | 32.96 | B | C |
| ATOM | 3800 | O | ASN | B | 446 | 31.299 | -5.611 | 44.957 | 1.00 | 33.62 | B | O |
| ATOM | 3801 | N | PRO | B | 447 | 31.291 | -7.273 | 43.425 | 1.00 | 32.62 | B | N |
| ATOM | 3802 | CD | PRO | B | 447 | 31.730 | -8.009 | 42.231 | 1.00 | 31.78 | B | C |
| ATOM | 3803 | CA | PRO | B | 447 | 29.914 | -7.642 | 43.741 | 1.00 | 31.66 | B | C |
| ATOM | 3804 | CB | PRO | B | 447 | 29.600 | -8.696 | 42.677 | 1.00 | 31.74 | B | C |
| ATOM | 3805 | CG | PRO | B | 447 | 30.933 | -9.224 | 42.321 | 1.00 | 33.21 | B | C |
| ATOM | 3806 | C | PRO | B | 447 | 29.764 | -8.154 | 45.170 | 1.00 | 30.73 | B | C |
| ATOM | 3807 | O | PRO | B | 447 | 28.700 | -8.006 | 45.775 | 1.00 | 31.11 | B | O |
| ATOM | 3808 | N | GLU | B | 448 | 30.821 | -8.745 | 45.714 | 1.00 | 28.72 | B | N |
| ATOM | 3809 | CA | GLU | B | 448 | 30.780 | -9.232 | 47.090 | 1.00 | 28.57 | B | C |
| ATOM | 3810 | CB | GLU | B | 448 | 31.939 | -10.212 | 47.375 | 1.00 | 30.99 | B | C |
| ATOM | 3811 | CG | GLU | B | 448 | 31.731 | -11.602 | 46.751 | 1.00 | 33.06 | B | C |
| ATOM | 3812 | CD | GLU | B | 448 | 33.005 | -12.472 | 46.636 | 1.00 | 36.08 | B | C |
| ATOM | 3813 | OE1 | GLU | B | 448 | 34.123 | -12.041 | 47.012 | 1.00 | 36.67 | B | O |
| ATOM | 3814 | OE2 | GLU | B | 448 | 32.876 | -13.621 | 46.152 | 1.00 | 38.01 | B | O |
| ATOM | 3815 | C | GLU | B | 448 | 30.781 | -8.078 | 48.090 | 1.00 | 26.75 | B | C |
| ATOM | 3816 | O | GLU | B | 448 | 30.198 | -8.176 | 49.167 | 1.00 | 26.20 | B | O |
| ATOM | 3817 | N | VAL | B | 449 | 31.490 | -7.003 | 47.748 | 1.00 | 25.55 | B | N |
| ATOM | 3818 | CA | VAL | B | 449 | 31.567 | -5.813 | 48.610 | 1.00 | 24.36 | B | C |
| ATOM | 3819 | CB | VAL | B | 449 | 32.621 | -4.782 | 48.117 | 1.00 | 23.81 | B | C |
| ATOM | 3820 | CG1 | VAL | B | 449 | 32.626 | -3.529 | 48.984 | 1.00 | 20.94 | B | C |
| ATOM | 3821 | CG2 | VAL | B | 449 | 34.005 | -5.406 | 48.125 | 1.00 | 24.68 | B | C |
| ATOM | 3822 | C | VAL | B | 449 | 30.214 | -5.167 | 48.675 | 1.00 | 24.60 | B | C |
| ATOM | 3823 | O | VAL | B | 449 | 29.782 | -4.718 | 49.744 | 1.00 | 24.94 | B | O |
| ATOM | 3824 | N | ILE | B | 450 | 29.539 | -5.167 | 47.529 | 1.00 | 24.86 | B | N |
| ATOM | 3825 | CA | ILE | B | 450 | 28.205 | -4.619 | 47.414 | 1.00 | 25.23 | B | C |
| ATOM | 3826 | CB | ILE | B | 450 | 27.675 | -4.631 | 46.001 | 1.00 | 25.00 | B | C |
| ATOM | 3827 | CG2 | ILE | B | 450 | 26.424 | -3.795 | 45.932 | 1.00 | 23.89 | B | C |

Figure 13

| | | | | | | | | | | | |
|---|---|---|---|---|---|---|---|---|---|---|---|
| ATOM | 3828 | CG1 | ILE | B | 450 | 28.669 | -3.990 | 45.079 | 1.00 24.40 | B | C |
| ATOM | 3829 | CD1 | ILE | B | 450 | 28.752 | -2.549 | 45.286 | 1.00 27.73 | B | C |
| ATOM | 3830 | C | ILE | B | 450 | 27.227 | -5.405 | 48.247 | 1.00 26.12 | B | C |
| ATOM | 3831 | O | ILE | B | 450 | 26.457 | -4.789 | 48.971 | 1.00 26.42 | B | O |
| ATOM | 3832 | N | GLN | B | 451 | 27.252 | -6.748 | 48.171 | 1.00 26.73 | B | N |
| ATOM | 3833 | CA | GLN | B | 451 | 26.299 | -7.504 | 48.965 | 1.00 27.94 | B | C |
| ATOM | 3834 | CB | GLN | B | 451 | 26.013 | -8.911 | 48.433 | 1.00 31.34 | B | C |
| ATOM | 3835 | CG | GLN | B | 451 | 27.177 | -9.849 | 48.297 | 1.00 37.43 | B | C |
| ATOM | 3836 | CD | GLN | B | 451 | 26.957 | -10.843 | 47.182 | 1.00 40.52 | B | C |
| ATOM | 3837 | OE1 | GLN | B | 451 | 27.262 | -12.040 | 47.310 | 1.00 43.57 | B | O |
| ATOM | 3838 | NE2 | GLN | B | 451 | 26.471 | -10.343 | 46.053 | 1.00 39.95 | B | N |
| ATOM | 3839 | C | GLN | B | 451 | 26.625 | -7.481 | 50.426 | 1.00 25.95 | B | C |
| ATOM | 3840 | O | GLN | B | 451 | 25.716 | -7.514 | 51.235 | 1.00 26.55 | B | O |
| ATOM | 3841 | N | ASN | B | 452 | 27.893 | -7.282 | 50.766 | 1.00 25.09 | B | N |
| ATOM | 3842 | CA | ASN | B | 452 | 28.282 | -7.178 | 52.163 | 1.00 24.50 | B | C |
| ATOM | 3843 | CB | ASN | B | 452 | 29.777 | -7.405 | 52.317 | 1.00 25.64 | B | C |
| ATOM | 3844 | CG | ASN | B | 452 | 30.103 | -8.842 | 52.624 | 1.00 27.64 | B | C |
| ATOM | 3845 | OD1 | ASN | B | 452 | 30.242 | -9.214 | 53.782 | 1.00 29.21 | B | O |
| ATOM | 3846 | ND2 | ASN | B | 452 | 30.190 | -9.668 | 51.592 | 1.00 26.10 | B | N |
| ATOM | 3847 | C | ASN | B | 452 | 27.872 | -5.804 | 52.717 | 1.00 23.74 | B | C |
| ATOM | 3848 | O | ASN | B | 452 | 27.331 | -5.718 | 53.810 | 1.00 22.38 | B | O |
| ATOM | 3849 | N | LEU | B | 453 | 28.100 | -4.738 | 51.945 | 1.00 25.07 | B | N |
| ATOM | 3850 | CA | LEU | B | 453 | 27.702 | -3.407 | 52.381 | 1.00 25.34 | B | C |
| ATOM | 3851 | CB | LEU | B | 453 | 28.201 | -2.333 | 51.447 | 1.00 24.08 | B | C |
| ATOM | 3852 | CG | LEU | B | 453 | 29.718 | -2.098 | 51.529 | 1.00 24.10 | B | C |
| ATOM | 3853 | CD1 | LEU | B | 453 | 30.064 | -1.048 | 50.528 | 1.00 21.55 | B | C |
| ATOM | 3854 | CD2 | LEU | B | 453 | 30.201 | -1.719 | 52.935 | 1.00 22.94 | B | C |
| ATOM | 3855 | C | LEU | B | 453 | 26.193 | -3.343 | 52.581 | 1.00 26.47 | B | C |
| ATOM | 3856 | O | LEU | B | 453 | 25.775 | -2.722 | 53.581 | 1.00 27.18 | B | O |
| ATOM | 3857 | N | GLU | B | 454 | 25.404 | -4.087 | 51.768 | 1.00 26.84 | B | N |
| ATOM | 3858 | CA | GLU | B | 454 | 23.937 | -4.095 | 51.911 | 1.00 28.29 | B | C |
| ATOM | 3859 | CB | GLU | B | 454 | 23.207 | -5.001 | 50.898 | 1.00 32.35 | B | C |
| ATOM | 3860 | CG | GLU | B | 454 | 23.181 | -4.644 | 49.370 | 1.00 39.47 | B | C |
| ATOM | 3861 | CD | GLU | B | 454 | 23.017 | -5.901 | 48.443 | 1.00 43.78 | B | C |
| ATOM | 3862 | OE1 | GLU | B | 454 | 23.398 | -5.835 | 47.246 | 1.00 45.61 | B | O |
| ATOM | 3863 | OE2 | GLU | B | 454 | 22.535 | -6.959 | 48.918 | 1.00 46.03 | B | O |
| ATOM | 3864 | C | GLU | B | 454 | 23.623 | -4.657 | 53.298 | 1.00 27.23 | B | C |
| ATOM | 3865 | O | GLU | B | 454 | 22.664 | -4.226 | 53.902 | 1.00 27.03 | B | O |
| ATOM | 3866 | N | ARG | B | 455 | 24.440 | -5.600 | 53.805 | 1.00 26.72 | B | N |
| ATOM | 3867 | CA | ARG | B | 455 | 24.245 | -6.228 | 55.127 | 1.00 25.68 | B | C |
| ATOM | 3868 | CB | ARG | B | 455 | 24.708 | -7.715 | 55.128 | 1.00 27.59 | B | C |
| ATOM | 3869 | CG | ARG | B | 455 | 24.097 | -8.691 | 54.072 | 1.00 31.15 | B | C |
| ATOM | 3870 | CD | ARG | B | 455 | 24.617 | -10.164 | 54.216 | 1.00 35.34 | B | C |
| ATOM | 3871 | NE | ARG | B | 455 | 26.057 | -10.166 | 54.507 | 1.00 42.36 | B | N |
| ATOM | 3872 | CZ | ARG | B | 455 | 26.629 | -10.481 | 55.686 | 1.00 45.49 | B | C |
| ATOM | 3873 | NH1 | ARG | B | 455 | 25.896 | -10.878 | 56.732 | 1.00 46.79 | B | N |
| ATOM | 3874 | NH2 | ARG | B | 455 | 27.895 | -10.121 | 55.919 | 1.00 45.82 | B | N |
| ATOM | 3875 | C | ARG | B | 455 | 24.972 | -5.477 | 56.256 | 1.00 23.40 | B | C |
| ATOM | 3876 | O | ARG | B | 455 | 24.970 | -5.941 | 57.384 | 1.00 23.12 | B | O |
| ATOM | 3877 | N | GLY | B | 456 | 25.570 | -4.321 | 55.953 | 1.00 22.49 | B | N |
| ATOM | 3878 | CA | GLY | B | 456 | 26.275 | -3.499 | 56.938 | 1.00 19.03 | B | C |
| ATOM | 3879 | C | GLY | B | 456 | 27.696 | -3.903 | 57.265 | 1.00 18.57 | B | C |
| ATOM | 3880 | O | GLY | B | 456 | 28.221 | -3.531 | 58.300 | 1.00 18.55 | B | O |
| ATOM | 3881 | N | TYR | B | 457 | 28.322 | -4.645 | 56.379 | 1.00 18.08 | B | N |
| ATOM | 3882 | CA | TYR | B | 457 | 29.656 | -5.111 | 56.647 | 1.00 19.95 | B | C |
| ATOM | 3883 | CB | TYR | B | 457 | 30.046 | -6.192 | 55.629 | 1.00 19.86 | B | C |
| ATOM | 3884 | CG | TYR | B | 457 | 31.445 | -6.764 | 55.790 | 1.00 19.61 | B | C |
| ATOM | 3885 | CD1 | TYR | B | 457 | 31.675 | -7.976 | 56.477 | 1.00 19.68 | B | C |
| ATOM | 3886 | CE1 | TYR | B | 457 | 32.974 | -8.489 | 56.643 | 1.00 17.82 | B | C |
| ATOM | 3887 | CD2 | TYR | B | 457 | 32.548 | -6.090 | 55.272 | 1.00 21.21 | B | C |

Figure 13

| ATOM | 3888 | CE2 | TYR | B | 457 | 33.847 | -6.598 | 55.431 | 1.00 | 21.51 | B | C |
| ATOM | 3889 | CZ | TYR | B | 457 | 34.051 | -7.775 | 56.107 | 1.00 | 20.05 | B | C |
| ATOM | 3890 | OH | TYR | B | 457 | 35.376 | -8.135 | 56.223 | 1.00 | 22.61 | B | O |
| ATOM | 3891 | C | TYR | B | 457 | 30.741 | -4.055 | 56.796 | 1.00 | 21.33 | B | C |
| ATOM | 3892 | O | TYR | B | 457 | 30.727 | -3.044 | 56.089 | 1.00 | 24.31 | B | O |
| ATOM | 3893 | N | ARG | B | 458 | 31.594 | -4.229 | 57.808 | 1.00 | 20.64 | B | N |
| ATOM | 3894 | CA | ARG | B | 458 | 32.727 | -3.340 | 58.039 | 1.00 | 20.60 | B | C |
| ATOM | 3895 | CB | ARG | B | 458 | 32.529 | -2.491 | 59.288 | 1.00 | 20.92 | B | C |
| ATOM | 3896 | CG | ARG | B | 458 | 31.344 | -1.550 | 59.186 | 1.00 | 21.24 | B | C |
| ATOM | 3897 | CD | ARG | B | 458 | 31.458 | -0.653 | 57.941 | 1.00 | 21.32 | B | C |
| ATOM | 3898 | NE | ARG | B | 458 | 30.436 | 0.391 | 57.943 | 1.00 | 20.58 | B | N |
| ATOM | 3899 | CZ | ARG | B | 458 | 29.387 | 0.383 | 57.135 | 1.00 | 19.55 | B | C |
| ATOM | 3900 | NH1 | ARG | B | 458 | 29.251 | -0.594 | 56.279 | 1.00 | 20.05 | B | N |
| ATOM | 3901 | NH2 | ARG | B | 458 | 28.463 | 1.313 | 57.213 | 1.00 | 19.77 | B | N |
| ATOM | 3902 | C | ARG | B | 458 | 33.960 | -4.199 | 58.197 | 1.00 | 20.99 | B | C |
| ATOM | 3903 | O | ARG | B | 458 | 33.928 | -5.274 | 58.821 | 1.00 | 19.75 | B | O |
| ATOM | 3904 | N | MET | B | 459 | 35.045 | -3.744 | 57.579 | 1.00 | 21.54 | B | N |
| ATOM | 3905 | CA | MET | B | 459 | 36.316 | -4.447 | 57.673 | 1.00 | 21.19 | B | C |
| ATOM | 3906 | CB | MET | B | 459 | 37.373 | -3.815 | 56.786 | 1.00 | 22.59 | B | C |
| ATOM | 3907 | CG | MET | B | 459 | 37.197 | -3.959 | 55.282 | 1.00 | 23.70 | B | C |
| ATOM | 3908 | SD | MET | B | 459 | 38.735 | -3.333 | 54.531 | 1.00 | 27.52 | B | S |
| ATOM | 3909 | CE | MET | B | 459 | 38.343 | -1.661 | 54.306 | 1.00 | 24.48 | B | C |
| ATOM | 3910 | C | MET | B | 459 | 36.782 | -4.343 | 59.109 | 1.00 | 20.21 | B | C |
| ATOM | 3911 | O | MET | B | 459 | 36.539 | -3.353 | 59.793 | 1.00 | 17.58 | B | O |
| ATOM | 3912 | N | VAL | B | 460 | 37.414 | -5.416 | 59.549 | 1.00 | 20.98 | B | N |
| ATOM | 3913 | CA | VAL | B | 460 | 37.958 | -5.566 | 60.896 | 1.00 | 21.43 | B | C |
| ATOM | 3914 | CB | VAL | B | 460 | 38.354 | -7.039 | 61.126 | 1.00 | 19.37 | B | C |
| ATOM | 3915 | CG1 | VAL | B | 460 | 37.187 | -7.922 | 60.889 | 1.00 | 16.97 | B | C |
| ATOM | 3916 | CG2 | VAL | B | 460 | 39.440 | -7.431 | 60.191 | 1.00 | 17.42 | B | C |
| ATOM | 3917 | C | VAL | B | 460 | 39.205 | -4.683 | 61.031 | 1.00 | 23.06 | B | C |
| ATOM | 3918 | O | VAL | B | 460 | 39.675 | -4.120 | 60.043 | 1.00 | 23.02 | B | O |
| ATOM | 3919 | N | ARG | B | 461 | 39.742 | -4.579 | 62.238 | 1.00 | 25.26 | B | N |
| ATOM | 3920 | CA | ARG | B | 461 | 40.963 | -3.804 | 62.439 | 1.00 | 28.75 | B | C |
| ATOM | 3921 | CB | ARG | B | 461 | 41.291 | -3.661 | 63.928 | 1.00 | 30.07 | B | C |
| ATOM | 3922 | CG | ARG | B | 461 | 42.380 | -2.673 | 64.290 | 1.00 | 31.89 | B | C |
| ATOM | 3923 | CD | ARG | B | 461 | 42.655 | -2.684 | 65.790 | 1.00 | 34.59 | B | C |
| ATOM | 3924 | NE | ARG | B | 461 | 43.047 | -4.035 | 66.198 | 1.00 | 39.30 | B | N |
| ATOM | 3925 | CZ | ARG | B | 461 | 44.216 | -4.614 | 65.889 | 1.00 | 41.64 | B | C |
| ATOM | 3926 | NH1 | ARG | B | 461 | 45.151 | -3.958 | 65.189 | 1.00 | 41.77 | B | N |
| ATOM | 3927 | NH2 | ARG | B | 461 | 44.398 | -5.906 | 66.142 | 1.00 | 40.87 | B | N |
| ATOM | 3928 | C | ARG | B | 461 | 42.089 | -4.556 | 61.704 | 1.00 | 30.69 | B | C |
| ATOM | 3929 | O | ARG | B | 461 | 42.205 | -5.791 | 61.764 | 1.00 | 30.50 | B | O |
| ATOM | 3930 | N | PRO | B | 462 | 42.810 | -3.833 | 60.847 | 1.00 | 33.03 | B | N |
| ATOM | 3931 | CD | PRO | B | 462 | 42.479 | -2.478 | 60.365 | 1.00 | 32.03 | B | C |
| ATOM | 3932 | CA | PRO | B | 462 | 43.916 | -4.403 | 60.068 | 1.00 | 34.54 | B | C |
| ATOM | 3933 | CB | PRO | B | 462 | 44.288 | -3.245 | 59.133 | 1.00 | 32.71 | B | C |
| ATOM | 3934 | CG | PRO | B | 462 | 43.000 | -2.509 | 58.968 | 1.00 | 31.70 | B | C |
| ATOM | 3935 | C | PRO | B | 462 | 45.114 | -4.776 | 60.943 | 1.00 | 35.92 | B | C |
| ATOM | 3936 | O | PRO | B | 462 | 45.302 | -4.181 | 62.010 | 1.00 | 36.57 | B | O |
| ATOM | 3937 | N | ASP | B | 463 | 45.906 | -5.764 | 60.514 | 1.00 | 37.21 | B | N |
| ATOM | 3938 | CA | ASP | B | 463 | 47.095 | -6.112 | 61.281 | 1.00 | 38.71 | B | C |
| ATOM | 3939 | CB | ASP | B | 463 | 47.856 | -7.308 | 60.680 | 1.00 | 40.11 | B | C |
| ATOM | 3940 | CG | ASP | B | 463 | 47.119 | -8.638 | 60.828 | 1.00 | 42.06 | B | C |
| ATOM | 3941 | OD1 | ASP | B | 463 | 46.286 | -8.832 | 61.740 | 1.00 | 42.79 | B | O |
| ATOM | 3942 | OD2 | ASP | B | 463 | 47.403 | -9.533 | 60.019 | 1.00 | 44.26 | B | O |
| ATOM | 3943 | C | ASP | B | 463 | 48.029 | -4.897 | 61.321 | 1.00 | 39.10 | B | C |
| ATOM | 3944 | O | ASP | B | 463 | 48.393 | -4.343 | 60.274 | 1.00 | 38.71 | B | O |
| ATOM | 3945 | N | ASN | B | 464 | 48.430 | -4.532 | 62.539 | 1.00 | 39.90 | B | N |
| ATOM | 3946 | CA | ASN | B | 464 | 49.335 | -3.420 | 62.829 | 1.00 | 41.37 | B | C |
| ATOM | 3947 | CB | ASN | B | 464 | 50.712 | -3.642 | 62.175 | 1.00 | 45.18 | B | C |

Figure 13

| | | | | | | | | | | | |
|---|---|---|---|---|---|---|---|---|---|---|---|
| ATOM | 3948 | CG | ASN | B | 464 | 51.404 | -4.962 | 62.686 | 1.00 | 48.63 | B C |
| ATOM | 3949 | OD1 | ASN | B | 464 | 51.680 | -5.124 | 63.896 | 1.00 | 48.85 | B O |
| ATOM | 3950 | ND2 | ASN | B | 464 | 51.655 | -5.901 | 61.765 | 1.00 | 48.59 | B N |
| ATOM | 3951 | C | ASN | B | 464 | 48.748 | -2.043 | 62.551 | 1.00 | 41.49 | B C |
| ATOM | 3952 | O | ASN | B | 464 | 49.366 | -1.179 | 61.920 | 1.00 | 41.72 | B O |
| ATOM | 3953 | N | CYS | B | 465 | 47.596 | -1.838 | 63.192 | 1.00 | 40.09 | B N |
| ATOM | 3954 | CA | CYS | B | 465 | 46.783 | -0.633 | 63.123 | 1.00 | 37.14 | B C |
| ATOM | 3955 | CB | CYS | B | 465 | 45.513 | -0.900 | 62.272 | 1.00 | 36.73 | B C |
| ATOM | 3956 | SG | CYS | B | 465 | 44.284 | 0.422 | 62.352 | 1.00 | 35.47 | B S |
| ATOM | 3957 | C | CYS | B | 465 | 46.359 | -0.346 | 64.549 | 1.00 | 35.21 | B C |
| ATOM | 3958 | O | CYS | B | 465 | 45.858 | -1.241 | 65.214 | 1.00 | 35.56 | B O |
| ATOM | 3959 | N | PRO | B | 466 | 46.547 | 0.896 | 65.030 | 1.00 | 33.00 | B N |
| ATOM | 3960 | CD | PRO | B | 466 | 47.324 | 1.988 | 64.422 | 1.00 | 31.93 | B C |
| ATOM | 3961 | CA | PRO | B | 466 | 46.148 | 1.226 | 66.404 | 1.00 | 31.56 | B C |
| ATOM | 3962 | CB | PRO | B | 466 | 46.723 | 2.638 | 66.597 | 1.00 | 31.03 | B C |
| ATOM | 3963 | CG | PRO | B | 466 | 47.829 | 2.700 | 65.622 | 1.00 | 30.65 | B C |
| ATOM | 3964 | C | PRO | B | 466 | 44.611 | 1.208 | 66.579 | 1.00 | 32.03 | B C |
| ATOM | 3965 | O | PRO | B | 466 | 43.865 | 1.487 | 65.635 | 1.00 | 31.10 | B O |
| ATOM | 3966 | N | GLU | B | 467 | 44.133 | 0.932 | 67.794 | 1.00 | 32.85 | B N |
| ATOM | 3967 | CA | GLU | B | 467 | 42.678 | 0.887 | 68.022 | 1.00 | 32.63 | B C |
| ATOM | 3968 | CB | GLU | B | 467 | 42.296 | 0.388 | 69.422 | 1.00 | 32.81 | B C |
| ATOM | 3969 | CG | GLU | B | 467 | 41.619 | -1.008 | 69.410 | 1.00 | 35.68 | B C |
| ATOM | 3970 | CD | GLU | B | 467 | 40.178 | -1.084 | 68.842 | 1.00 | 36.31 | B C |
| ATOM | 3971 | OE1 | GLU | B | 467 | 39.923 | -1.951 | 67.958 | 1.00 | 36.30 | B O |
| ATOM | 3972 | OE2 | GLU | B | 467 | 39.287 | -0.343 | 69.337 | 1.00 | 37.23 | B O |
| ATOM | 3973 | C | GLU | B | 467 | 42.000 | 2.205 | 67.802 | 1.00 | 31.82 | B C |
| ATOM | 3974 | O | GLU | B | 467 | 40.882 | 2.245 | 67.311 | 1.00 | 31.65 | B O |
| ATOM | 3975 | N | GLU | B | 468 | 42.641 | 3.275 | 68.240 | 1.00 | 31.64 | B N |
| ATOM | 3976 | CA | GLU | B | 468 | 42.066 | 4.592 | 68.070 | 1.00 | 32.01 | B C |
| ATOM | 3977 | CB | GLU | B | 468 | 42.872 | 5.633 | 68.850 | 1.00 | 37.37 | B C |
| ATOM | 3978 | CG | GLU | B | 468 | 43.113 | 5.302 | 70.348 | 1.00 | 44.00 | B C |
| ATOM | 3979 | CD | GLU | B | 468 | 44.169 | 4.156 | 70.612 | 1.00 | 48.84 | B C |
| ATOM | 3980 | OE1 | GLU | B | 468 | 45.089 | 3.899 | 69.761 | 1.00 | 49.06 | B O |
| ATOM | 3981 | OE2 | GLU | B | 468 | 44.071 | 3.511 | 71.699 | 1.00 | 51.46 | B O |
| ATOM | 3982 | C | GLU | B | 468 | 42.027 | 4.899 | 66.551 | 1.00 | 29.42 | B C |
| ATOM | 3983 | O | GLU | B | 468 | 41.041 | 5.447 | 66.073 | 1.00 | 28.02 | B O |
| ATOM | 3984 | N | LEU | B | 469 | 43.029 | 4.451 | 65.783 | 1.00 | 27.26 | B N |
| ATOM | 3985 | CA | LEU | B | 469 | 43.002 | 4.676 | 64.344 | 1.00 | 25.83 | B C |
| ATOM | 3986 | CB | LEU | B | 469 | 44.315 | 4.290 | 63.674 | 1.00 | 24.84 | B C |
| ATOM | 3987 | CG | LEU | B | 469 | 44.341 | 4.522 | 62.155 | 1.00 | 23.76 | B C |
| ATOM | 3988 | CD1 | LEU | B | 469 | 43.924 | 5.960 | 61.818 | 1.00 | 23.84 | B C |
| ATOM | 3989 | CD2 | LEU | B | 469 | 45.689 | 4.229 | 61.606 | 1.00 | 20.98 | B C |
| ATOM | 3990 | C | LEU | B | 469 | 41.840 | 3.884 | 63.727 | 1.00 | 25.33 | B C |
| ATOM | 3991 | O | LEU | B | 469 | 41.170 | 4.366 | 62.817 | 1.00 | 25.46 | B O |
| ATOM | 3992 | N | TYR | B | 470 | 41.568 | 2.686 | 64.244 | 1.00 | 25.53 | B N |
| ATOM | 3993 | CA | TYR | B | 470 | 40.447 | 1.882 | 63.734 | 1.00 | 24.77 | B C |
| ATOM | 3994 | CB | TYR | B | 470 | 40.508 | 0.437 | 64.276 | 1.00 | 23.23 | B C |
| ATOM | 3995 | CG | TYR | B | 470 | 39.378 | -0.444 | 63.818 | 1.00 | 21.69 | B C |
| ATOM | 3996 | CD1 | TYR | B | 470 | 39.259 | -0.810 | 62.474 | 1.00 | 23.11 | B C |
| ATOM | 3997 | CE1 | TYR | B | 470 | 38.228 | -1.628 | 62.013 | 1.00 | 23.17 | B C |
| ATOM | 3998 | CD2 | TYR | B | 470 | 38.439 | -0.908 | 64.714 | 1.00 | 21.28 | B C |
| ATOM | 3999 | CE2 | TYR | B | 470 | 37.398 | -1.726 | 64.286 | 1.00 | 22.80 | B C |
| ATOM | 4000 | CZ | TYR | B | 470 | 37.283 | -2.091 | 62.915 | 1.00 | 23.75 | B C |
| ATOM | 4001 | OH | TYR | B | 470 | 36.213 | -2.859 | 62.442 | 1.00 | 22.93 | B O |
| ATOM | 4002 | C | TYR | B | 470 | 39.080 | 2.542 | 64.066 | 1.00 | 24.73 | B C |
| ATOM | 4003 | O | TYR | B | 470 | 38.158 | 2.516 | 63.247 | 1.00 | 23.63 | B O |
| ATOM | 4004 | N | GLN | B | 471 | 38.954 | 3.107 | 65.267 | 1.00 | 24.36 | B N |
| ATOM | 4005 | CA | GLN | B | 471 | 37.708 | 3.737 | 65.643 | 1.00 | 24.82 | B C |
| ATOM | 4006 | CB | GLN | B | 471 | 37.638 | 4.041 | 67.138 | 1.00 | 26.31 | B C |
| ATOM | 4007 | CG | GLN | B | 471 | 37.570 | 2.797 | 68.012 | 1.00 | 29.43 | B C |

Figure 13

| | | | | | | | | | | |
|---|---|---|---|---|---|---|---|---|---|---|
| ATOM | 4008 | CD | GLN | B | 471 | 36.492 | 1.752 | 67.573 | 1.00 31.73 | B | C |
| ATOM | 4009 | OE1 | GLN | B | 471 | 35.298 | 2.078 | 67.355 | 1.00 34.76 | B | O |
| ATOM | 4010 | NE2 | GLN | B | 471 | 36.903 | 0.488 | 67.512 | 1.00 29.75 | B | N |
| ATOM | 4011 | C | GLN | B | 471 | 37.466 | 4.967 | 64.766 | 1.00 24.55 | B | C |
| ATOM | 4012 | O | GLN | B | 471 | 36.311 | 5.314 | 64.478 | 1.00 24.41 | B | O |
| ATOM | 4013 | N | LEU | B | 472 | 38.552 | 5.560 | 64.265 | 1.00 22.55 | B | N |
| ATOM | 4014 | CA | LEU | B | 472 | 38.425 | 6.687 | 63.349 | 1.00 21.16 | B | C |
| ATOM | 4015 | CB | LEU | B | 472 | 39.750 | 7.419 | 63.136 | 1.00 20.65 | B | C |
| ATOM | 4016 | CG | LEU | B | 472 | 39.771 | 8.942 | 63.339 | 1.00 22.34 | B | C |
| ATOM | 4017 | CD1 | LEU | B | 472 | 39.070 | 9.345 | 64.656 | 1.00 20.02 | B | C |
| ATOM | 4018 | CD2 | LEU | B | 472 | 41.220 | 9.428 | 63.313 | 1.00 20.89 | B | C |
| ATOM | 4019 | C | LEU | B | 472 | 37.926 | 6.103 | 62.012 | 1.00 21.46 | B | C |
| ATOM | 4020 | O | LEU | B | 472 | 37.012 | 6.663 | 61.401 | 1.00 22.94 | B | O |
| ATOM | 4021 | N | MET | B | 473 | 38.420 | 4.929 | 61.609 | 1.00 20.36 | B | N |
| ATOM | 4022 | CA | MET | B | 473 | 37.964 | 4.361 | 60.347 | 1.00 19.91 | B | C |
| ATOM | 4023 | CB | MET | B | 473 | 38.679 | 3.064 | 60.042 | 1.00 18.92 | B | C |
| ATOM | 4024 | CG | MET | B | 473 | 40.135 | 3.247 | 59.791 | 1.00 16.09 | B | C |
| ATOM | 4025 | SD | MET | B | 473 | 40.916 | 1.722 | 59.896 | 1.00 17.40 | B | S |
| ATOM | 4026 | CE | MET | B | 473 | 42.546 | 2.017 | 59.275 | 1.00 9.53 | B | C |
| ATOM | 4027 | C | MET | B | 473 | 36.470 | 4.081 | 60.440 | 1.00 20.36 | B | C |
| ATOM | 4028 | O | MET | B | 473 | 35.715 | 4.257 | 59.479 | 1.00 20.00 | B | O |
| ATOM | 4029 | N | ARG | B | 474 | 36.038 | 3.643 | 61.622 | 1.00 21.95 | B | N |
| ATOM | 4030 | CA | ARG | B | 474 | 34.623 | 3.341 | 61.857 | 1.00 21.19 | B | C |
| ATOM | 4031 | CB | ARG | B | 474 | 34.459 | 2.563 | 63.169 | 1.00 21.73 | B | C |
| ATOM | 4032 | CG | ARG | B | 474 | 35.107 | 1.126 | 63.064 | 1.00 23.02 | B | C |
| ATOM | 4033 | CD | ARG | B | 474 | 34.552 | 0.284 | 61.884 | 1.00 20.84 | B | C |
| ATOM | 4034 | NE | ARG | B | 474 | 33.154 | -0.053 | 62.127 | 1.00 22.69 | B | N |
| ATOM | 4035 | CZ | ARG | B | 474 | 32.716 | -1.149 | 62.729 | 1.00 24.01 | B | C |
| ATOM | 4036 | NH1 | ARG | B | 474 | 33.538 | -2.095 | 63.173 | 1.00 23.80 | B | N |
| ATOM | 4037 | NH2 | ARG | B | 474 | 31.430 | -1.225 | 63.012 | 1.00 24.80 | B | N |
| ATOM | 4038 | C | ARG | B | 474 | 33.734 | 4.560 | 61.754 | 1.00 21.94 | B | C |
| ATOM | 4039 | O | ARG | B | 474 | 32.637 | 4.464 | 61.201 | 1.00 23.25 | B | O |
| ATOM | 4040 | N | LEU | B | 475 | 34.232 | 5.715 | 62.211 | 1.00 22.68 | B | N |
| ATOM | 4041 | CA | LEU | B | 475 | 33.470 | 6.969 | 62.135 | 1.00 21.91 | B | C |
| ATOM | 4042 | CB | LEU | B | 475 | 34.139 | 8.085 | 62.957 | 1.00 22.22 | B | C |
| ATOM | 4043 | CG | LEU | B | 475 | 34.029 | 7.788 | 64.456 | 1.00 23.83 | B | C |
| ATOM | 4044 | CD1 | LEU | B | 475 | 34.906 | 8.639 | 65.360 | 1.00 22.21 | B | C |
| ATOM | 4045 | CD2 | LEU | B | 475 | 32.534 | 7.893 | 64.834 | 1.00 22.73 | B | C |
| ATOM | 4046 | C | LEU | B | 475 | 33.442 | 7.371 | 60.673 | 1.00 20.67 | B | C |
| ATOM | 4047 | O | LEU | B | 475 | 32.486 | 7.957 | 60.211 | 1.00 20.48 | B | O |
| ATOM | 4048 | N | CYS | B | 476 | 34.485 | 7.034 | 59.921 | 1.00 20.34 | B | N |
| ATOM | 4049 | CA | CYS | B | 476 | 34.454 | 7.410 | 58.505 | 1.00 19.42 | B | C |
| ATOM | 4050 | CB | CYS | B | 476 | 35.843 | 7.394 | 57.873 | 1.00 19.51 | B | C |
| ATOM | 4051 | SG | CYS | B | 476 | 37.117 | 8.377 | 58.670 | 1.00 21.99 | B | S |
| ATOM | 4052 | C | CYS | B | 476 | 33.459 | 6.514 | 57.708 | 1.00 18.84 | B | C |
| ATOM | 4053 | O | CYS | B | 476 | 32.935 | 6.928 | 56.666 | 1.00 17.92 | B | O |
| ATOM | 4054 | N | TRP | B | 477 | 33.136 | 5.335 | 58.260 | 1.00 17.93 | B | N |
| ATOM | 4055 | CA | TRP | B | 477 | 32.219 | 4.385 | 57.630 | 1.00 16.78 | B | C |
| ATOM | 4056 | CB | TRP | B | 477 | 32.794 | 2.945 | 57.636 | 1.00 17.13 | B | C |
| ATOM | 4057 | CG | TRP | B | 477 | 34.156 | 2.819 | 57.010 | 1.00 17.25 | B | C |
| ATOM | 4058 | CD2 | TRP | B | 477 | 35.211 | 1.936 | 57.415 | 1.00 17.01 | B | C |
| ATOM | 4059 | CE2 | TRP | B | 477 | 36.315 | 2.207 | 56.598 | 1.00 18.41 | B | C |
| ATOM | 4060 | CE3 | TRP | B | 477 | 35.339 | 0.946 | 58.393 | 1.00 18.70 | B | C |
| ATOM | 4061 | CD1 | TRP | B | 477 | 34.654 | 3.554 | 55.979 | 1.00 17.25 | B | C |
| ATOM | 4062 | NE1 | TRP | B | 477 | 35.949 | 3.208 | 55.730 | 1.00 16.59 | B | N |
| ATOM | 4063 | CZ2 | TRP | B | 477 | 37.527 | 1.508 | 56.719 | 1.00 16.56 | B | C |
| ATOM | 4064 | CZ3 | TRP | B | 477 | 36.559 | 0.253 | 58.506 | 1.00 17.52 | B | C |
| ATOM | 4065 | CH2 | TRP | B | 477 | 37.619 | 0.547 | 57.680 | 1.00 15.99 | B | C |
| ATOM | 4066 | C | TRP | B | 477 | 30.814 | 4.366 | 58.213 | 1.00 17.47 | B | C |
| ATOM | 4067 | O | TRP | B | 477 | 30.055 | 3.429 | 57.941 | 1.00 18.09 | B | O |

Figure 13

```
ATOM   4068  N    LYS B 478      30.426   5.383  58.983  1.00 17.54           B  N
ATOM   4069  CA   LYS B 478      29.056   5.387  59.522  1.00 17.31           B  C
ATOM   4070  CB   LYS B 478      28.778   6.647  60.325  1.00 16.48           B  C
ATOM   4071  CG   LYS B 478      29.492   6.704  61.639  1.00 17.99           B  C
ATOM   4072  CD   LYS B 478      29.134   5.592  62.562  1.00 17.82           B  C
ATOM   4073  CE   LYS B 478      27.931   5.891  63.380  1.00 19.06           B  C
ATOM   4074  NZ   LYS B 478      27.406   4.640  64.106  1.00 22.08           B  N
ATOM   4075  C    LYS B 478      28.101   5.266  58.350  1.00 17.12           B  C
ATOM   4076  O    LYS B 478      28.365   5.809  57.275  1.00 17.46           B  O
ATOM   4077  N    GLU B 479      27.024   4.524  58.537  1.00 18.36           B  N
ATOM   4078  CA   GLU B 479      26.096   4.301  57.440  1.00 20.09           B  C
ATOM   4079  CB   GLU B 479      24.980   3.342  57.903  1.00 18.78           B  C
ATOM   4080  CG   GLU B 479      24.058   2.853  56.813  1.00 18.26           B  C
ATOM   4081  CD   GLU B 479      24.815   2.176  55.671  1.00 19.42           B  C
ATOM   4082  OE1  GLU B 479      25.898   1.566  55.836  1.00 20.02           B  O
ATOM   4083  OE2  GLU B 479      24.277   2.215  54.581  1.00 16.75           B  O
ATOM   4084  C    GLU B 479      25.510   5.592  56.860  1.00 21.90           B  C
ATOM   4085  O    GLU B 479      25.306   5.754  55.638  1.00 22.62           B  O
ATOM   4086  N    ARG B 480      25.193   6.499  57.777  1.00 22.58           B  N
ATOM   4087  CA   ARG B 480      24.597   7.764  57.425  1.00 22.59           B  C
ATOM   4088  CB   ARG B 480      23.621   8.200  58.493  1.00 24.22           B  C
ATOM   4089  CG   ARG B 480      22.437   7.371  58.688  1.00 25.65           B  C
ATOM   4090  CD   ARG B 480      22.025   7.662  60.086  1.00 32.57           B  C
ATOM   4091  NE   ARG B 480      20.661   7.238  60.347  1.00 40.11           B  N
ATOM   4092  CZ   ARG B 480      20.082   7.267  61.542  1.00 43.47           B  C
ATOM   4093  NH1  ARG B 480      20.747   7.739  62.615  1.00 42.62           B  N
ATOM   4094  NH2  ARG B 480      18.829   6.833  61.645  1.00 44.99           B  N
ATOM   4095  C    ARG B 480      25.706   8.794  57.387  1.00 22.68           B  C
ATOM   4096  O    ARG B 480      26.433   8.942  58.362  1.00 22.75           B  O
ATOM   4097  N    PRO B 481      25.757   9.606  56.317  1.00 23.12           B  N
ATOM   4098  CD   PRO B 481      24.784   9.553  55.215  1.00 23.12           B  C
ATOM   4099  CA   PRO B 481      26.722  10.672  56.049  1.00 22.71           B  C
ATOM   4100  CB   PRO B 481      26.125  11.344  54.819  1.00 22.55           B  C
ATOM   4101  CG   PRO B 481      25.538  10.237  54.100  1.00 22.97           B  C
ATOM   4102  C    PRO B 481      26.919  11.691  57.166  1.00 22.92           B  C
ATOM   4103  O    PRO B 481      28.052  11.974  57.588  1.00 23.13           B  O
ATOM   4104  N    GLU B 482      25.809  12.204  57.666  1.00 21.96           B  N
ATOM   4105  CA   GLU B 482      25.831  13.214  58.713  1.00 21.57           B  C
ATOM   4106  CB   GLU B 482      24.392  13.595  59.089  1.00 21.67           B  C
ATOM   4107  CG   GLU B 482      23.613  12.509  59.824  1.00 22.21           B  C
ATOM   4108  CD   GLU B 482      22.533  11.802  58.968  1.00 23.51           B  C
ATOM   4109  OE1  GLU B 482      22.778  11.533  57.766  1.00 23.54           B  O
ATOM   4110  OE2  GLU B 482      21.439  11.494  59.513  1.00 23.32           B  O
ATOM   4111  C    GLU B 482      26.617  12.812  59.966  1.00 21.81           B  C
ATOM   4112  O    GLU B 482      27.040  13.667  60.747  1.00 22.17           B  O
ATOM   4113  N    ASP B 483      26.807  11.501  60.142  1.00 21.50           B  N
ATOM   4114  CA   ASP B 483      27.485  10.893  61.286  1.00 21.16           B  C
ATOM   4115  CB   ASP B 483      26.826   9.543  61.573  1.00 20.75           B  C
ATOM   4116  CG   ASP B 483      25.454   9.675  62.202  1.00 22.46           B  C
ATOM   4117  OD1  ASP B 483      25.178  10.663  62.895  1.00 22.62           B  O
ATOM   4118  OD2  ASP B 483      24.643   8.758  62.048  1.00 25.80           B  O
ATOM   4119  C    ASP B 483      28.980  10.706  61.127  1.00 21.63           B  C
ATOM   4120  O    ASP B 483      29.657  10.219  62.063  1.00 20.73           B  O
ATOM   4121  N    ARG B 484      29.465  10.971  59.915  1.00 21.55           B  N
ATOM   4122  CA   ARG B 484      30.897  10.842  59.586  1.00 21.08           B  C
ATOM   4123  CB   ARG B 484      31.111  10.433  58.109  1.00 20.58           B  C
ATOM   4124  CG   ARG B 484      30.145   9.396  57.605  1.00 19.10           B  C
ATOM   4125  CD   ARG B 484      30.423   9.067  56.158  1.00 20.40           B  C
ATOM   4126  NE   ARG B 484      29.616   7.915  55.745  1.00 21.38           B  N
ATOM   4127  CZ   ARG B 484      28.987   7.810  54.580  1.00 21.64           B  C
```

Figure 13

| | | | | | | | | | | | |
|---|---|---|---|---|---|---|---|---|---|---|---|
| ATOM | 4128 | NH1 | ARG | B | 484 | 29.094 | 8.793 | 53.690 | 1.00 | 19.64 | B | N |
| ATOM | 4129 | NH2 | ARG | B | 484 | 28.150 | 6.793 | 54.367 | 1.00 | 19.02 | B | N |
| ATOM | 4130 | C | ARG | B | 484 | 31.533 | 12.197 | 59.879 | 1.00 | 22.02 | B | C |
| ATOM | 4131 | O | ARG | B | 484 | 30.942 | 13.232 | 59.593 | 1.00 | 21.90 | B | O |
| ATOM | 4132 | N | PRO | B | 485 | 32.782 | 12.204 | 60.361 | 1.00 | 24.17 | B | N |
| ATOM | 4133 | CD | PRO | B | 485 | 33.732 | 11.105 | 60.199 | 1.00 | 22.33 | B | C |
| ATOM | 4134 | CA | PRO | B | 485 | 33.500 | 13.437 | 60.710 | 1.00 | 22.90 | B | C |
| ATOM | 4135 | CB | PRO | B | 485 | 34.784 | 12.923 | 61.386 | 1.00 | 23.00 | B | C |
| ATOM | 4136 | CG | PRO | B | 485 | 34.676 | 11.404 | 61.273 | 1.00 | 24.00 | B | C |
| ATOM | 4137 | C | PRO | B | 485 | 33.865 | 14.325 | 59.534 | 1.00 | 24.46 | B | C |
| ATOM | 4138 | O | PRO | B | 485 | 33.913 | 13.891 | 58.372 | 1.00 | 24.67 | B | O |
| ATOM | 4139 | N | THR | B | 486 | 34.194 | 15.566 | 59.876 | 1.00 | 24.42 | B | N |
| ATOM | 4140 | CA | THR | B | 486 | 34.609 | 16.538 | 58.876 | 1.00 | 22.66 | B | C |
| ATOM | 4141 | CB | THR | B | 486 | 34.438 | 17.967 | 59.373 | 1.00 | 20.48 | B | C |
| ATOM | 4142 | OG1 | THR | B | 486 | 35.101 | 18.104 | 60.621 | 1.00 | 23.35 | B | O |
| ATOM | 4143 | CG2 | THR | B | 486 | 33.040 | 18.303 | 59.526 | 1.00 | 16.60 | B | C |
| ATOM | 4144 | C | THR | B | 486 | 36.111 | 16.253 | 58.667 | 1.00 | 22.72 | B | C |
| ATOM | 4145 | O | THR | B | 486 | 36.773 | 15.776 | 59.578 | 1.00 | 21.67 | B | O |
| ATOM | 4146 | N | PHE | B | 487 | 36.654 | 16.549 | 57.491 | 1.00 | 21.72 | B | N |
| ATOM | 4147 | CA | PHE | B | 487 | 38.056 | 16.282 | 57.250 | 1.00 | 21.08 | B | C |
| ATOM | 4148 | CB | PHE | B | 487 | 38.397 | 16.547 | 55.819 | 1.00 | 19.77 | B | C |
| ATOM | 4149 | CG | PHE | B | 487 | 38.150 | 15.401 | 54.933 | 1.00 | 18.71 | B | C |
| ATOM | 4150 | CD1 | PHE | B | 487 | 38.881 | 14.227 | 55.060 | 1.00 | 16.00 | B | C |
| ATOM | 4151 | CD2 | PHE | B | 487 | 37.209 | 15.503 | 53.932 | 1.00 | 18.70 | B | C |
| ATOM | 4152 | CE1 | PHE | B | 487 | 38.674 | 13.185 | 54.199 | 1.00 | 14.82 | B | C |
| ATOM | 4153 | CE2 | PHE | B | 487 | 37.000 | 14.460 | 53.067 | 1.00 | 18.31 | B | C |
| ATOM | 4154 | CZ | PHE | B | 487 | 37.734 | 13.299 | 53.197 | 1.00 | 17.45 | B | C |
| ATOM | 4155 | C | PHE | B | 487 | 38.827 | 17.230 | 58.113 | 1.00 | 23.30 | B | C |
| ATOM | 4156 | O | PHE | B | 487 | 40.009 | 17.073 | 58.289 | 1.00 | 24.95 | B | O |
| ATOM | 4157 | N | ASP | B | 488 | 38.148 | 18.260 | 58.628 | 1.00 | 25.33 | B | N |
| ATOM | 4158 | CA | ASP | B | 488 | 38.735 | 19.254 | 59.532 | 1.00 | 24.28 | B | C |
| ATOM | 4159 | CB | ASP | B | 488 | 37.790 | 20.464 | 59.626 | 1.00 | 25.59 | B | C |
| ATOM | 4160 | CG | ASP | B | 488 | 38.231 | 21.505 | 60.668 | 1.00 | 29.12 | B | C |
| ATOM | 4161 | OD1 | ASP | B | 488 | 39.461 | 21.769 | 60.799 | 1.00 | 29.70 | B | O |
| ATOM | 4162 | OD2 | ASP | B | 488 | 37.333 | 22.054 | 61.368 | 1.00 | 28.10 | B | O |
| ATOM | 4163 | C | ASP | B | 488 | 38.937 | 18.534 | 60.878 | 1.00 | 23.86 | B | C |
| ATOM | 4164 | O | ASP | B | 488 | 39.959 | 18.685 | 61.516 | 1.00 | 23.15 | B | O |
| ATOM | 4165 | N | TYR | B | 489 | 37.996 | 17.690 | 61.284 | 1.00 | 23.96 | B | N |
| ATOM | 4166 | CA | TYR | B | 489 | 38.191 | 16.918 | 62.516 | 1.00 | 23.54 | B | C |
| ATOM | 4167 | CB | TYR | B | 489 | 36.913 | 16.267 | 62.972 | 1.00 | 20.90 | B | C |
| ATOM | 4168 | CG | TYR | B | 489 | 37.121 | 15.283 | 64.088 | 1.00 | 18.14 | B | C |
| ATOM | 4169 | CD1 | TYR | B | 489 | 37.393 | 15.708 | 65.364 | 1.00 | 17.39 | B | C |
| ATOM | 4170 | CE1 | TYR | B | 489 | 37.596 | 14.797 | 66.394 | 1.00 | 16.70 | B | C |
| ATOM | 4171 | CD2 | TYR | B | 489 | 37.059 | 13.920 | 63.866 | 1.00 | 17.34 | B | C |
| ATOM | 4172 | CE2 | TYR | B | 489 | 37.264 | 13.012 | 64.895 | 1.00 | 15.86 | B | C |
| ATOM | 4173 | CZ | TYR | B | 489 | 37.527 | 13.455 | 66.151 | 1.00 | 16.30 | B | C |
| ATOM | 4174 | OH | TYR | B | 489 | 37.708 | 12.583 | 67.185 | 1.00 | 15.99 | B | O |
| ATOM | 4175 | C | TYR | B | 489 | 39.239 | 15.830 | 62.299 | 1.00 | 25.79 | B | C |
| ATOM | 4176 | O | TYR | B | 489 | 40.098 | 15.632 | 63.158 | 1.00 | 27.79 | B | O |
| ATOM | 4177 | N | LEU | B | 490 | 39.189 | 15.164 | 61.140 | 1.00 | 26.21 | B | N |
| ATOM | 4178 | CA | LEU | B | 490 | 40.141 | 14.115 | 60.803 | 1.00 | 27.31 | B | C |
| ATOM | 4179 | CB | LEU | B | 490 | 39.825 | 13.493 | 59.443 | 1.00 | 28.51 | B | C |
| ATOM | 4180 | CG | LEU | B | 490 | 38.635 | 12.524 | 59.485 | 1.00 | 29.74 | B | C |
| ATOM | 4181 | CD1 | LEU | B | 490 | 38.210 | 12.161 | 58.049 | 1.00 | 29.89 | B | C |
| ATOM | 4182 | CD2 | LEU | B | 490 | 38.978 | 11.277 | 60.311 | 1.00 | 29.87 | B | C |
| ATOM | 4183 | C | LEU | B | 490 | 41.564 | 14.640 | 60.800 | 1.00 | 28.17 | B | C |
| ATOM | 4184 | O | LEU | B | 490 | 42.454 | 13.985 | 61.348 | 1.00 | 28.22 | B | O |
| ATOM | 4185 | N | ARG | B | 491 | 41.771 | 15.829 | 60.228 | 1.00 | 28.39 | B | N |
| ATOM | 4186 | CA | ARG | B | 491 | 43.099 | 16.432 | 60.184 | 1.00 | 30.74 | B | C |
| ATOM | 4187 | CB | ARG | B | 491 | 43.133 | 17.771 | 59.451 | 1.00 | 30.82 | B | C |

Figure 13

| | | | | | | | | | | |
|---|---|---|---|---|---|---|---|---|---|---|
| ATOM | 4188 | CG | ARG | B | 491 | 44.462 | 18.509 | 59.706 | 1.00 33.67 | B C |
| ATOM | 4189 | CD | ARG | B | 491 | 44.431 | 20.009 | 59.273 | 1.00 40.17 | B C |
| ATOM | 4190 | NE | ARG | B | 491 | 43.259 | 20.672 | 59.855 | 1.00 44.94 | B N |
| ATOM | 4191 | CZ | ARG | B | 491 | 43.157 | 21.000 | 61.139 | 1.00 45.68 | B C |
| ATOM | 4192 | NH1 | ARG | B | 491 | 44.174 | 20.750 | 61.970 | 1.00 44.49 | B N |
| ATOM | 4193 | NH2 | ARG | B | 491 | 42.006 | 21.478 | 61.598 | 1.00 44.34 | B N |
| ATOM | 4194 | C | ARG | B | 491 | 43.602 | 16.679 | 61.583 | 1.00 31.94 | B C |
| ATOM | 4195 | O | ARG | B | 491 | 44.783 | 16.513 | 61.857 | 1.00 32.63 | B O |
| ATOM | 4196 | N | SER | B | 492 | 42.724 | 17.215 | 62.416 | 1.00 32.57 | B N |
| ATOM | 4197 | CA | SER | B | 492 | 43.068 | 17.533 | 63.786 | 1.00 33.72 | B C |
| ATOM | 4198 | CB | SER | B | 492 | 41.842 | 18.064 | 64.523 | 1.00 35.24 | B C |
| ATOM | 4199 | OG | SER | B | 492 | 41.625 | 19.402 | 64.128 | 1.00 37.26 | B O |
| ATOM | 4200 | C | SER | B | 492 | 43.620 | 16.371 | 64.529 | 1.00 33.61 | B C |
| ATOM | 4201 | O | SER | B | 492 | 44.747 | 16.406 | 65.008 | 1.00 33.77 | B O |
| ATOM | 4202 | N | VAL | B | 493 | 42.811 | 15.329 | 64.586 | 1.00 33.97 | B N |
| ATOM | 4203 | CA | VAL | B | 493 | 43.131 | 14.116 | 65.301 | 1.00 33.97 | B C |
| ATOM | 4204 | CB | VAL | B | 493 | 41.806 | 13.317 | 65.511 | 1.00 34.85 | B C |
| ATOM | 4205 | CG1 | VAL | B | 493 | 41.107 | 13.035 | 64.164 | 1.00 36.00 | B C |
| ATOM | 4206 | CG2 | VAL | B | 493 | 42.068 | 12.040 | 66.295 | 1.00 35.59 | B C |
| ATOM | 4207 | C | VAL | B | 493 | 44.306 | 13.314 | 64.689 | 1.00 33.93 | B C |
| ATOM | 4208 | O | VAL | B | 493 | 45.101 | 12.726 | 65.422 | 1.00 33.52 | B O |
| ATOM | 4209 | N | LEU | B | 494 | 44.492 | 13.384 | 63.370 | 1.00 34.31 | B N |
| ATOM | 4210 | CA | LEU | B | 494 | 45.612 | 12.676 | 62.746 | 1.00 34.96 | B C |
| ATOM | 4211 | CB | LEU | B | 494 | 45.404 | 12.533 | 61.247 | 1.00 32.40 | B C |
| ATOM | 4212 | CG | LEU | B | 494 | 44.345 | 11.483 | 61.001 | 1.00 30.25 | B C |
| ATOM | 4213 | CD1 | LEU | B | 494 | 44.031 | 11.434 | 59.569 | 1.00 28.20 | B C |
| ATOM | 4214 | CD2 | LEU | B | 494 | 44.820 | 10.132 | 61.541 | 1.00 30.54 | B C |
| ATOM | 4215 | C | LEU | B | 494 | 46.944 | 13.358 | 63.011 | 1.00 36.52 | B C |
| ATOM | 4216 | O | LEU | B | 494 | 47.959 | 12.700 | 63.107 | 1.00 36.52 | B O |
| ATOM | 4217 | N | GLU | B | 495 | 46.940 | 14.676 | 63.143 | 1.00 39.25 | B N |
| ATOM | 4218 | CA | GLU | B | 495 | 48.173 | 15.418 | 63.418 | 1.00 42.40 | B C |
| ATOM | 4219 | CB | GLU | B | 495 | 47.923 | 16.908 | 63.316 | 1.00 43.53 | B C |
| ATOM | 4220 | CG | GLU | B | 495 | 48.002 | 17.453 | 61.926 | 1.00 46.37 | B C |
| ATOM | 4221 | CD | GLU | B | 495 | 47.836 | 18.934 | 61.887 | 1.00 48.24 | B C |
| ATOM | 4222 | OE1 | GLU | B | 495 | 47.808 | 19.563 | 62.970 | 1.00 50.76 | B O |
| ATOM | 4223 | OE2 | GLU | B | 495 | 47.732 | 19.471 | 60.765 | 1.00 49.02 | B O |
| ATOM | 4224 | C | GLU | B | 495 | 48.670 | 15.165 | 64.822 | 1.00 43.59 | B C |
| ATOM | 4225 | O | GLU | B | 495 | 49.869 | 14.979 | 65.028 | 1.00 44.07 | B O |
| ATOM | 4226 | N | ASP | B | 496 | 47.731 | 15.238 | 65.773 | 1.00 44.64 | B N |
| ATOM | 4227 | CA | ASP | B | 496 | 47.984 | 15.054 | 67.195 | 1.00 45.94 | B C |
| ATOM | 4228 | CB | ASP | B | 496 | 46.990 | 15.925 | 68.008 | 1.00 45.49 | B C |
| ATOM | 4229 | CG | ASP | B | 496 | 47.249 | 17.471 | 67.842 | 1.00 46.39 | B C |
| ATOM | 4230 | OD1 | ASP | B | 496 | 48.395 | 17.886 | 67.492 | 1.00 46.15 | B O |
| ATOM | 4231 | OD2 | ASP | B | 496 | 46.294 | 18.272 | 68.064 | 1.00 46.26 | B O |
| ATOM | 4232 | C | ASP | B | 496 | 47.966 | 13.596 | 67.685 | 1.00 47.19 | B C |
| ATOM | 4233 | O | ASP | B | 496 | 48.132 | 13.340 | 68.875 | 1.00 48.37 | B O |
| ATOM | 4234 | N | PHE | B | 497 | 47.876 | 12.638 | 66.770 | 1.00 48.00 | B N |
| ATOM | 4235 | CA | PHE | B | 497 | 47.799 | 11.218 | 67.148 | 1.00 48.48 | B C |
| ATOM | 4236 | CB | PHE | B | 497 | 47.768 | 10.345 | 65.903 | 1.00 47.63 | B C |
| ATOM | 4237 | CG | PHE | B | 497 | 47.091 | 9.035 | 66.124 | 1.00 48.06 | B C |
| ATOM | 4238 | CD1 | PHE | B | 497 | 45.707 | 8.925 | 65.989 | 1.00 48.49 | B C |
| ATOM | 4239 | CD2 | PHE | B | 497 | 47.829 | 7.907 | 66.492 | 1.00 48.47 | B C |
| ATOM | 4240 | CE1 | PHE | B | 497 | 45.073 | 7.718 | 66.216 | 1.00 48.47 | B C |
| ATOM | 4241 | CE2 | PHE | B | 497 | 47.214 | 6.694 | 66.720 | 1.00 48.06 | B C |
| ATOM | 4242 | CZ | PHE | B | 497 | 45.829 | 6.591 | 66.587 | 1.00 48.63 | B C |
| ATOM | 4243 | C | PHE | B | 497 | 48.826 | 10.677 | 68.167 | 1.00 48.97 | B C |
| ATOM | 4244 | O | PHE | B | 497 | 48.501 | 9.807 | 68.970 | 1.00 48.23 | B O |
| ATOM | 4245 | N | PHE | B | 498 | 50.074 | 11.140 | 68.079 | 1.00 50.79 | B N |
| ATOM | 4246 | CA | PHE | B | 498 | 51.154 | 10.761 | 69.025 | 1.00 52.12 | B C |
| ATOM | 4247 | CB | PHE | B | 498 | 51.293 | 9.239 | 69.265 | 1.00 52.63 | B C |

Figure 13

| | | | | | | | | | | |
|---|---|---|---|---|---|---|---|---|---|---|
| ATOM | 4248 | CG | PHE | B | 498 | 51.440 | 8.421 | 68.020 | 1.00 52.99 | B | C |
| ATOM | 4249 | CD1 | PHE | B | 498 | 51.946 | 8.968 | 66.850 | 1.00 52.50 | B | C |
| ATOM | 4250 | CD2 | PHE | B | 498 | 50.995 | 7.107 | 68.011 | 1.00 53.16 | B | C |
| ATOM | 4251 | CE1 | PHE | B | 498 | 51.987 | 8.215 | 65.687 | 1.00 53.30 | B | C |
| ATOM | 4252 | CE2 | PHE | B | 498 | 51.034 | 6.346 | 66.850 | 1.00 53.47 | B | C |
| ATOM | 4253 | CZ | PHE | B | 498 | 51.530 | 6.899 | 65.687 | 1.00 53.59 | B | C |
| ATOM | 4254 | C | PHE | B | 498 | 52.513 | 11.334 | 68.685 | 1.00 52.18 | B | C |
| ATOM | 4255 | O | PHE | B | 498 | 52.654 | 12.549 | 68.908 | 1.00 52.66 | B | O |
| ATOM | 4256 | OH2 | H2O | B | 600 | 34.116 | 0.760 | 50.674 | 1.00 32.30 | B | O |
| ATOM | 4257 | OH2 | H2O | B | 601 | 30.321 | 20.046 | 60.698 | 1.00 67.52 | B | O |
| ATOM | 4258 | OH2 | H2O | B | 602 | 27.345 | -0.872 | 59.747 | 1.00 20.40 | B | O |
| ATOM | 4259 | OH2 | H2O | B | 604 | 35.206 | 20.754 | 62.867 | 1.00 29.07 | B | O |
| ATOM | 4260 | OH2 | H2O | B | 605 | 22.875 | -2.040 | 57.861 | 1.00 52.64 | B | O |
| ATOM | 4261 | OH2 | H2O | B | 606 | 35.928 | 9.667 | 46.985 | 1.00 40.53 | B | O |
| ATOM | 4262 | OH2 | H2O | B | 607 | 25.467 | 6.306 | 60.778 | 1.00 18.38 | B | O |
| ATOM | 4263 | OH2 | H2O | B | 608 | 29.459 | 13.667 | 62.746 | 1.00 51.08 | B | O |
| ATOM | 4264 | OH2 | H2O | B | 609 | 27.603 | -7.257 | 58.566 | 1.00 30.73 | B | O |
| ATOM | 4265 | OH2 | H2O | B | 610 | 34.874 | -1.398 | 55.660 | 1.00 11.40 | B | O |
| ATOM | 4266 | OH2 | H2O | B | 611 | 34.253 | 4.617 | 65.958 | 1.00 22.90 | B | O |
| ATOM | 4267 | OH2 | H2O | B | 612 | 29.533 | 17.386 | 59.594 | 1.00 32.20 | B | O |
| ATOM | 4268 | OH2 | H2O | B | 613 | 28.355 | -5.211 | 60.586 | 1.00 50.44 | B | O |
| ATOM | 4269 | OH2 | H2O | B | 614 | 37.897 | 13.413 | 41.210 | 1.00 19.15 | B | O |
| ATOM | 4270 | OH2 | H2O | B | 615 | 18.999 | 15.117 | 63.042 | 1.00 27.60 | B | O |
| ATOM | 4271 | OH2 | H2O | B | 616 | 27.189 | 16.407 | 60.230 | 1.00 34.19 | B | O |
| ATOM | 4272 | OH2 | H2O | B | 617 | 30.999 | -6.783 | 60.238 | 1.00 60.13 | B | O |
| ATOM | 4273 | OH2 | H2O | B | 618 | 36.955 | -1.760 | 44.102 | 1.00 24.19 | B | O |
| ATOM | 4274 | OH2 | H2O | B | 619 | 27.706 | 18.070 | 55.959 | 1.00 69.77 | B | O |
| ATOM | 4275 | OH2 | H2O | B | 620 | 30.020 | -3.638 | 63.214 | 1.00 30.76 | B | O |
| ATOM | 4276 | OH2 | H2O | B | 621 | 58.732 | 8.702 | 39.589 | 1.00 42.86 | B | O |
| ATOM | 4277 | OH2 | H2O | B | 622 | 32.891 | 22.267 | 61.777 | 1.00 45.32 | B | O |
| ATOM | 4278 | OH2 | H2O | B | 623 | 25.071 | -0.589 | 58.033 | 1.00 41.82 | B | O |
| ATOM | 4279 | OH2 | H2O | B | 624 | 64.629 | 10.825 | 38.214 | 1.00 35.91 | B | O |
| ATOM | 4280 | OH2 | H2O | B | 625 | 49.034 | 17.991 | 58.275 | 1.00 27.47 | B | O |
| ATOM | 4281 | OH2 | H2O | B | 626 | 44.077 | 2.989 | 45.740 | 1.00 26.16 | B | O |
| ATOM | 4282 | OH2 | H2O | B | 627 | 32.681 | 17.093 | 56.131 | 1.00 17.67 | B | O |
| ATOM | 4283 | OH2 | H2O | B | 628 | 32.755 | 7.470 | 48.443 | 1.00 19.51 | B | O |
| ATOM | 4284 | OH2 | H2O | B | 630 | 37.229 | 8.149 | 67.344 | 1.00 54.24 | B | O |
| ATOM | 4285 | OH2 | H2O | B | 631 | 62.541 | 23.518 | 26.499 | 1.00 28.69 | B | O |
| ATOM | 4286 | OH2 | H2O | B | 632 | 34.188 | -4.929 | 61.718 | 1.00 30.51 | B | O |
| ATOM | 4287 | OH2 | H2O | B | 633 | 46.006 | 10.050 | 40.194 | 1.00 34.78 | B | O |
| ATOM | 4288 | OH2 | H2O | B | 634 | 46.030 | 23.865 | 55.237 | 1.00 18.81 | B | O |
| ATOM | 4289 | OH2 | H2O | B | 635 | 27.323 | 11.584 | 50.247 | 1.00 34.84 | B | O |
| ATOM | 4290 | OH2 | H2O | B | 636 | 26.682 | 10.613 | 65.295 | 1.00 21.34 | B | O |
| ATOM | 4291 | OH2 | H2O | B | 638 | 20.548 | 14.565 | 65.451 | 1.00 31.15 | B | O |
| ATOM | 4292 | OH2 | H2O | B | 639 | 44.718 | 12.130 | 68.223 | 1.00 52.23 | B | O |
| ATOM | 4293 | OH2 | H2O | B | 640 | 27.133 | -0.393 | 54.466 | 1.00 32.58 | B | O |
| ATOM | 4294 | OH2 | H2O | B | 641 | 25.880 | 16.782 | 57.591 | 1.00 23.59 | B | O |
| ATOM | 4295 | OH2 | H2O | B | 642 | 48.018 | 23.200 | 44.560 | 1.00 30.89 | B | O |
| ATOM | 4296 | OH2 | H2O | B | 643 | 55.259 | 0.150 | 26.663 | 1.00 76.79 | B | O |
| ATOM | 4297 | OH2 | H2O | B | 644 | 31.567 | 1.708 | 60.481 | 1.00 43.07 | B | O |
| ATOM | 4298 | OH2 | H2O | B | 645 | 24.245 | -0.640 | 50.584 | 1.00 31.79 | B | O |
| ATOM | 4299 | OH2 | H2O | B | 646 | 57.512 | 21.177 | 18.682 | 1.00 54.89 | B | O |
| ATOM | 4300 | OH2 | H2O | B | 647 | 32.762 | -12.871 | 53.506 | 1.00 33.57 | B | O |
| ATOM | 4301 | OH2 | H2O | B | 648 | 29.561 | 18.136 | 49.181 | 1.00 22.27 | B | O |
| ATOM | 4302 | OH2 | H2O | B | 649 | 15.601 | 17.263 | 62.569 | 1.00 26.39 | B | O |
| ATOM | 4303 | OH2 | H2O | B | 650 | 40.701 | -5.224 | 57.479 | 1.00 24.71 | B | O |
| ATOM | 4304 | OH2 | H2O | B | 651 | 31.845 | 25.495 | 58.619 | 1.00 37.90 | B | O |
| ATOM | 4305 | OH2 | H2O | B | 652 | 27.305 | 2.111 | 61.038 | 1.00 42.59 | B | O |
| ATOM | 4306 | OH2 | H2O | B | 653 | 32.291 | 0.421 | 48.804 | 1.00 16.29 | B | O |
| ATOM | 4307 | OH2 | H2O | B | 654 | 32.329 | -7.991 | 64.681 | 1.00 25.11 | B | O |

Figure 13

```
ATOM   4308  OH2 H2O B 655      52.884    1.963   32.885  1.00 44.22      B    O
ATOM   4309  OH2 H2O B 656      33.648   19.542   43.582  1.00 41.01      B    O
ATOM   4310  OH2 H2O B 657      30.264   19.776   53.476  1.00 74.47      B    O
ATOM   4311  OH2 H2O B 658      27.190   -1.608   65.841  1.00 45.60      B    O
ATOM   4312  OH2 H2O B 659      38.290   -5.029   64.556  1.00 15.49      B    O
ATOM   4313  OH2 H2O B 660      52.538    1.298   38.698  1.00 52.22      B    O
ATOM   4314  OH2 H2O B 661      43.221    7.748   36.329  1.00 28.66      B    O
ATOM   4315  OH2 H2O B 662      22.617   12.389   63.256  1.00 55.06      B    O
ATOM   4316  OH2 H2O B 663      35.213  -11.278   56.607  1.00 52.17      B    O
ATOM   4317  OH2 H2O B 664      55.041    1.082   39.411  1.00 44.42      B    O
ATOM   4318  OH2 H2O B 665      31.480   20.261   56.834  1.00 59.71      B    O
ATOM   4319  OH2 H2O B 666      26.242   -1.552   62.186  1.00 46.80      B    O
ATOM   4320  OH2 H2O B 667      37.417   22.123   56.249  1.00 33.68      B    O
ATOM   4321  OH2 H2O B 668      51.402   -0.436   60.313  1.00 54.61      B    O
ATOM   4322  OH2 H2O B 669      33.891   21.763   57.847  1.00 39.96      B    O
ATOM   4323  OH2 H2O B 670      23.282   -1.093   62.330  1.00 57.85      B    O
ATOM   4324  OH2 H2O B 671      26.628   14.956   53.150  1.00 28.46      B    O
ATOM   4325  OH2 H2O B 672      34.875   20.279   40.564  1.00 44.06      B    O
ATOM   4326  OH2 H2O B 673      62.253    1.859   47.908  1.00 33.88      B    O
ATOM   4327  OH2 H2O B 674      43.294   22.184   55.668  1.00 36.86      B    O
ATOM   4328  OH2 H2O B 675      25.885   -1.756   48.429  1.00 23.16      B    O
ATOM   4329  OH2 H2O B 676      60.177   18.499   41.513  1.00 35.60      B    O
ATOM   4330  OH2 H2O B 677      34.145    7.926   45.870  1.00 29.03      B    O
ATOM   4331  OH2 H2O B 678      23.201    4.398   53.121  1.00 41.98      B    O
ATOM   4332  OH2 H2O B 679      43.423    1.651   43.565  1.00 52.43      B    O
ATOM   4333  OH2 H2O B 680      60.716    6.703   28.316  1.00 64.52      B    O
ATOM   4334  OH2 H2O B 681      22.302    3.980   50.398  1.00 35.96      B    O
ATOM   4335  OH2 H2O B 682      58.231   19.905   40.446  1.00 41.64      B    O
ATOM   4336  OH2 H2O B 683      47.875    5.833   40.180  1.00 32.00      B    O
ATOM   4337  OH2 H2O B 684      43.239   -2.194   52.585  1.00 23.70      B    O
ATOM   4338  OH2 H2O B 685      24.105    0.227   52.855  1.00 11.58      B    O
ATOM   4339  OH2 H2O B 686      45.923   -1.112   69.163  1.00 62.32      B    O
ATOM   4340  OH2 H2O B 687      26.837   -3.551   64.056  1.00 34.69      B    O
ATOM   4341  OH2 H2O B 688      62.564    9.488   48.424  1.00 45.23      B    O
ATOM   4342  OH2 H2O B 689      23.803   -2.062   46.685  1.00 33.34      B    O
ATOM   4343  OH2 H2O B 690      33.359   17.466   26.898  1.00 27.16      B    O
ATOM   4344  OH2 H2O B 691      47.730   24.162   40.279  1.00 55.12      B    O
ATOM   4345  OH2 H2O B 692      41.107    0.866   41.565  1.00 23.92      B    O
ATOM   4346  OH2 H2O B 693      45.092   -0.643   47.617  1.00 24.59      B    O
ATOM   4347  OH2 H2O B 694      46.068   22.489   42.256  1.00 54.01      B    O
ATOM   4348  OH2 H2O B 695      19.161   12.689   66.542  1.00 52.53      B    O
ATOM   4349  OH2 H2O B 696      59.738    5.858   58.491  1.00 45.63      B    O
ATOM   4350  OH2 H2O B 697      39.783    6.909   68.053  1.00 55.70      B    O
ATOM   4351  OH2 H2O B 698      53.547   10.968   25.400  1.00 33.68      B    O
ATOM   4352  OH2 H2O B 699      23.636    1.084   60.258  1.00 35.59      B    O
ATOM   4353  OH2 H2O B 700      35.230   11.808   68.167  1.00 61.25      B    O
ATOM   4354  OH2 H2O B 701      62.191   10.557   36.290  1.00 55.55      B    O
END
```

Figure 13

```
CRYST1   57.884   44.625  121.969  90.00  89.88  90.00 P21           1
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.017276  0.000000 -0.000036        0.00000
SCALE2      0.000000  0.022409  0.000000        0.00000
SCALE3      0.000000  0.000000  0.008199        0.00000
ATOM      1  CB  TRP A 238      18.838  -5.505  28.111  1.00 61.83           C
ATOM      2  CG  TRP A 238      18.525  -6.105  26.773  1.00 61.45           C
ATOM      3  CD2 TRP A 238      19.145  -5.778  25.524  1.00 61.34           C
ATOM      4  CE2 TRP A 238      18.536  -6.579  24.534  1.00 61.04           C
ATOM      5  CE3 TRP A 238      20.157  -4.884  25.146  1.00 61.56           C
ATOM      6  CD1 TRP A 238      17.595  -7.065  26.500  1.00 61.19           C
ATOM      7  NE1 TRP A 238      17.595  -7.356  25.157  1.00 61.67           N
ATOM      8  CZ2 TRP A 238      18.905  -6.515  23.187  1.00 61.60           C
ATOM      9  CZ3 TRP A 238      20.523  -4.819  23.805  1.00 61.26           C
ATOM     10  CH2 TRP A 238      19.897  -5.631  22.841  1.00 61.51           C
ATOM     11  C   TRP A 238      20.133  -5.660  30.233  1.00 60.64           C
ATOM     12  O   TRP A 238      20.808  -4.646  30.043  1.00 60.44           O
ATOM     13  N   TRP A 238      18.679  -7.563  29.483  1.00 61.65           N
ATOM     14  CA  TRP A 238      19.578  -6.454  29.056  1.00 61.02           C
ATOM     15  N   GLU A 239      19.842  -6.113  31.448  1.00 59.66           N
ATOM     16  CA  GLU A 239      20.348  -5.442  32.640  1.00 59.06           C
ATOM     17  CB  GLU A 239      19.641  -5.959  33.898  1.00 60.29           C
ATOM     18  CG  GLU A 239      18.197  -5.527  34.067  1.00 63.14           C
ATOM     19  CD  GLU A 239      17.307  -5.945  32.913  1.00 64.85           C
ATOM     20  OE1 GLU A 239      17.427  -7.101  32.449  1.00 65.20           O
ATOM     21  OE2 GLU A 239      16.475  -5.117  32.480  1.00 65.32           O
ATOM     22  C   GLU A 239      21.839  -5.745  32.750  1.00 57.45           C
ATOM     23  O   GLU A 239      22.273  -6.857  32.462  1.00 56.96           O
ATOM     24  N   VAL A 240      22.625  -4.754  33.149  1.00 55.94           N
ATOM     25  CA  VAL A 240      24.058  -4.957  33.307  1.00 55.34           C
ATOM     26  CB  VAL A 240      24.865  -4.443  32.081  1.00 55.03           C
ATOM     27  CG1 VAL A 240      24.444  -5.198  30.836  1.00 55.76           C
ATOM     28  CG2 VAL A 240      24.669  -2.941  31.906  1.00 54.21           C
ATOM     29  C   VAL A 240      24.524  -4.225  34.552  1.00 54.68           C
ATOM     30  O   VAL A 240      23.979  -3.183  34.910  1.00 54.89           O
ATOM     31  N   PRO A 241      25.532  -4.773  35.242  1.00 53.98           N
ATOM     32  CD  PRO A 241      26.107  -6.118  35.066  1.00 54.68           C
ATOM     33  CA  PRO A 241      26.048  -4.139  36.456  1.00 53.79           C
ATOM     34  CB  PRO A 241      27.094  -5.139  36.946  1.00 53.40           C
ATOM     35  CG  PRO A 241      26.543  -6.454  36.470  1.00 54.50           C
ATOM     36  C   PRO A 241      26.651  -2.764  36.179  1.00 53.41           C
ATOM     37  O   PRO A 241      27.549  -2.626  35.345  1.00 52.93           O
ATOM     38  N   ARG A 242      26.147  -1.752  36.877  1.00 52.73           N
ATOM     39  CA  ARG A 242      26.647  -0.390  36.726  1.00 53.26           C
ATOM     40  CB  ARG A 242      26.290   0.434  37.959  1.00 55.18           C
ATOM     41  CG  ARG A 242      26.962   1.794  38.016  1.00 56.80           C
ATOM     42  CD  ARG A 242      26.295   2.747  37.062  1.00 59.03           C
ATOM     43  NE  ARG A 242      24.860   2.822  37.323  1.00 61.56           N
ATOM     44  CZ  ARG A 242      24.335   3.212  38.478  1.00 60.99           C
```

Figure 14

```
ATOM    45  NH1 ARG A 242      25.129   3.566  39.479  1.00 60.60           N
ATOM    46  NH2 ARG A 242      23.018   3.241  38.635  1.00 62.49           N
ATOM    47  C   ARG A 242      28.162  -0.417  36.586  1.00 53.04           C
ATOM    48  O   ARG A 242      28.741   0.260  35.733  1.00 52.44           O
ATOM    49  N   GLU A 243      28.786  -1.210  37.449  1.00 52.23           N
ATOM    50  CA  GLU A 243      30.230  -1.360  37.487  1.00 52.19           C
ATOM    51  CB  GLU A 243      30.598  -2.476  38.473  1.00 54.28           C
ATOM    52  CG  GLU A 243      30.229  -2.175  39.931  1.00 56.90           C
ATOM    53  CD  GLU A 243      28.742  -1.907  40.146  1.00 57.79           C
ATOM    54  OE1 GLU A 243      27.921  -2.799  39.842  1.00 58.40           O
ATOM    55  OE2 GLU A 243      28.393  -0.804  40.625  1.00 58.63           O
ATOM    56  C   GLU A 243      30.865  -1.633  36.124  1.00 50.46           C
ATOM    57  O   GLU A 243      31.993  -1.217  35.876  1.00 49.83           O
ATOM    58  N   THR A 244      30.145  -2.320  35.239  1.00 49.35           N
ATOM    59  CA  THR A 244      30.680  -2.630  33.912  1.00 49.12           C
ATOM    60  CB  THR A 244      29.879  -3.750  33.210  1.00 48.55           C
ATOM    61  OG1 THR A 244      28.548  -3.297  32.934  1.00 49.87           O
ATOM    62  CG2 THR A 244      29.820  -4.984  34.074  1.00 47.66           C
ATOM    63  C   THR A 244      30.691  -1.414  32.986  1.00 49.16           C
ATOM    64  O   THR A 244      30.887  -1.547  31.778  1.00 49.44           O
ATOM    65  N   LEU A 245      30.481  -0.228  33.548  1.00 48.57           N
ATOM    66  CA  LEU A 245      30.474   0.983  32.747  1.00 47.75           C
ATOM    67  CB  LEU A 245      29.033   1.406  32.423  1.00 48.68           C
ATOM    68  CG  LEU A 245      28.229   0.547  31.445  1.00 49.28           C
ATOM    69  CD1 LEU A 245      27.790  -0.735  32.127  1.00 50.38           C
ATOM    70  CD2 LEU A 245      27.013   1.320  30.979  1.00 50.64           C
ATOM    71  C   LEU A 245      31.188   2.145  33.420  1.00 46.98           C
ATOM    72  O   LEU A 245      31.117   2.324  34.640  1.00 46.54           O
ATOM    73  N   LYS A 246      31.881   2.935  32.608  1.00 45.00           N
ATOM    74  CA  LYS A 246      32.579   4.108  33.096  1.00 44.30           C
ATOM    75  CB  LYS A 246      34.098   3.919  33.026  1.00 45.18           C
ATOM    76  CG  LYS A 246      34.876   5.182  33.403  1.00 44.33           C
ATOM    77  CD  LYS A 246      36.352   4.908  33.673  1.00 44.98           C
ATOM    78  CE  LYS A 246      37.043   4.284  32.481  1.00 44.17           C
ATOM    79  NZ  LYS A 246      38.481   4.041  32.791  1.00 45.70           N
ATOM    80  C   LYS A 246      32.181   5.317  32.260  1.00 44.63           C
ATOM    81  O   LYS A 246      32.518   5.402  31.079  1.00 42.95           O
ATOM    82  N   LEU A 247      31.438   6.237  32.867  1.00 45.11           N
ATOM    83  CA  LEU A 247      31.033   7.448  32.177  1.00 45.97           C
ATOM    84  CB  LEU A 247      29.867   8.124  32.907  1.00 45.83           C
ATOM    85  CG  LEU A 247      28.473   7.571  32.570  1.00 44.27           C
ATOM    86  CD1 LEU A 247      28.479   6.047  32.579  1.00 44.36           C
ATOM    87  CD2 LEU A 247      27.463   8.116  33.560  1.00 44.96           C
ATOM    88  C   LEU A 247      32.268   8.333  32.164  1.00 46.94           C
ATOM    89  O   LEU A 247      32.826   8.668  33.211  1.00 47.00           O
ATOM    90  N   VAL A 248      32.707   8.683  30.963  1.00 46.42           N
ATOM    91  CA  VAL A 248      33.898   9.497  30.799  1.00 46.23           C
ATOM    92  CB  VAL A 248      34.721   8.993  29.590  1.00 46.05           C
ATOM    93  CG1 VAL A 248      36.012   9.788  29.456  1.00 45.40           C
ATOM    94  CG2 VAL A 248      35.014   7.519  29.757  1.00 46.73           C
ATOM    95  C   VAL A 248      33.610  10.978  30.608  1.00 46.18           C
ATOM    96  O   VAL A 248      34.172  11.827  31.307  1.00 44.22           O
ATOM    97  N   GLU A 249      32.722  11.282  29.666  1.00 45.75           N
ATOM    98  CA  GLU A 249      32.398  12.666  29.346  1.00 45.81           C
ATOM    99  CB  GLU A 249      33.132  13.054  28.066  1.00 46.80           C
ATOM   100  CG  GLU A 249      33.032  14.510  27.678  1.00 48.28           C
ATOM   101  CD  GLU A 249      33.669  14.760  26.328  1.00 49.20           C
ATOM   102  OE1 GLU A 249      34.590  13.997  25.958  1.00 46.97           O
ATOM   103  OE2 GLU A 249      33.257  15.717  25.641  1.00 51.89           O
ATOM   104  C   GLU A 249      30.906  12.899  29.149  1.00 45.54           C
```

Figure 14

| ATOM | 105 | O | GLU | A | 249 | 30.207 | 12.052 | 28.591 | 1.00 | 44.52 | O |
| ATOM | 106 | N | ARG | A | 250 | 30.429 | 14.057 | 29.595 | 1.00 | 44.35 | N |
| ATOM | 107 | CA | ARG | A | 250 | 29.024 | 14.392 | 29.443 | 1.00 | 45.17 | C |
| ATOM | 108 | CB | ARG | A | 250 | 28.555 | 15.298 | 30.584 | 1.00 | 44.03 | C |
| ATOM | 109 | CG | ARG | A | 250 | 27.047 | 15.507 | 30.577 | 1.00 | 44.79 | C |
| ATOM | 110 | CD | ARG | A | 250 | 26.558 | 16.198 | 31.827 | 1.00 | 43.82 | C |
| ATOM | 111 | NE | ARG | A | 250 | 26.993 | 17.585 | 31.886 | 1.00 | 47.71 | N |
| ATOM | 112 | CZ | ARG | A | 250 | 26.649 | 18.427 | 32.852 | 1.00 | 47.98 | C |
| ATOM | 113 | NH1 | ARG | A | 250 | 25.869 | 18.016 | 33.841 | 1.00 | 49.60 | N |
| ATOM | 114 | NH2 | ARG | A | 250 | 27.068 | 19.683 | 32.823 | 1.00 | 50.23 | N |
| ATOM | 115 | C | ARG | A | 250 | 28.796 | 15.081 | 28.099 | 1.00 | 44.02 | C |
| ATOM | 116 | O | ARG | A | 250 | 29.355 | 16.143 | 27.831 | 1.00 | 45.14 | O |
| ATOM | 117 | N | LEU | A | 251 | 27.973 | 14.467 | 27.255 | 1.00 | 44.05 | N |
| ATOM | 118 | CA | LEU | A | 251 | 27.677 | 15.011 | 25.935 | 1.00 | 41.58 | C |
| ATOM | 119 | CB | LEU | A | 251 | 27.296 | 13.875 | 24.985 | 1.00 | 40.87 | C |
| ATOM | 120 | CG | LEU | A | 251 | 28.323 | 12.750 | 24.848 | 1.00 | 38.58 | C |
| ATOM | 121 | CD1 | LEU | A | 251 | 27.742 | 11.604 | 24.050 | 1.00 | 36.76 | C |
| ATOM | 122 | CD2 | LEU | A | 251 | 29.589 | 13.279 | 24.196 | 1.00 | 40.26 | C |
| ATOM | 123 | C | LEU | A | 251 | 26.551 | 16.045 | 26.004 | 1.00 | 42.28 | C |
| ATOM | 124 | O | LEU | A | 251 | 26.470 | 16.950 | 25.169 | 1.00 | 41.26 | O |
| ATOM | 125 | N | GLY | A | 252 | 25.687 | 15.916 | 27.007 | 1.00 | 41.25 | N |
| ATOM | 126 | CA | GLY | A | 252 | 24.595 | 16.859 | 27.148 | 1.00 | 39.25 | C |
| ATOM | 127 | C | GLY | A | 252 | 23.801 | 16.702 | 28.432 | 1.00 | 39.83 | C |
| ATOM | 128 | O | GLY | A | 252 | 23.721 | 15.615 | 29.002 | 1.00 | 37.73 | O |
| ATOM | 129 | N | ALA | A | 253 | 23.211 | 17.803 | 28.886 | 1.00 | 40.09 | N |
| ATOM | 130 | CA | ALA | A | 253 | 22.406 | 17.802 | 30.095 | 1.00 | 40.92 | C |
| ATOM | 131 | CB | ALA | A | 253 | 23.176 | 18.468 | 31.250 | 1.00 | 40.71 | C |
| ATOM | 132 | C | ALA | A | 253 | 21.115 | 18.560 | 29.814 | 1.00 | 41.67 | C |
| ATOM | 133 | O | ALA | A | 253 | 21.144 | 19.644 | 29.226 | 1.00 | 42.50 | O |
| ATOM | 134 | N | GLY | A | 254 | 19.989 | 17.987 | 30.233 | 1.00 | 41.35 | N |
| ATOM | 135 | CA | GLY | A | 254 | 18.706 | 18.627 | 30.017 | 1.00 | 41.63 | C |
| ATOM | 136 | C | GLY | A | 254 | 17.629 | 18.303 | 31.042 | 1.00 | 42.64 | C |
| ATOM | 137 | O | GLY | A | 254 | 17.771 | 17.407 | 31.874 | 1.00 | 42.41 | O |
| ATOM | 138 | N | GLN | A | 255 | 16.531 | 19.043 | 30.942 | 1.00 | 42.90 | N |
| ATOM | 139 | CA | GLN | A | 255 | 15.367 | 18.924 | 31.817 | 1.00 | 44.04 | C |
| ATOM | 140 | CB | GLN | A | 255 | 14.144 | 19.442 | 31.049 | 1.00 | 46.26 | C |
| ATOM | 141 | CG | GLN | A | 255 | 12.834 | 19.410 | 31.801 | 1.00 | 51.85 | C |
| ATOM | 142 | CD | GLN | A | 255 | 11.715 | 20.093 | 31.024 | 1.00 | 53.61 | C |
| ATOM | 143 | OE1 | GLN | A | 255 | 11.749 | 21.307 | 30.805 | 1.00 | 55.27 | O |
| ATOM | 144 | NE2 | GLN | A | 255 | 10.724 | 19.313 | 30.596 | 1.00 | 54.17 | N |
| ATOM | 145 | C | GLN | A | 255 | 15.065 | 17.542 | 32.418 | 1.00 | 42.48 | C |
| ATOM | 146 | O | GLN | A | 255 | 14.710 | 17.446 | 33.596 | 1.00 | 44.25 | O |
| ATOM | 147 | N | PHE | A | 256 | 15.198 | 16.484 | 31.624 | 1.00 | 40.55 | N |
| ATOM | 148 | CA | PHE | A | 256 | 14.902 | 15.124 | 32.092 | 1.00 | 39.86 | C |
| ATOM | 149 | CB | PHE | A | 256 | 14.051 | 14.360 | 31.064 | 1.00 | 39.32 | C |
| ATOM | 150 | CG | PHE | A | 256 | 12.651 | 14.881 | 30.894 | 1.00 | 39.06 | C |
| ATOM | 151 | CD1 | PHE | A | 256 | 12.143 | 15.874 | 31.724 | 1.00 | 39.92 | C |
| ATOM | 152 | CD2 | PHE | A | 256 | 11.833 | 14.360 | 29.891 | 1.00 | 40.73 | C |
| ATOM | 153 | CE1 | PHE | A | 256 | 10.839 | 16.344 | 31.560 | 1.00 | 41.73 | C |
| ATOM | 154 | CE2 | PHE | A | 256 | 10.524 | 14.824 | 29.717 | 1.00 | 41.72 | C |
| ATOM | 155 | CZ | PHE | A | 256 | 10.028 | 15.817 | 30.552 | 1.00 | 40.53 | C |
| ATOM | 156 | C | PHE | A | 256 | 16.122 | 14.258 | 32.377 | 1.00 | 38.91 | C |
| ATOM | 157 | O | PHE | A | 256 | 15.980 | 13.077 | 32.699 | 1.00 | 37.85 | O |
| ATOM | 158 | N | GLY | A | 257 | 17.318 | 14.810 | 32.227 | 1.00 | 39.26 | N |
| ATOM | 159 | CA | GLY | A | 257 | 18.497 | 13.997 | 32.473 | 1.00 | 38.92 | C |
| ATOM | 160 | C | GLY | A | 257 | 19.707 | 14.432 | 31.675 | 1.00 | 38.59 | C |
| ATOM | 161 | O | GLY | A | 257 | 19.797 | 15.589 | 31.257 | 1.00 | 36.75 | O |
| ATOM | 162 | N | GLU | A | 258 | 20.630 | 13.496 | 31.455 | 1.00 | 38.66 | N |
| ATOM | 163 | CA | GLU | A | 258 | 21.864 | 13.778 | 30.730 | 1.00 | 38.89 | C |
| ATOM | 164 | CB | GLU | A | 258 | 22.997 | 14.041 | 31.727 | 1.00 | 40.32 | C |

Figure 14

| ATOM | 165 | CG | GLU A 258 | 22.633 | 14.994 | 32.854 | 1.00 | 44.85 | C |
| ATOM | 166 | CD | GLU A 258 | 23.769 | 15.181 | 33.850 | 1.00 | 47.11 | C |
| ATOM | 167 | OE1 | GLU A 258 | 24.423 | 14.176 | 34.203 | 1.00 | 49.01 | O |
| ATOM | 168 | OE2 | GLU A 258 | 23.996 | 16.329 | 34.288 | 1.00 | 48.76 | O |
| ATOM | 169 | C | GLU A 258 | 22.278 | 12.624 | 29.826 | 1.00 | 37.70 | C |
| ATOM | 170 | O | GLU A 258 | 21.739 | 11.521 | 29.915 | 1.00 | 37.54 | O |
| ATOM | 171 | N | VAL A 259 | 23.250 | 12.896 | 28.960 | 1.00 | 36.86 | N |
| ATOM | 172 | CA | VAL A 259 | 23.792 | 11.897 | 28.049 | 1.00 | 36.90 | C |
| ATOM | 173 | CB | VAL A 259 | 23.425 | 12.196 | 26.588 | 1.00 | 35.84 | C |
| ATOM | 174 | CG1 | VAL A 259 | 24.047 | 11.149 | 25.683 | 1.00 | 36.75 | C |
| ATOM | 175 | CG2 | VAL A 259 | 21.911 | 12.214 | 26.420 | 1.00 | 36.98 | C |
| ATOM | 176 | C | VAL A 259 | 25.312 | 11.946 | 28.166 | 1.00 | 36.87 | C |
| ATOM | 177 | O | VAL A 259 | 25.895 | 13.028 | 28.145 | 1.00 | 35.52 | O |
| ATOM | 178 | N | TRP A 260 | 25.946 | 10.780 | 28.278 | 1.00 | 38.01 | N |
| ATOM | 179 | CA | TRP A 260 | 27.404 | 10.707 | 28.407 | 1.00 | 38.65 | C |
| ATOM | 180 | CB | TRP A 260 | 27.823 | 10.258 | 29.818 | 1.00 | 37.94 | C |
| ATOM | 181 | CG | TRP A 260 | 27.521 | 11.193 | 30.931 | 1.00 | 39.84 | C |
| ATOM | 182 | CD2 | TRP A 260 | 28.474 | 11.827 | 31.799 | 1.00 | 40.56 | C |
| ATOM | 183 | CE2 | TRP A 260 | 27.742 | 12.572 | 32.748 | 1.00 | 41.31 | C |
| ATOM | 184 | CE3 | TRP A 260 | 29.876 | 11.835 | 31.867 | 1.00 | 42.08 | C |
| ATOM | 185 | CD1 | TRP A 260 | 26.288 | 11.572 | 31.373 | 1.00 | 38.65 | C |
| ATOM | 186 | NE1 | TRP A 260 | 26.411 | 12.400 | 32.464 | 1.00 | 40.71 | N |
| ATOM | 187 | CZ2 | TRP A 260 | 28.363 | 13.320 | 33.757 | 1.00 | 41.89 | C |
| ATOM | 188 | CZ3 | TRP A 260 | 30.496 | 12.581 | 32.869 | 1.00 | 40.99 | C |
| ATOM | 189 | CH2 | TRP A 260 | 29.736 | 13.313 | 33.801 | 1.00 | 42.08 | C |
| ATOM | 190 | C | TRP A 260 | 28.035 | 9.717 | 27.445 | 1.00 | 38.32 | C |
| ATOM | 191 | O | TRP A 260 | 27.377 | 8.807 | 26.937 | 1.00 | 38.94 | O |
| ATOM | 192 | N | MET A 261 | 29.328 | 9.909 | 27.213 | 1.00 | 38.30 | N |
| ATOM | 193 | CA | MET A 261 | 30.110 | 8.998 | 26.402 | 1.00 | 38.74 | C |
| ATOM | 194 | CB | MET A 261 | 31.046 | 9.749 | 25.458 | 1.00 | 40.48 | C |
| ATOM | 195 | CG | MET A 261 | 32.104 | 8.871 | 24.786 | 1.00 | 41.42 | C |
| ATOM | 196 | SD | MET A 261 | 33.456 | 8.369 | 25.909 | 1.00 | 43.64 | S |
| ATOM | 197 | CE | MET A 261 | 34.069 | 9.968 | 26.393 | 1.00 | 43.83 | C |
| ATOM | 198 | C | MET A 261 | 30.920 | 8.257 | 27.451 | 1.00 | 39.87 | C |
| ATOM | 199 | O | MET A 261 | 31.414 | 8.853 | 28.403 | 1.00 | 38.68 | O |
| ATOM | 200 | N | GLY A 262 | 31.037 | 6.952 | 27.296 | 1.00 | 41.70 | N |
| ATOM | 201 | CA | GLY A 262 | 31.798 | 6.189 | 28.256 | 1.00 | 43.47 | C |
| ATOM | 202 | C | GLY A 262 | 32.147 | 4.886 | 27.603 | 1.00 | 45.50 | C |
| ATOM | 203 | O | GLY A 262 | 31.846 | 4.681 | 26.427 | 1.00 | 46.78 | O |
| ATOM | 204 | N | TYR A 263 | 32.790 | 4.002 | 28.350 | 1.00 | 46.55 | N |
| ATOM | 205 | CA | TYR A 263 | 33.153 | 2.717 | 27.795 | 1.00 | 47.58 | C |
| ATOM | 206 | CB | TYR A 263 | 34.667 | 2.538 | 27.821 | 1.00 | 47.10 | C |
| ATOM | 207 | CG | TYR A 263 | 35.356 | 3.543 | 26.938 | 1.00 | 45.02 | C |
| ATOM | 208 | CD1 | TYR A 263 | 35.487 | 4.877 | 27.337 | 1.00 | 45.22 | C |
| ATOM | 209 | CE1 | TYR A 263 | 36.050 | 5.823 | 26.500 | 1.00 | 44.23 | C |
| ATOM | 210 | CD2 | TYR A 263 | 35.813 | 3.182 | 25.675 | 1.00 | 43.84 | C |
| ATOM | 211 | CE2 | TYR A 263 | 36.377 | 4.120 | 24.826 | 1.00 | 43.79 | C |
| ATOM | 212 | CZ | TYR A 263 | 36.493 | 5.437 | 25.241 | 1.00 | 43.76 | C |
| ATOM | 213 | OH | TYR A 263 | 37.057 | 6.369 | 24.405 | 1.00 | 43.10 | O |
| ATOM | 214 | C | TYR A 263 | 32.456 | 1.606 | 28.540 | 1.00 | 48.84 | C |
| ATOM | 215 | O | TYR A 263 | 32.266 | 1.674 | 29.755 | 1.00 | 47.70 | O |
| ATOM | 216 | N | TYR A 264 | 32.070 | 0.591 | 27.781 | 1.00 | 50.20 | N |
| ATOM | 217 | CA | TYR A 264 | 31.356 | -0.560 | 28.295 | 1.00 | 52.65 | C |
| ATOM | 218 | CB | TYR A 264 | 30.092 | -0.755 | 27.453 | 1.00 | 53.53 | C |
| ATOM | 219 | CG | TYR A 264 | 29.288 | -1.995 | 27.749 | 1.00 | 56.76 | C |
| ATOM | 220 | CD1 | TYR A 264 | 28.860 | -2.290 | 29.047 | 1.00 | 56.24 | C |
| ATOM | 221 | CE1 | TYR A 264 | 28.077 | -3.418 | 29.303 | 1.00 | 57.72 | C |
| ATOM | 222 | CD2 | TYR A 264 | 28.915 | -2.860 | 26.715 | 1.00 | 56.71 | C |
| ATOM | 223 | CE2 | TYR A 264 | 28.136 | -3.986 | 26.961 | 1.00 | 57.41 | C |
| ATOM | 224 | CZ | TYR A 264 | 27.720 | -4.259 | 28.253 | 1.00 | 57.60 | C |

Figure 14

| | | | | | | | | | | |
|---|---|---|---|---|---|---|---|---|---|---|
| ATOM | 225 | OH | TYR | A | 264 | 26.952 | -5.376 | 28.485 | 1.00 60.44 | O |
| ATOM | 226 | C | TYR | A | 264 | 32.268 | -1.771 | 28.213 | 1.00 53.26 | C |
| ATOM | 227 | O | TYR | A | 264 | 32.705 | -2.159 | 27.128 | 1.00 51.36 | O |
| ATOM | 228 | N | ASN | A | 265 | 32.564 | -2.347 | 29.374 | 1.00 55.09 | N |
| ATOM | 229 | CA | ASN | A | 265 | 33.437 | -3.513 | 29.472 | 1.00 56.89 | C |
| ATOM | 230 | CB | ASN | A | 265 | 32.929 | -4.653 | 28.584 | 1.00 58.08 | C |
| ATOM | 231 | CG | ASN | A | 265 | 31.544 | -5.121 | 28.978 | 1.00 60.16 | C |
| ATOM | 232 | OD1 | ASN | A | 265 | 31.269 | -5.366 | 30.155 | 1.00 61.22 | O |
| ATOM | 233 | ND2 | ASN | A | 265 | 30.663 | -5.261 | 27.990 | 1.00 60.96 | N |
| ATOM | 234 | C | ASN | A | 265 | 34.880 | -3.180 | 29.101 | 1.00 57.54 | C |
| ATOM | 235 | O | ASN | A | 265 | 35.596 | -4.006 | 28.528 | 1.00 57.99 | O |
| ATOM | 236 | N | GLY | A | 266 | 35.296 | -1.957 | 29.409 | 1.00 57.57 | N |
| ATOM | 237 | CA | GLY | A | 266 | 36.662 | -1.561 | 29.135 | 1.00 57.77 | C |
| ATOM | 238 | C | GLY | A | 266 | 36.995 | -0.896 | 27.814 | 1.00 58.88 | C |
| ATOM | 239 | O | GLY | A | 266 | 37.534 | 0.210 | 27.815 | 1.00 60.23 | O |
| ATOM | 240 | N | HIS | A | 267 | 36.681 | -1.534 | 26.688 | 1.00 58.27 | N |
| ATOM | 241 | CA | HIS | A | 267 | 37.034 | -0.946 | 25.394 | 1.00 57.74 | C |
| ATOM | 242 | CB | HIS | A | 267 | 38.050 | -1.845 | 24.680 | 1.00 59.37 | C |
| ATOM | 243 | CG | HIS | A | 267 | 39.360 | -1.961 | 25.394 | 1.00 62.05 | C |
| ATOM | 244 | CD2 | HIS | A | 267 | 40.622 | -1.673 | 24.993 | 1.00 62.21 | C |
| ATOM | 245 | ND1 | HIS | A | 267 | 39.465 | -2.423 | 26.689 | 1.00 62.81 | N |
| ATOM | 246 | CE1 | HIS | A | 267 | 40.734 | -2.413 | 27.056 | 1.00 63.09 | C |
| ATOM | 247 | NE2 | HIS | A | 267 | 41.457 | -1.963 | 26.045 | 1.00 63.53 | N |
| ATOM | 248 | C | HIS | A | 267 | 35.916 | -0.604 | 24.411 | 1.00 56.23 | C |
| ATOM | 249 | O | HIS | A | 267 | 36.197 | -0.292 | 23.253 | 1.00 54.77 | O |
| ATOM | 250 | N | THR | A | 268 | 34.661 | -0.658 | 24.844 | 1.00 54.42 | N |
| ATOM | 251 | CA | THR | A | 268 | 33.566 | -0.329 | 23.933 | 1.00 52.80 | C |
| ATOM | 252 | CB | THR | A | 268 | 32.448 | -1.390 | 23.981 | 1.00 52.67 | C |
| ATOM | 253 | OG1 | THR | A | 268 | 32.937 | -2.618 | 23.428 | 1.00 51.69 | O |
| ATOM | 254 | CG2 | THR | A | 268 | 31.238 | -0.934 | 23.177 | 1.00 54.79 | C |
| ATOM | 255 | C | THR | A | 268 | 32.979 | 1.040 | 24.239 | 1.00 51.28 | C |
| ATOM | 256 | O | THR | A | 268 | 32.355 | 1.247 | 25.283 | 1.00 51.44 | O |
| ATOM | 257 | N | LYS | A | 269 | 33.191 | 1.975 | 23.320 | 1.00 49.25 | N |
| ATOM | 258 | CA | LYS | A | 269 | 32.693 | 3.330 | 23.475 | 1.00 46.02 | C |
| ATOM | 259 | CB | LYS | A | 269 | 33.321 | 4.239 | 22.417 | 1.00 46.33 | C |
| ATOM | 260 | CG | LYS | A | 269 | 33.401 | 5.701 | 22.828 | 1.00 46.37 | C |
| ATOM | 261 | CD | LYS | A | 269 | 34.334 | 6.488 | 21.904 | 1.00 46.48 | C |
| ATOM | 262 | CE | LYS | A | 269 | 34.487 | 7.927 | 22.378 | 1.00 47.29 | C |
| ATOM | 263 | NZ | LYS | A | 269 | 35.283 | 8.767 | 21.437 | 1.00 48.31 | N |
| ATOM | 264 | C | LYS | A | 269 | 31.176 | 3.293 | 23.335 | 1.00 44.52 | C |
| ATOM | 265 | O | LYS | A | 269 | 30.641 | 2.671 | 22.416 | 1.00 44.50 | O |
| ATOM | 266 | N | VAL | A | 270 | 30.483 | 3.949 | 24.255 | 1.00 41.45 | N |
| ATOM | 267 | CA | VAL | A | 270 | 29.030 | 3.946 | 24.228 | 1.00 39.11 | C |
| ATOM | 268 | CB | VAL | A | 270 | 28.448 | 2.870 | 25.184 | 1.00 38.30 | C |
| ATOM | 269 | CG1 | VAL | A | 270 | 28.839 | 1.480 | 24.725 | 1.00 38.67 | C |
| ATOM | 270 | CG2 | VAL | A | 270 | 28.951 | 3.118 | 26.597 | 1.00 37.78 | C |
| ATOM | 271 | C | VAL | A | 270 | 28.441 | 5.275 | 24.651 | 1.00 37.97 | C |
| ATOM | 272 | O | VAL | A | 270 | 29.125 | 6.128 | 25.211 | 1.00 37.67 | O |
| ATOM | 273 | N | ALA | A | 271 | 27.157 | 5.438 | 24.361 | 1.00 37.90 | N |
| ATOM | 274 | CA | ALA | A | 271 | 26.425 | 6.629 | 24.754 | 1.00 36.20 | C |
| ATOM | 275 | CB | ALA | A | 271 | 25.592 | 7.129 | 23.612 | 1.00 37.40 | C |
| ATOM | 276 | C | ALA | A | 271 | 25.525 | 6.143 | 25.886 | 1.00 35.52 | C |
| ATOM | 277 | O | ALA | A | 271 | 24.918 | 5.075 | 25.778 | 1.00 35.23 | O |
| ATOM | 278 | N | VAL | A | 272 | 25.450 | 6.915 | 26.964 | 1.00 35.63 | N |
| ATOM | 279 | CA | VAL | A | 272 | 24.643 | 6.539 | 28.116 | 1.00 35.91 | C |
| ATOM | 280 | CB | VAL | A | 272 | 25.534 | 6.221 | 29.346 | 1.00 36.61 | C |
| ATOM | 281 | CG1 | VAL | A | 272 | 24.664 | 5.761 | 30.519 | 1.00 35.37 | C |
| ATOM | 282 | CG2 | VAL | A | 272 | 26.577 | 5.172 | 28.988 | 1.00 36.93 | C |
| ATOM | 283 | C | VAL | A | 272 | 23.702 | 7.667 | 28.506 | 1.00 35.85 | C |
| ATOM | 284 | O | VAL | A | 272 | 24.149 | 8.769 | 28.822 | 1.00 38.34 | O |

Figure 14

```
ATOM    285  N   LYS A 273      22.400    7.400   28.477  1.00 35.81           N
ATOM    286  CA  LYS A 273      21.421    8.412   28.859  1.00 34.60           C
ATOM    287  CB  LYS A 273      20.249    8.457   27.862  1.00 34.16           C
ATOM    288  CG  LYS A 273      19.193    9.509   28.186  1.00 34.37           C
ATOM    289  CD  LYS A 273      18.020    9.500   27.191  1.00 38.27           C
ATOM    290  CE  LYS A 273      18.405   10.043   25.813  1.00 39.94           C
ATOM    291  NZ  LYS A 273      17.268   10.004   24.828  1.00 39.30           N
ATOM    292  C   LYS A 273      20.911    8.051   30.248  1.00 34.54           C
ATOM    293  O   LYS A 273      20.427    6.944   30.473  1.00 31.98           O
ATOM    294  N   SER A 274      21.037    8.991   31.175  1.00 36.02           N
ATOM    295  CA  SER A 274      20.595    8.774   32.539  1.00 40.19           C
ATOM    296  CB  SER A 274      21.722    9.112   33.520  1.00 40.29           C
ATOM    297  OG  SER A 274      22.092   10.477   33.439  1.00 43.30           O
ATOM    298  C   SER A 274      19.368    9.632   32.817  1.00 42.16           C
ATOM    299  O   SER A 274      19.273   10.777   32.364  1.00 45.25           O
ATOM    300  N   LEU A 275      18.422    9.066   33.553  1.00 43.74           N
ATOM    301  CA  LEU A 275      17.178    9.762   33.880  1.00 44.30           C
ATOM    302  CB  LEU A 275      16.036    8.748   34.021  1.00 44.04           C
ATOM    303  CG  LEU A 275      14.739    9.254   34.666  1.00 42.86           C
ATOM    304  CD1 LEU A 275      14.060   10.282   33.761  1.00 41.46           C
ATOM    305  CD2 LEU A 275      13.812    8.077   34.924  1.00 43.96           C
ATOM    306  C   LEU A 275      17.264   10.579   35.158  1.00 44.77           C
ATOM    307  O   LEU A 275      17.738   10.091   36.181  1.00 44.47           O
ATOM    308  N   LYS A 276      16.818   11.829   35.095  1.00 44.71           N
ATOM    309  CA  LYS A 276      16.809   12.663   36.288  1.00 45.61           C
ATOM    310  CB  LYS A 276      16.620   14.140   35.927  1.00 46.74           C
ATOM    311  CG  LYS A 276      16.479   15.049   37.138  1.00 48.02           C
ATOM    312  CD  LYS A 276      16.491   16.518   36.751  1.00 48.76           C
ATOM    313  CE  LYS A 276      17.836   16.940   36.197  1.00 49.52           C
ATOM    314  NZ  LYS A 276      17.858   18.390   35.854  1.00 51.83           N
ATOM    315  C   LYS A 276      15.615   12.157   37.095  1.00 45.20           C
ATOM    316  O   LYS A 276      14.492   12.109   36.586  1.00 42.43           O
ATOM    317  N   GLN A 277      15.865   11.760   38.340  1.00 45.48           N
ATOM    318  CA  GLN A 277      14.815   11.236   39.211  1.00 45.81           C
ATOM    319  CB  GLN A 277      15.389   10.892   40.592  1.00 46.92           C
ATOM    320  CG  GLN A 277      14.474   10.019   41.439  1.00 48.19           C
ATOM    321  CD  GLN A 277      15.195    9.385   42.615  1.00 49.00           C
ATOM    322  OE1 GLN A 277      15.730   10.083   43.477  1.00 49.39           O
ATOM    323  NE2 GLN A 277      15.215    8.055   42.653  1.00 48.32           N
ATOM    324  C   GLN A 277      13.667   12.223   39.360  1.00 44.65           C
ATOM    325  O   GLN A 277      13.883   13.399   39.652  1.00 45.75           O
ATOM    326  N   GLY A 278      12.447   11.740   39.150  1.00 44.16           N
ATOM    327  CA  GLY A 278      11.283   12.603   39.265  1.00 43.65           C
ATOM    328  C   GLY A 278      10.732   13.061   37.924  1.00 43.82           C
ATOM    329  O   GLY A 278       9.533   13.296   37.788  1.00 42.66           O
ATOM    330  N   SER A 279      11.606   13.189   36.929  1.00 43.22           N
ATOM    331  CA  SER A 279      11.204   13.629   35.592  1.00 43.13           C
ATOM    332  CB  SER A 279      12.366   13.449   34.614  1.00 40.90           C
ATOM    333  OG  SER A 279      13.452   14.272   34.991  1.00 43.69           O
ATOM    334  C   SER A 279       9.995   12.861   35.083  1.00 43.39           C
ATOM    335  O   SER A 279       8.984   13.447   34.697  1.00 44.69           O
ATOM    336  N   MET A 280      10.131   11.544   35.069  1.00 43.33           N
ATOM    337  CA  MET A 280       9.080   10.638   34.642  1.00 43.61           C
ATOM    338  CB  MET A 280       9.165   10.387   33.133  1.00 43.43           C
ATOM    339  CG  MET A 280      10.490    9.802   32.653  1.00 42.51           C
ATOM    340  SD  MET A 280      10.724   10.025   30.871  1.00 43.19           S
ATOM    341  CE  MET A 280      10.019    8.575   30.269  1.00 41.93           C
ATOM    342  C   MET A 280       9.363    9.361   35.424  1.00 44.30           C
ATOM    343  O   MET A 280      10.299    9.325   36.224  1.00 42.96           O
ATOM    344  N   SER A 281       8.559    8.326   35.221  1.00 45.30           N
```

Figure 14

| | | | | | | | | | | |
|---|---|---|---|---|---|---|---|---|---|---|
| ATOM | 345 | CA | SER | A | 281 | 8.791 | 7.074 | 35.928 | 1.00 47.08 | C |
| ATOM | 346 | CB | SER | A | 281 | 7.497 | 6.274 | 36.040 | 1.00 46.44 | C |
| ATOM | 347 | OG | SER | A | 281 | 7.116 | 5.766 | 34.778 | 1.00 45.88 | O |
| ATOM | 348 | C | SER | A | 281 | 9.824 | 6.246 | 35.171 | 1.00 48.48 | C |
| ATOM | 349 | O | SER | A | 281 | 10.047 | 6.453 | 33.975 | 1.00 48.21 | O |
| ATOM | 350 | N | PRO | A | 282 | 10.484 | 5.305 | 35.864 | 1.00 50.08 | N |
| ATOM | 351 | CD | PRO | A | 282 | 10.525 | 5.161 | 37.331 | 1.00 49.32 | C |
| ATOM | 352 | CA | PRO | A | 282 | 11.493 | 4.445 | 35.234 | 1.00 50.75 | C |
| ATOM | 353 | CB | PRO | A | 282 | 11.957 | 3.565 | 36.391 | 1.00 50.28 | C |
| ATOM | 354 | CG | PRO | A | 282 | 11.875 | 4.503 | 37.551 | 1.00 49.25 | C |
| ATOM | 355 | C | PRO | A | 282 | 10.929 | 3.631 | 34.067 | 1.00 51.51 | C |
| ATOM | 356 | O | PRO | A | 282 | 11.612 | 3.424 | 33.061 | 1.00 53.03 | O |
| ATOM | 357 | N | ASP | A | 283 | 9.685 | 3.175 | 34.199 | 1.00 52.17 | N |
| ATOM | 358 | CA | ASP | A | 283 | 9.039 | 2.385 | 33.145 | 1.00 52.65 | C |
| ATOM | 359 | CB | ASP | A | 283 | 7.667 | 1.891 | 33.612 | 1.00 55.07 | C |
| ATOM | 360 | CG | ASP | A | 283 | 7.766 | 0.800 | 34.659 | 1.00 57.35 | C |
| ATOM | 361 | OD1 | ASP | A | 283 | 8.164 | -0.333 | 34.305 | 1.00 57.65 | O |
| ATOM | 362 | OD2 | ASP | A | 283 | 7.453 | 1.078 | 35.838 | 1.00 57.97 | O |
| ATOM | 363 | C | ASP | A | 283 | 8.867 | 3.196 | 31.864 | 1.00 52.73 | C |
| ATOM | 364 | O | ASP | A | 283 | 9.073 | 2.692 | 30.754 | 1.00 51.98 | O |
| ATOM | 365 | N | ALA | A | 284 | 8.478 | 4.455 | 32.026 | 1.00 52.50 | N |
| ATOM | 366 | CA | ALA | A | 284 | 8.286 | 5.337 | 30.887 | 1.00 52.50 | C |
| ATOM | 367 | CB | ALA | A | 284 | 7.647 | 6.640 | 31.346 | 1.00 52.63 | C |
| ATOM | 368 | C | ALA | A | 284 | 9.642 | 5.611 | 30.236 | 1.00 52.04 | C |
| ATOM | 369 | O | ALA | A | 284 | 9.749 | 5.701 | 29.013 | 1.00 52.42 | O |
| ATOM | 370 | N | PHE | A | 285 | 10.673 | 5.741 | 31.066 | 1.00 51.55 | N |
| ATOM | 371 | CA | PHE | A | 285 | 12.020 | 6.011 | 30.583 | 1.00 50.56 | C |
| ATOM | 372 | CB | PHE | A | 285 | 12.965 | 6.272 | 31.762 | 1.00 50.26 | C |
| ATOM | 373 | CG | PHE | A | 285 | 14.367 | 6.649 | 31.354 | 1.00 48.38 | C |
| ATOM | 374 | CD1 | PHE | A | 285 | 14.621 | 7.861 | 30.716 | 1.00 48.49 | C |
| ATOM | 375 | CD2 | PHE | A | 285 | 15.430 | 5.787 | 31.602 | 1.00 47.80 | C |
| ATOM | 376 | CE1 | PHE | A | 285 | 15.912 | 8.210 | 30.334 | 1.00 48.80 | C |
| ATOM | 377 | CE2 | PHE | A | 285 | 16.730 | 6.124 | 31.224 | 1.00 47.76 | C |
| ATOM | 378 | CZ | PHE | A | 285 | 16.971 | 7.338 | 30.589 | 1.00 49.39 | C |
| ATOM | 379 | C | PHE | A | 285 | 12.532 | 4.845 | 29.757 | 1.00 51.15 | C |
| ATOM | 380 | O | PHE | A | 285 | 12.973 | 5.028 | 28.629 | 1.00 51.60 | O |
| ATOM | 381 | N | LEU | A | 286 | 12.457 | 3.642 | 30.320 | 1.00 52.67 | N |
| ATOM | 382 | CA | LEU | A | 286 | 12.919 | 2.442 | 29.636 | 1.00 54.11 | C |
| ATOM | 383 | CB | LEU | A | 286 | 12.889 | 1.246 | 30.592 | 1.00 54.73 | C |
| ATOM | 384 | CG | LEU | A | 286 | 13.641 | 1.362 | 31.924 | 1.00 56.04 | C |
| ATOM | 385 | CD1 | LEU | A | 286 | 13.392 | 0.105 | 32.745 | 1.00 55.14 | C |
| ATOM | 386 | CD2 | LEU | A | 286 | 15.131 | 1.551 | 31.684 | 1.00 54.53 | C |
| ATOM | 387 | C | LEU | A | 286 | 12.085 | 2.117 | 28.398 | 1.00 55.10 | C |
| ATOM | 388 | O | LEU | A | 286 | 12.320 | 1.105 | 27.737 | 1.00 54.96 | O |
| ATOM | 389 | N | ALA | A | 287 | 11.113 | 2.973 | 28.091 | 1.00 55.13 | N |
| ATOM | 390 | CA | ALA | A | 287 | 10.248 | 2.762 | 26.935 | 1.00 55.64 | C |
| ATOM | 391 | CB | ALA | A | 287 | 9.144 | 3.818 | 26.905 | 1.00 56.80 | C |
| ATOM | 392 | C | ALA | A | 287 | 11.047 | 2.797 | 25.634 | 1.00 55.77 | C |
| ATOM | 393 | O | ALA | A | 287 | 10.879 | 1.932 | 24.774 | 1.00 54.60 | O |
| ATOM | 394 | N | GLU | A | 288 | 11.914 | 3.798 | 25.500 | 1.00 55.86 | N |
| ATOM | 395 | CA | GLU | A | 288 | 12.747 | 3.942 | 24.309 | 1.00 56.18 | C |
| ATOM | 396 | CB | GLU | A | 288 | 13.667 | 5.165 | 24.434 | 1.00 57.47 | C |
| ATOM | 397 | CG | GLU | A | 288 | 12.944 | 6.487 | 24.680 | 1.00 58.41 | C |
| ATOM | 398 | CD | GLU | A | 288 | 12.422 | 6.635 | 26.107 | 1.00 59.54 | C |
| ATOM | 399 | OE1 | GLU | A | 288 | 13.229 | 6.947 | 27.012 | 1.00 58.98 | O |
| ATOM | 400 | OE2 | GLU | A | 288 | 11.205 | 6.437 | 26.328 | 1.00 58.53 | O |
| ATOM | 401 | C | GLU | A | 288 | 13.595 | 2.690 | 24.118 | 1.00 55.59 | C |
| ATOM | 402 | O | GLU | A | 288 | 13.848 | 2.267 | 22.992 | 1.00 54.08 | O |
| ATOM | 403 | N | ALA | A | 289 | 14.038 | 2.106 | 25.228 | 1.00 55.77 | N |
| ATOM | 404 | CA | ALA | A | 289 | 14.857 | 0.897 | 25.188 | 1.00 55.44 | C |

Figure 14

```
ATOM    405  CB  ALA A 289      15.367   0.562  26.586  1.00 55.43           C
ATOM    406  C   ALA A 289      14.030  -0.260  24.642  1.00 55.49           C
ATOM    407  O   ALA A 289      14.466  -0.980  23.740  1.00 55.41           O
ATOM    408  N   ASN A 290      12.834  -0.424  25.203  1.00 55.36           N
ATOM    409  CA  ASN A 290      11.905  -1.469  24.801  1.00 55.58           C
ATOM    410  CB  ASN A 290      10.564  -1.259  25.505  1.00 56.82           C
ATOM    411  CG  ASN A 290      10.704  -1.196  27.011  1.00 58.96           C
ATOM    412  OD1 ASN A 290       9.752  -0.872  27.722  1.00 59.75           O
ATOM    413  ND2 ASN A 290      11.896  -1.512  27.508  1.00 60.40           N
ATOM    414  C   ASN A 290      11.695  -1.449  23.291  1.00 55.49           C
ATOM    415  O   ASN A 290      11.587  -2.497  22.651  1.00 55.58           O
ATOM    416  N   LEU A 291      11.631  -0.244  22.731  1.00 54.95           N
ATOM    417  CA  LEU A 291      11.436  -0.063  21.300  1.00 54.38           C
ATOM    418  CB  LEU A 291      11.089   1.401  21.010  1.00 54.11           C
ATOM    419  CG  LEU A 291       9.743   1.870  21.582  1.00 54.26           C
ATOM    420  CD1 LEU A 291       9.622   3.380  21.476  1.00 54.08           C
ATOM    421  CD2 LEU A 291       8.607   1.180  20.845  1.00 52.84           C
ATOM    422  C   LEU A 291      12.662  -0.487  20.490  1.00 53.96           C
ATOM    423  O   LEU A 291      12.532  -1.134  19.452  1.00 52.76           O
ATOM    424  N   MET A 292      13.852  -0.126  20.960  1.00 53.76           N
ATOM    425  CA  MET A 292      15.061  -0.502  20.243  1.00 54.97           C
ATOM    426  CB  MET A 292      16.280   0.197  20.840  1.00 54.91           C
ATOM    427  CG  MET A 292      16.392   1.657  20.446  1.00 55.66           C
ATOM    428  SD  MET A 292      17.881   2.453  21.103  1.00 55.95           S
ATOM    429  CE  MET A 292      17.235   3.105  22.630  1.00 54.00           C
ATOM    430  C   MET A 292      15.252  -2.015  20.257  1.00 55.83           C
ATOM    431  O   MET A 292      15.843  -2.582  19.337  1.00 55.69           O
ATOM    432  N   LYS A 293      14.742  -2.668  21.299  1.00 56.90           N
ATOM    433  CA  LYS A 293      14.840  -4.121  21.403  1.00 58.07           C
ATOM    434  CB  LYS A 293      14.328  -4.613  22.765  1.00 59.28           C
ATOM    435  CG  LYS A 293      15.128  -4.160  23.975  1.00 61.32           C
ATOM    436  CD  LYS A 293      14.714  -4.962  25.206  1.00 61.67           C
ATOM    437  CE  LYS A 293      15.445  -4.501  26.453  1.00 62.64           C
ATOM    438  NZ  LYS A 293      15.085  -3.104  26.810  1.00 65.60           N
ATOM    439  C   LYS A 293      13.989  -4.758  20.305  1.00 57.41           C
ATOM    440  O   LYS A 293      14.407  -5.720  19.659  1.00 58.21           O
ATOM    441  N   GLN A 294      12.792  -4.214  20.103  1.00 56.16           N
ATOM    442  CA  GLN A 294      11.871  -4.731  19.095  1.00 56.22           C
ATOM    443  CB  GLN A 294      10.467  -4.164  19.332  1.00 57.31           C
ATOM    444  CG  GLN A 294       9.808  -4.645  20.620  1.00 57.88           C
ATOM    445  CD  GLN A 294       9.688  -6.158  20.673  1.00 60.13           C
ATOM    446  OE1 GLN A 294      10.187  -6.804  21.600  1.00 59.80           O
ATOM    447  NE2 GLN A 294       9.022  -6.735  19.672  1.00 60.65           N
ATOM    448  C   GLN A 294      12.297  -4.442  17.656  1.00 55.67           C
ATOM    449  O   GLN A 294      12.182  -5.303  16.783  1.00 56.38           O
ATOM    450  N   LEU A 295      12.790  -3.230  17.413  1.00 54.73           N
ATOM    451  CA  LEU A 295      13.206  -2.832  16.075  1.00 54.20           C
ATOM    452  CB  LEU A 295      12.497  -1.534  15.672  1.00 54.49           C
ATOM    453  CG  LEU A 295      10.997  -1.666  15.396  1.00 55.08           C
ATOM    454  CD1 LEU A 295      10.349  -0.297  15.288  1.00 55.52           C
ATOM    455  CD2 LEU A 295      10.801  -2.456  14.113  1.00 55.74           C
ATOM    456  C   LEU A 295      14.710  -2.663  15.917  1.00 53.33           C
ATOM    457  O   LEU A 295      15.288  -1.683  16.378  1.00 53.90           O
ATOM    458  N   GLN A 296      15.333  -3.629  15.253  1.00 52.40           N
ATOM    459  CA  GLN A 296      16.766  -3.596  15.011  1.00 51.48           C
ATOM    460  CB  GLN A 296      17.434  -4.820  15.633  1.00 52.38           C
ATOM    461  CG  GLN A 296      17.653  -4.677  17.127  1.00 54.67           C
ATOM    462  CD  GLN A 296      17.950  -5.999  17.798  1.00 55.42           C
ATOM    463  OE1 GLN A 296      18.766  -6.784  17.319  1.00 56.26           O
ATOM    464  NE2 GLN A 296      17.290  -6.250  18.922  1.00 55.57           N
```

Figure 14

```
ATOM    465  C   GLN A 296      17.048  -3.533  13.515  1.00 49.60           C
ATOM    466  O   GLN A 296      16.568  -4.360  12.733  1.00 49.65           O
ATOM    467  N   HIS A 297      17.824  -2.530  13.130  1.00 47.22           N
ATOM    468  CA  HIS A 297      18.164  -2.314  11.733  1.00 45.86           C
ATOM    469  CB  HIS A 297      17.009  -1.573  11.047  1.00 44.20           C
ATOM    470  CG  HIS A 297      17.101  -1.541   9.554  1.00 42.64           C
ATOM    471  CD2 HIS A 297      16.551  -2.340   8.612  1.00 42.47           C
ATOM    472  ND1 HIS A 297      17.822  -0.586   8.872  1.00 41.93           N
ATOM    473  CE1 HIS A 297      17.711  -0.796   7.573  1.00 42.47           C
ATOM    474  NE2 HIS A 297      16.944  -1.855   7.388  1.00 41.78           N
ATOM    475  C   HIS A 297      19.441  -1.487  11.703  1.00 44.88           C
ATOM    476  O   HIS A 297      19.775  -0.825  12.679  1.00 43.76           O
ATOM    477  N   GLN A 298      20.156  -1.523  10.586  1.00 46.03           N
ATOM    478  CA  GLN A 298      21.396  -0.773  10.475  1.00 46.40           C
ATOM    479  CB  GLN A 298      22.197  -1.273   9.270  1.00 49.01           C
ATOM    480  CG  GLN A 298      22.706  -2.697   9.473  1.00 53.42           C
ATOM    481  CD  GLN A 298      23.527  -2.849  10.758  1.00 56.21           C
ATOM    482  OE1 GLN A 298      23.741  -3.962  11.249  1.00 55.88           O
ATOM    483  NE2 GLN A 298      23.995  -1.722  11.300  1.00 55.67           N
ATOM    484  C   GLN A 298      21.215   0.740  10.409  1.00 44.96           C
ATOM    485  O   GLN A 298      22.169   1.495  10.616  1.00 42.40           O
ATOM    486  N   ARG A 299      19.990   1.185  10.140  1.00 43.76           N
ATOM    487  CA  ARG A 299      19.710   2.619  10.067  1.00 42.70           C
ATOM    488  CB  ARG A 299      18.848   2.925   8.843  1.00 41.39           C
ATOM    489  CG  ARG A 299      19.455   2.424   7.536  1.00 42.77           C

ATOM    490  CD  ARG A 299      20.889   2.906   7.361  1.00 44.71           C
ATOM    491  NE  ARG A 299      21.441   2.477   6.080  1.00 46.92           N
ATOM    492  CZ  ARG A 299      22.715   2.607   5.722  1.00 47.55           C
ATOM    493  NH1 ARG A 299      23.591   3.160   6.551  1.00 47.71           N
ATOM    494  NH2 ARG A 299      23.110   2.184   4.528  1.00 45.53           N
ATOM    495  C   ARG A 299      19.018   3.114  11.338  1.00 42.21           C
ATOM    496  O   ARG A 299      18.499   4.234  11.391  1.00 41.54           O
ATOM    497  N   LEU A 300      19.012   2.267  12.360  1.00 41.12           N
ATOM    498  CA  LEU A 300      18.410   2.612  13.644  1.00 41.22           C
ATOM    499  CB  LEU A 300      17.227   1.682  13.946  1.00 40.58           C
ATOM    500  CG  LEU A 300      15.831   2.194  13.556  1.00 40.03           C
ATOM    501  CD1 LEU A 300      15.785   2.495  12.072  1.00 39.89           C
ATOM    502  CD2 LEU A 300      14.777   1.158  13.924  1.00 40.32           C
ATOM    503  C   LEU A 300      19.460   2.490  14.744  1.00 41.40           C
ATOM    504  O   LEU A 300      20.249   1.552  14.742  1.00 40.94           O
ATOM    505  N   VAL A 301      19.480   3.444  15.670  1.00 42.25           N
ATOM    506  CA  VAL A 301      20.428   3.413  16.779  1.00 42.79           C
ATOM    507  CB  VAL A 301      20.180   4.580  17.750  1.00 41.46           C
ATOM    508  CG1 VAL A 301      20.980   4.380  19.025  1.00 43.41           C
ATOM    509  CG2 VAL A 301      20.554   5.888  17.084  1.00 41.18           C
ATOM    510  C   VAL A 301      20.266   2.100  17.543  1.00 44.38           C
ATOM    511  O   VAL A 301      19.150   1.727  17.913  1.00 43.58           O
ATOM    512  N   ARG A 302      21.376   1.404  17.781  1.00 46.28           N
ATOM    513  CA  ARG A 302      21.344   0.126  18.494  1.00 48.56           C
ATOM    514  CB  ARG A 302      22.384  -0.841  17.917  1.00 50.93           C
ATOM    515  CG  ARG A 302      22.443  -2.172  18.662  1.00 53.79           C
ATOM    516  CD  ARG A 302      23.711  -2.968  18.361  1.00 57.02           C
ATOM    517  NE  ARG A 302      23.759  -4.207  19.142  1.00 59.67           N
ATOM    518  CZ  ARG A 302      24.826  -4.995  19.253  1.00 60.74           C
ATOM    519  NH1 ARG A 302      25.958  -4.683  18.632  1.00 61.12           N
ATOM    520  NH2 ARG A 302      24.763  -6.095  19.995  1.00 61.49           N
ATOM    521  C   ARG A 302      21.594   0.260  19.994  1.00 48.69           C
ATOM    522  O   ARG A 302      22.566   0.883  20.414  1.00 49.77           O
ATOM    523  N   LEU A 303      20.714  -0.335  20.795  1.00 48.82           N
```

Figure 14

| ATOM | 524 | CA  | LEU A 303 | 20.840 | -0.315 | 22.254 | 1.00 | 48.45 | C |
| ATOM | 525 | CB  | LEU A 303 | 19.468 | -0.501 | 22.904 | 1.00 | 48.63 | C |
| ATOM | 526 | CG  | LEU A 303 | 19.472 | -0.912 | 24.382 | 1.00 | 48.52 | C |
| ATOM | 527 | CD1 | LEU A 303 | 19.933 | 0.253  | 25.238 | 1.00 | 49.06 | C |
| ATOM | 528 | CD2 | LEU A 303 | 18.083 | -1.356 | 24.804 | 1.00 | 47.82 | C |
| ATOM | 529 | C   | LEU A 303 | 21.763 | -1.446 | 22.703 | 1.00 | 48.52 | C |
| ATOM | 530 | O   | LEU A 303 | 21.717 | -2.546 | 22.146 | 1.00 | 47.15 | O |
| ATOM | 531 | N   | TYR A 304 | 22.601 | -1.182 | 23.704 | 1.00 | 49.74 | N |
| ATOM | 532 | CA  | TYR A 304 | 23.513 | -2.209 | 24.202 | 1.00 | 50.23 | C |
| ATOM | 533 | CB  | TYR A 304 | 24.946 | -1.679 | 24.310 | 1.00 | 51.31 | C |
| ATOM | 534 | CG  | TYR A 304 | 25.719 | -1.736 | 23.014 | 1.00 | 50.64 | C |
| ATOM | 535 | CD1 | TYR A 304 | 25.305 | -2.560 | 21.973 | 1.00 | 52.58 | C |
| ATOM | 536 | CE1 | TYR A 304 | 26.022 | -2.633 | 20.784 | 1.00 | 54.46 | C |
| ATOM | 537 | CD2 | TYR A 304 | 26.875 | -0.983 | 22.837 | 1.00 | 51.71 | C |
| ATOM | 538 | CE2 | TYR A 304 | 27.604 | -1.050 | 21.649 | 1.00 | 52.67 | C |
| ATOM | 539 | CZ  | TYR A 304 | 27.169 | -1.879 | 20.626 | 1.00 | 53.84 | C |
| ATOM | 540 | OH  | TYR A 304 | 27.874 | -1.959 | 19.446 | 1.00 | 55.42 | O |
| ATOM | 541 | C   | TYR A 304 | 23.104 | -2.788 | 25.544 | 1.00 | 50.37 | C |
| ATOM | 542 | O   | TYR A 304 | 23.219 | -3.996 | 25.761 | 1.00 | 50.85 | O |
| ATOM | 543 | N   | ALA A 305 | 22.625 | -1.935 | 26.444 | 1.00 | 49.69 | N |
| ATOM | 544 | CA  | ALA A 305 | 22.228 | -2.402 | 27.757 | 1.00 | 48.45 | C |
| ATOM | 545 | CB  | ALA A 305 | 23.467 | -2.805 | 28.548 | 1.00 | 48.40 | C |
| ATOM | 546 | C   | ALA A 305 | 21.446 | -1.348 | 28.523 | 1.00 | 49.38 | C |
| ATOM | 547 | O   | ALA A 305 | 21.307 | -0.208 | 28.075 | 1.00 | 47.57 | O |
| ATOM | 548 | N   | VAL A 306 | 20.941 | -1.745 | 29.686 | 1.00 | 49.54 | N |
| ATOM | 549 | CA  | VAL A 306 | 20.183 | -0.854 | 30.550 | 1.00 | 51.27 | C |
| ATOM | 550 | CB  | VAL A 306 | 18.658 | -1.102 | 30.413 | 1.00 | 51.44 | C |
| ATOM | 551 | CG1 | VAL A 306 | 18.207 | -0.850 | 28.978 | 1.00 | 50.91 | C |
| ATOM | 552 | CG2 | VAL A 306 | 18.327 | -2.530 | 30.818 | 1.00 | 52.49 | C |
| ATOM | 553 | C   | VAL A 306 | 20.590 | -1.088 | 32.003 | 1.00 | 52.37 | C |
| ATOM | 554 | O   | VAL A 306 | 21.044 | -2.176 | 32.363 | 1.00 | 52.58 | O |
| ATOM | 555 | N   | VAL A 307 | 20.451 | -0.050 | 32.823 | 1.00 | 53.68 | N |
| ATOM | 556 | CA  | VAL A 307 | 20.754 | -0.120 | 34.250 | 1.00 | 54.88 | C |
| ATOM | 557 | CB  | VAL A 307 | 21.887 | 0.856  | 34.637 | 1.00 | 53.54 | C |
| ATOM | 558 | CG1 | VAL A 307 | 22.100 | 0.843  | 36.145 | 1.00 | 54.06 | C |
| ATOM | 559 | CG2 | VAL A 307 | 23.173 | 0.454  | 33.930 | 1.00 | 54.06 | C |
| ATOM | 560 | C   | VAL A 307 | 19.445 | 0.290  | 34.927 | 1.00 | 55.84 | C |
| ATOM | 561 | O   | VAL A 307 | 19.064 | 1.463  | 34.905 | 1.00 | 56.29 | O |
| ATOM | 562 | N   | THR A 308 | 18.761 | -0.681 | 35.524 | 1.00 | 57.04 | N |
| ATOM | 563 | CA  | THR A 308 | 17.462 | -0.434 | 36.145 | 1.00 | 57.09 | C |
| ATOM | 564 | CB  | THR A 308 | 16.554 | -1.657 | 35.959 | 1.00 | 56.31 | C |
| ATOM | 565 | OG1 | THR A 308 | 17.269 | -2.840 | 36.319 | 1.00 | 56.55 | O |
| ATOM | 566 | CG2 | THR A 308 | 16.114 | -1.770 | 34.508 | 1.00 | 55.78 | C |
| ATOM | 567 | C   | THR A 308 | 17.385 | 0.018  | 37.602 | 1.00 | 57.64 | C |
| ATOM | 568 | O   | THR A 308 | 16.410 | -0.269 | 38.291 | 1.00 | 58.37 | O |
| ATOM | 569 | N   | GLN A 309 | 18.399 | 0.734  | 38.070 | 1.00 | 57.73 | N |
| ATOM | 570 | CA  | GLN A 309 | 18.388 | 1.258  | 39.428 | 1.00 | 57.33 | C |
| ATOM | 571 | CB  | GLN A 309 | 19.288 | 0.428  | 40.345 | 1.00 | 58.28 | C |
| ATOM | 572 | CG  | GLN A 309 | 18.653 | -0.874 | 40.812 | 1.00 | 60.68 | C |
| ATOM | 573 | CD  | GLN A 309 | 17.266 | -0.673 | 41.423 | 1.00 | 61.74 | C |
| ATOM | 574 | OE1 | GLN A 309 | 17.086 | 0.117  | 42.355 | 1.00 | 62.41 | O |
| ATOM | 575 | NE2 | GLN A 309 | 16.279 | -1.393 | 40.897 | 1.00 | 61.97 | N |
| ATOM | 576 | C   | GLN A 309 | 18.855 | 2.709  | 39.398 | 1.00 | 57.23 | C |
| ATOM | 577 | O   | GLN A 309 | 19.939 | 3.011  | 38.904 | 1.00 | 56.86 | O |
| ATOM | 578 | N   | GLU A 310 | 18.025 | 3.608  | 39.918 | 1.00 | 57.68 | N |
| ATOM | 579 | CA  | GLU A 310 | 18.357 | 5.027  | 39.926 | 1.00 | 57.52 | C |
| ATOM | 580 | CB  | GLU A 310 | 17.340 | 5.810  | 40.769 | 1.00 | 59.49 | C |
| ATOM | 581 | CG  | GLU A 310 | 16.534 | 4.977  | 41.764 | 1.00 | 61.62 | C |
| ATOM | 582 | CD  | GLU A 310 | 15.189 | 4.513  | 41.206 | 1.00 | 63.46 | C |
| ATOM | 583 | OE1 | GLU A 310 | 14.362 | 5.378  | 40.838 | 1.00 | 62.27 | O |

Figure 14

| ATOM | 584 | OE2 | GLU A 310 | 14.955 | 3.284 | 41.144 | 1.00 | 64.23 | O |
| ATOM | 585 | C | GLU A 310 | 19.776 | 5.289 | 40.429 | 1.00 | 56.62 | C |
| ATOM | 586 | O | GLU A 310 | 20.171 | 4.792 | 41.483 | 1.00 | 57.17 | O |
| ATOM | 587 | N | PRO A 311 | 20.571 | 6.058 | 39.662 | 1.00 | 54.74 | N |
| ATOM | 588 | CD | PRO A 311 | 21.892 | 6.535 | 40.104 | 1.00 | 54.52 | C |
| ATOM | 589 | CA | PRO A 311 | 20.197 | 6.669 | 38.377 | 1.00 | 53.04 | C |
| ATOM | 590 | CB | PRO A 311 | 21.313 | 7.689 | 38.141 | 1.00 | 53.07 | C |
| ATOM | 591 | CG | PRO A 311 | 22.496 | 7.050 | 38.810 | 1.00 | 55.47 | C |
| ATOM | 592 | C | PRO A 311 | 20.063 | 5.666 | 37.224 | 1.00 | 51.40 | C |
| ATOM | 593 | O | PRO A 311 | 21.018 | 4.963 | 36.881 | 1.00 | 52.10 | O |
| ATOM | 594 | N | ILE A 312 | 18.867 | 5.618 | 36.637 | 1.00 | 49.42 | N |
| ATOM | 595 | CA | ILE A 312 | 18.545 | 4.718 | 35.525 | 1.00 | 46.96 | C |
| ATOM | 596 | CB | ILE A 312 | 17.070 | 4.858 | 35.103 | 1.00 | 47.01 | C |
| ATOM | 597 | CG2 | ILE A 312 | 16.674 | 3.674 | 34.229 | 1.00 | 45.32 | C |
| ATOM | 598 | CG1 | ILE A 312 | 16.177 | 4.987 | 36.340 | 1.00 | 47.12 | C |
| ATOM | 599 | CD1 | ILE A 312 | 16.273 | 3.833 | 37.307 | 1.00 | 48.47 | C |
| ATOM | 600 | C | ILE A 312 | 19.392 | 5.011 | 34.288 | 1.00 | 45.21 | C |
| ATOM | 601 | O | ILE A 312 | 19.612 | 6.173 | 33.945 | 1.00 | 44.29 | O |
| ATOM | 602 | N | TYR A 313 | 19.832 | 3.954 | 33.609 | 1.00 | 43.41 | N |
| ATOM | 603 | CA | TYR A 313 | 20.664 | 4.092 | 32.412 | 1.00 | 43.47 | C |
| ATOM | 604 | CB | TYR A 313 | 22.081 | 3.546 | 32.643 | 1.00 | 42.35 | C |
| ATOM | 605 | CG | TYR A 313 | 23.010 | 4.333 | 33.534 | 1.00 | 42.23 | C |
| ATOM | 606 | CD1 | TYR A 313 | 22.638 | 5.555 | 34.080 | 1.00 | 41.44 | C |
| ATOM | 607 | CE1 | TYR A 313 | 23.513 | 6.277 | 34.884 | 1.00 | 42.15 | C |
| ATOM | 608 | CD2 | TYR A 313 | 24.288 | 3.845 | 33.813 | 1.00 | 43.13 | C |
| ATOM | 609 | CE2 | TYR A 313 | 25.172 | 4.553 | 34.613 | 1.00 | 42.92 | C |
| ATOM | 610 | CZ | TYR A 313 | 24.781 | 5.769 | 35.144 | 1.00 | 42.62 | C |
| ATOM | 611 | OH | TYR A 313 | 25.662 | 6.483 | 35.911 | 1.00 | 41.94 | O |
| ATOM | 612 | C | TYR A 313 | 20.149 | 3.338 | 31.196 | 1.00 | 42.19 | C |
| ATOM | 613 | O | TYR A 313 | 19.610 | 2.242 | 31.317 | 1.00 | 43.54 | O |
| ATOM | 614 | N | ILE A 314 | 20.348 | 3.936 | 30.023 | 1.00 | 41.40 | N |
| ATOM | 615 | CA | ILE A 314 | 20.037 | 3.300 | 28.747 | 1.00 | 39.56 | C |
| ATOM | 616 | CB | ILE A 314 | 18.918 | 4.005 | 27.957 | 1.00 | 40.04 | C |
| ATOM | 617 | CG2 | ILE A 314 | 18.818 | 3.394 | 26.576 | 1.00 | 38.89 | C |
| ATOM | 618 | CG1 | ILE A 314 | 17.576 | 3.843 | 28.672 | 1.00 | 41.58 | C |
| ATOM | 619 | CD1 | ILE A 314 | 16.420 | 4.567 | 27.980 | 1.00 | 42.97 | C |
| ATOM | 620 | C | ILE A 314 | 21.371 | 3.487 | 28.011 | 1.00 | 38.83 | C |
| ATOM | 621 | O | ILE A 314 | 21.883 | 4.608 | 27.931 | 1.00 | 38.04 | O |
| ATOM | 622 | N | ILE A 315 | 21.931 | 2.405 | 27.486 | 1.00 | 37.01 | N |
| ATOM | 623 | CA | ILE A 315 | 23.228 | 2.475 | 26.821 | 1.00 | 39.12 | C |
| ATOM | 624 | CB | ILE A 315 | 24.292 | 1.663 | 27.624 | 1.00 | 39.21 | C |
| ATOM | 625 | CG2 | ILE A 315 | 25.680 | 1.859 | 27.017 | 1.00 | 38.56 | C |
| ATOM | 626 | CG1 | ILE A 315 | 24.304 | 2.109 | 29.093 | 1.00 | 39.64 | C |
| ATOM | 627 | CD1 | ILE A 315 | 23.212 | 1.477 | 29.976 | 1.00 | 40.14 | C |
| ATOM | 628 | C | ILE A 315 | 23.198 | 1.956 | 25.384 | 1.00 | 38.26 | C |
| ATOM | 629 | O | ILE A 315 | 22.708 | 0.863 | 25.129 | 1.00 | 40.59 | O |
| ATOM | 630 | N | THR A 316 | 23.731 | 2.741 | 24.450 | 1.00 | 37.40 | N |
| ATOM | 631 | CA | THR A 316 | 23.751 | 2.339 | 23.047 | 1.00 | 37.25 | C |
| ATOM | 632 | CB | THR A 316 | 22.727 | 3.127 | 22.205 | 1.00 | 38.60 | C |
| ATOM | 633 | OG1 | THR A 316 | 23.167 | 4.486 | 22.067 | 1.00 | 35.99 | O |
| ATOM | 634 | CG2 | THR A 316 | 21.361 | 3.110 | 22.871 | 1.00 | 38.46 | C |
| ATOM | 635 | C | THR A 316 | 25.103 | 2.598 | 22.418 | 1.00 | 37.53 | C |
| ATOM | 636 | O | THR A 316 | 26.024 | 3.097 | 23.064 | 1.00 | 35.25 | O |
| ATOM | 637 | N | GLU A 317 | 25.210 | 2.255 | 21.140 | 1.00 | 39.12 | N |
| ATOM | 638 | CA | GLU A 317 | 26.433 | 2.497 | 20.409 | 1.00 | 39.65 | C |
| ATOM | 639 | CB | GLU A 317 | 26.308 | 2.006 | 18.967 | 1.00 | 42.14 | C |
| ATOM | 640 | CG | GLU A 317 | 25.367 | 2.843 | 18.116 | 1.00 | 45.03 | C |
| ATOM | 641 | CD | GLU A 317 | 25.143 | 2.251 | 16.746 | 1.00 | 46.25 | C |
| ATOM | 642 | OE1 | GLU A 317 | 26.138 | 2.028 | 16.022 | 1.00 | 48.48 | O |
| ATOM | 643 | OE2 | GLU A 317 | 23.972 | 2.007 | 16.394 | 1.00 | 46.79 | O |

Figure 14

| | | | | | | | | | |
|---|---|---|---|---|---|---|---|---|---|
| ATOM | 644 | C | GLU | A | 317 | 26.615 | 4.010 | 20.424 | 1.00 39.19 | C |
| ATOM | 645 | O | GLU | A | 317 | 25.642 | 4.765 | 20.499 | 1.00 40.23 | O |
| ATOM | 646 | N | TYR | A | 318 | 27.864 | 4.445 | 20.378 | 1.00 37.72 | N |
| ATOM | 647 | CA | TYR | A | 318 | 28.194 | 5.858 | 20.377 | 1.00 36.02 | C |
| ATOM | 648 | CB | TYR | A | 318 | 29.562 | 6.034 | 21.040 | 1.00 35.78 | C |
| ATOM | 649 | CG | TYR | A | 318 | 30.166 | 7.414 | 20.953 | 1.00 37.20 | C |
| ATOM | 650 | CD1 | TYR | A | 318 | 29.753 | 8.438 | 21.804 | 1.00 35.24 | C |
| ATOM | 651 | CE1 | TYR | A | 318 | 30.364 | 9.692 | 21.772 | 1.00 37.97 | C |
| ATOM | 652 | CD2 | TYR | A | 318 | 31.203 | 7.676 | 20.054 | 1.00 37.59 | C |
| ATOM | 653 | CE2 | TYR | A | 318 | 31.817 | 8.918 | 20.015 | 1.00 38.87 | C |
| ATOM | 654 | CZ | TYR | A | 318 | 31.400 | 9.918 | 20.872 | 1.00 38.89 | C |
| ATOM | 655 | OH | TYR | A | 318 | 32.031 | 11.135 | 20.830 | 1.00 41.30 | O |
| ATOM | 656 | C | TYR | A | 318 | 28.222 | 6.355 | 18.924 | 1.00 35.66 | C |
| ATOM | 657 | O | TYR | A | 318 | 28.563 | 5.601 | 18.014 | 1.00 35.81 | O |
| ATOM | 658 | N | MET | A | 319 | 27.839 | 7.610 | 18.715 | 1.00 35.56 | N |
| ATOM | 659 | CA | MET | A | 319 | 27.839 | 8.210 | 17.378 | 1.00 36.43 | C |
| ATOM | 660 | CB | MET | A | 319 | 26.412 | 8.568 | 16.934 | 1.00 35.78 | C |
| ATOM | 661 | CG | MET | A | 319 | 25.466 | 7.389 | 16.799 | 1.00 33.26 | C |
| ATOM | 662 | SD | MET | A | 319 | 25.902 | 6.237 | 15.499 | 1.00 38.41 | S |
| ATOM | 663 | CE | MET | A | 319 | 25.267 | 7.119 | 14.031 | 1.00 36.72 | C |
| ATOM | 664 | C | MET | A | 319 | 28.696 | 9.469 | 17.468 | 1.00 36.39 | C |
| ATOM | 665 | O | MET | A | 319 | 28.281 | 10.478 | 18.039 | 1.00 35.93 | O |
| ATOM | 666 | N | GLU | A | 320 | 29.896 | 9.380 | 16.903 | 1.00 37.90 | N |
| ATOM | 667 | CA | GLU | A | 320 | 30.887 | 10.453 | 16.915 | 1.00 38.53 | C |
| ATOM | 668 | CB | GLU | A | 320 | 32.066 | 10.069 | 16.018 | 1.00 41.31 | C |
| ATOM | 669 | CG | GLU | A | 320 | 33.149 | 11.128 | 15.913 | 1.00 45.22 | C |
| ATOM | 670 | CD | GLU | A | 320 | 33.802 | 11.433 | 17.248 | 1.00 47.27 | C |
| ATOM | 671 | OE1 | GLU | A | 320 | 34.163 | 10.472 | 17.958 | 1.00 49.61 | O |
| ATOM | 672 | OE2 | GLU | A | 320 | 33.963 | 12.628 | 17.584 | 1.00 48.31 | O |
| ATOM | 673 | C | GLU | A | 320 | 30.415 | 11.843 | 16.527 | 1.00 38.04 | C |
| ATOM | 674 | O | GLU | A | 320 | 30.871 | 12.835 | 17.101 | 1.00 36.82 | O |
| ATOM | 675 | N | ASN | A | 321 | 29.517 | 11.936 | 15.553 | 1.00 34.21 | N |
| ATOM | 676 | CA | ASN | A | 321 | 29.068 | 13.251 | 15.128 | 1.00 34.53 | C |
| ATOM | 677 | CB | ASN | A | 321 | 29.047 | 13.309 | 13.598 | 1.00 35.03 | C |
| ATOM | 678 | CG | ASN | A | 321 | 30.455 | 13.299 | 13.015 | 1.00 38.22 | C |
| ATOM | 679 | OD1 | ASN | A | 321 | 31.278 | 14.148 | 13.359 | 1.00 39.65 | O |
| ATOM | 680 | ND2 | ASN | A | 321 | 30.743 | 12.333 | 12.153 | 1.00 39.25 | N |
| ATOM | 681 | C | ASN | A | 321 | 27.747 | 13.709 | 15.737 | 1.00 34.98 | C |
| ATOM | 682 | O | ASN | A | 321 | 27.249 | 14.793 | 15.433 | 1.00 35.93 | O |
| ATOM | 683 | N | GLY | A | 322 | 27.201 | 12.889 | 16.626 | 1.00 34.65 | N |
| ATOM | 684 | CA | GLY | A | 322 | 25.973 | 13.256 | 17.300 | 1.00 33.93 | C |
| ATOM | 685 | C | GLY | A | 322 | 24.802 | 13.588 | 16.397 | 1.00 33.44 | C |
| ATOM | 686 | O | GLY | A | 322 | 24.640 | 12.988 | 15.337 | 1.00 32.24 | O |
| ATOM | 687 | N | SER | A | 323 | 23.996 | 14.555 | 16.828 | 1.00 33.48 | N |
| ATOM | 688 | CA | SER | A | 323 | 22.799 | 14.967 | 16.100 | 1.00 35.20 | C |
| ATOM | 689 | CB | SER | A | 323 | 21.986 | 15.939 | 16.959 | 1.00 35.65 | C |
| ATOM | 690 | OG | SER | A | 323 | 20.723 | 16.186 | 16.372 | 1.00 41.61 | O |
| ATOM | 691 | C | SER | A | 323 | 23.035 | 15.593 | 14.730 | 1.00 34.60 | C |
| ATOM | 692 | O | SER | A | 323 | 23.819 | 16.538 | 14.589 | 1.00 33.43 | O |
| ATOM | 693 | N | LEU | A | 324 | 22.324 | 15.071 | 13.733 | 1.00 33.58 | N |
| ATOM | 694 | CA | LEU | A | 324 | 22.427 | 15.560 | 12.361 | 1.00 33.81 | C |
| ATOM | 695 | CB | LEU | A | 324 | 21.412 | 14.843 | 11.455 | 1.00 32.35 | C |
| ATOM | 696 | CG | LEU | A | 324 | 21.270 | 15.396 | 10.024 | 1.00 31.15 | C |
| ATOM | 697 | CD1 | LEU | A | 324 | 22.576 | 15.217 | 9.261 | 1.00 30.12 | C |
| ATOM | 698 | CD2 | LEU | A | 324 | 20.141 | 14.671 | 9.302 | 1.00 31.33 | C |
| ATOM | 699 | C | LEU | A | 324 | 22.203 | 17.058 | 12.260 | 1.00 33.85 | C |
| ATOM | 700 | O | LEU | A | 324 | 22.937 | 17.757 | 11.564 | 1.00 34.67 | O |
| ATOM | 701 | N | VAL | A | 325 | 21.188 | 17.548 | 12.951 | 1.00 34.89 | N |
| ATOM | 702 | CA | VAL | A | 325 | 20.858 | 18.963 | 12.910 | 1.00 37.69 | C |
| ATOM | 703 | CB | VAL | A | 325 | 19.567 | 19.249 | 13.730 | 1.00 36.17 | C |

Figure 14

```
ATOM    704  CG1 VAL A 325      19.843  19.132  15.212  1.00 37.06           C
ATOM    705  CG2 VAL A 325      19.024  20.630  13.380  1.00 38.24           C
ATOM    706  C   VAL A 325      22.010  19.850  13.406  1.00 38.03           C
ATOM    707  O   VAL A 325      22.111  21.026  13.023  1.00 36.79           O
ATOM    708  N   ASP A 326      22.877  19.276  14.240  1.00 38.22           N
ATOM    709  CA  ASP A 326      24.035  19.998  14.787  1.00 38.36           C
ATOM    710  CB  ASP A 326      24.407  19.462  16.178  1.00 38.66           C
ATOM    711  CG  ASP A 326      23.344  19.746  17.221  1.00 41.04           C
ATOM    712  OD1 ASP A 326      22.851  20.890  17.258  1.00 41.86           O
ATOM    713  OD2 ASP A 326      23.014  18.835  18.012  1.00 41.43           O
ATOM    714  C   ASP A 326      25.243  19.844  13.868  1.00 38.28           C
ATOM    715  O   ASP A 326      25.978  20.800  13.603  1.00 38.73           O
ATOM    716  N   PHE A 327      25.443  18.625  13.389  1.00 38.11           N
ATOM    717  CA  PHE A 327      26.554  18.323  12.505  1.00 37.01           C
ATOM    718  CB  PHE A 327      26.555  16.833  12.157  1.00 36.89           C
ATOM    719  CG  PHE A 327      27.621  16.442  11.166  1.00 39.92           C
ATOM    720  CD1 PHE A 327      28.969  16.479  11.522  1.00 40.56           C
ATOM    721  CD2 PHE A 327      27.281  16.074   9.871  1.00 39.66           C
ATOM    722  CE1 PHE A 327      29.964  16.159  10.600  1.00 40.85           C
ATOM    723  CE2 PHE A 327      28.271  15.750   8.938  1.00 42.49           C
ATOM    724  CZ  PHE A 327      29.616  15.794   9.307  1.00 42.47           C
ATOM    725  C   PHE A 327      26.474  19.134  11.217  1.00 38.70           C
ATOM    726  O   PHE A 327      27.500  19.534  10.667  1.00 35.42           O
ATOM    727  N   LEU A 328      25.252  19.361  10.737  1.00 38.98           N
ATOM    728  CA  LEU A 328      25.042  20.099   9.500  1.00 40.77           C
ATOM    729  CB  LEU A 328      23.551  20.115   9.131  1.00 41.03           C
ATOM    730  CG  LEU A 328      22.943  18.777   8.697  1.00 40.94           C
ATOM    731  CD1 LEU A 328      21.480  18.977   8.323  1.00 42.73           C
ATOM    732  CD2 LEU A 328      23.730  18.206   7.522  1.00 42.46           C
ATOM    733  C   LEU A 328      25.561  21.522   9.582  1.00 42.45           C
ATOM    734  O   LEU A 328      25.915  22.115   8.560  1.00 42.54           O
ATOM    735  N   LYS A 329      25.606  22.056  10.801  1.00 44.00           N
ATOM    736  CA  LYS A 329      26.071  23.417  11.054  1.00 44.55           C
ATOM    737  CB  LYS A 329      25.377  23.996  12.289  1.00 45.37           C
ATOM    738  CG  LYS A 329      23.880  24.217  12.148  1.00 47.27           C
ATOM    739  CD  LYS A 329      23.303  24.798  13.437  1.00 47.84           C
ATOM    740  CE  LYS A 329      21.801  24.992  13.338  1.00 49.10           C
ATOM    741  NZ  LYS A 329      21.097  23.711  13.028  1.00 50.30           N
ATOM    742  C   LYS A 329      27.579  23.503  11.268  1.00 45.61           C
ATOM    743  O   LYS A 329      28.147  24.592  11.236  1.00 45.79           O
ATOM    744  N   THR A 330      28.225  22.362  11.494  1.00 45.78           N
ATOM    745  CA  THR A 330      29.670  22.337  11.716  1.00 45.99           C
ATOM    746  CB  THR A 330      30.132  20.986  12.284  1.00 45.33           C
ATOM    747  OG1 THR A 330      29.994  19.972  11.280  1.00 43.44           O
ATOM    748  CG2 THR A 330      29.307  20.618  13.506  1.00 43.92           C
ATOM    749  C   THR A 330      30.438  22.573  10.418  1.00 46.94           C
ATOM    750  O   THR A 330      29.897  22.399   9.323  1.00 48.18           O
ATOM    751  N   PRO A 331      31.715  22.975  10.527  1.00 47.08           N
ATOM    752  CD  PRO A 331      32.453  23.285  11.767  1.00 47.49           C
ATOM    753  CA  PRO A 331      32.549  23.229   9.349  1.00 46.95           C
ATOM    754  CB  PRO A 331      33.943  23.384   9.947  1.00 47.10           C
ATOM    755  CG  PRO A 331      33.655  24.058  11.251  1.00 47.30           C
ATOM    756  C   PRO A 331      32.468  22.085   8.345  1.00 46.98           C
ATOM    757  O   PRO A 331      32.214  22.305   7.160  1.00 47.76           O
ATOM    758  N   SER A 332      32.677  20.865   8.828  1.00 46.76           N
ATOM    759  CA  SER A 332      32.624  19.681   7.981  1.00 45.95           C
ATOM    760  CB  SER A 332      33.033  18.435   8.776  1.00 45.34           C
ATOM    761  OG  SER A 332      34.407  18.480   9.125  1.00 50.25           O
ATOM    762  C   SER A 332      31.216  19.488   7.427  1.00 44.87           C
ATOM    763  O   SER A 332      31.043  18.992   6.316  1.00 43.88           O
```

Figure 14

| | | | | | | | | | | |
|---|---|---|---|---|---|---|---|---|---|---|
| ATOM | 764 | N | GLY | A | 333 | 30.216 | 19.874 | 8.213 | 1.00 44.41 | N |
| ATOM | 765 | CA | GLY | A | 333 | 28.842 | 19.736 | 7.769 | 1.00 43.79 | C |
| ATOM | 766 | C | GLY | A | 333 | 28.522 | 20.681 | 6.625 | 1.00 44.38 | C |
| ATOM | 767 | O | GLY | A | 333 | 28.068 | 20.254 | 5.560 | 1.00 43.45 | O |
| ATOM | 768 | N | ILE | A | 334 | 28.770 | 21.968 | 6.847 | 1.00 44.51 | N |
| ATOM | 769 | CA | ILE | A | 334 | 28.509 | 23.003 | 5.848 | 1.00 46.01 | C |
| ATOM | 770 | CB | ILE | A | 334 | 29.054 | 24.378 | 6.339 | 1.00 47.19 | C |
| ATOM | 771 | CG2 | ILE | A | 334 | 29.035 | 25.398 | 5.210 | 1.00 47.56 | C |
| ATOM | 772 | CG1 | ILE | A | 334 | 28.211 | 24.882 | 7.512 | 1.00 48.35 | C |
| ATOM | 773 | CD1 | ILE | A | 334 | 26.731 | 25.054 | 7.180 | 1.00 52.45 | C |
| ATOM | 774 | C | ILE | A | 334 | 29.079 | 22.702 | 4.459 | 1.00 45.87 | C |
| ATOM | 775 | O | ILE | A | 334 | 28.475 | 23.066 | 3.446 | 1.00 44.84 | O |
| ATOM | 776 | N | LYS | A | 335 | 30.219 | 22.015 | 4.414 | 1.00 45.22 | N |
| ATOM | 777 | CA | LYS | A | 335 | 30.873 | 21.701 | 3.145 | 1.00 45.97 | C |
| ATOM | 778 | CB | LYS | A | 335 | 32.386 | 21.590 | 3.357 | 1.00 46.44 | C |
| ATOM | 779 | CG | LYS | A | 335 | 33.012 | 22.842 | 3.936 | 1.00 48.10 | C |
| ATOM | 780 | CD | LYS | A | 335 | 34.498 | 22.636 | 4.210 | 1.00 52.02 | C |
| ATOM | 781 | CE | LYS | A | 335 | 35.106 | 23.846 | 4.903 | 1.00 52.28 | C |
| ATOM | 782 | NZ | LYS | A | 335 | 36.512 | 23.590 | 5.314 | 1.00 55.59 | N |
| ATOM | 783 | C | LYS | A | 335 | 30.388 | 20.460 | 2.398 | 1.00 45.29 | C |
| ATOM | 784 | O | LYS | A | 335 | 30.848 | 20.194 | 1.287 | 1.00 44.72 | O |
| ATOM | 785 | N | LEU | A | 336 | 29.470 | 19.701 | 2.988 | 1.00 44.34 | N |
| ATOM | 786 | CA | LEU | A | 336 | 28.963 | 18.492 | 2.327 | 1.00 43.20 | C |
| ATOM | 787 | CB | LEU | A | 336 | 27.912 | 17.804 | 3.211 | 1.00 44.02 | C |
| ATOM | 788 | CG | LEU | A | 336 | 28.415 | 17.176 | 4.519 | 1.00 44.36 | C |
| ATOM | 789 | CD1 | LEU | A | 336 | 27.293 | 16.355 | 5.152 | 1.00 43.51 | C |
| ATOM | 790 | CD2 | LEU | A | 336 | 29.622 | 16.291 | 4.236 | 1.00 43.29 | C |
| ATOM | 791 | C | LEU | A | 336 | 28.360 | 18.773 | 0.949 | 1.00 41.77 | C |
| ATOM | 792 | O | LEU | A | 336 | 27.664 | 19.768 | 0.766 | 1.00 41.22 | O |
| ATOM | 793 | N | THR | A | 337 | 28.637 | 17.903 | -0.020 | 1.00 40.82 | N |
| ATOM | 794 | CA | THR | A | 337 | 28.088 | 18.074 | -1.366 | 1.00 41.94 | C |
| ATOM | 795 | CB | THR | A | 337 | 28.853 | 17.242 | -2.412 | 1.00 42.11 | C |
| ATOM | 796 | OG1 | THR | A | 337 | 28.625 | 15.848 | -2.175 | 1.00 42.53 | O |
| ATOM | 797 | CG2 | THR | A | 337 | 30.346 | 17.540 | -2.345 | 1.00 42.51 | C |
| ATOM | 798 | C | THR | A | 337 | 26.629 | 17.616 | -1.393 | 1.00 40.48 | C |
| ATOM | 799 | O | THR | A | 337 | 26.204 | 16.843 | -0.535 | 1.00 39.81 | O |
| ATOM | 800 | N | ILE | A | 338 | 25.872 | 18.088 | -2.379 | 1.00 40.49 | N |
| ATOM | 801 | CA | ILE | A | 338 | 24.463 | 17.726 | -2.515 | 1.00 39.87 | C |
| ATOM | 802 | CB | ILE | A | 338 | 23.804 | 18.468 | -3.720 | 1.00 40.16 | C |
| ATOM | 803 | CG2 | ILE | A | 338 | 24.495 | 18.085 | -5.017 | 1.00 38.68 | C |
| ATOM | 804 | CG1 | ILE | A | 338 | 22.309 | 18.148 | -3.786 | 1.00 38.40 | C |
| ATOM | 805 | CD1 | ILE | A | 338 | 21.523 | 18.709 | -2.635 | 1.00 41.17 | C |
| ATOM | 806 | C | ILE | A | 338 | 24.330 | 16.213 | -2.686 | 1.00 40.15 | C |
| ATOM | 807 | O | ILE | A | 338 | 23.325 | 15.609 | -2.287 | 1.00 39.87 | O |
| ATOM | 808 | N | ASN | A | 339 | 25.358 | 15.605 | -3.268 | 1.00 40.31 | N |
| ATOM | 809 | CA | ASN | A | 339 | 25.387 | 14.158 | -3.476 | 1.00 40.11 | C |
| ATOM | 810 | CB | ASN | A | 339 | 26.632 | 13.763 | -4.271 | 1.00 41.67 | C |
| ATOM | 811 | CG | ASN | A | 339 | 26.650 | 14.358 | -5.659 | 1.00 44.48 | C |
| ATOM | 812 | OD1 | ASN | A | 339 | 26.225 | 13.724 | -6.623 | 1.00 47.51 | O |
| ATOM | 813 | ND2 | ASN | A | 339 | 27.131 | 15.592 | -5.767 | 1.00 43.64 | N |
| ATOM | 814 | C | ASN | A | 339 | 25.420 | 13.437 | -2.130 | 1.00 39.02 | C |
| ATOM | 815 | O | ASN | A | 339 | 24.711 | 12.453 | -1.920 | 1.00 38.97 | O |
| ATOM | 816 | N | LYS | A | 340 | 26.254 | 13.929 | -1.221 | 1.00 37.68 | N |
| ATOM | 817 | CA | LYS | A | 340 | 26.381 | 13.313 | 0.094 | 1.00 36.95 | C |
| ATOM | 818 | CB | LYS | A | 340 | 27.612 | 13.858 | 0.819 | 1.00 39.66 | C |
| ATOM | 819 | CG | LYS | A | 340 | 27.843 | 13.223 | 2.191 | 1.00 44.60 | C |
| ATOM | 820 | CD | LYS | A | 340 | 27.861 | 11.691 | 2.102 | 1.00 45.75 | C |
| ATOM | 821 | CE | LYS | A | 340 | 27.959 | 11.053 | 3.486 | 1.00 46.99 | C |
| ATOM | 822 | NZ | LYS | A | 340 | 27.879 | 9.561 | 3.447 | 1.00 46.76 | N |
| ATOM | 823 | C | LYS | A | 340 | 25.129 | 13.526 | 0.949 | 1.00 36.22 | C |

Figure 14

| ATOM | 824 | O   | LYS A 340 | 24.690 | 12.615 | 1.637  | 1.00 | 35.05 | O |
|------|-----|-----|-----------|--------|--------|--------|------|-------|---|
| ATOM | 825 | N   | LEU A 341 | 24.559 | 14.725 | 0.904  | 1.00 | 35.02 | N |
| ATOM | 826 | CA  | LEU A 341 | 23.354 | 15.013 | 1.671  | 1.00 | 36.20 | C |
| ATOM | 827 | CB  | LEU A 341 | 22.932 | 16.470 | 1.483  | 1.00 | 35.22 | C |
| ATOM | 828 | CG  | LEU A 341 | 23.878 | 17.559 | 2.003  | 1.00 | 34.31 | C |
| ATOM | 829 | CD1 | LEU A 341 | 23.349 | 18.929 | 1.569  | 1.00 | 34.42 | C |
| ATOM | 830 | CD2 | LEU A 341 | 23.995 | 17.484 | 3.518  | 1.00 | 32.96 | C |
| ATOM | 831 | C   | LEU A 341 | 22.244 | 14.091 | 1.186  | 1.00 | 37.21 | C |
| ATOM | 832 | O   | LEU A 341 | 21.496 | 13.531 | 1.986  | 1.00 | 37.19 | O |
| ATOM | 833 | N   | LEU A 342 | 22.154 | 13.929 | -0.131 | 1.00 | 37.23 | N |
| ATOM | 834 | CA  | LEU A 342 | 21.142 | 13.068 | -0.730 | 1.00 | 38.18 | C |
| ATOM | 835 | CB  | LEU A 342 | 21.250 | 13.112 | -2.255 | 1.00 | 40.03 | C |
| ATOM | 836 | CG  | LEU A 342 | 20.290 | 14.047 | -2.991 | 1.00 | 41.96 | C |
| ATOM | 837 | CD1 | LEU A 342 | 18.867 | 13.519 | -2.877 | 1.00 | 44.89 | C |
| ATOM | 838 | CD2 | LEU A 342 | 20.390 | 15.443 | -2.407 | 1.00 | 44.32 | C |
| ATOM | 839 | C   | LEU A 342 | 21.281 | 11.630 | -0.245 | 1.00 | 37.95 | C |
| ATOM | 840 | O   | LEU A 342 | 20.287 | 10.951 | 0.000  | 1.00 | 37.24 | O |
| ATOM | 841 | N   | ASP A 343 | 22.519 | 11.170 | -0.108 | 1.00 | 37.09 | N |
| ATOM | 842 | CA  | ASP A 343 | 22.767 | 9.811  | 0.347  | 1.00 | 38.52 | C |
| ATOM | 843 | CB  | ASP A 343 | 24.249 | 9.461  | 0.185  | 1.00 | 43.12 | C |
| ATOM | 844 | CG  | ASP A 343 | 24.569 | 8.051  | 0.665  | 1.00 | 46.45 | C |
| ATOM | 845 | OD1 | ASP A 343 | 24.160 | 7.080  | -0.016 | 1.00 | 47.73 | O |
| ATOM | 846 | OD2 | ASP A 343 | 25.217 | 7.920  | 1.726  | 1.00 | 47.50 | O |
| ATOM | 847 | C   | ASP A 343 | 22.357 | 9.663  | 1.815  | 1.00 | 37.20 | C |
| ATOM | 848 | O   | ASP A 343 | 21.811 | 8.639  | 2.225  | 1.00 | 34.62 | O |
| ATOM | 849 | N   | MET A 344 | 22.640 | 10.686 | 2.613  | 1.00 | 35.56 | N |
| ATOM | 850 | CA  | MET A 344 | 22.269 | 10.644 | 4.018  | 1.00 | 35.75 | C |
| ATOM | 851 | CB  | MET A 344 | 22.772 | 11.902 | 4.726  | 1.00 | 37.39 | C |
| ATOM | 852 | CG  | MET A 344 | 24.293 | 11.955 | 4.843  | 1.00 | 40.59 | C |
| ATOM | 853 | SD  | MET A 344 | 24.859 | 13.519 | 5.504  | 1.00 | 44.60 | S |
| ATOM | 854 | CE  | MET A 344 | 24.609 | 13.272 | 7.246  | 1.00 | 43.13 | C |
| ATOM | 855 | C   | MET A 344 | 20.747 | 10.553 | 4.092  | 1.00 | 34.30 | C |
| ATOM | 856 | O   | MET A 344 | 20.197 | 9.732  | 4.822  | 1.00 | 33.76 | O |
| ATOM | 857 | N   | ALA A 345 | 20.077 | 11.396 | 3.309  | 1.00 | 32.57 | N |
| ATOM | 858 | CA  | ALA A 345 | 18.617 | 11.417 | 3.265  | 1.00 | 30.34 | C |
| ATOM | 859 | CB  | ALA A 345 | 18.139 | 12.478 | 2.278  | 1.00 | 29.75 | C |
| ATOM | 860 | C   | ALA A 345 | 18.095 | 10.044 | 2.858  | 1.00 | 29.68 | C |
| ATOM | 861 | O   | ALA A 345 | 17.087 | 9.582  | 3.379  | 1.00 | 28.85 | O |
| ATOM | 862 | N   | ALA A 346 | 18.787 | 9.386  | 1.935  | 1.00 | 29.31 | N |
| ATOM | 863 | CA  | ALA A 346 | 18.373 | 8.059  | 1.485  | 1.00 | 30.62 | C |
| ATOM | 864 | CB  | ALA A 346 | 19.239 | 7.603  | 0.301  | 1.00 | 30.13 | C |
| ATOM | 865 | C   | ALA A 346 | 18.467 | 7.048  | 2.631  | 1.00 | 31.98 | C |
| ATOM | 866 | O   | ALA A 346 | 17.594 | 6.185  | 2.779  | 1.00 | 32.52 | O |
| ATOM | 867 | N   | GLN A 347 | 19.529 | 7.154  | 3.430  | 1.00 | 31.04 | N |
| ATOM | 868 | CA  | GLN A 347 | 19.738 | 6.258  | 4.575  | 1.00 | 30.97 | C |
| ATOM | 869 | CB  | GLN A 347 | 21.070 | 6.562  | 5.265  | 1.00 | 30.67 | C |
| ATOM | 870 | CG  | GLN A 347 | 22.271 | 6.420  | 4.367  | 1.00 | 36.55 | C |
| ATOM | 871 | CD  | GLN A 347 | 23.570 | 6.517  | 5.126  | 1.00 | 37.79 | C |
| ATOM | 872 | OE1 | GLN A 347 | 24.636 | 6.637  | 4.528  | 1.00 | 43.06 | O |
| ATOM | 873 | NE2 | GLN A 347 | 23.492 | 6.456  | 6.446  | 1.00 | 38.37 | N |
| ATOM | 874 | C   | GLN A 347 | 18.615 | 6.408  | 5.597  | 1.00 | 29.43 | C |
| ATOM | 875 | O   | GLN A 347 | 18.162 | 5.432  | 6.177  | 1.00 | 29.27 | O |
| ATOM | 876 | N   | ILE A 348 | 18.193 | 7.646  | 5.821  | 1.00 | 29.59 | N |
| ATOM | 877 | CA  | ILE A 348 | 17.110 | 7.943  | 6.752  | 1.00 | 30.22 | C |
| ATOM | 878 | CB  | ILE A 348 | 16.952 | 9.485  | 6.932  | 1.00 | 29.56 | C |
| ATOM | 879 | CG2 | ILE A 348 | 15.740 | 9.801  | 7.813  | 1.00 | 28.72 | C |
| ATOM | 880 | CG1 | ILE A 348 | 18.239 | 10.061 | 7.541  | 1.00 | 28.88 | C |
| ATOM | 881 | CD1 | ILE A 348 | 18.274 | 11.579 | 7.623  | 1.00 | 28.72 | C |
| ATOM | 882 | C   | ILE A 348 | 15.812 | 7.339  | 6.199  | 1.00 | 31.95 | C |
| ATOM | 883 | O   | ILE A 348 | 15.071 | 6.666  | 6.920  | 1.00 | 31.78 | O |

Figure 14

| | | | | | | | | | |
|---|---|---|---|---|---|---|---|---|---|
| ATOM | 884 | N | ALA | A | 349 | 15.552 | 7.565 | 4.911 | 1.00 30.63 | N |
| ATOM | 885 | CA | ALA | A | 349 | 14.345 | 7.029 | 4.285 | 1.00 30.38 | C |
| ATOM | 886 | CB | ALA | A | 349 | 14.254 | 7.491 | 2.832 | 1.00 29.96 | C |
| ATOM | 887 | C | ALA | A | 349 | 14.353 | 5.502 | 4.361 | 1.00 30.22 | C |
| ATOM | 888 | O | ALA | A | 349 | 13.302 | 4.869 | 4.471 | 1.00 29.84 | O |
| ATOM | 889 | N | GLU | A | 350 | 15.541 | 4.908 | 4.310 | 1.00 30.43 | N |
| ATOM | 890 | CA | GLU | A | 350 | 15.653 | 3.453 | 4.385 | 1.00 30.64 | C |
| ATOM | 891 | CB | GLU | A | 350 | 17.095 | 3.022 | 4.133 | 1.00 35.80 | C |
| ATOM | 892 | CG | GLU | A | 350 | 17.285 | 1.516 | 4.056 | 1.00 38.47 | C |
| ATOM | 893 | CD | GLU | A | 350 | 18.751 | 1.123 | 4.078 | 1.00 43.45 | C |
| ATOM | 894 | OE1 | GLU | A | 350 | 19.556 | 1.803 | 3.409 | 1.00 44.20 | O |
| ATOM | 895 | OE2 | GLU | A | 350 | 19.098 | 0.134 | 4.759 | 1.00 44.63 | O |
| ATOM | 896 | C | GLU | A | 350 | 15.218 | 2.976 | 5.763 | 1.00 29.60 | C |
| ATOM | 897 | O | GLU | A | 350 | 14.488 | 1.991 | 5.897 | 1.00 30.30 | O |
| ATOM | 898 | N | GLY | A | 351 | 15.691 | 3.666 | 6.791 | 1.00 28.42 | N |
| ATOM | 899 | CA | GLY | A | 351 | 15.318 | 3.300 | 8.140 | 1.00 28.10 | C |
| ATOM | 900 | C | GLY | A | 351 | 13.821 | 3.468 | 8.346 | 1.00 29.67 | C |
| ATOM | 901 | O | GLY | A | 351 | 13.190 | 2.666 | 9.039 | 1.00 29.39 | O |
| ATOM | 902 | N | MET | A | 352 | 13.238 | 4.508 | 7.751 | 1.00 26.50 | N |
| ATOM | 903 | CA | MET | A | 352 | 11.805 | 4.722 | 7.910 | 1.00 27.29 | C |
| ATOM | 904 | CB | MET | A | 352 | 11.404 | 6.135 | 7.465 | 1.00 27.91 | C |
| ATOM | 905 | CG | MET | A | 352 | 11.848 | 7.227 | 8.436 | 1.00 28.27 | C |
| ATOM | 906 | SD | MET | A | 352 | 11.265 | 6.989 | 10.153 | 1.00 30.56 | S |
| ATOM | 907 | CE | MET | A | 352 | 9.449 | 7.096 | 9.920 | 1.00 27.40 | C |
| ATOM | 908 | C | MET | A | 352 | 11.014 | 3.684 | 7.136 | 1.00 28.58 | C |
| ATOM | 909 | O | MET | A | 352 | 9.901 | 3.310 | 7.542 | 1.00 28.35 | O |
| ATOM | 910 | N | ALA | A | 353 | 11.585 | 3.211 | 6.027 | 1.00 28.82 | N |
| ATOM | 911 | CA | ALA | A | 353 | 10.936 | 2.188 | 5.214 | 1.00 29.35 | C |
| ATOM | 912 | CB | ALA | A | 353 | 11.719 | 1.955 | 3.928 | 1.00 29.01 | C |
| ATOM | 913 | C | ALA | A | 353 | 10.842 | 0.885 | 6.023 | 1.00 31.83 | C |
| ATOM | 914 | O | ALA | A | 353 | 9.909 | 0.104 | 5.854 | 1.00 31.94 | O |
| ATOM | 915 | N | PHE | A | 354 | 11.809 | 0.648 | 6.904 | 1.00 33.79 | N |
| ATOM | 916 | CA | PHE | A | 354 | 11.768 | -0.551 | 7.738 | 1.00 34.42 | C |
| ATOM | 917 | CB | PHE | A | 354 | 13.123 | -0.777 | 8.395 | 1.00 38.05 | C |
| ATOM | 918 | CG | PHE | A | 354 | 13.170 | -1.967 | 9.317 | 1.00 37.42 | C |
| ATOM | 919 | CD1 | PHE | A | 354 | 13.146 | -3.259 | 8.807 | 1.00 39.70 | C |
| ATOM | 920 | CD2 | PHE | A | 354 | 13.289 | -1.788 | 10.692 | 1.00 39.51 | C |
| ATOM | 921 | CE1 | PHE | A | 354 | 13.249 | -4.370 | 9.661 | 1.00 39.65 | C |
| ATOM | 922 | CE2 | PHE | A | 354 | 13.393 | -2.889 | 11.556 | 1.00 40.01 | C |
| ATOM | 923 | CZ | PHE | A | 354 | 13.374 | -4.179 | 11.035 | 1.00 39.20 | C |
| ATOM | 924 | C | PHE | A | 354 | 10.690 | -0.343 | 8.804 | 1.00 35.04 | C |
| ATOM | 925 | O | PHE | A | 354 | 9.855 | -1.217 | 9.043 | 1.00 36.26 | O |
| ATOM | 926 | N | ILE | A | 355 | 10.714 | 0.823 | 9.442 | 1.00 33.51 | N |
| ATOM | 927 | CA | ILE | A | 355 | 9.733 | 1.165 | 10.463 | 1.00 33.24 | C |
| ATOM | 928 | CB | ILE | A | 355 | 9.968 | 2.602 | 10.976 | 1.00 32.25 | C |
| ATOM | 929 | CG2 | ILE | A | 355 | 8.709 | 3.125 | 11.682 | 1.00 28.18 | C |
| ATOM | 930 | CG1 | ILE | A | 355 | 11.222 | 2.624 | 11.865 | 1.00 32.80 | C |
| ATOM | 931 | CD1 | ILE | A | 355 | 11.652 | 4.008 | 12.337 | 1.00 30.52 | C |
| ATOM | 932 | C | ILE | A | 355 | 8.316 | 1.045 | 9.885 | 1.00 35.65 | C |
| ATOM | 933 | O | ILE | A | 355 | 7.421 | 0.474 | 10.516 | 1.00 35.64 | O |
| ATOM | 934 | N | GLU | A | 356 | 8.127 | 1.594 | 8.689 | 1.00 34.61 | N |
| ATOM | 935 | CA | GLU | A | 356 | 6.849 | 1.545 | 7.988 | 1.00 37.08 | C |
| ATOM | 936 | CB | GLU | A | 356 | 6.961 | 2.330 | 6.677 | 1.00 35.69 | C |
| ATOM | 937 | CG | GLU | A | 356 | 5.915 | 2.019 | 5.607 | 1.00 36.48 | C |
| ATOM | 938 | CD | GLU | A | 356 | 6.106 | 2.881 | 4.358 | 1.00 37.93 | C |
| ATOM | 939 | OE1 | GLU | A | 356 | 5.636 | 4.033 | 4.362 | 1.00 35.88 | O |
| ATOM | 940 | OE2 | GLU | A | 356 | 6.742 | 2.422 | 3.377 | 1.00 38.11 | O |
| ATOM | 941 | C | GLU | A | 356 | 6.439 | 0.098 | 7.696 | 1.00 39.39 | C |
| ATOM | 942 | O | GLU | A | 356 | 5.313 | -0.312 | 7.987 | 1.00 39.69 | O |
| ATOM | 943 | N | GLU | A | 357 | 7.365 | -0.667 | 7.127 | 1.00 41.24 | N |

Figure 14

| | | | | | | | | | |
|---|---|---|---|---|---|---|---|---|---|
| ATOM | 944 | CA | GLU | A | 357 | 7.119 | -2.062 | 6.785 | 1.00 44.40 | C |
| ATOM | 945 | CB | GLU | A | 357 | 8.323 | -2.611 | 5.996 | 1.00 46.55 | C |
| ATOM | 946 | CG | GLU | A | 357 | 9.082 | -3.767 | 6.627 | 1.00 49.01 | C |
| ATOM | 947 | CD | GLU | A | 357 | 8.353 | -5.086 | 6.480 | 1.00 51.08 | C |
| ATOM | 948 | OE1 | GLU | A | 357 | 7.994 | -5.432 | 5.334 | 1.00 52.28 | O |
| ATOM | 949 | OE2 | GLU | A | 357 | 8.142 | -5.773 | 7.503 | 1.00 51.13 | O |
| ATOM | 950 | C | GLU | A | 357 | 6.835 | -2.921 | 8.014 | 1.00 44.38 | C |
| ATOM | 951 | O | GLU | A | 357 | 6.179 | -3.964 | 7.910 | 1.00 45.35 | O |
| ATOM | 952 | N | ARG | A | 358 | 7.322 | -2.477 | 9.172 | 1.00 44.26 | N |
| ATOM | 953 | CA | ARG | A | 358 | 7.130 | -3.196 | 10.426 | 1.00 44.29 | C |
| ATOM | 954 | CB | ARG | A | 358 | 8.365 | -3.058 | 11.319 | 1.00 45.20 | C |
| ATOM | 955 | CG | ARG | A | 358 | 9.616 | -3.756 | 10.776 | 1.00 48.89 | C |
| ATOM | 956 | CD | ARG | A | 358 | 9.473 | -5.274 | 10.798 | 1.00 50.98 | C |
| ATOM | 957 | NE | ARG | A | 358 | 9.276 | -5.789 | 12.153 | 1.00 54.97 | N |
| ATOM | 958 | CZ | ARG | A | 358 | 10.169 | -5.692 | 13.138 | 1.00 55.09 | C |
| ATOM | 959 | NH1 | ARG | A | 358 | 11.334 | -5.097 | 12.926 | 1.00 56.31 | N |
| ATOM | 960 | NH2 | ARG | A | 358 | 9.895 | -6.183 | 14.342 | 1.00 55.91 | N |
| ATOM | 961 | C | ARG | A | 358 | 5.900 | -2.694 | 11.170 | 1.00 44.10 | C |
| ATOM | 962 | O | ARG | A | 358 | 5.671 | -3.053 | 12.321 | 1.00 43.44 | O |
| ATOM | 963 | N | ASN | A | 359 | 5.116 | -1.854 | 10.508 | 1.00 43.53 | N |
| ATOM | 964 | CA | ASN | A | 359 | 3.887 | -1.320 | 11.084 | 1.00 43.19 | C |
| ATOM | 965 | CB | ASN | A | 359 | 2.923 | -2.469 | 11.387 | 1.00 46.78 | C |
| ATOM | 966 | CG | ASN | A | 359 | 2.401 | -3.128 | 10.133 | 1.00 50.06 | C |
| ATOM | 967 | OD1 | ASN | A | 359 | 1.809 | -2.469 | 9.272 | 1.00 52.91 | O |
| ATOM | 968 | ND2 | ASN | A | 359 | 2.616 | -4.435 | 10.016 | 1.00 51.35 | N |
| ATOM | 969 | C | ASN | A | 359 | 4.032 | -0.432 | 12.320 | 1.00 41.40 | C |
| ATOM | 970 | O | ASN | A | 359 | 3.132 | -0.381 | 13.163 | 1.00 39.75 | O |
| ATOM | 971 | N | TYR | A | 360 | 5.162 | 0.262 | 12.431 | 1.00 38.99 | N |
| ATOM | 972 | CA | TYR | A | 360 | 5.385 | 1.184 | 13.539 | 1.00 38.07 | C |
| ATOM | 973 | CB | TYR | A | 360 | 6.758 | 0.964 | 14.192 | 1.00 40.47 | C |
| ATOM | 974 | CG | TYR | A | 360 | 6.876 | -0.233 | 15.112 | 1.00 43.05 | C |
| ATOM | 975 | CD1 | TYR | A | 360 | 6.945 | -1.525 | 14.605 | 1.00 43.67 | C |
| ATOM | 976 | CE1 | TYR | A | 360 | 7.095 | -2.633 | 15.455 | 1.00 46.33 | C |
| ATOM | 977 | CD2 | TYR | A | 360 | 6.953 | -0.065 | 16.497 | 1.00 45.60 | C |
| ATOM | 978 | CE2 | TYR | A | 360 | 7.099 | -1.167 | 17.361 | 1.00 47.80 | C |
| ATOM | 979 | CZ | TYR | A | 360 | 7.171 | -2.446 | 16.826 | 1.00 46.64 | C |
| ATOM | 980 | OH | TYR | A | 360 | 7.323 | -3.536 | 17.654 | 1.00 50.76 | O |
| ATOM | 981 | C | TYR | A | 360 | 5.356 | 2.606 | 12.969 | 1.00 37.09 | C |
| ATOM | 982 | O | TYR | A | 360 | 5.281 | 2.797 | 11.755 | 1.00 34.09 | O |
| ATOM | 983 | N | ILE | A | 361 | 5.410 | 3.592 | 13.856 | 1.00 35.39 | N |
| ATOM | 984 | CA | ILE | A | 361 | 5.444 | 4.994 | 13.459 | 1.00 37.33 | C |
| ATOM | 985 | CB | ILE | A | 361 | 4.073 | 5.712 | 13.683 | 1.00 35.70 | C |
| ATOM | 986 | CG2 | ILE | A | 361 | 3.059 | 5.191 | 12.688 | 1.00 36.49 | C |
| ATOM | 987 | CG1 | ILE | A | 361 | 3.558 | 5.497 | 15.111 | 1.00 39.72 | C |
| ATOM | 988 | CD1 | ILE | A | 361 | 4.158 | 6.419 | 16.157 | 1.00 40.32 | C |
| ATOM | 989 | C | ILE | A | 361 | 6.523 | 5.641 | 14.311 | 1.00 37.10 | C |
| ATOM | 990 | O | ILE | A | 361 | 6.841 | 5.141 | 15.389 | 1.00 38.07 | O |
| ATOM | 991 | N | HIS | A | 362 | 7.096 | 6.742 | 13.836 | 1.00 37.60 | N |
| ATOM | 992 | CA | HIS | A | 362 | 8.146 | 7.429 | 14.590 | 1.00 36.30 | C |
| ATOM | 993 | CB | HIS | A | 362 | 9.167 | 8.045 | 13.624 | 1.00 36.27 | C |
| ATOM | 994 | CG | HIS | A | 362 | 10.403 | 8.570 | 14.295 | 1.00 33.34 | C |
| ATOM | 995 | CD2 | HIS | A | 362 | 11.714 | 8.329 | 14.061 | 1.00 34.22 | C |
| ATOM | 996 | ND1 | HIS | A | 362 | 10.362 | 9.475 | 15.331 | 1.00 32.05 | N |
| ATOM | 997 | CE1 | HIS | A | 362 | 11.594 | 9.772 | 15.708 | 1.00 33.81 | C |
| ATOM | 998 | NE2 | HIS | A | 362 | 12.435 | 9.088 | 14.951 | 1.00 32.00 | N |
| ATOM | 999 | C | HIS | A | 362 | 7.559 | 8.525 | 15.467 | 1.00 37.29 | C |
| ATOM | 1000 | O | HIS | A | 362 | 7.849 | 8.589 | 16.660 | 1.00 38.45 | O |
| ATOM | 1001 | N | ARG | A | 363 | 6.742 | 9.374 | 14.849 | 1.00 35.25 | N |
| ATOM | 1002 | CA | ARG | A | 363 | 6.073 | 10.515 | 15.468 | 1.00 34.13 | C |
| ATOM | 1003 | CB | ARG | A | 363 | 5.119 | 10.067 | 16.596 | 1.00 37.88 | C |

Figure 14

| | | | | | | | | | | |
|---|---|---|---|---|---|---|---|---|---|---|
| ATOM | 1004 | CG | ARG | A | 363 | 5.755 | 9.683 | 17.903 | 1.00 43.36 | C |
| ATOM | 1005 | CD | ARG | A | 363 | 4.729 | 9.088 | 18.880 | 1.00 46.15 | C |
| ATOM | 1006 | NE | ARG | A | 363 | 3.595 | 9.967 | 19.156 | 1.00 49.62 | N |
| ATOM | 1007 | CZ | ARG | A | 363 | 2.395 | 9.851 | 18.590 | 1.00 51.45 | C |
| ATOM | 1008 | NH1 | ARG | A | 363 | 2.161 | 8.885 | 17.711 | 1.00 51.98 | N |
| ATOM | 1009 | NH2 | ARG | A | 363 | 1.429 | 10.704 | 18.898 | 1.00 50.99 | N |
| ATOM | 1010 | C | ARG | A | 363 | 6.983 | 11.658 | 15.945 | 1.00 33.13 | C |
| ATOM | 1011 | O | ARG | A | 363 | 6.489 | 12.730 | 16.284 | 1.00 31.60 | O |
| ATOM | 1012 | N | ASP | A | 364 | 8.301 | 11.461 | 15.954 | 1.00 31.17 | N |
| ATOM | 1013 | CA | ASP | A | 364 | 9.204 | 12.551 | 16.361 | 1.00 30.49 | C |
| ATOM | 1014 | CB | ASP | A | 364 | 9.748 | 12.305 | 17.769 | 1.00 31.72 | C |
| ATOM | 1015 | CG | ASP | A | 364 | 8.733 | 12.625 | 18.853 | 1.00 32.95 | C |
| ATOM | 1016 | OD1 | ASP | A | 364 | 8.382 | 13.820 | 19.012 | 1.00 35.93 | O |
| ATOM | 1017 | OD2 | ASP | A | 364 | 8.292 | 11.682 | 19.548 | 1.00 31.59 | O |
| ATOM | 1018 | C | ASP | A | 364 | 10.357 | 12.686 | 15.370 | 1.00 28.89 | C |
| ATOM | 1019 | O | ASP | A | 364 | 11.478 | 13.060 | 15.723 | 1.00 29.05 | O |
| ATOM | 1020 | N | LEU | A | 365 | 10.061 | 12.383 | 14.117 | 1.00 26.24 | N |
| ATOM | 1021 | CA | LEU | A | 365 | 11.047 | 12.430 | 13.058 | 1.00 25.36 | C |
| ATOM | 1022 | CB | LEU | A | 365 | 10.484 | 11.729 | 11.823 | 1.00 24.87 | C |
| ATOM | 1023 | CG | LEU | A | 365 | 11.375 | 11.691 | 10.586 | 1.00 25.36 | C |
| ATOM | 1024 | CD1 | LEU | A | 365 | 12.693 | 10.992 | 10.920 | 1.00 27.68 | C |
| ATOM | 1025 | CD2 | LEU | A | 365 | 10.650 | 10.965 | 9.468 | 1.00 26.79 | C |
| ATOM | 1026 | C | LEU | A | 365 | 11.464 | 13.851 | 12.691 | 1.00 25.80 | C |
| ATOM | 1027 | O | LEU | A | 365 | 10.628 | 14.670 | 12.335 | 1.00 23.64 | O |
| ATOM | 1028 | N | ARG | A | 366 | 12.764 | 14.123 | 12.796 | 1.00 25.47 | N |
| ATOM | 1029 | CA | ARG | A | 366 | 13.359 | 15.412 | 12.438 | 1.00 24.98 | C |
| ATOM | 1030 | CB | ARG | A | 366 | 12.856 | 16.554 | 13.331 | 1.00 27.33 | C |
| ATOM | 1031 | CG | ARG | A | 366 | 12.958 | 16.327 | 14.837 | 1.00 30.49 | C |
| ATOM | 1032 | CD | ARG | A | 366 | 12.444 | 17.552 | 15.576 | 1.00 31.87 | C |
| ATOM | 1033 | NE | ARG | A | 366 | 12.514 | 17.423 | 17.033 | 1.00 32.79 | N |
| ATOM | 1034 | CZ | ARG | A | 366 | 11.602 | 16.814 | 17.786 | 1.00 31.20 | C |
| ATOM | 1035 | NH1 | ARG | A | 366 | 10.526 | 16.261 | 17.239 | 1.00 29.79 | N |
| ATOM | 1036 | NH2 | ARG | A | 366 | 11.772 | 16.753 | 19.099 | 1.00 28.17 | N |
| ATOM | 1037 | C | ARG | A | 366 | 14.872 | 15.284 | 12.532 | 1.00 26.84 | C |
| ATOM | 1038 | O | ARG | A | 366 | 15.382 | 14.322 | 13.114 | 1.00 25.13 | O |
| ATOM | 1039 | N | ALA | A | 367 | 15.591 | 16.229 | 11.937 | 1.00 25.88 | N |
| ATOM | 1040 | CA | ALA | A | 367 | 17.046 | 16.161 | 11.945 | 1.00 29.33 | C |
| ATOM | 1041 | CB | ALA | A | 367 | 17.636 | 17.393 | 11.260 | 1.00 29.11 | C |
| ATOM | 1042 | C | ALA | A | 367 | 17.597 | 16.023 | 13.364 | 1.00 30.66 | C |
| ATOM | 1043 | O | ALA | A | 367 | 18.548 | 15.277 | 13.593 | 1.00 31.49 | O |
| ATOM | 1044 | N | ALA | A | 368 | 16.986 | 16.720 | 14.319 | 1.00 29.17 | N |
| ATOM | 1045 | CA | ALA | A | 368 | 17.447 | 16.666 | 15.700 | 1.00 30.23 | C |
| ATOM | 1046 | CB | ALA | A | 368 | 16.575 | 17.558 | 16.580 | 1.00 29.76 | C |
| ATOM | 1047 | C | ALA | A | 368 | 17.474 | 15.242 | 16.257 | 1.00 30.60 | C |
| ATOM | 1048 | O | ALA | A | 368 | 18.238 | 14.951 | 17.189 | 1.00 30.93 | O |
| ATOM | 1049 | N | ASN | A | 369 | 16.651 | 14.358 | 15.688 | 1.00 29.96 | N |
| ATOM | 1050 | CA | ASN | A | 369 | 16.587 | 12.973 | 16.145 | 1.00 29.87 | C |
| ATOM | 1051 | CB | ASN | A | 369 | 15.146 | 12.594 | 16.492 | 1.00 32.19 | C |
| ATOM | 1052 | CG | ASN | A | 369 | 14.630 | 13.360 | 17.677 | 1.00 30.64 | C |
| ATOM | 1053 | OD1 | ASN | A | 369 | 15.348 | 13.530 | 18.653 | 1.00 33.56 | O |
| ATOM | 1054 | ND2 | ASN | A | 369 | 13.385 | 13.822 | 17.609 | 1.00 29.60 | N |
| ATOM | 1055 | C | ASN | A | 369 | 17.180 | 11.954 | 15.187 | 1.00 31.28 | C |
| ATOM | 1056 | O | ASN | A | 369 | 16.728 | 10.807 | 15.118 | 1.00 32.58 | O |
| ATOM | 1057 | N | ILE | A | 370 | 18.197 | 12.395 | 14.453 | 1.00 30.43 | N |
| ATOM | 1058 | CA | ILE | A | 370 | 18.945 | 11.563 | 13.524 | 1.00 29.18 | C |
| ATOM | 1059 | CB | ILE | A | 370 | 18.893 | 12.139 | 12.089 | 1.00 28.81 | C |
| ATOM | 1060 | CG2 | ILE | A | 370 | 19.861 | 11.374 | 11.178 | 1.00 28.32 | C |
| ATOM | 1061 | CG1 | ILE | A | 370 | 17.463 | 12.066 | 11.539 | 1.00 26.83 | C |
| ATOM | 1062 | CD1 | ILE | A | 370 | 16.924 | 10.656 | 11.428 | 1.00 24.87 | C |
| ATOM | 1063 | C | ILE | A | 370 | 20.382 | 11.695 | 14.066 | 1.00 30.30 | C |

Figure 14

| | | | | | | | | | | |
|---|---|---|---|---|---|---|---|---|---|---|
| ATOM | 1064 | O | ILE | A | 370 | 20.834 | 12.805 | 14.334 | 1.00 29.07 | O |
| ATOM | 1065 | N | LEU | A | 371 | 21.077 | 10.584 | 14.282 | 1.00 29.57 | N |
| ATOM | 1066 | CA | LEU | A | 371 | 22.437 | 10.676 | 14.788 | 1.00 31.28 | C |
| ATOM | 1067 | CB | LEU | A | 371 | 22.618 | 9.765 | 16.010 | 1.00 32.00 | C |
| ATOM | 1068 | CG | LEU | A | 371 | 21.773 | 10.170 | 17.233 | 1.00 31.87 | C |
| ATOM | 1069 | CD1 | LEU | A | 371 | 21.865 | 9.119 | 18.322 | 1.00 31.20 | C |
| ATOM | 1070 | CD2 | LEU | A | 371 | 22.255 | 11.512 | 17.769 | 1.00 35.35 | C |
| ATOM | 1071 | C | LEU | A | 371 | 23.408 | 10.318 | 13.659 | 1.00 31.79 | C |
| ATOM | 1072 | O | LEU | A | 371 | 23.072 | 9.541 | 12.775 | 1.00 32.11 | O |
| ATOM | 1073 | N | VAL | A | 372 | 24.606 | 10.898 | 13.690 | 1.00 33.99 | N |
| ATOM | 1074 | CA | VAL | A | 372 | 25.592 | 10.670 | 12.633 | 1.00 34.10 | C |
| ATOM | 1075 | CB | VAL | A | 372 | 25.882 | 11.988 | 11.883 | 1.00 34.96 | C |
| ATOM | 1076 | CG1 | VAL | A | 372 | 26.746 | 11.720 | 10.656 | 1.00 34.45 | C |
| ATOM | 1077 | CG2 | VAL | A | 372 | 24.578 | 12.665 | 11.491 | 1.00 35.63 | C |
| ATOM | 1078 | C | VAL | A | 372 | 26.911 | 10.109 | 13.157 | 1.00 35.13 | C |
| ATOM | 1079 | O | VAL | A | 372 | 27.500 | 10.653 | 14.089 | 1.00 34.79 | O |
| ATOM | 1080 | N | SER | A | 373 | 27.379 | 9.017 | 12.565 | 1.00 36.50 | N |
| ATOM | 1081 | CA | SER | A | 373 | 28.638 | 8.422 | 13.016 | 1.00 40.24 | C |
| ATOM | 1082 | CB | SER | A | 373 | 28.681 | 6.934 | 12.667 | 1.00 39.52 | C |
| ATOM | 1083 | OG | SER | A | 373 | 28.707 | 6.736 | 11.269 | 1.00 37.83 | O |
| ATOM | 1084 | C | SER | A | 373 | 29.831 | 9.133 | 12.376 | 1.00 40.55 | C |
| ATOM | 1085 | O | SER | A | 373 | 29.659 | 10.039 | 11.564 | 1.00 40.47 | O |
| ATOM | 1086 | N | ASP | A | 374 | 31.038 | 8.726 | 12.750 | 1.00 42.72 | N |
| ATOM | 1087 | CA | ASP | A | 374 | 32.238 | 9.332 | 12.185 | 1.00 45.77 | C |
| ATOM | 1088 | CB | ASP | A | 374 | 33.486 | 8.832 | 12.922 | 1.00 47.91 | C |
| ATOM | 1089 | CG | ASP | A | 374 | 33.538 | 7.326 | 13.015 | 1.00 51.04 | C |
| ATOM | 1090 | OD1 | ASP | A | 374 | 33.401 | 6.659 | 11.967 | 1.00 49.72 | O |
| ATOM | 1091 | OD2 | ASP | A | 374 | 33.720 | 6.810 | 14.142 | 1.00 54.02 | O |
| ATOM | 1092 | C | ASP | A | 374 | 32.354 | 9.042 | 10.682 | 1.00 45.66 | C |
| ATOM | 1093 | O | ASP | A | 374 | 33.007 | 9.790 | 9.953 | 1.00 46.59 | O |
| ATOM | 1094 | N | THR | A | 375 | 31.722 | 7.964 | 10.222 | 1.00 46.46 | N |
| ATOM | 1095 | CA | THR | A | 375 | 31.741 | 7.611 | 8.801 | 1.00 47.34 | C |
| ATOM | 1096 | CB | THR | A | 375 | 31.516 | 6.100 | 8.572 | 1.00 48.71 | C |
| ATOM | 1097 | OG1 | THR | A | 375 | 30.271 | 5.706 | 9.158 | 1.00 51.02 | O |
| ATOM | 1098 | CG2 | THR | A | 375 | 32.647 | 5.286 | 9.188 | 1.00 49.09 | C |
| ATOM | 1099 | C | THR | A | 375 | 30.633 | 8.381 | 8.080 | 1.00 48.28 | C |
| ATOM | 1100 | O | THR | A | 375 | 30.476 | 8.287 | 6.866 | 1.00 48.99 | O |
| ATOM | 1101 | N | LEU | A | 376 | 29.863 | 9.140 | 8.851 | 1.00 48.40 | N |
| ATOM | 1102 | CA | LEU | A | 376 | 28.780 | 9.949 | 8.320 | 1.00 48.19 | C |
| ATOM | 1103 | CB | LEU | A | 376 | 29.270 | 10.796 | 7.146 | 1.00 48.90 | C |
| ATOM | 1104 | CG | LEU | A | 376 | 30.317 | 11.849 | 7.509 | 1.00 50.53 | C |
| ATOM | 1105 | CD1 | LEU | A | 376 | 30.563 | 12.761 | 6.314 | 1.00 49.59 | C |
| ATOM | 1106 | CD2 | LEU | A | 376 | 29.833 | 12.654 | 8.703 | 1.00 49.43 | C |
| ATOM | 1107 | C | LEU | A | 376 | 27.536 | 9.186 | 7.904 | 1.00 48.13 | C |
| ATOM | 1108 | O | LEU | A | 376 | 26.714 | 9.711 | 7.155 | 1.00 49.65 | O |
| ATOM | 1109 | N | SER | A | 377 | 27.395 | 7.947 | 8.364 | 1.00 46.68 | N |
| ATOM | 1110 | CA | SER | A | 377 | 26.194 | 7.186 | 8.047 | 1.00 44.34 | C |
| ATOM | 1111 | CB | SER | A | 377 | 26.440 | 5.680 | 8.189 | 1.00 45.45 | C |
| ATOM | 1112 | OG | SER | A | 377 | 26.708 | 5.321 | 9.532 | 1.00 49.11 | O |
| ATOM | 1113 | C | SER | A | 377 | 25.156 | 7.662 | 9.070 | 1.00 42.65 | C |
| ATOM | 1114 | O | SER | A | 377 | 25.511 | 8.042 | 10.187 | 1.00 41.40 | O |
| ATOM | 1115 | N | CYS | A | 378 | 23.883 | 7.657 | 8.694 | 1.00 40.87 | N |
| ATOM | 1116 | CA | CYS | A | 378 | 22.835 | 8.118 | 9.602 | 1.00 39.58 | C |
| ATOM | 1117 | CB | CYS | A | 378 | 21.898 | 9.072 | 8.864 | 1.00 40.22 | C |
| ATOM | 1118 | SG | CYS | A | 378 | 22.696 | 10.591 | 8.328 | 1.00 41.71 | S |
| ATOM | 1119 | C | CYS | A | 378 | 22.016 | 7.003 | 10.243 | 1.00 38.40 | C |
| ATOM | 1120 | O | CYS | A | 378 | 21.881 | 5.914 | 9.688 | 1.00 39.12 | O |
| ATOM | 1121 | N | LYS | A | 379 | 21.472 | 7.283 | 11.423 | 1.00 37.63 | N |
| ATOM | 1122 | CA | LYS | A | 379 | 20.645 | 6.317 | 12.129 | 1.00 37.97 | C |
| ATOM | 1123 | CB | LYS | A | 379 | 21.486 | 5.503 | 13.115 | 1.00 39.26 | C |

Figure 14

```
ATOM   1124  CG   LYS A 379      22.528   4.643  12.422  1.00 41.20           C
ATOM   1125  CD   LYS A 379      23.365   3.852  13.408  1.00 42.52           C
ATOM   1126  CE   LYS A 379      24.426   3.042  12.680  1.00 42.05           C
ATOM   1127  NZ   LYS A 379      25.210   2.200  13.617  1.00 44.19           N
ATOM   1128  C    LYS A 379      19.505   7.016  12.847  1.00 36.44           C
ATOM   1129  O    LYS A 379      19.673   8.086  13.429  1.00 35.40           O
ATOM   1130  N    ILE A 380      18.333   6.394  12.791  1.00 35.59           N
ATOM   1131  CA   ILE A 380      17.141   6.951  13.401  1.00 33.71           C
ATOM   1132  CB   ILE A 380      15.894   6.371  12.732  1.00 33.62           C
ATOM   1133  CG2  ILE A 380      14.651   6.991  13.330  1.00 31.88           C
ATOM   1134  CG1  ILE A 380      15.969   6.626  11.221  1.00 32.80           C
ATOM   1135  CD1  ILE A 380      14.885   5.955  10.430  1.00 33.72           C
ATOM   1136  C    ILE A 380      17.084   6.692  14.900  1.00 33.81           C
ATOM   1137  O    ILE A 380      17.236   5.559  15.351  1.00 32.66           O
ATOM   1138  N    ALA A 381      16.874   7.762  15.661  1.00 34.48           N
ATOM   1139  CA   ALA A 381      16.785   7.665  17.110  1.00 36.65           C
ATOM   1140  CB   ALA A 381      17.817   8.561  17.744  1.00 37.98           C
ATOM   1141  C    ALA A 381      15.397   8.058  17.598  1.00 36.57           C
ATOM   1142  O    ALA A 381      14.610   8.650  16.861  1.00 36.03           O
ATOM   1143  N    ASP A 382      15.118   7.721  18.851  1.00 39.09           N
ATOM   1144  CA   ASP A 382      13.854   8.028  19.523  1.00 40.47           C
ATOM   1145  CB   ASP A 382      13.891   9.451  20.097  1.00 42.78           C
ATOM   1146  CG   ASP A 382      14.710   9.544  21.369  1.00 46.96           C
ATOM   1147  OD1  ASP A 382      14.425   8.778  22.317  1.00 49.78           O
ATOM   1148  OD2  ASP A 382      15.640  10.378  21.423  1.00 49.44           O
ATOM   1149  C    ASP A 382      12.584   7.858  18.710  1.00 40.36           C
ATOM   1150  O    ASP A 382      11.759   8.769  18.641  1.00 40.42           O
ATOM   1151  N    PHE A 383      12.418   6.678  18.127  1.00 40.64           N
ATOM   1152  CA   PHE A 383      11.237   6.368  17.335  1.00 43.62           C
ATOM   1153  CB   PHE A 383      11.637   5.586  16.090  1.00 45.00           C
ATOM   1154  CG   PHE A 383      12.362   4.312  16.401  1.00 48.27           C
ATOM   1155  CD1  PHE A 383      13.717   4.329  16.718  1.00 49.22           C
ATOM   1156  CD2  PHE A 383      11.677   3.101  16.450  1.00 48.67           C
ATOM   1157  CE1  PHE A 383      14.379   3.157  17.084  1.00 51.20           C
ATOM   1158  CE2  PHE A 383      12.330   1.927  16.815  1.00 50.41           C
ATOM   1159  CZ   PHE A 383      13.680   1.953  17.133  1.00 49.24           C
ATOM   1160  C    PHE A 383      10.276   5.498  18.143  1.00 43.59           C
ATOM   1161  O    PHE A 383      10.642   4.949  19.177  1.00 43.67           O
ATOM   1162  N    GLY A 384       9.052   5.373  17.641  1.00 43.65           N
ATOM   1163  CA   GLY A 384       8.048   4.531  18.268  1.00 43.90           C
ATOM   1164  C    GLY A 384       7.520   4.909  19.633  1.00 44.40           C
ATOM   1165  O    GLY A 384       6.699   4.181  20.183  1.00 44.43           O
ATOM   1166  N    LEU A 385       7.979   6.026  20.188  1.00 44.95           N
ATOM   1167  CA   LEU A 385       7.512   6.448  21.502  1.00 47.39           C
ATOM   1168  CB   LEU A 385       8.303   7.662  21.989  1.00 46.04           C
ATOM   1169  CG   LEU A 385       9.783   7.442  22.313  1.00 47.05           C
ATOM   1170  CD1  LEU A 385      10.420   8.761  22.696  1.00 44.57           C
ATOM   1171  CD2  LEU A 385       9.923   6.421  23.437  1.00 45.11           C
ATOM   1172  C    LEU A 385       6.029   6.796  21.442  1.00 49.29           C
ATOM   1173  O    LEU A 385       5.480   6.997  20.362  1.00 49.78           O
ATOM   1174  N    ALA A 386       5.382   6.858  22.601  1.00 50.52           N
ATOM   1175  CA   ALA A 386       3.965   7.196  22.653  1.00 51.62           C
ATOM   1176  CB   ALA A 386       3.268   6.384  23.740  1.00 51.52           C
ATOM   1177  C    ALA A 386       3.796   8.685  22.926  1.00 51.76           C
ATOM   1178  O    ALA A 386       2.683   9.203  22.921  1.00 52.68           O
ATOM   1179  N    ARG A 387       4.904   9.377  23.165  1.00 51.75           N
ATOM   1180  CA   ARG A 387       4.835  10.802  23.447  1.00 50.72           C
ATOM   1181  CB   ARG A 387       5.276  11.078  24.890  1.00 50.70           C
ATOM   1182  CG   ARG A 387       6.764  10.902  25.139  1.00 51.66           C
ATOM   1183  CD   ARG A 387       7.101  11.016  26.620  1.00 51.52           C
```

Figure 14

```
ATOM   1184  NE   ARG A 387       8.537  10.905  26.871  1.00 51.18           N
ATOM   1185  CZ   ARG A 387       9.413  11.886  26.677  1.00 50.72           C
ATOM   1186  NH1  ARG A 387       9.007  13.067  26.231  1.00 47.99           N
ATOM   1187  NH2  ARG A 387      10.700  11.683  26.927  1.00 51.72           N
ATOM   1188  C    ARG A 387       5.693  11.621  22.496  1.00 50.18           C
ATOM   1189  O    ARG A 387       6.667  11.125  21.929  1.00 50.21           O
ATOM   1190  N    LEU A 388       5.317  12.880  22.314  1.00 48.41           N
ATOM   1191  CA   LEU A 388       6.090  13.763  21.468  1.00 46.87           C
ATOM   1192  CB   LEU A 388       5.212  14.915  20.985  1.00 47.24           C
ATOM   1193  CG   LEU A 388       3.919  14.442  20.299  1.00 49.39           C
ATOM   1194  CD1  LEU A 388       3.137  15.639  19.790  1.00 49.65           C
ATOM   1195  CD2  LEU A 388       4.249  13.492  19.142  1.00 46.28           C
ATOM   1196  C    LEU A 388       7.205  14.260  22.387  1.00 45.79           C
ATOM   1197  O    LEU A 388       6.942  14.614  23.537  1.00 44.97           O
ATOM   1198  N    ILE A 389       8.446  14.256  21.905  1.00 43.45           N
ATOM   1199  CA   ILE A 389       9.554  14.709  22.734  1.00 41.16           C
ATOM   1200  CB   ILE A 389      10.717  13.700  22.719  1.00 41.37           C
ATOM   1201  CG2  ILE A 389      10.200  12.301  23.046  1.00 39.83           C
ATOM   1202  CG1  ILE A 389      11.393  13.700  21.347  1.00 41.69           C
ATOM   1203  CD1  ILE A 389      12.588  12.770  21.247  1.00 40.04           C
ATOM   1204  C    ILE A 389      10.091  16.066  22.298  1.00 41.44           C
ATOM   1205  O    ILE A 389       9.839  16.525  21.181  1.00 39.03           O
ATOM   1206  N    GLU A 390      10.811  16.715  23.202  1.00 39.82           N
ATOM   1207  CA   GLU A 390      11.410  18.002  22.913  1.00 42.75           C
ATOM   1208  CB   GLU A 390      11.072  19.023  24.000  1.00 43.37           C
ATOM   1209  CG   GLU A 390       9.709  19.675  23.851  1.00 47.16           C
ATOM   1210  CD   GLU A 390       9.413  20.666  24.970  1.00 49.87           C
ATOM   1211  OE1  GLU A 390       9.202  20.222  26.120  1.00 49.46           O
ATOM   1212  OE2  GLU A 390       9.402  21.889  24.704  1.00 50.40           O
ATOM   1213  C    GLU A 390      12.910  17.769  22.859  1.00 42.67           C
ATOM   1214  O    GLU A 390      13.413  16.806  23.434  1.00 43.28           O
ATOM   1215  N    ASP A 391      13.630  18.644  22.177  1.00 43.02           N
ATOM   1216  CA   ASP A 391      15.073  18.474  22.066  1.00 44.17           C
ATOM   1217  CB   ASP A 391      15.577  19.164  20.802  1.00 45.89           C
ATOM   1218  CG   ASP A 391      14.915  18.624  19.546  1.00 47.93           C
ATOM   1219  OD1  ASP A 391      14.863  17.382  19.388  1.00 49.53           O
ATOM   1220  OD2  ASP A 391      14.454  19.434  18.718  1.00 47.49           O
ATOM   1221  C    ASP A 391      15.870  18.962  23.278  1.00 43.79           C
ATOM   1222  O    ASP A 391      17.085  18.801  23.318  1.00 44.74           O
ATOM   1223  N    ASN A 392      15.201  19.550  24.265  1.00 42.93           N
ATOM   1224  CA   ASN A 392      15.914  20.042  25.441  1.00 44.38           C
ATOM   1225  CB   ASN A 392      15.502  21.490  25.755  1.00 46.40           C
ATOM   1226  CG   ASN A 392      14.044  21.612  26.139  1.00 47.97           C
ATOM   1227  OD1  ASN A 392      13.171  21.073  25.466  1.00 52.00           O
ATOM   1228  ND2  ASN A 392      13.772  22.331  27.220  1.00 48.81           N
ATOM   1229  C    ASN A 392      15.704  19.161  26.667  1.00 43.17           C
ATOM   1230  O    ASN A 392      15.824  19.625  27.799  1.00 43.04           O
ATOM   1231  N    GLU A 393      15.401  17.886  26.436  1.00 41.57           N
ATOM   1232  CA   GLU A 393      15.175  16.954  27.531  1.00 41.29           C
ATOM   1233  CB   GLU A 393      14.243  15.820  27.084  1.00 40.65           C
ATOM   1234  CG   GLU A 393      12.881  16.324  26.570  1.00 39.28           C
ATOM   1235  CD   GLU A 393      11.888  15.214  26.271  1.00 38.45           C
ATOM   1236  OE1  GLU A 393      12.292  14.042  26.158  1.00 39.77           O
ATOM   1237  OE2  GLU A 393      10.689  15.524  26.136  1.00 39.90           O
ATOM   1238  C    GLU A 393      16.481  16.378  28.071  1.00 41.97           C
ATOM   1239  O    GLU A 393      16.591  16.114  29.266  1.00 41.22           O
ATOM   1240  N    TYR A 394      17.467  16.195  27.194  1.00 41.68           N
ATOM   1241  CA   TYR A 394      18.760  15.641  27.596  1.00 42.36           C
ATOM   1242  CB   TYR A 394      18.867  14.197  27.100  1.00 42.66           C
ATOM   1243  CG   TYR A 394      17.760  13.319  27.633  1.00 43.64           C
```

Figure 14

| | | | | | | | | | |
|---|---|---|---|---|---|---|---|---|---|
| ATOM | 1244 | CD1 | TYR | A | 394 | 17.707 | 12.977 | 28.986 | 1.00 44.55 | C |
| ATOM | 1245 | CE1 | TYR | A | 394 | 16.665 | 12.210 | 29.497 | 1.00 44.30 | C |
| ATOM | 1246 | CD2 | TYR | A | 394 | 16.738 | 12.862 | 26.799 | 1.00 43.17 | C |
| ATOM | 1247 | CE2 | TYR | A | 394 | 15.689 | 12.089 | 27.300 | 1.00 42.83 | C |
| ATOM | 1248 | CZ | TYR | A | 394 | 15.656 | 11.767 | 28.652 | 1.00 44.69 | C |
| ATOM | 1249 | OH | TYR | A | 394 | 14.620 | 11.010 | 29.162 | 1.00 44.03 | O |
| ATOM | 1250 | C | TYR | A | 394 | 19.942 | 16.470 | 27.073 | 1.00 45.03 | C |
| ATOM | 1251 | O | TYR | A | 394 | 21.098 | 16.037 | 27.149 | 1.00 44.72 | O |
| ATOM | 1252 | N | THR | A | 395 | 19.642 | 17.658 | 26.546 | 1.00 45.53 | N |
| ATOM | 1253 | CA | THR | A | 395 | 20.648 | 18.587 | 26.017 | 1.00 47.93 | C |
| ATOM | 1254 | CB | THR | A | 395 | 20.863 | 18.436 | 24.486 | 1.00 49.15 | C |
| ATOM | 1255 | OG1 | THR | A | 395 | 21.122 | 17.066 | 24.150 | 1.00 50.99 | O |
| ATOM | 1256 | CG2 | THR | A | 395 | 22.046 | 19.288 | 24.045 | 1.00 49.96 | C |
| ATOM | 1257 | C | THR | A | 395 | 20.116 | 19.997 | 26.243 | 1.00 48.84 | C |
| ATOM | 1258 | O | THR | A | 395 | 18.907 | 20.217 | 26.217 | 1.00 48.55 | O |
| ATOM | 1259 | N | ALA | A | 396 | 21.012 | 20.957 | 26.444 | 1.00 50.51 | N |
| ATOM | 1260 | CA | ALA | A | 396 | 20.591 | 22.334 | 26.667 | 1.00 53.12 | C |
| ATOM | 1261 | CB | ALA | A | 396 | 21.629 | 23.066 | 27.512 | 1.00 53.81 | C |
| ATOM | 1262 | C | ALA | A | 396 | 20.360 | 23.078 | 25.355 | 1.00 55.19 | C |
| ATOM | 1263 | O | ALA | A | 396 | 21.108 | 23.991 | 25.014 | 1.00 56.58 | O |
| ATOM | 1264 | N | ARG | A | 397 | 19.324 | 22.680 | 24.622 | 1.00 57.05 | N |
| ATOM | 1265 | CA | ARG | A | 397 | 18.980 | 23.316 | 23.352 | 1.00 57.71 | C |
| ATOM | 1266 | CB | ARG | A | 397 | 18.084 | 22.398 | 22.511 | 1.00 58.37 | C |
| ATOM | 1267 | CG | ARG | A | 397 | 18.812 | 21.245 | 21.827 | 1.00 58.76 | C |
| ATOM | 1268 | CD | ARG | A | 397 | 19.779 | 21.755 | 20.779 | 1.00 60.35 | C |
| ATOM | 1269 | NE | ARG | A | 397 | 20.514 | 20.677 | 20.124 | 1.00 62.46 | N |
| ATOM | 1270 | CZ | ARG | A | 397 | 19.953 | 19.723 | 19.387 | 1.00 64.00 | C |
| ATOM | 1271 | NH1 | ARG | A | 397 | 18.640 | 19.706 | 19.202 | 1.00 64.86 | N |
| ATOM | 1272 | NH2 | ARG | A | 397 | 20.702 | 18.778 | 18.839 | 1.00 63.99 | N |
| ATOM | 1273 | C | ARG | A | 397 | 18.259 | 24.634 | 23.602 | 1.00 58.03 | C |
| ATOM | 1274 | O | ARG | A | 397 | 18.869 | 25.617 | 24.022 | 1.00 57.93 | O |
| ATOM | 1275 | N | PRO | A | 403 | 8.147 | 21.137 | 18.707 | 1.00 40.64 | N |
| ATOM | 1276 | CD | PRO | A | 403 | 8.323 | 20.187 | 19.816 | 1.00 40.68 | C |
| ATOM | 1277 | CA | PRO | A | 403 | 8.357 | 20.482 | 17.411 | 1.00 40.53 | C |
| ATOM | 1278 | CB | PRO | A | 403 | 8.772 | 19.062 | 17.803 | 1.00 40.97 | C |
| ATOM | 1279 | CG | PRO | A | 403 | 8.105 | 18.860 | 19.139 | 1.00 40.38 | C |
| ATOM | 1280 | C | PRO | A | 403 | 7.125 | 20.527 | 16.491 | 1.00 42.05 | C |
| ATOM | 1281 | O | PRO | A | 403 | 6.887 | 19.617 | 15.672 | 1.00 42.14 | O |
| ATOM | 1282 | N | ILE | A | 404 | 6.358 | 21.607 | 16.619 | 1.00 39.92 | N |
| ATOM | 1283 | CA | ILE | A | 404 | 5.159 | 21.797 | 15.810 | 1.00 36.50 | C |
| ATOM | 1284 | CB | ILE | A | 404 | 4.380 | 23.063 | 16.281 | 1.00 37.50 | C |
| ATOM | 1285 | CG2 | ILE | A | 404 | 3.480 | 23.597 | 15.174 | 1.00 37.96 | C |
| ATOM | 1286 | CG1 | ILE | A | 404 | 3.542 | 22.720 | 17.513 | 1.00 40.25 | C |
| ATOM | 1287 | CD1 | ILE | A | 404 | 2.474 | 21.661 | 17.235 | 1.00 43.44 | C |
| ATOM | 1288 | C | ILE | A | 404 | 5.478 | 21.910 | 14.316 | 1.00 34.34 | C |
| ATOM | 1289 | O | ILE | A | 404 | 4.715 | 21.422 | 13.480 | 1.00 30.38 | O |
| ATOM | 1290 | N | LYS | A | 405 | 6.614 | 22.521 | 13.993 | 1.00 30.39 | N |
| ATOM | 1291 | CA | LYS | A | 405 | 7.020 | 22.726 | 12.602 | 1.00 30.75 | C |
| ATOM | 1292 | CB | LYS | A | 405 | 8.246 | 23.641 | 12.545 | 1.00 30.14 | C |
| ATOM | 1293 | CG | LYS | A | 405 | 7.963 | 25.058 | 13.042 | 1.00 31.17 | C |
| ATOM | 1294 | CD | LYS | A | 405 | 9.198 | 25.923 | 12.938 | 1.00 29.16 | C |
| ATOM | 1295 | CE | LYS | A | 405 | 8.855 | 27.395 | 13.159 | 1.00 32.45 | C |
| ATOM | 1296 | NZ | LYS | A | 405 | 9.918 | 28.275 | 12.586 | 1.00 32.43 | N |
| ATOM | 1297 | C | LYS | A | 405 | 7.274 | 21.489 | 11.733 | 1.00 28.85 | C |
| ATOM | 1298 | O | LYS | A | 405 | 7.536 | 21.620 | 10.545 | 1.00 26.70 | O |
| ATOM | 1299 | N | TRP | A | 406 | 7.198 | 20.302 | 12.324 | 1.00 30.02 | N |
| ATOM | 1300 | CA | TRP | A | 406 | 7.395 | 19.038 | 11.596 | 1.00 27.17 | C |
| ATOM | 1301 | CB | TRP | A | 406 | 8.535 | 18.215 | 12.236 | 1.00 30.16 | C |
| ATOM | 1302 | CG | TRP | A | 406 | 9.926 | 18.796 | 12.107 | 1.00 29.41 | C |
| ATOM | 1303 | CD2 | TRP | A | 406 | 10.507 | 19.809 | 12.926 | 1.00 30.53 | C |

Figure 14

| | | | | | | | | | |
|---|---|---|---|---|---|---|---|---|---|
| ATOM | 1304 | CE2 | TRP | A | 406 | 11.820 | 20.027 | 12.453 | 1.00 29.78 | C |
| ATOM | 1305 | CE3 | TRP | A | 406 | 10.047 | 20.559 | 14.019 | 1.00 31.69 | C |
| ATOM | 1306 | CD1 | TRP | A | 406 | 10.883 | 18.448 | 11.194 | 1.00 30.90 | C |
| ATOM | 1307 | NE1 | TRP | A | 406 | 12.023 | 19.182 | 11.396 | 1.00 28.26 | N |
| ATOM | 1308 | CZ2 | TRP | A | 406 | 12.679 | 20.963 | 13.031 | 1.00 32.33 | C |
| ATOM | 1309 | CZ3 | TRP | A | 406 | 10.907 | 21.493 | 14.597 | 1.00 33.88 | C |
| ATOM | 1310 | CH2 | TRP | A | 406 | 12.208 | 21.684 | 14.098 | 1.00 32.62 | C |
| ATOM | 1311 | C | TRP | A | 406 | 6.101 | 18.207 | 11.676 | 1.00 28.13 | C |
| ATOM | 1312 | O | TRP | A | 406 | 6.032 | 17.102 | 11.141 | 1.00 28.08 | O |
| ATOM | 1313 | N | THR | A | 407 | 5.084 | 18.733 | 12.355 | 1.00 27.85 | N |
| ATOM | 1314 | CA | THR | A | 407 | 3.820 | 18.006 | 12.531 | 1.00 28.63 | C |
| ATOM | 1315 | CB | THR | A | 407 | 3.141 | 18.430 | 13.848 | 1.00 27.98 | C |
| ATOM | 1316 | OG1 | THR | A | 407 | 4.111 | 18.428 | 14.899 | 1.00 29.55 | O |
| ATOM | 1317 | CG2 | THR | A | 407 | 2.021 | 17.471 | 14.207 | 1.00 31.58 | C |
| ATOM | 1318 | C | THR | A | 407 | 2.808 | 18.181 | 11.385 | 1.00 28.93 | C |
| ATOM | 1319 | O | THR | A | 407 | 2.463 | 19.306 | 11.016 | 1.00 28.31 | O |
| ATOM | 1320 | N | ALA | A | 408 | 2.338 | 17.066 | 10.821 | 1.00 28.61 | N |
| ATOM | 1321 | CA | ALA | A | 408 | 1.366 | 17.119 | 9.722 | 1.00 28.93 | C |
| ATOM | 1322 | CB | ALA | A | 408 | 1.117 | 15.717 | 9.165 | 1.00 28.04 | C |
| ATOM | 1323 | C | ALA | A | 408 | 0.055 | 17.734 | 10.211 | 1.00 29.93 | C |
| ATOM | 1324 | O | ALA | A | 408 | -0.272 | 17.643 | 11.392 | 1.00 31.37 | O |
| ATOM | 1325 | N | PRO | A | 409 | -0.720 | 18.358 | 9.302 | 1.00 30.79 | N |
| ATOM | 1326 | CD | PRO | A | 409 | -0.435 | 18.436 | 7.858 | 1.00 29.61 | C |
| ATOM | 1327 | CA | PRO | A | 409 | -2.003 | 19.002 | 9.627 | 1.00 31.06 | C |
| ATOM | 1328 | CB | PRO | A | 409 | -2.545 | 19.437 | 8.262 | 1.00 33.03 | C |
| ATOM | 1329 | CG | PRO | A | 409 | -1.300 | 19.592 | 7.413 | 1.00 32.78 | C |
| ATOM | 1330 | C | PRO | A | 409 | -3.012 | 18.137 | 10.387 | 1.00 31.90 | C |
| ATOM | 1331 | O | PRO | A | 409 | -3.644 | 18.607 | 11.338 | 1.00 29.28 | O |
| ATOM | 1332 | N | GLU | A | 410 | -3.166 | 16.884 | 9.970 | 1.00 31.61 | N |
| ATOM | 1333 | CA | GLU | A | 410 | -4.115 | 15.995 | 10.627 | 1.00 33.09 | C |
| ATOM | 1334 | CB | GLU | A | 410 | -4.306 | 14.700 | 9.803 | 1.00 32.15 | C |
| ATOM | 1335 | CG | GLU | A | 410 | -3.159 | 13.678 | 9.861 | 1.00 31.72 | C |
| ATOM | 1336 | CD | GLU | A | 410 | -2.051 | 13.928 | 8.836 | 1.00 29.45 | C |
| ATOM | 1337 | OE1 | GLU | A | 410 | -2.075 | 14.963 | 8.143 | 1.00 28.18 | O |
| ATOM | 1338 | OE2 | GLU | A | 410 | -1.146 | 13.081 | 8.731 | 1.00 30.85 | O |
| ATOM | 1339 | C | GLU | A | 410 | -3.671 | 15.685 | 12.066 | 1.00 33.89 | C |
| ATOM | 1340 | O | GLU | A | 410 | -4.498 | 15.439 | 12.946 | 1.00 32.85 | O |
| ATOM | 1341 | N | ALA | A | 411 | -2.364 | 15.722 | 12.311 | 1.00 35.19 | N |
| ATOM | 1342 | CA | ALA | A | 411 | -1.831 | 15.463 | 13.648 | 1.00 34.43 | C |
| ATOM | 1343 | CB | ALA | A | 411 | -0.338 | 15.182 | 13.574 | 1.00 33.55 | C |
| ATOM | 1344 | C | ALA | A | 411 | -2.087 | 16.681 | 14.524 | 1.00 36.25 | C |
| ATOM | 1345 | O | ALA | A | 411 | -2.423 | 16.555 | 15.700 | 1.00 36.19 | O |
| ATOM | 1346 | N | ILE | A | 412 | -1.932 | 17.863 | 13.937 | 1.00 37.52 | N |
| ATOM | 1347 | CA | ILE | A | 412 | -2.158 | 19.111 | 14.654 | 1.00 37.97 | C |
| ATOM | 1348 | CB | ILE | A | 412 | -1.762 | 20.323 | 13.800 | 1.00 38.95 | C |
| ATOM | 1349 | CG2 | ILE | A | 412 | -2.099 | 21.600 | 14.532 | 1.00 37.26 | C |
| ATOM | 1350 | CG1 | ILE | A | 412 | -0.272 | 20.270 | 13.470 | 1.00 38.18 | C |
| ATOM | 1351 | CD1 | ILE | A | 412 | 0.153 | 21.291 | 12.453 | 1.00 36.97 | C |
| ATOM | 1352 | C | ILE | A | 412 | -3.625 | 19.286 | 15.033 | 1.00 40.75 | C |
| ATOM | 1353 | O | ILE | A | 412 | -3.953 | 19.580 | 16.191 | 1.00 41.33 | O |
| ATOM | 1354 | N | ASN | A | 413 | -4.507 | 19.095 | 14.056 | 1.00 40.69 | N |
| ATOM | 1355 | CA | ASN | A | 413 | -5.937 | 19.279 | 14.272 | 1.00 43.01 | C |
| ATOM | 1356 | CB | ASN | A | 413 | -6.629 | 19.539 | 12.932 | 1.00 44.20 | C |
| ATOM | 1357 | CG | ASN | A | 413 | -6.017 | 20.697 | 12.193 | 1.00 44.93 | C |
| ATOM | 1358 | OD1 | ASN | A | 413 | -5.567 | 21.661 | 12.813 | 1.00 46.82 | O |
| ATOM | 1359 | ND2 | ASN | A | 413 | -5.998 | 20.619 | 10.866 | 1.00 44.98 | N |
| ATOM | 1360 | C | ASN | A | 413 | -6.698 | 18.184 | 15.000 | 1.00 44.02 | C |
| ATOM | 1361 | O | ASN | A | 413 | -7.579 | 18.472 | 15.811 | 1.00 43.72 | O |
| ATOM | 1362 | N | TYR | A | 414 | -6.367 | 16.929 | 14.719 | 1.00 45.87 | N |
| ATOM | 1363 | CA | TYR | A | 414 | -7.098 | 15.831 | 15.333 | 1.00 45.98 | C |

Figure 14

| | | | | | | | | | |
|---|---|---|---|---|---|---|---|---|---|
| ATOM | 1364 | CB | TYR | A | 414 | -7.806 | 15.057 | 14.228 | 1.00 46.83 | C |
| ATOM | 1365 | CG | TYR | A | 414 | -8.653 | 15.965 | 13.369 | 1.00 48.85 | C |
| ATOM | 1366 | CD1 | TYR | A | 414 | -9.786 | 16.594 | 13.894 | 1.00 50.01 | C |
| ATOM | 1367 | CE1 | TYR | A | 414 | -10.548 | 17.467 | 13.119 | 1.00 50.08 | C |
| ATOM | 1368 | CD2 | TYR | A | 414 | -8.304 | 16.232 | 12.044 | 1.00 49.26 | C |
| ATOM | 1369 | CE2 | TYR | A | 414 | -9.058 | 17.100 | 11.264 | 1.00 49.62 | C |
| ATOM | 1370 | CZ | TYR | A | 414 | -10.179 | 17.714 | 11.808 | 1.00 51.18 | C |
| ATOM | 1371 | OH | TYR | A | 414 | -10.935 | 18.571 | 11.035 | 1.00 55.18 | O |
| ATOM | 1372 | C | TYR | A | 414 | -6.283 | 14.891 | 16.208 | 1.00 46.03 | C |
| ATOM | 1373 | O | TYR | A | 414 | -6.845 | 14.095 | 16.969 | 1.00 45.61 | O |
| ATOM | 1374 | N | GLY | A | 415 | -4.964 | 14.991 | 16.108 | 1.00 44.96 | N |
| ATOM | 1375 | CA | GLY | A | 415 | -4.106 | 14.140 | 16.901 | 1.00 43.68 | C |
| ATOM | 1376 | C | GLY | A | 415 | -3.932 | 12.782 | 16.263 | 1.00 43.26 | C |
| ATOM | 1377 | O | GLY | A | 415 | -3.495 | 11.838 | 16.916 | 1.00 44.05 | O |
| ATOM | 1378 | N | THR | A | 416 | -4.271 | 12.666 | 14.985 | 1.00 43.04 | N |
| ATOM | 1379 | CA | THR | A | 416 | -4.113 | 11.386 | 14.308 | 1.00 42.88 | C |
| ATOM | 1380 | CB | THR | A | 416 | -5.144 | 11.188 | 13.161 | 1.00 43.50 | C |
| ATOM | 1381 | OG1 | THR | A | 416 | -4.465 | 11.161 | 11.898 | 1.00 45.01 | O |
| ATOM | 1382 | CG2 | THR | A | 416 | -6.176 | 12.303 | 13.161 | 1.00 41.95 | C |
| ATOM | 1383 | C | THR | A | 416 | -2.702 | 11.285 | 13.740 | 1.00 41.81 | C |
| ATOM | 1384 | O | THR | A | 416 | -2.298 | 12.061 | 12.869 | 1.00 42.38 | O |
| ATOM | 1385 | N | PHE | A | 417 | -1.955 | 10.321 | 14.256 | 1.00 39.02 | N |
| ATOM | 1386 | CA | PHE | A | 417 | -0.591 | 10.087 | 13.830 | 1.00 37.16 | C |
| ATOM | 1387 | CB | PHE | A | 417 | 0.332 | 10.062 | 15.046 | 1.00 37.76 | C |
| ATOM | 1388 | CG | PHE | A | 417 | 0.690 | 11.418 | 15.565 | 1.00 38.65 | C |
| ATOM | 1389 | CD1 | PHE | A | 417 | 1.777 | 12.111 | 15.035 | 1.00 39.82 | C |
| ATOM | 1390 | CD2 | PHE | A | 417 | -0.048 | 12.004 | 16.595 | 1.00 40.33 | C |
| ATOM | 1391 | CE1 | PHE | A | 417 | 2.136 | 13.363 | 15.515 | 1.00 38.26 | C |
| ATOM | 1392 | CE2 | PHE | A | 417 | 0.300 | 13.264 | 17.092 | 1.00 40.11 | C |
| ATOM | 1393 | CZ | PHE | A | 417 | 1.397 | 13.944 | 16.549 | 1.00 39.72 | C |
| ATOM | 1394 | C | PHE | A | 417 | -0.514 | 8.750 | 13.113 | 1.00 35.86 | C |
| ATOM | 1395 | O | PHE | A | 417 | -0.989 | 7.739 | 13.628 | 1.00 35.83 | O |
| ATOM | 1396 | N | THR | A | 418 | 0.062 | 8.752 | 11.916 | 1.00 33.72 | N |
| ATOM | 1397 | CA | THR | A | 418 | 0.229 | 7.523 | 11.146 | 1.00 30.24 | C |
| ATOM | 1398 | CB | THR | A | 418 | -0.842 | 7.356 | 10.044 | 1.00 31.58 | C |
| ATOM | 1399 | OG1 | THR | A | 418 | -0.573 | 8.270 | 8.975 | 1.00 29.41 | O |
| ATOM | 1400 | CG2 | THR | A | 418 | -2.241 | 7.601 | 10.602 | 1.00 32.49 | C |
| ATOM | 1401 | C | THR | A | 418 | 1.581 | 7.632 | 10.461 | 1.00 31.70 | C |
| ATOM | 1402 | O | THR | A | 418 | 2.283 | 8.647 | 10.602 | 1.00 30.00 | O |
| ATOM | 1403 | N | ILE | A | 419 | 1.951 | 6.591 | 9.723 | 1.00 28.13 | N |
| ATOM | 1404 | CA | ILE | A | 419 | 3.215 | 6.601 | 9.031 | 1.00 29.16 | C |
| ATOM | 1405 | CB | ILE | A | 419 | 3.493 | 5.242 | 8.333 | 1.00 28.49 | C |
| ATOM | 1406 | CG2 | ILE | A | 419 | 2.468 | 5.002 | 7.233 | 1.00 30.69 | C |
| ATOM | 1407 | CG1 | ILE | A | 419 | 4.910 | 5.228 | 7.741 | 1.00 29.90 | C |
| ATOM | 1408 | CD1 | ILE | A | 419 | 6.037 | 5.281 | 8.781 | 1.00 29.26 | C |
| ATOM | 1409 | C | ILE | A | 419 | 3.158 | 7.730 | 7.995 | 1.00 27.31 | C |
| ATOM | 1410 | O | ILE | A | 419 | 4.188 | 8.229 | 7.577 | 1.00 27.50 | O |
| ATOM | 1411 | N | LYS | A | 420 | 1.951 | 8.136 | 7.595 | 1.00 25.88 | N |
| ATOM | 1412 | CA | LYS | A | 420 | 1.805 | 9.220 | 6.617 | 1.00 25.71 | C |
| ATOM | 1413 | CB | LYS | A | 420 | 0.370 | 9.272 | 6.044 | 1.00 26.13 | C |
| ATOM | 1414 | CG | LYS | A | 420 | 0.017 | 8.115 | 5.099 | 1.00 26.34 | C |
| ATOM | 1415 | CD | LYS | A | 420 | 1.143 | 7.898 | 4.059 | 1.00 27.81 | C |
| ATOM | 1416 | CE | LYS | A | 420 | 0.731 | 6.917 | 2.971 | 1.00 28.12 | C |
| ATOM | 1417 | NZ | LYS | A | 420 | 1.848 | 6.576 | 2.049 | 1.00 27.74 | N |
| ATOM | 1418 | C | LYS | A | 420 | 2.160 | 10.575 | 7.243 | 1.00 24.73 | C |
| ATOM | 1419 | O | LYS | A | 420 | 2.590 | 11.497 | 6.544 | 1.00 23.80 | O |
| ATOM | 1420 | N | SER | A | 421 | 1.969 | 10.713 | 8.550 | 1.00 24.60 | N |
| ATOM | 1421 | CA | SER | A | 421 | 2.334 | 11.976 | 9.169 | 1.00 28.12 | C |
| ATOM | 1422 | CB | SER | A | 421 | 1.619 | 12.187 | 10.506 | 1.00 29.86 | C |
| ATOM | 1423 | OG | SER | A | 421 | 1.946 | 11.209 | 11.464 | 1.00 36.68 | O |

Figure 14

```
ATOM   1424  C    SER A 421       3.847  11.987   9.325  1.00 27.47           C
ATOM   1425  O    SER A 421       4.460  13.050   9.392  1.00 26.12           O
ATOM   1426  N    ASP A 422       4.461  10.807   9.370  1.00 26.36           N
ATOM   1427  CA   ASP A 422       5.920  10.763   9.448  1.00 26.22           C
ATOM   1428  CB   ASP A 422       6.446   9.367   9.770  1.00 27.77           C
ATOM   1429  CG   ASP A 422       6.225   8.970  11.213  1.00 30.93           C
ATOM   1430  OD1  ASP A 422       6.309   9.842  12.110  1.00 28.96           O
ATOM   1431  OD2  ASP A 422       5.990   7.765  11.451  1.00 31.85           O
ATOM   1432  C    ASP A 422       6.482  11.195   8.092  1.00 24.96           C
ATOM   1433  O    ASP A 422       7.497  11.890   8.039  1.00 24.79           O
ATOM   1434  N    VAL A 423       5.839  10.755   7.003  1.00 22.54           N
ATOM   1435  CA   VAL A 423       6.263  11.126   5.658  1.00 23.59           C
ATOM   1436  CB   VAL A 423       5.335  10.524   4.561  1.00 24.76           C
ATOM   1437  CG1  VAL A 423       5.670  11.152   3.188  1.00 26.68           C
ATOM   1438  CG2  VAL A 423       5.524   9.013   4.476  1.00 23.66           C
ATOM   1439  C    VAL A 423       6.229  12.658   5.564  1.00 24.08           C
ATOM   1440  O    VAL A 423       7.122  13.267   4.977  1.00 25.67           O
ATOM   1441  N    TRP A 424       5.206  13.283   6.139  1.00 23.10           N
ATOM   1442  CA   TRP A 424       5.149  14.751   6.119  1.00 23.70           C
ATOM   1443  CB   TRP A 424       3.887  15.260   6.826  1.00 23.06           C
ATOM   1444  CG   TRP A 424       3.857  16.758   7.051  1.00 25.71           C
ATOM   1445  CD2  TRP A 424       3.029  17.717   6.375  1.00 26.50           C
ATOM   1446  CE2  TRP A 424       3.331  18.987   6.920  1.00 28.82           C
ATOM   1447  CE3  TRP A 424       2.063  17.628   5.365  1.00 28.32           C
ATOM   1448  CD1  TRP A 424       4.608  17.469   7.951  1.00 23.23           C
ATOM   1449  NE1  TRP A 424       4.298  18.805   7.874  1.00 24.76           N
ATOM   1450  CZ2  TRP A 424       2.695  20.164   6.487  1.00 29.01           C
ATOM   1451  CZ3  TRP A 424       1.435  18.796   4.935  1.00 29.57           C
ATOM   1452  CH2  TRP A 424       1.755  20.046   5.497  1.00 28.53           C
ATOM   1453  C    TRP A 424       6.407  15.268   6.838  1.00 23.10           C
ATOM   1454  O    TRP A 424       7.111  16.139   6.331  1.00 22.80           O
ATOM   1455  N    SER A 425       6.681  14.715   8.014  1.00 22.00           N
ATOM   1456  CA   SER A 425       7.861  15.104   8.794  1.00 23.17           C
ATOM   1457  CB   SER A 425       7.960  14.281  10.091  1.00 23.78           C
ATOM   1458  OG   SER A 425       6.898  14.579  10.996  1.00 26.37           O
ATOM   1459  C    SER A 425       9.130  14.899   7.963  1.00 23.47           C
ATOM   1460  O    SER A 425      10.033  15.737   7.993  1.00 24.60           O
ATOM   1461  N    PHE A 426       9.206  13.789   7.225  1.00 23.43           N
ATOM   1462  CA   PHE A 426      10.388  13.525   6.393  1.00 25.02           C
ATOM   1463  CB   PHE A 426      10.247  12.199   5.628  1.00 23.93           C
ATOM   1464  CG   PHE A 426      11.479  11.813   4.855  1.00 26.21           C
ATOM   1465  CD1  PHE A 426      12.635  11.400   5.520  1.00 28.16           C
ATOM   1466  CD2  PHE A 426      11.508  11.913   3.463  1.00 27.08           C
ATOM   1467  CE1  PHE A 426      13.791  11.100   4.817  1.00 28.06           C
ATOM   1468  CE2  PHE A 426      12.667  11.611   2.749  1.00 28.58           C
ATOM   1469  CZ   PHE A 426      13.812  11.205   3.427  1.00 29.73           C
ATOM   1470  C    PHE A 426      10.590  14.681   5.399  1.00 25.85           C
ATOM   1471  O    PHE A 426      11.705  15.171   5.224  1.00 26.87           O
ATOM   1472  N    GLY A 427       9.510  15.102   4.741  1.00 26.79           N
ATOM   1473  CA   GLY A 427       9.599  16.227   3.820  1.00 23.73           C
ATOM   1474  C    GLY A 427      10.192  17.440   4.537  1.00 24.77           C
ATOM   1475  O    GLY A 427      11.067  18.118   4.003  1.00 23.53           O
ATOM   1476  N    ILE A 428       9.718  17.726   5.750  1.00 23.42           N
ATOM   1477  CA   ILE A 428      10.262  18.864   6.495  1.00 25.46           C
ATOM   1478  CB   ILE A 428       9.490  19.096   7.830  1.00 25.11           C
ATOM   1479  CG2  ILE A 428      10.075  20.283   8.572  1.00 23.63           C
ATOM   1480  CG1  ILE A 428       8.001  19.369   7.553  1.00 24.26           C
ATOM   1481  CD1  ILE A 428       7.748  20.609   6.646  1.00 22.17           C
ATOM   1482  C    ILE A 428      11.754  18.600   6.777  1.00 25.82           C
ATOM   1483  O    ILE A 428      12.599  19.487   6.624  1.00 25.99           O
```

Figure 14

```
ATOM   1484  N    LEU A 429      12.081  17.371   7.156  1.00 26.01           N
ATOM   1485  CA   LEU A 429      13.466  16.997   7.447  1.00 25.92           C
ATOM   1486  CB   LEU A 429      13.531  15.513   7.851  1.00 25.22           C
ATOM   1487  CG   LEU A 429      14.782  14.989   8.572  1.00 29.54           C
ATOM   1488  CD1  LEU A 429      14.524  13.580   9.122  1.00 28.51           C
ATOM   1489  CD2  LEU A 429      15.950  14.981   7.638  1.00 29.26           C
ATOM   1490  C    LEU A 429      14.359  17.242   6.221  1.00 27.45           C
ATOM   1491  O    LEU A 429      15.523  17.652   6.361  1.00 27.93           O
ATOM   1492  N    LEU A 430      13.835  16.975   5.025  1.00 26.79           N
ATOM   1493  CA   LEU A 430      14.617  17.178   3.800  1.00 26.33           C
ATOM   1494  CB   LEU A 430      13.815  16.737   2.565  1.00 27.22           C
ATOM   1495  CG   LEU A 430      13.693  15.220   2.337  1.00 25.20           C
ATOM   1496  CD1  LEU A 430      12.663  14.933   1.245  1.00 26.66           C
ATOM   1497  CD2  LEU A 430      15.056  14.647   1.971  1.00 24.83           C
ATOM   1498  C    LEU A 430      15.053  18.634   3.647  1.00 25.97           C
ATOM   1499  O    LEU A 430      16.141  18.913   3.155  1.00 27.17           O
ATOM   1500  N    THR A 431      14.207  19.559   4.075  1.00 26.04           N
ATOM   1501  CA   THR A 431      14.549  20.969   3.981  1.00 27.93           C
ATOM   1502  CB   THR A 431      13.310  21.883   4.258  1.00 25.40           C
ATOM   1503  OG1  THR A 431      12.921  21.787   5.625  1.00 25.58           O
ATOM   1504  CG2  THR A 431      12.141  21.466   3.370  1.00 22.62           C
ATOM   1505  C    THR A 431      15.699  21.287   4.957  1.00 29.44           C
ATOM   1506  O    THR A 431      16.594  22.083   4.630  1.00 28.88           O
ATOM   1507  N    GLU A 432      15.693  20.654   6.137  1.00 28.74           N
ATOM   1508  CA   GLU A 432      16.774  20.853   7.106  1.00 30.01           C
ATOM   1509  CB   GLU A 432      16.514  20.060   8.399  1.00 30.74           C
ATOM   1510  CG   GLU A 432      15.351  20.554   9.268  1.00 31.62           C
ATOM   1511  CD   GLU A 432      15.239  19.781  10.586  1.00 32.79           C
ATOM   1512  OE1  GLU A 432      14.697  18.651  10.586  1.00 31.61           O
ATOM   1513  OE2  GLU A 432      15.711  20.305  11.622  1.00 30.80           O
ATOM   1514  C    GLU A 432      18.104  20.355   6.502  1.00 30.78           C
ATOM   1515  O    GLU A 432      19.152  20.977   6.664  1.00 30.98           O
ATOM   1516  N    ILE A 433      18.042  19.216   5.821  1.00 29.35           N
ATOM   1517  CA   ILE A 433      19.208  18.593   5.214  1.00 31.67           C
ATOM   1518  CB   ILE A 433      18.835  17.194   4.680  1.00 31.03           C
ATOM   1519  CG2  ILE A 433      19.867  16.702   3.702  1.00 29.09           C
ATOM   1520  CG1  ILE A 433      18.672  16.225   5.855  1.00 28.12           C
ATOM   1521  CD1  ILE A 433      18.381  14.796   5.423  1.00 33.94           C
ATOM   1522  C    ILE A 433      19.884  19.390   4.093  1.00 34.17           C
ATOM   1523  O    ILE A 433      21.117  19.408   4.002  1.00 34.00           O
ATOM   1524  N    VAL A 434      19.095  20.059   3.254  1.00 34.21           N
ATOM   1525  CA   VAL A 434      19.659  20.820   2.147  1.00 36.88           C
ATOM   1526  CB   VAL A 434      18.726  20.785   0.909  1.00 36.97           C
ATOM   1527  CG1  VAL A 434      18.531  19.343   0.451  1.00 36.14           C
ATOM   1528  CG2  VAL A 434      17.393  21.451   1.234  1.00 34.60           C
ATOM   1529  C    VAL A 434      20.004  22.271   2.456  1.00 37.21           C
ATOM   1530  O    VAL A 434      20.632  22.940   1.635  1.00 39.38           O
ATOM   1531  N    THR A 435      19.599  22.760   3.625  1.00 37.64           N
ATOM   1532  CA   THR A 435      19.897  24.139   4.015  1.00 38.27           C
ATOM   1533  CB   THR A 435      18.648  24.873   4.536  1.00 36.71           C
ATOM   1534  OG1  THR A 435      18.075  24.124   5.619  1.00 34.77           O
ATOM   1535  CG2  THR A 435      17.619  25.057   3.417  1.00 33.01           C
ATOM   1536  C    THR A 435      20.935  24.124   5.130  1.00 39.57           C
ATOM   1537  O    THR A 435      21.181  25.138   5.782  1.00 39.50           O
ATOM   1538  N    HIS A 436      21.517  22.953   5.356  1.00 41.66           N
ATOM   1539  CA   HIS A 436      22.531  22.771   6.381  1.00 42.12           C
ATOM   1540  CB   HIS A 436      23.740  23.643   6.055  1.00 44.51           C
ATOM   1541  CG   HIS A 436      24.427  23.244   4.786  1.00 46.08           C
ATOM   1542  CD2  HIS A 436      24.441  23.819   3.560  1.00 47.23           C
```

Figure 14

| | | | | | | | | | |
|---|---|---|---|---|---|---|---|---|---|
| ATOM | 1543 | ND1 | HIS | A | 436 | 25.152 | 22.077 | 4.669 | 1.00 47.39 | N |
| ATOM | 1544 | CE1 | HIS | A | 436 | 25.579 | 21.948 | 3.425 | 1.00 46.73 | C |
| ATOM | 1545 | NE2 | HIS | A | 436 | 25.160 | 22.991 | 2.731 | 1.00 48.50 | N |
| ATOM | 1546 | C | HIS | A | 436 | 22.043 | 23.022 | 7.803 | 1.00 42.40 | C |
| ATOM | 1547 | O | HIS | A | 436 | 22.748 | 23.605 | 8.623 | 1.00 40.32 | O |
| ATOM | 1548 | N | GLY | A | 437 | 20.829 | 22.570 | 8.093 | 1.00 41.14 | N |
| ATOM | 1549 | CA | GLY | A | 437 | 20.304 | 22.722 | 9.434 | 1.00 41.48 | C |
| ATOM | 1550 | C | GLY | A | 437 | 19.385 | 23.896 | 9.683 | 1.00 41.43 | C |
| ATOM | 1551 | O | GLY | A | 437 | 18.931 | 24.080 | 10.814 | 1.00 42.39 | O |
| ATOM | 1552 | N | ARG | A | 438 | 19.095 | 24.691 | 8.658 | 1.00 41.34 | N |
| ATOM | 1553 | CA | ARG | A | 438 | 18.206 | 25.832 | 8.853 | 1.00 41.65 | C |
| ATOM | 1554 | CB | ARG | A | 438 | 17.934 | 26.559 | 7.531 | 1.00 43.30 | C |
| ATOM | 1555 | CG | ARG | A | 438 | 17.044 | 27.810 | 7.687 | 1.00 44.13 | C |
| ATOM | 1556 | CD | ARG | A | 438 | 16.278 | 28.144 | 6.410 | 1.00 46.01 | C |
| ATOM | 1557 | NE | ARG | A | 438 | 15.116 | 27.270 | 6.232 | 1.00 47.60 | N |
| ATOM | 1558 | CZ | ARG | A | 438 | 14.406 | 27.176 | 5.112 | 1.00 48.76 | C |
| ATOM | 1559 | NH1 | ARG | A | 438 | 14.725 | 27.902 | 4.050 | 1.00 50.71 | N |
| ATOM | 1560 | NH2 | ARG | A | 438 | 13.374 | 26.348 | 5.049 | 1.00 50.21 | N |
| ATOM | 1561 | C | ARG | A | 438 | 16.872 | 25.358 | 9.421 | 1.00 41.38 | C |
| ATOM | 1562 | O | ARG | A | 438 | 16.372 | 24.293 | 9.045 | 1.00 39.37 | O |
| ATOM | 1563 | N | ILE | A | 439 | 16.309 | 26.157 | 10.325 | 1.00 40.93 | N |
| ATOM | 1564 | CA | ILE | A | 439 | 15.014 | 25.872 | 10.942 | 1.00 41.28 | C |
| ATOM | 1565 | CB | ILE | A | 439 | 14.663 | 26.916 | 12.023 | 1.00 43.54 | C |
| ATOM | 1566 | CG2 | ILE | A | 439 | 13.342 | 26.544 | 12.703 | 1.00 43.49 | C |
| ATOM | 1567 | CG1 | ILE | A | 439 | 15.783 | 27.007 | 13.059 | 1.00 45.63 | C |
| ATOM | 1568 | CD1 | ILE | A | 439 | 15.561 | 28.097 | 14.103 | 1.00 47.01 | C |
| ATOM | 1569 | C | ILE | A | 439 | 13.926 | 25.968 | 9.871 | 1.00 40.65 | C |
| ATOM | 1570 | O | ILE | A | 439 | 14.009 | 26.802 | 8.972 | 1.00 39.92 | O |
| ATOM | 1571 | N | PRO | A | 440 | 12.893 | 25.113 | 9.948 | 1.00 40.06 | N |
| ATOM | 1572 | CD | PRO | A | 440 | 12.780 | 23.907 | 10.785 | 1.00 39.78 | C |
| ATOM | 1573 | CA | PRO | A | 440 | 11.816 | 25.168 | 8.949 | 1.00 38.59 | C |
| ATOM | 1574 | CB | PRO | A | 440 | 11.025 | 23.890 | 9.221 | 1.00 40.17 | C |
| ATOM | 1575 | CG | PRO | A | 440 | 12.068 | 22.955 | 9.861 | 1.00 39.71 | C |
| ATOM | 1576 | C | PRO | A | 440 | 10.963 | 26.428 | 9.165 | 1.00 38.77 | C |
| ATOM | 1577 | O | PRO | A | 440 | 10.921 | 26.970 | 10.272 | 1.00 38.51 | O |
| ATOM | 1578 | N | TYR | A | 441 | 10.283 | 26.888 | 8.118 | 1.00 36.14 | N |
| ATOM | 1579 | CA | TYR | A | 441 | 9.433 | 28.075 | 8.225 | 1.00 35.87 | C |
| ATOM | 1580 | CB | TYR | A | 441 | 8.169 | 27.725 | 9.021 | 1.00 33.60 | C |
| ATOM | 1581 | CG | TYR | A | 441 | 7.408 | 26.522 | 8.481 | 1.00 33.54 | C |
| ATOM | 1582 | CD1 | TYR | A | 441 | 6.514 | 26.651 | 7.408 | 1.00 32.00 | C |
| ATOM | 1583 | CE1 | TYR | A | 441 | 5.818 | 25.528 | 6.896 | 1.00 30.74 | C |
| ATOM | 1584 | CD2 | TYR | A | 441 | 7.592 | 25.251 | 9.034 | 1.00 31.51 | C |
| ATOM | 1585 | CE2 | TYR | A | 441 | 6.907 | 24.130 | 8.538 | 1.00 30.72 | C |
| ATOM | 1586 | CZ | TYR | A | 441 | 6.022 | 24.275 | 7.466 | 1.00 32.52 | C |
| ATOM | 1587 | OH | TYR | A | 441 | 5.360 | 23.168 | 6.967 | 1.00 27.95 | O |
| ATOM | 1588 | C | TYR | A | 441 | 10.189 | 29.245 | 8.895 | 1.00 37.44 | C |
| ATOM | 1589 | O | TYR | A | 441 | 9.696 | 29.870 | 9.834 | 1.00 35.73 | O |
| ATOM | 1590 | N | PRO | A | 442 | 11.389 | 29.573 | 8.382 | 1.00 39.30 | N |
| ATOM | 1591 | CD | PRO | A | 442 | 11.875 | 29.174 | 7.051 | 1.00 37.81 | C |
| ATOM | 1592 | CA | PRO | A | 442 | 12.214 | 30.658 | 8.930 | 1.00 41.76 | C |
| ATOM | 1593 | CB | PRO | A | 442 | 13.343 | 30.782 | 7.910 | 1.00 41.06 | C |
| ATOM | 1594 | CG | PRO | A | 442 | 12.659 | 30.391 | 6.625 | 1.00 41.13 | C |
| ATOM | 1595 | C | PRO | A | 442 | 11.448 | 31.965 | 9.114 | 1.00 44.40 | C |
| ATOM | 1596 | O | PRO | A | 442 | 10.849 | 32.486 | 8.173 | 1.00 44.80 | O |
| ATOM | 1597 | N | GLY | A | 443 | 11.467 | 32.482 | 10.339 | 1.00 45.57 | N |
| ATOM | 1598 | CA | GLY | A | 443 | 10.772 | 33.724 | 10.628 | 1.00 46.98 | C |
| ATOM | 1599 | C | GLY | A | 443 | 9.348 | 33.548 | 11.122 | 1.00 47.62 | C |
| ATOM | 1600 | O | GLY | A | 443 | 8.633 | 34.529 | 11.328 | 1.00 48.39 | O |
| ATOM | 1601 | N | MET | A | 444 | 8.933 | 32.300 | 11.322 | 1.00 47.38 | N |
| ATOM | 1602 | CA | MET | A | 444 | 7.577 | 32.015 | 11.777 | 1.00 46.24 | C |

Figure 14

| | | | | | | | | | |
|---|---|---|---|---|---|---|---|---|---|
| ATOM | 1603 | CB  | MET | A | 444 |  6.867 | 31.090 | 10.772 | 1.00 46.12 | C |
| ATOM | 1604 | CG  | MET | A | 444 |  6.548 | 31.725 |  9.422 | 1.00 46.13 | C |
| ATOM | 1605 | SD  | MET | A | 444 |  5.724 | 30.596 |  8.235 | 1.00 46.78 | S |
| ATOM | 1606 | CE  | MET | A | 444 |  4.528 | 29.866 |  9.225 | 1.00 43.23 | C |
| ATOM | 1607 | C   | MET | A | 444 |  7.573 | 31.356 | 13.151 | 1.00 45.12 | C |
| ATOM | 1608 | O   | MET | A | 444 |  8.461 | 30.567 | 13.468 | 1.00 46.43 | O |
| ATOM | 1609 | N   | THR | A | 445 |  6.578 | 31.686 | 13.965 | 1.00 43.94 | N |
| ATOM | 1610 | CA  | THR | A | 445 |  6.447 | 31.083 | 15.284 | 1.00 43.61 | C |
| ATOM | 1611 | CB  | THR | A | 445 |  5.756 | 32.036 | 16.290 | 1.00 44.45 | C |
| ATOM | 1612 | OG1 | THR | A | 445 |  4.442 | 32.357 | 15.821 | 1.00 46.87 | O |
| ATOM | 1613 | CG2 | THR | A | 445 |  6.556 | 33.320 | 16.459 | 1.00 45.41 | C |
| ATOM | 1614 | C   | THR | A | 445 |  5.561 | 29.855 | 15.101 | 1.00 42.81 | C |
| ATOM | 1615 | O   | THR | A | 445 |  4.975 | 29.663 | 14.032 | 1.00 42.57 | O |
| ATOM | 1616 | N   | ASN | A | 446 |  5.464 | 29.022 | 16.132 | 1.00 41.95 | N |
| ATOM | 1617 | CA  | ASN | A | 446 |  4.622 | 27.836 | 16.051 | 1.00 42.02 | C |
| ATOM | 1618 | CB  | ASN | A | 446 |  4.645 | 27.059 | 17.372 | 1.00 41.43 | C |
| ATOM | 1619 | CG  | ASN | A | 446 |  5.912 | 26.246 | 17.547 | 1.00 41.85 | C |
| ATOM | 1620 | OD1 | ASN | A | 446 |  6.798 | 26.273 | 16.695 | 1.00 40.31 | O |
| ATOM | 1621 | ND2 | ASN | A | 446 |  6.003 | 25.514 | 18.656 | 1.00 40.92 | N |
| ATOM | 1622 | C   | ASN | A | 446 |  3.181 | 28.205 | 15.692 | 1.00 41.58 | C |
| ATOM | 1623 | O   | ASN | A | 446 |  2.561 | 27.547 | 14.859 | 1.00 40.42 | O |
| ATOM | 1624 | N   | PRO | A | 447 |  2.630 | 29.260 | 16.322 | 1.00 42.21 | N |
| ATOM | 1625 | CD  | PRO | A | 447 |  3.151 | 29.975 | 17.504 | 1.00 43.11 | C |
| ATOM | 1626 | CA  | PRO | A | 447 |  1.250 | 29.671 | 16.024 | 1.00 41.73 | C |
| ATOM | 1627 | CB  | PRO | A | 447 |  0.930 | 30.668 | 17.142 | 1.00 43.30 | C |
| ATOM | 1628 | CG  | PRO | A | 447 |  2.290 | 31.206 | 17.538 | 1.00 43.87 | C |
| ATOM | 1629 | C   | PRO | A | 447 |  1.056 | 30.259 | 14.622 | 1.00 41.27 | C |
| ATOM | 1630 | O   | PRO | A | 447 | -0.026 | 30.154 | 14.050 | 1.00 41.52 | O |
| ATOM | 1631 | N   | GLU | A | 448 |  2.095 | 30.887 | 14.078 | 1.00 40.36 | N |
| ATOM | 1632 | CA  | GLU | A | 448 |  2.016 | 31.448 | 12.735 | 1.00 40.08 | C |
| ATOM | 1633 | CB  | GLU | A | 448 |  3.181 | 32.397 | 12.480 | 1.00 41.23 | C |
| ATOM | 1634 | CG  | GLU | A | 448 |  2.964 | 33.784 | 13.045 | 1.00 46.53 | C |
| ATOM | 1635 | CD  | GLU | A | 448 |  4.249 | 34.571 | 13.165 | 1.00 46.81 | C |
| ATOM | 1636 | OE1 | GLU | A | 448 |  4.990 | 34.688 | 12.165 | 1.00 51.33 | O |
| ATOM | 1637 | OE2 | GLU | A | 448 |  4.513 | 35.078 | 14.268 | 1.00 50.85 | O |
| ATOM | 1638 | C   | GLU | A | 448 |  2.063 | 30.291 | 11.745 | 1.00 39.47 | C |
| ATOM | 1639 | O   | GLU | A | 448 |  1.435 | 30.337 | 10.688 | 1.00 39.13 | O |
| ATOM | 1640 | N   | VAL | A | 449 |  2.817 | 29.254 | 12.093 | 1.00 37.05 | N |
| ATOM | 1641 | CA  | VAL | A | 449 |  2.893 | 28.087 | 11.236 | 1.00 35.88 | C |
| ATOM | 1642 | CB  | VAL | A | 449 |  3.922 | 27.060 | 11.762 | 1.00 36.38 | C |
| ATOM | 1643 | CG1 | VAL | A | 449 |  3.761 | 25.719 | 11.026 | 1.00 34.01 | C |
| ATOM | 1644 | CG2 | VAL | A | 449 |  5.330 | 27.596 | 11.546 | 1.00 35.43 | C |
| ATOM | 1645 | C   | VAL | A | 449 |  1.502 | 27.470 | 11.204 | 1.00 34.45 | C |
| ATOM | 1646 | O   | VAL | A | 449 |  0.974 | 27.190 | 10.134 | 1.00 32.47 | O |
| ATOM | 1647 | N   | ILE | A | 450 |  0.903 | 27.298 | 12.382 | 1.00 35.58 | N |
| ATOM | 1648 | CA  | ILE | A | 450 | -0.437 | 26.716 | 12.508 | 1.00 37.70 | C |
| ATOM | 1649 | CB  | ILE | A | 450 | -0.893 | 26.686 | 13.986 | 1.00 37.65 | C |
| ATOM | 1650 | CG2 | ILE | A | 450 | -2.329 | 26.184 | 14.077 | 1.00 37.48 | C |
| ATOM | 1651 | CG1 | ILE | A | 450 |  0.073 | 25.832 | 14.817 | 1.00 39.85 | C |
| ATOM | 1652 | CD1 | ILE | A | 450 |  0.183 | 24.381 | 14.377 | 1.00 39.98 | C |
| ATOM | 1653 | C   | ILE | A | 450 | -1.480 | 27.479 | 11.681 | 1.00 38.02 | C |
| ATOM | 1654 | O   | ILE | A | 450 | -2.297 | 26.867 | 10.992 | 1.00 38.66 | O |
| ATOM | 1655 | N   | GLN | A | 451 | -1.458 | 28.808 | 11.767 | 1.00 36.81 | N |
| ATOM | 1656 | CA  | GLN | A | 451 | -2.383 | 29.656 | 11.006 | 1.00 36.89 | C |
| ATOM | 1657 | CB  | GLN | A | 451 | -2.199 | 31.128 | 11.384 | 1.00 38.68 | C |
| ATOM | 1658 | CG  | GLN | A | 451 | -2.779 | 31.524 | 12.743 | 1.00 43.54 | C |
| ATOM | 1659 | CD  | GLN | A | 451 | -1.981 | 32.626 | 13.417 | 1.00 46.18 | C |
| ATOM | 1660 | OE1 | GLN | A | 451 | -1.544 | 33.579 | 12.767 | 1.00 48.28 | O |
| ATOM | 1661 | NE2 | GLN | A | 451 | -1.791 | 32.503 | 14.729 | 1.00 46.38 | N |
| ATOM | 1662 | C   | GLN | A | 451 | -2.162 | 29.514 |  9.502 | 1.00 34.21 | C |

Figure 14

| | | | | | | | | | | |
|---|---|---|---|---|---|---|---|---|---|---|
| ATOM | 1663 | O   | GLN | A | 451 | -3.113 | 29.413 | 8.743  | 1.00 31.85 | O |
| ATOM | 1664 | N   | ASN | A | 452 | -0.899 | 29.523 | 9.085  | 1.00 33.92 | N |
| ATOM | 1665 | CA  | ASN | A | 452 | -0.544 | 29.399 | 7.678  | 1.00 32.77 | C |
| ATOM | 1666 | CB  | ASN | A | 452 | 0.946  | 29.692 | 7.493  | 1.00 34.54 | C |
| ATOM | 1667 | CG  | ASN | A | 452 | 1.207  | 31.137 | 7.107  | 1.00 38.56 | C |
| ATOM | 1668 | OD1 | ASN | A | 452 | 0.999  | 31.525 | 5.963  | 1.00 36.93 | O |
| ATOM | 1669 | ND2 | ASN | A | 452 | 1.653  | 31.940 | 8.064  | 1.00 39.38 | N |
| ATOM | 1670 | C   | ASN | A | 452 | -0.889 | 28.033 | 7.079  | 1.00 33.41 | C |
| ATOM | 1671 | O   | ASN | A | 452 | -1.305 | 27.947 | 5.921  | 1.00 30.86 | O |
| ATOM | 1672 | N   | LEU | A | 453 | -0.709 | 26.968 | 7.857  | 1.00 32.03 | N |
| ATOM | 1673 | CA  | LEU | A | 453 | -1.032 | 25.627 | 7.371  | 1.00 32.39 | C |
| ATOM | 1674 | CB  | LEU | A | 453 | -0.562 | 24.561 | 8.366  | 1.00 31.95 | C |
| ATOM | 1675 | CG  | LEU | A | 453 | 0.967  | 24.475 | 8.442  | 1.00 34.91 | C |
| ATOM | 1676 | CD1 | LEU | A | 453 | 1.397  | 23.415 | 9.466  | 1.00 34.09 | C |
| ATOM | 1677 | CD2 | LEU | A | 453 | 1.513  | 24.149 | 7.054  | 1.00 34.01 | C |
| ATOM | 1678 | C   | LEU | A | 453 | -2.538 | 25.542 | 7.195  | 1.00 31.86 | C |
| ATOM | 1679 | O   | LEU | A | 453 | -3.041 | 24.801 | 6.346  | 1.00 30.08 | O |
| ATOM | 1680 | N   | GLU | A | 454 | -3.256 | 26.310 | 8.010  | 1.00 32.77 | N |
| ATOM | 1681 | CA  | GLU | A | 454 | -4.709 | 26.319 | 7.929  | 1.00 34.95 | C |
| ATOM | 1682 | CB  | GLU | A | 454 | -5.300 | 27.246 | 8.998  | 1.00 36.97 | C |
| ATOM | 1683 | CG  | GLU | A | 454 | -4.953 | 26.837 | 10.425 | 1.00 43.43 | C |
| ATOM | 1684 | CD  | GLU | A | 454 | -5.485 | 27.804 | 11.478 | 1.00 47.30 | C |
| ATOM | 1685 | OE1 | GLU | A | 454 | -5.532 | 29.025 | 11.207 | 1.00 47.63 | O |
| ATOM | 1686 | OE2 | GLU | A | 454 | -5.837 | 27.340 | 12.585 | 1.00 50.64 | O |
| ATOM | 1687 | C   | GLU | A | 454 | -5.082 | 26.817 | 6.537  | 1.00 33.76 | C |
| ATOM | 1688 | O   | GLU | A | 454 | -6.077 | 26.382 | 5.955  | 1.00 34.09 | O |
| ATOM | 1689 | N   | ARG | A | 455 | -4.259 | 27.717 | 6.005  | 1.00 31.87 | N |
| ATOM | 1690 | CA  | ARG | A | 455 | -4.500 | 28.297 | 4.684  | 1.00 34.22 | C |
| ATOM | 1691 | CB  | ARG | A | 455 | -3.972 | 29.742 | 4.618  | 1.00 35.09 | C |
| ATOM | 1692 | CG  | ARG | A | 455 | -4.292 | 30.602 | 5.827  | 1.00 37.82 | C |
| ATOM | 1693 | CD  | ARG | A | 455 | -4.121 | 32.088 | 5.514  | 1.00 38.00 | C |
| ATOM | 1694 | NE  | ARG | A | 455 | -3.663 | 32.835 | 6.679  | 1.00 44.24 | N |
| ATOM | 1695 | CZ  | ARG | A | 455 | -2.410 | 33.234 | 6.872  | 1.00 44.34 | C |
| ATOM | 1696 | NH1 | ARG | A | 455 | -1.473 | 32.971 | 5.972  | 1.00 45.42 | N |
| ATOM | 1697 | NH2 | ARG | A | 455 | -2.090 | 33.892 | 7.975  | 1.00 50.40 | N |
| ATOM | 1698 | C   | ARG | A | 455 | -3.854 | 27.491 | 3.553  | 1.00 32.48 | C |
| ATOM | 1699 | O   | ARG | A | 455 | -3.877 | 27.923 | 2.398  | 1.00 32.77 | O |
| ATOM | 1700 | N   | GLY | A | 456 | -3.258 | 26.345 | 3.889  | 1.00 31.91 | N |
| ATOM | 1701 | CA  | GLY | A | 456 | -2.640 | 25.498 | 2.881  | 1.00 29.30 | C |
| ATOM | 1702 | C   | GLY | A | 456 | -1.253 | 25.930 | 2.449  | 1.00 29.86 | C |
| ATOM | 1703 | O   | GLY | A | 456 | -0.751 | 25.500 | 1.420  | 1.00 30.02 | O |
| ATOM | 1704 | N   | TYR | A | 457 | -0.615 | 26.778 | 3.242  | 1.00 28.04 | N |
| ATOM | 1705 | CA  | TYR | A | 457 | 0.720  | 27.245 | 2.918  | 1.00 29.14 | C |
| ATOM | 1706 | CB  | TYR | A | 457 | 1.163  | 28.249 | 3.984  | 1.00 30.57 | C |
| ATOM | 1707 | CG  | TYR | A | 457 | 2.575  | 28.727 | 3.818  | 1.00 32.01 | C |
| ATOM | 1708 | CD1 | TYR | A | 457 | 3.642  | 28.041 | 4.400  | 1.00 33.86 | C |
| ATOM | 1709 | CE1 | TYR | A | 457 | 4.953  | 28.519 | 4.279  | 1.00 32.55 | C |
| ATOM | 1710 | CD2 | TYR | A | 457 | 2.846  | 29.897 | 3.105  | 1.00 31.43 | C |
| ATOM | 1711 | CE2 | TYR | A | 457 | 4.137  | 30.380 | 2.979  | 1.00 31.97 | C |
| ATOM | 1712 | CZ  | TYR | A | 457 | 5.188  | 29.691 | 3.567  | 1.00 33.00 | C |
| ATOM | 1713 | OH  | TYR | A | 457 | 6.464  | 30.185 | 3.439  | 1.00 31.14 | O |
| ATOM | 1714 | C   | TYR | A | 457 | 1.753  | 26.112 | 2.840  | 1.00 29.22 | C |
| ATOM | 1715 | O   | TYR | A | 457 | 1.663  | 25.128 | 3.576  | 1.00 27.11 | O |
| ATOM | 1716 | N   | ARG | A | 458 | 2.748  | 26.276 | 1.972  | 1.00 28.27 | N |
| ATOM | 1717 | CA  | ARG | A | 458 | 3.813  | 25.289 | 1.824  | 1.00 30.98 | C |
| ATOM | 1718 | CB  | ARG | A | 458 | 3.556  | 24.365 | 0.614  | 1.00 30.44 | C |
| ATOM | 1719 | CG  | ARG | A | 458 | 2.333  | 23.441 | 0.730  | 1.00 28.57 | C |
| ATOM | 1720 | CD  | ARG | A | 458 | 2.561  | 22.347 | 1.755  | 1.00 33.15 | C |
| ATOM | 1721 | NE  | ARG | A | 458 | 1.449  | 21.402 | 1.871  | 1.00 30.05 | N |
| ATOM | 1722 | CZ  | ARG | A | 458 | 0.328  | 21.630 | 2.546  | 1.00 30.42 | C |

Figure 14

| | | | | | | | | | | |
|---|---|---|---|---|---|---|---|---|---|---|
| ATOM | 1723 | NH1 | ARG | A | 458 | 0.144 | 22.784 | 3.180 | 1.00 30.40 | N |
| ATOM | 1724 | NH2 | ARG | A | 458 | -0.607 | 20.696 | 2.603 | 1.00 30.10 | N |
| ATOM | 1725 | C | ARG | A | 458 | 5.111 | 26.058 | 1.618 | 1.00 32.43 | C |
| ATOM | 1726 | O | ARG | A | 458 | 5.126 | 27.053 | 0.895 | 1.00 31.71 | O |
| ATOM | 1727 | N | MET | A | 459 | 6.187 | 25.621 | 2.270 | 1.00 32.27 | N |
| ATOM | 1728 | CA | MET | A | 459 | 7.477 | 26.289 | 2.115 | 1.00 32.97 | C |
| ATOM | 1729 | CB | MET | A | 459 | 8.581 | 25.566 | 2.903 | 1.00 31.73 | C |
| ATOM | 1730 | CG | MET | A | 459 | 8.662 | 25.921 | 4.381 | 1.00 32.95 | C |
| ATOM | 1731 | SD | MET | A | 459 | 10.019 | 25.032 | 5.209 | 1.00 34.83 | S |
| ATOM | 1732 | CE | MET | A | 459 | 9.241 | 23.479 | 5.556 | 1.00 36.96 | C |
| ATOM | 1733 | C | MET | A | 459 | 7.854 | 26.289 | 0.644 | 1.00 32.71 | C |
| ATOM | 1734 | O | MET | A | 459 | 7.430 | 25.420 | -0.118 | 1.00 31.27 | O |
| ATOM | 1735 | N | VAL | A | 460 | 8.682 | 27.256 | 0.263 | 1.00 33.67 | N |
| ATOM | 1736 | CA | VAL | A | 460 | 9.143 | 27.396 | -1.107 | 1.00 35.10 | C |
| ATOM | 1737 | CB | VAL | A | 460 | 9.448 | 28.884 | -1.435 | 1.00 36.59 | C |
| ATOM | 1738 | CG1 | VAL | A | 460 | 8.325 | 29.776 | -0.912 | 1.00 37.72 | C |
| ATOM | 1739 | CG2 | VAL | A | 460 | 10.765 | 29.292 | -0.822 | 1.00 37.01 | C |
| ATOM | 1740 | C | VAL | A | 460 | 10.411 | 26.568 | -1.313 | 1.00 34.23 | C |
| ATOM | 1741 | O | VAL | A | 460 | 11.001 | 26.069 | -0.353 | 1.00 34.71 | O |
| ATOM | 1742 | N | ARG | A | 461 | 10.826 | 26.410 | -2.563 | 1.00 34.89 | N |
| ATOM | 1743 | CA | ARG | A | 461 | 12.034 | 25.645 | -2.856 | 1.00 36.06 | C |
| ATOM | 1744 | CB | ARG | A | 461 | 12.257 | 25.544 | -4.367 | 1.00 36.69 | C |
| ATOM | 1745 | CG | ARG | A | 461 | 13.480 | 24.708 | -4.747 | 1.00 40.49 | C |
| ATOM | 1746 | CD | ARG | A | 461 | 13.662 | 24.639 | -6.255 | 1.00 43.76 | C |
| ATOM | 1747 | NE | ARG | A | 461 | 13.991 | 25.933 | -6.855 | 1.00 47.01 | N |
| ATOM | 1748 | CZ | ARG | A | 461 | 15.194 | 26.499 | -6.808 | 1.00 50.85 | C |
| ATOM | 1749 | NH1 | ARG | A | 461 | 16.197 | 25.886 | -6.185 | 1.00 50.45 | N |
| ATOM | 1750 | NH2 | ARG | A | 461 | 15.407 | 27.672 | -7.398 | 1.00 49.87 | N |
| ATOM | 1751 | C | ARG | A | 461 | 13.246 | 26.315 | -2.203 | 1.00 36.53 | C |
| ATOM | 1752 | O | ARG | A | 461 | 13.533 | 27.480 | -2.458 | 1.00 34.42 | O |
| ATOM | 1753 | N | PRO | A | 462 | 13.962 | 25.587 | -1.335 | 1.00 37.50 | N |
| ATOM | 1754 | CD | PRO | A | 462 | 13.663 | 24.273 | -0.743 | 1.00 36.38 | C |
| ATOM | 1755 | CA | PRO | A | 462 | 15.131 | 26.196 | -0.691 | 1.00 37.88 | C |
| ATOM | 1756 | CB | PRO | A | 462 | 15.541 | 25.150 | 0.346 | 1.00 37.98 | C |
| ATOM | 1757 | CG | PRO | A | 462 | 14.250 | 24.418 | 0.631 | 1.00 36.14 | C |
| ATOM | 1758 | C | PRO | A | 462 | 16.240 | 26.449 | -1.703 | 1.00 38.97 | C |
| ATOM | 1759 | O | PRO | A | 462 | 16.322 | 25.763 | -2.720 | 1.00 36.71 | O |
| ATOM | 1760 | N | ASP | A | 463 | 17.088 | 27.434 | -1.421 | 1.00 41.76 | N |
| ATOM | 1761 | CA | ASP | A | 463 | 18.197 | 27.755 | -2.309 | 1.00 45.03 | C |
| ATOM | 1762 | CB | ASP | A | 463 | 18.967 | 28.972 | -1.790 | 1.00 46.54 | C |
| ATOM | 1763 | CG | ASP | A | 463 | 18.134 | 30.238 | -1.811 | 1.00 47.40 | C |
| ATOM | 1764 | OD1 | ASP | A | 463 | 17.596 | 30.584 | -2.886 | 1.00 48.34 | O |
| ATOM | 1765 | OD2 | ASP | A | 463 | 18.020 | 30.887 | -0.753 | 1.00 47.86 | O |
| ATOM | 1766 | C | ASP | A | 463 | 19.141 | 26.565 | -2.429 | 1.00 46.55 | C |
| ATOM | 1767 | O | ASP | A | 463 | 19.432 | 25.885 | -1.441 | 1.00 46.59 | O |
| ATOM | 1768 | N | ASN | A | 464 | 19.614 | 26.320 | -3.646 | 1.00 47.78 | N |
| ATOM | 1769 | CA | ASN | A | 464 | 20.523 | 25.212 | -3.898 | 1.00 49.52 | C |
| ATOM | 1770 | CB | ASN | A | 464 | 21.836 | 25.433 | -3.142 | 1.00 51.66 | C |
| ATOM | 1771 | CG | ASN | A | 464 | 22.654 | 26.566 | -3.732 | 1.00 52.86 | C |
| ATOM | 1772 | OD1 | ASN | A | 464 | 23.196 | 26.443 | -4.827 | 1.00 54.37 | O |
| ATOM | 1773 | ND2 | ASN | A | 464 | 22.730 | 27.685 | -3.016 | 1.00 53.82 | N |
| ATOM | 1774 | C | ASN | A | 464 | 19.896 | 23.875 | -3.521 | 1.00 49.80 | C |
| ATOM | 1775 | O | ASN | A | 464 | 20.516 | 23.034 | -2.864 | 1.00 50.50 | O |
| ATOM | 1776 | N | CYS | A | 465 | 18.643 | 23.709 | -3.939 | 1.00 48.00 | N |
| ATOM | 1777 | CA | CYS | A | 465 | 17.876 | 22.486 | -3.721 | 1.00 45.19 | C |
| ATOM | 1778 | CB | CYS | A | 465 | 16.686 | 22.744 | -2.788 | 1.00 44.04 | C |
| ATOM | 1779 | SG | CYS | A | 465 | 15.439 | 21.420 | -2.799 | 1.00 41.50 | S |
| ATOM | 1780 | C | CYS | A | 465 | 17.366 | 22.035 | -5.088 | 1.00 43.23 | C |
| ATOM | 1781 | O | CYS | A | 465 | 16.579 | 22.734 | -5.722 | 1.00 43.71 | O |
| ATOM | 1782 | N | PRO | A | 466 | 17.816 | 20.869 | -5.565 | 1.00 41.88 | N |

Figure 14

```
ATOM   1783  CD  PRO A 466      18.782  19.933  -4.962  1.00 41.78           C
ATOM   1784  CA  PRO A 466      17.356  20.389  -6.872  1.00 41.23           C
ATOM   1785  CB  PRO A 466      17.861  18.953  -6.904  1.00 40.86           C
ATOM   1786  CG  PRO A 466      19.163  19.055  -6.141  1.00 41.97           C
ATOM   1787  C   PRO A 466      15.837  20.466  -7.005  1.00 40.73           C
ATOM   1788  O   PRO A 466      15.106  20.185  -6.048  1.00 40.08           O
ATOM   1789  N   GLU A 467      15.363  20.841  -8.189  1.00 39.05           N
ATOM   1790  CA  GLU A 467      13.929  20.945  -8.434  1.00 39.41           C
ATOM   1791  CB  GLU A 467      13.651  21.393  -9.871  1.00 41.01           C
ATOM   1792  CG  GLU A 467      12.959  22.743  -9.972  1.00 44.98           C
ATOM   1793  CD  GLU A 467      11.680  22.823  -9.141  1.00 47.99           C
ATOM   1794  OE1 GLU A 467      10.759  22.013  -9.381  1.00 51.39           O
ATOM   1795  OE2 GLU A 467      11.589  23.702  -8.251  1.00 47.41           O
ATOM   1796  C   GLU A 467      13.204  19.632  -8.191  1.00 39.01           C
ATOM   1797  O   GLU A 467      12.098  19.618  -7.663  1.00 37.73           O
ATOM   1798  N   GLU A 468      13.824  18.529  -8.599  1.00 38.73           N
ATOM   1799  CA  GLU A 468      13.222  17.217  -8.429  1.00 40.94           C
ATOM   1800  CB  GLU A 468      14.069  16.157  -9.138  1.00 43.52           C
ATOM   1801  CG  GLU A 468      14.556  16.588 -10.520  1.00 46.95           C
ATOM   1802  CD  GLU A 468      15.780  17.497 -10.455  1.00 49.63           C
ATOM   1803  OE1 GLU A 468      16.886  16.990 -10.166  1.00 50.88           O
ATOM   1804  OE2 GLU A 468      15.634  18.718 -10.680  1.00 51.04           O
ATOM   1805  C   GLU A 468      13.086  16.887  -6.943  1.00 39.45           C
ATOM   1806  O   GLU A 468      12.159  16.200  -6.529  1.00 40.84           O
ATOM   1807  N   LEU A 469      14.014  17.384  -6.138  1.00 38.69           N
ATOM   1808  CA  LEU A 469      13.957  17.141  -4.704  1.00 35.87           C
ATOM   1809  CB  LEU A 469      15.270  17.561  -4.040  1.00 35.32           C
ATOM   1810  CG  LEU A 469      15.385  17.265  -2.543  1.00 35.62           C
ATOM   1811  CD1 LEU A 469      15.169  15.775  -2.314  1.00 33.81           C
ATOM   1812  CD2 LEU A 469      16.760  17.703  -2.022  1.00 32.55           C
ATOM   1813  C   LEU A 469      12.793  17.944  -4.116  1.00 34.32           C
ATOM   1814  O   LEU A 469      12.027  17.437  -3.283  1.00 31.77           O
ATOM   1815  N   TYR A 470      12.658  19.196  -4.550  1.00 31.75           N
ATOM   1816  CA  TYR A 470      11.578  20.047  -4.049  1.00 31.67           C
ATOM   1817  CB  TYR A 470      11.623  21.450  -4.675  1.00 32.31           C
ATOM   1818  CG  TYR A 470      10.507  22.354  -4.175  1.00 30.75           C
ATOM   1819  CD1 TYR A 470      10.411  22.688  -2.827  1.00 31.12           C
ATOM   1820  CE1 TYR A 470       9.368  23.483  -2.347  1.00 30.37           C
ATOM   1821  CD2 TYR A 470       9.524  22.842  -5.047  1.00 31.64           C
ATOM   1822  CE2 TYR A 470       8.474  23.637  -4.580  1.00 29.72           C
ATOM   1823  CZ  TYR A 470       8.399  23.955  -3.227  1.00 30.34           C
ATOM   1824  OH  TYR A 470       7.360  24.731  -2.743  1.00 32.51           O
ATOM   1825  C   TYR A 470      10.220  19.421  -4.346  1.00 30.68           C
ATOM   1826  O   TYR A 470       9.327  19.447  -3.509  1.00 29.36           O
ATOM   1827  N   GLN A 471      10.066  18.862  -5.540  1.00 29.51           N
ATOM   1828  CA  GLN A 471       8.802  18.242  -5.905  1.00 31.10           C
ATOM   1829  CB  GLN A 471       8.817  17.833  -7.384  1.00 33.53           C
ATOM   1830  CG  GLN A 471       8.721  19.029  -8.325  1.00 37.69           C
ATOM   1831  CD  GLN A 471       7.394  19.761  -8.179  1.00 42.03           C
ATOM   1832  OE1 GLN A 471       6.328  19.180  -8.382  1.00 43.34           O
ATOM   1833  NE2 GLN A 471       7.454  21.044  -7.819  1.00 43.66           N
ATOM   1834  C   GLN A 471       8.548  17.041  -5.011  1.00 29.86           C
ATOM   1835  O   GLN A 471       7.403  16.760  -4.640  1.00 28.19           O
ATOM   1836  N   LEU A 472       9.614  16.336  -4.652  1.00 28.72           N
ATOM   1837  CA  LEU A 472       9.471  15.183  -3.768  1.00 27.83           C
ATOM   1838  CB  LEU A 472      10.819  14.484  -3.584  1.00 30.00           C
ATOM   1839  CG  LEU A 472      10.720  12.995  -3.246  1.00 33.29           C
ATOM   1840  CD1 LEU A 472       9.961  12.277  -4.367  1.00 30.79           C
ATOM   1841  CD2 LEU A 472      12.129  12.402  -3.080  1.00 34.24           C
ATOM   1842  C   LEU A 472       8.950  15.702  -2.428  1.00 26.51           C
```

Figure 14

| | | | | | | | | | |
|---|---|---|---|---|---|---|---|---|---|
| ATOM | 1843 | O | LEU | A | 472 | 8.118 | 15.071 | -1.778 | 1.00 25.57 | O |
| ATOM | 1844 | N | MET | A | 473 | 9.434 | 16.871 | -2.021 | 1.00 27.10 | N |
| ATOM | 1845 | CA | MET | A | 473 | 8.989 | 17.475 | -0.766 | 1.00 25.99 | C |
| ATOM | 1846 | CB | MET | A | 473 | 9.763 | 18.753 | -0.469 | 1.00 26.71 | C |
| ATOM | 1847 | CG | MET | A | 473 | 11.248 | 18.585 | -0.212 | 1.00 28.71 | C |
| ATOM | 1848 | SD | MET | A | 473 | 12.016 | 20.224 | -0.159 | 1.00 30.85 | S |
| ATOM | 1849 | CE | MET | A | 473 | 13.737 | 19.781 | 0.142 | 1.00 28.04 | C |
| ATOM | 1850 | C | MET | A | 473 | 7.505 | 17.817 | -0.824 | 1.00 26.11 | C |
| ATOM | 1851 | O | MET | A | 473 | 6.784 | 17.637 | 0.159 | 1.00 23.38 | O |
| ATOM | 1852 | N | ARG | A | 474 | 7.041 | 18.312 | -1.970 | 1.00 26.17 | N |
| ATOM | 1853 | CA | ARG | A | 474 | 5.627 | 18.677 | -2.077 | 1.00 27.59 | C |
| ATOM | 1854 | CB | ARG | A | 474 | 5.359 | 19.481 | -3.359 | 1.00 28.89 | C |
| ATOM | 1855 | CG | ARG | A | 474 | 6.062 | 20.863 | -3.389 | 1.00 32.21 | C |
| ATOM | 1856 | CD | ARG | A | 474 | 5.675 | 21.741 | -2.191 | 1.00 31.56 | C |
| ATOM | 1857 | NE | ARG | A | 474 | 4.282 | 22.175 | -2.236 | 1.00 31.92 | N |
| ATOM | 1858 | CZ | ARG | A | 474 | 3.837 | 23.219 | -2.937 | 1.00 32.59 | C |
| ATOM | 1859 | NH1 | ARG | A | 474 | 4.668 | 23.961 | -3.661 | 1.00 31.79 | N |
| ATOM | 1860 | NH2 | ARG | A | 474 | 2.550 | 23.514 | -2.925 | 1.00 30.36 | N |
| ATOM | 1861 | C | ARG | A | 474 | 4.738 | 17.439 | -2.023 | 1.00 26.32 | C |
| ATOM | 1862 | O | ARG | A | 474 | 3.590 | 17.517 | -1.588 | 1.00 22.83 | O |
| ATOM | 1863 | N | LEU | A | 475 | 5.269 | 16.297 | -2.459 | 1.00 28.51 | N |
| ATOM | 1864 | CA | LEU | A | 475 | 4.494 | 15.056 | -2.409 | 1.00 28.75 | C |
| ATOM | 1865 | CB | LEU | A | 475 | 5.207 | 13.923 | -3.154 | 1.00 30.72 | C |
| ATOM | 1866 | CG | LEU | A | 475 | 5.305 | 14.008 | -4.683 | 1.00 35.35 | C |
| ATOM | 1867 | CD1 | LEU | A | 475 | 5.895 | 12.699 | -5.232 | 1.00 34.72 | C |
| ATOM | 1868 | CD2 | LEU | A | 475 | 3.919 | 14.254 | -5.279 | 1.00 35.23 | C |
| ATOM | 1869 | C | LEU | A | 475 | 4.323 | 14.681 | -0.938 | 1.00 26.17 | C |
| ATOM | 1870 | O | LEU | A | 475 | 3.239 | 14.305 | -0.508 | 1.00 28.37 | O |
| ATOM | 1871 | N | CYS | A | 476 | 5.401 | 14.813 | -0.168 | 1.00 27.57 | N |
| ATOM | 1872 | CA | CYS | A | 476 | 5.379 | 14.499 | 1.255 | 1.00 25.42 | C |
| ATOM | 1873 | CB | CYS | A | 476 | 6.774 | 14.659 | 1.875 | 1.00 25.11 | C |
| ATOM | 1874 | SG | CYS | A | 476 | 8.006 | 13.482 | 1.331 | 1.00 30.64 | S |
| ATOM | 1875 | C | CYS | A | 476 | 4.421 | 15.422 | 1.982 | 1.00 25.32 | C |
| ATOM | 1876 | O | CYS | A | 476 | 3.870 | 15.049 | 3.022 | 1.00 24.12 | O |
| ATOM | 1877 | N | TRP | A | 477 | 4.222 | 16.624 | 1.436 | 1.00 25.42 | N |
| ATOM | 1878 | CA | TRP | A | 477 | 3.330 | 17.595 | 2.070 | 1.00 27.06 | C |
| ATOM | 1879 | CB | TRP | A | 477 | 3.949 | 19.008 | 2.053 | 1.00 26.44 | C |
| ATOM | 1880 | CG | TRP | A | 477 | 5.327 | 19.112 | 2.680 | 1.00 25.45 | C |
| ATOM | 1881 | CD2 | TRP | A | 477 | 6.355 | 20.049 | 2.332 | 1.00 25.49 | C |
| ATOM | 1882 | CE2 | TRP | A | 477 | 7.468 | 19.776 | 3.157 | 1.00 25.40 | C |
| ATOM | 1883 | CE3 | TRP | A | 477 | 6.443 | 21.095 | 1.406 | 1.00 24.01 | C |
| ATOM | 1884 | CD1 | TRP | A | 477 | 5.844 | 18.332 | 3.684 | 1.00 26.92 | C |
| ATOM | 1885 | NE1 | TRP | A | 477 | 7.132 | 18.724 | 3.969 | 1.00 25.56 | N |
| ATOM | 1886 | CZ2 | TRP | A | 477 | 8.654 | 20.514 | 3.081 | 1.00 27.20 | C |
| ATOM | 1887 | CZ3 | TRP | A | 477 | 7.633 | 21.834 | 1.332 | 1.00 24.83 | C |
| ATOM | 1888 | CH2 | TRP | A | 477 | 8.716 | 21.534 | 2.166 | 1.00 26.61 | C |
| ATOM | 1889 | C | TRP | A | 477 | 1.927 | 17.656 | 1.474 | 1.00 27.54 | C |
| ATOM | 1890 | O | TRP | A | 477 | 1.227 | 18.660 | 1.622 | 1.00 26.00 | O |
| ATOM | 1891 | N | LYS | A | 478 | 1.502 | 16.600 | 0.787 | 1.00 29.77 | N |
| ATOM | 1892 | CA | LYS | A | 478 | 0.151 | 16.616 | 0.237 | 1.00 30.03 | C |
| ATOM | 1893 | CB | LYS | A | 478 | -0.159 | 15.323 | -0.517 | 1.00 31.29 | C |
| ATOM | 1894 | CG | LYS | A | 478 | 0.390 | 15.282 | -1.934 | 1.00 31.34 | C |
| ATOM | 1895 | CD | LYS | A | 478 | -0.220 | 16.392 | -2.778 | 1.00 37.36 | C |
| ATOM | 1896 | CE | LYS | A | 478 | 0.075 | 16.180 | -4.255 | 1.00 39.43 | C |
| ATOM | 1897 | NZ | LYS | A | 478 | -0.643 | 17.172 | -5.104 | 1.00 47.40 | N |
| ATOM | 1898 | C | LYS | A | 478 | -0.754 | 16.745 | 1.452 | 1.00 31.07 | C |
| ATOM | 1899 | O | LYS | A | 478 | -0.454 | 16.176 | 2.514 | 1.00 28.50 | O |
| ATOM | 1900 | N | GLU | A | 479 | -1.842 | 17.499 | 1.305 | 1.00 29.45 | N |
| ATOM | 1901 | CA | GLU | A | 479 | -2.783 | 17.728 | 2.409 | 1.00 29.57 | C |
| ATOM | 1902 | CB | GLU | A | 479 | -3.877 | 18.721 | 1.981 | 1.00 28.64 | C |

Figure 14

```
ATOM   1903  CG   GLU A 479      -4.827  19.184   3.100  1.00 31.59           C
ATOM   1904  CD   GLU A 479      -4.163  20.110   4.117  1.00 31.28           C
ATOM   1905  OE1  GLU A 479      -3.197  20.814   3.754  1.00 32.11           O
ATOM   1906  OE2  GLU A 479      -4.619  20.146   5.281  1.00 32.54           O
ATOM   1907  C    GLU A 479      -3.427  16.426   2.890  1.00 29.91           C
ATOM   1908  O    GLU A 479      -3.517  16.186   4.099  1.00 29.11           O
ATOM   1909  N    ARG A 480      -3.878  15.593   1.953  1.00 29.51           N
ATOM   1910  CA   ARG A 480      -4.506  14.317   2.309  1.00 32.27           C
ATOM   1911  CB   ARG A 480      -5.461  13.852   1.197  1.00 34.88           C
ATOM   1912  CG   ARG A 480      -6.624  14.815   0.906  1.00 41.88           C
ATOM   1913  CD   ARG A 480      -7.442  14.337  -0.296  1.00 46.63           C
ATOM   1914  NE   ARG A 480      -8.615  15.173  -0.538  1.00 51.55           N
ATOM   1915  CZ   ARG A 480      -9.454  15.010  -1.557  1.00 53.51           C
ATOM   1916  NH1  ARG A 480      -9.254  14.038  -2.438  1.00 55.32           N
ATOM   1917  NH2  ARG A 480     -10.492  15.824  -1.701  1.00 56.06           N
ATOM   1918  C    ARG A 480      -3.403  13.276   2.509  1.00 28.38           C
ATOM   1919  O    ARG A 480      -2.580  13.067   1.625  1.00 28.68           O
ATOM   1920  N    PRO A 481      -3.383  12.605   3.672  1.00 29.18           N
ATOM   1921  CD   PRO A 481      -4.362  12.718   4.767  1.00 29.38           C
ATOM   1922  CA   PRO A 481      -2.374  11.587   3.986  1.00 28.52           C
ATOM   1923  CB   PRO A 481      -2.888  10.980   5.299  1.00 29.40           C
ATOM   1924  CG   PRO A 481      -3.606  12.123   5.933  1.00 32.21           C
ATOM   1925  C    PRO A 481      -2.195  10.531   2.897  1.00 27.98           C
ATOM   1926  O    PRO A 481      -1.065  10.179   2.542  1.00 24.43           O
ATOM   1927  N    GLU A 482      -3.311  10.044   2.355  1.00 28.34           N
ATOM   1928  CA   GLU A 482      -3.261   9.015   1.323  1.00 28.92           C
ATOM   1929  CB   GLU A 482      -4.680   8.572   0.933  1.00 33.12           C
ATOM   1930  CG   GLU A 482      -5.517   9.660   0.266  1.00 36.04           C
ATOM   1931  CD   GLU A 482      -6.385  10.416   1.252  1.00 37.28           C
ATOM   1932  OE1  GLU A 482      -5.919  10.688   2.371  1.00 37.26           O
ATOM   1933  OE2  GLU A 482      -7.541  10.741   0.896  1.00 39.28           O
ATOM   1934  C    GLU A 482      -2.508   9.440   0.075  1.00 27.97           C
ATOM   1935  O    GLU A 482      -2.040   8.588  -0.688  1.00 28.56           O
ATOM   1936  N    ASP A 483      -2.382  10.750  -0.154  1.00 26.18           N
ATOM   1937  CA   ASP A 483      -1.681  11.219  -1.336  1.00 25.81           C
ATOM   1938  CB   ASP A 483      -2.265  12.552  -1.816  1.00 28.16           C
ATOM   1939  CG   ASP A 483      -3.693  12.396  -2.330  1.00 34.34           C
ATOM   1940  OD1  ASP A 483      -3.896  11.582  -3.251  1.00 36.12           O
ATOM   1941  OD2  ASP A 483      -4.607  13.062  -1.813  1.00 32.63           O
ATOM   1942  C    ASP A 483      -0.170  11.331  -1.150  1.00 26.15           C
ATOM   1943  O    ASP A 483       0.562  11.541  -2.117  1.00 23.42           O
ATOM   1944  N    ARG A 484       0.297  11.174   0.084  1.00 25.26           N
ATOM   1945  CA   ARG A 484       1.734  11.236   0.349  1.00 28.45           C
ATOM   1946  CB   ARG A 484       2.003  11.555   1.823  1.00 29.18           C
ATOM   1947  CG   ARG A 484       1.415  12.881   2.256  1.00 29.10           C
ATOM   1948  CD   ARG A 484       1.435  13.044   3.747  1.00 26.00           C
ATOM   1949  NE   ARG A 484       0.452  14.049   4.126  1.00 26.22           N
ATOM   1950  CZ   ARG A 484      -0.070  14.186   5.332  1.00 25.90           C
ATOM   1951  NH1  ARG A 484       0.309  13.381   6.311  1.00 28.02           N
ATOM   1952  NH2  ARG A 484      -1.024  15.094   5.539  1.00 28.06           N
ATOM   1953  C    ARG A 484       2.313   9.879   0.011  1.00 28.61           C
ATOM   1954  O    ARG A 484       1.711   8.863   0.317  1.00 28.38           O
ATOM   1955  N    PRO A 485       3.502   9.851  -0.614  1.00 30.21           N
ATOM   1956  CD   PRO A 485       4.363  11.021  -0.867  1.00 30.35           C
ATOM   1957  CA   PRO A 485       4.175   8.608  -1.004  1.00 30.35           C
ATOM   1958  CB   PRO A 485       5.357   9.109  -1.819  1.00 31.71           C
ATOM   1959  CG   PRO A 485       5.722  10.388  -1.099  1.00 33.59           C
ATOM   1960  C    PRO A 485       4.612   7.744   0.182  1.00 30.84           C
ATOM   1961  O    PRO A 485       4.577   8.183   1.330  1.00 29.21           O
ATOM   1962  N    THR A 486       5.014   6.510  -0.111  1.00 28.35           N.
```

Figure 14

```
ATOM   1963  CA   THR A 486       5.470   5.581   0.917  1.00 27.03           C
ATOM   1964  CB   THR A 486       5.271   4.109   0.476  1.00 27.65           C
ATOM   1965  OG1  THR A 486       5.926   3.904  -0.788  1.00 28.87           O
ATOM   1966  CG2  THR A 486       3.781   3.767   0.347  1.00 30.43           C
ATOM   1967  C    THR A 486       6.972   5.805   1.114  1.00 25.67           C
ATOM   1968  O    THR A 486       7.627   6.366   0.242  1.00 24.41           O
ATOM   1969  N    PHE A 487       7.515   5.382   2.256  1.00 25.31           N
ATOM   1970  CA   PHE A 487       8.948   5.537   2.486  1.00 25.80           C
ATOM   1971  CB   PHE A 487       9.298   5.268   3.945  1.00 24.70           C
ATOM   1972  CG   PHE A 487       9.097   6.457   4.834  1.00 25.23           C
ATOM   1973  CD1  PHE A 487       9.903   7.580   4.706  1.00 24.85           C
ATOM   1974  CD2  PHE A 487       8.106   6.453   5.800  1.00 22.46           C
ATOM   1975  CE1  PHE A 487       9.718   8.691   5.540  1.00 24.50           C
ATOM   1976  CE2  PHE A 487       7.913   7.550   6.634  1.00 27.07           C
ATOM   1977  CZ   PHE A 487       8.718   8.669   6.505  1.00 22.73           C
ATOM   1978  C    PHE A 487       9.693   4.575   1.584  1.00 28.32           C
ATOM   1979  O    PHE A 487      10.864   4.782   1.264  1.00 29.69           O
ATOM   1980  N    ASP A 488       9.003   3.512   1.186  1.00 30.60           N
ATOM   1981  CA   ASP A 488       9.561   2.515   0.280  1.00 32.68           C
ATOM   1982  CB   ASP A 488       8.508   1.411   0.083  1.00 36.03           C
ATOM   1983  CG   ASP A 488       8.971   0.285  -0.831  1.00 41.57           C
ATOM   1984  OD1  ASP A 488      10.183  -0.036  -0.862  1.00 42.32           O
ATOM   1985  OD2  ASP A 488       8.092  -0.295  -1.511  1.00 40.41           O
ATOM   1986  C    ASP A 488       9.872   3.269  -1.030  1.00 33.93           C
ATOM   1987  O    ASP A 488      10.939   3.091  -1.634  1.00 34.36           O
ATOM   1988  N    TYR A 489       8.945   4.132  -1.451  1.00 31.10           N
ATOM   1989  CA   TYR A 489       9.126   4.923  -2.673  1.00 30.58           C
ATOM   1990  CB   TYR A 489       7.813   5.605  -3.077  1.00 29.80           C
ATOM   1991  CG   TYR A 489       7.987   6.585  -4.213  1.00 32.19           C
ATOM   1992  CD1  TYR A 489       8.185   6.139  -5.519  1.00 33.73           C
ATOM   1993  CE1  TYR A 489       8.388   7.035  -6.567  1.00 34.24           C
ATOM   1994  CD2  TYR A 489       7.994   7.962  -3.980  1.00 35.60           C
ATOM   1995  CE2  TYR A 489       8.200   8.876  -5.029  1.00 34.87           C
ATOM   1996  CZ   TYR A 489       8.399   8.400  -6.314  1.00 36.68           C
ATOM   1997  OH   TYR A 489       8.645   9.278  -7.342  1.00 36.29           O
ATOM   1998  C    TYR A 489      10.205   5.998  -2.497  1.00 30.18           C
ATOM   1999  O    TYR A 489      11.099   6.143  -3.335  1.00 28.32           O
ATOM   2000  N    LEU A 490      10.103   6.757  -1.407  1.00 30.28           N
ATOM   2001  CA   LEU A 490      11.072   7.812  -1.117  1.00 31.29           C
ATOM   2002  CB   LEU A 490      10.743   8.454   0.226  1.00 29.98           C
ATOM   2003  CG   LEU A 490       9.453   9.279   0.216  1.00 31.26           C
ATOM   2004  CD1  LEU A 490       8.957   9.488   1.640  1.00 29.53           C
ATOM   2005  CD2  LEU A 490       9.712  10.604  -0.509  1.00 30.28           C
ATOM   2006  C    LEU A 490      12.507   7.272  -1.103  1.00 31.51           C
ATOM   2007  O    LEU A 490      13.408   7.898  -1.638  1.00 30.51           O
ATOM   2008  N    ARG A 491      12.717   6.116  -0.478  1.00 32.94           N
ATOM   2009  CA   ARG A 491      14.051   5.524  -0.439  1.00 35.57           C
ATOM   2010  CB   ARG A 491      14.029   4.213   0.346  1.00 38.33           C
ATOM   2011  CG   ARG A 491      15.309   3.390   0.208  1.00 42.83           C
ATOM   2012  CD   ARG A 491      15.025   1.924   0.458  1.00 46.90           C
ATOM   2013  NE   ARG A 491      13.915   1.453  -0.366  1.00 50.84           N
ATOM   2014  CZ   ARG A 491      13.952   1.329  -1.690  1.00 53.10           C
ATOM   2015  NH1  ARG A 491      15.053   1.637  -2.367  1.00 54.36           N
ATOM   2016  NH2  ARG A 491      12.876   0.908  -2.342  1.00 53.99           N
ATOM   2017  C    ARG A 491      14.573   5.265  -1.864  1.00 36.74           C
ATOM   2018  O    ARG A 491      15.731   5.567  -2.170  1.00 36.27           O
ATOM   2019  N    SER A 492      13.710   4.719  -2.723  1.00 36.27           N
ATOM   2020  CA   SER A 492      14.054   4.408  -4.114  1.00 39.50           C
ATOM   2021  CB   SER A 492      12.863   3.781  -4.843  1.00 38.62           C
ATOM   2022  OG   SER A 492      12.582   2.488  -4.349  1.00 44.46           O
```

Figure 14

```
ATOM   2023  C   SER A 492      14.513    5.610   -4.926  1.00 39.50           C
ATOM   2024  O   SER A 492      15.530    5.545   -5.612  1.00 39.65           O
ATOM   2025  N   VAL A 493      13.762    6.705   -4.861  1.00 40.53           N
ATOM   2026  CA  VAL A 493      14.125    7.891   -5.630  1.00 40.60           C
ATOM   2027  CB  VAL A 493      12.951    8.910   -5.670  1.00 42.07           C
ATOM   2028  CG1 VAL A 493      12.528    9.275   -4.271  1.00 42.94           C
ATOM   2029  CG2 VAL A 493      13.357   10.146   -6.450  1.00 40.54           C
ATOM   2030  C   VAL A 493      15.398    8.563   -5.102  1.00 41.41           C
ATOM   2031  O   VAL A 493      16.213    9.069   -5.886  1.00 39.77           O
ATOM   2032  N   LEU A 494      15.581    8.538   -3.782  1.00 40.35           N
ATOM   2033  CA  LEU A 494      16.749    9.151   -3.163  1.00 40.60           C
ATOM   2034  CB  LEU A 494      16.521    9.331   -1.655  1.00 36.59           C
ATOM   2035  CG  LEU A 494      15.421   10.310   -1.224  1.00 37.59           C
ATOM   2036  CD1 LEU A 494      15.221   10.247    0.277  1.00 33.91           C
ATOM   2037  CD2 LEU A 494      15.786   11.720   -1.651  1.00 34.92           C
ATOM   2038  C   LEU A 494      18.055    8.384   -3.394  1.00 42.06           C
ATOM   2039  O   LEU A 494      19.108    8.999   -3.561  1.00 42.31           O
ATOM   2040  N   GLU A 495      17.994    7.055   -3.402  1.00 43.06           N
ATOM   2041  CA  GLU A 495      19.198    6.249   -3.599  1.00 46.91           C
ATOM   2042  CB  GLU A 495      18.942    4.786   -3.227  1.00 48.72           C
ATOM   2043  CG  GLU A 495      18.486    4.583   -1.796  1.00 52.53           C
ATOM   2044  CD  GLU A 495      18.430    3.123   -1.391  1.00 55.05           C
ATOM   2045  OE1 GLU A 495      18.003    2.288   -2.222  1.00 56.61           O
ATOM   2046  OE2 GLU A 495      18.802    2.815   -0.234  1.00 56.67           O
ATOM   2047  C   GLU A 495      19.725    6.314   -5.027  1.00 48.50           C
ATOM   2048  O   GLU A 495      20.901    6.034   -5.274  1.00 49.45           O
ATOM   2049  N   ASP A 496      18.849    6.673   -5.960  1.00 50.62           N
ATOM   2050  CA  ASP A 496      19.211    6.786   -7.370  1.00 53.10           C
ATOM   2051  CB  ASP A 496      18.374    5.823   -8.227  1.00 54.31           C
ATOM   2052  CG  ASP A 496      18.620    4.365   -7.897  1.00 56.03           C
ATOM   2053  OD1 ASP A 496      18.521    3.990   -6.709  1.00 59.17           O
ATOM   2054  OD2 ASP A 496      18.900    3.585   -8.831  1.00 56.48           O
ATOM   2055  C   ASP A 496      18.959    8.208   -7.862  1.00 53.70           C
ATOM   2056  O   ASP A 496      18.659    8.408   -9.037  1.00 56.05           O
ATOM   2057  N   PHE A 497      19.081    9.197   -6.981  1.00 53.68           N
ATOM   2058  CA  PHE A 497      18.829   10.579   -7.381  1.00 53.21           C
ATOM   2059  CB  PHE A 497      18.936   11.523   -6.184  1.00 51.88           C
ATOM   2060  CG  PHE A 497      18.173   12.808   -6.365  1.00 51.41           C
ATOM   2061  CD1 PHE A 497      16.782   12.818   -6.310  1.00 51.61           C
ATOM   2062  CD2 PHE A 497      18.842   14.001   -6.624  1.00 51.68           C
ATOM   2063  CE1 PHE A 497      16.068   13.995   -6.513  1.00 51.18           C
ATOM   2064  CE2 PHE A 497      18.137   15.187   -6.830  1.00 50.76           C
ATOM   2065  CZ  PHE A 497      16.748   15.184   -6.774  1.00 51.16           C
ATOM   2066  C   PHE A 497      19.768   11.049   -8.495  1.00 53.94           C
ATOM   2067  O   PHE A 497      19.331   11.696   -9.449  1.00 52.26           O
ATOM   2068  N   PHE A 498      21.056   10.748   -8.356  1.00 55.22           N
ATOM   2069  CA  PHE A 498      22.048   11.101   -9.374  1.00 57.56           C
ATOM   2070  CB  PHE A 498      22.058   12.616   -9.676  1.00 58.32           C
ATOM   2071  CG  PHE A 498      22.173   13.500   -8.461  1.00 59.19           C
ATOM   2072  CD1 PHE A 498      22.936   13.121   -7.362  1.00 59.16           C
ATOM   2073  CD2 PHE A 498      21.532   14.739   -8.434  1.00 59.36           C
ATOM   2074  CE1 PHE A 498      23.055   13.962   -6.254  1.00 59.14           C
ATOM   2075  CE2 PHE A 498      21.648   15.587   -7.333  1.00 58.49           C
ATOM   2076  CZ  PHE A 498      22.410   15.197   -6.242  1.00 59.34           C
ATOM   2077  C   PHE A 498      23.459   10.636   -9.029  1.00 58.12           C
ATOM   2078  O   PHE A 498      24.014    9.873   -9.854  1.00 58.50           O
ATOM   2079  OXT PHE A 498      24.005   10.970   -7.960  1.00 40.86           O
ATOM   2080  CB  TRP B 238      47.735   27.860   31.762  1.00 62.00           C
ATOM   2081  CG  TRP B 238      47.280   28.449   33.066  1.00 62.16           C
ATOM   2082  CD2 TRP B 238      47.851   28.211   34.358  1.00 61.83           C
```

Figure 14

```
ATOM   2083  CE2 TRP B 238      47.121  28.985  35.286  1.00 61.20           C
ATOM   2084  CE3 TRP B 238      48.911  27.419  34.820  1.00 62.42           C
ATOM   2085  CD1 TRP B 238      46.256  29.333  33.258  1.00 62.03           C
ATOM   2086  NE1 TRP B 238      46.154  29.659  34.588  1.00 61.34           N
ATOM   2087  CZ2 TRP B 238      47.416  28.991  36.651  1.00 61.24           C
ATOM   2088  CZ3 TRP B 238      49.206  27.425  36.180  1.00 62.06           C
ATOM   2089  CH2 TRP B 238      48.457  28.208  37.079  1.00 62.12           C
ATOM   2090  C   TRP B 238      49.038  28.122  29.650  1.00 61.09           C
ATOM   2091  O   TRP B 238      49.902  27.263  29.840  1.00 60.90           O
ATOM   2092  N   TRP B 238      47.435  29.905  30.390  1.00 61.40           N
ATOM   2093  CA  TRP B 238      48.413  28.867  30.828  1.00 61.27           C
ATOM   2094  N   GLU B 239      48.596  28.437  28.436  1.00 60.29           N
ATOM   2095  CA  GLU B 239      49.148  27.789  27.252  1.00 59.48           C
ATOM   2096  CB  GLU B 239      48.447  28.277  25.979  1.00 60.60           C
ATOM   2097  CG  GLU B 239      47.055  27.725  25.728  1.00 63.28           C
ATOM   2098  CD  GLU B 239      46.042  28.163  26.765  1.00 63.99           C
ATOM   2099  OE1 GLU B 239      46.031  29.362  27.122  1.00 65.43           O
ATOM   2100  OE2 GLU B 239      45.245  27.310  27.211  1.00 64.34           O
ATOM   2101  C   GLU B 239      50.629  28.130  27.151  1.00 57.94           C
ATOM   2102  O   GLU B 239      51.027  29.261  27.405  1.00 58.51           O
ATOM   2103  N   VAL B 240      51.447  27.151  26.790  1.00 56.38           N
ATOM   2104  CA  VAL B 240      52.877  27.385  26.638  1.00 55.63           C
ATOM   2105  CB  VAL B 240      53.680  26.946  27.892  1.00 54.83           C
ATOM   2106  CG1 VAL B 240      53.215  27.739  29.100  1.00 54.11           C
ATOM   2107  CG2 VAL B 240      53.527  25.452  28.126  1.00 54.24           C
ATOM   2108  C   VAL B 240      53.376  26.619  25.422  1.00 55.39           C
ATOM   2109  O   VAL B 240      52.907  25.517  25.131  1.00 55.09           O
ATOM   2110  N   PRO B 241      54.328  27.202  24.684  1.00 54.71           N
ATOM   2111  CD  PRO B 241      54.881  28.561  24.831  1.00 55.02           C
ATOM   2112  CA  PRO B 241      54.868  26.540  23.495  1.00 53.99           C
ATOM   2113  CB  PRO B 241      55.907  27.539  22.989  1.00 54.81           C
ATOM   2114  CG  PRO B 241      55.333  28.866  23.424  1.00 55.01           C
ATOM   2115  C   PRO B 241      55.476  25.171  23.799  1.00 53.60           C
ATOM   2116  O   PRO B 241      56.325  25.036  24.687  1.00 52.54           O
ATOM   2117  N   ARG B 242      55.033  24.163  23.055  1.00 52.40           N
ATOM   2118  CA  ARG B 242      55.522  22.797  23.207  1.00 52.73           C
ATOM   2119  CB  ARG B 242      55.122  21.970  21.987  1.00 54.58           C
ATOM   2120  CG  ARG B 242      55.717  20.578  21.961  1.00 57.12           C
ATOM   2121  CD  ARG B 242      55.022  19.685  22.952  1.00 59.77           C
ATOM   2122  NE  ARG B 242      53.607  19.515  22.623  1.00 62.49           N
ATOM   2123  CZ  ARG B 242      53.164  19.016  21.473  1.00 61.88           C
ATOM   2124  NH1 ARG B 242      54.026  18.637  20.538  1.00 60.80           N
ATOM   2125  NH2 ARG B 242      51.860  18.891  21.260  1.00 61.08           N
ATOM   2126  C   ARG B 242      57.042  22.757  23.350  1.00 52.05           C
ATOM   2127  O   ARG B 242      57.588  22.026  24.185  1.00 49.12           O
ATOM   2128  N   GLU B 243      57.714  23.547  22.519  1.00 51.15           N
ATOM   2129  CA  GLU B 243      59.168  23.624  22.517  1.00 51.57           C
ATOM   2130  CB  GLU B 243      59.637  24.718  21.551  1.00 52.65           C
ATOM   2131  CG  GLU B 243      59.351  24.439  20.071  1.00 55.19           C
ATOM   2132  CD  GLU B 243      57.864  24.374  19.734  1.00 56.94           C
ATOM   2133  OE1 GLU B 243      57.140  25.361  19.996  1.00 58.59           O
ATOM   2134  OE2 GLU B 243      57.420  23.336  19.196  1.00 57.68           O
ATOM   2135  C   GLU B 243      59.747  23.883  23.907  1.00 50.43           C
ATOM   2136  O   GLU B 243      60.887  23.511  24.184  1.00 49.47           O
ATOM   2137  N   THR B 244      58.970  24.517  24.783  1.00 49.04           N
ATOM   2138  CA  THR B 244      59.458  24.796  26.134  1.00 48.90           C
ATOM   2139  CB  THR B 244      58.644  25.914  26.832  1.00 48.33           C
ATOM   2140  OG1 THR B 244      57.349  25.419  27.205  1.00 49.01           O
ATOM   2141  CG2 THR B 244      58.476  27.100  25.908  1.00 46.71           C
ATOM   2142  C   THR B 244      59.379  23.542  27.000  1.00 47.78           C
```

Figure 14

| | | | | | | | | | | |
|---|---|---|---|---|---|---|---|---|---|---|
| ATOM | 2143 | O | THR | B | 244 | 59.524 | 23.615 | 28.219 | 1.00 49.17 | O |
| ATOM | 2144 | N | LEU | B | 245 | 59.155 | 22.397 | 26.364 | 1.00 46.55 | N |
| ATOM | 2145 | CA | LEU | B | 245 | 59.032 | 21.128 | 27.077 | 1.00 46.44 | C |
| ATOM | 2146 | CB | LEU | B | 245 | 57.554 | 20.692 | 27.146 | 1.00 45.38 | C |
| ATOM | 2147 | CG | LEU | B | 245 | 56.568 | 21.392 | 28.090 | 1.00 46.88 | C |
| ATOM | 2148 | CD1 | LEU | B | 245 | 56.563 | 22.878 | 27.831 | 1.00 48.45 | C |
| ATOM | 2149 | CD2 | LEU | B | 245 | 55.166 | 20.819 | 27.885 | 1.00 45.48 | C |
| ATOM | 2150 | C | LEU | B | 245 | 59.835 | 19.983 | 26.464 | 1.00 46.52 | C |
| ATOM | 2151 | O | LEU | B | 245 | 59.789 | 19.743 | 25.251 | 1.00 45.45 | O |
| ATOM | 2152 | N | LYS | B | 246 | 60.560 | 19.266 | 27.314 | 1.00 44.47 | N |
| ATOM | 2153 | CA | LYS | B | 246 | 61.318 | 18.120 | 26.858 | 1.00 44.15 | C |
| ATOM | 2154 | CB | LYS | B | 246 | 62.829 | 18.360 | 26.974 | 1.00 44.24 | C |
| ATOM | 2155 | CG | LYS | B | 246 | 63.662 | 17.199 | 26.432 | 1.00 43.47 | C |
| ATOM | 2156 | CD | LYS | B | 246 | 65.132 | 17.581 | 26.206 | 1.00 44.26 | C |
| ATOM | 2157 | CE | LYS | B | 246 | 65.841 | 17.962 | 27.496 | 1.00 42.98 | C |
| ATOM | 2158 | NZ | LYS | B | 246 | 67.300 | 18.200 | 27.276 | 1.00 43.38 | N |
| ATOM | 2159 | C | LYS | B | 246 | 60.913 | 16.921 | 27.704 | 1.00 44.38 | C |
| ATOM | 2160 | O | LYS | B | 246 | 61.281 | 16.824 | 28.876 | 1.00 44.62 | O |
| ATOM | 2161 | N | LEU | B | 247 | 60.125 | 16.028 | 27.116 | 1.00 43.79 | N |
| ATOM | 2162 | CA | LEU | B | 247 | 59.700 | 14.830 | 27.815 | 1.00 44.38 | C |
| ATOM | 2163 | CB | LEU | B | 247 | 58.505 | 14.188 | 27.104 | 1.00 44.16 | C |
| ATOM | 2164 | CG | LEU | B | 247 | 57.127 | 14.770 | 27.464 | 1.00 43.06 | C |
| ATOM | 2165 | CD1 | LEU | B | 247 | 57.120 | 16.278 | 27.293 | 1.00 42.11 | C |
| ATOM | 2166 | CD2 | LEU | B | 247 | 56.063 | 14.126 | 26.595 | 1.00 42.97 | C |
| ATOM | 2167 | C | LEU | B | 247 | 60.904 | 13.905 | 27.813 | 1.00 45.01 | C |
| ATOM | 2168 | O | LEU | B | 247 | 61.401 | 13.511 | 26.757 | 1.00 44.25 | O |
| ATOM | 2169 | N | VAL | B | 248 | 61.387 | 13.580 | 29.005 | 1.00 44.10 | N |
| ATOM | 2170 | CA | VAL | B | 248 | 62.557 | 12.732 | 29.134 | 1.00 44.31 | C |
| ATOM | 2171 | CB | VAL | B | 248 | 63.431 | 13.205 | 30.324 | 1.00 44.31 | C |
| ATOM | 2172 | CG1 | VAL | B | 248 | 64.548 | 12.202 | 30.610 | 1.00 44.51 | C |
| ATOM | 2173 | CG2 | VAL | B | 248 | 64.023 | 14.557 | 30.000 | 1.00 42.94 | C |
| ATOM | 2174 | C | VAL | B | 248 | 62.249 | 11.254 | 29.301 | 1.00 45.12 | C |
| ATOM | 2175 | O | VAL | B | 248 | 62.768 | 10.418 | 28.561 | 1.00 44.68 | O |
| ATOM | 2176 | N | GLU | B | 249 | 61.387 | 10.936 | 30.262 | 1.00 45.05 | N |
| ATOM | 2177 | CA | GLU | B | 249 | 61.069 | 9.548 | 30.552 | 1.00 44.52 | C |
| ATOM | 2178 | CB | GLU | B | 249 | 61.853 | 9.120 | 31.789 | 1.00 45.81 | C |
| ATOM | 2179 | CG | GLU | B | 249 | 61.729 | 7.667 | 32.176 | 1.00 47.07 | C |
| ATOM | 2180 | CD | GLU | B | 249 | 62.324 | 7.416 | 33.549 | 1.00 48.29 | C |
| ATOM | 2181 | OE1 | GLU | B | 249 | 63.342 | 8.061 | 33.879 | 1.00 47.02 | O |
| ATOM | 2182 | OE2 | GLU | B | 249 | 61.780 | 6.577 | 34.294 | 1.00 51.10 | O |
| ATOM | 2183 | C | GLU | B | 249 | 59.587 | 9.320 | 30.803 | 1.00 44.34 | C |
| ATOM | 2184 | O | GLU | B | 249 | 58.949 | 10.077 | 31.540 | 1.00 43.23 | O |
| ATOM | 2185 | N | ARG | B | 250 | 59.055 | 8.258 | 30.206 | 1.00 43.03 | N |
| ATOM | 2186 | CA | ARG | B | 250 | 57.657 | 7.925 | 30.378 | 1.00 43.99 | C |
| ATOM | 2187 | CB | ARG | B | 250 | 57.183 | 6.974 | 29.274 | 1.00 43.76 | C |
| ATOM | 2188 | CG | ARG | B | 250 | 55.686 | 6.711 | 29.336 | 1.00 45.39 | C |
| ATOM | 2189 | CD | ARG | B | 250 | 55.179 | 6.003 | 28.107 | 1.00 45.63 | C |
| ATOM | 2190 | NE | ARG | B | 250 | 55.478 | 4.578 | 28.127 | 1.00 48.42 | N |
| ATOM | 2191 | CZ | ARG | B | 250 | 55.166 | 3.745 | 27.141 | 1.00 48.83 | C |
| ATOM | 2192 | NH1 | ARG | B | 250 | 54.552 | 4.204 | 26.061 | 1.00 49.99 | N |
| ATOM | 2193 | NH2 | ARG | B | 250 | 55.456 | 2.453 | 27.240 | 1.00 49.75 | N |
| ATOM | 2194 | C | ARG | B | 250 | 57.450 | 7.270 | 31.741 | 1.00 43.13 | C |
| ATOM | 2195 | O | ARG | B | 250 | 57.985 | 6.192 | 32.010 | 1.00 43.53 | O |
| ATOM | 2196 | N | LEU | B | 251 | 56.682 | 7.939 | 32.598 | 1.00 43.16 | N |
| ATOM | 2197 | CA | LEU | B | 251 | 56.384 | 7.428 | 33.929 | 1.00 40.82 | C |
| ATOM | 2198 | CB | LEU | B | 251 | 55.922 | 8.572 | 34.836 | 1.00 40.38 | C |
| ATOM | 2199 | CG | LEU | B | 251 | 56.977 | 9.666 | 35.056 | 1.00 40.36 | C |
| ATOM | 2200 | CD1 | LEU | B | 251 | 56.410 | 10.798 | 35.894 | 1.00 38.66 | C |
| ATOM | 2201 | CD2 | LEU | B | 251 | 58.204 | 9.068 | 35.738 | 1.00 39.59 | C |
| ATOM | 2202 | C | LEU | B | 251 | 55.310 | 6.345 | 33.844 | 1.00 41.81 | C |

Figure 14

| | | | | | | | | | | |
|---|---|---|---|---|---|---|---|---|---|---|
| ATOM | 2203 | O | LEU | B | 251 | 55.288 | 5.414 | 34.652 | 1.00 41.78 | O |
| ATOM | 2204 | N | GLY | B | 252 | 54.419 | 6.466 | 32.859 | 1.00 40.74 | N |
| ATOM | 2205 | CA | GLY | B | 252 | 53.372 | 5.472 | 32.694 | 1.00 38.58 | C |
| ATOM | 2206 | C | GLY | B | 252 | 52.517 | 5.646 | 31.451 | 1.00 37.77 | C |
| ATOM | 2207 | O | GLY | B | 252 | 52.407 | 6.741 | 30.900 | 1.00 35.28 | O |
| ATOM | 2208 | N | ALA | B | 253 | 51.899 | 4.552 | 31.018 | 1.00 38.43 | N |
| ATOM | 2209 | CA | ALA | B | 253 | 51.037 | 4.574 | 29.848 | 1.00 39.13 | C |
| ATOM | 2210 | CB | ALA | B | 253 | 51.790 | 4.023 | 28.630 | 1.00 40.89 | C |
| ATOM | 2211 | C | ALA | B | 253 | 49.774 | 3.752 | 30.106 | 1.00 39.12 | C |
| ATOM | 2212 | O | ALA | B | 253 | 49.845 | 2.630 | 30.607 | 1.00 40.08 | O |
| ATOM | 2213 | N | GLY | B | 254 | 48.624 | 4.314 | 29.753 | 1.00 38.56 | N |
| ATOM | 2214 | CA | GLY | B | 254 | 47.373 | 3.618 | 29.967 | 1.00 38.34 | C |
| ATOM | 2215 | C | GLY | B | 254 | 46.370 | 3.736 | 28.831 | 1.00 39.81 | C |
| ATOM | 2216 | O | GLY | B | 254 | 46.702 | 4.083 | 27.705 | 1.00 39.34 | O |
| ATOM | 2217 | N | GLN | B | 255 | 45.114 | 3.464 | 29.148 | 1.00 40.40 | N |
| ATOM | 2218 | CA | GLN | B | 255 | 44.047 | 3.492 | 28.159 | 1.00 42.03 | C |
| ATOM | 2219 | CB | GLN | B | 255 | 42.774 | 2.939 | 28.805 | 1.00 45.38 | C |
| ATOM | 2220 | CG | GLN | B | 255 | 41.762 | 2.383 | 27.820 | 1.00 50.17 | C |
| ATOM | 2221 | CD | GLN | B | 255 | 40.730 | 1.494 | 28.488 | 1.00 51.96 | C |
| ATOM | 2222 | OE1 | GLN | B | 255 | 39.859 | 0.937 | 27.822 | 1.00 54.25 | O |
| ATOM | 2223 | NE2 | GLN | B | 255 | 40.828 | 1.350 | 29.810 | 1.00 54.04 | N |
| ATOM | 2224 | C | GLN | B | 255 | 43.763 | 4.856 | 27.517 | 1.00 40.36 | C |
| ATOM | 2225 | O | GLN | B | 255 | 43.435 | 4.927 | 26.330 | 1.00 41.63 | O |
| ATOM | 2226 | N | PHE | B | 256 | 43.887 | 5.930 | 28.289 | 1.00 38.02 | N |
| ATOM | 2227 | CA | PHE | B | 256 | 43.611 | 7.270 | 27.778 | 1.00 38.06 | C |
| ATOM | 2228 | CB | PHE | B | 256 | 42.761 | 8.068 | 28.771 | 1.00 38.78 | C |
| ATOM | 2229 | CG | PHE | B | 256 | 41.374 | 7.530 | 28.969 | 1.00 40.99 | C |
| ATOM | 2230 | CD1 | PHE | B | 256 | 40.849 | 6.564 | 28.113 | 1.00 41.56 | C |
| ATOM | 2231 | CD2 | PHE | B | 256 | 40.584 | 8.002 | 30.016 | 1.00 40.22 | C |
| ATOM | 2232 | CE1 | PHE | B | 256 | 39.555 | 6.071 | 28.295 | 1.00 43.47 | C |
| ATOM | 2233 | CE2 | PHE | B | 256 | 39.288 | 7.518 | 30.207 | 1.00 44.37 | C |
| ATOM | 2234 | CZ | PHE | B | 256 | 38.773 | 6.547 | 29.343 | 1.00 43.34 | C |
| ATOM | 2235 | C | PHE | B | 256 | 44.843 | 8.102 | 27.456 | 1.00 36.74 | C |
| ATOM | 2236 | O | PHE | B | 256 | 44.713 | 9.253 | 27.045 | 1.00 34.99 | O |
| ATOM | 2237 | N | GLY | B | 257 | 46.033 | 7.543 | 27.654 | 1.00 37.62 | N |
| ATOM | 2238 | CA | GLY | B | 257 | 47.232 | 8.311 | 27.370 | 1.00 38.13 | C |
| ATOM | 2239 | C | GLY | B | 257 | 48.436 | 7.891 | 28.189 | 1.00 38.59 | C |
| ATOM | 2240 | O | GLY | B | 257 | 48.512 | 6.752 | 28.657 | 1.00 38.61 | O |
| ATOM | 2241 | N | GLU | B | 258 | 49.369 | 8.819 | 28.377 | 1.00 37.25 | N |
| ATOM | 2242 | CA | GLU | B | 258 | 50.591 | 8.530 | 29.115 | 1.00 37.41 | C |
| ATOM | 2243 | CB | GLU | B | 258 | 51.738 | 8.243 | 28.131 | 1.00 38.49 | C |
| ATOM | 2244 | CG | GLU | B | 258 | 51.348 | 7.380 | 26.942 | 1.00 43.60 | C |
| ATOM | 2245 | CD | GLU | B | 258 | 52.516 | 7.098 | 26.004 | 1.00 46.43 | C |
| ATOM | 2246 | OE1 | GLU | B | 258 | 53.221 | 8.056 | 25.620 | 1.00 47.24 | O |
| ATOM | 2247 | OE2 | GLU | B | 258 | 52.723 | 5.917 | 25.640 | 1.00 49.09 | O |
| ATOM | 2248 | C | GLU | B | 258 | 51.009 | 9.684 | 30.019 | 1.00 36.21 | C |
| ATOM | 2249 | O | GLU | B | 258 | 50.518 | 10.808 | 29.882 | 1.00 35.85 | O |
| ATOM | 2250 | N | VAL | B | 259 | 51.921 | 9.386 | 30.945 | 1.00 34.77 | N |
| ATOM | 2251 | CA | VAL | B | 259 | 52.473 | 10.383 | 31.851 | 1.00 33.64 | C |
| ATOM | 2252 | CB | VAL | B | 259 | 52.112 | 10.096 | 33.311 | 1.00 32.90 | C |
| ATOM | 2253 | CG1 | VAL | B | 259 | 52.810 | 11.104 | 34.204 | 1.00 35.59 | C |
| ATOM | 2254 | CG2 | VAL | B | 259 | 50.599 | 10.187 | 33.508 | 1.00 35.89 | C |
| ATOM | 2255 | C | VAL | B | 259 | 53.992 | 10.317 | 31.711 | 1.00 33.82 | C |
| ATOM | 2256 | O | VAL | B | 259 | 54.565 | 9.227 | 31.714 | 1.00 31.20 | O |
| ATOM | 2257 | N | TRP | B | 260 | 54.630 | 11.480 | 31.597 | 1.00 35.22 | N |
| ATOM | 2258 | CA | TRP | B | 260 | 56.087 | 11.578 | 31.437 | 1.00 37.87 | C |
| ATOM | 2259 | CB | TRP | B | 260 | 56.450 | 12.011 | 30.002 | 1.00 38.51 | C |
| ATOM | 2260 | CG | TRP | B | 260 | 56.171 | 11.014 | 28.929 | 1.00 41.40 | C |
| ATOM | 2261 | CD2 | TRP | B | 260 | 57.133 | 10.405 | 28.057 | 1.00 42.81 | C |
| ATOM | 2262 | CE2 | TRP | B | 260 | 56.427 | 9.534 | 27.200 | 1.00 43.60 | C |

Figure 14

| ATOM | 2263 | CE3 | TRP | B | 260 | 58.525 | 10.512 | 27.917 | 1.00 | 44.54 | C |
|------|------|-----|-----|---|-----|--------|--------|--------|------|-------|---|
| ATOM | 2264 | CD1 | TRP | B | 260 | 54.957 | 10.502 | 28.577 | 1.00 | 41.44 | C |
| ATOM | 2265 | NE1 | TRP | B | 260 | 55.101 | 9.609 | 27.540 | 1.00 | 41.00 | N |
| ATOM | 2266 | CZ2 | TRP | B | 260 | 57.062 | 8.773 | 26.217 | 1.00 | 43.20 | C |
| ATOM | 2267 | CZ3 | TRP | B | 260 | 59.158 | 9.756 | 26.939 | 1.00 | 44.12 | C |
| ATOM | 2268 | CH2 | TRP | B | 260 | 58.424 | 8.897 | 26.102 | 1.00 | 45.36 | C |
| ATOM | 2269 | C | TRP | B | 260 | 56.740 | 12.591 | 32.374 | 1.00 | 37.38 | C |
| ATOM | 2270 | O | TRP | B | 260 | 56.117 | 13.561 | 32.800 | 1.00 | 39.25 | O |
| ATOM | 2271 | N | MET | B | 261 | 58.010 | 12.360 | 32.684 | 1.00 | 38.12 | N |
| ATOM | 2272 | CA | MET | B | 261 | 58.773 | 13.301 | 33.489 | 1.00 | 36.90 | C |
| ATOM | 2273 | CB | MET | B | 261 | 59.758 | 12.586 | 34.414 | 1.00 | 37.27 | C |
| ATOM | 2274 | CG | MET | B | 261 | 60.723 | 13.529 | 35.151 | 1.00 | 36.35 | C |
| ATOM | 2275 | SD | MET | B | 261 | 62.073 | 14.179 | 34.106 | 1.00 | 42.05 | S |
| ATOM | 2276 | CE | MET | B | 261 | 62.868 | 12.668 | 33.680 | 1.00 | 38.70 | C |
| ATOM | 2277 | C | MET | B | 261 | 59.542 | 14.079 | 32.429 | 1.00 | 37.15 | C |
| ATOM | 2278 | O | MET | B | 261 | 59.855 | 13.543 | 31.374 | 1.00 | 35.33 | O |
| ATOM | 2279 | N | GLY | B | 262 | 59.821 | 15.342 | 32.700 | 1.00 | 38.84 | N |
| ATOM | 2280 | CA | GLY | B | 262 | 60.548 | 16.137 | 31.736 | 1.00 | 41.95 | C |
| ATOM | 2281 | C | GLY | B | 262 | 60.932 | 17.446 | 32.369 | 1.00 | 43.92 | C |
| ATOM | 2282 | O | GLY | B | 262 | 60.769 | 17.628 | 33.579 | 1.00 | 46.18 | O |
| ATOM | 2283 | N | TYR | B | 263 | 61.446 | 18.364 | 31.565 | 1.00 | 44.97 | N |
| ATOM | 2284 | CA | TYR | B | 263 | 61.831 | 19.657 | 32.095 | 1.00 | 46.02 | C |
| ATOM | 2285 | CB | TYR | B | 263 | 63.346 | 19.835 | 32.014 | 1.00 | 45.19 | C |
| ATOM | 2286 | CG | TYR | B | 263 | 64.076 | 18.863 | 32.907 | 1.00 | 44.62 | C |
| ATOM | 2287 | CD1 | TYR | B | 263 | 64.209 | 17.525 | 32.541 | 1.00 | 44.66 | C |
| ATOM | 2288 | CE1 | TYR | B | 263 | 64.817 | 16.608 | 33.378 | 1.00 | 45.12 | C |
| ATOM | 2289 | CD2 | TYR | B | 263 | 64.576 | 19.266 | 34.144 | 1.00 | 42.84 | C |
| ATOM | 2290 | CE2 | TYR | B | 263 | 65.187 | 18.355 | 34.997 | 1.00 | 44.04 | C |
| ATOM | 2291 | CZ | TYR | B | 263 | 65.302 | 17.028 | 34.607 | 1.00 | 43.45 | C |
| ATOM | 2292 | OH | TYR | B | 263 | 65.889 | 16.108 | 35.438 | 1.00 | 43.18 | O |
| ATOM | 2293 | C | TYR | B | 263 | 61.121 | 20.797 | 31.403 | 1.00 | 48.09 | C |
| ATOM | 2294 | O | TYR | B | 263 | 60.826 | 20.744 | 30.207 | 1.00 | 47.88 | O |
| ATOM | 2295 | N | TYR | B | 264 | 60.849 | 21.826 | 32.192 | 1.00 | 50.13 | N |
| ATOM | 2296 | CA | TYR | B | 264 | 60.154 | 23.021 | 31.753 | 1.00 | 52.79 | C |
| ATOM | 2297 | CB | TYR | B | 264 | 59.012 | 23.285 | 32.738 | 1.00 | 54.42 | C |
| ATOM | 2298 | CG | TYR | B | 264 | 58.141 | 24.490 | 32.481 | 1.00 | 57.02 | C |
| ATOM | 2299 | CD1 | TYR | B | 264 | 57.628 | 24.762 | 31.211 | 1.00 | 57.10 | C |
| ATOM | 2300 | CE1 | TYR | B | 264 | 56.742 | 25.826 | 31.009 | 1.00 | 57.94 | C |
| ATOM | 2301 | CD2 | TYR | B | 264 | 57.753 | 25.314 | 33.539 | 1.00 | 57.79 | C |
| ATOM | 2302 | CE2 | TYR | B | 264 | 56.872 | 26.376 | 33.350 | 1.00 | 57.46 | C |
| ATOM | 2303 | CZ | TYR | B | 264 | 56.369 | 26.625 | 32.089 | 1.00 | 56.84 | C |
| ATOM | 2304 | OH | TYR | B | 264 | 55.479 | 27.663 | 31.924 | 1.00 | 57.55 | O |
| ATOM | 2305 | C | TYR | B | 264 | 61.187 | 24.140 | 31.773 | 1.00 | 53.82 | C |
| ATOM | 2306 | O | TYR | B | 264 | 61.667 | 24.534 | 32.838 | 1.00 | 52.37 | O |
| ATOM | 2307 | N | ASN | B | 265 | 61.541 | 24.627 | 30.585 | 1.00 | 54.70 | N |
| ATOM | 2308 | CA | ASN | B | 265 | 62.534 | 25.686 | 30.438 | 1.00 | 55.83 | C |
| ATOM | 2309 | CB | ASN | B | 265 | 62.136 | 26.920 | 31.252 | 1.00 | 57.39 | C |
| ATOM | 2310 | CG | ASN | B | 265 | 60.850 | 27.546 | 30.761 | 1.00 | 59.35 | C |
| ATOM | 2311 | OD1 | ASN | B | 265 | 60.716 | 27.864 | 29.576 | 1.00 | 60.50 | O |
| ATOM | 2312 | ND2 | ASN | B | 265 | 59.893 | 27.730 | 31.667 | 1.00 | 60.41 | N |
| ATOM | 2313 | C | ASN | B | 265 | 63.911 | 25.190 | 30.873 | 1.00 | 55.92 | C |
| ATOM | 2314 | O | ASN | B | 265 | 64.660 | 25.901 | 31.544 | 1.00 | 55.88 | O |
| ATOM | 2315 | N | GLY | B | 266 | 64.222 | 23.954 | 30.490 | 1.00 | 55.61 | N |
| ATOM | 2316 | CA | GLY | B | 266 | 65.507 | 23.352 | 30.798 | 1.00 | 56.09 | C |
| ATOM | 2317 | C | GLY | B | 266 | 65.987 | 23.307 | 32.239 | 1.00 | 57.07 | C |
| ATOM | 2318 | O | GLY | B | 266 | 67.125 | 22.889 | 32.479 | 1.00 | 58.12 | O |
| ATOM | 2319 | N | HIS | B | 267 | 65.165 | 23.727 | 33.199 | 1.00 | 56.68 | N |
| ATOM | 2320 | CA | HIS | B | 267 | 65.591 | 23.694 | 34.600 | 1.00 | 57.02 | C |
| ATOM | 2321 | CB | HIS | B | 267 | 66.213 | 25.039 | 35.004 | 1.00 | 59.15 | C |
| ATOM | 2322 | CG | HIS | B | 267 | 67.530 | 25.320 | 34.342 | 1.00 | 61.04 | C |

Figure 14

| | | | | | | | | | |
|---|---|---|---|---|---|---|---|---|---|
| ATOM | 2323 | CD2 | HIS | B | 267 | 68.790 | 25.355 | 34.839 | 1.00 62.14 | C |
| ATOM | 2324 | ND1 | HIS | B | 267 | 67.644 | 25.590 | 32.995 | 1.00 61.04 | N |
| ATOM | 2325 | CE1 | HIS | B | 267 | 68.916 | 25.779 | 32.690 | 1.00 61.03 | C |
| ATOM | 2326 | NE2 | HIS | B | 267 | 69.632 | 25.642 | 33.791 | 1.00 62.10 | N |
| ATOM | 2327 | C | HIS | B | 267 | 64.510 | 23.317 | 35.612 | 1.00 56.16 | C |
| ATOM | 2328 | O | HIS | B | 267 | 64.808 | 23.113 | 36.790 | 1.00 55.99 | O |
| ATOM | 2329 | N | THR | B | 268 | 63.262 | 23.223 | 35.168 | 1.00 54.00 | N |
| ATOM | 2330 | CA | THR | B | 268 | 62.177 | 22.862 | 36.079 | 1.00 52.16 | C |
| ATOM | 2331 | CB | THR | B | 268 | 61.025 | 23.880 | 35.996 | 1.00 53.09 | C |
| ATOM | 2332 | OG1 | THR | B | 268 | 61.539 | 25.199 | 36.221 | 1.00 54.90 | O |
| ATOM | 2333 | CG2 | THR | B | 268 | 59.968 | 23.580 | 37.048 | 1.00 53.08 | C |
| ATOM | 2334 | C | THR | B | 268 | 61.650 | 21.474 | 35.745 | 1.00 49.95 | C |
| ATOM | 2335 | O | THR | B | 268 | 61.149 | 21.241 | 34.647 | 1.00 50.37 | O |
| ATOM | 2336 | N | LYS | B | 269 | 61.779 | 20.549 | 36.692 | 1.00 47.50 | N |
| ATOM | 2337 | CA | LYS | B | 269 | 61.316 | 19.177 | 36.492 | 1.00 44.76 | C |
| ATOM | 2338 | CB | LYS | B | 269 | 61.976 | 18.243 | 37.515 | 1.00 44.35 | C |
| ATOM | 2339 | CG | LYS | B | 269 | 61.973 | 16.765 | 37.126 | 1.00 44.94 | C |
| ATOM | 2340 | CD | LYS | B | 269 | 62.929 | 15.945 | 38.013 | 1.00 45.28 | C |
| ATOM | 2341 | CE | LYS | B | 269 | 63.075 | 14.515 | 37.504 | 1.00 47.07 | C |
| ATOM | 2342 | NZ | LYS | B | 269 | 63.853 | 13.636 | 38.433 | 1.00 46.31 | N |
| ATOM | 2343 | C | LYS | B | 269 | 59.793 | 19.158 | 36.639 | 1.00 43.27 | C |
| ATOM | 2344 | O | LYS | B | 269 | 59.234 | 19.784 | 37.543 | 1.00 42.17 | O |
| ATOM | 2345 | N | VAL | B | 270 | 59.124 | 18.450 | 35.737 | 1.00 41.13 | N |
| ATOM | 2346 | CA | VAL | B | 270 | 57.670 | 18.393 | 35.763 | 1.00 38.45 | C |
| ATOM | 2347 | CB | VAL | B | 270 | 57.054 | 19.439 | 34.799 | 1.00 36.91 | C |
| ATOM | 2348 | CG1 | VAL | B | 270 | 57.422 | 20.839 | 35.231 | 1.00 38.93 | C |
| ATOM | 2349 | CG2 | VAL | B | 270 | 57.551 | 19.188 | 33.384 | 1.00 38.57 | C |
| ATOM | 2350 | C | VAL | B | 270 | 57.150 | 17.032 | 35.335 | 1.00 37.79 | C |
| ATOM | 2351 | O | VAL | B | 270 | 57.904 | 16.187 | 34.851 | 1.00 35.75 | O |
| ATOM | 2352 | N | ALA | B | 271 | 55.850 | 16.830 | 35.533 | 1.00 37.06 | N |
| ATOM | 2353 | CA | ALA | B | 271 | 55.180 | 15.607 | 35.118 | 1.00 36.09 | C |
| ATOM | 2354 | CB | ALA | B | 271 | 54.295 | 15.088 | 36.229 | 1.00 38.81 | C |
| ATOM | 2355 | C | ALA | B | 271 | 54.326 | 16.076 | 33.941 | 1.00 35.73 | C |
| ATOM | 2356 | O | ALA | B | 271 | 53.816 | 17.192 | 33.965 | 1.00 33.89 | O |
| ATOM | 2357 | N | VAL | B | 272 | 54.172 | 15.249 | 32.913 | 1.00 35.84 | N |
| ATOM | 2358 | CA | VAL | B | 272 | 53.387 | 15.655 | 31.754 | 1.00 35.09 | C |
| ATOM | 2359 | CB | VAL | B | 272 | 54.310 | 16.022 | 30.550 | 1.00 36.93 | C |
| ATOM | 2360 | CG1 | VAL | B | 272 | 53.473 | 16.351 | 29.311 | 1.00 36.30 | C |
| ATOM | 2361 | CG2 | VAL | B | 272 | 55.190 | 17.217 | 30.919 | 1.00 37.31 | C |
| ATOM | 2362 | C | VAL | B | 272 | 52.449 | 14.543 | 31.345 | 1.00 34.64 | C |
| ATOM | 2363 | O | VAL | B | 272 | 52.894 | 13.443 | 31.006 | 1.00 35.21 | O |
| ATOM | 2364 | N | LYS | B | 273 | 51.148 | 14.820 | 31.396 | 1.00 33.37 | N |
| ATOM | 2365 | CA | LYS | B | 273 | 50.156 | 13.821 | 31.014 | 1.00 33.34 | C |
| ATOM | 2366 | CB | LYS | B | 273 | 48.970 | 13.811 | 32.005 | 1.00 32.90 | C |
| ATOM | 2367 | CG | LYS | B | 273 | 47.912 | 12.737 | 31.716 | 1.00 34.74 | C |
| ATOM | 2368 | CD | LYS | B | 273 | 46.730 | 12.760 | 32.705 | 1.00 37.44 | C |
| ATOM | 2369 | CE | LYS | B | 273 | 47.120 | 12.271 | 34.114 | 1.00 39.50 | C |
| ATOM | 2370 | NZ | LYS | B | 273 | 45.959 | 12.325 | 35.096 | 1.00 37.78 | N |
| ATOM | 2371 | C | LYS | B | 273 | 49.682 | 14.196 | 29.620 | 1.00 34.51 | C |
| ATOM | 2372 | O | LYS | B | 273 | 49.252 | 15.326 | 29.387 | 1.00 31.68 | O |
| ATOM | 2373 | N | SER | B | 274 | 49.785 | 13.252 | 28.689 | 1.00 36.06 | N |
| ATOM | 2374 | CA | SER | B | 274 | 49.367 | 13.504 | 27.325 | 1.00 40.37 | C |
| ATOM | 2375 | CB | SER | B | 274 | 50.479 | 13.136 | 26.335 | 1.00 41.57 | C |
| ATOM | 2376 | OG | SER | B | 274 | 50.641 | 11.733 | 26.230 | 1.00 44.94 | O |
| ATOM | 2377 | C | SER | B | 274 | 48.117 | 12.697 | 27.034 | 1.00 41.81 | C |
| ATOM | 2378 | O | SER | B | 274 | 47.962 | 11.566 | 27.505 | 1.00 43.07 | O |
| ATOM | 2379 | N | LEU | B | 275 | 47.219 | 13.293 | 26.263 | 1.00 43.48 | N |
| ATOM | 2380 | CA | LEU | B | 275 | 45.958 | 12.657 | 25.924 | 1.00 44.89 | C |
| ATOM | 2381 | CB | LEU | B | 275 | 44.862 | 13.715 | 25.818 | 1.00 45.01 | C |
| ATOM | 2382 | CG | LEU | B | 275 | 43.518 | 13.322 | 25.195 | 1.00 45.49 | C |

Figure 14

```
ATOM   2383  CD1 LEU B 275      42.854  12.176  25.968  1.00 43.00           C
ATOM   2384  CD2 LEU B 275      42.624  14.552  25.191  1.00 45.52           C
ATOM   2385  C   LEU B 275      46.021  11.875  24.633  1.00 46.13           C
ATOM   2386  O   LEU B 275      46.519  12.372  23.623  1.00 46.75           O
ATOM   2387  N   LYS B 276      45.524  10.642  24.675  1.00 46.32           N
ATOM   2388  CA  LYS B 276      45.487   9.799  23.489  1.00 46.59           C
ATOM   2389  CB  LYS B 276      45.330   8.327  23.877  1.00 46.64           C
ATOM   2390  CG  LYS B 276      45.268   7.385  22.683  1.00 47.94           C
ATOM   2391  CD  LYS B 276      45.125   5.940  23.125  1.00 49.17           C
ATOM   2392  CE  LYS B 276      46.282   5.515  24.012  1.00 50.87           C
ATOM   2393  NZ  LYS B 276      46.092   4.143  24.564  1.00 52.68           N
ATOM   2394  C   LYS B 276      44.261  10.270  22.720  1.00 45.75           C
ATOM   2395  O   LYS B 276      43.137  10.134  23.198  1.00 43.08           O
ATOM   2396  N   GLN B 277      44.485  10.844  21.539  1.00 46.97           N
ATOM   2397  CA  GLN B 277      43.394  11.368  20.716  1.00 46.44           C
ATOM   2398  CB  GLN B 277      43.926  11.772  19.332  1.00 47.08           C
ATOM   2399  CG  GLN B 277      43.043  12.771  18.595  1.00 48.53           C
ATOM   2400  CD  GLN B 277      43.640  13.213  17.268  1.00 50.66           C
ATOM   2401  OE1 GLN B 277      43.815  12.407  16.351  1.00 51.20           O
ATOM   2402  NE2 GLN B 277      43.955  14.500  17.160  1.00 49.49           N
ATOM   2403  C   GLN B 277      42.274  10.346  20.564  1.00 45.50           C
ATOM   2404  O   GLN B 277      42.524   9.181  20.270  1.00 45.02           O
ATOM   2405  N   GLY B 278      41.038  10.786  20.787  1.00 45.91           N
ATOM   2406  CA  GLY B 278      39.898   9.890  20.656  1.00 44.95           C
ATOM   2407  C   GLY B 278      39.352   9.341  21.964  1.00 45.02           C
ATOM   2408  O   GLY B 278      38.163   9.023  22.061  1.00 42.56           O
ATOM   2409  N   SER B 279      40.220   9.215  22.966  1.00 45.20           N
ATOM   2410  CA  SER B 279      39.829   8.695  24.276  1.00 44.48           C
ATOM   2411  CB  SER B 279      41.011   8.777  25.251  1.00 44.31           C
ATOM   2412  OG  SER B 279      42.084   7.953  24.826  1.00 44.41           O
ATOM   2413  C   SER B 279      38.663   9.511  24.815  1.00 45.08           C
ATOM   2414  O   SER B 279      37.661   8.966  25.278  1.00 45.50           O
ATOM   2415  N   MET B 280      38.825  10.828  24.755  1.00 44.87           N
ATOM   2416  CA  MET B 280      37.816  11.783  25.192  1.00 45.17           C
ATOM   2417  CB  MET B 280      37.895  12.007  26.704  1.00 44.52           C
ATOM   2418  CG  MET B 280      39.192  12.638  27.184  1.00 44.45           C
ATOM   2419  SD  MET B 280      39.475  12.356  28.948  1.00 43.12           S
ATOM   2420  CE  MET B 280      38.887  13.804  29.640  1.00 42.17           C
ATOM   2421  C   MET B 280      38.140  13.074  24.454  1.00 45.43           C
ATOM   2422  O   MET B 280      39.103  13.126  23.689  1.00 44.87           O
ATOM   2423  N   SER B 281      37.350  14.116  24.677  1.00 46.59           N
ATOM   2424  CA  SER B 281      37.606  15.378  24.001  1.00 48.15           C
ATOM   2425  CB  SER B 281      36.308  16.169  23.835  1.00 48.52           C
ATOM   2426  OG  SER B 281      35.835  16.640  25.083  1.00 50.06           O
ATOM   2427  C   SER B 281      38.609  16.216  24.779  1.00 49.24           C
ATOM   2428  O   SER B 281      38.794  16.028  25.985  1.00 48.44           O
ATOM   2429  N   PRO B 282      39.297  17.142  24.088  1.00 49.76           N
ATOM   2430  CD  PRO B 282      39.395  17.278  22.623  1.00 49.28           C
ATOM   2431  CA  PRO B 282      40.274  18.005  24.752  1.00 50.37           C
ATOM   2432  CB  PRO B 282      40.656  18.985  23.651  1.00 49.65           C
ATOM   2433  CG  PRO B 282      40.677  18.087  22.449  1.00 49.57           C
ATOM   2434  C   PRO B 282      39.678  18.694  25.978  1.00 50.90           C
ATOM   2435  O   PRO B 282      40.222  18.583  27.081  1.00 51.80           O
ATOM   2436  N   ASP B 283      38.557  19.391  25.785  1.00 51.90           N
ATOM   2437  CA  ASP B 283      37.882  20.096  26.877  1.00 52.47           C
ATOM   2438  CB  ASP B 283      36.506  20.595  26.429  1.00 54.67           C
ATOM   2439  CG  ASP B 283      36.592  21.691  25.387  1.00 56.71           C
ATOM   2440  OD1 ASP B 283      37.178  22.754  25.691  1.00 56.20           O
ATOM   2441  OD2 ASP B 283      36.074  21.492  24.266  1.00 56.98           O
ATOM   2442  C   ASP B 283      37.707  19.195  28.096  1.00 52.35           C
```

Figure 14

| | | | | | | | | | | |
|---|---|---|---|---|---|---|---|---|---|---|
| ATOM | 2443 | O | ASP | B | 283 | 37.926 | 19.614 | 29.235 | 1.00 51.96 | O |
| ATOM | 2444 | N | ALA | B | 284 | 37.297 | 17.956 | 27.848 | 1.00 51.91 | N |
| ATOM | 2445 | CA | ALA | B | 284 | 37.099 | 16.998 | 28.925 | 1.00 52.02 | C |
| ATOM | 2446 | CB | ALA | B | 284 | 36.513 | 15.706 | 28.372 | 1.00 51.39 | C |
| ATOM | 2447 | C | ALA | B | 284 | 38.443 | 16.725 | 29.597 | 1.00 51.81 | C |
| ATOM | 2448 | O | ALA | B | 284 | 38.536 | 16.684 | 30.821 | 1.00 52.74 | O |
| ATOM | 2449 | N | PHE | B | 285 | 39.480 | 16.534 | 28.785 | 1.00 50.90 | N |
| ATOM | 2450 | CA | PHE | B | 285 | 40.814 | 16.266 | 29.303 | 1.00 50.22 | C |
| ATOM | 2451 | CB | PHE | B | 285 | 41.783 | 15.989 | 28.153 | 1.00 48.64 | C |
| ATOM | 2452 | CG | PHE | B | 285 | 43.174 | 15.623 | 28.599 | 1.00 47.62 | C |
| ATOM | 2453 | CD1 | PHE | B | 285 | 43.410 | 14.435 | 29.289 | 1.00 47.25 | C |
| ATOM | 2454 | CD2 | PHE | B | 285 | 44.251 | 16.459 | 28.317 | 1.00 46.68 | C |
| ATOM | 2455 | CE1 | PHE | B | 285 | 44.703 | 14.085 | 29.692 | 1.00 48.38 | C |
| ATOM | 2456 | CE2 | PHE | B | 285 | 45.550 | 16.121 | 28.714 | 1.00 46.76 | C |
| ATOM | 2457 | CZ | PHE | B | 285 | 45.776 | 14.930 | 29.402 | 1.00 48.18 | C |
| ATOM | 2458 | C | PHE | B | 285 | 41.298 | 17.458 | 30.108 | 1.00 50.80 | C |
| ATOM | 2459 | O | PHE | B | 285 | 41.718 | 17.313 | 31.252 | 1.00 51.33 | O |
| ATOM | 2460 | N | LEU | B | 286 | 41.218 | 18.639 | 29.506 | 1.00 52.16 | N |
| ATOM | 2461 | CA | LEU | B | 286 | 41.650 | 19.867 | 30.158 | 1.00 53.39 | C |
| ATOM | 2462 | CB | LEU | B | 286 | 41.641 | 21.021 | 29.149 | 1.00 54.06 | C |
| ATOM | 2463 | CG | LEU | B | 286 | 42.577 | 20.854 | 27.942 | 1.00 55.16 | C |
| ATOM | 2464 | CD1 | LEU | B | 286 | 42.282 | 21.929 | 26.905 | 1.00 56.00 | C |
| ATOM | 2465 | CD2 | LEU | B | 286 | 44.030 | 20.927 | 28.392 | 1.00 53.80 | C |
| ATOM | 2466 | C | LEU | B | 286 | 40.796 | 20.224 | 31.373 | 1.00 54.57 | C |
| ATOM | 2467 | O | LEU | B | 286 | 41.072 | 21.207 | 32.067 | 1.00 55.03 | O |
| ATOM | 2468 | N | ALA | B | 287 | 39.766 | 19.424 | 31.639 | 1.00 55.38 | N |
| ATOM | 2469 | CA | ALA | B | 287 | 38.887 | 19.674 | 32.777 | 1.00 54.60 | C |
| ATOM | 2470 | CB | ALA | B | 287 | 37.717 | 18.702 | 32.758 | 1.00 55.41 | C |
| ATOM | 2471 | C | ALA | B | 287 | 39.660 | 19.544 | 34.085 | 1.00 55.00 | C |
| ATOM | 2472 | O | ALA | B | 287 | 39.467 | 20.339 | 35.007 | 1.00 53.14 | O |
| ATOM | 2473 | N | GLU | B | 288 | 40.534 | 18.541 | 34.162 | 1.00 55.47 | N |
| ATOM | 2474 | CA | GLU | B | 288 | 41.345 | 18.319 | 35.359 | 1.00 56.09 | C |
| ATOM | 2475 | CB | GLU | B | 288 | 42.241 | 17.078 | 35.198 | 1.00 57.36 | C |
| ATOM | 2476 | CG | GLU | B | 288 | 41.493 | 15.752 | 35.042 | 1.00 59.03 | C |
| ATOM | 2477 | CD | GLU | B | 288 | 41.068 | 15.459 | 33.605 | 1.00 60.80 | C |
| ATOM | 2478 | OE1 | GLU | B | 288 | 41.949 | 15.132 | 32.774 | 1.00 58.87 | O |
| ATOM | 2479 | OE2 | GLU | B | 288 | 39.853 | 15.552 | 33.310 | 1.00 59.89 | O |
| ATOM | 2480 | C | GLU | B | 288 | 42.222 | 19.534 | 35.642 | 1.00 55.71 | C |
| ATOM | 2481 | O | GLU | B | 288 | 42.453 | 19.886 | 36.798 | 1.00 54.88 | O |
| ATOM | 2482 | N | ALA | B | 289 | 42.705 | 20.171 | 34.578 | 1.00 55.44 | N |
| ATOM | 2483 | CA | ALA | B | 289 | 43.559 | 21.347 | 34.699 | 1.00 55.39 | C |
| ATOM | 2484 | CB | ALA | B | 289 | 44.218 | 21.655 | 33.357 | 1.00 55.90 | C |
| ATOM | 2485 | C | ALA | B | 289 | 42.787 | 22.564 | 35.195 | 1.00 55.35 | C |
| ATOM | 2486 | O | ALA | B | 289 | 43.287 | 23.328 | 36.024 | 1.00 55.60 | O |
| ATOM | 2487 | N | ASN | B | 290 | 41.571 | 22.746 | 34.683 | 1.00 55.26 | N |
| ATOM | 2488 | CA | ASN | B | 290 | 40.727 | 23.871 | 35.080 | 1.00 55.27 | C |
| ATOM | 2489 | CB | ASN | B | 290 | 39.411 | 23.844 | 34.297 | 1.00 56.92 | C |
| ATOM | 2490 | CG | ASN | B | 290 | 39.600 | 24.192 | 32.832 | 1.00 58.51 | C |
| ATOM | 2491 | OD1 | ASN | B | 290 | 38.682 | 24.048 | 32.022 | 1.00 60.43 | O |
| ATOM | 2492 | ND2 | ASN | B | 290 | 40.792 | 24.662 | 32.487 | 1.00 59.57 | N |
| ATOM | 2493 | C | ASN | B | 290 | 40.443 | 23.828 | 36.576 | 1.00 54.79 | C |
| ATOM | 2494 | O | ASN | B | 290 | 40.298 | 24.866 | 37.226 | 1.00 54.19 | O |
| ATOM | 2495 | N | LEU | B | 291 | 40.363 | 22.615 | 37.112 | 1.00 54.09 | N |
| ATOM | 2496 | CA | LEU | B | 291 | 40.112 | 22.403 | 38.528 | 1.00 53.33 | C |
| ATOM | 2497 | CB | LEU | B | 291 | 39.745 | 20.938 | 38.773 | 1.00 53.71 | C |
| ATOM | 2498 | CG | LEU | B | 291 | 38.383 | 20.529 | 38.205 | 1.00 54.00 | C |
| ATOM | 2499 | CD1 | LEU | B | 291 | 38.208 | 19.019 | 38.284 | 1.00 55.80 | C |
| ATOM | 2500 | CD2 | LEU | B | 291 | 37.288 | 21.251 | 38.971 | 1.00 53.31 | C |
| ATOM | 2501 | C | LEU | B | 291 | 41.333 | 22.780 | 39.361 | 1.00 53.32 | C |
| ATOM | 2502 | O | LEU | B | 291 | 41.205 | 23.434 | 40.396 | 1.00 51.95 | O |

Figure 14

| | | | | | | | | | |
|---|---|---|---|---|---|---|---|---|---|
| ATOM | 2503 | N | MET | B | 292 | 42.515 | 22.361 | 38.917 | 1.00 53.58 | N |
| ATOM | 2504 | CA | MET | B | 292 | 43.741 | 22.683 | 39.636 | 1.00 54.40 | C |
| ATOM | 2505 | CB | MET | B | 292 | 44.943 | 22.000 | 38.987 | 1.00 55.07 | C |
| ATOM | 2506 | CG | MET | B | 292 | 45.077 | 20.529 | 39.342 | 1.00 54.79 | C |
| ATOM | 2507 | SD | MET | B | 292 | 46.533 | 19.755 | 38.603 | 1.00 53.89 | S |
| ATOM | 2508 | CE | MET | B | 292 | 45.796 | 18.997 | 37.200 | 1.00 53.16 | C |
| ATOM | 2509 | C | MET | B | 292 | 43.943 | 24.193 | 39.667 | 1.00 55.34 | C |
| ATOM | 2510 | O | MET | B | 292 | 44.590 | 24.723 | 40.572 | 1.00 55.26 | O |
| ATOM | 2511 | N | LYS | B | 293 | 43.383 | 24.885 | 38.677 | 1.00 56.40 | N |
| ATOM | 2512 | CA | LYS | B | 293 | 43.476 | 26.339 | 38.622 | 1.00 57.00 | C |
| ATOM | 2513 | CB | LYS | B | 293 | 42.907 | 26.879 | 37.306 | 1.00 57.87 | C |
| ATOM | 2514 | CG | LYS | B | 293 | 43.699 | 26.538 | 36.058 | 1.00 59.88 | C |
| ATOM | 2515 | CD | LYS | B | 293 | 43.290 | 27.462 | 34.916 | 1.00 60.70 | C |
| ATOM | 2516 | CE | LYS | B | 293 | 43.997 | 27.112 | 33.624 | 1.00 61.64 | C |
| ATOM | 2517 | NZ | LYS | B | 293 | 43.618 | 25.759 | 33.147 | 1.00 63.74 | N |
| ATOM | 2518 | C | LYS | B | 293 | 42.662 | 26.911 | 39.775 | 1.00 56.65 | C |
| ATOM | 2519 | O | LYS | B | 293 | 43.192 | 27.605 | 40.641 | 1.00 57.54 | O |
| ATOM | 2520 | N | GLN | B | 294 | 41.368 | 26.610 | 39.775 | 1.00 55.62 | N |
| ATOM | 2521 | CA | GLN | B | 294 | 40.449 | 27.084 | 40.806 | 1.00 55.78 | C |
| ATOM | 2522 | CB | GLN | B | 294 | 39.058 | 26.479 | 40.581 | 1.00 56.09 | C |
| ATOM | 2523 | CG | GLN | B | 294 | 38.254 | 27.165 | 39.482 | 1.00 58.15 | C |
| ATOM | 2524 | CD | GLN | B | 294 | 37.730 | 28.527 | 39.910 | 1.00 59.10 | C |
| ATOM | 2525 | OE1 | GLN | B | 294 | 38.472 | 29.352 | 40.446 | 1.00 59.56 | O |
| ATOM | 2526 | NE2 | GLN | B | 294 | 36.444 | 28.770 | 39.666 | 1.00 59.22 | N |
| ATOM | 2527 | C | GLN | B | 294 | 40.895 | 26.789 | 42.238 | 1.00 55.69 | C |
| ATOM | 2528 | O | GLN | B | 294 | 40.654 | 27.589 | 43.149 | 1.00 56.01 | O |
| ATOM | 2529 | N | LEU | B | 295 | 41.539 | 25.643 | 42.442 | 1.00 54.88 | N |
| ATOM | 2530 | CA | LEU | B | 295 | 41.985 | 25.271 | 43.776 | 1.00 53.91 | C |
| ATOM | 2531 | CB | LEU | B | 295 | 41.243 | 24.015 | 44.241 | 1.00 53.97 | C |
| ATOM | 2532 | CG | LEU | B | 295 | 39.736 | 24.234 | 44.402 | 1.00 54.06 | C |
| ATOM | 2533 | CD1 | LEU | B | 295 | 39.063 | 22.955 | 44.861 | 1.00 54.89 | C |
| ATOM | 2534 | CD2 | LEU | B | 295 | 39.497 | 25.350 | 45.407 | 1.00 54.65 | C |
| ATOM | 2535 | C | LEU | B | 295 | 43.486 | 25.064 | 43.895 | 1.00 53.33 | C |
| ATOM | 2536 | O | LEU | B | 295 | 44.048 | 24.121 | 43.340 | 1.00 54.70 | O |
| ATOM | 2537 | N | GLN | B | 296 | 44.128 | 25.966 | 44.632 | 1.00 51.71 | N |
| ATOM | 2538 | CA | GLN | B | 296 | 45.564 | 25.906 | 44.856 | 1.00 50.22 | C |
| ATOM | 2539 | CB | GLN | B | 296 | 46.239 | 27.147 | 44.272 | 1.00 51.59 | C |
| ATOM | 2540 | CG | GLN | B | 296 | 46.490 | 27.044 | 42.776 | 1.00 53.60 | C |
| ATOM | 2541 | CD | GLN | B | 296 | 46.915 | 28.361 | 42.158 | 1.00 55.22 | C |
| ATOM | 2542 | OE1 | GLN | B | 296 | 47.851 | 29.012 | 42.628 | 1.00 54.94 | O |
| ATOM | 2543 | NE2 | GLN | B | 296 | 46.228 | 28.759 | 41.093 | 1.00 55.67 | N |
| ATOM | 2544 | C | GLN | B | 296 | 45.834 | 25.797 | 46.348 | 1.00 47.45 | C |
| ATOM | 2545 | O | GLN | B | 296 | 45.254 | 26.530 | 47.152 | 1.00 47.19 | O |
| ATOM | 2546 | N | HIS | B | 297 | 46.716 | 24.875 | 46.715 | 1.00 44.39 | N |
| ATOM | 2547 | CA | HIS | B | 297 | 47.030 | 24.656 | 48.119 | 1.00 43.31 | C |
| ATOM | 2548 | CB | HIS | B | 297 | 45.840 | 23.944 | 48.787 | 1.00 41.17 | C |
| ATOM | 2549 | CG | HIS | B | 297 | 45.892 | 23.928 | 50.284 | 1.00 40.08 | C |
| ATOM | 2550 | CD2 | HIS | B | 297 | 45.276 | 24.704 | 51.203 | 1.00 39.03 | C |
| ATOM | 2551 | ND1 | HIS | B | 297 | 46.637 | 23.012 | 50.995 | 1.00 40.78 | N |
| ATOM | 2552 | CE1 | HIS | B | 297 | 46.474 | 23.223 | 52.288 | 1.00 40.02 | C |
| ATOM | 2553 | NE2 | HIS | B | 297 | 45.652 | 24.245 | 52.442 | 1.00 39.97 | N |
| ATOM | 2554 | C | HIS | B | 297 | 48.296 | 23.810 | 48.211 | 1.00 41.65 | C |
| ATOM | 2555 | O | HIS | B | 297 | 48.660 | 23.132 | 47.257 | 1.00 40.30 | O |
| ATOM | 2556 | N | GLN | B | 298 | 48.964 | 23.855 | 49.355 | 1.00 42.96 | N |
| ATOM | 2557 | CA | GLN | B | 298 | 50.186 | 23.089 | 49.545 | 1.00 44.67 | C |
| ATOM | 2558 | CB | GLN | B | 298 | 50.852 | 23.478 | 50.865 | 1.00 48.30 | C |
| ATOM | 2559 | CG | GLN | B | 298 | 52.194 | 24.191 | 50.699 | 1.00 52.58 | C |
| ATOM | 2560 | CD | GLN | B | 298 | 53.231 | 23.358 | 49.953 | 1.00 54.77 | C |
| ATOM | 2561 | OE1 | GLN | B | 298 | 53.072 | 23.055 | 48.766 | 1.00 54.64 | O |

Figure 14

| ATOM | 2562 | NE2 | GLN | B | 298 | 54.304 | 22.990 | 50.650 | 1.00 | 55.66 | N |
|------|------|-----|-----|---|-----|--------|--------|--------|------|-------|---|
| ATOM | 2563 | C | GLN | B | 298 | 49.959 | 21.581 | 49.525 | 1.00 | 43.84 | C |
| ATOM | 2564 | O | GLN | B | 298 | 50.889 | 20.814 | 49.270 | 1.00 | 42.58 | O |
| ATOM | 2565 | N | ARG | B | 299 | 48.726 | 21.160 | 49.786 | 1.00 | 42.41 | N |
| ATOM | 2566 | CA | ARG | B | 299 | 48.404 | 19.737 | 49.810 | 1.00 | 41.91 | C |
| ATOM | 2567 | CB | ARG | B | 299 | 47.512 | 19.429 | 51.016 | 1.00 | 42.42 | C |
| ATOM | 2568 | CG | ARG | B | 299 | 48.065 | 19.962 | 52.336 | 1.00 | 43.54 | C |
| ATOM | 2569 | CD | ARG | B | 299 | 49.541 | 19.606 | 52.511 | 1.00 | 46.33 | C |
| ATOM | 2570 | NE | ARG | B | 299 | 50.054 | 20.019 | 53.814 | 1.00 | 48.22 | N |
| ATOM | 2571 | CZ | ARG | B | 299 | 51.338 | 19.995 | 54.159 | 1.00 | 48.54 | C |
| ATOM | 2572 | NH1 | ARG | B | 299 | 52.257 | 19.580 | 53.294 | 1.00 | 49.22 | N |
| ATOM | 2573 | NH2 | ARG | B | 299 | 51.703 | 20.381 | 55.375 | 1.00 | 47.69 | N |
| ATOM | 2574 | C | ARG | B | 299 | 47.738 | 19.249 | 48.520 | 1.00 | 41.87 | C |
| ATOM | 2575 | O | ARG | B | 299 | 47.300 | 18.097 | 48.427 | 1.00 | 40.57 | O |
| ATOM | 2576 | N | LEU | B | 300 | 47.673 | 20.130 | 47.527 | 1.00 | 41.49 | N |
| ATOM | 2577 | CA | LEU | B | 300 | 47.082 | 19.794 | 46.231 | 1.00 | 41.57 | C |
| ATOM | 2578 | CB | LEU | B | 300 | 45.875 | 20.690 | 45.951 | 1.00 | 41.23 | C |
| ATOM | 2579 | CG | LEU | B | 300 | 44.499 | 20.192 | 46.408 | 1.00 | 40.02 | C |
| ATOM | 2580 | CD1 | LEU | B | 300 | 44.551 | 19.745 | 47.856 | 1.00 | 38.59 | C |
| ATOM | 2581 | CD2 | LEU | B | 300 | 43.477 | 21.300 | 46.215 | 1.00 | 38.73 | C |
| ATOM | 2582 | C | LEU | B | 300 | 48.110 | 19.966 | 45.113 | 1.00 | 42.40 | C |
| ATOM | 2583 | O | LEU | B | 300 | 48.774 | 20.995 | 45.035 | 1.00 | 41.45 | O |
| ATOM | 2584 | N | VAL | B | 301 | 48.232 | 18.959 | 44.251 | 1.00 | 42.36 | N |
| ATOM | 2585 | CA | VAL | B | 301 | 49.176 | 19.014 | 43.141 | 1.00 | 42.90 | C |
| ATOM | 2586 | CB | VAL | B | 301 | 49.004 | 17.792 | 42.219 | 1.00 | 41.71 | C |
| ATOM | 2587 | CG1 | VAL | B | 301 | 49.925 | 17.908 | 41.012 | 1.00 | 43.90 | C |
| ATOM | 2588 | CG2 | VAL | B | 301 | 49.308 | 16.520 | 42.991 | 1.00 | 40.02 | C |
| ATOM | 2589 | C | VAL | B | 301 | 48.943 | 20.299 | 42.339 | 1.00 | 44.73 | C |
| ATOM | 2590 | O | VAL | B | 301 | 47.844 | 20.529 | 41.827 | 1.00 | 43.79 | O |
| ATOM | 2591 | N | ARG | B | 302 | 49.983 | 21.126 | 42.239 | 1.00 | 45.20 | N |
| ATOM | 2592 | CA | ARG | B | 302 | 49.912 | 22.401 | 41.525 | 1.00 | 46.88 | C |
| ATOM | 2593 | CB | ARG | B | 302 | 50.918 | 23.390 | 42.121 | 1.00 | 49.08 | C |
| ATOM | 2594 | CG | ARG | B | 302 | 50.963 | 24.730 | 41.398 | 1.00 | 52.77 | C |
| ATOM | 2595 | CD | ARG | B | 302 | 52.209 | 25.541 | 41.751 | 1.00 | 55.84 | C |
| ATOM | 2596 | NE | ARG | B | 302 | 52.191 | 26.858 | 41.110 | 1.00 | 58.89 | N |
| ATOM | 2597 | CZ | ARG | B | 302 | 53.226 | 27.692 | 41.066 | 1.00 | 59.71 | C |
| ATOM | 2598 | NH1 | ARG | B | 302 | 54.381 | 27.357 | 41.626 | 1.00 | 61.07 | N |
| ATOM | 2599 | NH2 | ARG | B | 302 | 53.105 | 28.865 | 40.459 | 1.00 | 61.03 | N |
| ATOM | 2600 | C | ARG | B | 302 | 50.175 | 22.292 | 40.024 | 1.00 | 47.08 | C |
| ATOM | 2601 | O | ARG | B | 302 | 51.125 | 21.641 | 39.602 | 1.00 | 47.87 | O |
| ATOM | 2602 | N | LEU | B | 303 | 49.335 | 22.947 | 39.227 | 1.00 | 47.37 | N |
| ATOM | 2603 | CA | LEU | B | 303 | 49.477 | 22.946 | 37.771 | 1.00 | 47.32 | C |
| ATOM | 2604 | CB | LEU | B | 303 | 48.128 | 23.247 | 37.108 | 1.00 | 47.44 | C |
| ATOM | 2605 | CG | LEU | B | 303 | 48.105 | 23.360 | 35.582 | 1.00 | 46.10 | C |
| ATOM | 2606 | CD1 | LEU | B | 303 | 47.991 | 21.976 | 34.973 | 1.00 | 47.88 | C |
| ATOM | 2607 | CD2 | LEU | B | 303 | 46.927 | 24.213 | 35.140 | 1.00 | 47.52 | C |
| ATOM | 2608 | C | LEU | B | 303 | 50.486 | 24.018 | 37.362 | 1.00 | 47.03 | C |
| ATOM | 2609 | O | LEU | B | 303 | 50.597 | 25.054 | 38.019 | 1.00 | 45.49 | O |
| ATOM | 2610 | N | TYR | B | 304 | 51.223 | 23.764 | 36.281 | 1.00 | 48.44 | N |
| ATOM | 2611 | CA | TYR | B | 304 | 52.209 | 24.728 | 35.787 | 1.00 | 48.93 | C |
| ATOM | 2612 | CB | TYR | B | 304 | 53.567 | 24.065 | 35.536 | 1.00 | 50.50 | C |
| ATOM | 2613 | CG | TYR | B | 304 | 54.409 | 23.839 | 36.770 | 1.00 | 51.63 | C |
| ATOM | 2614 | CD1 | TYR | B | 304 | 54.402 | 24.751 | 37.825 | 1.00 | 53.42 | C |
| ATOM | 2615 | CE1 | TYR | B | 304 | 55.210 | 24.559 | 38.951 | 1.00 | 54.10 | C |
| ATOM | 2616 | CD2 | TYR | B | 304 | 55.249 | 22.729 | 36.866 | 1.00 | 52.37 | C |
| ATOM | 2617 | CE2 | TYR | B | 304 | 56.063 | 22.531 | 37.982 | 1.00 | 52.59 | C |
| ATOM | 2618 | CZ | TYR | B | 304 | 56.038 | 23.445 | 39.020 | 1.00 | 53.19 | C |
| ATOM | 2619 | OH | TYR | B | 304 | 56.824 | 23.234 | 40.133 | 1.00 | 54.22 | O |
| ATOM | 2620 | C | TYR | B | 304 | 51.750 | 25.382 | 34.492 | 1.00 | 48.46 | C |
| ATOM | 2621 | O | TYR | B | 304 | 51.888 | 26.590 | 34.316 | 1.00 | 48.26 | O |

Figure 14

```
ATOM   2622  N    ALA B 305      51.206  24.578  33.587  1.00 48.82           N
ATOM   2623  CA   ALA B 305      50.744  25.092  32.310  1.00 49.12           C
ATOM   2624  CB   ALA B 305      51.922  25.678  31.535  1.00 48.59           C
ATOM   2625  C    ALA B 305      50.096  23.974  31.510  1.00 49.93           C
ATOM   2626  O    ALA B 305      50.096  22.816  31.932  1.00 49.89           O
ATOM   2627  N    VAL B 306      49.551  24.326  30.351  1.00 50.30           N
ATOM   2628  CA   VAL B 306      48.905  23.353  29.479  1.00 50.81           C
ATOM   2629  CB   VAL B 306      47.367  23.433  29.601  1.00 50.98           C
ATOM   2630  CG1  VAL B 306      46.927  23.070  31.019  1.00 50.00           C
ATOM   2631  CG2  VAL B 306      46.899  24.834  29.252  1.00 50.85           C
ATOM   2632  C    VAL B 306      49.283  23.614  28.027  1.00 52.27           C
ATOM   2633  O    VAL B 306      49.687  24.722  27.669  1.00 52.07           O
ATOM   2634  N    VAL B 307      49.160  22.580  27.202  1.00 53.31           N
ATOM   2635  CA   VAL B 307      49.447  22.667  25.772  1.00 54.97           C
ATOM   2636  CB   VAL B 307      50.635  21.753  25.379  1.00 54.06           C
ATOM   2637  CG1  VAL B 307      50.847  21.785  23.868  1.00 53.80           C
ATOM   2638  CG2  VAL B 307      51.897  22.216  26.094  1.00 52.99           C
ATOM   2639  C    VAL B 307      48.163  22.199  25.084  1.00 55.45           C
ATOM   2640  O    VAL B 307      47.925  21.000  24.942  1.00 54.89           O
ATOM   2641  N    THR B 308      47.346  23.162  24.663  1.00 57.00           N
ATOM   2642  CA   THR B 308      46.047  22.889  24.046  1.00 57.63           C
ATOM   2643  CB   THR B 308      45.092  24.067  24.295  1.00 57.27           O
ATOM   2644  OG1  THR B 308      45.747  25.290  23.949  1.00 58.15           C
ATOM   2645  CG2  THR B 308      44.681  24.118  25.754  1.00 56.91           C
ATOM   2646  C    THR B 308      45.943  22.518  22.567  1.00 58.19           C
ATOM   2647  O    THR B 308      44.997  22.923  21.894  1.00 58.83           O
ATOM   2648  N    GLN B 309      46.889  21.738  22.058  1.00 58.47           N
ATOM   2649  CA   GLN B 309      46.830  21.319  20.666  1.00 58.61           C
ATOM   2650  CB   GLN B 309      47.694  22.233  19.797  1.00 59.90           C
ATOM   2651  CG   GLN B 309      47.032  22.617  18.478  1.00 62.27           C
ATOM   2652  CD   GLN B 309      46.667  21.408  17.636  1.00 62.92           C
ATOM   2653  OE1  GLN B 309      47.542  20.689  17.149  1.00 63.18           O
ATOM   2654  NE2  GLN B 309      45.369  21.175  17.465  1.00 62.99           N
ATOM   2655  C    GLN B 309      47.326  19.881  20.582  1.00 58.70           C
ATOM   2656  O    GLN B 309      48.496  19.607  20.850  1.00 58.99           O
ATOM   2657  N    GLU B 310      46.432  18.961  20.229  1.00 58.97           N
ATOM   2658  CA   GLU B 310      46.787  17.546  20.139  1.00 58.33           C
ATOM   2659  CB   GLU B 310      45.723  16.767  19.353  1.00 59.81           C
ATOM   2660  CG   GLU B 310      44.989  17.581  18.307  1.00 62.02           C
ATOM   2661  CD   GLU B 310      43.640  18.068  18.806  1.00 63.23           C
ATOM   2662  OE1  GLU B 310      42.762  17.216  19.056  1.00 62.67           O
ATOM   2663  OE2  GLU B 310      43.457  19.296  18.950  1.00 64.20           O
ATOM   2664  C    GLU B 310      48.151  17.334  19.506  1.00 56.78           C
ATOM   2665  O    GLU B 310      48.441  17.899  18.457  1.00 58.17           O
ATOM   2666  N    PRO B 311      49.016  16.524  20.146  1.00 54.91           N
ATOM   2667  CD   PRO B 311      50.371  16.242  19.642  1.00 54.26           C
ATOM   2668  CA   PRO B 311      48.773  15.816  21.412  1.00 52.52           C
ATOM   2669  CB   PRO B 311      49.967  14.876  21.513  1.00 53.01           C
ATOM   2670  CG   PRO B 311      51.064  15.685  20.867  1.00 54.81           C
ATOM   2671  C    PRO B 311      48.677  16.760  22.607  1.00 50.65           C
ATOM   2672  O    PRO B 311      49.640  17.444  22.946  1.00 49.80           O
ATOM   2673  N    ILE B 312      47.505  16.783  23.234  1.00 49.10           N
ATOM   2674  CA   ILE B 312      47.240  17.636  24.386  1.00 47.00           C
ATOM   2675  CB   ILE B 312      45.773  17.508  24.838  1.00 47.78           C
ATOM   2676  CG2  ILE B 312      45.414  18.659  25.766  1.00 47.29           C
ATOM   2677  CG1  ILE B 312      44.847  17.501  23.620  1.00 48.67           C
ATOM   2678  CD1  ILE B 312      44.833  18.796  22.837  1.00 48.34           C
ATOM   2679  C    ILE B 312      48.136  17.281  25.575  1.00 45.29           C
ATOM   2680  O    ILE B 312      48.389  16.107  25.855  1.00 44.58           O
ATOM   2681  N    TYR B 313      48.608  18.308  26.270  1.00 43.04           N
```

Figure 14

| | | | | | | | | | |
|---|---|---|---|---|---|---|---|---|---|
| ATOM | 2682 | CA | TYR | B | 313 | 49.468 | 18.132 | 27.433 | 1.00 42.57 | C |
| ATOM | 2683 | CB | TYR | B | 313 | 50.882 | 18.675 | 27.176 | 1.00 41.45 | C |
| ATOM | 2684 | CG | TYR | B | 313 | 51.787 | 17.867 | 26.277 | 1.00 42.07 | C |
| ATOM | 2685 | CD1 | TYR | B | 313 | 51.384 | 16.645 | 25.746 | 1.00 40.64 | C |
| ATOM | 2686 | CE1 | TYR | B | 313 | 52.242 | 15.891 | 24.943 | 1.00 43.13 | C |
| ATOM | 2687 | CD2 | TYR | B | 313 | 53.075 | 18.324 | 25.980 | 1.00 42.54 | C |
| ATOM | 2688 | CE2 | TYR | B | 313 | 53.937 | 17.580 | 25.179 | 1.00 43.74 | C |
| ATOM | 2689 | CZ | TYR | B | 313 | 53.517 | 16.367 | 24.666 | 1.00 42.54 | C |
| ATOM | 2690 | OH | TYR | B | 313 | 54.372 | 15.627 | 23.889 | 1.00 44.90 | O |
| ATOM | 2691 | C | TYR | B | 313 | 48.945 | 18.905 | 28.631 | 1.00 41.72 | C |
| ATOM | 2692 | O | TYR | B | 313 | 48.358 | 19.976 | 28.480 | 1.00 41.96 | O |
| ATOM | 2693 | N | ILE | B | 314 | 49.163 | 18.347 | 29.819 | 1.00 40.12 | N |
| ATOM | 2694 | CA | ILE | B | 314 | 48.839 | 19.018 | 31.070 | 1.00 39.17 | C |
| ATOM | 2695 | CB | ILE | B | 314 | 47.696 | 18.354 | 31.865 | 1.00 40.21 | C |
| ATOM | 2696 | CG2 | ILE | B | 314 | 47.607 | 19.004 | 33.233 | 1.00 36.29 | C |
| ATOM | 2697 | CG1 | ILE | B | 314 | 46.363 | 18.514 | 31.127 | 1.00 40.69 | C |
| ATOM | 2698 | CD1 | ILE | B | 314 | 45.181 | 17.919 | 31.877 | 1.00 43.05 | C |
| ATOM | 2699 | C | ILE | B | 314 | 50.145 | 18.832 | 31.844 | 1.00 38.42 | C |
| ATOM | 2700 | O | ILE | B | 314 | 50.615 | 17.707 | 31.998 | 1.00 36.70 | O |
| ATOM | 2701 | N | ILE | B | 315 | 50.730 | 19.924 | 32.319 | 1.00 36.61 | N |
| ATOM | 2702 | CA | ILE | B | 315 | 52.002 | 19.835 | 33.019 | 1.00 39.30 | C |
| ATOM | 2703 | CB | ILE | B | 315 | 53.100 | 20.630 | 32.257 | 1.00 39.53 | C |
| ATOM | 2704 | CG2 | ILE | B | 315 | 54.476 | 20.339 | 32.838 | 1.00 39.54 | C |
| ATOM | 2705 | CG1 | ILE | B | 315 | 53.101 | 20.240 | 30.776 | 1.00 39.86 | C |
| ATOM | 2706 | CD1 | ILE | B | 315 | 52.077 | 20.986 | 29.925 | 1.00 38.53 | C |
| ATOM | 2707 | C | ILE | B | 315 | 51.892 | 20.352 | 34.445 | 1.00 37.83 | C |
| ATOM | 2708 | O | ILE | B | 315 | 51.324 | 21.414 | 34.682 | 1.00 40.08 | O |
| ATOM | 2709 | N | THR | B | 316 | 52.440 | 19.593 | 35.390 | 1.00 36.53 | N |
| ATOM | 2710 | CA | THR | B | 316 | 52.389 | 19.965 | 36.801 | 1.00 36.24 | C |
| ATOM | 2711 | CB | THR | B | 316 | 51.390 | 19.100 | 37.590 | 1.00 35.83 | C |
| ATOM | 2712 | OG1 | THR | B | 316 | 51.946 | 17.788 | 37.775 | 1.00 34.56 | O |
| ATOM | 2713 | CG2 | THR | B | 316 | 50.077 | 18.974 | 36.842 | 1.00 37.20 | C |
| ATOM | 2714 | C | THR | B | 316 | 53.728 | 19.714 | 37.460 | 1.00 35.37 | C |
| ATOM | 2715 | O | THR | B | 316 | 54.645 | 19.174 | 36.851 | 1.00 33.45 | O |
| ATOM | 2716 | N | GLU | B | 317 | 53.813 | 20.086 | 38.732 | 1.00 37.45 | N |
| ATOM | 2717 | CA | GLU | B | 317 | 55.019 | 19.855 | 39.499 | 1.00 38.36 | C |
| ATOM | 2718 | CB | GLU | B | 317 | 54.831 | 20.299 | 40.946 | 1.00 40.50 | C |
| ATOM | 2719 | CG | GLU | B | 317 | 53.728 | 19.549 | 41.668 | 1.00 43.61 | C |
| ATOM | 2720 | CD | GLU | B | 317 | 53.641 | 19.916 | 43.125 | 1.00 44.39 | C |
| ATOM | 2721 | OE1 | GLU | B | 317 | 54.660 | 19.764 | 43.825 | 1.00 48.22 | O |
| ATOM | 2722 | OE2 | GLU | B | 317 | 52.565 | 20.359 | 43.573 | 1.00 46.11 | O |
| ATOM | 2723 | C | GLU | B | 317 | 55.246 | 18.350 | 39.458 | 1.00 38.51 | C |
| ATOM | 2724 | O | GLU | B | 317 | 54.303 | 17.571 | 39.298 | 1.00 39.34 | O |
| ATOM | 2725 | N | TYR | B | 318 | 56.501 | 17.949 | 39.589 | 1.00 37.15 | N |
| ATOM | 2726 | CA | TYR | B | 318 | 56.876 | 16.551 | 39.569 | 1.00 37.06 | C |
| ATOM | 2727 | CB | TYR | B | 318 | 58.262 | 16.421 | 38.927 | 1.00 35.83 | C |
| ATOM | 2728 | CG | TYR | B | 318 | 58.876 | 15.045 | 38.995 | 1.00 37.88 | C |
| ATOM | 2729 | CD1 | TYR | B | 318 | 58.434 | 14.011 | 38.170 | 1.00 37.61 | C |
| ATOM | 2730 | CE1 | TYR | B | 318 | 59.017 | 12.751 | 38.224 | 1.00 38.52 | C |
| ATOM | 2731 | CD2 | TYR | B | 318 | 59.917 | 14.780 | 39.882 | 1.00 38.55 | C |
| ATOM | 2732 | CE2 | TYR | B | 318 | 60.508 | 13.526 | 39.944 | 1.00 39.14 | C |
| ATOM | 2733 | CZ | TYR | B | 318 | 60.057 | 12.520 | 39.118 | 1.00 39.31 | C |
| ATOM | 2734 | OH | TYR | B | 318 | 60.650 | 11.289 | 39.193 | 1.00 40.10 | O |
| ATOM | 2735 | C | TYR | B | 318 | 56.892 | 16.026 | 41.009 | 1.00 36.80 | C |
| ATOM | 2736 | O | TYR | B | 318 | 57.221 | 16.760 | 41.943 | 1.00 37.33 | O |
| ATOM | 2737 | N | MET | B | 319 | 56.521 | 14.763 | 41.189 | 1.00 36.43 | N |
| ATOM | 2738 | CA | MET | B | 319 | 56.512 | 14.163 | 42.527 | 1.00 35.98 | C |
| ATOM | 2739 | CB | MET | B | 319 | 55.082 | 13.801 | 42.942 | 1.00 37.08 | C |
| ATOM | 2740 | CG | MET | B | 319 | 54.140 | 14.981 | 43.067 | 1.00 36.74 | C |
| ATOM | 2741 | SD | MET | B | 319 | 54.564 | 16.154 | 44.380 | 1.00 40.46 | S |

Figure 14

| | | | | | | | | | | |
|---|---|---|---|---|---|---|---|---|---|---|
| ATOM | 2742 | CE | MET | B | 319 | 53.876 | 15.333 | 45.863 | 1.00 40.33 | C |
| ATOM | 2743 | C | MET | B | 319 | 57.386 | 12.918 | 42.482 | 1.00 34.93 | C |
| ATOM | 2744 | O | MET | B | 319 | 56.973 | 11.881 | 41.984 | 1.00 33.30 | O |
| ATOM | 2745 | N | GLU | B | 320 | 58.602 | 13.054 | 43.004 | 1.00 36.81 | N |
| ATOM | 2746 | CA | GLU | B | 320 | 59.607 | 12.000 | 43.023 | 1.00 36.55 | C |
| ATOM | 2747 | CB | GLU | B | 320 | 60.767 | 12.398 | 43.940 | 1.00 39.94 | C |
| ATOM | 2748 | CG | GLU | B | 320 | 61.880 | 11.354 | 44.044 | 1.00 45.85 | C |
| ATOM | 2749 | CD | GLU | B | 320 | 62.462 | 10.976 | 42.691 | 1.00 49.19 | C |
| ATOM | 2750 | OE1 | GLU | B | 320 | 62.849 | 11.892 | 41.937 | 1.00 52.42 | O |
| ATOM | 2751 | OE2 | GLU | B | 320 | 62.542 | 9.766 | 42.383 | 1.00 51.05 | O |
| ATOM | 2752 | C | GLU | B | 320 | 59.156 | 10.605 | 43.399 | 1.00 36.52 | C |
| ATOM | 2753 | O | GLU | B | 320 | 59.650 | 9.634 | 42.835 | 1.00 33.89 | O |
| ATOM | 2754 | N | ASN | B | 321 | 58.230 | 10.487 | 44.345 | 1.00 34.98 | N |
| ATOM | 2755 | CA | ASN | B | 321 | 57.803 | 9.161 | 44.761 | 1.00 36.08 | C |
| ATOM | 2756 | CB | ASN | B | 321 | 57.855 | 9.063 | 46.288 | 1.00 35.73 | C |
| ATOM | 2757 | CG | ASN | B | 321 | 59.288 | 8.959 | 46.807 | 1.00 37.15 | C |
| ATOM | 2758 | OD1 | ASN | B | 321 | 60.030 | 8.059 | 46.410 | 1.00 39.28 | O |
| ATOM | 2759 | ND2 | ASN | B | 321 | 59.682 | 9.875 | 47.681 | 1.00 35.29 | N |
| ATOM | 2760 | C | ASN | B | 321 | 56.460 | 8.696 | 44.215 | 1.00 36.64 | C |
| ATOM | 2761 | O | ASN | B | 321 | 55.928 | 7.670 | 44.640 | 1.00 38.17 | O |
| ATOM | 2762 | N | GLY | B | 322 | 55.935 | 9.445 | 43.252 | 1.00 36.25 | N |
| ATOM | 2763 | CA | GLY | B | 322 | 54.682 | 9.088 | 42.611 | 1.00 35.11 | C |
| ATOM | 2764 | C | GLY | B | 322 | 53.491 | 8.776 | 43.500 | 1.00 34.55 | C |
| ATOM | 2765 | O | GLY | B | 322 | 53.296 | 9.401 | 44.541 | 1.00 34.42 | O |
| ATOM | 2766 | N | SER | B | 323 | 52.704 | 7.795 | 43.067 | 1.00 33.45 | N |
| ATOM | 2767 | CA | SER | B | 323 | 51.489 | 7.376 | 43.756 | 1.00 34.53 | C |
| ATOM | 2768 | CB | SER | B | 323 | 50.714 | 6.405 | 42.860 | 1.00 34.45 | C |
| ATOM | 2769 | OG | SER | B | 323 | 49.565 | 5.918 | 43.520 | 1.00 40.39 | O |
| ATOM | 2770 | C | SER | B | 323 | 51.697 | 6.759 | 45.136 | 1.00 33.87 | C |
| ATOM | 2771 | O | SER | B | 323 | 52.458 | 5.797 | 45.306 | 1.00 33.72 | O |
| ATOM | 2772 | N | LEU | B | 324 | 51.002 | 7.323 | 46.120 | 1.00 32.62 | N |
| ATOM | 2773 | CA | LEU | B | 324 | 51.096 | 6.862 | 47.496 | 1.00 30.77 | C |
| ATOM | 2774 | CB | LEU | B | 324 | 50.074 | 7.592 | 48.377 | 1.00 30.02 | C |
| ATOM | 2775 | CG | LEU | B | 324 | 49.945 | 7.084 | 49.819 | 1.00 29.75 | C |
| ATOM | 2776 | CD1 | LEU | B | 324 | 51.273 | 7.270 | 50.582 | 1.00 29.00 | C |
| ATOM | 2777 | CD2 | LEU | B | 324 | 48.815 | 7.828 | 50.511 | 1.00 27.17 | C |
| ATOM | 2778 | C | LEU | B | 324 | 50.888 | 5.365 | 47.634 | 1.00 31.34 | C |
| ATOM | 2779 | O | LEU | B | 324 | 51.626 | 4.693 | 48.357 | 1.00 30.85 | O |
| ATOM | 2780 | N | VAL | B | 325 | 49.880 | 4.844 | 46.948 | 1.00 32.30 | N |
| ATOM | 2781 | CA | VAL | B | 325 | 49.575 | 3.423 | 47.017 | 1.00 34.46 | C |
| ATOM | 2782 | CB | VAL | B | 325 | 48.317 | 3.085 | 46.167 | 1.00 31.93 | C |
| ATOM | 2783 | CG1 | VAL | B | 325 | 48.661 | 3.070 | 44.699 | 1.00 30.88 | C |
| ATOM | 2784 | CG2 | VAL | B | 325 | 47.720 | 1.758 | 46.607 | 1.00 32.23 | C |
| ATOM | 2785 | C | VAL | B | 325 | 50.769 | 2.575 | 46.565 | 1.00 35.17 | C |
| ATOM | 2786 | O | VAL | B | 325 | 50.973 | 1.467 | 47.065 | 1.00 36.72 | O |
| ATOM | 2787 | N | ASP | B | 326 | 51.558 | 3.100 | 45.629 | 1.00 36.13 | N |
| ATOM | 2788 | CA | ASP | B | 326 | 52.738 | 2.390 | 45.121 | 1.00 36.45 | C |
| ATOM | 2789 | CB | ASP | B | 326 | 53.137 | 2.907 | 43.731 | 1.00 36.70 | C |
| ATOM | 2790 | CG | ASP | B | 326 | 52.133 | 2.545 | 42.653 | 1.00 39.56 | C |
| ATOM | 2791 | OD1 | ASP | B | 326 | 51.780 | 1.357 | 42.550 | 1.00 40.86 | O |
| ATOM | 2792 | OD2 | ASP | B | 326 | 51.701 | 3.446 | 41.901 | 1.00 41.43 | O |
| ATOM | 2793 | C | ASP | B | 326 | 53.919 | 2.578 | 46.072 | 1.00 36.86 | C |
| ATOM | 2794 | O | ASP | B | 326 | 54.626 | 1.626 | 46.406 | 1.00 38.15 | O |
| ATOM | 2795 | N | PHE | B | 327 | 54.127 | 3.816 | 46.503 | 1.00 36.96 | N |
| ATOM | 2796 | CA | PHE | B | 327 | 55.216 | 4.137 | 47.409 | 1.00 36.37 | C |
| ATOM | 2797 | CB | PHE | B | 327 | 55.202 | 5.624 | 47.753 | 1.00 36.47 | C |
| ATOM | 2798 | CG | PHE | B | 327 | 56.307 | 6.033 | 48.688 | 1.00 38.12 | C |
| ATOM | 2799 | CD1 | PHE | B | 327 | 57.629 | 6.069 | 48.248 | 1.00 39.36 | C |
| ATOM | 2800 | CD2 | PHE | B | 327 | 56.035 | 6.341 | 50.014 | 1.00 38.75 | C |
| ATOM | 2801 | CE1 | PHE | B | 327 | 58.666 | 6.407 | 49.122 | 1.00 41.05 | C |

Figure 14

```
ATOM   2802  CE2 PHE B 327      57.063    6.680   50.896  1.00 41.57           C
ATOM   2803  CZ  PHE B 327      58.380    6.711   50.447  1.00 40.91           C
ATOM   2804  C   PHE B 327      55.142    3.326   48.700  1.00 39.00           C
ATOM   2805  O   PHE B 327      56.175    2.948   49.261  1.00 36.58           O
ATOM   2806  N   LEU B 328      53.920    3.066   49.170  1.00 38.73           N
ATOM   2807  CA  LEU B 328      53.725    2.310   50.402  1.00 41.01           C
ATOM   2808  CB  LEU B 328      52.246    2.345   50.822  1.00 41.80           C
ATOM   2809  CG  LEU B 328      51.707    3.710   51.273  1.00 42.03           C
ATOM   2810  CD1 LEU B 328      50.215    3.636   51.491  1.00 43.02           C
ATOM   2811  CD2 LEU B 328      52.414    4.150   52.550  1.00 42.61           C
ATOM   2812  C   LEU B 328      54.203    0.869   50.246  1.00 41.98           C
ATOM   2813  O   LEU B 328      54.513    0.199   51.233  1.00 41.85           O
ATOM   2814  N   LYS B 329      54.266    0.398   49.004  1.00 43.62           N
ATOM   2815  CA  LYS B 329      54.723   -0.960   48.724  1.00 45.34           C
ATOM   2816  CB  LYS B 329      54.003   -1.538   47.502  1.00 46.46           C
ATOM   2817  CG  LYS B 329      52.560   -1.981   47.724  1.00 47.56           C
ATOM   2818  CD  LYS B 329      52.070   -2.751   46.498  1.00 48.77           C
ATOM   2819  CE  LYS B 329      50.578   -3.017   46.530  1.00 48.50           C
ATOM   2820  NZ  LYS B 329      49.787   -1.751   46.428  1.00 52.01           N
ATOM   2821  C   LYS B 329      56.234   -1.045   48.489  1.00 46.02           C
ATOM   2822  O   LYS B 329      56.789   -2.138   48.456  1.00 46.79           O
ATOM   2823  N   THR B 330      56.901    0.093   48.322  1.00 47.00           N
ATOM   2824  CA  THR B 330      58.352    0.087   48.100  1.00 47.23           C
ATOM   2825  CB  THR B 330      58.848    1.419   47.500  1.00 47.20           C
ATOM   2826  OG1 THR B 330      58.686    2.467   48.462  1.00 45.87           O
ATOM   2827  CG2 THR B 330      58.076    1.761   46.233  1.00 46.71           C
ATOM   2828  C   THR B 330      59.119   -0.143   49.405  1.00 48.81           C
ATOM   2829  O   THR B 330      58.588    0.068   50.496  1.00 49.36           O
ATOM   2830  N   PRO B 331      60.390   -0.572   49.307  1.00 49.90           N
ATOM   2831  CD  PRO B 331      61.093   -0.912   48.055  1.00 49.02           C
ATOM   2832  CA  PRO B 331      61.248   -0.833   50.470  1.00 49.15           C
ATOM   2833  CB  PRO B 331      62.619   -1.012   49.838  1.00 49.18           C
ATOM   2834  CG  PRO B 331      62.283   -1.702   48.559  1.00 49.72           C
ATOM   2835  C   PRO B 331      61.225    0.289   51.515  1.00 50.04           C
ATOM   2836  O   PRO B 331      61.122    0.030   52.713  1.00 50.70           O
ATOM   2837  N   SER B 332      61.320    1.537   51.060  1.00 49.74           N
ATOM   2838  CA  SER B 332      61.293    2.674   51.972  1.00 48.42           C
ATOM   2839  CB  SER B 332      61.808    3.935   51.271  1.00 48.24           C
ATOM   2840  OG  SER B 332      63.180    3.805   50.931  1.00 51.00           O
ATOM   2841  C   SER B 332      59.879    2.919   52.502  1.00 47.36           C
ATOM   2842  O   SER B 332      59.702    3.496   53.573  1.00 46.72           O
ATOM   2843  N   GLY B 333      58.875    2.485   51.746  1.00 46.77           N
ATOM   2844  CA  GLY B 333      57.501    2.666   52.180  1.00 45.81           C
ATOM   2845  C   GLY B 333      57.143    1.701   53.296  1.00 45.43           C
ATOM   2846  O   GLY B 333      56.546    2.090   54.303  1.00 45.14           O
ATOM   2847  N   ILE B 334      57.520    0.439   53.111  1.00 44.92           N
ATOM   2848  CA  ILE B 334      57.259   -0.615   54.082  1.00 46.18           C
ATOM   2849  CB  ILE B 334      57.816   -1.976   53.566  1.00 47.07           C
ATOM   2850  CG2 ILE B 334      57.849   -3.005   54.690  1.00 48.94           C
ATOM   2851  CG1 ILE B 334      56.954   -2.488   52.407  1.00 46.95           C
ATOM   2852  CD1 ILE B 334      55.513   -2.777   52.796  1.00 49.58           C
ATOM   2853  C   ILE B 334      57.845   -0.319   55.464  1.00 46.68           C
ATOM   2854  O   ILE B 334      57.251   -0.682   56.484  1.00 46.75           O
ATOM   2855  N   LYS B 335      58.991    0.359   55.493  1.00 46.21           N
ATOM   2856  CA  LYS B 335      59.680    0.696   56.741  1.00 47.11           C
ATOM   2857  CB  LYS B 335      61.163    0.967   56.464  1.00 47.50           C
ATOM   2858  CG  LYS B 335      61.949   -0.218   55.927  1.00 51.09           C
ATOM   2859  CD  LYS B 335      63.372    0.212   55.559  1.00 52.32           C
ATOM   2860  CE  LYS B 335      64.139   -0.912   54.877  1.00 54.86           C
ATOM   2861  NZ  LYS B 335      65.459   -0.454   54.338  1.00 54.21           N
```

Figure 14

| ATOM | 2862 | C   | LYS | B | 335 | 59.124 | 1.876  | 57.546 | 1.00 | 46.39 | C |
|------|------|-----|-----|---|-----|--------|--------|--------|------|-------|---|
| ATOM | 2863 | O   | LYS | B | 335 | 59.380 | 1.978  | 58.744 | 1.00 | 46.15 | O |
| ATOM | 2864 | N   | LEU | B | 336 | 58.388 | 2.777  | 56.898 | 1.00 | 45.43 | N |
| ATOM | 2865 | CA  | LEU | B | 336 | 57.835 | 3.940  | 57.595 | 1.00 | 44.86 | C |
| ATOM | 2866 | CB  | LEU | B | 336 | 56.843 | 4.689  | 56.695 | 1.00 | 45.42 | C |
| ATOM | 2867 | CG  | LEU | B | 336 | 57.409 | 5.393  | 55.459 | 1.00 | 43.34 | C |
| ATOM | 2868 | CD1 | LEU | B | 336 | 56.270 | 6.057  | 54.699 | 1.00 | 44.23 | C |
| ATOM | 2869 | CD2 | LEU | B | 336 | 58.450 | 6.418  | 55.875 | 1.00 | 41.78 | C |
| ATOM | 2870 | C   | LEU | B | 336 | 57.143 | 3.584  | 58.908 | 1.00 | 44.08 | C |
| ATOM | 2871 | O   | LEU | B | 336 | 56.452 | 2.570  | 59.006 | 1.00 | 43.70 | O |
| ATOM | 2872 | N   | THR | B | 337 | 57.331 | 4.429  | 59.913 | 1.00 | 43.90 | N |
| ATOM | 2873 | CA  | THR | B | 337 | 56.724 | 4.210  | 61.218 | 1.00 | 44.23 | C |
| ATOM | 2874 | CB  | THR | B | 337 | 57.473 | 4.983  | 62.312 | 1.00 | 45.23 | C |
| ATOM | 2875 | OG1 | THR | B | 337 | 57.301 | 6.393  | 62.103 | 1.00 | 46.55 | O |
| ATOM | 2876 | CG2 | THR | B | 337 | 58.960 | 4.640  | 62.278 | 1.00 | 45.14 | C |
| ATOM | 2877 | C   | THR | B | 337 | 55.270 | 4.667  | 61.223 | 1.00 | 43.08 | C |
| ATOM | 2878 | O   | THR | B | 337 | 54.844 | 5.437  | 60.362 | 1.00 | 42.76 | O |
| ATOM | 2879 | N   | ILE | B | 338 | 54.512 | 4.190  | 62.201 | 1.00 | 41.66 | N |
| ATOM | 2880 | CA  | ILE | B | 338 | 53.108 | 4.551  | 62.320 | 1.00 | 41.80 | C |
| ATOM | 2881 | CB  | ILE | B | 338 | 52.453 | 3.798  | 63.518 | 1.00 | 42.04 | C |
| ATOM | 2882 | CG2 | ILE | B | 338 | 53.158 | 4.165  | 64.814 | 1.00 | 41.71 | C |
| ATOM | 2883 | CG1 | ILE | B | 338 | 50.954 | 4.105  | 63.585 | 1.00 | 41.43 | C |
| ATOM | 2884 | CD1 | ILE | B | 338 | 50.179 | 3.603  | 62.386 | 1.00 | 41.65 | C |
| ATOM | 2885 | C   | ILE | B | 338 | 52.981 | 6.067  | 62.496 | 1.00 | 41.02 | C |
| ATOM | 2886 | O   | ILE | B | 338 | 51.986 | 6.675  | 62.095 | 1.00 | 40.95 | O |
| ATOM | 2887 | N   | ASN | B | 339 | 54.002 | 6.677  | 63.084 | 1.00 | 40.88 | N |
| ATOM | 2888 | CA  | ASN | B | 339 | 54.011 | 8.121  | 63.302 | 1.00 | 41.40 | C |
| ATOM | 2889 | CB  | ASN | B | 339 | 55.217 | 8.509  | 64.162 | 1.00 | 43.42 | C |
| ATOM | 2890 | CG  | ASN | B | 339 | 55.215 | 7.817  | 65.511 | 1.00 | 45.50 | C |
| ATOM | 2891 | OD1 | ASN | B | 339 | 54.474 | 8.195  | 66.419 | 1.00 | 48.09 | O |
| ATOM | 2892 | ND2 | ASN | B | 339 | 56.036 | 6.788  | 65.643 | 1.00 | 47.27 | N |
| ATOM | 2893 | C   | ASN | B | 339 | 54.069 | 8.871  | 61.972 | 1.00 | 41.07 | C |
| ATOM | 2894 | O   | ASN | B | 339 | 53.360 | 9.860  | 61.771 | 1.00 | 41.72 | O |
| ATOM | 2895 | N   | LYS | B | 340 | 54.922 | 8.405  | 61.067 | 1.00 | 39.90 | N |
| ATOM | 2896 | CA  | LYS | B | 340 | 55.056 | 9.047  | 59.771 | 1.00 | 39.35 | C |
| ATOM | 2897 | CB  | LYS | B | 340 | 56.294 | 8.529  | 59.031 | 1.00 | 41.44 | C |
| ATOM | 2898 | CG  | LYS | B | 340 | 56.489 | 9.183  | 57.661 | 1.00 | 44.44 | C |
| ATOM | 2899 | CD  | LYS | B | 340 | 56.506 | 10.711 | 57.776 | 1.00 | 45.61 | C |
| ATOM | 2900 | CE  | LYS | B | 340 | 56.548 | 11.378 | 56.403 | 1.00 | 46.66 | C |
| ATOM | 2901 | NZ  | LYS | B | 340 | 56.468 | 12.871 | 56.472 | 1.00 | 45.90 | N |
| ATOM | 2902 | C   | LYS | B | 340 | 53.814 | 8.828  | 58.915 | 1.00 | 37.64 | C |
| ATOM | 2903 | O   | LYS | B | 340 | 53.365 | 9.736  | 58.228 | 1.00 | 37.31 | O |
| ATOM | 2904 | N   | LEU | B | 341 | 53.256 | 7.624  | 58.963 | 1.00 | 37.08 | N |
| ATOM | 2905 | CA  | LEU | B | 341 | 52.056 | 7.317  | 58.192 | 1.00 | 37.68 | C |
| ATOM | 2906 | CB  | LEU | B | 341 | 51.681 | 5.843  | 58.359 | 1.00 | 36.94 | C |
| ATOM | 2907 | CG  | LEU | B | 341 | 52.675 | 4.810  | 57.819 | 1.00 | 35.58 | C |
| ATOM | 2908 | CD1 | LEU | B | 341 | 52.183 | 3.404  | 58.161 | 1.00 | 34.09 | C |
| ATOM | 2909 | CD2 | LEU | B | 341 | 52.825 | 4.976  | 56.316 | 1.00 | 34.75 | C |
| ATOM | 2910 | C   | LEU | B | 341 | 50.895 | 8.200  | 58.645 | 1.00 | 38.51 | C |
| ATOM | 2911 | O   | LEU | B | 341 | 50.066 | 8.622  | 57.830 | 1.00 | 37.65 | O |
| ATOM | 2912 | N   | LEU | B | 342 | 50.834 | 8.466  | 59.947 | 1.00 | 38.14 | N |
| ATOM | 2913 | CA  | LEU | B | 342 | 49.785 | 9.308  | 60.510 | 1.00 | 39.61 | C |
| ATOM | 2914 | CB  | LEU | B | 342 | 49.799 | 9.235  | 62.043 | 1.00 | 41.07 | C |
| ATOM | 2915 | CG  | LEU | B | 342 | 48.901 | 8.211  | 62.751 | 1.00 | 44.62 | C |
| ATOM | 2916 | CD1 | LEU | B | 342 | 47.449 | 8.697  | 62.762 | 1.00 | 44.75 | C |
| ATOM | 2917 | CD2 | LEU | B | 342 | 49.014 | 6.859  | 62.057 | 1.00 | 45.30 | C |
| ATOM | 2918 | C   | LEU | B | 342 | 49.957 | 10.755 | 60.052 | 1.00 | 38.92 | C |
| ATOM | 2919 | O   | LEU | B | 342 | 48.975 | 11.450 | 59.807 | 1.00 | 38.29 | O |
| ATOM | 2920 | N   | ASP | B | 343 | 51.200 | 11.216 | 59.935 | 1.00 | 38.88 | N |
| ATOM | 2921 | CA  | ASP | B | 343 | 51.434 | 12.586 | 59.479 | 1.00 | 39.70 | C |

Figure 14

| | | | | | | | | | | |
|---|---|---|---|---|---|---|---|---|---|---|
| ATOM | 2922 | CB  | ASP B 343 | 52.908 | 12.975 | 59.597 | 1.00 | 43.71 | C |
| ATOM | 2923 | CG  | ASP B 343 | 53.195 | 14.344 | 58.979 | 1.00 | 46.40 | C |
| ATOM | 2924 | OD1 | ASP B 343 | 52.651 | 15.351 | 59.487 | 1.00 | 48.64 | O |
| ATOM | 2925 | OD2 | ASP B 343 | 53.948 | 14.413 | 57.979 | 1.00 | 46.30 | O |
| ATOM | 2926 | C   | ASP B 343 | 51.018 | 12.710 | 58.017 | 1.00 | 38.52 | C |
| ATOM | 2927 | O   | ASP B 343 | 50.501 | 13.744 | 57.587 | 1.00 | 36.53 | O |
| ATOM | 2928 | N   | MET B 344 | 51.262 | 11.650 | 57.252 | 1.00 | 36.70 | N |
| ATOM | 2929 | CA  | MET B 344 | 50.895 | 11.644 | 55.845 | 1.00 | 35.82 | C |
| ATOM | 2930 | CB  | MET B 344 | 51.449 | 10.389 | 55.167 | 1.00 | 37.31 | C |
| ATOM | 2931 | CG  | MET B 344 | 52.978 | 10.381 | 55.110 | 1.00 | 41.14 | C |
| ATOM | 2932 | SD  | MET B 344 | 53.640 |  8.912 | 54.335 | 1.00 | 45.15 | S |
| ATOM | 2933 | CE  | MET B 344 | 53.927 |  9.483 | 52.660 | 1.00 | 43.85 | C |
| ATOM | 2934 | C   | MET B 344 | 49.371 | 11.681 | 55.749 | 1.00 | 34.04 | C |
| ATOM | 2935 | O   | MET B 344 | 48.807 | 12.360 | 54.896 | 1.00 | 32.57 | O |
| ATOM | 2936 | N   | ALA B 345 | 48.715 | 10.951 | 56.643 | 1.00 | 31.46 | N |
| ATOM | 2937 | CA  | ALA B 345 | 47.261 | 10.915 | 56.671 | 1.00 | 29.58 | C |
| ATOM | 2938 | CB  | ALA B 345 | 46.784 |  9.869 | 57.676 | 1.00 | 28.05 | C |
| ATOM | 2939 | C   | ALA B 345 | 46.768 | 12.305 | 57.066 | 1.00 | 28.59 | C |
| ATOM | 2940 | O   | ALA B 345 | 45.765 | 12.785 | 56.551 | 1.00 | 27.93 | O |
| ATOM | 2941 | N   | ALA B 346 | 47.485 | 12.952 | 57.977 | 1.00 | 28.56 | N |
| ATOM | 2942 | CA  | ALA B 346 | 47.115 | 14.295 | 58.418 | 1.00 | 29.52 | C |
| ATOM | 2943 | CB  | ALA B 346 | 48.047 | 14.760 | 59.541 | 1.00 | 28.32 | C |
| ATOM | 2944 | C   | ALA B 346 | 47.170 | 15.271 | 57.244 | 1.00 | 30.53 | C |
| ATOM | 2945 | O   | ALA B 346 | 46.239 | 16.043 | 57.036 | 1.00 | 31.00 | O |
| ATOM | 2946 | N   | GLN B 347 | 48.263 | 15.230 | 56.475 | 1.00 | 30.68 | N |
| ATOM | 2947 | CA  | GLN B 347 | 48.425 | 16.115 | 55.311 | 1.00 | 31.64 | C |
| ATOM | 2948 | CB  | GLN B 347 | 49.737 | 15.805 | 54.579 | 1.00 | 32.20 | C |
| ATOM | 2949 | CG  | GLN B 347 | 50.967 | 15.888 | 55.455 | 1.00 | 36.51 | C |
| ATOM | 2950 | CD  | GLN B 347 | 52.226 | 15.559 | 54.693 | 1.00 | 38.71 | C |
| ATOM | 2951 | OE1 | GLN B 347 | 53.209 | 15.096 | 55.267 | 1.00 | 43.79 | O |
| ATOM | 2952 | NE2 | GLN B 347 | 52.210 | 15.806 | 53.395 | 1.00 | 38.28 | N |
| ATOM | 2953 | C   | GLN B 347 | 47.268 | 15.986 | 54.315 | 1.00 | 30.18 | C |
| ATOM | 2954 | O   | GLN B 347 | 46.782 | 16.985 | 53.783 | 1.00 | 30.05 | O |
| ATOM | 2955 | N   | ILE B 348 | 46.848 | 14.752 | 54.064 | 1.00 | 28.11 | N |
| ATOM | 2956 | CA  | ILE B 348 | 45.749 | 14.470 | 53.150 | 1.00 | 29.65 | C |
| ATOM | 2957 | CB  | ILE B 348 | 45.581 | 12.935 | 52.966 | 1.00 | 30.10 | C |
| ATOM | 2958 | CG2 | ILE B 348 | 44.374 | 12.624 | 52.067 | 1.00 | 30.28 | C |
| ATOM | 2959 | CG1 | ILE B 348 | 46.864 | 12.352 | 52.365 | 1.00 | 29.61 | C |
| ATOM | 2960 | CD1 | ILE B 348 | 46.872 | 10.843 | 52.263 | 1.00 | 29.72 | C |
| ATOM | 2961 | C   | ILE B 348 | 44.451 | 15.081 | 53.698 | 1.00 | 32.44 | C |
| ATOM | 2962 | O   | ILE B 348 | 43.727 | 15.782 | 52.979 | 1.00 | 31.96 | O |
| ATOM | 2963 | N   | ALA B 349 | 44.171 | 14.837 | 54.974 | 1.00 | 30.42 | N |
| ATOM | 2964 | CA  | ALA B 349 | 42.961 | 15.383 | 55.579 | 1.00 | 32.25 | C |
| ATOM | 2965 | CB  | ALA B 349 | 42.844 | 14.947 | 57.031 | 1.00 | 30.11 | C |
| ATOM | 2966 | C   | ALA B 349 | 43.007 | 16.904 | 55.490 | 1.00 | 32.34 | C |
| ATOM | 2967 | O   | ALA B 349 | 41.969 | 17.557 | 55.367 | 1.00 | 32.61 | O |
| ATOM | 2968 | N   | GLU B 350 | 44.210 | 17.463 | 55.560 | 1.00 | 31.58 | N |
| ATOM | 2969 | CA  | GLU B 350 | 44.364 | 18.908 | 55.468 | 1.00 | 31.73 | C |
| ATOM | 2970 | CB  | GLU B 350 | 45.828 | 19.309 | 55.644 | 1.00 | 36.13 | C |
| ATOM | 2971 | CG  | GLU B 350 | 46.042 | 20.819 | 55.702 | 1.00 | 40.46 | C |
| ATOM | 2972 | CD  | GLU B 350 | 47.512 | 21.216 | 55.619 | 1.00 | 43.91 | C |
| ATOM | 2973 | OE1 | GLU B 350 | 48.337 | 20.653 | 56.371 | 1.00 | 44.81 | O |
| ATOM | 2974 | OE2 | GLU B 350 | 47.841 | 22.104 | 54.801 | 1.00 | 45.99 | O |
| ATOM | 2975 | C   | GLU B 350 | 43.869 | 19.374 | 54.101 | 1.00 | 29.41 | C |
| ATOM | 2976 | O   | GLU B 350 | 43.059 | 20.297 | 54.004 | 1.00 | 29.71 | O |
| ATOM | 2977 | N   | GLY B 351 | 44.361 | 18.731 | 53.047 | 1.00 | 28.62 | N |
| ATOM | 2978 | CA  | GLY B 351 | 43.945 | 19.094 | 51.702 | 1.00 | 28.49 | C |
| ATOM | 2979 | C   | GLY B 351 | 42.443 | 18.918 | 51.534 | 1.00 | 30.57 | C |
| ATOM | 2980 | O   | GLY B 351 | 41.755 | 19.804 | 51.008 | 1.00 | 30.18 | O |
| ATOM | 2981 | N   | MET B 352 | 41.921 | 17.782 | 51.995 | 1.00 | 27.21 | N |

Figure 14

| | | | | | | | | | |
|---|---|---|---|---|---|---|---|---|---|
| ATOM | 2982 | CA | MET | B | 352 | 40.492 | 17.526 | 51.877 | 1.00 28.60 | C |
| ATOM | 2983 | CB | MET | B | 352 | 40.138 | 16.107 | 52.360 | 1.00 27.23 | C |
| ATOM | 2984 | CG | MET | B | 352 | 40.520 | 15.004 | 51.350 | 1.00 28.64 | C |
| ATOM | 2985 | SD | MET | B | 352 | 39.872 | 15.289 | 49.646 | 1.00 30.87 | S |
| ATOM | 2986 | CE | MET | B | 352 | 38.065 | 15.359 | 49.986 | 1.00 25.36 | C |
| ATOM | 2987 | C | MET | B | 352 | 39.702 | 18.571 | 52.653 | 1.00 27.41 | C |
| ATOM | 2988 | O | MET | B | 352 | 38.624 | 18.991 | 52.214 | 1.00 28.72 | O |
| ATOM | 2989 | N | ALA | B | 353 | 40.245 | 18.991 | 53.794 | 1.00 29.24 | N |
| ATOM | 2990 | CA | ALA | B | 353 | 39.621 | 20.023 | 54.620 | 1.00 32.42 | C |
| ATOM | 2991 | CB | ALA | B | 353 | 40.463 | 20.284 | 55.867 | 1.00 33.06 | C |
| ATOM | 2992 | C | ALA | B | 353 | 39.501 | 21.310 | 53.796 | 1.00 34.20 | C |
| ATOM | 2993 | O | ALA | B | 353 | 38.477 | 21.993 | 53.831 | 1.00 36.31 | O |
| ATOM | 2994 | N | PHE | B | 354 | 40.550 | 21.650 | 53.054 | 1.00 36.11 | N |
| ATOM | 2995 | CA | PHE | B | 354 | 40.505 | 22.856 | 52.222 | 1.00 35.37 | C |
| ATOM | 2996 | CB | PHE | B | 354 | 41.850 | 23.088 | 51.541 | 1.00 38.00 | C |
| ATOM | 2997 | CG | PHE | B | 354 | 41.879 | 24.311 | 50.656 | 1.00 38.56 | C |
| ATOM | 2998 | CD1 | PHE | B | 354 | 41.645 | 25.576 | 51.190 | 1.00 39.87 | C |
| ATOM | 2999 | CD2 | PHE | B | 354 | 42.139 | 24.194 | 49.296 | 1.00 39.86 | C |
| ATOM | 3000 | CE1 | PHE | B | 354 | 41.671 | 26.717 | 50.372 | 1.00 40.92 | C |
| ATOM | 3001 | CE2 | PHE | B | 354 | 42.168 | 25.325 | 48.473 | 1.00 39.66 | C |
| ATOM | 3002 | CZ | PHE | B | 354 | 41.932 | 26.587 | 49.015 | 1.00 40.16 | C |
| ATOM | 3003 | C | PHE | B | 354 | 39.417 | 22.705 | 51.159 | 1.00 34.65 | C |
| ATOM | 3004 | O | PHE | B | 354 | 38.610 | 23.607 | 50.946 | 1.00 35.60 | O |
| ATOM | 3005 | N | ILE | B | 355 | 39.413 | 21.560 | 50.487 | 1.00 33.34 | N |
| ATOM | 3006 | CA | ILE | B | 355 | 38.426 | 21.271 | 49.457 | 1.00 32.71 | C |
| ATOM | 3007 | CB | ILE | B | 355 | 38.642 | 19.850 | 48.900 | 1.00 31.59 | C |
| ATOM | 3008 | CG2 | ILE | B | 355 | 37.423 | 19.395 | 48.113 | 1.00 29.37 | C |
| ATOM | 3009 | CG1 | ILE | B | 355 | 39.934 | 19.829 | 48.071 | 1.00 30.26 | C |
| ATOM | 3010 | CD1 | ILE | B | 355 | 40.349 | 18.459 | 47.579 | 1.00 32.68 | C |
| ATOM | 3011 | C | ILE | B | 355 | 37.036 | 21.404 | 50.073 | 1.00 33.66 | C |
| ATOM | 3012 | O | ILE | B | 355 | 36.124 | 21.957 | 49.464 | 1.00 33.11 | O |
| ATOM | 3013 | N | GLU | B | 356 | 36.895 | 20.904 | 51.294 | 1.00 34.66 | N |
| ATOM | 3014 | CA | GLU | B | 356 | 35.635 | 20.971 | 52.029 | 1.00 36.89 | C |
| ATOM | 3015 | CB | GLU | B | 356 | 35.755 | 20.165 | 53.321 | 1.00 35.98 | C |
| ATOM | 3016 | CG | GLU | B | 356 | 34.627 | 20.380 | 54.326 | 1.00 37.28 | C |
| ATOM | 3017 | CD | GLU | B | 356 | 34.794 | 19.512 | 55.552 | 1.00 36.60 | C |
| ATOM | 3018 | OE1 | GLU | B | 356 | 34.357 | 18.345 | 55.507 | 1.00 37.27 | O |
| ATOM | 3019 | OE2 | GLU | B | 356 | 35.383 | 19.986 | 56.553 | 1.00 37.10 | O |
| ATOM | 3020 | C | GLU | B | 356 | 35.222 | 22.406 | 52.363 | 1.00 38.33 | C |
| ATOM | 3021 | O | GLU | B | 356 | 34.067 | 22.785 | 52.184 | 1.00 38.01 | O |
| ATOM | 3022 | N | GLU | B | 357 | 36.160 | 23.210 | 52.851 | 1.00 41.29 | N |
| ATOM | 3023 | CA | GLU | B | 357 | 35.822 | 24.590 | 53.192 | 1.00 44.14 | C |
| ATOM | 3024 | CB | GLU | B | 357 | 36.977 | 25.248 | 53.978 | 1.00 46.08 | C |
| ATOM | 3025 | CG | GLU | B | 357 | 37.647 | 26.472 | 53.349 | 1.00 49.71 | C |
| ATOM | 3026 | CD | GLU | B | 357 | 36.763 | 27.704 | 53.338 | 1.00 51.78 | C |
| ATOM | 3027 | OE1 | GLU | B | 357 | 36.184 | 28.030 | 54.399 | 1.00 52.36 | O |
| ATOM | 3028 | OE2 | GLU | B | 357 | 36.654 | 28.349 | 52.272 | 1.00 51.61 | O |
| ATOM | 3029 | C | GLU | B | 357 | 35.471 | 25.388 | 51.941 | 1.00 43.90 | C |
| ATOM | 3030 | O | GLU | B | 357 | 34.668 | 26.315 | 51.999 | 1.00 43.46 | O |
| ATOM | 3031 | N | ARG | B | 358 | 36.052 | 25.009 | 50.803 | 1.00 44.88 | N |
| ATOM | 3032 | CA | ARG | B | 358 | 35.786 | 25.710 | 49.557 | 1.00 44.19 | C |
| ATOM | 3033 | CB | ARG | B | 358 | 37.021 | 25.674 | 48.651 | 1.00 46.04 | C |
| ATOM | 3034 | CG | ARG | B | 358 | 38.208 | 26.466 | 49.207 | 1.00 49.81 | C |
| ATOM | 3035 | CD | ARG | B | 358 | 37.850 | 27.939 | 49.422 | 1.00 51.00 | C |
| ATOM | 3036 | NE | ARG | B | 358 | 37.754 | 28.670 | 48.163 | 1.00 54.61 | N |
| ATOM | 3037 | CZ | ARG | B | 358 | 38.803 | 29.147 | 47.495 | 1.00 57.97 | C |
| ATOM | 3038 | NH1 | ARG | B | 358 | 40.034 | 28.976 | 47.970 | 1.00 58.78 | N |
| ATOM | 3039 | NH2 | ARG | B | 358 | 38.626 | 29.787 | 46.344 | 1.00 58.83 | N |
| ATOM | 3040 | C | ARG | B | 358 | 34.568 | 25.154 | 48.819 | 1.00 44.06 | C |
| ATOM | 3041 | O | ARG | B | 358 | 34.306 | 25.520 | 47.678 | 1.00 42.22 | O |

Figure 14

| | | | | | | | | | | |
|---|---|---|---|---|---|---|---|---|---|---|
| ATOM | 3042 | N | ASN | B | 359 | 33.831 | 24.271 | 49.483 | 1.00 42.22 | N |
| ATOM | 3043 | CA | ASN | B | 359 | 32.619 | 23.675 | 48.921 | 1.00 41.30 | C |
| ATOM | 3044 | CB | ASN | B | 359 | 31.585 | 24.770 | 48.642 | 1.00 44.96 | C |
| ATOM | 3045 | CG | ASN | B | 359 | 31.198 | 25.536 | 49.889 | 1.00 47.64 | C |
| ATOM | 3046 | OD1 | ASN | B | 359 | 30.675 | 24.968 | 50.851 | 1.00 49.30 | O |
| ATOM | 3047 | ND2 | ASN | B | 359 | 31.453 | 26.840 | 49.881 | 1.00 49.21 | N |
| ATOM | 3048 | C | ASN | B | 359 | 32.764 | 22.793 | 47.675 | 1.00 39.07 | C |
| ATOM | 3049 | O | ASN | B | 359 | 31.870 | 22.766 | 46.824 | 1.00 37.02 | O |
| ATOM | 3050 | N | TYR | B | 360 | 33.884 | 22.083 | 47.559 | 1.00 36.94 | N |
| ATOM | 3051 | CA | TYR | B | 360 | 34.087 | 21.161 | 46.441 | 1.00 37.13 | C |
| ATOM | 3052 | CB | TYR | B | 360 | 35.449 | 21.375 | 45.757 | 1.00 38.59 | C |
| ATOM | 3053 | CG | TYR | B | 360 | 35.540 | 22.532 | 44.780 | 1.00 41.24 | C |
| ATOM | 3054 | CD1 | TYR | B | 360 | 35.576 | 23.850 | 45.227 | 1.00 40.73 | C |
| ATOM | 3055 | CE1 | TYR | B | 360 | 35.688 | 24.917 | 44.333 | 1.00 44.03 | C |
| ATOM | 3056 | CD2 | TYR | B | 360 | 35.616 | 22.301 | 43.402 | 1.00 43.62 | C |
| ATOM | 3057 | CE2 | TYR | B | 360 | 35.730 | 23.369 | 42.489 | 1.00 46.60 | C |
| ATOM | 3058 | CZ | TYR | B | 360 | 35.764 | 24.673 | 42.970 | 1.00 45.36 | C |
| ATOM | 3059 | OH | TYR | B | 360 | 35.853 | 25.732 | 42.098 | 1.00 48.21 | O |
| ATOM | 3060 | C | TYR | B | 360 | 34.074 | 19.734 | 47.012 | 1.00 36.23 | C |
| ATOM | 3061 | O | TYR | B | 360 | 34.070 | 19.541 | 48.230 | 1.00 34.29 | O |
| ATOM | 3062 | N | ILE | B | 361 | 34.068 | 18.744 | 46.129 | 1.00 35.14 | N |
| ATOM | 3063 | CA | ILE | B | 361 | 34.120 | 17.354 | 46.552 | 1.00 37.85 | C |
| ATOM | 3064 | CB | ILE | B | 361 | 32.759 | 16.617 | 46.372 | 1.00 37.98 | C |
| ATOM | 3065 | CG2 | ILE | B | 361 | 31.692 | 17.276 | 47.246 | 1.00 38.49 | C |
| ATOM | 3066 | CG1 | ILE | B | 361 | 32.336 | 16.618 | 44.907 | 1.00 39.27 | C |
| ATOM | 3067 | CD1 | ILE | B | 361 | 31.060 | 15.841 | 44.655 | 1.00 40.68 | C |
| ATOM | 3068 | C | ILE | B | 361 | 35.187 | 16.712 | 45.683 | 1.00 37.45 | C |
| ATOM | 3069 | O | ILE | B | 361 | 35.514 | 17.236 | 44.615 | 1.00 38.51 | O |
| ATOM | 3070 | N | HIS | B | 362 | 35.750 | 15.598 | 46.137 | 1.00 37.70 | N |
| ATOM | 3071 | CA | HIS | B | 362 | 36.791 | 14.925 | 45.367 | 1.00 35.30 | C |
| ATOM | 3072 | CB | HIS | B | 362 | 37.768 | 14.214 | 46.301 | 1.00 35.57 | C |
| ATOM | 3073 | CG | HIS | B | 362 | 39.029 | 13.767 | 45.630 | 1.00 33.36 | C |
| ATOM | 3074 | CD2 | HIS | B | 362 | 40.325 | 14.069 | 45.874 | 1.00 33.33 | C |
| ATOM | 3075 | ND1 | HIS | B | 362 | 39.033 | 12.923 | 44.540 | 1.00 33.01 | N |
| ATOM | 3076 | CE1 | HIS | B | 362 | 40.276 | 12.729 | 44.137 | 1.00 36.18 | C |
| ATOM | 3077 | NE2 | HIS | B | 362 | 41.080 | 13.415 | 44.930 | 1.00 34.94 | N |
| ATOM | 3078 | C | HIS | B | 362 | 36.182 | 13.926 | 44.396 | 1.00 36.00 | C |
| ATOM | 3079 | O | HIS | B | 362 | 36.406 | 14.018 | 43.187 | 1.00 36.36 | O |
| ATOM | 3080 | N | ARG | B | 363 | 35.434 | 12.966 | 44.940 | 1.00 35.60 | N |
| ATOM | 3081 | CA | ARG | B | 363 | 34.753 | 11.936 | 44.162 | 1.00 34.32 | C |
| ATOM | 3082 | CB | ARG | B | 363 | 34.204 | 12.533 | 42.852 | 1.00 36.66 | C |
| ATOM | 3083 | CG | ARG | B | 363 | 33.096 | 11.710 | 42.217 | 1.00 42.03 | C |
| ATOM | 3084 | CD | ARG | B | 363 | 32.675 | 12.239 | 40.836 | 1.00 46.75 | C |
| ATOM | 3085 | NE | ARG | B | 363 | 31.488 | 13.095 | 40.881 | 1.00 50.80 | N |
| ATOM | 3086 | CZ | ARG | B | 363 | 31.463 | 14.331 | 41.375 | 1.00 52.74 | C |
| ATOM | 3087 | NH1 | ARG | B | 363 | 32.566 | 14.877 | 41.874 | 1.00 55.43 | N |
| ATOM | 3088 | NH2 | ARG | B | 363 | 30.329 | 15.022 | 41.372 | 1.00 53.78 | N |
| ATOM | 3089 | C | ARG | B | 363 | 35.628 | 10.718 | 43.844 | 1.00 33.47 | C |
| ATOM | 3090 | O | ARG | B | 363 | 35.111 | 9.628 | 43.614 | 1.00 30.85 | O |
| ATOM | 3091 | N | ASP | B | 364 | 36.948 | 10.892 | 43.838 | 1.00 32.00 | N |
| ATOM | 3092 | CA | ASP | B | 364 | 37.846 | 9.773 | 43.519 | 1.00 33.47 | C |
| ATOM | 3093 | CB | ASP | B | 364 | 38.433 | 9.964 | 42.108 | 1.00 34.88 | C |
| ATOM | 3094 | CG | ASP | B | 364 | 37.441 | 9.640 | 40.995 | 1.00 36.42 | C |
| ATOM | 3095 | OD1 | ASP | B | 364 | 37.132 | 8.439 | 40.794 | 1.00 40.06 | O |
| ATOM | 3096 | OD2 | ASP | B | 364 | 36.977 | 10.581 | 40.311 | 1.00 35.79 | O |
| ATOM | 3097 | C | ASP | B | 364 | 38.986 | 9.655 | 44.529 | 1.00 31.71 | C |
| ATOM | 3098 | O | ASP | B | 364 | 40.120 | 9.280 | 44.186 | 1.00 29.47 | O |
| ATOM | 3099 | N | LEU | B | 365 | 38.684 | 9.974 | 45.781 | 1.00 28.98 | N |
| ATOM | 3100 | CA | LEU | B | 365 | 39.681 | 9.936 | 46.831 | 1.00 28.75 | C |
| ATOM | 3101 | CB | LEU | B | 365 | 39.143 | 10.654 | 48.090 | 1.00 26.83 | C |

Figure 14

```
ATOM   3102  CG   LEU B 365      40.086  10.814  49.295  1.00 25.64           C
ATOM   3103  CD1  LEU B 365      41.296  11.654  48.879  1.00 27.55           C
ATOM   3104  CD2  LEU B 365      39.374  11.492  50.468  1.00 22.65           C
ATOM   3105  C    LEU B 365      40.114   8.512  47.184  1.00 29.79           C
ATOM   3106  O    LEU B 365      39.291   7.689  47.582  1.00 28.17           O
ATOM   3107  N    ARG B 366      41.406   8.230  47.011  1.00 27.04           N
ATOM   3108  CA   ARG B 366      41.993   6.931  47.352  1.00 27.49           C
ATOM   3109  CB   ARG B 366      41.491   5.815  46.421  1.00 30.31           C
ATOM   3110  CG   ARG B 366      41.660   6.049  44.913  1.00 31.22           C
ATOM   3111  CD   ARG B 366      41.040   4.876  44.150  1.00 32.32           C
ATOM   3112  NE   ARG B 366      41.153   5.030  42.703  1.00 31.78           N
ATOM   3113  CZ   ARG B 366      40.239   5.617  41.939  1.00 32.14           C
ATOM   3114  NH1  ARG B 366      39.124   6.103  42.477  1.00 29.42           N
ATOM   3115  NH2  ARG B 366      40.454   5.741  40.641  1.00 27.61           N
ATOM   3116  C    ARG B 366      43.512   7.067  47.306  1.00 29.29           C
ATOM   3117  O    ARG B 366      44.032   8.051  46.768  1.00 27.81           O
ATOM   3118  N    ALA B 367      44.240   6.117  47.884  1.00 26.56           N
ATOM   3119  CA   ALA B 367      45.689   6.258  47.889  1.00 27.68           C
ATOM   3120  CB   ALA B 367      46.335   5.095  48.636  1.00 29.11           C
ATOM   3121  C    ALA B 367      46.249   6.369  46.467  1.00 27.57           C
ATOM   3122  O    ALA B 367      47.230   7.076  46.232  1.00 29.00           O
ATOM   3123  N    ALA B 368      45.609   5.697  45.515  1.00 26.69           N
ATOM   3124  CA   ALA B 368      46.065   5.737  44.127  1.00 29.61           C
ATOM   3125  CB   ALA B 368      45.162   4.877  43.247  1.00 29.25           C
ATOM   3126  C    ALA B 368      46.105   7.162  43.582  1.00 29.54           C
ATOM   3127  O    ALA B 368      46.860   7.453  42.649  1.00 30.17           O
ATOM   3128  N    ASN B 369      45.301   8.048  44.164  1.00 27.95           N
ATOM   3129  CA   ASN B 369      45.258   9.429  43.705  1.00 29.71           C
ATOM   3130  CB   ASN B 369      43.820   9.818  43.334  1.00 30.76           C
ATOM   3131  CG   ASN B 369      43.302   9.041  42.133  1.00 33.30           C
ATOM   3132  OD1  ASN B 369      44.012   8.888  41.140  1.00 36.38           O
ATOM   3133  ND2  ASN B 369      42.061   8.565  42.208  1.00 29.99           N
ATOM   3134  C    ASN B 369      45.863  10.450  44.671  1.00 29.36           C
ATOM   3135  O    ASN B 369      45.427  11.602  44.730  1.00 30.87           O
ATOM   3136  N    ILE B 370      46.864  10.005  45.426  1.00 28.12           N
ATOM   3137  CA   ILE B 370      47.614  10.853  46.351  1.00 28.30           C
ATOM   3138  CB   ILE B 370      47.566  10.315  47.809  1.00 28.00           C
ATOM   3139  CG2  ILE B 370      48.525  11.127  48.702  1.00 27.35           C
ATOM   3140  CG1  ILE B 370      46.136  10.400  48.368  1.00 25.42           C
ATOM   3141  CD1  ILE B 370      45.593  11.803  48.433  1.00 23.66           C
ATOM   3142  C    ILE B 370      49.063  10.740  45.819  1.00 30.31           C
ATOM   3143  O    ILE B 370      49.539   9.637  45.557  1.00 30.15           O
ATOM   3144  N    LEU B 371      49.740  11.863  45.605  1.00 32.16           N
ATOM   3145  CA   LEU B 371      51.117  11.814  45.112  1.00 33.48           C
ATOM   3146  CB   LEU B 371      51.314  12.782  43.944  1.00 34.73           C
ATOM   3147  CG   LEU B 371      50.581  12.416  42.649  1.00 34.75           C
ATOM   3148  CD1  LEU B 371      50.692  13.566  41.660  1.00 33.64           C
ATOM   3149  CD2  LEU B 371      51.180  11.148  42.060  1.00 37.23           C
ATOM   3150  C    LEU B 371      52.077  12.154  46.243  1.00 33.88           C
ATOM   3151  O    LEU B 371      51.757  12.968  47.101  1.00 33.78           O
ATOM   3152  N    VAL B 372      53.262  11.544  46.220  1.00 35.40           N
ATOM   3153  CA   VAL B 372      54.258  11.752  47.265  1.00 34.47           C
ATOM   3154  CB   VAL B 372      54.542  10.421  47.986  1.00 35.81           C
ATOM   3155  CG1  VAL B 372      55.466  10.655  49.173  1.00 34.67           C
ATOM   3156  CG2  VAL B 372      53.225   9.778  48.426  1.00 36.69           C
ATOM   3157  C    VAL B 372      55.587  12.315  46.745  1.00 36.02           C
ATOM   3158  O    VAL B 372      56.165  11.789  45.791  1.00 35.15           O
ATOM   3159  N    SER B 373      56.078  13.373  47.385  1.00 36.80           N
ATOM   3160  CA   SER B 373      57.338  13.982  46.966  1.00 40.30           C
ATOM   3161  CB   SER B 373      57.366  15.464  47.353  1.00 41.10           C
```

Figure 14

```
ATOM   3162  OG  SER B 373      57.276  15.640  48.755  1.00 42.08           O
ATOM   3163  C   SER B 373      58.556  13.273  47.557  1.00 41.20           C
ATOM   3164  O   SER B 373      58.429  12.378  48.390  1.00 40.19           O
ATOM   3165  N   ASP B 374      59.743  13.668  47.106  1.00 44.41           N
ATOM   3166  CA  ASP B 374      60.977  13.070  47.597  1.00 45.69           C
ATOM   3167  CB  ASP B 374      62.188  13.660  46.861  1.00 47.95           C
ATOM   3168  CG  ASP B 374      62.144  15.175  46.784  1.00 51.20           C
ATOM   3169  OD1 ASP B 374      61.813  15.812  47.810  1.00 51.23           O
ATOM   3170  OD2 ASP B 374      62.444  15.729  45.701  1.00 52.92           O
ATOM   3171  C   ASP B 374      61.105  13.310  49.097  1.00 45.81           C
ATOM   3172  O   ASP B 374      61.736  12.523  49.804  1.00 46.89           O
ATOM   3173  N   THR B 375      60.497  14.393  49.578  1.00 45.53           N
ATOM   3174  CA  THR B 375      60.528  14.731  51.000  1.00 46.58           C
ATOM   3175  CB  THR B 375      60.334  16.236  51.226  1.00 46.67           C
ATOM   3176  OG1 THR B 375      59.115  16.651  50.598  1.00 48.97           O
ATOM   3177  CG2 THR B 375      61.502  17.022  50.653  1.00 46.94           C
ATOM   3178  C   THR B 375      59.432  13.998  51.771  1.00 46.80           C
ATOM   3179  O   THR B 375      59.347  14.105  52.992  1.00 46.47           O
ATOM   3180  N   LEU B 376      58.584  13.278  51.043  1.00 47.46           N
ATOM   3181  CA  LEU B 376      57.493  12.503  51.629  1.00 47.03           C
ATOM   3182  CB  LEU B 376      57.978  11.748  52.873  1.00 47.85           C
ATOM   3183  CG  LEU B 376      58.912  10.583  52.550  1.00 49.34           C
ATOM   3184  CD1 LEU B 376      59.217   9.772  53.809  1.00 48.75           C
ATOM   3185  CD2 LEU B 376      58.245   9.709  51.506  1.00 49.17           C
ATOM   3186  C   LEU B 376      56.217  13.258  51.963  1.00 46.03           C
ATOM   3187  O   LEU B 376      55.347  12.725  52.647  1.00 46.17           O
ATOM   3188  N   SER B 377      56.101  14.499  51.502  1.00 44.95           N
ATOM   3189  CA  SER B 377      54.879  15.248  51.748  1.00 43.48           C
ATOM   3190  CB  SER B 377      55.113  16.757  51.600  1.00 45.13           C
ATOM   3191  OG  SER B 377      55.719  17.077  50.363  1.00 49.87           O
ATOM   3192  C   SER B 377      53.866  14.738  50.719  1.00 41.42           C
ATOM   3193  O   SER B 377      54.232  14.384  49.595  1.00 40.39           O
ATOM   3194  N   CYS B 378      52.600  14.672  51.116  1.00 38.94           N
ATOM   3195  CA  CYS B 378      51.540  14.175  50.242  1.00 38.33           C
ATOM   3196  CB  CYS B 378      50.611  13.246  51.027  1.00 38.29           C
ATOM   3197  SG  CYS B 378      51.408  11.724  51.559  1.00 39.40           S
ATOM   3198  C   CYS B 378      50.710  15.274  49.603  1.00 37.09           C
ATOM   3199  O   CYS B 378      50.510  16.332  50.188  1.00 37.97           O
ATOM   3200  N   LYS B 379      50.221  15.009  48.398  1.00 35.85           N
ATOM   3201  CA  LYS B 379      49.399  15.971  47.689  1.00 36.78           C
ATOM   3202  CB  LYS B 379      50.251  16.786  46.711  1.00 36.90           C
ATOM   3203  CG  LYS B 379      51.225  17.699  47.431  1.00 39.24           C
ATOM   3204  CD  LYS B 379      52.041  18.570  46.489  1.00 42.87           C
ATOM   3205  CE  LYS B 379      53.081  19.367  47.272  1.00 41.97           C
ATOM   3206  NZ  LYS B 379      53.980  20.127  46.372  1.00 44.78           N
ATOM   3207  C   LYS B 379      48.264  15.266  46.971  1.00 34.87           C
ATOM   3208  O   LYS B 379      48.449  14.215  46.363  1.00 36.05           O
ATOM   3209  N   ILE B 380      47.082  15.858  47.074  1.00 35.22           N
ATOM   3210  CA  ILE B 380      45.873  15.314  46.477  1.00 33.88           C
ATOM   3211  CB  ILE B 380      44.631  15.900  47.191  1.00 34.22           C
ATOM   3212  CG2 ILE B 380      43.364  15.274  46.638  1.00 32.06           C
ATOM   3213  CG1 ILE B 380      44.750  15.638  48.703  1.00 34.36           C
ATOM   3214  CD1 ILE B 380      43.649  16.250  49.542  1.00 34.41           C
ATOM   3215  C   ILE B 380      45.792  15.589  44.974  1.00 34.94           C
ATOM   3216  O   ILE B 380      45.947  16.731  44.524  1.00 32.29           O
ATOM   3217  N   ALA B 381      45.552  14.529  44.210  1.00 34.58           N
ATOM   3218  CA  ALA B 381      45.437  14.630  42.762  1.00 38.28           C
ATOM   3219  CB  ALA B 381      46.448  13.695  42.096  1.00 39.06           C
ATOM   3220  C   ALA B 381      44.025  14.288  42.276  1.00 38.56           C
ATOM   3221  O   ALA B 381      43.211  13.727  43.014  1.00 38.03           O
```

Figure 14

```
ATOM   3222  N   ASP B 382      43.763  14.633  41.022  1.00 40.16           N
ATOM   3223  CA  ASP B 382      42.488  14.375  40.359  1.00 40.96           C
ATOM   3224  CB  ASP B 382      42.501  12.989  39.701  1.00 42.63           C
ATOM   3225  CG  ASP B 382      43.319  12.961  38.424  1.00 46.63           C
ATOM   3226  OD1 ASP B 382      43.272  13.964  37.675  1.00 48.07           O
ATOM   3227  OD2 ASP B 382      43.998  11.944  38.159  1.00 47.87           O
ATOM   3228  C   ASP B 382      41.238  14.515  41.205  1.00 40.13           C
ATOM   3229  O   ASP B 382      40.493  13.559  41.391  1.00 40.18           O
ATOM   3230  N   PHE B 383      40.999  15.721  41.698  1.00 40.10           N
ATOM   3231  CA  PHE B 383      39.819  15.994  42.499  1.00 41.54           C
ATOM   3232  CB  PHE B 383      40.209  16.721  43.781  1.00 43.01           C
ATOM   3233  CG  PHE B 383      40.818  18.071  43.542  1.00 46.60           C
ATOM   3234  CD1 PHE B 383      42.156  18.193  43.172  1.00 48.80           C
ATOM   3235  CD2 PHE B 383      40.042  19.221  43.638  1.00 48.00           C
ATOM   3236  CE1 PHE B 383      42.712  19.444  42.897  1.00 50.44           C
ATOM   3237  CE2 PHE B 383      40.584  20.472  43.367  1.00 49.65           C
ATOM   3238  CZ  PHE B 383      41.922  20.586  42.995  1.00 49.89           C
ATOM   3239  C   PHE B 383      38.865  16.891  41.707  1.00 41.59           C
ATOM   3240  O   PHE B 383      39.217  17.409  40.648  1.00 41.46           O
ATOM   3241  N   GLY B 384      37.662  17.073  42.239  1.00 41.45           N
ATOM   3242  CA  GLY B 384      36.678  17.935  41.614  1.00 42.24           C
ATOM   3243  C   GLY B 384      36.171  17.515  40.256  1.00 43.82           C
ATOM   3244  O   GLY B 384      35.433  18.266  39.621  1.00 44.21           O
ATOM   3245  N   LEU B 385      36.557  16.331  39.799  1.00 45.63           N
ATOM   3246  CA  LEU B 385      36.105  15.858  38.497  1.00 47.71           C
ATOM   3247  CB  LEU B 385      36.932  14.645  38.048  1.00 47.15           C
ATOM   3248  CG  LEU B 385      38.384  14.915  37.626  1.00 47.92           C
ATOM   3249  CD1 LEU B 385      39.087  13.595  37.358  1.00 46.31           C
ATOM   3250  CD2 LEU B 385      38.416  15.807  36.383  1.00 45.60           C
ATOM   3251  C   LEU B 385      34.628  15.492  38.555  1.00 49.14           C
ATOM   3252  O   LEU B 385      34.076  15.272  39.633  1.00 49.98           O
ATOM   3253  N   ALA B 386      33.987  15.440  37.394  1.00 50.78           N
ATOM   3254  CA  ALA B 386      32.572  15.092  37.333  1.00 51.98           C
ATOM   3255  CB  ALA B 386      31.851  15.993  36.337  1.00 52.55           C
ATOM   3256  C   ALA B 386      32.413  13.631  36.930  1.00 52.27           C
ATOM   3257  O   ALA B 386      31.302  13.154  36.699  1.00 53.16           O
ATOM   3258  N   ARG B 387      33.532  12.921  36.835  1.00 52.46           N
ATOM   3259  CA  ARG B 387      33.496  11.511  36.470  1.00 50.65           C
ATOM   3260  CB  ARG B 387      33.974  11.315  35.024  1.00 50.28           C
ATOM   3261  CG  ARG B 387      35.469  11.522  34.781  1.00 50.60           C
ATOM   3262  CD  ARG B 387      35.802  11.368  33.293  1.00 50.09           C
ATOM   3263  NE  ARG B 387      37.237  11.419  33.013  1.00 49.26           N
ATOM   3264  CZ  ARG B 387      38.066  10.384  33.127  1.00 49.83           C
ATOM   3265  NH1 ARG B 387      37.617   9.198  33.516  1.00 48.10           N
ATOM   3266  NH2 ARG B 387      39.354  10.532  32.841  1.00 51.22           N
ATOM   3267  C   ARG B 387      34.367  10.699  37.408  1.00 49.69           C
ATOM   3268  O   ARG B 387      35.298  11.228  38.010  1.00 49.66           O
ATOM   3269  N   LEU B 388      34.042   9.419  37.555  1.00 48.28           N
ATOM   3270  CA  LEU B 388      34.840   8.531  38.385  1.00 45.97           C
ATOM   3271  CB  LEU B 388      34.006   7.346  38.864  1.00 46.69           C
ATOM   3272  CG  LEU B 388      32.729   7.655  39.656  1.00 49.70           C
ATOM   3273  CD1 LEU B 388      32.122   6.348  40.142  1.00 48.41           C
ATOM   3274  CD2 LEU B 388      33.034   8.579  40.837  1.00 47.70           C
ATOM   3275  C   LEU B 388      35.955   8.041  37.461  1.00 44.54           C
ATOM   3276  O   LEU B 388      35.685   7.615  36.344  1.00 42.57           O
ATOM   3277  N   ILE B 389      37.202   8.116  37.910  1.00 42.68           N
ATOM   3278  CA  ILE B 389      38.312   7.670  37.082  1.00 40.96           C
ATOM   3279  CB  ILE B 389      39.489   8.667  37.131  1.00 41.45           C
ATOM   3280  CG2 ILE B 389      39.027  10.048  36.667  1.00 42.04           C
ATOM   3281  CG1 ILE B 389      40.056   8.742  38.549  1.00 40.88           C
```

Figure 14

| ATOM | 3282 | CD1 | ILE B 389 | 41.219 | 9.713 | 38.699 | 1.00 | 37.47 | C |
| ATOM | 3283 | C | ILE B 389 | 38.831 | 6.304 | 37.508 | 1.00 | 40.88 | C |
| ATOM | 3284 | O | ILE B 389 | 38.606 | 5.864 | 38.633 | 1.00 | 38.52 | O |
| ATOM | 3285 | N | GLU B 390 | 39.503 | 5.626 | 36.588 | 1.00 | 40.37 | N |
| ATOM | 3286 | CA | GLU B 390 | 40.088 | 4.328 | 36.873 | 1.00 | 42.08 | C |
| ATOM | 3287 | CB | GLU B 390 | 39.732 | 3.313 | 35.786 | 1.00 | 43.40 | C |
| ATOM | 3288 | CG | GLU B 390 | 38.282 | 2.876 | 35.802 | 1.00 | 46.53 | C |
| ATOM | 3289 | CD | GLU B 390 | 37.992 | 1.785 | 34.789 | 1.00 | 48.33 | C |
| ATOM | 3290 | OE1 | GLU B 390 | 38.196 | 2.022 | 33.584 | 1.00 | 48.16 | O |
| ATOM | 3291 | OE2 | GLU B 390 | 37.563 | 0.687 | 35.199 | 1.00 | 49.44 | O |
| ATOM | 3292 | C | GLU B 390 | 41.593 | 4.541 | 36.917 | 1.00 | 42.48 | C |
| ATOM | 3293 | O | GLU B 390 | 42.126 | 5.413 | 36.221 | 1.00 | 41.92 | O |
| ATOM | 3294 | N | ASP B 391 | 42.278 | 3.746 | 37.729 | 1.00 | 42.60 | N |
| ATOM | 3295 | CA | ASP B 391 | 43.729 | 3.875 | 37.874 | 1.00 | 44.21 | C |
| ATOM | 3296 | CB | ASP B 391 | 44.184 | 3.071 | 39.091 | 1.00 | 44.94 | C |
| ATOM | 3297 | CG | ASP B 391 | 43.494 | 3.521 | 40.360 | 1.00 | 47.04 | C |
| ATOM | 3298 | OD2 | ASP B 391 | 43.604 | 2.832 | 41.393 | 1.00 | 48.79 | O |
| ATOM | 3299 | OD1 | ASP B 391 | 42.834 | 4.582 | 40.322 | 1.00 | 48.24 | O |
| ATOM | 3300 | C | ASP B 391 | 44.549 | 3.473 | 36.642 | 1.00 | 44.04 | C |
| ATOM | 3301 | O | ASP B 391 | 45.723 | 3.835 | 36.533 | 1.00 | 44.77 | O |
| ATOM | 3302 | N | ASN B 392 | 43.945 | 2.742 | 35.711 | 1.00 | 42.44 | N |
| ATOM | 3303 | CA | ASN B 392 | 44.682 | 2.322 | 34.522 | 1.00 | 43.84 | C |
| ATOM | 3304 | CB | ASN B 392 | 44.350 | 0.860 | 34.181 | 1.00 | 45.22 | C |
| ATOM | 3305 | CG | ASN B 392 | 42.947 | 0.690 | 33.653 | 1.00 | 47.37 | C |
| ATOM | 3306 | OD1 | ASN B 392 | 42.074 | 1.511 | 33.913 | 1.00 | 48.22 | O |
| ATOM | 3307 | ND2 | ASN B 392 | 42.719 | -0.388 | 32.914 | 1.00 | 48.88 | N |
| ATOM | 3308 | C | ASN B 392 | 44.440 | 3.224 | 33.307 | 1.00 | 41.99 | C |
| ATOM | 3309 | O | ASN B 392 | 44.593 | 2.796 | 32.168 | 1.00 | 41.72 | O |
| ATOM | 3310 | N | GLU B 393 | 44.074 | 4.478 | 33.549 | 1.00 | 39.98 | N |
| ATOM | 3311 | CA | GLU B 393 | 43.836 | 5.395 | 32.449 | 1.00 | 40.18 | C |
| ATOM | 3312 | CB | GLU B 393 | 42.925 | 6.537 | 32.893 | 1.00 | 38.92 | C |
| ATOM | 3313 | CG | GLU B 393 | 41.495 | 6.093 | 33.198 | 1.00 | 40.42 | C |
| ATOM | 3314 | CD | GLU B 393 | 40.568 | 7.260 | 33.479 | 1.00 | 41.70 | C |
| ATOM | 3315 | OE1 | GLU B 393 | 41.068 | 8.400 | 33.600 | 1.00 | 41.12 | O |
| ATOM | 3316 | OE2 | GLU B 393 | 39.339 | 7.037 | 33.584 | 1.00 | 43.46 | O |
| ATOM | 3317 | C | GLU B 393 | 45.143 | 5.960 | 31.881 | 1.00 | 40.27 | C |
| ATOM | 3318 | O | GLU B 393 | 45.270 | 6.127 | 30.670 | 1.00 | 38.47 | O |
| ATOM | 3319 | N | TYR B 394 | 46.107 | 6.239 | 32.752 | 1.00 | 40.78 | N |
| ATOM | 3320 | CA | TYR B 394 | 47.395 | 6.791 | 32.322 | 1.00 | 42.40 | C |
| ATOM | 3321 | CB | TYR B 394 | 47.517 | 8.232 | 32.813 | 1.00 | 41.96 | C |
| ATOM | 3322 | CG | TYR B 394 | 46.437 | 9.123 | 32.252 | 1.00 | 42.54 | C |
| ATOM | 3323 | CD1 | TYR B 394 | 46.503 | 9.580 | 30.932 | 1.00 | 42.25 | C |
| ATOM | 3324 | CE1 | TYR B 394 | 45.478 | 10.340 | 30.381 | 1.00 | 41.26 | C |
| ATOM | 3325 | CD2 | TYR B 394 | 45.315 | 9.454 | 33.012 | 1.00 | 41.82 | C |
| ATOM | 3326 | CE2 | TYR B 394 | 44.277 | 10.214 | 32.470 | 1.00 | 42.41 | C |
| ATOM | 3327 | CZ | TYR B 394 | 44.366 | 10.651 | 31.150 | 1.00 | 43.71 | C |
| ATOM | 3328 | OH | TYR B 394 | 43.334 | 11.374 | 30.590 | 1.00 | 44.31 | O |
| ATOM | 3329 | C | TYR B 394 | 48.590 | 5.963 | 32.806 | 1.00 | 44.79 | C |
| ATOM | 3330 | O | TYR B 394 | 49.744 | 6.398 | 32.706 | 1.00 | 44.23 | O |
| ATOM | 3331 | N | THR B 395 | 48.303 | 4.769 | 33.316 | 1.00 | 45.51 | N |
| ATOM | 3332 | CA | THR B 395 | 49.333 | 3.860 | 33.808 | 1.00 | 48.79 | C |
| ATOM | 3333 | CB | THR B 395 | 49.572 | 4.005 | 35.330 | 1.00 | 50.01 | C |
| ATOM | 3334 | OG1 | THR B 395 | 49.413 | 5.375 | 35.727 | 1.00 | 51.53 | O |
| ATOM | 3335 | CG2 | THR B 395 | 50.983 | 3.533 | 35.683 | 1.00 | 50.89 | C |
| ATOM | 3336 | C | THR B 395 | 48.860 | 2.433 | 33.585 | 1.00 | 49.55 | C |
| ATOM | 3337 | O | THR B 395 | 47.658 | 2.178 | 33.519 | 1.00 | 49.37 | O |
| ATOM | 3338 | N | ALA B 396 | 49.800 | 1.503 | 33.487 | 1.00 | 50.82 | N |
| ATOM | 3339 | CA | ALA B 396 | 49.451 | 0.104 | 33.303 | 1.00 | 53.34 | C |
| ATOM | 3340 | CB | ALA B 396 | 50.601 | -0.643 | 32.641 | 1.00 | 54.48 | C |
| ATOM | 3341 | C | ALA B 396 | 49.157 | -0.492 | 34.677 | 1.00 | 55.23 | C |

Figure 14

| ATOM | 3342 | O | ALA | B | 396 | 50.000 | -0.460 | 35.570 | 1.00 | 56.11 | O |
|------|------|-----|------|---|-----|--------|--------|--------|------|-------|---|
| ATOM | 3343 | N | ARG | B | 397 | 47.950 | -1.019 | 34.850 | 1.00 | 56.98 | N |
| ATOM | 3344 | CA | ARG | B | 397 | 47.568 | -1.620 | 36.118 | 1.00 | 57.94 | C |
| ATOM | 3345 | CB | ARG | B | 397 | 46.559 | -0.733 | 36.849 | 1.00 | 58.60 | C |
| ATOM | 3346 | CG | ARG | B | 397 | 47.104 | 0.604 | 37.323 | 1.00 | 59.72 | C |
| ATOM | 3347 | CD | ARG | B | 397 | 48.024 | 0.462 | 38.521 | 1.00 | 59.24 | C |
| ATOM | 3348 | NE | ARG | B | 397 | 48.336 | 1.767 | 39.100 | 1.00 | 61.40 | N |
| ATOM | 3349 | CZ | ARG | B | 397 | 49.062 | 1.953 | 40.200 | 1.00 | 62.58 | C |
| ATOM | 3350 | NH1 | ARG | B | 397 | 49.563 | 0.914 | 40.855 | 1.00 | 63.40 | N |
| ATOM | 3351 | NH2 | ARG | B | 397 | 49.283 | 3.183 | 40.648 | 1.00 | 62.52 | N |
| ATOM | 3352 | C | ARG | B | 397 | 46.961 | -2.994 | 35.870 | 1.00 | 58.21 | C |
| ATOM | 3353 | O | ARG | B | 397 | 47.648 | -4.012 | 35.991 | 1.00 | 58.89 | O |
| ATOM | 3354 | N | PRO | B | 403 | 37.025 | 1.210 | 41.387 | 1.00 | 40.60 | N |
| ATOM | 3355 | CD | PRO | B | 403 | 37.152 | 2.093 | 40.218 | 1.00 | 40.28 | C |
| ATOM | 3356 | CA | PRO | B | 403 | 37.090 | 1.981 | 42.636 | 1.00 | 40.38 | C |
| ATOM | 3357 | CB | PRO | B | 403 | 37.388 | 3.398 | 42.151 | 1.00 | 41.12 | C |
| ATOM | 3358 | CG | PRO | B | 403 | 36.757 | 3.432 | 40.789 | 1.00 | 41.59 | C |
| ATOM | 3359 | C | PRO | B | 403 | 35.817 | 1.889 | 43.487 | 1.00 | 40.42 | C |
| ATOM | 3360 | O | PRO | B | 403 | 35.515 | 2.769 | 44.315 | 1.00 | 39.86 | O |
| ATOM | 3361 | N | ILE | B | 404 | 35.072 | 0.809 | 43.287 | 1.00 | 38.75 | N |
| ATOM | 3362 | CA | ILE | B | 404 | 33.857 | 0.599 | 44.053 | 1.00 | 36.04 | C |
| ATOM | 3363 | CB | ILE | B | 404 | 33.114 | -0.683 | 43.573 | 1.00 | 37.00 | C |
| ATOM | 3364 | CG2 | ILE | B | 404 | 32.173 | -1.209 | 44.661 | 1.00 | 39.37 | C |
| ATOM | 3365 | CG1 | ILE | B | 404 | 32.325 | -0.362 | 42.308 | 1.00 | 39.61 | C |
| ATOM | 3366 | CD1 | ILE | B | 404 | 31.342 | 0.783 | 42.492 | 1.00 | 41.71 | C |
| ATOM | 3367 | C | ILE | B | 404 | 34.199 | 0.496 | 45.540 | 1.00 | 32.68 | C |
| ATOM | 3368 | O | ILE | B | 404 | 33.458 | 0.996 | 46.385 | 1.00 | 30.06 | O |
| ATOM | 3369 | N | LYS | B | 405 | 35.341 | -0.112 | 45.849 | 1.00 | 30.57 | N |
| ATOM | 3370 | CA | LYS | B | 405 | 35.761 | -0.296 | 47.240 | 1.00 | 29.40 | C |
| ATOM | 3371 | CB | LYS | B | 405 | 37.013 | -1.184 | 47.294 | 1.00 | 28.96 | C |
| ATOM | 3372 | CG | LYS | B | 405 | 36.716 | -2.644 | 46.944 | 1.00 | 28.84 | C |
| ATOM | 3373 | CD | LYS | B | 405 | 37.972 | -3.484 | 46.890 | 1.00 | 27.28 | C |
| ATOM | 3374 | CE | LYS | B | 405 | 37.638 | -4.976 | 46.837 | 1.00 | 30.17 | C |
| ATOM | 3375 | NZ | LYS | B | 405 | 38.763 | -5.814 | 47.387 | 1.00 | 26.91 | N |
| ATOM | 3376 | C | LYS | B | 405 | 35.967 | 0.960 | 48.101 | 1.00 | 27.96 | C |
| ATOM | 3377 | O | LYS | B | 405 | 36.135 | 0.852 | 49.308 | 1.00 | 25.19 | O |
| ATOM | 3378 | N | TRP | B | 406 | 35.951 | 2.143 | 47.496 | 1.00 | 28.56 | N |
| ATOM | 3379 | CA | TRP | B | 406 | 36.114 | 3.383 | 48.267 | 1.00 | 27.46 | C |
| ATOM | 3380 | CB | TRP | B | 406 | 37.243 | 4.241 | 47.678 | 1.00 | 29.92 | C |
| ATOM | 3381 | CG | TRP | B | 406 | 38.621 | 3.654 | 47.808 | 1.00 | 29.89 | C |
| ATOM | 3382 | CD2 | TRP | B | 406 | 39.195 | 2.618 | 47.001 | 1.00 | 30.44 | C |
| ATOM | 3383 | CE2 | TRP | B | 406 | 40.512 | 2.409 | 47.462 | 1.00 | 30.55 | C |
| ATOM | 3384 | CE3 | TRP | B | 406 | 38.721 | 1.846 | 45.930 | 1.00 | 30.73 | C |
| ATOM | 3385 | CD1 | TRP | B | 406 | 39.583 | 4.020 | 48.701 | 1.00 | 29.61 | C |
| ATOM | 3386 | NE1 | TRP | B | 406 | 40.725 | 3.276 | 48.500 | 1.00 | 31.61 | N |
| ATOM | 3387 | CZ2 | TRP | B | 406 | 41.366 | 1.460 | 46.891 | 1.00 | 31.54 | C |
| ATOM | 3388 | CZ3 | TRP | B | 406 | 39.575 | 0.897 | 45.360 | 1.00 | 32.72 | C |
| ATOM | 3389 | CH2 | TRP | B | 406 | 40.883 | 0.715 | 45.845 | 1.00 | 31.59 | C |
| ATOM | 3390 | C | TRP | B | 406 | 34.820 | 4.198 | 48.222 | 1.00 | 28.65 | C |
| ATOM | 3391 | O | TRP | B | 406 | 34.737 | 5.286 | 48.798 | 1.00 | 28.34 | O |
| ATOM | 3392 | N | THR | B | 407 | 33.814 | 3.670 | 47.531 | 1.00 | 29.54 | N |
| ATOM | 3393 | CA | THR | B | 407 | 32.540 | 4.368 | 47.354 | 1.00 | 30.08 | C |
| ATOM | 3394 | CB | THR | B | 407 | 31.872 | 3.919 | 46.047 | 1.00 | 30.37 | C |
| ATOM | 3395 | OG1 | THR | B | 407 | 32.850 | 3.917 | 45.008 | 1.00 | 34.38 | O |
| ATOM | 3396 | CG2 | THR | B | 407 | 30.733 | 4.866 | 45.663 | 1.00 | 32.52 | C |
| ATOM | 3397 | C | THR | B | 407 | 31.529 | 4.196 | 48.489 | 1.00 | 29.13 | C |
| ATOM | 3398 | O | THR | B | 407 | 31.230 | 3.069 | 48.902 | 1.00 | 26.60 | O |
| ATOM | 3399 | N | ALA | B | 408 | 30.996 | 5.317 | 48.979 | 1.00 | 27.13 | N |
| ATOM | 3400 | CA | ALA | B | 408 | 30.015 | 5.288 | 50.067 | 1.00 | 26.76 | C |
| ATOM | 3401 | CB | ALA | B | 408 | 29.779 | 6.706 | 50.611 | 1.00 | 26.05 | C |

Figure 14

```
ATOM   3402  C    ALA B 408      28.696    4.676   49.602  1.00 27.00           C
ATOM   3403  O    ALA B 408      28.306    4.821   48.448  1.00 27.27           O
ATOM   3404  N    PRO B 409      27.977    4.002   50.514  1.00 27.82           N
ATOM   3405  CD   PRO B 409      28.332    3.790   51.926  1.00 26.88           C
ATOM   3406  CA   PRO B 409      26.694    3.363   50.192  1.00 29.01           C
ATOM   3407  CB   PRO B 409      26.162    2.948   51.561  1.00 29.90           C
ATOM   3408  CG   PRO B 409      27.433    2.646   52.324  1.00 30.15           C
ATOM   3409  C    PRO B 409      25.690    4.221   49.427  1.00 30.18           C
ATOM   3410  O    PRO B 409      25.077    3.751   48.464  1.00 26.63           O
ATOM   3411  N    GLU B 410      25.518    5.471   49.859  1.00 30.24           N
ATOM   3412  CA   GLU B 410      24.560    6.350   49.203  1.00 31.85           C
ATOM   3413  CB   GLU B 410      24.362    7.648   50.012  1.00 30.44           C
ATOM   3414  CG   GLU B 410      25.534    8.632   49.973  1.00 31.36           C
ATOM   3415  CD   GLU B 410      26.598    8.360   51.034  1.00 28.89           C
ATOM   3416  OE1  GLU B 410      26.578    7.291   51.669  1.00 29.11           O
ATOM   3417  OE2  GLU B 410      27.468    9.226   51.228  1.00 32.20           O
ATOM   3418  C    GLU B 410      24.990    6.667   47.769  1.00 33.59           C
ATOM   3419  O    GLU B 410      24.149    6.878   46.892  1.00 34.83           O
ATOM   3420  N    ALA B 411      26.294    6.701   47.527  1.00 34.38           N
ATOM   3421  CA   ALA B 411      26.803    6.973   46.184  1.00 34.84           C
ATOM   3422  CB   ALA B 411      28.291    7.280   46.236  1.00 31.98           C
ATOM   3423  C    ALA B 411      26.558    5.748   45.318  1.00 36.28           C
ATOM   3424  O    ALA B 411      26.217    5.855   44.139  1.00 35.96           O
ATOM   3425  N    ILE B 412      26.731    4.575   45.916  1.00 37.17           N
ATOM   3426  CA   ILE B 412      26.523    3.328   45.198  1.00 38.52           C
ATOM   3427  CB   ILE B 412      26.955    2.120   46.046  1.00 38.93           C
ATOM   3428  CG2  ILE B 412      26.561    0.826   45.342  1.00 38.79           C
ATOM   3429  CG1  ILE B 412      28.462    2.175   46.293  1.00 38.22           C
ATOM   3430  CD1  ILE B 412      28.953    1.169   47.290  1.00 39.23           C
ATOM   3431  C    ILE B 412      25.063    3.128   44.810  1.00 40.71           C
ATOM   3432  O    ILE B 412      24.751    2.890   43.641  1.00 41.22           O
ATOM   3433  N    ASN B 413      24.168    3.239   45.789  1.00 40.81           N
ATOM   3434  CA   ASN B 413      22.742    3.015   45.541  1.00 44.08           C
ATOM   3435  CB   ASN B 413      22.034    2.678   46.855  1.00 43.44           C
ATOM   3436  CG   ASN B 413      22.699    1.547   47.591  1.00 44.20           C
ATOM   3437  OD1  ASN B 413      23.033    0.520   46.996  1.00 45.69           O
ATOM   3438  ND2  ASN B 413      22.895    1.720   48.897  1.00 43.72           N
ATOM   3439  C    ASN B 413      21.949    4.112   44.846  1.00 45.02           C
ATOM   3440  O    ASN B 413      21.038    3.821   44.071  1.00 44.93           O
ATOM   3441  N    TYR B 414      22.289    5.369   45.118  1.00 46.12           N
ATOM   3442  CA   TYR B 414      21.543    6.480   44.545  1.00 46.85           C
ATOM   3443  CB   TYR B 414      20.806    7.196   45.675  1.00 47.67           C
ATOM   3444  CG   TYR B 414      19.962    6.233   46.478  1.00 49.58           C
ATOM   3445  CD1  TYR B 414      18.915    5.529   45.874  1.00 50.82           C
ATOM   3446  CE1  TYR B 414      18.173    4.583   46.584  1.00 50.08           C
ATOM   3447  CD2  TYR B 414      20.246    5.970   47.820  1.00 50.49           C
ATOM   3448  CE2  TYR B 414      19.511    5.028   48.537  1.00 51.60           C
ATOM   3449  CZ   TYR B 414      18.475    4.337   47.912  1.00 51.99           C
ATOM   3450  OH   TYR B 414      17.750    3.397   48.614  1.00 53.34           O
ATOM   3451  C    TYR B 414      22.367    7.463   43.728  1.00 46.84           C
ATOM   3452  O    TYR B 414      21.821    8.357   43.070  1.00 46.58           O
ATOM   3453  N    GLY B 415      23.681    7.288   43.757  1.00 46.17           N
ATOM   3454  CA   GLY B 415      24.546    8.169   43.005  1.00 45.45           C
ATOM   3455  C    GLY B 415      24.679    9.532   43.644  1.00 45.05           C
ATOM   3456  O    GLY B 415      24.967   10.508   42.951  1.00 46.54           O
ATOM   3457  N    THR B 416      24.465    9.624   44.951  1.00 44.77           N
ATOM   3458  CA   THR B 416      24.605   10.917   45.609  1.00 44.14           C
ATOM   3459  CB   THR B 416      23.562   11.142   46.727  1.00 45.78           C
ATOM   3460  OG1  THR B 416      24.215   11.097   48.002  1.00 47.81           O
ATOM   3461  CG2  THR B 416      22.462   10.095   46.671  1.00 42.62           C
```

Figure 14

| | | | | | | | | | | |
|---|---|---|---|---|---|---|---|---|---|---|
|ATOM|3462|C|THR|B|416|26.003|11.038|46.209|1.00 43.22|C|
|ATOM|3463|O|THR|B|416|26.370|10.315|47.141|1.00 43.82|O|
|ATOM|3464|N|PHE|B|417|26.782|11.952|45.638|1.00 39.76|N|
|ATOM|3465|CA|PHE|B|417|28.145|12.218|46.067|1.00 36.84|C|
|ATOM|3466|CB|PHE|B|417|29.086|12.240|44.862|1.00 38.36|C|
|ATOM|3467|CG|PHE|B|417|29.249|10.912|44.180|1.00 39.69|C|
|ATOM|3468|CD1|PHE|B|417|30.224|10.012|44.609|1.00 41.02|C|
|ATOM|3469|CD2|PHE|B|417|28.441|10.564|43.095|1.00 41.81|C|
|ATOM|3470|CE1|PHE|B|417|30.402|8.782|43.972|1.00 41.57|C|
|ATOM|3471|CE2|PHE|B|417|28.610|9.329|42.444|1.00 43.53|C|
|ATOM|3472|CZ|PHE|B|417|29.597|8.439|42.891|1.00 42.44|C|
|ATOM|3473|C|PHE|B|417|28.193|13.586|46.741|1.00 36.14|C|
|ATOM|3474|O|PHE|B|417|27.716|14.579|46.185|1.00 34.19|O|
|ATOM|3475|N|THR|B|418|28.757|13.629|47.941|1.00 32.31|N|
|ATOM|3476|CA|THR|B|418|28.904|14.874|48.677|1.00 30.78|C|
|ATOM|3477|CB|THR|B|418|27.857|15.036|49.791|1.00 31.75|C|
|ATOM|3478|OG1|THR|B|418|28.109|14.065|50.811|1.00 29.29|O|
|ATOM|3479|CG2|THR|B|418|26.441|14.874|49.244|1.00 32.63|C|
|ATOM|3480|C|THR|B|418|30.260|14.774|49.352|1.00 30.44|C|
|ATOM|3481|O|THR|B|418|30.979|13.783|49.178|1.00 29.89|O|
|ATOM|3482|N|ILE|B|419|30.608|15.790|50.129|1.00 28.39|N|
|ATOM|3483|CA|ILE|B|419|31.874|15.772|50.825|1.00 27.94|C|
|ATOM|3484|CB|ILE|B|419|32.151|17.122|51.537|1.00 27.92|C|
|ATOM|3485|CG2|ILE|B|419|31.195|17.294|52.727|1.00 29.10|C|
|ATOM|3486|CG1|ILE|B|419|33.606|17.164|52.035|1.00 31.29|C|
|ATOM|3487|CD1|ILE|B|419|34.658|17.211|50.921|1.00 29.11|C|
|ATOM|3488|C|ILE|B|419|31.799|14.636|51.850|1.00 26.22|C|
|ATOM|3489|O|ILE|B|419|32.818|14.118|52.272|1.00 26.00|O|
|ATOM|3490|N|LYS|B|420|30.592|14.245|52.249|1.00 25.51|N|
|ATOM|3491|CA|LYS|B|420|30.466|13.147|53.216|1.00 27.14|C|
|ATOM|3492|CB|LYS|B|420|29.038|13.064|53.791|1.00 26.86|C|
|ATOM|3493|CG|LYS|B|420|28.705|14.152|54.816|1.00 25.25|C|
|ATOM|3494|CD|LYS|B|420|29.856|14.371|55.818|1.00 27.32|C|
|ATOM|3495|CE|LYS|B|420|29.474|15.405|56.869|1.00 26.42|C|
|ATOM|3496|NZ|LYS|B|420|30.574|15.796|57.794|1.00 26.09|N|
|ATOM|3497|C|LYS|B|420|30.844|11.821|52.542|1.00 25.83|C|
|ATOM|3498|O|LYS|B|420|31.322|10.895|53.199|1.00 25.09|O|
|ATOM|3499|N|SER|B|421|30.623|11.736|51.233|1.00 27.15|N|
|ATOM|3500|CA|SER|B|421|30.986|10.536|50.476|1.00 28.98|C|
|ATOM|3501|CB|SER|B|421|30.536|10.664|49.019|1.00 31.56|C|
|ATOM|3502|OG|SER|B|421|29.166|11.025|48.925|1.00 38.08|O|
|ATOM|3503|C|SER|B|421|32.518|10.405|50.521|1.00 29.40|C|
|ATOM|3504|O|SER|B|421|33.054|9.300|50.666|1.00 28.17|O|
|ATOM|3505|N|ASP|B|422|33.217|11.533|50.405|1.00 25.10|N|
|ATOM|3506|CA|ASP|B|422|34.686|11.516|50.437|1.00 24.44|C|
|ATOM|3507|CB|ASP|B|422|35.290|12.884|50.089|1.00 25.79|C|
|ATOM|3508|CG|ASP|B|422|34.960|13.347|48.686|1.00 30.18|C|
|ATOM|3509|OD1|ASP|B|422|35.121|12.570|47.724|1.00 32.32|O|
|ATOM|3510|OD2|ASP|B|422|34.570|14.519|48.534|1.00 34.42|O|
|ATOM|3511|C|ASP|B|422|35.193|11.128|51.819|1.00 23.25|C|
|ATOM|3512|O|ASP|B|422|36.254|10.504|51.934|1.00 22.58|O|
|ATOM|3513|N|VAL|B|423|34.468|11.536|52.866|1.00 21.50|N|
|ATOM|3514|CA|VAL|B|423|34.857|11.190|54.227|1.00 22.61|C|
|ATOM|3515|CB|VAL|B|423|33.869|11.749|55.280|1.00 24.44|C|
|ATOM|3516|CG1|VAL|B|423|34.076|11.027|56.627|1.00 27.93|C|
|ATOM|3517|CG2|VAL|B|423|34.096|13.247|55.458|1.00 21.28|C|
|ATOM|3518|C|VAL|B|423|34.886|9.672|54.339|1.00 22.88|C|
|ATOM|3519|O|VAL|B|423|35.784|9.104|54.964|1.00 22.59|O|
|ATOM|3520|N|TRP|B|424|33.898|9.023|53.730|1.00 22.08|N|
|ATOM|3521|CA|TRP|B|424|33.840|7.557|53.731|1.00 25.02|C|

Figure 14

| | | | | | | | | | |
|---|---|---|---|---|---|---|---|---|---|
| ATOM | 3522 | CB | TRP | B | 424 | 32.583 | 7.067 | 52.989 | 1.00 22.26 | C |
| ATOM | 3523 | CG | TRP | B | 424 | 32.539 | 5.577 | 52.782 | 1.00 26.08 | C |
| ATOM | 3524 | CD2 | TRP | B | 424 | 31.701 | 4.635 | 53.462 | 1.00 27.24 | C |
| ATOM | 3525 | CE2 | TRP | B | 424 | 32.016 | 3.352 | 52.952 | 1.00 29.86 | C |
| ATOM | 3526 | CE3 | TRP | B | 424 | 30.717 | 4.747 | 54.452 | 1.00 29.96 | C |
| ATOM | 3527 | CD1 | TRP | B | 424 | 33.307 | 4.843 | 51.911 | 1.00 24.44 | C |
| ATOM | 3528 | NE1 | TRP | B | 424 | 32.998 | 3.513 | 52.010 | 1.00 25.25 | N |
| ATOM | 3529 | CZ2 | TRP | B | 424 | 31.382 | 2.190 | 53.400 | 1.00 27.11 | C |
| ATOM | 3530 | CZ3 | TRP | B | 424 | 30.084 | 3.584 | 54.897 | 1.00 31.00 | C |
| ATOM | 3531 | CH2 | TRP | B | 424 | 30.423 | 2.325 | 54.370 | 1.00 28.61 | C |
| ATOM | 3532 | C | TRP | B | 424 | 35.106 | 7.066 | 53.005 | 1.00 22.69 | C |
| ATOM | 3533 | O | TRP | B | 424 | 35.853 | 6.226 | 53.519 | 1.00 23.03 | O |
| ATOM | 3534 | N | SER | B | 425 | 35.341 | 7.620 | 51.822 | 1.00 22.81 | N |
| ATOM | 3535 | CA | SER | B | 425 | 36.511 | 7.255 | 51.015 | 1.00 23.08 | C |
| ATOM | 3536 | CB | SER | B | 425 | 36.607 | 8.144 | 49.758 | 1.00 21.27 | C |
| ATOM | 3537 | OG | SER | B | 425 | 35.550 | 7.886 | 48.839 | 1.00 22.25 | O |
| ATOM | 3538 | C | SER | B | 425 | 37.787 | 7.412 | 51.831 | 1.00 23.55 | C |
| ATOM | 3539 | O | SER | B | 425 | 38.683 | 6.568 | 51.766 | 1.00 26.21 | O |
| ATOM | 3540 | N | PHE | B | 426 | 37.871 | 8.497 | 52.598 | 1.00 24.35 | N |
| ATOM | 3541 | CA | PHE | B | 426 | 39.055 | 8.756 | 53.415 | 1.00 25.70 | C |
| ATOM | 3542 | CB | PHE | B | 426 | 38.948 | 10.120 | 54.109 | 1.00 23.57 | C |
| ATOM | 3543 | CG | PHE | B | 426 | 40.157 | 10.476 | 54.925 | 1.00 24.60 | C |
| ATOM | 3544 | CD1 | PHE | B | 426 | 41.333 | 10.892 | 54.305 | 1.00 25.09 | C |
| ATOM | 3545 | CD2 | PHE | B | 426 | 40.143 | 10.345 | 56.313 | 1.00 24.86 | C |
| ATOM | 3546 | CE1 | PHE | B | 426 | 42.473 | 11.165 | 55.048 | 1.00 25.07 | C |
| ATOM | 3547 | CE2 | PHE | B | 426 | 41.272 | 10.612 | 57.061 | 1.00 22.70 | C |
| ATOM | 3548 | CZ | PHE | B | 426 | 42.449 | 11.025 | 56.428 | 1.00 24.49 | C |
| ATOM | 3549 | C | PHE | B | 426 | 39.258 | 7.664 | 54.466 | 1.00 25.64 | C |
| ATOM | 3550 | O | PHE | B | 426 | 40.387 | 7.267 | 54.751 | 1.00 27.87 | O |
| ATOM | 3551 | N | GLY | B | 427 | 38.168 | 7.200 | 55.067 | 1.00 27.74 | N |
| ATOM | 3552 | CA | GLY | B | 427 | 38.283 | 6.131 | 56.046 | 1.00 24.48 | C |
| ATOM | 3553 | C | GLY | B | 427 | 38.854 | 4.891 | 55.359 | 1.00 24.80 | C |
| ATOM | 3554 | O | GLY | B | 427 | 39.676 | 4.183 | 55.936 | 1.00 24.02 | O |
| ATOM | 3555 | N | ILE | B | 428 | 38.414 | 4.611 | 54.129 | 1.00 23.61 | N |
| ATOM | 3556 | CA | ILE | B | 428 | 38.941 | 3.441 | 53.407 | 1.00 25.36 | C |
| ATOM | 3557 | CB | ILE | B | 428 | 38.180 | 3.196 | 52.074 | 1.00 24.70 | C |
| ATOM | 3558 | CG2 | ILE | B | 428 | 38.802 | 2.039 | 51.325 | 1.00 23.35 | C |
| ATOM | 3559 | CG1 | ILE | B | 428 | 36.698 | 2.893 | 52.348 | 1.00 25.02 | C |
| ATOM | 3560 | CD1 | ILE | B | 428 | 36.464 | 1.600 | 53.154 | 1.00 22.54 | C |
| ATOM | 3561 | C | ILE | B | 428 | 40.429 | 3.696 | 53.111 | 1.00 27.09 | C |
| ATOM | 3562 | O | ILE | B | 428 | 41.267 | 2.805 | 53.245 | 1.00 25.97 | O |
| ATOM | 3563 | N | LEU | B | 429 | 40.761 | 4.931 | 52.737 | 1.00 26.33 | N |
| ATOM | 3564 | CA | LEU | B | 429 | 42.146 | 5.283 | 52.436 | 1.00 26.74 | C |
| ATOM | 3565 | CB | LEU | B | 429 | 42.230 | 6.751 | 51.967 | 1.00 25.85 | C |
| ATOM | 3566 | CG | LEU | B | 429 | 43.493 | 7.209 | 51.218 | 1.00 32.50 | C |
| ATOM | 3567 | CD1 | LEU | B | 429 | 43.220 | 8.512 | 50.430 | 1.00 31.43 | C |
| ATOM | 3568 | CD2 | LEU | B | 429 | 44.623 | 7.401 | 52.200 | 1.00 30.13 | C |
| ATOM | 3569 | C | LEU | B | 429 | 43.032 | 5.054 | 53.672 | 1.00 27.11 | C |
| ATOM | 3570 | O | LEU | B | 429 | 44.197 | 4.651 | 53.545 | 1.00 27.35 | O |
| ATOM | 3571 | N | LEU | B | 430 | 42.494 | 5.310 | 54.864 | 1.00 25.89 | N |
| ATOM | 3572 | CA | LEU | B | 430 | 43.271 | 5.106 | 56.080 | 1.00 25.42 | C |
| ATOM | 3573 | CB | LEU | B | 430 | 42.483 | 5.545 | 57.321 | 1.00 26.31 | C |
| ATOM | 3574 | CG | LEU | B | 430 | 42.386 | 7.051 | 57.603 | 1.00 26.11 | C |
| ATOM | 3575 | CD1 | LEU | B | 430 | 41.490 | 7.262 | 58.834 | 1.00 26.87 | C |
| ATOM | 3576 | CD2 | LEU | B | 430 | 43.779 | 7.647 | 57.839 | 1.00 27.77 | C |
| ATOM | 3577 | C | LEU | B | 430 | 43.695 | 3.637 | 56.221 | 1.00 25.72 | C |
| ATOM | 3578 | O | LEU | B | 430 | 44.777 | 3.352 | 56.739 | 1.00 25.80 | O |
| ATOM | 3579 | N | THR | B | 431 | 42.857 | 2.716 | 55.748 | 1.00 25.61 | N |
| ATOM | 3580 | CA | THR | B | 431 | 43.204 | 1.306 | 55.829 | 1.00 27.05 | C |

Figure 14

| | | | | | | | | | | |
|---|---|---|---|---|---|---|---|---|---|---|
| ATOM | 3581 | CB | THR | B | 431 | 41.986 | 0.359 | 55.534 | 1.00 24.59 | C |
| ATOM | 3582 | OG1 | THR | B | 431 | 41.545 | 0.501 | 54.181 | 1.00 26.55 | O |
| ATOM | 3583 | CG2 | THR | B | 431 | 40.829 | 0.679 | 56.489 | 1.00 22.87 | C |
| ATOM | 3584 | C | THR | B | 431 | 44.375 | 1.029 | 54.874 | 1.00 28.98 | C |
| ATOM | 3585 | O | THR | B | 431 | 45.302 | 0.293 | 55.240 | 1.00 28.37 | O |
| ATOM | 3586 | N | GLU | B | 432 | 44.354 | 1.643 | 53.684 | 1.00 28.53 | N |
| ATOM | 3587 | CA | GLU | B | 432 | 45.460 | 1.470 | 52.723 | 1.00 29.79 | C |
| ATOM | 3588 | CB | GLU | B | 432 | 45.205 | 2.240 | 51.414 | 1.00 30.37 | C |
| ATOM | 3589 | CG | GLU | B | 432 | 44.030 | 1.751 | 50.554 | 1.00 30.72 | C |
| ATOM | 3590 | CD | GLU | B | 432 | 43.922 | 2.520 | 49.230 | 1.00 32.44 | C |
| ATOM | 3591 | OE1 | GLU | B | 432 | 43.410 | 3.670 | 49.218 | 1.00 31.46 | O |
| ATOM | 3592 | OE2 | GLU | B | 432 | 44.370 | 1.975 | 48.198 | 1.00 31.29 | O |
| ATOM | 3593 | C | GLU | B | 432 | 46.777 | 1.989 | 53.320 | 1.00 29.99 | C |
| ATOM | 3594 | O | GLU | B | 432 | 47.832 | 1.396 | 53.113 | 1.00 30.14 | O |
| ATOM | 3595 | N | ILE | B | 433 | 46.710 | 3.106 | 54.044 | 1.00 30.32 | N |
| ATOM | 3596 | CA | ILE | B | 433 | 47.895 | 3.712 | 54.647 | 1.00 32.89 | C |
| ATOM | 3597 | CB | ILE | B | 433 | 47.590 | 5.129 | 55.180 | 1.00 33.42 | C |
| ATOM | 3598 | CG2 | ILE | B | 433 | 48.746 | 5.641 | 56.019 | 1.00 34.25 | C |
| ATOM | 3599 | CG1 | ILE | B | 433 | 47.336 | 6.083 | 54.007 | 1.00 32.40 | C |
| ATOM | 3600 | CD1 | ILE | B | 433 | 47.080 | 7.507 | 54.447 | 1.00 33.06 | C |
| ATOM | 3601 | C | ILE | B | 433 | 48.542 | 2.920 | 55.783 | 1.00 35.13 | C |
| ATOM | 3602 | O | ILE | B | 433 | 49.775 | 2.929 | 55.918 | 1.00 37.32 | O |
| ATOM | 3603 | N | VAL | B | 434 | 47.733 | 2.247 | 56.599 | 1.00 34.76 | N |
| ATOM | 3604 | CA | VAL | B | 434 | 48.275 | 1.477 | 57.714 | 1.00 36.31 | C |
| ATOM | 3605 | CB | VAL | B | 434 | 47.322 | 1.504 | 58.942 | 1.00 37.37 | C |
| ATOM | 3606 | CG1 | VAL | B | 434 | 47.171 | 2.935 | 59.445 | 1.00 35.52 | C |
| ATOM | 3607 | CG2 | VAL | B | 434 | 45.966 | 0.910 | 58.576 | 1.00 34.92 | C |
| ATOM | 3608 | C | VAL | B | 434 | 48.613 | 0.024 | 57.378 | 1.00 36.18 | C |
| ATOM | 3609 | O | VAL | B | 434 | 49.205 | -0.675 | 58.195 | 1.00 37.88 | O |
| ATOM | 3610 | N | THR | B | 435 | 48.240 | -0.431 | 56.184 | 1.00 36.69 | N |
| ATOM | 3611 | CA | THR | B | 435 | 48.531 | -1.802 | 55.759 | 1.00 36.65 | C |
| ATOM | 3612 | CB | THR | B | 435 | 47.265 | -2.519 | 55.242 | 1.00 36.23 | C |
| ATOM | 3613 | OG1 | THR | B | 435 | 46.723 | -1.795 | 54.123 | 1.00 33.61 | O |
| ATOM | 3614 | CG2 | THR | B | 435 | 46.213 | -2.627 | 56.360 | 1.00 35.41 | C |
| ATOM | 3615 | C | THR | B | 435 | 49.574 | -1.782 | 54.637 | 1.00 38.77 | C |
| ATOM | 3616 | O | THR | B | 435 | 49.748 | -2.759 | 53.901 | 1.00 37.87 | O |
| ATOM | 3617 | N | HIS | B | 436 | 50.249 | -0.647 | 54.509 | 1.00 40.23 | N |
| ATOM | 3618 | CA | HIS | B | 436 | 51.275 | -0.461 | 53.501 | 1.00 41.79 | C |
| ATOM | 3619 | CB | HIS | B | 436 | 52.435 | -1.411 | 53.782 | 1.00 43.44 | C |
| ATOM | 3620 | CG | HIS | B | 436 | 53.082 | -1.170 | 55.111 | 1.00 45.53 | C |
| ATOM | 3621 | CD2 | HIS | B | 436 | 53.088 | -1.905 | 56.248 | 1.00 47.25 | C |
| ATOM | 3622 | ND1 | HIS | B | 436 | 53.774 | -0.014 | 55.400 | 1.00 46.45 | N |
| ATOM | 3623 | CE1 | HIS | B | 436 | 54.175 | -0.045 | 56.659 | 1.00 47.48 | C |
| ATOM | 3624 | NE2 | HIS | B | 436 | 53.769 | -1.182 | 57.197 | 1.00 47.76 | N |
| ATOM | 3625 | C | HIS | B | 436 | 50.783 | -0.618 | 52.070 | 1.00 41.99 | C |
| ATOM | 3626 | O | HIS | B | 436 | 51.550 | -0.972 | 51.177 | 1.00 42.31 | O |
| ATOM | 3627 | N | GLY | B | 437 | 49.503 | -0.343 | 51.846 | 1.00 41.02 | N |
| ATOM | 3628 | CA | GLY | B | 437 | 48.980 | -0.438 | 50.499 | 1.00 40.16 | C |
| ATOM | 3629 | C | GLY | B | 437 | 48.052 | -1.598 | 50.199 | 1.00 39.85 | C |
| ATOM | 3630 | O | GLY | B | 437 | 47.612 | -1.747 | 49.059 | 1.00 39.15 | O |
| ATOM | 3631 | N | ARG | B | 438 | 47.751 | -2.426 | 51.191 | 1.00 39.78 | N |
| ATOM | 3632 | CA | ARG | B | 438 | 46.843 | -3.542 | 50.950 | 1.00 40.15 | C |
| ATOM | 3633 | CB | ARG | B | 438 | 46.552 | -4.314 | 52.241 | 1.00 42.45 | C |
| ATOM | 3634 | CG | ARG | B | 438 | 45.562 | -5.473 | 52.052 | 1.00 44.54 | C |
| ATOM | 3635 | CD | ARG | B | 438 | 44.810 | -5.816 | 53.343 | 1.00 47.28 | C |
| ATOM | 3636 | NE | ARG | B | 438 | 43.966 | -4.700 | 53.777 | 1.00 48.76 | N |
| ATOM | 3637 | CZ | ARG | B | 438 | 43.213 | -4.695 | 54.876 | 1.00 47.98 | C |
| ATOM | 3638 | NH1 | ARG | B | 438 | 43.177 | -5.753 | 55.676 | 1.00 45.56 | N |
| ATOM | 3639 | NH2 | ARG | B | 438 | 42.505 | -3.615 | 55.186 | 1.00 46.70 | N |
| ATOM | 3640 | C | ARG | B | 438 | 45.530 | -2.985 | 50.417 | 1.00 38.55 | C |

Figure 14

| ATOM | 3641 | O | ARG | B | 438 | 45.060 | -1.951 | 50.888 | 1.00 | 36.75 | O |
|------|------|-----|-----|---|-----|--------|--------|--------|------|-------|---|
| ATOM | 3642 | N | ILE | B | 439 | 44.954 | -3.664 | 49.428 | 1.00 | 37.87 | N |
| ATOM | 3643 | CA | ILE | B | 439 | 43.677 | -3.269 | 48.846 | 1.00 | 37.27 | C |
| ATOM | 3644 | CB | ILE | B | 439 | 43.329 | -4.134 | 47.606 | 1.00 | 40.58 | C |
| ATOM | 3645 | CG2 | ILE | B | 439 | 41.877 | -3.904 | 47.182 | 1.00 | 39.37 | C |
| ATOM | 3646 | CG1 | ILE | B | 439 | 44.258 | -3.779 | 46.441 | 1.00 | 42.67 | C |
| ATOM | 3647 | CD1 | ILE | B | 439 | 44.010 | -4.600 | 45.185 | 1.00 | 45.41 | C |
| ATOM | 3648 | C | ILE | B | 439 | 42.597 | -3.466 | 49.904 | 1.00 | 37.18 | C |
| ATOM | 3649 | O | ILE | B | 439 | 42.705 | -4.349 | 50.756 | 1.00 | 36.64 | O |
| ATOM | 3650 | N | PRO | B | 440 | 41.553 | -2.626 | 49.887 | 1.00 | 37.50 | N |
| ATOM | 3651 | CD | PRO | B | 440 | 41.392 | -1.375 | 49.128 | 1.00 | 36.36 | C |
| ATOM | 3652 | CA | PRO | B | 440 | 40.485 | -2.777 | 50.886 | 1.00 | 36.75 | C |
| ATOM | 3653 | CB | PRO | B | 440 | 39.607 | -1.551 | 50.644 | 1.00 | 35.50 | C |
| ATOM | 3654 | CG | PRO | B | 440 | 40.588 | -0.531 | 50.084 | 1.00 | 36.81 | C |
| ATOM | 3655 | C | PRO | B | 440 | 39.712 | -4.081 | 50.684 | 1.00 | 36.70 | C |
| ATOM | 3656 | O | PRO | B | 440 | 39.750 | -4.668 | 49.601 | 1.00 | 36.40 | O |
| ATOM | 3657 | N | TYR | B | 441 | 39.017 | -4.531 | 51.724 | 1.00 | 35.06 | N |
| ATOM | 3658 | CA | TYR | B | 441 | 38.218 | -5.749 | 51.631 | 1.00 | 35.81 | C |
| ATOM | 3659 | CB | TYR | B | 441 | 36.934 | -5.449 | 50.835 | 1.00 | 31.55 | C |
| ATOM | 3660 | CG | TYR | B | 441 | 36.127 | -4.260 | 51.351 | 1.00 | 32.86 | C |
| ATOM | 3661 | CD1 | TYR | B | 441 | 35.255 | -4.395 | 52.443 | 1.00 | 30.56 | C |
| ATOM | 3662 | CE1 | TYR | B | 441 | 34.532 | -3.296 | 52.945 | 1.00 | 30.45 | C |
| ATOM | 3663 | CD2 | TYR | B | 441 | 36.256 | -2.991 | 50.766 | 1.00 | 30.99 | C |
| ATOM | 3664 | CE2 | TYR | B | 441 | 35.534 | -1.880 | 51.255 | 1.00 | 29.37 | C |
| ATOM | 3665 | CZ | TYR | B | 441 | 34.678 | -2.044 | 52.348 | 1.00 | 29.97 | C |
| ATOM | 3666 | OH | TYR | B | 441 | 33.988 | -0.967 | 52.846 | 1.00 | 27.65 | O |
| ATOM | 3667 | C | TYR | B | 441 | 39.024 | -6.862 | 50.937 | 1.00 | 36.92 | C |
| ATOM | 3668 | O | TYR | B | 441 | 38.614 | -7.382 | 49.903 | 1.00 | 35.82 | O |
| ATOM | 3669 | N | PRO | B | 442 | 40.181 | -7.245 | 51.510 | 1.00 | 39.55 | N |
| ATOM | 3670 | CD | PRO | B | 442 | 40.718 | -6.863 | 52.828 | 1.00 | 39.41 | C |
| ATOM | 3671 | CA | PRO | B | 442 | 41.000 | -8.297 | 50.892 | 1.00 | 41.17 | C |
| ATOM | 3672 | CB | PRO | B | 442 | 42.191 | -8.411 | 51.838 | 1.00 | 41.89 | C |
| ATOM | 3673 | CG | PRO | B | 442 | 41.594 | -8.043 | 53.176 | 1.00 | 42.51 | C |
| ATOM | 3674 | C | PRO | B | 442 | 40.246 | -9.609 | 50.723 | 1.00 | 43.60 | C |
| ATOM | 3675 | O | PRO | B | 442 | 39.717 | -10.169 | 51.683 | 1.00 | 43.34 | O |
| ATOM | 3676 | N | GLY | B | 443 | 40.187 | -10.084 | 49.484 | 1.00 | 44.95 | N |
| ATOM | 3677 | CA | GLY | B | 443 | 39.485 | -11.320 | 49.200 | 1.00 | 46.56 | C |
| ATOM | 3678 | C | GLY | B | 443 | 38.075 | -11.121 | 48.673 | 1.00 | 46.69 | C |
| ATOM | 3679 | O | GLY | B | 443 | 37.394 | -12.096 | 48.354 | 1.00 | 48.35 | O |
| ATOM | 3680 | N | MET | B | 444 | 37.630 | -9.872 | 48.568 | 1.00 | 45.45 | N |
| ATOM | 3681 | CA | MET | B | 444 | 36.283 | -9.578 | 48.079 | 1.00 | 44.64 | C |
| ATOM | 3682 | CB | MET | B | 444 | 35.545 | -8.645 | 49.061 | 1.00 | 43.11 | C |
| ATOM | 3683 | CG | MET | B | 444 | 35.182 | -9.255 | 50.404 | 1.00 | 44.28 | C |
| ATOM | 3684 | SD | MET | B | 444 | 34.331 | -8.080 | 51.523 | 1.00 | 45.06 | S |
| ATOM | 3685 | CE | MET | B | 444 | 32.916 | -7.757 | 50.641 | 1.00 | 42.48 | C |
| ATOM | 3686 | C | MET | B | 444 | 36.271 | -8.923 | 46.698 | 1.00 | 43.86 | C |
| ATOM | 3687 | O | MET | B | 444 | 37.106 | -8.067 | 46.410 | 1.00 | 45.03 | O |
| ATOM | 3688 | N | THR | B | 445 | 35.318 | -9.317 | 45.856 | 1.00 | 42.90 | N |
| ATOM | 3689 | CA | THR | B | 445 | 35.176 | -8.730 | 44.525 | 1.00 | 42.58 | C |
| ATOM | 3690 | CB | THR | B | 445 | 34.525 | -9.705 | 43.516 | 1.00 | 42.55 | C |
| ATOM | 3691 | OG1 | THR | B | 445 | 33.144 | -9.897 | 43.854 | 1.00 | 44.06 | O |
| ATOM | 3692 | CG2 | THR | B | 445 | 35.244 | -11.052 | 43.519 | 1.00 | 45.65 | C |
| ATOM | 3693 | C | THR | B | 445 | 34.233 | -7.541 | 44.689 | 1.00 | 42.19 | C |
| ATOM | 3694 | O | THR | B | 445 | 33.585 | -7.411 | 45.726 | 1.00 | 41.28 | O |
| ATOM | 3695 | N | ASN | B | 446 | 34.147 | -6.687 | 43.674 | 1.00 | 40.79 | N |
| ATOM | 3696 | CA | ASN | B | 446 | 33.266 | -5.525 | 43.739 | 1.00 | 41.78 | C |
| ATOM | 3697 | CB | ASN | B | 446 | 33.291 | -4.747 | 42.419 | 1.00 | 41.25 | C |
| ATOM | 3698 | CG | ASN | B | 446 | 34.547 | -3.925 | 42.259 | 1.00 | 41.04 | C |
| ATOM | 3699 | OD1 | ASN | B | 446 | 35.267 | -3.686 | 43.221 | 1.00 | 40.96 | O |
| ATOM | 3700 | ND2 | ASN | B | 446 | 34.805 | -3.468 | 41.040 | 1.00 | 41.93 | N |

Figure 14

```
ATOM   3701  C    ASN B 446      31.822  -5.899  44.093  1.00 40.84           C
ATOM   3702  O    ASN B 446      31.225  -5.301  44.983  1.00 41.62           O
ATOM   3703  N    PRO B 447      31.231  -6.868  43.380  1.00 41.73           N
ATOM   3704  CD   PRO B 447      31.603  -7.426  42.065  1.00 40.80           C
ATOM   3705  CA   PRO B 447      29.851  -7.223  43.738  1.00 39.93           C
ATOM   3706  CB   PRO B 447      29.420  -8.166  42.606  1.00 40.76           C
ATOM   3707  CG   PRO B 447      30.734  -8.642  41.987  1.00 41.85           C
ATOM   3708  C    PRO B 447      29.727  -7.856  45.134  1.00 39.33           C
ATOM   3709  O    PRO B 447      28.646  -7.884  45.720  1.00 37.02           O
ATOM   3710  N    GLU B 448      30.846  -8.349  45.661  1.00 39.44           N
ATOM   3711  CA   GLU B 448      30.888  -8.971  46.983  1.00 39.30           C
ATOM   3712  CB   GLU B 448      32.155  -9.807  47.126  1.00 41.83           C
ATOM   3713  CG   GLU B 448      31.902 -11.281  47.343  1.00 45.80           C
ATOM   3714  CD   GLU B 448      32.994 -12.135  46.741  1.00 46.81           C
ATOM   3715  OE1  GLU B 448      34.167 -11.964  47.134  1.00 49.50           O
ATOM   3716  OE2  GLU B 448      32.679 -12.970  45.867  1.00 48.78           O
ATOM   3717  C    GLU B 448      30.890  -7.889  48.049  1.00 39.13           C
ATOM   3718  O    GLU B 448      30.340  -8.068  49.146  1.00 35.73           O
ATOM   3719  N    VAL B 449      31.534  -6.775  47.721  1.00 36.33           N
ATOM   3720  CA   VAL B 449      31.589  -5.651  48.636  1.00 36.74           C
ATOM   3721  CB   VAL B 449      32.606  -4.585  48.151  1.00 36.44           C
ATOM   3722  CG1  VAL B 449      32.532  -3.339  49.029  1.00 34.54           C
ATOM   3723  CG2  VAL B 449      34.011  -5.163  48.200  1.00 34.82           C
ATOM   3724  C    VAL B 449      30.187  -5.061  48.679  1.00 35.77           C
ATOM   3725  O    VAL B 449      29.621  -4.862  49.750  1.00 35.11           O
ATOM   3726  N    ILE B 450      29.626  -4.810  47.500  1.00 35.78           N
ATOM   3727  CA   ILE B 450      28.288  -4.241  47.386  1.00 37.98           C
ATOM   3728  CB   ILE B 450      27.840  -4.191  45.909  1.00 37.91           C
ATOM   3729  CG2  ILE B 450      26.404  -3.711  45.808  1.00 38.39           C
ATOM   3730  CG1  ILE B 450      28.792  -3.302  45.097  1.00 41.08           C
ATOM   3731  CD1  ILE B 450      28.799  -1.851  45.499  1.00 41.48           C
ATOM   3732  C    ILE B 450      27.273  -5.059  48.194  1.00 36.75           C
ATOM   3733  O    ILE B 450      26.459  -4.502  48.920  1.00 35.96           O
ATOM   3734  N    GLN B 451      27.319  -6.382  48.061  1.00 36.87           N
ATOM   3735  CA   GLN B 451      26.390  -7.232  48.801  1.00 36.46           C
ATOM   3736  CB   GLN B 451      26.497  -8.682  48.323  1.00 39.96           C
ATOM   3737  CG   GLN B 451      25.851  -8.900  46.957  1.00 43.51           C
ATOM   3738  CD   GLN B 451      26.280 -10.193  46.301  1.00 46.53           C
ATOM   3739  OE1  GLN B 451      26.261 -11.250  46.925  1.00 48.19           O
ATOM   3740  NE2  GLN B 451      26.659 -10.116  45.023  1.00 48.37           N
ATOM   3741  C    GLN B 451      26.643  -7.156  50.294  1.00 33.18           C
ATOM   3742  O    GLN B 451      25.717  -7.224  51.087  1.00 31.09           O
ATOM   3743  N    ASN B 452      27.905  -7.010  50.677  1.00 33.46           N
ATOM   3744  CA   ASN B 452      28.261  -6.924  52.085  1.00 32.51           C
ATOM   3745  CB   ASN B 452      29.762  -7.166  52.251  1.00 34.24           C
ATOM   3746  CG   ASN B 452      30.074  -8.613  52.583  1.00 38.07           C
ATOM   3747  OD1  ASN B 452      29.853  -9.059  53.706  1.00 35.00           O
ATOM   3748  ND2  ASN B 452      30.572  -9.362  51.595  1.00 39.00           N
ATOM   3749  C    ASN B 452      27.840  -5.602  52.730  1.00 32.64           C
ATOM   3750  O    ASN B 452      27.375  -5.590  53.870  1.00 30.71           O
ATOM   3751  N    LEU B 453      28.000  -4.495  52.005  1.00 31.35           N
ATOM   3752  CA   LEU B 453      27.599  -3.185  52.517  1.00 29.35           C
ATOM   3753  CB   LEU B 453      28.037  -2.076  51.549  1.00 30.09           C
ATOM   3754  CG   LEU B 453      29.544  -1.826  51.585  1.00 31.23           C
ATOM   3755  CD1  LEU B 453      29.959  -0.797  50.522  1.00 32.23           C
ATOM   3756  CD2  LEU B 453      29.915  -1.365  52.987  1.00 32.13           C
ATOM   3757  C    LEU B 453      26.090  -3.146  52.683  1.00 28.20           C
ATOM   3758  O    LEU B 453      25.574  -2.477  53.572  1.00 27.37           O
ATOM   3759  N    GLU B 454      25.385  -3.863  51.815  1.00 29.57           N
ATOM   3760  CA   GLU B 454      23.932  -3.918  51.879  1.00 32.24           C
```

Figure 14

| | | | | | | | | | |
|---|---|---|---|---|---|---|---|---|---|
| ATOM | 3761 | CB | GLU | B | 454 | 23.400 | -4.827 | 50.758 | 1.00 34.69 | C |
| ATOM | 3762 | CG | GLU | B | 454 | 23.650 | -4.256 | 49.351 | 1.00 41.92 | C |
| ATOM | 3763 | CD | GLU | B | 454 | 23.223 | -5.182 | 48.209 | 1.00 45.82 | C |
| ATOM | 3764 | OE1 | GLU | B | 454 | 22.684 | -6.281 | 48.481 | 1.00 47.58 | O |
| ATOM | 3765 | OE2 | GLU | B | 454 | 23.430 | -4.801 | 47.033 | 1.00 48.35 | O |
| ATOM | 3766 | C | GLU | B | 454 | 23.550 | -4.459 | 53.270 | 1.00 32.28 | C |
| ATOM | 3767 | O | GLU | B | 454 | 22.542 | -4.052 | 53.859 | 1.00 31.21 | O |
| ATOM | 3768 | N | ARG | B | 455 | 24.388 | -5.351 | 53.799 | 1.00 30.88 | N |
| ATOM | 3769 | CA | ARG | B | 455 | 24.156 | -5.931 | 55.125 | 1.00 32.26 | C |
| ATOM | 3770 | CB | ARG | B | 455 | 24.686 | -7.369 | 55.197 | 1.00 34.73 | C |
| ATOM | 3771 | CG | ARG | B | 455 | 24.210 | -8.313 | 54.124 | 1.00 39.09 | C |
| ATOM | 3772 | CD | ARG | B | 455 | 24.615 | -9.745 | 54.492 | 1.00 40.99 | C |
| ATOM | 3773 | NE | ARG | B | 455 | 24.525 | -10.642 | 53.351 | 1.00 46.75 | N |
| ATOM | 3774 | CZ | ARG | B | 455 | 25.569 | -11.033 | 52.632 | 1.00 46.44 | C |
| ATOM | 3775 | NH1 | ARG | B | 455 | 26.787 | -10.609 | 52.942 | 1.00 46.57 | N |
| ATOM | 3776 | NH2 | ARG | B | 455 | 25.389 | -11.834 | 51.592 | 1.00 49.99 | N |
| ATOM | 3777 | C | ARG | B | 455 | 24.836 | -5.130 | 56.249 | 1.00 29.85 | C |
| ATOM | 3778 | O | ARG | B | 455 | 24.896 | -5.604 | 57.379 | 1.00 27.72 | O |
| ATOM | 3779 | N | GLY | B | 456 | 25.377 | -3.948 | 55.938 | 1.00 29.05 | N |
| ATOM | 3780 | CA | GLY | B | 456 | 26.010 | -3.133 | 56.970 | 1.00 27.21 | C |
| ATOM | 3781 | C | GLY | B | 456 | 27.420 | -3.538 | 57.374 | 1.00 28.51 | C |
| ATOM | 3782 | O | GLY | B | 456 | 27.960 | -3.049 | 58.359 | 1.00 28.27 | O |
| ATOM | 3783 | N | TYR | B | 457 | 28.040 | -4.414 | 56.597 | 1.00 26.98 | N |
| ATOM | 3784 | CA | TYR | B | 457 | 29.390 | -4.863 | 56.895 | 1.00 29.78 | C |
| ATOM | 3785 | CB | TYR | B | 457 | 29.812 | -5.887 | 55.838 | 1.00 29.53 | C |
| ATOM | 3786 | CG | TYR | B | 457 | 31.224 | -6.375 | 55.978 | 1.00 30.71 | C |
| ATOM | 3787 | CD2 | TYR | B | 457 | 32.271 | -5.750 | 55.301 | 1.00 32.89 | C |
| ATOM | 3788 | CE2 | TYR | B | 457 | 33.580 | -6.228 | 55.401 | 1.00 32.61 | C |
| ATOM | 3789 | CD1 | TYR | B | 457 | 31.515 | -7.489 | 56.764 | 1.00 31.20 | C |
| ATOM | 3790 | CE1 | TYR | B | 457 | 32.810 | -7.976 | 56.875 | 1.00 32.03 | C |
| ATOM | 3791 | CZ | TYR | B | 457 | 33.840 | -7.340 | 56.189 | 1.00 33.88 | C |
| ATOM | 3792 | OH | TYR | B | 457 | 35.126 | -7.808 | 56.305 | 1.00 32.61 | O |
| ATOM | 3793 | C | TYR | B | 457 | 30.436 | -3.734 | 56.951 | 1.00 28.66 | C |
| ATOM | 3794 | O | TYR | B | 457 | 30.399 | -2.800 | 56.148 | 1.00 28.56 | O |
| ATOM | 3795 | N | ARG | B | 458 | 31.369 | -3.843 | 57.892 | 1.00 26.75 | N |
| ATOM | 3796 | CA | ARG | B | 458 | 32.458 | -2.871 | 58.045 | 1.00 30.39 | C |
| ATOM | 3797 | CB | ARG | B | 458 | 32.245 | -1.979 | 59.282 | 1.00 28.33 | C |
| ATOM | 3798 | CG | ARG | B | 458 | 31.063 | -1.014 | 59.197 | 1.00 28.57 | C |
| ATOM | 3799 | CD | ARG | B | 458 | 31.287 | 0.027 | 58.109 | 1.00 32.68 | C |
| ATOM | 3800 | NE | ARG | B | 458 | 30.154 | 0.935 | 57.929 | 1.00 30.09 | N |
| ATOM | 3801 | CZ | ARG | B | 458 | 29.039 | 0.646 | 57.267 | 1.00 27.90 | C |
| ATOM | 3802 | NH1 | ARG | B | 458 | 28.868 | -0.542 | 56.704 | 1.00 32.08 | N |
| ATOM | 3803 | NH2 | ARG | B | 458 | 28.094 | 1.562 | 57.152 | 1.00 29.06 | N |
| ATOM | 3804 | C | ARG | B | 458 | 33.735 | -3.690 | 58.238 | 1.00 30.65 | C |
| ATOM | 3805 | O | ARG | B | 458 | 33.687 | -4.736 | 58.882 | 1.00 31.91 | O |
| ATOM | 3806 | N | MET | B | 459 | 34.855 | -3.239 | 57.673 | 1.00 29.39 | N |
| ATOM | 3807 | CA | MET | B | 459 | 36.130 | -3.940 | 57.832 | 1.00 29.83 | C |
| ATOM | 3808 | CB | MET | B | 459 | 37.256 | -3.262 | 57.022 | 1.00 27.86 | C |
| ATOM | 3809 | CG | MET | B | 459 | 37.204 | -3.436 | 55.503 | 1.00 30.36 | C |
| ATOM | 3810 | SD | MET | B | 459 | 38.710 | -2.787 | 54.634 | 1.00 31.51 | S |
| ATOM | 3811 | CE | MET | B | 459 | 38.288 | -1.060 | 54.490 | 1.00 33.90 | C |
| ATOM | 3812 | C | MET | B | 459 | 36.532 | -3.943 | 59.302 | 1.00 31.14 | C |
| ATOM | 3813 | O | MET | B | 459 | 36.179 | -3.036 | 60.050 | 1.00 31.91 | O |
| ATOM | 3814 | N | VAL | B | 460 | 37.285 | -4.962 | 59.709 | 1.00 33.77 | N |
| ATOM | 3815 | CA | VAL | B | 460 | 37.749 | -5.078 | 61.086 | 1.00 34.11 | C |
| ATOM | 3816 | CB | VAL | B | 460 | 38.026 | -6.553 | 61.462 | 1.00 34.98 | C |
| ATOM | 3817 | CG1 | VAL | B | 460 | 36.805 | -7.406 | 61.153 | 1.00 37.54 | C |
| ATOM | 3818 | CG2 | VAL | B | 460 | 39.231 | -7.072 | 60.692 | 1.00 35.80 | C |
| ATOM | 3819 | C | VAL | B | 460 | 39.048 | -4.285 | 61.206 | 1.00 34.24 | C |
| ATOM | 3820 | O | VAL | B | 460 | 39.603 | -3.853 | 60.196 | 1.00 33.74 | O |

Figure 14

| ATOM | 3821 | N   | ARG | B | 461 | 39.541 | -4.110 | 62.428 | 1.00 | 34.04 | N |
| ATOM | 3822 | CA  | ARG | B | 461 | 40.773 | -3.365 | 62.640 | 1.00 | 36.06 | C |
| ATOM | 3823 | CB  | ARG | B | 461 | 41.036 | -3.193 | 64.136 | 1.00 | 37.80 | C |
| ATOM | 3824 | CG  | ARG | B | 461 | 42.235 | -2.307 | 64.450 | 1.00 | 38.86 | C |
| ATOM | 3825 | CD  | ARG | B | 461 | 42.313 | -2.012 | 65.937 | 1.00 | 41.20 | C |
| ATOM | 3826 | NE  | ARG | B | 461 | 42.421 | -3.227 | 66.741 | 1.00 | 45.69 | N |
| ATOM | 3827 | CZ  | ARG | B | 461 | 43.488 | -4.020 | 66.759 | 1.00 | 48.58 | C |
| ATOM | 3828 | NH1 | ARG | B | 461 | 44.546 | -3.727 | 66.010 | 1.00 | 50.24 | N |
| ATOM | 3829 | NH2 | ARG | B | 461 | 43.509 | -5.093 | 67.538 | 1.00 | 48.06 | N |
| ATOM | 3830 | C   | ARG | B | 461 | 41.979 | -4.019 | 61.962 | 1.00 | 36.15 | C |
| ATOM | 3831 | O   | ARG | B | 461 | 42.278 | -5.192 | 62.177 | 1.00 | 34.27 | O |
| ATOM | 3832 | N   | PRO | B | 462 | 42.683 | -3.267 | 61.108 | 1.00 | 37.42 | N |
| ATOM | 3833 | CD  | PRO | B | 462 | 42.346 | -1.982 | 60.478 | 1.00 | 36.85 | C |
| ATOM | 3834 | CA  | PRO | B | 462 | 43.841 | -3.876 | 60.450 | 1.00 | 38.60 | C |
| ATOM | 3835 | CB  | PRO | B | 462 | 44.254 | -2.812 | 59.439 | 1.00 | 38.58 | C |
| ATOM | 3836 | CG  | PRO | B | 462 | 42.951 | -2.146 | 59.119 | 1.00 | 34.49 | C |
| ATOM | 3837 | C   | PRO | B | 462 | 44.946 | -4.180 | 61.454 | 1.00 | 40.50 | C |
| ATOM | 3838 | O   | PRO | B | 462 | 44.970 | -3.608 | 62.549 | 1.00 | 38.75 | O |
| ATOM | 3839 | N   | ASP | B | 463 | 45.843 | -5.093 | 61.091 | 1.00 | 42.58 | N |
| ATOM | 3840 | CA  | ASP | B | 463 | 46.948 | -5.432 | 61.970 | 1.00 | 46.19 | C |
| ATOM | 3841 | CB  | ASP | B | 463 | 47.741 | -6.632 | 61.433 | 1.00 | 46.96 | C |
| ATOM | 3842 | CG  | ASP | B | 463 | 46.965 | -7.929 | 61.514 | 1.00 | 47.12 | C |
| ATOM | 3843 | OD1 | ASP | B | 463 | 46.351 | -8.207 | 62.573 | 1.00 | 47.52 | O |
| ATOM | 3844 | OD2 | ASP | B | 463 | 46.982 | -8.680 | 60.519 | 1.00 | 48.79 | O |
| ATOM | 3845 | C   | ASP | B | 463 | 47.870 | -4.225 | 62.092 | 1.00 | 47.26 | C |
| ATOM | 3846 | O   | ASP | B | 463 | 48.163 | -3.540 | 61.103 | 1.00 | 47.57 | O |
| ATOM | 3847 | N   | ASN | B | 464 | 48.319 | -3.969 | 63.312 | 1.00 | 48.14 | N |
| ATOM | 3848 | CA  | ASN | B | 464 | 49.200 | -2.851 | 63.577 | 1.00 | 49.67 | C |
| ATOM | 3849 | CB  | ASN | B | 464 | 50.517 | -3.035 | 62.827 | 1.00 | 52.24 | C |
| ATOM | 3850 | CG  | ASN | B | 464 | 51.256 | -4.292 | 63.263 | 1.00 | 53.94 | C |
| ATOM | 3851 | OD1 | ASN | B | 464 | 51.518 | -4.493 | 64.451 | 1.00 | 53.32 | O |
| ATOM | 3852 | ND2 | ASN | B | 464 | 51.593 | -5.143 | 62.303 | 1.00 | 55.77 | N |
| ATOM | 3853 | C   | ASN | B | 464 | 48.538 | -1.527 | 63.211 | 1.00 | 50.04 | C |
| ATOM | 3854 | O   | ASN | B | 464 | 49.104 | -0.697 | 62.489 | 1.00 | 51.43 | O |
| ATOM | 3855 | N   | CYS | B | 465 | 47.318 | -1.358 | 63.709 | 1.00 | 47.88 | N |
| ATOM | 3856 | CA  | CYS | B | 465 | 46.544 | -0.143 | 63.515 | 1.00 | 44.72 | C |
| ATOM | 3857 | CB  | CYS | B | 465 | 45.328 | -0.377 | 62.618 | 1.00 | 44.00 | C |
| ATOM | 3858 | SG  | CYS | B | 465 | 44.123 |  0.989 | 62.718 | 1.00 | 39.33 | S |
| ATOM | 3859 | C   | CYS | B | 465 | 46.053 |  0.275 | 64.888 | 1.00 | 43.38 | C |
| ATOM | 3860 | O   | CYS | B | 465 | 45.284 | -0.445 | 65.519 | 1.00 | 44.40 | O |
| ATOM | 3861 | N   | PRO | B | 466 | 46.504 |  1.434 | 65.377 | 1.00 | 41.31 | N |
| ATOM | 3862 | CD  | PRO | B | 466 | 47.528 |  2.342 | 64.830 | 1.00 | 41.93 | C |
| ATOM | 3863 | CA  | PRO | B | 466 | 46.057 |  1.885 | 66.694 | 1.00 | 41.55 | C |
| ATOM | 3864 | CB  | PRO | B | 466 | 46.576 |  3.314 | 66.758 | 1.00 | 41.36 | C |
| ATOM | 3865 | CG  | PRO | B | 466 | 47.888 |  3.195 | 66.048 | 1.00 | 42.06 | C |
| ATOM | 3866 | C   | PRO | B | 466 | 44.543 |  1.806 | 66.813 | 1.00 | 40.99 | C |
| ATOM | 3867 | O   | PRO | B | 466 | 43.813 |  2.152 | 65.879 | 1.00 | 39.27 | O |
| ATOM | 3868 | N   | GLU | B | 467 | 44.084 |  1.334 | 67.964 | 1.00 | 39.58 | N |
| ATOM | 3869 | CA  | GLU | B | 467 | 42.666 |  1.198 | 68.236 | 1.00 | 39.97 | C |
| ATOM | 3870 | CB  | GLU | B | 467 | 42.460 |  0.784 | 69.690 | 1.00 | 42.12 | C |
| ATOM | 3871 | CG  | GLU | B | 467 | 41.500 | -0.371 | 69.866 | 1.00 | 48.07 | C |
| ATOM | 3872 | CD  | GLU | B | 467 | 40.103 | -0.049 | 69.384 | 1.00 | 50.37 | C |
| ATOM | 3873 | OE1 | GLU | B | 467 | 39.510 |  0.928 | 69.896 | 1.00 | 54.29 | O |
| ATOM | 3874 | OE2 | GLU | B | 467 | 39.596 | -0.772 | 68.498 | 1.00 | 51.66 | O |
| ATOM | 3875 | C   | GLU | B | 467 | 41.930 |  2.505 | 67.974 | 1.00 | 38.34 | C |
| ATOM | 3876 | O   | GLU | B | 467 | 40.883 |  2.521 | 67.342 | 1.00 | 37.25 | O |
| ATOM | 3877 | N   | GLU | B | 468 | 42.481 |  3.604 | 68.467 | 1.00 | 37.71 | N |
| ATOM | 3878 | CA  | GLU | B | 468 | 41.844 |  4.900 | 68.281 | 1.00 | 39.01 | C |
| ATOM | 3879 | CB  | GLU | B | 468 | 42.650 |  5.979 | 69.010 | 1.00 | 41.82 | C |
| ATOM | 3880 | CG  | GLU | B | 468 | 43.152 |  5.542 | 70.387 | 1.00 | 44.79 | C |

Figure 14

```
ATOM   3881  CD   GLU B 468      44.495   4.826  70.320  1.00 47.78           C
ATOM   3882  OE1  GLU B 468      45.523   5.515  70.144  1.00 49.30           O
ATOM   3883  OE2  GLU B 468      44.526   3.578  70.432  1.00 48.28           O
ATOM   3884  C    GLU B 468      41.712   5.234  66.789  1.00 37.33           C
ATOM   3885  O    GLU B 468      40.751   5.870  66.368  1.00 37.72           O
ATOM   3886  N    LEU B 469      42.676   4.798  65.988  1.00 36.18           N
ATOM   3887  CA   LEU B 469      42.622   5.062  64.552  1.00 34.02           C
ATOM   3888  CB   LEU B 469      43.934   4.661  63.876  1.00 33.88           C
ATOM   3889  CG   LEU B 469      43.963   5.005  62.383  1.00 35.77           C
ATOM   3890  CD1  LEU B 469      43.627   6.494  62.197  1.00 35.89           C
ATOM   3891  CD2  LEU B 469      45.338   4.679  61.802  1.00 33.60           C
ATOM   3892  C    LEU B 469      41.462   4.297  63.919  1.00 33.08           C
ATOM   3893  O    LEU B 469      40.738   4.835  63.070  1.00 31.81           O
ATOM   3894  N    TYR B 470      41.288   3.038  64.322  1.00 30.86           N
ATOM   3895  CA   TYR B 470      40.188   2.233  63.790  1.00 30.79           C
ATOM   3896  CB   TYR B 470      40.224   0.801  64.349  1.00 30.69           C
ATOM   3897  CG   TYR B 470      39.070  -0.069  63.883  1.00 30.68           C
ATOM   3898  CD1  TYR B 470      38.879  -0.342  62.528  1.00 29.79           C
ATOM   3899  CE1  TYR B 470      37.835  -1.152  62.090  1.00 29.23           C
ATOM   3900  CD2  TYR B 470      38.174  -0.633  64.801  1.00 33.14           C
ATOM   3901  CE2  TYR B 470      37.115  -1.454  64.372  1.00 31.84           C
ATOM   3902  CZ   TYR B 470      36.955  -1.708  63.015  1.00 31.96           C
ATOM   3903  OH   TYR B 470      35.932  -2.525  62.571  1.00 30.47           O
ATOM   3904  C    TYR B 470      38.853   2.885  64.154  1.00 30.14           C
ATOM   3905  O    TYR B 470      37.919   2.875  63.359  1.00 29.84           O
ATOM   3906  N    GLN B 471      38.756   3.455  65.352  1.00 29.09           N
ATOM   3907  CA   GLN B 471      37.506   4.096  65.740  1.00 30.89           C
ATOM   3908  CB   GLN B 471      37.532   4.485  67.226  1.00 32.99           C
ATOM   3909  CG   GLN B 471      37.559   3.282  68.176  1.00 37.72           C
ATOM   3910  CD   GLN B 471      36.291   2.448  68.085  1.00 41.81           C
ATOM   3911  OE1  GLN B 471      35.181   2.964  68.255  1.00 44.05           O
ATOM   3912  NE2  GLN B 471      36.446   1.153  67.810  1.00 41.90           N
ATOM   3913  C    GLN B 471      37.252   5.320  64.852  1.00 29.06           C
ATOM   3914  O    GLN B 471      36.107   5.611  64.501  1.00 28.86           O
ATOM   3915  N    LEU B 472      38.315   6.020  64.465  1.00 28.50           N
ATOM   3916  CA   LEU B 472      38.152   7.182  63.588  1.00 28.79           C
ATOM   3917  CB   LEU B 472      39.490   7.901  63.396  1.00 31.12           C
ATOM   3918  CG   LEU B 472      39.416   9.401  63.082  1.00 33.11           C
ATOM   3919  CD1  LEU B 472      38.717  10.120  64.239  1.00 30.32           C
ATOM   3920  CD2  LEU B 472      40.826   9.965  62.879  1.00 36.15           C
ATOM   3921  C    LEU B 472      37.631   6.640  62.253  1.00 28.77           C
ATOM   3922  O    LEU B 472      36.746   7.225  61.624  1.00 28.28           O
ATOM   3923  N    MET B 473      38.170   5.501  61.835  1.00 27.66           N
ATOM   3924  CA   MET B 473      37.727   4.875  60.597  1.00 26.63           C
ATOM   3925  CB   MET B 473      38.476   3.568  60.351  1.00 29.55           C
ATOM   3926  CG   MET B 473      39.970   3.696  60.061  1.00 29.98           C
ATOM   3927  SD   MET B 473      40.638   2.022  59.899  1.00 34.37           S
ATOM   3928  CE   MET B 473      42.362   2.367  59.473  1.00 32.33           C
ATOM   3929  C    MET B 473      36.234   4.564  60.645  1.00 26.83           C
ATOM   3930  O    MET B 473      35.511   4.841  59.689  1.00 26.06           O
ATOM   3931  N    ARG B 474      35.774   3.985  61.758  1.00 27.06           N
ATOM   3932  CA   ARG B 474      34.363   3.619  61.899  1.00 27.84           C
ATOM   3933  CB   ARG B 474      34.128   2.849  63.209  1.00 29.52           C
ATOM   3934  CG   ARG B 474      34.857   1.496  63.297  1.00 31.75           C
ATOM   3935  CD   ARG B 474      34.483   0.585  62.132  1.00 33.57           C
ATOM   3936  NE   ARG B 474      33.062   0.272  62.121  1.00 31.76           N
ATOM   3937  CZ   ARG B 474      32.519  -0.785  62.725  1.00 34.66           C
ATOM   3938  NH1  ARG B 474      33.283  -1.646  63.388  1.00 29.81           N
ATOM   3939  NH2  ARG B 474      31.205  -0.969  62.677  1.00 31.13           N
ATOM   3940  C    ARG B 474      33.465   4.854  61.849  1.00 26.60           C
```

Figure 14

| | | | | | | | | | | |
|---|---|---|---|---|---|---|---|---|---|---|
| ATOM | 3941 | O | ARG | B | 474 | 32.309 | 4.782 | 61.436 | 1.00 24.33 | O |
| ATOM | 3942 | N | LEU | B | 475 | 34.002 | 5.993 | 62.265 | 1.00 26.11 | N |
| ATOM | 3943 | CA | LEU | B | 475 | 33.229 | 7.225 | 62.222 | 1.00 26.20 | C |
| ATOM | 3944 | CB | LEU | B | 475 | 33.913 | 8.322 | 63.044 | 1.00 27.46 | C |
| ATOM | 3945 | CG | LEU | B | 475 | 33.942 | 8.101 | 64.561 | 1.00 32.19 | C |
| ATOM | 3946 | CD1 | LEU | B | 475 | 34.654 | 9.270 | 65.217 | 1.00 32.97 | C |
| ATOM | 3947 | CD2 | LEU | B | 475 | 32.516 | 7.976 | 65.111 | 1.00 33.53 | C |
| ATOM | 3948 | C | LEU | B | 475 | 33.074 | 7.665 | 60.767 | 1.00 23.90 | C |
| ATOM | 3949 | O | LEU | B | 475 | 32.028 | 8.202 | 60.382 | 1.00 26.95 | O |
| ATOM | 3950 | N | CYS | B | 476 | 34.110 | 7.420 | 59.960 | 1.00 25.24 | N |
| ATOM | 3951 | CA | CYS | B | 476 | 34.077 | 7.782 | 58.546 | 1.00 25.08 | C |
| ATOM | 3952 | CB | CYS | B | 476 | 35.464 | 7.635 | 57.896 | 1.00 24.68 | C |
| ATOM | 3953 | SG | CYS | B | 476 | 36.736 | 8.742 | 58.537 | 1.00 29.95 | S |
| ATOM | 3954 | C | CYS | B | 476 | 33.093 | 6.896 | 57.805 | 1.00 24.50 | C |
| ATOM | 3955 | O | CYS | B | 476 | 32.541 | 7.291 | 56.776 | 1.00 22.87 | O |
| ATOM | 3956 | N | TRP | B | 477 | 32.889 | 5.688 | 58.329 | 1.00 25.41 | N |
| ATOM | 3957 | CA | TRP | B | 477 | 31.980 | 4.742 | 57.698 | 1.00 28.02 | C |
| ATOM | 3958 | CB | TRP | B | 477 | 32.593 | 3.336 | 57.674 | 1.00 27.74 | C |
| ATOM | 3959 | CG | TRP | B | 477 | 33.965 | 3.274 | 57.099 | 1.00 28.15 | C |
| ATOM | 3960 | CD2 | TRP | B | 477 | 35.000 | 2.353 | 57.463 | 1.00 27.48 | C |
| ATOM | 3961 | CE2 | TRP | B | 477 | 36.115 | 2.635 | 56.648 | 1.00 26.56 | C |
| ATOM | 3962 | CE3 | TRP | B | 477 | 35.091 | 1.312 | 58.394 | 1.00 25.73 | C |
| ATOM | 3963 | CD1 | TRP | B | 477 | 34.479 | 4.058 | 56.104 | 1.00 28.10 | C |
| ATOM | 3964 | NE1 | TRP | B | 477 | 35.774 | 3.681 | 55.831 | 1.00 26.56 | N |
| ATOM | 3965 | CZ2 | TRP | B | 477 | 37.306 | 1.912 | 56.735 | 1.00 26.67 | C |
| ATOM | 3966 | CZ3 | TRP | B | 477 | 36.278 | 0.597 | 58.481 | 1.00 25.85 | C |
| ATOM | 3967 | CH2 | TRP | B | 477 | 37.369 | 0.903 | 57.655 | 1.00 27.30 | C |
| ATOM | 3968 | C | TRP | B | 477 | 30.584 | 4.663 | 58.328 | 1.00 29.25 | C |
| ATOM | 3969 | O | TRP | B | 477 | 29.911 | 3.626 | 58.240 | 1.00 27.44 | O |
| ATOM | 3970 | N | LYS | B | 478 | 30.139 | 5.737 | 58.971 | 1.00 28.05 | N |
| ATOM | 3971 | CA | LYS | B | 478 | 28.796 | 5.701 | 59.542 | 1.00 29.52 | C |
| ATOM | 3972 | CB | LYS | B | 478 | 28.484 | 6.996 | 60.293 | 1.00 27.93 | C |
| ATOM | 3973 | CG | LYS | B | 478 | 29.027 | 7.008 | 61.702 | 1.00 29.09 | C |
| ATOM | 3974 | CD | LYS | B | 478 | 28.392 | 5.885 | 62.504 | 1.00 35.41 | C |
| ATOM | 3975 | CE | LYS | B | 478 | 28.979 | 5.773 | 63.888 | 1.00 38.26 | C |
| ATOM | 3976 | NZ | LYS | B | 478 | 28.647 | 4.423 | 64.455 | 1.00 45.67 | N |
| ATOM | 3977 | C | LYS | B | 478 | 27.862 | 5.539 | 58.348 | 1.00 29.74 | C |
| ATOM | 3978 | O | LYS | B | 478 | 28.147 | 6.060 | 57.265 | 1.00 28.37 | O |
| ATOM | 3979 | N | GLU | B | 479 | 26.763 | 4.815 | 58.536 | 1.00 28.86 | N |
| ATOM | 3980 | CA | GLU | B | 479 | 25.811 | 4.583 | 57.449 | 1.00 28.31 | C |
| ATOM | 3981 | CB | GLU | B | 479 | 24.695 | 3.634 | 57.900 | 1.00 29.74 | C |
| ATOM | 3982 | CG | GLU | B | 479 | 23.774 | 3.143 | 56.770 | 1.00 31.70 | C |
| ATOM | 3983 | CD | GLU | B | 479 | 24.497 | 2.243 | 55.766 | 1.00 31.99 | C |
| ATOM | 3984 | OE1 | GLU | B | 479 | 25.446 | 1.530 | 56.176 | 1.00 28.87 | O |
| ATOM | 3985 | OE2 | GLU | B | 479 | 24.108 | 2.238 | 54.576 | 1.00 30.89 | O |
| ATOM | 3986 | C | GLU | B | 479 | 25.195 | 5.899 | 56.982 | 1.00 28.58 | C |
| ATOM | 3987 | O | GLU | B | 479 | 25.097 | 6.150 | 55.784 | 1.00 28.55 | O |
| ATOM | 3988 | N | ARG | B | 480 | 24.765 | 6.729 | 57.924 | 1.00 28.93 | N |
| ATOM | 3989 | CA | ARG | B | 480 | 24.176 | 8.015 | 57.570 | 1.00 32.20 | C |
| ATOM | 3990 | CB | ARG | B | 480 | 23.263 | 8.499 | 58.692 | 1.00 34.18 | C |
| ATOM | 3991 | CG | ARG | B | 480 | 22.030 | 7.602 | 58.930 | 1.00 39.46 | C |
| ATOM | 3992 | CD | ARG | B | 480 | 21.206 | 8.094 | 60.118 | 1.00 44.02 | C |
| ATOM | 3993 | NE | ARG | B | 480 | 19.955 | 7.352 | 60.261 | 1.00 49.31 | N |
| ATOM | 3994 | CZ | ARG | B | 480 | 19.068 | 7.554 | 61.232 | 1.00 51.49 | C |
| ATOM | 3995 | NH1 | ARG | B | 480 | 19.289 | 8.478 | 62.159 | 1.00 53.49 | N |
| ATOM | 3996 | NH2 | ARG | B | 480 | 17.954 | 6.833 | 61.276 | 1.00 53.24 | N |
| ATOM | 3997 | C | ARG | B | 480 | 25.313 | 9.018 | 57.350 | 1.00 28.43 | C |
| ATOM | 3998 | O | ARG | B | 480 | 26.182 | 9.160 | 58.200 | 1.00 29.70 | O |
| ATOM | 3999 | N | PRO | B | 481 | 25.314 | 9.731 | 56.212 | 1.00 28.22 | N |
| ATOM | 4000 | CD | PRO | B | 481 | 24.362 | 9.660 | 55.093 | 1.00 28.90 | C |

Figure 14

| ATOM | 4001 | CA  | PRO | B | 481 | 26.370 | 10.707 | 55.924 | 1.00 | 27.49 | C |
|------|------|-----|-----|---|-----|--------|--------|--------|------|-------|---|
| ATOM | 4002 | CB  | PRO | B | 481 | 25.963 | 11.262 | 54.553 | 1.00 | 28.25 | C |
| ATOM | 4003 | CG  | PRO | B | 481 | 25.207 | 10.141 | 53.946 | 1.00 | 31.47 | C |
| ATOM | 4004 | C   | PRO | B | 481 | 26.519 | 11.812 | 56.980 | 1.00 | 26.90 | C |
| ATOM | 4005 | O   | PRO | B | 481 | 27.632 | 12.220 | 57.304 | 1.00 | 23.43 | O |
| ATOM | 4006 | N   | GLU | B | 482 | 25.405 | 12.285 | 57.531 | 1.00 | 28.04 | N |
| ATOM | 4007 | CA  | GLU | B | 482 | 25.471 | 13.354 | 58.530 | 1.00 | 28.72 | C |
| ATOM | 4008 | CB  | GLU | B | 482 | 24.058 | 13.867 | 58.860 | 1.00 | 33.41 | C |
| ATOM | 4009 | CG  | GLU | B | 482 | 23.179 | 12.849 | 59.577 | 1.00 | 34.29 | C |
| ATOM | 4010 | CD  | GLU | B | 482 | 22.321 | 12.019 | 58.635 | 1.00 | 36.63 | C |
| ATOM | 4011 | OE1 | GLU | B | 482 | 22.712 | 11.793 | 57.470 | 1.00 | 36.69 | O |
| ATOM | 4012 | OE2 | GLU | B | 482 | 21.240 | 11.581 | 59.076 | 1.00 | 40.47 | O |
| ATOM | 4013 | C   | GLU | B | 482 | 26.186 | 12.919 | 59.815 | 1.00 | 29.01 | C |
| ATOM | 4014 | O   | GLU | B | 482 | 26.623 | 13.765 | 60.605 | 1.00 | 27.80 | O |
| ATOM | 4015 | N   | ASP | B | 483 | 26.303 | 11.608 | 60.039 | 1.00 | 27.65 | N |
| ATOM | 4016 | CA  | ASP | B | 483 | 26.993 | 11.120 | 61.229 | 1.00 | 27.38 | C |
| ATOM | 4017 | CB  | ASP | B | 483 | 26.393 |  9.794 | 61.700 | 1.00 | 29.12 | C |
| ATOM | 4018 | CG  | ASP | B | 483 | 24.963 |  9.959 | 62.195 | 1.00 | 33.72 | C |
| ATOM | 4019 | OD1 | ASP | B | 483 | 24.743 | 10.807 | 63.086 | 1.00 | 32.73 | O |
| ATOM | 4020 | OD2 | ASP | B | 483 | 24.069 |  9.252 | 61.697 | 1.00 | 32.66 | O |
| ATOM | 4021 | C   | ASP | B | 483 | 28.511 | 10.968 | 61.034 | 1.00 | 27.91 | C |
| ATOM | 4022 | O   | ASP | B | 483 | 29.231 | 10.674 | 61.983 | 1.00 | 26.95 | O |
| ATOM | 4023 | N   | ARG | B | 484 | 28.993 | 11.172 | 59.810 | 1.00 | 25.90 | N |
| ATOM | 4024 | CA  | ARG | B | 484 | 30.435 | 11.090 | 59.544 | 1.00 | 26.31 | C |
| ATOM | 4025 | CB  | ARG | B | 484 | 30.693 | 10.754 | 58.077 | 1.00 | 28.04 | C |
| ATOM | 4026 | CG  | ARG | B | 484 | 30.107 |  9.427 | 57.644 | 1.00 | 25.56 | C |
| ATOM | 4027 | CD  | ARG | B | 484 | 30.135 |  9.275 | 56.155 | 1.00 | 24.34 | C |
| ATOM | 4028 | NE  | ARG | B | 484 | 29.122 |  8.315 | 55.745 | 1.00 | 25.08 | N |
| ATOM | 4029 | CZ  | ARG | B | 484 | 28.649 |  8.187 | 54.518 | 1.00 | 23.88 | C |
| ATOM | 4030 | NH1 | ARG | B | 484 | 29.103 |  8.961 | 53.544 | 1.00 | 25.81 | N |
| ATOM | 4031 | NH2 | ARG | B | 484 | 27.695 |  7.293 | 54.273 | 1.00 | 27.48 | N |
| ATOM | 4032 | C   | ARG | B | 484 | 31.039 | 12.453 | 59.863 | 1.00 | 28.46 | C |
| ATOM | 4033 | O   | ARG | B | 484 | 30.455 | 13.478 | 59.537 | 1.00 | 27.04 | O |
| ATOM | 4034 | N   | PRO | B | 485 | 32.231 | 12.478 | 60.474 | 1.00 | 28.18 | N |
| ATOM | 4035 | CD  | PRO | B | 485 | 33.112 | 11.323 | 60.721 | 1.00 | 28.78 | C |
| ATOM | 4036 | CA  | PRO | B | 485 | 32.905 | 13.727 | 60.838 | 1.00 | 30.85 | C |
| ATOM | 4037 | CB  | PRO | B | 485 | 34.095 | 13.242 | 61.654 | 1.00 | 29.07 | C |
| ATOM | 4038 | CG  | PRO | B | 485 | 34.466 | 11.987 | 60.923 | 1.00 | 33.87 | C |
| ATOM | 4039 | C   | PRO | B | 485 | 33.337 | 14.610 | 59.666 | 1.00 | 30.63 | C |
| ATOM | 4040 | O   | PRO | B | 485 | 33.333 | 14.189 | 58.508 | 1.00 | 31.02 | O |
| ATOM | 4041 | N   | THR | B | 486 | 33.718 | 15.841 | 59.994 | 1.00 | 27.95 | N |
| ATOM | 4042 | CA  | THR | B | 486 | 34.172 | 16.811 | 59.005 | 1.00 | 29.22 | C |
| ATOM | 4043 | CB  | THR | B | 486 | 34.046 | 18.238 | 59.537 | 1.00 | 25.56 | C |
| ATOM | 4044 | OG1 | THR | B | 486 | 34.861 | 18.365 | 60.712 | 1.00 | 29.14 | O |
| ATOM | 4045 | CG2 | THR | B | 486 | 32.596 | 18.560 | 59.886 | 1.00 | 29.73 | C |
| ATOM | 4046 | C   | THR | B | 486 | 35.656 | 16.551 | 58.760 | 1.00 | 27.53 | C |
| ATOM | 4047 | O   | THR | B | 486 | 36.314 | 15.954 | 59.601 | 1.00 | 27.33 | O |
| ATOM | 4048 | N   | PHE | B | 487 | 36.183 | 16.996 | 57.620 | 1.00 | 27.73 | N |
| ATOM | 4049 | CA  | PHE | B | 487 | 37.599 | 16.779 | 57.347 | 1.00 | 28.19 | C |
| ATOM | 4050 | CB  | PHE | B | 487 | 37.928 | 17.075 | 55.886 | 1.00 | 26.46 | C |
| ATOM | 4051 | CG  | PHE | B | 487 | 37.668 | 15.914 | 54.957 | 1.00 | 27.93 | C |
| ATOM | 4052 | CD1 | PHE | B | 487 | 38.395 | 14.735 | 55.078 | 1.00 | 26.77 | C |
| ATOM | 4053 | CD2 | PHE | B | 487 | 36.703 | 16.005 | 53.963 | 1.00 | 26.14 | C |
| ATOM | 4054 | CE1 | PHE | B | 487 | 38.161 | 13.659 | 54.210 | 1.00 | 28.28 | C |
| ATOM | 4055 | CE2 | PHE | B | 487 | 36.459 | 14.937 | 53.093 | 1.00 | 29.59 | C |
| ATOM | 4056 | CZ  | PHE | B | 487 | 37.191 | 13.761 | 53.216 | 1.00 | 25.53 | C |
| ATOM | 4057 | C   | PHE | B | 487 | 38.422 | 17.665 | 58.271 | 1.00 | 31.15 | C |
| ATOM | 4058 | O   | PHE | B | 487 | 39.596 | 17.388 | 58.545 | 1.00 | 31.12 | O |
| ATOM | 4059 | N   | ASP | B | 488 | 37.779 | 18.735 | 58.735 | 1.00 | 32.17 | N |
| ATOM | 4060 | CA  | ASP | B | 488 | 38.369 | 19.694 | 59.657 | 1.00 | 34.99 | C |

Figure 14

| ATOM | 4061 | CB | ASP | B | 488 | 37.370 | 20.841 | 59.857 | 1.00 | 37.79 | C |
| ATOM | 4062 | CG | ASP | B | 488 | 37.896 | 21.936 | 60.757 | 1.00 | 41.42 | C |
| ATOM | 4063 | OD1 | ASP | B | 488 | 39.134 | 22.079 | 60.862 | 1.00 | 42.88 | O |
| ATOM | 4064 | OD2 | ASP | B | 488 | 37.056 | 22.660 | 61.340 | 1.00 | 40.15 | O |
| ATOM | 4065 | C | ASP | B | 488 | 38.640 | 18.945 | 60.967 | 1.00 | 34.86 | C |
| ATOM | 4066 | O | ASP | B | 488 | 39.717 | 19.061 | 61.556 | 1.00 | 36.13 | O |
| ATOM | 4067 | N | TYR | B | 489 | 37.660 | 18.164 | 61.415 | 1.00 | 33.26 | N |
| ATOM | 4068 | CA | TYR | B | 489 | 37.823 | 17.370 | 62.634 | 1.00 | 31.87 | C |
| ATOM | 4069 | CB | TYR | B | 489 | 36.508 | 16.672 | 63.011 | 1.00 | 31.57 | C |
| ATOM | 4070 | CG | TYR | B | 489 | 36.672 | 15.665 | 64.133 | 1.00 | 32.25 | C |
| ATOM | 4071 | CD1 | TYR | B | 489 | 36.876 | 16.085 | 65.446 | 1.00 | 32.98 | C |
| ATOM | 4072 | CE1 | TYR | B | 489 | 37.067 | 15.170 | 66.475 | 1.00 | 35.02 | C |
| ATOM | 4073 | CD2 | TYR | B | 489 | 36.659 | 14.294 | 63.875 | 1.00 | 34.67 | C |
| ATOM | 4074 | CE2 | TYR | B | 489 | 36.850 | 13.356 | 64.908 | 1.00 | 31.70 | C |
| ATOM | 4075 | CZ | TYR | B | 489 | 37.056 | 13.807 | 66.199 | 1.00 | 34.32 | C |
| ATOM | 4076 | OH | TYR | B | 489 | 37.290 | 12.910 | 67.214 | 1.00 | 35.22 | O |
| ATOM | 4077 | C | TYR | B | 489 | 38.914 | 16.312 | 62.425 | 1.00 | 31.62 | C |
| ATOM | 4078 | O | TYR | B | 489 | 39.846 | 16.190 | 63.229 | 1.00 | 30.86 | O |
| ATOM | 4079 | N | LEU | B | 490 | 38.795 | 15.551 | 61.337 | 1.00 | 31.14 | N |
| ATOM | 4080 | CA | LEU | B | 490 | 39.770 | 14.508 | 61.021 | 1.00 | 30.62 | C |
| ATOM | 4081 | CB | LEU | B | 490 | 39.438 | 13.882 | 59.664 | 1.00 | 30.98 | C |
| ATOM | 4082 | CG | LEU | B | 490 | 38.157 | 13.039 | 59.707 | 1.00 | 30.06 | C |
| ATOM | 4083 | CD1 | LEU | B | 490 | 37.670 | 12.702 | 58.295 | 1.00 | 28.67 | C |
| ATOM | 4084 | CD2 | LEU | B | 490 | 38.434 | 11.780 | 60.512 | 1.00 | 30.24 | C |
| ATOM | 4085 | C | LEU | B | 490 | 41.188 | 15.071 | 61.012 | 1.00 | 32.56 | C |
| ATOM | 4086 | O | LEU | B | 490 | 42.107 | 14.468 | 61.561 | 1.00 | 29.64 | O |
| ATOM | 4087 | N | ARG | B | 491 | 41.370 | 16.228 | 60.378 | 1.00 | 34.35 | N |
| ATOM | 4088 | CA | ARG | B | 491 | 42.685 | 16.859 | 60.351 | 1.00 | 37.05 | C |
| ATOM | 4089 | CB | ARG | B | 491 | 42.617 | 18.185 | 59.591 | 1.00 | 40.20 | C |
| ATOM | 4090 | CG | ARG | B | 491 | 43.930 | 18.951 | 59.610 | 1.00 | 43.78 | C |
| ATOM | 4091 | CD | ARG | B | 491 | 43.693 | 20.440 | 59.454 | 1.00 | 47.40 | C |
| ATOM | 4092 | NE | ARG | B | 491 | 42.978 | 20.985 | 60.602 | 1.00 | 52.69 | N |
| ATOM | 4093 | CZ | ARG | B | 491 | 43.418 | 20.912 | 61.855 | 1.00 | 55.19 | C |
| ATOM | 4094 | NH1 | ARG | B | 491 | 44.573 | 20.317 | 62.120 | 1.00 | 56.98 | N |
| ATOM | 4095 | NH2 | ARG | B | 491 | 42.707 | 21.431 | 62.847 | 1.00 | 55.31 | N |
| ATOM | 4096 | C | ARG | B | 491 | 43.186 | 17.124 | 61.783 | 1.00 | 36.93 | C |
| ATOM | 4097 | O | ARG | B | 491 | 44.339 | 16.833 | 62.116 | 1.00 | 38.21 | O |
| ATOM | 4098 | N | SER | B | 492 | 42.314 | 17.665 | 62.629 | 1.00 | 36.87 | N |
| ATOM | 4099 | CA | SER | B | 492 | 42.674 | 17.975 | 64.013 | 1.00 | 38.16 | C |
| ATOM | 4100 | CB | SER | B | 492 | 41.468 | 18.526 | 64.772 | 1.00 | 37.21 | C |
| ATOM | 4101 | OG | SER | B | 492 | 41.043 | 19.761 | 64.244 | 1.00 | 41.68 | O |
| ATOM | 4102 | C | SER | B | 492 | 43.218 | 16.776 | 64.783 | 1.00 | 39.21 | C |
| ATOM | 4103 | O | SER | B | 492 | 44.312 | 16.829 | 65.346 | 1.00 | 39.76 | O |
| ATOM | 4104 | N | VAL | B | 493 | 42.448 | 15.693 | 64.809 | 1.00 | 39.94 | N |
| ATOM | 4105 | CA | VAL | B | 493 | 42.860 | 14.493 | 65.536 | 1.00 | 40.63 | C |
| ATOM | 4106 | CB | VAL | B | 493 | 41.684 | 13.477 | 65.641 | 1.00 | 41.26 | C |
| ATOM | 4107 | CG1 | VAL | B | 493 | 40.936 | 13.408 | 64.329 | 1.00 | 39.79 | C |
| ATOM | 4108 | CG2 | VAL | B | 493 | 42.206 | 12.098 | 66.019 | 1.00 | 41.71 | C |
| ATOM | 4109 | C | VAL | B | 493 | 44.091 | 13.805 | 64.941 | 1.00 | 40.48 | C |
| ATOM | 4110 | O | VAL | B | 493 | 44.902 | 13.226 | 65.671 | 1.00 | 39.93 | O |
| ATOM | 4111 | N | LEU | B | 494 | 44.252 | 13.873 | 63.626 | 1.00 | 39.45 | N |
| ATOM | 4112 | CA | LEU | B | 494 | 45.401 | 13.221 | 63.011 | 1.00 | 39.52 | C |
| ATOM | 4113 | CB | LEU | B | 494 | 45.171 | 13.055 | 61.505 | 1.00 | 36.11 | C |
| ATOM | 4114 | CG | LEU | B | 494 | 44.065 | 12.038 | 61.170 | 1.00 | 36.94 | C |
| ATOM | 4115 | CD1 | LEU | B | 494 | 43.847 | 11.953 | 59.677 | 1.00 | 36.23 | C |
| ATOM | 4116 | CD2 | LEU | B | 494 | 44.449 | 10.670 | 61.717 | 1.00 | 34.93 | C |
| ATOM | 4117 | C | LEU | B | 494 | 46.735 | 13.919 | 63.288 | 1.00 | 40.84 | C |
| ATOM | 4118 | O | LEU | B | 494 | 47.731 | 13.257 | 63.576 | 1.00 | 40.60 | O |
| ATOM | 4119 | N | GLU | B | 495 | 46.757 | 15.247 | 63.221 | 1.00 | 43.55 | N |
| ATOM | 4120 | CA | GLU | B | 495 | 47.990 | 15.993 | 63.465 | 1.00 | 47.77 | C |

Figure 14

```
ATOM   4121  CB   GLU B 495      47.781   17.488   63.210  1.00 49.99           C
ATOM   4122  CG   GLU B 495      47.224   17.831   61.843  1.00 53.35           C
ATOM   4123  CD   GLU B 495      47.229   19.323   61.576  1.00 55.14           C
ATOM   4124  OE1  GLU B 495      47.002   20.094   62.535  1.00 56.50           O
ATOM   4125  OE2  GLU B 495      47.450   19.721   60.408  1.00 55.73           O
ATOM   4126  C    GLU B 495      48.500   15.803   64.895  1.00 49.60           C
ATOM   4127  O    GLU B 495      49.702   15.688   65.127  1.00 51.19           O
ATOM   4128  N    ASP B 496      47.579   15.776   65.849  1.00 51.54           N
ATOM   4129  CA   ASP B 496      47.931   15.606   67.254  1.00 53.10           C
ATOM   4130  CB   ASP B 496      47.155   16.610   68.115  1.00 53.42           C
ATOM   4131  CG   ASP B 496      47.548   18.052   67.844  1.00 55.31           C
ATOM   4132  OD1  ASP B 496      47.774   18.408   66.669  1.00 58.00           O
ATOM   4133  OD2  ASP B 496      47.611   18.839   68.810  1.00 55.97           O
ATOM   4134  C    ASP B 496      47.604   14.194   67.730  1.00 53.63           C
ATOM   4135  O    ASP B 496      47.218   14.007   68.881  1.00 55.74           O
ATOM   4136  N    PHE B 497      47.758   13.198   66.859  1.00 53.53           N
ATOM   4137  CA   PHE B 497      47.442   11.826   67.250  1.00 52.95           C
ATOM   4138  CB   PHE B 497      47.567   10.874   66.057  1.00 51.55           C
ATOM   4139  CG   PHE B 497      46.838    9.575   66.255  1.00 50.48           C
ATOM   4140  CD1  PHE B 497      45.446    9.542   66.246  1.00 51.44           C
ATOM   4141  CD2  PHE B 497      47.534    8.397   66.504  1.00 51.30           C
ATOM   4142  CE1  PHE B 497      44.757    8.359   66.484  1.00 49.68           C
ATOM   4143  CE2  PHE B 497      46.856    7.204   66.745  1.00 50.97           C
ATOM   4144  CZ   PHE B 497      45.464    7.188   66.736  1.00 51.57           C
ATOM   4145  C    PHE B 497      48.324   11.329   68.396  1.00 54.06           C
ATOM   4146  O    PHE B 497      47.852   10.637   69.301  1.00 52.65           O
ATOM   4147  N    PHE B 498      49.609   11.668   68.343  1.00 55.25           N
ATOM   4148  CA   PHE B 498      50.555   11.290   69.392  1.00 57.21           C
ATOM   4149  CB   PHE B 498      50.684    9.760   69.519  1.00 57.68           C
ATOM   4150  CG   PHE B 498      50.908    9.043   68.217  1.00 58.49           C
ATOM   4151  CD1  PHE B 498      51.460    9.697   67.121  1.00 58.48           C
ATOM   4152  CD2  PHE B 498      50.566    7.699   68.093  1.00 58.85           C
ATOM   4153  CE1  PHE B 498      51.664    9.024   65.920  1.00 58.77           C
ATOM   4154  CE2  PHE B 498      50.767    7.017   66.898  1.00 57.93           C
ATOM   4155  CZ   PHE B 498      51.315    7.682   65.811  1.00 58.29           C
ATOM   4156  C    PHE B 498      51.932   11.901   69.173  1.00 57.62           C
ATOM   4157  O    PHE B 498      52.390   12.587   70.111  1.00 58.07           O
ATOM   4158  OXT  PHE B 498      52.547   11.742   68.102  1.00 40.86           O
ATOM   4159  C1   LIG A 500      23.655    9.978   21.562  1.00 25.23           C
ATOM   4160  C2   LIG A 500      24.700   10.926   21.282  1.00 28.58           C
ATOM   4161  C3   LIG A 500      22.473   10.459   22.203  1.00 25.15           C
ATOM   4162  N1   LIG A 500      23.394    8.593   21.362  1.00 25.77           N
ATOM   4163  C4   LIG A 500      24.488   12.352   21.600  1.00 27.52           C
ATOM   4164  C5   LIG A 500      26.070   10.567   20.703  1.00 27.88           C
ATOM   4165  N2   LIG A 500      21.666    9.414   22.420  1.00 23.01           N
ATOM   4166  C6   LIG A 500      22.290   11.814   22.488  1.00 26.42           C
ATOM   4167  C7   LIG A 500      22.181    8.331   21.945  1.00 24.74           C
ATOM   4168  C8   LIG A 500      24.180    7.519   20.722  1.00 27.19           C
ATOM   4169  C9   LIG A 500      25.534   13.312   21.331  1.00 28.24           C
ATOM   4170  C10  LIG A 500      23.262   12.761   22.189  1.00 28.78           C
ATOM   4171  N3   LIG A 500      26.959   11.536   20.510  1.00 28.65           N
ATOM   4172  O1   LIG A 500      26.401    9.422   20.421  1.00 26.88           O
ATOM   4173  N4   LIG A 500      21.597    7.050   22.011  1.00 23.39           N
ATOM   4174  C11  LIG A 500      26.718   12.891   20.808  1.00 29.63           C
ATOM   4175  C12  LIG A 500      25.330   14.802   21.649  1.00 31.20           C
ATOM   4176  C13  LIG A 500      20.332    6.984   22.744  1.00 19.60           C
ATOM   4177  C14  LIG A 500      27.821   13.884   20.547  1.00 30.39           C
ATOM   4178  C15  LIG A 500      19.035    7.036   22.044  1.00 22.81           C
ATOM   4179  C16  LIG A 500      20.325    6.852   24.176  1.00 22.38           C
ATOM   4180  C17  LIG A 500      29.022   13.486   20.033  1.00 29.27           C
```

Figure 14

| | | | | | | | | | |
|---|---|---|---|---|---|---|---|---|---|
| ATOM | 4181 | C18 | LIG A 500 | 17.825 | 6.962 | 22.769 | 0.00 | 21.29 | C |
| ATOM | 4182 | CL1 | LIG A 500 | 19.051 | 7.182 | 20.334 | 1.00 | 18.63 | CL |
| ATOM | 4183 | C19 | LIG A 500 | 19.095 | 6.781 | 24.875 | 0.00 | 21.05 | C |
| ATOM | 4184 | CL2 | LIG A 500 | 21.847 | 6.782 | 25.053 | 1.00 | 17.96 | CL |
| ATOM | 4185 | C20 | LIG A 500 | 30.138 | 14.493 | 19.777 | 0.00 | 23.85 | C |
| ATOM | 4186 | C21 | LIG A 500 | 17.857 | 6.836 | 24.177 | 0.00 | 21.12 | C |
| ATOM | 4187 | N5 | LIG A 500 | 29.605 | 15.765 | 19.211 | 0.00 | 21.13 | N |
| ATOM | 4188 | C22 | LIG A 500 | 30.075 | 16.891 | 20.056 | 0.00 | 19.66 | C |
| ATOM | 4189 | C23 | LIG A 500 | 30.064 | 15.948 | 17.790 | 0.00 | 19.66 | C |
| ATOM | 4190 | C24 | LIG A 500 | 28.873 | 17.685 | 20.572 | 0.00 | 19.17 | C |
| ATOM | 4191 | C25 | LIG A 500 | 31.607 | 16.027 | 17.614 | 0.00 | 19.17 | C |
| ATOM | 4192 | C1 | LIG B 500 | 52.361 | 12.602 | 38.393 | 1.00 | 24.51 | C |
| ATOM | 4193 | C2 | LIG B 500 | 53.438 | 11.698 | 38.680 | 1.00 | 29.64 | C |
| ATOM | 4194 | C3 | LIG B 500 | 51.185 | 12.074 | 37.752 | 1.00 | 25.97 | C |
| ATOM | 4195 | N1 | LIG B 500 | 52.067 | 13.971 | 38.587 | 1.00 | 25.92 | N |
| ATOM | 4196 | C4 | LIG B 500 | 53.275 | 10.268 | 38.374 | 1.00 | 29.73 | C |
| ATOM | 4197 | C5 | LIG B 500 | 54.793 | 12.105 | 39.258 | 1.00 | 28.41 | C |
| ATOM | 4198 | N2 | LIG B 500 | 50.333 | 13.101 | 37.518 | 1.00 | 23.89 | N |
| ATOM | 4199 | C6 | LIG B 500 | 51.055 | 10.719 | 37.483 | 1.00 | 26.89 | C |
| ATOM | 4200 | C7 | LIG B 500 | 50.838 | 14.206 | 37.989 | 1.00 | 25.86 | C |
| ATOM | 4201 | C8 | LIG B 500 | 52.852 | 15.059 | 39.237 | 1.00 | 26.45 | C |
| ATOM | 4202 | C9 | LIG B 500 | 54.352 | 9.350 | 38.645 | 1.00 | 29.96 | C |
| ATOM | 4203 | C10 | LIG B 500 | 52.052 | 9.811 | 37.785 | 1.00 | 29.65 | C |
| ATOM | 4204 | N3 | LIG B 500 | 55.711 | 11.180 | 39.455 | 1.00 | 29.54 | N |
| ATOM | 4205 | O1 | LIG B 500 | 55.085 | 13.254 | 39.533 | 1.00 | 27.40 | O |
| ATOM | 4206 | N4 | LIG B 500 | 50.231 | 15.471 | 37.900 | 1.00 | 24.76 | N |
| ATOM | 4207 | C11 | LIG B 500 | 55.520 | 9.819 | 39.165 | 1.00 | 31.89 | C |
| ATOM | 4208 | C12 | LIG B 500 | 54.198 | 7.859 | 38.336 | 1.00 | 30.77 | C |
| ATOM | 4209 | C13 | LIG B 500 | 48.945 | 15.489 | 37.158 | 1.00 | 18.46 | C |
| ATOM | 4210 | C14 | LIG B 500 | 56.657 | 8.877 | 39.417 | 1.00 | 31.51 | C |
| ATOM | 4211 | C15 | LIG B 500 | 47.644 | 15.438 | 37.864 | 1.00 | 21.45 | C |
| ATOM | 4212 | C16 | LIG B 500 | 48.932 | 15.570 | 35.722 | 1.00 | 22.11 | C |
| ATOM | 4213 | C17 | LIG B 500 | 57.848 | 9.314 | 39.914 | 1.00 | 30.80 | C |
| ATOM | 4214 | C18 | LIG B 500 | 46.435 | 15.465 | 37.136 | 0.00 | 20.25 | C |
| ATOM | 4215 | CL1 | LIG B 500 | 47.651 | 15.345 | 39.574 | 1.00 | 17.21 | CL |
| ATOM | 4216 | C19 | LIG B 500 | 47.701 | 15.597 | 35.022 | 0.00 | 20.54 | C |
| ATOM | 4217 | CL2 | LIG B 500 | 50.461 | 15.636 | 34.846 | 1.00 | 16.65 | CL |
| ATOM | 4218 | C20 | LIG B 500 | 58.996 | 8.342 | 40.157 | 0.00 | 24.66 | C |
| ATOM | 4219 | C21 | LIG B 500 | 46.464 | 15.543 | 35.724 | 0.00 | 20.57 | C |
| ATOM | 4220 | N5 | LIG B 500 | 58.503 | 6.989 | 40.542 | 0.00 | 21.58 | N |
| ATOM | 4221 | C22 | LIG B 500 | 59.096 | 5.991 | 39.615 | 0.00 | 19.82 | C |
| ATOM | 4222 | C23 | LIG B 500 | 58.875 | 6.671 | 41.966 | 0.00 | 19.82 | C |
| ATOM | 4223 | C24 | LIG B 500 | 57.983 | 5.148 | 38.983 | 0.00 | 19.24 | C |
| ATOM | 4224 | C25 | LIG B 500 | 60.405 | 6.601 | 42.233 | 0.00 | 19.24 | C |
| END | | | | | | | | | |

Figure 14

```
CRYST1   57.190   44.480  120.050  90.00   90.00   90.00 P21              1
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.017486  0.000000  0.000000        0.00000
SCALE2      0.000000  0.022482  0.000000        0.00000
SCALE3      0.000000  0.000000  0.008330        0.00000
ATOM      1  CB  TRP A 238      18.903  -5.542  27.799  1.00 63.46           C
ATOM      2  CG  TRP A 238      18.355  -6.163  26.544  1.00 62.95           C
ATOM      3  CD2 TRP A 238      18.749  -5.862  25.202  1.00 62.26           C
ATOM      4  CE2 TRP A 238      17.928  -6.621  24.346  1.00 62.13           C
ATOM      5  CE3 TRP A 238      19.716  -5.021  24.641  1.00 62.02           C
ATOM      6  CD1 TRP A 238      17.343  -7.076  26.451  1.00 62.70           C
ATOM      7  NE1 TRP A 238      17.078  -7.354  25.132  1.00 62.34           N
ATOM      8  CZ2 TRP A 238      18.041  -6.562  22.957  1.00 62.21           C
ATOM      9  CZ3 TRP A 238      19.827  -4.965  23.266  1.00 61.74           C
ATOM     10  CH2 TRP A 238      18.994  -5.729  22.438  1.00 61.98           C
ATOM     11  C   TRP A 238      20.119  -5.742  29.954  1.00 64.34           C
ATOM     12  O   TRP A 238      20.920  -4.815  29.844  1.00 64.29           O
ATOM     13  N   TRP A 238      18.766  -7.648  29.103  1.00 64.81           N
ATOM     14  CA  TRP A 238      19.645  -6.507  28.724  1.00 64.43           C
ATOM     15  N   GLU A 239      19.616  -6.120  31.125  1.00 55.92           N
ATOM     16  CA  GLU A 239      20.012  -5.461  32.363  1.00 56.38           C
ATOM     17  CB  GLU A 239      19.070  -5.860  33.506  1.00 96.84           C
ATOM     18  CG  GLU A 239      17.624  -5.363  33.372  1.00 99.66           C
ATOM     19  CD  GLU A 239      16.814  -6.089  32.296  1.00101.73           C
ATOM     20  OE1 GLU A 239      16.717  -7.338  32.347  1.00102.49           O
ATOM     21  OE2 GLU A 239      16.261  -5.407  31.401  1.00102.49           O
ATOM     22  C   GLU A 239      21.456  -5.855  32.706  1.00 55.49           C
ATOM     23  O   GLU A 239      21.822  -7.025  32.617  1.00 55.21           O
ATOM     24  N   VAL A 240      22.279  -4.878  33.078  1.00 64.06           N
ATOM     25  CA  VAL A 240      23.673  -5.157  33.425  1.00 62.84           C
ATOM     26  CB  VAL A 240      24.646  -4.833  32.257  1.00 53.71           C
ATOM     27  CG1 VAL A 240      24.208  -5.550  30.992  1.00 52.90           C
ATOM     28  CG2 VAL A 240      24.730  -3.320  32.045  1.00 52.82           C
ATOM     29  C   VAL A 240      24.115  -4.346  34.629  1.00 62.07           C
ATOM     30  O   VAL A 240      23.495  -3.342  34.975  1.00 62.50           O
ATOM     31  N   PRO A 241      25.196  -4.782  35.292  1.00 44.68           N
ATOM     32  CD  PRO A 241      25.821  -6.109  35.162  1.00 51.78           C
ATOM     33  CA  PRO A 241      25.716  -4.074  36.465  1.00 44.55           C
ATOM     34  CB  PRO A 241      26.758  -5.048  37.023  1.00 51.97           C
ATOM     35  CG  PRO A 241      26.236  -6.394  36.579  1.00 52.08           C
ATOM     36  C   PRO A 241      26.329  -2.723  36.090  1.00 44.35           C
ATOM     37  O   PRO A 241      26.916  -2.569  35.017  1.00 44.23           O
ATOM     38  N   ARG A 242      26.179  -1.745  36.976  1.00 51.09           N
ATOM     39  CA  ARG A 242      26.721  -0.408  36.752  1.00 51.05           C
ATOM     40  CB  ARG A 242      26.438   0.466  37.973  1.00 64.23           C
ATOM     41  CG  ARG A 242      26.698   1.929  37.758  1.00 65.04           C
ATOM     42  CD  ARG A 242      25.678   2.488  36.797  1.00 67.84           C
ATOM     43  NE  ARG A 242      24.325   2.443  37.352  1.00 68.55           N
ATOM     44  CZ  ARG A 242      23.944   3.120  38.428  1.00 66.94           C
```

Figure 15

| | | | | | | | | | |
|---|---|---|---|---|---|---|---|---|---|
| ATOM | 45 | NH1 | ARG | A | 242 | 24.811 | 3.894 | 39.062 | 1.00 67.95 | N |
| ATOM | 46 | NH2 | ARG | A | 242 | 22.701 | 3.019 | 38.874 | 1.00 66.70 | N |
| ATOM | 47 | C | ARG | A | 242 | 28.236 | -0.482 | 36.523 | 1.00 51.05 | C |
| ATOM | 48 | O | ARG | A | 242 | 28.801 | 0.237 | 35.691 | 1.00 50.33 | O |
| ATOM | 49 | N | GLU | A | 243 | 28.871 | -1.369 | 37.281 | 1.00 52.35 | N |
| ATOM | 50 | CA | GLU | A | 243 | 30.309 | -1.595 | 37.244 | 1.00 52.57 | C |
| ATOM | 51 | CB | GLU | A | 243 | 30.653 | -2.772 | 38.158 | 1.00 77.99 | C |
| ATOM | 52 | CG | GLU | A | 243 | 30.204 | -2.584 | 39.606 | 1.00 81.11 | C |
| ATOM | 53 | CD | GLU | A | 243 | 28.698 | -2.374 | 39.741 | 1.00 82.02 | C |
| ATOM | 54 | OE1 | GLU | A | 243 | 27.927 | -3.226 | 39.247 | 1.00 81.62 | O |
| ATOM | 55 | OE2 | GLU | A | 243 | 28.289 | -1.359 | 40.348 | 1.00 83.30 | O |
| ATOM | 56 | C | GLU | A | 243 | 30.886 | -1.849 | 35.850 | 1.00 52.03 | C |
| ATOM | 57 | O | GLU | A | 243 | 32.054 | -1.543 | 35.587 | 1.00 51.82 | O |
| ATOM | 58 | N | THR | A | 244 | 30.076 | -2.413 | 34.962 | 1.00 44.64 | N |
| ATOM | 59 | CA | THR | A | 244 | 30.527 | -2.705 | 33.609 | 1.00 43.97 | C |
| ATOM | 60 | CB | THR | A | 244 | 29.588 | -3.706 | 32.926 | 1.00 51.31 | C |
| ATOM | 61 | OG1 | THR | A | 244 | 28.313 | -3.085 | 32.703 | 1.00 52.22 | O |
| ATOM | 62 | CG2 | THR | A | 244 | 29.394 | -4.934 | 33.808 | 1.00 50.74 | C |
| ATOM | 63 | C | THR | A | 244 | 30.570 | -1.437 | 32.766 | 1.00 43.17 | C |
| ATOM | 64 | O | THR | A | 244 | 30.858 | -1.482 | 31.576 | 1.00 42.78 | O |
| ATOM | 65 | N | LEU | A | 245 | 30.303 | -0.303 | 33.400 | 1.00 48.16 | N |
| ATOM | 66 | CA | LEU | A | 245 | 30.281 | 0.972 | 32.703 | 1.00 48.02 | C |
| ATOM | 67 | CB | LEU | A | 245 | 28.836 | 1.437 | 32.537 | 1.00 58.09 | C |
| ATOM | 68 | CG | LEU | A | 245 | 27.925 | 0.685 | 31.582 | 1.00 57.70 | C |
| ATOM | 69 | CD1 | LEU | A | 245 | 26.487 | 1.134 | 31.801 | 1.00 58.58 | C |
| ATOM | 70 | CD2 | LEU | A | 245 | 28.369 | 0.955 | 30.157 | 1.00 58.65 | C |
| ATOM | 71 | C | LEU | A | 245 | 31.058 | 2.105 | 33.361 | 1.00 47.95 | C |
| ATOM | 72 | O | LEU | A | 245 | 31.009 | 2.300 | 34.579 | 1.00 47.18 | O |
| ATOM | 73 | N | LYS | A | 246 | 31.761 | 2.869 | 32.537 | 1.00 48.48 | N |
| ATOM | 74 | CA | LYS | A | 246 | 32.488 | 4.019 | 33.036 | 1.00 48.71 | C |
| ATOM | 75 | CB | LYS | A | 246 | 34.000 | 3.841 | 32.911 | 1.00 57.58 | C |
| ATOM | 76 | CG | LYS | A | 246 | 34.769 | 5.069 | 33.398 | 1.00 58.94 | C |
| ATOM | 77 | CD | LYS | A | 246 | 36.226 | 4.758 | 33.709 | 1.00 60.16 | C |
| ATOM | 78 | CE | LYS | A | 246 | 36.961 | 4.215 | 32.487 | 1.00 60.54 | C |
| ATOM | 79 | NZ | LYS | A | 246 | 38.360 | 3.808 | 32.821 | 1.00 59.85 | N |
| ATOM | 80 | C | LYS | A | 246 | 32.058 | 5.246 | 32.254 | 1.00 47.88 | C |
| ATOM | 81 | O | LYS | A | 246 | 32.318 | 5.356 | 31.062 | 1.00 48.00 | O |
| ATOM | 82 | N | LEU | A | 247 | 31.369 | 6.151 | 32.931 | 1.00 53.08 | N |
| ATOM | 83 | CA | LEU | A | 247 | 30.925 | 7.386 | 32.318 | 1.00 52.92 | C |
| ATOM | 84 | CB | LEU | A | 247 | 29.796 | 8.010 | 33.143 | 1.00 50.84 | C |
| ATOM | 85 | CG | LEU | A | 247 | 28.381 | 7.574 | 32.739 | 1.00 51.30 | C |
| ATOM | 86 | CD1 | LEU | A | 247 | 28.250 | 6.062 | 32.772 | 1.00 50.96 | C |
| ATOM | 87 | CD2 | LEU | A | 247 | 27.373 | 8.230 | 33.671 | 1.00 52.08 | C |
| ATOM | 88 | C | LEU | A | 247 | 32.139 | 8.295 | 32.277 | 1.00 53.15 | C |
| ATOM | 89 | O | LEU | A | 247 | 32.696 | 8.658 | 33.317 | 1.00 53.16 | O |
| ATOM | 90 | N | VAL | A | 248 | 32.557 | 8.659 | 31.071 | 1.00 46.84 | N |
| ATOM | 91 | CA | VAL | A | 248 | 33.737 | 9.493 | 30.914 | 1.00 46.63 | C |
| ATOM | 92 | CB | VAL | A | 248 | 34.613 | 8.966 | 29.775 | 1.00 48.58 | C |
| ATOM | 93 | CG1 | VAL | A | 248 | 35.801 | 9.894 | 29.552 | 1.00 49.01 | C |
| ATOM | 94 | CG2 | VAL | A | 248 | 35.072 | 7.564 | 30.098 | 1.00 49.01 | C |
| ATOM | 95 | C | VAL | A | 248 | 33.511 | 10.970 | 30.674 | 1.00 46.04 | C |
| ATOM | 96 | O | VAL | A | 248 | 34.145 | 11.804 | 31.314 | 1.00 46.24 | O |
| ATOM | 97 | N | GLU | A | 249 | 32.594 | 11.294 | 29.767 | 1.00 46.35 | N |
| ATOM | 98 | CA | GLU | A | 249 | 32.344 | 12.684 | 29.396 | 1.00 45.11 | C |
| ATOM | 99 | CB | GLU | A | 249 | 33.093 | 12.948 | 28.091 | 1.00 49.87 | C |
| ATOM | 100 | CG | GLU | A | 249 | 33.282 | 14.387 | 27.700 | 1.00 49.59 | C |
| ATOM | 101 | CD | GLU | A | 249 | 34.024 | 14.502 | 26.379 | 1.00 49.44 | C |
| ATOM | 102 | OE1 | GLU | A | 249 | 34.755 | 13.547 | 26.020 | 1.00 47.96 | O |
| ATOM | 103 | OE2 | GLU | A | 249 | 33.880 | 15.541 | 25.709 | 1.00 49.51 | O |
| ATOM | 104 | C | GLU | A | 249 | 30.854 | 13.002 | 29.210 | 1.00 44.26 | C |

Figure 15

| | | | | | | | | | | |
|---|---|---|---|---|---|---|---|---|---|---|
| ATOM | 105 | O | GLU | A | 249 | 30.112 | 12.199 | 28.655 | 1.00 43.93 | O |
| ATOM | 106 | N | ARG | A | 250 | 30.427 | 14.177 | 29.660 | 1.00 47.41 | N |
| ATOM | 107 | CA | ARG | A | 250 | 29.032 | 14.568 | 29.520 | 1.00 47.17 | C |
| ATOM | 108 | CB | ARG | A | 250 | 28.592 | 15.474 | 30.679 | 1.00 48.93 | C |
| ATOM | 109 | CG | ARG | A | 250 | 27.078 | 15.669 | 30.750 | 1.00 50.04 | C |
| ATOM | 110 | CD | ARG | A | 250 | 26.631 | 16.496 | 31.957 | 1.00 51.59 | C |
| ATOM | 111 | NE | ARG | A | 250 | 27.024 | 17.902 | 31.853 | 1.00 53.42 | N |
| ATOM | 112 | CZ | ARG | A | 250 | 26.619 | 18.859 | 32.687 | 1.00 53.96 | C |
| ATOM | 113 | NH1 | ARG | A | 250 | 25.802 | 18.571 | 33.696 | 1.00 52.54 | N |
| ATOM | 114 | NH2 | ARG | A | 250 | 27.027 | 20.109 | 32.506 | 1.00 55.29 | N |
| ATOM | 115 | C | ARG | A | 250 | 28.805 | 15.295 | 28.199 | 1.00 46.65 | C |
| ATOM | 116 | O | ARG | A | 250 | 29.341 | 16.379 | 27.977 | 1.00 47.47 | O |
| ATOM | 117 | N | LEU | A | 251 | 28.012 | 14.685 | 27.327 | 1.00 48.52 | N |
| ATOM | 118 | CA | LEU | A | 251 | 27.696 | 15.257 | 26.031 | 1.00 47.05 | C |
| ATOM | 119 | CB | LEU | A | 251 | 27.244 | 14.152 | 25.073 | 1.00 35.19 | C |
| ATOM | 120 | CG | LEU | A | 251 | 28.258 | 13.020 | 24.884 | 1.00 33.59 | C |
| ATOM | 121 | CD1 | LEU | A | 251 | 27.649 | 11.890 | 24.065 | 1.00 32.52 | C |
| ATOM | 122 | CD2 | LEU | A | 251 | 29.513 | 13.568 | 24.218 | 1.00 32.70 | C |
| ATOM | 123 | C | LEU | A | 251 | 26.602 | 16.315 | 26.178 | 1.00 47.42 | C |
| ATOM | 124 | O | LEU | A | 251 | 26.595 | 17.312 | 25.462 | 1.00 48.38 | O |
| ATOM | 125 | N | GLY | A | 252 | 25.680 | 16.111 | 27.114 | 1.00 43.32 | N |
| ATOM | 126 | CA | GLY | A | 252 | 24.625 | 17.093 | 27.301 | 1.00 42.45 | C |
| ATOM | 127 | C | GLY | A | 252 | 23.813 | 16.959 | 28.578 | 1.00 42.64 | C |
| ATOM | 128 | O | GLY | A | 252 | 23.700 | 15.875 | 29.146 | 1.00 42.24 | O |
| ATOM | 129 | N | ALA | A | 253 | 23.243 | 18.073 | 29.030 | 1.00 40.34 | N |
| ATOM | 130 | CA | ALA | A | 253 | 22.420 | 18.087 | 30.235 | 1.00 40.89 | C |
| ATOM | 131 | CB | ALA | A | 253 | 23.151 | 18.804 | 31.369 | 1.00 35.47 | C |
| ATOM | 132 | C | ALA | A | 253 | 21.094 | 18.785 | 29.941 | 1.00 41.65 | C |
| ATOM | 133 | O | ALA | A | 253 | 21.068 | 19.904 | 29.419 | 1.00 40.84 | O |
| ATOM | 134 | N | GLY | A | 254 | 19.997 | 18.113 | 30.284 | 1.00 44.05 | N |
| ATOM | 135 | CA | GLY | A | 254 | 18.681 | 18.667 | 30.045 | 1.00 45.13 | C |
| ATOM | 136 | C | GLY | A | 254 | 17.663 | 18.444 | 31.149 | 1.00 46.03 | C |
| ATOM | 137 | O | GLY | A | 254 | 17.969 | 17.906 | 32.211 | 1.00 47.18 | O |
| ATOM | 138 | N | GLN | A | 255 | 16.428 | 18.841 | 30.872 | 1.00 53.27 | N |
| ATOM | 139 | CA | GLN | A | 255 | 15.329 | 18.742 | 31.825 | 1.00 52.91 | C |
| ATOM | 140 | CB | GLN | A | 255 | 14.065 | 19.289 | 31.163 | 1.00 79.19 | C |
| ATOM | 141 | CG | GLN | A | 255 | 12.894 | 19.545 | 32.100 | 1.00 83.64 | C |
| ATOM | 142 | CD | GLN | A | 255 | 11.712 | 20.174 | 31.377 | 1.00 85.79 | C |
| ATOM | 143 | OE1 | GLN | A | 255 | 11.855 | 21.209 | 30.712 | 1.00 87.12 | O |
| ATOM | 144 | NE2 | GLN | A | 255 | 10.539 | 19.554 | 31.501 | 1.00 85.74 | N |
| ATOM | 145 | C | GLN | A | 255 | 15.057 | 17.346 | 32.389 | 1.00 52.57 | C |
| ATOM | 146 | O | GLN | A | 255 | 14.696 | 17.207 | 33.562 | 1.00 53.43 | O |
| ATOM | 147 | N | PHE | A | 256 | 15.231 | 16.312 | 31.569 | 1.00 38.10 | N |
| ATOM | 148 | CA | PHE | A | 256 | 14.962 | 14.950 | 32.014 | 1.00 36.53 | C |
| ATOM | 149 | CB | PHE | A | 256 | 14.099 | 14.223 | 30.973 | 1.00 45.60 | C |
| ATOM | 150 | CG | PHE | A | 256 | 12.739 | 14.833 | 30.778 | 1.00 45.42 | C |
| ATOM | 151 | CD1 | PHE | A | 256 | 12.172 | 15.623 | 31.766 | 1.00 45.54 | C |
| ATOM | 152 | CD2 | PHE | A | 256 | 12.016 | 14.594 | 29.622 | 1.00 45.03 | C |
| ATOM | 153 | CE1 | PHE | A | 256 | 10.911 | 16.158 | 31.605 | 1.00 45.53 | C |
| ATOM | 154 | CE2 | PHE | A | 256 | 10.753 | 15.129 | 29.456 | 1.00 45.08 | C |
| ATOM | 155 | CZ | PHE | A | 256 | 10.199 | 15.911 | 30.449 | 1.00 44.63 | C |
| ATOM | 156 | C | PHE | A | 256 | 16.184 | 14.088 | 32.343 | 1.00 35.73 | C |
| ATOM | 157 | O | PHE | A | 256 | 16.042 | 12.936 | 32.736 | 1.00 34.44 | O |
| ATOM | 158 | N | GLY | A | 257 | 17.381 | 14.638 | 32.178 | 1.00 41.49 | N |
| ATOM | 159 | CA | GLY | A | 257 | 18.573 | 13.867 | 32.475 | 1.00 40.53 | C |
| ATOM | 160 | C | GLY | A | 257 | 19.770 | 14.307 | 31.662 | 1.00 39.97 | C |
| ATOM | 161 | O | GLY | A | 257 | 19.855 | 15.456 | 31.244 | 1.00 38.99 | O |
| ATOM | 162 | N | GLU | A | 258 | 20.702 | 13.390 | 31.438 | 1.00 41.03 | N |
| ATOM | 163 | CA | GLU | A | 258 | 21.902 | 13.714 | 30.679 | 1.00 41.33 | C |
| ATOM | 164 | CB | GLU | A | 258 | 23.060 | 14.026 | 31.631 | 1.00 51.36 | C |

Figure 15

```
ATOM    165  CG   GLU A 258      22.699  14.887  32.834  1.00 53.24           C
ATOM    166  CD   GLU A 258      23.877  15.053  33.785  1.00 55.55           C
ATOM    167  OE1  GLU A 258      24.593  14.052  34.017  1.00 55.87           O
ATOM    168  OE2  GLU A 258      24.087  16.172  34.304  1.00 55.98           O
ATOM    169  C    GLU A 258      22.318  12.566  29.775  1.00 40.61           C
ATOM    170  O    GLU A 258      21.832  11.440  29.900  1.00 40.93           O
ATOM    171  N    VAL A 259      23.219  12.866  28.852  1.00 39.92           N
ATOM    172  CA   VAL A 259      23.748  11.854  27.951  1.00 39.68           C
ATOM    173  CB   VAL A 259      23.387  12.136  26.485  1.00 39.51           C
ATOM    174  CG1  VAL A 259      24.051  11.099  25.588  1.00 37.91           C
ATOM    175  CG2  VAL A 259      21.861  12.112  26.308  1.00 38.83           C
ATOM    176  C    VAL A 259      25.267  11.874  28.110  1.00 39.81           C
ATOM    177  O    VAL A 259      25.884  12.938  28.152  1.00 39.70           O
ATOM    178  N    TRP A 260      25.859  10.694  28.208  1.00 43.21           N
ATOM    179  CA   TRP A 260      27.296  10.583  28.390  1.00 43.98           C
ATOM    180  CB   TRP A 260      27.619  10.069  29.799  1.00 44.67           C
ATOM    181  CG   TRP A 260      27.362  11.028  30.909  1.00 46.32           C
ATOM    182  CD2  TRP A 260      28.345  11.621  31.769  1.00 46.96           C
ATOM    183  CE2  TRP A 260      27.658  12.427  32.691  1.00 47.63           C
ATOM    184  CE3  TRP A 260      29.737  11.543  31.847  1.00 46.80           C
ATOM    185  CD1  TRP A 260      26.154  11.491  31.332  1.00 46.35           C
ATOM    186  NE1  TRP A 260      26.322  12.332  32.405  1.00 47.51           N
ATOM    187  CZ2  TRP A 260      28.318  13.155  33.681  1.00 48.56           C
ATOM    188  CZ3  TRP A 260      30.388  12.263  32.826  1.00 46.81           C
ATOM    189  CH2  TRP A 260      29.682  13.059  33.730  1.00 48.39           C
ATOM    190  C    TRP A 260      27.975   9.639  27.422  1.00 43.51           C
ATOM    191  O    TRP A 260      27.365   8.692  26.913  1.00 43.38           O
ATOM    192  N    MET A 261      29.250   9.913  27.171  1.00 39.84           N
ATOM    193  CA   MET A 261      30.070   9.035  26.351  1.00 40.09           C
ATOM    194  CB   MET A 261      31.112   9.812  25.547  1.00 43.94           C
ATOM    195  CG   MET A 261      32.017   8.921  24.684  1.00 44.81           C
ATOM    196  SD   MET A 261      33.309   7.985  25.563  1.00 45.85           S
ATOM    197  CE   MET A 261      34.455   9.297  25.962  1.00 43.93           C
ATOM    198  C    MET A 261      30.771   8.232  27.431  1.00 39.91           C
ATOM    199  O    MET A 261      31.156   8.781  28.459  1.00 39.22           O
ATOM    200  N    GLY A 262      30.911   6.935  27.219  1.00 41.78           N
ATOM    201  CA   GLY A 262      31.580   6.121  28.206  1.00 42.79           C
ATOM    202  C    GLY A 262      32.095   4.878  27.532  1.00 43.70           C
ATOM    203  O    GLY A 262      32.089   4.787  26.306  1.00 44.11           O
ATOM    204  N    TYR A 263      32.556   3.923  28.326  1.00 39.96           N
ATOM    205  CA   TYR A 263      33.040   2.679  27.766  1.00 41.23           C
ATOM    206  CB   TYR A 263      34.553   2.550  27.948  1.00 42.95           C
ATOM    207  CG   TYR A 263      35.307   3.577  27.145  1.00 40.60           C
ATOM    208  CD1  TYR A 263      35.577   4.838  27.671  1.00 40.24           C
ATOM    209  CE1  TYR A 263      36.194   5.807  26.913  1.00 38.58           C
ATOM    210  CD2  TYR A 263      35.681   3.319  25.835  1.00 39.16           C
ATOM    211  CE2  TYR A 263      36.296   4.287  25.068  1.00 39.38           C
ATOM    212  CZ   TYR A 263      36.548   5.528  25.613  1.00 39.25           C
ATOM    213  OH   TYR A 263      37.143   6.500  24.848  1.00 40.76           O
ATOM    214  C    TYR A 263      32.308   1.525  28.417  1.00 42.84           C
ATOM    215  O    TYR A 263      32.085   1.506  29.629  1.00 43.03           O
ATOM    216  N    TYR A 264      31.917   0.569  27.593  1.00 48.13           N
ATOM    217  CA   TYR A 264      31.177  -0.582  28.063  1.00 50.92           C
ATOM    218  CB   TYR A 264      29.958  -0.775  27.155  1.00 65.73           C
ATOM    219  CG   TYR A 264      29.058  -1.927  27.514  1.00 67.93           C
ATOM    220  CD1  TYR A 264      28.672  -2.155  28.828  1.00 68.51           C
ATOM    221  CE1  TYR A 264      27.823  -3.201  29.150  1.00 68.74           C
ATOM    222  CD2  TYR A 264      28.568  -2.776  26.527  1.00 68.26           C
ATOM    223  CE2  TYR A 264      27.723  -3.817  26.837  1.00 68.27           C
ATOM    224  CZ   TYR A 264      27.353  -4.027  28.148  1.00 68.85           C
```

Figure 15

| | | | | | | | | | |
|---|---|---|---|---|---|---|---|---|---|
| ATOM | 225 | OH | TYR | A | 264 | 26.516 | -5.075 | 28.449 | 1.00 69.61 | O |
| ATOM | 226 | C | TYR | A | 264 | 32.091 | -1.803 | 28.060 | 1.00 52.23 | C |
| ATOM | 227 | O | TYR | A | 264 | 32.613 | -2.199 | 27.019 | 1.00 52.03 | O |
| ATOM | 228 | N | ASN | A | 265 | 32.291 | -2.381 | 29.238 | 1.00 61.70 | N |
| ATOM | 229 | CA | ASN | A | 265 | 33.153 | -3.547 | 29.391 | 1.00 64.03 | C |
| ATOM | 230 | CB | ASN | A | 265 | 32.691 | -4.689 | 28.477 | 1.00 63.53 | C |
| ATOM | 231 | CG | ASN | A | 265 | 31.322 | -5.229 | 28.861 | 1.00 65.08 | C |
| ATOM | 232 | OD1 | ASN | A | 265 | 31.102 | -5.639 | 30.002 | 1.00 65.15 | O |
| ATOM | 233 | ND2 | ASN | A | 265 | 30.395 | -5.240 | 27.905 | 1.00 64.62 | N |
| ATOM | 234 | C | ASN | A | 265 | 34.619 | -3.214 | 29.100 | 1.00 65.00 | C |
| ATOM | 235 | O | ASN | A | 265 | 35.402 | -4.093 | 28.740 | 1.00 65.54 | O |
| ATOM | 236 | N | GLY | A | 266 | 34.987 | -1.943 | 29.240 | 1.00 57.02 | N |
| ATOM | 237 | CA | GLY | A | 266 | 36.372 | -1.565 | 29.018 | 1.00 57.27 | C |
| ATOM | 238 | C | GLY | A | 266 | 36.770 | -0.861 | 27.733 | 1.00 57.72 | C |
| ATOM | 239 | O | GLY | A | 266 | 37.415 | 0.188 | 27.787 | 1.00 57.93 | O |
| ATOM | 240 | N | HIS | A | 267 | 36.399 | -1.412 | 26.580 | 1.00 70.53 | N |
| ATOM | 241 | CA | HIS | A | 267 | 36.785 | -0.795 | 25.313 | 1.00 70.38 | C |
| ATOM | 242 | CB | HIS | A | 267 | 37.809 | -1.687 | 24.602 | 1.00116.55 | C |
| ATOM | 243 | CG | HIS | A | 267 | 39.166 | -1.674 | 25.240 | 1.00118.84 | C |
| ATOM | 244 | CD2 | HIS | A | 267 | 40.392 | -1.416 | 24.722 | 1.00119.26 | C |
| ATOM | 245 | ND1 | HIS | A | 267 | 39.370 | -1.975 | 26.572 | 1.00120.07 | N |
| ATOM | 246 | CE1 | HIS | A | 267 | 40.661 | -1.902 | 26.846 | 1.00120.69 | C |
| ATOM | 247 | NE2 | HIS | A | 267 | 41.302 | -1.565 | 25.740 | 1.00120.33 | N |
| ATOM | 248 | C | HIS | A | 267 | 35.684 | -0.408 | 24.325 | 1.00 68.90 | C |
| ATOM | 249 | O | HIS | A | 267 | 35.953 | 0.303 | 23.361 | 1.00 69.21 | O |
| ATOM | 250 | N | THR | A | 268 | 34.457 | -0.869 | 24.540 | 1.00 60.88 | N |
| ATOM | 251 | CA | THR | A | 268 | 33.364 | -0.514 | 23.630 | 1.00 58.41 | C |
| ATOM | 252 | CB | THR | A | 268 | 32.189 | -1.498 | 23.731 | 1.00 54.76 | C |
| ATOM | 253 | OG1 | THR | A | 268 | 32.629 | -2.811 | 23.377 | 1.00 55.10 | O |
| ATOM | 254 | CG2 | THR | A | 268 | 31.060 | -1.074 | 22.792 | 1.00 54.87 | C |
| ATOM | 255 | C | THR | A | 268 | 32.830 | 0.876 | 23.959 | 1.00 55.95 | C |
| ATOM | 256 | O | THR | A | 268 | 32.203 | 1.077 | 24.995 | 1.00 56.24 | O |
| ATOM | 257 | N | LYS | A | 269 | 33.082 | 1.832 | 23.075 | 1.00 46.18 | N |
| ATOM | 258 | CA | LYS | A | 269 | 32.625 | 3.199 | 23.278 | 1.00 44.22 | C |
| ATOM | 259 | CB | LYS | A | 269 | 33.252 | 4.111 | 22.224 | 1.00 48.56 | C |
| ATOM | 260 | CG | LYS | A | 269 | 33.132 | 5.593 | 22.516 | 1.00 48.82 | C |
| ATOM | 261 | CD | LYS | A | 269 | 34.112 | 6.369 | 21.659 | 1.00 49.71 | C |
| ATOM | 262 | CE | LYS | A | 269 | 34.363 | 7.753 | 22.225 | 1.00 50.40 | C |
| ATOM | 263 | NZ | LYS | A | 269 | 35.538 | 8.395 | 21.574 | 1.00 51.68 | N |
| ATOM | 264 | C | LYS | A | 269 | 31.093 | 3.235 | 23.186 | 1.00 42.43 | C |
| ATOM | 265 | O | LYS | A | 269 | 30.505 | 2.653 | 22.274 | 1.00 41.79 | O |
| ATOM | 266 | N | VAL | A | 270 | 30.451 | 3.918 | 24.130 | 1.00 37.29 | N |
| ATOM | 267 | CA | VAL | A | 270 | 28.990 | 3.983 | 24.145 | 1.00 34.75 | C |
| ATOM | 268 | CB | VAL | A | 270 | 28.386 | 2.944 | 25.127 | 1.00 32.01 | C |
| ATOM | 269 | CG1 | VAL | A | 270 | 28.650 | 1.521 | 24.644 | 1.00 28.83 | C |
| ATOM | 270 | CG2 | VAL | A | 270 | 28.977 | 3.174 | 26.524 | 1.00 29.81 | C |
| ATOM | 271 | C | VAL | A | 270 | 28.426 | 5.326 | 24.570 | 1.00 33.73 | C |
| ATOM | 272 | O | VAL | A | 270 | 29.119 | 6.166 | 25.133 | 1.00 33.86 | O |
| ATOM | 273 | N | ALA | A | 271 | 27.150 | 5.523 | 24.269 | 1.00 38.49 | N |
| ATOM | 274 | CA | ALA | A | 271 | 26.447 | 6.721 | 24.688 | 1.00 37.36 | C |
| ATOM | 275 | CB | ALA | A | 271 | 25.556 | 7.244 | 23.587 | 1.00 37.62 | C |
| ATOM | 276 | C | ALA | A | 271 | 25.601 | 6.179 | 25.826 | 1.00 36.26 | C |
| ATOM | 277 | O | ALA | A | 271 | 25.069 | 5.075 | 25.731 | 1.00 35.37 | O |
| ATOM | 278 | N | VAL | A | 272 | 25.491 | 6.941 | 26.902 | 1.00 36.77 | N |
| ATOM | 279 | CA | VAL | A | 272 | 24.714 | 6.510 | 28.047 | 1.00 35.91 | C |
| ATOM | 280 | CB | VAL | A | 272 | 25.622 | 6.193 | 29.266 | 1.00 35.66 | C |
| ATOM | 281 | CG1 | VAL | A | 272 | 24.779 | 5.643 | 30.416 | 1.00 33.08 | C |
| ATOM | 282 | CG2 | VAL | A | 272 | 26.700 | 5.191 | 28.866 | 1.00 35.54 | C |
| ATOM | 283 | C | VAL | A | 272 | 23.744 | 7.602 | 28.445 | 1.00 36.36 | C |
| ATOM | 284 | O | VAL | A | 272 | 24.153 | 8.711 | 28.790 | 1.00 36.26 | O |

Figure 15

| | | | | | | | | | |
|---|---|---|---|---|---|---|---|---|---|
| ATOM | 285 | N | LYS | A | 273 | 22.453 | 7.292 | 28.383 | 1.00 36.34 | N |
| ATOM | 286 | CA | LYS | A | 273 | 21.448 | 8.267 | 28.776 | 1.00 37.08 | C |
| ATOM | 287 | CB | LYS | A | 273 | 20.262 | 8.267 | 27.804 | 1.00 39.42 | C |
| ATOM | 288 | CG | LYS | A | 273 | 19.116 | 9.163 | 28.254 | 1.00 40.27 | C |
| ATOM | 289 | CD | LYS | A | 273 | 17.937 | 9.109 | 27.289 | 1.00 40.90 | C |
| ATOM | 290 | CE | LYS | A | 273 | 18.259 | 9.797 | 25.981 | 1.00 42.32 | C |
| ATOM | 291 | NZ | LYS | A | 273 | 17.111 | 9.756 | 25.035 | 1.00 44.41 | N |
| ATOM | 292 | C | LYS | A | 273 | 20.970 | 7.930 | 30.180 | 1.00 37.12 | C |
| ATOM | 293 | O | LYS | A | 273 | 20.494 | 6.822 | 30.442 | 1.00 36.64 | O |
| ATOM | 294 | N | SER | A | 274 | 21.115 | 8.881 | 31.091 | 1.00 39.59 | N |
| ATOM | 295 | CA | SER | A | 274 | 20.684 | 8.649 | 32.457 | 1.00 41.39 | C |
| ATOM | 296 | CB | SER | A | 274 | 21.826 | 8.914 | 33.436 | 1.00 39.02 | C |
| ATOM | 297 | OG | SER | A | 274 | 22.285 | 10.241 | 33.304 | 1.00 41.56 | O |
| ATOM | 298 | C | SER | A | 274 | 19.502 | 9.545 | 32.783 | 1.00 42.16 | C |
| ATOM | 299 | O | SER | A | 274 | 19.475 | 10.729 | 32.437 | 1.00 42.42 | O |
| ATOM | 300 | N | LEU | A | 275 | 18.527 | 8.954 | 33.459 | 1.00 47.95 | N |
| ATOM | 301 | CA | LEU | A | 275 | 17.312 | 9.646 | 33.853 | 1.00 48.72 | C |
| ATOM | 302 | CB | LEU | A | 275 | 16.193 | 8.624 | 34.073 | 1.00 40.13 | C |
| ATOM | 303 | CG | LEU | A | 275 | 14.918 | 9.154 | 34.732 | 1.00 40.53 | C |
| ATOM | 304 | CD1 | LEU | A | 275 | 14.252 | 10.179 | 33.813 | 1.00 39.86 | C |
| ATOM | 305 | CD2 | LEU | A | 275 | 13.983 | 8.003 | 35.034 | 1.00 38.23 | C |
| ATOM | 306 | C | LEU | A | 275 | 17.489 | 10.466 | 35.121 | 1.00 49.34 | C |
| ATOM | 307 | O | LEU | A | 275 | 18.081 | 10.008 | 36.093 | 1.00 49.55 | O |
| ATOM | 308 | N | LYS | A | 276 | 16.990 | 11.693 | 35.101 | 1.00 45.00 | N |
| ATOM | 309 | CA | LYS | A | 276 | 17.044 | 12.540 | 36.286 | 1.00 46.76 | C |
| ATOM | 310 | CB | LYS | A | 276 | 16.887 | 14.014 | 35.899 | 1.00 60.44 | C |
| ATOM | 311 | CG | LYS | A | 276 | 16.930 | 14.980 | 37.078 | 1.00 62.85 | C |
| ATOM | 312 | CD | LYS | A | 276 | 16.490 | 16.377 | 36.660 | 1.00 64.99 | C |
| ATOM | 313 | CE | LYS | A | 276 | 17.262 | 16.853 | 35.433 | 1.00 65.57 | C |
| ATOM | 314 | NZ | LYS | A | 276 | 16.729 | 18.137 | 34.892 | 1.00 67.20 | N |
| ATOM | 315 | C | LYS | A | 276 | 15.818 | 12.076 | 37.077 | 1.00 47.37 | C |
| ATOM | 316 | O | LYS | A | 276 | 14.709 | 12.074 | 36.542 | 1.00 46.81 | O |
| ATOM | 317 | N | GLN | A | 277 | 16.003 | 11.670 | 38.329 | 1.00 45.67 | N |
| ATOM | 318 | CA | GLN | A | 277 | 14.872 | 11.196 | 39.120 | 1.00 47.19 | C |
| ATOM | 319 | CB | GLN | A | 277 | 15.320 | 10.720 | 40.508 | 1.00 81.54 | C |
| ATOM | 320 | CG | GLN | A | 277 | 14.212 | 9.936 | 41.229 | 1.00 84.53 | C |
| ATOM | 321 | CD | GLN | A | 277 | 14.666 | 9.293 | 42.524 | 1.00 86.36 | C |
| ATOM | 322 | OE1 | GLN | A | 277 | 15.002 | 9.983 | 43.492 | 1.00 87.93 | O |
| ATOM | 323 | NE2 | GLN | A | 277 | 14.675 | 7.960 | 42.552 | 1.00 86.31 | N |
| ATOM | 324 | C | GLN | A | 277 | 13.773 | 12.245 | 39.268 | 1.00 47.16 | C |
| ATOM | 325 | O | GLN | A | 277 | 14.041 | 13.436 | 39.442 | 1.00 47.00 | O |
| ATOM | 326 | N | GLY | A | 278 | 12.529 | 11.790 | 39.183 | 1.00 61.59 | N |
| ATOM | 327 | CA | GLY | A | 278 | 11.404 | 12.695 | 39.301 | 1.00 61.97 | C |
| ATOM | 328 | C | GLY | A | 278 | 10.852 | 13.151 | 37.961 | 1.00 62.47 | C |
| ATOM | 329 | O | GLY | A | 278 | 9.652 | 13.436 | 37.847 | 1.00 63.29 | O |
| ATOM | 330 | N | SER | A | 279 | 11.714 | 13.224 | 36.947 | 1.00 47.28 | N |
| ATOM | 331 | CA | SER | A | 279 | 11.293 | 13.650 | 35.615 | 1.00 46.86 | C |
| ATOM | 332 | CB | SER | A | 279 | 12.446 | 13.492 | 34.621 | 1.00 49.12 | C |
| ATOM | 333 | OG | SER | A | 279 | 13.471 | 14.418 | 34.905 | 1.00 49.36 | O |
| ATOM | 334 | C | SER | A | 279 | 10.106 | 12.816 | 35.158 | 1.00 46.65 | C |
| ATOM | 335 | O | SER | A | 279 | 9.035 | 13.338 | 34.858 | 1.00 46.67 | O |
| ATOM | 336 | N | MET | A | 280 | 10.324 | 11.510 | 35.104 | 1.00 49.90 | N |
| ATOM | 337 | CA | MET | A | 280 | 9.302 | 10.556 | 34.716 | 1.00 49.49 | C |
| ATOM | 338 | CB | MET | A | 280 | 9.339 | 10.311 | 33.204 | 1.00 48.57 | C |
| ATOM | 339 | CG | MET | A | 280 | 10.588 | 9.607 | 32.703 | 1.00 47.93 | C |
| ATOM | 340 | SD | MET | A | 280 | 10.802 | 9.755 | 30.916 | 1.00 48.32 | S |
| ATOM | 341 | CE | MET | A | 280 | 10.023 | 8.315 | 30.366 | 1.00 49.14 | C |
| ATOM | 342 | C | MET | A | 280 | 9.660 | 9.289 | 35.480 | 1.00 49.78 | C |
| ATOM | 343 | O | MET | A | 280 | 10.691 | 9.238 | 36.156 | 1.00 50.24 | O |
| ATOM | 344 | N | SER | A | 281 | 8.826 | 8.266 | 35.383 | 1.00 46.62 | N |

Figure 15

| | | | | | | | | | | |
|---|---|---|---|---|---|---|---|---|---|---|
|ATOM|345|CA|SER|A|281|9.099|7.032|36.099|1.00 46.95|C|
|ATOM|346|CB|SER|A|281|7.800|6.269|36.349|1.00 45.61|C|
|ATOM|347|OG|SER|A|281|7.384|5.577|35.185|1.00 45.48|O|
|ATOM|348|C|SER|A|281|10.064|6.135|35.334|1.00 47.96|C|
|ATOM|349|O|SER|A|281|10.138|6.175|34.103|1.00 47.75|O|
|ATOM|350|N|PRO|A|282|10.822|5.310|36.067|1.00 50.63|N|
|ATOM|351|CD|PRO|A|282|10.878|5.308|37.541|1.00 49.03|C|
|ATOM|352|CA|PRO|A|282|11.797|4.374|35.513|1.00 50.95|C|
|ATOM|353|CB|PRO|A|282|12.126|3.502|36.712|1.00 49.30|C|
|ATOM|354|CG|PRO|A|282|12.135|4.503|37.817|1.00 48.30|C|
|ATOM|355|C|PRO|A|282|11.229|3.578|34.341|1.00 51.90|C|
|ATOM|356|O|PRO|A|282|11.820|3.539|33.261|1.00 52.25|O|
|ATOM|357|N|ASP|A|283|10.080|2.950|34.562|1.00 54.76|N|
|ATOM|358|CA|ASP|A|283|9.410|2.155|33.531|1.00 55.68|C|
|ATOM|359|CB|ASP|A|283|8.079|1.617|34.073|1.00 66.99|C|
|ATOM|360|CG|ASP|A|283|8.270|0.487|35.070|1.00 68.22|C|
|ATOM|361|OD1|ASP|A|283|8.690|-0.608|34.644|1.00 69.23|O|
|ATOM|362|OD2|ASP|A|283|8.010|0.692|36.275|1.00 68.95|O|
|ATOM|363|C|ASP|A|283|9.160|2.963|32.258|1.00 55.54|C|
|ATOM|364|O|ASP|A|283|9.391|2.483|31.145|1.00 55.99|O|
|ATOM|365|N|ALA|A|284|8.678|4.189|32.427|1.00 62.63|N|
|ATOM|366|CA|ALA|A|284|8.406|5.071|31.298|1.00 62.21|C|
|ATOM|367|CB|ALA|A|284|7.760|6.356|31.788|1.00 40.82|C|
|ATOM|368|C|ALA|A|284|9.708|5.388|30.570|1.00 62.32|C|
|ATOM|369|O|ALA|A|284|9.742|5.486|29.343|1.00 63.19|O|
|ATOM|370|N|PHE|A|285|10.776|5.573|31.339|1.00 46.92|N|
|ATOM|371|CA|PHE|A|285|12.086|5.875|30.779|1.00 45.68|C|
|ATOM|372|CB|PHE|A|285|13.059|6.240|31.905|1.00 44.46|C|
|ATOM|373|CG|PHE|A|285|14.442|6.600|31.431|1.00 43.38|C|
|ATOM|374|CD1|PHE|A|285|14.659|7.746|30.672|1.00 42.44|C|
|ATOM|375|CD2|PHE|A|285|15.529|5.807|31.766|1.00 41.82|C|
|ATOM|376|CE1|PHE|A|285|15.931|8.091|30.263|1.00 41.06|C|
|ATOM|377|CE2|PHE|A|285|16.805|6.144|31.361|1.00 40.70|C|
|ATOM|378|CZ|PHE|A|285|17.009|7.288|30.610|1.00 41.67|C|
|ATOM|379|C|PHE|A|285|12.584|4.641|30.044|1.00 46.30|C|
|ATOM|380|O|PHE|A|285|12.977|4.713|28.882|1.00 46.24|O|
|ATOM|381|N|LEU|A|286|12.546|3.505|30.731|1.00 46.83|N|
|ATOM|382|CA|LEU|A|286|13.002|2.247|30.166|1.00 48.11|C|
|ATOM|383|CB|LEU|A|286|13.056|1.179|31.258|1.00 59.34|C|
|ATOM|384|CG|LEU|A|286|14.109|1.472|32.332|1.00 60.58|C|
|ATOM|385|CD1|LEU|A|286|13.985|0.483|33.482|1.00 60.35|C|
|ATOM|386|CD2|LEU|A|286|15.495|1.412|31.702|1.00 60.34|C|
|ATOM|387|C|LEU|A|286|12.139|1.768|29.009|1.00 49.12|C|
|ATOM|388|O|LEU|A|286|12.521|0.847|28.286|1.00 49.17|O|
|ATOM|389|N|ALA|A|287|10.981|2.401|28.829|1.00 66.45|N|
|ATOM|390|CA|ALA|A|287|10.063|2.038|27.753|1.00 66.84|C|
|ATOM|391|CB|ALA|A|287|8.788|2.863|27.856|1.00 68.32|C|
|ATOM|392|C|ALA|A|287|10.725|2.272|26.406|1.00 67.12|C|
|ATOM|393|O|ALA|A|287|10.661|1.428|25.510|1.00 67.77|O|
|ATOM|394|N|GLU|A|288|11.363|3.430|26.281|1.00 65.92|N|
|ATOM|395|CA|GLU|A|288|12.061|3.827|25.064|1.00 65.71|C|
|ATOM|396|CB|GLU|A|288|12.806|5.144|25.306|1.00 89.38|C|
|ATOM|397|CG|GLU|A|288|11.906|6.373|25.308|1.00 91.26|C|
|ATOM|398|CD|GLU|A|288|12.088|7.257|26.528|1.00 92.38|C|
|ATOM|399|OE1|GLU|A|288|13.234|7.683|26.805|1.00 93.50|O|
|ATOM|400|OE2|GLU|A|288|11.072|7.533|27.205|1.00 92.20|O|
|ATOM|401|C|GLU|A|288|13.042|2.772|24.580|1.00 65.06|C|
|ATOM|402|O|GLU|A|288|13.172|2.534|23.377|1.00 65.37|O|
|ATOM|403|N|ALA|A|289|13.734|2.143|25.525|1.00 51.23|N|
|ATOM|404|CA|ALA|A|289|14.715|1.116|25.203|1.00 49.85|C|

Figure 15

```
ATOM    405  CB  ALA A 289      15.487   0.725  26.460  1.00 48.35           C
ATOM    406  C   ALA A 289      14.052  -0.108  24.590  1.00 49.03           C
ATOM    407  O   ALA A 289      14.557  -0.676  23.622  1.00 48.61           O
ATOM    408  N   ASN A 290      12.918  -0.506  25.158  1.00 52.35           N
ATOM    409  CA  ASN A 290      12.175  -1.668  24.675  1.00 52.48           C
ATOM    410  CB  ASN A 290      10.814  -1.744  25.372  1.00 75.48           C
ATOM    411  CG  ASN A 290      10.935  -1.847  26.882  1.00 76.90           C
ATOM    412  OD1 ASN A 290       9.950  -1.693  27.612  1.00 77.70           O
ATOM    413  ND2 ASN A 290      12.146  -2.112  27.359  1.00 76.88           N
ATOM    414  C   ASN A 290      11.969  -1.599  23.165  1.00 51.99           C
ATOM    415  O   ASN A 290      11.943  -2.621  22.488  1.00 51.85           O
ATOM    416  N   LEU A 291      11.827  -0.383  22.649  1.00 54.59           N
ATOM    417  CA  LEU A 291      11.622  -0.159  21.223  1.00 54.00           C
ATOM    418  CB  LEU A 291      11.334   1.322  20.963  1.00 55.60           C
ATOM    419  CG  LEU A 291      10.031   1.858  21.558  1.00 55.96           C
ATOM    420  CD1 LEU A 291      10.009   3.381  21.471  1.00 57.16           C
ATOM    421  CD2 LEU A 291       8.856   1.261  20.818  1.00 55.16           C
ATOM    422  C   LEU A 291      12.823  -0.600  20.401  1.00 53.54           C
ATOM    423  O   LEU A 291      12.670  -1.200  19.338  1.00 52.97           O
ATOM    424  N   MET A 292      14.022  -0.292  20.883  1.00 45.65           N
ATOM    425  CA  MET A 292      15.229  -0.684  20.165  1.00 45.81           C
ATOM    426  CB  MET A 292      16.442   0.043  20.735  1.00 51.09           C
ATOM    427  CG  MET A 292      16.541   1.484  20.268  1.00 50.92           C
ATOM    428  SD  MET A 292      17.797   2.427  21.123  1.00 48.38           S
ATOM    429  CE  MET A 292      16.784   3.150  22.379  1.00 47.44           C
ATOM    430  C   MET A 292      15.424  -2.191  20.241  1.00 46.34           C
ATOM    431  O   MET A 292      16.054  -2.790  19.372  1.00 46.13           O
ATOM    432  N   LYS A 293      14.875  -2.803  21.282  1.00 50.81           N
ATOM    433  CA  LYS A 293      14.978  -4.245  21.440  1.00 52.13           C
ATOM    434  CB  LYS A 293      14.336  -4.701  22.755  1.00 60.79           C
ATOM    435  CG  LYS A 293      14.965  -4.162  24.030  1.00 61.61           C
ATOM    436  CD  LYS A 293      14.473  -4.980  25.229  1.00 62.82           C
ATOM    437  CE  LYS A 293      15.106  -4.546  26.545  1.00 62.99           C
ATOM    438  NZ  LYS A 293      14.600  -3.226  27.014  1.00 63.49           N
ATOM    439  C   LYS A 293      14.245  -4.915  20.282  1.00 52.94           C
ATOM    440  O   LYS A 293      14.799  -5.760  19.582  1.00 53.34           O
ATOM    441  N   GLN A 294      12.996  -4.512  20.081  1.00 64.11           N
ATOM    442  CA  GLN A 294      12.147  -5.080  19.041  1.00 65.10           C
ATOM    443  CB  GLN A 294      10.696  -4.649  19.278  1.00 97.65           C
ATOM    444  CG  GLN A 294      10.236  -4.850  20.718  1.00100.88           C
ATOM    445  CD  GLN A 294      10.407  -6.286  21.202  1.00103.28           C
ATOM    446  OE1 GLN A 294      10.456  -6.545  22.408  1.00104.34           O
ATOM    447  NE2 GLN A 294      10.491  -7.229  20.261  1.00104.44           N
ATOM    448  C   GLN A 294      12.550  -4.763  17.604  1.00 64.45           C
ATOM    449  O   GLN A 294      12.602  -5.665  16.760  1.00 64.88           O
ATOM    450  N   LEU A 295      12.824  -3.493  17.320  1.00 53.67           N
ATOM    451  CA  LEU A 295      13.210  -3.087  15.967  1.00 52.42           C
ATOM    452  CB  LEU A 295      12.467  -1.810  15.549  1.00 59.63           C
ATOM    453  CG  LEU A 295      10.962  -1.895  15.273  1.00 59.76           C
ATOM    454  CD1 LEU A 295      10.447  -0.540  14.822  1.00 60.35           C
ATOM    455  CD2 LEU A 295      10.699  -2.927  14.196  1.00 60.74           C
ATOM    456  C   LEU A 295      14.708  -2.852  15.835  1.00 50.85           C
ATOM    457  O   LEU A 295      15.242  -1.879  16.364  1.00 50.81           O
ATOM    458  N   GLN A 296      15.379  -3.742  15.117  1.00 49.29           N
ATOM    459  CA  GLN A 296      16.813  -3.620  14.910  1.00 48.13           C
ATOM    460  CB  GLN A 296      17.528  -4.820  15.532  1.00 61.95           C
ATOM    461  CG  GLN A 296      17.428  -4.826  17.059  1.00 64.25           C
ATOM    462  CD  GLN A 296      17.801  -6.157  17.680  1.00 65.33           C
ATOM    463  OE1 GLN A 296      18.872  -6.704  17.413  1.00 67.04           O
ATOM    464  NE2 GLN A 296      16.920  -6.683  18.521  1.00 64.30           N
```

Figure 15

| | | | | | | | | | | |
|---|---|---|---|---|---|---|---|---|---|---|
| ATOM | 465 | C | GLN | A | 296 | 17.123 | -3.495 | 13.424 | 1.00 46.89 | C |
| ATOM | 466 | O | GLN | A | 296 | 16.561 | -4.207 | 12.594 | 1.00 46.90 | O |
| ATOM | 467 | N | HIS | A | 297 | 18.016 | -2.571 | 13.092 | 1.00 45.46 | N |
| ATOM | 468 | CA | HIS | A | 297 | 18.371 | -2.330 | 11.704 | 1.00 44.39 | C |
| ATOM | 469 | CB | HIS | A | 297 | 17.200 | -1.620 | 11.000 | 1.00 38.04 | C |
| ATOM | 470 | CG | HIS | A | 297 | 17.297 | -1.602 | 9.505 | 1.00 36.49 | C |
| ATOM | 471 | CD2 | HIS | A | 297 | 16.643 | -2.321 | 8.562 | 1.00 35.89 | C |
| ATOM | 472 | ND1 | HIS | A | 297 | 18.133 | -0.746 | 8.822 | 1.00 35.38 | N |
| ATOM | 473 | CE1 | HIS | A | 297 | 17.989 | -0.937 | 7.522 | 1.00 34.71 | C |
| ATOM | 474 | NE2 | HIS | A | 297 | 17.092 | -1.889 | 7.338 | 1.00 35.52 | N |
| ATOM | 475 | C | HIS | A | 297 | 19.614 | -1.456 | 11.691 | 1.00 44.17 | C |
| ATOM | 476 | O | HIS | A | 297 | 19.845 | -0.682 | 12.620 | 1.00 44.16 | O |
| ATOM | 477 | N | GLN | A | 298 | 20.413 | -1.583 | 10.641 | 1.00 42.22 | N |
| ATOM | 478 | CA | GLN | A | 298 | 21.625 | -0.793 | 10.525 | 1.00 43.47 | C |
| ATOM | 479 | CB | GLN | A | 298 | 22.413 | -1.207 | 9.278 | 1.00 86.30 | C |
| ATOM | 480 | CG | GLN | A | 298 | 23.088 | -2.561 | 9.424 | 1.00 90.00 | C |
| ATOM | 481 | CD | GLN | A | 298 | 24.046 | -2.615 | 10.610 | 1.00 91.62 | C |
| ATOM | 482 | OE1 | GLN | A | 298 | 24.495 | -3.693 | 11.011 | 1.00 93.07 | O |
| ATOM | 483 | NE2 | GLN | A | 298 | 24.368 | -1.449 | 11.171 | 1.00 90.52 | N |
| ATOM | 484 | C | GLN | A | 298 | 21.347 | 0.701 | 10.490 | 1.00 42.43 | C |
| ATOM | 485 | O | GLN | A | 298 | 22.213 | 1.500 | 10.830 | 1.00 41.12 | O |
| ATOM | 486 | N | ARG | A | 299 | 20.138 | 1.075 | 10.083 | 1.00 48.89 | N |
| ATOM | 487 | CA | ARG | A | 299 | 19.766 | 2.486 | 10.014 | 1.00 48.46 | C |
| ATOM | 488 | CB | ARG | A | 299 | 18.774 | 2.718 | 8.873 | 1.00 51.92 | C |
| ATOM | 489 | CG | ARG | A | 299 | 19.323 | 2.368 | 7.514 | 1.00 51.25 | C |
| ATOM | 490 | CD | ARG | A | 299 | 20.700 | 2.972 | 7.337 | 1.00 53.30 | C |
| ATOM | 491 | NE | ARG | A | 299 | 21.235 | 2.700 | 6.011 | 1.00 55.11 | N |
| ATOM | 492 | CZ | ARG | A | 299 | 22.527 | 2.731 | 5.710 | 1.00 56.77 | C |
| ATOM | 493 | NH1 | ARG | A | 299 | 23.422 | 3.018 | 6.650 | 1.00 56.41 | N |
| ATOM | 494 | NH2 | ARG | A | 299 | 22.922 | 2.477 | 4.468 | 1.00 57.60 | N |
| ATOM | 495 | C | ARG | A | 299 | 19.162 | 2.991 | 11.320 | 1.00 48.17 | C |
| ATOM | 496 | O | ARG | A | 299 | 18.836 | 4.171 | 11.441 | 1.00 48.36 | O |
| ATOM | 497 | N | LEU | A | 300 | 19.008 | 2.096 | 12.292 | 1.00 42.69 | N |
| ATOM | 498 | CA | LEU | A | 300 | 18.455 | 2.468 | 13.589 | 1.00 42.70 | C |
| ATOM | 499 | CB | LEU | A | 300 | 17.242 | 1.587 | 13.930 | 1.00 38.87 | C |
| ATOM | 500 | CG | LEU | A | 300 | 15.856 | 2.053 | 13.457 | 1.00 37.74 | C |
| ATOM | 501 | CD1 | LEU | A | 300 | 15.834 | 2.216 | 11.950 | 1.00 35.79 | C |
| ATOM | 502 | CD2 | LEU | A | 300 | 14.811 | 1.046 | 13.905 | 1.00 37.28 | C |
| ATOM | 503 | C | LEU | A | 300 | 19.512 | 2.324 | 14.682 | 1.00 42.54 | C |
| ATOM | 504 | O | LEU | A | 300 | 20.301 | 1.394 | 14.661 | 1.00 43.84 | O |
| ATOM | 505 | N | VAL | A | 301 | 19.526 | 3.249 | 15.631 | 1.00 41.33 | N |
| ATOM | 506 | CA | VAL | A | 301 | 20.479 | 3.198 | 16.730 | 1.00 41.19 | C |
| ATOM | 507 | CB | VAL | A | 301 | 20.259 | 4.369 | 17.707 | 1.00 36.92 | C |
| ATOM | 508 | CG1 | VAL | A | 301 | 21.110 | 4.171 | 18.953 | 1.00 36.51 | C |
| ATOM | 509 | CG2 | VAL | A | 301 | 20.605 | 5.694 | 17.018 | 1.00 35.79 | C |
| ATOM | 510 | C | VAL | A | 301 | 20.337 | 1.883 | 17.493 | 1.00 41.64 | C |
| ATOM | 511 | O | VAL | A | 301 | 19.243 | 1.521 | 17.930 | 1.00 41.36 | O |
| ATOM | 512 | N | ARG | A | 302 | 21.452 | 1.175 | 17.651 | 1.00 48.52 | N |
| ATOM | 513 | CA | ARG | A | 302 | 21.460 | -0.108 | 18.340 | 1.00 49.95 | C |
| ATOM | 514 | CB | ARG | A | 302 | 22.612 | -0.974 | 17.817 | 1.00 66.39 | C |
| ATOM | 515 | CG | ARG | A | 302 | 22.779 | -2.279 | 18.568 | 1.00 69.57 | C |
| ATOM | 516 | CD | ARG | A | 302 | 24.051 | -3.006 | 18.166 | 1.00 72.14 | C |
| ATOM | 517 | NE | ARG | A | 302 | 24.318 | -4.131 | 19.061 | 1.00 74.72 | N |
| ATOM | 518 | CZ | ARG | A | 302 | 25.358 | -4.950 | 18.950 | 1.00 76.44 | C |
| ATOM | 519 | NH1 | ARG | A | 302 | 26.241 | -4.780 | 17.975 | 1.00 76.49 | N |
| ATOM | 520 | NH2 | ARG | A | 302 | 25.518 | -5.937 | 19.821 | 1.00 77.90 | N |
| ATOM | 521 | C | ARG | A | 302 | 21.578 | 0.009 | 19.858 | 1.00 50.09 | C |
| ATOM | 522 | O | ARG | A | 302 | 22.443 | 0.727 | 20.373 | 1.00 50.45 | O |
| ATOM | 523 | N | LEU | A | 303 | 20.710 | -0.708 | 20.566 | 1.00 44.31 | N |
| ATOM | 524 | CA | LEU | A | 303 | 20.720 | -0.711 | 22.027 | 1.00 44.04 | C |

Figure 15

| | | | | | | | | | | |
|---|---|---|---|---|---|---|---|---|---|---|
| ATOM | 525 | CB  | LEU | A | 303 | 19.321 | -0.982 | 22.579 | 1.00 42.30 | C |
| ATOM | 526 | CG  | LEU | A | 303 | 19.323 | -1.252 | 24.088 | 1.00 41.28 | C |
| ATOM | 527 | CD1 | LEU | A | 303 | 19.466 |  0.064 | 24.828 | 1.00 40.04 | C |
| ATOM | 528 | CD2 | LEU | A | 303 | 18.053 | -1.962 | 24.503 | 1.00 40.57 | C |
| ATOM | 529 | C   | LEU | A | 303 | 21.662 | -1.785 | 22.561 | 1.00 44.55 | C |
| ATOM | 530 | O   | LEU | A | 303 | 21.663 | -2.917 | 22.078 | 1.00 44.58 | O |
| ATOM | 531 | N   | TYR | A | 304 | 22.463 | -1.436 | 23.561 | 1.00 46.12 | N |
| ATOM | 532 | CA  | TYR | A | 304 | 23.374 | -2.407 | 24.145 | 1.00 47.10 | C |
| ATOM | 533 | CB  | TYR | A | 304 | 24.771 | -1.806 | 24.338 | 1.00 58.42 | C |
| ATOM | 534 | CG  | TYR | A | 304 | 25.555 | -1.630 | 23.055 | 1.00 59.23 | C |
| ATOM | 535 | CD1 | TYR | A | 304 | 25.244 | -2.367 | 21.926 | 1.00 60.51 | C |
| ATOM | 536 | CE1 | TYR | A | 304 | 25.984 | -2.240 | 20.762 | 1.00 62.27 | C |
| ATOM | 537 | CD2 | TYR | A | 304 | 26.633 | -0.755 | 22.990 | 1.00 60.23 | C |
| ATOM | 538 | CE2 | TYR | A | 304 | 27.383 | -0.622 | 21.833 | 1.00 60.73 | C |
| ATOM | 539 | CZ  | TYR | A | 304 | 27.051 | -1.368 | 20.721 | 1.00 61.14 | C |
| ATOM | 540 | OH  | TYR | A | 304 | 27.775 | -1.245 | 19.562 | 1.00 62.32 | O |
| ATOM | 541 | C   | TYR | A | 304 | 22.862 | -2.929 | 25.485 | 1.00 47.22 | C |
| ATOM | 542 | O   | TYR | A | 304 | 22.833 | -4.131 | 25.723 | 1.00 47.57 | O |
| ATOM | 543 | N   | ALA | A | 305 | 22.438 | -2.026 | 26.356 | 1.00 42.73 | N |
| ATOM | 544 | CA  | ALA | A | 305 | 21.965 | -2.445 | 27.661 | 1.00 43.16 | C |
| ATOM | 545 | CB  | ALA | A | 305 | 23.139 | -2.964 | 28.488 | 1.00 49.81 | C |
| ATOM | 546 | C   | ALA | A | 305 | 21.277 | -1.322 | 28.409 | 1.00 43.56 | C |
| ATOM | 547 | O   | ALA | A | 305 | 21.204 | -0.183 | 27.938 | 1.00 43.15 | O |
| ATOM | 548 | N   | VAL | A | 306 | 20.780 | -1.664 | 29.591 | 1.00 51.71 | N |
| ATOM | 549 | CA  | VAL | A | 306 | 20.103 | -0.718 | 30.456 | 1.00 52.73 | C |
| ATOM | 550 | CB  | VAL | A | 306 | 18.568 | -0.849 | 30.357 | 1.00 51.97 | C |
| ATOM | 551 | CG1 | VAL | A | 306 | 18.112 | -0.702 | 28.911 | 1.00 50.79 | C |
| ATOM | 552 | CG2 | VAL | A | 306 | 18.131 | -2.186 | 30.934 | 1.00 51.59 | C |
| ATOM | 553 | C   | VAL | A | 306 | 20.502 | -1.026 | 31.892 | 1.00 54.07 | C |
| ATOM | 554 | O   | VAL | A | 306 | 20.901 | -2.150 | 32.203 | 1.00 55.03 | O |
| ATOM | 555 | N   | VAL | A | 307 | 20.407 | -0.020 | 32.755 | 1.00 46.62 | N |
| ATOM | 556 | CA  | VAL | A | 307 | 20.711 | -0.174 | 34.172 | 1.00 47.62 | C |
| ATOM | 557 | CB  | VAL | A | 307 | 21.914 |  0.700 | 34.600 | 1.00 49.18 | C |
| ATOM | 558 | CG1 | VAL | A | 307 | 22.136 |  0.592 | 36.099 | 1.00 48.34 | C |
| ATOM | 559 | CG2 | VAL | A | 307 | 23.160 |  0.247 | 33.863 | 1.00 49.33 | C |
| ATOM | 560 | C   | VAL | A | 307 | 19.447 |  0.262 | 34.914 | 1.00 48.34 | C |
| ATOM | 561 | O   | VAL | A | 307 | 19.072 |  1.435 | 34.896 | 1.00 47.72 | O |
| ATOM | 562 | N   | THR | A | 308 | 18.802 | -0.698 | 35.567 | 1.00 68.73 | N |
| ATOM | 563 | CA  | THR | A | 308 | 17.549 | -0.464 | 36.281 | 1.00 70.31 | C |
| ATOM | 564 | CB  | THR | A | 308 | 16.758 | -1.775 | 36.392 | 1.00 57.18 | C |
| ATOM | 565 | OG1 | THR | A | 308 | 17.555 | -2.759 | 37.061 | 1.00 57.96 | O |
| ATOM | 566 | CG2 | THR | A | 308 | 16.397 | -2.285 | 35.005 | 1.00 56.60 | C |
| ATOM | 567 | C   | THR | A | 308 | 17.600 |  0.188 | 37.661 | 1.00 70.88 | C |
| ATOM | 568 | O   | THR | A | 308 | 16.553 |  0.454 | 38.254 | 1.00 71.22 | O |
| ATOM | 569 | N   | GLN | A | 309 | 18.797 |  0.445 | 38.178 | 1.00 50.20 | N |
| ATOM | 570 | CA  | GLN | A | 309 | 18.920 |  1.100 | 39.476 | 1.00 50.32 | C |
| ATOM | 571 | CB  | GLN | A | 309 | 20.007 |  0.437 | 40.323 | 1.00 87.44 | C |
| ATOM | 572 | CG  | GLN | A | 309 | 19.483 | -0.686 | 41.187 | 1.00 90.13 | C |
| ATOM | 573 | CD  | GLN | A | 309 | 18.319 | -0.238 | 42.049 | 1.00 91.69 | C |
| ATOM | 574 | OE1 | GLN | A | 309 | 18.462 |  0.663 | 42.878 | 1.00 92.69 | O |
| ATOM | 575 | NE2 | GLN | A | 309 | 17.155 | -0.860 | 41.856 | 1.00 91.82 | N |
| ATOM | 576 | C   | GLN | A | 309 | 19.232 |  2.580 | 39.318 | 1.00 49.44 | C |
| ATOM | 577 | O   | GLN | A | 309 | 20.035 |  2.966 | 38.470 | 1.00 49.59 | O |
| ATOM | 578 | N   | GLU | A | 310 | 18.596 |  3.401 | 40.148 | 1.00 60.83 | N |
| ATOM | 579 | CA  | GLU | A | 310 | 18.783 |  4.848 | 40.112 | 1.00 59.91 | C |
| ATOM | 580 | CB  | GLU | A | 310 | 17.952 |  5.511 | 41.213 | 1.00 86.64 | C |
| ATOM | 581 | CG  | GLU | A | 310 | 16.586 |  4.875 | 41.448 | 1.00 89.10 | C |
| ATOM | 582 | CD  | GLU | A | 310 | 15.574 |  5.200 | 40.362 | 1.00 89.74 | C |
| ATOM | 583 | OE1 | GLU | A | 310 | 15.241 |  6.393 | 40.193 | 1.00 90.82 | O |
| ATOM | 584 | OE2 | GLU | A | 310 | 15.108 |  4.262 | 39.682 | 1.00 90.04 | O |

Figure 15

| | | | | | | | | | | |
|---|---|---|---|---|---|---|---|---|---|---|
| ATOM | 585 | C | GLU | A | 310 | 20.252 | 5.226 | 40.306 | 1.00 58.48 | C |
| ATOM | 586 | O | GLU | A | 310 | 20.906 | 4.757 | 41.239 | 1.00 58.35 | O |
| ATOM | 587 | N | PRO | A | 311 | 20.788 | 6.079 | 39.416 | 1.00 57.52 | N |
| ATOM | 588 | CD | PRO | A | 311 | 22.104 | 6.734 | 39.527 | 1.00 54.22 | C |
| ATOM | 589 | CA | PRO | A | 311 | 20.018 | 6.632 | 38.299 | 1.00 56.11 | C |
| ATOM | 590 | CB | PRO | A | 311 | 20.810 | 7.878 | 37.921 | 1.00 53.45 | C |
| ATOM | 591 | CG | PRO | A | 311 | 22.229 | 7.451 | 38.196 | 1.00 55.12 | C |
| ATOM | 592 | C | PRO | A | 311 | 19.930 | 5.622 | 37.160 | 1.00 54.42 | C |
| ATOM | 593 | O | PRO | A | 311 | 20.899 | 4.923 | 36.868 | 1.00 54.29 | O |
| ATOM | 594 | N | ILE | A | 312 | 18.760 | 5.536 | 36.537 | 1.00 44.18 | N |
| ATOM | 595 | CA | ILE | A | 312 | 18.541 | 4.609 | 35.431 | 1.00 41.83 | C |
| ATOM | 596 | CB | ILE | A | 312 | 17.079 | 4.671 | 34.938 | 1.00 52.41 | C |
| ATOM | 597 | CG2 | ILE | A | 312 | 16.851 | 3.629 | 33.854 | 1.00 53.20 | C |
| ATOM | 598 | CG1 | ILE | A | 312 | 16.124 | 4.429 | 36.104 | 1.00 53.47 | C |
| ATOM | 599 | CD1 | ILE | A | 312 | 16.276 | 3.070 | 36.731 | 1.00 54.92 | C |
| ATOM | 600 | C | ILE | A | 312 | 19.467 | 4.939 | 34.252 | 1.00 39.80 | C |
| ATOM | 601 | O | ILE | A | 312 | 19.766 | 6.105 | 33.980 | 1.00 37.54 | O |
| ATOM | 602 | N | TYR | A | 313 | 19.912 | 3.896 | 33.558 | 1.00 37.43 | N |
| ATOM | 603 | CA | TYR | A | 313 | 20.803 | 4.055 | 32.414 | 1.00 36.69 | C |
| ATOM | 604 | CB | TYR | A | 313 | 22.205 | 3.494 | 32.719 | 1.00 39.47 | C |
| ATOM | 605 | CG | TYR | A | 313 | 23.135 | 4.351 | 33.550 | 1.00 38.65 | C |
| ATOM | 606 | CD1 | TYR | A | 313 | 22.735 | 5.579 | 34.050 | 1.00 38.80 | C |
| ATOM | 607 | CE1 | TYR | A | 313 | 23.606 | 6.366 | 34.803 | 1.00 39.22 | C |
| ATOM | 608 | CD2 | TYR | A | 313 | 24.435 | 3.924 | 33.825 | 1.00 38.65 | C |
| ATOM | 609 | CE2 | TYR | A | 313 | 25.312 | 4.702 | 34.575 | 1.00 37.79 | C |
| ATOM | 610 | CZ | TYR | A | 313 | 24.892 | 5.920 | 35.061 | 1.00 39.01 | C |
| ATOM | 611 | OH | TYR | A | 313 | 25.748 | 6.705 | 35.808 | 1.00 40.21 | O |
| ATOM | 612 | C | TYR | A | 313 | 20.309 | 3.323 | 31.173 | 1.00 36.12 | C |
| ATOM | 613 | O | TYR | A | 313 | 19.789 | 2.207 | 31.250 | 1.00 35.70 | O |
| ATOM | 614 | N | ILE | A | 314 | 20.480 | 3.965 | 30.027 | 1.00 36.43 | N |
| ATOM | 615 | CA | ILE | A | 314 | 20.161 | 3.342 | 28.754 | 1.00 35.60 | C |
| ATOM | 616 | CB | ILE | A | 314 | 19.036 | 4.064 | 27.997 | 1.00 41.49 | C |
| ATOM | 617 | CG2 | ILE | A | 314 | 18.833 | 3.405 | 26.635 | 1.00 39.64 | C |
| ATOM | 618 | CG1 | ILE | A | 314 | 17.737 | 3.998 | 28.806 | 1.00 41.67 | C |
| ATOM | 619 | CD1 | ILE | A | 314 | 16.572 | 4.726 | 28.166 | 1.00 40.97 | C |
| ATOM | 620 | C | ILE | A | 314 | 21.475 | 3.476 | 27.991 | 1.00 35.06 | C |
| ATOM | 621 | O | ILE | A | 314 | 22.006 | 4.578 | 27.849 | 1.00 35.66 | O |
| ATOM | 622 | N | ILE | A | 315 | 22.012 | 2.358 | 27.522 | 1.00 39.18 | N |
| ATOM | 623 | CA | ILE | A | 315 | 23.283 | 2.373 | 26.811 | 1.00 39.42 | C |
| ATOM | 624 | CB | ILE | A | 315 | 24.346 | 1.461 | 27.514 | 1.00 38.44 | C |
| ATOM | 625 | CG2 | ILE | A | 315 | 25.720 | 1.661 | 26.885 | 1.00 38.15 | C |
| ATOM | 626 | CG1 | ILE | A | 315 | 24.421 | 1.778 | 29.009 | 1.00 38.59 | C |
| ATOM | 627 | CD1 | ILE | A | 315 | 23.538 | 0.885 | 29.867 | 1.00 39.98 | C |
| ATOM | 628 | C | ILE | A | 315 | 23.137 | 1.901 | 25.375 | 1.00 38.81 | C |
| ATOM | 629 | O | ILE | A | 315 | 22.605 | 0.823 | 25.117 | 1.00 39.12 | O |
| ATOM | 630 | N | THR | A | 316 | 23.617 | 2.714 | 24.441 | 1.00 36.31 | N |
| ATOM | 631 | CA | THR | A | 316 | 23.560 | 2.368 | 23.029 | 1.00 35.84 | C |
| ATOM | 632 | CB | THR | A | 316 | 22.585 | 3.263 | 22.263 | 1.00 36.91 | C |
| ATOM | 633 | OG1 | THR | A | 316 | 23.138 | 4.588 | 22.169 | 1.00 36.39 | O |
| ATOM | 634 | CG2 | THR | A | 316 | 21.229 | 3.306 | 22.966 | 1.00 35.24 | C |
| ATOM | 635 | C | THR | A | 316 | 24.929 | 2.587 | 22.407 | 1.00 36.52 | C |
| ATOM | 636 | O | THR | A | 316 | 25.831 | 3.134 | 23.048 | 1.00 35.80 | O |
| ATOM | 637 | N | GLU | A | 317 | 25.073 | 2.165 | 21.154 | 1.00 38.47 | N |
| ATOM | 638 | CA | GLU | A | 317 | 26.318 | 2.365 | 20.427 | 1.00 38.73 | C |
| ATOM | 639 | CB | GLU | A | 317 | 26.178 | 1.903 | 18.973 | 1.00 40.62 | C |
| ATOM | 640 | CG | GLU | A | 317 | 25.211 | 2.753 | 18.134 | 1.00 41.79 | C |
| ATOM | 641 | CD | GLU | A | 317 | 25.039 | 2.224 | 16.722 | 1.00 44.18 | C |
| ATOM | 642 | OE1 | GLU | A | 317 | 26.060 | 2.030 | 16.021 | 1.00 47.12 | O |
| ATOM | 643 | OE2 | GLU | A | 317 | 23.884 | 1.999 | 16.307 | 1.00 44.42 | O |
| ATOM | 644 | C | GLU | A | 317 | 26.582 | 3.872 | 20.451 | 1.00 38.80 | C |

Figure 15

| | | | | | | | | | | |
|---|---|---|---|---|---|---|---|---|---|---|
| ATOM | 645 | O | GLU | A | 317 | 25.668 | 4.675 | 20.665 | 1.00 38.14 | O |
| ATOM | 646 | N | TYR | A | 318 | 27.833 | 4.244 | 20.222 | 1.00 36.25 | N |
| ATOM | 647 | CA | TYR | A | 318 | 28.227 | 5.642 | 20.221 | 1.00 35.90 | C |
| ATOM | 648 | CB | TYR | A | 318 | 29.641 | 5.763 | 20.796 | 1.00 38.19 | C |
| ATOM | 649 | CG | TYR | A | 318 | 30.156 | 7.176 | 20.862 | 1.00 38.75 | C |
| ATOM | 650 | CD1 | TYR | A | 318 | 29.600 | 8.094 | 21.744 | 1.00 39.77 | C |
| ATOM | 651 | CE1 | TYR | A | 318 | 30.056 | 9.401 | 21.795 | 1.00 40.20 | C |
| ATOM | 652 | CD2 | TYR | A | 318 | 31.186 | 7.603 | 20.030 | 1.00 37.86 | C |
| ATOM | 653 | CE2 | TYR | A | 318 | 31.644 | 8.901 | 20.071 | 1.00 37.11 | C |
| ATOM | 654 | CZ | TYR | A | 318 | 31.077 | 9.793 | 20.953 | 1.00 39.05 | C |
| ATOM | 655 | OH | TYR | A | 318 | 31.526 | 11.082 | 21.009 | 1.00 41.32 | O |
| ATOM | 656 | C | TYR | A | 318 | 28.176 | 6.245 | 18.807 | 1.00 35.78 | C |
| ATOM | 657 | O | TYR | A | 318 | 28.567 | 5.605 | 17.833 | 1.00 34.72 | O |
| ATOM | 658 | N | MET | A | 319 | 27.669 | 7.470 | 18.705 | 1.00 35.95 | N |
| ATOM | 659 | CA | MET | A | 319 | 27.599 | 8.157 | 17.420 | 1.00 37.17 | C |
| ATOM | 660 | CB | MET | A | 319 | 26.156 | 8.564 | 17.091 | 1.00 39.60 | C |
| ATOM | 661 | CG | MET | A | 319 | 25.199 | 7.387 | 16.867 | 1.00 40.05 | C |
| ATOM | 662 | SD | MET | A | 319 | 25.686 | 6.267 | 15.531 | 1.00 43.26 | S |
| ATOM | 663 | CE | MET | A | 319 | 24.906 | 7.111 | 14.102 | 1.00 42.03 | C |
| ATOM | 664 | C | MET | A | 319 | 28.503 | 9.386 | 17.485 | 1.00 37.31 | C |
| ATOM | 665 | O | MET | A | 319 | 28.128 | 10.431 | 18.013 | 1.00 36.88 | O |
| ATOM | 666 | N | GLU | A | 320 | 29.697 | 9.229 | 16.932 | 1.00 39.62 | N |
| ATOM | 667 | CA | GLU | A | 320 | 30.738 | 10.248 | 16.903 | 1.00 40.18 | C |
| ATOM | 668 | CB | GLU | A | 320 | 31.894 | 9.755 | 16.030 | 1.00 65.19 | C |
| ATOM | 669 | CG | GLU | A | 320 | 33.170 | 10.564 | 16.181 | 1.00 68.85 | C |
| ATOM | 670 | CD | GLU | A | 320 | 33.427 | 10.973 | 17.616 | 1.00 70.04 | C |
| ATOM | 671 | OE1 | GLU | A | 320 | 33.570 | 10.079 | 18.481 | 1.00 72.68 | O |
| ATOM | 672 | OE2 | GLU | A | 320 | 33.482 | 12.186 | 17.881 | 1.00 71.22 | O |
| ATOM | 673 | C | GLU | A | 320 | 30.377 | 11.674 | 16.483 | 1.00 40.07 | C |
| ATOM | 674 | O | GLU | A | 320 | 30.965 | 12.626 | 16.992 | 1.00 40.22 | O |
| ATOM | 675 | N | ASN | A | 321 | 29.427 | 11.843 | 15.570 | 1.00 42.10 | N |
| ATOM | 676 | CA | ASN | A | 321 | 29.077 | 13.189 | 15.131 | 1.00 41.80 | C |
| ATOM | 677 | CB | ASN | A | 321 | 29.107 | 13.256 | 13.598 | 1.00 36.05 | C |
| ATOM | 678 | CG | ASN | A | 321 | 30.530 | 13.196 | 13.052 | 1.00 35.96 | C |
| ATOM | 679 | OD1 | ASN | A | 321 | 31.375 | 14.010 | 13.418 | 1.00 33.93 | O |
| ATOM | 680 | ND2 | ASN | A | 321 | 30.799 | 12.229 | 12.186 | 1.00 35.07 | N |
| ATOM | 681 | C | ASN | A | 321 | 27.756 | 13.726 | 15.671 | 1.00 42.15 | C |
| ATOM | 682 | O | ASN | A | 321 | 27.270 | 14.767 | 15.227 | 1.00 41.91 | O |
| ATOM | 683 | N | GLY | A | 322 | 27.188 | 13.012 | 16.637 | 1.00 37.86 | N |
| ATOM | 684 | CA | GLY | A | 322 | 25.944 | 13.427 | 17.256 | 1.00 37.52 | C |
| ATOM | 685 | C | GLY | A | 322 | 24.715 | 13.586 | 16.373 | 1.00 37.89 | C |
| ATOM | 686 | O | GLY | A | 322 | 24.523 | 12.864 | 15.389 | 1.00 37.06 | O |
| ATOM | 687 | N | SER | A | 323 | 23.877 | 14.549 | 16.751 | 1.00 38.11 | N |
| ATOM | 688 | CA | SER | A | 323 | 22.634 | 14.848 | 16.056 | 1.00 38.61 | C |
| ATOM | 689 | CB | SER | A | 323 | 21.737 | 15.710 | 16.945 | 1.00 46.44 | C |
| ATOM | 690 | OG | SER | A | 323 | 20.807 | 16.439 | 16.170 | 1.00 49.77 | O |
| ATOM | 691 | C | SER | A | 323 | 22.856 | 15.541 | 14.727 | 1.00 38.54 | C |
| ATOM | 692 | O | SER | A | 323 | 23.609 | 16.508 | 14.635 | 1.00 37.90 | O |
| ATOM | 693 | N | LEU | A | 324 | 22.175 | 15.049 | 13.698 | 1.00 38.26 | N |
| ATOM | 694 | CA | LEU | A | 324 | 22.315 | 15.608 | 12.357 | 1.00 38.42 | C |
| ATOM | 695 | CB | LEU | A | 324 | 21.380 | 14.864 | 11.396 | 1.00 35.00 | C |
| ATOM | 696 | CG | LEU | A | 324 | 21.237 | 15.350 | 9.951 | 1.00 34.55 | C |
| ATOM | 697 | CD1 | LEU | A | 324 | 22.526 | 15.127 | 9.169 | 1.00 31.86 | C |
| ATOM | 698 | CD2 | LEU | A | 324 | 20.077 | 14.589 | 9.301 | 1.00 33.39 | C |
| ATOM | 699 | C | LEU | A | 324 | 22.053 | 17.119 | 12.295 | 1.00 38.05 | C |
| ATOM | 700 | O | LEU | A | 324 | 22.748 | 17.842 | 11.597 | 1.00 38.43 | O |
| ATOM | 701 | N | VAL | A | 325 | 21.056 | 17.599 | 13.026 | 1.00 41.26 | N |
| ATOM | 702 | CA | VAL | A | 325 | 20.744 | 19.026 | 12.996 | 1.00 41.11 | C |
| ATOM | 703 | CB | VAL | A | 325 | 19.477 | 19.352 | 13.842 | 1.00 31.57 | C |
| ATOM | 704 | CG1 | VAL | A | 325 | 19.808 | 19.360 | 15.319 | 1.00 29.40 | C |

Figure 15

| | | | | | | | | | |
|---|---|---|---|---|---|---|---|---|---|
| ATOM | 705 | CG2 | VAL | A | 325 | 18.878 | 20.687 | 13.396 | 1.00 30.66 | C |
| ATOM | 706 | C | VAL | A | 325 | 21.921 | 19.886 | 13.460 | 1.00 42.04 | C |
| ATOM | 707 | O | VAL | A | 325 | 22.038 | 21.048 | 13.056 | 1.00 42.46 | O |
| ATOM | 708 | N | ASP | A | 326 | 22.792 | 19.321 | 14.297 | 1.00 41.83 | N |
| ATOM | 709 | CA | ASP | A | 326 | 23.970 | 20.053 | 14.777 | 1.00 42.84 | C |
| ATOM | 710 | CB | ASP | A | 326 | 24.359 | 19.638 | 16.205 | 1.00 41.88 | C |
| ATOM | 711 | CG | ASP | A | 326 | 23.306 | 20.001 | 17.227 | 1.00 42.36 | C |
| ATOM | 712 | OD1 | ASP | A | 326 | 22.762 | 21.116 | 17.155 | 1.00 43.66 | O |
| ATOM | 713 | OD2 | ASP | A | 326 | 23.027 | 19.173 | 18.115 | 1.00 44.54 | O |
| ATOM | 714 | C | ASP | A | 326 | 25.166 | 19.817 | 13.865 | 1.00 43.16 | C |
| ATOM | 715 | O | ASP | A | 326 | 25.935 | 20.737 | 13.594 | 1.00 43.57 | O |
| ATOM | 716 | N | PHE | A | 327 | 25.326 | 18.585 | 13.393 | 1.00 42.99 | N |
| ATOM | 717 | CA | PHE | A | 327 | 26.444 | 18.268 | 12.518 | 1.00 43.65 | C |
| ATOM | 718 | CB | PHE | A | 327 | 26.462 | 16.784 | 12.168 | 1.00 43.44 | C |
| ATOM | 719 | CG | PHE | A | 327 | 27.498 | 16.427 | 11.140 | 1.00 43.22 | C |
| ATOM | 720 | CD1 | PHE | A | 327 | 28.849 | 16.572 | 11.421 | 1.00 44.07 | C |
| ATOM | 721 | CD2 | PHE | A | 327 | 27.128 | 15.979 | 9.889 | 1.00 44.26 | C |
| ATOM | 722 | CE1 | PHE | A | 327 | 29.810 | 16.277 | 10.468 | 1.00 43.29 | C |
| ATOM | 723 | CE2 | PHE | A | 327 | 28.085 | 15.681 | 8.931 | 1.00 44.47 | C |
| ATOM | 724 | CZ | PHE | A | 327 | 29.427 | 15.833 | 9.225 | 1.00 43.23 | C |
| ATOM | 725 | C | PHE | A | 327 | 26.414 | 19.063 | 11.220 | 1.00 45.17 | C |
| ATOM | 726 | O | PHE | A | 327 | 27.460 | 19.495 | 10.721 | 1.00 45.71 | O |
| ATOM | 727 | N | LEU | A | 328 | 25.219 | 19.231 | 10.663 | 1.00 38.53 | N |
| ATOM | 728 | CA | LEU | A | 328 | 25.053 | 19.958 | 9.416 | 1.00 39.42 | C |
| ATOM | 729 | CB | LEU | A | 328 | 23.570 | 20.027 | 9.044 | 1.00 45.79 | C |
| ATOM | 730 | CG | LEU | A | 328 | 22.891 | 18.718 | 8.649 | 1.00 45.11 | C |
| ATOM | 731 | CD1 | LEU | A | 328 | 21.391 | 18.888 | 8.729 | 1.00 45.72 | C |
| ATOM | 732 | CD2 | LEU | A | 328 | 23.322 | 18.322 | 7.247 | 1.00 45.31 | C |
| ATOM | 733 | C | LEU | A | 328 | 25.614 | 21.368 | 9.508 | 1.00 40.31 | C |
| ATOM | 734 | O | LEU | A | 328 | 26.064 | 21.933 | 8.511 | 1.00 39.56 | O |
| ATOM | 735 | N | LYS | A | 329 | 25.584 | 21.930 | 10.710 | 1.00 57.84 | N |
| ATOM | 736 | CA | LYS | A | 329 | 26.069 | 23.286 | 10.938 | 1.00 59.37 | C |
| ATOM | 737 | CB | LYS | A | 329 | 25.378 | 23.894 | 12.163 | 1.00 57.78 | C |
| ATOM | 738 | CG | LYS | A | 329 | 23.860 | 24.058 | 12.035 | 1.00 58.59 | C |
| ATOM | 739 | CD | LYS | A | 329 | 23.289 | 24.715 | 13.293 | 1.00 58.15 | C |
| ATOM | 740 | CE | LYS | A | 329 | 21.790 | 24.958 | 13.195 | 1.00 58.55 | C |
| ATOM | 741 | NZ | LYS | A | 329 | 21.006 | 23.690 | 13.137 | 1.00 59.61 | N |
| ATOM | 742 | C | LYS | A | 329 | 27.583 | 23.389 | 11.118 | 1.00 59.88 | C |
| ATOM | 743 | O | LYS | A | 329 | 28.146 | 24.471 | 10.963 | 1.00 60.56 | O |
| ATOM | 744 | N | THR | A | 330 | 28.239 | 22.277 | 11.442 | 1.00 48.52 | N |
| ATOM | 745 | CA | THR | A | 330 | 29.688 | 22.285 | 11.644 | 1.00 48.68 | C |
| ATOM | 746 | CB | THR | A | 330 | 30.201 | 20.926 | 12.197 | 1.00 45.47 | C |
| ATOM | 747 | OG1 | THR | A | 330 | 30.158 | 19.937 | 11.162 | 1.00 45.12 | O |
| ATOM | 748 | CG2 | THR | A | 330 | 29.357 | 20.466 | 13.371 | 1.00 44.95 | C |
| ATOM | 749 | C | THR | A | 330 | 30.437 | 22.560 | 10.342 | 1.00 49.20 | C |
| ATOM | 750 | O | THR | A | 330 | 29.916 | 22.321 | 9.255 | 1.00 49.10 | O |
| ATOM | 751 | N | PRO | A | 331 | 31.675 | 23.076 | 10.443 | 1.00 51.38 | N |
| ATOM | 752 | CD | PRO | A | 331 | 32.330 | 23.555 | 11.676 | 1.00 60.29 | C |
| ATOM | 753 | CA | PRO | A | 331 | 32.501 | 23.377 | 9.269 | 1.00 51.81 | C |
| ATOM | 754 | CB | PRO | A | 331 | 33.861 | 23.697 | 9.883 | 1.00 60.53 | C |
| ATOM | 755 | CG | PRO | A | 331 | 33.470 | 24.423 | 11.135 | 1.00 60.06 | C |
| ATOM | 756 | C | PRO | A | 331 | 32.550 | 22.186 | 8.318 | 1.00 52.30 | C |
| ATOM | 757 | O | PRO | A | 331 | 32.645 | 22.362 | 7.107 | 1.00 52.88 | O |
| ATOM | 758 | N | SER | A | 332 | 32.480 | 20.976 | 8.870 | 1.00 55.30 | N |
| ATOM | 759 | CA | SER | A | 332 | 32.495 | 19.770 | 8.045 | 1.00 55.79 | C |
| ATOM | 760 | CB | SER | A | 332 | 32.807 | 18.529 | 8.886 | 1.00 55.44 | C |
| ATOM | 761 | OG | SER | A | 332 | 34.165 | 18.505 | 9.277 | 1.00 57.09 | O |
| ATOM | 762 | C | SER | A | 332 | 31.148 | 19.578 | 7.365 | 1.00 55.91 | C |
| ATOM | 763 | O | SER | A | 332 | 31.080 | 19.251 | 6.184 | 1.00 56.30 | O |
| ATOM | 764 | N | GLY | A | 333 | 30.074 | 19.769 | 8.124 | 1.00 50.90 | N |

Figure 15

| | | | | | | | | | | |
|---|---|---|---|---|---|---|---|---|---|---|
| ATOM | 765 | CA | GLY | A | 333 | 28.752 | 19.606 | 7.557 | 1.00 50.79 | C |
| ATOM | 766 | C | GLY | A | 333 | 28.535 | 20.600 | 6.443 | 1.00 50.51 | C |
| ATOM | 767 | O | GLY | A | 333 | 28.227 | 20.225 | 5.313 | 1.00 50.27 | O |
| ATOM | 768 | N | ILE | A | 334 | 28.698 | 21.877 | 6.772 | 1.00 51.52 | N |
| ATOM | 769 | CA | ILE | A | 334 | 28.529 | 22.971 | 5.819 | 1.00 51.64 | C |
| ATOM | 770 | CB | ILE | A | 334 | 29.154 | 24.270 | 6.360 | 1.00 61.71 | C |
| ATOM | 771 | CG2 | ILE | A | 334 | 29.297 | 25.286 | 5.240 | 1.00 63.23 | C |
| ATOM | 772 | CG1 | ILE | A | 334 | 28.298 | 24.824 | 7.491 | 1.00 61.75 | C |
| ATOM | 773 | CD1 | ILE | A | 334 | 26.881 | 25.138 | 7.077 | 1.00 62.75 | C |
| ATOM | 774 | C | ILE | A | 334 | 29.154 | 22.681 | 4.461 | 1.00 50.87 | C |
| ATOM | 775 | O | ILE | A | 334 | 28.671 | 23.149 | 3.437 | 1.00 50.71 | O |
| ATOM | 776 | N | LYS | A | 335 | 30.217 | 21.886 | 4.456 | 1.00 58.93 | N |
| ATOM | 777 | CA | LYS | A | 335 | 30.920 | 21.558 | 3.224 | 1.00 58.45 | C |
| ATOM | 778 | CB | LYS | A | 335 | 32.419 | 21.416 | 3.506 | 1.00 65.45 | C |
| ATOM | 779 | CG | LYS | A | 335 | 33.052 | 22.646 | 4.151 | 1.00 66.80 | C |
| ATOM | 780 | CD | LYS | A | 335 | 34.569 | 22.486 | 4.263 | 1.00 68.99 | C |
| ATOM | 781 | CE | LYS | A | 335 | 35.224 | 23.719 | 4.869 | 1.00 69.89 | C |
| ATOM | 782 | NZ | LYS | A | 335 | 36.709 | 23.701 | 4.688 | 1.00 71.54 | N |
| ATOM | 783 | C | LYS | A | 335 | 30.425 | 20.310 | 2.506 | 1.00 57.55 | C |
| ATOM | 784 | O | LYS | A | 335 | 30.998 | 19.918 | 1.488 | 1.00 57.61 | O |
| ATOM | 785 | N | LEU | A | 336 | 29.369 | 19.683 | 3.016 | 1.00 51.10 | N |
| ATOM | 786 | CA | LEU | A | 336 | 28.850 | 18.478 | 2.370 | 1.00 49.91 | C |
| ATOM | 787 | CB | LEU | A | 336 | 27.768 | 17.823 | 3.235 | 1.00 43.32 | C |
| ATOM | 788 | CG | LEU | A | 336 | 28.240 | 17.289 | 4.592 | 1.00 42.23 | C |
| ATOM | 789 | CD1 | LEU | A | 336 | 27.108 | 16.571 | 5.275 | 1.00 41.98 | C |
| ATOM | 790 | CD2 | LEU | A | 336 | 29.418 | 16.341 | 4.393 | 1.00 42.26 | C |
| ATOM | 791 | C | LEU | A | 336 | 28.279 | 18.799 | 0.993 | 1.00 50.01 | C |
| ATOM | 792 | O | LEU | A | 336 | 27.662 | 19.848 | 0.788 | 1.00 50.14 | O |
| ATOM | 793 | N | THR | A | 337 | 28.500 | 17.894 | 0.045 | 1.00 50.93 | N |
| ATOM | 794 | CA | THR | A | 337 | 28.004 | 18.080 | -1.310 | 1.00 50.51 | C |
| ATOM | 795 | CB | THR | A | 337 | 28.787 | 17.193 | -2.330 | 1.00 51.51 | C |
| ATOM | 796 | OG1 | THR | A | 337 | 28.619 | 15.804 | -2.007 | 1.00 50.14 | O |
| ATOM | 797 | CG2 | THR | A | 337 | 30.281 | 17.532 | -2.293 | 1.00 51.11 | C |
| ATOM | 798 | C | THR | A | 337 | 26.530 | 17.694 | -1.330 | 1.00 49.67 | C |
| ATOM | 799 | O | THR | A | 337 | 26.053 | 17.027 | -0.416 | 1.00 50.14 | O |
| ATOM | 800 | N | ILE | A | 338 | 25.812 | 18.115 | -2.363 | 1.00 40.50 | N |
| ATOM | 801 | CA | ILE | A | 338 | 24.399 | 17.789 | -2.473 | 1.00 39.53 | C |
| ATOM | 802 | CB | ILE | A | 338 | 23.739 | 18.528 | -3.671 | 1.00 38.44 | C |
| ATOM | 803 | CG2 | ILE | A | 338 | 24.469 | 18.193 | -4.959 | 1.00 37.54 | C |
| ATOM | 804 | CG1 | ILE | A | 338 | 22.253 | 18.157 | -3.768 | 1.00 37.10 | C |
| ATOM | 805 | CD1 | ILE | A | 338 | 21.386 | 18.713 | -2.645 | 1.00 35.50 | C |
| ATOM | 806 | C | ILE | A | 338 | 24.266 | 16.279 | -2.643 | 1.00 39.03 | C |
| ATOM | 807 | O | ILE | A | 338 | 23.274 | 15.688 | -2.221 | 1.00 38.11 | O |
| ATOM | 808 | N | ASN | A | 339 | 25.279 | 15.673 | -3.265 | 1.00 41.79 | N |
| ATOM | 809 | CA | ASN | A | 339 | 25.342 | 14.225 | -3.487 | 1.00 41.98 | C |
| ATOM | 810 | CB | ASN | A | 339 | 26.634 | 13.846 | -4.233 | 1.00 51.94 | C |
| ATOM | 811 | CG | ASN | A | 339 | 26.569 | 14.126 | -5.727 | 1.00 52.87 | C |
| ATOM | 812 | OD1 | ASN | A | 339 | 26.007 | 13.346 | -6.496 | 1.00 51.41 | O |
| ATOM | 813 | ND2 | ASN | A | 339 | 27.151 | 15.246 | -6.141 | 1.00 52.93 | N |
| ATOM | 814 | C | ASN | A | 339 | 25.356 | 13.513 | -2.130 | 1.00 41.87 | C |
| ATOM | 815 | O | ASN | A | 339 | 24.577 | 12.601 | -1.887 | 1.00 41.71 | O |
| ATOM | 816 | N | LYS | A | 340 | 26.268 | 13.933 | -1.258 | 1.00 45.63 | N |
| ATOM | 817 | CA | LYS | A | 340 | 26.399 | 13.348 | 0.074 | 1.00 45.49 | C |
| ATOM | 818 | CB | LYS | A | 340 | 27.595 | 13.968 | 0.807 | 1.00 50.45 | C |
| ATOM | 819 | CG | LYS | A | 340 | 27.856 | 13.377 | 2.181 | 1.00 52.37 | C |
| ATOM | 820 | CD | LYS | A | 340 | 28.132 | 11.878 | 2.083 | 1.00 54.13 | C |
| ATOM | 821 | CE | LYS | A | 340 | 28.024 | 11.197 | 3.435 | 1.00 55.24 | C |
| ATOM | 822 | NZ | LYS | A | 340 | 27.978 | 9.711 | 3.292 | 1.00 57.54 | N |
| ATOM | 823 | C | LYS | A | 340 | 25.127 | 13.573 | 0.888 | 1.00 44.72 | C |
| ATOM | 824 | O | LYS | A | 340 | 24.622 | 12.656 | 1.531 | 1.00 45.41 | O |

Figure 15

| | | | | | | | | | | |
|---|---|---|---|---|---|---|---|---|---|---|
| ATOM | 825 | N | LEU | A | 341 | 24.607 | 14.793 | 0.854 | 1.00 39.49 | N |
| ATOM | 826 | CA | LEU | A | 341 | 23.396 | 15.121 | 1.587 | 1.00 39.46 | C |
| ATOM | 827 | CB | LEU | A | 341 | 23.041 | 16.596 | 1.366 | 1.00 36.20 | C |
| ATOM | 828 | CG | LEU | A | 341 | 24.079 | 17.571 | 1.942 | 1.00 35.56 | C |
| ATOM | 829 | CD1 | LEU | A | 341 | 23.645 | 19.011 | 1.695 | 1.00 33.84 | C |
| ATOM | 830 | CD2 | LEU | A | 341 | 24.241 | 17.301 | 3.433 | 1.00 34.67 | C |
| ATOM | 831 | C | LEU | A | 341 | 22.242 | 14.224 | 1.146 | 1.00 39.91 | C |
| ATOM | 832 | O | LEU | A | 341 | 21.406 | 13.811 | 1.963 | 1.00 39.99 | O |
| ATOM | 833 | N | LEU | A | 342 | 22.214 | 13.927 | -0.150 | 1.00 39.04 | N |
| ATOM | 834 | CA | LEU | A | 342 | 21.190 | 13.078 | -0.738 | 1.00 39.25 | C |
| ATOM | 835 | CB | LEU | A | 342 | 21.284 | 13.127 | -2.267 | 1.00 52.08 | C |
| ATOM | 836 | CG | LEU | A | 342 | 20.017 | 13.559 | -3.017 | 1.00 53.69 | C |
| ATOM | 837 | CD1 | LEU | A | 342 | 18.873 | 12.672 | -2.582 | 1.00 55.26 | C |
| ATOM | 838 | CD2 | LEU | A | 342 | 19.685 | 15.020 | -2.732 | 1.00 52.47 | C |
| ATOM | 839 | C | LEU | A | 342 | 21.362 | 11.636 | -0.259 | 1.00 39.23 | C |
| ATOM | 840 | O | LEU | A | 342 | 20.374 | 10.921 | -0.063 | 1.00 38.63 | O |
| ATOM | 841 | N | ASP | A | 343 | 22.613 | 11.205 | -0.096 | 1.00 36.60 | N |
| ATOM | 842 | CA | ASP | A | 343 | 22.869 | 9.854 | 0.378 | 1.00 37.01 | C |
| ATOM | 843 | CB | ASP | A | 343 | 24.348 | 9.489 | 0.260 | 1.00 69.22 | C |
| ATOM | 844 | CG | ASP | A | 343 | 24.622 | 8.051 | 0.692 | 1.00 73.15 | C |
| ATOM | 845 | OD1 | ASP | A | 343 | 23.856 | 7.159 | 0.260 | 1.00 74.70 | O |
| ATOM | 846 | OD2 | ASP | A | 343 | 25.597 | 7.811 | 1.450 | 1.00 74.39 | O |
| ATOM | 847 | C | ASP | A | 343 | 22.434 | 9.756 | 1.837 | 1.00 35.78 | C |
| ATOM | 848 | O | ASP | A | 343 | 21.882 | 8.743 | 2.263 | 1.00 34.86 | O |
| ATOM | 849 | N | MET | A | 344 | 22.689 | 10.807 | 2.606 | 1.00 38.17 | N |
| ATOM | 850 | CA | MET | A | 344 | 22.277 | 10.801 | 4.001 | 1.00 37.65 | C |
| ATOM | 851 | CB | MET | A | 344 | 22.697 | 12.102 | 4.692 | 1.00 44.24 | C |
| ATOM | 852 | CG | MET | A | 344 | 24.202 | 12.358 | 4.661 | 1.00 46.30 | C |
| ATOM | 853 | SD | MET | A | 344 | 24.666 | 13.732 | 5.724 | 1.00 49.44 | S |
| ATOM | 854 | CE | MET | A | 344 | 25.747 | 12.916 | 6.895 | 1.00 48.97 | C |
| ATOM | 855 | C | MET | A | 344 | 20.753 | 10.644 | 4.057 | 1.00 36.54 | C |
| ATOM | 856 | O | MET | A | 344 | 20.241 | 9.810 | 4.791 | 1.00 35.90 | O |
| ATOM | 857 | N | ALA | A | 345 | 20.044 | 11.440 | 3.256 | 1.00 38.13 | N |
| ATOM | 858 | CA | ALA | A | 345 | 18.589 | 11.411 | 3.209 | 1.00 36.46 | C |
| ATOM | 859 | CB | ALA | A | 345 | 18.092 | 12.449 | 2.225 | 1.00 34.87 | C |
| ATOM | 860 | C | ALA | A | 345 | 18.058 | 10.033 | 2.832 | 1.00 36.17 | C |
| ATOM | 861 | O | ALA | A | 345 | 17.054 | 9.577 | 3.385 | 1.00 35.07 | O |
| ATOM | 862 | N | ALA | A | 346 | 18.724 | 9.369 | 1.888 | 1.00 37.29 | N |
| ATOM | 863 | CA | ALA | A | 346 | 18.302 | 8.036 | 1.472 | 1.00 37.66 | C |
| ATOM | 864 | CB | ALA | A | 346 | 19.153 | 7.543 | 0.297 | 1.00 31.73 | C |
| ATOM | 865 | C | ALA | A | 346 | 18.413 | 7.070 | 2.643 | 1.00 37.95 | C |
| ATOM | 866 | O | ALA | A | 346 | 17.529 | 6.241 | 2.861 | 1.00 38.33 | O |
| ATOM | 867 | N | GLN | A | 347 | 19.503 | 7.170 | 3.397 | 1.00 35.14 | N |
| ATOM | 868 | CA | GLN | A | 347 | 19.691 | 6.285 | 4.550 | 1.00 36.01 | C |
| ATOM | 869 | CB | GLN | A | 347 | 21.049 | 6.552 | 5.213 | 1.00 43.95 | C |
| ATOM | 870 | CG | GLN | A | 347 | 22.235 | 6.081 | 4.371 | 1.00 46.14 | C |
| ATOM | 871 | CD | GLN | A | 347 | 23.569 | 6.560 | 4.912 | 1.00 48.87 | C |
| ATOM | 872 | OE1 | GLN | A | 347 | 24.631 | 6.147 | 4.435 | 1.00 52.09 | O |
| ATOM | 873 | NE2 | GLN | A | 347 | 23.527 | 7.431 | 5.903 | 1.00 48.73 | N |
| ATOM | 874 | C | GLN | A | 347 | 18.569 | 6.456 | 5.578 | 1.00 34.58 | C |
| ATOM | 875 | O | GLN | A | 347 | 18.121 | 5.476 | 6.184 | 1.00 35.22 | O |
| ATOM | 876 | N | ILE | A | 348 | 18.123 | 7.694 | 5.773 | 1.00 29.36 | N |
| ATOM | 877 | CA | ILE | A | 348 | 17.054 | 7.977 | 6.716 | 1.00 28.76 | C |
| ATOM | 878 | CB | ILE | A | 348 | 16.876 | 9.500 | 6.920 | 1.00 28.50 | C |
| ATOM | 879 | CG2 | ILE | A | 348 | 15.707 | 9.779 | 7.887 | 1.00 26.52 | C |
| ATOM | 880 | CG1 | ILE | A | 348 | 18.187 | 10.092 | 7.453 | 1.00 28.17 | C · |
| ATOM | 881 | CD1 | ILE | A | 348 | 18.223 | 11.609 | 7.499 | 1.00 28.01 | C |
| ATOM | 882 | C | ILE | A | 348 | 15.757 | 7.385 | 6.180 | 1.00 29.01 | C |
| ATOM | 883 | O | ILE | A | 348 | 15.006 | 6.753 | 6.915 | 1.00 29.32 | O |
| ATOM | 884 | N | ALA | A | 349 | 15.497 | 7.605 | 4.894 | 1.00 30.99 | N |

Figure 15

| | | | | | | | | | |
|---|---|---|---|---|---|---|---|---|---|
| ATOM | 885 | CA | ALA | A | 349 | 14.305 | 7.070 | 4.260 | 1.00 31.07 | C |
| ATOM | 886 | CB | ALA | A | 349 | 14.259 | 7.493 | 2.792 | 1.00 21.64 | C |
| ATOM | 887 | C | ALA | A | 349 | 14.355 | 5.536 | 4.371 | 1.00 31.95 | C |
| ATOM | 888 | O | ALA | A | 349 | 13.328 | 4.880 | 4.551 | 1.00 30.61 | O |
| ATOM | 889 | N | GLU | A | 350 | 15.561 | 4.980 | 4.260 | 1.00 33.26 | N |
| ATOM | 890 | CA | GLU | A | 350 | 15.749 | 3.534 | 4.354 | 1.00 34.86 | C |
| ATOM | 891 | CB | GLU | A | 350 | 17.225 | 3.176 | 4.155 | 1.00 40.47 | C |
| ATOM | 892 | CG | GLU | A | 350 | 17.452 | 1.731 | 3.759 | 1.00 44.15 | C |
| ATOM | 893 | CD | GLU | A | 350 | 18.886 | 1.270 | 3.961 | 1.00 45.07 | C |
| ATOM | 894 | OE1 | GLU | A | 350 | 19.821 | 2.049 | 3.693 | 1.00 44.86 | O |
| ATOM | 895 | OE2 | GLU | A | 350 | 19.075 | 0.112 | 4.382 | 1.00 48.13 | O |
| ATOM | 896 | C | GLU | A | 350 | 15.280 | 3.063 | 5.733 | 1.00 34.02 | C |
| ATOM | 897 | O | GLU | A | 350 | 14.498 | 2.131 | 5.843 | 1.00 34.89 | O |
| ATOM | 898 | N | GLY | A | 351 | 15.752 | 3.722 | 6.782 | 1.00 30.91 | N |
| ATOM | 899 | CA | GLY | A | 351 | 15.334 | 3.354 | 8.124 | 1.00 30.25 | C |
| ATOM | 900 | C | GLY | A | 351 | 13.826 | 3.478 | 8.287 | 1.00 29.69 | C |
| ATOM | 901 | O | GLY | A | 351 | 13.178 | 2.560 | 8.795 | 1.00 29.24 | O |
| ATOM | 902 | N | MET | A | 352 | 13.263 | 4.605 | 7.846 | 1.00 30.11 | N |
| ATOM | 903 | CA | MET | A | 352 | 11.819 | 4.824 | 7.948 | 1.00 29.98 | C |
| ATOM | 904 | CB | MET | A | 352 | 11.441 | 6.230 | 7.475 | 1.00 29.73 | C |
| ATOM | 905 | CG | MET | A | 352 | 11.898 | 7.347 | 8.424 | 1.00 31.12 | C |
| ATOM | 906 | SD | MET | A | 352 | 11.359 | 7.078 | 10.141 | 1.00 30.26 | S |
| ATOM | 907 | CE | MET | A | 352 | 9.620 | 6.787 | 9.895 | 1.00 27.64 | C |
| ATOM | 908 | C | MET | A | 352 | 11.066 | 3.785 | 7.131 | 1.00 30.42 | C |
| ATOM | 909 | O | MET | A | 352 | 9.931 | 3.421 | 7.464 | 1.00 29.69 | O |
| ATOM | 910 | N | ALA | A | 353 | 11.700 | 3.316 | 6.057 | 1.00 31.22 | N |
| ATOM | 911 | CA | ALA | A | 353 | 11.098 | 2.294 | 5.215 | 1.00 32.58 | C |
| ATOM | 912 | CB | ALA | A | 353 | 11.958 | 2.062 | 3.975 | 1.00 30.78 | C |
| ATOM | 913 | C | ALA | A | 353 | 10.969 | 0.999 | 6.040 | 1.00 33.57 | C |
| ATOM | 914 | O | ALA | A | 353 | 9.990 | 0.267 | 5.925 | 1.00 32.99 | O |
| ATOM | 915 | N | PHE | A | 354 | 11.958 | 0.729 | 6.887 | 1.00 40.72 | N |
| ATOM | 916 | CA | PHE | A | 354 | 11.916 | -0.462 | 7.737 | 1.00 41.71 | C |
| ATOM | 917 | CB | PHE | A | 354 | 13.248 | -0.668 | 8.455 | 1.00 44.26 | C |
| ATOM | 918 | CG | PHE | A | 354 | 13.269 | -1.868 | 9.372 | 1.00 46.20 | C |
| ATOM | 919 | CD1 | PHE | A | 354 | 13.087 | -3.149 | 8.869 | 1.00 45.78 | C |
| ATOM | 920 | CD2 | PHE | A | 354 | 13.515 | -1.717 | 10.732 | 1.00 45.58 | C |
| ATOM | 921 | CE1 | PHE | A | 354 | 13.157 | -4.257 | 9.704 | 1.00 46.14 | C |
| ATOM | 922 | CE2 | PHE | A | 354 | 13.586 | -2.819 | 11.570 | 1.00 45.80 | C |
| ATOM | 923 | CZ | PHE | A | 354 | 13.408 | -4.092 | 11.054 | 1.00 46.23 | C |
| ATOM | 924 | C | PHE | A | 354 | 10.821 | -0.312 | 8.781 | 1.00 41.74 | C |
| ATOM | 925 | O | PHE | A | 354 | 10.058 | -1.239 | 9.040 | 1.00 42.57 | O |
| ATOM | 926 | N | ILE | A | 355 | 10.760 | 0.859 | 9.397 | 1.00 41.08 | N |
| ATOM | 927 | CA | ILE | A | 355 | 9.747 | 1.127 | 10.414 | 1.00 41.02 | C |
| ATOM | 928 | CB | ILE | A | 355 | 9.989 | 2.521 | 11.027 | 1.00 33.79 | C |
| ATOM | 929 | CG2 | ILE | A | 355 | 8.758 | 2.991 | 11.819 | 1.00 33.24 | C |
| ATOM | 930 | CG1 | ILE | A | 355 | 11.261 | 2.465 | 11.880 | 1.00 32.18 | C |
| ATOM | 931 | CD1 | ILE | A | 355 | 11.738 | 3.805 | 12.382 | 1.00 30.62 | C |
| ATOM | 932 | C | ILE | A | 355 | 8.353 | 1.026 | 9.784 | 1.00 40.99 | C |
| ATOM | 933 | O | ILE | A | 355 | 7.427 | 0.478 | 10.372 | 1.00 41.47 | O |
| ATOM | 934 | N | GLU | A | 356 | 8.221 | 1.545 | 8.572 | 1.00 34.53 | N |
| ATOM | 935 | CA | GLU | A | 356 | 6.962 | 1.494 | 7.842 | 1.00 34.87 | C |
| ATOM | 936 | CB | GLU | A | 356 | 7.133 | 2.248 | 6.518 | 1.00 34.43 | C |
| ATOM | 937 | CG | GLU | A | 356 | 6.024 | 2.105 | 5.490 | 1.00 33.72 | C |
| ATOM | 938 | CD | GLU | A | 356 | 6.256 | 3.015 | 4.284 | 1.00 32.79 | C |
| ATOM | 939 | OE1 | GLU | A | 356 | 5.889 | 4.197 | 4.355 | 1.00 33.14 | O |
| ATOM | 940 | OE2 | GLU | A | 356 | 6.833 | 2.561 | 3.270 | 1.00 34.75 | O |
| ATOM | 941 | C | GLU | A | 356 | 6.594 | 0.029 | 7.594 | 1.00 36.26 | C |
| ATOM | 942 | O | GLU | A | 356 | 5.463 | -0.398 | 7.844 | 1.00 35.38 | O |
| ATOM | 943 | N | GLU | A | 357 | 7.572 | -0.730 | 7.111 | 1.00 42.12 | N |
| ATOM | 944 | CA | GLU | A | 357 | 7.412 | -2.148 | 6.813 | 1.00 44.76 | C |

Figure 15

| | | | | | | | | | |
|---|---|---|---|---|---|---|---|---|---|
| ATOM | 945 | CB | GLU | A | 357 | 8.735 | -2.698 | 6.263 | 1.00 70.42 | C |
| ATOM | 946 | CG | GLU | A | 357 | 9.099 | -4.104 | 6.713 | 1.00 74.44 | C |
| ATOM | 947 | CD | GLU | A | 357 | 8.068 | -5.134 | 6.318 | 1.00 77.02 | C |
| ATOM | 948 | OE1 | GLU | A | 357 | 7.650 | -5.122 | 5.137 | 1.00 78.42 | O |
| ATOM | 949 | OE2 | GLU | A | 357 | 7.682 | -5.957 | 7.187 | 1.00 78.51 | O |
| ATOM | 950 | C | GLU | A | 357 | 6.950 | -2.972 | 8.018 | 1.00 45.28 | C |
| ATOM | 951 | O | GLU | A | 357 | 6.118 | -3.868 | 7.878 | 1.00 45.10 | O |
| ATOM | 952 | N | ARG | A | 358 | 7.481 | -2.653 | 9.196 | 1.00 41.89 | N |
| ATOM | 953 | CA | ARG | A | 358 | 7.135 | -3.364 | 10.422 | 1.00 42.55 | C |
| ATOM | 954 | CB | ARG | A | 358 | 8.346 | -3.392 | 11.363 | 1.00 55.36 | C |
| ATOM | 955 | CG | ARG | A | 358 | 9.551 | -4.148 | 10.806 | 1.00 57.90 | C |
| ATOM | 956 | CD | ARG | A | 358 | 9.287 | -5.655 | 10.689 | 1.00 58.82 | C |
| ATOM | 957 | NE | ARG | A | 358 | 9.397 | -6.336 | 11.975 | 1.00 61.20 | N |
| ATOM | 958 | CZ | ARG | A | 358 | 10.520 | -6.867 | 12.456 | 1.00 63.82 | C |
| ATOM | 959 | NH1 | ARG | A | 358 | 11.650 | -6.811 | 11.756 | 1.00 64.07 | N |
| ATOM | 960 | NH2 | ARG | A | 358 | 10.520 | -7.449 | 13.651 | 1.00 64.27 | N |
| ATOM | 961 | C | ARG | A | 358 | 5.927 | -2.749 | 11.129 | 1.00 42.64 | C |
| ATOM | 962 | O | ARG | A | 358 | 5.655 | -3.040 | 12.293 | 1.00 42.39 | O |
| ATOM | 963 | N | ASN | A | 359 | 5.204 | -1.892 | 10.418 | 1.00 40.95 | N |
| ATOM | 964 | CA | ASN | A | 359 | 4.009 | -1.254 | 10.957 | 1.00 40.16 | C |
| ATOM | 965 | CB | ASN | A | 359 | 2.922 | -2.312 | 11.183 | 1.00 76.95 | C |
| ATOM | 966 | CG | ASN | A | 359 | 2.596 | -3.114 | 9.916 | 1.00 79.50 | C |
| ATOM | 967 | OD1 | ASN | A | 359 | 2.331 | -2.553 | 8.843 | 1.00 80.06 | O |
| ATOM | 968 | ND2 | ASN | A | 359 | 2.594 | -4.441 | 10.047 | 1.00 81.62 | N |
| ATOM | 969 | C | ASN | A | 359 | 4.196 | -0.425 | 12.244 | 1.00 39.19 | C |
| ATOM | 970 | O | ASN | A | 359 | 3.332 | -0.422 | 13.120 | 1.00 38.60 | O |
| ATOM | 971 | N | TYR | A | 360 | 5.322 | 0.269 | 12.368 | 1.00 36.51 | N |
| ATOM | 972 | CA | TYR | A | 360 | 5.547 | 1.124 | 13.533 | 1.00 36.64 | C |
| ATOM | 973 | CB | TYR | A | 360 | 6.924 | 0.878 | 14.160 | 1.00 54.60 | C |
| ATOM | 974 | CG | TYR | A | 360 | 6.987 | -0.296 | 15.102 | 1.00 56.92 | C |
| ATOM | 975 | CD1 | TYR | A | 360 | 6.918 | -1.598 | 14.625 | 1.00 57.73 | C |
| ATOM | 976 | CE1 | TYR | A | 360 | 6.946 | -2.675 | 15.486 | 1.00 59.40 | C |
| ATOM | 977 | CD2 | TYR | A | 360 | 7.091 | -0.102 | 16.474 | 1.00 57.86 | C |
| ATOM | 978 | CE2 | TYR | A | 360 | 7.120 | -1.172 | 17.347 | 1.00 59.71 | C |
| ATOM | 979 | CZ | TYR | A | 360 | 7.046 | -2.457 | 16.846 | 1.00 60.61 | C |
| ATOM | 980 | OH | TYR | A | 360 | 7.060 | -3.532 | 17.705 | 1.00 64.09 | O |
| ATOM | 981 | C | TYR | A | 360 | 5.503 | 2.554 | 13.031 | 1.00 35.29 | C |
| ATOM | 982 | O | TYR | A | 360 | 5.373 | 2.772 | 11.834 | 1.00 33.46 | O |
| ATOM | 983 | N | ILE | A | 361 | 5.609 | 3.521 | 13.939 | 1.00 51.30 | N |
| ATOM | 984 | CA | ILE | A | 361 | 5.647 | 4.927 | 13.545 | 1.00 51.49 | C |
| ATOM | 985 | CB | ILE | A | 361 | 4.243 | 5.593 | 13.604 | 1.00 47.32 | C |
| ATOM | 986 | CG2 | ILE | A | 361 | 3.371 | 5.061 | 12.454 | 1.00 44.86 | C |
| ATOM | 987 | CG1 | ILE | A | 361 | 3.582 | 5.345 | 14.955 | 1.00 48.04 | C |
| ATOM | 988 | CD1 | ILE | A | 361 | 4.097 | 6.225 | 16.074 | 1.00 50.21 | C |
| ATOM | 989 | C | ILE | A | 361 | 6.646 | 5.705 | 14.403 | 1.00 51.71 | C |
| ATOM | 990 | O | ILE | A | 361 | 6.820 | 5.421 | 15.594 | 1.00 52.26 | O |
| ATOM | 991 | N | HIS | A | 362 | 7.317 | 6.680 | 13.803 | 1.00 39.70 | N |
| ATOM | 992 | CA | HIS | A | 362 | 8.290 | 7.440 | 14.566 | 1.00 38.49 | C |
| ATOM | 993 | CB | HIS | A | 362 | 9.282 | 8.149 | 13.640 | 1.00 36.70 | C |
| ATOM | 994 | CG | HIS | A | 362 | 10.485 | 8.685 | 14.349 | 1.00 33.79 | C |
| ATOM | 995 | CD2 | HIS | A | 362 | 11.806 | 8.457 | 14.163 | 1.00 33.04 | C |
| ATOM | 996 | ND1 | HIS | A | 362 | 10.394 | 9.570 | 15.403 | 1.00 35.06 | N |
| ATOM | 997 | CE1 | HIS | A | 362 | 11.611 | 9.864 | 15.833 | 1.00 33.43 | C |
| ATOM | 998 | NE2 | HIS | A | 362 | 12.485 | 9.199 | 15.097 | 1.00 31.68 | N |
| ATOM | 999 | C | HIS | A | 362 | 7.606 | 8.453 | 15.452 | 1.00 37.79 | C |
| ATOM | 1000 | O | HIS | A | 362 | 7.742 | 8.399 | 16.672 | 1.00 37.41 | O |
| ATOM | 1001 | N | ARG | A | 363 | 6.877 | 9.376 | 14.825 | 1.00 40.12 | N |
| ATOM | 1002 | CA | ARG | A | 363 | 6.145 | 10.430 | 15.531 | 1.00 38.57 | C |
| ATOM | 1003 | CB | ARG | A | 363 | 5.457 | 9.853 | 16.772 | 1.00 50.26 | C |
| ATOM | 1004 | CG | ARG | A | 363 | 4.690 | 10.885 | 17.573 | 1.00 54.62 | C |

Figure 15

```
ATOM   1005  CD   ARG A 363      4.628  10.518  19.054  1.00 58.85           C
ATOM   1006  NE   ARG A 363      3.282  10.133  19.461  1.00 62.41           N
ATOM   1007  CZ   ARG A 363      2.630   9.082  18.982  1.00 63.82           C
ATOM   1008  NH1  ARG A 363      3.203   8.300  18.082  1.00 64.48           N
ATOM   1009  NH2  ARG A 363      1.393   8.829  19.386  1.00 65.05           N
ATOM   1010  C    ARG A 363      7.019  11.618  15.939  1.00 36.83           C
ATOM   1011  O    ARG A 363      6.513  12.708  16.204  1.00 35.75           O
ATOM   1012  N    ASP A 364      8.329  11.419  15.992  1.00 35.62           N
ATOM   1013  CA   ASP A 364      9.227  12.508  16.375  1.00 35.08           C
ATOM   1014  CB   ASP A 364      9.848  12.226  17.753  1.00 32.45           C
ATOM   1015  CG   ASP A 364      8.859  12.424  18.899  1.00 33.91           C
ATOM   1016  OD1  ASP A 364      8.380  13.566  19.095  1.00 32.69           O
ATOM   1017  OD2  ASP A 364      8.563  11.432  19.603  1.00 34.01           O
ATOM   1018  C    ASP A 364     10.335  12.716  15.343  1.00 34.29           C
ATOM   1019  O    ASP A 364     11.417  13.218  15.662  1.00 34.15           O
ATOM   1020  N    LEU A 365     10.050  12.346  14.102  1.00 30.50           N
ATOM   1021  CA   LEU A 365     11.015  12.459  13.033  1.00 30.87           C
ATOM   1022  CB   LEU A 365     10.502  11.726  11.792  1.00 27.78           C
ATOM   1023  CG   LEU A 365     11.480  11.703  10.607  1.00 28.47           C
ATOM   1024  CD1  LEU A 365     12.759  10.945  11.006  1.00 28.29           C
ATOM   1025  CD2  LEU A 365     10.819  11.042   9.406  1.00 26.49           C
ATOM   1026  C    LEU A 365     11.395  13.889  12.645  1.00 31.93           C
ATOM   1027  O    LEU A 365     10.545  14.671  12.187  1.00 32.43           O
ATOM   1028  N    ARG A 366     12.681  14.202  12.820  1.00 32.94           N
ATOM   1029  CA   ARG A 366     13.281  15.492  12.469  1.00 32.38           C
ATOM   1030  CB   ARG A 366     12.774  16.623  13.375  1.00 28.96           C
ATOM   1031  CG   ARG A 366     12.986  16.480  14.872  1.00 30.82           C
ATOM   1032  CD   ARG A 366     12.537  17.789  15.543  1.00 34.88           C
ATOM   1033  NE   ARG A 366     12.583  17.762  17.005  1.00 37.25           N
ATOM   1034  CZ   ARG A 366     11.707  17.113  17.767  1.00 37.19           C
ATOM   1035  NH1  ARG A 366     10.710  16.436  17.210  1.00 36.87           N
ATOM   1036  NH2  ARG A 366     11.839  17.125  19.088  1.00 37.50           N
ATOM   1037  C    ARG A 366     14.808  15.351  12.557  1.00 32.76           C
ATOM   1038  O    ARG A 366     15.304  14.420  13.181  1.00 32.66           O
ATOM   1039  N    ALA A 367     15.548  16.253  11.919  1.00 29.45           N
ATOM   1040  CA   ALA A 367     17.004  16.166  11.920  1.00 30.44           C
ATOM   1041  CB   ALA A 367     17.587  17.344  11.164  1.00 37.58           C
ATOM   1042  C    ALA A 367     17.641  16.061  13.315  1.00 31.09           C
ATOM   1043  O    ALA A 367     18.662  15.392  13.490  1.00 31.08           O
ATOM   1044  N    ALA A 368     17.040  16.712  14.306  1.00 30.93           N
ATOM   1045  CA   ALA A 368     17.569  16.663  15.658  1.00 30.60           C
ATOM   1046  CB   ALA A 368     16.703  17.490  16.601  1.00 31.44           C
ATOM   1047  C    ALA A 368     17.589  15.229  16.130  1.00 31.63           C
ATOM   1048  O    ALA A 368     18.401  14.861  16.980  1.00 32.27           O
ATOM   1049  N    ASN A 369     16.694  14.415  15.573  1.00 33.36           N
ATOM   1050  CA   ASN A 369     16.594  13.033  15.990  1.00 33.04           C
ATOM   1051  CB   ASN A 369     15.133  12.703  16.319  1.00 36.44           C
ATOM   1052  CG   ASN A 369     14.649  13.457  17.555  1.00 37.35           C
ATOM   1053  OD1  ASN A 369     15.368  13.521  18.566  1.00 38.38           O
ATOM   1054  ND2  ASN A 369     13.443  14.021  17.491  1.00 33.25           N
ATOM   1055  C    ASN A 369     17.205  12.002  15.072  1.00 32.44           C
ATOM   1056  O    ASN A 369     16.810  10.839  15.062  1.00 33.21           O
ATOM   1057  N    ILE A 370     18.163  12.447  14.276  1.00 33.15           N
ATOM   1058  CA   ILE A 370     18.912  11.553  13.401  1.00 32.19           C
ATOM   1059  CB   ILE A 370     18.915  12.026  11.940  1.00 27.93           C
ATOM   1060  CG2  ILE A 370     19.852  11.134  11.108  1.00 26.92           C
ATOM   1061  CG1  ILE A 370     17.479  12.025  11.382  1.00 27.32           C
ATOM   1062  CD1  ILE A 370     16.768  10.690  11.431  1.00 22.59           C
ATOM   1063  C    ILE A 370     20.319  11.704  13.975  1.00 32.80           C
ATOM   1064  O    ILE A 370     20.743  12.821  14.291  1.00 33.03           O
```

Figure 15

```
ATOM   1065  N    LEU A 371      21.020  10.592  14.148  1.00 31.09           N
ATOM   1066  CA   LEU A 371      22.377  10.618  14.680  1.00 31.97           C
ATOM   1067  CB   LEU A 371      22.484   9.650  15.861  1.00 34.04           C
ATOM   1068  CG   LEU A 371      21.519   9.996  17.013  1.00 34.80           C
ATOM   1069  CD1  LEU A 371      21.525   8.908  18.059  1.00 34.20           C
ATOM   1070  CD2  LEU A 371      21.915  11.321  17.627  1.00 34.36           C
ATOM   1071  C    LEU A 371      23.371  10.250  13.566  1.00 32.41           C
ATOM   1072  O    LEU A 371      23.080   9.412  12.710  1.00 32.89           O
ATOM   1073  N    VAL A 372      24.533  10.892  13.578  1.00 32.16           N
ATOM   1074  CA   VAL A 372      25.556  10.670  12.558  1.00 33.13           C
ATOM   1075  CB   VAL A 372      25.930  12.014  11.877  1.00 35.52           C
ATOM   1076  CG1  VAL A 372      26.802  11.764  10.638  1.00 35.13           C
ATOM   1077  CG2  VAL A 372      24.653  12.758  11.480  1.00 34.71           C
ATOM   1078  C    VAL A 372      26.821   9.995  13.084  1.00 33.40           C
ATOM   1079  O    VAL A 372      27.430  10.440  14.058  1.00 32.45           O
ATOM   1080  N    SER A 373      27.216   8.914  12.423  1.00 39.08           N
ATOM   1081  CA   SER A 373      28.402   8.166  12.828  1.00 41.92           C
ATOM   1082  CB   SER A 373      28.337   6.746  12.290  1.00 42.59           C
ATOM   1083  OG   SER A 373      28.619   6.738  10.902  1.00 44.21           O
ATOM   1084  C    SER A 373      29.678   8.826  12.310  1.00 43.83           C
ATOM   1085  O    SER A 373      29.632   9.774  11.522  1.00 44.09           O
ATOM   1086  N    ASP A 374      30.816   8.310  12.759  1.00 50.09           N
ATOM   1087  CA   ASP A 374      32.111   8.829  12.353  1.00 51.44           C
ATOM   1088  CB   ASP A 374      33.232   8.131  13.131  1.00 62.33           C
ATOM   1089  CG   ASP A 374      33.084   6.627  13.153  1.00 63.70           C
ATOM   1090  OD1  ASP A 374      32.793   6.034  12.093  1.00 64.02           O
ATOM   1091  OD2  ASP A 374      33.268   6.035  14.237  1.00 67.14           O
ATOM   1092  C    ASP A 374      32.317   8.651  10.857  1.00 52.51           C
ATOM   1093  O    ASP A 374      33.150   9.333  10.255  1.00 52.99           O
ATOM   1094  N    THR A 375      31.561   7.732  10.259  1.00 49.91           N
ATOM   1095  CA   THR A 375      31.645   7.482   8.820  1.00 50.00           C
ATOM   1096  CB   THR A 375      31.261   6.035   8.467  1.00 58.92           C
ATOM   1097  OG1  THR A 375      29.876   5.829   8.765  1.00 60.71           O
ATOM   1098  CG2  THR A 375      32.093   5.043   9.269  1.00 59.92           C
ATOM   1099  C    THR A 375      30.654   8.391   8.106  1.00 49.54           C
ATOM   1100  O    THR A 375      30.462   8.286   6.894  1.00 50.29           O
ATOM   1101  N    LEU A 376      30.014   9.269   8.870  1.00 50.38           N
ATOM   1102  CA   LEU A 376      29.019  10.196   8.333  1.00 49.66           C
ATOM   1103  CB   LEU A 376      29.583  10.964   7.137  1.00 47.58           C
ATOM   1104  CG   LEU A 376      30.780  11.842   7.497  1.00 47.64           C
ATOM   1105  CD1  LEU A 376      31.187  12.675   6.299  1.00 47.96           C
ATOM   1106  CD2  LEU A 376      30.406  12.731   8.671  1.00 48.01           C
ATOM   1107  C    LEU A 376      27.725   9.505   7.925  1.00 48.27           C
ATOM   1108  O    LEU A 376      26.940  10.058   7.157  1.00 48.28           O
ATOM   1109  N    SER A 377      27.508   8.295   8.431  1.00 37.39           N
ATOM   1110  CA   SER A 377      26.291   7.561   8.117  1.00 36.41           C
ATOM   1111  CB   SER A 377      26.552   6.055   8.103  1.00 59.75           C
ATOM   1112  OG   SER A 377      26.959   5.590   9.376  1.00 63.60           O
ATOM   1113  C    SER A 377      25.240   7.915   9.163  1.00 34.81           C
ATOM   1114  O    SER A 377      25.535   8.023  10.351  1.00 33.99           O
ATOM   1115  N    CYS A 378      24.007   8.099   8.712  1.00 40.25           N
ATOM   1116  CA   CYS A 378      22.930   8.478   9.606  1.00 38.89           C
ATOM   1117  CB   CYS A 378      21.981   9.434   8.882  1.00 41.38           C
ATOM   1118  SG   CYS A 378      22.762  10.952   8.273  1.00 42.18           S
ATOM   1119  C    CYS A 378      22.147   7.296  10.149  1.00 38.46           C
ATOM   1120  O    CYS A 378      22.065   6.247   9.518  1.00 38.26           O
ATOM   1121  N    LYS A 379      21.588   7.476  11.338  1.00 34.42           N
ATOM   1122  CA   LYS A 379      20.776   6.451  11.969  1.00 34.78           C
ATOM   1123  CB   LYS A 379      21.583   5.655  12.994  1.00 42.45           C
ATOM   1124  CG   LYS A 379      22.652   4.778  12.388  1.00 43.01           C
```

Figure 15

```
ATOM   1125  CD   LYS A 379      23.248    3.844   13.426  1.00 44.16           C
ATOM   1126  CE   LYS A 379      24.301    2.938   12.803  1.00 44.31           C
ATOM   1127  NZ   LYS A 379      24.683    1.841   13.729  1.00 47.43           N
ATOM   1128  C    LYS A 379      19.590    7.109   12.656  1.00 33.95           C
ATOM   1129  O    LYS A 379      19.699    8.210   13.205  1.00 33.84           O
ATOM   1130  N    ILE A 380      18.459    6.424   12.618  1.00 37.42           N
ATOM   1131  CA   ILE A 380      17.235    6.922   13.222  1.00 37.47           C
ATOM   1132  CB   ILE A 380      16.003    6.214   12.632  1.00 39.42           C
ATOM   1133  CG2  ILE A 380      14.764    6.630   13.407  1.00 37.68           C
ATOM   1134  CG1  ILE A 380      15.896    6.526   11.129  1.00 38.81           C
ATOM   1135  CD1  ILE A 380      14.734    5.854   10.448  1.00 40.12           C
ATOM   1136  C    ILE A 380      17.230    6.721   14.728  1.00 37.84           C
ATOM   1137  O    ILE A 380      17.512    5.621   15.228  1.00 37.75           O
ATOM   1138  N    ALA A 381      16.901    7.792   15.440  1.00 34.66           N
ATOM   1139  CA   ALA A 381      16.850    7.779   16.893  1.00 35.67           C
ATOM   1140  CB   ALA A 381      17.844    8.799   17.449  1.00 35.15           C
ATOM   1141  C    ALA A 381      15.450    8.100   17.408  1.00 35.99           C
ATOM   1142  O    ALA A 381      14.653    8.739   16.726  1.00 34.32           O
ATOM   1143  N    ASP A 382      15.186    7.653   18.632  1.00 41.60           N
ATOM   1144  CA   ASP A 382      13.922    7.878   19.336  1.00 42.90           C
ATOM   1145  CB   ASP A 382      13.948    9.248   20.030  1.00 48.09           C
ATOM   1146  CG   ASP A 382      14.782    9.235   21.313  1.00 50.59           C
ATOM   1147  OD1  ASP A 382      14.610    8.292   22.119  1.00 52.56           O
ATOM   1148  OD2  ASP A 382      15.592   10.158   21.521  1.00 49.31           O
ATOM   1149  C    ASP A 382      12.628    7.730   18.550  1.00 42.63           C
ATOM   1150  O    ASP A 382      11.792    8.633   18.526  1.00 42.03           O
ATOM   1151  N    PHE A 383      12.468    6.568   17.934  1.00 38.23           N
ATOM   1152  CA   PHE A 383      11.279    6.232   17.158  1.00 40.09           C
ATOM   1153  CB   PHE A 383      11.678    5.461   15.901  1.00 50.94           C
ATOM   1154  CG   PHE A 383      12.585    4.297   16.179  1.00 51.82           C
ATOM   1155  CD1  PHE A 383      13.953    4.483   16.291  1.00 51.75           C
ATOM   1156  CD2  PHE A 383      12.065    3.031   16.393  1.00 53.50           C
ATOM   1157  CE1  PHE A 383      14.789    3.431   16.615  1.00 53.43           C
ATOM   1158  CE2  PHE A 383      12.895    1.968   16.719  1.00 53.85           C
ATOM   1159  CZ   PHE A 383      14.260    2.168   16.832  1.00 54.01           C
ATOM   1160  C    PHE A 383      10.363    5.336   17.998  1.00 40.79           C
ATOM   1161  O    PHE A 383      10.795    4.739   18.987  1.00 40.94           O
ATOM   1162  N    GLY A 384       9.104    5.231   17.584  1.00 44.45           N
ATOM   1163  CA   GLY A 384       8.160    4.380   18.285  1.00 44.94           C
ATOM   1164  C    GLY A 384       7.665    4.925   19.604  1.00 45.83           C
ATOM   1165  O    GLY A 384       6.840    4.300   20.254  1.00 46.08           O
ATOM   1166  N    LEU A 385       8.172    6.082   20.013  1.00 49.97           N
ATOM   1167  CA   LEU A 385       7.746    6.689   21.262  1.00 51.32           C
ATOM   1168  CB   LEU A 385       8.490    8.002   21.515  1.00 47.14           C
ATOM   1169  CG   LEU A 385       9.710    7.927   22.430  1.00 48.10           C
ATOM   1170  CD1  LEU A 385      10.320    9.310   22.622  1.00 47.84           C
ATOM   1171  CD2  LEU A 385       9.271    7.351   23.761  1.00 48.42           C
ATOM   1172  C    LEU A 385       6.254    6.971   21.267  1.00 52.50           C
ATOM   1173  O    LEU A 385       5.680    7.383   20.259  1.00 52.41           O
ATOM   1174  N    ALA A 386       5.635    6.745   22.419  1.00 90.13           N
ATOM   1175  CA   ALA A 386       4.212    6.994   22.586  1.00 91.01           C
ATOM   1176  CB   ALA A 386       3.661    6.132   23.721  1.00 60.72           C
ATOM   1177  C    ALA A 386       4.011    8.472   22.905  1.00 91.13           C
ATOM   1178  O    ALA A 386       2.883    8.961   22.910  1.00 92.37           O
ATOM   1179  N    ARG A 387       5.104    9.181   23.168  1.00 63.27           N
ATOM   1180  CA   ARG A 387       5.019   10.604   23.499  1.00 62.65           C
ATOM   1181  CB   ARG A 387       5.479   10.833   24.948  1.00 50.36           C
ATOM   1182  CG   ARG A 387       6.982   10.619   25.177  1.00 50.00           C
ATOM   1183  CD   ARG A 387       7.374   10.835   26.633  1.00 50.13           C
ATOM   1184  NE   ARG A 387       8.793   10.580   26.878  1.00 52.08           N
```

Figure 15

```
ATOM   1185  CZ   ARG A 387       9.759  11.488  26.761  1.00 52.24           C
ATOM   1186  NH1  ARG A 387       9.475  12.734  26.408  1.00 51.05           N
ATOM   1187  NH2  ARG A 387      11.019  11.145  26.992  1.00 54.26           N
ATOM   1188  C    ARG A 387       5.860  11.475  22.568  1.00 62.03           C
ATOM   1189  O    ARG A 387       6.839  11.009  21.990  1.00 62.05           O
ATOM   1190  N    LEU A 388       5.459  12.737  22.416  1.00 47.06           N
ATOM   1191  CA   LEU A 388       6.201  13.687  21.595  1.00 46.41           C
ATOM   1192  CB   LEU A 388       5.293  14.827  21.132  1.00 59.33           C
ATOM   1193  CG   LEU A 388       4.111  14.485  20.216  1.00 60.96           C
ATOM   1194  CD1  LEU A 388       3.271  15.729  19.989  1.00 61.16           C
ATOM   1195  CD2  LEU A 388       4.623  13.941  18.887  1.00 60.76           C
ATOM   1196  C    LEU A 388       7.295  14.243  22.510  1.00 45.74           C
ATOM   1197  O    LEU A 388       7.044  14.497  23.685  1.00 45.88           O
ATOM   1198  N    ILE A 389       8.504  14.420  21.980  1.00 42.57           N
ATOM   1199  CA   ILE A 389       9.611  14.924  22.784  1.00 41.71           C
ATOM   1200  CB   ILE A 389      10.826  13.955  22.758  1.00 43.27           C
ATOM   1201  CG2  ILE A 389      10.428  12.584  23.294  1.00 43.09           C
ATOM   1202  CG1  ILE A 389      11.360  13.828  21.327  1.00 42.53           C
ATOM   1203  CD1  ILE A 389      12.483  12.830  21.172  1.00 42.37           C
ATOM   1204  C    ILE A 389      10.113  16.295  22.353  1.00 41.67           C
ATOM   1205  O    ILE A 389       9.805  16.789  21.264  1.00 40.97           O
ATOM   1206  N    GLU A 390      10.896  16.903  23.232  1.00 52.34           N
ATOM   1207  CA   GLU A 390      11.491  18.198  22.966  1.00 53.13           C
ATOM   1208  CB   GLU A 390      11.229  19.175  24.106  1.00 52.35           C
ATOM   1209  CG   GLU A 390       9.782  19.580  24.248  1.00 54.65           C
ATOM   1210  CD   GLU A 390       9.624  20.719  25.218  1.00 56.14           C
ATOM   1211  OE1  GLU A 390      10.184  20.620  26.334  1.00 58.12           O
ATOM   1212  OE2  GLU A 390       8.950  21.711  24.868  1.00 56.80           O
ATOM   1213  C    GLU A 390      12.980  17.987  22.808  1.00 53.02           C
ATOM   1214  O    GLU A 390      13.566  17.088  23.411  1.00 53.30           O
ATOM   1215  N    ASP A 391      13.599  18.827  21.997  1.00 51.14           N
ATOM   1216  CA   ASP A 391      15.020  18.690  21.755  1.00 51.63           C
ATOM   1217  CB   ASP A 391      15.366  19.392  20.437  1.00 54.41           C
ATOM   1218  CG   ASP A 391      14.524  18.883  19.284  1.00 54.04           C
ATOM   1219  OD1  ASP A 391      14.214  17.672  19.278  1.00 54.41           O
ATOM   1220  OD2  ASP A 391      14.177  19.677  18.386  1.00 55.48           O
ATOM   1221  C    ASP A 391      15.905  19.189  22.895  1.00 51.44           C
ATOM   1222  O    ASP A 391      17.126  19.220  22.756  1.00 52.12           O
ATOM   1223  N    ASN A 392      15.297  19.537  24.030  1.00 47.92           N
ATOM   1224  CA   ASN A 392      16.058  20.047  25.175  1.00 47.56           C
ATOM   1225  CB   ASN A 392      15.689  21.506  25.429  1.00 51.73           C
ATOM   1226  CG   ASN A 392      14.286  21.660  25.985  1.00 53.08           C
ATOM   1227  OD1  ASN A 392      13.536  20.691  26.101  1.00 53.14           O
ATOM   1228  ND2  ASN A 392      13.921  22.889  26.326  1.00 54.65           N
ATOM   1229  C    ASN A 392      15.849  19.264  26.467  1.00 47.16           C
ATOM   1230  O    ASN A 392      16.092  19.771  27.563  1.00 47.13           O
ATOM   1231  N    GLU A 393      15.401  18.027  26.357  1.00 46.22           N
ATOM   1232  CA   GLU A 393      15.157  17.254  27.557  1.00 46.55           C
ATOM   1233  CB   GLU A 393      14.091  16.206  27.266  1.00 51.75           C
ATOM   1234  CG   GLU A 393      12.940  16.777  26.447  1.00 50.14           C
ATOM   1235  CD   GLU A 393      11.868  15.761  26.173  1.00 48.80           C
ATOM   1236  OE1  GLU A 393      12.214  14.577  25.983  1.00 48.60           O
ATOM   1237  OE2  GLU A 393      10.680  16.147  26.140  1.00 49.98           O
ATOM   1238  C    GLU A 393      16.439  16.621  28.079  1.00 46.64           C
ATOM   1239  O    GLU A 393      16.585  16.400  29.278  1.00 46.33           O
ATOM   1240  N    TYR A 394      17.377  16.363  27.178  1.00 47.91           N
ATOM   1241  CA   TYR A 394      18.653  15.764  27.550  1.00 48.72           C
ATOM   1242  CB   TYR A 394      18.751  14.353  26.966  1.00 46.19           C
ATOM   1243  CG   TYR A 394      17.718  13.405  27.528  1.00 44.68           C
ATOM   1244  CD1  TYR A 394      17.776  13.003  28.857  1.00 43.57           C
```

Figure 15

```
ATOM   1245  CE1 TYR A 394      16.816  12.159  29.389  1.00 42.76           C
ATOM   1246  CD2 TYR A 394      16.666  12.937  26.742  1.00 42.43           C
ATOM   1247  CE2 TYR A 394      15.702  12.093  27.265  1.00 41.14           C
ATOM   1248  CZ  TYR A 394      15.784  11.708  28.590  1.00 41.87           C
ATOM   1249  OH  TYR A 394      14.844  10.867  29.129  1.00 41.05           O
ATOM   1250  C   TYR A 394      19.839  16.607  27.090  1.00 50.57           C
ATOM   1251  O   TYR A 394      20.990  16.193  27.227  1.00 50.84           O
ATOM   1252  N   THR A 395      19.562  17.795  26.556  1.00 54.28           N
ATOM   1253  CA  THR A 395      20.624  18.680  26.088  1.00 56.33           C
ATOM   1254  CB  THR A 395      21.014  18.352  24.638  1.00 84.63           C
ATOM   1255  OG1 THR A 395      21.026  16.928  24.458  1.00 87.46           O
ATOM   1256  CG2 THR A 395      22.403  18.900  24.325  1.00 84.86           C
ATOM   1257  C   THR A 395      20.197  20.146  26.155  1.00 57.20           C
ATOM   1258  O   THR A 395      19.029  20.471  25.961  1.00 57.62           O
ATOM   1259  N   ALA A 396      21.152  21.027  26.427  1.00 67.84           N
ATOM   1260  CA  ALA A 396      20.882  22.458  26.521  1.00 69.02           C
ATOM   1261  CB  ALA A 396      22.103  23.176  27.084  1.00 74.28           C
ATOM   1262  C   ALA A 396      20.500  23.061  25.167  1.00 69.69           C
ATOM   1263  O   ALA A 396      21.156  22.807  24.155  1.00 69.69           O
ATOM   1264  N   ARG A 397      19.437  23.861  25.163  1.00 78.51           N
ATOM   1265  CA  ARG A 397      18.946  24.507  23.945  1.00 78.76           C
ATOM   1266  CB  ARG A 397      17.885  23.628  23.270  1.00 59.10           C
ATOM   1267  CG  ARG A 397      18.449  22.397  22.588  1.00 58.83           C
ATOM   1268  CD  ARG A 397      19.246  22.793  21.355  1.00 59.09           C
ATOM   1269  NE  ARG A 397      20.113  21.723  20.863  1.00 59.64           N
ATOM   1270  CZ  ARG A 397      19.692  20.511  20.519  1.00 59.34           C
ATOM   1271  NH1 ARG A 397      18.408  20.198  20.614  1.00 60.03           N
ATOM   1272  NH2 ARG A 397      20.558  19.614  20.073  1.00 59.32           N
ATOM   1273  C   ARG A 397      18.352  25.882  24.247  1.00 78.90           C
ATOM   1274  O   ARG A 397      17.939  26.156  25.375  1.00 79.06           O
ATOM   1275  N   PRO A 403       7.990  21.502  18.710  1.00 65.60           N
ATOM   1276  CD  PRO A 403       8.126  20.586  19.857  1.00 67.29           C
ATOM   1277  CA  PRO A 403       8.343  20.826  17.455  1.00 64.51           C
ATOM   1278  CB  PRO A 403       8.823  19.447  17.923  1.00 66.09           C
ATOM   1279  CG  PRO A 403       8.043  19.225  19.184  1.00 67.08           C
ATOM   1280  C   PRO A 403       7.180  20.740  16.467  1.00 63.23           C
ATOM   1281  O   PRO A 403       7.077  19.777  15.680  1.00 63.45           O
ATOM   1282  N   ILE A 404       6.327  21.766  16.488  1.00 36.21           N
ATOM   1283  CA  ILE A 404       5.154  21.819  15.615  1.00 33.58           C
ATOM   1284  CB  ILE A 404       4.237  23.010  15.967  1.00 50.87           C
ATOM   1285  CG2 ILE A 404       2.898  22.831  15.298  1.00 52.91           C
ATOM   1286  CG1 ILE A 404       4.039  23.111  17.480  1.00 52.80           C
ATOM   1287  CD1 ILE A 404       3.647  21.810  18.145  1.00 54.82           C
ATOM   1288  C   ILE A 404       5.470  21.923  14.118  1.00 30.53           C
ATOM   1289  O   ILE A 404       4.690  21.464  13.294  1.00 30.25           O
ATOM   1290  N   LYS A 405       6.611  22.511  13.776  1.00 32.74           N
ATOM   1291  CA  LYS A 405       7.008  22.704  12.382  1.00 32.27           C
ATOM   1292  CB  LYS A 405       8.241  23.611  12.314  1.00 34.36           C
ATOM   1293  CG  LYS A 405       7.939  25.050  12.738  1.00 35.12           C
ATOM   1294  CD  LYS A 405       9.158  25.955  12.655  1.00 34.55           C
ATOM   1295  CE  LYS A 405       8.731  27.399  12.924  1.00 36.63           C
ATOM   1296  NZ  LYS A 405       9.717  28.381  12.414  1.00 37.10           N
ATOM   1297  C   LYS A 405       7.262  21.452  11.555  1.00 31.27           C
ATOM   1298  O   LYS A 405       7.525  21.546  10.363  1.00 30.86           O
ATOM   1299  N   TRP A 406       7.176  20.289  12.193  1.00 35.01           N
ATOM   1300  CA  TRP A 406       7.389  19.003  11.535  1.00 34.27           C
ATOM   1301  CB  TRP A 406       8.492  18.236  12.268  1.00 30.81           C
ATOM   1302  CG  TRP A 406       9.896  18.757  12.068  1.00 32.47           C
ATOM   1303  CD2 TRP A 406      10.566  19.771  12.841  1.00 31.49           C
ATOM   1304  CE2 TRP A 406      11.858  19.930  12.295  1.00 31.43           C
```

Figure 15

```
ATOM   1305  CE3 TRP A 406      10.198  20.559  13.938  1.00 33.28           C
ATOM   1306  CD1 TRP A 406      10.792  18.358  11.109  1.00 30.95           C
ATOM   1307  NE1 TRP A 406      11.972  19.059  11.241  1.00 31.06           N
ATOM   1308  CZ2 TRP A 406      12.780  20.842  12.808  1.00 31.84           C
ATOM   1309  CZ3 TRP A 406      11.114  21.464  14.445  1.00 32.02           C
ATOM   1310  CH2 TRP A 406      12.391  21.597  13.879  1.00 31.63           C
ATOM   1311  C   TRP A 406       6.097  18.167  11.570  1.00 34.44           C
ATOM   1312  O   TRP A 406       6.038  17.073  11.000  1.00 34.64           O
ATOM   1313  N   THR A 407       5.069  18.675  12.245  1.00 28.08           N
ATOM   1314  CA  THR A 407       3.808  17.947  12.391  1.00 28.04           C
ATOM   1315  CB  THR A 407       3.149  18.305  13.737  1.00 36.29           C
ATOM   1316  OG1 THR A 407       4.102  18.097  14.783  1.00 38.53           O
ATOM   1317  CG2 THR A 407       1.914  17.431  14.006  1.00 35.54           C
ATOM   1318  C   THR A 407       2.791  18.163  11.264  1.00 28.37           C
ATOM   1319  O   THR A 407       2.474  19.302  10.892  1.00 28.44           O
ATOM   1320  N   ALA A 408       2.286  17.058  10.724  1.00 30.10           N
ATOM   1321  CA  ALA A 408       1.313  17.099   9.639  1.00 29.97           C
ATOM   1322  CB  ALA A 408       1.081  15.689   9.088  1.00 28.07           C
ATOM   1323  C   ALA A 408       0.000  17.689  10.135  1.00 29.39           C
ATOM   1324  O   ALA A 408      -0.341  17.563  11.310  1.00 29.98           O
ATOM   1325  N   PRO A 409      -0.766  18.319   9.233  1.00 28.48           N
ATOM   1326  CD  PRO A 409      -0.463  18.483   7.803  1.00 31.47           C
ATOM   1327  CA  PRO A 409      -2.053  18.938   9.572  1.00 28.85           C
ATOM   1328  CB  PRO A 409      -2.595  19.375   8.212  1.00 31.99           C
ATOM   1329  CG  PRO A 409      -1.353  19.647   7.423  1.00 31.83           C
ATOM   1330  C   PRO A 409      -3.039  18.052  10.344  1.00 29.09           C
ATOM   1331  O   PRO A 409      -3.610  18.490  11.348  1.00 26.94           O
ATOM   1332  N   GLU A 410      -3.236  16.813   9.881  1.00 29.19           N
ATOM   1333  CA  GLU A 410      -4.166  15.904  10.550  1.00 30.63           C
ATOM   1334  CB  GLU A 410      -4.344  14.593   9.746  1.00 30.68           C
ATOM   1335  CG  GLU A 410      -3.144  13.637   9.716  1.00 29.43           C
ATOM   1336  CD  GLU A 410      -2.048  14.055   8.738  1.00 29.23           C
ATOM   1337  OE1 GLU A 410      -2.147  15.141   8.142  1.00 29.54           O
ATOM   1338  OE2 GLU A 410      -1.078  13.294   8.565  1.00 28.77           O
ATOM   1339  C   GLU A 410      -3.719  15.606  11.984  1.00 31.10           C
ATOM   1340  O   GLU A 410      -4.541  15.344  12.863  1.00 31.53           O
ATOM   1341  N   ALA A 411      -2.417  15.682  12.229  1.00 33.26           N
ATOM   1342  CA  ALA A 411      -1.889  15.430  13.563  1.00 34.50           C
ATOM   1343  CB  ALA A 411      -0.398  15.088  13.480  1.00 29.03           C
ATOM   1344  C   ALA A 411      -2.112  16.658  14.450  1.00 35.93           C
ATOM   1345  O   ALA A 411      -2.480  16.544  15.622  1.00 35.73           O
ATOM   1346  N   ILE A 412      -1.881  17.836  13.882  1.00 33.98           N
ATOM   1347  CA  ILE A 412      -2.084  19.073  14.606  1.00 35.17           C
ATOM   1348  CB  ILE A 412      -1.686  20.285  13.766  1.00 37.96           C
ATOM   1349  CG2 ILE A 412      -2.073  21.564  14.508  1.00 38.96           C
ATOM   1350  CG1 ILE A 412      -0.185  20.249  13.472  1.00 38.42           C
ATOM   1351  CD1 ILE A 412       0.256  21.237  12.438  1.00 37.80           C
ATOM   1352  C   ILE A 412      -3.554  19.266  14.975  1.00 36.80           C
ATOM   1353  O   ILE A 412      -3.885  19.565  16.123  1.00 36.44           O
ATOM   1354  N   ASN A 413      -4.434  19.080  13.994  1.00 41.27           N
ATOM   1355  CA  ASN A 413      -5.860  19.299  14.210  1.00 41.91           C
ATOM   1356  CB  ASN A 413      -6.550  19.616  12.876  1.00 42.51           C
ATOM   1357  CG  ASN A 413      -5.985  20.863  12.212  1.00 43.69           C
ATOM   1358  OD1 ASN A 413      -5.603  21.820  12.888  1.00 44.88           O
ATOM   1359  ND2 ASN A 413      -5.942  20.861  10.888  1.00 43.89           N
ATOM   1360  C   ASN A 413      -6.656  18.225  14.933  1.00 41.50           C
ATOM   1361  O   ASN A 413      -7.615  18.549  15.618  1.00 40.74           O
ATOM   1362  N   TYR A 414      -6.265  16.961  14.792  1.00 38.01           N
ATOM   1363  CA  TYR A 414      -7.000  15.862  15.421  1.00 38.04           C
ATOM   1364  CB  TYR A 414      -7.802  15.105  14.360  1.00 46.71           C
```

Figure 15

```
ATOM   1365  CG   TYR A 414      -8.751  15.994  13.608  1.00 47.76           C
ATOM   1366  CD1  TYR A 414      -9.930  16.431  14.194  1.00 48.40           C
ATOM   1367  CE1  TYR A 414     -10.768  17.309  13.537  1.00 48.73           C
ATOM   1368  CD2  TYR A 414      -8.438  16.458  12.341  1.00 47.63           C
ATOM   1369  CE2  TYR A 414      -9.267  17.337  11.678  1.00 49.07           C
ATOM   1370  CZ   TYR A 414     -10.430  17.758  12.282  1.00 49.07           C
ATOM   1371  OH   TYR A 414     -11.251  18.643  11.632  1.00 52.51           O
ATOM   1372  C    TYR A 414      -6.112  14.876  16.155  1.00 37.92           C
ATOM   1373  O    TYR A 414      -6.579  13.828  16.592  1.00 37.63           O
ATOM   1374  N    GLY A 415      -4.832  15.206  16.275  1.00 42.45           N
ATOM   1375  CA   GLY A 415      -3.912  14.316  16.953  1.00 42.29           C
ATOM   1376  C    GLY A 415      -3.847  12.928  16.340  1.00 42.44           C
ATOM   1377  O    GLY A 415      -3.547  11.968  17.032  1.00 43.71           O
ATOM   1378  N    THR A 416      -4.129  12.818  15.045  1.00 46.84           N
ATOM   1379  CA   THR A 416      -4.082  11.533  14.355  1.00 46.14           C
ATOM   1380  CB   THR A 416      -5.222  11.421  13.303  1.00 39.03           C
ATOM   1381  OG1  THR A 416      -4.804  10.600  12.204  1.00 41.62           O
ATOM   1382  CG2  THR A 416      -5.615  12.769  12.814  1.00 38.75           C
ATOM   1383  C    THR A 416      -2.714  11.341  13.705  1.00 45.61           C
ATOM   1384  O    THR A 416      -2.387  11.956  12.688  1.00 46.63           O
ATOM   1385  N    PHE A 417      -1.915  10.486  14.330  1.00 36.58           N
ATOM   1386  CA   PHE A 417      -0.560  10.187  13.890  1.00 35.09           C
ATOM   1387  CB   PHE A 417       0.393  10.209  15.095  1.00 36.61           C
ATOM   1388  CG   PHE A 417       0.654  11.586  15.649  1.00 36.92           C
ATOM   1389  CD2  PHE A 417       1.729  12.344  15.191  1.00 37.04           C
ATOM   1390  CD1  PHE A 417      -0.166  12.122  16.636  1.00 36.35           C
ATOM   1391  CE2  PHE A 417       1.982  13.613  15.714  1.00 37.17           C
ATOM   1392  CE1  PHE A 417       0.081  13.391  17.159  1.00 36.56           C
ATOM   1393  CZ   PHE A 417       1.159  14.136  16.695  1.00 35.84           C
ATOM   1394  C    PHE A 417      -0.475   8.827  13.219  1.00 33.88           C
ATOM   1395  O    PHE A 417      -0.989   7.841  13.733  1.00 33.34           O
ATOM   1396  N    THR A 418       0.194   8.789  12.074  1.00 31.14           N
ATOM   1397  CA   THR A 418       0.382   7.564  11.318  1.00 29.26           C
ATOM   1398  CB   THR A 418      -0.719   7.374  10.257  1.00 33.83           C
ATOM   1399  OG1  THR A 418      -0.491   8.280   9.167  1.00 33.96           O
ATOM   1400  CG2  THR A 418      -2.101   7.647  10.865  1.00 32.81           C
ATOM   1401  C    THR A 418       1.719   7.671  10.596  1.00 28.63           C
ATOM   1402  O    THR A 418       2.460   8.649  10.764  1.00 27.96           O
ATOM   1403  N    ILE A 419       2.029   6.665   9.792  1.00 28.58           N
ATOM   1404  CA   ILE A 419       3.267   6.662   9.035  1.00 28.30           C
ATOM   1405  CB   ILE A 419       3.483   5.310   8.317  1.00 29.27           C
ATOM   1406  CG2  ILE A 419       2.409   5.088   7.242  1.00 27.31           C
ATOM   1407  CG1  ILE A 419       4.892   5.273   7.715  1.00 29.74           C
ATOM   1408  CD1  ILE A 419       5.990   5.233   8.756  1.00 29.25           C
ATOM   1409  C    ILE A 419       3.240   7.802   8.004  1.00 27.97           C
ATOM   1410  O    ILE A 419       4.276   8.327   7.614  1.00 27.69           O
ATOM   1411  N    LYS A 420       2.043   8.186   7.576  1.00 32.06           N
ATOM   1412  CA   LYS A 420       1.902   9.272   6.609  1.00 31.65           C
ATOM   1413  CB   LYS A 420       0.485   9.314   6.039  1.00 26.13           C
ATOM   1414  CG   LYS A 420       0.165   8.149   5.132  1.00 26.22           C
ATOM   1415  CD   LYS A 420       1.220   7.995   4.073  1.00 26.20           C
ATOM   1416  CE   LYS A 420       0.852   6.925   3.062  1.00 25.73           C
ATOM   1417  NZ   LYS A 420       1.927   6.827   2.043  1.00 26.43           N
ATOM   1418  C    LYS A 420       2.246  10.613   7.253  1.00 30.81           C
ATOM   1419  O    LYS A 420       2.766  11.516   6.593  1.00 30.76           O
ATOM   1420  N    SER A 421       1.948  10.770   8.535  1.00 28.45           N
ATOM   1421  CA   SER A 421       2.323  12.020   9.152  1.00 28.66           C
ATOM   1422  CB   SER A 421       1.559  12.268  10.468  1.00 30.07           C
ATOM   1423  OG   SER A 421       1.572  11.176  11.357  1.00 36.35           O
ATOM   1424  C    SER A 421       3.846  12.007   9.315  1.00 28.59           C
```

Figure 15

| ATOM | 1425 | O   | SER | A | 421 | 4.475  | 13.056 | 9.325  | 1.00 | 29.84 | O |
|------|------|-----|-----|---|-----|--------|--------|--------|------|-------|---|
| ATOM | 1426 | N   | ASP | A | 422 | 4.460  | 10.828 | 9.396  | 1.00 | 30.05 | N |
| ATOM | 1427 | CA  | ASP | A | 422 | 5.924  | 10.787 | 9.484  | 1.00 | 29.67 | C |
| ATOM | 1428 | CB  | ASP | A | 422 | 6.480  | 9.381  | 9.776  | 1.00 | 29.79 | C |
| ATOM | 1429 | CG  | ASP | A | 422 | 6.286  | 8.931  | 11.211 | 1.00 | 29.63 | C |
| ATOM | 1430 | OD1 | ASP | A | 422 | 6.289  | 9.760  | 12.144 | 1.00 | 27.98 | O |
| ATOM | 1431 | OD2 | ASP | A | 422 | 6.158  | 7.707  | 11.402 | 1.00 | 30.78 | O |
| ATOM | 1432 | C   | ASP | A | 422 | 6.469  | 11.207 | 8.111  | 1.00 | 29.17 | C |
| ATOM | 1433 | O   | ASP | A | 422 | 7.478  | 11.913 | 8.029  | 1.00 | 29.69 | O |
| ATOM | 1434 | N   | VAL | A | 423 | 5.823  | 10.746 | 7.039  | 1.00 | 26.48 | N |
| ATOM | 1435 | CA  | VAL | A | 423 | 6.251  | 11.104 | 5.686  | 1.00 | 25.32 | C |
| ATOM | 1436 | CB  | VAL | A | 423 | 5.330  | 10.487 | 4.595  | 1.00 | 27.54 | C |
| ATOM | 1437 | CG1 | VAL | A | 423 | 5.586  | 11.191 | 3.226  | 1.00 | 26.08 | C |
| ATOM | 1438 | CG2 | VAL | A | 423 | 5.616  | 8.963  | 4.461  | 1.00 | 26.32 | C |
| ATOM | 1439 | C   | VAL | A | 423 | 6.259  | 12.630 | 5.537  | 1.00 | 25.26 | C |
| ATOM | 1440 | O   | VAL | A | 423 | 7.150  | 13.182 | 4.897  | 1.00 | 24.33 | O |
| ATOM | 1441 | N   | TRP | A | 424 | 5.269  | 13.296 | 6.137  | 1.00 | 23.00 | N |
| ATOM | 1442 | CA  | TRP | A | 424 | 5.185  | 14.760 | 6.102  | 1.00 | 23.55 | C |
| ATOM | 1443 | CB  | TRP | A | 424 | 3.898  | 15.237 | 6.790  | 1.00 | 26.89 | C |
| ATOM | 1444 | CG  | TRP | A | 424 | 3.805  | 16.729 | 7.005  | 1.00 | 27.63 | C |
| ATOM | 1445 | CD2 | TRP | A | 424 | 2.948  | 17.648 | 6.321  | 1.00 | 26.80 | C |
| ATOM | 1446 | CE2 | TRP | A | 424 | 3.263  | 18.941 | 6.795  | 1.00 | 27.70 | C |
| ATOM | 1447 | CE3 | TRP | A | 424 | 1.948  | 17.507 | 5.349  | 1.00 | 27.90 | C |
| ATOM | 1448 | CD1 | TRP | A | 424 | 4.575  | 17.486 | 7.847  | 1.00 | 27.19 | C |
| ATOM | 1449 | NE1 | TRP | A | 424 | 4.260  | 18.804 | 7.723  | 1.00 | 25.21 | N |
| ATOM | 1450 | CZ2 | TRP | A | 424 | 2.611  | 20.092 | 6.331  | 1.00 | 26.72 | C |
| ATOM | 1451 | CZ3 | TRP | A | 424 | 1.306  | 18.643 | 4.890  | 1.00 | 28.42 | C |
| ATOM | 1452 | CH2 | TRP | A | 424 | 1.640  | 19.923 | 5.382  | 1.00 | 27.49 | C |
| ATOM | 1453 | C   | TRP | A | 424 | 6.424  | 15.274 | 6.836  | 1.00 | 24.55 | C |
| ATOM | 1454 | O   | TRP | A | 424 | 7.154  | 16.124 | 6.323  | 1.00 | 24.71 | O |
| ATOM | 1455 | N   | SER | A | 425 | 6.678  | 14.735 | 8.027  | 1.00 | 26.43 | N |
| ATOM | 1456 | CA  | SER | A | 425 | 7.852  | 15.134 | 8.801  | 1.00 | 27.99 | C |
| ATOM | 1457 | CB  | SER | A | 425 | 7.948  | 14.341 | 10.116 | 1.00 | 30.07 | C |
| ATOM | 1458 | OG  | SER | A | 425 | 6.928  | 14.724 | 11.022 | 1.00 | 28.88 | O |
| ATOM | 1459 | C   | SER | A | 425 | 9.130  | 14.917 | 7.995  | 1.00 | 29.17 | C |
| ATOM | 1460 | O   | SER | A | 425 | 10.012 | 15.769 | 8.004  | 1.00 | 30.89 | O |
| ATOM | 1461 | N   | PHE | A | 426 | 9.248  | 13.779 | 7.309  | 1.00 | 29.82 | N |
| ATOM | 1462 | CA  | PHE | A | 426 | 10.444 | 13.528 | 6.503  | 1.00 | 29.43 | C |
| ATOM | 1463 | CB  | PHE | A | 426 | 10.376 | 12.163 | 5.794  | 1.00 | 24.41 | C |
| ATOM | 1464 | CG  | PHE | A | 426 | 11.600 | 11.849 | 4.958  | 1.00 | 24.73 | C |
| ATOM | 1465 | CD1 | PHE | A | 426 | 12.760 | 11.352 | 5.550  | 1.00 | 25.16 | C |
| ATOM | 1466 | CD2 | PHE | A | 426 | 11.587 | 12.038 | 3.581  | 1.00 | 25.10 | C |
| ATOM | 1467 | CE1 | PHE | A | 426 | 13.876 | 11.048 | 4.791  | 1.00 | 25.51 | C |
| ATOM | 1468 | CE2 | PHE | A | 426 | 12.702 | 11.736 | 2.805  | 1.00 | 25.08 | C |
| ATOM | 1469 | CZ  | PHE | A | 426 | 13.853 | 11.238 | 3.411  | 1.00 | 26.46 | C |
| ATOM | 1470 | C   | PHE | A | 426 | 10.597 | 14.629 | 5.449  | 1.00 | 28.92 | C |
| ATOM | 1471 | O   | PHE | A | 426 | 11.718 | 15.000 | 5.088  | 1.00 | 28.91 | O |
| ATOM | 1472 | N   | GLY | A | 427 | 9.467  | 15.124 | 4.942  | 1.00 | 29.45 | N |
| ATOM | 1473 | CA  | GLY | A | 427 | 9.498  | 16.196 | 3.958  | 1.00 | 27.23 | C |
| ATOM | 1474 | C   | GLY | A | 427 | 10.138 | 17.442 | 4.561  | 1.00 | 27.21 | C |
| ATOM | 1475 | O   | GLY | A | 427 | 10.975 | 18.077 | 3.935  | 1.00 | 28.26 | O |
| ATOM | 1476 | N   | ILE | A | 428 | 9.752  | 17.798 | 5.785  | 1.00 | 26.44 | N |
| ATOM | 1477 | CA  | ILE | A | 428 | 10.332 | 18.963 | 6.442  | 1.00 | 26.40 | C |
| ATOM | 1478 | CB  | ILE | A | 428 | 9.655  | 19.262 | 7.804  | 1.00 | 27.40 | C |
| ATOM | 1479 | CG2 | ILE | A | 428 | 10.286 | 20.511 | 8.433  | 1.00 | 27.22 | C |
| ATOM | 1480 | CG1 | ILE | A | 428 | 8.144  | 19.467 | 7.630  | 1.00 | 26.33 | C |
| ATOM | 1481 | CD1 | ILE | A | 428 | 7.754  | 20.641 | 6.720  | 1.00 | 26.24 | C |
| ATOM | 1482 | C   | ILE | A | 428 | 11.818 | 18.669 | 6.684  | 1.00 | 26.97 | C |
| ATOM | 1483 | O   | ILE | A | 428 | 12.673 | 19.540 | 6.506  | 1.00 | 25.75 | O |
| ATOM | 1484 | N   | LEU | A | 429 | 12.126 | 17.428 | 7.059  | 1.00 | 26.51 | N |

Figure 15

```
ATOM   1485  CA   LEU A 429      13.511  17.035   7.326  1.00 26.93           C
ATOM   1486  CB   LEU A 429      13.565  15.562   7.784  1.00 25.83           C
ATOM   1487  CG   LEU A 429      14.754  15.100   8.650  1.00 25.09           C
ATOM   1488  CD1  LEU A 429      14.445  13.742   9.284  1.00 26.02           C
ATOM   1489  CD2  LEU A 429      16.014  15.020   7.813  1.00 23.30           C
ATOM   1490  C    LEU A 429      14.408  17.260   6.092  1.00 27.04           C
ATOM   1491  O    LEU A 429      15.590  17.584   6.230  1.00 26.70           O
ATOM   1492  N    LEU A 430      13.842  17.088   4.896  1.00 25.44           N
ATOM   1493  CA   LEU A 430      14.592  17.306   3.666  1.00 25.33           C
ATOM   1494  CB   LEU A 430      13.754  16.927   2.431  1.00 26.57           C
ATOM   1495  CG   LEU A 430      13.448  15.435   2.194  1.00 27.05           C
ATOM   1496  CD1  LEU A 430      12.612  15.254   0.912  1.00 27.20           C
ATOM   1497  CD2  LEU A 430      14.755  14.652   2.089  1.00 28.00           C
ATOM   1498  C    LEU A 430      15.050  18.769   3.567  1.00 26.12           C
ATOM   1499  O    LEU A 430      16.158  19.038   3.111  1.00 26.78           O
ATOM   1500  N    THR A 431      14.211  19.710   3.998  1.00 32.52           N
ATOM   1501  CA   THR A 431      14.598  21.119   3.943  1.00 33.49           C
ATOM   1502  CB   THR A 431      13.418  22.102   4.284  1.00 24.78           C
ATOM   1503  OG1  THR A 431      13.015  21.951   5.655  1.00 24.37           O
ATOM   1504  CG2  THR A 431      12.226  21.854   3.353  1.00 23.31           C
ATOM   1505  C    THR A 431      15.770  21.379   4.890  1.00 34.51           C
ATOM   1506  O    THR A 431      16.682  22.141   4.556  1.00 35.05           O
ATOM   1507  N    GLU A 432      15.758  20.733   6.056  1.00 29.67           N
ATOM   1508  CA   GLU A 432      16.845  20.883   7.027  1.00 29.83           C
ATOM   1509  CB   GLU A 432      16.555  20.088   8.308  1.00 32.47           C
ATOM   1510  CG   GLU A 432      15.524  20.698   9.237  1.00 33.96           C
ATOM   1511  CD   GLU A 432      15.270  19.834  10.468  1.00 34.78           C
ATOM   1512  OE1  GLU A 432      14.688  18.730  10.337  1.00 33.97           O
ATOM   1513  OE2  GLU A 432      15.664  20.264  11.574  1.00 37.02           O
ATOM   1514  C    GLU A 432      18.159  20.377   6.437  1.00 30.61           C
ATOM   1515  O    GLU A 432      19.206  20.993   6.602  1.00 31.57           O
ATOM   1516  N    ILE A 433      18.094  19.245   5.747  1.00 29.46           N
ATOM   1517  CA   ILE A 433      19.278  18.650   5.155  1.00 30.49           C
ATOM   1518  CB   ILE A 433      18.943  17.284   4.537  1.00 32.56           C
ATOM   1519  CG2  ILE A 433      20.072  16.842   3.611  1.00 33.22           C
ATOM   1520  CG1  ILE A 433      18.718  16.262   5.661  1.00 33.66           C
ATOM   1521  CD1  ILE A 433      18.448  14.842   5.191  1.00 32.16           C
ATOM   1522  C    ILE A 433      19.997  19.501   4.107  1.00 31.06           C
ATOM   1523  O    ILE A 433      21.209  19.686   4.177  1.00 30.43           O
ATOM   1524  N    VAL A 434      19.249  20.025   3.145  1.00 38.41           N
ATOM   1525  CA   VAL A 434      19.851  20.822   2.085  1.00 39.33           C
ATOM   1526  CB   VAL A 434      19.002  20.770   0.807  1.00 37.83           C
ATOM   1527  CG1  VAL A 434      18.902  19.332   0.321  1.00 37.92           C
ATOM   1528  CG2  VAL A 434      17.619  21.354   1.071  1.00 37.82           C
ATOM   1529  C    VAL A 434      20.117  22.278   2.453  1.00 39.82           C
ATOM   1530  O    VAL A 434      20.765  22.990   1.704  1.00 41.28           O
ATOM   1531  N    THR A 435      19.623  22.720   3.601  1.00 35.35           N
ATOM   1532  CA   THR A 435      19.853  24.089   4.045  1.00 36.18           C
ATOM   1533  CB   THR A 435      18.584  24.715   4.598  1.00 37.82           C
ATOM   1534  OG1  THR A 435      18.061  23.863   5.625  1.00 38.39           O
ATOM   1535  CG2  THR A 435      17.554  24.915   3.496  1.00 35.46           C
ATOM   1536  C    THR A 435      20.892  24.069   5.170  1.00 37.73           C
ATOM   1537  O    THR A 435      21.131  25.079   5.830  1.00 37.44           O
ATOM   1538  N    HIS A 436      21.483  22.898   5.384  1.00 45.57           N
ATOM   1539  CA   HIS A 436      22.492  22.694   6.408  1.00 46.65           C
ATOM   1540  CB   HIS A 436      23.750  23.497   6.051  1.00 57.23           C
ATOM   1541  CG   HIS A 436      24.504  22.928   4.887  1.00 57.96           C
ATOM   1542  CD2  HIS A 436      24.575  23.320   3.593  1.00 58.55           C
ATOM   1543  ND1  HIS A 436      25.228  21.757   4.972  1.00 58.91           N
ATOM   1544  CE1  HIS A 436      25.711  21.450   3.782  1.00 58.33           C
```

Figure 15

| | | | | | | | | | |
|---|---|---|---|---|---|---|---|---|---|
| ATOM | 1545 | NE2 | HIS | A | 436 | 25.328 | 22.382 | 2.927 | 1.00 60.11 | N |
| ATOM | 1546 | C | HIS | A | 436 | 22.019 | 22.988 | 7.835 | 1.00 47.05 | C |
| ATOM | 1547 | O | HIS | A | 436 | 22.716 | 23.623 | 8.627 | 1.00 46.36 | O |
| ATOM | 1548 | N | GLY | A | 437 | 20.821 | 22.511 | 8.157 | 1.00 41.84 | N |
| ATOM | 1549 | CA | GLY | A | 437 | 20.300 | 22.691 | 9.499 | 1.00 42.42 | C |
| ATOM | 1550 | C | GLY | A | 437 | 19.398 | 23.879 | 9.758 | 1.00 42.52 | C |
| ATOM | 1551 | O | GLY | A | 437 | 19.019 | 24.117 | 10.903 | 1.00 43.28 | O |
| ATOM | 1552 | N | ARG | A | 438 | 19.051 | 24.623 | 8.716 | 1.00 35.47 | N |
| ATOM | 1553 | CA | ARG | A | 438 | 18.189 | 25.780 | 8.880 | 1.00 36.62 | C |
| ATOM | 1554 | CB | ARG | A | 438 | 18.004 | 26.509 | 7.543 | 1.00 51.85 | C |
| ATOM | 1555 | CG | ARG | A | 438 | 17.124 | 27.772 | 7.626 | 1.00 54.81 | C |
| ATOM | 1556 | CD | ARG | A | 438 | 16.447 | 28.079 | 6.279 | 1.00 57.15 | C |
| ATOM | 1557 | NE | ARG | A | 438 | 15.304 | 27.195 | 6.036 | 1.00 58.01 | N |
| ATOM | 1558 | CZ | ARG | A | 438 | 14.690 | 27.060 | 4.864 | 1.00 58.81 | C |
| ATOM | 1559 | NH1 | ARG | A | 438 | 15.109 | 27.746 | 3.810 | 1.00 58.91 | N |
| ATOM | 1560 | NH2 | ARG | A | 438 | 13.651 | 26.242 | 4.748 | 1.00 59.34 | N |
| ATOM | 1561 | C | ARG | A | 438 | 16.823 | 25.366 | 9.419 | 1.00 36.16 | C |
| ATOM | 1562 | O | ARG | A | 438 | 16.282 | 24.322 | 9.051 | 1.00 35.63 | O |
| ATOM | 1563 | N | ILE | A | 439 | 16.271 | 26.197 | 10.294 | 1.00 43.51 | N |
| ATOM | 1564 | CA | ILE | A | 439 | 14.963 | 25.943 | 10.883 | 1.00 43.54 | C |
| ATOM | 1565 | CB | ILE | A | 439 | 14.695 | 26.918 | 12.049 | 1.00 55.22 | C |
| ATOM | 1566 | CG2 | ILE | A | 439 | 13.336 | 26.634 | 12.687 | 1.00 56.37 | C |
| ATOM | 1567 | CG1 | ILE | A | 439 | 15.799 | 26.761 | 13.099 | 1.00 57.36 | C |
| ATOM | 1568 | CD1 | ILE | A | 439 | 15.705 | 27.734 | 14.256 | 1.00 58.77 | C |
| ATOM | 1569 | C | ILE | A | 439 | 13.879 | 26.106 | 9.814 | 1.00 42.73 | C |
| ATOM | 1570 | O | ILE | A | 439 | 13.949 | 26.996 | 8.967 | 1.00 42.67 | O |
| ATOM | 1571 | N | PRO | A | 440 | 12.875 | 25.222 | 9.825 | 1.00 42.72 | N |
| ATOM | 1572 | CD | PRO | A | 440 | 12.833 | 23.973 | 10.602 | 1.00 36.01 | C |
| ATOM | 1573 | CA | PRO | A | 440 | 11.772 | 25.266 | 8.856 | 1.00 41.64 | C |
| ATOM | 1574 | CB | PRO | A | 440 | 10.993 | 23.989 | 9.173 | 1.00 35.59 | C |
| ATOM | 1575 | CG | PRO | A | 440 | 12.064 | 23.070 | 9.687 | 1.00 35.30 | C |
| ATOM | 1576 | C | PRO | A | 440 | 10.921 | 26.523 | 9.024 | 1.00 40.08 | C |
| ATOM | 1577 | O | PRO | A | 440 | 10.840 | 27.073 | 10.118 | 1.00 39.83 | O |
| ATOM | 1578 | N | TYR | A | 441 | 10.285 | 26.973 | 7.946 | 1.00 30.28 | N |
| ATOM | 1579 | CA | TYR | A | 441 | 9.443 | 28.166 | 8.007 | 1.00 29.47 | C |
| ATOM | 1580 | CB | TYR | A | 441 | 8.195 | 27.881 | 8.849 | 1.00 34.23 | C |
| ATOM | 1581 | CG | TYR | A | 441 | 7.365 | 26.711 | 8.361 | 1.00 33.59 | C |
| ATOM | 1582 | CD1 | TYR | A | 441 | 6.507 | 26.846 | 7.271 | 1.00 32.19 | C |
| ATOM | 1583 | CE1 | TYR | A | 441 | 5.783 | 25.772 | 6.795 | 1.00 31.41 | C |
| ATOM | 1584 | CD2 | TYR | A | 441 | 7.471 | 25.459 | 8.965 | 1.00 33.18 | C |
| ATOM | 1585 | CE2 | TYR | A | 441 | 6.750 | 24.375 | 8.497 | 1.00 31.47 | C |
| ATOM | 1586 | CZ | TYR | A | 441 | 5.911 | 24.538 | 7.408 | 1.00 33.53 | C |
| ATOM | 1587 | OH | TYR | A | 441 | 5.226 | 23.462 | 6.904 | 1.00 33.15 | O |
| ATOM | 1588 | C | TYR | A | 441 | 10.241 | 29.307 | 8.650 | 1.00 30.34 | C |
| ATOM | 1589 | O | TYR | A | 441 | 9.844 | 29.862 | 9.671 | 1.00 29.33 | O |
| ATOM | 1590 | N | PRO | A | 442 | 11.388 | 29.662 | 8.059 | 1.00 44.15 | N |
| ATOM | 1591 | CD | PRO | A | 442 | 11.917 | 29.236 | 6.751 | 1.00 37.96 | C |
| ATOM | 1592 | CA | PRO | A | 442 | 12.198 | 30.743 | 8.626 | 1.00 46.70 | C |
| ATOM | 1593 | CB | PRO | A | 442 | 13.400 | 30.786 | 7.692 | 1.00 40.21 | C |
| ATOM | 1594 | CG | PRO | A | 442 | 12.801 | 30.400 | 6.373 | 1.00 39.16 | C |
| ATOM | 1595 | C | PRO | A | 442 | 11.428 | 32.061 | 8.664 | 1.00 48.51 | C |
| ATOM | 1596 | O | PRO | A | 442 | 11.074 | 32.612 | 7.626 | 1.00 50.63 | O |
| ATOM | 1597 | N | GLY | A | 443 | 11.147 | 32.554 | 9.862 | 1.00 51.44 | N |
| ATOM | 1598 | CA | GLY | A | 443 | 10.422 | 33.805 | 9.965 | 1.00 53.84 | C |
| ATOM | 1599 | C | GLY | A | 443 | 8.995 | 33.653 | 10.442 | 1.00 54.63 | C |
| ATOM | 1600 | O | GLY | A | 443 | 8.192 | 34.576 | 10.315 | 1.00 54.83 | O |
| ATOM | 1601 | N | MET | A | 444 | 8.676 | 32.484 | 10.988 | 1.00 52.24 | N |
| ATOM | 1602 | CA | MET | A | 444 | 7.336 | 32.228 | 11.498 | 1.00 52.63 | C |
| ATOM | 1603 | CB | MET | A | 444 | 6.556 | 31.277 | 10.579 | 1.00 46.90 | C |
| ATOM | 1604 | CG | MET | A | 444 | 6.359 | 31.721 | 9.146 | 1.00 47.75 | C |

Figure 15

| | | | | | | | | | | |
|---|---|---|---|---|---|---|---|---|---|---|
| ATOM | 1605 | SD | MET | A | 444 | 5.288 | 30.535 | 8.259 | 1.00 48.11 | S |
| ATOM | 1606 | CE | MET | A | 444 | 3.874 | 30.628 | 9.209 | 1.00 49.41 | C |
| ATOM | 1607 | C | MET | A | 444 | 7.434 | 31.567 | 12.861 | 1.00 52.61 | C |
| ATOM | 1608 | O | MET | A | 444 | 8.305 | 30.724 | 13.090 | 1.00 53.04 | O |
| ATOM | 1609 | N | THR | A | 445 | 6.548 | 31.958 | 13.765 | 1.00 47.17 | N |
| ATOM | 1610 | CA | THR | A | 445 | 6.503 | 31.351 | 15.083 | 1.00 47.11 | C |
| ATOM | 1611 | CB | THR | A | 445 | 5.875 | 32.297 | 16.119 | 1.00 46.35 | C |
| ATOM | 1612 | OG1 | THR | A | 445 | 4.528 | 32.601 | 15.733 | 1.00 45.97 | O |
| ATOM | 1613 | CG2 | THR | A | 445 | 6.683 | 33.588 | 16.220 | 1.00 46.81 | C |
| ATOM | 1614 | C | THR | A | 445 | 5.580 | 30.146 | 14.901 | 1.00 46.82 | C |
| ATOM | 1615 | O | THR | A | 445 | 4.975 | 29.983 | 13.842 | 1.00 46.80 | O |
| ATOM | 1616 | N | ASN | A | 446 | 5.455 | 29.310 | 15.921 | 1.00 50.71 | N |
| ATOM | 1617 | CA | ASN | A | 446 | 4.588 | 28.145 | 15.812 | 1.00 51.00 | C |
| ATOM | 1618 | CB | ASN | A | 446 | 4.648 | 27.311 | 17.095 | 1.00 45.19 | C |
| ATOM | 1619 | CG | ASN | A | 446 | 5.997 | 26.658 | 17.295 | 1.00 45.57 | C |
| ATOM | 1620 | OD1 | ASN | A | 446 | 6.790 | 26.551 | 16.358 | 1.00 45.81 | O |
| ATOM | 1621 | ND2 | ASN | A | 446 | 6.261 | 26.203 | 18.512 | 1.00 45.47 | N |
| ATOM | 1622 | C | ASN | A | 446 | 3.137 | 28.502 | 15.490 | 1.00 50.54 | C |
| ATOM | 1623 | O | ASN | A | 446 | 2.557 | 27.969 | 14.546 | 1.00 50.04 | O |
| ATOM | 1624 | N | PRO | A | 447 | 2.530 | 29.412 | 16.269 | 1.00 54.80 | N |
| ATOM | 1625 | CD | PRO | A | 447 | 3.041 | 30.178 | 17.422 | 1.00 45.99 | C |
| ATOM | 1626 | CA | PRO | A | 447 | 1.139 | 29.765 | 15.978 | 1.00 53.40 | C |
| ATOM | 1627 | CB | PRO | A | 447 | 0.780 | 30.731 | 17.111 | 1.00 44.93 | C |
| ATOM | 1628 | CG | PRO | A | 447 | 2.088 | 31.336 | 17.476 | 1.00 45.60 | C |
| ATOM | 1629 | C | PRO | A | 447 | 0.985 | 30.365 | 14.584 | 1.00 52.46 | C |
| ATOM | 1630 | O | PRO | A | 447 | -0.083 | 30.273 | 13.974 | 1.00 51.69 | O |
| ATOM | 1631 | N | GLU | A | 448 | 2.060 | 30.965 | 14.081 | 1.00 42.93 | N |
| ATOM | 1632 | CA | GLU | A | 448 | 2.034 | 31.547 | 12.749 | 1.00 41.92 | C |
| ATOM | 1633 | CB | GLU | A | 448 | 3.260 | 32.441 | 12.518 | 1.00 54.61 | C |
| ATOM | 1634 | CG | GLU | A | 448 | 3.003 | 33.918 | 12.857 | 1.00 57.82 | C |
| ATOM | 1635 | CD | GLU | A | 448 | 4.270 | 34.752 | 12.948 | 1.00 58.25 | C |
| ATOM | 1636 | OE1 | GLU | A | 448 | 5.124 | 34.670 | 12.043 | 1.00 58.59 | O |
| ATOM | 1637 | OE2 | GLU | A | 448 | 4.407 | 35.503 | 13.935 | 1.00 61.40 | O |
| ATOM | 1638 | C | GLU | A | 448 | 2.011 | 30.401 | 11.750 | 1.00 40.67 | C |
| ATOM | 1639 | O | GLU | A | 448 | 1.186 | 30.392 | 10.829 | 1.00 39.84 | O |
| ATOM | 1640 | N | VAL | A | 449 | 2.912 | 29.434 | 11.934 | 1.00 34.36 | N |
| ATOM | 1641 | CA | VAL | A | 449 | 2.953 | 28.278 | 11.047 | 1.00 32.48 | C |
| ATOM | 1642 | CB | VAL | A | 449 | 4.007 | 27.228 | 11.495 | 1.00 35.58 | C |
| ATOM | 1643 | CG1 | VAL | A | 449 | 3.738 | 25.883 | 10.807 | 1.00 33.49 | C |
| ATOM | 1644 | CG2 | VAL | A | 449 | 5.405 | 27.714 | 11.145 | 1.00 33.38 | C |
| ATOM | 1645 | C | VAL | A | 449 | 1.579 | 27.635 | 11.037 | 1.00 31.75 | C |
| ATOM | 1646 | O | VAL | A | 449 | 1.062 | 27.285 | 9.981 | 1.00 31.25 | O |
| ATOM | 1647 | N | ILE | A | 450 | 0.986 | 27.499 | 12.218 | 1.00 38.69 | N |
| ATOM | 1648 | CA | ILE | A | 450 | -0.335 | 26.899 | 12.338 | 1.00 39.34 | C |
| ATOM | 1649 | CB | ILE | A | 450 | -0.832 | 26.912 | 13.804 | 1.00 48.89 | C |
| ATOM | 1650 | CG2 | ILE | A | 450 | -2.233 | 26.310 | 13.889 | 1.00 47.74 | C |
| ATOM | 1651 | CG1 | ILE | A | 450 | 0.140 | 26.132 | 14.695 | 1.00 50.22 | C |
| ATOM | 1652 | CD1 | ILE | A | 450 | 0.343 | 24.706 | 14.278 | 1.00 50.37 | C |
| ATOM | 1653 | C | ILE | A | 450 | -1.356 | 27.646 | 11.473 | 1.00 39.41 | C |
| ATOM | 1654 | O | ILE | A | 450 | -2.127 | 27.023 | 10.745 | 1.00 38.95 | O |
| ATOM | 1655 | N | GLN | A | 451 | -1.358 | 28.977 | 11.562 | 1.00 35.91 | N |
| ATOM | 1656 | CA | GLN | A | 451 | -2.289 | 29.795 | 10.778 | 1.00 34.89 | C |
| ATOM | 1657 | CB | GLN | A | 451 | -2.098 | 31.290 | 11.064 | 1.00 43.11 | C |
| ATOM | 1658 | CG | GLN | A | 451 | -2.301 | 31.718 | 12.506 | 1.00 47.51 | C |
| ATOM | 1659 | CD | GLN | A | 451 | -1.805 | 33.142 | 12.764 | 1.00 49.87 | C |
| ATOM | 1660 | OE1 | GLN | A | 451 | -2.360 | 34.110 | 12.248 | 1.00 53.45 | O |
| ATOM | 1661 | NE2 | GLN | A | 451 | -0.751 | 33.269 | 13.555 | 1.00 50.66 | N |
| ATOM | 1662 | C | GLN | A | 451 | -2.080 | 29.564 | 9.289 | 1.00 32.67 | C |
| ATOM | 1663 | O | GLN | A | 451 | -3.034 | 29.444 | 8.535 | 1.00 31.77 | O |
| ATOM | 1664 | N | ASN | A | 452 | -0.822 | 29.514 | 8.875 | 1.00 30.65 | N |

Figure 15

| ATOM | 1665 | CA | ASN | A | 452 | -0.494 | 29.318 | 7.476 | 1.00 | 30.67 | C |
| ATOM | 1666 | CB | ASN | A | 452 | 0.991 | 29.619 | 7.251 | 1.00 | 32.01 | C |
| ATOM | 1667 | CG | ASN | A | 452 | 1.258 | 31.120 | 7.027 | 1.00 | 34.70 | C |
| ATOM | 1668 | OD1 | ASN | A | 452 | 1.064 | 31.639 | 5.931 | 1.00 | 34.81 | O |
| ATOM | 1669 | ND2 | ASN | A | 452 | 1.686 | 31.813 | 8.073 | 1.00 | 34.36 | N |
| ATOM | 1670 | C | ASN | A | 452 | -0.882 | 27.929 | 6.941 | 1.00 | 30.47 | C |
| ATOM | 1671 | O | ASN | A | 452 | -1.346 | 27.819 | 5.808 | 1.00 | 29.91 | O |
| ATOM | 1672 | N | LEU | A | 453 | -0.709 | 26.881 | 7.744 | 1.00 | 34.96 | N |
| ATOM | 1673 | CA | LEU | A | 453 | -1.089 | 25.538 | 7.302 | 1.00 | 34.91 | C |
| ATOM | 1674 | CB | LEU | A | 453 | -0.564 | 24.461 | 8.261 | 1.00 | 31.97 | C |
| ATOM | 1675 | CG | LEU | A | 453 | 0.950 | 24.238 | 8.210 | 1.00 | 32.72 | C |
| ATOM | 1676 | CD1 | LEU | A | 453 | 1.352 | 23.172 | 9.218 | 1.00 | 32.59 | C |
| ATOM | 1677 | CD2 | LEU | A | 453 | 1.355 | 23.826 | 6.793 | 1.00 | 32.97 | C |
| ATOM | 1678 | C | LEU | A | 453 | -2.608 | 25.461 | 7.217 | 1.00 | 35.04 | C |
| ATOM | 1679 | O | LEU | A | 453 | -3.158 | 24.716 | 6.415 | 1.00 | 33.15 | O |
| ATOM | 1680 | N | GLU | A | 454 | -3.296 | 26.238 | 8.045 | 1.00 | 30.55 | N |
| ATOM | 1681 | CA | GLU | A | 454 | -4.747 | 26.237 | 7.977 | 1.00 | 32.46 | C |
| ATOM | 1682 | CB | GLU | A | 454 | -5.342 | 27.155 | 9.047 | 1.00 | 51.42 | C |
| ATOM | 1683 | CG | GLU | A | 454 | -4.837 | 26.858 | 10.440 | 1.00 | 55.68 | C |
| ATOM | 1684 | CD | GLU | A | 454 | -5.607 | 27.597 | 11.512 | 1.00 | 58.20 | C |
| ATOM | 1685 | OE1 | GLU | A | 454 | -5.894 | 28.800 | 11.320 | 1.00 | 59.23 | O |
| ATOM | 1686 | OE2 | GLU | A | 454 | -5.916 | 26.973 | 12.550 | 1.00 | 59.43 | O |
| ATOM | 1687 | C | GLU | A | 454 | -5.170 | 26.726 | 6.584 | 1.00 | 31.75 | C |
| ATOM | 1688 | O | GLU | A | 454 | -6.237 | 26.373 | 6.097 | 1.00 | 31.66 | O |
| ATOM | 1689 | N | ARG | A | 455 | -4.308 | 27.524 | 5.954 | 1.00 | 34.19 | N |
| ATOM | 1690 | CA | ARG | A | 455 | -4.557 | 28.075 | 4.619 | 1.00 | 33.97 | C |
| ATOM | 1691 | CB | ARG | A | 455 | -4.121 | 29.543 | 4.558 | 1.00 | 39.01 | C |
| ATOM | 1692 | CG | ARG | A | 455 | -4.733 | 30.417 | 5.615 | 1.00 | 41.28 | C |
| ATOM | 1693 | CD | ARG | A | 455 | -4.371 | 31.874 | 5.360 | 1.00 | 43.91 | C |
| ATOM | 1694 | NE | ARG | A | 455 | -4.494 | 32.645 | 6.589 | 1.00 | 47.58 | N |
| ATOM | 1695 | CZ | ARG | A | 455 | -3.470 | 33.192 | 7.234 | 1.00 | 46.84 | C |
| ATOM | 1696 | NH1 | ARG | A | 455 | -2.236 | 33.065 | 6.765 | 1.00 | 43.70 | N |
| ATOM | 1697 | NH2 | ARG | A | 455 | -3.694 | 33.858 | 8.358 | 1.00 | 49.51 | N |
| ATOM | 1698 | C | ARG | A | 455 | -3.842 | 27.328 | 3.494 | 1.00 | 31.47 | C |
| ATOM | 1699 | O | ARG | A | 455 | -3.735 | 27.840 | 2.375 | 1.00 | 29.91 | O |
| ATOM | 1700 | N | GLY | A | 456 | -3.332 | 26.137 | 3.801 | 1.00 | 28.85 | N |
| ATOM | 1701 | CA | GLY | A | 456 | -2.657 | 25.332 | 2.795 | 1.00 | 26.90 | C |
| ATOM | 1702 | C | GLY | A | 456 | -1.284 | 25.814 | 2.378 | 1.00 | 26.63 | C |
| ATOM | 1703 | O | GLY | A | 456 | -0.818 | 25.505 | 1.290 | 1.00 | 27.82 | O |
| ATOM | 1704 | N | TYR | A | 457 | -0.622 | 26.561 | 3.245 | 1.00 | 29.25 | N |
| ATOM | 1705 | CA | TYR | A | 457 | 0.700 | 27.093 | 2.937 | 1.00 | 30.05 | C |
| ATOM | 1706 | CB | TYR | A | 457 | 1.099 | 28.121 | 4.013 | 1.00 | 28.92 | C |
| ATOM | 1707 | CG | TYR | A | 457 | 2.483 | 28.697 | 3.855 | 1.00 | 29.19 | C |
| ATOM | 1708 | CD1 | TYR | A | 457 | 3.590 | 28.082 | 4.440 | 1.00 | 29.53 | C |
| ATOM | 1709 | CE1 | TYR | A | 457 | 4.870 | 28.609 | 4.273 | 1.00 | 29.64 | C |
| ATOM | 1710 | CD2 | TYR | A | 457 | 2.690 | 29.862 | 3.097 | 1.00 | 29.70 | C |
| ATOM | 1711 | CE2 | TYR | A | 457 | 3.947 | 30.394 | 2.928 | 1.00 | 28.55 | C |
| ATOM | 1712 | CZ | TYR | A | 457 | 5.037 | 29.766 | 3.513 | 1.00 | 30.82 | C |
| ATOM | 1713 | OH | TYR | A | 457 | 6.293 | 30.290 | 3.317 | 1.00 | 32.48 | O |
| ATOM | 1714 | C | TYR | A | 457 | 1.770 | 25.999 | 2.837 | 1.00 | 31.20 | C |
| ATOM | 1715 | O | TYR | A | 457 | 1.732 | 25.021 | 3.579 | 1.00 | 32.87 | O |
| ATOM | 1716 | N | ARG | A | 458 | 2.712 | 26.175 | 1.915 | 1.00 | 27.60 | N |
| ATOM | 1717 | CA | ARG | A | 458 | 3.808 | 25.240 | 1.731 | 1.00 | 29.11 | C |
| ATOM | 1718 | CB | ARG | A | 458 | 3.550 | 24.312 | 0.528 | 1.00 | 30.90 | C |
| ATOM | 1719 | CG | ARG | A | 458 | 2.318 | 23.412 | 0.673 | 1.00 | 29.59 | C |
| ATOM | 1720 | CD | ARG | A | 458 | 2.493 | 22.400 | 1.798 | 1.00 | 28.89 | C |
| ATOM | 1721 | NE | ARG | A | 458 | 1.384 | 21.456 | 1.869 | 1.00 | 27.25 | N |
| ATOM | 1722 | CZ | ARG | A | 458 | 0.243 | 21.671 | 2.512 | 1.00 | 27.74 | C |
| ATOM | 1723 | NH1 | ARG | A | 458 | 0.039 | 22.812 | 3.164 | 1.00 | 29.18 | N |
| ATOM | 1724 | NH2 | ARG | A | 458 | -0.703 | 20.741 | 2.499 | 1.00 | 27.52 | N |

Figure 15

| ATOM | 1725 | C | ARG A 458 | 5.076 | 26.047 | 1.490 | 1.00 | 29.63 | C |
|------|------|-----|-----------|--------|--------|--------|------|-------|---|
| ATOM | 1726 | O | ARG A 458 | 5.054 | 27.040 | 0.760 | 1.00 | 30.07 | O |
| ATOM | 1727 | N | MET A 459 | 6.172 | 25.640 | 2.117 | 1.00 | 29.59 | N |
| ATOM | 1728 | CA | MET A 459 | 7.439 | 26.337 | 1.935 | 1.00 | 30.99 | C |
| ATOM | 1729 | CB | MET A 459 | 8.556 | 25.681 | 2.741 | 1.00 | 34.09 | C |
| ATOM | 1730 | CG | MET A 459 | 8.508 | 25.899 | 4.235 | 1.00 | 37.29 | C |
| ATOM | 1731 | SD | MET A 459 | 9.988 | 25.163 | 4.981 | 1.00 | 37.60 | S |
| ATOM | 1732 | CE | MET A 459 | 9.349 | 23.518 | 5.394 | 1.00 | 37.71 | C |
| ATOM | 1733 | C | MET A 459 | 7.832 | 26.285 | 0.470 | 1.00 | 30.80 | C |
| ATOM | 1734 | O | MET A 459 | 7.515 | 25.323 | -0.227 | 1.00 | 30.40 | O |
| ATOM | 1735 | N | VAL A 460 | 8.535 | 27.314 | 0.014 | 1.00 | 34.64 | N |
| ATOM | 1736 | CA | VAL A 460 | 8.994 | 27.364 | -1.367 | 1.00 | 35.60 | C |
| ATOM | 1737 | CB | VAL A 460 | 9.297 | 28.820 | -1.806 | 1.00 | 31.50 | C |
| ATOM | 1738 | CG1 | VAL A 460 | 8.131 | 29.719 | -1.443 | 1.00 | 31.09 | C |
| ATOM | 1739 | CG2 | VAL A 460 | 10.566 | 29.316 | -1.135 | 1.00 | 32.51 | C |
| ATOM | 1740 | C | VAL A 460 | 10.284 | 26.551 | -1.437 | 1.00 | 36.20 | C |
| ATOM | 1741 | O | VAL A 460 | 10.772 | 26.058 | -0.423 | 1.00 | 36.23 | O |
| ATOM | 1742 | N | ARG A 461 | 10.842 | 26.420 | -2.628 | 1.00 | 35.11 | N |
| ATOM | 1743 | CA | ARG A 461 | 12.074 | 25.672 | -2.781 | 1.00 | 37.85 | C |
| ATOM | 1744 | CB | ARG A 461 | 12.414 | 25.498 | -4.255 | 1.00 | 46.17 | C |
| ATOM | 1745 | CG | ARG A 461 | 13.726 | 24.782 | -4.515 | 1.00 | 50.21 | C |
| ATOM | 1746 | CD | ARG A 461 | 13.853 | 24.424 | -5.983 | 1.00 | 52.91 | C |
| ATOM | 1747 | NE | ARG A 461 | 14.049 | 25.595 | -6.831 | 1.00 | 55.86 | N |
| ATOM | 1748 | CZ | ARG A 461 | 15.197 | 26.257 | -6.934 | 1.00 | 58.41 | C |
| ATOM | 1749 | NH1 | ARG A 461 | 16.256 | 25.859 | -6.235 | 1.00 | 59.92 | N |
| ATOM | 1750 | NH2 | ARG A 461 | 15.290 | 27.309 | -7.742 | 1.00 | 58.47 | N |
| ATOM | 1751 | C | ARG A 461 | 13.208 | 26.395 | -2.068 | 1.00 | 39.08 | C |
| ATOM | 1752 | O | ARG A 461 | 13.434 | 27.590 | -2.287 | 1.00 | 39.49 | O |
| ATOM | 1753 | N | PRO A 462 | 13.916 | 25.685 | -1.176 | 1.00 | 36.00 | N |
| ATOM | 1754 | CD | PRO A 462 | 13.595 | 24.329 | -0.702 | 1.00 | 31.31 | C |
| ATOM | 1755 | CA | PRO A 462 | 15.038 | 26.256 | -0.422 | 1.00 | 36.70 | C |
| ATOM | 1756 | CB | PRO A 462 | 15.375 | 25.155 | 0.597 | 1.00 | 32.42 | C |
| ATOM | 1757 | CG | PRO A 462 | 14.093 | 24.368 | 0.720 | 1.00 | 31.09 | C |
| ATOM | 1758 | C | PRO A 462 | 16.191 | 26.502 | -1.392 | 1.00 | 37.68 | C |
| ATOM | 1759 | O | PRO A 462 | 16.272 | 25.853 | -2.434 | 1.00 | 37.16 | O |
| ATOM | 1760 | N | ASP A 463 | 17.076 | 27.432 | -1.061 | 1.00 | 46.40 | N |
| ATOM | 1761 | CA | ASP A 463 | 18.202 | 27.724 | -1.940 | 1.00 | 49.29 | C |
| ATOM | 1762 | CB | ASP A 463 | 19.043 | 28.881 | -1.388 | 1.00 | 62.43 | C |
| ATOM | 1763 | CG | ASP A 463 | 18.304 | 30.205 | -1.418 | 1.00 | 63.18 | C |
| ATOM | 1764 | OD1 | ASP A 463 | 17.529 | 30.437 | -2.370 | 1.00 | 63.26 | O |
| ATOM | 1765 | OD2 | ASP A 463 | 18.506 | 31.019 | -0.492 | 1.00 | 66.24 | O |
| ATOM | 1766 | C | ASP A 463 | 19.083 | 26.503 | -2.140 | 1.00 | 50.38 | C |
| ATOM | 1767 | O | ASP A 463 | 19.251 | 25.694 | -1.230 | 1.00 | 50.95 | O |
| ATOM | 1768 | N | ASN A 464 | 19.635 | 26.376 | -3.344 | 1.00 | 58.73 | N |
| ATOM | 1769 | CA | ASN A 464 | 20.506 | 25.258 | -3.700 | 1.00 | 59.62 | C |
| ATOM | 1770 | CB | ASN A 464 | 21.822 | 25.334 | -2.917 | 1.00 | 93.45 | C |
| ATOM | 1771 | CG | ASN A 464 | 22.653 | 26.565 | -3.281 | 1.00 | 96.19 | C |
| ATOM | 1772 | OD1 | ASN A 464 | 22.832 | 26.885 | -4.462 | 1.00 | 97.97 | O |
| ATOM | 1773 | ND2 | ASN A 464 | 23.170 | 27.253 | -2.270 | 1.00 | 96.07 | N |
| ATOM | 1774 | C | ASN A 464 | 19.858 | 23.887 | -3.495 | 1.00 | 59.76 | C |
| ATOM | 1775 | O | ASN A 464 | 20.524 | 22.926 | -3.104 | 1.00 | 60.63 | O |
| ATOM | 1776 | N | CYS A 465 | 18.554 | 23.810 | -3.750 | 1.00 | 51.39 | N |
| ATOM | 1777 | CA | CYS A 465 | 17.815 | 22.559 | -3.635 | 1.00 | 49.32 | C |
| ATOM | 1778 | CB | CYS A 465 | 16.635 | 22.714 | -2.666 | 1.00 | 47.48 | C |
| ATOM | 1779 | SG | CYS A 465 | 15.425 | 21.345 | -2.692 | 1.00 | 46.41 | S |
| ATOM | 1780 | C | CYS A 465 | 17.299 | 22.187 | -5.026 | 1.00 | 48.11 | C |
| ATOM | 1781 | O | CYS A 465 | 16.595 | 22.956 | -5.666 | 1.00 | 48.12 | O |
| ATOM | 1782 | N | PRO A 466 | 17.671 | 21.003 | -5.521 | 1.00 | 46.97 | N |
| ATOM | 1783 | CD | PRO A 466 | 18.640 | 20.061 | -4.937 | 1.00 | 41.67 | C |
| ATOM | 1784 | CA | PRO A 466 | 17.228 | 20.551 | -6.845 | 1.00 | 46.29 | C |

Figure 15

| | | | | | | | | | | |
|---|---|---|---|---|---|---|---|---|---|---|
| ATOM | 1785 | CB | PRO | A | 466 | 17.778 | 19.136 | -6.920 | 1.00 41.22 | C |
| ATOM | 1786 | CG | PRO | A | 466 | 19.046 | 19.238 | -6.140 | 1.00 42.18 | C |
| ATOM | 1787 | C | PRO | A | 466 | 15.697 | 20.582 | -6.962 | 1.00 46.46 | C |
| ATOM | 1788 | O | PRO | A | 466 | 14.989 | 20.239 | -6.012 | 1.00 46.56 | O |
| ATOM | 1789 | N | GLU | A | 467 | 15.195 | 20.993 | -8.123 | 1.00 45.37 | N |
| ATOM | 1790 | CA | GLU | A | 467 | 13.754 | 21.065 | -8.363 | 1.00 44.98 | C |
| ATOM | 1791 | CB | GLU | A | 467 | 13.455 | 21.484 | -9.809 | 1.00 43.56 | C |
| ATOM | 1792 | CG | GLU | A | 467 | 12.780 | 22.852 | -9.937 | 1.00 46.08 | C |
| ATOM | 1793 | CD | GLU | A | 467 | 11.483 | 22.968 | -9.143 | 1.00 46.25 | C |
| ATOM | 1794 | OE1 | GLU | A | 467 | 10.522 | 22.230 | -9.443 | 1.00 48.07 | O |
| ATOM | 1795 | OE2 | GLU | A | 467 | 11.428 | 23.803 | -8.220 | 1.00 45.80 | O |
| ATOM | 1796 | C | GLU | A | 467 | 13.083 | 19.727 | -8.108 | 1.00 44.35 | C |
| ATOM | 1797 | O | GLU | A | 467 | 11.974 | 19.670 | -7.576 | 1.00 43.76 | O |
| ATOM | 1798 | N | GLU | A | 468 | 13.755 | 18.656 | -8.523 | 1.00 39.03 | N |
| ATOM | 1799 | CA | GLU | A | 468 | 13.230 | 17.319 | -8.347 | 1.00 38.35 | C |
| ATOM | 1800 | CB | GLU | A | 468 | 14.122 | 16.297 | -9.052 | 1.00 79.20 | C |
| ATOM | 1801 | CG | GLU | A | 468 | 14.517 | 16.670 | -10.474 | 1.00 84.00 | C |
| ATOM | 1802 | CD | GLU | A | 468 | 15.870 | 17.359 | -10.522 | 1.00 87.66 | C |
| ATOM | 1803 | OE1 | GLU | A | 468 | 16.880 | 16.710 | -10.150 | 1.00 90.55 | O |
| ATOM | 1804 | OE2 | GLU | A | 468 | 15.928 | 18.542 | -10.922 | 1.00 88.47 | O |
| ATOM | 1805 | C | GLU | A | 468 | 13.150 | 17.001 | -6.861 | 1.00 37.30 | C |
| ATOM | 1806 | O | GLU | A | 468 | 12.247 | 16.289 | -6.422 | 1.00 37.03 | O |
| ATOM | 1807 | N | LEU | A | 469 | 14.095 | 17.529 | -6.085 | 1.00 36.11 | N |
| ATOM | 1808 | CA | LEU | A | 469 | 14.081 | 17.287 | -4.652 | 1.00 34.25 | C |
| ATOM | 1809 | CB | LEU | A | 469 | 15.377 | 17.767 | -3.992 | 1.00 45.43 | C |
| ATOM | 1810 | CG | LEU | A | 469 | 15.453 | 17.393 | -2.508 | 1.00 46.99 | C |
| ATOM | 1811 | CD1 | LEU | A | 469 | 15.233 | 15.885 | -2.350 | 1.00 45.88 | C |
| ATOM | 1812 | CD2 | LEU | A | 469 | 16.807 | 17.795 | -1.938 | 1.00 46.09 | C |
| ATOM | 1813 | C | LEU | A | 469 | 12.897 | 18.028 | -4.066 | 1.00 32.59 | C |
| ATOM | 1814 | O | LEU | A | 469 | 12.160 | 17.483 | -3.246 | 1.00 30.86 | O |
| ATOM | 1815 | N | TYR | A | 470 | 12.713 | 19.272 | -4.508 | 1.00 35.86 | N |
| ATOM | 1816 | CA | TYR | A | 470 | 11.603 | 20.095 | -4.037 | 1.00 34.08 | C |
| ATOM | 1817 | CB | TYR | A | 470 | 11.661 | 21.484 | -4.671 | 1.00 30.13 | C |
| ATOM | 1818 | CG | TYR | A | 470 | 10.519 | 22.377 | -4.229 | 1.00 30.28 | C |
| ATOM | 1819 | CD1 | TYR | A | 470 | 10.337 | 22.675 | -2.881 | 1.00 27.79 | C |
| ATOM | 1820 | CE1 | TYR | A | 470 | 9.294 | 23.463 | -2.457 | 1.00 29.69 | C |
| ATOM | 1821 | CD2 | TYR | A | 470 | 9.617 | 22.907 | -5.151 | 1.00 29.69 | C |
| ATOM | 1822 | CE2 | TYR | A | 470 | 8.560 | 23.708 | -4.730 | 1.00 31.03 | C |
| ATOM | 1823 | CZ | TYR | A | 470 | 8.402 | 23.979 | -3.373 | 1.00 30.98 | C |
| ATOM | 1824 | OH | TYR | A | 470 | 7.334 | 24.730 | -2.923 | 1.00 30.05 | O |
| ATOM | 1825 | C | TYR | A | 470 | 10.241 | 19.466 | -4.345 | 1.00 33.74 | C |
| ATOM | 1826 | O | TYR | A | 470 | 9.320 | 19.529 | -3.531 | 1.00 32.99 | O |
| ATOM | 1827 | N | GLN | A | 471 | 10.101 | 18.875 | -5.528 | 1.00 33.30 | N |
| ATOM | 1828 | CA | GLN | A | 471 | 8.832 | 18.251 | -5.870 | 1.00 35.19 | C |
| ATOM | 1829 | CB | GLN | A | 471 | 8.775 | 17.897 | -7.361 | 1.00 37.76 | C |
| ATOM | 1830 | CG | GLN | A | 471 | 8.679 | 19.121 | -8.261 | 1.00 40.44 | C |
| ATOM | 1831 | CD | GLN | A | 471 | 7.463 | 19.996 | -7.946 | 1.00 44.32 | C |
| ATOM | 1832 | OE1 | GLN | A | 471 | 6.325 | 19.514 | -7.901 | 1.00 45.25 | O |
| ATOM | 1833 | NE2 | GLN | A | 471 | 7.701 | 21.289 | -7.740 | 1.00 44.62 | N |
| ATOM | 1834 | C | GLN | A | 471 | 8.586 | 17.014 | -5.003 | 1.00 33.92 | C |
| ATOM | 1835 | O | GLN | A | 471 | 7.439 | 16.662 | -4.733 | 1.00 33.86 | O |
| ATOM | 1836 | N | LEU | A | 472 | 9.661 | 16.366 | -4.563 | 1.00 32.63 | N |
| ATOM | 1837 | CA | LEU | A | 472 | 9.534 | 15.201 | -3.678 | 1.00 32.79 | C |
| ATOM | 1838 | CB | LEU | A | 472 | 10.907 | 14.576 | -3.408 | 1.00 45.55 | C |
| ATOM | 1839 | CG | LEU | A | 472 | 11.060 | 13.094 | -3.769 | 1.00 50.41 | C |
| ATOM | 1840 | CD1 | LEU | A | 472 | 10.634 | 12.876 | -5.210 | 1.00 49.45 | C |
| ATOM | 1841 | CD2 | LEU | A | 472 | 12.514 | 12.644 | -3.559 | 1.00 51.04 | C |
| ATOM | 1842 | C | LEU | A | 472 | 8.930 | 15.710 | -2.360 | 1.00 31.05 | C |
| ATOM | 1843 | O | LEU | A | 472 | 8.000 | 15.115 | -1.807 | 1.00 30.45 | O |
| ATOM | 1844 | N | MET | A | 473 | 9.465 | 16.828 | -1.881 | 1.00 25.63 | N |

Figure 15

| | | | | | | | | | | |
|---|---|---|---|---|---|---|---|---|---|---|
| ATOM | 1845 | CA | MET | A | 473 | 8.988 | 17.444 | -0.648 | 1.00 | 25.49 | C |
| ATOM | 1846 | CB | MET | A | 473 | 9.743 | 18.737 | -0.357 | 1.00 | 29.58 | C |
| ATOM | 1847 | CG | MET | A | 473 | 11.249 | 18.619 | -0.340 | 1.00 | 30.41 | C |
| ATOM | 1848 | SD | MET | A | 473 | 12.040 | 20.262 | -0.291 | 1.00 | 32.01 | S |
| ATOM | 1849 | CE | MET | A | 473 | 13.696 | 19.781 | 0.290 | 1.00 | 29.97 | C |
| ATOM | 1850 | C | MET | A | 473 | 7.501 | 17.757 | -0.745 | 1.00 | 24.88 | C |
| ATOM | 1851 | O | MET | A | 473 | 6.755 | 17.493 | 0.188 | 1.00 | 24.00 | O |
| ATOM | 1852 | N | ARG | A | 474 | 7.078 | 18.310 | -1.878 | 1.00 | 28.31 | N |
| ATOM | 1853 | CA | ARG | A | 474 | 5.674 | 18.658 | -2.078 | 1.00 | 28.66 | C |
| ATOM | 1854 | CB | ARG | A | 474 | 5.471 | 19.376 | -3.425 | 1.00 | 33.18 | C |
| ATOM | 1855 | CG | ARG | A | 474 | 6.126 | 20.776 | -3.504 | 1.00 | 34.48 | C |
| ATOM | 1856 | CD | ARG | A | 474 | 5.622 | 21.704 | -2.393 | 1.00 | 34.15 | C |
| ATOM | 1857 | NE | ARG | A | 474 | 4.195 | 21.964 | -2.516 | 1.00 | 34.03 | N |
| ATOM | 1858 | CZ | ARG | A | 474 | 3.663 | 23.054 | -3.061 | 1.00 | 34.25 | C |
| ATOM | 1859 | NH1 | ARG | A | 474 | 4.439 | 24.027 | -3.535 | 1.00 | 29.71 | N |
| ATOM | 1860 | NH2 | ARG | A | 474 | 2.344 | 23.152 | -3.156 | 1.00 | 30.63 | N |
| ATOM | 1861 | C | ARG | A | 474 | 4.800 | 17.418 | -2.006 | 1.00 | 28.44 | C |
| ATOM | 1862 | O | ARG | A | 474 | 3.679 | 17.465 | -1.499 | 1.00 | 28.37 | O |
| ATOM | 1863 | N | LEU | A | 475 | 5.298 | 16.298 | -2.509 | 1.00 | 27.28 | N |
| ATOM | 1864 | CA | LEU | A | 475 | 4.521 | 15.070 | -2.430 | 1.00 | 27.23 | C |
| ATOM | 1865 | CB | LEU | A | 475 | 5.223 | 13.940 | -3.188 | 1.00 | 33.39 | C |
| ATOM | 1866 | CG | LEU | A | 475 | 5.141 | 14.145 | -4.703 | 1.00 | 36.34 | C |
| ATOM | 1867 | CD1 | LEU | A | 475 | 5.901 | 13.042 | -5.436 | 1.00 | 33.94 | C |
| ATOM | 1868 | CD2 | LEU | A | 475 | 3.658 | 14.173 | -5.110 | 1.00 | 35.55 | C |
| ATOM | 1869 | C | LEU | A | 475 | 4.364 | 14.706 | -0.964 | 1.00 | 25.99 | C |
| ATOM | 1870 | O | LEU | A | 475 | 3.291 | 14.337 | -0.524 | 1.00 | 25.97 | O |
| ATOM | 1871 | N | CYS | A | 476 | 5.450 | 14.823 | -0.205 | 1.00 | 28.84 | N |
| ATOM | 1872 | CA | CYS | A | 476 | 5.414 | 14.515 | 1.220 | 1.00 | 28.40 | C |
| ATOM | 1873 | CB | CYS | A | 476 | 6.800 | 14.667 | 1.859 | 1.00 | 29.89 | C |
| ATOM | 1874 | SG | CYS | A | 476 | 8.058 | 13.466 | 1.369 | 1.00 | 33.75 | S |
| ATOM | 1875 | C | CYS | A | 476 | 4.453 | 15.460 | 1.926 | 1.00 | 28.66 | C |
| ATOM | 1876 | O | CYS | A | 476 | 3.916 | 15.130 | 2.985 | 1.00 | 29.27 | O |
| ATOM | 1877 | N | TRP | A | 477 | 4.226 | 16.637 | 1.351 | 1.00 | 28.97 | N |
| ATOM | 1878 | CA | TRP | A | 477 | 3.336 | 17.587 | 2.004 | 1.00 | 30.34 | C |
| ATOM | 1879 | CB | TRP | A | 477 | 3.929 | 19.003 | 1.980 | 1.00 | 31.28 | C |
| ATOM | 1880 | CG | TRP | A | 477 | 5.297 | 19.110 | 2.553 | 1.00 | 31.55 | C |
| ATOM | 1881 | CD2 | TRP | A | 477 | 6.305 | 20.057 | 2.179 | 1.00 | 31.67 | C |
| ATOM | 1882 | CE2 | TRP | A | 477 | 7.415 | 19.831 | 3.009 | 1.00 | 32.00 | C |
| ATOM | 1883 | CE3 | TRP | A | 477 | 6.371 | 21.077 | 1.218 | 1.00 | 33.54 | C |
| ATOM | 1884 | CD1 | TRP | A | 477 | 5.823 | 18.364 | 3.569 | 1.00 | 31.91 | C |
| ATOM | 1885 | NE1 | TRP | A | 477 | 7.096 | 18.790 | 3.850 | 1.00 | 33.10 | N |
| ATOM | 1886 | CZ2 | TRP | A | 477 | 8.589 | 20.584 | 2.913 | 1.00 | 31.17 | C |
| ATOM | 1887 | CZ3 | TRP | A | 477 | 7.544 | 21.829 | 1.118 | 1.00 | 33.85 | C |
| ATOM | 1888 | CH2 | TRP | A | 477 | 8.636 | 21.573 | 1.965 | 1.00 | 32.29 | C |
| ATOM | 1889 | C | TRP | A | 477 | 1.916 | 17.648 | 1.449 | 1.00 | 29.98 | C |
| ATOM | 1890 | O | TRP | A | 477 | 1.222 | 18.647 | 1.656 | 1.00 | 29.18 | O |
| ATOM | 1891 | N | LYS | A | 478 | 1.489 | 16.606 | 0.740 | 1.00 | 28.28 | N |
| ATOM | 1892 | CA | LYS | A | 478 | 0.124 | 16.575 | 0.198 | 1.00 | 28.38 | C |
| ATOM | 1893 | CB | LYS | A | 478 | -0.140 | 15.269 | -0.561 | 1.00 | 35.61 | C |
| ATOM | 1894 | CG | LYS | A | 478 | 0.606 | 15.134 | -1.895 | 1.00 | 38.34 | C |
| ATOM | 1895 | CD | LYS | A | 478 | 0.210 | 16.244 | -2.852 | 1.00 | 41.22 | C |
| ATOM | 1896 | CE | LYS | A | 478 | -1.283 | 16.211 | -3.138 | 1.00 | 43.56 | C |
| ATOM | 1897 | NZ | LYS | A | 478 | -1.730 | 17.339 | -4.012 | 1.00 | 48.15 | N |
| ATOM | 1898 | C | LYS | A | 478 | -0.800 | 16.656 | 1.399 | 1.00 | 27.67 | C |
| ATOM | 1899 | O | LYS | A | 478 | -0.539 | 16.023 | 2.425 | 1.00 | 26.87 | O |
| ATOM | 1900 | N | GLU | A | 479 | -1.864 | 17.443 | 1.275 | 1.00 | 30.41 | N |
| ATOM | 1901 | CA | GLU | A | 479 | -2.826 | 17.624 | 2.353 | 1.00 | 30.94 | C |
| ATOM | 1902 | CB | GLU | A | 479 | -3.975 | 18.536 | 1.903 | 1.00 | 25.59 | C |
| ATOM | 1903 | CG | GLU | A | 479 | -4.953 | 18.910 | 3.032 | 1.00 | 25.97 | C |
| ATOM | 1904 | CD | GLU | A | 479 | -4.279 | 19.719 | 4.152 | 1.00 | 26.67 | C |

Figure 15

```
ATOM   1905  OE1 GLU A 479      -3.364  20.504   3.839  1.00 26.17           O
ATOM   1906  OE2 GLU A 479      -4.666  19.580   5.333  1.00 27.64           O
ATOM   1907  C   GLU A 479      -3.407  16.293   2.853  1.00 31.51           C
ATOM   1908  O   GLU A 479      -3.436  16.042   4.047  1.00 32.51           O
ATOM   1909  N   ARG A 480      -3.893  15.463   1.937  1.00 28.01           N
ATOM   1910  CA  ARG A 480      -4.471  14.166   2.303  1.00 29.70           C
ATOM   1911  CB  ARG A 480      -5.433  13.679   1.219  1.00 44.70           C
ATOM   1912  CG  ARG A 480      -6.656  14.568   1.044  1.00 49.98           C
ATOM   1913  CD  ARG A 480      -7.525  14.110  -0.117  1.00 53.87           C
ATOM   1914  NE  ARG A 480      -8.660  15.006  -0.288  1.00 59.97           N
ATOM   1915  CZ  ARG A 480      -9.628  14.848  -1.186  1.00 62.37           C
ATOM   1916  NH1 ARG A 480      -9.617  13.812  -2.021  1.00 64.16           N
ATOM   1917  NH2 ARG A 480     -10.614  15.738  -1.247  1.00 62.89           N
ATOM   1918  C   ARG A 480      -3.331  13.178   2.466  1.00 28.01           C
ATOM   1919  O   ARG A 480      -2.496  13.039   1.574  1.00 28.00           O
ATOM   1920  N   PRO A 481      -3.270  12.497   3.617  1.00 26.25           N
ATOM   1921  CD  PRO A 481      -4.242  12.527   4.725  1.00 31.45           C
ATOM   1922  CA  PRO A 481      -2.205  11.522   3.885  1.00 26.04           C
ATOM   1923  CB  PRO A 481      -2.593  10.944   5.243  1.00 30.84           C
ATOM   1924  CG  PRO A 481      -3.404  12.064   5.890  1.00 31.22           C
ATOM   1925  C   PRO A 481      -2.050  10.439   2.823  1.00 25.61           C
ATOM   1926  O   PRO A 481      -0.932  10.047   2.507  1.00 25.16           O
ATOM   1927  N   GLU A 482      -3.161   9.963   2.259  1.00 30.69           N
ATOM   1928  CA  GLU A 482      -3.089   8.903   1.252  1.00 31.04           C
ATOM   1929  CB  GLU A 482      -4.495   8.391   0.886  1.00 29.57           C
ATOM   1930  CG  GLU A 482      -5.371   9.404   0.161  1.00 30.25           C
ATOM   1931  CD  GLU A 482      -6.227  10.232   1.094  1.00 30.52           C
ATOM   1932  OE1 GLU A 482      -5.892  10.357   2.285  1.00 32.79           O
ATOM   1933  OE2 GLU A 482      -7.244  10.774   0.628  1.00 33.34           O
ATOM   1934  C   GLU A 482      -2.343   9.338  -0.012  1.00 31.77           C
ATOM   1935  O   GLU A 482      -1.839   8.503  -0.758  1.00 32.51           O
ATOM   1936  N   ASP A 483      -2.262  10.645  -0.259  1.00 29.60           N
ATOM   1937  CA  ASP A 483      -1.543  11.122  -1.439  1.00 29.19           C
ATOM   1938  CB  ASP A 483      -2.130  12.438  -1.943  1.00 32.23           C
ATOM   1939  CG  ASP A 483      -3.543  12.275  -2.437  1.00 33.72           C
ATOM   1940  OD1 ASP A 483      -3.838  11.226  -3.042  1.00 36.47           O
ATOM   1941  OD2 ASP A 483      -4.353  13.183  -2.225  1.00 34.27           O
ATOM   1942  C   ASP A 483      -0.061  11.293  -1.175  1.00 28.75           C
ATOM   1943  O   ASP A 483       0.698  11.641  -2.066  1.00 29.30           O
ATOM   1944  N   ARG A 484       0.374  11.065   0.050  1.00 29.09           N
ATOM   1945  CA  ARG A 484       1.803  11.193   0.302  1.00 29.11           C
ATOM   1946  CB  ARG A 484       2.063  11.536   1.772  1.00 28.27           C
ATOM   1947  CG  ARG A 484       1.395  12.820   2.209  1.00 26.98           C
ATOM   1948  CD  ARG A 484       1.560  13.099   3.699  1.00 26.27           C
ATOM   1949  NE  ARG A 484       0.622  14.134   4.098  1.00 25.08           N
ATOM   1950  CZ  ARG A 484       0.112  14.291   5.315  1.00 25.28           C
ATOM   1951  NH1 ARG A 484       0.455  13.473   6.308  1.00 23.96           N
ATOM   1952  NH2 ARG A 484      -0.794  15.245   5.519  1.00 23.67           N
ATOM   1953  C   ARG A 484       2.436   9.852  -0.061  1.00 28.74           C
ATOM   1954  O   ARG A 484       1.826   8.806   0.112  1.00 28.36           O
ATOM   1955  N   PRO A 485       3.671   9.873  -0.575  1.00 28.45           N
ATOM   1956  CD  PRO A 485       4.506  11.046  -0.894  1.00 31.90           C
ATOM   1957  CA  PRO A 485       4.342   8.627  -0.946  1.00 27.62           C
ATOM   1958  CB  PRO A 485       5.573   9.117  -1.702  1.00 33.93           C
ATOM   1959  CG  PRO A 485       5.878  10.431  -1.017  1.00 33.65           C
ATOM   1960  C   PRO A 485       4.721   7.765   0.251  1.00 28.85           C
ATOM   1961  O   PRO A 485       4.671   8.212   1.399  1.00 29.41           O
ATOM   1962  N   THR A 486       5.092   6.522  -0.023  1.00 26.69           N
ATOM   1963  CA  THR A 486       5.525   5.613   1.027  1.00 26.00           C
ATOM   1964  CB  THR A 486       5.387   4.135   0.614  1.00 28.77           C
```

Figure 15

| | | | | | | | | | |
|---|---|---|---|---|---|---|---|---|---|
| ATOM | 1965 | OG1 | THR | A | 486 | 6.122 | 3.928 | -0.604 | 1.00 29.80 | O |
| ATOM | 1966 | CG2 | THR | A | 486 | 3.935 | 3.741 | 0.424 | 1.00 26.72 | C |
| ATOM | 1967 | C | THR | A | 486 | 7.024 | 5.874 | 1.199 | 1.00 26.12 | C |
| ATOM | 1968 | O | THR | A | 486 | 7.665 | 6.445 | 0.322 | 1.00 24.18 | O |
| ATOM | 1969 | N | PHE | A | 487 | 7.574 | 5.447 | 2.326 | 1.00 27.11 | N |
| ATOM | 1970 | CA | PHE | A | 487 | 8.992 | 5.608 | 2.552 | 1.00 28.49 | C |
| ATOM | 1971 | CB | PHE | A | 487 | 9.335 | 5.324 | 4.009 | 1.00 28.56 | C |
| ATOM | 1972 | CG | PHE | A | 487 | 9.144 | 6.505 | 4.908 | 1.00 28.05 | C |
| ATOM | 1973 | CD1 | PHE | A | 487 | 9.958 | 7.622 | 4.783 | 1.00 27.07 | C |
| ATOM | 1974 | CD2 | PHE | A | 487 | 8.173 | 6.493 | 5.895 | 1.00 27.61 | C |
| ATOM | 1975 | CE1 | PHE | A | 487 | 9.811 | 8.708 | 5.637 | 1.00 27.83 | C |
| ATOM | 1976 | CE2 | PHE | A | 487 | 8.018 | 7.577 | 6.751 | 1.00 28.93 | C |
| ATOM | 1977 | CZ | PHE | A | 487 | 8.838 | 8.684 | 6.624 | 1.00 26.66 | C |
| ATOM | 1978 | C | PHE | A | 487 | 9.736 | 4.658 | 1.635 | 1.00 30.15 | C |
| ATOM | 1979 | O | PHE | A | 487 | 10.904 | 4.886 | 1.308 | 1.00 30.08 | O |
| ATOM | 1980 | N | ASP | A | 488 | 9.046 | 3.597 | 1.221 | 1.00 31.48 | N |
| ATOM | 1981 | CA | ASP | A | 488 | 9.631 | 2.617 | 0.312 | 1.00 33.20 | C |
| ATOM | 1982 | CB | ASP | A | 488 | 8.663 | 1.436 | 0.102 | 1.00 41.17 | C |
| ATOM | 1983 | CG | ASP | A | 488 | 9.153 | 0.453 | -0.953 | 1.00 44.10 | C |
| ATOM | 1984 | OD1 | ASP | A | 488 | 10.378 | 0.382 | -1.173 | 1.00 46.93 | O |
| ATOM | 1985 | OD2 | ASP | A | 488 | 8.314 | -0.254 | -1.554 | 1.00 44.51 | O |
| ATOM | 1986 | C | ASP | A | 488 | 9.939 | 3.318 | -1.014 | 1.00 33.03 | C |
| ATOM | 1987 | O | ASP | A | 488 | 10.955 | 3.044 | -1.646 | 1.00 33.13 | O |
| ATOM | 1988 | N | TYR | A | 489 | 9.064 | 4.229 | -1.424 | 1.00 32.43 | N |
| ATOM | 1989 | CA | TYR | A | 489 | 9.276 | 4.988 | -2.657 | 1.00 32.96 | C |
| ATOM | 1990 | CB | TYR | A | 489 | 7.976 | 5.665 | -3.110 | 1.00 31.37 | C |
| ATOM | 1991 | CG | TYR | A | 489 | 8.177 | 6.610 | -4.271 | 1.00 29.71 | C |
| ATOM | 1992 | CD1 | TYR | A | 489 | 8.493 | 6.129 | -5.540 | 1.00 28.51 | C |
| ATOM | 1993 | CE1 | TYR | A | 489 | 8.729 | 6.994 | -6.591 | 1.00 29.16 | C |
| ATOM | 1994 | CD2 | TYR | A | 489 | 8.098 | 7.991 | -4.086 | 1.00 29.94 | C |
| ATOM | 1995 | CE2 | TYR | A | 489 | 8.331 | 8.865 | -5.119 | 1.00 28.38 | C |
| ATOM | 1996 | CZ | TYR | A | 489 | 8.652 | 8.369 | -6.373 | 1.00 31.15 | C |
| ATOM | 1997 | OH | TYR | A | 489 | 8.942 | 9.246 | -7.385 | 1.00 30.87 | O |
| ATOM | 1998 | C | TYR | A | 489 | 10.366 | 6.052 | -2.454 | 1.00 33.23 | C |
| ATOM | 1999 | O | TYR | A | 489 | 11.291 | 6.162 | -3.264 | 1.00 33.31 | O |
| ATOM | 2000 | N | LEU | A | 490 | 10.257 | 6.826 | -1.376 | 1.00 29.41 | N |
| ATOM | 2001 | CA | LEU | A | 490 | 11.244 | 7.866 | -1.065 | 1.00 29.69 | C |
| ATOM | 2002 | CB | LEU | A | 490 | 10.909 | 8.518 | 0.284 | 1.00 29.50 | C |
| ATOM | 2003 | CG | LEU | A | 490 | 9.618 | 9.355 | 0.300 | 1.00 29.31 | C |
| ATOM | 2004 | CD1 | LEU | A | 490 | 9.280 | 9.836 | 1.694 | 1.00 27.67 | C |
| ATOM | 2005 | CD2 | LEU | A | 490 | 9.804 | 10.537 | -0.628 | 1.00 28.41 | C |
| ATOM | 2006 | C | LEU | A | 490 | 12.672 | 7.303 | -1.043 | 1.00 31.01 | C |
| ATOM | 2007 | O | LEU | A | 490 | 13.611 | 7.928 | -1.542 | 1.00 29.29 | O |
| ATOM | 2008 | N | ARG | A | 491 | 12.828 | 6.116 | -0.459 | 1.00 37.55 | N |
| ATOM | 2009 | CA | ARG | A | 491 | 14.127 | 5.471 | -0.402 | 1.00 39.86 | C |
| ATOM | 2010 | CB | ARG | A | 491 | 14.019 | 4.128 | 0.326 | 1.00 51.49 | C |
| ATOM | 2011 | CG | ARG | A | 491 | 15.306 | 3.302 | 0.294 | 1.00 53.95 | C |
| ATOM | 2012 | CD | ARG | A | 491 | 15.078 | 1.886 | 0.792 | 1.00 57.09 | C |
| ATOM | 2013 | NE | ARG | A | 491 | 14.035 | 1.206 | 0.027 | 1.00 61.80 | N |
| ATOM | 2014 | CZ | ARG | A | 491 | 14.082 | 1.002 | -1.287 | 1.00 63.50 | C |
| ATOM | 2015 | NH1 | ARG | A | 491 | 15.128 | 1.419 | -1.990 | 1.00 64.63 | N |
| ATOM | 2016 | NH2 | ARG | A | 491 | 13.072 | 0.399 | -1.904 | 1.00 64.45 | N |
| ATOM | 2017 | C | ARG | A | 491 | 14.646 | 5.248 | -1.827 | 1.00 40.82 | C |
| ATOM | 2018 | O | ARG | A | 491 | 15.751 | 5.680 | -2.176 | 1.00 41.16 | O |
| ATOM | 2019 | N | SER | A | 492 | 13.833 | 4.590 | -2.650 | 1.00 38.68 | N |
| ATOM | 2020 | CA | SER | A | 492 | 14.211 | 4.299 | -4.026 | 1.00 39.73 | C |
| ATOM | 2021 | CB | SER | A | 492 | 13.070 | 3.571 | -4.739 | 1.00 52.04 | C |
| ATOM | 2022 | OG | SER | A | 492 | 12.867 | 2.289 | -4.164 | 1.00 57.77 | O |
| ATOM | 2023 | C | SER | A | 492 | 14.626 | 5.519 | -4.839 | 1.00 39.51 | C |
| ATOM | 2024 | O | SER | A | 492 | 15.689 | 5.525 | -5.449 | 1.00 39.41 | O |

Figure 15

| | | | | | | | | | | |
|---|---|---|---|---|---|---|---|---|---|---|
|ATOM|2025|N  |VAL|A|493|13.793| 6.551|-4.849|1.00 40.43|N|
|ATOM|2026|CA |VAL|A|493|14.107| 7.754|-5.609|1.00 40.78|C|
|ATOM|2027|CB |VAL|A|493|12.884| 8.706|-5.676|1.00 54.37|C|
|ATOM|2028|CG1|VAL|A|493|12.251| 8.829|-4.308|1.00 54.89|C|
|ATOM|2029|CG2|VAL|A|493|13.320|10.094|-6.189|1.00 54.39|C|
|ATOM|2030|C  |VAL|A|493|15.317| 8.513|-5.068|1.00 40.46|C|
|ATOM|2031|O  |VAL|A|493|16.084| 9.076|-5.838|1.00 40.15|O|
|ATOM|2032|N  |LEU|A|494|15.505| 8.525|-3.751|1.00 37.40|N|
|ATOM|2033|CA |LEU|A|494|16.654| 9.232|-3.191|1.00 38.21|C|
|ATOM|2034|CB |LEU|A|494|16.473| 9.469|-1.683|1.00 35.08|C|
|ATOM|2035|CG |LEU|A|494|15.378|10.495|-1.365|1.00 35.17|C|
|ATOM|2036|CD1|LEU|A|494|15.155|10.608| 0.125|1.00 33.39|C|
|ATOM|2037|CD2|LEU|A|494|15.776|11.839|-1.948|1.00 34.76|C|
|ATOM|2038|C  |LEU|A|494|17.962| 8.490|-3.462|1.00 38.88|C|
|ATOM|2039|O  |LEU|A|494|18.971| 9.112|-3.758|1.00 37.59|O|
|ATOM|2040|N  |GLU|A|495|17.936| 7.163|-3.376|1.00 43.46|N|
|ATOM|2041|CA |GLU|A|495|19.138| 6.367|-3.624|1.00 46.48|C|
|ATOM|2042|CB |GLU|A|495|18.883| 4.884|-3.336|1.00 61.14|C|
|ATOM|2043|CG |GLU|A|495|18.419| 4.589|-1.914|1.00 63.93|C|
|ATOM|2044|CD |GLU|A|495|18.439| 3.109|-1.579|1.00 64.59|C|
|ATOM|2045|OE1|GLU|A|495|17.846| 2.313|-2.343|1.00 65.71|O|
|ATOM|2046|OE2|GLU|A|495|19.043| 2.745|-0.548|1.00 65.24|O|
|ATOM|2047|C  |GLU|A|495|19.645| 6.512|-5.057|1.00 48.03|C|
|ATOM|2048|O  |GLU|A|495|20.846| 6.446|-5.299|1.00 47.97|O|
|ATOM|2049|N  |ASP|A|496|18.736| 6.704|-6.008|1.00 49.48|N|
|ATOM|2050|CA |ASP|A|496|19.145| 6.848|-7.401|1.00 51.38|C|
|ATOM|2051|CB |ASP|A|496|18.432| 5.806|-8.278|1.00 72.15|C|
|ATOM|2052|CG |ASP|A|496|18.941| 4.389|-8.034|1.00 74.04|C|
|ATOM|2053|OD1|ASP|A|496|18.613| 3.809|-6.975|1.00 74.20|O|
|ATOM|2054|OD2|ASP|A|496|19.680| 3.859|-8.897|1.00 74.51|O|
|ATOM|2055|C  |ASP|A|496|18.912| 8.245|-7.969|1.00 51.72|C|
|ATOM|2056|O  |ASP|A|496|18.753| 8.408|-9.173|1.00 51.76|O|
|ATOM|2057|N  |PHE|A|497|18.913| 9.249|-7.097|1.00 49.91|N|
|ATOM|2058|CA |PHE|A|497|18.703|10.634|-7.514|1.00 50.34|C|
|ATOM|2059|CB |PHE|A|497|18.809|11.558|-6.301|1.00 47.64|C|
|ATOM|2060|CG |PHE|A|497|18.109|12.869|-6.476|1.00 45.96|C|
|ATOM|2061|CD1|PHE|A|497|16.726|12.934|-6.463|1.00 45.82|C|
|ATOM|2062|CD2|PHE|A|497|18.830|14.037|-6.649|1.00 45.53|C|
|ATOM|2063|CE1|PHE|A|497|16.078|14.139|-6.620|1.00 45.10|C|
|ATOM|2064|CE2|PHE|A|497|18.187|15.245|-6.806|1.00 44.89|C|
|ATOM|2065|CZ |PHE|A|497|16.810|15.297|-6.791|1.00 45.19|C|
|ATOM|2066|C  |PHE|A|497|19.718|11.059|-8.587|1.00 51.61|C|
|ATOM|2067|O  |PHE|A|497|19.384|11.803|-9.504|1.00 51.33|O|
|ATOM|2068|N  |PHE|A|498|20.955|10.595|-8.454|1.00 81.82|N|
|ATOM|2069|CA |PHE|A|498|22.018|10.895|-9.421|1.00 84.10|C|
|ATOM|2070|CB |PHE|A|498|22.150|12.409|-9.677|1.00 74.78|C|
|ATOM|2071|CG |PHE|A|498|22.319|13.236|-8.430|1.00 76.37|C|
|ATOM|2072|CD1|PHE|A|498|22.696|12.653|-7.228|1.00 76.35|C|
|ATOM|2073|CD2|PHE|A|498|22.092|14.604|-8.463|1.00 76.09|C|
|ATOM|2074|CE1|PHE|A|498|22.839|13.416|-6.086|1.00 77.09|C|
|ATOM|2075|CE2|PHE|A|498|22.235|15.373|-7.325|1.00 77.09|C|
|ATOM|2076|CZ |PHE|A|498|22.608|14.779|-6.132|1.00 77.02|C|
|ATOM|2077|C  |PHE|A|498|23.369|10.337|-8.986|1.00 84.44|C|
|ATOM|2078|O  |PHE|A|498|24.188| 9.955|-9.822|1.00 85.33|O|
|ATOM|2079|C1 |LIG|A|500|23.518| 9.793|21.462|1.00 32.79|C|
|ATOM|2080|C2 |LIG|A|500|24.606|10.750|21.186|1.00 35.47|C|
|ATOM|2081|C3 |LIG|A|500|22.310|10.307|22.096|1.00 33.31|C|
|ATOM|2082|N1 |LIG|A|500|23.245| 8.408|21.299|1.00 31.28|N|
|ATOM|2083|C4 |LIG|A|500|24.386|12.243|21.563|1.00 35.40|C|
|ATOM|2084|C5 |LIG|A|500|25.949|10.428|20.576|1.00 36.53|C|

Figure 15

| | | | | | | | | | | |
|---|---|---|---|---|---|---|---|---|---|---|
| ATOM | 2085 | N2 | LIG | A | 500 | 21.497 | 9.262 | 22.284 | 1.00 31.61 | N |
| ATOM | 2086 | C6 | LIG | A | 500 | 22.143 | 11.699 | 22.426 | 1.00 33.97 | C |
| ATOM | 2087 | C7 | LIG | A | 500 | 22.038 | 8.178 | 21.833 | 1.00 30.31 | C |
| ATOM | 2088 | C8 | LIG | A | 500 | 24.051 | 7.336 | 20.712 | 1.00 33.47 | C |
| ATOM | 2089 | C9 | LIG | A | 500 | 25.450 | 13.225 | 21.310 | 1.00 36.40 | C |
| ATOM | 2090 | C10 | LIG | A | 500 | 23.131 | 12.632 | 22.166 | 1.00 35.67 | C |
| ATOM | 2091 | N3 | LIG | A | 500 | 26.864 | 11.431 | 20.400 | 1.00 36.53 | N |
| ATOM | 2092 | O1 | LIG | A | 500 | 26.257 | 9.317 | 20.247 | 1.00 37.65 | O |
| ATOM | 2093 | N4 | LIG | A | 500 | 21.466 | 6.936 | 21.907 | 1.00 30.04 | N |
| ATOM | 2094 | C11 | LIG | A | 500 | 26.653 | 12.785 | 20.743 | 1.00 36.99 | C |
| ATOM | 2095 | C12 | LIG | A | 500 | 25.250 | 14.711 | 21.672 | 1.00 35.92 | C |
| ATOM | 2096 | C13 | LIG | A | 500 | 20.224 | 6.749 | 22.539 | 1.00 28.81 | C |
| ATOM | 2097 | C14 | LIG | A | 500 | 27.743 | 13.757 | 20.493 | 1.00 39.99 | C |
| ATOM | 2098 | C15 | LIG | A | 500 | 18.983 | 6.749 | 21.792 | 1.00 30.10 | C |
| ATOM | 2099 | C16 | LIG | A | 500 | 20.207 | 6.547 | 23.972 | 1.00 28.98 | C |
| ATOM | 2100 | C17 | LIG | A | 500 | 28.907 | 13.418 | 19.924 | 1.00 44.60 | C |
| ATOM | 2101 | C18 | LIG | A | 500 | 17.740 | 6.546 | 22.478 | 1.00 30.66 | C |
| ATOM | 2102 | CL1 | LIG | A | 500 | 18.990 | 6.987 | 20.087 | 1.00 21.50 | C |
| ATOM | 2103 | C19 | LIG | A | 500 | 18.953 | 6.344 | 24.636 | 1.00 29.90 | C |
| ATOM | 2104 | CL2 | LIG | A | 500 | 21.714 | 6.536 | 24.917 | 1.00 18.64 | C |
| ATOM | 2105 | C20 | LIG | A | 500 | 29.971 | 14.481 | 19.665 | 1.00 48.22 | C |
| ATOM | 2106 | C21 | LIG | A | 500 | 17.733 | 6.344 | 23.887 | 1.00 32.28 | C |
| ATOM | 2107 | N5 | LIG | A | 500 | 29.949 | 15.785 | 18.884 | 1.00 51.08 | N |
| ATOM | 2108 | C22 | LIG | A | 500 | 30.936 | 15.633 | 17.790 | 1.00 52.97 | C |
| ATOM | 2109 | C23 | LIG | A | 500 | 28.629 | 16.071 | 18.269 | 1.00 51.50 | C |
| ATOM | 2110 | C24 | LIG | A | 500 | 32.242 | 16.383 | 18.093 | 1.00 54.80 | C |
| ATOM | 2111 | C25 | LIG | A | 500 | 33.339 | 15.362 | 18.378 | 1.00 55.26 | C |
| ATOM | 2112 | N6 | LIG | A | 500 | 34.233 | 15.214 | 17.219 | 1.00 56.88 | N |
| ATOM | 2113 | C26 | LIG | A | 500 | 35.281 | 14.253 | 17.615 | 1.00 56.66 | C |
| ATOM | 2114 | CB | TRP | B | 238 | 47.622 | 27.926 | 32.119 | 1.00 63.46 | C |
| ATOM | 2115 | CG | TRP | B | 238 | 47.074 | 28.545 | 33.374 | 1.00 62.95 | C |
| ATOM | 2116 | CD2 | TRP | B | 238 | 47.466 | 28.241 | 34.716 | 1.00 62.26 | C |
| ATOM | 2117 | CE2 | TRP | B | 238 | 46.644 | 28.999 | 35.574 | 1.00 62.13 | C |
| ATOM | 2118 | CE3 | TRP | B | 238 | 48.431 | 27.398 | 35.276 | 1.00 62.02 | C |
| ATOM | 2119 | CD1 | TRP | B | 238 | 46.062 | 29.459 | 33.469 | 1.00 62.70 | C |
| ATOM | 2120 | NE1 | TRP | B | 238 | 45.796 | 29.735 | 34.788 | 1.00 62.34 | N |
| ATOM | 2121 | CZ2 | TRP | B | 238 | 46.757 | 28.937 | 36.962 | 1.00 62.21 | C |
| ATOM | 2122 | CZ3 | TRP | B | 238 | 48.542 | 27.339 | 36.652 | 1.00 61.74 | C |
| ATOM | 2123 | CH2 | TRP | B | 238 | 47.708 | 28.102 | 37.480 | 1.00 61.98 | C |
| ATOM | 2124 | C | TRP | B | 238 | 48.840 | 28.130 | 29.965 | 1.00 64.34 | C |
| ATOM | 2125 | O | TRP | B | 238 | 49.639 | 27.202 | 30.074 | 1.00 64.29 | O |
| ATOM | 2126 | N | TRP | B | 238 | 47.487 | 30.035 | 30.819 | 1.00 64.81 | N |
| ATOM | 2127 | CA | TRP | B | 238 | 48.366 | 28.893 | 31.196 | 1.00 64.43 | C |
| ATOM | 2128 | N | GLU | B | 239 | 48.338 | 28.511 | 28.794 | 1.00 55.92 | N |
| ATOM | 2129 | CA | GLU | B | 239 | 48.734 | 27.854 | 27.556 | 1.00 56.38 | C |
| ATOM | 2130 | CB | GLU | B | 239 | 47.794 | 28.257 | 26.412 | 1.00 96.84 | C |
| ATOM | 2131 | CG | GLU | B | 239 | 46.347 | 27.760 | 26.545 | 1.00 99.66 | C |
| ATOM | 2132 | CD | GLU | B | 239 | 45.537 | 28.485 | 27.622 | 1.00101.73 | C |
| ATOM | 2133 | OE1 | GLU | B | 239 | 45.441 | 29.734 | 27.572 | 1.00102.49 | O |
| ATOM | 2134 | OE2 | GLU | B | 239 | 44.983 | 27.802 | 28.514 | 1.00102.49 | O |
| ATOM | 2135 | C | GLU | B | 239 | 50.179 | 28.248 | 27.214 | 1.00 55.49 | C |
| ATOM | 2136 | O | GLU | B | 239 | 50.546 | 29.417 | 27.307 | 1.00 55.21 | O |
| ATOM | 2137 | N | VAL | B | 240 | 51.001 | 27.271 | 26.841 | 1.00 64.06 | N |
| ATOM | 2138 | CA | VAL | B | 240 | 52.396 | 27.549 | 26.496 | 1.00 62.84 | C |
| ATOM | 2139 | CB | VAL | B | 240 | 53.368 | 27.222 | 27.664 | 1.00 53.71 | C |
| ATOM | 2140 | CG1 | VAL | B | 240 | 52.929 | 27.936 | 28.930 | 1.00 52.90 | C |
| ATOM | 2141 | CG2 | VAL | B | 240 | 53.450 | 25.709 | 27.873 | 1.00 52.82 | C |
| ATOM | 2142 | C | VAL | B | 240 | 52.838 | 26.741 | 25.291 | 1.00 62.07 | C |
| ATOM | 2143 | O | VAL | B | 240 | 52.218 | 25.738 | 24.942 | 1.00 62.50 | O |
| ATOM | 2144 | N | PRO | B | 241 | 53.921 | 27.177 | 24.630 | 1.00 44.68 | N |

Figure 15

```
ATOM   2145  CD  PRO B 241      54.547  28.503  24.763  1.00 51.78           C
ATOM   2146  CA  PRO B 241      54.440  26.471  23.455  1.00 44.55           C
ATOM   2147  CB  PRO B 241      55.484  27.446  22.901  1.00 51.97           C
ATOM   2148  CG  PRO B 241      54.963  28.791  23.346  1.00 52.08           C
ATOM   2149  C   PRO B 241      55.052  25.118  23.828  1.00 44.35           C
ATOM   2150  O   PRO B 241      55.638  24.962  24.901  1.00 44.23           O
ATOM   2151  N   ARG B 242      54.902  24.143  22.940  1.00 51.09           N
ATOM   2152  CA  ARG B 242      55.442  22.805  23.161  1.00 51.05           C
ATOM   2153  CB  ARG B 242      55.160  21.934  21.938  1.00 64.23           C
ATOM   2154  CG  ARG B 242      55.419  20.470  22.151  1.00 65.04           C
ATOM   2155  CD  ARG B 242      54.398  19.910  23.109  1.00 67.84           C
ATOM   2156  NE  ARG B 242      53.044  19.957  22.553  1.00 68.55           N
ATOM   2157  CZ  ARG B 242      52.664  19.283  21.475  1.00 66.94           C
ATOM   2158  NH1 ARG B 242      53.531  18.509  20.841  1.00 67.95           N
ATOM   2159  NH2 ARG B 242      51.421  19.385  21.029  1.00 66.70           N
ATOM   2160  C   ARG B 242      56.958  22.877  23.392  1.00 51.05           C
ATOM   2161  O   ARG B 242      57.522  22.156  24.222  1.00 50.33           O
ATOM   2162  N   GLU B 243      57.594  23.765  22.636  1.00 52.35           N
ATOM   2163  CA  GLU B 243      59.032  23.989  22.674  1.00 52.57           C
ATOM   2164  CB  GLU B 243      59.378  25.168  21.763  1.00 77.99           C
ATOM   2165  CG  GLU B 243      58.929  24.983  20.315  1.00 81.11           C
ATOM   2166  CD  GLU B 243      57.424  24.775  20.178  1.00 82.02           C
ATOM   2167  OE1 GLU B 243      56.654  25.627  20.673  1.00 81.62           O
ATOM   2168  OE2 GLU B 243      57.015  23.762  19.569  1.00 83.30           O
ATOM   2169  C   GLU B 243      59.609  24.241  24.070  1.00 52.03           C
ATOM   2170  O   GLU B 243      60.775  23.932  24.333  1.00 51.82           O
ATOM   2171  N   THR B 244      58.798  24.803  24.959  1.00 44.64           N
ATOM   2172  CA  THR B 244      59.248  25.092  26.312  1.00 43.97           C
ATOM   2173  CB  THR B 244      58.309  26.092  26.996  1.00 51.31           C
ATOM   2174  OG1 THR B 244      57.034  25.471  27.218  1.00 52.22           O
ATOM   2175  CG2 THR B 244      58.117  27.322  26.117  1.00 50.74           C
ATOM   2176  C   THR B 244      59.289  23.822  27.152  1.00 43.17           C
ATOM   2177  O   THR B 244      59.576  23.864  28.343  1.00 42.78           O
ATOM   2178  N   LEU B 245      59.021  22.690  26.516  1.00 48.16           N
ATOM   2179  CA  LEU B 245      58.998  21.413  27.210  1.00 48.02           C
ATOM   2180  CB  LEU B 245      57.553  20.949  27.375  1.00 58.09           C
ATOM   2181  CG  LEU B 245      56.641  21.700  28.330  1.00 57.70           C
ATOM   2182  CD1 LEU B 245      55.203  21.252  28.109  1.00 58.58           C
ATOM   2183  CD2 LEU B 245      57.084  21.426  29.755  1.00 58.65           C
ATOM   2184  C   LEU B 245      59.775  20.281  26.550  1.00 47.95           C
ATOM   2185  O   LEU B 245      59.727  20.089  25.332  1.00 47.18           O
ATOM   2186  N   LYS B 246      60.476  19.514  27.374  1.00 48.48           N
ATOM   2187  CA  LYS B 246      61.202  18.364  26.872  1.00 48.71           C
ATOM   2188  CB  LYS B 246      62.715  18.542  26.999  1.00 57.58           C
ATOM   2189  CG  LYS B 246      63.483  17.314  26.511  1.00 58.94           C
ATOM   2190  CD  LYS B 246      64.941  17.624  26.201  1.00 60.16           C
ATOM   2191  CE  LYS B 246      65.675  18.163  27.424  1.00 60.54           C
ATOM   2192  NZ  LYS B 246      67.075  18.571  27.093  1.00 59.85           N
ATOM   2193  C   LYS B 246      60.771  17.137  27.651  1.00 47.88           C
ATOM   2194  O   LYS B 246      61.030  17.024  28.844  1.00 48.00           O
ATOM   2195  N   LEU B 247      60.082  16.233  26.972  1.00 53.08           N
ATOM   2196  CA  LEU B 247      59.637  14.998  27.582  1.00 52.92           C
ATOM   2197  CB  LEU B 247      58.508  14.376  26.755  1.00 50.84           C
ATOM   2198  CG  LEU B 247      57.092  14.813  27.158  1.00 51.30           C
ATOM   2199  CD1 LEU B 247      56.963  16.325  27.129  1.00 50.96           C
ATOM.  2200  CD2 LEU B 247      56.085  14.159  26.224  1.00 52.08           C
ATOM   2201  C   LEU B 247      60.850  14.087  27.623  1.00 53.15           C
ATOM   2202  O   LEU B 247      61.407  13.726  26.582  1.00 53.16           O
ATOM   2203  N   VAL B 248      61.266  13.721  28.828  1.00 46.84           N
ATOM   2204  CA  VAL B 248      62.445  12.886  28.984  1.00 46.63           C
```

Figure 15

| | | | | | | | | | | |
|---|---|---|---|---|---|---|---|---|---|---|
| ATOM | 2205 | CB | VAL | B | 248 | 63.321 | 13.409 | 30.125 | 1.00 48.58 | C |
| ATOM | 2206 | CG1 | VAL | B | 248 | 64.508 | 12.480 | 30.346 | 1.00 49.01 | C |
| ATOM | 2207 | CG2 | VAL | B | 248 | 63.782 | 14.812 | 29.805 | 1.00 49.01 | C |
| ATOM | 2208 | C | VAL | B | 248 | 62.218 | 11.408 | 29.221 | 1.00 46.04 | C |
| ATOM | 2209 | O | VAL | B | 248 | 62.851 | 10.575 | 28.580 | 1.00 46.24 | O |
| ATOM | 2210 | N | GLU | B | 249 | 61.300 | 11.083 | 30.126 | 1.00 46.35 | N |
| ATOM | 2211 | CA | GLU | B | 249 | 61.048 | 9.692 | 30.494 | 1.00 45.11 | C |
| ATOM | 2212 | CB | GLU | B | 249 | 61.796 | 9.425 | 31.799 | 1.00 49.87 | C |
| ATOM | 2213 | CG | GLU | B | 249 | 61.984 | 7.985 | 32.187 | 1.00 49.59 | C |
| ATOM | 2214 | CD | GLU | B | 249 | 62.724 | 7.867 | 33.508 | 1.00 49.44 | C |
| ATOM | 2215 | OE1 | GLU | B | 249 | 63.455 | 8.820 | 33.870 | 1.00 47.96 | O |
| ATOM | 2216 | OE2 | GLU | B | 249 | 62.579 | 6.826 | 34.177 | 1.00 49.51 | O |
| ATOM | 2217 | C | GLU | B | 249 | 59.558 | 9.376 | 30.678 | 1.00 44.26 | C |
| ATOM | 2218 | O | GLU | B | 249 | 58.816 | 10.177 | 31.235 | 1.00 43.93 | O |
| ATOM | 2219 | N | ARG | B | 250 | 59.130 | 8.201 | 30.225 | 1.00 47.41 | N |
| ATOM | 2220 | CA | ARG | B | 250 | 57.735 | 7.811 | 30.363 | 1.00 47.17 | C |
| ATOM | 2221 | CB | ARG | B | 250 | 57.295 | 6.908 | 29.202 | 1.00 48.93 | C |
| ATOM | 2222 | CG | ARG | B | 250 | 55.781 | 6.715 | 29.129 | 1.00 50.04 | C |
| ATOM | 2223 | CD | ARG | B | 250 | 55.334 | 5.891 | 27.920 | 1.00 51.59 | C |
| ATOM | 2224 | NE | ARG | B | 250 | 55.726 | 4.484 | 28.021 | 1.00 53.42 | N |
| ATOM | 2225 | CZ | ARG | B | 250 | 55.321 | 3.529 | 27.186 | 1.00 53.96 | C |
| ATOM | 2226 | NH1 | ARG | B | 250 | 54.504 | 3.820 | 26.177 | 1.00 52.54 | N |
| ATOM | 2227 | NH2 | ARG | B | 250 | 55.728 | 2.279 | 27.364 | 1.00 55.29 | N |
| ATOM | 2228 | C | ARG | B | 250 | 57.506 | 7.082 | 31.683 | 1.00 46.65 | C |
| ATOM | 2229 | O | ARG | B | 250 | 58.041 | 5.997 | 31.903 | 1.00 47.47 | O |
| ATOM | 2230 | N | LEU | B | 251 | 56.713 | 7.691 | 32.555 | 1.00 48.52 | N |
| ATOM | 2231 | CA | LEU | B | 251 | 56.396 | 7.116 | 33.850 | 1.00 47.05 | C |
| ATOM | 2232 | CB | LEU | B | 251 | 55.944 | 8.220 | 34.810 | 1.00 35.19 | C |
| ATOM | 2233 | CG | LEU | B | 251 | 56.958 | 9.350 | 35.002 | 1.00 33.59 | C |
| ATOM | 2234 | CD1 | LEU | B | 251 | 56.350 | 10.479 | 35.823 | 1.00 32.52 | C |
| ATOM | 2235 | CD2 | LEU | B | 251 | 58.212 | 8.800 | 35.668 | 1.00 32.70 | C |
| ATOM | 2236 | C | LEU | B | 251 | 55.300 | 6.059 | 33.700 | 1.00 47.42 | C |
| ATOM | 2237 | O | LEU | B | 251 | 55.292 | 5.061 | 34.414 | 1.00 48.38 | O |
| ATOM | 2238 | N | GLY | B | 252 | 54.379 | 6.266 | 32.764 | 1.00 43.32 | N |
| ATOM | 2239 | CA | GLY | B | 252 | 53.324 | 5.285 | 32.574 | 1.00 42.45 | C |
| ATOM | 2240 | C | GLY | B | 252 | 52.513 | 5.423 | 31.296 | 1.00 42.64 | C |
| ATOM | 2241 | O | GLY | B | 252 | 52.402 | 6.508 | 30.731 | 1.00 42.24 | O |
| ATOM | 2242 | N | ALA | B | 253 | 51.942 | 4.311 | 30.841 | 1.00 40.34 | N |
| ATOM | 2243 | CA | ALA | B | 253 | 51.121 | 4.299 | 29.636 | 1.00 40.89 | C |
| ATOM | 2244 | CB | ALA | B | 253 | 51.852 | 3.584 | 28.500 | 1.00 35.47 | C |
| ATOM | 2245 | C | ALA | B | 253 | 49.793 | 3.602 | 29.927 | 1.00 41.65 | C |
| ATOM | 2246 | O | ALA | B | 253 | 49.766 | 2.482 | 30.446 | 1.00 40.84 | O |
| ATOM | 2247 | N | GLY | B | 254 | 48.697 | 4.276 | 29.584 | 1.00 44.05 | N |
| ATOM | 2248 | CA | GLY | B | 254 | 47.381 | 3.722 | 29.821 | 1.00 45.13 | C |
| ATOM | 2249 | C | GLY | B | 254 | 46.364 | 3.949 | 28.717 | 1.00 46.03 | C |
| ATOM | 2250 | O | GLY | B | 254 | 46.671 | 4.489 | 27.657 | 1.00 47.18 | O |
| ATOM | 2251 | N | GLN | B | 255 | 45.128 | 3.553 | 28.992 | 1.00 53.27 | N |
| ATOM | 2252 | CA | GLN | B | 255 | 44.030 | 3.654 | 28.039 | 1.00 52.91 | C |
| ATOM | 2253 | CB | GLN | B | 255 | 42.765 | 3.107 | 28.698 | 1.00 79.19 | C |
| ATOM | 2254 | CG | GLN | B | 255 | 41.594 | 2.854 | 27.760 | 1.00 83.64 | C |
| ATOM | 2255 | CD | GLN | B | 255 | 40.412 | 2.225 | 28.480 | 1.00 85.79 | C |
| ATOM | 2256 | OE1 | GLN | B | 255 | 40.553 | 1.188 | 29.143 | 1.00 87.12 | O |
| ATOM | 2257 | NE2 | GLN | B | 255 | 39.239 | 2.846 | 28.356 | 1.00 85.74 | N |
| ATOM | 2258 | C | GLN | B | 255 | 43.760 | 5.052 | 27.477 | 1.00 52.57 | C |
| ATOM | 2259 | O | GLN | B | 255 | 43.399 | 5.194 | 26.304 | 1.00 53.43 | O |
| ATOM | 2260 | N | PHE | B | 256 | 43.934 | 6.084 | 28.300 | 1.00 38.10 | N |
| ATOM | 2261 | CA | PHE | B | 256 | 43.666 | 7.447 | 27.857 | 1.00 36.53 | C |
| ATOM | 2262 | CB | PHE | B | 256 | 42.804 | 8.172 | 28.899 | 1.00 45.60 | C |
| ATOM | 2263 | CG | PHE | B | 256 | 41.443 | 7.564 | 29.092 | 1.00 45.42 | C |
| ATOM | 2264 | CD1 | PHE | B | 256 | 40.875 | 6.776 | 28.101 | 1.00 45.54 | C |

Figure 15

| ATOM | 2265 | CD2 | PHE | B | 256 | 40.719 | 7.800 | 30.247 | 1.00 | 45.03 | C |
| ATOM | 2266 | CE1 | PHE | B | 256 | 39.615 | 6.241 | 28.261 | 1.00 | 45.53 | C |
| ATOM | 2267 | CE2 | PHE | B | 256 | 39.455 | 7.266 | 30.411 | 1.00 | 45.08 | C |
| ATOM | 2268 | CZ | PHE | B | 256 | 38.901 | 6.487 | 29.416 | 1.00 | 44.63 | C |
| ATOM | 2269 | C | PHE | B | 256 | 44.890 | 8.309 | 27.531 | 1.00 | 35.73 | C |
| ATOM | 2270 | O | PHE | B | 256 | 44.748 | 9.462 | 27.141 | 1.00 | 34.44 | O |
| ATOM | 2271 | N | GLY | B | 257 | 46.086 | 7.758 | 27.696 | 1.00 | 41.49 | N |
| ATOM | 2272 | CA | GLY | B | 257 | 47.279 | 8.528 | 27.402 | 1.00 | 40.53 | C |
| ATOM | 2273 | C | GLY | B | 257 | 48.475 | 8.085 | 28.214 | 1.00 | 39.97 | C |
| ATOM | 2274 | O | GLY | B | 257 | 48.558 | 6.935 | 28.630 | 1.00 | 38.99 | O |
| ATOM | 2275 | N | GLU | B | 258 | 49.407 | 9.001 | 28.441 | 1.00 | 41.03 | N |
| ATOM | 2276 | CA | GLU | B | 258 | 50.606 | 8.674 | 29.200 | 1.00 | 41.33 | C |
| ATOM | 2277 | CB | GLU | B | 258 | 51.765 | 8.363 | 28.248 | 1.00 | 51.36 | C |
| ATOM | 2278 | CG | GLU | B | 258 | 51.405 | 7.505 | 27.043 | 1.00 | 53.24 | C |
| ATOM | 2279 | CD | GLU | B | 258 | 52.583 | 7.340 | 26.093 | 1.00 | 55.55 | C |
| ATOM | 2280 | OE1 | GLU | B | 258 | 53.300 | 8.341 | 25.864 | 1.00 | 55.87 | O |
| ATOM | 2281 | OE2 | GLU | B | 258 | 52.793 | 6.222 | 25.572 | 1.00 | 55.98 | O |
| ATOM | 2282 | C | GLU | B | 258 | 51.023 | 9.819 | 30.107 | 1.00 | 40.61 | C |
| ATOM | 2283 | O | GLU | B | 258 | 50.538 | 10.946 | 29.984 | 1.00 | 40.93 | O |
| ATOM | 2284 | N | VAL | B | 259 | 51.922 | 9.517 | 31.030 | 1.00 | 39.92 | N |
| ATOM | 2285 | CA | VAL | B | 259 | 52.452 | 10.526 | 31.934 | 1.00 | 39.68 | C |
| ATOM | 2286 | CB | VAL | B | 259 | 52.089 | 10.242 | 33.399 | 1.00 | 39.51 | C |
| ATOM | 2287 | CG1 | VAL | B | 259 | 52.754 | 11.277 | 34.299 | 1.00 | 37.91 | C |
| ATOM | 2288 | CG2 | VAL | B | 259 | 50.563 | 10.267 | 33.575 | 1.00 | 38.83 | C |
| ATOM | 2289 | C | VAL | B | 259 | 53.971 | 10.506 | 31.776 | 1.00 | 39.81 | C |
| ATOM | 2290 | O | VAL | B | 259 | 54.587 | 9.441 | 31.733 | 1.00 | 39.70 | O |
| ATOM | 2291 | N | TRP | B | 260 | 54.564 | 11.686 | 31.681 | 1.00 | 43.21 | N |
| ATOM | 2292 | CA | TRP | B | 260 | 56.002 | 11.796 | 31.501 | 1.00 | 43.98 | C |
| ATOM | 2293 | CB | TRP | B | 260 | 56.326 | 12.313 | 30.093 | 1.00 | 44.67 | C |
| ATOM | 2294 | CG | TRP | B | 260 | 56.069 | 11.356 | 28.980 | 1.00 | 46.32 | C |
| ATOM | 2295 | CD2 | TRP | B | 260 | 57.052 | 10.764 | 28.120 | 1.00 | 46.96 | C |
| ATOM | 2296 | CE2 | TRP | B | 260 | 56.366 | 9.960 | 27.195 | 1.00 | 47.63 | C |
| ATOM | 2297 | CE3 | TRP | B | 260 | 58.445 | 10.841 | 28.043 | 1.00 | 46.80 | C |
| ATOM | 2298 | CD1 | TRP | B | 260 | 54.861 | 10.895 | 28.555 | 1.00 | 46.35 | C |
| ATOM | 2299 | NE1 | TRP | B | 260 | 55.029 | 10.056 | 27.481 | 1.00 | 47.51 | N |
| ATOM | 2300 | CZ2 | TRP | B | 260 | 57.025 | 9.234 | 26.204 | 1.00 | 48.56 | C |
| ATOM | 2301 | CZ3 | TRP | B | 260 | 59.095 | 10.122 | 27.063 | 1.00 | 46.81 | C |
| ATOM | 2302 | CH2 | TRP | B | 260 | 58.389 | 9.329 | 26.157 | 1.00 | 48.39 | C |
| ATOM | 2303 | C | TRP | B | 260 | 56.681 | 12.737 | 32.471 | 1.00 | 43.51 | C |
| ATOM | 2304 | O | TRP | B | 260 | 56.071 | 13.684 | 32.981 | 1.00 | 43.38 | O |
| ATOM | 2305 | N | MET | B | 261 | 57.955 | 12.461 | 32.722 | 1.00 | 39.84 | N |
| ATOM | 2306 | CA | MET | B | 261 | 58.775 | 13.336 | 33.545 | 1.00 | 40.09 | C |
| ATOM | 2307 | CB | MET | B | 261 | 59.815 | 12.557 | 34.348 | 1.00 | 43.94 | C |
| ATOM | 2308 | CG | MET | B | 261 | 60.721 | 13.446 | 35.214 | 1.00 | 44.81 | C |
| ATOM | 2309 | SD | MET | B | 261 | 62.014 | 14.383 | 34.338 | 1.00 | 45.85 | S |
| ATOM | 2310 | CE | MET | B | 261 | 63.160 | 13.070 | 33.937 | 1.00 | 43.93 | C |
| ATOM | 2311 | C | MET | B | 261 | 59.477 | 14.141 | 32.467 | 1.00 | 39.91 | C |
| ATOM | 2312 | O | MET | B | 261 | 59.863 | 13.594 | 31.438 | 1.00 | 39.22 | O |
| ATOM | 2313 | N | GLY | B | 262 | 59.619 | 15.438 | 32.682 | 1.00 | 41.78 | N |
| ATOM | 2314 | CA | GLY | B | 262 | 60.289 | 16.253 | 31.698 | 1.00 | 42.79 | C |
| ATOM | 2315 | C | GLY | B | 262 | 60.805 | 17.494 | 32.374 | 1.00 | 43.70 | C |
| ATOM | 2316 | O | GLY | B | 262 | 60.797 | 17.583 | 33.601 | 1.00 | 44.11 | O |
| ATOM | 2317 | N | TYR | B | 263 | 61.267 | 18.451 | 31.583 | 1.00 | 39.96 | N |
| ATOM | 2318 | CA | TYR | B | 263 | 61.752 | 19.694 | 32.146 | 1.00 | 41.23 | C |
| ATOM | 2319 | CB | TYR | B | 263 | 63.265 | 19.821 | 31.965 | 1.00 | 42.95 | C |
| ATOM | 2320 | CG | TYR | B | 263 | 64.017 | 18.792 | 32.767 | 1.00 | 40.60 | C |
| ATOM | 2321 | CD1 | TYR | B | 263 | 64.287 | 17.532 | 32.238 | 1.00 | 40.24 | C |
| ATOM | 2322 | CE1 | TYR | B | 263 | 64.903 | 16.560 | 32.995 | 1.00 | 38.58 | C |
| ATOM | 2323 | CD2 | TYR | B | 263 | 64.390 | 19.047 | 34.078 | 1.00 | 39.16 | C |
| ATOM | 2324 | CE2 | TYR | B | 263 | 65.004 | 18.077 | 34.843 | 1.00 | 39.38 | C |

Figure 15

| ATOM | 2325 | CZ | TYR | B | 263 | 65.255 | 16.837 | 34.296 | 1.00 | 39.25 | C |
|------|------|------|-----|---|-----|--------|--------|--------|------|-------|---|
| ATOM | 2326 | OH | TYR | B | 263 | 65.849 | 15.863 | 35.059 | 1.00 | 40.76 | O |
| ATOM | 2327 | C | TYR | B | 263 | 61.021 | 20.849 | 31.497 | 1.00 | 42.84 | C |
| ATOM | 2328 | O | TYR | B | 263 | 60.799 | 20.871 | 30.285 | 1.00 | 43.03 | O |
| ATOM | 2329 | N | TYR | B | 264 | 60.631 | 21.803 | 32.322 | 1.00 | 48.13 | N |
| ATOM | 2330 | CA | TYR | B | 264 | 59.891 | 22.956 | 31.855 | 1.00 | 50.92 | C |
| ATOM | 2331 | CB | TYR | B | 264 | 58.673 | 23.148 | 32.762 | 1.00 | 65.73 | C |
| ATOM | 2332 | CG | TYR | B | 264 | 57.773 | 24.302 | 32.404 | 1.00 | 67.93 | C |
| ATOM | 2333 | CD1 | TYR | B | 264 | 57.389 | 24.534 | 31.091 | 1.00 | 68.51 | C |
| ATOM | 2334 | CE1 | TYR | B | 264 | 56.540 | 25.581 | 30.770 | 1.00 | 68.74 | C |
| ATOM | 2335 | CD2 | TYR | B | 264 | 57.283 | 25.149 | 33.392 | 1.00 | 68.26 | C |
| ATOM | 2336 | CE2 | TYR | B | 264 | 56.439 | 26.192 | 33.084 | 1.00 | 68.27 | C |
| ATOM | 2337 | CZ | TYR | B | 264 | 56.071 | 26.405 | 31.774 | 1.00 | 68.85 | C |
| ATOM | 2338 | OH | TYR | B | 264 | 55.235 | 27.454 | 31.474 | 1.00 | 69.61 | O |
| ATOM | 2339 | C | TYR | B | 264 | 60.807 | 24.177 | 31.861 | 1.00 | 52.23 | C |
| ATOM | 2340 | O | TYR | B | 264 | 61.328 | 24.570 | 32.903 | 1.00 | 52.03 | O |
| ATOM | 2341 | N | ASN | B | 265 | 61.008 | 24.757 | 30.684 | 1.00 | 61.70 | N |
| ATOM | 2342 | CA | ASN | B | 265 | 61.871 | 25.922 | 30.534 | 1.00 | 64.03 | C |
| ATOM | 2343 | CB | ASN | B | 265 | 61.410 | 27.063 | 31.450 | 1.00 | 63.53 | C |
| ATOM | 2344 | CG | ASN | B | 265 | 60.041 | 27.605 | 31.066 | 1.00 | 65.08 | C |
| ATOM | 2345 | OD1 | ASN | B | 265 | 59.822 | 28.018 | 29.926 | 1.00 | 65.15 | O |
| ATOM | 2346 | ND2 | ASN | B | 265 | 59.114 | 27.615 | 32.022 | 1.00 | 64.62 | N |
| ATOM | 2347 | C | ASN | B | 265 | 63.337 | 25.587 | 30.826 | 1.00 | 65.00 | C |
| ATOM | 2348 | O | ASN | B | 265 | 64.120 | 26.465 | 31.188 | 1.00 | 65.54 | O |
| ATOM | 2349 | N | GLY | B | 266 | 63.704 | 24.317 | 30.684 | 1.00 | 57.02 | N |
| ATOM | 2350 | CA | GLY | B | 266 | 65.088 | 23.937 | 30.906 | 1.00 | 57.27 | C |
| ATOM | 2351 | C | GLY | B | 266 | 65.485 | 23.230 | 32.189 | 1.00 | 57.72 | C |
| ATOM | 2352 | O | GLY | B | 266 | 66.129 | 22.181 | 32.134 | 1.00 | 57.93 | O |
| ATOM | 2353 | N | HIS | B | 267 | 65.113 | 23.778 | 33.343 | 1.00 | 70.53 | N |
| ATOM | 2354 | CA | HIS | B | 267 | 65.498 | 23.159 | 34.610 | 1.00 | 70.38 | C |
| ATOM | 2355 | CB | HIS | B | 267 | 66.522 | 24.048 | 35.323 | 1.00 | 116.55 | C |
| ATOM | 2356 | CG | HIS | B | 267 | 67.879 | 24.036 | 34.686 | 1.00 | 118.84 | C |
| ATOM | 2357 | CD2 | HIS | B | 267 | 69.105 | 23.776 | 35.204 | 1.00 | 119.26 | C |
| ATOM | 2358 | ND1 | HIS | B | 267 | 68.084 | 24.339 | 33.355 | 1.00 | 120.07 | N |
| ATOM | 2359 | CE1 | HIS | B | 267 | 69.375 | 24.266 | 33.082 | 1.00 | 120.69 | C |
| ATOM | 2360 | NE2 | HIS | B | 267 | 70.016 | 23.926 | 34.187 | 1.00 | 120.33 | N |
| ATOM | 2361 | C | HIS | B | 267 | 64.396 | 22.771 | 35.596 | 1.00 | 68.90 | C |
| ATOM | 2362 | O | HIS | B | 267 | 64.663 | 22.057 | 36.558 | 1.00 | 69.21 | O |
| ATOM | 2363 | N | THR | B | 268 | 63.169 | 23.233 | 35.381 | 1.00 | 60.88 | N |
| ATOM | 2364 | CA | THR | B | 268 | 62.075 | 22.877 | 36.289 | 1.00 | 58.41 | C |
| ATOM | 2365 | CB | THR | B | 268 | 60.901 | 23.862 | 36.189 | 1.00 | 54.76 | C |
| ATOM | 2366 | OG1 | THR | B | 268 | 61.342 | 25.174 | 36.547 | 1.00 | 55.10 | O |
| ATOM | 2367 | CG2 | THR | B | 268 | 59.771 | 23.437 | 37.126 | 1.00 | 54.87 | C |
| ATOM | 2368 | C | THR | B | 268 | 61.541 | 21.488 | 35.957 | 1.00 | 55.95 | C |
| ATOM | 2369 | O | THR | B | 268 | 60.914 | 21.290 | 34.920 | 1.00 | 56.24 | O |
| ATOM | 2370 | N | LYS | B | 269 | 61.791 | 20.531 | 36.839 | 1.00 | 46.18 | N |
| ATOM | 2371 | CA | LYS | B | 269 | 61.332 | 19.165 | 36.633 | 1.00 | 44.22 | C |
| ATOM | 2372 | CB | LYS | B | 269 | 61.957 | 18.249 | 37.685 | 1.00 | 48.56 | C |
| ATOM | 2373 | CG | LYS | B | 269 | 61.837 | 16.768 | 37.390 | 1.00 | 48.82 | C |
| ATOM | 2374 | CD | LYS | B | 269 | 62.815 | 15.989 | 38.246 | 1.00 | 49.71 | C |
| ATOM | 2375 | CE | LYS | B | 269 | 63.065 | 14.607 | 37.677 | 1.00 | 50.40 | C |
| ATOM | 2376 | NZ | LYS | B | 269 | 64.239 | 13.962 | 38.328 | 1.00 | 51.68 | N |
| ATOM | 2377 | C | LYS | B | 269 | 59.800 | 19.129 | 36.724 | 1.00 | 42.43 | C |
| ATOM | 2378 | O | LYS | B | 269 | 59.212 | 19.710 | 37.636 | 1.00 | 41.79 | O |
| ATOM | 2379 | N | VAL | B | 270 | 59.158 | 18.449 | 35.777 | 1.00 | 37.29 | N |
| ATOM | 2380 | CA | VAL | B | 270 | 57.697 | 18.385 | 35.761 | 1.00 | 34.75 | C |
| ATOM | 2381 | CB | VAL | B | 270 | 57.096 | 19.426 | 34.781 | 1.00 | 32.01 | C |
| ATOM | 2382 | CG1 | VAL | B | 270 | 57.360 | 20.849 | 35.267 | 1.00 | 28.83 | C |
| ATOM | 2383 | CG2 | VAL | B | 270 | 57.687 | 19.199 | 33.384 | 1.00 | 29.81 | C |
| ATOM | 2384 | C | VAL | B | 270 | 57.133 | 17.044 | 35.332 | 1.00 | 33.73 | C |

Figure 15

| | | | | | | | | | | |
|---|---|---|---|---|---|---|---|---|---|---|
| ATOM | 2385 | O | VAL | B | 270 | 57.826 | 16.204 | 34.768 | 1.00 33.86 | O |
| ATOM | 2386 | N | ALA | B | 271 | 55.856 | 16.847 | 35.632 | 1.00 38.49 | N |
| ATOM | 2387 | CA | ALA | B | 271 | 55.153 | 15.650 | 35.210 | 1.00 37.36 | C |
| ATOM | 2388 | CB | ALA | B | 271 | 54.261 | 15.126 | 36.309 | 1.00 37.62 | C |
| ATOM | 2389 | C | ALA | B | 271 | 54.308 | 16.196 | 34.072 | 1.00 36.26 | C |
| ATOM | 2390 | O | ALA | B | 271 | 53.777 | 17.300 | 34.169 | 1.00 35.37 | O |
| ATOM | 2391 | N | VAL | B | 272 | 54.199 | 15.436 | 32.995 | 1.00 36.77 | N |
| ATOM | 2392 | CA | VAL | B | 272 | 53.422 | 15.870 | 31.850 | 1.00 35.91 | C |
| ATOM | 2393 | CB | VAL | B | 272 | 54.332 | 16.189 | 30.633 | 1.00 35.66 | C |
| ATOM | 2394 | CG1 | VAL | B | 272 | 53.491 | 16.742 | 29.483 | 1.00 33.08 | C |
| ATOM | 2395 | CG2 | VAL | B | 272 | 55.411 | 17.189 | 31.036 | 1.00 35.54 | C |
| ATOM | 2396 | C | VAL | B | 272 | 52.452 | 14.780 | 31.449 | 1.00 36.36 | C |
| ATOM | 2397 | O | VAL | B | 272 | 52.860 | 13.671 | 31.102 | 1.00 36.26 | O |
| ATOM | 2398 | N | LYS | B | 273 | 51.161 | 15.091 | 31.511 | 1.00 36.34 | N |
| ATOM | 2399 | CA | LYS | B | 273 | 50.156 | 14.117 | 31.115 | 1.00 37.08 | C |
| ATOM | 2400 | CB | LYS | B | 273 | 48.969 | 14.116 | 32.085 | 1.00 39.42 | C |
| ATOM | 2401 | CG | LYS | B | 273 | 47.822 | 13.222 | 31.633 | 1.00 40.27 | C |
| ATOM | 2402 | CD | LYS | B | 273 | 46.643 | 13.275 | 32.596 | 1.00 40.90 | C |
| ATOM | 2403 | CE | LYS | B | 273 | 46.963 | 12.584 | 33.903 | 1.00 42.32 | C |
| ATOM | 2404 | NZ | LYS | B | 273 | 45.814 | 12.624 | 34.849 | 1.00 44.41 | N |
| ATOM | 2405 | C | LYS | B | 273 | 49.679 | 14.458 | 29.711 | 1.00 37.12 | C |
| ATOM | 2406 | O | LYS | B | 273 | 49.205 | 15.567 | 29.451 | 1.00 36.64 | O |
| ATOM | 2407 | N | SER | B | 274 | 49.824 | 13.509 | 28.798 | 1.00 39.59 | N |
| ATOM | 2408 | CA | SER | B | 274 | 49.394 | 13.744 | 27.432 | 1.00 41.39 | C |
| ATOM | 2409 | CB | SER | B | 274 | 50.537 | 13.480 | 26.453 | 1.00 39.02 | C |
| ATOM | 2410 | OG | SER | B | 274 | 50.995 | 12.152 | 26.583 | 1.00 41.56 | O |
| ATOM | 2411 | C | SER | B | 274 | 48.211 | 12.850 | 27.103 | 1.00 42.16 | C |
| ATOM | 2412 | O | SER | B | 274 | 48.184 | 11.665 | 27.447 | 1.00 42.42 | O |
| ATOM | 2413 | N | LEU | B | 275 | 47.238 | 13.443 | 26.428 | 1.00 47.95 | N |
| ATOM | 2414 | CA | LEU | B | 275 | 46.023 | 12.753 | 26.031 | 1.00 48.72 | C |
| ATOM | 2415 | CB | LEU | B | 275 | 44.905 | 13.776 | 25.813 | 1.00 40.13 | C |
| ATOM | 2416 | CG | LEU | B | 275 | 43.630 | 13.249 | 25.151 | 1.00 40.53 | C |
| ATOM | 2417 | CD1 | LEU | B | 275 | 42.962 | 12.222 | 26.067 | 1.00 39.86 | C |
| ATOM | 2418 | CD2 | LEU | B | 275 | 42.696 | 14.401 | 24.851 | 1.00 38.23 | C |
| ATOM | 2419 | C | LEU | B | 275 | 46.200 | 11.935 | 24.761 | 1.00 49.34 | C |
| ATOM | 2420 | O | LEU | B | 275 | 46.793 | 12.395 | 23.791 | 1.00 49.55 | O |
| ATOM | 2421 | N | LYS | B | 276 | 45.700 | 10.709 | 24.779 | 1.00 45.00 | N |
| ATOM | 2422 | CA | LYS | B | 276 | 45.754 | 9.865 | 23.592 | 1.00 46.76 | C |
| ATOM | 2423 | CB | LYS | B | 276 | 45.596 | 8.389 | 23.976 | 1.00 60.44 | C |
| ATOM | 2424 | CG | LYS | B | 276 | 45.639 | 7.426 | 22.794 | 1.00 62.85 | C |
| ATOM | 2425 | CD | LYS | B | 276 | 45.197 | 6.029 | 23.209 | 1.00 64.99 | C |
| ATOM | 2426 | CE | LYS | B | 276 | 45.967 | 5.549 | 24.436 | 1.00 65.57 | C |
| ATOM | 2427 | NZ | LYS | B | 276 | 45.433 | 4.265 | 24.973 | 1.00 67.20 | N |
| ATOM | 2428 | C | LYS | B | 276 | 44.529 | 10.330 | 22.801 | 1.00 47.37 | C |
| ATOM | 2429 | O | LYS | B | 276 | 43.419 | 10.333 | 23.335 | 1.00 46.81 | O |
| ATOM | 2430 | N | GLN | B | 277 | 44.716 | 10.739 | 21.550 | 1.00 45.67 | N |
| ATOM | 2431 | CA | GLN | B | 277 | 43.586 | 11.216 | 20.758 | 1.00 47.19 | C |
| ATOM | 2432 | CB | GLN | B | 277 | 44.035 | 11.694 | 19.373 | 1.00 81.54 | C |
| ATOM | 2433 | CG | GLN | B | 277 | 42.928 | 12.481 | 18.652 | 1.00 84.53 | C |
| ATOM | 2434 | CD | GLN | B | 277 | 43.384 | 13.127 | 17.358 | 1.00 86.36 | C |
| ATOM | 2435 | OE1 | GLN | B | 277 | 43.720 | 12.439 | 16.390 | 1.00 87.93 | O |
| ATOM | 2436 | NE2 | GLN | B | 277 | 43.395 | 14.460 | 17.333 | 1.00 86.31 | N |
| ATOM | 2437 | C | GLN | B | 277 | 42.486 | 10.168 | 20.608 | 1.00 47.16 | C |
| ATOM | 2438 | O | GLN | B | 277 | 42.753 | 8.977 | 20.432 | 1.00 47.00 | O |
| ATOM | 2439 | N | GLY | B | 278 | 41.242 | 10.624 | 20.693 | 1.00 61.59 | N |
| ATOM | 2440 | CA | GLY | B | 278 | 40.116 | 9.720 | 20.571 | 1.00 61.97 | C |
| ATOM | 2441 | C | GLY | B | 278 | 39.563 | 9.262 | 21.911 | 1.00 62.47 | C |
| ATOM | 2442 | O | GLY | B | 278 | 38.363 | 8.978 | 22.023 | 1.00 63.29 | O |
| ATOM | 2443 | N | SER | B | 279 | 40.424 | 9.186 | 22.925 | 1.00 47.28 | N |
| ATOM | 2444 | CA | SER | B | 279 | 40.002 | 8.758 | 24.256 | 1.00 46.86 | C |

Figure 15

```
ATOM   2445  CB   SER B 279      41.154   8.913  25.251  1.00 49.12           C
ATOM   2446  OG   SER B 279      42.178   7.987  24.966  1.00 49.36           O
ATOM   2447  C    SER B 279      38.815   9.591  24.713  1.00 46.65           C
ATOM   2448  O    SER B 279      37.743   9.070  25.011  1.00 46.67           O
ATOM   2449  N    MET B 280      39.034  10.898  24.770  1.00 49.90           N
ATOM   2450  CA   MET B 280      38.012  11.852  25.160  1.00 49.49           C
ATOM   2451  CB   MET B 280      38.048  12.094  26.673  1.00 48.57           C
ATOM   2452  CG   MET B 280      39.297  12.795  27.175  1.00 47.93           C
ATOM   2453  SD   MET B 280      39.510  12.643  28.963  1.00 48.32           S
ATOM   2454  CE   MET B 280      38.732  14.083  29.515  1.00 49.14           C
ATOM   2455  C    MET B 280      38.373  13.120  24.399  1.00 49.78           C
ATOM   2456  O    MET B 280      39.404  13.172  23.724  1.00 50.24           O
ATOM   2457  N    SER B 281      37.539  14.143  24.497  1.00 46.62           N
ATOM   2458  CA   SER B 281      37.813  15.379  23.784  1.00 46.95           C
ATOM   2459  CB   SER B 281      36.515  16.143  23.534  1.00 45.61           C
ATOM   2460  OG   SER B 281      36.100  16.833  24.699  1.00 45.48           O
ATOM   2461  C    SER B 281      38.779  16.273  24.551  1.00 47.96           C
ATOM   2462  O    SER B 281      38.852  16.231  25.783  1.00 47.75           O
ATOM   2463  N    PRO B 282      39.538  17.099  23.821  1.00 50.63           N
ATOM   2464  CD   PRO B 282      39.595  17.105  22.347  1.00 49.03           C
ATOM   2465  CA   PRO B 282      40.514  18.034  24.377  1.00 50.95           C
ATOM   2466  CB   PRO B 282      40.844  18.908  23.181  1.00 49.30           C
ATOM   2467  CG   PRO B 282      40.853  17.909  22.074  1.00 48.30           C
ATOM   2468  C    PRO B 282      39.945  18.827  25.551  1.00 51.90           C
ATOM   2469  O    PRO B 282      40.535  18.863  26.632  1.00 52.25           O
ATOM   2470  N    ASP B 283      38.797  19.456  25.330  1.00 54.76           N
ATOM   2471  CA   ASP B 283      38.127  20.249  26.362  1.00 55.68           C
ATOM   2472  CB   ASP B 283      36.796  20.790  25.821  1.00 66.99           C
ATOM   2473  CG   ASP B 283      36.989  21.922  24.826  1.00 68.22           C
ATOM   2474  OD1  ASP B 283      37.410  23.016  25.255  1.00 69.23           O
ATOM   2475  OD2  ASP B 283      36.730  21.719  23.620  1.00 68.95           O
ATOM   2476  C    ASP B 283      37.875  19.439  27.634  1.00 55.54           C
ATOM   2477  O    ASP B 283      38.105  19.917  28.748  1.00 55.99           O
ATOM   2478  N    ALA B 284      37.392  18.214  27.462  1.00 62.63           N
ATOM   2479  CA   ALA B 284      37.119  17.330  28.588  1.00 62.21           C
ATOM   2480  CB   ALA B 284      36.472  16.047  28.096  1.00 40.82           C
ATOM   2481  C    ALA B 284      38.419  17.010  29.317  1.00 62.32           C
ATOM   2482  O    ALA B 284      38.452  16.910  30.544  1.00 63.19           O
ATOM   2483  N    PHE B 285      39.488  16.826  28.548  1.00 46.92           N
ATOM   2484  CA   PHE B 285      40.797  16.522  29.109  1.00 45.68           C
ATOM   2485  CB   PHE B 285      41.771  16.158  27.983  1.00 44.46           C
ATOM   2486  CG   PHE B 285      43.153  15.796  28.457  1.00 43.38           C
ATOM   2487  CD1  PHE B 285      43.369  14.648  29.214  1.00 42.44           C
ATOM   2488  CD2  PHE B 285      44.241  16.589  28.125  1.00 41.82           C
ATOM   2489  CE1  PHE B 285      44.640  14.301  29.623  1.00 41.06           C
ATOM   2490  CE2  PHE B 285      45.516  16.250  28.530  1.00 40.70           C
ATOM   2491  CZ   PHE B 285      45.719  15.104  29.279  1.00 41.67           C
ATOM   2492  C    PHE B 285      41.296  17.754  29.847  1.00 46.30           C
ATOM   2493  O    PHE B 285      41.688  17.679  31.009  1.00 46.24           O
ATOM   2494  N    LEU B 286      41.259  18.891  29.162  1.00 46.83           N
ATOM   2495  CA   LEU B 286      41.716  20.148  29.731  1.00 48.11           C
ATOM   2496  CB   LEU B 286      41.772  21.218  28.641  1.00 59.34           C
ATOM   2497  CG   LEU B 286      42.826  20.927  27.567  1.00 60.58           C
ATOM   2498  CD1  LEU B 286      42.703  21.918  26.419  1.00 60.35           C
ATOM   2499  CD2  LEU B 286      44.211  20.984  28.198  1.00 60.34           C
ATOM   2500  C    LEU B 286      40.853  20.625  30.887  1.00 49.12           C
ATOM   2501  O    LEU B 286      41.235  21.544  31.613  1.00 49.17           O
ATOM   2502  N    ALA B 287      39.694  19.993  31.065  1.00 66.45           N
ATOM   2503  CA   ALA B 287      38.775  20.354  32.142  1.00 66.84           C
ATOM   2504  CB   ALA B 287      37.500  19.531  32.035  1.00 68.32           C
```

Figure 15

| ATOM | 2505 | C | ALA | B | 287 | 39.436 | 20.117 | 33.489 | 1.00 | 67.12 | C |
|------|------|---|-----|---|-----|--------|--------|--------|------|-------|---|
| ATOM | 2506 | O | ALA | B | 287 | 39.372 | 20.959 | 34.386 | 1.00 | 67.77 | O |
| ATOM | 2507 | N | GLU | B | 288 | 40.073 | 18.958 | 33.611 | 1.00 | 65.92 | N |
| ATOM | 2508 | CA | GLU | B | 288 | 40.770 | 18.558 | 34.828 | 1.00 | 65.71 | C |
| ATOM | 2509 | CB | GLU | B | 288 | 41.514 | 17.240 | 34.584 | 1.00 | 89.38 | C |
| ATOM | 2510 | CG | GLU | B | 288 | 40.613 | 16.013 | 34.579 | 1.00 | 91.26 | C |
| ATOM | 2511 | CD | GLU | B | 288 | 40.794 | 15.131 | 33.357 | 1.00 | 92.38 | C |
| ATOM | 2512 | OE1 | GLU | B | 288 | 41.940 | 14.704 | 33.080 | 1.00 | 93.50 | O |
| ATOM | 2513 | OE2 | GLU | B | 288 | 39.779 | 14.857 | 32.679 | 1.00 | 92.20 | O |
| ATOM | 2514 | C | GLU | B | 288 | 41.751 | 19.611 | 35.315 | 1.00 | 65.06 | C |
| ATOM | 2515 | O | GLU | B | 288 | 41.880 | 19.847 | 36.519 | 1.00 | 65.37 | O |
| ATOM | 2516 | N | ALA | B | 289 | 42.444 | 20.241 | 34.373 | 1.00 | 51.23 | N |
| ATOM | 2517 | CA | ALA | B | 289 | 43.426 | 21.267 | 34.698 | 1.00 | 49.85 | C |
| ATOM | 2518 | CB | ALA | B | 289 | 44.199 | 21.659 | 33.442 | 1.00 | 48.35 | C |
| ATOM | 2519 | C | ALA | B | 289 | 42.763 | 22.490 | 35.312 | 1.00 | 49.03 | C |
| ATOM | 2520 | O | ALA | B | 289 | 43.268 | 23.056 | 36.282 | 1.00 | 48.61 | O |
| ATOM | 2521 | N | ASN | B | 290 | 41.630 | 22.890 | 34.745 | 1.00 | 52.35 | N |
| ATOM | 2522 | CA | ASN | B | 290 | 40.888 | 24.052 | 35.229 | 1.00 | 52.48 | C |
| ATOM | 2523 | CB | ASN | B | 290 | 39.527 | 24.131 | 34.531 | 1.00 | 75.48 | C |
| ATOM | 2524 | CG | ASN | B | 290 | 39.650 | 24.236 | 33.021 | 1.00 | 76.90 | C |
| ATOM | 2525 | OD1 | ASN | B | 290 | 38.665 | 24.085 | 32.290 | 1.00 | 77.70 | O |
| ATOM | 2526 | ND2 | ASN | B | 290 | 40.861 | 24.501 | 32.546 | 1.00 | 76.88 | N |
| ATOM | 2527 | C | ASN | B | 290 | 40.681 | 23.980 | 36.739 | 1.00 | 51.99 | C |
| ATOM | 2528 | O | ASN | B | 290 | 40.655 | 25.000 | 37.418 | 1.00 | 51.85 | O |
| ATOM | 2529 | N | LEU | B | 291 | 40.537 | 22.762 | 37.252 | 1.00 | 54.59 | N |
| ATOM | 2530 | CA | LEU | B | 291 | 40.331 | 22.536 | 38.677 | 1.00 | 54.00 | C |
| ATOM | 2531 | CB | LEU | B | 291 | 40.042 | 21.055 | 38.934 | 1.00 | 55.60 | C |
| ATOM | 2532 | CG | LEU | B | 291 | 38.738 | 20.521 | 38.337 | 1.00 | 55.96 | C |
| ATOM | 2533 | CD1 | LEU | B | 291 | 38.715 | 18.998 | 38.421 | 1.00 | 57.16 | C |
| ATOM | 2534 | CD2 | LEU | B | 291 | 37.564 | 21.117 | 39.077 | 1.00 | 55.16 | C |
| ATOM | 2535 | C | LEU | B | 291 | 41.531 | 22.974 | 39.501 | 1.00 | 53.54 | C |
| ATOM | 2536 | O | LEU | B | 291 | 41.378 | 23.572 | 40.566 | 1.00 | 52.97 | O |
| ATOM | 2537 | N | MET | B | 292 | 42.730 | 22.666 | 39.019 | 1.00 | 45.65 | N |
| ATOM | 2538 | CA | MET | B | 292 | 43.937 | 23.055 | 39.740 | 1.00 | 45.81 | C |
| ATOM | 2539 | CB | MET | B | 292 | 45.150 | 22.329 | 39.169 | 1.00 | 51.09 | C |
| ATOM | 2540 | CG | MET | B | 292 | 45.247 | 20.887 | 39.633 | 1.00 | 50.92 | C |
| ATOM | 2541 | SD | MET | B | 292 | 46.503 | 19.944 | 38.776 | 1.00 | 48.38 | S |
| ATOM | 2542 | CE | MET | B | 292 | 45.491 | 19.225 | 37.518 | 1.00 | 47.44 | C |
| ATOM | 2543 | C | MET | B | 292 | 44.134 | 24.562 | 39.667 | 1.00 | 46.34 | C |
| ATOM | 2544 | O | MET | B | 292 | 44.764 | 25.159 | 40.538 | 1.00 | 46.13 | O |
| ATOM | 2545 | N | LYS | B | 293 | 43.586 | 25.177 | 38.626 | 1.00 | 50.81 | N |
| ATOM | 2546 | CA | LYS | B | 293 | 43.690 | 26.619 | 38.472 | 1.00 | 52.13 | C |
| ATOM | 2547 | CB | LYS | B | 293 | 43.050 | 27.078 | 37.158 | 1.00 | 60.79 | C |
| ATOM | 2548 | CG | LYS | B | 293 | 43.679 | 26.542 | 35.882 | 1.00 | 61.61 | C |
| ATOM | 2549 | CD | LYS | B | 293 | 43.190 | 27.363 | 34.684 | 1.00 | 62.82 | C |
| ATOM | 2550 | CE | LYS | B | 293 | 43.823 | 26.931 | 33.368 | 1.00 | 62.99 | C |
| ATOM | 2551 | NZ | LYS | B | 293 | 43.316 | 25.612 | 32.896 | 1.00 | 63.49 | N |
| ATOM | 2552 | C | LYS | B | 293 | 42.957 | 27.288 | 39.630 | 1.00 | 52.94 | C |
| ATOM | 2553 | O | LYS | B | 293 | 43.511 | 28.131 | 40.333 | 1.00 | 53.34 | O |
| ATOM | 2554 | N | GLN | B | 294 | 41.707 | 26.885 | 39.829 | 1.00 | 64.11 | N |
| ATOM | 2555 | CA | GLN | B | 294 | 40.858 | 27.452 | 40.870 | 1.00 | 65.10 | C |
| ATOM | 2556 | CB | GLN | B | 294 | 39.407 | 27.023 | 40.631 | 1.00 | 97.65 | C |
| ATOM | 2557 | CG | GLN | B | 294 | 38.948 | 27.227 | 39.192 | 1.00 | 100.88 | C |
| ATOM | 2558 | CD | GLN | B | 294 | 39.121 | 28.664 | 38.710 | 1.00 | 103.28 | C |
| ATOM | 2559 | OE1 | GLN | B | 294 | 39.171 | 28.926 | 37.505 | 1.00 | 104.34 | O |
| ATOM | 2560 | NE2 | GLN | B | 294 | 39.205 | 29.605 | 39.653 | 1.00 | 104.44 | N |
| ATOM | 2561 | C | GLN | B | 294 | 41.260 | 27.132 | 42.306 | 1.00 | 64.45 | C |
| ATOM | 2562 | O | GLN | B | 294 | 41.312 | 28.032 | 43.153 | 1.00 | 64.88 | O |
| ATOM | 2563 | N | LEU | B | 295 | 41.532 | 25.860 | 42.588 | 1.00 | 53.67 | N |
| ATOM | 2564 | CA | LEU | B | 295 | 41.917 | 25.452 | 43.941 | 1.00 | 52.42 | C |

Figure 15

| ATOM | 2565 | CB  | LEU | B | 295 | 41.173 | 24.174 | 44.356 | 1.00 | 59.63 | C |
|------|------|-----|-----|---|-----|--------|--------|--------|------|-------|---|
| ATOM | 2566 | CG  | LEU | B | 295 | 39.667 | 24.260 | 44.630 | 1.00 | 59.76 | C |
| ATOM | 2567 | CD1 | LEU | B | 295 | 39.151 | 22.904 | 45.078 | 1.00 | 60.35 | C |
| ATOM | 2568 | CD2 | LEU | B | 295 | 39.404 | 25.290 | 45.710 | 1.00 | 60.74 | C |
| ATOM | 2569 | C   | LEU | B | 295 | 43.414 | 25.215 | 44.073 | 1.00 | 50.85 | C |
| ATOM | 2570 | O   | LEU | B | 295 | 43.948 | 24.242 | 43.543 | 1.00 | 50.81 | O |
| ATOM | 2571 | N   | GLN | B | 296 | 44.086 | 26.103 | 44.794 | 1.00 | 49.29 | N |
| ATOM | 2572 | CA  | GLN | B | 296 | 45.520 | 25.979 | 45.002 | 1.00 | 48.13 | C |
| ATOM | 2573 | CB  | GLN | B | 296 | 46.236 | 27.180 | 44.383 | 1.00 | 61.95 | C |
| ATOM | 2574 | CG  | GLN | B | 296 | 46.138 | 27.189 | 42.856 | 1.00 | 64.25 | C |
| ATOM | 2575 | CD  | GLN | B | 296 | 46.512 | 28.521 | 42.238 | 1.00 | 65.33 | C |
| ATOM | 2576 | OE1 | GLN | B | 296 | 47.584 | 29.066 | 42.507 | 1.00 | 67.04 | O |
| ATOM | 2577 | NE2 | GLN | B | 296 | 45.632 | 29.049 | 41.398 | 1.00 | 64.30 | N |
| ATOM | 2578 | C   | GLN | B | 296 | 45.828 | 25.851 | 46.488 | 1.00 | 46.89 | C |
| ATOM | 2579 | O   | GLN | B | 296 | 45.266 | 26.561 | 47.319 | 1.00 | 46.90 | O |
| ATOM | 2580 | N   | HIS | B | 297 | 46.720 | 24.925 | 46.819 | 1.00 | 45.46 | N |
| ATOM | 2581 | CA  | HIS | B | 297 | 47.074 | 24.681 | 48.207 | 1.00 | 44.39 | C |
| ATOM | 2582 | CB  | HIS | B | 297 | 45.902 | 23.970 | 48.908 | 1.00 | 38.04 | C |
| ATOM | 2583 | CG  | HIS | B | 297 | 45.998 | 23.949 | 50.403 | 1.00 | 36.49 | C |
| ATOM | 2584 | CD2 | HIS | B | 297 | 45.344 | 24.667 | 51.347 | 1.00 | 35.89 | C |
| ATOM | 2585 | ND1 | HIS | B | 297 | 46.832 | 23.091 | 51.085 | 1.00 | 35.38 | N |
| ATOM | 2586 | CE1 | HIS | B | 297 | 46.687 | 23.280 | 52.385 | 1.00 | 34.71 | C |
| ATOM | 2587 | NE2 | HIS | B | 297 | 45.791 | 24.232 | 52.571 | 1.00 | 35.52 | N |
| ATOM | 2588 | C   | HIS | B | 297 | 48.316 | 23.805 | 48.219 | 1.00 | 44.17 | C |
| ATOM | 2589 | O   | HIS | B | 297 | 48.547 | 23.033 | 47.288 | 1.00 | 44.16 | O |
| ATOM | 2590 | N   | GLN | B | 298 | 49.115 | 23.929 | 49.270 | 1.00 | 42.22 | N |
| ATOM | 2591 | CA  | GLN | B | 298 | 50.326 | 23.138 | 49.385 | 1.00 | 43.47 | C |
| ATOM | 2592 | CB  | GLN | B | 298 | 51.113 | 23.550 | 50.633 | 1.00 | 86.30 | C |
| ATOM | 2593 | CG  | GLN | B | 298 | 51.789 | 24.903 | 50.491 | 1.00 | 90.00 | C |
| ATOM | 2594 | CD  | GLN | B | 298 | 52.748 | 24.959 | 49.306 | 1.00 | 91.62 | C |
| ATOM | 2595 | OE1 | GLN | B | 298 | 53.198 | 26.037 | 48.907 | 1.00 | 93.07 | O |
| ATOM | 2596 | NE2 | GLN | B | 298 | 53.069 | 23.794 | 48.743 | 1.00 | 90.52 | N |
| ATOM | 2597 | C   | GLN | B | 298 | 50.046 | 21.644 | 49.416 | 1.00 | 42.43 | C |
| ATOM | 2598 | O   | GLN | B | 298 | 50.911 | 20.846 | 49.075 | 1.00 | 41.12 | O |
| ATOM | 2599 | N   | ARG | B | 299 | 48.836 | 21.271 | 49.822 | 1.00 | 48.89 | N |
| ATOM | 2600 | CA  | ARG | B | 299 | 48.463 | 19.860 | 49.888 | 1.00 | 48.46 | C |
| ATOM | 2601 | CB  | ARG | B | 299 | 47.470 | 19.626 | 51.027 | 1.00 | 51.92 | C |
| ATOM | 2602 | CG  | ARG | B | 299 | 48.019 | 19.973 | 52.387 | 1.00 | 51.25 | C |
| ATOM | 2603 | CD  | ARG | B | 299 | 49.395 | 19.368 | 52.565 | 1.00 | 53.30 | C |
| ATOM | 2604 | NE  | ARG | B | 299 | 49.929 | 19.636 | 53.891 | 1.00 | 55.11 | N |
| ATOM | 2605 | CZ  | ARG | B | 299 | 51.220 | 19.604 | 54.193 | 1.00 | 56.77 | C |
| ATOM | 2606 | NH1 | ARG | B | 299 | 52.116 | 19.317 | 53.253 | 1.00 | 56.41 | N |
| ATOM | 2607 | NH2 | ARG | B | 299 | 51.615 | 19.854 | 55.436 | 1.00 | 57.60 | N |
| ATOM | 2608 | C   | ARG | B | 299 | 47.859 | 19.358 | 48.579 | 1.00 | 48.17 | C |
| ATOM | 2609 | O   | ARG | B | 299 | 47.533 | 18.179 | 48.456 | 1.00 | 48.36 | O |
| ATOM | 2610 | N   | LEU | B | 300 | 47.708 | 20.256 | 47.609 | 1.00 | 42.69 | N |
| ATOM | 2611 | CA  | LEU | B | 300 | 47.155 | 19.887 | 46.312 | 1.00 | 42.70 | C |
| ATOM | 2612 | CB  | LEU | B | 300 | 45.943 | 20.769 | 45.971 | 1.00 | 38.87 | C |
| ATOM | 2613 | CG  | LEU | B | 300 | 44.557 | 20.304 | 46.443 | 1.00 | 37.74 | C |
| ATOM | 2614 | CD1 | LEU | B | 300 | 44.533 | 20.137 | 47.949 | 1.00 | 35.79 | C |
| ATOM | 2615 | CD2 | LEU | B | 300 | 43.512 | 21.312 | 45.995 | 1.00 | 37.28 | C |
| ATOM | 2616 | C   | LEU | B | 300 | 48.213 | 20.032 | 45.220 | 1.00 | 42.54 | C |
| ATOM | 2617 | O   | LEU | B | 300 | 49.003 | 20.961 | 45.243 | 1.00 | 43.84 | O |
| ATOM | 2618 | N   | VAL | B | 301 | 48.228 | 19.109 | 44.269 | 1.00 | 41.33 | N |
| ATOM | 2619 | CA  | VAL | B | 301 | 49.181 | 19.162 | 43.171 | 1.00 | 41.19 | C |
| ATOM | 2620 | CB  | VAL | B | 301 | 48.960 | 17.993 | 42.190 | 1.00 | 36.92 | C |
| ATOM | 2621 | CG1 | VAL | B | 301 | 49.814 | 18.193 | 40.946 | 1.00 | 36.51 | C |
| ATOM | 2622 | CG2 | VAL | B | 301 | 49.305 | 16.666 | 42.877 | 1.00 | 35.79 | C |
| ATOM | 2623 | C   | VAL | B | 301 | 49.041 | 20.479 | 42.411 | 1.00 | 41.64 | C |
| ATOM | 2624 | O   | VAL | B | 301 | 47.947 | 20.842 | 41.973 | 1.00 | 41.36 | O |

Figure 15

| ATOM | 2625 | N   | ARG | B | 302 | 50.156 | 21.186 | 42.255 | 1.00 | 48.52 | N |
| ATOM | 2626 | CA  | ARG | B | 302 | 50.166 | 22.471 | 41.569 | 1.00 | 49.95 | C |
| ATOM | 2627 | CB  | ARG | B | 302 | 51.318 | 23.334 | 42.094 | 1.00 | 66.39 | C |
| ATOM | 2628 | CG  | ARG | B | 302 | 51.487 | 24.641 | 41.346 | 1.00 | 69.57 | C |
| ATOM | 2629 | CD  | ARG | B | 302 | 52.760 | 25.366 | 41.751 | 1.00 | 72.14 | C |
| ATOM | 2630 | NE  | ARG | B | 302 | 53.028 | 26.492 | 40.858 | 1.00 | 74.72 | N |
| ATOM | 2631 | CZ  | ARG | B | 302 | 54.069 | 27.310 | 40.972 | 1.00 | 76.44 | C |
| ATOM | 2632 | NH1 | ARG | B | 302 | 54.951 | 27.137 | 41.947 | 1.00 | 76.49 | N |
| ATOM | 2633 | NH2 | ARG | B | 302 | 54.231 | 28.299 | 40.103 | 1.00 | 77.90 | N |
| ATOM | 2634 | C   | ARG | B | 302 | 50.286 | 22.356 | 40.050 | 1.00 | 50.09 | C |
| ATOM | 2635 | O   | ARG | B | 302 | 51.150 | 21.639 | 39.534 | 1.00 | 50.45 | O |
| ATOM | 2636 | N   | LEU | B | 303 | 49.419 | 23.076 | 39.343 | 1.00 | 44.31 | N |
| ATOM | 2637 | CA  | LEU | B | 303 | 49.430 | 23.082 | 37.882 | 1.00 | 44.04 | C |
| ATOM | 2638 | CB  | LEU | B | 303 | 48.032 | 23.355 | 37.329 | 1.00 | 42.30 | C |
| ATOM | 2639 | CG  | LEU | B | 303 | 48.035 | 23.628 | 35.821 | 1.00 | 41.28 | C |
| ATOM | 2640 | CD1 | LEU | B | 303 | 48.178 | 22.314 | 35.078 | 1.00 | 40.04 | C |
| ATOM | 2641 | CD2 | LEU | B | 303 | 46.766 | 24.340 | 35.406 | 1.00 | 40.57 | C |
| ATOM | 2642 | C   | LEU | B | 303 | 50.373 | 24.156 | 37.351 | 1.00 | 44.55 | C |
| ATOM | 2643 | O   | LEU | B | 303 | 50.375 | 25.287 | 37.837 | 1.00 | 44.58 | O |
| ATOM | 2644 | N   | TYR | B | 304 | 51.174 | 23.809 | 36.351 | 1.00 | 46.12 | N |
| ATOM | 2645 | CA  | TYR | B | 304 | 52.087 | 24.780 | 35.770 | 1.00 | 47.10 | C |
| ATOM | 2646 | CB  | TYR | B | 304 | 53.484 | 24.178 | 35.577 | 1.00 | 58.42 | C |
| ATOM | 2647 | CG  | TYR | B | 304 | 54.266 | 23.998 | 36.859 | 1.00 | 59.23 | C |
| ATOM | 2648 | CD1 | TYR | B | 304 | 53.955 | 24.733 | 37.990 | 1.00 | 60.51 | C |
| ATOM | 2649 | CE1 | TYR | B | 304 | 54.694 | 24.603 | 39.154 | 1.00 | 62.27 | C |
| ATOM | 2650 | CD2 | TYR | B | 304 | 55.344 | 23.123 | 36.924 | 1.00 | 60.23 | C |
| ATOM | 2651 | CE2 | TYR | B | 304 | 56.092 | 22.987 | 38.081 | 1.00 | 60.73 | C |
| ATOM | 2652 | CZ  | TYR | B | 304 | 55.760 | 23.731 | 39.194 | 1.00 | 61.14 | C |
| ATOM | 2653 | OH  | TYR | B | 304 | 56.483 | 23.605 | 40.354 | 1.00 | 62.32 | O |
| ATOM | 2654 | C   | TYR | B | 304 | 51.577 | 25.305 | 34.431 | 1.00 | 47.22 | C |
| ATOM | 2655 | O   | TYR | B | 304 | 51.549 | 26.508 | 34.195 | 1.00 | 47.57 | O |
| ATOM | 2656 | N   | ALA | B | 305 | 51.152 | 24.404 | 33.557 | 1.00 | 42.73 | N |
| ATOM | 2657 | CA  | ALA | B | 305 | 50.681 | 24.826 | 32.253 | 1.00 | 43.16 | C |
| ATOM | 2658 | CB  | ALA | B | 305 | 51.857 | 25.346 | 31.428 | 1.00 | 49.81 | C |
| ATOM | 2659 | C   | ALA | B | 305 | 49.993 | 23.706 | 31.501 | 1.00 | 43.56 | C |
| ATOM | 2660 | O   | ALA | B | 305 | 49.919 | 22.566 | 31.970 | 1.00 | 43.15 | O |
| ATOM | 2661 | N   | VAL | B | 306 | 49.497 | 24.051 | 30.320 | 1.00 | 51.71 | N |
| ATOM | 2662 | CA  | VAL | B | 306 | 48.820 | 23.107 | 29.452 | 1.00 | 52.73 | C |
| ATOM | 2663 | CB  | VAL | B | 306 | 47.285 | 23.239 | 29.550 | 1.00 | 51.97 | C |
| ATOM | 2664 | CG1 | VAL | B | 306 | 46.827 | 23.089 | 30.996 | 1.00 | 50.79 | C |
| ATOM | 2665 | CG2 | VAL | B | 306 | 46.849 | 24.578 | 28.976 | 1.00 | 51.59 | C |
| ATOM | 2666 | C   | VAL | B | 306 | 49.221 | 23.418 | 28.017 | 1.00 | 54.07 | C |
| ATOM | 2667 | O   | VAL | B | 306 | 49.620 | 24.542 | 27.709 | 1.00 | 55.03 | O |
| ATOM | 2668 | N   | VAL | B | 307 | 49.125 | 22.414 | 27.153 | 1.00 | 46.62 | N |
| ATOM | 2669 | CA  | VAL | B | 307 | 49.430 | 22.571 | 25.736 | 1.00 | 47.62 | C |
| ATOM | 2670 | CB  | VAL | B | 307 | 50.633 | 21.696 | 25.307 | 1.00 | 49.18 | C |
| ATOM | 2671 | CG1 | VAL | B | 307 | 50.856 | 21.808 | 23.809 | 1.00 | 48.34 | C |
| ATOM | 2672 | CG2 | VAL | B | 307 | 51.879 | 22.147 | 26.046 | 1.00 | 49.33 | C |
| ATOM | 2673 | C   | VAL | B | 307 | 48.167 | 22.137 | 24.992 | 1.00 | 48.34 | C |
| ATOM | 2674 | O   | VAL | B | 307 | 47.790 | 20.964 | 25.007 | 1.00 | 47.72 | O |
| ATOM | 2675 | N   | THR | B | 308 | 47.523 | 23.099 | 24.341 | 1.00 | 68.73 | N |
| ATOM | 2676 | CA  | THR | B | 308 | 46.270 | 22.867 | 23.625 | 1.00 | 70.31 | C |
| ATOM | 2677 | CB  | THR | B | 308 | 45.481 | 24.179 | 23.516 | 1.00 | 57.18 | C |
| ATOM | 2678 | OG1 | THR | B | 308 | 46.279 | 25.165 | 22.850 | 1.00 | 57.96 | O |
| ATOM | 2679 | CG2 | THR | B | 308 | 45.119 | 24.687 | 24.904 | 1.00 | 56.60 | C |
| ATOM | 2680 | C   | THR | B | 308 | 46.322 | 22.218 | 22.243 | 1.00 | 70.88 | C |
| ATOM | 2681 | O   | THR | B | 308 | 45.275 | 21.955 | 21.649 | 1.00 | 71.22 | O |
| ATOM | 2682 | N   | GLN | B | 309 | 47.519 | 21.962 | 21.727 | 1.00 | 50.20 | N |
| ATOM | 2683 | CA  | GLN | B | 309 | 47.643 | 21.310 | 20.428 | 1.00 | 50.32 | C |
| ATOM | 2684 | CB  | GLN | B | 309 | 48.731 | 21.973 | 19.583 | 1.00 | 87.44 | C |

Figure 15

```
ATOM   2685  CG   GLN B 309      48.208  23.099  18.721  1.00 90.13           C
ATOM   2686  CD   GLN B 309      47.045  22.653  17.857  1.00 91.69           C
ATOM   2687  OE1  GLN B 309      47.188  21.754  17.026  1.00 92.69           O
ATOM   2688  NE2  GLN B 309      45.881  23.276  18.051  1.00 91.82           N
ATOM   2689  C    GLN B 309      47.953  19.829  20.583  1.00 49.44           C
ATOM   2690  O    GLN B 309      48.755  19.441  21.430  1.00 49.59           O
ATOM   2691  N    GLU B 310      47.317  19.010  19.751  1.00 60.83           N
ATOM   2692  CA   GLU B 310      47.503  17.563  19.784  1.00 59.91           C
ATOM   2693  CB   GLU B 310      46.672  16.903  18.681  1.00 86.64           C
ATOM   2694  CG   GLU B 310      45.307  17.541  18.445  1.00 89.10           C
ATOM   2695  CD   GLU B 310      44.294  17.214  19.530  1.00 89.74           C
ATOM   2696  OE1  GLU B 310      43.960  16.021  19.696  1.00 90.82           O
ATOM   2697  OE2  GLU B 310      43.828  18.151  20.212  1.00 90.04           O
ATOM   2698  C    GLU B 310      48.972  17.184  19.590  1.00 58.48           C
ATOM   2699  O    GLU B 310      49.627  17.654  18.658  1.00 58.35           O
ATOM   2700  N    PRO B 311      49.506  16.329  20.478  1.00 57.52           N
ATOM   2701  CD   PRO B 311      50.822  15.673  20.367  1.00 54.22           C
ATOM   2702  CA   PRO B 311      48.735  15.774  21.593  1.00 56.11           C
ATOM   2703  CB   PRO B 311      49.526  14.526  21.969  1.00 53.45           C
ATOM   2704  CG   PRO B 311      50.945  14.952  21.697  1.00 55.12           C
ATOM   2705  C    PRO B 311      48.647  16.781  22.735  1.00 54.42           C
ATOM   2706  O    PRO B 311      49.616  17.479  23.029  1.00 54.29           O
ATOM   2707  N    ILE B 312      47.476  16.867  23.357  1.00 44.18           N
ATOM   2708  CA   ILE B 312      47.258  17.792  24.465  1.00 41.83           C
ATOM   2709  CB   ILE B 312      45.794  17.730  24.956  1.00 52.41           C
ATOM   2710  CG2  ILE B 312      45.566  18.770  26.043  1.00 53.20           C
ATOM   2711  CG1  ILE B 312      44.841  17.976  23.790  1.00 53.47           C
ATOM   2712  CD1  ILE B 312      44.995  19.335  23.166  1.00 54.92           C
ATOM   2713  C    ILE B 312      48.182  17.459  25.644  1.00 39.80           C
ATOM   2714  O    ILE B 312      48.479  16.292  25.914  1.00 37.54           O
ATOM   2715  N    TYR B 313      48.627  18.500  26.341  1.00 37.43           N
ATOM   2716  CA   TYR B 313      49.518  18.338  27.485  1.00 36.69           C
ATOM   2717  CB   TYR B 313      50.920  18.898  27.182  1.00 39.47           C
ATOM   2718  CG   TYR B 313      51.850  18.042  26.350  1.00 38.65           C
ATOM   2719  CD1  TYR B 313      51.449  16.815  25.847  1.00 38.80           C
ATOM   2720  CE1  TYR B 313      52.320  16.030  25.093  1.00 39.22           C
ATOM   2721  CD2  TYR B 313      53.151  18.469  26.077  1.00 38.65           C
ATOM   2722  CE2  TYR B 313      54.028  17.691  25.326  1.00 37.79           C
ATOM   2723  CZ   TYR B 313      53.607  16.474  24.838  1.00 39.01           C
ATOM   2724  OH   TYR B 313      54.463  15.690  24.089  1.00 40.21           O
ATOM   2725  C    TYR B 313      49.023  19.067  28.727  1.00 36.12           C
ATOM   2726  O    TYR B 313      48.504  20.184  28.652  1.00 35.70           O
ATOM   2727  N    ILE B 314      49.192  18.422  29.872  1.00 36.43           N
ATOM   2728  CA   ILE B 314      48.873  19.044  31.146  1.00 35.60           C
ATOM   2729  CB   ILE B 314      47.746  18.321  31.901  1.00 41.49           C
ATOM   2730  CG2  ILE B 314      47.543  18.977  33.263  1.00 39.64           C
ATOM   2731  CG1  ILE B 314      46.449  18.389  31.090  1.00 41.67           C
ATOM   2732  CD1  ILE B 314      45.282  17.662  31.728  1.00 40.97           C
ATOM   2733  C    ILE B 314      50.186  18.906  31.910  1.00 35.06           C
ATOM   2734  O    ILE B 314      50.716  17.804  32.050  1.00 35.66           O
ATOM   2735  N    ILE B 315      50.724  20.024  32.381  1.00 39.18           N
ATOM   2736  CA   ILE B 315      51.994  20.005  33.094  1.00 39.42           C
ATOM   2737  CB   ILE B 315      53.059  20.919  32.393  1.00 38.44           C
ATOM   2738  CG2  ILE B 315      54.432  20.716  33.023  1.00 38.15           C
ATOM   2739  CG1  ILE B 315      53.135  20.604  30.898  1.00 38.59           C
ATOM   2740  CD1  ILE B 315      52.253  21.500  30.041  1.00 39.98           C
ATOM   2741  C    ILE B 315      51.847  20.475  34.530  1.00 38.81           C
ATOM   2742  O    ILE B 315      51.316  21.553  34.791  1.00 39.12           O
ATOM   2743  N    THR B 316      52.326  19.660  35.463  1.00 36.31           N
ATOM   2744  CA   THR B 316      52.268  20.003  36.876  1.00 35.84           C
```

Figure 15

```
ATOM   2745  CB   THR B 316      51.292  19.106  37.639  1.00 36.91           C
ATOM   2746  OG1  THR B 316      51.844  17.781  37.731  1.00 36.39           O
ATOM   2747  CG2  THR B 316      49.936  19.067  36.935  1.00 35.24           C
ATOM   2748  C    THR B 316      53.636  19.780  37.498  1.00 36.52           C
ATOM   2749  O    THR B 316      54.538  19.235  36.857  1.00 35.80           O
ATOM   2750  N    GLU B 317      53.780  20.200  38.753  1.00 38.47           N
ATOM   2751  CA   GLU B 317      55.024  19.997  39.480  1.00 38.73           C
ATOM   2752  CB   GLU B 317      54.883  20.457  40.935  1.00 40.62           C
ATOM   2753  CG   GLU B 317      53.914  19.606  41.771  1.00 41.79           C
ATOM   2754  CD   GLU B 317      53.742  20.132  43.184  1.00 44.18           C
ATOM   2755  OE1  GLU B 317      54.762  20.323  43.887  1.00 47.12           O
ATOM   2756  OE2  GLU B 317      52.587  20.356  43.599  1.00 44.42           O
ATOM   2757  C    GLU B 317      55.287  18.491  39.453  1.00 38.80           C
ATOM   2758  O    GLU B 317      54.372  17.689  39.237  1.00 38.14           O
ATOM   2759  N    TYR B 318      56.537  18.116  39.683  1.00 36.25           N
ATOM   2760  CA   TYR B 318      56.930  16.719  39.681  1.00 35.90           C
ATOM   2761  CB   TYR B 318      58.344  16.598  39.107  1.00 38.19           C
ATOM   2762  CG   TYR B 318      58.858  15.184  39.038  1.00 38.75           C
ATOM   2763  CD1  TYR B 318      58.302  14.269  38.154  1.00 39.77           C
ATOM   2764  CE1  TYR B 318      58.756  12.961  38.100  1.00 40.20           C
ATOM   2765  CD2  TYR B 318      59.887  14.754  39.870  1.00 37.86           C
ATOM   2766  CE2  TYR B 318      60.344  13.456  39.826  1.00 37.11           C
ATOM   2767  CZ   TYR B 318      59.777  12.567  38.942  1.00 39.05           C
ATOM   2768  OH   TYR B 318      60.225  11.277  38.884  1.00 41.32           O
ATOM   2769  C    TYR B 318      56.877  16.112  41.093  1.00 35.78           C
ATOM   2770  O    TYR B 318      57.268  16.750  42.069  1.00 34.72           O
ATOM   2771  N    MET B 319      56.369  14.888  41.193  1.00 35.95           N
ATOM   2772  CA   MET B 319      56.297  14.198  42.476  1.00 37.17           C
ATOM   2773  CB   MET B 319      54.854  13.792  42.802  1.00 39.60           C
ATOM   2774  CG   MET B 319      53.898  14.969  43.029  1.00 40.05           C
ATOM   2775  SD   MET B 319      54.384  16.086  44.367  1.00 43.26           S
ATOM   2776  CE   MET B 319      53.602  15.239  45.793  1.00 42.03           C
ATOM   2777  C    MET B 319      57.200  12.968  42.409  1.00 37.31           C
ATOM   2778  O    MET B 319      56.825  11.925  41.878  1.00 36.88           O
ATOM   2779  N    GLU B 320      58.394  13.123  42.963  1.00 39.62           N
ATOM   2780  CA   GLU B 320      59.434  12.103  42.991  1.00 40.18           C
ATOM   2781  CB   GLU B 320      60.590  12.593  43.866  1.00 65.19           C
ATOM   2782  CG   GLU B 320      61.866  11.784  43.714  1.00 68.85           C
ATOM   2783  CD   GLU B 320      62.124  11.378  42.278  1.00 70.04           C
ATOM   2784  OE1  GLU B 320      62.267  12.273  41.415  1.00 72.68           O
ATOM   2785  OE2  GLU B 320      62.177  10.165  42.011  1.00 71.22           O
ATOM   2786  C    GLU B 320      59.072  10.676  43.408  1.00 40.07           C
ATOM   2787  O    GLU B 320      59.659   9.725  42.897  1.00 40.22           O
ATOM   2788  N    ASN B 321      58.121  10.506  44.319  1.00 42.10           N
ATOM   2789  CA   ASN B 321      57.769   9.160  44.755  1.00 41.80           C
ATOM   2790  CB   ASN B 321      57.798   9.090  46.288  1.00 36.05           C
ATOM   2791  CG   ASN B 321      59.221   9.148  46.836  1.00 35.96           C
ATOM   2792  OD1  ASN B 321      60.065   8.334  46.468  1.00 33.93           O
ATOM   2793  ND2  ASN B 321      59.489  10.112  47.704  1.00 35.07           N
ATOM   2794  C    ASN B 321      56.448   8.625  44.213  1.00 42.15           C
ATOM   2795  O    ASN B 321      55.961   7.583  44.654  1.00 41.91           O
ATOM   2796  N    GLY B 322      55.882   9.342  43.248  1.00 37.86           N
ATOM   2797  CA   GLY B 322      54.638   8.929  42.628  1.00 37.52           C
ATOM   2798  C    GLY B 322      53.408   8.770  43.509  1.00 37.89           C
ATOM   2799  O    GLY B 322      53.216   9.490  44.494  1.00 37.06           O
ATOM   2800  N    SER B 323      52.570   7.808  43.128  1.00 38.11           N
ATOM   2801  CA   SER B 323      51.326   7.508  43.822  1.00 38.61           C
ATOM   2802  CB   SER B 323      50.429   6.649  42.930  1.00 46.44           C
ATOM   2803  OG   SER B 323      49.497   5.919  43.703  1.00 49.77           O
ATOM   2804  C    SER B 323      51.546   6.813  45.149  1.00 38.54           C
```

Figure 15

| ATOM | 2805 | O   | SER | B | 323 | 52.298 | 5.845  | 45.239 | 1.00 | 37.90 | O |
|------|------|-----|-----|---|-----|--------|--------|--------|------|-------|---|
| ATOM | 2806 | N   | LEU | B | 324 | 50.865 | 7.303  | 46.179 | 1.00 | 38.26 | N |
| ATOM | 2807 | CA  | LEU | B | 324 | 51.003 | 6.741  | 47.519 | 1.00 | 38.42 | C |
| ATOM | 2808 | CB  | LEU | B | 324 | 50.068 | 7.484  | 48.480 | 1.00 | 35.00 | C |
| ATOM | 2809 | CG  | LEU | B | 324 | 49.923 | 6.994  | 49.925 | 1.00 | 34.55 | C |
| ATOM | 2810 | CD1 | LEU | B | 324 | 51.212 | 7.215  | 50.708 | 1.00 | 31.86 | C |
| ATOM | 2811 | CD2 | LEU | B | 324 | 48.764 | 7.755  | 50.575 | 1.00 | 33.39 | C |
| ATOM | 2812 | C   | LEU | B | 324 | 50.739 | 5.230  | 47.578 | 1.00 | 38.05 | C |
| ATOM | 2813 | O   | LEU | B | 324 | 51.433 | 4.505  | 48.274 | 1.00 | 38.43 | O |
| ATOM | 2814 | N   | VAL | B | 325 | 49.742 | 4.752  | 46.844 | 1.00 | 41.26 | N |
| ATOM | 2815 | CA  | VAL | B | 325 | 49.430 | 3.325  | 46.871 | 1.00 | 41.11 | C |
| ATOM | 2816 | CB  | VAL | B | 325 | 48.162 | 3.002  | 46.023 | 1.00 | 31.57 | C |
| ATOM | 2817 | CG1 | VAL | B | 325 | 48.495 | 2.998  | 44.547 | 1.00 | 29.40 | C |
| ATOM | 2818 | CG2 | VAL | B | 325 | 47.563 | 1.667  | 46.466 | 1.00 | 30.66 | C |
| ATOM | 2819 | C   | VAL | B | 325 | 50.606 | 2.466  | 46.406 | 1.00 | 42.04 | C |
| ATOM | 2820 | O   | VAL | B | 325 | 50.722 | 1.303  | 46.808 | 1.00 | 42.46 | O |
| ATOM | 2821 | N   | ASP | B | 326 | 51.478 | 3.031  | 45.571 | 1.00 | 41.83 | N |
| ATOM | 2822 | CA  | ASP | B | 326 | 52.656 | 2.299  | 45.090 | 1.00 | 42.84 | C |
| ATOM | 2823 | CB  | ASP | B | 326 | 53.046 | 2.717  | 43.664 | 1.00 | 41.88 | C |
| ATOM | 2824 | CG  | ASP | B | 326 | 51.994 | 2.358  | 42.640 | 1.00 | 42.36 | C |
| ATOM | 2825 | OD1 | ASP | B | 326 | 51.449 | 1.242  | 42.710 | 1.00 | 43.66 | O |
| ATOM | 2826 | OD2 | ASP | B | 326 | 51.716 | 3.187  | 41.754 | 1.00 | 44.54 | O |
| ATOM | 2827 | C   | ASP | B | 326 | 53.851 | 2.533  | 46.004 | 1.00 | 43.16 | C |
| ATOM | 2828 | O   | ASP | B | 326 | 54.620 | 1.612  | 46.274 | 1.00 | 43.57 | O |
| ATOM | 2829 | N   | PHE | B | 327 | 54.012 | 3.763  | 46.479 | 1.00 | 42.99 | N |
| ATOM | 2830 | CA  | PHE | B | 327 | 55.129 | 4.078  | 47.355 | 1.00 | 43.65 | C |
| ATOM | 2831 | CB  | PHE | B | 327 | 55.148 | 5.561  | 47.708 | 1.00 | 43.44 | C |
| ATOM | 2832 | CG  | PHE | B | 327 | 56.185 | 5.914  | 48.738 | 1.00 | 43.22 | C |
| ATOM | 2833 | CD1 | PHE | B | 327 | 57.535 | 5.769  | 48.458 | 1.00 | 44.07 | C |
| ATOM | 2834 | CD2 | PHE | B | 327 | 55.814 | 6.361  | 49.990 | 1.00 | 44.26 | C |
| ATOM | 2835 | CE1 | PHE | B | 327 | 58.495 | 6.061  | 49.413 | 1.00 | 43.29 | C |
| ATOM | 2836 | CE2 | PHE | B | 327 | 56.770 | 6.655  | 50.950 | 1.00 | 44.47 | C |
| ATOM | 2837 | CZ  | PHE | B | 327 | 58.112 | 6.503  | 50.656 | 1.00 | 43.23 | C |
| ATOM | 2838 | C   | PHE | B | 327 | 55.097 | 3.280  | 48.652 | 1.00 | 45.17 | C |
| ATOM | 2839 | O   | PHE | B | 327 | 56.143 | 2.846  | 49.150 | 1.00 | 45.71 | O |
| ATOM | 2840 | N   | LEU | B | 328 | 53.902 | 3.112  | 49.208 | 1.00 | 38.53 | N |
| ATOM | 2841 | CA  | LEU | B | 328 | 53.734 | 2.382  | 50.453 | 1.00 | 39.42 | C |
| ATOM | 2842 | CB  | LEU | B | 328 | 52.251 | 2.314  | 50.823 | 1.00 | 45.79 | C |
| ATOM | 2843 | CG  | LEU | B | 328 | 51.573 | 3.622  | 51.221 | 1.00 | 45.11 | C |
| ATOM | 2844 | CD1 | LEU | B | 328 | 50.073 | 3.454  | 51.139 | 1.00 | 45.72 | C |
| ATOM | 2845 | CD2 | LEU | B | 328 | 52.004 | 4.015  | 52.624 | 1.00 | 45.31 | C |
| ATOM | 2846 | C   | LEU | B | 328 | 54.294 | 0.972  | 50.358 | 1.00 | 40.31 | C |
| ATOM | 2847 | O   | LEU | B | 328 | 54.743 | 0.405  | 51.354 | 1.00 | 39.56 | O |
| ATOM | 2848 | N   | LYS | B | 329 | 54.265 | 0.413  | 49.154 | 1.00 | 57.84 | N |
| ATOM | 2849 | CA  | LYS | B | 329 | 54.749 | -0.943 | 48.924 | 1.00 | 59.37 | C |
| ATOM | 2850 | CB  | LYS | B | 329 | 54.059 | -1.548 | 47.698 | 1.00 | 57.78 | C |
| ATOM | 2851 | CG  | LYS | B | 329 | 52.540 | -1.711 | 47.824 | 1.00 | 58.59 | C |
| ATOM | 2852 | CD  | LYS | B | 329 | 51.969 | -2.365 | 46.564 | 1.00 | 58.15 | C |
| ATOM | 2853 | CE  | LYS | B | 329 | 50.470 | -2.607 | 46.660 | 1.00 | 58.55 | C |
| ATOM | 2854 | NZ  | LYS | B | 329 | 49.688 | -1.339 | 46.720 | 1.00 | 59.61 | N |
| ATOM | 2855 | C   | LYS | B | 329 | 56.263 | -1.048 | 48.745 | 1.00 | 59.88 | C |
| ATOM | 2856 | O   | LYS | B | 329 | 56.825 | -2.130 | 48.899 | 1.00 | 60.56 | O |
| ATOM | 2857 | N   | THR | B | 330 | 56.921 | 0.065  | 48.424 | 1.00 | 48.52 | N |
| ATOM | 2858 | CA  | THR | B | 330 | 58.369 | 0.056  | 48.223 | 1.00 | 48.68 | C |
| ATOM | 2859 | CB  | THR | B | 330 | 58.885 | 1.415  | 47.673 | 1.00 | 45.47 | C |
| ATOM | 2860 | OG1 | THR | B | 330 | 58.841 | 2.402  | 48.711 | 1.00 | 45.12 | O |
| ATOM | 2861 | CG2 | THR | B | 330 | 58.042 | 1.879  | 46.501 | 1.00 | 44.95 | C |
| ATOM | 2862 | C   | THR | B | 330 | 59.117 | -0.223 | 49.525 | 1.00 | 49.20 | C |
| ATOM | 2863 | O   | THR | B | 330 | 58.596 | 0.015  | 50.613 | 1.00 | 49.10 | O |
| ATOM | 2864 | N   | PRO | B | 331 | 60.355 | -0.739 | 49.424 | 1.00 | 51.38 | N |

Figure 15

```
ATOM   2865  CD   PRO B 331      61.010  -1.216  48.191  1.00 60.29           C
ATOM   2866  CA   PRO B 331      61.179  -1.043  50.599  1.00 51.81           C
ATOM   2867  CB   PRO B 331      62.539  -1.363  49.985  1.00 60.53           C
ATOM   2868  CG   PRO B 331      62.149  -2.087  48.731  1.00 60.06           C
ATOM   2869  C    PRO B 331      61.229   0.145  51.552  1.00 52.30           C
ATOM   2870  O    PRO B 331      61.323  -0.033  52.762  1.00 52.88           O
ATOM   2871  N    SER B 332      61.160   1.357  51.003  1.00 55.30           N
ATOM   2872  CA   SER B 332      61.175   2.561  51.830  1.00 55.79           C
ATOM   2873  CB   SER B 332      61.489   3.804  50.992  1.00 55.44           C
ATOM   2874  OG   SER B 332      62.848   3.827  50.603  1.00 57.09           O
ATOM   2875  C    SER B 332      59.828   2.752  52.509  1.00 55.91           C
ATOM   2876  O    SER B 332      59.759   3.077  53.691  1.00 56.30           O
ATOM   2877  N    GLY B 333      58.755   2.564  51.749  1.00 50.90           N
ATOM   2878  CA   GLY B 333      57.433   2.728  52.315  1.00 50.79           C
ATOM   2879  C    GLY B 333      57.213   1.731  53.427  1.00 50.51           C
ATOM   2880  O    GLY B 333      56.905   2.103  54.558  1.00 50.27           O
ATOM   2881  N    ILE B 334      57.376   0.454  53.095  1.00 51.52           N
ATOM   2882  CA   ILE B 334      57.205  -0.641  54.046  1.00 51.64           C
ATOM   2883  CB   ILE B 334      57.830  -1.940  53.502  1.00 61.71           C
ATOM   2884  CG2  ILE B 334      57.970  -2.959  54.621  1.00 63.23           C
ATOM   2885  CG1  ILE B 334      56.974  -2.491  52.370  1.00 61.75           C
ATOM   2886  CD1  ILE B 334      55.556  -2.805  52.783  1.00 62.75           C
ATOM   2887  C    ILE B 334      57.829  -0.355  55.405  1.00 50.87           C
ATOM   2888  O    ILE B 334      57.345  -0.824  56.427  1.00 50.71           O
ATOM   2889  N    LYS B 335      58.893   0.439  55.413  1.00 58.93           N
ATOM   2890  CA   LYS B 335      59.596   0.764  56.646  1.00 58.45           C
ATOM   2891  CB   LYS B 335      61.094   0.905  56.366  1.00 65.45           C
ATOM   2892  CG   LYS B 335      61.727  -0.324  55.718  1.00 66.80           C
ATOM   2893  CD   LYS B 335      63.244  -0.165  55.608  1.00 68.99           C
ATOM   2894  CE   LYS B 335      63.899  -1.397  55.000  1.00 69.89           C
ATOM   2895  NZ   LYS B 335      65.384  -1.381  55.182  1.00 71.54           N
ATOM   2896  C    LYS B 335      59.101   2.011  57.367  1.00 57.55           C
ATOM   2897  O    LYS B 335      59.673   2.400  58.386  1.00 57.61           O
ATOM   2898  N    LEU B 336      58.046   2.640  56.856  1.00 51.10           N
ATOM   2899  CA   LEU B 336      57.527   3.844  57.505  1.00 49.91           C
ATOM   2900  CB   LEU B 336      56.447   4.502  56.640  1.00 43.32           C
ATOM   2901  CG   LEU B 336      56.920   5.038  55.285  1.00 42.23           C
ATOM   2902  CD1  LEU B 336      55.790   5.758  54.602  1.00 41.98           C
ATOM   2903  CD2  LEU B 336      58.099   5.985  55.486  1.00 42.26           C
ATOM   2904  C    LEU B 336      56.955   3.520  58.881  1.00 50.01           C
ATOM   2905  O    LEU B 336      56.337   2.472  59.083  1.00 50.14           O
ATOM   2906  N    THR B 337      57.176   4.424  59.831  1.00 50.93           N
ATOM   2907  CA   THR B 337      56.678   4.235  61.185  1.00 50.51           C
ATOM   2908  CB   THR B 337      57.461   5.119  62.208  1.00 51.51           C
ATOM   2909  OG1  THR B 337      57.295   6.509  61.888  1.00 50.14           O
ATOM   2910  CG2  THR B 337      58.955   4.779  62.171  1.00 51.11           C
ATOM   2911  C    THR B 337      55.205   4.622  61.205  1.00 49.67           C
ATOM   2912  O    THR B 337      54.729   5.291  60.291  1.00 50.14           O
ATOM   2913  N    ILE B 338      54.486   4.199  62.236  1.00 40.50           N
ATOM   2914  CA   ILE B 338      53.073   4.527  62.345  1.00 39.53           C
ATOM   2915  CB   ILE B 338      52.411   3.785  63.542  1.00 38.44           C
ATOM   2916  CG2  ILE B 338      53.140   4.118  64.831  1.00 37.54           C
ATOM   2917  CG1  ILE B 338      50.926   4.158  63.638  1.00 37.10           C
ATOM   2918  CD1  ILE B 338      50.059   3.605  62.513  1.00 35.50           C
ATOM   2919  C    ILE B 338      52.941   6.036  62.519  1.00 39.03           C
ATOM   2920  O    ILE B 338      51.950   6.629  62.097  1.00 38.11           O
ATOM   2921  N    ASN B 339      53.954   6.640  63.143  1.00 41.79           N
ATOM   2922  CA   ASN B 339      54.018   8.088  63.368  1.00 41.98           C
ATOM   2923  CB   ASN B 339      55.310   8.463  64.116  1.00 51.94           C
ATOM   2924  CG   ASN B 339      55.243   8.180  65.609  1.00 52.87           C
```

Figure 15

```
ATOM   2925  OD1 ASN B 339      54.681    8.959   66.379  1.00 51.41           O
ATOM   2926  ND2 ASN B 339      55.824    7.059   66.021  1.00 52.93           N
ATOM   2927  C   ASN B 339      54.033    8.803   62.012  1.00 41.87           C
ATOM   2928  O   ASN B 339      53.256    9.715   61.771  1.00 41.71           O
ATOM   2929  N   LYS B 340      54.946    8.383   61.141  1.00 45.63           N
ATOM   2930  CA  LYS B 340      55.079    8.972   59.810  1.00 45.49           C
ATOM   2931  CB  LYS B 340      56.275    8.352   59.077  1.00 50.45           C
ATOM   2932  CG  LYS B 340      56.538    8.945   57.704  1.00 52.37           C
ATOM   2933  CD  LYS B 340      56.814   10.444   57.805  1.00 54.13           C
ATOM   2934  CE  LYS B 340      56.708   11.128   56.455  1.00 55.24           C
ATOM   2935  NZ  LYS B 340      56.663   12.614   56.601  1.00 57.54           N
ATOM   2936  C   LYS B 340      53.807    8.749   58.994  1.00 44.72           C
ATOM   2937  O   LYS B 340      53.304    9.668   58.353  1.00 45.41           O
ATOM   2938  N   LEU B 341      53.286    7.529   59.026  1.00 39.49           N
ATOM   2939  CA  LEU B 341      52.075    7.204   58.290  1.00 39.46           C
ATOM   2940  CB  LEU B 341      51.719    5.729   58.508  1.00 36.20           C
ATOM   2941  CG  LEU B 341      52.756    4.754   57.931  1.00 35.56           C
ATOM   2942  CD1 LEU B 341      52.321    3.314   58.174  1.00 33.84           C
ATOM   2943  CD2 LEU B 341      52.920    5.027   56.441  1.00 34.67           C
ATOM   2944  C   LEU B 341      50.922    8.101   58.732  1.00 39.91           C
ATOM   2945  O   LEU B 341      50.086    8.517   57.916  1.00 39.99           O
ATOM   2946  N   LEU B 342      50.893    8.395   60.029  1.00 39.04           N
ATOM   2947  CA  LEU B 342      49.869    9.244   60.618  1.00 39.25           C
ATOM   2948  CB  LEU B 342      49.962    9.192   62.147  1.00 52.08           C
ATOM   2949  CG  LEU B 342      48.694    8.759   62.895  1.00 53.69           C
ATOM   2950  CD1 LEU B 342      47.552    9.648   62.461  1.00 55.26           C
ATOM   2951  CD2 LEU B 342      48.361    7.299   62.607  1.00 52.47           C
ATOM   2952  C   LEU B 342      50.043   10.686   60.142  1.00 39.23           C
ATOM   2953  O   LEU B 342      49.056   11.403   59.947  1.00 38.63           O
ATOM   2954  N   ASP B 343      51.294   11.117   59.981  1.00 36.60           N
ATOM   2955  CA  ASP B 343      51.552   12.469   59.510  1.00 37.01           C
ATOM   2956  CB  ASP B 343      53.031   12.833   59.630  1.00 69.22           C
ATOM   2957  CG  ASP B 343      53.307   14.271   59.201  1.00 73.15           C
ATOM   2958  OD1 ASP B 343      52.542   15.163   59.634  1.00 74.70           O
ATOM   2959  OD2 ASP B 343      54.282   14.512   58.444  1.00 74.39           O
ATOM   2960  C   ASP B 343      51.119   12.570   58.051  1.00 35.78           C
ATOM   2961  O   ASP B 343      50.567   13.584   57.626  1.00 34.86           O
ATOM   2962  N   MET B 344      51.372   11.521   57.280  1.00 38.17           N
ATOM   2963  CA  MET B 344      50.962   11.530   55.885  1.00 37.65           C
ATOM   2964  CB  MET B 344      51.382   10.231   55.192  1.00 44.24           C
ATOM   2965  CG  MET B 344      52.886    9.972   55.223  1.00 46.30           C
ATOM   2966  SD  MET B 344      53.350    8.601   54.158  1.00 49.44           S
ATOM   2967  CE  MET B 344      54.433    9.418   52.989  1.00 48.97           C
ATOM   2968  C   MET B 344      49.438   11.689   55.827  1.00 36.54           C
ATOM   2969  O   MET B 344      48.928   12.524   55.096  1.00 35.90           O
ATOM   2970  N   ALA B 345      48.728   10.891   56.626  1.00 38.13           N
ATOM   2971  CA  ALA B 345      47.273   10.921   56.673  1.00 36.46           C
ATOM   2972  CB  ALA B 345      46.774    9.882   57.654  1.00 34.87           C
ATOM   2973  C   ALA B 345      46.743   12.300   57.052  1.00 36.17           C
ATOM   2974  O   ALA B 345      45.740   12.758   56.499  1.00 35.07           O
ATOM   2975  N   ALA B 346      47.408   12.960   57.998  1.00 37.29           N
ATOM   2976  CA  ALA B 346      46.987   14.293   58.416  1.00 37.66           C
ATOM   2977  CB  ALA B 346      47.838   14.783   59.593  1.00 31.73           C
ATOM   2978  C   ALA B 346      47.100   15.261   57.248  1.00 37.95           C
ATOM   2979  O   ALA B 346      46.217   16.092   57.030  1.00 38.33           O
ATOM   2980  N   GLN B 347      48.191   15.162   56.494  1.00 35.14           N
ATOM   2981  CA  GLN B 347      48.381   16.050   55.343  1.00 36.01           C
ATOM   2982  CB  GLN B 347      49.739   15.783   54.680  1.00 43.95           C
ATOM   2983  CG  GLN B 347      50.924   16.251   55.524  1.00 46.14           C
ATOM   2984  CD  GLN B 347      52.259   15.772   54.984  1.00 48.87           C
```

Figure 15

| | | | | | | | | | | |
|---|---|---|---|---|---|---|---|---|---|---|
| ATOM | 2985 | OE1 | GLN | B | 347 | 53.321 | 16.183 | 55.463 | 1.00 52.09 | O |
| ATOM | 2986 | NE2 | GLN | B | 347 | 52.217 | 14.903 | 53.991 | 1.00 48.73 | N |
| ATOM | 2987 | C | GLN | B | 347 | 47.259 | 15.882 | 54.314 | 1.00 34.58 | C |
| ATOM | 2988 | O | GLN | B | 347 | 46.812 | 16.863 | 53.710 | 1.00 35.22 | O |
| ATOM | 2989 | N | ILE | B | 348 | 46.812 | 14.645 | 54.116 | 1.00 29.36 | N |
| ATOM | 2990 | CA | ILE | B | 348 | 45.744 | 14.365 | 53.171 | 1.00 28.76 | C |
| ATOM | 2991 | CB | ILE | B | 348 | 45.565 | 12.842 | 52.964 | 1.00 28.50 | C |
| ATOM | 2992 | CG2 | ILE | B | 348 | 44.396 | 12.566 | 51.996 | 1.00 26.52 | C |
| ATOM | 2993 | CG1 | ILE | B | 348 | 46.875 | 12.250 | 52.431 | 1.00 28.17 | C |
| ATOM | 2994 | CD1 | ILE | B | 348 | 46.910 | 10.733 | 52.382 | 1.00 28.01 | C |
| ATOM | 2995 | C | ILE | B | 348 | 44.447 | 14.957 | 53.707 | 1.00 29.01 | C |
| ATOM | 2996 | O | ILE | B | 348 | 43.697 | 15.591 | 52.973 | 1.00 29.32 | O |
| ATOM | 2997 | N | ALA | B | 349 | 44.186 | 14.734 | 54.993 | 1.00 30.99 | N |
| ATOM | 2998 | CA | ALA | B | 349 | 42.994 | 15.268 | 55.627 | 1.00 31.07 | C |
| ATOM | 2999 | CB | ALA | B | 349 | 42.946 | 14.843 | 57.094 | 1.00 21.64 | C |
| ATOM | 3000 | C | ALA | B | 349 | 43.045 | 16.803 | 55.519 | 1.00 31.95 | C |
| ATOM | 3001 | O | ALA | B | 349 | 42.019 | 17.460 | 55.340 | 1.00 30.61 | O |
| ATOM | 3002 | N | GLU | B | 350 | 44.251 | 17.358 | 55.633 | 1.00 33.26 | N |
| ATOM | 3003 | CA | GLU | B | 350 | 44.441 | 18.804 | 55.542 | 1.00 34.86 | C |
| ATOM | 3004 | CB | GLU | B | 350 | 45.917 | 19.159 | 55.743 | 1.00 40.47 | C |
| ATOM | 3005 | CG | GLU | B | 350 | 46.144 | 20.604 | 56.142 | 1.00 44.15 | C |
| ATOM | 3006 | CD | GLU | B | 350 | 47.580 | 21.064 | 55.942 | 1.00 45.07 | C |
| ATOM | 3007 | OE1 | GLU | B | 350 | 48.514 | 20.283 | 56.209 | 1.00 44.86 | O |
| ATOM | 3008 | OE2 | GLU | B | 350 | 47.770 | 22.222 | 55.523 | 1.00 48.13 | O |
| ATOM | 3009 | C | GLU | B | 350 | 43.973 | 19.277 | 54.163 | 1.00 34.02 | C |
| ATOM | 3010 | O | GLU | B | 350 | 43.192 | 20.211 | 54.055 | 1.00 34.89 | O |
| ATOM | 3011 | N | GLY | B | 351 | 44.445 | 18.620 | 53.113 | 1.00 30.91 | N |
| ATOM | 3012 | CA | GLY | B | 351 | 44.028 | 18.991 | 51.772 | 1.00 30.25 | C |
| ATOM | 3013 | C | GLY | B | 351 | 42.521 | 18.869 | 51.608 | 1.00 29.69 | C |
| ATOM | 3014 | O | GLY | B | 351 | 41.874 | 19.789 | 51.101 | 1.00 29.24 | O |
| ATOM | 3015 | N | MET | B | 352 | 41.957 | 17.742 | 52.046 | 1.00 30.11 | N |
| ATOM | 3016 | CA | MET | B | 352 | 40.513 | 17.524 | 51.942 | 1.00 29.98 | C |
| ATOM | 3017 | CB | MET | B | 352 | 40.133 | 16.118 | 52.412 | 1.00 29.73 | C |
| ATOM | 3018 | CG | MET | B | 352 | 40.589 | 15.003 | 51.461 | 1.00 31.12 | C |
| ATOM | 3019 | SD | MET | B | 352 | 40.052 | 15.276 | 49.744 | 1.00 30.26 | S |
| ATOM | 3020 | CE | MET | B | 352 | 38.313 | 15.567 | 49.989 | 1.00 27.64 | C |
| ATOM | 3021 | C | MET | B | 352 | 39.760 | 18.562 | 52.761 | 1.00 30.42 | C |
| ATOM | 3022 | O | MET | B | 352 | 38.625 | 18.928 | 52.427 | 1.00 29.69 | O |
| ATOM | 3023 | N | ALA | B | 353 | 40.393 | 19.028 | 53.836 | 1.00 31.22 | N |
| ATOM | 3024 | CA | ALA | B | 353 | 39.791 | 20.049 | 54.680 | 1.00 32.58 | C |
| ATOM | 3025 | CB | ALA | B | 353 | 40.651 | 20.278 | 55.921 | 1.00 30.78 | C |
| ATOM | 3026 | C | ALA | B | 353 | 39.665 | 21.346 | 53.857 | 1.00 33.57 | C |
| ATOM | 3027 | O | ALA | B | 353 | 38.686 | 22.078 | 53.973 | 1.00 32.99 | O |
| ATOM | 3028 | N | PHE | B | 354 | 40.655 | 21.617 | 53.012 | 1.00 40.72 | N |
| ATOM | 3029 | CA | PHE | B | 354 | 40.614 | 22.810 | 52.164 | 1.00 41.71 | C |
| ATOM | 3030 | CB | PHE | B | 354 | 41.947 | 23.016 | 51.448 | 1.00 44.26 | C |
| ATOM | 3031 | CG | PHE | B | 354 | 41.969 | 24.218 | 50.533 | 1.00 46.20 | C |
| ATOM | 3032 | CD1 | PHE | B | 354 | 41.788 | 25.498 | 51.039 | 1.00 45.78 | C |
| ATOM | 3033 | CD2 | PHE | B | 354 | 42.216 | 24.070 | 49.174 | 1.00 45.58 | C |
| ATOM | 3034 | CE1 | PHE | B | 354 | 41.860 | 26.608 | 50.207 | 1.00 46.14 | C |
| ATOM | 3035 | CE2 | PHE | B | 354 | 42.289 | 25.174 | 48.338 | 1.00 45.80 | C |
| ATOM | 3036 | CZ | PHE | B | 354 | 42.112 | 26.446 | 48.856 | 1.00 46.23 | C |
| ATOM | 3037 | C | PHE | B | 354 | 39.519 | 22.663 | 51.119 | 1.00 41.74 | C |
| ATOM | 3038 | O | PHE | B | 354 | 38.758 | 23.592 | 50.861 | 1.00 42.57 | O |
| ATOM | 3039 | N | ILE | B | 355 | 39.458 | 21.493 | 50.500 | 1.00 41.08 | N |
| ATOM | 3040 | CA | ILE | B | 355 | 38.446 | 21.228 | 49.482 | 1.00 41.02 | C |
| ATOM | 3041 | CB | ILE | B | 355 | 38.687 | 19.836 | 48.866 | 1.00 33.79 | C |
| ATOM | 3042 | CG2 | ILE | B | 355 | 37.456 | 19.369 | 48.073 | 1.00 33.24 | C |
| ATOM | 3043 | CG1 | ILE | B | 355 | 39.960 | 19.892 | 48.015 | 1.00 32.18 | C |
| ATOM | 3044 | CD1 | ILE | B | 355 | 40.436 | 18.553 | 47.510 | 1.00 30.62 | C |

Figure 15

| ATOM | 3045 | C | ILE | B | 355 | 37.051 | 21.329 | 50.111 | 1.00 | 40.99 | C |
|------|------|------|------|---|-----|--------|--------|--------|------|-------|---|
| ATOM | 3046 | O | ILE | B | 355 | 36.126 | 21.879 | 49.523 | 1.00 | 41.47 | O |
| ATOM | 3047 | N | GLU | B | 356 | 36.918 | 20.808 | 51.321 | 1.00 | 34.53 | N |
| ATOM | 3048 | CA | GLU | B | 356 | 35.658 | 20.859 | 52.051 | 1.00 | 34.87 | C |
| ATOM | 3049 | CB | GLU | B | 356 | 35.828 | 20.101 | 53.373 | 1.00 | 34.43 | C |
| ATOM | 3050 | CG | GLU | B | 356 | 34.718 | 20.243 | 54.401 | 1.00 | 33.72 | C |
| ATOM | 3051 | CD | GLU | B | 356 | 34.949 | 19.331 | 55.605 | 1.00 | 32.79 | C |
| ATOM | 3052 | OE1 | GLU | B | 356 | 34.580 | 18.149 | 55.532 | 1.00 | 33.14 | O |
| ATOM | 3053 | OE2 | GLU | B | 356 | 35.524 | 19.782 | 56.621 | 1.00 | 34.75 | O |
| ATOM | 3054 | C | GLU | B | 356 | 35.291 | 22.323 | 52.301 | 1.00 | 36.26 | C |
| ATOM | 3055 | O | GLU | B | 356 | 34.161 | 22.752 | 52.052 | 1.00 | 35.38 | O |
| ATOM | 3056 | N | GLU | B | 357 | 36.270 | 23.080 | 52.787 | 1.00 | 42.12 | N |
| ATOM | 3057 | CA | GLU | B | 357 | 36.110 | 24.498 | 53.088 | 1.00 | 44.76 | C |
| ATOM | 3058 | CB | GLU | B | 357 | 37.433 | 25.045 | 53.640 | 1.00 | 70.42 | C |
| ATOM | 3059 | CG | GLU | B | 357 | 37.799 | 26.452 | 53.194 | 1.00 | 74.44 | C |
| ATOM | 3060 | CD | GLU | B | 357 | 36.769 | 27.482 | 53.590 | 1.00 | 77.02 | C |
| ATOM | 3061 | OE1 | GLU | B | 357 | 36.350 | 27.468 | 54.771 | 1.00 | 78.42 | O |
| ATOM | 3062 | OE2 | GLU | B | 357 | 36.385 | 28.308 | 52.722 | 1.00 | 78.51 | O |
| ATOM | 3063 | C | GLU | B | 357 | 35.651 | 25.325 | 51.884 | 1.00 | 45.28 | C |
| ATOM | 3064 | O | GLU | B | 357 | 34.818 | 26.221 | 52.025 | 1.00 | 45.10 | O |
| ATOM | 3065 | N | ARG | B | 358 | 36.182 | 25.007 | 50.706 | 1.00 | 41.89 | N |
| ATOM | 3066 | CA | ARG | B | 358 | 35.838 | 25.722 | 49.481 | 1.00 | 42.55 | C |
| ATOM | 3067 | CB | ARG | B | 358 | 37.049 | 25.751 | 48.541 | 1.00 | 55.36 | C |
| ATOM | 3068 | CG | ARG | B | 358 | 38.255 | 26.504 | 49.101 | 1.00 | 57.90 | C |
| ATOM | 3069 | CD | ARG | B | 358 | 37.991 | 28.011 | 49.221 | 1.00 | 58.82 | C |
| ATOM | 3070 | NE | ARG | B | 358 | 38.103 | 28.695 | 47.937 | 1.00 | 61.20 | N |
| ATOM | 3071 | CZ | ARG | B | 358 | 39.227 | 29.226 | 47.458 | 1.00 | 63.82 | C |
| ATOM | 3072 | NH1 | ARG | B | 358 | 40.357 | 29.167 | 48.158 | 1.00 | 64.07 | N |
| ATOM | 3073 | NH2 | ARG | B | 358 | 39.229 | 29.811 | 46.264 | 1.00 | 64.27 | N |
| ATOM | 3074 | C | ARG | B | 358 | 34.629 | 25.109 | 48.773 | 1.00 | 42.64 | C |
| ATOM | 3075 | O | ARG | B | 358 | 34.359 | 25.403 | 47.608 | 1.00 | 42.39 | O |
| ATOM | 3076 | N | ASN | B | 359 | 33.906 | 24.251 | 49.480 | 1.00 | 40.95 | N |
| ATOM | 3077 | CA | ASN | B | 359 | 32.710 | 23.616 | 48.939 | 1.00 | 40.16 | C |
| ATOM | 3078 | CB | ASN | B | 359 | 31.624 | 24.675 | 48.715 | 1.00 | 76.95 | C |
| ATOM | 3079 | CG | ASN | B | 359 | 31.298 | 25.475 | 49.983 | 1.00 | 79.50 | C |
| ATOM | 3080 | OD1 | ASN | B | 359 | 31.031 | 24.912 | 51.055 | 1.00 | 80.06 | O |
| ATOM | 3081 | ND2 | ASN | B | 359 | 31.297 | 26.802 | 49.855 | 1.00 | 81.62 | N |
| ATOM | 3082 | C | ASN | B | 359 | 32.898 | 22.790 | 47.650 | 1.00 | 39.19 | C |
| ATOM | 3083 | O | ASN | B | 359 | 32.034 | 22.789 | 46.774 | 1.00 | 38.60 | O |
| ATOM | 3084 | N | TYR | B | 360 | 34.023 | 22.095 | 47.526 | 1.00 | 36.51 | N |
| ATOM | 3085 | CA | TYR | B | 360 | 34.248 | 21.242 | 46.360 | 1.00 | 36.64 | C |
| ATOM | 3086 | CB | TYR | B | 360 | 35.626 | 21.488 | 45.734 | 1.00 | 54.60 | C |
| ATOM | 3087 | CG | TYR | B | 360 | 35.691 | 22.664 | 44.795 | 1.00 | 56.92 | C |
| ATOM | 3088 | CD1 | TYR | B | 360 | 35.622 | 23.965 | 45.275 | 1.00 | 57.73 | C |
| ATOM | 3089 | CE1 | TYR | B | 360 | 35.653 | 25.043 | 44.416 | 1.00 | 59.40 | C |
| ATOM | 3090 | CD2 | TYR | B | 360 | 35.796 | 22.473 | 43.422 | 1.00 | 57.86 | C |
| ATOM | 3091 | CE2 | TYR | B | 360 | 35.826 | 23.545 | 42.552 | 1.00 | 59.71 | C |
| ATOM | 3092 | CZ | TYR | B | 360 | 35.753 | 24.828 | 43.055 | 1.00 | 60.61 | C |
| ATOM | 3093 | OH | TYR | B | 360 | 35.769 | 25.905 | 42.198 | 1.00 | 64.09 | O |
| ATOM | 3094 | C | TYR | B | 360 | 34.202 | 19.811 | 46.859 | 1.00 | 35.29 | C |
| ATOM | 3095 | O | TYR | B | 360 | 34.072 | 19.590 | 48.055 | 1.00 | 33.46 | O |
| ATOM | 3096 | N | ILE | B | 361 | 34.309 | 18.845 | 45.948 | 1.00 | 51.30 | N |
| ATOM | 3097 | CA | ILE | B | 361 | 34.345 | 17.439 | 46.339 | 1.00 | 51.49 | C |
| ATOM | 3098 | CB | ILE | B | 361 | 32.941 | 16.774 | 46.278 | 1.00 | 47.32 | C |
| ATOM | 3099 | CG2 | ILE | B | 361 | 32.068 | 17.305 | 47.429 | 1.00 | 44.86 | C |
| ATOM | 3100 | CG1 | ILE | B | 361 | 32.280 | 17.025 | 44.927 | 1.00 | 48.04 | C |
| ATOM | 3101 | CD1 | ILE | B | 361 | 32.796 | 16.147 | 43.807 | 1.00 | 50.21 | C |
| ATOM | 3102 | C | ILE | B | 361 | 35.344 | 16.662 | 45.481 | 1.00 | 51.71 | C |
| ATOM | 3103 | O | ILE | B | 361 | 35.519 | 16.948 | 44.290 | 1.00 | 52.26 | O |
| ATOM | 3104 | N | HIS | B | 362 | 36.014 | 15.685 | 46.079 | 1.00 | 39.70 | N |

Figure 15

| | | | | | | | | | |
|---|---|---|---|---|---|---|---|---|---|
| ATOM | 3105 | CA | HIS | B | 362 | 36.987 | 14.926 | 45.316 | 1.00 38.49 | C |
| ATOM | 3106 | CB | HIS | B | 362 | 37.977 | 14.214 | 46.241 | 1.00 36.70 | C |
| ATOM | 3107 | CG | HIS | B | 362 | 39.180 | 13.678 | 45.531 | 1.00 33.79 | C |
| ATOM | 3108 | CD2 | HIS | B | 362 | 40.501 | 13.905 | 45.719 | 1.00 33.04 | C |
| ATOM | 3109 | ND1 | HIS | B | 362 | 39.090 | 12.796 | 44.475 | 1.00 35.06 | N |
| ATOM | 3110 | CE1 | HIS | B | 362 | 40.306 | 12.502 | 44.046 | 1.00 33.43 | C |
| ATOM | 3111 | NE2 | HIS | B | 362 | 41.180 | 13.164 | 44.785 | 1.00 31.68 | N |
| ATOM | 3112 | C | HIS | B | 362 | 36.302 | 13.915 | 44.427 | 1.00 37.79 | C |
| ATOM | 3113 | O | HIS | B | 362 | 36.439 | 13.971 | 43.207 | 1.00 37.41 | O |
| ATOM | 3114 | N | ARG | B | 363 | 35.572 | 12.992 | 45.052 | 1.00 40.12 | N |
| ATOM | 3115 | CA | ARG | B | 363 | 34.840 | 11.940 | 44.342 | 1.00 38.57 | C |
| ATOM | 3116 | CB | ARG | B | 363 | 34.154 | 12.520 | 43.102 | 1.00 50.26 | C |
| ATOM | 3117 | CG | ARG | B | 363 | 33.386 | 11.490 | 42.298 | 1.00 54.62 | C |
| ATOM | 3118 | CD | ARG | B | 363 | 33.326 | 11.860 | 40.817 | 1.00 58.85 | C |
| ATOM | 3119 | NE | ARG | B | 363 | 31.980 | 12.248 | 40.411 | 1.00 62.41 | N |
| ATOM | 3120 | CZ | ARG | B | 363 | 31.329 | 13.298 | 40.892 | 1.00 63.82 | C |
| ATOM | 3121 | NH1 | ARG | B | 363 | 31.902 | 14.077 | 41.793 | 1.00 64.48 | N |
| ATOM | 3122 | NH2 | ARG | B | 363 | 30.092 | 13.553 | 40.487 | 1.00 65.05 | N |
| ATOM | 3123 | C | ARG | B | 363 | 35.713 | 10.751 | 43.933 | 1.00 36.83 | C |
| ATOM | 3124 | O | ARG | B | 363 | 35.207 | 9.663 | 43.665 | 1.00 35.75 | O |
| ATOM | 3125 | N | ASP | B | 364 | 37.023 | 10.949 | 43.882 | 1.00 35.62 | N |
| ATOM | 3126 | CA | ASP | B | 364 | 37.920 | 9.861 | 43.496 | 1.00 35.08 | C |
| ATOM | 3127 | CB | ASP | B | 364 | 38.543 | 10.145 | 42.119 | 1.00 32.45 | C |
| ATOM | 3128 | CG | ASP | B | 364 | 37.554 | 9.950 | 40.972 | 1.00 33.91 | C |
| ATOM | 3129 | OD1 | ASP | B | 364 | 37.076 | 8.809 | 40.773 | 1.00 32.69 | O |
| ATOM | 3130 | OD2 | ASP | B | 364 | 37.260 | 10.944 | 40.271 | 1.00 34.01 | O |
| ATOM | 3131 | C | ASP | B | 364 | 39.028 | 9.649 | 44.529 | 1.00 34.29 | C |
| ATOM | 3132 | O | ASP | B | 364 | 40.109 | 9.148 | 44.210 | 1.00 34.15 | O |
| ATOM | 3133 | N | LEU | B | 365 | 38.742 | 10.017 | 45.771 | 1.00 30.50 | N |
| ATOM | 3134 | CA | LEU | B | 365 | 39.706 | 9.901 | 46.840 | 1.00 30.87 | C |
| ATOM | 3135 | CB | LEU | B | 365 | 39.193 | 10.632 | 48.082 | 1.00 27.78 | C |
| ATOM | 3136 | CG | LEU | B | 365 | 40.170 | 10.652 | 49.268 | 1.00 28.47 | C |
| ATOM | 3137 | CD1 | LEU | B | 365 | 41.450 | 11.409 | 48.872 | 1.00 28.29 | C |
| ATOM | 3138 | CD2 | LEU | B | 365 | 39.508 | 11.311 | 50.469 | 1.00 26.49 | C |
| ATOM | 3139 | C | LEU | B | 365 | 40.084 | 8.470 | 47.226 | 1.00 31.93 | C |
| ATOM | 3140 | O | LEU | B | 365 | 39.234 | 7.688 | 47.681 | 1.00 32.43 | O |
| ATOM | 3141 | N | ARG | B | 366 | 41.370 | 8.156 | 47.051 | 1.00 32.94 | N |
| ATOM | 3142 | CA | ARG | B | 366 | 41.969 | 6.864 | 47.400 | 1.00 32.38 | C |
| ATOM | 3143 | CB | ARG | B | 366 | 41.462 | 5.736 | 46.491 | 1.00 28.96 | C |
| ATOM | 3144 | CG | ARG | B | 366 | 41.676 | 5.882 | 44.995 | 1.00 30.82 | C |
| ATOM | 3145 | CD | ARG | B | 366 | 41.225 | 4.575 | 44.320 | 1.00 34.88 | C |
| ATOM | 3146 | NE | ARG | B | 366 | 41.272 | 4.605 | 42.858 | 1.00 37.25 | N |
| ATOM | 3147 | CZ | ARG | B | 366 | 40.398 | 5.257 | 42.096 | 1.00 37.19 | C |
| ATOM | 3148 | NH1 | ARG | B | 366 | 39.402 | 5.933 | 42.654 | 1.00 36.87 | N |
| ATOM | 3149 | NH2 | ARG | B | 366 | 40.531 | 5.248 | 40.775 | 1.00 37.50 | N |
| ATOM | 3150 | C | ARG | B | 366 | 43.496 | 7.005 | 47.313 | 1.00 32.76 | C |
| ATOM | 3151 | O | ARG | B | 366 | 43.994 | 7.936 | 46.692 | 1.00 32.66 | O |
| ATOM | 3152 | N | ALA | B | 367 | 44.235 | 6.100 | 47.950 | 1.00 29.45 | N |
| ATOM | 3153 | CA | ALA | B | 367 | 45.690 | 6.187 | 47.950 | 1.00 30.44 | C |
| ATOM | 3154 | CB | ALA | B | 367 | 46.272 | 5.006 | 48.704 | 1.00 37.58 | C |
| ATOM | 3155 | C | ALA | B | 367 | 46.329 | 6.293 | 46.556 | 1.00 31.09 | C |
| ATOM | 3156 | O | ALA | B | 367 | 47.351 | 6.962 | 46.383 | 1.00 31.08 | O |
| ATOM | 3157 | N | ALA | B | 368 | 45.728 | 5.646 | 45.563 | 1.00 30.93 | N |
| ATOM | 3158 | CA | ALA | B | 368 | 46.258 | 5.697 | 44.212 | 1.00 30.60 | C |
| ATOM | 3159 | CB | ALA | B | 368 | 45.393 | 4.872 | 43.266 | 1.00 31.44 | C |
| ATOM | 3160 | C | ALA | B | 368 | 46.280 | 7.132 | 43.743 | 1.00 31.63 | C |
| ATOM | 3161 | O | ALA | B | 368 | 47.093 | 7.501 | 42.894 | 1.00 32.27 | O |
| ATOM | 3162 | N | ASN | B | 369 | 45.385 | 7.945 | 44.301 | 1.00 33.36 | N |
| ATOM | 3163 | CA | ASN | B | 369 | 45.287 | 9.329 | 43.886 | 1.00 33.04 | C |
| ATOM | 3164 | CB | ASN | B | 369 | 43.826 | 9.660 | 43.556 | 1.00 36.44 | C |

Figure 15

| | | | | | | | | | |
|---|---|---|---|---|---|---|---|---|---|
| ATOM | 3165 | CG | ASN | B | 369 | 43.343 | 8.910 | 42.319 | 1.00 37.35 | C |
| ATOM | 3166 | OD1 | ASN | B | 369 | 44.063 | 8.847 | 41.308 | 1.00 38.38 | O |
| ATOM | 3167 | ND2 | ASN | B | 369 | 42.137 | 8.347 | 42.380 | 1.00 33.25 | N |
| ATOM | 3168 | C | ASN | B | 369 | 45.898 | 10.357 | 44.807 | 1.00 32.44 | C |
| ATOM | 3169 | O | ASN | B | 369 | 45.504 | 11.520 | 44.819 | 1.00 33.21 | O |
| ATOM | 3170 | N | ILE | B | 370 | 46.856 | 9.909 | 45.603 | 1.00 33.15 | N |
| ATOM | 3171 | CA | ILE | B | 370 | 47.604 | 10.801 | 46.481 | 1.00 32.19 | C |
| ATOM | 3172 | CB | ILE | B | 370 | 47.606 | 10.325 | 47.940 | 1.00 27.93 | C |
| ATOM | 3173 | CG2 | ILE | B | 370 | 48.543 | 11.214 | 48.775 | 1.00 26.92 | C |
| ATOM | 3174 | CG1 | ILE | B | 370 | 46.169 | 10.326 | 48.497 | 1.00 27.32 | C |
| ATOM | 3175 | CD1 | ILE | B | 370 | 45.459 | 11.662 | 48.451 | 1.00 22.59 | C |
| ATOM | 3176 | C | ILE | B | 370 | 49.012 | 10.650 | 45.908 | 1.00 32.80 | C |
| ATOM | 3177 | O | ILE | B | 370 | 49.435 | 9.533 | 45.590 | 1.00 33.03 | O |
| ATOM | 3178 | N | LEU | B | 371 | 49.713 | 11.762 | 45.737 | 1.00 31.09 | N |
| ATOM | 3179 | CA | LEU | B | 371 | 51.071 | 11.736 | 45.206 | 1.00 31.97 | C |
| ATOM | 3180 | CB | LEU | B | 371 | 51.180 | 12.706 | 44.027 | 1.00 34.04 | C |
| ATOM | 3181 | CG | LEU | B | 371 | 50.215 | 12.364 | 42.873 | 1.00 34.80 | C |
| ATOM | 3182 | CD1 | LEU | B | 371 | 50.223 | 13.453 | 41.830 | 1.00 34.20 | C |
| ATOM | 3183 | CD2 | LEU | B | 371 | 50.611 | 11.039 | 42.257 | 1.00 34.36 | C |
| ATOM | 3184 | C | LEU | B | 371 | 52.064 | 12.100 | 46.322 | 1.00 32.41 | C |
| ATOM | 3185 | O | LEU | B | 371 | 51.773 | 12.937 | 47.179 | 1.00 32.89 | O |
| ATOM | 3186 | N | VAL | B | 372 | 53.226 | 11.457 | 46.310 | 1.00 32.16 | N |
| ATOM | 3187 | CA | VAL | B | 372 | 54.248 | 11.676 | 47.331 | 1.00 33.13 | C |
| ATOM | 3188 | CB | VAL | B | 372 | 54.621 | 10.331 | 48.009 | 1.00 35.52 | C |
| ATOM | 3189 | CG1 | VAL | B | 372 | 55.492 | 10.578 | 49.249 | 1.00 35.13 | C |
| ATOM | 3190 | CG2 | VAL | B | 372 | 53.343 | 9.587 | 48.403 | 1.00 34.71 | C |
| ATOM | 3191 | C | VAL | B | 372 | 55.514 | 12.351 | 46.807 | 1.00 33.40 | C |
| ATOM | 3192 | O | VAL | B | 372 | 56.124 | 11.908 | 45.832 | 1.00 32.45 | O |
| ATOM | 3193 | N | SER | B | 373 | 55.910 | 13.430 | 47.471 | 1.00 39.08 | N |
| ATOM | 3194 | CA | SER | B | 373 | 57.097 | 14.179 | 47.068 | 1.00 41.92 | C |
| ATOM | 3195 | CB | SER | B | 373 | 57.033 | 15.597 | 47.609 | 1.00 42.59 | C |
| ATOM | 3196 | OG | SER | B | 373 | 57.313 | 15.603 | 48.997 | 1.00 44.21 | O |
| ATOM | 3197 | C | SER | B | 373 | 58.372 | 13.516 | 47.586 | 1.00 43.83 | C |
| ATOM | 3198 | O | SER | B | 373 | 58.324 | 12.567 | 48.372 | 1.00 44.09 | O |
| ATOM | 3199 | N | ASP | B | 374 | 59.511 | 14.032 | 47.139 | 1.00 50.09 | N |
| ATOM | 3200 | CA | ASP | B | 374 | 60.804 | 13.511 | 47.545 | 1.00 51.44 | C |
| ATOM | 3201 | CB | ASP | B | 374 | 61.927 | 14.210 | 46.769 | 1.00 62.33 | C |
| ATOM | 3202 | CG | ASP | B | 374 | 61.780 | 15.714 | 46.751 | 1.00 63.70 | C |
| ATOM | 3203 | OD1 | ASP | B | 374 | 61.489 | 16.306 | 47.812 | 1.00 64.02 | O |
| ATOM | 3204 | OD2 | ASP | B | 374 | 61.965 | 16.308 | 45.668 | 1.00 67.14 | O |
| ATOM | 3205 | C | ASP | B | 374 | 61.010 | 13.686 | 49.042 | 1.00 52.51 | C |
| ATOM | 3206 | O | ASP | B | 374 | 61.841 | 13.002 | 49.643 | 1.00 52.99 | O |
| ATOM | 3207 | N | THR | B | 375 | 60.254 | 14.605 | 49.641 | 1.00 49.91 | N |
| ATOM | 3208 | CA | THR | B | 375 | 60.337 | 14.852 | 51.081 | 1.00 50.00 | C |
| ATOM | 3209 | CB | THR | B | 375 | 59.954 | 16.298 | 51.436 | 1.00 58.92 | C |
| ATOM | 3210 | OG1 | THR | B | 375 | 58.569 | 16.505 | 51.138 | 1.00 60.71 | O |
| ATOM | 3211 | CG2 | THR | B | 375 | 60.787 | 17.291 | 50.637 | 1.00 59.92 | C |
| ATOM | 3212 | C | THR | B | 375 | 59.344 | 13.941 | 51.792 | 1.00 49.54 | C |
| ATOM | 3213 | O | THR | B | 375 | 59.152 | 14.044 | 53.004 | 1.00 50.29 | O |
| ATOM | 3214 | N | LEU | B | 376 | 58.705 | 13.066 | 51.025 | 1.00 50.38 | N |
| ATOM | 3215 | CA | LEU | B | 376 | 57.708 | 12.138 | 51.560 | 1.00 49.66 | C |
| ATOM | 3216 | CB | LEU | B | 376 | 58.271 | 11.367 | 52.754 | 1.00 47.58 | C |
| ATOM | 3217 | CG | LEU | B | 376 | 59.467 | 10.490 | 52.394 | 1.00 47.64 | C |
| ATOM | 3218 | CD1 | LEU | B | 376 | 59.872 | 9.653 | 53.590 | 1.00 47.96 | C |
| ATOM | 3219 | CD2 | LEU | B | 376 | 59.094 | 9.603 | 51.217 | 1.00 48.01 | C |
| ATOM | 3220 | C | LEU | B | 376 | 56.415 | 12.829 | 51.968 | 1.00 48.27 | C |
| ATOM | 3221 | O | LEU | B | 376 | 55.629 | 12.276 | 52.734 | 1.00 48.28 | O |
| ATOM | 3222 | N | SER | B | 377 | 56.199 | 14.041 | 51.464 | 1.00 37.39 | N |
| ATOM | 3223 | CA | SER | B | 377 | 54.982 | 14.775 | 51.779 | 1.00 36.41 | C |
| ATOM | 3224 | CB | SER | B | 377 | 55.245 | 16.281 | 51.796 | 1.00 59.75 | C |

Figure 15

| ATOM | 3225 | OG  | SER | B | 377 | 55.653 | 16.748 | 50.525 | 1.00 | 63.60 | O |
|------|------|-----|-----|---|-----|--------|--------|--------|------|-------|---|
| ATOM | 3226 | C   | SER | B | 377 | 53.931 | 14.425 | 50.732 | 1.00 | 34.81 | C |
| ATOM | 3227 | O   | SER | B | 377 | 54.228 | 14.319 | 49.544 | 1.00 | 33.99 | O |
| ATOM | 3228 | N   | CYS | B | 378 | 52.699 | 14.240 | 51.181 | 1.00 | 40.25 | N |
| ATOM | 3229 | CA  | CYS | B | 378 | 51.622 | 13.865 | 50.285 | 1.00 | 38.89 | C |
| ATOM | 3230 | CB  | CYS | B | 378 | 50.671 | 12.908 | 51.007 | 1.00 | 41.38 | C |
| ATOM | 3231 | SG  | CYS | B | 378 | 51.451 | 11.388 | 51.612 | 1.00 | 42.18 | S |
| ATOM | 3232 | C   | CYS | B | 378 | 50.840 | 15.048 | 49.744 | 1.00 | 38.46 | C |
| ATOM | 3233 | O   | CYS | B | 378 | 50.759 | 16.096 | 50.377 | 1.00 | 38.26 | O |
| ATOM | 3234 | N   | LYS | B | 379 | 50.282 | 14.871 | 48.554 | 1.00 | 34.42 | N |
| ATOM | 3235 | CA  | LYS | B | 379 | 49.471 | 15.899 | 47.925 | 1.00 | 34.78 | C |
| ATOM | 3236 | CB  | LYS | B | 379 | 50.280 | 16.696 | 46.902 | 1.00 | 42.45 | C |
| ATOM | 3237 | CG  | LYS | B | 379 | 51.349 | 17.571 | 47.511 | 1.00 | 43.01 | C |
| ATOM | 3238 | CD  | LYS | B | 379 | 51.947 | 18.506 | 46.475 | 1.00 | 44.16 | C |
| ATOM | 3239 | CE  | LYS | B | 379 | 53.000 | 19.410 | 47.101 | 1.00 | 44.31 | C |
| ATOM | 3240 | NZ  | LYS | B | 379 | 53.384 | 20.509 | 46.178 | 1.00 | 47.43 | N |
| ATOM | 3241 | C   | LYS | B | 379 | 48.286 | 15.243 | 47.235 | 1.00 | 33.95 | C |
| ATOM | 3242 | O   | LYS | B | 379 | 48.394 | 14.143 | 46.685 | 1.00 | 33.84 | O |
| ATOM | 3243 | N   | ILE | B | 380 | 47.155 | 15.929 | 47.274 | 1.00 | 37.42 | N |
| ATOM | 3244 | CA  | ILE | B | 380 | 45.931 | 15.433 | 46.668 | 1.00 | 37.47 | C |
| ATOM | 3245 | CB  | ILE | B | 380 | 44.699 | 16.141 | 47.258 | 1.00 | 39.42 | C |
| ATOM | 3246 | CG2 | ILE | B | 380 | 43.461 | 15.728 | 46.481 | 1.00 | 37.68 | C |
| ATOM | 3247 | CG1 | ILE | B | 380 | 44.591 | 15.826 | 48.761 | 1.00 | 38.81 | C |
| ATOM | 3248 | CD1 | ILE | B | 380 | 43.428 | 16.497 | 49.442 | 1.00 | 40.12 | C |
| ATOM | 3249 | C   | ILE | B | 380 | 45.928 | 15.637 | 45.163 | 1.00 | 37.84 | C |
| ATOM | 3250 | O   | ILE | B | 380 | 46.211 | 16.738 | 44.664 | 1.00 | 37.75 | O |
| ATOM | 3251 | N   | ALA | B | 381 | 45.598 | 14.568 | 44.448 | 1.00 | 34.66 | N |
| ATOM | 3252 | CA  | ALA | B | 381 | 45.548 | 14.584 | 42.995 | 1.00 | 35.67 | C |
| ATOM | 3253 | CB  | ALA | B | 381 | 46.542 | 13.564 | 42.438 | 1.00 | 35.15 | C |
| ATOM | 3254 | C   | ALA | B | 381 | 44.149 | 14.266 | 42.478 | 1.00 | 35.99 | C |
| ATOM | 3255 | O   | ALA | B | 381 | 43.350 | 13.625 | 43.158 | 1.00 | 34.32 | O |
| ATOM | 3256 | N   | ASP | B | 382 | 43.886 | 14.715 | 41.255 | 1.00 | 41.60 | N |
| ATOM | 3257 | CA  | ASP | B | 382 | 42.622 | 14.492 | 40.549 | 1.00 | 42.90 | C |
| ATOM | 3258 | CB  | ASP | B | 382 | 42.647 | 13.125 | 39.852 | 1.00 | 48.09 | C |
| ATOM | 3259 | CG  | ASP | B | 382 | 43.483 | 13.140 | 38.570 | 1.00 | 50.59 | C |
| ATOM | 3260 | OD1 | ASP | B | 382 | 43.312 | 14.084 | 37.766 | 1.00 | 52.56 | O |
| ATOM | 3261 | OD2 | ASP | B | 382 | 44.292 | 12.216 | 38.360 | 1.00 | 49.31 | O |
| ATOM | 3262 | C   | ASP | B | 382 | 41.328 | 14.641 | 41.335 | 1.00 | 42.63 | C |
| ATOM | 3263 | O   | ASP | B | 382 | 40.491 | 13.738 | 41.356 | 1.00 | 42.03 | O |
| ATOM | 3264 | N   | PHE | B | 383 | 41.169 | 15.802 | 41.952 | 1.00 | 38.23 | N |
| ATOM | 3265 | CA  | PHE | B | 383 | 39.978 | 16.136 | 42.728 | 1.00 | 40.09 | C |
| ATOM | 3266 | CB  | PHE | B | 383 | 40.378 | 16.904 | 43.987 | 1.00 | 50.94 | C |
| ATOM | 3267 | CG  | PHE | B | 383 | 41.286 | 18.068 | 43.712 | 1.00 | 51.82 | C |
| ATOM | 3268 | CD1 | PHE | B | 383 | 42.653 | 17.882 | 43.601 | 1.00 | 51.75 | C |
| ATOM | 3269 | CD2 | PHE | B | 383 | 40.767 | 19.335 | 43.501 | 1.00 | 53.50 | C |
| ATOM | 3270 | CE1 | PHE | B | 383 | 43.491 | 18.934 | 43.280 | 1.00 | 53.43 | C |
| ATOM | 3271 | CE2 | PHE | B | 383 | 41.598 | 20.398 | 43.177 | 1.00 | 53.85 | C |
| ATOM | 3272 | CZ  | PHE | B | 383 | 42.963 | 20.197 | 43.065 | 1.00 | 54.01 | C |
| ATOM | 3273 | C   | PHE | B | 383 | 39.064 | 17.035 | 41.890 | 1.00 | 40.79 | C |
| ATOM | 3274 | O   | PHE | B | 383 | 39.497 | 17.634 | 40.902 | 1.00 | 40.94 | O |
| ATOM | 3275 | N   | GLY | B | 384 | 37.805 | 17.140 | 42.303 | 1.00 | 44.45 | N |
| ATOM | 3276 | CA  | GLY | B | 384 | 36.863 | 17.994 | 41.603 | 1.00 | 44.94 | C |
| ATOM | 3277 | C   | GLY | B | 384 | 36.368 | 17.452 | 40.282 | 1.00 | 45.83 | C |
| ATOM | 3278 | O   | GLY | B | 384 | 35.544 | 18.079 | 39.633 | 1.00 | 46.08 | O |
| ATOM | 3279 | N   | LEU | B | 385 | 36.875 | 16.296 | 39.871 | 1.00 | 49.97 | N |
| ATOM | 3280 | CA  | LEU | B | 385 | 36.449 | 15.691 | 38.620 | 1.00 | 51.32 | C |
| ATOM | 3281 | CB  | LEU | B | 385 | 37.192 | 14.378 | 38.366 | 1.00 | 47.14 | C |
| ATOM | 3282 | CG  | LEU | B | 385 | 38.413 | 14.454 | 37.452 | 1.00 | 48.10 | C |
| ATOM | 3283 | CD1 | LEU | B | 385 | 39.021 | 13.071 | 37.257 | 1.00 | 47.84 | C |
| ATOM | 3284 | CD2 | LEU | B | 385 | 37.976 | 15.034 | 36.122 | 1.00 | 48.42 | C |

Figure 15

```
ATOM   3285  C    LEU B 385      34.957  15.411  38.614  1.00 52.50           C
ATOM   3286  O    LEU B 385      34.382  14.997  39.621  1.00 52.41           O
ATOM   3287  N    ALA B 386      34.339  15.640  37.462  1.00 90.13           N
ATOM   3288  CA   ALA B 386      32.916  15.392  37.293  1.00 91.01           C
ATOM   3289  CB   ALA B 386      32.366  16.257  36.159  1.00 60.72           C
ATOM   3290  C    ALA B 386      32.713  13.915  36.970  1.00 91.13           C
ATOM   3291  O    ALA B 386      31.585  13.427  36.963  1.00 92.37           O
ATOM   3292  N    ARG B 387      33.806  13.205  36.708  1.00 63.27           N
ATOM   3293  CA   ARG B 387      33.721  11.784  36.373  1.00 62.65           C
ATOM   3294  CB   ARG B 387      34.181  11.557  34.924  1.00 50.36           C
ATOM   3295  CG   ARG B 387      35.684  11.771  34.697  1.00 50.00           C
ATOM   3296  CD   ARG B 387      36.078  11.557  33.241  1.00 50.13           C
ATOM   3297  NE   ARG B 387      37.497  11.812  32.998  1.00 52.08           N
ATOM   3298  CZ   ARG B 387      38.462  10.902  33.113  1.00 52.24           C
ATOM   3299  NH1  ARG B 387      38.177   9.656  33.463  1.00 51.05           N
ATOM   3300  NH2  ARG B 387      39.723  11.245  32.883  1.00 54.26           N
ATOM   3301  C    ARG B 387      34.559  10.910  37.303  1.00 62.03           C
ATOM   3302  O    ARG B 387      35.538  11.374  37.883  1.00 62.05           O
ATOM   3303  N    LEU B 388      34.157   9.648  37.452  1.00 47.06           N
ATOM   3304  CA   LEU B 388      34.898   8.695  38.271  1.00 46.41           C
ATOM   3305  CB   LEU B 388      33.989   7.556  38.732  1.00 59.33           C
ATOM   3306  CG   LEU B 388      32.807   7.897  39.647  1.00 60.96           C
ATOM   3307  CD1  LEU B 388      31.965   6.653  39.871  1.00 61.16           C
ATOM   3308  CD2  LEU B 388      33.317   8.437  40.977  1.00 60.76           C
ATOM   3309  C    LEU B 388      35.993   8.140  37.356  1.00 45.74           C
ATOM   3310  O    LEU B 388      35.742   7.889  36.180  1.00 45.88           O
ATOM   3311  N    ILE B 389      37.200   7.961  37.887  1.00 42.57           N
ATOM   3312  CA   ILE B 389      38.308   7.457  37.083  1.00 41.71           C
ATOM   3313  CB   ILE B 389      39.524   8.426  37.112  1.00 43.27           C
ATOM   3314  CG2  ILE B 389      39.127   9.799  36.579  1.00 43.09           C
ATOM   3315  CG1  ILE B 389      40.056   8.549  38.543  1.00 42.53           C
ATOM   3316  CD1  ILE B 389      41.180   9.546  38.702  1.00 42.37           C
ATOM   3317  C    ILE B 389      38.809   6.086  37.511  1.00 41.67           C
ATOM   3318  O    ILE B 389      38.499   5.590  38.599  1.00 40.97           O
ATOM   3319  N    GLU B 390      39.592   5.479  36.632  1.00 52.34           N
ATOM   3320  CA   GLU B 390      40.185   4.183  36.896  1.00 53.13           C
ATOM   3321  CB   GLU B 390      39.924   3.209  35.753  1.00 52.35           C
ATOM   3322  CG   GLU B 390      38.477   2.805  35.609  1.00 54.65           C
ATOM   3323  CD   GLU B 390      38.318   1.668  34.636  1.00 56.14           C
ATOM   3324  OE1  GLU B 390      38.879   1.769  33.521  1.00 58.12           O
ATOM   3325  OE2  GLU B 390      37.643   0.676  34.984  1.00 56.80           O
ATOM   3326  C    GLU B 390      41.675   4.392  37.055  1.00 53.02           C
ATOM   3327  O    GLU B 390      42.262   5.292  36.454  1.00 53.30           O
ATOM   3328  N    ASP B 391      42.292   3.550  37.864  1.00 51.14           N
ATOM   3329  CA   ASP B 391      43.713   3.685  38.109  1.00 51.63           C
ATOM   3330  CB   ASP B 391      44.057   2.980  39.424  1.00 54.41           C
ATOM   3331  CG   ASP B 391      43.215   3.487  40.578  1.00 54.04           C
ATOM   3332  OD1  ASP B 391      42.906   4.699  40.587  1.00 54.41           O
ATOM   3333  OD2  ASP B 391      42.866   2.691  41.475  1.00 55.48           O
ATOM   3334  C    ASP B 391      44.598   3.188  36.968  1.00 51.44           C
ATOM   3335  O    ASP B 391      45.819   3.155  37.107  1.00 52.12           O
ATOM   3336  N    ASN B 392      43.991   2.843  35.832  1.00 47.92           N
ATOM   3337  CA   ASN B 392      44.753   2.334  34.686  1.00 47.56           C
ATOM   3338  CB   ASN B 392      44.382   0.876  34.429  1.00 51.73           C
ATOM   3339  CG   ASN B 392      42.979   0.724  33.872  1.00 53.08           C
ATOM   3340  OD1  ASN B 392      42.231   1.695  33.757  1.00 53.14           O
ATOM   3341  ND2  ASN B 392      42.614  -0.504  33.527  1.00 54.65           N
ATOM   3342  C    ASN B 392      44.545   3.121  33.395  1.00 47.16           C
ATOM   3343  O    ASN B 392      44.789   2.616  32.299  1.00 47.13           O
ATOM   3344  N    GLU B 393      44.098   4.357  33.508  1.00 46.22           N
```

Figure 15

```
ATOM   3345  CA  GLU B 393      43.855   5.133  32.310  1.00 46.55           C
ATOM   3346  CB  GLU B 393      42.791   6.181  32.602  1.00 51.75           C
ATOM   3347  CG  GLU B 393      41.639   5.610  33.418  1.00 50.14           C
ATOM   3348  CD  GLU B 393      40.567   6.626  33.694  1.00 48.80           C
ATOM   3349  OE1 GLU B 393      40.914   7.809  33.886  1.00 48.60           O
ATOM   3350  OE2 GLU B 393      39.379   6.241  33.725  1.00 49.98           O
ATOM   3351  C   GLU B 393      45.138   5.766  31.789  1.00 46.64           C
ATOM   3352  O   GLU B 393      45.286   5.990  30.591  1.00 46.33           O
ATOM   3353  N   TYR B 394      46.077   6.022  32.692  1.00 47.91           N
ATOM   3354  CA  TYR B 394      47.354   6.620  32.323  1.00 48.72           C
ATOM   3355  CB  TYR B 394      47.452   8.030  32.910  1.00 46.19           C
ATOM   3356  CG  TYR B 394      46.420   8.980  32.348  1.00 44.68           C
ATOM   3357  CD1 TYR B 394      46.480   9.385  31.021  1.00 43.57           C
ATOM   3358  CE1 TYR B 394      45.521  10.230  30.490  1.00 42.76           C
ATOM   3359  CD2 TYR B 394      45.368   9.448  33.135  1.00 42.43           C
ATOM   3360  CE2 TYR B 394      44.405  10.293  32.613  1.00 41.14           C
ATOM   3361  CZ  TYR B 394      44.488  10.681  31.288  1.00 41.87           C
ATOM   3362  OH  TYR B 394      43.550  11.524  30.750  1.00 41.05           O
ATOM   3363  C   TYR B 394      48.539   5.775  32.782  1.00 50.57           C
ATOM   3364  O   TYR B 394      49.689   6.188  32.647  1.00 50.84           O
ATOM   3365  N   THR B 395      48.260   4.587  33.313  1.00 54.28           N
ATOM   3366  CA  THR B 395      49.321   3.699  33.779  1.00 56.33           C
ATOM   3367  CB  THR B 395      49.710   4.024  35.231  1.00 84.63           C
ATOM   3368  OG1 THR B 395      49.722   5.447  35.414  1.00 87.46           O
ATOM   3369  CG2 THR B 395      51.098   3.475  35.544  1.00 84.86           C
ATOM   3370  C   THR B 395      48.893   2.234  33.709  1.00 57.20           C
ATOM   3371  O   THR B 395      47.724   1.910  33.902  1.00 57.62           O
ATOM   3372  N   ALA B 396      49.847   1.352  33.436  1.00 67.84           N
ATOM   3373  CA  ALA B 396      49.576  -0.078  33.339  1.00 69.02           C
ATOM   3374  CB  ALA B 396      50.796  -0.796  32.775  1.00 74.28           C
ATOM   3375  C   ALA B 396      49.192  -0.683  34.691  1.00 69.69           C
ATOM   3376  O   ALA B 396      49.847  -0.432  35.704  1.00 69.69           O
ATOM   3377  N   ARG B 397      48.128  -1.483  34.693  1.00 78.51           N
ATOM   3378  CA  ARG B 397      47.636  -2.131  35.909  1.00 78.76           C
ATOM   3379  CB  ARG B 397      46.574  -1.252  36.585  1.00 59.10           C
ATOM   3380  CG  ARG B 397      47.140  -0.024  37.270  1.00 58.83           C
ATOM   3381  CD  ARG B 397      47.935  -0.423  38.503  1.00 59.09           C
ATOM   3382  NE  ARG B 397      48.802   0.646  38.998  1.00 59.64           N
ATOM   3383  CZ  ARG B 397      48.382   1.857  39.344  1.00 59.34           C
ATOM   3384  NH1 ARG B 397      47.099   2.172  39.248  1.00 60.03           N
ATOM   3385  NH2 ARG B 397      49.249   2.753  39.793  1.00 59.32           N
ATOM   3386  C   ARG B 397      47.041  -3.504  35.603  1.00 78.90           C
ATOM   3387  O   ARG B 397      46.628  -3.776  34.474  1.00 79.06           O
ATOM   3388  N   PRO B 403      36.678   0.872  41.142  1.00 65.60           N
ATOM   3389  CD  PRO B 403      36.816   1.791  39.996  1.00 67.29           C
ATOM   3390  CA  PRO B 403      37.031   1.546  42.399  1.00 64.51           C
ATOM   3391  CB  PRO B 403      37.512   2.925  41.934  1.00 66.09           C
ATOM   3392  CG  PRO B 403      36.733   3.151  40.672  1.00 67.08           C
ATOM   3393  C   PRO B 403      35.867   1.630  43.385  1.00 63.23           C
ATOM   3394  O   PRO B 403      35.764   2.592  44.174  1.00 63.45           O
ATOM   3395  N   ILE B 404      35.013   0.605  43.362  1.00 36.21           N
ATOM   3396  CA  ILE B 404      33.839   0.552  44.234  1.00 33.58           C
ATOM   3397  CB  ILE B 404      32.921  -0.638  43.878  1.00 50.87           C
ATOM   3398  CG2 ILE B 404      31.582  -0.459  44.546  1.00 52.91           C
ATOM   3399  CG1 ILE B 404      32.725  -0.735  42.365  1.00 52.80           C
ATOM   3400  CD1 ILE B 404      32.334   0.567  41.702  1.00 54.82           C
ATOM   3401  C   ILE B 404      34.154   0.445  45.730  1.00 30.53           C
ATOM   3402  O   ILE B 404      33.373   0.902  46.555  1.00 30.25           O
ATOM   3403  N   LYS B 405      35.294  -0.145  46.072  1.00 32.74           N
ATOM   3404  CA  LYS B 405      35.690  -0.342  47.466  1.00 32.27           C
```

Figure 15

| | | | | | | | | | |
|---|---|---|---|---|---|---|---|---|---|
| ATOM | 3405 | CB | LYS | B | 405 | 36.921 | -1.250 | 47.533 | 1.00 34.36 | C |
| ATOM | 3406 | CG | LYS | B | 405 | 36.619 | -2.688 | 47.106 | 1.00 35.12 | C |
| ATOM | 3407 | CD | LYS | B | 405 | 37.837 | -3.594 | 47.188 | 1.00 34.55 | C |
| ATOM | 3408 | CE | LYS | B | 405 | 37.409 | -5.037 | 46.915 | 1.00 36.63 | C |
| ATOM | 3409 | NZ | LYS | B | 405 | 38.394 | -6.021 | 47.424 | 1.00 37.10 | N |
| ATOM | 3410 | C | LYS | B | 405 | 35.944 | 0.909 | 48.296 | 1.00 31.27 | C |
| ATOM | 3411 | O | LYS | B | 405 | 36.206 | 0.812 | 49.488 | 1.00 30.86 | O |
| ATOM | 3412 | N | TRP | B | 406 | 35.860 | 2.072 | 47.661 | 1.00 35.01 | N |
| ATOM | 3413 | CA | TRP | B | 406 | 36.073 | 3.357 | 48.321 | 1.00 34.27 | C |
| ATOM | 3414 | CB | TRP | B | 406 | 37.177 | 4.124 | 47.591 | 1.00 30.81 | C |
| ATOM | 3415 | CG | TRP | B | 406 | 38.581 | 3.602 | 47.791 | 1.00 32.47 | C |
| ATOM | 3416 | CD2 | TRP | B | 406 | 39.251 | 2.589 | 47.016 | 1.00 31.49 | C |
| ATOM | 3417 | CE2 | TRP | B | 406 | 40.542 | 2.428 | 47.563 | 1.00 31.43 | C |
| ATOM | 3418 | CE3 | TRP | B | 406 | 38.883 | 1.804 | 45.918 | 1.00 33.28 | C |
| ATOM | 3419 | CD1 | TRP | B | 406 | 39.476 | 3.998 | 48.751 | 1.00 30.95 | C |
| ATOM | 3420 | NE1 | TRP | B | 406 | 40.656 | 3.296 | 48.618 | 1.00 31.06 | N |
| ATOM | 3421 | CZ2 | TRP | B | 406 | 41.464 | 1.516 | 47.049 | 1.00 31.84 | C |
| ATOM | 3422 | CZ3 | TRP | B | 406 | 39.799 | 0.899 | 45.409 | 1.00 32.02 | C |
| ATOM | 3423 | CH2 | TRP | B | 406 | 41.075 | 0.764 | 45.975 | 1.00 31.63 | C |
| ATOM | 3424 | C | TRP | B | 406 | 34.782 | 4.195 | 48.287 | 1.00 34.44 | C |
| ATOM | 3425 | O | TRP | B | 406 | 34.724 | 5.287 | 48.859 | 1.00 34.64 | O |
| ATOM | 3426 | N | THR | B | 407 | 33.754 | 3.689 | 47.610 | 1.00 28.08 | N |
| ATOM | 3427 | CA | THR | B | 407 | 32.493 | 4.418 | 47.464 | 1.00 28.04 | C |
| ATOM | 3428 | CB | THR | B | 407 | 31.836 | 4.063 | 46.117 | 1.00 36.29 | C |
| ATOM | 3429 | OG1 | THR | B | 407 | 32.790 | 4.272 | 45.072 | 1.00 38.53 | O |
| ATOM | 3430 | CG2 | THR | B | 407 | 30.601 | 4.939 | 45.849 | 1.00 35.54 | C |
| ATOM | 3431 | C | THR | B | 407 | 31.476 | 4.200 | 48.590 | 1.00 28.37 | C |
| ATOM | 3432 | O | THR | B | 407 | 31.157 | 3.061 | 48.959 | 1.00 28.44 | O |
| ATOM | 3433 | N | ALA | B | 408 | 30.971 | 5.305 | 49.132 | 1.00 30.10 | N |
| ATOM | 3434 | CA | ALA | B | 408 | 29.998 | 5.262 | 50.216 | 1.00 29.97 | C |
| ATOM | 3435 | CB | ALA | B | 408 | 29.766 | 6.671 | 50.770 | 1.00 28.07 | C |
| ATOM | 3436 | C | ALA | B | 408 | 28.684 | 4.675 | 49.718 | 1.00 29.39 | C |
| ATOM | 3437 | O | ALA | B | 408 | 28.344 | 4.803 | 48.543 | 1.00 29.98 | O |
| ATOM | 3438 | N | PRO | B | 409 | 27.917 | 4.043 | 50.618 | 1.00 28.48 | N |
| ATOM | 3439 | CD | PRO | B | 409 | 28.218 | 3.876 | 52.048 | 1.00 31.47 | C |
| ATOM | 3440 | CA | PRO | B | 409 | 26.630 | 3.426 | 50.277 | 1.00 28.85 | C |
| ATOM | 3441 | CB | PRO | B | 409 | 26.086 | 2.987 | 51.635 | 1.00 31.99 | C |
| ATOM | 3442 | CG | PRO | B | 409 | 27.328 | 2.712 | 52.425 | 1.00 31.83 | C |
| ATOM | 3443 | C | PRO | B | 409 | 25.645 | 4.315 | 49.506 | 1.00 29.09 | C |
| ATOM | 3444 | O | PRO | B | 409 | 25.075 | 3.879 | 48.501 | 1.00 26.94 | O |
| ATOM | 3445 | N | GLU | B | 410 | 25.449 | 5.552 | 49.971 | 1.00 29.19 | N |
| ATOM | 3446 | CA | GLU | B | 410 | 24.520 | 6.463 | 49.303 | 1.00 30.63 | C |
| ATOM | 3447 | CB | GLU | B | 410 | 24.342 | 7.774 | 50.110 | 1.00 30.68 | C |
| ATOM | 3448 | CG | GLU | B | 410 | 25.544 | 8.728 | 50.143 | 1.00 29.43 | C |
| ATOM | 3449 | CD | GLU | B | 410 | 26.638 | 8.307 | 51.121 | 1.00 29.23 | C |
| ATOM | 3450 | OE1 | GLU | B | 410 | 26.538 | 7.220 | 51.715 | 1.00 29.54 | O |
| ATOM | 3451 | OE2 | GLU | B | 410 | 27.609 | 9.067 | 51.296 | 1.00 28.77 | O |
| ATOM | 3452 | C | GLU | B | 410 | 24.968 | 6.764 | 47.870 | 1.00 31.10 | C |
| ATOM | 3453 | O | GLU | B | 410 | 24.148 | 7.029 | 46.992 | 1.00 31.53 | O |
| ATOM | 3454 | N | ALA | B | 411 | 26.271 | 6.688 | 47.626 | 1.00 33.26 | N |
| ATOM | 3455 | CA | ALA | B | 411 | 26.800 | 6.942 | 46.293 | 1.00 34.50 | C |
| ATOM | 3456 | CB | ALA | B | 411 | 28.291 | 7.283 | 46.378 | 1.00 29.03 | C |
| ATOM | 3457 | C | ALA | B | 411 | 26.577 | 5.716 | 45.403 | 1.00 35.93 | C |
| ATOM | 3458 | O | ALA | B | 411 | 26.209 | 5.834 | 44.232 | 1.00 35.73 | O |
| ATOM | 3459 | N | ILE | B | 412 | 26.807 | 4.537 | 45.969 | 1.00 33.98 | N |
| ATOM | 3460 | CA | ILE | B | 412 | 26.602 | 3.302 | 45.242 | 1.00 35.17 | C |
| ATOM | 3461 | CB | ILE | B | 412 | 26.999 | 2.087 | 46.080 | 1.00 37.96 | C |
| ATOM | 3462 | CG2 | ILE | B | 412 | 26.612 | 0.811 | 45.335 | 1.00 38.96 | C |
| ATOM | 3463 | CG1 | ILE | B | 412 | 28.499 | 2.121 | 46.376 | 1.00 38.42 | C |
| ATOM | 3464 | CD1 | ILE | B | 412 | 28.939 | 1.131 | 47.408 | 1.00 37.80 | C |

Figure 15

| | | | | | | | | | | |
|---|---|---|---|---|---|---|---|---|---|---|
| ATOM | 3465 | C   | ILE | B | 412 | 25.133 | 3.110  | 44.871 | 1.00 36.80 | C |
| ATOM | 3466 | O   | ILE | B | 412 | 24.802 | 2.814  | 43.723 | 1.00 36.44 | O |
| ATOM | 3467 | N   | ASN | B | 413 | 24.252 | 3.295  | 45.852 | 1.00 41.27 | N |
| ATOM | 3468 | CA  | ASN | B | 413 | 22.826 | 3.078  | 45.635 | 1.00 41.91 | C |
| ATOM | 3469 | CB  | ASN | B | 413 | 22.135 | 2.759  | 46.968 | 1.00 42.51 | C |
| ATOM | 3470 | CG  | ASN | B | 413 | 22.698 | 1.510  | 47.629 | 1.00 43.69 | C |
| ATOM | 3471 | OD1 | ASN | B | 413 | 23.079 | 0.554  | 46.952 | 1.00 44.88 | O |
| ATOM | 3472 | ND2 | ASN | B | 413 | 22.740 | 1.510  | 48.953 | 1.00 43.89 | N |
| ATOM | 3473 | C   | ASN | B | 413 | 22.032 | 4.154  | 44.913 | 1.00 41.50 | C |
| ATOM | 3474 | O   | ASN | B | 413 | 21.073 | 3.833  | 44.227 | 1.00 40.74 | O |
| ATOM | 3475 | N   | TYR | B | 414 | 22.424 | 5.417  | 45.058 | 1.00 38.01 | N |
| ATOM | 3476 | CA  | TYR | B | 414 | 21.690 | 6.518  | 44.430 | 1.00 38.04 | C |
| ATOM | 3477 | CB  | TYR | B | 414 | 20.888 | 7.274  | 45.492 | 1.00 46.71 | C |
| ATOM | 3478 | CG  | TYR | B | 414 | 19.937 | 6.384  | 46.241 | 1.00 47.76 | C |
| ATOM | 3479 | CD1 | TYR | B | 414 | 18.758 | 5.950  | 45.653 | 1.00 48.40 | C |
| ATOM | 3480 | CE1 | TYR | B | 414 | 17.919 | 5.071  | 46.308 | 1.00 48.73 | C |
| ATOM | 3481 | CD2 | TYR | B | 414 | 20.249 | 5.917  | 47.508 | 1.00 47.63 | C |
| ATOM | 3482 | CE2 | TYR | B | 414 | 19.418 | 5.038  | 48.168 | 1.00 49.07 | C |
| ATOM | 3483 | CZ  | TYR | B | 414 | 18.256 | 4.619  | 47.562 | 1.00 49.07 | C |
| ATOM | 3484 | OH  | TYR | B | 414 | 17.433 | 3.733  | 48.210 | 1.00 52.51 | O |
| ATOM | 3485 | C   | TYR | B | 414 | 22.580 | 7.505  | 43.699 | 1.00 37.92 | C |
| ATOM | 3486 | O   | TYR | B | 414 | 22.113 | 8.555  | 43.264 | 1.00 37.63 | O |
| ATOM | 3487 | N   | GLY | B | 415 | 23.860 | 7.174  | 43.579 | 1.00 42.45 | N |
| ATOM | 3488 | CA  | GLY | B | 415 | 24.781 | 8.065  | 42.904 | 1.00 42.29 | C |
| ATOM | 3489 | C   | GLY | B | 415 | 24.846 | 9.452  | 43.520 | 1.00 42.44 | C |
| ATOM | 3490 | O   | GLY | B | 415 | 25.148 | 10.413 | 42.830 | 1.00 43.71 | O |
| ATOM | 3491 | N   | THR | B | 416 | 24.563 | 9.559  | 44.815 | 1.00 46.84 | N |
| ATOM | 3492 | CA  | THR | B | 416 | 24.611 | 10.843 | 45.507 | 1.00 46.14 | C |
| ATOM | 3493 | CB  | THR | B | 416 | 23.470 | 10.954 | 46.558 | 1.00 39.03 | C |
| ATOM | 3494 | OG1 | THR | B | 416 | 23.889 | 11.772 | 47.661 | 1.00 41.62 | O |
| ATOM | 3495 | CG2 | THR | B | 416 | 23.076 | 9.605  | 47.044 | 1.00 38.75 | C |
| ATOM | 3496 | C   | THR | B | 416 | 25.979 | 11.032 | 46.159 | 1.00 45.61 | C |
| ATOM | 3497 | O   | THR | B | 416 | 26.304 | 10.415 | 47.175 | 1.00 46.63 | O |
| ATOM | 3498 | N   | PHE | B | 417 | 26.779 | 11.888 | 45.537 | 1.00 36.58 | N |
| ATOM | 3499 | CA  | PHE | B | 417 | 28.134 | 12.184 | 45.979 | 1.00 35.09 | C |
| ATOM | 3500 | CB  | PHE | B | 417 | 29.087 | 12.164 | 44.774 | 1.00 36.61 | C |
| ATOM | 3501 | CG  | PHE | B | 417 | 29.348 | 10.788 | 44.217 | 1.00 36.92 | C |
| ATOM | 3502 | CD2 | PHE | B | 417 | 30.422 | 10.028 | 44.674 | 1.00 37.04 | C |
| ATOM | 3503 | CD1 | PHE | B | 417 | 28.528 | 10.255 | 43.229 | 1.00 36.35 | C |
| ATOM | 3504 | CE2 | PHE | B | 417 | 30.675 | 8.760  | 44.150 | 1.00 37.17 | C |
| ATOM | 3505 | CE1 | PHE | B | 417 | 28.775 | 8.987  | 42.703 | 1.00 36.56 | C |
| ATOM | 3506 | CZ  | PHE | B | 417 | 29.852 | 8.241  | 43.166 | 1.00 35.84 | C |
| ATOM | 3507 | C   | PHE | B | 417 | 28.219 | 13.544 | 46.653 | 1.00 33.88 | C |
| ATOM | 3508 | O   | PHE | B | 417 | 27.706 | 14.531 | 46.140 | 1.00 33.34 | O |
| ATOM | 3509 | N   | THR | B | 418 | 28.887 | 13.579 | 47.798 | 1.00 31.14 | N |
| ATOM | 3510 | CA  | THR | B | 418 | 29.076 | 14.802 | 48.557 | 1.00 29.26 | C |
| ATOM | 3511 | CB  | THR | B | 418 | 27.974 | 14.990 | 49.617 | 1.00 33.83 | C |
| ATOM | 3512 | OG1 | THR | B | 418 | 28.201 | 14.082 | 50.705 | 1.00 33.96 | O |
| ATOM | 3513 | CG2 | THR | B | 418 | 26.592 | 14.720 | 49.007 | 1.00 32.81 | C |
| ATOM | 3514 | C   | THR | B | 418 | 30.412 | 14.692 | 49.279 | 1.00 28.63 | C |
| ATOM | 3515 | O   | THR | B | 418 | 31.153 | 13.713 | 49.110 | 1.00 27.96 | O |
| ATOM | 3516 | N   | ILE | B | 419 | 30.722 | 15.696 | 50.086 | 1.00 28.58 | N |
| ATOM | 3517 | CA  | ILE | B | 419 | 31.960 | 15.696 | 50.844 | 1.00 28.30 | C |
| ATOM | 3518 | CB  | ILE | B | 419 | 32.177 | 17.046 | 51.565 | 1.00 29.27 | C |
| ATOM | 3519 | CG2 | ILE | B | 419 | 31.102 | 17.268 | 52.640 | 1.00 27.31 | C |
| ATOM | 3520 | CG1 | ILE | B | 419 | 33.585 | 17.081 | 52.168 | 1.00 29.74 | C |
| ATOM | 3521 | CD1 | ILE | B | 419 | 34.684 | 17.122 | 51.128 | 1.00 29.25 | C |
| ATOM | 3522 | C   | ILE | B | 419 | 31.931 | 14.554 | 51.873 | 1.00 27.97 | C |
| ATOM | 3523 | O   | ILE | B | 419 | 32.966 | 14.027 | 52.262 | 1.00 27.69 | O |
| ATOM | 3524 | N   | LYS | B | 420 | 30.734 | 14.171 | 52.299 | 1.00 32.06 | N |

Figure 15

| ATOM | 3525 | CA | LYS | B | 420 | 30.591 | 13.082 | 53.264 | 1.00 | 31.65 | C |
| --- | --- | --- | --- | --- | --- | --- | --- | --- | --- | --- | --- |
| ATOM | 3526 | CB | LYS | B | 420 | 29.173 | 13.040 | 53.832 | 1.00 | 26.13 | C |
| ATOM | 3527 | CG | LYS | B | 420 | 28.853 | 14.203 | 54.741 | 1.00 | 26.22 | C |
| ATOM | 3528 | CD | LYS | B | 420 | 29.907 | 14.355 | 55.801 | 1.00 | 26.20 | C |
| ATOM | 3529 | CE | LYS | B | 420 | 29.540 | 15.423 | 56.815 | 1.00 | 25.73 | C |
| ATOM | 3530 | NZ | LYS | B | 420 | 30.614 | 15.517 | 57.835 | 1.00 | 26.43 | N |
| ATOM | 3531 | C | LYS | B | 420 | 30.934 | 11.742 | 52.617 | 1.00 | 30.81 | C |
| ATOM | 3532 | O | LYS | B | 420 | 31.453 | 10.837 | 53.275 | 1.00 | 30.76 | O |
| ATOM | 3533 | N | SER | B | 421 | 30.637 | 11.589 | 51.334 | 1.00 | 28.45 | N |
| ATOM | 3534 | CA | SER | B | 421 | 31.011 | 10.339 | 50.714 | 1.00 | 28.66 | C |
| ATOM | 3535 | CB | SER | B | 421 | 30.248 | 10.094 | 49.398 | 1.00 | 30.07 | C |
| ATOM | 3536 | OG | SER | B | 421 | 30.263 | 11.189 | 48.511 | 1.00 | 36.35 | O |
| ATOM | 3537 | C | SER | B | 421 | 32.535 | 10.351 | 50.553 | 1.00 | 28.59 | C |
| ATOM | 3538 | O | SER | B | 421 | 33.162 | 9.302 | 50.541 | 1.00 | 29.84 | O |
| ATOM | 3539 | N | ASP | B | 422 | 33.150 | 11.530 | 50.476 | 1.00 | 30.05 | N |
| ATOM | 3540 | CA | ASP | B | 422 | 34.614 | 11.570 | 50.388 | 1.00 | 29.67 | C |
| ATOM | 3541 | CB | ASP | B | 422 | 35.171 | 12.976 | 50.100 | 1.00 | 29.79 | C |
| ATOM | 3542 | CG | ASP | B | 422 | 34.978 | 13.430 | 48.666 | 1.00 | 29.63 | C |
| ATOM | 3543 | OD1 | ASP | B | 422 | 34.982 | 12.602 | 47.731 | 1.00 | 27.98 | O |
| ATOM | 3544 | OD2 | ASP | B | 422 | 34.852 | 14.654 | 48.477 | 1.00 | 30.78 | O |
| ATOM | 3545 | C | ASP | B | 422 | 35.158 | 11.146 | 51.761 | 1.00 | 29.17 | C |
| ATOM | 3546 | O | ASP | B | 422 | 36.166 | 10.439 | 51.842 | 1.00 | 29.69 | O |
| ATOM | 3547 | N | VAL | B | 423 | 34.510 | 11.606 | 52.833 | 1.00 | 26.48 | N |
| ATOM | 3548 | CA | VAL | B | 423 | 34.937 | 11.244 | 54.186 | 1.00 | 25.32 | C |
| ATOM | 3549 | CB | VAL | B | 423 | 34.016 | 11.860 | 55.278 | 1.00 | 27.54 | C |
| ATOM | 3550 | CG1 | VAL | B | 423 | 34.270 | 11.153 | 56.645 | 1.00 | 26.08 | C |
| ATOM | 3551 | CG2 | VAL | B | 423 | 34.303 | 13.383 | 55.415 | 1.00 | 26.32 | C |
| ATOM | 3552 | C | VAL | B | 423 | 34.943 | 9.718 | 54.331 | 1.00 | 25.26 | C |
| ATOM | 3553 | O | VAL | B | 423 | 35.833 | 9.164 | 54.971 | 1.00 | 24.33 | O |
| ATOM | 3554 | N | TRP | B | 424 | 33.954 | 9.055 | 53.729 | 1.00 | 23.00 | N |
| ATOM | 3555 | CA | TRP | B | 424 | 33.869 | 7.590 | 53.761 | 1.00 | 23.55 | C |
| ATOM | 3556 | CB | TRP | B | 424 | 32.581 | 7.116 | 53.072 | 1.00 | 26.89 | C |
| ATOM | 3557 | CG | TRP | B | 424 | 32.488 | 5.624 | 52.853 | 1.00 | 27.63 | C |
| ATOM | 3558 | CD2 | TRP | B | 424 | 31.629 | 4.705 | 53.535 | 1.00 | 26.80 | C |
| ATOM | 3559 | CE2 | TRP | B | 424 | 31.943 | 3.413 | 53.058 | 1.00 | 27.70 | C |
| ATOM | 3560 | CE3 | TRP | B | 424 | 30.628 | 4.844 | 54.506 | 1.00 | 27.90 | C |
| ATOM | 3561 | CD1 | TRP | B | 424 | 33.257 | 4.869 | 52.010 | 1.00 | 27.19 | C |
| ATOM | 3562 | NE1 | TRP | B | 424 | 32.941 | 3.550 | 52.131 | 1.00 | 25.21 | N |
| ATOM | 3563 | CZ2 | TRP | B | 424 | 31.290 | 2.262 | 53.519 | 1.00 | 26.72 | C |
| ATOM | 3564 | CZ3 | TRP | B | 424 | 29.985 | 3.708 | 54.962 | 1.00 | 28.42 | C |
| ATOM | 3565 | CH2 | TRP | B | 424 | 30.318 | 2.429 | 54.468 | 1.00 | 27.49 | C |
| ATOM | 3566 | C | TRP | B | 424 | 35.108 | 7.077 | 53.027 | 1.00 | 24.55 | C |
| ATOM | 3567 | O | TRP | B | 424 | 35.836 | 6.225 | 53.539 | 1.00 | 24.71 | O |
| ATOM | 3568 | N | SER | B | 425 | 35.363 | 7.618 | 51.837 | 1.00 | 26.43 | N |
| ATOM | 3569 | CA | SER | B | 425 | 36.537 | 7.220 | 51.064 | 1.00 | 27.99 | C |
| ATOM | 3570 | CB | SER | B | 425 | 36.635 | 8.016 | 49.751 | 1.00 | 30.07 | C |
| ATOM | 3571 | OG | SER | B | 425 | 35.615 | 7.636 | 48.843 | 1.00 | 28.88 | O |
| ATOM | 3572 | C | SER | B | 425 | 37.815 | 7.434 | 51.871 | 1.00 | 29.17 | C |
| ATOM | 3573 | O | SER | B | 425 | 38.696 | 6.581 | 51.861 | 1.00 | 30.89 | O |
| ATOM | 3574 | N | PHE | B | 426 | 37.933 | 8.570 | 52.560 | 1.00 | 29.82 | N |
| ATOM | 3575 | CA | PHE | B | 426 | 39.129 | 8.819 | 53.368 | 1.00 | 29.43 | C |
| ATOM | 3576 | CB | PHE | B | 426 | 39.061 | 10.182 | 54.079 | 1.00 | 24.41 | C |
| ATOM | 3577 | CG | PHE | B | 426 | 40.285 | 10.493 | 54.917 | 1.00 | 24.73 | C |
| ATOM | 3578 | CD1 | PHE | B | 426 | 41.446 | 10.991 | 54.327 | 1.00 | 25.16 | C |
| ATOM | 3579 | CD2 | PHE | B | 426 | 40.270 | 10.301 | 56.293 | 1.00 | 25.10 | C |
| ATOM | 3580 | CE1 | PHE | B | 426 | 42.561 | 11.292 | 55.088 | 1.00 | 25.51 | C |
| ATOM | 3581 | CE2 | PHE | B | 426 | 41.385 | 10.601 | 57.071 | 1.00 | 25.08 | C |
| ATOM | 3582 | CZ | PHE | B | 426 | 42.537 | 11.099 | 56.467 | 1.00 | 26.46 | C |
| ATOM | 3583 | C | PHE | B | 426 | 39.280 | 7.715 | 54.419 | 1.00 | 28.92 | C |
| ATOM | 3584 | O | PHE | B | 426 | 40.400 | 7.342 | 54.781 | 1.00 | 28.91 | O |

Figure 15

| | | | | | | | | | | |
|---|---|---|---|---|---|---|---|---|---|---|
| ATOM | 3585 | N | GLY | B | 427 | 38.149 | 7.220 | 54.924 | 1.00 29.45 | N |
| ATOM | 3586 | CA | GLY | B | 427 | 38.178 | 6.146 | 55.906 | 1.00 27.23 | C |
| ATOM | 3587 | C | GLY | B | 427 | 38.818 | 4.901 | 55.301 | 1.00 27.21 | C |
| ATOM | 3588 | O | GLY | B | 427 | 39.654 | 4.263 | 55.926 | 1.00 28.26 | O |
| ATOM | 3589 | N | ILE | B | 428 | 38.433 | 4.547 | 54.076 | 1.00 26.44 | N |
| ATOM | 3590 | CA | ILE | B | 428 | 39.012 | 3.383 | 53.417 | 1.00 26.40 | C |
| ATOM | 3591 | CB | ILE | B | 428 | 38.336 | 3.088 | 52.053 | 1.00 27.40 | C |
| ATOM | 3592 | CG2 | ILE | B | 428 | 38.966 | 1.840 | 51.422 | 1.00 27.22 | C |
| ATOM | 3593 | CG1 | ILE | B | 428 | 36.824 | 2.885 | 52.226 | 1.00 26.33 | C |
| ATOM | 3594 | CD1 | ILE | B | 428 | 36.433 | 1.709 | 53.133 | 1.00 26.24 | C |
| ATOM | 3595 | C | ILE | B | 428 | 40.499 | 3.677 | 53.177 | 1.00 26.97 | C |
| ATOM | 3596 | O | ILE | B | 428 | 41.353 | 2.805 | 53.353 | 1.00 25.75 | O |
| ATOM | 3597 | N | LEU | B | 429 | 40.808 | 4.919 | 52.804 | 1.00 26.51 | N |
| ATOM | 3598 | CA | LEU | B | 429 | 42.193 | 5.311 | 52.539 | 1.00 26.93 | C |
| ATOM | 3599 | CB | LEU | B | 429 | 42.249 | 6.784 | 52.084 | 1.00 25.83 | C |
| ATOM | 3600 | CG | LEU | B | 429 | 43.440 | 7.247 | 51.220 | 1.00 25.09 | C |
| ATOM | 3601 | CD1 | LEU | B | 429 | 43.132 | 8.607 | 50.589 | 1.00 26.02 | C |
| ATOM | 3602 | CD2 | LEU | B | 429 | 44.699 | 7.324 | 52.058 | 1.00 23.30 | C |
| ATOM | 3603 | C | LEU | B | 429 | 43.089 | 5.083 | 53.774 | 1.00 27.04 | C |
| ATOM | 3604 | O | LEU | B | 429 | 44.271 | 4.758 | 53.636 | 1.00 26.70 | O |
| ATOM | 3605 | N | LEU | B | 430 | 42.523 | 5.252 | 54.969 | 1.00 25.44 | N |
| ATOM | 3606 | CA | LEU | B | 430 | 43.272 | 5.031 | 56.200 | 1.00 25.33 | C |
| ATOM | 3607 | CB | LEU | B | 430 | 42.432 | 5.408 | 57.435 | 1.00 26.57 | C |
| ATOM | 3608 | CG | LEU | B | 430 | 42.128 | 6.900 | 57.675 | 1.00 27.05 | C |
| ATOM | 3609 | CD1 | LEU | B | 430 | 41.291 | 7.079 | 58.956 | 1.00 27.20 | C |
| ATOM | 3610 | CD2 | LEU | B | 430 | 43.435 | 7.682 | 57.782 | 1.00 28.00 | C |
| ATOM | 3611 | C | LEU | B | 430 | 43.728 | 3.567 | 56.296 | 1.00 26.12 | C |
| ATOM | 3612 | O | LEU | B | 430 | 44.835 | 3.296 | 56.752 | 1.00 26.78 | O |
| ATOM | 3613 | N | THR | B | 431 | 42.889 | 2.628 | 55.862 | 1.00 32.52 | N |
| ATOM | 3614 | CA | THR | B | 431 | 43.274 | 1.218 | 55.915 | 1.00 33.49 | C |
| ATOM | 3615 | CB | THR | B | 431 | 42.094 | 0.237 | 55.570 | 1.00 24.78 | C |
| ATOM | 3616 | OG1 | THR | B | 431 | 41.692 | 0.392 | 54.199 | 1.00 24.37 | O |
| ATOM | 3617 | CG2 | THR | B | 431 | 40.901 | 0.484 | 56.501 | 1.00 23.31 | C |
| ATOM | 3618 | C | THR | B | 431 | 44.447 | 0.960 | 54.968 | 1.00 34.51 | C |
| ATOM | 3619 | O | THR | B | 431 | 45.358 | 0.196 | 55.301 | 1.00 35.05 | O |
| ATOM | 3620 | N | GLU | B | 432 | 44.436 | 1.608 | 53.803 | 1.00 29.67 | N |
| ATOM | 3621 | CA | GLU | B | 432 | 45.524 | 1.459 | 52.833 | 1.00 29.83 | C |
| ATOM | 3622 | CB | GLU | B | 432 | 45.235 | 2.258 | 51.553 | 1.00 32.47 | C |
| ATOM | 3623 | CG | GLU | B | 432 | 44.205 | 1.650 | 50.622 | 1.00 33.96 | C |
| ATOM | 3624 | CD | GLU | B | 432 | 43.952 | 2.517 | 49.393 | 1.00 34.78 | C |
| ATOM | 3625 | OE1 | GLU | B | 432 | 43.372 | 3.621 | 49.526 | 1.00 33.97 | O |
| ATOM | 3626 | OE2 | GLU | B | 432 | 44.347 | 2.089 | 48.286 | 1.00 37.02 | O |
| ATOM | 3627 | C | GLU | B | 432 | 46.838 | 1.963 | 53.426 | 1.00 30.61 | C |
| ATOM | 3628 | O | GLU | B | 432 | 47.885 | 1.346 | 53.259 | 1.00 31.57 | O |
| ATOM | 3629 | N | ILE | B | 433 | 46.774 | 3.093 | 54.117 | 1.00 29.46 | N |
| ATOM | 3630 | CA | ILE | B | 433 | 47.957 | 3.687 | 54.711 | 1.00 30.49 | C |
| ATOM | 3631 | CB | ILE | B | 433 | 47.623 | 5.051 | 55.333 | 1.00 32.56 | C |
| ATOM | 3632 | CG2 | ILE | B | 433 | 48.751 | 5.490 | 56.260 | 1.00 33.22 | C |
| ATOM | 3633 | CG1 | ILE | B | 433 | 47.400 | 6.075 | 54.210 | 1.00 33.66 | C |
| ATOM | 3634 | CD1 | ILE | B | 433 | 47.131 | 7.495 | 54.683 | 1.00 32.16 | C |
| ATOM | 3635 | C | ILE | B | 433 | 48.675 | 2.833 | 55.758 | 1.00 31.06 | C |
| ATOM | 3636 | O | ILE | B | 433 | 49.887 | 2.647 | 55.689 | 1.00 30.43 | O |
| ATOM | 3637 | N | VAL | B | 434 | 47.926 | 2.307 | 56.719 | 1.00 38.41 | N |
| ATOM | 3638 | CA | VAL | B | 434 | 48.526 | 1.508 | 57.778 | 1.00 39.33 | C |
| ATOM | 3639 | CB | VAL | B | 434 | 47.675 | 1.557 | 59.055 | 1.00 37.83 | C |
| ATOM | 3640 | CG1 | VAL | B | 434 | 47.577 | 2.994 | 59.544 | 1.00 37.92 | C |
| ATOM | 3641 | CG2 | VAL | B | 434 | 46.293 | 0.975 | 58.788 | 1.00 37.82 | C |
| ATOM | 3642 | C | VAL | B | 434 | 48.791 | 0.051 | 57.407 | 1.00 39.82 | C |
| ATOM | 3643 | O | VAL | B | 434 | 49.438 | -0.662 | 58.155 | 1.00 41.28 | O |
| ATOM | 3644 | N | THR | B | 435 | 48.297 | -0.387 | 56.257 | 1.00 35.35 | N |

Figure 15

```
ATOM   3645  CA  THR B 435      48.527  -1.756  55.810  1.00 36.18           C
ATOM   3646  CB  THR B 435      47.258  -2.379  55.255  1.00 37.82           C
ATOM   3647  OG1 THR B 435      46.736  -1.524  54.229  1.00 38.39           O
ATOM   3648  CG2 THR B 435      46.227  -2.580  56.356  1.00 35.46           C
ATOM   3649  C   THR B 435      49.566  -1.735  54.687  1.00 37.73           C
ATOM   3650  O   THR B 435      49.805  -2.743  54.025  1.00 37.44           O
ATOM   3651  N   HIS B 436      50.159  -0.563  54.475  1.00 45.57           N
ATOM   3652  CA  HIS B 436      51.168  -0.358  53.453  1.00 46.65           C
ATOM   3653  CB  HIS B 436      52.426  -1.163  53.809  1.00 57.23           C
ATOM   3654  CG  HIS B 436      53.179  -0.597  54.975  1.00 57.96           C
ATOM   3655  CD2 HIS B 436      53.249  -0.992  56.268  1.00 58.55           C
ATOM   3656  ND1 HIS B 436      53.904   0.573  54.893  1.00 58.91           N
ATOM   3657  CE1 HIS B 436      54.386   0.878  56.084  1.00 58.33           C
ATOM   3658  NE2 HIS B 436      54.003  -0.056  56.937  1.00 60.11           N
ATOM   3659  C   HIS B 436      50.697  -0.648  52.024  1.00 47.05           C
ATOM   3660  O   HIS B 436      51.394  -1.283  51.232  1.00 46.36           O
ATOM   3661  N   GLY B 437      49.499  -0.170  51.702  1.00 41.84           N
ATOM   3662  CA  GLY B 437      48.980  -0.347  50.360  1.00 42.42           C
ATOM   3663  C   GLY B 437      48.076  -1.533  50.098  1.00 42.52           C
ATOM   3664  O   GLY B 437      47.699  -1.768  48.952  1.00 43.28           O
ATOM   3665  N   ARG B 438      47.728  -2.279  51.138  1.00 35.47           N
ATOM   3666  CA  ARG B 438      46.865  -3.435  50.971  1.00 36.62           C
ATOM   3667  CB  ARG B 438      46.679  -4.166  52.306  1.00 51.85           C
ATOM   3668  CG  ARG B 438      45.797  -5.428  52.220  1.00 54.81           C
ATOM   3669  CD  ARG B 438      45.119  -5.738  53.565  1.00 57.15           C
ATOM   3670  NE  ARG B 438      43.977  -4.854  53.809  1.00 58.01           N
ATOM   3671  CZ  ARG B 438      43.362  -4.721  54.981  1.00 58.81           C
ATOM   3672  NH1 ARG B 438      43.779  -5.409  56.034  1.00 58.91           N
ATOM   3673  NH2 ARG B 438      42.324  -3.902  55.098  1.00 59.34           N
ATOM   3674  C   ARG B 438      45.500  -3.019  50.431  1.00 36.16           C
ATOM   3675  O   ARG B 438      44.960  -1.975  50.801  1.00 35.63           O
ATOM   3676  N   ILE B 439      44.948  -3.848  49.554  1.00 43.51           N
ATOM   3677  CA  ILE B 439      43.641  -3.591  48.965  1.00 43.54           C
ATOM   3678  CB  ILE B 439      43.373  -4.563  47.796  1.00 55.22           C
ATOM   3679  CG2 ILE B 439      42.014  -4.276  47.158  1.00 56.37           C
ATOM   3680  CG1 ILE B 439      44.478  -4.405  46.748  1.00 57.36           C
ATOM   3681  CD1 ILE B 439      44.384  -5.375  45.588  1.00 58.77           C
ATOM   3682  C   ILE B 439      42.555  -3.755  50.032  1.00 42.73           C
ATOM   3683  O   ILE B 439      42.625  -4.647  50.878  1.00 42.67           O
ATOM   3684  N   PRO B 440      41.552  -2.870  50.023  1.00 42.72           N
ATOM   3685  CD  PRO B 440      41.513  -1.620  49.248  1.00 36.01           C
ATOM   3686  CA  PRO B 440      40.449  -2.915  50.990  1.00 41.64           C
ATOM   3687  CB  PRO B 440      39.671  -1.637  50.676  1.00 35.59           C
ATOM   3688  CG  PRO B 440      40.743  -0.718  50.165  1.00 35.30           C
ATOM   3689  C   PRO B 440      39.597  -4.172  50.819  1.00 40.08           C
ATOM   3690  O   PRO B 440      39.516  -4.719  49.724  1.00 39.83           O
ATOM   3691  N   TYR B 441      38.960  -4.623  51.896  1.00 30.28           N
ATOM   3692  CA  TYR B 441      38.116  -5.815  51.832  1.00 29.47           C
ATOM   3693  CB  TYR B 441      36.869  -5.527  50.989  1.00 34.23           C
ATOM   3694  CG  TYR B 441      36.040  -4.357  51.479  1.00 33.59           C
ATOM   3695  CD1 TYR B 441      35.181  -4.495  52.568  1.00 32.19           C
ATOM   3696  CE1 TYR B 441      34.458  -3.420  53.045  1.00 31.41           C
ATOM   3697  CD2 TYR B 441      36.148  -3.105  50.878  1.00 33.18           C
ATOM   3698  CE2 TYR B 441      35.427  -2.020  51.347  1.00 31.47           C
ATOM   3699  CZ  TYR B 441      34.587  -2.186  52.435  1.00 33.53           C
ATOM   3700  OH  TYR B 441      33.902  -1.110  52.941  1.00 33.15           O
ATOM   3701  C   TYR B 441      38.914  -6.956  51.187  1.00 30.34           C
ATOM   3702  O   TYR B 441      38.517  -7.508  50.164  1.00 29.33           O
ATOM   3703  N   PRO B 442      40.060  -7.313  51.778  1.00 44.15           N
ATOM   3704  CD  PRO B 442      40.589  -6.891  53.087  1.00 37.96           C
```

Figure 15

| ATOM | 3705 | CA | PRO | B | 442 | 40.869 | -8.393 | 51.209 | 1.00 | 46.70 | C |
|------|------|----|-----|---|-----|--------|--------|--------|------|-------|---|
| ATOM | 3706 | CB | PRO | B | 442 | 42.071 | -8.439 | 52.144 | 1.00 | 40.21 | C |
| ATOM | 3707 | CG | PRO | B | 442 | 41.471 | -8.055 | 53.464 | 1.00 | 39.16 | C |
| ATOM | 3708 | C | PRO | B | 442 | 40.099 | -9.710 | 51.167 | 1.00 | 48.51 | C |
| ATOM | 3709 | O | PRO | B | 442 | 39.743 | -10.263 | 52.204 | 1.00 | 50.63 | O |
| ATOM | 3710 | N | GLY | B | 443 | 39.818 | -10.200 | 49.968 | 1.00 | 51.44 | N |
| ATOM | 3711 | CA | GLY | B | 443 | 39.092 | -11.451 | 49.862 | 1.00 | 53.84 | C |
| ATOM | 3712 | C | GLY | B | 443 | 37.666 | -11.296 | 49.384 | 1.00 | 54.63 | C |
| ATOM | 3713 | O | GLY | B | 443 | 36.861 | -12.219 | 49.508 | 1.00 | 54.83 | O |
| ATOM | 3714 | N | MET | B | 444 | 37.348 | -10.126 | 48.841 | 1.00 | 52.24 | N |
| ATOM | 3715 | CA | MET | B | 444 | 36.009 | -9.868 | 48.330 | 1.00 | 52.63 | C |
| ATOM | 3716 | CB | MET | B | 444 | 35.229 | -8.919 | 49.251 | 1.00 | 46.90 | C |
| ATOM | 3717 | CG | MET | B | 444 | 35.030 | -9.365 | 50.682 | 1.00 | 47.75 | C |
| ATOM | 3718 | SD | MET | B | 444 | 33.960 | -8.180 | 51.571 | 1.00 | 48.11 | S |
| ATOM | 3719 | CE | MET | B | 444 | 32.546 | -8.270 | 50.619 | 1.00 | 49.41 | C |
| ATOM | 3720 | C | MET | B | 444 | 36.109 | -9.204 | 46.969 | 1.00 | 52.61 | C |
| ATOM | 3721 | O | MET | B | 444 | 36.980 | -8.362 | 46.742 | 1.00 | 53.04 | O |
| ATOM | 3722 | N | THR | B | 445 | 35.223 | -9.593 | 46.063 | 1.00 | 47.17 | N |
| ATOM | 3723 | CA | THR | B | 445 | 35.179 | -8.982 | 44.746 | 1.00 | 47.11 | C |
| ATOM | 3724 | CB | THR | B | 445 | 34.552 | -9.926 | 43.708 | 1.00 | 46.35 | C |
| ATOM | 3725 | OG1 | THR | B | 445 | 33.204 | -10.229 | 44.092 | 1.00 | 45.97 | O |
| ATOM | 3726 | CG2 | THR | B | 445 | 35.359 | -11.217 | 43.605 | 1.00 | 46.81 | C |
| ATOM | 3727 | C | THR | B | 445 | 34.257 | -7.777 | 44.930 | 1.00 | 46.82 | C |
| ATOM | 3728 | O | THR | B | 445 | 33.652 | -7.616 | 45.989 | 1.00 | 46.80 | O |
| ATOM | 3729 | N | ASN | B | 446 | 34.134 | -6.939 | 43.911 | 1.00 | 50.71 | N |
| ATOM | 3730 | CA | ASN | B | 446 | 33.268 | -5.774 | 44.022 | 1.00 | 51.00 | C |
| ATOM | 3731 | CB | ASN | B | 446 | 33.329 | -4.936 | 42.741 | 1.00 | 45.19 | C |
| ATOM | 3732 | CG | ASN | B | 446 | 34.679 | -4.285 | 42.544 | 1.00 | 45.57 | C |
| ATOM | 3733 | OD1 | ASN | B | 446 | 35.471 | -4.180 | 43.481 | 1.00 | 45.81 | O |
| ATOM | 3734 | ND2 | ASN | B | 446 | 34.944 | -3.827 | 41.328 | 1.00 | 45.47 | N |
| ATOM | 3735 | C | ASN | B | 446 | 31.816 | -6.130 | 44.342 | 1.00 | 50.54 | C |
| ATOM | 3736 | O | ASN | B | 446 | 31.236 | -5.598 | 45.287 | 1.00 | 50.04 | O |
| ATOM | 3737 | N | PRO | B | 447 | 31.209 | -7.037 | 43.561 | 1.00 | 54.80 | N |
| ATOM | 3738 | CD | PRO | B | 447 | 31.721 | -7.802 | 42.407 | 1.00 | 45.99 | C |
| ATOM | 3739 | CA | PRO | B | 447 | 29.818 | -7.390 | 43.850 | 1.00 | 53.40 | C |
| ATOM | 3740 | CB | PRO | B | 447 | 29.459 | -8.353 | 42.715 | 1.00 | 44.93 | C |
| ATOM | 3741 | CG | PRO | B | 447 | 30.767 | -8.958 | 42.349 | 1.00 | 45.60 | C |
| ATOM | 3742 | C | PRO | B | 447 | 29.662 | -7.993 | 45.242 | 1.00 | 52.46 | C |
| ATOM | 3743 | O | PRO | B | 447 | 28.593 | -7.901 | 45.853 | 1.00 | 51.69 | O |
| ATOM | 3744 | N | GLU | B | 448 | 30.736 | -8.595 | 45.745 | 1.00 | 42.93 | N |
| ATOM | 3745 | CA | GLU | B | 448 | 30.709 | -9.180 | 47.076 | 1.00 | 41.92 | C |
| ATOM | 3746 | CB | GLU | B | 448 | 31.933 | -10.076 | 47.307 | 1.00 | 54.61 | C |
| ATOM | 3747 | CG | GLU | B | 448 | 31.675 | -11.552 | 46.964 | 1.00 | 57.82 | C |
| ATOM | 3748 | CD | GLU | B | 448 | 32.942 | -12.386 | 46.872 | 1.00 | 58.25 | C |
| ATOM | 3749 | OE1 | GLU | B | 448 | 33.796 | -12.307 | 47.778 | 1.00 | 58.59 | O |
| ATOM | 3750 | OE2 | GLU | B | 448 | 33.079 | -13.135 | 45.883 | 1.00 | 61.40 | O |
| ATOM | 3751 | C | GLU | B | 448 | 30.685 | -8.036 | 48.077 | 1.00 | 40.67 | C |
| ATOM | 3752 | O | GLU | B | 448 | 29.860 | -8.028 | 48.997 | 1.00 | 39.84 | O |
| ATOM | 3753 | N | VAL | B | 449 | 31.587 | -7.069 | 47.897 | 1.00 | 34.36 | N |
| ATOM | 3754 | CA | VAL | B | 449 | 31.629 | -5.916 | 48.785 | 1.00 | 32.48 | C |
| ATOM | 3755 | CB | VAL | B | 449 | 32.684 | -4.865 | 48.341 | 1.00 | 35.58 | C |
| ATOM | 3756 | CG1 | VAL | B | 449 | 32.416 | -3.522 | 49.032 | 1.00 | 33.49 | C |
| ATOM | 3757 | CG2 | VAL | B | 449 | 34.082 | -5.353 | 48.691 | 1.00 | 33.38 | C |
| ATOM | 3758 | C | VAL | B | 449 | 30.256 | -5.271 | 48.796 | 1.00 | 31.75 | C |
| ATOM | 3759 | O | VAL | B | 449 | 29.738 | -4.923 | 49.853 | 1.00 | 31.25 | O |
| ATOM | 3760 | N | ILE | B | 450 | 29.663 | -5.132 | 47.615 | 1.00 | 38.69 | N |
| ATOM | 3761 | CA | ILE | B | 450 | 28.343 | -4.530 | 47.495 | 1.00 | 39.34 | C |
| ATOM | 3762 | CB | ILE | B | 450 | 27.847 | -4.540 | 46.028 | 1.00 | 48.89 | C |
| ATOM | 3763 | CG2 | ILE | B | 450 | 26.447 | -3.937 | 45.944 | 1.00 | 47.74 | C |
| ATOM | 3764 | CG1 | ILE | B | 450 | 28.821 | -3.759 | 45.140 | 1.00 | 50.22 | C |

Figure 15

| | | | | | | | | | |
|---|---|---|---|---|---|---|---|---|---|
| ATOM | 3765 | CD1 | ILE | B | 450 | 29.025 | -2.334 | 45.560 | 1.00 50.37 | C |
| ATOM | 3766 | C | ILE | B | 450 | 27.321 | -5.279 | 48.358 | 1.00 39.41 | C |
| ATOM | 3767 | O | ILE | B | 450 | 26.549 | -4.656 | 49.087 | 1.00 38.95 | O |
| ATOM | 3768 | N | GLN | B | 451 | 27.318 | -6.610 | 48.266 | 1.00 35.91 | N |
| ATOM | 3769 | CA | GLN | B | 451 | 26.385 | -7.428 | 49.048 | 1.00 34.89 | C |
| ATOM | 3770 | CB | GLN | B | 451 | 26.575 | -8.922 | 48.758 | 1.00 43.11 | C |
| ATOM | 3771 | CG | GLN | B | 451 | 26.373 | -9.348 | 47.315 | 1.00 47.51 | C |
| ATOM | 3772 | CD | GLN | B | 451 | 26.868 | -10.772 | 47.055 | 1.00 49.87 | C |
| ATOM | 3773 | OE1 | GLN | B | 451 | 26.312 | -11.740 | 47.569 | 1.00 53.45 | O |
| ATOM | 3774 | NE2 | GLN | B | 451 | 27.923 | -10.897 | 46.264 | 1.00 50.66 | N |
| ATOM | 3775 | C | GLN | B | 451 | 26.593 | -7.201 | 50.537 | 1.00 32.67 | C |
| ATOM | 3776 | O | GLN | B | 451 | 25.639 | -7.081 | 51.291 | 1.00 31.77 | O |
| ATOM | 3777 | N | ASN | B | 452 | 27.851 | -7.153 | 50.952 | 1.00 30.65 | N |
| ATOM | 3778 | CA | ASN | B | 452 | 28.178 | -6.959 | 52.351 | 1.00 30.67 | C |
| ATOM | 3779 | CB | ASN | B | 452 | 29.663 | -7.262 | 52.577 | 1.00 32.01 | C |
| ATOM | 3780 | CG | ASN | B | 452 | 29.928 | -8.764 | 52.799 | 1.00 34.70 | C |
| ATOM | 3781 | OD1 | ASN | B | 452 | 29.732 | -9.285 | 53.893 | 1.00 34.81 | O |
| ATOM | 3782 | ND2 | ASN | B | 452 | 30.356 | -9.456 | 51.752 | 1.00 34.36 | N |
| ATOM | 3783 | C | ASN | B | 452 | 27.790 | -5.572 | 52.890 | 1.00 30.47 | C |
| ATOM | 3784 | O | ASN | B | 452 | 27.326 | -5.464 | 54.022 | 1.00 29.91 | O |
| ATOM | 3785 | N | LEU | B | 453 | 27.965 | -4.522 | 52.089 | 1.00 34.96 | N |
| ATOM | 3786 | CA | LEU | B | 453 | 27.586 | -3.180 | 52.533 | 1.00 34.91 | C |
| ATOM | 3787 | CB | LEU | B | 453 | 28.113 | -2.101 | 51.577 | 1.00 31.97 | C |
| ATOM | 3788 | CG | LEU | B | 453 | 29.627 | -1.879 | 51.630 | 1.00 32.72 | C |
| ATOM | 3789 | CD1 | LEU | B | 453 | 30.030 | -0.812 | 50.625 | 1.00 32.59 | C |
| ATOM | 3790 | CD2 | LEU | B | 453 | 30.031 | -1.471 | 53.048 | 1.00 32.97 | C |
| ATOM | 3791 | C | LEU | B | 453 | 26.067 | -3.102 | 52.617 | 1.00 35.04 | C |
| ATOM | 3792 | O | LEU | B | 453 | 25.517 | -2.357 | 53.420 | 1.00 33.15 | O |
| ATOM | 3793 | N | GLU | B | 454 | 25.379 | -3.876 | 51.787 | 1.00 30.55 | N |
| ATOM | 3794 | CA | GLU | B | 454 | 23.928 | -3.874 | 51.854 | 1.00 32.46 | C |
| ATOM | 3795 | CB | GLU | B | 454 | 23.333 | -4.789 | 50.782 | 1.00 51.42 | C |
| ATOM | 3796 | CG | GLU | B | 454 | 23.840 | -4.490 | 49.389 | 1.00 55.68 | C |
| ATOM | 3797 | CD | GLU | B | 454 | 23.070 | -5.226 | 48.315 | 1.00 58.20 | C |
| ATOM | 3798 | OE1 | GLU | B | 454 | 22.782 | -6.429 | 48.505 | 1.00 59.23 | O |
| ATOM | 3799 | OE2 | GLU | B | 454 | 22.763 | -4.599 | 47.278 | 1.00 59.43 | O |
| ATOM | 3800 | C | GLU | B | 454 | 23.503 | -4.365 | 53.246 | 1.00 31.75 | C |
| ATOM | 3801 | O | GLU | B | 454 | 22.436 | -4.013 | 53.733 | 1.00 31.66 | O |
| ATOM | 3802 | N | ARG | B | 455 | 24.365 | -5.166 | 53.874 | 1.00 34.19 | N |
| ATOM | 3803 | CA | ARG | B | 455 | 24.114 | -5.720 | 55.208 | 1.00 33.97 | C |
| ATOM | 3804 | CB | ARG | B | 455 | 24.548 | -7.187 | 55.267 | 1.00 39.01 | C |
| ATOM | 3805 | CG | ARG | B | 455 | 23.936 | -8.059 | 54.207 | 1.00 41.28 | C |
| ATOM | 3806 | CD | ARG | B | 455 | 24.297 | -9.517 | 54.459 | 1.00 43.91 | C |
| ATOM | 3807 | NE | ARG | B | 455 | 24.174 | -10.286 | 53.228 | 1.00 47.58 | N |
| ATOM | 3808 | CZ | ARG | B | 455 | 25.198 | -10.832 | 52.583 | 1.00 46.84 | C |
| ATOM | 3809 | NH1 | ARG | B | 455 | 26.433 | -10.707 | 53.053 | 1.00 43.70 | N |
| ATOM | 3810 | NH2 | ARG | B | 455 | 24.975 | -11.495 | 51.457 | 1.00 49.51 | N |
| ATOM | 3811 | C | ARG | B | 455 | 24.828 | -4.975 | 56.336 | 1.00 31.47 | C |
| ATOM | 3812 | O | ARG | B | 455 | 24.934 | -5.490 | 57.454 | 1.00 29.91 | O |
| ATOM | 3813 | N | GLY | B | 456 | 25.340 | -3.784 | 56.032 | 1.00 28.85 | N |
| ATOM | 3814 | CA | GLY | B | 456 | 26.015 | -2.982 | 57.039 | 1.00 26.90 | C |
| ATOM | 3815 | C | GLY | B | 456 | 27.387 | -3.466 | 57.457 | 1.00 26.63 | C |
| ATOM | 3816 | O | GLY | B | 456 | 27.852 | -3.160 | 58.545 | 1.00 27.82 | O |
| ATOM | 3817 | N | TYR | B | 457 | 28.049 | -4.212 | 56.588 | 1.00 29.25 | N |
| ATOM | 3818 | CA | TYR | B | 457 | 29.370 | -4.745 | 56.896 | 1.00 30.05 | C |
| ATOM | 3819 | CB | TYR | B | 457 | 29.769 | -5.772 | 55.819 | 1.00 28.92 | C |
| ATOM | 3820 | CG | TYR | B | 457 | 31.153 | -6.349 | 55.977 | 1.00 29.19 | C |
| ATOM | 3821 | CD1 | TYR | B | 457 | 32.260 | -5.734 | 55.394 | 1.00 29.53 | C |
| ATOM | 3822 | CE1 | TYR | B | 457 | 33.540 | -6.262 | 55.561 | 1.00 29.64 | C |
| ATOM | 3823 | CD2 | TYR | B | 457 | 31.358 | -7.516 | 56.732 | 1.00 29.70 | C |
| ATOM | 3824 | CE2 | TYR | B | 457 | 32.615 | -8.049 | 56.901 | 1.00 28.55 | C |

Figure 15

| ATOM | 3825 | CZ | TYR | B | 457 | 33.705 | -7.421 | 56.318 | 1.00 | 30.82 | C |
| ATOM | 3826 | OH | TYR | B | 457 | 34.961 | -7.947 | 56.514 | 1.00 | 32.48 | O |
| ATOM | 3827 | C | TYR | B | 457 | 30.441 | -3.653 | 56.999 | 1.00 | 31.20 | C |
| ATOM | 3828 | O | TYR | B | 457 | 30.404 | -2.673 | 56.260 | 1.00 | 32.87 | O |
| ATOM | 3829 | N | ARG | B | 458 | 31.383 | -3.831 | 57.922 | 1.00 | 27.60 | N |
| ATOM | 3830 | CA | ARG | B | 458 | 32.479 | -2.898 | 58.109 | 1.00 | 29.11 | C |
| ATOM | 3831 | CB | ARG | B | 458 | 32.220 | -1.972 | 59.314 | 1.00 | 30.90 | C |
| ATOM | 3832 | CG | ARG | B | 458 | 30.989 | -1.071 | 59.169 | 1.00 | 29.59 | C |
| ATOM | 3833 | CD | ARG | B | 458 | 31.167 | -0.056 | 58.047 | 1.00 | 28.89 | C |
| ATOM | 3834 | NE | ARG | B | 458 | 30.058 | 0.888 | 57.977 | 1.00 | 27.25 | N |
| ATOM | 3835 | CZ | ARG | B | 458 | 28.918 | 0.676 | 57.333 | 1.00 | 27.74 | C |
| ATOM | 3836 | NH1 | ARG | B | 458 | 28.713 | -0.463 | 56.678 | 1.00 | 29.18 | N |
| ATOM | 3837 | NH2 | ARG | B | 458 | 27.972 | 1.607 | 57.347 | 1.00 | 27.52 | N |
| ATOM | 3838 | C | ARG | B | 458 | 33.746 | -3.707 | 58.349 | 1.00 | 29.63 | C |
| ATOM | 3839 | O | ARG | B | 458 | 33.723 | -4.701 | 59.077 | 1.00 | 30.07 | O |
| ATOM | 3840 | N | MET | B | 459 | 34.843 | -3.299 | 57.724 | 1.00 | 29.59 | N |
| ATOM | 3841 | CA | MET | B | 459 | 36.109 | -3.998 | 57.906 | 1.00 | 30.99 | C |
| ATOM | 3842 | CB | MET | B | 459 | 37.227 | -3.341 | 57.102 | 1.00 | 34.09 | C |
| ATOM | 3843 | CG | MET | B | 459 | 37.181 | -3.555 | 55.607 | 1.00 | 37.29 | C |
| ATOM | 3844 | SD | MET | B | 459 | 38.662 | -2.819 | 54.864 | 1.00 | 37.60 | S |
| ATOM | 3845 | CE | MET | B | 459 | 38.025 | -1.173 | 54.455 | 1.00 | 37.71 | C |
| ATOM | 3846 | C | MET | B | 459 | 36.501 | -3.949 | 59.371 | 1.00 | 30.80 | C |
| ATOM | 3847 | O | MET | B | 459 | 36.184 | -2.988 | 60.070 | 1.00 | 30.40 | O |
| ATOM | 3848 | N | VAL | B | 460 | 37.202 | -4.979 | 59.826 | 1.00 | 34.64 | N |
| ATOM | 3849 | CA | VAL | B | 460 | 37.661 | -5.033 | 61.207 | 1.00 | 35.60 | C |
| ATOM | 3850 | CB | VAL | B | 460 | 37.962 | -6.490 | 61.642 | 1.00 | 31.50 | C |
| ATOM | 3851 | CG1 | VAL | B | 460 | 36.795 | -7.387 | 61.277 | 1.00 | 31.09 | C |
| ATOM | 3852 | CG2 | VAL | B | 460 | 39.231 | -6.986 | 60.972 | 1.00 | 32.51 | C |
| ATOM | 3853 | C | VAL | B | 460 | 38.951 | -4.221 | 61.280 | 1.00 | 36.20 | C |
| ATOM | 3854 | O | VAL | B | 460 | 39.440 | -3.726 | 60.267 | 1.00 | 36.23 | O |
| ATOM | 3855 | N | ARG | B | 461 | 39.508 | -4.093 | 62.471 | 1.00 | 35.11 | N |
| ATOM | 3856 | CA | ARG | B | 461 | 40.741 | -3.347 | 62.626 | 1.00 | 37.85 | C |
| ATOM | 3857 | CB | ARG | B | 461 | 41.079 | -3.176 | 64.102 | 1.00 | 46.17 | C |
| ATOM | 3858 | CG | ARG | B | 461 | 42.392 | -2.462 | 64.364 | 1.00 | 50.21 | C |
| ATOM | 3859 | CD | ARG | B | 461 | 42.518 | -2.107 | 65.832 | 1.00 | 52.91 | C |
| ATOM | 3860 | NE | ARG | B | 461 | 42.713 | -3.280 | 66.679 | 1.00 | 55.86 | N |
| ATOM | 3861 | CZ | ARG | B | 461 | 43.860 | -3.943 | 66.781 | 1.00 | 58.41 | C |
| ATOM | 3862 | NH1 | ARG | B | 461 | 44.920 | -3.545 | 66.084 | 1.00 | 59.92 | N |
| ATOM | 3863 | NH2 | ARG | B | 461 | 43.951 | -4.997 | 67.587 | 1.00 | 58.47 | N |
| ATOM | 3864 | C | ARG | B | 461 | 41.874 | -4.069 | 61.913 | 1.00 | 39.08 | C |
| ATOM | 3865 | O | ARG | B | 461 | 42.100 | -5.265 | 62.130 | 1.00 | 39.49 | O |
| ATOM | 3866 | N | PRO | B | 462 | 42.584 | -3.357 | 61.023 | 1.00 | 36.00 | N |
| ATOM | 3867 | CD | PRO | B | 462 | 42.265 | -2.000 | 60.551 | 1.00 | 31.31 | C |
| ATOM | 3868 | CA | PRO | B | 462 | 43.706 | -3.927 | 60.269 | 1.00 | 36.70 | C |
| ATOM | 3869 | CB | PRO | B | 462 | 44.045 | -2.825 | 59.253 | 1.00 | 32.42 | C |
| ATOM | 3870 | CG | PRO | B | 462 | 42.764 | -2.037 | 59.130 | 1.00 | 31.09 | C |
| ATOM | 3871 | C | PRO | B | 462 | 44.858 | -4.177 | 61.240 | 1.00 | 37.68 | C |
| ATOM | 3872 | O | PRO | B | 462 | 44.939 | -3.530 | 62.283 | 1.00 | 37.16 | O |
| ATOM | 3873 | N | ASP | B | 463 | 45.743 | -5.108 | 60.907 | 1.00 | 46.40 | N |
| ATOM | 3874 | CA | ASP | B | 463 | 46.867 | -5.401 | 61.786 | 1.00 | 49.29 | C |
| ATOM | 3875 | CB | ASP | B | 463 | 47.708 | -6.559 | 61.233 | 1.00 | 62.43 | C |
| ATOM | 3876 | CG | ASP | B | 463 | 46.968 | -7.882 | 61.260 | 1.00 | 63.18 | C |
| ATOM | 3877 | OD1 | ASP | B | 463 | 46.192 | -8.116 | 62.210 | 1.00 | 63.26 | O |
| ATOM | 3878 | OD2 | ASP | B | 463 | 47.170 | -8.694 | 60.332 | 1.00 | 66.24 | O |
| ATOM | 3879 | C | ASP | B | 463 | 47.749 | -4.182 | 61.989 | 1.00 | 50.38 | C |
| ATOM | 3880 | O | ASP | B | 463 | 47.919 | -3.371 | 61.082 | 1.00 | 50.95 | O |
| ATOM | 3881 | N | ASN | B | 464 | 48.301 | -4.058 | 63.194 | 1.00 | 58.73 | N |
| ATOM | 3882 | CA | ASN | B | 464 | 49.172 | -2.942 | 63.553 | 1.00 | 59.62 | C |
| ATOM | 3883 | CB | ASN | B | 464 | 50.489 | -3.017 | 62.772 | 1.00 | 93.45 | C |
| ATOM | 3884 | CG | ASN | B | 464 | 51.318 | -4.250 | 63.134 | 1.00 | 96.19 | C |

Figure 15

| | | | | | | | | | |
|---|---|---|---|---|---|---|---|---|---|
| ATOM | 3885 | OD1 | ASN | B | 464 | 51.496 | -4.572 | 64.314 | 1.00 97.97 | O |
| ATOM | 3886 | ND2 | ASN | B | 464 | 51.836 | -4.936 | 62.121 | 1.00 96.07 | N |
| ATOM | 3887 | C | ASN | B | 464 | 48.525 | -1.570 | 63.351 | 1.00 59.76 | C |
| ATOM | 3888 | O | ASN | B | 464 | 49.193 | -0.609 | 62.962 | 1.00 60.63 | O |
| ATOM | 3889 | N | CYS | B | 465 | 47.222 | -1.492 | 63.605 | 1.00 51.39 | N |
| ATOM | 3890 | CA | CYS | B | 465 | 46.483 | -0.240 | 63.492 | 1.00 49.32 | C |
| ATOM | 3891 | CB | CYS | B | 465 | 45.304 | -0.393 | 62.521 | 1.00 47.48 | C |
| ATOM | 3892 | SG | CYS | B | 465 | 44.096 | 0.978 | 62.550 | 1.00 46.41 | S |
| ATOM | 3893 | C | CYS | B | 465 | 45.967 | 0.130 | 64.883 | 1.00 48.11 | C |
| ATOM | 3894 | O | CYS | B | 465 | 45.261 | -0.641 | 65.521 | 1.00 48.12 | O |
| ATOM | 3895 | N | PRO | B | 466 | 46.340 | 1.312 | 65.381 | 1.00 46.97 | N |
| ATOM | 3896 | CD | PRO | B | 466 | 47.309 | 2.254 | 64.800 | 1.00 41.67 | C |
| ATOM | 3897 | CA | PRO | B | 466 | 45.895 | 1.761 | 66.706 | 1.00 46.29 | C |
| ATOM | 3898 | CB | PRO | B | 466 | 46.446 | 3.176 | 66.784 | 1.00 41.22 | C |
| ATOM | 3899 | CG | PRO | B | 466 | 47.715 | 3.074 | 66.005 | 1.00 42.18 | C |
| ATOM | 3900 | C | PRO | B | 466 | 44.365 | 1.731 | 66.822 | 1.00 46.46 | C |
| ATOM | 3901 | O | PRO | B | 466 | 43.657 | 2.077 | 65.872 | 1.00 46.56 | O |
| ATOM | 3902 | N | GLU | B | 467 | 43.862 | 1.318 | 67.982 | 1.00 45.37 | N |
| ATOM | 3903 | CA | GLU | B | 467 | 42.420 | 1.248 | 68.220 | 1.00 44.98 | C |
| ATOM | 3904 | CB | GLU | B | 467 | 42.119 | 0.826 | 69.665 | 1.00 43.56 | C |
| ATOM | 3905 | CG | GLU | B | 467 | 41.443 | -0.542 | 69.790 | 1.00 46.08 | C |
| ATOM | 3906 | CD | GLU | B | 467 | 40.147 | -0.656 | 68.994 | 1.00 46.25 | C |
| ATOM | 3907 | OE1 | GLU | B | 467 | 39.186 | 0.083 | 69.295 | 1.00 48.07 | O |
| ATOM | 3908 | OE2 | GLU | B | 467 | 40.092 | -1.489 | 68.069 | 1.00 45.80 | O |
| ATOM | 3909 | C | GLU | B | 467 | 41.751 | 2.587 | 67.967 | 1.00 44.35 | C |
| ATOM | 3910 | O | GLU | B | 467 | 40.642 | 2.645 | 67.434 | 1.00 43.76 | O |
| ATOM | 3911 | N | GLU | B | 468 | 42.423 | 3.656 | 68.385 | 1.00 39.03 | N |
| ATOM | 3912 | CA | GLU | B | 468 | 41.899 | 4.994 | 68.212 | 1.00 38.35 | C |
| ATOM | 3913 | CB | GLU | B | 468 | 42.792 | 6.014 | 68.919 | 1.00 79.20 | C |
| ATOM | 3914 | CG | GLU | B | 468 | 43.185 | 5.637 | 70.341 | 1.00 84.00 | C |
| ATOM | 3915 | CD | GLU | B | 468 | 44.538 | 4.947 | 70.389 | 1.00 87.66 | C |
| ATOM | 3916 | OE1 | GLU | B | 468 | 45.548 | 5.595 | 70.019 | 1.00 90.55 | O |
| ATOM | 3917 | OE2 | GLU | B | 468 | 44.595 | 3.763 | 70.786 | 1.00 88.47 | O |
| ATOM | 3918 | C | GLU | B | 468 | 41.821 | 5.315 | 66.726 | 1.00 37.30 | C |
| ATOM | 3919 | O | GLU | B | 468 | 40.919 | 6.029 | 66.288 | 1.00 37.03 | O |
| ATOM | 3920 | N | LEU | B | 469 | 42.766 | 4.788 | 65.949 | 1.00 36.11 | N |
| ATOM | 3921 | CA | LEU | B | 469 | 42.754 | 5.033 | 64.517 | 1.00 34.25 | C |
| ATOM | 3922 | CB | LEU | B | 469 | 44.049 | 4.553 | 63.857 | 1.00 45.43 | C |
| ATOM | 3923 | CG | LEU | B | 469 | 44.128 | 4.930 | 62.374 | 1.00 46.99 | C |
| ATOM | 3924 | CD1 | LEU | B | 469 | 43.909 | 6.439 | 62.219 | 1.00 45.88 | C |
| ATOM | 3925 | CD2 | LEU | B | 469 | 45.481 | 4.529 | 61.804 | 1.00 46.09 | C |
| ATOM | 3926 | C | LEU | B | 469 | 41.570 | 4.294 | 63.929 | 1.00 32.59 | C |
| ATOM | 3927 | O | LEU | B | 469 | 40.834 | 4.841 | 63.109 | 1.00 30.86 | O |
| ATOM | 3928 | N | TYR | B | 470 | 41.383 | 3.049 | 64.367 | 1.00 35.86 | N |
| ATOM | 3929 | CA | TYR | B | 470 | 40.274 | 2.229 | 63.894 | 1.00 34.08 | C |
| ATOM | 3930 | CB | TYR | B | 470 | 40.330 | 0.838 | 64.526 | 1.00 30.13 | C |
| ATOM | 3931 | CG | TYR | B | 470 | 39.187 | -0.053 | 64.080 | 1.00 30.28 | C |
| ATOM | 3932 | CD1 | TYR | B | 470 | 39.006 | -0.348 | 62.732 | 1.00 27.79 | C |
| ATOM | 3933 | CE1 | TYR | B | 470 | 37.963 | -1.134 | 62.306 | 1.00 29.69 | C |
| ATOM | 3934 | CD2 | TYR | B | 470 | 38.284 | -0.584 | 65.001 | 1.00 29.69 | C |
| ATOM | 3935 | CE2 | TYR | B | 470 | 37.227 | -1.384 | 64.578 | 1.00 31.03 | C |
| ATOM | 3936 | CZ | TYR | B | 470 | 37.070 | -1.652 | 63.220 | 1.00 30.98 | C |
| ATOM | 3937 | OH | TYR | B | 470 | 36.002 | -2.400 | 62.767 | 1.00 30.05 | O |
| ATOM | 3938 | C | TYR | B | 470 | 38.912 | 2.858 | 64.203 | 1.00 33.74 | C |
| ATOM | 3939 | O | TYR | B | 470 | 37.991 | 2.798 | 63.387 | 1.00 32.99 | O |
| ATOM | 3940 | N | GLN | B | 471 | 38.772 | 3.446 | 65.387 | 1.00 33.30 | N |
| ATOM | 3941 | CA | GLN | B | 471 | 37.503 | 4.071 | 65.729 | 1.00 35.19 | C |
| ATOM | 3942 | CB | GLN | B | 471 | 37.445 | 4.421 | 67.220 | 1.00 37.76 | C |
| ATOM | 3943 | CG | GLN | B | 471 | 37.346 | 3.196 | 68.118 | 1.00 40.44 | C |
| ATOM | 3944 | CD | GLN | B | 471 | 36.131 | 2.323 | 67.800 | 1.00 44.32 | C |

Figure 15

| | | | | | | | | | |
|---|---|---|---|---|---|---|---|---|---|
| ATOM | 3945 | OE1 | GLN B 471 | 34.993 | 2.806 | 67.755 | 1.00 | 45.25 | O |
| ATOM | 3946 | NE2 | GLN B 471 | 36.367 | 1.029 | 67.591 | 1.00 | 44.62 | N |
| ATOM | 3947 | C | GLN B 471 | 37.259 | 5.310 | 64.864 | 1.00 | 33.92 | C |
| ATOM | 3948 | O | GLN B 471 | 36.112 | 5.663 | 64.594 | 1.00 | 33.86 | O |
| ATOM | 3949 | N | LEU B 472 | 38.334 | 5.958 | 64.427 | 1.00 | 32.63 | N |
| ATOM | 3950 | CA | LEU B 472 | 38.209 | 7.125 | 63.544 | 1.00 | 32.79 | C |
| ATOM | 3951 | CB | LEU B 472 | 39.583 | 7.749 | 63.276 | 1.00 | 45.55 | C |
| ATOM | 3952 | CG | LEU B 472 | 39.737 | 9.230 | 63.641 | 1.00 | 50.41 | C |
| ATOM | 3953 | CD1 | LEU B 472 | 39.310 | 9.445 | 65.082 | 1.00 | 49.45 | C |
| ATOM | 3954 | CD2 | LEU B 472 | 41.191 | 9.679 | 63.433 | 1.00 | 51.04 | C |
| ATOM | 3955 | C | LEU B 472 | 37.606 | 6.619 | 62.225 | 1.00 | 31.05 | C |
| ATOM | 3956 | O | LEU B 472 | 36.677 | 7.216 | 61.671 | 1.00 | 30.45 | O |
| ATOM | 3957 | N | MET B 473 | 38.140 | 5.502 | 61.743 | 1.00 | 25.63 | N |
| ATOM | 3958 | CA | MET B 473 | 37.664 | 4.889 | 60.509 | 1.00 | 25.49 | C |
| ATOM | 3959 | CB | MET B 473 | 38.418 | 3.595 | 60.216 | 1.00 | 29.58 | C |
| ATOM | 3960 | CG | MET B 473 | 39.924 | 3.712 | 60.200 | 1.00 | 30.41 | C |
| ATOM | 3961 | SD | MET B 473 | 40.714 | 2.069 | 60.148 | 1.00 | 32.01 | S |
| ATOM | 3962 | CE | MET B 473 | 42.371 | 2.550 | 59.570 | 1.00 | 29.97 | C |
| ATOM | 3963 | C | MET B 473 | 36.176 | 4.577 | 60.604 | 1.00 | 24.88 | C |
| ATOM | 3964 | O | MET B 473 | 35.432 | 4.843 | 59.671 | 1.00 | 24.00 | O |
| ATOM | 3965 | N | ARG B 474 | 35.751 | 4.021 | 61.735 | 1.00 | 28.31 | N |
| ATOM | 3966 | CA | ARG B 474 | 34.348 | 3.675 | 61.934 | 1.00 | 28.66 | C |
| ATOM | 3967 | CB | ARG B 474 | 34.142 | 2.954 | 63.279 | 1.00 | 33.18 | C |
| ATOM | 3968 | CG | ARG B 474 | 34.796 | 1.553 | 63.355 | 1.00 | 34.48 | C |
| ATOM | 3969 | CD | ARG B 474 | 34.292 | 0.628 | 62.242 | 1.00 | 34.15 | C |
| ATOM | 3970 | NE | ARG B 474 | 32.865 | 0.369 | 62.364 | 1.00 | 34.03 | N |
| ATOM | 3971 | CZ | ARG B 474 | 32.332 | -0.722 | 62.905 | 1.00 | 34.25 | C |
| ATOM | 3972 | NH1 | ARG B 474 | 33.107 | -1.697 | 63.378 | 1.00 | 29.71 | N |
| ATOM | 3973 | NH2 | ARG B 474 | 31.012 | -0.819 | 62.999 | 1.00 | 30.63 | N |
| ATOM | 3974 | C | ARG B 474 | 33.474 | 4.916 | 61.863 | 1.00 | 28.44 | C |
| ATOM | 3975 | O | ARG B 474 | 32.354 | 4.871 | 61.356 | 1.00 | 28.37 | O |
| ATOM | 3976 | N | LEU B 475 | 33.973 | 6.034 | 62.369 | 1.00 | 27.28 | N |
| ATOM | 3977 | CA | LEU B 475 | 33.197 | 7.263 | 62.292 | 1.00 | 27.23 | C |
| ATOM | 3978 | CB | LEU B 475 | 33.900 | 8.391 | 63.053 | 1.00 | 33.39 | C |
| ATOM | 3979 | CG | LEU B 475 | 33.816 | 8.182 | 64.567 | 1.00 | 36.34 | C |
| ATOM | 3980 | CD1 | LEU B 475 | 34.576 | 9.283 | 65.303 | 1.00 | 33.94 | C |
| ATOM | 3981 | CD2 | LEU B 475 | 32.332 | 8.155 | 64.973 | 1.00 | 35.55 | C |
| ATOM | 3982 | C | LEU B 475 | 33.042 | 7.630 | 60.827 | 1.00 | 25.99 | C |
| ATOM | 3983 | O | LEU B 475 | 31.969 | 8.000 | 60.387 | 1.00 | 25.97 | O |
| ATOM | 3984 | N | CYS B 476 | 34.128 | 7.514 | 60.069 | 1.00 | 28.84 | N |
| ATOM | 3985 | CA | CYS B 476 | 34.093 | 7.825 | 58.644 | 1.00 | 28.40 | C |
| ATOM | 3986 | CB | CYS B 476 | 35.480 | 7.673 | 58.006 | 1.00 | 29.89 | C |
| ATOM | 3987 | SG | CYS B 476 | 36.739 | 8.872 | 58.499 | 1.00 | 33.75 | S |
| ATOM | 3988 | C | CYS B 476 | 33.133 | 6.882 | 57.935 | 1.00 | 28.66 | C |
| ATOM | 3989 | O | CYS B 476 | 32.596 | 7.215 | 56.877 | 1.00 | 29.27 | O |
| ATOM | 3990 | N | TRP B 477 | 32.904 | 5.704 | 58.507 | 1.00 | 28.97 | N |
| ATOM | 3991 | CA | TRP B 477 | 32.013 | 4.757 | 57.852 | 1.00 | 30.34 | C |
| ATOM | 3992 | CB | TRP B 477 | 32.606 | 3.340 | 57.873 | 1.00 | 31.28 | C |
| ATOM | 3993 | CG | TRP B 477 | 33.974 | 3.233 | 57.301 | 1.00 | 31.55 | C |
| ATOM | 3994 | CD2 | TRP B 477 | 34.980 | 2.284 | 57.674 | 1.00 | 31.67 | C |
| ATOM | 3995 | CE2 | TRP B 477 | 36.092 | 2.511 | 56.845 | 1.00 | 32.00 | C |
| ATOM | 3996 | CE3 | TRP B 477 | 35.045 | 1.262 | 58.633 | 1.00 | 33.54 | C |
| ATOM | 3997 | CD1 | TRP B 477 | 34.501 | 3.981 | 56.288 | 1.00 | 31.91 | C |
| ATOM | 3998 | NE1 | TRP B 477 | 35.774 | 3.554 | 56.006 | 1.00 | 33.10 | N |
| ATOM | 3999 | CZ2 | TRP B 477 | 37.265 | 1.756 | 56.941 | 1.00 | 31.17 | C |
| ATOM | 4000 | CZ3 | TRP B 477 | 36.217 | 0.508 | 58.732 | 1.00 | 33.85 | C |
| ATOM | 4001 | CH2 | TRP B 477 | 37.311 | 0.766 | 57.886 | 1.00 | 32.29 | C |
| ATOM | 4002 | C | TRP B 477 | 30.593 | 4.695 | 58.406 | 1.00 | 29.98 | C |
| ATOM | 4003 | O | TRP B 477 | 29.899 | 3.697 | 58.196 | 1.00 | 29.18 | O |
| ATOM | 4004 | N | LYS B 478 | 30.166 | 5.736 | 59.116 | 1.00 | 28.28 | N |

Figure 15

| | | | | | | | | | | |
|---|---|---|---|---|---|---|---|---|---|---|
| ATOM | 4005 | CA | LYS | B | 478 | 28.801 | 5.767 | 59.657 | 1.00 28.38 | C |
| ATOM | 4006 | CB | LYS | B | 478 | 28.537 | 7.072 | 60.419 | 1.00 35.61 | C |
| ATOM | 4007 | CG | LYS | B | 478 | 29.283 | 7.204 | 61.754 | 1.00 38.34 | C |
| ATOM | 4008 | CD | LYS | B | 478 | 28.885 | 6.092 | 62.708 | 1.00 41.22 | C |
| ATOM | 4009 | CE | LYS | B | 478 | 27.392 | 6.125 | 62.993 | 1.00 43.56 | C |
| ATOM | 4010 | NZ | LYS | B | 478 | 26.943 | 4.996 | 63.864 | 1.00 48.15 | N |
| ATOM | 4011 | C | LYS | B | 478 | 27.878 | 5.690 | 58.455 | 1.00 27.67 | C |
| ATOM | 4012 | O | LYS | B | 478 | 28.141 | 6.324 | 57.431 | 1.00 26.87 | O |
| ATOM | 4013 | N | GLU | B | 479 | 26.813 | 4.903 | 58.577 | 1.00 30.41 | N |
| ATOM | 4014 | CA | GLU | B | 479 | 25.852 | 4.725 | 57.497 | 1.00 30.94 | C |
| ATOM | 4015 | CB | GLU | B | 479 | 24.702 | 3.813 | 57.944 | 1.00 25.59 | C |
| ATOM | 4016 | CG | GLU | B | 479 | 23.725 | 3.443 | 56.814 | 1.00 25.97 | C |
| ATOM | 4017 | CD | GLU | B | 479 | 24.398 | 2.636 | 55.694 | 1.00 26.67 | C |
| ATOM | 4018 | OE1 | GLU | B | 479 | 25.312 | 1.849 | 56.005 | 1.00 26.17 | O |
| ATOM | 4019 | OE2 | GLU | B | 479 | 24.012 | 2.777 | 54.512 | 1.00 27.64 | O |
| ATOM | 4020 | C | GLU | B | 479 | 25.272 | 6.058 | 57.001 | 1.00 31.51 | C |
| ATOM | 4021 | O | GLU | B | 479 | 25.245 | 6.311 | 55.806 | 1.00 32.51 | O |
| ATOM | 4022 | N | ARG | B | 480 | 24.787 | 6.886 | 57.918 | 1.00 28.01 | N |
| ATOM | 4023 | CA | ARG | B | 480 | 24.210 | 8.185 | 57.554 | 1.00 29.70 | C |
| ATOM | 4024 | CB | ARG | B | 480 | 23.248 | 8.670 | 58.638 | 1.00 44.70 | C |
| ATOM | 4025 | CG | ARG | B | 480 | 22.024 | 7.782 | 58.810 | 1.00 49.98 | C |
| ATOM | 4026 | CD | ARG | B | 480 | 21.154 | 8.238 | 59.971 | 1.00 53.87 | C |
| ATOM | 4027 | NE | ARG | B | 480 | 20.018 | 7.343 | 60.140 | 1.00 59.97 | N |
| ATOM | 4028 | CZ | ARG | B | 480 | 19.049 | 7.499 | 61.037 | 1.00 62.37 | C |
| ATOM | 4029 | NH1 | ARG | B | 480 | 19.061 | 8.534 | 61.874 | 1.00 64.16 | N |
| ATOM | 4030 | NH2 | ARG | B | 480 | 18.063 | 6.610 | 61.095 | 1.00 62.89 | N |
| ATOM | 4031 | C | ARG | B | 480 | 25.351 | 9.172 | 57.393 | 1.00 28.01 | C |
| ATOM | 4032 | O | ARG | B | 480 | 26.185 | 9.308 | 58.287 | 1.00 28.00 | O |
| ATOM | 4033 | N | PRO | B | 481 | 25.413 | 9.856 | 56.244 | 1.00 26.25 | N |
| ATOM | 4034 | CD | PRO | B | 481 | 24.442 | 9.828 | 55.136 | 1.00 31.45 | C |
| ATOM | 4035 | CA | PRO | B | 481 | 26.480 | 10.830 | 55.979 | 1.00 26.04 | C |
| ATOM | 4036 | CB | PRO | B | 481 | 26.093 | 11.412 | 54.622 | 1.00 30.84 | C |
| ATOM | 4037 | CG | PRO | B | 481 | 25.282 | 10.293 | 53.972 | 1.00 31.22 | C |
| ATOM | 4038 | C | PRO | B | 481 | 26.635 | 11.910 | 57.044 | 1.00 25.61 | C |
| ATOM | 4039 | O | PRO | B | 481 | 27.753 | 12.301 | 57.362 | 1.00 25.16 | O |
| ATOM | 4040 | N | GLU | B | 482 | 25.524 | 12.386 | 57.608 | 1.00 30.69 | N |
| ATOM | 4041 | CA | GLU | B | 482 | 25.595 | 13.444 | 58.617 | 1.00 31.04 | C |
| ATOM | 4042 | CB | GLU | B | 482 | 24.190 | 13.957 | 58.983 | 1.00 29.57 | C |
| ATOM | 4043 | CG | GLU | B | 482 | 23.312 | 12.943 | 59.705 | 1.00 30.25 | C |
| ATOM | 4044 | CD | GLU | B | 482 | 22.456 | 12.117 | 58.769 | 1.00 30.52 | C |
| ATOM | 4045 | OE1 | GLU | B | 482 | 22.792 | 11.994 | 57.579 | 1.00 32.79 | O |
| ATOM | 4046 | OE2 | GLU | B | 482 | 21.439 | 11.575 | 59.234 | 1.00 33.34 | O |
| ATOM | 4047 | C | GLU | B | 482 | 26.340 | 13.006 | 59.881 | 1.00 31.77 | C |
| ATOM | 4048 | O | GLU | B | 482 | 26.844 | 13.839 | 60.629 | 1.00 32.51 | O |
| ATOM | 4049 | N | ASP | B | 483 | 26.420 | 11.698 | 60.125 | 1.00 29.60 | N |
| ATOM | 4050 | CA | ASP | B | 483 | 27.137 | 11.219 | 61.304 | 1.00 29.19 | C |
| ATOM | 4051 | CB | ASP | B | 483 | 26.549 | 9.902 | 61.806 | 1.00 32.23 | C |
| ATOM | 4052 | CG | ASP | B | 483 | 25.135 | 10.065 | 62.299 | 1.00 33.72 | C |
| ATOM | 4053 | OD1 | ASP | B | 483 | 24.841 | 11.112 | 62.905 | 1.00 36.47 | O |
| ATOM | 4054 | OD2 | ASP | B | 483 | 24.325 | 9.158 | 62.084 | 1.00 34.27 | O |
| ATOM | 4055 | C | ASP | B | 483 | 28.619 | 11.046 | 61.042 | 1.00 28.75 | C |
| ATOM | 4056 | O | ASP | B | 483 | 29.377 | 10.696 | 61.932 | 1.00 29.30 | O |
| ATOM | 4057 | N | ARG | B | 484 | 29.055 | 11.277 | 59.817 | 1.00 29.09 | N |
| ATOM | 4058 | CA | ARG | B | 484 | 30.485 | 11.148 | 59.567 | 1.00 29.11 | C |
| ATOM | 4059 | CB | ARG | B | 484 | 30.746 | 10.808 | 58.095 | 1.00 28.27 | C |
| ATOM | 4060 | CG | ARG | B | 484 | 30.077 | 9.525 | 57.656 | 1.00 26.98 | C |
| ATOM | 4061 | CD | ARG | B | 484 | 30.243 | 9.250 | 56.165 | 1.00 26.27 | C |
| ATOM | 4062 | NE | ARG | B | 484 | 29.304 | 8.216 | 55.763 | 1.00 25.08 | N |
| ATOM | 4063 | CZ | ARG | B | 484 | 28.795 | 8.062 | 54.545 | 1.00 25.28 | C |
| ATOM | 4064 | NH1 | ARG | B | 484 | 29.140 | 8.882 | 53.554 | 1.00 23.96 | N |

Figure 15

| ATOM | 4065 | NH2 | ARG | B | 484 | 27.889 | 7.110  | 54.339 | 1.00 | 23.67 | N |
| ---- | ---- | --- | --- | - | --- | ------ | ------ | ------ | ---- | ----- | - |
| ATOM | 4066 | C   | ARG | B | 484 | 31.118 | 12.487 | 59.932 | 1.00 | 28.74 | C |
| ATOM | 4067 | O   | ARG | B | 484 | 30.510 | 13.534 | 59.761 | 1.00 | 28.36 | O |
| ATOM | 4068 | N   | PRO | B | 485 | 32.353 | 12.465 | 60.447 | 1.00 | 28.45 | N |
| ATOM | 4069 | CD  | PRO | B | 485 | 33.187 | 11.290 | 60.765 | 1.00 | 31.90 | C |
| ATOM | 4070 | CA  | PRO | B | 485 | 33.025 | 13.709 | 60.822 | 1.00 | 27.62 | C |
| ATOM | 4071 | CB  | PRO | B | 485 | 34.255 | 13.217 | 61.577 | 1.00 | 33.93 | C |
| ATOM | 4072 | CG  | PRO | B | 485 | 34.559 | 11.903 | 60.890 | 1.00 | 33.65 | C |
| ATOM | 4073 | C   | PRO | B | 485 | 33.405 | 14.573 | 59.627 | 1.00 | 28.85 | C |
| ATOM | 4074 | O   | PRO | B | 485 | 33.356 | 14.129 | 58.478 | 1.00 | 29.41 | O |
| ATOM | 4075 | N   | THR | B | 486 | 33.778 | 15.816 | 59.904 | 1.00 | 26.69 | N |
| ATOM | 4076 | CA  | THR | B | 486 | 34.213 | 16.726 | 58.856 | 1.00 | 26.00 | C |
| ATOM | 4077 | CB  | THR | B | 486 | 34.075 | 18.204 | 59.272 | 1.00 | 28.77 | C |
| ATOM | 4078 | OG1 | THR | B | 486 | 34.809 | 18.408 | 60.491 | 1.00 | 29.80 | O |
| ATOM | 4079 | CG2 | THR | B | 486 | 32.623 | 18.598 | 59.462 | 1.00 | 26.72 | C |
| ATOM | 4080 | C   | THR | B | 486 | 35.711 | 16.464 | 58.685 | 1.00 | 26.12 | C |
| ATOM | 4081 | O   | THR | B | 486 | 36.351 | 15.891 | 59.561 | 1.00 | 24.18 | O |
| ATOM | 4082 | N   | PHE | B | 487 | 36.262 | 16.893 | 57.560 | 1.00 | 27.11 | N |
| ATOM | 4083 | CA  | PHE | B | 487 | 37.681 | 16.732 | 57.334 | 1.00 | 28.49 | C |
| ATOM | 4084 | CB  | PHE | B | 487 | 38.025 | 17.018 | 55.877 | 1.00 | 28.56 | C |
| ATOM | 4085 | CG  | PHE | B | 487 | 37.833 | 15.839 | 54.976 | 1.00 | 28.05 | C |
| ATOM | 4086 | CD1 | PHE | B | 487 | 38.646 | 14.721 | 55.100 | 1.00 | 27.07 | C |
| ATOM | 4087 | CD2 | PHE | B | 487 | 36.863 | 15.855 | 53.989 | 1.00 | 27.61 | C |
| ATOM | 4088 | CE1 | PHE | B | 487 | 38.500 | 13.637 | 54.243 | 1.00 | 27.83 | C |
| ATOM | 4089 | CE2 | PHE | B | 487 | 36.708 | 14.773 | 53.130 | 1.00 | 28.93 | C |
| ATOM | 4090 | CZ  | PHE | B | 487 | 37.527 | 13.664 | 53.255 | 1.00 | 26.66 | C |
| ATOM | 4091 | C   | PHE | B | 487 | 38.424 | 17.679 | 58.253 | 1.00 | 30.15 | C |
| ATOM | 4092 | O   | PHE | B | 487 | 39.592 | 17.450 | 58.581 | 1.00 | 30.08 | O |
| ATOM | 4093 | N   | ASP | B | 488 | 37.735 | 18.740 | 58.669 | 1.00 | 31.48 | N |
| ATOM | 4094 | CA  | ASP | B | 488 | 38.320 | 19.718 | 59.580 | 1.00 | 33.20 | C |
| ATOM | 4095 | CB  | ASP | B | 488 | 37.353 | 20.898 | 59.793 | 1.00 | 41.17 | C |
| ATOM | 4096 | CG  | ASP | B | 488 | 37.843 | 21.878 | 60.850 | 1.00 | 44.10 | C |
| ATOM | 4097 | OD1 | ASP | B | 488 | 39.068 | 21.948 | 61.071 | 1.00 | 46.93 | O |
| ATOM | 4098 | OD2 | ASP | B | 488 | 37.004 | 22.585 | 61.452 | 1.00 | 44.51 | O |
| ATOM | 4099 | C   | ASP | B | 488 | 38.627 | 19.014 | 60.905 | 1.00 | 33.03 | C |
| ATOM | 4100 | O   | ASP | B | 488 | 39.642 | 19.285 | 61.539 | 1.00 | 33.13 | O |
| ATOM | 4101 | N   | TYR | B | 489 | 37.750 | 18.102 | 61.313 | 1.00 | 32.43 | N |
| ATOM | 4102 | CA  | TYR | B | 489 | 37.961 | 17.341 | 62.545 | 1.00 | 32.96 | C |
| ATOM | 4103 | CB  | TYR | B | 489 | 36.660 | 16.663 | 62.995 | 1.00 | 31.37 | C |
| ATOM | 4104 | CG  | TYR | B | 489 | 36.859 | 15.716 | 64.154 | 1.00 | 29.71 | C |
| ATOM | 4105 | CD1 | TYR | B | 489 | 37.175 | 16.194 | 65.425 | 1.00 | 28.51 | C |
| ATOM | 4106 | CE1 | TYR | B | 489 | 37.409 | 15.327 | 66.474 | 1.00 | 29.16 | C |
| ATOM | 4107 | CD2 | TYR | B | 489 | 36.779 | 14.336 | 63.966 | 1.00 | 29.94 | C |
| ATOM | 4108 | CE2 | TYR | B | 489 | 37.010 | 13.459 | 64.997 | 1.00 | 28.38 | C |
| ATOM | 4109 | CZ  | TYR | B | 489 | 37.330 | 13.952 | 66.252 | 1.00 | 31.15 | C |
| ATOM | 4110 | OH  | TYR | B | 489 | 37.620 | 13.073 | 67.263 | 1.00 | 30.87 | O |
| ATOM | 4111 | C   | TYR | B | 489 | 39.050 | 16.276 | 62.341 | 1.00 | 33.23 | C |
| ATOM | 4112 | O   | TYR | B | 489 | 39.974 | 16.163 | 63.151 | 1.00 | 33.31 | O |
| ATOM | 4113 | N   | LEU | B | 490 | 38.941 | 15.504 | 61.260 | 1.00 | 29.41 | N |
| ATOM | 4114 | CA  | LEU | B | 490 | 39.927 | 14.463 | 60.948 | 1.00 | 29.69 | C |
| ATOM | 4115 | CB  | LEU | B | 490 | 39.593 | 13.815 | 59.598 | 1.00 | 29.50 | C |
| ATOM | 4116 | CG  | LEU | B | 490 | 38.301 | 12.980 | 59.578 | 1.00 | 29.31 | C |
| ATOM | 4117 | CD1 | LEU | B | 490 | 37.964 | 12.501 | 58.183 | 1.00 | 27.67 | C |
| ATOM | 4118 | CD2 | LEU | B | 490 | 38.486 | 11.795 | 60.504 | 1.00 | 28.41 | C |
| ATOM | 4119 | C   | LEU | B | 490 | 41.356 | 15.026 | 60.928 | 1.00 | 31.01 | C |
| ATOM | 4120 | O   | LEU | B | 490 | 42.294 | 14.399 | 61.427 | 1.00 | 29.29 | O |
| ATOM | 4121 | N   | ARG | B | 491 | 41.513 | 16.214 | 60.347 | 1.00 | 37.55 | N |
| ATOM | 4122 | CA  | ARG | B | 491 | 42.813 | 16.858 | 60.293 | 1.00 | 39.86 | C |
| ATOM | 4123 | CB  | ARG | B | 491 | 42.707 | 18.202 | 59.567 | 1.00 | 51.49 | C |
| ATOM | 4124 | CG  | ARG | B | 491 | 43.995 | 19.027 | 59.602 | 1.00 | 53.95 | C |

Figure 15

```
ATOM   4125  CD   ARG B 491      43.769  20.444  59.107  1.00 57.09           C
ATOM   4126  NE   ARG B 491      42.725  21.124  59.872  1.00 61.80           N
ATOM   4127  CZ   ARG B 491      42.771  21.325  61.187  1.00 63.50           C
ATOM   4128  NH1  ARG B 491      43.816  20.906  61.889  1.00 64.63           N
ATOM   4129  NH2  ARG B 491      41.762  21.928  61.804  1.00 64.45           N
ATOM   4130  C    ARG B 491      43.331  17.077  61.718  1.00 40.82           C
ATOM   4131  O    ARG B 491      44.435  16.644  62.068  1.00 41.16           O
ATOM   4132  N    SER B 492      42.518  17.734  62.542  1.00 38.68           N
ATOM   4133  CA   SER B 492      42.895  18.022  63.919  1.00 39.73           C
ATOM   4134  CB   SER B 492      41.754  18.750  64.632  1.00 52.04           C
ATOM   4135  OG   SER B 492      41.553  20.033  64.060  1.00 57.77           O
ATOM   4136  C    SER B 492      43.309  16.800  64.729  1.00 39.51           C
ATOM   4137  O    SER B 492      44.371  16.792  65.341  1.00 39.41           O
ATOM   4138  N    VAL B 493      42.474  15.769  64.736  1.00 40.43           N
ATOM   4139  CA   VAL B 493      42.787  14.564  65.495  1.00 40.78           C
ATOM   4140  CB   VAL B 493      41.563  13.613  65.559  1.00 54.37           C
ATOM   4141  CG1  VAL B 493      40.931  13.493  64.190  1.00 54.89           C
ATOM   4142  CG2  VAL B 493      41.998  12.223  66.069  1.00 54.39           C
ATOM   4143  C    VAL B 493      43.996  13.805  64.953  1.00 40.46           C
ATOM   4144  O    VAL B 493      44.763  13.239  65.723  1.00 40.15           O
ATOM   4145  N    LEU B 494      44.186  13.796  63.636  1.00 37.40           N
ATOM   4146  CA   LEU B 494      45.334  13.088  63.075  1.00 38.21           C
ATOM   4147  CB   LEU B 494      45.155  12.855  61.567  1.00 35.08           C
ATOM   4148  CG   LEU B 494      44.059  11.831  61.246  1.00 35.17           C
ATOM   4149  CD1  LEU B 494      43.837  11.721  59.756  1.00 33.39           C
ATOM   4150  CD2  LEU B 494      44.455  10.485  61.826  1.00 34.76           C
ATOM   4151  C    LEU B 494      46.643  13.829  63.349  1.00 38.88           C
ATOM   4152  O    LEU B 494      47.651  13.206  63.644  1.00 37.59           O
ATOM   4153  N    GLU B 495      46.618  15.156  63.266  1.00 43.46           N
ATOM   4154  CA   GLU B 495      47.821  15.950  63.517  1.00 46.48           C
ATOM   4155  CB   GLU B 495      47.567  17.435  63.231  1.00 61.14           C
ATOM   4156  CG   GLU B 495      47.105  17.732  61.810  1.00 63.93           C
ATOM   4157  CD   GLU B 495      47.126  19.213  61.478  1.00 64.59           C
ATOM   4158  OE1  GLU B 495      46.533  20.009  62.243  1.00 65.71           O
ATOM   4159  OE2  GLU B 495      47.731  19.579  60.448  1.00 65.24           O
ATOM   4160  C    GLU B 495      48.327  15.803  64.949  1.00 48.03           C
ATOM   4161  O    GLU B 495      49.527  15.867  65.193  1.00 47.97           O
ATOM   4162  N    ASP B 496      47.417  15.609  65.899  1.00 49.48           N
ATOM   4163  CA   ASP B 496      47.824  15.462  67.292  1.00 51.38           C
ATOM   4164  CB   ASP B 496      47.112  16.502  68.172  1.00 72.15           C
ATOM   4165  CG   ASP B 496      47.622  17.920  67.931  1.00 74.04           C
ATOM   4166  OD1  ASP B 496      47.295  18.502  66.873  1.00 74.20           O
ATOM   4167  OD2  ASP B 496      48.361  18.447  68.796  1.00 74.51           O
ATOM   4168  C    ASP B 496      47.590  14.064  67.857  1.00 51.72           C
ATOM   4169  O    ASP B 496      47.429  13.899  69.061  1.00 51.76           O
ATOM   4170  N    PHE B 497      47.590  13.061  66.984  1.00 49.91           N
ATOM   4171  CA   PHE B 497      47.379  11.676  67.397  1.00 50.34           C
ATOM   4172  CB   PHE B 497      47.485  10.754  66.182  1.00 47.64           C
ATOM   4173  CG   PHE B 497      46.783   9.444  66.354  1.00 45.96           C
ATOM   4174  CD1  PHE B 497      45.401   9.380  66.340  1.00 45.82           C
ATOM   4175  CD2  PHE B 497      47.504   8.274  66.525  1.00 45.53           C
ATOM   4176  CE1  PHE B 497      44.751   8.174  66.493  1.00 45.10           C
ATOM   4177  CE2  PHE B 497      46.860   7.067  66.679  1.00 44.89           C
ATOM   4178  CZ   PHE B 497      45.482   7.016  66.663  1.00 45.19           C
ATOM   4179  C    PHE B 497      48.392  11.247  68.470  1.00 51.61           C
ATOM   4180  O    PHE B 497      48.057  10.501  69.386  1.00 51.33           O
ATOM   4181  N    PHE B 498      49.630  11.711  68.339  1.00 81.82           N
ATOM   4182  CA   PHE B 498      50.692  11.408  69.307  1.00 84.10           C
ATOM   4183  CB   PHE B 498      50.822   9.893  69.559  1.00 74.78           C
ATOM   4184  CG   PHE B 498      50.992   9.069  68.310  1.00 76.37           C
```

Figure 15

| ATOM | 4185 | CD1 | PHE | B | 498 | 51.371 | 9.654 | 67.110 | 1.00 | 76.35 | C |
| --- | --- | --- | --- | --- | --- | --- | --- | --- | --- | --- | --- |
| ATOM | 4186 | CD2 | PHE | B | 498 | 50.764 | 7.701 | 68.341 | 1.00 | 76.09 | C |
| ATOM | 4187 | CE1 | PHE | B | 498 | 51.513 | 8.893 | 65.967 | 1.00 | 77.09 | C |
| ATOM | 4188 | CE2 | PHE | B | 498 | 50.906 | 6.935 | 67.201 | 1.00 | 77.09 | C |
| ATOM | 4189 | CZ | PHE | B | 498 | 51.281 | 7.531 | 66.010 | 1.00 | 77.02 | C |
| ATOM | 4190 | C | PHE | B | 498 | 52.044 | 11.966 | 68.874 | 1.00 | 84.44 | C |
| ATOM | 4191 | O | PHE | B | 498 | 52.862 | 12.345 | 69.711 | 1.00 | 85.33 | O |
| ATOM | 4192 | C1 | LIG | B | 500 | 52.218 | 12.574 | 38.427 | 1.00 | 32.79 | C |
| ATOM | 4193 | C2 | LIG | B | 500 | 53.306 | 11.615 | 38.701 | 1.00 | 35.47 | C |
| ATOM | 4194 | C3 | LIG | B | 500 | 51.010 | 12.063 | 37.791 | 1.00 | 33.31 | C |
| ATOM | 4195 | N1 | LIG | B | 500 | 51.947 | 13.959 | 38.593 | 1.00 | 31.28 | N |
| ATOM | 4196 | C4 | LIG | B | 500 | 53.084 | 10.124 | 38.321 | 1.00 | 35.40 | C |
| ATOM | 4197 | C5 | LIG | B | 500 | 54.648 | 11.935 | 39.314 | 1.00 | 36.53 | C |
| ATOM | 4198 | N2 | LIG | B | 500 | 50.199 | 13.108 | 37.604 | 1.00 | 31.61 | N |
| ATOM | 4199 | C6 | LIG | B | 500 | 50.843 | 10.671 | 37.458 | 1.00 | 33.97 | C |
| ATOM | 4200 | C7 | LIG | B | 500 | 50.740 | 14.191 | 38.058 | 1.00 | 30.31 | C |
| ATOM | 4201 | C8 | LIG | B | 500 | 52.753 | 15.029 | 39.183 | 1.00 | 33.47 | C |
| ATOM | 4202 | C9 | LIG | B | 500 | 54.148 | 9.140 | 38.573 | 1.00 | 36.40 | C |
| ATOM | 4203 | C10 | LIG | B | 500 | 51.829 | 9.737 | 37.716 | 1.00 | 35.67 | C |
| ATOM | 4204 | N3 | LIG | B | 500 | 55.562 | 10.931 | 39.488 | 1.00 | 36.53 | N |
| ATOM | 4205 | O1 | LIG | B | 500 | 54.957 | 13.045 | 39.646 | 1.00 | 37.65 | O |
| ATOM | 4206 | N4 | LIG | B | 500 | 50.169 | 15.434 | 37.986 | 1.00 | 30.04 | N |
| ATOM | 4207 | C11 | LIG | B | 500 | 55.351 | 9.578 | 39.142 | 1.00 | 36.99 | C |
| ATOM | 4208 | C12 | LIG | B | 500 | 53.947 | 7.656 | 38.208 | 1.00 | 35.92 | C |
| ATOM | 4209 | C13 | LIG | B | 500 | 48.927 | 15.623 | 37.353 | 1.00 | 28.81 | C |
| ATOM | 4210 | C14 | LIG | B | 500 | 56.439 | 8.604 | 39.391 | 1.00 | 39.99 | C |
| ATOM | 4211 | C15 | LIG | B | 500 | 47.686 | 15.623 | 38.100 | 1.00 | 30.10 | C |
| ATOM | 4212 | C16 | LIG | B | 500 | 48.912 | 15.829 | 35.921 | 1.00 | 28.98 | C |
| ATOM | 4213 | C17 | LIG | B | 500 | 57.603 | 8.941 | 39.962 | 1.00 | 44.60 | C |
| ATOM | 4214 | C18 | LIG | B | 500 | 46.444 | 15.828 | 37.413 | 1.00 | 30.66 | C |
| ATOM | 4215 | CL1 | LIG | B | 500 | 47.691 | 15.381 | 39.804 | 1.00 | 21.50 | C |
| ATOM | 4216 | C19 | LIG | B | 500 | 47.659 | 16.034 | 35.257 | 1.00 | 29.90 | C |
| ATOM | 4217 | CL2 | LIG | B | 500 | 50.420 | 15.840 | 34.977 | 1.00 | 18.64 | C |
| ATOM | 4218 | C20 | LIG | B | 500 | 58.666 | 7.877 | 40.219 | 1.00 | 48.22 | C |
| ATOM | 4219 | C21 | LIG | B | 500 | 46.439 | 16.033 | 36.004 | 1.00 | 32.28 | C |
| ATOM | 4220 | N5 | LIG | B | 500 | 58.642 | 6.571 | 40.997 | 1.00 | 51.08 | N |
| ATOM | 4221 | C22 | LIG | B | 500 | 59.628 | 6.720 | 42.093 | 1.00 | 52.97 | C |
| ATOM | 4222 | C23 | LIG | B | 500 | 57.321 | 6.285 | 41.611 | 1.00 | 51.50 | C |
| ATOM | 4223 | C24 | LIG | B | 500 | 60.934 | 5.970 | 41.789 | 1.00 | 54.80 | C |
| ATOM | 4224 | C25 | LIG | B | 500 | 62.032 | 6.990 | 41.507 | 1.00 | 55.26 | C |
| ATOM | 4225 | N6 | LIG | B | 500 | 62.925 | 7.135 | 42.667 | 1.00 | 56.88 | N |
| ATOM | 4226 | C26 | LIG | B | 500 | 63.974 | 8.095 | 42.274 | 1.00 | 56.66 | C |
| ATOM | 4227 | OH2 | TIP | | 1 | 36.090 | 9.892 | 47.063 | 1.00 | 24.16 | O |
| ATOM | 4228 | OH2 | TIP | | 2 | 34.485 | -0.935 | 55.954 | 1.00 | 31.87 | O |
| ATOM | 4229 | OH2 | TIP | | 3 | 26.680 | -0.268 | 54.800 | 1.00 | 30.79 | O |
| ATOM | 4230 | OH2 | TIP | | 4 | 32.262 | 0.555 | 48.936 | 1.00 | 28.89 | O |
| ATOM | 4231 | OH2 | TIP | | 5 | 33.834 | 1.039 | 51.077 | 1.00 | 32.31 | O |
| ATOM | 4232 | OH2 | TIP | | 6 | 32.069 | 17.179 | 56.066 | 1.00 | 30.60 | O |
| ATOM | 4233 | OH2 | TIP | | 7 | 27.058 | -0.731 | 59.657 | 1.00 | 30.01 | O |
| ATOM | 4234 | OH2 | TIP | | 8 | 34.453 | 20.581 | 62.202 | 1.00 | 35.57 | O |
| ATOM | 4235 | OH2 | TIP | | 9 | 26.687 | 16.484 | 60.066 | 1.00 | 29.14 | O |
| ATOM | 4236 | OH2 | TIP | | 10 | 29.599 | 15.066 | 61.995 | 1.00 | 38.94 | O |
| ATOM | 4237 | OH2 | TIP | | 11 | 47.461 | 12.277 | 37.440 | 1.00 | 44.38 | O |
| ATOM | 4238 | OH2 | TIP | | 12 | 31.231 | 2.294 | 60.859 | 1.00 | 37.30 | O |
| ATOM | 4239 | OH2 | TIP | | 13 | 33.953 | -4.711 | 61.767 | 1.00 | 35.69 | O |
| ATOM | 4240 | OH2 | TIP | | 14 | 37.930 | 13.430 | 41.094 | 1.00 | 43.45 | O |
| ATOM | 4241 | OH2 | TIP | | 15 | 32.542 | 7.801 | 48.371 | 1.00 | 37.37 | O |
| ATOM | 4242 | OH2 | TIP | | 16 | 24.705 | 6.649 | 60.893 | 1.00 | 36.84 | O |
| ATOM | 4243 | OH2 | TIP | | 17 | 38.114 | -4.708 | 64.954 | 1.00 | 33.74 | O |
| ATOM | 4244 | OH2 | TIP | | 18 | 44.108 | 3.457 | 45.928 | 1.00 | 33.11 | O |

Figure 15

```
ATOM   4245  OH2  TIP   19    23.514    0.356   53.212  1.00 39.44      O
ATOM   4246  OH2  TIP   20    59.040   15.609   44.798  1.00 49.48      O
ATOM   4247  OH2  TIP   21    26.291   11.127   65.075  1.00 38.15      O
ATOM   4248  OH2  TIP   22    27.972   -9.190   56.164  1.00 44.94      O
ATOM   4249  OH2  TIP   23    53.317    5.539   41.295  1.00 44.50      O
ATOM   4250  OH2  TIP   24    29.290   18.354   49.575  1.00 37.57      O
ATOM   4251  OH2  TIP   25    25.533   14.805   55.514  1.00 36.40      O
ATOM   4252  OH2  TIP   26    24.943    0.179   58.260  1.00 44.44      O
ATOM   4253  OH2  TIP   27    34.196    7.421   45.713  1.00 50.28      O
ATOM   4254  OH2  TIP   28    40.719   -4.570   57.993  1.00 40.52      O
ATOM   4255  OH2  TIP   29    43.143   -1.783   52.900  1.00 46.67      O
ATOM   4256  OH2  TIP   30    28.248   -4.517   60.801  1.00 42.61      O
ATOM   4257  OH2  TIP   31    35.052   30.029   55.720  1.00 46.85      O
ATOM   4258  OH2  TIP   32    22.867   14.278   55.740  1.00 42.48      O
ATOM   4259  OH2  TIP   33    24.178    6.684   53.436  1.00 36.41      O
ATOM   4260  OH2  TIP   34    29.576   -3.229   63.262  1.00 38.19      O
ATOM   4261  OH2  TIP   35    43.733   14.399   35.082  1.00 49.91      O
ATOM   4262  OH2  TIP   36    45.993   14.649   22.445  1.00 45.16      O
ATOM   4263  OH2  TIP   37    33.979    4.988   66.389  1.00 42.14      O
ATOM   4264  OH2  TIP   38    61.601   26.859   20.271  1.00 44.53      O
ATOM   4265  OH2  TIP   39    62.488    8.270   27.171  1.00 49.15      O
ATOM   4266  OH2  TIP   40    31.520   19.974   49.521  1.00 43.72      O
ATOM   4267  OH2  TIP   41    32.574   11.249   46.945  1.00 47.74      O
ATOM   4268  OH2  TIP   42    40.926   13.285   21.437  1.00 45.85      O
ATOM   4269  OH2  TIP   43    57.038    5.023   44.732  1.00 46.72      O
ATOM   4270  OH2  TIP   44    37.064   -7.391   54.777  1.00 44.44      O
ATOM   4271  OH2  TIP   45    45.535   24.412   55.362  1.00 52.31      O
ATOM   4272  OH2  TIP   46    28.829   10.040   64.523  1.00 38.76      O
ATOM   4273  OH2  TIP   47    58.300   20.112   40.333  1.00 56.65      O
ATOM   4274  OH2  TIP   48    25.910   13.524   43.373  1.00 43.67      O
ATOM   4275  OH2  TIP   49    61.036    5.038   32.867  1.00 50.64      O
ATOM   4276  OH2  TIP   50    46.009    6.905   35.712  1.00 54.29      O
ATOM   4277  OH2  TIP   51    23.796   -0.769   50.586  1.00 44.10      O
ATOM   4278  OH2  TIP   52    51.290   22.228   45.884  1.00 51.44      O
ATOM   4279  OH2  TIP   53    44.870   -0.598   47.767  1.00 52.00      O
ATOM   4280  OH2  TIP   54    38.169    6.478   45.108  1.00 42.59      O
ATOM   4281  OH2  TIP   55    35.393    8.587   33.709  1.00 50.18      O
ATOM   4282  OH2  TIP   56    44.676   17.036   39.968  1.00 50.16      O
ATOM   4283  OH2  TIP   57    48.807    4.818   26.040  1.00 54.64      O
ATOM   4284  OH2  TIP   58    27.158   11.614   50.295  1.00 53.27      O
ATOM   4285  OH2  TIP   59    52.636    1.710   32.376  1.00 52.26      O
ATOM   4286  OH2  TIP   60    20.321   11.960   61.633  1.00 53.07      O
ATOM   4287  OH2  TIP   61    60.772    6.386   28.257  1.00 42.42      O
ATOM   4288  OH2  TIP   62    45.900   -6.273   58.274  1.00 56.94      O
ATOM   4289  OH2  TIP   63    22.642    4.486   53.118  1.00 43.53      O
ATOM   4290  OH2  TIP   64    22.121    4.011   50.501  1.00 49.68      O
ATOM   4291  OH2  TIP   65    36.905   -1.700   44.055  1.00 42.82      O
ATOM   4292  OH2  TIP   66     7.399   12.471   12.807  1.00 24.16      O
ATOM   4293  OH2  TIP   67     5.811   23.280    3.891  1.00 31.87      O
ATOM   4294  OH2  TIP   68    -1.995   22.622    5.041  1.00 30.79      O
ATOM   4295  OH2  TIP   69     3.580   21.807   10.911  1.00 28.89      O
ATOM   4296  OH2  TIP   70     5.154   21.317    8.773  1.00 32.31      O
ATOM   4297  OH2  TIP   71     3.379    5.168    3.816  1.00 30.60      O
ATOM   4298  OH2  TIP   72    -1.613   23.075    0.183  1.00 30.01      O
ATOM   4299  OH2  TIP   73     5.765    1.751   -2.311  1.00 35.57      O
ATOM   4300  OH2  TIP   74    -1.999    5.859   -0.190  1.00 29.14      O
ATOM   4301  OH2  TIP   75     0.916    7.271   -2.119  1.00 38.94      O
ATOM   4302  OH2  TIP   76    18.760   10.096   22.445  1.00 44.38      O
ATOM   4303  OH2  TIP   77     2.558   20.044   -1.009  1.00 37.30      O
ATOM   4304  OH2  TIP   78     5.287   27.044   -1.930  1.00 35.69      O
```

Figure 15

```
ATOM   4305  OH2 TIP    79      9.231    8.944   18.785  1.00 43.45           O
ATOM   4306  OH2 TIP    80      3.854   14.562   11.492  1.00 37.37           O
ATOM   4307  OH2 TIP    81     -3.972   15.694   -1.039  1.00 36.84           O
ATOM   4308  OH2 TIP    82      9.451   27.031   -5.114  1.00 33.74           O
ATOM   4309  OH2 TIP    83     15.422   18.901   13.935  1.00 33.11           O
ATOM   4310  OH2 TIP    84     -5.164   22.005    6.627  1.00 39.44           O
ATOM   4311  OH2 TIP    85     30.342    6.739   15.103  1.00 49.48           O
ATOM   4312  OH2 TIP    86     -2.387   11.206   -5.211  1.00 38.15           O
ATOM   4313  OH2 TIP    87     -0.695   31.540    3.659  1.00 44.94           O
ATOM   4314  OH2 TIP    88     24.625   16.821   18.580  1.00 44.50           O
ATOM   4315  OH2 TIP    89      0.594    4.010   10.308  1.00 37.57           O
ATOM   4316  OH2 TIP    90     -3.155    7.549    4.358  1.00 36.40           O
ATOM   4317  OH2 TIP    91     -3.731   22.169    1.580  1.00 44.44           O
ATOM   4318  OH2 TIP    92      5.506   14.946   14.151  1.00 50.28           O
ATOM   4319  OH2 TIP    93     12.049   26.905    1.850  1.00 40.52           O
ATOM   4320  OH2 TIP    94     14.467   24.127    6.951  1.00 46.67           O
ATOM   4321  OH2 TIP    95     -0.420   26.857   -0.968  1.00 42.61           O
ATOM   4322  OH2 TIP    96      6.351   -7.684    4.192  1.00 46.85           O
ATOM   4323  OH2 TIP    97     -5.821    8.078    4.128  1.00 42.48           O
ATOM   4324  OH2 TIP    98     -4.505   15.675    6.417  1.00 36.41           O
ATOM   4325  OH2 TIP    99      0.910   25.563   -3.425  1.00 38.19           O
ATOM   4326  OH2 TIP   100     15.028    7.983   24.804  1.00 49.91           O
ATOM   4327  OH2 TIP   101     17.278    7.758   37.443  1.00 45.16           O
ATOM   4328  OH2 TIP   102      5.308   17.336   -6.531  1.00 42.14           O
ATOM   4329  OH2 TIP   103     32.874   -4.461   39.656  1.00 44.53           O
ATOM   4330  OH2 TIP   104     33.782   14.112   32.717  1.00 49.15           O
ATOM   4331  OH2 TIP   105      2.822    2.388   10.367  1.00 43.72           O
ATOM   4332  OH2 TIP   106      3.882   11.117   12.925  1.00 47.74           O
ATOM   4333  OH2 TIP   107     12.212    9.128   38.444  1.00 45.85           O
ATOM   4334  OH2 TIP   108     28.349   17.327   15.145  1.00 46.72           O
ATOM   4335  OH2 TIP   109      8.394   29.737    5.057  1.00 44.44           O
ATOM   4336  OH2 TIP   110     16.838   -2.075    4.547  1.00 52.31           O
ATOM   4337  OH2 TIP   111      0.152   12.292   -4.658  1.00 38.76           O
ATOM   4338  OH2 TIP   112     29.595    2.246   19.577  1.00 56.65           O
ATOM   4339  OH2 TIP   113     -2.787    8.855   16.496  1.00 43.67           O
ATOM   4340  OH2 TIP   114     32.338   17.333   27.014  1.00 50.64           O
ATOM   4341  OH2 TIP   115     17.311   15.473   24.160  1.00 54.29           O
ATOM   4342  OH2 TIP   116     -4.883   23.135    9.251  1.00 44.10           O
ATOM   4343  OH2 TIP   117     22.587    0.124   14.024  1.00 51.44           O
ATOM   4344  OH2 TIP   118     16.189   22.951   12.088  1.00 52.00           O
ATOM   4345  OH2 TIP   119      9.480   15.887   14.756  1.00 42.59           O
ATOM   4346  OH2 TIP   120      6.692   13.805   26.158  1.00 50.18           O
ATOM   4347  OH2 TIP   121     15.973    5.335   19.924  1.00 50.16           O
ATOM   4348  OH2 TIP   122     20.103   17.578   33.830  1.00 54.64           O
ATOM   4349  OH2 TIP   123     -1.532   10.749    9.572  1.00 53.27           O
ATOM   4350  OH2 TIP   124     23.940   20.670   27.490  1.00 52.26           O
ATOM   4351  OH2 TIP   125     -8.359   10.386   -1.772  1.00 53.07           O
ATOM   4352  OH2 TIP   126     32.069   15.995   31.626  1.00 42.42           O
ATOM   4353  OH2 TIP   127     17.232   28.603    1.570  1.00 56.94           O
ATOM   4354  OH2 TIP   128     -6.040   17.876    6.729  1.00 43.53           O
ATOM   4355  OH2 TIP   129     -6.562   18.357    9.345  1.00 49.68           O
ATOM   4356  OH2 TIP   130      8.222   24.069   15.792  1.00 42.82           O
END
```

Figure 15

METHOD OF IDENTIFYING INHIBITORS OF LCK

CROSS REFERENCE TO RELATED APPLICATION

This application claims the benefit of U.S. Provisional Application No. 60/310,051 filed Aug. 3, 2001.

BACKGROUND OF THE INVENTION

A breakdown in self-tolerance can result in the immune system raising an arsenal against the body's own defenses leading to diseases caused by inappropriate T lymphocyte (T-cell) responses. These include autoimmune diseases (multiple sclerosis, psoriasis, rheumatoid arthritis, Crohn's disease, lupus erythromatosis, etc.) and chronic inflammatory diseases. Similarly, graft rejection following transplant surgery is a significant clinical issue and arises due to recognition of foreign antigens from the graft by the host immune system. As T-cells are the key regulators of these immune system assaults, an inhibitor of T-cell function should have broad application as therapeutic agents in these diseases. Currently, the leading medicinal agent for the treatment of graft rejection is cyclosporin A (CsA), approved by the Food and Drug Administration in 1983. CsA inhibits the catalytic function of calcineurin, a phosphatase that plays a key role in signal transduction from the T-cell receptor (TcR) to the nucleus. Calcineurin is ubiquitously expressed and is involved in many other transduction pathways. As a result, CsA has a very narrow therapeutic index and suffers from its propensity to cause kidney failure, liver damage and ulcers. Safer drugs that are able to modulate the immune response with fewer side effects are needed.

Lck (lymphocyte cell kinase), a Src-family protein tyrosine kinase expressed primarily in T-cells, plays an essential role in the immune response. Crucially, Lck is upstream of calcineurin in the TcR signaling cascade. Productive antigen-induced T-cell activation is characterized by the appearance of a Lck-driven, hyperphosphorylated TcR ζ chain and by phosphorylation-dependent catalytic activation of the Syk-family kinase ZAP-70 by Lck after docking of ZAP-70 tandem SH2 domains to the phosphorylated amino acids (ITAM motif) in the ζ chain. Activated ZAP-70 phosphorylates several substrates that serve as adapter proteins for binding of downstream signaling molecules. This signaling cascade culminates in transcriptional activation of genes involved in cytokine release (particularly IL-2), and ultimately in T-cell clonal expansion in response to an autocrine growth pathway as a prelude to raising an immune response.

Lck is one of eight known members of the human Src-family of protein tyrosine kinases, the others being Src, Fyn, Lyn, Hck, Blk, Yes and Fgr. As a consequence of alternate mRNA splicing, Fyn exists as two distinct gene products, Fyn(T) and Fyn(B) that differ in their ATP binding sites. All Src-family kinases have a similar structure, comprised of an N-terminal Src-homology ("SH") 4 ("SH4") domain, a "unique" domain, an SH3 domain, an SH2 domain, a catalytic domain (also known as the SH1 domain or the kinase domain) and a short C-terminal tail. Activity is regulated by tyrosine phosphorylation at two sites. Phosphorylation of a tyrosine (Tyr-505, Src numbering) in the C-terminal tail leads to down-regulation by promoting an intramolecular interaction between the tail and the SH2 domain. In vivo, the protein phosphatase CD-45 is thought to dephosphorylate this terminal tyrosine to allow autophosphorylation of a tyrosine (Tyr-394) in the activation loop segment of the kinase domain to generate catalytically-competent Lck.

The eight known mammalian members of the Src-family break down into two sub-families. Lck is most similar to Hck, Lyn and Blk (identities greater than 65% between any two members). The other sub-family consists of Src, Yes, Fyn and Fgr (identities greater than 70% between any two members). These kinases have higher similarity when the catalytic domains alone are compared (in some cases greater than 90%). Residues that are important for Src-family kinase activity and/or substrate specificity have been identified by X-ray crystal structures and by structural modeling studies, and are highly conserved among family members. This high level of similarity presents a challenge for designing even partially specific inhibitors.

Genetic data clearly validate Lck as a target. Severe Combined Immune Deficiency (SCID)-like phenotypes have been observed in mice rendered Lck-deficient by homologous recombination. Individuals with mutations in the gene encoding ZAP-70 have been identified and present with an absence of peripheral $CD8^+$ T-cells and normal levels of peripheral $CD4^+$ T-cells that are unable to signal through the TcR. A single instance of a human disease-associated defect in Lck expression has been reported. The infant described exhibits the clinical features of SCID, has selective $CD4^+$ lymphopenia and lacks expression of the CD28 co-stimulatory molecule on $CD8^+$ T-cells. Lck protein in the patient is expressed at <10% of the level observed in control T-cells. T-cells from this patient had defective proliferative responses to mitogens and IL-2, while some TcR proximal signaling events (e.g. mobilization of intracellular calcium) did not seem to be impaired.

Selective and non-selective kinase inhibitors have been shown to block T-cell receptor-dependent effects in cellular assays, thus validating inhibitors as modulators of T-cell function. Given the genetic and pharmacologic data for the role of Lck in T-cell activation, Lck appears to be a target suited to therapeutic intervention in indications where the disease process is T-cell dependent. Selective inhibition of Lck function therefore represents an attractive target for therapeutic intervention in the treatment of autoimmune and inflammatory diseases and also in organ transplantation. Given the very restricted cellular expression pattern for the target enzyme, the mechanism-based toxicity of selective Lck inhibitors should result in fewer side effects than cyclosporine A or corticosteroids.

Several crystal structures have been reported of Src-family protein kinases. Among these are:
1. a structure of the catalytic domain of human Lck in the activated state, that is, phosphorylated on Tyr-394 in the activation loop (Yamaguchi & Hendrickson, 1996);
2. a structure of human Src (SH3, SH2, catalytic domain, and C-terminal tail) in the autoinhibited state, that is not phosphorylated on Tyr-416 in the activation loop, but instead phosphorylated on Tyr-527 in the C-terminal tail (numbering of amino acid residues corresponds to the gene for chicken c-Src) (Xu et al., 1997);
3. a structure of human Hck (SH3, SH2, catalytic domain, and C-terminal tail) in the autoinhibited state, that is not phosphorylated on Tyr-416 in the activation loop, but instead phosphorylated on Tyr-527 in the C-terminal tail (numbering of amino acid residues corresponds to the gene for chicken c-Src) (Sicheri et al., 1997);
4. a structure of an autoinhibited human Hck/ligand complex (ligand PP1) (Schindler et al., 1999);
5. five structures of human Src (SH3, SH2, catalytic domain, and C-terminal tail) in the autoinhibited state, that is not phosphorylated on Tyr-416 in the activation loop, but instead phosphorylated on Tyr-527 in the C-terminal tail (numbering of amino acid residues corresponds to the gene for chicken c-Src), of which one structure is a Src/ligand complex (ligand AMP-PNP) (Xu et al., 1999);

6. a structure of chicken Src (SH3, SH2, catalytic domain, and C-terminal tail) in the autoinhibited state, that is not phosphorylated on Tyr-416 in the activation loop, but instead phosphorylated on Tyr-527 in the C-terminal tail (Williams et al., 1997);

7. three structures of the catalytic domain of activated human Lck/ligand complexes (ligands AMP-PNP, staurosporine, and PP2) (Zhu et al., 1999).

Crystal structures have been determined also for the kinase domains of a wide variety of protein tyrosine and serine/threonine kinases outside of the Src-family, for example Abl (Schindler et al., 2000), Tie2 (Shewchuk et al., 2000), insulin receptor (Hubbard et al., 1994), FGF receptor (Mohammadi et al., 1996), VEGF receptor (McTigue et al., 1999), cAMP-dependent protein kinase (Knighton et al., 1991), cyclin-dependent kinase 2 (Cdk2) (Schulze-Gahmen et al., 1996), PAK1 (Lei et al., 2000), GSK-3β (Dajani et al., 2001), among others.

Crystal structures have also been determined for the kinase domains of certain protein kinases complexed to other proteins, for example Cdk2 complexed to cyclin A (Chan et al., 2001), and Cdk2 complexed to cyclin A and p27Kip1 (Russo et al., 1996), among others.

In addition, crystal structures have been determined for certain non-catalytic domains of some protein kinases, for example a regulatory subunit of cAMP-dependent protein kinase (Su et al., 1995), an SH2 domain of a Src-family protein tyrosine kinase (Waksman et al., 1992), and an SH3 domain of a Src-family protein tyrosine kinase (Noble et al., 1993), among others.

Three-dimensional structures for certain non-catalytic domains of some protein kinases have also been determined using other techniques, such as nuclear magnetic resonance (NMR). Examples include an SH2 domain of Syk (Narula et al., 1995) and the SH2 and SH3 domains of Abl (Gosser et al., 1995), among others.

Previously determined crystal structures of Src-family protein tyrosine kinases, especially those of Lck, Hck, and Src, all suffer defects that limit their usefulness in guiding the design of improved inhibitors. These limitations include, among others:

1. structures determined without ligands bound to the protein tyrosine kinase, for example the structure of the catalytic domain of human Lck in the activated state referred to above (Yamaguchi & Hendrickson, 1996);
2. structures determined of kinase/ligand complexes wherein the ligands bind weakly to the kinase, for example the structure of an activated human Lck catalytic domain/ligand complex (ligand AMP-PNP) referred to above (Zhu et al., 1999);
3. structures determined of kinase/ligand complexes wherein the ligands exhibit non-specific binding to a variety of kinases, for example the structure of an autoinhibited human Hck/ligand complex (ligand PP1) referred to above (Schindler et al., 1999);
4. structures determined of kinase/ligand complexes wherein potential ligand binding sites in the kinase catalytic domain are not accessed by the ligands, for example the structure of an autoinhibited human Hck/ligand complex (ligand PP1) referred to above (Schindler et al., 1999), as well as the three structures of activated human Lck catalytic domain/ligand complexes (ligands AMP-PNP, staurosporine, and PP2) referred to above (Zhu et al., 1999). These structures do not teach how a ligand should be designed in order to best interact with potential binding sites.

A further limitation of the prior art has been that the structures of Src-family protein tyrosine kinases referred to above, especially those of Lck, Hck, and Src, all were determined using catalytically-active enzymes. The intrinsic catalytic activity of these kinases limits which phosphorylation states of the kinase are experimentally-accessible. It is well-known that the regulation of Src-family protein tyrosine kinases is regulated in part by differential phosphorylation (Superti-Furga, 1995).

Yet another limitation of the prior art has been that all previous crystal structures of Lck have been determined using an activated Lck catalytic domain that is phosphorylated at Tyr-394 (Yamaguchi & Hendrickson, 1996; Zhu et al., 1999). Other prior work on another Src-family protein tyrosine kinase, Hck, has demonstrated, however, that the phosphorylation state of the corresponding residue in Hck (Tyr-416; numbering of amino acid residues corresponds to the gene for chicken c-Src) likely alters the ability of Hck to bind ligands (Schindler et al., 1999). While this latter Hck crystal structure does not teach how a ligand should be designed in order to best interact with potential binding sites on Hck, let alone Lck, it is clear that experimental access to crystal structures of Src-family protein tyrosine kinases in several different phosphorylation states is desirable, but not yet achieved. Furthermore, it is not clear which phosphorylation state of a Src-family protein tyrosine kinase such as Lck is the therapeutically-relevant target for inhibition, or indeed whether several different phosphorylation states are all therapeutically-relevant targets, but under different conditions (such as disease state, tissue, etc.).

A final limitation of the prior art has been that all previous crystal structures of Lck, Hck, and Src determined as a kinase/ligand complex have been determined with inhibitors that do not access or contact amino acid residues that are unique to that particular kinase within the Src family. Examples include the structure of an autoinhibited human Hck/ligand complex (ligand PP1) referred to above (Schindler et al., 1999); the three structures of activated human Lck catalytic domain/ligand complexes (ligands AMP-PNP, staurosporine, and PP2) referred to above (Zhu et al., 1999); and the structure of an autoinhibited Src/ligand complex (ligand AMP-PNP) referred to above (Xu et al., 1999). Thus, these structures do not teach how a ligand should be designed in order to best interact with unique binding sites that could provide binding selectivity within the Src family.

Due to its role in T cell-mediated immune responses, Lck is a potential target for therapies aimed at controlling autoimmune and inflammatory diseases, cancer and also in treating organ transplant rejection. The development of biochemical assays for Lck has enabled drug discovery to proceed along the pathways of identifying lead Lck inhibitors by high-throughput screening of compound libraries and by testing compounds that mimic substrate structure. As discussed above, however, rational, structure-based design has not been possible up to this point because of the lack of accurate three-dimensional structural data for Lck complexed to appropriate ligands.

SUMMARY OF THE INVENTION

The present invention relates to a polypeptide which comprises the catalytic domain of Lck, a crystalline form of this polypeptide, and the use of structural information derived from the crystalline form of the polypeptide for designing and/or identifying potential inhibitors of the binding of one or more native ligands to either the catalytic domain of Lck or intact Lck.

In one embodiment, the present invention relates to a polypeptide comprising the catalytic domain of Lck and having the amino acid sequence set forth in SEQ ID NO. 2. In another embodiment, the invention relates to a crystalline form of this polypeptide or the polypeptide complexed with a ligand.

In another embodiment, the invention provides a method of determining the three dimensional structure of a crystalline polypeptide comprising the Lck catalytic domain. In one embodiment, the method comprises the steps of (1) obtaining a crystal of the polypeptide comprising the catalytic domain of Lck; (2) obtaining x-ray diffraction data for said crystal; and (3) solving the crystal structure of said crystal. The method optionally comprises the additional step of obtaining the polypeptide, with the three dimensional structure to be determined, prior to obtaining the crystal of said peptide.

In another embodiment, the method comprises the steps of (1) obtaining a crystal of the polypeptide comprising the catalytic domain of Lck; (2) obtaining x-ray diffraction data for said crystal; and (3) solving the crystal structure of said crystal by using said x-ray diffraction data and the atomic coordinates for the Lck catalytic domain of a second polypeptide. The method optionally comprises the additional step of obtaining the polypeptide, with the three dimensional structure to be determined, prior to obtaining the crystal of said peptide.

The invention further relates to a method for identifying a compound which inhibits the biological activity of Lck by, for example, inhibiting the catalytic activity of Lck by inhibiting the binding of natural substrates such as a tyrosine-containing polypeptide or a protein or ATP, to Lck. Such a compound is referred to herein as an "Lck inhibitor". The method comprises the steps of (1) using a three-dimensional structure of Lck as defined by the atomic coordinates of the catalytic domain of Lck; (2) employing the three dimensional structure to design or select a potential inhibitor; and (3) assessing the ability of the selected compound to inhibit the catalytic activity of Lck. The method can also include the step of providing the compound designed or selected in step 2, for example, by synthesizing the compound or obtaining the compound from a compound library. In addition, the method can include the step of assessing the ability of the identified compound to bind to the catalytic domain of Lck and/or assessing the ability of the identified compound to inhibit the binding of a natural ligand of Lck.

In another embodiment, the method for identifying a compound which inhibits the biological activity of Lck, comprises the step of determining the ability of one or more functional groups and/or moieties of the compound, when present in, or bound to, the Lck catalytic domain, to interact with one or more subsites of the Lck catalytic domain. Generally, the Lck catalytic domain is defined by the conserved homologous sequences when compared to other known protein tyrosine kinases. If the compound is able to interact with a preselected number or set of subsites, or has a calculated interaction energy within a desired or preselected range, the compound is identified as a potential inhibitor of Lck.

The invention further provides a method of designing a compound which is a potential inhibitor of the biological activity of Lck. The method includes the steps of (1) identifying one or more functional groups capable of interacting with one or more subsites of the Lek catalytic domain; and (2) identifying a scaffold which presents the functional group, or functional groups, identified in step 1 in a suitable orientation for interacting with one or more subsites of the Lck catalytic domain. The compound which results from attachment of the identified functional groups or moieties to the identified scaffold is a potential inhibitor of Lck. The Lck catalytic domain is, generally, defined by the atomic coordinates of a polypeptide comprising the Lck catalytic domain.

In yet another embodiment, the invention provides compounds which inhibit the biological activity of Lck and which fit, or bind to, the Lck catalytic domain. Such compounds typically comprise one or more functional groups which, when the compound is bound in the Lck catalytic domain, interact with one or more subsites of the catalytic domain. Generally, the Lck catalytic domain is defined by the conserved homologous sequence when compared to other known protein tyrosine kinases. In a particular embodiment, the Lck inhibitor is a compound which is identified or designed by a method of the present invention.

The present invention further provides a method for treating a condition mediated by Lck in a patient. The method comprises administering to the patient a therapeutically or prophylactically effective amount of a compound which inhibits the biological activity of Lck, such as an Lck inhibitor of the invention, for example, a compound identified as an Lck inhibitor or designed to inhibit Lck by a method of the present invention.

The present invention provides several advantages. For example, the invention provides the first detailed three dimensional structures of the catalytic domain of an Lck protein to which potent and selective Lck inhibitors are bound. In addition, the invention provides the first detailed three dimensional structures of the catalytic domain of Lck/inhibitor complexes in which the Lck inhibitors access previously-inaccessible binding sites. The invention further provides the first detailed three dimensional structures of the catalytic domain of Lck, both alone and with inhibitors bound to the Lck catalytic domain, in which the Lck protein is not phosphorylated at Tyr-394. The methods described herein can be used to facilitate formation of Lck crystals which diffract to high resolution. These structures enable the rational development of inhibitors of Lck by permitting the design and/or identification of molecular structures having features which facilitate binding to the Lck catalytic domain. The methods of use of the structures disclosed herein, thus, permit more rapid discovery of compounds which are potentially useful for the treatment of conditions which are mediated, at least in part, by Lck activity.

The crystalline unphosphorylated human Lck(237-501, D364N) polypeptide/inhibitor complex wherein the inhibitor is of the formula (1):

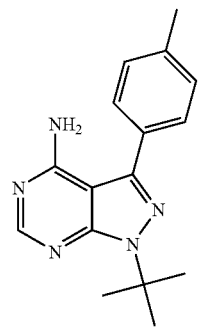

The crystalline unphosphorylated human Lck(237-501, D364N) polypeptide/inhibitor complex wherein the inhibitor is of the formula (2):

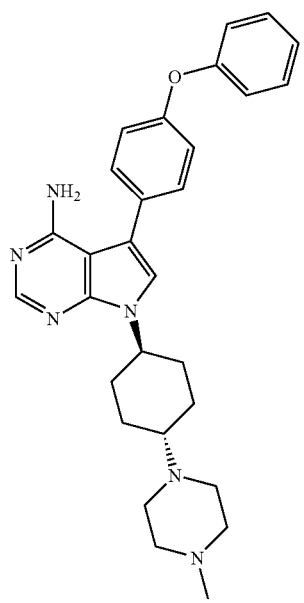

The crystalline unphosphorylated human Lck(237-501, D364N) polypeptide/inhibitor complex wherein the inhibitor is of the formula (3):

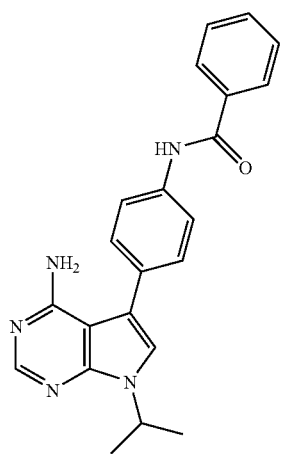

The crystalline unphosphorylated human Lck(237-501, D364N) polypeptide/inhibitor complex wherein the inhibitor is of the formula (4):

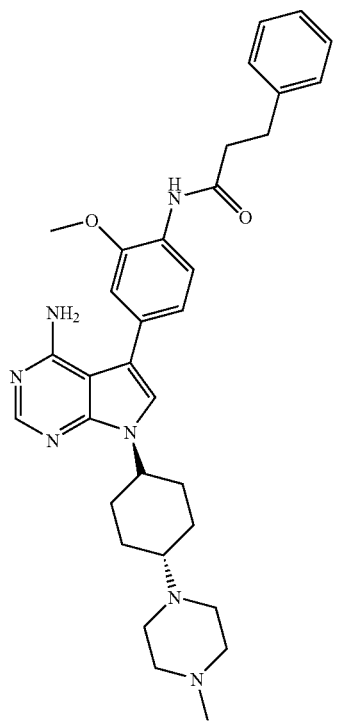

The crystalline unphosphorylated human Lck(237-501, D364N) polypeptide/inhibitor complex wherein the inhibitor is of the formula (5):

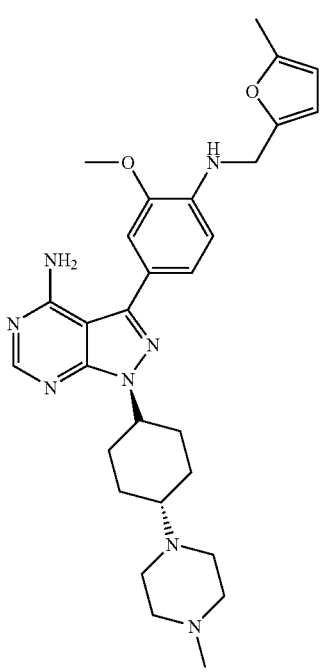

The crystalline unphosphorylated human Lck(237-501, D364N) polypeptide/inhibitor complex wherein the inhibitor is of the formula (6):

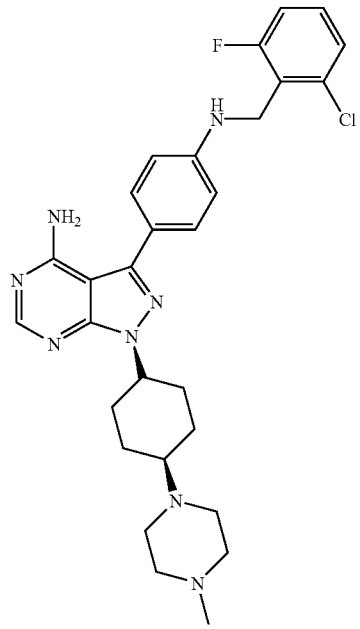

The crystalline unphosphorylated human Lck(237-501, D364N) polypeptide/inhibitor complex wherein the inhibitor is of the formula (7):

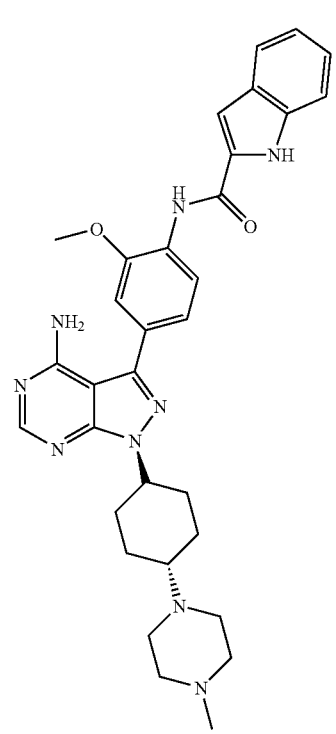

The crystalline unphosphorylated human Lck(237-501, D364N) polypeptide/inhibitor complex wherein the inhibitor is of the formula (8):

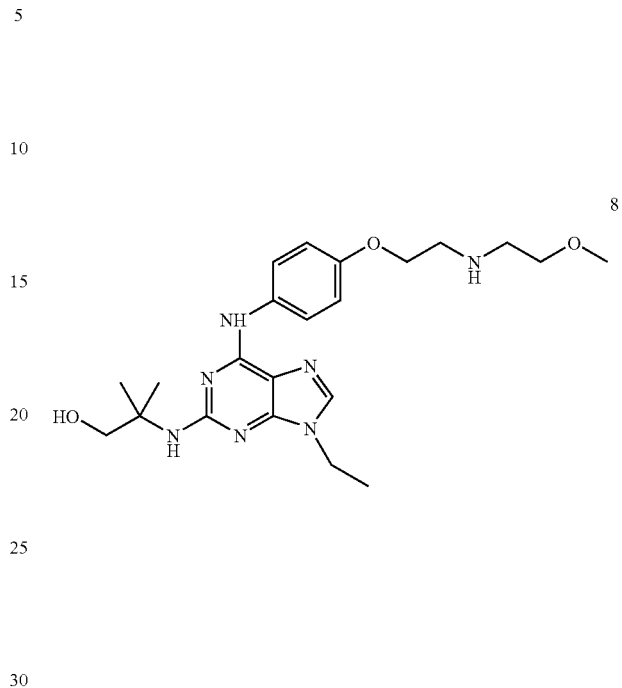

The crystalline unphosphorylated human Lck(237-501, D364N) polypeptide/inhibitor complex wherein the inhibitor is of the formula (9):

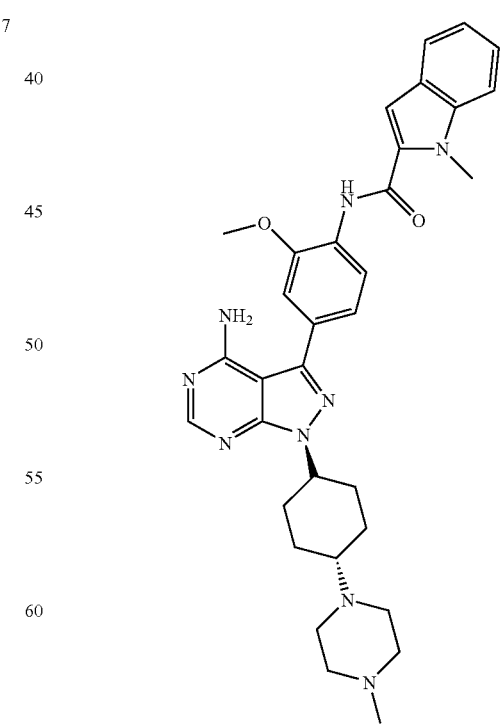

The crystalline unphosphorylated human Lck(237-501, D364N) polypeptide/inhibitor complex wherein the inhibitor is of the formula (10):

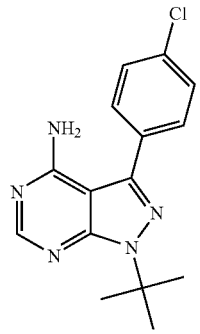

The crystalline unphosphorylated human Lck(237-501, D364N) polypeptide/inhibitor complex wherein the inhibitor is of the formula (11):

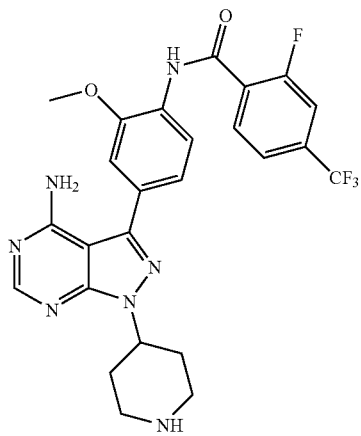

The crystalline unphosphorylated human Lck(237-501, D364N) polypeptide/inhibitor complex wherein the inhibitor is of the formula (12):

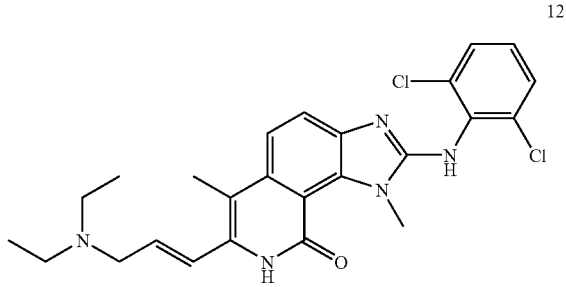

The crystalline unphosphorylated human Lck(237-501, D364N) polypeptide/inhibitor complex wherein the inhibitor is of the formula (13):

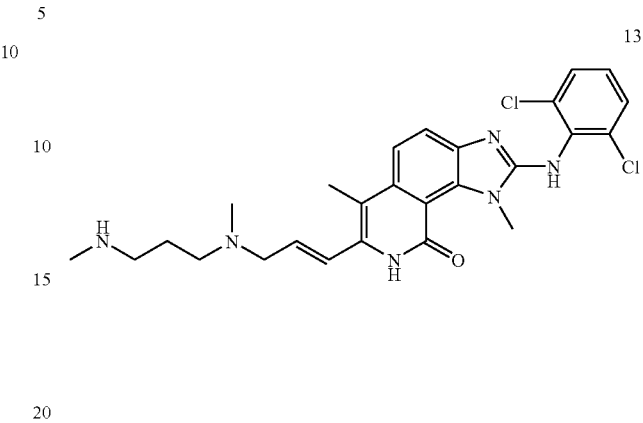

A crystalline polypeptide comprising the catalytic domain amino acids 231-501 of SEQ ID NO. 1 of an Lck protein. The foregoing crystalline polypeptide wherein the crystallographic space group is P2(1) or P2(1)2(1)2(1). Any of the foregoing crystalline polypeptide, which comprises one or more non-conservative point mutations. Any of the foregoing crystalline polypeptide wherein the polypeptide comprises the catalytic domain of a vertebral, preferably mammalian, more preferably human Lck protein. Any of the foregoing crystalline polypeptide comprising where the polypeptide comprises the Asp-364-Asn non-conservative mutation. Any of the foregoing crystalline polypeptide which comprises human Lck amino acids 237-501 of SEQ ID NO. 2 and having unit cell parameters wherein a is about 57 Å, b is about 44 Å, c is about 120 Å, α is about 90°, β is about 90°, and γ is about 90°, more preferably the unit cell parameters are a is about 57.6 Å, b is about 44.5 Å, c is about 119.8 Å, α is about 90.0°, β is about 89.9°, γ is about 90.0°.

The crystal structure atomic coordinates of the crystalline polypeptide that are set forth in FIG. 13.

Any of the foregoing crystalline polypeptide wherein the polypeptide is modified by phosphorylation.

Any of the foregoing crystalline polypeptide wherein the phosphorylation modification is at Tyr-394.

Any of the foregoing crystalline polypeptide wherein the polypeptide is not modified by phosphorylation.

Any of the foregoing crystalline polypeptide which comprises the catalytic domain of an Lck protein which comprises one or more deletion mutations that lie outside of the Lck active site comprised of amino acids 249-261, 271-273, 285-292 301-305, 314-326, 368-371, and 381-398 of SEQ ID NO. 1.

Any of the foregoing crystalline polypeptide which comprises the catalytic domain of the human Lck protein, one or more non-conservative point mutations; and one or more deletion mutations that lie outside of the Lck active site comprised of amino acids 249-261, 271-273, 285-292 301-305, 314-326, 368-371, and 381-398 of SEQ ID NO. 1.

A crystalline polypeptide/inhibitor complex comprising the catalytic domain of an Lck protein and a inhibitor and having unit cell parameters wherein a is about 57 Å, b is about 44 Å, c is about 120 Å, α is about 90°, β is about 90°, and γ is about 90°, more preferably the unit cell parameters are a is about 57 Å, b is about 45 Å, c is about 120 Å, α is about 90°, β is about 90°, and γ is about 90°. Preferably the crystalline polypeptide/inhibitor complex where the crystallographic space group is P2(1) or P2(1)2(1)2(1).

Any of the foregoing crystalline polypeptide/inhibitor complex, which comprises one or more non-conservative point mutations.

Any of the foregoing crystalline polypeptide/inhibitor complex where the polypeptide is vertebral, preferably mammalian, more preferably human Lck protein.

Any of the foregoing crystalline polypeptide/inhibitor complex comprising the entire amino acid sequence of SEQ ID NO. 1, and wherein the polypeptide contains Asp-364-Asn mutation.

Any of the foregoing crystalline polypeptide/inhibitor complex wherein the polypeptide comprises human Lck amino acids 237-501 of SEQ ID NO. 1.

The crystalline polypeptide/inhibitor complex wherein the inhibitor is of the formula (1):

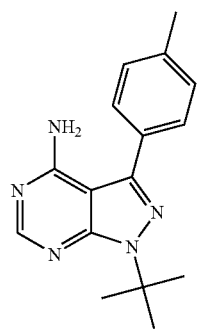

The crystalline polypeptide/inhibitor-1 complex having unit cell parameters wherein a is about 57 Å, b is about 44 Å, c is about 120 Å, α is about 90°, β is about 90°, and γ is about 90°, more preferably the unit cell parameters are a is about 57.6 Å, b is about 44.6 Å, c is about 121.6 Å, α is about 90.0°, β is about 90.2°, and γ is about 90.0°.

The crystal structure atomic coordinates of the crystalline polypeptide/inhibitor complex that are set forth in FIG. 4.

The crystalline polypeptide/inhibitor complex wherein the inhibitor is of the formula (2):

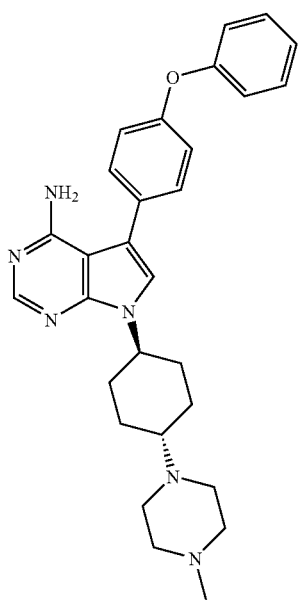

The crystalline polypeptide/inhibitor-2 complex having unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.4 Å, c is about 119.9 Å, α is about 90.0°, β is about 90.1°, and γ is about 90.0°.

The crystal structure atomic coordinates of the crystalline polypeptide/inhibitor complex that are set forth in FIG. 5.

The crystalline polypeptide/inhibitor complex wherein the inhibitor is of the formula (3):

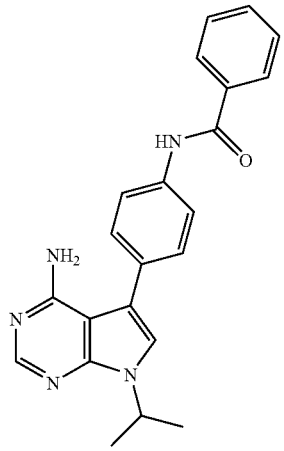

The crystalline polypeptide/inhibitor-3 complex having unit cell parameters wherein a is about 57 Å, b is about 44 Å, c is about 120 Å, α is about 90°, β is about 90°, and γ about 90°, more preferably the unit cell parameters are a is about 57.3 Å, b is about 44.3 Å, c is about 120.8 Å, α is about 90.0°, β is about 90.0°, and γ is about 90.0°.

The crystal structure atomic coordinates of the crystalline polypeptide/inhibitor complex that are set forth in FIG. 6.

The crystalline polypeptide/inhibitor complex wherein the inhibitor is of the formula (4):

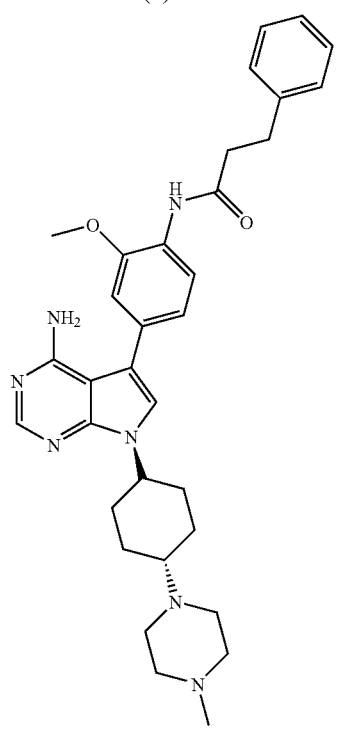

The crystalline polypeptide/inhibitor-4 complex having unit cell parameters wherein a is about 57 Å, b is about 44 Å, c is about 120 Å, α is about 90°, β is about 90°, and γ is about 90°, more preferably the unit cell parameters are a is about 57.8 Å, b is about 44.4 Å, c is about 126.2 Å, α is about 90.0°, β is about 90.0°, and γ is about 90.0°.

The crystal structure atomic coordinates of the crystalline polypeptide/inhibitor complex that are set forth in FIG. 7.

The crystalline polypeptide/inhibitor complex wherein the inhibitor is of the formula (5):

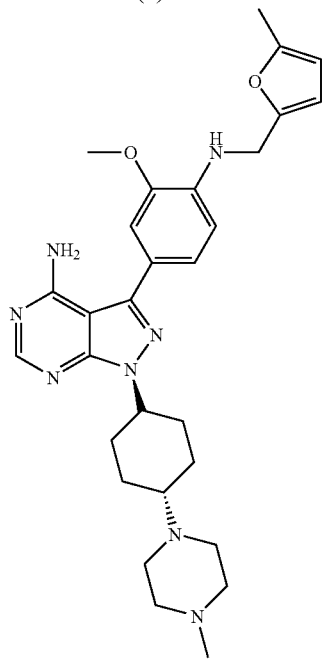

5

The crystalline polypeptide/inhibitor-5 complex having unit cell parameters wherein a is about 57 Å, b is about 44 Å, c is about 120 Å, α is about 90°, β is about 90°, and γ is about 90°, more preferably the unit cell parameters are a is about 57.6 Å, b is about 44.6 Å, c is about 120.0 Å, α is about 90.0°, β is about 90.1°, and γ is about 90.0°.

The crystal structure atomic coordinates of the crystalline polypeptide/inhibitor complex that are set forth in FIG. 8.

The crystalline polypeptide/inhibitor complex wherein the inhibitor is of the formula (6):

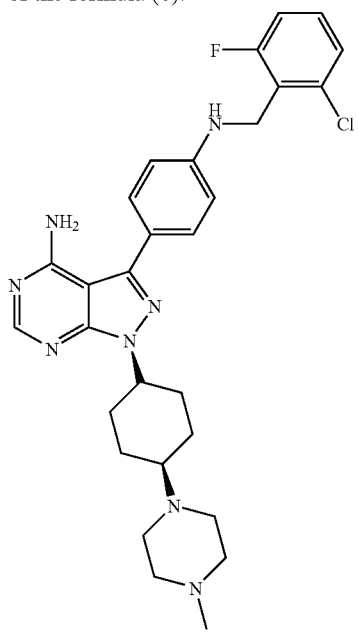

6

The crystalline polypeptide/inhibitor-6 complex having unit cell parameters wherein a is about 57 Å, b is about 44 Å, c is about 120 Å, α is about 90°, β is about 90°, and γ is about 90°, more preferably the unit cell parameters are a is about 56.8 Å, b is about 44.5 Å, c is about 120.2 Å, α is about 90.0°, β is about 90.0°, and γ is about 90.0°.

The crystal structure atomic coordinates of the crystalline polypeptide/inhibitor complex that are set forth in FIG. 9.

The crystalline polypeptide/inhibitor complex wherein the inhibitor is of the formula (7):

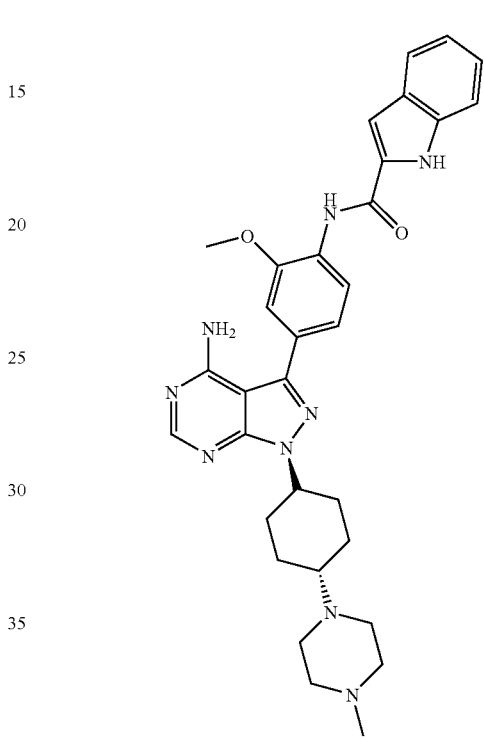

7

The crystalline polypeptide/inhibitor-7 complex having unit cell parameters wherein a is about 57 Å, b is about 44 Å, c is about 120 Å, α is about 90°, β is about 90°, and γ is about 90°, more preferably the unit cell parameters are a is about 57.4 Å, b is about 44.7 Å, c is about 119.8 Å, α is about 90.0°, β is about 90.0°, and γ is about 90.0°.

The crystal structure atomic coordinates of the crystalline polypeptide/inhibitor complex that are set forth in FIG. 10.

The crystalline polypeptide/inhibitor complex wherein the inhibitor is of the formula (8):

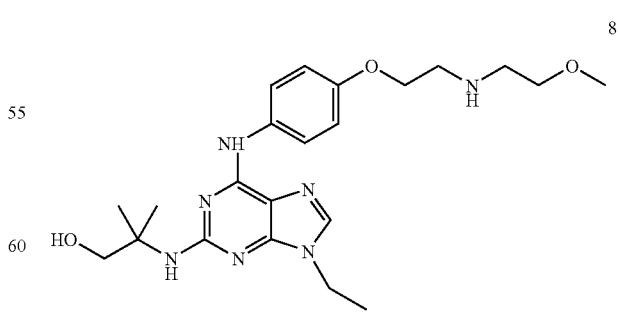

8

The crystalline polypeptide/inhibitor-8 complex having unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.4 Å, c is about 120.7 Å, α is about 90.0°, β is about 90.0°, and γ is about 90.0°.

The crystal structure atomic coordinates of the crystalline polypeptide/inhibitor complex that are set forth in FIG. 11.

The crystalline polypeptide/inhibitor complex wherein the inhibitor is of the formula (9):

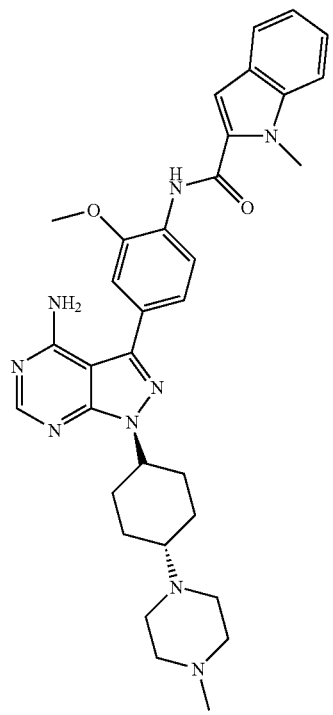

9

The crystalline polypeptide/inhibitor-9 complex having unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.2 Å, c is about 118.3 Å, α is about 90.0°, β is about 89.9°, and γ is about 90.0°.

The crystal structure atomic coordinates of the crystalline polypeptide/inhibitor complex that are set forth in FIG. 12.

The crystalline polypeptide/inhibitor complex wherein the inhibitor is of the formula (12):

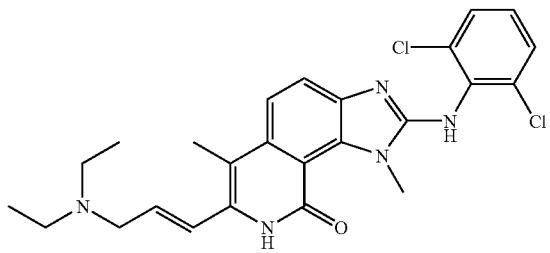

12

The crystalline polypeptide/inhibitor-12 complex having unit cell parameters wherein a is about 57 Å, b is about 44 Å, c is about 120 Å, α is about 90°, β is about 90°, and γ is about 90°, more preferably the unit cell parameters are a is about 57.9 Å, b is about 44.6 Å, c is about 122.0 Å, α is about 90.0°, β is about 89.9°, γ is about 90.0°.

The crystal structure atomic coordinates of the crystalline polypeptide/inhibitor complex that are set forth in FIG. 14.

The crystalline polypeptide/inhibitor complex wherein the inhibitor is of the formula (13):

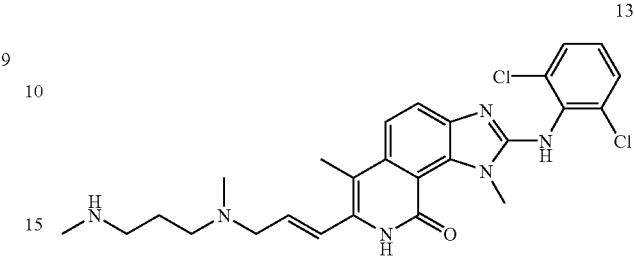

13

The crystalline polypeptide/inhibitor-13 complex having unit cell parameters wherein a is about 57 Å, b is about 44 Å, c is about 120 Å, α is about 90°, β is about 90°, and γ is about 90°, more preferably the unit cell parameters are a is about 57.2 Å, b is about 44.5 Å, c is about 120.1 Å, α is about 90.0°, β is about 90.0°, and γ is about 90.0°.

The crystal structure atomic coordinates of the crystalline polypeptide/inhibitor complex that are set forth in FIG. 15.

A method for determining the three dimensional structure of a first polypeptide comprising all or part of an Lck protein, wherein the Lck protein is not phosphorylated and/or comprises one or more non-conservative point mutations, said method comprising the steps of:
  (a) obtaining a crystal of the first polypeptide;
  (b) using said crystal structure atomic coordindinates of a second polypeptide, said second polypeptide comprising the catalytic domain of the Lck protein.
  (c) obtaining the atomic coordinates of a crystal of a polypeptide comprising all or part of an Lck protein;

The foregoing method wherein the crystal of the first polypeptide comprises the first polypeptide complexed with a inhibitor.

Any of the foregoing methods wherein the first polypeptide is human Lck protein.

A method for identifying a compound which is an inhibitor of an Lck protein, wherein the Lck protein is not phosphorylated and/or comprises one or more non-conservative point mutations, said method comprising the steps of:
  (a) obtaining the atomic coordinates of a crystal of a polypeptide comprising all or part of an Lck protein;
  (b) using said crystal structure atomic coordinates to define the active subsites of Lck; and
  (c) identifying a compound which binds to one or more active subsites; wherein the compound which binds to the active subsite or subsites is an inhibitor of the Lck.

The foregoing method, further comprising the step of:
  (d) assessing the ability of the compound identified in step (c) to inhibit Lck.

Any of the foregoing methods wherein the Lck protein is a human Lck protein.

Any of the foregoing wherein the crystal has unit cell parameters wherein a is about 57.6 Å, b is about 44.5 Å, c is about 119.8 Å, α is about 90.0°, β is about 89.9°, γ is about 90.0°.

A method for identifying a compound which is a selective inhibitor of an Lck protein, wherein the Lck protein is not phosphorylated and/or comprises one or more non-conservative point mutations, said method comprising the steps of:

(a) obtaining a crystal of a polypeptide comprising all of part of an Lck protein;
(b) obtaining the crystal structure atomic coordinates of the crystal;
(c) using said atomic coordinates to define active subsites uniqe to Lck; and
(d) using said atomic coordinates and sequences or structures of related polypeptides to define active subsites uniqe to Lck; and
(e) identifying a compound which binds to one or more active subsites at least one of which is unique to Lck; wherein the compound which binds to the active subsite or subsites is a selective inhibitor of Lck.

The foregoing method, further comprising the step of:
(f) assessing the ability of the compound identified in step (e) to selectively inhibit Lck.

Any of the foregoing methods wherein the Lck protein is a human Lck protein.

Any of the foregoing wherein the crystal has unit cell parameters wherein a is about 57 Å, b is about 44 Å, c is about 120 Å, α is about 90°, β is about 90°, and γ is about 90°, more preferably the unit cell parameters are a is about 57.2 Å, b is about 44.5 Å, c is about 120.1 Å, α is about 90.0°, β is about 90.0°, and γ is about 90°.

A method for identifying a compound which is an inhibitor of an Lck protein, said method comprising the steps of:
(a) obtaining the crystal structure atomic coordinates of a crystal of a polypeptide/inhibItor complex, said polypeptide comprising all or part of an Lck protein provided that the inhibitor in the complex is not AMP-PNP, staurosporine, or inhibitor 10, which have the formulas shown below:

AMP-PNP

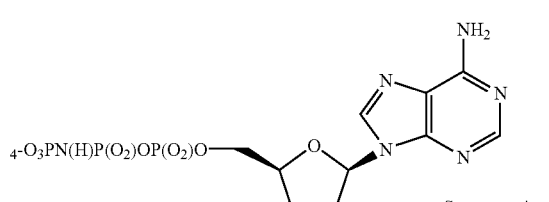

Staurosporine

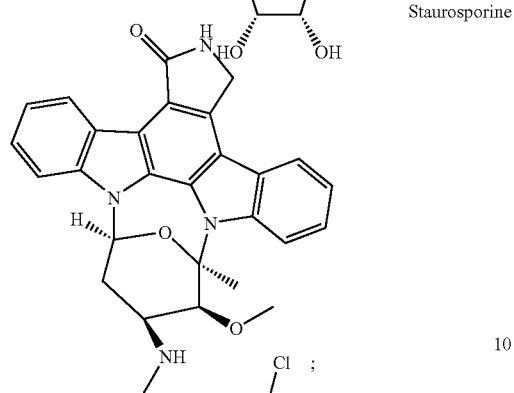

10

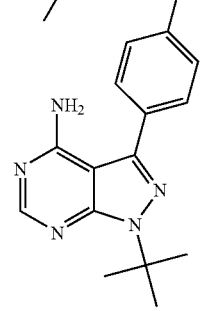

(b) using said atomic coordinates to define the active subsites of Lck; and
(c) identifying a compound which binds to one or more active subsites; wherein the compound which binds to the active subsite or subsites is an inhibitor of the Lck.

Any of the foregoing methods, further comprising the step of:
(d) assessing the ability of the compound identified in step (c) to inhibit Lck.

Any of the foregoing methods wherein the point mutation is Asp-364-Asn; and comprises human Lck amino acids 237-501 of SEQ ID NO. 1.

Any of the foregoing methods pertaining to crystalline/inhibitor complexes wherein the inhibitor is of the formula (1):

1 preferably wherein the crystal has unit cell parameters wherein a is about 57 Å, b is about 44 Å, c is about 120 Å, α is about 90°, β is about 90°, and γ is about 90°, more preferably the unit cell parameters are a is about 57.6 Å, b is about 44.6 Å, c is about 121.6 Å, α is about 90.0°, β is about 90.2°, and γ is about 90.0°;

wherein the inhibitor is of the formula (2):

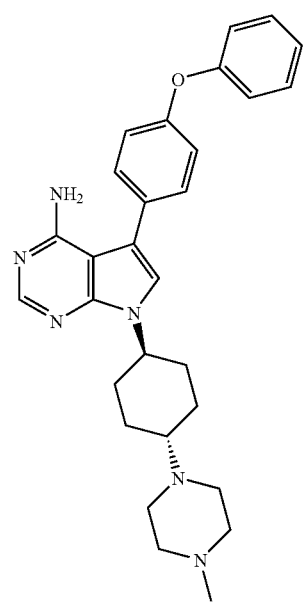

2 preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.4 Å, c is about 119.9 Å, α is about 90.0°, β is about 90.1°, and γ is about 90.0°;

wherein the inhibitor is of the formula (3):

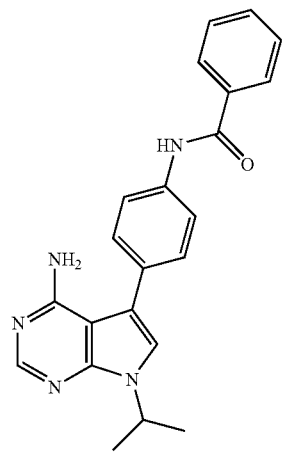

(3)

preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.3 Å, b is about 44.3 Å, c is about 120.8 Å, α is about 90.0°, β is about 90.0°, and γ is about 90.0°;

wherein the inhibitor is of the formula (4):

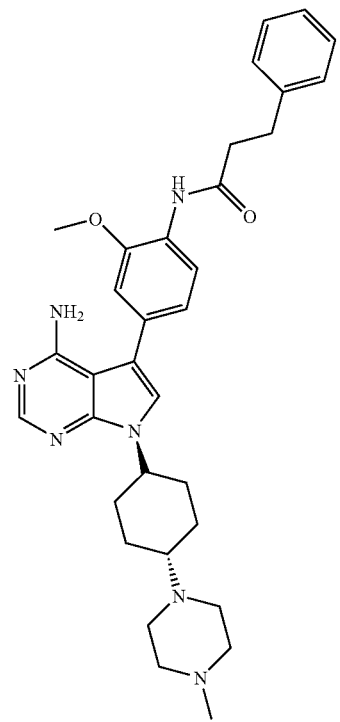

(4)

preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.8 Å, b is about 44.4 Å, c is about 126.2 Å, α is about 90.0°, β is about 90.0°, and γ is about 90.0°;

wherein the inhibitor is of the formula (5):

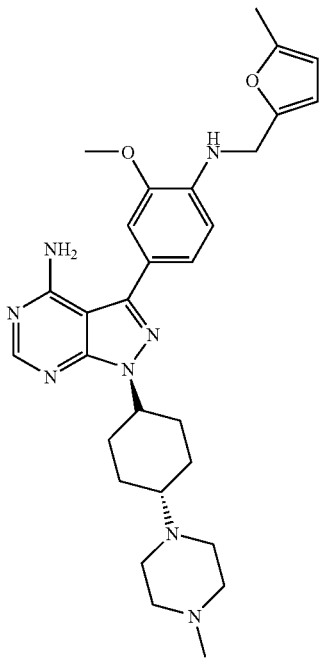

(5)

preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.6 Å, b is about 44.6 Å, c is about 120.0 Å, α is about 90.0°, β is about 90.1°, and γ is about 90.0°;

wherein the inhibitor is of the formula (6):

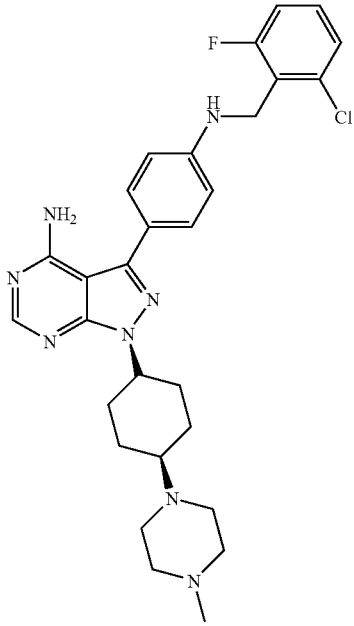

(6)

preferably, wherein the crystal has unit cell parameters wherein a is about 57 Å, b is about 44 Å, c is about 120 Å, α is about 90°, β is about 90°, and γ is about 90°, more preferably the unit cell parameters are a is about 56.8 Å, b is about 44.5 Å, c is about 120.2 Å, α is about 90.0°, β is about 90.0°, and γ is about 90.0°;

wherein the inhibitor is of the formula (7):

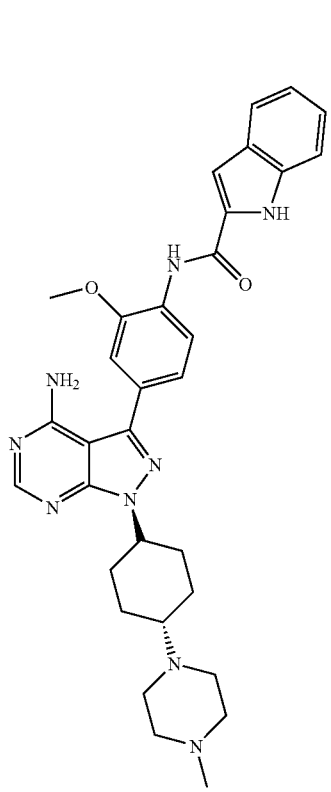

7 preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.4 Å, b is about 44.7 Å, c is about 119.8 Å, α is about 90.0°, β is about 90.0°, and γ is about 90.0°;

wherein the inhibitor is of the formula (8):

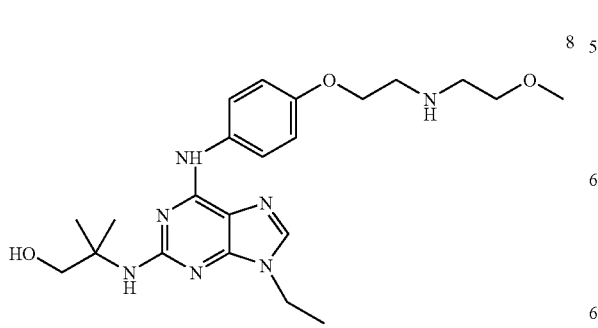

8 preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.4 Å, c is about 120.7 Å, α is about 90.0°, β is about 90.0°, and γ is about 90.0°;

wherein the inhibitor is of the formula (9):

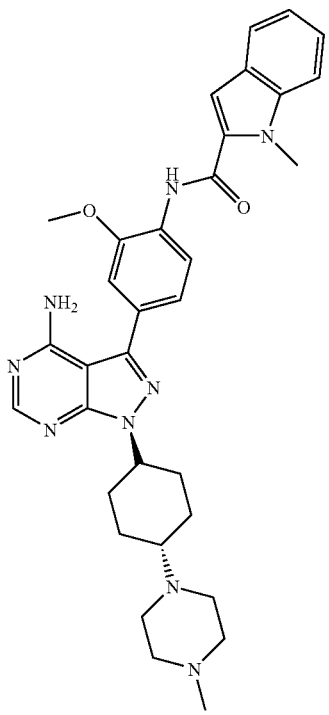

9 preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.1 Å, b is about 44.2 Å, c is about 118.3 Å, α is about 90.0°, β is about 89.9°, γ is about 90.0°;

wherein the inhibitor is of the formula (12):

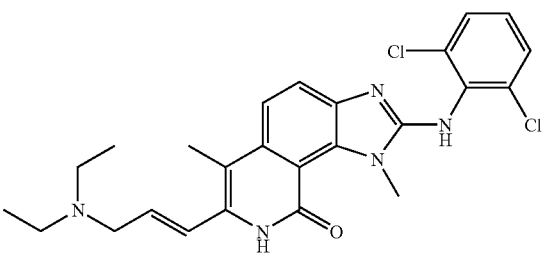

12 preferably, wherein the crystal has unit cell parameters a is about 57 Å, b is about 44 Å, c is about 120 Å, α is about 90°, β is about 90°, and γ about 90°, more preferably the unit cell parameters are a is about 57.9 Å, b is about 44.6 Å, c is about 122.0 Å, α is about 90.0°, β is about 89.9°, and γ is about 90.0°; and wherein the inhibitor is of the formula (13):

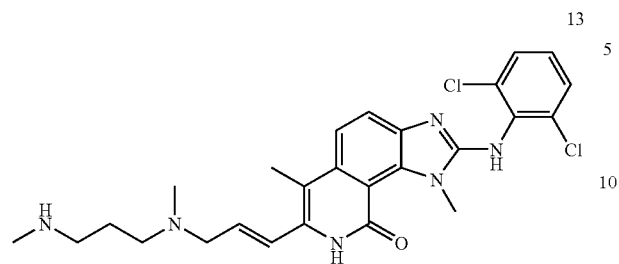

preferably, wherein the crystal has unit cell parameters wherein a is about 57 Å, b is about 44 Å, c is about 120 Å, α is about 90°, β is about 90°, and γ is about 90°, more preferably the unit cell parameters are a is about 57.2 Å, b is about 44.5 Å, c is about 120.1 Å, α is about 90.0°, β is about 90.0°, and γ is about 90.0°.

A method of identifying a compound which is a potential inhibitor of an Lck protein, said method comprising the step of designing a compound that will interact with one or more subsites in the catalytic domain of the Lck protein, based upon the crystal structure atomic coordinates of a polypeptide comprising the catalytic domain; wherein said compound is identified as a potential inhibitor of the Lck protein.

The foregoing method wherein the Lck protein is human Lck protein.

Any of the foregoing methods wherein the polypeptide: (a) contains the non-conservative Asp-364-Asn mutation; and (b) comprises human Lck amino acids 237-501 of SEQ ID NO. 1.

Any of the foregoing methods wherein the crystal structure atomic coordinates are set forth in FIG. 4, FIG. 5, FIG. 6, FIG. 7, FIG. 8, FIG. 9, FIG. 10, FIG. 11, FIG. 12, FIG. 13, FIG. 14, or FIG. 15.

Any of the foregoing methods wherein the compound interacts with: one or more of subsites 1 through 10; two or more of subsites 1 through 10; three or more of subsites 1 through 10; a set of subsites comprising subsite 1 and subsite 2; a set of subsites comprising subsite 1, subsite 2 and subsite 3; a set of subsites comprising subsite 1, subsite 2 and subsite 8; a set of subsites comprising subsite 1, subsite 2, subsite 3 and subsite 8; a set of subsites comprising subsite 1, subsite 2, subsite 3 and subsite 4; a set of subsites comprising subsite 1, subsite 2, subsite 3 and subsite 5; a set of subsites comprising subsite 1, subsite 2, subsite 3 and subsite 6; a set of subsites comprising subsite 1, subsite 2, subsite 3 and subsite 7; a set of subsites comprising subsite 1, subsite 2, subsite 3 and subsite 9; a set of subsites comprising subsite 1, subsite 2, subsite 3 and subsite 10; a set of subsites comprising subsite 1, subsite 2, subsite 8 and subsite 4; a set of subsites comprising subsite 1, subsite 2, subsite 8 and subsite 5; a set of subsites comprising subsite 1, subsite 2, subsite 8 and subsite 6; a set of subsites comprising subsite 1, subsite 2, subsite 8 and subsite 7; a set of subsites comprising subsite 1, subsite 2, subsite 8 and subsite 9; a set of subsites comprising subsite 1, subsite 2, subsite 8 and subsite 10; a set of subsites comprising subsite 1, subsite 2, subsite 3, subsite 4 and subsite 8; a set of subsites comprising subsite 1, subsite 2, subsite 3, subsite 5 and subsite 8; a set of subsites comprising subsite 1, subsite 2, subsite 3, subsite 6 and subsite 8; a set of subsites comprising subsite 1, subsite 2, subsite 3, subsite 7 and subsite 8; a set of subsites comprising subsite 1, subsite 2, subsite 3 and subsite 8 and subsite 9; a set of subsites comprising subsite 1, subsite 2, subsite 3, subsite 8 and subsite 10; or a set of subsites comprising subsite 1, subsite 2, subsite 3, subsite 5, subsite 6, subsite 7 and subsite 8.

An Lck inhibitor comprising two or more of the following elements:

(a) a hydrogen bond donor positioned to interact with Glu-317 of human Lck (SEQ ID NO. 1);

(b) a hydrogen bond acceptor positioned to interact with Met-319 of human Lck (SEQ ID NO. 1);

(c) a hydrogen bond donor positioned to interact with Met-319 of human Lck (SEQ ID NO. 1);

(d) a hydrogen bond acceptor positioned to interact with the side chain of Thr-316 of human Lck (SEQ ID NO. 1);

(e) a hydrophobic moiety positioned to interact with one or more of Leu-251, Val-259, Val-270, Ala-271, Val-272, Val-301, Thr-316, Ile-370, Leu-371, methylene carbon atoms of Lys-379 of human Lck (SEQ ID NO. 1);

(f) a hydrogen bond donor or positively charged moiety positioned to interact with Asp-326 of human Lck (SEQ ID NO. 1);

(g) a hydrogen bond donor positioned to interact with one or more of Leu-251, Ser-323 of human Lck (SEQ ID NO. 1);

(h) a hydrogen bond acceptor positioned to interact with one or more of Gly-322, Ser-323 of human Lck (SEQ ID NO. 1);

(i) a hydrogen bond donor positioned to interact with one or more of Asp-364, Arg-366, Asn-369 of human Lck (SEQ ID NO. 1);

(j) a hydrogen bond acceptor positioned to interact with one or more of Asp-364, Arg-366, Asn-369 of human Lck (SEQ ID NO. 1);

(k) a hydrogen bond donor positioned to interact with Glu-249, Arg-250, Gly-252, Ala-252, Gly-254, Gln-255, Phe-256, Gly-257, Glu-258, Trp-260, Met-261 of human Lck (SEQ ID NO. 1);

(l) a hydrogen bond acceptor positioned to interact with Glu-249, Arg-250, Gly-252, Ala-252, Gly-254, Gln-255, Phe-256, Gly-257, Glu-258, Trp-260, Met-261 of human Lck (SEQ ID NO. 1);

(m) a hydrophobic moiety positioned to interact with Glu-249, Arg-250, Gly-252, Ala-252, Gly-254, Gln-255, Phe-256, Gly-257, Glu-258, Trp-260, Met-261 of human Lck (SEQ ID NO. 1);

(n) a hydrogen bond donor positioned to interact with one or more of Asp-382, Phe-383, Gly-384 of human Lck (SEQ ID NO. 1);

(o) hydrogen bond acceptor positioned to interact with one or more of Asp-382, Phe-383, Gly-384 of human Lck (SEQ ID NO. 1);

(p) a hydrophobic moiety positioned to interact with one or more of Asp-382, Phe-383, Gly-384 of human Lck (SEQ ID NO. 1);

(q) a hydrogen bond acceptor positioned to interact with Lys-273 of human Lck (SEQ ID NO. 1);

(r) a hydrophobic moiety positioned to interact with Lys-273 human Lck (SEQ ID NO. 1);

(s) a hydrophobic moiety positioned to interact with one or more of Phe-285, Leu-286, Glu-288, Ala-289, Leu-291, Met-292, Leu-295, Leu-300, Leu-303, Ile-314, Ile-315, Ile-380, Ala-381, Leu-385 of human Lck (SEQ ID NO. 1);

(t) a hydrogen bond acceptor positioned to interact with one or more of Arg-302, Val-325, His-362, Asp-364, Ala-368 of human Lck (SEQ ID NO. 1);

(u) a hydrogen bond donor positioned to interact with one or more of Arg-302, Val-325, His-362, Asp-364, Ala-368 of human Lck (SEQ ID NO. 1);

(v) a hydrophobic moiety positioned to interact with one or more of Arg-302, Val-325, His-362, Asp-364, Ala-368 of human Lck (SEQ ID NO. 1);

(w) a hydrogen bond donor positioned to interact with one or more of Ala-386, Arg-387, Leu-388, Ile-389, Glu-390, Asp-391, Asn-392, Glu-393, Tyr-394, Thr-395, Ala-396, Arg-397 of human Lck (SEQ ID NO. 1);

(x) a hydrogen bond acceptor positioned to interact with one or more of Ala-386, Arg-387, Leu-388, Ile-389, Glu-390, Asp-391, Asn-392, Glu-393, Tyr-394, Thr-395, Ala-396, Arg-397 of human Lck (SEQ ID NO. 1); or (y) a hydrophobic moiety positioned to interact with one or more of Ala-386, Arg-387, Leu-388, Ile-389, Glu-390, Asp-391, Asn-392, Glu-393, Tyr-394, Thr-395, Ala-396, Arg-397 of human Lck (SEQ ID NO. 1).

A selective Lck inhibitor comprising one or more of elements (a) to (y) and additionally element:

(z) a hydrogen bond donor or positively charged moeity, or hydrogen bond donors or positively charged moieties, positioned to interact with one or more of Tyr-318 and Glu-320 of human Lck (SEQ ID NO. 1).

The Lck inhibitor of the foregoing comprising: (b) and (e); (e) and at least one of (a), (b) and (c); (e) and at least two of (a), (b) and (c).

Any of the foregoing Lck inhibitor further comprising (d).
Any of the foregoing Lck inhibitor further comprising (f).
Any of the foregoing Lck inhibitor further comprising one or more of (g), or (h).
Any of the foregoing Lck inhibitor further comprising one or more of (i), or (j).
Any of the foregoing Lck inhibitor further comprising one or more of (k), (l), or (m).
Any of the foregoing Lck inhibitor further comprising one or more of (n), (o), or (p).
Any of the foregoing Lck inhibitor further comprising one or more of (q), or (r).
Any of the foregoing Lck inhibitor further comprising (s).
Any of the foregoing Lck inhibitor further comprising one or more of (t), (u), or (v).
Any of the foregoing Lck inhibitor further comprising one or more of (w), (x), or (y).
Any of the foregoing Lck inhibitor further comprising one or more of (n), (o), or (p).
Any of the foregoing Lck inhibitor further comprising one or more of (q), or (r).
Any of the foregoing Lck inhibitor further comprising (s).
Any of the foregoing Lck inhibitor further comprising one or more of (n), (o), or (p).
Any of the foregoing Lck inhibitor further comprising one or more of (q), or (r).
Any of the foregoing Lck inhibitor further comprising (s).
Any of the foregoing Lck inhibitor further comprising one or more of (q), or (r).
Any of the foregoing Lck inhibitors further comprising (z).
Said Lck inhibitor being a potentially selective Lck inhibitor.

A method of identifying a compound which is a potential selective inhibitor of an Lck protein, said method comprising the step of designing a compound that will interact with one or more subsites in the catalytic domain of the Lck protein at least one of which is unique to the Lck protein, based upon the crystal structure atomic coordinates of a polypeptide comprising the catalytic domain; wherein said compound is identified as a potential selective inhibitor of the Lck protein.

The foregoing method wherein the Lck protein is human Lck protein.

The foregoing method wherein the polypeptide: (a) contains the non-conservative Asp-364-Asn mutation; and (b) comprises human Lck amino acids 237-501 of SEQ ID NO. 1.

The foregoing method wherein the crystal structure atomic coordinates are set forth in FIG. 4, FIG. 5, FIG. 6, FIG. 7, FIG. 8, FIG. 9, FIG. 10, FIG. 11, FIG. 12, FIG. 13, FIG. 14, or FIG. 15.

The foregoing method wherein the compound interacts with: one or more of subsites 1 through 10; two or more of subsites 1 through 10; three or more of subsites 1 through 10; a set of subsites comprising subsite 1 and subsite 2; a set of subsites comprising subsite 1, subsite 2 and subsite 3; a set of subsites comprising subsite 1, subsite 2 and subsite 8; a set of subsites comprising subsite 1, subsite 2, subsite 3 and subsite 8; a set of subsites comprising subsite 1, subsite 2, subsite 3 and subsite 4; a set of subsites comprising subsite 1, subsite 2, subsite 3 and subsite 5; a set of subsites comprising subsite 1, subsite 2, subsite 3 and subsite 6; a set of subsites comprising subsite 1, subsite 2, subsite 3 and subsite 7; a set of subsites comprising subsite 1, subsite 2, subsite 3 and subsite 9; a set of subsites comprising subsite 1, subsite 2, subsite 3 and subsite 10; a set of subsites comprising subsite 1, subsite 2, subsite 8 and subsite 4; a set of subsites comprising subsite 1, subsite 2, subsite 8 and subsite 5; a set of subsites comprising subsite 1, subsite 2, subsite 8 and subsite 6; a set of subsites comprising subsite 1, subsite 2, subsite 8 and subsite 7; a set of subsites comprising subsite 1, subsite 2, subsite 8 and subsite 9; a set of subsites comprising subsite 1, subsite 2, subsite 8 and subsite 10; a set of subsites comprising subsite 1, subsite 2, subsite 3, subsite 4 and subsite 8; a set of subsites comprising subsite 1, subsite 2, subsite 3, subsite 5 and subsite 8; a set of subsites comprising subsite 1, subsite 2, subsite 3, subsite 6 and subsite 8; a set of subsites comprising subsite 1, subsite 2, subsite 3, subsite 7 and subsite 8; a set of subsites comprising subsite 1, subsite 2, subsite 3, subsite 8 and subsite 9; a set of subsites comprising subsite 1, subsite 2, subsite 3, subsite 8 and subsite 10; a set of subsites comprising subsite 1, subsite 2, subsite 3, subsite 5, subsite 6, subsite 7 and subsite 8;

A selective Lck inhibitor being the Lck inhibitor of the foregoing method further comprising:

(z) a hydrogen bond donor or positively charged moiety, or hydrogen bond donors or positively charged moieties, positioned to interact with one or more of Tyr-318 and Glu-320 of human Lck (SEQ ID NO. 1).

A method of obtaining three-dimensional coordinates of a second polypeptide having at least 90% homology to a crystalline polypeptide comprising the catalytic domain amino acids 249-261, 271-273, 285-292, 301-305, 314-326, 368-371, and 381-398 of Lck by:

(a) obtaining three-dimensional coordinates of the crystalline polypeptide;
(b) aligning the sequence of the second polypeptide to the sequence of the catalytic domain;
(c) transferring the atomic coordinates of the first polypeptide to the corresponding sequence of the second polypeptide; and
(d) applying molecular modeling methods to obtain final coordinates of the second polypeptide.

A method according to the foregoing method wherein the second polypeptide is at least 80% homologous to the crystalline polypeptide comprising the catalytic domain of Lck.

A method according to the foregoing method wherein the second polypeptide is at least 70% homologous to the crystalline polypeptide comprising the catalytic domain of Lck.

The three-dimensional coordinates of the second polypeptide obtained according to any of the foregoing methods.

The method according to any of the foregoing methods wherein the second polypeptide comprises the catalytic domain of one or more of human Blk, Fgr, Yes, Fyn, Lyn, Hck, Lck, Src.

The invention further relates to a method for identifying a compound which preferentially inhibits the biological activity of Lck over proteins of related sequence and structure by, for example, inhibiting the catalytic activity of Lck by preferentially inhibiting the binding of natural substrates such as a tyrosine-containing polypeptide or a protein or ATP, to Lck. Such a compound is referred to herein as a "selective Lck inhibitor". By "selective", we mean that the concentration of the compound that inhibits the catalytic activity of Lck by 50% (the "$IC_{50}$") is at least 10-fold lower than the $IC_{50}$ of the compound that inhibits a protein of related sequence and structure. In other words, the $IC_{50}$ ratio is 10. Preferably, the $IC_{50}$ ratio is 30. More preferably, the $IC_{50}$ ratio is 100. Most preferably, the $IC_{50}$ ratio is 200.

The method of identifying a compound which preferentially inhibits the biological activity of Lck over proteins of related sequence and structure comprises the steps of (1) using a three-dimensional structure of Lck as defined by the atomic coordinates of the catalytic domain of Lck; (2) employing the three-dimensional structure to design or select a potential inhibitor which preferentially contacts residues or cavities unique to Lck; and (3) assessing the ability of the selected inhbitor to inhibit the catalytic activity of Lck more significantly than the catalytic activity of polypeptides related by sequence or structure. The method can also include the step of providing the compound designed or selected in step 2, for example, by synthesizing the compound or obtaining the compound from a compound library. In addition, the method can include the step of assessing the ability of the identified compound to bind to the catalytic domain of Lck and/or assessing the ability of the identified compound to inhibit the binding of a natural ligand of Lck. In addition, the method can include the step of assessing the ability of the identified compound to bind to polypeptides related to the catalytic domain of Lck by sequence or structure and/or assessing the ability of the identified compound to inhibit the binding of a natural ligand to polypeptides related to the catalytic domain of Lck by sequence or structure.

In another embodiment, the method for identifying a compound which selectively inhibits the biological activity of Lck comprises the step of determining the ability of one or more functional groups and/or moieties of the compound, when present in, or bound to, the Lck catalytic domain, to interact with one or more subsites of the Lck catalytic domain, at least one of which is unique to the Lck catalytic domain. Generally, the Lck catalytic domain is defined by the conserved homologous sequences when compared to other known protein tyrosine kinases. If the compound is able to interact with a preselected number or set of subsites at least one of which is unique to Lck, or has a calculated interaction energy within a desired or preselected range, the compound is identified as a potential selective inhibitor of Lck.

The invention further provides a method of designing a compound which is a potential selective inhibitor of the biological activity of Lck. The method includes the steps of (1) identifying one or more functional groups capable of interacting with one or more subsites of the Lck catalytic domain, at least one of which is unique to Lck; and (2) identifying a scaffold which presents the functional group, or functional groups, identified in step 1 in a suitable orientation for interacting with one or more subsites of the Lck catalytic domain, at least one of which subsites is unique to Lck. The compound which results from attachment of the identified functional groups or moieties to the identified scaffold is a potential selective inhibitor of Lck. The Lck catalytic domain is, generally, defined by the atomic coordinates of a polypeptide comprising the Lck catalytic domain.

In yet another embodiment, the invention provides compounds which selectively inhibit the biological activity of Lck and which preferentially fit, or bind to, the Lck catalytic domain with respect to polypeptides related to the catalytic domain of Lck by sequence or structure. Such compounds typically comprise one or more functional groups which, when the compound is bound in the Lck catalytic domain, interact with one or more subsites of the catalytic domain at least one of which is unique to Lck. Generally, the Lck catalytic domain is defined by the conserved homologous sequence when compared to other known protein tyrosine kinases. In a particular embodiment, the selective Lck inhibitor is a compound which is identified or designed by a method of the present invention.

A method for identifying a compound which is a selective inhibitor of an Lck protein, said method comprising the steps of:
(a) obtaining a crystal of a polypeptide comprising all or part of an Lck protein, wherein the polypeptide contains Lck residue Tyr-318;
(b) obtaining the atomic coordinates of said crystal;
(c) using said atomic coordinates to define the active subsites of Lck; and
(d) identifying a compound which binds to one or more of said active subsites, at least one of which is the active subsite that contains Lck residue Tyr-318; wherein the compound which binds to the active subsite or subsites is a selective inhibitor of the Lck.

The foregoing method further comprising the step of:
(e) assessing the ability of the compound identified in step (d) to selectively inhibit Lck.

A selective inhibitor of an Lck protein wherein said inhibitor contains a hydrogen bond donor or positively charged moiety, or hydrogen bond donors or positively charged moieties, positioned to interact with the side chain of Tyr-318 provided that the inhibitor is not

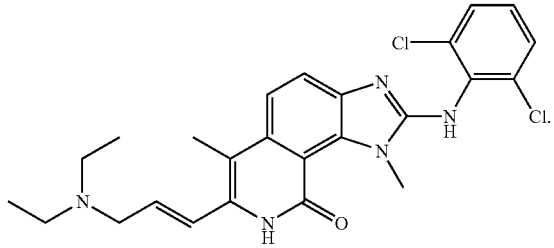

A method for identifying a compound which is a selective inhibitor of an Lck protein, said method comprising the steps of:
(a) obtaining a crystal of a polypeptide comprising all or part of an Lck protein, wherein the polypeptide contains Lck residue Glu-320;
(b) obtaining the atomic coordinates of said crystal;
(c) using said atomic coordinates to define the active subsites of Lck; and (d) identifying a compound which binds to one or more of said active subsites, at least one of which is the active subsite that contains Lck residue Glu-320; wherein the compound which binds to the active subsite or subsites is a selective inhibitor of the Lck.

The foregoing method, further comprising the step of:

(e) assessing the ability of the compound identified in step (d) to selectively inhibit Lck.

A selective inhibitor of an Lck protein wherein said inhibitor contains a hydrogen bond donor or positively charged moiety, or hydrogen bond donors or positively charged moieties, positioned to interact with the side chain of Glu-320.

A method for identifying a compound which is a selective inhibitor of an Lck protein, said method comprising the steps of:

(a) obtaining a crystal of a polypeptide comprising all or part of an Lck protein, wherein the polypeptide contains Lck residues Tyr-318 and Glu-320;

(b) obtaining the atomic coordinates of said crystal;

(c) using said atomic coordinates to define the active subsites of Lck; and (d) identifying a compound which binds to one or more of said active subsites, at least one of which is the active subsite that contains Lck residue Tyr-318 and Glu-320; wherein the compound which binds to the active subsite or subsites is a selective inhibitor of the Lck.

The foregoing method, further comprising the step of:

(e) assessing the ability of the compound identified in step (d) to selectively inhibit Lck.

A selective inhibitor of an Lck protein wherein said inhibitor contains a hydrogen bond donor or positively charged moiety, or hydrogen bond donors or positively charged moieties, positioned to interact with the side chains of both Tyr-318 and Glu-320.

BRIEF DESCRIPTION OF THE DRAWINGS

FIG. 1 Amino acid sequence of the human Lck protein. The complete sequence, amino acid residues 1-509, are shown. From the amino-terminus to the carboxy-terminus, the organization of the major functional domains of Lck is as follows: (1) the Src-homology ("SH") 4 ("SH4") domain (extends from about residue 2 to about residue 15); (2) the "unique" domain (extends from about residue 20 to about residue 60); (3) the SH3 domain (extends from about residue 65 to about residue 120); (4) the SH2 domain (extends from about residue 125 to about residue 220); (5) the SH1 domain (also known as the "catalytic domain" or the "kinase domain") (extends from about residue 235 to about residue 501); and (6) the "tail" (extends from about residue 503 to about residue 509) (SEQ ID NO. 1).

FIG. 2 Amino acid sequence of a polypeptide that approximates the catalytic domain of the human Lck protein. The polypeptide comprises amino acid residues 237 to 501 of the human Lck protein, with a non-conservative Asp-364-Asn point mutation (marked by an plus sign (+)). A phosphorylation site, at Tyr-394, is marked by an asterix (*) (SEQ ID NO. 2).

FIG. 3 Amino acid sequence of a polypeptide that approximates the catalytic domain of the human Lck protein. The polypeptide comprises amino acid residues 231 to 501 of the human Lck protein, with a non-conservative Asp-364-Asn point mutation (marked by an plus sign (+)). A phosphorylation site, at Tyr-394, is marked by an asterix (*) (SEQ ID NO. 3).

FIG. 4 presents the atomic coordinates for the SEQ ID NO. 2/Inhibitor 1 complex.

FIG. 5 presents the atomic coordinates for the SEQ ID NO. 2/Inhibitor 2 complex.

FIG. 6 presents the atomic coordinates for the SEQ ID NO. 2/Inhibitor 3 complex.

FIG. 7 presents the atomic coordinates for the SEQ ID NO. 2/Inhibitor 4 complex.

FIG. 8 presents the atomic coordinates for the SEQ ID NO. 2/Inhibitor 5 complex.

FIG. 9 presents the atomic coordinates for the SEQ ID NO. 2/Inhibitor 6 complex.

FIG. 10 presents the atomic coordinates for the SEQ ID NO. 2/Inhibitor 7 complex.

FIG. 11 presents the atomic coordinates for the SEQ ID NO. 2/Inhibitor 8 complex.

FIG. 12 presents the atomic coordinates for the SEQ ID NO. 2/Inhibitor 9 complex.

FIG. 13 presents the atomic coordinates for the SEQ ID NO. 2.

FIG. 14 presents the atomic coordinates for the SEQ ID NO. 2/Inhibitor 12 complex.

FIG. 15 presents the atomic coordinates for the SEQ ID NO. 2/Inhibitor 13 complex.

DETAILED DESCRIPTION OF THE INVENTION

The present invention relates to the x-ray crystallographic study of polypeptides comprising the catalytic domain of Lck. The atomic coordinates which result from this study are of use in identifying compounds which fit in the catalytic domain and are, therefore, potential inhibitors of Lck. These Lck inhibitors are of use in methods of treating a patient having a condition which is modulated by or dependent upon Lck activity, for example, a condition dependent on inappropriate or undesired stimulation of the immune system (multiple sclerosis, psoriasis, rheumatoid arthritis, Crohn's disease, lupus erythromatosis, chronic inflammatory diseases, and graft rejection following transplant surgery).

The following abbreviations and acronyms are used in this patent application: "ATP" refers to adenosine triphosphate; "SH" refers to Src homology; "AMP-PNP" refers to 5'-adenylimidodiphosphate; "DTT" refers to dithiothreitol; "PP1" refers to inhibitor 1; "wild-type" or "wildtype" refers to the unaltered, natural amino acid sequence of a protein. Amino acid substitution ("point") mutations are represented by the wild-type amino acid residue type, the residue number, and the mutated amino acid residue type. For example, point mutation of aspartate 364 to asparagine is represented as either "Asp-364-Asn" or "D364N", using the standard three- or one-letter abbreviations for amino acids.

Crystal Structures of Unphosphorylated Human Lck:

The Examples herein describe the preparation and crystallization of polypeptides comprising the catalytic domain of human Lck. As used herein, the term "catalytic domain" (or "kinase domain" or "SH1 domain") refers to a specific module, common to all protein tyrosine kinases and protein serine/threonine kinases that bind ATP. This specific module contains the substrate binding site, the site where ATP binds, including the metal-ion binding region, and the site where the phosphoryl transfer between ATP and the substrate occurs. For Lck, the catalytic domain is defined by amino acid residues from about residue 235 to about residue 501 of SEQ ID NO. 1 (see FIG. 1). Specific amino acid residues included in the catalytic domain that make interactions with bound ATP or inhibitors are discussed in more detail below.

The amino acid sequence of native human Lck (SEQ ID NO. Error! Reference source not found.; see Error! Reference source not found.) is taken as defined in SWISS-PROT World Wide Web Address: expasy.ch; Entry Name: LCK_HUMAN; Primary Accession Number: P06239), with the addition of the probable initiator N-terminal methionine residue ("residue 0" in the SWISS-PROT entry). Thus, the amino acid numbers presented in SEQ ID NO. Error! Reference source not found. comprise residues 1-509 (residue 1 being said methionine) rather than 1-508 (as in SWISS-PROT).

Lck is subject to autophosphorylation and transphosphorylation by other proteins. Phosphorylation state is a particularly important post-translational modification to consider. A wild-type Lck expression construct (i.e., without any substitutions or mutations in the Lck amino acid sequence) generally provides catalytically-active Lck protein, that is subject to autophosphorylation. This results in low yields during recombinant Lck protein expression and difficulty in protein purification (due to phosphorylation state heterogeneity). Wild-type Lck expressed in the ways previously described in the literature (Yamaguchi & Hendrickson, 1996; Zhu et al., 1999), precisely because these methods provide catalytically-active Lck phosphorylated at amino acid Tyr-394, limits one's ability to obtain crystals of Lck, complexed to inhibitors, that accurately present the unphosphorylated state of the enzyme which, as discussed above, is a possible target, distinct from phosphorylated Lck, for therapeutic intervention. Lck expression constructs that contain amino acid substitutions or mutations in the Lck amino acid sequence that are "conservative", that is, which do not substantially alter the catalytic or structural properties of the Lck protein, suffer from the same deficiencies. As described in the Examples, we have prepared mutated Lck expression constructs that contain "non-conservative" mutations, that is amino acid substitutions or mutations in the Lck amino acid sequence that do substantially alter the catalytic (or structural properties) of the Lck protein. In particular, two LLk expression constructs that produce Lck amino acid residues 237-501, with Asp-364 mutated to asparagine ("Lck(237-501, D364N)"; SEQ ID NO. 2; see FIG. 2), and Lck amino acid residues 231-501, with Asp-364 mutated to asparagine ("Lck(231-501, D364N)"; SEQ ID NO.3; see FIG. 3), both produce catalytically-inactive Lck in the unphosphorylated state. Both proteins could optionally be phosphorylated, using a catalytic amount of wild-type Lck and ATP, at residue Tyr-394.

As described in the Examples, both non-conservatively mutated forms of the catalytic domain of human Lck have been crystallized under a wide variety of conditions. In particular, Lck(237-501, D364N), in the unphosphorylated state, has been crystallized in the monoclinic space group P2(1), a=57.61 Å, b=44.64 Å, c=121.58 Å, β=90.17°. The term "space group" is a term of art that refers to the collection of symmetry elements of the unit cell of a crystal. The term "unit cell" is a term of art that refers to the fundamental repeating unit, akin to a building block, of a crystal. These crystals are distinct from all crystals that have been previously reported in the literature for any Lck protein (Yamaguchi & Hendrickson, 1996; Zhu et al., 1999). In particular, their unit cell is different, as is the molecular packing of the Lck molecules within their unit cell.

Seven parameters uniquely describe the symmetry and geometrical characteristics of a crystal. These parameters are the space group (symmetry), the three unit cell axial lengths "a", "b", and "c", and the three unit cell interaxial angles "α", "β", and "γ" (geometry). "Unit cell axial length" and "unit cell interaxial angle" are terms of art that refer to the three-dimensional geometrical characteristics of the unit cell, in essence its length, width, and height, and whether the building block is a perpendicular or oblique parallelepiped. The unit cell axial lengths and interaxial angles can vary by as much as ±10% without substantively altering the arrangement of the molecules within the unit cell. Thus, when we refer to each of the unit cell axial lengths and interaxial angles as being "about" a particular value, it is to be understood that we mean that any combination of these unit cell axial lengths and interaxial angles can vary by as much as ±10% from the stated values. Similarly, in particular cases, the space group of a crystal (and often in conjunction the unit cell parameters) can be altered to provide what appears to be, at first, a different crystal with altered symmetry (and geometrical) characteristics. Actually, however, this apparently new crystal is just another way of describing substantively the same crystalline form. As decribed below and in the examples in detail, we have crystallized Lck(237-501, D364N), in the unphosphorylated state, in the monoclinic space group P2(1), and in the orthorhombic space group P2(1)2(1)2(1). These two crystals, although they appear to be distinct, are not substantively different from one another, and can be considered interchangeable. With regard to all of the above discussion of crystal parameter variation either providing or not providing substantively the same crystals, all of the Lck crystalline forms we present here are distinct from all crystals that have been previously reported in the literature for any Lck protein (Yamaguchi & Hendrickson, 1996; Zhu et al., 1999). The monoclinic unit cell reported here contains two molecules of the catalytic domain of Lck in the crystallographic asymmetric unit. The term "asymmetric unit" is a term of art that refers to the unique portion of a crystal's molecular contents that can be expanded, using mathematical symmetry operations that are particular to a specific space group and which are familiar to one skilled in the art, to produce first the intact unit cell, and then by application of mathematical translational symmetry operations, the entire macroscopic crystal. Furthermore, the new crystals we report here have the advantage of being prepared in the presence of potent and selective inhibitors of human Lck. A shown by crystallographic structure determination, our new Lck crystals indeed contain not only two molecules of the catalytic domain of Lck in the crystallographic asymmetric unit, but also two molecules of an Lck inhibitor, and many ordered water molecules. As discussed extensively above, previous crystal structures of Lck have not been determined in the presence of such inhibitors.

The monoclinic unit cell of the crystals reported above appears to possess pseudo-orthorhombic symmetry. That is, the crystals approximate crystals that possess a more highly-symmetric unit cell that has slightly different dimensions. In particular, Lck(237-501, D364N), in the unphosphorylated state, can be considered to have also been crystallized in the orthorhombic space group P2(1)2(1)2(1), a=57.61 Å, b=44.72 Å, c=121.64 Å (the unit cell angle β is equal to 90° by definition in an orthorhombic space group; the unit cell lengths are slightly different because the unit cell angle β was constrained to be equal to 90°). This orthorhombic crystal form of Lck(237-501, D364N), in the unphosphorylated state contains half as many molecules in the crystallographic asymmetric unit as the monoclinic crystal form mentioned above, that is one molecule of the catalytic domain of Lck, one molecule of an Lck inhibitor, and half as many ordered water molecules. Furthermore, as is apparent to one skilled in the art, additional crystal forms that do not differ substantively from the monoclinic or orthorhombic forms described above can be obtained by slight modification of the protein or the crystallization conditions (such as the inhibitor used). These other crystals forms, which might be in different space groups, as demonstrated above for the monoclinic and orthorhombic forms, should be considered as equivalent to the crystal forms reported here.

As described in the Examples, certain of these crystals were examined by x-ray crystallography and atomic coordinates for the polypeptides were obtained. In certain cases, the polypeptide was unligated, that is, not complexed with a ligand. In other cases, the polypeptide was complexed with a ligand and the atomic coordinates of the ligand bound to the Lck catalytic domain were also obtained.

The atomic coordinates for eleven crystal structures of human Lck(237-501, D364N), in the unphosphorylated state and complexed to certain Lck inhibitors, that were examined by x-ray crystallography are presented in FIG. 4, FIG. 5, FIG. 6, FIG. 7, FIG. 8, FIG. 9, FIG. 10, FIG. 11, FIG. 12, FIG. 14, and FIG. 15. The term "atomic coordinates" (or "structural coordinates") is a term of art that refers to mathematical three-dimensional coordinates of the atoms in the material derived from mathematical equations related to the patterns obtained on diffraction of x-rays by the atoms (x-ray scattering centers) of a crystalline material. The diffraction data are used to calculate an electron density map of the unit cell of the crystal. These electron density maps are used to establish the positions of the individual atoms within the unit cell of the crystal. Atomic coordinates can be transformed, as is known to those skilled in the art, to different coordinate systems without affecting the relative positions of the atoms. Such transformed atomic coordinates should be considered as equivalent to the original coordinates. The atomic coordinates for a crystal structure of Lck(237-501, D364N), in the unphosphorylated state and not complexed to an inhibitors; that was examined by x-ray crystallography are presented in FIG. 13.

In particular, eleven high resolution crystal structures were obtained for human Lck(237-501, D364N), in the unphosphorylated state (SEQ ID NO. 2), complexed with one of eleven different Lck inhibitors shown below:

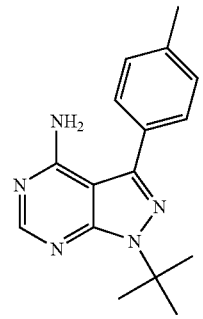

1

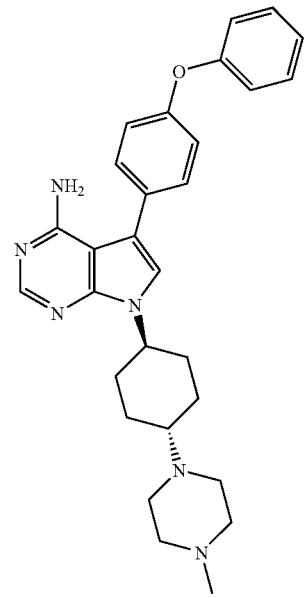

2

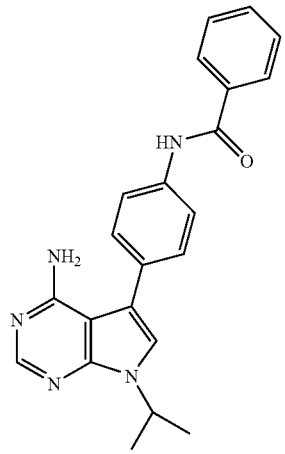

3

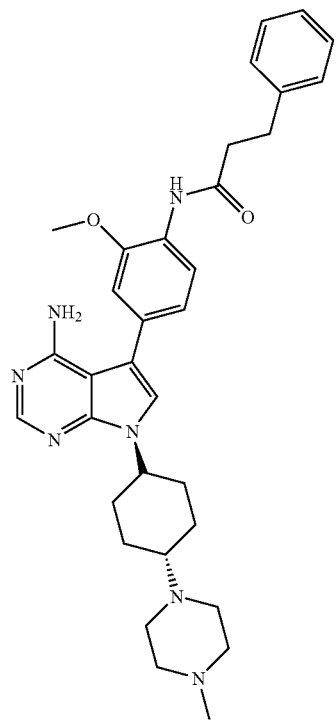
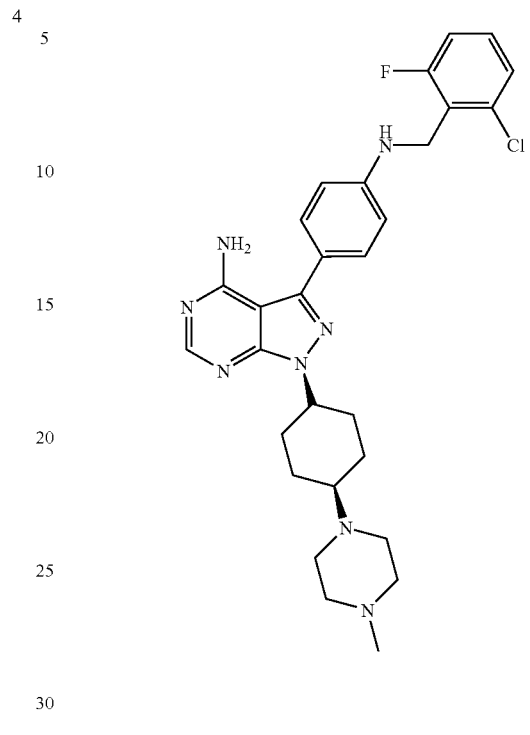
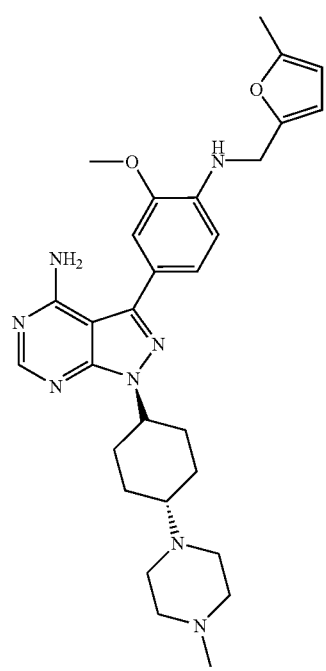
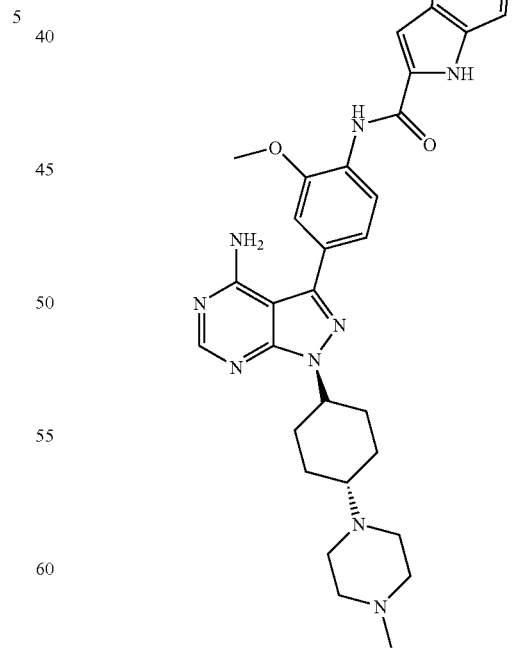

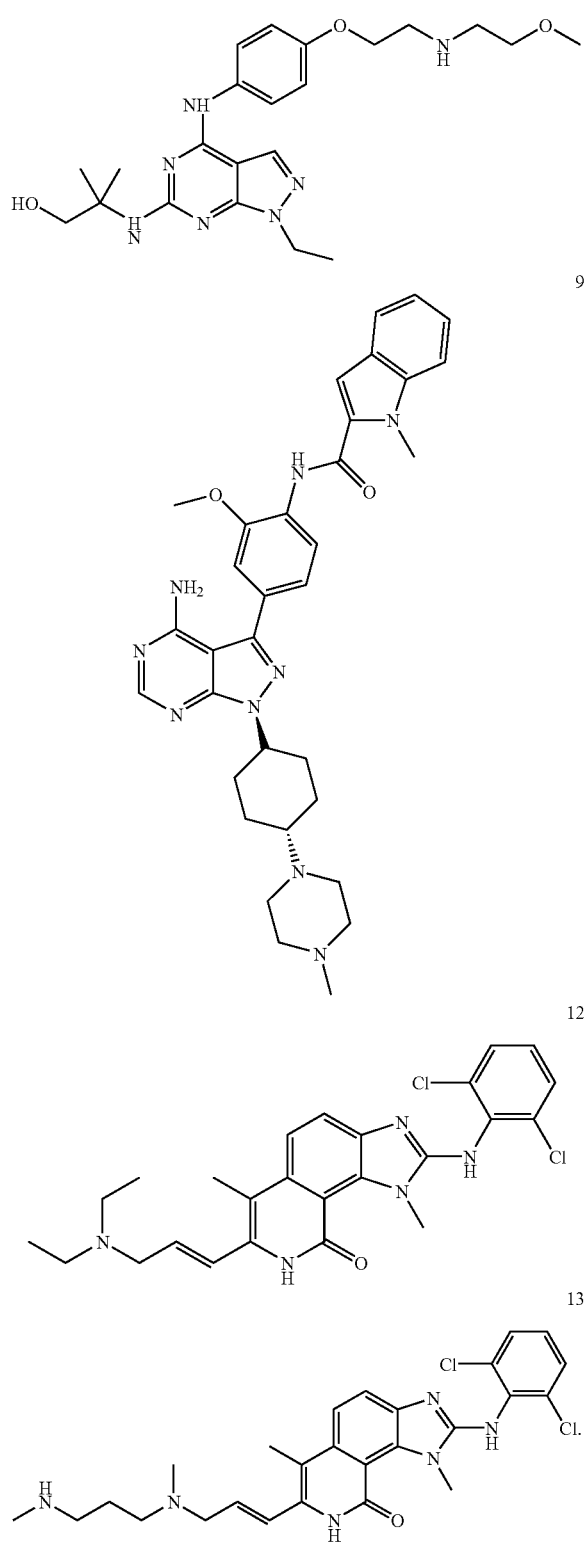

8

9

12

13

Crystals were also obtained of human Lck(231-501, D364N), in the phosphorylated state (SEQ ID NO. 3), complexed with one of two different Lck inhibitors shown below:

In particular, the crystalline phosphorylated human Lck (231-501, D364N) polypeptide/inhibitor complex was obtained wherein the inhibitor is of the formula (10):

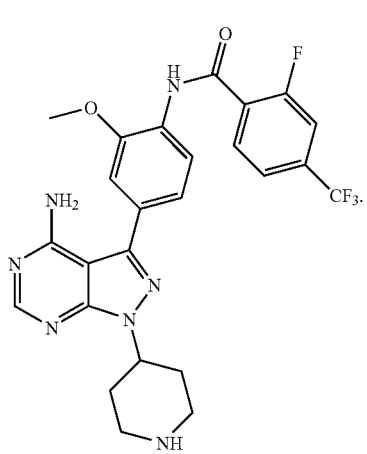

10

In particular, the crystalline phosphorylated human Lck (231-501, D364N) polypeptide/inhibitor complex was obtained wherein the inhibitor is of the formula (11):

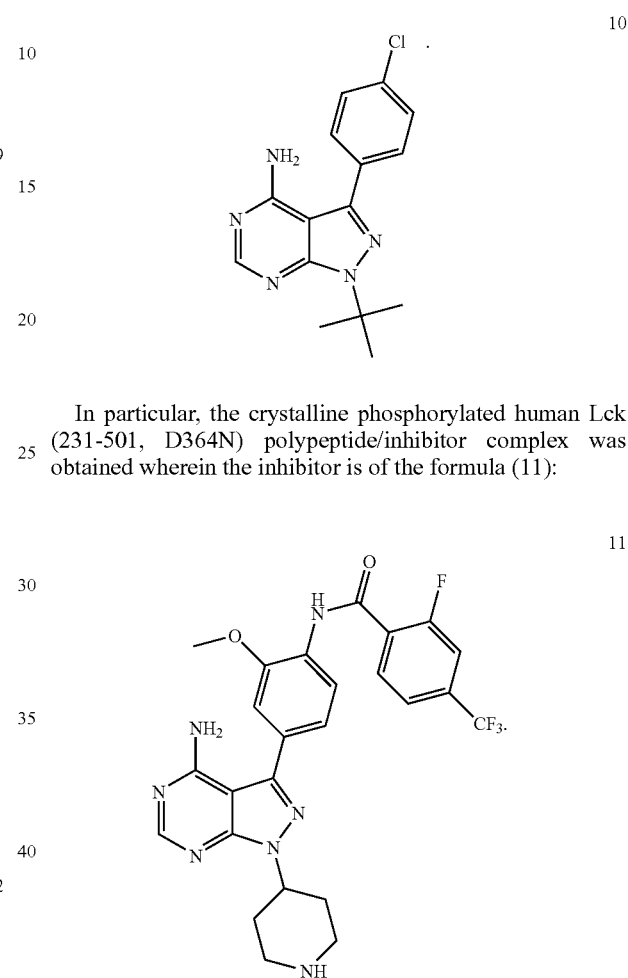

11

In particular, a high resolution crystal structures was also obtained for human Lck(237-501, D364N), in the unphosphorylated state (SEQ ID NO. 2), not bound to any inhibitor (the "apoenzyme").

Overall Inhibitor Binding Considerations:

The structures of the catalytic domain of Lck that we have determined all adopt a recognizable kinase fold. The inhibitors bind in the ATP binding site, a cleft between the N- and C-terminal lobes. Using the nomenclature originally adopted for c-AMP dependent protein kinase (Knighton et al., 1991), the ATP binding regions comprises residues located in β-strands 1-5, αC, αD, the hinge region that connects β5 to αD, β-strands 6 and 7, the catalytic loop, β-strands 8 and 9 and the activation loop. The activation loop contains the highly-conserved Asp-Phe-Gly amino acid sequence motif. In our Lck structures, βstrands 6 and 9 are not well formed as the activation loop has adopted a nontraditional conformation.

Binding Subsites and Interactions:

Analysis of the three dimensional structure of the Lck catalytic domain has indicated the presence of a number of subsites, each of which includes molecular functional groups capable of interacting with complementary moieties of an inhibitor. Subsites 1 through 10 of the Lck catalytic domain are defined below. A summary of the properties of the chemical moieties present at each subsite is given below. Subsites are characterized below according to the properties of chemical moieties with which they are complementary, or with which they can interact. Such moieties can include hydrogen bond acceptors, such as hydroxyl, amino, ether, thioether, carboxyl, P=O, and carbonyl groups, halogen atoms, such as fluorine, chlorine, bromine and iodine atoms; and other groups including a heteroatom having at least one lone pair of electrons, such as groups containing trivalent phosphorous, di- and tetravalent sulfur, oxygen and nitrogen atoms; hydrogen bond donors, such as hydroxyl, thiol, an amide proton, amine protons, carboxylic acid groups and any of the groups listed under hydrogen atom acceptors to which a hydrogen atom is bonded; hydrophobic groups, such as linear, branched or cyclic alkyl, ether or thioalkyl groups; linear, branched or cyclic alkenyl groups; linear, branched or cyclic alkynyl groups; aryl groups, such as mono- and polycyclic aromatic hydrocarbyl groups and mono- and polycyclic heterocyclic or heteroaryl groups; positively charged groups, such as primary, secondary, tertiary and quaternary ammonium groups, imidazolium and other protonated heteroalkyl and heteroaryl moieties, substituted and unsubstituted guanidinium groups, sulfonium groups and phosphonium groups; and negatively charged groups, such as carboxylate, phenolate, thiolate, sulfonamide, sulfamate, boronate, vanadate, sulfonate, sulfinate, phosphinate, tetrazolate and other heteroaryl anions, heterocyclic N-oxides, and phosphonate groups. A given chemical moiety can contain one or more of these groups The residue numbers cited below apply to human Lck (SEQ ID NO. 1).

Subsite 1: The hinge region

The inhibitor binding residues in the hinge region comprise hydrogen bonding partners, some of which bind to the purine core of ATP. Carbonyl oxygen atoms of Glu-317, Met-319 and Glu-320 and backbone N—H of Met-319 are accessible. The side chains of Thr-316, Tyr-318 and Glu-320 are also available as a hydrogen bonding partners. Most inhibitor binding residues in the eight human Src-family kinases are absolutely conserved. Notably, however, residue Tyr-318 is present only in Lck, Blk, Src, Lyn, and Fyn (phenylalanine in Hck, Yes, and Fgr), and Glu-320 is found only in Lck (alanine in Hck, Blk, and Lyn; serine in Src and Yes; asparagine in Fyn; and cysteine in Fgr).

Subsite 2: The purine core binding region

The purine ring of ATP is traditionally involved in hydrogen bonds with residues of the hinge region as noted above. In addition to these electrostatic interactions, hydrophobic residues stabilize and orient the molecule in the binding site. The residues comprising these interactions include Leu-251, Val-259, Val-270, Ala-271, Val-272, Val-301, Thr-316, Ile-370, Leu-371, and methylene carbon atoms of Lys-379.

Subsite 3: The extended sugar pocket

The ribose moiety of ATP traditionally interacts with residues of the N- and C-lobes of the kinase as well as molecules of the aqueous environment. Since a sugar residue is the interaction partner, most of the interactions are electrostatic in nature. These interactions can be formed with the backbone carbonyl oxygen atoms of Leu-251 and Ser-323, backbone N—H atoms of Gly-322 and Ser-323, and side chain atoms of Ser-323 and Asp-326.

Subsite 4: The γ-phosphate binding region

The charged triphosphate group of ATP is stabilized by specific interactions with the protein, in addition to metal cations and solvent. The specific residues which comprise this region include Asp-364, Arg-366 and Asn-369.

Subsite 5: The nucleotide binding loop

The nucleotide binding loop is a flexible loop located in the N-terminal lobe of the kinase which helps define the size and shape of the ATP binding site. In principle, residues in the range of 249-261 are part of this structural element. A number of interactions have already been assigned to a different subsite however, so in order to avoid confusion, this nucleotide binding loop interaction partners are here considered to comprise residues Glu-249, Arg-250, Gly-252, Aal-252, Gly-254, Gln-255, Phe-256, Gly-257, Glu-258, Trp-260, and Met-261. Both hydrogen bonding and hydrophobic interactions are possible with this subsite.

Subsite 6: The activation loop

The activation loop of protein kinases includes the conserved Asp-Phe-Gly amino acid sequence motif and structurally indicates the activation state of the Src-family of kinases which includes Lck. The specific residues which comprise this region/motif include Asp-382, Phe-383 and Gly-384. Structurally, the activation loop extends further, however residues too far beyond Gly-384 are outside of ATP binding region.

Subsite 7: The catalytic lysine

Lys-273 participates in the hydrolysis of ATP and phosphorylation of substrate tyrosine residues. In the case of non-hydrolyzable inhibitors, Lys-273 can donate hydrogen bonds and participate in hydrophobic interactions though its methylene carbon atoms.

Subsite 8: The distal hydrophobic pocket

One of the most significant binding opportunities present in the ATP binding region of Lck and other kinases is not accessed by ATP. The pocket is formed from residues of several different structural motifs including αC, β4, β5, β7, β8 and the activation loop. The interactions are predominately hydrophobic. The specific residues which comprise this region include Phe-285, Leu-286, Glu-288, Ala-289, Leu-291, Met-292, Leu-295, Leu-300, Leu-303, Ile-314, Ile-315, Ile-380, Ala-381 and Leu-385.

Subsite 9: Miscellaneous interaction partners

Several residues are in close proximity to the ATP binding site, but are not conveniently categorized as part of a specific structural motif. These residues include Arg-302, Val-325, His-362, Asp-364 and Ala-368. Both hydrogen bonding and hydrophobic interactions are possible with this subsite.

Subsite 10: The alternate conformation of the activation loop

It was mentioned above that residues in the activation loop too far downstream of the conserved Asp-Phe-Gly amino acid sequence motif generally do not interact with ATP site binders. It was also mentioned however, that the activation loop is in a non-traditional orientation in our structures. Therefore, a number of residues in the downstream portion of the activation loop are in close proximity to our inhibitors in these structures. The specific residues which comprise these interaction partners include Ala-386, Arg-387, Leu-388, Ile-389, Glu-390, Asp-391, Asn-392, Glu-393, Tyr-394, Thr-395, Ala-396 and Arg-397.

Structure-Based Drug Design:

The comparison of sequences and determination of percent identity and homology between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991). In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available on Mar. 29, 2000 at http://www.gcg.com), using either a Blossom 62 matrix or a PAM250 matrix, and a gap weight of, for example, 16, 14, 12, 10, 8, 6, or 4 and a length weight of, for example, 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available on Mar. 29, 2000 at http://www.gcg.com), using a NWSgapdna.CMP matrix and a gap weight of, for example, 40, 50, 60, 70, or 80 and a length weight of, for example, 1, 2, 3, 4, 5, or 6. In another embodiment, the percent identity between two amino acid or nucleotide sequences is determined using the algorithm of E. Meyers and W. Miller (*CABIOS*, 4:11-17 (1989)) which has been incorporated into the ALIGN program (version 2.0), using, for example, a PAM120 weight residue table, a gap length penalty of 12 and a gap penalty of 4.

The protein sequences of the present invention can further be used as a "query sequence" to perform a search against databases to, for example, identify other family members or related sequences. Such searches can be performed using the NBLAST and XBLAST programs (version 2.0) of Altschul, et al. (*J. Mol. Biol.* 215:403-10 (1990)). BLAST protein searches can be performed with the XBLAST program, for example, score=50, word length=3, to obtain amino acid sequences homologous to the proteins of the invention. To obtain gapped alignments for comparison purposes, gapped BLAST can be utilized as described in Altschul et al., (*Nucleic Acids Res.* 25(17):3389-3402 (1997)). When utilizing BLAST and gapped BLAST programs, the default parameters of the respective programs (e.g., XBLAST and NBLAST) can be used as given on Mar. 29, 2000 at World Wide Web address www/ncbi./nlm./nih.gov.

Homology for amino acid sequences can be defined in terms of the parameters set by the Advanced Blast search available from NCBI (the National Center for Biotechnology Information; see, for Advanced BLAST, World Wide Web address: ncbi.nlm.nih.gov/cgi bin/BLAST/nph-newblast?J-form=1 (on Mar. 29, 2000)). These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found on related website pages and in Altschul, S. F. et al., *Nucleic Acids Res.* 25:3389-3402 (1997).

In one embodiment, the invention relates to a method of determining the three dimensional structure of a first polypeptide comprising the catalytic domain of a Lck protein. The method includes the steps of (1) obtaining a crystal comprising the first polypeptide; (2) obtaining x-ray diffraction data for said crystal; and (3) using the x-ray diffraction data and the atomic coordinates of a second polypeptide comprising the catalytic domain of a Lck protein to solve the crystal structure of the first polypeptide, thereby determining the three dimensional structure of the first polypeptide. The second polypeptide can include the same Lck catalytic domain as the first polypeptide, or a different Lck catalytic domain. Either or both of the first and second polypeptides can, optionally, be complexed with a ligand. That is, the crystal of the first polypeptide can comprise a complex of the first polypeptide with a ligand. The atomic coordinates of the second polypeptide can, optionally, include the atomic coordinates of a ligand molecule bound to the second polypeptide. The atomic coordinates of the second polypeptide, generally, have been previously obtained, for example, by x-ray crystallographic analysis of a crystal comprising the second polypeptide or a complex of the second polypeptide with a ligand. The atomic coordinates of the second polypeptide can be used to solve the crystal structure using methods known in the art, for example, molecular replacement or isomorphous replacement. Preferably, the second polypeptide comprises the catalytic domain of a mammalin Lck, more preferably, human Lck.

The invention also provides a method of identifying a compound which is a potential inhibitor of Lck. The method comprises the steps of (1) obtaining a crystal of a polypeptide comprising the catalytic domain of Lck; (2) obtaining the atomic coordinates of the polypeptide by x-ray diffraction studies using said crystal; (3) using said atomic coordinates to define the catalytic domain of Lck; and (4) identifying a compound which fits the catalytic domain. The method can further include the steps of obtaining, for example, from a compound library, or synthesizing the compound identified in step 4, and assessing the ability of the identified compound to inhibit Lck enzymatic activity.

The invention also provides a method of identifying a compound which is a potential selective inhibitor of Lck. The method comprises the steps of: (1) obtaining a crystal of a polypeptide comprising the catalytic domain of Lck; (2) obtaining the atomic coordinates of the polypeptide by x-ray diffraction studies using said crystal; (3) using said atomic coordinates to define the catalytic domain of Lck; and (4) identifying a compound which fits the catalytic domain preferentially making contact with residues or sites unique to Lck. The method can further include the steps of obtaining, for example, from a compound library, or synthesizing the compound identified in step 4, and assessing the ability of the identified compound to inhibit Lck enzymatic activity.

The polypeptide preferably comprises the catalytic domain of a mammalian Lck. More preferably the polypeptide comprises the catalytic domain of human Lck. In a preferred embodiment, the polypeptide is a polypeptide of the present invention, as described above.

The polypeptide can be crystallized using methods known in the art, such as the methods described in the Examples, to afford polypeptide crystals which are suitable for x-ray diffraction studies. A crystalline polypeptide/ligand complex can be produced by soaking the resulting crystalline polypeptide in a solution including the ligand. Preferably, the ligand solution is in a solvent in which the polypeptide is insoluble.

The atomic coordinates of the polypeptide (and ligand) can be determined, for example, by x-ray crystallography using methods known in the art. The data obtained from the crystallography can be used to generate atomic coordinates, for example, of the atoms of the polypeptide and ligand, if present. As is known in the art, solution and refinement of the x-ray crystal structure can result in the determination of coordinates for some or all of the non-hydrogen atoms. The atomic coordinates can be used, as is known in the art, to generate a three-dimensional structure of the Lck catalytic domain. This structure can then be used to assess the ability of any given compound, preferably using computer-based methods, to fit into the catalytic domain.

A compound fits into the catalytic domain if it is of a suitable size and shape to physically reside in the catalytic domain, that is, if it has a shape which is complementary to the catalytic domain and can reside in the catalytic domain without significant unfavorable steric or van der Waals interactions. Preferably, the compound includes one or more functional groups and/or moieties which interact with one or more subsites within the catalytic domain. Computational methods for evaluating the ability of a compound to fit into the catalytic domain, as defined by the atomic coordinates of the polypeptide, are known in the art, and representative examples are provided below.

In another embodiment, the method of identifying a potential inhibitor of Lck comprises the step of determining the ability of one or more functional groups and/or moieties of the compound, when present in the Lck catalytic domain, to interact with one or more subsites of the Lck catalytic domain. Preferably, the Lck catalytic domain is defined by the atomic coordinates of a polypeptide comprising the Lck catalytic domain. If the compound is able to interact with a preselected number or set of subsites, the compound is identified as a potential inhibitor of Lck.

A functional group or moiety of the compound is said to "interact" with a subsite of the Lck catalytic domain if it participates in an energetically favorable, or stabilizing, interaction with one or more complementary moieties within the subsite. Two chemical moieties are "complementary" if they are capable, when suitably positioned, of participating in an attractive, or stabilizing, interaction, such as an electrostatic or van der Waals interaction. Typically, the attractive interaction is an ion-ion (or salt bridge), ion-dipole, dipole-dipole, hydrogen bond, pi-pi or hydrophobic interaction. For example, a negatively charged moiety and a positively charged moiety are complementary because, if suitably positioned, they can form a salt bridge. Likewise, a hydrogen bond donor and a hydrogen bond acceptor are complementary if suitably positioned.

Typically, an assessment of interactions between the test compound and the Lck catalytic domain may employ computer-based computational methods, such as those known in the art, in which possible interactions of a compound with the protein, as defined by atomic coordinates, are evaluated with respect to interaction strength by calculating the interaction energy upon binding the compound to the protein. Compounds which have calculated interaction energies within a preselected range or which otherwise, in the opinion of the computational chemist employing the method, have the greatest potential as Lck inhibitors, can then be provided, for example, from a compound library or via synthesis, and assayed for the ability to inhibit Lck. The interaction energy for a given compound generally depends upon the ability of the compound to interact with one or more subsites within the protein catalytic domain.

In one embodiment, the atomic coordinates used in the method are the atomic coordinates set forth in the Figures of this application. It is to be understood that the atomic coordinates set forth in the Figures can be transformed, for example, into a different coordinate system, in ways known to those skilled in the art without substantially changing the three-dimensional structure represented thereby.

In certain cases, a moiety of the compound can interact with a subsite via two or more individual interactions. A moiety of the compound and a subsite can interact if they have complementary properties and are positioned in sufficient proximity and in a suitable orientation for a stabilizing interaction to occur. The possible range of distances for the moiety of the compound and the subsite depends upon the distance dependence of the interaction, as is known in the art. For example, a hydrogen bond typically occurs when a hydrogen bond donor atom, which bears a hydrogen atom, and a hydrogen bond acceptor atom are separated by about 2.5 Å and about 3.5 Å. Hydrogen bonds are well known in the art (Pimentel et al., *The Hydrogen Bond*, San Francisco: Freeman (1960)). Generally, the overall interaction, or binding, between the compound and the Lck catalytic domain will depend upon the number and strength of these individual interactions.

The ability of a test compound to interact with one or more subsites of the catalytic domain of Lck can be determined by computationally evaluating interactions between functional groups, or moieties, of the test compound and one or more amino acid side chains in a particular protein subsite, such as the subsites described hereinabove. Typically, a compound which is capable of participating in stabilizing interactions with a preselected number of subsites, preferably without simultaneously participating in significant destabilizing interactions, is identified as a potential inhibitor of Lck. Such a compound will interact with one or more subsites, preferably with two or more subsites and, more preferably, with three or more subsites.

Suitable methods, as are known in the art, can be used to identify chemical moieties, fragments or functional groups which are capable of interacting favorably with a particular subsite or set of subsites. These methods include, but are not limited to: interactive molecular graphics; molecular mechanics; conformational analysis; energy evaluation; docking; database searching; pharmacophore modeling; de novo design and property estimation. These methods can also be employed to assemble chemical moieties, fragments or functional groups into a single inhibitor molecule. These same methods can also be used to determine whether a given chemical moiety, fragment or functional group is able to interact favorably with a particular subsite or set of subsites.

In one embodiment, the design of potential human Lck inhibitors begins from the general perspective of three-dimensional shape and electrostatic complementarity for the catalytic domain, encompassing the subsites described hereinabove, and subsequently, interactive molecular modeling techniques can be applied by one skilled in the art to visually inspect the quality of the fit of a candidate inhibitor modeled into the binding site. Suitable visualization programs include INSIGHTII (Molecular Simulations Inc., San Diego, Calif.), QUANTA (Molecular Simulations Inc., San Diego, Calif.), SYBYL (Tripos Inc., St Louis, Mo.), RASMOL (Roger Sayle et al., *Trends Biochem. Sci.* 20: 374-376 (1995)), GRASP (Nicholls et al., *Proteins* 11: 281-289 (1991)), and MIDAS (Ferrin et al., *J. Mol. Graphics* 6: 13-27 (1988)).

A further embodiment of the present invention utilizes a database searching program which is capable of scanning a database of small molecules of known three-dimensional structure for candidates which fit into the target protein site. Suitable software programs include CATALYST (Molecular Simulations Inc., San Diego, Calif.), UNITY (Tripos Inc., St Louis, Mo.), FLEXX (Rarey et al., *J. Mol. Biol.* 261: 470-489 (1996)), CHEM-3DBS (Oxford Molecular Group, Oxford, UK), DOCK (Kuntz et al., *J. Mol. Biol* 161: 269-288 (1982)), and MACCS-3D (MDL Information Systems Inc., San Leandro, Calif.). It is not expected that the molecules found in the search will necessarily be leads themselves, since a complete evaluation of all interactions will necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that the scaffold, functional groups, linkers and/or monomers may be changed to maximize the electrostatic, hydrogen bonding, and hydrophobic interactions with the enzyme. Goodford (Goodford *J Med Chem* 28:849-857 (1985)) has produced a computer program, GRID, which seeks to determine regions of high affinity for different chemical groups (termed probes) on the molecular surface of the binding site. GRID hence provides a tool for suggesting modifications to known ligands that might enhance binding.

A range of factors, including electrostatic interactions, hydrogen bonding, hydrophobic interactions, desolvation effects, conformational strain or mobility, chelation and cooperative interaction and motions of ligand and enzyme, all influence the binding effect and should be taken into account in attempts to design bioactive inhibitors.

Yet another embodiment of a computer-assisted molecular design method for identifying inhibitors comprises searching for fragments which fit into a binding region subsite and link to a predefined scaffold. The scaffold itself may be identified in such a manner. Programs suitable for the searching of such functional groups and monomers include LUDI (Boehm, *J Comp. Aid. Mol. Des.* 6:61-78 (1992)), CAVEAT (Bartlett et al. in "Molecular Recognition in Chemical and Biological Problems", special publication of *The Royal Chem. Soc.*, 78:182-196 (1989)) and MCSS (Miranker et al. *Proteins* 11: 29-34 (1991)).

Yet another embodiment of a computer-assisted molecular design method for identifying inhibitors of the subject phosphatase comprises the de novo synthesis of potential inhibitors by algorithmic connection of small molecular fragments that will exhibit the desired structural and electrostatic complementarity with the active site of the enzyme. The methodology employs a large template set of small molecules with are iteratively pieced together in a model of the Lck active site. Programs suitable for this task include GROW (Moon et al. *Proteins* 11:314-328 (1991)) and SPROUT (Gillet et al. *J Comp. Aid. Mol. Des.* 7:127 (1993)).

In yet another embodiment, the suitability of inhibitor candidates can be determined using an empirical scoring function, which can rank the binding affinities for a set of inhibitors. For an example of such a method see Muegge et al. and references therein (Muegge et al., *J Med. Chem.* 42:791-804 (1999)).

Other modeling techniques can be used in accordance with this invention, for example, those described by Cohen et al. (J. Med. Chem. 33: 883-894 (1994)); Navia et al. (*Current Opinions in Structural Biology* 2: 202-210 (1992)); Baldwin et al. (*J. Med. Chem.* 32: 2510-2513 (1989)); Appelt et al. (*J. Med. Chem.* 34: 1925-1934 (1991)); and Ealick et al. (*Proc. Nat. Acad. Sci. USA* 88: 11540-11544 (1991)).

As described in the Examples, the crystal structures of unphosphorylated Lck(237-501, D364N), alone or complexed to inhibitors or ligands, can be used to aid in the design of Lck inhibitors. For example, the three-dimensional atomic coordinates of the unphosphorylated Lck(237-501, D364N) .inhibitor 7 crystal structure (FIG. 10) were used to design the novel Lck inhibitor trans-3-[4-(1H-3-indazolylamino)phenyl]-1-[4-(4-methylpiperazino) cyclohexyl]-1H-pyrazolo[3,4-d]pyrimidin-4-amine (15).

First, in consideration of how the indolamide portion of inhibitor 7 is bound to Lck, the molecular fragment 14 shown below was conceived. Three-dimensional atomic coordinates for fragment 14 were then calculated by using standard molecular modeling techniques (computer program CORINA).

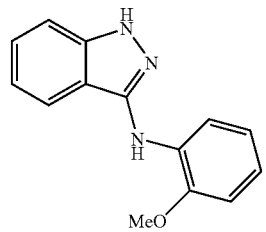

Using standard molecular modeling techniques (computer program INSIGHT II), the atomic coordinates of the fragment 14 and of the unphosphorylated Lck(237-501, D364N) .inhibitor 7 complex (FIG. 10) were superimposed. In particular, the phenyl ring of fragment 14 was superimposed on the phenyl ring of inhibitor 7 in an orientation such that the indazolyl moiety of fragment 14 occupied the space of the indolamide in the Lck crystal structure. The position of fragment 14 was adjusted so that the overlap of N2 of the indazolyl moiety with the amide carbonyl oxygen atom of inhibitor 7 was maximized, and so that unfavorable van der Waals contacts between the amino acid residues of Lck and fragment 14 were minimized. Visual examination of the modeled complex indicated that favorable interactions between the protein and proposed inhibitor could be realized by an inhibitor in a conformation involving minimal strain. Thus, the molecular modeling demonstrated that the aminoindazolyl moiety could serve as a replacement for the indolylamide moiety.

The designed compound, trans-3-[4-(1H-3-indazolylamino)phenyl]-1-[4-(4-methylpiperazino)cyclohexyl]-1H-pyrazolo[3,4-d]pyrimidin4-amine, inhibitor 15 below, was synthesized and tested for Lck inhibitory properties. It was found to be a potent inhibitor of human Lck.

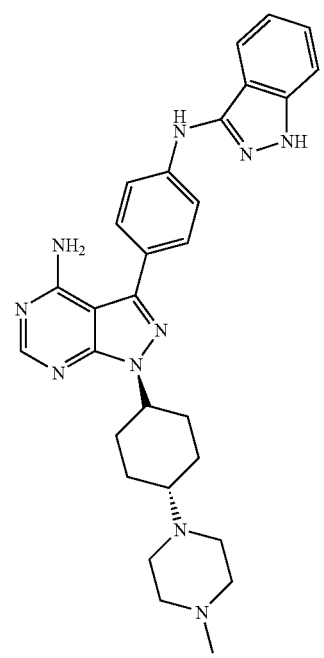

This invention is further illustrated by the following examples which should not be construed as limiting. The contents of all references, patents and published patent applications cited throughout this application are hereby incorporated by reference.

EXAMPLES

Example 1

Protein Purification 1.1. Purification of Human Lck(237-501, D364N) in an Unphosphorylated State.

Human Lck(237-501, D364N) [SEQ ID NO. 2], which contains an amino-terminal $(His)_6$ affinity purification tag followed by a tobacco etch virus (TEV) protease cleavage peptide, was expressed by recombinant baculovirus infection of *Spodoptera frugiperda* (Sf9) cells. The following procedure was carried out at about 4° C. unless specified otherwise. Cells from a 10 liter culture (stored frozen at about −80° C.) were thawed and re-suspended in 250 mL of a lysis buffer containing 20 mM Tris, pH 8.0, 50 mM NaCl, 10% (v/v) glycerol, 1% Triton X-100, and 10 "protease tabs" (EDTA-free complete protease inhibitor; Boehringer Mannheim, Part No. 1-873-580). After about 30 min of incubation on ice, the cell lysate was centrifuged (GSA rotor, 12,500 rpm, 25 min). A 5 mL Hi-Trap chelating Sepharose affinity column (Pharmacia-Amersham) was prepared by washing with 25 mL of water, charging with 50 mL of 100 mM $NiCl_2$, washing with 25 mL of water, washing with 10 mL of IMAC Buffer A (50 mM HEPES, pH 7.5, 10% (v/v) glycerol, 300 mM NaCl) containing 500 mM imidazole (IMAC Buffer B), and finally washing with 15 mL of IMAC Buffer A. The cell lysate supernatant was diluted with one volume of IMAC Buffer A and applied to the affinity column at 4 mL/min flow rate. The column was washed with IMAC buffer A until non-specifically-bound proteins were eluted (monitored by UV absorbance at 280 nm). The column was washed with an 82.5:12.5 mixture of IMAC Buffers A:B until the absorbance was reestablished. Lck 237-501 (D364N) was eluted with a 50:50 mixture of IMAC Buffers A:B. Fractions containing a protein concentration greater than 0.3 mg/mL (determined with a Coomassie protein assay; BioRad) were pooled. TEV protease (1000 Units of TEV protease/6 mg of estimated protein) was added to the eluted $(HiS)_6$ Lck(237-501, D364N), and the mixture was placed in a 6,000-8,000 MWCO dialysis bag and dialyzed against 100 volumes of 20 mM Tris, pH 8.0, 25 mM NaCl, and 2 mM DTT overnight at about 12° C. A MonoQ 10/10 (Pharmacia-Amersham) anion exchange column was washed with 40 mL of Q Buffer A (20 mM Bis-Tris, pH 7.0) containing 500 mM NaCl (Q Buffer B) and then 40 mL of Q Buffer A. The dialyzed Lck 237-501 (D364N) sample was centrifuged to remove any precipitated protein, filtered (0.2 μm), and loaded onto the MonoQ column (4 mL/min flow rate). The column was washed with 5-7 column volumes (~50 mL) of Q Buffer A, until the UV absorbance returned to baseline. Then, Lck(237-501, D364N) was eluted with linear gradient of 0-0.5 M NaCl (100% Buffer A to 100% Buffer B, 50 column volumes [~400 mL total volume]). Fractions containing a protein concentration greater than 0.2 mg/mL were pooled. DTT (final concentration, 10 mM), $NaN_3$ (final concentration, 3 mM), and optionally an inhibitor (1.2-fold molar excess) were added. The sample was concentrated to ~20 mg/mL using an Ultrafree-15 Biomax 10 K MWCO centrifugal filter device (Millipore) and frozen at −80° C. This concentrated sample was used in crystallographic experiments described below. Sample purity was assessed with SDS-PAGE, native PAGE, and LC/MS total mass analysis (including phosphopeptide mapping), which revealed that the Lck (237-501, D364N) was not phosphorylated.

1.2. Purification of Human Lck(237-501, D364N) in a Phosphorylated State.

Human Lck(237-501, D364N) [SEQ ID NO. 2] phosphorylated at Tyr-394 was prepared as above for the unphosphorylated protein, with the following modification. After the dialysis/TEV cleavage step, the sample was transferred to a second dialysis bag and dialyzed against 100 volumes of 50 mM MOPSO, pH 6.5, 25 mM NaCl, 10 mM $MgCl_2$, 2 mM $MnCl_2$, 2.5 mM DTT, 100 μM $Na_3VO_4$ at about 4° C. for about 3-5 h. After centrifugation to remove precipitate, a catalytic amount (1% on a molar basis) of human Lck 1-509 [SEQ ID NO. 1; also expressed by recombinant baculovirus infection of Sf9 cells, and purified in a manner similar to Lck(237-501, D364N)] and ATP (final concentration, 1 mM) were added to the dialysate. The sample was incubated overnight at about 12° C. The purification was completed as described above for unphosphorylated Lck(237-501, D364N). The sample was concentrated to ~15-25 mg/mL using an Ultrafree-15 Biomax 10 K MWCO centrifugal filter device (Millipore) and frozen at about −80° C. This concentrated sample was used in crystallographic experiments also described below. Sample purity was assessed with SDS-PAGE, native PAGE, and LCIMS total mass analysis (including phosphopeptide mapping), which revealed that the Lck (237-501, D364N) was essentially homogeneously phosphorylated at Tyr-394.

1.3. Purification of Human Lck(231-501, D364N) in an Unphosphorylated or a Phosphorylated State.

Human Lck(231-501, D364N) [SEQ ID NO. 3] was expressed by recombinant baculovirus infection of Sf9 cells, and purified in a manner similar to unphosphorylated Lck (237-501, D364N) as described above. Unphosphorylated Lck(231-501, D364N) was then phosphorylated, by incubation with ATP and wild-type Lck in a manner similar to that used to prepare phosphorylated Lck(237-501, D364N) as described above, to produce Lck(231-501, D364N) phosphorylated at Tyr-394. The sample was concentrated to ~20 mg/mL using an Ultrafree-15 Biomax 10 K MWCO centrifugal filter device (Millipore). This concentrated sample was used in crystallographic experiments also described below. Sample purity was assessed with SDS-PAGE, native PAGE, and LC/MS total mass analysis (including phosphopeptide mapping), which revealed that the Lck(231-501, D364N) was essentially homogeneously phosphorylated at Tyr-394.

Example 2

Protein Crystallization 2.1. Crystallization of Human Lck(237-501, D364N) in an Unphosphorylated State in the Presence of Inhibitor 1.

Frozen human Lck(237-501, D364N) in an unphosphorylated state, prepared as described above, was thawed on ice. Lck(237-501, D364N) was mixed with a DMSO solution of inhibitor 1. The inhibitor stock solution concentration and amounts used were adjusted so that the final concentration of DMSO was less than 5% and the final concentration of the inhibitor was at least 1 mM. For example, 60 μL of unphosphorylated Lck(237-501, D364N) (20-25 mg/mL) was mixed with 1 μL of a 60 mM stock solution of inhibitor 1. The protein/inhibitor mixture (2 μl) was mixed with 2 μL of a reservoir solution consisting of 3-14% (w/v) poly(ethylene glycol) (PEG) 8000, 100 mM Na-HEPES, pH 6.5-7.2, including optionally 0-8% ethylene glycol, also including optionally 0-0.5% β-octylglucopyranoside, and suspended over the reservoir on the underside of a siliconized glass cover slip at about 4° C. Bipyramidal crystals appeared usually within one week. Crystals were also prepared under related conditions, by varying the concentration of the protein, the identity of the inhibitor, the temperature, the mode of crystallization (for example, sitting rather than hanging drops; or 24-well versus 96-well plates), the identity or amount of the precipitating agent, the identity or amount of the buffer, the pH of the buffer, by adding certain salts or other additives, etc., without making a substantive change to the crystallization conditions outlined above in Example 2.1. Crystals of unphosphorylated human Lck(237-501, D364N) in the presence of inhibitor 2 were also obtained under conditions outlined in Table 1. Additional conditions for obtaining crystals of unphosphorylated human Lck(237-501, D364N) in the presence of various inhibitors are outlined in Table 2.

TABLE 1

Additional Conditions for Producing Crystals of Human Lck(237-501, D364N) in an Unphosphorylated State.

| Inhibitor | Protein Concentration (mg/mL) | Precipitant | Crystal Morphology |
|---|---|---|---|
| 1 | 10 | 10% PEG 20,000, 0.1 M Na-MES pH 6.5 | Brick-like crystals |
| 1 | 10 | 30% PEG monomethyl ether 5000, 0.1 M Na-MES pH 6.5, 0.2 M NH$_4$SO$_4$ | Needle clusters |
| 1 | 10 | 16% PEG 4000, 10% 2-propanol, 0.1 M Na-HEPES pH 7.5, 0.2 M NH$_4$SO$_4$ | Needle clusters |
| 2 | 15 | 20% PEG 4000, 0.1 M Bis-Tris Acetate pH 6.5 | Needles |
| 2 | 15 | 28% PEG 4000, 0.2 M NH$_4$SO$_4$ 0.1 M Na-POPSO pH 8.0 | Needles |
| 2 | 15 | 20-30% MPD, 0.1 M Tris Acetate pH 8.5 | Needles |
| 2 | 15 | 20-30% MPD, 0.1 M AMPD Acetate pH 9.0 | Needles |
| 2 | 15 | 20-30% MPD, 0.1 M Diethanolamine Acetate pH 9.5 | Needles |
| 2 | 4.8 | 0.8 M (NH$_4$)$_2$SO$_4$, Bis-Tris pH 6-7 | Needles |
| 2 | 4.8 | 10-25% PEG 6000, 0.1 M Tris Hydrochloride pH 8.3-8.8, 0.25 M Li$_2$SO$_4$ | Needles |
| 2 | 100 | 40% PEG 400, 0.1 M Bis-Tris Acetate pH 6.5 | Needles |
| 2 | 100 | 28% PEG 4000, 0.1 M Bis-Tris Acetate pH 6.5 | Needles |
| 2 | 91 | 12% MPD, 0.1 M Na-HEPES pH 7.5, 0.1 M tri-Sodium Citrate | Needles |
| Mg-AMP-PNP | 60 | 20% Ethanol, 0.1 M Tris Hydrochloride pH 8.5 | Needles |
| Mg-AMP-PNP | 60 | 20% PEG 3350, 0.2 M Na$_2$HPO$_4$ | Needles |
| 2 | 100 | 1 M MgCl$_2$, 0.05 M Bicine Hydrochloride pH 9.0 | Needles |

*All crystallization experiments were carried out at about 4° C., except for the last entry (20° C.).

agent, the identity or amount of the buffer, the pH of the buffer, by adding certain salts or other additives, etc., without making a substantive change to the crystallization conditions outlined above. Crystals of unphosphorylated human Lck (237-501, D364N) in the presence of inhibitor 1 were also obtained under human conditions outlined in Table 1.

2.2. Crystallization of Human Lck(237-501, D364N) in an Unphosphorylated State in the Presence of Inhibitor 2.

Frozen human Lck(237-501, D364N) in an unphosphorylated state, prepared as described above, as the complex with ~0.025 mM inhibitor 2, was thawed on ice. The unphosphorylated Lck(237-501, D364N).inhibitor 2 complex (2 μl; 91 mg/ml) was mixed with 2 μL of a reservoir solution consisting of 2-12.5% (w/v) poly(ethylene glycol) (PEG) 4000, 100 mM Bis-Tris ride, pH 5.9-7.0, including optionally 0-0.25% β-octylglucopyranoside, and suspended over the reservoir on the underside of a siliconized glass cover slip at about 4° C. Plate-like crystals appeared usually within one week. Crystals were also prepared under related conditions, by varying the concentration of the protein, the identity of the inhibitor, the temperature, the mode of crystallization (for example,

TABLE 2

Altered Crystallization Parameters that Are Considered Equivalent for Producing Crystals of Human Lck(237-501, D364N) in an Unphosphorylated State.

| Crystallization Parameter | Equivalents |
|---|---|
| Protein concentration | 20 mg/mL optimal range 5-100 mg/mL limits 1.0-200 mg/mL |
| Buffer concentration | 100 mM optimal range 50-250 mM limits 5-500 mM |
| pH | 7.2 optimal range 2-12 |
| Buffer Identity | Buffers capable of buffering in a similar pH range expected to give similar results |
| Precipitant | PEG 8000 optimal Range 1.0-1.5 M Limits 0.7-1.8 M |

TABLE 2-continued

Altered Crystallization Parameters that Are Considered Equivalent for Producing Crystals of Human Lck(237-501, D364N) in an Unphosphorylated State.

| Crystallization Parameter | Equivalents |
|---|---|
| Precipitant Identity | Precipitants of a similar molecular structure (such as different PEG molecular weights, PEG monomethyl ethers, etc.) expected to give similar results |
| Additive parameters | 4% ethylene glycol optimal range 0-20% Glycerol, similar molecules, or mixtures in various ratios, should also give similar results |
| Additive identities | Examples which have been successfully added: 0-0.5% β-Octylglucopyranoside Similar mild detergents, or mixtures in various ratios, should also give similar results |
| Drop volumes and ratios | 2 μL protein + 2 μL precipitant solution optimal Total volume range: up to 200 μL, assuming a sitting geometry for larger volumes Volume Ratio range: 1 part protein to 0.25-4.0 parts well solution |
| Precipitant volume (for 4 μL crystallization drop) | Range 500-1000 μL Limits 100-large volume (limited by the distance between the drop and the surface of the well solution allowed by the vessel geometry, see below) |
| Drop - precipitant solution distance | 1 cm optimal Range 0.2-2 cm Limits: 0.1-5 cm |
| Temperature | About 4° C. optimal limits 0-25° C. |
| Ligands | Inhibitor 1 optimal Inhibitors 2-11, 13 analogs Expect similar results from inhibitors that bind under crystallization conditions with $K_d$ values <1 mM |
| Constructs | Variants in amino acid sequence that crystallize in essentially the same space groups or unit cells should be considered equivalent Additional constructs would include deletion of unstructured termini as determined by crystal structure of this construct. For example, deletion of the C-terminal 3 residues (leaving amino acid residues 237- |

TABLE 2-continued

Altered Crystallization Parameters that Are Considered Equivalent for Producing Crystals of Human Lck(237-501, D364N) in an Unphosphorylated State.

| Crystallization Parameter | Equivalents |
|---|---|
| | 498) is likely to yield similar results |
| Post-translational modification | Variants in post-translational modification that crystallize in essentially the same space groups or unit cells should be considered equivalent |
| Other crystallization methods that should give at least equivalent results | Low gravity Temperature oscillations Presence of cryoprotectant (such as the 20% glycerol added before data collection) Variations in crystallization tray geometry Batch-method crystallization (e.g. under oil) Data collection temperature (range: −270 to +100° C.) |

2.3 Crystallization of Human Lck(231-501, D364N) in a Phosphorylated State in the Presence of Inhibitor 10.

Frozen human Lck(231-501, D364N) in a phosphorylated state, prepared as described above, was thawed on ice. Lck (231-501, D364N) was mixed with a DMSO solution of inhibitor 10. The inhibitor stock solution concentration and amounts used were adjusted so that the final concentration of DMSO was less than 5% and the final concentration of the inhibitor was at least 1 mM. For example, 60 μL of phosphorylated Lck(231-501, D364N) (25 mg/mL) was mixed with 1 μL of a 60 mM stock solution of inhibitor 10. The protein/inhibitor mixture (2 μl) was mixed with 2 μL of a reservoir solution consisting of 30% (w/v) poly(ethylene glycol) (PEG) 8000, 100 mM sodium cacodylate, pH 6.5, and 0.2 M $(NH_4)_2SO_4$, and suspended over the reservoir on the underside of a siliconized glass cover slip at about 4° C. Long needle-shaped crystals appeared usually within one week. Crystals were also prepared under related conditions, by varying the concentration of the protein, identity of the inhibitor, the temperature, the mode of crystallization (for example, sitting rather than hanging drops; or 24-well versus 96-well plates), the identity or amount of the precipitating agent, the identity or amount of the buffer, the pH of the buffer, by adding certain salts or other additives, etc., without making a substantive change to the crystallization conditions outlined above. Crystals of human Lck(231-501, D364N) in a phosphorylated state were also obtained under conditions outlined in Table 3.

TABLE 3

Additional Conditions for Producing Crystals of Human Lck(231-501, D364N) in a Phosphorylated State.

| Protein Concentration (mg/mL) | Inhibitor | Precipitant * | Crystal Morphology |
|---|---|---|---|
| 25 | 10 | 0.2 M NH$_4$OAc, 0.1 M NaOAc pH 4.6, 30% PEG 4000 | Needle clusters |
| 25 | 10 | 0.1 M Sodium Citrate pH 5.6, 20% 2-propanol, 20% PEG 4000 | Micro crystals |
| 25 | 10 | 30% PEG 1500 | Micro crystals |
| 25 | 10 | 2 M NaCl, 10% PEG 6000 | Needle clusters |
| 25 | 10 | 10% PEG 1000, 10% PEG 8000 | Needles |
| 25 | 10 | 0.1 M NaOAc pH 4.6, 2 M NaCl | Needle clusters |
| 25 | 10 | 0.01 M FeCl$_3$, 0.1 M Sodium Citrate pH 5.6, 10% Jeffamine M-600 | Needle clusters |

TABLE 3-continued

Additional Conditions for Producing Crystals of Human Lck(231-501, D364N) in a Phosphorylated State.

| Protein Concentration (mg/mL) | Inhibitor | Precipitant * | Crystal Morphology |
|---|---|---|---|
| 25 | 10 | 0.05 M CsCl, 0.1 M Na-MES pH 6.5, 30% Jeffamine M-600 | Needle clusters |
| 25 | 10 | 0.2 M (NH$_4$)SO$_4$ 0.1 M Na-MES pH 6.5, 30% PEG monomethyl ether 5000 | Long fibrous needle clusters |
| 25 | 10 | 0.01 M ZnSO$_4$, 0.1 M Na-MES pH 6.5, 25% PEG monomethyl ether 550 | Needle clusters |
| 25 | 10 | 0.1 M Na-HEPES pH 7.5, 20% Jeffamine M-600 | Needle clusters |
| 25 | 10 | 6-10% PEG 8000, 0.1 M Na-HEPES pH 6.5-7.2, 0-8% ethylene glycol | Needles and frost-like crystals |
| 25 | 10 | 10-14% PEG 8000, 0.1 M Na-HEPES pH 6.5-7.2, 0-8% ethylene glycol | Needles, stacked plates and frost-like crystals |
| 25 | 10 | 1-2 M (NH$_4$)$_2$SO$_4$, 0.1 M Bis-Tris Hydrochloride pH 6.5-7.2 | Needle clusters, multiple crystals |
| 25 | 10 | 5-30% PEG 6000, 0.1 M Tris Hydrochloride pH 8.1-9.3, 0.25 M Li$_2$SO$_4$ | Irregular crystals and needle clusters |
| 25 | 10 | 5-30% PEG 8000, 0.1 M Sodium Cacodylate pH 6-7.4, 0.2 M (NH$_4$)$_2$SO$_4$ | Long, thin needles and needle clusters |
| 25 | 10 | 10-14% PEG 8000, 0.1 M Tris Hydrochloride pH 8.1-9.3, 0.25% β-octylglucopyranoside | Small crystals, stacked plates, irregular plates |
| 17 | 10 | 5-30% PEG 8000, 0.1 M Sodium Cacodylate pH 6-7.4, 0.2 M (NH$_4$)$_2$SO$_4$, 0.25% β-octylglucopyranoside | Needle clusters |
| 17 | 10 | 0.1-2 M NaCl, 0.1 M Na-HEPES pH 6.5-7.2, 12% PEG 8000, 0.25% β-octylglucopyranoside | Tiny single needles, small frost-like crystals |
| 17 | 10 | 0.1-0.25 M (NH$_4$)$_2$SO$_4$, 0.1 M Na-HEPES pH 6.5-7.2, 12% PEG 8000, 0.25% β-octylglucopyranoside | Needle clusters, single needles, frost-like crystals |
| 17 | 10 | 0.1-0.25 M Li$_2$SO$_4$, 0.1 M Na-HEPES pH 6.5-7.2, 12% PEG 8000, 0.25% β-octylglucopyranoside | Needle clusters |
| 17 | 10 | 5-15% PEG 8000, 0.1 M Sodium Cacodylate pH 6-7.4, 0.2 M (NH$_4$)$_2$SO$_4$ | Needle clusters |
| 17 | 11 | 5-15% PEG 8000, 0.1 M Sodium Cacodylate pH 6-7.4, 0.2 M (NH$_4$)$_2$SO$_4$ | Needle clusters and irregular crystals |
| 17 | 11 | 10-14% PEG 8000, 0.1 M Na-HEPES pH 6.5-7.2, 0-8% ethylene glycol, 0.25% β-octylglucopyranoside | Small irregular crystals |

* All crystallization experiments were carried out at about 4° C.

Example 3

Determination of Unphosphorylated Human Lck(237-501, D364N).Inhibitor Complex and Unphosphorylated Human Lck(237-501, D364N) Apoenzyme Crystal Structures 3.1 Cryoprotection and Flash Cooling of an Unphosphorylated Lck(237-501, D364N).Inhibitor 1 Crystal.

A buffer containing 18% (w/v) PEG 8000, 0.1 M Na-HEPES, pH 6.9, and 2 mM inhibitor 1 was prepared, placed in a glass depression well, and cooled to about 4° C. An unphosphorylated Lck(237-501, D364N).inhibitor 1 complex crystal crystallized as described above (Example 2.1) was introduced into this buffer using a fiber loop. After 5 min, the crystal was transferred through a series of cryoprotective buffers containing 18% (w/v) PEG 8000, 0.1 M Na-HEPES, pH 6.9, 2 mM inhibitor 1, and 5, 10, and 20% (v/v) glycerol (5 min each). The crystal was picked up with a fiber loop and flash-cooled by plunging into liquid nitrogen. The crystal was stored in a liquid nitrogen refrigerator until x-ray diffraction data were collected.

3.2 Improvement of an Unphosphorylated Lck(237-501, D364N).Inhibitor 1 Complex Crystal Mosaicity and Diffraction Limit by Annealing.

An unphosphorylated Lck(237-501, D364N).inhibitor 1 complex crystal flashed cooled as above was annealed by thawing in a cryoprotective buffer containing 18% (w/v) PEG 8000, 0.1 M Na-HEPES, pH 6.9, 2 mM inhibitor 1, and 20% (v/v) glycerol at 4° C. After 5 min, the crystal was picked up with a fiber loop and flash-cooled again by plunging into liquid nitrogen. The crystal was stored in a liquid nitrogen refrigerator until x-ray diffraction data were collected. This protocol was also used to anneal similar crystals from which preliminary x-ray diffraction data had already been collected.

3.3. X-ray Diffraction Data Collection from an Unphosphorylated Lck(237-501, D364N).Inhibitor 1 Complex Crystal (Crystal 1).

X-ray diffraction data were collected from crystal 1 on a Siemens SRA rotating anode generator (50 kV, 108 mA, 40% bias, graphite-monochromated Cu K$_\alpha$ radiation) equipped with a MAR Research image plate detector using the rotation method. The Lck crystal was maintained at a temperature of 100 K with an Oxford Cryosystems Cryostream cooler during data collection. For each frame of data (130 total) the crystal was rotated by 0.75°. The data were processed with the CCP4 Suite of programs (Collaborative Computational Project, Number 4, 1994). After determining the crystal orientations with REFIX (Kabsch, 1993) and IDXREF (Collaborative Computational Project, 1994), the data were integrated (in space group P2(1), a=57.61 Å, b=44.64 Å, c=121.58 Å, β=90.17°; unit cell information for all crystals are summarized in Table 4) with MOSFLM (Leslie, 1992), scaled and merged with SCALA (Evans, 1997), and placed on an absolute scale and reduced to structure factor amplitudes with TRUNCATE (French & Wilson, 1978). Five percent of the unique reflections were assigned, in a random fashion, to the "free" set, for calculation of the free R-factor ($R_{free}$) (Brünger, 1992); the remaining 95% of the reflections constituted the "working" set, for calculation of the R-factor (R). These data are summarized in Table 5. Because the unit cell appeared to possess pseudo-orthorhombic symmetry, the data were also integrated and scaled in space group P2(1)2(1)2(1), a=57.61 Å, b=44.72 Å, c=121.64 Å (the unit cell angle β is equal to 90° by definition; the unit cell lengths are slightly different because the unit cell symmetry was constrained to be orthorhombic; see Table 4). These orthorhombic-reprocessed data are summarized in Table 5.

3.4. Molecular Replacement Solution of the Unphosphorylated Lck(237-501, D364N).Inhibitor 1 Complex Crystal Structure (Crystal 1).

A self-rotation function was calculated with the unphosphorylated Lck(237-501, D364N).inhibitor 1 complex crystal (crystal 1) data described above, using the program AMORE (Navaza, 1994), in space group P2(1). As suspected from the pseudo-orthorhombic symmetry, 2-fold rotation axes were detected not only along b (as required by P2(1) crystallographic symmetry), but also along a and c (as required by P2(1)2(1)2(1) crystallographic symmetry). Consideration of the unit cell volume coupled with the molecular weight of Lck(237-501, D364N) (Matthews, 1968) suggested that the P2(1)2(1)2(1) unit cell contained two molecules of Lck(237-501, D364N) in the asymmetric unit, related by a two-fold screw axis along a (or equivalently, along c). For ease of computation, a cross-rotation function was calculated (AMORE) with the Lck(237-501, D364N).inhibitor 1 complex crystal data in the orthorhombic space group P2(1)2(1)2(1) rather than in the monoclinic space group P2(1). The search model was the crystal structure of activated Lck reported previously (Protein Data Bank entry 3Lck; (Yamaguchi & Hendrickson, 1996)). The cross-rotation function had one obvious solution, at Eulerian angles [142.64, 17.69, 262.48], which was 17.1 standard deviations above the mean level of the cross-rotation function; the next highest peak was 6.0 standard deviations above the mean. The translation function was calculated (AMORE) in space groups P222, P222$_1$, P22$_1$2, P2(1)22, P2(1)2$_1$2, P2(1)22$_1$, P22$_1$2$_1$, and P2(1)2(1)2(1). One solution was again obvious, in space group P2(1)2(1)2 (1), at a fractional translation of [0.2314, 0.2623, 0.3684], with an R-factor of 45.6% and a correlation coefficient of 39.0% (15-3.25 Å resolution). The orientation parameters of this solution were improved slightly by rigid-body fitting (AMORE) to provide an R-factor of 45.4% and a correlation coefficient of 38.6% (15-3.25 Å resolution). Finally, this solution was transformed back into the monoclinic P2(1) unit cell by orienting the Lck molecule according to the above fitting parameters, generating the non-crystallographic symmetry copies of the molecule (coordinate transformations x, y, z and ½-x, -y, ½+z), and lastly by shifting the origin (which is defined differently in P2(1) and P2(1)2(1)2(1)) by applying another coordinate transformation (x, y, z-¼) to both molecules.

3.5. Refinement of the Unphosphorylated Lck(237-501, D364N).Inhibitor 1 Complex Crystal Structure (Crystal 1).

The refinement of the unphosphorylated Lck(237-501, D364N).Inhibitor 1 complex crystal structure (crystal 1) began with the transformed coordinates, described above, in space group P2(1). Refinement began, using the program X-PLOR (Brünger et al., 1987), with rigid-body refinement, which resulted in an R of 44.0% ($R_{free}$ 46.8%) for all reflections with |F|>2.0σ$_F$ between 15 and 3.0 Å resolution. The coordinate transformation relating the two Lck molecules in the asymmetric unit, A and B, were defined by a least-squares superimposition of A onto B using the molecular graphics program O (Jones et al., 1991). Further refinement with X-PLOR (bulk solvent correction, overall temperature factor refinement [first cycle only], Powell minimization, and individual temperature factor refinement, all the while including progressively higher resolution data) alternated with manual rebuilding of the structural coordinates (the "model") using the molecular graphics program O. Throughout this process, and all subsequent refinement, the non-crystallographic symmetry was constrained according to the coordinate transformation defined above. Six such alternating cycles resulted in an R of 26.8% ($R_{free}$ 29.2%) for all reflections with |F|>0.0σ$_F$ between 15 and 2.0 Å resolution. Slowcool simulated annealing molecular dynamics refinement (Brünger et al., 1987) (X-PLOR; 3000K to 300K) followed by two more cycles of Powell minimization and rebuilding resulting in an R of 25.4% ($R_{free}$ 28.5%) for all reflections with |F|>0.0σ$_F$ between 15 and 2.0 Å resolution. Examination of SigmaA-weighted $2F_o$-$F_c$ and $F_o$-$F_c$ electron-density maps (Read, 1986) clearly revealed the presence of inhibitor 1 in the Lck active site. Coordinates for the inhibitor were added to the model, and a final round of refinement resulted in an R of 25.4% ($R_{free}$ 28.5%) for all reflections with |F|>0.0σ$_F$ between 15 and 2.0 Å resolution. The quality of the model was assessed with the PROCHECK (Laskowski et al., 1993), WHATIF (Vriend, 1990), and WHATCHECK (Hooft et al., 1996) computer programs. This model (molecule A) included Lck residues 238-397 and 403-498, 102 water molecules, and inhibitor 1. Molecule B was generated from molecule A by the coordinate transformation defined above. Residue 237, residues 398-402, and residues 499-501 were not located in the electron-density maps and were not included in the structural coordinates. These data are summarized in Table 6. The three-dimensional coordinates of the model are shown in FIG. 4.

3.6. Soaking of an Unphosphorylated Lck(237-501, D364N) .Inhibitor 1 Complex Crystal with Inhibitor 2.

A buffer containing 18% (w/v) PEG 8000, 0.1 M Na-HEPES, pH 6.9, and 2 mM inhibitor 2 was prepared, placed in a glass depression well, and cooled to about 4° C. An unphosphorylated Lck(237-501, D364N).inhibitor 1 complex crystal was introduced into this buffer using a fiber loop. After 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 6.9, 2 mM inhibitor 2, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.7. X-ray Diffraction Data Collection from an Unphosphorylated Lck(237-501, D364N).Inhibitor 2 Complex Crystal (Crystal 2).

A total of 200 X-ray diffraction data frames (0.5° each) were collected from crystal 2 essentially as described above for crystal 1. The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.8. Refinement of the Unphosphorylated Lck(237-501, D364N).Inhibitor 2 Complex Crystal Structure (Crystal 2).

The refined structural coordinates for crystal 1 were further refined against the diffraction data collected from the unphosphorylated Lck(237-501, D364N).inhibitor 2 complex crystal (crystal 2) using X-PLOR. First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 22.6% ($R_{free}$ 25.1%) for all reflections with $|F|>0.0\sigma_F$ between 15 and 2.50 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 5.

3.9. Soaking of an Unphosphorylated Lck(237-501, D364N) .Inhibitor 1 Complex Crystal with Inhibitor 3.

A buffer containing 18% (w/v) PEG 8000, 0.1 M Na-HEPES, pH 6.9, and 2 mM inhibitor 3 was prepared, placed in a glass depression well, and cooled to 4° C. An unphosphorylated Lck(237-501, D364N).inhibitor 1 complex crystal was introduced into this buffer using a fiber loop. After 5 min, the crystal was transferred to a depression well containing fresh buffer. The well was sealed and the crystal was allowed to soak for 18 h at 4° C. Next, the crystal was transferred through a series of cryoprotective buffers containing 18% (w/v) PEG 8000, 0.1 M Na-HEPES, pH 6.9, 2 mM inhibitor 3, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.10. X-ray Diffraction Data Collection from an Unphosphorylated Lck(237-501, D364N).Inhibitor 3 Complex Crystal (Crystal 3).

A total of 124 X-ray diffraction data frames (0.6° each) were collected from crystal 3 essentially as described above for crystal 1. The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.11. Refinement of the Unphosphorylated Lck(237-501, D364N).Inhibitor 3 Complex Crystal Structure (Crystal 3).

The refined structural coordinates for crystal 1 were further refined against the diffraction data collected from the unphosphorylated Lck(237-501, D364N).inhibitor 3 complex crystal (crystal 3) using X-PLOR. First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 22.1% ($R_{free}$ 25.1%) for all reflections with $|F|>0.0\sigma_F$ between 15 and 2.35 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 6.

3.12. Soaking of an Unphosphorylated Lck(237-501, D364N).Inhibitor 1 Complex Crystal with Inhibitor 4.

A buffer containing 18% (w/v) PEG 8000, 0.1 M Na-HEPES, pH 6.9, and 2 mM inhibitor 4 was prepared, placed in a glass depression well, and cooled to 4° C. An unphosphorylated Lck(237-501, D364N).inhibitor 1 complex crystal was introduced into this buffer using a fiber loop. After 5 min, the crystal was transferred to a depression well containing fresh buffer. The well was sealed and the crystal was allowed to soak for 18 h at 4° C. Next, the crystal was transferred through a series of cryoprotective buffers containing 18% (w/v) PEG 8000, 0.1 M Na-HEPES, pH 6.9, 2 mM inhibitor 4, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.13. X-ray Diffraction Data Collection from an Unphosphorylated Lck(237-501, D364N).Inhibitor 4 Complex Crystal (Crystal 4).

A total of 240 X-ray diffraction data frames (0.5° each) were collected from crystal 4 essentially as described above for crystal 1 (Osmic multilayer optics-monochromated and -focused Cu $k_\alpha$ radiation). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.14. Refinement of the Unphosphorylated Lck(237-501, D364N).Inhibitor 4 Complex Crystal Structure (Crystal 4).

The refined structural coordinates for crystal 1 were further refined against the diffraction data collected from the unphosphorylated Lck(237-501, D364N).inhibitor 4 complex crystal (crystal 4) using X-PLOR. First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 24.5% ($R_{free}$ 27.3%) for all reflections with $|F|>0.0\sigma_F$ between 15 and 2.10 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 7.

3.15. Soaking of an Unphosphorylated Lck(237-501, D364N).Inhibitor 1 Complex Crystal with Inhibitor 5.

A buffer containing 18% (w/v) PEG 8000, 0.1 M Na-HEPES, pH 6.9, and 2 mM inhibitor 5 was prepared, placed in a glass depression well, and cooled to 4° C. An unphosphorylated Lck(237-501, D364N).inhibitor 1 complex crystal was introduced into this buffer using a fiber loop. After 5 min, the crystal was transferred to a depression well containing fresh buffer. The well was sealed and the crystal was allowed to soak for 18 h at 4° C. Next, the crystal was transferred through a series of cryoprotective buffers containing 18% (w/v) PEG 8000, 0.1 M Na-HEPES, pH 6.9, 2 mM inhibitor 5, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.16. X-ray Diffraction Data Collection from an Unphosphorylated Lck(237-501, D364N).Inhibitor 5 Complex Crystal (Crystal 5).

A total of 110 X-ray diffraction data frames (1.0° each) were collected from crystal 5 essentially as described above for crystal 1 (Osmic multilayer optics-monochromated and -focused Cu $k_\alpha$ radiation). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.17. Refinement of the Unphosphorylated Lck(237-501, D364N).Inhibitor 5 Complex Crystal Structure (Crystal 5).

The refined structural coordinates for crystal 1 were further refined against the diffraction data collected from the unphosphorylated Lck(237-501, D364N).inhibitor 5 complex crystal (crystal 5) using X-PLOR. First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 22.4% ($R_{free}$ 24.8%) for all reflections with $|F|>0.0\sigma_F$ between 15 and 2.35 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 8.

3.18. Soaking of an Unphosphorylated Lck(237-501, D364N).Inhibitor 1 Complex Crystal with Inhibitor 6.

A buffer containing 18% (w/v) PEG 8000, 0.1 M Na-HEPES, pH 6.9, and 2 mM inhibitor 6 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 6.9, 2 mM inhibitor 6, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.19. X-ray Diffraction Data Collection from an Unphosphorylated Lck(237-501, D364N).Inhibitor 6 Complex Crystal (Crystal 6).

A total of 240 X-ray diffraction data frames (0.5° each) were collected from crystal 6 essentially as described above for crystal 1 (Osmic multilayer optics-monochromated and -focused Cu $K_\alpha$ radiation). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.20. Refinement of the Unphosphorylated Lck(237-501, D364N).Inhibitor 6 Complex Crystal Structure (Crystal 6).

The refined structural coordinates for crystal 1 were further refined against the diffraction data collected from the unphosphorylated Lck(237-501, D364N).inhibitor 6 complex crystal (crystal 6) using X-PLOR. First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 24.4% ($R_{free}$ 27.2%) for all reflections with $|F|>0.0\sigma_F$ between 15 and 2.10 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 9.

3.21. Soaking of an Unphosphorylated Lck(237-501, D364N).Inhibitor 1 Complex Crystal with Inhibitor 7.

A buffer containing 18% (w/v) PEG 8000, 0.1 M Na-HEPES, pH 6.9, and 2 mM inhibitor 7 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 6.9, 2 mM inhibitor 7, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.22. X-ray Diffraction Data Collection from an Unphosphorylated Lck(237-501, D364N).Inhibitor 7 Complex Crystal (Crystal 7).

A total of 196 X-ray diffraction data frames (0.5° each) were collected from crystal 7 essentially as described above for crystal 1 (Osmic multilayer optics-monochromated and -focused Cu $K_\alpha$ radiation). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.23. Refinement of the Unphosphorylated Lck(237-501, D364N).Inhibitor 7 Complex Crystal Structure (Crystal 7).

The refined structural coordinates for crystal 1 were further refined against the diffraction data collected from the unphosphorylated Lck(237-501, D364N).inhibitor 7 complex crystal (crystal 7) using X-PLOR. First, the coordinates for inhibitor 1 were removed from the coordinates. Refinement alternated with manual rebuilding of the structural coordinates (the "model") using the molecular graphics program o. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 24.1% ($R_{free}$ 26.7%) for all reflections with $|F|>0.0\sigma_F$ between 15 and 2.15 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 10.

3.24. Soaking of an Unphosphorylated Lck(237-501, D364N).Inhibitor 1 Complex Crystal with Inhibitor 8.

A buffer containing 18% (w/v) PEG 8000, 0.1 M Na-HEPES, pH 6.9, and 2 mM inhibitor 8 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 5 days at about 4° C. Next, the crystal was transferred through a series of cryoprotective buffers containing 18% (w/v) PEG 8000, 0.1 M Na-HEPES, pH 6.9, 2 mM inhibitor 8, and 5, 10, and 20% (v/v) glycerol (about 5 min each). The crystal was picked up with a fiber loop and flash-cooled by plunging into liquid nitrogen. The crystal was stored in a liquid nitrogen refrigerator until diffraction data were collected.

3.25. X-ray Diffraction Data Collection from an Unphosphorylated Lck(237-501, D364N).Inhibitor 8 Complex Crystal (Crystal 8).

A total of 180 X-ray diffraction data frames (0.5° each) were collected from crystal 8 essentially as described above for crystal 1 (Rigaku RU-200 rotating anode generator, 50 kV, 100 mA, 40% bias, mirror-focused Cu $K_\alpha$ radiation, MAR Research image plate detector). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.26. Refinement of the Unphosphorylated Lck(237-501, D364N).Inhibitor 8 Complex Crystal Structure (Crystal 8).

The refined structural coordinates for crystal 1 were further refined against the diffraction data collected from the unphosphorylated Lck(237-501, D364N).inhibitor 8 complex crystal (crystal 8) using X-PLOR. First, the coordinates for inhibitor 1 were removed from the coordinates. Refinement alternated with manual rebuilding of the structural coordinates (the "model") using the molecular graphics program o. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 26.3% ($R_{free}$ 28.6%) for all reflections with $|F|>0.0\sigma_F$ between 30 and 2.10 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 11.

3.27. Soaking of an Unphosphorylated Lck(237-501, D364N).Inhibitor 1 Complex Crystal with Inhibitor 9.

A buffer containing 18% (w/v) PEG 8000, 0.1 M Na-HEPES, pH 6.9, and 2 mM inhibitor 9 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 6.9, 2 mM inhibitor 9, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.28. X-ray Diffraction Data Collection from an Unphosphorylated Lck(237-501, D364N).Inhibitor 9 Complex Crystal (Crystal 9).

A total of 240 X-ray diffraction data frames (0.5° each) were collected from crystal 9 essentially as described above for crystal 1 (National Synchrotron Light Source, beamline X26C, x-ray wavelength 1.1 Å, ADSC Quantum 4 CCD detector). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.29. Refinement of the Unphosphorylated Lck(237-501, D364N).Inhibitor 9 Complex Crystal Structure (Crystal 9).

The refined structural coordinates for crystal 1 were further refined against the diffraction data collected from the unphosphorylated Lck(237-501, D364N).inhibitor 9 complex crystal (crystal 9) using X-PLOR. First, the coordinates for inhibitor 1 were removed from the coordinates. Refinement alternated with manual rebuilding of the structural coordinates (the "model") using the molecular graphics program o. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 27.4% ($R_{free}$ 30.0%) for all reflections with $|F|>0.0\sigma_F$ between 20 and 2.25 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 12.

3.30. Preparation of an Unphosphorylated Lck(237-501, D364N) Apoenzyme Crystal.

A buffer containing 18% (w/v) PEG 8000 and 0.1 M Na-HEPES, pH 6.9 was prepared, placed in a glass depression well, and cooled to about 4° C. An unphosphorylated Lck (237-501, D364N).inhibitor 1 complex crystal was introduced into this buffer using a fiber loop. After 5 min, the crystal was transferred to a depression well containing fresh buffer. The well was sealed and the crystal was allowed to soak for about 5 days at about 4° C. Next, the crystal was transferred through a series of cryoprotective buffers containing 18% (w/v) PEG 8000, 0.1 M Na-HEPES, pH 6.9, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

3.31. X-ray Diffraction Data Collection from an Unphosphorylated Lck(237-501, D364N) Apoenzyme Crystal (Crystal 10).

A total of 55 X-ray diffraction data frames (0.8° each) were collected from crystal 10 essentially as described above for crystal 1 (Rigaku RU-200 rotating anode generator, 50 kV, 100 mA, 40% bias, mirror-focused Cu $K_\alpha$ radiation, Rigaku RAXIS-IV image plate detector). The crystal was maintained at a temperature of 100 K during data collection. The data were processed in space group P2(1), as described for crystal 1. The unique reflections were assigned to the same "free" and "working" sets as used for crystal 1. The unit cell information is summarized in Table 4, and the data processing statistics are summarized in Table 5.

3.32. Refinement of the Unphosphorylated Lck(237-501, D364N) Apoenzyme Structure (Crystal 10).

The refined structural coordinates for crystal 1 were further refined against the diffraction data collected from the unphosphorylated Lck(237-501, D364N) apoenzyme crystal (crystal 10) using X-PLOR. First, the coordinates for inhibitor 1 were removed from the coordinates. Refinement alternated with manual rebuilding of the structural coordinates (the "model") using the molecular graphics program o. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 23.1% ($R_{free}$ 27.1%) for all reflections with $|F|>0.0\sigma_F$ between 30 and 2.70 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 13.

3.33. Cryoprotection and Flash Cooling of an Unphosphorylated Lck(237-501, D364N).Inhibitor 2 Crystal.

A buffer containing 15% (w/v) PEG 4000, 0.1 M Bis-Tris hydrochloride, pH 7.0, and 1 mM inhibitor 2 was prepared, placed in a glass depression well, and cooled to 4° C. An unphosphorylated Lck(237-501, D364N).inhibitor 2 complex crystal crystallized as described above (Example 2.2) was introduced into this buffer using a fiber loop. After 5 min, the crystal was transferred through a series of cryoprotective buffers containing 15% (w/v) PEG 4000, 0.1 M Bis-Tris hydrochloride, pH 7.0, 1 mM inhibitor 2, and 5, 10, and 20% (v/v) glycerol (5 min each). The crystal was picked up with a fiber loop and flash-cooled by plunging into liquid nitrogen. The crystal was stored in a liquid nitrogen refrigerator until x-ray diffraction data were collected.

3.34. X-ray Diffraction Characterization of an Unphosphorylated Lck(237-501, D364N).Inhibitor 2 Complex Crystal (Crystal 11).

An X-ray diffraction data frame (1.0°) were collected from crystal 11 essentially as described above for crystal 1 (Stanford Synchrotron Radiation Laboratory, beamline 7-1, x-ray wavelength 1.08 Å, MAR Research image plate detector). The crystal was maintained at a temperature of 100 K during data collection. The data were indexed with MOSFLM (Leslie, 1992) in space group P2(1), a=89 Å, b=133 Å, c=131 Å, β=109°. The unit cell information is summarized in Table 4.

TABLE 4

Summary of Crystallographic Unit Cell Information for Unphosphorylated Lck(237-501, D364N) Crystals.

| Crystal | Inhibitor | Space Group | a (Å) | b (Å) | c (Å) | β (°) |
|---|---|---|---|---|---|---|
| 1 | 1 | P2(1) | 57.6114 | 44.6415 | 121.5802 | 90.1744 |
| 1 | 1 | P2(1)2(1)2(1) | 57.6127 | 44.7239 | 121.6432 | 90 |
| 2 | 2 | P2(1) | 57.1351 | 44.4372 | 119.8807 | 90.0611 |
| 3 | 3 | P2(1) | 57.2509 | 44.3348 | 120.7773 | 90.0123 |
| 4 | 4 | P2(1) | 57.7547 | 44.3607 | 126.1668 | 90.0054 |
| 5 | 5 | P2(1) | 57.6434 | 44.6093 | 120.0287 | 90.0726 |
| 6 | 6 | P2(1) | 56.8231 | 44.4862 | 120.1543 | 90.0022 |
| 7 | 7 | P2(1) | 57.3756 | 44.6799 | 119.8213 | 90.0183 |
| 8 | 8 | P2(1) | 57.1386 | 44.3706 | 120.7324 | 89.9859 |
| 9 | 9 | P2(1) | 57.0985 | 44.2486 | 118.3230 | 89.9493 |
| 10 | — | P2(1) | 57.6021 | 44.4520 | 119.7686 | 89.8907 |
| 11 | 2 | P2(1) | 89 | 133 | 131 | 109 |
| 12 | 12 | P2(1) | 57.884 | 44.625 | 121.969 | 89.875 |
| 13 | 13 | P2(1)2(1)2(1) | 57.19 | 44.48 | 120.05 | 90 |

TABLE 5

Summary of X-ray Diffraction Data Collection Statistics for Unphosphorylated Lck(237-501, D364N) Crystals.

| Crystal | Inhibitor | Space Group | Resolution (Å) | Unique Reflections | $R_{sym}$ (%)* | $<I/\sigma_1>$ * | Coverage (%)* | Multiplicity * |
|---|---|---|---|---|---|---|---|---|
| 1 | 1 | P2(1) | 15.0-2.00 (2.07-2.00) | 39,046 | 0.074 (0.469) | 6.4 (1.3) | 92.7 (87.6) | 1.9 (1.8) |
| 1 | 1 | P2(1)2(1)2(1) | 15.0-2.00 (2.07-2.00) | 21,716 | 0.090 (0.552) | 7.3 (1.5) | 99.0 (98.3) | 3.3 (3.0) |
| 2 | 2 | P2(1) | 15.0-2.50 (2.61-2.50) | 20,555 | 0.117 (0.511) | 6.1 (1.7) | 97.3 (97.2) | 2.1 (2.1) |
| 3 | 3 | P2(1) | 15.0-2.35 (2.45-2.35) | 20,880 | 0.097 (0.484) | 5.7 (1.3) | 81.4 (61.5) | 1.6 (1.4) |
| 4 | 4 | P2(1) | 15.0-2.10 (2.15-2.10) | 37,198 | 0.060 (0.458) | 8.9 (2.0) | 98.7 (99.6) | 2.3 (2.3) |
| 5 | 5 | P2(1) | 15.0-2.35 (2.43-2.35) | 25,322 | 0.066 (0.418) | 8.6 (2.1) | 98.1 (97.9) | 2.2 (2.1) |
| 6 | 6 | P2(1) | 15.0-2.10 (2.07-2.10) | 40,136 | 0.056 (0.442) | 8.8 (2.2) | 98.0 (96.5) | 2.4 (2.4) |
| 7 | 7 | P2(1) | 15.0-2.15 (2.23-2.15) | 28,733 | 0.069 (0.374) | 8.3 (1.6) | 86.0 (49.6) | 1.9 (1.2) |
| 8 | 8 | P2(1) | 30.0-2.10 (2.17-2.10) | 32,298 | 0.092 (0.387) | 6.3 (2.2) | 91.0 (63.5) | 1.6 (1.2) |
| 9 | 9 | P2(1) | 20.0-2.25 (2.33-2.25) | 28,209 | 0.065 (0.508) | 5.9 (1.5) | 99.2 (99.8) | 2.3 (2.4) |
| 10 | — | P2(1) | 30.0-2.70 (2.79-2.70) | 11,226 | 0.092 (0.420) | 6.5 (1.4) | 67.6 (71.0) | 1.3 (1.3) |
| 12 | 12 | P2(1) | 50-2.00 (2.07-2.00) | 36,699 | 5.4 (33.7) | 25.2 (1.91) | 86.4 (92.9) | 2.3 (2.1) |
| 13 | 13 | P2(1)2(1)2(1) | 50-2.20 (2.29-2.20) | 15,290 | 4.6 (34.5) | 30.0 (3.6) | 95.5 (85.0) | 3.4 (2.8) |

*Highest resolution shell in parentheses.

TABLE 6

Summary of Crystallographic Refinement Statistics for Unphosphorylated Lck(237-501, D364N) Crystal Structures.

| Crystal | Inhibitor | Resolution (Å) | $R_{free}$ (%) | R (%) |
|---|---|---|---|---|
| 1 | 1 | 15.0-2.00 | 28.5 | 25.4 |
| 2 | 2 | 15.0-2.50 | 25.1 | 22.6 |
| 3 | 3 | 15.0-2.35 | 25.1 | 22.1 |
| 4 | 4 | 15.0-2.10 | 27.3 | 24.5 |
| 5 | 5 | 15.0-2.35 | 24.8 | 22.4 |
| 6 | 6 | 15.0-2.10 | 27.2 | 24.4 |
| 7 | 7 | 15.0-2.15 | 26.7 | 24.1 |
| 8 | 8 | 30.0-2.10 | 28.6 | 26.3 |
| 9 | 9 | 20.0-2.25 | 30.0 | 27.4 |
| 10 | — | 30.0-2.70 | 27.1 | 23.1 |
| 12 | 12 | 50-2.00 | 33.0 | 30.0 |
| 13 | 13 | 50-2.20 | 26.7 | 23.7 |

References:

Brünger, A. T. (1992). "The free R value: a novel statistical quantity for assessing the accuracy of crystal structures." *Nature* 355: 472-474.

Brünger, A. T., Adams. P. D., Clore, G. M., Gros, P., Grosse-Kunstleve, R. W., Jiang, J.-S., Kuszwski, J., Nilges, N., Pannu, N. S., Read, R. J., Rice, L. M., Simonson, T. & Warren, G. L. (1998). "Crystollography & NMR system (CNS): A new software system for macrocmolecular structure determination." *Acta Crystallogr.* D54: 905-921.

Brünger, A. T., Kuriyan, J. & Karplus, M. (1987). "Crystallographic R factor refinement by molecular dynamics." *Science* 235: 1049-1053.

Chan, J. H., Hong J. S. Hunter, R. N., 3rd, Orr, G. F., Cowan, J. R., Sherman, D. B., Sparks, S. M., Reitter, B. E., Andrews, C. W., 3rd, Hazen, R. J., St Clair, M., Boone, L. R., Ferris, R. G., Creech, K. L., Roberts, G. B., Short, S. A., Weaver, K., Ott, R. J., Ren, J., Hopkins, A., Stuart, D. I. & Stammers, D. K. (2001). "Inhibitor binding to active and inactive cdk2. the crystal structure of cdk2-cyclin a/indirubin-5-sulphonate." *J Med Chem* 9: 389-397.

Collaborative Computational Project, N. (1994). "The CCP4 suite: programs for protein crystallography." *Acta Crystallogr.* D50: 760-763.

Dajani, R., Fraser, E., Roe, S. M., Young, N., Good, V., Dale, T. C. & Pearl, L. H. (2001). "Crystal structure of glycogen synthase kinase 3 beta. structural basis for phosphate-primed substrate specificity and autoinhibition." *Cell* 105: 721-732.

Evans, P. R. (1997). "SCALA." *Joint CCP4 and ESF-EACBM Newsletter* 33: 22-24.

French, S. & Wilson, K. (1978). "Truncate." *Acta Crystallogr.* A34: 517-525.

Gosser, Y. Q., Zheng, J., Overduin, M., Mayer, B. J. & Cowburn, D. (1995). "The solution structure of Abl SH3, and its relationship to SH2 in the SH(32) construct." *J Mol Biol* 3: 1075-1086.

Hooft, R. W. W., Vriend, G., Sander, C. & Abola, E. E. (1996). "Errors in protein structures." *Nature* 381: 272.

Hubbard, S. R., Wei, L., Ellis, L. & Hendrickson, W. A. (1994). "Crystal structure of the tyrosine kinase domain of the human insulin receptor." *Science* 372: 746-754.

Jones, T. A., Zou, J. Y., Cowan, S. W. & Kjelgaard, M. (1991). "Improved methods for building protein models in electron density maps and the location of errors in these models." *Acta Crystallogr.* A47: 110-119.

Kabsch, W. (1993). "Automatic processing of rotation diffraction data from crystals of initially unknown symmetry and cell constants." *J. Appl. Crystallogr.* 26: 795-800.

Knighton, D. R., Zheng, J. H., Ten Eyck, L. F., Ashford, V. A., Xuong, N. H., Taylor, S. S. & Sowadski, J. M. (1991). "Crystal structure of the catalytic subunit of cyclic adenosine monophosphate-dependent protein kinase." *Science* 253: 407-414.

Laskowski, R. A., MacArthur, M. W., Moss, D. S. & Thornton, J. M. (1993). "PROCHECK: a program to check the stereochemical quality of protein structures." *J. Appl. Crystallogr.* 26: 283-291.

Lei, M., Lu, W., Meng, W., Parrini, M. C., Eck, M. J., Mayer, B. J. & Harrison, S. C. (2000). "Structure of PAK1 in an autoinhibited conformation reveals a multistage activation switch." *Biochemistry* 102: 387-397.

Leslie, A. G. W. (1992). MOSFLM. CCP4 and ESF-EACMB Newsletter on Protein Crystallography, Daresbury Laboratory, Warrington, U.K.

Matthews, B. W. (1968). "Solvent content of protein crystals." *J. Mol Biol.* 33: 491-497.

McTigue, M. A., Wickersham, J. A., Pinko, C., Showalter, R. E., Parast, C. V., Tempczyk-Russell, A., Gehring, M. R., Mroczkowski, B., Kan, C. C., Villafranca, J. E. & Appelt, K. (1999). "Crystal structure of the kinase domain of human vascular endothelial growth factor receptor 2: a key enzyme in angiogenesis." *FEMS Microbiol Rev* 7: 319-330.

Mohammadi, M., Schlessinger, J. & Hubbard, S. R. (1996). "Structure of the FGF receptor tyrosine kinase domain reveals a novel autoinhibitory mechanism." *Cell* 86: 577-587.

Narula, S. S., Yuan, R. W., Adams, S. E., Green, O. M., Green, J., Philips, T. B., Zydowsky, L. D., Botfield, M. C., Hatada, M., Laird, E. R. & et al. (1995). "Solution structure of the C-terminal SH2 domain of the human tyrosine kinase Syk complexed with a phosphotyrosine pentapeptide." *Structure* 3: 1061-1073.

Navaza, J. (1994). "AMoRe: an automated package for molecular replacement." *Acta Crystallogr.* A50: 157-163.

Noble, M. E., Musacchio, A., Saraste, M., Courtneidge, S. A. & Wierenga, R. K. (1993). "Crystal structure of the SH3 domain in human Fyn; comparison of the three-dimensional structures of SH3 domains in tyrosine kinases and spectrin." *Drug Metab Dispos* 12: 2617-2624.

Otwinowski, Z. & Minor, W. (1997). "Processing of x-ray diffraction data collected in oscillation mode." *Meth. Enzymol.* 276: 307-326.

Read, R. J. (1986). "Improved Fourier coefficients for maps using phases from partial structures with errors." *Acta Crystallogr.* A42: 140-149.

Russo, A. A., Jeffrey, P. D., Patten, A. K., Massague, J. & Pavletich, N. P. (1996). "Crystal structure of the p27Kip1 cyclin-dependent-kinase inhibitor bound to the cyclin A-Cdk2 complex." *Biochem Biophys Res Commun* 382: 325-331.

Schindler, T., Bornmann, W., Pellicena, P., Miller, W. T., Clarkson, B. & Kuriyan, J. (2000). "Structural mechanism for STI-571 inhibition of abelson tyrosine kinase." *J Mol Biol* 289: 1938-1942.

Schindler, T., Sicheri, F., Pico, A., Gazit, A., Levitzki, A. & Kuriyan, J. (1999). "Crystal structure of Hck in complex with a Src family-selective tyrosine kinase inhibitor." *Mol Cell* 3: 639-648.

Schulze-Gahmen, U., De Bondt, H. L. & Kim, S. H. (1996). "High-resolution crystal structures of human cyclin-dependent kinase 2 with and without ATP: bound waters and natural ligand as guides for inhibitor design." *Structure* 39: 4540-4546.

Shewchuk, L. M., Hassell, A. M., Ellis, B., Holmes, W. D., Davis, R., Horne, E. L., Kadwell, S. H., McKee, D. D. & Moore, J. T. (2000). "Structure of the Tie2 RTK domain: self-inhibition by the nucleotide binding loop, activation loop, and C-terminal tail." *J Cell Sci* 8: 1105-1113.

Sicheri, F., Moarefi, I. & Kuriyan, J. (1997). "Crystal structure of the Src family tyrosine kinase Hck." *Nature* 385: 602-609.

Su, Y., Dostmann, W. R., Herberg, F. W., Durick, K., Xuong, N. H., Ten Eyck, L., Taylor, S. S. & Varughese, K. I. (1995). "Regulatory subunit of protein kinase A: structure of deletion mutant with cAMP binding domains." *Eur J Biochem* 269: 807-813.

Superti-Furga, G. (1995). "Regulation of the Src protein tyrosine kinase." *FEBS Lett* 369: 62-66.

Vriend, G. (1990). "WHATIF: a molecular modelling and drug design program." *J. Mol. Graphics* 8: 52-56.

Waksman, G., Kominos, D., Robertson, S. C., Pant, N., Baltimore, D., Birge, R. B., Cowburn, D., Hanafusa, H., Mayer, B. J., Overduin, M. & et al. (1992). "Crystal structure of the phosphotyrosine recognition domain SH2 of v-src complexed with tyrosine-phosphorylated peptides." *Science* 358: 646-653.

Williams, J. C., Weijland, A., Gonfloni, S., Thompson, A., Courtneidge, S. A., Superti-Furga, G. & Wierenga, R. K. (1997). "The 2.35 Å crystal structure of the inactivated form of chicken Src: a dynamic molecule with multiple regulatory interactions." *Biochemistry* 274: 757-775.

Xu, W., Doshi, A., Lei, M., Eck, M. J. & Harrison, S. C. (1999). "Crystal structures of c-Src reveal features of its autoinhibitory mechanism." *Mol Cell* 3: 629-638.

Xu, W., Harrison, S. C. & Eck, M. J. (1997). "Three-dimensional structure of the tyrosine kinase c-Src." *Nature* 385: 595-602.

Yamaguchi, H. & Hendrickson, W. A. (1996). "Structural basis for activation of human lymphocyte kinase Lck upon tyrosine phosphorylation." *J Med Chem* 384: 484-489.

Zhu, X., Kim, J. L., Newcomb, J. R., Rose, P. E., Stover, D. R., Toledo, L. M., Zhao, H. & Morgenstern, K. A. (1999). "Structural analysis of the lymphocyte-specific kinase Lck in complex with non-selective and Src family selective kinase inhibitors." *Structure Fold Des* 7: 651-661.

Example 4

Preparation of Inhibitor 7, trans-N2-(4-{4-Amino-1-[4-(4-methylpiperazino)cyclohexyl]-1H-pyrazolo[3,4-d]pyrimidin-3-yl}-2-methoxyphenyl)-1H-2-indolecarboxamide (tris-maleate salt)

4.1. Synthesis of trans-tert-Butyl N-(4-{4-amino-1-[4-(4-methylpiperazino)cyclohexyl]-1H-pyrazol[3,4-d]pyrimidin-3-yl}-2-methoxyphenyl)carbamate.

trans-3-Iodo-1-[4-(4-methylpiperazino)cyclohexyl]-1H-pyrazolo[3,4-d]pyrimidin-4-amine (4.0 g, 9.06 mmol), tert-butyl N-[2-methoxy-4-(4,4,5,5-tetramethyl-1,3,2-dioxaborolan-2-yl)phenyl]carbamate (3.48 g, 9.97 mmol), palladium tetrakistriphenyphosphine (0.63 g, 0.64 mmol) and sodium carbonate (2.30 g, 21.75 mmol) were mixed with ethylene glycol dimethyl ether (100 mL) and water (50 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-tert-butyl N-(4-{4-amino-1-[4-(4-methylpiperazino)cyclohexyl]-1H-pyrazolo[3,4-d]pyrimidin-3-yl}-2-methoxyphenyl)carbamate (4.75 g, 98%). $^1$H NMR (DMSO-d$_6$) δ 1.48 (m, 11H), 2.02 (m, 6H), 2.15 (s, 3H), 2.35 (m, 5H), 2.53 (m, 4H), 3.87 (s, 3H), 4.64 (m, 1H), 7.20 (m, 2H), 7.90 (d, J=8.15, 1H), 8.03 (s, 1H), 8.22 (s, 1H).

4.2. Synthesis of trans-3-(4-Amino-3-methoxyphenyl)-1-[4-(4-methylpiperazino)cyclohexyl]-1H-pyrazolo[3,4-d]pyrimidin4-amine.

A mixture of trifluoroacetic acid/dichloromethane (20:80, 150 mL) was added to a solution of N-(4-{4-amino-1-[4-(4-methylpiperazino)cyclohexyl]-1H-pyrazolo[3,4-d]pyrimidin-3-yl}-2-methoxyphenyl)carbamate (4.75 g, 8.85 mmol) in dichloromethane (100 mL) at about 0° C. About 2 hours later, the ice-bath was removed and the solvents were evaporated and the residue was dissolved in dichloromethane. Sodium hydroxide (1.0N) was added to adjust the pH to about 10. The solid formed upon removal of organic solvent was collect by filtration to give trans-3-(4-amino-3-methoxyphenyl)-1-[4-(4-methylpiperazino)cyclohexyl]-1H-pyrazolo[3,4-d]pyrimidin-4-amine (3.85 g, 100%). $^1$H NMR (DMSO-d$_6$) δ 1.44(m, 2H), 1.96 (m, 6H), 2.21 (s, 3H), 2.33 (m, 5H), 2.53 (m, 4H), 3.83 (s, 3H), 4.60 (m, 1H), 5.03 (bs, 2H), 6.76 (d, J=7.91 Hz, 1H), 6.98 (d, J=7.89 Hz), 7.03 (m, 2H), 8.19 (s, 1H).

4.3. Synthesis of trans-N2-(4-{4-Amino-1-[4-(4-methylpiperazino)cyclohexyl]-1H-pyra-zolo[3,4-d]pyrimidin-3-yl}-2-methoxyphenyl)-1H-2-indolecarboxamide.

To 1H-2-indolecarboxylic acid (0.738 g, 4.58 mmol) in dichloromethane (14 mL) was added oxalyl chloride (4 mL, 45.8 mmol) and DMF (1 drop). The reaction mixture was stirred overnight. Solvent was evaporated and the residue was dissolved in dichloromethane (5 mL). Half of the dichloromethane solution (2.5 mL) was added to a solution of trans-3-(4-amino-3-methoxyphenyl)-1-[4-(4-methylpiperazino)cyclohexyl]-1H-pyrazolo[3,4-d]pyrimidin-4-amine (0.50 g, 1.145 mmol) in pyridine (6 mL) at 0° C. After 30 minutes, the solid as collected by filtration. Water was then added to the solid and the pH of the solution was adjusted to 10 with sodium hydroxide (1.0N). The aqueous was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-N2-(4-{4-amino-1-[4-(4-methylpiperazino)cyclohexyl]-1H-pyrazolo[3,4-d]pyrimidin-3-yl}-2-methoxyphenyl)-1H-2-indolecarboxamide (0.312 g, 47%). $^1$H NMR (DMSO-d$_6$) δ 1.49 (m, 2H), 2.05 (m, 6H), 2.15 (s, 3H), 2.32 (m, 5H), 2.51 (m, 4H), 3.97 (s, 3H), 4.66 (m, 1H), 7.10 (m, 1H), 7.22 (m 1H), 7.30 (d, J=7.98 Hz), 8.11 (d, J=8.14 Hz, 1H), 8.24 (s, 1H), 9.44 (s, 1H).

4.4. Synthesis of Inhibitor 7, trans-N2-(4-{4-Amino-1-[4-(4-methylpiperazino)cyclohexyl]-1H-pyrazolo[3,4-d]pyrimidin-3-yl}-2-methoxyphenyl)-1H-2-indolecarboxamide (tris-maleate salt).

trans-N2-(4-{4-Amino-1-[4-(4-methylpiperazino)cyclohexyl]-1H-pyrazolo[3,4-d]pyrimidin-3-yl}-2-methoxyphenyl)-1H-2-indolecarboxamide (312 mg, 0.539 mmol) was dissolved in hot ethyl acetate (35 mL) and maleic acid (187 mg, 1.614 mmol) in hot ethyl acetate (5 mL) was added. The reaction mixture was stirred at room temperature for 5 hours. The solid was collected by filtration to give inhibitor 7, trans-N2-(4-{4-Amino-1-[4-(4-methylpiperazino)cyclohexyl]-1H-pyrazolo[3,4-d]pyrimidin-3-yl}-2-methoxyphenyl)-1H-2-indolecarboxamide, tris-maleate salt (473 mg, 95%). $^1$H NMR (DMSO-d$_6$) δ 1.60 (m, 2H), 2.09 (m, 6H), 2.68 (s, 3H), 2.84-3.19 (bm, 9H), 3.97 (s, 3H), 4.73 (m, 1H), 6.17 (s, 6H), 7.11 (m, 1H), 7.25 (m, 1H), 7.30 (m, 1H), 7.34 (s, 1H), 7.41 (s, 1H), 7.49 (d, J=8.21, 1H), 7.68 (d, J=8.02 Hz, 1H), 8.13 (d, J=8.15 Hz, 1H), 8.26 (s, 1H), 9.44 (s, 1H), 11.38 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonium acetate buffer, pH 4.5), 3.0 mL/min.): MH$^+$=580.4, R$_t$=2.01 min.

Example 5

Structure-Based Design, Synthesis and Lck Inhibition Testing of a Human Lck Inhibitor, Inhibitor 15, trans-3-[4-(1H-3-Indazolylamino)phenyl]-1-[4-(4-methylpiperazino)cyclohexyl]-1H-pyrazolo[3,4-d]pyrimidin-4-amine (acetate salt)

5.1. Structure-Based Design of Inhibitor 15, trans-3-[4-(1H-3-Indazolylamino)phenyl]-1-[4-(4-methylpiperazino) cyclohexyl]-1H-pyrazolo[3,4-d]pyrimidin-4-amine (acetate salt).

Molecular fragment 14 was constructed as a SMILES string (chemical structure drawing computer program ISIS Draw), and three-dimensional coordinates were then calculated by using the molecular modeling program CORINA.

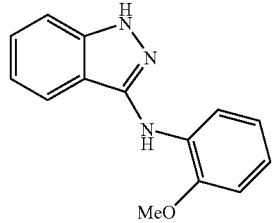

14

The coordinates of fragment 14 were transferred into the molecular modeling program INSIGHT II, into which the three-dimensional atomic coordinates (FIG. 10) of the unphosphorylated Lck(237-501, D364N).inhibitor 7 complex structure had been loaded. Using the tools of INSIGHT II, the phenyl ring of fragment 14 was superimposed on the phenyl ring of inhibitor 7 in an orientation such that the indazolyl moiety of fragment 14 occupied the space of the indolamide in the Lck crystal structure. The position of fragment 14 was adjusted so that the overlap of N2 of the indazolyl moiety with the amide carbonyl oxygen atom of inhibitor 7 was maximized, and so that unfavorable van der Waals contacts between the amino acid residues of Lck and fragment 14 were minimized. Visual examination of the modeled complex indicated that favorable interactions between the protein and proposed inhibitor could be realized by an inhibitor in a conformation involving minimal strain.

The molecular modeling demonstrated that the aminoindazolyl moiety could serve as a replacement for the indolylamide moiety.

Using these results the compound trans-3-[4-(1H-3-indazolylamino)phenyl]-1-[4-(4-methylpiperazino)cyclohexyl]-1H-pyrazolo[3,4-d]pyrimidin-4-amine, inhibitor 15 was designed by attaching an aminoindazolyl moiety to the core inhibitor structure. The compound was synthesized as an acetate salt as described below.

5.2. Synthesis of N1-(4-bromophenyl)-2-fluoro-1-benzenecarbohydrazonamide.

N1-(4-bromophenyl)-2-fluoro-1-benzenecarbothioamide (1.50 g, 0.00485 mol) and a 1 M solution of hydrazine in tetrahydrofuran (6.3 mL, 0.0063 mol) were heated in absolute ethanol (25 mL) at reflux under nitrogen atmosphere for 14 hours. Additional 3 mL of a 1M solution of hydrazine in tetrahydrofuran was added and the stirring at reflux was continued for another 6 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated to yield N1-(4-bromophenyl)-2-fluoro-1-benzenecarbohydrazonamide (1.54 g, 0.0050 mol) as a tan solid. TLC (ethyl acetate/heptane 1:3) $R_f$ 0.10.

5.3. Synthesis of N-(4-bromophenyl)-N-(1H3-indazolyl) amine.

To a solution of N1-(4-bromophenyl)-2-fluoro-1-benzenecarbohydrazonamide (1.2 g, 0.00391 mol) in N-methyl pyrrolidinone (25 mL), potassium tert-butoxide (0.50 g, 0.0041 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was purified by flash chromatography on silica using ethyl acetate/n-heptane (1:5) as mobile phase to yield N-(4-bromophenyl)-N-(1H-3-indazolyl)amine (0.29 g, 0.0010 mol) as a white solid. $^1$H NMR (DMSO-$d_6$, 400 MHz), δ 12.06 (s, 1H), 9.03 (s, 1H), 7.93 (d, 1H), 7.65 (d, 2H), 7.35 (m, 4H), 7.03 (dd, 1H). TLC (ethyl acetate/heptane 1:3) $R_f$ 0.26.

5.4. Synthesis of N-(1H-3-indazolyl)-N-[4-(4,4,5,5-tetramethyl-1,3,2-dioxaborolan-2-yl)phenyl]amine.

A mixture of N-(4-bromophenyl)-N-(1H-3-indazolyl) amine (0.29 g, 0.00101 mol), diboron pinacol ester (0.31 g, 0.00121 mol), [1.1′-bis(diphenylphosphino)ferrocene]-dichloropalladium (II) complex with dichloromethane (1:1) (0.025 g, 0.00003 mol) and potassium acetate (0.294 g, 0.003 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:3) as mobile phase to yield N-(1H-3-indazolyl)-N-[4-(4,4,5,5-tetramethyl-1,3,2-dioxaborolan-2-yl)phenyl]amine (0.064 g, 0.000191 mol) as an off-white solid. $^1$H NMR (DMSO-$d_6$, 400 MHz) δ 12.09 (s, 1H), 9.06 (s, 1H), 7.94 (d, 1H), 7.64 (d, 2H), 7.57 (d, 2H), 7.35 (m, 2H), 7.03 (dd, 1H), 1.28 (s, 12H). TLC (ethyl acetate/heptane 1:3) $R_f$ 0.21.

5.5. Synthesis of Inhibitor 15, trans-3-[4-(1H-3-Indazolylamino)phenyl]-1-[4-(4-methylpiperazino)cyclohexyl]-1H-pyrazolo[3,4-d]pyrimidin4-amine (acetate salt).

A mixture of N-(1H-3-indazolyl)-N-[4-(4,4,5,5-tetramethyl-1,3,2-dioxaborolan-2-yl)phenyl]amine (0.064 g, 0.000191 mol), trans-3-iodo-1-[4-(4-methylpiperazino)-cyclohexyl]-1H-pyrazolo[3,4-d]pyrimidin-4-amine (0.070 g, 0.000159 mol), tetrakis-(triphenylphosphine)palladium (0.011 g, 0.0000095 mol) and sodium carbonate (0.042 g, 0.000398 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 µm, 25 cm; 10-60% acetonitrile-0.1M ammonium acetate over 25 min, 21 mL/min) to yield trans-3-[4-(1H-3-indazolylamino)phenyl]-1-[4-(4-methylpiperazino)cyclohexyl]-1H-pyrazolo[3,4-d]pyrimidin-4-amine acetate (0.035 g, 0.000060 mol) as a white solid. $^1$H NMR (DMSO-$d_6$, 400 MHz) δ 12.09 (s, 1H), 9.14 (s, 1H), 8.21 (s, 1H), 7.99 (d, 1H), 7.83 (d, 2H), 7.55 (d, 2H), 7.37 (m, 2H), 7.06 (t, 1H), 4.64 (m, 1H), 2.6-2.2 (br, 9H), 2.13 (s, 3H), 2.05 (m, 6H), 1.91 (s, 3H), 1.49 (m, 2H); RP-HPCL (Delta Pak C18, 5 µm, 300 A, 15 cm; 5%-85% acetonitrile–0.1M ammonium acetate over 20 min, 1 mL/min) $R_t$ 12.96 min. MS: MH$^+$ 523.

5.6. Lck Inhibition Assay of Inhibitor 15, trans-3-[4-(1H3-Indazolylamino)phenyl]-1-[4-(4-methylpiperazino) cyclohexyl]-1H-pyrazolo[3,4-d]pyrimidin4-amine.

The inhibitor 15 was tested in an Lck inhibition assay (described in Example 6:) and was found to be a potent inhibitor of Lck.

Example 6

In Vitro Potency Test of Lck Inhibitors 6.1. Enzyme Linked Immunosorbent Assay (ELISA) for Protein Tyrosine Kinases.

The in vitro potency of compounds in inhibiting Lck may be determined by the procedures detailed below. The potency of compounds can be determined by the amount of inhibition of the phosphorylation of an exogenous substrate (e.g., synthetic peptide (Z. Songyang et al., *Nature.* 373:536-539) by a test compound relative to control. Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology, 2d ed.*, edited by Rose and Friedman, pp 359-371 Am. Soc. of Microbiology, Washington, D.C. The disclosed protocol was adapted for determining activity with respect to a specific protein tyrosine kinase, e.g. Lck. For example, preferred protocols for conducting the ELISA experiments are provided below. Adaptation of these protocols for determining the activity of a compound against other protein tyrosine kinases, for example Hck, are well within the abilities of those skilled in the art. For purposes of determining inhibitor selectivity, a universal protein tyrosine kinase substrate (e.g. a random copolymer of poly(Glu$_4$Tyr), 20,000-50,000 MW) was employed together with ATP (typically 5 µM) at concentrations approximately twice the apparent Km in the assay. The following procedure was used to assay the inhibitory effect of compounds of this invention on Lck protein tyrosine kinase activity:

Buffers and Solutions:

PGT [poly(Glu$_4$Tyr)]: Store powder at −20° C. Dissolve powder in phosphate buffered saline (PBS) for 50 mg/ml solution. Store 1 ml aliquots at −20° C. When making plates dilute to 250 μg/ml in Gibco PBS. Reaction Buffer: 100 mM Hepes, 20 mM MgCl$_2$, 4 mM MnCl$_2$, 5 mM DTT, 0.02% BSA, 200 μM NaVO$_4$, pH 7.1. ATP: Store aliquots of 100 mM at −20° C. Dilute to 20 μM in water. Washing Buffer: PBS with 0.1% Tween 20. Antibody Diluting Buffer: 0.1% bovine serum albumin (BSA) in PBS. TMB Substrate: Mix TMB substrate and Peroxide solutions 9:1 just before use or use K-Blue Substrate from Neogen. Stop Solution: 1 M Phosphoric acid.

Procedure:

1. Plate Preparation:

Dilute PGT stock (50 mg/ml, frozen) in PBS to 250 μg/ml. Add 125 μl per well of Corning modified flat bottom high affinity ELISA plates (Corning #25805-96). Add 125 μl PBS to blank wells. Cover with sealing tape and incubate overnight at 37° C. Wash 1× with 250 μl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water. Prepare reaction buffer. Prepare enzyme solution so that desired units are in 50 μl, e.g. for Lck make to 1 ng/μl for a total of 50 ng per well in the reactions. Store on ice. Make 4×ATP solution to 20 μM from 100 mM stock in water. Store on ice. Add 50 μl of the enzyme solution per well (typically 5-50 ng enzyme/well depending on the specific activity of the kinase). Add 25 μl 4×inhibitor. Add 25 μl 4×ATP for inhibitor assay. Incubate for 10 min at room temperature. Stop reaction by adding 50 μl 0.05N HCl per well. Wash plate. Final Concentrations for Reaction: 5 μM ATP, 5% DMSO.

3. Antibody Binding:

Dilute 1 mg/ml aliquot of PY20-HRP (Pierce) antibody (an anti-phosphotyrosine antibody) to 50 ng/ml in 0.1% BSA in PBS by a 2 step dilution (100×, then 200×). Add 100 μl Ab per well. Incubate 1 hr at room temperature. Incubate 1 hr at 4° C. Wash 4×plate.

4. Color reaction:

Prepare TMB substrate and add 100 μl per well. Monitor OD at 650 nm until 0.6 is reached. Stop with 1 M phosphoric acid. Shake on plate reader. Read OD immediately at 450 nm. Optimal incubation times and enzyme reaction conditions vary slightly with enzyme preparations and are determined empirically for each lot.

Example 7

Purification and Crystallization of the Catalytic Domain of Human Lck 7.1. Purification of the Catalytic Domain of Human Lck.

The catalytic domain of human Lck (amino acid residues from about 235 to about 501 of SEQ ID NO. 1, optionally containing non-conservative mutations), which optionally contains an amino-terminal or carboxy-terminal affinity purification tag (e.g. (His)$_n$, glutathione-S-transferase, etc.) that is optionally separated from the Lck catalytic domain by a cleavage site (e.g. TEV protease, thrombin, etc.) is expressed by recombinant baculovirus infection of Sf9 cells. The recombinant protein is purified at a convenient temperature (e.g. 4° C.). Cells from an Sf9 culture are thawed and resuspended in an appropriate lysis buffer (e.g. 20 mM Tris, pH 8.0, 50 mM NaCl, 10% (v/v) glycerol, 1% Triton X-100, and protease inhibitors). After an incubation period, the cell lysate is centrifuged. An appropriate purification column is prepared (e.g. Hi-Trap chelating Sepharose, Pharmacia-Amersham). The cell lysate supernatant is applied to the purification column; proteins are eluted using appropriate buffers (e.g. 50 mM HEPES, pH 7.5, 10% (v/v) glycerol, 300 mM NaCl containing varying amounts of imidazole). Additional purification steps are used to provide the Lck (fusion) protein in appropriate purity (e.g. >90%). The optional affinity purification tag is removed by proteolysis or other cleavage method (e.g. TEV protease). Additional purification steps are used to provide the catalytic domain of human Lck in appropriate purity (e.g. >95%) (e.g. MonoQ (Pharmacia-Amersham) anion exchange chromatography). Fractions containing the catalytic domain of human Lck are pooled, optionally additives (e.g. DTT, an inhibitor, etc.) are added to the protein sample, and the sample is concentrated to an appropriate concentration for crystallization (e.g. 20 mg/mL). The sample may optionally be stored prior to crystallization (e.g. frozen at −80° C.).

7.2. Crystallization of the Catalytic Domain of Human Lck.

The catalytic domain of human Lck (which optionally contains non-conservative mutations), prepared as described above, is optionally mixed with additives (such as ligands or inhibitors). The protein sample is crystallized by mixing with a precipitating agent (e.g. 2-12.5% (w/v) poly(ethylene glycol) (PEG) 4000, 100 mM Bis-Tris hydrochloride, pH 5.9-7.0). Crystallization is performed by incubating this mixture in any of a variety of methods (e.g. suspending over a reservoir of a precipitating agent or other solution on the underside of a siliconized glass cover slip) at an appropriate temperature (e.g. 4° C.). Crystals are also prepared under related conditions, by varying the concentration of the protein, the identity of the optional ligands or inhibitors, the temperature, the mode of crystallization (for example, sitting rather than hanging drops; or 24-well versus 96-well plates), the identity or amount of the precipitating agent, the identity or amount of the buffer, the pH of the buffer, by adding certain salts or other additives, etc.

Example 8

Determination of Additional Unphosphorylated Human Lck(237-501, D364N).Inhibitor Complex Crystal Structures 8.1. Soaking of an Unphosphorylated Lck(237-501, D364N) .Inhibitor 1 Complex Crystal with Inhibitor 12.

A buffer containing 18% (w/v) PEG 8000, 0.1 M Na-HEPES, pH 7.0, and 1 mM inhibitor 12 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 7.0, 1 mM inhibitor 12, and 5, 10, and 20% (v/v) glycerol (5 min each). The crystal was picked up with a fiber loop and flash-cooled by plunging into liquid nitrogen. The crystal was stored in a liquid nitrogen refrigerator until diffraction data were collected.

8.2. X-ray Diffraction Data Collection from an Unphosphorylated Lck(237-501, D364N).Inhibitor 12 Complex Crystal (Crystal 12).

A total of 230 X-ray diffraction data frames (0.5° each) were collected from crystal 12 essentially as described above for crystal 1 (Nonius FR-591 rotating anode generator, 50 kV, 100 mA, mirror-focused Cu $k_\alpha$ radiation, MAR 345 image plate detector). The crystal was maintained at a temperature of 100 K during data collection. The data were processed in space group P2(1) using the HKL2000 suite of computer programs (Otwinowski & Minor, 1997). The scaled and merged data output by SCALEPACK (Otwinowski & Minor, 1997) were placed on an absolute scale and reduced to structure factor amplitudes with TRUNCATE (French & Wilson, 1978). The unique reflections were assigned to the same "free" and "working" sets as used for crystal 1. The unit cell information is summarized in Table 4, and the data processing statistics are summarized in Table 5.

8.3. Refinement of the Unphosphorylated Lck(237-501, D364N).Inhibitor 12 Complex Crystal Structure (Crystal 12).

The refined structural coordinates for crystal 1 were further refined against the diffraction data collected from the unphosphorylated Lck(237-501, D364N).inhibitor 12 complex crystal (crystal 12) using CNX (Commercial version of CNS; (Brünger et al., 1998)). First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. As described for crystal 1, the non-crystallographic symmetry was constrained according to a coordinate transformation defined after rigid body refinement. This procedure resulted in an R of 30.0% ($R_{free}$ 33.0%) for all reflections with |F|>0.0$\sigma_F$ between 50 and 2.0 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 14.

8.4. Soaking of an Unphosphorylated Lck(237-501, D364N) .Inhibitor 1 Complex Crystal with Inhibitor 13.

A buffer containing 18% (w/v) PEG 8000, 0.1 M Na-HEPES, pH 7.0, and 1 mM inhibitor 13 was prepared, placed in a glass depression well, and cooled to about 4° C. An unphosphorylated Lck(237-501, D364N).inhibitor 1 complex crystal was introduced into this buffer using a fiber loop. After about 5 min, the crystal was transferred to a depression well containing fresh buffer. The well was sealed and the crystal was allowed to soak for about 18 h at about 4° C. Next, the crystal was transferred through a series of cryoprotective buffers containing 18% (w/v) PEG 8000, 0.1 M Na-HEPES, pH 7.0, 1 mM inhibitor 13, and 5, 10, and 20% (v/v) glycerol (5 min each). The crystal was picked up with a fiber loop and flash-cooled placing it directly in the cryogenic gaseous nitrogen stream on the x-ray generator. X-ray diffraction data were then collected.

8.5. X-ray Diffraction Data Collection from an Unphosphorylated Lck(237-501, D364N).Inhibitor 13 Complex Crystal (Crystal 13).

A total of 125 X-ray diffraction data frames (1.0° each) were collected from crystal 13 essentially as described above for crystal 1 (Nonius FR-591 rotating anode generator, 50 kV, 100 mA, mirror-focused Cu $K_\alpha$ radiation, MAR 345 image plate detector). The crystal was maintained at a temperature of 100 K during data collection. The data were processed as described for crystal 12, but in space group P2(1)2(1)2(1) instead of space group P2(1), as described for crystal 1. Five percent of the unique reflections were assigned, in a random fashion, to the "free" set, for calculation of the free R-factor ($R_{free}$) (Brünger, 1992); the remaining 95% of the reflections constituted the "working" set, for calculation of the R-factor (R). The unit cell information is summarized in Table 4, and the data processing statistics are summarized in Table 5.

8.6. Refinement of the Unphosphorylated Lck(237-501, D364N).Inhibitor 13 Complex Crystal Structure (Crystal 13).

The refined structural coordinates for crystal 1 were further refined against the diffraction data collected from the unphosphorylated Lck(237-501, D364N).inhibitor 13 complex crystal (crystal 13) using CNX (Brünger et al., 1998). First, the coordinates for inhibitor 1 were removed from the coordinates. Refinement alternated with manual rebuilding of the structural coordinates (the "model") using the molecular graphics program O. Rigid-body and overall temperature factor refinement were followed by bulk solvent correction, Powell minimization, and individual temperature factor refinement. This procedure resulted in an R of 23.7% ($R_{free}$ 26.7%) for all reflections with |F|>0.0$\sigma_F$ between 50 and 2.20 Å resolution. The quality of the model was assessed with the PROCHECK (Laskowski et al., 1993), WHATIF (Vriend, 1990), and WHATCHECK (Hooft et al., 1996) computer programs. These data are summarized in Table 6. The three-dimensional coordinates of the model are shown in FIG. 15.

Example 9

Synthesis and Inhibition Testing of Human Lck Inhibitors Which Are Selective for Lck over Hck 9.1. Synthesis of Inhibitor 12, 2-(2,6-dichloroanilino)-7-[(E)-3-(diethylamino)-1-propenyl]-1,6-dimethyl-8,9-dihydro-1H-imidazo[4,5-h]isoquinolin-9-one.

Inhibitor 12 was synthesized as reported by Snow et al. (2001).

9.2. Lck Inhibition Assay of Inhibitor 12, 2-(2,6-dichloroanilino)-7-[(E)-3-(diethylamino)-1-propenyl]-1,6-dimethyl-8,9-dihydro-1H-imidazo[4,5-h]isoquinolin-9-one.

The inhibitor 12 was tested in an Lck inhibition assay (described in Example 6:) and was found to be a potent inhibitor of Lck. It was also found to inhibit Lck selectively over Hck.

9.3. Synthesis of Inhibitor 13, 2-(2,6-dichloroanilino)-1,6-dimethyl-7-((E)-3-{methyl[3(meth-ylamino)propyl] amino}-1-propenyl)-8,9-dihydro-1H-imidazo[4,5-h]isoquinolin-9-one.

A solution of tris(dibenzylidineacetone)dipalladium (0) (0.016 g, 0.01697 mmol) in tetrahydrofuran under nitrogen atmosphere was treated with triphenylphosphine (0.007 g, 0.0255 mmol). The reaction mixture was stirred for about 20 minutes under a nitrogen atmosphere. A solution of 1-[2-(2, 6-dichloroanilino)-1,6-dimethyl-9-oxo-8,9-dihydro-1H-imidazo[4,5-h]isoquinolin-7-yl]allyl acetate (Snow et al., 2001) (0.080 g, 0.1697 mmol) in tetrahydrofuran was added to the palladium solution. Triethylamine (0.052 g, 0.509 mmol) and N,N'-dimethyl-1,3-propanediamine (0.087 g, 0.8485 mmol) were added to the reaction solution. The reaction mixture was stirred at room temperature for 15 hours under a nitrogen atmosphere. Tetrahydrofuran was removed from the reaction mixture under reduced pressure. Acetic acid (0.5 mL) and dimethylformamide (5 mL) were added. The reaction mixture was filtered through a Gelman filter disk and was then purified by preparative HPLC chromatography. The preparative column afforded 0.012 g (14%) of pure 13, 2-(2,6-dichloroanilino)-1,6-dimethyl-7-((E)-3-{methyl[3-(methylamino)propyl]amino}-1-propenyl)-8,9-dihydro-1H-imidazo[4,5-h]isoquinolin-9-one. $^1$H NMR (CDCl$_3$, 400 MHz) δ 7.8572-7.8355 (d, 1H J=8.68 Hz), 7.5408-7.5189 (d, 1H, J=8.76 Hz), 7.399-7.366 (m, 2H), 7.118-7.078 (t, 1H) 6.786-6.746 (m, 1H), 6.312-6.256 (m, 1H), 4.288 (s, 3H), 3.213-3.199 (m, 2H), 2.696-2.663 (t, 2H), 2.518-2.483 (t, 2H), 2.443 (s, 3H), 2.377 (s, 3H), 2.24 (s, 3H), 1.740-1.689 (m, 2H)); LCMS (Thermoquest AQA single-quad MS, Genesis C18 column, 3 μm particle size, 33×4.6 mm; 70% 50 mM ammonium acetate in water to 95% CH$_3$CN over 6 min, 0.8 to 0.5 mL/min) R$_t$ 2.05 min (100%), M$^+$ 513.5 and 515.5.

9.4. Lck Inhibition Assay of Inhibitor 13, 2-(2,6-dichloroanilino)-1,6-dimethyl-7-((E)-3-{methyl[3-(methylamino)propyl]amino}-1-propenyl)-8,9-dihydro-1H-imidazo[4,5-h]isoquinolin-9-one.

The inhibitor 13 was tested in an Lck inhibition assay (described in Example 6:) and was found to be a potent inhibitor of Lck. It was also found to inhibit Lck selectively over Hck.

References:

Snow, R. J., Cardozo, M. G., Goldberg, D., Hammach, A., Morwick, T., Moss, N., Patel, U. R., Prokopowicz, A. S., III, Takahashi, H., Tschantz, M. A., Wang, X. "Heterocyclic compounds useful as inhibitors of tyrosine kineases." PCT Int. Appl. (2001), WO 01/25238 A2 (Apr. 12, 2001).

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a compound which is a potential inhibitor of a human Lck (lymphocyte cell kinase) protein, said method comprising the step of designing a compound that will interact with one or more subsites selected from the group consisting of Subsite 1, Subsite 2, Subsite 3, Subsite 5, Subsite 6, Subsite 7, Subsite 8, Subsite 9 and Subsite 10 of SEQ ID NO. 2 in the catalytic domain of the Lck protein, based upon the crystal structure atomic coordinates of a polypeptide SEQ ID NO. 2 that contains the non-conservative Asp-364-Asn mutation and displaying said compound.

2. The method of claim 1 wherein the crystal structure atomic coordinates are set forth in FIG. 4, FIG. 5, FIG. 6, FIG. 7, FIG. 8, FIG. 9, FIG. 10, FIG. 11, or FIG. 12.

3. The method of claim 1 wherein the compound interacts with one or more of the subsites selected from the group consisting of Subsite 1, Subsite 2, Subsite 3, Subsite 5, Subsite 6, Subsite 7, Subsite 8, Subsite 9 and Subsite 10 of SEQ. ID NO. 2.

* * * * *

SEQUENCE LISTING

```
<160> NUMBER OF SEQ ID NOS: 3

<210> SEQ ID NO 1
<211> LENGTH: 509
<212> TYPE: PRT
<213> ORGANISM: Homo sapiens
<220> FEATURE:
<221> NAME/KEY: DOMAIN
<222> LOCATION: (2)...(15)
<223> OTHER INFORMATION: SH4 domain
<220> FEATURE:
<221> NAME/KEY: DOMAIN
<222> LOCATION: (20)...(60)
<223> OTHER INFORMATION: "unique" domain
<220> FEATURE:
<221> NAME/KEY: DOMAIN
<222> LOCATION: (65)...(120)
<223> OTHER INFORMATION: SH3 domain
<220> FEATURE:
<221> NAME/KEY: DOMAIN
<222> LOCATION: (5)...(220)
<223> OTHER INFORMATION: SH2 domain
<220> FEATURE:
<221> NAME/KEY: DOMAIN
<222> LOCATION: (235)...(501)
<223> OTHER INFORMATION: SH1 domain
<220> FEATURE:
<221> NAME/KEY: DOMAIN
<222> LOCATION: (503)...(509)
<223> OTHER INFORMATION: poly(A) tail

<400> SEQUENCE: 1

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80
```

-continued

```
Gly Phe Glu Lys Gly Glu Gln Leu Arg Ile Leu Glu Gln Ser Gly Glu
                 85                  90                  95
Trp Trp Lys Ala Gln Ser Leu Thr Thr Gly Gln Glu Gly Phe Ile Pro
            100                 105                 110
Phe Asn Phe Val Ala Lys Ala Asn Ser Leu Glu Pro Glu Pro Trp Phe
        115                 120                 125
Phe Lys Asn Leu Ser Arg Lys Asp Ala Glu Arg Gln Leu Leu Ala Pro
    130                 135                 140
Gly Asn Thr His Gly Ser Phe Leu Ile Arg Glu Ser Glu Ser Thr Ala
145                 150                 155                 160
Gly Ser Phe Ser Leu Ser Val Arg Asp Phe Asp Gln Asn Gln Gly Glu
                165                 170                 175
Val Val Lys His Tyr Lys Ile Arg Asn Leu Asp Asn Gly Gly Phe Tyr
            180                 185                 190
Ile Ser Pro Arg Ile Thr Phe Pro Gly Leu His Glu Leu Val Arg His
        195                 200                 205
Tyr Thr Asn Ala Ser Asp Gly Leu Cys Thr Arg Leu Ser Arg Pro Cys
    210                 215                 220
Gln Thr Gln Lys Pro Gln Lys Pro Trp Trp Glu Asp Glu Trp Glu Val
225                 230                 235                 240
Pro Arg Glu Thr Leu Lys Leu Val Glu Arg Leu Gly Ala Gly Gln Phe
                245                 250                 255
Gly Glu Val Trp Met Gly Tyr Tyr Asn Gly His Thr Lys Val Ala Val
            260                 265                 270
Lys Ser Leu Lys Gln Gly Ser Met Ser Pro Asp Ala Phe Leu Ala Glu
        275                 280                 285
Ala Asn Leu Met Lys Gln Leu Gln His Gln Arg Leu Val Arg Leu Tyr
    290                 295                 300
Ala Val Val Thr Gln Glu Pro Ile Tyr Ile Ile Thr Glu Tyr Met Glu
305                 310                 315                 320
Asn Gly Ser Leu Val Asp Phe Leu Lys Thr Pro Ser Gly Ile Lys Leu
                325                 330                 335
Thr Ile Asn Lys Leu Leu Asp Met Ala Ala Gln Ile Ala Glu Gly Met
            340                 345                 350
Ala Phe Ile Glu Glu Arg Asn Tyr Ile His Arg Asp Leu Arg Ala Ala
        355                 360                 365
Asn Ile Leu Val Ser Asp Thr Leu Ser Cys Lys Ile Ala Asp Phe Gly
    370                 375                 380
Leu Ala Arg Leu Ile Glu Asp Asn Glu Tyr Thr Ala Arg Glu Gly Ala
385                 390                 395                 400
Lys Phe Pro Ile Lys Trp Thr Ala Pro Glu Ala Ile Asn Tyr Gly Thr
                405                 410                 415
Phe Thr Ile Lys Ser Asp Val Trp Ser Phe Gly Ile Leu Leu Thr Glu
            420                 425                 430
Ile Val Thr His Gly Arg Ile Pro Tyr Pro Gly Met Thr Asn Pro Glu
        435                 440                 445
Val Ile Gln Asn Leu Glu Arg Gly Tyr Arg Met Val Arg Pro Asp Asn
    450                 455                 460
Cys Pro Glu Glu Leu Tyr Gln Leu Met Arg Leu Cys Trp Lys Glu Arg
465                 470                 475                 480
Pro Glu Asp Arg Pro Thr Phe Asp Tyr Leu Arg Ser Val Leu Glu Asp
                485                 490                 495
```

```
Phe Phe Thr Ala Thr Glu Gly Gln Tyr Gln Pro Gln Pro
            500                 505

<210> SEQ ID NO 2
<211> LENGTH: 265
<212> TYPE: PRT
<213> ORGANISM: Homo sapiens
<220> FEATURE:
<221> NAME/KEY: MUTAGEN
<222> LOCATION: (364)
<223> OTHER INFORMATION: non-conservative D364N mutation
<220> FEATURE:
<221> NAME/KEY: PHOSPHORYLATION
<222> LOCATION: (394)

<400> SEQUENCE: 2

Glu Trp Glu Val Pro Arg Glu Thr Leu Lys Leu Val Glu Arg Leu Gly
 1               5                  10                  15

Ala Gly Gln Phe Gly Glu Val Trp Met Gly Tyr Tyr Asn Gly His Thr
             20                  25                  30

Lys Val Ala Val Lys Ser Leu Lys Gln Gly Ser Met Ser Pro Asp Ala
         35                  40                  45

Phe Leu Ala Glu Ala Asn Leu Met Lys Gln Leu Gln His Gln Arg Leu
 50                  55                  60

Val Arg Leu Tyr Ala Val Val Thr Gln Glu Pro Ile Tyr Ile Ile Thr
 65                  70                  75                  80

Glu Tyr Met Glu Asn Gly Ser Leu Val Asp Phe Leu Lys Thr Pro Ser
                 85                  90                  95

Gly Ile Lys Leu Thr Ile Asn Lys Leu Leu Asp Met Ala Ala Gln Ile
            100                 105                 110

Ala Glu Gly Met Ala Phe Ile Glu Glu Arg Asn Tyr Ile His Arg Asn
        115                 120                 125

Leu Arg Ala Ala Asn Ile Leu Val Ser Asp Thr Leu Ser Cys Lys Ile
130                 135                 140

Ala Asp Phe Gly Leu Ala Arg Leu Ile Glu Asp Asn Glu Tyr Thr Ala
145                 150                 155                 160

Arg Glu Gly Ala Lys Phe Pro Ile Lys Trp Thr Ala Pro Glu Ala Ile
                165                 170                 175

Asn Tyr Gly Thr Phe Thr Ile Lys Ser Asp Val Trp Ser Phe Gly Ile
            180                 185                 190

Leu Leu Thr Glu Ile Val Thr His Gly Arg Ile Pro Tyr Pro Gly Met
        195                 200                 205

Thr Asn Pro Glu Val Ile Gln Asn Leu Glu Arg Gly Tyr Arg Met Val
    210                 215                 220

Arg Pro Asp Asn Cys Pro Glu Glu Leu Tyr Gln Leu Met Arg Leu Cys
225                 230                 235                 240

Trp Lys Glu Arg Pro Glu Asp Arg Pro Thr Phe Asp Tyr Leu Arg Ser
                245                 250                 255

Val Leu Glu Asp Phe Phe Thr Ala Thr
            260                 265

<210> SEQ ID NO 3
<211> LENGTH: 271
<212> TYPE: PRT
<213> ORGANISM: Homo sapiens
<220> FEATURE:
<221> NAME/KEY: MUTAGEN
<222> LOCATION: (364)
<223> OTHER INFORMATION: non-conservative Asp-364-Asn mutation
<220> FEATURE:
```

-continued

```
<221> NAME/KEY: PHOSPHORYLATION
<222> LOCATION: (394)

<400> SEQUENCE: 3

Lys Pro Trp Trp Glu Asp Glu Trp Val Pro Arg Glu Thr Leu Lys
1               5                   10                  15

Leu Val Glu Arg Leu Gly Ala Gly Gln Phe Gly Glu Val Trp Met Gly
            20                  25                  30

Tyr Tyr Asn Gly His Thr Lys Val Ala Val Lys Ser Leu Lys Gln Gly
        35                  40                  45

Ser Met Ser Pro Asp Ala Phe Leu Ala Glu Ala Asn Leu Met Lys Gln
    50                  55                  60

Leu Gln His Gln Arg Leu Val Arg Leu Tyr Ala Val Val Thr Gln Glu
65                  70                  75                  80

Pro Ile Tyr Ile Ile Thr Glu Tyr Met Glu Asn Gly Ser Leu Val Asp
                85                  90                  95

Phe Leu Lys Thr Pro Ser Gly Ile Lys Leu Thr Ile Asn Lys Leu Leu
            100                 105                 110

Asp Met Ala Ala Gln Ile Ala Glu Gly Met Ala Phe Ile Glu Glu Arg
        115                 120                 125

Asn Tyr Ile His Arg Asn Leu Arg Ala Ala Asn Ile Leu Val Ser Asp
    130                 135                 140

Thr Leu Ser Cys Lys Ile Ala Asp Phe Gly Leu Ala Arg Leu Ile Glu
145                 150                 155                 160

Asp Asn Glu Tyr Thr Ala Arg Gln Gly Ala Lys Phe Pro Ile Lys Trp
                165                 170                 175

Thr Ala Pro Glu Ala Ile Asn Tyr Gly Thr Phe Thr Ile Lys Ser Asp
            180                 185                 190

Val Trp Ser Phe Gly Ile Leu Leu Thr Glu Ile Val Thr His Gly Arg
        195                 200                 205

Ile Pro Tyr Pro Gly Met Thr Asn Pro Glu Val Ile Gln Asn Leu Glu
    210                 215                 220

Arg Gly Tyr Arg Met Val Arg Pro Asp Asn Cys Pro Glu Glu Leu Tyr
225                 230                 235                 240

Gln Leu Met Arg Leu Cys Trp Lys Glu Arg Pro Glu Asp Arg Pro Thr
                245                 250                 255

Phe Asp Tyr Leu Arg Ser Val Leu Glu Asp Phe Phe Thr Ala Thr
            260                 265                 270
```